(12) United States Patent
Chakravarty et al.

(10) Patent No.: US 7,822,782 B2
(45) Date of Patent: Oct. 26, 2010

(54) APPLICATION PACKAGE TO AUTOMATICALLY IDENTIFY SOME SINGLE STRANDED RNA VIRUSES FROM CHARACTERISTIC RESIDUES OF CAPSID PROTEIN OR NUCLEOTIDE SEQUENCES

(75) Inventors: Sugoto Chakravarty, Houston, TX (US); Dianhui Zhu, Houston, TX (US); George E. Fox, Manuel, TX (US)

(73) Assignee: The University of Houston System, Houston, TX (US)

(*) Notice: Subject to any disclaimer, the term of this patent is extended or adjusted under 35 U.S.C. 154(b) by 308 days.

(21) Appl. No.: 11/903,564

(22) Filed: Sep. 21, 2007

(65) Prior Publication Data

US 2008/0195612 A1  Aug. 14, 2008

Related U.S. Application Data

(60) Provisional application No. 60/846,206, filed on Sep. 21, 2006.

(51) Int. Cl.
*G06F 7/00* (2006.01)
*G06F 17/30* (2006.01)

(52) U.S. Cl. ...................................... 707/802; 707/808
(58) Field of Classification Search ............... 707/1–10, 707/104.1, 200–206; 702/19, 20; 530/350
See application file for complete search history.

(56) References Cited

U.S. PATENT DOCUMENTS

| 6,738,502 B1* | 5/2004 | Coleman et al. ............. 382/133 |
| 7,363,166 B2* | 4/2008 | Brahmachari et al. ......... 702/19 |
| 2006/0218182 A1* | 9/2006 | Giffard et al. ............ 707/104.1 |

OTHER PUBLICATIONS

Rambally, A visualization approach to motif discovery in DNA sequences, Mar. 22-23, 2007, IEEE, 348-353.*
Davies et al., Optimal structure for automatic processing of DNA sequences, Sep. 1999, IEEE, 1044-1056.*

* cited by examiner

*Primary Examiner*—Jean B Fleurantin
(74) *Attorney, Agent, or Firm*—Robert W Strozier

(57) ABSTRACT

A system implemented on a computer is disclosed for automatically identifying strains of partial or complete capsid sequences of picorna and caliciviruses, two of the most highly diverse ssRNA virus families.

37 Claims, 782 Drawing Sheets

MMMASKDATSSMDGASGAGQLVPEVNASDPLAMDPVAGSSTAVAATAGQVNPIDPWIINNF 60
VQAPQGEFTISPNNTPGDVLRDISLGPHLNPFLLHLSQMYNGWVCGNMRVRIMLAGNAFTA 120
GKIIMCIPPGFGSHNLTIAQATLPHVIADVRILDPIEVPLEDVRNVLFNNNDRNQQTM 180
RLVQMLYTPLRTGGGTGDSFVVAGRVMTCPSPDFNFLAILVPPTVEQKTRPFTLPNIPLSS 240
LSNSRAPLRISSMGISTDAIVQSVQFQNGRCTLDGRLVGTTPVSLSHVAKIRGTSNGTVTN 300
LTELDGTPFHPFEGPAPIGFPDLGGCDWHINMTQFGHSSQTQYDVDITPDTFVPHLGSIQ 360
ANGIGSGNYVGVLSWISPPSHPSGSQVDLWKIPNYGSSITEATHLAPSVYPPGFGEVLMI 420
FMSKMPGPGAYNLPCLLPQEYISHLASEQAPTVGEAALIHYVDPDTGRNLGEFKAYPDGF 480
LTCVPNGASSGPQQLPINGVFVFMSWVSRFYQLKPVGTASSARGRLGLRR 530

FIG. 2B

Query sequence number: 55  (1)
Query file: C:\seq.txt  (2)
Query organism name: NV|Seacroft|tr|Q9IV37 Capsid protein - Human calicivirus Seacroft/90/UK. (Searching Noro database) (3)

Proceeding path: -->G2-->G2-->G2-->.-->G5--> G9-->G10-->G11-->G10 (4)

P2 (GII) | P3 (GII) | P4 P5 (GIIa) | P6 (GIIa3) | P7 (GIIa3_2) | P8 | P9 | P10 (5)

Analysis indicates that the input sequence belongs to group/class 10 of partition 10.
This group consists of the following sequences
51_NV|Arg320 (Q9PYA7)
52_NV|Japan (23830)
53_NV|Arg320 (Q9PYA7)
54_NV|Bitberg (Q915D2)
55_NV|Oberhausen (Q916E5) (6)
56_NV|Bham132 (Q9IV46)
57_NV|Rbh (Q9IV40)
58_NV|minireovirus (U02030)
59_NV|Toronto (Q66296)
61_NV|Mexico (Q68291)
62_NV|Mexico (Q68291)
60_NV|Auckland (U46039)
Conclusion: This query sequence is closest to 58_NV|minireovirus in Noro database

FIG. 3

Receptor

Antibody

N₁, P₁, N₂, C₁, N₃, P₃, N₄

Capsid

FIG. 4D

Altered receptor & antibody binding

N₁, P₁, N₂, C₁, N₃, P₃, N₄

Altered capsid

FIG. 4E

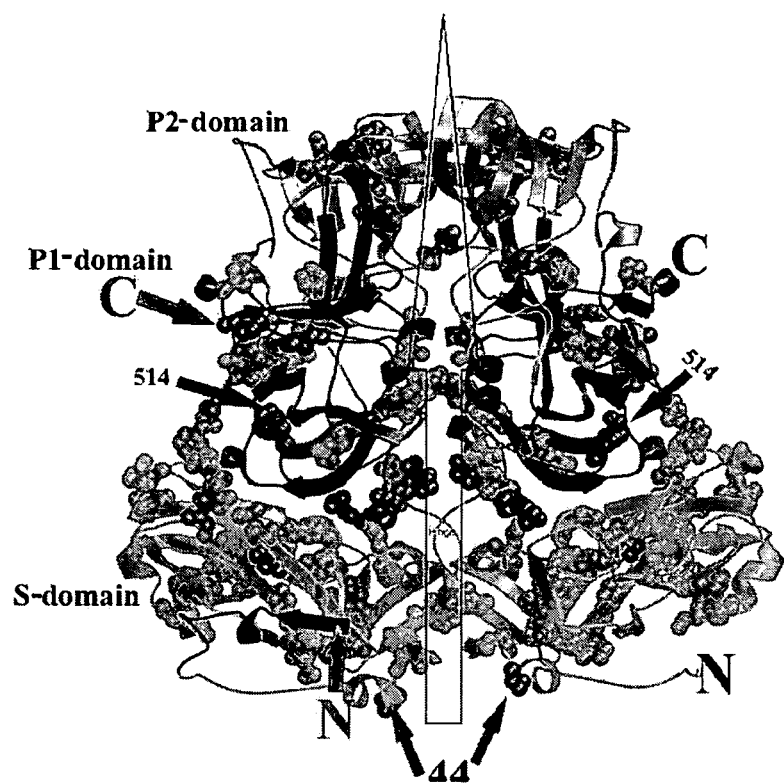
FIG. 7A
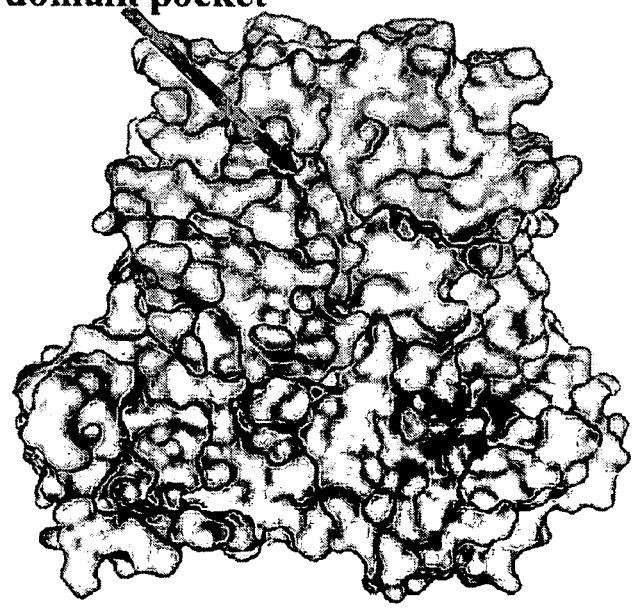
FIG. 7B

```
  1  Partitions P02-P05: (CLASS_B contains HRV14; CLASS_A contains HRV16)
  2  ===============================================================================
  3  CLASS_B      -M---G-ET---E-PLGR-ACVH----I-N--------┃   ┃---...L---W---
  4  CLASS_A      ----T--E---E-PLGR--C-----------------┃...┃...------W---
  5  SUMMARY      -------E---E-PLGR--C-----------------┃   ┃--------W---
  6
  7  Partition  P06: (CLASS_1 contains HRV14; CLASS_2 contains HRV16)
  8  ===============================================================================
  9  CLASS_1 ⇒B   -M---G-ET---E-PLGR-ACVH----I-N--------┃   ┃---...L---W---
 10  CLASS_2      ----T--EH--E-PLGR-GC--H--------------┃...┃...------W---
 11  CLASS_3  ⇒A  ITDQTRDETSIESPLGRSGCIA-----T---------┃...┃...--D---G-G--TWK-S
 12  CLASS_4      -TDQT-DEHS-ESFLGRS-C----------H------┃...┃..-Y---...-N---W-I-
 13  CLASS_5      I-DQTR-ETS-ESFLGRAGC----I-L----HD-...┃...┃...Y-.....------W-I-
 14  SUMMARY      --------EX--E-FLGR--C----------------┃...┃...--------X-----W---
 15
 16  Partition  P07: (CLASS_1contains HRV14; CLASS_5 contains HRV16)
 17  ===============================================================================
 18  CLASS_1      YM-F-GSETD-E-FLGRAACVH----I-NK--------┃...┃...N-----...-LFNDW-I-
 19  CLASS_2      YMH--GSET--ENFLGRSACVHITEI-N--P------┃   ┃---THK-Q...-LF-DWK--
 20  CLASS_3  ⇒B  -MHY-GSETTLENPLGRAACVHVVEI-NK---D----┃...┃..-H-----...LLPN-WKI-
 21  CLASS_4      YMHYDG-ETS-ESPLGR-ACVHV--IENK-P------┃...┃..-HK-Q...KL--DWKIN
 22  CLASS_5      QSSQTLDEMSVESPLGRSGCIHES-LDI-.--.....┃...┃...YN-.....QSPTKW-IN
 23  CLASS_6      ----T--EM--E-FLGRSGC-H-------Y-------┃...┃...Y-----..-N---W---
 24  CLASS_7      -TSQTRDEMSIESFLGRSGCVHISRIKVDY-D.....┃...┃...YNG---..-NFT-WKIT
 25  CLASS_8      -NFQTRDEMSIESFLGRSGCIMISTLE---Y------┃...┃...YNG-G...-NFIQWPIN
 26  CLASS_9      QTSQTRDEMSLESFLGRSGCIMESKL-----------┃...┃...Y---.....-NF--W-IN
 27  CLASS_10 ⇒A  QTS-TRDEMS-ESFLGR-GCIH-STI-----------┃...┃..-Y.....------W-IT
 28  CLASS_11     QT---TRDEMSIESFLGRSGC-H-S-I----------┃...┃...H--.....-----W--N
 29  CLASS_12     ITDQTRDETSIESPLGRSGCIA-----T---------┃...┃...--D---G-G--TWK-S
 30  CLASS_13     ITDQTRDEMSIESFLGRSGC---I--L-LDB---...┃...┃...Y-AEG...KNP-TWKIN
 31  CLASS_14     -TDQT-DEMS-ESFLGRS-C-A-I-T----H------┃...┃..-YN--....-N-S-W-IT
 32  CLASS_15     I-DQTR-ETS-ESFLGRAGC----I-L----HD-...┃...┃...Y-.....------W-I-
 33  SUMMARY      --------EX--E-FLGR--C----------------┃...┃...--------X-----W---
 34
 35  Partition  P08: (CLASS_1contains HRV14; CLASS_5 contains HRV16)
 36  ===============================================================================
 37  CLASS_1      YMHF-GSETD-E-PLGRAACVH----I-NK--------┃...┃...N-----...-LFNDW-I-
 38  CLASS_2  ⇒B  YMH--GSET--ENFLGRSACVHITEI-N--P------┃   ┃---THK-Q...-LF-DWK--
 39  CLASS_3      -MHY-GSETTLENPLGRAACVHVVEI-NK---D----┃...┃..-H-----...LLPN-NKI-
 40  CLASS_4      YMHYDG-ETS-ESPLGR-ACVHV--IENK-P------┃...┃..-HK-Q...KL--DWKIN
 41  CLASS_5      QSSQTLDEMSVESPLGRSGCIHES-LDI-.--.....┃...┃...YN-.....QSPTKW-IN
 42  CLASS_6      QTSQT---EM---ESFLGRSGCIH-SKL-V--Y----┃...┃...Y---.....-NF--W-IN
 43  CLASS_7      QTS-TRDEMS-E-FLGRSGC-H-S-L-V--Y------┃...┃...YN-----.-NF---W--W
 44  CLASS_8      QTSQTRDEMSIESFLGRSGC-HMSKL-VNYDN.....┃...┃...YNTGE...MNI-THQIN
 45  CLASS_9      Q----TRDEMSLESFLGRSGC--MISKL--IDY----┃...┃...Y---S-...-NFTIWKIN
 46  CLASS_10     Q--QTRDEMS-ESFLGRSGC-HIS-L-I-Y-------┃...┃...YN----..KNFY-WQIN
 47  CLASS_11     ----QTRDEMS-ESFLGRSGC-H----L----Y----┃...┃...YN----.NNF--WQI-
 48  CLASS_12     QTSQTRDEMS-ESFLGRSGC--H-ST-NI-Y------┃...┃...YDD---..-NF--WKI-
 49  CLASS_13     -TSQTRDEMSIESFLGRSGCVHISRIKVDY-D.....┃...┃...YNG---..-NFT-WKIT
 50  CLASS_14     -NFQTRDEMSIESFLGRSGCIHISTLE---Y------┃...┃...YNG-G....-NFTQWPIN
 51  CLASS_15 ⇒A  QTSQTRDEMSLESFLGRSGCIHESKL-----------┃...┃...Y---.....-NF--W-IN
 52  CLASS_16     QTSQTRDEMSIESFLGRSGCIH-STI-V---------┃...┃..-Y.-E....--F--WQIT
 53  CLASS_17     QTSQTRDEMS-ESFLGR-GCIH-STIT--N-------┃...┃..-Y.----..-H---W-IT
 54  CLASS_18     QTS-TRDEMSVESFLGRSGCCIHISTIT---K-----┃...┃..-Y.----..--F--W-IT
 55  CLASS_19     QT--QTRDEMSIESFLGRSGCVH-S-I----------┃...┃....H--....---R-W-IN
 56  CLASS_20     QTS-TRDEMSIESFLGRSGCCIHVSTIK-NQA.....┃...┃....H--....KFDRWN-W
 57  CLASS_21     ITDQTRDETSIESFLGRSGCIA-----T---------┃...┃...--D---G-G--TWK-S
 58  CLASS_22     ITDQTRDEMS-ESFLGRSGCIAIIHTDLDH---Q...┃...┃...YNAPG...KNFSQWKIT
 59  CLASS_23     ITDQTRDEMSIESFLGRSSCIA-IHT----H------┃...┃..-YN-PG...KN-S-W-IT
 60  CLASS_24     -TDQTRDEMS-ESFLGRSAC-A-IHT-L-H-------┃...┃..-YN--G...-N-S-W-IT
 61  CLASS_25     ITDQTRDEMSIESFLGRSGC-AIIET-LNHE------┃...┃...YNA---..QNFSKWKIT
 62  CLASS_26     ITDQTR-ETSLESFLGRAGCIKIIALELDHDN.....┃...┃...YD......--FRTWGIN
 63  SUMMARY      --------EX--E-FLGR-XC-X--------------┃...┃...--------X-----W---
 64
 65  Partition  P09: (CLASS_2contains HRV14; CLASS_9 contains HRV16)
 66  ===============================================================================
 67  CLASS_1      YMHFNGSETD-ESPLGRAACVHITEIENKN-------┃...┃...N-K---...KLPNDWKIN
 68  CLASS_2      YMHFNGSETD-ECPLGRAACVHVTEI-NK---GI-..┃...┃...NH----...KLPNDWKI-
 69  CLASS_3      YMHFNGSETD-E-FLGRAACVHMV-IVNKRP------┃...┃...NQK---...-LFNDWRIH
 70  CLASS_4      YMH-TGSET--LENFLGRSACVHITEI--NKLP--P-┃-G-┃M-NTHKEQ...-LFNDWKI-
 71  CLASS_5      YMHF-GSETTLENFLGRSACVHITEI-N--P----T-┃E-T┃...THKEQ...KLF-DWK--
```

FIG. S1

Partition P09 - contd-

```
 72 CLASS_6    LMHY-GSETTLEHFLGRAACVHVVEI-HKR-TD--    ...   ...-HK--...LLFNDWKI-
 73 CLASS_7  ⇒B -MHYTGSETTLEHFLGRAACVHVVEI-HN-PTD-E   ...   ...EH--Q...LLFN-WKIN
 74 CLASS_8    YMHYDGTETS-ESFLGRAACVHV---IENKLP----   ...   ...-HK-Q...KL-NDWKIN
 75 CLASS_9    QSSQTLDEMSVESFLGRSGCIHES-LDI-.--...    ...   ...YN-.....QSFIKW-IN
 76 CLASS_10   QTSQTLDEM--ESFLGRSGCIH-SKL-V-YE-...    ...   ...Y---.-..KMF-TWKIN
 77 CLASS_11   QTSQT--EMSVESFLGRSGCIHMSKL-V-YDN...    ...   ...YD...-..-NF-KWQIN
 78 CLASS_12   QTS-TRDEMSIESFLGRSGCIH-SKLVVDY--...    ...   ...YN--T...KMF--WQIN
 79 CLASS_13   QTSQTRDEMSIESFLGRSGCIHMSKL-VNYDN...    ...   ...YNTGE....NNI-TWQIN
 80 CLASS_14   Q----TRDEMSLESFLGRSGC-HIGKL-IDY---    ...   ...Y--S-...-NFIIWRIN
 81 CLASS_15   QTSQTRDEMS-ESFLGRSGC-HIS-LKI-Y--...    ...   ...YN--G...KMFTKWQIN
 82 CLASS_16   QHTQTRDEMSIESFLGRSGCIHI---L----Y-G...  ...   ...YND-G...NNF--WQIT
 83 CLASS_17   --SQTRDEMS-ESFLGRSGCIHIGHL-V-YT-...    ...   ...YN-EG...NNF--WQI-
 84 CLASS_18   QTSQTRDEMS-ESFLGRSGCIHMSTLNI-YDN...    ...   ...YDDS-....NFKVWKIN
 85 CLASS_19   -TSQTRDEMSIESFLGRSGCVHISRIKVDY-D...    ...   ...YNG--...-NFI-WKIT
 86 CLASS_20   -NFQTRDEMSIESFLGRSGCIHISTLE---Y--...   ...   ...YNG-G...-NFTQNPIN
 87 CLASS_21   QTSQTRDEMSLESFLGRSGCIHESKLEVIL-N...    ...   ...YN-....-NF-VW-IN
 88 CLASS_22 ⇒A QTSQTRDEMSLESFLGRSGCIHESKL--E----...  ...   ...YD-.....-NF-TWNIN
 89 CLASS_23   QTSQTRDEMSIESFLGRSGCIHTSTITV----...    ...   ...-Y.NE...HIFD-WQIT
 90 CLASS_24   QTSQTRDEMSIESFLGRSGCIHISTINV---K...    ...   ...TY.DE...SKFR-WQIT
 91 CLASS_25   QTSQTRDEMSIESFLGRSGCIHISTITV-N-L...    ...   ...-Y.D-...-HFD-WQIT
 92 CLASS_26   QTSQTRDEMSIESFLGRAGCIHESTITIQNDV...    ...   ...EY.ND...HHF--WDIT
 93 CLASS_27   QTSQTRDEMSVESFLGRSGCIHISTITV-K-I...    ...   ...-Y.D-...GHF-KW-IT
 94 CLASS_28   QTTQTRDEMSIESFLGRSGCVHTSTIET-L-....    ......H-...-RFK-WNIN
 95 CLASS_29   QT-QTRDEMSIESFLGRSGCVH-S-I------...    ......H-...-K-KVWHIN
 96 CLASS_30   QTS-TRDEMSIESFLGRSGCIHVSTIK-NQA....    ......H-...-KFDKWN-N
 97 CLASS_31   ITDQTRDETSIESFLGRSGCIAK-KLDT-..-...    ...GDYDT--GVGF-TWKIS
 98 CLASS_32   ITDQTRDETSIESFLGRSGCIA-I-F-T---K...    ...---D-.IG-G-KIWK-S
 99 CLASS_33   ITDQTRDEMS-ESFLGRSGCIAIIHTDLDH---Q...  ...YNAPG...KMFSQWRIT
100 CLASS_34   ITDQTKDEMSIESFLGRSGC-AIIET-LNHE---.    ...YNA--...QNFSKWRIT
101 CLASS_35   ITDQTR-ETSLESFLGRAGCIKIIALELDHDN...    ...YD.......--FRTWGIN
    SUMMARY   -------EX--E-FLGRXXC-X---X--------    ----X-------X------W---
```

FIG. S1 CONT'D

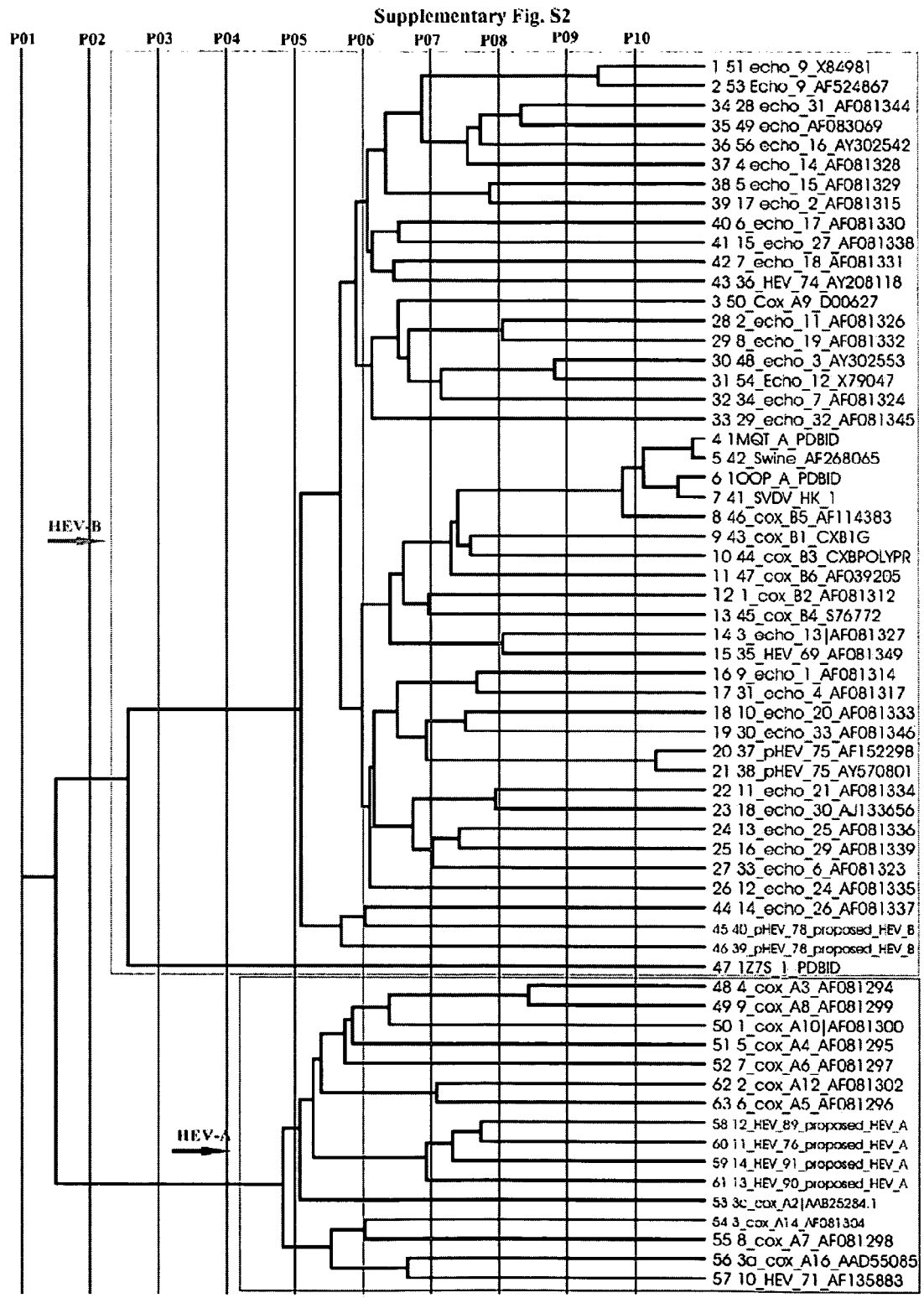
FIG. S2

FIG. S3

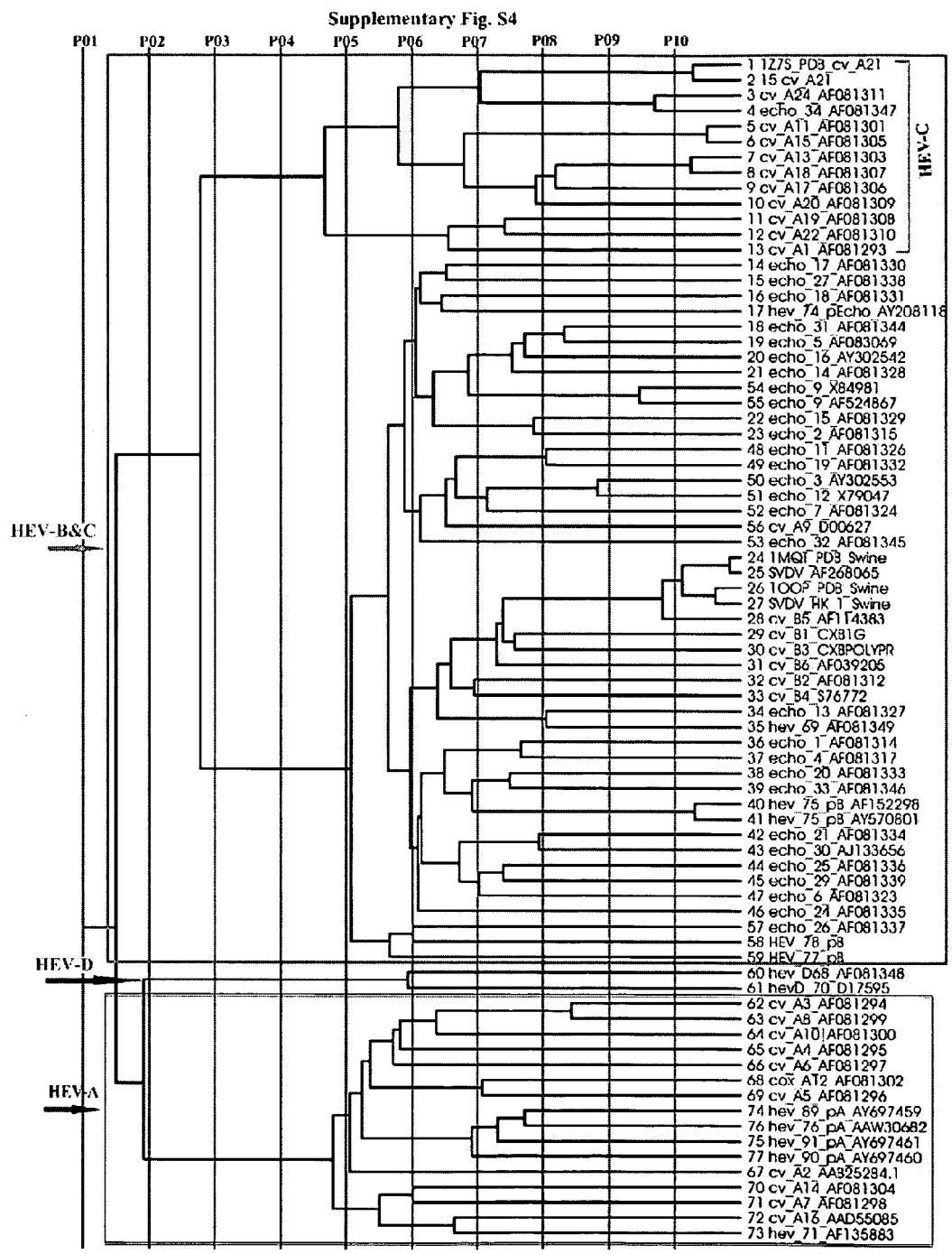
FIG. S4

Rhino_cDNA_DB.fasta                                                    9/20/2007 5:08 PM

```
  1 >1_HRV1A1|d
  2 AATCCAGTAGAAAACTACATTGATGAAGTTTTAAATGAAGTTTTAGTAGTGCCGAATATA
  3 AAAGAAAGTCATCACACTACATCAAACTCTGCCCCACTTTTAGATGCTGCAGAGACGGGA
  4 CACACCAGTAATGTTCAACCAGAAGATGCTATAGAGACAAGGTATGTTATAACATCACAA
  5 ACAAGAGATGAGATGAGTATAGAAAGTTTCCTTGGTAGATCTGGTTGTGTCCACATCTCA
  6 AGAATAAAGGTTGATTACACTGACTATAATGGACAGGACATAAATTTCACAAAATGGAAA
  7 ATCACACTACAGGAAATGGCACAGATTAGGAGAAAATTTGAATTGTTTACATATGTCAGG
  8 TTTGACTCAGAAATAACCTTGGTGCCTTGTATTGCTGGTAGAGGAGACGACATTGGACAT
  9 ATTGTAATGCAATATATGTATGTTCCTCCAGGAGCTCCAATTCCTTCAAAAAGAAACGAT
 10 TTCTCATGGCAATCAGGCACCAATATGTCAATATTCTGGCAACATGGACAGCCATTTCCT
 11 AGATTTTCTTTACCATTTCTTAGCATTGCATCAGCTTATTATATGTTTTATGATGGATAT
 12 GATGGAGACAACACTTCTTCCAAGTATGGTAGCGTAGTTACTAATGATATGGGTACTATA
 13 TGCTCAAGAATAGTTACAGAAAAACAGAAACATTCTGTTGTCATCACAACACACATATAT
 14 CATAAAGCTAAACACACAAAAGCTTGGTGTCCTAGGCCCCCTAGAGCTGTCCCTTACACA
 15 CATAGTCATGTGACTAATTATATGCCAGAAACAGGTGACGTGACAACAGCCATAGTCCGC
 16 AGAAACACTATAACAACTGCA
 17 >2_HRV1A2|d
 18 AATCCAGTAGAAAACTACATTGATGAAGTTTTAAATGAAGTTTTAGTAGTGCCGAATATA
 19 AAAGAAAGTCATCACACTACATCAAACTCTGCCCCACTTTTAGATGCTGCAGAGACGGGA
 20 CACACCAGTAATGTTCAACCAGAAGATGCTATAGAGACAAGGTATGTTATAACATCACAA
 21 ACAAGAGATGAGATGAGTATAGAAAGTTTCCTTGGTAGATCTGGTTGTGTCCACATCTCA
 22 AGAATAAAGGTTGATTACACTGACTATAATGGACAGGACATAAATTTCACAAAATGGAAA
 23 ATCACACTACAGGAAATGGCACAGATTAGGAGAAAATTTGAATTGTTTACATATGTCAGG
 24 TTTGACTCAGAAATAACCTTGGTGCCTTGTATTGCTGGTAGAGGAGACGACATTGGACAT
 25 ATTGTAATGCAATATATGTATGTTCCTCCAGGAGCTCCAATTCCTTCAAAAAGAAACGAT
 26 TTCTCATGGCAATCAGGCACCAATATGTCAATATTCTGGCAACATGGACAGCCATTTCCT
 27 AGATTTTCTTTACCATTTCTTAGCATTGCATCAGCTTATTATATGTTTTATGATGGATAT
 28 GATGGAGACAACACTTCTTCCAAGTATGGTAGCGTAGTTACTAATGATATGGGTACTATA
 29 TGCTCAAGAATAGTTACAGAAAAACAGAAACATTCTGTTGTCATCACAACACACATATAT
 30 CATAAAGCTAAACACACAAAAGCTTGGTGTCCTAGGCCCCCTAGAGCTGTCCCTTACACA
 31 CATAGTCATGTGACTAATTATATGCCAGAAACAGGTGACGTGACAACAGCCATAGTCCGC
 32 AGAAACACTATAACAACTGCG
 33 >3_HRV1A|cD
 34 AATCCAGTAGAAAACTACATTGATGAAGTTTTAAATGAAGTTTTAGTAGTGCCGAATATA
 35 AAAGAAAGTCATCACACTACATCAAACTCTGCCCCACTTTTAGATGCTGCAGAGACGGGA
 36 CACACCAGTAATGTTCAACCAGAAGATGCTATAGAGACAAGGTATGTTATAACATCACAA
 37 ACAAGAGATGAGATGAGTATAGAAAGTTTCCTTGGTAGATCTGGTTGTGTCCACATCTCA
 38 AGAATAAAGGTTGATTACACTGACTATAATGGACAGGACATAAATTTCACAAAATGGAAA
 39 ATCACACTACAGGAAATGGCACAGATTAGGAGAAAATTTGAATTGTTTACATATGTCAGG
 40 TTTGACTCAGAAATAACCTTGGTGCCTTGTATTGCTGGTAGAGGAGACGACATTGGACAT
 41 ATTGTAATGCAATATATGTATGTTCCTCCAGGAGCTCCAATTCCTTCAAAAAGAAACGAT
 42 TTCTCATGGCAATCAGGCACCAATATGTCAATATTCTGGCAACATGGACAGCCATTTCCT
 43 AGATTTTCTTTACCATTTCTTAGCATTGCATCAGCTTATTATATGTTTTATGATGGATAT
 44 GATGGAGACAACACTTCTTCCAAGTATGGTAGCGTAGTTACTAATGATATGGGTACTATA
 45 TGCTCAAGAATAGTTACAGAAAAACAGAAACATTCTGTTGTCATCACAACACACATATAT
 46 CATAAAGCTAAACACACAAAAGCTTGGTGTCCTAGGCCCCCTAGAGCTGTCCCTTACACA
 47 CATAGTCATGTGACTAATTATATGCCAGAAACAGGTGACGTGACAACAGCCATAGTCCGC
 48 AGAAACACTATAACAACTGCT
 49 >4_HRV1B1|d
 50 AATCCAGTGGAAAATTACATTGATGAAGTTTTAAATGAAGTTCTAGTAGTACCAAATATA
 51 AAAGAAAGCCATCACACTACATCAAATTCTGCTCCACTCTTGGATGCTGCAGAGACAGGA
 52 CACACCAGTAATGTACAACCAGAGGATGCTATAGAAACAAGATATGTTATGACATCACAA
 53 ACAAGAGATGAGATGAGTATAGAAAGTTTCTTGGTAGATCTGGCTGTGTGCATATTTCA
 54 AGAATAAAGGTTGATTACAATGACTACAATGGAGTGAACAAAAACTTTACAACATGGAAA
 55 ATCACACTGCAGGAGATGGCACAAATTAGAAGAAAATTCGAACTATTTACTTATGTTAGG
 56 TTTGATTCAGAAGTAACTTTAGTACCCTGTATTGCTGGTAGAGGAGATGACATTGGTCAT
 57 GTTGTAATGCAGTATATGTATGTTCCCCCAGGAGCTCCAATTCCAAAAACAAGAAATGAT
 58 TTCTCATGGCAATCAGGCACTAATATGTCAATATTCTGGCAACATGGACAACCGTTCCCT
 59 AGATTCTCTTTACCATTTCTTAGCATTGCATCAGCTTATACATGTTTTATGGATGGATAT
 60 GATGGAGATAATTCCTCTTCCAAATATGGTAGTATAGTCACCAATGATATGGGAACCATA
 61 TGTTCAAGAATAGTTACAGAGAAGCAGGAACACCCTGTCGTTATTACAACACACATATAT
 62 CACAAAGCTAAACACACAAAAGCTTGGTGTCCTAGACCTCCTAGAGCTGTTCCTTACACA
 63 CATAGTCGTGTAACTAATTATGTACCAAAAACAGGTGATGTGACAACAGCTATAGTTCCT
 64 AGAGCTAGCATGAAAACTGTA
 65 >5_HRV1B2|d
```

FIG. D1

Rhino_cDNA_DB.fasta                                                9/20/2007 5:08 PM

```
 66 AATCCAGTGGAAAATTACATTGATGAAGTTTTAAATGAAGTTCTAGTAGTACCAAATATA
 67 AAAGAAAGCCATCACACTACATCAAATTCTGCTCCACTCTTGGATGCTGCAGAGACAGGA
 68 CACACCAGTAATGTACAACCAGAGGATGCTATAGAAACAAGATATGTTATGACATCACAA
 69 ACAAGAGATGAGATGAGTATAGAAAGTTTTCTTGGTAGATCTGGCTGTGTGCATATTTCA
 70 AGAATAAAGGTTGATTACAATGACTACAATGGAGTGAACAAAAACTTTACAACATGGAAA
 71 ATCACACTGCAGGAGATGGCACAAATTAGAAGAAAATTCGAACTATTTACTTATGTTAGG
 72 TTTGATTCAGAAGTAACTTTAGTACCCTGTATTGCTGGTAGAGGAGATGACATTGGTCAT
 73 GTTGTAATGCAGTATATGTATGTTCCCCCAGGAGCTCCAATTCCAAAAACAAGAAATGAT
 74 TTCTCATGGCAATCAGGCACTAATATGTCAATATTCTGGCAACATGGACAACCGTTCCCT
 75 AGATTCTCTTTACCATTTCTTAGCATTGCATCAGCTTATTACATGTTTTATGATGGATAT
 76 GATGGAGATAATTCCTCTTCCAAATATGGTAGTATAGTCACCAATGATATGGGAACCATA
 77 TGTTCAAGAATAGTTACAGAGAAGCAGGAACACCCTGTCGTTATTACAACACACATATAT
 78 CACAAAGCTAAACACACAAAAGCTTGGTGTCCTAGACCTCCTAGAGCTGTTCCTTACACA
 79 CATAGTCGTGTAACTAATTATGTACCAAAAACAGGTGATGTGACAACAGCTATAGTTCCT
 80 AGAGCTAGCATGAAAACTGTC
 81 >6_HRV1B
 82 AATCCAGTGGAAAATTACATTGATGAAGTTTTAAATGAAGTTCTAGTAGTACCAAATATA
 83 AAAGAAAGCCATCACACTACATCAAATTCTGCTCCACTCTTGGATGCTGCAGAGACAGGA
 84 CACACCAGTAATGTACAACCAGAGGATGCTATAGAAACAAGATATGTTATGACATCACAA
 85 ACAAGAGATGAGATGAGTATAGAAAGTTTTCTTGGTAGATCTGGCTGTGTGCATATTTCA
 86 AGAATAAAGGTTGATTACAATGACTACAATGGAGTGAACAAAAACTTTACAACATGGAAA
 87 ATCACACTGCAGGAGATGGCACAAATTAGAAGAAAATTCGAACTATTTACTTATGTTAGG
 88 TTTGATTCAGAAGTAACTTTAGTACCCTGTATTGCTGGTAGAGGAGATGACATTGGTCAT
 89 GTTGTAATGCAGTATATGTATGTTCCCCCAGGAGCTCCAATTCCAAAAACAAGAAATGAT
 90 TTCTCATGGCAATCAGGCACTAATATGTCAATATTCTGGCAACATGGACAACCGTTCCCT
 91 AGATTCTCTTTACCATTTCTTAGCATTGCATCAGCTTATTACATGTTTTATGATGGATAT
 92 GATGGAGATAATTCCTCTTCCAAATATGGTAGTATAGTCACCAATGATATGGGAACCATA
 93 TGTTCAAGAATAGTTACAGAGAAGCAGGAACACCCTGTCGTTATTACAACACACATATAT
 94 CACAAAGCTAAACACACAAAAGCTTGGTGTCCTAGACCTCCTAGAGCTGTTCCTTACACA
 95 CATAGTCGTGTAACTAATTATGTACCAAAAACAGGTGATGTGACAACAGCTATAGTTCCT
 96 AGAGCTAGCATGAAAACTGTT
 97 >7_HRV40a|d
 98 AACCCCGTTGAAAGGTATGTTGATGAGGTTCTTAATGAAGTTCTGGTAGTTCCAAATATC
 99 AGAGAGAGCCATCCAACTACATCAAATTCGGCCCCTGCCTTGGATGCAGCAGAGACTGGA
100 CATACAAGCAACATACAACCTGAAGATACAATAGAAACAAGATTTGTGCAGACATCACAA
101 ACTAGAGATGAAATGAGCATAGAGAGTTTCTTGGGAAGATCTGGGTGCATTCATATATCC
102 ACAATTACAGTGGATAACAGTTTGGAATATGATGACCACCACTTTGATAAGTGGCAGATA
103 ACCATACAAGAGATGTCACAAATTAGGAGAAAATTTGAATTCTTTACATATGCTAGGTTT
104 GATTCAGAAATTACCTTAGTTCCTTGTATAGCCGGTAAGGGTGAAGACATTGGACACATT
105 GTGATGCAATATATGTATGTACCCCCTGGCGCACCCATACCAAAGAAAAGAAATGATTAC
106 ACATGGCAGTCAGGCACTAATGCTTCTGTATTCTGGCAACATGGTCAAACTTTCCCTAGA
107 TTTTCTTTACCTTTCCTAAGCATAGCTTCAGCATACTACATGTTTTATGATGGATACGAT
108 GGTGATACATCGACCTCAAGATATGGCACATCAGTCACTAACCATATGGGAACGCTATGC
109 TCAAGAATAGTCACCAACAAGCAGCAGCATGAAGTTGAGATTACCACACGTATATATCAC
110 AAGGCCAAGCATATTAAAGCATGGTGTCCAAGGGCCCCAAGAGCAGTACCTTACACACAT
111 ACACACTCAACAAATTATAAACCTCAAGAAGGTGAAGTCCAGATTTTCCTCAAAGAGAGA
112 GCCAGCCTAACAACAGTA
113 >8_HRV40b|d
114 AACCCCGTTGAAAGGTATGTTGATGAGGTTCTTAATGAAGTTCTGGTAGTTCCAAATATC
115 AGAGAGAGCCATCCAACTACATCAAATTCGGCCCCTGCCTTGGATGCAGCAGAGACTGGA
116 CATACAAGCAACATACAACCTGAAGATACAATAGAAACAAGATTTGTGCAGACATCACAA
117 ACTAGAGATGAAATGAGCATAGAGAGTTTCTTGGGAAGATCTGGGTGCATTCATATATCC
118 ACAATTACAGTGGATAACAGTTTGGAATATGATGACCACCACTTTGATAAGTGGCAGATA
119 ACCATACAAGAGATGTCACAAATTAGGAGAAAATTTGAATTCTTTACATATGCTAGGTTT
120 GATTCAGAAATTACCTTAGTTCCTTGTATAGCCGGTAAGGGTGAAGACATTGGACACATT
121 GTGATGCAATATATGTATGTACCCCCTGGCGCACCCATACCAAAGAAAAGAAATGATTAC
122 ACATGGCAGTCAGGCACTAATGCTTCTGTATTCTGGCAACATGGTCAAACTTTCCCTAGA
123 TTTTCTTTACCTTTCCTAAGCATAGCTTCAGCATACTACATGTTTTATGATGGATACGAT
124 GGTGATACATCGACCTCAAGATATGGCACATCAGTCACTAACCATATGGGAACGCTATGC
125 TCAAGAATAGTCACCAACAAGCAGCAGCATGAAGTTGAGATTACCACACGTATATATCAC
126 AAGGCCAAGCATATTAAAGCATGGTGTCCAAGGGCCCCAAGAGCAGTACCTTACACACAT
127 ACACACTCAACAAATTATAAACCTCAAGAAGGTGAAGTCCAGATTTTCCTCAAAGAGAGA
128 GCCAGCCTAACAACAGTC
129 >9_HRV40
130 AACCCCGTTGAAAGGTATGTTGATGAGGTTCTTAATGAAGTTCTGGTAGTTCCAAATATC
```

FIG. D1 CONT'D

Rhino_cDNA_DB.fasta                                                    9/20/2007 5:08 PM

```
131 AGAGAGAGCCATCCAACTACATCAAATTCGGCCCCTGCCTTGGATGCAGCAGAGACTGGA
132 CATACAAGCAACATACAACCTGAAGATACAATAGAAACAAGATTTGTGCAGACATCACAA
133 ACTAGAGATGAAATGAGCATAGAGAGTTTCTTGGGAAGATCTGGGTGCATTCATATATCC
134 ACAATTACAGTGGATAACAGTTTGGAATATGATGACCACCACTTTGATAAGTGGCAGATA
135 ACCATACAAGAGATGTCACAAATTAGGAGAAAATTTGAATTCTTTACATATGCTAGGTTT
136 GATTCAGAAATTACCTTAGTTCCTTGTATAGCCGGTAAGGGTGAAGACATTGGACACATT
137 GTGATGCAATATATGTATGTACCCCCTGGCGCACCCATACCAAAGAAAAGAAATGATTAC
138 ACATGGCAGTCAGGCACTAATGCTTCTGTATTCTGGCAACATGGTCAAACTTTCCCTAGA
139 TTTTCTTTACCTTTCCTAAGCATAGCTTCAGCATACTACATGTTTTATGATGGATACGAT
140 GGTGATACATCGACCTCAAGATATGGCACATCAGTCACTAACCATATGGGAACGCTATGC
141 TCAAGAATAGTCACCAACAAGCAGCAGCATGAAGTTGAGATTACCACACGTATATATCAC
142 AAGGCCAAGCATATTAAAGCATGGTGTCCAAGGGCCCCAAGAGCAGTACCTTACACACAT
143 ACACACTCAACAAATTATAAACCTCAAGAAGGTGAAGTCCAGATTTTCCTCAAAGAGAGA
144 GCCAGCCTAACAACAGTT
145 >10_HRV85
146 AATCCTGTTGAAAAATACGTTGATGAAGTCCTTAATGAGGTTCTAGTGGTTCCAAATATC
147 AAAGAGAGTCACCCAACTATATCAAATTCAGCTCCTGCTTTGGATGCAGCAGAGACTGGC
148 CATACAAGTAGTACACAGCCCGAGGATACAATAGAGACCAGGTTTGTTCAAACTTCACAG
149 ACTAGGGATGAAATGAGTTTAGAAAGTTTCTTGGGAAGATCTGGATGTATCCATATATCT
150 ACAATTACTGTGAATAACAACCTAGATTATGATGAAAATCACTTTGATCAGTGGCAGATA
151 ACTATACAGGAAATGGCACAAATTAGAAGGAAGTTTGAGTTCTTTACTTACACTAGATTT
152 GATTCAGAAATCACTTTAGTCCCTTGTATAGCTGGAAAGGGTGATGATATTGGACACATT
153 GTAATGCAGTATATGTATGTGCCCCCCGGAGCACCAATACCAAGGAAAAGAGATGATTAC
154 ACATGGCAATCAGGTACTAATGCTTCCGTGTTTTGGCAACATGGGCAAACTTTCCCCAGA
155 TTTTCCTTACCTTTCTTGAGTGTTGCTTCAGCATATTACATGTTTTATGATGGTTATGAT
156 GGTGATACACCAGGCTCAATGTATGGGACGTCAGTCACCAACCACATGGGAACACTGTGC
157 TCGAGGATAGTTACCAACAAACAGCAGCATGAGGTTGAAATCACCACGCGTGTGTATCAT
158 AAGGCCAAGCATGTAAAGGCTTGGTGTCCAAGAGCACCAAGAGCGGTGCCTTATACACAC
159 ACACGCTCAACCAACTATGTGCCACAAGATGGTGAAGTTAAGATCTTCCTCAAAGAGAGA
160 GCTAGTTTAACCACAGCA
161 >11_HRV85a|
162 AATCCTGTTGAAAAATACGTTGATGAAGTCCTTAATGAGGTTCTAGTGGTTCCAAATATC
163 AAAGAGAGTCACCCAACTATATCAAATTCAGCTCCTGCTTTGGATGCAGCAGAGACTGGC
164 CATACAAGTAGTACACAGCCCGAGGATACAATAGAGACCAGGTTTGTTCAAACTTCACAG
165 ACTAGGGATGAAATGAGTTTAGAAAGTTTCTTGGGAAGATCTGGATGTATCCATATATCT
166 ACAATTACTGTGAATAACAACCTAGATTATGATGAAAATCACTTTGATCAGTGGCAGATA
167 ACTATACAGGAAATGGCACAAATTAGAAGGAAGTTTGAGTTCTTTACTTACACTAGATTT
168 GATTCAGAAATCACTTTAGTCCCTTGTATAGCTGGAAAGGGTGATGATATTGGACACATT
169 GTAATGCAGTATATGTATGTGCCCCCCGGAGCACCAATACCAAGGAAAAGAGATGATTAC
170 ACATGGCAATCAGGTACTAATGCTTCCGTGTTTTGGCAACATGGGCAAACTTTCCCCAGA
171 TTTTCCTTACCTTTCTTGAGTGTTGCTTCAGCATATTACATGTTTTATGATGGTTATGAT
172 GGTGATACACCAGGCTCAATGTATGGGACGTCAGTCACCAACCACATGGGAACACTGTGC
173 TCGAGGATAGTTACCAACAAACAGCAGCATGAGGTTGAAATCACCACGCGTGTGTATCAT
174 AAGGCCAAGCATGTAAAGGCTTGGTGTCCAAGAGCACCAAGAGCGGTGCCTTATACACAC
175 ACACGCTCAACCAACTATGTGCCACAAGATGGTGAAGTTAAGATCTTCCTCAAAGAGAGA
176 GCTAGTTTAACCACAGCG
177 >12_HRV85b|
178 AATCCTGTTGAAAAATACGTTGATGAAGTCCTTAATGAGGTTCTAGTGGTTCCAAATATC
179 AAAGAGAGTCACCCAACTATATCAAATTCAGCTCCTGCTTTGGATGCAGCAGAGACTGGC
180 CATACAAGTAGTACACAGCCCGAGGATACAATAGAGACCAGGTTTGTTCAAACTTCACAG
181 ACTAGGGATGAAATGAGTTTAGAAAGTTTCTTGGGAAGATCTGGATGTATCCATATATCT
182 ACAATTACTGTGAATAACAACCTAGATTATGATGAAAATCACTTTGATCAGTGGCAGATA
183 ACTATACAGGAAATGGCACAAATTAGAAGGAAGTTTGAGTTCTTTACTTACACTAGATTT
184 GATTCAGAAATCACTTTAGTCCCTTGTATAGCTGGAAAGGGTGATGATATTGGACACATT
185 GTAATGCAGTATATGTATGTGCCCCCCGGAGCACCAATACCAAGGAAAAGAGATGATTAC
186 ACATGGCAATCAGGTACTAATGCTTCCGTGTTTTGGCAACATGGGCAAACTTTCCCCAGA
187 TTTTCCTTACCTTTCTTGAGTGTTGCTTCAGCATATTACATGTTTTATGATGGTTATGAT
188 GGTGATACACCAGGCTCAATGTATGGGACGTCAGTCACCAACCACATGGGAACACTGTGC
189 TCGAGGATAGTTACCAACAAACAGCAGCATGAGGTTGAAATCACCACGCGTGTGTATCAT
190 AAGGCCAAGCATGTAAAGGCTTGGTGTCCAAGAGCACCAAGAGCGGTGCCTTATACACAC
191 ACACGCTCAACCAACTATGTGCCACAAGATGGTGAAGTTAAGATCTTCCTCAAAGAGAGA
192 GCTAGTTTAACCACAGCT
193 >13_HRV56a|
194 AACCCAGTTGAGAGATATGTAGATGATGTTTTAAATGAAGTTTTAGTTGTTCCAAATATT
195 AGGGAGAGCCATCCATCCACATCAAATTCTGCCCCTGCATTAGATGCTGCTGAAACTGGC
```

FIG. D1 CONT'D

Rhino cDNA_DB.fasta                                                    9/20/2007 5:08 PM

```
196 CATACTAGTGCAATCCAACCAGAAGACACTATAGAAACCAGATATGTACAGACATCACAA
197 ACTAGGGATGAAATGAGTATAGAGAGTTTTCTAGGTAGATCAGGTTGTATACATATATCA
198 ACTATAACTGTGGATAATGATGTAGATTATAATTCAAAGCATTATAATAAATGGCAAATA
199 ACCTTACAAGAAATGGCTCAAGTTAGGCGTAAATTTGAATTCTTTACTTATGTCAGATTT
200 GATTCAGAGGTTACTTTGGTACCTTGTGTAGCCGGCAAGGGAGATGATATTGGACACATT
201 GTAATGCAATACATGTATGTGCCTCCTGGTGCACCACTTCCAAACTCAAGAGATGATTTT
202 ACATGGCAATCTGGCACCAATGCTTCTGTCTTTTGGCAACATGGCCAAGCTTTCCCCAGA
203 TTCTCTCTACCTTTCTTAAGTATTGCTTCTGCTTATTACATGTTTTATGATGGTTATGAT
204 GGAGACACTTCAAGCTCCAGATATGGTACATCAGTTACAAACCACATGGGGACACTCTGT
205 TCAAGAATTGTGACAAATAAACAACTTCATCCTGTTGAAGTCACAACTCGTGTATATCAT
206 AAGGCAAAGCATATTCGAGCATGGTGTCCTAGAGCACCAAGGGCTGTGCCTTATACACAT
207 GCTCACGTCACCAATTATAAACCACAAGATGGTGATGTACAGATCTTCTTAAAACCCAGA
208 CCCAGCCTAACAACATTA
209 >14_HRV56bI
210 AACCCAGTTGAGAGATATGTAGATGATGTTTTAAATGAAGTTTTAGTTGTTCCAAATATT
211 AGGGAGAGCCATCCATCCACATCAAATTCTGCCCCTGCATTAGATGCTGCTGAAACTGGC
212 CATACTAGTGCAATCCAACCAGAAGACACTATAGAAACCAGATATGTACAGACATCACAA
213 ACTAGGGATGAAATGAGTATAGAGAGTTTTCTAGGTAGATCAGGTTGTATACATATATCA
214 ACTATAACTGTGGATAATGATGTAGATTATAATTCAAAGCATTATAATAAATGGCAAATA
215 ACCTTACAAGAAATGGCTCAAGTTAGGCGTAAATTTGAATTCTTTACTTATGTCAGATTT
216 GATTCAGAGGTTACTTTGGTACCTTGTGTAGCCGGCAAGGGAGATGATATTGGACACATT
217 GTAATGCAATACATGTATGTGCCTCCTGGTGCACCACTTCCAAACTCAAGAGATGATTTT
218 ACATGGCAATCTGGCACCAATGCTTCTGTCTTTTGGCAACATGGCCAAGCTTTCCCCAGA
219 TTCTCTCTACCTTTCTTAAGTATTGCTTCTGCTTATTACATGTTTTATGATGGTTATGAT
220 GGAGACACTTCAAGCTCCAGATATGGTACATCAGTTACAAACCACATGGGGACACTCTGT
221 TCAAGAATTGTGACAAATAAACAACTTCATCCTGTTGAAGTCACAACTCGTGTATATCAT
222 AAGGCAAAGCATATTCGAGCATGGTGTCCTAGAGCACCAAGGGCTGTGCCTTATACACAT
223 GCTCACGTCACCAATTATAAACCACAAGATGGTGATGTACAGATCTTCTTAAAACCCAGA
224 CCCAGCCTAACAACATTG
225 >15_HRV56
226 AACCCAGTTGAGAGATATGTAGATGATGTTTTAAATGAAGTTTTAGTTGTTCCAAATATT
227 AGGGAGAGCCATCCATCCACATCAAATTCTGCCCCTGCATTAGATGCTGCTGAAACTGGC
228 CATACTAGTGCAATCCAACCAGAAGACACTATAGAAACCAGATATGTACAGACATCACAA
229 ACTAGGGATGAAATGAGTATAGAGAGTTTTCTAGGTAGATCAGGTTGTATACATATATCA
230 ACTATAACTGTGGATAATGATGTAGATTATAATTCAAAGCATTATAATAAATGGCAAATA
231 ACCTTACAAGAAATGGCTCAAGTTAGGCGTAAATTTGAATTCTTTACTTATGTCAGATTT
232 GATTCAGAGGTTACTTTGGTACCTTGTGTAGCCGGCAAGGGAGATGATATTGGACACATT
233 GTAATGCAATACATGTATGTGCCTCCTGGTGCACCACTTCCAAACTCAAGAGATGATTTT
234 ACATGGCAATCTGGCACCAATGCTTCTGTCTTTTGGCAACATGGCCAAGCTTTCCCCAGA
235 TTCTCTCTACCTTTCTTAAGTATTGCTTCTGCTTATTACATGTTTTATGATGGTTATGAT
236 GGAGACACTTCAAGCTCCAGATATGGTACATCAGTTACAAACCACATGGGGACACTCTGT
237 TCAAGAATTGTGACAAATAAACAACTTCATCCTGTTGAAGTCACAACTCGTGTATATCAT
238 AAGGCAAAGCATATTCGAGCATGGTGTCCTAGAGCACCAAGGGCTGTGCCTTATACACAT
239 GCTCACGTCACCAATTATAAACCACAAGATGGTGATGTACAGATCTTCTTAAAACCCAGA
240 CCCAGCCTAACAACATTT
241 >16_HRV54
242 AATCCTGTAGAAAGATATGTTGATGAAGTGTTAAATGAAGTGTTAGTTGTCCCAAACATT
243 AGAGAAAGTCATCCAGCTACATCTAATTCAGCCCCTCGCGCTAAGATGCGGCAGAAACTGGA
244 CACACTAGTGGAGTACAACCCGAGGACACCATAGAAACAAGATTTGTGCAGACATCACAA
245 ACTAGAGATGAAATGAGCATAGAAAGTTTTCTAGGCAGGGCTGGTTGCATACATGAATCC
246 ACCATTACAATTCAAAATGATGTAGAATACAATGATCACCATTTTAAGAAATGGGATATA
247 ACATTACAAGAGATGGCACAAATACGAAGGAAATTTGAATTCTTTACTTATGTTAGGTTT
248 GATTCAGAAATTACTCTAGTCCCCTGTATAGCTGGTAAGGGAGTTGATATTGGACACATT
249 GTCATGCAATTCATGTATGTACCGCCTGGTGCACCAAAACCAGAAAAAAGGAATGATTAC
250 ACCTGGGAGTCAAGCACAAACCCTTCTATATTTTGGCAACATGGCCAAGCTTATCAAGA
251 TTCTCTTTACCATTTTTAAGTATTGCTTCTGCTTACTACATGTTTTATGATGGGTATGAT
252 GGTGACGCACCTGGATCAAGATATGGGACTTCAGTTACCAATCATATGGGTACTTTGTGT
253 TCAAGAGTGGTTACTGATAAACAAAAACACCCAGTTGAAATCACCACACGGGTGTATCAC
254 AAGGCAAAACACATTAGAGCATGGTGTCCACGTGCACCTAGGGCTGTCCCATACACACAT
255 ACTAGATCAACAAATTACATGCCACGGGAGGGTGATCCAACAATTTTCCTTAAACACAGG
256 ACAAACCTTGTAACAGCT
257 >17_HRV98
258 AATCCTGTAGAGAGATATGTTGATGAAGTATTAAATGAAGTGTTAGTTGTTCCAAACATT
259 AAAGAAAGTCATCCAGCTACATCTAATTCGGCCCCTACACTAGATGCAGCAGAAACTGGG
260 CACACTAGTGGAATACAACCTGAGGATACTATAGAAACAAGATATGTGCAGACATCACAA
```

FIG. D1 CONT'D

Rhino cDNA DB.fasta                                             9/20/2007 5:08 PM

```
261 ACCAGAGATGAAATGAGTATAGAAAGTTTTCTAGGTAGGGCCGGTTGTATACATGAATCT
262 ACTATCACTATTCAAAATGATGTAGAATATAACGATCATCATTTTAGACAATGGGATATA
263 ACATTACAAGAAATGGCACAAATTCGAAGAAAATTTGAATTCTTTACTTATGTTAGATTT
264 GATTCAGAAGTTACCTTAGTTCCTTGCATAGCTGGCAAGGGAGCTGACATTGGACACATT
265 GTCATGCAATTCATGTATGTTCCACCTGGTGCACCTAAACCTAAAAAGAGGAATGATTAT
266 ACTTGGGAATCAAGCACAAACCCTTCTATATTCTGGCAGCATGGTCAGGCCTATCCAAGA
267 TTTTCTCTACCATTCTTGAGCATTGCATCTGCTTACTACATGTTTTACGATGGGTATGAT
268 GGTGATGCACCTGGATCAAGATATGGAACCTCAGTCACTAATCACATGGGCACTTTGTGT
269 TCAAGAGTAGTTACTGGCAAACAAGAACACCCAGTTGAAATCACTACACGTGTGTACCAC
270 AAAGCAAAACACATTAGAGCATGGTGTCCACGTGCACCTAGAGCTGTTCCATACACACAC
271 ACTAGATCAACTAATTACATGCCTCAAGATGGTGAACCAACAATCTTTCTTAAGCATAGA
272 AAAGATCTTGTAACAGCT
273 >18_HRV59a|
274 AACCCAGTGGAAAACTATGTTAATGATGTACTTAATGAGGTTTTAGTAGTACCAAATATA
275 CAGGAAAGCCACCCAACCACCTCAAATGCTGCTCCAGCATTAGATGCAGCAGAGACTGGA
276 CATACAAGCAGTATACAACCTGAGGATACCATAGAAACAAGATATGTTCAGACATCACAA
277 ACTAGAGATGAGATGAGTGTAGAAAGTTTCTTAGGTAGATCTGGGTGTATACATATTTCA
278 ACTATTACTGTCAATAAAGACATAAAATATGATGATGGACACTTTCTTAAATGGCCTATA
279 ACATTACAAGAGATGGCACAAATTAGGAGAAAAATTTGAATTCTTCACATATGTTAGATTT
280 GACTCAGAAATCACTTTGGTGCCTTGCATAGCTGGAAAAGGGGATGACATTGGTCATATA
281 GTCATGCAATATATGTATGTTCCACCAGGTGCTCCACTGCCCACAAAGAGAGATGATTAC
282 ACATGGCAATCTGGTACTAATGCTTCAATATTCTGGCAACATGGACAAACATTCCCAAGA
283 TTTTCATTGCCCTTCCTGAGCATAGCATCAGCTTATTACATGTTTTATGATGGTTATGAT
284 GGAGATAAATCTGAATCTAGGTATGGTGTGTCTGTAACCAACCACATGGGCACTTTATGT
285 TCTAGAATAGTTACAAACAGTCAGGAGCATCCAGTGGAGGTTGTCACACGTGTGTATCAC
286 AAAGCTAAACACGTCAAAGCCTGGTGCCCTAGAGCTCCTAGAGCAGTCCCTTACACACAC
287 AGCTACGTAACTAACTACAAGATTGCTGGAAAAGAACCTGAAATTTTCTTAAAACCAAGA
288 ATGAATATTACAACAGCA
289 >19_HRV59b|
290 AACCCAGTGGAAAACTATGTTAATGATGTACTTAATGAGGTTTTAGTAGTACCAAATATA
291 CAGGAAAGCCACCCAACCACCTCAAATGCTGCTCCAGCATTAGATGCAGCAGAGACTGGA
292 CATACAAGCAGTATACAACCTGAGGATACCATAGAAACAAGATATGTTCAGACATCACAA
293 ACTAGAGATGAGATGAGTGTAGAAAGTTTCTTAGGTAGATCTGGGTGTATACATATTTCA
294 ACTATTACTGTCAATAAAGACATAAAATATGATGATGGACACTTTCTTAAATGGCCTATA
295 ACATTACAAGAGATGGCACAAATTAGGAGAAAAATTTGAATTCTTCACATATGTTAGATTT
296 GACTCAGAAATCACTTTGGTGCCTTGCATAGCTGGAAAAGGGGATGACATTGGTCATATA
297 GTCATGCAATATATGTATGTTCCACCAGGTGCTCCACTGCCCACAAAGAGAGATGATTAC
298 ACATGGCAATCTGGTACTAATGCTTCAATATTCTGGCAACATGGACAAACATTCCCAAGA
299 TTTTCATTGCCCTTCCTGAGCATAGCATCAGCTTATTACATGTTTTATGATGGTTATGAT
300 GGAGATAAATCTGAATCTAGGTATGGTGTGTCTGTAACCAACCACATGGGCACTTTATGT
301 TCTAGAATAGTTACAAACAGTCAGGAGCATCCAGTGGAGGTTGTCACACGTGTGTATCAC
302 AAAGCTAAACACGTCAAAGCCTGGTGCCCTAGAGCTCCTAGAGCAGTCCCTTACACACAC
303 AGCTACGTAACTAACTACAAGATTGCTGGAAAAGAACCTGAAATTTTCTTAAAACCAAGA
304 ATGAATATTACAACAGCG
305 >20_HRV59
306 AACCCAGTGGAAAACTATGTTAATGATGTACTTAATGAGGTTTTAGTAGTACCAAATATA
307 CAGGAAAGCCACCCAACCACCTCAAATGCTGCTCCAGCATTAGATGCAGCAGAGACTGGA
308 CATACAAGCAGTATACAACCTGAGGATACCATAGAAACAAGATATGTTCAGACATCACAA
309 ACTAGAGATGAGATGAGTGTAGAAAGTTTCTTAGGTAGATCTGGGTGTATACATATTTCA
310 ACTATTACTGTCAATAAAGACATAAAATATGATGATGGACACTTTCTTAAATGGCCTATA
311 ACATTACAAGAGATGGCACAAATTAGGAGAAAATTTGAATTCTTCACATATGTTAGATTT
312 GACTCAGAAATCACTTTGGTGCCTTGCATAGCTGGAAAAGGGGATGACATTGGTCATATA
313 GTCATGCAATATATGTATGTTCCACCAGGTGCTCCACTGCCCACAAAGAGAGATGATTAC
314 ACATGGCAATCTGGTACTAATGCTTCAATATTCTGGCAACATGGACAAACATTCCCAAGA
315 TTTTCATTGCCCTTCCTGAGCATAGCATCAGCTTATTACATGTTTTATGATGGTTATGAT
316 GGAGATAAATCTGAATCTAGGTATGGTGTGTCTGTAACCAACCACATGGGCACTTTATGT
317 TCTAGAATAGTTACAAACAGTCAGGAGCATCCAGTGGAGGTTGTCACACGTGTGTATCAC
318 AAAGCTAAACACGTCAAAGCCTGGTGCCCTAGAGCTCCTAGAGCAGTCCCTTACACACAC
319 AGCTACGTAACTAACTACAAGATTGCTGGAAAAGAACCTGAAATTTTCTTAAAACCAAGA
320 ATGAATATTACAACAGCT
321 >21_HRV63
322 AATCCAGTAGAGAATTATGTAAATGATGTTCTTAATGAAGTGTTAGTTGTTCCAAACATA
323 CAAGAAAGCCATCCAACCACATCAAACGCTGCTCCTGTACTTGATGCTGCGGAAACAGGA
324 CACACAAGCAGTATACAACCTGAGGATACTGTAGAAACTAGATATGTGCAAACGTCTCAA
325 ACAAGGGATGAAATGAGTGTAGAGAGCTTTCTTGGTAGATCAGGATGCATACACATATCA
```

FIG. D1 CONT'D

Rhino_cDNA_DB.fasta                                              9/20/2007 5:08 PM

```
326 ACTATCACTGTTGACAAAACCATTGACTATGACACTGGACATTTTAATAAATGGCAAATA
327 ACATTACAAGAGATGGCACAAATTAGAAGGAAATTTGAATTCTTCACATATGTCAGATTT
328 GATTCAGAAGTCACTCTTGTACCATGTATAGCAGGAAAAGGTGATGACATTGGTCATATA
329 GTTATGCAGTACATGTACGTTCCACCCGGTGCCCCTCTACCCACCCGAAGAGAAGATTAC
330 ACATGGCAATCTGGCACTAATGCTTCAATATTCTGGCAACATGGACAAGCTTTTCCAAGG
331 TTTTCTCTACCTTTCTTGAGTATTGCATCAGCATATTACATGTTTTATGATGGATATGAT
332 GGAGATAAATCAAGCTCTAGGTATGGTGTTTCAGTTACTAACCACATGGGGACTTTATGT
333 TCTAGAATTGTAACAAACAGCCAAGAACATCCAGTTGAGGTGACTACACGTGTATATCAT
334 AAAGCTAAACACATCAGAGCCTGGTGCCCAAGAGCTCCTAGGGCTGTTCCATACACACAT
335 AGTTATGTCACTAACTATAAAATTACAGGACAGGAGACTGAAATTTTCTTAAAACCTAGA
336 GCAACTATCAAGACAGCA
337 >22_HRV63b|
338 AATCCAGTAGAGAATTATGTAAATGATGTTCTTAATGAAGTGTTAGTTGTTCCAAACATA
339 CAAGAAAGCCATCCAACCACATCAAACGCTGCTCCTGTACTTGATGCTGCGGAAACAGGA
340 CACACAAGCAGTATACAACCTGAGGATACTGTAGAAACTAGATATGTGCAAACGTCTCAA
341 ACAAGGGATGAAATGAGTGTAGAGAGCTTTCTTGGTAGATCAGGATGCATACACATATCA
342 ACTATCACTGTTGACAAAACCATTGACTATGACACTGGACATTTTAATAAATGGCAAATA
343 ACATTACAAGAGATGGCACAAATTAGAAGGAAATTTGAATTCTTCACATATGTCAGATTT
344 GATTCAGAAGTCACTCTTGTACCATGTATAGCAGGAAAAGGTGATGACATTGGTCATATA
345 GTTATGCAGTACATGTACGTTCCACCCGGTGCCCCTCTACCCACCCGAAGAGAAGATTAC
346 ACATGGCAATCTGGCACTAATGCTTCAATATTCTGGCAACATGGACAAGCTTTTCCAAGG
347 TTTTCTCTACCTTTCTTGAGTATTGCATCAGCATATTACATGTTTTATGATGGATATGAT
348 GGAGATAAATCAAGCTCTAGGTATGGTGTTTCAGTTACTAACCACATGGGGACTTTATGT
349 TCTAGAATTGTAACAAACAGCCAAGAACATCCAGTTGAGGTGACTACACGTGTATATCAT
350 AAAGCTAAACACATCAGAGCCTGGTGCCCAAGAGCTCCTAGGGCTGTTCCATACACACAT
351 AGTTATGTCACTAACTATAAAATTACAGGACAGGAGACTGAAATTTTCTTAAAACCTAGA
352 GCAACTATCAAGACAGCG
353 >23_HRV63a|
354 AATCCAGTAGAGAATTATGTAAATGATGTTCTTAATGAAGTGTTAGTTGTTCCAAACATA
355 CAAGAAAGCCATCCAACCACATCAAACGCTGCTCCTGTACTTGATGCTGCGGAAACAGGA
356 CACACAAGCAGTATACAACCTGAGGATACTGTAGAAACTAGATATGTGCAAACGTCTCAA
357 ACAAGGGATGAAATGAGTGTAGAGAGCTTTCTTGGTAGATCAGGATGCATACACATATCA
358 ACTATCACTGTTGACAAAACCATTGACTATGACACTGGACATTTTAATAAATGGCAAATA
359 ACATTACAAGAGATGGCACAAATTAGAAGGAAATTTGAATTCTTCACATATGTCAGATTT
360 GATTCAGAAGTCACTCTTGTACCATGTATAGCAGGAAAAGGTGATGACATTGGTCATATA
361 GTTATGCAGTACATGTACGTTCCACCCGGTGCCCCTCTACCCACCCGAAGAGAAGATTAC
362 ACATGGCAATCTGGCACTAATGCTTCAATATTCTGGCAACATGGACAAGCTTTTCCAAGG
363 TTTTCTCTACCTTTCTTGAGTATTGCATCAGCATATTACATGTTTTATGATGGATATGAT
364 GGAGATAAATCAAGCTCTAGGTATGGTGTTTCAGTTACTAACCACATGGGGACTTTATGT
365 TCTAGAATTGTAACAAACAGCCAAGAACATCCAGTTGAGGTGACTACACGTGTATATCAT
366 AAAGCTAAACACATCAGAGCCTGGTGCCCAAGAGCTCCTAGGGCTGTTCCATACACACAT
367 AGTTATGTCACTAACTATAAAATTACAGGACAGGAGACTGAAATTTTCTTAAAACCTAGA
368 GCAACTATCAAGACAGCT
369 >24_HRV39
370 AATCCAGTAGAAAATTATATAGATGAAGTATTAAATGAGGTATTAGTTGTTCCTAATATA
371 AGAGAGAGCCATCCAACTACATCTAATGCAGCTACAGCTTTGGATGCTGCTGAAACTGGA
372 CACACAAGTAGCACCCAGCCTGAAGACACAATTGAAACAAGATATGTGCAAACCTCACAT
373 ACTAGGGATGAAATGAGCGTTGAAAGTTTCTTAGGCAGATCTGGCTGTATTCACATTTCC
374 ACAATTACTATGAAGAAGGAGAACTATAATGATCATAATTTTGTGGATTGGAAAATTACT
375 TTGCAGGAGATGGCACAGGTTAGAAGGAAATTTGAAATGTTCACCTATGTTAGATTTGAC
376 TCAGAGATTACTTTAGTCCCATGCATAGCTGGAAGAGGTGAAGATATTGGACACATAGTA
377 ATGCAATACATGTATGTCCCACCTGGTGCACCTGTACCTAAGAAGAGAGATGATTACACA
378 TGGCAATCTGGAACAAATGCCTCAGTTTTCTGGCAACACGGACAGCCTTACCCTAGATTT
379 TCATTACCATTTCTAAGCATAGCCTCAGCATATTATATGTTCTATGATGGATATGATGGT
380 GATAAATCGTCATCTAGGTATGGTGTTTCTGTCACTAATGATATGGGTACACTTTGCACT
381 AGAATTGTAACAAACCAACAGGAACACCTAGTGGAGGTTACAACCAGAGTTTACCATAAA
382 GCCAAGCATGTTAAAGCATGGTGCCCTAGGGCTCCCAGAGCAGTCCCTTACACACACAGC
383 AATGTTACAAATTACAAAGTACGGGACGGTGAACCAACACTCTTTATAAAATCAAGAGAG
384 AATCTTACCACACAGCT
385 >25_HRV39a|
386 AATCCAGTAGAAAATTATATAGATGAAGTATTAAATGAGGTATTAGTTGTTCCTAATATA
387 AGAGAGAGCCATCCAACTACATCTAATGCAGCTACAGCTTTGGATGCTGCTGAAACTGGA
388 CACACAAGTAGCACCCAGCCTGAAGACACAATTGAAACAAGATATGTGCAAACCTCACAT
389 ACTAGGGATGAAATGAGCGTTGAAAGTTTCTTAGGCAGATCTGGCTGTATTCACATTTCC
390 ACAATTACTATGAAGAAGGAGAACTATAATGATCATAATTTTGTGGATTGGAAAATTACT
```

FIG. D1 CONT'D

Rhino_cDNA_DB.fasta                                                          9/20/2007 5:08 PM

```
391 TTGCAGGAGATGGCACAGGTTAGAAGGAAATTTGAAATGTTCACCTATGTTAGATTTGAC
392 TCAGAGATTACTTTAGTCCCATGCATAGCTGGAAGAGGTGAAGATATTGGACACATAGTA
393 ATGCAATACATGTATGTCCCACCTGGTGCACCTGTACCTAAGAAGAGAGATGATTACACA
394 TGGCAATCTGGAACAAATGCCTCAGTTTTCTGGCAACACGGACAGCCTTACCCTAGATTT
395 TCATTACCATTTCTAAGCATAGCCTCAGCATATTATATGTTCTATGATGGATATGATGGT
396 GATAAATCGTCATCTAGGTATGGTGTTTCTGTCACTAATGATATGGGTACACTTTGCACT
397 AGAATTGTAACAAACCAACAGGAACACCTAGTGGAGGTTACAACCAGAGTTTACCATAAA
398 GCCAAGCATGTTAAAGCATGGTGCCCTAGGGCTCCCAGAGCAGTCCCTTACACACACAGC
399 AATGTTACAAATTACAAAGTACGGGACGGTGAACCAACACTCTTTATAAAATCAAGAGAG
400 AATCTTACCACAGCA
401 >26_HRV39b|
402 AATCCAGTAGAAAATTATATAGATGGAGTATTAAATGAGGTATTAGTTGTTCCTAATATA
403 AGAGAGAGCCATCCAACTACATCTAATGCAGCTCCAGCTTTGGATGCTGCTGAAACTGGA
404 CACACAAGTAGCATCCAACCTGAAGACACAATTGAAACAAGATATGTGCAAACCTCACAT
405 ACTAGGGATGAAATGAGTGTTGAAAGTTTCTTAGGCAGATCTGGCTGTATTCACATTTCC
406 ACAATTACTATGAAGAAGGAGAACTATAATGAACATAATTTTGTGGATTGGAAAATTACT
407 TTGCAGGAGATGGCACAGGTTAGAAGGAAATTTGAAATGTTCACCTACGTTAGATTTGAC
408 TCAGAGATTACTTTAGTCCCATGCATAGCTGGAAGAGGTGAAGATATTGGACACATAGTA
409 ATGCAATACATGTATGTCCCACCCGGTGCACCTGTACCTAAGAAGAGAGATGATTACACA
410 TGGCAATCTGGAACAAATGCCTCAGTTTTCTGGCAACACGGACAGCCTTACCCTAGATTT
411 TCATTACCATTTCTAAGCATAGCCTCAGCATATTATATGTTCTATGATGGATATGATGGT
412 GATAAATCGTCATCTAGGTATGGTGTTTCTGTCACTAATGATATGGGTACACTTTGCACT
413 AGAATTGTAACAAACCAACAGAAACACCTAGTGGAGGTTACAACCAGAGTTTACCATACA
414 GCCAAGCATGTTAAAGCATGGTGCCCTAGGGCTCCCAGAGCAGTCCCTTACACACACAGC
415 AATGTTACAAATTACAAAGTACGGGACGGTGAACCAACACTCTTTATAAAACCAAGAGAG
416 AATCTTACCACAGCT
417 >27_HRV10a|
418 AATCCAGTTGAAAATTACATTGATAATGTACTTAATGAAGTCCTAGTGGTACCCAACATC
419 AGAGAAAGTCATCCAAGCACCTCTAACTCTGCCCCAATTCTGATGCAGCTGAGACTGGT
420 CATACCAGTAGTGTACAACCAGAAGATACGGTTGAAACACGATATGTGCAAACATCCCAG
421 ACGAGAGATGAAATGAGTATTGAAAGTTTTCTTGGCAGGTCAGGTTGTATACACACCTCA
422 ACAATAACTGTTAATAATACAAGACCCTACAATGAACACACTTTTGACACATGGCAAATA
423 ACTCTACAAGAAATGGCCCAAATTAGAAGGAAATTTGAAATGTTACATATGTTAGATTT
424 GACTCAGAAGTCACTTTAGTACCTTGCATCGCAGGCAAGGGCGATGACATAGGTCACATA
425 GTTATGCAATATATGTATGTGCCACCTGGGGCTCCAGTACCAACTAAGAGAGATGATTTT
426 GCTTGGCAGTCGGGAACAAATGCATCAGTCTTCTGGCAACATGGACAACCTTTCCCTAGA
427 TTTTCTTTACCCTTCTTAAGCATTGCATCTGCTTACTACATGTTCTATGATGGTTATGAT
428 GGTGATACACATGACTCACGTTATGGCACAACAGTGATAAATCACATGGGCACTTTGTGC
429 ATGCGAATAGTCACAAACCAGCAAGCACATGAGGTGGAAATTACCACCAGTGTTTATCAC
430 AAAGCCAAGCATGTCAAAGCATGGTGTCCAAGACCACCCAGAGCTGTACCATATACACAT
431 GCCCATTCCACAAATTACAAACCACATGGCAAAGAATTACAAATATTTATTAGGTCTAGA
432 GATGATCCCAAAGTAGTAACTGCA
433 >28_HRV10b|
434 AATCCAGTTGAAAATTACATTGATAATGTACTTAATGAAGTCCTAGTGGTACCCAACATC
435 AGAGAAAGTCATCCAAGCACCTCTAACTCTGCCCCAATTCTGATGCAGCTGAGACTGGT
436 CATACCAGTAGTGTACAACCAGAAGATACGGTTGAAACACGATATGTGCAAACATCCCAG
437 ACGAGAGATGAAATGAGTATTGAAAGTTTTCTTGGCAGGTCAGGTTGTATACACACCTCA
438 ACAATAACTGTTAATAATACAAGACCCTACAATGAACACACTTTTGACACATGGCAAATA
439 ACTCTACAAGAAATGGCCCAAATTAGAAGGAAATTTGAAATGTTACATATGTTAGATTT
440 GACTCAGAAGTCACTTTAGTACCTTGCATCGCAGGCAAGGGCGATGACATAGGTCACATA
441 GTTATGCAATATATGTATGTGCCACCTGGGGCTCCAGTACCAACTAAGAGAGATGATTTT
442 GCTTGGCAGTCGGGAACAAATGCATCAGTCTTCTGGCAACATGGACAACCTTTCCCTAGA
443 TTTTCTTTACCCTTCTTAAGCATTGCATCTGCTTACTACATGTTCTATGATGGTTATGAT
444 GGTGATACACATGACTCACGTTATGGCACAACAGTGATAAATCACATGGGCACTTTGTGC
445 ATGCGAATAGTCACAAACCAGCAAGCACATGAGGTGGAAATTACCACCAGTGTTTATCAC
446 AAAGCCAAGCATGTCAAAGCATGGTGTCCAAGACCACCCAGAGCTGTACCATATACACAT
447 GCCCATTCCACAAATTACAAACCACATGGCAAAGAATTACAAATATTTATTAGGTCTAGA
448 GATGATCCCAAAGTAGTAACTGCC
449 >29_HRV10
450 AATCCAGTTGAAAATTACATTGATAATGTACTTAATGAAGTCCTAGTGGTACCCAACATC
451 AGAGAAAGTCATCCAAGCACCTCTAACTCTGCCCCAATTCTGATGCAGCTGAGACTGGT
452 CATACCAGTAGTGTACAACCAGAAGATACGGTTGAAACACGATATGTGCAAACATCCCAG
453 ACGAGAGATGAAATGAGTATTGAAAGTTTTCTTGGCAGGTCAGGTTGTATACACACCTCA
454 ACAATAACTGTTAATAATACAAGACCCTACAATGAACACACTTTTGACACATGGCAAATA
455 ACTCTACAAGAAATGGCCCAAATTAGAAGGAAATTTGAAATGTTACATATGTTAGATTT
```

FIG. D1 CONT'D

Rhino cDNA DB.fasta                                                        9/20/2007 5:08 PM

```
456  GACTCAGAAGTCACTTTAGTACCTTGCATCGCAGGCAAGGGCGATGACATAGGTCACATA
457  GTTATGCAATATATGTATGTGCCACCTGGGGCTCCAGTACCAACTAAGAGAGATGATTTT
458  GCTTGGCAGTCGGGAACAAATGCATCAGTCTTCTGGCAACATGGACAACCTTTCCCTAGA
459  TTTTCTTTACCCTTCTTAAGCATTGCATCTGCTTACTACATGTTCTATGATGGTTATGAT
460  GGTGATACACATGACTCACGTTATGGCACAACAGTGATAAATCACATGGGCACTTTGTGC
461  ATGCGAATAGTCACAAACCAGCAAGCACATGAGGTGGAAATTACCACCAGTGTTTATCAC
462  AAAGCCAAGCATGTCAAAGCATGGTGTCCAAGACCACCCAGAGCTGTACCATATACACAT
463  GCCCATTCCACAAATTACAAACCACATGGCAAAGAATTACAAATATTTATTAGGTCTAGA
464  GATGATCCCAAAGTAGTAACTGCT
465  >30_HRV100a
466  AATCCAGTAGAAAATTATGTTGAAGGTGTGCTGAATGAAGTACTAGTGGTACCTAATATT
467  AGAGAGAGCCATCCAAGCACCTCAAACTCTGCTCCAATCCTTGATGCTGCTGAAACTGGC
468  CACACTAGTAATGTGCAACCTGAAGATACAGTTGAAACTCGATATGTGCAGACATCACAG
469  ACCAGGGATGAAATGAGTATTGAGAGCTTTCTTGGAAGATCTGGTTGTATACACACCTCA
470  ACAATTACTGTAAGTAAAATGAAAAATTATAATGAGCACACTTTTGACAAATGGCAAATA
471  ACCCTACAGGAAATGGCCCAAATTAGAAGGAAATTTGAAATGTTTACATATGTCAGATTT
472  GACTCAGAAATCACATTGGTACCCTGTATTGCAGGAAAAGGAGATGACATAGGGCATATC
473  GTAATGCAGTACATGTATGTGCCACCTGGAGCTCCAGTTCCAACAAAAAGGGATGATTTT
474  GCATGGCAATCAGGCACAAATGCATCAGTTTTTTGGCAGCATGGGCAGCCATTCCCTAGA
475  ATTTCTTTACCTTTCTTGAGCATTGCTTCTGCATACTACATGTTTTATGATGGATATGAT
476  GGTGATACACATGATTCACACTATGGTACTACTGTAATTAACCACATGGGTACACTTTGT
477  ATGAGGATAGTTACAAATCAGCAAGCACATGAGGTGGAAATTACTACTAATATCTATCAC
478  AAGGCCAAACATGTTAAAGCTTGGTGCCCAAGACCACCTCGGGCTGTGCCGTACACACAT
479  AGTCACTCTACAAATTACAAACCACATGAGGGTGATGTAAAGATTTTCATTAGACCCAGA
480  GATGATCCAAAGTTTGTAACTGCA
481  >31_HRV100b
482  AATCCAGTAGAAAATTATGTTGAAGGTGTGCTGAATGAAGTACTAGTGGTACCTAATATT
483  AGAGAGAGCCATCCAAGCACCTCAAACTCTGCTCCAATCCTTGATGCTGCTGAAACTGGC
484  CACACTAGTAATGTGCAACCTGAAGATACAGTTGAAACTCGATATGTGCAGACATCACAG
485  ACCAGGGATGAAATGAGTATTGAGAGCTTTCTTGGAAGATCTGGTTGTATACACACCTCA
486  ACAATTACTGTAAGTAAAATGAAAAATTATAATGAGCACACTTTTGACAAATGGCAAATA
487  ACCCTACAGGAAATGGCCCAAATTAGAAGGAAATTTGAAATGTTTACATATGTCAGATTT
488  GACTCAGAAATCACATTGGTACCCTGTATTGCAGGAAAAGGAGATGACATAGGGCATATC
489  GTAATGCAGTACATGTATGTGCCACCTGGAGCTCCAGTTCCAACAAAAAGGGATGATTTT
490  GCATGGCAATCAGGCACAAATGCATCAGTTTTTTGGCAGCATGGGCAGCCATTCCCTAGA
491  ATTTCTTTACCTTTCTTGAGCATTGCTTCTGCATACTACATGTTTTATGATGGATATGAT
492  GGTGATACACATGATTCACACTATGGTACTACTGTAATTAACCACATGGGTACACTTTGT
493  ATGAGGATAGTTACAAATCAGCAAGCACATGAGGTGGAAATTACTACTAATATCTATCAC
494  AAGGCCAAACATGTTAAAGCTTGGTGCCCAAGACCACCTCGGGCTGTGCCGTACACACAT
495  AGTCACTCTACAAATTACAAACCACATGAGGGTGATGTAAAGATTTTCATTAGACCCAGA
496  GATGATCCAAAGTTTGTAACTGCG
497  >32_HRV100
498  AATCCAGTAGAAAATTATGTTGAAGGTGTGCTGAATGAAGTACTAGTGGTACCTAATATT
499  AGAGAGAGCCATCCAAGCACCTCAAACTCTGCTCCAATCCTTGATGCTGCTGAAACTGGC
500  CACACTAGTAATGTGCAACCTGAAGATACAGTTGAAACTCGATATGTGCAGACATCACAG
501  ACCAGGGATGAAATGAGTATTGAGAGCTTTCTTGGAAGATCTGGTTGTATACACACCTCA
502  ACAATTACTGTAAGTAAAATGAAAAATTATAATGAGCACACTTTTGACAAATGGCAAATA
503  ACCCTACAGGAAATGGCCCAAATTAGAAGGAAATTTGAAATGTTTACATATGTCAGATTT
504  GACTCAGAAATCACATTGGTACCCTGTATTGCAGGAAAAGGAGATGACATAGGGCATATC
505  GTAATGCAGTACATGTATGTGCCACCTGGAGCTCCAGTTCCAACAAAAAGGGATGATTTT
506  GCATGGCAATCAGGCACAAATGCATCAGTTTTTTGGCAGCATGGGCAGCCATTCCCTAGA
507  ATTTCTTTACCTTTCTTGAGCATTGCTTCTGCATACTACATGTTTTATGATGGATATGAT
508  GGTGATACACATGATTCACACTATGGTACTACTGTAATTAACCACATGGGTACACTTTGT
509  ATGAGGATAGTTACAAATCAGCAAGCACATGAGGTGGAAATTACTACTAATATCTATCAC
510  AAGGCCAAACATGTTAAAGCTTGGTGCCCAAGACCACCTCGGGCTGTGCCGTACACACAT
511  AGTCACTCTACAAATTACAAACCACATGAGGGTGATGTAAAGATTTTCATTAGACCCAGA
512  GATGATCCAAAGTTTGTAACTGCT
513  >33_HRV66
514  AATCCAGTTGAAGATTATGTTGAGGGTGTTTTAAATGAAGTTTTAGTAGTACCAAACATC
515  AAGGAAAGCCATCCAAGCACATCAAATGCTGCCCCAATACTAGATGCAGCTGAAACAGGT
516  CACACTAGTAAAGTACAACCAGAAGATACAGTTGAGACTCGTTACGTGCAAACATCACAG
517  ACTAGAGATGAAATGAGCATAGAAAGTTTTCTAGGTAGGTCAGGATGTATCCATATATCA
518  ACAATTAATGTGGATAGCACAAAAACATATGATGAATCCAAATTTAGAACATGGCAAATT
519  ACATTGCAAGAAATGGCTCAAATCAGACGCAAATTTGAGATGTTCACATATGTTAGGTTT
520  GATTCTGAAATTACATTAGTCCCATGCATTGCAGGAAAGGGTGATGATATAGGACATATT
```

FIG. D1 CONT'D

Rhino cDNA_DB.fasta                                              9/20/2007 5:08 PM

```
521 GTGATGCAATACATGTATGTACCACCTGGAGCCCCAATTCCAGATAATAGAACACACTTT
522 GCTTGGCAATCAGGAACAAATGCATCTATATTCTGGCAACTTGGACAACCATTCCCAAGA
523 TTCTCGCTACCTTTTCTAGGCATAGCTTCAGCATATTACATGTTCTATGATGGTTATGAT
524 GGAGATACTCCTGGGTCTCGTTATGGAACCACAGTAGTTAATCATATGGGTACATTATGT
525 ATTAGGATTGTTACAAATGAACAGCACCATAATGTTGAAATTACTACTAGAGTATACCAT
526 AAGGCTAAGCATGTTAAAGCCTGGTGTCCTAGACCACTTAGAGCTGTACCATACACAACT
527 GTAAACTCAACCAATTATATGCCTCATACTGGTGATCTGCAAATTTTCATTAAACCTAGA
528 ACAGATCCAAAAGTAGTCAATGTA
529 >34_HRV66b|
530 AATCCAGTTGAAGATTATGTTGAGGGTGTTTTAAATGAAGTTTTAGTAGTACCAAACATC
531 AAGGAAAGCCATCCAAGCACATCAAATGCTGCCCCAATACTAGATGCAGCTGAAACAGGT
532 CACACTAGTAAAGTACAACCAGAAGATACAGTTGAGACTCGTTACGTGCAAACATCACAG
533 ACTAGAGATGAAATGAGCATAGAAAGTTTTCTAGGTAGGTCAGGATGTATCCATATATCA
534 ACAATTAATGTGGATAGCACAAAAACATATGATGAATCCAAATTTAGAACATGGCAAATT
535 ACATTGCAAGAAATGGCTCAAATCAGACGCAAATTTGAGATGTTCACATATGTTAGGTTT
536 GATTCTGAAATTACATTAGTCCCATGCATTGCAGGAAAGGGTGATGATATAGGACATATT
537 GTGATGCAATACATGTATGTACCACCTGGAGCCCCAATTCCAGATAATAGAACACACTTT
538 GCTTGGCAATCAGGAACAAATGCATCTATATTCTGGCAACTTGGACAACCATTCCCAAGA
539 TTCTCGCTACCTTTTCTAGGCATAGCTTCAGCATATTACATGTTCTATGATGGTTATGAT
540 GGAGATACTCCTGGGTCTCGTTATGGAACCACAGTAGTTAATCATATGGGTACATTATGT
541 ATTAGGATTGTTACAAATGAACAGCACCATAATGTTGAAATTACTACTAGAGTATACCAT
542 AAGGCTAAGCATGTTAAAGCCTGGTGTCCTAGACCACTTAGAGCTGTACCATACACAACT
543 GTAAACTCAACCAATTATATGCCTCATACTGGTGATCTGCAAATTTTCATTAAACCTAGA
544 ACAGATCCAAAAGTAGTCAATGTG
545 >35_HRV66a|
546 AATCCAGTTGAAGATTATGTTGAGGGTGTTTTAAATGAAGTTTTAGTAGTACCAAACATC
547 AAGGAAAGCCATCCAAGCACATCAAATGCTGCCCCAATACTAGATGCAGCTGAAACAGGT
548 CACACTAGTAAAGTACAACCAGAAGATACAGTTGAGACTCGTTACGTGCAAACATCACAG
549 ACTAGAGATGAAATGAGCATAGAAAGTTTTCTAGGTAGGTCAGGATGTATCCATATATCA
550 ACAATTAATGTGGATAGCACAAAAACATATGATGAATCCAAATTTAGAACATGGCAAATT
551 ACATTGCAAGAAATGGCTCAAATCAGACGCAAATTTGAGATGTTCACATATGTTAGGTTT
552 GATTCTGAAATTACATTAGTCCCATGCATTGCAGGAAAGGGTGATGATATAGGACATATT
553 GTGATGCAATACATGTATGTACCACCTGGAGCCCCAATTCCAGATAATAGAACACACTTT
554 GCTTGGCAATCAGGAACAAATGCATCTATATTCTGGCAACTTGGACAACCATTCCCAAGA
555 TTCTCGCTACCTTTTCTAGGCATAGCTTCAGCATATTACATGTTCTATGATGGTTATGAT
556 GGAGATACTCCTGGGTCTCGTTATGGAACCACAGTAGTTAATCATATGGGTACATTATGT
557 ATTAGGATTGTTACAAATGAACAGCACCATAATGTTGAAATTACTACTAGAGTATACCAT
558 AAGGCTAAGCATGTTAAAGCCTGGTGTCCTAGACCACTTAGAGCTGTACCATACACAACT
559 GTAAACTCAACCAATTATATGCCTCATACTGGTGATCTGCAAATTTTCATTAAACCTAGA
560 ACAGATCCAAAAGTAGTCAATGTC
561 >36_HRV77a|
562 AATCCAGTTGAGGACTATATCGATAATGTACTTAATGAAGTCTTAGTAGTACCAAATACC
563 AAGGAGAGTCATCCAAGCACTTCTAACTCTGCTCCTATACTAGATGCAGCTGAAACAGGC
564 CATACTAGTAGTGTGCAACCAGAAGATACAGTTGAGACCCGCTATGTACAAACTTCCCAG
565 ACAAGGGATGAGATGAGTATTGAGAGCTTTCTGGGTAGGTCTGGTTGTATTCACATTTCA
566 ACAATAAATGTAGAAGATGGTAAAACTTATGATGAATCTAAATTTAGAAAATGGCAAATT
567 ACACTACAAGAAATGGCTCAAATTAGGCGCAAATTTGAAATGTTTACATATGTAAGATTT
568 GATTCAGAAATTACATTGGTCCCATGTATTGCTGGAAAAGGTGATGACATAGGACATGTT
569 GTCATGCAATACATGTATGTACCACCAGGGGCACCCATACCAGATAGCAGGACTCATTTT
570 GCATGGCAGTCAGGGACTAATGCATCAATATTCTGGCAACATGGACAACCATTCCCAAGA
571 TTTTCACTACCTTTTCTGAGTATTGCTTCAGCTTACTACATGTTTTATGATGGCTATGAT
572 GGGGATACCTATGAATCACGTTATGGTACTACAGTGGTTAATCACATGGGCACACTGTGC
573 ATTAGAATAGTCACTAATCAGCAAAATCATGAGGTTGAAATCACCACTAGAGTATACCAC
574 AAGGCTAAACATATTAAAGCTTGGTGTCCCAGACCACCTAGAGCTGTACCATACACAGCA
575 GTAGATTCAACAAATTACAAACCTATGAGAGGGGATGTACAAATCTTTATTAAAGAGAGA
576 GCAAGCCCAAAAGTAGTTACTTTG
577 >37_HRV77b|
578 AATCCAGTTGAGGACTATATCGATAATGTACTTAATGAAGTCTTAGTAGTACCAAATACC
579 AAGGAGAGTCATCCAAGCACTTCTAACTCTGCTCCTATACTAGATGCAGCTGAAACAGGC
580 CATACTAGTAGTGTGCAACCAGAAGATACAGTTGAGACCCGCTATGTACAAACTTCCCAG
581 ACAAGGGATGAGATGAGTATTGAGAGCTTTCTGGGTAGGTCTGGTTGTATTCACATTTCA
582 ACAATAAATGTAGAAGATGGTAAAACTTATGATGAATCTAAATTTAGAAAATGGCAAATT
583 ACACTACAAGAAATGGCTCAAATTAGGCGCAAATTTGAAATGTTTACATATGTAAGATTT
584 GATTCAGAAATTACATTGGTCCCATGTATTGCTGGAAAAGGTGATGACATAGGACATGTT
585 GTCATGCAATACATGTATGTACCACCAGGGGCACCCATACCAGATAGCAGGACTCATTTT
```

FIG. D1 CONT'D

Rhino cDNA_DB.fasta                                              9/20/2007 5:08 PM

```
586  GCATGGCAGTCAGGGACTAATGCATCAATATTCTGGCAACATGGACAACCATTCCCAAGA
587  TTTTCACTACCTTTTCTGAGTATTGCTTCAGCTTACTACATGTTTTATGATGGCTATGAT
588  GGGGATACCTATGAATCACGTTATGGTACTACAGTGGTTAATCACATGGGCACACTGTGC
589  ATTAGAATAGTCACTAATCAGCAAAATCATGAGGTTGAAATCACCACTAGAGTATACCAC
590  AAGGCTAAACATATTAAAGCTTGGTGTCCCAGACCACCTAGAGCTGTACCATACACAGCA
591  GTAGATTCAACAAATTACAAACCTATGAGAGGGGATGTACAAATCTTTATTAAAGAGAGA
592  GCAAGCCCAAAAGTAGTTACTTTA
593  >38_HRV77
594  AATCCAGTTGAGGACTATATCGATAATGTACTTAATGAAGTCTTAGTAGTACCAAATACC
595  AAGGAGAGTCATCCAAGCACTTCTAACTCTGCTCCTATACTAGATGCAGCTGAAACAGGC
596  CATACTAGTAGTGTGCAACCAGAAGATACAGTTGAGACCCGCTATGTACAAACTTCCCAG
597  ACAAGGGATGAGATGAGTATTGAGAGCTTTCTGGGTAGGTCTGGTTGTATTCACATTTCA
598  ACAATAAATGTAGAAGATGGTAAAACTTATGATGAATCTAAATTTAGAAAATGGCAAATT
599  ACACTACAAGAAATGGCTCAAATTAGGCGCAAATTTGAAATGTTTACATATGTAAGATTT
600  GATTCAGAAATTACATTGGTCCCATGTATTGCTGGAAAAGGTGATGACATAGGACATGTT
601  GTCATGCAATACATGTATGTACCACCAGGGGCACCCATACCAGATAGCAGGACTCATTTT
602  GCATGGCAGTCAGGGACTAATGCATCAATATTCTGGCAACATGGACAACCATTCCCAAGA
603  TTTTCACTACCTTTTCTGAGTATTGCTTCAGCTTACTACATGTTTTATGATGGCTATGAT
604  GGGGATACCTATGAATCACGTTATGGTACTACAGTGGTTAATCACATGGGCACACTGTGC
605  ATTAGAATAGTCACTAATCAGCAAAATCATGAGGTTGAAATCACCACTAGAGTATACCAC
606  AAGGCTAAACATATTAAAGCTTGGTGTCCCAGACCACCTAGAGCTGTACCATACACAGCA
607  GTAGATTCAACAAATTACAAACCTATGAGAGGGGATGTACAAATCTTTATTAAAGAGAGA
608  GCAAGCCCAAAAGTAGTTACTTTT
609  >39_HRV62a
610  AATCCAATTGAAAATTATGTAGATCAAGTACTTAATGAAGTTTTAGTTGTACCAAATATT
611  AAAGAAAGTCACCCTAGTACGTCAAACTCTGCCCCAATTCTAGATGCTGCTGAAACCGGA
612  CACACTAGTAATGTACAACCAGAAGACACTATTGAAACCCGTCATGTTCAAACCACACAA
613  ACTAGAGATGAAATGAGCATTGAGAGCTTCTTGGTAGGTCAGGGTGCGTACACACTTCA
614  ACAATTGAAACAACGCTTAGTCATAAAGATAGATTCAAAACATGGAATATTAACTTACAA
615  GAGATGGCTCAAATCAGGAGAAAGTTTGAAATGTTTACATATGTAAGATTTGATTCAGAA
616  ATAACCCTGGTTCCATCTATTGCAGGACGTGGTGCAGATATAGGTCACATAGTTATGCAA
617  TATATGTATGTACCACCTGGGGCTCCACTACCAACAGACAGAAAGCATTTTGCCTGGCAA
618  TCAAGTACTAATGCATCAATATTTTGGCAACATGGGCAACCCTTTCCTAGATTTTCATTA
619  CCTTTTTTGAGTGTTGCATCTGCTTATTACATGTTTTATGATGGCTATAATGGTGATGAC
620  TATACAGCAAAATACGGTACCACCGTGGTTAATCGTATGGGGGCACTGTGTATGAGGATT
621  GTCACAAACAAACAAGTTCATGATGTTGAGGTCACAACTAATATTTACCACAAGGCTAAG
622  CATGTAAAAGCGTGGTGCCCGCGGCCGCCCAGAGCTGTTCCATATAAATATGTTGATTTC
623  AATAATTATGCAGCCAGTGATAGTGTTGACATTTTTATAAAATCAAGGCAAAACTTGCAA
624  ACAGCT
625  >40_HRV62b
626  AATCCAATTGAAAATTATGTAGATCAAGTACTTAATGAAGTTTTAGTTGTACCAAATATT
627  AAAGAAAGTCACCCTAGTACGTCAAACTCTGCCCCAATTCTAGATGCTGCTGAAACCGGA
628  CACACTAGTAATGTACAACCAGAAGACACTATTGAAACCCGTTATGTTCAAACCACACAA
629  ACTAGAGATGAAATGAGCATTGAGAGCTTCTTGGTAGGTCAGGGTGCGTACACACTTCA
630  ACAATTGAAACAACGCTTAGTCATAAAGATAGATTCAAAACATGGAATATTAACTTACAA
631  GAGATGGCTCAAATCAGGAGAAAGTTTGAAATGTTTACATATGTAAGATTTGATTCAGAA
632  ATAACCCTGGTTCCATCTATTGCAGGACGTGGTGCAGATATAGGTCACATAGTTATGCAA
633  TATATGTATGTACCACCTGGGGCTCCACTACCAACAGACAGAAAGCATTTTGCCTGGCAA
634  TCAAGTACTAATGCATCAATATTTTGGCAACATGGGCAACCCTTTCCTAGATTTTCATTA
635  CCTTTTTTGAGTGTTGCATCTGCTTATTACATGTTTTATGATGGCTATAATGGTGATGAC
636  TATACAGCAAAATACGGTACCACCGTGGTTAATCGTATGGGGGCACTGTGTATGAGGATT
637  GTCACAAACAAACAAGTTCATGATGTTGAGGTCACAACTAATATTTACCACAAGGCTAAG
638  CATGTAAAAGCGTGGTGCCCTAGACCACCTAGAGCTGTTCCATATAAATATGTTGATTTC
639  AATAATTATGCAGCCAGTGATAGTGTTGACATTTTTATAAAATCAAGGCAAAACTTGCAA
640  ACAGC
641  >41_HRV25
642  AATCCAATTGAAAATTATGTAGATCAAGTACTTAATGAGGTTCTAGTCGTACCAAATATT
643  AAAGAAAGTCACCCAAGCACATCAAATTCTGCCCCAATTCTAGATGCTGCTGAAACTGGA
644  CACACTAGCAATGTGCAACCAGAGGATACCATTGAAACTCGTTATGTTCAAACCACACAA
645  ACTAGAGATGAAATGAGTATTGAAAGTTTTCTGGTAGGTCAGGGTGTGTACACATTTCA
646  ACAATTGAAACAAAACTTAAACATGATGAAAGATTTAAAATATGGAATATCAATTTACAA
647  GAAATGGCTCAAATTAGGAGAAAGTTTGAGATGTTTACATATGTGAGATTTGATTCAGAG
648  ATAACCCTAGTTCCATCTATTGCAGGACGTGGTGCAGATATAGGTCACATAGTTATGCAA
649  TATATGTATGTGCCACCTGGAGCCCCATTACCAACAGACAGAAAACACTTTGCATGGCAA
650  TCAAGTACTAATGCATCAATATTTTGGCAACATGGACAACCCTTCCCTAGATTTTCATTG
```

FIG. D1 CONT'D

Rhino cDNA DB.fasta                                          9/20/2007 5:08 PM

```
651 CCATTTCTGAGTGTTGCATCTGCTTATTACATGTTTTATGATGGCTATAATGGTGATGAT
652 CACACAGCGAGATATGGTACCACTGTGGTTAACCGTATGGGAGCACTGTGCATGAGAATT
653 GTCACAAATAAACAAGTCCATGATGTTGAGGTTACAACTAACATTTACCATAAAGCTAAG
654 CATGTAAAAGCATGGTGCCCTAGACCACCTAGAGCTGTCCCATATAAATATGTTGACTTC
655 AATAATTATGCAGCCAGTGATAATGTTGACATCTTTATACAACCAAGAAACAGTTTAAAA
656 ACAGCT
657 >42_HRV29a
658 AACCCAGTTGAAAACTATGTGGATGAGGTGCTTAATGAAGTTTTAGTTGTGCCTAACATC
659 AGGGAGAGCCACCCAAGCACGTCCAACTCTGCACCAATCTTGGATGCTGCTGAGACTGGA
660 CATACTAGTAATGTACAACCAGAAGATACCATTGAGACTCGTTATGTACAAACCTCACAT
661 ACTAGAGATGAAATGAGCATTGAAAGTTTCTTGGGTAGATCAGGATGTATACATGTTTCA
662 ACAATAAAAGCAAATCAGGCACATGACGCCAAGTTCGATAAATGGAATGTTAACTTACAA
663 GAAATGGCTCAAATTAGGCGCAAATTTGAAATGTTCACATATGTGAGATTTGACTCAGAA
664 ATAACTCTGGTTCTTTGCATTGCAGGACGTGGTAATGATATAGGTCACATAGTTATGCAG
665 TACATGTATGTACCACCTGGAGCTCCAGTACCAAATGACAGAAATCATTTTGCATGGCAA
666 TCAGGGACTAATGCATCAATATTCTGGCAACATGGTCAGCCTTTCCCAAGATTTTCATTA
667 CCATTCCTAAGTGTTGCATCTGCTTATTACATGTTTTATGATGGTTACAATGGAGGTGAT
668 CATACAGCAACTTATGGCACCACAGTGGTTAACCGGATGGGGACGCTTTGTGTCAGAATT
669 GTTACAGGCAAACAAGCTCATGATGTTCAAGTTACAACAAGTATCTATCATAAAGCTAAA
670 CATGTAAAGGCGTGGTGTCCTAGACCACCAAGAGTTGTCCCATACAAGTATGTTGGCCTA
671 ACTAATTACACACTTAAAGAAGAAGATCCAGTTGTGGAATCCAGACCAAGCTTAATGACA
672 GCT
673 >43_HRV29b
674 AACCCAGTTGAAAACTATGTGGATGAGGTGCTTAATGAAGTTTTAGTTGTGCCTAACATC
675 AGGGAGAGCCACCCAAGCACGTCCAACTCTGCACCAATCTTGGATGCTGCTGAGACTGGA
676 CATACTAGTAATGTACAACCAGAAGATACCATTGAGACTCGTTATGTACAAACCTCACAT
677 ACTAGAGATGAAATGAGCATTGAAAGTTTTCTTGGTAGATCAGGATGTATACATGTTTCA
678 ACAATAAAAGCAAATCAGGCACATGACGCCAAGTTCGATAAATGGAATGTTAACTTACAA
679 GAAATGGCTCAAATTAGGCGCAAATTTGAAATGTTCACATATGTGAGATTTGACTCAGAA
680 ATAACTCTGGTTCCATGCATTGCAGGACGTGGTAATGATATAGGTCACATAGTTATGCAG
681 TACATGTATGTACCACCTGGAGCTCCAGTACCAAATGACAGAAATCATTTTGCATGGCAA
682 TCAGGGACTAATGCATCAATATTCTGGCAACATGGTCAGCCTTTCCCAAGATTTTCATTA
683 CCATTCCTAAGTGTTGCATCTGCTTATTACATGTTTTATGATGGTTACAATGGAGGTGAT
684 CATACAGCAACTTATGGCACCACAGTGGTTAACCGGATGGGGACGCTTTGTGTCAGAATT
685 GTTACAGGCAAACAAGCTCATGATGTTCAAGTTACAACAAGTATCTATCATAAAGCTAAA
686 CATGTAAAGGCGTGGTGTCCTAGACCACCAAGAGTTGTCCCATACAAGTATGTTGGCCTA
687 ACTAATTACACACTTAAAGAAGAAGATACAGTTGTGGAATCCAGACCAAGCTTAATGACA
688 GCT
689 >44_HRV44a
690 AACCCAGTTGAAAATTATGTGGATGAAGTACTTAATGAAGTCTTAGTTGTGCCTAATATC
691 AGAGAGAGCCACCCAAGCACATCTAACTCTGCTCCAATTTTGGATGCTGCTGAAACTGGA
692 CATACTAGTAATGTACAACCAGAAGATACCATTGAGACTCGATATGTACAAACCTCACAA
693 ACTAGAGATGAAATGAGCATTGAAAGTTTTCTTGGCAGATCAGGGTGTATACATGTTTCA
694 ACAATAAAGACAAATCAGGCACACAATACCAAGTTTGATAAATGGAATATCAACTTACAA
695 GAAATGGCTCAAATTAGACGCAAATTTGAAATGTTCACATATGTGAGATTTGATTCGGAA
696 ATAACTCTAGTTCCATGCATTGCAGGACATGGTGATGATATAGGCCACATAGTTATGCAG
697 TACATGTATGTACCACCTGGAGCTCCAGTACCAGATGACAGAAACCACTTTGCATGGCAA
698 TCGGGGACTAATGCATCAATATTCTGGCAACATGGTCAACCTTTCCCAAGATTTTCATTG
699 CCATTTCTAAGTGTTGCATCTGCCTATTACATGTTTTATGACGGTTATAATGGAGGTGAT
700 CATACAGCAACTTATGGCACCACAGTGGTTAACCGGATGGGGACGCTTTGCGTCAGGATC
701 GTTACGGGCAAACAGGCTCATGATGTCCAAGTTACAACAAGCATTTATCACAAAGCTAAA
702 CATGTAAAAGCATGGTGCCCTAGACCACCAAGGGTTGTCCCATACAAGTATGTTGGCCTA
703 ACTAATTACACACTTAAAGAAACAGATACAGTTGTGGAACCTAGACACAGCATAATGACA
704 GCT
705 >45_HRV44b
706 AACCCAGTTGAAAATTATGTGGATGAAGTACTTAATGAAGTCTTAGTTGTGCCTAATATC
707 AGAGAGAGCCACCCAAGCATATCTAACTCTGCTCCAATTTTGGATGCTGCTGAAACTGGA
708 CATACTAGTAATGTACAACCAGAAGATACCATTGAGACTCGATATGTACAAACCTCACAA
709 ACTAGAGATGAAATGAGCATTGAAAGTTTTCTTGGCAGATCAGGGTGTATACATGTTTCA
710 ACAATAAAGACAAATCAGGCACACAATACCAAGTTTGATAAATGGAATATCAACTTACAA
711 GAAATGGCTCAAATTAGACGCAAATTTGAAATGTTCACATATGTGAGATTTGATTCAGAA
712 ATAACTCTAGTTCCATGCATTGCAGGACGTGGTGATGATATAGGCCACATAGTTATGCAG
713 TACATGTATGTACCACCTGGAGCTCCAGTACCAGATGACAGAATCCACTTTGCATGGCAA
714 TCGGGGAATAATGCATCAATATTCTGGCAACATGGTCAACCTTTCCCAAGATTTTCATTG
715 CCATTTCTAAGTGTTGCATCTGCCTATTACATGTTTTATGACGGTTATAATGGAGGTGAT
```

FIG. D1 CONT'D

Rhino cDNA_DB.fasta                                              9/20/2007 5:08 PM

```
716 CATACAGCAACTTATGGCACCACAGTGGTTAACCGGATGGGGACGCTTTGCGTCAGGATC
717 GTTACGGGCAAACAGGCTCATGATGTCCAAGTTACAACAAGCATTTATCACAAAGCTAAA
718 CATGTAAAAGCATGGTGCCCTAGACCACCAAGGGTTGTCCCATACAAGTATGTTGGCCTA
719 ACTAATTACACACTTAAAGAAACAGATACAGTTGTGGAACCTAGACACAGCATAATGACA
720 GCT
721 >46_HRV31
722 AATCCAGTTGAAAACTATGTGGAAGAGGTTCTTAATGAAGTCTTAGTAGTACCTAATATC
723 AAAGAAAGCCATCCAAGCACATCTAATTCTGCCCCAATCCTGGACGCTGCTGAAACTGGA
724 CACACTAGTAATGTACAACCAGAAGATACAATTGAAACTCGCTACGTGCAAACATCACAA
725 ACAAGAGATGAAATGAGCATTGAAAGTTTCCTTGGTAGGTCAGGATGTGTACATACTTCA
726 ATAATAGAACCAGATGGACTCCATGATAGCAAATATAAAGTATGGCACATTAATTTACAA
727 GAGATGGCCCAGATTAGGCGAAAATTTGAAATGTTCACATATGTAAGATTTGATTCAGAA
728 GTGACCATAGTTCCATGCATTGCAGGACATGGTAGTGACATAGGCCATATAGTCATGCAA
729 TACATGTATGTACCACCTGGGGCCCCAGTACCAACAAATAGAAAACATTTTGCATGGCAA
730 TCAGGTACTAATGCATCGATTTTCTGGCAACATGGACAACCCTTTCCAAGATTTACATTA
731 CCCTTTTTGAGTGTCGCATCCGCTTATTACATGTTTTATGATGGTTATGATGGAGACAAA
732 AGTGGAGCCAAGTATGGTACTACAGTAGTTAATCGCATGGGTGCACTATGCATGAGAGTT
733 GTCACTAACAAACAAGCTCATAAAGTTGAAATCACAACCAATATTTACCATAAGGCCAAA
734 CATGTTAAGGCATGGTGTCCTAGGCCCCCTAGAGCAGTTCCATACAGGGTATGTGGATCA
735 ACAAACTACAAACCTGATGAAAATGAAGTTACAATCTTTGTTAAACACAGGGATAATCCA
736 AAGATTATCACAGCA
737 >47_HRV31a|
738 AATCCAGTTGAAAACTATGTGGAAGAGGTTCTTAATGAAGTCTTAGTAGTACCTAATATC
739 AAAGAAAGCCATCCAAGCACATCTAATTCTGCCCCAATCCTGGACGCTGCTGAAACTGGA
740 CACACTAGTAATGTACAACCAGAAGATACAATTGAAACTCGCTACGTGCAAACATCACAA
741 ACAAGAGATGAAATGAGCATTGAAAGTTTCCTTGGTAGGTCAGGATGTGTACATACTTCA
742 ATAATAGAACCAGATGGACTCCATGATAGCAAATATAAAGTATGGCACATTAATTTACAA
743 GAGATGGCCCAGATTAGGCGAAAATTTGAAATGTTCACATATGTAAGATTTGATTCAGAA
744 GTGACCATAGTTCCATGCATTGCAGGACATGGTAGTGACATAGGCCATATAGTCATGCAA
745 TACATGTATGTACCACCTGGGGCCCCAGTACCAACAAATAGAAAACATTTTGCATGGCAA
746 TCAGGTACTAATGCATCGATTTTCTGGCAACATGGACAACCCTTTCCAAGATTTACATTA
747 CCCTTTTTGAGTGTCGCATCCGCTTATTACATGTTTTATGATGGTTATGATGGAGACAAA
748 AGTGGAGCCAAGTATGGTACTACAGTAGTTAATCGCATGGGTGCACTATGCATGAGAGTT
749 GTCACTAACAAACAAGCTCATAAAGTTGAAATCACAACCAATATTTACCATAAGGCCAAA
750 CATGTTAAGGCATGGTGTCCTAGGCCCCCTAGAGCAGTTCCATACAGGGTATGTGGATCA
751 ACAAACTACAAACCTGATGAAAATGAAGTTACAATCTTTGTTAAACACAGGGATAATCCA
752 AAGATTATCACAGCT
753 >48_HRV31b|
754 AATCCAGTTGAAAACTATGTGGAAGAGGTTCTTAATGAAGTCTTAGTAGTACCTAATATC
755 AAAGAAAGCCATCCAAGCACATCTAATTCTGCCCCAATCCTGGACGCTGCTGAAACTGGA
756 CACACTAGTAATGTACAACCAGAAGATACAATTGAAACTCGCTACGTGCAAACATCACAA
757 ACAAGAGATGAAATGAGCATTGAAAGTTTCCTTGGTAGGTCAGGATGTGTACATACTTCA
758 ATAATAGAACCAGATGGACTCCATGATAGCAAATATAAAGTATGGCACATTAATTTACAA
759 GAGATGGCCCAGATTAGGCGAAAATTTGAAATGTTCACATATGTAAGATTTGATTCAGAA
760 GTGACCATAGTTCCATGCATTGCAGGACATGGTAGTGACATAGGCCATATAGTCATGCAA
761 TACATGTATGTACCACCTGGGGCCCCAGTACCAACAAATAGAAAACATTTTGCATGGCAA
762 TCAGGTACTAATGCATCGATTTTCTGGCAACATGGACAACCCTTTCCAAGATTTACATTA
763 CCCTTTTTGAGTGTCGCATCCGCTTATTACATGTTTTATGATGGTTATGATGGAGACAAA
764 AGTGGAGCCAAGTATGGTACTACAGTAGTTAATCGCATGGGTGCACTATGCATGAGAGTT
765 GTCACTAACAAACAAGCTCATAAAGTTGAAATCACAACCAATATTTACCATAAGGCCAAA
766 CATGTAAAGGCATGGTGTCCTAGGCCACCTAGAGCAGTTCCATACAGGTATGTTGGATCA
767 ACAAACTACAAACCTGATGAAAATGAAGTTACAATCTTTGTTAAACACAGGGATAATCCA
768 AAGATTATCACAGCA
769 >49_HRV47
770 AACCCAGTCGAAAATTATGTGGAAGAGGTACTTAATGAGGTCTTAGTTGTACCAAATATC
771 AAAGAAAGTCATCCAAGTACATCCAACTCTGCCCCGATTTTAGATGCTGCTGAAACTGGA
772 CACACTAGCAATGTACAGCCAGAAGATACAATTGAAACTCGATATGTACAAACAGCACAA
773 ACAAGAGATGAAATGAGCATTGAGAGCTTCCTTGGCAGGTCAGGATGTGTGCATTCCTCA
774 ACAATAAAATCAGATGAAGCAACACATTAATAAATTTAAAGTATGGCACATTAATTTACAA
775 GAAATGGCCCAGATCAGGCGTAAATATGAAATGTTTACATATGTAAGATTTGATTCAGAA
776 GTAACCATGGTTCCATGTATTGCAGGGTATGGTGATGACATAGGTCACATAGTTATGCAA
777 TACATGTATGTGCCGCCTGGGGCTCCAGTGCCAACAAGTAGAGAGCACTTTGCATGGCAG
778 TCAGGTACCAATGCATCAACTTTCTGGCAACAAGGGCAACCCTTTCCAAGATTTTCATTA
779 CCATTTTTGAGTGTTGCATCTGCTTATTACATGTTTTATGATGGCTATAATGGTGACAGA
780 AGTGGAGCCAAGTATGGCACCACAGTGGTCAATCGCATGGGTGCATTGTGTATGAGAGTT
```

Rhino_cDNA_DB.fasta                                               9/20/2007 5:08 PM

```
781  GTAACAAACAAGCAACTCCATAAAGTTGAAATCACAACTAACATCTACCATAAAGCCAAG
782  CATGTGAAAGCATGGTGTCCTAGACCACCTAGAGCTGTTCCATATAGATATGTTGGATCA
783  ACAAATTACAAACCTGATCAAGGAGAAGTTGCAATTTTCATTGAGCATAGAGAAATCCA
784  AAATTCATTACAGCA
785  >50_HRV47a|
786  AACCCAGTCGAAAATTATGTGGAAGAGGTACTTAATGAGGTCTTAGTTGTACCAAATATC
787  AAAGAAAGTCATCCAAGTACATCCAACTCTGCCCCGATTTTAGATGCTGCTGAAACTGGA
788  CACACTAGCAATGTACAGCCAGAAGATACAATTGAAACTCGATATGTACAAACAGCACAA
789  ACAAGAGATGAAATGAGCATTGAGAGCTTCCTTGGCAGGTCAGGATGTGTGCATTCCTCA
790  ACAATAAAATCAGATGAGCAACACATTAATAAATTTAAAGTATGGCACATTAATTTACAA
791  GAAATGGCCCAGATCAGGCGTAAATATGAAATGTTTACATATGTAAGATTTGATTCAGAA
792  GTAACCATGGTTCCATGTATTGCAGGGTATGGTGATGACATAGGTCACATAGTTATGCAA
793  TACATGTATGTGCCGCCTGGGGCTCCAGTGCCAACAAGTAGAGAGCACTTTGCATGGCAG
794  TCAGGTACCAATGCATCAACTTTCTGGCAACAAGGGCAACCCTTTCCAAGATTTTCATTA
795  CCATTTTTGAGTGTTGCATCTGCTTATTACATGTTTTATGATGGCTATAATGGTGACAGA
796  AGTGGAGCCAAGTATGGCACCACAGTGGTCAATCGCATGGGTGCATTGTGTATGAGAGTT
797  GTAACAAACAAGCAACTCCATAAAGTTGAAATCACAACTAACATCTACCATAAAGCCAAG
798  CATGTGAAAGCATGGTGTCCTAGACCACCTAGAGCTGTTCCATATAGATATGTTGGATCA
799  ACAAATTACAAACCTGATCAAGGAGAAGTTGCAATTTTCATTGAGCATAGAGAAATCCA
800  AAATTCATTACAGCT
801  >51_HRV47b|
802  AACCCAGTCGAAAATTATGTGGAAGAGGTACTTAATGAGGTCTTAGTTGTACCAAATATC
803  AAAGAAAGTCATCCAAGTACATCCAACTCTGCCCCGATTTTAGATGCTGCTGAAACTGGA
804  CACACTAGCAATGTACAGCCAGAAGATACAATTGAAACTCGATATGTACAAACAGCACAA
805  ACAAGAGATGAAATGAGCATTGAGAGCTTCCTTGGCAGGTCAGGATGTGTGCATTCCTCA
806  ACAATACAATCAAATGAGCAACACATTAATAAATTTAAAGTATGGCACATTAATTTACAA
807  GAAATGGCCCAGATCAGGCGTAAATATGAAATGTTTACATATGTAAGATTTGATTCAGAA
808  GTAACCATGGTTCCATGTATTGCAGGGTATGGTGATGACATAGGTCACATAGTTATGCAA
809  TACATGTATGTGCCGCCTGGGGCTCCAGTGCCAACAAGTAGAGAGCACTTTGCATGGCAG
810  TCAGGTACCAATGCATCAATTTTCTGGCAACAAGGGCAACCCTTTCCAAGATTTTCATTA
811  CCATTTTTGAGTGTTGCATCTGCTTATTACATGTTTTATGATGGCTATAATGGTGACAGA
812  AGTGGAGCCAAGTATGGCACCACAGTGGTCAATCGCATGGGTGCATTGTGTATGAGAGTT
813  GTAACAAACAAGCAACTCCATAAAGTTGAAATCACAACTAACATCTACCATAAAGCCAAG
814  CATGTGAAAGCATGGTGTCCTAGACCACCTAGAGCTGTTCCATATAGATATGTTGGATCA
815  ACAAATTACAAACCTGATCAAGGAGAAGTTGCAATTTTCATTGAGCATAGAGAAATCCA
816  AAATTCATTACAGCA
817  >52_HRV11
818  AACCCAGTGGAGGATTATGTTGATGGAATTCTAAATGAGGTTTTAGTTGTACCTAATATA
819  AAGGAGAGCCAAGCTACCACATCAAACTCAGCACCTGCTCTAGATGCAGCTGAAACCGGA
820  CATACTAGCAAAGTGCAGCCAGAGGATATGATTGAGACTAGATATGTGCAGACTTCACAG
821  ACTCTTGATGAAATGAGCATTGAGAGCTTCCTAGGTAGATCTGGTTGTATTCACATGTCC
822  AAGTTAATTGTGCAGTATGAAGACTATAATGGAAAGAAAAACTTTAACACATGGAAATA
823  AACTTGCAAGAGATGGCACAAATTAGAAGGAAATTTGAAATGTTCACATACACTAGATTT
824  GATTCAGAGATCACATTGGTGCCTTGTATAGCTGCAAAAGGAAATGATATTGGTCATGTT
825  GTAATGCAATATATGTATGTCCCACCAGGTGCTCCAGTTCCAGAGAAAAGAGATGATTAT
826  ACATGGCAATCAGGAACAAATGCATCTATTTTCTGGCAATATGGTCAAACATACCCAAGA
827  TTTTCTCTACCTTTCATGAGTATAGCCTCAGCATATTACATGTTTTATGATGGATATGAT
828  GGGAGATCAACCAAACTCCAGATATGGTAATATAGTTACCAATGATATGGGCACTCTGTGT
829  TATAGAATAGTAACTGATGACCATAGACACAAAATTGAAGTCACAACTAGGGTGTATCAT
830  AAAGCAAAGCATGTGAAGGTGTGGTGTCCAAGACCACCTAGAGCTGTAGAATATACTCAC
831  ACTCATGTAACCAATTACAAACCACAGGAAGGACAGGTGAAAACAGCTGTCAAGGCTAGG
832  AAAACAATTAAAACAGCA
833  >53_HRV11b|
834  AACCCAGTGGAGGATTATGTTGATGGAATTCTAAATGAGGTTTTAGTTGTACCTAATATA
835  AAGGAGAGCCAAGCTACCACATCAAACTCAGCACCTGCTCTAGATGCAGCTGAAACCGGA
836  CATACTAGCAAAGTGCAGCCAGAGGATATGATTGAGACTAGATATGTGCAGACTTCACAG
837  ACTCTTGATGAAATGAGCATTGAGAGCTTCCTAGGTAGATCTGGTTGTATTCACATGTCC
838  AAGTTAATTGTGCAGTATGAAGACTATAATGGAAAGAAAAACTTTAACACATGGAAATA
839  AACTTGCAAGAGATGGCACAAATTAGAAGGAAATTTGAAATGTTCACATACACTAGATTT
840  GATTCAGAGATCACATTGGTGCCTTGTATAGCTGCAAAAGGAAATGATATTGGTCATGTT
841  GTAATGCAATATATGTATGTCCCACCAGGTGCTCCAGTTCCAGAGAAAAGAGATGATTAT
842  ACATGGCAATCAGGAACAAATGCATCTATTTTCTGGCAATATGGTCAAACATACCCAAGA
843  TTTTCTCTACCTTTCATGAGTATAGCCTCAGCATATTACATGTTTTATGATGGATATGAT
844  GGGAGATCAACCAAACTCCAGATATGGTAATATAGTTACCAATGATATGGGCACTCTGTGT
845  TATAGAATAGTAACTGATGACCATAGACACAAAATTGAAGTCACAACTAGGGTGTATCAT
```

FIG. D1 CONT'D

Rhino cDNA_DB.fasta                                              9/20/2007 5:08 PM

```
846 AAAGCAAAGCATGTGAAGGTGTGGTGTCCAAGACCACCTAGAGCTGTAGAATATACTCAC
847 ACTCATGTAACCAATTACAAACCACAGGAAGGACAGGTGAAAACAGCTGTCAAGGCTAGG
848 AAAACAATTAAAACAGCG
849 >54_HRV11a|
850 AACCCAGTGGAGGATTATGTTGATGGAATTCTAAATGAGGTTTTAGTTGTACCTAATATA
851 AAGGAGAGCCAAGCTACCACATCAAACTCAGCACCTGCTCTAGATGCAGCTGAAACCGGA
852 CATACTAGCAAAGTGCAGCCAGAGGATATGATTGAGACTAGATATGTGCAGACTTCACAG
853 ACTCTTGATGAAATGAGCATTGAGAGCTTCCTAGGTAGATCTGGTTGTATTCACATGTCC
854 AAGTTAATTGTGCAGTATGAAGACTATAATGGAAAGAAAAACTTTAACACATGGAAATA
855 AACTTGCAAGAGATGGCACAAATTAGAAGGAAATTTGAAATGTTCACATACACTAGATTT
856 GATTCAGAGATCACATTGGTGCCTTGTATAGCTGCAAAAGGAAATGATATTGGTCATGTT
857 GTAATGCAATATATGTATGTCCCACCAGGTGCTCCAGTTCCAGAGAAAAGAGATGATTAT
858 ACATGGCAATCAGGAACAAATGCATCTATTTTCTGGCAATATGGTCAAACATACCCAAGA
859 TTTTCTCTACCTTTCATGAGTATAGCCTCAGCATATTACATGTTTTATGATGGATATGAT
860 GGAGATCAACCAAACTCCAGATATGGTAATATAGTTACCAATGATATGGGCACTCTGTGT
861 TATAGAATAGTAACTGATGACCATAGACACAAAATTGAAGTCACAACTAGGGTGTATCAT
862 AAAGCAAAGCATGTGAAGGTGTGGTGTCCAAGACCACCTAGAGCTGTAGAATATACTCAC
863 ACTCATGTAACCAATTACAAACCACAGGAAGGACAGGTGAAAACAGCTGTCAAGGCTAGG
864 AAAACAATTAAAACAGCT
865 >55_HRV76
866 AACCCAGTTGAAAATTACGTGGATGAGATATTAAATGAGGTTCTTGTAGTACCAAACATC
867 AAAGAGAGTCAGGCTACCACATCAAATGCAGCACCTGCTTTGGATGCAGCTGAGACTGGG
868 CACACAAGCAGCGTTCAACCAGAGGACATGGTTGAGACTAGGTATGTGCAAACATCACAA
869 ACTCTTGATGAGATGTGTATGGAGAGTTTCTTAGGGAGATCTGGTTGTATTCATATTTCA
870 AAGCTAGTTGTAGAATATGAGGGATATGATGATACAAAAAACTTTAAGACATGGAAATA
871 AACCTACAAGAAATGGCACAAGTTAGAAGAAAATTTGAGATGTTTACATATACTAGATTT
872 GATTCAGAAGTTACTCTAGTTCCTTCTATAGCTGCCAAAGGGGATGACATTGGTCATGTA
873 GTGATGCAATACATGTATGTCCCACCAGGCGCTCCAGTTCCAAAGAAGAGAGATGACTAC
874 ACATGGCAGTCAGGAACCAATGCATCTATTTTCTGGCAATATGGACAAACATACCCTAGG
875 TTTTCATTACCCTTTCTAAGTATAGCTTCAGCTTATTACATGTTTTATGATGGATATGAT
876 GGAGACCAACCTAGTTCTAGGTATGGTAATATAGTTACCAATGACATGGGCACCCTATGT
877 TCCAGGATAGTAACTGATGATCATAAGCACAAGATTGAAGTTACAACAAGAATATATCAC
878 AAAGCAAAGCATGTTAAGGTATGGTGCCCGAGACCACCTAGAGCTGTAGAGTATACATAC
879 ACCCATGTAACAAACTACAAACCACATTCTGGTGATGTGCAAACAGCTATTAGACCAAGA
880 GCAACAATTAAGACTGCA
881 >56_HRV76b|
882 AACCCAGTTGAAAATTACGTGGATGAGATATTAAATGAGGTTCTTGTAGTACCAAACATC
883 AAAGAGAGTCAGGCTACCACATCAAATGCAGCACCTGCTTTGGATGCAGCTGAGACTGGG
884 CACACAAGCAGCGTTCAACCAGAGGACATGGTTGAGACTAGGTATGTGCAAACATCACAA
885 ACTCTTGATGAGATGTGTATGGAGAGTTTCTTAGGGAGATCTGGTTGTATTCATATTTCA
886 AAGCTAGTTGTAGAATATGAGGGATATGATGATACAAAAAACTTTAAGACATGGAAATA
887 AACCTACAAGAAATGGCACAAGTTAGAAGAAAATTTGAGATGTTTACATATACTAGATTT
888 GATTCAGAAGTTACTCTAGTTCCTTCTATAGCTGCCAAAGGGGATGACATTGGTCATGTA
889 GTGATGCAATACATGTATGTCCCACCAGGCGCTCCAGTTCCAAAGAAGAGAGATGACTAC
890 ACATGGCAGTCAGGAACCAATGCATCTATTTTCTGGCAATATGGACAAACATACCCTAGG
891 TTTTCATTACCCTTTCTAAGTATAGCTTCAGCTTATTACATGTTTTATGATGGATATGAT
892 GGAGACCAACCTAGTTCTAGGTATGGTAATATAGTTACCAATGACATGGGCACCCTATGT
893 TCCAGGATAGTAACTGATGATCATAAGCACAAGATTGAAGTTACAACAAGAATATATCAC
894 AAAGCAAAGCATGTTAAGGTATGGTGCCCGAGACCACCTAGAGCTGTAGAGTATACATAC
895 ACCCATGTAACAAACTACAAACCACATTCTGGTGATGTGCAAACAGCTATTAGACCAAGA
896 GCAACAATTAAGACTGCG
897 >57_HRV76a|
898 AACCCAGTTGAAAATTACGTGGATGAGATATTAAATGAGGTTCTTGTAGTACCAAACATC
899 AAAGAGAGTCAGGCTACCACATCAAATGCAGCACCTGCTTTGGATGCAGCTGAGACTGGG
900 CACACAAGCAGCGTTCAACCAGAGGACATGGTTGAGACTAGGTATGTGCAAACATCACAA
901 ACTCTTGATGAGATGTGTATGGAGAGTTTCTTAGGGAGATCTGGTTGTATTCATATTTCA
902 AAGCTAGTTGTAGAATATGAGGGATATGATGATACAAAAAACTTTAAGACATGGAAATA
903 AACCTACAAGAAATGGCACAAGTTAGAAGAAAATTTGAGATGTTTACATATACTAGATTT
904 GATTCAGAAGTTACTCTAGTTCCTTCTATAGCTGCCAAAGGGGATGACATTGGTCATGTA
905 GTGATGCAATACATGTATGTCCCACCAGGCGCTCCAGTTCCAAAGAAGAGAGATGACTAC
906 ACATGGCAGTCAGGAACCAATGCATCTATTTTCTGGCAATATGGACAAACATACCCTAGG
907 TTTTCATTACCCTTTCTAAGTATAGCTTCAGCTTATTACATGTTTTATGATGGATATGAT
908 GGAGACCAACCTAGTTCTAGGTATGGTAATATAGTTACCAATGACATGGGCACCCTATGT
909 TCCAGGATAGTAACTGATGATCATAAGCACAAGATTGAAGTTACAACAAGAATATATCAC
910 AAAGCAAAGCATGTTAAGGTATGGTGCCCGAGACCACCTAGAGCTGTAGAGTATACATAC
```

FIG. D1 CONT'D

Rhino_cDNA_DB.fasta                                                9/20/2007 5:08 PM

```
911 ACCCATGTAACAAACTACAAACCACATTCTGGTGATGTGCAAACAGCTATTAGACCAAGA
912 GCAACAATTAAGACTGCT
913 >58_HRV33
914 AATCCAGTAGAGAATTATATAGAAGAGGTGTTGAATGAGGTTTTAGTAGTGCCTAATATC
915 AGAGAGAGTCAAGCAACCACATCAAATTCAGCACCTGCCTTAGATGCAGCTGAGACTGGA
916 CACACTAATAATGTACAACCAGAAGATATGATTGAAACAAGATATGTACAAACATCACAA
917 ACTCTTGATGAGATGAGTGTGGAAAGCTTCTTAGGAAGGTCTGGTTGCATTCACATGTCA
918 AAATTAGTAGTGAAATATGAAGACTATAATGAGAAAAAGAATTTTATGACATGGAAAATA
919 AATCTACAAGAGATGGCACAGATTAGGAGGAAATTTGAAATGTTTACATATGCCAGATTT
920 GATTCAGAGATCACCCTAGTCCCTTCTATAGCTGCCCAGGGAGATGATGTTGGTCATGTT
921 GTAATGCAGTACATGTATGTCCCACCAGGTGCACCAGCTCCAGAAAAGAGAGATGATTAC
922 ACATGGCAATCAGGAACAAATGCATCTGTCTTTTGGCAATATGGACAAACATATCCTAGG
923 TTCTCATTACCTTTCCTTAGCATAGCTTCAGCATATTACATGTTCTATGATGGATATGAT
924 GGGGACCAACCCAATTCCAGGTATGGTAATATGGTTACCAATGACATGGGCACTTTATGC
925 TCTAGAATAGTTACAGATAATCATAAGCATCCAATAGAAGTTACAACAAGAGTATACCAT
926 AAAGCAAAACATGTCAAAGTCTGGTGCCCAAGACCACCTAGAGCTGTGGAATACACCCAT
927 ACTCATGTTACAAATTATAAATCAACAACTCGTGAAGTGAAGACAGCTATTAGACCAAGA
928 GCAACAATCAAGACTGCA
929 >59_HRV33b|
930 AATCCAGTAGAGAATTATATAGAAGAGGTGTTGAATGAGGTTTTAGTAGTGCCTAATATC
931 AGAGAGAGTCAAGCAACCACATCAAATTCAGCACCTGCCTTAGATGCAGCTGAGACTGGA
932 CACACTAATAATGTACAACCAGAAGATATGATTGAAACAAGATATGTACAAACATCACAA
933 ACTCTTGATGAGATGAGTGTGGAAAGCTTCTTAGGAAGGTCTGGTTGCATTCACATGTCA
934 AAATTAGTAGTGAAATATGAAGACTATAATGAGAAAAAGAATTTTATGACATGGAAAATA
935 AATCTACAAGAGATGGCACAGATTAGGAGGAAATTTGAAATGTTTACATATGCCAGATTT
936 GATTCAGAGATCACCCTAGTCCCTTCTATAGCTGCCCAGGGAGATGATGTTGGTCATGTT
937 GTAATGCAGTACATGTATGTCCCACCAGGTGCACCAGCTCCAGAAAAGAGAGATGATTAC
938 ACATGGCAATCAGGAACAAATGCATCTGTCTTTTGGCAATATGGACAAACATATCCTAGG
939 TTCTCATTACCTTTCCTTAGCATAGCTTCAGCATATTACATGTTCTATGATGGATATGAT
940 GGGGACCAACCCAATTCCAGGTATGGTAATATGGTTACCAATGACATGGGCACTTTATGC
941 TCTAGAATAGTTACAGATAATCATAAGCATCCAATAGAAGTTACAACAAGAGTATACCAT
942 AAAGCAAAACATGTCAAAGTCTGGTGCCCAAGACCACCTAGAGCTGTGGAATACACCCAT
943 ACTCATGTTACAAATTATAAATCAACAACTCGTGAAGTGAAGACAGCTATTAGACCAAGA
944 GCAACAATCAAGACTGCG
945 >60_HRV33a|
946 AATCCAGTAGAGAATTATATAGAAGAGGTGTTGAATGAGGTTTTAGTAGTGCCTAATATC
947 AGAGAGAGTCAAGCAACCACATCAAATTCAGCACCTGCCTTAGATGCAGCTGAGACTGGA
948 CACACTAATAATGTACAACCAGAAGATATGATTGAAACAAGATATGTACAAACATCACAA
949 ACTCTTGATGAGATGAGTGTGGAAAGCTTCTTAGGAAGGTCTGGTTGCATTCACATGTCA
950 AAATTAGTAGTGAAATATGAAGACTATAATGAGAAAAAGAATTTTATGACATGGAAAATA
951 AATCTACAAGAGATGGCACAGATTAGGAGGAAATTTGAAATGTTTACATATGCCAGATTT
952 GATTCAGAGATCACCCTAGTCCCTTCTATAGCTGCCCAGGGAGATGATGTTGGTCATGTT
953 GTAATGCAGTACATGTATGTCCCACCAGGTGCACCAGCTCCAGAAAAGAGAGATGATTAC
954 ACATGGCAATCAGGAACAAATGCATCTGTCTTTTGGCAATATGGACAAACATATCCTAGG
955 TTCTCATTACCTTTCCTTAGCATAGCTTCAGCATATTACATGTTCTATGATGGATATGAT
956 GGGGACCAACCCAATTCCAGGTATGGTAATATGGTTACCAATGACATGGGCACTTTATGC
957 TCTAGAATAGTTACAGATAATCATAAGCATCCAATAGAAGTTACAACAAGAGTATACCAT
958 AAAGCAAAACATGTCAAAGTCTGGTGCCCAAGACCACCTAGAGCTGTGGAATACACCCAT
959 ACTCATGTTACAAATTATAAATCAACAACTCGTGAAGTGAAGACAGCTATTAGACCAAGA
960 GCAACAATCAAGACTGCT
961 >61_HRV24a|
962 AACCCAGTAGAAAATTATATAGATGAGGTTTTGAATGAAGTACTGGTTGTGCCTAATATT9
963 AAGGAAAGTAAACCATCAACATCAAACTCAGCACCAGCTTTGGATGCAGCAGAAACTGGA
964 CATACGAGTAGCGTGCAGCCAGAAGATATGGTTGAAACAGATATGTCCAAACATCACAA
965 ACATTACATGAGATGAGTGTTGAAAGTTTCTTGGGTAGATCAGGTTGCATACACATGTCC
966 AAGTTGACTGTGGATTATGACAATTATGATACAAAAAATTTTTTCAAATGGCAAATAAAT
967 CTACAAGAAATGGCCCAAGTCAGAAGAAAATTTGAATTATTCACATATACTAGATTTGAC
968 TCTGAGATTACAATAGTTCCATCCATAGCTGGCAAGGGAGATGATGATCATTGGTCATGGTA
969 ATGCAGTACATGTATATACCACCTGGAGCACCAGTCCCAACAAAGAGAGATGATTATACA
970 TGGCAATCAGGAACAAATGCATCTGTCTTTTGGCAACATGGACAAACCTATCCTAGATTT
971 TCCCTTCCTTTTCTGAGTGTAGCCTCTGCATATTACATGTTTTATGATGGATATGATGGT
972 GATCAACACGACTCAGTGTATGGTTCAGTTGTTACAAACGACATGGGAACTCTATGCTAT
973 AGAATAGTCACTGACAAGCATAATCACCAAATAGAAATTACAACAAGAATATACCACAAA
974 GCAAAGCACATTAAGGTCTGGTGTCCAAGGCCACCCAGAGCTGTTGAGTATACACATACT
975 CACGTGACCAATTATAAGCATCAGACTCGTGAAGTCAAGACAGCAATTGAACCTAGAAGA
```

FIG. D1 CONT'D

Rhino cDNA DB.fasta                                      9/20/2007 5:08 PM

```
 976  GGAATTAAAACAGTG
 977  >62_HRV24b|
 978  AACCCAGTAGAAAATTATATAGATGAGGTTTTGAATGAAGTACTGGTTGTGCCTAATATT
 979  AAGGAAAGTAAACCATCAACATCAAACTCAGCACCAGCTTTGGATGCAGCAGAAACTGGA
 980  CATACGAGTAGCGTGCAGCCAGAAGATATGGTTGAAACTAGATATGTCCAAACATCACAA
 981  ACATTACATGAGATGAGTGTTGAAAGTTTCTTGGGTAGATCAGGTTGCATACACATGTCC
 982  AAGTTGACTGTGGATTATGACAATTATGATACAAAAAATTTTTTCAAATGGCAAATAAAT
 983  CTACAAGAAATGGCCCAAGTCAGAAGAAAATTTGAATTATTCACATATACTAGATTTGAC
 984  TCTGAGATTACAATAGTTCCATCCATAGCTGGCAAGGGAGATGACATTGGACATGTTGTA
 985  ATGCAGTACATGTATATACCACCTGGAGCACCAGTCCCAACAAAGAGAGATGATTATACA
 986  TGGCAATCAGGAACAAATGCATCTGTCTTTTGGCAACATGGACAAACCTATCCTAGATTT
 987  TCCCTTCCTTTTCTGAGTGTAGCCTCTGCATATTACATGTTTTATGATGGATATGATGGT
 988  GATCAACACGACTCAGTGTATGGTTCAGTTGTTACAAACGACATGGGAACTCTATGCTAT
 989  AGAATAGTCACTGACAAGCATAATCACCAAATAGAAATTACAACAAGAATATACCACAAA
 990  GCAAAGCACATTAAGGTCTGGTGTCCAAGGCCACCCAGAGCTGTTGAGTATACACATACT
 991  CACGTGACCAATTATAAGCATCAGACTCGTGAAGTCAAGACAGCAATTGAACCTAGAAGA
 992  GGAATTAAAACAGTC
 993  >63_HRV24
 994  AACCCAGTAGAAAATTATATAGATGAGGTTTTGAATGAAGTACTGGTTGTGCCTAATATT
 995  AAGGAAAGTAAACCATCAACATCAAACTCAGCACCAGCTTTGGATGCAGCAGAAACTGGA
 996  CATACGAGTAGCGTGCAGCCAGAAGATATGGTTGAAACTAGATATGTCCAAACATCACAA
 997  ACATTACATGAGATGAGTGTTGAAAGTTTCTTGGGTAGATCAGGTTGCATACACATGTCC
 998  AAGTTGACTGTGGATTATGACAATTATGATACAAAAAATTTTTTCAAATGGCAAATAAAT
 999  CTACAAGAAATGGCCCAAGTCAGAAGAAAATTTGAATTATTCACATATACTAGATTTGAC
1000  TCTGAGATTACAATAGTTCCATCCATAGCTGGCAAGGGAGATGACATTGGACATGTTGTA
1001  ATGCAGTACATGTATATACCACCTGGAGCACCAGTCCCAACAAAGAGAGATGATTATACA
1002  TGGCAATCAGGAACAAATGCATCTGTCTTTTGGCAACATGGACAAACCTATCCTAGATTT
1003  TCCCTTCCTTTTCTGAGTGTAGCCTCTGCATATTACATGTTTTATGATGGATATGATGGT
1004  GATCAACACGACTCAGTGTATGGTTCAGTTGTTACAAACGACATGGGAACTCTATGCTAT
1005  AGAATAGTCACTGACAAGCATAATCACCAAATAGAAATTACAACAAGAATATACCACAAA
1006  GCAAAGCACATTAAGGTCTGGTGTCCAAGGCCACCCAGAGCTGTTGAGTATACACATACT
1007  CACGTGACCAATTATAAGCATCAGACTCGTGAAGTCAAGACAGCAATTGAACCTAGAAGA
1008  GGAATTAAAACAGTT
1009  >64_HRV90
1010  AATCCAGTGGAAAATTATATAGATGAAGTCCTAAATGAGGTATTGGTTGTCCCTAATATT
1011  AAGGAAAGTAAACCTTCAACTTCAAACTCAGCGCCAGCTTTAGATGCAGCAGAAACCGGA
1012  CATACTAGTGATGTCCAGCCAGAAGATGTGGTAGAGACCAGATACGTGCAAACATCACAA
1013  ACAAGAGATGAAATGAGTGTTGAAAGTTTTCTAGGGAGATCAGGTTGCATTCATATGTCA
1014  AAATTAGTTGTAAACTATGATAATTATGATGAAAACAACTTCCATAAATGGCAAATTAAC
1015  CTGCAAGAGATGGCACAGATTAGAAGAAAATTTGAATTGTTTACATATGCTAGATTTGAT
1016  TCTGAAATTACAATAGTACCATCTATAGCTGGCAAGGGCAATGATATTGGACATGTTGTG
1017  ATGCAATACATGTATATACCACCTGGGGCACCAGTACCTGAGAAGAGGGATGATTATGCA
1018  TGGCAATCAGGCACTAATGCATCTATCTTTTGGCAACATGGACAAACATACCCTAGATTT
1019  TCACTTCCTTTCTTAAGTATAGCTTCTGCATACTATATGTTTTATGATGGATATGATGGT
1020  GACCAAACTGATTCGAGATATGGTACCATTGTTACTAATGATATGGGAACCTTATGTTAT
1021  AGAATAGTTACAGATGAACATGCCCACAAAATAGAGATCACTACAAGAATATACCATAAA
1022  GCAAAACACATTAAGGTTTGGTGTCCAAGACCACCTAGGGCAGTTGAATACACACACACT
1023  CATGTAACAAACTACAAACATGCAACACGTGAACTTAAGACTGCAATTAGGCCCAGGAAA
1024  ACAATCACAACAGCA
1025  >65_HRV90a|
1026  AATCCAGTGGAAAATTATATAGATGAAGTCCTAAATGAGGTATTGGTTGTCCCTAATATT
1027  AAGGAAAGTAAACCTTCAACTTCAAACTCAGCGCCAGCTTTAGATGCAGCAGAAACCGGA
1028  CATACTAGTGATGTCCAGCCAGAAGATGTGGTAGAGACCAGATACGTGCAAACATCACAA
1029  ACAAGAGATGAAATGAGTGTTGAAAGTTTTCTAGGGAGATCAGGTTGCATTCATATGTCA
1030  AAATTAGTTGTAAACTATGATAATTATGATGAAAACAACTTCCATAAATGGCAAATTAAC
1031  CTGCAAGAGATGGCACAGATTAGAAGAAAATTTGAATTGTTTACATATGCTAGATTTGAT
1032  TCTGAAATTACAATAGTACCATCTATAGCTGGCAAGGGCAATGATATTGGACATGTTGTG
1033  ATGCAATACATGTATATACCACCTGGGGCACCAGTACCTGAGAAGAGGGATGATTATGCA
1034  TGGCAATCAGGCACTAATGCATCTATCTTTTGGCAACATGGACAAACATACCCTAGATTT
1035  TCACTTCCTTTCTTAAGTATAGCTTCTGCATACTATATGTTTTATGATGGATATGATGGT
1036  GACCAAACTGATTCGAGATATGGTACCATTGTTACTAATGATATGGGAACCTTATGTTAT
1037  AGAATAGTTACAGATGAACATGCCCACAAAATAGAGATCACTACAAGAATATACCATAAA
1038  GCAAAACACATTAAGGTTTGGTGTCCAAGACCACCTAGGGCAGTTGAATACACACACACT
1039  CATGTAACAAACTACAAACATGCAACACGTGAACTTAAGACTGCAATTAGGCCCAGGAAA
1040  ACAATCACAACAGCG
```

FIG. D1 CONT'D

Rhino_cDNA_DB.fasta                                                 9/20/2007 5:08 PM

```
1041 >66_HRV90b|
1042 AATCCAGTGGAAAATTATATAGATGAAGTCCTAAATGAGGTATTGGTTGTCCCTAATATT
1043 AAGGAAAGTAAACCTTCAACTTCAAACTCAGCGCCAGCTTTAGATGCAGCAGAAACCGGA
1044 CATACTAGTGATGTCCAGCCAGAAGATGTGGTAGAGACCAGATACGTGCAAACATCACAA
1045 ACAAGAGATGAAATGAGTGTTGAAAGTTTTCTAGGGAGATCAGGTTGCATTCATATGTCA
1046 AAATTAGTTGTAAACTATGATAATTATGATGAAAACAACTTCCATAAATGGCAAATTAAC
1047 CTGCAAGAGATGGCACAGATTAGAAGAAAATTTGAATTGTTTACATATGCTAGATTTGAT
1048 TCTGAAATTACAATAGTACCATCTATAGCTGGCAAGGGCAATGATATTGGACATGTTGTG
1049 ATGCAATACATGTATATACCACCTGGGGCACCAGTACCTGAGAAGAGGGATGATTATGCA
1050 TGGCAATCAGGCACTAATGCATCTATCTTTTGGCAACATGGACAAACATACCCTAGATTT
1051 TCACTTCCTTTCTTAAGTATAGCTTCTGCATACTATATGTTTTATGATGGATATGATGGT
1052 GACCAAACTGATTCGAGATATGGTACCATTGTTACTAATGATATGGGAACCTTATGTTAT
1053 AGAATAGTTACAGATGAACATGCCCACAAAATAGAGATCACTACAAGAATATACCATAAA
1054 GCAAAACACATTAAGGTTTGGTGTCCAAGACCACCTAGGGCAGTTGAATACACACACACT
1055 CATGTAACAAACTACAAACATGCAACACGTGAACTTAAGACTGCAATTAGGCCCAGGAAA
1056 ACAATCACAACAGCT
1057 >67_HRV34
1058 AATCCAGTTGAAAATTACATAGATGAGGTACTAAATGAGGTATTGGTTGTACCAAACATT1
1059 AAAGAAAGCCAAGCCACCACATCAAACTCTGCCCCCGCACTGGATGCAGCTGAGACTGGT
1060 CACACTAGCAGTGTACAACCTGAAGATATGATTGAGACCAGGTACGTACAAACATCACAA
1061 ACAAGAGATGAAATGAGCATTGAGAGTTTCCTGGGTAGGTCTGGCTGTATACACATGTCC
1062 AAACTTGTTGTAGATTATGAAAATTACAATGCAAAAACAAAGAACTTTATGACATGGCAA
1063 ATTAATTTACAGGAAATGGCACAGATTAGAAGGAAATTTGAAATGTTCACCTACGTCAGA
1064 TTTGATTCTGAAGTCACCCTAGTACCATCAATAGCGGCCAAAGGTGATGATATTGGACAT
1065 GTTGTGATGCAATACATGTATGTACCACCAGGTGCACCAATACCTAAAACTAGAGATGAT
1066 TTTGCATGGCAATCTGGAACAAATGCCTCAATATTTTGGCAACATGGTCAAACATACCCT
1067 AGATTTTCCCTCCCTTTCTTAAGCATAGCCTCAGCATACTACATGTTTTATGATGGATAT
1068 GATGGTGATCAACATGATTCAAGATATGGTACAGTAGTGACTAATGACATGGGTACTTTA
1069 TGCTCCAGAATTGTAACTGATGAACACCAAAACAGAGTAGAAATAACAACTAGAGTTTAT
1070 CACAAAGCTAAACATGTAAAAACCTGGTGTCCAAGACCACCAAGAGCTGTTGAGTACACA
1071 CACACACATGTTACTAACTACAAAGTTAGGGGTAAAACTGAGAAGACTGCAATCAAACAC
1072 AGAGCAAAGATCACAATGGCC
1073 >68_HRV34b|
1074 AATCCAGTTGAAAATTACATAGATGAGGTACTAAATGAGGTATTGGTTGTACCAAACATT
1075 AAAGAAAGCCAAGCCACCACATCAAACTCTGCCCCCGCACTGGATGCAGCTGAGACTGGT
1076 CACACTAGCAGTGTACAACCTGAAGATATGATTGAGACCAGGTACGTACAAACATCACAA
1077 ACAAGAGATGAAATGAGCATTGAGAGTTTCCTGGGTAGGTCTGGCTGTATACACATGTCC
1078 AAACTTGTTGTAGATTATGAAAATTACAATGCAAAAACAAAGAACTTTATGACATGGCAA
1079 ATTAATTTACAGGAAATGGCACAGATTAGAAGGAAATTTGAAATGTTCACCTACGTCAGA
1080 TTTGATTCTGAAGTCACCCTAGTACCATCAATAGCGGCCAAAGGTGATGATATTGGACAT
1081 GTTGTGATGCAATACATGTATGTACCACCAGGTGCACCAATACCTAAAACTAGAGATGAT
1082 TTTGCATGGCAATCTGGAACAAATGCCTCAATATTTTGGCAACATGGTCAAACATACCCT
1083 AGATTTTCCCTCCCTTTCTTAAGCATAGCCTCAGCATACTACATGTTTTATGATGGATAT
1084 GATGGTGATCAACATGATTCAAGATATGGTACAGTAGTGACTAATGACATGGGTACTTTA
1085 TGCTCCAGAATTGTAACTGATGAACACCAAAACAGAGTAGAAATAACAACTAGAGTTTAT
1086 CACAAAGCTAAACATGTAAAAACCTGGTGTCCAAGACCACCAAGAGCTGTTGAGTACACA
1087 CACACACATGTTACTAACTACAAAGTTAGGGGTAAAACTGAGAAGACTGCAATCAAACAC
1088 AGAGCAAAGATCACAATGGCA
1089 >69_HRV34a|
1090 AATCCAGTTGAAAATTACATAGATGAGGTACTAAATGAGGTATTGGTTGTACCAAACATT
1091 AAAGAAAGCCAAGCCACCACATCAAACTCTGCCCCCGCACTGGATGCAGCTGAGACTGGT
1092 CACACTAGCAGTGTACAACCTGAAGATATGATTGAGACCAGGTACGTACAAACATCACAA
1093 ACAAGAGATGAAATGAGCATTGAGAGTTTCCTGGGTAGGTCTGGCTGTATACACATGTCC
1094 AAACTTGTTGTAGATTATGAAAATTACAATGCAAAAACAAAGAACTTTATGACATGGCAA
1095 ATTAATTTACAGGAAATGGCACAGATTAGAAGGAAATTTGAAATGTTCACCTACGTCAGA
1096 TTTGATTCTGAAGTCACCCTAGTACCATCAATAGCGGCCAAAGGTGATGATATTGGACAT
1097 GTTGTGATGCAATACATGTATGTACCACCAGGTGCACCAATACCTAAAACTAGAGATGAT
1098 TTTGCATGGCAATCTGGAACAAATGCCTCAATATTTTGGCAACATGGTCAAACATACCCT
1099 AGATTTTCCCTCCCTTTCTTAAGCATAGCCTCAGCATACTACATGTTTTATGATGGATAT
1100 GATGGTGATCAACATGATTCAAGATATGGTACAGTAGTGACTAATGACATGGGTACTTTA
1101 TGCTCCAGAATTGTAACTGATGAACACCAAAACAGAGTAGAAATAACAACTAGAGTTTAT
1102 CACAAAGCTAAACATGTAAAAACCTGGTGTCCAAGACCACCAAGAGCTGTTGAGTACACA
1103 CACACACATGTTACTAACTACAAAGTTAGGGGTAAAACTGAGAAGACTGCAATCAAACAC
1104 AGAGCAAAGATCACAATGGCT
1105 >70_HRV50a|
```

FIG. D1 CONT'D

Rhino_cDNA_DB.fasta                                                    9/20/2007 5:08 PM

```
1106  AATCCAGTGGAGAATTACATAGATGAAGTATTAAATGAGGTATTAGTTGTCCCAAATATC
1107  AAGGAGAGTCAAGCCACTACATCAAACTCTGCCCCTGCTTTAGATGCAGCTGAAACTGGA
1108  CACACAAGTAATGTGCAGCCTGAAGATATGCTTGAAACTAGATATGTGCAAACATCGCAT
1109  ACAAGAGATGAAATGAGCATTGAAAGTTTCCTAGGTAGATCTGGTTGTATACATATATCT
1110  AAATTAGTTGTTGATTATGATGGTTACAATGAGGAAACAAAGAACTTCAAGAAATGGCAA
1111  ATCAACCTACAAGAAATGGCACAGATCAGAAGGAAATTTGAGATGTTCACCTATGTGAGG
1112  TTTAATTCTGAGGTCACATTAGTACCATCCATAGCTGCCAAGGGTGTTGATATTGGACAT
1113  GTTGTCATGCAATACATGTATGTCCCACCAGGTGCACCAATACCCAAGACTAGGGATGAT
1114  TTTGCCTGGCAATCTGGAACTAATGCTTCAATCTTTTGGCAACATGGTCAAACATACCCT
1115  AGATTCTCTCTACCATTCTTGAGTATAGCATCTGCATATTACATGTTTTATGATGGTTAT
1116  GATGGTGATAAATCTACATCCAGGTATGGTACAGTAGTTACCAATGACATGGGCACTTTG
1117  TGTTCTAGGATTGTCACTGATGAGCACCAAAATAAAGTGGAAATCACAACCAGAGTATAC
1118  CATAAAGCCAAACACATAAAAGTCTGGTGTCCAAGACCACCAAGAGCTGTTGAATACACA
1119  CACACCCATGTCACTAACTACAAGAAAAGTGATGCTACTGAGAAGACTGCAATTGCAACT
1120  AGACCAAAGATCACAGTGGCA
1121  >71_HRV50b|
1122  AATCCAGTGGAGAATTACATAGATGAAGTATTAAATGAGGTATTAGTTGTCCCAAATATC
1123  AAGGAGAGTCAAGCCACTACATCAAACTCTGCCCCTGCTTTAGATGCAGCTGAAACTGGA
1124  CACACAAGTAATGTGCAGCCTGAAGATATGCTTGAAACTAGATATGTGCAAACATCGCAT
1125  ACAAGAGATGAAATGAGCATTGAAAGTTTCCTAGGTAGATCTGGTTGTATACATATATCT
1126  AAATTAGTTGTTGATTATGATGGTTACAATGAGGAAACAAAGAACTTCAAGAAATGGCAA
1127  ATCAACCTACAAGAAATGGCACAGATCAGAAGGAAATTTGAGATGTTCACCTATGTGAGG
1128  TTTAATTCTGAGGTCACATTAGTACCATCCATAGCTGCCAAGGGTGTTGATATTGGACAT
1129  GTTGTCATGCAATACATGTATGTCCCACCAGGTGCACCAATACCCAAGACTAGGGATGAT
1130  TTTGCCTGGCAATCTGGAACTAATGCTTCAATCTTTTGGCAACATGGTCAAACATACCCT
1131  AGATTCTCTCTACCATTCTTGAGTATAGCATCTGCATATTACATGTTTTATGATGGTTAT
1132  GATGGTGATAAATCTACATCCAGGTATGGTACAGTAGTTACCAATGACATGGGCACTTTG
1133  TGTTCTAGGATTGTCACTGATGAGCACCAAAATAAAGTGGAAATCACAACCAGAGTATAC
1134  CATAAAGCCAAACACATAAAAGTCTGGTGTCCAAGACCACCAAGAGCTGTTGAATACACA
1135  CACACCCATGTCACTAACTACAAGAAAAGTGATGCTACTGAGAAGACTGCAATTGCAACT
1136  AGACCAAAGATCACAGTGGCG
1137  >72_HRV50
1138  AATCCAGTGGAGAATTACATAGATGAAGTATTAAATGAGGTATTAGTTGTCCCAAATATC
1139  AAGGAGAGTCAAGCCACTACATCAAACTCTGCCCCTGCTTTAGATGCAGCTGAAACTGGA
1140  CACACAAGTAATGTGCAGCCTGAAGATATGCTTGAAACTAGATATGTGCAAACATCGCAT
1141  ACAAGAGATGAAATGAGCATTGAAAGTTTCCTAGGTAGATCTGGTTGTATACATATATCT
1142  AAATTAGTTGTTGATTATGATGGTTACAATGAGGAAACAAAGAACTTCAAGAAATGGCAA
1143  ATCAACCTACAAGAAATGGCACAGATCAGAAGGAAATTTGAGATGTTCACCTATGTGAGG
1144  TTTAATTCTGAGGTCACATTAGTACCATCCATAGCTGCCAAGGGTGTTGATATTGGACAT
1145  GTTGTCATGCAATACATGTATGTCCCACCAGGTGCACCAATACCCAAGACTAGGGATGAT
1146  TTTGCCTGGCAATCTGGAACTAATGCTTCAATCTTTTGGCAACATGGTCAAACATACCCT
1147  AGATTCTCTCTACCATTCTTGAGTATAGCATCTGCATATTACATGTTTTATGATGGTTAT
1148  GATGGTGATAAATCTACATCCAGGTATGGTACAGTAGTTACCAATGACATGGGCACTTTG
1149  TGTTCTAGGATTGTCACTGATGAGCACCAAAATAAAGTGGAAATCACAACCAGAGTATAC
1150  CATAAAGCCAAACACATAAAAGTCTGGTGTCCAAGACCACCAAGAGCTGTTGAATACACA
1151  CACACCCATGTCACTAACTACAAGAAAAGTGATGCTACTGAGAAGACTGCAATTGCAACT
1152  AGACCAAAGATCACAGTGGCT
1153  >73_HRV18a|
1154  AATCCAGTAGAGAATTATATAGATGAAGTACTTAATGAAGTGTTAGTGGTCCCAAATGTG
1155  AATGAAAGTCACGCAATTACATCAAATTCAGCCCCTGCTTTAGATGCCGCTGAAACTGGT
1156  CACACCAGCAATGTGCAACCTGAAGATATGATTGAGACTAGGTATGTACAAACATCACAA
1157  ACAAGAGATGAAATGAGTATAGAGTGTTTTCTAGGCAGATCAGGGTGTATACATATCTCC
1158  AAGTTAGTTGTACATTATGAAGATTATAATGCAGAAACAAGGAACTTTGTAAAATGGCAA
1159  ATAAATCTACAGGAAATGGCCCAGATTAGGAGAAAATTTGAGATGTTTACATATGTTAGA
1160  TTTGATTCAGAAATTACACTAGTACCATCTGTAGCTGCTAAGGGTGATGACATAGGACAT
1161  ATTGTTATGCAGTACATGTATGTTCCTCCAGGAGCACCAATACCAAAAACCAGAGATGAT
1162  TTTGCCTGGCAATCTGGAACAAATGCATCAATCTTCTGGCAACATGGTCAAACATACCCC
1163  AGATTTTCACTTCCTTTCCTCAGTATAGCATCAGCTTATTACATGTTCTATGATGGCTAC
1164  GACGGTGACCAGACCTCATCGCGGTATGGCACAGTTGCAACAAATGACATGGGTACCTTG
1165  TGCTCTAGAATAGTCACAGATAAACATAAGAATGAGGTGGAAATAACAACCAGAATATAC
1166  CACAAGGCAAAACATGTTAAAGCATGGTGCCCAAGGCCACCGAGAGCTGTGGAGTACACA
1167  CATACACATGTAACTAACTACAAGCCTAAGGAAGGAAGAGAGAAAACTGCCATAGTACCC
1168  AGAGCAAGGATTACAATGGCA
1169  >74_HRV18b|
1170  AATCCAGTAGAGAATTATATAGATGAAGTACTTAATGAAGTGTTAGTGGTCCCAAATGTG
```

FIG. D1 CONT'D

Rhino cDNA_DB.fasta                                                    9/20/2007 5:08 PM

```
1171 AATGAAAGTCACGCAATTACATCAAATTCAGCCCCTGCTTTAGATGCCGCTGAAACTGGT
1172 CACACCAGCAATGTGCAACCTGAAGATATGATTGAGACTAGGTATGTACAAACATCACAA
1173 ACAAGAGATGAAATGAGTATAGAGTGTTTTCTAGGCAGATCAGGGTGTATACATATCTCC
1174 AAGTTAGTTGTACATTATGAAGATTATAATGCAGAAACAAGGAACTTTGTAAAATGGCAA
1175 ATAAATCTACAGGAAATGGCCCAGATTAGGAGAAAATTTGAGATGTTTACATATGTTAGA
1176 TTTGATTCAGAAATTACACTAGTACCATCTGTAGCTGCTAAGGGTGATGACATAGGACAT
1177 ATTGTTATGCAGTACATGTATGTTCCTCCAGGAGCACCAATACCAAAAACCAGAGATGAT
1178 TTTGCCTGGCAATCTGGAACAAATGCATCAATCTTCTGGCAACATGGTCAAACATACCCC
1179 AGATTTTCACTTCCTTTCCTCAGTATAGCATCAGCTTATTACATGTTCTATGATGGCTAC
1180 GACGGTGACCAGACCTCATCGCGGTATGGCACAGTTGCAACAAATGACATGGGTACCTTG
1181 TGCTCTAGAATAGTCACAGATAAACATAAGAATGAGGTGGAAATAACAACCAGAATATAC
1182 CACAAGGCAAAACATGTTAAAGCATGGTGCCCAAGGCCACCGAGAGCTGTGGAGTACACA
1183 CATACACATGTAACTAACTACAAGCCTAAGGAAGGAAGAGAGAAAACTGCCATAGTACCC
1184 AGAGCAAGGATTACAATGGCG
1185 >75_HRV18
1186 AATCCAGTAGAGAATTATATAGATGAAGTACTTAATGAAGTGTTAGTGGTCCCAAATGTG
1187 AATGAAAGTCACGCAATTACATCAAATTCAGCCCCTGCTTTAGATGCCGCTGAAACTGGT
1188 CACACCAGCAATGTGCAACCTGAAGATATGATTGAGACTAGGTATGTACAAACATCACAA
1189 ACAAGAGATGAAATGAGTATAGAGTGTTTTCTAGGCAGATCAGGGTGTATACATATCTCC
1190 AAGTTAGTTGTACATTATGAAGATTATAATGCAGAAACAAGGAACTTTGTAAAATGGCAA
1191 ATAAATCTACAGGAAATGGCCCAGATTAGGAGAAAATTTGAGATGTTTACATATGTTAGA
1192 TTTGATTCAGAAATTACACTAGTACCATCTGTAGCTGCTAAGGGTGATGACATAGGACAT
1193 ATTGTTATGCAGTACATGTATGTTCCTCCAGGAGCACCAATACCAAAAACCAGAGATGAT
1194 TTTGCCTGGCAATCTGGAACAAATGCATCAATCTTCTGGCAACATGGTCAAACATACCCC
1195 AGATTTTCACTTCCTTTCCTCAGTATAGCATCAGCTTATTACATGTTCTATGATGGCTAC
1196 GACGGTGACCAGACCTCATCGCGGTATGGCACAGTTGCAACAAATGACATGGGTACCTTG
1197 TGCTCTAGAATAGTCACAGATAAACATAAGAATGAGGTGGAAATAACAACCAGAATATAC
1198 CACAAGGCAAAACATGTTAAAGCATGGTGCCCAAGGCCACCGAGAGCTGTGGAGTACACA
1199 CATACACATGTAACTAACTACAAGCCTAAGGAAGGAAGAGAGAAAACTGCCATAGTACCC
1200 AGAGCAAGGATTACAATGGCT
1201 >76_HRV55
1202 AATCCTGTAGAGAGATATGTTGATGAAGTCCTGAATGAAGTGCTAGTAGTTCCAAATATT
1203 AGGGAGAGTCAAGCAGCAACATCAAATTCAGCTCCAGTACTAGATGCAGCAGAAACTGGG
1204 CATACAAGCAATGTACAACCAGAAGATGTAATTGAGACAAGATATGTTCAGACATCACAA
1205 ACTCGTGATGAGATGAGCATTGAAAGTTTTCTAGGTAGATCAGGATGTGTACATATATCA
1206 GAGTTAGTTGTTCATTATGAAGAATATAACAAAGAGGGAAAAAATTTTACTAAGTGGCAA
1207 GTAAACATCCAAGAGATGGCTCAGATTAGAAGAAAATTTGAAATGTTCACCTATACTAGA
1208 TTTGATTCAGAAGTTACATTAGTACCCTCTATTGCTGCAAAGGGAGATGACATTGGACAT
1209 GTAGTCATGCAATACATGTATGTTCCACCTGGAGCACCAATTCCAAAGACAAGAGAAGAT
1210 TATGCTTGGCAATCAGGGACCAATGCATCTATCTTTTGGCAACATGGGCAAACATACCCT
1211 AGATTTTCACTTCCTTTCCTAAGTATAGCTTCTGCTTATTACATGTTCTATGATGGATAT
1212 GATGGTGACCAAACTGAGTCACGCTATGGCACTGTAGTCACTAATGACATGGGTACTTTA
1213 TGTTCTAGAATAATAACTGATAACCATAAGCACCCAATTGAAGTGACGACAAGAGTCTAT
1214 CATAAAGCTAAACACATCAAAGCATGGTGCCCACGACCACCTAGGGCTGTTAATACACA
1215 CACACACATGTCACAAATTACAAGAAGACTGATGGCACAGAAAAGACAGCAATTGAATAC
1216 AGAAGGGACATTAAAACAGTG
1217 >77_HRV55b|
1218 AATCCTGTAGAGAGATATGTTGATGAAGTCCTGAATGAAGTGCTAGTAGTTCCAAATATT
1219 AGGGAGAGTCAAGCAGCAACATCAAATTCAGCTCCAGTACTAGATGCAGCAGAAACTGGG
1220 CATACAAGCAATGTACAACCAGAAGATGTAATTGAGACAAGATATGTTCAGACATCACAA
1221 ACTCGTGATGAGATGAGCATTGAAAGTTTTCTAGGTAGATCAGGATGTGTACATATATCA
1222 GAGTTAGTTGTTCATTATGAAGAATATAACAAAGAGGGAAAAAATTTTACTAAGTGGCAA
1223 GTAAACATCCAAGAGATGGCTCAGATTAGAAGAAAATTTGAAATGTTCACCTATACTAGA
1224 TTTGATTCAGAAGTTACATTAGTACCCTCTATTGCTGCAAAGGGAGATGACATTGGACAT
1225 GTAGTCATGCAATACATGTATGTTCCACCTGGAGCACCAATTCCAAAGACAAGAGAAGAT
1226 TATGCTTGGCAATCAGGGACCAATGCATCTATCTTTTGGCAACATGGGCAAACATACCCT
1227 AGATTTTCACTTCCTTTCCTAAGTATAGCTTCTGCTTATTACATGTTCTATGATGGATAT
1228 GATGGTGACCAAACTGAGTCACGCTATGGCACTGTAGTCACTAATGACATGGGTACTTTA
1229 TGTTCTAGAATAATAACTGATAACCATAAGCACCCAATTGAAGTGACGACAAGAGTCTAT
1230 CATAAAGCTAAACACATCAAAGCATGGTGCCCACGACCACCTAGGGCTGTTAATACACA
1231 CACACACATGTCACAAATTACAAGAAGACTGATGGCACAGAAAAGACAGCAATTGAATAC
1232 AGAAGGGACATTAAAACAGTC
1233 >78_HRV55a|
1234 AATCCTGTAGAGAGATATGTTGATGAAGTCCTGAATGAAGTGCTAGTAGTTCCAAATATT
1235 AGGGAGAGTCAAGCAGCAACATCAAATTCAGCTCCAGTACTAGATGCAGCAGAAACTGGG
```

FIG. D1 CONT'D

Rhino_cDNA_DB.fasta                                        9/20/2007 5:08 PM

```
1236 CATACAAGCAATGTACAACCAGAAGATGTAATTGAGACAAGATATGTTCAGACATCACAA
1237 ACTCGTGATGAGATGAGCATTGAAAGTTTTCTAGGTAGATCAGGATGTGTACATATATCA
1238 GAGTTAGTTGTTCATTATGAAGAATATAACAAAGAGGGAAAAAATTTTACTAAGTGGCAA
1239 GTAAACATCCAAGAGATGGCTCAGATTAGAAGAAAATTTGAAATGTTCACCTATACTAGA
1240 TTTGATTCAGAAGTTACATTAGTACCCTCTATTGCTGCAAAGGGAGATGACATTGGACAT
1241 GTAGTCATGCAATACATGTATGTTCCACCTGGAGCACCAATTCCAAAGACAAGAGAAGAT
1242 TATGCTTGGCAATCAGGGACCAATGCATCTATCTTTTGGCAACATGGGCAAACATACCCT
1243 AGATTTTCACTTCCTTTCCTAAGTATAGCTTCTGCTTATTACATGTTCTATGATGGATAT
1244 GATGGTGACCAAACTGAGTCACGCTATGGCACTGTAGTCACTAATGACATGGGTACTTTA
1245 TGTTCTAGAATAATAACTGATAACCATAAGCACCCAATTGAAGTGACGACAAGAGTCTAT
1246 CATAAAGCTAAACACATCAAAGCATGGTGCCCACGACCACCTAGGGCTGTTGAATACACA
1247 CACACACATGTCACAAATTACAAGAAGACTGATGGCACAGAAAAGACAGCAATTGAATAC
1248 AGAAGGGACATTAAAACAGTA
1249 >79_HRV57
1250 AACCCAGTAGAAAATTTTGTGGATGAGATCTTGAATGAAGTTTTGGTGGTTCCAGATATC
1251 AAACAAAGTCAAGCAACAACATCAAACTCAGCACCTGCATTGGATGCAGCTGAAACTGGA
1252 CACACTAGTAATGTACAACCGGAAGACATGATTGAAACTAGATATGTCCAGACATCACAA
1253 ACACGTGATGAAATGAGTCTTGAGAGCTTCTTAGGAAGATCTGGCTGCATTCATATTTCA
1254 GAGCTTAAGGTAAAATATGAAAATTACAACACAGAGAATTTCACTAAATGGGAAATAAAT
1255 CTACAAGAAATGGCACAAATCAGAAGAAAATTTGAACTATTTACATATGTTAGGTTTGAT
1256 TCTGAAGTTACATTAGTTCCCTCCATAGCTGCTCAAGGTGAGGATATAGGCCATGTTGTA
1257 ATGCAATACATGTATGTCCCTCCTGGGGCACCAATTCCAAAAACAAGAGAGGATTATACA
1258 TGGCAATCTGGTACCAATGCTTCAATATTTTGGCAACATGGTCAAACATACCCTAGATTT
1259 TCCTTGCCTTTCTTAAGTATAGCCTCAGCATATTACATGTTTTATGATGGATATGATGGT
1260 GACCAAACTGAATCAAGATATGGTACTGTAGTCACTAATGACATGGGCACTTTATGTTCT
1261 AGAATTGTTACTGACCAGCACACACATCCCATAAAAATAACAACCAGAGTGTATCACAAA
1262 GCCAAACATGTCAAAGCCTGGTGCCCTAGACCACCACGGGCATCGAGTACACACATACA
1263 CATGTTACTAATTATAAAATAAAAGATAGACAAGAAGAAACAGCAATTAAATATAGAAGG
1264 GACATTAAAATTGTTAAGAATGTG
1265 >80_HRV57a|
1266 AACCCAGTAGAAAATTTTGTGGATGAGATCTTGAATGAAGTTTTGGTGGTTCCAGATATC
1267 AAACAAAGTCAAGCAACAACATCAAACTCAGCACCTGCATTGGATGCAGCTGAAACTGGA
1268 CACACTAGTAATGTACAACCGGAAGACATGATTGAAACTAGATATGTCCAGACATCACAA
1269 ACACGTGATGAAATGAGTCTTGAGAGCTTCTTAGGAAGATCTGGCTGCATTCATATTTCA
1270 GAGCTTAAGGTAAAATATGAAAATTACAACACAGAGAATTTCACTAAATGGGAAATAAAT
1271 CTACAAGAAATGGCACAAATCAGAAGAAAATTTGAACTATTTACATATGTTAGGTTTGAT
1272 TCTGAAGTTACATTAGTTCCCTCCATAGCTGCTCAAGGTGAGGATATAGGCCATGTTGTA
1273 ATGCAATACATGTATGTCCCTCCTGGGGCACCAATTCCAAAAACAAGAGAGGATTATACA
1274 TGGCAATCTGGTACCAATGCTTCAATATTTTGGCAACATGGTCAAACATACCCTAGATTT
1275 TCCTTGCCTTTCTTAAGTATAGCCTCAGCATATTACATGTTTTATGATGGATATGATGGT
1276 GACCAAACTGAATCAAGATATGGTACTGTAGTCACTAATGACATGGGCACTTTATGTTCT
1277 AGAATTGTTACTGACCAGCACACACATCCCATAAAAATAACAACCAGAGTGTATCACAAA
1278 GCCAAACATGTCAAAGCCTGGTGCCCTAGACCACCACGGGCATCGAGTACACACATACA
1279 CATGTTACTAATTATAAAATAAAAGATAGACAAGAAGAAACAGCAATTAAATATAGAAGG
1280 GACATTAAAATTGTTAAGAATGTA
1281 >81_HRV57b|
1282 AACCCAGTAGAAAATTTTGTGGATGAGATCTTGAATGAAGTTTTGGTGGTTCCAGATATC
1283 AAACAAAGTCAAGCAACAACATCAAACTCAGCACCTGCATTGGATGCAGCTGAAACTGGA
1284 CACACTAGTAATGTACAACCGGAAGACATGATTGAAACTAGATATGTCCAGACATCACAA
1285 ACACGTGATGAAATGAGTCTTGAGAGCTTCTTAGGAAGATCTGGCTGCATTCATATTTCA
1286 GAGCTTAAGGTAAAATATGAAAATTACAACACAGAGAATTTCACTAAATGGGAAATAAAT
1287 CTACAAGAAATGGCACAAATCAGAAGAAAATTTGAACTATTTACATATGTTAGGTTTGAT
1288 TCTGAAGTTACATTAGTTCCCTCCATAGCTGCTCAAGGTGAGGATATAGGCCATGTTGTA
1289 ATGCAATACATGTATGTCCCTCCTGGGGCACCAATTCCAAAAACAAGAGAGGATTATACA
1290 TGGCAATCTGGTACCAATGCTTCAATATTTTGGCAACATGGTCAAACATACCCTAGATTT
1291 TCCTTGCCTTTCTTAAGTATAGCCTCAGCATATTACATGTTTTATGATGGATATGATGGT
1292 GACCAAACTGAATCAAGATATGGTACTGTAGTCACTAATGACATGGGCACTTTATGTTCT
1293 AGAATTGTTACTGACCAGCACACACATCCCATAAAAATAACAACCAGAGTGTATCACAAA
1294 GCCAAACATGTCAAAGCCTGGTGCCCTAGACCACCACGGGCATCGAGTACACACATACA
1295 CATGTTACTAATTATAAAATAAAAGATAGACAAGAAGAAACAGCAATTAAATATAGAAGG
1296 GACATTAAAATTGTTAAGAATGTC
1297 >82_HRV21
1298 AATCCTGTAGAGAATTATATAGATGAAGTCCTAAATGAAGTCTTAGTAGTGCCAAATATC
1299 AGAGAGAGTCATGGAACAACATCAAACTCTGCTCCCGCACTTGATGCTGCAGAAACTGGA
1300 CACACTAGTAATGTACAGCCGGAGGATATGGTTGAAACAAGGTATGTTCAGACATCACAA
```

FIG. D1 CONT'D

Rhino cDNA_DB.fasta                                                9/20/2007 5:08 PM

```
1301 ACACGTGATGAAATGAGTATTGAAAGTTTTCTGGGCAGATCAGGGTGCATTCACATGTCA
1302 AAATTAGTAGTTAACTATGATAATTACAATACTGGAGAAAATAACATTAGTACATGGCAA
1303 ATAAATATTAAAGAGATGGCACAAATTAGGAGAAAATTTGAAATGTTCACCTATACTAGA
1304 TTTGATTCAGAAATAACTTTGGTGCCGTCAATTGCAGCTAGAACGGGTGACATAGGACAT
1305 GTTGTAATGCAATATATGTATGTCCCACCAGGTGCTCCAATTCCAAAAACTAGGGAAGAT
1306 TTTGCTTGGCAGTCAGGCACTAATGCATCCATTTTCTGGCAGCATGGCCAGACTTATCCT
1307 AGATTTTCATTACCCTTCCTTAGTATAGCATCAGCATACTACATGTTTTATGATGGTTAT
1308 GATGGTGACCAGACTGACTCACAATATGGTGCAGTAGTAACTAATGATATGGGATCTCTA
1309 TGCTACAGAATAGTAACTGGCCAGCATAAGCATAAGATAGAAGTGACCACAAGAATATAC
1310 CATAAGGCAAAGCATGTTAAAGCTTGGTGCCCCAGACCACCGAGGGCCGTTAATACACA
1311 CATACACACGTAACCAATTACAAAATTGCAAATCATGAAGTCACTTCTGCAGTTGAGTCC
1312 AGAAGAACAATTGTCACAGTT
1313 >83_HRVHan
1314 AATCCTGTAGAGAATTACGTAGATGAAGTTCTAAATGAGGTCTTAGTAGTGCCAAATATC
1315 AGAGAGAGTCATGGAACAACATCAAACTCTGCTCCCGCACTTGATGCTGCAGAAACTGGG
1316 CACACTAGTAATGTACAACCAGAGGATATGGTTGAAACAAGGTATGTTCAGACATCACAA
1317 ACACGTGATGAAATGAGTATTGAAAGTTTTCTAGGCAGATCAGGGTGTATCCACATGTCA
1318 AAATTAATAGTTAACTATGACAACTACAATACTGGAGAAAATAACATTAATACATGGCAA
1319 ATAAATATTAAAGAGATGGCACAAATTAGGAGAAAATTTGAAATGTTCACCTATACTAGA
1320 TTTGATTCAGAAATAACTTTGGTACCGTCAATTGCAGCTAAAGCGGGTGACATAGGACAT
1321 GTTGTGATGCAATATATGTATGTCCCACCAGGTGCTCCAATTCCAAAAACTAGGGAAGAT
1322 TTTGCTTGGCAATCAGGTACCAATGCATCCATTTTCTGGCAGCATGGTCAAACTTATCCT
1323 AGATTTTCACTACCCTTCCTTAGTATAGCATCAGCATATTACATGTTTTATGATGGTTAT
1324 GATGGTGATCAGACTGACTCACAATATGGTGCAGTGGTGACTAATGATATGGGATCTCTA
1325 TGCTATAGAATAGTAACTGATCAGCATAAGCACAAGATAGAAGTGACCACAAGAATATAC
1326 CATAAGGCAAAGCATGTTAAAGCTTGGTGCCCTAGACCACCGAGGGCCGTTAATACACA
1327 CATACACATGTAACCAATTACAAAATTGCAAATAAAGATGTCACTTCTGCAGTTGAGTCC
1328 AGAAGAACAATTGTCACAGTT
1329 >84_HRV4
1330 AATCCTGTTGAAAATTATGTTGATGAAATTTTAAATCAAGTTCTTGTAGTCCCAAACACT
1331 GTAGAAAGTCATTCAACAACATCCAATGCAGCCCCTGCACTTGATGCAGCTGAAACTGGG
1332 CATACTAGCCAGGTGCAACCTGAAGACATGGTAGAGACAAGGTCAGTACATAATTTCCAA
1333 ACCAGAGATGAAATGAGTATTGAAAGTTTCTTGGGCAGATCTGGTTGCATACATATTTCA
1334 ACACTTGAAGTAAATTATGATGATTATAATGGGACAGGCATAAATTTTACCCAATGGCCA
1335 ATCAACTTGCAAGAAATGGCACAAATTAGAAGAAAGTATGAATTGTTCACATACTTAAGG
1336 TTTGATTCTGAAATTACCCTTGTTCCTTGCATTGCAGCAAAAAGCAATGATATAGGCCAT
1337 GTGGTAATGCAGTACATGTATGTACCACCAGGTGCGCCAATTCCAAAAACTAGGAAAGAT
1338 TATGCATGGCAATCTGGCACAAATGCATCTGTTTTCTGGCAACATGGTCAAACATTTCCA
1339 AGATTTTCCTTACCTTTTCTGAGCATAGCATCAGCATATTACATGTTTTATGATGGATAT
1340 GAAGGTGACCAAAAAACATCCCGTTATGGCACAATTGCAAGCAACCACATGGGAACATTA
1341 TGTTCTAGGATAGTTACAGAAGAACACCAAAATCAAATCGAGATAACTACCAGGATATAT
1342 CATAAAGCCAAGCATATCAAAGCTTGGTGCCCAAGACCACCCAGAGCTGTTAATACACA
1343 CACACACATGTCACAAATTATAAAAGAGAAGGAAAGGAGGTAGAAACAGCCATAGTATCT
1344 AGGAGGGATATCAAAATTGTCAATGCA
1345 >85_HRV43b|
1346 AATCCTGTTGAAAATTATGTTGATGAAATTTTAAATCAAGTTCTTGTAGTCCCAAACACT
1347 GTAGAAAGTCATTCAACAACATCCAATGCAGCCCCTGCACTTGATGCAGCTGAAACTGGG
1348 CATACTAGCCAGGTGCAACCTGAAGACATGGTAGAGACAAGGTCAGTACATAATTTCCAA
1349 ACCAGAGATGAAATGAGTATTGAAAGTTTCTTGGGCAGATCTGGTTGCATACATATTTCA
1350 ACACTTGAAGTAAATTATGATGATTATAATGGGACAGGCATAAATTTTACCCAATGGCCA
1351 ATCAACTTGCAAGAAATGGCACAAATTAGAAGAAAGTATGAATTGTTCACATACTTAAGG
1352 TTTGATTCTGAAATTACCCTTGTTCCTTGCATTGCAGCAAAAAGCAATGATATAGGCCAT
1353 GTGGTAATGCAGTACATGTATGTACCACCAGGTGCGCCAATTCCAAAAACTAGGAAAGAT
1354 TATGCATGGCAATCTGGCACAAATGCATCTGTTTTCTGGCAACATGGTCAAACATTTCCA
1355 AGATTTTCCTTACCTTTTCTGAGCATAGCATCAGCATATTACATGTTTTATGATGGATAT
1356 GAAGGTGACCAAAAAACATCCCGTTATGGCACAATTGCAAGCAACCACATGGGAACATTA
1357 TGTTCTAGGATAGTTACAGAAGAACACCAAAATCAAATCGAGATAACTACCAGGATATAT
1358 CATAAAGCCAAGCATATCAAAGCTTGGTGCCCAAGACCACCCAGAGCTGTTAATACACA
1359 CACACACATGTCACAAATTATAAAAGAGAAGGAAAGGAGGTAGAAACAGCCATAGTATCT
1360 AGGAGGGATATCAAAATTGTCAATGCG
1361 >86_HRV43a|
1362 AATCCTGTTGAAAATTATGTTGATGAAATTTTAAATCAAGTTCTTGTAGTCCCAAACACT
1363 GTAGAAAGTCATTCAACAACATCCAATGCAGCCCCTGCACTTGATGCAGCTGAAACTGGG
1364 CATACTAGCCAGGTGCAACCTGAAGACATGGTAGAGACAAGGTCAGTACATAATTTCCAA
1365 ACCAGAGATGAAATGAGTATTGAAAGTTTCTTGGGCAGATCTGGTTGCATACATATTTCA
```

FIG. D1 CONT'D

```
Rhino cDNA DB.fasta                                              9/20/2007 5:08 PM 1366  ACACTTGAAGTAAATTATGATGATTATAATGGGACAGGCATAAATTTTACCCAATGGCCA
1367  ATCAACTTGCAAGAAATGGCACAAATTAGAAGAAAGTATGAATTGTTCACATACTTAAGG
1368  TTTGATTCTGAAATTACCCTTGTTCCTTGCATTGCAGCAAAAAGCAATGATATAGGCCAT
1369  GTGGTAATGCAGTACATGTATGTACCACCAGGTGCGCCAATTCCAAAAACTAGGAAAGAT
1370  TATGCATGGCAATCTGGCACAAATGCATCTGTTTTCTGGCAACATGGTCAAACATTTCCA
1371  AGATTTTCCTTACCTTTTCTGAGCATAGCATCAGCATATTACATGTTTTATGATGGATAT
1372  GAAGGTGACCAAAAAACATCCCGTTATGGCACAATTGCAAGCAACCACATGGGAACATTA
1373  TGTTCTAGGATAGTTACAGAAGAACACCAAAATCAAATCGAGATAACTACCAGGATATAT
1374  CATAAAGCCAAGCATATCAAAGCTTGGTGCCCAAGACCACCCAGAGCTGTTAATACACA
1375  CACACACATGTCACAAATTATAAAAGAGAAGGAAAGGAGGTAGAAACAGCCATAGTATCT
1376  AGGAGGGATATCAAAATTGTCAATGCT
1377  >87_HRV75
1378  AATCCAGTTGAAAATTATGTGGATGAAATTTTAAACCAAGTTCTGGTAGTTCCAAACACC
1379  ATGGAGAGCCATCCAACAACGTCTAATGCTGCTCCAGCTTTAGATGCAGCTGAAACTGGC
1380  CATACCAGCCATGTTCAACCAGAAGACATGTTAGAAACAAGGCAAGTACAAAATTTCCAA
1381  ACTAGAGATGAGATGAGTATTGAGAGTTTCCTAGGCAGATCTGGATGTATTCATATTTCA
1382  ACACTTGAGATGGATTATACAAACTATAATGGAGAAGGCAAAAACTTCACTCAGTGGCCA
1383  ATCAATCTACAGGAAATGGCTCAAATTAGAAGGAAATATGAATTATTTACATATCTTAGA
1384  TTTGATTCAGAGGTTACTCTGGTGCCATGCATTGCAGCTAAAGGGAATGACATAGGCCAT
1385  GTAGTAATGCAATATATGTATGTACCACCAGGAGCACCAATACCAACAACTAGAAAAGAT
1386  TATGCATGGCAATCTGGAACAAATGCATCTGTATTTGGCAACATGGACAAACATTTCCA
1387  AGATTTTCACTACCATTTCTGAGCATTGCATCAGCATATTACATGTTTTATGATGGATAT
1388  GAAGGGGATCAAAATACATCCCGTTATGGCACCATTGCTAGTAATCACATGGGGACACTG
1389  TGTTCTAGAATAGTTACAGAAGAACATCGAAATAAAGTTGAAGTAACCACTAGAATATAT
1390  CACAAAGCCAAACATATAAAAGCTTGGTGTCCGAGGCCGCCCAGGGCTGTTAATACACA
1391  TTTAGACGTGTAACAAATTACAAAAGAGATGGACAACAAGTTGAGATTGCTATTGAGCCC
1392  AGAAGAGATGTTAAGTTTGTAAATGCA
1393  >88_HRV75b|
1394  AATCCAGTTGAAAATTATGTGGATGAAATTTTAAACCAAGTTCTGGTAGTTCCAAACACC
1395  ATGGAGAGCCATCCAACAACGTCTAATGCTGCTCCAGCTTTAGATGCAGCTGAAACTGGC
1396  CATACCAGCCATGTTCAACCAGAAGACATGTTAGAAACAAGGCAAGTACAAAATTTCCAA
1397  ACTAGAGATGAGATGAGTATTGAGAGTTTCCTAGGCAGATCTGGATGTATTCATATTTCA
1398  ACACTTGAGATGGATTATACAAACTATAATGGAGAAGGCAAAAACTTCACTCAGTGGCCA
1399  ATCAATCTACAGGAAATGGCTCAAATTAGAAGGAAATATGAATTATTTACATATCTTAGA
1400  TTTGATTCAGAGGTTACTCTGGTGCCATGCATTGCAGCTAAAGGGAATGACATAGGCCAT
1401  GTAGTAATGCAATATATGTATGTACCACCAGGAGCACCAATACCAACAACTAGAAAAGAT
1402  TATGCATGGCAATCTGGAACAAATGCATCTGTATTTGGCAACATGGACAAACATTTCCA
1403  AGATTTTCACTACCATTTCTGAGCATTGCATCAGCATATTACATGTTTTATGATGGATAT
1404  GAAGGGGATCAAAATACATCCCGTTATGGCACCATTGCTAGTAATCACATGGGGACACTG
1405  TGTTCTAGAATAGTTACAGAAGAACATCGAAATAAAGTTGAAGTAACCACTAGAATATAT
1406  CACAAAGCCAAACATATAAAAGCTTGGTGTCCGAGGCCGCCCAGGGCTGTTAATACACA
1407  TTTAGACGTGTAACAAATTACAAAAGAGATGGACAACAAGTTGAGATTGCTATTGAGCCC
1408  AGAAGAGATGTTAAGTTTGTAAATGCG
1409  >89_HRV75a|
1410  AATCCAGTTGAAAATTATGTGGATGAAATTTTAAACCAAGTTCTGGTAGTTCCAAACACC
1411  ATGGAGAGCCATCCAACAACGTCTAATGCTGCTCCAGCTTTAGATGCAGCTGAAACTGGC
1412  CATACCAGCCATGTTCAACCAGAAGACATGTTAGAAACAAGGCAAGTACAAAATTTCCAA
1413  ACTAGAGATGAGATGAGTATTGAGAGTTTCCTAGGCAGATCTGGATGTATTCATATTTCA
1414  ACACTTGAGATGGATTATACAAACTATAATGGAGAAGGCAAAAACTTCACTCAGTGGCCA
1415  ATCAATCTACAGGAAATGGCTCAAATTAGAAGGAAATATGAATTATTTACATATCTTAGA
1416  TTTGATTCAGAGGTTACTCTGGTGCCATGCATTGCAGCTAAAGGGAATGACATAGGCCAT
1417  GTAGTAATGCAATATATGTATGTACCACCAGGAGCACCAATACCAACAACTAGAAAAGAT
1418  TATGCATGGCAATCTGGAACAAATGCATCTGTATTTGGCAACATGGACAAACATTTCCA
1419  AGATTTTCACTACCATTTCTGAGCATTGCATCAGCATATTACATGTTTTATGATGGATAT
1420  GAAGGGGATCAAAATACATCCCGTTATGGCACCATTGCTAGTAATCACATGGGGACACTG
1421  TGTTCTAGAATAGTTACAGAAGAACATCGAAATAAAGTTGAAGTAACCACTAGAATATAT
1422  CACAAAGCCAAACATATAAAAGCTTGGTGTCCGAGGCCGCCCAGGGCTGTTAATACACA
1423  TTTAGACGTGTAACAAATTACAAAAGAGATGGACAACAAGTTGAGATTGCTATTGAGCCC
1424  AGAAGAGATGTTAAGTTTGTAAATGCT
1425  >96_HRV9a|
1426  AATCCAGTGGAGAATTACATAGATCAGGTGCTTAATGAGGTTTTGGTAGTCCCAAACATT
1427  AAAGAGAGCAACCCTACAACCTCTAACTCAGCTCCAGCTCTAGATGCTGCTGAGACAGGC
1428  CATACTAGCAATGTTCAACCTGAAGACATGATTGAAACACGTTATGTGCAGACATCACAA
1429  ACCAGAGATGAAATGAGTCTTGAAAGCTTCTTAGGGAGATCAGGTTGTATACACATATCT
1430  AAATTGAATATTGATTACAGTGACTATGATAAGAGTGTTGAAAATTTCACAATCTGGAAA
```

FIG. D1 CONT'D

Rhino_cDNA_DB.fasta                                                       9/20/2007 5:08 PM

```
1431 ATAAATATAAAGGAAATGGCCCAGATCAGGAGGAAATTTGAATTGTTTACATATGCAAGA
1432 TTTGACTCTGAAATAACATTGGTCCCGTGTATAGCAGCAGAAAGTGATAGCGTTGGCCAT
1433 GTTGTTATGCAGTACATGTATGTACCACCAGGGGCACCTTTACCAAGGACTAGAGATGAT
1434 TATGCATGGCAATCAGGCACAAATGCTTCCATCTTTTGGCAACATGGACAATCATATCCC
1435 AGATTTTCACTTCCGTTTTTGAGCATTGCCTCTGCATATTACATGTTCTATGATGGTTAT
1436 GATGGTGGACCAGATTCTCTGTATGGAACAATTGTAACAAATGATATGGGATCTTTATGT
1437 TCCCGTGTAGTTACTGAAGAGCATGGACCCCGTGTCAAAATTTCAACCAGAATATATCAC
1438 AAAGCCAAACATGTTAAAGCCTGGTGCCCAAGACCTCCTAGGGCAGTTGAGTATATACAT
1439 ACACATGTCACAAATTACAAGCCAAGCACAGGCGATTATGCCACAGTTATACCAGTTAGA
1440 GACAATGTTAGGGCAGTAAAGAATGTC
1441 >97_HRV9b|
1442 AATCCAGTGGAGAATTACATAGATCAGGTGCTTAATGAGGTTTTGGTAGTCCCAAACATT
1443 AAAGAGAGCAACCCTACAACCTCTAACTCAGCTCCAGCTCTAGATGCTGCTGAGACAGGC
1444 CATACTAGCAATGTTCAACCTGAAGACATGATTGAAACACGTTATGTGCAGACATCACAA
1445 ACCAGAGATGAAATGAGTCTTGAAAGCTTCTTAGGGGAGATCAGGTTGTATACACATATCT
1446 AAATTGAATATTGATTACAGTGACTATGATAAGAGTGTTGAAAATTTCACAATCTGGAAA
1447 ATAAATATAAAGGAAATGGCCCAGATCAGGAGGAAATTTGAATTGTTTACATATGCAAGA
1448 TTTGACTCTGAAATAACATTGGTCCCGTGTATAGCAGCAGAAAGTGATAGCGTTGGCCAT
1449 GTTGTTATGCAGTACATGTATGTACCACCAGGGGCACCTTTACCAAGGACTAGAGATGAT
1450 TATGCATGGCAATCAGGCACAAATGCTTCCATCTTTTGGCAACATGGACAATCATATCCC
1451 AGATTTTCACTTCCGTTTTTGAGCATTGCCTCTGCATATTACATGTTCTATGATGGTTAT
1452 GATGGTGGACCAGATTCTCTGTATGGAACAATTGTAACAAATGATATGGGATCTTTATGT
1453 TCCCGTGTAGTTACTGAAGAGCATGGACCCCGTGTCAAAATTTCAACCAGAATATATCAC
1454 AAAGCCAAACATGTTAAAGCCTGGTGCCCAAGACCTCCTAGGGCAGTTGAGTATATACAT
1455 ACACATGTCACAAATTACAAGCCAAGCACAGGCGATTATGCCACAGTTATACCAGTTAGA
1456 GACAATGTTAGGGCAGTAAAGAATGTG
1457 >98_HRV9
1458 AATCCAGTGGAGAATTACATAGATCAGGTGCTTAATGAGGTTTTGGTAGTCCCAAACATT
1459 AAAGAGAGCAACCCTACAACCTCTAACTCAGCTCCAGCTCTAGATGCTGCTGAGACAGGC
1460 CATACTAGCAATGTTCAACCTGAAGACATGATTGAAACACGTTATGTGCAGACATCACAA
1461 ACCAGAGATGAAATGAGTCTTGAAAGCTTCTTAGGGGAGATCAGGTTGTATACACATATCT
1462 AAATTGAATATTGATTACAGTGACTATGATAAGAGTGTTGAAAATTTCACAATCTGGAAA
1463 ATAAATATAAAGGAAATGGCCCAGATCAGGAGGAAATTTGAATTGTTTACATATGCAAGA
1464 TTTGACTCTGAAATAACATTGGTCCCGTGTATAGCAGCAGAAAGTGATAGCGTTGGCCAT
1465 GTTGTTATGCAGTACATGTATGTACCACCAGGGGCACCTTTACCAAGGACTAGAGATGAT
1466 TATGCATGGCAATCAGGCACAAATGCTTCCATCTTTTGGCAACATGGACAATCATATCCC
1467 AGATTTTCACTTCCGTTTTTGAGCATTGCCTCTGCATATTACATGTTCTATGATGGTTAT
1468 GATGGTGGACCAGATTCTCTGTATGGAACAATTGTAACAAATGATATGGGATCTTTATGT
1469 TCCCGTGTAGTTACTGAAGAGCATGGACCCCGTGTCAAAATTTCAACCAGAATATATCAC
1470 AAAGCCAAACATGTTAAAGCCTGGTGCCCAAGACCTCCTAGGGCAGTTGAGTATATACAT
1471 ACACATGTCACAAATTACAAGCCAAGCACAGGCGATTATGCCACAGTTATACCAGTTAGA
1472 GACAATGTTAGGGCAGTAAAGAATGTA
1473 >99_HRV32
1474 AATCCTGTGGAGAATTACATAGATCAAGTTTTAAATGAAGTTTTGGTAGTTCCAAACATC
1475 AAAGAAAGCAATCCCACAACCTCTAATTCAGCCCCAGCCTTAGATGCTGCCGAAACAGGT
1476 CATACCAGTAATGTTCAACCTGAAGACATGATTGAAACACGTTATGTGCAAACAACACAC
1477 ACTAGAGATGAGATGAGTCTTGAGAGCTTCTTAGGGAGGTCAGGATGTGTACATATATCC
1478 AAATTAGATATTGATTATACCAATTACAATAAAAGTGTTAAGAATTTCACAATTTGGAAG
1479 ATAAATATAAAAGAAATGGCCCAGATTAGGAGAAAATTTGAGTTGTTTACATACACAAGG
1480 TTTGATTCTGAAATAACATTAGTACCTTGTATAGCTGCAGAAAGTGACAGCATTGGTCAT
1481 GTTGTTATGCAGTACATGTATGTACCACCAGGGTCCTCTACCACAAGCAAGAGATGAC
1482 TACACATGGCAATCTGGCACGAATGCATCTATCTTTTGGCAGCATGGACAGGCATATCCC
1483 AGGTTTTCACTTCCATTTCTAAGTATTGCCTCTGCATACTACATGTTTTATGATGGTTAT
1484 GATGGTGGGCCAGATTCACAATATGGAACAATTGTAACAAATGATATGGGTTCCCTGTGT
1485 TCTCGTATAGTCACCGAAGAGCACGGATCCCGTGTTGATATTTCAACTAGGGTATATCAC
1486 AAAGCTAAACACGTCAAAGCTTGGTGCCCACGACCACCTAGGGCAGTTGAATATACACAT
1487 ACACATGTTACAAATTACAAACCAAGCACAGGTGATTACACCACAGCCATACAAACCAGA
1488 GAGCATGTTAGAGCAGTCAAAAATGTA
1489 >100_HRV32a
1490 AATCCTGTGGAGAATTACATAGATCAAGTTTTAAATGAAGTTTTGGTAGTTCCAAACATC
1491 AAAGAAAGCAATCCCACAACCTCTAATTCAGCCCCAGCCTTAGATGCTGCCGAAACAGGT
1492 CATACCAGTAATGTTCAACCTGAAGACATGATTGAAACACGTTATGTGCAAACAACACAC
1493 ACTAGAGATGAGATGAGTCTTGAGAGCTTCTTAGGGAGGTCAGGATGTGTACATATATCC
1494 AAATTAGATATTGATTATACCAATTACAATAAAAGTGTTAAGAATTTCACAATTTGGAAG
1495 ATAAATATAAAAGAAATGGCCCAGATTAGGAGAAAATTTGAGTTGTTTACATACACAAGG
```

FIG. D1 CONT'D

```
Rhino_cDNA_DB.fasta                                              9/20/2007 5:08 PM
1496 TTTGATTCTGAAATAACATTAGTACCTTGTATAGCTGCAGAAAGTGACAGCATTGGTCAT
1497 GTTGTTATGCAGTACATGTATGTACCACCAGGGGCTCCTCTACCACAAGCAAGAGATGAC
1498 TACACATGGCAATCTGGCACGAATGCATCTATCTTTTGGCAGCATGGACAGGCATATCCC
1499 AGGTTTTCACTTCCATTTCTAAGTATTGCCTCTGCATACTACATGTTTTATGATGGTTAT
1500 GATGGTGGGCCAGATTCACAATATGGAACAATTGTAACAAATGATATGGGTTCCCTGTGT
1501 TCTCGTATAGTCACCGAAGAGCACGGATCCCGTGTTGATATTTCAACTAGGGTATATCAC
1502 AAAGCTAAACACGTCAAAGCTTGGTGCCCACGACCACCTAGGGCAGTTGAATATACACAT
1503 ACACATGTTACAAATTACAAACCAAGCACAGGTGATTACACCACAGCCATACAAACCAGA
1504 GAGCATGTTAGAGCAGTCAAAAATGTG
1505 >101_HRV32b
1506 AATCCTGTGGAGAATTACATAGATCAAGTTTTAAATGAAGTTTTGGTAGTTCCAAACATC
1507 AAAGAAAGCAATCCCACAACCTCTAATTCAGCCCCAGCCTTAGATGCTGCCGAAACAGGT
1508 CATACCAGTAATGTTCAACCTGAAGACATGATTGAAACACGTTATGTGCAAACAACACAC
1509 ACTAGAGATGAGATGAGTCTTGAGAGCTTCTTAGGGAGGTCAGGATGTGTACATATATCC
1510 AAATTAGATATTGATTATACCAATTACAATAAAAGTGTTAAGAATTTCACAATTTGGAAG
1511 ATAAATATAAAAGAAATGGCCCAGATTAGGAGAAAATTTGAGTTGTTTACATACACAAGG
1512 TTTGATTCTGAAATAACATTAGTACCTTGTATAGCTGCAGAAAGTGACAGCATTGGTCAT
1513 GTTGTTATGCAGTACATGTATGTACCACCAAGGGGCTCCTCTACCACAAGCAAGAGATGAC
1514 TACACATGGCAATCTGGCACGAATGCATCTATCTTTTGGCAGCATGGACAGGCATATCCC
1515 AGGTTTTCACTTCCATTTCTAAGTATTGCCTCTGCATACTACATGTTTTATGATGGTTAT
1516 GATGGTGGGCCAGATTCACAATATGGAACAATTGTAACAAATGATATGGGTTCCCTGTGT
1517 TCTCGTATAGTCACCGAAGAGCACGGATCCCGTGTTGATATTTCAACTAGGGTATATCAC
1518 AAAGCTAAACACGTCAAAGCTTGGTGCCCACGACCACCTAGGGCAGTTGAATATACACAT
1519 ACACATGTTACAAATTACAAACCAAGCACAGGTGATTACACCACAGCCATACAAACCAGA
1520 GAGCATGTTAGAGCAGTCAAAAATGTC
1521 >102_HRV67
1522 AACCCAGTAGAAGATTATGTAGATCAGGTATTGAATGAGGTCCTGGTGGTGCCAAATATA
1523 AAGCAAAGTGAACCCACGACTTCCAATTCAGCCCCAGCTCTAGATGCTGCTGAGACAGGT
1524 CACACTAGCAGTGTACAACCTGAAGATATGATCGAGACTCGTTATGTACAGGCATCAAAT
1525 ACCAGAGATGAAATGAGTCTCGAGAGCTTTCTTGGAAGGTCAGGCTGTATTCATATATCA
1526 AAATTGAATATTGATTATAATGCATATGATGAAAGTAGGGACAATTTCACAATTTGGAAA
1527 ATAAATATAAAAGAAATGGCCCAGATTAGGAGGAAATTTGAACTATTCACATATACAAGA
1528 TTTGATTCTGAGATAACACTGGTACCATGCATAGCTGCAGAGAGTGACAGCATTGGGCAT
1529 GTTGTAATGCAATATATGTATGTACCTCCAGGAGCACCATTACCAACAAAAAGAGATGAC
1530 TACACATGGCAATCAGGTACAAATGCATCCATCTTTTGGCAACATGGACAATCATACCCC
1531 AGATTCTCACTACCATTCTTAAGTATTGCCTCTGCTTATTACATGTTTTATGATGGCTAT
1532 GATGGTGGACCAGATTCACTATATGGCACCATAGTAACTAATGATATGGGTTCCTTGTGT
1533 TCGCGTATAGTTACTGAAGAACATGGTTCTCGCGTAAAAATTGCAACGCGGGTGTATCAT
1534 AAGGCTAAACATGTAAAAGCTTGGTGCCCAAGGCCCCCTAGAGCAGTTGAATACATACAC
1535 ACACATGTTACAAACTATAGACCAGAAACAGGTGAGGCTCAAACGGTTATACCTGTTAGA
1536 GCAGATGTTAGAACAATTAGAAATGTA
1537 >103_HRV67a
1538 AACCCAGTAGAAGATTATGTAGATCAGGTATTGAATGAGGTCCTGGTGGTGCCAAATATA
1539 AAGCAAAGTGAACCCACGACTTCCAATTCAGCCCCAGCTCTAGATGCTGCTGAGACAGGT
1540 CACACTAGCAGTGTACAACCTGAAGATATGATCGAGACTCGTTATGTACAGGCATCAAAT
1541 ACCAGAGATGAAATGAGTCTCGAGAGCTTTCTTGGAAGGTCAGGCTGTATTCATATATCA
1542 AAATTGAATATTGATTATAATGCATATGATGAAAGTAGGGACAATTTCACAATTTGGAAA
1543 ATAAATATAAAAGAAATGGCCCAGATTAGGAGGAAATTTGAACTATTCACATATACAAGA
1544 TTTGATTCTGAGATAACACTGGTACCATGCATAGCTGCAGAGAGTGACAGCATTGGGCAT
1545 GTTGTAATGCAATATATGTATGTACCTCCAGGAGCACCATTACCAACAAAAAGAGATGAC
1546 TACACATGGCAATCAGGTACAAATGCATCCATCTTTTGGCAACATGGACAATCATACCCC
1547 AGATTCTCACTACCATTCTTAAGTATTGCCTCTGCTTATTACATGTTTTATGATGGCTAT
1548 GATGGTGGACCAGATTCACTATATGGCACCATAGTAACTAATGATATGGGTTCCTTGTGT
1549 TCGCGTATAGTTACTGAAGAACATGGTTCTCGCGTAAAAATTGCAACGCGGGTGTATCAT
1550 AAGGCTAAACATGTAAAAGCTTGGTGCCCAAGGCCCCCTAGAGCAGTTGAATACATACAC
1551 ACACATGTTACAAACTATAGACCAGAAACAGGTGAGGCTCAAACGGTTATACCTGTTAGA
1552 GCAGATGTTAGAACAATTAGAAATGTC
1553 >104_HRV67b
1554 AACCCAGTAGAAGATTATGTAGATCAGGTATTGAATGAGGTCCTGGTGGTGCCAAATATA
1555 AAGCAAAGTGAACCCACGACTTCCAATTCAGCCCCAGCTCTAGATGCTGCTGAGACAGGT
1556 CACACTAGCAGTGTACAACCTGAAGATATGATCGAGACTCGTTATGTACAGGCATCAAAT
1557 ACCAGAGATGAAATGAGTCTCGAGAGCTTTCTTGGAAGGTCAGGCTGTATTCATATATCA
1558 AAATTGAATATTGATTATAATGCATATGATGAAAGTAGGGACAATTTCACAATTTGGAAA
1559 ATAAATATAAAAGAAATGGCCCAGATTAGGAGGAAATTTGAACTATTCACATATACAAGA
1560 TTTGATTCTGAGATAACACTGGTACCATGCATAGCTGCAGAGAGTGACAGCATTGGGCAT
```

FIG. D1 CONT'D

Rhino cDNA DB.fasta                                                              9/20/2007 5:08 PM

```
1561 GTTGTAATGCAATATATGTATGTACCTCCAGGAGCACCATTACCAACAAAAAGAGATGAC
1562 TACACATGGCAATCAGGTACAAATGCATCCATCTTTTGGCAACATGGACAATCATACCCC
1563 AGATTCTCACTACCATTCTTAAGTATTGCCTCTGCTTATTACATGTTTTATGATGGCTAT
1564 GATGGTGGACCAGATTCACTATATGGCACCATAGTAACTAATGATATGGGTTCCTTGTGT
1565 TCGCGTATAGTTACTGAAGAACATGGTTCTCGCGTAAAAATTGCAACGCGGGTGTATCAT
1566 AAGGCTAAACATGTAAAAGCTTGGTGCCCAAGGCCCCCTAGAGCAGTTGAATACATACAC
1567 ACACATGTTACAAACTATAGACCAGAAACAGGTGAGGCTCAAACGGTTATACCTGTTAGA
1568 GCAGATGTTAGAACAATTAGAAATGTT
1569 >105_HRV15
1570 AACCCAGTGGAGAATTACATAGATGAAGTGTTAAATGAGGTTCTAGTAGTTCCAAACATT
1571 AAGGAGAGTCACTCAAGCACATCCAACTCAGCACCAGCACTAGATGCAGCTGAGACCGGC
1572 CATACTAGCAGTGTTCAACCTGAGGATATGATTGAAACTCGTTACGTCCAAACATCACAG
1573 ACCAGAGATGAAATGAGTATTGAGAGCTTCCTTGGTAGATCAGGGTGTGTCCATATTTCT
1574 GATTTGAAAATACATTATGAAGATTATAATAAAGATGGGAAAAACTTTACTAAATGGCAA
1575 ATTAATCTCAAAGAAATGGCCCAGATTAGAAGGAAATTTGAGTTATTCACATATGTAAGG
1576 TTTGATTCAGAAATAACACTTGTACCATGCATTGCAGCAAAGAGTGATAACATCGGTCAT
1577 GTTGTCATGCAATATATGTATGTTCCTCCGGGAGCCCCTTTACCCAATAAAAGGAATGAT
1578 TACACATGGCAATCAGGTACAAATGCCTCTGTTTTCTGGCAACATGGTCAACCTTACCCC
1579 AGATTTTCTTTGCCTTTTCTCAGCATTGCATCTGCTTACTACATGTTCTATGATGGATAT
1580 GATGGAGATTCCACTGAATCACATTATGGTACAGTGGTCACTAATGACATGGGGACACTG
1581 TGTTCTAGAATAGTAACTGAAGAGCATGGGACACGTGTAGAGATTACAACTAGAGTGTAT
1582 CACAAAGCTAAACATGTAAAGGCTTGGTGCCCCAGACCCCCTAGAGCAGTGGAATATACA
1583 CACACACATGTCACAAATTACAAACCACAAGATGGTGATGTAACTACAGTTATTCCAACT
1584 AGAGAAAATGTTAGAGCTATAGTAAATGTT
1585 >106_HRV15a
1586 AACCCAGTGGAGAATTACATAGATGAAGTGTTAAATGAGGTTCTAGTAGTTCCAAACATT
1587 AAGGAGAGTCACTCAAGCACATCCAACTCAGCACCAGCACTAGATGCAGCTGAGACCGGC
1588 CATACTAGCAGTGTTCAACCTGAGGATATGATTGAAACTCGTTACGTCCAAACATCACAG
1589 ACCAGAGATGAAATGAGTATTGAGAGCTTCCTTGGTAGATCAGGGTGTGTCCATATTTCT
1590 GATTTGAAAATACATTATGAAGATTATAATAAAGATGGGAAAAACTTTACTAAATGGCAA
1591 ATTAATCTCAAAGAAATGGCCCAGATTAGAAGGAAATTTGAGTTATTCACATATGTAAGG
1592 TTTGATTCAGAAATAACACTTGTACCATGCATTGCAGCAAAGAGTGATAACATCGGTCAT
1593 GTTGTCATGCAATATATGTATGTTCCTCCGGGAGCCCCTTTACCCAATAAAAGGAATGAT
1594 TACACATGGCAATCAGGTACAAATGCCTCTGTTTTCTGGCAACATGGTCAACCTTACCCC
1595 AGATTTTCTTTGCCTTTTCTCAGCATTGCATCTGCTTACTACATGTTCTATGATGGATAT
1596 GATGGAGATTCCACTGAATCACATTATGGTACAGTGGTCACTAATGACATGGGGACACTG
1597 TGTTCTAGAATAGTAACTGAAGAGCATGGGACACGTGTAGAGATTACAACTAGAGTGTAT
1598 CACAAAGCTAAACATGTAAAGGCTTGGTGCCCCAGACCCCCTAGAGCAGTGGAATATACA
1599 CACACACATGTCACAAATTACAAACCACAAGATGGTGATGTAACTACAGTTATTCCAACT
1600 AGAGAAAATGTTAGAGCTATAGTAAATGTA
1601 >107_HRV15b
1602 AACCCAGTGGAGAATTACATAGATGAAGTGTTAAATGAGGTTCTAGTAGTTCCAAACATT
1603 AAGGAGAGTCACTCAAGCACATCCAACTCAGCACCAGCACTAGATGCAGCTGAGACCGGC
1604 CATACTAGCAGTGTTCAACCTGAGGATATGATTGAAACTCGTTACGTCCAAACATCACAG
1605 ACCAGAGATGAAATGAGTATTGAGAGCTTCCTTGGTAGATCAGGGTGTGTCCATATTTCT
1606 GATTTGAAAATACATTATGAAGATTATAATAAAGATGGGAAAAACTTTACTAAATGGCAA
1607 ATTAATCTCAAAGAAATGGCCCAGATTAGAAGGAAATTTGAGTTATTCACATATGTAAGG
1608 TTTGATTCAGAAATAACACTTGTACCATGCATTGCAGCAAAGAGTGATAACATCGGTCAT
1609 GTTGTCATGCAATATATGTATGTTCCTCCGGGAGCCCCTTTACCCAATAAAAGGAATGAT
1610 TACACATGGCAATCAGGTACAAATGCCTCTGTTTTCTGGCAACATGGTCAACCTTACCCC
1611 AGATTTTCTTTGCCTTTTCTCAGCATTGCATCTGCTTACTACATGTTCTATGATGGATAT
1612 GATGGAGATTCCACTGAATCACATTATGGTACAGTGGTCACTAATGACATGGGGACACTG
1613 TGTTCTAGAATAGTAACTGAAGAGCATGGGACACGTGTAGAGATTACAACTAGAGTGTAT
1614 CACAAAGCTAAACATGTAAAGGCTTGGTGCCCCAGACCCCCTAGAGCAGTGGAATATACA
1615 CACACACATGTCACAAATTACAAACCACAAGATGGTGATGTAACTACAGTTATTCCAACT
1616 AGAGAAAATGTTAGAGCTATAGTAAATGTC
1617 >108_HRV74a
1618 AACCCAGTGGAGAATTACATAGATGAAGTGTTGAATGAAGTGTTAGTTGTTCCAAATATT
1619 AGAGAAAGCCATTCAAGTACTTCAAACTCAGCACCAGCACTGGATGCAGCTGAAACTGGC
1620 CATACCAGTAATGTGCAACCAGAAGATATGGTTGAGACACGCTATGTGCAAACCTCACAG
1621 ACAAGAGATGAGATGAGTGTAGAAAGTTTTCTTGGAAGATCAGGATGCATCCATATCTCA
1622 CATCTAAAAATTGATTATACAAACTATAATGTTAAAGGGAAGAATTTTACTAAATGTTAGA
1623 ATAAATCTTAAAGAAATGGCACAGATTAGGAGAAAATTTGAGTTGTTCACATATGTTAGA
1624 TTTGACTCAGAAGTGACATTAGTTCCATGCATTGCTGCTAAAAGTGACAACATTGGCCAT
1625 GTTGTTATGCAATACATGTATGTCCCCCCAGGAGCACCTTTACCCAAGAAAAGAGATGAT
```

FIG. D1 CONT'D

Rhino_cDNA_DB.fasta                                                    9/20/2007 5:08 PM

```
1626 TACACATGGCAATCTGGCACAAATGCATCTGTGTTTTGGCAGCATGGACAGCCATACCCT
1627 AGATTCTCATTACCTTTCCTTAGCATAGCATCTGCTTATTACATGTTTTATGATGGATAT
1628 GATGGAGACTCTACTGAATCACATTATGGTACAGTAGTAACAAATGACATGGGAACTCTA
1629 TGTTCTAGAATTGTGACTGAAGAACACGATGCACGTGTGGAAATTACAACTAGAGTGTAC
1630 CATAAAGCAAAGCATGTGAAGGCATGGTGTCCTAGACCCCCTAGAGCAGTTGAATATACT
1631 CACACACATGTCACAAATTACAAACCACAAGAAGGTGACGTAACTACAGTCATCCCAACT
1632 AGGAGATCAATAGTGAATGTA
1633 >109_HRV74b
1634 AACCCAGTGGAGAATTACATAGATGAAGTGTTGAATGAAGTGTTAGTTGTTCCAAATATT
1635 AGAGAAAGCCATTCAAGTACTTCAAACTCAGCACCAGCACTGGATGCAGCTGAAACTGGC
1636 CATACCAGTAATGTGCAACCAGAAGATATGGTTGAGACACGCTATGTGCAAACCTCACAG
1637 ACAAGAGATGAGATGAGTGTAGAAAGTTTTCTTGGAAGATCAGGATGCATCCATATCTCA
1638 CATCTAAAAATTGATTATACAAACTATAATGTTAAAGGGAAGAATTTTACTAAATGGCAA
1639 ATAAATCTTAAAGAAATGGCACAGATTAGGAGAAAATTTGAGTTGTTCACATATGTTAGA
1640 TTTGACTCAGAAGTGACATTAGTTCCATGCATTGCTGCTAAAAGTGACAACATTGGCCAT
1641 GTTGTTATGCAATACATGTATGTCCCCCCAGGAGCACCTTTACCCAAGAAAAGAGATGAT
1642 TACACATGGCAATCTGGCACAAATGCATCTGTGTTTTGGCAGCATGGACAGCCATACCCT
1643 AGATTCTCATTACCTTTCCTTAGCATAGCATCTGCTTATTACATGTTTTATGATGGATAT
1644 GATGGAGACTCTACTGAATCACATTATGGTACAGTAGTAACAAATGACATGGGAACTCTA
1645 TGTTCTAGAATTGTGACTGAAGAACACGATGCACGTGTGGAAATTACAACTAGAGTGTAC
1646 CATAAAGCAAAGCATGTGAAGGCATGGTGTCCTAGACCCCCTAGAGCAGTTGAATATACT
1647 CACACACATGTCACAAATTACAAACCACAAGAAGGTGACGTAACTACAGTCATCCCAACT
1648 AGGAGATCAATAGTGAATGTC
1649 >110_HRV74
1650 AACCCAGTGGAGAATTACATAGATGAAGTGTTGAATGAAGTGTTAGTTGTTCCAAATATT
1651 AGAGAAAGCCATTCAAGTACTTCAAACTCAGCACCAGCACTGGATGCAGCTGAAACTGGC
1652 CATACCAGTAATGTGCAACCAGAAGATATGGTTGAGACACGCTATGTGCAAACCTCACAG
1653 ACAAGAGATGAGATGAGTGTAGAAAGTTTTCTTGGAAGATCAGGATGCATCCATATCTCA
1654 CATCTAAAAATTGATTATACAAACTATAATGTTAAAGGGAAGAATTTTACTAAATGGCAA
1655 ATAAATCTTAAAGAAATGGCACAGATTAGGAGAAAATTTGAGTTGTTCACATATGTTAGA
1656 TTTGACTCAGAAGTGACATTAGTTCCATGCATTGCTGCTAAAAGTGACAACATTGGCCAT
1657 GTTGTTATGCAATACATGTATGTCCCCCCAGGAGCACCTTTACCCAAGAAAAGAGATGAT
1658 TACACATGGCAATCTGGCACAAATGCATCTGTGTTTTGGCAGCATGGACAGCCATACCCT
1659 AGATTCTCATTACCTTTCCTTAGCATAGCATCTGCTTATTACATGTTTTATGATGGATAT
1660 GATGGAGACTCTACTGAATCACATTATGGTACAGTAGTAACAAATGACATGGGAACTCTA
1661 TGTTCTAGAATTGTGACTGAAGAACACGATGCACGTGTGGAAATTACAACTAGAGTGTAC
1662 CATAAAGCAAAGCATGTGAAGGCATGGTGTCCTAGACCCCCTAGAGCAGTTGAATATACT
1663 CACACACATGTCACAAATTACAAACCACAAGAAGGTGACGTAACTACAGTCATCCCAACT
1664 AGGAGATCAATAGTGAATGTT
1665 >111_HRV38a
1666 AACCCAGTAGAGGAATACATAGATGGAGTCTTGAATGAGGTTCTTGTGGTTCCGAACATT
1667 AAGGAAAGCCACTCCAGCACATCAAATTCAGCACCAGCATTAGATGCTGCTGAGACTGGA
1668 CACACCAGTAATGTGCAGCCTGAGGATATGATTGAAACTCGCTATGTACAGACATCACAA
1669 ACTAGAGATGAAATGAGTGTAGAAAGTTTTCTAGGAAGATCAGGTTGTGTACATATATCC
1670 AATCTTGACATAGATTACATTAATTACAACTCTGAAGACAAAAACTTTACAACATGGCAA
1671 ATCAATCTCAAAGAAATGGCTCAAATCAGAAGAAAGTTTGAAATGTTTACATATGTGAGA
1672 TTTGATTCAGAAGTTACATTAGTCCCATGTATAGCAGCACAAAATGAAGGTGTGGGGCAT
1673 GTTGTTATGCAGTATATGTATGTCCCTCCAGGGGCACCATTACCCAGGAAGAGAGATGAT
1674 TACACTTGGCAATCTGGTACAAATGCCTCTGTTTTCTGGCAATATGGTCAGACATATCCT
1675 CGATTTTCCTTACCTTTCTTAAGCATTGCATCTGTCTATTATATGTTTTATGATGGATAT
1676 GATGGGGACTCAACAGAATCACATTATGGGACAGCGGTGACCAATGATATGGGGACACTT
1677 TGTTCAAGAATAGTCACTGAAAATCATGGGACCCAAGTGAAGATAACAACTAGAATTTAT
1678 CATAAGGCAAAACATGTAAAAGCCTGGTGTCCAAGACCCCCAAGGGCAGTTGAATATAGA
1679 CATACACATGTTAACAATTACAAACCAGACCAAGGGGAAGTAACCACTATGATTCCAACT
1680 AGAACCAACATAAGAACCATCGTAAATGTA
1681 >112_HRV38b
1682 AACCCAGTAGAGGAATACATAGATGGAGTCTTGAATGAGGTTCTTGTGGTTCCGAACATT
1683 AAGGAAAGCCACTCCAGCACATCAAATTCAGCACCAGCATTAGATGCTGCTGAGACTGGA
1684 CACACCAGTAATGTGCAGCCTGAGGATATGATTGAAACTCGCTATGTACAGACATCACAA
1685 ACTAGAGATGAAATGAGTGTAGAAAGTTTTCTAGGAAGATCAGGTTGTGTACATATATCC
1686 AATCTTGACATAGATTACATTAATTACAACTCTGAAGACAAAAACTTTACAACATGGCAA
1687 ATCAATCTCAAAGAAATGGCTCAAATCAGAAGAAAGTTTGAAATGTTTACATATGTGAGA
1688 TTTGATTCAGAAGTTACATTAGTCCCATGTATAGCAGCACAAAATGAAGGTGTGGGGCAT
1689 GTTGTTATGCAGTATATGTATGTCCCTCCAGGGGCACCATTACCCAGGAAGAGAGATGAT
1690 TACACTTGGCAATCTGGTACAAATGCCTCTGTTTTCTGGCAATATGGTCAGACATATCCT
```

FIG. D1 CONT'D

Rhino_cDNA_DB.fasta                                              9/20/2007 5:08 PM

```
1691 CGATTTTCCTTACCTTTCTTAAGCATTGCATCTGTCTATTATATGTTTTATGATGGATAT
1692 GATGGGGACTCAACAGAATCACATTATGGGACAGCGGTGACCAATGATATGGGGACACTT
1693 TGTTCAAGAATAGTCACTGAAAATCATGGGACCCAAGTGAAGATAACAACTAGAATTTAT
1694 CATAAGGCAAAACATGTAAAAGCCTGGTGTCCAAGACCCCCAAGGGCAGTTGAATATAGA
1695 CATACACATGTTAACAATTACAAACCAGACCAAGGGGAAGTAACCACTATGATTCCAACT
1696 AGAACCAACATAAGAACCATCGTAAATGTC
1697 >113_HRV38
1698 AACCCAGTAGAGGAATACATAGATGGAGTCTTGAATGAGGTTCTTGTGGTTCCGAACATT
1699 AAGGAAAGCCACTCCAGCACATCAAATTCAGCACCAGCATTAGATGCTGCTGAGACTGGA
1700 CACACCAGTAATGTGCAGCCTGAGGATATGATTGAAACTCGCTATGTACAGACATCACAA
1701 ACTAGAGATGAAATGAGTGTAGAAAGTTTTCTAGGAAGATCAGGTTGTGTACATATATCC
1702 AATCTTGACATAGATTACATTAATTACAACTCTGAAGACAAAAACTTTACAACATGGCAA
1703 ATCAATCTCAAAGAAATGGCTCAAATCAGAAGAAAGTTTGAAATGTTTACATATGTAAGA
1704 TTTGATTCAGAAGTTACATTAGTCCCATGTATAGCAGCACAAAATGAAGGTGTGGGGCAT
1705 GTTGTTATGCAGTATATGTATGTCCCTCCAGGGGCACCATTACCCAGGAAGAGAGATGAT
1706 TACACTTGGCAATCTGGTACAAATGCCTCTGTTTTCTGGCAATATGGTCAGACATATCCT
1707 CGATTTTCCTTACCTTTCTTAAGCATTGCATCTGTCTATTATATGTTTTATGATGGATAT
1708 GATGGGGACTCAACAGAATCACATTATGGGACAGCGGTGACCAATGATATGGGGACACTT
1709 TGTTCAAGAATAGTCACTGAAAATCATGGGACCCAAGTGAAGATAACAACTAGAATTTAT
1710 CATAAGGCAAAACATGTAAAAGCCTGGTGTCCAAGACCCCCAAGGGCAGTTGAATATAGA
1711 CATACACATGTTAACAATTACAAACCAGACCAAGGGGAAGTAACCACTATGATTCCAACT
1712 AGAACCAACATAAGAACCATCGTAAATGTT
1713 >114_HRV60
1714 AATCCAGTAGAAAGCTACATAGATGGGGTCTTAAACGAAGTCCTTGTGGTTCCAAACATT
1715 AGGGAGAGCCAACCCACTACTTCTAATTCTGCTCCAGCATTGGATGCTGCTGAGACTGGT
1716 CACACTAGTAATGTACAGCCTGAGGACGTGATTGAAACACGTTATGTGCAGATTACACAA
1717 ACTAGAGATGAGATGAGTGTTGAGAGCTTCCTCGGCAGATCTGGATGTATTCATATTTCC
1718 AAATTAGAAATTGACTATAGTAACTACAATGAGGAGAATAAAAATTTCACAACTTGGCAA
1719 ATTAACCTAAAGGAAATGGCACAAATAAGAAGAAAGTTTGAATTATTTACATATGTAAGA
1720 TTTGATTCAGAATTGACTCTGGTCCCATGCATAGCAGCAAAAAATGATGGCATAGGTCAT
1721 GTTGTCATGCAATACATGTATGTCCCCCCAGGAGCACCATTACCTACTAAAAGAGACGAT
1722 TACACATGGCAATCTGGCACAAATGCTTCTGTATTTTGGCAGCATGGACAAACATACCCT
1723 AGATTTTCACTTCCATTTCTAAGTATTGCATCTGCCTACTACATGTTTTATGATGGTTAT
1724 GATGGTCACTCAACTGAATCACATTATGGGACGGTTGTGACCAATGACATGGGAACGTTG
1725 TGCTCCAGAATAGTTACTGAACACCATGGTACACAGGTTCACGTCGCAACAAGAATATAT
1726 CATAAAGCAAAGCATGTTAAGGCTTGGTGTCCAAGACCTCCAAGGGCAGTTGAATATAGA
1727 CACACACATGTAAACAACTATAGACCAGATGATGGAGAAGCAGCCATAACAATCCCCATT
1728 AGAACTGATATACGAGCAATCAGAACAGTT
1729 >115_HRV60a
1730 AATCCAGTAGAAAGCTACATAGATGGGGTCTTAAACGAAGTCCTTGTGGTTCCAAACATT
1731 AGGGAGAGCCAACCCACTACTTCTAATTCTGCTCCAGCATTGGATGCTGCTGAGACTGGT
1732 CACACTAGTAATGTACAGCCTGAGGACGTGATTGAAACACGTTATGTGCAGATTACACAA
1733 ACTAGAGATGAGATGAGTGTTGAGAGCTTCCTCGGCAGATCTGGATGTATTCATATTTCC
1734 AAATTAGAAATTGACTATAGTAACTACAATGAGGAGAATAAAAATTTCACAACTTGGCAA
1735 ATTAACCTAAAGGAAATGGCACAAATAAGAAGAAAGTTTGAATTATTTACATATGTAAGA
1736 TTTGATTCAGAATTGACTCTGGTCCCATGCATAGCAGCAAAAAATGATGGCATAGGTCAT
1737 GTTGTCATGCAATACATGTATGTCCCCCCAGGAGCACCATTACCTACTAAAAGAGACGAT
1738 TACACATGGCAATCTGGCACAAATGCTTCTGTATTTTGGCAGCATGGACAAACATACCCT
1739 AGATTTTCACTTCCATTTCTAAGTATTGCATCTGCCTACTACATGTTTTATGATGGTTAT
1740 GATGGTCACTCAACTGAATCACATTATGGGACGGTTGTGACCAATGACATGGGAACGTTG
1741 TGCTCCAGAATAGTTACTGAACACCATGGTACACAGGTTCACGTCGCAACAAGAATATAT
1742 CATAAAGCAAAGCATGTTAAGGCTTGGTGTCCAAGACCTCCAAGGGCAGTTGAATATAGA
1743 CACACACATGTAAACAACTATAGACCAGATGATGGAGAAGCAGCCATAACAATCCCCATT
1744 AGAACTGATATACGAGCAATCAGAACAGTA
1745 >116_HRV60b
1746 AATCCAGTAGAAAGCTACATAGATGGGGTCTTAAACGAAGTCCTTGTGGTTCCAAACATT
1747 AGGGAGAGCCAACCCACTACTTCTAATTCTGCTCCAGCATTGGATGCTGCTGAGACTGGT
1748 CACACTAGTAATGTACAGCCTGAGGACGTGATTGAAACACGTTATGTGCAGATTACACAA
1749 ACTAGAGATGAGATGAGTGTTGAGAGCTTCCTCGGCAGATCTGGATGTATTCATATTTCC
1750 AAATTAGAAATTGACTATAGTAACTACAATGAGGAGAATAAAAATTTCACAACTTGGCAA
1751 ATTAACCTAAAGGAAATGGCACAAATAAGAAGAAAGTTTGAATTATTTACATATGTAAGA
1752 TTTGATTCAGAATTGACTCTGGTCCCATGCATAGCAGCAAAAAATGATGGCATAGGTCAT
1753 GTTGTCATGCAATACATGTATGTCCCCCCAGGAGCACCATTACCTACTAAAAGAGACGAT
1754 TACACATGGCAATCTGGCACAAATGCTTCTGTATTTTGGCAGCATGGACAAACATACCCT
1755 AGATTTTCACTTCCATTTCTAAGTATTGCATCTGCCTACTACATGTTTTATGATGGTTAT
```

FIG. D1 CONT'D

```
Rhino_cDNA_DB.fasta                                              9/20/2007 5:08 PM 1756 GATGGTCACTCAACTGAATCACATTATGGGACGGTTGTGACCAATGACATGGGAACGTTG
1757 TGCTCCAGAATAGTTACTGAACACCATGGTACACAGGTTCACGTCGCAACAAGAATATAT
1758 CATAAAGCAAAGCATGTTAAGGCTTGGTGTCCAAGACCTCCAAGGGCAGTTGAATATAGA
1759 CACACACATGTAAACAACTATAGACCAGATGATGGAGAAGCAGCCATAACAATCCCCATT
1760 AGAACTGATATACGAGCAATCAGAACAGTG
1761 >117_HRV64a
1762 AACCCAGTTGAACAATACATTGATGGTGTGTTGAATGAAGTTTTGATTGTCCCAAACATC
1763 AATGAGAGCCATCCCAGCACTTCCAATGCAGCGCCAGCTTTAGATGCAGCTGAGACCGGA
1764 CACACCAGTAATGTACAGCCTGAAGATATGATTGAAACGCGCTATGTACAAAACACTCAA
1765 ACTAGAGATGAAATGAGCATTGAGAGTTTCTTGGGCAGGTCTGGTTGTATACACATATCA
1766 GATTTAAAAGTAAATTATACTGGGTATAATGATGAAGGTAACAATTTTAACAAATGGCAG
1767 ATCACCTTGAAAGAAATGGCTCAGATAAGAAGGAAGTATGAATTATTTACATATGTTAGA
1768 TTTGATTCTGAAATAACCTTAGTGCCTTGCATATCTTCTCAGAGTGCTAACATTGGTCAT
1769 GTTGTTATGCAATATATGTATGTCCCTCCTGGAGCTCCAATACCAACCAAAAGAAATGAT
1770 TACGTCTGGCAGTCAGGCACCAATGCATCCATCTTTTGGCAACACGGTCAACCATACCCT
1771 CGATTTTCTCTCCCTTTCCTTAGCATAGCCTCAGCATATTACATGTTTTATGATGGTTAT
1772 GACGGTGGACCTGGTTCCCGTTATGGCGCAGTGGTGACAAATGATATGGGCACTTTGTGT
1773 TCTAGAATTGTGACTGAGGAACACACAACACAGGTCAACATCACTACTAGGGTTTATCAC
1774 AAAGCAAAACATGTCAAGGCATGGTGTCCACGGCCCCCAAGAGCTGTTGGATATACACAT
1775 ACAAATGTCACCAATTATAAACCATCCAAAGGAGAATACACACCACCCGTTCCGTCACGT
1776 AACAGCCCCAGAGATATTGTCACAGTG
1777 >118_HRV64b
1778 AACCCAGTTGAACAATACATTGATGGTGTGTTGAATGAAGTTTTGATTGTCCCAAACATC
1779 AATGAGAGCCATCCCAGCACTTCCAATGCAGCGCCAGCTTTAGATGCAGCTGAGACCGGA
1780 CACACCAGTAATGTACAGCCTGAAGATATGATTGAAACGCGCTATGTACAAAACACTCAA
1781 ACTAGAGATGAAATGAGCATTGAGAGTTTCTTGGGCAGGTCTGGTTGTATACACATATCA
1782 GATTTAAAAGTAAATTATACTGGGTATAATGATGAAGGTAACAATTTTAACAAATGGCAG
1783 ATCACCTTGAAAGAAATGGCTCAGATAAGAAGGAAGTATGAATTATTTACATATGTTAGA
1784 TTTGATTCTGAAATAACCTTAGTGCCTTGCATATCTTCTCAGAGTGCTAACATTGGTCAT
1785 GTTGTTATGCAATATATGTATGTCCCTCCTGGAGCTCCAATACCAACCAAAAGAAATGAT
1786 TACGTCTGGCAGTCAGGCACCAATGCATCCATCTTTTGGCAACACGGTCAACCATACCCT
1787 CGATTTTCTCTCCCTTTCCTTAGCATAGCCTCAGCATATTACATGTTTTATGATGGTTAT
1788 GACGGTGGACCTGGTTCCCGTTATGGGCAGTGGTGACAAATGATATGGGCACTTTGTGT
1789 TCTAGAATTGTGACTGAGGAACACACAACACAGGTCAACATCACTACTAGGGTTTATCAC
1790 AAAGCAAAACATGTCAAGGCATGGTGTCCACGGCCCCCAAGAGCTGTTGGATATACACAT
1791 ACAAATGTCACCAATTATAAACCATCCAAAGGAGAATACACACCACCCGTTCCGTCACGT
1792 AACAGCCCCAGAGATATTGTCACAGTG
1793 >119_HRV64
1794 AACCCAGTTGAACAATACATTGATGGTGTGTTGAATGAAGTTTTGATTGTCCCAAACATC
1795 AATGAGAGCCATCCCAGCACTTCCAATGCAGCGCCAGCTTTAGATGCAGCTGAGACCGGA
1796 CACACCAGTAATGTACAGCCTGAAGATATGATTGAAACGCGCTATGTACAAAACACTCAA
1797 ACTAGAGATGAAATGAGCATTGAGAGTTTCTTGGGCAGGTCTGGTTGTATACACATATCA
1798 GATTTAAAAGTAAATTATACTGGGTATAATGATGAAGGTAACAATTTTAACAAATGGCAG
1799 ATCACCTTGAAAGAAATGGCTCAGATAAGAAGGAAGTATGAATTATTTACATATGTTAGA
1800 TTTGATTCTGAAATAACCTTAGTGCCTTGCATATCTTCTCAGAGTGCTAACATTGGTCAT
1801 GTTGTTATGCAATATATGTATGTCCCTCCTGGAGCTCCAATACCAACCAAAAGAAATGAT
1802 TACGTCTGGCAGTCAGGCACCAATGCATCCATCTTTTGGCAACACGGTCAACCATACCCT
1803 CGATTTTCTCTCCCTTTCCTTAGCATAGCCTCAGCATATTACATGTTTTATGATGGTTAT
1804 GACGGTGGACCTGGTTCCCGTTATGGCGCAGTGGTGACAAATGATATGGGCACTTTGTGT
1805 TCTAGAATTGTGACTGAGGAACACACAACACAGGTCAACATCACTACTAGGGTTTATCAC
1806 AAAGCAAAACATGTCAAGGCATGGTGTCCACGGCCCCCAAGAGCTGTTGGATATACACAT
1807 ACAAATGTCACCAATTATAAACCATCCAAAGGAGAATACACACCACCCGTTCCGTCACGT
1808 AACAGCCCCAGAGATATTGTCACAGTA
1809 >120_HRV94a
1810 AATCCAGTTGAGAAATACATTGATGGTGTATTGAATGAAGTTTTAGTTGTTCCAAATATC
1811 AATGAGAGTCACCCTAGCACATCCAATGCAGCGCCAGCCTTAGATGCTGCCGAAACTGGA
1812 CACACAAGCAATGTACAACCTGAGGATATGATTGAAACACGCTATGTACAAAACACTCAA
1813 ACAAGGGATGAAATGAGCATTGAAAGCTTCTTGGGAAGATCTGGCTGTATACACATAGCA
1814 CATCTAGAGATCAAGTATGATGGTTACAATGATGCTGGCAACAATTTCCAATCATGGCAA
1815 ATTACCCTAAAAGAAATGGCACAAATAAGAAGGAAATTTGAACTATTTACTTATGTTAGA
1816 TTTGATTCAGAAATAACTTTAGTACCTTGCATATCATCCAAAGTGCTAATATTGGTCAT
1817 GTTGTCATGCAGTACATGTATGTTCCTCCTGGAGCTCCAAAACCAGACAAAAGAGATGAT
1818 TATGTTTGGCAATCAGGAACTAATGCATCTATATTCTGGCAACATGGTCAACCCTACCCT
1819 CGATTCTCACTTCCATTTCTTAGTATAGCCTCAGCATATTACATGTTCTATGATGGTTAT
1820 GATGGTGGACCTGGCTCACGCTATGGCACAGTGGTGACAAATGACATGGGAACATTATGC
```

FIG. D1 CONT'D

Rhino_cDNA_DB.fasta                                                9/20/2007 5:08 PM

```
1821 TCCAGGATTGTGACTGAGGAGCACAAGACACAGGTTAACATCACTACTAGAGTGTACCAC
1822 AAAGCAAAACATGTGAAAGCGTGGTGCCCGCGCCCTCCAAGAGCTGTTGGATACACACAT
1823 ACGCATGTCACTAATTACAAACCATCTGAAGGGGAGTACAAGCCACCTGTCCCAGTTAGG
1824 AATAGCCCCAGAGACATTGTCACAGTG
1825 >121_HRV94b
1826 AATCCAGTTGAGAAATACATTGATGGTGTATTGAATGAAGTTTTAGTTGTTCCAAATATC
1827 AATGAGAGTCACCCTAGCACATCCAATGCAGCGCCAGCCTTAGATGCTGCCGAAACTGGA
1828 CACACAAGCAATGTACAACCTGAGGATATGATTGAAACACGCTATGTACAAAACACTCAA
1829 ACAAGGGATGAAATGAGCATTGAAAGCTTCTTGGGAAGATCTGGCTGTATACACATAGCA
1830 CATCTAGAGATCAAGTATGATGGTTACAATGATGCTGGCAACAATTTCCAATCATGGCAA
1831 ATTACCCTAAAAGAAATGGCACAAATAAGAAGGAAATTTGAACTATTTACTTATGTTAGA
1832 TTTGATTCAGAAATAACTTTAGTACCTTGCATATCATCTCAAAGTGCTAATATTGGTCAT
1833 GTTGTCATGCAGTACATGTATGTTCCTCCTGGAGCTCCAAAACCAGACAAAAGAGATGAT
1834 TATGTTTGGCAATCAGGAACTAATGCATCTATATTCTGGCAACATGGTCAACCCTACCCT
1835 CGATTCTCACTTCCATTTCTTAGTATAGCCTCAGCATATTACATGTTCTATGATGGTTAT
1836 GATGGTGGACCTGGCTCACGCTATGGCACAGTGGTGACAAATGACATGGGAACATTATGC
1837 TCCAGGATTGTGACTGAGGAGCACAAGACACAGGTTAACATCACTACTAGAGTGTACCAC
1838 AAAGCAAAACATGTGAAAGCGTGGTGCCCGCGCCCTCCAAGAGCTGTTGGATACACACAT
1839 ACGCATGTCACTAATTACAAACCATCTGAAGGGGAGTACAAGCCACCTGTCCCAGTTAGG
1840 AATAGCCCCAGAGACATTGTCACAGTC
1841 >122_HRV94
1842 AATCCAGTTGAGAAATACATTGATGGTGTATTGAATGAAGTTTTAGTTGTTCCAAATATC
1843 AATGAGAGTCACCCTAGCACATCCAATGCAGCGCCAGCCTTAGATGCTGCCGAAACTGGA
1844 CACACAAGCAATGTACAACCTGAGGATATGATTGAAACACGCTATGTACAAAACACTCAA
1845 ACAAGGGATGAAATGAGCATTGAAAGCTTCTTGGGAAGATCTGGCTGTATACACATAGCA
1846 CATCTAGAGATCAAGTATGATGGTTACAATGATGCTGGCAACAATTTCCAATCATGGCAA
1847 ATTACCCTAAAAGAAATGGCACAAATAAGAAGGAAATTTGAACTATTTACTTATGTTAGA
1848 TTTGATTCAGAAATAACTTTAGTACCTTGCATATCATCTCAAAGTGCTAATATTGGTCAT
1849 GTTGTCATGCAGTACATGTATGTTCCTCCTGGAGCTCCAAAACCAGACAAAAGAGATGAT
1850 TATGTTTGGCAATCAGGAACTAATGCATCTATATTCTGGCAACATGGTCAACCCTACCCT
1851 CGATTCTCACTTCCATTTCTTAGTATAGCCTCAGCATATTACATGTTCTATGATGGTTAT
1852 GATGGTGGACCTGGCTCACGCTATGGCACAGTGGTGACAAATGACATGGGAACATTATGC
1853 TCCAGGATTGTGACTGAGGAGCACAAGACACAGGTTAACATCACTACTAGAGTGTACCAC
1854 AAAGCAAAACATGTGAAAGCGTGGTGCCCGCGCCCTCCAAGAGCTGTTGGATACACACAT
1855 ACGCATGTCACTAATTACAAACCATCTGAAGGGGAGTACAAGCCACCTGTCCCAGTTAGG
1856 AATAGCCCCAGAGACATTGTCACAGTA
1857 >123_HRV22
1858 AACCCTGTAGAGAAATACATTGATGGTGTATTGAATGAAGTATTGGTTGTTCCAAACACA
1859 AATGAAAGTCACCCCAGTACATCAAATGCTGCACCAGCACTAGATGCTGCTGAAACTGGA
1860 CACACAAGCAATGTGCAGCCAGAAGACATGATAGAAACACGCTATGTGTTAAATTCACAA
1861 ACTAGAGATGAAATGAGTATTGAGAGCTTCCTGGGAAGATCTGGTTGCATACATATATCA
1862 CACTTAGAAGTAAAATACACAGGGTATAATGAAGAGGGTAATAACTTTAACATATGGCAA
1863 ATTAACCTTAAAGAGATGGCTCAGATAAGAAGGAAGTTTGAGCTATTTACATATCTCAGG
1864 TTTGATTCTGAAATCACTTTGGTACCATGCATTGCTTCACAAAGTAAAAACATTGGTCAT
1865 GTGGTCATGCAATACATGTATGTTCCGCCTGGAGCTCCTAAACCTGAAAAGAGAGATGAC
1866 TACACATGGCAATCTGGCACTAATGCATCTGTTTTCTGGCAGCATGGTCAACCTTATCCC
1867 CGATTCTCACTCCCTTTCCTCAGTGTAGCTTCAGCATATTACATGTTTTATGATGGGTAT
1868 GATGAGGTCCCGGATCACGTTATGGAGCAGTGGTAACAAATGATATGGGCACACTGTGC
1869 TCTAGGATTGTGACTGAAGAACACCAGACACAAGTCAAAATTACAACTAGAGTGTACCAC
1870 AAAGCAAAACATGTAAAGGCATGGTGCCCACGTCCTCCAAGAGCTGTTGGATATACACAC
1871 ACACATGTGACAAACTACAAACCATCTGTAGGGGATTACACACTACCTATCCCAACAAGA
1872 GCCAACCCTAGACAAATTTTGAATGTA
1873 >124_HRV22a
1874 AACCCTGTAGAGAAATACATTGATGGTGTATTGAATGAAGTATTGGTTGTTCCAAACACA
1875 AATGAAAGTCACCCCAGTACATCAAATGCTGCACCAGCACTAGATGCTGCTGAAACTGGA
1876 CACACAAGCAATGTGCAGCCAGAAGACATGATAGAAACACGCTATGTGTTAAATTCACAA
1877 ACTAGAGATGAAATGAGTATTGAGAGCTTCCTGGGAAGATCTGGTTGCATACATATATCA
1878 CACTTAGAAGTAAAATACACAGGGTATAATGAAGAGGGTAATAACTTTAACATATGGCAA
1879 ATTAACCTTAAAGAGATGGCTCAGATAAGAAGGAAGTTTGAGCTATTTACATATCTCAGG
1880 TTTGATTCTGAAATCACTTTGGTACCATGCATTGCTTCACAAAGTAAAAACATTGGTCAT
1881 GTGGTCATGCAATACATGTATGTTCCGCCTGGAGCTCCTAAACCTGAAAAGAGAGATGAC
1882 TACACATGGCAATCTGGCACTAATGCATCTGTTTTCTGGCAGCATGGTCAACCTTATCCC
1883 CGATTCTCACTCCCTTTCCTCAGTGTAGCTTCAGCATATTACATGTTTTATGATGGGTAT
1884 GATGGAGGTCCCGGATCACGTTATGGAGCAGTGGTAACAAATGATATGGGCACACTGTGC
1885 TCTAGGATTGTGACTGAAGAACACCAGACACAAGTCAAAATTACAACTAGAGTGTACCAC
```

FIG. D1 CONT'D

Rhino cDNA DB.fasta                                                    9/20/2007 5:08 PM

```
1886 AAAGCAAAACATGTAAAGGCATGGTGCCCACGTCCTCCAAGAGCTGTTGGATATACACAC
1887 ACACATGTGACAAACTACAAACCATCTGTAGGGGATTACACACTACCTATCCCAACAAGA
1888 GCCAACCCTAGACAAATTTTGAATGTG
1889 >125_HRV22b
1890 AACCCTGTAGAGAAATACATTGATGGTGTATTGAATGAAGTATTGGTTGTTCCAAACACA
1891 AATGAAAGTCACCCCAGTACATCAAATGCTGCACCAGCACTAGATGCTGCTGAAACTGGA
1892 CACACAAGCAATGTGCAGCCAGAAGACATGATAGAAACACGCTATGTGTTAAATTCACAA
1893 ACTAGAGATGAAATGAGTATTGAGAGCTTCCTGGGAAGATCTGGTTGCATACATATATCA
1894 CACTTAGAAGTAAAATACACAGGGTATAATGAAGAGGGTAATAACTTTAACATATGGCAA
1895 ATTAACCTTAAAGAGATGGCTCAGATAAGAAGGAAGTTTGAGCTATTTACATATCTCAGG
1896 TTTGATTCTGAAATCACTTTGGTACCATGCATTGCTTCACAAAGTAAAAACATTGGTCAT
1897 GTGGTCATGCAATACATGTATGTTCCGCCTGGAGCTCCTAAACCTGAAAAGAGAGATGAC
1898 TACACATGGCAATCTGGCACTAATGCATCTGTTTTCTGGCAGCATGGTCAACCTTATCCC
1899 CGATTCTCACTCCCTTTCCTCAGTGTAGCTTCAGCATATTACATGTTTTATGATGGGTAT
1900 GATGGAGGTCCCGGATCACGTTATGGAGCAGTGGTAACAAATGATATGGGCACACTGTGC
1901 TCTAGGATTGTGACTGAAGAACACCAGACACAAGTCAAAATTACAACTAGAGTGTACCAC
1902 AAAGCAAAACATGTAAAGGCATGGTGCCCACGTCCTCCAAGAGCTGTTGGATATACACAC
1903 ACACATGTGACAAACTACAAACCATCTGTAGGGGATTACACACTACCTATCCCAACAAGA
1904 GCCAACCCTAGACAAATTTTGAATGTC
1905 >126_HRV82
1906 AATCCAGTTGAAAAGTATGTTGATAGTGTTTTAAACGAGGTATTAGTTGTTCCTAACATT
1907 AATGAAAGTCATCCTAGTACTTCAAATTCAGCTCCTGCCTTGGACGCTGCAGAGACAGGA
1908 CATACAAGTACTGTTCAACCTGAGGACATGATTGAAACACGGTATGTTCAAACATCACAA
1909 ACTAGAGATGAGATGAGCCTTGAGAGTTTCCTAGGGAGATCTGGCTGCATACACATATCA
1910 CACCTAAATGTCAGATACACTGATTATAATGAAGGTAATAACTTTAGATCATGGCAAATA
1911 AGCATAAAGGAAATGGCACAAATTAGAAGGAAGTTTGAACTTTTCACATATGTGAGATTT
1912 GATTCAGAAATTACTTTAGTGCCTTGCATAGCCTCTCAAAGTAATGATATTGGGCATGTA
1913 GTGATGCAATACATGTATGTCCCACCAGGTGCTCCTAAACCAGAAAAGAGAGACGACTAC
1914 ACTTGGCAATCTGGAACTAATGCTTCAATTTTCTGGCAACATGGACAACCTTACCCTCGC
1915 TTCTCACTTCCTTTCTTGAGTATAGCCTCAGCTTACTATATGTTCTATGATGGCTATGAT
1916 GGTGATGCTCCCGGATCGCGATACGGGACCATAGTGACAAATGACATGGGTACACTGTGT
1917 TCTAGAATTGTAACTGAAGAACACCAGACTCAAGTCAGCATTACCACAAGAATATATCAC
1918 AAAGCAAAACATGTGAAAGCGTGGTGTCCACGACCCCCGAGGGCTGTGGGTTATACACAC
1919 ACACATGTTACCAACTACAAGCCATCACAGGGAGATTACAGTGTTGTTATTCCAGTTAGA
1920 GAGAGTCCCAGACAGATTCTTAATGTA
1921 >127_HRV82b
1922 AATCCAGTTGAAAAGTATGTTGATAGTGTTTTAAACGAGGTATTAGTTGTTCCTAACATT
1923 AATGAAAGTCATCCTAGTACTTCAAATTCAGCTCCTGCCTTGGACGCTGCAGAGACAGGA
1924 CATACAAGTACTGTTCAACCTGAGGACATGATTGAAACACGGTATGTTCAAACATCACAA
1925 ACTAGAGATGAGATGAGCCTTGAGAGTTTCCTAGGGAGATCTGGCTGCATACACATATCA
1926 CACCTAAATGTCAGATACACTGATTATAATGAAGGTAATAACTTTAGATCATGGCAAATA
1927 AGCATAAAGGAAATGGCACAAATTAGAAGGAAGTTTGAACTTTTCACATATGTGAGATTT
1928 GATTCAGAAATTACTTTAGTGCCTTGCATAGCCTCTCAAAGTAATGATATTGGGCATGTA
1929 GTGATGCAATACATGTATGTCCCACCAGGTGCTCCTAAACCAGAAAAGAGAGACGACTAC
1930 ACTTGGCAATCTGGAACTAATGCTTCAATTTTCTGGCAACATGGACAACCTTACCCTCGC
1931 TTCTCACTTCCTTTCTTGAGTATAGCCTCAGCTTACTATATGTTCTATGATGGCTATGAT
1932 GGTGATGCTCCCGGATCGCGATACGGGACCATAGTGACAAATGACATGGGTACACTGTGT
1933 TCTAGAATTGTAACTGAAGAACACCAGACTCAAGTCAGCATTACCACAAGAATATATCAC
1934 AAAGCAAAACATGTGAAAGCGTGGTGTCCACGACCCCCGAGGGCTGTGGGTTATACACAC
1935 ACACATGTTACCAACTACAAGCCATCACAGGGAGATTACAGTGTTGTTATTCCAGTTAGA
1936 GAGAGTCCCAGACAGATTCTTAATGTT
1937 >128_HRV82a
1938 AATCCAGTTGAAAAGTATGTTGATAGTGTTTTAAACGAGGTATTAGTTGTTCCTAACATT
1939 AATGAAAGTCATCCTAGTACTTCAAATTCAGCTCCTGCCTTGGACGCTGCAGAGACAGGA
1940 CATACAAGTACTGTTCAACCTGAGGACATGATTGAAACACGGTATGTTCAAACATCACAA
1941 ACTAGAGATGAGATGAGCCTTGAGAGTTTCCTAGGGAGATCTGGCTGCATACACATATCA
1942 CACCTAAATGTCAGATACACTGATTATAATGAAGGTAATAACTTTAGATCATGGCAAATA
1943 AGCATAAAGGAAATGGCACAAATTAGAAGGAAGTTTGAACTTTTCACATATGTGAGATTT
1944 GATTCAGAAATTACTTTAGTGCCTTGCATAGCCTCTCAAAGTAATGATATTGGGCATGTA
1945 GTGATGCAATACATGTATGTCCCACCAGGTGCTCCTAAACCAGAAAAGAGAGACGACTAC
1946 ACTTGGCAATCTGGAACTAATGCTTCAATTTTCTGGCAACATGGACAACCTTACCCTCGC
1947 TTCTCACTTCCTTTCTTGAGTATAGCCTCAGCTTACTATATGTTCTATGATGGCTATGAT
1948 GGTGATGCTCCCGGATCGCGATACGGGACCATAGTGACAAATGACATGGGTACACTGTGT
1949 TCTAGAATTGTAACTGAAGAACACCAGACTCAAGTCAGCATTACCACAAGAATATATCAC
1950 AAAGCAAAACATGTGAAAGCGTGGTGTCCACGACCCCCGAGGGCTGTGGGTTATACACAC
```

FIG. D1 CONT'D

Rhino_cDNA_DB.fasta                                                                9/20/2007 5:08 PM

```
1951 ACACATGTTACCAACTACAAGCCATCACAGGGAGATTACAGTGTTGTTATTCCAGTTAGA
1952 GAGAGTCCCAGACAGATTCTTAATGTC
1953 >129_HRV19
1954 AATCCTGTAGAGAAATATGTGGACACCATTCTGAATGAGGTGCTAGTTGTCCCAAATATC
1955 AATGAAAGTCATCCAAGTACATCAAATGCTGCTCCTGCCTTAGATGCAGCCGAGACAGGA
1956 CATACTAGCAATGTACAGCCTGAGGACATGATCGAAACACGCTATGTTCAAACGTCCCAG
1957 ACTAGGGATGAAATGAGCATAGAAAGTTTTCTTGGCAGATCCGGTTGTGTACATGTTTCA
1958 GAGCTCCAATTAGATTATACCAATTACAATCAAGAAAATAATAATTTCAAAACTTGGCAA
1959 ATAAACTTGAAAGAAATGGCACAGATTAGAAGAAAATTTGAACTTTTCACTTACCTCAGA
1960 TTTGATTCAGAGGTAACATTAGTCCCTTGCATAGCTGCTAAAAGTAAAAACATTGGACAT
1961 GTTGTTATGCAATACATGTATGTGCCTCCTGGTGCTCCTATCCCAAAAACTAGAAATGAT
1962 TACACATGGCAATCAGGTACTAATGCATCTATATTTTGGCAACATGGTCAACCATACCCA
1963 AGATTTTCATTACCTTTTCTAAGTATAGCTTCTGCATATTACATGTTTTATGATGGGTAT
1964 GATGGAGATTCACCAGGATCCCGCTATGGAACAATAGTAACTAATGATATGGGAACCTTA
1965 TGCTCCAGAATAGTAACTGATGAACACCAAACACAGGTTGCAATCACAACTAGAGTATAT
1966 CATAAAGCTAAACATATAAAAGCTTGGTGCCCACGACCACCCAGAGCCGTGGAATATACC
1967 CACACTCATGTGACTAATTATAAACCCCAGACAGGTGAAGTCACTCTTCCAATTGAAATA
1968 AGAGATAACCCTAGACATATAAAGAATGTA
1969 >130_HRV19a
1970 AATCCTGTAGAGAAATATGTGGACACCATTCTGAATGAGGTGCTAGTTGTCCCAAATATC
1971 AATGAAAGTCATCCAAGTACATCAAATGCTGCTCCTGCCTTAGATGCAGCCGAGACAGGA
1972 CATACTAGCAATGTACAGCCTGAGGACATGATCGAAACACGCTATGTTCAAACGTCCCAG
1973 ACTAGGGATGAAATGAGCATAGAAAGTTTTCTTGGCAGATCCGGTTGTGTACATGTTTCA
1974 GAGCTCCAATTAGATTATACCAATTACAATCAAGAAAATAATAATTTCAAAACTTGGCAA
1975 ATAAACTTGAAAGAAATGGCACAGATTAGAAGAAAATTTGAACTTTTCACTTACCTCAGA
1976 TTTGATTCAGAGGTAACATTAGTCCCTTGCATAGCTGCTAAAAGTAAAAACATTGGACAT
1977 GTTGTTATGCAATACATGTATGTGCCTCCTGGTGCTCCTATCCCAAAAACTAGAAATGAT
1978 TACACATGGCAATCAGGTACTAATGCATCTATATTTTGGCAACATGGTCAACCATACCCA
1979 AGATTTTCATTACCTTTTCTAAGTATAGCTTCTGCATATTACATGTTTTATGATGGGTAT
1980 GATGGAGATTCACCAGGATCCCGCTATGGAACAATAGTAACTAATGATATGGGAACCTTA
1981 TGCTCCAGAATAGTAACTGATGAACACCAAACACAGGTTGCAATCACAACTAGAGTATAT
1982 CATAAAGCTAAACATATAAAAGCTTGGTGCCCACGACCACCCAGAGCCGTGGAATATACC
1983 CACACTCATGTGACTAATTATAAACCCCAGACAGGTGAAGTCACTCTTCCAATTGAAATA
1984 AGAGATAACCCTAGACATATAAAGAATGTG
1985 >131_HRV19b
1986 AATCCTGTAGAGAAATATGTGGACACCATTCTGAATGAGGTGCTAGTTGTCCCAAATATC
1987 AATGAAAGTCATCCAAGTACATCAAATGCTGCTCCTGCCTTAGATGCAGCCGAGACAGGA
1988 CATACTAGCAATGTACAGCCTGAGGACATGATCGAAACACGCTATGTTCAAACGTCCCAG
1989 ACTAGGGATGAAATGAGCATAGAAAGTTTTCTTGGCAGATCCGGTTGTGTACATGTTTCA
1990 GAGCTCCAATTAGATTATACCAATTACAATCAAGAAAATAATAATTTCAAAACTTGGCAA
1991 ATAAACTTGAAAGAAATGGCACAGATTAGAAGAAAATTTGAACTTTTCACTTACCTCAGA
1992 TTTGATTCAGAGGTAACATTAGTCCCTTGCATAGCTGCTAAAAGTAAAAACATTGGACAT
1993 GTTGTTATGCAATACATGTATGTGCCTCCTGGTGCTCCTATCCCAAAAACTAGAAATGAT
1994 TACACATGGCAATCAGGTACTAATGCATCTATATTTTGGCAACATGGTCAACCATACCCA
1995 AGATTTTCATTACCTTTTCTAAGTATAGCTTCTGCATATTACATGTTTTATGATGGGTAT
1996 GATGGAGATTCACCAGGATCCCGCTATGGAACAATAGTAACTAATGATATGGGAACCTTA
1997 TGCTCCAGAATAGTAACTGATGAACACCAAACACAGGTTGCAATCACAACTAGAGTATAT
1998 CATAAAGCTAAACATATAAAAGCTTGGTGCCCACGACCACCCAGAGCCGTGGAATATACC
1999 CACACTCATGTGACTAATTATAAACCCCAGACAGGTGAAGTCACTCTTCCAATTGAAATA
2000 AGAGATAACCCTAGACATATAAAGAATGTC
2001 >132_HRV1
2002 AATCCTGTTGAAAGGTATGTAGATGAAGTCTTGAATGAAGTTCTTGTAGTACCAAATATC
2003 AGTGAAAGTAGCTCAACTACATCTAATTCAGCTCCAGCCTTAGATGCTGCAGAAACTGGC
2004 CACACAAGCAGTGTACAACCAGAAGACATGGTTGAAACACGTTATGTCCAAACTTCACAA
2005 ACTAGGGATGAAATGAGTGTTGAGAGCTTTTTAGGCAGATCTGGTTGTATACACATGTCT
2006 ACCATGAACATAGATTATACTAATTATGATGATTCTGTTAATAATTTTGTGAAATGGAAA
2007 ATAAGTTTGCAAGAAATGGCCCAAGTGCGCAGAAAATTTGAGTTGTTCACCTATGTAAGA
2008 TTTGATTCAGAAATAACAATTGTGCCATGTATAGCCGGGCAAGGTGGTGATGTCGGACAT
2009 GTTGTTATGCAATACATGTATGTACCGCCCGGTGCACCCCTTCCAACGAAGAGAAATGAT
2010 TACACATGGCAATCTGGCACCAATGCATCTGTTTTCTGGCAACATGGTCAAATTTACCCC
2011 CGATTCTCTTTACCATTTCTTAGTATTGCATCTGCATATTATATGTTTTATGATGGATAT
2012 AATGGAGATTCCTCAGATGCACGCTATGGGACAACAATCACTAATGATATGGGCACACTT
2013 TGCTTCAGAATAGTAACTGAAGAACATACTAACAAGGTCAAGGTTACAACTAGAATCTAT
2014 CATAAAGCTAAACATGTCAAAGCATGGTGTCCTAGACCTCCCAGAGCTGTTGAATATACT
2015 AATGTGCATGTTACAAACTACAAACCAGGGACAGGAGATGTTGCAGTCTCCATTGTACCT
```

FIG. D1 CONT'D

Rhino_cDNA_DB.fasta                                                      9/20/2007 5:08 PM

```
2016 AGAGCAAATGTTAGGGAAATTAGAAACTTT
2017 >133_HRV13a
2018 AATCCTGTTGAAAGGTATGTAGATGAAGTCTTGAATGAAGTTCTTGTAGTACCAAATATC
2019 AGTGAAAGTAGCTCAACTACATCTAATTCAGCTCCAGCCTTAGATGCTGCAGAAACTGGC
2020 CACACAAGCAGTGTACAACCAGAAGACATGGTTGAAACACGTTATGTCCAAACTTCACAA
2021 ACTAGGGATGAAATGAGTGTTGAGAGCTTTTTAGGCAGATCTGGTTGTATACACATGTCT
2022 ACCATGAACATAGATTATACTAATTATGATGATTCTGTTAATAATTTTGTGAAATGGAAA
2023 ATAAGTTTGCAAGAAATGGCCCAAGTGCGCAGAAAATTTGAGTTGTTCACCTATGTAAGA
2024 TTTGATTCAGAAATAACAATTGTGCCATGTATAGCCGGGCAAGGTGGTGATGTCGGACAT
2025 GTTGTTATGCAATACATGTATGTACCGCCCGGTGCACCCCTTCCAACGAAGAGAAATGAT
2026 TACACATGGCAATCTGGCACCAATGCATCTGTTTTCTGGCAACATGGTCAAATTTACCCC
2027 CGATTCTCTTTACCATTTCTTAGTATTGCATCTGCATATTATATGTTTTATGATGGATAT
2028 AATGGAGATTCCTCAGATGCACGCTATGGGACAACAATCACTAATGATATGGGCACACTT
2029 TGCTTCAGAATAGTAACTGAAGAACATACTAACAAGGTCAAGGTTACAACTAGAATCTAT
2030 CATAAAGCTAAACATGTCAAAGCATGGTGTCCTAGACCTCCCAGAGCTGTTGAATATACT
2031 AATGTGCATGTTACAAACTACAAACCAGGGACAGGAGATGTTGCAGTCTCCATTGTACCT
2032 AGAGCAAATGTTAGGGAAATTAGAAACTTG
2033 >134_HRV13b
2034 AATCCTGTTGAAAGGTATGTAGATGAAGTCTTGAATGAAGTTCTTGTAGTACCAAATATC
2035 AGTGAAAGTAGCTCAACTACATCTAATTCAGCTCCAGCCTTAGATGCTGCAGAAACTGGC
2036 CACACAAGCAGTGTACAACCAGAAGACATGGTTGAAACACGTTATGTCCAAACTTCACAA
2037 ACTAGGGATGAAATGAGTGTTGAGAGCTTTTTAGGCAGATCTGGTTGTATACACATGTCT
2038 ACCATGAACATAGATTATACTAATTATGATGATTCTGTTAATAATTTTGTGAAATGGAAA
2039 ATAAGTTTGCAAGAAATGGCCCAAGTGCGCAGAAAATTTGAGTTGTTCACCTATGTAAGA
2040 TTTGATTCAGAAATAACAATTGTGCCATGTATAGCCGGGCAAGGTGGTGATGTCGGACAT
2041 GTTGTTATGCAATACATGTATGTACCGCCCGGTGCACCCCTTCCAACGAAGAGAAATGAT
2042 TACACATGGCAATCTGGCACCAATGCATCTGTTTTCTGGCAACATGGTCAAATTTACCCC
2043 CGATTCTCTTTACCATTTCTTAGTATTGCATCTGCATATTATATGTTTTATGATGGATAT
2044 AATGGAGATTCCTCAGATGCACGCTATGGGACAACAATCACTAATGATATGGGCACACTT
2045 TGCTTCAGAATAGTAACTGAAGAACATACTAACAAGGTCAAGGTTACAACTAGAATCTAT
2046 CATAAAGCTAAACATGTCAAAGCATGGTGTCCTAGACCTCCCAGAGCTGTTGAATATACT
2047 AATGTGCATGTTACAAACTACAAACCAGGGACAGGAGATGTTGCAGTCTCCATTGTACCT
2048 AGAGCAAATGTTAGGGAAATTAGAAACTTA
2049 >135_HRV41
2050 AATCCTGTAGAAAGGTATGTGGATGAGGTCCTGAATGAGGTTCTTGTGGTACCAAATATT
2051 AGTGAAAGCAGTCCAACTACTTCTAATTCAGCTCCAGCCCTAGATGCAGCAGAGACTGGT
2052 CATACCAGTAATGTACAACCAGAGGACATGATTGAAACACGATATGTCCAAACCTCACAA
2053 ACTAGAGATGAAATGAGCATAGAAAGCTTTTTAGGTAGATCAGGCTGTGTACATAAGTCC
2054 ACTTTGAATATAGATTATACTGATTATGATGATTCTATCCAGAACTTCAAGAAGTGGAAA
2055 ATTAGCTTACAGGAGATGGCCCAAGTACGTAGAAAGTTTGAGTTTTTTACGTATGTTAGA
2056 TTTGACTCAGAAATAACAATTGTGCCAAGTATAGCTGGACAGGGTAGTGATGTCGGACAT
2057 GTTGTCATGCAATACATGTTCGTACCACCTGGCGCACCCCTCCCAGAAAAGAGAGATGAT
2058 TACACATGGCAATCTGGCACCAATGCATCTGTATTCTGGCAGTATGGTCAAGTTTACCCT
2059 AGGTTTTCTCTACCATTTCTTAGCATTGCTTCCGCATATTACATGTTTTATGATGGTTAT
2060 GAAGAAGGCTCTACAAATGCACGCTATGGAACAACAGTCACAAATGACATGGGTACATTA
2061 TGCTTTAGAATAGTTACTGAAGAACACACCAACAAAGTTAAGGTCACAACTAGAGTTTAC
2062 CACAAAGCTAAACATGTTAAAGCATGGTGTCCTAGACCTCCCAGGGCTGTGGAGTACACC
2063 AATGTGCATGTCACAAATTACAAACCAAAAGCAGGAGCAGAGATTGTGGCTTCTGTCAGA
2064 CCTAGAGACAATGTTAGACAAGTAAGAAATTAT
2065 >136_HRV41a
2066 AATCCTGTAGAAAGGTATGTGGATGAGGTCCTGAATGAGGTTCTTGTGGTACCAAATATT
2067 AGTGAAAGCAGTCCAACTACTTCTAATTCAGCTCCAGCCCTAGATGCAGCAGAGACTGGT
2068 CATACCAGTAATGTACAACCAGAGGACATGATTGAAACACGATATGTCCAAACCTCACAA
2069 ACTAGAGATGAAATGAGCATAGAAAGCTTTTTAGGTAGATCAGGCTGTGTACATAAGTCC
2070 ACTTTGAATATAGATTATACTGATTATGATGATTCTATCCAGAACTTCAAGAAGTGGAAA
2071 ATTAGCTTACAGGAGATGGCCCAAGTACGTAGAAAGTTTGAGTTTTTTACGTATGTTAGA
2072 TTTGACTCAGAAATAACAATTGTGCCAAGTATAGCTGGACAGGGTAGTGATGTCGGACAT
2073 GTTGTCATGCAATACATGTTCGTACCACCTGGCGCACCCCTCCCAGAAAAGAGAGATGAT
2074 TACACATGGCAATCTGGCACCAATGCATCTGTATTCTGGCAGTATGGTCAAGTTTACCCT
2075 AGGTTTTCTCTACCATTTCTTAGCATTGCTTCCGCATATTACATGTTTTATGATGGTTAT
2076 GAAGAAGGCTCTACAAATGCACGCTATGGAACAACAGTCACAAATGACATGGGTACATTA
2077 TGCTTTAGAATAGTTACTGAAGAACACACCAACAAAGTTAAGGTCACAACTAGAGTTTAC
2078 CACAAAGCTAAACATGTTAAAGCATGGTGTCCTAGACCTCCCAGGGCTGTGGAGTACACC
2079 AATGTGCATGTCACAAATTACAAACCAAAAGCAGGAGCAGAGATTGTGGCTTCTGTCAGA
2080 CCTAGAGACAATGTTAGACAAGTAAGAAATTAG
```

FIG. D1 CONT'D

Rhino_cDNA_DB.fasta                                                                      9/20/2007 5:08 PM

```
2081  >137_HRV41b
2082  AATCCTGTAGAAAGGTATGTGGATGAGGTCCTGAATGAGGTTCTTGTGGTACCAAATATT
2083  AGTGAAAGCAGTCCAACTACTTCTAATTCAGCTCCAGCCCTAGATGCAGCAGAGACTGGT
2084  CATACCAGTAATGTACAACCAGAGGACATGATTGAAACACGATATGTCCAAACCTCACAA
2085  ACTAGAGATGAAATGAGCATAGAAAGCTTTTTAGGTAGATCAGGCTGTGTACATAAGTCC
2086  ACTTTGAATATAGATTATACTGATTATGATGATTCTATCCAGAACTTCAAGAAGTGGAAA
2087  ATTAGCTTACAGGAGATGGCCCAAGTACGTAGAAAGTTTGAGTTTTTTACGTATGTTAGA
2088  TTTGACTCAGAAATAACAATTGTGCCAAGTATAGCTGGACAGGGTAGTGATGTCGGACAT
2089  GTTGTCATGCAATACATGTTCGTCACCTGGCGCACCCTCCCAGAAAAGAGAGATGAT
2090  TACACATGGCAATCTGGCACCAATGCATCTGTATTCTGGCAGTATGGTCAAGTTTACCCT
2091  AGGTTTTCTCTACCATTTCTTAGCATTGCTTCCGCATATTACATGTTTTATGATGGTTAT
2092  GAAGAAGGCTCTACAAATGCACGCTATGGAACAACAGTCACAAATGACATGGGTACATTA
2093  TGCTTTAGAATAGTTACTGAAGAACACACCAACAAAGTTAAGGTCACAACTAGAGTTTAC
2094  CACAAAGCTAAACATGTTAAAGCATGGTGTCCTAGACCTCCCAGGGCTGTGGAGTACACC
2095  AATGTGCATGTCACAAATTACAAACCAAAAGCAGGAGCAGAGATTGTGGCTTCTGTCAGA
2096  CCTAGAGACAATGTTAGACAAGTAAGAAATTAC
2097  >138_HRV7
2098  AATCCTGTAGAAAGATATGTAGATGAAGTTTTGAATGAAGTCCTTGTAGTACCCAATATC
2099  AATGAAAGTAATCCAACTACATCCAACTCAGCACCTGCACTGGACGCTGCAGAAACTGGC
2100  CATACCAGTGGTGTACAACCAGAAGACATGATTGAGACCCGTTATGTCCAAACATCACAG
2101  ACTAGAGATGAAATGAGCATTGAAAGCTTCCTTGGCAGGTCAGGTTGTATACACATGTCA
2102  ACTATGAATATAAATTATGAAAATTATGATGATGCTCCTGAAAATTTTACCAAATGGAAA
2103  ATAAGTTTACAAGAGATGGCTCAAATACGTAGGAAATTTGAATTATTCACCTATGTAAGA
2104  TTTGATTCAGAAGTGACAATTGTACCATGTATAGCTGGTCAAAGTGGAGATGTGGGACAT
2105  GTAGTTATGCAGTATATGTATGTCCCACCTGGAGCCCCTCTACCCACAAAAAGAAATGAC
2106  TACACATGGCAGTCCGGCACTAATGCATCAGTATTCTGGCAACATGGTCAAACTTACCCC
2107  AGATTCTCATTACCATTCCTTAGTATAGCATCCGCATATTATATGTTTTATGATGGATAT
2108  GATGGTGACTCCACACAATCACATTATGGCACCACAGTAGTTAATGACATGGGCACATTA
2109  TGCTTTAGGATAGTGACTGAAGAACACACTAGCAGGGTAAAGGTTACTACTAGAATCTAT
2110  CATAAGGCTAAACATGTTAAAGCTTGGTGTCCAAGACCTCCTAGGGCAGTAGAATATACA
2111  AATGCACATGTGACCAATTATAAACCCACTGATGGAGAAGTTACTACTGCCATTAGGCAT
2112  AGAGATAATGTTAGAGCCATCCAAAATTTT
2113  >139_HRV73b
2114  AATCCTGTAGAAAGATATGTAGATGAAGTTTTGAATGAAGTCCTTGTAGTACCCAATATC
2115  AATGAAAGTAATCCAACTACATCCAACTCAGCACCTGCACTGGACGCTGCAGAAACTGGC
2116  CATACCAGTGGTGTACAACCAGAAGACATGATTGAGACCCGTTATGTCCAAACATCACAG
2117  ACTAGAGATGAAATGAGCATTGAAAGCTTCCTTGGCAGGTCAGGTTGTATACACATGTCA
2118  ACTATGAATATAAATTATGAAAATTATGATGATGCTCCTGAAAATTTTACCAAATGGAAA
2119  ATAAGTTTACAAGAGATGGCTCAAATACGTAGGAAATTTGAATTATTCACCTATGTAAGA
2120  TTTGATTCAGAAGTGACAATTGTACCATGTATAGCTGGTCAAAGTGGAGATGTGGGACAT
2121  GTAGTTATGCAGTATATGTATGTCCCACCTGGAGCCCCTCTACCCACAAAAAGAAATGAC
2122  TACACATGGCAGTCCGGCACTAATGCATCAGTATTCTGGCAACATGGTCAAACTTACCCC
2123  AGATTCTCATTACCATTCCTTAGTATAGCATCCGCATATTATATGTTTTATGATGGATAT
2124  GATGGTGACTCCACACAATCACATTATGGCACCACAGTAGTTAATGACATGGGCACATTA
2125  TGCTTTAGGATAGTGACTGAAGAACACACTAGCAGGGTAAAGGTTACTACTAGAATCTAT
2126  CATAAGGCTAAACATGTTAAAGCTTGGTGTCCAAGACCTCCTAGGGCAGTAGAATATACA
2127  AATGCACATGTGACCAATTATAAACCCACTGATGGAGAAGTTACTACTGCCATTAGGCAT
2128  AGAGATAATGTTAGAGCCATCCAAAATTTG
2129  >140_HRV73a
2130  AATCCTGTAGAAAGATATGTAGATGAAGTTTTGAATGAAGTCCTTGTAGTACCCAATATC
2131  AATGAAAGTAATCCAACTACATCCAACTCAGCACCTGCACTGGACGCTGCAGAAACTGGC
2132  CATACCAGTGGTGTACAACCAGAAGACATGATTGAGACCCGTTATGTCCAAACATCACAG
2133  ACTAGAGATGAAATGAGCATTGAAAGCTTCCTTGGCAGGTCAGGTTGTATACACATGTCA
2134  ACTATGAATATAAATTATGAAAATTATGATGATGCTCCTGAAAATTTTACCAAATGGAAA
2135  ATAAGTTTACAAGAGATGGCTCAAATACGTAGGAAATTTGAATTATTCACCTATGTAAGA
2136  TTTGATTCAGAAGTGACAATTGTACCATGTATAGCTGGTCAAAGTGGAGATGTGGGACAT
2137  GTAGTTATGCAGTATATGTATGTCCCACCTGGAGCCCCTCTACCCACAAAAAGAAATGAC
2138  TACACATGGCAGTCCGGCACTAATGCATCAGTATTCTGGCAACATGGTCAAACTTACCCC
2139  AGATTCTCATTACCATTCCTTAGTATAGCATCCGCATATTATATGTTTTATGATGGATAT
2140  GATGGTGACTCCACACAATCACATTATGGCACCACAGTAGTTAATGACATGGGCACATTA
2141  TGCTTTAGGATAGTGACTGAAGAACACACTAGCAGGGTAAAGGTTACTACTAGAATCTAT
2142  CATAAGGCTAAACATGTTAAAGCTTGGTGTCCAAGACCTCCTAGGGCAGTAGAATATACA
2143  AATGCACATGTGACCAATTATAAACCCACTGATGGAGAAGTTACTACTGCCATTAGGCAT
2144  AGAGATAATGTTAGAGCCATCCAAAATTTC
2145  >141_HRV61
```

FIG. D1 CONT'D

Rhino_cDNA_DB.fasta                                                    9/20/2007 5:08 PM

```
2146 AACCCTGTGGAAAGATATGTAGATGAAGTTTAAATGAAGTGCTTGTAGTCCCAAACATT
2147 AATCAGAGCAACCCTACAACATCCAACTCAGCACCAGTCTTAGACGCTGCTGAAACAGGT
2148 CATACCAGCAATGTTCAACCGGAGGACACGATTGAAACACGATATGTTCAAACCTCACAG
2149 ACAAGAGATGAAATGAGTGTAGAAAGTTTCTTGGGTAGATCAGGGTGCATACATATGTCA
2150 ACATTAAATATAAACTATGATAACTATGATGATTCTATTGAAAACTTCAAGGTGTGGAAA
2151 ATAAACCTGCAAGAGATGGCACAAATACGTAGAAAATTTGAGTTGTTCACATATGCTAGA
2152 TTTGATTCAGAGATTACAATTGTACCTTGTGTTGCTGGGCAAGGTGGTGACATTGGACAC
2153 GTGGTCATGCAATACATGTATGTTCCACCTGGTGCACCTACACCTGAGAAAAGAAATGAT
2154 TTCACATGGCAATCAGGCACAAATGCATCTGTTTTCTGGCAACATGGTCAAGCTTATCCC
2155 AGATTTTCATTACCATTCCTAAGTATTGCATCTGCATATTATATGTTTTATGATGGTTAT
2156 GATGGAGATTCTGAAATAACGCGCTATGGAACATCAGTGACAAATGATATGGGTGCATTG
2157 TGCTTTAGAATAGTAACTGAACAGCATACAAATCAAGTTAAAATCACAACTAGGATTTAC
2158 CATAAAGCTAAACATGTTAAAGTCTGGTGTCCTAGACCCCCCAGAGCAGTGGAATATACT
2159 AATGTGCATTTGACCAATTACAAGCCCAAAGATAGTGAAAAACAAGTTACCACTTTCATC
2160 AAACCTAGAGCTAACTTAAGAGAGATTAGAACATTT
2161 >142_HRV61a
2162 AACCCTGTGGAAAGATATGTAGATGAAGTTTAAATGAAGTGCTTGTAGTCCCAAACATT
2163 AATCAGAGCAACCCTACAACATCCAACTCAGCACCAGTCTTAGACGCTGCTGAAACAGGT
2164 CATACCAGCAATGTTCAACCGGAGGACACGATTGAAACACGATATGTTCAAACCTCACAG
2165 ACAAGAGATGAAATGAGTGTAGAAAGTTTCTTGGGTAGATCAGGGTGCATACATATGTCA
2166 ACATTAAATATAAACTATGATAACTATGATGATTCTATTGAAAACTTCAAGGTGTGGAAA
2167 ATAAACCTGCAAGAGATGGCACAAATACGTAGAAAATTTGAGTTGTTCACATATGCTAGA
2168 TTTGATTCAGAGATTACAATTGTACCTTGTGTTGCTGGGCAAGGTGGTGACATTGGACAC
2169 GTGGTCATGCAATACATGTATGTTCCACCTGGTGCACCTACACCTGAGAAAAGAAATGAT
2170 TTCACATGGCAATCAGGCACAAATGCATCTGTTTTCTGGCAACATGGTCAAGCTTATCCC
2171 AGATTTTCATTACCATTCCTAAGTATTGCATCTGCATATTATATGTTTTATGATGGTTAT
2172 GATGGAGATTCTGAAATAACGCGCTATGGAACATCAGTGACAAATGATATGGGTGCATTG
2173 TGCTTTAGAATAGTAACTGAACAGCATACAAATCAAGTTAAAATCACAACTAGGATTTAC
2174 CATAAAGCTAAACATGTTAAAGTCTGGTGTCCTAGACCCCCCAGAGCAGTGGAATATACT
2175 AATGTGCATTTGACCAATTACAAGCCCAAAGATAGTGAAAAACAAGTTACCACTTTCATC
2176 AAACCTAGAGCTAACTTAAGAGAGATTAGAACATTT
2177 >143_HRV61b
2178 AACCCTGTGGAAAGATATGTAGATGAAGTTTAAATGAAGTGCTTGTAGTCCCAAACATT
2179 AATCAGAGCAACCCTACAACATCCAACTCAGCACCAGTCTTAGACGCTGCTGAAACAGGT
2180 CATACCAGCAATGTTCAACCGGAGGACACGATTGAAACACGATATGTTCAAACCTCACAG
2181 ACAAGAGATGAAATGAGTGTAGAAAGTTTCTTGGGTAGATCAGGGTGCATACATATGTCA
2182 ACATTAAATATAAACTATGATAACTATGATGATTCTATTGAAAACTTCAAGGTGTGGAAA
2183 ATAAACCTGCAAGAGATGGCACAAATACGTAGAAAATTTGAGTTGTTCACATATGCTAGA
2184 TTTGATTCAGAGATTACAATTGTACCTTGTGTTGCTGGGCAAGGTGGTGACATTGGACAC
2185 GTGGTCATGCAATACATGTATGTTCCACCTGGTGCACCTACACCTGAGAAAAGAAATGAT
2186 TTCACATGGCAATCAGGCACAAATGCATCTGTTTTCTGGCAACATGGTCAAGCTTATCCC
2187 AGATTTTCATTACCATTCCTAAGTATTGCATCTGCATATTATATGTTTTATGATGGTTAT
2188 GATGGAGATTCTGAAATAACGCGCTATGGAACATCAGTGACAAATGATATGGGTGCATTG
2189 TGCTTTAGAATAGTAACTGAACAGCATACAAATCAAGTTAAAATCACAACTAGGATTTAC
2190 CATAAAGCTAAACATGTTAAAGTCTGGTGTCCTAGACCCCCCAGAGCAGTGGAATATACT
2191 AATGTGCATTTGACCAATTACAAGCCCAAAGATAGTGAAAAACAAGTTACCACTTTCATC
2192 AAACCTAGAGCTAACTTAAGAGAGATTAGAACATTT
2193 >144_HRV96
2194 AACCCTGTAGAGAGATATGTAGATGAAGTCTTGAATGAGGTTCTTGTAGTCCCTAATATT
2195 AATGAAAGTTACCCAACAACTTCCAATTCAGCCCCAGTGCTAGATGCCGCTGAAACAGGT
2196 CATACTAGCAATGTCCAACCAGAGGATATGATTGAGACTCGATATGTTCAGACATCGCAG
2197 ACGAGAGATGAAATGAGCATTGAGAGCTTTTGGGTAGATCAGGGTGTATACACATGTCA
2198 ACATTAAACATAGATTATGACAATTATGATGACTCCCCTAAGAATTTTAAGGTGTGGAAA
2199 ATAAATCTACAAGAAATGGCTCAAATTCGCAGGAAGTTTGAACTGTTCACTTATGCTAGA
2200 TTTGATTCAGAGATAACAATTGTTCCATGTGTTGCTGTGCAGAGTGGTGATATTGGTCAT
2201 GTGGTCATGCAATATATGTATGTTCCACCAGGTGCCCCCACACCTGAGAAGAGAGATGAC
2202 TTTACATGGCAATCAGGCACAAATGCATCTGTGTTTTGGCAGCACGGGCAAGCATATCCT
2203 AGATTTTCACTGCCTTTCCTTAGTATTGCCTCTGCATATTACATGTTTTATGATGGATAT
2204 GATGGTGACTCTGAATCAACACGCTATGGAACATCTGTTACCAATGACATGGGCACTTTA
2205 TGTTTTAGAATAGTGACAGAGGAACACACCAACAAGGTCAAAATTACAACCAGAGTTTAC
2206 CACAAAGCTAAACATGTTAAGGTGTGGTGCCCGAGACCCCCTAGAGCAGTTGAATACACA
2207 AATGTGCATCTCACAAATTATAAACCCAACAATGAGGTTACCACTTTTATCAAACCTAGA
2208 GAAAATCTAAGGGATATTAGAAATTTT
2209 >145_HRV96b
2210 AACCCTGTAGAGAGATATGTAGATGAAGTCTTGAATGAGGTTCTTGTAGTCCCTAATATT
```

Rhino cDNA DB.fasta                                                    9/20/2007 5:08 PM

```
2211 AATGAAAGTTACCCAACAACTTCCAATTCAGCCCCAGTGCTAGATGCCGCTGAAACAGGT
2212 CATACTAGCAATGTCCAACCAGAGGATATGATTGAGACTCGATATGTTCAGACATCGCAG
2213 ACGAGAGATGAAATGAGCATTGAGAGCTTTTTGGGTAGATCAGGGTGTATACACATGTCA
2214 ACATTAAACATAGATTATGACAATTATGATGACTCCCCTAAGAATTTTAAGGTGTGGAAA
2215 ATAAATCTACAAGAAATGGCTCAAATTCGCAGGAAGTTTGAACTGTTCACTTATGCTAGA
2216 TTTGATTCAGAGATAACAATTGTTCCATGTGTTGCTGTGCAGAGTGGTGATATTGGTCAT
2217 GTGGTCATGCAATATATGTATGTTCCACCAGGTGCCCCCACACCTGAGAAGAGAGATGAC
2218 TTTACATGGCAATCAGGCACAAATGCATCTGTGTTTTGGCAGCACGGGCAAGCATATCCT
2219 AGATTTTCACTGCCTTTCCTTAGTATTGCCTCTGCATATTACATGTTTTATGATGGATAT
2220 GATGGTGACTCTGAATCAACACGCTATGGAACATCTGTTACCAATGACATGGGCACTTTA
2221 TGTTTTAGAATAGTGACAGAGGAACACACCAACAAGGTCAAAATTACAACCAGAGTTTAC
2222 CACAAAGCTAAACATGTTAAGGTGTGGTGCCCGAGACCCCCTAGAGCAGTTGAATACACA
2223 AATGTGCATCTCACAAATTATAAACCCAACAATGAGGTTACCACTTTTATCAAACCTAGA
2224 GAAAATCTAAGGGATATTAGAAATTTA
2225 >146_HRV96a
2226 AACCCTGTAGAGAGATATGTAGATGAAGTCTTGAATGAGGTTCTTGTAGTCCCTAATATT
2227 AATGAAAGTTACCCAACAACTTCCAATTCAGCCCCAGTGCTAGATGCCGCTGAAACAGGT
2228 CATACTAGCAATGTCCAACCAGAGGATATGATTGAGACTCGATATGTTCAGACATCGCAG
2229 ACGAGAGATGAAATGAGCATTGAGAGCTTTTTGGGTAGATCAGGGTGTATACACATGTCA
2230 ACATTAAACATAGATTATGACAATTATGATGACTCCCCTAAGAATTTTAAGGTGTGGAAA
2231 ATAAATCTACAAGAAATGGCTCAAATTCGCAGGAAGTTTGAACTGTTCACTTATGCTAGA
2232 TTTGATTCAGAGATAACAATTGTTCCATGTGTTGCTGTGCAGAGTGGTGATATTGGTCAT
2233 GTGGTCATGCAATATATGTATGTTCCACCAGGTGCCCCCACACCTGAGAAGAGAGATGAC
2234 TTTACATGGCAATCAGGCACAAATGCATCTGTGTTTTGGCAGCACGGGCAAGCATATCCT
2235 AGATTTTCACTGCCTTTCCTTAGTATTGCCTCTGCATATTACATGTTTTATGATGGATAT
2236 GATGGTGACTCTGAATCAACACGCTATGGAACATCTGTTACCAATGACATGGGCACTTTA
2237 TGTTTTAGAATAGTGACAGAGGAACACACCAACAAGGTCAAAATTACAACCAGAGTTTAC
2238 CACAAAGCTAAACATGTTAAGGTGTGGTGCCCGAGACCCCCTAGAGCAGTTGAATACACA
2239 AATGTGCATCTCACAAATTATAAACCCAACAATGAGGTTACCACTTTTATCAAACCTAGA
2240 GAAAATCTAAGGGATATTAGAAATTTC
2241 >90_HRV16a|
2242 AATCCAGTGGAAAGATATGTAGATGAAGTCTTAAATGAAGTGTTAGTAGTGCCCAATATT
2243 AATGAGAGCCACCCTACCACATCAAATGCGGCCCCAGTTTTGGATGCTGCTGAAACAGGA
2244 CATACCAATAAGATACAGCCAGAAGACACTATAGAAACCAGATATGTGCAATCTTCACAG
2245 ACATTGGATGAAATGAGTGTGGAAAGCTTCCTAGGCAGATCGGGGTGCATCCATGAATCA
2246 GTGTTGGATATTGTGGACAATTACAATGATCAAAGTTTCACTAAATGGAAGATAAACCTG
2247 CAAGAAATGGCACAAATTAGAAGAAAATTTGAAATGTTTACTTATGCAAGATTTGACTCT
2248 GAAATTACTATGGTACCAAGTGTAGCAGCCAAAGATGGTCACATTGGTCATATAGTCATG
2249 CAATATATGTATGTACCACCAGGAGCACCTATACCAACAACTAGAAATGACTATGCTTGG
2250 CAATCTGGAACAAATGCATCTGTATTTTGGCAGCATGGGCAACCTTTCCCTCGCTTTTCA
2251 CTTCCCTTTTTGAGTATTGCATCAGCATATTACATGTTTTATGATGGTTATGATGGAGAC
2252 ACATATAAATCCAGATATGGAACTGTAGTCACCAATGACATGGGAACTTTGTGTTCGCGT
2253 ATTGTGACCAGTGAGCAATTACACAAAGTCAAAGTGGTAACAAGGATATATCACAAAGCC
2254 AAACACACCAAAGCTTGGTGCCCAAGACCACCCAGAGCTGTTCAATACTCACATACACAT
2255 ACCACCAACTACAAATTGAGTTCAGAAGTACACAATGATGTGGCTATAAGACCTAGAACA
2256 AATCTAACAACTGTA
2257 >91_HRV16b|
2258 AATCCAGTGGAAAGATATGTAGATGAAGTCTTAAATGAAGTGTTAGTAGTGCCCAATATT
2259 AATGAGAGCCACCCTACCACATCAAATGCGGCCCCAGTTTTGGATGCTGCTGAAACAGGA
2260 CATACCAATAAGATACAGCCAGAAGACACTATAGAAACCAGATATGTGCAATCTTCACAG
2261 ACATTGGATGAAATGAGTGTGGAAAGCTTCCTAGGCAGATCGGGGTGCATCCATGAATCA
2262 GTGTTGGATATTGTGGACAATTACAATGATCAAAGTTTCACTAAATGGAAGATAAACCTG
2263 CAAGAAATGGCACAAATTAGAAGAAAATTTGAAATGTTTACTTATGCAAGATTTGACTCT
2264 GAAATTACTATGGTACCAAGTGTAGCAGCCAAAGATGGTCACATTGGTCATATAGTCATG
2265 CAATATATGTATGTACCACCAGGAGCACCTATACCAACAACTAGAAATGACTATGCTTGG
2266 CAATCTGGAACAAATGCATCTGTATTTTGGCAGCATGGGCAACCTTTCCCTCGCTTTTCA
2267 CTTCCCTTTTTGAGTATTGCATCAGCATATTACATGTTTTATGATGGTTATGATGGAGAC
2268 ACATATAAATCCAGATATGGAACTGTAGTCACCAATGACATGGGAACTTTGTGTTCGCGT
2269 ATTGTGACCAGTGAGCAATTACACAAAGTCAAAGTGGTAACAAGGATATATCACAAAGCC
2270 AAACACACCAAAGCTTGGTGCCCAAGACCACCCAGAGCTGTTCAATACTCACATACACAT
2271 ACCACCAACTACAAATTGAGTTCAGAAGTACACAATGATGTGGCTATAAGACCTAGAACA
2272 AATCTAACAACTGTC
2273 >92_1AYM_A
2274 AATCCAGTGGAAAGATATGTAGATGAAGTCTTAAATGAAGTGTTAGTAGTGCCCAATATT
2275 AATGAGAGCCACCCTACCACATCAAATGCGGCCCCAGTTTTGGATGCTGCTGAAACAGGA
```

FIG. D1 CONT'D

Rhino_cDNA_DB.fasta                                    9/20/2007 5:08 PM

```
2276  CATACCAATAAGATACAGCCAGAAGACACTATAGAAACCAGATATGTGCAATCTTCACAG
2277  ACATTGGATGAAATGAGTGTGGAAAGCTTCCTAGGCAGATCGGGGTGCATCCATGAATCA
2278  GTGTTGGATATTGTGGACAATTACAATGATCAAAGTTTCACTAAATGGAAGATAAACCTG
2279  CAAGAAATGGCACAAATTAGAAGAAAATTTGAAATGTTTACTTATGCAAGATTTGACTCT
2280  GAAATTACTATGGTACCAAGTGTAGCAGCCAAAGATGGTCACATTGGTCATATAGTCATG
2281  CAATATATGTATGTACCACCAGGAGCACCTATACCAACAACTAGAAATGACTATGCTTGG
2282  CAATCTGGAACAAATGCATCTGTATTTTGGCAGCATGGGCAACCTTTCCCTCGCTTTTCA
2283  CTTCCCTTTTTGAGTATTGCATCAGCATATTACATGTTTTATGATGGTTATGATGGAGAC
2284  ACATATAAATCCAGATATGGAACTGTAGTCACCAATGACATGGGAACTTTGTGTTCGCGT
2285  ATTGTGACCAGTGAGCAATTACACAAAGTCAAAGTGGTAACAAGGATATATCACAAAGCC
2286  AAACACACCAAAGCTTGGTGCCCAAGACCACCCAGAGCTGTTCAATACTCACATACACAT
2287  ACCACCAACTACAAATTGAGTTCAGAAGTACACAATGATGTGGCTATAAGACCTAGAACA
2288  AATCTAACAACTGTT
2289  >93_HRV81a|
2290  AACCCAGTGGAGCGGTATGTGGATGAAGTCTTAAATGAGGTATTGGTAGTCCCTAATATT
2291  AATGAAAGCCACCCTACAACATCTAATTCAGCTCCTGTTTTAGATGCAGCTGAAACTGGA
2292  CACACCAGTAATATACAACCTGAGGATACTATTGAGACCAGATATGTACAATCTTCACAG
2293  ACACTGGATGAAATGAGTGTAGAAAGTTTTTTAGGCAGATCAGGTTGCATTCATGAATCC
2294  ATATTGGACATTAAAGAGGATTACAATACCCAGAGCTTTACTAAATGGAAAATTAACTTA
2295  CAAGAGATGGCACAGATTAGGAGAAAGTTTGAAATGTTCACATACACTAGATTTAACTCT
2296  GAGATTACACTGGTACCAAGTATTGCAAACAAGGAAGGTCATATTGGTCATATAGTAATG
2297  CAATACATGTATGTACCACCAGGAGCACCCATTCCAACAACTAGAGAAGACTATGCTTGG
2298  CAATCTGGAACAAATGCATCTATATTCTGGCAACATGGGCAACCCTTTCCCCGGTTTTCA
2299  CTCCCTTTTCTAAGTGTAGCATCAGCATATTACATGTTCTATGATGGATATGATGGTGAT
2300  ACTTATCACTCCAGATACGGGACTGTAGTCACTAATGATATGGGAACATTATGCTCACGG
2301  ATAGTGACAAGTGAGCAAGTGCACAAGGTGAAAATAGTAACAAGAATATATCACAAAGCT
2302  AAGCACACCAAAGCTTGGTGTCCAAGACCACCCAGGGCTGTTCAGTACACACATACACAT
2303  GTAACTAATTATAAATTAGAAACAGATGTCCACACTAGTGTAGCCATAAAACCTAGAACA
2304  AGTCTAACAAATGTG
2305  >94_HRV81b|
2306  AACCCAGTGGAGCGGTATGTGGATGAAGTCTTAAATGAGGTATTGGTAGTCCCTAATATT
2307  AATGAAAGCCACCCTACAACATCTAATTCAGCTCCTGTTTTAGATGCAGCTGAAACTGGA
2308  CACACCAGTAATATACAACCTGAGGATACTATTGAGACCAGATATGTACAATCTTCACAG
2309  ACACTGGATGAAATGAGTGTAGAAAGTTTTTTAGGCAGATCAGGTTGCATTCATGAATCC
2310  ATATTGGACATTAAAGAGGATTACAATACCCAGAGCTTTACTAAATGGAAAATTAACTTA
2311  CAAGAGATGGCACAGATTAGGAGAAAGTTTGAAATGTTCACATACACTAGATTTAACTCT
2312  GAGATTACACTGGTACCAAGTATTGCAAACAAGGAAGGTCATATTGGTCATATAGTAATG
2313  CAATACATGTATGTACCACCAGGAGCACCCATTCCAACAACTAGAGAAGACTATGCTTGG
2314  CAATCTGGAACAAATGCATCTATATTCTGGCAACATGGGCAACCCTTTCCCCGGTTTTCA
2315  CTCCCTTTTCTAAGTGTAGCATCAGCATATTACATGTTCTATGATGGATATGATGGTGAT
2316  ACTTATCACTCCAGATACGGGACTGTAGTCACTAATGATATGGGAACATTATGCTCACGG
2317  ATAGTGACAAGTGAGCAAGTGCACAAGGTGAAAATAGTAACAAGAATATATCACAAAGCT
2318  AAGCACACCAAAGCTTGGTGTCCAAGACCACCCAGGGCTGTTCAGTACACACATACACAT
2319  GTAACTAATTATAAATTAGAAACAGATGTCCACACTAGTGTAGCCATAAAACCTAGAACA
2320  AGTCTAACAAATGTC
2321  >95_HRV81
2322  AACCCAGTGGAGCGGTATGTGGATGAAGTCTTAAATGAGGTATTGGTAGTCCCTAATATT
2323  AATGAAAGCCACCCTACAACATCTAATTCAGCTCCTGTTTTAGATGCAGCTGAAACTGGA
2324  CACACCAGTAATATACAACCTGAGGATACTATTGAGACCAGATATGTACAATCTTCACAG
2325  ACACTGGATGAAATGAGTGTAGAAAGTTTTTTAGGCAGATCAGGTTGCATTCATGAATCC
2326  ATATTGGACATTAAAGAGGATTACAATACCCAGAGCTTTACTAAATGGAAAATTAACTTA
2327  CAAGAGATGGCACAGATTAGGAGAAAGTTTGAAATGTTCACATACACTAGATTTAACTCT
2328  GAGATTACACTGGTACCAAGTATTGCAAACAAGGAAGGTCATATTGGTCATATAGTAATG
2329  CAATACATGTATGTACCACCAGGAGCACCCATTCCAACAACTAGAGAAGACTATGCTTGG
2330  CAATCTGGAACAAATGCATCTATATTCTGGCAACATGGGCAACCCTTTCCCCGGTTTTCA
2331  CTCCCTTTTCTAAGTGTAGCATCAGCATATTACATGTTCTATGATGGATATGATGGTGAT
2332  ACTTATCACTCCAGATACGGGACTGTAGTCACTAATGATATGGGAACATTATGCTCACGG
2333  ATAGTGACAAGTGAGCAAGTGCACAAGGTGAAAATAGTAACAAGAATATATCACAAAGCT
2334  AAGCACACCAAAGCTTGGTGTCCAAGACCACCCAGGGCTGTTCAGTACACACATACACAT
2335  GTAACTAATTATAAATTAGAAACAGATGTCCACACTAGTGTAGCCATAAAACCTAGAACA
2336  AGTCTAACAAATGTT
2337  >147_HRV
2338  AACCCTGTTGAGAATTATATAGATGAAGTTCTTAATGAAGTTTTAGTTGTCCCAAATATT
2339  AATAGTAGTAACCCCACAACATCAAATTCTGCCCCAGCATTAGATGCTGCAGAAACAGGG
2340  CACACTAGTAGTGTTCAACCAGAGGATGTCATTGAAACTAGGTATGTGCAGACATCACAA
```

FIG. D1 CONT'D

Rhino_cDNA_DB.fasta                                                9/20/2007 5:08 PM

```
2341 ACAAGAGATGAAATGAGTTTAGAGAGTTTTCTTGGCAGATCAGGATGCATACATGAATCT
2342 AAATTAGAGGTTACACTTGCAAATTATAACAAGGAGAATTTTACAGTGTGGGCTATTAAT
2343 ATACAAGAAATGGCTCAAATTAGAAGGAAATTTGAATTGTTCACCTATACTAGGTTTGAT
2344 TCTGAAATAACCCTAGTTCCATGCATTTCCGCCCTTAGTCAGGACATTGGACACATCACA
2345 ATGCAATACATGTATGTTCCACCTGGTGCACCGGTGCCCAATAGTAGGGACGATTATGCA
2346 TGGCAGTCTGGCACTAATGCCTCTGTTTTCTGGCAACATGGACAGGCTTATCCAAGATTT
2347 TCCTTACCTTTCCTAAGTGTGGCATCTGCTTATTACATGTTTTATGATGGGTATGATGAA
2348 CAAGATCAAAACTATGGTACAGCAAGCACAAATAACATGGGGTCACTATGCTCTAGGATA
2349 GTAACAGAGAAACACATTCATAAGGTACATATAATGACAAGAATCTATCACAAGGCTAAA
2350 CATGTCAAGGCATGGTGTCCACGCCCACCCAGAGCGCTTGAGTATACTCGTGCTCACCGC
2351 ACTAATTTTAAAATTGAGGATAGGAGTATTCAGACAGCAATTGTGACCAGACCAATTATC
2352 ACTACAGCT
2353 >148_HRV2a|
2354 AACCCTGTTGAGAATTATATAGATGAAGTTCTTAATGAAGTTTTAGTTGTCCCAAATATT
2355 AATAGTAGTAACCCCACAACATCAAATTCTGCCCCAGCATTAGATGCTGCAGAAACAGGG
2356 CACACTAGTAGTGTTCAACCAGAGGATGTCATTGAAACTAGGTATGTGCAGACATCACAA
2357 ACAAGAGATGAAATGAGTTTAGAGAGTTTTCTTGGCAGATCAGGATGCATACATGAATCT
2358 AAATTAGAGGTTACACTTGCAAATTATAACAAGGAGAATTTTACAGTGTGGGCTATTAAT
2359 ATACAAGAAATGGCTCAAATTAGAAGGAAATTTGAATTGTTCACCTATACTAGGTTTGAT
2360 TCTGAAATAACCCTAGTTCCATGCATTTCCGCCCTTAGTCAGGACATTGGACACATCACA
2361 ATGCAATACATGTATGTTCCACCTGGTGCACCGGTGCCCAATAGTAGGGACGATTATGCA
2362 TGGCAGTCTGGCACTAATGCCTCTGTTTTCTGGCAACATGGACAGGCTTATCCAAGATTT
2363 TCCTTACCTTTCCTAAGTGTGGCATCTGCTTATTACATGTTTTATGATGGGTATGATGAA
2364 CAAGATCAAAACTATGGTACAGCAAGCACAAATAACATGGGGTCACTATGCTCTAGGATA
2365 GTAACAGAGAAACACATTCATAAGGTACATATAATGACAAGAATCTATCACAAGGCTAAA
2366 CATGTCAAGGCATGGTGTCCACGCCCACCCAGAGCGCTTGAGTATACTCGTGCTCACCGC
2367 ACTAATTTTAAAATTGAGGATAGGAGTATTCAGACAGCAATTGTGACCAGACCAATTATC
2368 ACTACAGCA
2369 >149_HRV2b|
2370 AACCCTGTTGAGAATTATATAGATGAAGTTCTTAATGAAGTTTTAGTTGTCCCAAATATT
2371 AATAGTAGTAACCCCACAACATCAAATTCTGCCCCAGCATTAGATGCTGCAGAAACAGGG
2372 CACACTAGTAGTGTTCAACCAGAGGATGTCATTGAAACTAGGTATGTGCAGACATCACAA
2373 ACAAGAGATGAAATGAGTTTAGAGAGTTTTCTTGGCAGATCAGGATGCATACATGAATCT
2374 AAATTAGAGGTTACACTTGCAAATTATAACAAGGAGAATTTTACAGTGTGGGCTATTAAT
2375 ATACAAGAAATGGCTCAAATTAGAAGGAAATTTGAATTGTTCACCTATACTAGGTTTGAT
2376 TCTGAAATAACCCTAGTTCCATGCATTTCCGCCCTTAGTCAGGACATTGGACACATCACA
2377 ATGCAATACATGTATGTTCCACCTGGTGCACCGGTGCCCAATAGTAGGGACGATTATGCA
2378 TGGCAGTCTGGCACTAATGCCTCTGTTTTCTGGCAACATGGACAGGCTTATCCAAGATTT
2379 TCCTTACCTTTCCTAAGTGTGGCATCTGCTTATTACATGTTTTATGATGGGTATGATGAA
2380 CAAGATCAAAACTATGGTACAGCAAGCACAAATAACATGGGGTCACTATGCTCTAGGATA
2381 GTAACAGAGAAACACATTCATAAGGTACATATAATGACAAGAATCTATCACAAGGCTAAA
2382 CATGTCAAGGCATGGTGTCCACGCCCACCCAGAGCGCTTGAGTATACTCGTGCTCACCGC
2383 ACTAATTTTAAAATTGAGGATAGGAGTATTCAGACAGCAATTGTGACCAGACCAATTATC
2384 ACTACAGCG
2385 >150_HRV49a
2386 AATCCTGTTGAACACTACATAGATGAGGTCCTTAATGAGGTTTTAGTTGTTCCAAATATT
2387 AATAGTAGTCACCCCACGACATCAAACTCTGCTCCAGCATTAGATGCTGCAGAAACAGGG
2388 CACACTAGCAATGTGCAACCTGAAGATGTCATTGAAACCAGATATGTACAGACATCACAA
2389 ACAAGAGATGAAATGAGTTTAGAGAGTTTTCTTGGTAGGTCAGGGTGTATACATGAATCC
2390 AAACTAGAGGTCACACTTACAAATTACAATGAAAATAATTTCAAAGTATGGAACATCAAT
2391 TTGCAAGAAATGGCCCAGATCAGAAGAAAATTTGAACTGTTTACTTACACTAGATTCGAT
2392 TCTGAAATAACCTTGGTTCCATGCATTTCTGCACTTAGCAAGGATATTGGACACATTACA
2393 ATGCAATACATGTATGTGCCGCCAGGTGCACCTGTACCAAAGAGCAGAGATGATTATGCA
2394 TGGCAGTCTGGCACTAATGCATCTGTTTTCTGGCAACATGGGCAAGCATACCCAAGATTT
2395 TCTCTACCCTTTTTGAGTGTAGCTTCAGCTTACTACATGTTTTATGATGGATATAATGAA
2396 CAGGGCCAAAATTATGGTACGGTAAGTACAAACAACATGGGATCATTATGCTCTAGGATA
2397 GTAACAGAGAAACACATTCACAGTATGCATATCATGACAAGAATCTATCATAAAGCTAAA
2398 CACGTCAAAGCATGGTGTCCGCGCCCACCCAGAGCACTTGAATATACTCGCGCTCACCGT
2399 ACTAATTTCAAAGTTGAAGACAGAGACATTAAAACAGGAATCACATCCAGAGCAATTATT
2400 ACAACAGCG
2401 >151_HRV49b
2402 AATCCTGTTGAACACTACATAGATGAGGTCCTTAATGAGGTTTTAGTTGTTCCAAATATT
2403 AATAGTAGTCACCCCACGACATCAAACTCTGCTCCAGCATTAGATGCTGCAGAAACAGGG
2404 CACACTAGCAATGTGCAACCTGAAGATGTCATTGAAACCAGATATGTACAGACATCACAA
2405 ACAAGAGATGAAATGAGTTTAGAGAGTTTTCTTGGTAGGTCAGGGTGTATACATGAATCC
```

FIG. D1 CONT'D

Rhino cDNA DB.fasta                                    9/20/2007 5:08 PM

```
2406 AAACTAGAGGTCACACTTACAAATTACAATGAAAATAATTTCAAAGTATGGAACATCAAT
2407 TTGCAAGAAATGGCCCAGATCAGAAGAAAATTTGAACTGTTTACTTACACTAGATTCGAT
2408 TCTGAAATAACCTTGGTTCCATGCATTTCTGCACTTAGCAAGGATATTGGACACATTACA
2409 ATGCAATACATGTATGTGCCGCCAGGTGCACCTGTACCAAAGAGCAGAGATGATTATGCA
2410 TGGCAGTCTGGCACTAATGCATCTGTTTTCTGGCAACATGGGCAAGCATACCCAAGATTT
2411 TCTCTACCCTTTTTGAGTGTAGCTTCAGCTTACTACATGTTTTATGATGGATATAATGAA
2412 CAGGGCCAAAATTATGGTACGGTAAGTACAAACAACATGGGATCATTATGCTCTAGGATA
2413 GTAACAGAGAAACACATTCACAGTATGCATATCATGACAAGAATCTATCATAAAGCTAAA
2414 CACGTCAAAGCATGGTGTCCGCGCCCACCCAGAGCACTTGAATATACTCGCGCTCACCGT
2415 ACTAATTTCAAAGTTGAAGACAGAGACATTAAAACAGGAATCACATCCAGAGCAATTATT
2416 ACAACAGCA
2417 >152_HRV49
2418 AATCCTGTTGAACACTACATAGATGAGGTCCTTAATGAGGTTTTAGTTGTTCCAAATATT
2419 AATAGTAGTCACCCCACGACATCAAACTCTGCTCCAGCATTAGATGCTGCAGAAACAGGG
2420 CACACTAGCAATGTGCAACCTGAAGATGTCATTGAAACCAGATATGTACAGACATCACAA
2421 ACAAGAGATGAAATGAGTTTAGAGAGTTTCTTGGTAGGTCAGGGTGTATACATGAATCC
2422 AAACTAGAGGTCACACTTACAAATTACAATGAAAATAATTTCAAAGTATGGAACATCAAT
2423 TTGCAAGAAATGGCCCAGATCAGAAGAAAATTTGAACTGTTTACTTACACTAGATTCGAT
2424 TCTGAAATAACCTTGGTTCCATGCATTTCTGCACTTAGCAAGGATATTGGACACATTACA
2425 ATGCAATACATGTATGTGCCGCCAGGTGCACCTGTACCAAAGAGCAGAGATGATTATGCA
2426 TGGCAGTCTGGCACTAATGCATCTGTTTTCTGGCAACATGGGCAAGCATACCCAAGATTT
2427 TCTCTACCCTTTTTGAGTGTAGCTTCAGCTTACTACATGTTTTATGATGGATATAATGAA
2428 CAGGGCCAAAATTATGGTACGGTAAGTACAAACAACATGGGATCATTATGCTCTAGGATA
2429 GTAACAGAGAAACACATTCACAGTATGCATATCATGACAAGAATCTATCATAAAGCTAAA
2430 CACGTCAAAGCATGGTGTCCGCGCCCACCCAGAGCACTTGAATATACTCGCGCTCACCGT
2431 ACTAATTTCAAAGTTGAAGACAGAGACATTAAAACAGGAATCACATCCAGAGCAATTATT
2432 ACAACAGCT
2433 >153_HRV23a
2434 AATCCAATTGAGAACTATGTAGATGAAGTTCTTAATGAAGTCTTAGTTGTTCCCAATATC
2435 AATAGTAGTCATCCCACAACATCAAACTCTGCTCCAGCATTAGACGCTGCGGAAACGGGT
2436 CACACTAGTAATGTTCAACCAGAAGATGTCATTGAAACCAGGTACGTTCAAACATCACAA
2437 ACAAGAGATGAAATGAGTTTAGAAAGTTTCCTTGGTAGGTCAGGGTGTATACATGAATCT
2438 AAATTAAAAGTTGAGATCGGAAACTATGATGAAAACAATTTTAATACTTGGAATATTAAT
2439 TTACAGGAAATGGCCCAAATCAGAAGAAAGTTTGAACTGTTTACTTACACTAGATTTGAT
2440 TCTGAAATTACTTTGGTTCCATGCATTTCTGCTCTTCAAGATATTGGTCACATCACA
2441 ATGCAGTATATGTATGTCCCACCAGGTGCTCCAATACCGGAAAGTAGAAATGACTATGCA
2442 TGGCAATCTGGAACAAATGCGTCCATTTTTTGGCAACATGGACAAACATATCCAAGGTTC
2443 TCCTTACCCTTTTTGAGTGTGGCATCTGCTTATTACATGTTTTATGATGGATACAATGAG
2444 AAAGGCACGCATTATGGAACAGTTAGCACAAACAACATGGGCACATTGTGCTCCAGAGTG
2445 GTAACAGAGAAACACATTCATGATATGCGGATAATGACAAGGGTCTACCACAAAGCTAAA
2446 CATGTCAAAGCATGGTGTCCGCGGCCACCCAGAGCACTTGAATACACACGCGCTCACCGT
2447 ACTAATTTCAAAATTGAAGGTGAAAATGTCAAATCAAGGGTTGCACATAGACCTGCAGTG
2448 ATAACAGCG
2449 >154_HRV23b
2450 AATCCAATTGAGAACTATGTAGATGAAGTTCTTAATGAAGTCTTAGTTGTTCCCAATATC
2451 AATAGTAGTCATCCCACAACATCAAACTCTGCTCCAGCATTAGACGCTGCGGAAACGGGT
2452 CACACTAGTAATGTTCAACCAGAAGATGTCATTGAAACCAGGTACGTTCAAACATCACAA
2453 ACAAGAGATGAAATGAGTTTAGAAAGTTTCCTTGGTAGGTCAGGGTGTATACATGAATCT
2454 AAATTAAAAGTTGAGATCGGAAACTATGATGAAAACAATTTTAATACTTGGAATATTAAT
2455 TTACAGGAAATGGCCCAAATCAGAAGAAAGTTTGAACTGTTTACTTACACTAGATTTGAT
2456 TCTGAAATTACTTTGGTTCCATGCATTTCTGCTCTTAGTCAAGATATTGGTCACATCACA
2457 ATGCAGTATATGTATGTCCCACCAGGTGCTCCAATACCGGAAAGTAGAAATGACTATGCA
2458 TGGCAATCTGGAACAAATGCGTCCATTTTTTGGCAACATGGACAAACATATCCAAGGTTC
2459 TCCTTACCCTTTTTGAGTGTGGCATCTGCTTATTACATGTTTTATGATGGATACAATGAG
2460 AAAGGCACGCATTATGGAACAGTTAGCACAAACAACATGGGCACATTGTGCTCCAGAGTG
2461 GTAACAGAGAAACACATTCATGATATGCGGATAATGACAAGGGTCTACCACAAAGCTAAA
2462 CATGTCAAAGCATGGTGTCCGCGGCCACCCAGAGCACTTGAATACACACGCGCTCACCGT
2463 ACTAATTTCAAAATTGAAGGTGAAAATGTCAAATCAAGGGTTGCACATAGACCTGCAGTG
2464 ATAACAGCA
2465 >155_HRV2
2466 AATCCAATTGAGAACTATGTAGATGAAGTTCTTAATGAAGTCTTAGTTGTTCCCAATATC
2467 AATAGTAGTCATCCCACAACATCAAACTCTGCTCCAGCATTAGACGCTGCGGAAACGGGT
2468 CACACTAGTAATGTTCAACCAGAAGATGTCATTGAAACCAGGTACGTTCAAACATCACAA
2469 ACAAGAGATGAAATGAGTTTAGAAAGTTTCCTTGGTAGGTCAGGGTGTATACATGAATCT
2470 AAATTAAAAGTTGAGATCGGAAACTATGATGAAAACAATTTTAATACTTGGAATATTAAT
```

FIG. D1 CONT'D

Rhino cDNA DB.fasta                                             9/20/2007 5:08 PM

```
2471 TTACAGGAAATGGCCCAAATCAGAAGAAAGTTTGAACTGTTTACTTACACTAGATTTGAT
2472 TCTGAAATTACTTTGGTTCCATGCATTTCTGCTCTTAGTCAAGATATTGGTCACATCACA
2473 ATGCAGTATATGTATGTCCCACCAGGTGCTCCAATACCGGAAAGTAGAAATGACTATGCA
2474 TGGCAATCTGGAACAAATGCGTCCATTTTTTGGCAACATGGACAAACATATCCAAGGTTC
2475 TCCTTACCCTTTTTGAGTGTGGCATCTGCTTATTACATGTTTTATGATGGATACAATGAG
2476 AAAGGCACGCATTATGGAACAGTTAGCACAAACAACATGGGCACATTGTGCTCCAGAGTG
2477 GTAACAGAGAAACACATTCATGATATGCGGATAATGACAAGGGTCTACCACAAAGCTAAA
2478 CATGTCAAAGCATGGTGTCCGCGGCCACCCAGAGCACTTGAATACACACGCGCTCACCGT
2479 ACTAATTTCAAAATTGAAGGTGAAAATGTCAAATCAAGGGTTGCACATAGACCTGCAGTG
2480 ATAACAGCT
2481 >156_HRV30a
2482 AACCCGGTTGAAAATTTTGTAGATGAAGTTCTTAGTGAAGTTTTAGTTGTTCCAAACATT
2483 AACAGTAGTCACCCTACTACATCAAACTCTGCTCCGGCATTAGATGCTGCAGAAACAGGA
2484 CATACTAGTAATGTTCAACCTGAAGATGTCATTGAAACTAGATATGTTCAAACATCACAA
2485 ACAAGGGATGAAATGAGTTTAGAAAGCTTTCTTGGTAGATCAGGATGTATACACGAGTCT
2486 AAATTAGAACTTGAGCTTGCACACTATGATAAAAAGAACTTTACCACATGGAATATTAAT
2487 CTTCAAGAAATGGCCCAAATTAGAAGAAAATTTGAGCTATTCACTTACACTAGATTTGAT
2488 TCTGAGATAACCTTGGTTCCGTGTATTTCAGCTCTCAGCCAAGATATCGGACACATTACA
2489 ATGCAGTATATGTATGTTCCACCTGGCGCTCCAATTCCCGAGAGCAGAAATGACTATGCA
2490 TGGCAGTCTGGAACAAATGCATCTGTTTTTTGGCAACACGGACAAACATACCCAAGATTC
2491 TCCCTACCATTTTTGAGTGTAGCATCTGCTTATTACATGTTCTATGATGGATACAATGAG
2492 GGAGGCACAAATTATGGTACAGTGAGCACAAACAACATGGGCACACTGTGTTCCAGAGTG
2493 GTAACAGAAAAACACATTCATGATGTGCGCATAATGACAAGGGTCTACCACAAGGCTAAA
2494 CATGTCAAAGCGTGGTGTCCACGGCCACCTAGGGCGCTTGAGTATACCCGTGCTCATCGC
2495 ACCAATTTTAAAATTGATGGCAGGGAAGTTAAATCAAGGGTTGAACACAGAGCTAGGGTG
2496 ACGACAGCA
2497 >157_HRV30b
2498 AACCCGGTTGAAAATTTTGTAGATGAAGTTCTTAGTGAAGTTTTAGTTGTTCCAAACATT
2499 AACAGTAGTCACCCTACTACATCAAACTCTGCTCCGGCATTAGATGCTGCAGAAACAGGA
2500 CATACTAGTAATGTTCAACCTGAAGATGTCATTGAAACTAGATATGTTCAAACATCACAA
2501 ACAAGGGATGAAATGAGTTTAGAAAGCTTTCTTGGTAGATCAGGATGTATACACGAGTCT
2502 AAATTAGAACTTGAGCTTGCACACTATGATAAAAAGAACTTTACCACATGGAATATTAAT
2503 CTTCAAGAAATGGCCCAAATTAGAAGAAAATTTGAGCTATTCACTTACACTAGATTTGAT
2504 TCTGAGATAACCTTGGTTCCGTGTATTTCAGCTCTCAGCCAAGATATCGGACACATTACA
2505 ATGCAGTATATGTATGTTCCACCTGGCGCTCCAATTCCCGAGAGCAGAAATGACTATGCA
2506 TGGCAGTCTGGAACAAATGCATCTGTTTTTTGGCAACACGGACAAACATACCCAAGATTC
2507 TCCCTACCATTTTTGAGTGTAGCATCTGCTTATTACATGTTCTATGATGGATACAATGAG
2508 GGAGGCACAAATTATGGTACAGTGAGCACAAACAACATGGGCACACTGTGTTCCAGAGTG
2509 GTAACAGAAAAACACATTCATGATGTGCGCATAATGACAAGGGTCTACCACAAGGCTAAA
2510 CATGTCAAAGCGTGGTGTCCACGGCCACCTAGGGCGCTTGAGTATACCCGTGCTCATCGC
2511 ACCAATTTTAAAATTGATGGCAGGGAAGTTAAATCAAGGGTTGAACACAGAGCTAGGGTG
2512 ACGACAGCG
2513 >158_HRV30
2514 AACCCGGTTGAAAATTTTGTAGATGAAGTTCTTAGTGAAGTTTTAGTTGTTCCAAACATT
2515 AACAGTAGTCACCCTACTACATCAAACTCTGCTCCGGCATTAGATGCTGCAGAAACAGGA
2516 CATACTAGTAATGTTCAACCTGAAGATGTCATTGAAACTAGATATGTTCAAACATCACAA
2517 ACAAGGGATGAAATGAGTTTAGAAAGCTTTCTTGGTAGATCAGGATGTATACACGAGTCT
2518 AAATTAGAACTTGAGCTTGCACACTATGATAAAAAGAACTTTACCACATGGAATATTAAT
2519 CTTCAAGAAATGGCCCAAATTAGAAGAAAATTTGAGCTATTCACTTACACTAGATTTGAT
2520 TCTGAGATAACCTTGGTTCCGTGTATTTCAGCTCTCAGCCAAGATATCGGACACATTACA
2521 ATGCAGTATATGTATGTTCCACCTGGCGCTCCAATTCCCGAGAGCAGAAATGACTATGCA
2522 TGGCAGTCTGGAACAAATGCATCTGTTTTTTGGCAACACGGACAAACATACCCAAGATTC
2523 TCCCTACCATTTTTGAGTGTAGCATCTGCTTATTACATGTTCTATGATGGATACAATGAG
2524 GGAGGCACAAATTATGGTACAGTGAGCACAAACAACATGGGCACACTGTGTTCCAGAGTG
2525 GTAACAGAAAAACACATTCATGATGTGCGCATAATGACAAGGGTCTACCACAAGGCTAAA
2526 CATGTCAAAGCGTGGTGTCCACGGCCACCTAGGGCGCTTGAGTATACCCGTGCTCATCGC
2527 ACCAATTTTAAAATTGATGGCAGGGAAGTTAAATCAAGGGTTGAACACAGAGCTAGGGTG
2528 ACGACAGCT
2529 >159_HRV7
2530 AACCCGGTAGAGAATTATGTAGATAGCTTACTAAATGAAGTATTAGTGGTACCTAATATT
2531 CAGCCAAGTACATCTGTTTCAAGTCACTCTGTACCAGCATTGGATGCTGCAGAGACTGGA
2532 CATACTAGTTCTGTTCAACCTGAAGATATGATCGAGACAAGGTATGTCATAACAGACCAA
2533 ACAAGGGATGAAACTAGTATAGAGAGTTTCTTAGGTAGATCTGGATGTATTGCTAAAGTT
2534 AAACTTGACACAACACAGGGTGACTATGACACAGGCAAAGGTGTTGGTTTCACTACATGG
2535 AAAATCAGCTTACAAGAAATGGCACAAATCAGAAGAAAGTTTGAACTATTCACATACACT
```

FIG. D1 CONT'D

Rhino_cDNA_DB.fasta                                                                                                      9/20/2007 5:08 PM

```
2536  AGATTTGATTCTGAGATAACAATAGTCACAGCAGCAGCAGCACAAGGTAATGATATTGGA
2537  CATATAGTTATGCAATTTATGTATGTACCTCCAGGGGCCCCAGTTCCAATAAAACGCGAA
2538  GATTATACATGGCAATCAGGAACAAATGCTTCTATATTTTGGCAGGAGGGTCAACCATAC
2539  CCTAGATTCACAATTCCTTTTATGAGTATTGCATCAGCTTATTATATGTTCTATGATGGA
2540  TATGATGGTGATGATGCGTCATCCAAATATGGTTCCGTAGTAACCAATGACATGGGAACC
2541  ATATGTGTTAGACTAGTTACATCTACACAAAAACACAATTTAAAGATTGTGAGTCGCATT
2542  TACCACAAAGCCAAACATATAAAAGCATGGTGCCCACGCCCACCACGAGCTGTGCCTTAT
2543  CAACACACTCACTCCACCAACTATGTGCCACAAAATGGAGAGGTCGCAACTCAAATCAAA
2544  ACCAGAGCCAATCTTTTCACCCTCAAATCAGCT
2545  >160_HRV7b|
2546  AACCCGGTAGAGAATTATGTAGATAGCTTACTAAATGAAGTATTAGTGGTACCTAATATT
2547  CAGCCAAGTACATCTGTTTCAAGTCACTCTGTACCAGCATTGGATGCTGCAGAGACTGGA
2548  CATACTAGTTCTGTTCAACCTGAAGATATGATCGAGACAAGGTATGTCATAACAGACCAA
2549  ACAAGGGATGAAACTAGTATAGAGAGTTTCTTAGGTAGATCTGGATGTATTGCTAAAGTT
2550  AAACTTGACACAACACAGGGTGACTATGACACAGGCAAAGGTGTTGGTTTCACTACATGG
2551  AAAATCAGCTTACAAGAAATGGCACAAATCAGAAGAAAGTTTGAACTATTCACATACACT
2552  AGATTTGATTCTGAGATAACAATAGTCACAGCAGCAGCAGCACAAGGTAATGATATTGGA
2553  CATATAGTTATGCAATTTATGTATGTACCTCCAGGGGCCCCAGTTCCAATAAAACGCGAA
2554  GATTATACATGGCAATCAGGAACAAATGCTTCTATATTTTGGCAGGAGGGTCAACCATAC
2555  CCTAGATTCACAATTCCTTTTATGAGTATTGCATCAGCTTATTATATGTTCTATGATGGA
2556  TATGATGGTGATGATGCGTCATCCAAATATGGTTCCGTAGTAACCAATGACATGGGAACC
2557  ATATGTGTTAGACTAGTTACATCTACACAAAAACACAATTTAAAGATTGTGAGTCGCATT
2558  TACCACAAAGCCAAACATATAAAAGCATGGTGCCCACGCCCACCACGAGCTGTGCCTTAT
2559  CAACACACTCACTCCACCAACTATGTGCCACAAAATGGAGAGGTCGCAACTCAAATCAAA
2560  ACCAGAGCCAATCTTTTCACCCTCAAATCAGCA
2561  >161_HRV7a|
2562  AACCCGGTAGAGAATTATGTAGATAGCTTACTAAATGAAGTATTAGTGGTACCTAATATT
2563  CAGCCAAGTACATCTGTTTCAAGTCACTCTGTACCAGCATTGGATGCTGCAGAGACTGGA
2564  CATACTAGTTCTGTTCAACCTGAAGATATGATCGAGACAAGGTATGTCATAACAGACCAA
2565  ACAAGGGATGAAACTAGTATAGAGAGTTTCTTAGGTAGATCTGGATGTATTGCTAAAGTT
2566  AAACTTGACACAACACAGGGTGACTATGACACAGGCAAAGGTGTTGGTTTCACTACATGG
2567  AAAATCAGCTTACAAGAAATGGCACAAATCAGAAGAAAGTTTGAACTATTCACATACACT
2568  AGATTTGATTCTGAGATAACAATAGTCACAGCAGCAGCAGCACAAGGTAATGATATTGGA
2569  CATATAGTTATGCAATTTATGTATGTACCTCCAGGGGCCCCAGTTCCAATAAAACGCGAA
2570  GATTATACATGGCAATCAGGAACAAATGCTTCTATATTTTGGCAGGAGGGTCAACCATAC
2571  CCTAGATTCACAATTCCTTTTATGAGTATTGCATCAGCTTATTATATGTTCTATGATGGA
2572  TATGATGGTGATGATGCGTCATCCAAATATGGTTCCGTAGTAACCAATGACATGGGAACC
2573  ATATGTGTTAGACTAGTTACATCTACACAAAAACACAATTTAAAGATTGTGAGTCGCATT
2574  TACCACAAAGCCAAACATATAAAAGCATGGTGCCCACGCCCACCACGAGCTGTGCCTTAT
2575  CAACACACTCACTCCACCAACTATGTGCCACAAAATGGAGAGGTCGCAACTCAAATCAAA
2576  ACCAGAGCCAATCTTTTCACCCTCAAATCAGCG
2577  >162_HRV88
2578  AATCCAGTAGAAAACTATGTAGATAACTTGTTAAACGAAGTGCTAGTAGTTCCTAACATT
2579  CAACCTAGCACATCCGTTTCAAGTCACTCTGTGCCAGCTCTGGATGCTGCGGAAACAGGG
2580  CATACTAGTTCTGTTCAACCTGAAGATATGATAGAAACTAGATATGTTATAACAGATCAA
2581  ACAAGGGATGAAACCAGCATTGAAAGCTTTCTGGGTAGGTCTGGATGCATAGCAAAAATT
2582  AAACTTGACACAAATGAAGGTGATTACGACACAATAGGTGTTGGATTTGTAACATGGAAG
2583  ATTAGCTTGCAAGAAATGGCACAAATCAGGAGAAAATTTGAATTGTTTACATACACTAGA
2584  TTTGACTCAGAAATAACAATAGTCACAGCAGCTGCAGCACAAGGTGATGATACTGGACAT
2585  ATAGTACTGCAATTCATGTATGTGCCTCCAGGTGCACCAATTCCCAAGAAACGTGATGAT
2586  TACACATGGCAGTCAGGAACAAATGCATCTGTGTTCTGGCAAGAAGGACAACCATACCCA
2587  AGATTACCATTCCCTTTATGAGTATTGCATCAGCTTACTATATGTTTTATGATGGATAT
2588  GATGGTGATGATGCATCATCTAGGTATGGCTCAGTGGTAACTAATGATATGGGAACTATA
2589  TGTATTAGATTGGTCACCTCCACCCAAAAGCATAAACTGAATATCATTAGCCGTATATAT
2590  CACAAGGCTAAACATATAAAGGCATGGTGTCCACGCCCACCAAGAGCCGTACCTTATCAG
2591  CACACACACTCCACCAATTATGTACCAACAGATGGGGAAGTAGCAACTCAAATCAAAACC
2592  AGACGAGATGTTTACACTGTTACCACTGCT
2593  >163_HRV88a
2594  AATCCAGTAGAAAACTATGTAGATAACTTGTTAAACGAAGTGCTAGTAGTTCCTAACATT
2595  CAACCTAGCACATCCGTTTCAAGTCACTCTGTGCCAGCTCTGGATGCTGCGGAAACAGGG
2596  CATACTAGTTCTGTTCAACCTGAAGATATGATAGAAACTAGATATGTTATAACAGATCAA
2597  ACAAGGGATGAAACCAGCATTGAAAGCTTTCTGGGTAGGTCTGGATGCATAGCAAAAATT
2598  AAACTTGACACAAATGAAGGTGATTACGACACAATAGGTGTTGGATTTGTAACATGGAAG
2599  ATTAGCTTGCAAGAAATGGCACAAATCAGGAGAAAATTTGAATTGTTTACATACACTAGA
2600  TTTGACTCAGAAATAACAATAGTCACAGCAGCTGCAGCACAAGGTGATGATACTGGACAT
```

FIG. D1 CONT'D

Rhino_cDNA_DB.fasta                                              9/20/2007 5:08 PM

```
2601 ATAGTACTGCAATTCATGTATGTGCCTCCAGGTGCACCAATTCCCAAGAAACGTGATGAT
2602 TACACATGGCAGTCAGGAACAAATGCATCTGTGTTCTGGCAAGAAGGACAACCATACCCA
2603 AGATTTACCATTCCCTTTATGAGTATTGCATCAGCTTACTATATGTTTTATGATGGATAT
2604 GATGGTGATGATGCATCATCTAGGTATGGCTCAGTGGTAACTAATGATATGGGAACTATA
2605 TGTATTAGATTGGTCACCTCCACCCAAAAGCATAAACTGAATATCATTAGCCGTATATAT
2606 CACAAGGCTAAACATATAAAGGCATGGTGTCCACGCCCACCAAGAGCCGTACCTTATCAG
2607 CACACACACTCCACCAATTATGTACCAACAGATGGGGAAGTAGCAACTCAAATCAAAACC
2608 AGACGAGATGTTTACACTGTTACCACTGCA
2609 >164_HRV88b
2610 AATCCAGTAGAAAACTATGTAGATAACTTGTTAAACGAAGTGCTAGTAGTTCCTAACATT
2611 CAACCTAGCACATCCGTTTCAAGTCACTCTGTGCCAGCTCTGGATGCTGCGGAAACAGGG
2612 CATACTAGTTCTGTTCAACCTGAAGATATGATAGAAACTAGATATGTTATAACAGATCAA
2613 ACAAGGGATGAAACCAGCATTGAAAGCTTTCTGGGTAGGTCTGGATGCATAGCAAAAATT
2614 AAACTTGACACAAATGAAGGTGATTACGACACAATAGGTGTTGGATTTGTAACATGGAAG
2615 ATTAGCTTGCAAGAAATGGCACAAATCAGGAGAAATTTGAATTGTTTACATACACTAGA
2616 TTTGACTCAGAAATAACAATAGTCACAGCAGCTGCAGCACAAGGTGATGATACTGGACAT
2617 ATAGTACTGCAATTCATGTATGTGCCTCCAGGTGCACCAATTCCCAAGAAACGTGATGAT
2618 TACACATGGCAGTCAGGAACAAATGCATCTGTGTTCTGGCAAGAAGGACAACCATACCCA
2619 AGATTTACCATTCCCTTTATGAGTATTGCATCAGCTTACTATATGTTTTATGATGGATAT
2620 GATGGTGATGATGCATCATCTAGGTATGGCTCAGTGGTAACTAATGATATGGGAACTATA
2621 TGTATTAGATTGGTCACCTCCACCCAAAAGCATAAACTGAATATCATTAGCCGTATATAT
2622 CACAAGGCTAAACATATAAAGGCATGGTGTCCACGCCCACCAAGAGCCGTACCTTATCAG
2623 CACACACACTCCACCAATTATGTACCAACAGATGGGGAAGTAGCAACTCAAATCAAAACC
2624 AGACGAGATGTTTACACTGTTACCACTGCG
2625 >165_HRV36a
2626 AATCCAGTTGAAAATTACATAGATAATGTATTAAATGAAGTACTTGTAGTGCCAAACATC
2627 CAACCTAGTTCATCTGTGTCAAGTCATTCAGCTCCCGCCTTAGACGCTGCGGAAACTGGA
2628 CATACCAGCTCTGTCCAACCAGAGGACATGATCGAGACCAGATATGTCATAACTGATCAA
2629 ACAAGAGATGAGACAAGTATTGAAAGCTTCTTAGGTAGGTCAGGGTGCATAGCTATGATA
2630 GAATTTAGCACAAGTAGTGATAAAGATGAACATGATGAAATTGGCAAGGGATTCAAAACA
2631 TGGAAGATTAGTCTTCAAGAAATGGCACAAATTAGAAGGAAATATGAATTGTTTACATAC
2632 ACAAGATTTGACTCAGAAATAACAATAGTCACCGCAGCTGCAGTGCAGGGAGATGATAGT
2633 GGGCATGTAGTATTACAATTCATGTATGTACCTCCAGGAGCGCCTGTTCCTGTGAAGCGT
2634 GATGACTACACATGGCAATCAGGGACAAATGCATCTGTGTTCTGGCAAGAAGGGCAACCA
2635 TATCCTAGATTTACAATCCCCTTTATGAGTATTGCATCAGCTTATTATATGTTTTATGAT
2636 GGTTATGATGGTGATAATGCCGCATCAAAATATGGATCTGTGGTTACTAACGACATGGGA
2637 ACCATATGTGTTAGAATAGTTACATCCAACCAAAAACATGATTTAAATATTGTATGCCGC
2638 ATTTATCATAAAGCTAAACACATAAAGGCCTGGTGCCCGCGTCCACCAAGGGCCGTTCCT
2639 TACCAACACACACATTCCACTAATTATATACCATACAAAGGTGAGATCACAACCCAAATT
2640 AAAACCAGACCTAATGTCTTCACTGTA
2641 >166_HRV36b
2642 AATCCAGTTGAAAATTACATAGATAATGTATTAAATGAAGTACTTGTAGTGCCAAACATC
2643 CAACCTAGTTCATCTGTGTCAAGTCATTCAGCTCCCGCCTTAGACGCTGCGGAAACTGGA
2644 CATACCAGCTCTGTCCAACCAGAGGACATGATCGAGACCAGATATGTCATAACTGATCAA
2645 ACAAGAGATGAGACAAGTATTGAAAGCTTCTTAGGTAGGTCAGGGTGCATAGCTATGATA
2646 GAATTTAGCACAAGTAGTGATAAAGATGAACATGATGAAATTGGCAAGGGATTCAAAACA
2647 TGGAAGATTAGTCTTCAAGAAATGGCACAAATTAGAAGGAAATATGAATTGTTTACATAC
2648 ACAAGATTTGACTCAGAAATAACAATAGTCACCGCAGCTGCAGTGCAGGGAGATGATAGT
2649 GGGCATGTAGTATTACAATTCATGTATGTACCTCCAGGAGCGCCTGTTCCTGTGAAGCGT
2650 GATGACTACACATGGCAATCAGGGACAAATGCATCTGTGTTCTGGCAAGAAGGGCAACCA
2651 TATCCTAGATTTACAATCCCCTTTATGAGTATTGCATCAGCTTATTATATGTTTTATGAT
2652 GGTTATGATGGTGATAATGCCGCATCAAAATATGGATCTGTGGTTACTAACGACATGGGA
2653 ACCATATGTGTTAGAATAGTTACATCCAACCAAAAACATGATTTAAATATTGTATGCCGC
2654 ATTTATCATAAAGCTAAACACATAAAGGCCTGGTGCCCGCGTCCACCAAGGGCCGTTCCT
2655 TACCAACACACACATTCCACTAATTATATACCATACAAAGGTGAGATCACAACCCAAATT
2656 AAAACCAGACCTAATGTCTTCACTGTG
2657 >167_HRV36
2658 AATCCAGTTGAAAATTACATAGATAATGTATTAAATGAAGTACTTGTAGTGCCAAACATC
2659 CAACCTAGTTCATCTGTGTCAAGTCATTCAGCTCCCGCCTTAGACGCTGCGGAAACTGGA
2660 CATACCAGCTCTGTCCAACCAGAGGACATGATCGAGACCAGATATGTCATAACTGATCAA
2661 ACAAGAGATGAGACAAGTATTGAAAGCTTCTTAGGTAGGTCAGGGTGCATAGCTATGATA
2662 GAATTTAGCACAAGTAGTGATAAAGATGAACATGATGAAATTGGCAAGGGATTCAAAACA
2663 TGGAAGATTAGTCTTCAAGAAATGGCACAAATTAGAAGGAAATATGAATTGTTTACATAC
2664 ACAAGATTTGACTCAGAAATAACAATAGTCACCGCAGCTGCAGTGCAGGGAGATGATAGT
2665 GGGCATGTAGTATTACAATTCATGTATGTACCTCCAGGAGCGCCTGTTCCTGTGAAGCGT
```

FIG. D1 CONT'D

Rhino_cDNA_DB.fasta                                                                 9/20/2007 5:08 PM

```
2666 GATGACTACACATGGCAATCAGGGACAAATGCATCTGTGTTCTGGCAAGAAGGGCAACCA
2667 TATCCTAGATTTACAATCCCCTTTATGAGTATTGCATCAGCTTATTATATGTTTTATGAT
2668 GGTTATGATGGTGATAATGCCGCATCAAAATATGGATCTGTGGTTACTAACGACATGGGA
2669 ACCATATGTGTTAGAATAGTTACATCCAACCAAAAACATGATTTAAATATTGTATGCCGC
2670 ATTTATCATAAAGCTAAACACATAAAGGCCTGGTGCCCGCGTCCACCAAGGGCCGTTCCT
2671 TACCAACACACACATTCCACTAATTATATACCATACAAAGGTGAGATCACAACCCAAATT
2672 AAAACCAGACCTAATGTCTTCACTGTT
2673 >168_HRV89a
2674 AACCCAGTTGAAAATTATATAGATAGTGTATTAAATGAAGTTCTTGTGGTGCCAAATATC
2675 CAACCTAGCACATCTGTGTCAAGTCATGCAGCGCCTGCATTGGATGCTGCGGAAACCGGA
2676 CACACCAGCTCTGTTCAACCTGAAGATATGATTGAAACTAGATATGTTATAACTGATCAA
2677 ACAAGGGATGAAACAAGTATTGAGAGTTTCTTAGGTAGGTCAGGGTGTATCGCTATGATA
2678 GAATTTAATACAAGTAGTGATAAAACTGAACATGATAAAATTGGTAAAGGATTCAAAACA
2679 TGGAAGGTTAGTCTTCAAGAAATGGCACAAATCAGAAGAAAATATGAATTATTCACATAT
2680 ACAAGATTTGATTCAGAGATAACAATAGTCACTGCAGCCGCAGCTCAAGGAAATGATAGT
2681 GGACATATAGTATTGCAATTTATGTATGTACCCCCAGGAGCACCTGTCCCCGAAAAACGT
2682 GATGATTACACATGGCAATCAGGAACAAATGCATCTGTGTTCTGGCAAGAAGGACAACCA
2683 TACCCCAGATTCACAATCCCTTTTATGAGCATTGCATCAGCCTATTACATGTTTTATGAT
2684 GGTTATGATGGTGATAGTGCAGCATCAAAATACGGTTCTGTAGTCACTAATGATATGGGA
2685 ACCATATGTGTTAGAATAGTGACATCCAACCAAAAACATGATTTAAATATTGTGTGCCGC
2686 ATTTACCACAAGGCCAAACATATAAAAGCATGGTGTCCTCGCCCACCAAGGGCTGTTGCC
2687 TATCAACACACACACTCAACCAATTACATACCATCCAATGGTGAGGCCACAACTCAGATT
2688 AAAACCAGACCTGATGTTTTTACCGTTACAAACGTG
2689 >169_HRV89b
2690 AACCCAGTTGAAAATTATATAGATAGTGTATTAAATGAAGTTCTTGTGGTGCCAAATATC
2691 CAACCTAGCACATCTGTGTCAAGTCATGCAGCGCCTGCATTGGATGCTGCGGAAACCGGA
2692 CACACCAGCTCTGTTCAACCTGAAGATATGATTGAAACTAGATATGTTATAACTGATCAA
2693 ACAAGGGATGAAACAAGTATTGAGAGTTTCTTAGGTAGGTCAGGGTGTATCGCTATGATA
2694 GAATTTAATACAAGTAGTGATAAAACTGAACATGATAAAATTGGTAAAGGATTCAAAACA
2695 TGGAAGGTTAGTCTTCAAGAAATGGCACAAATCAGAAGAAAATATGAATTATTCACATAT
2696 ACAAGATTTGATTCAGAGATAACAATAGTCACTGCAGCCGCAGCTCAAGGAAATGATAGT
2697 GGACATATAGTATTGCAATTTATGTATGTACCCCCAGGAGCACCTGTCCCCGAAAAACGT
2698 GATGATTACACATGGCAATCAGGAACAAATGCATCTGTGTTCTGGCAAGAAGGACAACCA
2699 TACCCCAGATTCACAATCCCTTTTATGAGCATTGCATCAGCCTATTACATGTTTTATGAT
2700 GGTTATGATGGTGATAGTGCAGCATCAAAATACGGTTCTGTAGTCACTAATGATATGGGA
2701 ACCATATGTGTTAGAATAGTGACATCCAACCAAAAACATGATTTAAATATTGTGTGCCGC
2702 ATTTACCACAAGGCCAAACATATAAAAGCATGGTGTCCTCGCCCACCAAGGGCTGTTGCC
2703 TATCAACACACACACTCAACCAATTACATACCATCCAATGGTGAGGCCACAACTCAGATT
2704 AAAACCAGACCTGATGTTTTTACCGTTACAAACGTA
2705 >170_HRV89
2706 AACCCAGTTGAAAATTATATAGATAGTGTATTAAATGAAGTTCTTGTGGTGCCAAATATC
2707 CAACCTAGCACATCTGTGTCAAGTCATGCAGCGCCTGCATTGGATGCTGCGGAAACCGGA
2708 CACACCAGCTCTGTTCAACCTGAAGATATGATTGAAACTAGATATGTTATAACTGATCAA
2709 ACAAGGGATGAAACAAGTATTGAGAGTTTCTTAGGTAGGTCAGGGTGTATCGCTATGATA
2710 GAATTTAATACAAGTAGTGATAAAACTGAACATGATAAAATTGGTAAAGGATTCAAAACA
2711 TGGAAGGTTAGTCTTCAAGAAATGGCACAAATCAGAAGAAAATATGAATTATTCACATAT
2712 ACAAGATTTGATTCAGAGATAACAATAGTCACTGCAGCCGCAGCTCAAGGAAATGATAGT
2713 GGACATATAGTATTGCAATTTATGTATGTACCCCCAGGAGCACCTGTCCCCGAAAAACGT
2714 GATGATTACACATGGCAATCAGGAACAAATGCATCTGTGTTCTGGCAAGAAGGACAACCA
2715 TACCCCAGATTCACAATCCCTTTTATGAGCATTGCATCAGCCTATTACATGTTTTATGAT
2716 GGTTATGATGGTGATAGTGCAGCATCAAAATACGGTTCTGTAGTCACTAATGATATGGGA
2717 ACCATATGTGTTAGAATAGTGACATCCAACCAAAAACATGATTTAAATATTGTGTGCCGC
2718 ATTTACCACAAGGCCAAACATATAAAAGCATGGTGTCCTCGCCCACCAAGGGCTGTTGCC
2719 TATCAACACACACACTCAACCAATTACATACCATCCAATGGTGAGGCCACAACTCAGATT
2720 AAAACCAGACCTGATGTTTTTACCGTTACAAACGTC
2721 >171_HRV58
2722 AATCCAGTAGAAAATTACATAGATAATGTGTTAAATGAAGTACTTGTAGTTCAAATATC
2723 CAACCTAGTACATCTGTATCAAGTCATTCTGTGCCTGCCTTGGATGCTGCAGAAACGGGA
2724 CACACAAGTTCTGTTCAGCCTGAGGATATGATTGAAACTAGATATGTTATCACAGATCAA
2725 ACAAGAGATGAAACTAGCATTGAAAGCTTTTTAGGTAGATCTGGTTGCATTGCTATCATA
2726 AAATTTAACACAAATAAGACTAATTATGATGACATAGGTGTAGGATACAAAACATGGAAA
2727 ATTAGCCTTCAAGAGATGGCACAAATTAGAAGGAAATTTGAGTTGTTTACATATACAAGA
2728 TTTGACTCAGAGATTACAATAGTCACTGCAGCAGCTGCTCAAGGAGAAGATAATGGACAT
2729 ATTGTGTTACAATTTATGTATGTACCCCCAGGAGCACCTGTACCCAAGAATCGTGATGAC
2730 TTTACATGGCAATCAGGCACAAATGCATCTGTTTCTGGCAGGAAGGACAACCATACCCT
```

FIG. D1 CONT'D

Rhino_cDNA_DB.fasta                                                9/20/2007 5:08 PM

```
2731 AGATTTACAATCCCTTTTATGAGCATTGCATCAGCTTACTATATGTTTTATGATGGCTAT
2732 GATGGTGATGATGCTAAATCAATATATGGTTCTGTGGTAACAAATGACATGGGAACTATA
2733 TGTGTTAGAATAGTCACATCCAAACAAAGACACAATTTAAACATTGTCTGTCGCATTTAC
2734 CACAAAGCCAAGCATATAAAAGCATGGTGTCCACGCCCACCAAGGGCTGTTCCTTATCAA
2735 TTCACACATTCTACTAATTACATACCAGATAGTGGTGAGGTAACAACACAAATCAAACCC
2736 AGAACCAATGTTTTTACTATTACATCTGCT
2737 >172_HRV58a
2738 AATCCAGTAGAAAATTACATAGATAATGTGTTAAATGAAGTACTTGTAGTTCCAAATATC
2739 CAACCTAGTACATCTGTATCAAGTCATTCTGTGCCTGCCTTGGATGCTGCAGAAACGGGA
2740 CACACAAGTTCTGTTCAGCCTGAGGATATGATTGAAACTAGATATGTTATCACAGATCAA
2741 ACAAGAGATGAAACTAGCATTGAAAGCTTTTTAGGTAGATCTGGTTGCATTGCTATCATA
2742 AAATTTAACACAAATAAGACTAATTATGATGACATAGGTGTAGGATACAAAACATGGAAA
2743 ATTAGCCTTCAAGAGATGGCACAAATTAGAAGGAAATTTGAGTTGTTTACATATACAAGA
2744 TTTGACTCAGAGATTACAATAGTCACTGCAGCAGCTGCTCAAGGAGAAGATAATGGACAT
2745 ATTGTGTTACAATTTATGTATGTACCCCCAGGAGCACCTGTACCCAAGAATCGTGATGAC
2746 TTTACATGGCAATCAGGCACAAATGCATCTGTTTTCTGGCAGGAAGGACAACCATACCCT
2747 AGATTTACAATCCCTTTTATGAGCATTGCATCAGCTTACTATATGTTTTATGATGGCTAT
2748 GATGGTGATGATGCTAAATCAATATATGGTTCTGTGGTAACAAATGACATGGGAACTATA
2749 TGTGTTAGAATAGTCACATCCAAACAAAGACACAATTTAAACATTGTCTGTCGCATTTAC
2750 CACAAAGCCAAGCATATAAAAGCATGGTGTCCACGCCCACCAAGGGCTGTTCCTTATCAA
2751 TTCACACATTCTACTAATTACATACCAGATAGTGGTGAGGTAACAACACAAATCAAACCC
2752 AGAACCAATGTTTTTACTATTACATCTGCA
2753 >173_HRV58b
2754 AATCCAGTAGAAAATTACATAGATAATGTGTTAAATGAAGTACTTGTAGTTCCAAATATC
2755 CAACCTAGTACATCTGTATCAAGTCATTCTGTGCCTGCCTTGGATGCTGCAGAAACGGGA
2756 CACACAAGTTCTGTTCAGCCTGAGGATATGATTGAAACTAGATATGTTATCACAGATCAA
2757 ACAAGAGATGAAACTAGCATTGAAAGCTTTTTAGGTAGATCTGGTTGCATTGCTATCATA
2758 AAATTTAACACAAATAAGACTAATTATGATGACATAGGTGTAGGATACAAAACATGGAAA
2759 ATTAGCCTTCAAGAGATGGCACAAATTAGAAGGAAATTTGAGTTGTTTACATATACAAGA
2760 TTTGACTCAGAGATTACAATAGTCACTGCAGCAGCTGCTCAAGGAGAAGATAATGGACAT
2761 ATTGTGTTACAATTTATGTATGTACCCCCAGGAGCACCTGTACCCAAGAATCGTGATGAC
2762 TTTACATGGCAATCAGGCACAAATGCATCTGTTTTCTGGCAGGAAGGACAACCATACCCT
2763 AGATTTACAATCCCTTTTATGAGCATTGCATCAGCTTACTATATGTTTTATGATGGCTAT
2764 GATGGTGATGATGCTAAATCAATATATGGTTCTGTGGTAACAAATGACATGGGAACTATA
2765 TGTGTTAGAATAGTCACATCCAAACAAAGACACAATTTAAACATTGTCTGTCGCATTTAC
2766 CACAAAGCCAAGCATATAAAAGCATGGTGTCCACGCCCACCAAGGGCTGTTCCTTATCAA
2767 TTCACACATTCTACTAATTACATACCAGATAGTGGTGAGGTAACAACACAAATCAAACCC
2768 AGAACCAATGTTTTTACTATTACATCTGCC
2769 >174_HRV12a
2770 AATCCAGTAGAGAGATATGTTGATGAGGTGCTAAATGAAGTTCTAGTTGTTCCAAACATA
2771 AACAAAAGTAATGGGCAGTTATCAAACGCAGCACCAGCGTTGGACGCTGCAGAAACTGGT
2772 CATACCAGCCAAACACAACCAGAAGATGTGATTGAAACCAGGTATGTGATTACAGACCAG
2773 ACTAGAGATGAGATGTCAATTGAATCTTTCCTTGGTCGGTCCGGATGCATTTCAATTATC
2774 GAATTGGATTTAGACCATGAAGGTTATTCAGCAGAAGGGAAAAACTTTAAAACATGGAAG
2775 ATAAATCTTAAGGAAATGGCCCAGATTAGAAGGAAAAATGAGCTTTTCACCTACTTAAGG
2776 TTTGATTCTGAAATCACCATTGTTCCAAGCAATGCAGCAATAGAAGGAAGCAATGGTCAC
2777 GTGGTGGTCCAATACATGTATGTACCTCCTGGTGCCCCACTACCCAAAAAACGTGATGAT
2778 TACACATGGCAATCTGGCACCAACGCCTCAGTTTTTTGGCAGGAAGGTCAACCTTACCCC
2779 AGATTCACAATCCCTTTTATTAGTATTGCCTCAGCATATTACATGTTTTATGATGGTTAT
2780 GCTGATGACAACCCAAGTGCACCTTATGGAACTGTAGTTACCAATGACATGGGTTCACTG
2781 TGTGTCAGAATAGTTACAGACCAGCAAAAACATAAAGTTAAGATTACCAGTAGAATATAC
2782 CATAAAGCAAAACATATCAGTGCCTGGGGCCCTAGACCACCAAGAGCTGTACCATACCAG
2783 CATATACACAATCCAAATTACAAGACAAGTAATGGAGTTCCAGACAATAGAGTCAAACTC
2784 AGAGAGACACTCACCACAGTA
2785 >175_HRV12b
2786 AATCCAGTAGAGAGATATGTTGATGAGGTGCTAAATGAAGTTCTAGTTGTTCCAAACATA
2787 AACAAAAGTAATGGGCAGTTATCAAACGCAGCACCAGCGTTGGACGCTGCAGAAACTGGT
2788 CATACCAGCCAAACACAACCAGAAGATGTGATTGAAACCAGGTATGTGATTACAGACCAG
2789 ACTAGAGATGAGATGTCAATTGAATCTTTCCTTGGTCGGTCCGGATGCATTTCAATTATC
2790 GAATTGGATTTAGACCATGAAGGTTATTCAGCAGAAGGGAAAAACTTTAAAACATGGAAG
2791 ATAAATCTTAAGGAAATGGCCCAGATTAGAAGGAAAAATGAGCTTTTCACCTACTTAAGG
2792 TTTGATTCTGAAATCACCATTGTTCCAAGCAATGCAGCAATAGAAGGAAGCAATGGTCAC
2793 GTGGTGGTCCAATACATGTATGTACCTCCTGGTGCCCCACTACCCAAAAAACGTGATGAT
2794 TACACATGGCAATCTGGCACCAACGCCTCAGTTTTTTGGCAGGAAGGTCAACCTTACCCC
2795 AGATTCACAATCCCTTTTATTAGTATTGCCTCAGCATATTACATGTTTTATGATGGTTAT
```

FIG. D1 CONT'D

```
Rhino cDNA DB.fasta                                            9/20/2007 5:08 PM 2796  GCTGATGACAACCCAAGTGCACCTTATGGAACTGTAGTTACCAATGACATGGGTTCACTG
2797  TGTGTCAGAATAGTTACAGACCAGCAAAAACATAAAGTTAAGATTACCAGTAGAATATAC
2798  CATAAAGCAAAACATATCAGTGCCTGGGGCCCTAGACCACCAAGAGCTGTACCATACCAG
2799  CATATACACAATCCAAATTACAAGACAAGTAATGGAGTTCCAGACAATAGAGTCAAACTC
2800  AGAGAGACACTCACCACAGTG
2801  >176_HRV1
2802  AATCCAGTAGAGAGATATGTTGATGAGGTGCTAAATGAAGTTCTAGTTGTTCCAAACATA
2803  AACAAAAGTAATGGGCAGTTATCAAACGCAGCACCAGCGTTGGACGCTGCAGAAACTGGT
2804  CATACCAGCCAAACACAACCAGAAGATGTGATTGAAACCAGGTATGTGATTACAGACCAG
2805  ACTAGAGATGAGATGTCAATTGAATCTTTCCTTGGTCGGTCCGGATGCATTTCAATTATC
2806  GAATTGGATTTAGACCATGAAGGTTATTCAGCAGAAGGGAAAAACTTTAAAACATGGAAG
2807  ATAAATCTTAAGGAAATGGCCCAGATTAGAAGGAAAAATGAGCTTTTCACCTACTTAAGG
2808  TTTGATTCTGAAATCACCATTGTTCCAAGCAATGCAGCAATAGAAGGAAGCAATGGTCAC
2809  GTGGTGGTCCAATACATGTATGTACCTCCTGGTGCCCCACTACCCAAAAAACGTGATGAT
2810  TACACATGGCAATCTGGCACCAACGCCTCAGTTTTTTGGCAGGAAGGTCAACCTTACCCC
2811  AGATTCACAATCCCTTTTATTAGTATTGCCTCAGCATATTACATGTTTTATGATGGTTAT
2812  GCTGATGACAACCCAAGTGCACCTTATGGAACTGTAGTTACCAATGACATGGGTTCACTG
2813  TGTGTCAGAATAGTTACAGACCAGCAAAAACATAAAGTTAAGATTACCAGTAGAATATAC
2814  CATAAAGCAAAACATATCAGTGCCTGGGGCCCTAGACCACCAAGAGCTGTACCATACCAG
2815  CATATACACAATCCAAATTACAAGACAAGTAATGGAGTTCCAGACAATAGAGTCAAACTC
2816  AGAGAGACACTCACCACAGTT
2817  >177_HRV78a
2818  AATCCAGTGGAAGAATATGTTGATCAGGTTTTAAATGAGGTTTTAGTTGTTCCAAACATA
2819  AAAGAAAGTAAACCCCAGTCTAGCAACTCCGCTCCAGTTTTGGACGCTGCAGAAACAGGT
2820  CATACGAACCAAGTACAGCCTGAAGACACCATAGAAACTAGATATGTTATAACTGACCAG
2821  ACAAGAGATGAAATGAGCATTGAAAGTTTCCTCGGAAGATCAGGTTGTGCAACAATTATG
2822  AGACTAGAATTGGACCACACTGATTACAATGCTGAAGGGAAAAATTTTACAACGTGGAAA
2823  ATCAACTTACAGGAGATGGCCCAGATTAGAAGAAAGAATGAGATGTTCACATATCTCAGA
2824  TTTGATTCAGAAATCACTCTTGTGTGTGCAGTGGCCTCACAAGGAGACAATAATGGACAT
2825  GTGGTGCTTCAATTTATGTTTGTTCCACCTGGAGCCCCTATACCAAAGAAGAGAGATGAC
2826  TATACTTGGCAGTCAGGCACCAATGCATCTGTGTTTTGGCAACAAGGTCAAACATACCCC
2827  AGGTTCTCTATACCATTTTCTAGTATTGCCTCAGCTTATTACATGTTTTATGATGGATAC
2828  TCGGATGACAGCACATCCTCTCCATATGGCACTGTAGTTACCAATGACATGGGTACACTG
2829  TGTATGAGGATGGTTACAGATCAACAACAACATAAGGTCACAATTACAGCTAGAGTCTAC
2830  CACAAGGCCAAACATATTAGTGCATGGGGCCCAAGACCTCCTAGAGCTGTACCTTATCAG
2831  CACATATATAACCCTAATTATAAAACTGAAGAAGGAACTCCAGACACCAAAGTGGCAATT
2832  AGAGCTAATATTAAAACTGTA
2833  >178_HRV78b
2834  AATCCAGTGGAAGAATATGTTGATCAGGTTTTAAATGAGGTTTTAGTTGTTCCAAACATA
2835  AAAGAAAGTAAACCCCAGTCTAGCAACTCCGCTCCAGTTTTGGACGCTGCAGAAACAGGT
2836  CATACGAACCAAGTACAGCCTGAAGACACCATAGAAACTAGATATGTTATAACTGACCAA
2837  ACAAGAGATGAAATGAGCATTGAAAGTTTCCTCGGAAGATCAGGTTGTGCAACAATTATG
2838  AGACTAGAATTGGACCACACTGATTACAATGCTGAAGGGAAAAATTTTACAACGTGGAAA
2839  ATCAACTTACAGGAGATGGCCCAGATTAGAAGAAAGAATGAGATGTTCACATATCTCAGA
2840  TTTGATTCAGAAATCACTCTTGTGTGTGCAGTGGCCTCACAAGGAGACAATAATGGACAT
2841  GTGGTGCTTCAATTTATGTTTGTTCCACCTGGAGCCCCTATACCAAAGAAGAGAGATGAC
2842  TATACTTGGCAGTCAGGCACCAATGCATCTGTGTTTTGGCAACAAGGTCAAACATACCCC
2843  AGGTTCTCTATACCATTTTCTAGTATTGCCTCAGCTTATTACATGTTTTATGATGGATAC
2844  TCGGATGACAGCACATCCTCTCCATATGGCACTGTAGTTACCAATGACATGGGTACACTG
2845  TGTATGAGGATGGTTACAGATCAACAACAACATAAGGTCACAATTACAGCTAGAGTCTAC
2846  CACAAGGCCAAACATATTAGTGCATGGGGCCCAAGACCTCCTAGAGCTGTACCTTATCAG
2847  CACATATATAACCCTAATTATAAAACTGAAGAAGGAACTCCAGACACCAAAGTGGCAATT
2848  AGAGCTAATATTAAAACTGTG
2849  >179_HRV78
2850  AATCCAGTGGAAGAATATGTTGATCAGGTTTTAAATGAGGTTTTAGTTGTTCCAAACATA
2851  AAAGAAAGTAAACCCCAGTCTAGCAACTCCGCTCCAGTTTTGGACGCTGCAGAAACAGGT
2852  CATACGAACCAAGTACAGCCTGAAGACACCATAGAAACTAGATATGTTATAACTGACCAA
2853  ACAAGAGATGAAATGAGCATTGAAAGTTTCCTCGGAAGATCAGGTTGTGCAACAATTATG
2854  AGACTAGAATTGGACCACACTGATTACAATGCTGAAGGGAAAAATTTTACAACGTGGAAA
2855  ATCAACTTACAGGAGATGGCCCAGATTAGAAGAAAGAATGAGATGTTCACATATCTCAGA
2856  TTTGATTCAGAAATCACTCTTGTGTGTGCAGTGGCCTCACAAGGAGACAATAATGGACAT
2857  GTGGTGCTTCAATTTATGTTTGTTCCACCTGGAGCCCCTATACCAAAGAAGAGAGATGAC
2858  TATACTTGGCAGTCAGGCACCAATGCATCTGTGTTTTGGCAACAAGGTCAAACATACCCC
2859  AGGTTCTCTATACCATTTTCTAGTATTGCCTCAGCTTATTACATGTTTTATGATGGATAC
2860  TCGGATGACAGCACATCCTCTCCATATGGCACTGTAGTTACCAATGACATGGGTACACTG
```

FIG. D1 CONT'D

```
Rhino_cDNA_DB.fasta                                              9/20/2007 5:08 PM
2861  TGTATGAGGATGGTTACAGATCAACAACAACATAAGGTCACAATTACAGCTAGAGTCTAC
2862  CACAAGGCCAAACATATTAGTGCATGGGGCCCAAGACCTCCTAGAGCTGTACCTTATCAG
2863  CACATATATAACCCTAATTATAAAACTGAAGAAGGAACTCCAGACACCAAAGTGGCAATT
2864  AGAGCTAATATTAAAACTGTT
2865  >180_HRV20
2866  AACCCAGTGGAAAGGTACACAGAAGCTATTTTAAATGAAGTTCTTGTAGTTCCAAATATC
2867  ACATCTAGTAACTCCCAAACATCAAATGCAGCACCAGCACTAGATGCTGCTGAGACAGGA
2868  CACACAAACCAGGTCCAGCCAGAAGATATGGTCGAGACACGGTATGTAATTACTGATCAG
2869  ACCCGTGATGAAATGAGTGTGGAAAGTTTTCTTGGTAGATCTGGTTGCATTGCTATCATA
2870  CATACTGACTTAGATCATGAAGCACAAACAATATAATGCACCCGGAAAAAATTTCTCTCAG
2871  TGGAAGATCACAATCAAGGAAATGGCTCAAATCAGAAGAAAATGTGAGCTCTTTACATAC
2872  CTCAGATTTGATTCTGAGATTACAATAGTAGCAACAGTAGCTGCACTAGGTCGGGATAAT
2873  GGGCATGTTGTTTTACAGTATATGTATGTACCACCAGGGGCACCAATACCAAAGACTAGA
2874  GATGACTACACATGGCAATCAGGGACAAATGCATCAGTATTTTGGCAGCAGGGCCAACCT
2875  TACCCCAGATTTACCATTCCATTTATGAGTATAGCTTCAGCATATTATATGTTTTATGAT
2876  GGTTATGAAGATGATAAGGGAAGTGTGTATGGGTCTGTTGTCACAAACGATATGGGCACA
2877  TTGTGTGTTCGTATTGTGACTGAGCAGCAGACACATAAGGTTAAGATAACCAGTAGGATA
2878  TTCCACAAGGCAAAGCATATTAGTGCATGGTGTCCAAGGGCCCCAAGAGCAGTGCCTTAT
2879  CAACACACTAAGAGCACAAACTTAGTGCCAAGGACAGGTGAAATTACAACTCATATCAGA
2880  TTCAGAAACACTGTCAAAGATCTAACATACCCCACAGAAATGACGAATGTT
2881  >181_HRV20a
2882  AACCCAGTGGAAAGGTACACAGAAGCTATTTTAAATGAAGTTCTTGTAGTTCCAAATATC
2883  ACATCTAGTAACTCCCAAACATCAAATGCAGCACCAGCACTAGATGCTGCTGAGACAGGA
2884  CACACAAACCAGGTCCAGCCAGAAGATATGGTCGAGACACGGTATGTAATTACTGATCAG
2885  ACCCGTGATGAAATGAGTGTGGAAAGTTTTCTTGGTAGATCTGGTTGCATTGCTATCATA
2886  CATACTGACTTAGATCATGAAGCACAACAATATAATGCACCCGGAAAAAATTTCTCTCAG
2887  TGGAAGATCACAATCAAGGAAATGGCTCAAATCAGAAGAAAATGTGAGCTCTTTACATAC
2888  CTCAGATTTGATTCTGAGATTACAATAGTAGCAACAGTAGCTGCACTAGGTCGGGATAAT
2889  GGGCATGTTGTTTTACAGTATATGTATGTACCACCAGGGGCACCAATACCAAAGACTAGA
2890  GATGACTACACATGGCAATCAGGGACAAATGCATCAGTATTTTGGCAGCAGGGCCAACCT
2891  TACCCCAGATTTACCATTCCATTTATGAGTATAGCTTCAGCATATTATATGTTTTATGAT
2892  GGTTATGAAGATGATAAGGGAAGTGTGTATGGGTCTGTTGTCACAAACGATATGGGCACA
2893  TTGTGTGTTCGTATTGTGACTGAGCAGCAGACACATAAGGTTAAGATAACCAGTAGGATA
2894  TTCCACAAGGCAAAGCATATTAGTGCATGGTGTCCAAGGGCCCCAAGAGCAGTGCCTTAT
2895  CAACACACTAAGAGCACAAACTTAGTGCCAAGGACAGGTGAAATTACAACTCATATCAGA
2896  TTCAGAAACACTGTCAAAGATCTAACATACCCCACAGAAATGACGAATGTA
2897  >182_HRV20b
2898  AACCCAGTGGAAAGGTACACAGAAGCTATTTTAAATGAAGTTCTTGTAGTTCCAAATATC
2899  ACATCTAGTAACTCCCAAACATCAAATGCAGCACCAGCACTAGATGCTGCTGAGACAGGA
2900  CACACAAACCAGGTCCAGCCAGAAGATATGGTCGAGACACGGTATGTAATTACTGATCAG
2901  ACCCGTGATGAAATGAGTGTGGAAAGTTTTCTTGGTAGATCTGGTTGCATTGCTATCATA
2902  CATACTGACTTAGATCATGAAGCACAACAATATAATGCACCCGGAAAAAATTTCTCTCAG
2903  TGGAAGATCACAATCAAGGAAATGGCTCAAATCAGAAGAAAATGTGAGCTCTTTACATAC
2904  CTCAGATTTGATTCTGAGATTACAATAGTAGCAACAGTAGCTGCACTAGGTCGGGATAAT
2905  GGGCATGTTGTTTTACAGTATATGTATGTACCACCAGGGGCACCAATACCAAAGACTAGA
2906  GATGACTACACATGGCAATCAGGGACAAATGCATCAGTATTTTGGCAGCAGGGCCAACCT
2907  TACCCCAGATTTACCATTCCATTTATGAGTATAGCTTCAGCATATTATATGTTTTATGAT
2908  GGTTATGAAGATGATAAGGGAAGTGTGTATGGGTCTGTTGTCACAAACGATATGGGCACA
2909  TTGTGTGTTCGTATTGTGACTGAGCAGCAGACACATAAGGTTAAGATAACCAGTAGGATA
2910  TTCCACAAGGCAAAGCATATTAGTGCATGGTGTCCAAGGGCCCCAAGAGCAGTGCCTTAT
2911  CAACACACTAAGAGCACAAACTTAGTGCCAAGGACAGGTGAAATTACAACTCATATCAGA
2912  TTCAGAAACACTGTCAAAGATCTAACATACCCCACAGAAATGACGAATGTG
2913  >183_HRV68
2914  AACCCAGTGAAAAATACACAGAAGCCGTTCTTAATGAGGTCCTTGTGGTTCCAAACATA
2915  CCAGCAAGTAATACCCAAACTTCAAATGCAGCCCCAGCCTTAGATGCTGCTGAGACTGGA
2916  CATACAAACCAAGTCCAACCAGAAGATGTGGTTGAAACACGCTATGTCATAACAGACCAG
2917  ACAAGGGATGAAATGAGCATAGAGAGCTTCCTCGGTAGGTCAGGTTGCATTGCAATCATA
2918  CATACTGACTTAGATCACAATGAGGATCAGTACAATGCACCTGGAAAAAACTTCTCCCAA
2919  TGGAAAATTACAATTAAGGAAATGGCTCAAATTAGAAGAAAGTGTGAACTATTCACATAC
2920  CTTAGGTTTGACTCTGAGATTACAATAGTAGCAACAATAGCTGCTCTTGGAAAAGATAAT
2921  GGCCATGTGGTTTTACAGTACATGTATGTGCCGCCAGGGGCACCCATACCAAAAACTAGA
2922  GATGATTACACATGGCAGTCAGGCACTAATGCATCAGTGTTTTGGCAACAAGGACAACCT
2923  TACCCCAGATTTACCATTCCATTTATGAGTATAGCTTCAGCATATTATATGTTTTATGAT
2924  GGATATGAGGATGACAAAGGAAGTGTGTATGGATCTGTTGTTACAAATGATATGGGCACA
2925  TTATGTGTCCGTATTGTGACTGAGCAGCAGACACATAGGGTCAAAATAACCAGCAGAATA
```

FIG. D1 CONT'D

Rhino cDNA_DB.fasta                                                    9/20/2007 5:08 PM

```
2926 TTCCATAAAGCAAAACATATTAGTGCGTGGTGTCCAAGAGCTCCAAGAGCAGTGCCCTAC
2927 CAGCACACCAGAAGTACAAACTTAGTACCAAAGGAAGGTGATATTAAAACTCATATTAAA
2928 TTTAGGAATACTGTTAAAGATTTGGCATATCCTCCAGAATTAGCAAACCTT
2929 >184_HRV68a
2930 AACCCAGTTGAAAAATACACAGAAGCCGTTCTTAATGAGGTCCTTGTGGTTCCAAACATA
2931 CCAGCAAGTAATACCCAAACTTCAAATGCAGCCCCAGCCTTAGATGCTGCTGAGACTGGA
2932 CATACAAACCAAGTCCAACCAGAAGATGTGGTTGAAACACGCTATGTCATAACAGACCAG
2933 ACAAGGGATGAAATGAGCATAGAGAGCTTCCTCGGTAGGTCAGGTTGCATTGCAATCATA
2934 CATACTGACTTAGATCACAATGAGGATCAGTACAATGCACCTGGAAAAAAACTTCTCCCAA
2935 TGGAAAATTACAATTAAGGAAATGGCTCAAATTAGAAGAAAGTGTGAACTATTCACATAC
2936 CTTAGGTTTGACTCTGAGATTACAATAGTAGCAACAATAGCTGCTCTTGGAAAAGATAAT
2937 GGCCATGTGGTTTTACAGTACATGTATGTGCCGCCAGGGGCACCCATACCAAAAACTAGA
2938 GATGATTACACATGGCAGTCAGGCACTAATGCATCAGTGTTTTGGCAACAAGGACAACCT
2939 TACCCCAGATTTACCATTCCATTTATGAGTATAGCTTCAGCATATTATATGTTTTATGAT
2940 GGATATGAGGATGACAAAGGAAGTGTGTATGGATCTGTTGTTACAAATGATATGGGCACA
2941 TTATGTGTCCGTATTGTGACTGAGCAGCAGACACATAGGGTCAAAATAACCAGCAGAATA
2942 TTCCATAAAGCAAAACATATTAGTGCGTGGTGTCCAAGAGCTCCAAGAGCAGTGCCCTAC
2943 CAGCACACCAGAAGTACAAACTTAGTACCAAAGGAAGGTGATATTAAAACTCATATTAAA
2944 TTTAGGAATACTGTTAAAGATTTGGCATATCCTCCAGAATTAGCAAACCTT
2945 >185_HRV68b
2946 AACCCAGTTGAAAAATACACAGAAGCCGTTCTTAATGAGGTCCTTGTGGTTCCAAACATA
2947 CCAGCAAGTAATACCCAAACTTCAAATGCAGCCCCAGCCTTAGATGCTGCTGAGACTGGA
2948 CATACAAACCAAGTCCAACCAGAAGATGTGGTTGAAACACGCTATGTCATAACAGACCAG
2949 ACAAGGGATGAAATGAGCATAGAGAGCTTCCTCGGTAGGTCAGGTTGCATTGCAATCATA
2950 CATACTGACTTAGATCACAATGAGGATCAGTACAATGCACCTGGAAAAAAACTTCTCCCAA
2951 TGGAAAATTACAATTAAGGAAATGGCTCAAATTAGAAGAAAGTGTGAACTATTCACATAC
2952 CTTAGGTTTGACTCTGAGATTACAATAGTAGCAACAATAGCTGCTCTTGGAAAAGATAAT
2953 GGCCATGTGGTTTTACAGTACATGTATGTGCCGCCAGGGGCACCCATACCAAAAACTAGA
2954 GATGATTACACATGGCAGTCAGGCACTAATGCATCAGTGTTTTGGCAACAAGGACAACCT
2955 TACCCCAGATTTACCATTCCATTTATGAGTATAGCTTCAGCATATTATATGTTTTATGAT
2956 GGATATGAGGATGACAAAGGAAGTGTGTATGGATCTGTTGTTACAAATGATATGGGCACA
2957 TTATGTGTCCGTATTGTGACTGAGCAGCAGACACATAGGGTCAAAATAACCAGCAGAATA
2958 TTCCATAAAGCAAAACATATTAGTGCGTGGTGTCCAAGAGCTCCAAGAGCAGTGCCCTAC
2959 CAGCACACCAGAAGTACAAACTTAGTACCAAAGGAAGGTGATATTAAAACTCATATTAAA
2960 TTTAGGAATACTGTTAAAGATTTGGCATATCCTCCAGAATTAGCAAACCTT
2961 >186_HRV28
2962 AATCCAGTTGAAAAATATACTGAAGCACTACTTAATGAAGTGCTTGTTGTGCCAAACATC
2963 AATCCTAGCAACGCACAAACTACAAATGCAGCTCCCGCTCTCGATGCCGCTGAGACGGGG
2964 CACACAAGCCAAACACAACCTGAAGACATGGTTGAGACTAGGTATGTAATCACAGATCAG
2965 ACCCGTGATGAAATGAGTATAGAGAGTTTCTTAGGTAGGTCTAGTTGCATTGCAATAATC
2966 CATACTGATGTTGTGCATGAAACAGACAAGTACAACCACCCAGGGAAGAATTTTAGTAAA
2967 TGGAATATCACTCTCAAAGAAATGGCCCAAATCAGAAGAAAGTGTGAAATGTTTACATAT
2968 CTCAGATTTGATTCTGAAATTACTATAGTGGTGTCAGTTGCAAGTAAAGGTGATGATAAT
2969 GGGCATGTAGTTATGCAATATATGTATGTACCTCCAGGAGCCCCCATCCCCACTACCAGA
2970 AATGATTACACATGGCAATCCAGTACCAATGCCTCTGTTTTCTGGCAACAAGGACAACCA
2971 TATCCCAGATTCACTATACCTTTTATGAGTATTGCCTCAGCTTATTACATGTTTTATGAT
2972 GGTTATGAAGATGACAATGGAACTACCTATGGTGCAGTGGTTACAAATCATATGGGAACA
2973 CTCTGTGCTCGCATAGTAACTGAACAACAGAAGCATGAAGTCAAAATAACCAGCATAATA
2974 TTCCACAAAGCTAAACATGTCAGTGCATGGTGCCCCAGACCTCCACGCGCTGTAGCTTAT
2975 CAACATACATACAGTCCAAACTTTGTGCCTCAGGAAGGTGATGTTGAGACTCATATTAAA
2976 TTTAGAACAGATGTTAAACAGATCACAACAGTT
2977 >187_HRV28a
2978 AATCCAGTTGAAAAATATACTGAAGCACTACTTAATGAAGTGCTTGTTGTGCCAAACATC
2979 AATCCTAGCAACGCACAAACTACAAATGCAGCTCCCGCTCTCGATGCCGCTGAGACGGGG
2980 CACACAAGCCAAACACAACCTGAAGACATGGTTGAGACTAGGTATGTAATCACAGATCAG
2981 ACCCGTGATGAAATGAGTATAGAGAGTTTCTTAGGTAGGTCTAGTTGCATTGCAATAATC
2982 CATACTGATGTTGTGCATGAAACAGACAAGTACAACCACCCAGGGAAGAATTTTAGTAAA
2983 TGGAATATCACTCTCAAAGAAATGGCCCAAATCAGAAGAAAGTGTGAAATGTTTACATAT
2984 CTCAGATTTGATTCTGAAATTACTATAGTGGTGTCAGTTGCAAGTAAAGGTGATGATAAT
2985 GGGCATGTAGTTATGCAATATATGTATGTACCTCCAGGAGCCCCCATCCCCACTACCAGA
2986 AATGATTACACATGGCAATCCAGTACCAATGCCTCTGTTTTCTGGCAACAAGGACAACCA
2987 TATCCCAGATTCACTATACCTTTTATGAGTATTGCCTCAGCTTATTACATGTTTTATGAT
2988 GGTTATGAAGATGACAATGGAACTACCTATGGTGCAGTGGTTACAAATCATATGGGAACA
2989 CTCTGTGCTCGCATAGTAACTGAACAACAGAAGCATGAAGTCAAAATAACCAGCATAATA
2990 TTCCACAAAGCTAAACATGTCAGTGCATGGTGCCCCAGACCTCCACGCGCTGTAGCTTAT
```

FIG. D1 CONT'D

Rhino cDNA DB.fasta                                                9/20/2007 5:08 PM

```
2991 CAACATACATACAGTCCAAACTTTGTGCCTCAGGAAGGTGATGTTGAGACTCATATTAAA
2992 TTTAGAACAGATGTTAAACAGATCACAACAGTA
2993 >188_HRV28b
2994 AATCCAGTTGAAAAATATACTGAAGCACTACTTAATGAAGTGCTTGTTGTGCCAAACATC
2995 AATCCTAGCAACGCACAAACTACAAATGCAGCTCCCGCTCTCGATGCCGCTGAGACGGGG
2996 CACACAAGCCAAACACAACCTGAAGCATGGTTGAGACTAGGTATGTAATCACAGATCAG
2997 ACCCGTGATGAAATGAGTATAGAGAGTTTCTTAGGTAGGTCTAGTTGCATTGCAATAATC
2998 CATACTGATGTTGTGCATGAAACAGACAAGTACAACCACCCAGGGAAGAATTTTAGTAAA
2999 TGGAATATCACTCTCAAAGAAATGGCCCAAATCAGAAGAAAGTGTGAAATGTTTACATAT
3000 CTCAGATTTGATTCTGAAATTACTATAGTGGTGTCAGTTGCAAGTAAAGGTGATGATAAT
3001 GGGCATGTAGTTATGCAATATATGTATGTACCTCCAGGAGCCCCCATCCCCACTACCAGA
3002 AATGATTACACATGGCAATCCAGTACCAATGCCTCTGTTTTCTGGCAACAAGGACAACCA
3003 TATCCCAGATTCACTATACCTTTTATGAGTATTGCCTCAGCTTATTACATGTTTTATGAT
3004 GGTTATGAAGATGACAATGGAACTACCTATGGTGCAGTGGTTACAAATCATATGGGAACA
3005 CTCTGTGCTCGCATAGTAACTGAACAACAGAAGCATGAAGTCAAAATAACCAGCATAATA
3006 TTCCACAAAGCTAAACATGTCAGTGCATGGTGCCCCAGACCTCCACGCGCTGTAGCTTAT
3007 CAACATACATACAGTCCAAACTTTGTGCCTCAGGAAGGTGATGTTGAGACTCATATTAAA
3008 TTTAGAACAGATGTTAAACAGATCACAACAGTC
3009 >189_HRV53a
3010 AACCCGGTAGAGAAATACACAGAGGCTATCTTAAATGAAGTATTAGTAGTCCCAAACATT
3011 AATGCAAGCAATCCACAAACTTCAAATTCAGCACCAGCACTAGATGCTGCAGAAACGGGT
3012 CATACAAGTCAGACACAACCTGAGGACATGCTGGAAACTAGATATGTCATCACAGACCAA
3013 ACCCGGGATGAAATGAGCATTGAAAGTTTCTTAGGCAGATCAAGTTGCATTGCTGAGATC
3014 CATACCAATTTAGACCATACTGGATACAATGAGCCTGGGAAAAACCACTCAGAATGGAAG
3015 ATTACACTCAAAGAAATGGCCCAGATTAGAAGGAAATGTGAGATGTTCACATATCTTAGA
3016 TTTGATTCAGAAATAACTATAGTGGTATCAGTGGCTAGTAAACAAGGGAATAACGGGCAC
3017 GTGGTGATACAATACATGTATGTACCACCGGGTGCTCCAATACCCAAAACCAGAGATGAC
3018 TATACCTGGCAATCTGGAACTAATGCTTCAGTCTTTTGGCAACAAGGACAACCATACCCT
3019 AGATTCACAATCCCTTTCATGAGTATTGCGTCAGCATATTATATGTTCTATGATGGGTAT
3020 GAAGATGACAATGGCACCACTTATGGGGCTGTTGTTACTAATGATATGGGAACACTTTGT
3021 GTGCGCATAGTGACTGAGCAACAGAAAAATGAGGTCAAGATAACCAGTAGGATTTATCAC
3022 AAGGCTAAACATATCAGTGCATGGTGTCAAGACCACCAAGAGCAGTTGCATATCAACAC
3023 ACATATAGCCCAAATTTTGTACCGCAAACAGGAACAGTTGAAACTCACATTAAGTTCAGA
3024 CCTGATGTTAAAGATGTAACATCAGTAATGACAGCT
3025 >190_HRV53b
3026 AACCCGGTAGAGAAATACACAGAGGCTATCTTAAATGAAGTATTAGTAGTCCCAAACATT
3027 AATGCAAGCAATCCACAAACTTCAAATTCAGCACCAGCACTAGATGCTGCAGAAACGGGT
3028 CATACAAGTCAGACACAACCTGAGGACATGCTGGAAACTAGATATGTCATCACAGACCAA
3029 ACCCGGGATGAAATGAGCATTGAAAGTTTCTTAGGCAGATCAAGTTGCATTGCTGAGATC
3030 CATACCAATTTAGACCATACTGGATACAATGAGCCTGGGAAAAACCACTCAGAATGGAAG
3031 ATTACACTCAAAGAAATGGCCCAGATTAGAAGGAAATGTGAGATGTTCACATATCTTAGA
3032 TTTGATTCAGAAATAACTATAGTGGTATCAGTGGCTAGTAAACAAGGGAATAACGGGCAC
3033 GTGGTGATACAATACATGTATGTACCACCGGGTGCTCCAATACCCAAAACCAGAGATGAC
3034 TATACCTGGCAATCTGGAACTAATGCTTCAGTCTTTTGGCAACAAGGACAACCATACCCT
3035 AGATTCACAATCCCTTTCATGAGTATTGCGTCAGCATATTATATGTTCTATGATGGGTAT
3036 GAAGATGACAATGGCACCACTTATGGGGCTGTTGTTACTAATGATATGGGAACACTTTGT
3037 GTGCGCATAGTGACTGAGCAACAGAAAAATGAGGTCAAGATAACCAGTAGGATTTATCAC
3038 AAGGCTAAACATATCAGTGCATGGTGTCCAAGACCACCAAGAGCAGTTGCATATCAACAC
3039 ACATATAGCCCAAATTTTGTACCGCAAACAGGAACAGTTGAAACTCACATTAAGTTCAGA
3040 CCTGATGTTAAAGATGTAACATCAGTAATGACAGCT
3041 >191_HRV5
3042 AACCCGGTAGAGAAATACACAGAGGCTATCTTAAATGAAGTATTAGTAGTCCCAAACATT
3043 AATGCAAGCAATCCACAAACTTCAAATTCAGCACCAGCACTAGATGCTGCAGAAACGGGT
3044 CATACAAGTCAGACACAACCTGAGGACATGCTGGAAACTAGATATGTCATCACAGACCAA
3045 ACCCGGGATGAAATGAGCATTGAAAGTTTCTTAGGCAGATCAAGTTGCATTGCTGAGATC
3046 CATACCAATTTAGACCATACTGGATACAATGAGCCTGGGAAAAACCACTCAGAATGGAAG
3047 ATTACACTCAAAGAAATGGCCCAGATTAGAAGGAAATGTGAGATGTTCACATATCTTAGA
3048 TTTGATTCAGAAATAACTATAGTGGTATCAGTGGCTAGTAAACAAGGGAATAACGGGCAC
3049 GTGGTGATACAATACATGTATGTACCACCGGGTGCTCCAATACCCAAAACCAGAGATGAC
3050 TATACCTGGCAATCTGGAACTAATGCTTCAGTCTTTTGGCAACAAGGACAACCATACCCT
3051 AGATTCACAATCCCTTTCATGAGTATTGCGTCAGCATATTATATGTTCTATGATGGGTAT
3052 GAAGATGACAATGGCACCACTTATGGGGCTGTTGTTACTAATGATATGGGAACACTTTGT
3053 GTGCGCATAGTGACTGAGCAACAGAAAAATGAGGTCAAGATAACCAGTAGGATTTATCAC
3054 AAGGCTAAACATATCAGTGCATGGTGTCCAAGACCACCAAGAGCAGTTGCATATCAACAC
3055 ACATATAGCCCAAATTTTGTACCGCAAACAGGAACAGTTGAAACTCACATTAAGTTCAGA
```

FIG. D1 CONT'D

Rhino cDNA DB.fasta                                    9/20/2007 5:08 PM

```
3056 CCTGATGTTAAAGATGTAACATCAGTAATGACAGCA
3057 >192_HRV46a
3058 AATCCAGTGGAAAAATATACAGAAGCTGTTCTTAATGAGGTCCTTGTAGTACCTAACATC
3059 AATGCCAGTAGTGGACATACATCTAATTCAGCTCCAGCACTTGATGCAGCAGAAACTGGA
3060 CACACTAGCCAGATACAACCAGAAGACATGATAGAAACCAGATATGTTATCACAGACCAA
3061 ACAAAAGATGAAATGAGTATAGAAAGTTTTCTAGGAAGGTCAGGCTGCATTGCCATTATT
3062 GAGACAGAATTGAATCATGAAGAAGGGAAATACAATGCAGAAGATCAAAACTTCTCAAAA
3063 TGGAAAATAACACTGTTGGAAATGGCACAAATCAGAAGAAAGTGTGAACTTTTTACATAT
3064 CTCAGATTTGATTCAGAAATAACAATAGTCACCACATTGGCAGGCCAAGGGGATGATATT
3065 GGACATGTGGTCATACAATATATGTATGTGCCTCCTGGTGCTCCATTACCGAGATATCGG
3066 AATGATTATACTTGGCAGTCTGGTACTAATGCTTCAGTGTTCTGGCAGCAAGGGCAGCCA
3067 TACCCTAGATTCACTATCCCGTTCATGAGTATAGCCTCAGCATATTACATGTTTTATGAT
3068 GGCTACGAAAGTGATAAAGGCAAGATCTATGGAACTGCAGTCACCAATGATATGGGAACT
3069 ATATGTGTCAGAATTGTTACCGAACAACAAAAACATAAGGTTCTTATAACTAGCAGAATA
3070 TATCACAAGGCTAAACACATTAAAGCATGGTGCCCCAGGGCACCCAGAGCAGTCCCATAT
3071 CAACATATTTATAATCCAAATTTCAAGACTACTCAACCTGAGACTATACCAGATACTCAT
3072 ATTGGAATTAGAAGGGATATAAAGTACATTAAAACAGCA
3073 >193_HRV46b
3074 AATCCAGTGGAAAAATATACAGAAGCTGTTCTTAATGAGGTCCTTGTAGTACCTAACATC
3075 AATGCCAGTAGTGGACATACATCTAATTCAGCTCCAGCACTTGATGCAGCAGAAACTGGA
3076 CACACTAGCCAGATACAACCAGAAGACATGATAGAAACCAGATATGTTATCACAGACCAA
3077 ACAAAAGATGAAATGAGTATAGAAAGTTTTCTAGGAAGGTCAGGCTGCATTGCCATTATT
3078 GAGACAGAATTGAATCATGAAGAAGGGAAATACAATGCAGAAGATCAAAACTTCTCAAAA
3079 TGGAAAATAACACTGTTGGAAATGGCACAAATCAGAAGAAAGTGTGAACTTTTTACATAT
3080 CTCAGATTTGATTCAGAAATAACAATAGTCACCACATTGGCAGGCCAAGGGGATGATATT
3081 GGACATGTGGTCATACAATATATGTATGTGCCTCCTGGTGCTCCATTACCGAGATATCGG
3082 AATGATTATACTTGGCAGTCTGGTACTAATGCTTCAGTGTTCTGGCAGCAAGGGCAGCCA
3083 TACCCTAGATTCACTATCCCGTTCATGAGTATAGCCTCAGCATATTACATGTTTTATGAT
3084 GGCTACGAAAGTGATAAAGGCAAGATCTATGGAACTGCAGTCACCAATGATATGGGAACT
3085 ATATGTGTCAGAATTGTTACCGAACAACAAAAACATAAGGTTCTTATAACTAGCAGAATA
3086 TATCACAAGGCTAAACACATTAAAGCATGGTGCCCCAGGGCACCCAGAGCAGTCCCATAT
3087 CAACATATTTATAATCCAAATTTCAAGACTACTCAACCTGAGACTATACCAGATACTCAT
3088 ATTGGAATTAGAAGGGATATAAAGTACATTAAAACAGCC
3089 >194_HRV46
3090 AATCCAGTGGAAAAATATACAGAAGCTGTTCTTAATGAGGTCCTTGTAGTACCTAACATC
3091 AATGCCAGTAGTGGACATACATCTAATTCAGCTCCAGCACTTGATGCAGCAGAAACTGGA
3092 CACACTAGCCAGATACAACCAGAAGACATGATAGAAACCAGATATGTTATCACAGACCAA
3093 ACAAAAGATGAAATGAGTATAGAAAGTTTTCTAGGAAGGTCAGGCTGCATTGCCATTATT
3094 GAGACAGAATTGAATCATGAAGAAGGGAAATACAATGCAGAAGATCAAAACTTCTCAAAA
3095 TGGAAAATAACACTGTTGGAAATGGCACAAATCAGAAGAAAGTGTGAACTTTTTACATAT
3096 CTCAGATTTGATTCAGAAATAACAATAGTCACCACATTGGCAGGCCAAGGGGATGATATT
3097 GGACATGTGGTCATACAATATATGTATGTGCCTCCTGGTGCTCCATTACCGAGATATCGG
3098 AATGATTATACTTGGCAGTCTGGTACTAATGCTTCAGTGTTCTGGCAGCAAGGGCAGCCA
3099 TACCCTAGATTCACTATCCCGTTCATGAGTATAGCCTCAGCATATTACATGTTTTATGAT
3100 GGCTACGAAAGTGATAAAGGCAAGATCTATGGAACTGCAGTCACCAATGATATGGGAACT
3101 ATATGTGTCAGAATTGTTACCGAACAACAAAAACATAAGGTTCTTATAACTAGCAGAATA
3102 TATCACAAGGCTAAACACATTAAAGCATGGTGCCCCAGGGCACCCAGAGCAGTCCCATAT
3103 CAACATATTTATAATCCAAATTTCAAGACTACTCAACCTGAGACTATACCAGATACTCAT
3104 ATTGGAATTAGAAGGGATATAAAGTACATTAAAACAGCT
3105 >195_HRV80a
3106 AATCCAGTCGAAAAATACACAGAAGCAATCCTCAATGAAGTTCTTGTTGTACCAAACATC
3107 AGTGCTAGCAATGGACATACATCAAACTCAGCTCCAACACTTGATGCAGCAGAAACTGGT
3108 CACACTAGCCAGGTGCAACCAGAAGACATGATAGAAACTAGATATGTTATTACTGATCAG
3109 ACAAAGGATGAGATGAGCATTGAAAGTTTCTTAGGAAGATCTGGTTGTGTTGCTATCATT
3110 GAAACCAAATTAAACCATGAAACAGACATGTACAATGCTGATGGTCAGAATTTTTCAAAG
3111 TGGAAAATAACATTAATGGAAATGGCACAAATTAGAAGAAAGTGTGAGCTTTTCACTTAC
3112 CTCAGATTTGACTCAGAAATAACAATAGTAACTACCTTAGCAGGACAAGGGGAGGACATT
3113 GGTCATGTAGTTATTCAATACATGTACGTACCACCAGGGGCCCCGTTGCCAAACAAACGC
3114 AATGATTATACTTGGCAGTCTGGCACGAATGCTTCAGTCTTCTGGCAACAGGGGTCAGCCA
3115 TACCCCAGATTCACTATTCCATTCATGAGTATAGCCTCAGCTTATTACATGTTCTATGAT
3116 GGGTATGAGAGTGATAAAGGCAACATTTATGGAACAGCAGTTACCAATGATATGGGAACC
3117 CTGTGTGCTAGAATTGTTACAGAACAACAGAAACATAAAGTCCTAATCACCAGCAGAATA
3118 TATCACAAAGCTAAACACATCAAAGCATGGTGTCCAAGAGCACCTAGAGCAGTCCCATAC
3119 CAACATACCTACAGCCCAAATTTCAAAAACACTGATGAATCTATACCAGATACACAAATT
3120 AAAATCAGAGATAATATCAGGCAGGTTAGAACAGTA
```

FIG. D1 CONT'D

Rhino cDNA DB.fasta                                              9/20/2007 5:08 PM

```
3121 >196_HRV80b
3122 AATCCAGTCGAAAAATACACAGAAGCAATCCTCAATGAAGTTCTTGTTGTACCAAACATC
3123 AGTGCTAGCAATGGACATACATCAAACTCAGCTCCAACACTTGATGCAGCAGAAACTGGT
3124 CACACTAGCCAGGTGCAACCAGAAGACATGATAGAAACTAGATATGTTATTACTGATCAG
3125 ACAAAGGATGAGATGAGCATTGAAAGTTTCTTAGGAAGATCTGGTTGTGTTGCTATCATT
3126 GAAACCAAATTAAACCATGAAACAGACATGTACAATGCTGATGGTCAGAATTTTTCAAAG
3127 TGGAAAATAACATTAATGGAAATGGCACAAATTAGAAGAAAGTGTGAGCTTTTCACTTAC
3128 CTCAGATTTGACTCAGAAATAACAATAGTAACTACCTTAGCAGGACAAGGGGAGGACATT
3129 GGTCATGTAGTTATTCAATACATGTACGTACCACCAGGGGCCCCGTTGCCAAACAAACGC
3130 AATGATTATACTTGGCAGTCTGGCACGAATGCTTCAGTCTTCTGGCAACAGGGTCAGCCA
3131 TACCCCAGATTCACTATTCCATTCATGAGTATAGCCTCAGCTTATTACATGTTCTATGAT
3132 GGGTATGAGAGTGATAAAGGCAACATTTATGGAACAGCAGTTACCAATGATATGGGAACC
3133 CTGTGTGCTAGAATTGTTACAGAACAACAGAAACATAAAGTCCTAATCACCAGCAGAATA
3134 TATCACAAAGCTAAACACATCAAAGCATGGTGTCCAAGAGCACCTAGAGCAGTCCCATAC
3135 CAACATACCTACAGCCCAAATTTCAAAAACACTGATGAATCTATACCAGATACACAAATT
3136 AAAATCAGAGATAATATCAGGCAGGTTAGAACAGTC
3137 >197_HRV80
3138 AATCCAGTCGAAAAATACACAGAAGCAATCCTCAATGAAGTTCTTGTTGTACCAAACATC
3139 AGTGCTAGCAATGGACATACATCAAACTCAGCTCCAACACTTGATGCAGCAGAAACTGGT
3140 CACACTAGCCAGGTGCAACCAGAAGACATGATAGAAACTAGATATGTTATTACTGATCAG
3141 ACAAAGGATGAGATGAGCATTGAAAGTTTCTTAGGAAGATCTGGTTGTGTTGCTATCATT
3142 GAAACCAAATTAAACCATGAAACAGACATGTACAATGCTGATGGTCAGAATTTTTCAAAG
3143 TGGAAAATAACATTAATGGAAATGGCACAAATTAGAAGAAAGTGTGAGCTTTTCACTTAC
3144 CTCAGATTTGACTCAGAAATAACAATAGTAACTACCTTAGCAGGACAAGGGGAGGACATT
3145 GGTCATGTAGTTATTCAATACATGTACGTACCACCAGGGGCCCCGTTGCCAAACAAACGC
3146 AATGATTATACTTGGCAGTCTGGCACGAATGCTTCAGTCTTCTGGCAACAGGGTCAGCCA
3147 TACCCCAGATTCACTATTCCATTCATGAGTATAGCCTCAGCTTATTACATGTTCTATGAT
3148 GGGTATGAGAGTGATAAAGGCAACATTTATGGAACAGCAGTTACCAATGATATGGGAACC
3149 CTGTGTGCTAGAATTGTTACAGAACAACAGAAACATAAAGTCCTAATCACCAGCAGAATA
3150 TATCACAAAGCTAAACACATCAAAGCATGGTGTCCAAGAGCACCTAGAGCAGTCCCATAC
3151 CAACATACCTACAGCCCAAATTTCAAAAACACTGATGAATCTATACCAGATACACAAATT
3152 AAAATCAGAGATAATATCAGGCAGGTTAGAACAGTT
3153 >198_HRV51
3154 AACCCTGTTGAAAAATATACAGAGGCTTTACTCAATGAAGTGTTGGTGGTTCCCAACATA
3155 CAACCTAGCAGTGGGCACACATCTAATGCTGCACCAGCTCTAGATGCTGCTGAGACAGGA
3156 CATACTAGTCAAGTTCAACCAGAAGATATGGTAGAGACCAGGTATGTTGTCACAGACCAA
3157 ACTAGAGATGAAATGAGTATAGAGAGTTTCTTGGGTAGATCTGCTTGCGTAGCAATCATC
3158 CATACAAACCTTGAGCATGTTGAAGCAGACAGACAAGCCTACAATGCAAAAGGGAAAAAT
3159 TTCTCTACATGGAAAATTACACTCAAAGAAATGGCTCAAATTAGAAGAAAGTGTGAACTT
3160 TTCACATACTTAAGATTTGATTCAGAGATCACTATAGTTGCTACCATTGCTGGACAGGGT
3161 GATGACATAGGGCACATTGTACTTCAATACATGTATGTACCCCCTGGAGGACCAGTTCCA
3162 CTTACTAGGAAAGATGATGAGTGGCAATCAGGAACTAATGCTTCAGTATTCTGGCAACAT
3163 GGACAACCATACCCTAGATTTACAATCCCTTTTGTAAGCATAGCCTCAGCATACTACATG
3164 TTTTATGATGGGTATGAAGGTGATAGTTTGACCTCACAGTACGGTTCAGTAGTCACAAAT
3165 GCTATGGGGACACTATGTGTTCGTGTGGTCACAGAGCAACAAAAACATGAGGTTAACATA
3166 ACTAGCAGGATTTACCACAAAGCCAAACATGTCAGTGCATGGTGCCCTCGTCCTCCTCGT
3167 GCTGTAGCCTACCAACACACATACAGTACAAACTTCGTTCCAAAAGAGGGATTTGAAGGC
3168 TTGAAAACTCAGATTAAAACTAGGGCAGACATCAAACTTGTGAACTTT
3169 >199_HRV51a
3170 AACCCTGTTGAAAAATATACAGAGGCTTTACTCAATGAAGTGTTGGTGGTTCCCAACATA
3171 CAACCTAGCAGTGGGCACACATCTAATGCTGCACCAGCTCTAGATGCTGCTGAGACAGGA
3172 CATACTAGTCAAGTTCAACCAGAAGATATGGTAGAGACCAGGTATGTTGTCACAGACCAA
3173 ACTAGAGATGAAATGAGTATAGAGAGTTTCTTGGGTAGATCTGCTTGCGTAGCAATCATC
3174 CATACAAACCTTGAGCATGTTGAAGCAGACAGACAAGCCTACAATGCAAAAGGGAAAAAT
3175 TTCTCTACATGGAAAATTACACTCAAAGAAATGGCTCAAATTAGAAGAAAGTGTGAACTT
3176 TTCACATACTTAAGATTTGATTCAGAGATCACTATAGTTGCTACCATTGCTGGACAGGGT
3177 GATGACATAGGGCACATTGTACTTCAATACATGTATGTACCCCCTGGAGGACCAGTTCCA
3178 CTTACTAGGAAAGATGATGAGTGGCAATCAGGAACTAATGCTTCAGTATTCTGGCAACAT
3179 GGACAACCATACCCTAGATTTACAATCCCTTTTGTAAGCATAGCCTCAGCATACTACATG
3180 TTTTATGATGGGTATGAAGGTGATAGTTTGACCTCACAGTACGGTTCAGTAGTCACAAAT
3181 GCTATGGGGACACTATGTGTTCGTGTGGTCACAGAGCAACAAAAACATGAGGTTAACATA
3182 ACTAGCAGGATTTACCACAAAGCCAAACATGTCAGTGCATGGTGCCCTCGTCCTCCTCGT
3183 GCTGTAGCCTACCAACACACATACAGTACAAACTTCGTTCCAAAAGAGGGATTTGAAGGC
3184 TTGAAAACTCAGATTAAAACTAGGGCAGACATCAAACTTGTGAACTTA
3185 >200_HRV51b
```

FIG. D1 CONT'D

Rhino cDNA_DB.fasta                                                9/20/2007 5:08 PM

```
3186 AACCCTGTTGAAAAATATACAGAGGCTTTACTCAATGAAGTGTTGGTGGTTCCCAACATA
3187 CAACCTAGCAGTGGGCACACATCTAATGCTGCACCAGCTCTAGATGCTGCTGAGACAGGA
3188 CATACTAGTCAAGTTCAACCAGAAGATATGGTAGAGACCAGGTATGTTGTCACAGACCAA
3189 ACTAGAGATGAAATGAGTATAGAGAGTTTCTTGGGTAGATCTGCTTGCGTAGCAATCATC
3190 CATACAAACCTTGAGCATGTTGAAGCAGACAGACAAGCCTACAATGCAAAAGGGAAAAAT
3191 TTCTCTACATGGAAAATTACACTCAAAGAAATGGCTCAAATTAGAAGAAAGTGTGAACTT
3192 TTCACATACTTAAGATTTGATTCAGAGATCACTATAGTTGCTACCATTGCTGGACAGGGT
3193 GATGACATAGGGCACATTGTACTTCAATACATGTATGTACCCCCTGGAGGACCAGTTCCA
3194 CTTACTAGGAAAGATGATGAGTGGCAATCAGGAACTAATGCTTCAGTATTCTGGCAACAT
3195 GGACAACCATACCCTAGATTTACAATCCCTTTTGTAAGCATAGCCTCAGCATACTACATG
3196 TTTTATGATGGGTATGAAGGTGATAGTTTGACCTCACAGTACGGTTCAGTAGTCACAAAT
3197 GCTATGGGGACACTATGTGTTCGTGTGGTCACAGAGCAACAAAAACATGAGGTTAACATA
3198 ACTAGCAGGATTTACCACAAAGCCAAACATGTCAGTGCATGGTGCCCTCGTCCTCCTCGT
3199 GCTGTAGCCTACCAACACACATACAGTACAAACTTCGTTCCAAAAGAGGGATTTGAAGGC
3200 TTGAAAACTCAGATTAAAACTAGGGCAGACATCAAACTTGTGAACTTG
3201 >201_HRV65a
3202 AATCCAATTGAGAAGTATACAGAAGCTCTACTTAATGAAGTGTTGGTGGTCCCAAATATA
3203 CAAGCTAGTAATGGGCATACATCTAATGCTGCACCAGCTTTAGATGCTGCTGAAACAGGA
3204 CACACTAGTCAAGTTCAACCAGAGGATGTGATAGAACCAGATATGTCATCACAGATCAA
3205 ACCAGAGATGAGATGAGCGTAGAGAGTTTCCTGGGCAGATCTGCCTGCATAGCAGTCATT
3206 CACACAGATCTTAAACATGACCATGAAGGCCAAAATGTTTACAATGACGAAGGCAGAAAT
3207 TTCTCTGCTTGGGAAATTACACTCAAGGAAATGGCTCAAATTAGGAGAAAGTGTGAACTC
3208 TTCACCTATTTGCGCTTTGACTCAGAAATTACCATAGTGGCTACTATAGCTGGACAAGGT
3209 GATGACATAGGGCACATAGTGCTTCAATATATGTATGTGCCTCCTGGTGGTCCTGTTCCA
3210 AAAACTAGAAAAGATGAAGAGTGGCAGACAGGAACTAATGCTTCAGTCTTTTGGCAGCAT
3211 GGTCAACCATACCCCAGATTTACAATTCCTTTTGTGAGTATTGCCTCAGCATATTACATG
3212 TTCTATGATGGTTATGAGGGTGATGACCCAAATTCAAAATATGGTTCAGTGGTTACTAAT
3213 GCTATGGGCACACTATATGTGCGTGTGGTTACAGAAAGGCAAAAACATGAAGTCAACATA
3214 ACCAGTAGAATATATCATAAAGCTAAACACATCAGTGCTTGGTGTCCACGACCTCCCCGA
3215 GCAGTAGCTTACCAACACACATACAGTACAAATTTTGTTCCTAGCGGAGGTCTTACAAAC
3216 CTAAGAACCCAAATTAAAACCAGAGATAACATTAAAATTGTAAACTTG
3217 >202_HRV65b
3218 AATCCAATTGAGAAGTATACAGAAGCTCTACTTAATGAAGTGTTGGTGGTCCCAAATATA
3219 CAAGCTAGTAATGGGCATACATCTAATGCTGCACCAGCTTTAGATGCTGCTGAAACAGGA
3220 CACACTAGTCAAGTTCAACCAGAGGATGTGATAGAAACCAGATATGTCATCACAGATCAA
3221 ACCAGAGATGAGATGAGCGTAGAGAGTTTCCTGGGCAGATCTGCCTGCATAGCAGTCATT
3222 CACACAGATCTTAAACATGACCATGAAGGCCAAAATGTTTACAATGACGAAGGCAGAAAT
3223 TTCTCTGCTTGGGAAATTACACTCAAGGAAATGGCTCAAATTAGGAGAAAGTGTGAACTC
3224 TTCACCTATTTGCGCTTTGACTCAGAAATTACCATAGTGGCTACTATAGCTGGACAAGGT
3225 GATGACATAGGGCACATAGTGCTTCAATATATGTATGTGCCTCCTGGTGGTCCTGTTCCA
3226 AAAACTAGAAAAGATGAAGAGTGGCAGACAGGAACTAATGCTTCAGTCTTTTGGCAGCAT
3227 GGTCAACCATACCCCAGATTTACAATTCCTTTTGTGAGTATTGCCTCAGCATATTACATG
3228 TTCTATGATGGTTATGAGGGTGATGACCCAAATTCAAAATATGGTTCAGTGGTTACTAAT
3229 GCTATGGGCACACTATATGTGCGTGTGGTTACAGAAAGGCAAAAACATGAAGTCAACATA
3230 ACCAGTAGAATATATCATAAAGCTAAACACATCAGTGCTTGGTGTCCACGACCTCCCCGA
3231 GCAGTAGCTTACCAACACACATACAGTACAAATTTTGTTCCTAGCGGAGGTCTTACAAAC
3232 CTAAGAACCCAAATTAAAACCAGAGATAACATTAAAATTGTAAACTTA
3233 >203_HRV65
3234 AATCCAATTGAGAAGTATACAGAAGCTCTACTTAATGAAGTGTTGGTGGTCCCAAATATA
3235 CAAGCTAGTAATGGGCATACATCTAATGCTGCACCAGCTTTAGATGCTGCTGAAACAGGA
3236 CACACTAGTCAAGTTCAACCAGAGGATGTGATAGAAACCAGATATGTCATCACAGATCAA
3237 ACCAGAGATGAGATGAGCGTAGAGAGTTTCCTGGGCAGATCTGCCTGCATAGCAGTCATT
3238 CACACAGATCTTAAACATGACCATGAAGGCCAAAATGTTTACAATGACGAAGGCAGAAAT
3239 TTCTCTGCTTGGGAAATTACACTCAAGGAAATGGCTCAAATTAGGAGAAAGTGTGAACTC
3240 TTCACCTATTTGCGCTTTGACTCAGAAATTACCATAGTGGCTACTATAGCTGGACAAGGT
3241 GATGACATAGGGCACATAGTGCTTCAATATATGTATGTGCCTCCTGGTGGTCCTGTTCCA
3242 AAAACTAGAAAAGATGAAGAGTGGCAGACAGGAACTAATGCTTCAGTCTTTTGGCAGCAT
3243 GGTCAACCATACCCCAGATTTACAATTCCTTTTGTGAGTATTGCCTCAGCATATTACATG
3244 TTCTATGATGGTTATGAGGGTGATGACCCAAATTCAAAATATGGTTCAGTGGTTACTAAT
3245 GCTATGGGCACACTATATGTGCGTGTGGTTACAGAAAGGCAAAAACATGAAGTCAACATA
3246 ACCAGTAGAATATATCATAAAGCTAAACACATCAGTGCTTGGTGTCCACGACCTCCCCGA
3247 GCAGTAGCTTACCAACACACATACAGTACAAATTTTGTTCCTAGCGGAGGTCTTACAAAC
3248 CTAAGAACCCAAATTAAAACCAGAGATAACATTAAAATTGTAAACTTT
3249 >204_HRV71a
3250 AATCCTGTAGAAAAATATACAGAAGCAATACTCAATGAGGTTCTAGTTGTGCCAAATATA
```

FIG. D1 CONT'D

Rhino cDNA DB.fasta                                              9/20/2007 5:08 PM

```
3251  CAACCTAGTAATGGACATACCTCAAACTCAGCACCAGCCTTAGATGCAGCAGAAACTGGG
3252  CATACCAACCAAGTACAACCAGAAGATGTTATGGAAACCAGATATGTGATCACTGATCAA
3253  ACTAGGGATGAAATGAGCATTGAGAGCTTCTTGGGCAGATCTGCATGCATAGCTACCATA
3254  CACACTAAATTAGTACATGGAGAGGAGGGTGTTTATAATATGAAAGGTAACAATCTCTCA
3255  AAGTGGCAGATTACACTCAAAGAAATGGCTCAGATCAGGAGGAAATGTGAACTCTTCACA
3256  TACCTGCGCTTTGATTCAGAGATAACAATTGTAGCTACACTAGCAGGGCAAGGAGATGAT
3257  TTAGGACATATTGTACTCCAGTACATGTATGTTCCCCCAGGTGGTCCAATACCAGAGACC
3258  AGGGATGCCGATGAATGGCAGTCTGGAACTAATGCATCAGTCTTTTGGCAGCACGGCCAA
3259  CCATACCCAAGGTTTACAATCCCCTTCATAAGCATTGCATCAGCATATTACATGTTCTAT
3260  GATGGGTATGAAGGTGATGCCCTCAGTTCTAAATATGGCTCAGTAGTTACTAATGCCATG
3261  GGCACCTTATGTGTTCGTGTGGTTACAGAACAGCAAAGCAACACAGTCAACATAACAAGT
3262  AGGATTTATCACAAAGCCAAACATGTCAGAGCATGGTGTCCTAGACCCCCCAGAGCAGTA
3263  GCCTACCAATCAACATATACCACAAATTTTGTTCCACAAGACGGGATCAATTCCATTAAA
3264  ACCAAAATCAAAATCAGAAGAGACATTAAAGAGGTCAGCAACTAA
3265  >205_HRV71b
3266  AATCCTGTAGAAAAATATACAGAAGCAATACTCAATGAGGTTCTAGTTGTGCCAAATATA
3267  CAACCTAGTAATGGACATACCTCAAACTCAGCACCAGCCTTAGATGCAGCAGAAACTGGG
3268  CATACCAACCAAGTACAACCAGAAGATGTTATGGAAACCAGATATGTGATCACTGATCAA
3269  ACTAGGGATGAAATGAGCATTGAGAGCTTCTTGGGCAGATCTGCATGCATAGCTACCATA
3270  CACACTAAATTAGTACATGGAGAGGAGGGTGTTTATAATATGAAAGGTAACAATCTCTCA
3271  AAGTGGCAGATTACACTCAAAGAAATGGCTCAGATCAGGAGGAAATGTGAACTCTTCACA
3272  TACCTGCGCTTTGATTCAGAGATAACAATTGTAGCTACACTAGCAGGGCAAGGAGATGAT
3273  TTAGGACATATTGTACTCCAGTACATGTATGTTCCCCCAGGTGGTCCAATACCAGAGACC
3274  AGGGATGCCGATGAATGGCAGTCTGGAACTAATGCATCAGTCTTTTGGCAGCACGGCCAA
3275  CCATACCCAAGGTTTACAATCCCCTTCATAAGCATTGCATCAGCATATTACATGTTCTAT
3276  GATGGGTATGAAGGTGATGCCCTCAGTTCTAAATATGGCTCAGTAGTTACTAATGCCATG
3277  GGCACCTTATGTGTTCGTGTGGTTACAGAACAGCAAAGCAACACAGTCAACATAACAAGT
3278  AGGATTTATCACAAAGCCAAACATGTCAGAGCATGGTGTCCTAGACCCCCCAGAGCAGTA
3279  GCCTACCAATCAACATATACCACAAATTTTGTTCCACAAGACGGGATCAATTCCATTAAA
3280  ACCAAAATCAAAATCAGAAGAGACATTAAAGAGGTCAGCAACTAG
3281  >206_HRV71
3282  AATCCTGTAGAAAAATATACAGAAGCAATACTCAATGAGGTTCTAGTTGTGCCAAATATA
3283  CAACCTAGTAATGGACATACCTCAAACTCAGCACCAGCCTTAGATGCAGCAGAAACTGGG
3284  CATACCAACCAAGTACAACCAGAAGATGTTATGGAAACCAGATATGTGATCACTGATCAA
3285  ACTAGGGATGAAATGAGCATTGAGAGCTTCTTGGGCAGATCTGCATGCATAGCTACCATA
3286  CACACTAAATTAGTACATGGAGAGGAGGGTGTTTATAATATGAAAGGTAACAATCTCTCA
3287  AAGTGGCAGATTACACTCAAAGAAATGGCTCAGATCAGGAGGAAATGTGAACTCTTCACA
3288  TACCTGCGCTTTGATTCAGAGATAACAATTGTAGCTACACTAGCAGGGCAAGGAGATGAT
3289  TTAGGACATATTGTACTCCAGTACATGTATGTTCCCCCAGGTGGTCCAATACCAGAGACC
3290  AGGGATGCCGATGAATGGCAGTCTGGAACTAATGCATCAGTCTTTTGGCAGCACGGCCAA
3291  CCATACCCAAGGTTTACAATCCCCTTCATAAGCATTGCATCAGCATATTACATGTTCTAT
3292  GATGGGTATGAAGGTGATGCCCTCAGTTCTAAATATGGCTCAGTAGTTACTAATGCCATG
3293  GGCACCTTATGTGTTCGTGTGGTTACAGAACAGCAAAGCAACACAGTCAACATAACAAGT
3294  AGGATTTATCACAAAGCCAAACATGTCAGAGCATGGTGTCCTAGACCCCCCAGAGCAGTA
3295  GCCTACCAATCAACATATACCACAAATTTTGTTCCACAAGACGGGATCAATTCCATTAAA
3296  ACCAAAATCAAAATCAGAAGAGACATTAAAGAGGTCAGCAACTAT
3297  >207_HRV8
3298  AACCCTATTGAACAATTCACAGAGGCAGTATTAAACGAGGTTCTTGTAGTTCCAAACACA
3299  CAAGCTAGTAATGGATCTATAGCAAATTCAGCACCAGCCTTAGATGCAGCAGAGACTGGG
3300  CACACAAGTTCAGTGCAACCTGAAGATCTTATAGAGACTAGGTATGTAATTACAGATCAA
3301  ACTAGGCATGAGACATCACTGGAATCTTTCTTGGGTAGAGCAGGATGCATTAAAATCATT
3302  GCATTAGAACTAGATCATGACAACTATGATGAAAGTTTCAGGACCTGGGGAATAAACATA
3303  CAAGAGATGTCACAAATTAGAAGGAAATTTGAGATGTTCACTTATGTAAGATTTGATTCA
3304  GAGATAACAATTGTACCATGTATTGCAGCTATAAAAGGTGACCTTGGACACATAGTCCTT
3305  CAATACATGTATGTTCCCCCGGGTGCACCTCTTCCAGATAAAAGGATGCACGATGCCTGG
3306  CAAACCAGTACAAATGCCTCAGTCTTCTGGCAAGTTGGACAAACTTATCCCAGATTCACC
3307  ATACCTTTCTCCAGCATAGCATCAGCTTATTACATGTTCTATGATGGTTATGATTCAGAT
3308  GGTTTAGATGCTATTTATGGTATTCCTGTTACAAATCACATGGGCACAATATGTGTGAGA
3309  ATGGTGACAGATAAACAGAAAATTAAAACTAAAATTGATTCAAGAATATACCTGAAAGCA
3310  AAGCACATTAAAGCTTGGTGTCCTAGACCCCCCAGAGCAGTTACGTATAACCATATATAC
3311  AACCCCAATTATGTTAGAGAGGGAGTAACACCAGAAACTAAGGTTAAATATAGAGCTGAA
3312  GTCACAACCATT
3313  >208_HRV95
3314  AACCCTATTGAACAATTCACAGAGGCAGTATTAAACGAGGTTCTTGTAGTTCCAAATACA
3315  CAAGCCAGTAATGGATCTATAGCAAATTCAGCACCAGCATTAGATGCAGCAGAGACTGGA
```

FIG. D1 CONT'D

Rhino_cDNA_DB.fasta                                                                      9/20/2007 5:08 PM

```
3316  CACACAAGTTCAGTGCAACCTGAAGATCTTATAGAGACTAGGTATGTAATTACAGATCAA
3317  ACTAGGTATGAGACATCACTGGAATCTTTCTTGGGTAGAGCAGGATGCATTAAAATTATT
3318  GCATTAGAACTAGATCATGACAACTATGATAAAAATTTCAGGACCTGGGGAATAAACATA
3319  CAAGAGATGTCACAAATTAGAAGGAAATTTGAAATGTTCACTTATGTAAGATTTGATTCA
3320  GAGATAACAATTGTACCATGTATTGCAGCTATAGAAGGTGACCTTGGACACATAGTCCTC
3321  CAATACATGTATGTTCCCCGGGTGCACCTCTTCCAGATAAAAGGATGCACGATGCCTGG
3322  CAAACCAGTACAAATGCCTCAGTCTTCTGGCAAGTTGGACAGACTTATCCCAGATTCACC
3323  ATACCTTTCTCCAGTATAGCATCAGCTTATTACATGTTCTATGATGGTTATGATTCAGAT
3324  GGTTTAGATGCTATTTATGGTATTCCTGTTACAAATCACATGGGCACAATATGTGTGAGA
3325  ATGGTGACAGATAAACAGAAAATTAAAACTAAAATTGATTCAAGAATATACCTGAAAGCA
3326  AAGCATATTAAAGCTTGGTGTCCTAGACCCCCAGAGCAGTTACGTATAACCATATATAC
3327  AACCCCAATTATGTTAGAGAGGGAGTAACACCAGAAACTAAGGTCAAATATAGAGCTGAA
3328  GTCACAACCATT
3329  >209_HRV45
3330  AACCCTGTTGAACAATTTGCAGAAGCAGTCCTTGATCAAGTATTAGTAGTTCCAAACACT
3331  CGACCCAGCGATGGGTTGATTGCAAACTCAGCCCCAGCTTTGGATGCAGCTGAAACTGGA
3332  CACACCAGTTCAGTGCAGCCTGAGGACCTTATAGAGACTAGATATGTGATTGCAGACCAA
3333  ACCAGACATGAAACCTCCATTGAATCTTTTTTGGGTAGGGCTGGATGTGTGGCCAATATT
3334  AGTTTAGACATTAACCATGATGACTACCAAAAGAATTACAAAAATTGGGCAATTAGTTTA
3335  CAAGAAATGTCACAAATTAGGAGGAAATTTGAAATGTTTACATATGTCAGATTTGATTCC
3336  GAAATAACAATAGTACCATGTGTTGCTGCCACAGAAGGTAACTTGGGACACATTGTTGTG
3337  CAATACATGTTTGTACCACCAGGAGCACCTCTCCCTGTTAGTAGAACTGACAACACTTGG
3338  CAATCTAGCACAAATGCATCAGTCTTTTGGCAGGTTGGTCAAACTTATCCCAGATTTTCT
3339  ATACCTTTCTCAAGTATAGCTTCAGCTTACTACATGTTTTATGATGGATACGACACTGAT
3340  GGCACAGATGCAGTGTATGGTGTTAGTGTGACTAACCATATGGGGACTATATGTGTTAGA
3341  ATTGTTACAGACCAACAACAACATAGAGTTAAGATCGACTCCATGGTATATCTAAAAGCT
3342  AAACACATCAAGGCATGGTGTCCCAGACCTCCAAGAGCAGTCACATATAACCATACATAT
3343  AATCCAAATTATGTTAGGGCTGATGAAACAGCCACAAAAGTCCAAACTAGAGCAAATGTC
3344  ACAACAGTA
3345  >210_HRV45a
3346  AACCCTGTTGAACAATTTGCAGAAGCAGTCCTTGATCAAGTATTAGTAGTTCCAAACACT
3347  CGACCCAGCGATGGGTTGATTGCAAACTCAGCCCCAGCTTTGGATGCAGCTGAAACTGGA
3348  CACACCAGTTCAGTGCAGCCTGAGGACCTTATAGAGACTAGATATGTGATTGCAGACCAA
3349  ACCAGACATGAAACCTCCATTGAATCTTTTTTGGGTAGGGCTGGATGTGTGGCCAATATT
3350  AGTTTAGACATTAACCATGATGACTACCAAAAGAATTACAAAAATTGGGCAATTAGTTTA
3351  CAAGAAATGTCACAAATTAGGAGGAAATTTGAAATGTTTACATATGTCAGATTTGATTCC
3352  GAAATAACAATAGTACCATGTGTTGCTGCCACAGAAGGTAACTTGGGACACATTGTTGTG
3353  CAATACATGTTTGTACCACCAGGAGCACCTCTCCCTGTTAGTAGAACTGACAACACTTGG
3354  CAATCTAGCACAAATGCATCAGTCTTTTGGCAGGTTGGTCAAACTTATCCCAGATTTTCT
3355  ATACCTTTCTCAAGTATAGCTTCAGCTTACTACATGTTTTATGATGGATACGACACTGAT
3356  GGCACAGATGCAGTGTATGGTGTTAGTGTGACTAACCATATGGGGACTATATGTGTTAGA
3357  ATTGTTACAGACCAACAACAACATAGAGTTAAGATCGACTCCATGGTATATCTAAAAGCT
3358  AAACACATCAAGGCATGGTGTCCCAGACCTCCAAGAGCAGTCACATATAACCATACATAT
3359  AATCCAAATTATGTTAGGGCTGATGAAACAGCCACAAAAGTCCAAACTAGAGCAAATGTC
3360  ACAACAGTG
3361  >211_HRV45b
3362  AACCCTGTTGAACAATTTGCAGAAGCAGTCCTTGATCAAGTATTAGTAGTTCCAAACACT
3363  CGACCCAGCGATGGGTTGATTGCAAACTCAGCCCCAGCTTTGGATGCAGCTGAAACTGGA
3364  CACACCAGTTCAGTGCAGCCTGAGGACCTTATAGAGACTAGATATGTGATTGCAGACCAA
3365  ACCAGACATGAAACCTCCATTGAATCTTTTTTGGGTAGGGCTGGATGTGTGGCCAATATT
3366  AGTTTAGACATTAACCATGATGACTACCAAAAGAATTACAAAAATTGGGCAATTAGTTTA
3367  CAAGAAATGTCACAAATTAGGAGGAAATTTGAAATGTTTACATATGTCAGATTTGATTCC
3368  GAAATAACAATAGTACCATGTGTTGCTGCCACAGAAGGTAACTTGGGACACATTGTTGTG
3369  CAATACATGTTTGTACCACCAGGAGCACCTCTCCCTGTTAGTAGAACTGACAACACTTGG
3370  CAATCTAGCACAAATGCATCAGTCTTTTGGCAGGTTGGTCAAACTTATCCCAGATTTTCT
3371  ATACCTTTCTCAAGTATAGCTTCAGCTTACTACATGTTTTATGATGGATACGACACTGAT
3372  GGCACAGATGCAGTGTATGGTGTTAGTGTGACTAACCATATGGGGACTATATGTGTTAGA
3373  ATTGTTACAGACCAACAACAACATAGAGTTAAGATCGACTCCATGGTATATCTAAAAGCT
3374  AAACACATCAAGGCATGGTGTCCCAGACCTCCAAGAGCAGTCACATATAACCATACATAT
3375  AATCCAAATTATGTTAGGGCTGATGAAACAGCCACAAAAGTCCAAACTAGAGCAAATGTC
3376  ACAACAGTT
3377  >212_HRV6
3378  >213_HRV6a|
3379  >214_HRV6b|
3380  >215_HRV37
```

FIG. D1 CONT'D

Rhino cDNA DB.fasta                                              9/20/2007 5:08 PM

```
3381  >216_HRV37a
3382  >217_HRV37b
3383  >218_HRV3
3384  >219_HRV3a|
3385  >220_HRV3b|
3386  >221_HRV14
3387  >222_HRV14a
3388  >223_HRV14b
3389  >224_HRV72
3390  >225_HRV72a
3391  >226_HRV72b
3392  >227_HRV83
3393  >228_HRV83a
3394  >229_HRV83b
3395  >230_HRV92
3396  >231_HRV92a
3397  >232_HRV92b
3398  >233_HRV79
3399  >234_HRV79a
3400  >235_HRV79b
3401  >236_HRV35
3402  >237_HRV35a
3403  >238_HRV35b
3404  >239_1HRV86
3405  >240_1HRV86
3406  >241_1HRV86
3407  >242_HRV70
3408  >243_HRV70a
3409  >244_HRV70b
3410  >245_HRV91
3411  >246_HRV91a
3412  >247_HRV91b
3413  >248_HRV17
3414  >249_HRV17a
3415  >250_HRV17b
3416  >251_HRV69
3417  >252_HRV69a
3418  >253_HRV69b
3419  >254_HRV48
3420  >255_HRV48a
3421  >256_HRV48b
3422  >257_HRV52
3423  >258_HRV52a
3424  >259_HRV52b
3425  >260_HRV4
3426  >261_HRV4a|
3427  >262_HRV4b|
3428  >263_HRV99
3429  >264_HRV99a
3430  >265_HRV99b
3431  >266_HRV5
3432  >267_HRV5a|
3433  >268_HRV5b|
3434  >269_HRV42
3435  >270_HRV42a
3436  >271_HRV42b
3437  >272_HRV26
3438  >273_HRV26a
3439  >274_HRV26b
3440  >275_HRV27
3441  >276_HRV27a
3442  >277_HRV27b
3443  >278_HRV93
3444  >279_HRV93a
3445  >280_HRV93b
```

FIG. D1 CONT'D

```
Rhino cDNA DB.fasta                                          9/20/2007 5:08 PM
3446  >281_HRV97
3447  >282_HRV97a
3448  >283_HRV97b
3449  >284_HRV84
3450  >285_HRV84a
3451  >286_HRV84b
3452  >287_HRV87
3453  >288_HRV87a
3454  >289_HRV87b
3455
```

FIG. D1 CONT'D read_database_sequence.pl                                    9/20/2007 5:06 PM

```perl
 1  #!/usr/bin/perl -w
 2
 3  use strict;
 4
 5
 6
 7
 8
 9  my ($trace01File, @group01, @alignSeq01, @summaryInfo01);
10  $trace01File="01.trace";
11  readPartitionInfor($trace01File, \@group01, \@alignSeq01, \@summaryInfo01);
12
13  my ($i, $j, $k);
14  for($i=0;$i<@group01;$i++)
15  {
16      for($j=0;$j<@{$group01[$i]};$j++)
17      {
18          print ">$group01[$i][$j]\n";
19
20          my $counter=1;
21
22          my @a = @{$alignSeq01[$i][$j]};
23
24          for($k=0;$k<@a;$k++)
25          {
26              if($a[$k] ne '-')
27              {
28                  print "$a[$k]";
29
30                  if($counter==60)
31                  {
32                      $counter=0;
33                      print "\n";
34                  }
35                  $counter++;
36              }
37          }
38
39          if($counter !=1 ) {print "\n";}
40      }
41  }
42
43  sub readPartitionInfor
44  {
45      my($fileName, $currGrpRef, $currAlignRef, $summaryInfoRef)=@_;
46      my ($flag, $i, $j, @elements, $grpID);
47      my ($name, $seq, $seqIndex);
48
49      open (INPUT, $fileName) or die "cannot open $fileName";
50
51      $flag=0;
52      while(<INPUT>)
53      {
54          chomp();
55          if (/^\s*$/)
56          {$seqIndex=0;next;}
57
58          if(/>>>>>/)
59          {
60              $flag=1; next;
61          }
62
63          if(/Summary:/)
64          {
```

FIG. D2 read_database_sequence.pl                                    9/20/2007 5:06 PM

```
 65            $flag=2; next;
 66         }
 67
 68         if($flag==0)
 69         {
 70            @elements = split(" ", $_);
 71
 72            $elements[1] =~/(.+?):/;
 73            $grpID=$1-1;
 74            #print "$grpID\n";
 75            push(@{$currGrpRef->[$grpID]}, $elements[2]);
 76            next;
 77         }
 78
 79
 80         if($flag==1)
 81         {
 82            if(/Group\s+(\d+)/)
 83            {
 84               $grpID=$1-1;
 85               $seqIndex=0;
 86               next;
 87            }
 88            ($name, $seq) = split(" ", $_);
 89
 90            if(exists $currAlignRef->[$grpID]->[$seqIndex])
 91            {
 92               push(@{$currAlignRef->[$grpID]->[$seqIndex]}, split("",$seq));
 93            }
 94            else
 95            {
 96               @{$currAlignRef->[$grpID]->[$seqIndex]}=split("", $seq);
 97            }
 98            $seqIndex++;
 99
100            next;
101         }
102
103         if($flag==2)
104         {
105            ($name, $seq) = split(" ", $_);
106
107            if(exists $summaryInfoRef->[$seqIndex])
108            {
109               push(@{$summaryInfoRef->[$seqIndex]}, split("",$seq));
110            }
111            else
112            {
113               @{$summaryInfoRef->[$seqIndex]}=split("",$seq);
114            }
115            $seqIndex++;
116         }
117
118
119      }
120
121      #for($i=0;$i<@{$summaryInfoRef};$i++)
122      #{
123         #print "$i\t$summaryInfoRef->[$i]\n";
124      #}
125      #for($i=0;$i<@{$currAlignRef};$i++)
126      #{
127         #print "$i\n";
128         #for($j=0;$j<@{$currAlignRef->[$i]};$j++)
```

FIG. D2 CONT'D read_database_sequence.pl                9/20/2007 5:06 PM

```
129        #{
130            #print "$currGrpRef->[$i]->[$j] ";
131            #print "$j\t$currAlignRef->[$i]->[$j]\n "
132        #}
133        #print "\n";
134     #}
135  }
136
137
```

FIG. D2 CONT'D group_info-1.txt                                                    9/20/2007 5:06 PM

```
  1  Partition 1
  2  Group 1:
  3  1_HRV1A1|d 2_HRV1A2|d 3_HRV1A|cD 4_HRV1B1|d 5_HRV1B2|d 6_HRV1B 7_HRV40a|d 8_HRV40b|d 9_H
  4  11_HRV85a| 12_HRV85b| 13_HRV56a| 14_HRV56b| 15_HRV56 16_HRV54 17_HRV98 18_HRV59a| 19_HRV
  5  21_HRV63 22_HRV63b| 23_HRV63a| 24_HRV39 25_HRV39a| 26_HRV39b| 27_HRV10a| 28_HRV10b| 29_H
  6  31_HRV100b 32_HRV100 33_HRV66 34_HRV66b| 35_HRV66a| 36_HRV77a| 37_HRV77b| 38_HRV77 39_HR
  7  41_HRV25 42_HRV29a 43_HRV29b 44_HRV44a 45_HRV44b 46_HRV31 47_HRV31a| 48_HRV31b| 49_HRV47
  8  51_HRV47b| 52_HRV11 53_HRV11b| 54_HRV11a| 55_HRV76 56_HRV76b| 57_HRV76a| 58_HRV33 59_HRV
  9  61_HRV24a| 62_HRV24b| 63_HRV24 64_HRV90 65_HRV90a| 66_HRV90b| 67_HRV34 68_HRV34b| 69_HRV
 10  71_HRV50b| 72_HRV50 73_HRV18a| 74_HRV18b| 75_HRV18 76_HRV55 77_HRV55b| 78_HRV55a| 79_HRV
 11  81_HRV57b| 82_HRV21 83_HRVHan 84_HRV43 85_HRV43b| 86_HRV43a| 87_HRV75 88_HRV75b| 89_HRV7
 12  97_HRV9b|d 98_HRV9 99_HRV32 100_HRV32a 101_HRV32b 102_HRV67 103_HRV67a 104_HRV67b 105_HR
 13  107_HRV15b 108_HRV74a 109_HRV74b 110_HRV74 111_HRV38a 112_HRV38b 113_HRV38 114_HRV60 115
 14  117_HRV64b 118_HRV64b 119_HRV64 120_HRV94a 121_HRV94b 122_HRV94 123_HRV22 124_HRV22a 125
 15  127_HRV82b 128_HRV82a 129_HRV19 130_HRV19a 131_HRV19b 132_HRV13 133_HRV13a 134_HRV13b 13
 16  137_HRV41b 138_HRV73 139_HRV73b 140_HRV73a 141_HRV61 142_HRV61a 143_HRV61b 144_HRV96 145
 17  90_HRV16a| 91_HRV16b| 92_1AYM_A 93_HRV81a| 94_HRV81b| 95_HRV81 147_HRV2 148_HRV2a| 149_H
 18  151_HRV49b| 152_HRV49 153_HRV23a 154_HRV23b 155_HRV23 156_HRV30a 157_HRV30b 158_HRV30 159
 19  161_HRV7a| 162_HRV88 163_HRV88a 164_HRV88b 165_HRV36a 166_HRV36b 167_HRV36 168_HRV89a 16
 20  171_HRV58 172_HRV58a 173_HRV58b 174_HRV12a 175_HRV12b 176_HRV12 177_HRV78a 178_HRV78b 17
 21  181_HRV20a 182_HRV20b 183_HRV68 184_HRV68a 185_HRV68b 186_HRV28 187_HRV28a 188_HRV28b 18
 22  191_HRV53 192_HRV46a 193_HRV46b 194_HRV46 195_HRV80a 196_HRV80b 197_HRV80 198_HRV51 199_
 23  201_HRV65a 202_HRV65b 203_HRV65 204_HRV71a 205_HRV71b 206_HRV71 207_HRV8 208_HRV95 209_H
 24  211_HRV45b 212_HRV6 213_HRV6a| 214_HRV6b| 215_HRV37 216_HRV37a 217_HRV37b 218_HRV3 219_H
 25  221_HRV14 222_HRV14a 223_HRV14b 224_HRV72 225_HRV72a 226_HRV72b 227_HRV83 228_HRV83a 229
 26  231_HRV92a 232_HRV92b 233_HRV79 234_HRV79a 235_HRV79b 236_HRV35 237_HRV35a 238_HRV35b 23
 27  241_1HRV86 242_HRV70 243_HRV70a 244_HRV70b 245_HRV91 246_HRV91a 247_HRV91b 248_HRV17 249
 28  251_HRV69 252_HRV69a 253_HRV69b 254_HRV48 255_HRV48a 256_HRV48b 257_HRV52 258_HRV52a 259
 29  261_HRV4a| 262_HRV4b| 263_HRV99 264_HRV99a 265_HRV99b 266_HRV5 267_HRV5a| 268_HRV5b| 269
 30  271_HRV42b 272_HRV26 273_HRV26a 274_HRV26b 275_HRV27 276_HRV27a 277_HRV27b 278_HRV93 279
 31  281_HRV97 282_HRV97a 283_HRV97b 284_HRV84 285_HRV84a 286_HRV84b 287_HRV87 288_HRV87a 289
 32
 33  Partition 2
 34  Group 1:
 35  1_HRV1A1|d 2_HRV1A2|d 3_HRV1A|cD 4_HRV1B1|d 5_HRV1B2|d 6_HRV1B 7_HRV40a|d 8_HRV40b|d 9_H
 36  11_HRV85a| 12_HRV85b| 13_HRV56a| 14_HRV56b| 15_HRV56 16_HRV54 17_HRV98 18_HRV59a| 19_HRV
 37  21_HRV63 22_HRV63b| 23_HRV63a| 24_HRV39 25_HRV39a| 26_HRV39b| 27_HRV10a| 28_HRV10b| 29_H
 38  31_HRV100b 32_HRV100 33_HRV66 34_HRV66b| 35_HRV66a| 36_HRV77a| 37_HRV77b| 38_HRV77 39_HR
 39  41_HRV25 42_HRV29a 43_HRV29b 44_HRV44a 45_HRV44b 46_HRV31 47_HRV31a| 48_HRV31b| 49_HRV47
 40  51_HRV47b| 52_HRV11 53_HRV11b| 54_HRV11a| 55_HRV76 56_HRV76b| 57_HRV76a| 58_HRV33 59_HRV
 41  61_HRV24a| 62_HRV24b| 63_HRV24 64_HRV90 65_HRV90a| 66_HRV90b| 67_HRV34 68_HRV34b| 69_HRV
 42  71_HRV50b| 72_HRV50 73_HRV18a| 74_HRV18b| 75_HRV18 76_HRV55 77_HRV55b| 78_HRV55a| 79_HRV
 43  81_HRV57b| 82_HRV21 83_HRVHan 84_HRV43 85_HRV43b| 86_HRV43a| 87_HRV75 88_HRV75b| 89_HRV7
 44  97_HRV9b|d 98_HRV9 99_HRV32 100_HRV32a 101_HRV32b 102_HRV67 103_HRV67a 104_HRV67b 105_HR
 45  107_HRV15b 108_HRV74a 109_HRV74b 110_HRV74 111_HRV38a 112_HRV38b 113_HRV38 114_HRV60 115
 46  117_HRV64b 118_HRV64b 119_HRV64 120_HRV94a 121_HRV94b 122_HRV94 123_HRV22 124_HRV22a 125
 47  127_HRV82b 128_HRV82a 129_HRV19 130_HRV19a 131_HRV19b 132_HRV13 133_HRV13a 134_HRV13b 13
 48  137_HRV41b 138_HRV73 139_HRV73b 140_HRV73a 141_HRV61 142_HRV61a 143_HRV61b 144_HRV96 145
 49  90_HRV16a| 91_HRV16b| 92_1AYM_A 93_HRV81a| 94_HRV81b| 95_HRV81 147_HRV2 148_HRV2a| 149_H
 50  151_HRV49b| 152_HRV49 153_HRV23a 154_HRV23b 155_HRV23 156_HRV30a 157_HRV30b 158_HRV30 159
 51  161_HRV7a| 162_HRV88 163_HRV88a 164_HRV88b 165_HRV36a 166_HRV36b 167_HRV36 168_HRV89a 16
 52  171_HRV58 172_HRV58a 173_HRV58b 174_HRV12a 175_HRV12b 176_HRV12 177_HRV78a 178_HRV78b 17
 53  181_HRV20a 182_HRV20b 183_HRV68 184_HRV68a 185_HRV68b 186_HRV28 187_HRV28a 188_HRV28b 18
 54  191_HRV53 192_HRV46a 193_HRV46b 194_HRV46 195_HRV80a 196_HRV80b 197_HRV80 198_HRV51 199_
 55  201_HRV65a 202_HRV65b 203_HRV65 204_HRV71a 205_HRV71b 206_HRV71 207_HRV8 208_HRV95 209_H
 56  211_HRV45b
 57
 58  Partition 3
 59  Group 1:
 60  1_HRV1A1|d 2_HRV1A2|d 3_HRV1A|cD 4_HRV1B1|d 5_HRV1B2|d 6_HRV1B 7_HRV40a|d 8_HRV40b|d 9_H
 61  11_HRV85a| 12_HRV85b| 13_HRV56a| 14_HRV56b| 15_HRV56 16_HRV54 17_HRV98 18_HRV59a| 19_HRV
 62  21_HRV63 22_HRV63b| 23_HRV63a| 24_HRV39 25_HRV39a| 26_HRV39b| 27_HRV10a| 28_HRV10b| 29_H
 63  31_HRV100b 32_HRV100 33_HRV66 34_HRV66b| 35_HRV66a| 36_HRV77a| 37_HRV77b| 38_HRV77 39_HR
 64  41_HRV25 42_HRV29a 43_HRV29b 44_HRV44a 45_HRV44b 46_HRV31 47_HRV31a| 48_HRV31b| 49_HRV47
```

FIG. D3

```
group_info-1.txt                                                            9/20/2007 5:06 PM 65  51_HRV47b| 52_HRV11 53_HRV11b| 54_HRV11a| 55_HRV76 56_HRV76b| 57_HRV76a| 58_HRV33 59_HRV
 66  61_HRV24a| 62_HRV24b| 63_HRV24 64_HRV90 65_HRV90a| 66_HRV90b| 67_HRV34 68_HRV34b| 69_HRV
 67  71_HRV50b| 72_HRV50 73_HRV18a| 74_HRV18b| 75_HRV18 76_HRV55 77_HRV55b| 78_HRV55a| 79_HRV
 68  81_HRV57b| 82_HRV21 83_HRVHan 84_HRV43 85_HRV43b| 86_HRV43a| 87_HRV75 88_HRV75b| 89_HRV7
 69  97_HRV9b|d 98_HRV9 99_HRV32 100_HRV32a 101_HRV32b 102_HRV67 103_HRV67a 104_HRV67b 105_HR
 70  107_HRV15b 108_HRV74a 109_HRV74b 110_HRV74 111_HRV38a 112_HRV38b 113_HRV38 114_HRV60 115
 71  117_HRV64a 118_HRV64b 119_HRV64 120_HRV94a 121_HRV94b 122_HRV94 123_HRV22 124_HRV22a
 72  127_HRV82b 128_HRV82a 129_HRV19 130_HRV19a 131_HRV19b 132_HRV13 133_HRV13a 134_HRV13b 13
 73  137_HRV41b 138_HRV73 139_HRV73b 140_HRV73a 141_HRV61 142_HRV61a 143_HRV61b 144_HRV96 145
 74  90_HRV16a| 91_HRV16b| 92_1AYM_A 93_HRV81a| 94_HRV81b| 95_HRV81 147_HRV2 148_HRV2a| 149_H
 75  151_HRV49b| 152_HRV49 153_HRV23a 154_HRV23b 155_HRV23 156_HRV30a 157_HRV30b 158_HRV30 159
 76  161_HRV7a| 162_HRV88 163_HRV88a 164_HRV88b 165_HRV36a 166_HRV36b 167_HRV36 168_HRV89a 16
 77  171_HRV58 172_HRV58a 173_HRV58b 174_HRV12a 175_HRV12b 176_HRV12 177_HRV78a 178_HRV78b 17
 78  181_HRV20a 182_HRV20b 183_HRV68 184_HRV68a 185_HRV68b 186_HRV28 187_HRV28a 188_HRV28b 18
 79  191_HRV53 192_HRV46a 193_HRV46b 194_HRV46 195_HRV80a 196_HRV80b 197_HRV80 198_HRV51 199_
 80  201_HRV65a 202_HRV65b 203_HRV65 204_HRV71a 205_HRV71b 206_HRV71 207_HRV8 208_HRV95 209_H
 81  211_HRV45b
 82
 83  Partition 4
 84  Group 1:
 85  1_HRV1A1|d 2_HRV1A2|d 3_HRV1A|cD 4_HRV1B1|d 5_HRV1B2|d 6_HRV1B 7_HRV40a|d 8_HRV40b|d 9_H
 86  11_HRV85a| 12_HRV85b| 13_HRV56a| 14_HRV56b| 15_HRV56 16_HRV54 17_HRV98 18_HRV59a| 19_HRV
 87  21_HRV63 22_HRV63b| 23_HRV63a| 24_HRV39 25_HRV39a| 26_HRV39b| 27_HRV10a| 28_HRV10b| 29_H
 88  31_HRV100b 32_HRV100 33_HRV66 34_HRV66b| 35_HRV66a| 36_HRV77a| 37_HRV77b| 38_HRV77 39_HR
 89  41_HRV25 42_HRV29a 43_HRV29b 44_HRV44a 45_HRV44b 46_HRV31 47_HRV31a| 48_HRV31b| 49_HRV47
 90  51_HRV47b| 52_HRV11 53_HRV11b| 54_HRV11a| 55_HRV76 56_HRV76b| 57_HRV76a| 58_HRV33 59_HRV
 91  61_HRV24a| 62_HRV24b| 63_HRV24 64_HRV90 65_HRV90a| 66_HRV90b| 67_HRV34 68_HRV34b| 69_HRV
 92  71_HRV50b| 72_HRV50 73_HRV18a| 74_HRV18b| 75_HRV18 76_HRV55 77_HRV55b| 78_HRV55a| 79_HRV
 93  81_HRV57b| 82_HRV21 83_HRVHan 84_HRV43 85_HRV43b| 86_HRV43a| 87_HRV75 88_HRV75b| 89_HRV7
 94  97_HRV9b|d 98_HRV9 99_HRV32 100_HRV32a 101_HRV32b 102_HRV67 103_HRV67a 104_HRV67b 105_HR
 95  107_HRV15b 108_HRV74a 109_HRV74b 110_HRV74 111_HRV38a 112_HRV38b 113_HRV38 114_HRV60 115
 96  117_HRV64a 118_HRV64b 119_HRV64 120_HRV94a 121_HRV94b 122_HRV94 123_HRV22 124_HRV22a 125
 97  127_HRV82b 128_HRV82a 129_HRV19 130_HRV19a 131_HRV19b 132_HRV13 133_HRV13a 134_HRV13b 13
 98  137_HRV41b 138_HRV73 139_HRV73b 140_HRV73a 141_HRV61 142_HRV61a 143_HRV61b 144_HRV96 145
 99  90_HRV16a| 91_HRV16b| 92_1AYM_A 93_HRV81a| 94_HRV81b| 95_HRV81 147_HRV2 148_HRV2a| 149_H
100  151_HRV49b| 152_HRV49 153_HRV23a 154_HRV23b 155_HRV23 156_HRV30a 157_HRV30b 158_HRV30 159
101  161_HRV7a| 162_HRV88 163_HRV88a 164_HRV88b 165_HRV36a 166_HRV36b 167_HRV36 168_HRV89a 16
102  171_HRV58 172_HRV58a 173_HRV58b 174_HRV12a 175_HRV12b 176_HRV12 177_HRV78a 178_HRV78b 17
103  181_HRV20a 182_HRV20b 183_HRV68 184_HRV68a 185_HRV68b 186_HRV28 187_HRV28a 188_HRV28b 18
104  191_HRV53 192_HRV46a 193_HRV46b 194_HRV46 195_HRV80a 196_HRV80b 197_HRV80 198_HRV51 199_
105  201_HRV65a 202_HRV65b 203_HRV65 204_HRV71a 205_HRV71b 206_HRV71 207_HRV8 208_HRV95 209_H
106  211_HRV45b
107
108  Partition 5
109  Group 1:
110  1_HRV1A1|d 2_HRV1A2|d 3_HRV1A|cD 4_HRV1B1|d 5_HRV1B2|d 6_HRV1B 7_HRV40a|d 8_HRV40b|d 9_H
111  11_HRV85a| 12_HRV85b| 13_HRV56a| 14_HRV56b| 15_HRV56 16_HRV54 17_HRV98 18_HRV59a| 19_HRV
112  21_HRV63 22_HRV63b| 23_HRV63a| 24_HRV39 25_HRV39a| 26_HRV39b| 27_HRV10a| 28_HRV10b| 29_H
113  31_HRV100b 32_HRV100 33_HRV66 34_HRV66b| 35_HRV66a| 36_HRV77a| 37_HRV77b| 38_HRV77 39_HR
114  41_HRV25 42_HRV29a 43_HRV29b 44_HRV44a 45_HRV44b 46_HRV31 47_HRV31a| 48_HRV31b| 49_HRV47
115  51_HRV47b| 52_HRV11 53_HRV11b| 54_HRV11a| 55_HRV76 56_HRV76b| 57_HRV76a| 58_HRV33 59_HRV
116  61_HRV24a| 62_HRV24b| 63_HRV24 64_HRV90 65_HRV90a| 66_HRV90b| 67_HRV34 68_HRV34b| 69_HRV
117  71_HRV50b| 72_HRV50 73_HRV18a| 74_HRV18b| 75_HRV18 76_HRV55 77_HRV55b| 78_HRV55a| 79_HRV
118  81_HRV57b| 82_HRV21 83_HRVHan 84_HRV43 85_HRV43b| 86_HRV43a| 87_HRV75 88_HRV75b| 89_HRV7
119  97_HRV9b|d 98_HRV9 99_HRV32 100_HRV32a 101_HRV32b 102_HRV67 103_HRV67a 104_HRV67b 105_HR
120  107_HRV15b 108_HRV74a 109_HRV74b 110_HRV74 111_HRV38a 112_HRV38b 113_HRV38 114_HRV60 115
121  117_HRV64a 118_HRV64b 119_HRV64 120_HRV94a 121_HRV94b 122_HRV94 123_HRV22 124_HRV22a 125
122  127_HRV82b 128_HRV82a 129_HRV19 130_HRV19a 131_HRV19b 132_HRV13 133_HRV13a 134_HRV13b 13
123  137_HRV41b 138_HRV73 139_HRV73b 140_HRV73a 141_HRV61 142_HRV61a 143_HRV61b 144_HRV96 145
124  90_HRV16a| 91_HRV16b| 92_1AYM_A 93_HRV81a| 94_HRV81b| 95_HRV81 147_HRV2 148_HRV2a| 149_H
125  151_HRV49b| 152_HRV49 153_HRV23a 154_HRV23b 155_HRV23 156_HRV30a 157_HRV30b 158_HRV30 159
126  161_HRV7a| 162_HRV88 163_HRV88a 164_HRV88b 165_HRV36a 166_HRV36b 167_HRV36 168_HRV89a 16
127  171_HRV58 172_HRV58a 173_HRV58b 174_HRV12a 175_HRV12b 176_HRV12 177_HRV78a 178_HRV78b 17
128  181_HRV20a 182_HRV20b 183_HRV68 184_HRV68a 185_HRV68b 186_HRV28 187_HRV28a 188_HRV28b 18
```

FIG. D3 CONT'D

```
group_info-1.txt                                                      9/20/2007 5:06 PM
129  191_HRV53 192_HRV46a 193_HRV46b 194_HRV46 195_HRV80a 196_HRV80b 197_HRV80 198_HRV51 199_
130  201_HRV65a 202_HRV65b 203_HRV65 204_HRV71a 205_HRV71b 206_HRV71 207_HRV8 208_HRV95 209_H
131  211_HRV45b
132
133  Partition 6
134  Group 1:
135  1_HRV1A1|d 2_HRV1A2|d 3_HRV1A|cD 4_HRV1B1|d 5_HRV1B2|d 6_HRV1B 7_HRV40a|d 8_HRV40b|d 9_H
136  11_HRV85a| 12_HRV85b| 13_HRV56a| 14_HRV56b| 15_HRV56 16_HRV54 17_HRV98 18_HRV59a| 19_HRV
137  21_HRV63 22_HRV63b| 23_HRV63a| 24_HRV39 25_HRV39a| 26_HRV39b| 27_HRV10a| 28_HRV10b| 29_H
138  31_HRV100b 32_HRV100 33_HRV66 34_HRV66b| 35_HRV66a| 36_HRV77a| 37_HRV77b| 38_HRV77 39_HR
139  41_HRV25 42_HRV29a 43_HRV29b 44_HRV44a 45_HRV44b 46_HRV31 47_HRV31a| 48_HRV31b| 49_HRV47
140  51_HRV47b| 52_HRV11 53_HRV11b| 54_HRV11a| 55_HRV76 56_HRV76b| 57_HRV76a| 58_HRV33 59_HRV
141  61_HRV24a| 62_HRV24b| 63_HRV24 64_HRV90 65_HRV90a| 66_HRV90b| 67_HRV34 68_HRV34b| 69_HRV
142  71_HRV50b| 72_HRV50 73_HRV18a| 74_HRV18b| 75_HRV18 76_HRV55 77_HRV55b| 78_HRV55a| 79_HRV
143  81_HRV57b| 82_HRV21 83_HRVHan 84_HRV43 85_HRV43b| 86_HRV43a| 87_HRV75 88_HRV75b| 89_HRV7
144  97_HRV9b|d 98_HRV9 99_HRV32 100_HRV32a 101_HRV32b 102_HRV67 103_HRV67a 104_HRV67b 105_HR
145  107_HRV15b 108_HRV74a 109_HRV74b 110_HRV74 111_HRV38a 112_HRV38b 113_HRV38 114_HRV60 115
146  117_HRV64a 118_HRV64b 119_HRV64 120_HRV94 121_HRV94b 122_HRV94 123_HRV22 124_HRV22a 125
147  127_HRV82b 128_HRV82a 129_HRV19 130_HRV19a 131_HRV19b 132_HRV13 133_HRV13a 134_HRV13b 13
148  137_HRV41b 138_HRV73 139_HRV73b 140_HRV73a 141_HRV61 142_HRV61a 143_HRV61b 144_HRV96 145
149  90_HRV16b| 91_HRV16b| 92_1AYM_A 93_HRV81a| 94_HRV81b| 95_HRV81 147_HRV2 148_HRV2a| 149_H
150  151_HRV49b 152_HRV49 153_HRV23a 154_HRV23b 155_HRV23 156_HRV30a 157_HRV30b 158_HRV30 159
151  161_HRV7a| 162_HRV88 163_HRV88a 164_HRV88b 165_HRV36a 166_HRV36b 167_HRV36 168_HRV89a 16
152  171_HRV58 172_HRV58a 173_HRV58b 174_HRV12a 175_HRV12b 176_HRV12 177_HRV78a 178_HRV78b 17
153  181_HRV20a 182_HRV20b 183_HRV68 184_HRV68a 185_HRV68b 186_HRV28 187_HRV28a 188_HRV28b 18
154  191_HRV53 192_HRV46a 193_HRV46b 194_HRV46 195_HRV80a 196_HRV80b 197_HRV80 198_HRV51 199_
155  201_HRV65a 202_HRV65b 203_HRV65 204_HRV71a 205_HRV71b 206_HRV71 207_HRV8 208_HRV95 209_H
156  211_HRV45b
157
158  Partition 7
159  Group 1:
160  1_HRV1A1|d 2_HRV1A2|d 3_HRV1A|cD 4_HRV1B1|d 5_HRV1B2|d 6_HRV1B 7_HRV40a|d 8_HRV40b|d 9_H
161  11_HRV85a| 12_HRV85b| 13_HRV56a| 14_HRV56b| 15_HRV56 16_HRV54 17_HRV98 18_HRV59a| 19_HRV
162  21_HRV63 22_HRV63b| 23_HRV63a| 24_HRV39 25_HRV39a| 26_HRV39b| 27_HRV10a| 28_HRV10b| 29_H
163  31_HRV100b 32_HRV100 33_HRV66 34_HRV66b| 35_HRV66a| 36_HRV77a| 37_HRV77b| 38_HRV77 39_HR
164  41_HRV25 42_HRV29a 43_HRV29b 44_HRV44a 45_HRV44b 46_HRV31 47_HRV31a| 48_HRV31b| 49_HRV47
165  51_HRV47b| 52_HRV11 53_HRV11b| 54_HRV11a| 55_HRV76 56_HRV76b| 57_HRV76a| 58_HRV33 59_HRV
166  61_HRV24a| 62_HRV24b| 63_HRV24 64_HRV90 65_HRV90a| 66_HRV90b| 67_HRV34 68_HRV34b| 69_HRV
167  71_HRV50b| 72_HRV50 73_HRV18a| 74_HRV18b| 75_HRV18 76_HRV55 77_HRV55b| 78_HRV55a| 79_HRV
168  81_HRV57b| 82_HRV21 83_HRVHan 84_HRV43 85_HRV43b| 86_HRV43a| 87_HRV75 88_HRV75b| 89_HRV7
169  97_HRV9b|d 98_HRV9 99_HRV32 100_HRV32a 101_HRV32b 102_HRV67 103_HRV67a 104_HRV67b 105_HR
170  107_HRV15b 108_HRV74a 109_HRV74b 110_HRV74 111_HRV38a 112_HRV38b 113_HRV38 114_HRV60 115
171  117_HRV64a 118_HRV64b 119_HRV64 120_HRV94 121_HRV94b 122_HRV94 123_HRV22 124_HRV22a 125
172  127_HRV82b 128_HRV82a 129_HRV19 130_HRV19a 131_HRV19b 132_HRV13 133_HRV13a 134_HRV13b 13
173  137_HRV41b 138_HRV73 139_HRV73b 140_HRV73a 141_HRV61 142_HRV61a 143_HRV61b 144_HRV96 145
174  90_HRV16a| 91_HRV16b| 92_1AYM_A 93_HRV81a| 94_HRV81b| 95_HRV81 147_HRV2 148_HRV2a| 149_H
175  151_HRV49b 152_HRV49 153_HRV23a 154_HRV23b 155_HRV23 156_HRV30a 157_HRV30b 158_HRV30 159
176  161_HRV7a| 162_HRV88 163_HRV88a 164_HRV88b 165_HRV36a 166_HRV36b 167_HRV36 168_HRV89a 16
177  171_HRV58 172_HRV58a 173_HRV58b 174_HRV12a 175_HRV12b 176_HRV12 177_HRV78a 178_HRV78b 17
178  181_HRV20a 182_HRV20b 183_HRV68 184_HRV68a 185_HRV68b 186_HRV28 187_HRV28a 188_HRV28b 18
179  191_HRV53 192_HRV46a 193_HRV46b 194_HRV46 195_HRV80a 196_HRV80b 197_HRV80 198_HRV51 199_
180  201_HRV65a 202_HRV65b 203_HRV65 204_HRV71a 205_HRV71b 206_HRV71 207_HRV8 208_HRV95 209_H
181  211_HRV45b
182
183  Partition 8
184  Group 1:
185  1_HRV1A1|d 2_HRV1A2|d 3_HRV1A|cD 4_HRV1B1|d 5_HRV1B2|d 6_HRV1B 7_HRV40a|d 8_HRV40b|d 9_H
186  11_HRV85a| 12_HRV85b| 13_HRV56a| 14_HRV56b| 15_HRV56 16_HRV54 17_HRV98 18_HRV59a| 19_HRV
187  21_HRV63 22_HRV63b| 23_HRV63a| 24_HRV39 25_HRV39a| 26_HRV39b| 27_HRV10a| 28_HRV10b| 29_H
188  31_HRV100b 32_HRV100 33_HRV66 34_HRV66b| 35_HRV66a| 36_HRV77a| 37_HRV77b| 38_HRV77 39_HR
189  41_HRV25 42_HRV29a 43_HRV29b 44_HRV44a 45_HRV44b 46_HRV31 47_HRV31a| 48_HRV31b| 49_HRV47
190  51_HRV47b| 52_HRV11 53_HRV11b| 54_HRV11a| 55_HRV76 56_HRV76b| 57_HRV76a| 58_HRV33 59_HRV
191  61_HRV24a| 62_HRV24b| 63_HRV24 64_HRV90 65_HRV90a| 66_HRV90b| 67_HRV34 68_HRV34b| 69_HRV
192  71_HRV50b| 72_HRV50 73_HRV18a| 74_HRV18b| 75_HRV18 76_HRV55 77_HRV55b| 78_HRV55a| 79_HRV
```

FIG. D3 CONT'D

```
group_info-1.txt                                                           9/20/2007 5:06 PM 193 81_HRV57b| 82_HRV21 83_HRVHan 84_HRV43 85_HRV43b| 86_HRV43a| 87_HRV75 88_HRV75b| 89_HRV7
194 97_HRV9b|d 98_HRV9 99_HRV32 100_HRV32a 101_HRV32b 102_HRV67 103_HRV67a 104_HRV67b 105_HR
195 107_HRV15b 108_HRV74a 109_HRV74b 110_HRV74 111_HRV38a 112_HRV38b 113_HRV38 114_HRV60 115
196 117_HRV64a 118_HRV64b 119_HRV64 120_HRV94a 121_HRV94b 122_HRV94 123_HRV22 124_HRV22a 125
197 127_HRV82b 128_HRV82a 129_HRV19 130_HRV19a 131_HRV19b 132_HRV13 133_HRV13a 134_HRV13b 13
198 137_HRV41b 138_HRV73 139_HRV73b 140_HRV73a 141_HRV61 142_HRV61a 143_HRV61b 144_HRV96 145
199 90_HRV16a| 91_HRV16b| 92_1AYM_A 93_HRV81a| 94_HRV81b| 95_HRV81
200
201 Group 2:
202 147_HRV2 148_HRV2a| 149_HRV2b| 150_HRV49a 151_HRV49b 152_HRV49 153_HRV23a 154_HRV23b 155
203 157_HRV30b 158_HRV30
204
205 Group 3:
206 159_HRV7 160_HRV7b| 161_HRV7a| 162_HRV88 163_HRV88a 164_HRV88b 165_HRV36a 166_HRV36b 167
207 169_HRV89b 170_HRV89 171_HRV58 172_HRV58a 173_HRV58b
208
209 Group 4:
210 174_HRV12a 175_HRV12b 176_HRV12 177_HRV78a 178_HRV78b 179_HRV78
211
212 Group 5:
213 180_HRV20 181_HRV20a 182_HRV20b 183_HRV68 184_HRV68a 185_HRV68b 186_HRV28 187_HRV28a 188
214 190_HRV53b 191_HRV53 192_HRV46a 193_HRV46b 194_HRV46 195_HRV80a 196_HRV80b 197_HRV80 198
215 200_HRV51b 201_HRV65a 202_HRV65b 203_HRV65 204_HRV71a 205_HRV71b 206_HRV71
216
217 Group 6:
218 207_HRV8 208_HRV95 209_HRV45 210_HRV45a 211_HRV45b
219
220 Partition 9
221 Group 1:
222 1_HRV1A1|d 2_HRV1A2|d 3_HRV1A|cD 4_HRV1B1|d 5_HRV1B2|d 6_HRV1B
223
224 Group 2:
225 7_HRV40a|d 8_HRV40b|d 9_HRV40 10_HRV85 11_HRV85a| 12_HRV85b|
226
227 Group 3:
228 13_HRV56a| 14_HRV56b| 15_HRV56
229
230 Group 4:
231 16_HRV54 17_HRV98
232
233 Group 5:
234 18_HRV59a| 19_HRV59b| 20_HRV59 21_HRV63 22_HRV63b| 23_HRV63a|
235
236 Group 6:
237 24_HRV39 25_HRV39a| 26_HRV39b|
238
239 Group 7:
240 27_HRV10a| 28_HRV10b| 29_HRV10 30_HRV100a 31_HRV100b 32_HRV100
241
242 Group 8:
243 33_HRV66 34_HRV66b| 35_HRV66a| 36_HRV77a| 37_HRV77b| 38_HRV77
244
245 Group 9:
246 39_HRV62a 40_HRV62b 41_HRV25 42_HRV29a 43_HRV29b 44_HRV44a 45_HRV44b
247
248 Group 10:
249 46_HRV31 47_HRV31a| 48_HRV31b| 49_HRV47 50_HRV47a| 51_HRV47b|
250
251 Group 11:
252 52_HRV11 53_HRV11b| 54_HRV11a| 55_HRV76 56_HRV76b| 57_HRV76a| 58_HRV33 59_HRV33b| 60_HRV
253
254 Group 12:
255 61_HRV24a| 62_HRV24b| 63_HRV24 64_HRV90 65_HRV90a| 66_HRV90b|
256
```

FIG. D3 CONT'D group_info-1.txt                                                          9/20/2007 5:06 PM

```
257 Group 13:
258 67_HRV34 68_HRV34b| 69_HRV34a| 70_HRV50a| 71_HRV50b| 72_HRV50 73_HRV18a| 74_HRV18b| 75_H
259
260 Group 14:
261 76_HRV55 77_HRV55b| 78_HRV55a|
262
263 Group 15:
264 79_HRV57 80_HRV57a| 81_HRV57b|
265
266 Group 16:
267 82_HRV21 83_HRVHan
268
269 Group 17:
270 84_HRV43 85_HRV43b| 86_HRV43a| 87_HRV75 88_HRV75b| 89_HRV75a|
271
272 Group 18:
273 96_HRV9a|d 97_HRV9b|d 98_HRV9 99_HRV32 100_HRV32a 101_HRV32b 102_HRV67 103_HRV67a 104_HR
274
275 Group 19:
276 105_HRV15 106_HRV15a 107_HRV15b 108_HRV74a 109_HRV74b 110_HRV74
277
278 Group 20:
279 111_HRV38a 112_HRV38b 113_HRV38
280
281 Group 21:
282 114_HRV60 115_HRV60a 116_HRV60b
283
284 Group 22:
285 117_HRV64a 118_HRV64b 119_HRV64 120_HRV94a 121_HRV94b 122_HRV94 123_HRV22 124_HRV22a 125
286
287 Group 23:
288 126_HRV82 127_HRV82b 128_HRV82a
289
290 Group 24:
291 129_HRV19 130_HRV19a 131_HRV19b
292
293 Group 25:
294 132_HRV13 133_HRV13a 134_HRV13b 135_HRV41 136_HRV41a 137_HRV41b
295
296 Group 26:
297 138_HRV73 139_HRV73b 140_HRV73a
298
299 Group 27:
300 141_HRV61 142_HRV61a 143_HRV61b 144_HRV96 145_HRV96b 146_HRV96a
301
302 Group 28:
303 90_HRV16a| 91_HRV16b| 92_1AYM_A 93_HRV81a| 94_HRV81b| 95_HRV81
304
305 Group 29:
306 147_HRV2 148_HRV2a| 149_HRV2b| 150_HRV49a 151_HRV49b 152_HRV49 153_HRV23a 154_HRV23b 155
307 157_HRV30b 158_HRV30
308
309 Group 30:
310 159_HRV7 160_HRV7b| 161_HRV7a| 162_HRV88 163_HRV88a 164_HRV88b 165_HRV36a 166_HRV36b 167
311 169_HRV89b 170_HRV89 171_HRV58 172_HRV58a 173_HRV58b
312
313 Group 31:
314 174_HRV12a 175_HRV12b 176_HRV12
315
316 Group 32:
317 177_HRV78a 178_HRV78b 179_HRV78
318
319 Group 33:
320 180_HRV20 181_HRV20a 182_HRV20b 183_HRV68 184_HRV68a 185_HRV68b
```

FIG. D3 CONT'D group_info-1.txt                                                                 9/20/2007 5:06 PM

```
321
322 Group 34:
323 186_HRV28 187_HRV28a 188_HRV28b
324
325 Group 35:
326 189_HRV53a 190_HRV53b 191_HRV53
327
328 Group 36:
329 192_HRV46a 193_HRV46b 194_HRV46 195_HRV80a 196_HRV80b 197_HRV80
330
331 Group 37:
332 198_HRV51 199_HRV51a 200_HRV51b 201_HRV65a 202_HRV65b 203_HRV65
333
334 Group 38:
335 204_HRV71a 205_HRV71b 206_HRV71
336
337 Group 39:
338 207_HRV8 208_HRV95
339
340 Group 40:
341 209_HRV45 210_HRV45a 211_HRV45b
342
343 Partition 10
344 Group 1:
345 1_HRV1A1|d 2_HRV1A2|d 3_HRV1A|cD
346
347 Group 2:
348 4_HRV1B1|d 5_HRV1B2|d 6_HRV1B
349
350 Group 3:
351 7_HRV40a|d 8_HRV40b|d 9_HRV40
352
353 Group 4:
354 10_HRV85 11_HRV85a| 12_HRV85b|
355
356 Group 5:
357 13_HRV56a| 14_HRV56b| 15_HRV56
358
359 Group 6:
360 18_HRV59a| 19_HRV59b| 20_HRV59
361
362 Group 7:
363 21_HRV63 22_HRV63b| 23_HRV63a|
364
365 Group 8:
366 24_HRV39 25_HRV39a| 26_HRV39b|
367
368 Group 9:
369 27_HRV10a| 28_HRV10b| 29_HRV10
370
371 Group 10:
372 30_HRV100a 31_HRV100b 32_HRV100
373
374 Group 11:
375 33_HRV66 34_HRV66b| 35_HRV66a|
376
377 Group 12:
378 36_HRV77a| 37_HRV77b| 38_HRV77
379
380 Group 13:
381 39_HRV62a 40_HRV62b 41_HRV25
382
383 Group 14:
384 42_HRV29a 43_HRV29b 44_HRV44a 45_HRV44b
```

FIG. D3 CONT'D

```
group_info-1.txt                                              9/20/2007 5:06 PM
385
386 Group 15:
387 46_HRV31 47_HRV31a| 48_HRV31b|
388
389 Group 16:
390 49_HRV47 50_HRV47a| 51_HRV47b|
391
392 Group 17:
393 52_HRV11 53_HRV11b| 54_HRV11a|
394
395 Group 18:
396 55_HRV76 56_HRV76b| 57_HRV76a|
397
398 Group 19:
399 58_HRV33 59_HRV33b| 60_HRV33a|
400
401 Group 20:
402 61_HRV24a| 62_HRV24b| 63_HRV24
403
404 Group 21:
405 64_HRV90 65_HRV90a| 66_HRV90b|
406
407 Group 22:
408 67_HRV34 68_HRV34b| 69_HRV34a|
409
410 Group 23:
411 70_HRV50a| 71_HRV50b| 72_HRV50
412
413 Group 24:
414 73_HRV18a| 74_HRV18b| 75_HRV18
415
416 Group 25:
417 76_HRV55 77_HRV55b| 78_HRV55a|
418
419 Group 26:
420 79_HRV57 80_HRV57a| 81_HRV57b|
421
422 Group 27:
423 82_HRV21 83_HRVHan
424
425 Group 28:
426 84_HRV43 85_HRV43b| 86_HRV43a|
427
428 Group 29:
429 87_HRV75 88_HRV75b| 89_HRV75a|
430
431 Group 30:
432 96_HRV9a|d 97_HRV9b|d 98_HRV9
433
434 Group 31:
435 99_HRV32 100_HRV32a 101_HRV32b
436
437 Group 32:
438 102_HRV67 103_HRV67a 104_HRV67b
439
440 Group 33:
441 105_HRV15 106_HRV15a 107_HRV15b
442
443 Group 34:
444 108_HRV74a 109_HRV74b 110_HRV74
445
446 Group 35:
447 111_HRV38a 112_HRV38b 113_HRV38
448
```

FIG. D3 CONT'D group_info-1.txt                                                                                                                9/20/2007 5:06 PM

```
449 Group 36:
450 114_HRV60 115_HRV60a 116_HRV60b
451
452 Group 37:
453 117_HRV64a 118_HRV64b 119_HRV64
454
455 Group 38:
456 120_HRV94a 121_HRV94b 122_HRV94
457
458 Group 39:
459 123_HRV22 124_HRV22a 125_HRV22b
460
461 Group 40:
462 126_HRV82 127_HRV82b 128_HRV82a
463
464 Group 41:
465 129_HRV19 130_HRV19a 131_HRV19b
466
467 Group 42:
468 132_HRV13 133_HRV13a 134_HRV13b
469
470 Group 43:
471 135_HRV41 136_HRV41a 137_HRV41b
472
473 Group 44:
474 138_HRV73 139_HRV73b 140_HRV73a
475
476 Group 45:
477 141_HRV61 142_HRV61a 143_HRV61b
478
479 Group 46:
480 144_HRV96 145_HRV96b 146_HRV96a
481
482 Group 47:
483 90_HRV16a| 91_HRV16b| 92_1AYM_A
484
485 Group 48:
486 93_HRV81a| 94_HRV81b| 95_HRV81
487
488 Group 49:
489 147_HRV2 148_HRV2a| 149_HRV2b|
490
491 Group 50:
492 150_HRV49a 151_HRV49b 152_HRV49
493
494 Group 51:
495 153_HRV23a 154_HRV23b 155_HRV23
496
497 Group 52:
498 156_HRV30a 157_HRV30b 158_HRV30
499
500 Group 53:
501 159_HRV7 160_HRV7b| 161_HRV7a|
502
503 Group 54:
504 162_HRV88 163_HRV88a 164_HRV88b
505
506 Group 55:
507 165_HRV36a 166_HRV36b 167_HRV36
508
509 Group 56:
510 168_HRV89a 169_HRV89b 170_HRV89
511
512 Group 57:
```

FIG. D3 CONT'D group_info-1.txt                                                    9/20/2007 5:06 PM

```
513 171_HRV58 172_HRV58a 173_HRV58b
514
515 Group 58:
516 174_HRV12a 175_HRV12b 176_HRV12
517
518 Group 59:
519 177_HRV78a 178_HRV78b 179_HRV78
520
521 Group 60:
522 180_HRV20 181_HRV20a 182_HRV20b
523
524 Group 61:
525 183_HRV68 184_HRV68a 185_HRV68b
526
527 Group 62:
528 186_HRV28 187_HRV28a 188_HRV28b
529
530 Group 63:
531 189_HRV53a 190_HRV53b 191_HRV53
532
533 Group 64:
534 192_HRV46a 193_HRV46b 194_HRV46
535
536 Group 65:
537 195_HRV80a 196_HRV80b 197_HRV80
538
539 Group 66:
540 198_HRV51 199_HRV51a 200_HRV51b
541
542 Group 67:
543 201_HRV65a 202_HRV65b 203_HRV65
544
545 Group 68:
546 204_HRV71a 205_HRV71b 206_HRV71
547
548 Group 69:
549 207_HRV8 208_HRV95
550
551 Group 70:
552 209_HRV45 210_HRV45a 211_HRV45b
553
554
```

FIG. D3 CONT'D

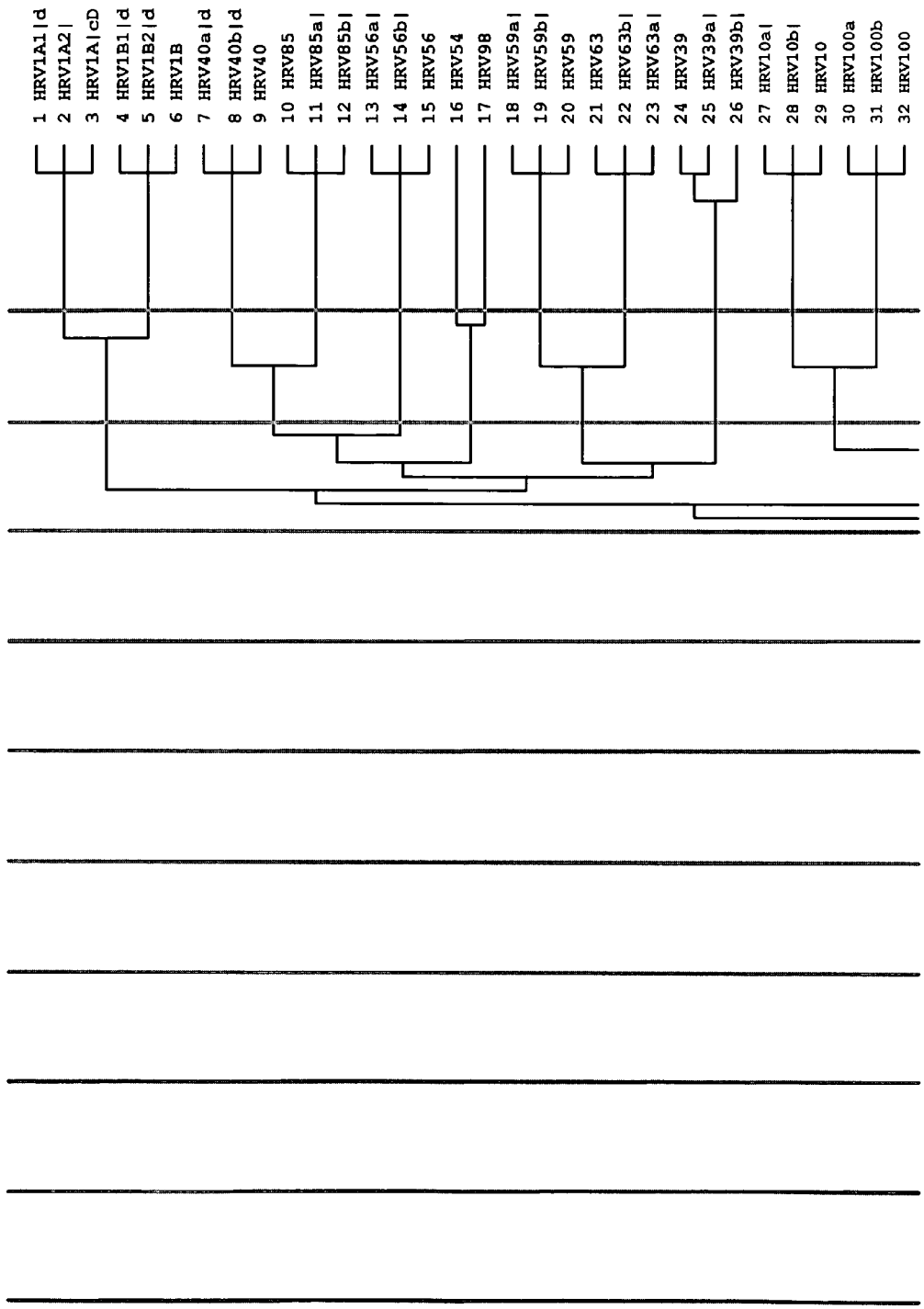
FIG. D4

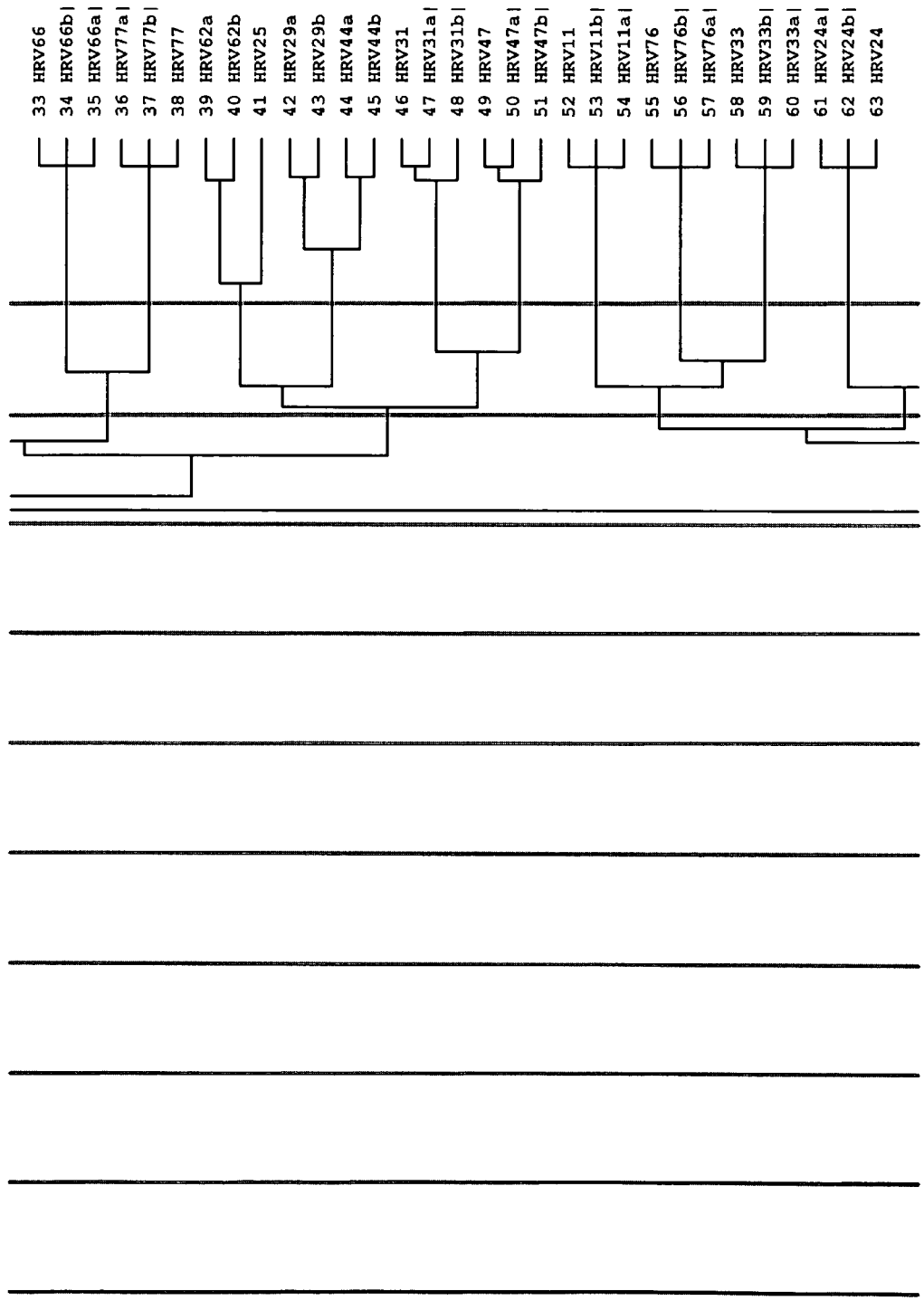
FIG. D4 CONT'D

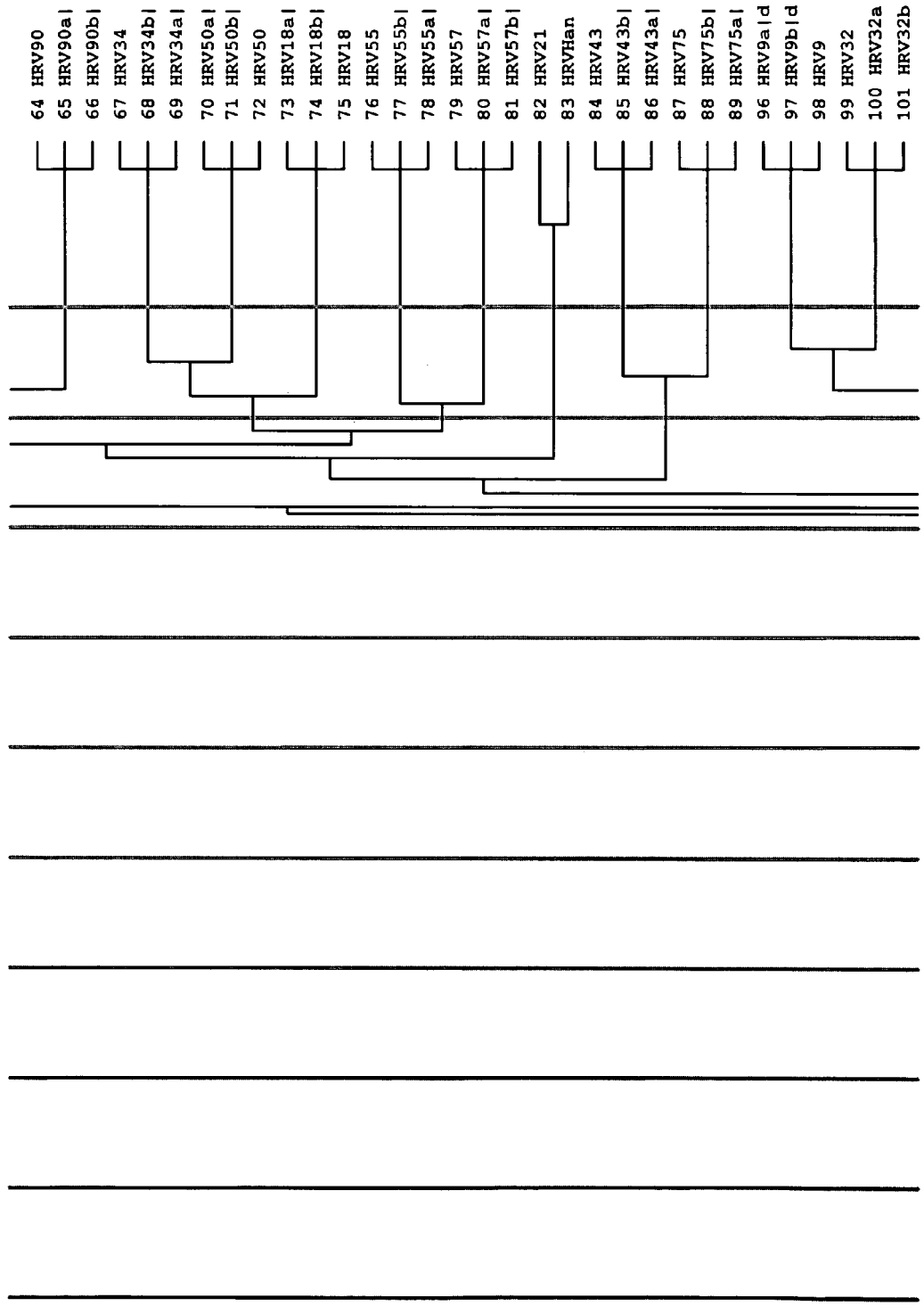
FIG. D4 CONT'D

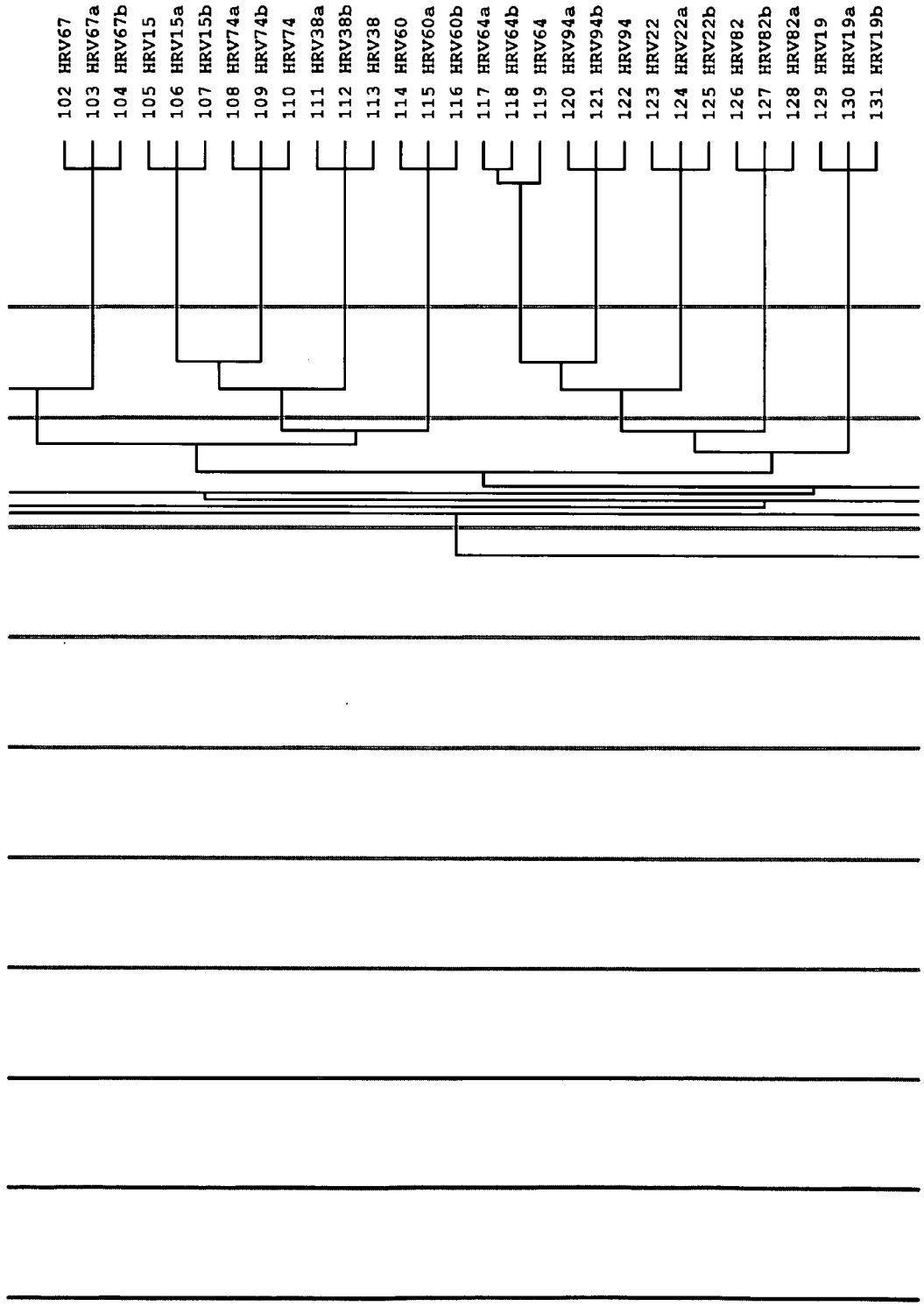
FIG. D4 CONT'D

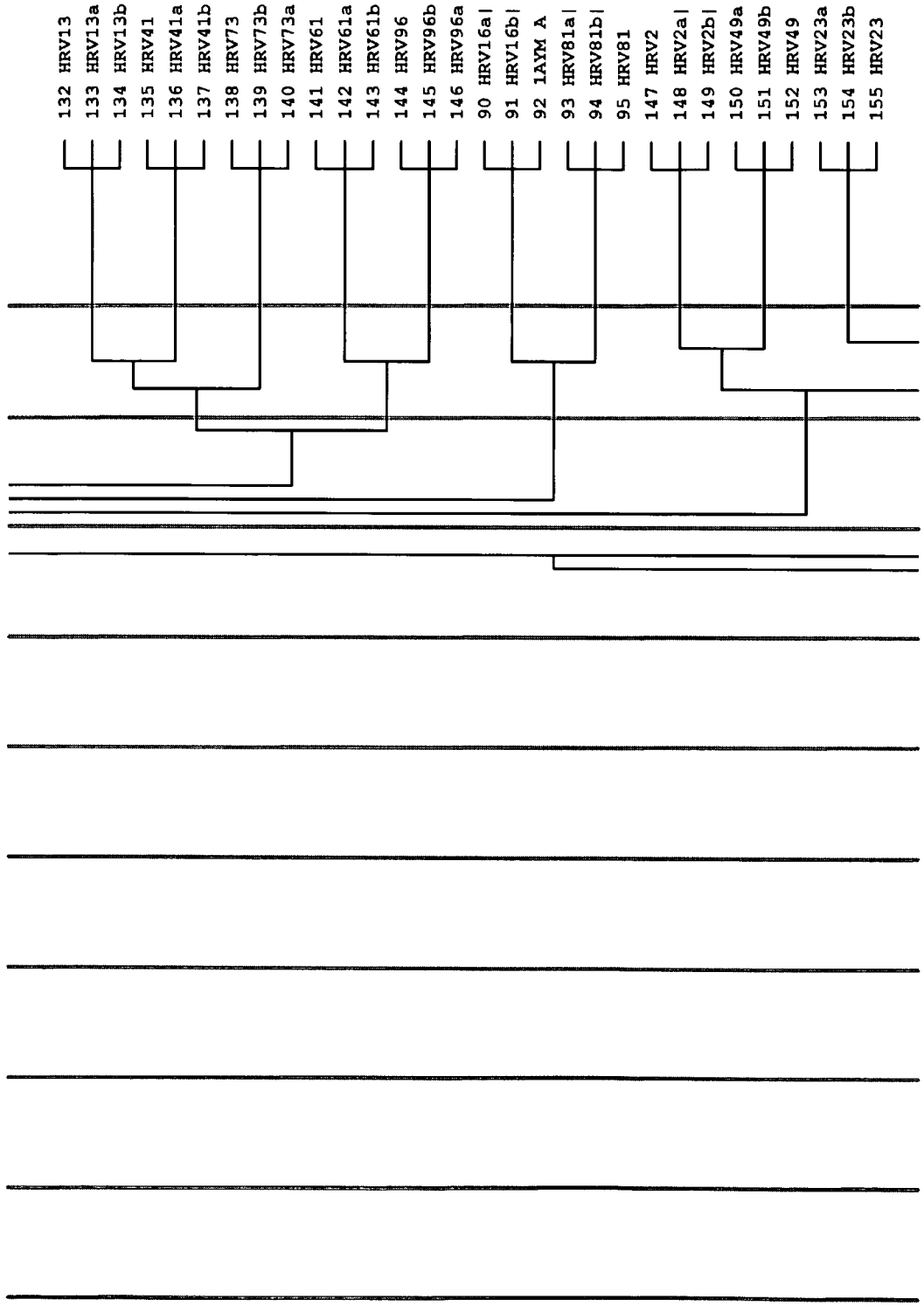
FIG. D4 CONT'D

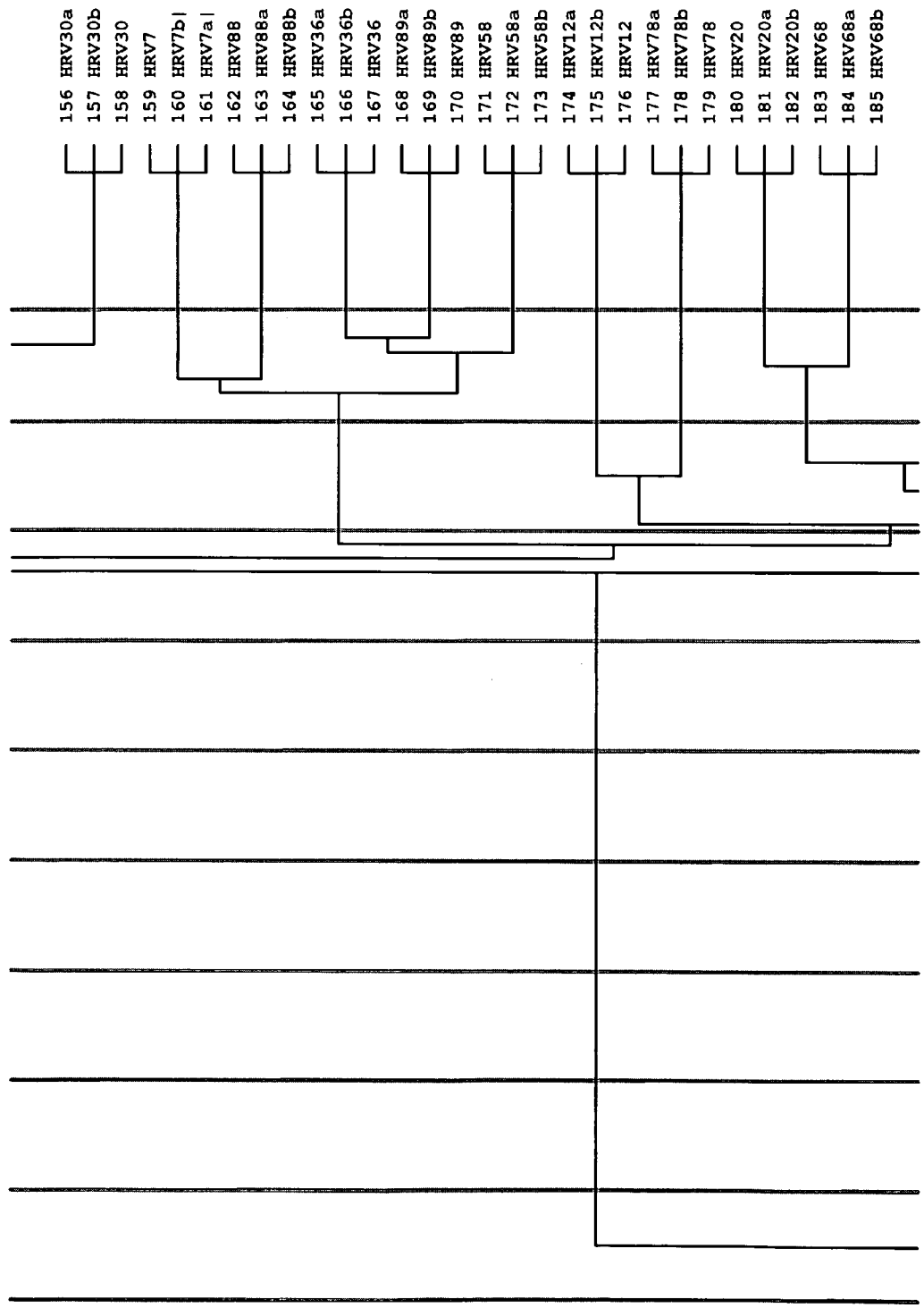
FIG. D4 CONT'D

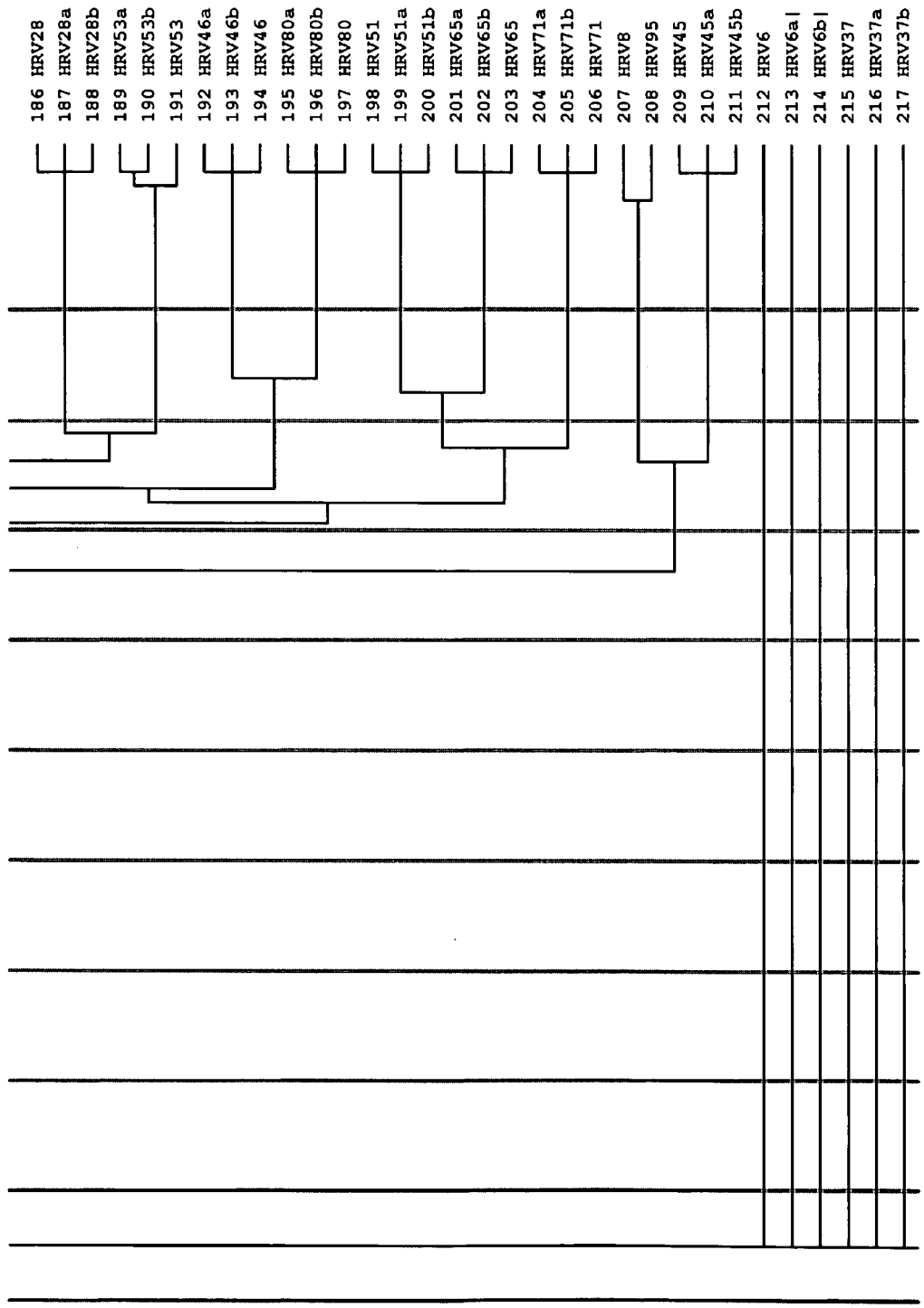
FIG. D4 CONT'D

| | 218 HRV3 | 219 HRV3a | 220 HRV3b | 221 HRV14 | 222 HRV14a | 223 HRV14b | 224 HRV72 | 225 HRV72a | 226 HRV72b | 227 HRV83 | 228 HRV83a | 229 HRV83b | 230 HRV92 | 231 HRV92a | 232 HRV92b | 233 HRV79 | 234 HRV79a | 235 HRV79b | 236 HRV35 | 237 HRV35a | 238 HRV35b | 239 1HRV86 | 240 1HRV86 | 241 1HRV86 | 242 HRV70 | 243 HRV70a | 244 HRV70b | 245 HRV91 | 246 HRV91a | 247 HRV91b | 248 HRV17 | 249 HRV17a |
|---|---|---|---|---|---|---|---|---|---|---|---|---|---|---|---|---|---|---|---|---|---|---|---|---|---|---|---|---|---|---|---|---|

FIG. D4 CONT'D

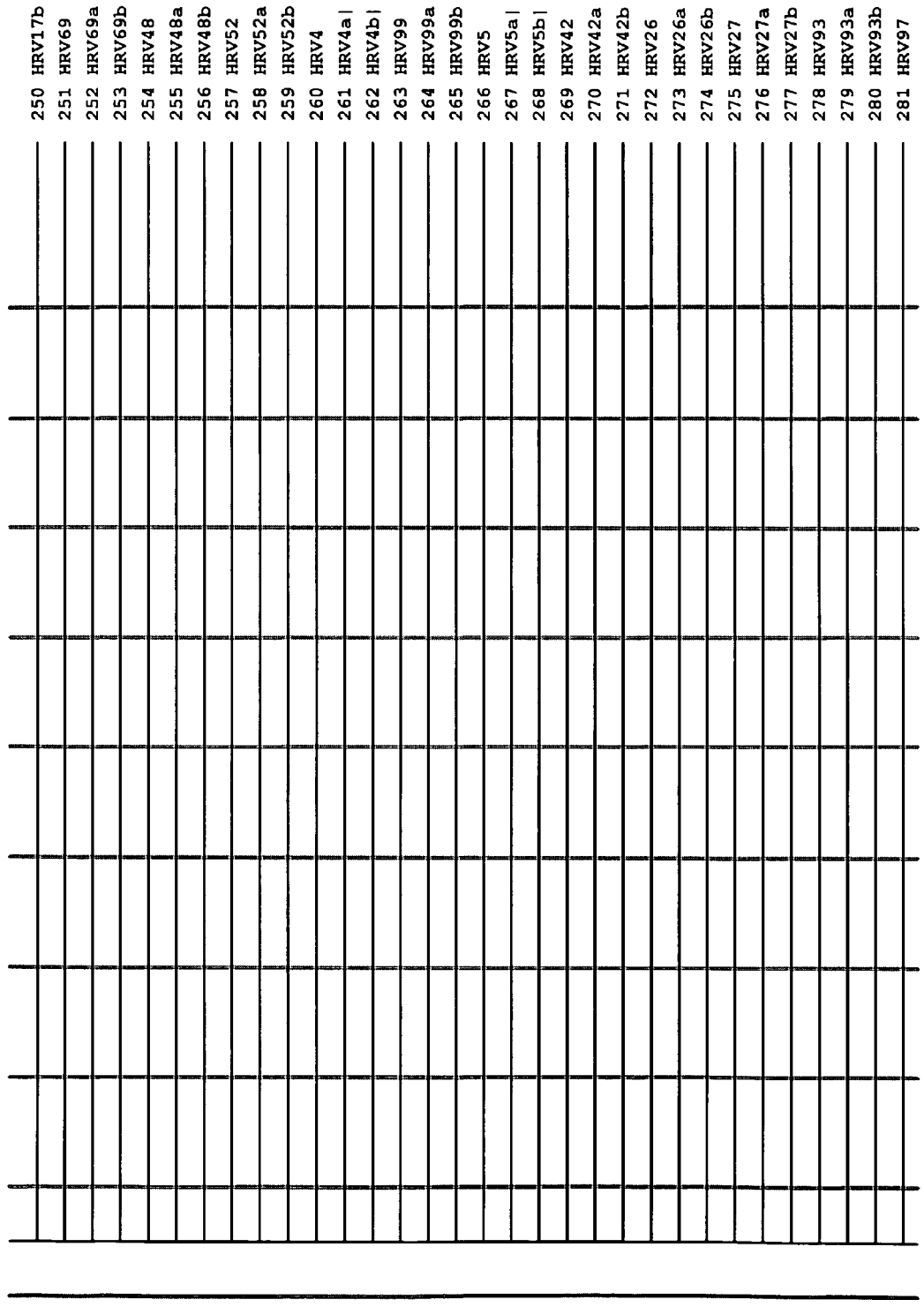
FIG. D4 CONT'D

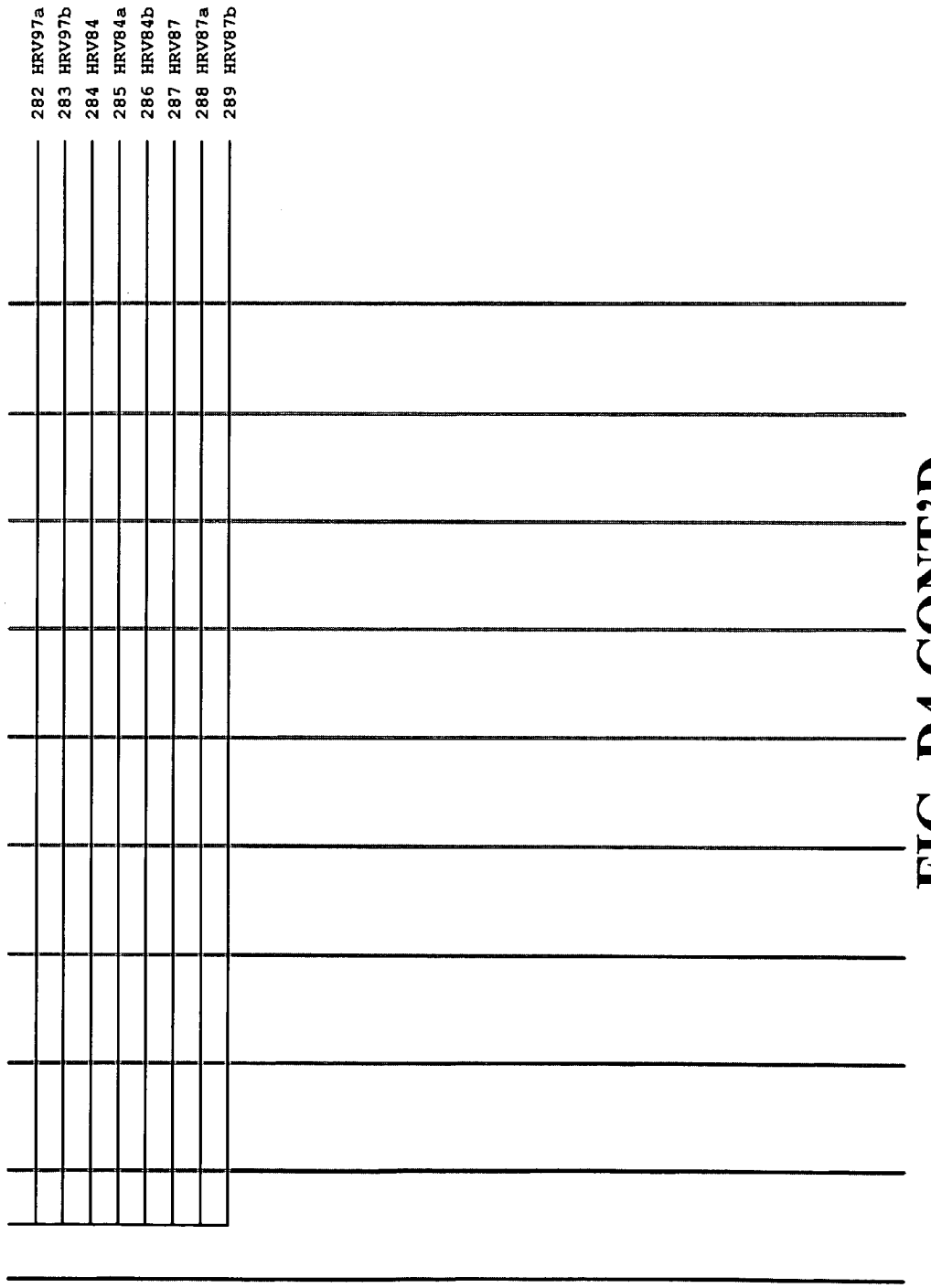

01.trace                                                                9/20/2007 4:58 PM

```
 1 Group 1:  1_HRV1A1|d
 2 Group 1:  2_HRV1A2|d
 3 Group 1:  3_HRV1A|cD
 4 Group 1:  4_HRV1B1|d
 5 Group 1:  5_HRV1B2|d
 6 Group 1:  6_HRV1B
 7 Group 1:  7_HRV40a|d
 8 Group 1:  8_HRV40b|d
 9 Group 1:  9_HRV40
10 Group 1: 10_HRV85
11 Group 1: 11_HRV85a|
12 Group 1: 12_HRV85b|
13 Group 1: 13_HRV56a|
14 Group 1: 14_HRV56b|
15 Group 1: 15_HRV56
16 Group 1: 16_HRV54
17 Group 1: 17_HRV98
18 Group 1: 18_HRV59a|
19 Group 1: 19_HRV59b|
20 Group 1: 20_HRV59
21 Group 1: 21_HRV63
22 Group 1: 22_HRV63b|
23 Group 1: 23_HRV63a|
24 Group 1: 24_HRV39
25 Group 1: 25_HRV39a|
26 Group 1: 26_HRV39b|
27 Group 1: 27_HRV10a|
28 Group 1: 28_HRV10b|
29 Group 1: 29_HRV10
30 Group 1: 30_HRV100a
31 Group 1: 31_HRV100b
32 Group 1: 32_HRV100
33 Group 1: 33_HRV66
34 Group 1: 34_HRV66b|
35 Group 1: 35_HRV66a|
36 Group 1: 36_HRV77a|
37 Group 1: 37_HRV77b|
38 Group 1: 38_HRV77
39 Group 1: 39_HRV62a
40 Group 1: 40_HRV62b
41 Group 1: 41_HRV25
42 Group 1: 42_HRV29a
43 Group 1: 43_HRV29b
44 Group 1: 44_HRV44a
45 Group 1: 45_HRV44b
46 Group 1: 46_HRV31
47 Group 1: 47_HRV31a|
48 Group 1: 48_HRV31b|
49 Group 1: 49_HRV47
50 Group 1: 50_HRV47a|
51 Group 1: 51_HRV47b|
52 Group 1: 52_HRV11
53 Group 1: 53_HRV11b|
54 Group 1: 54_HRV11a|
55 Group 1: 55_HRV76
56 Group 1: 56_HRV76b|
57 Group 1: 57_HRV76a|
58 Group 1: 58_HRV33
59 Group 1: 59_HRV33b|
60 Group 1: 60_HRV33a|
61 Group 1: 61_HRV24a|
62 Group 1: 62_HRV24b|
63 Group 1: 63_HRV24
64 Group 1: 64_HRV90
```

FIG. D5

01.trace                                                              9/20/2007 4:58 PM

```
 65 Group 1:  65_HRV90a|
 66 Group 1:  66_HRV90b|
 67 Group 1:  67_HRV34
 68 Group 1:  68_HRV34b|
 69 Group 1:  69_HRV34a|
 70 Group 1:  70_HRV50a|
 71 Group 1:  71_HRV50b|
 72 Group 1:  72_HRV50
 73 Group 1:  73_HRV18a|
 74 Group 1:  74_HRV18b|
 75 Group 1:  75_HRV18
 76 Group 1:  76_HRV55
 77 Group 1:  77_HRV55b|
 78 Group 1:  78_HRV55a|
 79 Group 1:  79_HRV57
 80 Group 1:  80_HRV57a|
 81 Group 1:  81_HRV57b|
 82 Group 1:  82_HRV21
 83 Group 1:  83_HRVHan
 84 Group 1:  84_HRV43
 85 Group 1:  85_HRV43b|
 86 Group 1:  86_HRV43a|
 87 Group 1:  87_HRV75
 88 Group 1:  88_HRV75b|
 89 Group 1:  89_HRV75a|
 90 Group 1:  96_HRV9a|d
 91 Group 1:  97_HRV9b|d
 92 Group 1:  98_HRV9
 93 Group 1:  99_HRV32
 94 Group 1:  100_HRV32a
 95 Group 1:  101_HRV32b
 96 Group 1:  102_HRV67
 97 Group 1:  103_HRV67a
 98 Group 1:  104_HRV67b
 99 Group 1:  105_HRV15
100 Group 1:  106_HRV15a
101 Group 1:  107_HRV15b
102 Group 1:  108_HRV74a
103 Group 1:  109_HRV74b
104 Group 1:  110_HRV74
105 Group 1:  111_HRV38a
106 Group 1:  112_HRV38b
107 Group 1:  113_HRV38
108 Group 1:  114_HRV60
109 Group 1:  115_HRV60a
110 Group 1:  116_HRV60b
111 Group 1:  117_HRV64a
112 Group 1:  118_HRV64b
113 Group 1:  119_HRV64
114 Group 1:  120_HRV94a
115 Group 1:  121_HRV94b
116 Group 1:  122_HRV94
117 Group 1:  123_HRV22
118 Group 1:  124_HRV22a
119 Group 1:  125_HRV22b
120 Group 1:  126_HRV82
121 Group 1:  127_HRV82b
122 Group 1:  128_HRV82a
123 Group 1:  129_HRV19
124 Group 1:  130_HRV19a
125 Group 1:  131_HRV19b
126 Group 1:  132_HRV13
127 Group 1:  133_HRV13a
128 Group 1:  134_HRV13b
```

FIG. D5 CONT'D

01.trace                                                                 9/20/2007 4:58 PM

```
129 Group 1: 135_HRV41
130 Group 1: 136_HRV41a
131 Group 1: 137_HRV41b
132 Group 1: 138_HRV73
133 Group 1: 139_HRV73b
134 Group 1: 140_HRV73a
135 Group 1: 141_HRV61
136 Group 1: 142_HRV61a
137 Group 1: 143_HRV61b
138 Group 1: 144_HRV96
139 Group 1: 145_HRV96b
140 Group 1: 146_HRV96a
141 Group 1: 90_HRV16a|
142 Group 1: 91_HRV16b|
143 Group 1: 92_1AYM_A
144 Group 1: 93_HRV81a|
145 Group 1: 94_HRV81b|
146 Group 1: 95_HRV81
147 Group 1: 147_HRV2
148 Group 1: 148_HRV2a|
149 Group 1: 149_HRV2b|
150 Group 1: 150_HRV49a
151 Group 1: 151_HRV49b
152 Group 1: 152_HRV49
153 Group 1: 153_HRV23a
154 Group 1: 154_HRV23b
155 Group 1: 155_HRV23
156 Group 1: 156_HRV30a
157 Group 1: 157_HRV30b
158 Group 1: 158_HRV30
159 Group 1: 159_HRV7
160 Group 1: 160_HRV7b|
161 Group 1: 161_HRV7a|
162 Group 1: 162_HRV88
163 Group 1: 163_HRV88a
164 Group 1: 164_HRV88b
165 Group 1: 165_HRV36a
166 Group 1: 166_HRV36b
167 Group 1: 167_HRV36
168 Group 1: 168_HRV89a
169 Group 1: 169_HRV89b
170 Group 1: 170_HRV89
171 Group 1: 171_HRV58
172 Group 1: 172_HRV58a
173 Group 1: 173_HRV58b
174 Group 1: 174_HRV12a
175 Group 1: 175_HRV12b
176 Group 1: 176_HRV12
177 Group 1: 177_HRV78a
178 Group 1: 178_HRV78b
179 Group 1: 179_HRV78
180 Group 1: 180_HRV20
181 Group 1: 181_HRV20a
182 Group 1: 182_HRV20b
183 Group 1: 183_HRV68
184 Group 1: 184_HRV68a
185 Group 1: 185_HRV68b
186 Group 1: 186_HRV28
187 Group 1: 187_HRV28a
188 Group 1: 188_HRV28b
189 Group 1: 189_HRV53a
190 Group 1: 190_HRV53b
191 Group 1: 191_HRV53
192 Group 1: 192_HRV46a
```

FIG. D5 CONT'D 01.trace                                                             9/20/2007 4:58 PM

```
193 Group 1: 193_HRV46b
194 Group 1: 194_HRV46
195 Group 1: 195_HRV80a
196 Group 1: 196_HRV80b
197 Group 1: 197_HRV80
198 Group 1: 198_HRV51
199 Group 1: 199_HRV51a
200 Group 1: 200_HRV51b
201 Group 1: 201_HRV65a
202 Group 1: 202_HRV65b
203 Group 1: 203_HRV65
204 Group 1: 204_HRV71a
205 Group 1: 205_HRV71b
206 Group 1: 206_HRV71
207 Group 1: 207_HRV8
208 Group 1: 208_HRV95
209 Group 1: 209_HRV45
210 Group 1: 210_HRV45a
211 Group 1: 211_HRV45b
212 Group 1: 212_HRV6
213 Group 1: 213_HRV6a|
214 Group 1: 214_HRV6b|
215 Group 1: 215_HRV37
216 Group 1: 216_HRV37a
217 Group 1: 217_HRV37b
218 Group 1: 218_HRV3
219 Group 1: 219_HRV3a|
220 Group 1: 220_HRV3b|
221 Group 1: 221_HRV14
222 Group 1: 222_HRV14a
223 Group 1: 223_HRV14b
224 Group 1: 224_HRV72
225 Group 1: 225_HRV72a
226 Group 1: 226_HRV72b
227 Group 1: 227_HRV83
228 Group 1: 228_HRV83a
229 Group 1: 229_HRV83b
230 Group 1: 230_HRV92
231 Group 1: 231_HRV92a
232 Group 1: 232_HRV92b
233 Group 1: 233_HRV79
234 Group 1: 234_HRV79a
235 Group 1: 235_HRV79b
236 Group 1: 236_HRV35
237 Group 1: 237_HRV35a
238 Group 1: 238_HRV35b
239 Group 1: 239_1HRV86
240 Group 1: 240_1HRV86
241 Group 1: 241_1HRV86
242 Group 1: 242_HRV70
243 Group 1: 243_HRV70a
244 Group 1: 244_HRV70b
245 Group 1: 245_HRV91
246 Group 1: 246_HRV91a
247 Group 1: 247_HRV91b
248 Group 1: 248_HRV17
249 Group 1: 249_HRV17a
250 Group 1: 250_HRV17b
251 Group 1: 251_HRV69
252 Group 1: 252_HRV69a
253 Group 1: 253_HRV69b
254 Group 1: 254_HRV48
255 Group 1: 255_HRV48a
256 Group 1: 256_HRV48b
```

FIG. D5 CONT'D 01.trace                                                                    9/20/2007 4:58 PM

```
257 Group 1: 257_HRV52
258 Group 1: 258_HRV52a
259 Group 1: 259_HRV52b
260 Group 1: 260_HRV4
261 Group 1: 261_HRV4a|
262 Group 1: 262_HRV4b|
263 Group 1: 263_HRV99
264 Group 1: 264_HRV99a
265 Group 1: 265_HRV99b
266 Group 1: 266_HRV5
267 Group 1: 267_HRV5a|
268 Group 1: 268_HRV5b|
269 Group 1: 269_HRV42
270 Group 1: 270_HRV42a
271 Group 1: 271_HRV42b
272 Group 1: 272_HRV26
273 Group 1: 273_HRV26a
274 Group 1: 274_HRV26b
275 Group 1: 275_HRV27
276 Group 1: 276_HRV27a
277 Group 1: 277_HRV27b
278 Group 1: 278_HRV93
279 Group 1: 279_HRV93a
280 Group 1: 280_HRV93b
281 Group 1: 281_HRV97
282 Group 1: 282_HRV97a
283 Group 1: 283_HRV97b
284 Group 1: 284_HRV84
285 Group 1: 285_HRV84a
286 Group 1: 286_HRV84b
287 Group 1: 287_HRV87
288 Group 1: 288_HRV87a
289 Group 1: 289_HRV87b
290
291
292 >>>>>
293
294
295
296 Group 1:
297
298  1_HRV1A1|d   AATCCAGTAGAAAACTACATTGATGAAGTTTTAAATGAAGTTTTAGTAGTGCCGAATATA
299  2_HRV1A2|d   AATCCAGTAGAAAACTACATTGATGAAGTTTTAAATGAAGTTTTAGTAGTGCCGAATATA
300  3_HRV1A|cD   AATCCAGTAGAAAACTACATTGATGAAGTTTTAAATGAAGTTTTAGTAGTGCCGAATATA
301  4_HRV1B1|d   AATCCAGTGGAAAATTACATTGATGAAGTTTTAAATGAAGTTCTAGTAGTACCAAATATA
302  5_HRV1B2|d   AATCCAGTGGAAAATTACATTGATGAAGTTTTAAATGAAGTTCTAGTAGTACCAAATATA
303  6_HRV1B      AATCCAGTGGAAAATTACATTGATGAAGTTTTAAATGAAGTTCTAGTAGTACCAAATATA
304  7_HRV40a|d   AACCCCGTTGAAAGGTATGTTGATGAGGTTCTTAATGAAGTTCTGGTAGTTCCAAATATC
305  8_HRV40b|d   AACCCCGTTGAAAGGTATGTTGATGAGGTTCTTAATGAAGTTCTGGTAGTTCCAAATATC
306  9_HRV40      AACCCCGTTGAAAGGTATGTTGATGAGGTTCTTAATGAAGTTCTGGTAGTTCCAAATATC
307 10_HRV85      AATCCTGTTGAAAAATACGTTGATGAAGTCCTTAATGAGGTTCTAGTGGTTCCAAATATC
308 11_HRV85a|    AATCCTGTTGAAAAATACGTTGATGAAGTCCTTAATGAGGTTCTAGTGGTTCCAAATATC
309 12_HRV85b|    AATCCTGTTGAAAAATACGTTGATGAAGTCCTTAATGAGGTTCTAGTGGTTCCAAATATC
310 13_HRV56a|    AACCCAGTTGAGAGATATGTAGATGATGTTTTAAATGAAGTTTTAGTTGTTCCAAATATT
311 14_HRV56b|    AACCCAGTTGAGAGATATGTAGATGATGTTTTAAATGAAGTTTTAGTTGTTCCAAATATT
312 15_HRV56      AACCCAGTTGAGAGATATGTAGATGATGTTTTAAATGAAGTTTTAGTTGTTCCAAATATT
313 16_HRV54      AATCCTGTAGAAAGATATGTTGATGAAGTGTTAAATGAAGTGTTAGTTGTCCCAAACATT
314 17_HRV98      AATCCTGTAGAGAGATATGTTGATGAAGTATTAAATGAAGTGTTAGTTGTTCCAAACATT
315 18_HRV59a|    AACCCAGTGGAAAACTATGTTAATGATGTACTTAATGAGGTTTTAGTAGTACCAAATATA
316 19_HRV59b|    AACCCAGTGGAAAACTATGTTAATGATGTACTTAATGAGGTTTTAGTAGTACCAAATATA
317 20_HRV59      AACCCAGTGGAAAACTATGTTAATGATGTACTTAATGAGGTTTTAGTAGTACCAAATATA
318 21_HRV63      AATCCAGTAGAGAATTATGTAAATGATGTTCTTAATGAAGTGTTAGTTGTTCCAAACATA
319 22_HRV63b|    AATCCAGTAGAGAATTATGTAAATGATGTTCTTAATGAAGTGTTAGTTGTTCCAAACATA
320 23_HRV63a|    AATCCAGTAGAGAATTATGTAAATGATGTTCTTAATGAAGTGTTAGTTGTTCCAAACATA
```

FIG. D5 CONT'D

01.trace                                                                          9/20/2007 4:58 PM

```
321 24_HRV39    AATCCAGTAGAAAATTATATAGATGAAGTATTAAATGAGGTATTAGTTGTTCCTAATATA
322 25_HRV39a|  AATCCAGTAGAAAATTATATAGATGAAGTATTAAATGAGGTATTAGTTGTTCCTAATATA
323 26_HRV39b|  AATCCAGTAGAAAATTATATAGATGGAGTATTAAATGAGGTATTAGTTGTTCCTAATATA
324 27_HRV10a|  AATCCAGTTGAAAATTACATTGATAATGTACTTAATGAAGTCCTAGTGGTACCCAACATC
325 28_HRV10b|  AATCCAGTTGAAAATTACATTGATAATGTACTTAATGAAGTCCTAGTGGTACCCAACATC
326 29_HRV10    AATCCAGTTGAAAATTACATTGATAATGTACTTAATGAAGTCCTAGTGGTACCCAACATC
327 30_HRV100a  AATCCAGTAGAAAATTATGTTGAAGGTGTGCTGAATGAAGTACTAGTGGTACCTAATATT
328 31_HRV100b  AATCCAGTAGAAAATTATGTTGAAGGTGTGCTGAATGAAGTACTAGTGGTACCTAATATT
329 32_HRV100   AATCCAGTAGAAAATTATGTTGAAGGTGTGCTGAATGAAGTACTAGTGGTACCTAATATT
330 33_HRV66    AATCCAGTTGAAGATTATGTTGAGGGTGTTTTAAATGAAGTTTTAGTAGTACCAAACATC
331 34_HRV66b|  AATCCAGTTGAAGATTATGTTGAGGGTGTTTTAAATGAAGTTTTAGTAGTACCAAACATC
332 35_HRV66a|  AATCCAGTTGAAGATTATGTTGAGGGTGTTTTAAATGAAGTTTTAGTAGTACCAAACATC
333 36_HRV77a|  AATCCAGTTGAGGACTATATCGATAATGTACTTAATGAAGTCTTAGTAGTACCAAATACC
334 37_HRV77b|  AATCCAGTTGAGGACTATATCGATAATGTACTTAATGAAGTCTTAGTAGTACCAAATACC
335 38_HRV77    AATCCAGTTGAGGACTATATCGATAATGTACTTAATGAAGTCTTAGTAGTACCAAATACC
336 39_HRV62a   AATCCAATTGAAAATTATGTAGATCAAGTACTTAATGAAGTTTTAGTTGTACCAAATATT
337 40_HRV62b   AATCCAATTGAAAATTATGTAGATCAAGTACTTAATGAAGTTTTAGTTGTACCAAATATT
338 41_HRV25    AATCCAATTGAAAATTATGTAGATCAAGTACTTAATGAGGTTCTAGTCGTACCAAATATT
339 42_HRV29a   AACCCAGTTGAAAACTATGTGGATGAGGTGCTTAATGAAGTTTTAGTTGTGCCTAACATC
340 43_HRV29b   AACCCAGTTGAAAACTATGTGGATGAGGTGCTTAATGAAGTTTTAGTTGTGCCTAACATC
341 44_HRV44a   AACCCAGTTGAAAATTATGTGGATGAAGTACTTAATGAAGTCTTAGTTGTGCCTAATATC
342 45_HRV44b   AACCCAGTTGAAAATTATGTGGATGAAGTACTTAATGAAGTCTTAGTTGTGCCTAATATC
343 46_HRV31    AATCCAGTTGAAAACTATGTGGAAGAGGTTCTTAATGAAGTCTTAGTAGTACCTAATATC
344 47_HRV31a|  AATCCAGTTGAAAACTATGTGGAAGAGGTCTTAATGAAGTCTTAGTAGTACCTAATATC
345 48_HRV31b|  AATCCAGTTGAAAACTATGTGGAAGAGGTCTTAATGAAGTCTTAGTAGTACCTAATATC
346 49_HRV47    AACCCAGTCGAAAATTATGTGGAAGAGGTACTTAATGAGGTCTTAGTTGTACCAAATATC
347 50_HRV47a|  AACCCAGTCGAAAATTATGTGGAAGAGGTACTTAATGAGGTCTTAGTTGTACCAAATATC
348 51_HRV47b|  AACCCAGTCGAAAATTATGTGGAAGAGGTACTTAATGAGGTCTTAGTTGTACCAAATATC
349 52_HRV11    AACCCAGTGGAGGATTATGTTGATGGAATTCTAAATGAGGTTTTAGTTGTACCTAATATA
350 53_HRV11b|  AACCCAGTGGAGGATTATGTTGATGGAATTCTAAATGAGGTTTTAGTTGTACCTAATATA
351 54_HRV11a|  AACCCAGTGGAGGATTATGTTGATGGAATTCTAAATGAGGTTTTAGTTGTACCTAATATA
352 55_HRV76    AACCCAGTTGAAAATTACGTGGATGAGATATTAAATGAGGTTCTTGTAGTACCAAACATC
353 56_HRV76b|  AACCCAGTTGAAAATTACGTGGATGAGATATTAAATGAGGTTCTTGTAGTACCAAACATC
354 57_HRV76a|  AACCCAGTTGAAAATTACGTGGATGAGATATTAAATGAGGTTCTTGTAGTACCAAACATC
355 58_HRV33    AATCCAGTAGAGAATTATATAGAAGAGGTGTTGAATGAGGTTTTAGTAGTGCCTAATATC
356 59_HRV33b|  AATCCAGTAGAGAATTATATAGAAGAGGTGTTGAATGAGGTTTTTAGTAGTGCCTAATATC
357 60_HRV33a|  AATCCAGTAGAGAATTATATAGAAGAGGTGTTGAATGAGGTTTTAGTAGTGCCTAATATC
358 61_HRV24a|  AACCCAGTAGAAAATTATATAGATGAGGTTTTGAATGAAGTACTGGTTGTGCCTAATATT
359 62_HRV24b|  AACCCAGTAGAAAATTATATAGATGAGGTTTTGAATGAAGTACTGGTTGTGCCTAATATT
360 63_HRV24    AACCCAGTAGAAAATTATATAGATGAGGTTTTGAATGAAGTACTGGTTGTGCCTAATATT
361 64_HRV90    AATCCAGTGGAAAATTATATAGATGAAGTCCTAAATGAGGTATTGGTTGTCCCTAATATT
362 65_HRV90a|  AATCCAGTGGAAAATTATATAGATGAAGTCCTAAATGAGGTATTGGTTGTCCCTAATATT
363 66_HRV90b|  AATCCAGTGGAAAATTATATAGATGAAGTCCTAAATGAGGTATTGGTTGTCCCTAATATT
364 67_HRV34    AATCCAGTTGAAAATTACATAGATGAGGTACTAAATGAGGTATTGGTTGTACCAAACATT
365 68_HRV34b|  AATCCAGTTGAAAATTACATAGATGAGGTACTAAATGAGGTATTGGTTGTACCAAACATT
366 69_HRV34a|  AATCCAGTTGAAAATTACATAGATGAGGTACTAAATGAGGTATTGGTTGTACCAAACATT
367 70_HRV50a|  AATCCAGTGGAGAATTACATAGATGAAGTATTAAATGAGGTATTAGTTGTCCCAAATATC
368 71_HRV50b|  AATCCAGTGGAGAATTACATAGATGAAGTATTAAATGAGGTATTAGTTGTCCCAAATATC
369 72_HRV50    AATCCAGTGGAGAATTACATAGATGAAGTATTAAATGAGGTATTAGTTGTCCCAAATATC
370 73_HRV18a|  AATCCAGTAGAGAATTATATAGATGAAGTACTTAATGAAGTGTTAGTGGTCCCAAATGTG
371 74_HRV18b|  AATCCAGTAGAGAATTATATAGATGAAGTACTTAATGAAGTGTTAGTGGTCCCAAATGTG
372 75_HRV18    AATCCAGTAGAGAATTATATAGATGAAGTACTTAATGAAGTGTTAGTGGTCCCAAATGTG
373 76_HRV55    AATCCTGTAGAGAGATATGTTGATGAAGTCCTGAATGAAGTGCTAGTAGTTCCAAATATT
374 77_HRV55b|  AATCCTGTAGAGAGATATGTTGATGAAGTCCTGAATGAAGTGCTAGTAGTTCCAAATATT
375 78_HRV55a|  AATCCTGTAGAGAGATATGTTGATGAAGTCCTGAATGAAGTGCTAGTAGTTCCAAATATT
376 79_HRV57    AACCCAGTAGAAAATTTTGTGGATGAGATCTTGAATGAAGTTTTGGTGGTTCCAGATATC
377 80_HRV57a|  AACCCAGTAGAAAATTTTGTGGATGAGATCTTGAATGAAGTTTTGGTGGTTCCAGATATC
378 81_HRV57b|  AACCCAGTAGAAAATTTTGTGGATGAGATCTTGAATGAAGTTTTGGTGGTTCCAGATATC
379 82_HRV21    AATCCTGTAGAGAATTATATAGATGAAGTCCTAAATGAAGTCTTAGTAGTGCCAAATATC
380 83_HRVHan   AATCCTGTAGAGAATTACGTAGATGAAGTTCTAAATGAGGTCTTAGTAGTGCCAAATATC
381 84_HRV43    AATCCTGTTGAAAATTATGTTGATGAAATTTAAATCAAGTTCTTGTAGTCCCAAACACT
382 85_HRV43b|  AATCCTGTTGAAAATTATGTTGATGAAATTTTAAATCAAGTTCTTGTAGTCCCAAACACT
383 86_HRV43a|  AATCCTGTTGAAAATTATGTTGATGAAATTTTAAATCAAGTTCTTGTAGTCCCAAACACT
384 87_HRV75    AATCCAGTTGAAAATTATGTGGATGAAATTTTAAACCAAGTTCTGGTAGTTCCAAACACC
```

FIG. D5 CONT'D 01.trace                                                                          9/20/2007 4:58 PM

```
385  88_HRV75b|    AATCCAGTTGAAAATTATGTGGATGAAATTTTAAACCAAGTTCTGGTAGTTCCAAACACC
386  89_HRV75a|    AATCCAGTTGAAAATTATGTGGATGAAATTTTAAACCAAGTTCTGGTAGTTCCAAACACC
387  96_HRV9a|d    AATCCAGTGGAGAATTACATAGATCAGGTGCTTAATGAGGTTTTGGTAGTCCCAAACATT
388  97_HRV9b|d    AATCCAGTGGAGAATTACATAGATCAGGTGCTTAATGAGGTTTTGGTAGTCCCAAACATT
389  98_HRV9       AATCCAGTGGAGAATTACATAGATCAGGTGCTTAATGAGGTTTTGGTAGTCCCAAACATT
390  99_HRV32      AATCCTGTGGAGAATTACATAGATCAAGTTTTAAATGAAGTTTTGGTAGTTCCAAACATC
391  100_HRV32a    AATCCTGTGGAGAATTACATAGATCAAGTTTTAAATGAAGTTTTGGTAGTTCCAAACATC
392  101_HRV32b    AATCCTGTGGAGAATTACATAGATCAAGTTTTAAATGAAGTTTTGGTAGTTCCAAACATC
393  102_HRV67     AACCCAGTAGAAGATTATGTAGATCAGGTATTGAATGAGGTCCTGGTGGTGCCAAATATA
394  103_HRV67a    AACCCAGTAGAAGATTATGTAGATCAGGTATTGAATGAGGTCCTGGTGGTGCCAAATATA
395  104_HRV67b    AACCCAGTAGAAGATTATGTAGATCAGGTATTGAATGAGGTCCTGGTGGTGCCAAATATA
396  105_HRV15     AACCCAGTGGAGAATTACATAGATGAAGTGTTAAATGAGGTTCTAGTAGTTCCAAACATT
397  106_HRV15a    AACCCAGTGGAGAATTACATAGATGAAGTGTTAAATGAGGTTCTAGTAGTTCCAAACATT
398  107_HRV15b    AACCCAGTGGAGAATTACATAGATGAAGTGTTAAATGAGGTTCTAGTAGTTCCAAACATT
399  108_HRV74a    AACCCAGTGGAGAATTACATAGATGAAGTGTTGAATGAAGTGTTAGTTGTTCCAAATATT
400  109_HRV74b    AACCCAGTGGAGAATTACATAGATGAAGTGTTGAATGAAGTGTTAGTTGTTCCAAATATT
401  110_HRV74     AACCCAGTGGAGAATTACATAGATGAAGTGTTGAATGAAGTGTTAGTTGTTCCAAATATT
402  111_HRV38a    AACCCAGTAGAGGAATACATAGATGGAGTCTTGAATGAGGTTCTTGTGGTTCCGAACATT
403  112_HRV38b    AACCCAGTAGAGGAATACATAGATGGAGTCTTGAATGAGGTTCTTGTGGTTCCGAACATT
404  113_HRV38     AACCCAGTAGAGGAATACATAGATGGAGTCTTGAATGAGGTTCTTGTGGTTCCGAACATT
405  114_HRV60     AATCCAGTAGAAAGCTACATAGATGGGGTCTTAAACGAAGTCCTTGTGGTTCCAAACATT
406  115_HRV60a    AATCCAGTAGAAAGCTACATAGATGGGGTCTTAAACGAAGTCCTTGTGGTTCCAAACATT
407  116_HRV60b    AATCCAGTAGAAAGCTACATAGATGGGGTCTTAAACGAAGTCCTTGTGGTTCCAAACATT
408  117_HRV64a    AACCCAGTTGAACAATACATTGATGGTGTGTTGAATGAAGTTTTGATTGTCCCAAACATC
409  118_HRV64b    AACCCAGTTGAACAATACATTGATGGTGTGTTGAATGAAGTTTTGATTGTCCCAAACATC
410  119_HRV64     AACCCAGTTGAACAATACATTGATGGTGTGTTGAATGAAGTTTTGATTGTCCCAAACATC
411  120_HRV94a    AATCCAGTTGAGAAATACATTGATGGTGTATTGAATGAAGTTTTAGTTGTTCCAAATATC
412  121_HRV94b    AATCCAGTTGAGAAATACATTGATGGTGTATTGAATGAAGTTTTAGTTGTTCCAAATATC
413  122_HRV94     AATCCAGTTGAGAAATACATTGATGGTGTATTGAATGAAGTTTTAGTTGTTCCAAATATC
414  123_HRV22     AACCCTGTAGAGAAATACATTGATGGTGTATTGAATGAAGTATTGGTTGTTCCAAACACA
415  124_HRV22a    AACCCTGTAGAGAAATACATTGATGGTGTATTGAATGAAGTATTGGTTGTTCCAAACACA
416  125_HRV22b    AACCCTGTAGAGAAATACATTGATGGTGTATTGAATGAAGTATTGGTTGTTCCAAACACA
417  126_HRV82     AATCCAGTTGAAAAGTATGTTGATAGTGTTTTAAACGAGGTATTAGTTGTTCCTAACATT
418  127_HRV82b    AATCCAGTTGAAAAGTATGTTGATAGTGTTTTAAACGAGGTATTAGTTGTTCCTAACATT
419  128_HRV82a    AATCCAGTTGAAAAGTATGTTGATAGTGTTTTAAACGAGGTATTAGTTGTTCCTAACATT
420  129_HRV19     AATCCTGTAGAGAAATATGTGGACACCATTCTGAATGAGGTGCTAGTTGTCCCAAATATC
421  130_HRV19a    AATCCTGTAGAGAAATATGTGGACACCATTCTGAATGAGGTGCTAGTTGTCCCAAATATC
422  131_HRV19b    AATCCTGTAGAGAAATATGTGGACACCATTCTGAATGAGGTGCTAGTTGTCCCAAATATC
423  132_HRV13     AATCCTGTTGAAAGGTATGTAGATGAAGTCTTGAATGAAGTTCTTGTAGTACCAAATATC
424  133_HRV13a    AATCCTGTTGAAAGGTATGTAGATGAAGTCTTGAATGAAGTTCTTGTAGTACCAAATATC
425  134_HRV13b    AATCCTGTTGAAAGGTATGTAGATGAAGTCTTGAATGAAGTTCTTGTAGTACCAAATATC
426  135_HRV41     AATCCTGTAGAAAGGTATGTGGATGAGGTCCTGAATGAGGTTCTTGTGGTACCAAATATT
427  136_HRV41a    AATCCTGTAGAAAGGTATGTGGATGAGGTCCTGAATGAGGTTCTTGTGGTACCAAATATT
428  137_HRV41b    AATCCTGTAGAAAGGTATGTGGATGAGGTCCTGAATGAGGTTCTTGTGGTACCAAATATT
429  138_HRV73     AATCCTGTAGAAAGATATGTAGATGAAGTTTTGAATGAAGTCCTTGTAGTACCAATATC
430  139_HRV73b    AATCCTGTAGAAAGATATGTAGATGAAGTTTTGAATGAAGTCCTTGTAGTACCCAATATC
431  140_HRV73a    AATCCTGTAGAAAGATATGTAGATGAAGTTTTGAATGAAGTCCTTGTAGTACCAATATC
432  141_HRV61     AACCCTGTGGAAAGATATGTAGATGAAGTTTTTAAATGAAGTGCTTGTAGTCCCAAACATT
433  142_HRV61a    AACCCTGTGGAAAGATATGTAGATGAAGTTTTAAATGAAGTGCTTGTAGTCCCAAACATT
434  143_HRV61b    AACCCTGTGGAAAGATATGTAGATGAAGTTTTAAATGAAGTGCTTGTAGTCCCAAACATT
435  144_HRV96     AACCCTGTAGAGAGATATGTAGATGAAGTCTTGAATGAGGTTCTTGTAGTCCCTAATATT
436  145_HRV96b    AACCCTGTAGAGAGATATGTAGATGAAGTCTTGAATGAGGTTCTTGTAGTCCCTAATATT
437  146_HRV96a    AACCCTGTAGAGAGATATGTAGATGAAGTCTTGAATGAGGTTCTTGTAGTCCCTAATATT
438  90_HRV16a|    AATCCAGTGGAAAGATATGTAGATGAAGTCTTAAATGAAGTGTTAGTAGTGCCAATATT
439  91_HRV16b|    AATCCAGTGGAAAGATATGTAGATGAAGTCTTAAATGAAGTGTTAGTAGTGCCAATATT
440  92_1AYM_A     AATCCAGTGGAAAGATATGTAGATGAAGTCTTAAATGAAGTGTTAGTAGTGCCAATATT
441  93_HRV81a|    AACCCAGTGGAGCGGTATGTGGATGAAGTCTTAAATGAGGTATTGGTAGTCCCTAATATT
442  94_HRV81b|    AACCCAGTGGAGCGGTATGTGGATGAAGTCTTAAATGAGGTATTGGTAGTCCCTAATATT
443  95_HRV81      AACCCAGTGGAGCGGTATGTGGATGAAGTCTTAAATGAGGTATTGGTAGTCCCTAATATT
444  147_HRV2      AACCCTGTTGAAAATTATATAGATGAAGTTCTTAATGAAGTTTTAGTTGTCCCAAATATT
445  148_HRV2a|    AACCCTGTTGAGAATTATATAGATGAAGTTCTTAATGAAGTTTTAGTTGTGCCAAATATT
446  149_HRV2b|    AACCCTGTTGAGAATTATATAGATGAAGTTCTTAATGAAGTTTTAGTTGTCCCAAATATT
447  150_HRV49a    AATCCTGTTGAACACTACATAGATGAGGTCCTTAATGAGGTTTTAGTTGTTCCAAATATT
448  151_HRV49b    AATCCTGTTGAACACTACATAGATGAGGTCCTTAATGAGGTTTTAGTTGTTCCAAATATT
```

FIG. D5 CONT'D 01.trace                                                                9/20/2007 4:58 PM

```
449  152_HRV49    AATCCTGTTGAACACTACATAGATGAGGTCCTTAATGAGGTTTTAGTTGTTCCAAATATT
450  153_HRV23a   AATCCAATTGAGAACTATGTAGATGAAGTTCTTAATGAAGTCTTAGTTGTTCCCAATATC
451  154_HRV23b   AATCCAATTGAGAACTATGTAGATGAAGTTCTTAATGAAGTCTTAGTTGTTCCTAACATC
452  155_HRV23    AATCCAATTGAGAACTATGTAGATGAAGTTCTTAATGAAGTCTTAGTTGTTCCCAATATC
453  156_HRV30a   AACCCGGTTGAAAATTTTGTAGATGAAGTTCTTAGTGAAGTTTTAGTTGTTCCAAACATT
454  157_HRV30b   AACCCGGTTGAAAATTTTGTAGATGAAGTTCTTAGTGAAGTTTTAGTTGTTCCAAACATT
455  158_HRV30    AACCCGGTTGAAAATTTTGTAGATGAAGTTCTTAGTGAAGTACTTGTAGTGCCAAACATA
456  159_HRV7     AACCCGGTAGAGAATTATGTAGATAGCTTACTAAATGAAGTATTAGTGGTACCTAATATT
457  160_HRV7b    AACCCGGTAGAGAATTATGTAGATAGCTTACTAAATGAAGTATTAGTGGTACCTAATATT
458  161_HRV7a    AACCCGGTAGAGAATTATGTAGATAGCTTACTAAATGAAGTATTAGTGGTACCTAATATT
459  162_HRV88    AATCCAGTAGAAAACTATGTAGATAACTTGTTAAACGAAGTGCTAGTAGTTCCTAACATT
460  163_HRV88a   AATCCAGTAGAAAACTATGTAGATAACTTGTTAAACGAAGTGCTAGTAGTTCCTAACATT
461  164_HRV88b   AATCCAGTAGAAAACTATGTAGATAACTTGTTAAACGAAGTGCTAGTAGTTCCTAACATT
462  165_HRV36a   AATCCAGTTGAAAATTACATAGATAATGTATTAAATGAAGTACTTGTAGTGCCAAACATC
463  166_HRV36b   AATCCAGTTGAAAATTACATAGATAATGTATTAAATGAAGTACTTGTAGTGCCAAACATC
464  167_HRV36    AATCCAGTTGAAAATTACATAGATAATGTATTAAATGAAGTACTTGTAGTGCCAAACATC
465  168_HRV89a   AACCCAGTTGAAAATTATATAGATAGTGTATTAAATGAAGTTCTTGTGGTGCCAAATATC
466  169_HRV89b   AACCCAGTTGAAAATTATATAGATAGTGTATTAAATGAAGTTCTTGTGGTGCCAAATATC
467  170_HRV89    AACCCAGTTGAAAATTATATAGATAGTGTATTAAATGAAGTTCTTGTGGTGCCAAATATC
468  171_HRV58    AATCCAGTAGAAAATTACATAGATAATGTGTTAAATGAAGTACTTGTAGTTCCAAATATC
469  172_HRV58a   AATCCAGTAGAAAATTACATAGATAATGTGTTAAATGAAGTACTTGTAGTTCCAAATATC
470  173_HRV58b   AATCCAGTAGAAAATTACATAGATAATGTGTTAAATGAAGTACTTGTAGTTCCAAATATC
471  174_HRV12a   AATCCAGTAGAGAGATATGTTGATGAGGTGCTAAATGAAGTTCTAGTTGTTCCAAACATA
472  175_HRV12b   AATCCAGTAGAGAGATATGTTGATGAGGTGCTAAATGAAGTTCTAGTTGTTCCAAACATA
473  176_HRV12    AATCCAGTAGAGAGATATGTTGATGAGGTGCTAAATGAAGTACTTGTTGTTCCAAACATA
474  177_HRV78a   AATCCAGTGGAAGAATATGTTGATCAGGTTTTAAATGAGGTTTTAGTTGTTCCAAACATA
475  178_HRV78b   AATCCAGTGGAAGAATATGTTGATCAGGTTTTAAATGAGGTTTTAGTTGTTCCAAACATA
476  179_HRV78    AATCCAGTGGAAGAATATGTTGATCAGGTTTTAAATGAGGTTTTAGTTGTTCCAAACATA
477  180_HRV20    AACCCAGTGGAAAGGTACACAGAAGCTATTTAAATGAAGTTCTTGTAGTTCCAAATATC
478  181_HRV20a   AACCCAGTGGAAAGGTACACAGAAGCTATTTAAATGAAGTTCTTGTAGTTCCAAATATC
479  182_HRV20b   AACCCAGTGGAAAGGTACACAGAAGCTATTTAAATGAAGTTCTTGTAGTTCCAAATATC
480  183_HRV68    AACCCAGTTGAAAATACACAGAAGCCGTTCTTAATGAGGTCCTTGTGGTTCCAAACATA
481  184_HRV68a   AACCCAGTTGAAAATACACAGAAGCCGTTCTTAATGAGGTCCTTGTGGTTCCAAACATA
482  185_HRV68b   AACCCAGTTGAAAATACACAGAAGCCGTTCTTAATGAGGTCCTTGTGGTTCCAAACATA
483  186_HRV28    AATCCAGTTGAAAATATACTGAAGCACTACTTAATGAAGTGCTTGTTGTGCCAAACATC
484  187_HRV28a   AATCCAGTTGAAAATATACTGAAGCACTACTTAATGAAGTGCTTGTTGTGCCAAACATC
485  188_HRV28b   AATCCAGTTGAAAATATACTGAAGCACTACTTAATGAAGTGCTTGTTGTGCCAAACATC
486  189_HRV53a   AACCCGGTAGAGAAAATACACAGAGGCTATCTTAAATGAAGTATTAGTAGTCCCAAACATT
487  190_HRV53b   AACCCGGTAGAGAAAATACACAGAGGCTATCTTAAATGAAGTATTAGTAGTCCCAAACATT
488  191_HRV53    AACCCGGTAGAGAAAATACACAGAGGCTATCTTAAATGAAGTATTAGTAGTCCCAAACATT
489  192_HRV46a   AATCCAGTGGAAAATATACAGAAGCTGTTCTTAATGAGGTCCTTGTAGTACCTAACATC
490  193_HRV46b   AATCCAGTGGAAAATATACAGAAGCTGTTCTTAATGAGGTCCTTGTAGTACCTAACATC
491  194_HRV46    AATCCAGTGGAAAATATACAGAAGCTGTTCTTAATGAGGTCCTTGTAGTACCTAACATC
492  195_HRV80a   AATCCAGTCGAAAATACACAGAAGCAATCCTCAATGAAGTTCTTGTTGTACCAAACATC
493  196_HRV80b   AATCCAGTCGAAAATACACAGAAGCAATCCTCAATGAAGTTCTTGTTGTACCAAACATC
494  197_HRV80    AATCCAGTCGAAAATACACAGAAGCAATCCTCAATGAAGTTCTTGTTGTACCAAACATC
495  198_HRV51    AACCCTGTTGAAAATATACAGAGGCTTTACTCAATGAAGTGTTGGTGGTTCCCAACATA
496  199_HRV51a   AACCCTGTTGAAAATATACAGAGGCTTTACTCAATGAAGTGTTGGTGGTTCCCAACATA
497  200_HRV51b   AACCCTGTTGAAAATATACAGAGGCTTTACTCAATGAAGTGTTGGTGGTTCCCAACATA
498  201_HRV65a   AATCCAATTGAGAAGTATACAGAAGCTCTACTTAATGAAGTGTTGGTGGTCCCAAATATA
499  202_HRV65b   AATCCAATTGAGAAGTATACAGAAGCTCTACTTAATGAAGTGTTGGTGGTCCCAAATATA
500  203_HRV65    AATCCAATTGAGAAGTATACAGAAGCTCTACTTAATGAAGTGTTGGTGGTCCCAAATATA
501  204_HRV71a   AATCCTGTAGAAAAATATACAGAAGCAATACTCAATGAGGTTCTAGTTGTGCCAAATATA
502  205_HRV71b   AATCCTGTAGAAAAATATACAGAAGCAATACTCAATGAGGTTCTAGTTGTGCCAAATATA
503  206_HRV71    AATCCTGTAGAAAAATATACAGAAGCAATACTCAATGAGGTTCTAGTTGTGCCAAATATA
504  207_HRV8     AACCCTATTGAACAATTCACAGAGGCAGTATTAAACGAGGTTCTTGTAGTTCCAAACACA
505  208_HRV95    AACCCTATTGAACAATTCACAGAGGCAGTATTAAACGAGGTTCTTGTAGTTCCAAATACA
506  209_HRV45    AACCCTGTTGAACAATTTGCAGAAGCAGTCCTTGATCAAGTATTAGTAGTTCCAAACACT
507  210_HRV45a   AACCCTGTTGAACAATTTGCAGAAGCAGTCCTTGATCAAGTATTAGTAGTTCCAAACACT
508  211_HRV45b   AACCCTGTTGAACAATTTGCAGAAGCAGTCCTTGATCAAGTATTAGTAGTTCCAAACACT
509  212_HRV6     ------------------------------------------------------------
510  213_HRV6a    ------------------------------------------------------------
511  214_HRV6b    ------------------------------------------------------------
512  215_HRV37    ------------------------------------------------------------
```

FIG. D5 CONT'D 01.trace　　　　　　　　　　　　　　　　　　　　　　　　　　　　　　　　　9/20/2007 4:58 PM

```
513  216_HRV37a    ------------------------------------------------------------
514  217_HRV37b    ------------------------------------------------------------
515  218_HRV3      ------------------------------------------------------------
516  219_HRV3a|    ------------------------------------------------------------
517  220_HRV3b|    ------------------------------------------------------------
518  221_HRV14     ------------------------------------------------------------
519  222_HRV14a    ------------------------------------------------------------
520  223_HRV14b    ------------------------------------------------------------
521  224_HRV72     ------------------------------------------------------------
522  225_HRV72a    ------------------------------------------------------------
523  226_HRV72b    ------------------------------------------------------------
524  227_HRV83     ------------------------------------------------------------
525  228_HRV83a    ------------------------------------------------------------
526  229_HRV83b    ------------------------------------------------------------
527  230_HRV92     ------------------------------------------------------------
528  231_HRV92a    ------------------------------------------------------------
529  232_HRV92b    ------------------------------------------------------------
530  233_HRV79     ------------------------------------------------------------
531  234_HRV79a    ------------------------------------------------------------
532  235_HRV79b    ------------------------------------------------------------
533  236_HRV35     ------------------------------------------------------------
534  237_HRV35a    ------------------------------------------------------------
535  238_HRV35b    ------------------------------------------------------------
536  239_1HRV86    ------------------------------------------------------------
537  240_1HRV86    ------------------------------------------------------------
538  241_1HRV86    ------------------------------------------------------------
539  242_HRV70     ------------------------------------------------------------
540  243_HRV70a    ------------------------------------------------------------
541  244_HRV70b    ------------------------------------------------------------
542  245_HRV91     ------------------------------------------------------------
543  246_HRV91a    ------------------------------------------------------------
544  247_HRV91b    ------------------------------------------------------------
545  248_HRV17     ------------------------------------------------------------
546  249_HRV17a    ------------------------------------------------------------
547  250_HRV17b    ------------------------------------------------------------
548  251_HRV69     ------------------------------------------------------------
549  252_HRV69a    ------------------------------------------------------------
550  253_HRV69b    ------------------------------------------------------------
551  254_HRV48     ------------------------------------------------------------
552  255_HRV48a    ------------------------------------------------------------
553  256_HRV48b    ------------------------------------------------------------
554  257_HRV52     ------------------------------------------------------------
555  258_HRV52a    ------------------------------------------------------------
556  259_HRV52b    ------------------------------------------------------------
557  260_HRV4      ------------------------------------------------------------
558  261_HRV4a|    ------------------------------------------------------------
559  262_HRV4b|    ------------------------------------------------------------
560  263_HRV99     ------------------------------------------------------------
561  264_HRV99a    ------------------------------------------------------------
562  265_HRV99b    ------------------------------------------------------------
563  266_HRV5      ------------------------------------------------------------
564  267_HRV5a|    ------------------------------------------------------------
565  268_HRV5b|    ------------------------------------------------------------
566  269_HRV42     ------------------------------------------------------------
567  270_HRV42a    ------------------------------------------------------------
568  271_HRV42b    ------------------------------------------------------------
569  272_HRV26     ------------------------------------------------------------
570  273_HRV26a    ------------------------------------------------------------
571  274_HRV26b    ------------------------------------------------------------
572  275_HRV27     ------------------------------------------------------------
573  276_HRV27a    ------------------------------------------------------------
574  277_HRV27b    ------------------------------------------------------------
575  278_HRV93     ------------------------------------------------------------
576  279_HRV93a    ------------------------------------------------------------
```

FIG. D5 CONT'D

01.trace  9/20/2007 4:58 PM

```
577 280_HRV93b      ------------------------------------------------------------
578 281_HRV97       ------------------------------------------------------------
579 282_HRV97a      ------------------------------------------------------------
580 283_HRV97b      ------------------------------------------------------------
581 284_HRV84       ------------------------------------------------------------
582 285_HRV84a      ------------------------------------------------------------
583 286_HRV84b      ------------------------------------------------------------
584 287_HRV87       ------------------------------------------------------------
585 288_HRV87a      ------------------------------------------------------------
586 289_HRV87b      ------------------------------------------------------------
587 GROUP_1         ------------------------------------------------------------
588
589   1_HRV1A1|d    AAAGAAAGTCATCACACTACATCAAACTCTGCCCCACTTTTAGATGCTGCAGAGACGGGA
590   2_HRV1A2|d    AAAGAAAGTCATCACACTACATCAAACTCTGCCCCACTTTTAGATGCTGCAGAGACGGGA
591   3_HRV1A|cD    AAAGAAAGTCATCACACTACATCAAACTCTGCCCCACTTTTAGATGCTGCAGAGACGGGA
592   4_HRV1B1|d    AAAGAAAGCCATCACACTACATCAAATTCTGCTCCACTCTTGGATGCTGCAGAGACAGGA
593   5_HRV1B2|d    AAAGAAAGCCATCACACTACATCAAATTCTGCTCCACTCTTGGATGCTGCAGAGACAGGA
594   6_HRV1B       AAAGAAAGCCATCACACTACATCAAATTCTGCTCCACTCTTGGATGCTGCAGAGACAGGA
595   7_HRV40a|d    AGAGAGAGCCATCCAACTACATCAAATTCGGCCCCTGCCTTGGATGCAGCAGAGACTGGA
596   8_HRV40b|d    AGAGAGAGCCATCCAACTACATCAAATTCGGCCCCTGCCTTGGATGCAGCAGAGACTGGA
597   9_HRV40       AGAGAGAGCCATCCAACTACATCAAATTCGGCCCCTGCCTTGGATGCAGCAGAGACTGGA
598  10_HRV85       AAAGAGAGTCACCCAACTATATCAAATTCAGCTCCTGCTTTGGATGCAGCAGAGACTGGC
599  11_HRV85a|     AAAGAGAGTCACCCAACTATATCAAATTCAGCTCCTGCTTTGGATGCAGCAGAGACTGGC
600  12_HRV85b|     AAAGAGAGTCACCCAACTATATCAAATTCAGCTCCTGCTTTGGATGCAGCAGAGACTGGC
601  13_HRV56a|     AGGGAGAGCCATCCATCCACATCAAATTCTGCCCCTGCATTAGATGCTGCTGAAACTGGC
602  14_HRV56b|     AGGGAGAGCCATCCATCCACATCAAATTCTGCCCCTGCATTAGATGCTGCTGAAACTGGC
603  15_HRV56       AGGGAGAGCCATCCATCCACATCAAATTCTGCCCCTGCATTAGATGCTGCTGAAACTGGC
604  16_HRV54       AGAGAAAGTCATCCAGCTACATCTAATTCAGCCCTAGCTAGATGCGGCAGAAACTGGA
605  17_HRV98       AAAGAAAGTCATCCAGCTACATCTAATTCGGCCCCTACACTAGATGCAGCAGAAACTGGG
606  18_HRV59a|     CAGGAAAGCCACCCAACCACCTCAAATGCTGCTCCAGCATTAGATGCAGCAGAGACTGGA
607  19_HRV59b|     CAGGAAAGCCACCCAACCACCTCAAATGCTGCTCCAGCATTAGATGCAGCAGAGACTGGA
608  20_HRV59       CAGGAAAGCCACCCAACCACCTCAAATGCTGCTCCAGCATTAGATGCAGCAGAGACTGGA
609  21_HRV63       CAAGAAAGCCATCCAACCACATCAAACGCTGCTCCTGTACTTGATGCTGCGGAAACAGGA
610  22_HRV63b|     CAAGAAAGCCATCCAACCACATCAAACGCTGCTCCTGTACTTGATGCTGCGGAAACAGGA
611  23_HRV63a|     CAAGAAAGCCATCCAACCACATCAAACGCTGCTCCTGTACTTGATGCTGCGGAAACAGGA
612  24_HRV39       AGAGAGAGCCATCCAACTACATCTAATGCAGCTACAGCTTTGGATGCTGCTGAAACTGGA
613  25_HRV39a|     AGAGAGAGCCATCCAACTACATCTAATGCAGCTACAGCTTTGGATGCTGCTGAAACTGGA
614  26_HRV39b|     AGAGAGAGCCATCCAACTACATCTAATGCAGCTCCAGCTTTGGATGCTGCTGAAACTGGA
615  27_HRV10a|     AGAGAAAGTCATCCAAGCACCTCTAACTCTGCCCCAATTCTCGATGCAGCTGAGACTGGT
616  28_HRV10b|     AGAGAAAGTCATCCAAGCACCTCTAACTCTGCCCCAATTCTCGATGCAGCTGAGACTGGT
617  29_HRV10       AGAGAAAGTCATCCAAGCACCTCTAACTCTGCCCCAATTCTCGATGCAGCTGAGACTGGT
618  30_HRV100a     AGAGAGAGCCATCCAAGCACCTCAAACTCTGCTCCAATCCTTGATGCTGCTGAAACTGGC
619  31_HRV100b     AGAGAGAGCCATCCAAGCACCTCAAACTCTGCTCCAATCCTTGATGCTGCTGAAACTGGC
620  32_HRV100      AGAGAGAGCCATCCAAGCACCTCAAACTCTGCTCCAATCCTTGATGCTGCTGAAACTGGC
621  33_HRV66       AAGGAAAGCCATCCAAGCACATCAAATGCTGCCCCAATACTAGATGCAGCTGAAACAGGT
622  34_HRV66b|     AAGGAAAGCCATCCAAGCACATCAAATGCTGCCCCAATACTAGATGCAGCTGAAACAGGT
623  35_HRV66a|     AAGGAAAGCCATCCAAGCACATCAAATGCTGCCCCAATACTAGATGCAGCTGAAACAGGT
624  36_HRV77a|     AAGGAGAGTCATCCAAGCACTTCTAACTCTGCTCCTATACTAGATGCAGCTGAAACAGGC
625  37_HRV77b|     AAGGAGAGTCATCCAAGCACTTCTAACTCTGCTCCTATACTAGATGCAGCTGAAACAGGC
626  38_HRV77       AAGGAGAGTCATCCAAGCACTTCTAACTCTGCTCCTATACTAGATGCAGCTGAAACAGGC
627  39_HRV62a      AAAGAAAGTCACCCTAGTACGTCAAACTCTGCCCCAATTCTAGATGCTGCTGAAACCGGA
628  40_HRV62b      AAAGAAAGTCACCCTAGTACGTCAAACTCTGCCCCAATTCTAGATGCTGCTGAAACCGGA
629  41_HRV25       AAAGAAAGTCACCCAAGCACATCAAATTCTGCCCCAATTCTAGATGCTGCTGAAACTGGA
630  42_HRV29a      AGGGAGAGCCACCCAAGCACGTCCAACTCTGCACCAATCTTGGATGCTGCTGAGACTGGA
631  43_HRV29b      AGGGAGAGCCACCCAAGCACGTCCAACTCTGCACCAATCTTGGATGCTGCTGAGACTGGA
632  44_HRV44a      AGAGAGAGCCACCCAAGCACATCTAACTCTGCTCCAATTTTGGATGCTGCTGAAACTGGA
633  45_HRV44b      AGAGAGAGCCACCCAAGCATATCTAACTCTGCTCCAATTTTGGATGCTGCTGAAACTGGA
634  46_HRV31       AAAGAAAGCCATCCAAGCACATCTAATTCTGCCCCAATCCTGGACGCTGCTGAAACTGGA
635  47_HRV31a|     AAAGAAAGCCATCCAAGCACATCTAATTCTGCCCCAATCCTGGACGCTGCTGAAACTGGA
636  48_HRV31b|     AAAGAAAGCCATCCAAGCACATCTAATTCTGCCCCAATCCTGGACGCTGCTGAAACTGGA
637  49_HRV47       AAAGAAAGTCATCCAAGTACATCCAACTCTGCCCCCGATTTTAGATGCTGCTGAAACTGGA
638  50_HRV47a|     AAAGAAAGTCATCCAAGTACATCCAACTCTGCCCCCGATTTTAGATGCTGCTGAAACTGGA
639  51_HRV47b|     AAAGAAAGTCATCCAAGTACATCCAACTCTGCCCCCGATTTTAGATGCTGCTGAAACTGGA
640  52_HRV11       AAGGAGAGCCAAGCTACCACATCAAACTCAGCACCTGCTCTAGATGCAGCTGAAACCGGA
```

FIG. D5 CONT'D

01.trace                                                                   9/20/2007 4:58 PM

```
641  53_HRV11b|    AAGGAGAGCCAAGCTACCACATCAAACTCAGCACCTGCTCTAGATGCAGCTGAAACCGGA
642  54_HRV11a|    AAGGAGAGCCAAGCTACCACATCAAACTCAGCACCTGCTCTAGATGCAGCTGAAACCGGA
643  55_HRV76     AAAGAGAGTCAGGCTACCACATCAAATGCAGCACCTGCTTTGGATGCAGCTGAGACTGGG
644  56_HRV76b|    AAAGAGAGTCAGGCTACCACATCAAATGCAGCACCTGCTTTGGATGCAGCTGAGACTGGG
645  57_HRV76a|    AAAGAGAGTCAGGCTACCACATCAAATGCAGCACCTGCTTTGGATGCAGCTGAGACTGGG
646  58_HRV33     AGAGAGAGTCAAGCAACCACATCAAATTCAGCACCTGCCTTAGATGCAGCTGAGACTGGA
647  59_HRV33b|    AGAGAGAGTCAAGCAACCACATCAAATTCAGCACCTGCCTTAGATGCAGCTGAGACTGGA
648  60_HRV33a|    AGAGAGAGTCAAGCAACCACATCAAATTCAGCACCTGCCTTAGATGCAGCTGAGACTGGA
649  61_HRV24a|    AAGGAAAGTAAACCATCAACATCAAACTCAGCACCAGCTTTGGATGCAGCAGAAACTGGA
650  62_HRV24b|    AAGGAAAGTAAACCATCAACATCAAACTCAGCACCAGCTTTGGATGCAGCAGAAACTGGA
651  63_HRV24     AAGGAAAGTAAACCATCAACATCAAACTCAGCACCAGCTTTGGATGCAGCAGAAACTGGA
652  64_HRV90     AAGGAAAGTAAACCTTCAACTTCAAACTCAGCGCCAGCTTTAGATGCAGCAGAAACCGGA
653  65_HRV90a|    AAGGAAAGTAAACCTTCAACTTCAAACTCAGCGCCAGCTTTAGATGCAGCAGAAACCGGA
654  66_HRV90b|    AAGGAAAGTAAACCTTCAACTTCAAACTCAGCGCCAGCTTTAGATGCAGCAGAAACCGGA
655  67_HRV34     AAAGAAAGCCAAGCCACCACATCAAACTCTGCCCCCGCACTGGATGCAGCTGAGACTGGT
656  68_HRV34b|    AAAGAAAGCCAAGCCACCACATCAAACTCTGCCCCCGCACTGGATGCAGCTGAGACTGGT
657  69_HRV34a|    AAAGAAAGCCAAGCCACCACATCAAACTCTGCCCCCGCACTGGATGCAGCTGAGACTGGT
658  70_HRV50a|    AAGGAGAGTCAAGCCACTACATCAAACTCTGCCCCTGCTTTAGATGCAGCTGAAACTGGA
659  71_HRV50b|    AAGGAGAGTCAAGCCACTACATCAAACTCTGCCCCTGCTTTAGATGCAGCTGAAACTGGA
660  72_HRV50     AAGGAGAGTCAAGCCACTACATCAAACTCTGCCCCTGCTTTAGATGCAGCTGAAACTGGA
661  73_HRV18a|    AATGAAAGTCACGCAATTACATCAAATTCAGCCCCTGCTTTAGATGCCGCTGAAACTGGT
662  74_HRV18b|    AATGAAAGTCACGCAATTACATCAAATTCAGCCCCTGCTTTAGATGCCGCTGAAACTGGT
663  75_HRV18     AATGAAAGTCACGCAATTACATCAAATTCAGCCCCTGCTTTAGATGCCGCTGAAACTGGT
664  76_HRV55     AGGGAGAGTCAAGCAGCAACATCAAATTCAGCTCCAGTACTAGATGCAGCAGAAACTGGG
665  77_HRV55b|    AGGGAGAGTCAAGCAGCAACATCAAATTCAGCTCCAGTACTAGATGCAGCAGAAACTGGG
666  78_HRV55a|    AGGGAGAGTCAAGCAGCAACATCAAATTCAGCTCCAGTACTAGATGCAGCAGAAACTGGG
667  79_HRV57     AAACAAAGTCAAGCAACAACATCAAACTCAGCACCTGCATTGGATGCAGCTGAAACTGGA
668  80_HRV57a|    AAACAAAGTCAAGCAACAACATCAAACTCAGCACCTGCATTGGATGCAGCTGAAACTGGA
669  81_HRV57b|    AAACAAAGTCAAGCAACAACATCAAACTCAGCACCTGCATTGGATGCAGCTGAAACTGGA
670  82_HRV21     AGAGAGAGTCATGGAACAACATCAAACTCTGCTCCCGCACTTGATGCTGCAGAAACTGGA
671  83_HRVHan    AGAGAGAGTCATGGAACAACATCAAACTCTGCTCCCGCACTTGATGCTGCAGAAACTGGG
672  84_HRV43     GTAGAAAGTCATTCAACAACATCCAATGCAGCCCCTGCACTTGATGCAGCTGAAACTGGG
673  85_HRV43b|    GTAGAAAGTCATTCAACAACATCCAATGCAGCCCCTGCACTTGATGCAGCTGAAACTGGG
674  86_HRV43a|    GTAGAAAGTCATTCAACAACATCCAATGCAGCCCCTGCACTTGATGCAGCTGAAACTGGG
675  87_HRV75     ATGGAGAGCCATCCAACAACGTCTAATGCTGCTCCAGCTTTAGATGCAGCTGAAACTGGC
676  88_HRV75b|    ATGGAGAGCCATCCAACAACGTCTAATGCTGCTCCAGCTTTAGATGCAGCTGAAACTGGC
677  89_HRV75a|    ATGGAGAGCCATCCAACAACGTCTAATGCTGCTCCAGCTTTAGATGCAGCTGAAACTGGC
678  96_HRV9a|d    AAAGAGAGCAACCCTACAACCTCTAACTCAGCTCCAGCTCTAGATGCTGCTGAGACAGGC
679  97_HRV9b|d    AAAGAGAGCAACCCTACAACCTCTAACTCAGCTCCAGCTCTAGATGCTGCTGAGACAGGC
680  98_HRV9      AAAGAGAGCAACCCTACAACCTCTAACTCAGCTCCAGCTCTAGATGCTGCTGAGACAGGC
681  99_HRV32     AAAGAGAGCAATCCCACAACCTCTCAGCCCCAGCCTTAGATGCTGCCGAAACAGGT
682  100_HRV32a    AAAGAAAGCAATCCCACAACCTCTAATTCAGCCCCAGCCTTAGATGCTGCCGAAACAGGT
683  101_HRV32b    AAAGAAAGCAATCCCACAACCTCTAATTCAGCCCCAGCCTTAGATGCTGCCGAAACAGGT
684  102_HRV67    AAGCAAAGTGAACCCACGACTTCCAATTCAGCCCCAGCTCTAGATGCTGCTGAGACAGGT
685  103_HRV67a    AAGCAAAGTGAACCCACGACTTCCAATTCAGCCCCAGCTCTAGATGCTGCTGAGACAGGT
686  104_HRV67b    AAGCAAAGTGAACCCACGACTTCCAATTCAGCCCCAGCTCTAGATGCTGCTGAGACAGGT
687  105_HRV15    AAGGAGAGTCACTCAAGCACATCCAACTCAGCACCAGCACTAGATGCAGCTGAGACCGGC
688  106_HRV15a   AAGGAGAGTCACTCAAGCACATCCAACTCAGCACCAGCACTAGATGCAGCTGAGACCGGC
689  107_HRV15b   AAGGAGAGTCACTCAAGCACATCCAACTCAGCACCAGCACTAGATGCAGCTGAGACCGGC
690  108_HRV74a   AGAGAAAGCCATTCAAGTACTTCAAACTCAGCACCAGCACTGGATGCAGCTGAAACTGGC
691  109_HRV74b   AGAGAAAGCCATTCAAGTACTTCAAACTCAGCACCAGCACTGGATGCAGCTGAAACTGGC
692  110_HRV74    AGAGAAAGCCATTCAAGTACTTCAAACTCAGCACCAGCACTGGATGCAGCTGAAACTGGC
693  111_HRV38a   AAGGAAAGCCACTCCAGCACATCAAATTCAGCACCAGCATTAGATGCTGCTGAGACTGGA
694  112_HRV38b   AAGGAAAGCCACTCCAGCACATCAAATTCAGCACCAGCATTAGATGCTGCTGAGACTGGA
695  113_HRV38    AAGGAAAGCCACTCCAGCACATCAAATTCAGCACCAGCATTAGATGCTGCTGAGACTGGA
696  114_HRV60    AGGGAGAGCCAACCCACTACTTCTAATTCTGCTCCAGCATTGGATGCTGCTGAGACTGGT
697  115_HRV60a   AGGGAGAGCCAACCCACTACTTCTAATTCTGCTCCAGCATTGGATGCTGCTGAGACTGGT
698  116_HRV60b   AGGGAGAGCCAACCCACTACTTCTAATTCTGCTCCAGCATTGGATGCTGCTGAGACTGGT
699  117_HRV64a   AATGAGAGCCATCCCAGCACTTCCAATGCAGCGCCAGCTTTAGATGCAGCTGAGACCGGA
700  118_HRV64b   AATGAGAGCCATCCCAGCACTTCCAATGCAGCGCCAGCTTTAGATGCAGCTGAGACCGGA
701  119_HRV64    AATGAGAGCCATCCCAGCACTTCCAATGCAGCGCCAGCTTTAGATGCAGCTGAGACCGGA
702  120_HRV94a   AATGAGAGTCACCCTAGCACATCCAATGCAGCGCCAGCCTTAGATGCTGCCGAAACTGGA
703  121_HRV94b   AATGAGAGTCACCCTAGCACATCCAATGCAGCGCCAGCCTTAGATGCTGCCGAAACTGGA
704  122_HRV94    AATGAGAGTCACCCTAGCACATCCAATGCAGCGCCAGCCTTAGATGCTGCCGAAACTGGA
```

FIG. D5 CONT'D 01.trace                                                              9/20/2007 4:58 PM

```
705 123_HRV22    AATGAAAGTCACCCCAGTACATCAAATGCTGCACCAGCACTAGATGCTGCTGAAACTGGA
706 124_HRV22a   AATGAAAGTCACCCCAGTACATCAAATGCTGCACCAGCACTAGATGCTGCTGAAACTGGA
707 125_HRV22b   AATGAAAGTCACCCCAGTACATCAAATGCTGCACCAGCACTAGATGCTGCTGAAACTGGA
708 126_HRV82    AATGAAAGTCATCCTAGTACTTCAAATTCAGCTCCTGCCTTGGACGCTGCAGAGACAGGA
709 127_HRV82b   AATGAAAGTCATCCTAGTACTTCAAATTCAGCTCCTGCCTTGGACGCTGCAGAGACAGGA
710 128_HRV82a   AATGAAAGTCATCCTAGTACTTCAAATTCAGCTCCTGCCTTGGACGCTGCAGAGACAGGA
711 129_HRV19    AATGAAAGTCATCCAAGTACATCAAATGCTGCTCCTGCCTTAGATGCAGCCGAGACAGGA
712 130_HRV19a   AATGAAAGTCATCCAAGTACATCAAATGCTGCTCCTGCCTTAGATGCAGCCGAGACAGGA
713 131_HRV19b   AATGAAAGTCATCCAAGTACATCAAATGCTGCTCCTGCCTTAGATGCAGCCGAGACAGGA
714 132_HRV13    AGTGAAAGTAGCTCAACTACATCTAATTCAGCTCCAGCCTTAGATGCTGCAGAAACTGGC
715 133_HRV13a   AGTGAAAGTAGCTCAACTACATCTAATTCAGCTCCAGCCTTAGATGCTGCAGAAACTGGC
716 134_HRV13b   AGTGAAAGTAGCTCAACTACATCTAATTCAGCTCCAGCCTTAGATGCTGCAGAAACTGGC
717 135_HRV41    AGTGAAAGCAGTCCAACTACTTCTAATTCAGCTCCAGCCCTAGATGCAGCAGAGACTGGT
718 136_HRV41a   AGTGAAAGCAGTCCAACTACTTCTAATTCAGCTCCAGCCCTAGATGCAGCAGAGACTGGT
719 137_HRV41b   AGTGAAAGCAGTCCAACTACTTCTAATTCAGCTCCAGCCCTAGATGCAGCAGAGACTGGT
720 138_HRV73    AATGAAAGTAATCCAACTACATCCAACTCAGCACCTGCACTGGACGCTGCAGAAACTGGC
721 139_HRV73b   AATGAAAGTAATCCAACTACATCCAACTCAGCACCTGCACTGGACGCTGCAGAAACTGGC
722 140_HRV73a   AATGAAAGTAATCCAACTACATCCAACTCAGCACCTGCACTGGACGCTGCAGAAACTGGC
723 141_HRV61    AATCAGAGCAACCCTACAACATCCAACTCAGCACCAGTCTTAGACGCTGCTGAAACAGGT
724 142_HRV61a   AATCAGAGCAACCCTACAACATCCAACTCAGCACCAGTCTTAGACGCTGCTGAAACAGGT
725 143_HRV61b   AATCAGAGCAACCCTACAACATCCAACTCAGCACCAGTCTTAGACGCTGCTGAAACAGGT
726 144_HRV96    AATGAAAGTTACCCAACAACTTCCAATTCAGCCCCAGTGCTAGATGCCGCTGAAACAGGT
727 145_HRV96b   AATGAAAGTTACCCAACAACTTCCAATTCAGCCCCAGTGCTAGATGCCGCTGAAACAGGT
728 146_HRV96a   AATGAAAGTTACCCAACAACTTCCAATTCAGCCCCAGTGCTAGATGCCGCTGAAACAGGT
729 90_HRV16a|   AATGAGAGCCACCCTACCACATCAAATGCGGCCCCAGTTTTGGATGCTGCTGAAACAGGA
730 91_HRV16b|   AATGAGAGCCACCCTACCACATCAAATGCGGCCCCAGTTTTGGATGCTGCTGAAACAGGA
731 92_1AYM_A    AATGAGAGCCACCCTACCACATCAAATGCGGCCCCAGTTTTGGATGCTGCTGAAACAGGA
732 93_HRV81a|   AATGAAAGCCACCCTACAACATCTAATTCAGCTCCTGTTTTAGATGCAGCTGAAACTGGA
733 94_HRV81b|   AATGAAAGCCACCCTACAACATCTAATTCAGCTCCTGTTTTAGATGCAGCTGAAACTGGA
734 95_HRV81     AATGAAAGCCACCCTACAACATCTAATTCAGCTCCTGTTTTAGATGCAGCTGAAACTGGA
735 147_HRV2     AATAGTAGTAACCCCACAACATCAAATTCTGCCCCAGCATTAGATGCTGCAGAAACAGGG
736 148_HRV2a|   AATAGTAGTAACCCCACAACATCAAATTCTGCCCCAGCATTAGATGCTGCAGAAACAGGG
737 149_HRV2b|   AATAGTAGTAACCCCACAACATCAAATTCTGCCCCAGCATTAGATGCTGCAGAAACAGGG
738 150_HRV49a   AATAGTAGTCACCCCACGACATCAAACTCTGCTCCAGCATTAGATGCTGCAGAAACAGGG
739 151_HRV49b   AATAGTAGTCACCCCACGACATCAAACTCTGCTCCAGCATTAGATGCTGCAGAAACAGGG
740 152_HRV49    AATAGTAGTCACCCCACGACATCAAACTCTGCTCCAGCATTAGATGCTGCAGAAACAGGG
741 153_HRV23a   AATAGTAGTCATCCCACAACATCAAACTCTGCTCCAGCATTAGACGCTGCGGAAACGGGT
742 154_HRV23b   AATAGTAGTCATCCCACAACATCAAACTCTGCTCCAGCATTAGACGCTGCGGAAACGGGT
743 155_HRV23    AATAGTAGTCATCCCACAACATCAAACTCTGCTCCAGCATTAGACGCTGCGGAAACGGGT
744 156_HRV30a   AACAGTAGTCACCCTACTACATCAAACTCTGCTCCGGCATTAGATGCTGCAGAAACAGGA
745 157_HRV30b   AACAGTAGTCACCCTACTACATCAAACTCTGCTCCGGCATTAGATGCTGCAGAAACAGGA
746 158_HRV30    AACAGTAGTCACCCTACTACATCAAACTCTGCTCCGGCATTAGATGCTGCAGAAACAGGA
747 159_HRV7     CAGCCAAGTACATCTGTTTCAAGTCACTCTGTACCAGCATTGGATGCTGCAGAGACTGGA
748 160_HRV7b|   CAGCCAAGTACATCTGTTTCAAGTCACTCTGTACCAGCATTGGATGCTGCAGAGACTGGA
749 161_HRV7a|   CAGCCAAGTACATCTGTTTCAAGTCACTCTGTACCAGCATTGGATGCTGCAGAGACTGGA
750 162_HRV88    CAACCTAGCACATCCGTTTCAAGTCACTCTGTGCCAGCTCTGGATGCTGCGGAAACAGGG
751 163_HRV88a   CAACCTAGCACATCCGTTTCAAGTCACTCTGTGCCAGCTCTGGATGCTGCGGAAACAGGG
752 164_HRV88b   CAACCTAGCACATCCGTTTCAAGTCACTCTGTGCCAGCTCTGGATGCTGCGGAAACAGGG
753 165_HRV36a   CAACCTAGTTCATCTGTGTCAAGTCATTCAGCTCCCGCCTTAGACGCTGCGGAAACTGGA
754 166_HRV36b   CAACCTAGTTCATCTGTGTCAAGTCATTCAGCTCCCGCCTTAGACGCTGCGGAAACTGGA
755 167_HRV36    CAACCTAGTTCATCTGTGTCAAGTCATTCAGCTCCCGCCTTAGACGCTGCGGAAACTGGA
756 168_HRV89a   CAACCTAGCACATCTGTGTCAAGTCATGCAGCGCCTGCATTGGATGCTGCGGAAACCGGA
757 169_HRV89b   CAACCTAGCACATCTGTGTCAAGTCATGCAGCGCCTGCATTGGATGCTGCGGAAACCGGA
758 170_HRV89    CAACCTAGCACATCTGTGTCAAGTCATGCAGCGCCTGCATTGGATGCTGCGGAAACCGGA
759 171_HRV58    CAACCTAGTACATCTGTATCAAGTCATTCTGTGCCTGCCTTGGATGCTGCAGAAACGGGA
760 172_HRV58a   CAACCTAGTACATCTGTATCAAGTCATTCTGTGCCTGCCTTGGATGCTGCAGAAACGGGA
761 173_HRV58b   CAACCTAGTACATCTGTATCAAGTCATTCTGTGCCTGCCTTGGATGCTGCAGAAACGGGA
762 174_HRV12a   AACAAAAGTAATGGGCAGTTATCAAACGCAGCACCAGCGTTGGACGCTGCAGAAACTGGT
763 175_HRV12b   AACAAAAGTAATGGGCAGTTATCAAACGCAGCACCAGCGTTGGACGCTGCAGAAACTGGT
764 176_HRV12    AACAAAAGTAATGGGCAGTTATCAAACGCAGCACCAGCGTTGGACGCTGCAGAAACTGGT
765 177_HRV78a   AAAGAAAGTAAACCCCAGTCTAGCAACTCCGCTCCAGTTTTGGACGCTGCAGAAACAGGT
766 178_HRV78b   AAAGAAAGTAAACCCCAGTCTAGCAACTCCGCTCCAGTTTTGGACGCTGCAGAAACAGGT
767 179_HRV78    AAAGAAAGTAAACCCCAGTCTAGCAACTCCGCTCCAGTTTTGGACGCTGCAGAAACAGGT
768 180_HRV20    ACATCTAGTAACTCCCAAACATCAAATGCAGCACCAGCACTAGATGCTGCTGAGACAGGA
```

FIG. D5 CONT'D 01.trace                                                                                      9/20/2007 4:58 PM

```
769 181_HRV20a   ACATCTAGTAACTCCCAAACATCAAATGCAGCACCAGCACTAGATGCTGCTGAGACAGGA
770 182_HRV20b   ACATCTAGTAACTCCCAAACATCAAATGCAGCACCAGCACTAGATGCTGCTGAGACAGGA
771 183_HRV68    CCAGCAAGTAATACCCAAACTTCAAATGCAGCCCCAGCCTTAGATGCTGCTGAGACTGGA
772 184_HRV68a   CCAGCAAGTAATACCCAAACTTCAAATGCAGCCCCAGCCTTAGATGCTGCTGAGACTGGA
773 185_HRV68b   CCAGCAAGTAATACCCAAACTTCAAATGCAGCCCCAGCCTTAGATGCTGCTGAGACTGGA
774 186_HRV28    AATCCTAGCAACGCACAAACTACAAATGCAGCTCCCGCTCTCGATGCCGCTGAGACGGGG
775 187_HRV28a   AATCCTAGCAACGCACAAACTACAAATGCAGCTCCCGCTCTCGATGCCGCTGAGACGGGG
776 188_HRV28b   AATCCTAGCAACGCACAAACTACAAATGCAGCTCCCGCTCTCGATGCCGCTGAGACGGGG
777 189_HRV53a   AATGCAAGCAATCCACAAACTTCAAATTCAGCACCAGCACTAGATGCTGCAGAAACGGGT
778 190_HRV53b   AATGCAAGCAATCCACAAACTTCAAATTCAGCACCAGCACTAGATGCTGCAGAAACGGGT
779 191_HRV53    AATGCAAGCAATCCACAAACTTCAAATTCAGCACCAGCACTAGATGCTGCAGAAACGGGT
780 192_HRV46a   AATGCCAGTAGTGGACATACATCTAATTCAGCTCCAGCACTTGATGCAGCAGAAACTGGA
781 193_HRV46b   AATGCCAGTAGTGGACATACATCTAATTCAGCTCCAGCACTTGATGCAGCAGAAACTGGA
782 194_HRV46    AATGCCAGTAGTGGACATACATCTAATTCAGCTCCAGCACTTGATGCAGCAGAAACTGGA
783 195_HRV80a   AGTGCTAGCAATGGACATACATCAAACTCAGCTCCAACACTTGATGCAGCAGAAACTGGT
784 196_HRV80b   AGTGCTAGCAATGGACATACATCAAACTCAGCTCCAACACTTGATGCAGCAGAAACTGGT
785 197_HRV80    AGTGCTAGCAATGGACATACATCAAACTCAGCTCCAACACTTGATGCAGCAGAAACTGGT
786 198_HRV51    CAACCTAGCAGTGGGCACACATCTAATGCTGCACCAGCTCTAGATGCTGCTGAGACAGGA
787 199_HRV51a   CAACCTAGCAGTGGGCACACATCTAATGCTGCACCAGCTCTAGATGCTGCTGAGACAGGA
788 200_HRV51b   CAACCTAGCAGTGGGCACACATCTAATGCTGCACCAGCTCTAGATGCTGCTGAGACAGGA
789 201_HRV65a   CAAGCTAGTAATGGGCATACATCTAATGCTGCACCAGCTTTAGATGCTGCTGAAACAGGA
790 202_HRV65b   CAAGCTAGTAATGGGCATACATCTAATGCTGCACCAGCTTTAGATGCTGCTGAAACAGGA
791 203_HRV65    CAAGCTAGTAATGGGCATACATCTAATGCTGCACCAGCTTTAGATGCTGCTGAAACAGGA
792 204_HRV71a   CAACCTAGTAATGGACATACCTCAAACTCAGCACCAGCCTTAGATGCAGCAGAAACTGGG
793 205_HRV71b   CAACCTAGTAATGGACATACCTCAAACTCAGCACCAGCCTTAGATGCAGCAGAAACTGGG
794 206_HRV71    CAACCTAGTAATGGACATACCTCAAACTCAGCACCAGCCTTAGATGCAGCAGAAACTGGG
795 207_HRV8     CAAGCTAGTAATGGATCTATAGCAAATTCAGCACCAGCATTAGATGCAGCAGAGACTGGA
796 208_HRV95    CAAGCCAGTAATGGATCTATAGCAAATTCAGCACCAGCATTAGATGCAGCAGAGACTGGA
797 209_HRV45    CGACCCAGCGATGGGTTGATTGCAAACTCAGCCCCAGCTTTGGATGCAGCTGAAACTGGA
798 210_HRV45a   CGACCCAGCGATGGGTTGATTGCAAACTCAGCCCCAGCTTTGGATGCAGCTGAAACTGGA
799 211_HRV45b   CGACCCAGCGATGGGTTGATTGCAAACTCAGCCCCAGCTTTGGATGCAGCTGAAACTGGA
800 212_HRV6     ------------------------------------------------------------
801 213_HRV6a|   ------------------------------------------------------------
802 214_HRV6b|   ------------------------------------------------------------
803 215_HRV37    ------------------------------------------------------------
804 216_HRV37a   ------------------------------------------------------------
805 217_HRV37b   ------------------------------------------------------------
806 218_HRV3     ------------------------------------------------------------
807 219_HRV3a|   ------------------------------------------------------------
808 220_HRV3b|   ------------------------------------------------------------
809 221_HRV14    ------------------------------------------------------------
810 222_HRV14a   ------------------------------------------------------------
811 223_HRV14b   ------------------------------------------------------------
812 224_HRV72    ------------------------------------------------------------
813 225_HRV72a   ------------------------------------------------------------
814 226_HRV72b   ------------------------------------------------------------
815 227_HRV83    ------------------------------------------------------------
816 228_HRV83a   ------------------------------------------------------------
817 229_HRV83b   ------------------------------------------------------------
818 230_HRV92    ------------------------------------------------------------
819 231_HRV92a   ------------------------------------------------------------
820 232_HRV92b   ------------------------------------------------------------
821 233_HRV79    ------------------------------------------------------------
822 234_HRV79a   ------------------------------------------------------------
823 235_HRV79b   ------------------------------------------------------------
824 236_HRV35    ------------------------------------------------------------
825 237_HRV35a   ------------------------------------------------------------
826 238_HRV35b   ------------------------------------------------------------
827 239_1HRV86   ------------------------------------------------------------
828 240_1HRV86   ------------------------------------------------------------
829 241_1HRV86   ------------------------------------------------------------
830 242_HRV70    ------------------------------------------------------------
831 243_HRV70a   ------------------------------------------------------------
832 244_HRV70b   ------------------------------------------------------------
```

FIG. D5 CONT'D 01.trace                                                                                                                           9/20/2007 4:58 PM

```
833  245_HRV91      ------------------------------------------------------------------
834  246_HRV91a     ------------------------------------------------------------------
835  247_HRV91b     ------------------------------------------------------------------
836  248_HRV17      ------------------------------------------------------------------
837  249_HRV17a     ------------------------------------------------------------------
838  250_HRV17b     ------------------------------------------------------------------
839  251_HRV69      ------------------------------------------------------------------
840  252_HRV69a     ------------------------------------------------------------------
841  253_HRV69b     ------------------------------------------------------------------
842  254_HRV48      ------------------------------------------------------------------
843  255_HRV48a     ------------------------------------------------------------------
844  256_HRV48b     ------------------------------------------------------------------
845  257_HRV52      ------------------------------------------------------------------
846  258_HRV52a     ------------------------------------------------------------------
847  259_HRV52b     ------------------------------------------------------------------
848  260_HRV4       ------------------------------------------------------------------
849  261_HRV4a|     ------------------------------------------------------------------
850  262_HRV4b|     ------------------------------------------------------------------
851  263_HRV99      ------------------------------------------------------------------
852  264_HRV99a     ------------------------------------------------------------------
853  265_HRV99b     ------------------------------------------------------------------
854  266_HRV5       ------------------------------------------------------------------
855  267_HRV5a|     ------------------------------------------------------------------
856  268_HRV5b|     ------------------------------------------------------------------
857  269_HRV42      ------------------------------------------------------------------
858  270_HRV42a     ------------------------------------------------------------------
859  271_HRV42b     ------------------------------------------------------------------
860  272_HRV26      ------------------------------------------------------------------
861  273_HRV26a     ------------------------------------------------------------------
862  274_HRV26b     ------------------------------------------------------------------
863  275_HRV27      ------------------------------------------------------------------
864  276_HRV27a     ------------------------------------------------------------------
865  277_HRV27b     ------------------------------------------------------------------
866  278_HRV93      ------------------------------------------------------------------
867  279_HRV93a     ------------------------------------------------------------------
868  280_HRV93b     ------------------------------------------------------------------
869  281_HRV97      ------------------------------------------------------------------
870  282_HRV97a     ------------------------------------------------------------------
871  283_HRV97b     ------------------------------------------------------------------
872  284_HRV84      ------------------------------------------------------------------
873  285_HRV84a     ------------------------------------------------------------------
874  286_HRV84b     ------------------------------------------------------------------
875  287_HRV87      ------------------------------------------------------------------
876  288_HRV87a     ------------------------------------------------------------------
877  289_HRV87b     ------------------------------------------------------------------
878  GROUP_1        ------------------------------------------------------------------
879
880   1_HRV1A1|d    CACACCAGTAATGTTCAACCAGAAGATGCTATAGAGACAAGGTATGTTATAACATCACAA
881   2_HRV1A2|d    CACACCAGTAATGTTCAACCAGAAGATGCTATAGAGACAAGGTATGTTATAACATCACAA
882   3_HRV1A|cD    CACACCAGTAATGTTCAACCAGAAGATGCTATAGAGACAAGGTATGTTATAACATCACAA
883   4_HRV1B1|d    CACACCAGTAATGTACAACCAGAGGATGCTATAGAAACAAGATATGTTATGACATCACAA
884   5_HRV1B2|d    CACACCAGTAATGTACAACCAGAGGATGCTATAGAAACAAGATATGTTATGACATCACAA
885   6_HRV1B       CACACCAGTAATGTACAACCAGAGGATGCTATAGAAACAAGATATGTTATGACATCACAA
886   7_HRV40a|d    CATACAAGCAACATACAACCTGAAGATACAATAGAAACAAGATTTGTGCAGACATCACAA
887   8_HRV40b|d    CATACAAGCAACATACAACCTGAAGATACAATAGAAACAAGATTTGTGCAGACATCACAA
888   9_HRV40       CATACAAGCAACATACAACCTGAAGATACAATAGAAACAAGATTTGTGCAGACATCACAA
889  10_HRV85       CATACAAGTAGTACACAGCCCGAGGATACAATAGAGACCAGGTTTGTTCAAACTTCACAG
890  11_HRV85a|     CATACAAGTAGTACACAGCCCGAGGATACAATAGAGACCAGGTTTGTTCAAACTTCACAG
891  12_HRV85b|     CATACAAGTAGTACACAGCCCGAGGATACAATAGAGACCAGGTTTGTTCAAACTTCACAG
892  13_HRV56a|     CATACTAGTGCAATCCAACCAGAAGACACTATAGAAACCAGATATGTACAGACATCACAA
893  14_HRV56b|     CATACTAGTGCAATCCAACCAGAAGACACTATAGAAACCAGATATGTACAGACATCACAA
894  15_HRV56       CATACTAGTGCAATCCAACCAGAAGACACTATAGAAACCAGATATGTACAGACATCACAA
895  16_HRV54       CACACTAGTGGAGTACAACCCGAGGACACCATAGAAACAAGATTTGTGCAGACATCACAA
896  17_HRV98       CACACTAGTGGAATACAACCTGAGGATACTATAGAAACAAGATATGTGCAGACATCACAA
```

FIG. D5 CONT'D

01.trace                                                                 9/20/2007 4:58 PM

```
897  18_HRV59a|    CATACAAGCAGTATACAACCTGAGGATACCATAGAAACAAGATATGTTCAGACATCACAA
898  19_HRV59b|    CATACAAGCAGTATACAACCTGAGGATACCATAGAAACAAGATATGTTCAGACATCACAA
899  20_HRV59      CATACAAGCAGTATACAACCTGAGGATACCATAGAAACAAGATATGTTCAGACATCACAA
900  21_HRV63      CACACAAGCAGTATACAACCTGAGGATACTGTAGAAACTAGATATGTGCAAACGTCTCAA
901  22_HRV63b|    CACACAAGCAGTATACAACCTGAGGATACTGTAGAAACTAGATATGTGCAAACGTCTCAA
902  23_HRV63a|    CACACAAGCAGTATACAACCTGAGGATACTGTAGAAACTAGATATGTGCAAACGTCTCAA
903  24_HRV39      CACACAAGTAGCACCCAGCCTGAAGACACAATTGAAACAAGATATGTGCAAACCTCACAT
904  25_HRV39a|    CACACAAGTAGCACCCAGCCTGAAGACACAATTGAAACAAGATATGTGCAAACCTCACAT
905  26_HRV39b|    CACACAAGTAGCATCCAACCTGAAGACACAATTGAAACAAGATATGTGCAAACCTCACAT
906  27_HRV10a|    CATACCAGTAGTGTACAACCAGAAGATACGGTTGAAACACGATATGTGCAAACATCCCAG
907  28_HRV10b|    CATACCAGTAGTGTACAACCAGAAGATACGGTTGAAACACGATATGTGCAAACATCCCAG
908  29_HRV10      CATACCAGTAGTGTACAACCAGAAGATACGGTTGAAACACGATATGTGCAAACATCCCAG
909  30_HRV100a    CACACTAGTAATGTGCAACCTGAAGATACAGTTGAAACTCGATATGTGCAGACATCACAG
910  31_HRV100b    CACACTAGTAATGTGCAACCTGAAGATACAGTTGAAACTCGATATGTGCAGACATCACAG
911  32_HRV100     CACACTAGTAATGTGCAACCTGAAGATACAGTTGAAACTCGATATGTGCAGACATCACAG
912  33_HRV66      CACACTAGTAAAGTACAACCAGAAGATACAGTTGAGACTCGTTACGTGCAAACATCACAG
913  34_HRV66b|    CACACTAGTAAAGTACAACCAGAAGATACAGTTGAGACTCGTTACGTGCAAACATCACAG
914  35_HRV66a|    CACACTAGTAAAGTACAACCAGAAGATACAGTTGAGACTCGTTACGTGCAAACATCACAG
915  36_HRV77a|    CATACTAGTAGTGTGCAACCAGAAGATACAGTTGAGACCCGCTATGTACAAACTTCCCAG
916  37_HRV77b|    CATACTAGTAGTGTGCAACCAGAAGATACAGTTGAGACCCGCTATGTACAAACTTCCCAG
917  38_HRV77      CATACTAGTAGTGTGCAACCAGAAGATACAGTTGAGACCCGCTATGTACAAACTTCCCAG
918  39_HRV62a     CACACTAGTAATGTACAACCAGAAGACACTATTGAAACCCGTCATGTTCAAACCACACAA
919  40_HRV62b     CACACTAGTAATGTACAACCAGAAGACACTATTGAAACCCGTTATGTTCAAACCACACAA
920  41_HRV25      CACACTAGCAATGTGCAACCAGAGGATACCATTGAAACTCGTTATGTTCAAACCACACAA
921  42_HRV29a     CATACTAGTAATGTACAACCAGAAGATACCATTGAGACTCGTTATGTACAAACCTCACAT
922  43_HRV29b     CATACTAGTAATGTACAACCAGAAGATACCATTGAGACTCGTTATGTACAAACCTCACAT
923  44_HRV44a     CATACTAGTAATGTACAACCAGAAGATACCATTGAGACTCGATATGTACAAACCTCACAA
924  45_HRV44b     CATACTAGTAATGTACAACCAGAAGATACCATTGAGACTCGATATGTACAAACCTCACAA
925  46_HRV31      CACACTAGTAATGTACAACCAGAAGATACAATTGAAACTCGCTACGTGCAAACATCACAA
926  47_HRV31a|    CACACTAGTAATGTACAACCAGAAGATACAATTGAAACTCGCTACGTGCAAACATCACAA
927  48_HRV31b|    CACACTAGTAATGTACAACCAGAAGATACAATTGAAACTCGCTACGTGCAAACATCACAA
928  49_HRV47      CACACTAGCAATGTACAGCCAGAAGATACAATTGAAACTCGATATGTACAAACAGCACAA
929  50_HRV47a|    CACACTAGCAATGTACAGCCAGAAGATACAATTGAAACTCGATATGTACAAACAGCACAA
930  51_HRV47b|    CACACTAGCAATGTACAGCCAGAAGATACAATTGAAACTCGATATGTACAAACAGCACAA
931  52_HRV11      CATACTAGCAAAGTGCAGCCAGAGGATATGATTGAGACTAGATATGTGCAGACTTCACAG
932  53_HRV11b|    CATACTAGCAAAGTGCAGCCAGAGGATATGATTGAGACTAGATATGTGCAGACTTCACAG
933  54_HRV11a|    CATACTAGCAAAGTGCAGCCAGAGGATATGATTGAGACTAGATATGTGCAGACTTCACAG
934  55_HRV76      CACACAAGCAGCGTTCAACCAGAGGACATGGTTGAGACTAGGTATGTGCAAACATCACAA
935  56_HRV76b|    CACACAAGCAGCGTTCAACCAGAGGACATGGTTGAGACTAGGTATGTGCAAACATCACAA
936  57_HRV76a|    CACACAAGCAGCGTTCAACCAGAGGACATGGTTGAGACTAGGTATGTGCAAACATCACAA
937  58_HRV33      CACACTAATAATGTACAACCAGAAGATATGATTGAAACAAGATATGTACAAACATCACAA
938  59_HRV33b|    CACACTAATAATGTACAACCAGAAGATATGATTGAAACAAGATATGTACAAACATCACAA
939  60_HRV33a|    CACACTAATAATGTACAACCAGAAGATATGATTGAAACAAGATATGTACAAACATCACAA
940  61_HRV24a|    CATACGAGTAGCGTGCAGCCAGAAGATATGGTTGAAACTAGATATGTCCAAACATCACAA
941  62_HRV24b|    CATACGAGTAGCGTGCAGCCAGAAGATATGGTTGAAACTAGATATGTCCAAACATCACAA
942  63_HRV24      CATACGAGTAGCGTGCAGCCAGAAGATATGGTTGAAACTAGATATGTCCAAACATCACAA
943  64_HRV90      CATACTAGTGATGTCCAGCCAGAAGATGTGGTAGAGACCAGATACGTGCAAACATCACAA
944  65_HRV90a|    CATACTAGTGATGTCCAGCCAGAAGATGTGGTAGAGACCAGATACGTGCAAACATCACAA
945  66_HRV90b|    CATACTAGTGATGTCCAGCCAGAAGATGTGGTAGAGACCAGATACGTGCAAACATCACAA
946  67_HRV34      CACACTAGCAGTGTACAACCTGAAGATATGATTGAGACCAGGTACGTACAAACATCACAA
947  68_HRV34b|    CACACTAGCAGTGTACAACCTGAAGATATGATTGAGACCAGGTACGTACAAACATCACAA
948  69_HRV34a|    CACACTAGCAGTGTACAACCTGAAGATATGATTGAGACCAGGTACGTACAAACATCACAA
949  70_HRV50a|    CACACAAGTAATGTGCAGCCTGAAGATATGCTTGAAACTAGATATGTGCAAACATCGCAT
950  71_HRV50b|    CACACAAGTAATGTGCAGCCTGAAGATATGCTTGAAACTAGATATGTGCAAACATCGCAT
951  72_HRV50      CACACAAGTAATGTGCAGCCTGAAGATATGCTTGAAACTAGATATGTGCAAACATCGCAT
952  73_HRV18a|    CACACCAGCAATGTGCAACCTGAAGATATGATTGAGACTAGGTATGTACAAACATCACAA
953  74_HRV18b|    CACACCAGCAATGTGCAACCTGAAGATATGATTGAGACTAGGTATGTACAAACATCACAA
954  75_HRV18      CACACCAGCAATGTGCAACCTGAAGATATGATTGAGACTAGGTATGTACAAACATCACAA
955  76_HRV55      CATACAAGCAATGTACAACCAGAAGATGTAATTGAGACAAGATATGTTCAGACATCACAA
956  77_HRV55b|    CATACAAGCAATGTACAACCAGAAGATGTAATTGAGACAAGATATGTTCAGACATCACAA
957  78_HRV55a|    CATACAAGCAATGTACAACCAGAAGATGTAATTGAGACAAGATATGTTCAGACATCACAA
958  79_HRV57      CACACTAGTAATGTACAACCGGAAGACATGATTGAAACTAGATATGTCCAGACATCACAA
959  80_HRV57a|    CACACTAGTAATGTACAACCGGAAGACATGATTGAAACTAGATATGTCCAGACATCACAA
960  81_HRV57b|    CACACTAGTAATGTACAACCGGAAGACATGATTGAAACTAGATATGTCCAGACATCACAA
```

FIG. D5 CONT'D 01.trace                                                                  9/20/2007 4:58 PM

```
 961  82_HRV21      CACACTAGTAATGTACAGCCGGAGGATATGGTTGAAACAAGGTATGTTCAGACATCACAA
 962  83_HRVHan     CACACTAGTAATGTACAACCAGAGGATATGGTTGAAACAAGGTATGTTCAGACATCACAA
 963  84_HRV43      CATACTAGCCAGGTGCAACCTGAAGACATGGTAGAGACAAGGTCAGTACATAATTTCCAA
 964  85_HRV43b|    CATACTAGCCAGGTGCAACCTGAAGACATGGTAGAGACAAGGTCAGTACATAATTTCCAA
 965  86_HRV43a|    CATACTAGCCAGGTGCAACCTGAAGACATGGTAGAGACAAGGTCAGTACATAATTTCCAA
 966  87_HRV75      CATACCAGCCATGTTCAACCAGAAGACATGTTAGAAACAAGGCAAGTACAAAATTTCCAA
 967  88_HRV75b|    CATACCAGCCATGTTCAACCAGAAGACATGTTAGAAACAAGGCAAGTACAAAATTTCCAA
 968  89_HRV75a|    CATACCAGCCATGTTCAACCAGAAGACATGTTAGAAACAAGGCAAGTACAAAATTTCCAA
 969  96_HRV9a|d    CATACTAGCAATGTTCAACCTGAAGACATGATTGAAACACGTTATGTGCAGACATCACAA
 970  97_HRV9b|d    CATACTAGCAATGTTCAACCTGAAGACATGATTGAAACACGTTATGTGCAGACATCACAA
 971  98_HRV9       CATACTAGCAATGTTCAACCTGAAGACATGATTGAAACACGTTATGTGCAGACATCACAA
 972  99_HRV32      CATACCAGTAATGTTCAACCTGAAGACATGATTGAAACACGTTATGTGCAAACAACACAC
 973 100_HRV32a     CATACCAGTAATGTTCAACCTGAAGACATGATTGAAACACGTTATGTGCAAACAACACAC
 974 101_HRV32b     CATACCAGTAATGTTCAACCTGAAGACATGATTGAAACACGTTATGTGCAAACAACACAC
 975 102_HRV67      CACACTAGCAGTGTACAACCTGAAGATATGATCGAGACTCGTTATGTACAGGCATCAAAT
 976 103_HRV67a     CACACTAGCAGTGTACAACCTGAAGATATGATCGAGACTCGTTATGTACAGGCATCAAAT
 977 104_HRV67b     CACACTAGCAGTGTACAACCTGAAGATATGATCGAGACTCGTTATGTACAGGCATCAAAT
 978 105_HRV15      CATACTAGCAGTGTTCAACCTGAGGATATGATTGAAACTCGTTACGTCCAAACATCACAG
 979 106_HRV15a     CATACTAGCAGTGTTCAACCTGAGGATATGATTGAAACTCGTTACGTCCAAACATCACAG
 980 107_HRV15b     CATACTAGCAGTGTTCAACCTGAGGATATGATTGAAACTCGTTACGTCCAAACATCACAG
 981 108_HRV74a     CATACCAGTAATGTGCAACCAGAAGATATGGTTGAGACACGCTATGTGCAAACCTCACAG
 982 109_HRV74b     CATACCAGTAATGTGCAACCAGAAGATATGGTTGAGACACGCTATGTGCAAACCTCACAG
 983 110_HRV74      CATACCAGTAATGTGCAACCAGAAGATATGGTTGAGACACGCTATGTGCAAACCTCACAG
 984 111_HRV38a     CACACCAGTAATGTGCAACCTGAGGATATGATTGAAACTCGTTATGTACAGACATCACAA
 985 112_HRV38b     CACACCAGTAATGTGCAGCCTGAGGATATGATTGAAACTCGCTATGTACAGACATCACAA
 986 113_HRV38      CACACCAGTAATGTGCAGCCTGAGGATATGATTGAAACTCGCTATGTACAGACATCACAA
 987 114_HRV60      CACACTAGTAATGTACAGCCTGAGGACGTGATTGAAACACGTTATGTGCAGATTACACAA
 988 115_HRV60a     CACACTAGTAATGTACAGCCTGAGGACGTGATTGAAACACGTTATGTGCAGATTACACAA
 989 116_HRV60b     CACACTAGTAATGTACAGCCTGAGGACGTGATTGAAACACGTTATGTGCAGATTACACAA
 990 117_HRV64a     CACACCAGTAATGTACAGCCTGAAGATATGATTGAAACGCGCTATGTACAAAACACTCAA
 991 118_HRV64b     CACACCAGTAATGTACAGCCTGAAGATATGATTGAAACGCGCTATGTACAAAACACTCAA
 992 119_HRV64      CACACCAGTAATGTACAGCCTGAAGATATGATTGAAACGCGCTATGTACAAAACACTCAA
 993 120_HRV94a     CACACAAGCAATGTACAACCTGAGGATATGATTGAAACACGCTATGTACAAAACACTCAA
 994 121_HRV94b     CACACAAGCAATGTACAACCTGAGGATATGATTGAAACACGCTATGTACAAAACACTCAA
 995 122_HRV94      CACACAAGCAATGTACAACCTGAGGATATGATTGAAACACGCTATGTACAAAACACTCAA
 996 123_HRV22      CACACAAGCAATGTGCAGCCAGAAGACATGATAGAAACACGCTATGTGTTAAATTCACAA
 997 124_HRV22a     CACACAAGCAATGTGCAGCCAGAAGACATGATAGAAACACGCTATGTGTTAAATTCACAA
 998 125_HRV22b     CACACAAGCAATGTGCAGCCAGAAGACATGATAGAAACACGCTATGTGTTAAATTCACAA
 999 126_HRV82      CATACAAGTACTGTTCAACCTGAGGACATGATTGAAACACGGTATGTTCAAACATCACAA
1000 127_HRV82b     CATACAAGTACTGTTCAACCTGAGGACATGATTGAAACACGGTATGTTCAAACATCACAA
1001 128_HRV82a     CATACAAGTACTGTTCAACCTGAGGACATGATTGAAACACGGTATGTTCAAACATCACAA
1002 129_HRV19      CATACTAGCAATGTACAGCCTGAGGACATGATCGAAACACGCTATGTTCAAACGTCCCAG
1003 130_HRV19a     CATACTAGCAATGTACAGCCTGAGGACATGATCGAAACACGCTATGTTCAAACGTCCCAG
1004 131_HRV19b     CATACTAGCAATGTACAGCCTGAGGACATGATCGAAACACGCTATGTTCAAACGTCCCAG
1005 132_HRV13      CACACAAGCAGTGTACAACCAGAAGACATGGTTGAAACACGTTATGTCCAAACTTCACAA
1006 133_HRV13a     CACACAAGCAGTGTACAACCAGAAGACATGGTTGAAACACGTTATGTCCAAACTTCACAA
1007 134_HRV13b     CACACAAGCAGTGTACAACCAGAAGACATGGTTGAAACACGTTATGTCCAAACTTCACAA
1008 135_HRV41      CATACCAGTAATGTACAACCAGAGGACATGATTGAAACACGATATGTCCAAACCTCACAA
1009 136_HRV41a     CATACCAGTAATGTACAACCAGAGGACATGATTGAAACACGATATGTCCAAACCTCACAA
1010 137_HRV41b     CATACCAGTAATGTACAACCAGAGGACATGATTGAAACACGATATGTCCAAACCTCACAA
1011 138_HRV73      CATACCAGTGGTGTACAACCAGAAGACATGATTGAGACCCGTTATGTCCAAACATCACAG
1012 139_HRV73b     CATACCAGTGGTGTACAACCAGAAGACATGATTGAGACCCGTTATGTCCAAACATCACAG
1013 140_HRV73a     CATACCAGTGGTGTACAACCAGAAGACATGATTGAGACCCGTTATGTCCAAACATCACAG
1014 141_HRV61      CATACCAGCAATGTTCAACCGGAGGACACGATTGAAACACGATATGTTCAAACCTCACAG
1015 142_HRV61a     CATACCAGCAATGTTCAACCGGAGGACACGATTGAAACACGATATGTTCAAACCTCACAG
1016 143_HRV61b     CATACCAGCAATGTTCAACCGGAGGACACGATTGAAACACGATATGTTCAAACCTCACAG
1017 144_HRV96      CATACTAGCAATGTCCAACCAGAGGATATGATTGAGACTCGATATGTTCAGACATCGCAG
1018 145_HRV96b     CATACTAGCAATGTCCAACCAGAGGATATGATTGAGACTCGATATGTTCAGACATCGCAG
1019 146_HRV96a     CATACTAGCAATGTCCAACCAGAGGATATGATTGAGACTCGATATGTTCAGACATCGCAG
1020  90_HRV16a|    CATACCAATAAGATACAGCCAGAAGACACTATAGAAACCAGATATGTGCAATCTTCACAG
1021  91_HRV16b|    CATACCAATAAGATACAGCCAGAAGACACTATAGAAACCAGATATGTGCAATCTTCACAG
1022  92_1AYM_A     CATACCAATAAGATACAGCCAGAAGACACTATAGAAACCAGATATGTGCAATCTTCACAG
1023  93_HRV81a|    CACACCAGTAATATACAACCTGAGGATACTATTGAGACCAGATATGTACAATCTTCACAG
1024  94_HRV81b|    CACACCAGTAATATACAACCTGAGGATACTATTGAGACCAGATATGTACAATCTTCACAG
```

FIG. D5 CONT'D

```
01.trace                                                              9/20/2007 4:58 PM 1025  95_HRV81    CACACCAGTAATATACAACCTGAGGATACTATTGAGACCAGATATGTACAATCTTCACAG
1026 147_HRV2     CACACTAGTAGTGTTCAACCAGAGGATGTCATTGAAACTAGGTATGTGCAGACATCACAA
1027 148_HRV2a|   CACACTAGTAGTGTTCAACCAGAGGATGTCATTGAAACTAGGTATGTGCAGACATCACAA
1028 149_HRV2b|   CACACTAGTAGTGTTCAACCAGAGGATGTCATTGAAACTAGGTATGTGCAGACATCACAA
1029 150_HRV49a   CACACTAGCAATGTGCAACCTGAAGATGTCATTGAAACCAGATATGTACAGACATCACAA
1030 151_HRV49b   CACACTAGCAATGTGCAACCTGAAGATGTCATTGAAACCAGATATGTACAGACATCACAA
1031 152_HRV49    CACACTAGCAATGTGCAACCTGAAGATGTCATTGAAACCAGATATGTACAGACATCACAA
1032 153_HRV23a   CACACTAGTAATGTTCAACCAGAAGATGTCATTGAAACCAGGTACGTTCAAACATCACAA
1033 154_HRV23b   CACACTAGTAATGTTCAACCAGAAGATGTCATTGAAACCAGGTACGTTCAAACATCACAA
1034 155_HRV23    CACACTAGTAATGTTCAACCAGAAGATGTCATTGAAACCAGGTACGTTCAAACATCACAA
1035 156_HRV30a   CATACTAGTAATGTTCAACCTGAAGATGTCATTGAAACTAGATATGTTCAAACATCACAA
1036 157_HRV30b   CATACTAGTAATGTTCAACCTGAAGATGTCATTGAAACTAGATATGTTCAAACATCACAA
1037 158_HRV30    CATACTAGTAATGTTCAACCTGAAGATGTCATTGAAACTAGATATGTTCAAACATCACAA
1038 159_HRV7     CATACTAGTTCTGTTCAACCTGAAGATATGATCGAGACAAGGTATGTCATAACAGACCAA
1039 160_HRV7b|   CATACTAGTTCTGTTCAACCTGAAGATATGATCGAGACAAGGTATGTCATAACAGACCAA
1040 161_HRV7a|   CATACTAGTTCTGTTCAACCTGAAGATATGATCGAGACAAGGTATGTCATAACAGACCAA
1041 162_HRV88    CATACTAGTTCTGTTCAACCTGAAGATATGATAGAAACTAGATATGTTATAACAGATCAA
1042 163_HRV88a   CATACTAGTTCTGTTCAACCTGAAGATATGATAGAAACTAGATATGTTATAACAGATCAA
1043 164_HRV88b   CATACTAGTTCTGTTCAACCTGAAGATATGATAGAAACTAGATATGTTATAACAGATCAA
1044 165_HRV36a   CATACCAGCTCTGTCCAACCAGAGGACATGATCGAGACCAGATATGTCATAACTGATCAA
1045 166_HRV36b   CATACCAGCTCTGTCCAACCAGAGGACATGATCGAGACCAGATATGTCATAACTGATCAA
1046 167_HRV36    CATACCAGCTCTGTCCAACCAGAGGACATGATCGAGACCAGATATGTCATAACTGATCAA
1047 168_HRV89a   CACACCAGCTCTGTTCAACCTGAAGATATGTTGAAACTAGATATGTTATAACTGATCAA
1048 169_HRV89b   CACACCAGCTCTGTTCAACCTGAAGATATGATTGAAACTAGATATGTTATAACTGATCAA
1049 170_HRV89    CACACCAGCTCTGTTCAACCTGAAGATATGATTGAAACTAGATATGTTATAACTGATCAA
1050 171_HRV58    CACACAAGTTCTGTTCAGCCTGAGGATATGATTGAAACTAGATATGTTATCACAGATCAA
1051 172_HRV58a   CACACAAGTTCTGTTCAGCCTGAGGATATGATTGAAACTAGATATGTTATCACAGATCAA
1052 173_HRV58b   CACACAAGTTCTGTTCAGCCTGAGGATATGATTGAAACTAGATATGTTATCACAGATCAA
1053 174_HRV12a   CATACCAGCCAAACACAACCAGAAGATGTGATTGAAACCAGGTATGTGATTACAGACCAG
1054 175_HRV12b   CATACCAGCCAAACACAACCAGAAGATGTGATTGAAACCAGGTATGTGATTACAGACCAG
1055 176_HRV12    CATACCAGCCAAACACAACCAGAAGATGTGATTGAAACCAGGTATGTGATTACAGACCAG
1056 177_HRV78a   CATACGAACCAAGTACAGCCTGAAGACACCATAGAAACTAGATATGTTATAACTGACCAA
1057 178_HRV78b   CATACGAACCAAGTACAGCCTGAAGACACCATAGAAACTAGATATGTTATAACTGACCAA
1058 179_HRV78    CATACGAACCAAGTACAGCCTGAAGACACCATAGAAACTAGATATGTTATAACTGACCAA
1059 180_HRV20    CACACAAACCAGGTCCAGCCAGAAGATATGGTCGAGACACGGTATGTAATTACTGATCAG
1060 181_HRV20a   CACACAAACCAGGTCCAGCCAGAAGATATGGTCGAGACACGGTATGTAATTACTGATCAG
1061 182_HRV20b   CACACAAACCAGGTCCAGCCAGAAGATATGGTCGAGACACGGTATGTAATTACTGATCAG
1062 183_HRV68    CATACAAACCAAGTCCAACCAGAAGATGTGGTTGAAACACGCTATGTCATAACAGACCAG
1063 184_HRV68a   CATACAAACCAAGTCCAACCAGAAGATGTGGTTGAAACACGCTATGTCATAACAGACCAG
1064 185_HRV68b   CATACAAACCAAGTCCAACCAGAAGATGTGGTTGAAACACGCTATGTCATAACAGACCAG
1065 186_HRV28    CACACAAGCCAAACACAACCTGAAGACATGGTTGAGACTAGGTATGTAATCACAGATCAG
1066 187_HRV28a   CACACAAGCCAAACACAACCTGAAGACATGGTTGAGACTAGGTATGTAATCACAGATCAG
1067 188_HRV28b   CACACAAGCCAAACACAACCTGAAGACATGGTTGAGACTAGGTATGTAATCACAGATCAG
1068 189_HRV53a   CATACAAGTCAGACACAACCTGAGGACATGCTGGAAACTAGATATGTCATCACAGACCAA
1069 190_HRV53b   CATACAAGTCAGACACAACCTGAGGACATGCTGGAAACTAGATATGTCATCACAGACCAA
1070 191_HRV53    CATACAAGTCAGACACAACCTGAGGACATGCTGGAAACTAGATATGTCATCACAGACCAA
1071 192_HRV46a   CACACTAGCCAGATACAACCAGAAGACATGATAGAAACCAGATATGTTATCACAGACCAA
1072 193_HRV46b   CACACTAGCCAGATACAACCAGAAGACATGATAGAAACCAGATATGTTATCACAGACCAA
1073 194_HRV46    CACACTAGCCAGATACAACCAGAAGACATGATAGAAACCAGATATGTTATCACAGACCAA
1074 195_HRV80a   CACACTAGCCAGGTGCAACCAGAAGACATGATAGAAACTAGATATGTTATTACTGATCAG
1075 196_HRV80b   CACACTAGCCAGGTGCAACCAGAAGACATGATAGAAACTAGATATGTTATTACTGATCAG
1076 197_HRV80    CACACTAGCCAGGTGCAACCAGAAGACATGATAGAAACTAGATATGTTATTACTGATCAG
1077 198_HRV51    CATACTAGTCAAGTTCAACCAGAAGATATGGTAGAGACCAGGTATGTTGTCACAGACCAA
1078 199_HRV51a   CATACTAGTCAAGTTCAACCAGAAGATATGGTAGAGACCAGGTATGTTGTCACAGACCAA
1079 200_HRV51b   CATACTAGTCAAGTTCAACCAGAAGATATGGTAGAGACCAGGTATGTTGTCACAGACCAA
1080 201_HRV65a   CACACTAGTCAAGTTCAACCAGAGGATGTGATAGAAACCAGATATGTCATCACAGATCAA
1081 202_HRV65b   CACACTAGTCAAGTTCAACCAGAGGATGTGATAGAAACCAGATATGTCATCACAGATCAA
1082 203_HRV65    CACACTAGTCAAGTTCAACCAGAGGATGTGATAGAAACCAGATATGTCATCACAGATCAA
1083 204_HRV71a   CATACCAACCAAGTACAACCAGAAGATGTTATGGAAACCAGATATGTGATCACTGATCAA
1084 205_HRV71b   CATACCAACCAAGTACAACCAGAAGATGTTATGGAAACCAGATATGTGATCACTGATCAA
1085 206_HRV71    CATACCAACCAAGTACAACCAGAAGATGTTATGGAAACCAGATATGTGATCACTGATCAA
1086 207_HRV8     CACACAAGTTCAGTGCAACCTGAAGATCTTATAGAGACTAGGTATGTAATTACAGATCAA
1087 208_HRV95    CACACAAGTTCAGTGCAACCTGAAGATCTTATAGAGACTAGGTATGTAATTACAGATCAA
1088 209_HRV45    CACACCAGTTCAGTGCAGCCTGAGGACCTTATAGAGACTAGATATGTGATTGCAGACCAA
```

FIG. D5 CONT'D 01.trace                                                                 9/20/2007 4:58 PM

```
1089  210_HRV45a   CACACCAGTTCAGTGCAGCCTGAGGACCTTATAGAGACTAGATATGTGATTGCAGACCAA
1090  211_HRV45b   CACACCAGTTCAGTGCAGCCTGAGGACCTTATAGAGACTAGATATGTGATTGCAGACCAA
1091  212_HRV6     ------------------------------------------------------------
1092  213_HRV6a|   ------------------------------------------------------------
1093  214_HRV6b|   ------------------------------------------------------------
1094  215_HRV37    ------------------------------------------------------------
1095  216_HRV37a   ------------------------------------------------------------
1096  217_HRV37b   ------------------------------------------------------------
1097  218_HRV3     ------------------------------------------------------------
1098  219_HRV3a|   ------------------------------------------------------------
1099  220_HRV3b|   ------------------------------------------------------------
1100  221_HRV14    ------------------------------------------------------------
1101  222_HRV14a   ------------------------------------------------------------
1102  223_HRV14b   ------------------------------------------------------------
1103  224_HRV72    ------------------------------------------------------------
1104  225_HRV72a   ------------------------------------------------------------
1105  226_HRV72b   ------------------------------------------------------------
1106  227_HRV83    ------------------------------------------------------------
1107  228_HRV83a   ------------------------------------------------------------
1108  229_HRV83b   ------------------------------------------------------------
1109  230_HRV92    ------------------------------------------------------------
1110  231_HRV92a   ------------------------------------------------------------
1111  232_HRV92b   ------------------------------------------------------------
1112  233_HRV79    ------------------------------------------------------------
1113  234_HRV79a   ------------------------------------------------------------
1114  235_HRV79b   ------------------------------------------------------------
1115  236_HRV35    ------------------------------------------------------------
1116  237_HRV35a   ------------------------------------------------------------
1117  238_HRV35b   ------------------------------------------------------------
1118  239_1HRV86   ------------------------------------------------------------
1119  240_1HRV86   ------------------------------------------------------------
1120  241_1HRV86   ------------------------------------------------------------
1121  242_HRV70    ------------------------------------------------------------
1122  243_HRV70a   ------------------------------------------------------------
1123  244_HRV70b   ------------------------------------------------------------
1124  245_HRV91    ------------------------------------------------------------
1125  246_HRV91a   ------------------------------------------------------------
1126  247_HRV91b   ------------------------------------------------------------
1127  248_HRV17    ------------------------------------------------------------
1128  249_HRV17a   ------------------------------------------------------------
1129  250_HRV17b   ------------------------------------------------------------
1130  251_HRV69    ------------------------------------------------------------
1131  252_HRV69a   ------------------------------------------------------------
1132  253_HRV69b   ------------------------------------------------------------
1133  254_HRV48    ------------------------------------------------------------
1134  255_HRV48a   ------------------------------------------------------------
1135  256_HRV48b   ------------------------------------------------------------
1136  257_HRV52    ------------------------------------------------------------
1137  258_HRV52a   ------------------------------------------------------------
1138  259_HRV52b   ------------------------------------------------------------
1139  260_HRV4     ------------------------------------------------------------
1140  261_HRV4a|   ------------------------------------------------------------
1141  262_HRV4b|   ------------------------------------------------------------
1142  263_HRV99    ------------------------------------------------------------
1143  264_HRV99a   ------------------------------------------------------------
1144  265_HRV99b   ------------------------------------------------------------
1145  266_HRV5     ------------------------------------------------------------
1146  267_HRV5a|   ------------------------------------------------------------
1147  268_HRV5b|   ------------------------------------------------------------
1148  269_HRV42    ------------------------------------------------------------
1149  270_HRV42a   ------------------------------------------------------------
1150  271_HRV42b   ------------------------------------------------------------
1151  272_HRV26    ------------------------------------------------------------
1152  273_HRV26a   ------------------------------------------------------------
```

FIG. D5 CONT'D 01.trace                                                                 9/20/2007 4:58 PM

```
1153  274_HRV26b     ------------------------------------------------------------
1154  275_HRV27      ------------------------------------------------------------
1155  276_HRV27a     ------------------------------------------------------------
1156  277_HRV27b     ------------------------------------------------------------
1157  278_HRV93      ------------------------------------------------------------
1158  279_HRV93a     ------------------------------------------------------------
1159  280_HRV93b     ------------------------------------------------------------
1160  281_HRV97      ------------------------------------------------------------
1161  282_HRV97a     ------------------------------------------------------------
1162  283_HRV97b     ------------------------------------------------------------
1163  284_HRV84      ------------------------------------------------------------
1164  285_HRV84a     ------------------------------------------------------------
1165  286_HRV84b     ------------------------------------------------------------
1166  287_HRV87      ------------------------------------------------------------
1167  288_HRV87a     ------------------------------------------------------------
1168  289_HRV87b     ------------------------------------------------------------
1169  GROUP_1        ------------------------------------------------------------
1170
1171  1_HRV1A1|d     ACAAGAGATGAGATGAGTATAGAAAGTTTCCTTGGTAGATCTGGTTGTGTCCACATCTCA
1172  2_HRV1A2|d     ACAAGAGATGAGATGAGTATAGAAAGTTTCCTTGGTAGATCTGGTTGTGTCCACATCTCA
1173  3_HRV1A|cD     ACAAGAGATGAGATGAGTATAGAAAGTTTCCTTGGTAGATCTGGTTGTGTCCACATCTCA
1174  4_HRV1B1|d     ACAAGAGATGAGATGAGTATAGAAAGTTTCTTGGTAGATCTGGCTGTGTGCATATTTCA
1175  5_HRV1B2|d     ACAAGAGATGAGATGAGTATAGAAAGTTTCTTGGTAGATCTGGCTGTGTGCATATTTCA
1176  6_HRV1B        ACAAGAGATGAGATGAGTATAGAAAGTTTCTTGGTAGATCTGGCTGTGTGCATATTTCA
1177  7_HRV40a|d     ACTAGAGATGAAATGAGCATAGAGAGTTTCTTGGGAAGATCTGGGTGCATTCATATATCC
1178  8_HRV40b|d     ACTAGAGATGAAATGAGCATAGAGAGTTTCTTGGGAAGATCTGGGTGCATTCATATATCC
1179  9_HRV40        ACTAGAGATGAAATGAGCATAGAGAGTTTCTTGGGAAGATCTGGGTGCATTCATATATCC
1180  10_HRV85       ACTAGGGATGAAATGAGTTTAGAAAGTTTCTTGGGAAGATCTGGATGTATCCATATATCT
1181  11_HRV85a|     ACTAGGGATGAAATGAGTTTAGAAAGTTTCTTGGGAAGATCTGGATGTATCCATATATCT
1182  12_HRV85b|     ACTAGGGATGAAATGAGTTTAGAAAGTTTCTTGGGAAGATCTGGATGTATCCATATATCT
1183  13_HRV56a|     ACTAGGGATGAAATGAGTATAGAGAGTTTTCTAGGTAGATCAGGTTGTATACATATATCA
1184  14_HRV56b|     ACTAGGGATGAAATGAGTATAGAGAGTTTTCTAGGTAGATCAGGTTGTATACATATATCA
1185  15_HRV56       ACTAGGGATGAAATGAGTATAGAGAGTTTTCTAGGTAGATCAGGTTGTATACATATATCA
1186  16_HRV54       ACTAGAGATGAAATGAGCATAGAGAGTTTCTAGGCAGGGCTGGTTGCATACATGAATCC
1187  17_HRV98       ACCAGAGATGAAATGAGTATAGAAAGTTTCTAGGTAGGGCCGGTTGTATACATGAATCT
1188  18_HRV59a|     ACTAGAGATGAGATGAGTGTAGAAAGTTTCTTAGGTAGATCTGGGTGTATACATATTTCA
1189  19_HRV59b|     ACTAGAGATGAGATGAGTGTAGAAAGTTTCTTAGGTAGATCTGGGTGTATACATATTTCA
1190  20_HRV59       ACTAGAGATGAGATGAGTGTAGAAAGTTTCTTAGGTAGATCTGGGTGTATACATATTTCA
1191  21_HRV63       ACAAGGGATGAAATGAGTGTAGAGAGCTTTCTTGGTAGATCAGGATGCATACACATATCA
1192  22_HRV63b|     ACAAGGGATGAAATGAGTGTAGAGAGCTTTCTTGGTAGATCAGGATGCATACACATATCA
1193  23_HRV63a|     ACAAGGGATGAAATGAGTGTAGAGAGCTTTCTTGGTAGATCAGGATGCATACACATATCA
1194  24_HRV39       ACTAGGGATGAAATGAGCGTTGAAAGTTTCTTAGGCAGATCTGGCTGTATTCACATTTCC
1195  25_HRV39a|     ACTAGGGATGAAATGAGCGTTGAAAGTTTCTTAGGCAGATCTGGCTGTATTCACATTTCC
1196  26_HRV39b|     ACTAGGGATGAAATGAGCGTTGAAAGTTTCTTAGGCAGATCTGGCTGTATTCACATTTCC
1197  27_HRV10a|     ACGAGAGATGAAATGAGTATTGAAAGTTTCTTGGCAGGTCAGGTTGTATACACACCTCA
1198  28_HRV10b|     ACGAGAGATGAAATGAGTATTGAAAGTTTCTTGGCAGGTCAGGTTGTATACACACCTCA
1199  29_HRV10       ACGAGAGATGAAATGAGTATTGAAAGTTTCTTGGCAGGTCAGGTTGTATACACACCTCA
1200  30_HRV100a     ACCAGGGATGAAATGAGCTTTCTTGGAAGATCTTGGTTGTATACACACCTCA
1201  31_HRV100b     ACCAGGGATGAAATGAGTATTGAGAGCTTTCTTGGAAGATCTGGTTGTATACACACCTCA
1202  32_HRV100      ACCAGGGATGAAATGAGTATTGAGAGCTTTCTTGGAAGATCTGGTTGTATACACACCTCA
1203  33_HRV66       ACTAGAGATGAAATGAGCATAGAAAGTTTTCTAGGTAGGTCAGGATGTATCCATATATCA
1204  34_HRV66b|     ACTAGAGATGAAATGAGCATAGAAAGTTTTCTAGGTAGGTCAGGATGTATCCATATATCA
1205  35_HRV66a|     ACTAGAGATGAAATGAGCATAGAAAGTTTTCTAGGTAGGTCAGGATGTATCCATATATCA
1206  36_HRV77a|     ACAAGGGATGAGATGAGTATTGAGAGCTTTCTGGGTAGGTCTGGTTGTATTCACATTTCA
1207  37_HRV77b|     ACAAGGGATGAGATGAGTATTGAGAGCTTTCTGGGTAGGTCTGGTTGTATTCACATTTCA
1208  38_HRV77       ACAAGGGATGAGATGAGTATTGAGAGCTTTCTGGGTAGGTCTGGTTGTATTCACATTTCA
1209  39_HRV62a      ACTAGAGATGAAATGAGCATTGAGAGCTTTCTTGGTAGGTCAGGGTGCGTACACACTTCA
1210  40_HRV62b      ACTAGAGATGAAATGAGCATTGAGAGCTTTCTTGGTAGGTCAGGGTGCGTACACACTTCA
1211  41_HRV25       ACTAGAGATGAAATGAGTATTGAAAGTTTCTTGGTAGGTCAGGGTGCGTACATACTTCA
1212  42_HRV29a      ACAAGAGATGAAATGAGCATTGAAAGTTTCTTGGGTAGATCAGGATGTATACATGTTTCA
1213  43_HRV29b      ACAAGAGATGAAATGAGCATTGAAAGTTTCTTGGGTAGATCAGGATGTATACATGTTTCA
1214  44_HRV44a      ACTAGAGATGAAATGAGCATTGAAAGTTTCTTGGCAGATCAGGGTGTATACATGTTTCA
1215  45_HRV44b      ACTAGAGATGAAATGAGCATTGAAAGTTTCTTGGCAGATCAGGGTGTATACATGTTTCA
1216  46_HRV31       ACAAGAGATGAAATGAGCATTGAAAGTTTCCTTGGTAGGTCAGGATGTGTACATACTTCA
```

FIG. D5 CONT'D

01.trace                                                                9/20/2007 4:58 PM

| | | |
|---|---|---|
| 1217 | 47_HRV31a\| | ACAAGAGATGAAATGAGCATTGAAAGTTTCCTTGGTAGGTCAGGATGTGTACATACTTCA |
| 1218 | 48_HRV31b\| | ACAAGAGATGAAATGAGCATTGAAAGTTTCCTTGGTAGGTCAGGATGTGTACATACTTCA |
| 1219 | 49_HRV47 | ACAAGAGATGAAATGAGCATTGAGAGCTTCCTTGGCAGGTCAGGATGTGTGCATTCCTCA |
| 1220 | 50_HRV47a\| | ACAAGAGATGAAATGAGCATTGAGAGCTTCCTTGGCAGGTCAGGATGTGTGCATTCCTCA |
| 1221 | 51_HRV47b\| | ACAAGAGATGAAATGAGCATTGAGAGCTTCCTTGGCAGGTCAGGATGTGTGCATTCCTCA |
| 1222 | 52_HRV11 | ACTCTTGATGAAATGAGCATTGAGAGCTTCCTAGGTAGATCTGGTTGTATTCACATGTCC |
| 1223 | 53_HRV11b\| | ACTCTTGATGAAATGAGCATTGAGAGCTTCCTAGGTAGATCTGGTTGTATTCACATGTCC |
| 1224 | 54_HRV11a\| | ACTCTTGATGAAATGAGCATTGAGAGCTTCCTAGGTAGATCTGGTTGTATTCACATGTCC |
| 1225 | 55_HRV76 | ACTCTTGATGAGATGTGTATGGAGAGTTTCTTAGGGAGATCTGGTTGTATTCATATTTCA |
| 1226 | 56_HRV76b\| | ACTCTTGATGAGATGTGTATGGAGAGTTTCTTAGGGAGATCTGGTTGTATTCATATTTCA |
| 1227 | 57_HRV76a\| | ACTCTTGATGAGATGTGTATGGAGAGTTTCTTAGGGAGATCTGGTTGTATTCATATTTCA |
| 1228 | 58_HRV33 | ACTCTTGATGAGATGAGTGTGGAAAGCTTCTTAGGAAGGTCTGGTTGCATTCACATGTCA |
| 1229 | 59_HRV33b\| | ACTCTTGATGAGATGAGTGTGGAAAGCTTCTTAGGAAGGTCTGGTTGCATTCACATGTCA |
| 1230 | 60_HRV33a\| | ACTCTTGATGAGATGAGTGTGGAAAGCTTCTTAGGAAGGTCTGGTTGCATTCACATGTCA |
| 1231 | 61_HRV24a\| | ACATTACATGAGATGAGTGTTGAAAGTTTCTTGGGTAGATCAGGTTGCATACACATGTCC |
| 1232 | 62_HRV24b\| | ACATTACATGAGATGAGTGTTGAAAGTTTCTTGGGTAGATCAGGTTGCATACACATGTCC |
| 1233 | 63_HRV24 | ACATTACATGAGATGAGTGTTGAAAGTTTCTTGGGTAGATCAGGTTGCATACACATGTCC |
| 1234 | 64_HRV90 | ACAAGAGATGAAATGAGTGTTGAAAGTTTTCTAGGGAGATCAGGTTGCATTCATATGTCA |
| 1235 | 65_HRV90a\| | ACAAGAGATGAAATGAGTGTTGAAAGTTTTCTAGGGAGATCAGGTTGCATTCATATGTCA |
| 1236 | 66_HRV90b\| | ACAAGAGATGAAATGAGTGTTGAAAGTTTTCTAGGGAGATCAGGTTGCATTCATATGTCA |
| 1237 | 67_HRV34 | ACAAGAGATGAAATGAGCATTGAGAGTTTCCTGGGTAGGTCTGGCTGTATACACATGTCC |
| 1238 | 68_HRV34b\| | ACAAGAGATGAAATGAGCATTGAGAGTTTCCTGGGTAGGTCTGGCTGTATACACATGTCC |
| 1239 | 69_HRV34a\| | ACAAGAGATGAAATGAGCATTGAGAGTTTCCTGGGTAGGTCTGGCTGTATACACATGTCC |
| 1240 | 70_HRV50a\| | ACAAGAGATGAAATGAGCATTGAAAGTTTCCTAGGTAGATCTGGTTGTATACATATATCT |
| 1241 | 71_HRV50b\| | ACAAGAGATGAAATGAGCATTGAAAGTTTCCTAGGTAGATCTGGTTGTATACATATATCT |
| 1242 | 72_HRV50 | ACAAGAGATGAAATGAGCATTGAAAGTTTCCTAGGTAGATCTGGTTGTATACATATATCT |
| 1243 | 73_HRV18a\| | ACAAGAGATGAAATGAGTATAGAGTGTTTTCTAGGCAGATCAGGGTGTATACATATCTCC |
| 1244 | 74_HRV18b\| | ACAAGAGATGAAATGAGTATAGAGTGTTTTCTAGGCAGATCAGGGTGTATACATATCTCC |
| 1245 | 75_HRV18 | ACAAGAGATGAAATGAGTATAGAGTGTTTTCTAGGCAGATCAGGGTGTATACATATCTCC |
| 1246 | 76_HRV55 | ACTCGTGATGAGATGAGCATTGAAAGTTTTCTAGGTAGATCAGGATGTGTACATATATCA |
| 1247 | 77_HRV55b\| | ACTCGTGATGAGATGAGCATTGAAAGTTTTCTAGGTAGATCAGGATGTGTACATATATCA |
| 1248 | 78_HRV55a\| | ACTCGTGATGAGATGAGCATTGAAAGTTTTCTAGGTAGATCAGGATGTGTACATATATCA |
| 1249 | 79_HRV57 | ACACGTGATGAAATGAGTCTTGAGAGCTTCTTAGGAAGATCTGGCTGCATTCATATTTCA |
| 1250 | 80_HRV57a\| | ACACGTGATGAAATGAGTCTTGAGAGCTTCTTAGGAAGATCTGGCTGCATTCATATTTCA |
| 1251 | 81_HRV57b\| | ACACGTGATGAAATGAGTCTTGAGAGCTTCTTAGGAAGATCTGGCTGCATTCATATTTCA |
| 1252 | 82_HRV21 | ACACGTGATGAAATGAGTATTGAAAGTTTTCTGGGCAGATCAGGGTGCATTCACATGTCA |
| 1253 | 83_HRVHan | ACACGTGATGAAATGAGTATTGAAAGCTTCTTAGGCAGATCAGGATGTATCCACATGTCA |
| 1254 | 84_HRV43 | ACCAGAGATGAAATGAGTATTGAAAGTTTCTTGGGCAGATCTGGTTGCATACATATTTCA |
| 1255 | 85_HRV43b\| | ACCAGAGATGAAATGAGTATTGAAAGTTTCTTGGGCAGATCTGGTTGCATACATATTTCA |
| 1256 | 86_HRV43a\| | ACCAGAGATGAAATGAGTATTGAAAGTTTCTTGGGCAGATCTGGTTGCATACATATTTCA |
| 1257 | 87_HRV75 | ACTAGAGATGAGATGAGTATTGAGAGTTTCCTAGGCAGATCTGGATGTATTCATATTTCA |
| 1258 | 88_HRV75b\| | ACTAGAGATGAGATGAGTATTGAGAGTTTCCTAGGCAGATCTGGATGTATTCATATTTCA |
| 1259 | 89_HRV75a\| | ACTAGAGATGAGATGAGTATTGAGAGTTTCCTAGGCAGATCTGGATGTATTCATATTTCA |
| 1260 | 96_HRV9a\|d | ACCAGAGATGAAATGAGTCTTGAAAGCTTCTTAGGGAGATCAGGTTGTATACACATATCT |
| 1261 | 97_HRV9b\|d | ACCAGAGATGAAATGAGTCTTGAAAGCTTCTTAGGGAGATCAGGTTGTATACACATATCT |
| 1262 | 98_HRV9 | ACCAGAGATGAAATGAGTCTTGAAAGCTTCTTAGGGAGATCAGGTTGTATACACATATCT |
| 1263 | 99_HRV32 | ACTAGAGATGAGATGAGTCTTGAGAGCTTCTTAGGGAGGTCAGGATGTGTACATATATCC |
| 1264 | 100_HRV32a | ACTAGAGATGAGATGAGTCTTGAGAGCTTCTTAGGGAGGTCAGGATGTGTACATATATCC |
| 1265 | 101_HRV32b | ACTAGAGATGAGATGAGTCTTGAGAGCTTCTTAGGGAGGTCAGGATGTGTACATATATCC |
| 1266 | 102_HRV67 | ACCAGAGATGAAATGAGTCTCGAGAGCTTTCTTGGAAGGTCAGGCTGTATTCATATATCA |
| 1267 | 103_HRV67a | ACCAGAGATGAAATGAGTCTCGAGAGCTTTCTTGGAAGGTCAGGCTGTATTCATATATCA |
| 1268 | 104_HRV67b | ACCAGAGATGAAATGAGTCTCGAGAGCTTTCTTGGAAGGTCAGGCTGTATTCATATATCA |
| 1269 | 105_HRV15 | ACCAGAGATGAAATGAGTATTGAGAGCTTCCTTGGTAGATCAGGGTGTGTCCATATTTCT |
| 1270 | 106_HRV15a | ACCAGAGATGAAATGAGTATTGAGAGCTTCCTTGGTAGATCAGGGTGTGTCCATATTTCT |
| 1271 | 107_HRV15b | ACCAGAGATGAAATGAGTATTGAGAGCTTCCTTGGTAGATCAGGGTGTGTCCATATTTCT |
| 1272 | 108_HRV74a | ACAAGAGATGAGATGAGTGTAGAAAGTTTTCTTGGAAGATCAGGATGCATCCATATCTCA |
| 1273 | 109_HRV74b | ACAAGAGATGAGATGAGTGTAGAAAGTTTTCTTGGAAGATCAGGATGCATCCATATCTCA |
| 1274 | 110_HRV74 | ACAAGAGATGAGATGAGTGTAGAAAGTTTTCTTGGAAGATCAGGATGCATCCATATCTCA |
| 1275 | 111_HRV38a | ACTAGAGATGAAATGAGTGTAGAAAGTTTTCTAGGAAGATCAGGTTGTGTACATATATCC |
| 1276 | 112_HRV38b | ACTAGAGATGAAATGAGTGTAGAAAGTTTTCTAGGAAGATCAGGTTGTGTACATATATCC |
| 1277 | 113_HRV38 | ACTAGAGATGAAATGAGTGTAGAAAGTTTTCTAGGAAGATCAGGTTGTGTACATATATCC |
| 1278 | 114_HRV60 | ACTAGAGATGAGATGAGTGTTGAGAGCTTCCTCGGCAGATCTGGATGTATTCATATTTCC |
| 1279 | 115_HRV60a | ACTAGAGATGAGATGAGTGTTGAGAGCTTCCTCGGCAGATCTGGATGTATTCATATTTCC |
| 1280 | 116_HRV60b | ACTAGAGATGAGATGAGTGTTGAGAGCTTCCTCGGCAGATCTGGATGTATTCATATTTCC |

FIG. D5 CONT'D 01.trace                                                                9/20/2007 4:58 PM

```
1281  117_HRV64a   ACTAGAGATGAAATGAGCATTGAGAGTTTCTTGGGCAGGTCTGGTTGTATACACATATCA
1282  118_HRV64b   ACTAGAGATGAAATGAGCATTGAGAGTTTCTTGGGCAGGTCTGGTTGTATACACATATCA
1283  119_HRV64    ACTAGAGATGAAATGAGCATTGAGAGTTTCTTGGGCAGGTCTGGTTGTATACACATATCA
1284  120_HRV94a   ACAAGGGATGAAATGAGCATTGAAAGCTTCTTGGGAAGATCTGGCTGTATACACATAGCA
1285  121_HRV94b   ACAAGGGATGAAATGAGCATTGAAAGCTTCCTGGGAAGATCTGGCTGTATACACATAGCA
1286  122_HRV94    ACAAGGGATGAAATGAGCATTGAAAGCTTCTTGGGAAGATCTGGCTGTATACACATAGCA
1287  123_HRV22    ACTAGAGATGAAATGAGTATTGAGAGCTTCCTGGGAAGATCTGGTTGCATACATATATCA
1288  124_HRV22a   ACTAGAGATGAAATGAGTATTGAGAGCTTCCTGGGAAGATCTGGTTGCATACATATATCA
1289  125_HRV22b   ACTAGAGATGAAATGAGTATTGAGAGCTTCCTGGGAAGATCTGGTTGCATACATATATCA
1290  126_HRV82    ACTAGAGATGAGCCTTGAGAGTTTCCTAGGGAGATCTGGCTGCATACACATATCA
1291  127_HRV82b   ACTAGAGATGAGATGAGCCTTGAGAGTTTCCTAGGGAGATCTGGCTGCATACACATATCA
1292  128_HRV82a   ACTAGAGATGAGATGAGCCTTGAGAGTTTCCTAGGGAGATCTGGCTGCATACACATATCA
1293  129_HRV19    ACTAGGGATGAAATGAGCATAGAAAGTTTTCTTGGCAGATCCGGTTGTGTACATGTTTCA
1294  130_HRV19a   ACTAGGGATGAAATGAGCATAGAAAGTTTTCTTGGCAGATCCGGTTGTGTACATGTTTCA
1295  131_HRV19b   ACTAGGGATGAAATGAGCATAGAAAGTTTTCTTGGCAGATCCGGTTGTGTACATGTTTCA
1296  132_HRV13    ACTAGGGATGAAATGAGTGTTGAGAGCTTTTTAGGCAGATCTGGTTGTATACACATGTCT
1297  133_HRV13a   ACTAGGGATGAAATGAGTGTTGAGAGCTTTTTAGGCAGATCTGGTTGTATACACATGTCT
1298  134_HRV13b   ACTAGGGATGAAATGAGTGTTGAGAGCTTTTTAGGCAGATCTGGTTGTATACACATGTCT
1299  135_HRV41    ACTAGAGATGAAATGAGCATAGAAAGCTTTTTAGGTAGATCAGGCTGTGTACATAAGTCC
1300  136_HRV41a   ACTAGAGATGAAATGAGCATAGAAAGCTTTTTAGGTAGATCAGGCTGTGTACATAAGTCC
1301  137_HRV41b   ACTAGAGATGAAATGAGCATAGAAAGCTTTTTAGGTAGATCAGGCTGTGTACATAAGTCC
1302  138_HRV73    ACTAGAGATGAAATGAGCATTGAAAGCTTCCTTGGCAGGTCAGGTTGTATACACATGTCA
1303  139_HRV73b   ACTAGAGATGAAATGAGCATTGAAAGCTTCCTTGGCAGGTCAGGTTGTATACACATGTCA
1304  140_HRV73a   ACTAGAGATGAAATGAGCATTGAAAGCTTCCTTGGCAGGTCAGGTTGTATACACATGTCA
1305  141_HRV61    ACAAGAGATGAAATGAGTGTAGAAAGTTTCTTGGGTAGATCAGGGTGCATACATATGTCA
1306  142_HRV61a   ACAAGAGATGAAATGAGTGTAGAAAGTTTCTTGGGTAGATCAGGGTGCATACATATGTCA
1307  143_HRV61b   ACAAGAGATGAAATGAGTGTAGAAAGTTTCTTGGGTAGATCAGGGTGCATACATATGTCA
1308  144_HRV96    ACGAGAGATGAAATGAGCATTGAGAGCTTTTTGGGTAGATCAGGGTGTATACACATGTCA
1309  145_HRV96b   ACGAGAGATGAAATGAGCATTGAGAGCTTTTTGGGTAGATCAGGGTGTATACACATGTCA
1310  146_HRV96a   ACGAGAGATGAAATGAGCATTGAGAGCTTTTTGGGTAGATCAGGGTGTATACACATGTCA
1311  90_HRV16a|   ACATTGGATGAAATGAGTGTGGAAAGCTTCCTAGGCAGATCGGGGTGCATCCATGAATCA
1312  91_HRV16b|   ACATTGGATGAAATGAGTGTGGAAAGCTTCCTAGGCAGATCGGGGTGCATCCATGAATCA
1313  92_1AYM_A    ACATTGGATGAAATGAGTGTGGAAAGCTTCCTAGGCAGATCGGGGTGCATCCATGAATCA
1314  93_HRV81a|   ACACTGGATGAAATGAGTGTAGAAAGTTTTTTAGGCAGATCAGGTTGCATTCATGAATCC
1315  94_HRV81b|   ACACTGGATGAAATGAGTGTAGAAAGTTTTTTAGGCAGATCAGGTTGCATTCATGAATCC
1316  95_HRV81     ACACTGGATGAAATGAGTGTAGAAAGTTTTTTAGGCAGATCAGGTTGCATTCATGAATCC
1317  147_HRV2     ACAAGAGATGAAATGAGTTTAGAGAGTTTCTTGGCAGATCAGGATGCATACATGAATCT
1318  148_HRV2a|   ACAAGAGATGAAATGAGTTTAGAGAGTTTTCTTGGCAGATCAGGATGCATACATGAATCT
1319  149_HRV2b|   ACAAGAGATGAAATGAGTTTAGAGAGTTTTCTTGGCAGATCAGGATGCATACATGAATCT
1320  150_HRV49a   ACAAGAGATGAAATGAGTTTAGAGAGTTTCTTGGTAGGTCAGGGTGTATACATGAATCC
1321  151_HRV49b   ACAAGAGATGAAATGAGTTTAGAGAGTTTCTTGGTAGGTCAGGGTGTATACATGAATCC
1322  152_HRV49    ACAAGAGATGAAATGAGTTTAGAGAGTTTCTTGGTAGGTCAGGGTGTATACATGAATCC
1323  153_HRV23a   ACAAGAGATGAAATGAGTTTAGAAAGTTTCCTTGGTAGGTCAGGGTGTATACATGAATCT
1324  154_HRV23b   ACAAGAGATGAAATGAGTTTAGAAAGTTTCCTTGGTAGGTCAGGGTGTATACATGAATCT
1325  155_HRV23    ACAAGAGATGAAATGAGTTTAGAAAGTTTCCTTGGTAGGTCAGGGTGTATACATGAATCT
1326  156_HRV30a   ACAAGGGATGAAATGAGTTTAGAAAGCTTTCTTGGTAGATCAGGATGTATACACGAGTCT
1327  157_HRV30b   ACAAGGGATGAAATGAGTTTAGAAAGCTTTCTTGGTAGATCAGGATGTATACACGAGTCT
1328  158_HRV30    ACAAGGGATGAAATGAGTTTAGAAAGCTTTCTTGGTAGATCAGGATGTATACACGAGTCT
1329  159_HRV7     ACAAGGGATGAAACTAGTATAGAGAGTTTCTTAGGTAGATCTGGATGTATTGCTAAAGTT
1330  160_HRV7b|   ACAAGGGATGAAACTAGTATAGAGAGTTTCTTAGGTAGATCTGGATGTATTGCTAAAGTT
1331  161_HRV7a|   ACAAGGGATGAAACTAGTATAGAGAGTTTCTTAGGTAGATCTGGATGTATTGCTAAAGTT
1332  162_HRV88    ACAAGGGATGAAACCAGCATTGAAAGCTTTCTGGGTAGGTCTGGATGCATAGCAAAAATT
1333  163_HRV88a   ACAAGGGATGAAACCAGCATTGAAAGCTTTCTGGGTAGGTCTGGATGCATAGCAAAAATT
1334  164_HRV88b   ACAAGGGATGAAACCAGCATTGAAAGCTTTCTGGGTAGGTCTGGATGCATAGCAAAAATT
1335  165_HRV36a   ACAAGAGATGAGACAAGTATTGAAAGCTTCTTAGGTAGGTCAGGGTGCATAGCTATGATA
1336  166_HRV36b   ACAAGAGATGAGACAAGTATTGAAAGCTTCTTAGGTAGGTCAGGGTGCATAGCTATGATA
1337  167_HRV36    ACAAGAGATGAGACAAGTATTGAAAGCTTCTTAGGTAGGTCAGGGTGCATAGCTATGATA
1338  168_HRV89a   ACAAGGGATGAAACAAGTATTGAGAGTTTCTTAGGTAGGTCAGGGTGTATCGCTATGATA
1339  169_HRV89b   ACAAGGGATGAAACAAGTATTGAGAGTTTCTTAGGTAGGTCAGGGTGTATCGCTATGATA
1340  170_HRV89    ACAAGGGATGAAACAAGTATTGAGAGTTTCTTAGGTAGGTCAGGGTGTATCGCTATGATA
1341  171_HRV58    ACAAGAGATGAAACTAGCATTGAAAGCTTTTTAGGTAGATCTGGTTGCATTGCTATCATA
1342  172_HRV58a   ACAAGAGATGAAACTAGCATTGAAAGCTTTTTAGGTAGATCTGGTTGCATTGCTATCATA
1343  173_HRV58b   ACAAGAGATGAAACTAGCATTGAAAGCTTTTTAGGTAGATCTGGTTGCATTGCTATCATA
1344  174_HRV12a   ACTAGAGATGAGATGTCAATTGAATCTTTCCTTGGTCGGTCCGGATGCATTTCAATTATC
```

FIG. D5 CONT'D

01.trace 9/20/2007 4:58 PM

| | | |
|---|---|---|
| 1345 | 175_HRV12b | ACTAGAGATGAGATGTCAATTGAATCTTTCCTTGGTCGGTCCGGATGCATTTCAATTATC |
| 1346 | 176_HRV12 | ACTAGAGATGAGATGTCAATTGAATCTTTCCTTGGTCGGTCCGGATGCATTTCAATTATC |
| 1347 | 177_HRV78a | ACAAGAGATGAAATGAGCATTGAAAGTTTCCTCGGAAGATCAGGTTGTGCAACAATTATG |
| 1348 | 178_HRV78b | ACAAGAGATGAAATGAGCATTGAAAGTTTCCTCGGAAGATCAGGTTGTGCAACAATTATG |
| 1349 | 179_HRV78 | ACAAGAGATGAAATGAGCATTGAAAGTTTCCTCGGAAGATCAGGTTGTGCAACAATTATG |
| 1350 | 180_HRV20 | ACCCGTGATGAAATGAGTGTGGAAAGTTTTCTTGGTAGATCTGGTTGCATTGCTATCATA |
| 1351 | 181_HRV20a | ACCCGTGATGAAATGAGTGTGGAAAGTTTTCTTGGTAGATCTGGTTGCATTGCTATCATA |
| 1352 | 182_HRV20b | ACCCGTGATGAAATGAGTGTGGAAAGTTTTCTTGGTAGATCTGGTTGCATTGCTATCATA |
| 1353 | 183_HRV68 | ACAAGGGATGAAATGAGCATAGAGAGCTTCCTCGGTAGGTCAGGTTGCATTGCAATCATA |
| 1354 | 184_HRV68a | ACAAGGGATGAAATGAGCATAGAGAGCTTCCTCGGTAGGTCAGGTTGCATTGCAATCATA |
| 1355 | 185_HRV68b | ACAAGGGATGAAATGAGCATAGAGAGCTTCCTCGGTAGGTCAGGTTGCATTGCAATCATA |
| 1356 | 186_HRV28 | ACCCGTGATGAAATGAGTATAGAGAGTTTCTTAGGTAGGTCTAGTTGCATTGCAATAATC |
| 1357 | 187_HRV28a | ACCCGTGATGAAATGAGTATAGAGAGTTTCTTAGGTAGGTCTAGTTGCATTGCAATAATC |
| 1358 | 188_HRV28b | ACCCGTGATGAAATGAGTATAGAGAGTTTCTTAGGTAGGTCTAGTTGCATTGCAATAATC |
| 1359 | 189_HRV53a | ACCCGGGATGAAATGAGCATTGAAAGTTTCTTAGGCAGATCAAGTTGCATTGCTGAGATC |
| 1360 | 190_HRV53b | ACCCGGGATGAAATGAGCATTGAAAGTTTCTTAGGCAGATCAAGTTGCATTGCTGAGATC |
| 1361 | 191_HRV53 | ACCCGGGATGAAATGAGCATTGAAAGTTTCTTAGGCAGATCAAGTTGCATTGCTGAGATC |
| 1362 | 192_HRV46a | ACAAAAGATGAAATGAGTATAGAAAGTTTTCTAGGAAGGTCAGGCTGCATTGCCATTATT |
| 1363 | 193_HRV46b | ACAAAAGATGAAATGAGTATAGAAAGTTTTCTAGGAAGGTCAGGCTGCATTGCCATTATT |
| 1364 | 194_HRV46 | ACAAAAGATGAAATGAGTATAGAAAGTTTTCTAGGAAGGTCAGGCTGCATTGCCATTATT |
| 1365 | 195_HRV80a | ACAAGGATGAGATGAGCATTGAAAGTTTCTTAGGAAGATCTGGTTGTGTTGCTATCATT |
| 1366 | 196_HRV80b | ACAAGGATGAGATGAGCATTGAAAGTTTCTTAGGAAGATCTGGTTGTGTTGCTATCATT |
| 1367 | 197_HRV80 | ACAAAGGATGAGATGAGCATTGAAAGTTTCTTAGGAAGATCTGGTTGTGTTGCTATCATT |
| 1368 | 198_HRV51 | ACTAGAGATGAAATGAGTATAGAGAGTTTCTTGGGTAGATCTGCTTGCGTAGCAATCATC |
| 1369 | 199_HRV51a | ACTAGAGATGAAATGAGTATAGAGAGTTTCTTGGGTAGATCTGCTTGCGTAGCAATCATC |
| 1370 | 200_HRV51b | ACTAGAGATGAAATGAGTATAGAGAGTTTCTTGGGTAGATCTGCTTGCGTAGCAATCATC |
| 1371 | 201_HRV65a | ACCAGAGATGAGATGAGCGTAGAGAGTTTCCTGGGCAGATCTGCCTGCATAGCAGTCATT |
| 1372 | 202_HRV65b | ACCAGAGATGAGATGAGCGTAGAGAGTTTCCTGGGCAGATCTGCCTGCATAGCAGTCATT |
| 1373 | 203_HRV65 | ACCAGAGATGAGATGAGCGTAGAGAGTTTCCTGGGCAGATCTGCCTGCATAGCAGTCATT |
| 1374 | 204_HRV71a | ACTAGGGATGAAATGAGCATTGAGAGCTTCTTGGGCAGATCTGCATGCATAGCTACCATA |
| 1375 | 205_HRV71b | ACTAGGGATGAAATGAGCATTGAGAGCTTCTTGGGCAGATCTGCATGCATAGCTACCATA |
| 1376 | 206_HRV71 | ACTAGGGATGAAATGAGCATTGAGAGCTTCTTGGGCAGATCTGCATGCATAGCTACCATA |
| 1377 | 207_HRV8 | ACTAGGCATGAGACATCACTGGAATCTTTCTTGGGTAGAGCAGGATGCATTAAAATCATT |
| 1378 | 208_HRV95 | ACTAGGTATGAGACATCACTGGAATCTTTCTTGGGTAGAGCAGGATGCATTAAAATTATT |
| 1379 | 209_HRV45 | ACCAGACATGAAACCTCCATTGAATCTTTTTGGGTAGGGCTGGATGTGTGGCCAATATT |
| 1380 | 210_HRV45a | ACCAGACATGAAACCTCCATTGAATCTTTTTGGGTAGGGCTGGATGTGTGGCCAATATT |
| 1381 | 211_HRV45b | ACCAGACATGAAACCTCCATTGAATCTTTTTGGGTAGGGCTGGATGTGTGGCCAATATT |
| 1382 | 212_HRV6 | ------------------------------------------------------------ |
| 1383 | 213_HRV6a | ------------------------------------------------------------ |
| 1384 | 214_HRV6b | ------------------------------------------------------------ |
| 1385 | 215_HRV37 | ------------------------------------------------------------ |
| 1386 | 216_HRV37a | ------------------------------------------------------------ |
| 1387 | 217_HRV37b | ------------------------------------------------------------ |
| 1388 | 218_HRV3 | ------------------------------------------------------------ |
| 1389 | 219_HRV3a | ------------------------------------------------------------ |
| 1390 | 220_HRV3b | ------------------------------------------------------------ |
| 1391 | 221_HRV14 | ------------------------------------------------------------ |
| 1392 | 222_HRV14a | ------------------------------------------------------------ |
| 1393 | 223_HRV14b | ------------------------------------------------------------ |
| 1394 | 224_HRV72 | ------------------------------------------------------------ |
| 1395 | 225_HRV72a | ------------------------------------------------------------ |
| 1396 | 226_HRV72b | ------------------------------------------------------------ |
| 1397 | 227_HRV83 | ------------------------------------------------------------ |
| 1398 | 228_HRV83a | ------------------------------------------------------------ |
| 1399 | 229_HRV83b | ------------------------------------------------------------ |
| 1400 | 230_HRV92 | ------------------------------------------------------------ |
| 1401 | 231_HRV92a | ------------------------------------------------------------ |
| 1402 | 232_HRV92b | ------------------------------------------------------------ |
| 1403 | 233_HRV79 | ------------------------------------------------------------ |
| 1404 | 234_HRV79a | ------------------------------------------------------------ |
| 1405 | 235_HRV79b | ------------------------------------------------------------ |
| 1406 | 236_HRV35 | ------------------------------------------------------------ |
| 1407 | 237_HRV35a | ------------------------------------------------------------ |
| 1408 | 238_HRV35b | ------------------------------------------------------------ |

FIG. D5 CONT'D

01.trace                                                                9/20/2007 4:58 PM

```
1409  239_1HRV86    ------------------------------------------------------------
1410  240_1HRV86    ------------------------------------------------------------
1411  241_1HRV86    ------------------------------------------------------------
1412  242_HRV70     ------------------------------------------------------------
1413  243_HRV70a    ------------------------------------------------------------
1414  244_HRV70b    ------------------------------------------------------------
1415  245_HRV91     ------------------------------------------------------------
1416  246_HRV91a    ------------------------------------------------------------
1417  247_HRV91b    ------------------------------------------------------------
1418  248_HRV17     ------------------------------------------------------------
1419  249_HRV17a    ------------------------------------------------------------
1420  250_HRV17b    ------------------------------------------------------------
1421  251_HRV69     ------------------------------------------------------------
1422  252_HRV69a    ------------------------------------------------------------
1423  253_HRV69b    ------------------------------------------------------------
1424  254_HRV48     ------------------------------------------------------------
1425  255_HRV48a    ------------------------------------------------------------
1426  256_HRV48b    ------------------------------------------------------------
1427  257_HRV52     ------------------------------------------------------------
1428  258_HRV52a    ------------------------------------------------------------
1429  259_HRV52b    ------------------------------------------------------------
1430  260_HRV4      ------------------------------------------------------------
1431  261_HRV4a|    ------------------------------------------------------------
1432  262_HRV4b|    ------------------------------------------------------------
1433  263_HRV99     ------------------------------------------------------------
1434  264_HRV99a    ------------------------------------------------------------
1435  265_HRV99b    ------------------------------------------------------------
1436  266_HRV5      ------------------------------------------------------------
1437  267_HRV5a|    ------------------------------------------------------------
1438  268_HRV5b|    ------------------------------------------------------------
1439  269_HRV42     ------------------------------------------------------------
1440  270_HRV42a    ------------------------------------------------------------
1441  271_HRV42b    ------------------------------------------------------------
1442  272_HRV26     ------------------------------------------------------------
1443  273_HRV26a    ------------------------------------------------------------
1444  274_HRV26b    ------------------------------------------------------------
1445  275_HRV27     ------------------------------------------------------------
1446  276_HRV27a    ------------------------------------------------------------
1447  277_HRV27b    ------------------------------------------------------------
1448  278_HRV93     ------------------------------------------------------------
1449  279_HRV93a    ------------------------------------------------------------
1450  280_HRV93b    ------------------------------------------------------------
1451  281_HRV97     ------------------------------------------------------------
1452  282_HRV97a    ------------------------------------------------------------
1453  283_HRV97b    ------------------------------------------------------------
1454  284_HRV84     ------------------------------------------------------------
1455  285_HRV84a    ------------------------------------------------------------
1456  286_HRV84b    ------------------------------------------------------------
1457  287_HRV87     ------------------------------------------------------------
1458  288_HRV87a    ------------------------------------------------------------
1459  289_HRV87b    ------------------------------------------------------------
1460  GROUP_1       ------------------------------------------------------------
1461
1462  1_HRV1A1|d    AGAATAAAGGTTGATTACACTGAC---------------TATAATGGA---CAGGACATA
1463  2_HRV1A2|d    AGAATAAAGGTTGATTACACTGAC---------------TATAATGGA---CAGGACATA
1464  3_HRV1A|cD    AGAATAAAGGTTGATTACACTGAC---------------TATAATGGA---CAGGACATA
1465  4_HRV1B1|d    AGAATAAAGGTTGATTACAATGAC---------------TACAATGGA---GTGAACAAA
1466  5_HRV1B2|d    AGAATAAAGGTTGATTACAATGAC---------------TACAATGGA---GTGAACAAA
1467  6_HRV1B       AGAATAAAGGTTGATTACAATGAC---------------TACAATGGA---GTGAACAAA
1468  7_HRV40a|d    ACAATTACAGTGGATAACAGTTTG---------------GAATATG------ATGACCAC
1469  8_HRV40b|d    ACAATTACAGTGGATAACAGTTTG---------------GAATATG------ATGACCAC
1470  9_HRV40       ACAATTACAGTGGATAACAGTTTG---------------GAATATG------ATGACCAC
1471  10_HRV85      ACAATTACTGTGAATAACAACCTA---------------GATTATG------ATGAAAAT
1472  11_HRV85a|    ACAATTACTGTGAATAACAACCTA---------------GATTATG------ATGAAAAT
```

FIG. D5 CONT'D

01.trace                                                                                             9/20/2007 4:58 PM

```
1473  12_HRV85b|    ACAATTACTGTGAATAACAACCTA--------------GATTATG------ATGAAAAT
1474  13_HRV56a|    ACTATAACTGTGGATAATGATGTA--------------GATTATA------ATTCAAAG
1475  14_HRV56b|    ACTATAACTGTGGATAATGATGTA--------------GATTATA------ATTCAAAG
1476  15_HRV56     ACTATAACTGTGGATAATGATGTA--------------GATTATA------ATTCAAAG
1477  16_HRV54     ACCATTACAATTCAAAATGATGTA--------------GAATACA------ATGATCAC
1478  17_HRV98     ACTATCACTATTCAAAATGATGTA--------------GAATATA------ACGATCAT
1479  18_HRV59a|    ACTATTACTGTCAATAAAGACATA--------------AAATATG------ATGATGGA
1480  19_HRV59b|    ACTATTACTGTCAATAAAGACATA--------------AAATATG------ATGATGGA
1481  20_HRV59     ACTATTACTGTCAATAAAGACATA--------------AAATATG------ATGATGGA
1482  21_HRV63     ACTATCACTGTTGACAAAACCATT--------------GACTATG------ACACTGGA
1483  22_HRV63b|    ACTATCACTGTTGACAAAACCATT--------------GACTATG------ACACTGGA
1484  23_HRV63a|    ACTATCACTGTTGACAAAACCATT--------------GACTATG------ACACTGGA
1485  24_HRV39     ACAATTACTATGAAGAAGGAG-----------------AACTATA------ATGATCAT
1486  25_HRV39a|    ACAATTACTATGAAGAAGGAG-----------------AACTATA------ATGATCAT
1487  26_HRV39b|    ACAATTACTATGAAGAAGGAG-----------------AACTATA------ATGAACAT
1488  27_HRV10a|    ACAATAACTGTTAATAATACAAGA--------------CCCTACA------ATGAACAC
1489  28_HRV10b|    ACAATAACTGTTAATAATACAAGA--------------CCCTACA------ATGAACAC
1490  29_HRV10     ACAATAACTGTTAATAATACAAGA--------------CCCTACA------ATGAACAC
1491  30_HRV100a    ACAATTACTGTAAGTAAAATGAAA--------------AATTATA------ATGAGCAC
1492  31_HRV100b    ACAATTACTGTAAGTAAAATGAAA--------------AATTATA------ATGAGCAC
1493  32_HRV100     ACAATTACTGTAAGTAAAATGAAA--------------AATTATA------ATGAGCAC
1494  33_HRV66     ACAATTAATGTGGATAGCACAAAA--------------ACATATG------ATGAATCC
1495  34_HRV66b|    ACAATTAATGTGGATAGCACAAAA--------------ACATATG------ATGAATCC
1496  35_HRV66a|    ACAATTAATGTGGATAGCACAAAA--------------ACATATG------ATGAATCC
1497  36_HRV77a|    ACAATAAATGTAGAAGATGGTAAA--------------ACTTATG------ATGAATCT
1498  37_HRV77b|    ACAATAAATGTAGAAGATGGTAAA--------------ACTTATG------ATGAATCT
1499  38_HRV77     ACAATAAATGTAGAAGATGGTAAA--------------ACTTATG------ATGAATCT
1500  39_HRV62a    ACAATTGAA---------ACAACG--------------CTTAGTC------ATAAAGAT
1501  40_HRV62b    ACAATTGAA---------ACAACG--------------CTTAGTC------ATAAAGAT
1502  41_HRV25     ACAATTGAA---------ACAAAA--------------CTTAAAC------ATGATGAA
1503  42_HRV29a    ACAATAAAA---------GCAAAT--------------CAGGCAC------ATGACGCC
1504  43_HRV29b    ACAATAAAA---------GCAAAT--------------CAGGCAC------ATGACGCC
1505  44_HRV44a    ACAATAAAG---------ACAAAT--------------CAGGCAC------ACAATACC
1506  45_HRV44b    ACAATAAAG---------ACAAAT--------------CAGGCAC------ACAATACC
1507  46_HRV31     ATAATAGAA---------CCAGAT--------------GGACTCC------ATGATAGC
1508  47_HRV31a|    ATAATAGAA---------CCAGAT--------------GGACTCC------ATGATAGC
1509  48_HRV31b|    ATAATAGAA---------CCAGAT--------------GGACTCC------ATGATAGC
1510  49_HRV47     ACAATAAAA---------TCAGAT--------------GAGCAAC------ACATTAAT
1511  50_HRV47a|    ACAATAAAA---------TCAGAT--------------GAGCAAC------ACATTAAT
1512  51_HRV47b|    ACAATACAA---------TCAAAT--------------GAGCAAC------ACATTAAT
1513  52_HRV11     AAGTTAATTGTGCAGTATGAAGAC--------------TATAAT------GGAAAGAAA
1514  53_HRV11b|    AAGTTAATTGTGCAGTATGAAGAC--------------TATAAT------GGAAAGAAA
1515  54_HRV11a|    AAGTTAATTGTGCAGTATGAAGAC--------------TATAAT------GGAAAGAAA
1516  55_HRV76     AAGCTAGTTGTAGAATATGAGGGA--------------TATGAT------GATACAAAA
1517  56_HRV76b|    AAGCTAGTTGTAGAATATGAGGGA--------------TATGAT------GATACAAAA
1518  57_HRV76a|    AAGCTAGTTGTAGAATATGAGGGA--------------TATGAT------GATACAAAA
1519  58_HRV33     AAATTAGTAGTGAAATATGAAGAC--------------TATAAT------GAGAAAAAG
1520  59_HRV33b|    AAATTAGTAGTGAAATATGAAGAC--------------TATAAT------GAGAAAAAG
1521  60_HRV33a|    AAATTAGTAGTGAAATATGAAGAC--------------TATAAT------GAGAAAAAG
1522  61_HRV24a|    AAGTTGACTGTGGATTAT---GAC--------------AATTAT------GATACAAAA
1523  62_HRV24b|    AAGTTGACTGTGGATTAT---GAC--------------AATTAT------GATACAAAA
1524  63_HRV24     AAGTTGACTGTGGATTAT---GAC--------------AATTAT------GATACAAAA
1525  64_HRV90     AAATTAGTTGTAAACTAT---GAT--------------AATTAT------GATGAAAAC
1526  65_HRV90a|    AAATTAGTTGTAAACTAT---GAT--------------AATTAT------GATGAAAAC
1527  66_HRV90b|    AAATTAGTTGTAAACTAT---GAT--------------AATTAT------GATGAAAAC
1528  67_HRV34     AAACTTGTTGTAGATTATGAAAAT--------------TACAATGCA---AAAACAAAG
1529  68_HRV34b|    AAACTTGTTGTAGATTATGAAAAT--------------TACAATGCA---AAAACAAAG
1530  69_HRV34a|    AAACTTGTTGTAGATTATGAAAAT--------------TACAATGCA---AAAACAAAG
1531  70_HRV50a|    AAATTAGTTGTTGATTATGATGGT--------------TACAATGAG---GAAACAAAG
1532  71_HRV50b|    AAATTAGTTGTTGATTATGATGGT--------------TACAATGAG---GAAACAAAG
1533  72_HRV50     AAATTAGTTGTTGATTATGATGGT--------------TACAATGAG---GAAACAAAG
1534  73_HRV18a|    AAGTTAGTTGTACATTATGAAGAT--------------TATAATGCA---GAAACAAGG
1535  74_HRV18b|    AAGTTAGTTGTACATTATGAAGAT--------------TATAATGCA---GAAACAAGG
1536  75_HRV18     AAGTTAGTTGTACATTATGAAGAT--------------TATAATGCA---GAAACAAGG
```

FIG. D5 CONT'D 01.trace                                                                                                       9/20/2007 4:58 PM

```
1537  76_HRV55      GAGTTAGTTGTTCATTATGAAGAA---------------TATAACAAA---GAGGGAAAA
1538  77_HRV55b|    GAGTTAGTTGTTCATTATGAAGAA---------------TATAACAAA---GAGGGAAAA
1539  78_HRV55a|    GAGTTAGTTGTTCATTATGAAGAA---------------TATAACAAA---GAGGGAAAA
1540  79_HRV57      GAGCTTAAGGTAAAATATGAAAAT---------------TACAACACA---GAG------
1541  80_HRV57a|    GAGCTTAAGGTAAAATATGAAAAT---------------TACAACACA---GAG------
1542  81_HRV57b|    GAGCTTAAGGTAAAATATGAAAAT---------------TACAACACA---GAG------
1543  82_HRV21      AAATTAGTAGTTAACTATGATAAT---------------TACAATACT---GGAGAAAAT
1544  83_HRVHan     AAATTAATAGTTAACTATGACAAC---------------TACAATACT---GGAGAAAAT
1545  84_HRV43      ACACTTGAAGTAAATTATGATGAT---------------TATAATGGG---ACAGGCATA
1546  85_HRV43b|    ACACTTGAAGTAAATTATGATGAT---------------TATAATGGG---ACAGGCATA
1547  86_HRV43a|    ACACTTGAAGTAAATTATGATGAT---------------TATAATGGG---ACAGGCATA
1548  87_HRV75      ACACTTGAGATGGATTATACAAAC---------------TATAATGGA---GAAGGCAAA
1549  88_HRV75b|    ACACTTGAGATGGATTATACAAAC---------------TATAATGGA---GAAGGCAAA
1550  89_HRV75a|    ACACTTGAGATGGATTATACAAAC---------------TATAATGGA---GAAGGCAAA
1551  96_HRV9a|d    AAATTGAATATTGATTACAGTGAC---------------TATGATAAG---AGTGTTGAA
1552  97_HRV9b|d    AAATTGAATATTGATTACAGTGAC---------------TATGATAAG---AGTGTTGAA
1553  98_HRV9       AAATTGAATATTGATTACAGTGAC---------------TATGATAAG---AGTGTTGAA
1554  99_HRV32      AAATTAGATATTGATTATACCAAT---------------TACAATAAA---AGTGTTAAG
1555  100_HRV32a    AAATTAGATATTGATTATACCAAT---------------TACAATAAA---AGTGTTAAG
1556  101_HRV32b    AAATTAGATATTGATTATACCAAT---------------TACAATAAA---AGTGTTAAG
1557  102_HRV67     AAATTGAATATTGATTATAATGCA---------------TATGATGAA---AGTAGGGAC
1558  103_HRV67a    AAATTGAATATTGATTATAATGCA---------------TATGATGAA---AGTAGGGAC
1559  104_HRV67b    AAATTGAATATTGATTATAATGCA---------------TATGATGAA---AGTAGGGAC
1560  105_HRV15     GATTTGAAAATACATTATGAAGAT---------------TATAATAAA---GATGGGAAA
1561  106_HRV15a    GATTTGAAAATACATTATGAAGAT---------------TATAATAAA---GATGGGAAA
1562  107_HRV15b    GATTTGAAAATACATTATGAAGAT---------------TATAATAAA---GATGGGAAA
1563  108_HRV74a    CATCTAAAAATTGATTATACAAAC---------------TATAATGTT---AAAGGGAAG
1564  109_HRV74b    CATCTAAAAATTGATTATACAAAC---------------TATAATGTT---AAAGGGAAG
1565  110_HRV74     CATCTAAAAATTGATTATACAAAC---------------TATAATGTT---AAAGGGAAG
1566  111_HRV38a    AATCTTGACATAGATTACATTAAT---------------TACAACTCT---GAAGACAAA
1567  112_HRV38b    AATCTTGACATAGATTACATTAAT---------------TACAACTCT---GAAGACAAA
1568  113_HRV38     AATCTTGACATAGATTACATTAAT---------------TACAACTCT---GAAGACAAA
1569  114_HRV60     AAATTAGAAATTGACTATAGTAAC---------------TACAATGAG---GAGAATAAA
1570  115_HRV60a    AAATTAGAAATTGACTATAGTAAC---------------TACAATGAG---GAGAATAAA
1571  116_HRV60b    AAATTAGAAATTGACTATAGTAAC---------------TACAATGAG---GAGAATAAA
1572  117_HRV64a    GATTTAAAAGTAAATTATACTGGG---------------TATAATGAT---GAAGGTAAC
1573  118_HRV64b    GATTTAAAAGTAAATTATACTGGG---------------TATAATGAT---GAAGGTAAC
1574  119_HRV64     GATTTAAAAGTAAATTATACTGGG---------------TATAATGAT---GAAGGTAAC
1575  120_HRV94a    CATCTAGAGATCAAGTATGATGGT---------------TACAATGAT---GCTGGCAAC
1576  121_HRV94b    CATCTAGAGATCAAGTATGATGGT---------------TACAATGAT---GCTGGCAAC
1577  122_HRV94     CATCTAGAGATCAAGTATGATGGT---------------TACAATGAT---GCTGGCAAC
1578  123_HRV22     CACTTAGAAGTAAAATACACAGGG---------------TATAATGAA---GAGGGTAAT
1579  124_HRV22a    CACTTAGAAGTAAAATACACAGGG---------------TATAATGAA---GAGGGTAAT
1580  125_HRV22b    CACTTAGAAGTAAAATACACAGGG---------------TATAATGAA---GAGGGTAAT
1581  126_HRV82     CACCTAAATGTCAGATACACTG-----------------ATTATAAT---GAAGGTAAT
1582  127_HRV82b    CACCTAAATGTCAGATACACTG-----------------ATTATAAT---GAAGGTAAT
1583  128_HRV82a    CACCTAAATGTCAGATACACTG-----------------ATTATAAT---GAAGGTAAT
1584  129_HRV19     GAGCTCCAATTAGATTATACCAAT---------------TACAATCAA---GAAAATAAT
1585  130_HRV19a    GAGCTCCAATTAGATTATACCAAT---------------TACAATCAA---GAAAATAAT
1586  131_HRV19b    GAGCTCCAATTAGATTATACCAAT---------------TACAATCAA---GAAAATAAT
1587  132_HRV13     ACCATGAACATAGATTATACTAAT---------------TATGATGAT---TCTGTTAAT
1588  133_HRV13a    ACCATGAACATAGATTATACTAAT---------------TATGATGAT---TCTGTTAAT
1589  134_HRV13b    ACCATGAACATAGATTATACTAAT---------------TATGATGAT---TCTGTTAAT
1590  135_HRV41     ACTTTGAATATAGATTATACTGAT---------------TATGATGAT---TCTATCCAG
1591  136_HRV41a    ACTTTGAATATAGATTATACTGAT---------------TATGATGAT---TCTATCCAG
1592  137_HRV41b    ACTTTGAATATAGATTATACTGAT---------------TATGATGAT---TCTATCCAG
1593  138_HRV73     ACTATGAATATAAATTATGAAAAT---------------TATGATGAT---GCTCCTGAA
1594  139_HRV73b    ACTATGAATATAAATTATGAAAAT---------------TATGATGAT---GCTCCTGAA
1595  140_HRV73a    ACTATGAATATAAATTATGAAAAT---------------TATGATGAT---GCTCCTGAA
1596  141_HRV61     ACATTAAATATAAACTATGATAAC---------------TATGATGAT---TCTATTGAA
1597  142_HRV61a    ACATTAAATATAAACTATGATAAC---------------TATGATGAT---TCTATTGAA
1598  143_HRV61b    ACATTAAATATAAACTATGATAAC---------------TATGATGAT---TCTATTGAA
1599  144_HRV96     ACATTAAACATAGATTATGACAAT---------------TATGATGAC---TCCCCTAAG
1600  145_HRV96b    ACATTAAACATAGATTATGACAAT---------------TATGATGAC---TCCCCTAAG
```

FIG. D5 CONT'D 01.trace                                                                9/20/2007 4:58 PM

```
1601  146_HRV96a   ACATTAAACATAGATTATGACAAT---------------TATGATGAC---TCCCCTAAG
1602   90_HRV16a|  GTGTTGGATATTGTGGACAATTAC---------------AATGAT-----------CAA
1603   91_HRV16b|  GTGTTGGATATTGTGGACAATTAC---------------AATGAT-----------CAA
1604   92_1AYM_A   GTGTTGGATATTGTGGACAATTAC---------------AATGAT-----------CAA
1605   93_HRV81a|  ATATTGGACATTAAAGAGGATTAC---------------AATACC-----------CAG
1606   94_HRV81b|  ATATTGGACATTAAAGAGGATTAC---------------AATACC-----------CAG
1607   95_HRV81    ATATTGGACATTAAAGAGGATTAC---------------AATACC-----------CAG
1608  147_HRV2     AAATTAGAGGTTACACTTGCAAAT---------------TATAACA---------AGGAG
1609  148_HRV2a|   AAATTAGAGGTTACACTTGCAAAT---------------TATAACA---------AGGAG
1610  149_HRV2b|   AAATTAGAGGTTACACTTGCAAAT---------------TATAACA---------AGGAG
1611  150_HRV49a   AAACTAGAGGTCACACTTACAAAT---------------TACAATG---------AAAAT
1612  151_HRV49b   AAACTAGAGGTCACACTTACAAAT---------------TACAATG---------AAAAT
1613  152_HRV49    AAACTAGAGGTCACACTTACAAAT---------------TACAATG---------AAAAT
1614  153_HRV23a   AAATTAAAAGTTGAGATCGGAAAC---------------TATGATG---------AAAAC
1615  154_HRV23b   AAATTAAAAGTTGAGATCGGAAAC---------------TATGATG---------AAAAC
1616  155_HRV23    AAATTAAAAGTTGAGATCGGAAAC---------------TATGATG---------AAAAC
1617  156_HRV30a   AAATTAGAACTTGAGCTTGCACAC---------------TATGATA---------AAAAG
1618  157_HRV30b   AAATTAGAACTTGAGCTTGCACAC---------------TATGATA---------AAAAG
1619  158_HRV30    AAATTAGAACTTGAGCTTGCACAC---------------TATGATA---------AAAAG
1620  159_HRV7     AAACTTGACACAA------CACAGGGT---------GACTATGACACAGGCAAAGGTGTT
1621  160_HRV7b|   AAACTTGACACAA------CACAGGGT---------GACTATGACACAGGCAAAGGTGTT
1622  161_HRV7a|   AAACTTGACACAA------CACAGGGT---------GACTATGACACAGGCAAAGGTGTT
1623  162_HRV88    AAACTTGACACAA------ATGAAGGT---------GATTACGACACA---ATAGGTGTT
1624  163_HRV88a   AAACTTGACACAA------ATGAAGGT---------GATTACGACACA---ATAGGTGTT
1625  164_HRV88b   AAACTTGACACAA------ATGAAGGT---------GATTACGACACA---ATAGGTGTT
1626  165_HRV36a   GAATTTAGCACAAGTAGTGATAAAGAT--------GAACATGATGAA---ATTGGCAAG
1627  166_HRV36b   GAATTTAGCACAAGTAGTGATAAAGAT--------GAACATGATGAA---ATTGGCAAG
1628  167_HRV36    GAATTTAGCACAAGTAGTGATAAAGAT--------GAACATGATGAA---ATTGGCAAG
1629  168_HRV89a   GAATTTAATACAAGTAGTGATAAAACT--------GAACATGATAAA---ATTGGTAAA
1630  169_HRV89b   GAATTTAATACAAGTAGTGATAAAACT--------GAACATGATAAA---ATTGGTAAA
1631  170_HRV89    GAATTTAATACAAGTAGTGATAAAACT--------GAACATGATAAA---ATTGGTAAA
1632  171_HRV58    AAATTTAACACAA------ATAAGACT---------AATTATGATGAC---ATAGGTGTA
1633  172_HRV58a   AAATTTAACACAA------ATAAGACT---------AATTATGATGAC---ATAGGTGTA
1634  173_HRV58b   AAATTTAACACAA------ATAAGACT---------AATTATGATGAC---ATAGGTGTA
1635  174_HRV12a   GAATTGGATTTAGACCATGAAGGT---------------TATTCAGCA---GAAGGGAAA
1636  175_HRV12b   GAATTGGATTTAGACCATGAAGGT---------------TATTCAGCA---GAAGGGAAA
1637  176_HRV12    GAATTGGATTTAGACCATGAAGGT---------------TATTCAGCA---GAAGGGAAA
1638  177_HRV78a   AGACTAGAATTGGACCACACTGAT---------------TACAATGCT---GAAGGGAAA
1639  178_HRV78b   AGACTAGAATTGGACCACACTGAT---------------TACAATGCT---GAAGGGAAA
1640  179_HRV78    AGACTAGAATTGGACCACACTGAT---------------TACAATGCT---GAAGGGAAA
1641  180_HRV20    CATACTGACTTAGATCATGAAGCACAA---------CAATATAATGCA---CCCGGAAAA
1642  181_HRV20a   CATACTGACTTAGATCATGAAGCACAA---------CAATATAATGCA---CCCGGAAAA
1643  182_HRV20b   CATACTGACTTAGATCATGAAGCACAA---------CAATATAATGCA---CCCGGAAAA
1644  183_HRV68    CATACTGACTTAGATCACAATGAGGAT---------CAGTACAATGCA---CCTGGAAAA
1645  184_HRV68a   CATACTGACTTAGATCACAATGAGGAT---------CAGTACAATGCA---CCTGGAAAA
1646  185_HRV68b   CATACTGACTTAGATCACAATGAGGAT---------CAGTACAATGCA---CCTGGAAAA
1647  186_HRV28    CATACTGATGTTGTGCATGAAACAGAC---------AAGTACAACCAC---CCAGGGAAG
1648  187_HRV28a   CATACTGATGTTGTGCATGAAACAGAC---------AAGTACAACCAC---CCAGGGAAG
1649  188_HRV28b   CATACTGATGTTGTGCATGAAACAGAC---------AAGTACAACCAC---CCAGGGAAG
1650  189_HRV53a   CATACCAATTTAGACCAT---ACTG-----------GATACAATGAG---CCTGGGAAA
1651  190_HRV53b   CATACCAATTTAGACCAT---ACTG-----------GATACAATGAG---CCTGGGAAA
1652  191_HRV53    CATACCAATTTAGACCAT---ACTG-----------GATACAATGAG---CCTGGGAAA
1653  192_HRV46a   GAGACAGAATTGAATCATGAAGAAGGG---------AAATACAATGCA---GAAGATCAA
1654  193_HRV46b   GAGACAGAATTGAATCATGAAGAAGGG---------AAATACAATGCA---GAAGATCAA
1655  194_HRV46    GAGACAGAATTGAATCATGAAGAAGGG---------AAATACAATGCA---GAAGATCAA
1656  195_HRV80a   GAAACCAAATTAAACCATGAAACAGAC---------ATGTACAATGCT---GATGGTCAG
1657  196_HRV80b   GAAACCAAATTAAACCATGAAACAGAC---------ATGTACAATGCT---GATGGTCAG
1658  197_HRV80    GAAACCAAATTAAACCATGAAACAGAC---------ATGTACAATGCT---GATGGTCAG
1659  198_HRV51    CATACAAACCTTGAGCATGTTGAAGCAGACAGACAAGCCTACAATGCA---AAAGGGAAA
1660  199_HRV51a   CATACAAACCTTGAGCATGTTGAAGCAGACAGACAAGCCTACAATGCA---AAAGGGAAA
1661  200_HRV51b   CATACAAACCTTGAGCATGTTGAAGCAGACAGACAAGCCTACAATGCA---AAAGGGAAA
1662  201_HRV65a   CACACAGATCTTAAACATGACCATGAAGGCCAAAATGTTTACAATGAC---GAAGGCAGA
1663  202_HRV65b   CACACAGATCTTAAACATGACCATGAAGGCCAAAATGTTTACAATGAC---GAAGGCAGA
1664  203_HRV65    CACACAGATCTTAAACATGACCATGAAGGCCAAAATGTTTACAATGAC---GAAGGCAGA
```

FIG. D5 CONT'D 01.trace                                                          9/20/2007 4:58 PM

```
1665 204_HRV71a   CACACTAAATTAGTACATGGAGAGGAGGG------TGTTTATAATATG---AAAGGTAAC
1666 205_HRV71b   CACACTAAATTAGTACATGGAGAGGAGGG------TGTTTATAATATG---AAAGGTAAC
1667 206_HRV71    CACACTAAATTAGTACATGGAGAGGAGGG------TGTTTATAATATG---AAAGGTAAC
1668 207_HRV8     GCATTAGAACTAGATCATGACAAC--------------TATGATGAA------------
1669 208_HRV95    GCATTAGAACTAGATCATGACAAC--------------TATGATAAA------------
1670 209_HRV45    AGTTTAGACATTAACCATGATGAC--------------TACCAAAAG------------
1671 210_HRV45a   AGTTTAGACATTAACCATGATGAC--------------TACCAAAAG------------
1672 211_HRV45b   AGTTTAGACATTAACCATGATGAC--------------TACCAAAAG------------
1673 212_HRV6     ------------------------------------------------------------
1674 213_HRV6a|   ------------------------------------------------------------
1675 214_HRV6b|   ------------------------------------------------------------
1676 215_HRV37    ------------------------------------------------------------
1677 216_HRV37a   ------------------------------------------------------------
1678 217_HRV37b   ------------------------------------------------------------
1679 218_HRV3     ------------------------------------------------------------
1680 219_HRV3a|   ------------------------------------------------------------
1681 220_HRV3b|   ------------------------------------------------------------
1682 221_HRV14    ------------------------------------------------------------
1683 222_HRV14a   ------------------------------------------------------------
1684 223_HRV14b   ------------------------------------------------------------
1685 224_HRV72    ------------------------------------------------------------
1686 225_HRV72a   ------------------------------------------------------------
1687 226_HRV72b   ------------------------------------------------------------
1688 227_HRV83    ------------------------------------------------------------
1689 228_HRV83a   ------------------------------------------------------------
1690 229_HRV83b   ------------------------------------------------------------
1691 230_HRV92    ------------------------------------------------------------
1692 231_HRV92a   ------------------------------------------------------------
1693 232_HRV92b   ------------------------------------------------------------
1694 233_HRV79    ------------------------------------------------------------
1695 234_HRV79a   ------------------------------------------------------------
1696 235_HRV79b   ------------------------------------------------------------
1697 236_HRV35    ------------------------------------------------------------
1698 237_HRV35a   ------------------------------------------------------------
1699 238_HRV35b   ------------------------------------------------------------
1700 239_1HRV86   ------------------------------------------------------------
1701 240_1HRV86   ------------------------------------------------------------
1702 241_1HRV86   ------------------------------------------------------------
1703 242_HRV70    ------------------------------------------------------------
1704 243_HRV70a   ------------------------------------------------------------
1705 244_HRV70b   ------------------------------------------------------------
1706 245_HRV91    ------------------------------------------------------------
1707 246_HRV91a   ------------------------------------------------------------
1708 247_HRV91b   ------------------------------------------------------------
1709 248_HRV17    ------------------------------------------------------------
1710 249_HRV17a   ------------------------------------------------------------
1711 250_HRV17b   ------------------------------------------------------------
1712 251_HRV69    ------------------------------------------------------------
1713 252_HRV69a   ------------------------------------------------------------
1714 253_HRV69b   ------------------------------------------------------------
1715 254_HRV48    ------------------------------------------------------------
1716 255_HRV48a   ------------------------------------------------------------
1717 256_HRV48b   ------------------------------------------------------------
1718 257_HRV52    ------------------------------------------------------------
1719 258_HRV52a   ------------------------------------------------------------
1720 259_HRV52b   ------------------------------------------------------------
1721 260_HRV4     ------------------------------------------------------------
1722 261_HRV4a|   ------------------------------------------------------------
1723 262_HRV4b|   ------------------------------------------------------------
1724 263_HRV99    ------------------------------------------------------------
1725 264_HRV99a   ------------------------------------------------------------
1726 265_HRV99b   ------------------------------------------------------------
1727 266_HRV5     ------------------------------------------------------------
1728 267_HRV5a|   ------------------------------------------------------------
```

FIG. D5 CONT'D

01.trace                                                                    9/20/2007 4:58 PM

```
1729 268_HRV5b|     ----------------------------------------------------------------
1730 269_HRV42      ----------------------------------------------------------------
1731 270_HRV42a     ----------------------------------------------------------------
1732 271_HRV42b     ----------------------------------------------------------------
1733 272_HRV26      ----------------------------------------------------------------
1734 273_HRV26a     ----------------------------------------------------------------
1735 274_HRV26b     ----------------------------------------------------------------
1736 275_HRV27      ----------------------------------------------------------------
1737 276_HRV27a     ----------------------------------------------------------------
1738 277_HRV27b     ----------------------------------------------------------------
1739 278_HRV93      ----------------------------------------------------------------
1740 279_HRV93a     ----------------------------------------------------------------
1741 280_HRV93b     ----------------------------------------------------------------
1742 281_HRV97      ----------------------------------------------------------------
1743 282_HRV97a     ----------------------------------------------------------------
1744 283_HRV97b     ----------------------------------------------------------------
1745 284_HRV84      ----------------------------------------------------------------
1746 285_HRV84a     ----------------------------------------------------------------
1747 286_HRV84b     ----------------------------------------------------------------
1748 287_HRV87      ----------------------------------------------------------------
1749 288_HRV87a     ----------------------------------------------------------------
1750 289_HRV87b     ----------------------------------------------------------------
1751 GROUP_1        ----------------------------------------------------------------
1752
1753  1_HRV1A1|d    AATTTCACAAAATGGAAAATCACACTACAGGAAATGGCACAGATTAGGAGAAAATTTGAA
1754  2_HRV1A2|d    AATTTCACAAAATGGAAAATCACACTACAGGAAATGGCACAGATTAGGAGAAAATTTGAA
1755  3_HRV1A|cD    AATTTCACAAAATGGAAAATCACACTACAGGAAATGGCACAGATTAGGAGAAAATTTGAA
1756  4_HRV1B1|d    AACTTTACAACATGGAAAATCACACTGCAGGAGATGGCACAAATTAGAAGAAAATTCGAA
1757  5_HRV1B2|d    AACTTTACAACATGGAAAATCACACTGCAGGAGATGGCACAAATTAGAAGAAAATTCGAA
1758  6_HRV1B       AACTTTACAACATGGAAAATCACACTGCAGGAGATGGCACAAATTAGAAGAAAATTCGAA
1759  7_HRV40a|d    CACTTTGATAAGTGGCAGATAACCATACAAGAGATGTCACAAATTAGGAGAAAATTTGAA
1760  8_HRV40b|d    CACTTTGATAAGTGGCAGATAACCATACAAGAGATGTCACAAATTAGGAGAAAATTTGAA
1761  9_HRV40       CACTTTGATAAGTGGCAGATAACCATACAAGAGATGTCACAAATTAGGAGAAAATTTGAA
1762 10_HRV85       CACTTTGATCAGTGGCAGATAACTATACAGGAAATGGCACAAATTAGAAGGAAGTTTGAG
1763 11_HRV85a|     CACTTTGATCAGTGGCAGATAACTATACAGGAAATGGCACAAATTAGAAGGAAGTTTGAG
1764 12_HRV85b|     CACTTTGATCAGTGGCAGATAACTATACAGGAAATGGCACAAATTAGAAGGAAGTTTGAG
1765 13_HRV56a|     CATTATAATAAATGGCAAATAACCTTACAAGAAATGGCTCAAGTTAGGCGTAAATTTGAA
1766 14_HRV56b|     CATTATAATAAATGGCAAATAACCTTACAAGAAATGGCTCAAGTTAGGCGTAAATTTGAA
1767 15_HRV56       CATTATAATAAATGGCAAATAACCTTACAAGAAATGGCTCAAGTTAGGCGTAAATTTGAA
1768 16_HRV54       CATTTTAAGAAATGGGATATAACATTACAAGAGATGGCACAAATACGAAGGAAATTTGAA
1769 17_HRV98       CATTTTAGACAATGGGATATAACATTACAAGAAATGGCACAAATTCGAAGAAAATTTGAA
1770 18_HRV59a|     CACTTTCTTAAATGGCCTATAACATTACAAGAGATGGCACAAATTAGGAGAAAATTTGAA
1771 19_HRV59b|     CACTTTCTTAAATGGCCTATAACATTACAAGAGATGGCACAAATTAGGAGAAAATTTGAA
1772 20_HRV59       CACTTTCTTAAATGGCCTATAACATTACAAGAGATGGCACAAATTAGGAGAAAATTTGAA
1773 21_HRV63       CATTTTAATAAATGGCAAATAACATTACAAGAGATGGCACAAATTAGAAGGAAATTTGAA
1774 22_HRV63b|     CATTTTAAATAAATGGCAAATAACATTACAAGAGATGGCACAAATTAGAAGGAAATTTGAA
1775 23_HRV63a|     CATTTTAATAAATGGCAAATAACATTACAAGAGATGGCACAAATTAGAAGGAAATTTGAA
1776 24_HRV39       AATTTTGTGGATTGGAAAATTACTTTGCAGGAGATGGCACAGGTTAGAAGGAAATTTGAA
1777 25_HRV39a|     AATTTTGTGGATTGGAAAATTACTTTGCAGGAGATGGCACAGGTTAGAAGGAAATTTGAA
1778 26_HRV39b|     AATTTTGTGGATTGGAAAATTACTTTGCAGGAGATGGCACAGGTTAGAAGGAAATTTGAA
1779 27_HRV10a|     ACTTTTGACACATGGCAAATAACTCTACAAGAAATGGCCCAAATTAGAAGGAAATTTGAA
1780 28_HRV10b|     ACTTTTGACACATGGCAAATAACTCTACAAGAAATGGCCCAAATTAGAAGGAAATTTGAA
1781 29_HRV10       ACTTTTGACACATGGCAAATAACTCTACAAGAAATGGCCCAAATTAGAAGGAAATTTGAA
1782 30_HRV100a     ACTTTTGACAAATGGCAAATAACCCTACAGGAAATGGCCCAAATTAGAAGGAAATTTGAA
1783 31_HRV100b     ACTTTGACAAATGGCAAATAACCCTACAGGAAATGGCCCAAATTAGAAGGAAATTTGAA
1784 32_HRV100      ACTTTTGACAAATGGCAAATAACCCTACAGGAAATGGCCCAAATTAGAAGGAAATTTGAA
1785 33_HRV66       AAATTTAGAACATGGCAAATTACATTGCAAGAAATGGCTCAAATCAGACGCAAATTTGAG
1786 34_HRV66b|     AAATTTAGAACATGGCAAATTACATTGCAAGAAATGGCTCAAATCAGACGCAAATTTGAG
1787 35_HRV66a|     AAATTTAGAACATGGCAAATTACATTGCAAGAAATGGCTCAAATCAGACGCAAATTTGAG
1788 36_HRV77a|     AAATTTAGAAAATGGCAAATTACACTACAAGAAATGGCTCAAATTAGGCGCAAATTTGAA
1789 37_HRV77b|     AAATTTAGAAAATGGCAAATTACACTACAAGAAATGGCTCAAATTAGGCGCAAATTTGAA
1790 38_HRV77       AAATTTAGAAAATGGCAAATTACACTACAAGAAATGGCTCAAATTAGGCGCAAATTTGAA
1791 39_HRV62a      AGATTCAAAACATGGAATATTAACTTACAAGAGATGGCTCAAATCAGGAGAAAGTTTGAA
1792 40_HRV62b      AGATTCAAAACATGGAATATTAACTTACAAGAGATGGCTCAAATCAGGAGAAAGTTTGAA
```

01.trace                                                                9/20/2007 4:58 PM

```
1793  41_HRV25    AGATTTAAAATATGGAATATCAATTTACAAGAAATGGCTCAAATTAGGAGAAAGTTTGAG
1794  42_HRV29a   AAGTTCGATAAATGGAATGTTAACTTACAAGAAATGGCTCAAATTAGGCGCAAATTTGAA
1795  43_HRV29b   AAGTTCGATAAATGGAATGTTAACTTACAAGAAATGGCTCAAATTAGGCGCAAATTTGAA
1796  44_HRV44a   AAGTTTGATAAATGGAATATCAACTTACAAGAAATGGCTCAAATTAGACGCAAATTTGAA
1797  45_HRV44b   AAGTTTGATAAATGGAATATCAACTTACAAGAAATGGCTCAAATTAGACGCAAATTTGAA
1798  46_HRV31    AAATATAAAGTATGGCACATTAATTTACAAGAGATGGCCCAGATTAGGCGAAAATTTGAA
1799  47_HRV31a|  AAATATAAAGTATGGCACATTAATTTACAAGAGATGGCCCAGATTAGGCGAAAATTTGAA
1800  48_HRV31b|  AAATATAAAGTATGGCACATTAATTTACAAGAGATGGCCCAGATTAGGCGAAAATTTGAA
1801  49_HRV47    AAATTTAAAGTATGGCACATTAATTTACAAGAAATGGCCCAGATCAGGCGTAAATATGAA
1802  50_HRV47a|  AAATTTAAAGTATGGCACATTAATTTACAAGAAATGGCCCAGATCAGGCGTAAATATGAA
1803  51_HRV47b|  AAATTTAAAGTATGGCACATTAATTTACAAGAAATGGCCCAGATCAGGCGTAAATATGAA
1804  52_HRV11    AACTTTAACACATGGAAAATAAACTTGCAAGAGATGGCACAAATTAGAAGGAAATTTGAA
1805  53_HRV11b|  AACTTTAACACATGGAAAATAAACTTGCAAGAGATGGCACAAATTAGAAGGAAATTTGAA
1806  54_HRV11a|  AACTTTAACACATGGAAAATAAACTTGCAAGAGATGGCACAAATTAGAAGGAAATTTGAA
1807  55_HRV76    AACTTTAAGACATGGAAAATAAACCTACAAGAAATGGCACAAGTTAGAAGAAAATTTGAG
1808  56_HRV76b|  AACTTTAAGACATGGAAAATAAACCTACAAGAAATGGCACAAGTTAGAAGAAAATTTGAG
1809  57_HRV76a|  AACTTTAAGACATGGAAAATAAACCTACAAGAAATGGCACAAGTTAGAAGAAAATTTGAG
1810  58_HRV33    AATTTTATGACATGGAAAATAAATCTACAAGAGATGGCACAGATTAGGAGGAAATTTGAA
1811  59_HRV33b|  AATTTTATGACATGGAAAATAAATCTACAAGAGATGGCACAGATTAGGAGGAAATTTGAA
1812  60_HRV33a|  AATTTTATGACATGGAAAATAAATCTACAAGAGATGGCACAGATTAGGAGGAAATTTGAA
1813  61_HRV24a|  AATTTTTTCAAATGGCAAATAAATCTACAAGAAATGGCCCAAGTCAGAAGAAAATTTGAA
1814  62_HRV24b|  AATTTTTTCAAATGGCAAATAAATCTACAAGAAATGGCCCAAGTCAGAAGAAAATTTGAA
1815  63_HRV24    AATTTTTTCAAATGGCAAATAAATCTACAAGAAATGGCCCAAGTCAGAAGAAAATTTGAA
1816  64_HRV90    AACTTCCATAAATGGCAAATTAACCTGCAAGAGATGGCACAGATTAGAAGAAAATTTGAA
1817  65_HRV90a|  AACTTCCATAAATGGCAAATTAACCTGCAAGAGATGGCACAGATTAGAAGAAAATTTGAA
1818  66_HRV90b|  AACTTCCATAAATGGCAAATTAACCTGCAAGAGATGGCACAGATTAGAAGAAAATTTGAA
1819  67_HRV34    AACTTTATGACATGGCAAATTAATTTACAGGAAATGGCACAGATTAGAAGGAAATTTGAA
1820  68_HRV34b|  AACTTTATGACATGGCAAATTAATTTACAGGAAATGGCACAGATTAGAAGGAAATTTGAA
1821  69_HRV34a|  AACTTTATGACATGGCAAATTAATTTACAGGAAATGGCACAGATTAGAAGGAAATTTGAA
1822  70_HRV50a|  AACTTCAAGAAATGGCAAATCAACCTACAAGAAATGGCACAGATCAGAAGGAAATTTGAG
1823  71_HRV50b|  AACTTCAAGAAATGGCAAATCAACCTACAAGAAATGGCACAGATCAGAAGGAAATTTGAG
1824  72_HRV50    AACTTCAAGAAATGGCAAATCAACCTACAAGAAATGGCACAGATCAGAAGGAAATTTGAG
1825  73_HRV18a|  AACTTTGTAAAATGGCAAATAAATCTACAGGAAATGGCCCAGATTAGGAGAAAATTTGAG
1826  74_HRV18b|  AACTTTGTAAAATGGCAAATAAATCTACAGGAAATGGCCCAGATTAGGAGAAAATTTGAG
1827  75_HRV18    AACTTTGTAAAATGGCAAATAAATCTACAGGAAATGGCCCAGATTAGGAGAAAATTTGAG
1828  76_HRV55    AATTTTACTAAGTGGCAAGTAAACATCCAAGAGATGGCTCAGATTAGAAGAAAATTTGAA
1829  77_HRV55b|  AATTTTACTAAGTGGCAAGTAAACATCCAAGAGATGGCTCAGATTAGAAGAAAATTTGAA
1830  78_HRV55a|  AATTTTACTAAGTGGCAAGTAAACATCCAAGAGATGGCTCAGATTAGAAGAAAATTTGAA
1831  79_HRV57    AATTTCACTAAATGGGAAATAAATCTACAAGAAATGGCACAAATCAGAAGAAAATTTGAA
1832  80_HRV57a|  AATTTCACTAAATGGGAAATAAATCTACAAGAAATGGCACAAATCAGAAGAAAATTTGAA
1833  81_HRV57b|  AATTTCACTAAATGGGAAATAAATCTACAAGAAATGGCACAAATCAGAAGAAAATTTGAA
1834  82_HRV21    AACATTAGTACATGGCAAATAAATATTAAAGAGATGGCACAAATTAGGAGAAAATTTGAA
1835  83_HRVHan   AACATTAATACATGGCAAATAAATATTAAAGAGATGGCACAAATTAGGAGAAAATTTGAA
1836  84_HRV43    AATTTTACCCAATGGCCAATCAACTTGCAAGAAATGGCACAAATTAGAAGAAAAGTATGAA
1837  85_HRV43b|  AATTTTACCCAATGGCCAATCAACTTGCAAGAAATGGCACAAATTAGAAGAAAAGTATGAA
1838  86_HRV43a|  AATTTTACCCAATGGCCAATCAACTTGCAAGAAATGGCACAAATTAGAAGAAAAGTATGAA
1839  87_HRV75    AACTTCACTCAGTGGCCAATCAATCTACAGGAAATGGCTCAAATTAGAAGGAAATATGAA
1840  88_HRV75b|  AACTTCACTCAGTGGCCAATCAATCTACAGGAAATGGCTCAAATTAGAAGGAAATATGAA
1841  89_HRV75a|  AACTTCACTCAGTGGCCAATCAATCTACAGGAAATGGCTCAAATTAGAAGGAAATATGAA
1842  96_HRV9a|d  AATTTCACAATCTGGAAAATAAATATAAAGGAAATGGCCCAGATCAGGAGGAAATTTGAA
1843  97_HRV9b|d  AATTTCACAATCTGGAAAATAAATATAAAGGAAATGGCCCAGATCAGGAGGAAATTTGAA
1844  98_HRV9     AATTTCACAATCTGGAAAATAAATATAAAGGAAATGGCCCAGATCAGGAGGAAATTTGAA
1845  99_HRV32    AATTTCACAATTTGGAAGATAAATATAAAAGAAATGGCCCAGATCAGGAGAAAATTTGAG
1846  100_HRV32a  AATTTCACAATTTGGAAGATAAATATAAAAGAAATGGCCCAGATTAGGAGAAAATTTGAG
1847  101_HRV32b  AATTTCACAATTTGGAAGATAAATATAAAAGAAATGGCCCAGATTAGGAGAAAATTTGAG
1848  102_HRV67   AATTTCACAATTTGGAAAATAAATATAAAAGAAATGGCCCAGATTAGGAGGAAATTTGAA
1849  103_HRV67a  AATTTCACAATTTGGAAAATAAATATAAAAGAAATGGCCCAGATTAGGAGGAAATTTGAA
1850  104_HRV67b  AATTTCACAATTTGGAAAATAAATATAAAAGAAATGGCCCAGATTAGGAGGAAATTTGAA
1851  105_HRV15   AACTTTACTAAATGGCAAATTAATCTCAAAGAAATGGCCCAGATTAGAAGAAAATTTGAG
1852  106_HRV15a  AACTTTACTAAATGGCAAATTAATCTCAAAGAAATGGCCCAGATTAGAAGAAAATTTGAG
1853  107_HRV15b  AACTTTACTAAATGGCAAATTAATCTCAAAGAAATGGCCCAGATTAGAAGAAAATTTGAG
1854  108_HRV74a  AATTTTACTAAATGGCAAATAAATCTTAAAGAAATGGCACAGATTAGGAGAAAATTTGAG
1855  109_HRV74b  AATTTTACTAAATGGCAAATAAATCTTAAAGAAATGGCACAGATTAGGAGAAAATTTGAG
1856  110_HRV74   AATTTTACTAAATGGCAAATAAATCTTAAAGAAATGGCACAGATTAGGAGAAAATTTGAG
```

FIG. D5 CONT'D

01.trace                                                                                      9/20/2007 4:58 PM

```
1857 111_HRV38a    AACTTTACAACATGGCAAATCAATCTCAAAGAAATGGCTCAAATCAGAAGAAAGTTTGAA
1858 112_HRV38b    AACTTTACAACATGGCAAATCAATCTCAAAGAAATGGCTCAAATCAGAAGAAAGTTTGAA
1859 113_HRV38     AACTTTACAACATGGCAAATCAATCTCAAAGAAATGGCTCAAATCAGAAGAAAGTTTGAA
1860 114_HRV60     AATTTCACAACTTGGCAAATTAACCTAAAGGAAATGGCACAAATAAGAAGAAAGTTTGAA
1861 115_HRV60a    AATTTCACAACTTGGCAAATTAACCTAAAGGAAATGGCACAAATAAGAAGAAAGTTTGAA
1862 116_HRV60b    AATTTCACAACTTGGCAAATTAACCTAAAGGAAATGGCACAAATAAGAAGAAAGTTTGAA
1863 117_HRV64a    AATTTTAACAAATGGCAGATCACCTTGAAAGAAATGGCTCAGATAAGAAGGAAGTATGAA
1864 118_HRV64b    AATTTTAACAAATGGCAGATCACCTTGAAAGAAATGGCTCAGATAAGAAGGAAGTATGAA
1865 119_HRV64     AATTTTAACAAATGGCAGATCACCTTGAAAGAAATGGCTCAGATAAGAAGGAAGTATGAA
1866 120_HRV94a    AATTTCCAATCATGGCAAATTACCCTAAAAGAAATGGCACAAATAAGAAGGAAATTTGAA
1867 121_HRV94b    AATTTCCAATCATGGCAAATTACCCTAAAAGAAATGGCACAAATAAGAAGGAAATTTGAA
1868 122_HRV94     AATTTCCAATCATGGCAAATTACCCTAAAAGAAATGGCACAAATAAGAAGGAAATTTGAA
1869 123_HRV22     AACTTTAACATATGGCAAATTAACCTTAAAGAGATGGCTCAGATAAGAAGGAAGTTTGAG
1870 124_HRV22a    AACTTTAACATATGGCAAATTAACCTTAAAGAGATGGCTCAGATAAGAAGGAAGTTTGAG
1871 125_HRV22b    AACTTTAACATATGGCAAATTAACCTTAAAGAGATGGCTCAGATAAGAAGGAAGTTTGAG
1872 126_HRV82     AACTTTAGATCATGGCAAATAAGCATAAAGGAAATGGCACAAATTAGAAGGAAGTTTGAA
1873 127_HRV82b    AACTTTAGATCATGGCAAATAAGCATAAAGGAAATGGCACAAATTAGAAGGAAGTTTGAA
1874 128_HRV82a    AACTTTAGATCATGGCAAATAAGCATAAAGGAAATGGCACAAATTAGAAGGAAGTTTGAA
1875 129_HRV19     AATTTCAAAACTTGGCAAATAAACTTGAAAGAAATGGCACAGATTAGAAGAAAATTTGAA
1876 130_HRV19a    AATTTCAAAACTTGGCAAATAAACTTGAAAGAAATGGCACAGATTAGAAGAAAATTTGAA
1877 131_HRV19b    AATTTCAAAACTTGGCAAATAAACTTGAAAGAAATGGCACAGATTAGAAGAAAATTTGAA
1878 132_HRV13     AATTTTGTGAAATGGAAAATAAGTTTGCAAGAAATGGCCCAAGTGCGCAGAAAATTTGAG
1879 133_HRV13a    AATTTTGTGAAATGGAAAATAAGTTTGCAAGAAATGGCCCAAGTGCGCAGAAAATTTGAG
1880 134_HRV13b    AATTTTGTGAAATGGAAAATAAGTTTGCAAGAAATGGCCCAAGTGCGCAGAAAATTTGAG
1881 135_HRV41     AACTTCAAGAAGTGGAAAATTAGCTTACAGGAGATGGCCCAAGTACGTAGAAAGTTTGAG
1882 136_HRV41a    AACTTCAAGAAGTGGAAAATTAGCTTACAGGAGATGGCCCAAGTACGTAGAAAGTTTGAG
1883 137_HRV41b    AACTTCAAGAAGTGGAAAATTAGCTTACAGGAGATGGCCCAAGTACGTAGAAAGTTTGAG
1884 138_HRV73     AATTTTACCAAATGGAAAATAAGTTTACAAGAGATGGCTCAAATACGTAGGAAATTTGAA
1885 139_HRV73b    AATTTTACCAAATGGAAAATAAGTTTACAAGAGATGGCTCAAATACGTAGGAAATTTGAA
1886 140_HRV73a    AATTTTACCAAATGGAAAATAAGTTTACAAGAGATGGCTCAAATACGTAGGAAATTTGAA
1887 141_HRV61     AACTTCAAGGTGTGGAAAATAAACCTGCAAGAGATGGCACAAATACGTAGAAAATTTGAG
1888 142_HRV61a    AACTTCAAGGTGTGGAAAATAAACCTGCAAGAGATGGCACAAATACGTAGAAAATTTGAG
1889 143_HRV61b    AACTTCAAGGTGTGGAAAATAAACCTGCAAGAGATGGCACAAATACGTAGAAAATTTGAG
1890 144_HRV96     AATTTTAAGGTGTGGAAAATAAATCTACAAGAAATGGCTCAAATTCGCAGGAAGTTTGAA
1891 145_HRV96b    AATTTTAAGGTGTGGAAAATAAATCTACAAGAAATGGCTCAAATTCGCAGGAAGTTTGAA
1892 146_HRV96a    AATTTTAAGGTGTGGAAAATAAATCTACAAGAAATGGCTCAAATTCGCAGGAAGTTTGAA
1893  90_HRV16a|   AGTTTCACTAAATGGAAGATAAACCTGCAAGAAATGGCACAAATTAGAAGAAAATTTGAA
1894  91_HRV16b|   AGTTTCACTAAATGGAAGATAAACCTGCAAGAAATGGCACAAATTAGAAGAAAATTTGAA
1895  92_1AYM_A    AGTTTCACTAAATGGAAGATAAACCTGCAAGAAATGGCACAAATTAGAAGAAAATTTGAA
1896  93_HRV81a|   AGCTTTACTAAATGGAAAATTAACTTACAAGAGATGGCACAGATTAGGAGAAAGTTTGAA
1897  94_HRV81b|   AGCTTTACTAAATGGAAAATTAACTTACAAGAGATGGCACAGATTAGGAGAAAGTTTGAA
1898  95_HRV81     AGCTTTACTAAATGGAAAATTAACTTACAAGAGATGGCACAGATTAGGAGAAAGTTTGAA
1899 147_HRV2      AATTTTACAGTGTGGGCTATTAATATACAAGAAATGGCTCAAATTAGAAGGAAATTTGAA
1900 148_HRV2a|    AATTTTACAGTGTGGGCTATTAATATACAAGAAATGGCTCAAATTAGAAGGAAATTTGAA
1901 149_HRV2b|    AATTTTACAGTGTGGGCTATTAATATACAAGAAATGGCTCAAATTAGAAGGAAATTTGAA
1902 150_HRV49a    AATTTCAAAGTATGGAACATCAATTTGCAAGAAATGGCCCAGATCAGAAGAAAATTTGAA
1903 151_HRV49b    AATTTCAAAGTATGGAACATCAATTTGCAAGAAATGGCCCAGATCAGAAGAAAATTTGAA
1904 152_HRV49     AATTTCAAAGTATGGAACATCAATTTGCAAGAAATGGCCCAGATCAGAAGAAAATTTGAA
1905 153_HRV23a    AATTTTAATACTTGGAATATTAATTTACAGGAAATGGCCCAAATCAGAAGAAAGTTTGAA
1906 154_HRV23b    AATTTTAATACTTGGAATATTAATTTACAGGAAATGGCCCAAATCAGAAGAAAGTTTGAA
1907 155_HRV23     AATTTTAATACTTGGAATATTAATTTACAGGAAATGGCCCAAATCAGAAGAAAGTTTGAA
1908 156_HRV30a    AACTTTACCACATGGAATATTAATCTTCAAGAAATGGCCCAAATTAGAAGAAAATTTGAG
1909 157_HRV30b    AACTTTACCACATGGAATATTAATCTTCAAGAAATGGCCCAAATTAGAAGAAAATTTGAG
1910 158_HRV30     AACTTTACCACATGGAATATTAATCTTCAAGAAATGGCCCAAATTAGAAGAAAATTTGAG
1911 159_HRV7      GGTTTCACTACATGGAAAATCAGCTTACAAGAAATGGCACAAATCAGAAGAAAGTTTGAA
1912 160_HRV7b|    GGTTTCACTACATGGAAAATCAGCTTACAAGAAATGGCACAAATCAGAAGAAAGTTTGAA
1913 161_HRV7a|    GGTTTCACTACATGGAAAATCAGCTTACAAGAAATGGCACAAATCAGAAGAAAGTTTGAA
1914 162_HRV88     GGATTTGTAACATGGAAGATTAGCTTGCAAGAAATGGCACAAATCAGGAGAAAATTTGAA
1915 163_HRV88a    GGATTTGTAACATGGAAGATTAGCTTGCAAGAAATGGCACAAATCAGGAGAAAATTTGAA
1916 164_HRV88b    GGATTTGTAACATGGAAGATTAGCTTGCAAGAAATGGCACAAATCAGGAGAAAATTTGAA
1917 165_HRV36a    GGATTCAAAACATGGAAGATTAGTCTTCAAGAAATGGCACAAATTAGAAGGAAATATGAA
1918 166_HRV36b    GGATTCAAAACATGGAAGATTAGTCTTCAAGAAATGGCACAAATTAGAAGGAAATATGAA
1919 167_HRV36     GGATTCAAAACATGGAAGATTAGTCTTCAAGAAATGGCACAAATTAGAAGGAAATATGAA
1920 168_HRV89a    GGATTCAAAACATGGAAGGTTAGTCTTCAAGAAATGGCACAAATCAGAAGAAAATATGAA
```

FIG. D5 CONT'D

01.trace                                                              9/20/2007 4:58 PM

| | | |
|---|---|---|
| 1921 | 169_HRV89b | GGATTCAAAACATGGAAGGTTAGTCTTCAAGAAATGGCACAAATCAGAAGAAAATATGAA |
| 1922 | 170_HRV89 | GGATTCAAAACATGGAAGGTTAGTCTTCAAGAAATGGCACAAATCAGAAGAAAATATGAA |
| 1923 | 171_HRV58 | GGATACAAAACATGGAAAATTAGCCTTCAAGAGATGGCACAAATTAGAAGGAAATTTGAG |
| 1924 | 172_HRV58a | GGATACAAAACATGGAAAATTAGCCTTCAAGAGATGGCACAAATTAGAAGGAAATTTGAG |
| 1925 | 173_HRV58b | GGATACAAAACATGGAAAATTAGCCTTCAAGAGATGGCACAAATTAGAAGGAAATTTGAG |
| 1926 | 174_HRV12a | AACTTTAAAACATGGAAGATAAATCTTAAGGAAATGGCCCAGATTAGAAGGAAAAATGAG |
| 1927 | 175_HRV12b | AACTTTAAAACATGGAAGATAAATCTTAAGGAAATGGCCCAGATTAGAAGGAAAAATGAG |
| 1928 | 176_HRV12 | AACTTTAAAACATGGAAGATAAATCTTAAGGAAATGGCCCAGATTAGAAGGAAAAATGAG |
| 1929 | 177_HRV78a | AATTTTACAACGTGGAAAATCAACTTACAGGAGATGGCCCAGATTAGAAGAAAGAATGAG |
| 1930 | 178_HRV78b | AATTTTACAACGTGGAAAATCAACTTACAGGAGATGGCCCAGATTAGAAGAAAGAATGAG |
| 1931 | 179_HRV78 | AATTTTACAACGTGGAAAATCAACTTACAGGAGATGGCCCAGATTAGAAGAAAGAATGAG |
| 1932 | 180_HRV20 | AATTTCTCTCAGTGGAAGATCACAATCAAGGAAATGGCTCAAATCAGAAGAAAATGTGAG |
| 1933 | 181_HRV20a | AATTTCTCTCAGTGGAAGATCACAATCAAGGAAATGGCTCAAATCAGAAGAAAATGTGAG |
| 1934 | 182_HRV20b | AATTTCTCTCAGTGGAAGATCACAATCAAGGAAATGGCTCAAATCAGAAGAAAATGTGAG |
| 1935 | 183_HRV68 | AACTTCTCCCAATGGAAAATTACAATTAAGGAAATGGCTCAAATTAGAAGAAAGTGTGAA |
| 1936 | 184_HRV68a | AACTTCTCCCAATGGAAAATTACAATTAAGGAAATGGCTCAAATTAGAAGAAAGTGTGAA |
| 1937 | 185_HRV68b | AACTTCTCCCAATGGAAAATTACAATTAAGGAAATGGCTCAAATTAGAAGAAAGTGTGAA |
| 1938 | 186_HRV28 | AATTTTAGTAAATGGAATATCACTCTCAAAGAAATGGCCCAAATCAGAAGAAAGTGTGAA |
| 1939 | 187_HRV28a | AATTTTAGTAAATGGAATATCACTCTCAAAGAAATGGCCCAAATCAGAAGAAAGTGTGAA |
| 1940 | 188_HRV28b | AATTTTAGTAAATGGAATATCACTCTCAAAGAAATGGCCCAAATCAGAAGAAAGTGTGAA |
| 1941 | 189_HRV53a | AACCACTCAGAATGGAAGATTACACTCAAAGAAATGGCCCAGATTAGAAGGAAATGTGAG |
| 1942 | 190_HRV53b | AACCACTCAGAATGGAAGATTACACTCAAAGAAATGGCCCAGATTAGAAGGAAATGTGAG |
| 1943 | 191_HRV53 | AACCACTCAGAATGGAAGATTACACTCAAAGAAATGGCCCAGATTAGAAGGAAATGTGAG |
| 1944 | 192_HRV46a | AACTTCTCAAAATGGAAAATAACACTGTTGGAAATGGCACAAATCAGAAGAAAGTGTGAA |
| 1945 | 193_HRV46b | AACTTCTCAAAATGGAAAATAACACTGTTGGAAATGGCACAAATCAGAAGAAAGTGTGAA |
| 1946 | 194_HRV46 | AACTTCTCAAAATGGAAAATAACACTGTTGGAAATGGCACAAATCAGAAGAAAGTGTGAA |
| 1947 | 195_HRV80a | AATTTTTCAAAGTGGAAAATAACATTAATGGAAATGGCACAAATTAGAAGAAAGTGTGAG |
| 1948 | 196_HRV80b | AATTTTTCAAAGTGGAAAATAACATTAATGGAAATGGCACAAATTAGAAGAAAGTGTGAG |
| 1949 | 197_HRV80 | AATTTTTCAAAGTGGAAAATAACATTAATGGAAATGGCACAAATTAGAAGAAAGTGTGAG |
| 1950 | 198_HRV51 | AATTTCTCTACATGGAAAATTACACTCAAAGAAATGGCTCAAATTAGAAGAAAGTGTGAA |
| 1951 | 199_HRV51a | AATTTCTCTACATGGAAAATTACACTCAAAGAAATGGCTCAAATTAGAAGAAAGTGTGAA |
| 1952 | 200_HRV51b | AATTTCTCTACATGGAAAATTACACTCAAAGAAATGGCTCAAATTAGAAGAAAGTGTGAA |
| 1953 | 201_HRV65a | AATTTCTCTGCTTGGGAAATTACACTCAAGGAAATGGCTCAAATTAGGAGAAAGTGTGAA |
| 1954 | 202_HRV65b | AATTTCTCTGCTTGGGAAATTACACTCAAGGAAATGGCTCAAATTAGGAGAAAGTGTGAA |
| 1955 | 203_HRV65 | AATTTCTCTGCTTGGGAAATTACACTCAAGGAAATGGCTCAAATTAGGAGAAAGTGTGAA |
| 1956 | 204_HRV71a | AATCTCTCAAAGTGGCAGATTACACTCAAAGAAATGGCTCAGATCAGGAGGAAATGTGAA |
| 1957 | 205_HRV71b | AATCTCTCAAAGTGGCAGATTACACTCAAAGAAATGGCTCAGATCAGGAGGAAATGTGAA |
| 1958 | 206_HRV71 | AATCTCTCAAAGTGGCAGATTACACTCAAAGAAATGGCTCAGATCAGGAGGAAATGTGAA |
| 1959 | 207_HRV8 | AGTTTCAGGACCTGGGGAATAAACATACAAGAGATGTCACAAATTAGAAGGAAATTTGAG |
| 1960 | 208_HRV95 | AATTTCAGGACCTGGGGAATAAACATACAAGAGATGTCACAAATTAGAAGGAAATTTGAA |
| 1961 | 209_HRV45 | AATTACAAAAATTGGGCAATTAGTTTACAAGAAATGTCACAAATTAGGAGGAAATTTGAA |
| 1962 | 210_HRV45a | AATTACAAAAATTGGGCAATTAGTTTACAAGAAATGTCACAAATTAGGAGGAAATTTGAA |
| 1963 | 211_HRV45b | AATTACAAAAATTGGGCAATTAGTTTACAAGAAATGTCACAAATTAGGAGGAAATTTGAA |
| 1964 | 212_HRV6 | ------------------------------------------------------------ |
| 1965 | 213_HRV6a | ------------------------------------------------------------ |
| 1966 | 214_HRV6b | ------------------------------------------------------------ |
| 1967 | 215_HRV37 | ------------------------------------------------------------ |
| 1968 | 216_HRV37a | ------------------------------------------------------------ |
| 1969 | 217_HRV37b | ------------------------------------------------------------ |
| 1970 | 218_HRV3 | ------------------------------------------------------------ |
| 1971 | 219_HRV3a | ------------------------------------------------------------ |
| 1972 | 220_HRV3b | ------------------------------------------------------------ |
| 1973 | 221_HRV14 | ------------------------------------------------------------ |
| 1974 | 222_HRV14a | ------------------------------------------------------------ |
| 1975 | 223_HRV14b | ------------------------------------------------------------ |
| 1976 | 224_HRV72 | ------------------------------------------------------------ |
| 1977 | 225_HRV72a | ------------------------------------------------------------ |
| 1978 | 226_HRV72b | ------------------------------------------------------------ |
| 1979 | 227_HRV83 | ------------------------------------------------------------ |
| 1980 | 228_HRV83a | ------------------------------------------------------------ |
| 1981 | 229_HRV83b | ------------------------------------------------------------ |
| 1982 | 230_HRV92 | ------------------------------------------------------------ |
| 1983 | 231_HRV92a | ------------------------------------------------------------ |
| 1984 | 232_HRV92b | ------------------------------------------------------------ |

FIG. D5 CONT'D

01.trace                                                              9/20/2007 4:58 PM

```
1985 233_HRV79      ------------------------------------------------------------
1986 234_HRV79a     ------------------------------------------------------------
1987 235_HRV79b     ------------------------------------------------------------
1988 236_HRV35      ------------------------------------------------------------
1989 237_HRV35a     ------------------------------------------------------------
1990 238_HRV35b     ------------------------------------------------------------
1991 239_1HRV86     ------------------------------------------------------------
1992 240_1HRV86     ------------------------------------------------------------
1993 241_1HRV86     ------------------------------------------------------------
1994 242_HRV70      ------------------------------------------------------------
1995 243_HRV70a     ------------------------------------------------------------
1996 244_HRV70b     ------------------------------------------------------------
1997 245_HRV91      ------------------------------------------------------------
1998 246_HRV91a     ------------------------------------------------------------
1999 247_HRV91b     ------------------------------------------------------------
2000 248_HRV17      ------------------------------------------------------------
2001 249_HRV17a     ------------------------------------------------------------
2002 250_HRV17b     ------------------------------------------------------------
2003 251_HRV69      ------------------------------------------------------------
2004 252_HRV69a     ------------------------------------------------------------
2005 253_HRV69b     ------------------------------------------------------------
2006 254_HRV48      ------------------------------------------------------------
2007 255_HRV48a     ------------------------------------------------------------
2008 256_HRV48b     ------------------------------------------------------------
2009 257_HRV52      ------------------------------------------------------------
2010 258_HRV52a     ------------------------------------------------------------
2011 259_HRV52b     ------------------------------------------------------------
2012 260_HRV4       ------------------------------------------------------------
2013 261_HRV4a|     ------------------------------------------------------------
2014 262_HRV4b|     ------------------------------------------------------------
2015 263_HRV99      ------------------------------------------------------------
2016 264_HRV99a     ------------------------------------------------------------
2017 265_HRV99b     ------------------------------------------------------------
2018 266_HRV5       ------------------------------------------------------------
2019 267_HRV5a|     ------------------------------------------------------------
2020 268_HRV5b|     ------------------------------------------------------------
2021 269_HRV42      ------------------------------------------------------------
2022 270_HRV42a     ------------------------------------------------------------
2023 271_HRV42b     ------------------------------------------------------------
2024 272_HRV26      ------------------------------------------------------------
2025 273_HRV26a     ------------------------------------------------------------
2026 274_HRV26b     ------------------------------------------------------------
2027 275_HRV27      ------------------------------------------------------------
2028 276_HRV27a     ------------------------------------------------------------
2029 277_HRV27b     ------------------------------------------------------------
2030 278_HRV93      ------------------------------------------------------------
2031 279_HRV93a     ------------------------------------------------------------
2032 280_HRV93b     ------------------------------------------------------------
2033 281_HRV97      ------------------------------------------------------------
2034 282_HRV97a     ------------------------------------------------------------
2035 283_HRV97b     ------------------------------------------------------------
2036 284_HRV84      ------------------------------------------------------------
2037 285_HRV84a     ------------------------------------------------------------
2038 286_HRV84b     ------------------------------------------------------------
2039 287_HRV87      ------------------------------------------------------------
2040 288_HRV87a     ------------------------------------------------------------
2041 289_HRV87b     ------------------------------------------------------------
2042 GROUP_1        ------------------------------------------------------------
2043
2044 1_HRV1A1|d     TTGTTTACATATGTCAGGTTTGACTCAGAAATAACCTTGG-TGCCTTGTATTGCTGGTAG
2045 2_HRV1A2|d     TTGTTTACATATGTCAGGTTTGACTCAGAAATAACCTTGG-TGCCTTGTATTGCTGGTAG
2046 3_HRV1A|cD     TTGTTTACATATGTCAGGTTTGACTCAGAAATAACCTTGG-TGCCTTGTATTGCTGGTAG
2047 4_HRV1B1|d     CTATTTACTTATGTTAGGTTTGATTCAGAAGTAACTTTAG-TACCCTGTATTGCTGGTAG
2048 5_HRV1B2|d     CTATTTACTTATGTTAGGTTTGATTCAGAAGTAACTTTAG-TACCCTGTATTGCTGGTAG
```

FIG. D5 CONT'D

01.trace                                                                  9/20/2007 4:58 PM

```
2049  6_HRV1B       CTATTTACTTATGTTAGGTTTGATTCAGAAGTAACTTTAG-TACCCTGTATTGCTGGTAG
2050  7_HRV40a|d    TTCTTTACATATGCTAGGTTTGATTCAGAAATTACCTTAG-TTCCTTGTATAGCCGGTAA
2051  8_HRV40b|d    TTCTTTACATATGCTAGGTTTGATTCAGAAATTACCTTAG-TTCCTTGTATAGCCGGTAA
2052  9_HRV40       TTCTTTACATATGCTAGGTTTGATTCAGAAATTACCTTAG-TTCCTTGTATAGCCGGTAA
2053  10_HRV85      TTCTTTACTTACACTAGATTTGATTCAGAAATCACTTTAG-TCCCTTGTATAGCTGGAAA
2054  11_HRV85a|    TTCTTTACTTACACTAGATTTGATTCAGAAATCACTTTAG-TCCCTTGTATAGCTGGAAA
2055  12_HRV85b|    TTCTTTACTTACACTAGATTTGATTCAGAAATCACTTTAG-TCCCTTGTATAGCTGGAAA
2056  13_HRV56a|    TTCTTTACTTATGTCAGATTTGATTCAGAGGTTACTTTGG-TACCTTGTGTAGCCGGCAA
2057  14_HRV56b|    TTCTTTACTTATGTCAGATTTGATTCAGAGGTTACTTTGG-TACCTTGTGTAGCCGGCAA
2058  15_HRV56      TTCTTTACTTATGTCAGATTTGATTCAGAGGTTACTTTGG-TACCTTGTGTAGCCGGCAA
2059  16_HRV54      TTCTTTACTTATGTTAGGTTTGATTCAGAAATTACTCTAG-TCCCCTGTATAGCTGGTAA
2060  17_HRV98      TTCTTTACTTATGTTAGATTTGATTCAGAAGTTACCTTAG-TTCCTTGCATAGCTGGCAA
2061  18_HRV59a|    TTCTTCACATATGTTAGATTTGACTCAGAAATCACTTTGG-TGCCTTGCATAGCTGGAAA
2062  19_HRV59b|    TTCTTCACATATGTTAGATTTGACTCAGAAATCACTTTGG-TGCCTTGCATAGCTGGAAA
2063  20_HRV59      TTCTTCACATATGTTAGATTTGACTCAGAAATCACTTTGG-TGCCTTGCATAGCTGGAAA
2064  21_HRV63      TTCTTCACATATGTCAGATTTGATTCAGAAGTCACTCTTG-TACCATGTATAGCAGGAAA
2065  22_HRV63b|    TTCTTCACATATGTCAGATTTGATTCAGAAGTCACTCTTG-TACCATGTATAGCAGGAAA
2066  23_HRV63a|    TTCTTCACATATGTCAGATTTGATTCAGAAGTCACTCTTG-TACCATGTATAGCAGGAAA
2067  24_HRV39      ATGTTCACCTATGTTAGATTTGACTCAGAGATTACTTTAG-TCCCATGCATAGCTGGAAG
2068  25_HRV39a|    ATGTTCACCTATGTTAGATTTGACTCAGAGATTACTTTAG-TCCCATGCATAGCTGGAAG
2069  26_HRV39b|    ATGTTCACCTACGTTAGATTTGACTCAGAGATTACTTTAG-TCCCATGCATAGCTGGAAG
2070  27_HRV10a|    ATGTTTACATATGTTAGATTTGACTCAGAAGTCACTTTAG-TACCTTGCATCGCAGGCAA
2071  28_HRV10b|    ATGTTTACATATGTTAGATTTGACTCAGAAGTCACTTTAG-TACCTTGCATCGCAGGCAA
2072  29_HRV10      ATGTTTACATATGTTAGATTTGACTCAGAAGTCACTTTAG-TACCTTGCATCGCAGGCAA
2073  30_HRV100a    ATGTTTACATATGTCAGATTTGACTCAGAAATCACATTGG-TACCCTGTATTGCAGGAAA
2074  31_HRV100b    ATGTTTACATATGTCAGATTTGACTCAGAAATCACATTGG-TACCCTGTATTGCAGGAAA
2075  32_HRV100     ATGTTTACATATGTCAGATTTGACTCAGAAATCACATTGG-TACCCTGTATTGCAGGAAA
2076  33_HRV66      ATGTTCACATATGTTAGGTTTGATTCTGAAATTACATTAG-TCCCATGCATTGCAGGAAA
2077  34_HRV66b|    ATGTTCACATATGTTAGGTTTGATTCTGAAATTACATTAG-TCCCATGCATTGCAGGAAA
2078  35_HRV66a|    ATGTTCACATATGTTAGGTTTGATTCTGAAATTACATTAG-TCCCATGCATTGCAGGAAA
2079  36_HRV77a|    ATGTTTACATATGTAAGATTTGATTCAGAAATTACATTGG-TCCCATGTATTGCTGGAAA
2080  37_HRV77b|    ATGTTTACATATGTAAGATTTGATTCAGAAATTACATTGG-TCCCATGTATTGCTGGAAA
2081  38_HRV77      ATGTTTACATATGTAAGATTTGATTCAGAAATTACATTGG-TCCCATGTATTGCTGGAAA
2082  39_HRV62a     ATGTTTACATATGTAAGATTTGATTCAGAAATAACCCTGG-TTCCATCTATTGCAGGACG
2083  40_HRV62b     ATGTTTACATATGTAAGATTTGATTCAGAAATAACCCTGG-TTCCATCTATTGCAGGACG
2084  41_HRV25      ATGTTTACATATGTGAGATTTGATTCAGAGATAACCCTAG-TTCCATCTATTGCAGGACG
2085  42_HRV29a     ATGTTCACATATGTGAGATTTGACTCAGAAATAACTCTGG-TTCTTTGCATTGCAGGACG
2086  43_HRV29b     ATGTTCACATATGTGAGATTTGACTCAGAAATAACTCTGG-TTCCATGCATTGCAGGACG
2087  44_HRV44a     ATGTTCACATATGTGAGATTTGATTCGGAAATAACTCTAG-TTCCATGCATTGCAGGACA
2088  45_HRV44b     ATGTTCACATATGTGAGATTTGATTCAGAAATAACTCTAG-TTCCATGCATTGCAGGACG
2089  46_HRV31      ATGTTCACATATGTAAGATTTGATTCAGAAGTGACCATAG-TTCCATGCATTGCAGGACA
2090  47_HRV31a|    ATGTTCACATATGTAAGATTTGATTCAGAAGTGACCATAG-TTCCATGCATTGCAGGACA
2091  48_HRV31b|    ATGTTCACATATGTAAGATTTGATTCAGAAGTGACCATAG-TTCCATGCATTGCAGGACA
2092  49_HRV47      ATGTTTACATATGTAAGATTTGATTCAGAAGTAACCATGG-TTCCATGTATTGCAGGGTA
2093  50_HRV47a|    ATGTTTACATATGTAAGATTTGATTCAGAAGTAACCATGG-TTCCATGTATTGCAGGGTA
2094  51_HRV47b|    ATGTTTACATATGTAAGATTTGATTCAGAAGTAACCATGG-TTCCATGTATTGCAGGGTA
2095  52_HRV11      ATGTTCACATACACTAGATTTGATTCAGAGATCACATTGG-TGCCTTGTATAGCTGCAAA
2096  53_HRV11b|    ATGTTCACATACACTAGATTTGATTCAGAGATCACATTGG-TGCCTTGTATAGCTGCAAA
2097  54_HRV11a|    ATGTTCACATACACTAGATTTGATTCAGAGATCACATTGG-TGCCTTGTATAGCTGCAAA
2098  55_HRV76      ATGTTTACATATACTAGATTTGATTCAGAAGTTACTCTAG-TTCCTTCTATAGCTGCCAA
2099  56_HRV76b|    ATGTTTACATATACTAGATTTGATTCAGAAGTTACTCTAG-TTCCTTCTATAGCTGCCAA
2100  57_HRV76a|    ATGTTTACATATACTAGATTTGATTCAGAAGTTACTCTAG-TTCCTTCTATAGCTGCCAA
2101  58_HRV33      ATGTTTACATATGCCAGATTTGATTCAGAGATCACCCTAG-TCCCTTCTATAGCTGCCCA
2102  59_HRV33b|    ATGTTTACATATGCCAGATTTGATTCAGAGATCACCCTAG-TCCCTTCTATAGCTGCCCA
2103  60_HRV33a|    ATGTTTACATATGCCAGATTTGATTCAGAGATCACCCTAG-TCCCTTCTATAGCTGCCCA
2104  61_HRV24a|    TTATTCACATATACTAGATTTGACTCTGAGATTACAATAG-TTCCATCCATAGCTGGCAA
2105  62_HRV24b|    TTATTCACATATACTAGATTTGACTCTGAGATTACAATAG-TTCCATCCATAGCTGGCAA
2106  63_HRV24      TTATTCACATATACTAGATTTGACTCTGAGATTACAATAG-TTCCATCCATAGCTGGCAA
2107  64_HRV90      TTGTTTACATATGCTAGATTTGATTCAGAAATTACAATAG-TACCATCTATAGCTGGCAA
2108  65_HRV90a|    TTGTTTACATATGCTAGATTTGATTCTGAAATTACAATAG-TACCATCTATAGCTGGCAA
2109  66_HRV90b|    TTGTTTACATATGCTAGATTTGATTCTGAAATTACAATAG-TACCATCTATAGCTGGCAA
2110  67_HRV34      ATGTTCACCTACGTCAGATTTGATTCTGAAGTCACCCTAG-TACCATCAATAGCGGCCAA
2111  68_HRV34b|    ATGTTCACCTACGTCAGATTTGATTCTGAAGTCACCCTAG-TACCATCAATAGCGGCCAA
2112  69_HRV34a|    ATGTTCACCTACGTCAGATTTGATTCTGAAGTCACCCTAG-TACCATCAATAGCGGCCAA
```

FIG. D5 CONT'D 01.trace											9/20/2007 4:58 PM

```
2113  70_HRV50a|    ATGTTCACCTATGTGAGGTTTAATTCTGAGGTCACATTAG-TACCATCCATAGCTGCCAA
2114  71_HRV50b|    ATGTTCACCTATGTGAGGTTTAATTCTGAGGTCACATTAG-TACCATCCATAGCTGCCAA
2115  72_HRV50     ATGTTCACCTATGTGAGGTTTAATTCTGAGGTCACATTAG-TACCATCCATAGCTGCCAA
2116  73_HRV18a|    ATGTTTACATATGTTAGATTTGATTCAGAAATTACACTAG-TACCATCTGTAGCTGCTAA
2117  74_HRV18b|    ATGTTTACATATGTTAGATTTGATTCAGAAATTACACTAG-TACCATCTGTAGCTGCTAA
2118  75_HRV18     ATGTTTACATATGTTAGATTTGATTCAGAAATTACACTAG-TACCATCTGTAGCTGCTAA
2119  76_HRV55     ATGTTCACCTATACTAGATTTGATTCAGAAGTTACATTAG-TACCCTCTATTGCTGCAAA
2120  77_HRV55b|    ATGTTCACCTATACTAGATTTGATTCAGAAGTTACATTAG-TACCCTCTATTGCTGCAAA
2121  78_HRV55a|    ATGTTCACCTATACTAGATTTGATTCAGAAGTTACATTAG-TACCCTCTATTGCTGCAAA
2122  79_HRV57     CTATTTACATATGTTAGGTTTGATTCTGAAGTTACATTAG-TTCCCTCCATAGCTGCTCA
2123  80_HRV57a|    CTATTTACATATGTTAGGTTTGATTCTGAAGTTACATTAG-TTCCCTCCATAGCTGCTCA
2124  81_HRV57b|    CTATTTACATATGTTAGGTTTGATTCTGAAGTTACATTAG-TTCCCTCCATAGCTGCTCA
2125  82_HRV21     ATGTTCACCTATACTAGATTTGATTCAGAAATAACTTTGG-TGCCGTCAATTGCAGCTAG
2126  83_HRVHan    ATGTTCACCTATACTAGATTTGATTCAGAAATAACTTTGG-TACCGTCAATTGCAGCTAA
2127  84_HRV43     TTGTTCACATACTTAAGGTTTGATTCTGAAATTACCCTTG-TTCCTTGCATTGCAGCAAA
2128  85_HRV43b|    TTGTTCACATACTTAAGGTTTGATTCTGAAATTACCCTTG-TTCCTTGCATTGCAGCAAA
2129  86_HRV43a|    TTGTTCACATACTTAAGGTTTGATTCTGAAATTACCCTTG-TTCCTTGCATTGCAGCAAA
2130  87_HRV75     TTATTTACATATCTTAGATTTGATTCAGAGGTTACTCTGG-TGCCATGCATTGCAGCTAA
2131  88_HRV75b|    TTATTTACATATCTTAGATTTGATTCAGAGGTTACTCTGG-TGCCATGCATTGCAGCTAA
2132  89_HRV75a|    TTATTTACATATCTTAGATTTGATTCAGAGGTTACTCTGG-TGCCATGCATTGCAGCTAA
2133  96_HRV9a|d    TTGTTTACATATGCAAGATTTGACTCTGAAATAACATTGG-TCCCGTGTATAGCAGCAGA
2134  97_HRV9b|d    TTGTTTACATATGCAAGATTTGACTCTGAAATAACATTGG-TCCCGTGTATAGCAGCAGA
2135  98_HRV9      TTGTTTACATATGCAAGATTTGACTCTGAAATAACATTGG-TCCCGTGTATAGCAGCAGA
2136  99_HRV32     TTGTTTACATACACAAGGTTTGATTCTGAAATAACATTAG-TACCTTGTATAGCTGCAGA
2137 100_HRV32a    TTGTTTACATACACAAGGTTTGATTCTGAAATAACATTAG-TACCTTGTATAGCTGCAGA
2138 101_HRV32b    TTGTTTACATACACAAGGTTTGATTCTGAAATAACATTAG-TACCTTGTATAGCTGCAGA
2139 102_HRV67     CTATTCACATATACAAGATTTGATTCTGAGATAACACTGG-TACCATGCATAGCTGCAGA
2140 103_HRV67a    CTATTCACATATACAAGATTTGATTCTGAGATAACACTGG-TACCATGCATAGCTGCAGA
2141 104_HRV67b    CTATTCACATATACAAGATTTGATTCTGAGATAACACTGG-TACCATGCATAGCTGCAGA
2142 105_HRV15     TTATTCACATATGTAAGGTTTGATTCAGAAATAACACTTG-TACCATGCATTGCAGCAAA
2143 106_HRV15a    TTATTCACATATGTAAGGTTTGATTCAGAAATAACACTTG-TACCATGCATTGCAGCAAA
2144 107_HRV15b    TTATTCACATATGTAAGGTTTGATTCAGAAATAACACTTG-TACCATGCATTGCAGCAAA
2145 108_HRV74a    TTGTTCACATATGTTAGATTTGACTCAGAAGTGACATTAG-TTCCATGCATTGCTGCTAA
2146 109_HRV74b    TTGTTCACATATGTTAGATTTGACTCAGAAGTGACATTAG-TTCCATGCATTGCTGCTAA
2147 110_HRV74     TTGTTCACATATGTTAGATTTGACTCAGAAGTGACATTAG-TTCCATGCATTGCTGCTAA
2148 111_HRV38a    ATGTTTACATATGTGAGATTTGATTCAGAAGTTACATTAG-TCCCATGTATAGCAGCACA
2149 112_HRV38b    ATGTTTACATATGTGAGATTTGATTCAGAAGTTACATTAG-TCCCATGTATAGCAGCACA
2150 113_HRV38     ATGTTTACATATGTGAGATTTGATTCAGAAGTTACATTAG-TCCCATGTATAGCAGCACA
2151 114_HRV60     TTATTTACATATGTAAGATTTGATTCAGAATTGACTCTGG-TCCCATGCATAGCAGCAAA
2152 115_HRV60a    TTATTTACATATGTAAGATTTGATTCAGAATTGACTCTGG-TCCCATGCATAGCAGCAAA
2153 116_HRV60b    TTATTTACATATGTAAGATTTGATTCAGAATTGACTCTGG-TCCCATGCATAGCAGCAAA
2154 117_HRV64a    TTATTTACATATGTTAGATTTGATTCTGAAATAACCTTAG-TGCCTTGCATATCTTCTCA
2155 118_HRV64b    TTATTTACATATGTTAGATTTGATTCTGAAATAACCTTAG-TGCCTTGCATATCTTCTCA
2156 119_HRV64     TTATTTACATATGTTAGATTTGATTCTGAAATAACCTTAG-TGCCTTGCATATCTTCTCA
2157 120_HRV94a    CTATTTACTTATGTTAGATTTGATTCAGAAATAACTTTAG-TACCTTGCATATCATCTCA
2158 121_HRV94b    CTATTTACTTATGTTAGATTTGATTCAGAAATAACTTTAG-TACCTTGCATATCATCTCA
2159 122_HRV94     CTATTTACTTATGTTAGATTTGATTCAGAAATAACTTTAG-TACCTTGCATATCATCTCA
2160 123_HRV22     CTATTTACATATCTCAGGTTTGATTCTGAAATCACTTTGG-TACCATGCATTGCTTCACA
2161 124_HRV22a    CTATTTACATATCTCAGGTTTGATTCTGAAATCACTTTGG-TACCATGCATTGCTTCACA
2162 125_HRV22b    CTATTTACATATCTCAGGTTTGATTCTGAAATCACTTTGG-TACCATGCATTGCTTCACA
2163 126_HRV82     CTTTTCACATATGTGAGATTTGATTCAGAAATTACTTTAG-TGCCTTGCATAGCCTCTCA
2164 127_HRV82b    CTTTTCACATATGTGAGATTTGATTCAGAAATTACTTTAG-TGCCTTGCATAGCCTCTCA
2165 128_HRV82a    CTTTTCACATATGTGAGATTTGATTCAGAAATTACTTTAG-TGCCTTGCATAGCCTCTCA
2166 129_HRV19     CTTTTCACTTACCTCAGATTTGATTCAGAGGTAACATTAG-TCCCTTGCATAGCTGCTAA
2167 130_HRV19a    CTTTTCACTTACCTCAGATTTGATTCAGAGGTAACATTAG-TCCCTTGCATAGCTGCTAA
2168 131_HRV19b    CTTTTCACTTACCTCAGATTTGATTCAGAGGTAACATTAG-TCCCTTGCATAGCTGCTAA
2169 132_HRV13     TTGTTCACCTATGTAAGATTTGATTCAGAAATAACAATTG-TGCCATGTATAGCCGGGCA
2170 133_HRV13a    TTGTTCACCTATGTAAGATTTGATTCAGAAATAACAATTG-TGCCATGTATAGCCGGGCA
2171 134_HRV13b    TTGTTCACCTATGTAAGATTTGATTCAGAAATAACAATTG-TGCCATGTATAGCCGGGCA
2172 135_HRV41     TTTTTTACGTATGTTAGATTTGACTCAGAAATAACAATTG-TGCCAAGTATAGCTGGACA
2173 136_HRV41a    TTTTTTACGTATGTTAGATTTGACTCAGAAATAACAATTG-TGCCAAGTATAGCTGGACA
2174 137_HRV41b    TTTTTTACGTATGTTAGATTTGACTCAGAAATAACAATTG-TGCCAAGTATAGCTGGACA
2175 138_HRV73     TTATTCACCTATGTAAGATTTGATTCAGAAGTGACAATTG-TACCATGTATAGCTGGTCA
2176 139_HRV73b    TTATTCACCTATGTAAGATTTGATTCAGAAGTGACAATTG-TACCATGTATAGCTGGTCA
```

FIG. D5 CONT'D

01.trace                                                                 9/20/2007 4:58 PM

```
2177 140_HRV73a    TTATTCACCTATGTAAGATTTGATTCAGAAGTGACAATTG-TACCATGTATAGCTGGTCA
2178 141_HRV61     TTGTTCACATATGCTAGATTTGATTCAGACAATTG-TACCTTGTGTTGCTGGGCA
2179 142_HRV61a    TTGTTCACATATGCTAGATTTGATTCAGAGATTACAATTG-TACCTTGTGTTGCTGGGCA
2180 143_HRV61b    TTGTTCACATATGCTAGATTTGATTCAGAGATTACAATTG-TACCTTGTGTTGCTGGGCA
2181 144_HRV96     CTGTTCACTTATGCTAGATTTGATTCAGAGATAACAATTG-TTCCATGTGTTGCTGTGCA
2182 145_HRV96b    CTGTTCACTTATGCTAGATTTGATTCAGAGATAACAATTG-TTCCATGTGTTGCTGTGCA
2183 146_HRV96a    CTGTTCACTTATGCTAGATTTGATTCAGAGATAACAATTG-TTCCATGTGTTGCTGTGCA
2184  90_HRV16a|   ATGTTTACTTATGCAAGATTTGACTCTGAAATTACTATGG-TACCAAGTGTAGCAGCCAA
2185  91_HRV16b|   ATGTTTACTTATGCAAGATTTGACTCTGAAATTACTATGG-TACCAAGTGTAGCAGCCAA
2186  92_1AYM_A    ATGTTTACTTATGCAAGATTTGACTCTGAAATTACTATGG-TACCAAGTGTAGCAGCCAA
2187  93_HRV81a|   ATGTTCACATACACTAGATTTAACTCTGAGATTACACTGG-TACCAAGTATTGCAAACAA
2188  94_HRV81b|   ATGTTCACATACACTAGATTTAACTCTGAGATTACACTGG-TACCAAGTATTGCAAACAA
2189  95_HRV81     ATGTTCACATACACTAGATTTAACTCTGAGATTACACTGG-TACCAAGTATTGCAAACAA
2190 147_HRV2      TTGTTCACCTATACTAGGTTTGATTCTGAAATAACCCTAG-TTCCATGCATTTCCGCCCT
2191 148_HRV2a|    TTGTTCACCTATACTAGGTTTGATTCTGAAATAACCCTAG-TTCCATGCATTTCCGCCCT
2192 149_HRV2b|    TTGTTCACCTATACTAGGTTTGATTCTGAAATAACCCTAG-TTCCATGCATTTCCGCCCT
2193 150_HRV49a    CTGTTTACTTACACTAGATTCGATTCTGAAATAACCTTGG-TTCCATGCATTTCTGCACT
2194 151_HRV49b    CTGTTTACTTACACTAGATTCGATTCTGAAATAACCTTGG-TTCCATGCATTTCTGCACT
2195 152_HRV49     CTGTTTACTTACACTAGATTCGATTCTGAAATAACCTTGG-TTCCATGCATTTCTGCACT
2196 153_HRV23a    CTGTTTACTTACACTAGATTTGATTCTGAAATTACTTTGG-TTCCATGCATTTCTGCTCT
2197 154_HRV23b    CTGTTTACTTACACTAGATTTGATTCTGAAATTACTTTGG-TTCCATGCATTTCTGCTCT
2198 155_HRV23     CTGTTTACTTACACTAGATTTGATTCTGAAATTACTTTGG-TTCCATGCATTTCTGCTCT
2199 156_HRV30a    CTATTCACTTACACTAGATTTGATTCTGAGATAACCTTGG-TTCCGTGTATTTCAGCTCT
2200 157_HRV30b    CTATTCACTTACACTAGATTTGATTCTGAGATAACCTTGG-TTCCGTGTATTTCAGCTCT
2201 158_HRV30     CTATTCACTTACACTAGATTTGATTCTGAGATAACCTTGG-TTCCGTGTATTTCAGCTCT
2202 159_HRV7      CTATTCACATACACTAGATTTGATTCTGAGATAACAATAG-TCACAGCAGCAGCAGCACA
2203 160_HRV7b|    CTATTCACATACACTAGATTTGATTCTGAGATAACAATAG-TCACAGCAGCAGCAGCACA
2204 161_HRV7a|    CTATTCACATACACTAGATTTGATTCTGAGATAACAATAG-TCACAGCAGCAGCAGCACA
2205 162_HRV88     TTGTTTACATACACTAGATTTGACTCAGAAATAACAATAG-TCACAGCAGCTGCAGCACA
2206 163_HRV88a    TTGTTTACATACACTAGATTTGACTCAGAAATAACAATAG-TCACAGCAGCTGCAGCACA
2207 164_HRV88b    TTGTTTACATACACTAGATTTGACTCAGAAATAACAATAG-TCACAGCAGCTGCAGCACA
2208 165_HRV36a    TTGTTTACATACACAAGATTTGACTCAGAAATAACAATAG-TCACCGCAGCTGCAGTGCA
2209 166_HRV36b    TTGTTTACATACACAAGATTTGACTCAGAAATAACAATAG-TCACCGCAGCTGCAGTGCA
2210 167_HRV36     TTGTTTACATACACAAGATTTGACTCAGAAATAACAATAG-TCACCGCAGCTGCAGTGCA
2211 168_HRV89a    TTATTCACATATACAAGATTTGATTCAGAGATAACAATAG-TCACTGCAGCCGCAGCTCA
2212 169_HRV89b    TTATTCACATATACAAGATTTGATTCAGAGATAACAATAG-TCACTGCAGCCGCAGCTCA
2213 170_HRV89     TTATTCACATATACAAGATTTGATTCAGAGATAACAATAG-TCACTGCAGCCGCAGCTCA
2214 171_HRV58     TTGTTTACATATACAAGATTTGACTCAGAGATTACAATAG-TCACTGCAGCAGCTGCTCA
2215 172_HRV58a    TTGTTTACATATACAAGATTTGACTCAGAGATTACAATAG-TCACTGCAGCAGCTGCTCA
2216 173_HRV58b    TTGTTTACATATACAAGATTTGACTCAGAGATTACAATAG-TCACTGCAGCAGCTGCTCA
2217 174_HRV12a    CTTTTCACCTACTTAAGGTTTGATTCTGAAATCACCATTGTTCCAAGCAATG-CAGCAAT
2218 175_HRV12b    CTTTTCACCTACTTAAGGTTTGATTCTGAAATCACCATTGTTCCAAGCAATG-CAGCAAT
2219 176_HRV12     CTTTTCACCTACTTAAGGTTTGATTCTGAAATCACCATTGTTCCAAGCAATG-CAGCAAT
2220 177_HRV78a    ATGTTCACATATCTCAGATTTGATTCAGAAATCACTCTTG-TGTGTGCAGTGGCCTCACA
2221 178_HRV78b    ATGTTCACATATCTCAGATTTGATTCAGAAATCACTCTTG-TGTGTGCAGTGGCCTCACA
2222 179_HRV78     ATGTTCACATATCTCAGATTTGATTCAGAAATCACTCTTG-TGTGTGCAGTGGCCTCACA
2223 180_HRV20     CTCTTTACATACCTCAGATTTGATTCTGAGATTACAATAG-TAGCAACAGTAGCTGCACT
2224 181_HRV20a    CTCTTTACATACCTCAGATTTGATTCTGAGATTACAATAG-TAGCAACAGTAGCTGCACT
2225 182_HRV20b    CTCTTTACATACCTCAGATTTGATTCTGAGATTACAATAG-TAGCAACAGTAGCTGCACT
2226 183_HRV68     CTATTCACATACCTTAGGTTTGACTCTGAGATTACAATAG-TAGCAACAATAGCTGCTCT
2227 184_HRV68a    CTATTCACATACCTTAGGTTTGACTCTGAGATTACAATAG-TAGCAACAATAGCTGCTCT
2228 185_HRV68b    CTATTCACATACCTTAGGTTTGACTCTGAGATTACAATAG-TAGCAACAATAGCTGCTCT
2229 186_HRV28     ATGTTTACATATCTCAGATTTGATTCTGAAATTACTATAG-TGGTGTCAGTTGCAAGTAA
2230 187_HRV28a    ATGTTTACATATCTCAGATTTGATTCTGAAATTACTATAG-TGGTGTCAGTTGCAAGTAA
2231 188_HRV28b    ATGTTTACATATCTCAGATTTGATTCTGAAATTACTATAG-TGGTGTCAGTTGCAAGTAA
2232 189_HRV53a    ATGTTCACATATCTTAGATTTGATTCAGAAATAACTATAG-TGGTATCAGTGGCTAGTAA
2233 190_HRV53b    ATGTTCACATATCTTAGATTTGATTCAGAAATAACTATAG-TGGTATCAGTGGCTAGTAA
2234 191_HRV53     ATGTTCACATATCTTAGATTTGATTCAGAAATAACTATAG-TGGTATCAGTGGCTAGTAA
2235 192_HRV46a    CTTTTTACATATCTCAGATTTGATTCAGAAATAACAATAG-TCACCACATTGGCAGGCCA
2236 193_HRV46b    CTTTTTACATATCTCAGATTTGATTCAGAAATAACAATAG-TCACCACATTGGCAGGCCA
2237 194_HRV46     CTTTTTACATATCTCAGATTTGATTCAGAAATAACAATAG-TCACCACATTGGCAGGCCA
2238 195_HRV80a    CTTTTCACTTACCTCAGATTTGACTCAGAAATAACAATAG-TAACTACCTTAGCAGGACA
2239 196_HRV80b    CTTTTCACTTACCTCAGATTTGACTCAGAAATAACAATAG-TAACTACCTTAGCAGGACA
2240 197_HRV80     CTTTTCACTTACCTCAGATTTGACTCAGAAATAACAATAG-TAACTACCTTAGCAGGACA
```

FIG. D5 CONT'D 01.trace                                                              9/20/2007 4:58 PM

```
2241 198_HRV51   CTTTTCACATACTTAAGATTTGATTCAGAGATCACTATAG-TTGCTACCATTGCTGGACA
2242 199_HRV51a  CTTTTCACATACTTAAGATTTGATTCAGAGATCACTATAG-TTGCTACCATTGCTGGACA
2243 200_HRV51b  CTTTTCACATACTTAAGATTTGATTCAGAGATCACTATAG-TTGCTACCATTGCTGGACA
2244 201_HRV65a  CTCTTCACCTATTTGCGCTTTGACTCAGAAATTACCATAG-TGGCTACTATAGCTGGACA
2245 202_HRV65b  CTCTTCACCTATTTGCGCTTTGACTCAGAAATTACCATAG-TGGCTACTATAGCTGGACA
2246 203_HRV65   CTCTTCACCTATTTGCGCTTTGACTCAGAAATTACCATAG-TGGCTACTATAGCTGGACA
2247 204_HRV71a  CTCTTCACATACCTGCGCTTTGATTCAGAGATAACAATTG-TAGCTACACTAGCAGGGCA
2248 205_HRV71b  CTCTTCACATACCTGCGCTTTGATTCAGAGATAACAATTG-TAGCTACACTAGCAGGGCA
2249 206_HRV71   CTCTTCACATACCTGCGCTTTGATTCAGAGATAACAATTG-TAGCTACACTAGCAGGGCA
2250 207_HRV8    ATGTTCACTTATGTAAGATTTGATTCAGAGATAACAATTG-TACCATGTATTGCAGCTAT
2251 208_HRV95   ATGTTCACTTATGTAAGATTTGATTCAGAGATAACAATTG-TACCATGTATTGCAGCTAT
2252 209_HRV45   ATGTTTACATATGTCAGATTTGATTCCGAAATAACAATAG-TACCATGTGTTGCTGCCAC
2253 210_HRV45a  ATGTTTACATATGTCAGATTTGATTCCGAAATAACAATAG-TACCATGTGTTGCTGCCAC
2254 211_HRV45b  ATGTTTACATATGTCAGATTTGATTCCGAAATAACAATAG-TACCATGTGTTGCTGCCAC
2255 212_HRV6    ------------------------------------------------------------
2256 213_HRV6a|  ------------------------------------------------------------
2257 214_HRV6b|  ------------------------------------------------------------
2258 215_HRV37   ------------------------------------------------------------
2259 216_HRV37a  ------------------------------------------------------------
2260 217_HRV37b  ------------------------------------------------------------
2261 218_HRV3    ------------------------------------------------------------
2262 219_HRV3a|  ------------------------------------------------------------
2263 220_HRV3b|  ------------------------------------------------------------
2264 221_HRV14   ------------------------------------------------------------
2265 222_HRV14a  ------------------------------------------------------------
2266 223_HRV14b  ------------------------------------------------------------
2267 224_HRV72   ------------------------------------------------------------
2268 225_HRV72a  ------------------------------------------------------------
2269 226_HRV72b  ------------------------------------------------------------
2270 227_HRV83   ------------------------------------------------------------
2271 228_HRV83a  ------------------------------------------------------------
2272 229_HRV83b  ------------------------------------------------------------
2273 230_HRV92   ------------------------------------------------------------
2274 231_HRV92a  ------------------------------------------------------------
2275 232_HRV92b  ------------------------------------------------------------
2276 233_HRV79   ------------------------------------------------------------
2277 234_HRV79a  ------------------------------------------------------------
2278 235_HRV79b  ------------------------------------------------------------
2279 236_HRV35   ------------------------------------------------------------
2280 237_HRV35a  ------------------------------------------------------------
2281 238_HRV35b  ------------------------------------------------------------
2282 239_1HRV86  ------------------------------------------------------------
2283 240_1HRV86  ------------------------------------------------------------
2284 241_1HRV86  ------------------------------------------------------------
2285 242_HRV70   ------------------------------------------------------------
2286 243_HRV70a  ------------------------------------------------------------
2287 244_HRV70b  ------------------------------------------------------------
2288 245_HRV91   ------------------------------------------------------------
2289 246_HRV91a  ------------------------------------------------------------
2290 247_HRV91b  ------------------------------------------------------------
2291 248_HRV17   ------------------------------------------------------------
2292 249_HRV17a  ------------------------------------------------------------
2293 250_HRV17b  ------------------------------------------------------------
2294 251_HRV69   ------------------------------------------------------------
2295 252_HRV69a  ------------------------------------------------------------
2296 253_HRV69b  ------------------------------------------------------------
2297 254_HRV48   ------------------------------------------------------------
2298 255_HRV48a  ------------------------------------------------------------
2299 256_HRV48b  ------------------------------------------------------------
2300 257_HRV52   ------------------------------------------------------------
2301 258_HRV52a  ------------------------------------------------------------
2302 259_HRV52b  ------------------------------------------------------------
2303 260_HRV4    ------------------------------------------------------------
2304 261_HRV4a|  ------------------------------------------------------------
```

FIG. D5 CONT'D

01.trace                                                                          9/20/2007 4:58 PM

```
2305  262_HRV4b|      ------------------------------------------------------------
2306  263_HRV99       ------------------------------------------------------------
2307  264_HRV99a      ------------------------------------------------------------
2308  265_HRV99b      ------------------------------------------------------------
2309  266_HRV5        ------------------------------------------------------------
2310  267_HRV5a|      ------------------------------------------------------------
2311  268_HRV5b|      ------------------------------------------------------------
2312  269_HRV42       ------------------------------------------------------------
2313  270_HRV42a      ------------------------------------------------------------
2314  271_HRV42b      ------------------------------------------------------------
2315  272_HRV26       ------------------------------------------------------------
2316  273_HRV26a      ------------------------------------------------------------
2317  274_HRV26b      ------------------------------------------------------------
2318  275_HRV27       ------------------------------------------------------------
2319  276_HRV27a      ------------------------------------------------------------
2320  277_HRV27b      ------------------------------------------------------------
2321  278_HRV93       ------------------------------------------------------------
2322  279_HRV93a      ------------------------------------------------------------
2323  280_HRV93b      ------------------------------------------------------------
2324  281_HRV97       ------------------------------------------------------------
2325  282_HRV97a      ------------------------------------------------------------
2326  283_HRV97b      ------------------------------------------------------------
2327  284_HRV84       ------------------------------------------------------------
2328  285_HRV84a      ------------------------------------------------------------
2329  286_HRV84b      ------------------------------------------------------------
2330  287_HRV87       ------------------------------------------------------------
2331  288_HRV87a      ------------------------------------------------------------
2332  289_HRV87b      ------------------------------------------------------------
2333  GROUP_1         ------------------------------------------------------------
2334
2335  1_HRV1A1|d      AGGAGACGACATTGGACATATTGTAATGCAATATATGTATGTTCCTCCAGGAGCTCCAAT
2336  2_HRV1A2|d      AGGAGACGACATTGGACATATTGTAATGCAATATATGTATGTTCCTCCAGGAGCTCCAAT
2337  3_HRV1A|cD      AGGAGACGACATTGGACATATTGTAATGCAATATATGTATGTTCCTCCAGGAGCTCCAAT
2338  4_HRV1B1|d      AGGAGATGACATTGGTCATGTTGTAATGCAGTATATGTATGTTCCCCCAGGAGCTCCAAT
2339  5_HRV1B2|d      AGGAGATGACATTGGTCATGTTGTAATGCAGTATATGTATGTTCCCCCAGGAGCTCCAAT
2340  6_HRV1B         AGGAGATGACATTGGTCATGTTGTAATGCAGTATATGTATGTTCCCCCAGGAGCTCCAAT
2341  7_HRV40a|d      GGGTGAAGACATTGGACACATTGTGATGCAATATATGTATGTACCCCCTGGCGCACCCAT
2342  8_HRV40b|d      GGGTGAAGACATTGGACACATTGTGATGCAATATATGTATGTACCCCCTGGCGCACCCAT
2343  9_HRV40         GGGTGAAGACATTGGACACATTGTGATGCAATATATGTATGTACCCCCTGGCGCACCCAT
2344  10_HRV85        GGGTGATGATATTGGACACATTGTAATGCAGTATATGTATGTGCCCCCCGGAGCACCAAT
2345  11_HRV85a|      GGGTGATGATATTGGACACATTGTAATGCAGTATATGTATGTGCCCCCCGGAGCACCAAT
2346  12_HRV85b|      GGGTGATGATATTGGACACATTGTAATGCAGTATATGTATGTGCCCCCCGGAGCACCAAT
2347  13_HRV56a|      GGGAGATGATATTGGACACATTGTAATGCAATACATGTATGTGCCTCCTGGTGCACCACT
2348  14_HRV56b|      GGGAGATGATATTGGACACATTGTAATGCAATACATGTATGTGCCTCCTGGTGCACCACT
2349  15_HRV56        GGGAGATGATATTGGACACATTGTAATGCAATACATGTATGTGCCTCCTGGTGCACCACT
2350  16_HRV54        GGGAGTTGATATTGGACACATTGTCATGCAATTCATGTATGTGCCTCCTGGTGCACCAAA
2351  17_HRV98        GGGAGCTGACATTGGACACATTGTCATGCAATTCATGTATGTTCCACCTGGTGCACCTAA
2352  18_HRV59a|      AGGGGATGACATTGGTCATATAGTCATGCAATATATGTATGTTCCACCAGGTGCTCCACT
2353  19_HRV59b|      AGGGGATGACATTGGTCATATAGTCATGCAATATATGTATGTTCCACCAGGTGCTCCACT
2354  20_HRV59        AGGGGATGACATTGGTCATATAGTCATGCAATATATGTATGTTCCACCAGGTGCTCCACT
2355  21_HRV63        AGGTGATGACATTGGTCATATAGTTATGCAGTACATGTACGTTCCACCCGGTGCCCCTCT
2356  22_HRV63b|      AGGTGATGACATTGGTCATATAGTTATGCAGTACATGTACGTTCCACCCGGTGCCCCTCT
2357  23_HRV63a|      AGGTGATGACATTGGTCATATAGTTATGCAGTACATGTACGTTCCACCCGGTGCCCCTCT
2358  24_HRV39        AGGTGAAGATATTGGACACATAGTAATGCAATACATGTATGTCCCCACCTGGTGCACCTGT
2359  25_HRV39a|      AGGTGAAGATATTGGACACATAGTAATGCAATACATGTATGTCCCCACCTGGTGCACCTGT
2360  26_HRV39b|      AGGTGAAGATATTGGACACATAGTAATGCAATACATGTATGTCCCCACCCGGTGCACCTGT
2361  27_HRV10a|      GGGCGATGACATAGGTCACATAGTTATGCAATATATGTATGTGCCACCTGGGGCTCCAGT
2362  28_HRV10b|      GGGCGATGACATAGGTCACATAGTTATGCAATATATGTATGTGCCACCTGGGGCTCCAGT
2363  29_HRV10        GGGCGATGACATAGGTCACATAGTTATGCAATATATGTATGTGCCACCTGGGGCTCCAGT
2364  30_HRV100a      AGGAGATGACATAGGGCATATCGTAATGCAGTACATGTATGTGCCACCTGGAGCTCCAGT
2365  31_HRV100b      AGGAGATGACATAGGGCATATCGTAATGCAGTACATGTATGTGCCACCTGGAGCTCCAGT
2366  32_HRV100       AGGAGATGACATAGGGCATATCGTAATGCAGTACATGTATGTGCCACCTGGAGCTCCAGT
2367  33_HRV66        GGGTGATGATATAGGACATATTGTGATGCAATACATGTATGTACCACCTGGAGCCCCAAT
2368  34_HRV66b|      GGGTGATGATATAGGACATATTGTGATGCAATACATGTATGTACCACCTGGAGCCCCAAT
```

FIG. D5 CONT'D

01.trace                                                                 9/20/2007 4:58 PM

| | | |
|---|---|---|
| 2369 | 35_HRV66a| | GGGTGATGATATAGGACATATTGTGATGCAATACATGTATGTACCACCTGGAGCCCCAAT |
| 2370 | 36_HRV77a| | AGGTGATGACATAGGACATGTTGTCATGCAATACATGTATGTACCACCAGGGGCACCCAT |
| 2371 | 37_HRV77b| | AGGTGATGACATAGGACATGTTGTCATGCAATACATGTATGTACCACCAGGGGCACCCAT |
| 2372 | 38_HRV77 | AGGTGATGACATAGGACATGTTGTCATGCAATACATGTATGTACCACCAGGGGCACCCAT |
| 2373 | 39_HRV62a | TGGTGCAGATATAGGTCACATAGTTATGCAATATATGTATGTACCACCTGGGGCTCCACT |
| 2374 | 40_HRV62b | TGGTGCAGATATAGGTCACATAGTTATGCAATATATGTATGTACCACCTGGGGCTCCACT |
| 2375 | 41_HRV25 | TGGTGCAGATATAGGTCACATAGTTATGCAATATATGTATGTGCCACCTGGAGCCCCATT |
| 2376 | 42_HRV29a | TGGTAATGATATAGGTCACATAGTTATGCAGTACATGTATGTACCACCTGGAGCTCCAGT |
| 2377 | 43_HRV29b | TGGTAATGATATAGGTCACATAGTTATGCAGTACATGTATGTACCACCTGGAGCTCCAGT |
| 2378 | 44_HRV44a | TGGTGATGATATAGGCCACATAGTTATGCAGTACATGTATGTACCACCTGGAGCTCCAGT |
| 2379 | 45_HRV44b | TGGTGATGATATAGGCCACATAGTTATGCAGTACATGTATGTACCACCTGGAGCTCCAGT |
| 2380 | 46_HRV31 | TGGTAGTGACATAGGCCATATAGTCATGCAATACATGTATGTACCACCTGGGGCCCCAGT |
| 2381 | 47_HRV31a| | TGGTAGTGACATAGGCCATATAGTCATGCAATACATGTATGTACCACCTGGGGCCCCAGT |
| 2382 | 48_HRV31b| | TGGTAGTGACATAGGCCATATAGTCATGCAATACATGTATGTACCACCTGGGGCCCCAGT |
| 2383 | 49_HRV47 | TGGTGATGACATAGGTCACATAGTTATGCAATACATGTATGTGCCGCCTGGGGCTCCAGT |
| 2384 | 50_HRV47a| | TGGTGATGACATAGGTCACATAGTTATGCAATACATGTATGTGCCGCCTGGGGCTCCAGT |
| 2385 | 51_HRV47b| | TGGTGATGACATAGGTCACATAGTTATGCAATACATGTATGTGCCGCCTGGGGCTCCAGT |
| 2386 | 52_HRV11 | AGGAAATGATATTGGTCATGTTGTAATGCAATATATGTATGTCCCACCAGGTGCTCCAGT |
| 2387 | 53_HRV11b| | AGGAAATGATATTGGTCATGTTGTAATGCAATATATGTATGTCCCACCAGGTGCTCCAGT |
| 2388 | 54_HRV11a| | AGGAAATGATATTGGTCATGTTGTAATGCAATATATGTATGTCCCACCAGGTGCTCCAGT |
| 2389 | 55_HRV76 | AGGGGATGACATTGGTCATGTAGTGATGCAATACATGTATGTCCCACCAGGCGCTCCAGT |
| 2390 | 56_HRV76b| | AGGGGATGACATTGGTCATGTAGTGATGCAATACATGTATGTCCCACCAGGCGCTCCAGT |
| 2391 | 57_HRV76a| | AGGGGATGACATTGGTCATGTAGTGATGCAATACATGTATGTCCCACCAGGCGCTCCAGT |
| 2392 | 58_HRV33 | GGGAGATGATGTTGGTCATGTTGTAATGCAGTACATGTATGTCCCACCAGGTGCACCAGC |
| 2393 | 59_HRV33b| | GGGAGATGATGTTGGTCATGTTGTAATGCAGTACATGTATGTCCCACCAGGTGCACCAGC |
| 2394 | 60_HRV33a| | GGGAGATGATGTTGGTCATGTTGTAATGCAGTACATGTATGTCCCACCAGGTGCACCAGC |
| 2395 | 61_HRV24a| | GGGAGATGACATTGGACATGTTGTAATGCAGTACATGTATATACCACCTGGAGCACCAGT |
| 2396 | 62_HRV24b| | GGGAGATGACATTGGACATGTTGTAATGCAGTACATGTATATACCACCTGGAGCACCAGT |
| 2397 | 63_HRV24 | GGGAGATGACATTGGACATGTTGTAATGCAGTACATGTATATACCACCTGGAGCACCAGT |
| 2398 | 64_HRV90 | GGGCAATGATATTGGACATGTTGTGATGCAATACATGTATATACCACCTGGGGCACCAGT |
| 2399 | 65_HRV90a| | GGGCAATGATATTGGACATGTTGTGATGCAATACATGTATATACCACCTGGGGCACCAGT |
| 2400 | 66_HRV90b| | GGGCAATGATATTGGACATGTTGTGATGCAATACATGTATATACCACCTGGGGCACCAGT |
| 2401 | 67_HRV34 | AGGTGATGATATTGGACATGTTGTGATGCAATACATGTATGTACCACCAGGTGCACCAAT |
| 2402 | 68_HRV34b| | AGGTGATGATATTGGACATGTTGTGATGCAATACATGTATGTACCACCAGGTGCACCAAT |
| 2403 | 69_HRV34a| | AGGTGATGATATTGGACATGTTGTGATGCAATACATGTATGTACCACCAGGTGCACCAAT |
| 2404 | 70_HRV50a| | GGGTGTTGATATTGGACATGTTGTCATGCAATACATGTATGTCCCACCAGGTGCACCAAT |
| 2405 | 71_HRV50b| | GGGTGTTGATATTGGACATGTTGTCATGCAATACATGTATGTCCCACCAGGTGCACCAAT |
| 2406 | 72_HRV50 | GGGTGTTGATATTGGACATGTTGTCATGCAATACATGTATGTCCCACCAGGTGCACCAAT |
| 2407 | 73_HRV18a| | GGGTGATGACATAGGACATATTGTTATGCAGTACATGTATGTTCCTCCAGGAGCACCAAT |
| 2408 | 74_HRV18b| | GGGTGATGACATAGGACATATTGTTATGCAGTACATGTATGTTCCTCCAGGAGCACCAAT |
| 2409 | 75_HRV18 | GGGTGATGACATAGGACATATTGTTATGCAGTACATGTATGTTCCTCCAGGAGCACCAAT |
| 2410 | 76_HRV55 | GGGAGATGACATTGGACATGTAGTCATGCAATACATGTATGTTCCACCTGGAGCACCAAT |
| 2411 | 77_HRV55b| | GGGAGATGACATTGGACATGTAGTCATGCAATACATGTATGTTCCACCTGGAGCACCAAT |
| 2412 | 78_HRV55a| | GGGAGATGACATTGGACATGTAGTCATGCAATACATGTATGTTCCACCTGGAGCACCAAT |
| 2413 | 79_HRV57 | AGGTGAGGATATAGGCCATGTTGTAATGCAATACATGTATGTCCCTCCTGGGGCACCAAT |
| 2414 | 80_HRV57a| | AGGTGAGGATATAGGCCATGTTGTAATGCAATACATGTATGTCCCTCCTGGGGCACCAAT |
| 2415 | 81_HRV57b| | AGGTGAGGATATAGGCCATGTTGTAATGCAATACATGTATGTCCCTCCTGGGGCACCAAT |
| 2416 | 82_HRV21 | AACGGGTGACATAGGCCATGTTGTAATGCAATATATGTATGTCCCACCAGGTGCTCCAAT |
| 2417 | 83_HRVHan | AGCGGGTGACATAGGACATGTTGTGATGCAATATATGTATGTCCCACCAGGTGCTCCAAT |
| 2418 | 84_HRV43 | AAGCAATGATATAGGCCATGTGGTAATGCAGTACATGTATGTACCACCAGGTGCGCCAAT |
| 2419 | 85_HRV43b| | AAGCAATGATATAGGCCATGTGGTAATGCAGTACATGTATGTACCACCAGGTGCGCCAAT |
| 2420 | 86_HRV43a| | AAGCAATGATATAGGCCATGTGGTAATGCAGTACATGTATGTACCACCAGGTGCGCCAAT |
| 2421 | 87_HRV75 | AGGGAATGACATAGGCCATGTAGTAATGCAATACATGTATGTACCACCAGGAGCACCAAT |
| 2422 | 88_HRV75b| | AGGGAATGACATAGGCCATGTAGTAATGCAATACATGTATGTACCACCAGGAGCACCAAT |
| 2423 | 89_HRV75a| | AGGGAATGACATAGGCCATGTAGTAATGCAATACATGTATGTACCACCAGGAGCACCAAT |
| 2424 | 96_HRV9a|d | AAGTGATAGCGTTGGCCATGTTGTTATGCAGTACATGTATGTACCACCAGGGGCACCTTT |
| 2425 | 97_HRV9b|d | AAGTGATAGCGTTGGCCATGTTGTTATGCAGTACATGTATGTACCACCAGGGGCACCTTT |
| 2426 | 98_HRV9 | AAGTGATAGCGTTGGCCATGTTGTTATGCAGTACATGTATGTACCACCAGGGGCACCTTT |
| 2427 | 99_HRV32 | AAGTGACAGCATTGGTCATGTTGTTATGCAGTACATGTATGTACCACCAGGGGCTCCTCT |
| 2428 | 100_HRV32a | AAGTGACAGCATTGGTCATGTTGTTATGCAGTACATGTATGTACCACCAGGGGCTCCTCT |
| 2429 | 101_HRV32b | AAGTGACAGCATTGGTCATGTTGTTATGCAGTACATGTATGTACCACCAGGGGCTCCTCT |
| 2430 | 102_HRV67 | GAGTGACAGCATTGGGCATGTTGTAATGCAATATATGTATGTACCTCCAGGAGCACCATT |
| 2431 | 103_HRV67a | GAGTGACAGCATTGGGCATGTTGTAATGCAATATATGTATGTACCTCCAGGAGCACCATT |
| 2432 | 104_HRV67b | GAGTGACAGCATTGGGCATGTTGTAATGCAATATATGTATGTACCTCCAGGAGCACCATT |

FIG. D5 CONT'D

01.trace                                                                9/20/2007 4:58 PM

```
2433 105_HRV15   GAGTGATAACATCGGTCATGTTGTCATGCAATATATGTATGTTCCTCCGGGAGCCCCTTT
2434 106_HRV15a  GAGTGATAACATCGGTCATGTTGTCATGCAATATATGTATGTTCCTCCGGGAGCCCCTTT
2435 107_HRV15b  GAGTGATAACATCGGTCATGTTGTCATGCAATATATGTATGTTCCTCCGGGAGCCCCTTT
2436 108_HRV74a  AAGTGACAACATTGGCCATGTTGTTATGCAATACATGTATGTCCCCCCAGGAGCACCTTT
2437 109_HRV74b  AAGTGACAACATTGGCCATGTTGTTATGCAATACATGTATGTCCCCCCAGGAGCACCTTT
2438 110_HRV74   AAGTGACAACATTGGCCATGTTGTTATGCAATACATGTATGTCCCCCCAGGAGCACCTTT
2439 111_HRV38a  AAATGAAGGTGTGGGGCATGTTGTTATGCAGTATATGTATGTCCCTCCAGGGGCACCATT
2440 112_HRV38b  AAATGAAGGTGTGGGGCATGTTGTTATGCAGTATATGTATGTCCCTCCAGGGGCACCATT
2441 113_HRV38   AAATGAAGGTGTGGGGCATGTTGTTATGCAGTATATGTATGTCCCTCCAGGGGCACCATT
2442 114_HRV60   AAATGATGGCATAGGTCATGTTGTCATGCAATACATGTATGTCCCCCCAGGAGCACCATT
2443 115_HRV60a  AAATGATGGCATAGGTCATGTTGTCATGCAATACATGTATGTCCCCCCAGGAGCACCATT
2444 116_HRV60b  AAATGATGGCATAGGTCATGTTGTCATGCAATACATGTATGTCCCCCCAGGAGCACCATT
2445 117_HRV64a  GAGTGCTAACATTGGTCATGTTGTTATGCAATATATGTATGTCCCTCCTGGAGCTCCAAT
2446 118_HRV64b  GAGTGCTAACATTGGTCATGTTGTTATGCAATATATGTATGTCCCTCCTGGAGCTCCAAT
2447 119_HRV64   GAGTGCTAACATTGGTCATGTTGTTATGCAATATATGTATGTCCCTCCTGGAGCTCCAAT
2448 120_HRV94a  AAGTGCTAATATTGGTCATGTTGTCATGCAGTACATGTATGTTCCTCCTGGAGCTCCAAA
2449 121_HRV94b  AAGTGCTAATATTGGTCATGTTGTCATGCAGTACATGTATGTTCCTCCTGGAGCTCCAAA
2450 122_HRV94   AAGTGCTAATATTGGTCATGTTGTCATGCAGTACATGTATGTTCCTCCTGGAGCTCCAAA
2451 123_HRV22   AAGTAAAAACATTGGTCATGTGGTCATGCAATACATGTATGTTCCGCCTGGAGCTCCTAA
2452 124_HRV22a  AAGTAAAAACATTGGTCATGTGGTCATGCAATACATGTATGTTCCGCCTGGAGCTCCTAA
2453 125_HRV22b  AAGTAAAAACATTGGTCATGTGGTCATGCAATACATGTATGTTCCGCCTGGAGCTCCTAA
2454 126_HRV82   AAGTAATGATATTGGGCATGTAGTGATGCAATACATGTATGTCCCACCAGGTGCTCCTAA
2455 127_HRV82b  AAGTAATGATATTGGGCATGTAGTGATGCAATACATGTATGTCCCACCAGGTGCTCCTAA
2456 128_HRV82a  AAGTAATGATATTGGGCATGTAGTGATGCAATACATGTATGTCCCACCAGGTGCTCCTAA
2457 129_HRV19   AAGTAAAAACATTGGACATGTTGTTATGCAATACATGTATGTGCCTCCTGGTGCTCCTAT
2458 130_HRV19a  AAGTAAAAACATTGGACATGTTGTTATGCAATACATGTATGTGCCTCCTGGTGCTCCTAT
2459 131_HRV19b  AAGTAAAAACATTGGACATGTTGTTATGCAATACATGTATGTGCCTCCTGGTGCTCCTAT
2460 132_HRV13   AGGTGGTGATGTCGGACATGTTGTTATGCAATACATGTATGTACCGCCCGGTGCACCCCT
2461 133_HRV13a  AGGTGGTGATGTCGGACATGTTGTTATGCAATACATGTATGTACCGCCCGGTGCACCCCT
2462 134_HRV13b  AGGTGGTGATGTCGGACATGTTGTTATGCAATACATGTATGTACCGCCCGGTGCACCCCT
2463 135_HRV41   GGGTAGTGATGTCGGACATGTTGTCATGCAATACATGTTCGTACCACCTGGCGCACCCCT
2464 136_HRV41a  GGGTAGTGATGTCGGACATGTTGTCATGCAATACATGTTCGTACCACCTGGCGCACCCCT
2465 137_HRV41b  GGGTAGTGATGTCGGACATGTTGTCATGCAATACATGTTCGTACCACCTGGCGCACCCCT
2466 138_HRV73   AAGTGGAGATGTGGGACATGTAGTTATGCAGTATATGTATGTCCCACCTGGAGCCCCTCT
2467 139_HRV73b  AAGTGGAGATGTGGGACATGTAGTTATGCAGTATATGTATGTCCCACCTGGAGCCCCTCT
2468 140_HRV73a  AAGTGGAGATGTGGGACATGTAGTTATGCAGTATATGTATGTCCCACCTGGAGCCCCTCT
2469 141_HRV61   AGGTGGTGACATTGGACACGTGGTCATGCAATACATGTATGTTCCACCTGGTGCACCTAC
2470 142_HRV61a  AGGTGGTGACATTGGACACGTGGTCATGCAATACATGTATGTTCCACCTGGTGCACCTAC
2471 143_HRV61b  AGGTGGTGACATTGGACACGTGGTCATGCAATACATGTATGTTCCACCTGGTGCACCTAC
2472 144_HRV96   GAGTGGTGATATTGGTCATGTGGTCATGCAATATATGTATGTTCCACCAGGTGCCCCCAC
2473 145_HRV96b  GAGTGGTGATATTGGTCATGTGGTCATGCAATATATGTATGTTCCACCAGGTGCCCCCAC
2474 146_HRV96a  GAGTGGTGATATTGGTCATGTGGTCATGCAATATATGTATGTTCCACCAGGTGCCCCCAC
2475  90_HRV16a| AGATGGTCACATTGGTCATATAGTCATGCAATATATGTATGTACCACCAGGAGCACCTAT
2476  91_HRV16b| AGATGGTCACATTGGTCATATAGTCATGCAATATATGTATGTACCACCAGGAGCACCTAT
2477  92_1AYM_A  AGATGGTCACATTGGTCATATAGTCATGCAATATATGTATGTACCACCAGGAGCACCTAT
2478  93_HRV81a| GGAAGGTCATATTGGTCATATAGTAATGCAATACATGTATGTACCACCAGGAGCACCCAT
2479  94_HRV81b| GGAAGGTCATATTGGTCATATAGTAATGCAATACATGTATGTACCACCAGGAGCACCCAT
2480  95_HRV81   GGAAGGTCATATTGGTCATATAGTAATGCAATACATGTATGTACCACCAGGAGCACCCAT
2481 147_HRV2    TAGTCAGGACATTGGACACATCACAATGCAATACATGTATGTTCCACCTGGTGCACCGGT
2482 148_HRV2a|  TAGTCAGGACATTGGACACATCACAATGCAATACATGTATGTTCCACCTGGTGCACCGGT
2483 149_HRV2b|  TAGTCAGGACATTGGACACATCACAATGCAATACATGTATGTTCCACCTGGTGCACCGGT
2484 150_HRV49a  TAGCAAGGATATTGGACACATTACAATGCAATACATGTATGTGCCGCCAGGTGCACCTGT
2485 151_HRV49b  TAGCAAGGATATTGGACACATTACAATGCAATACATGTATGTGCCGCCAGGTGCACCTGT
2486 152_HRV49   TAGCAAGGATATTGGACACATTACAATGCAATACATGTATGTGCCGCCAGGTGCACCTGT
2487 153_HRV23a  TAGTCAAGATATTGGTCACATCACAATGCAGTATATGTATGTCCCACCAGGTGCTCCAAT
2488 154_HRV23b  TAGTCAAGATATTGGTCACATCACAATGCAGTATATGTATGTCCCACCAGGTGCTCCAAT
2489 155_HRV23   TAGTCAAGATATTGGTCACATCACAATGCAGTATATGTATGTCCCACCAGGTGCTCCAAT
2490 156_HRV30a  CAGCCAAGATATCGGACACATTACAATGCAGTATATGTATGTTCCACCTGGCGCTCCAAT
2491 157_HRV30b  CAGCCAAGATATCGGACACATTACAATGCAGTATATGTATGTTCCACCTGGCGCTCCAAT
2492 158_HRV30   CAGCCAAGATATCGGACACATTACAATGCAGTATATGTATGTTCCACCTGGCGCTCCAAT
2493 159_HRV7    AGGTAATGATATTGGACATATAGTTATGCAATTTATGTATGTACCTCCAGGGGCCCCAGT
2494 160_HRV7b|  AGGTAATGATATTGGACATATAGTTATGCAATTTATGTATGTACCTCCAGGGGCCCCAGT
2495 161_HRV7a|  AGGTAATGATATTGGACATATAGTTATGCAATTTATGTATGTACCTCCAGGGGCCCCAGT
2496 162_HRV88   AGGTGATGATACTGGACATATAGTACTGCAATTCATGTATGTGCCTCCAGGTGCACCAAT
```

FIG. D5 CONT'D

01.trace                                                                9/20/2007 4:58 PM

```
2497  163_HRV88a   AGGTGATGATACTGGACATATAGTACTGCAATTCATGTATGTGCCTCCAGGTGCACCAAT
2498  164_HRV88b   AGGTGATGATACTGGACATATAGTACTGCAATTCATGTATGTGCCTCCAGGTGCACCAAT
2499  165_HRV36a   GGGAGATGATAGTGGGCATGTAGTATTACAATTCATGTATGTACCTCCAGGAGCGCCTGT
2500  166_HRV36b   GGGAGATGATAGTGGGCATGTAGTATTACAATTCATGTATGTACCTCCAGGAGCGCCTGT
2501  167_HRV36    GGGAGATGATAGTGGGCATGTAGTATTACAATTCATGTATGTACCTCCAGGAGCGCCTGT
2502  168_HRV89a   AGGAAATGATAGTGGACATATAGTATTGCAATTTATGTATGTACCCCCAGGAGCACCTGT
2503  169_HRV89b   AGGAAATGATAGTGGACATATAGTATTGCAATTTATGTATGTACCCCCAGGAGCACCTGT
2504  170_HRV89    AGGAAATGATAGTGGACATATAGTATTGCAATTTATGTATGTACCCCCAGGAGCACCTGT
2505  171_HRV58    AGGAGAAGATAATGGACATATTGTGTTACAATTTATGTATGTACCCCCAGGAGCACCTGT
2506  172_HRV58a   AGGAGAAGATAATGGACATATTGTGTTACAATTTATGTATGTACCCCCAGGAGCACCTGT
2507  173_HRV58b   AGGAGAAGATAATGGACATATTGTGTTACAATTTATGTATGTACCCCCAGGAGCACCTGT
2508  174_HRV12a   AGAAGGAAGCAATGGTCACGTGGTGGTCCAATACATGTATGTACCTCCTGGTGCCCCACT
2509  175_HRV12b   AGAAGGAAGCAATGGTCACGTGGTGGTCCAATACATGTATGTACCTCCTGGTGCCCCACT
2510  176_HRV12    AGAAGGAAGCAATGGTCACGTGGTGGTCCAATACATGTATGTACCTCCTGGTGCCCCACT
2511  177_HRV78a   AGGAGACAATAATGGACATGTGGTGCTTCAATTTATGTTTGTTCCACCTGGAGCCCCTAT
2512  178_HRV78b   AGGAGACAATAATGGACATGTGGTGCTTCAATTTATGTTTGTTCCACCTGGAGCCCCTAT
2513  179_HRV78    AGGAGACAATAATGGACATGTGGTGCTTCAATTTATGTTTGTTCCACCTGGAGCCCCTAT
2514  180_HRV20    AGGTCGGGATAATGGGCATGTTGTTTTACAGTATATGTATGTACCACCAGGGGCACCAAT
2515  181_HRV20a   AGGTCGGGATAATGGGCATGTTGTTTTACAGTATATGTATGTACCACCAGGGGCACCAAT
2516  182_HRV20b   AGGTCGGGATAATGGGCATGTTGTTTTACAGTATATGTATGTACCACCAGGGGCACCAAT
2517  183_HRV68    TGGAAAAGATAATGGCCATGTGGTTTTACAGTACATGTATGTGCCGCCAGGGGCACCCAT
2518  184_HRV68a   TGGAAAAGATAATGGCCATGTGGTTTTACAGTACATGTATGTGCCGCCAGGGGCACCCAT
2519  185_HRV68b   TGGAAAAGATAATGGCCATGTGGTTTTACAGTACATGTATGTGCCGCCAGGGGCACCCAT
2520  186_HRV28    AGGTGATGATAATGGGCATGTAGTTATGCAATATATGTATGTACCTCCAGGAGCCCCCAT
2521  187_HRV28a   AGGTGATGATAATGGGCATGTAGTTATGCAATATATGTATGTACCTCCAGGAGCCCCCAT
2522  188_HRV28b   AGGTGATGATAATGGGCATGTAGTTATGCAATATATGTATGTACCTCCAGGAGCCCCCAT
2523  189_HRV53a   ACAAGGGAATAACGGGCACGTGGTGATACAATACATGTATGTACCACCGGGTGCTCCAAT
2524  190_HRV53b   ACAAGGGAATAACGGGCACGTGGTGATACAATACATGTATGTACCACCGGGTGCTCCAAT
2525  191_HRV53    ACAAGGGAATAACGGGCACGTGGTGATACAATACATGTATGTACCACCGGGTGCTCCAAT
2526  192_HRV46a   AGGGGATGATATTGGACATGTGGTCATACAATATATGTATGTGCCTCCTGGTGCTCCATT
2527  193_HRV46b   AGGGGATGATATTGGACATGTGGTCATACAATATATGTATGTGCCTCCTGGTGCTCCATT
2528  194_HRV46    AGGGGATGATATTGGACATGTGGTCATACAATATATGTATGTGCCTCCTGGTGCTCCATT
2529  195_HRV80a   AGGGGAGGACATTGGTCATGTAGTTATTCAATACATGTACGTACCACCAGGGGCCCCGTT
2530  196_HRV80b   AGGGGAGGACATTGGTCATGTAGTTATTCAATACATGTACGTACCACCAGGGGCCCCGTT
2531  197_HRV80    AGGGGAGGACATTGGTCATGTAGTTATTCAATACATGTACGTACCACCAGGGGCCCCGTT
2532  198_HRV51    GGGTGATGACATAGGGCACATTGTACTTCAATACATGTATGTACCCCCTGGAGGACCAGT
2533  199_HRV51a   GGGTGATGACATAGGGCACATTGTACTTCAATACATGTATGTACCCCCTGGAGGACCAGT
2534  200_HRV51b   GGGTGATGACATAGGGCACATTGTACTTCAATACATGTATGTACCCCCTGGAGGACCAGT
2535  201_HRV65a   AGGTGATGACATAGGGCACATAGTGCTTCAATATATGTATGTGCCTCCTGGTGGTCCTGT
2536  202_HRV65b   AGGTGATGACATAGGGCACATAGTGCTTCAATATATGTATGTGCCTCCTGGTGGTCCTGT
2537  203_HRV65    AGGTGATGACATAGGGCACATAGTGCTTCAATATATGTATGTGCCTCCTGGTGGTCCTGT
2538  204_HRV71a   AGGAGATGATTTAGGACATATTGTACTCCAGTACATGTATGTTCCCCCAGGTGGTCCAAT
2539  205_HRV71b   AGGAGATGATTTAGGACATATTGTACTCCAGTACATGTATGTTCCCCCAGGTGGTCCAAT
2540  206_HRV71    AGGAGATGATTTAGGACATATTGTACTCCAGTACATGTATGTTCCCCCAGGTGGTCCAAT
2541  207_HRV8     AAAAGGTGACCTTGGACACATAGTCCTTCAATACATGTATTTCCCCCGGGTGCACCTCT
2542  208_HRV95    AGAAGGTGACCTTGGACACATAGTCCTCCAATACATGTATGTTCCCCCGGGTGCACCTCT
2543  209_HRV45    AGAAGGTAACTTGGGACACATTGTTGTGCAATACATGTTTGTACCACCAGGAGCACCTCT
2544  210_HRV45a   AGAAGGTAACTTGGGACACATTGTTGTGCAATACATGTTTGTACCACCAGGAGCACCTCT
2545  211_HRV45b   AGAAGGTAACTTGGGACACATTGTTGTGCAATACATGTTTGTACCACCAGGAGCACCTCT
2546  212_HRV6     ------------------------------------------------------------
2547  213_HRV6a|   ------------------------------------------------------------
2548  214_HRV6b|   ------------------------------------------------------------
2549  215_HRV37    ------------------------------------------------------------
2550  216_HRV37a   ------------------------------------------------------------
2551  217_HRV37b   ------------------------------------------------------------
2552  218_HRV3     ------------------------------------------------------------
2553  219_HRV3a|   ------------------------------------------------------------
2554  220_HRV3b|   ------------------------------------------------------------
2555  221_HRV14    ------------------------------------------------------------
2556  222_HRV14a   ------------------------------------------------------------
2557  223_HRV14b   ------------------------------------------------------------
2558  224_HRV72    ------------------------------------------------------------
2559  225_HRV72a   ------------------------------------------------------------
2560  226_HRV72b   ------------------------------------------------------------
```

FIG. D5 CONT'D 01.trace                                                              9/20/2007 4:58 PM

```
2561 227_HRV83     ----------------------------------------------------------------
2562 228_HRV83a    ----------------------------------------------------------------
2563 229_HRV83b    ----------------------------------------------------------------
2564 230_HRV92     ----------------------------------------------------------------
2565 231_HRV92a    ----------------------------------------------------------------
2566 232_HRV92b    ----------------------------------------------------------------
2567 233_HRV79     ----------------------------------------------------------------
2568 234_HRV79a    ----------------------------------------------------------------
2569 235_HRV79b    ----------------------------------------------------------------
2570 236_HRV35     ----------------------------------------------------------------
2571 237_HRV35a    ----------------------------------------------------------------
2572 238_HRV35b    ----------------------------------------------------------------
2573 239_1HRV86    ----------------------------------------------------------------
2574 240_1HRV86    ----------------------------------------------------------------
2575 241_1HRV86    ----------------------------------------------------------------
2576 242_HRV70     ----------------------------------------------------------------
2577 243_HRV70a    ----------------------------------------------------------------
2578 244_HRV70b    ----------------------------------------------------------------
2579 245_HRV91     ----------------------------------------------------------------
2580 246_HRV91a    ----------------------------------------------------------------
2581 247_HRV91b    ----------------------------------------------------------------
2582 248_HRV17     ----------------------------------------------------------------
2583 249_HRV17a    ----------------------------------------------------------------
2584 250_HRV17b    ----------------------------------------------------------------
2585 251_HRV69     ----------------------------------------------------------------
2586 252_HRV69a    ----------------------------------------------------------------
2587 253_HRV69b    ----------------------------------------------------------------
2588 254_HRV48     ----------------------------------------------------------------
2589 255_HRV48a    ----------------------------------------------------------------
2590 256_HRV48b    ----------------------------------------------------------------
2591 257_HRV52     ----------------------------------------------------------------
2592 258_HRV52a    ----------------------------------------------------------------
2593 259_HRV52b    ----------------------------------------------------------------
2594 260_HRV4      ----------------------------------------------------------------
2595 261_HRV4a|    ----------------------------------------------------------------
2596 262_HRV4b|    ----------------------------------------------------------------
2597 263_HRV99     ----------------------------------------------------------------
2598 264_HRV99a    ----------------------------------------------------------------
2599 265_HRV99b    ----------------------------------------------------------------
2600 266_HRV5      ----------------------------------------------------------------
2601 267_HRV5a|    ----------------------------------------------------------------
2602 268_HRV5b|    ----------------------------------------------------------------
2603 269_HRV42     ----------------------------------------------------------------
2604 270_HRV42a    ----------------------------------------------------------------
2605 271_HRV42b    ----------------------------------------------------------------
2606 272_HRV26     ----------------------------------------------------------------
2607 273_HRV26a    ----------------------------------------------------------------
2608 274_HRV26b    ----------------------------------------------------------------
2609 275_HRV27     ----------------------------------------------------------------
2610 276_HRV27a    ----------------------------------------------------------------
2611 277_HRV27b    ----------------------------------------------------------------
2612 278_HRV93     ----------------------------------------------------------------
2613 279_HRV93a    ----------------------------------------------------------------
2614 280_HRV93b    ----------------------------------------------------------------
2615 281_HRV97     ----------------------------------------------------------------
2616 282_HRV97a    ----------------------------------------------------------------
2617 283_HRV97b    ----------------------------------------------------------------
2618 284_HRV84     ----------------------------------------------------------------
2619 285_HRV84a    ----------------------------------------------------------------
2620 286_HRV84b    ----------------------------------------------------------------
2621 287_HRV87     ----------------------------------------------------------------
2622 288_HRV87a    ----------------------------------------------------------------
2623 289_HRV87b    ----------------------------------------------------------------
2624 GROUP 1       ----------------------------------------------------------------
```

FIG. D5 CONT'D

01.trace                                                                                      9/20/2007 4:58 PM

```
2625
2626  1_HRV1A1|d     TCCTTCAAAAAGAAACGATTTCTCATGGCAATCAGGCACCAATATGTCAATATTCTGGCA
2627  2_HRV1A2|d     TCCTTCAAAAAGAAACGATTTCTCATGGCAATCAGGCACCAATATGTCAATATTCTGGCA
2628  3_HRV1A|cD     TCCTTCAAAAAGAAACGATTTCTCATGGCAATCAGGCACCAATATGTCAATATTCTGGCA
2629  4_HRV1B1|d     TCCAAAAACAAGAAATGATTTCTCATGGCAATCAGGCACTAATATGTCAATATTCTGGCA
2630  5_HRV1B2|d     TCCAAAAACAAGAAATGATTTCTCATGGCAATCAGGCACTAATATGTCAATATTCTGGCA
2631  6_HRV1B        TCCAAAAACAAGAAATGATTTCTCATGGCAATCAGGCACTAATATGTCAATATTCTGGCA
2632  7_HRV40a|d     ACCAAAGAAAAGAAATGATTACACATGGCAGTCAGGCACTAATGCTTCTGTATTCTGGCA
2633  8_HRV40b|d     ACCAAAGAAAAGAAATGATTACACATGGCAGTCAGGCACTAATGCTTCTGTATTCTGGCA
2634  9_HRV40        ACCAAAGAAAAGAAATGATTACACATGGCAGTCAGGCACTAATGCTTCTGTATTCTGGCA
2635  10_HRV85       ACCAAGGAAAAGAGATGATTACACATGGCAATCAGGTACTAATGCTTCCGTGTTTTGGCA
2636  11_HRV85a|     ACCAAGGAAAAGAGATGATTACACATGGCAATCAGGTACTAATGCTTCCGTGTTTTGGCA
2637  12_HRV85b|     ACCAAGGAAAAGAGATGATTACACATGGCAATCAGGTACTAATGCTTCCGTGTTTTGGCA
2638  13_HRV56a|     TCCAAACTCAAGAGATGATTTTACATGGCAATCTGGCACCAATGCTTCTGTCTTTTGGCA
2639  14_HRV56b|     TCCAAACTCAAGAGATGATTTTACATGGCAATCTGGCACCAATGCTTCTGTCTTTTGGCA
2640  15_HRV56       TCCAAACTCAAGAGATGATTTTACATGGCAATCTGGCACCAATGCTTCTGTCTTTTGGCA
2641  16_HRV54       ACCAGAAAAAAGGAATGATTACACCTGGGAGTCAAGCACAAACCCTTCTATATTTTGGCA
2642  17_HRV98       ACCTAAAAAGAGGAATGATTATACTTGGGAATCAAGCACAAACCCTTCTATATTCTGGCA
2643  18_HRV59a|     GCCCACAAAGAGAGATGATTACACATGGCAATCTGGTACTAATGCTTCAATATTCTGGCA
2644  19_HRV59b|     GCCCACAAAGAGAGATGATTACACATGGCAATCTGGTACTAATGCTTCAATATTCTGGCA
2645  20_HRV59       GCCCACAAAGAGAGATGATTACACATGGCAATCTGGTACTAATGCTTCAATATTCTGGCA
2646  21_HRV63       ACCCACCCGAAGAGAAGATTACACATGGCAATCTGGCACTAATGCTTCAATATTCTGGCA
2647  22_HRV63b|     ACCCACCCGAAGAGAAGATTACACATGGCAATCTGGCACTAATGCTTCAATATTCTGGCA
2648  23_HRV63a|     ACCCACCCGAAGAGAAGATTACACATGGCAATCTGCCACTAATGCTTCAATATTCTGGCA
2649  24_HRV39       ACCTAAGAAGAGAGATGATTACACATGGCAATCTGGAACAAATGCCTCAGTTTTCTGGCA
2650  25_HRV39a|     ACCTAAGAAGAGAGATGATTACACATGGCAATCTGGAACAAATGCCTCAGTTTTCTGGCA
2651  26_HRV39b|     ACCTAAGAAGAGAGATGATTACACATGGCAATCTGGAACAAATGCCTCAGTTTTCTGGCA
2652  27_HRV10a|     ACCAACTAAGAGAGATGATTTTGCTTGGCAGTCGGGAACAAATGCATCAGTCTTCTGGCA
2653  28_HRV10b|     ACCAACTAAGAGAGATGATTTTGCTTGGCAGTCGGGAACAAATGCATCAGTCTTCTGGCA
2654  29_HRV10       ACCAACTAAGAGAGATGATTTTGCTTGGCAGTCGGGAACAAATGCATCAGTCTTCTGGCA
2655  30_HRV100a     TCCAACAAAAAGGGATGATTTTGCATGGCAATCAGGCACAAATGCATCAGTTTTTTGGCA
2656  31_HRV100b     TCCAACAAAAAGGGATGATTTTGCATGGCAATCAGGCACAAATGCATCAGTTTTTTGGCA
2657  32_HRV100      TCCAACAAAAAGGGATGATTTTGCATGGCAATCAGGCACAAATGCATCAGTTTTTTGGCA
2658  33_HRV66       TCCAGATAATAGAACACACTTTGCTTGGCAATCAGGAACAAATGCATCTATATTCTGGCA
2659  34_HRV66b|     TCCAGATAATAGAACACACTTTGCTTGGCAATCAGGAACAAATGCATCTATATTCTGGCA
2660  35_HRV66a|     TCCAGATAATAGAACACACTTTGCTTGGCAATCAGGAACAAATGCATCTATATTCTGGCA
2661  36_HRV77a|     ACCAGATAGCAGGACTCATTTTGCATGGCAGTCAGGGACTAATGCATCAATATTCTGGCA
2662  37_HRV77b|     ACCAGATAGCAGGACTCATTTTGCATGGCAGTCAGGGACTAATGCATCAATATTCTGGCA
2663  38_HRV77       ACCAGATAGCAGGACTCATTTTGCATGGCAGTCAGGGACTAATGCATCAATATTCTGGCA
2664  39_HRV62a      ACCAACAGACAGAAAGCATTTTGCCTGGCAATCAAGTACTAATGCATCAATATTTTGGCA
2665  40_HRV62b      ACCAACAGACAGAAAGCATTTTGCCTGGCAATCAAGTACTAATGCATCAATATTTTGGCA
2666  41_HRV25       ACCAACAGACAGAAAACACTTTGCATGGCAATCAAGTACTAATGCATCAATATTTTGGCA
2667  42_HRV29a      ACCAAATGACAGAAATCATTTTGCATGGCAATCAGGGACTAATGCATCAATATTCTGGCA
2668  43_HRV29b      ACCAAATGACAGAAATCATTTTGCATGGCAATCAGGGACTAATGCATCAATATTCTGGCA
2669  44_HRV44a      ACCAGATGACAGAAACCACTTTGCATGGCAATCGGGGACTAATGCATCAATATTCTGGCA
2670  45_HRV44b      ACCAGATGACAGAATCCACTTTGCATGGCAATCGGGGAATAATGCATCAATATTCTGGCA
2671  46_HRV31       ACCAACAAATAGAAAACATTTTGCATGGCAATCAGGTACTAATGCATCGATTTTCTGGCA
2672  47_HRV31a|     ACCAACAAATAGAAAACATTTTGCATGGCAATCAGGTACTAATGCATCGATTTTCTGGCA
2673  48_HRV31b|     ACCAACAAATAGAAAACATTTTGCATGGCAATCAGGTACTAATGCATCGATTTTCTGGCA
2674  49_HRV47       GCCAACAAGTAGAGAGCACTTTGCATGGCAGTCAGGTACCAATGCATCAACTTTCTGGCA
2675  50_HRV47a|     GCCAACAAGTAGAGAGCACTTTGCATGGCAGTCAGGTACCAATGCATCAACTTTCTGGCA
2676  51_HRV47b|     GCCAACAAGTAGAGAGCACTTTGCATGGCAGTCAGGTACCAATGCATCAATTTTCTGGCA
2677  52_HRV11       TCCAGAGAAAAGAGATGATTATACATGGCAATCAGGAACAAATGCATCTATTTTCTGGCA
2678  53_HRV11b|     TCCAGAGAAAAGAGATGATTATACATGGCAATCAGGAACAAATGCATCTATTTTCTGGCA
2679  54_HRV11a|     TCCAGAGAAAAGAGATGATTATACATGGCAATCAGGAACAAATGCATCTATTTTCTGGCA
2680  55_HRV76       TCCAAAGAAGAGAGATGACTACACATGGCAGTCAGGAACCAATGCATCTATTTTCTGGCA
2681  56_HRV76b|     TCCAAAGAAGAGAGATGACTACACATGGCAGTCAGGAACCAATGCATCTATTTTCTGGCA
2682  57_HRV76a|     TCCAAAGAAGAGAGATGACTACACATGGCAGTCAGGAACCAATGCATCTATTTTCTGGCA
2683  58_HRV33       TCCAGAAAAGAGAGATGATTACACATGGCAATCAGGAACAAATGCATCTGTCTTTTGGCA
2684  59_HRV33b|     TCCAGAAAAGAGAGATGATTACACATGGCAATCAGGAACAAATGCATCTGTCTTTTGGCA
2685  60_HRV33a|     TCCAGAAAAGAGAGATGATTACACATGGCAATCAGGAACAAATGCATCTGTCTTTTGGCA
2686  61_HRV24a|     CCCAACAAAGAGAGATGATTATACATGGCAATCAGGAACAAATGCATCTGTCTTTTGGCA
2687  62_HRV24b|     CCCAACAAAGAGAGATGATTATACATGGCAATCAGGAACAAATGCATCTGTCTTTTGGCA
2688  63_HRV24       CCCAACAAAGAGAGATGATTATACATGGCAATCAGGAACAAATGCATCTGTCTTTTGGCA
```

FIG. D5 CONT'D 01.trace                                                                 9/20/2007 4:58 PM

```
2689  64_HRV90     ACCTGAGAAGAGGGATGATTATGCATGGCAATCAGGCACTAATGCATCTATCTTTTGGCA
2690  65_HRV90a|   ACCTGAGAAGAGGGATGATTATGCATGGCAATCAGGCACTAATGCATCTATCTTTTGGCA
2691  66_HRV90b|   ACCTGAGAAGAGGGATGATTATGCATGGCAATCAGGCACTAATGCATCTATCTTTTGGCA
2692  67_HRV34     ACCTAAAACTAGAGATGATTTTGCATGGCAATCTGGAACAAATGCCTCAATATTTTGGCA
2693  68_HRV34b|   ACCTAAAACTAGAGATGATTTTGCATGGCAATCTGGAACAAATGCCTCAATATTTTGGCA
2694  69_HRV34a|   ACCTAAAACTAGAGATGATTTTGCATGGCAATCTGGAACAAATGCCTCAATATTTTGGCA
2695  70_HRV50a|   ACCCAAGACTAGGGATGATTTTGCCTGGCAATCTGGAACTAATGCTTCAATCTTTTGGCA
2696  71_HRV50b|   ACCCAAGACTAGGGATGATTTTGCCTGGCAATCTGGAACTAATGCTTCAATCTTTTGGCA
2697  72_HRV50     ACCCAAGACTAGGGATGATTTTGCCTGGCAATCTGGAACTAATGCTTCAATCTTTTGGCA
2698  73_HRV18a|   ACCAAAAACCAGAGATGATTTTGCCTGGCAATCTGGAACAAATGCATCAATCTTCTGGCA
2699  74_HRV18b|   ACCAAAAACCAGAGATGATTTTGCCTGGCAATCTGGAACAAATGCATCAATCTTCTGGCA
2700  75_HRV18     ACCAAAAACCAGAGATGATTTTGCCTGGCAATCTGGAACAAATGCATCAATCTTCTGGCA
2701  76_HRV55     TCCAAAGACAAGAGAAGATTATGCTTGGCAATCAGGGACCAATGCATCTATCTTTTGGCA
2702  77_HRV55b|   TCCAAAGACAAGAGAAGATTATGCTTGGCAATCAGGGACCAATGCATCTATCTTTTGGCA
2703  78_HRV55a|   TCCAAAGACAAGAGAAGATTATGCTTGGCAATCAGGGACCAATGCATCTATCTTTTGGCA
2704  79_HRV57     TCCAAAAACAAGAGAGGATTATACATGGCAATCTGGTACCAATGCTTCAATATTTTGGCA
2705  80_HRV57a|   TCCAAAAACAAGAGAGGATTATACATGGCAATCTGGTACCAATGCTTCAATATTTTGGCA
2706  81_HRV57b|   TCCAAAAACAAGAGAGGATTATACATGGCAATCTGGTACCAATGCTTCAATATTTTGGCA
2707  82_HRV21     TCCAAAAACTAGGGAAGATTTTGCTTGGCAGTCAGGCACTAATGCATCCATTTTCTGGCA
2708  83_HRVHan    TCCAAAAACTAGGGAAGATTTTGCTTGGCAATCAGGTACCAATGCATCCATTTTCTGGCA
2709  84_HRV43     TCCAAAAACTAGGAAAGATTATGCATGGCAATCTGGCACAAATGCATCTGTTTTCTGGCA
2710  85_HRV43b|   TCCAAAAACTAGGAAAGATTATGCATGGCAATCTGGCACAAATGCATCTGTTTTCTGGCA
2711  86_HRV43a|   TCCAAAAACTAGGAAAGATTATGCATGGCAATCTGGCACAAATGCATCTGTTTTCTGGCA
2712  87_HRV75     ACCAACAACTAGAAAAGATTATGCATGGCAATCTGGAACAAATGCATCGTATTTTGGCA
2713  88_HRV75b|   ACCAACAACTAGAAAAGATTATGCATGGCAATCTGGAACAAATGCATCTGTATTTTGGCA
2714  89_HRV75a|   ACCAACAACTAGAAAAGATTATGCATGGCAATCTGGAACAAATGCATCTGTATTTTGGCA
2715  96_HRV9a|d   ACCAAGGACTAGAGATGATTATGCATGGCAATCAGGCACAAATGCTTCCATCTTTTGGCA
2716  97_HRV9b|d   ACCAAGGACTAGAGATGATTATGCATGGCAATCAGGCACAAATGCTTCCATCTTTTGGCA
2717  98_HRV9      ACCAAGGACTAGAGATGATTATGCATGGCAATCAGGCACAAATGCTTCCATCTTTTGGCA
2718  99_HRV32     ACCACAAGCAAGAGATGACTACACATGGCAATCTGGCACGAATGCATCTATCTTTTGGCA
2719  100_HRV32a   ACCACAAGCAAGAGATGACTACACATGGCAATCTGGCACGAATGCATCTATCTTTTGGCA
2720  101_HRV32b   ACCACAAGCAAGAGATGACTACACATGGCAATCTGGCACGAATGCATCTATCTTTTGGCA
2721  102_HRV67    ACCAACAAAAGAGATGACTACACATGGCAATCAGGTACAAATGCATCCATCTTTTGGCA
2722  103_HRV67a   ACCAACAAAAGAGATGACTACACATGGCAATCAGGTACAAATGCATCCATCTTTTGGCA
2723  104_HRV67b   ACCAACAAAAGAGATGACTACACATGGCAATCAGGTACAAATGCATCCATCTTTTGGCA
2724  105_HRV15    ACCCAATAAAAGGAATGATTACACATGGCAATCAGGTACAAATGCCTCTGTTTTCTGGCA
2725  106_HRV15a   ACCCAATAAAAGGAATGATTACACATGGCAATCAGGTACAAATGCCTCTGTTTTCTGGCA
2726  107_HRV15b   ACCCAATAAAAGGAATGATTACACATGGCAATCAGGTACAAATGCCTCTGTTTTCTGGCA
2727  108_HRV74a   ACCCAAGAAAAGAGATGATTACACATGGCAATCTGGCACAAATGCATCTGTGTTTTGGCA
2728  109_HRV74b   ACCCAAGAAAAGAGATGATTACACATGGCAATCTGGCACAAATGCATCTGTGTTTTGGCA
2729  110_HRV74    ACCCAAGAAAAGAGATGATTACACATGGCAATCTGGCACAAATGCATCTGTGTTTTGGCA
2730  111_HRV38a   ACCCAGGAAGAGAGATGATTACACTTGGCAATCTGGTACAAATGCCTCTGTTTTCTGGCA
2731  112_HRV38b   ACCCAGGAAGAGAGATGATTACACTTGGCAATCTGGTACAAATGCCTCTGTTTTCTGGCA
2732  113_HRV38    ACCCAGGAAGAGAGATGATTACACTTGGCAATCTGGTACAAATGCCTCTGTTTTCTGGCA
2733  114_HRV60    ACCTACTAAAAGAGACGATTACACATGGCAATCTGGCACAAATGCTTCTGTATTTTGGCA
2734  115_HRV60a   ACCTACTAAAAGAGACGATTACACATGGCAATCTGGCACAAATGCTTCTGTATTTTGGCA
2735  116_HRV60b   ACCTACTAAAAGAGACGATTACACATGGCAATCTGGCACAAATGCTTCTGTATTTTGGCA
2736  117_HRV64a   ACCAACCAAAAGAAATGATTACGTCTGGCAGTCAGGCACCAATGCATCCATCTTTTGGCA
2737  118_HRV64b   ACCAACCAAAAGAAATGATTACGTCTGGCAGTCAGGCACCAATGCATCCATCTTTTGGCA
2738  119_HRV64    ACCAACCAAAAGAAATGATTACGTCTGGCAGTCAGGCACCAATGCATCCATCTTTTGGCA
2739  120_HRV94a   ACCAGACAAAAGAGATGATTATGTTTGGCAATCAGGAACTAATGCATCTATATTCTGGCA
2740  121_HRV94b   ACCAGACAAAAGAGATGATTATGTTTGGCAATCAGGAACTAATGCATCTATATTCTGGCA
2741  122_HRV94    ACCAGACAAAAGAGATGATTATGTTTGGCAATCAGGAACTAATGCATCTATATTCTGGCA
2742  123_HRV22    ACCTGAAAAGAGAGATGACTACACATGGCAATCTGGCACTAATGCATCTGTTTTCTGGCA
2743  124_HRV22a   ACCTGAAAAGAGAGATGACTACACATGGCAATCTGGCACTAATGCATCTGTTTTCTGGCA
2744  125_HRV22b   ACCTGAAAAGAGAGATGACTACACATGGCAATCTGGCACTAATGCATCTGTTTTCTGGCA
2745  126_HRV82    ACCAGAAAAGAGAGACGACTACACTTGGCAATCTGGAACTAATGCTTCAATTTTCTGGCA
2746  127_HRV82b   ACCAGAAAAGAGAGACGACTACACTTGGCAATCTGGAACTAATGCTTCAATTTTCTGGCA
2747  128_HRV82a   ACCAGAAAAGAGAGACGACTACACTTGGCAATCTGGAACTAATGCTTCAATTTTCTGGCA
2748  129_HRV19    CCCAAAAACTAGAAATGATTACACATGGCAATCAGGTACTAATGCATCTATATTTTGGCA
2749  130_HRV19a   CCCAAAAACTAGAAATGATTACACATGGCAATCAGGTACTAATGCATCTATATTTTGGCA
2750  131_HRV19b   CCCAAAAACTAGAAATGATTACACATGGCAATCAGGTACTAATGCATCTATATTTTGGCA
2751  132_HRV13    TCCAACGAAGAGAAATGATTACACATGGCAATCTGGCACCAATGCATCTGTTTTCTGGCA
2752  133_HRV13a   TCCAACGAAGAGAAATGATTACACATGGCAATCTGGCACCAATGCATCTGTTTTCTGGCA
```

FIG. D5 CONT'D 01.trace                                                                                               9/20/2007 4:58 PM

```
2753  134_HRV13b    TCCAACGAAGAGAAATGATTACACATGGCAATCTGGCACCAATGCATCTGTTTTCTGGCA
2754  135_HRV41     CCCAGAAAAGAGAGATGATTACACATGGCAATCTGGCACCAATGCATCTGTATTCTGGCA
2755  136_HRV41a    CCCAGAAAAGAGAGATGATTACACATGGCAATCTGGCACCAATGCATCTGTATTCTGGCA
2756  137_HRV41b    CCCAGAAAAGAGAGATGATTACACATGGCAATCTGGCACCAATGCATCTGTATTCTGGCA
2757  138_HRV73     ACCCACAAAAGAAATGACTACACATGGCAGTCCGGCACTAATGCATCAGTATTCTGGCA
2758  139_HRV73b    ACCCACAAAAGAAATGACTACACATGGCAGTCCGGCACTAATGCATCAGTATTCTGGCA
2759  140_HRV73a    ACCCACAAAAGAAATGACTACACATGGCAGTCCGGCACTAATGCATCAGTATTCTGGCA
2760  141_HRV61     ACCTGAGAAAAGAAATGATTTCACATGGCAATCAGGCACAAATGCATCTGTTTTCTGGCA
2761  142_HRV61a    ACCTGAGAAAAGAAATGATTTCACATGGCAATCAGGCACAAATGCATCTGTTTTCTGGCA
2762  143_HRV61b    ACCTGAGAAAAGAAATGATTTCACATGGCAATCAGGCACAAATGCATCTGTTTTCTGGCA
2763  144_HRV96     ACCTGAGAAGAGAGATGACTTTACATGGCAATCAGGCACAAATGCATCTGTGTTTTGGCA
2764  145_HRV96b    ACCTGAGAAGAGAGATGACTTTACATGGCAATCAGGCACAAATGCATCTGTGTTTTGGCA
2765  146_HRV96a    ACCTGAGAAGAGAGATGACTTTACATGGCAATCAGGCACAAATGCATCTGTGTTTTGGCA
2766  90_HRV16a|    ACCAACAACTAGAAATGACTATGCTTGGCAATCTGGAACAAATGCATCTGTATTTTGGCA
2767  91_HRV16b|    ACCAACAACTAGAAATGACTATGCTTGGCAATCTGGAACAAATGCATCTGTATTTTGGCA
2768  92_1AYM_A     ACCAACAACTAGAAATGACTATGCTTGGCAATCTGGAACAAATGCATCTGTATTTTGGCA
2769  93_HRV81a|    TCCAACAACTAGAGAAGACTATGCTTGGCAATCTGGAACAAATGCATCTATATTCTGGCA
2770  94_HRV81b|    TCCAACAACTAGAGAAGACTATGCTTGGCAATCTGGAACAAATGCATCTATATTCTGGCA
2771  95_HRV81      TCCAACAACTAGAGAAGACTATGCTTGGCAATCTGGAACAAATGCATCTATATTCTGGCA
2772  147_HRV2      GCCCAATAGTAGGGACGATTATGCATGGCAGTCTGGCACTAATGCCTCTGTTTTCTGGCA
2773  148_HRV2a|    GCCCAATAGTAGGGACGATTATGCATGGCAGTCTGGCACTAATGCCTCTGTTTTCTGGCA
2774  149_HRV2b|    GCCCAATAGTAGGGACGATTATGCATGGCAGTCTGGCACTAATGCCTCTGTTTTCTGGCA
2775  150_HRV49a    ACCAAAGAGCAGAGATGATTATGCATGGCAGTCTGGCACTAATGCATCTGTTTTCTGGCA
2776  151_HRV49b    ACCAAAGAGCAGAGATGATTATGCATGGCAGTCTGGCACTAATGCATCTGTTTTCTGGCA
2777  152_HRV49     ACCAAAGAGCAGAGATGATTATGCATGGCAGTCTGGCACTAATGCATCTGTTTTCTGGCA
2778  153_HRV23a    ACCGGAAAGTAGAAATGACTATGCATGGCAATCTGGAACAAATGCGTCCATTTTTTGGCA
2779  154_HRV23b    ACCGGAAAGTAGAAATGACTATGCATGGCAATCTGGAACAAATGCGTCCATTTTTTGGCA
2780  155_HRV23     ACCGGAAAGTAGAAATGACTATGCATGGCAATCTGGAACAAATGCGTCCATTTTTTGGCA
2781  156_HRV30a    TCCCGAGAGCAGAAATGACTATGCATGGCAGTCTGGAACAAATGCATCTGTTTTTTGGCA
2782  157_HRV30b    TCCCGAGAGCAGAAATGACTATGCATGGCAGTCTGGAACAAATGCATCTGTTTTTTGGCA
2783  158_HRV30     TCCCGAGAGCAGAAATGACTATGCATGGCAGTCTGGAACAAATGCATCTGTTTTTTGGCA
2784  159_HRV7      TCCAATAAAACGCGAAGATTATACATGGCAATCAGGAACAAATGCTTCTATATTTTGGCA
2785  160_HRV7b|    TCCAATAAAACGCGAAGATTATACATGGCAATCAGGAACAAATGCTTCTATATTTTGGCA
2786  161_HRV7a|    TCCAATAAAACGCGAAGATTATACATGGCAATCAGGAACAAATGCTTCTATATTTTGGCA
2787  162_HRV88     TCCCAAGAAACGTGATGATTACACATGGCAGTCAGGAACAAATGCATCTGTGTTCTGGCA
2788  163_HRV88a    TCCCAAGAAACGTGATGATTACACATGGCAGTCAGGAACAAATGCATCTGTGTTCTGGCA
2789  164_HRV88b    TCCCAAGAAACGTGATGATTACACATGGCAGTCAGGAACAAATGCATCTGTGTTCTGGCA
2790  165_HRV36a    TCCTGTGAAGCGTGATGACTACACATGGCAATCAGGGACAAATGCATCTGTGTTCTGGCA
2791  166_HRV36b    TCCTGTGAAGCGTGATGACTACACATGGCAATCAGGGACAAATGCATCTGTGTTCTGGCA
2792  167_HRV36     TCCTGTGAAGCGTGATGACTACACATGGCAATCAGGGACAAATGCATCTGTGTTCTGGCA
2793  168_HRV89a    CCCCGAAAAACGTGATGATTACACATGGCAATCAGGAACAAATGCATCTGTGTTCTGGCA
2794  169_HRV89b    CCCCGAAAAACGTGATGATTACACATGGCAATCAGGAACAAATGCATCTGTGTTCTGGCA
2795  170_HRV89     CCCCGAAAAACGTGATGATTACACATGGCAATCAGGAACAAATGCATCTGTGTTCTGGCA
2796  171_HRV58     ACCCAAGAATCGTGATGACTTTACATGGCAATCAGGCACAAATGCATCTGTTTTCTGGCA
2797  172_HRV58a    ACCCAAGAATCGTGATGACTTTACATGGCAATCAGGCACAAATGCATCTGTTTTCTGGCA
2798  173_HRV58b    ACCCAAGAATCGTGATGACTTTACATGGCAATCAGGCACAAATGCATCTGTTTTCTGGCA
2799  174_HRV12a    ACCCAAAAAACGTGATGATTACACATGGCAATCTGGCACCAACGCCTCAGTTTTTTGGCA
2800  175_HRV12b    ACCCAAAAAACGTGATGATTACACATGGCAATCTGGCACCAACGCCTCAGTTTTTTGGCA
2801  176_HRV12     ACCCAAAAAACGTGATGATTACACATGGCAATCTGGCACCAACGCCTCAGTTTTTTGGCA
2802  177_HRV78a    ACCAAAGAAGAGAGATGACTATACTTGGCAGTCAGGCACCAATGCATCTGTGTTTTGGCA
2803  178_HRV78b    ACCAAAGAAGAGAGATGACTATACTTGGCAGTCAGGCACCAATGCATCTGTGTTTTGGCA
2804  179_HRV78     ACCAAAGAAGAGAGATGACTATACTTGGCAGTCAGGCACCAATGCATCTGTGTTTTGGCA
2805  180_HRV20     ACCAAAGACTAGAGATGACTACACATGGCAATCAGGGACAAATGCATCAGTATTTTGGCA
2806  181_HRV20a    ACCAAAGACTAGAGATGACTACACATGGCAATCAGGGACAAATGCATCAGTATTTTGGCA
2807  182_HRV20b    ACCAAAGACTAGAGATGACTACACATGGCAATCAGGGACAAATGCATCAGTATTTTGGCA
2808  183_HRV68     ACCAAAAACTAGAGATGATTACACATGGCAGTCAGGCACTAATGCATCAGTGTTTTGGCA
2809  184_HRV68a    ACCAAAAACTAGAGATGATTACACATGGCAGTCAGGCACTAATGCATCAGTGTTTTGGCA
2810  185_HRV68b    ACCAAAAACTAGAGATGATTACACATGGCAGTCAGGCACTAATGCATCAGTGTTTTGGCA
2811  186_HRV28     CCCCACTACCAGAAATGATTACACATGGCAATCCAGTACCAATGCCTCTGTTTTCTGGCA
2812  187_HRV28a    CCCCACTACCAGAAATGATTACACATGGCAATCCAGTACCAATGCCTCTGTTTTCTGGCA
2813  188_HRV28b    CCCCACTACCAGAAATGATTACACATGGCAATCCAGTACCAATGCCTCTGTTTTCTGGCA
2814  189_HRV53a    ACCCAAAACCAGAGATGACTATACCTGGCAATCTGGAACTAATGCTTCAGTCTTTTGGCA
2815  190_HRV53b    ACCCAAAACCAGAGATGACTATACCTGGCAATCTGGAACTAATGCTTCAGTCTTTTGGCA
2816  191_HRV53     ACCCAAAACCAGAGATGACTATACCTGGCAATCTGGAACTAATGCTTCAGTCTTTTGGCA
```

FIG. D5 CONT'D 01.trace                                                                    9/20/2007 4:58 PM

```
2817  192_HRV46a   ACCGAGATATCGGAATGATTATACTTGGCAGTCTGGTACTAATGCTTCAGTGTTCTGGCA
2818  193_HRV46b   ACCGAGATATCGGAATGATTATACTTGGCAGTCTGGTACTAATGCTTCAGTGTTCTGGCA
2819  194_HRV46    ACCGAGATATCGGAATGATTATACTTGGCAGTCTGGTACTAATGCTTCAGTGTTCTGGCA
2820  195_HRV80a   GCCAAACAAACGCAATGATTATACTTGGCAGTCTGGCACGAATGCTTCAGTCTTCTGGCA
2821  196_HRV80b   GCCAAACAAACGCAATGATTATACTTGGCAGTCTGGCACGAATGCTTCAGTCTTCTGGCA
2822  197_HRV80    GCCAAACAAACGCAATGATTATACTTGGCAGTCTGGCACGAATGCTTCAGTCTTCTGGCA
2823  198_HRV51    TCCACTTACTAGGAAAGATGATGAGTGGCAATCAGGAACTAATGCTTCAGTATTCTGGCA
2824  199_HRV51a   TCCACTTACTAGGAAAGATGATGAGTGGCAATCAGGAACTAATGCTTCAGTATTCTGGCA
2825  200_HRV51b   TCCACTTACTAGGAAAGATGATGAGTGGCAATCAGGAACTAATGCTTCAGTATTCTGGCA
2826  201_HRV65a   TCCAAAAACTAGAAAAGATGAAGAGTGGCAGACAGGAACTAATGCTTCAGTCTTTTGGCA
2827  202_HRV65b   TCCAAAAACTAGAAAAGATGAAGAGTGGCAGACAGGAACTAATGCTTCAGTCTTTTGGCA
2828  203_HRV65    TCCAAAAACTAGAAAAGATGAAGAGTGGCAGACAGGAACTAATGCTTCAGTCTTTTGGCA
2829  204_HRV71a   ACCAGAGACCAGGGATGCCGATGAATGGCAGTCTGGAACTAATGCATCAGTCTTTTGGCA
2830  205_HRV71b   ACCAGAGACCAGGGATGCCGATGAATGGCAGTCTGGAACTAATGCATCAGTCTTTTGGCA
2831  206_HRV71    ACCAGAGACCAGGGATGCCGATGAATGGCAGTCTGGAACTAATGCATCAGTCTTTTGGCA
2832  207_HRV8     TCCAGATAAAAGGATGCACGATGCCTGGCAAACCAGTACAAATGCCTCAGTCTTCTGGCA
2833  208_HRV95    TCCAGATAAAAGGATGCACGATGCCTGGCAAACCAGTACAAATGCCTCAGTCTTCTGGCA
2834  209_HRV45    CCCTGTTAGTAGAACTGACAACACTTGGCAATCTAGCACAAATGCATCAGTCTTTTGGCA
2835  210_HRV45a   CCCTGTTAGTAGAACTGACAACACTTGGCAATCTAGCACAAATGCATCAGTCTTTTGGCA
2836  211_HRV45b   CCCTGTTAGTAGAACTGACAACACTTGGCAATCTAGCACAAATGCATCAGTCTTTTGGCA
2837  212_HRV6     ------------------------------------------------------------
2838  213_HRV6a|   ------------------------------------------------------------
2839  214_HRV6b|   ------------------------------------------------------------
2840  215_HRV37    ------------------------------------------------------------
2841  216_HRV37a   ------------------------------------------------------------
2842  217_HRV37b   ------------------------------------------------------------
2843  218_HRV3     ------------------------------------------------------------
2844  219_HRV3a|   ------------------------------------------------------------
2845  220_HRV3b|   ------------------------------------------------------------
2846  221_HRV14    ------------------------------------------------------------
2847  222_HRV14a   ------------------------------------------------------------
2848  223_HRV14b   ------------------------------------------------------------
2849  224_HRV72    ------------------------------------------------------------
2850  225_HRV72a   ------------------------------------------------------------
2851  226_HRV72b   ------------------------------------------------------------
2852  227_HRV83    ------------------------------------------------------------
2853  228_HRV83a   ------------------------------------------------------------
2854  229_HRV83b   ------------------------------------------------------------
2855  230_HRV92    ------------------------------------------------------------
2856  231_HRV92a   ------------------------------------------------------------
2857  232_HRV92b   ------------------------------------------------------------
2858  233_HRV79    ------------------------------------------------------------
2859  234_HRV79a   ------------------------------------------------------------
2860  235_HRV79b   ------------------------------------------------------------
2861  236_HRV35    ------------------------------------------------------------
2862  237_HRV35a   ------------------------------------------------------------
2863  238_HRV35b   ------------------------------------------------------------
2864  239_1HRV86   ------------------------------------------------------------
2865  240_1HRV86   ------------------------------------------------------------
2866  241_1HRV86   ------------------------------------------------------------
2867  242_HRV70    ------------------------------------------------------------
2868  243_HRV70a   ------------------------------------------------------------
2869  244_HRV70b   ------------------------------------------------------------
2870  245_HRV91    ------------------------------------------------------------
2871  246_HRV91a   ------------------------------------------------------------
2872  247_HRV91b   ------------------------------------------------------------
2873  248_HRV17    ------------------------------------------------------------
2874  249_HRV17a   ------------------------------------------------------------
2875  250_HRV17b   ------------------------------------------------------------
2876  251_HRV69    ------------------------------------------------------------
2877  252_HRV69a   ------------------------------------------------------------
2878  253_HRV69b   ------------------------------------------------------------
2879  254_HRV48    ------------------------------------------------------------
2880  255_HRV48a   ------------------------------------------------------------
```

FIG. D5 CONT'D

01.trace                                                                  9/20/2007 4:58 PM

```
2881  256_HRV48b    ------------------------------------------------------------
2882  257_HRV52     ------------------------------------------------------------
2883  258_HRV52a    ------------------------------------------------------------
2884  259_HRV52b    ------------------------------------------------------------
2885  260_HRV4      ------------------------------------------------------------
2886  261_HRV4a|    ------------------------------------------------------------
2887  262_HRV4b|    ------------------------------------------------------------
2888  263_HRV99     ------------------------------------------------------------
2889  264_HRV99a    ------------------------------------------------------------
2890  265_HRV99b    ------------------------------------------------------------
2891  266_HRV5      ------------------------------------------------------------
2892  267_HRV5a|    ------------------------------------------------------------
2893  268_HRV5b|    ------------------------------------------------------------
2894  269_HRV42     ------------------------------------------------------------
2895  270_HRV42a    ------------------------------------------------------------
2896  271_HRV42b    ------------------------------------------------------------
2897  272_HRV26     ------------------------------------------------------------
2898  273_HRV26a    ------------------------------------------------------------
2899  274_HRV26b    ------------------------------------------------------------
2900  275_HRV27     ------------------------------------------------------------
2901  276_HRV27a    ------------------------------------------------------------
2902  277_HRV27b    ------------------------------------------------------------
2903  278_HRV93     ------------------------------------------------------------
2904  279_HRV93a    ------------------------------------------------------------
2905  280_HRV93b    ------------------------------------------------------------
2906  281_HRV97     ------------------------------------------------------------
2907  282_HRV97a    ------------------------------------------------------------
2908  283_HRV97b    ------------------------------------------------------------
2909  284_HRV84     ------------------------------------------------------------
2910  285_HRV84a    ------------------------------------------------------------
2911  286_HRV84b    ------------------------------------------------------------
2912  287_HRV87     ------------------------------------------------------------
2913  288_HRV87a    ------------------------------------------------------------
2914  289_HRV87b    ------------------------------------------------------------
2915  GROUP_1       ------------------------------------------------------------
2916
2917   1_HRV1A1|d   ACATGGACAGCCATTTCCTAGATTTTCTTTACCATTTCTTAGCATTGCATCAGCTTATTA
2918   2_HRV1A2|d   ACATGGACAGCCATTTCCTAGATTTTCTTTACCATTTCTTAGCATTGCATCAGCTTATTA
2919   3_HRV1A|cD   ACATGGACAGCCATTTCCTAGATTTTCTTTACCATTTCTTAGCATTGCATCAGCTTATTA
2920   4_HRV1B1|d   ACATGGACAACCGTTCCCTAGATTCTCTTTACCATTTCTTAGCATTGCATCAGCTTATTA
2921   5_HRV1B2|d   ACATGGACAACCGTTCCCTAGATTCTCTTTACCATTTCTTAGCATTGCATCAGCTTATTA
2922   6_HRV1B      ACATGGACAACCGTTCCCTAGATTCTCTTTACCATTTCTTAGCATTGCATCAGCTTATTA
2923   7_HRV40a|d   ACATGGTCAAACTTTCCCTAGATTTTCTTTACCTTTCCTAAGCATAGCTTCAGCATACTA
2924   8_HRV40b|d   ACATGGTCAAACTTTCCCTAGATTTTCTTTACCTTTCCTAAGCATAGCTTCAGCATACTA
2925   9_HRV40      ACATGGTCAAACTTTCCCTAGATTTTCTTTACCTTTCCTAAGCATAGCTTCAGCATACTA
2926  10_HRV85      ACATGGGCAAACTTTCCCCAGATTTTCCTTACCTTTCTTGAGTGTTGCTTCAGCATATTA
2927  11_HRV85a|    ACATGGGCAAACTTTCCCCAGATTTTCCTTACCTTTCTTGAGTGTTGCTTCAGCATATTA
2928  12_HRV85b|    ACATGGGCAAACTTTCCCCAGATTTTCCTTACCTTTCTTGAGTGTTGCTTCAGCATATTA
2929  13_HRV56a|    ACATGGCCAAGCTTTCCCCAGATTCTCTCTACCTTTCTTAAGTATTGCTTCTGCTTATTA
2930  14_HRV56b|    ACATGGCCAAGCTTTCCCCAGATTCTCTCTACCTTTCTTAAGTATTGCTTCTGCTTATTA
2931  15_HRV56      ACATGGCCAAGCTTTCCCCAGATTCTCTCTACCTTTCTTAAGTATTGCTTCTGCTTATTA
2932  16_HRV54      ACATGGCCAAGCTTATCCAAGATTCTCTTTACCATTTTAAGTATTGCATCTGCTTACTA
2933  17_HRV98      GCATGGTCAGGCCTATCCAAGATTTTCTCTACCATTCTTGAGCATTGCATCTGCTTACTA
2934  18_HRV59a|    ACATGGACAAACATTCCCAAGATTTTCATTGCCCTTCCTGAGCATAGCATCAGCTTATTA
2935  19_HRV59b|    ACATGGACAAACATTCCCAAGATTTTCATTGCCCTTCCTGAGCATAGCATCAGCTTATTA
2936  20_HRV59      ACATGGACAAACATTCCCAAGATTTTCATTGCCCTTCCTGAGCATAGCATCAGCTTATTA
2937  21_HRV63      ACATGGACAAGCTTTTCCAAGGTTTTCTCTACCTTTCTTGAGTATTGCATCAGCATATTA
2938  22_HRV63b|    ACATGGACAAGCTTTTCCAAGGTTTTCTCTACCTTTCTTGAGTATTGCATCAGCATATTA
2939  23_HRV63a|    ACATGGACAAGCTTTTCCAAGGTTTTCTCTACCTTTCTTGAGTATTGCATCAGCATATTA
2940  24_HRV39      ACACGGACAGCCTTACCCTAGATTTTCATTACCATTTCTAAGCATAGCCTCAGCATATTA
2941  25_HRV39a|    ACACGGACAGCCTTACCCTAGATTTTCATTACCATTTCTAAGCATAGCCTCAGCATATTA
2942  26_HRV39b|    ACACGGACAGCCTTACCCTAGATTTTCATTACCATTTCTAAGCATAGCCTCAGCATATTA
2943  27_HRV10a|    ACATGGACAACCTTTCCCTAGATTTTCTTTACCCTTCTTAAGCATTGCATCTGCTTACTA
2944  28_HRV10b|    ACATGGACAACCTTTCCCTAGATTTTCTTTACCCTTCTTAAGCATTGCATCTGCTTACTA
```

FIG. D5 CONT'D 01.trace                                                                                        9/20/2007 4:58 PM

```
2945  29_HRV10      ACATGGACAACCTTTCCCTAGATTTTCTTTACCCTTCTTAAGCATTGCATCTGCTTACTA
2946  30_HRV100a    GCATGGGCAGCCATTCCCTAGAATTTCTTTACCTTTCTTGAGCATTGCTTCTGCATACTA
2947  31_HRV100b    GCATGGGCAGCCATTCCCTAGAATTTCTTTACCTTTCTTGAGCATTGCTTCTGCATACTA
2948  32_HRV100     GCATGGGCAGCCATTCCCTAGAATTTCTTTACCTTTCTTGAGCATTGCTTCTGCATACTA
2949  33_HRV66      ACTTGGACAACCATTCCCAAGATTCTCGCTACCTTTTCTAGGCATAGCTTCAGCATATTA
2950  34_HRV66b|    ACTTGGACAACCATTCCCAAGATTCTCGCTACCTTTTCTAGGCATAGCTTCAGCATATTA
2951  35_HRV66a|    ACTTGGACAACCATTCCCAAGATTCTCGCTACCTTTTCTAGGCATAGCTTCAGCATATTA
2952  36_HRV77a|    ACATGGACAACCATTCCCAAGATTTTCACTACCTTTTCTGAGTATTGCTTCAGCTTACTA
2953  37_HRV77b|    ACATGGACAACCATTCCCAAGATTTTCACTACCTTTTCTGAGTATTGCTTCAGCTTACTA
2954  38_HRV77      ACATGGACAACCATTCCCAAGATTTTCACTACCTTTTCTGAGTATTGCTTCAGCTTACTA
2955  39_HRV62a     ACATGGGCAACCCTTTCCTAGATTTTCATTACCTTTTTTGAGTGTTGCATCTGCTTATTA
2956  40_HRV62b     ACATGGGCAACCCTTTCCTAGATTTTCATTACCTTTTTTGAGTGTTGCATCTGCTTATTA
2957  41_HRV25      ACATGGACAACCCTTCCCTAGATTTTCATTGCCATTTCTGAGTGTTGCATCTGCTTATTA
2958  42_HRV29a     ACATGGTCAGCCTTTCCCAAGATTTTCATTACCATTCCTAAGTGTTGCATCTGCTTATTA
2959  43_HRV29b     ACATGGTCAGCCTTTCCCAAGATTTTCATTACCATTCCTAAGTGTTGCATCTGCTTATTA
2960  44_HRV44a     ACATGGTCAACCTTTCCCAAGATTTTCATTGCCATTTCTAAGTGTTGCATCTGCCTATTA
2961  45_HRV44b     ACATGGTCAACCTTTCCCAAGATTTTCATTGCCATTTCTAAGTGTTGCATCTGCCTATTA
2962  46_HRV31      ACATGGACAACCCTTTCCAAGATTTACATTACCCTTTTGAGTGTCGCATCCGCTTATTA
2963  47_HRV31a|    ACATGGACAACCCTTTCCAAGATTTACATTACCCTTTTGAGTGTCGCATCCGCTTATTA
2964  48_HRV31b|    ACATGGACAACCCTTTCCAAGATTTACATTACCCTTTTGAGTGTCGCATCCGCTTATTA
2965  49_HRV47      ACAAGGGCAACCCTTTCCAAGATTTTCATTACCATTTTTGAGTGTTGCATCTGCTTATTA
2966  50_HRV47a|    ACAAGGGCAACCCTTTCCAAGATTTTCATTACCATTTTTGAGTGTTGCATCTGCTTATTA
2967  51_HRV47b|    ACAAGGGCAACCCTTTCCAAGATTTTCATTACCATTTTTGAGTGTTGCATCTGCTTATTA
2968  52_HRV11      ATATGGTCAAACATACCCAAGATTTCTCTACCTTTCATGAGTATAGCCTCAGCATATTA
2969  53_HRV11b|    ATATGGTCAAACATACCCAAGATTTTCTCTACCTTTCATGAGTATAGCCTCAGCATATTA
2970  54_HRV11a|    ATATGGTCAAACATACCCAAGATTTTCTCTACCTTTCATGAGTATAGCCTCAGCATATTA
2971  55_HRV76      ATATGGACAAACATACCCTAGGTTTTCATTACCCTTTCTAAGTATAGCTTCAGCTTATTA
2972  56_HRV76b|    ATATGGACAAACATACCCTAGGTTTTCATTACCCTTTCTAAGTATAGCTTCAGCTTATTA
2973  57_HRV76a|    ATATGGACAAACATACCCTAGGTTTTCATTACCCTTTCTAAGTATAGCTTCAGCTTATTA
2974  58_HRV33      ATATGGACAAACATATCCTAGGTTCTCATTACCTTTTCCTTAGCATAGCTTCAGCATATTA
2975  59_HRV33b|    ATATGGACAAACATATCCTAGGTTCTCATTACCTTTCCTTAGCATAGCTTCAGCATATTA
2976  60_HRV33a|    ATATGGACAAACATATCCTAGGTTCTCATTACCTTTCCTTAGCATAGCTTCAGCATATTA
2977  61_HRV24a|    ACATGGACAAACCTATCCTAGATTTTCCTTTCTGAGTGTAGCCTCTGCATATTA
2978  62_HRV24b|    ACATGGACAAACCTATCCTAGATTTTCCCTTCCTTTTCTGAGTGTAGCCTCTGCATATTA
2979  63_HRV24      ACATGGACAAACCTATCCTAGATTTTCCCTTCCTTTTCTGAGTGTAGCCTCTGCATATTA
2980  64_HRV90      ACATGGACAAACATACCCTAGATTTTCACTTCCTTTCTTAAGTATAGCTTCTGCATACTA
2981  65_HRV90a|    ACATGGACAAACATACCCTAGATTTTCACTTCCTTTCTTAAGTATAGCTTCTGCATACTA
2982  66_HRV90b|    ACATGGACAAACATACCCTAGATTTTCACTTCCTTTCTTAAGTATAGCTTCTGCATACTA
2983  67_HRV34      ACATGGTCAAACATACCCTAGATTTTCCCTCCCTTTCTTAAGCATAGCCTCAGCATACTA
2984  68_HRV34b|    ACATGGTCAAACATACCCTAGATTTTCCCTCCCTTTCTTAAGCATAGCCTCAGCATACTA
2985  69_HRV34a|    ACATGGTCAAACATACCCTAGATTTTCCCTCCCTTTCTTAAGCATAGCCTCAGCATACTA
2986  70_HRV50a|    ACATGGTCAAACATACCCTAGATTCTCTCTACCATTCTTGAGTATAGCATCTGCATATTA
2987  71_HRV50b|    ACATGGTCAAACATACCCTAGATTCTCTCTACCATTCTTGAGTATAGCATCTGCATATTA
2988  72_HRV50      ACATGGTCAAACATACCCTAGATTCTCTCTACCATTCTTGAGTATAGCATCTGCATATTA
2989  73_HRV18a|    ACATGGTCAAACATACCCCAGATTTTCACTTCCTTTCCTCAGTATAGCATCAGCTTATTA
2990  74_HRV18b|    ACATGGTCAAACATACCCCAGATTTTCACTTCCTTTCCTCAGTATAGCATCAGCTTATTA
2991  75_HRV18      ACATGGTCAAACATACCCCAGATTTTCACTTCCTTTCCTCAGTATAGCATCAGCTTATTA
2992  76_HRV55      ACATGGGCAAACATACCCTAGATTTTCACTTCCTTTCCTAAGTATAGCTTCTGCTTATTA
2993  77_HRV55b|    ACATGGGCAAACATACCCTAGATTTTCACTTCCTTTCCTAAGTATAGCTTCTGCTTATTA
2994  78_HRV55a|    ACATGGGCAAACATACCCTAGATTTTCACTTCCTTTCCTAAGTATAGCTTCTGCTTATTA
2995  79_HRV57      ACATGGTCAAACATACCCTAGATTTTCCTTGCCTTTCTTAAGTATAGCCTCAGCATATTA
2996  80_HRV57a|    ACATGGTCAAACATACCCTAGATTTTCCTTGCCTTTCTTAAGTATAGCCTCAGCATATTA
2997  81_HRV57b|    ACATGGTCAAACATACCCTAGATTTTCCTTGCCTTTCTTAAGTATAGCCTCAGCATATTA
2998  82_HRV21      GCATGGCCAGACTTATCCTAGATTTTCATTACCCTTCCTTAGTATAGCATCAGCATACTA
2999  83_HRVHan     GCATGGTCAAACTTATCCTAGATTTTCACTACCCTTCCTTAGTATAGCATCAGCATATTA
3000  84_HRV43      ACATGGTCAAACATTTCCAAGATTTTCCTTACCTTTTCTGAGCATAGCATCAGCATATTA
3001  85_HRV43b|    ACATGGTCAAACATTTCCAAGATTTTCCTTACCTTTTCTGAGCATAGCATCAGCATATTA
3002  86_HRV43a|    ACATGGTCAAACATTTCCAAGATTTTCCTTACCTTTTCTGAGCATAGCATCAGCATATTA
3003  87_HRV75      ACATGGACAAACATTCCAAGATTTTCACTACCATTTCTGAGCATTGCATCAGCATATTA
3004  88_HRV75b|    ACATGGACAAACATTTCCAAGATTTTCACTACCATTTCTGAGCATTGCATCAGCATATTA
3005  89_HRV75a|    ACATGGACAAACATTTCCAAGATTTTCACTACCATTTCTGAGCATTGCATCAGCATATTA
3006  96_HRV9a|d    ACATGGACAATCATATCCCAGATTTTCACTTCCGTTTTGAGCATTGCCTCTGCATATTA
3007  97_HRV9b|d    ACATGGACAATCATATCCCAGATTTTCACTTCCGTTTTGAGCATTGCCTCTGCATATTA
3008  98_HRV9       ACATGGACAATCATATCCCAGATTTTCACTTCCGTTTTGAGCATTGCCTCTGCATATTA
```

FIG. D5 CONT'D 01.trace                                                                 9/20/2007 4:58 PM

```
3009  99_HRV32    GCATGGACAGGCATATCCCAGGTTTTCACTTCCATTTCTAAGTATTGCCTCTGCATACTA
3010  100_HRV32a   GCATGGACAGGCATATCCCAGGTTTTCACTTCCATTTCTAAGTATTGCCTCTGCATACTA
3011  101_HRV32b   GCATGGACAGGCATATCCCAGGTTTTCACTTCCATTTCTAAGTATTGCCTCTGCATACTA
3012  102_HRV67    ACATGGACAATCATACCCCAGATTCTCACTACCATTCTTAAGTATTGCCTCTGCTTATTA
3013  103_HRV67a   ACATGGACAATCATACCCCAGATTCTCACTACCATTCTTAAGTATTGCCTCTGCTTATTA
3014  104_HRV67b   ACATGGACAATCATACCCCAGATTCTCACTACCATTCTTAAGTATTGCCTCTGCTTATTA
3015  105_HRV15    ACATGGTCAACCTTACCCCAGATTTTCTTTGCCTTTTCTCAGCATTGCATCTGCTTACTA
3016  106_HRV15a   ACATGGTCAACCTTACCCCAGATTTTCTTTGCCTTTTCTCAGCATTGCATCTGCTTACTA
3017  107_HRV15b   ACATGGTCAACCTTACCCCAGATTTTCTTTGCCTTTTCTCAGCATTGCATCTGCTTACTA
3018  108_HRV74a   GCATGGACAGCCATACCCTAGATTCTCATTACCTTTCCTTAGCATAGCATCTGCTTATTA
3019  109_HRV74b   GCATGGACAGCCATACCCTAGATTCTCATTACCTTTCCTTAGCATAGCATCTGCTTATTA
3020  110_HRV74    GCATGGACAGCCATACCCTAGATTCTCATTACCTTTCCTTAGCATAGCATCTGCTTATTA
3021  111_HRV38a   ATATGGTCAGACATATCCTCGATTTTCCTTACCTTTCTTAAGCATTGCATCTGTCTATTA
3022  112_HRV38b   ATATGGTCAGACATATCCTCGATTTTCCTTACCTTTCTTAAGCATTGCATCTGTCTATTA
3023  113_HRV38    ATATGGTCAGACATATCCTCGATTTTCCTTACCTTTCTTAAGCATTGCATCTGTCTATTA
3024  114_HRV60    GCATGGACAAACATACCCTAGATTTTCACTTCCATTTCTAAGTATTGCATCTGCCTACTA
3025  115_HRV60a   GCATGGACAAACATACCCTAGATTTTCACTTCCATTTCTAAGTATTGCATCTGCCTACTA
3026  116_HRV60b   GCATGGACAAACATACCCTAGATTTTCACTTCCATTTCTAAGTATTGCATCTGCCTACTA
3027  117_HRV64a   ACACGGTCAACCATACCCTCGATTTTCTCTCCCTTTCCTTAGCATAGCCTCAGCATATTA
3028  118_HRV64b   ACACGGTCAACCATACCCTCGATTTTCTCTCCCTTTCCTTAGCATAGCCTCAGCATATTA
3029  119_HRV64    ACACGGTCAACCATACCCTCGATTTTCTCTCCCTTTCCTTAGCATAGCCTCAGCATATTA
3030  120_HRV94a   ACATGGTCAACCCTACCCTCGATTCTCACTTCCATTTCTTAGTATAGCCTCAGCATATTA
3031  121_HRV94b   ACATGGTCAACCCTACCCTCGATTCTCACTTCCATTTCTTAGTATAGCCTCAGCATATTA
3032  122_HRV94    ACATGGTCAACCCTACCCTCGATTCTCACTTCCATTTCTTAGTATAGCCTCAGCATATTA
3033  123_HRV22    GCATGGTCAACCTTATCCCCGATTCTCACTCCCTTTCCTCAGTGTAGCTTCAGCATATTA
3034  124_HRV22a   GCATGGTCAACCTTATCCCCGATTCTCACTCCCTTTCCTCAGTGTAGCTTCAGCATATTA
3035  125_HRV22b   GCATGGTCAACCTTATCCCCGATTCTCACTCCCTTTCCTCAGTGTAGCTTCAGCATATTA
3036  126_HRV82    ACATGGACAACCTTACCCTCGCTTCTCACTTCCTTTCTTGAGTATAGCCTCAGCTTACTA
3037  127_HRV82b   ACATGGACAACCTTACCCTCGCTTCTCACTTCCTTTCTTGAGTATAGCCTCAGCTTACTA
3038  128_HRV82a   ACATGGACAACCTTACCCTCGCTTCTCACTTCCTTTCTTGAGTATAGCCTCAGCTTACTA
3039  129_HRV19    ACATGGTCAACCATACCCAAGATTTTCATTACCTTTTCTAAGTATAGCTTCTGCATATTA
3040  130_HRV19a   ACATGGTCAACCATACCCAAGATTTTCATTACCTTTTCTAAGTATAGCTTCTGCATATTA
3041  131_HRV19b   ACATGGTCAACCATACCCAAGATTTTCATTACCTTTTCTAAGTATAGCTTCTGCATATTA
3042  132_HRV13    ACATGGTCAAATTTACCCCCGATTCTCTTTACCATTTCTTAGTATTGCATCTGCATATTA
3043  133_HRV13a   ACATGGTCAAATTTACCCCCGATTCTCTTTACCATTTCTTAGTATTGCATCTGCATATTA
3044  134_HRV13b   ACATGGTCAAATTTACCCCCGATTCTCTTTACCATTTCTTAGTATTGCATCTGCATATTA
3045  135_HRV41    GTATGGTCAAGTTTACCCTAGGTTTTCTCTACCATTTCTTAGCATTGCTTCCGCATATTA
3046  136_HRV41a   GTATGGTCAAGTTTACCCTAGGTTTTCTCTACCATTTCTTAGCATTGCTTCCGCATATTA
3047  137_HRV41b   GTATGGTCAAGTTTACCCTAGGTTTTCTCTACCATTTCTTAGCATTGCTTCCGCATATTA
3048  138_HRV73    ACATGGTCAAACTTACCCCAGATTCTCATTACCATTCCTTAGTATAGCATCCGCATATTA
3049  139_HRV73b   ACATGGTCAAACTTACCCCAGATTCTCATTACCATTCCTTAGTATAGCATCCGCATATTA
3050  140_HRV73a   ACATGGTCAAACTTACCCCAGATTCTCATTACCATTCCTTAGTATAGCATCCGCATATTA
3051  141_HRV61    ACATGGTCAAGCTTATCCCAGATTTTCATTACCATTCCTAAGTATTGCATCTGCATATTA
3052  142_HRV61a   ACATGGTCAAGCTTATCCCAGATTTTCATTACCATTCCTAAGTATTGCATCTGCATATTA
3053  143_HRV61b   ACATGGTCAAGCTTATCCCAGATTTTCATTACCATTCCTAAGTATTGCATCTGCATATTA
3054  144_HRV96    GCACGGGCAAGCATATCCTAGATTTTCACTGCCTTTCCTTAGTATTGCCTCTGCATATTA
3055  145_HRV96b   GCACGGGCAAGCATATCCTAGATTTTCACTGCCTTTCCTTAGTATTGCCTCTGCATATTA
3056  146_HRV96a   GCACGGGCAAGCATATCCTAGATTTTCACTGCCTTTCCTTAGTATTGCCTCTGCATATTA
3057  90_HRV16a|   GCATGGGCAACCTTTCCCTCGCTTTTCACTTCCCTTTTTGAGTATTGCATCAGCATATTA
3058  91_HRV16b|   GCATGGGCAACCTTTCCCTCGCTTTTCACTTCCCTTTTTGAGTATTGCATCAGCATATTA
3059  92_1AYM_A    GCATGGGCAACCTTTCCCTCGCTTTTCACTTCCCTTTTTGAGTATTGCATCAGCATATTA
3060  93_HRV81a|   ACATGGGCAACCCTTTCCCCGGTTTTCACTCCCTTTTCTAAGTGTAGCATCAGCATATTA
3061  94_HRV81b|   ACATGGGCAACCCTTTCCCCGGTTTTCACTCCCTTTTCTAAGTGTAGCATCAGCATATTA
3062  95_HRV81     ACATGGGCAACCCTTTCCCCGGTTTTCACTCCCTTTTCTAAGTGTAGCATCAGCATATTA
3063  147_HRV2     ACATGGACAGGCTTATCCAAGATTTTCCTTACCTTTCCTAAGTGTGGCATCTGCTTATTA
3064  148_HRV2a|   ACATGGACAGGCTTATCCAAGATTTTCCTTACCTTTCCTAAGTGTGGCATCTGCTTATTA
3065  149_HRV2b|   ACATGGACAGGCTTATCCAAGATTTTCCTTACCTTTCCTAAGTGTGGCATCTGCTTATTA
3066  150_HRV49a   ACATGGGCAAGCATACCCAAGATTTCTCTACCCTTTTTGAGTGTAGCTTCAGCTTACTA
3067  151_HRV49b   ACATGGGCAAGCATACCCAAGATTTTCTCTACCCTTTTTGAGTGTAGCTTCAGCTTACTA
3068  152_HRV49    ACATGGGCAAGCATACCCAAGATTTTCTCTACCCTTTTTGAGTGTAGCTTCAGCTTACTA
3069  153_HRV23a   ACATGGACAAACATATCCAAGGTTCTCCTTACCCTTTTTGAGTGTGGCATCTGCTTATTA
3070  154_HRV23b   ACATGGACAAACATATCCAAGGTTCTCCTTACCCTTTTTGAGTGTGGCATCTGCTTATTA
3071  155_HRV23    ACATGGACAAACATATCCAAGGTTCTCCTTACCCTTTTTGAGTGTGGCATCTGCTTATTA
3072  156_HRV30a   ACACGGACAAACATACCCAAGATTCTCCCTACCATTTTTGAGTGTAGCATCTGCTTATTA
```

FIG. D5 CONT'D 01.trace                                                                9/20/2007 4:58 PM

```
3073 157_HRV30b   ACACGGACAAACATACCCAAGATTCTCCCTACCATTTTTGAGTGTAGCATCTGCTTATTA
3074 158_HRV30    ACACGGACAAACATACCCAAGATTCTCCCTACCATTTTTGAGTGTAGCATCTGCTTATTA
3075 159_HRV7     GGAGGGTCAACCATACCCTAGATTCACAATTCCTTTTATGAGTATTGCATCAGCTTATTA
3076 160_HRV7b|   GGAGGGTCAACCATACCCTAGATTCACAATTCCTTTTATGAGTATTGCATCAGCTTATTA
3077 161_HRV7a|   GGAGGGTCAACCATACCCTAGATTCACAATTCCTTTTATGAGTATTGCATCAGCTTATTA
3078 162_HRV88    AGAAGGACAACCATACCCAAGATTTACCATTCCCTTTATGAGTATTGCATCAGCTTACTA
3079 163_HRV88a   AGAAGGACAACCATACCCAAGATTTACCATTCCCTTTATGAGTATTGCATCAGCTTACTA
3080 164_HRV88b   AGAAGGACAACCATACCCAAGATTTACCATTCCCTTTATGAGTATTGCATCAGCTTACTA
3081 165_HRV36a   AGAAGGGCAACCATATCCTAGATTTACAATCCCCTTTATGAGTATTGCATCAGCTTATTA
3082 166_HRV36b   AGAAGGGCAACCATACCCTAGATTTACAATCCCCTTTATGAGTATTGCATCAGCTTATTA
3083 167_HRV36    AGAAGGGCAACCATATCCTAGATTTACAATCCCCTTTATGAGTATTGCATCAGCTTATTA
3084 168_HRV89a   AGAAGGACAACCATACCCCAGATTCACAATCCCTTTTATGAGCATTGCATCAGCCTATTA
3085 169_HRV89b   AGAAGGACAACCATACCCCAGATTCACAATCCCTTTTATGAGCATTGCATCAGCCTATTA
3086 170_HRV89    AGAAGGACAACCATACCCCAGATTCACAATCCCTTTTATGAGCATTGCATCAGCCTATTA
3087 171_HRV58    GGAAGGACAACCATACCCTAGATTTACAATCCCTTTTATGAGTATTGCATCAGCTTACTA
3088 172_HRV58a   GGAAGGACAACCATACCCTAGATTTACAATCCCTTTTATGAGCATTGCATCAGCTTACTA
3089 173_HRV58b   GGAAGGACAACCATACCCTAGATTTACAATCCCTTTTATGAGCATTGCATCAGCTTACTA
3090 174_HRV12a   GGAAGGTCAACCTTACCCCAGATTCACAATCCCTTTTATTAGTATTGCCTCAGCATATTA
3091 175_HRV12b   GGAAGGTCAACCTTACCCCAGATTCACAATCCCTTTTATTAGTATTGCCTCAGCATATTA
3092 176_HRV12    GGAAGGTCAACCTTACCCCAGATTCACAATCCCTTTTATTAGTATTGCCTCAGCATATTA
3093 177_HRV78a   ACAAGGTCAAACATACCCCAGGTTCTCTATACCATTTTCTAGTATTGCCTCAGCTTATTA
3094 178_HRV78b   ACAAGGTCAAACATACCCCAGGTTCTCTATACCATTTTCTAGTATTGCCTCAGCTTATTA
3095 179_HRV78    ACAAGGTCAAACATACCCCAGGTTCTCTATACCATTTTCTAGTATTGCCTCAGCTTATTA
3096 180_HRV20    GCAGGGCCAACCTTACCCCAGATTTACCATTCCATTTATGAGTATAGCTTCAGCATATTA
3097 181_HRV20a   GCAGGGCCAACCTTACCCCAGATTTACCATTCCATTTATGAGTATAGCTTCAGCATATTA
3098 182_HRV20b   GCAGGGCCAACCTTACCCCAGATTTACCATTCCATTTATGAGTATAGCTTCAGCATATTA
3099 183_HRV68    ACAAGGACAACCTTACCCCAGATTTACCATTCCATTTATGAGTATAGCTTCAGCATATTA
3100 184_HRV68a   ACAAGGACAACCTTACCCCAGATTTACCATTCCATTTATGAGTATAGCTTCAGCATATTA
3101 185_HRV68b   ACAAGGACAACCTTACCCCAGATTTACCATTCCATTTATGAGTATAGCTTCAGCATATTA
3102 186_HRV28    ACAAGGACAACCATATCCCAGATTCACTATACCTTTTATGAGTATTGCCTCAGCTTATTA
3103 187_HRV28a   ACAAGGACAACCATATCCCAGATTCACTATACCTTTTATGAGTATTGCCTCAGCTTATTA
3104 188_HRV28b   ACAAGGACAACCATATCCCAGATTCACTATACCTTTTATGAGTATTGCCTCAGCTTATTA
3105 189_HRV53a   ACAAGGACAACCATACCCTAGATTCACAATCCCTTTCATGAGTATTGCGTCAGCATATTA
3106 190_HRV53b   ACAAGGACAACCATACCCTAGATTCACAATCCCTTTCATGAGTATTGCGTCAGCATATTA
3107 191_HRV53    ACAAGGACAACCATACCCTAGATTCACAATCCCTTTCATGAGTATTGCGTCAGCATATTA
3108 192_HRV46a   GCAAGGGCAGCCATACCCTAGATTCACTATCCCGTTCATGAGTATAGCCTCAGCATATTA
3109 193_HRV46b   GCAAGGGCAGCCATACCCTAGATTCACTATCCCGTTCATGAGTATAGCCTCAGCATATTA
3110 194_HRV46    GCAAGGGCAGCCATACCCTAGATTCACTATCCCGTTCATGAGTATAGCCTCAGCATATTA
3111 195_HRV80a   ACAGGGTCAGCCATACCCCAGATTCACTATTCCATTCATGAGTATAGCCTCAGCTTATTA
3112 196_HRV80b   ACAGGGTCAGCCATACCCCAGATTCACTATTCCATTCATGAGTATAGCCTCAGCTTATTA
3113 197_HRV80    ACAGGGTCAGCCATACCCCAGATTCACTATTCCATTCATGAGTATAGCCTCAGCTTATTA
3114 198_HRV51    ACATGGACAACCATACCCTAGATTTACAATCCCTTTTGTAAGCATAGCCTCAGCATACTA
3115 199_HRV51a   ACATGGACAACCATACCCTAGATTTACAATCCCTTTTGTAAGCATAGCCTCAGCATACTA
3116 200_HRV51b   ACATGGACAACCATACCCTAGATTTACAATCCCTTTTGTAAGCATAGCCTCAGCATACTA
3117 201_HRV65a   GCATGGTCAACCATACCCCAGATTTACAATTCCTTTTGTGAGTATTGCCTCAGCATATTA
3118 202_HRV65b   GCATGGTCAACCATACCCCAGATTTACAATTCCTTTTGTGAGTATTGCCTCAGCATATTA
3119 203_HRV65    GCATGGTCAACCATACCCCAGATTTACAATTCCTTTTGTGAGTATTGCCTCAGCATATTA
3120 204_HRV71a   GCACGGCCAACCATACCCAAGGTTTACAATCCCCTTCATAAGCATTGCATCAGCATATTA
3121 205_HRV71b   GCACGGCCAACCATACCCAAGGTTTACAATCCCCTTCATAAGCATTGCATCAGCATATTA
3122 206_HRV71    GCACGGCCAACCATACCCAAGGTTTACAATCCCCTTCATAAGCATTGCATCAGCATATTA
3123 207_HRV8     AGTTGGACAAACTTATCCCAGATTCACCATACCTTCTCCAGCATAGCATCAGCTTATTA
3124 208_HRV95    AGTTGGACAGACTTATCCCAGATTCACCATACCTTTCTCCAGTATAGCATCAGCTTATTA
3125 209_HRV45    GGTTGGTCAAACTTATCCCAGATTTTCTATACCTTTCTCAAGTATAGCTTCAGCTTACTA
3126 210_HRV45a   GGTTGGTCAAACTTATCCCAGATTTTCTATACCTTTCTCAAGTATAGCTTCAGCTTACTA
3127 211_HRV45b   GGTTGGTCAAACTTATCCCAGATTTTCTATACCTTTCTCAAGTATAGCTTCAGCTTACTA
3128 212_HRV6     ------------------------------------------------------------
3129 213_HRV6a|   ------------------------------------------------------------
3130 214_HRV6b|   ------------------------------------------------------------
3131 215_HRV37    ------------------------------------------------------------
3132 216_HRV37a   ------------------------------------------------------------
3133 217_HRV37b   ------------------------------------------------------------
3134 218_HRV3     ------------------------------------------------------------
3135 219_HRV3a|   ------------------------------------------------------------
3136 220_HRV3b|   ------------------------------------------------------------
```

FIG. D5 CONT'D 01.trace 9/20/2007 4:58 PM

```
3137 221_HRV14    ------------------------------------------------
3138 222_HRV14a   ------------------------------------------------
3139 223_HRV14b   ------------------------------------------------
3140 224_HRV72    ------------------------------------------------
3141 225_HRV72a   ------------------------------------------------
3142 226_HRV72b   ------------------------------------------------
3143 227_HRV83    ------------------------------------------------
3144 228_HRV83a   ------------------------------------------------
3145 229_HRV83b   ------------------------------------------------
3146 230_HRV92    ------------------------------------------------
3147 231_HRV92a   ------------------------------------------------
3148 232_HRV92b   ------------------------------------------------
3149 233_HRV79    ------------------------------------------------
3150 234_HRV79a   ------------------------------------------------
3151 235_HRV79b   ------------------------------------------------
3152 236_HRV35    ------------------------------------------------
3153 237_HRV35a   ------------------------------------------------
3154 238_HRV35b   ------------------------------------------------
3155 239_1HRV86   ------------------------------------------------
3156 240_1HRV86   ------------------------------------------------
3157 241_1HRV86   ------------------------------------------------
3158 242_HRV70    ------------------------------------------------
3159 243_HRV70a   ------------------------------------------------
3160 244_HRV70b   ------------------------------------------------
3161 245_HRV91    ------------------------------------------------
3162 246_HRV91a   ------------------------------------------------
3163 247_HRV91b   ------------------------------------------------
3164 248_HRV17    ------------------------------------------------
3165 249_HRV17a   ------------------------------------------------
3166 250_HRV17b   ------------------------------------------------
3167 251_HRV69    ------------------------------------------------
3168 252_HRV69a   ------------------------------------------------
3169 253_HRV69b   ------------------------------------------------
3170 254_HRV48    ------------------------------------------------
3171 255_HRV48a   ------------------------------------------------
3172 256_HRV48b   ------------------------------------------------
3173 257_HRV52    ------------------------------------------------
3174 258_HRV52a   ------------------------------------------------
3175 259_HRV52b   ------------------------------------------------
3176 260_HRV4     ------------------------------------------------
3177 261_HRV4a|   ------------------------------------------------
3178 262_HRV4b|   ------------------------------------------------
3179 263_HRV99    ------------------------------------------------
3180 264_HRV99a   ------------------------------------------------
3181 265_HRV99b   ------------------------------------------------
3182 266_HRV5     ------------------------------------------------
3183 267_HRV5a|   ------------------------------------------------
3184 268_HRV5b|   ------------------------------------------------
3185 269_HRV42    ------------------------------------------------
3186 270_HRV42a   ------------------------------------------------
3187 271_HRV42b   ------------------------------------------------
3188 272_HRV26    ------------------------------------------------
3189 273_HRV26a   ------------------------------------------------
3190 274_HRV26b   ------------------------------------------------
3191 275_HRV27    ------------------------------------------------
3192 276_HRV27a   ------------------------------------------------
3193 277_HRV27b   ------------------------------------------------
3194 278_HRV93    ------------------------------------------------
3195 279_HRV93a   ------------------------------------------------
3196 280_HRV93b   ------------------------------------------------
3197 281_HRV97    ------------------------------------------------
3198 282_HRV97a   ------------------------------------------------
3199 283_HRV97b   ------------------------------------------------
3200 284_HRV84    ------------------------------------------------
```

FIG. D5 CONT'D

01.trace                                                                9/20/2007 4:58 PM

```
3201  285_HRV84a         ------------------------------------------------------------
3202  286_HRV84b         ------------------------------------------------------------
3203  287_HRV87          ------------------------------------------------------------
3204  288_HRV87a         ------------------------------------------------------------
3205  289_HRV87b         ------------------------------------------------------------
3206  GROUP_1            ------------------------------------------------------------
3207
3208   1_HRV1A1|d        TATGTTTTATGATGGATATGATGGAGACAACACTTCTTCCAAGTATGGTAGCGTAGTTAC
3209   2_HRV1A2|d        TATGTTTTATGATGGATATGATGGAGACAACACTTCTTCCAAGTATGGTAGCGTAGTTAC
3210   3_HRV1A|cD        TATGTTTTATGATGGATATGATGGAGACAACACTTCTTCCAAGTATGGTAGCGTAGTTAC
3211   4_HRV1B1|d        CATGTTTTATGATGGATATGATGGAGATAATTCCTCTTCCAAATATGGTAGTATAGTCAC
3212   5_HRV1B2|d        CATGTTTTATGATGGATATGATGGAGATAATTCCTCTTCCAAATATGGTAGTATAGTCAC
3213   6_HRV1B           CATGTTTTATGATGGATATGATGGAGATAATTCCTCTTCCAAATATGGTAGTATAGTCAC
3214   7_HRV40a|d        CATGTTTTATGATGGATACGATGGTGATACATCGACCTCAAGATATGGCACATCAGTCAC
3215   8_HRV40b|d        CATGTTTTATGATGGATACGATGGTGATACATCGACCTCAAGATATGGCACATCAGTCAC
3216   9_HRV40           CATGTTTTATGATGGATACGATGGTGATACATCGACCTCAAGATATGGCACATCAGTCAC
3217  10_HRV85           CATGTTTTATGATGGTTATGATGGTGATACACCAGGCTCAATGTATGGGACGTCAGTCAC
3218  11_HRV85a|         CATGTTTTATGATGGTTATGATGGTGATACACCAGGCTCAATGTATGGGACGTCAGTCAC
3219  12_HRV85b|         CATGTTTTATGATGGTTATGATGGTGATACACCAGGCTCAATGTATGGGACGTCAGTCAC
3220  13_HRV56a|         CATGTTTTATGATGGTTATGATGGAGACACTTCAAGCTCCAGATATGGTACATCAGTTAC
3221  14_HRV56b|         CATGTTTTATGATGGTTATGATGGAGACACTTCAAGCTCCAGATATGGTACATCAGTTAC
3222  15_HRV56           CATGTTTTATGATGGTTATGATGGAGACACTTCAAGCTCCAGATATGGTACATCAGTTAC
3223  16_HRV54           CATGTTTTATGATGGGTATGATGGTGACGCACCTGGATCAAGATATGGGACTTCAGTTAC
3224  17_HRV98           CATGTTTTACGATGGGTATGATGGTGATGCACCTGGATCAAGATATGGAACCTCAGTCAC
3225  18_HRV59a|         CATGTTTTATGATGGTTATGATGGAGATAAATCTGAATCTAGGTATGGTGTGTCTGTAAC
3226  19_HRV59b|         CATGTTTTATGATGGTTATGATGGAGATAAATCTGAATCTAGGTATGGTGTGTCTGTAAC
3227  20_HRV59           CATGTTTTATGATGGTTATGATGGAGATAAATCTGAATCTAGGTATGGTGTGTCTGTAAC
3228  21_HRV63           CATGTTTTATGATGGATATGATGGAGATAAATCAAGCTCTAGGTATGGTGTTTCAGTTAC
3229  22_HRV63b|         CATGTTTTATGATGGATATGATGGAGATAAATCAAGCTCTAGGTATGGTGTTTCAGTTAC
3230  23_HRV63a|         CATGTTTTATGATGGATATGATGGAGATAAATCAAGCTCTAGGTATGGTGTTTCAGTTAC
3231  24_HRV39           TATGTTCTATGATGGATATGATGGTGATAAATCGTCATCTAGGTATGGTGTTTCTGTCAC
3232  25_HRV39a|         TATGTTCTATGATGGATATGATGGTGATAAATCGTCATCTAGGTATGGTGTTTCTGTCAC
3233  26_HRV39b|         TATGTTCTATGATGGATATGATGGTGATAAATCGTCATCTAGGTATGGTGTTTCTGTCAC
3234  27_HRV10a|         CATGTTCTATGATGGTTATGATGGTGATACACATGACTCACGTTATGGCACAACAGTGAT
3235  28_HRV10b|         CATGTTCTATGATGGTTATGATGGTGATACACATGACTCACGTTATGGCACAACAGTGAT
3236  29_HRV10           CATGTTCTATGATGGTTATGATGGTGATACACATGACTCACGTTATGGCACAACAGTGAT
3237  30_HRV100a         CATGTTTTATGATGGATATGATGGTGATACACATGATTCACACTATGGTACTACTGTAAT
3238  31_HRV100b         CATGTTTTATGATGGATATGATGGTGATACACATGATTCACACTATGGTACTACTGTAAT
3239  32_HRV100          CATGTTTTATGATGGATATGATGGTGATACACATGATTCACACTATGGTACTACTGTAAT
3240  33_HRV66           CATGTTCTATGATGGTTATGATGGAGATACTCCTGGGTCTCGTTATGGAACCACAGTAGT
3241  34_HRV66b|         CATGTTCTATGATGGTTATGATGGAGATACTCCTGGGTCTCGTTATGGAACCACAGTAGT
3242  35_HRV66a|         CATGTTCTATGATGGTTATGATGGAGATACTCCTGGGTCTCGTTATGGAACCACAGTAGT
3243  36_HRV77a|         CATGTTTTATGATGGCTATGATGGGGATACCTATGAATCACGTTATGGTACTACAGTGGT
3244  37_HRV77b|         CATGTTTTATGATGGCTATGATGGGGATACCTATGAATCACGTTATGGTACTACAGTGGT
3245  38_HRV77           CATGTTTTATGATGGCTATGATGGGGATACCTATGAATCACGTTATGGTACTACAGTGGT
3246  39_HRV62a          CATGTTTTATGATGGCTATAATGGTGATGACTATACAGCAAAATACGGTACCACCGTGGT
3247  40_HRV62b          CATGTTTTATGATGGCTATAATGGTGATGACTATACAGCAAAATACGGTACCACCGTGGT
3248  41_HRV25           CATGTTTTATGATGGCTATAATGGTGATGATCACACAGCGAGATATGGTACCACTGTGGT
3249  42_HRV29a          CATGTTTTATGATGGTTACAATGGAGGTGATCATACAGCAACTTATGGCACCACAGTGGT
3250  43_HRV29b          CATGTTTTATGATGGTTACAATGGAGGTGATCATACAGCAACTTATGGCACCACAGTGGT
3251  44_HRV44a          CATGTTTTATGACGGTTATAATGGAGGTGATCATACAGCAACTTATGGCACCACAGTGGT
3252  45_HRV44b          CATGTTTTATGACGGTTATAATGGAGGTGATCATACAGCAACTTATGGCACCACAGTGGT
3253  46_HRV31           CATGTTTTATGATGGTTATGATGGAGACAAAAGTGGAGCCAAGTATGGTACTACAGTAGT
3254  47_HRV31a|         CATGTTTTATGATGGTTATGATGGAGACAAAAGTGGAGCCAAGTATGGTACTACAGTAGT
3255  48_HRV31b|         CATGTTTTATGATGGTTATGATGGAGACAAAAGTGGAGCCAAGTATGGTACTACAGTAGT
3256  49_HRV47           CATGTTTTATGATGGCTATAATGGTGACAGAAGTGGAGCCAAGTATGGCACCACAGTGGT
3257  50_HRV47a|         CATGTTTTATGATGGCTATAATGGTGACAGAAGTGGAGCCAAGTATGGCACCACAGTGGT
3258  51_HRV47b|         CATGTTTTATGATGGCTATAATGGTGACAGAAGTGGAGCCAAGTATGGCACCACAGTGGT
3259  52_HRV11           CATGTTTTATGATGGATATGATGGAGATCAACCAAACTCCAGATATGGTAATATAGTTAC
3260  53_HRV11b|         CATGTTTTATGATGGATATGATGGAGATCAACCAAACTCCAGATATGGTAATATAGTTAC
3261  54_HRV11a|         CATGTTTTATGATGGATATGATGGAGATCAACCAAACTCCAGATATGGTAATATAGTTAC
3262  55_HRV76           CATGTTTTATGATGGATATGATGGAGACCAACCTAGTTCTAGGTATGGTAATATAGTTAC
3263  56_HRV76b|         CATGTTTTATGATGGATATGATGGAGACCAACCTAGTTCTAGGTATGGTAATATAGTTAC
3264  57_HRV76a|         CATGTTTTATGATGGATATGATGGAGACCAACCTAGTTCTAGGTATGGTAATATAGTTAC
```

FIG. D5 CONT'D 01.trace                                                                    9/20/2007 4:58 PM

```
3265  58_HRV33     CATGTTCTATGATGGATATGATGGGGACCAACCCAATTCCAGGTATGGTAATATGGTTAC
3266  59_HRV33b|   CATGTTCTATGATGGATATGATGGGGACCAACCCAATTCCAGGTATGGTAATATGGTTAC
3267  60_HRV33a|   CATGTTCTATGATGGATATGATGGGGACCAACCCAATTCCAGGTATGGTAATATGGTTAC
3268  61_HRV24a|   CATGTTTTATGATGGATATGATGGTGATCAACACGACTCAGTGTATGGTTCAGTTGTTAC
3269  62_HRV24b|   CATGTTTTATGATGGATATGATGGTGATCAACACGACTCAGTGTATGGTTCAGTTGTTAC
3270  63_HRV24     CATGTTTTATGATGGATATGATGGTGATCAACACGACTCAGTGTATGGTTCAGTTGTTAC
3271  64_HRV90     TATGTTTTATGATGGATATGATGGTGACCAAACTGATTCGAGATATGGTACCATTGTTAC
3272  65_HRV90a|   TATGTTTTATGATGGATATGATGGTGACCAAACTGATTCGAGATATGGTACCATTGTTAC
3273  66_HRV90b|   TATGTTTTATGATGGATATGATGGTGACCAAACTGATTCGAGATATGGTACCATTGTTAC
3274  67_HRV34     CATGTTTTATGATGGATATGATGGTGATCAACATGATTCAAGATATGGTACAGTAGTGAC
3275  68_HRV34b|   CATGTTTTATGATGGATATGATGGTGATCAACATGATTCAAGATATGGTACAGTAGTGAC
3276  69_HRV34a|   CATGTTTTATGATGGATATGATGGTGATCAACATGATTCAAGATATGGTACAGTAGTGAC
3277  70_HRV50a|   CATGTTTTATGATGGTTATGATGGTGATAAATCTACATCCAGGTATGGTACAGTAGTTAC
3278  71_HRV50b|   CATGTTTTATGATGGTTATGATGGTGATAAATCTACATCCAGGTATGGTACAGTAGTTAC
3279  72_HRV50     CATGTTTTATGATGGTTATGATGGTGATAAATCTACATCCAGGTATGGTACAGTAGTTAC
3280  73_HRV18a|   CATGTTCTATGATGGCTACGACGGTGACCAGACCTCATCGCGGTATGGCACAGTTGCAAC
3281  74_HRV18b|   CATGTTCTATGATGGCTACGACGGTGACCAGACCTCATCGCGGTATGGCACAGTTGCAAC
3282  75_HRV18     CATGTTCTATGATGGCTACGACGGTGACCAGACCTCATCGCGGTATGGCACAGTTGCAAC
3283  76_HRV55     CATGTTCTATGATGGATATGATGGTGACCAAACTGAGTCACGCTATGGCACTGTAGTCAC
3284  77_HRV55b|   CATGTTCTATGATGGATATGATGGTGACCAAACTGAGTCACGCTATGGCACTGTAGTCAC
3285  78_HRV55a|   CATGTTCTATGATGGATATGATGGTGACCAAACTGAGTCACGCTATGGCACTGTAGTCAC
3286  79_HRV57     CATGTTTTATGATGGATATGATGGTGACCAAACTGAATCAAGATATGGTACTGTAGTCAC
3287  80_HRV57a|   CATGTTTTATGATGGATATGATGGTGACCAAACTGAATCAAGATATGGTACTGTAGTCAC
3288  81_HRV57b|   CATGTTTTATGATGGATATGATGGTGACCAAACTGAATCAAGATATGGTACTGTAGTCAC
3289  82_HRV21     CATGTTTTATGATGGTTATGATGGTGACCAGACTGACTCACAATATGGTGCAGTAGTAAC
3290  83_HRVHan    CATGTTTTATGATGGTTATGATGGTGATCAGACTGACTCACAATATGGTGCAGTGGTGAC
3291  84_HRV43     CATGTTTTATGATGGATATGAAGGTGACCAAAAAACATCCCGTTATGGCACAATTGCAAG
3292  85_HRV43b|   CATGTTTTATGATGGATATGAAGGTGACCAAAAAACATCCCGTTATGGCACAATTGCAAG
3293  86_HRV43a|   CATGTTTTATGATGGATATGAAGGTGACCAAAAAACATCCCGTTATGGCACAATTGCAAG
3294  87_HRV75     CATGTTTTATGATGGATATGAAGGGGATCAAAATACATCCCGTTATGGCACCATTGCTAG
3295  88_HRV75b|   CATGTTTTATGATGGATATGAAGGGGATCAAAATACATCCCGTTATGGCACCATTGCTAG
3296  89_HRV75a|   CATGTTTTATGATGGATATGAAGGGGATCAAAATACATCCCGTTATGGCACCATTGCTAG
3297  96_HRV9a|d   CATGTTCTATGATGGTTATGATGGTGG---ACCAGATTCTCTGTATGGAACAATTGTAAC
3298  97_HRV9b|d   CATGTTCTATGATGGTTATGATGGTGG---ACCAGATTCTCTGTATGGAACAATTGTAAC
3299  98_HRV9      CATGTTCTATGATGGTTATGATGGTGG---ACCAGATTCTCTGTATGGAACAATTGTAAC
3300  99_HRV32     CATGTTTTATGATGGTTATGATGGTGG---GCCAGATTCACAATATGGAACAATTGTAAC
3301  100_HRV32a   CATGTTTTATGATGGTTATGATGGTGG---GCCAGATTCACAATATGGAACAATTGTAAC
3302  101_HRV32b   CATGTTTTATGATGGTTATGATGGTGG---GCCAGATTCACAATATGGAACAATTGTAAC
3303  102_HRV67    CATGTTTTATGATGGCTATGATGGTGG---ACCAGATTCACTATATGGCACCATAGTAAC
3304  103_HRV67a   CATGTTTTATGATGGCTATGATGGTGG---ACCAGATTCACTATATGGCACCATAGTAAC
3305  104_HRV67b   CATGTTTTATGATGGCTATGATGGTGG---ACCAGATTCACTATATGGCACCATAGTAAC
3306  105_HRV15    CATGTTCTATGATGGATATGATGGAGATTCCACTGAATCACATTATGGTACAGTGGTCAC
3307  106_HRV15a   CATGTTCTATGATGGATATGATGGAGATTCCACTGAATCACATTATGGTACAGTGGTCAC
3308  107_HRV15b   CATGTTCTATGATGGATATGATGGAGATTCCACTGAATCACATTATGGTACAGTGGTCAC
3309  108_HRV74a   CATGTTTTATGATGGATATGATGGAGACTCTACTGAATCACATTATGGTACAGTAGTAAC
3310  109_HRV74b   CATGTTTTATGATGGATATGATGGAGACTCTACTGAATCACATTATGGTACAGTAGTAAC
3311  110_HRV74    CATGTTTTATGATGGATATGATGGAGACTCTACTGAATCACATTATGGTACAGTAGTAAC
3312  111_HRV38a   TATGTTTTATGATGGATATGATGGGGACTCAACAGAATCACATTATGGGACAGCGGTGAC
3313  112_HRV38b   TATGTTTTATGATGGATATGATGGGGACTCAACAGAATCACATTATGGGACAGCGGTGAC
3314  113_HRV38    TATGTTTTATGATGGATATGATGGGGACTCAACAGAATCACATTATGGGACAGCGGTGAC
3315  114_HRV60    CATGTTTTATGATGGTTATGATGGTCACTCAACTGAATCACATTATGGGACGGTTGTGAC
3316  115_HRV60a   CATGTTTTATGATGGTTATGATGGTCACTCAACTGAATCACATTATGGGACGGTTGTGAC
3317  116_HRV60b   CATGTTTTATGATGGTTATGATGGTCACTCAACTGAATCACATTATGGGACGGTTGTGAC
3318  117_HRV64a   CATGTTTTATGATGGTTATGACGGTGG---ACCTGGTTCCCGTTATGGCGCAGTGGTGAC
3319  118_HRV64b   CATGTTTTATGATGGTTATGACGGTGG---ACCTGGTTCCCGTTATGGCGCAGTGGTGAC
3320  119_HRV64    CATGTTTTATGATGGTTATGACGGTGG---ACCTGGTTCCCGTTATGGCGCAGTGGTGAC
3321  120_HRV94a   CATGTTCTATGATGGTTATGATGGTGG---ACCTGGCTCACGCTATGGCACAGTGGTGAC
3322  121_HRV94b   CATGTTCTATGATGGTTATGATGGTGG---ACCTGGCTCACGCTATGGCACAGTGGTGAC
3323  122_HRV94    CATGTTCTATGATGGTTATGATGGTGG---ACCTGGCTCACGCTATGGCACAGTGGTGAC
3324  123_HRV22    CATGTTTTATGATGGGTATGATGGAGG---TCCCGGATCACGTTATGGAGCAGTGGTAAC
3325  124_HRV22a   CATGTTTTATGATGGGTATGATGGAGG---TCCCGGATCACGTTATGGAGCAGTGGTAAC
3326  125_HRV22b   CATGTTTTATGATGGGTATGATGGAGG---TCCCGGATCACGTTATGGAGCAGTGGTAAC
3327  126_HRV82    TATGTTCTATGATGGCTATGATGGTGATGCTCCCGGATCGCGATACGGGACCATAGTGAC
3328  127_HRV82b   TATGTTCTATGATGGCTATGATGGTGATGCTCCCGGATCGCGATACGGGACCATAGTGAC
```

FIG. D5 CONT'D 01.trace                                                                                         9/20/2007 4:58 PM

```
3329  128_HRV82a    TATGTTCTATGATGGCTATGATGGTGATGCTCCCGGATCGCGATACGGGACCATAGTGAC
3330  129_HRV19     CATGTTTTATGATGGGTATGATGGAGATTCACCAGGATCCCGCTATGGAACAATAGTAAC
3331  130_HRV19a    CATGTTTTATGATGGGTATGATGGAGATTCACCAGGATCCCGCTATGGAACAATAGTAAC
3332  131_HRV19b    CATGTTTTATGATGGGTATGATGGAGATTCACCAGGATCCCGCTATGGAACAATAGTAAC
3333  132_HRV13     TATGTTTTATGATGGATATAATGGAGATTCCTCAGATGCACGCTATGGGACAACAATCAC
3334  133_HRV13a    TATGTTTTATGATGGATATAATGGAGATTCCTCAGATGCACGCTATGGGACAACAATCAC
3335  134_HRV13b    TATGTTTTATGATGGATATAATGGAGATTCCTCAGATGCACGCTATGGGACAACAATCAC
3336  135_HRV41     CATGTTTTATGATGGTTATGAAGAAGGCTCTACAAATGCACGCTATGGAACAACAGTCAC
3337  136_HRV41a    CATGTTTTATGATGGTTATGAAGAAGGCTCTACAAATGCACGCTATGGAACAACAGTCAC
3338  137_HRV41b    CATGTTTTATGATGGTTATGAAGAAGGCTCTACAAATGCACGCTATGGAACAACAGTCAC
3339  138_HRV73     TATGTTTTATGATGGATATGATGGTGACTCCACACAATCACATTATGGCACCACAGTAGT
3340  139_HRV73b    TATGTTTTATGATGGATATGATGGTGACTCCACACAATCACATTATGGCACCACAGTAGT
3341  140_HRV73a    TATGTTTTATGATGGATATGATGGTGACTCCACACAATCACATTATGGCACCACAGTAGT
3342  141_HRV61     TATGTTTTATGATGGTTATGATGGAGATTCTGAAATAACGCGCTATGGAACATCAGTGAC
3343  142_HRV61a    TATGTTTTATGATGGTTATGATGGAGATTCTGAAATAACGCGCTATGGAACATCAGTGAC
3344  143_HRV61b    TATGTTTTATGATGGTTATGATGGAGATTCTGAAATAACGCGCTATGGAACATCAGTGAC
3345  144_HRV96     CATGTTTTATGATGGATATGATGGTGACTCTGAATCAACACGCTATGGAACATCTGTTAC
3346  145_HRV96b    CATGTTTTATGATGGATATGATGGTGACTCTGAATCAACACGCTATGGAACATCTGTTAC
3347  146_HRV96a    CATGTTTTATGATGGATATGATGGTGACTCTGAATCAACACGCTATGGAACATCTGTTAC
3348  90_HRV16a|    CATGTTTTATGATGGTTATGATGGAGACACATATAAATCCAGATATGGAACTGTAGTCAC
3349  91_HRV16b|    CATGTTTTATGATGGTTATGATGGAGACACATATAAATCCAGATATGGAACTGTAGTCAC
3350  92_1AYM_A     CATGTTTTATGATGGTTATGATGGAGACACATATAAATCCAGATATGGAACTGTAGTCAC
3351  93_HRV81a|    CATGTTCTATGATGGATATGATGGTGATACTTATCACTCCAGATACGGGACTGTAGTCAC
3352  94_HRV81b|    CATGTTCTATGATGGATATGATGGTGATACTTATCACTCCAGATACGGGACTGTAGTCAC
3353  95_HRV81      CATGTTCTATGATGGATATGATGGTGATACTTATCACTCCAGATACGGGACTGTAGTCAC
3354  147_HRV2      CATGTTTTATGATGGGTATGATG------AACAAGATCAAAACTATGGTACAGCAAGCAC
3355  148_HRV2a|    CATGTTTTATGATGGGTATGATG------AACAAGATCAAAACTATGGTACAGCAAGCAC
3356  149_HRV2b|    CATGTTTTATGATGGGTATGATG------AACAAGATCAAAACTATGGTACAGCAAGCAC
3357  150_HRV49a    CATGTTTTATGATGGATATAATG------AACAGGGCCAAAATTATGGTACGGTAAGTAC
3358  151_HRV49b    CATGTTTTATGATGGATATAATG------AACAGGGCCAAAATTATGGTACGGTAAGTAC
3359  152_HRV49     CATGTTTTATGATGGATATAATG------AACAGGGCCAAAATTATGGTACGGTAAGTAC
3360  153_HRV23a    CATGTTTTATGATGGATACAATG------AGAAAGGCACGCATTATGGAACAGTTAGCAC
3361  154_HRV23b    CATGTTTTATGATGGATACAATG------AGAAAGGCACGCATTATGGAACAGTTAGCAC
3362  155_HRV23     CATGTTTTATGATGGATACAATG------AGAAAGGCACGCATTATGGAACAGTTAGCAC
3363  156_HRV30a    CATGTTCTATGATGGATACAATG------AGGGAGGCACAAATTATGGTACAGTGAGCAC
3364  157_HRV30b    CATGTTCTATGATGGATACAATG------AGGGAGGCACAAATTATGGTACAGTGAGCAC
3365  158_HRV30     CATGTTCTATGATGGATACAATG------AGGGAGGCACAAATTATGGTACAGTGAGCAC
3366  159_HRV7      TATGTTCTATGATGGATATGATGGTGATGATGCGTCATCCAAATATGGTTCCGTAGTAAC
3367  160_HRV7b|    TATGTTCTATGATGGATATGATGGTGATGATGCGTCATCCAAATATGGTTCCGTAGTAAC
3368  161_HRV7a|    TATGTTCTATGATGGATATGATGGTGATGATGCGTCATCCAAATATGGTTCCGTAGTAAC
3369  162_HRV88     TATGTTTTATGATGGATATGATGGTGATGATGCGTCATCATCTAGGTATGGCTCAGTGGTAAC
3370  163_HRV88a    TATGTTTTATGATGGATATGATGGTGATGATGCATCATCTAGGTATGGCTCAGTGGTAAC
3371  164_HRV88b    TATGTTTTATGATGGATATGATGGTGATGATGCATCATCTAGGTATGGCTCAGTGGTAAC
3372  165_HRV36a    TATGTTTTATGATGGTTATGATGGTGATAATGCCGCATCAAAATATGGATCTGTGGTTAC
3373  166_HRV36b    TATGTTTTATGATGGTTATGATGGTGATAATGCCGCATCAAAATATGGATCTGTGGTTAC
3374  167_HRV36     TATGTTTTATGATGGTTATGATGGTGATAATGCCGCATCAAAATATGGATCTGTGGTTAC
3375  168_HRV89a    CATGTTTTATGATGGTTATGATGGTGATAGTGCAGCATCAAAATACGGTTCTGTAGTCAC
3376  169_HRV89b    CATGTTTTATGATGGTTATGATGGTGATAGTGCAGCATCAAAATACGGTTCTGTAGTCAC
3377  170_HRV89     CATGTTTTATGATGGTTATGATGGTGATAGTGCAGCATCAAAATACGGTTCTGTAGTCAC
3378  171_HRV58     TATGTTTTATGATGGCTATGATGGTGATGATGCTAAATCAATATATGGTTCTGTGGTAAC
3379  172_HRV58a    TATGTTTTATGATGGCTATGATGGTGATGATGCTAAATCAATATATGGTTCTGTGGTAAC
3380  173_HRV58b    TATGTTTTATGATGGCTATGATGGTGATGATGCTAAATCAATATATGGTTCTGTGGTAAC
3381  174_HRV12a    CATGTTTTATGATGGTTATGCTGATGACAACCCAAGTGCACCTTATGGAACTGTAGTTAC
3382  175_HRV12b    CATGTTTTATGATGGTTATGCTGATGACAACCCAAGTGCACCTTATGGAACTGTAGTTAC
3383  176_HRV12     CATGTTTTATGATGGTTATGCTGATGACAACCCAAGTGCACCTTATGGAACTGTAGTTAC
3384  177_HRV78a    CATGTTTTATGATGGATACTCGGATGACAGCACATCCTCTCCATATGGCACTGTAGTTAC
3385  178_HRV78b    CATGTTTTATGATGGATACTCGGATGACAGCACATCCTCTCCATATGGCACTGTAGTTAC
3386  179_HRV78     CATGTTTTATGATGGATACTCGGATGACAGCACATCCTCTCCATATGGCACTGTAGTTAC
3387  180_HRV20     TATGTTTTATGATGGTTATGAAGATGATAAGG---GAAGTGTGTATGGGTCTGTTGTCAC
3388  181_HRV20a    TATGTTTTATGATGGTTATGAAGATGATAAGG---GAAGTGTGTATGGGTCTGTTGTCAC
3389  182_HRV20b    TATGTTTTATGATGGTTATGAAGATGATAAGG---GAAGTGTGTATGGGTCTGTTGTCAC
3390  183_HRV68     TATGTTTTATGATGGATATGAGGATGACAAAG---GAAGTGTGTATGGATCTGTTGTTAC
3391  184_HRV68a    TATGTTTTATGATGGATATGAGGATGACAAAG---GAAGTGTGTATGGATCTGTTGTTAC
3392  185_HRV68b    TATGTTTTATGATGGATATGAGGATGACAAAG---GAAGTGTGTATGGATCTGTTGTTAC
```

FIG. D5 CONT'D 01.trace                                                                9/20/2007 4:58 PM

```
3393  186_HRV28    CATGTTTTATGATGGTTATGAAGATGACAATG---GAACTACCTATGGTGCAGTGGTTAC
3394  187_HRV28a   CATGTTTTATGATGGTTATGAAGATGACAATG---GAACTACCTATGGTGCAGTGGTTAC
3395  188_HRV28b   CATGTTTTATGATGGTTATGAAGATGACAATG---GAACTACCTATGGTGCAGTGGTTAC
3396  189_HRV53a   TATGTTCTATGATGGGTATGAAGATGACAATG---GCACCACTTATGGGGCTGTTGTTAC
3397  190_HRV53b   TATGTTCTATGATGGGTATGAAGATGACAATG---GCACCACTTATGGGGCTGTTGTTAC
3398  191_HRV53    TATGTTCTATGATGGGTATGAAGATGACAATG---GCACCACTTATGGGGCTGTTGTTAC
3399  192_HRV46a   CATGTTTTATGATGGCTACGAAAGTGATAAAG---GCAAGATCTATGGAACTGCAGTCAC
3400  193_HRV46b   CATGTTTTATGATGGCTACGAAAGTGATAAAG---GCAAGATCTATGGAACTGCAGTCAC
3401  194_HRV46    CATGTTTTATGATGGCTACGAAAGTGATAAAG---GCAAGATCTATGGAACTGCAGTCAC
3402  195_HRV80a   CATGTTCTATGATGGGTATGAGAGTGATAAAG---GCAACATTTATGGAACAGCAGTTAC
3403  196_HRV80b   CATGTTCTATGATGGGTATGAGAGTGATAAAG---GCAACATTTATGGAACAGCAGTTAC
3404  197_HRV80    CATGTTCTATGATGGGTATGAGAGTGATAAAG---GCAACATTTATGGAACAGCAGTTAC
3405  198_HRV51    CATGTTTTATGATGGGTATGAAGGTGATAGTTTGACCTCACAGTACGGTTCAGTAGTCAC
3406  199_HRV51a   CATGTTTTATGATGGGTATGAAGGTGATAGTTTGACCTCACAGTACGGTTCAGTAGTCAC
3407  200_HRV51b   CATGTTTTATGATGGGTATGAAGGTGATAGTTTGACCTCACAGTACGGTTCAGTAGTCAC
3408  201_HRV65a   CATGTTCTATGATGGTTATGAGGGTGATGACCCAAATTCAAAATATGGTTCAGTGGTTAC
3409  202_HRV65b   CATGTTCTATGATGGTTATGAGGGTGATGACCCAAATTCAAAATATGGTTCAGTGGTTAC
3410  203_HRV65    CATGTTCTATGATGGTTATGAGGGTGATGACCCAAATTCAAAATATGGTTCAGTGGTTAC
3411  204_HRV71a   CATGTTCTATGATGGGTATGAAGGTGATGCCCTCAGTTCTAAATATGGCTCAGTAGTTAC
3412  205_HRV71b   CATGTTCTATGATGGGTATGAAGGTGATGCCCTCAGTTCTAAATATGGCTCAGTAGTTAC
3413  206_HRV71    CATGTTCTATGATGGGTATGAAGGTGATGCCCTCAGTTCTAAATATGGCTCAGTAGTTAC
3414  207_HRV8     CATGTTCTATGATGGTTATGATTCAGATGGTTTAGATGCTATTTATGGTATTCCTGTTAC
3415  208_HRV95    CATGTTCTATGATGGTTATGATTCAGATGGTTTAGATGCTATTTATGGTATTCCTGTTAC
3416  209_HRV45    CATGTTTTATGATGGATACGACACTGATGGCACAGATGCAGTGTATGGTGTTAGTGTGAC
3417  210_HRV45a   CATGTTTTATGATGGATACGACACTGATGGCACAGATGCAGTGTATGGTGTTAGTGTGAC
3418  211_HRV45b   CATGTTTTATGATGGATACGACACTGATGGCACAGATGCAGTGTATGGTGTTAGTGTGAC
3419  212_HRV6     ------------------------------------------------------------
3420  213_HRV6a|   ------------------------------------------------------------
3421  214_HRV6b|   ------------------------------------------------------------
3422  215_HRV37    ------------------------------------------------------------
3423  216_HRV37a   ------------------------------------------------------------
3424  217_HRV37b   ------------------------------------------------------------
3425  218_HRV3     ------------------------------------------------------------
3426  219_HRV3a|   ------------------------------------------------------------
3427  220_HRV3b|   ------------------------------------------------------------
3428  221_HRV14    ------------------------------------------------------------
3429  222_HRV14a   ------------------------------------------------------------
3430  223_HRV14b   ------------------------------------------------------------
3431  224_HRV72    ------------------------------------------------------------
3432  225_HRV72a   ------------------------------------------------------------
3433  226_HRV72b   ------------------------------------------------------------
3434  227_HRV83    ------------------------------------------------------------
3435  228_HRV83a   ------------------------------------------------------------
3436  229_HRV83b   ------------------------------------------------------------
3437  230_HRV92    ------------------------------------------------------------
3438  231_HRV92a   ------------------------------------------------------------
3439  232_HRV92b   ------------------------------------------------------------
3440  233_HRV79    ------------------------------------------------------------
3441  234_HRV79a   ------------------------------------------------------------
3442  235_HRV79b   ------------------------------------------------------------
3443  236_HRV35    ------------------------------------------------------------
3444  237_HRV35a   ------------------------------------------------------------
3445  238_HRV35b   ------------------------------------------------------------
3446  239_1HRV86   ------------------------------------------------------------
3447  240_1HRV86   ------------------------------------------------------------
3448  241_1HRV86   ------------------------------------------------------------
3449  242_HRV70    ------------------------------------------------------------
3450  243_HRV70a   ------------------------------------------------------------
3451  244_HRV70b   ------------------------------------------------------------
3452  245_HRV91    ------------------------------------------------------------
3453  246_HRV91a   ------------------------------------------------------------
3454  247_HRV91b   ------------------------------------------------------------
3455  248_HRV17    ------------------------------------------------------------
3456  249_HRV17a   ------------------------------------------------------------
```

FIG. D5 CONT'D 01.trace                                                                 9/20/2007 4:58 PM

| | | |
|---|---|---|
| 3457 | 250_HRV17b | ------------------------------------------------------------ |
| 3458 | 251_HRV69 | ------------------------------------------------------------ |
| 3459 | 252_HRV69a | ------------------------------------------------------------ |
| 3460 | 253_HRV69b | ------------------------------------------------------------ |
| 3461 | 254_HRV48 | ------------------------------------------------------------ |
| 3462 | 255_HRV48a | ------------------------------------------------------------ |
| 3463 | 256_HRV48b | ------------------------------------------------------------ |
| 3464 | 257_HRV52 | ------------------------------------------------------------ |
| 3465 | 258_HRV52a | ------------------------------------------------------------ |
| 3466 | 259_HRV52b | ------------------------------------------------------------ |
| 3467 | 260_HRV4 | ------------------------------------------------------------ |
| 3468 | 261_HRV4a\| | ------------------------------------------------------------ |
| 3469 | 262_HRV4b\| | ------------------------------------------------------------ |
| 3470 | 263_HRV99 | ------------------------------------------------------------ |
| 3471 | 264_HRV99a | ------------------------------------------------------------ |
| 3472 | 265_HRV99b | ------------------------------------------------------------ |
| 3473 | 266_HRV5 | ------------------------------------------------------------ |
| 3474 | 267_HRV5a\| | ------------------------------------------------------------ |
| 3475 | 268_HRV5b\| | ------------------------------------------------------------ |
| 3476 | 269_HRV42 | ------------------------------------------------------------ |
| 3477 | 270_HRV42a | ------------------------------------------------------------ |
| 3478 | 271_HRV42b | ------------------------------------------------------------ |
| 3479 | 272_HRV26 | ------------------------------------------------------------ |
| 3480 | 273_HRV26a | ------------------------------------------------------------ |
| 3481 | 274_HRV26b | ------------------------------------------------------------ |
| 3482 | 275_HRV27 | ------------------------------------------------------------ |
| 3483 | 276_HRV27a | ------------------------------------------------------------ |
| 3484 | 277_HRV27b | ------------------------------------------------------------ |
| 3485 | 278_HRV93 | ------------------------------------------------------------ |
| 3486 | 279_HRV93a | ------------------------------------------------------------ |
| 3487 | 280_HRV93b | ------------------------------------------------------------ |
| 3488 | 281_HRV97 | ------------------------------------------------------------ |
| 3489 | 282_HRV97a | ------------------------------------------------------------ |
| 3490 | 283_HRV97b | ------------------------------------------------------------ |
| 3491 | 284_HRV84 | ------------------------------------------------------------ |
| 3492 | 285_HRV84a | ------------------------------------------------------------ |
| 3493 | 286_HRV84b | ------------------------------------------------------------ |
| 3494 | 287_HRV87 | ------------------------------------------------------------ |
| 3495 | 288_HRV87a | ------------------------------------------------------------ |
| 3496 | 289_HRV87b | ------------------------------------------------------------ |
| 3497 | GROUP_1 | ------------------------------------------------------------ |
| 3498 | | |
| 3499 | 1_HRV1A1\|d | TAATGATATGGGTACTATATGCTCAAGAATAGTTACAGAAAAACAGAAACATTCTGTTGT |
| 3500 | 2_HRV1A2\|d | TAATGATATGGGTACTATATGCTCAAGAATAGTTACAGAAAAACAGAAACATTCTGTTGT |
| 3501 | 3_HRV1A\|cD | TAATGATATGGGTACTATATGCTCAAGAATAGTTACAGAAAAACAGAAACATTCTGTTGT |
| 3502 | 4_HRV1B1\|d | CAATGATATGGGAACCATATGTTCAAGAATAGTTACAGAGAAGCAGGAACACCCTGTCGT |
| 3503 | 5_HRV1B2\|d | CAATGATATGGGAACCATATGTTCAAGAATAGTTACAGAGAAGCAGGAACACCCTGTCGT |
| 3504 | 6_HRV1B | CAATGATATGGGAACCATATGTTCAAGAATAGTTACAGAGAAGCAGGAACACCCTGTCGT |
| 3505 | 7_HRV40a\|d | TAACCATATGGGAACGCTATGCTCAAGAATAGTCACCAACAAGCAGCAGCATGAAGTTGA |
| 3506 | 8_HRV40b\|d | TAACCATATGGGAACGCTATGCTCAAGAATAGTCACCAACAAGCAGCAGCATGAAGTTGA |
| 3507 | 9_HRV40 | TAACCATATGGGAACGCTATGCTCAAGAATAGTCACCAACAAGCAGCAGCATGAAGTTGA |
| 3508 | 10_HRV85 | CAACCACATGGGAACACTGTGCTCGAGGATAGTTACCAACAAACAGCAGCATGAGGTTGA |
| 3509 | 11_HRV85a\| | CAACCACATGGGAACACTGTGCTCGAGGATAGTTACCAACAAACAGCAGCATGAGGTTGA |
| 3510 | 12_HRV85b\| | CAACCACATGGGAACACTGTGCTCGAGGATAGTTACCAACAAACAGCAGCATGAGGTTGA |
| 3511 | 13_HRV56a\| | AAACCACATGGGGACACTCTGTTCAAGAATTGTGACAAATAAACAACTTCATCCTGTTGA |
| 3512 | 14_HRV56b\| | AAACCACATGGGGACACTCTGTTCAAGAATTGTGACAAATAAACAACTTCATCCTGTTGA |
| 3513 | 15_HRV56 | AAACCACATGGGGACACTCTGTTCAAGAATTGTGACAAATAAACAACTTCATCCTGTTGA |
| 3514 | 16_HRV54 | CAATCATATGGGTACTTTGTGTTCAAGAATGGTTACTGATAAACAAAAACACCCAGTTGA |
| 3515 | 17_HRV98 | TAATCACATGGGCACTTTGTGTTCAAGAGTAGTTACTGGCAAACAAGAACACCCAGTTGA |
| 3516 | 18_HRV59a\| | CAACCACATGGGCACTTTATGTTCTAGAATAGTTACAAACAGTCAGGAGCATCCAGTGGA |
| 3517 | 19_HRV59b\| | CAACCACATGGGCACTTTATGTTCTAGAATAGTTACAAACAGTCAGGAGCATCCAGTGGA |
| 3518 | 20_HRV59 | CAACCACATGGGCACTTTATGTTCTAGAATAGTTACAAACAGTCAGGAGCATCCAGTTGA |
| 3519 | 21_HRV63 | TAACCATATGGGGACTTTATGTTCTAGAATTGTAACAAACAGCCAAGAACATCCAGTTGA |
| 3520 | 22_HRV63b\| | TAACCACATGGGGGACTTTATGTTCTAGAATTGTAACAAACAGCCAAGAACATCCAGTTGA |

FIG. D5 CONT'D 01.trace                                                                                                    9/20/2007 4:58 PM

```
3521  23_HRV63a|   TAACCACATGGGGACTTTATGTTCTAGAATTGTAACAAACAGCCAAGAACATCCAGTTGA
3522  24_HRV39     TAATGATATGGGTACACTTTGCACTAGAATTGTAACAAACCAACAGGAACACCTAGTGGA
3523  25_HRV39a|   TAATGATATGGGTACACTTTGCACTAGAATTGTAACAAACCAACAGGAACACCTAGTGGA
3524  26_HRV39b|   TAATGATATGGGTACACTTTGCACTAGAATTGTAACAAACCAACAGAAACACCTAGTGGA
3525  27_HRV10a|   AAATCACATGGGCACTTTGTGCATGCGAATAGTCACAAACCAGCAAGCACATGAGGTGGA
3526  28_HRV10b|   AAATCACATGGGCACTTTGTGCATGCGAATAGTCACAAACCAGCAAGCACATGAGGTGGA
3527  29_HRV10     AAATCACATGGGCACTTTGTGCATGCGAATAGTCACAAACCAGCAAGCACATGAGGTGGA
3528  30_HRV100a   TAACCACATGGGTACACTTTGTATGAGGATAGTTACAAATCAGCAAGCACATGAGGTGGA
3529  31_HRV100b   TAACCACATGGGTACACTTTGTATGAGGATAGTTACAAATCAGCAAGCACATGAGGTGGA
3530  32_HRV100    TAACCACATGGGTACACTTTGTATGAGGATAGTTACAAATCAGCAAGCACATGAGGTGGA
3531  33_HRV66     TAATCATATGGGTACATTATGTATTAGGATTGTTACAAATGAACAGCACCATAATGTTGA
3532  34_HRV66b|   TAATCATATGGGTACATTATGTATTAGGATTGTTACAAATGAACAGCACCATAATGTTGA
3533  35_HRV66a|   TAATCATATGGGTACATTATGTATTAGGATTGTTACAAATGAACAGCACCATAATGTTGA
3534  36_HRV77a|   TAATCACATGGGCACACTGTGCATTAGAATAGTCACTAATCAGCAAAATCATGAGGTTGA
3535  37_HRV77b|   TAATCACATGGGCACACTGTGCATTAGAATAGTCACTAATCAGCAAAATCATGAGGTTGA
3536  38_HRV77     TAATCACATGGGCACACTGTGCATTAGAATAGTCACTAATCAGCAAAATCATGAGGTTGA
3537  39_HRV62a    TAATCGTATGGGGGCACTGTGTATGAGGATTGTCACAAACAAACAAGTTCATGATGTTGA
3538  40_HRV62b    TAATCGTATGGGGGCACTGTGTATGAGGATTGTCACAAACAAACAAGTTCATGATGTTGA
3539  41_HRV25     TAACCGTATGGGAGCACTGTGCATGAGAATTGTCACAAATAAACAAGTCCATGATGTTGA
3540  42_HRV29a    TAACCGGATGGGGACGCTTTGTGTCAGAATTGTTACAGGCAAACAAGCTCATGATGTTCA
3541  43_HRV29b    TAACCGGATGGGGACGCTTTGTGTCAGAATTGTTACAGGCAAACAAGCTCATGATGTTCA
3542  44_HRV44a    TAACCGGATGGGGACGCTTTGCGTCAGGATCGTTACGGGCAAACAGGCTCATGATGTCCA
3543  45_HRV44b    TAACCGGATGGGGACGCTTTGCGTCAGGATCGTTACGGGCAAACAGGCTCATGATGTCCA
3544  46_HRV31     TAATCGCATGGGTGCACTATGCATGAGAGTTGTCACTAACAAACAAGCTCATAAAGTTGA
3545  47_HRV31a|   TAATCGCATGGGTGCACTATGCATGAGAGTTGTCACTAACAAACAAGCTCATAAAGTTGA
3546  48_HRV31b|   TAATCGCATGGGTGCACTATGCATGAGAGTTGTCACTAACAAACAAGCTCATAAAGTTGA
3547  49_HRV47     CAATCGCATGGGTGCATTGTGTATGAGAGTTGTAACAAACAAGCAACTCCATAAAGTTGA
3548  50_HRV47a|   CAATCGCATGGGTGCATTGTGTATGAGAGTTGTAACAAACAAGCAACTCCATAAAGTTGA
3549  51_HRV47b|   CAATCGCATGGGTGCATTGTGTATGAGAGTTGTAACAAACAAGCAACTCCATAAAGTTGA
3550  52_HRV11     CAATGATATGGGCACTCTGTGTTATAGAATAGTAACTGATGACCATAGACACAAAATTGA
3551  53_HRV11b|   CAATGATATGGGCACTCTGTGTTATAGAATAGTAACTGATGACCATAGACACAAAATTGA
3552  54_HRV11a|   CAATGATATGGGCACTCTGTGTTATAGAATAGTAACTGATGACCATAGACACAAAATTGA
3553  55_HRV76     CAATGACATGGGCACCCTATGTTCCAGGATAGTAACTGATGATCATAAGCACAAGATTGA
3554  56_HRV76b|   CAATGACATGGGCACCCTATGTTCCAGGATAGTAACTGATGATCATAAGCACAAGATTGA
3555  57_HRV76a|   CAATGACATGGGCACCCTATGTTCCAGGATAGTAACTGATGATCATAAGCACAAGATTGA
3556  58_HRV33     CAATGACATGGGCACTTTATGCTCTAGAATAGTTACAGATAATCATAAGCATCCAATAGA
3557  59_HRV33b|   CAATGACATGGGCACTTTATGCTCTAGAATAGTTACAGATAATCATAAGCATCCAATAGA
3558  60_HRV33a|   CAATGACATGGGCACTTTATGCTCTAGAATAGTTACAGATAATCATAAGCATCCAATAGA
3559  61_HRV24a|   AAACGACATGGGAACTCTATGCTATAGAATAGTCACTGACAAGCATAATCACCAAATAGA
3560  62_HRV24b|   AAACGACATGGGAACTCTATGCTATAGAATAGTCACTGACAAGCATAATCACCAAATAGA
3561  63_HRV24     AAACGACATGGGAACTCTATGCTATAGAATAGTCACTGACAAGCATAATCACCAAATAGA
3562  64_HRV90     TAATGATATGGGAACCTTATGTTATAGAATAGTTACAGATGAACATGCCCACAAAATAGA
3563  65_HRV90a|   TAATGATATGGGAACCTTATGTTATAGAATAGTTACAGATGAACATGCCCACAAAATAGA
3564  66_HRV90b|   TAATGATATGGGAACCTTATGTTATAGAATAGTTACAGATGAACATGCCCACAAAATAGA
3565  67_HRV34     TAATGACATGGGTACTTTATGCTCCAGAATTGTAACTGATGAACACCAAAACAGAGTAGA
3566  68_HRV34b|   TAATGACATGGGTACTTTATGCTCCAGAATTGTAACTGATGAACACCAAAACAGAGTAGA
3567  69_HRV34a|   TAATGACATGGGTACTTTATGCTCCAGAATTGTAACTGATGAACACCAAAACAGAGTAGA
3568  70_HRV50a    CAATGACATGGGCACTTTGTGTTCTAGGATTGTCACTGATGAGCACCAAAATAAAGTGGA
3569  71_HRV50b    CAATGACATGGGCACTTTGTGTTCTAGGATTGTCACTGATGAGCACCAAAATAAAGTGGA
3570  72_HRV50     CAATGACATGGGCACTTTGTGTTCTAGGATTGTCACTGATGAGCACCAAAATAAAGTGGA
3571  73_HRV18a|   AAATGACATGGGTACCTTGTGCTCTAGAATAGTCACAGATAAACATAAGAATGAGGTGGA
3572  74_HRV18b|   AAATGACATGGGTACCTTGTGCTCTAGAATAGTCACAGATAAACATAAGAATGAGGTGGA
3573  75_HRV18     AAATGACATGGGTACCTTGTGCTCTAGAATAGTCACAGATAAACATAAGAATGAGGTGGA
3574  76_HRV55     TAATGACATGGGTACTTTATGTTCTAGAATAATAACTGATAACCATAAGCACCCAATTGA
3575  77_HRV55b|   TAATGACATGGGTACTTTATGTTTCTAGAATAATAACTGATAACCATAAGCACCCAATTGA
3576  78_HRV55a|   TAATGACATGGGTACTTTATGTTCTAGAATAATAACTGATAACCATAAGCACCCAATTGA
3577  79_HRV57     TAATGACATGGGCACTTTATGTTCTAGAATTGTTACTGACCAGCACACACATCCCATAAA
3578  80_HRV57a|   TAATGACATGGGCACTTTATGTTCTAGAATTGTTACTGACCAGCACACACATCCCATAAA
3579  81_HRV57b|   TAATGACATGGGCACTTTATGTTCTAGAATTGTTACTGACCAGCACACACATCCCATAAA
3580  82_HRV21     TAATGATATGGGATCTCTATGCTACAGAATAGTAACTGGCCAGCACAAGCATAAGATAGA
3581  83_HRVHan    TAATGATATGGGATCTCTATGCTATAGAATAGTAACTGATCAGCATAAGCACAAGATAGA
3582  84_HRV43     CAACCACATGGGAACATTATGTTCTAGGATAGTTACAGAAGAACACCAAAATCAAATCGA
3583  85_HRV43b|   CAACCACATGGGAACATTATGTTCTAGGATAGTTACAGAAGAACACCAAAATCAAATCGA
3584  86_HRV43a|   CAACCACATGGGAACATTATGTTCTAGGATAGTTACAGAAGAACACCAAAATCAAATCGA
```

FIG. D5 CONT'D 01.trace                                                                                                9/20/2007 4:58 PM

```
3585  87_HRV75     TAATCACATGGGGACACTGTGTTCTAGAATAGTTACAGAAGAACATCGAAATAAAGTTGA
3586  88_HRV75b|   TAATCACATGGGGACACTGTGTTCTAGAATAGTTACAGAAGAACATCGAAATAAAGTTGA
3587  89_HRV75a|   TAATCACATGGGGACACTGTGTTCTAGAATAGTTACAGAAGAACATCGAAATAAAGTTGA
3588  96_HRV9a|d   AAATGATATGGGATCTTTATGTTCCCGTGTAGTTACTGAAGAGCATGGACCCCGTGTCAA
3589  97_HRV9b|d   AAATGATATGGGATCTTTATGTTCCCGTGTAGTTACTGAAGAGCATGGACCCCGTGTCAA
3590  98_HRV9      AAATGATATGGGATCTTTATGTTCCCGTGTAGTTACTGAAGAGCATGGACCCCGTGTCAA
3591  99_HRV32     AAATGATATGGGTTCCCTGTGTTCTCGTATAGTCACCGAAGAGCACGGATCCCGTGTTGA
3592  100_HRV32a   AAATGATATGGGTTCCCTGTGTTCTCGTATAGTCACCGAAGAGCACGGATCCCGTGTTGA
3593  101_HRV32b   AAATGATATGGGTTCCCTGTGTTCTCGTATAGTCACCGAAGAGCACGGATCCCGTGTTGA
3594  102_HRV67    TAATGATATGGGTTCCTTGTGTTCGCGTATAGTTACTGAAGAACATGGTTCTCGCGTAAA
3595  103_HRV67a   TAATGATATGGGTTCCTTGTGTTCGCGTATAGTTACTGAAGAACATGGTTCTCGCGTAAA
3596  104_HRV67b   TAATGATATGGGTTCCTTGTGTTCGCGTATAGTTACTGAAGAACATGGTTCTCGCGTAAA
3597  105_HRV15    TAATGACATGGGGACACTGTGTTCTAGAATAGTAACTGAAGAGCATGGGACACGTGTAGA
3598  106_HRV15a   TAATGACATGGGGACACTGTGTTCTAGAATAGTAACTGAAGAGCATGGGACACGTGTAGA
3599  107_HRV15b   TAATGACATGGGGACACTGTGTTCTAGAATAGTAACTGAAGAGCATGGGACACGTGTAGA
3600  108_HRV74a   AAATGACATGGGAACTCTATGTTCTAGAATTGTGACTGAAGAACACGATGCACGTGTGGA
3601  109_HRV74b   AAATGACATGGGAACTCTATGTTCTAGAATTGTGACTGAAGAACACGATGCACGTGTGGA
3602  110_HRV74    AAATGACATGGGAACTCTATGTTCTAGAATTGTGACTGAAGAACACGATGCACGTGTGGA
3603  111_HRV38a   CAATGATATGGGGACACTTTGTTCAAGAATAGTCACTGAAAATCATGGGACCCAAGTGAA
3604  112_HRV38b   CAATGATATGGGGACACTTTGTTCAAGAATAGTCACTGAAAATCATGGGACCCAAGTGAA
3605  113_HRV38    CAATGATATGGGGACACTTTGTTCAAGAATAGTCACTGAAAATCATGGGACCCAAGTGAA
3606  114_HRV60    CAATGACATGGGAACGTTGTGCTCCAGAATAGTTACTGAACACCATGGTACACAGGTTCA
3607  115_HRV60a   CAATGACATGGGAACGTTGTGCTCCAGAATAGTTACTGAACACCATGGTACACAGGTTCA
3608  116_HRV60b   CAATGACATGGGAACGTTGTGCTCCAGAATAGTTACTGAACACCATGGTACACAGGTTCA
3609  117_HRV64    AAATGATATGGGCACTTTGTGTTCTAGAATTGTGACTGAGGAACACAACACAGGTCAA
3610  118_HRV64b   AAATGATATGGGCACTTTGTGTTCTAGAATTGTGACTGAGGAACACACAACACAGGTCAA
3611  119_HRV64    AAATGATATGGGCACTTTGTGTTCTAGAATTGTGACTGAGGAACACACAACACAGGTCAA
3612  120_HRV94a   AAATGACATGGGAACATTATGCTCCAGGATTGTGACTGAGGAGCACAAGACACAGGTTAA
3613  121_HRV94b   AAATGACATGGGAACATTATGCTCCAGGATTGTGACTGAGGAGCACAAGACACAGGTTAA
3614  122_HRV94    AAATGACATGGGAACATTATGCTCCAGGATTGTGACTGAGGAGCACAAGACACAGGTTAA
3615  123_HRV22    AAATGATATGGGCACACTGTGCTCTAGGATTGTGACTGAAGAACACCAGACACAAGTCAA
3616  124_HRV22a   AAATGATATGGGCACACTGTGCTCTAGGATTGTGACTGAAGAACACCAGACACAAGTCAA
3617  125_HRV22b   AAATGATATGGGCACACTGTGCTCTAGGATTGTGACTGAAGAACACCAGACACAAGTCAA
3618  126_HRV82    AAATGACATGGGTACACTGTGTTCTAGAATTGTAACTGAAGAACACCAGACTCAAGTCAG
3619  127_HRV82b   AAATGACATGGGTACACTGTGTTCTAGAATTGTAACTGAAGAACACCAGACTCAAGTCAG
3620  128_HRV82a   AAATGACATGGGTACACTGTGTTCTAGAATTGTAACTGAAGAACACCAGACTCAAGTCAG
3621  129_HRV19    TAATGATATGGGAACCTTATGCTCCAGAATAGTAACTGATGAACACCAAACACAGGTTGC
3622  130_HRV19a   TAATGATATGGGAACCTTATGCTCCAGAATAGTAACTGATGAACACCAAACACAGGTTGC
3623  131_HRV19b   TAATGATATGGGAACCTTATGCTCCAGAATAGTAACTGATGAACACCAAACACAGGTTGC
3624  132_HRV13    TAATGATATGGGCACACTTTGCTTCAGAATAGTAACTGAAGAACATACTAACAAGGTCAA
3625  133_HRV13a   TAATGATATGGGCACACTTTGCTTCAGAATAGTAACTGAAGAACATACTAACAAGGTCAA
3626  134_HRV13b   TAATGATATGGGCACACTTTGCTTCAGAATAGTAACTGAAGAACATACTAACAAGGTCAA
3627  135_HRV41    AAATGACATGGGTACATTATGCTTTAGAATAGTTACTGAAGAACACACCAACAAAGTTAA
3628  136_HRV41a   AAATGACATGGGTACATTATGCTTTAGAATAGTTACTGAAGAACACACCAACAAAGTTAA
3629  137_HRV41b   AAATGACATGGGTACATTATGCTTTAGAATAGTTACTGAAGAACACACCAACAAAGTTAA
3630  138_HRV73    TAATGACATGGGCACATTATGCTTTAGGATAGTGACTGAAGAACACACTAGCAGGGTAAA
3631  139_HRV73b   TAATGACATGGGCACATTATGCTTTAGGATAGTGACTGAAGAACACACTAGCAGGGTAAA
3632  140_HRV73a   TAATGACATGGGCACATTATGCTTTAGGATAGTGACTGAAGAACACACTAGCAGGGTAAA
3633  141_HRV61    AAATGATATGGGTGCATTGTGCTTTAGAATAGTAACTGAACAGCATACAAATCAAGTTAA
3634  142_HRV61a   AAATGATATGGGTGCATTGTGCTTTAGAATAGTAACTGAACAGCATACAAATCAAGTTAA
3635  143_HRV61b   AAATGATATGGGTGCATTGTGCTTTAGAATAGTAACTGAACAGCATACAAATCAAGTTAA
3636  144_HRV96    CAATGACATGGGCACTTTATGTTTTAGAATAGTGACAGAGGAACACACCAACAAGGTCAA
3637  145_HRV96b   CAATGACATGGGCACTTTATGTTTTAGAATAGTGACAGAGGAACACACCAACAAGGTCAA
3638  146_HRV96a   CAATGACATGGGCACTTTATGTTTTAGAATAGTGACAGAGGAACACACCAACAAGGTCAA
3639  90_HRV16a|   CAATGACATGGGAACTTTGTGTTCGCGTATTGTGACCAGTGAGCAATTACACAAAGTCAA
3640  91_HRV16b|   CAATGACATGGGAACTTTGTGTTCGCGTATTGTGACCAGTGAGCAATTACACAAAGTCAA
3641  92_1AYM_A    CAATGACATGGGAACTTTGTGTTCGCGTATTGTGACCAGTGAGCAATTACACAAAGTCAA
3642  93_HRV81a|   TAATGATATGGGAACATTATGCTCACGGATAGTGACAAGTGAGCAAGTGCACAAGGTGAA
3643  94_HRV81b|   TAATGATATGGGAACATTATGCTCACGGATAGTGACAAGTGAGCAAGTGCACAAGGTGAA
3644  95_HRV81     TAATGATATGGGAACATTATGCTCACGGATAGTGACAAGTGAGCAAGTGCACAAGGTGAA
3645  147_HRV2     AAATAACATGGGGTCACTATGCTCTAGGATAGTAACAGAGAAACACATTCATAAGGTACA
3646  148_HRV2a|   AAATAACATGGGGTCACTATGCTCTAGGATAGTAACAGAGAAACACATTCATAAGGTACA
3647  149_HRV2b|   AAATAACATGGGGTCACTATGCTCTAGGATAGTAACAGAGAAACACATTCATAAGGTACA
3648  150_HRV49a   AAACAACATGGGATCATTATGCTCTAGGATAGTAACAGAGAAACACATTCACAGTATGCA
```

FIG. D5 CONT'D 01.trace                                                                                          9/20/2007 4:58 PM

```
3649  151_HRV49b    AAACAACATGGGATCATTATGCTCTAGGATAGTAACAGAGAAACACATTCACAGTATGCA
3650  152_HRV49     AAACAACATGGGATCATTATGCTCTAGGATAGTAACAGAGAAACACATTCACAGTATGCA
3651  153_HRV23a    AAACAACATGGGCACATTGTGCTCCAGAGTGGTAACAGAGAAACACATTCATGATATGCG
3652  154_HRV23b    AAACAACATGGGCACATTGTGCTCCAGAGTGGTAACAGAGAAACACATTCATGATATGCG
3653  155_HRV23     AAACAACATGGGCACATTGTGCTCCAGAGTGGTAACAGAGAAACACATTCATGATATGCG
3654  156_HRV30a    AAACAACATGGGCACACTGTGTTCCAGAGTGGTAACAGAAAAACACATTCATGATGTGCG
3655  157_HRV30b    AAACAACATGGGCACACTGTGTTCCAGAGTGGTAACAGAAAAACACATTCATGATGTGCG
3656  158_HRV30     AAACAACATGGGCACACTGTGTTCCAGAGTGGTAACAGAAAAACACATTCATGATGTGCG
3657  159_HRV7      CAATGACATGGGAACCATATGTGTTAGACTAGTTACATCTACACAAAAACACAATTTAAA
3658  160_HRV7b|    CAATGACATGGGAACCATATGTGTTAGACTAGTTACATCTACACAAAAACACAATTTAAA
3659  161_HRV7a|    CAATGACATGGGAACCATATGTGTTAGACTAGTTACATCTACACAAAAACACAATTTAAA
3660  162_HRV88     TAATGATATGGGAACTATATGTATTAGATTGGTCACCTCCACCCAAAAGCATAAACTGAA
3661  163_HRV88a    TAATGATATGGGAACTATATGTATTAGATTGGTCACCTCCACCCAAAAGCATAAACTGAA
3662  164_HRV88b    TAATGATATGGGAACTATATGTATTAGATTGGTCACCTCCACCCAAAAGCATAAACTGAA
3663  165_HRV36a    TAACGACATGGGAACCATATGTGTTAGAATAGTTACATCCAACCAAAAACATGATTTAAA
3664  166_HRV36b    TAACGACATGGGAACCATATGTGTTAGAATAGTTACATCCAACCAAAAACATGATTTAAA
3665  167_HRV36     TAACGACATGGGAACCATATGTGTTAGAATAGTTACATCCAACCAAAAACATGATTTAAA
3666  168_HRV89a    TAATGATATGGGAACCATATGTGTTAGAATAGTGACATCCAACCAAAAACATGATTTAAA
3667  169_HRV89b    TAATGATATGGGAACCATATGTGTTAGAATAGTGACATCCAACCAAAAACATGATTTAAA
3668  170_HRV89     TAATGATATGGGAACCATATGTGTTAGAATAGTGACATCCAACCAAAAACATGATTTAAA
3669  171_HRV58     AAATGACATGGGAACTATATGTGTTAGAATAGTCACATCCAAACAAAGACACAATTTAAA
3670  172_HRV58a    AAATGACATGGGAACTATATGTGTTAGAATAGTCACATCCAAACAAAGACACAATTTAAA
3671  173_HRV58b    AAATGACATGGGAACTATATGTGTTAGAATAGTCACATCCAAACAAAGACACAATTTAAA
3672  174_HRV12a    CAATGACATGGGTTCACTGTGTGTCAGAATAGTTACAGACCAGCAAAAACATAAAGTTAA
3673  175_HRV12b    CAATGACATGGGTTCACTGTGTGTCAGAATAGTTACAGACCAGCAAAAACATAAAGTTAA
3674  176_HRV12     CAATGACATGGGTTCACTGTGTGTCAGAATAGTTACAGACCAGCAAAAACATAAAGTTAA
3675  177_HRV78a    CAATGACATGGGTACACTGTGTATGAGGATGGTTACAGATCAACAACAACATAAGGTCAC
3676  178_HRV78b    CAATGACATGGGTACACTGTGTATGAGGATGGTTACAGATCAACAACAACATAAGGTCAC
3677  179_HRV78     CAATGACATGGGTACACTGTGTATGAGGATGGTTACAGATCAACAACAACATAAGGTCAC
3678  180_HRV20     AAACGATATGGGCACATTGTGTGTTCGTATTGTGACTGAGCAGCAGACACATAAGGTTAA
3679  181_HRV20a    AAACGATATGGGCACATTGTGTGTTCGTATTGTGACTGAGCAGCAGACACATAAGGTTAA
3680  182_HRV20b    AAACGATATGGGCACATTGTGTGTTCGTATTGTGACTGAGCAGCAGACACATAAGGTTAA
3681  183_HRV68     AAATGATATGGGCACATTATGTGTCCGTATTGTGACTGAGCAGCAGACACATAGGGTCAA
3682  184_HRV68a    AAATGATATGGGCACATTATGTGTCCGTATTGTGACTGAGCAGCAGACACATAGGGTCAA
3683  185_HRV68b    AAATGATATGGGCACATTATGTGTCCGTATTGTGACTGAGCAGCAGACACATAGGGTCAA
3684  186_HRV28     AAATCATATGGGAACACTCTGTGCTCGCATAGTAACTGAACAACAGAAGCATGAAGTCAA
3685  187_HRV28a    AAATCATATGGGAACACTCTGTGCTCGCATAGTAACTGAACAACAGAAGCATGAAGTCAA
3686  188_HRV28b    AAATCATATGGGAACACTCTGTGCTCGCATAGTAACTGAACAACAGAAGCATGAAGTCAA
3687  189_HRV53a    TAATGATATGGGAACACTTTGTGTGCGCATAGTGACTGAGCAACAGAAAAATGAGGTCAA
3688  190_HRV53b    TAATGATATGGGAACACTTTGTGTGCGCATAGTGACTGAGCAACAGAAAAATGAGGTCAA
3689  191_HRV53     TAATGATATGGGAACACTTTGTGTGCGCATAGTGACTGAGCAACAGAAAAATGAGGTCAA
3690  192_HRV46a    CAATGATATGGGAACTATATGTGTCAGAATTGTTACCGAACAACAAAAACATAAGGTTCT
3691  193_HRV46b    CAATGATATGGGAACTATATGTGTCAGAATTGTTACCGAACAACAAAAACATAAGGTTCT
3692  194_HRV46     CAATGATATGGGAACTATATGTGTCAGAATTGTTACCGAACAACAAAAACATAAGGTTCT
3693  195_HRV80a    CAATGATATGGGAACCCTGTGTGCTAGAATTGTTACAGAACAACAGAAACATAAAGTCCT
3694  196_HRV80b    CAATGATATGGGAACCCTGTGTGCTAGAATTGTTACAGAACAACAGAAACATAAAGTCCT
3695  197_HRV80     CAATGATATGGGAACCCTGTGTGCTAGAATTGTTACAGAACAACAGAAACATAAAGTCCT
3696  198_HRV51     AAATGCTATGGGGACACTATGTGTTCGTGTGGTCACAGAGCAACAAAAACATGAGGTTAA
3697  199_HRV51a    AAATGCTATGGGGACACTATGTGTTCGTGTGGTCACAGAGCAACAAAAACATGAGGTTAA
3698  200_HRV51b    AAATGCTATGGGGACACTATGTGTTCGTGTGGTCACAGAGCAACAAAAACATGAGGTTAA
3699  201_HRV65a    TAATGCTATGGGCACACTATATGTGCGTGTGGTTACAGAAAGGCAAAAACATGAAGTCAA
3700  202_HRV65b    TAATGCTATGGGCACACTATATGTGCGTGTGGTTACAGAAAGGCAAAAACATGAAGTCAA
3701  203_HRV65     TAATGCTATGGGCACACTATATGTGCGTGTGGTTACAGAAAGGCAAAAACATGAAGTCAA
3702  204_HRV71a    TAATGCCATGGGCACCTTATGTGTTCGTGTGGTTACAGACAGCAAAGCAACACAGTCAA
3703  205_HRV71b    TAATGCCATGGGCACCTTATGTGTTCGTGTGGTTACAGAACAGCAAAGCAACACAGTCAA
3704  206_HRV71     TAATGCCATGGGCACCTTATGTGTTCGTGTGGTTACAGAACAGCAAAGCAACACAGTCAA
3705  207_HRV8      AAATCACATGGGCACAATATGTGTGAGAATGGTGACAGATAAACAGAAAATTAAAACTAA
3706  208_HRV95     AAATCACATGGGCACAATATGTGTGAGAATGGTGACAGATAAACAGAAAATTAAAACTAA
3707  209_HRV45     TAACCATATGGGGACTATATGTGTTAGAATTGTTACAGACCAACAACAACATAGAGTTAA
3708  210_HRV45a    TAACCATATGGGGACTATATGTGTTAGAATTGTTACAGACCAACAACAACATAGAGTTAA
3709  211_HRV45b    TAACCATATGGGGACTATATGTGTTAGAATTGTTACAGACCAACAACAACATAGAGTTAA
3710  212_HRV6      ------------------------------------------------------------
3711  213_HRV6a|    ------------------------------------------------------------
3712  214_HRV6b|    ------------------------------------------------------------
```

FIG. D5 CONT'D

01.trace                                                                9/20/2007 4:58 PM

```
3713  215_HRV37    ------------------------------------------------------------
3714  216_HRV37a   ------------------------------------------------------------
3715  217_HRV37b   ------------------------------------------------------------
3716  218_HRV3     ------------------------------------------------------------
3717  219_HRV3a|   ------------------------------------------------------------
3718  220_HRV3b|   ------------------------------------------------------------
3719  221_HRV14    ------------------------------------------------------------
3720  222_HRV14a   ------------------------------------------------------------
3721  223_HRV14b   ------------------------------------------------------------
3722  224_HRV72    ------------------------------------------------------------
3723  225_HRV72a   ------------------------------------------------------------
3724  226_HRV72b   ------------------------------------------------------------
3725  227_HRV83    ------------------------------------------------------------
3726  228_HRV83a   ------------------------------------------------------------
3727  229_HRV83b   ------------------------------------------------------------
3728  230_HRV92    ------------------------------------------------------------
3729  231_HRV92a   ------------------------------------------------------------
3730  232_HRV92b   ------------------------------------------------------------
3731  233_HRV79    ------------------------------------------------------------
3732  234_HRV79a   ------------------------------------------------------------
3733  235_HRV79b   ------------------------------------------------------------
3734  236_HRV35    ------------------------------------------------------------
3735  237_HRV35a   ------------------------------------------------------------
3736  238_HRV35b   ------------------------------------------------------------
3737  239_1HRV86   ------------------------------------------------------------
3738  240_1HRV86   ------------------------------------------------------------
3739  241_1HRV86   ------------------------------------------------------------
3740  242_HRV70    ------------------------------------------------------------
3741  243_HRV70a   ------------------------------------------------------------
3742  244_HRV70b   ------------------------------------------------------------
3743  245_HRV91    ------------------------------------------------------------
3744  246_HRV91a   ------------------------------------------------------------
3745  247_HRV91b   ------------------------------------------------------------
3746  248_HRV17    ------------------------------------------------------------
3747  249_HRV17a   ------------------------------------------------------------
3748  250_HRV17b   ------------------------------------------------------------
3749  251_HRV69    ------------------------------------------------------------
3750  252_HRV69a   ------------------------------------------------------------
3751  253_HRV69b   ------------------------------------------------------------
3752  254_HRV48    ------------------------------------------------------------
3753  255_HRV48a   ------------------------------------------------------------
3754  256_HRV48b   ------------------------------------------------------------
3755  257_HRV52    ------------------------------------------------------------
3756  258_HRV52a   ------------------------------------------------------------
3757  259_HRV52b   ------------------------------------------------------------
3758  260_HRV4     ------------------------------------------------------------
3759  261_HRV4a|   ------------------------------------------------------------
3760  262_HRV4b|   ------------------------------------------------------------
3761  263_HRV99    ------------------------------------------------------------
3762  264_HRV99a   ------------------------------------------------------------
3763  265_HRV99b   ------------------------------------------------------------
3764  266_HRV5     ------------------------------------------------------------
3765  267_HRV5a|   ------------------------------------------------------------
3766  268_HRV5b|   ------------------------------------------------------------
3767  269_HRV42    ------------------------------------------------------------
3768  270_HRV42a   ------------------------------------------------------------
3769  271_HRV42b   ------------------------------------------------------------
3770  272_HRV26    ------------------------------------------------------------
3771  273_HRV26a   ------------------------------------------------------------
3772  274_HRV26b   ------------------------------------------------------------
3773  275_HRV27    ------------------------------------------------------------
3774  276_HRV27a   ------------------------------------------------------------
3775  277_HRV27b   ------------------------------------------------------------
3776  278_HRV93    ------------------------------------------------------------
```

FIG. D5 CONT'D

01.trace                                                              9/20/2007 4:58 PM

```
3777  279_HRV93a       ------------------------------------------------------------
3778  280_HRV93b       ------------------------------------------------------------
3779  281_HRV97        ------------------------------------------------------------
3780  282_HRV97a       ------------------------------------------------------------
3781  283_HRV97b       ------------------------------------------------------------
3782  284_HRV84        ------------------------------------------------------------
3783  285_HRV84a       ------------------------------------------------------------
3784  286_HRV84b       ------------------------------------------------------------
3785  287_HRV87        ------------------------------------------------------------
3786  288_HRV87a       ------------------------------------------------------------
3787  289_HRV87b       ------------------------------------------------------------
3788  GROUP_1          ------------------------------------------------------------
3789
3790  1_HRV1A1|d       CATCACAACACACATATATCATAAAGCTAAACACACAAAAGCTTGGTGTCCTAGGCCCCC
3791  2_HRV1A2|d       CATCACAACACACATATATCATAAAGCTAAACACACAAAAGCTTGGTGTCCTAGGCCCCC
3792  3_HRV1A|cD       CATCACAACACACATATATCATAAAGCTAAACACACAAAAGCTTGGTGTCCTAGGCCCCC
3793  4_HRV1B1|d       TATTACAACACACATATATCACAAAGCTAAACACACAAAAGCTTGGTGTCCTAGACCTCC
3794  5_HRV1B2|d       TATTACAACACACATATATCACAAAGCTAAACACACAAAAGCTTGGTGTCCTAGACCTCC
3795  6_HRV1B          TATTACAACACACATATATCACAAAGCTAAACACACAAAAGCTTGGTGTCCTAGACCTCC
3796  7_HRV40a|d       GATTACCACACGTATATATCACAAGGCCAAGCATATTAAAGCATGGTGTCCAAGGGCCCC
3797  8_HRV40b|d       GATTACCACACGTATATATCACAAGGCCAAGCATATTAAAGCATGGTGTCCAAGGGCCCC
3798  9_HRV40          GATTACCACACGTATATATCACAAGGCCAAGCATATTAAAGCATGGTGTCCAAGGGCCCC
3799  10_HRV85         AATCACCACGCGTGTGTATCATAAGGCCAAGCATGTAAAGGCTTGGTGTCCAAGAGCACC
3800  11_HRV85a|       AATCACCACGCGTGTGTATCATAAGGCCAAGCATGTAAAGGCTTGGTGTCCAAGAGCACC
3801  12_HRV85b|       AATCACCACGCGTGTGTATCATAAGGCCAAGCATGTAAAGGCTTGGTGTCCAAGAGCACC
3802  13_HRV56a|       AGTCACAACTCGTGTATATCATAAGGCAAAGCATATTCGAGCATGGTGTCCTAGAGCACC
3803  14_HRV56b|       AGTCACAACTCGTGTATATCATAAGGCAAAGCATATTCGAGCATGGTGTCCTAGAGCACC
3804  15_HRV56         AGTCACAACTCGTGTATATCATAAGGCAAAGCATATTCGAGCATGGTGTCCTAGAGCACC
3805  16_HRV54         AATCACCACACGGGTGTATACACAAGGCAAAACACATTAGAGCATGGTGTCCACGTGCACC
3806  17_HRV98         AATCACTACACGTGTGTACCACAAAGCAAAACACATTAGAGCATGGTGTCCACGTGCACC
3807  18_HRV59a|       GGTTGTCACACGTGTGTATCACAAAGCTAAACACGTCAAAGCCTGGTGCCCTAGAGCTCC
3808  19_HRV59b|       GGTTGTCACACGTGTGTATCACAAAGCTAAACACGTCAAAGCCTGGTGCCCTAGAGCTCC
3809  20_HRV59         GGTTGTCACACGTGTGTATCACAAAGCTAAACACGTCAAAGCCTGGTGCCCTAGAGCTCC
3810  21_HRV63         GGTGACTACACGTGTATATCATAAAGCTAAACACATCAGAGCCTGGTGCCCAAGAGCTCC
3811  22_HRV63b|       GGTGACTACACGTGTATATCATAAAGCTAAACACATCAGAGCCTGGTGCCCAAGAGCTCC
3812  23_HRV63a|       GGTGACTACACGTGTATATCATAAAGCTAAACACATCAGAGCCTGGTGCCCAAGAGCTCC
3813  24_HRV39         GGTTACAACCAGAGTTTACCATAAAGCCAAGCATGTTAAAGCATGGTGCCCTAGGGCTCC
3814  25_HRV39a|       GGTTACAACCAGAGTTTACCATAAAGCCAAGCATGTTAAAGCATGGTGCCCTAGGGCTCC
3815  26_HRV39b|       GGTTACAACCAGAGTTTACCATAAAGCCAAGCATGTTAAAGCATGGTGCCCTAGGGCTCC
3816  27_HRV10a|       AATTACCACCAGTGTTTATCACAAAGCCAAGCATGTCAAAGCATGGTGTCCAAGACCACC
3817  28_HRV10b|       AATTACCACCAGTGTTTATCACAAAGCCAAGCATGTCAAAGCATGGTGTCCAAGACCACC
3818  29_HRV10         AATTACCACCAGTGTTTATCACAAAGCCAAGCATGTCAAAGCATGGTGTCCAAGACCACC
3819  30_HRV100a       AATTACTACTAATATCTATCACAAGGCCAAACATGTTAAAGCTTGGTGCCCAAGACCACC
3820  31_HRV100b       AATTACTACTAATATCTATCACAAGGCCAAACATGTTAAAGCTTGGTGCCCAAGACCACC
3821  32_HRV100        AATTACTACTAATATCTATCACAAGGCCAAACATGTTAAAGCTTGGTGCCCAAGACCACC
3822  33_HRV66         AATTACTACTAGAGTATACCATAAGGCTAAGCATGTTAAAGCCTGGTGTCCTAGACCACT
3823  34_HRV66b|       AATTACTACTAGAGTATACCATAAGGCTAAGCATGTTAAAGCCTGGTGTCCTAGACCACT
3824  35_HRV66a|       AATTACTACTAGAGTATACCATAAGGCTAAGCATGTTAAAGCCTGGTGTCCTAGACCACT
3825  36_HRV77a|       AATCACCACTAGAGTATACCACAAGGCTAAACATATTAAAGCTTGGTGTCCCAGACCACC
3826  37_HRV77b|       AATCACCACTAGAGTATACCACAAGGCTAAACATATTAAAGCATGGTGTCCCAGACCACC
3827  38_HRV77         AATCACCACTAGAGTATACCACAAGGCTAAACATATTAAAGCTTGGTGTCCCAGACCACC
3828  39_HRV62a        GGTCACAACTAATATTTACCACAAGGCTAAGCATGTAAAAGCGTGGTGCCCGCGGCCGCC
3829  40_HRV62b        GGTCACAACTAATATTTACCACAAGGCTAAGCATGTAAAAGCGTGGTGCCCTAGACCACC
3830  41_HRV25         GGTTACAACTAACATTTACCACAAGGCTAAGCATGTAAAAGCATGGTGCCCTAGACCACC
3831  42_HRV29a        AGTTACAACAAGTATCTATCATAAAGCTAAACATGTAAAGGCGTGGTGTCCTAGACCACC
3832  43_HRV29b        AGTTACAACAAGTATCTATCATAAAGCTAAACATGTAAAGGCGTGGTGTCCTAGACCACC
3833  44_HRV44a        AGTTACAACAAGCATTTATCACAAAGCTAAACATGTAAAAGCATGGTGCCCTAGACCACC
3834  45_HRV44b        AGTTACAACAAGCATTTATCACAAAGCTAAACATGTAAAAGCATGGTGCCCTAGACCACC
3835  46_HRV31         AATCACAACCAATATTTACCATAAGGCCAAACATGTTAAGGCATGGTGTCCTAGGCCCCC
3836  47_HRV31a|       AATCACAACCAATATTTACCATAAGGCCAAACATGTTAAGGCATGGTGTCCTAGGCCCCC
3837  48_HRV31b|       AATCACAACCAATATTTACCATAAGGCCAAACATGTAAAGGCATGGTGTCCTAGGCCACC
3838  49_HRV47         AATCACAACTAACATCTACCATAAAGCCAAGCATGTGAAAGCATGGTGTCCTAGACCACC
3839  50_HRV47a|       AATCACAACTAACATCTACCATAAAGCCAAGCATGTGAAAGCATGGTGTCCTAGACCACC
3840  51_HRV47b|       AATCACAACTAACATCTACCATAAAGCCAAGCATGTGAAAGCATGGTGTCCTAGACCACC
```

FIG. D5 CONT'D

01.trace                                                                 9/20/2007 4:58 PM

```
3841  52_HRV11     AGTCACAACTAGGGTGTATCATAAAGCAAAGCATGTGAAGGTGTGGTGTCCAAGACCACC
3842  53_HRV11b|   AGTCACAACTAGGGTGTATCATAAAGCAAAGCATGTGAAGGTGTGGTGTCCAAGACCACC
3843  54_HRV11a|   AGTCACAACTAGGGTGTATCATAAAGCAAAGCATGTGAAGGTGTGGTGTCCAAGACCACC
3844  55_HRV76     AGTTACAACAAGAATATATCACAAAGCAAAGCATGTTAAGGTATGGTGCCCGAGACCACC
3845  56_HRV76b|   AGTTACAACAAGAATATATCACAAAGCAAAGCATGTTAAGGTATGGTGCCCGAGACCACC
3846  57_HRV76a|   AGTTACAACAAGAATATATCACAAAGCAAAGCATGTTAAGGTATGGTGCCCGAGACCACC
3847  58_HRV33     AGTTACAACAAGAGTATACCATAAAGCAAAACATGTCAAAGTCTGGTGCCCAAGACCACC
3848  59_HRV33b|   AGTTACAACAAGAGTATACCATAAAGCAAAACATGTCAAAGTCTGGTGCCCAAGACCACC
3849  60_HRV33a|   AGTTACAACAAGAGTATACCATAAAGCAAAACATGTCAAAGTCTGGTGCCCAAGACCACC
3850  61_HRV24a|   AATTACAACAAGAATATACCACAAAGCAAAGCACATTAAGGTCTGGTGTCCAAGGCCACC
3851  62_HRV24b|   AATTACAACAAGAATATACCACAAAGCAAAGCACATTAAGGTCTGGTGTCCAAGGCCACC
3852  63_HRV24     AATTACAACAAGAATATACCACAAAGCAAAGCACATTAAGGTCTGGTGTCCAAGGCCACC
3853  64_HRV90     GATCACTACAAGAATATACCATAAAGCAAAACACATTAAGGTTTGGTGTCCAAGACCACC
3854  65_HRV90a|   GATCACTACAAGAATATACCATAAAGCAAAACACATTAAGGTTTGGTGTCCAAGACCACC
3855  66_HRV90b|   GATCACTACAAGAATATACCATAAAGCAAAACACATTAAGGTTTGGTGTCCAAGACCACC
3856  67_HRV34     AATAACAACTAGAGTTTATCACAAAGCTAAACATGTAAAAACCTGGTGTCCAAGACCACC
3857  68_HRV34b|   AATAACAACTAGAGTTTATCACAAAGCTAAACATGTAAAAACCTGGTGTCCAAGACCACC
3858  69_HRV34a|   AATAACAACTAGAGTTTATCACAAAGCTAAACATGTAAAAACCTGGTGTCCAAGACCACC
3859  70_HRV50a|   AATCACAACCAGAGTATACCATAAAGCCAAACACATAAAAGTCTGGTGTCCAAGACCACC
3860  71_HRV50b|   AATCACAACCAGAGTATACCATAAAGCCAAACACATAAAAGTCTGGTGTCCAAGACCACC
3861  72_HRV50     AATCACAACCAGAGTATACCATAAAGCCAAACACATAAAAGTCTGGTGTCCAAGACCACC
3862  73_HRV18a|   AATAACAACCAGAATATACCACAAGGCAAAACATGTTAAAGCATGGTGCCCAAGGCCACC
3863  74_HRV18b|   AATAACAACCAGAATATACCACAAGGCAAAACATGTTAAAGCATGGTGCCCAAGGCCACC
3864  75_HRV18     AATAACAACCAGAATATACCACAAGGCAAAACATGTTAAAGCATGGTGCCCAAGGCCACC
3865  76_HRV55     AGTGACGACAAGAGTCTATCATAAAGCTAAACACATCAAAGCATGGTGCCCACGACCACC
3866  77_HRV55b|   AGTGACGACAAGAGTCTATCATAAAGCTAAACACATCAAAGCATGGTGCCCACGACCACC
3867  78_HRV55a|   AGTGACGACAAGAGTCTATCATAAAGCTAAACACATCAAAGCATGGTGCCCACGACCACC
3868  79_HRV57     AATAACAACCAGAGTGTATCACAAAGCCAAACATGTCAAAGCCTGGTGCCCTAGACCACC
3869  80_HRV57a|   AATAACAACCAGAGTGTATCACAAAGCCAAACATGTCAAAGCCTGGTGCCCTAGACCACC
3870  81_HRV57b|   AATAACAACCAGAGTGTATCACAAAGCCAAACATGTCAAAGCCTGGTGCCCTAGACCACC
3871  82_HRV21     AGTGACCACAAGAATATACCATAAGGCAAAGCATGTTAAAGCTTGGTGCCCCAGACCACC
3872  83_HRVHan    AGTGACCACAAGAATATACCATAAGGCAAAGCATGTTAAAGCTTGGTGCCCTAGACCACC
3873  84_HRV43     GATAACTACCAGGATATATCATAAAGCCAAGCATATCAAAGCTTGGTGCCCAAGACCACC
3874  85_HRV43b|   GATAACTACCAGGATATATCATAAAGCCAAGCATATCAAAGCTTGGTGCCCAAGACCACC
3875  86_HRV43a|   GATAACTACCAGGATATATCATAAAGCCAAGCATATCAAAGCTTGGTGCCCAAGACCACC
3876  87_HRV75     AGTAACCACTAGAATATATCACAAAGCCAAACATATAAAAGCTTGGTGTCCGAGGCCGCC
3877  88_HRV75b|   AGTAACCACTAGAATATATCACAAAGCCAAACATATAAAAGCTTGGTGTCCGAGGCCGCC
3878  89_HRV75a|   AGTAACCACTAGAATATATCACAAAGCCAAACATATAAAAGCTTGGTGTCCGAGGCCGCC
3879  96_HRV9a|d   AATTTCAACCAGAATATATCACAAAGCCAAACATGTTAAAGCCTGGTGCCCAAGACCTCC
3880  97_HRV9b|d   AATTTCAACCAGAATATATCACAAAGCCAAACATGTTAAAGCCTGGTGCCCAAGACCTCC
3881  98_HRV9      AATTTCAACCAGAATATATCACAAAGCCAAACATGTTAAAGCCTGGTGCCCAAGACCTCC
3882  99_HRV32     TATTTCAACTAGGGTATATCACAAAGCTAAACACGTCAAAGCTTGGTGCCCACGACCACC
3883  100_HRV32a   TATTTCAACTAGGGTATATCACAAAGCTAAACACGTCAAAGCTTGGTGCCCACGACCACC
3884  101_HRV32b   TATTTCAACTAGGGTATATCACAAAGCTAAACACGTCAAAGCTTGGTGCCCACGACCACC
3885  102_HRV67    AATTGCAACGCGGGTGTATCATAAGGCTAAACATGTAAAAGCTTGGTGCCCAAGGCCCCC
3886  103_HRV67a   AATTGCAACGCGGGTGTATCATAAGGCTAAACATGTAAAAGCTTGGTGCCCAAGGCCCCC
3887  104_HRV67b   AATTGCAACGCGGGTGTATCATAAGGCTAAACATGTAAAAGCTTGGTGCCCAAGGCCCCC
3888  105_HRV15    GATTACAACTAGAGTGTATCACAAAGCTAAACATGTAAAGGCTTGGTGCCCCAGACCCCC
3889  106_HRV15a   GATTACAACTAGAGTGTATCACAAAGCTAAACATGTAAAGGCTTGGTGCCCCAGACCCCC
3890  107_HRV15b   GATTACAACTAGAGTGTATCACAAAGCTAAACATGTAAAGGCTTGGTGCCCCAGACCCCC
3891  108_HRV74a   AATTACAACTAGAGTGTACCATAAAGCAAAGCATGTGAAGGCATGGTGTCCTAGACCCCC
3892  109_HRV74b   AATTACAACTAGAGTGTACCATAAAGCAAAGCATGTGAAGGCATGGTGTCCTAGACCCCC
3893  110_HRV74    AATTACAACTAGAGTGTACCATAAAGCAAAGCATGTGAAGGCATGGTGTCCTAGACCCCC
3894  111_HRV38a   GATAACAACTAGAATTTATCATAAGGCAAAACATGTAAAAGCCTGGTGTCCAAGACCCCC
3895  112_HRV38b   GATAACAACTAGAATTTATCATAAGGCAAAACATGTAAAAGCCTGGTGTCCAAGACCCCC
3896  113_HRV38    GATAACAACTAGAATTTATCATAAGGCAAAACATGTAAAAGCCTGGTGTCCAAGACCCCC
3897  114_HRV60    CGTCGCAACAAGAATATATCATAAAGCAAAGCATGTTAAGGCTTGGTGTCCAAGACCTCC
3898  115_HRV60a   CGTCGCAACAAGAATATATCATAAAGCAAAGCATGTTAAGGCTTGGTGTCCAAGACCTCC
3899  116_HRV60b   CGTCGCAACAAGAATATATCATAAAGCAAAGCATGTTAAGGCTTGGTGTCCAAGACCTCC
3900  117_HRV64    CATCACTACTAGGGTTTATCACAAAGCAAAACATGTCAAGGCATGTGGTCCACGGCCCCC
3901  118_HRV64b   CATCACTACTAGGGTTTATCACAAAGCAAAACATGTCAAGGCATGTGGTCCACGGCCCCC
3902  119_HRV64    CATCACTACTAGGGTTTATCACAAAGCAAAACATGTCAAGGCATGGTGTCCACGGCCCCC
3903  120_HRV94a   CATCACTACTAGAGTGTACCACAAAGCAAAACATGTGAAAGCGTGGTGCCCGCGCCCTCC
3904  121_HRV94b   CATCACTACTAGAGTGTACCACAAAGCAAAACATGTGAAAGCGTGGTGCCCGCGCCCTCC
```

FIG. D5 CONT'D 01.trace                                                                      9/20/2007 4:58 PM

```
3905 122_HRV94    CATCACTACTAGAGTGTACCACAAAGCAAAACATGTGAAAGCGTGGTGCCCGCGCCCTCC
3906 123_HRV22    AATTACAACTAGAGTGTACCACAAAGCAAAACATGTAAAGGCATGGTGCCCACGTCCTCC
3907 124_HRV22a   AATTACAACTAGAGTGTACCACAAAGCAAAACATGTAAAGGCATGGTGCCCACGTCCTCC
3908 125_HRV22b   AATTACAACTAGAGTGTACCACAAAGCAAAACATGTAAAGGCATGGTGCCCACGTCCTCC
3909 126_HRV82    CATTACCACAAGAATATATCACAAAGCAAAACATGTGAAAGCGTGGTGTCCACGACCCCC
3910 127_HRV82b   CATTACCACAAGAATATATCACAAAGCAAAACATGTGAAAGCGTGGTGTCCACGACCCCC
3911 128_HRV82a   CATTACCACAAGAATATATCACAAAGCAAAACATGTGAAAGCGTGGTGTCCACGACCCCC
3912 129_HRV19    AATCACAACTAGAGTATATCATAAAGCTAAACATATAAAAGCTTGGTGCCCACGACCACC
3913 130_HRV19a   AATCACAACTAGAGTATATCATAAAGCTAAACATATAAAAGCTTGGTGCCCACGACCACC
3914 131_HRV19b   AATCACAACTAGAGTATATCATAAAGCTAAACATATAAAAGCTTGGTGCCCACGACCACC
3915 132_HRV13    GGTTACAACTAGAATCTATCATAAAGCTAAACATGTCAAAGCATGGTGTCCTAGACCTCC
3916 133_HRV13a   GGTTACAACTAGAATCTATCATAAAGCTAAACATGTCAAAGCATGGTGTCCTAGACCTCC
3917 134_HRV13b   GGTTACAACTAGAATCTATCATAAAGCTAAACATGTCAAAGCATGGTGTCCTAGACCTCC
3918 135_HRV41    GGTCACAACTAGAGTTTACCACAAAGCTAAACATGTTAAAGCATGGTGTCCTAGACCTCC
3919 136_HRV41a   GGTCACAACTAGAGTTTACCACAAAGCTAAACATGTTAAAGCATGGTGTCCTAGACCTCC
3920 137_HRV41b   GGTCACAACTAGAGTTTACCACAAAGCTAAACATGTTAAAGCATGGTGTCCTAGACCTCC
3921 138_HRV73    GGTTACTACTAGAATCTATCATAAGGCTAAACATGTTAAAGCTTGGTGTCCAAGACCTCC
3922 139_HRV73b   GGTTACTACTAGAATCTATCATAAGGCTAAACATGTTAAAGCTTGGTGTCCAAGACCTCC
3923 140_HRV73a   GGTTACTACTAGAATCTATCATAAGGCTAAACATGTTAAAGCTTGGTGTCCAAGACCTCC
3924 141_HRV61    AATCACAACTAGGATTTACCATAAAGCTAAACATGTTAAAGTCTGGTGTCCTAGACCCCC
3925 142_HRV61a   AATCACAACTAGGATTTACCATAAAGCTAAACATGTTAAAGTCTGGTGTCCTAGACCCCC
3926 143_HRV61b   AATCACAACTAGGATTTACCATAAAGCTAAACATGTTAAAGTCTGGTGTCCTAGACCCCC
3927 144_HRV96    AATTACAACCAGAGTTTACCACAAAGCTAAACATGTTAAGGTGTGGTGCCCGAGACCCCC
3928 145_HRV96b   AATTACAACCAGAGTTTACCACAAAGCTAAACATGTTAAGGTGTGGTGCCCGAGACCCCC
3929 146_HRV96a   AATTACAACCAGAGTTTACCACAAAGCTAAACATGTTAAGGTGTGGTGCCCGAGACCCCC
3930 90_HRV16a|   AGTGGTAACAAGGATATATCACAAAGCCAAACACACCAAAGCTTGGTGCCCAAGACCACC
3931 91_HRV16b|   AGTGGTAACAAGGATATATCACAAAGCCAAACACACCAAAGCTTGGTGCCCAAGACCACC
3932 92_1AYM_A    AGTGGTAACAAGGATATATCACAAAGCCAAACACACCAAAGCTTGGTGCCCAAGACCACC
3933 93_HRV81a|   AATAGTAACAAGAATATATCACAAAGCTAAGCACACCAAAGCTTGGTGTCCAAGACCACC
3934 94_HRV81b|   AATAGTAACAAGAATATATCACAAAGCTAAGCACACCAAAGCTTGGTGTCCAAGACCACC
3935 95_HRV81     AATAGTAACAAGAATATATCACAAAGCTAAGCACACCAAAGCTTGGTGTCCAAGACCACC
3936 147_HRV2     TATAATGACAAGAATCTATCACAAGGCTAAACATGTCAAGGCATGGTGTCCACGCCCACC
3937 148_HRV2a|   TATAATGACAAGAATCTATCACAAGGCTAAACATGTCAAGGCATGGTGTCCACGCCCACC
3938 149_HRV2b|   TATAATGACAAGAATCTATCACAAGGCTAAACATGTCAAGGCATGGTGTCCACGCCCACC
3939 150_HRV49a   TATCATGACAAGAATCTATCATAAAGCTAAACACGTCAAAGCATGGTGTCCGCGCCCACC
3940 151_HRV49b   TATCATGACAAGAATCTATCATAAAGCTAAACACGTCAAAGCATGGTGTCCGCGCCCACC
3941 152_HRV49    TATCATGACAAGAATCTATCATAAAGCTAAACACGTCAAAGCATGGTGTCCGCGCCCACC
3942 153_HRV23a   GATAATGACAAGGGTCTACCACAAAGCTAAACATGTCAAAGCATGGTGTCCGCGGCCACC
3943 154_HRV23b   GATAATGACAAGGGTCTACCACAAAGCTAAACATGTCAAAGCATGGTGTCCGCGGCCACC
3944 155_HRV23    GATAATGACAAGGGTCTACCACAAAGCTAAACATGTCAAAGCATGGTGTCCGCGGCCACC
3945 156_HRV30a   CATAATGACAAGGGTCTACCACAAGGCTAAACATGTCAAAGCGTGGTGTCCACGGCCACC
3946 157_HRV30b   CATAATGACAAGGGTCTACCACAAGGCTAAACATGTCAAAGCGTGGTGTCCACGGCCACC
3947 158_HRV30    CATAATGACAAGGGTCTACCACAAGGCTAAACATGTCAAAGCGTGGTGTCCACGGCCACC
3948 159_HRV7     GATTGTGAGTCGCATTTACCACAAAGCCAAACATATAAAAGCATGGTGCCCACGCCCACC
3949 160_HRV7b|   GATTGTGAGTCGCATTTACCACAAAGCCAAACATATAAAAGCATGGTGCCCACGCCCACC
3950 161_HRV7a|   GATTGTGAGTCGCATTTACCACAAAGCCAAACATATAAAAGCATGGTGCCCACGCCCACC
3951 162_HRV88    TATCATTAGCCGTATATATCACAAGGCTAAACATATAAAAGGCATGGTGTCCACGCCCACC
3952 163_HRV88a   TATCATTAGCCGTATATATCACAAGGCTAAACATATAAAAGGCATGGTGTCCACGCCCACC
3953 164_HRV88b   TATCATTAGCCGTATATATCACAAGGCTAAACATATAAAAGGCATGGTGTCCACGCCCACC
3954 165_HRV36a   TATTGTATGCCGCATTTATCATAAAGCTAAACACATAAAGGCCTGGTGCCCGCGTCCACC
3955 166_HRV36b   TATTGTATGCCGCATTTATCATAAAGCTAAACACATAAAGGCCTGGTGCCCGCGTCCACC
3956 167_HRV36    TATTGTATGCCGCATTTATCATAAAGCTAAACACATAAAGGCCTGGTGCCCGCGTCCACC
3957 168_HRV89a   TATTGTGTGCCGCATTTACCACAAGGCCAAACATATAAAAGCATGGTGTCCTCGCCCACC
3958 169_HRV89b   TATTGTGTGCCGCATTTACCACAAGGCCAAACATATAAAAGCATGGTGTCCTCGCCCACC
3959 170_HRV89    TATTGTGTGCCGCATTTACCACAAGGCCAAACATATAAAAGCATGGTGTCCTCGCCCACC
3960 171_HRV58    CATTGTCTGTCGCATTTACCACAAAGCCAAGCATATAAAAGCATGGTGTCCACGCCCACC
3961 172_HRV58a   CATTGTCTGTCGCATTTACCACAAAGCCAAGCATATAAAAGCATGGTGTCCACGCCCACC
3962 173_HRV58b   CATTGTCTGTCGCATTTACCACAAAGCCAAGCATATAAAAGCATGGTGTCCACGCCCACC
3963 174_HRV12a   GATTACCAGTAGAATATACCATAAACAAAACATATCAGTGCCTGGGGCCCTAGACCACC
3964 175_HRV12b   GATTACCAGTAGAATATACCATAAAGCAAAACATATCAGTGCCTGGGGCCCTAGACCACC
3965 176_HRV12    GATTACCAGTAGAATATACCATAAAGCAAAACATATCAGTGCCTGGGGCCCTAGACCACC
3966 177_HRV78a   AATTACAGCTAGAGTCTACCACAAGGCCAAACATATTAGTGCATGGGGCCCAAGACCTCC
3967 178_HRV78b   AATTACAGCTAGAGTCTACCACAAGGCCAAACATATTAGTGCATGGGGCCCAAGACCTCC
3968 179_HRV78    AATTACAGCTAGAGTCTACCACAAGGCCAAACATATTAGTGCATGGGGCCCAAGACCTCC
```

FIG. D5 CONT'D 01.trace                                                                                              9/20/2007 4:58 PM

```
3969 180_HRV20      GATAACCAGTAGGATATTCCACAAGGCAAAGCATATTAGTGCATGGTGTCCAAGGGCCCC
3970 181_HRV20a     GATAACCAGTAGGATATTCCACAAGGCAAAGCATATTAGTGCATGGTGTCCAAGGGCCCC
3971 182_HRV20b     GATAACCAGTAGGATATTCCACAAGGCAAAGCATATTAGTGCATGGTGTCCAAGGGCCCC
3972 183_HRV68      AATAACCAGCAGAATATTCCATAAAGCAAAACATATTAGTGCGTGGTGTCCAAGAGCTCC
3973 184_HRV68a     AATAACCAGCAGAATATTCCATAAAGCAAAACATATTAGTGCGTGGTGTCCAAGAGCTCC
3974 185_HRV68b     AATAACCAGCAGAATATTCCATAAAGCAAAACATATTAGTGCGTGGTGTCCAAGAGCTCC
3975 186_HRV28      AATAACCAGCATAATATTCCACAAAGCTAAACATGTCAGTGCATGGTGCCCCAGACCTCC
3976 187_HRV28a     AATAACCAGCATAATATTCCACAAAGCTAAACATGTCAGTGCATGGTGCCCCAGACCTCC
3977 188_HRV28b     AATAACCAGCATAATATTCCACAAAGCTAAACATGTCAGTGCATGGTGCCCCAGACCTCC
3978 189_HRV53a     GATAACCAGTAGGATTTATCACAAGGCTAAACATATCAGTGCATGGTGTCCAAGACCACC
3979 190_HRV53b     GATAACCAGTAGGATTTATCACAAGGCTAAACATATCAGTGCATGGTGTCCAAGACCACC
3980 191_HRV53      GATAACCAGTAGGATTTATCACAAGGCTAAACATATCAGTGCATGGTGTCCAAGACCACC
3981 192_HRV46a     TATAACTAGCAGAATATATCACAAGGCTAAACACATTAAAGCATGGTGCCCCAGGGCACC
3982 193_HRV46b     TATAACTAGCAGAATATATCACAAGGCTAAACACATTAAAGCATGGTGCCCCAGGGCACC
3983 194_HRV46      TATAACTAGCAGAATATATCACAAGGCTAAACACATTAAAGCATGGTGCCCCAGGGCACC
3984 195_HRV80a     AATCACCAGCAGAATATATCACAAAGCTAAACACATCAAAGCATGGTGTCCAAGAGCACC
3985 196_HRV80b     AATCACCAGCAGAATATATCACAAAGCTAAACACATCAAAGCATGGTGTCCAAGAGCACC
3986 197_HRV80      AATCACCAGCAGAATATATCACAAAGCTAAACACATCAAAGCATGGTGTCCAAGAGCACC
3987 198_HRV51      CATAACTAGCAGGATTTACCACAAAGCCAAACATGTCAGTGCATGGTGCCCTCGTCCTCC
3988 199_HRV51a     CATAACTAGCAGGATTTACCACAAAGCCAAACATGTCAGTGCATGGTGCCCTCGTCCTCC
3989 200_HRV51b     CATAACTAGCAGGATTTACCACAAAGCCAAACATGTCAGTGCATGGTGCCCTCGTCCTCC
3990 201_HRV65a     CATAACCAGTAGAATATATCATAAAGCTAAACACATCAGTGCTTGGTGTCCACGACCTCC
3991 202_HRV65b     CATAACCAGTAGAATATATCATAAAGCTAAACACATCAGTGCTTGGTGTCCACGACCTCC
3992 203_HRV65      CATAACCAGTAGAATATATCATAAAGCTAAACACATCAGTGCTTGGTGTCCACGACCTCC
3993 204_HRV71a     CATAACAAGTAGGATTTATCACAAAGCCAAACATGTCAGAGCATGGTGTCCTAGACCCCC
3994 205_HRV71b     CATAACAAGTAGGATTTATCACAAAGCCAAACATGTCAGAGCATGGTGTCCTAGACCCCC
3995 206_HRV71      CATAACAAGTAGGATTTATCACAAAGCCAAACATGTCAGAGCATGGTGTCCTAGACCCCC
3996 207_HRV8       AATTGATTCAAGAATATACCTGAAAGCAAAGCACATTAAAGCTTGGTGTCCTAGACCCCC
3997 208_HRV95      AATTGATTCAAGAATATACCTGAAAGCAAAGCATATTAAAGCTTGGTGTCCTAGACCCCC
3998 209_HRV45      GATCGACTCCATGGTATATCTAAAAGCTAAACACATCAAGGCATGGTGTCCCAGACCTCC
3999 210_HRV45a     GATCGACTCCATGGTATATCTAAAAGCTAAACACATCAAGGCATGGTGTCCCAGACCTCC
4000 211_HRV45b     GATCGACTCCATGGTATATCTAAAAGCTAAACACATCAAGGCATGGTGTCCCAGACCTCC
4001 212_HRV6       ------------------------------------------------------------
4002 213_HRV6a|     ------------------------------------------------------------
4003 214_HRV6b|     ------------------------------------------------------------
4004 215_HRV37      ------------------------------------------------------------
4005 216_HRV37a     ------------------------------------------------------------
4006 217_HRV37b     ------------------------------------------------------------
4007 218_HRV3       ------------------------------------------------------------
4008 219_HRV3a|     ------------------------------------------------------------
4009 220_HRV3b|     ------------------------------------------------------------
4010 221_HRV14      ------------------------------------------------------------
4011 222_HRV14a     ------------------------------------------------------------
4012 223_HRV14b     ------------------------------------------------------------
4013 224_HRV72      ------------------------------------------------------------
4014 225_HRV72a     ------------------------------------------------------------
4015 226_HRV72b     ------------------------------------------------------------
4016 227_HRV83      ------------------------------------------------------------
4017 228_HRV83a     ------------------------------------------------------------
4018 229_HRV83b     ------------------------------------------------------------
4019 230_HRV92      ------------------------------------------------------------
4020 231_HRV92a     ------------------------------------------------------------
4021 232_HRV92b     ------------------------------------------------------------
4022 233_HRV79      ------------------------------------------------------------
4023 234_HRV79a     ------------------------------------------------------------
4024 235_HRV79b     ------------------------------------------------------------
4025 236_HRV35      ------------------------------------------------------------
4026 237_HRV35a     ------------------------------------------------------------
4027 238_HRV35b     ------------------------------------------------------------
4028 239_1HRV86     ------------------------------------------------------------
4029 240_1HRV86     ------------------------------------------------------------
4030 241_1HRV86     ------------------------------------------------------------
4031 242_HRV70      ------------------------------------------------------------
4032 243_HRV70a     ------------------------------------------------------------
```

FIG. D5 CONT'D 01.trace                                                                                        9/20/2007 4:58 PM

```
4033 244_HRV70b     ------------------------------------------------------------
4034 245_HRV91      ------------------------------------------------------------
4035 246_HRV91a     ------------------------------------------------------------
4036 247_HRV91b     ------------------------------------------------------------
4037 248_HRV17      ------------------------------------------------------------
4038 249_HRV17a     ------------------------------------------------------------
4039 250_HRV17b     ------------------------------------------------------------
4040 251_HRV69      ------------------------------------------------------------
4041 252_HRV69a     ------------------------------------------------------------
4042 253_HRV69b     ------------------------------------------------------------
4043 254_HRV48      ------------------------------------------------------------
4044 255_HRV48a     ------------------------------------------------------------
4045 256_HRV48b     ------------------------------------------------------------
4046 257_HRV52      ------------------------------------------------------------
4047 258_HRV52a     ------------------------------------------------------------
4048 259_HRV52b     ------------------------------------------------------------
4049 260_HRV4       ------------------------------------------------------------
4050 261_HRV4a|     ------------------------------------------------------------
4051 262_HRV4b|     ------------------------------------------------------------
4052 263_HRV99      ------------------------------------------------------------
4053 264_HRV99a     ------------------------------------------------------------
4054 265_HRV99b     ------------------------------------------------------------
4055 266_HRV5       ------------------------------------------------------------
4056 267_HRV5a|     ------------------------------------------------------------
4057 268_HRV5b|     ------------------------------------------------------------
4058 269_HRV42      ------------------------------------------------------------
4059 270_HRV42a     ------------------------------------------------------------
4060 271_HRV42b     ------------------------------------------------------------
4061 272_HRV26      ------------------------------------------------------------
4062 273_HRV26a     ------------------------------------------------------------
4063 274_HRV26b     ------------------------------------------------------------
4064 275_HRV27      ------------------------------------------------------------
4065 276_HRV27a     ------------------------------------------------------------
4066 277_HRV27b     ------------------------------------------------------------
4067 278_HRV93      ------------------------------------------------------------
4068 279_HRV93a     ------------------------------------------------------------
4069 280_HRV93b     ------------------------------------------------------------
4070 281_HRV97      ------------------------------------------------------------
4071 282_HRV97a     ------------------------------------------------------------
4072 283_HRV97b     ------------------------------------------------------------
4073 284_HRV84      ------------------------------------------------------------
4074 285_HRV84a     ------------------------------------------------------------
4075 286_HRV84b     ------------------------------------------------------------
4076 287_HRV87      ------------------------------------------------------------
4077 288_HRV87a     ------------------------------------------------------------
4078 289_HRV87b     ------------------------------------------------------------
4079 GROUP_1        ------------------------------------------------------------
4080
4081  1_HRV1A1|d    TAGAGCTGTCCCTTACACA-CATAGTCATGTGACTAATTATATGC-CAGAAA---CAGGT
4082  2_HRV1A2|d    TAGAGCTGTCCCTTACACA-CATAGTCATGTGACTAATTATATGC-CAGAAA---CAGGT
4083  3_HRV1A|cD    TAGAGCTGTCCCTTACACA-CATAGTCATGTGACTAATTATATGC-CAGAAA---CAGGT
4084  4_HRV1B1|d    TAGAGCTGTTCCTTACACA-CATAGTCGTGTAACTAATTATGTAC-CAAAAA---CAGGT
4085  5_HRV1B2|d    TAGAGCTGTTCCTTACACA-CATAGTCGTGTAACTAATTATGTAC-CAAAAA---CAGGT
4086  6_HRV1B       TAGAGCTGTTCCTTACACA-CATAGTCGTGTAACTAATTATGTAC-CAAAAA---CAGGT
4087  7_HRV40a|d    AAGAGCAGTACCTTACACA-CATACACACTCAACAAATTATAAAC-CTCAAG---AAGGT
4088  8_HRV40b|d    AAGAGCAGTACCTTACACA-CATACACACTCAACAAATTATAAAC-CTCAAG---AAGGT
4089  9_HRV40       AAGAGCAGTACCTTACACA-CATACACACTCAACAAATTATAAAC-CTCAAG---AAGGT
4090 10_HRV85       AAGAGCGGTGCCTTATACA-CACACACGCTCAACCAACTATGTGC-CACAAG---ATGGT
4091 11_HRV85a|     AAGAGCGGTGCCTTATACA-CACACACGCTCAACCAACTATGTGC-CACAAG---ATGGT
4092 12_HRV85b|     AAGAGCGGTGCCTTATACA-CACACACGCTCAACCAACTATGTGC-CACAAG---ATGGT
4093 13_HRV56a|     AAGGGCTGTGCCTTATACA-CATGCTCACGTCACCAATTATAAAC-CACAAG---ATGGT
4094 14_HRV56b|     AAGGGCTGTGCCTTATACA-CATGCTCACGTCACCAATTATAAAC-CACAAG---ATGGT
4095 15_HRV56       AAGGGCTGTGCCTTATACA-CATGCTCACGTCACCAATTATAAAC-CACAAG---ATGGT
4096 16_HRV54       TAGGGCTGTCCCATACACA-CATACTAGATCAACAAATTACATGC-CACGGG---AGGGT
```

FIG. D5 CONT'D

01.trace                                                                                    9/20/2007 4:58 PM

```
4097  17_HRV98     TAGAGCTGTTCCATACACA-CACACTAGATCAACTAATTACATGC-CTCAAG---ATGGT
4098  18_HRV59a|   TAGAGCAGTCCCTTACACA-CACAGCTACGTAACTAACTACAAGATTGCTGG---AAAA-
4099  19_HRV59b|   TAGAGCAGTCCCTTACACA-CACAGCTACGTAACTAACTACAAGATTGCTGG---AAAA-
4100  20_HRV59     TAGAGCAGTCCCTTACACA-CACAGCTACGTAACTAACTACAAGATTGCTGG---AAAA-
4101  21_HRV63     TAGGGCTGTTCCATACACA-CATAGTTATGTCACTAACTATAAAATTACAGG---ACAG-
4102  22_HRV63b    TAGGGCTGTTCCATACACA-CATAGTTATGTCACTAACTATAAAATTACAGG---ACAG-
4103  23_HRV63a|   TAGGGCTGTTCCATACACA-CATAGTTATGTCACTAACTATAAAATTACAGG---ACAG-
4104  24_HRV39     CAGAGCAGTCCCTTACACA-CACAGCAATGTTACAAATTACAAAG-TACGGG---ACGGT
4105  25_HRV39a|   CAGAGCAGTCCCTTACACA-CACAGCAATGTTACAAATTACAAAG-TACGGG---ACGGT
4106  26_HRV39b|   CAGAGCAGTCCCTTACACA-CACAGCAATGTTACAAATTACAAAG-TACGGG---ACGGT
4107  27_HRV10a|   CAGAGCTGTACCATATACA-CATGCCCATTCCACAAATTACAAAC-CACATG---GCAAA
4108  28_HRV10b|   CAGAGCTGTACCATATACA-CATGCCCATTCCACAAATTACAAAC-CACATG---GCAAA
4109  29_HRV10     CAGAGCTGTACCATATACA-CATGCCCATTCCACAAATTACAAAC-CACATG---GCAAA
4110  30_HRV100a   TCGGGCTGTGCCGTACACA-CATAGTCACTCTACAAATTACAAAC-CACATG---AGGGT
4111  31_HRV100b   TCGGGCTGTGCCGTACACA-CATAGTCACTCTACAAATTACAAAC-CACATG---AGGGT
4112  32_HRV100    TCGGGCTGTGCCGTACACA-CATAGTCACTCTACAAATTACAAAC-CACATG---AGGGT
4113  33_HRV66     TAGAGCTGTACCATACACA-ACTGTAAACTCAACCAATTATATGC-CTCATA---CTGGT
4114  34_HRV66b    TAGAGCTGTACCATACACA-ACTGTAAACTCAACCAATTATATGC-CTCATA---CTGGT
4115  35_HRV66a|   TAGAGCTGTACCATACACA-ACTGTAAACTCAACCAATTATATGC-CTCATA---CTGGT
4116  36_HRV77a|   TAGAGCTGTACCATACACA-GCAGTAGATTCAACAAATTACAAAC-CTATGA---GAGGG
4117  37_HRV77b|   TAGAGCTGTACCATACACA-GCAGTAGATTCAACAAATTACAAAC-CTATGA---GAGGG
4118  38_HRV77     TAGAGCTGTACCATACACA-GCAGTAGATTCAACAAATTACAAAC-CTATGA---GAGGG
4119  39_HRV62a    CAGAGCTGTTCCATATAAA-TATGTTGATTTCAATAATTATGCAG-CCAGTG---ATAGT
4120  40_HRV62b    TAGAGCTGTTCCATATAAA-TATGTTGATTTCAATAATTATGCAG-CCAGTG---ATAGT
4121  41_HRV25     TAGAGCTGTCCCATATAAA-TATGTTCAATAATTATGCAG-CCAGTG---ATAAT
4122  42_HRV29a    AAGAGTTGTCCCATACAAG-TATGTTGGCCTAACTAATTACACAC-TTAAAG---AAGAA
4123  43_HRV29b    AAGAGTTGTCCCATACAAG-TATGTTGGCCTAACTAATTACACAC-TTAAAG---AAGAA
4124  44_HRV44a    AAGGGTTGTCCCATACAAG-TATGTTGGCCTAACTAATTACACAC-TTAAAG---AAACA
4125  45_HRV44b    AAGGGTTGTCCCATACAAG-TATGTTGGCCTAACTAATTACACAC-TTAAAG---AAACA
4126  46_HRV31     TAGAGCAGTTCCATACAGGGTATG-TGGATCAACAAACTACAAAC-CTGATG---AAAAT
4127  47_HRV31a|   TAGAGCAGTTCCATACAGGGTATG-TGGATCAACAAACTACAAAC-CTGATG---AAAAT
4128  48_HRV31b|   TAGAGCAGTTCCATACAGG-TATGTTGGATCAACAAACTACAAAC-CTGATG---AAAAT
4129  49_HRV47     TAGAGCTGTTCCATATAGA-TATGTTGGATCAACAAATTACAAAC-CTGATC---AAGGA
4130  50_HRV47a|   TAGAGCTGTTCCATATAGA-TATGTTGGATCAACAAATTACAAAC-CTGATC---AAGGA
4131  51_HRV47b|   TAGAGCTGTTCCATATAGA-TATGTTGGATCAACAAATTACAAAC-CTGATC---AAGGA
4132  52_HRV11     TAGAGCTGTAGAATATACT-CACACTCATGTAACCAATTACAAAC-CACAGG---AAGGA
4133  53_HRV11b|   TAGAGCTGTAGAATATACT-CACACTCATGTAACCAATTACAAAC-CACAGG---AAGGA
4134  54_HRV11a|   TAGAGCTGTAGAATATACT-CACACTCATGTAACCAATTACAAAC-CACAGG---AAGGA
4135  55_HRV76     TAGAGCTGTAGAGTATACA-TACACCCATGTAACAAACTACAAAC-CACATT---CTGGT
4136  56_HRV76b|   TAGAGCTGTAGAGTATACA-TACACCCATGTAACAAACTACAAAC-CACATT---CTGGT
4137  57_HRV76a|   TAGAGCTGTAGAGTATACA-TACACCCATGTAACAAACTACAAAC-CACATT---CTGGT
4138  58_HRV33     TAGAGCTGTGGAATACACC-CATACTCATGTTACAAATTATAAAT-CAACAA---CTCGT
4139  59_HRV33b|   TAGAGCTGTGGAATACACC-CATACTCATGTTACAAATTATAAAT-CAACAA---CTCGT
4140  60_HRV33a|   TAGAGCTGTGGAATACACC-CATACTCATGTTACAAATTATAAAT-CAACAA---CTCGT
4141  61_HRV24a|   CAGAGCTGTTGAGTATACA-CATACTCACGTGACCAATTATAAGC-ATCAGA---CTCGT
4142  62_HRV24b|   CAGAGCTGTTGAGTATACA-CATACTCACGTGACCAATTATAAGC-ATCAGA---CTCGT
4143  63_HRV24     CAGAGCTGTTGAGTATACA-CATACTCACGTGACCAATTATAAGC-ATCAGA---CTCGT
4144  64_HRV90     TAGGGCAGTTGAATACACA-CACACTCATGTAACAAACTACAAAC-ATGCAA---CACGT
4145  65_HRV90a|   TAGGGCAGTTGAATACACA-CACACTCATGTAACAAACTACAAAC-ATGCAA---CACGT
4146  66_HRV90b|   TAGGGCAGTTGAATACACA-CACACTCATGTAACAAACTACAAAC-ATGCAA---CACGT
4147  67_HRV34     AAGAGCTGTTGAGTACACA-CACACACATGTTACTAACTACAAAG-TTAGGG---GTAAA
4148  68_HRV34b|   AAGAGCTGTTGAGTACACA-CACACACATGTTACTAACTACAAAG-TTAGGG---GTAAA
4149  69_HRV34a|   AAGAGCTGTTGAGTACACA-CACACACATGTTACTAACTACAAAG-TTAGGG---GTAAA
4150  70_HRV50a|   AAGAGCTGTTGAATACACA-CACACCCATGTCACTAACTACAAGA-AAAGTG---ATGCT
4151  71_HRV50b|   AAGAGCTGTTGAATACACA-CACACCCATGTCACTAACTACAAGA-AAAGTG---ATGCT
4152  72_HRV50     AAGAGCTGTTGAATACACA-CACACCCATGTCACTAACTACAAGA-AAAGTG---ATGCT
4153  73_HRV18a|   GAGAGCTGTGGAGTACACA-CATACACATGTAACTAACTACAAGC-CTAAGG---AAGGA
4154  74_HRV18b|   GAGAGCTGTGGAGTACACA-CATACACATGTAACTAACTACAAGC-CTAAGG---AAGGA
4155  75_HRV18     GAGAGCTGTGGAGTACACA-CATACACATGTAACTAACTACAAGC-CTAAGG---AAGGA
4156  76_HRV55     TAGGGCTGTTGAATACACA-CACACACATGTCACAAATTACAAGA-AGACTG---ATGGC
4157  77_HRV55b|   TAGGGCTGTTGAATACACA-CACACACATGTCACAAATTACAAGA-AGACTG---ATGGC
4158  78_HRV55a|   TAGGGCTGTTGAATACACA-CACACACATGTCACAAATTACAAGA-AGACTG---ATGGC
4159  79_HRV57     ACGGGCTATCGAGTACACA-CATACACATGTTACTAATTATAAAA-TAAAAG---ATAGA
4160  80_HRV57a|   ACGGGCTATCGAGTACACA-CATACACATGTTACTAATTATAAAA-TAAAAG---ATAGA
```

FIG. D5 CONT'D 01.trace                                                                 9/20/2007 4:58 PM

```
4161  81_HRV57b|    ACGGGCTATCGAGTACACA-CATACACATGTTACTAATTATAAAA-TAAAAG---ATAGA
4162  82_HRV21      GAGGGCCGTTGAATACACA-CATACACACGTAACCAATTACAAAA-TTGCAA---ATCAT
4163  83_HRVHan     GAGGGCCGTTGAATACACA-CATACACATGTAACCAATTACAAAA-TTGCAA---ATAAA
4164  84_HRV43      CAGAGCTGTTGAATACACA-CACACACATGTCACAAATTATAAAA-GAGAAG---GAAAG
4165  85_HRV43b|    CAGAGCTGTTGAATACACA-CACACACATGTCACAAATTATAAAA-GAGAAG---GAAAG
4166  86_HRV43a|    CAGAGCTGTTGAATACACA-CACACACATGTCACAAATTATAAAA-GAGAAG---GAAAG
4167  87_HRV75      CAGGGCTGTTGAATACACA-TTTAGACGTGTAACAAATTACAAAA-GAGATG---GACAA
4168  88_HRV75b|    CAGGGCTGTTGAATACACA-TTTAGACGTGTAACAAATTACAAAA-GAGATG---GACAA
4169  89_HRV75a|    CAGGGCTGTTGAATACACA-TTTAGACGTGTAACAAATTACAAAA-GAGATG---GACAA
4170  96_HRV9a|d    TAGGGCAGTTGAGTATATA-CATACACATGTCACAAATTACAAGC-CAAGCA---CAGGC
4171  97_HRV9b|d    TAGGGCAGTTGAGTATATA-CATACACATGTCACAAATTACAAGC-CAAGCA---CAGGC
4172  98_HRV9       TAGGGCAGTTGAGTATATA-CATACACATGTCACAAATTACAAGC-CAAGCA---CAGGC
4173  99_HRV32      TAGGGCAGTTGAATATACA-CATACACATGTTACAAATTACAAAC-CAAGCA---CAGGT
4174  100_HRV32a    TAGGGCAGTTGAATATACA-CATACACATGTTACAAATTACAAAC-CAAGCA---CAGGT
4175  101_HRV32b    TAGGGCAGTTGAATATACA-CATACACATGTTACAAATTACAAAC-CAAGCA---CAGGT
4176  102_HRV67     TAGAGCAGTTGAATATACA-CACACACATGTTACAAACTATAGAC-CAGAAA---CAGGT
4177  103_HRV67a    TAGAGCAGTTGAATACATA-CACACACATGTTACAAACTATAGAC-CAGAAA---CAGGT
4178  104_HRV67b    TAGAGCAGTTGAATACATA-CACACACATGTTACAAACTATAGAC-CAGAAA---CAGGT
4179  105_HRV15     TAGAGCAGTGGAATATACA-CACACACATGTCACAAATTACAAAC-CACAAG---ATGGT
4180  106_HRV15a    TAGAGCAGTGGAATATACA-CACACACATGTCACAAATTACAAAC-CACAAG---ATGGT
4181  107_HRV15b    TAGAGCAGTGGAATATACA-CACACACATGTCACAAATTACAAAC-CACAAG---ATGGT
4182  108_HRV74a    TAGAGCAGTTGAATATACT-CACACACATGTCACAAATTACAAAC-CACAAG---AAGGT
4183  109_HRV74b    TAGAGCAGTTGAATATACT-CACACACATGTCACAAATTACAAAC-CACAAG---AAGGT
4184  110_HRV74     TAGAGCAGTTGAATATACT-CACACACATGTCACAAATTACAAAC-CACAAG---AAGGT
4185  111_HRV38a    AAGGGCAGTTGAATATAGA-CATACACATGTTAACAATTACAAAC-CAGACC---AAGGG
4186  112_HRV38b    AAGGGCAGTTGAATATAGA-CATACACATGTTAACAATTACAAAC-CAGACC---AAGGG
4187  113_HRV38     AAGGGCAGTTGAATATAGA-CATACACATGTTAACAATTACAAAC-CAGACC---AAGGG
4188  114_HRV60     AAGGGCAGTTGAATATAGA-CACACACATGTAAACAACTATAGAC-CAGATG---ATGGA
4189  115_HRV60a    AAGGGCAGTTGAATATAGA-CACACACATGTAAACAACTATAGAC-CAGATG---ATGGA
4190  116_HRV60b    AAGGGCAGTTGAATATAGA-CACACACATGTAAACAACTATAGAC-CAGATG---ATGGA
4191  117_HRV64a    AAGAGCTGTTGGATATACA-CATACAAATGTCACCAATTATAAAC-CATCCA---AAGGA
4192  118_HRV64b    AAGAGCTGTTGGATATACA-CATACAAATGTCACCAATTATAAAC-CATCCA---AAGGA
4193  119_HRV64     AAGAGCTGTTGGATATACA-CATACAAATGTCACCAATTATAAAC-CATCCA---AAGGA
4194  120_HRV94a    AAGAGCTGTTGGATACACA-CATACGCATGTCACTAATTACAAAC-CATCTG---AAGGG
4195  121_HRV94b    AAGAGCTGTTGGATACACA-CATACGCATGTCACTAATTACAAAC-CATCTG---AAGGG
4196  122_HRV94     AAGAGCTGTTGGATACACA-CATACGCATGTCACTAATTACAAAC-CATCTG---AAGGG
4197  123_HRV22     AAGAGCTGTTGGATATACA-CACACACATGTGACAAACTACAAAC-CATCTG---TAGGG
4198  124_HRV22a    AAGAGCTGTTGGATATACA-CACACACATGTGACAAACTACAAAC-CATCTG---TAGGG
4199  125_HRV22b    AAGAGCTGTTGGATATACA-CACACACATGTGACAAACTACAAAC-CATCTG---TAGGG
4200  126_HRV82     GAGGGCTGTGGGTTATACA-CACACACATGTTACCAACTACAAGC-CATCAC---AGGGA
4201  127_HRV82b    GAGGGCTGTGGGTTATACA-CACACACATGTTACCAACTACAAGC-CATCAC---AGGGA
4202  128_HRV82a    GAGGGCTGTGGGTTATACA-CACACACATGTTACCAACTACAAGC-CATCAC---AGGGA
4203  129_HRV19     CAGAGCCGTGGAATATACC-CACACTCATGTGACTAATTATAAAC-CCCAGA---CAGGT
4204  130_HRV19a    CAGAGCCGTGGAATATACC-CACACTCATGTGACTAATTATAAAC-CCCAGA---CAGGT
4205  131_HRV19b    CAGAGCCGTGGAATATACC-CACACTCATGTGACTAATTATAAAC-CCCAGA---CAGGT
4206  132_HRV13     CAGAGCTGTTGAATATACT-AATGTGCATGTTACAAACTACAAAC-CAGGGA---CAGGA
4207  133_HRV13a    CAGAGCTGTTGAATATACT-AATGTGCATGTTACAAACTACAAAC-CAGGGA---CAGGA
4208  134_HRV13b    CAGAGCTGTTGAATATACT-AATGTGCATGTTACAAACTACAAAC-CAGGGA---CAGGA
4209  135_HRV41     CAGGGCTGTGGAGTACACC-AATGTGCATGTCACAAATTACAAAC-CAAAAG---CAGGA
4210  136_HRV41a    CAGGGCTGTGGAGTACACC-AATGTGCATGTCACAAATTACAAAC-CAAAAG---CAGGA
4211  137_HRV41b    CAGGGCTGTGGAGTACACC-AATGTGCATGTCACAAATTACAAAC-CAAAAG---CAGGA
4212  138_HRV73     TAGGGCAGTAGAATATACA-AATGCACATGTGACCAATTATAAAC-CCACTG---ATGGA
4213  139_HRV73b    TAGGGCAGTAGAATATACA-AATGCACATGTGACCAATTATAAAC-CCACTG---ATGGA
4214  140_HRV73a    TAGGGCAGTAGAATATACA-AATGCACATGTGACCAATTATAAAC-CCACTG---ATGGA
4215  141_HRV61     CAGAGCAGTGGAATATACT-AATGTGCATTTGACCAATTACAAGC-CCAAAG---ATAGT
4216  142_HRV61a    CAGAGCAGTGGAATATACT-AATGTGCATTTGACCAATTACAAGC-CCAAAG---ATAGT
4217  143_HRV61b    CAGAGCAGTGGAATATACT-AATGTGCATTTGACCAATTACAAGC-CCAAAG---ATAGT
4218  144_HRV96     TAGAGCAGTTGAATACACA-AATGTGCATCTCACAAATTATAAAC-CCAACA---ATG--
4219  145_HRV96b    TAGAGCAGTTGAATACACA-AATGTGCATCTCACAAATTATAAAC-CCAACA---ATG--
4220  146_HRV96a    TAGAGCAGTTGAATACACA-AATGTGCATCTCACAAATTATAAAC-CCAACA---ATG--
4221  90_HRV16a|    CAGAGCTGTTCAATACTCA-CATACACATACCACCAACTACAAAT-TGAGTT---CAGAA
4222  91_HRV16b|    CAGAGCTGTTCAATACTCA-CATACACATACCACCAACTACAAAT-TGAGTT---CAGAA
4223  92_1AYM_A     CAGAGCTGTTCAATACTCA-CATACACATACCACCAACTACAAAT-TGAGTT---CAGAA
4224  93_HRV81a|    CAGGGCTGTTCAGTACACA-CATACACATGTAACTAATTATAAAT-TAGAAA---CAGAT
```

FIG. D5 CONT'D 01.trace                                                                9/20/2007 4:58 PM

```
4225  94_HRV81b|   CAGGGCTGTTCAGTACACA-CATACACATGTAACTAATTATAAAT-TAGAAA---CAGAT
4226  95_HRV81     CAGGGCTGTTCAGTACACA-CATACACATGTAACTAATTATAAAT-TAGAAA---CAGAT
4227  147_HRV2     CAGAGCGCTTGAGTATACT-CGTGCTCACCGCACTAATTTTAAAA-TTGAGG---ATAGG
4228  148_HRV2a|   CAGAGCGCTTGAGTATACT-CGTGCTCACCGCACTAATTTTAAAA-TTGAGG---ATAGG
4229  149_HRV2b|   CAGAGCGCTTGAGTATACT-CGTGCTCACCGCACTAATTTTAAAA-TTGAGG---ATAGG
4230  150_HRV49a   CAGAGCACTTGAATATACT-CGCGCTCACCGTACTAATTTCAAAG-TTGAAG---ACAGA
4231  151_HRV49b   CAGAGCACTTGAATATACT-CGCGCTCACCGTACTAATTTCAAAG-TTGAAG---ACAGA
4232  152_HRV49    CAGAGCACTTGAATATACT-CGCGCTCACCGTACTAATTTCAAAG-TTGAAG---ACAGA
4233  153_HRV23a   CAGAGCACTTGAATACACA-CGCGCTCACCGTACTAATTTCAAAA-TTGAAG---GTGAA
4234  154_HRV23b   CAGAGCACTTGAATACACA-CGCGCTCACCGTACTAATTTCAAAA-TTGAAG---GTGAA
4235  155_HRV23    CAGAGCACTTGAATACACA-CGCGCTCACCGTACTAATTTCAAAA-TTGAAG---GTGAA
4236  156_HRV30a   TAGGGCGCTTGAGTATACC-CGTGCTCATCGCACCAATTTTAAAA-TTGATG---GCAGG
4237  157_HRV30b   TAGGGCGCTTGAGTATACC-CGTGCTCATCGCACCAATTTTAAAA-TTGATG---GCAGG
4238  158_HRV30    TAGGGCGCTTGAGTATACC-CGTGCTCATCGCACCAATTTTAAAA-TTGATG---GCAGG
4239  159_HRV7     ACGAGCTGTGCCTTATCAA-CACACTCACTCCACCAACTATGTGC-CACAAA---ATGGA
4240  160_HRV7b|   ACGAGCTGTGCCTTATCAA-CACACTCACTCCACCAACTATGTGC-CACAAA---ATGGA
4241  161_HRV7a|   ACGAGCTGTGCCTTATCAA-CACACTCACTCCACCAACTATGTGC-CACAAA---ATGGA
4242  162_HRV88    AAGAGCCGTACCTTATCAG-CACACACACTCCACCAATTATGTAC-CAACAG---ATGGG
4243  163_HRV88a   AAGAGCCGTACCTTATCAG-CACACACACTCCACCAATTATGTAC-CAACAG---ATGGG
4244  164_HRV88b   AAGAGCCGTACCTTATCAG-CACACACACTCCACCAATTATGTAC-CAACAG---ATGGG
4245  165_HRV36a   AAGGGCCGTTCCTTACCAA-CACACACATTCCACTAATTATATAC-CATACA---AAGGT
4246  166_HRV36b   AAGGGCCGTTCCTTACCAA-CACACACATTCCACTAATTATATAC-CATACA---AAGGT
4247  167_HRV36    AAGGGCCGTTCCTTACCAA-CACACACATTCCACTAATTATATAC-CATACA---AAGGT
4248  168_HRV89a   AAGGGCTGTTGCCTATCAA-CACACACACTCAATTAATTACATAC-CATCCA---ATGGT
4249  169_HRV89b   AAGGGCTGTTGCCTATCAA-CACACACACTCAACCAATTACATAC-CATCCA---ATGGT
4250  170_HRV89    AAGGGCTGTTGCCTATCAA-CACACACACTCAACCAATTACATAC-CATCCA---ATGGT
4251  171_HRV58    AAGGGCTGTTCCTTATCAA-TTCACACATTCTACTAATTACATAC-CAGATA---GTGGT
4252  172_HRV58a   AAGGGCTGTTCCTTATCAA-TTCACACATTCTACTAATTACATAC-CAGATA---GTGGT
4253  173_HRV58b   AAGGGCTGTTCCTTATCAA-TTCACACATTCTACTAATTACATAC-CAGATA---GTGGT
4254  174_HRV12a   AAGAGCTGTACCATACCAG-CATATACACAATCCAAATTACAAGA-CAAGTA------AT
4255  175_HRV12b   AAGAGCTGTACCATACCAG-CATATACACAATCCAAATTACAAGA-CAAGTA------AT
4256  176_HRV12    AAGAGCTGTACCATACCAG-CATATACACAATCCAAATTACAAGA-CAAGTA------AT
4257  177_HRV78a   TAGAGCTGTACCTTATCAG-CACATATATAACCCTAATTATAAAA-CTGAAG------AA
4258  178_HRV78b   TAGAGCTGTACCTTATCAG-CACATATATAACCCTAATTATAAAA-CTGAAG------AA
4259  179_HRV78    TAGAGCTGTACCTTATCAG-CACATATATAACCCTAATTATAAAA-CTGAAG------AA
4260  180_HRV20    AAGAGCAGTGCCTTATCAA-CACACTAAGAGCACAAACTTAGTGC-CAAGGA---CAGGT
4261  181_HRV20a   AAGAGCAGTGCCTTATCAA-CACACTAAGAGCACAAACTTAGTGC-CAAGGA---CAGGT
4262  182_HRV20b   AAGAGCAGTGCCTTATCAA-CACACTAAGAGCACAAACTTAGTGC-CAAGGA---CAGGT
4263  183_HRV68    AAGAGCAGTGCCCTACCAG-CACACCAGAAGTACAAACTTAGTAC-CAAAGG---AAGGT
4264  184_HRV68a   AAGAGCAGTGCCCTACCAG-CACACCAGAAGTACAAACTTAGTAC-CAAAGG---AAGGT
4265  185_HRV68b   AAGAGCAGTGCCCTACCAG-CACACCAGAAGTACAAACTTAGTAC-CAAAGG---AAGGT
4266  186_HRV28    ACGCGCTGTAGCTTATCAA-CATACATACAGTCCAAACTTTGTGC-CTCAGG---AAGGT
4267  187_HRV28a   ACGCGCTGTAGCTTATCAA-CATACATACAGTCCAAACTTTGTGC-CTCAGG---AAGGT
4268  188_HRV28b   ACGCGCTGTAGCTTATCAA-CATACATACAGTCCAAACTTTGTGC-CTCAGG---AAGGT
4269  189_HRV53a   AAGAGCAGTTGCATATCAA-CACACATATAGCCCAAATTTTGTAC-CGCAAA---CAGGA
4270  190_HRV53b   AAGAGCAGTTGCATATCAA-CACACATATAGCCCAAATTTTGTAC-CGCAAA---CAGGA
4271  191_HRV53    AAGAGCAGTTGCATATCAA-CACACATATAGCCCAAATTTTGTAC-CGCAAA---CAGGA
4272  192_HRV46a   CAGAGCAGTCCCATATCAA-CATATTTATAATCCAAATTCAAGA-CTACTCAACCTGAG
4273  193_HRV46b   CAGAGCAGTCCCATATCAA-CATATTTATAATCCAAATTCAAGA-CTACTCAACCTGAG
4274  194_HRV46    CAGAGCAGTCCCATATCAA-CATATTTATAATCCAAATTCAAGA-CTACTCAACCTGAG
4275  195_HRV80a   TAGAGCAGTCCCATACCAA-CATACCTACAGCCCAAATTTCAAAA-ACACTG---ATGAA
4276  196_HRV80b   TAGAGCAGTCCCATACCAA-CATACCTACAGCCCAAATTTCAAAA-ACACTG---ATGAA
4277  197_HRV80    TAGAGCAGTCCCATACCAA-CATACCTACAGCCCAAATTTCAAAA-ACACTG---ATGAA
4278  198_HRV51    TCGTGCTGTAGCCTACCAA-CACACATACAGTACAAACTTCGTTC-CAAAAGAGGGATTT
4279  199_HRV51a   TCGTGCTGTAGCCTACCAA-CACACATACAGTACAAACTTCGTTC-CAAAAGAGGGATTT
4280  200_HRV51b   TCGTGCTGTAGCCTACCAA-CACACATACAGTACAAACTTCGTTC-CAAAAGAGGGATTT
4281  201_HRV65a   CCGAGCAGTAGCTTACCAA-CACACATACAGTACAAATTTTGTTC-CTAGCGGAGGTCTT
4282  202_HRV65b   CCGAGCAGTAGCTTACCAA-CACACATACAGTACAAATTTTGTTC-CTAGCGGAGGTCTT
4283  203_HRV65    CCGAGCAGTAGCTTACCAA-CACACATACAGTACAAATTTTGTTC-CTAGCGGAGGTCTT
4284  204_HRV71a   CAGAGCAGTAGCCTACCAA-TCAACATATACCACAAATTTTGTTC-CACAAGACGGGATC
4285  205_HRV71b   CAGAGCAGTAGCCTACCAA-TCAACATATACCACAAATTTTGTTC-CACAAGACGGGATC
4286  206_HRV71    CAGAGCAGTAGCCTACCAA-TCAACATATACCACAAATTTTGTTC-CACAAGACGGGATC
4287  207_HRV8     CAGAGCAGTTACGTATAAC-CATATATACAACCCCAATTATGTTA-GAGAGG------GA
4288  208_HRV95    CAGAGCAGTTACGTATAAC-CATATATACAACCCCAATTATGTTA-GAGAGG------GA
```

FIG. D5 CONT'D

```
01.trace                                                                9/20/2007 4:58 PM 4289  209_HRV45    AAGAGCAGTCACATATAAC-CATACATATAATCCAAATTATGTTA-GGGCTG------AT
4290  210_HRV45a   AAGAGCAGTCACATATAAC-CATACATATAATCCAAATTATGTTA-GGGCTG------AT
4291  211_HRV45b   AAGAGCAGTCACATATAAC-CATACATATAATCCAAATTATGTTA-GGGCTG------AT
4292  212_HRV6     ------------------------------------------------------------
4293  213_HRV6a|   ------------------------------------------------------------
4294  214_HRV6b|   ------------------------------------------------------------
4295  215_HRV37    ------------------------------------------------------------
4296  216_HRV37a   ------------------------------------------------------------
4297  217_HRV37b   ------------------------------------------------------------
4298  218_HRV3     ------------------------------------------------------------
4299  219_HRV3a|   ------------------------------------------------------------
4300  220_HRV3b|   ------------------------------------------------------------
4301  221_HRV14    ------------------------------------------------------------
4302  222_HRV14a   ------------------------------------------------------------
4303  223_HRV14b   ------------------------------------------------------------
4304  224_HRV72    ------------------------------------------------------------
4305  225_HRV72a   ------------------------------------------------------------
4306  226_HRV72b   ------------------------------------------------------------
4307  227_HRV83    ------------------------------------------------------------
4308  228_HRV83a   ------------------------------------------------------------
4309  229_HRV83b   ------------------------------------------------------------
4310  230_HRV92    ------------------------------------------------------------
4311  231_HRV92a   ------------------------------------------------------------
4312  232_HRV92b   ------------------------------------------------------------
4313  233_HRV79    ------------------------------------------------------------
4314  234_HRV79a   ------------------------------------------------------------
4315  235_HRV79b   ------------------------------------------------------------
4316  236_HRV35    ------------------------------------------------------------
4317  237_HRV35a   ------------------------------------------------------------
4318  238_HRV35b   ------------------------------------------------------------
4319  239_1HRV86   ------------------------------------------------------------
4320  240_1HRV86   ------------------------------------------------------------
4321  241_1HRV86   ------------------------------------------------------------
4322  242_HRV70    ------------------------------------------------------------
4323  243_HRV70a   ------------------------------------------------------------
4324  244_HRV70b   ------------------------------------------------------------
4325  245_HRV91    ------------------------------------------------------------
4326  246_HRV91a   ------------------------------------------------------------
4327  247_HRV91b   ------------------------------------------------------------
4328  248_HRV17    ------------------------------------------------------------
4329  249_HRV17a   ------------------------------------------------------------
4330  250_HRV17b   ------------------------------------------------------------
4331  251_HRV69    ------------------------------------------------------------
4332  252_HRV69a   ------------------------------------------------------------
4333  253_HRV69b   ------------------------------------------------------------
4334  254_HRV48    ------------------------------------------------------------
4335  255_HRV48a   ------------------------------------------------------------
4336  256_HRV48b   ------------------------------------------------------------
4337  257_HRV52    ------------------------------------------------------------
4338  258_HRV52a   ------------------------------------------------------------
4339  259_HRV52b   ------------------------------------------------------------
4340  260_HRV4     ------------------------------------------------------------
4341  261_HRV4a|   ------------------------------------------------------------
4342  262_HRV4b|   ------------------------------------------------------------
4343  263_HRV99    ------------------------------------------------------------
4344  264_HRV99a   ------------------------------------------------------------
4345  265_HRV99b   ------------------------------------------------------------
4346  266_HRV5     ------------------------------------------------------------
4347  267_HRV5a|   ------------------------------------------------------------
4348  268_HRV5b|   ------------------------------------------------------------
4349  269_HRV42    ------------------------------------------------------------
4350  270_HRV42a   ------------------------------------------------------------
4351  271_HRV42b   ------------------------------------------------------------
4352  272_HRV26    ------------------------------------------------------------
```

FIG. D5 CONT'D

01.trace                                                                 9/20/2007 4:58 PM

```
4353  273_HRV26a    ----------------------------------------------------------
4354  274_HRV26b    ----------------------------------------------------------
4355  275_HRV27     ----------------------------------------------------------
4356  276_HRV27a    ----------------------------------------------------------
4357  277_HRV27b    ----------------------------------------------------------
4358  278_HRV93     ----------------------------------------------------------
4359  279_HRV93a    ----------------------------------------------------------
4360  280_HRV93b    ----------------------------------------------------------
4361  281_HRV97     ----------------------------------------------------------
4362  282_HRV97a    ----------------------------------------------------------
4363  283_HRV97b    ----------------------------------------------------------
4364  284_HRV84     ----------------------------------------------------------
4365  285_HRV84a    ----------------------------------------------------------
4366  286_HRV84b    ----------------------------------------------------------
4367  287_HRV87     ----------------------------------------------------------
4368  288_HRV87a    ----------------------------------------------------------
4369  289_HRV87b    ----------------------------------------------------------
4370  GROUP_1       ----------------------------------------------------------
4371
4372  1_HRV1A1|d    GACG------TGACAACAG---CCATAGTCCGCAGAA------ACACTATAACAACTG--
4373  2_HRV1A2|d    GACG------TGACAACAG---CCATAGTCCGCAGAA------ACACTATAACAACTG--
4374  3_HRV1A|cD    GACG------TGACAACAG---CCATAGTCCGCAGAA------ACACTATAACAACTG--
4375  4_HRV1B1|d    GATG------TGACAACAG---CTATAGTTCCTAGAG------CTAGCATGAAAACTG--
4376  5_HRV1B2|d    GATG------TGACAACAG---CTATAGTTCCTAGAG------CTAGCATGAAAACTG--
4377  6_HRV1B       GATG------TGACAACAG---CTATAGTTCCTAGAG------CTAGCATGAAAACTG--
4378  7_HRV40a|d    GAAG------TCCAGATTT---TCCTCAAAGAGAGAG------CCAGCCTAACAACAG--
4379  8_HRV40b|d    GAAG------TCCAGATTT---TCCTCAAAGAGAGAG------CCAGCCTAACAACAG--
4380  9_HRV40       GAAG------TCCAGATTT---TCCTCAAAGAGAGAG------CCAGCCTAACAACAG--
4381  10_HRV85      GAAG------TTAAGATCT---TCCTCAAAGAGAGAG------CTAGTTTAACCACAG--
4382  11_HRV85a|    GAAG------TTAAGATCT---TCCTCAAAGAGAGAG------CTAGTTTAACCACAG--
4383  12_HRV85b|    GAAG------TTAAGATCT---TCCTCAAAGAGAGAG------CTAGTTTAACCACAG--
4384  13_HRV56a|    GATG------TACAGATCT---TCTTAAAACCCAGAC------CCAGCCTAACAACAT--
4385  14_HRV56b|    GATG------TACAGATCT---TCTTAAAACCCAGAC------CCAGCCTAACAACAT--
4386  15_HRV56      GATG------TACAGATCT---TCTTAAAACCCAGAC------CCAGCCTAACAACAT--
4387  16_HRV54      GATC------CAACAATTT---TCCTTAAACACAGGA------CAAACCTTGTAACAG--
4388  17_HRV98      GAAC------CAACAATCT---TTCTTAAGCATAGAA------AAGATCTTGTAACAG--
4389  18_HRV59a|    GAAC------CTGAAATTT---TCTTAAAACCAAGAA------TGAATATTACAACAG--
4390  19_HRV59b|    GAAC------CTGAAATTT---TCTTAAAACCAAGAA------TGAATATTACAACAG--
4391  20_HRV59      GAAC------CTGAAATTT---TCTTAAAACCAAGAA------TGAATATTACAACAG--
4392  21_HRV63      GAGA------CTGAAATTT---TCTTAAAACCTAGAG------CAACTATCAAGACAG--
4393  22_HRV63b|    GAGA------CTGAAATTT---TCTTAAAACCTAGAG------CAACTATCAAGACAG--
4394  23_HRV63a|    GAGA------CTGAAATTT---TCTTAAAACCTAGAG------CAACTATCAAGACAG--
4395  24_HRV39      GAAC------CAACACTCT---TTATAAAATCAAGAG------AGAATCTTACCACAG--
4396  25_HRV39a|    GAAC------CAACACTCT---TTATAAAATCAAGAG------AGAATCTTACCACAG--
4397  26_HRV39b|    GAAC------CAACACTCT---TTATAAAACCAAGAG------AGAATCTTACCACAG--
4398  27_HRV10a|    GAAT------TACAAATAT---TTATTAGGTCTAGAGATGATCCCAAAGTAGTAACTG--
4399  28_HRV10b|    GAAT------TACAAATAT---TTATTAGGTCTAGAGATGATCCCAAAGTAGTAACTG--
4400  29_HRV10      GAAT------TACAAATAT---TTATTAGGTCTAGAGATGATCCCAAAGTAGTAACTG--
4401  30_HRV100a    GATG------TAAAGATTT---TCATTAGACCCAGAGATGATCCAAAGTTTGTAACTG--
4402  31_HRV100b    GATG------TAAAGATTT---TCATTAGACCCAGAGATGATCCAAAGTTTGTAACTG--
4403  32_HRV100     GATG------TAAAGATTT---TCATTAGACCCAGAGATGATCCAAAGTTTGTAACTG--
4404  33_HRV66      GATC------TGCAAATTT---TCATTAAACCTAGAACAGATCCAAAAGTAGTCAATG--
4405  34_HRV66b|    GATC------TGCAAATTT---TCATTAAACCTAGAACAGATCCAAAAGTAGTCAATG--
4406  35_HRV66a|    GATC------TGCAAATTT---TCATTAAACCTAGAACAGATCCAAAAGTAGTCAATG--
4407  36_HRV77a|    GATG------TACAAATCT---TTATTAAAGAGAGCAAGCCCAAAAGTAGTTACTT--
4408  37_HRV77b|    GATG------TACAAATCT---TTATTAAAGAGAGCAAGCCCAAAAGTAGTTACTT--
4409  38_HRV77      GATG------TACAAATCT---TTATTAAAGAGAGCAAGCCCAAAAGTAGTTACTT--
4410  39_HRV62a     ---G------TTGACATTT---TTATAAAATCAAGG------CAAAACTTGCAAACAG--
4411  40_HRV62b     ---G------TTGACATTT---TTATAAAATCAAGG------CAAAACTTGCAAACAG--
4412  41_HRV25      ---G------TTGACATCT---TTATACAACCAAGA------AACAGTTTAAAAACAG--
4413  42_HRV29a     ---G------AT-CCAG-----TTGTGGAATCCAGA------CCAAGCTTAATGACAG--
4414  43_HRV29b     ---G------AT-ACAG-----TTGTGGAATCCAGA------CCAAGCTTAATGACAG--
4415  44_HRV44a     ---G------AT-ACAG-----TTGTGGAACCTAGA------CACAGCATAATGACAG--
4416  45_HRV44b     ---G------AT-ACAG-----TTGTGGAACCTAGA------CACAGCATAATGACAG--
```

FIG. D5 CONT'D 01.trace                                                                                    9/20/2007 4:58 PM

```
4417   46_HRV31     GAAG------TTACAATCT---TTGTTAAACACAGGGATAATCCAAAGATTATCACAG--
4418   47_HRV31a|   GAAG------TTACAATCT---TTGTTAAACACAGGGATAATCCAAAGATTATCACAG--
4419   48_HRV31b|   GAAG------TTACAATCT---TTGTTAAACACAGGGATAATCCAAAGATTATCACAG--
4420   49_HRV47     GAAG------TTGCAATTT---TCATTGAGCATAGAGAAAATCCAAAATTCATTACAG--
4421   50_HRV47a|   GAAG------TTGCAATTT---TCATTGAGCATAGAGAAAATCCAAAATTCATTACAG--
4422   51_HRV47b|   GAAG------TTGCAATTT---TCATTGAGCATAGAGAAAATCCAAAATTCATTACAG--
4423   52_HRV11     CAGG------TGAAAACAG---CTGTCAAGGCTAGGAAAACAATTAAAACAGCA------
4424   53_HRV11b|   CAGG------TGAAAACAG---CTGTCAAGGCTAGGAAAACAATTAAAACAGCG------
4425   54_HRV11a|   CAGG------TGAAAACAG---CTGTCAAGGCTAGGAAAACAATTAAAACAGCT------
4426   55_HRV76     GATG------TGCAAACAG---CTATTAGACCAAGAGCAACAATTAAGACTGCA------
4427   56_HRV76b|   GATG------TGCAAACAG---CTATTAGACCAAGAGCAACAATTAAGACTGCG------
4428   57_HRV76a|   GATG------TGCAAACAG---CTATTAGACCAAGAGCAACAATTAAGACTGCT------
4429   58_HRV33     GAAG------TGAAGCAG---CTATTAGACCAAGAGCAACAATCAAGACTGCA------
4430   59_HRV33b|   GAAG------TGAAGCAG---CTATTAGACCAAGAGCAACAATCAAGACTGCG------
4431   60_HRV33a|   GAAG------TGAAGCAG---CTATTAGACCAAGAGCAACAATCAAGACTGCT------
4432   61_HRV24a|   GAAG------TCAAGCAG---CAATTGAACCTAGAAGAGGAATTAAAACAGTG------
4433   62_HRV24b|   GAAG------TCAAGCAG---CAATTGAACCTAGAAGAGGAATTAAAACAGTC------
4434   63_HRV24     GAAG------TCAAGCAG---CAATTGAACCTAGAAGAGGAATTAAAACAGTT------
4435   64_HRV90     GAAC------TTAAGACTG---CAATTAGGCCCAGGAAAACAATCACAACAGCA------
4436   65_HRV90a|   GAAC------TTAAGACTG---CAATTAGGCCCAGGAAAACAATCACAACAGCG------
4437   66_HRV90b|   GAAC------TTAAGACTG---CAATTAGGCCCAGGAAAACAATCACAACAGCT------
4438   67_HRV34     ACTG------AGAAGACTG---CAATCAAACACAGAGCAAAGATCACAATGGCC------
4439   68_HRV34b|   ACTG------AGAAGACTG---CAATCAAACACAGAGCAAAGATCACAATGGCA------
4440   69_HRV34a|   ACTG------AGAAGACTG---CAATCAAACACAGAGCAAAGATCACAATGGCT------
4441   70_HRV50a|   ACTG------AGAAGACTG---CAATTGCAACTAGACCAAAGATCACAGTGGCA------
4442   71_HRV50b|   ACTG------AGAAGACTG---CAATTGCAACTAGACCAAAGATCACAGTGGCG------
4443   72_HRV50     ACTG------AGAAGACTG---CAATTGCAACTAGACCAAAGATCACAGTGGCT------
4444   73_HRV18a|   AGAG------AGAAACTG---CCATAGTACCCAGAGCAAGGATTACAATGGCA------
4445   74_HRV18b|   AGAG------AGAAAACTG---CCATAGTACCCAGAGCAAGGATTACAATGGCG------
4446   75_HRV18     AGAG------AGAAAACTG---CCATAGTACCCAGAGCAAGGATTACAATGGCT------
4447   76_HRV55     ACAG------AAAAGACAG---CAATTGAATACAGAAGGGACATTAAAACAGTG------
4448   77_HRV55b|   ACAG------AAAAGACAG---CAATTGAATACAGAAGGGACATTAAAACAGTC------
4449   78_HRV55a|   ACAG------AAAAGACAG---CAATTGAATACAGAAGGGACATTAAAACAGTA------
4450   79_HRV57     CAAG------AAGAAACAG---CAATTAAATATAGAAGGGACATTAAAATTGTTAAGA--
4451   80_HRV57a|   CAAG------AAGAAACAG---CAATTAAATATAGAAGGGACATTAAAATTGTTAAGA--
4452   81_HRV57b|   CAAG------AAGAAACAG---CAATTAAATATAGAAGGGACATTAAAATTGTTAAGA--
4453   82_HRV21     GAAG------TCACTTCTG---CAGTTGAGTCCAGAAGAACAATTGTCACAGTT------
4454   83_HRVHan    GATG------TCACTTCTG---CAGTTGAGTCCAGAAGAACAATTGTCACAGTT------
4455   84_HRV43     GAGG------TAGAAACAG---CCATAGTATCTAGGAGGGATATCAAAATTGTCAATG--
4456   85_HRV43b|   GAGG------TAGAAACAG---CCATAGTATCTAGGAGGGATATCAAAATTGTCAATG--
4457   86_HRV43a|   GAGG------TAGAAACAG---CCATAGTATCTAGGAGGGATATCAAAATTGTCAATG--
4458   87_HRV75     CAAG------TTGAGATTG---CTATTGAGCCCAGAAGAGATGTTAAGTTTGTAAATG--
4459   88_HRV75b|   CAAG------TTGAGATTG---CTATTGAGCCCAGAAGAGATGTTAAGTTTGTAAATG--
4460   89_HRV75a|   CAAG------TTGAGATTG---CTATTGAGCCCAGAAGAGATGTTAAGTTTGTAAATG--
4461   96_HRV9a|d   GATT------ATGCCACAG---TTATACCAGTTAGAGACAATGTTAGGGCAGTAAAGA--
4462   97_HRV9b|d   GATT------ATGCCACAG---TTATACCAGTTAGAGACAATGTTAGGGCAGTAAAGA--
4463   98_HRV9      GATT------ATGCCACAG---TTATACCAGTTAGAGACAATGTTAGGGCAGTAAAGA--
4464   99_HRV32     GATT------ACACCACAG---CCATACAAACCAGAGAGCATGTTAGAGCAGTCAAAA--
4465   100_HRV32a   GATT------ACACCACAG---CCATACAAACCAGAGAGCATGTTAGAGCAGTCAAAA--
4466   101_HRV32b   GATT------ACACCACAG---CCATACAAACCAGAGAGCATGTTAGAGCAGTCAAAA--
4467   102_HRV67    GAGG------CTCAAACGG---TTATACCTGTTAGAGCAGATGTTAGAACAATTAGAA--
4468   103_HRV67a   GAGG------CTCAAACGG---TTATACCTGTTAGAGCAGATGTTAGAACAATTAGAA--
4469   104_HRV67b   GAGG------CTCAAACGG---TTATACCTGTTAGAGCAGATGTTAGAACAATTAGAA--
4470   105_HRV15    GATG------TAACTACAG---TTATTCCAACTAGAGAAAATGTTAGAGCTATAGTAA--
4471   106_HRV15a   GATG------TAACTACAG---TTATTCCAACTAGAGAAAATGTTAGAGCTATAGTAA--
4472   107_HRV15b   GATG------TAACTACAG---TTATTCCAACTAGAGAAAATGTTAGAGCTATAGTAA--
4473   108_HRV74a   GACG------TAACTACAG---TCATCCCAACTAGG--------AGATCAATAGTGA--
4474   109_HRV74b   GACG------TAACTACAG---TCATCCCAACTAGG--------AGATCAATAGTGA--
4475   110_HRV74    GACG------TAACTACAG---TCATCCCAACTAGG--------AGATCAATAGTGA--
4476   111_HRV38a   GAAG------TAACCACTA---TGATTCCAACTAGAACCAACATAAGAACCATCGTAA--
4477   112_HRV38b   GAAG------TAACCACTA---TGATTCCAACTAGAACCAACATAAGAACCATCGTAA--
4478   113_HRV38    GAAG------TAACCACTA---TGATTCCAACTAGAACCAACATAAGAACCATCGTAA--
4479   114_HRV60    GAAG------CAGCCATAA---CAATCCCCATTAGAACTGATATACGAGCAATCAGAA--
4480   115_HRV60a   GAAG------CAGCCATAA---CAATCCCCATTAGAACTGATATACGAGCAATCAGAA--
```

FIG. D5 CONT'D 01.trace                                                                                                9/20/2007 4:58 PM

```
4481  116_HRV60b   GAAG------CAGCCATAA---CAATCCCCATTAGAACTGATATACGAGCAATCAGAA--
4482  117_HRV64a   GAAT------ACACACCAC---CCGTTCCGTCACGTAACAGCCCCAGAGATATTGTCA--
4483  118_HRV64b   GAAT------ACACACCAC---CCGTTCCGTCACGTAACAGCCCCAGAGATATTGTCA--
4484  119_HRV64    GAAT------ACACACCAC---CCGTTCCGTCACGTAACAGCCCCAGAGATATTGTCA--
4485  120_HRV94a   GAGT------ACAAGCCAC---CTGTCCCAGTTAGGAATAGCCCCAGAGACATTGTCA--
4486  121_HRV94b   GAGT------ACAAGCCAC---CTGTCCCAGTTAGGAATAGCCCCAGAGACATTGTCA--
4487  122_HRV94    GAGT------ACAAGCCAC---CTGTCCCAGTTAGGAATAGCCCCAGAGACATTGTCA--
4488  123_HRV22    GATT------ACACACTAC---CTATCCCAACAAGAGCCAACCCTAGACAAATTTTGA--
4489  124_HRV22a   GATT------ACACACTAC---CTATCCCAACAAGAGCCAACCCTAGACAAATTTTGA--
4490  125_HRV22b   GATT------ACACACTAC---CTATCCCAACAAGAGCCAACCCTAGACAAATTTTGA--
4491  126_HRV82    GATT------ACAGTGTTG---TTATTCCAGTTAGAGAGAGTCCCAGACAGATTCTTA--
4492  127_HRV82b   GATT------ACAGTGTTG---TTATTCCAGTTAGAGAGAGTCCCAGACAGATTCTTA--
4493  128_HRV82a   GATT------ACAGTGTTG---TTATTCCAGTTAGAGAGAGTCCCAGACAGATTCTTA--
4494  129_HRV19    GAAG------TCACTCTTC---CAATTGAAATAAGAGATAACCCTAGACATATAAAGA--
4495  130_HRV19a   GAAG------TCACTCTTC---CAATTGAAATAAGAGATAACCCTAGACATATAAAGA--
4496  131_HRV19b   GAAG------TCACTCTTC---CAATTGAAATAAGAGATAACCCTAGACATATAAAGA--
4497  132_HRV13    GATG------TTGCAGTCT---CCATTGTACCTAGAGCAAATGTTAGGGAAATTAGAA--
4498  133_HRV13a   GATG------TTGCAGTCT---CCATTGTACCTAGAGCAAATGTTAGGGAAATTAGAA--
4499  134_HRV13b   GATG------TTGCAGTCT---CCATTGTACCTAGAGCAAATGTTAGGGAAATTAGAA--
4500  135_HRV41    GCAGA---GATTGTGGCTT---CTGTCAGACCTAGAGACAATGTTAGACAAGTAAGAA--
4501  136_HRV41a   GCAGA---GATTGTGGCTT---CTGTCAGACCTAGAGACAATGTTAGACAAGTAAGAA--
4502  137_HRV41b   GCAGA---GATTGTGGCTT---CTGTCAGACCTAGAGACAATGTTAGACAAGTAAGAA--
4503  138_HRV73    GAAG------TTACTACTG---CCATTAGGCATAGAGATAATGTTAGAGCCATCCAAA--
4504  139_HRV73b   GAAG------TTACTACTG---CCATTAGGCATAGAGATAATGTTAGAGCCATCCAAA--
4505  140_HRV73a   GAAG------TTACTACTG---CCATTAGGCATAGAGATAATGTTAGAGCCATCCAAA--
4506  141_HRV61    GAAAAACAAGTTACCACTT---TCATCAAACCTAGAGCTAACTTAAGAGAGATTAGAA--
4507  142_HRV61a   GAAAAACAAGTTACCACTT---TCATCAAACCTAGAGCTAACTTAAGAGAGATTAGAA--
4508  143_HRV61b   GAAAAACAAGTTACCACTT---TCATCAAACCTAGAGCTAACTTAAGAGAGATTAGAA--
4509  144_HRV96    -------AGGTTACCACTT---TTATCAAACCTAGAGAAAATCTAAGGGATATTAGAA--
4510  145_HRV96b   -------AGGTTACCACTT---TTATCAAACCTAGAGAAAATCTAAGGGATATTAGAA--
4511  146_HRV96a   -------AGGTTACCACTT---TTATCAAACCTAGAGAAAATCTAAGGGATATTAGAA--.
4512  90_HRV16a|   GTAC------ACAATGATGTGGCTATAAGACCTAGAACAAATCTAACAACTGTA------
4513  91_HRV16b|   GTAC------ACAATGATGTGGCTATAAGACCTAGAACAAATCTAACAACTGTC------
4514  92_1AYM_A    GTAC------ACAATGATGTGGCTATAAGACCTAGAACAAATCTAACAACTGTT------
4515  93_HRV81a|   GTCC------ACACTAGTGTAGCCATAAAACCTAGAACAAGTCTAACAAATGTG------
4516  94_HRV81b|   GTCC------ACACTAGTGTAGCCATAAAACCTAGAACAAGTCTAACAAATGTC------
4517  95_HRV81     GTCC------ACACTAGTGTAGCCATAAAACCTAGAACAAGTCTAACAAATGTT------
4518  147_HRV2     AGTA------TTCAGACAG---CAATTGTGACCAGACCAATTATCACTACAGCT------
4519  148_HRV2a|   AGTA------TTCAGACAG---CAATTGTGACCAGACCAATTATCACTACAGCA------
4520  149_HRV2b|   AGTA------TTCAGACAG---CAATTGTGACCAGACCAATTATCACTACAGCG------
4521  150_HRV49a   GACA------TTAAAACAG---GAATCACATCCAGAGCAATTATTACAACAGCG------
4522  151_HRV49b   GACA------TTAAAACAG---GAATCACATCCAGAGCAATTATTACAACAGCA------
4523  152_HRV49    GACA------TTAAAACAG---GAATCACATCCAGAGCAATTATTACAACAGCT------
4524  153_HRV23a   AATG------TCAAATCAA---GGGTTGCACATAGACCTGCAGTGATAACAGCG------
4525  154_HRV23b   AATG------TCAAATCAA---GGGTTGCACATAGACCTGCAGTGATAACAGCG------
4526  155_HRV23    AATG------TCAAATCAA---GGGTTGCACATAGACCTGCAGTGATAACAGCT------
4527  156_HRV30a   GAAG------TTAAATCAA---GGGTTGAACACAGAGCTAGGGTGACGACAGCA------
4528  157_HRV30b   GAAG------TTAAATCAA---GGGTTGAACACAGAGCTAGGGTGACGACAGCG------
4529  158_HRV30    GAAG------TTAAATCAA---GGGTTGAACACAGAGCTAGGGTGACGACAGCT------
4530  159_HRV7     GAGG------TCGCA---ACTCAAATCAAAACCAGAGCCAATCTTTTCACCCTCAAAT--
4531  160_HRV7b|   GAGG------TCGCA---ACTCAAATCAAAACCAGAGCCAATCTTTTCACCCTCAAAT--
4532  161_HRV7a|   GAGG------TCGCA---ACTCAAATCAAAACCAGAGCCAATCTTTTCACCCTCAAAT--
4533  162_HRV88    GAAG------TAGCA---ACTCAAATCAAAACCAGACGAGATGTTTACACTGTTACCA--
4534  163_HRV88a   GAAG------TAGCA---ACTCAAATCAAAACCAGACGAGATGTTTACACTGTTACCA--
4535  164_HRV88b   GAAG------TAGCA---ACTCAAATCAAAACCAGACGAGATGTTTACACTGTTACCA--
4536  165_HRV36a   GAGA------TCACA---ACCCAAATTAAAACCAGACCTAATGTCTTCACTGTA------
4537  166_HRV36b   GAGA------TCACA---ACCCAAATTAAAACCAGACCTAATGTCTTCACTGTG------
4538  167_HRV36    GAGA------TCACA---ACCCAAATTAAAACCAGACCTAATGTCTTCACTGTT------
4539  168_HRV89a   GAGG------CCACA---ACTCAGATTAAAACCAGACCTGATGTTTTACCGTTACAA--
4540  169_HRV89b   GAGG------CCACA---ACTCAGATTAAAACCAGACCTGATGTTTTACCGTTACAA--
4541  170_HRV89    GAGG------CCACA---ACTCAGATTAAAACCAGACCTGATGTTTTACCGTTACAA--
4542  171_HRV58    GAGG------TAACA---ACACAAATCAAACCCAGAACCAATGTTTTTACTATTACAT--
4543  172_HRV58a   GAGG------TAACA---ACACAAATCAAACCCAGAACCAATGTTTTTACTATTACAT--
4544  173_HRV58b   GAGG------TAACA---ACACAAATCAAACCCAGAACCAATGTTTTTACTATTACAT--
```

FIG. D5 CONT'D 01.trace                                                                                       9/20/2007 4:58 PM

```
4545  174_HRV12a    GGAG------TTCCAGACAATAGAGTCAAACTCAGAGAGACACTCACCACAGTA------
4546  175_HRV12b    GGAG------TTCCAGACAATAGAGTCAAACTCAGAGAGACACTCACCACAGTG------
4547  176_HRV12     GGAG------TTCCAGACAATAGAGTCAAACTCAGAGAGACACTCACCACAGTT------
4548  177_HRV78a    GGAA------CTCCAGACACCAAAGTGGCAATTAGAGCTAATATTAAAACTGTA------
4549  178_HRV78b    GGAA------CTCCAGACACCAAAGTGGCAATTAGAGCTAATATTAAAACTGTG------
4550  179_HRV78     GGAA------CTCCAGACACCAAAGTGGCAATTAGAGCTAATATTAAAACTGTT------
4551  180_HRV20     GAAA------TTACA---ACTCATATCAGATTCAGAAACACTGTCAAAGATCTAACATAC
4552  181_HRV20a    GAAA------TTACA---ACTCATATCAGATTCAGAAACACTGTCAAAGATCTAACATAC
4553  182_HRV20b    GAAA------TTACA---ACTCATATCAGATTCAGAAACACTGTCAAAGATCTAACATAC
4554  183_HRV68     GATA------TTAAA---ACTCATATTAAATTTAGGAATACTGTTAAAGATTTGGCATAT
4555  184_HRV68a    GATA------TTAAA---ACTCATATTAAATTTAGGAATACTGTTAAAGATTTGGCATAT
4556  185_HRV68b    GATA------TTAAA---ACTCATATTAAATTTAGGAATACTGTTAAAGATTTGGCATAT
4557  186_HRV28     GATG------TTGAG---ACTCATATTAAATTTAGAACAGATGTTAAACAGATCACAA--
4558  187_HRV28a    GATG------TTGAG---ACTCATATTAAATTTAGAACAGATGTTAAACAGATCACAA--
4559  188_HRV28b    GATG------TTGAG---ACTCATATTAAATTTAGAACAGATGTTAAACAGATCACAA--
4560  189_HRV53a    ACAG------TTGAA---ACTCACATTAAGTTCAGACCTGATGTTAAAGATGTAACAT--
4561  190_HRV53b    ACAG------TTGAA---ACTCACATTAAGTTCAGACCTGATGTTAAAGATGTAACAT--
4562  191_HRV53     ACAG------TTGAA---ACTCACATTAAGTTCAGACCTGATGTTAAAGATGTAACAT--
4563  192_HRV46a    ACTA------TACCAGATACTCATATTGGAATTAGAAGGGATATAAAGTACATTAAAA--
4564  193_HRV46b    ACTA------TACCAGATACTCATATTGGAATTAGAAGGGATATAAAGTACATTAAAA--
4565  194_HRV46     ACTA------TACCAGATACTCATATTGGAATTAGAAGGGATATAAAGTACATTAAAA--
4566  195_HRV80a    TCTA------TACCAGATACACAAATTAAAATCAGAGATAATATCAGGCAGGTTAGAA--
4567  196_HRV80b    TCTA------TACCAGATACACAAATTAAAATCAGAGATAATATCAGGCAGGTTAGAA--
4568  197_HRV80     TCTA------TACCAGATACACAAATTAAAATCAGAGATAATATCAGGCAGGTTAGAA--
4569  198_HRV51     GAAG------GCTTGAAAACTCAGATTAAAACTAGGGCAGACATCAAACTTGTGAACT--
4570  199_HRV51a    GAAG------GCTTGAAAACTCAGATTAAAACTAGGGCAGACATCAAACTTGTGAACT--
4571  200_HRV51b    GAAG------GCTTGAAAACTCAGATTAAAACTAGGGCAGACATCAAACTTGTGAACT--
4572  201_HRV65a    ACAA------ACCTAAGAACCCAAATTAAAACCAGAGATAACATTAAAATTGTAAACT--
4573  202_HRV65b    ACAA------ACCTAAGAACCCAAATTAAAACCAGAGATAACATTAAAATTGTAAACT--
4574  203_HRV65     ACAA------ACCTAAGAACCCAAATTAAAACCAGAGATAACATTAAAATTGTAAACT--
4575  204_HRV71a    AATT------CCATTAAAACCAAAATCAAATCAGAAGAGACATTAAAGAGGTCAGCA--
4576  205_HRV71b    AATT------CCATTAAAACCAAAATCAAATCAGAAGAGACATTAAAGAGGTCAGCA--
4577  206_HRV71     AATT------CCATTAAAACCAAAATCAAATCAGAAGAGACATTAAAGAGGTCAGCA--
4578  207_HRV8      GTAA------CACCAGAAACTAAGGTAAATATAGAGCTGAAGTCACAACCATT------
4579  208_HRV95     GTAA------CACCAGAAACTAAGGTCAAATATAGAGCTGAAGTCACAACCATT------
4580  209_HRV45     GAAA------CAGCC---ACAAAAGTCCAAACTAGAGCAAATGTCACAACAGTA------
4581  210_HRV45a    GAAA------CAGCC---ACAAAAGTCCAAACTAGAGCAAATGTCACAACAGTG------
4582  211_HRV45b    GAAA------CAGCC---ACAAAAGTCCAAACTAGAGCAAATGTCACAACAGTT------
4583  212_HRV6      ------------------------------------------------------------
4584  213_HRV6a|    ------------------------------------------------------------
4585  214_HRV6b|    ------------------------------------------------------------
4586  215_HRV37     ------------------------------------------------------------
4587  216_HRV37a    ------------------------------------------------------------
4588  217_HRV37b    ------------------------------------------------------------
4589  218_HRV3      ------------------------------------------------------------
4590  219_HRV3a|    ------------------------------------------------------------
4591  220_HRV3b|    ------------------------------------------------------------
4592  221_HRV14     ------------------------------------------------------------
4593  222_HRV14a    ------------------------------------------------------------
4594  223_HRV14b    ------------------------------------------------------------
4595  224_HRV72     ------------------------------------------------------------
4596  225_HRV72a    ------------------------------------------------------------
4597  226_HRV72b    ------------------------------------------------------------
4598  227_HRV83     ------------------------------------------------------------
4599  228_HRV83a    ------------------------------------------------------------
4600  229_HRV83b    ------------------------------------------------------------
4601  230_HRV92     ------------------------------------------------------------
4602  231_HRV92a    ------------------------------------------------------------
4603  232_HRV92b    ------------------------------------------------------------
4604  233_HRV79     ------------------------------------------------------------
4605  234_HRV79a    ------------------------------------------------------------
4606  235_HRV79b    ------------------------------------------------------------
4607  236_HRV35     ------------------------------------------------------------
4608  237_HRV35a    ------------------------------------------------------------
```

FIG. D5 CONT'D 01.trace                                                              9/20/2007 4:58 PM

```
4609  238_HRV35b      ------------------------------------------------
4610  239_1HRV86      ------------------------------------------------
4611  240_1HRV86      ------------------------------------------------
4612  241_1HRV86      ------------------------------------------------
4613  242_HRV70       ------------------------------------------------
4614  243_HRV70a      ------------------------------------------------
4615  244_HRV70b      ------------------------------------------------
4616  245_HRV91       ------------------------------------------------
4617  246_HRV91a      ------------------------------------------------
4618  247_HRV91b      ------------------------------------------------
4619  248_HRV17       ------------------------------------------------
4620  249_HRV17a      ------------------------------------------------
4621  250_HRV17b      ------------------------------------------------
4622  251_HRV69       ------------------------------------------------
4623  252_HRV69a      ------------------------------------------------
4624  253_HRV69b      ------------------------------------------------
4625  254_HRV48       ------------------------------------------------
4626  255_HRV48a      ------------------------------------------------
4627  256_HRV48b      ------------------------------------------------
4628  257_HRV52       ------------------------------------------------
4629  258_HRV52a      ------------------------------------------------
4630  259_HRV52b      ------------------------------------------------
4631  260_HRV4        ------------------------------------------------
4632  261_HRV4a|      ------------------------------------------------
4633  262_HRV4b|      ------------------------------------------------
4634  263_HRV99       ------------------------------------------------
4635  264_HRV99a      ------------------------------------------------
4636  265_HRV99b      ------------------------------------------------
4637  266_HRV5        ------------------------------------------------
4638  267_HRV5a|      ------------------------------------------------
4639  268_HRV5b|      ------------------------------------------------
4640  269_HRV42       ------------------------------------------------
4641  270_HRV42a      ------------------------------------------------
4642  271_HRV42b      ------------------------------------------------
4643  272_HRV26       ------------------------------------------------
4644  273_HRV26a      ------------------------------------------------
4645  274_HRV26b      ------------------------------------------------
4646  275_HRV27       ------------------------------------------------
4647  276_HRV27a      ------------------------------------------------
4648  277_HRV27b      ------------------------------------------------
4649  278_HRV93       ------------------------------------------------
4650  279_HRV93a      ------------------------------------------------
4651  280_HRV93b      ------------------------------------------------
4652  281_HRV97       ------------------------------------------------
4653  282_HRV97a      ------------------------------------------------
4654  283_HRV97b      ------------------------------------------------
4655  284_HRV84       ------------------------------------------------
4656  285_HRV84a      ------------------------------------------------
4657  286_HRV84b      ------------------------------------------------
4658  287_HRV87       ------------------------------------------------
4659  288_HRV87a      ------------------------------------------------
4660  289_HRV87b      ------------------------------------------------
4661  GROUP_1         ------------------------------------------------
4662
4663  1_HRV1A1|d      ----CA------------------
4664  2_HRV1A2|d      ----CG------------------
4665  3_HRV1A|cD      ----CT------------------
4666  4_HRV1B1|d      ----TA------------------
4667  5_HRV1B2|d      ----TC------------------
4668  6_HRV1B         ----TT------------------
4669  7_HRV40a|d      ----TA------------------
4670  8_HRV40b|d      ----TC------------------
4671  9_HRV40         ----TT------------------
4672  10_HRV85        ----CA------------------
```

FIG. D5 CONT'D

01.trace                                                          9/20/2007 4:58 PM

```
4673  11_HRV85a|    ----CG---------------
4674  12_HRV85b|    ----CT---------------
4675  13_HRV56a|    ----TA---------------
4676  14_HRV56b|    ----TG---------------
4677  15_HRV56     ----TT---------------
4678  16_HRV54     ----CT---------------
4679  17_HRV98     ----CT---------------
4680  18_HRV59a|    ----CA---------------
4681  19_HRV59b|    ----CG---------------
4682  20_HRV59     ----CT---------------
4683  21_HRV63     ----CA---------------
4684  22_HRV63b|    ----CG---------------
4685  23_HRV63a|    ----CT---------------
4686  24_HRV39     ----CT---------------
4687  25_HRV39a|    ----CA---------------
4688  26_HRV39b|    ----CT---------------
4689  27_HRV10a|    ----CA---------------
4690  28_HRV10b|    ----CC---------------
4691  29_HRV10     ----CT---------------
4692  30_HRV100a   ----CA---------------
4693  31_HRV100b   ----CG---------------
4694  32_HRV100    ----CT---------------
4695  33_HRV66     ----TA---------------
4696  34_HRV66b|    ----TG---------------
4697  35_HRV66a|    ----TC---------------
4698  36_HRV77a|    ----TG---------------
4699  37_HRV77b|    ----TA---------------
4700  38_HRV77     ----TT---------------
4701  39_HRV62a    ----CT---------------
4702  40_HRV62b    ----C----------------
4703  41_HRV25     ----CT---------------
4704  42_HRV29a    ----CT---------------
4705  43_HRV29b    ----CT---------------
4706  44_HRV44a    ----CT---------------
4707  45_HRV44b    ----CT---------------
4708  46_HRV31     ----CA---------------
4709  47_HRV31a|    ----CT---------------
4710  48_HRV31b|    ----CA---------------
4711  49_HRV47     ----CA---------------
4712  50_HRV47a|    ----CT---------------
4713  51_HRV47b|    ----CA---------------
4714  52_HRV11     ---------------------
4715  53_HRV11b|    ---------------------
4716  54_HRV11a|    ---------------------
4717  55_HRV76     ---------------------
4718  56_HRV76b|    ---------------------
4719  57_HRV76a|    ---------------------
4720  58_HRV33     ---------------------
4721  59_HRV33b|    ---------------------
4722  60_HRV33a|    ---------------------
4723  61_HRV24a|    ---------------------
4724  62_HRV24b|    ---------------------
4725  63_HRV24     ---------------------
4726  64_HRV90     ---------------------
4727  65_HRV90a|    ---------------------
4728  66_HRV90b|    ---------------------
4729  67_HRV34     ---------------------
4730  68_HRV34b|    ---------------------
4731  69_HRV34a|    ---------------------
4732  70_HRV50a|    ---------------------
4733  71_HRV50b|    ---------------------
4734  72_HRV50     ---------------------
4735  73_HRV18a|    ---------------------
4736  74_HRV18b|    ---------------------
```

FIG. D5 CONT'D

01.trace                                                                  9/20/2007 4:58 PM

```
4737  75_HRV18       --------------------
4738  76_HRV55       --------------------
4739  77_HRV55b|     --------------------
4740  78_HRV55a|     --------------------
4741  79_HRV57       ----ATGTG-----------
4742  80_HRV57a|     ----ATGTA-----------
4743  81_HRV57b|     ----ATGTC-----------
4744  82_HRV21       --------------------
4745  83_HRVHan      --------------------
4746  84_HRV43       ----CA--------------
4747  85_HRV43b|     ----CG--------------
4748  86_HRV43a|     ----CT--------------
4749  87_HRV75       ----CA--------------
4750  88_HRV75b|     ----CG--------------
4751  89_HRV75a|     ----CT--------------
4752  96_HRV9a|d     ----ATGTC-----------
4753  97_HRV9b|d     ----ATGTG-----------
4754  98_HRV9        ----ATGTA-----------
4755  99_HRV32       ----ATGTA-----------
4756  100_HRV32a     ----ATGTG-----------
4757  101_HRV32b     ----ATGTC-----------
4758  102_HRV67      ----ATGTA-----------
4759  103_HRV67a     ----ATGTC-----------
4760  104_HRV67b     ----ATGTT-----------
4761  105_HRV15      ----ATGTT-----------
4762  106_HRV15a     ----ATGTA-----------
4763  107_HRV15b     ----ATGTC-----------
4764  108_HRV74a     ----ATGTA-----------
4765  109_HRV74b     ----ATGTC-----------
4766  110_HRV74      ----ATGTT-----------
4767  111_HRV38a     ----ATGTA-----------
4768  112_HRV38b     ----ATGTC-----------
4769  113_HRV38      ----ATGTT-----------
4770  114_HRV60      ----CAGTT-----------
4771  115_HRV60a     ----CAGTA-----------
4772  116_HRV60b     ----CAGTG-----------
4773  117_HRV64a     ----CAGTG-----------
4774  118_HRV64b     ----CAGTG-----------
4775  119_HRV64      ----CAGTA-----------
4776  120_HRV94a     ----CAGTG-----------
4777  121_HRV94b     ----CAGTC-----------
4778  122_HRV94      ----CAGTA-----------
4779  123_HRV22      ----ATGTA-----------
4780  124_HRV22a     ----ATGTG-----------
4781  125_HRV22b     ----ATGTC-----------
4782  126_HRV82      ----ATGTA-----------
4783  127_HRV82b     ----ATGTT-----------
4784  128_HRV82a     ----ATGTC-----------
4785  129_HRV19      ----ATGTA-----------
4786  130_HRV19a     ----ATGTG-----------
4787  131_HRV19b     ----ATGTC-----------
4788  132_HRV13      ----ACTTT-----------
4789  133_HRV13a     ----ACTTG-----------
4790  134_HRV13b     ----ACTTA-----------
4791  135_HRV41      ----ATTAT-----------
4792  136_HRV41a     ----ATTAG-----------
4793  137_HRV41b     ----ATTAC-----------
4794  138_HRV73      ----ATTTT-----------
4795  139_HRV73b     ----ATTTG-----------
4796  140_HRV73a     ----ATTTC-----------
4797  141_HRV61      ----CATTT-----------
4798  142_HRV61a     ----CATTT-----------
4799  143_HRV61b     ----CATTT-----------
4800  144_HRV96      ----ATTTT-----------
```

FIG. D5 CONT'D 01.trace                                                                 9/20/2007 4:58 PM

```
4801 145_HRV96b    ----ATTTA------------
4802 146_HRV96a    ----ATTTC------------
4803  90_HRV16a|   ---------------------
4804  91_HRV16b|   ---------------------
4805  92_1AYM_A    ---------------------
4806  93_HRV81a|   ---------------------
4807  94_HRV81b|   ---------------------
4808  95_HRV81     ---------------------
4809 147_HRV2      ---------------------
4810 148_HRV2a|    ---------------------
4811 149_HRV2b|    ---------------------
4812 150_HRV49a    ---------------------
4813 151_HRV49b    ---------------------
4814 152_HRV49     ---------------------
4815 153_HRV23a    ---------------------
4816 154_HRV23b    ---------------------
4817 155_HRV23     ---------------------
4818 156_HRV30a    ---------------------
4819 157_HRV30b    ---------------------
4820 158_HRV30     ---------------------
4821 159_HRV7      ----CAGCT------------
4822 160_HRV7b|    ----CAGCA------------
4823 161_HRV7a|    ----CAGCG------------
4824 162_HRV88     ----CTGCT------------
4825 163_HRV88a    ----CTGCA------------
4826 164_HRV88b    ----CTGCG------------
4827 165_HRV36a    ---------------------
4828 166_HRV36b    ---------------------
4829 167_HRV36     ---------------------
4830 168_HRV89a    ----ACGTG------------
4831 169_HRV89b    ----ACGTA------------
4832 170_HRV89     ----ACGTC------------
4833 171_HRV58     ----CTGCT------------
4834 172_HRV58a    ----CTGCA------------
4835 173_HRV58b    ----CTGCC------------
4836 174_HRV12a    ---------------------
4837 175_HRV12b    ---------------------
4838 176_HRV12     ---------------------
4839 177_HRV78a    ---------------------
4840 178_HRV78b    ---------------------
4841 179_HRV78     ---------------------
4842 180_HRV20     CCCACAGAAATGACGAATGTT
4843 181_HRV20a    CCCACAGAAATGACGAATGTA
4844 182_HRV20b    CCCACAGAAATGACGAATGTG
4845 183_HRV68     CCTCCAGAATTAGCAAACCTT
4846 184_HRV68a    CCTCCAGAATTAGCAAACCTT
4847 185_HRV68b    CCTCCAGAATTAGCAAACCTT
4848 186_HRV28     ----CAGTT------------
4849 187_HRV28a    ----CAGTA------------
4850 188_HRV28b    ----CAGTC------------
4851 189_HRV53a    ----CAGTAATGACAGCT---
4852 190_HRV53b    ----CAGTAATGACAGCT---
4853 191_HRV53     ----CAGTAATGACAGCA---
4854 192_HRV46a    ----CAGCA------------
4855 193_HRV46b    ----CAGCC------------
4856 194_HRV46     ----CAGCT------------
4857 195_HRV80a    ----CAGTA------------
4858 196_HRV80b    ----CAGTC------------
4859 197_HRV80     ----CAGTT------------
4860 198_HRV51     -----TT--------------
4861 199_HRV51a    -----TA--------------
4862 200_HRV51b    -----TG--------------
4863 201_HRV65a    -----TG--------------
4864 202_HRV65b    -----TA--------------
```

FIG. D5 CONT'D

01.trace                                                                9/20/2007 4:58 PM

```
4865 203_HRV65     -----TT--------------
4866 204_HRV71a    -----ACTAA-----------
4867 205_HRV71b    -----ACTAG-----------
4868 206_HRV71     -----ACTAT-----------
4869 207_HRV8      ---------------------
4870 208_HRV95     ---------------------
4871 209_HRV45     ---------------------
4872 210_HRV45a    ---------------------
4873 211_HRV45b    ---------------------
4874 212_HRV6      ---------------------
4875 213_HRV6a|    ---------------------
4876 214_HRV6b|    ---------------------
4877 215_HRV37     ---------------------
4878 216_HRV37a    ---------------------
4879 217_HRV37b    ---------------------
4880 218_HRV3      ---------------------
4881 219_HRV3a|    ---------------------
4882 220_HRV3b|    ---------------------
4883 221_HRV14     ---------------------
4884 222_HRV14a    ---------------------
4885 223_HRV14b    ---------------------
4886 224_HRV72     ---------------------
4887 225_HRV72a    ---------------------
4888 226_HRV72b    ---------------------
4889 227_HRV83     ---------------------
4890 228_HRV83a    ---------------------
4891 229_HRV83b    ---------------------
4892 230_HRV92     ---------------------
4893 231_HRV92a    ---------------------
4894 232_HRV92b    ---------------------
4895 233_HRV79     ---------------------
4896 234_HRV79a    ---------------------
4897 235_HRV79b    ---------------------
4898 236_HRV35     ---------------------
4899 237_HRV35a    ---------------------
4900 238_HRV35b    ---------------------
4901 239_1HRV86    ---------------------
4902 240_1HRV86    ---------------------
4903 241_1HRV86    ---------------------
4904 242_HRV70     ---------------------
4905 243_HRV70a    ---------------------
4906 244_HRV70b    ---------------------
4907 245_HRV91     ---------------------
4908 246_HRV91a    ---------------------
4909 247_HRV91b    ---------------------
4910 248_HRV17     ---------------------
4911 249_HRV17a    ---------------------
4912 250_HRV17b    ---------------------
4913 251_HRV69     ---------------------
4914 252_HRV69a    ---------------------
4915 253_HRV69b    ---------------------
4916 254_HRV48     ---------------------
4917 255_HRV48a    ---------------------
4918 256_HRV48b    ---------------------
4919 257_HRV52     ---------------------
4920 258_HRV52a    ---------------------
4921 259_HRV52b    ---------------------
4922 260_HRV4      ---------------------
4923 261_HRV4a|    ---------------------
4924 262_HRV4b|    ---------------------
4925 263_HRV99     ---------------------
4926 264_HRV99a    ---------------------
4927 265_HRV99b    ---------------------
4928 266_HRV5      ---------------------
```

FIG. D5 CONT'D 01.trace                                                              9/20/2007 4:58 PM

```
4929  267_HRV5a|      --------------------
4930  268_HRV5b|      --------------------
4931  269_HRV42       --------------------
4932  270_HRV42a      --------------------
4933  271_HRV42b      --------------------
4934  272_HRV26       --------------------
4935  273_HRV26a      --------------------
4936  274_HRV26b      --------------------
4937  275_HRV27       --------------------
4938  276_HRV27a      --------------------
4939  277_HRV27b      --------------------
4940  278_HRV93       --------------------
4941  279_HRV93a      --------------------
4942  280_HRV93b      --------------------
4943  281_HRV97       --------------------
4944  282_HRV97a      --------------------
4945  283_HRV97b      --------------------
4946  284_HRV84       --------------------
4947  285_HRV84a      --------------------
4948  286_HRV84b      --------------------
4949  287_HRV87       --------------------
4950  288_HRV87a      --------------------
4951  289_HRV87b      --------------------
4952  GROUP_1         --------------------
4953
4954
4955
4956  Summary:
4957
4958  GROUP_1         ------------------------------------------------------------
4959  SUMMARY         ------------------------------------------------------------
4960
4961  GROUP_1         ------------------------------------------------------------
4962  SUMMARY         ------------------------------------------------------------
4963
4964  GROUP_1         ------------------------------------------------------------
4965  SUMMARY         ------------------------------------------------------------
4966
4967  GROUP_1         ------------------------------------------------------------
4968  SUMMARY         ------------------------------------------------------------
4969
4970  GROUP_1         ------------------------------------------------------------
4971  SUMMARY         ------------------------------------------------------------
4972
4973  GROUP_1         ------------------------------------------------------------
4974  SUMMARY         ------------------------------------------------------------
4975
4976  GROUP_1         ------------------------------------------------------------
4977  SUMMARY         ------------------------------------------------------------
4978
4979  GROUP_1         ------------------------------------------------------------
4980  SUMMARY         ------------------------------------------------------------
4981
4982  GROUP_1         ------------------------------------------------------------
4983  SUMMARY         ------------------------------------------------------------
4984
4985  GROUP_1         ------------------------------------------------------------
4986  SUMMARY         ------------------------------------------------------------
4987
4988  GROUP_1         ------------------------------------------------------------
4989  SUMMARY         ------------------------------------------------------------
4990
4991  GROUP_1         ------------------------------------------------------------
4992  SUMMARY         ------------------------------------------------------------
```

FIG. D5 CONT'D

01.trace                                                                9/20/2007 4:58 PM
```
4993
4994 GROUP_1      ----------------------------------------------------------------
4995 SUMMARY      ----------------------------------------------------------------
4996
4997 GROUP_1      ----------------------------------------------------------------
4998 SUMMARY      ----------------------------------------------------------------
4999
5000 GROUP_1      ----------------------------------------------------------------
5001 SUMMARY      ----------------------------------------------------------------
5002
5003 GROUP_1      ---------------------
5004 SUMMARY      ---------------------
5005
5006
```

FIG. D5 CONT'D

```
02.trace                                                                    9/20/2007 4:59 PM 1  Group 1:  1_HRV1A1|d
    2  Group 1:  2_HRV1A2|d
    3  Group 1:  3_HRV1A|cD
    4  Group 1:  4_HRV1B1|d
    5  Group 1:  5_HRV1B2|d
    6  Group 1:  6_HRV1B
    7  Group 1:  7_HRV40a|d
    8  Group 1:  8_HRV40b|d
    9  Group 1:  9_HRV40
   10  Group 1:  10_HRV85
   11  Group 1:  11_HRV85a|
   12  Group 1:  12_HRV85b|
   13  Group 1:  13_HRV56a|
   14  Group 1:  14_HRV56b|
   15  Group 1:  15_HRV56
   16  Group 1:  16_HRV54
   17  Group 1:  17_HRV98
   18  Group 1:  18_HRV59a|
   19  Group 1:  19_HRV59b|
   20  Group 1:  20_HRV59
   21  Group 1:  21_HRV63
   22  Group 1:  22_HRV63b|
   23  Group 1:  23_HRV63a|
   24  Group 1:  24_HRV39
   25  Group 1:  25_HRV39a|
   26  Group 1:  26_HRV39b|
   27  Group 1:  27_HRV10a|
   28  Group 1:  28_HRV10b|
   29  Group 1:  29_HRV10
   30  Group 1:  30_HRV100a
   31  Group 1:  31_HRV100b
   32  Group 1:  32_HRV100
   33  Group 1:  33_HRV66
   34  Group 1:  34_HRV66b|
   35  Group 1:  35_HRV66a|
   36  Group 1:  36_HRV77a|
   37  Group 1:  37_HRV77b|
   38  Group 1:  38_HRV77
   39  Group 1:  39_HRV62a
   40  Group 1:  40_HRV62b
   41  Group 1:  41_HRV25
   42  Group 1:  42_HRV29a
   43  Group 1:  43_HRV29b
   44  Group 1:  44_HRV44a
   45  Group 1:  45_HRV44b
   46  Group 1:  46_HRV31
   47  Group 1:  47_HRV31a|
   48  Group 1:  48_HRV31b|
   49  Group 1:  49_HRV47
   50  Group 1:  50_HRV47a|
   51  Group 1:  51_HRV47b|
   52  Group 1:  52_HRV11
   53  Group 1:  53_HRV11b|
   54  Group 1:  54_HRV11a|
   55  Group 1:  55_HRV76
   56  Group 1:  56_HRV76b|
   57  Group 1:  57_HRV76a|
   58  Group 1:  58_HRV33
   59  Group 1:  59_HRV33b|
   60  Group 1:  60_HRV33a|
   61  Group 1:  61_HRV24a|
   62  Group 1:  62_HRV24b|
   63  Group 1:  63_HRV24
   64  Group 1:  64_HRV90
   65  Group 1:  65_HRV90a|
```

FIG. D6

02.trace                                                              9/20/2007 4:59 PM

```
 66 Group 1:  66_HRV90b|
 67 Group 1:  67_HRV34
 68 Group 1:  68_HRV34b|
 69 Group 1:  69_HRV34a|
 70 Group 1:  70_HRV50a|
 71 Group 1:  71_HRV50b|
 72 Group 1:  72_HRV50
 73 Group 1:  73_HRV18a|
 74 Group 1:  74_HRV18b|
 75 Group 1:  75_HRV18
 76 Group 1:  76_HRV55
 77 Group 1:  77_HRV55b|
 78 Group 1:  78_HRV55a|
 79 Group 1:  79_HRV57
 80 Group 1:  80_HRV57a|
 81 Group 1:  81_HRV57b|
 82 Group 1:  82_HRV21
 83 Group 1:  83_HRVHan
 84 Group 1:  84_HRV43
 85 Group 1:  85_HRV43b|
 86 Group 1:  86_HRV43a|
 87 Group 1:  87_HRV75
 88 Group 1:  88_HRV75b|
 89 Group 1:  89_HRV75a|
 90 Group 1:  96_HRV9a|d
 91 Group 1:  97_HRV9b|d
 92 Group 1:  98_HRV9
 93 Group 1:  99_HRV32
 94 Group 1: 100_HRV32a
 95 Group 1: 101_HRV32b
 96 Group 1: 102_HRV67
 97 Group 1: 103_HRV67a
 98 Group 1: 104_HRV67b
 99 Group 1: 105_HRV15
100 Group 1: 106_HRV15a
101 Group 1: 107_HRV15b
102 Group 1: 108_HRV74a
103 Group 1: 109_HRV74b
104 Group 1: 110_HRV74
105 Group 1: 111_HRV38a
106 Group 1: 112_HRV38b
107 Group 1: 113_HRV38
108 Group 1: 114_HRV60
109 Group 1: 115_HRV60a
110 Group 1: 116_HRV60b
111 Group 1: 117_HRV64a
112 Group 1: 118_HRV64b
113 Group 1: 119_HRV64
114 Group 1: 120_HRV94a
115 Group 1: 121_HRV94b
116 Group 1: 122_HRV94
117 Group 1: 123_HRV22
118 Group 1: 124_HRV22a
119 Group 1: 125_HRV22b
120 Group 1: 126_HRV82
121 Group 1: 127_HRV82b
122 Group 1: 128_HRV82a
123 Group 1: 129_HRV19
124 Group 1: 130_HRV19a
125 Group 1: 131_HRV19b
126 Group 1: 132_HRV13
127 Group 1: 133_HRV13a
128 Group 1: 134_HRV13b
129 Group 1: 135_HRV41
130 Group 1: 136_HRV41a
```

FIG. D6 CONT'D

```
02.trace                                                    9/20/2007 4:59 PM
    131 Group 1: 137_HRV41b
    132 Group 1: 138_HRV73
    133 Group 1: 139_HRV73b
    134 Group 1: 140_HRV73a
    135 Group 1: 141_HRV61
    136 Group 1: 142_HRV61a
    137 Group 1: 143_HRV61b
    138 Group 1: 144_HRV96
    139 Group 1: 145_HRV96b
    140 Group 1: 146_HRV96a
    141 Group 1: 90_HRV16a|
    142 Group 1: 91_HRV16b|
    143 Group 1: 92_1AYM_A
    144 Group 1: 93_HRV81a|
    145 Group 1: 94_HRV81b|
    146 Group 1: 95_HRV81
    147 Group 1: 147_HRV2
    148 Group 1: 148_HRV2a|
    149 Group 1: 149_HRV2b|
    150 Group 1: 150_HRV49a
    151 Group 1: 151_HRV49b
    152 Group 1: 152_HRV49
    153 Group 1: 153_HRV23a
    154 Group 1: 154_HRV23b
    155 Group 1: 155_HRV23
    156 Group 1: 156_HRV30a
    157 Group 1: 157_HRV30b
    158 Group 1: 158_HRV30
    159 Group 1: 159_HRV7
    160 Group 1: 160_HRV7b|
    161 Group 1: 161_HRV7a|
    162 Group 1: 162_HRV88
    163 Group 1: 163_HRV88a
    164 Group 1: 164_HRV88b
    165 Group 1: 165_HRV36a
    166 Group 1: 166_HRV36b
    167 Group 1: 167_HRV36
    168 Group 1: 168_HRV89a
    169 Group 1: 169_HRV89b
    170 Group 1: 170_HRV89
    171 Group 1: 171_HRV58
    172 Group 1: 172_HRV58a
    173 Group 1: 173_HRV58b
    174 Group 1: 174_HRV12a
    175 Group 1: 175_HRV12b
    176 Group 1: 176_HRV12
    177 Group 1: 177_HRV78a
    178 Group 1: 178_HRV78b
    179 Group 1: 179_HRV78
    180 Group 1: 180_HRV20
    181 Group 1: 181_HRV20a
    182 Group 1: 182_HRV20b
    183 Group 1: 183_HRV68
    184 Group 1: 184_HRV68a
    185 Group 1: 185_HRV68b
    186 Group 1: 186_HRV28
    187 Group 1: 187_HRV28a
    188 Group 1: 188_HRV28b
    189 Group 1: 189_HRV53a
    190 Group 1: 190_HRV53b
    191 Group 1: 191_HRV53
    192 Group 1: 192_HRV46a
    193 Group 1: 193_HRV46b
    194 Group 1: 194_HRV46
    195 Group 1: 195_HRV80a
```

FIG. D6 CONT'D

```
02.trace                                                                                    9/20/2007 4:59 PM 196  Group 1: 196_HRV80b
197  Group 1: 197_HRV80
198  Group 1: 198_HRV51
199  Group 1: 199_HRV51a
200  Group 1: 200_HRV51b
201  Group 1: 201_HRV65a
202  Group 1: 202_HRV65b
203  Group 1: 203_HRV65
204  Group 1: 204_HRV71a
205  Group 1: 205_HRV71b
206  Group 1: 206_HRV71
207  Group 1: 207_HRV8
208  Group 1: 208_HRV95
209  Group 1: 209_HRV45
210  Group 1: 210_HRV45a
211  Group 1: 211_HRV45b
212
213
214  >>>>
215
216
217
218  Group 1:
219
220   1_HRV1A1|d    AATCCAGTAGAAAACTACATTGATGAAGTTTTAAATGAAGTTTTAGTAGTGCCGAATATA
221   2_HRV1A2|d    AATCCAGTAGAAAACTACATTGATGAAGTTTTAAATGAAGTTTTAGTAGTGCCGAATATA
222   3_HRV1A|cD    AATCCAGTAGAAAACTACATTGATGAAGTTTTAAATGAAGTTTTAGTAGTGCCGAATATA
223   4_HRV1B1|d    AATCCAGTGGAAAATTACATTGATGAAGTTTTAAATGAAGTTCTAGTAGTACCAAATATA
224   5_HRV1B2|d    AATCCAGTGGAAAATTACATTGATGAAGTTTTAAATGAAGTTCTAGTAGTACCAAATATA
225   6_HRV1B       AATCCAGTGGAAAATTACATTGATGAAGTTTTAAATGAAGTTCTAGTAGTACCAAATATA
226   7_HRV40a|d    AACCCCGTTGAAAGGTATGTTGATGAGGTTCTTAATGAAGTTCTGGTAGTTCCAAATATC
227   8_HRV40b|d    AACCCCGTTGAAAGGTATGTTGATGATGTTCTTAATGAAGTTCTGGTAGTTCCAAATATC
228   9_HRV40       AACCCCGTTGAAAGGTATGTTGATGAGGTTCTTAATGAAGTTCTGGTAGTTCCAAATATC
229  10_HRV85       AATCCTGTTGAAAAATACGTTGATGAAGTCCTTAATGAGGTTCTAGTGGTTCCAAATATC
230  11_HRV85a|     AATCCTGTTGAAAAATACGTTGATGAAGTCCTTAATGAGGTTCTAGTGGTTCCAAATATC
231  12_HRV85b|     AATCCTGTTGAAAAATACGTTGATGAAGTCCTTAATGAGGTTCTAGTGGTTCCAAATATC
232  13_HRV56a|     AACCCAGTTGAGAGATATGTAGATGATGTTTTAAATGAAGTTTTAGTTGTTCCAAATATT
233  14_HRV56b|     AACCCAGTTGAGAGATATGTAGATGATGTTTTAAATGAAGTTTTAGTTGTTCCAAATATT
234  15_HRV56       AACCCAGTTGAGAGATATGTAGATGATGTTTTAAATGAAGTTTTAGTTGTTCCAAATATT
235  16_HRV54       AATCCTGTAGAAAGATATGTTGATCAAGTGTTAAATGAAGTGTTAGTTGTCCCAAACATT
236  17_HRV98       AATCCTGTAGAGAGATATGTTGATGAAGTATTAAATGAAGTGTTAGTTGTTCCAAACATT
237  18_HRV59a|     AACCCAGTGGAAAACTATGTTAATGATGTACTTAATGAGGTTTTAGTAGTACCAAATATA
238  19_HRV59b|     AACCCAGTGGAAAACTATGTTAATGATGTACTTAATGAGGTTTTAGTAGTACCAAATATA
239  20_HRV59       AACCCAGTGGAAAACTATGTTAATGATGTACTTAATGAGGTTTTAGTAGTACCAAATATA
240  21_HRV63       AATCCAGTAGAGAATTATGTAAATGATGTTCTTAATGAAGTGTTAGTTGTTCCAAACATA
241  22_HRV63b|     AATCCAGTAGAGAATTATGTAAATGATGTTCTTAATGAAGTGTTAGTTGTTCCAAACATA
242  23_HRV63a|     AATCCAGTAGAGAATTATGTAAATGATGTTCTTAATGAAGTGTTAGTTGTTCCAAACATA
243  24_HRV39       AATCCAGTAGAAAATTATATAGATGAAGTATTAAATGAGGTATTAGTTGTTCCTAATATA
244  25_HRV39a|     AATCCAGTAGAAAATTATATAGATGAAGTATTAAATGAGGTATTAGTTGTTCCTAATATA
245  26_HRV39b|     AATCCAGTAGAAAATTATATAGATGGAGTATTAAATGAGGTATTAGTTGTTCCTAATATA
246  27_HRV10a|     AATCCAGTTGAAAATTACATTGATAATGTACTTAATGAAGTCCTAGTGGTACCCAACATC
247  28_HRV10b|     AATCCAGTTGAAAATTACATTGATAATGTACTTAATGAAGTCCTAGTGGTACCCAACATC
248  29_HRV10       AATCCAGTTGAAAATTACATTGATAATGTACTTAATGAAGTCCTAGTGGTACCCAACATC
249  30_HRV100a     AATCCAGTAGAAAATTATGTTGAAGGTGTGCTGAATGAAGTACTAGTGGTACCTAATATT
250  31_HRV100b     AATCCAGTAGAAAATTATGTTGAAGGTGTGCTGAATGAAGTACTAGTGGTACCTAATATT
251  32_HRV100      AATCCAGTAGAAAATTATGTTGAAGGTGTGCTGAATGAAGTACTAGTGGTACCTAATATT
252  33_HRV66       AATCCAGTTGAAGATTATGTTGAGGGTGTTTTAAATGAAGTTTTAGTAGTACCAAACATC
253  34_HRV66b|     AATCCAGTTGAAGATTATGTTGAGGGTGTTTTAAATGAAGTTTTAGTAGTACCAAACATC
254  35_HRV66a|     AATCCAGTTGAAGATTATGTTGAGGGTGTTTTAAATGAAGTTTTAGTAGTACCAAACATC
255  36_HRV77a|     AATCCAGTTGAGGACTATATCGATAATGTACTTAATGAAGTCTTAGTAGTACCAAATACC
256  37_HRV77b|     AATCCAGTTGAGGACTATATCGATAATGTACTTAATGAAGTCTTAGTAGTACCAAATACC
257  38_HRV77       AATCCAGTTGAGGACTATATCGATAATGTACTTAATGAAGTCTTAGTAGTACCAAATACC
258  39_HRV62a      AATCCAATTGAAAATTATGTAGATCAAGTACTTAATGAAGTTTTAGTTGTACCAAATATT
259  40_HRV62b      AATCCAATTGAAAATTATGTAGATCAAGTACTTAATGAAGTTTTAGTTGTACCAAATATT
260  41_HRV25       AATCCAATTGAAAATTATGTAGATCAAGTACTTAATGAGGTTCTAGTCGTACCAAATATT
```

FIG. D6 CONT'D

```
02.trace                                                                         9/20/2007 4:59 PM 261  42_HRV29a     AACCCAGTTGAAAACTATGTGGATGAGGTGCTTAATGAAGTTTTAGTTGTGCCTAACATC
262  43_HRV29b     AACCCAGTTGAAAACTATGTGGATGAGGTGCTTAATGAAGTTTTAGTTGTGCCTAACATC
263  44_HRV44a     AACCCAGTTGAAAATTATGTGGATGAAGTACTTAATGAAGTCTTAGTTGTGCCTAATATC
264  45_HRV44b     AACCCAGTTGAAAATTATGTGGATGAAGTACTTAATGAAGTCTTAGTTGTGCCTAATATC
265  46_HRV31      AATCCAGTTGAAAACTATGTGGAAGAGGTTCTTAATGAAGTCTTAGTAGTACCTAATATC
266  47_HRV31a|    AATCCAGTTGAAAACTATGTGGAAGAGGTTCTTAATGAAGTCTTAGTAGTACCTAATATC
267  48_HRV31b|    AATCCAGTTGAAAACTATGTGGAAGAGGTTCTTAATGAAGTCTTAGTAGTACCTAATATC
268  49_HRV47      AACCCAGTCGAAAATTATGTGGAAGAGGTACTTAATGAGGTCTTAGTTGTACCAAATATC
269  50_HRV47a|    AACCCAGTCGAAAATTATGTGGAAGAGGTACTTAATGAGGTCTTAGTTGTACCAAATATC
270  51_HRV47b|    AACCCAGTCGAAAATTATGTGGAAGAGGTACTTAATGAGGTCTTAGTTGTACCAAATATC
271  52_HRV11      AACCCAGTGGAGGATTATGTTGATGGAATTCTAAATGAGGTTTTAGTTGTACCTAATATA
272  53_HRV11b|    AACCCAGTGGAGGATTATGTTGATGAATTCTAAATGAGGTTTTAGTTGTACCTAATATA
273  54_HRV11a|    AACCCAGTGGAGGATTATGTTGATGGAATTCTAAATGAGGTTTTAGTTGTACCTAATATA
274  55_HRV76      AACCCAGTTGAAAATTACGTGGATGAGATATTAAATGAGGTTCTTGTAGTACCAAACATC
275  56_HRV76b|    AACCCAGTTGAAAATTACGTGGATGAGATATTAAATGAGGTTCTTGTAGTACCAAACATC
276  57_HRV76a|    AACCCAGTTGAAAATTACGTGGATGAGATATTAAATGAGGTTCTTGTAGTACCAAACATC
277  58_HRV33      AATCCAGTAGAGAATTATATAGAAGAGGTGTTGAATGAGGTTTTAGTAGTGCCTAATATC
278  59_HRV33b|    AATCCAGTAGAGAATTATATAGAAGAGGTGTTGAATGAGGTTTTAGTAGTGCCTAATATC
279  60_HRV33a|    AATCCAGTAGAGAATTATATAGAAGAGGTGTTGAATGAGGTTTTAGTAGTGCCTAATATC
280  61_HRV24a|    AACCCAGTAGAAAATTATATAGATGAGGTTTGAATGAAGTACTGGTTGTGCCTAATATT
281  62_HRV24b|    AACCCAGTAGAAAATTATATAGATGAGGTTTTGAATGAAGTACTGGTTGTGCCTAATATT
282  63_HRV24      AACCCAGTAGAAAATTATATAGATGAGGTTTTGAATGAAGTACTGGTTGTGCCTAATATT
283  64_HRV90      AATCCAGTGGAAAATTATATAGATGAAGTCCTAAATGAGGTATTGGTTGTCCCTAATATT
284  65_HRV90a|    AATCCAGTGGAAAATTATATAGATGAAGTCCTAAATGAGGTATTGGTTGTCCCTAATATT
285  66_HRV90b|    AATCCAGTGGAAAATTATATAGATGAAGTCCTAAATGAGGTATTGGTTGTCCCTAATATT
286  67_HRV34      AATCCAGTTGAAAATTACATAGATGAGGTACTAAATGAGGTATTGGTTGTACCAAACATT
287  68_HRV34b|    AATCCAGTTGAAAATTACATAGATGAGGTACTAAATGAGGTATTGGTTGTACCAAACATT
288  69_HRV34a|    AATCCAGTTGAAAATTACATAGATGAGGTACTAAATGAGGTATTGGTTGTACCAAACATT
289  70_HRV50a|    AATCCAGTGGAGAATTACATAGATGAAGTATTAAATGAGGTATTAGTTGTCCCAAATATC
290  71_HRV50b|    AATCCAGTGGAGAATTACATAGATGAAGTATTAAATGAGGTATTAGTTGTCCCAAATATC
291  72_HRV50      AATCCAGTGGAGAATTACATAGATGAAGTATTAAATGAGGTATTAGTTGTCCCAAATATC
292  73_HRV18a|    AATCCAGTAGAGAATTATATAGATGAAGTACTTAATGAAGTGTTAGTGGTCCCAAATGTG
293  74_HRV18b|    AATCCAGTAGAGAATTATATAGATGAAGTACTTAATGAAGTGTTAGTGGTCCCAAATGTG
294  75_HRV18      AATCCAGTAGAGAATTATATAGATGAAGTACTTAATGAAGTGTTAGTGGTCCCAAATGTG
295  76_HRV55      AATCCTGTAGAGAGATATGTTGATGAAGTCCTGAATGAAGTGCTAGTAGTTCCAAATATT
296  77_HRV55b|    AATCCTGTAGAGAGATATGTTGATGAAGTCCTGAATGAAGTGCTAGTAGTTCCAAATATT
297  78_HRV55a|    AATCCTGTAGAGAGATATGTTGATGAAGTCCTGAATGAAGTGCTAGTAGTTCCAAATATT
298  79_HRV57      AACCCAGTAGAAAATTTTGTGGATGAGATCTTGAATGAAGTTTTGGTGGTTCCAGATATC
299  80_HRV57a|    AACCCAGTAGAAAATTTTGTGGATGAGATCTTGAATGAAGTTTTGGTGGTTCCAGATATC
300  81_HRV57b|    AACCCAGTAGAAAATTTTGTGGATGAGATCTTGAATGAAGTTTTGGTGGTTCCAGATATC
301  82_HRV21      AATCCTGTAGAGAATTATATAGATGAAGTCCTAAATGAAGTCTTAGTAGTGCCAAATATC
302  83_HRVHan     AATCCTGTAGAGAATTACGTAGATGAAGTTCTAAATGAGGTCTTAGTAGTGCCAAATATC
303  84_HRV43      AATCCTGTTGAAAATTATGTTGATGAAATTTAAATGAGGTTCTTGTAGTCCCAAACACT
304  85_HRV43b|    AATCCTGTTGAAAATTATGTTGATGAAATTTTAAATCAAGTTCTTGTAGTCCCAAACACT
305  86_HRV43a|    AATCCTGTTGAAAATTATGTTGATGAAATTTTAAATCAAGTTCTTGTAGTCCCAAACACT
306  87_HRV75      AATCCAGTTGAAAATTATGTGGATGAAATTTTAAACCAAGTTCTGGTAGTTCCAAACACC
307  88_HRV75b|    AATCCAGTTGAAAATTATGTGGATGAAATTTTAAACCAAGTTCTGGTAGTTCCAAACACC
308  89_HRV75a|    AATCCAGTTGAAAATTATGTGGATGAAATTTTAAACCAAGTTCTGGTAGTTCCAAACACC
309  96_HRV9a|d    AATCCAGTGGAGAATTACATAGATCAGGTGCTTAATGAGGTTTGGTAGTCCCAAACATT
310  97_HRV9b|d    AATCCAGTGGAGAATTACATAGATCAGGTGCTTAATGAGGTTTTGGTAGTCCCAAACATT
311  98_HRV9       AATCCAGTGGAGAATTACATAGATCAGGTGCTTAATGAGGTTTTGGTAGTCCCAAACATT
312  99_HRV32      AATCCTGTGGAGAATTACATAGATCAAGTTTTAAATGAAGTTTTGGTAGTTCCAAACATC
313  100_HRV32a    AATCCTGTGGAGAATTACATAGATCAAGTTTTAAATGAAGTTTTGGTAGTTCCAAACATC
314  101_HRV32b    AATCCTGTGGAGAATTACATAGATCAAGTTTTAAATGAAGTTTTGGTAGTTCCAAACATC
315  102_HRV67     AACCCAGTAGAAGATTATGTAGATCAGGTATTGAATGAGGTCCTGGTGGTGCCAAATATA
316  103_HRV67a    AACCCAGTAGAAGATTATGTAGATCAGGTATTGAATGAGGTCCTGGTGGTGCCAAATATA
317  104_HRV67b    AACCCAGTAGAAGATTATGTAGATCAGGTATTGAATGAGGTCCTGGTGGTGCCAAATATA
318  105_HRV15     AACCCAGTGGAGAATTACATAGATGAAGTGTAAATGAGGTTCTAGTAGTTCCAAACATT
319  106_HRV15a    AACCCAGTGGAGAATTACATAGATGAAGTGTAAATGAGGTTCTAGTAGTTCCAAACATT
320  107_HRV15b    AACCCAGTGGAGAATTACATAGATGAAGTGTAAATGAGGTTCTAGTAGTTCCAAACATT
321  108_HRV74a    AACCCAGTGGAGAATTACATAGATGAAGTGTTGAATGAAGTGTTAGTTGTTCCAAATATT
322  109_HRV74b    AACCCAGTGGAGAATTACATAGATGAAGTGTTGAATGAAGTGTTAGTTGTTCCAAATATT
323  110_HRV74     AACCCAGTGGAGAATTACATAGATGAAGTGTTGAATGAAGTGTTAGTTGTTCCAAATATT
324  111_HRV38a    AACCCAGTAGAGGAATACATAGATGGAGTCTTGAATGAGGTTCTTGTGGTTCCGAACATT
325  112_HRV38b    AACCCAGTAGAGGAATACATAGATGGAGTCTTGAATGAGGTTCTTGTGGTTCCGAACATT
```

FIG. D6 CONT'D

02.trace                                                        9/20/2007 4:59 PM

```
326 113_HRV38    AACCCAGTAGAGGAATACATAGATGGAGTCTTGAATGAGGTTCTTGTGGTTCCGAACATT
327 114_HRV60    AATCCAGTAGAAAGCTACATAGATGGGGTCTTAAACGAAGTCCTTGTGGTTCCAAACATT
328 115_HRV60a   AATCCAGTAGAAAGCTACATAGATGGGGTCTTAAACGAAGTCCTTGTGGTTCCAAACATT
329 116_HRV60b   AATCCAGTAGAAAGCTACATAGATGGGGTCTTAAACGAAGTCCTTGTGGTTCCAAACATT
330 117_HRV64a   AACCCAGTTGAACAATACATTGATGGTGTGTTGAATGAAGTTTTGATTGTCCCAAACATC
331 118_HRV64b   AACCCAGTTGAACAATACATTGATGGTGTGTTGAATGAAGTTTTGATTGTCCCAAACATC
332 119_HRV64    AACCCAGTTGAACAATACATTGATGGTGTGTTGAATGAAGTTTTGATTGTCCCAAACATC
333 120_HRV94a   AATCCAGTTGAGAAATACATTGATGGTGTATTGAATGAAGTTTTAGTTGTTCCAAATATC
334 121_HRV94b   AATCCAGTTGAGAAATACATTGATGGTGTATTGAATGAAGTTTTAGTTGTTCCAAATATC
335 122_HRV94    AATCCAGTTGAGAAATACATTGATGGTGTATTGAATGAAGTTTTAGTTGTTCCAAATATC
336 123_HRV22    AACCCTGTAGAGAAATACATTGATGGTGTATTGAATGAAGTATTGGTTGTTCCAAACACA
337 124_HRV22a   AACCCTGTAGAGAAATACATTGATGGTGTATTGAATGAAGTATTGGTTGTTCCAAACACA
338 125_HRV22b   AACCCTGTAGAGAAATACATTGATGGTGTATTGAATGAAGTATTGGTTGTTCCAAACACA
339 126_HRV82    AATCCAGTTGAAAGTATGTTGATAGTGTTTAAACGAGGTATTAGTTGTTCCTAACATT
340 127_HRV82b   AATCCAGTTGAAAGTATGTTGATAGTGTTTAAACGAGGTATTAGTTGTTCCTAACATT
341 128_HRV82a   AATCCAGTTGAAAGTATGTTGATAGTGTTTTAAACGAGGTATTAGTTGTTCCTAACATT
342 129_HRV19    AATCCTGTAGAGAAATATGTGGACACCATTCTGAATGAGGTGCTAGTTGTCCCAAATATC
343 130_HRV19a   AATCCTGTAGAGAAATATGTGGACACCATTCTGAATGAGGTGCTAGTTGTCCCAAATATC
344 131_HRV19b   AATCCTGTAGAGAAATATGTGGACACCATTCTGAATGAGGTGCTAGTTGTCCCAAATATC
345 132_HRV13    AATCCTGTTGAAAGGTATGTAGATGAAGTCTTGAATGAAGTTCTTGTAGTACCAAATATC
346 133_HRV13a   AATCCTGTTGAAAGGTATGTAGATGAAGTCTTGAATGAAGTTCTTGTAGTACCAAATATC
347 134_HRV13b   AATCCTGTTGAAAGGTATGTAGATGAAGTCTTGAATGAAGTTCTTGTAGTACCAAATATC
348 135_HRV41    AATCCTGTAGAAAGGTATGTGGATGAGGTCCTGAATGAGGTTCTTGTGGTACCAAATATT
349 136_HRV41a   AATCCTGTAGAAAGGTATGTGGATGAGGTCCTGAATGAGGTTCTTGTGGTACCAAATATT
350 137_HRV41b   AATCCTGTAGAAAGGTATGTGGATGAGGTCCTGAATGAGGTTCTTGTGGTACCAAATATT
351 138_HRV73    AATCCTGTAGAAAGATATGTAGATGAAGTTTTGAATGAAGTCCTTGTAGTACCCAATATC
352 139_HRV73b   AATCCTGTAGAAAGATATGTAGATGAAGTTTTGAATGAAGTCCTTGTAGTACCCAATATC
353 140_HRV73a   AATCCTGTAGAAAGATATGTAGATGAAGTTTTGAATGAAGTCCTTGTAGTACCCAATATC
354 141_HRV61    AACCCTGTGGAAAGATATGTAGATGAAGTTTTAAATGAAGTGCTTGTAGTCCCAAACATT
355 142_HRV61a   AACCCTGTGGAAAGATATGTAGATGAAGTTTTAAATGAAGTGCTTGTAGTCCCAAACATT
356 143_HRV61b   AACCCTGTGGAAAGATATGTAGATGAAGTTTTAAATGAAGTGCTTGTAGTCCCAAACATT
357 144_HRV96    AACCCTGTAGAGAGATATGTAGATGAAGTCTTGAATGAGGTTCTTGTAGTCCCTAATATT
358 145_HRV96b   AACCCTGTAGAGAGATATGTAGATGAAGTCTTGAATGAGGTTCTTGTAGTCCCTAATATT
359 146_HRV96a   AACCCTGTAGAGAGATATGTAGATGAAGTCTTGAATGAGGTTCTTGTAGTCCCTAATATT
360  90_HRV16a|  AATCCAGTGGAAAGATATGTAGATGAAGTCTTAAATGAAGTGTTAGTAGTGCCCAATATT
361  91_HRV16b|  AATCCAGTGGAAAGATATGTAGATGAAGTCTTAAATGAAGTGTTAGTAGTGCCCAATATT
362  92_1AYM_A   AATCCAGTGGAAAGATATGTAGATGAAGTCTTAAATGAAGTGTTAGTAGTGCCCAATATT
363  93_HRV81a|  AACCCAGTGGAGCGGTATGTAGATGAAGTCTTAAATGAGGTATTGGTAGTCCCTAATATT
364  94_HRV81b|  AACCCAGTGGAGCGGTATGTGGATGAAGTCTTAAATGAGGTATTGGTAGTCCCTAATATT
365  95_HRV81    AACCCAGTGGAGCGGTATGTGGATGAAGTCTTAAATGAGGTATTGGTAGTCCCTAATATT
366 147_HRV2     AACCCTGTTGAGAATTATATAGATGAAGTTCTTAATGAAGTTTTAGTTGTCCCAAATATT
367 148_HRV2a|   AACCCTGTTGAGAATTATATAGATGAAGTTCTTAATGAAGTTTTAGTTGTCCCAAATATT
368 149_HRV2b|   AACCCTGTTGAGAATTATATAGATGAAGTTCTTAATGAAGTTTTAGTTGTCCCAAATATT
369 150_HRV49a   AATCCTGTTGAACACTACATAGATGAGGTCCTTAATGAGGTTTTAGTTGTTCCAAATATT
370 151_HRV49b   AATCCTGTTGAACACTACATAGATGAGGTCCTTAATGAGGTTTTAGTTGTTCCAAATATT
371 152_HRV49    AATCCTGTTGAACACTACATAGATGAGGTCCTTAATGAGGTTTTAGTTGTTCCAAATATT
372 153_HRV23a   AATCCAATTGAGAACTATGTAGATGAAGTTCTTAATGAAGTCTTAGTTGTTCCCAATATC
373 154_HRV23b   AATCCAATTGAGAACTATGTAGATGAAGTTCTTAATGAAGTCTTAGTTGTTCCCAATATC
374 155_HRV23    AATCCAATTGAGAACTATGTAGATGAAGTTCTTAATGAAGTCTTAGTTGTTCCCAATATC
375 156_HRV30a   AACCCGGTTGAAAATTTTGTAGATGAAGTTCTTAGTGAAGTTTTAGTTGTTCCAAACATT
376 157_HRV30b   AACCCGGTTGAAAATTTTGTAGATGAAGTTCTTAGTGAAGTTTTAGTTGTTCCAAACATT
377 158_HRV30    AACCCGGTTGAAAATTTTGTAGATGAAGTTCTTAGTGAAGTTTTAGTTGTTCCAAACATT
378 159_HRV7     AACCCGGTAGAGAATTATGTAGATAGCTTACTAAATGAAGTATTAGTGGTACCTAATATT
379 160_HRV7b|   AACCCGGTAGAGAATTATGTAGATAGCTTACTAAATGAAGTATTAGTGGTACCTAATATT
380 161_HRV7a|   AACCCGGTAGAGAATTATGTAGATAGCTTACTAAATGAAGTATTAGTGGTACCTAATATT
381 162_HRV88    AATCCAGTAGAAAACTATGTAGATAACTTGTTAAACGAAGTGCTAGTAGTTCCTAACATT
382 163_HRV88a   AATCCAGTAGAAAACTATGTAGATAACTTGTTAAACGAAGTGCTAGTAGTTCCTAACATT
383 164_HRV88b   AATCCAGTAGAAAACTATGTAGATAACTTGTTAAACGAAGTGCTAGTAGTTCCTAACATT
384 165_HRV36a   AATCCAGTTGAAAATTACATAGATAATGTATTAAATGAAGTACTTGTAGTGCCAAACATC
385 166_HRV36b   AATCCAGTTGAAAATTACATAGATAATGTATTAAATGAAGTACTTGTAGTGCCAAACATC
386 167_HRV36    AATCCAGTTGAAAATTACATAGATAATGTATTAAATGAAGTACTTGTAGTGCCAAACATC
387 168_HRV89a   AACCCAGTTGAAAATTATATAGATAGTGTATTAAATGAAGTTCTTGTGGTGCCAAATATC
388 169_HRV89b   AACCCAGTTGAAAATTATATAGATAGTGTATTAAATGAAGTTCTTGTGGTGCCAAATATC
389 170_HRV89    AACCCAGTTGAAAATTATATAGATAGTGTATTAAATGAAGTTCTTGTGGTGCCAAATATC
390 171_HRV58    AATCCAGTAGAAAATTACATAGATAATGTGTTAAATGAAGTACTTGTAGTTCCAAATATC
```

FIG. D6 CONT'D

02.trace                                                                                                                9/20/2007 4:59 PM

```
391  172_HRV58a   AATCCAGTAGAAAAATTACATAGATAATGTGTTAAATGAAGTACTTGTAGTTCCAAATATC
392  173_HRV58b   AATCCAGTAGAAAAATTACATAGATAATGTGTTAAATGAAGTACTTGTAGTTCCAAATATC
393  174_HRV12a   AATCCAGTAGAGAGATATGTTGATGAGGTGCTAAATGAAGTTCTAGTTGTTCCAAACATA
394  175_HRV12b   AATCCAGTAGAGAGATATGTTGATGAGGTGCTAAATGAAGTTCTAGTTGTTCCAAACATA
395  176_HRV12    AATCCAGTAGAGAGATATGTTGATGAGGTGCTAAATGAAGTTCTAGTTGTTCCAAACATA
396  177_HRV78a   AATCCAGTGGAAGAATATGTTGATCAGGTTTTAAATGAGGTTTTAGTTGTTCCAAACATA
397  178_HRV78b   AATCCAGTGGAAGAATATGTTGATCAGGTTTTAAATGAGGTTTTAGTTGTTCCAAACATA
398  179_HRV78    AATCCAGTGGAAGAATATGTTGATCAGGTTTTAAATGAGGTTTTAGTTGTTCCAAACATA
399  180_HRV20    AACCCAGTGGAAAGGTACACAGAAGCTATTTTAAATGAAGTTCTTGTAGTTCCAAATATC
400  181_HRV20a   AACCCAGTGGAAAGGTACACAGAAGCTATTTTAAATGAAGTTCTTGTAGTTCCAAATATC
401  182_HRV20b   AACCCAGTGGAAAGGTACACAGAAGCTATTTTAAATGAAGTTCTTGTAGTTCCAAATATC
402  183_HRV68    AACCCAGTTGAAAAATACACAGAAGCCGTTCTTAATGAGGTCCTTGTGGTTCCAAACATA
403  184_HRV68a   AACCCAGTTGAAAAATACACAGAAGCCGTTCTTAATGAGGTCCTTGTGGTTCCAAACATA
404  185_HRV68b   AACCCAGTTGAAAAATACACAGAAGCCGTTCTTAATGAGGTCCTTGTGGTTCCAAACATA
405  186_HRV28    AATCCAGTTGAAAAATATACTGAAGCACTACTTAATGAAGTGCTTGTTGTGCCAAACATC
406  187_HRV28a   AATCCAGTTGAAAAATATACTGAAGCACTACTTAATGAAGTGCTTGTTGTGCCAAACATC
407  188_HRV28b   AATCCAGTTGAAAAATATACTGAAGCACTACTTAATGAAGTGCTTGTTGTGCCAAACATC
408  189_HRV53a   AACCCGGTAGAGAAATACACAGAGGCTATCTTAAATGAAGTATTAGTAGTCCCAAACATT
409  190_HRV53b   AACCCGGTAGAGAAATACACAGAGGCTATCTTAAATGAAGTATTAGTAGTCCCAAACATT
410  191_HRV53    AACCCGGTAGAGAAATACACAGAGGCTATCTTAAATGAAGTATTAGTAGTCCCAAACATT
411  192_HRV46a   AATCCAGTGGAAAAATATACAGAAGCTGTTCTTAATGAGGTCCTTGTAGTACCTAACATC
412  193_HRV46b   AATCCAGTGGAAAAATATACAGAAGCTGTTCTTAATGAGGTCCTTGTAGTACCTAACATC
413  194_HRV46    AATCCAGTGGAAAAATATACAGAAGCTGTTCTTAATGAGGTCCTTGTAGTACCTAACATC
414  195_HRV80a   AATCCAGTCGAAAAATACACAGAAGCAATCCTCAATGAAGTTCTTGTTGTACCAAACATC
415  196_HRV80b   AATCCAGTCGAAAAATACACAGAAGCAATCCTCAATGAAGTTCTTGTTGTACCAAACATC
416  197_HRV80    AATCCAGTCGAAAAATACACAGAAGCAATCCTCAATGAAGTTCTTGTTGTACCAAACATC
417  198_HRV51    AACCCTGTTGAAAAATATACAGAGGCTTTACTCAATGAAGTGTTGGTGGTTCCAACATA
418  199_HRV51a   AACCCTGTTGAAAAATATACAGAGGCTTTACTCAATGAAGTGTTGGTGGTTCCCAACATA
419  200_HRV51b   AACCCTGTTGAAAAATATACAGAGGCTTTACTCAATGAAGTGTTGGTGGTTCCCAACATA
420  201_HRV65a   AATCCAATTGAGAAGTATACAGAAGCTCTACTTAATGAAGTGTTGGTGGTCCCAAATATA
421  202_HRV65b   AATCCAATTGAGAAGTATACAGAAGCTCTACTTAATGAAGTGTTGGTGGTCCCAAATATA
422  203_HRV65    AATCCAATTGAGAAGTATACAGAAGCTCTACTTAATGAAGTGTTGGTGGTCCCAAATATA
423  204_HRV71a   AATCCTGTAGAAAAATATACAGAAGCAATACTCAATGAGGTTCTAGTTGTGCCAAATATA
424  205_HRV71b   AATCCTGTAGAAAAATATACAGAAGCAATACTCAATGAGGTTCTAGTTGTGCCAAATATA
425  206_HRV71    AATCCTGTAGAAAAATATACAGAAGCAATACTCAATGAGGTTCTAGTTGTGCCAAATATA
426  207_HRV8     AACCCTATTGAACAATTCACAGAGGCAGTATTAAACGAGGTTCTTGTAGTTCCAAACACA
427  208_HRV95    AACCCTATTGAACAATTCACAGAGGCAGTATTAAACGAGGTTCTTGTAGTTCCAAATACA
428  209_HRV45    AACCCTGTTGAACAATTTGCAGAAGCAGTCCTTGATCAAGTATTAGTAGTTCCAAACACT
429  210_HRV45a   AACCCTGTTGAACAATTTGCAGAAGCAGTCCTTGATCAAGTATTAGTAGTTCCAAACACT
430  211_HRV45b   AACCCTGTTGAACAATTTGCAGAAGCAGTCCTTGATCAAGTATTAGTAGTTCCAAACACT
431  GROUP_1      AA-CC--T-GA----T------A-----T--T-----A-GT--T--T-GT-CC--A----
432
433  1_HRV1A1|d   AAAGAAAGTCATCACACTACATCAAACTCTGCCCCACTTTTAGATGCTGCAGAGACGGGA
434  2_HRV1A2|d   AAAGAAAGTCATCACACTACATCAAACTCTGCCCCACTTTTAGATGCTGCAGAGACGGGA
435  3_HRV1A|cD   AAAGAAAGTCATCACACTACATCAAACTCTGCCCCACTTTTAGATGCTGCAGAGACGGGA
436  4_HRV1B1|d   AAAGAAAGCCATCACACTACATCAAATTCTGCTCCACTCTTGGATGCTGCAGAGACAGGA
437  5_HRV1B2|d   AAAGAAAGCCATCACACTACATCAAATTCTGCTCCACTCTTGGATGCTGCAGAGACAGGA
438  6_HRV1B      AAAGAAAGCCATCACACTACATCAAATTCTGCTCCACTCTTGGATGCTGCAGAGACAGGA
439  7_HRV40a|d   AGAGAGAGCCATCCAACTACATCAAATTCGGCCCCTGCCTTGGATGCAGCAGAGACTGGA
440  8_HRV40b|d   AGAGAGAGCCATCCAACTACATCAAATTCGGCCCCTGCCTTGGATGCAGCAGAGACTGGA
441  9_HRV40      AGAGAGAGCCATCCAACTACATCAAATTCGGCCCCTGCCTTGGATGCAGCAGAGACTGGA
442  10_HRV85     AAAGAGAGTCACCCAACTATATCAAATTCAGCTCCTGCTTTGGATGCAGCAGAGACTGGC
443  11_HRV85a|   AAAGAGAGTCACCCAACTATATCAAATTCAGCTCCTGCTTTGGATGCAGCAGAGACTGGC
444  12_HRV85b|   AAAGAGAGTCACCCAACTATATCAAATTCAGCTCCTGCTTTGGATGCAGCAGAGACTGGC
445  13_HRV56a|   AGGGAGAGCCATCCATCCACATCAAATTCTGCCCCTGCATTGATGCTGCTGAAACTGGC
446  14_HRV56b|   AGGGAGAGCCATCCATCCACATCAAATTCTGCCCCTGCATTAGATGCTGCTGAAACTGGC
447  15_HRV56     AGGGAGAGCCATCCATCCACATCAAATTCTGCCCCTGCATTAGATGCTGCTGAAACTGGC
448  16_HRV54     AGAGAAAGTCATCCAGCTACATCTAATTCAGCCCCTGCTAGTGCGGCAGAAACTGGA
449  17_HRV98     AAAGAAAGTCATCCAGCTACATCTAATTCGGCCCCTACACTGATGCAGCAGAAACTGGG
450  18_HRV59a|   CAGGAAAGCCACCCAACCACCTCAAATGCTGCTCCAGCATTAGATGCAGCAGAGACTGGA
451  19_HRV59b|   CAGGAAAGCCACCCAACCACCTCAAATGCTGCTCCAGCATTAGATGCAGCAGAGACTGGA
452  20_HRV59     CAGGAAAGCCACCCAACCACCTCAAATGCTGCTCCAGCATTAGATGCAGCAGAGACTGGA
453  21_HRV63     CAAGAAAGCCATCCAACCACATCAAACGCTGCTCCTGTACTTGATGCTGCGGAAACAGGA
454  22_HRV63b|   CAAGAAAGCCATCCAACCACATCAAACGCTGCTCCTGTACTTGATGCTGCGGAAACAGGA
455  23_HRV63a|   CAAGAAAGCCATCCAACCACATCAAACGCTGCTCCTGTACTTGATGCTGCGGAAACAGGA
```

FIG. D6 CONT'D 02.trace                                                           9/20/2007 4:59 PM

```
456  24_HRV39      AGAGAGAGCCATCCAACTACATCTAATGCAGCTACAGCTTTGGATGCTGCTGAAACTGGA
457  25_HRV39a|    AGAGAGAGCCATCCAACTACATCTAATGCAGCTACAGCTTTGGATGCTGCTGAAACTGGA
458  26_HRV39b|    AGAGAGAGCCATCCAACTACATCTAATGCAGCTCCAGCTTTGGATGCTGCTGAAACTGGA
459  27_HRV10a|    AGAGAAAGTCATCCAAGCACCTCTAACTCTGCCCCAATTCTCGATGCAGCTGAGACTGGT
460  28_HRV10b|    AGAGAAAGTCATCCAAGCACCTCTAACTCTGCCCCAATTCTCGATGCAGCTGAGACTGGT
461  29_HRV10      AGAGAAAGTCATCCAAGCACCTCTAACTCTGCCCCAATTCTCGATGCAGCTGAGACTGGT
462  30_HRV100a    AGAGAGAGCCATCCAAGCACCTCAAACTCTGCTCCAATCCTTGATGCTGCTGAAACTGGC
463  31_HRV100b    AGAGAGAGCCATCCAAGCACCTCAAACTCTGCTCCAATCCTTGATGCTGCTGAAACTGGC
464  32_HRV100     AGAGAGAGCCATCCAAGCACCTCAAACTCTGCTCCAATCCTTGATGCTGCTGAAACTGGC
465  33_HRV66      AAGGAAAGCCATCCAAGCACATCAAATGCTGCCCCAATACTAGATGCAGCTGAAACAGGT
466  34_HRV66b|    AAGGAAAGCCATCCAAGCACATCAAATGCTGCCCCAATACTAGATGCAGCTGAAACAGGT
467  35_HRV66a|    AAGGAAAGCCATCCAAGCACATCAAATGCTGCCCCAATACTAGATGCAGCTGAAACAGGT
468  36_HRV77a|    AAGGAGAGTCATCCAAGCACTTCTAACTCTGCTCCTATACTAGATGCAGCTGAAACAGGC
469  37_HRV77b|    AAGGAGAGTCATCCAAGCACTTCTAACTCTGCTCCTATACTAGATGCAGCTGAAACAGGC
470  38_HRV77      AAGGAGAGTCATCCAAGCACTTCTAACTCTGCTCCTATACTAGATGCAGCTGAAACAGGC
471  39_HRV62a     AAAGAAAGTCACCCTAGTACGTCAAACTCTGCCCCAATTCTAGATGCTGCTGAAACCGGA
472  40_HRV62b     AAAGAAAGTCACCCTAGTACGTCAAACTCTGCCCCAATTCTAGATGCTGCTGAAACCGGA
473  41_HRV25      AAAGAAAGTCACCCAAGCACATCAAATTCTGCCCCAATTCTAGATGCTGCTGAAACTGGA
474  42_HRV29a     AGGGAGAGCCACCCAAGCACGTCCAACTCTGCACCAATCTTGGATGCTGCTGAGACTGGA
475  43_HRV29b     AGGGAGAGCCACCCAAGCACGTCCAACTCTGCACCAATCTTGGATGCTGCTGAGACTGGA
476  44_HRV44a     AGAGAGAGCCACCCAAGCACATCTAACTCTGCTCCAATTTTGGATGCTGCTGAAACTGGA
477  45_HRV44b     AGAGAGAGCCACCCAAGCATATCTAACTCTGCTCCAATTTTGGATGCTGCTGAAACTGGA
478  46_HRV31      AAAGAAAGCCATCCAAGCACATCTAATTCTGCCCCAATCCTGGACGCTGCTGAAACTGGA
479  47_HRV31a|    AAAGAAAGCCATCCAAGCACATCTAATTCTGCCCCAATCCTGGACGCTGCTGAAACTGGA
480  48_HRV31b|    AAAGAAAGCCATCCAAGCACATCTAATTCTGCCCCAATCCTGGACGCTGCTGAAACTGGA
481  49_HRV47      AAAGAAAGTCATCCAAGTACATCCAACTCTGCCCCGATTTTAGATGCTGCTGAAACTGGA
482  50_HRV47a|    AAAGAAAGTCATCCAAGTACATCCAACTCTGCCCCGATTTTAGATGCTGCTGAAACTGGA
483  51_HRV47b|    AAAGAAAGTCATCCAAGTACATCCAACTCTGCCCCGATTTTAGATGCTGCTGAAACTGGA
484  52_HRV11      AAGGAGAGCCAAGCTACCACATCAAACTCAGCACCTGCTCTAGATGCAGCTGAAACCGGA
485  53_HRV11b|    AAGGAGAGCCAAGCTACCACATCAAACTCAGCACCTGCTCTAGATGCAGCTGAAACCGGA
486  54_HRV11a|    AAGGAGAGCCAAGCTACCACATCAAACTCAGCACCTGCTCTAGATGCAGCTGAAACCGGA
487  55_HRV76      AAAGAGAGTCAGGCTACCACATCAAATGCAGCACCTGCTTTGGATGCAGCTGAGACTGGG
488  56_HRV76b|    AAAGAGAGTCAGGCTACCACATCAAATGCAGCACCTGCTTTGGATGCAGCTGAGACTGGG
489  57_HRV76a|    AAAGAGAGTCAGGCTACCACATCAAATGCAGCACCTGCTTTGGATGCAGCTGAGACTGGG
490  58_HRV33      AGAGAGAGTCAAGCAACCACATCAAATTCAGCACCTGCCTTAGATGCAGCTGAGACTGGA
491  59_HRV33b|    AGAGAGAGTCAAGCAACCACATCAAATTCAGCACCTGCCTTAGATGCAGCTGAGACTGGA
492  60_HRV33a|    AGAGAGAGTCAAGCAACCACATCAAATTCAGCACCTGCCTTAGATGCAGCTGAGACTGGA
493  61_HRV24a|    AAGGAAAGTAAACCATCAACATCAAACTCAGCACCAGCTTTGGATGCAGCAGAAACTGGA
494  62_HRV24b|    AAGGAAAGTAAACCATCAACATCAAACTCAGCACCAGCTTTGGATGCAGCAGAAACTGGA
495  63_HRV24      AAGGAAAGTAAACCATCAACATCAAACTCAGCACCAGCTTTGGATGCAGCAGAAACTGGA
496  64_HRV90      AAGGAAAGTAAACCTTCAACTTCAAACTCAGCGCCAGCTTTAGATGCAGCAGAAACCGGA
497  65_HRV90a|    AAGGAAAGTAAACCTTCAACTTCAAACTCAGCGCCAGCTTTAGATGCAGCAGAAACCGGA
498  66_HRV90b|    AAGGAAAGTAAACCTTCAACTTCAAACTCAGCGCCAGCTTTAGATGCAGCAGAAACCGGA
499  67_HRV34      AAAGAAAGCCAAGCCACCACATCAAACTCTGCCCCCGCACTGGATGCAGCTGAGACTGGT
500  68_HRV34b|    AAAGAAAGCCAAGCCACCACATCAAACTCTGCCCCCGCACTGGATGCAGCTGAGACTGGT
501  69_HRV34a|    AAAGAAAGCCAAGCCACCACATCAAACTCTGCCCCCGCACTGGATGCAGCTGAGACTGGT
502  70_HRV50a|    AAGGAGAGTCAAGCCACTACATCAAACTCTGCCCCTGCTTTAGATGCAGCTGAAACTGGA
503  71_HRV50b|    AAGGAGAGTCAAGCCACTACATCAAACTCTGCCCCTGCTTTAGATGCAGCTGAAACTGGA
504  72_HRV50      AAGGAGAGTCAAGCCACTACATCAAACTCTGCCCCTGCTTTAGATGCAGCTGAAACTGGA
505  73_HRV18a|    AATGAAAGTCACGCAATTACATCAAATTCAGCCCCTGCTTTAGATGCCGCTGAAACTGGT
506  74_HRV18b|    AATGAAAGTCACGCAATTACATCAAATTCAGCCCCTGCTTTAGATGCCGCTGAAACTGGT
507  75_HRV18      AATGAAAGTCACGCAATTACATCAAATTCAGCCCCTGCTTTAGATGCCGCTGAAACTGGT
508  76_HRV55      AGGGAGAGTCAAGCAGCAACATCAAATTCAGCTCCAGTACTAGATGCAGCAGAAACTGGG
509  77_HRV55b|    AGGGAGAGTCAAGCAGCAACATCAAATTCAGCTCCAGTACTAGATGCAGCAGAAACTGGG
510  78_HRV55a|    AGGGAGAGTCAAGCAGCAACATCAAATTCAGCTCCAGTACTAGATGCAGCAGAAACTGGG
511  79_HRV57      AAACAAAGTCAAGCAACAACATCAAACTCAGCACCTGCATTGGATGCAGCTGAAACTGGA
512  80_HRV57a|    AAACAAAGTCAAGCAACAACATCAAACTCAGCACCTGCATTGGATGCAGCTGAAACTGGA
513  81_HRV57b|    AAACAAAGTCAAGCAACAACATCAAACTCAGCACCTGCATTGGATGCAGCTGAAACTGGA
514  82_HRV21      AGAGAGAGTCATGGAACAACATCAAACTCTGCTCCCGCACTTGATGCTGCAGAAACTGGA
515  83_HRVHan     AGAGAGAGTCATGGAACAACATCAAACTCTGCTCCCGCACTTGATGCTGCAGAAACTGGG
516  84_HRV43      GTAGAAAGTCATTCAACAACATCCAATGCAGCCCCTGCACTTGATGCAGCTGAAACTGGG
517  85_HRV43b|    GTAGAAAGTCATTCAACAACATCCAATGCAGCCCCTGCACTTGATGCAGCTGAAACTGGG
518  86_HRV43a|    GTAGAAAGTCATTCAACAACATCCAATGCAGCCCCTGCACTTGATGCAGCTGAAACTGGG
519  87_HRV75      ATGGAGAGCCATCCAACAACGTCTAATGCTGCTCCAGCTTTAGATGCAGCTGAAACTGGC
520  88_HRV75b|    ATGGAGAGCCATCCAACAACGTCTAATGCTGCTCCAGCTTTAGATGCAGCTGAAACTGGC
```

FIG. D6 CONT'D 02.trace                                                                9/20/2007 4:59 PM

```
521  89_HRV75a|    ATGGAGAGCCATCCAACAACGTCTAATGCTGCTCCAGCTTTAGATGCAGCTGAAACTGGC
522  96_HRV9a|d    AAAGAGAGCAACCCTACAACCTCTAACTCAGCTCCAGCTCTAGATGCTGCTGAGACAGGC
523  97_HRV9b|d    AAAGAGAGCAACCCTACAACCTCTAACTCAGCTCCAGCTCTAGATGCTGCTGAGACAGGC
524  98_HRV9       AAAGAGAGCAACCCTACAACCTCTAACTCAGCTCCAGCTCTAGATGCTGCTGAGACAGGC
525  99_HRV32      AAAGAAAGCAATCCCACAACCTCTAATTCAGCCCCAGCCTTAGATGCTGCCGAAACAGGT
526  100_HRV32a    AAAGAAAGCAATCCCACAACCTCTAATTCAGCCCCAGCCTTAGATGCTGCCGAAACAGGT
527  101_HRV32b    AAAGAAAGCAATCCCACAACCTCTAATTCAGCCCCAGCCTTAGATGCTGCCGAAACAGGT
528  102_HRV67     AAGCAAAGTGAACCCACGACTTCCAATTCAGCCCCAGCTCTAGATGCTGCTGAGACAGGT
529  103_HRV67a    AAGCAAAGTGAACCCACGACTTCCAATTCAGCCCCAGCTCTAGATGCTGCTGAGACAGGT
530  104_HRV67b    AAGCAAAGTGAACCCACGACTTCCAATTCAGCCCCAGCTCTAGATGCTGCTGAGACAGGT
531  105_HRV15     AAGGAGAGTCACTCAAGCACATCCAACTCAGCACCAGCACTAGATGCAGCTGAGACCGGC
532  106_HRV15a    AAGGAGAGTCACTCAAGCACATCCAACTCAGCACCAGCACTAGATGCAGCTGAGACCGGC
533  107_HRV15b    AAGGAGAGTCACTCAAGCACATCCAACTCAGCACCAGCACTAGATGCAGCTGAGACCGGC
534  108_HRV74a    AGAGAAAGCCATTCAAGTACTTCAAACTCAGCACCAGCACTGGATGCAGCTGAAACTGGC
535  109_HRV74b    AGAGAAAGCCATTCAAGTACTTCAAACTCAGCACCAGCACTGGATGCAGCTGAAACTGGC
536  110_HRV74     AGAGAAAGCCATTCAAGTACTTCAAACTCAGCACCAGCACTGGATGCAGCTGAAACTGGC
537  111_HRV38a    AAGGAAAGCCACTCCAGCACATCAAATTCAGCACCAGCATTAGATGCTGCTGAGACTGGA
538  112_HRV38b    AAGGAAAGCCACTCCAGCACATCAAATTCAGCACCAGCATTAGATGCTGCTGAGACTGGA
539  113_HRV38     AAGGAAAGCCACTCCAGCACATCAAATTCAGCACCAGCATTAGATGCTGCTGAGACTGGA
540  114_HRV60     AGGGAGAGCCAACCCACTACTTCTAATTCTGCTCCAGCATTGGATGCTGCTGAGACTGGT
541  115_HRV60a    AGGGAGAGCCAACCCACTACTTCTAATTCTGCTCCAGCATTGGATGCTGCTGAGACTGGT
542  116_HRV60b    AGGGAGAGCCAACCCACTACTTCTAATTCTGCTCCAGCATTGGATGCTGCTGAGACTGGT
543  117_HRV64a    AATGAGAGCCATCCCAGCACTTCCAATGCAGCGCCAGCTTTAGATGCAGCTGAGACCGGA
544  118_HRV64b    AATGAGAGCCATCCCAGCACTTCCAATGCAGCGCCAGCTTTAGATGCAGCTGAGACCGGA
545  119_HRV64     AATGAGAGCCATCCCAGCACTTCCAATGCAGCGCCAGCTTTAGATGCAGCTGAGACCGGA
546  120_HRV94a    AATGAGAGTCACCCTAGCACATCCAATGCAGCGCCAGCCTTAGATGCTGCCGAAACTGGA
547  121_HRV94b    AATGAGAGTCACCCTAGCACATCCAATGCAGCGCCAGCCTTAGATGCTGCCGAAACTGGA
548  122_HRV94     AATGAGAGTCACCCTAGCACATCCAATGCAGCGCCAGCCTTAGATGCTGCCGAAACTGGA
549  123_HRV22     AATGAAAGTCACCCCAGTACATCAAATGCTGCACCAGCACTAGATGCTGCTGAAACTGGA
550  124_HRV22a    AATGAAAGTCACCCCAGTACATCAAATGCTGCACCAGCACTAGATGCTGCTGAAACTGGA
551  125_HRV22b    AATGAAAGTCACCCCAGTACATCAAATGCTGCACCAGCACTAGATGCTGCTGAAACTGGA
552  126_HRV82     AATGAAAGTCATCCTAGTACTTCAAATTCAGCTCCTGCCTTGGACGCTGCAGAGACAGGA
553  127_HRV82b    AATGAAAGTCATCCTAGTACTTCAAATTCAGCTCCTGCCTTGGACGCTGCAGAGACAGGA
554  128_HRV82a    AATGAAAGTCATCCTAGTACTTCAAATTCAGCTCCTGCCTTGGACGCTGCAGAGACAGGA
555  129_HRV19     AATGAAAGTCATCCAAGTACATCAAATGCTGCTCCTGCCTTAGATGCAGCCGAGACAGGA
556  130_HRV19a    AATGAAAGTCATCCAAGTACATCAAATGCTGCTCCTGCCTTAGATGCAGCCGAGACAGGA
557  131_HRV19b    AATGAAAGTCATCCAAGTACATCAAATGCTGCTCCTGCCTTAGATGCAGCCGAGACAGGA
558  132_HRV13     AGTGAAAGTAGCTCAACTACATCTAATTCAGCTCCAGCCTTAGATGCTGCAGAAACTGGC
559  133_HRV13a    AGTGAAAGTAGCTCAACTACATCTAATTCAGCTCCAGCCTTAGATGCTGCAGAAACTGGC
560  134_HRV13b    AGTGAAAGTAGCTCAACTACATCTAATTCAGCTCCAGCCTTAGATGCTGCAGAAACTGGC
561  135_HRV41     AGTGAAAGCAGTCCAACTACTTCTAATTCAGCTCCAGCCCTAGATGCAGCAGAGACTGGT
562  136_HRV41a    AGTGAAAGCAGTCCAACTACTTCTAATTCAGCTCCAGCCCTAGATGCAGCAGAGACTGGT
563  137_HRV41b    AGTGAAAGCAGTCCAACTACTTCTAATTCAGCTCCAGCCCTAGATGCAGCAGAGACTGGT
564  138_HRV73     AATGAAAGTAATCCAACTACATCCAACTCAGCACCTGCACTGGACGCTGCAGAAACTGGC
565  139_HRV73b    AATGAAAGTAATCCAACTACATCCAACTCAGCACCTGCACTGGACGCTGCAGAAACTGGC
566  140_HRV73a    AATGAAAGTAATCCAACTACATCCAACTCAGCACCTGCACTGGACGCTGCAGAAACTGGC
567  141_HRV61     AATCAGAGCAACCCTACAACATCCAACTCAGCACCAGTCTTAGACGCTGCTGAAACAGGT
568  142_HRV61a    AATCAGAGCAACCCTACAACATCCAACTCAGCACCAGTCTTAGACGCTGCTGAAACAGGT
569  143_HRV61b    AATCAGAGCAACCCTACAACATCCAACTCAGCACCAGTCTTAGACGCTGCTGAAACAGGT
570  144_HRV96     AATGAAAGTTACCCAACAACTTCCAATTCAGCCCCAGTGCTAGATGCCGCTGAAACAGGT
571  145_HRV96b    AATGAAAGTTACCAACAACTTCCAATTCAGCCCCAGTGCTAGATGCCGCTGAAACAGGT
572  146_HRV96a    AATGAAAGTTACCCAACAACTTCCAATTCAGCCCCAGTGCTAGATGCCGCTGAAACAGGT
573  90_HRV16a|    AATGAGAGCCACCCTACCACATCAAATGCGGCCCAGTTTTGGATGCTGCTGAAACAGGA
574  91_HRV16b|    AATGAGAGCCACCCTACCACATCAAATGCGGCCCAGTTTTGGATGCTGCTGAAACAGGA
575  92_1AYM_A     AATGAGAGCCACCCTACCACATCAAATGCGGCCCAGTTTTGGATGCTGCTGAAACAGGA
576  93_HRV81a|    AATGAAAGCCACCCTACAACATCTAATTCAGCTCCTGTTTTAGATGCAGCTGAAACTGGA
577  94_HRV81b|    AATGAAAGCCACCCTACAACATCTAATTCAGCTCCTGTTTTAGATGCAGCTGAAACTGGA
578  95_HRV81      AATGAAAGCCACCCTACAACATCTAATTCAGCTCCTGTTTTAGATGCAGCTGAAACTGGA
579  147_HRV2      AATAGTAGTAACCCCACAACATCAAATTCTGCCCCAGCCTTAGATGCTGCAGAAACAGGG
580  148_HRV2a|    AATAGTAGTAACCCCACAACATCAAATTCTGCCCCAGCATTAGATGCTGCAGAAACAGGG
581  149_HRV2b|    AATAGTAGTAACCCCACAACATCAAATTCTGCCCCAGCATTAGATGCTGCAGAAACAGGG
582  150_HRV49a    AATAGTAGTCACCCCACGACATCAAATCTGCTCCAGCATTAGATGCTGCAGAAACAGGG
583  151_HRV49b    AATAGTAGTCACCCCACGACATCAAATCTGCTCCAGCATTAGATGCTGCAGAAACAGGG
584  152_HRV49     AATAGTAGTCACCCCACGACATCAAATCTGCTCCAGCATTAGATGCTGCAGAAACAGGG
585  153_HRV23a    AATAGTAGTCATCCCACAACATCAAACTCTGCTCCAGCATTAGACGCTGCGGAAACGGGT
```

FIG. D6 CONT'D 02.trace                                                                                              9/20/2007 4:59 PM

```
586  154_HRV23b    AATAGTAGTCATCCCACAACATCAAACTCTGCTCCAGCATTAGACGCTGCGGAAACGGGT
587  155_HRV23     AATAGTAGTCATCCCACAACATCAAACTCTGCTCCAGCATTAGACGCTGCGGAAACGGGT
588  156_HRV30a    AACAGTAGTCACCCTACTACATCAAACTCTGCTCCGGCATTAGATGCTGCAGAAACAGGA
589  157_HRV30b    AACAGTAGTCACCCTACTACATCAAACTCTGCTCCGGCATTAGATGCTGCAGAAACAGGA
590  158_HRV30     AACAGTAGTCACCCTACTACATCAAACTCTGCTCCGGCATTAGATGCTGCAGAAACAGGA
591  159_HRV7      CAGCCAAGTACATCTGTTTCAAGTCACTCTGTACCAGCATTGGATGCTGCAGAGACTGGA
592  160_HRV7b|    CAGCCAAGTACATCTGTTTCAAGTCACTCTGTACCAGCATTGGATGCTGCAGAGACTGGA
593  161_HRV7a|    CAGCCAAGTACATCTGTTTCAAGTCACTCTGTACCAGCATTGGATGCTGCAGAGACTGGA
594  162_HRV88     CAACCTAGCACATCCGTTTCAAGTCACTCTGTGCCAGCTCTGGATGCTGCGGAAACAGGG
595  163_HRV88a    CAACCTAGCACATCCGTTTCAAGTCACTCTGTGCCAGCTCTGGATGCTGCGGAAACAGGG
596  164_HRV88b    CAACCTAGCACATCCGTTTCAAGTCACTCTGTGCCAGCTCTGGATGCTGCGGAAACAGGG
597  165_HRV36a    CAACCTAGTTCATCTGTGTCAAGTCATTCAGCTCCCGCCTTAGACGCTGCGGAAACTGGA
598  166_HRV36b    CAACCTAGTTCATCTGTGTCAAGTCATTCAGCTCCCGCCTTAGACGCTGCGGAAACTGGA
599  167_HRV36     CAACCTAGTTCATCTGTGTCAAGTCATTCAGCTCCCGCCTTAGACGCTGCGGAAACTGGA
600  168_HRV89a    CAACCTAGCACATCTGTGTCAAGTCATGCAGCGCCTGCATTGGATGCTGCGGAAACCGGA
601  169_HRV89b    CAACCTAGCACATCTGTGTCAAGTCATGCAGCGCCTGCATTGGATGCTGCGGAAACCGGA
602  170_HRV89     CAACCTAGCACATCTGTGTCAAGTCATGCAGCGCCTGCATTGGATGCTGCGGAAACCGGA
603  171_HRV58     CAACCTAGTACATCTGTATCAAGTCATTCTGTGCCTGCCTTGGATGCTGCAGAAACGGGA
604  172_HRV58a    CAACCTAGTACATCTGTATCAAGTCATTCTGTGCCTGCCTTGGATGCTGCAGAAACGGGA
605  173_HRV58b    CAACCTAGTACATCTGTATCAAGTCATTCTGTGCCTGCCTTGGATGCTGCAGAAACGGGA
606  174_HRV12a    AACAAAAGTAATGGGCAGTTATCAAACGCAGCACCAGCGTTGGACGCTGCAGAAACTGGT
607  175_HRV12b    AACAAAAGTAATGGGCAGTTATCAAACGCAGCACCAGCGTTGGACGCTGCAGAAACTGGT
608  176_HRV12     AACAAAAGTAATGGGCAGTTATCAAACGCAGCACCAGCGTTGGACGCTGCAGAAACTGGT
609  177_HRV78a    AAAGAAAGTAAACCCCAGTCTAGCAACTCCGCTCCAGTTTTGGACGCTGCAGAAACAGGT
610  178_HRV78b    AAAGAAAGTAAACCCCAGTCTAGCAACTCCGCTCCAGTTTTGGACGCTGCAGAAACAGGT
611  179_HRV78     AAAGAAAGTAAACCCCAGTCTAGCAACTCCGCTCCAGTTTTGGACGCTGCAGAAACAGGT
612  180_HRV20     ACATCTAGTAACTCCCAAACATCAAATGCAGCACCAGCACTAGATGCTGCTGAGACAGGA
613  181_HRV20a    ACATCTAGTAACTCCCAAACATCAAATGCAGCACCAGCACTAGATGCTGCTGAGACAGGA
614  182_HRV20b    ACATCTAGTAACTCCCAAACATCAAATGCAGCACCAGCACTAGATGCTGCTGAGACAGGA
615  183_HRV68     CCAGCAAGTAATACCCAAACTTCAAATGCAGCCCCAGCCTTAGATGCTGCTGAGACTGGA
616  184_HRV68a    CCAGCAAGTAATACCCAAACTTCAAATGCAGCCCCAGCCTTAGATGCTGCTGAGACTGGA
617  185_HRV68b    CCAGCAAGTAATACCCAAACTTCAAATGCAGCCCCAGCCTTAGATGCTGCTGAGACTGGA
618  186_HRV28     AATCCTAGCAACGCACAAACTACAAATGCAGCTCCCGCTCTCGATGCCGCTGAGACGGGG
619  187_HRV28a    AATCCTAGCAACGCACAAACTACAAATGCAGCTCCCGCTCTCGATGCCGCTGAGACGGGG
620  188_HRV28b    AATCCTAGCAACGCACAAACTACAAATGCAGCTCCCGCTCTCGATGCCGCTGAGACGGGG
621  189_HRV53a    AATGCAAGCAATCCACAAACTTCAAATTCAGCACCAGCACTAGATGCTGCAGAAACGGGT
622  190_HRV53b    AATGCAAGCAATCCACAAACTTCAAATTCAGCACCAGCACTAGATGCTGCAGAAACGGGT
623  191_HRV53     AATGCAAGCAATCCACAAACTTCAAATTCAGCACCAGCACTAGATGCTGCAGAAACGGGT
624  192_HRV46a    AATGCCAGTAGTGGACATACATCTAATTCAGCTCCAGCACTTGATGCAGCAGAAACTGGA
625  193_HRV46b    AATGCCAGTAGTGGACATACATCTAATTCAGCTCCAGCACTTGATGCAGCAGAAACTGGA
626  194_HRV46     AATGCCAGTAGTGGACATACATCTAATTCAGCTCCAGCACTTGATGCAGCAGAAACTGGA
627  195_HRV80a    AGTGCTAGCAATGGACATACATCAAACTCAGCTCCAACACTTGATGCAGCAGAAACTGGT
628  196_HRV80b    AGTGCTAGCAATGGACATACATCAAACTCAGCTCCAACACTTGATGCAGCAGAAACTGGT
629  197_HRV80     AGTGCTAGCAATGGACATACATCAAACTCAGCTCCAACACTTGATGCAGCAGAAACTGGT
630  198_HRV51     CAACCTAGCAGTGGGCACACATCTAATGCTGCACCAGCTCTAGATGCTGCTGAGACAGGA
631  199_HRV51a    CAACCTAGCAGTGGGCACACATCTAATGCTGCACCAGCTCTAGATGCTGCTGAGACAGGA
632  200_HRV51b    CAACCTAGCAGTGGGCACACATCTAATGCTGCACCAGCTCTAGATGCTGCTGAGACAGGA
633  201_HRV65a    CAAGCTAGTAATGGGCATACATCTAATGCTGCACCAGCTTTAGATGCTGCTGAAACAGGA
634  202_HRV65b    CAAGCTAGTAATGGGCATACATCTAATGCTGCACCAGCTTTAGATGCTGCTGAAACAGGA
635  203_HRV65     CAAGCTAGTAATGGGCATACATCTAATGCTGCACCAGCTTTAGATGCTGCTGAAACAGGA
636  204_HRV71a    CAACCTAGTAATGGACATACCTCAAACTCAGCACCAGCCTTAGATGCAGCAGAAACTGGG
637  205_HRV71b    CAACCTAGTAATGGACATACCTCAAACTCAGCACCAGCCTTAGATGCAGCAGAAACTGGG
638  206_HRV71     CAACCTAGTAATGGACATACCTCAAACTCAGCACCAGCCTTAGATGCAGCAGAAACTGGG
639  207_HRV8      CAAGCTAGTAATGGATCTATAGCAAATTCAGCACCAGCATTAGATGCAGCAGAGACTGGA
640  208_HRV95     CAAGCCAGTAATGGATCTATAGCAAATTCAGCACCAGCATTAGATGCAGCAGAGACTGGA
641  209_HRV45     CGACCCAGCGATGGGTTGATTGCAAACTCAGCCCCAGCTTTGGATGCAGCTGAAACTGGA
642  210_HRV45a    CGACCCAGCGATGGGTTGATTGCAAACTCAGCCCCAGCTTTGGATGCAGCTGAAACTGGA
643  211_HRV45b    CGACCCAGCGATGGGTTGATTGCAAACTCAGCCCCAGCTTTGGATGCAGCTGAAACTGGA
644  GROUP_1       ------AG----------------A--C-G---C-----T-GA-GC-GC-GA-AC-GG-
645
646  1_HRV1A1|d    CACACCAGTAATGTTCAACCAGAAGATGCTATAGAGACAAGGTATGTTATAACATCACAA
647  2_HRV1A2|d    CACACCAGTAATGTTCAACCAGAAGATGCTATAGAGACAAGGTATGTTATAACATCACAA
648  3_HRV1A|cD    CACACCAGTAATGTTCAACCAGAAGATGCTATAGAGACAAGGTATGTTATAACATCACAA
649  4_HRV1B1|d    CACACCAGTAATGTACAACCAGAGGATGCTATAGAAACAAGATATGTTATGACATCACAA
650  5_HRV1B2|d    CACACCAGTAATGTACAACCAGAGGATGCTATAGAAACAAGATATGTTATGACATCACAA
```

FIG. D6 CONT'D 02.trace                                                                    9/20/2007 4:59 PM

```
651  6_HRV1B        CACACCAGTAATGTACAACCAGAGGATGCTATAGAAACAAGATATGTTATGACATCACAA
652  7_HRV40a|d     CATACAAGCAACATACAACCTGAAGATACAATAGAAACAAGATTTGTGCAGACATCACAA
653  8_HRV40b|d     CATACAAGCAACATACAACCTGAAGATACAATAGAAACAAGATTTGTGCAGACATCACAA
654  9_HRV40        CATACAAGCAACATACAACCTGAAGATACAATAGAAACAAGATTTGTGCAGACATCACAA
655  10_HRV85       CATACAAGTAGTACACAGCCCGAGGATACAATAGAGACCAGGTTTGTTCAAACTTCACAG
656  11_HRV85a|     CATACAAGTAGTACACAGCCCGAGGATACAATAGAGACCAGGTTTGTTCAAACTTCACAG
657  12_HRV85b|     CATACAAGTAGTACACAGCCCGAGGATACAATAGAGACCAGGTTTGTTCAAACTTCACAG
658  13_HRV56a|     CATACTAGTGCAATCCAACCAGAAGACACTATAGAAACCAGATATGTACAGACATCACAA
659  14_HRV56b|     CATACTAGTGCAATCCAACCAGAAGACACTATAGAAACCAGATATGTACAGACATCACAA
660  15_HRV56       CATACTAGTGCAATCCAACCAGAAGACACTATAGAAACCAGATATGTACAGACATCACAA
661  16_HRV54       CACACTAGTGGAGTACAACCCGAGGACACCATAGAAACAAGATTTGTGCAGACATCACAA
662  17_HRV98       CACACTAGTGGAATACAACCTGAGGATACTATAGAAACAAGATTTGTGCAGACATCACAA
663  18_HRV59a|     CATACAAGCAGTATACAACCTGAGGATACCATAGAAACAAGATATGTTCAGACATCACAA
664  19_HRV59b|     CATACAAGCAGTATACAACCTGAGGATACCATAGAAACAAGATATGTTCAGACATCACAA
665  20_HRV59       CATACAAGCAGTATACAACCTGAGGATACCATAGAAACAAGATATGTTCAGACATCACAA
666  21_HRV63       CACACAAGCAGTATACAACCTGAGGATACTGTAGAAACTAGATATGTGCAAACGTCTCAA
667  22_HRV63b|     CACACAAGCAGTATACAACCTGAGGATACTGTAGAAACTAGATATGTGCAAACGTCTCAA
668  23_HRV63a|     CACACAAGCAGTATACAACCTGAGGATACTGTAGAAACTAGATATGTGCAAACGTCTCAA
669  24_HRV39       CACACAAGTAGCACCCAGCCTGAAGACACAATTGAAACAAGATATGTGCAAACCTCACAT
670  25_HRV39a|     CACACAAGTAGCACCCAGCCTGAAGACACAATTGAAACAAGATATGTGCAAACCTCACAT
671  26_HRV39b|     CACACAAGTAGCATCCAACCTGAAGACACAATTGAAACAAGATATGTGCAAACCTCACAT
672  27_HRV10a|     CATACCAGTAGTGTACAACCAGAAGATACGGTTGAAACACGATATGTGCAAACATCCCAG
673  28_HRV10b|     CATACCAGTAGTGTACAACCAGAAGATACGGTTGAAACACGATATGTGCAAACATCCCAG
674  29_HRV10       CATACCAGTAGTGTACAACCAGAAGATACGGTTGAAACACGATATGTGCAAACATCCCAG
675  30_HRV100a     CACACTAGTAATGTGCAACCTGAAGATACAGTTGAAACTCGATATGTGCAGACATCACAG
676  31_HRV100b     CACACTAGTAATGTGCAACCTGAAGATACAGTTGAAACTCGATATGTGCAGACATCACAG
677  32_HRV100      CACACTAGTAATGTGCAACCTGAAGATACAGTTGAAACTCGATATGTGCAGACATCACAG
678  33_HRV66       CACACTAGTAAAGTACAACCAGAAGATACAGTTGAGACTCGTTACGTGCAAACATCACAG
679  34_HRV66b|     CACACTAGTAAAGTACAACCAGAAGATACAGTTGAGACTCGTTACGTGCAAACATCACAG
680  35_HRV66a|     CACACTAGTAAAGTACAACCAGAAGATACAGTTGAGACTCGTTACGTGCAAACATCACAG
681  36_HRV77a|     CATACTAGTAGTGTGCAACCAGAAGATACAGTTGAGACCCGCTATGTACAAACTTCCCAG
682  37_HRV77b|     CATACTAGTAGTGTGCAACCAGAAGATACAGTTGAGACCCGCTATGTACAAACTTCCCAG
683  38_HRV77       CATACTAGTAGTGTGCAACCAGAAGATACAGTTGAGACCCGCTATGTACAAACTTCCCAG
684  39_HRV62a      CACACTAGTAATGTACAACCAGAAGACACTATTGAAACCCGTCATGTTCAAACCACACAA
685  40_HRV62b      CACACTAGTAATGTACAACCAGAAGACACTATTGAAACCCGTTATGTTCAAACCACACAA
686  41_HRV25       CACACTAGCAATGTGCAACCAGAGGATACCATTGAAACTCGTTATGTTCAAACCACACAA
687  42_HRV29a      CATACTAGTAATGTACAACCAGAAGATACCATTGAGACTCGTTATGTACAAACCTCACAT
688  43_HRV29b      CATACTAGTAATGTACAACCAGAAGATACCATTGAGACTCGTTATGTACAAACCTCACAT
689  44_HRV44a      CATACTAGTAATGTACAACCAGAAGATACCATTGAGACTCGATATGTACAAACCTCACAA
690  45_HRV44b      CATACTAGTAATGTACAACCAGAAGATACCATTGAGACTCGATATGTACAAACCTCACAA
691  46_HRV31       CACACTAGTAATGTACAACCAGAAGATACAATTGAAACTCGCTACGTGCAAACATCACAA
692  47_HRV31a|     CACACTAGTAATGTACAACCAGAAGATACAATTGAAACTCGCTACGTGCAAACATCACAA
693  48_HRV31b|     CACACTAGTAATGTACAACCAGAAGATACAATTGAAACTCGCTACGTGCAAACATCACAA
694  49_HRV47       CACACTAGCAATGTACAGCCAGAAGATACAATTGAAACTCGATATGTACAAACAGCACAA
695  50_HRV47a|     CACACTAGCAATGTACAGCCAGAAGATACAATTGAAACTCGATATGTACAAACAGCACAA
696  51_HRV47b|     CACACTAGCAATGTACAGCCAGAAGATACAATTGAAACTCGATATGTACAAACAGCACAA
697  52_HRV11       CATACTAGCAAAGTGCAGCCAGAGGATATGATTGAGACTAGATATGTGCAGACTTCACAG
698  53_HRV11b|     CATACTAGCAAAGTGCAGCCAGAGGATATGATTGAGACTAGATATGTGCAGACTTCACAG
699  54_HRV11a|     CATACTAGCAAAGTGCAGCCAGAGGATATGATTGAGACTAGATATGTGCAGACTTCACAG
700  55_HRV76       CACACAAGCAGCGTTCAACCAGAGGACATGGTTGAGACTAGGTATGTGCAAACATCACAA
701  56_HRV76b|     CACACAAGCAGCGTTCAACCAGAGGACATGGTTGAGACTAGGTATGTGCAAACATCACAA
702  57_HRV76a|     CACACAAGCAGCGTTCAACCAGAGGACATGGTTGAGACTAGGTATGTGCAAACATCACAA
703  58_HRV33       CACACTAATAATGTACAACCAGAAGATATGATTGAAACAAGATATGTACAAACATCACAA
704  59_HRV33b|     CACACTAATAATGTACAACCAGAAGATATGATTGAAACAAGATATGTACAAACATCACAA
705  60_HRV33a|     CACACTAATAATGTACAACCAGAAGATATGATTGAAACAAGATATGTACAAACATCACAA
706  61_HRV24a|     CATACGAGTAGCGTGCAGCCAGAAGATATGGTTGAAACTAGATATGTCCAAACATCACAA
707  62_HRV24b|     CATACGAGTAGCGTGCAGCCAGAAGATATGGTTGAAACTAGATATGTCCAAACATCACAA
708  63_HRV24       CATACGAGTAGCGTGCAGCCAGAAGATATGGTTGAAACTAGATATGTCCAAACATCACAA
709  64_HRV90       CATACTAGTGATGTCCAGCCAGAAGATGTGGTAGAGACCAGATACGTGCAAACATCACAA
710  65_HRV90a|     CATACTAGTGATGTCCAGCCAGAAGATGTGGTAGAGACCAGATACGTGCAAACATCACAA
711  66_HRV90b|     CATACTAGTGATGTCCAGCCAGAAGATGTGGTAGAGACCAGATACGTGCAAACATCACAA
712  67_HRV34       CACACTAGCAGTGTACAACCTGAAGATATGATTGAGACCAGGTACGTACAAACATCACAA
713  68_HRV34b|     CACACTAGCAGTGTACAACCTGAAGATATGATTGAGACCAGGTACGTACAAACATCACAA
714  69_HRV34a|     CACACTAGCAGTGTACAACCTGAAGATATGATTGAGACCAGGTACGTACAAACATCACAA
715  70_HRV50a|     CACACAAGTAATGTGCAGCCTGAAGATATGCTTGAAACTAGATATGTGCAAACATCGCAT
```

FIG. D6 CONT'D

```
02.trace                                                           9/20/2007 4:59 PM 716  71_HRV50b|    CACACAAGTAATGTGCAGCCTGAAGATATGCTTGAAACTAGATATGTGCAAACATCGCAT
717  72_HRV50     CACACAAGTAATGTGCAGCCTGAAGATATGCTTGAAACTAGATATGTGCAAACATCGCAT
718  73_HRV18a|   CACACCAGCAATGTGCAACCTGAAGATATGATTGAGACTAGGTATGTACAAACATCACAA
719  74_HRV18b|   CACACCAGCAATGTGCAACCTGAAGATATGATTGAGACTAGGTATGTACAAACATCACAA
720  75_HRV18     CACACCAGCAATGTGCAACCTGAAGATATGATTGAGACTAGGTATGTACAAACATCACAA
721  76_HRV55     CATACAAGCAATGTACAACCAGAAGATGTAATTGAGACAAGATATGTTCAGACATCACAA
722  77_HRV55b|   CATACAAGCAATGTACAACCAGAAGATGTAATTGAGACAAGATATGTTCAGACATCACAA
723  78_HRV55a|   CATACAAGCAATGTACAACCAGAAGATGTAATTGAGACAAGATATGTTCAGACATCACAA
724  79_HRV57     CACACTAGTAATGTACAACCGGAAGACATGATTGAAACTAGATATGTCCAGACATCACAA
725  80_HRV57a|   CACACTAGTAATGTACAACCGGAAGACATGATTGAAACTAGATATGTCCAGACATCACAA
726  81_HRV57b|   CACACTAGTAATGTACAACCGGAAGACATGATTGAAACTAGATATGTCCAGACATCACAA
727  82_HRV21     CACACTAGTAATGTACAGCCGGAGGATATGGTTGAAACAAGGTATGTTCAGACATCACAA
728  83_HRVHan    CACACTAGTAATGTACAACCAGAGGATATGGTTGAAACAAGGTATGTTCAGACATCACAA
729  84_HRV43     CATACTAGCCAGGTGCAACCTGAAGACATGGTAGAGACAAGGTCAGTACATAATTTCCAA
730  85_HRV43b|   CATACTAGCCAGGTGCAACCTGAAGACATGGTAGAGACAAGGTCAGTACATAATTTCCAA
731  86_HRV43a|   CATACTAGCCAGGTGCAACCTGAAGACATGGTAGAGACAAGGTCAGTACATAATTTCCAA
732  87_HRV75     CATACCAGCCATGTTCAACCAGAAGACATGTTAGAAACAAGGCAAGTACAAAATTTCCAA
733  88_HRV75b|   CATACCAGCCATGTTCAACCAGAAGACATGTTAGAAACAAGGCAAGTACAAAATTTCCAA
734  89_HRV75a|   CATACCAGCCATGTTCAACCAGAAGACATGTTAGAAACAAGGCAAGTACAAAATTTCCAA
735  96_HRV9a|d   CATACTAGCAATGTTCAACCTGAAGACATGATTGAAACACGTTATGTGCAGACATCACAA
736  97_HRV9b|d   CATACTAGCAATGTTCAACCTGAAGACATGATTGAAACACGTTATGTGCAGACATCACAA
737  98_HRV9      CATACTAGCAATGTTCAACCTGAAGACATGATTGAAACACGTTATGTGCAGACATCACAA
738  99_HRV32     CATACCAGTAATGTTCAACCTGAAGACATGATTGAAACACGTTATGTGCAAACAACACAC
739  100_HRV32a   CATACCAGTAATGTTCAACCTGAAGACATGATTGAAACACGTTATGTGCAAACAACACAC
740  101_HRV32b   CATACCAGTAATGTTCAACCTGAAGACATGATTGAAACACGTTATGTGCAAACAACACAC
741  102_HRV67    CACACTAGCAGTGTACAACCTGAAGATATGATCGAGACTCGTTATGTACAGGCATCAAAT
742  103_HRV67a   CACACTAGCAGTGTACAACCTGAAGATATGATCGAGACTCGTTATGTACAGGCATCAAAT
743  104_HRV67b   CACACTAGCAGTGTACAACCTGAAGATATGATCGAGACTCGTTATGTACAGGCATCAAAT
744  105_HRV15    CATACTAGCAGTGTTCAACCTGAGGATATGATTGAAACTCGTTACGTCCAAACATCACAG
745  106_HRV15a   CATACTAGCAGTGTTCAACCTGAGGATATGATTGAAACTCGTTACGTCCAAACATCACAG
746  107_HRV15b   CATACTAGCAGTGTTCAACCTGAGGATATGATTGAAACTCGTTACGTCCAAACATCACAG
747  108_HRV74a   CATACCAGTAATGTGCAACCAGAAGATATGGTTGAGACACGCTATGTGCAAACCTCACAG
748  109_HRV74b   CATACCAGTAATGTGCAACCAGAAGATATGGTTGAGACACGCTATGTGCAAACCTCACAG
749  110_HRV74    CATACCAGTAATGTGCAACCAGAAGATATGGTTGAGACACGCTATGTGCAAACCTCACAG
750  111_HRV38a   CACACCAGTAATGTGCAGCCTGAGGATATGATTGAAACTCGCTATGTACAGACATCACAA
751  112_HRV38b   CACACCAGTAATGTGCAGCCTGAGGATATGATTGAAACTCGCTATGTACAGACATCACAA
752  113_HRV38    CACACCAGTAATGTGCAGCCTGAGGATATGATTGAAACTCGCTATGTACAGACATCACAA
753  114_HRV60    CACACTAGTAATGTACAGCCTGAGGACGTGATTGAAACACGTTATGTGCAGATTACACAA
754  115_HRV60a   CACACTAGTAATGTACAGCCTGAGGACGTGATTGAAACACGTTATGTGCAGATTACACAA
755  116_HRV60b   CACACTAGTAATGTACAGCCTGAGGACGTGATTGAAACACGTTATGTGCAGATTACACAA
756  117_HRV64a   CACACCAGTAATGTACAGCCTGAAGATATGATTGAAACGCGCTATGTACAAAACACTCAA
757  118_HRV64b   CACACCAGTAATGTACAGCCTGAAGATATGATTGAAACGCGCTATGTACAAAACACTCAA
758  119_HRV64    CACACCAGTAATGTACAGCCTGAAGATATGATTGAAACGCGCTATGTACAAAACACTCAA
759  120_HRV94a   CACACAAGCAATGTACAACCTGAGGATATGATTGAAACACGCTATGTACAAAACACTCAA
760  121_HRV94b   CACACAAGCAATGTACAACCTGAGGATATGATTGAAACACGCTATGTACAAAACACTCAA
761  122_HRV94    CACACAAGCAATGTACAACCTGAGGATATGATTGAAACACGCTATGTACAAAACACTCAA
762  123_HRV22    CACACAAGCAATGTGCAGCCAGAAGACATGATAGAAACGCGCTATGTGTTAAATTCACAA
763  124_HRV22a   CACACAAGCAATGTGCAGCCAGAAGACATGATAGAAACGCGCTATGTGTTAAATTCACAA
764  125_HRV22b   CACACAAGCAATGTGCAGCCAGAAGACATGATAGAAACGCGCTATGTGTTAAATTCACAA
765  126_HRV82    CATACAAGTACTGTTCAACCTGAGGACATGATTGAAACACGGTATGTTCAAACATCACAA
766  127_HRV82b   CATACAAGTACTGTTCAACCTGAGGACATGATTGAAACACGGTATGTTCAAACATCACAA
767  128_HRV82a   CATACAAGTACTGTTCAACCTGAGGACATGATTGAAACACGGTATGTTCAAACATCACAA
768  129_HRV19    CATACTAGCAATGTACAGCCTGAGGACATGATCGAAACACGCTATGTTCAAACGTCCCAG
769  130_HRV19a   CATACTAGCAATGTACAGCCTGAGGACATGATCGAAACACGCTATGTTCAAACGTCCCAG
770  131_HRV19b   CATACTAGCAATGTACAGCCTGAGGACATGATCGAAACACGCTATGTTCAAACGTCCCAG
771  132_HRV13    CACACAAGCAGTGTACAACCAGAAGACATGGTTGAAACACGTTATGTCCAAACTTCACAA
772  133_HRV13a   CACACAAGCAGTGTACAACCAGAAGACATGGTTGAAACACGTTATGTCCAAACTTCACAA
773  134_HRV13b   CACACAAGCAGTGTACAACCAGAAGACATGGTTGAAACACGTTATGTCCAAACTTCACAA
774  135_HRV41    CATACCAGTAATGTACAACCAGAGGACATGATTGAAACACGATATGTCCAAACCTCACAA
775  136_HRV41a   CATACCAGTAATGTACAACCAGAGGACATGATTGAAACACGATATGTCCAAACCTCACAA
776  137_HRV41b   CATACCAGTAATGTACAACCAGAGGACATGATTGAAACACGATATGTCCAAACCTCACAA
777  138_HRV73    CATACCAGTGGTGTACAACCAGAAGACATGATTGAGACCCGTTATGTCCAAACATCACAG
778  139_HRV73b   CATACCAGTGGTGTACAACCAGAAGACATGATTGAGACCCGTTATGTCCAAACATCACAG
779  140_HRV73a   CATACCAGTGGTGTACAACCAGAAGACATGATTGAGACCCGTTATGTCCAAACATCACAG
780  141_HRV61    CATACCAGCAATGTTCAACCGGAGGACACGATTGAAACACGATATGTTCAAACCTCACAG
```

FIG. D6 CONT'D

```
02.trace                                                                9/20/2007 4:59 PM 781 142_HRV61a      CATACCAGCAATGTTCAACCGGAGGACACGATTGAAACACGATATGTTCAAACCTCACAG
782 143_HRV61b      CATACCAGCAATGTTCAACCGGAGGACACGATTGAAACACGATATGTTCAAACCTCACAG
783 144_HRV96       CATACTAGCAATGTCCAACCAGAGGATATGATTGAGACTCGATATGTTCAGACATCGCAG
784 145_HRV96b      CATACTAGCAATGTCCAACCAGAGGATATGATTGAGACTCGATATGTTCAGACATCGCAG
785 146_HRV96a      CATACTAGCAATGTCCAACCAGAGGATATGATTGAGACTCGATATGTTCAGACATCGCAG
786  90_HRV16a|     CATACCAATAAGATACAGCCAGAAGACACTATAGAAACCAGATATGTGCAATCTTCACAG
787  91_HRV16b|     CATACCAATAAGATACAGCCAGAAGACACTATAGAAACCAGATATGTGCAATCTTCACAG
788  92_1AYM_A      CATACCAATAAGATACAGCCAGAAGACACTATAGAAACCAGATATGTGCAATCTTCACAG
789  93_HRV81a|     CACACCAGTAATATACAACCTGAGGATACTATTGAGACCAGATATGTACAATCTTCACAG
790  94_HRV81b|     CACACCAGTAATATACAACCTGAGGATACTATTGAGACCAGATATGTACAATCTTCACAG
791  95_HRV81       CACACCAGTAATATACAACCTGAGGATACTATTGAGACCAGATATGTACAATCTTCACAG
792 147_HRV2        CACACTAGTAGTGTTCAACCAGAGGATGTCATTGAAACTAGGTATGTGCAGACATCACAA
793 148_HRV2a|      CACACTAGTAGTGTTCAACCAGAGGATGTCATTGAAACTAGGTATGTGCAGACATCACAA
794 149_HRV2b|      CACACTAGTAGTGTTCAACCAGAGGATGTCATTGAAACTAGGTATGTGCAGACATCACAA
795 150_HRV49a      CACACTAGCAATGTGCAACCTGAAGATGTCATTGAAACCAGATATGTACAGACATCACAA
796 151_HRV49b      CACACTAGCAATGTGCAACCTGAAGATGTCATTGAAACCAGATATGTACAGACATCACAA
797 152_HRV49       CACACTAGCAATGTGCAACCTGAAGATGTCATTGAAACCAGATATGTACAGACATCACAA
798 153_HRV23a      CACACTAGTAATGTTCAACCAGAAGATGTCATTGAAACCAGGTACGTTCAAACATCACAA
799 154_HRV23b      CACACTAGTAATGTTCAACCAGAAGATGTCATTGAAACCAGGTACGTTCAAACATCACAA
800 155_HRV23       CACACTAGTAATGTTCAACCAGAAGATGTCATTGAAACCAGGTACGTTCAAACATCACAA
801 156_HRV30a      CATACTAGTAATGTTCAACCTGAAGATGTCATTGAAACTAGATATGTTCAAACATCACAA
802 157_HRV30b      CATACTAGTAATGTTCAACCTGAAGATGTCATTGAAACTAGATATGTTCAAACATCACAA
803 158_HRV30       CATACTAGTAATGTTCAACCTGAAGATGTCATTGAAACTAGATATGTTCAAACATCACAA
804 159_HRV7        CATACTAGTTCTGTTCAACCTGAAGATATGATCGAGACAAGGTATGTCATAACAGACCAA
805 160_HRV7b|      CATACTAGTTCTGTTCAACCTGAAGATATGATCGAGACAAGGTATGTCATAACAGACCAA
806 161_HRV7a|      CATACTAGTTCTGTTCAACCTGAAGATATGATCGAGACAAGGTATGTCATAACAGACCAA
807 162_HRV88       CATACTAGTTCTGTTCAACCTGAAGATATGATAGAAACTAGATATGTTATAACAGATCAA
808 163_HRV88a      CATACTAGTTCTGTTCAACCTGAAGATATGATAGAAACTAGATATGTTATAACAGATCAA
809 164_HRV88b      CATACTAGTTCTGTTCAACCTGAAGATATGATAGAAACTAGATATGTTATAACAGATCAA
810 165_HRV36a      CATACCAGCTCTGTCCAACCAGAGGACATGATCGAGACCAGATATGTCATAACTGATCAA
811 166_HRV36b      CATACCAGCTCTGTCCAACCAGAGGACATGATCGAGACCAGATATGTCATAACTGATCAA
812 167_HRV36       CATACCAGCTCTGTCCAACCAGAGGACATGATCGAGACCAGATATGTCATAACTGATCAA
813 168_HRV89a      CACACCAGCTCTGTTCAACCTGAAGATATGATTGAAACTAGATATGTTATAACTGATCAA
814 169_HRV89b      CACACCAGCTCTGTTCAACCTGAAGATATGATTGAAACTAGATATGTTATAACTGATCAA
815 170_HRV89       CACACCAGCTCTGTTCAACCTGAAGATATGATTGAAACTAGATATGTTATAACTGATCAA
816 171_HRV58       CACACAAGTTCTGTTCAGCCTGAGGATATGATTGAAACTAGATATGTTATCACAGATCAA
817 172_HRV58a      CACACAAGTTCTGTTCAGCCTGAGGATATGATTGAAACTAGATATGTTATCACAGATCAA
818 173_HRV58b      CACACAAGTTCTGTTCAGCCTGAGGATATGATTGAAACTAGATATGTTATCACAGATCAA
819 174_HRV12a      CATACCAGCCAAACACAACCAGAAGATGTGATTGAAACCAGGTATGTGATTACAGACCAG
820 175_HRV12b      CATACCAGCCAAACACAACCAGAAGATGTGATTGAAACCAGGTATGTGATTACAGACCAG
821 176_HRV12       CATACCAGCCAAACACAACCAGAAGATGTGATTGAAACCAGGTATGTGATTACAGACCAG
822 177_HRV78a      CATACGAACCAAGTACAGCCTGAAGACACCATAGAAACTAGATATGTTATAACTGACCAA
823 178_HRV78b      CATACGAACCAAGTACAGCCTGAAGACACCATAGAAACTAGATATGTTATAACTGACCAA
824 179_HRV78       CATACGAACCAAGTACAGCCTGAAGACACCATAGAAACTAGATATGTTATAACTGACCAA
825 180_HRV20       CACACAAACCAGGTCCAGCCAGAAGATATGGTCGAGACACGGTATGTAATTACTGATCAG
826 181_HRV20a      CACACAAACCAGGTCCAGCCAGAAGATATGGTCGAGACACGGTATGTAATTACTGATCAG
827 182_HRV20b      CACACAAACCAGGTCCAGCCAGAAGATATGGTCGAGACACGGTATGTAATTACTGATCAG
828 183_HRV68       CATACAAACCAAGTCCAACCAGAAGATGTGGTTGAAACACGCTATGTCATAACAGACCAG
829 184_HRV68a      CATACAAACCAAGTCCAACCAGAAGATGTGGTTGAAACACGCTATGTCATAACAGACCAG
830 185_HRV68b      CATACAAACCAAGTCCAACCAGAAGATGTGGTTGAAACACGCTATGTCATAACAGACCAG
831 186_HRV28       CACACAAGCCAAACACAACCTGAAGACATGGTTGAGACTAGGTATGTAATCACAGATCAG
832 187_HRV28a      CACACAAGCCAAACACAACCTGAAGACATGGTTGAGACTAGGTATGTAATCACAGATCAG
833 188_HRV28b      CACACAAGCCAAACACAACCTGAAGACATGGTTGAGACTAGGTATGTAATCACAGATCAG
834 189_HRV53a      CATACAAGTCAGACACAACCTGAGGACATGCTGGAAACTAGATATGTCATCACAGACCAA
835 190_HRV53b      CATACAAGTCAGACACAACCTGAGGACATGCTGGAAACTAGATATGTCATCACAGACCAA
836 191_HRV53       CATACAAGTCAGACACAACCTGAGGACATGCTGGAAACTAGATATGTCATCACAGACCAA
837 192_HRV46a      CACACTAGCCAGATACAACCAGAAGACATGATAGAAACCAGATATGTTATCACAGACCAA
838 193_HRV46b      CACACTAGCCAGATACAACCAGAAGACATGATAGAAACCAGATATGTTATCACAGACCAA
839 194_HRV46       CACACTAGCCAGATACAACCAGAAGACATGATAGAAACCAGATATGTTATCACAGACCAA
840 195_HRV80a      CACACTAGCCAGGTGCAACCAGAAGACATGATAGAAACTAGATATGTTATTACTGATCAG
841 196_HRV80b      CACACTAGCCAGGTGCAACCAGAAGACATGATAGAAACTAGATATGTTATTACTGATCAG
842 197_HRV80       CACACTAGCCAGGTGCAACCAGAAGACATGATAGAAACTAGATATGTTATTACTGATCAG
843 198_HRV51       CATACTAGTCAAGTTCAACCAGAAGATATGGTAGAGACCAGGTATGTTGTCACAGACCAA
844 199_HRV51a      CATACTAGTCAAGTTCAACCAGAAGATATGGTAGAGACCAGGTATGTTGTCACAGACCAA
845 200_HRV51b      CATACTAGTCAAGTTCAACCAGAAGATATGGTAGAGACCAGGTATGTTGTCACAGACCAA
```

FIG. D6 CONT'D

```
02.trace                                                                    9/20/2007 4:59 PM 846 201_HRV65a    CACACTAGTCAAGTTCAACCAGAGGATGTGATAGAAACCAGATATGTCATCACAGATCAA
847 202_HRV65b    CACACTAGTCAAGTTCAACCAGAGGATGTGATAGAAACCAGATATGTCATCACAGATCAA
848 203_HRV65     CACACTAGTCAAGTTCAACCAGAGGATGTGATAGAAACCAGATATGTCATCACAGATCAA
849 204_HRV71a    CATACCAACCAAGTACAACCAGAAGATGTTATGGAAACCAGATATGTGATCACTGATCAA
850 205_HRV71b    CATACCAACCAAGTACAACCAGAAGATGTTATGGAAACCAGATATGTGATCACTGATCAA
851 206_HRV71     CATACCAACCAAGTACAACCAGAAGATGTTATGGAAACCAGATATGTGATCACTGATCAA
852 207_HRV8      CACACAAGTTCAGTGCAACCTGAAGATCTTATAGAGACTAGGTATGTAATTACAGATCAA
853 208_HRV95     CACACAAGTTCAGTGCAACCTGAAGATCTTATAGAGACTAGGTATGTAATTACAGATCAA
854 209_HRV45     CACACCAGTTCAGTGCAGCCTGAGGACCTTATAGAGACTAGATATGTGATTGCAGACCAA
855 210_HRV45a    CACACCAGTTCAGTGCAGCCTGAGGACCTTATAGAGACTAGATATGTGATTGCAGACCAA
856 211_HRV45b    CACACCAGTTCAGTGCAGCCTGAGGACCTTATAGAGACTAGATATGTGATTGCAGACCAA
857 GROUP_1       CA-AC-A--------CA-CC-GA-GA-----T-GA-AC--G----GT----------A-
858
859 1_HRV1A1|d    ACAAGAGATGAGATGAGTATAGAAAGTTTCCTTGGTAGATCTGGTTGTGTCCACATCTCA
860 2_HRV1A2|d    ACAAGAGATGAGATGAGTATAGAAAGTTTCCTTGGTAGATCTGGTTGTGTCCACATCTCA
861 3_HRV1A|cD    ACAAGAGATGAGATGAGTATAGAAAGTTTCCTTGGTAGATCTGGTTGTGTCCACATCTCA
862 4_HRV1B1|d    ACAAGAGATGAGATGAGTATAGAAAGTTTTCTTGGTAGATCTGGCTGTGTGCATATTTCA
863 5_HRV1B2|d    ACAAGAGATGAGATGAGTATAGAAAGTTTTCTTGGTAGATCTGGCTGTGTGCATATTTCA
864 6_HRV1B       ACAAGAGATGAGATGAGTATAGAAAGTTTTCTTGGTAGATCTGGCTGTGTGCATATTTCA
865 7_HRV40a|d    ACTAGAGATGAAATGAGCATAGAGAGTTTCTTGGGAAGATCTGGGTGCATTCATATATCC
866 8_HRV40b|d    ACTAGAGATGAAATGAGCATAGAGAGTTTCTTGGGAAGATCTGGGTGCATTCATATATCC
867 9_HRV40       ACTAGAGATGAAATGAGCATAGAGAGTTTCTTGGGAAGATCTGGGTGCATTCATATATCC
868 10_HRV85      ACTAGGGATGAAATGAGTTTAGAAAGTTTCTTGGGAAGATCTGGATGTATCCATATATCT
869 11_HRV85a|    ACTAGGGATGAAATGAGTTTAGAAAGTTTCTTGGGAAGATCTGGATGTATCCATATATCT
870 12_HRV85b|    ACTAGGGATGAAATGAGTTTAGAAAGTTTCTTGGGAAGATCTGGATGTATCCATATATCT
871 13_HRV56a|    ACTAGGGATGAAATGAGTATAGAGAGTTTTCTAGGTAGATCAGGTTGTATACATATATCA
872 14_HRV56b|    ACTAGGGATGAAATGAGTATAGAGAGTTTTCTAGGTAGATCAGGTTGTATACATATATCA
873 15_HRV56      ACTAGAGATGAAATGAGTATAGAGAGTTTCTAGGTAGATCAGGTTGTATACATATATCA
874 16_HRV54      ACTAGAGATGAAATGAGCATAGAAAGTTTTCTAGGCAGGGCTGGTTGCATACATGAATCC
875 17_HRV98      ACCAGAGATGAAATGAGTATAGAAAGTTTTCTAGGTAGGGCCGGTTGTATACATGAATCT
876 18_HRV59a|    ACTAGAGATGAGTGAGTGTAGAAAGTTTCTTAGGTAGATCTGGGTGTATACATATTTCA
877 19_HRV59b|    ACTAGAGATGAGATGAGTGTAGAAAGTTTCTTAGGTAGATCTGGGTGTATACATATTTCA
878 20_HRV59      ACTAGAGATGAGATGAGTGTAGAAAGTTTCTTAGGTAGATCTGGGTGTATACATATTTCA
879 21_HRV63      ACAAGGGATGAAATGAGTGTAGAGAGCTTTCTTGGTAGATCAGGATGCATACACATATCA
880 22_HRV63b|    ACAAGGGATGAAATGAGTGTAGAGAGCTTTCTTGGTAGATCAGGATGCATACACATATCA
881 23_HRV63a|    ACAAGGGATGAAATGAGTGTAGAGAGCTTTCTTGGTAGATCAGGATGCATACACATATCA
882 24_HRV39      ACTAGGGATGAAATGAGCGTTGAAAGTTTCTTAGGCAGATCTGGCTGTATTCACATTTCC
883 25_HRV39a|    ACTAGGGATGAAATGAGCGTTGAAAGTTTCTTAGGCAGATCTGGCTGTATTCACATTTCC
884 26_HRV39b|    ACTAGGGATGAAATGAGTGTTGAAAGTTTCTTAGGCAGATCTGGCTGTATTCACATTTCC
885 27_HRV10a|    ACGAGAGATGAAATGAGTATTGAAAGTTTTCTTGGCAGGTCAGGTTGTATACACACCTCA
886 28_HRV10b|    ACGAGAGATGAAATGAGTATTGAAAGTTTTCTTGGCAGGTCAGGTTGTATACACACCTCA
887 29_HRV10      ACGAGAGATGAAATGAGTATTGAAAGTTTTCTTGGCAGGTCAGGTTGTATACACACCTCA
888 30_HRV100a    ACCAGGGATGAAATGAGTATTGAGAGCTTTCTTGGAAGATCTGGTTGTATACACACCTCA
889 31_HRV100b    ACCAGGGATGAAATGAGTATTGAGAGCTTTCTTGGAAGATCTGGTTGTATACACACCTCA
890 32_HRV100     ACCAGGGATGAAATGAGTATTGAGAGCTTTCTTGGAAGATCTGGTTGTATACACACCTCA
891 33_HRV66      ACTAGAGATGAACATAGAAAGTTTCTAGGTAGGTCAGGATGTATCCATATATCA
892 34_HRV66b|    ACTAGAGATGAAATGAGCATAGAAAGTTTTCTAGGTAGGTCAGGATGTATCCATATATCA
893 35_HRV66a|    ACTAGAGATGAAATGAGCATAGAAAGTTTCTAGGTAGGTCAGGATGTATCCATATATCA
894 36_HRV77a|    ACAAGGGATGAGATGAGTATTGAGAGCTTTCTGGGTAGGTCTGGTTGTATTCACATTTCA
895 37_HRV77b|    ACAAGGGATGAGATGAGTATTGAGAGCTTTCTGGGTAGGTCTGGTTGTATTCACATTTCA
896 38_HRV77      ACAAGGGATGAGATGAGTATTGAGAGCTTTCTGGGTAGGTCTGGTTGTATTCACATTTCA
897 39_HRV62a     ACTAGAGATGAAATGAGCATTGAGAGCTTTCTTGGTAGGTCAGGGTGCGTACACACTTCA
898 40_HRV62b     ACTAGAGATGAAATGAGCATTGAGAGCTTTCTTGGTAGGTCAGGGTGCGTACACACTTCA
899 41_HRV25      ACTAGAGATGAAATGAGTATTGAGAGCTTTCTTGGTAGGTCAGGGTGTGTACATACTTCA
900 42_HRV29a     ACTAGAGATGAAATGAGCATTGAAAGTTTCTTGGGTAGATCAGGATGTATACATGTTTCA
901 43_HRV29b     ACTAGAGATGAAATGAGCATTGAAAGTTTTCTTGGTAGATCAGGATGTATACATGTTTCA
902 44_HRV44a     ACTAGAGATGAAATGAGCATTGAAAGTTTTCTTGGCAGATCAGGGTGTATACATGTTTCA
903 45_HRV44b     ACTAGAGATGAAATGAGCATTGAAAGTTTTCTTGGCAGATCAGGGTGTATACATGTTTCA
904 46_HRV31      ACAAGAGATGAAATGAGCATTGAAAGTTTCCTTGGTAGGTCAGGATGTGTACATACTTCA
905 47_HRV31a|    ACAAGAGATGAAATGAGCATTGAAAGTTTCCTTGGTAGGTCAGGATGTGTACATACTTCA
906 48_HRV31b|    ACAAGAGATGAAATGAGCATTGAAAGTTTCCTTGGTAGGTCAGGATGTGTACATACTTCA
907 49_HRV47      ACAAGAGATGAAATGAGCATTGAGAGCTTCCTTGGCAGGTCAGGATGTGTGCATTCCTCA
908 50_HRV47a|    ACAAGAGATGAAATGAGCATTGAGAGCTTCCTTGGCAGGTCAGGATGTGTGCATTCCTCA
909 51_HRV47b|    ACAAGAGATGAAATGAGCATTGAGAGCTTCCTTGGCAGGTCAGGATGTGTGCATTCCTCA
910 52_HRV11      ACTCTTGATGAAATGAGCATTGAGAGCTTCCTAGGTAGATCTGGTTGTATTCACATGTCC
```

FIG. D6 CONT'D

02.trace                                                          9/20/2007 4:59 PM

```
911  53_HRV11b|     ACTCTTGATGAAATGAGCATTGAGAGCTTCCTAGGTAGATCTGGTTGTATTCACATGTCC
912  54_HRV11a|     ACTCTTGATGAAATGAGCATTGAGAGCTTCCTAGGTAGATCTGGTTGTATTCACATGTCC
913  55_HRV76       ACTCTTGATGAGATGTGTATGGAGAGTTTCTTAGGGAGATCTGGTTGTATTCATATTTCA
914  56_HRV76b|     ACTCTTGATGAGATGTGTATGGAGAGTTTCTTAGGGAGATCTGGTTGTATTCATATTTCA
915  57_HRV76a|     ACTCTTGATGAGATGTGTATGGAGAGTTTCTTAGGGAGATCTGGTTGTATTCATATTTCA
916  58_HRV33       ACTCTTGATGAGTGTGGAAAGCTTCTTAGGTAGGTCTGGTTGCATTCACATGTCA
917  59_HRV33b|     ACTCTTGATGAGATGAGTGTGGAAAGCTTCTTAGGAAGGTCTGGTTGCATTCACATGTCA
918  60_HRV33a|     ACTCTTGATGAGATGAGTGTGGAAAGCTTCTTAGGAAGGTCTGGTTGCATTCACATGTCA
919  61_HRV24a|     ACATTACATGAGATGAGTGTTGAAAGTTTCTTGGGTAGATCAGGTTGCATACACATGTCC
920  62_HRV24b|     ACATTACATGAGATGAGTGTTGAAAGTTTCTTGGGTAGATCAGGTTGCATACACATGTCC
921  63_HRV24       ACATTACATGAGATGAGTGTTGAAAGTTTCTTGGGTAGATCAGGTTGCATACACATGTCC
922  64_HRV90       ACAAGAGATGAAATGAGTGTTGAAAGTTTTCTAGGGAGATCAGGTTGCATTCATATGTCA
923  65_HRV90a|     ACAAGAGATGAAATGAGTGTTGAAAGTTTTCTAGGGAGATCAGGTTGCATTCATATGTCA
924  66_HRV90b|     ACAAGAGATGAAATGAGTGTTGAAAGTTTTCTAGGGAGATCAGGTTGCATTCATATGTCA
925  67_HRV34       ACAAGAGATGAAATGAGCATTGAGAGTTTCCTGGGTAGGTCTGGCTGTATACACATGTCC
926  68_HRV34b|     ACAAGAGATGAAATGAGCATTGAGAGTTTCCTGGGTAGGTCTGGCTGTATACACATGTCC
927  69_HRV34a|     ACAAGAGATGAAATGAGCATTGAGAGTTTCCTGGGTAGGTCTGGCTGTATACACATGTCC
928  70_HRV50a|     ACAAGAGATGAAATGAGCATTGAAAGTTTCCTAGGTAGATCTGGTTGTATACATATATCT
929  71_HRV50b|     ACAAGAGATGAAATGAGCATTGAAAGTTTCCTAGGTAGATCTGGTTGTATACATATATCT
930  72_HRV50       ACAAGAGATGAAATGAGCATTGAAAGTTTCCTAGGTAGATCTGGTTGTATACATATATCT
931  73_HRV18a|     ACAAGAGATGAAATGAGTATAGAGTGTTTTCTAGGCAGATCAGGGTGTATACATATCTCC
932  74_HRV18b|     ACAAGAGATGAAATGAGTATAGAGTGTTTTCTAGGCAGATCAGGGTGTATACATATCTCC
933  75_HRV18       ACAAGAGATGAAATGAGTATAGAGTGTTTTCTAGGCAGATCAGGGTGTATACATATCTCC
934  76_HRV55       ACTCGTGATGAGATGAGCATTGAAAGTTTCTAGGTAGATCAGGATGTGTACATATCA
935  77_HRV55b|     ACTCGTGATGAGATGAGCATTGAAAGTTTCTAGGTAGATCAGGATGTGTACATATCA
936  78_HRV55a|     ACTCGTGATGAGATGAGCATTGAAAGTTTCTAGGTAGATCAGGATGTGTACATATCA
937  79_HRV57       ACACGTGATGAAATGAGTCTTGAGAGCTTCTTAGGAAGATCTGGCTGCATTCATATTTCA
938  80_HRV57a|     ACACGTGATGAAATGAGTCTTGAGAGCTTCTTAGGAAGATCTGGCTGCATTCATATTTCA
939  81_HRV57b|     ACACGTGATGAAATGAGTCTTGAGAGCTTCTTAGGAAGATCTGGCTGCATTCATATTTCA
940  82_HRV21       ACACGTGATGAAATGAGTATTGAAAGTTTTCTGGGCAGATCAGGGTGCATTCACATGTCA
941  83_HRVHan      ACACGTGATGAAATGAGTATTGAAAGTTTTCTGGGCAGATCAGGGTGTATCCACATGTCA
942  84_HRV43       ACCAGAGATGAAATGAGTATTGAAAGTTTCTTGGGCAGATCTGGTTGCATACATATTTCA
943  85_HRV43b|     ACCAGAGATGAAATGAGTATTGAAAGTTTCTTGGGCAGATCTGGTTGCATACATATTTCA
944  86_HRV43a|     ACCAGAGATGAAATGAGTATTGAAAGTTTCTTGGGCAGATCTGGTTGCATACATATTTCA
945  87_HRV75       ACTAGAGATGAGATGAGTATTGAGAGTTTCCTAGGCAGATCTGGATGTATTCATATTTCA
946  88_HRV75b|     ACTAGAGATGAGATGAGTATTGAGAGTTTCCTAGGCAGATCTGGATGTATTCATATTTCA
947  89_HRV75a|     ACTAGAGATGAGATGAGTATTGAGAGTTTCCTAGGCAGATCTGGATGTATTCATATTTCA
948  96_HRV9a|d     ACCAGAGATGAGATGAGTCTTGAAAGCTTCTTAGGGAGATCAGGTTGTATACACATATCT
949  97_HRV9b|d     ACCAGAGATGAAATGAGTCTTGAAAGCTTCTTAGGGAGATCAGGTTGTATACACATATCT
950  98_HRV9        ACCAGAGATGAAATGAGTCTTGAAAGCTTCTTAGGGAGATCAGGTTGTATACACATATCT
951  99_HRV32       ACTAGAGATGAGATGAGTCTTGAGAGCTTCTTAGGGAGGTCAGGATGTGTACATATATCC
952 100_HRV32a      ACTAGAGATGAGATGAGTCTTGAGAGCTTCTTAGGGAGGTCAGGATGTGTACATATATCC
953 101_HRV32b      ACTAGAGATGAGATGAGTCTTGAGAGCTTCTTAGGGAGGTCAGGATGTGTACATATATCC
954 102_HRV67       ACCAGAGATGAAATGAGTCTCGAGAGCTTTCTTGGAAGGTCAGGCTGTATTCATATATCA
955 103_HRV67a      ACCAGAGATGAAATGAGTCTCGAGAGCTTTCTTGGAAGGTCAGGCTGTATTCATATATCA
956 104_HRV67b      ACCAGAGATGAAATGAGTCTCGAGAGCTTTCTTGGAAGGTCAGGCTGTATTCATATATCA
957 105_HRV15       ACCAGAGATGAAATGAGTATTGAGAGCTTCCTTGGTAGATCAGGGTGTGTCCATATTTCT
958 106_HRV15a      ACCAGAGATGAAATGAGTATTGAGAGCTTCCTTGGTAGATCAGGGTGTGTCCATATTTCT
959 107_HRV15b      ACCAGAGATGAAATGAGTATTGAGAGCTTCCTTGGTAGATCAGGGTGTGTCCATATTTCT
960 108_HRV74a      ACAAGAGATGAGATGAGTGTAGAAAAGTTTTCTTGGAAGATCAGGATGCATCCATATCTCA
961 109_HRV74b      ACAAGAGATGAGATGAGTGTAGAAAAGTTTTCTTGGAAGATCAGGATGCATCCATATCTCA
962 110_HRV74       ACAAGAGATGAGATGAGTGTAGAAAAGTTTTCTTGGAAGATCAGGATGCATCCATATCTCA
963 111_HRV38a      ACTAGAGATGAAATGAGTGTAGAAAGTTTCTAGGAAGATCAGGTTGTGTACATATATCC
964 112_HRV38b      ACTAGAGATGAAATGAGTGTAGAAAGTTTTCTAGGAAGATCAGGTTGTGTACATATATCC
965 113_HRV38       ACTAGAGATGAAATGAGTGTAGAAAGTTTTCTAGGAAGATCAGGTTGTGTACATATATCC
966 114_HRV60       ACTAGAGATGAGATGAGTGTTGAGAGCTTCCTCGGCAGATCTGGATGTATTCATATTTCC
967 115_HRV60a      ACTAGAGATGAGATGAGTGTTGAGAGCTTCCTCGGCAGATCTGGATGTATTCATATTTCC
968 116_HRV60b      ACTAGAGATGAGATGAGTGTTGAGAGCTTCCTCGGCAGATCTGGATGTATTCATATTTCC
969 117_HRV64a      ACTAGAGATGAAATGAGCATTGAGAGTTTCTTGGGCAGGTCTGGTTGTATACACATATCA
970 118_HRV64b      ACTAGAGATGAAATGAGCATTGAGAGTTTCTTGGGCAGGTCTGGTTGTATACACATATCA
971 119_HRV64       ACTAGAGATGAAATGAGCATTGAGAGTTTCTTGGGCAGGTCTGGTTGTATACACATATCA
972 120_HRV94a      ACAAGGGATGAAATGAGCATTGAAAGCTTCTTGGGAAGATCTGGCTGTATACACATAGCA
973 121_HRV94b      ACAAGGGATGAAATGAGCATTGAAAGCTTCTTGGGAAGATCTGGCTGTATACACATAGCA
974 122_HRV94       ACAAGGGATGAAATGAGCATTGAAAGCTTCTTGGGAAGATCTGGCTGTATACACATAGCA
975 123_HRV22       ACTAGAGATGAAATGAGTATTGAGAGCTTCCTGGGAAGATCTGGTTGCATACATATATCA
```

FIG. D6 CONT'D 02.trace                                                           9/20/2007 4:59 PM

```
 976  124_HRV22a    ACTAGAGATGAAATGAGTATTGAGAGCTTCCTGGGAAGATCTGGTTGCATACATATATCA
 977  125_HRV22b    ACTAGAGATGAAATGAGTATTGAGAGCTTCCTGGGAAGATCTGGTTGCATACATATATCA
 978  126_HRV82     ACTAGAGATGAGATGAGCCTTGAGAGTTTCCTAGGGAGATCTGGCTGCATACACATATCA
 979  127_HRV82b    ACTAGAGATGAGATGAGCCTTGAGAGTTTCCTAGGGAGATCTGGCTGCATACACATATCA
 980  128_HRV82a    ACTAGAGATGAGATGAGCCTTGAGAGTTTCCTAGGGAGATCTGGCTGCATACACATATCA
 981  129_HRV19     ACTAGGGATGAAATGAGCATAGAAAGTTTTCTTGGCAGATCCGGTTGTGTACATGTTTCA
 982  130_HRV19a    ACTAGGGATGAAATGAGCATAGAAAGTTTTCTTGGCAGATCCGGTTGTGTACATGTTTCA
 983  131_HRV19b    ACTAGGGATGAAATGAGCATAGAAAGTTTTCTTGGCAGATCCGGTTGTGTACATGTTTCA
 984  132_HRV13     ACTAGGGATGAAATGAGTGTTGAGAGCTTTTAGGCAGATCTGGTTGTATACACATGTCT
 985  133_HRV13a    ACTAGGGATGAAATGAGTGTTGAGAGCTTTTTAGGCAGATCTGGTTGTATACACATGTCT
 986  134_HRV13b    ACTAGGGATGAAATGAGTGTTGAGAGCTTTTTAGGCAGATCTGGTTGTATACACATGTCT
 987  135_HRV41     ACTAGAGATGAAATGAGCATAGAAAGCTTTTTAGGTAGATCAGGCTGTGTACATAAGTCC
 988  136_HRV41a    ACTAGAGATGAAATGAGCATAGAAAGCTTTTTAGGTAGATCAGGCTGTGTACATAAGTCC
 989  137_HRV41b    ACTAGAGATGAAATGAGCATAGAAAGCTTTTTAGGTAGATCAGGCTGTGTACATAAGTCC
 990  138_HRV73     ACTAGAGATGAAATGAGCATTGAAAGCTTCCTTGGCAGGTCAGGTTGTATACACATGTCA
 991  139_HRV73b    ACTAGAGATGAAATGAGCATTGAAAGCTTCCTTGGCAGGTCAGGTTGTATACACATGTCA
 992  140_HRV73a    ACTAGAGATGAAATGAGCATTGAAAGCTTCCTTGGCAGGTCAGGTTGTATACACATGTCA
 993  141_HRV61     ACAAGAGATGAAATGAGTGTAGAAAGTTTCTTGGGTAGATCAGGGTGCATACATATGTCA
 994  142_HRV61a    ACAAGAGATGAAATGAGTGTAGAAAGTTTCTTGGGTAGATCAGGGTGCATACATATGTCA
 995  143_HRV61b    ACAAGAGATGAAATGAGTGTAGAAAGTTTCTTGGGTAGATCAGGGTGCATACATATGTCA
 996  144_HRV96     ACGAGAGATGAAATGAGCATTGAGAGCTTTTTGGGTAGATCAGGGTGTATACACATGTCA
 997  145_HRV96b    ACGAGAGATGAAATGAGCATTGAGAGCTTTTTGGGTAGATCAGGGTGTATACACATGTCA
 998  146_HRV96a    ACGAGAGATGAAATGAGCATTGAGAGCTTTTTGGGTAGATCAGGGTGTATACACATGTCA
 999   90_HRV16a|   ACATTGGATGAAATGAGTGTGGAAAGCTTCCTAGGCAGATCGGGGTGCATCCATGAATCA
1000   91_HRV16b|   ACATTGGATGAAATGAGTGTGGAAAGCTTCCTAGGCAGATCGGGGTGCATCCATGAATCA
1001   92_1AYM_A    ACATTGGATGAAATGAGTGTGGAAAGCTTCCTAGGCAGATCGGGGTGCATCCATGAATCA
1002   93_HRV81a|   ACACTGGATGAAATGAGTGTAGAAAGTTTTTAGGCAGATCAGGTTGCATTCATGAATCC
1003   94_HRV81b|   ACACTGGATGAAATGAGTGTAGAAAGTTTTTAGGCAGATCAGGTTGCATTCATGAATCC
1004   95_HRV81     ACACTGGATGAAATGAGTGTAGAAAGTTTTTAGGCAGATCAGGTTGCATTCATGAATCC
1005  147_HRV2      ACAAGAGATGAAATGAGTTTAGAGAGTTTTCTTGGCAGATCAGGATGCATACATGAATCT
1006  148_HRV2a|    ACAAGAGATGAAATGAGTTTAGAGAGTTTTCTTGGCAGATCAGGATGCATACATGAATCT
1007  149_HRV2b|    ACAAGAGATGAAATGAGTTTAGAGAGTTTTCTTGGCAGATCAGGATGCATACATGAATCT
1008  150_HRV49a    ACAAGAGATGAAATGAGTTTAGAGAGTTTTCTTGGTAGGTCAGGGTGTATACATGAATCC
1009  151_HRV49b    ACAAGAGATGAAATGAGTTTAGAGAGTTTTCTTGGTAGGTCAGGGTGTATACATGAATCC
1010  152_HRV49     ACAAGAGATGAAATGAGTTTAGAGAGTTTTCTTGGTAGGTCAGGGTGTATACATGAATCC
1011  153_HRV23a    ACAAGAGATGAAATGAGTTTAGAAAGTTTCCTTGGTAGGTCAGGGTGTATACATGAATCT
1012  154_HRV23b    ACAAGAGATGAAATGAGTTTAGAAAGTTTCCTTGGTAGGTCAGGGTGTATACATGAATCT
1013  155_HRV23     ACAAGAGATGAAATGAGTTTAGAAAGTTTCCTTGGTAGGTCAGGGTGTATACATGAATCT
1014  156_HRV30a    ACAAGGGATGAAATGAGTTTAGAAAGCTTTCTTGGTAGATCAGGATGTATACACGAGTCT
1015  157_HRV30b    ACAAGGGATGAAATGAGTTTAGAAAGCTTTCTTGGTAGATCAGGATGTATACACGAGTCT
1016  158_HRV30     ACAAGGGATGAAATGAGTTTAGAAAGCTTTCTTGGTAGATCAGGATGTATACACGAGTCT
1017  159_HRV7      ACAAGGGATGAAACTAGTATAGAGAGTTTCTTAGGTAGATCTGGATGTATTGCTAAAGTT
1018  160_HRV7b|    ACAAGGGATGAAACTAGTATAGAGAGTTTCTTAGGTAGATCTGGATGTATTGCTAAAGTT
1019  161_HRV7a|    ACAAGGGATGAAACTAGTATAGAGAGTTTCTTAGGTAGATCTGGATGTATTGCTAAAGTT
1020  162_HRV88     ACAAGGGATGAAACCAGCATTGAAAGCTTTCTGGGTAGGTCTGGATGCATAGCAAAAATT
1021  163_HRV88a    ACAAGGGATGAAACCAGCATTGAAAGCTTTCTGGGTAGGTCTGGATGCATAGCAAAAATT
1022  164_HRV88b    ACAAGGGATGAAACCAGCATTGAAAGCTTTCTGGGTAGGTCTGGATGCATAGCAAAAATT
1023  165_HRV36a    ACAAGAGATGAGACAAGTATTGAAAGCTTCTTAGGTAGGTCAGGGTGCATAGCTATGATA
1024  166_HRV36b    ACAAGAGATGAGACAAGTATTGAAAGCTTCTTAGGTAGGTCAGGGTGCATAGCTATGATA
1025  167_HRV36     ACAAGAGATGAGACAAGTATTGAAAGCTTCTTAGGTAGGTCAGGGTGCATAGCTATGATA
1026  168_HRV89a    ACAAGGGATGAAACAAGTATTGAGAGTTTCTTAGGTAGGTCAGGGTGTATCGCTATGATA
1027  169_HRV89b    ACAAGGGATGAAACAAGTATTGAGAGTTTCTTAGGTAGGTCAGGGTGTATCGCTATGATA
1028  170_HRV89     ACAAGGGATGAAACAAGTATTGAGAGTTTCTTAGGTAGGTCAGGGTGTATCGCTATGATA
1029  171_HRV58     ACAAGAGATGAAACTAGCATTGAAAGCTTTTAGGTAGATCTGGTTGCATTGCTATCATA
1030  172_HRV58a    ACAAGAGATGAAACTAGCATTGAAAGCTTTTTAGGTAGATCTGGTTGCATTGCTATCATA
1031  173_HRV58b    ACAAGAGATGAAACTAGCATTGAAAGCTTTTTAGGTAGATCTGGTTGCATTGCTATCATA
1032  174_HRV12a    ACTAGAGATGAGATGTCAATTGAATCTTTCCTTGGTCGGTCCGGATGCATTTCAATTATC
1033  175_HRV12b    ACTAGAGATGAGATGTCAATTGAATCTTTCCTTGGTCGGTCCGGATGCATTTCAATTATC
1034  176_HRV12     ACTAGAGATGAGATGTCAATTGAATCTTTCCTTGGTCGGTCCGGATGCATTTCAATTATC
1035  177_HRV78a    ACAAGAGATGAAATGAGCATTGAAAGTTTCCTCGGAAGATCAGGTTGTGCAACAATTATG
1036  178_HRV78b    ACAAGAGATGAAATGAGCATTGAAAGTTTCCTCGGAAGATCAGGTTGTGCAACAATTATG
1037  179_HRV78     ACAAGAGATGAAATGAGCATTGAAAGTTTCCTCGGAAGATCAGGTTGTGCAACAATTATG
1038  180_HRV20     ACCCGTGATGAAATGAGTGTGGAAAGTTTTCTTGGTAGATCTGGTTGCATTGCTATCATA
1039  181_HRV20a    ACCCGTGATGAAATGAGTGTGGAAAGTTTTCTTGGTAGATCTGGTTGCATTGCTATCATA
1040  182_HRV20b    ACCCGTGATGAAATGAGTGTGGAAAGTTTTCTTGGTAGATCTGGTTGCATTGCTATCATA
```

FIG. D6 CONT'D

02.trace                                                              9/20/2007 4:59 PM

```
1041 183_HRV68     ACAAGGGATGAAATGAGCATAGAGAGCTTCCTCGGTAGGTCAGGTTGCATTGCAATCATA
1042 184_HRV68a    ACAAGGGATGAAATGAGCATAGAGAGCTTCCTCGGTAGGTCAGGTTGCATTGCAATCATA
1043 185_HRV68b    ACAAGGGATGAAATGAGCATAGAGAGCTTCCTCGGTAGGTCAGGTTGCATTGCAATCATA
1044 186_HRV28     ACCCGTGATGAAATGAGTATAGAGAGTTTCTTAGGTAGGTCTAGTTGCATTGCAATAATC
1045 187_HRV28a    ACCCGTGATGAAATGAGTATAGAGAGTTTCTTAGGTAGGTCTAGTTGCATTGCAATAATC
1046 188_HRV28b    ACCCGTGATGAAATGAGTATAGAGAGTTTCTTAGGTAGGTCTAGTTGCATTGCAATAATC
1047 189_HRV53a    ACCCGGGATGAAATGAGCATTGAAAGTTTCTTAGGCAGATCAAGTTGCATTGCTGAGATC
1048 190_HRV53b    ACCCGGGATGAAATGAGCATTGAAAGTTTCTTAGGCAGATCAAGTTGCATTGCTGAGATC
1049 191_HRV53     ACCCGGGATGAAATGAGCATTGAAAGTTTCTTAGGCAGATCAAGTTGCATTGCTGAGATC
1050 192_HRV46a    ACAAAAGATGAAATGAGTATAGAAAGTTTTCTAGGAAGGTCAGGCTGCATTGCCATTATT
1051 193_HRV46b    ACAAAAGATGAAATGAGTATAGAAAGTTTTCTAGGAAGGTCAGGCTGCATTGCCATTATT
1052 194_HRV46     ACAAAAGATGAAATGAGTATAGAAAGTTTTCTAGGAAGGTCAGGCTGCATTGCCATTATT
1053 195_HRV80a    ACAAAGGATGAGATGAGCATTGAAAGTTTCTTAGGAAGATCTGGTTGTGTTGCTATCATT
1054 196_HRV80b    ACAAAGGATGAGATGAGCATTGAAAGTTTCTTAGGAAGATCTGGTTGTGTTGCTATCATT
1055 197_HRV80     ACAAAGGATGAGATGAGCATTGAAAGTTTCTTAGGAAGATCTGGTTGTGTTGCTATCATT
1056 198_HRV51     ACTAGAGATGAAATGAGTATAGAGAGTTTCTTGGGTAGATCTGCTTGCGTAGCAATCATC
1057 199_HRV51a    ACTAGAGATGAAATGAGTATAGAGAGTTTCTTGGGTAGATCTGCTTGCGTAGCAATCATC
1058 200_HRV51b    ACTAGAGATGAAATGAGTATAGAGAGTTTCTTGGGTAGATCTGCTTGCGTAGCAATCATC
1059 201_HRV65a    ACCAGAGATGAGATGAGCGTAGAGAGTTTCCTGGGCAGATCTGCCTGCATAGCAGTCATT
1060 202_HRV65b    ACCAGAGATGAGATGAGCGTAGAGAGTTTCCTGGGCAGATCTGCCTGCATAGCAGTCATT
1061 203_HRV65     ACCAGAGATGAGATGAGCGTAGAGAGTTTCCTGGGCAGATCTGCCTGCATAGCAGTCATT
1062 204_HRV71a    ACTAGGGATGAAATGAGCATTGAGAGCTTCTTGGGCAGATCTGCATGCATAGCTACCATA
1063 205_HRV71b    ACTAGGGATGAAATGAGCATTGAGAGCTTCTTGGGCAGATCTGCATGCATAGCTACCATA
1064 206_HRV71     ACTAGGGATGAAATGAGCATTGAGAGCTTCTTGGGCAGATCTGCATGCATAGCTACCATA
1065 207_HRV8      ACTAGGCATGAGACATCACTGGAATCTTTCTTGGGTAGAGCAGGATGCATTAAAATCATT
1066 208_HRV95     ACTAGGTATGAGACATCACTGGAATCTTTCTTGGGTAGAGCAGGATGCATTAAAATTATT
1067 209_HRV45     ACCAGACATGAAACCTCCATTGAATCTTTTTGGGTAGGGCTGGATGTGTGGCCAATATT
1068 210_HRV45a    ACCAGACATGAAACCTCCATTGAATCTTTTTGGGTAGGGCTGGATGTGTGGCCAATATT
1069 211_HRV45b    ACCAGACATGAAACCTCCATTGAATCTTTTTGGGTAGGGCTGGATGTGTGGCCAATATT
1070 GROUP_1       AC-----ATGA-A------T-GA----TT--T-GG--G--C----TG------------
1071
1072 1_HRV1A1|d    AGAATAAAGGTTGATTACACTGAC---------------TATAATGGA---CAGGACATA
1073 2_HRV1A2|d    AGAATAAAGGTTGATTACACTGAC---------------TATAATGGA---CAGGACATA
1074 3_HRV1A|cD    AGAATAAAGGTTGATTACACTGAC---------------TATAATGGA---CAGGACATA
1075 4_HRV1B1|d    AGAATAAAGGTTGATTACAATGAC---------------TACAATGGA---GTGAACAAA
1076 5_HRV1B2|d    AGAATAAAGGTTGATTACAATGAC---------------TACAATGGA---GTGAACAAA
1077 6_HRV1B       AGAATAAAGGTTGATTACAATGAC---------------TACAATGGA---GTGAACAAA
1078 7_HRV40a|d    ACAATTACAGTGGATAACAGTTTG---------------GAATATG------ATGACCAC
1079 8_HRV40b|d    ACAATTACAGTGGATAACAGTTTG---------------GAATATG------ATGACCAC
1080 9_HRV40       ACAATTACAGTGGATAACAGTTTG---------------GAATATG------ATGACCAC
1081 10_HRV85      ACAATTACTGTGAATAACAACCTA---------------GATTATG------ATGAAAAT
1082 11_HRV85a|    ACAATTACTGTGAATAACAACCTA---------------GATTATG------ATGAAAAT
1083 12_HRV85b|    ACAATTACTGTGAATAACAACCTA---------------GATTATG------ATGAAAAT
1084 13_HRV56a|    ACTATAACTGTGGATAATGATGTA---------------GATTATA------ATTCAAAG
1085 14_HRV56b|    ACTATAACTGTGGATAATGATGTA---------------GATTATA------ATTCAAAG
1086 15_HRV56      ACTATAACTGTGGATAATGATGTA---------------GATTATA------ATTCAAAG
1087 16_HRV54      ACCATTACAATTCAAAATGATGTA---------------GAATACA------ATGATCAC
1088 17_HRV98      ACTATCACTATTCAAAATGATGTA---------------GAATATA------ACGATCAT
1089 18_HRV59a|    ACTATTACTGTCAATAAAGACATA---------------AAATATG------ATGATGGA
1090 19_HRV59b|    ACTATTACTGTCAATAAAGACATA---------------AAATATG------ATGATGGA
1091 20_HRV59      ACTATTACTGTCAATAAAGACATA---------------AAATATG------ATGATGGA
1092 21_HRV63      ACTATCACTGTTGACAAAACCATT---------------GACTATG------ACACTGGA
1093 22_HRV63b|    ACTATCACTGTTGACAAAACCATT---------------GACTATG------ACACTGGA
1094 23_HRV63a|    ACTATCACTGTTGACAAAACCATT---------------GACTATG------ACACTGGA
1095 24_HRV39      ACAATTACTATGAAGAAGGAG------------------AACTATA------ATGATCAT
1096 25_HRV39a|    ACAATTACTATGAAGAAGGAG------------------AACTATA------ATGATCAT
1097 26_HRV39b|    ACAATTACTATGAAGAAGGAG------------------AACTATA------ATGAACAT
1098 27_HRV10a|    ACAATAACTGTTAATAATACAAGA---------------CCCTACA------ATGAACAC
1099 28_HRV10b|    ACAATAACTGTTAATAATACAAGA---------------CCCTACA------ATGAACAC
1100 29_HRV10      ACAATAACTGTTAATAATACAAGA---------------CCCTACA------ATGAACAC
1101 30_HRV100a    ACAATTACTGTAAGTAAAATGAAA---------------AATTATA------ATGAGCAC
1102 31_HRV100b    ACAATTACTGTAAGTAAAATGAAA---------------AATTATA------ATGAGCAC
1103 32_HRV100     ACAATTACTGTAAGTAAAATGAAA---------------AATTATA------ATGAGCAC
1104 33_HRV66      ACAATTAATGTGGATAGCACAAAA---------------ACATATG------ATGAATCC
1105 34_HRV66b|    ACAATTAATGTGGATAGCACAAAA---------------ACATATG------ATGAATCC
```

FIG. D6 CONT'D

```
02.trace                                                              9/20/2007 4:59 PM 1106  35_HRV66a|    ACAATTAATGTGGATAGCACAAAA---------------ACATATG------ATGAATCC
1107  36_HRV77a|    ACAATAAATGTAGAAGATGGTAAA---------------ACTTATG------ATGAATCT
1108  37_HRV77b|    ACAATAAATGTAGAAGATGGTAAA---------------ACTTATG------ATGAATCT
1109  38_HRV77     ACAATAAATGTAGAAGATGGTAAA---------------ACTTATG------ATGAATCT
1110  39_HRV62a    ACAATTGAA--------ACAACG---------------CTTAGTC------ATAAAGAT
1111  40_HRV62b    ACAATTGAA--------ACAACG---------------CTTAGTC------ATAAAGAT
1112  41_HRV25     ACAATTGAA--------ACAAAA---------------CTTAAAC------ATGATGAA
1113  42_HRV29a    ACAATAAAA--------GCAAAT---------------CAGGCAC------ATGACGCC
1114  43_HRV29b    ACAATAAAA--------GCAAAT---------------CAGGCAC------ATGACGCC
1115  44_HRV44a    ACAATAAAG--------ACAAAT---------------CAGGCAC------ACAATACC
1116  45_HRV44b    ACAATAAAG--------ACAAAT---------------CAGGCAC------ACAATACC
1117  46_HRV31     ATAATAGAA--------CCAGAT---------------GGACTCC------ATGATAGC
1118  47_HRV31a|   ATAATAGAA--------CCAGAT---------------GGACTCC------ATGATAGC
1119  48_HRV31b|   ATAATAGAA--------CCAGAT---------------GGACTCC------ATGATAGC
1120  49_HRV47     ACAATAAAA--------TCAGAT---------------GAGCAAC------ACATTAAT
1121  50_HRV47a|   ACAATAAAA--------TCAGAT---------------GAGCAAC------ACATTAAT
1122  51_HRV47b|   ACAATACAA--------TCAAAT---------------GAGCAAC------ACATTAAT
1123  52_HRV11     AAGTTAATTGTGCAGTATGAAGAC---------------TATAAT------GGAAAGAAA
1124  53_HRV11b|   AAGTTAATTGTGCAGTATGAAGAC---------------TATAAT------GGAAAGAAA
1125  54_HRV11a|   AAGTTAATTGTGCAGTATGAAGAC---------------TATAAT------GGAAAGAAA
1126  55_HRV76     AAGCTAGTTGTAGAATATGAGGGA---------------TATGAT------GATACAAAA
1127  56_HRV76b|   AAGCTAGTTGTAGAATATGAGGGA---------------TATGAT------GATACAAAA
1128  57_HRV76a|   AAGCTAGTTGTAGAATATGAGGGA---------------TATGAT------GATACAAAA
1129  58_HRV33     AAATTAGTAGTGAAATATGAAGAC---------------TATAAT------GAGAAAAAG
1130  59_HRV33b|   AAATTAGTAGTGAAATATGAAGAC---------------TATAAT------GAGAAAAAG
1131  60_HRV33a|   AAATTAGTAGTGAAATATGAAGAC---------------TATAAT------GAGAAAAAG
1132  61_HRV24a|   AAGTTGACTGTGGATTAT---GAC---------------AATTAT------GATACAAAA
1133  62_HRV24b|   AAGTTGACTGTGGATTAT---GAC---------------AATTAT------GATACAAAA
1134  63_HRV24     AAGTTGACTGTGGATTAT---GAC---------------AATTAT------GATACAAAA
1135  64_HRV90     AAATTAGTTGTAAACTAT---GAT---------------AATTAT------GATGAAAAC
1136  65_HRV90a|   AAATTAGTTGTAAACTAT---GAT---------------AATTAT------GATGAAAAC
1137  66_HRV90b|   AAATTAGTTGTAAACTAT---GAT---------------AATTAT------GATGAAAAC
1138  67_HRV34     AAACTTGTTGTAGATTATGAAAAT---------------TACAATGCA---AAAACAAAG
1139  68_HRV34b|   AAACTTGTTGTAGATTATGAAAAT---------------TACAATGCA---AAAACAAAG
1140  69_HRV34a|   AAACTTGTTGTAGATTATGAAAAT---------------TACAATGCA---AAAACAAAG
1141  70_HRV50a|   AAATTAGTTGTTGATTATGATGGT---------------TACAATGAG---GAAACAAAG
1142  71_HRV50b|   AAATTAGTTGTTGATTATGATGGT---------------TACAATGAG---GAAACAAAG
1143  72_HRV50     AAATTAGTTGTTGATTATGATGGT---------------TACAATGAG---GAAACAAAG
1144  73_HRV18a|   AAGTTAGTTGTACATTATGAAGAT---------------TATAATGCA---GAAACAAGG
1145  74_HRV18b|   AAGTTAGTTGTACATTATGAAGAT---------------TATAATGCA---GAAACAAGG
1146  75_HRV18     AAGTTAGTTGTACATTATGAAGAT---------------TATAATGCA---GAAACAAGG
1147  76_HRV55     GAGTTAGTTGTTCATTATGAAGAA---------------TATAACAAA---GAGGGAAAA
1148  77_HRV55b|   GAGTTAGTTGTTCATTATGAAGAA---------------TATAACAAA---GAGGGAAAA
1149  78_HRV55a|   GAGTTAGTTGTTCATTATGAAGAA---------------TATAACAAA---GAGGGAAAA
1150  79_HRV57     GAGCTTAAGGTAAAATATGAAAAT---------------TACAACACA---GAG------
1151  80_HRV57a|   GAGCTTAAGGTAAAATATGAAAAT---------------TACAACACA---GAG------
1152  81_HRV57b|   GAGCTTAAGGTAAAATATGAAAAT---------------TACAACACA---GAG------
1153  82_HRV21     AAATTAGTAGTTAACTATGATAAT---------------TACAATACT---GGAGAAAAT
1154  83_HRVHan    AAATTAATAGTTAACTATGACAAC---------------TACAATACT---GGAGAAAAT
1155  84_HRV43     ACACTTGAAGTAAATTATGATGAT---------------TATAATGGG---ACAGGCATA
1156  85_HRV43b|   ACACTTGAAGTAAATTATGATGAT---------------TATAATGGG---ACAGGCATA
1157  86_HRV43a|   ACACTTGAAGTAAATTATGATGAT---------------TATAATGGG---ACAGGCATA
1158  87_HRV75     ACACTTGAGATGGATTATACAAAC---------------TATAATGGA---GAAGGCAAA
1159  88_HRV75b|   ACACTTGAGATGGATTATACAAAC---------------TATAATGGA---GAAGGCAAA
1160  89_HRV75a|   ACACTTGAGATGGATTATACAAAC---------------TATAATGGA---GAAGGCAAA
1161  96_HRV9a|d   AAATTGAATATTGATTACAGTGAC---------------TATGATAAG---AGTGTTGAA
1162  97_HRV9b|d   AAATTGAATATTGATTACAGTGAC---------------TATGATAAG---AGTGTTGAA
1163  98_HRV9      AAATTGAATATTGATTACAGTGAC---------------TATGATAAG---AGTGTTGAA
1164  99_HRV32     AAATTAGATATTGATTATACCAAT---------------TACAATAAA---AGTGTTAAG
1165  100_HRV32a   AAATTAGATATTGATTATACCAAT---------------TACAATAAA---AGTGTTAAG
1166  101_HRV32b   AAATTAGATATTGATTATACCAAT---------------TACAATAAA---AGTGTTAAG
1167  102_HRV67    AAATTGAATATTGATTATAATGCA---------------TATGATGAA---AGTAGGGAC
1168  103_HRV67a   AAATTGAATATTGATTATAATGCA---------------TATGATGAA---AGTAGGGAC
1169  104_HRV67b   AAATTGAATATTGATTATAATGCA---------------TATGATGAA---AGTAGGGAC
1170  105_HRV15    GATTTGAAAATACATTATGAAGAT---------------TATAATAAA---GATGGGAAA
```

FIG. D6 CONT'D

```
02.trace                                                              9/20/2007 4:59 PM 1171  106_HRV15a    GATTTGAAAATACATTATGAAGAT---------------TATAATAAA---GATGGGAAA
1172  107_HRV15b    GATTTGAAAATACATTATGAAGAT---------------TATAATAAA---GATGGGAAA
1173  108_HRV74a    CATCTAAAAATTGATTATACAAAC---------------TATAATGTT---AAAGGGAAG
1174  109_HRV74b    CATCTAAAAATTGATTATACAAAC---------------TATAATGTT---AAAGGGAAG
1175  110_HRV74     CATCTAAAAATTGATTATACAAAC---------------TATAATGTT---AAAGGGAAG
1176  111_HRV38a    AATCTTGACATAGATTACATTAAT---------------TACAACTCT---GAAGACAAA
1177  112_HRV38b    AATCTTGACATAGATTACATTAAT---------------TACAACTCT---GAAGACAAA
1178  113_HRV38     AATCTTGACATAGATTACATTAAT---------------TACAACTCT---GAAGACAAA
1179  114_HRV60     AAATTAGAAATTGACTATAGTAAC---------------TACAATGAG---GAGAATAAA
1180  115_HRV60a    AAATTAGAAATTGACTATAGTAAC---------------TACAATGAG---GAGAATAAA
1181  116_HRV60b    AAATTAGAAATTGACTATAGTAAC---------------TACAATGAG---GAGAATAAA
1182  117_HRV64a    GATTTAAAAGTAAATTATACTGGG---------------TATAATGAT---GAAGGTAAC
1183  118_HRV64b    GATTTAAAAGTAAATTATACTGGG---------------TATAATGAT---GAAGGTAAC
1184  119_HRV64     GATTTAAAAGTAAATTATACTGGG---------------TATAATGAT---GAAGGTAAC
1185  120_HRV94a    CATCTAGAGATCAAGTATGATGGT---------------TACAATGAT---GCTGGCAAC
1186  121_HRV94b    CATCTAGAGATCAAGTATGATGGT---------------TACAATGAT---GCTGGCAAC
1187  122_HRV94     CATCTAGAGATCAAGTATGATGGT---------------TACAATGAT---GCTGGCAAC
1188  123_HRV22     CACTTAGAAGTAAAATACACAGGG---------------TATAATGAA---GAGGGTAAT
1189  124_HRV22a    CACTTAGAAGTAAAATACACAGGG---------------TATAATGAA---GAGGGTAAT
1190  125_HRV22b    CACTTAGAAGTAAAATACACAGGG---------------TATAATGAA---GAGGGTAAT
1191  126_HRV82     CACCTAAATGTCAGATACACTG-----------------ATTATAAT---GAAGGTAAT
1192  127_HRV82b    CACCTAAATGTCAGATACACTG-----------------ATTATAAT---GAAGGTAAT
1193  128_HRV82a    CACCTAAATGTCAGATACACTG-----------------ATTATAAT---GAAGGTAAT
1194  129_HRV19     GAGCTCCAATTAGATTATACCAAT---------------TACAATCAA---GAAAATAAT
1195  130_HRV19a    GAGCTCCAATTAGATTATACCAAT---------------TACAATCAA---GAAAATAAT
1196  131_HRV19b    GAGCTCCAATTAGATTATACCAAT---------------TACAATCAA---GAAAATAAT
1197  132_HRV13     ACCATGAACATAGATTATACTAAT---------------TATGATGAT---TCTGTTAAT
1198  133_HRV13a    ACCATGAACATAGATTATACTAAT---------------TATGATGAT---TCTGTTAAT
1199  134_HRV13b    ACCATGAACATAGATTATACTAAT---------------TATGATGAT---TCTGTTAAT
1200  135_HRV41     ACTTTGAATATAGATTATACTGAT---------------TATGATGAT---TCTATCCAG
1201  136_HRV41a    ACTTTGAATATAGATTATACTGAT---------------TATGATGAT---TCTATCCAG
1202  137_HRV41b    ACTTTGAATATAGATTATACTGAT---------------TATGATGAT---TCTATCCAG
1203  138_HRV73     ACTATGAATATAAATTATGAAAAT---------------TATGATGAT---GCTCCTGAA
1204  139_HRV73b    ACTATGAATATAAATTATGAAAAT---------------TATGATGAT---GCTCCTGAA
1205  140_HRV73a    ACTATGAATATAAATTATGAAAAT---------------TATGATGAT---GCTCCTGAA
1206  141_HRV61     ACATTAAATATAAACTATGATAAC---------------TATGATGAT---TCTATTGAA
1207  142_HRV61a    ACATTAAATATAAACTATGATAAC---------------TATGATGAT---TCTATTGAA
1208  143_HRV61b    ACATTAAATATAAACTATGATAAC---------------TATGATGAT---TCTATTGAA
1209  144_HRV96     ACATTAAACATAGATTATGACAAT---------------TATGATGAC---TCCCCTAAG
1210  145_HRV96b    ACATTAAACATAGATTATGACAAT---------------TATGATGAC---TCCCCTAAG
1211  146_HRV96a    ACATTAAACATAGATTATGACAAT---------------TATGATGAC---TCCCCTAAG
1212  90_HRV16a|    GTGTTGGATATTGTGGACAATTAC---------------AATGAT------------CAA
1213  91_HRV16b|    GTGTTGGATATTGTGGACAATTAC---------------AATGAT------------CAA
1214  92_1AYM_A     GTGTTGGATATTGTGGACAATTAC---------------AATGAT------------CAA
1215  93_HRV81a|    ATATTGGACATTAAAGAGGATTAC---------------AATACC------------CAG
1216  94_HRV81b|    ATATTGGACATTAAAGAGGATTAC---------------AATACC------------CAG
1217  95_HRV81      ATATTGGACATTAAAGAGGATTAC---------------AATACC------------CAG
1218  147_HRV2      AAATTAGAGGTTACACTTGCAAAT---------------TATAACA---------AGGAG
1219  148_HRV2a|    AAATTAGAGGTTACACTTGCAAAT---------------TATAACA---------AGGAG
1220  149_HRV2b|    AAATTAGAGGTTACACTTGCAAAT---------------TATAACA---------AGGAG
1221  150_HRV49a    AAACTAGAGGTCACACTTACAAAT------------------TACAATG---------AAAAT
1222  151_HRV49b    AAACTAGAGGTCACACTTACAAAT------------------TACAATG---------AAAAT
1223  152_HRV49     AAACTAGAGGTCACACTTACAAAT------------------TACAATG---------AAAAT
1224  153_HRV23a    AAATTAAAAGTTGAGATCGGAAAC---------------TATGATG---------AAAAC
1225  154_HRV23b    AAATTAAAAGTTGAGATCGGAAAC---------------TATGATG---------AAAAC
1226  155_HRV23     AAATTAAAAGTTGAGATCGGAAAC---------------TATGATG---------AAAAC
1227  156_HRV30a    AAATTAGAACTTGAGCTTGCACAC---------------TATGATA---------AAAAG
1228  157_HRV30b    AAATTAGAACTTGAGCTTGCACAC---------------TATGATA---------AAAAG
1229  158_HRV30     AAATTAGAACTTGAGCTTGCACAC---------------TATGATA---------AAAAG
1230  159_HRV7      AAACTTGACACAA------CACAGGGT---------GACTATGACACAGGCAAAGGTGTT
1231  160_HRV7b|    AAACTTGACACAA------CACAGGGT---------GACTATGACACAGGCAAAGGTGTT
1232  161_HRV7a|    AAACTTGACACAA------CACAGGGT---------GACTATGACACAGGCAAAGGTGTT
1233  162_HRV88     AAACTTGACACAA------ATGAAGGT---------GATTACGACACA---ATAGGTGTT
1234  163_HRV88a    AAACTTGACACAA------ATGAAGGT---------GATTACGACACA---ATAGGTGTT
1235  164_HRV88b    AAACTTGACACAA------ATGAAGGT---------GATTACGACACA---ATAGGTGTT
```

FIG. D6 CONT'D

```
02.trace                                                                              9/20/2007 4:59 PM 1236  165_HRV36a     GAATTTAGCACAAGTAGTGATAAAGAT---------GAACATGATGAA---ATTGGCAAG
1237  166_HRV36b     GAATTTAGCACAAGTAGTGATAAAGAT---------GAACATGATGAA---ATTGGCAAG
1238  167_HRV36      GAATTTAGCACAAGTAGTGATAAAGAT---------GAACATGATGAA---ATTGGCAAG
1239  168_HRV89a     GAATTTAATACAAGTAGTGATAAAACT---------GAACATGATAAA---ATTGGTAAA
1240  169_HRV89b     GAATTTAATACAAGTAGTGATAAAACT---------GAACATGATAAA---ATTGGTAAA
1241  170_HRV89      GAATTTAATACAAGTAGTGATAAAACT---------GAACATGATAAA---ATTGGTAAA
1242  171_HRV58      AAATTTAACACAA------ATAAGACT---------AATTATGATGAC---ATAGGTGTA
1243  172_HRV58a     AAATTTAACACAA------ATAAGACT---------AATTATGATGAC---ATAGGTGTA
1244  173_HRV58b     AAATTTAACACAA------ATAAGACT---------AATTATGATGAC---ATAGGTGTA
1245  174_HRV12a     GAATTGGATTTAGACCATGAAGGT---------------TATTCAGCA---GAAGGGAAA
1246  175_HRV12b     GAATTGGATTTAGACCATGAAGGT---------------TATTCAGCA---GAAGGGAAA
1247  176_HRV12      GAATTGGATTTAGACCATGAAGGT---------------TATTCAGCA---GAAGGGAAA
1248  177_HRV78a     AGACTAGAATTGGACCACACTGAT---------------TACAATGCT---GAAGGGAAA
1249  178_HRV78b     AGACTAGAATTGGACCACACTGAT---------------TACAATGCT---GAAGGGAAA
1250  179_HRV78      AGACTAGAATTGGACCACACTGAT---------------TACAATGCT---GAAGGGAAA
1251  180_HRV20      CATACTGACTTAGATCATGAAGCACAA---------CAATATAATGCA---CCCGGAAAA
1252  181_HRV20a     CATACTGACTTAGATCATGAAGCACAA---------CAATATAATGCA---CCCGGAAAA
1253  182_HRV20b     CATACTGACTTAGATCATGAAGCACAA---------CAATATAATGCA---CCCGGAAAA
1254  183_HRV68      CATACTGACTTAGATCACAATGAGGAT---------CAGTACAATGCA---CCTGGAAAA
1255  184_HRV68a     CATACTGACTTAGATCACAATGAGGAT---------CAGTACAATGCA---CCTGGAAAA
1256  185_HRV68b     CATACTGACTTAGATCACAATGAGGAT---------CAGTACAATGCA---CCTGGAAAA
1257  186_HRV28      CATACTGATGTTGTGCATGAAACAGAC---------AAGTACAACCAC---CCAGGGAAG
1258  187_HRV28a     CATACTGATGTTGTGCATGAAACAGAC---------AAGTACAACCAC---CCAGGGAAG
1259  188_HRV28b     CATACTGATGTTGTGCATGAAACAGAC---------AAGTACAACCAC---CCAGGGAAG
1260  189_HRV53a     CATACCAATTTAGACCAT---ACTG-----------GATACAATGAG---CCTGGGAAA
1261  190_HRV53b     CATACCAATTTAGACCAT---ACTG-----------GATACAATGAG---CCTGGGAAA
1262  191_HRV53      CATACCAATTTAGACCAT---ACTG-----------GATACAATGAG---CCTGGGAAA
1263  192_HRV46a     GAGACAGAATTGAATCATGAAGAAGGG---------AAATACAATGCA---GAAGATCAA
1264  193_HRV46b     GAGACAGAATTGAATCATGAAGAAGGG---------AAATACAATGCA---GAAGATCAA
1265  194_HRV46      GAGACAGAATTGAATCATGAAGAAGGG---------AAATACAATGCA---GAAGATCAA
1266  195_HRV80a     GAAACCAAATTAAACCATGAAACAGAC---------ATGTACAATGCT---GATGGTCAG
1267  196_HRV80b     GAAACCAAATTAAACCATGAAACAGAC---------ATGTACAATGCT---GATGGTCAG
1268  197_HRV80      GAAACCAAATTAAACCATGAAACAGAC---------ATGTACAATGCT---GATGGTCAG
1269  198_HRV51      CATACAAACCTTGAGCATGTTGAAGCAGACAGACAAGCCTACAATGCA---AAAGGGAAA
1270  199_HRV51a     CATACAAACCTTGAGCATGTTGAAGCAGACAGACAAGCCTACAATGCA---AAAGGGAAA
1271  200_HRV51b     CATACAAACCTTGAGCATGTTGAAGCAGACAGACAAGCCTACAATGCA---AAAGGGAAA
1272  201_HRV65a     CACACAGATCTTAAACATGACCATGAAGGCCAAAATGTTTACAATGAC---GAAGGCAGA
1273  202_HRV65b     CACACAGATCTTAAACATGACCATGAAGGCCAAAATGTTTACAATGAC---GAAGGCAGA
1274  203_HRV65      CACACAGATCTTAAACATGACCATGAAGGCCAAAATGTTTACAATGAC---GAAGGCAGA
1275  204_HRV71a     CACACTAAATTAGTACATGGAGAGGAGGG------TGTTTATAATATG---AAAGGTAAC
1276  205_HRV71b     CACACTAAATTAGTACATGGAGAGGAGGG------TGTTTATAATATG---AAAGGTAAC
1277  206_HRV71      CACACTAAATTAGTACATGGAGAGGAGGG------TGTTTATAATATG---AAAGGTAAC
1278  207_HRV8       GCATTAGAACTAGATCATGACAAC---------------TATGATGAA------------
1279  208_HRV95      GCATTAGAACTAGATCATGACAAC---------------TATGATAAA------------
1280  209_HRV45      AGTTTAGACATTAACCATGATGAC---------------TACCAAAAG------------
1281  210_HRV45a     AGTTTAGACATTAACCATGATGAC---------------TACCAAAAG------------
1282  211_HRV45b     AGTTTAGACATTAACCATGATGAC---------------TACCAAAAG------------
1283  GROUP_1        ------------------------------------------------------------
1284
1285  1_HRVA1|d      AATTTCACAAAATGGAAAATCACACTACAGGAAATGGCACAGATTAGGAGAAAATTTGAA
1286  2_HRV1A2|d     AATTTCACAAAATGGAAAATCACACTACAGGAAATGGCACAGATTAGGAGAAAATTTGAA
1287  3_HRV1A|cD     AATTTCACAAAATGGAAAATCACACTACAGGAAATGGCACAGATTAGGAGAAAATTTGAA
1288  4_HRV1B1|d     AACTTTACAACATGGAAAATCACACTGCAGGAGATGGCACAAATTAGAAGAAAATTCGAA
1289  5_HRV1B2|d     AACTTTACAACATGGAAAATCACACTGCAGGAGATGGCACAAATTAGAAGAAAATTCGAA
1290  6_HRV1B        AACTTTACAACATGGAAAATCACACTGCAGGAGATGGCACAAATTAGAAGAAAATTCGAA
1291  7_HRV40a|d     CACTTTGATAAGTGGCAGATAACCATACAAGAGATGTCACAAATTAGGAGAAAATTTGAA
1292  8_HRV40b|d     CACTTTGATAAGTGGCAGATAACCATACAAGAGATGTCACAAATTAGGAGAAAATTTGAA
1293  9_HRV40        CACTTTGATAAGTGGCAGATAACCATACAAGAGATGTCACAAATTAGGAGAAAATTTGAA
1294  10_HRV85       CACTTTGATCAGTGGCAGATAACTATACAGGAAATGGCACAAATTAGAAGGAAGTTTGAG
1295  11_HRV85a|     CACTTTGATCAGTGGCAGATAACTATACAGGAAATGGCACAAATTAGAAGGAAGTTTGAG
1296  12_HRV85b|     CACTTTGATCAGTGGCAGATAACTATACAGGAAATGGCACAAATTAGAAGGAAGTTTGAG
1297  13_HRV56a|     CATTATAATAAATGGCAAATAACCTTACAAGAAATGGCTCAAGTTAGGCGTAAATTTGAA
1298  14_HRV56b|     CATTATAATAAATGGCAAATAACCTTACAAGAAATGGCTCAAGTTAGGCGTAAATTTGAA
1299  15_HRV56       CATTATAATAAATGGCAAATAACCTTACAAGAAATGGCTCAAGTTAGGCGTAAATTTGAA
1300  16_HRV54       CATTTTAAGAAATGGGATATAACATTACAAGAGATGGCTCACAAATACGAAGGAAATTTGAA
```

FIG. D6 CONT'D 02.trace                                                                9/20/2007 4:59 PM

```
1301  17_HRV98     CATTTTAGACAATGGGATATAACATTACAAGAAATGGCACAAATTCGAAGAAAATTTGAA
1302  18_HRV59a|   CACTTTCTTAAATGGCCTATAACATTACAAGAGATGGCACAAATTAGGAGAAAATTTGAA
1303  19_HRV59b|   CACTTTCTTAAATGGCCTATAACATTACAAGAGATGGCACAAATTAGGAGAAAATTTGAA
1304  20_HRV59     CACTTTCTTAAATGGCCTATAACATTACAAGAGATGGCACAAATTAGGAGAAATTTGAA
1305  21_HRV63     CATTTTAATAAATGGCAAATAACATTACAAGAGATGGCACAAATTAGAAGGAAATTTGAA
1306  22_HRV63b|   CATTTTAATAAATGGCAAATAACATTACAAGAGATGGCACAAATTAGAAGGAAATTTGAA
1307  23_HRV63a|   CATTTTAATAAATGGCAAATAACATTACAAGAGATGGCACAAATTAGAAGGAAATTTGAA
1308  24_HRV39     AATTTTGTGGATTGGAAAATTACTTTGCAGGAGATGGCACAGGTTAGAAGGAAATTTGAA
1309  25_HRV39a|   AATTTTGTGGATTGGAAAATTACTTTGCAGGAGATGGCACAGGTTAGAAGGAAATTTGAA
1310  26_HRV39b|   AATTTTGTGGATTGGAAAATTACTTTGCAGGAGATGGCACAGGTTAGAAGGAAATTTGAA
1311  27_HRV10a|   ACTTTTGACACATGGCAAATAACTCTACAAGAAATGGCCCAAATTAGAAGGAAATTTGAA
1312  28_HRV10b|   ACTTTTGACACATGGCAAATAACTCTACAAGAAATGGCCCAAATTAGAAGGAAATTTGAA
1313  29_HRV10     ACTTTTGACACATGGCAAATAACTCTACAAGAAATGGCCCAAATTAGAAGGAAATTTGAA
1314  30_HRV100a   ACTTTTGACAAATGGCAAATAACCCTACAGGAAATGGCCCAAATTAGAAGGAAATTTGAA
1315  31_HRV100b   ACTTTTGACAAATGGCAAATAACCCTACAGGAAATGGCCCAAATTAGAAGGAAATTTGAA
1316  32_HRV100    ACTTTTGACAAATGGCAAATAACCCTACAGGAAATGGCCCAAATTAGAAGGAAATTTGAA
1317  33_HRV66     AAATTTAGAACATGGCAAATTACATTGCAAGAAATGGCTCAAATCAGACGCAAATTTGAG
1318  34_HRV66b|   AAATTTAGAACATGGCAAATTACATTGCAAGAAATGGCTCAAATCAGACGCAAATTTGAG
1319  35_HRV66a|   AAATTTAGAACATGGCAAATTACATTGCAAGAAATGGCTCAAATCAGACGCAAATTTGAG
1320  36_HRV77a|   AAATTTAGAAAATGGCAAATTACACTACAAGAAATGGCTCAAATTAGGCGCAAATTTGAA
1321  37_HRV77b|   AAATTTAGAAAATGGCAAATTACACTACAAGAAATGGCTCAAATTAGGCGCAAATTTGAA
1322  38_HRV77     AAATTTAGAAAATGGCAAATTACACTACAAGAAATGGCTCAAATTAGGCGCAAATTTGAA
1323  39_HRV62a    AGATTCAAAACATGGAATATTAACTTACAAGAGATGGCTCAAATCAGGAGAAAGTTTGAA
1324  40_HRV62b    AGATTCAAAACATGGAATATTAACTTACAAGAGATGGCTCAAATCAGGAGAAAGTTTGAA
1325  41_HRV25     AGATTTAAAATATGGAATATCAATTTACAAGAAATGGCTCAAATTAGGAGAAAGTTTGAG
1326  42_HRV29a    AAGTTCGATAAATGGAATGTTAACTTACAAGAAATGGCTCAAATTAGGCGCAAATTTGAA
1327  43_HRV29b    AAGTTCGATAAATGGAATGTTAACTTACAAGAAATGGCTCAAATTAGGCGCAAATTTGAA
1328  44_HRV44a    AAGTTTGATAAATGGAATATCAACTTACAAGAAATGGCTCAAATTAGACGCAAATTTGAA
1329  45_HRV44b    AAGTTTGATAAATGGAATATCAACTTACAAGAAATGGCTCAAATTAGACGCAAATTTGAA
1330  46_HRV31     AAATATAAAGTATGGCACATTAATTTACAAGAGATGGCCCAGATTAGGCGAAAATTTGAA
1331  47_HRV31a|   AAATATAAAGTATGGCACATTAATTTACAAGAGATGGCCCAGATTAGGCGAAAATTTGAA
1332  48_HRV31b|   AAATATAAAGTATGGCACATTAATTTACAAGAGATGGCCCAGATTAGGCGAAAATTTGAA
1333  49_HRV47     AAATTTAAAGTATGGCACATTAATTTACAAGAAATGGCCCAGATCAGGCGTAAATATGAA
1334  50_HRV47a|   AAATTTAAAGTATGGCACATTAATTTACAAGAAATGGCCCAGATCAGGCGTAAATATGAA
1335  51_HRV47b|   AAATTTAAAGTATGGCACATTAATTTACAAGAAATGGCCCAGATCAGGCGTAAATATGAA
1336  52_HRV11     AACTTTAACACATGGAAAATAAACTTGCAAGAGATGGCACAAATTAGAAGGAAATTTGAA
1337  53_HRV11b|   AACTTTAACACATGGAAAATAAACTTGCAAGAGATGGCACAAATTAGAAGGAAATTTGAA
1338  54_HRV11a|   AACTTTAACACATGGAAAATAAACTTGCAAGAGATGGCACAAATTAGAAGGAAATTTGAA
1339  55_HRV76     AACTTTAAGACATGGAAAATAAACCTACAAGAAATGGCACAAGTTAGAAGAAAATTTGAG
1340  56_HRV76b|   AACTTTAAGACATGGAAAATAAACCTACAAGAAATGGCACAAGTTAGAAGAAAATTTGAG
1341  57_HRV76a|   AACTTTAAGACATGGAAAATAAACCTACAAGAAATGGCACAAGTTAGAAGAAAATTTGAG
1342  58_HRV33     AATTTTATGACATGGAAAATAAATCTACAAGAGATGGCACAGATTAGGAGGAAATTTGAA
1343  59_HRV33b|   AATTTTATGACATGGAAAATAAATCTACAAGAGATGGCACAGATTAGGAGGAAATTTGAA
1344  60_HRV33a|   AATTTTATGACATGGAAAATAAATCTACAAGAGATGGCACAGATTAGGAGGAAATTTGAA
1345  61_HRV24a|   AATTTTTTCAAATGGCAAATAAATCTACAAGAAATGGCCCAAGTCAGAAGAAAATTTGAA
1346  62_HRV24b|   AATTTTTTCAAATGGCAAATAAATCTACAAGAAATGGCCCAAGTCAGAAGAAAATTTGAA
1347  63_HRV24     AATTTTTTCAAATGGCAAATAAATCTACAAGAAATGGCCCAAGTCAGAAGAAAATTTGAA
1348  64_HRV90     AACTTCCATAAATGGCAAATTAACCTGCAAGAGATGGCACAGATTAGAAGAAAATTTGAA
1349  65_HRV90a|   AACTTCCATAAATGGCAAATTAACCTGCAAGAGATGGCACAGATTAGAAGAAAATTTGAA
1350  66_HRV90b|   AACTTCCATAAATGGCAAATTAACCTGCAAGAGATGGCACAGATTAGAAGAAAATTTGAA
1351  67_HRV34     AACTTTATGACATGGCAAATTAATTTACAGGAAATGGCACAGATTAGAAGGAAATTTGAA
1352  68_HRV34b|   AACTTTATGACATGGCAAATTAATTTACAGGAAATGGCACAGATTAGAAGGAAATTTGAA
1353  69_HRV34a|   AACTTTATGACATGGCAAATTAATTTACAGGAAATGGCACAGATTAGAAGGAAATTTGAA
1354  70_HRV50a|   AACTTCAAGAAATGGCAAATCAACCTACAAGAAATGGCACAGATCAGGAGGAAATTTGAG
1355  71_HRV50b|   AACTTCAAGAAATGGCAAATCAACCTACAAGAAATGGCACAGATCAGGAGGAAATTTGAG
1356  72_HRV50     AACTTCAAGAAATGGCAAATCAACCTACAAGAAATGGCACAGATCAGGAGGAAATTTGAG
1357  73_HRV18a|   AACTTTGTAAAATGGCAAATAAATCTACAGGAAATGGCCCAGATTAGGAGAAAATTTGAG
1358  74_HRV18b|   AACTTTGTAAAATGGCAAATAAATCTACAGGAAATGGCCCAGATTAGGAGAAAATTTGAG
1359  75_HRV18     AACTTTGTAAAATGGCAAATAAATCTACAGGAAATGGCCCAGATTAGGAGAAAATTTGAG
1360  76_HRV55     AATTTTACTAAGTGGCAAGTAAACATCCAAGAGATGGCTCAGATTAGAAGAAAATTTGAA
1361  77_HRV55b|   AATTTTACTAAGTGGCAAGTAAACATCCAAGAGATGGCTCAGATTAGAAGAAAATTTGAA
1362  78_HRV55a|   AATTTTACTAAGTGGCAAGTAAACATCCAAGAGATGGCTCAGATTAGAAGAAAATTTGAA
1363  79_HRV57     AATTTCACTAAATGGGAAATAAATCTACAAGAAATGGCACAAATCAGAAGAAAATTTGAA
1364  80_HRV57a|   AATTTCACTAAATGGGAAATAAATCTACAAGAAATGGCACAAATCAGAAGAAAATTTGAA
1365  81_HRV57b|   AATTTCACTAAATGGGAAATAAATCTACAAGAAATGGCACAAATCAGAAGAAAATTTGAA
```

FIG. D6 CONT'D

```
02.trace                                                                    9/20/2007 4:59 PM 1366  82_HRV21      AACATTAGTACATGGCAAATAAATATTAAAGAGATGGCACAAATTAGGAGAAAATTTGAA
1367  83_HRVHan     AACATTAATACATGGCAAATAAATATTAAAGAGATGGCACAAATTAGGAGAAAATTTGAA
1368  84_HRV43      AATTTTACCCAATGGCCAATCAACTTGCAAGAAATGGCACAAATTAGAAGAAAGTATGAA
1369  85_HRV43b|    AATTTTACCCAATGGCCAATCAACTTGCAAGAAATGGCACAAATTAGAAGAAAGTATGAA
1370  86_HRV43a|    AATTTTACCCAATGGCCAATCAACTTGCAAGAAATGGCACAAATTAGAAGAAAGTATGAA
1371  87_HRV75      AACTTCACTCAGTGGCCAATCAATCTACAGGAAATGGCTCAAATTAGAAGGAAATATGAA
1372  88_HRV75b|    AACTTCACTCAGTGGCCAATCAATCTACAGGAAATGGCTCAAATTAGAAGGAAATATGAA
1373  89_HRV75a|    AACTTCACTCAGTGGCCAATCAATCTACAGGAAATGGCTCAAATTAGAAGGAAATATGAA
1374  96_HRV9a|d    AATTTCACAATCTGGAAAATAAATATAAAGGAAATGGCCCAGATCAGGAGGAAATTTGAA
1375  97_HRV9b|d    AATTTCACAATCTGGAAAATAAATATAAAGGAAATGGCCCAGATCAGGAGGAAATTTGAA
1376  98_HRV9       AATTTCACAATCTGGAAAATAAATATAAAGGAAATGGCCCAGATCAGGAGGAAATTTGAA
1377  99_HRV32      AATTTCACAATTTGGAAGATAAATATAAAAGAAATGGCCCAGATTAGGAGAAAATTTGAG
1378  100_HRV32a    AATTTCACAATTTGGAAGATAAATATAAAAGAAATGGCCCAGATTAGGAGAAAATTTGAG
1379  101_HRV32b    AATTTCACAATTTGGAAGATAAATATAAAAGAAATGGCCCAGATTAGGAGAAAATTTGAG
1380  102_HRV67     AATTTCACAATTTGGAAAATAAATATAAAAGAAATGGCCCAGATTAGGAGGAAATTTGAA
1381  103_HRV67a    AATTTCACAATTTGGAAAATAAATATAAAAGAAATGGCCCAGATTAGGAGGAAATTTGAA
1382  104_HRV67b    AATTTCACAATTTGGAAAATAAATATAAAAGAAATGGCCCAGATTAGGAGGAAATTTGAA
1383  105_HRV15     AACTTTACTAAATGGCAAATTAATCTCAAAGAAATGGCCCAGATTAGAAGGAAATTTGAG
1384  106_HRV15a    AACTTTACTAAATGGCAAATTAATCTCAAAGAAATGGCCCAGATTAGAAGGAAATTTGAG
1385  107_HRV15b    AACTTTACTAAATGGCAAATTAATCTCAAAGAAATGGCCCAGATTAGAAGGAAATTTGAG
1386  108_HRV74a    AATTTTACTAAATGGCAAATAAATCTTAAAGAAATGGCACAGATTAGGAGAAAATTTGAG
1387  109_HRV74b    AATTTTACTAAATGGCAAATAAATCTTAAAGAAATGGCACAGATTAGGAGAAAATTTGAA
1388  110_HRV74     AATTTTACTAAATGGCAAATAAATCTTAAAGAAATGGCACAGATTAGGAGAAAATTTGAA
1389  111_HRV38a    AACTTTACAACATGGCAAATCAATCTCAAAGAAATGGCTCAAATCAGAAGAAAGTTTGAA
1390  112_HRV38b    AACTTTACAACATGGCAAATCAATCTCAAAGAAATGGCTCAAATCAGAAGAAAGTTTGAA
1391  113_HRV38     AACTTTACAACATGGCAAATCAATCTCAAAGAAATGGCTCAAATCAGAAGAAAGTTTGAA
1392  114_HRV60     AATTTCACAACTTGGCAAATTAACCTAAAGGAAATGGCACAAATAAGAAGAAAGTTTGAA
1393  115_HRV60a    AATTTCACAACTTGGCAAATTAACCTAAAGGAAATGGCACAAATAAGAAGAAAGTTTGAA
1394  116_HRV60b    AATTTCACAACTTGGCAAATTAACCTAAAGGAAATGGCACAAATAAGAAGAAAGTTTGAA
1395  117_HRV64a    AATTTTAACAAATGGCAGATCACCTTGAAAGAAATGGCTCAGATAAGAAGGAAGTATGAA
1396  118_HRV64b    AATTTTAACAAATGGCAGATCACCTTGAAAGAAATGGCTCAGATAAGAAGGAAGTATGAA
1397  119_HRV64     AATTTTAACAAATGGCAGATCACCTTGAAAGAAATGGCTCAGATAAGAAGGAAGTATGAA
1398  120_HRV94a    AATTTCCAATCATGGCAAATTACCCTAAAAGAAATGGCACAAATAAGAAGGAAATTTGAA
1399  121_HRV94b    AATTTCCAATCATGGCAAATTACCCTAAAAGAAATGGCACAAATAAGAAGGAAATTTGAA
1400  122_HRV94     AATTTCCAATCATGGCAAATTACCCTAAAAGAAATGGCACAAATAAGAAGGAAATTTGAA
1401  123_HRV22     AACTTTAACATATGGCAAATTAACCTTAAAGAGATGGCTCAGATAAGAAGGAAGTTTGAG
1402  124_HRV22a    AACTTTAACATATGGCAAATTAACCTTAAAGAGATGGCTCAGATAAGAAGGAAGTTTGAG
1403  125_HRV22b    AACTTTAACATATGGCAAATTAACCTTAAAGAGATGGCTCAGATAAGAAGGAAGTTTGAG
1404  126_HRV82     AACTTTAGATCATGGCAAATAAGCATAAAGGAAATGGCACAAATTAGAAGGAAGTTTGAA
1405  127_HRV82b    AACTTTAGATCATGGCAAATAAGCATAAAGGAAATGGCACAAATTAGAAGGAAGTTTGAA
1406  128_HRV82a    AACTTTAGATCATGGCAAATAAGCATAAAGGAAATGGCACAAATTAGAAGGAAGTTTGAA
1407  129_HRV19     AATTTCAAAACTTGGCAAATAAACTTGAAAGAAATGGCACAGATTAGAAGCAAAATTTGAA
1408  130_HRV19a    AATTTCAAAACTTGGCAAATAAACTTGAAAGAAATGGCACAGATTAGAAGCAAAATTTGAA
1409  131_HRV19b    AATTTCAAAACTTGGCAAATAAACTTGAAAGAAATGGCACAGATTAGAAGCAAAATTTGAA
1410  132_HRV13     AATTTTGTGAAATGGAAAATAAGTTTGCAAGAAATGGCCCAAGTGCGCAGAAAATTTGAG
1411  133_HRV13a    AATTTTGTGAAATGGAAAATAAGTTTGCAAGAAATGGCCCAAGTGCGCAGAAAATTTGAG
1412  134_HRV13b    AATTTTGTGAAATGGAAAATAAGTTTGCAAGAAATGGCCCAAGTGCGCAGAAAATTTGAG
1413  135_HRV41     AACTTCAAGAAGTGGAAAATTAGCTTACAGGAGATGGCCCAAGTACGTAGAAAGTTTGAA
1414  136_HRV41a    AACTTCAAGAAGTGGAAAATTAGCTTACAGGAGATGGCCCAAGTACGTAGAAAGTTTGAA
1415  137_HRV41b    AACTTCAAGAAGTGGAAAATTAGCTTACAGGAGATGGCCCAAGTACGTAGAAAGTTTGAG
1416  138_HRV73     AATTTTACCAAATGGAAAATAAGTTTACAAGAGATGGCTCAAATACGTAGGAAATTTGAA
1417  139_HRV73b    AATTTTACCAAATGGAAAATAAGTTTACAAGAGATGGCTCAAATACGTAGGAAATTTGAA
1418  140_HRV73a    AATTTTACCAAATGGAAAATAAGTTTACAAGAGATGGCTCAAATACGTAGGAAATTTGAA
1419  141_HRV61     AACTTCAAGGTGTGGAAAATAAACCTGCAAGAGATGGCACAAATACGTAGAAAATTTGAG
1420  142_HRV61a    AACTTCAAGGTGTGGAAAATAAACCTGCAAGAGATGGCACAAATACGTAGAAAATTTGAG
1421  143_HRV61b    AACTTCAAGGTGTGGAAAATAAACCTGCAAGAGATGGCACAAATACGTAGAAAATTTGAG
1422  144_HRV96     AATTTTAAGGTGTGGAAAATAAATCTACAAGAAATGGCTCAAATTCGCAGGAAGTTTGAA
1423  145_HRV96b    AATTTTAAGGTGTGGAAAATAAATCTACAAGAAATGGCTCAAATTCGCAGGAAGTTTGAA
1424  146_HRV96a    AATTTTAAGGTGTGGAAAATAAATCTACAAGAAATGGCTCAAATTCGCAGGAAGTTTGAA
1425  90_HRV16a|    AGTTTCACTAAATGGAAGATAAACCTGCAAGAAATGGCACAAATTAGAAGAAAATTTGAA
1426  91_HRV16b|    AGTTTCACTAAATGGAAGATAAACCTGCAAGAAATGGCACAAATTAGAAGAAAATTTGAA
1427  92_1AYM_A     AGTTTCACTAAATGGAAGATAAACCTGCAAGAAATGGCACAAATTAGAAGAAAATTTGAA
1428  93_HRV81a|    AGCTTTACTAAATGGAAAATTAACTTACAAGAGATGGCACAGATTAGGAGAAAGTTTGAA
1429  94_HRV81b|    AGCTTTACTAAATGGAAAATTAACTTACAAGAGATGGCACAGATTAGGAGAAAGTTTGAA
1430  95_HRV81      AGCTTTACTAAATGGAAAATTAACTTACAAGAGATGGCACAGATTAGGAGAAAGTTTGAA
```

FIG. D6 CONT'D

```
02.trace                                                                                9/20/2007 4:59 PM 1431 147_HRV2     AATTTTACAGTGTGGGCTATTAATATACAAGAAATGGCTCAAATTAGAAGGAAATTTGAA
1432 148_HRV2a|   AATTTTACAGTGTGGGCTATTAATATACAAGAAATGGCTCAAATTAGAAGGAAATTTGAA
1433 149_HRV2b|   AATTTTACAGTGTGGGCTATTAATATACAAGAAATGGCTCAAATTAGAAGGAAATTTGAA
1434 150_HRV49a   AATTTCAAAGTATGGAACATCAATTTGCAAGAAATGGCCCAGATCAGAAGAAAATTTGAA
1435 151_HRV49b   AATTTCAAAGTATGGAACATCAATTTGCAAGAAATGGCCCAGATCAGAAGAAAATTTGAA
1436 152_HRV49    AATTTCAAAGTATGGAACATCAATTTGCAAGAAATGGCCCAGATCAGAAGAAAATTTGAA
1437 153_HRV23a   AATTTTAATACTTGGAATATTAATTTACAGGAAATGGCCCAAATCAGAAGAAAGTTTGAA
1438 154_HRV23b   AATTTTAATACTTGGAATATTAATTTACAGGAAATGGCCCAAATCAGAAGAAAGTTTGAA
1439 155_HRV23    AATTTTAATACTTGGAATATTAATTTACAGGAAATGGCCCAAATCAGAAGAAAGTTTGAA
1440 156_HRV30a   AACTTTACCACATGGAATATTAATCTTCAAGAAATGGCCCAAATTAGAAGAAAATTTGAG
1441 157_HRV30b   AACTTTACCACATGGAATATTAATCTTCAAGAAATGGCCCAAATTAGAAGAAAATTTGAG
1442 158_HRV30    AACTTTACCACATGGAATATTAATCTTCAAGAAATGGCCCAAATTAGAAGAAAATTTGAG
1443 159_HRV7     GGTTTCACTACATGGAAAATCAGCTTACAAGAAATGGCACAAATCAGAAGAAAGTTTGAA
1444 160_HRV7b|   GGTTTCACTACATGGAAAATCAGCTTACAAGAAATGGCACAAATCAGAAGAAAGTTTGAA
1445 161_HRV7a|   GGTTTCACTACATGGAAAATCAGCTTACAAGAAATGGCACAAATCAGAAGAAAGTTTGAA
1446 162_HRV88    GGATTTGTAACATGGAAGATTAGCTTGCAAGAAATGGCACAAATCAGGAGAAAATTTGAA
1447 163_HRV88a   GGATTTGTAACATGGAAGATTAGCTTGCAAGAAATGGCACAAATCAGGAGAAAATTTGAA
1448 164_HRV88b   GGATTTGTAACATGGAAGATTAGCTTGCAAGAAATGGCACAAATCAGGAGAAAATTTGAA
1449 165_HRV36a   GGATTCAAAACATGGAAGATTAGTCTTCAAGAAATGGCACAAATTAGAAGGAAATATGAA
1450 166_HRV36b   GGATTCAAAACATGGAAGATTAGTCTTCAAGAAATGGCACAAATTAGAAGGAAATATGAA
1451 167_HRV36    GGATTCAAAACATGGAAGATTAGTCTTCAAGAAATGGCACAAATTAGAAGGAAATATGAA
1452 168_HRV89a   GGATTCAAAACATGGAAGGTTAGTCTTCAAGAAATGGCACAAATCAGAAGAAAATATGAA
1453 169_HRV89b   GGATTCAAAACATGGAAGGTTAGTCTTCAAGAAATGGCACAAATCAGAAGAAAATATGAA
1454 170_HRV89    GGATTCAAAACATGGAAGGTTAGTCTTCAAGAAATGGCACAAATCAGAAGAAAATATGAA
1455 171_HRV58    GGATACAAAACATGGAAAATTAGCCTTCAAGAGATGGCACAAATTAGAAGGAAATTTGAG
1456 172_HRV58a   GGATACAAAACATGGAAAATTAGCCTTCAAGAGATGGCACAAATTAGAAGGAAATTTGAG
1457 173_HRV58b   GGATACAAAACATGGAAAATTAGCCTTCAAGAGATGGCACAAATTAGAAGGAAATTTGAG
1458 174_HRV12a   AACTTTAAAACATGGAAGATAAATCTTAAGGAAATGGCCCAGATTAGAAGGAAAAATGAG
1459 175_HRV12b   AACTTTAAAACATGGAAGATAAATCTTAAGGAAATGGCCCAGATTAGAAGGAAAAATGAG
1460 176_HRV12    AACTTTAAAACATGGAAGATAAATCTTAAGGAAATGGCCCAGATTAGAAGGAAAAATGAG
1461 177_HRV78a   AATTTTACAACGTGGAAAATCAACTTACAGGAGATGGCCCAGATTAGAAGAAAAGAATGAG
1462 178_HRV78b   AATTTTACAACGTGGAAAATCAACTTACAGGAGATGGCCCAGATTAGAAGAAAGAATGAG
1463 179_HRV78    AATTTTACAACGTGGAAAATCAACTTACAGGAGATGGCCCAGATTAGAAGAAAGAATGAG
1464 180_HRV20    AATTTCTCTCAGTGGAAGATCACAATCAAGGAAATGGCTCAAATCAGAAGAAAATGTGAG
1465 181_HRV20a   AATTTCTCTCAGTGGAAGATCACAATCAAGGAAATGGCTCAAATCAGAAGAAAATGTGAG
1466 182_HRV20b   AATTTCTCTCAGTGGAAGATCACAATCAAGGAAATGGCTCAAATCAGAAGAAAATGTGAG
1467 183_HRV68    AACTTCTCCCAATGGAAAATTACAATTAAGGAAATGGCTCAAATTAGAAGAAAGTGTGAA
1468 184_HRV68a   AACTTCTCCCAATGGAAAATTACAATTAAGGAAATGGCTCAAATTAGAAGAAAGTGTGAA
1469 185_HRV68b   AACTTCTCCCAATGGAAAATTACAATTAAGGAAATGGCTCAAATTAGAAGAAAGTGTGAA
1470 186_HRV28    AATTTTAGTAAATGGAATATCACTCTCAAAGAAATGGCCCAAATCAGAAGAAAGTGTGAA
1471 187_HRV28a   AATTTTAGTAAATGGAATATCACTCTCAAAGAAATGGCCCAAATCAGAAGAAAGTGTGAA
1472 188_HRV28b   AATTTTAGTAAATGGAATATCACTCTCAAAGAAATGGCCCAAATCAGAAGAAAGTGTGAA
1473 189_HRV53a   AACCACTCAGAATGGAAGATTACACTCAAAGAAATGGCCCAGATTAGAAGGAAATGTGAG
1474 190_HRV53b   AACCACTCAGAATGGAAGATTACACTCAAAGAAATGGCCCAGATTAGAAGGAAATGTGAG
1475 191_HRV53    AACCACTCAGAATGGAAGATTACACTCAAAGAAATGGCCCAGATTAGAAGGAAATGTGAG
1476 192_HRV46a   AACTTCTCAAAATGGAAAATAACACTGTTGGAAATGGCACAAATCAGAAGAAAGTGTGAA
1477 193_HRV46b   AACTTCTCAAAATGGAAAATAACACTGTTGGAAATGGCACAAATCAGAAGAAAGTGTGAA
1478 194_HRV46    AACTTCTCAAAATGGAAAATAACACTGTTGGAAATGGCACAAATCAGAAGAAAGTGTGAA
1479 195_HRV80a   AATTTTTCAAAGTGGAAAATAACATTAATGGAAATGGCACAAATTAGAAGAAAGTGTGAG
1480 196_HRV80b   AATTTTTCAAAGTGGAAAATAACATTAATGGAAATGGCACAAATTAGAAGAAAGTGTGAG
1481 197_HRV80    AATTTTTCAAAGTGGAAAATAACATTAATGGAAATGGCACAAATTAGAAGAAAGTGTGAG
1482 198_HRV51    AATTTCTCTACATGGAAAATTACACTCAAAGAAATGGCTCAAATTAGAAGAAAGTGTGAA
1483 199_HRV51a   AATTTCTCTACATGGAAAATTACACTCAAAGAAATGGCTCAAATTAGAAGAAAGTGTGAA
1484 200_HRV51b   AATTTCTCTACATGGAAAATTACACTCAAAGAAATGGCTCAAATTAGAAGAAAGTGTGAA
1485 201_HRV65a   AATTTCTCTGCTTGGGAAATTACACTCAAGGAAATGGCTCAAATTAGGAGAAAGTGTGAA
1486 202_HRV65b   AATTTCTCTGCTTGGGAAATTACACTCAAGGAAATGGCTCAAATTAGGAGAAAGTGTGAA
1487 203_HRV65    AATTTCTCTGCTTGGGAAATTACACTCAAGGAAATGGCTCAAATTAGGAGAAAGTGTGAA
1488 204_HRV71a   AATCTCTCAAAGTGGCAGATTACACTCAAAGAAATGGCTCAGATCAGGAGGAAATGTGAA
1489 205_HRV71b   AATCTCTCAAAGTGGCAGATTACACTCAAAGAAATGGCTCAGATCAGGAGGAAATGTGAA
1490 206_HRV71    AATCTCTCAAAGTGGCAGATTACACTCAAAGAAATGGCTCAGATCAGGAGGAAATGTGAA
1491 207_HRV8     AGTTTCAGGACCTGGGGAATAAACATACAAGAGATGTCACAAATTAGAAGGAAATTTGAG
1492 208_HRV95    AATTTCAGGACCTGGGGAATAAACATACAAGAAATGTCACAAATTAGAAGGAAATTTGAA
1493 209_HRV45    AATTACAAAAATTGGGCAATTAGTTTACAAGAAATGTCACAAATTAGGAGGAAATTTGAA
1494 210_HRV45a   AATTACAAAAATTGGGCAATTAGTTTACAAGAAATGTCACAAATTAGGAGGAAATTTGAA
1495 211_HRV45b   AATTACAAAAATTGGGCAATTAGTTTACAAGAAATGTCACAAATTAGGAGGAAATTTGAA
```

FIG. D6 CONT'D

```
02.trace                                                               9/20/2007 4:59 PM 1496 GROUP_1         ------------TGG----T-A---T----GA-ATG-C-CA--T--G--G-AA----GA-
1497
1498  1_HRV1A1|d     TTGTTTACATATGTCAGGTTTGACTCAGAAATAACCTTGG-TGCCTTGTATTGCTGGTAG
1499  2_HRV1A2|d     TTGTTTACATATGTCAGGTTTGACTCAGAAATAACCTTGG-TGCCTTGTATTGCTGGTAG
1500  3_HRV1A|cD     TTGTTTACATATGTCAGGTTTGACTCAGAAATAACCTTGG-TGCCTTGTATTGCTGGTAG
1501  4_HRV1B1|d     CTATTTACTTATGTTAGGTTTGATTCAGAAGTAACTTTAG-TACCCTGTATTGCTGGTAG
1502  5_HRV1B2|d     CTATTTACTTATGTTAGGTTTGATTCAGAAGTAACTTTAG-TACCCTGTATTGCTGGTAG
1503  6_HRV1B        CTATTTACTTATGTTAGGTTTGATTCAGAAGTAACTTTAG-TACCCTGTATTGCTGGTAG
1504  7_HRV40a|d     TTCTTTACATATGCTAGGTTTGATTCAGAAATTACCTTAG-TTCCTTGTATAGCCGGTAA
1505  8_HRV40b|d     TTCTTTACATATGCTAGGTTTGATTCAGAAATTACCTTAG-TTCCTTGTATAGCCGGTAA
1506  9_HRV40        TTCTTTACATATGCTAGGTTTGATTCAGAAATTACCTTAG-TTCCTTGTATAGCCGGTAA
1507 10_HRV85        TTCTTTACTTACACTAGATTTGATTCAGAAATCACTTTAG-TCCCTTGTATAGCTGGAAA
1508 11_HRV85a|      TTCTTTACTTACACTAGATTTGATTCAGAAATCACTTTAG-TCCCTTGTATAGCTGGAAA
1509 12_HRV85b|      TTCTTTACTTACACTAGATTTGATTCAGAAATCACTTTAG-TCCCTTGTATAGCTGGAAA
1510 13_HRV56a|      TTCTTTACTTATGTCAGATTTGATTCAGAGGTTACTTTGG-TACCTTGTGTAGCCGGCAA
1511 14_HRV56b|      TTCTTTACTTATGTCAGATTTGATTCAGAGGTTACTTTGG-TACCTTGTGTAGCCGGCAA
1512 15_HRV56        TTCTTTACTTATGTCAGATTTGATTCAGAGGTTACTTTGG-TACCTTGTGTAGCCGGCAA
1513 16_HRV54        TTCTTTACTTATGTTAGGTTTGATTCAGAAATTACTCTAG-TCCCCTGTATAGCTGGTAA
1514 17_HRV98        TTCTTTACTTATGTTAGATTTGATTCAGAAGTTACCTTAG-TTCCTTGCATAGCTGGCAA
1515 18_HRV59a|      TTCTTCACATATGTTAGATTTGACTCAGAAATCACTTTGG-TGCCTTGCATAGCTGGAAA
1516 19_HRV59b|      TTCTTCACATATGTTAGATTTGACTCAGAAATCACTTTGG-TGCCTTGCATAGCTGGAAA
1517 20_HRV59        TTCTTCACATATGTTAGATTTGACTCAGAAATCACTTTGG-TGCCTTGCATAGCTGGAAA
1518 21_HRV63        TTCTTCACATATGTCAGATTTGATTCAGAAGTCACTCTTG-TACCATGTATAGCAGGAAA
1519 22_HRV63b|      TTCTTCACATATGTCAGATTTGATTCAGAAGTCACTCTTG-TACCATGTATAGCAGGAAA
1520 23_HRV63a|      TTCTTCACATATGTCAGATTTGATTCAGAAGTCACTCTTG-TACCATGTATAGCAGGAAA
1521 24_HRV39        ATGTTCACCTATGTTAGATTTGACTCAGAGATTACTTTAG-TCCCATGCATAGCTGGAAG
1522 25_HRV39a|      ATGTTCACCTATGTTAGATTTGACTCAGAGATTACTTTAG-TCCCATGCATAGCTGGAAG
1523 26_HRV39b|      ATGTTCACCTACGTTAGATTTGACTCAGAGATTACTTTAG-TCCCATGCATAGCTGGAAG
1524 27_HRV10a|      ATGTTTACATATGTTAGATTTGACTCAGAAGTCACTTTAG-TACCTTGCATCGCAGGCAA
1525 28_HRV10b|      ATGTTTACATATGTTAGATTTGACTCAGAAGTCACTTTAG-TACCTTGCATCGCAGGCAA
1526 29_HRV10        ATGTTTACATATGTTAGATTTGACTCAGAAGTCACTTTAG-TACCTTGCATCGCAGGCAA
1527 30_HRV100a      ATGTTTACATATGTCAGATTTGACTCAGAAATCACATTGG-TACCCTGTATTGCAGGAAA
1528 31_HRV100b      ATGTTTACATATGTCAGATTTGACTCAGAAATCACATTGG-TACCCTGTATTGCAGGAAA
1529 32_HRV100       ATGTTTACATATGTCAGATTTGACTCAGAAATCACATTGG-TACCCTGTATTGCAGGAAA
1530 33_HRV66        ATGTTCACATATGTTAGGTTTGATTCTGAAATTACATTAG-TCCCATGCATTGCAGGAAA
1531 34_HRV66b|      ATGTTCACATATGTTAGGTTTGATTCTGAAATTACATTAG-TCCCATGCATTGCAGGAAA
1532 35_HRV66a|      ATGTTCACATATGTTAGGTTTGATTCTGAAATTACATTAG-TCCCATGCATTGCAGGAAA
1533 36_HRV77a|      ATGTTACATATGTAAGATTTGATTCAGAAATTACATTGG-TCCCATGTATTGCTGGAAA
1534 37_HRV77b|      ATGTTTACATATGTAAGATTTGATTCAGAAATTACATTGG-TCCCATGTATTGCTGGAAA
1535 38_HRV77        ATGTTTACATATGTAAGATTTGATTCAGAAATTACATTGG-TCCCATGTATTGCTGGAAA
1536 39_HRV62a       ATGTTTACATATGTAAGATTTGATTCAGAAATAACCCTGG-TTCCATCTATTGCAGGACG
1537 40_HRV62b       ATGTTTACATATGTAAGATTTGATTCAGAAATAACCCTGG-TTCCATCTATTGCAGGACG
1538 41_HRV25        ATGTTTACATATGTGAGATTTGATTCAGAGATAACCCTAG-TTCCATCTATTGCAGGACG
1539 42_HRV29a       ATGTTCACATATGTGAGATTTGACTCAGAAATAACTCTGG-TTCTTTGCATTGCAGGACG
1540 43_HRV29b       ATGTTCACATATGTGAGATTTGACTCAGAAATAACTCTGG-TTCCATGCATTGCAGGACG
1541 44_HRV44a       ATGTTCACATATGTGAGATTTGATTCGGAAATAACTCTGG-TTCCATGCATTGCAGGACA
1542 45_HRV44b       ATGTTCACATATGTGAGATTTGATTCAGAAATAACTCTAG-TTCCATGCATTGCAGGACG
1543 46_HRV31        ATGTTCACATATGTAAGATTTGATTCAGAAGTGACCATAG-TTCCATGCATTGCAGGACA
1544 47_HRV31a|      ATGTTCACATATGTAAGATTTGATTCAGAAGTGACCATAG-TTCCATGCATTGCAGGACA
1545 48_HRV31b|      ATGTTCACATATGTAAGATTTGATTCAGAAGTGACCATAG-TTCCATGCATTGCAGGACA
1546 49_HRV47        ATGTTTACATATGTAAGATTTGATTCAGAAGTAACCATGG-TTCCATGTATTGCAGGGTA
1547 50_HRV47a|      ATGTTTACATATGTAAGATTTGATTCAGAAGTAACCATGG-TTCCATGTATTGCAGGGTA
1548 51_HRV47b|      ATGTTTACATATGTAAGATTTGATTCAGAAGTAACCATGG-TTCCATGTATTGCAGGGTA
1549 52_HRV11        ATGTTCACATACACTAGATTTGATTCAGAGATCACATTGG-TGCCTTGTATAGCTGCAAA
1550 53_HRV11b|      ATGTTCACATACACTAGATTTGATTCAGAGATCACATTGG-TGCCTTGTATAGCTGCAAA
1551 54_HRV11a|      ATGTTCACATACACTAGATTTGATTCAGAGATCACATTGG-TGCCTTGTATAGCTGCAAA
1552 55_HRV76        ATGTTTACATATACTAGATTTGATTCAGAAGTTACTCTAG-TTCCTTCTATAGCTGCCAA
1553 56_HRV76b|      ATGTTTACATATACTAGATTTGATTCAGAAGTTACTCTAG-TTCCTTCTATAGCTGCCAA
1554 57_HRV76a|      ATGTTTACATATACTAGATTTGATTCAGAAGTTACTCTAG-TTCCTTCTATAGCTGCCAA
1555 58_HRV33        ATGTTTACATATGCCAGATTTGATTCAGAGATCACCCTAG-TCCCTTCTATAGCTGCCCA
1556 59_HRV33b|      ATGTTTACATATGCCAGATTTGATTCAGAGATCACCCTAG-TCCCTTCTATAGCTGCCCA
1557 60_HRV33a|      ATGTTTACATATGCCAGATTTGATTCAGAGATCACCCTAG-TCCCTTCTATAGCTGCCCA
1558 61_HRV24a|      TTATTCACATATACTAGATTTGACTCTGAGATTACAATAG-TTCCATCCATAGCTGGCAA
1559 62_HRV24b|      TTATTCACATATACTAGATTTGACTCTGAGATTACAATAG-TTCCATCCATAGCTGGCAA
1560 63_HRV24        TTATTCACATATACTAGATTTGACTCTGAGATTACAATAG-TTCCATCCATAGCTGGCAA
```

FIG. D6 CONT'D

02.trace                                                                                    9/20/2007 4:59 PM

```
1561  64_HRV90      TTGTTTACATATGCTAGATTTGATTCTGAAATTACAATAG-TACCATCTATAGCTGGCAA
1562  65_HRV90a|    TTGTTTACATATGCTAGATTTGATTCTGAAATTACAATAG-TACCATCTATAGCTGGCAA
1563  66_HRV90b|    TTGTTTACATATGCTAGATTTGATTCTGAAATTACAATAG-TACCATCTATAGCTGGCAA
1564  67_HRV34      ATGTTCACCTACGTCAGATTTGATTCTGAAGTCACCCTAG-TACCATCAATAGCGGCCAA
1565  68_HRV34b|    ATGTTCACCTACGTCAGATTTGATTCTGAAGTCACCCTAG-TACCATCAATAGCGGCCAA
1566  69_HRV34a|    ATGTTCACCTACGTCAGATTTGATTCTGAAGTCACCCTAG-TACCATCAATAGCGGCCAA
1567  70_HRV50a|    ATGTTCACCTATGTGAGGTTTAATTCTGAGGTCACATTAG-TACCATCCATAGCTGCCAA
1568  71_HRV50b|    ATGTTCACCTATGTGAGGTTTAATTCTGAGGTCACATTAG-TACCATCCATAGCTGCCAA
1569  72_HRV50      ATGTTCACCTATGTGAGGTTTAATTCTGAGGTCACATTAG-TACCATCCATAGCTGCCAA
1570  73_HRV18a|    ATGTTTACATATGTTAGATTTGATTCAGAAATTACACTAG-TACCATCTGTAGCTGCTAA
1571  74_HRV18b|    ATGTTTACATATGTTAGATTTGATTCAGAAATTACACTAG-TACCATCTGTAGCTGCTAA
1572  75_HRV18      ATGTTTACATATGTTAGATTTGATTCAGAAATTACACTAG-TACCATCTGTAGCTGCTAA
1573  76_HRV55      ATGTTCACCTATACTAGATTTGATTCAGAAGTTACATTAG-TACCCTCTATTGCTGCAAA
1574  77_HRV55b|    ATGTTCACCTATACTAGATTTGATTCAGAAGTTACATTAG-TACCCTCTATTGCTGCAAA
1575  78_HRV55a|    ATGTTCACCTATACTAGATTTGATTCAGAAGTTACATTAG-TACCCTCTATTGCTGCAAA
1576  79_HRV57      CTATTTACATATGTTAGGTTTGATTCTGAAGTTACATTAG-TTCCCTCCATAGCTGCTCA
1577  80_HRV57a|    CTATTTACATATGTTAGGTTTGATTCTGAAGTTACATTAG-TTCCCTCCATAGCTGCTCA
1578  81_HRV57b|    CTATTTACATATGTTAGGTTTGATTCTGAAGTTACATTAG-TTCCCTCCATAGCTGCTCA
1579  82_HRV21      ATGTTCACCTATACTAGATTTGATTCAGAAATAACTTTGG-TGCCGTCAATTGCAGCTAG
1580  83_HRVHan     ATGTTCACCTATACTAGATTTGATTCAGAAATAACTTTGG-TACCGTCAATTGCAGCTAA
1581  84_HRV43      TTGTTCACATACTTAAGGTTTGATTCTGAAATTACCCTTG-TTCCTTGCATTGCAGCAAA
1582  85_HRV43b|    TTGTTCACATACTTAAGGTTTGATTCTGAAATTACCCTTG-TTCCTTGCATTGCAGCAAA
1583  86_HRV43a|    TTGTTCACATACTTAAGGTTTGATTCTGAAATTACCCTTG-TTCCTTGCATTGCAGCAAA
1584  87_HRV75      TTATTTACATATACTTAGATTTGATTCAGAGGTTACTCTGG-TGCCATGCATTGCAGCTAA
1585  88_HRV75b|    TTATTTACATATCTTAGATTTGATTCAGAGGTTACTCTGG-TGCCATGCATTGCAGCTAA
1586  89_HRV75a|    TTATTTACATATCTTAGATTTGATTCAGAGGTTACTCTGG-TGCCATGCATTGCAGCTAA
1587  96_HRV9a|d    TTGTTTACATATGCAAGATTTGACTCTGAAATAACATTGG-TCCCGTGTATAGCAGCAGA
1588  97_HRV9b|d    TTGTTTACATATGCAAGATTTGACTCTGAAATAACATTGG-TCCCGTGTATAGCAGCAGA
1589  98_HRV9       TTGTTTACATATGCAAGATTTGACTCTGAAATAACATTGG-TCCCGTGTATAGCAGCAGA
1590  99_HRV32      TTGTTTACATACACAAGGTTTGATTCTGAAATAACATTAG-TACCTTGTATAGCTGCAGA
1591  100_HRV32a    TTGTTTACATACACAAGGTTTGATTCTGAAATAACATTAG-TACCTTGTATAGCTGCAGA
1592  101_HRV32b    TTGTTTACATACACAAGGTTTGATTCTGAAATAACATTAG-TACCTTGTATAGCTGCAGA
1593  102_HRV67     CTATTCACATATACAAGATTTGATTCTGAGATAACACTGG-TACCATGCATAGCTGCAGA
1594  103_HRV67a    CTATTCACATATACAAGATTTGATTCTGAGATAACACTGG-TACCATGCATAGCTGCAGA
1595  104_HRV67b    CTATTCACATATACAAGATTTGATTCTGAGATAACACTGG-TACCATGCATAGCTGCAGA
1596  105_HRV15     TTATTCACATATGTAAGGTTTGATTCAGAAATAACACTTG-TACCATGCATTGCAGCAAA
1597  106_HRV15a    TTATTCACATATGTAAGGTTTGATTCAGAAATAACACTTG-TACCATGCATTGCAGCAAA
1598  107_HRV15b    TTATTCACATATGTAAGGTTTGATTCAGAAATAACACTTG-TACCATGCATTGCAGCAAA
1599  108_HRV74a    TTGTTCACATATGTTAGATTTGACTCAGAAGTGACATTAG-TTCCATGCATTGCTGCTAA
1600  109_HRV74b    TTGTTCACATATGTTAGATTTGACTCAGAAGTGACATTAG-TTCCATGCATTGCTGCTAA
1601  110_HRV74     TTGTTCACATATGTTAGATTTGACTCAGAAGTGACATTAG-TTCCATGCATTGCTGCTAA
1602  111_HRV38a    ATGTTTACATATGTGAGATTTGATTCAGAAGTTACATTAG-TCCCATGTATAGCAGCACA
1603  112_HRV38b    ATGTTTACATATGTGAGATTTGATTCAGAAGTTACATTAG-TCCCATGTATAGCAGCACA
1604  113_HRV38     ATGTTTACATATGTGAGATTTGATTCAGAAGTTACATTAG-TCCCATGTATAGCAGCACA
1605  114_HRV60     TTATTTACATATGTAAGATTTGATTCAGAATTGACTCTGG-TCCCATGCATAGCAGCAAA
1606  115_HRV60a    TTATTTACATATGTAAGATTTGATTCAGAATTGACTCTGG-TCCCATGCATAGCAGCAAA
1607  116_HRV60b    TTATTTACATATGTAAGATTTGATTCAGAATTGACTCTGG-TCCCATGCATAGCAGCAAA
1608  117_HRV64a    TTATTTACATATGTTAGATTTGATTCTGAAATAACCTTAG-TGCCTTGCATATCTTCTCA
1609  118_HRV64b    TTATTTACATATGTTAGATTTGATTCTGAAATAACCTTAG-TGCCTTGCATATCTTCTCA
1610  119_HRV64     TTATTTACATATGTTAGATTTGATTCTGAAATAACCTTAG-TGCCTTGCATATCTTCTCA
1611  120_HRV94a    CTATTTACTTATGTTAGATTTGATTCAGAAATAACTTTAG-TACCTTGCATATCATCTCA
1612  121_HRV94b    CTATTTACTTATGTTAGATTTGATTCAGAAATAACTTTAG-TACCTTGCATATCATCTCA
1613  122_HRV94     CTATTTACTTATGTTAGATTTGATTCAGAAATAACTTTAG-TACCTTGCATATCATCTCA
1614  123_HRV22     CTATTTACATATCTCAGGTTTGATTCTGAAATCACTTTGG-TACCATGCATTGCTTCACA
1615  124_HRV22a    CTATTTACATATCTCAGGTTTGATTCTGAAATCACTTTGG-TACCATGCATTGCTTCACA
1616  125_HRV22b    CTATTTACATATCTCAGGTTTGATTCTGAAATCACTTTGG-TACCATGCATTGCTTCACA
1617  126_HRV82     CTTTTCACATATGTGAGATTTGATTCAGAAATTACTTTAG-TGCCTTGCATAGCCTCTCA
1618  127_HRV82b    CTTTTCACATATGTGAGATTTGATTCAGAAATTACTTTAG-TGCCTTGCATAGCCTCTCA
1619  128_HRV82a    CTTTTCACATATGTGAGATTTGATTCAGAAATTACTTTAG-TGCCTTGCATAGCCTCTCA
1620  129_HRV19     CTTTTCACTTACCTCAGATTTGATTCAGAGGTAACATTAG-TCCCTTGCATAGCTGCTAA
1621  130_HRV19a    CTTTTCACTTACCTCAGATTTGATTCAGAGGTAACATTAG-TCCCTTGCATAGCTGCTAA
1622  131_HRV19b    CTTTTCACTTACCTCAGATTTGATTCAGAGGTAACATTAG-TCCCTTGCATAGCTGCTAA
1623  132_HRV13     TTGTTCACCTATGTAAGATTTGATTCAGAAATAACAATTG-TGCCATGTATAGCCGGGCA
1624  133_HRV13a    TTGTTCACCTATGTAAGATTTGATTCAGAAATAACAATTG-TGCCATGTATAGCCGGGCA
1625  134_HRV13b    TTGTTCACCTATGTAAGATTTGATTCAGAAATAACAATTG-TGCCATGTATAGCCGGGCA
```

FIG. D6 CONT'D

```
02.trace                                                                   9/20/2007 4:59 PM 1626 135_HRV41    TTTTTTACGTATGTTAGATTTGACTCAGAAATAACAATTG-TGCCAAGTATAGCTGGACA
1627 136_HRV41a   TTTTTTACGTATGTTAGATTTGACTCAGAAATAACAATTG-TGCCAAGTATAGCTGGACA
1628 137_HRV41b   TTTTTTACGTATGTTAGATTTGACTCAGAAATAACAATTG-TGCCAAGTATAGCTGGACA
1629 138_HRV73    TTATTCACCTATGTAAGATTTGATTCAGAAGTGACAATTG-TACCATGTATAGCTGGTCA
1630 139_HRV73b   TTATTCACCTATGTAAGATTTGATTCAGAAGTGACAATTG-TACCATGTATAGCTGGTCA
1631 140_HRV73a   TTATTCACCTATGTAAGATTTGATTCAGAAGTGACAATTG-TACCATGTATAGCTGGTCA
1632 141_HRV61    TTGTTCACATATGCTAGATTTGATTCAGAGATTACAATTG-TACCTTGTGTTGCTGGGCA
1633 142_HRV61a   TTGTTCACATATGCTAGATTTGATTCAGAGATTACAATTG-TACCTTGTGTTGCTGGGCA
1634 143_HRV61b   TTGTTCACATATGCTAGATTTGATTCAGAGATTACAATTG-TACCTTGTGTTGCTGGGCA
1635 144_HRV96    CTGTTCACTTATGCTAGATTTGATTCAGAGATAACAATTG-TTCCATGTGTTGCTGTGCA
1636 145_HRV96b   CTGTTCACTTATGCTAGATTTGATTCAGAGATAACAATTG-TTCCATGTGTTGCTGTGCA
1637 146_HRV96a   CTGTTCACTTATGCTAGATTTGATTCAGAGATAACAATTG-TTCCATGTGTTGCTGTGCA
1638  90_HRV16a|  ATGTTTACTTATGCAAGATTTGACTCTGAAATTACTATGG-TACCAAGTGTAGCAGCCAA
1639  91_HRV16b|  ATGTTTACTTATGCAAGATTTGACTCTGAAATTACTATGG-TACCAAGTGTAGCAGCCAA
1640  92_1AYM_A   ATGTTTACTTATGCAAGATTTGACTCTGAAATTACTATGG-TACCAAGTGTAGCAGCCAA
1641  93_HRV81a|  ATGTTCACATACACTAGATTTAACTCTGAGATTACACTGG-TACCAAGTATTGCAAACAA
1642  94_HRV81b|  ATGTTCACATACACTAGATTTAACTCTGAGATTACACTGG-TACCAAGTATTGCAAACAA
1643  95_HRV81    ATGTTCACATACACTAGATTTAACTCTGAGATTACACTGG-TACCAAGTATTGCAAACAA
1644 147_HRV2     TTGTTCACCTATACTAGGTTTGATTCTGAAATAACCCTAG-TTCCATGCATTTCCGCCCT
1645 148_HRV2a|   TTGTTCACCTATACTAGGTTTGATTCTGAAATAACCCTAG-TTCCATGCATTTCCGCCCT
1646 149_HRV2b|   TTGTTCACCTATACTAGGTTTGATTCTGAAATAACCCTAG-TTCCATGCATTTCCGCCCT
1647 150_HRV49a   CTGTTTACTTACACTAGATTCGATTCTGAAATAACCTTGG-TTCCATGCATTTCTGCACT
1648 151_HRV49b   CTGTTTACTTACACTAGATTCGATTCTGAAATAACCTTGG-TTCCATGCATTTCTGCACT
1649 152_HRV49    CTGTTTACTTACACTAGATTCGATTCTGAAATAACCTTGG-TTCCATGCATTTCTGCACT
1650 153_HRV23a   CTGTTTACTTACACTAGATTTGATTCTGAAATTACTTTGG-TTCCATGCATTTCTGCTCT
1651 154_HRV23b   CTGTTTACTTACACTAGATTTGATTCTGAAATTACTTTGG-TTCCATGCATTTCTGCTCT
1652 155_HRV23    CTGTTTACTTACACTAGATTTGATTCTGAAATTACTTTGG-TTCCATGCATTTCTGCTCT
1653 156_HRV30a   CTATTCACTTACACTAGATTTGATTCTGAGATAACCTTGG-TTCCGTGTATTTCAGCTCT
1654 157_HRV30b   CTATTCACTTACACTAGATTTGATTCTGAGATAACCTTGG-TTCCGTGTATTTCAGCTCT
1655 158_HRV30    CTATTCACTTACACTAGATTTGATTCTGAGATAACCTTGG-TTCCGTGTATTTCAGCTCT
1656 159_HRV7     CTATTCACATACACTAGATTTGATTCTGAGATAACAATAG-TCACAGCAGCAGCAGCACA
1657 160_HRV7b|   CTATTCACATACACTAGATTTGATTCTGAGATAACAATAG-TCACAGCAGCAGCAGCACA
1658 161_HRV7a|   CTATTCACATACACTAGATTTGATTCTGAGATAACAATAG-TCACAGCAGCAGCAGCACA
1659 162_HRV88    TTGTTTACATACACTAGATTTGACTCAGAAATAACAATAG-TCACAGCAGCTGCAGCACA
1660 163_HRV88a   TTGTTTACATACACTAGATTTGACTCAGAAATAACAATAG-TCACAGCAGCTGCAGCACA
1661 164_HRV88b   TTGTTTACATACACTAGATTTGACTCAGAAATAACAATAG-TCACAGCAGCTGCAGCACA
1662 165_HRV36a   TTGTTTACATACACAAGATTTGACTCAGAAATAACAATAG-TCACCGCAGCTGCAGTGCA
1663 166_HRV36b   TTGTTTACATACACAAGATTTGACTCAGAAATAACAATAG-TCACCGCAGCTGCAGTGCA
1664 167_HRV36    TTGTTTACATACACAAGATTTGACTCAGAAATAACAATAG-TCACCGCAGCTGCAGTGCA
1665 168_HRV89a   TTATTCACATATACAAGATTTGATTCAGAGATAACAATAG-TCACTGCAGCCGCAGCTCA
1666 169_HRV89b   TTATTCACATATACAAGATTTGATTCAGAGATAACAATAG-TCACTGCAGCCGCAGCTCA
1667 170_HRV89    TTATTCACATATACAAGATTTGATTCAGAGATAACAATAG-TCACTGCAGCCGCAGCTCA
1668 171_HRV58    TTGTTTACATATACAAGATTTGACTCAGAGATTACAATAG-TCACTGCAGCAGCTGCTCA
1669 172_HRV58a   TTGTTTACATATACAAGATTTGACTCAGAGATTACAATAG-TCACTGCAGCAGCTGCTCA
1670 173_HRV58b   TTGTTTACATATACAAGATTTGACTCAGAGATTACAATAG-TCACTGCAGCAGCTGCTCA
1671 174_HRV12a   CTTTTCACCTACTTAAGGTTTGATTCTGAAATCACCATTGTTCCAAGCAATG-CAGCAAT
1672 175_HRV12b   CTTTTCACCTACTTAAGGTTTGATTCTGAAATCACCATTGTTCCAAGCAATG-CAGCAAT
1673 176_HRV12    CTTTTCACCTACTTAAGGTTTGATTCTGAAATCACCATTGTTCCAAGCAATG-CAGCAAT
1674 177_HRV78a   ATGTTCACATATCTCAGATTTGATTCAGAAATCACTCTTG-TGTGTGCAGTGGCCTCACA
1675 178_HRV78b   ATGTTCACATATCTCAGATTTGATTCAGAAATCACTCTTG-TGTGTGCAGTGGCCTCACA
1676 179_HRV78    ATGTTCACATATCTCAGATTTGATTCAGAAATCACTCTTG-TGTGTGCAGTGGCCTCACA
1677 180_HRV20    CTCTTTACATACCTCAGATTTGATTCTGAGATTACAATAG-TAGCAACAGTAGCTGCACT
1678 181_HRV20a   CTCTTTACATACCTCAGATTTGATTCTGAGATTACAATAG-TAGCAACAGTAGCTGCACT
1679 182_HRV20b   CTCTTTACATACCTCAGATTTGATTCTGAGATTACAATAG-TAGCAACAGTAGCTGCACT
1680 183_HRV68    CTATTCACATACCTTAGGTTTGACTCTGAGATTACAATAG-TAGCAACAATAGCTGCTCT
1681 184_HRV68a   CTATTCACATACCTTAGGTTTGACTCTGAGATTACAATAG-TAGCAACAATAGCTGCTCT
1682 185_HRV68b   CTATTCACATACCTTAGGTTTGACTCTGAGATTACAATAG-TAGCAACAATAGCTGCTCT
1683 186_HRV28    ATGTTTACATATCTCAGATTTGATTCTGAAATTACTATAG-TGGTGTCAGTTGCAAGTAA
1684 187_HRV28a   ATGTTTACATATCTCAGATTTGATTCTGAAATTACTATAG-TGGTGTCAGTTGCAAGTAA
1685 188_HRV28b   ATGTTTACATATCTCAGATTTGATTCTGAAATTACTATAG-TGGTGTCAGTTGCAAGTAA
1686 189_HRV53a   ATGTTCACATACTTAGATTTGATTCAGAAATAACTATAG-TGGTATCAGTGGCTAGTAA
1687 190_HRV53b   ATGTTCACATACTTAGATTTGATTCAGAAATAACTATAG-TGGTATCAGTGGCTAGTAA
1688 191_HRV53    ATGTTCACATACTTAGATTTGATTCAGAAATAACTATAG-TGGTATCAGTGGCTAGTAA
1689 192_HRV46a   CTTTTACATATCTCAGATTTGATTCAGAAATAACAATAG-TCACCACATTGGCAGGCCA
1690 193_HRV46b   CTTTTACATATCTCAGATTTGATTCAGAAATAACAATAG-TCACCACATTGGCAGGCCA
```

FIG. D6 CONT'D

```
02.trace                                                          9/20/2007 4:59 PM 1691  194_HRV46     CTTTTTACATATCTCAGATTTGATTCAGAAATAACAATAG-TCACCACATTGGCAGGCCA
1692  195_HRV80a    CTTTTCACTTACCTCAGATTTGACTCAGAAATAACAATAG-TAACTACCTTAGCAGGACA
1693  196_HRV80b    CTTTTCACTTACCTCAGATTTGACTCAGAAATAACAATAG-TAACTACCTTAGCAGGACA
1694  197_HRV80     CTTTTCACTTACCTCAGATTTGACTCAGAAATAACAATAG-TAACTACCTTAGCAGGACA
1695  198_HRV51     CTTTTCACATACTTAAGATTTGATTCAGAGATCACTATAG-TTGCTACCATTGCTGGACA
1696  199_HRV51a    CTTTTCACATACTTAAGATTTGATTCAGAGATCACTATAG-TTGCTACCATTGCTGGACA
1697  200_HRV51b    CTTTTCACATACTTAAGATTTGATTCAGAGATCACTATAG-TTGCTACCATTGCTGGACA
1698  201_HRV65a    CTCTTCACCTATTTGCGCTTTGACTCAGAAATTACCATAG-TGGCTACTATAGCTGGACA
1699  202_HRV65b    CTCTTCACCTATTTGCGCTTTGACTCAGAAATTACCATAG-TGGCTACTATAGCTGGACA
1700  203_HRV65     CTCTTCACCTATTTGCGCTTTGACTCAGAAATTACCATAG-TGGCTACTATAGCTGGACA
1701  204_HRV71a    CTCTTCACATACCTGCGCTTTGATTCAGAGATAACAATTG-TAGCTACACTAGCAGGGCA
1702  205_HRV71b    CTCTTCACATACCTGCGCTTTGATTCAGAGATAACAATTG-TAGCTACACTAGCAGGGCA
1703  206_HRV71     CTCTTCACATACCTGCGCTTTGATTCAGAGATAACAATTG-TAGCTACACTAGCAGGGCA
1704  207_HRV8      ATGTTCACTTATGTAAGATTTGATTCAGAGATAACAATTG-TACCATGTATTGCAGCTAT
1705  208_HRV95     ATGTTCACTTATGTAAGATTTGATTCAGAGATAACAATTG-TACCATGTATTGCAGCTAT
1706  209_HRV45     ATGTTTACATATGTCAGATTTGATTCCGAAATAACAATAG-TACCATGTGTTGCTGCCAC
1707  210_HRV45a    ATGTTTACATATGTCAGATTTGATTCCGAAATAACAATAG-TACCATGTGTTGCTGCCAC
1708  211_HRV45b    ATGTTTACATATGTCAGATTTGATTCCGAAATAACAATAG-TACCATGTGTTGCTGCCAC
1709  GROUP_1       -T-TT-AC-TA-----G-TT--A-TC-GA--T-AC--T-G-T----------C------
1710
1711  1_HRV1A1|d    AGGAGACGACATTGGACATATTGTAATGCAATATATGTATGTTCCTCCAGGAGCTCCAAT
1712  2_HRV1A2|d    AGGAGACGACATTGGACATATTGTAATGCAATATATGTATGTTCCTCCAGGAGCTCCAAT
1713  3_HRV1A|cD    AGGAGACGACATTGGACATATTGTAATGCAATATATGTATGTTCCTCCAGGAGCTCCAAT
1714  4_HRV1B1|d    AGGAGATGACATTGGTCATGTTGTAATGCAGTATATGTATGTTCCCCCAGGAGCTCCAAT
1715  5_HRV1B2|d    AGGAGATGACATTGGTCATGTTGTAATGCAGTATATGTATGTTCCCCCAGGAGCTCCAAT
1716  6_HRV1B       AGGAGATGACATTGGTCATGTTGTAATGCAGTATATGTATGTTCCCCCAGGAGCTCCAAT
1717  7_HRV40a|d    GGGTGAAGACATTGGACACATTGTGATGCAATATATGTATGTACCCCCTGGCGCACCCAT
1718  8_HRV40b|d    GGGTGAAGACATTGGACACATTGTGATGCAATATATGTATGTACCCCCTGGCGCACCCAT
1719  9_HRV40       GGGTGAAGACATTGGACACATTGTGATGCAATATATGTATGTACCCCCTGGCGCACCCAT
1720  10_HRV85      GGGTGATGATATTGGACACATTGTAATGCAGTATATGTATGTGCCCCCCGGAGCACCAAT
1721  11_HRV85a|    GGGTGATGATATTGGACACATTGTAATGCAGTATATGTATGTGCCCCCCGGAGCACCAAT
1722  12_HRV85b|    GGGTGATGATATTGGACACATTGTAATGCAGTATATGTATGTGCCCCCCGGAGCACCAAT
1723  13_HRV56a|    GGGAGATGATATTGGACACATTGTAATGCAATACATGTATGTGCCTCCTGGTGCACCACT
1724  14_HRV56b|    GGGAGATGATATTGGACACATTGTAATGCAATACATGTATGTGCCTCCTGGTGCACCACT
1725  15_HRV56      GGGAGATGATATTGGACACATTGTAATGCAATACATGTATGTGCCTCCTGGTGCACCACT
1726  16_HRV54      GGGAGTTGATATTGGACACATTGTCATGCAATTCATGTATGTACCGCCTGGTGCACCAAA
1727  17_HRV98      GGGAGCTGACATTGGACACATTGTCATGCAATTCATGTATGTTCCACCTGGTGCACCTAA
1728  18_HRV59a|    AGGGGATGGTCATATAGTCATGCAATATATGTATGTGTCACCAGGTGCTCCACT
1729  19_HRV59b|    AGGGGATGACATTGGTCATATAGTCATGCAATATATGTATGTTCCACCAGGTGCTCCACT
1730  20_HRV59      AGGGGATGACATTGGTCATATAGTCATGCAATATATGTATGTTCCACCAGGTGCTCCACT
1731  21_HRV63      AGGTGATGACATTGGTCATATAGTTATGCAGTACATGTACGTTCCACCCGGTGCCCCTCT
1732  22_HRV63b|    AGGTGATGACATTGGTCATATAGTTATGCAGTACATGTACGTTCCACCCGGTGCCCCTCT
1733  23_HRV63a|    AGGTGATGACATTGGTCATATAGTTATGCAGTACATGTACGTTCCACCCGGTGCCCCTCT
1734  24_HRV39      AGGTGAAGATATTGGACACATAGTAATGCAATACATGTATGTCCCACCTGGTGCACCTGT
1735  25_HRV39a|    AGGTGAAGATATTGGACACATAGTAATGCAATACATGTATGTCCCACCTGGTGCACCTGT
1736  26_HRV39b|    AGGTGAAGATATTGGACACATAGTAATGCAATACATGTATGTCCCACCCGGTGCACCTGT
1737  27_HRV10a|    GGGCGATGACATAGGTCACATAGTTATGCAATATATGTATGTGCCACCTGGGGCTCCAGT
1738  28_HRV10b|    GGGCGATGACATAGGTCACATAGTTATGCAATATATGTATGTGCCACCTGGGGCTCCAGT
1739  29_HRV10      GGGCGATGACATAGGTCACATAGTTATGCAATATATGTATGTGCCACCTGGGGCTCCAGT
1740  30_HRV100a    AGGAGATGACATAGGGCATATCGTAATGCAGTACATGTATGTGCCACCTGGAGCTCCAGT
1741  31_HRV100b    AGGAGATGACATAGGGCATATCGTAATGCAGTACATGTATGTGCCACCTGGAGCTCCAGT
1742  32_HRV100     GGGAGATGACATAGGGCATATCGTAATGCAGTACATGTATGTGCCACCTGGAGCTCCAGT
1743  33_HRV66      GGGTGATGATATAGGACATATTGTGATGCAATACATGTATGTACCACCTGGAGCCCCAAT
1744  34_HRV66b|    GGGTGATGATATAGGACATATTGTGATGCAATACATGTATGTACCACCTGGAGCCCCAAT
1745  35_HRV66a|    GGGTGATGATATAGGACATATTGTGATGCAATACATGTATGTACCACCTGGAGCCCCAAT
1746  36_HRV77a|    AGGTGATGACATAGGACATGTTGTCATGCAATACATGTATGTACCACCAGGGGCACCCAT
1747  37_HRV77b|    AGGTGATGACATAGGACATGTTGTCATGCAATACATGTATGTACCACCAGGGGCACCCAT
1748  38_HRV77      AGGTGATGACATAGGACATGTTGTCATGCAATACATGTATGTACCACCAGGGGCACCCAT
1749  39_HRV62a     TGGTGCAGATATAGGTCACATAGTTATGCAATATATGTATGTACCACCTGGGGCTCCACT
1750  40_HRV62b     TGGTGCAGATATAGGTCACATAGTTATGCAATATATGTATGTACCACCTGGGGCTCCACT
1751  41_HRV25      TGGTGCAGATATAGGTCACATAGTTATGCAATATATGTATGTGCCACCTGGAGCCCCATT
1752  42_HRV29a     TGGTAATGATATAGGTCACATAGTTATGCAGTACATGTATGTACCACCTGGAGCTCCAGT
1753  43_HRV29b     TGGTAATGATATAGGTCACATAGTTATGCAGTACATGTATGTACCACCTGGAGCTCCAGT
1754  44_HRV44a     TGGTGATGATATAGGCCACATAGTTATGCAGTACATGTATGTACCACCTGGAGCTCCAGT
1755  45_HRV44b     TGGTGATGATATAGGCCACATAGTTATGCAGTACATGTATGTACCACCTGGAGCTCCAGT
```

FIG. D6 CONT'D

```
02.trace                                                        9/20/2007 4:59 PM 1756  46_HRV31    TGGTAGTGACATAGGCCATATAGTCATGCAATACATGTATGTACCACCTGGGGCCCCAGT
1757  47_HRV31a|  TGGTAGTGACATAGGCCATATAGTCATGCAATACATGTATGTACCACCTGGGGCCCCAGT
1758  48_HRV31b|  TGGTAGTGACATAGGCCATATAGTCATGCAATACATGTATGTACCACCTGGGGCCCCAGT
1759  49_HRV47    TGGTGATGACATAGGTCACATAGTTATGCAATACATGTATGTGCCGCCTGGGGCTCCAGT
1760  50_HRV47a|  TGGTGATGACATAGGTCACATAGTTATGCAATACATGTATGTGCCGCCTGGGGCTCCAGT
1761  51_HRV47b|  TGGTGATGACATAGGTCACATAGTTATGCAATACATGTATGTGCCGCCTGGGGCTCCAGT
1762  52_HRV11    AGGAAATGATATTGGTCATGTTGTAATGCAATATATGTATGTCCCACCAGGTGCTCCAGT
1763  53_HRV11b|  AGGAAATGATATTGGTCATGTTGTAATGCAATATATGTATGTCCCACCAGGTGCTCCAGT
1764  54_HRV11a|  AGGAAATGATATTGGTCATGTTGTAATGCAATATATGTATGTCCCACCAGGTGCTCCAGT
1765  55_HRV76    AGGGGATGACATTGGTCATGTAGTGATGCAATACATGTATGTCCCACCAGGCGCTCCAGT
1766  56_HRV76b|  AGGGGATGACATTGGTCATGTAGTGATGCAATACATGTATGTCCCACCAGGCGCTCCAGT
1767  57_HRV76a|  AGGGGATGACATTGGTCATGTAGTGATGCAATACATGTATGTCCCACCAGGCGCTCCAGT
1768  58_HRV33    GGGAGATGATGTTGGTCATGTTGTAATGCAGTACATGTATGTCCCACCAGGTGCACCAGC
1769  59_HRV33b|  GGGAGATGATGTTGGTCATGTTGTAATGCAGTACATGTATGTCCCACCAGGTGCACCAGC
1770  60_HRV33a|  GGGAGATGATGTTGGTCATGTTGTAATGCAGTACATGTATGTCCCACCAGGTGCACCAGC
1771  61_HRV24a|  GGGAGATGACATTGGACATGTTGTAATGCAGTACATGTATATACCACCTGGAGCACCAGT
1772  62_HRV24b|  GGGAGATGACATTGGACATGTTGTAATGCAGTACATGTATATACCACCTGGAGCACCAGT
1773  63_HRV24    GGGAGATGACATTGGACATGTTGTAATGCAGTACATGTATATACCACCTGGAGCACCAGT
1774  64_HRV90    GGGCAATGATATTGGACATGTTGTGATGCAATACATGTATATACCACCTGGGGCACCAGT
1775  65_HRV90a|  GGGCAATGATATTGGACATGTTGTGATGCAATACATGTATATACCACCTGGGGCACCAGT
1776  66_HRV90b|  GGGCAATGATATTGGACATGTTGTGATGCAATACATGTATATACCACCTGGGGCACCAGT
1777  67_HRV34    AGGTGATGATATTGGACATGTTGTGATGCAATACATGTATGTACCACCAGGTGCACCAAT
1778  68_HRV34b|  AGGTGATGATATTGGACATGTTGTGATGCAATACATGTATGTACCACCAGGTGCACCAAT
1779  69_HRV34a|  AGGTGATGATATTGGACATGTTGTGATGCAATACATGTATGTACCACCAGGTGCACCAAT
1780  70_HRV50a|  GGGTGTTGATATTGGACATGTTGTCATGCAATACATGTATGTCCCACCAGGTGCACCAAT
1781  71_HRV50b|  GGGTGTTGATATTGGACATGTTGTCATGCAATACATGTATGTCCCACCAGGTGCACCAAT
1782  72_HRV50    GGGTGTTGATATTGGACATGTTGTCATGCAATACATGTATGTCCCACCAGGTGCACCAAT
1783  73_HRV18a|  GGGTGATGACATAGGACATATTGTTATGCAGTACATGTATGTTCCTCCAGGAGCACCAAT
1784  74_HRV18b|  GGGTGATGACATAGGACATATTGTTATGCAGTACATGTATGTTCCTCCAGGAGCACCAAT
1785  75_HRV18    GGGTGATGACATAGGACATATTGTTATGCAGTACATGTATGTTCCTCCAGGAGCACCAAT
1786  76_HRV55    GGGAGACATTGGACATGTCATGCAATACATGTATGTTCCACCTGGAGCACCAAT
1787  77_HRV55b|  GGGAGATGACATTGGACATGTAGTCATGCAATACATGTATGTTCCACCTGGAGCACCAAT
1788  78_HRV55a|  GGGAGATGACATTGGACATGTAGTCATGCAATACATGTATGTTCCACCTGGAGCACCAAT
1789  79_HRV57    AGGTGAGGATATAGGCCATGTTGTAATGCAATACATGTATGTCCCTCCTGGGGCACCAAT
1790  80_HRV57a|  AGGTGAGGATATAGGCCATGTTGTAATGCAATACATGTATGTCCCTCCTGGGGCACCAAT
1791  81_HRV57b|  AGGTGAGGATATAGGCCATGTTGTAATGCAATACATGTATGTCCCTCCTGGGGCACCAAT
1792  82_HRV21    AACGGGTGACATAGGACATGTTGTAATGCAATATATGTATGTCCCACCAGGTGCTCCAAT
1793  83_HRVHan   AGCGGGTGACATAGGACATGTTGTGATGCAATATATGTATGTCCCACCAGGTGCTCCAAT
1794  84_HRV43    AAGCAATGATATAGGCCATGTGGTAATGCAGTACATGTATGTACCACCAGGTGCGCCAGT
1795  85_HRV43b|  AAGCAATGATATAGGCCATGTGGTAATGCAGTACATGTATGTACCACCAGGTGCGCCAAT
1796  86_HRV43a|  AAGCAATGATATAGGCCATGTGGTAATGCAGTACATGTATGTACCACCAGGTGCGCCAAT
1797  87_HRV75    AGGGAATGACATAGGCCATGTAGTCAATATATGTATGTACCACCAGGAGCACCAAT
1798  88_HRV75b|  AGGGAATGACATAGGCCATGTAGTAATGCAATATATGTATGTACCACCAGGAGCACCAAT
1799  89_HRV75a|  AGGGAATGACATAGGCCATGTAGTAATGCAATATATGTATGTACCACCAGGAGCACCAAT
1800  96_HRV9a|d  AAGTGATAGCGTTGGCCATGTTGTTATGCAGTACATGTATGTACCACCAGGGGCACCTTT
1801  97_HRV9b|d  AAGTGATAGCGTTGGCCATGTTGTTATGCAGTACATGTATGTACCACCAGGGGCACCTTT
1802  98_HRV9     AAGTGATAGCGTTGGCCATGTTGTTATGCAGTACATGTATGTACCACCAGGGGCACCTTT
1803  99_HRV32    AAGTGACAGCATTGGTCATGTTGTTATGCAGTACATGTATGTACCACCAGGGGCTCCTCT
1804  100_HRV32a  AAGTGACAGCATTGGTCATGTTGTTATGCAGTACATGTATGTACCACCAGGGGCTCCTCT
1805  101_HRV32b  AAGTGACAGCATTGGTCATGTTGTTATGCAGTACATGTATGTACCACCAGGGGCTCCTCT
1806  102_HRV67   GAGTGACAGCATTGGGCATGTTGTAATGCAATATATGTATGTACCTCCAGGAGCACCATT
1807  103_HRV67a  GAGTGACAGCATTGGGCATGTTGTAATGCAATATATGTATGTACCTCCAGGAGCACCATT
1808  104_HRV67b  GAGTGACAGCATTGGGCATGTTGTAATGCAATATATGTATGTACCTCCAGGAGCACCATT
1809  105_HRV15   GAGTGATAACATCGGTCATGTTGTCATGCAATATATGTATGTTCCTCGGGGAGCCCCTTT
1810  106_HRV15a  GAGTGATAACATCGGTCATGTTGTCATGCAATATATGTATGTTCCTCGGGGAGCCCCTTT
1811  107_HRV15b  GAGTGATAACATCGGTCATGTTGTCATGCAATATATGTATGTTCCTCGGGGAGCCCCTTT
1812  108_HRV74a  AAGTGACAACATTGGCCATGTTGTTATGCAATACATGTATGTCCCCCCAGGAGCACCTTT
1813  109_HRV74b  AAGTGACAACATTGGCCATGTTGTTATGCAATACATGTATGTCCCCCCAGGAGCACCTTT
1814  110_HRV74   AAGTGACAACATTGGCCATGTTGTTATGCAATACATGTATGTCCCCCCAGGAGCACCTTT
1815  111_HRV38a  AAATGAAGGTGTGGGGCATGTTGTTATGCAGTATATGTATGTCCCTCCAGGGGCACCATT
1816  112_HRV38b  AAATGAAGGTGTGGGGCATGTTGTTATGCAGTATATGTATGTCCCTCCAGGGGCACCATT
1817  113_HRV38   AAATGAAGGTGTGGGGCATGTTGTTATGCAGTATATGTATGTCCCTCCAGGGGCACCATT
1818  114_HRV60   AAATGATGGCATAGGTCATGTTGTCATGCAATACATGTATGTCCCCCCAGGAGCACCATT
1819  115_HRV60a  AAATGATGGCATAGGTCATGTTGTCATGCAATACATGTATGTCCCCCCAGGAGCACCATT
1820  116_HRV60b  AAATGATGGCATAGGTCATGTTGTCATGCAATACATGTATGTCCCCCCAGGAGCACCATT
```

FIG. D6 CONT'D

02.trace                                                                9/20/2007  4:59 PM

```
1821  117_HRV64a   GAGTGCTAACATTGGTCATGTTGTTATGCAATATATGTATGTCCCTCCTGGAGCTCCAAT
1822  118_HRV64b   GAGTGCTAACATTGGTCATGTTGTTATGCAATATATGTATGTCCCTCCTGGAGCTCCAAT
1823  119_HRV64    GAGTGCTAACATTGGTCATGTTGTTATGCAATATATGTATGTCCCTCCTGGAGCTCCAAT
1824  120_HRV94a   AAGTGCTAATATTGGTCATGTTGTCATGCAGTACATGTATGTTCCTCCTGGAGCTCCAAA
1825  121_HRV94b   AAGTGCTAATATTGGTCATGTTGTCATGCAGTACATGTATGTTCCTCCTGGAGCTCCAAA
1826  122_HRV94    AAGTGCTAATATTGGTCATGTTGTCATGCAGTACATGTATGTTCCTCCTGGAGCTCCAAA
1827  123_HRV22    AAGTAAAAACATTGGTCATGTGGTCATGCAATACATGTATGTTCCGCCTGGAGCTCCTAA
1828  124_HRV22a   AAGTAAAAACATTGGTCATGTGGTCATGCAATACATGTATGTTCCGCCTGGAGCTCCTAA
1829  125_HRV22b   AAGTAAAAACATTGGTCATGTGGTCATGCAATACATGTATGTTCCGCCTGGAGCTCCTAA
1830  126_HRV82    AAGTAATGATATTGGGCATGTAGTGATGCAATACATGTATGTCCCACCAGGTGCTCCTAA
1831  127_HRV82b   AAGTAATGATATTGGGCATGTAGTGATGCAATACATGTATGTCCCACCAGGTGCTCCTAA
1832  128_HRV82a   AAGTAATGATATTGGGCATGTAGTGATGCAATACATGTATGTCCCACCAGGTGCTCCTAA
1833  129_HRV19    AAGTAAAAACATTGGACATGTTGTTATGCAATACATGTATGTGCCTCCTGGTGCTCCTAT
1834  130_HRV19a   AAGTAAAAACATTGGACATGTTGTTATGCAATACATGTATGTGCCTCCTGGTGCTCCTAT
1835  131_HRV19b   AAGTAAAAACATTGGACATGTTGTTATGCAATACATGTATGTGCCTCCTGGTGCTCCTAT
1836  132_HRV13    AGGTGGTGATGTCGGACATGTTGTTATGCAATACATGTATGTACCGCCCGGTGCACCCCT
1837  133_HRV13a   AGGTGGTGATGTCGGACATGTTGTTATGCAATACATGTATGTACCGCCCGGTGCACCCCT
1838  134_HRV13b   AGGTGGTGATGTCGGACATGTTGTTATGCAATACATGTATGTACCGCCCGGTGCACCCCT
1839  135_HRV41    GGGTAGTGATGTCGGACATGTTGTCATGCAATACATGTTCGTACCACCTGGCGCACCCCT
1840  136_HRV41a   GGGTAGTGATGTCGGACATGTTGTCATGCAATACATGTTCGTACCACCTGGCGCACCCCT
1841  137_HRV41b   GGGTAGTGATGTCGGACATGTTGTCATGCAATACATGTTCGTACCACCTGGCGCACCCCT
1842  138_HRV73    AAGTGGAGATGTGGGACATGTAGTTATGCAGTATATGTATGTCCCACCTGGAGCCCCTCT
1843  139_HRV73b   AAGTGGAGATGTGGGACATGTAGTTATGCAGTATATGTATGTCCCACCTGGAGCCCCTCT
1844  140_HRV73a   AAGTGGAGATGTGGGACATGTAGTTATGCAGTATATGTATGTCCCACCTGGAGCCCCTCT
1845  141_HRV61    AGGTGGTGACATTGGACACGTGGTCATGCAATACATGTATGTTCCACCTGGTGCACCTAC
1846  142_HRV61a   AGGTGGTGACATTGGACACGTGGTCATGCAATACATGTATGTTCCACCTGGTGCACCTAC
1847  143_HRV61b   AGGTGGTGACATTGGACACGTGGTCATGCAATACATGTATGTTCCACCTGGTGCACCTAC
1848  144_HRV96    GAGTGGTGATATTGGTCATGTGGTCATGCAATATATGTATGTTCCACCAGGTGCCCCCAC
1849  145_HRV96b   GAGTGGTGATATTGGTCATGTGGTCATGCAATATATGTATGTTCCACCAGGTGCCCCCAC
1850  146_HRV96a   GAGTGGTGATATTGGTCATGTGGTCATGCAATATATGTATGTTCCACCAGGTGCCCCCAC
1851  90_HRV16a|   AGATGGTCACATTGGTCATATAGTCATGCAATATATGTATGTACCACCAGGAGCACCTAT
1852  91_HRV16b|   AGATGGTCACATTGGTCATATAGTCATGCAATATATGTATGTACCACCAGGAGCACCTAT
1853  92_1AYM_A    AGATGGTCACATTGGTCATATAGTCATGCAATATATGTATGTACCACCAGGAGCACCTAT
1854  93_HRV81a|   GGAAGGTCATATTGGTCATATAGTAATGCAATACATGTATGTACCACCAGGAGCACCCAT
1855  94_HRV81b|   GGAAGGTCATATTGGTCATATAGTAATGCAATACATGTATGTACCACCAGGAGCACCCAT
1856  95_HRV81     GGAAGGTCATATTGGTCATATAGTAATGCAATACATGTATGTACCACCAGGAGCACCCAT
1857  147_HRV2     TAGTCAGGACATTGGACACATCACAATGCAATACATGTATGTTCCACCTGGTGCACCGGT
1858  148_HRV2a|   TAGTCAGGACATTGGACACATCACAATGCAATACATGTATGTTCCACCTGGTGCACCGGT
1859  149_HRV2b|   TAGTCAGGACATTGGACACATCACAATGCAATACATGTATGTTCCACCTGGTGCACCGGT
1860  150_HRV49a   TAGCAAGGATATTGGACACATTACAATGCAATACATGTATGTGCCCGCCAGGTGCACCTGT
1861  151_HRV49b   TAGCAAGGATATTGGACACATTACAATGCAATACATGTATGTGCCCGCCAGGTGCACCTGT
1862  152_HRV49    TAGCAAGGATATTGGACACATTACAATGCAATACATGTATGTGCCCGCCAGGTGCACCTGT
1863  153_HRV23a   TAGTCAAGATATTGGTCACATCACAATGCAGTATATGTATGTCCCACCAGGTGCTCCAAT
1864  154_HRV23b   TAGTCAAGATATTGGTCACATCACAATGCAGTATATGTATGTCCCACCAGGTGCTCCAAT
1865  155_HRV23    TAGTCAAGATATTGGTCACATCACAATGCAGTATATGTATGTCCCACCAGGTGCTCCAAT
1866  156_HRV30a   CAGCCAAGATATCGGACACATTACAATGCAGTATATGTATGTCCCTGGCGCTCCAAT
1867  157_HRV30b   CAGCCAAGATATCGGACACATTACAATGCAGTATATGTATGTTCCACCTGGCGCTCCAAT
1868  158_HRV30    CAGCCAAGATATCGGACACATTACAATGCAGTATATGTATGTTCCACCTGGCGCTCCAAT
1869  159_HRV7     AGGTAATGATATTGGACATATAGTTATGCAATTTATGTATGTACCTCCAGGGGCCCCAGT
1870  160_HRV7b|   AGGTAATGATATTGGACATATAGTTATGCAATTTATGTATGTACCTCCAGGGGCCCCAGT
1871  161_HRV7a|   AGGTAATGATATTGGACATATAGTTATGCAATTTATGTATGTACCTCCAGGGGCCCCAGT
1872  162_HRV88    AGGTGATGATACTGGACATATAGTACTGCAATTCATGTATGTGCCTCCAGGTGCACCAAT
1873  163_HRV88a   AGGTGATGATACTGGACATATAGTACTGCAATTCATGTATGTGCCTCCAGGTGCACCAAT
1874  164_HRV88b   AGGTGATGATACTGGACATATAGTACTGCAATTCATGTATGTGCCTCCAGGTGCACCAAT
1875  165_HRV36a   GGGAGATGATAGTGGGCATGTAGTATTACAATTCATGTATGTACCTCCAGGAGCGCCTGT
1876  166_HRV36b   GGGAGATGATAGTGGGCATGTAGTATTACAATTCATGTATGTACCTCCAGGAGCGCCTGT
1877  167_HRV36    GGGAGATGATAGTGGGCATGTAGTATTACAATTCATGTATGTACCTCCAGGAGCGCCTGT
1878  168_HRV89a   AGGAAATGATAGTGGACATATAGTATTGCAATTTATGTATGTACCCCCAGGAGCACCTGT
1879  169_HRV89b   AGGAAATGATAGTGGACATATAGTATTGCAATTTATGTATGTACCCCCAGGAGCACCTGT
1880  170_HRV89    AGGAAATGATAGTGGACATATAGTATTGCAATTTATGTATGTACCCCCAGGAGCACCTGT
1881  171_HRV58    AGGAGAAGATAATGGACATATTGTGTTACAATTTATGTATGTACCCCCAGGAGCACCTGT
1882  172_HRV58a   AGGAGAAGATAATGGACATATTGTGTTACAATTTATGTATGTACCCCCAGGAGCACCTGT
1883  173_HRV58b   AGGAGAAGATAATGGACATATTGTGTTACAATTTATGTATGTACCCCCAGGAGCACCTGT
1884  174_HRV12a   AGAAGGAAGCAATGGTCACGTGGTGGTCCAATACATGTATGTACCTCCTGGTGCCCCACT
1885  175_HRV12b   AGAAGGAAGCAATGGTCACGTGGTGGTCCAATACATGTATGTACCTCCTGGTGCCCCACT
```

FIG. D6 CONT'D

02.trace                                                                9/20/2007 4:59 PM

```
1886 176_HRV12      AGAAGGAAGCAATGGTCACGTGGTGGTCCAATACATGTATGTACCTCCTGGTGCCCCACT
1887 177_HRV78a     AGGAGACAATAATGGACATGTGGTGCTTCAATTTATGTTTGTTCCACCTGGAGCCCCTAT
1888 178_HRV78b     AGGAGACAATAATGGACATGTGGTGCTTCAATTTATGTTTGTTCCACCTGGAGCCCCTAT
1889 179_HRV78      AGGAGACAATAATGGACATGTGGTGCTTCAATTTATGTTTGTTCCACCTGGAGCCCCTAT
1890 180_HRV20      AGGTCGGGATAATGGGCATGTTGTTTTACAGTATATGTATGTACCACCAGGGGCACCAAT
1891 181_HRV20a     AGGTCGGGATAATGGGCATGTTGTTTTACAGTATATGTATGTACCACCAGGGGCACCAAT
1892 182_HRV20b     AGGTCGGGATAATGGGCATGTTGTTTTACAGTATATGTATGTACCACCAGGGGCACCAAT
1893 183_HRV68      TGGAAAAGATAATGGCCATGTGGTTTTACAGTACATGTATGTGCCGCCAGGGGCACCCAT
1894 184_HRV68a     TGGAAAAGATAATGGCCATGTGGTTTTACAGTACATGTATGTGCCGCCAGGGGCACCCAT
1895 185_HRV68b     TGGAAAAGATAATGGCCATGTGGTTTTACAGTACATGTATGTGCCGCCAGGGGCACCCAT
1896 186_HRV28      AGGTGATGATAATGGGCATGTAGTTATGCAATATATGTATGTACCTCCAGGAGCCCCCAT
1897 187_HRV28a     AGGTGATGATAATGGGCATGTAGTTATGCAATATATGTATGTACCTCCAGGAGCCCCCAT
1898 188_HRV28b     AGGTGATGATAATGGGCATGTAGTTATGCAATATATGTATGTACCTCCAGGAGCCCCCAT
1899 189_HRV53a     ACAAGGGAATAACGGGCACGTGGTGATACAATACATGTATGTACCACCGGGTGCTCCAAT
1900 190_HRV53b     ACAAGGGAATAACGGGCACGTGGTGATACAATACATGTATGTACCACCGGGTGCTCCAAT
1901 191_HRV53      ACAAGGGAATAACGGGCACGTGGTGATACAATACATGTATGTACCACCGGGTGCTCCAAT
1902 192_HRV46a     AGGGGATGATATTGGACATGTGGTCATACAATATATGTATGTGCCTCCTGGTGCTCCATT
1903 193_HRV46b     AGGGGATGATATTGGACATGTGGTCATACAATATATGTATGTGCCTCCTGGTGCTCCATT
1904 194_HRV46      AGGGGATGATATTGGACATGTGGTCATACAATATATGTATGTGCCTCCTGGTGCTCCATT
1905 195_HRV80a     AGGGGAGGACATTGGTCATGTAGTTATTCAATACATGTACGTACCACCAGGGGCCCCGTT
1906 196_HRV80b     AGGGGAGGACATTGGTCATGTAGTTATTCAATACATGTACGTACCACCAGGGGCCCCGTT
1907 197_HRV80      AGGGGAGGACATTGGTCATGTAGTTATTCAATACATGTACGTACCACCAGGGGCCCCGTT
1908 198_HRV51      GGGTGATGACATAGGGCACATTGTACTTCAATACATGTATGTACCCCCTGGAGGACCAGT
1909 199_HRV51a     GGGTGATGACATAGGGCACATTGTACTTCAATACATGTATGTACCCCCTGGAGGACCAGT
1910 200_HRV51b     GGGTGATGACATAGGGCACATTGTACTTCAATACATGTATGTACCCCCTGGAGGACCAGT
1911 201_HRV65a     AGGTGATGACATAGGGCACATAGTGCTTCAATATATGTATGTGCCTCCTGGTGGTCCTGT
1912 202_HRV65b     AGGTGATGACATAGGGCACATAGTGCTTAATATATGTATGTGCCTCCTGGTGGTCCTGT
1913 203_HRV65      AGGTGATGACATAGGGCACATAGTGCTTCAATATATGTATGTGCCTCCTGGTGGTCCTGT
1914 204_HRV71a     AGGAGATGATTTAGGACATATTGTACTCCAGTACATGTATGTTCCCCCAGGTGGTCCAAT
1915 205_HRV71b     AGGAGATGATTTAGGACATATTGTACTCCAGTACATGTATGTTCCCCCAGGTGGTCCAAT
1916 206_HRV71      AGGAGATGATTTAGGACATATTGTACTCCAGTACATGTATGTTCCCCCAGGTGGTCCAAT
1917 207_HRV8       AAAAGGTGACCTTGGACACATAGTCCTTCAATACATGTATGTTCCCCCGGGTGCACCTCT
1918 208_HRV95      AGAAGGTGACCTTGGACACATAGTCCTCCAATACATGTATGTTCCCCCGGGTGCACCTCT
1919 209_HRV45      AGAAGGTAACTTGGGACACATTGTTGTGCAATACATGTTTGTACCACCAGGAGCACCTCT
1920 210_HRV45a     AGAAGGTAACTTGGGACACATTGTTGTGCAATACATGTTTGTACCACCAGGAGCACCTCT
1921 211_HRV45b     AGAAGGTAACTTGGGACACATTGTTGTGCAATACATGTTTGTACCACCAGGAGCACCTCT
1922 GROUP_1        -------------GG-CA--T-----T-CA-T---ATGT---T-CC-CC-GG-G--CC---
1923
1924 1_HRV1A1|d     TCCTTCAAAAAGAAACGATTTCTCATGGCAATCAGGCACCAATATGTCAATATTCTGGCA
1925 2_HRV1A2|d     TCCTTCAAAAAGAAACGATTTCTCATGGCAATCAGGCACCAATATGTCAATATTCTGGCA
1926 3_HRV1A|cD     TCCTTCAAAAAGAAACGATTTCTCATGGCAATCAGGCACCAATATGTCAATATTCTGGCA
1927 4_HRV1B1|d     TCCAAAAACAAGAAATGATTTCTCATGGCAATCAGGCACTAATATGTCAATATTCTGGCA
1928 5_HRV1B2|d     TCCAAAAACAAGAAATGATTTCTCATGGCAATCAGGCACTAATATGTCAATATTCTGGCA
1929 6_HRV1B        TCCAAAAACAAGAAATGATTTCTCATGGCAATCAGGCACTAATATGTCAATATTCTGGCA
1930 7_HRV40a|d     ACCAAAGAAAAGAAATTACACATGGCAGTCAGGCACTAATGCTTCTGTATTCTGGCA
1931 8_HRV40b|d     ACCAAAGAAAAGAAATGATTACACATGGCAGTCAGGCACTAATGCTTCTGTATTCTGGCA
1932 9_HRV40        ACCAAAGAAAAGAAATGATTACACATGGCAGTCAGGCACTAATGCTTCTGTATTCTGGCA
1933 10_HRV85       ACCAAGGAAAGAGATGATTACACATGGCAATCAGGTACTAATGCTTCCGTGTTTTGGCA
1934 11_HRV85a|     ACCAAGGAAAGAGATGATTACACATGGCAATCAGGTACTAATGCTTCCGTGTTTTGGCA
1935 12_HRV85b|     ACCAAGGAAAGAGATGATTACACATGGCAATCAGGTACTAATGCTTCCGTGTTTTGGCA
1936 13_HRV56a|     TCCAAACTCAAGAGATGATTTTACATGGCAATCTGGCACCAATGCTTCTGTCTTTTGGCA
1937 14_HRV56b|     TCCAAACTCAAGAGATGATTTTACATGGCAATCTGGCACCAATGCTTCTGTCTTTTGGCA
1938 15_HRV56       TCCAAACTCAAGAGATGATTTTACATGGCAATCTGGCACCAATGCTTCTGTCTTTTGGCA
1939 16_HRV54       ACCAGAAAAAAGGAATGATTACACCTGGGAGTCAAGCACAAACCCTTCTATATTTTGGCA
1940 17_HRV98       ACCTAAAAAGAGGAATGATTATACTTGGGAATCAAGCACAAACCCTTCTATATTCTGGCA
1941 18_HRV59a|     GCCCACAAAGAGAGATGATTACACATGGCAATCTGGTACTAATGCTTCAATATTCTGGCA
1942 19_HRV59b|     GCCCACAAAGAGAGATGATTACACATGGCAATCTGGTACTAATGCTTCAATATTCTGGCA
1943 20_HRV59       GCCCACAAAGAGAGATGATTACACATGGCAATCTGGTACTAATGCTTCAATATTCTGGCA
1944 21_HRV63       ACCCACCCGAAGAGAAGATTACACATGGCAATCTGGCACTAATGCTTCAATATTCTGGCA
1945 22_HRV63b|     ACCCACCCGAAGAGAAGATTACACATGGCAATCTGGCACTAATGCTTCAATATTCTGGCA
1946 23_HRV63a|     ACCCACCCGAAGAGAAGATTACACATGGCAATCTGGCACTAATGCTTCAATATTCTGGCA
1947 24_HRV39       ACCTAAGAAGAGAGATGATTACACATGGCAATCTGGAACAAATGCCTCAGTTTTCTGGCA
1948 25_HRV39a|     ACCTAAGAAGAGAGATGATTACACATGGCAATCTGGAACAAATGCCTCAGTTTTCTGGCA
1949 26_HRV39b|     ACCTAAGAAGAGAGATGATTACACATGGCAATCTGGAACAAATGCCTCAGTTTTCTGGCA
1950 27_HRV10a|     ACCAACTAAGAGAGATGATTTTGCTTGGCAGTCGGGAACAAATGCATCAGTCTTCTGGCA
```

FIG. D6 CONT'D 02.trace                                                                                    9/20/2007 4:59 PM

```
1951 28_HRV10b|    ACCAACTAAGAGAGATGATTTTGCTTGGCAGTCGGGAACAAATGCATCAGTCTTCTGGCA
1952 29_HRV10      ACCAACTAAGAGAGATGATTTTGCTTGGCAGTCGGGAACAAATGCATCAGTCTTCTGGCA
1953 30_HRV100a    TCCAACAAAAAGGGATGATTTTGCATGGCAATCAGGCACAAATGCATCAGTTTTTTGGCA
1954 31_HRV100b    TCCAACAAAAAGGGATGATTTTGCATGGCAATCAGGCACAAATGCATCAGTTTTTTGGCA
1955 32_HRV100     TCCAACAAAAAGGGATGATTTTGCATGGCAATCAGGCACAAATGCATCAGTTTTTTGGCA
1956 33_HRV66      TCCAGATAATAGAACACACTTTGCTTGGCAATCAGGAACAAATGCATCTATATTCTGGCA
1957 34_HRV66b|    TCCAGATAATAGAACACACTTTGCTTGGCAATCAGGAACAAATGCATCTATATTCTGGCA
1958 35_HRV66a|    TCCAGATAATAGAACACACTTTGCTTGGCAATCAGGAACAAATGCATCTATATTCTGGCA
1959 36_HRV77a|    ACCAGATAGCAGGACTCATTTTGCATGGCAGTCAGGGACTAATGCATCAATATTCTGGCA
1960 37_HRV77b|    ACCAGATAGCAGGACTCATTTTGCATGGCAGTCAGGGACTAATGCATCAATATTCTGGCA
1961 38_HRV77      ACCAGATAGCAGGACTCATTTTGCATGGCAGTCAGGGACTAATGCATCAATATTCTGGCA
1962 39_HRV62a     ACCAACAGACAGAAAGCATTTTGCCTGGCAATCAAGTACTAATGCATCAATATTTTGGCA
1963 40_HRV62b     ACCAACAGACAGAAAGCATTTTGCCTGGCAATCAAGTACTAATGCATCAATATTTTGGCA
1964 41_HRV25      ACCAACAGACAGAAAACACTTTGCATGGCAATCAAGTACTAATGCATCAATATTTTGGCA
1965 42_HRV29a     ACCAAATGACAGAAATCATTTTGCATGGCAATCAGGGACTAATGCATCAATATTCTGGCA
1966 43_HRV29b     ACCAAATGACAGAAATCATTTTGCATGGCAATCAGGGACTAATGCATCAATATTCTGGCA
1967 44_HRV44a     ACCAGATGACAGAAACCACTTTGCATGGCAATCGGGGACTAATGCATCAATATTCTGGCA
1968 45_HRV44b     ACCAGATGACAGAATCCACTTTGCATGGCAATCGGGGAATAATGCATCAATATTCTGGCA
1969 46_HRV31      ACCAACAAATAGAAAACATTTTGCATGGCAATCAGGTACTAATGCATCGATTTTCTGGCA
1970 47_HRV31a|    ACCAACAAATAGAAAACATTTTGCATGGCAATCAGGTACTAATGCATCGATTTTCTGGCA
1971 48_HRV31b|    ACCAACAAATAGAAAACATTTTGCATGGCAATCAGGTACTAATGCATCGATTTTCTGGCA
1972 49_HRV47      GCCAACAAGTAGAGAGCACTTTGCATGGCAGTCAGGTACCAATGCATCAACTTTCTGGCA
1973 50_HRV47a|    GCCAACAAGTAGAGAGCACTTTGCATGGCAGTCAGGTACCAATGCATCAACTTTCTGGCA
1974 51_HRV47b|    GCCAACAAGTAGAGAGCACTTTGCATGGCAGTCAGGTACCAATGCATCAATTTTCTGGCA
1975 52_HRV11      TCCAGAGAAAAGAGATGATTATACATGGCAATCAGGAACAAATGCATCTATTTTCTGGCA
1976 53_HRV11b|    TCCAGAGAAAAGAGATGATTATACATGGCAATCAGGAACAAATGCATCTATTTTCTGGCA
1977 54_HRV11a|    TCCAGAGAAAAGAGATGATTATACATGGCAATCAGGAACAAATGCATCTATTTTCTGGCA
1978 55_HRV76      TCCAAAGAAGAGAGATGACTACACATGGCAGTCAGGAACCAATGCATCTATTTTCTGGCA
1979 56_HRV76b|    TCCAAAGAAGAGAGATGACTACACATGGCAGTCAGGAACCAATGCATCTATTTTCTGGCA
1980 57_HRV76a|    TCCAAAGAAGAGAGATGACTACACATGGCAGTCAGGAACCAATGCATCTATTTTCTGGCA
1981 58_HRV33      TCCAGAAAAGAGAGATGATTACACATGGCAATCAGGAACAAATGCATCTGTCTTTTGGCA
1982 59_HRV33b|    TCCAGAAAAGAGAGATGATTACACATGGCAATCAGGAACAAATGCATCTGTCTTTTGGCA
1983 60_HRV33a|    TCCAGAAAAGAGAGATGATTACACATGGCAATCAGGAACAAATGCATCTGTCTTTTGGCA
1984 61_HRV24a|    CCCAACAAAGAGAGATGATTATACATGGCAATCAGGAACAAATGCATCTGTCTTTTGGCA
1985 62_HRV24b|    CCCAACAAAGAGAGATGATTATACATGGCAATCAGGAACAAATGCATCTGTCTTTTGGCA
1986 63_HRV24      CCCAACAAAGAGAGATGATTATACATGGCAATCAGGAACAAATGCATCTGTCTTTTGGCA
1987 64_HRV90      ACCTGAGAAGAGGGATGATTATGCATGGCAATCAGGCACTAATGCATCTATCTTTTGGCA
1988 65_HRV90a|    ACCTGAGAAGAGGGATGATTATGCATGGCAATCAGGCACTAATGCATCTATCTTTTGGCA
1989 66_HRV90b|    ACCTGAGAAGAGGGATGATTATGCATGGCAATCAGGCACTAATGCATCTATCTTTTGGCA
1990 67_HRV34      ACCTAAAACTAGAGATGATTTTGCATGGCAATCTGGAACAAATGCCTCAATATTTTGGCA
1991 68_HRV34b|    ACCTAAAACTAGAGATGATTTTGCATGGCAATCTGGAACAAATGCCTCAATATTTTGGCA
1992 69_HRV34a|    ACCTAAAACTAGAGATGATTTTGCATGGCAATCTGGAACAAATGCCTCAATATTTTGGCA
1993 70_HRV50a|    ACCCAAGACTAGGGATGATTTTGCCTGGCAATCTGGAACTAATGCTTCAATCTTTTGGCA
1994 71_HRV50b|    ACCCAAGACTAGGGATGATTTTGCCTGGCAATCTGGAACTAATGCTTCAATCTTTTGGCA
1995 72_HRV50      ACCCAAGACTAGGGATGATTTTGCCTGGCAATCTGGAACTAATGCTTCAATCTTTTGGCA
1996 73_HRV18a|    ACCAAAAACCAGAGATGATTTTGCCTGGCAATCTGGAACAAATGCATCAATCTTCTGGCA
1997 74_HRV18b|    ACCAAAAACCAGAGATGATTTTGCCTGGCAATCTGGAACAAATGCATCAATCTTCTGGCA
1998 75_HRV18      ACCAAAAACCAGAGATGATTTTGCCTGGCAATCTGGAACAAATGCATCAATCTTCTGGCA
1999 76_HRV55      TCCAAAGACAAGAGAAGATTATGCTTGGCAATCAGGGACCAATGCATCTATCTTTTGGCA
2000 77_HRV55b|    TCCAAAGACAAGAGAAGATTATGCTTGGCAATCAGGGACCAATGCATCTATCTTTTGGCA
2001 78_HRV55a|    TCCAAAGACAAGAGAAGATTATGCTTGGCAATCAGGGACCAATGCATCTATCTTTTGGCA
2002 79_HRV57      TCCAAAAACAAGAGAGGATTATACATGGCAATCTGGTACCAATGCTTCAATATTTTGGCA
2003 80_HRV57a|    TCCAAAAACAAGAGAGGATTATACATGGCAATCTGGTACCAATGCTTCAATATTTTGGCA
2004 81_HRV57b|    TCCAAAAACAAGAGAGGATTATACATGGCAATCTGGTACCAATGCTTCAATATTTTGGCA
2005 82_HRV21      TCCAAAAACTAGGGAAGATTTTGCTTGGCAGTCAGGCACTAATGCATCCATTTTCTGGCA
2006 83_HRVHan     TCCAAAAACTAGGGAAGATTTTGCTTGGCAATCAGGTACCAATGCATCCATTTTCTGGCA
2007 84_HRV43      TCCAAAAACTAGGGAAAGATTATGCATGGCAATCTGGCACAAATGCATCTGTTTTCTGGCA
2008 85_HRV43b|    TCCAAAAACTAGGGAAGATTATGCATGGCAATCTGGCACAAATGCATCTGTTTTCTGGCA
2009 86_HRV43a|    TCCAAAAACTAGGGAAAGATTATGCATGGCAATCTGGCACAAATGCATCTGTTTTCTGGCA
2010 87_HRV75      ACCAACAACTAGAAAAGATTATGCATGGCAATCTGGAACAAATGCATCTGTATTTTGGCA
2011 88_HRV75b|    ACCAACAACTAGAAAAGATTATGCATGGCAATCTGGAACAAATGCATCTGTATTTTGGCA
2012 89_HRV75a|    ACCAACAACTAGAAAAGATTATGCATGGCAATCTGGAACAAATGCATCTGTATTTTGGCA
2013 96_HRV9a|d    ACCAAGGACTAGAGATGATTATGCATGGCAATCAGGCACAAATGCTTCCATCTTTTGGCA
2014 97_HRV9b|d    ACCAAGGACTAGAGATGATTATGCATGGCAATCAGGCACAAATGCTTCCATCTTTTGGCA
2015 98_HRV9       ACCAAGGACTAGAGATGATTATGCATGGCAATCAGGCACAAATGCTTCCATCTTTTGGCA
```

FIG. D6 CONT'D 02.trace                                                                                              9/20/2007 4:59 PM

```
2016 99_HRV32    ACCACAAGCAAGAGATGACTACACATGGCAATCTGGCACGAATGCATCTATCTTTTGGCA
2017 100_HRV32a  ACCACAAGCAAGAGATGACTACACATGGCAATCTGGCACGAATGCATCTATCTTTTGGCA
2018 101_HRV32b  ACCACAAGCAAGAGATGACTACACATGGCAATCTGGCACGAATGCATCTATCTTTTGGCA
2019 102_HRV67   ACCAACAAAAAGAGATGACTACACATGGCAATCAGGTACAAATGCATCCATCTTTTGGCA
2020 103_HRV67a  ACCAACAAAAAGAGATGACTACACATGGCAATCAGGTACAAATGCATCCATCTTTTGGCA
2021 104_HRV67b  ACCAACAAAAAGAGATGACTACACATGGCAATCAGGTACAAATGCATCCATCTTTTGGCA
2022 105_HRV15   ACCCAATAAAAGGAATGATTACACATGGCAATCAGGTACAAATGCCTCTGTTTTCTGGCA
2023 106_HRV15a  ACCCAATAAAAGGAATGATTACACATGGCAATCAGGTACAAATGCCTCTGTTTTCTGGCA
2024 107_HRV15b  ACCCAATAAAAGGAATGATTACACATGGCAATCAGGTACAAATGCCTCTGTTTTCTGGCA
2025 108_HRV74a  ACCCAAGAAAAGAGATGATTACACATGGCAATCTGGCACAAATGCATCTGTGTTTTGGCA
2026 109_HRV74b  ACCCAAGAAAAGAGATGATTACACATGGCAATCTGGCACAAATGCATCTGTGTTTTGGCA
2027 110_HRV74   ACCCAAGAAAAGAGATGATTACACATGGCAATCTGGCACAAATGCATCTGTGTTTTGGCA
2028 111_HRV38a  ACCCAGGAAGAGAGATGATTACACTTGGCAATCTGGTACAAATGCCTCTGTTTTCTGGCA
2029 112_HRV38b  ACCCAGGAAGAGAGATGATTACACTTGGCAATCTGGTACAAATGCCTCTGTTTTCTGGCA
2030 113_HRV38   ACCCAGGAAGAGAGATGATTACACTTGGCAATCTGGTACAAATGCCTCTGTTTTCTGGCA
2031 114_HRV60   ACCTACTAAAAGAGACGATTACACATGGCAATCTGGCACAAATGCTTCTGTATTTTGGCA
2032 115_HRV60a  ACCTACTAAAAGAGACGATTACACATGGCAATCTGGCACAAATGCTTCTGTATTTTGGCA
2033 116_HRV60b  ACCTACTAAAAGAGACGATTACACATGGCAATCTGGCACAAATGCTTCTGTATTTTGGCA
2034 117_HRV64a  ACCAACCAAAAGAAATGATTACGTCTGGCAGTCAGGCACCAATGCATCCATCTTTTGGCA
2035 118_HRV64b  ACCAACCAAAAGAAATGATTACGTCTGGCAGTCAGGCACCAATGCATCCATCTTTTGGCA
2036 119_HRV64   ACCAACCAAAAGAAATGATTACGTCTGGCAGTCAGGCACCAATGCATCCATCTTTTGGCA
2037 120_HRV94a  ACCAGACAAAAGAGATGATTATGTTTGGCAATCAGGAACTAATGCATCTATATTCTGGCA
2038 121_HRV94b  ACCAGACAAAAGAGATGATTATGTTTGGCAATCAGGAACTAATGCATCTATATTCTGGCA
2039 122_HRV94   ACCAGACAAAAGAGATGATTATGTTTGGCAATCAGGAACTAATGCATCTATATTCTGGCA
2040 123_HRV22   ACCTGAAAAGAGAGATGACTACACATGGCAATCTGGCACTAATGCATCTGTTTTCTGGCA
2041 124_HRV22a  ACCTGAAAAGAGAGATGACTACACATGGCAATCTGGCACTAATGCATCTGTTTTCTGGCA
2042 125_HRV22b  ACCTGAAAAGAGAGATGACTACACATGGCAATCTGGCACTAATGCATCTGTTTTCTGGCA
2043 126_HRV82   ACCAGAAAAGAGAGACGACTACACTTGGCAATCTGGAACTAATGCTTCAATTTTCTGGCA
2044 127_HRV82b  ACCAGAAAAGAGAGACGACTACACTTGGCAATCTGGAACTAATGCTTCAATTTTCTGGCA
2045 128_HRV82a  ACCAGAAAAGAGAGACGACTACACTTGGCAATCTGGAACTAATGCTTCAATTTTCTGGCA
2046 129_HRV19   CCCAAAAACTAGAAATGATTACACATGGCAATCAGGTACTAATGCATCTATATTTTGGCA
2047 130_HRV19a  CCCAAAAACTAGAAATGATTACACATGGCAATCAGGTACTAATGCATCTATATTTTGGCA
2048 131_HRV19b  CCCAAAAACTAGAAATGATTACACATGGCAATCAGGTACTAATGCATCTATATTTTGGCA
2049 132_HRV13   TCCAACGAAGAGAAATGATTACACATGGCAATCTGGCACCAATGCATCTGTTTTCTGGCA
2050 133_HRV13a  TCCAACGAAGAGAAATGATTACACATGGCAATCTGGCACCAATGCATCTGTTTTCTGGCA
2051 134_HRV13b  TCCAACGAAGAGAAATGATTACACATGGCAATCTGGCACCAATGCATCTGTTTTCTGGCA
2052 135_HRV41   CCCAGAAAAGAGAGATGATTACACATGGCAATCTGGCACCAATGCATCTGTATTCTGGCA
2053 136_HRV41a  CCCAGAAAAGAGAGATGATTACACATGGCAATCTGGCACCAATGCATCTGTATTCTGGCA
2054 137_HRV41b  CCCAGAAAAGAGAGATGATTACACATGGCAATCTGGCACCAATGCATCTGTATTCTGGCA
2055 138_HRV73   ACCCACAAAAGAAATGACTACACATGGCAGTCCGGCACTAATGCATCAGTATTCTGGCA
2056 139_HRV73b  ACCCACAAAAGAAATGACTACACATGGCAGTCCGGCACTAATGCATCAGTATTCTGGCA
2057 140_HRV73a  ACCCACAAAAGAAATGACTACACATGGCAGTCCGGCACTAATGCATCAGTATTCTGGCA
2058 141_HRV61   ACCTGAGAAAAGAAATGATTTCACATGGCAATCAGGCACAAATGCATCTGTTTTCTGGCA
2059 142_HRV61a  ACCTGAGAAAAGAAATGATTTCACATGGCAATCAGGCACAAATGCATCTGTTTTCTGGCA
2060 143_HRV61b  ACCTGAGAAAAGAAATGATTTCACATGGCAATCAGGCACAAATGCATCTGTTTTCTGGCA
2061 144_HRV96   ACCTGAGAAGAGAGATGACTTTACATGGCAATCAGGCACAAATGCATCTGTGTTTTGGCA
2062 145_HRV96b  ACCTGAGAAGAGAGATGACTTTACATGGCAATCAGGCACAAATGCATCTGTGTTTTGGCA
2063 146_HRV96a  ACCTGAGAAGAGAGATGACTTTACATGGCAATCAGGCACAAATGCATCTGTGTTTTGGCA
2064 90_HRV16a|  ACCAACAACTAGAAATGACTATGCTTGGCAATCTGGAACAAATGCATCTGTATTTTGGCA
2065 91_HRV16b|  ACCAACAACTAGAAATGACTATGCTTGGCAATCTGGAACAAATGCATCTGTATTTTGGCA
2066 92_1AYM_A   ACCAACAACTAGAAATGACTATGCTTGGCAATCTGGAACAAATGCATCTGTATTTTGGCA
2067 93_HRV81a|  TCCAACAACTAGAGAAGACTATGCTTGGCAATCTGGAACAAATGCATCTATATTCTGGCA
2068 94_HRV81b|  TCCAACAACTAGAGAAGACTATGCTTGGCAATCTGGAACAAATGCATCTATATTCTGGCA
2069 95_HRV81    TCCAACAACTAGAGAAGACTATGCTTGGCAATCTGGAACAAATGCATCTATATTCTGGCA
2070 147_HRV2    GCCCAATAGTAGGGACGATTATGCATGGCAGTCTGGCACTAATGCCTCTGTTTTCTGGCA
2071 148_HRV2a|  GCCCAATAGTAGGGACGATTATGCATGGCAGTCTGGCACTAATGCCTCTGTTTTCTGGCA
2072 149_HRV2b|  GCCCAATAGTAGGGACGATTATGCATGGCAGTCTGGCACTAATGCCTCTGTTTTCTGGCA
2073 150_HRV49a  ACCAAAGAGCAGAGATGATTATGCATGGCAGTCTGGCACTAATGCATCTGTTTTCTGGCA
2074 151_HRV49b  ACCAAAGAGCAGAGATGATTATGCATGGCAGTCTGGCACTAATGCATCTGTTTTCTGGCA
2075 152_HRV49   ACCAAAGAGCAGAGATGATTATGCATGGCAGTCTGGCACTAATGCATCTGTTTTCTGGCA
2076 153_HRV23a  ACCGGAAAGTAGAAATGACTATGCATGGCAATCTGGAACAAATGCGTCCATTTTTTGGCA
2077 154_HRV23b  ACCGGAAAGTAGAAATGACTATGCATGGCAATCTGGAACAAATGCGTCCATTTTTTGGCA
2078 155_HRV23   ACCGGAAAGTAGAAATGACTATGCATGGCAATCTGGAACAAATGCGTCCATTTTTTGGCA
2079 156_HRV30a  TCCCGAGAGCAGAAATGACTATGCATGGCAGTCTGGAACAAATGCATCTGTTTTTTGGCA
2080 157_HRV30b  TCCCGAGAGCAGAAATGACTATGCATGGCAGTCTGGAACAAATGCATCTGTTTTTTGGCA
```

FIG. D6 CONT'D

```
02.trace                                                                                9/20/2007 4:59 PM 2081  158_HRV30    TCCCGAGAGCAGAAATGACTATGCATGGCAGTCTGGAACAAATGCATCTGTTTTTTGGCA
2082  159_HRV7     TCCAATAAAACGCGAAGATTATACATGGCAATCAGGAACAAATGCTTCTATATTTTGGCA
2083  160_HRV7b|   TCCAATAAAACGCGAAGATTATACATGGCAATCAGGAACAAATGCTTCTATATTTTGGCA
2084  161_HRV7a|   TCCAATAAAACGCGAAGATTATACATGGCAATCAGGAACAAATGCTTCTATATTTTGGCA
2085  162_HRV88    TCCCAAGAAACGTGATGATTACACATGGCAGTCAGGAACAAATGCATCTGTGTTCTGGCA
2086  163_HRV88a   TCCCAAGAAACGTGATGATTACACATGGCAGTCAGGAACAAATGCATCTGTGTTCTGGCA
2087  164_HRV88b   TCCCAAGAAACGTGATGATTACACATGGCAGTCAGGAACAAATGCATCTGTGTTCTGGCA
2088  165_HRV36a   TCCTGTGAAGCGTGATGACTACACATGGCAATCAGGGACAAATGCATCTGTGTTCTGGCA
2089  166_HRV36b   TCCTGTGAAGCGTGATGACTACACATGGCAATCAGGGACAAATGCATCTGTGTTCTGGCA
2090  167_HRV36    TCCTGTGAAGCGTGATGACTACACATGGCAATCAGGGACAAATGCATCTGTGTTCTGGCA
2091  168_HRV89a   CCCCGAAAAACGTGATGATTACACATGGCAATCAGGAACAAATGCATCTGTGTTCTGGCA
2092  169_HRV89b   CCCCGAAAAACGTGATGATTACACATGGCAATCAGGAACAAATGCATCTGTGTTCTGGCA
2093  170_HRV89    CCCCGAAAAACGTGATGATTACACATGGCAATCAGGAACAAATGCATCTGTGTTCTGGCA
2094  171_HRV58    ACCCAAGAATCGTGATGACTTTACATGGCAATCAGGCACAAATGCATCTGTTTTCTGGCA
2095  172_HRV58a   ACCCAAGAATCGTGATGACTTTACATGGCAATCAGGCACAAATGCATCTGTTTTCTGGCA
2096  173_HRV58b   ACCCAAGAATCGTGATGACTTTACATGGCAATCAGGCACAAATGCATCTGTTTTCTGGCA
2097  174_HRV12a   ACCCAAAAAACGTGATGATTACACATGGCAATCTGGCACCAACGCCTCAGTTTTTTGGCA
2098  175_HRV12b   ACCCAAAAAACGTGATGATTACACATGGCAATCTGGCACCAACGCCTCAGTTTTTTGGCA
2099  176_HRV12    ACCCAAAAAACGTGATGATTACACATGGCAATCTGGCACCAACGCCTCAGTTTTTTGGCA
2100  177_HRV78a   ACCAAAGAAGAGAGATGACTATACTTGGCAGTCAGGCACCAATGCATCTGTGTTTTGGCA
2101  178_HRV78b   ACCAAAGAAGAGAGATGACTATACTTGGCAGTCAGGCACCAATGCATCTGTGTTTTGGCA
2102  179_HRV78    ACCAAAGAAGAGAGATGACTATACTTGGCAGTCAGGCACCAATGCATCTGTGTTTTGGCA
2103  180_HRV20    ACCAAAGACTAGAGATGACTACACATGGCAATCAGGGACAAATGCATCAGTATTTTGGCA
2104  181_HRV20a   ACCAAAGACTAGAGATGACTACACATGGCAATCAGGGACAAATGCATCAGTATTTTGGCA
2105  182_HRV20b   ACCAAAGACTAGAGATGACTACACATGGCAATCAGGGACAAATGCATCAGTATTTTGGCA
2106  183_HRV68    ACCAAAAACTAGAGATGATTACACATGGCAGTCAGGCACTAATGCATCAGTGTTTTGGCA
2107  184_HRV68a   ACCAAAAACTAGAGATGATTACACATGGCAGTCAGGCACTAATGCATCAGTGTTTTGGCA
2108  185_HRV68b   ACCAAAAACTAGAGATGATTACACATGGCAGTCAGGCACTAATGCATCAGTGTTTTGGCA
2109  186_HRV28    CCCCACTACCAGAAATGATTACACATGGCAATCCAGTACCAATGCCTCTGTTTTCTGGCA
2110  187_HRV28a   CCCCACTACCAGAAATGATTACACATGGCAATCCAGTACCAATGCCTCTGTTTTCTGGCA
2111  188_HRV28b   CCCCACTACCAGAAATGATTACACATGGCAATCCAGTACCAATGCCTCTGTTTTCTGGCA
2112  189_HRV53a   ACCCAAAACCAGAGATGACTATACCTGGCAATCTGGAACTAATGCTTCAGTCTTTTGGCA
2113  190_HRV53b   ACCCAAAACCAGAGATGACTATACCTGGCAATCTGGAACTAATGCTTCAGTCTTTTGGCA
2114  191_HRV53    ACCCAAAACCAGAGATGACTATACCTGGCAATCTGGAACTAATGCTTCAGTCTTTTGGCA
2115  192_HRV46a   ACCGAGATATCGGAATGATTATACTTGGCAGTCTGGTACTAATGCTTCAGTGTTCTGGCA
2116  193_HRV46b   ACCGAGATATCGGAATGATTATACTTGGCAGTCTGGTACTAATGCTTCAGTGTTCTGGCA
2117  194_HRV46    ACCGAGATATCGGAATGATTATACTTGGCAGTCTGGTACTAATGCTTCAGTGTTCTGGCA
2118  195_HRV80a   GCCAAACAAACGCAATGATTATACTTGGCAGTCTGGCACGAATGCTTCAGTCTTCTGGCA
2119  196_HRV80b   GCCAAACAAACGCAATGATTATACTTGGCAGTCTGGCACGAATGCTTCAGTCTTCTGGCA
2120  197_HRV80    GCCAAACAAACGCAATGATTATACTTGGCAGTCTGGCACGAATGCTTCAGTCTTCTGGCA
2121  198_HRV51    TCCACTTACTAGGAAAGATGATGAGTGGCAATCAGGAACTAATGCTTCAGTATTCTGGCA
2122  199_HRV51a   TCCACTTACTAGGAAAGATGATGAGTGGCAATCAGGAACTAATGCTTCAGTATTCTGGCA
2123  200_HRV51b   TCCACTTACTAGGAAAGATGATGAGTGGCAATCAGGAACTAATGCTTCAGTATTCTGGCA
2124  201_HRV65a   TCCAAAAACTAGAAAAGATGAAGAGTGGCAGACAGGAACTAATGCTTCAGTCTTTTGGCA
2125  202_HRV65b   TCCAAAAACTAGAAAAGATGAAGAGTGGCAGACAGGAACTAATGCTTCAGTCTTTTGGCA
2126  203_HRV65    TCCAAAAACTAGAAAAGATGAAGAGTGGCAGACAGGAACTAATGCTTCAGTCTTTTGGCA
2127  204_HRV71a   ACCAGAGACCAGGGATGCCGATGAATGGCAGTCTGGAACTAATGCATCAGTCTTTTGGCA
2128  205_HRV71b   ACCAGAGACCAGGGATGCCGATGAATGGCAGTCTGGAACTAATGCATCAGTCTTTTGGCA
2129  206_HRV71    ACCAGAGACCAGGGATGCCGATGAATGGCAGTCTGGAACTAATGCATCAGTCTTTTGGCA
2130  207_HRV8     TCCAGATAAAAGGATGCACGATGCCTGGCAAACCAGTACAAATGCCTCAGTCTTCTGGCA
2131  208_HRV95    TCCAGATAAAAGGATGCACGATGCCTGGCAAACCAGTACAAATGCCTCAGTCTTCTGGCA
2132  209_HRV45    CCCTGTTAGTAGAACTGACAACACTTGGCAATCTAGCACAAATGCATCAGTCTTTTGGCA
2133  210_HRV45a   CCCTGTTAGTAGAACTGACAACACTTGGCAATCTAGCACAAATGCATCAGTCTTTTGGCA
2134  211_HRV45b   CCCTGTTAGTAGAACTGACAACACTTGGCAATCTAGCACAAATGCATCAGTCTTTTGGCA
2135  GROUP_1      -CC--------G-------------TGG-A--C--G-A---AA----TC----TT-TGGCA
2136
2137  1_HRV1A1|d   ACATGGACAGCCATTTCCTAGATTTTCTTTACCATTCTTAGCATTGCATCAGCTTATTA
2138  2_HRV1A2|d   ACATGGACAGCCATTTCCTAGATTTTCTTTACCATTCTTAGCATTGCATCAGCTTATTA
2139  3_HRV1A|cD   ACATGGACAGCCATTTCCTAGATTTTCTTTACCATTCTTAGCATTGCATCAGCTTATTA
2140  4_HRV1B1|d   ACATGGACAACCGTTCCCTAGATTCTCTTTACCATTCTTAGCATTGCATCAGCTTATTA
2141  5_HRV1B2|d   ACATGGACAACCGTTCCCTAGATTCTCTTTACCATTCTTAGCATTGCATCAGCTTATTA
2142  6_HRV1B      ACATGGACAACCGTTCCCTAGATTCTCTTTACCATTCTTAGCATTGCATCAGCTTATTA
2143  7_HRV40a|d   ACATGGTCAAACTTTCCCTAGATTTTCTTTACCTTTCCTAAGCATAGCTTCAGCATACTA
2144  8_HRV40b|d   ACATGGTCAAACTTTCCCTAGATTTTCTTTACCTTTCCTAAGCATAGCTTCAGCATACTA
2145  9_HRV40      ACATGGTCAAACTTTCCCTAGATTTTCTTTACCTTTCCTAAGCATAGCTTCAGCATACTA
```

FIG. D6 CONT'D

```
02.trace                                                                              9/20/2007 4:59 PM 2146 10_HRV85    ACATGGGCAAACTTTCCCCAGATTTTCCTTACCTTTCTTGAGTGTTGCTTCAGCATATTA
2147 11_HRV85a|  ACATGGGCAAACTTTCCCCAGATTTTCCTTACCTTTCTTGAGTGTTGCTTCAGCATATTA
2148 12_HRV85b|  ACATGGGCAAACTTTCCCCAGATTTTCCTTACCTTTCTTGAGTGTTGCTTCAGCATATTA
2149 13_HRV56a|  ACATGGCCAAGCTTTCCCCAGATTCTCTCTACCTTTCTTAAGTATTGCTTCTGCTTATTA
2150 14_HRV56b|  ACATGGCCAAGCTTTCCCCAGATTCTCTCTACCTTTCTTAAGTATTGCTTCTGCTTATTA
2151 15_HRV56    ACATGGCCAAGCTTTCCCCAGATTCTCTCTACCTTTCTTAAGTATTGCTTCTGCTTATTA
2152 16_HRV54    ACATGGCCAAGCTTATCCAAGATTCTCTTTACCATTTTTAAGTATTGCATCTGCTTACTA
2153 17_HRV98    GCATGGTCAGGCCTATCCAAGATTTTCTCTACCATTCTTGAGCATTGCATCTGCTTACTA
2154 18_HRV59a|  ACATGGACAAACATTCCCAAGATTTTCATTGCCCTTCCTGAGCATAGCATCAGCTTATTA
2155 19_HRV59b|  ACATGGACAAACATTCCCAAGATTTTCATTGCCCTTCCTGAGCATAGCATCAGCTTATTA
2156 20_HRV59    ACATGGACAAACATTCCCAAGATTTTCATTGCCCTTCCTGAGCATAGCATCAGCTTATTA
2157 21_HRV63    ACATGGACAAGCTTTTCCAAGGTTTTCTCTACCTTTCTTGAGTATTGCATCAGCATATTA
2158 22_HRV63b|  ACATGGACAAGCTTTTCCAAGGTTTTCTCTACCTTTCTTGAGTATTGCATCAGCATATTA
2159 23_HRV63a|  ACATGGACAAGCTTTTCCAAGGTTTTCTCTACCTTTCTTGAGTATTGCATCAGCATATTA
2160 24_HRV39    ACACGGACAGCCTTACCCTAGATTTTCATTACCATTTCTAAGCATAGCCTCAGCATATTA
2161 25_HRV39a|  ACACGGACAGCCTTACCCTAGATTTTCATTACCATTTCTAAGCATAGCCTCAGCATATTA
2162 26_HRV39b|  ACACGGACAGCCTTACCCTAGATTTTCATTACCATTTCTAAGCATAGCCTCAGCATATTA
2163 27_HRV10a|  ACATGGACAACCTTTCCCTAGATTTTCTTTACCCTTCTTAAGCATTGCATCTGCTTACTA
2164 28_HRV10b|  ACATGGACAACCTTTCCCTAGATTTTCTTTACCCTTCTTAAGCATTGCATCTGCTTACTA
2165 29_HRV10    ACATGGACAACCTTTCCCTAGATTTTCTTTACCCTTCTTAAGCATTGCATCTGCTTACTA
2166 30_HRV100a  GCATGGGCAGCCATTCCCTAGAATTTCTTTACCTTTCTTGAGCATTGCTTCTGCATACTA
2167 31_HRV100b  GCATGGGCAGCCATTCCCTAGAATTTCTTTACCTTTCTTGAGCATTGCTTCTGCATACTA
2168 32_HRV100   GCATGGGCAGCCATTCCCTAGAATTTCTTTACCTTTCTTGAGCATTGCTTCTGCATACTA
2169 33_HRV66    ACTTGGACAACCATTCCCAAGATTCTCGCTACCTTTTCTAGGCATAGCTTCAGCATATTA
2170 34_HRV66b|  ACTTGGACAACCATTCCCAAGATTCTCGCTACCTTTTCTAGGCATAGCTTCAGCATATTA
2171 35_HRV66a|  ACTTGGACAACCATTCCCAAGATTCTCGCTACCTTTTCTAGGCATAGCTTCAGCATATTA
2172 36_HRV77a|  ACATGGACAACCATTCCCAAGATTTTCACTACCTTTTCTGAGTATTGCTTCAGCTTACTA
2173 37_HRV77b|  ACATGGACAACCATTCCCAAGATTTTCACTACCTTTTCTGAGTATTGCTTCAGCTTACTA
2174 38_HRV77    ACATGGACAACCATTCCCAAGATTTTCACTACCTTTTCTGAGTATTGCTTCAGCTTACTA
2175 39_HRV62a   ACATGGGCAACCCTTTCCTAGATTTTCATTACCTTTTTGAGTGTTGCATCTGCTTATTA
2176 40_HRV62b   ACATGGGCAACCCTTTCCTAGATTTTCATTACCCTTTTTGAGTGTTGCATCTGCTTATTA
2177 41_HRV25    ACATGGACAACCCTTCCCTAGATTTTCATTGCCATTTCTGAGTGTTGCATCTGCTTATTA
2178 42_HRV29a   ACATGGTCAGCCTTTCCCAAGATTTTCATTACCATTCCTAAGTGTTGCATCTGCTTATTA
2179 43_HRV29b   ACATGGTCAGCCTTTCCCAAGATTTTCATTACCATTCCTAAGTGTTGCATCTGCTTATTA
2180 44_HRV44a   ACATGGTCAACCTTTCCCAAGATTTTCATTGCCATTTCTAAGTGTTGCATCTGCCTATTA
2181 45_HRV44b   ACATGGTCAACCTTTCCCAAGATTTTCATTGCCATTTCTAAGTGTTGCATCTGCCTATTA
2182 46_HRV31    ACATGGACAACCCTTTCCAAGATTTACATTACCCTTTTTGAGTGTCGCATCCGCTTATTA
2183 47_HRV31a|  ACATGGACAACCCTTTCCAAGATTTACATTACCCTTTTTGAGTGTCGCATCCGCTTATTA
2184 48_HRV31b|  ACATGGACAACCCTTTCCAAGATTTACATTACCCTTTTTGAGTGTCGCATCCGCTTATTA
2185 49_HRV47    ACAAGGGCAACCCTTTCCAAGATTTTCATTACCATTTTTGAGTGTTGCATCTGCTTATTA
2186 50_HRV47a|  ACAAGGGCAACCCTTTCCAAGATTTTCATTACCATTTTTGAGTGTTGCATCTGCTTATTA
2187 51_HRV47b|  ACAAGGGCAACCCTTTCCAAGATTTTCATTACCATTTTTGAGTGTTGCATCTGCTTATTA
2188 52_HRV11    ATATGGTCAAACATACCCAAGATTTTCTCTACCTTTCATGAGTATAGCCTCAGCATATTA
2189 53_HRV11b|  ATATGGTCAAACATACCCAAGATTTTCTCTACCTTTCATGAGTATAGCCTCAGCATATTA
2190 54_HRV11a|  ATATGGTCAAACATACCCAAGATTTTCTCTACCTTTCATGAGTATAGCCTCAGCATATTA
2191 55_HRV76    ATATGGACAAACATACCCTAGGTTTTCATTACCCTTTCTAAGTATAGCTTCAGCTTATTA
2192 56_HRV76b|  ATATGGACAAACATACCCTAGGTTTTCATTACCCTTTCTAAGTATAGCTTCAGCTTATTA
2193 57_HRV76a|  ATATGGACAAACATACCCTAGGTTTTCATTACCCTTTCTAAGTATAGCTTCAGCTTATTA
2194 58_HRV33    ATATGGACAAACATATCCTAGGTTCTCATTACCTTTCCTTAGCATAGCTTCAGCATATTA
2195 59_HRV33b|  ATATGGACAAACATATCCTAGGTTCTCATTACCTTTCCTTAGCATAGCTTCAGCATATTA
2196 60_HRV33a|  ATATGGACAAACATATCCTAGGTTCTCATTACCTTTCCTTAGCATAGCTTCAGCATATTA
2197 61_HRV24a|  ACATGGACAAACCTATCCTAGATTTTCCCTTCCTTTTCTGAGTGTAGCCTCTGCATATTA
2198 62_HRV24b|  ACATGGACAAACCTATCCTAGATTTTCCCTTCCTTTTCTGAGTGTAGCCTCTGCATATTA
2199 63_HRV24    ACATGGACAAACCTATCCTAGATTTTCCCTTCCTTTTCTGAGTGTAGCCTCTGCATATTA
2200 64_HRV90    ACATGGACAAACATACCCTAGATTTTCACTTCCTTTCTTAAGTATAGCTTCTGCATACTA
2201 65_HRV90a|  ACATGGACAAACATACCCTAGATTTTCACTTCCTTTCTTAAGTATAGCTTCTGCATACTA
2202 66_HRV90b|  ACATGGACAAACATACCCTAGATTTTCACTTCCTTTCTTAAGTATAGCTTCTGCATACTA
2203 67_HRV34    ACATGGTCAAACATACCCTAGATTTTCCCTCCCTTTCTTAAGCATAGCCTCAGCATACTA
2204 68_HRV34b|  ACATGGTCAAACATACCCTAGATTTTCCCTCCCTTTCTTAAGCATAGCCTCAGCATACTA
2205 69_HRV34a|  ACATGGTCAAACATACCCTAGATTTTCCCTCCCTTTCTTAAGCATAGCCTCAGCATACTA
2206 70_HRV50a|  ACATGGTCAAACATACCCTAGATTCTCTCTACCATTCTTGAGTATAGCATCTGCATATTA
2207 71_HRV50b|  ACATGGTCAAACATACCCTAGATTCTCTCTACCATTCTTGAGTATAGCATCTGCATATTA
2208 72_HRV50    ACATGGTCAAACATACCCTAGATTCTCTCTACCATTCTTGAGTATAGCATCTGCATATTA
2209 73_HRV18a|  ACATGGTCAAACATACCCCAGATTTTCACTTCCTTTCCTCAGTATAGCATCAGCTTATTA
2210 74_HRV18b|  ACATGGTCAAACATACCCCAGATTTTCACTTCCTTTCCTCAGTATAGCATCAGCTTATTA
```

FIG. D6 CONT'D

02.trace                                                                                        9/20/2007 4:59 PM

```
2211  75_HRV18     ACATGGTCAAACATACCCCAGATTTTCACTTCCTTTCCTCAGTATAGCATCAGCTTATTA
2212  76_HRV55     ACATGGGCAAACATACCCTAGATTTTCACTTCCTTTCCTAAGTATAGCTTCTGCTTATTA
2213  77_HRV55b|   ACATGGGCAAACATACCCTAGATTTTCACTTCCTTTCCTAAGTATAGCTTCTGCTTATTA
2214  78_HRV55a|   ACATGGGCAAACATACCCTAGATTTTCACTTCCTTTCCTAAGTATAGCTTCTGCTTATTA
2215  79_HRV57     ACATGGTCAAACATACCCTAGATTTTCCTTGCCTTTCTTAAGTATAGCCTCAGCATATTA
2216  80_HRV57a|   ACATGGTCAAACATACCCTAGATTTTCCTTGCCTTTCTTAAGTATAGCCTCAGCATATTA
2217  81_HRV57b|   ACATGGTCAAACATACCCTAGATTTTCCTTGCCTTTCTTAAGTATAGCCTCAGCATATTA
2218  82_HRV21     GCATGGCCAGACTTATCCTAGATTTTCATTACCCTTCCTTAGTATAGCATCAGCATACTA
2219  83_HRVHan    GCATGGTCAAACTTATCCTAGATTTTCACTACCCTTCCTTAGTATAGCATCAGCATATTA
2220  84_HRV43     ACATGGTCAAACATTTCCAAGATTTTCCTTACCTTTCTGAGCATAGCATCAGCATATTA
2221  85_HRV43b|   ACATGGTCAAACATTTCCAAGATTTTCCTTACCTTTCTGAGCATAGCATCAGCATATTA
2222  86_HRV43a|   ACATGGTCAAACATTTCCAAGATTTTCCTTACCTTTCTGAGCATAGCATCAGCATATTA
2223  87_HRV75     ACATGGACAAACATTTCCAAGATTTTCACTACCATTTCTGACCATTGCATCAGCATATTA
2224  88_HRV75b|   ACATGGACAAACATTTCCAAGATTTTCACTACCATTTCTGAGCATTGCATCAGCATATTA
2225  89_HRV75a|   ACATGGACAAACATTTCCAAGATTTTCACTACCATTTCTGAGCATTGCATCAGCATATTA
2226  96_HRV9a|d   ACATGGACAATCATATCCCAGATTTTCACTTCCGTTTTGAGCATTGCCTCTGCATATTA
2227  97_HRV9b|d   ACATGGACAATCATATCCCAGATTTTCACTTCCGTTTTGAGCATTGCCTCTGCATATTA
2228  98_HRV9      ACATGGACAATCATATCCCAGATTTTCACTTCCGTTTTGAGCATTGCCTCTGCATATTA
2229  99_HRV32     GCATGGACAGGCATATCCCAGGTTTTCACTTCCATTTCTAAGTATTGCCTCTGCATACTA
2230 100_HRV32a    GCATGGACAGGCATATCCCAGGTTTTCACTTCCATTTCTAAGTATTGCCTCTGCATACTA
2231 101_HRV32b    GCATGGACAGGCATATCCCAGGTTTTCACTTCCATTTCTAAGTATTGCCTCTGCATACTA
2232 102_HRV67     ACATGGACAATCATACCCCAGATTCTCACTACCATTCTTAAGTATTGCCTCTGCTTATTA
2233 103_HRV67a    ACATGGACAATCATACCCCAGATTCTCACTACCATTCTTAAGTATTGCCTCTGCTTATTA
2234 104_HRV67b    ACATGGACAATCATACCCCAGATTCTCACTACCATTCTTAAGTATTGCCTCTGCTTATTA
2235 105_HRV15     ACATGGTCAACCTTACCCCAGATTTTCTTTGCCTTTTCTCAGCATTGCATCTGCTTACTA
2236 106_HRV15a    ACATGGTCAACCTTACCCCAGATTTTCTTTGCCTTTTCTCAGCATTGCATCTGCTTACTA
2237 107_HRV15b    ACATGGTCAACCTTACCCCAGATTTTCTTTGCCTTTTCTCAGCATTGCATCTGCTTACTA
2238 108_HRV74a    GCATGGACAGCCATACCCTAGATTCTCATTACCTTTCCTTAGCATAGCATCTGCTTATTA
2239 109_HRV74b    GCATGGACAGCCATACCCTAGATTCTCATTACCTTTCCTTAGCATAGCATCTGCTTATTA
2240 110_HRV74     GCATGGACAGCCATACCCTAGATTCTCATTACCTTTCCTTAGCATAGCATCTGCTTATTA
2241 111_HRV38a    ATATGGTCAGACATATCCTCGATTTTCCTTACCTTTCTTAAGCATTGCATCTGTCTATTA
2242 112_HRV38b    ATATGGTCAGACATATCCTCGATTTTCCTTACCTTTCTTAAGCATTGCATCTGTCTATTA
2243 113_HRV38     ATATGGTCAGACATATCCTCGATTTTCCTTACCTTTCTTAAGCATTGCATCTGTCTATTA
2244 114_HRV60     GCATGGACAAACATACCCTAGATTTTCACTTCCATTTCTAAGTATTGCATCTGCCTACTA
2245 115_HRV60a    GCATGGACAAACATACCCTAGATTTTCACTTCCATTTCTAAGTATTGCATCTGCCTACTA
2246 116_HRV60b    GCATGGACAAACATACCCTAGATTTTCACTTCCATTTCTAAGTATTGCATCTGCCTACTA
2247 117_HRV64a    ACACGGTCAACCATACCCTCGATTTTCTCTCCCTTTCCTTAGCATAGCCTCAGCATATTA
2248 118_HRV64b    ACACGGTCAACCATACCCTCGATTTTCTCTCCCTTTCCTTAGCATAGCCTCAGCATATTA
2249 119_HRV64     ACACGGTCAACCATACCCTCGATTTTCTCTCCCTTTCCTTAGCATAGCCTCAGCATATTA
2250 120_HRV94a    ACATGGTCAACCCTACCCTCGATTCTCACTTCCATTTCTTAGTATAGCCTCAGCATATTA
2251 121_HRV94b    ACATGGTCAACCCTACCCTCGATTCTCACTTCCATTTCTTAGTATAGCCTCAGCATATTA
2252 122_HRV94     ACATGGTCAACCCTACCCTCGATTCTCACTTCCATTTCTTAGTATAGCCTCAGCATATTA
2253 123_HRV22     GCATGGTCAACCTTATCCCCGATTCTCACTCCCTTTCCTCAGTGTAGCTTCAGCATATTA
2254 124_HRV22a    GCATGGTCAACCTTATCCCCGATTCTCACTCCCTTTCCTCAGTGTAGCTTCAGCATATTA
2255 125_HRV22b    GCATGGTCAACCTTATCCCCGATTCTCACTCCCTTTCCTCAGTGTAGCTTCAGCATATTA
2256 126_HRV82     ACATGGACAACCTTACCCTCGCTTCTCACTTCCTTTCTTGAGTATAGCCTCAGCTTACTA
2257 127_HRV82b    ACATGGACAACCTTACCCTCGCTTCTCACTTCCTTTCTTGAGTATAGCCTCAGCTTACTA
2258 128_HRV82a    ACATGGACAACCTTACCCTCGCTTCTCACTTCCTTTCTTGAGTATAGCCTCAGCTTACTA
2259 129_HRV19     ACATGGTCAACCATACCCAAGATTTTCATTACCTTTTCTAAGTATAGCTTCTGCATATTA
2260 130_HRV19a    ACATGGTCAACCATACCCAAGATTTTCATTACCTTTTCTAAGTATAGCTTCTGCATATTA
2261 131_HRV19b    ACATGGTCAACCATACCCAAGATTTTCATTACCTTTTCTAAGTATAGCTTCTGCATATTA
2262 132_HRV13     ACATGGTCAAATTTACCCCCGATTCTCTTTACCATTTCTTAGTATTGCATCTGCATATTA
2263 133_HRV13a    ACATGGTCAAATTTACCCCCGATTCTCTTTACCATTTCTTAGTATTGCATCTGCATATTA
2264 134_HRV13b    ACATGGTCAAATTTACCCCCGATTCTCTTTACCATTTCTTAGTATTGCATCTGCATATTA
2265 135_HRV41     GTATGGTCAAGTTTACCCTAGGTTTTCTCTACCATTTCTTAGCATTGCTTCCGCATATTA
2266 136_HRV41a    GTATGGTCAAGTTTACCCTAGGTTTTCTCTACCATTTCTTAGCATTGCTTCCGCATATTA
2267 137_HRV41b    GTATGGTCAAGTTTACCCTAGGTTTTCTCTACCATTTCTTAGCATTGCTTCCGCATATTA
2268 138_HRV73     ACATGGTCAAACTTACCCCAGATTCTCATTACCATTCCTTAGTATAGCATCCGCATATTA
2269 139_HRV73b    ACATGGTCAAACTTACCCCAGATTCTCATTACCATTCCTTAGTATAGCATCCGCATATTA
2270 140_HRV73a    ACATGGTCAAACTTACCCCAGATTCTCATTACCATTCCTTAGTATAGCATCCGCATATTA
2271 141_HRV61     ACATGGTCAAGCTTATCCCAGATTTTCATTACCATTCCTAAGTATTGCATCTGCATATTA
2272 142_HRV61a    ACATGGTCAAGCTTATCCCAGATTTTCATTACCATTCCTAAGTATTGCATCTGCATATTA
2273 143_HRV61b    ACATGGTCAAGCTTATCCCAGATTTTCATTACCATTCCTAAGTATTGCATCTGCATATTA
2274 144_HRV96     GCACGGGCAAGCATATCCTAGATTTTCACTGCCTTTCCTTAGTATTGCCTCTGCATATTA
2275 145_HRV96b    GCACGGGCAAGCATATCCTAGATTTTCACTGCCTTTCCTTAGTATTGCCTCTGCATATTA
```

FIG. D6 CONT'D

```
02.trace                                                              9/20/2007 4:59 PM 2276  146_HRV96a   GCACGGGCAAGCATATCCTAGATTTTCACTGCCTTTCCTTAGTATTGCCTCTGCATATTA
2277   90_HRV16a|  GCATGGGCAACCTTTCCCTCGCTTTTCACTTCCCTTTTGAGTATTGCATCAGCATATTA
2278   91_HRV16b|  GCATGGGCAACCTTTCCCTCGCTTTTCACTTCCCTTTTGAGTATTGCATCAGCATATTA
2279   92_1AYM_A   GCATGGGCAACCTTTCCCTCGCTTTTCACTTCCCTTTTGAGTATTGCATCAGCATATTA
2280   93_HRV81a|  ACATGGGCAACCCTTTCCCCGGTTTTCACTCCCTTTTCTAAGTGTAGCATCAGCATATTA
2281   94_HRV81b|  ACATGGGCAACCCTTTCCCCGGTTTTCACTCCCTTTTCTAAGTGTAGCATCAGCATATTA
2282   95_HRV81    ACATGGGCAACCCTTTCCCCGGTTTTCACTCCCTTTTCTAAGTGTAGCATCAGCATATTA
2283  147_HRV2     ACATGGACAGGCTTATCCAAGATTTTCCTTACCTTTCCTAAGTGTGGCATCTGCTTATTA
2284  148_HRV2a|   ACATGGACAGGCTTATCCAAGATTTTCCTTACCTTTCCTAAGTGTGGCATCTGCTTATTA
2285  149_HRV2b|   ACATGGACAGGCTTATCCAAGATTTTCCTTACCTTTCCTAAGTGTGGCATCTGCTTATTA
2286  150_HRV49a   ACATGGGCAAGCATACCCAAGATTTCTCTACCCTTTTGAGTGTAGCTTCAGCTTACTA
2287  151_HRV49b   ACATGGGCAAGCATACCCAAGATTTTCTCTACCCTTTTGAGTGTAGCTTCAGCTTACTA
2288  152_HRV49    ACATGGGCAAGCATACCCAAGATTTTCTCTACCCTTTTGAGTGTAGCTTCAGCTTACTA
2289  153_HRV23a   ACATGGACAAACATATCCAAGGTTCTCCTTACCCTTTTGAGTGTGGCATCTGCTTATTA
2290  154_HRV23b   ACATGGACAAACATATCCAAGGTTCTCCTTACCCTTTTGAGTGTGGCATCTGCTTATTA
2291  155_HRV23    ACATGGACAAACATATCCAAGGTTCTCCTTACCCTTTTGAGTGTGGCATCTGCTTATTA
2292  156_HRV30a   ACACGGACAAACATACCCAAGATTCTCCCTACCATTTTGAGTGTAGCATCTGCTTATTA
2293  157_HRV30b   ACACGGACAAACATACCCAAGATTCTCCCTACCATTTTGAGTGTAGCATCTGCTTATTA
2294  158_HRV30    ACACGGACAAACATACCCAAGATTCTCCCTACCATTTTGAGTGTAGCATCTGCTTATTA
2295  159_HRV7     GGAGGGTCAACCATACCCTAGATTCACAATTCCTTTTATGAGTATTGCATCAGCTTATTA
2296  160_HRV7b|   GGAGGGTCAACCATACCCTAGATTCACAATTCCTTTTATGAGTATTGCATCAGCTTATTA
2297  161_HRV7a|   GGAGGGTCAACCATACCCTAGATTCACAATTCCTTTTATGAGTATTGCATCAGCTTATTA
2298  162_HRV88    AGAAGGACAACCATACCCAAGATTTACCATTCCCTTTATGAGTATTGCATCAGCTTACTA
2299  163_HRV88a   AGAAGGACAACCATACCCAAGATTTACCATTCCCTTTATGAGTATTGCATCAGCTTACTA
2300  164_HRV88b   AGAAGGACAACCATACCCAAGATTTACCATTCCCTTTATGAGTATTGCATCAGCTTACTA
2301  165_HRV36a   AGAAGGGCAACCATATCCTAGATTTACAATCCCTTTTATGAGTATTGCATCAGCTTATTA
2302  166_HRV36b   AGAAGGGCAACCATATCCTAGATTTACAATCCCCTTTATGAGTATTGCATCAGCTTATTA
2303  167_HRV36    AGAAGGGCAACCATATCCTAGATTTACAATCCCCTTTATGAGTATTGCATCAGCTTATTA
2304  168_HRV89a   AGAAGGACAACCATACCCCAGATTCACAATCCCTTTTATGAGCATTGCATCAGCCTATTA
2305  169_HRV89b   AGAAGGACAACCATACCCCAGATTCACAATCCCTTTTATGAGCATTGCATCAGCCTATTA
2306  170_HRV89    AGAAGGACAACCATACCCCAGATTCACAATCCCTTTTATGAGCATTGCATCAGCCTATTA
2307  171_HRV58    GGAAGGACAACCATACCCTAGATTTACAATCCCTTTTATGAGCATTGCATCAGCTTACTA
2308  172_HRV58a   GGAAGGACAACCATACCCTAGATTTACAATCCCTTTTATGAGCATTGCATCAGCTTACTA
2309  173_HRV58b   GGAAGGACAACCATACCCTAGATTTACAATCCCTTTTATGAGCATTGCATCAGCTTACTA
2310  174_HRV12a   GGAAGGTCAACCTTACCCCAGATTCACAATCCCTTTTATTAGTATTGCCTCAGCATATTA
2311  175_HRV12b   GGAAGGTCAACCTTACCCCAGATTCACAATCCCTTTTATTAGTATTGCCTCAGCATATTA
2312  176_HRV12    GGAAGGTCAACCTTACCCCAGATTCACAATCCCTTTTATTAGTATTGCCTCAGCATATTA
2313  177_HRV78a   ACAAGGTCAAACATACCCCAGGTTCTCTATACCATTTTCTAGTATTGCCTCAGCTTATTA
2314  178_HRV78b   ACAAGGTCAAACATACCCCAGGTTCTCTATACCATTTTCTAGTATTGCCTCAGCTTATTA
2315  179_HRV78    ACAAGGTCAAACATACCCCAGGTTCTCTATACCATTTTCTAGTATTGCCTCAGCTTATTA
2316  180_HRV20    GCAGGGCCAACCTTACCCCAGATTTACCATTCCATTTATGAGTATAGCTTCAGCATATTA
2317  181_HRV20a   GCAGGGCCAACCTTACCCCAGATTTACCATTCCATTTATGAGTATAGCTTCAGCATATTA
2318  182_HRV20b   GCAGGGCCAACCTTACCCCAGATTTACCATTCCATTTATGAGTATAGCTTCAGCATATTA
2319  183_HRV68    ACAAGGACAACCTTACCCCAGATTTACCATTCCATTTATGAGTATAGCTTCAGCATATTA
2320  184_HRV68a   ACAAGGACAACCTTACCCCAGATTTACCATTCCATTTATGAGTATAGCTTCAGCATATTA
2321  185_HRV68b   ACAAGGACAACCTTACCCCAGATTTACCATTCCATTTATGAGTATAGCTTCAGCATATTA
2322  186_HRV28    ACAAGGACAACCATATCCCAGATTCACTATACCTTTTATGAGTATTGCCTCAGCTTATTA
2323  187_HRV28a   ACAAGGACAACCATATCCCAGATTCACTATACCTTTTATGAGTATTGCCTCAGCTTATTA
2324  188_HRV28b   ACAAGGACAACCATATCCCAGATTCACTATACCTTTTATGAGTATTGCCTCAGCTTATTA
2325  189_HRV53a   ACAAGGACAACCATACCCTAGATTCACAATCCCTTTCATGAGTATTGCGTCAGCATATTA
2326  190_HRV53b   ACAAGGACAACCATACCCTAGATTCACAATCCCTTTCATGAGTATTGCGTCAGCATATTA
2327  191_HRV53    ACAAGGACAACCATACCCTAGATTCACAATCCCTTTCATGAGTATTGCGTCAGCATATTA
2328  192_HRV46a   GCAAGGGCAGCCATACCCTAGATTCACTATCCCGTTCATGAGTATAGCCTCAGCATATTA
2329  193_HRV46b   GCAAGGGCAGCCATACCCTAGATTCACTATCCCGTTCATGAGTATAGCCTCAGCATATTA
2330  194_HRV46    GCAAGGGCAGCCATACCCTAGATTCACTATCCCGTTCATGAGTATAGCCTCAGCATATTA
2331  195_HRV80a   ACAGGGTCAGCCATACCCCAGATTCACTATTCCATTCATGAGTATAGCCTCAGCTTATTA
2332  196_HRV80b   ACAGGGTCAGCCATACCCCAGATTCACTATTCCATTCATGAGTATAGCCTCAGCTTATTA
2333  197_HRV80    ACAGGGTCAGCCATACCCCAGATTCACTATTCCATTCATGAGTATAGCCTCAGCTTATTA
2334  198_HRV51    ACATGGACAACCATACCCTAGATTTACAATCCCTTTTGTAAGCATAGCCTCAGCATACTA
2335  199_HRV51a   ACATGGACAACCATACCCTAGATTTACAATCCCTTTTGTAAGCATAGCCTCAGCATACTA
2336  200_HRV51b   ACATGGACAACCATACCCTAGATTTACAATCCCTTTTGTAAGCATAGCCTCAGCATACTA
2337  201_HRV65a   GCATGGTCAACCATACCCCAGATTTACAATTCCTTTTGTGAGTATTGCCTCAGCATATTA
2338  202_HRV65b   GCATGGTCAACCATACCCCAGATTTACAATTCCTTTTGTGAGTATTGCCTCAGCATATTA
2339  203_HRV65    GCATGGTCAACCATACCCCAGATTTACAATTCCTTTTGTGAGTATTGCCTCAGCATATTA
2340  204_HRV71a   GCACGGCCAACCATACCCAAGGTTTACAATCCCCTTCATAAGCATTGCATCAGCATATTA
```

FIG. D6 CONT'D

```
02.trace                                                                9/20/2007 4:59 PM 2341  205_HRV71b   GCACGGCCAACCATACCCAAGGTTTACAATCCCCTTCATAAGCATTGCATCAGCATATTA
2342  206_HRV71    GCACGGCCAACCATACCCAAGGTTTACAATCCCCTTCATAAGCATTGCATCAGCATATTA
2343  207_HRV8     AGTTGGACAAACTTATCCCAGATTCACCATACCTTTCTCCAGCATAGCATCAGCTTATTA
2344  208_HRV95    AGTTGGACAGACTTATCCCAGATTCACCATACCTTTCTCCAGTATAGCATCAGCTTATTA
2345  209_HRV45    GGTTGGTCAAACTTATCCCAGATTTTCTATACCTTTCTCAAGTATAGCTTCAGCTTACTA
2346  210_HRV45a   GGTTGGTCAAACTTATCCCAGATTTTCTATACCTTTCTCAAGTATAGCTTCAGCTTACTA
2347  211_HRV45b   GGTTGGTCAAACTTATCCCAGATTTTCTATACCTTTCTCAAGTATAGCTTCAGCTTACTA
2348  GROUP_1      ----GG-CA----T--CC--G---T--C---T-CC-TT-----G--T-GC-TC-G---TA-TA
2349
2350  1_HRV1A1|d   TATGTTTTATGATGGATATGATGGAGACAACACTTCTTCCAAGTATGGTAGCGTAGTTAC
2351  2_HRV1A2|d   TATGTTTTATGATGGATATGATGGAGACAACACTTCTTCCAAGTATGGTAGCGTAGTTAC
2352  3_HRV1A|cD   TATGTTTTATGATGGATATGATGGAGACAACACTTCTTCCAAGTATGGTAGCGTAGTTAC
2353  4_HRV1B1|d   CATGTTTTATGATGGATATGATGGAGATAATTCCTCTTCCAAATATGGTAGTATAGTCAC
2354  5_HRV1B2|d   CATGTTTTATGATGGATATGATGGAGATAATTCCTCTTCCAAATATGGTAGTATAGTCAC
2355  6_HRV1B      CATGTTTTATGATGGATATGATGGAGATAATTCCTCTTCCAAATATGGTAGTATAGTCAC
2356  7_HRV40a|d   CATGTTTTATGATGGATACGATGGTGATACATCGACCTCAAGATATGGCACATCAGTCAC
2357  8_HRV40b|d   CATGTTTTATGATGGATACGATGGTGATACATCGACCTCAAGATATGGCACATCAGTCAC
2358  9_HRV40      CATGTTTTATGATGGATACGATGGTGATACATCGACCTCAAGATATGGCACATCAGTCAC
2359  10_HRV85     CATGTTTTATGATGGTTATGATGGTGATACACCAGGCTCAATGTATGGGACGTCAGTCAC
2360  11_HRV85a|   CATGTTTTATGATGGTTATGATGGTGATACACCAGGCTCAATGTATGGGACGTCAGTCAC
2361  12_HRV85b|   CATGTTTTATGATGGTTATGATGGTGATACACCAGGCTCAATGTATGGGACGTCAGTCAC
2362  13_HRV56a|   CATGTTTTATGATGGTTATGATGGAGACACTTCAAGCTCCAGATATGGTACATCAGTTAC
2363  14_HRV56b|   CATGTTTTATGATGGTTATGATGGAGACACTTCAAGCTCCAGATATGGTACATCAGTTAC
2364  15_HRV56     CATGTTTTATGATGGTTATGATGGAGACACTTCAAGCTCCAGATATGGTACATCAGTTAC
2365  16_HRV54     CATGTTTTATGATGGGTATGATGGTGACGCACCTGGATCAAGATATGGGACTTCAGTTAC
2366  17_HRV98     CATGTTTTACGATGGGTATGATGGTGATGCACCTGGATCAAGATATGGAACCTCAGTCAC
2367  18_HRV59a|   CATGTTTTATGATGGTTATGATGGAGATAAATCTGAATCTAGGTATGGTGTGTCTGTAAC
2368  19_HRV59b|   CATGTTTTATGATGGTTATGATGGAGATAAATCTGAATCTAGGTATGGTGTGTCTGTAAC
2369  20_HRV59     CATGTTTTATGATGGTTATGATGGAGATAAATCTGAATCTAGGTATGGTGTGTCTGTAAC
2370  21_HRV63     CATGTTTTATGATGGATATGATGGAGATAAATCAAGCTCTAGGTATGGTGTTTCAGTTAC
2371  22_HRV63b|   CATGTTTTATGATGGATATGATGGAGATAAATCAAGCTCTAGGTATGGTGTTTCAGTTAC
2372  23_HRV63a|   CATGTTTTATGATGGATATGATGGAGATAAATCAAGCTCTAGGTATGGTGTTTCAGTTAC
2373  24_HRV39     TATGTTCTATGATGGATATGATGGTGATAAATCGTCATCTAGGTATGGTGTTTCTGTCAC
2374  25_HRV39a|   TATGTTCTATGATGGATATGATGGTGATAAATCGTCATCTAGGTATGGTGTTTCTGTCAC
2375  26_HRV39b|   TATGTTCTATGATGGATATGATGGTGATAAATCGTCATCTAGGTATGGTGTTTCTGTCAC
2376  27_HRV10a|   CATGTTCTATGATGGTTATGATGGTGATACACATGACTCACGTTATGGCACAACAGTGAT
2377  28_HRV10b|   CATGTTCTATGATGGTTATGATGGTGATACACATGACTCACGTTATGGCACAACAGTGAT
2378  29_HRV10     CATGTTCTATGATGGTTATGATGGTGATACACATGACTCACGTTATGGCACAACAGTGAT
2379  30_HRV100a   CATGTTTTATGATGGATATGATGGTGATACACATGATTCACACTATGGTACTACTGTAAT
2380  31_HRV100b   CATGTTTTATGATGGATATGATGGTGATACACATGATTCACACTATGGTACTACTGTAAT
2381  32_HRV100    CATGTTTTATGATGGATATGATGGTGATACACATGATTCACACTATGGTACTACTGTAAT
2382  33_HRV66     CATGTTCTATGATGGTTATGATGGAGATACTCCTGGGTCTCGTTATGGAACCACAGTAGT
2383  34_HRV66b|   CATGTTCTATGATGGTTATGATGGAGATACTCCTGGGTCTCGTTATGGAACCACAGTAGT
2384  35_HRV66a|   CATGTTCTATGATGGTTATGATGGAGATACTCCTGGGTCTCGTTATGGAACCACAGTAGT
2385  36_HRV77a|   CATGTTTTATGATGGCTATGATGGGGATACCTATGAATCACGTTATGGTACTACAGTGGT
2386  37_HRV77b|   CATGTTTTATGATGGCTATGATGGGGATACCTATGAATCACGTTATGGTACTACAGTGGT
2387  38_HRV77     CATGTTTTATGATGGCTATGATGGGGATACCTATGAATCACGTTATGGTACTACAGTGGT
2388  39_HRV62a    CATGTTTTATGATGGCTATAATGGTGATGACTATACAGCAAAATACGGTACCACCGTGGT
2389  40_HRV62b    CATGTTTTATGATGGCTATAATGGTGATGACTATACAGCAAAATACGGTACCACCGTGGT
2390  41_HRV25     CATGTTTTATGATGGCTATAATGGTGATGATCACACAGCGAGATGGTACCACTGTGGT
2391  42_HRV29a    CATGTTTTATGATGGTTACAATGGAGGTGATCATACAGCAACTTATGCACCACAGTGGT
2392  43_HRV29b    CATGTTTTATGATGGTTACAATGGAGGTGATCATACAGCAACTTATGGCACCACAGTGGT
2393  44_HRV44a    CATGTTTTATGATGGCGTTATAATGGAGGTGATCATACAGCAACTTATGGCACCACAGTGGT
2394  45_HRV44b    CATGTTTTATGACGGTTATAATGGAGGTGATCATACAGCAACTTATGGCACCACAGTGGT
2395  46_HRV31     CATGTTTTATGATGGTTATGATGGAGACAAAAGTGGAGCCAAGTATGGTACTACAGTAGT
2396  47_HRV31a|   CATGTTTTATGATGGTTATGATGGAGACAAAAGTGGAGCCAAGTATGGTACTACAGTAGT
2397  48_HRV31b|   CATGTTTTATGATGGTTATGATGGAGACAAAAGTGGAGCCAAGTATGGTACTACAGTAGT
2398  49_HRV47     CATGTTTTATGATGGCTATAATGGTGACAGAAGTGGAGCCAAGTATGGCACCACAGTGGT
2399  50_HRV47a|   CATGTTTTATGATGGCTATAATGGTGACAGAAGTGGAGCCAAGTATGGCACCACAGTGGT
2400  51_HRV47b|   CATGTTTTATGATGGCTATAATGGTGACAGAAGTGGAGCCAAGTATGGCACCACAGTGGT
2401  52_HRV11     CATGTTTTATGATGGATATGATGGAGATCAACCAAACTCCAGATATGGTAATATAGTTAC
2402  53_HRV11b|   CATGTTTTATGATGGATATGATGGAGATCAACCAAACTCCAGATATGGTAATATAGTTAC
2403  54_HRV11a|   CATGTTTTATGATGGATATGATGGAGATCAACCAAACTCCAGATATGGTAATATAGTTAC
2404  55_HRV76     CATGTTTTATGATGGATATGATGGAGACCAACCTAGTTCTAGGTATGGTAATATAGTTAC
2405  56_HRV76b|   CATGTTTTATGATGGATATGATGGAGACCAACCTAGTTCTAGGTATGGTAATATAGTTAC
```

FIG. D6 CONT'D

```
02.trace                                                                    9/20/2007 4:59 PM 2406  57_HRV76a|   CATGTTTTATGATGGATATGATGGAGACCAACCTAGTTCTAGGTATGGTAATATAGTTAC
2407  58_HRV33     CATGTTCTATGATGGATATGATGGGGACCAACCCAATTCCAGGTATGGTAATATGGTTAC
2408  59_HRV33b|   CATGTTCTATGATGGATATGATGGGGACCAACCCAATTCCAGGTATGGTAATATGGTTAC
2409  60_HRV33a|   CATGTTCTATGATGGATATGATGGGGACCAACCCAATTCCAGGTATGGTAATATGGTTAC
2410  61_HRV24a|   CATGTTTTATGATGGATATGATGGTGATCAACACGACTCAGTGTATGGTTCAGTTGTTAC
2411  62_HRV24b|   CATGTTTTATGATGGATATGATGGTGATCAACACGACTCAGTGTATGGTTCAGTTGTTAC
2412  63_HRV24     CATGTTTTATGATGGATATGATGGTGATCAACACGACTCAGTGTATGGTTCAGTTGTTAC
2413  64_HRV90     TATGTTTTATGATGGATATGATGGTGACCAAACTGATTCGAGATATGGTACCATTGTTAC
2414  65_HRV90a|   TATGTTTTATGATGGATATGATGGTGACCAAACTGATTCGAGATATGGTACCATTGTTAC
2415  66_HRV90b|   TATGTTTTATGATGGATATGATGGTGACCAAACTGATTCGAGATATGGTACCATTGTTAC
2416  67_HRV34     CATGTTTTATGATGGATATGATGGTGATCAACATGATTCAAGATATGGTACAGTAGTGAC
2417  68_HRV34b|   CATGTTTTATGATGGATATGATGGTGATCAACATGATTCAAGATATGGTACAGTAGTGAC
2418  69_HRV34a|   CATGTTTTATGATGGATATGATGGTGATCAACATGATTCAAGATATGGTACAGTAGTGAC
2419  70_HRV50a|   CATGTTTTATGATGGTTATGATGGTGATAAATCTACATCCAGGTATGGTACAGTAGTTAC
2420  71_HRV50b|   CATGTTTTATGATGGTTATGATGGTGATAAATCTACATCCAGGTATGGTACAGTAGTTAC
2421  72_HRV50     CATGTTTTATGATGGTTATGATGGTGATAAATCTACATCCAGGTATGGTACAGTAGTTAC
2422  73_HRV18a|   CATGTTCTATGATGGCTACGACGGTGACCAGACCTCATCGCGGTATGGCACAGTTGCAAC
2423  74_HRV18b|   CATGTTCTATGATGGCTACGACGGTGACCAGACCTCATCGCGGTATGGCACAGTTGCAAC
2424  75_HRV18     CATGTTCTATGATGGCTACGACGGTGACCAGACCTCATCGCGGTATGGCACAGTTGCAAC
2425  76_HRV55     CATGTTCTATGATGGATATGATGGTGACCAAACTGAGTCACGCTATGGCACTGTAGTCAC
2426  77_HRV55b|   CATGTTCTATGATGGATATGATGGTGACCAAACTGAGTCACGCTATGGCACTGTAGTCAC
2427  78_HRV55a|   CATGTTCTATGATGGATATGATGGTGACCAAACTGAGTCACGCTATGGCACTGTAGTCAC
2428  79_HRV57     CATGTTTTATGATGGATATGATGGTGACCAAACTGAATCAAGATATGGTACTGTAGTCAC
2429  80_HRV57a|   CATGTTCTATGATGGATATGATGGTGACCAAACTGAATCAAGATATGGTACTGTAGTCAC
2430  81_HRV57b|   CATGTTTTATGATGGATATGATGGTGACCAAACTGAATCAAGATATGGTACTGTAGTCAC
2431  82_HRV21     CATGTTTTATGATGGTTATGATGGTGACCAGACTGACTCACAATATGGTGCAGTAGTAAC
2432  83_HRVHan    CATGTTTTATGATGGTTATGATGGTGATCAGACTGACTCACAATATGGTGCAGTGGTGAC
2433  84_HRV43     CATGTTTTATGATGGATATGAAGGTGACCAAAAAACATCCCGTTATGGCACAATTGCAAG
2434  85_HRV43b|   CATGTTTTATGATGGATATGAAGGTGACCAAAAAACATCCCGTTATGGCACAATTGCAAG
2435  86_HRV43a|   CATGTTTTATGATGGATATGAAGGTGACCAAAAAACATCCCGTTATGGCACAATTGCAAG
2436  87_HRV75     CATGTTTTATGATGGATATGAAGGGATCAAAATACATCCCGTTATGGCACCATTGCTAG
2437  88_HRV75b|   CATGTTTTATGATGGATATGAAGGGATCAAAATACATCCCGTTATGGCACCATTGCTAG
2438  89_HRV75a|   CATGTTTTATGATGGATATGAAGGGATCAAAATACATCCCGTTATGGCACCATTGCTAG
2439  96_HRV9a|d   CATGTTCTATGATGGTTATGATGGTGG---ACCAGATTCTCTGTATGGAACAATTGTAAC
2440  97_HRV9b|d   CATGTTCTATGATGGTTATGATGGTGG---ACCAGATTCTCTGTATGGAACAATTGTAAC
2441  98_HRV9      CATGTTCTATGATGGTTATGATGGTGG---ACCAGATTCTCTGTATGGAACAATTGTAAC
2442  99_HRV32     CATGTTTTATGATGGTTATGATGGTGG---GCCAGATTCACAATATGGAACAATTGTAAC
2443  100_HRV32a   CATGTTTTATGATGGTTATGATGGTGG---GCCAGATTCACAATATGGAACAATTGTAAC
2444  101_HRV32b   CATGTTTTATGATGGTTATGATGGTGG---GCCAGATTCACAATATGGAACAATTGTAAC
2445  102_HRV67    CATGTTTTATGATGGCTATGATGGTGG---ACCAGATTCACTATATGGCACCATAGTAAC
2446  103_HRV67a   CATGTTTTATGATGGCTATGATGGTGG---ACCAGATTCACTATATGGCACCATAGTAAC
2447  104_HRV67b   CATGTTTTATGATGGCTATGATGGTGG---ACCAGATTCACTATATGGCACCATAGTAAC
2448  105_HRV15    CATGTTCTATGATGGATATGATGGAGATTCCACTGAATCACATTATGGTACAGTGGTCAC
2449  106_HRV15a   CATGTTCTATGATGGATATGATGGAGATTCCACTGAATCACATTATGGTACAGTGGTCAC
2450  107_HRV15b   CATGTTCTATGATGGATATGATGGAGATTCCACTGAATCACATTATGGTACAGTGGTCAC
2451  108_HRV74a   CATGTTTTATGATGGATATGATGGAGACTCTACTGAATCACATTATGGTACAGTAGTAAC
2452  109_HRV74b   CATGTTTTATGATGGATATGATGGAGACTCTACTGAATCACATTATGGTACAGTAGTAAC
2453  110_HRV74    CATGTTTTATGATGGATATGATGGAGACTCTACTGAATCACATTATGGTACAGTAGTAAC
2454  111_HRV38a   TATGTTTTATGATGGATATGATGGGGACTCAACAGAATCACATTATGGGACAGCGGTGAC
2455  112_HRV38b   TATGTTTTATGATGGATATGATGGGGACTCAACAGAATCACATTATGGGACAGCGGTGAC
2456  113_HRV38    TATGTTTTATGATGGATATGATGGGGACTCAACAGAATCACATTATGGGACAGCGGTGAC
2457  114_HRV60    CATGTTTTATGATGGTTATGATGGTCACTCAACTGAATCACATTATGGGACGGTTGTGAC
2458  115_HRV60a   CATGTTTTATGATGGTTATGATGGTCACTCAACTGAATCACATTATGGGACGGTTGTGAC
2459  116_HRV60b   CATGTTTTATGATGGTTATGATGGTCACTCAACTGAATCACATTATGGGACGGTTGTGAC
2460  117_HRV64a   CATGTTTTATGATGGTTATGACGGTGG---ACCTGGTTCCCGTTATGGCGCAGTGGTGAC
2461  118_HRV64b   CATGTTTTATGATGGTTATGACGGTGG---ACCTGGTTCCCGTTATGGCGCAGTGGTGAC
2462  119_HRV64    CATGTTTTATGATGGTTATGACGGTGG---ACCTGGTTCCCGTTATGGCGCAGTGGTGAC
2463  120_HRV94a   CATGTTCTATGATGGTTATGATGGTGG---ACCTGGCTCACGCTATGGCACAGTGGTGAC
2464  121_HRV94b   CATGTTCTATGATGGTTATGATGGTGG---ACCTGGCTCACGCTATGGCACAGTGGTGAC
2465  122_HRV94    CATGTTCTATGATGGTTATGATGGTGG---ACCTGGCTCACGCTATGGCACAGTGGTGAC
2466  123_HRV22    CATGTTTTATGATGGGTATGATGGAGG---TCCCGGATCACGTTATGGAGCAGTGGTAAC
2467  124_HRV22a   CATGTTTTATGATGGGTATGATGGAGG---TCCCGGATCACGTTATGGAGCAGTGGTAAC
2468  125_HRV22b   CATGTTTTATGATGGGTATGATGGAGG---TCCCGGATCACGTTATGGAGCAGTGGTAAC
2469  126_HRV82    TATGTTCTATGATGGCTATGATGGTGATGCTCCCGGATCGCGATACGGGACCATAGTGAC
2470  127_HRV82b   TATGTTCTATGATGGCTATGATGGTGATGCTCCCGGATCGCGATACGGGACCATAGTGAC
```

FIG. D6 CONT'D

```
02.trace                                                                  9/20/2007 4:59 PM 2471 128_HRV82a   TATGTTCTATGATGGCTATGATGGTGATGCTCCCGGATCGCGATACGGGACCATAGTGAC
2472 129_HRV19    CATGTTTTATGATGGGTATGATGGAGATTCACCAGGATCCCGCTATGGAACAATAGTAAC
2473 130_HRV19a   CATGTTTTATGATGGGTATGATGGAGATTCACCAGGATCCCGCTATGGAACAATAGTAAC
2474 131_HRV19b   CATGTTTTATGATGGGTATGATGGAGATTCACCAGGATCCCGCTATGGAACAATAGTAAC
2475 132_HRV13    TATGTTTTATGATGGATATAATGGAGATTCCTCAGATGCACGCTATGGGACAACAATCAC
2476 133_HRV13a   TATGTTTTATGATGGATATAATGGAGATTCCTCAGATGCACGCTATGGGACAACAATCAC
2477 134_HRV13b   TATGTTTTATGATGGATATAATGGAGATTCCTCAGATGCACGCTATGGGACAACAATCAC
2478 135_HRV41    CATGTTTTATGATGGTTATGAAGAAGGCTCTACAAATGCACGCTATGGAACAACAGTCAC
2479 136_HRV41a   CATGTTTTATGATGGTTATGAAGAAGGCTCTACAAATGCACGCTATGGAACAACAGTCAC
2480 137_HRV41b   CATGTTTTATGATGGTTATGAAGAAGGCTCTACAAATGCACGCTATGGAACAACAGTCAC
2481 138_HRV73    TATGTTTTATGATGGATATGATGGTGACTCCACACAATCACATTATGGCACCACAGTAGT
2482 139_HRV73b   TATGTTTTATGATGGATATGATGGTGACTCCACACAATCACATTATGGCACCACAGTAGT
2483 140_HRV73a   TATGTTTTATGATGGATATGATGGTGACTCCACACAATCACATTATGGCACCACAGTAGT
2484 141_HRV61    TATGTTTTATGATGGTTATGATGGAGATTCTGAAATAACGCGCTATGGAACATCAGTGAC
2485 142_HRV61a   TATGTTTTATGATGGTTATGATGGAGATTCTGAAATAACGCGCTATGGAACATCAGTGAC
2486 143_HRV61b   TATGTTTTATGATGGTTATGATGGAGATTCTGAAATAACGCGCTATGGAACATCAGTGAC
2487 144_HRV96    CATGTTTTATGATGGATATGATGGTGACTCTGAATCAACACGCTATGGAACATCTGTTAC
2488 145_HRV96b   CATGTTTTATGATGGATATGATGGTGACTCTGAATCAACACGCTATGGAACATCTGTTAC
2489 146_HRV96a   CATGTTTTATGATGGATATGATGGTGACTCTGAATCAACACGCTATGGAACATCTGTTAC
2490 90_HRV16a|   CATGTTTTATGATGGTTATGATGGAGACACATATAAATCCAGATATGGAACTGTAGTCAC
2491 91_HRV16b|   CATGTTTTATGATGGTTATGATGGAGACACATATAAATCCAGATATGGAACTGTAGTCAC
2492 92_1AYM_A    CATGTTTTATGATGGTTATGATGGAGACACATATAAATCCAGATATGGAACTGTAGTCAC
2493 93_HRV81a|   CATGTTCTATGATGGATATGATGGTGATACTTATCACTCCAGATACGGGACTGTAGTCAC
2494 94_HRV81b|   CATGTTCTATGATGGATATGATGGTGATACTTATCACTCCAGATACGGGACTGTAGTCAC
2495 95_HRV81     CATGTTCTATGATGGATATGATGGTGATACTTATCACTCCAGATACGGGACTGTAGTCAC
2496 147_HRV2     CATGTTTTATGATGGGTATGATG------AACAAGATCAAAACTATGGTACAGCAAGCAC
2497 148_HRV2a|   CATGTTTTATGATGGGTATGATG------AACAAGATCAAAACTATGGTACAGCAAGCAC
2498 149_HRV2b|   CATGTTTTATGATGGGTATGATG------AACAAGATCAAAACTATGGTACAGCAAGCAC
2499 150_HRV49a   CATGTTTTATGATGGATATAATG------AACAGGGCCAAAATTATGGTACGGTAAGTAC
2500 151_HRV49b   CATGTTTTATGATGGATATAATG------AACAGGGCCAAAATTATGGTACGGTAAGTAC
2501 152_HRV49    CATGTTTTATGATGGATATAATG------AACAGGGCCAAAATTATGGTACGGTAAGTAC
2502 153_HRV23a   CATGTTTTATGATGGATACAATG------AGAAAGGCACGCATTATGGAACAGTTAGCAC
2503 154_HRV23b   CATGTTTTATGATGGATACAATG------AGAAAGGCACGCATTATGGAACAGTTAGCAC
2504 155_HRV23    CATGTTTTATGATGGATACAATG------AGAAAGGCACGCATTATGGAACAGTTAGCAC
2505 156_HRV30a   CATGTTCTATGATGGATACAATG------AGGGAGGCACAAATTATGGTACAGTGAGCAC
2506 157_HRV30b   CATGTTCTATGATGGATACAATG------AGGGAGGCACAAATTATGGTACAGTGAGCAC
2507 158_HRV30    CATGTTCTATGATGGATACAATG------AGGGAGGCACAAATTATGGTACAGTGAGCAC
2508 159_HRV7     TATGTTCTATGATGGATATGATGGTGATGATGCGTCATCCAAATATGGTTCCGTAGTAAC
2509 160_HRV7b|   TATGTTCTATGATGGATATGATGGTGATGATGCGTCATCCAAATATGGTTCCGTAGTAAC
2510 161_HRV7a|   TATGTTCTATGATGGATATGATGGTGATGATGCGTCATCCAAATATGGTTCCGTAGTAAC
2511 162_HRV88    TATGTTTTATGATGGATATGATGGTGATGATGCATCATCTAGGTATGGCTCAGTGGTAAC
2512 163_HRV88a   TATGTTTTATGATGGATATGATGGTGATGATGCATCATCTAGGTATGGCTCAGTGGTAAC
2513 164_HRV88b   TATGTTTTATGATGGATATGATGGTGATGATGCATCATCTAGGTATGGCTCAGTGGTAAC
2514 165_HRV36a   TATGTTTTATGATGGTTATGATGGTGATAATGCCGCATCAAAATATGGATCTGTGGTTAC
2515 166_HRV36b   TATGTTTTATGATGGTTATGATGGTGATAATGCCGCATCAAAATATGGATCTGTGGTTAC
2516 167_HRV36    TATGTTTTATGATGGTTATGATGGTGATAATGCCGCATCAAAATATGGATCTGTGGTTAC
2517 168_HRV89a   CATGTTTTATGATGGTTATGATGGTGATAGTGCAGCATCAAAATACGGTTCTGTAGTCAC
2518 169_HRV89b   CATGTTTTATGATGGTTATGATGGTGATAGTGCAGCATCAAAATACGGTTCTGTAGTCAC
2519 170_HRV89    CATGTTTTATGATGGTTATGATGGTGATAGTGCAGCATCAAAATACGGTTCTGTAGTCAC
2520 171_HRV58    TATGTTTTATGATGGTTATGATGGTGATGCTAAATCAATATATGGTTCTGTGGTAAC
2521 172_HRV58a   TATGTTTTATGATGGCTATGATGGTGATGATGCTAAATCAATATATGGTTCTGTGGTAAC
2522 173_HRV58b   TATGTTTTATGATGGCTATGATGGTGATGATGCTAAATCAATATATGGTTCTGTGGTAAC
2523 174_HRV12a   CATGTTTTATGATGGTTATGCTGATGACAACCCAAGTGCACCTTATGGAACTGTAGTTAC
2524 175_HRV12b   CATGTTTTATGATGGTTATGCTGATGACAACCCAAGTGCACCTTATGGAACTGTAGTTAC
2525 176_HRV12    CATGTTTTATGATGGTTATGCTGATGACAACCCAAGTGCACCTTATGGAACTGTAGTTAC
2526 177_HRV78a   CATGTTTTATGATGGATACTCGGATGACAGCACATCCTCTCCATATGGCACTGTAGTTAC
2527 178_HRV78b   CATGTTTTATGATGGATACTCGGATGACAGCACATCCTCTCCATATGGCACTGTAGTTAC
2528 179_HRV78    CATGTTTTATGATGGATACTCGGATGACAGCACATCCTCTCCATATGGCACTGTAGTTAC
2529 180_HRV20    TATGTTTTATGATGGTTATGAAGATGATAAGG---GAAGTGTGTATGGGTCTGTTGTCAC
2530 181_HRV20a   TATGTTTTATGATGGTTATGAAGATGATAAGG---GAAGTGTGTATGGGTCTGTTGTCAC
2531 182_HRV20b   TATGTTTTATGATGGTTATGAAGATGATAAGG---GAAGTGTGTATGGGTCTGTTGTCAC
2532 183_HRV68    TATGTTTTATGATGGATATGAGGATGACAAAG---GAAGTGTGTATGGATCTGTTGTTAC
2533 184_HRV68a   TATGTTTTATGATGGATATGAGGATGACAAAG---GAAGTGTGTATGGATCTGTTGTTAC
2534 185_HRV68b   TATGTTTTATGATGGATATGAGGATGACAAAG---GAAGTGTGTATGGATCTGTTGTTAC
2535 186_HRV28    CATGTTTTATGATGGTTATGAAGATGACAATG---GAACTACCTATGGTGCAGTGGTTAC
```

FIG. D6 CONT'D

```
02.trace                                                              9/20/2007 4:59 PM 2536  187_HRV28a   CATGTTTTATGATGGTTATGAAGATGACAATG---GAACTACCTATGGTGCAGTGGTTAC
2537  188_HRV28b   CATGTTTTATGATGGTTATGAAGATGACAATG---GAACTACCTATGGTGCAGTGGTTAC
2538  189_HRV53a   TATGTTCTATGATGGGTATGAAGATGACAATG---GCACCACTTATGGGGCTGTTGTTAC
2539  190_HRV53b   TATGTTCTATGATGGGTATGAAGATGACAATG---GCACCACTTATGGGGCTGTTGTTAC
2540  191_HRV53    TATGTTCTATGATGGGTATGAAGATGACAATG---GCACCACTTATGGGGCTGTTGTTAC
2541  192_HRV46a   CATGTTTTATGATGGCTACGAAAGTGATAAAG---GCAAGATCTATGGAACTGCAGTCAC
2542  193_HRV46b   CATGTTTTATGATGGCTACGAAAGTGATAAAG---GCAAGATCTATGGAACTGCAGTCAC
2543  194_HRV46    CATGTTTTATGATGGCTACGAAAGTGATAAAG---GCAAGATCTATGGAACTGCAGTCAC
2544  195_HRV80a   CATGTTCTATGATGGGTATGAGAGTGATAAAG---GCAACATTTATGGAACAGCAGTTAC
2545  196_HRV80b   CATGTTCTATGATGGGTATGAGAGTGATAAAG---GCAACATTTATGGAACAGCAGTTAC
2546  197_HRV80    CATGTTCTATGATGGGTATGAGAGTGATAAAG---GCAACATTTATGGAACAGCAGTTAC
2547  198_HRV51    CATGTTTTATGATGGGTATGAAGGTGATAGTTTGACCTCACAGTACGGTTCAGTAGTCAC
2548  199_HRV51a   CATGTTTTATGATGGGTATGAAGGTGATAGTTTGACCTCACAGTACGGTTCAGTAGTCAC
2549  200_HRV51b   CATGTTTTATGATGGGTATGAAGGTGATAGTTTGACCTCACAGTACGGTTCAGTAGTCAC
2550  201_HRV65a   CATGTTCTATGATGGTTATGAGGGTGATGACCCAAATTCAAAATATGGTTCAGTGGTTAC
2551  202_HRV65b   CATGTTCTATGATGGTTATGAGGGTGATGACCCAAATTCAAAATATGGTTCAGTGGTTAC
2552  203_HRV65    CATGTTCTATGATGGTTATGAGGGTGATGACCCAAATTCAAAATATGGTTCAGTGGTTAC
2553  204_HRV71a   CATGTTCTATGATGGGTATGAAGGTGATGCCCTCAGTTCTAAATATGGCTCAGTAGTTAC
2554  205_HRV71b   CATGTTCTATGATGGGTATGAAGGTGATGCCCTCAGTTCTAAATATGGCTCAGTAGTTAC
2555  206_HRV71    CATGTTCTATGATGGGTATGAAGGTGATGCCCTCAGTTCTAAATATGGCTCAGTAGTTAC
2556  207_HRV8     CATGTTCTATGATGGTTATGATTCAGATGGTTTAGATGCTATTTATGGTATTCCTGTTAC
2557  208_HRV95    CATGTTCTATGATGGTTATGATTCAGATGGTTTAGATGCTATTTATGGTATTCCTGTTAC
2558  209_HRV45    CATGTTTTATGATGGATACGACACTGATGGCACAGATGCAGTGTATGGTGTTAGTGTGAC
2559  210_HRV45a   CATGTTTTATGATGGATACGACACTGATGGCACAGATGCAGTGTATGGTGTTAGTGTGAC
2560  211_HRV45b   CATGTTTTATGATGGATACGACACTGATGGCACAGATGCAGTGTATGGTGTTAGTGTGAC
2561  GROUP_1      -ATGTT-TA-GA-GG-TA----------------------TA-GG-----------
2562
2563  1_HRV1A1|d   TAATGATATGGGTACTATATGCTCAAGAATAGTTACAGAAAAACAGAAACATTCTGTTGT
2564  2_HRV1A2|d   TAATGATATGGGTACTATATGCTCAAGAATAGTTACAGAAAAACAGAAACATTCTGTTGT
2565  3_HRV1A|cD   TAATGATATGGGTACTATATGCTCAAGAATAGTTACAGAAAAACAGAAACATTCTGTTGT
2566  4_HRV1B1|d   CAATGATATGGGAACCATATGTTCAAGAATAGTTACAGAGAAGCAGGAACACCCTGTCGT
2567  5_HRV1B2|d   CAATGATATGGGAACCATATGTTCAAGAATAGTTACAGAGAAGCAGGAACACCCTGTCGT
2568  6_HRV1B      CAATGATATGGGAACCATATGTTCAAGAATAGTTACAGAGAAGCAGGAACACCCTGTCGT
2569  7_HRV40a|d   TAACCATATGGGAACGCTATGCTCAAGAATAGTCACCAACAAGCAGCAGCATGAAGTTGA
2570  8_HRV40b|d   TAACCATATGGGAACGCTATGCTCAAGAATAGTCACCAACAAGCAGCAGCATGAAGTTGA
2571  9_HRV40      TAACCATATGGGAACGCTATGCTCAAGAATAGTCACCAACAAGCAGCAGCATGAAGTTGA
2572  10_HRV85     CAACCACATGGGAACACTGTGCTCGAGGATAGTTACCAACAAACAGCAGCATGAGGTTGA
2573  11_HRV85a|   CAACCACATGGGAACACTGTGCTCGAGGATAGTTACCAACAAACAGCAGCATGAGGTTGA
2574  12_HRV85b|   CAACCACATGGGAACACTGTGCTCGAGGATAGTTACCAACAAACAGCAGCATGAGGTTGA
2575  13_HRV56a|   AAACCACATGGGGACACTCTGTTCAAGAATTGTGACAAATAAACAACTTCATCCTGTTGA
2576  14_HRV56b|   AAACCACATGGGGACACTCTGTTCAAGAATTGTGACAAATAAACAACTTCATCCTGTTGA
2577  15_HRV56     AAACCACATGGGGACACTCTGTTCAAGAATTGTGACAAATAAACAACTTCATCCTGTTGA
2578  16_HRV54     CAATCATATGGGTACTTTGTGTTCAAGAGTACTGATAAACAAAAACACCCAGTTGA
2579  17_HRV98     TAATCACATGGGCACTTTGTGTTCAAGAGTAGTTACTGGCAAACAAGAACACCCAGTTGA
2580  18_HRV59a|   CAACCACATGGGCACTTTATGTTCTAGAATAGTTACAAACAGTCAGGAGCATCCAGTGGA
2581  19_HRV59b|   CAACCACATGGGCACTTTATGTTCTAGAATAGTTACAAACAGTCAGGAGCATCCAGTGGA
2582  20_HRV59     CAACCACATGGGCACTTTATGTTCTAGAATAGTTACAAACAGTCAGGAGCATCCAGTGGA
2583  21_HRV63     TAACCACATGGGGACTTTATGTTCTAGAATTGTAACAAACAGCCAAGAACATCCAGTTGA
2584  22_HRV63b|   TAACCACATGGGGACTTTATGTTCTAGAATTGTAACAAACAGCCAAGAACATCCAGTTGA
2585  23_HRV63a|   TAACCACATGGGGACTTTATGTTCTAGAATTGTAACAAACAGCCAAGAACATCCAGTTGA
2586  24_HRV39     TAATGATATGGGTACACTTTGCACTAGAATTGTAACAAACCAACAGGAACACCTAGTGGA
2587  25_HRV39a|   TAATGATATGGGTACACTTTGCACTAGAATTGTAACAAACCAACAGGAACACCTAGTGGA
2588  26_HRV39b|   TAATGATATGGGTACACTTTGCACTAGAATTGTAACAAACCAACAGAAACACCTAGTGGA
2589  27_HRV10a|   AAATCACATGGGCACTTTGTGCATGCGAATAGTCACAAACCAAGCAAGCACATGAGGTGGA
2590  28_HRV10b|   AAATCACATGGGCACTTTGTGCATGCGAATAGTCACAAACCAGCAAGCACATGAGGTGGA
2591  29_HRV10     AAATCACATGGGCACTTTGTGCATGCGAATAGTCACAAACCAGCAAGCACATGAGGTGGA
2592  30_HRV100a   TAACCACATGGGTACACTTTGTATGAGGATAGTTACAAATCAGCAAGCACATGAGGTGGA
2593  31_HRV100b   TAACCACATGGGTACACTTTGTATGAGGATAGTTACAAATCAGCAAGCACATGAGGTGGA
2594  32_HRV100    TAACCACATGGGTACACTTTGTATGAGGATAGTTACAAATCAGCAAGCACATGAGGTGGA
2595  33_HRV66     TAATCATATGGGTACATTATGTATTAGGATTGTTACAAATGAACAGCACCATAATGTTGA
2596  34_HRV66b|   TAATCATATGGGTACATTATGTATTAGGATTGTTACAAATGAACAGCACCATAATGTTGA
2597  35_HRV66a|   TAATCATATGGGTACATTATGTATTAGGATTGTTACAAATGAACAGCACCATAATGTTGA
2598  36_HRV77a|   TAATCACATGGGCACACTGTGCATTAGAATAGTCACTAATCAGCAAAATCATGAGGTTGA
2599  37_HRV77b|   TAATCACATGGGCACACTGTGCATTAGAATAGTCACTAATCAGCAAAATCATGAGGTTGA
2600  38_HRV77     TAATCACATGGGCACACTGTGCATTAGAATAGTCACTAATCAGCAAAATCATGAGGTTGA
```

FIG. D6 CONT'D

02.trace                                                                  9/20/2007 4:59 PM

```
2601  39_HRV62a      TAATCGTATGGGGGCACTGTGTATGAGGATTGTCACAAACAAACAAGTTCATGATGTTGA
2602  40_HRV62b      TAATCGTATGGGGGCACTGTGTATGAGGATTGTCACAAACAAACAAGTTCATGATGTTGA
2603  41_HRV25       TAACCGTATGGGAGCACTGTGCATGAGAATTGTCACAAATAAACAAGTCCATGATGTTGA
2604  42_HRV29a      TAACCGGATGGGGACGCTTTGTGTCAGAATTGTTACAGGCAAACAAGCTCATGATGTTCA
2605  43_HRV29b      TAACCGGATGGGGACGCTTTGTGTCAGAATTGTTACAGGCAAACAAGCTCATGATGTTCA
2606  44_HRV44a      TAACCGGATGGGGACGCTTTGCGTCAGGATCGTTACGGGCAAACAGGCTCATGATGTCCA
2607  45_HRV44b      TAACCGGATGGGGACGCTTTGCGTCAGGATCGTTACGGGCAAACAGGCTCATGATGTCCA
2608  46_HRV31       TAATCGCATGGGTGCACTATGCATGAGAGTTGTCACTAACAAACAAGCTCATAAAGTTGA
2609  47_HRV31a|     TAATCGCATGGGTGCACTATGCATGAGAGTTGTCACTAACAAACAAGCTCATAAAGTTGA
2610  48_HRV31b|     TAATCGCATGGGTGCACTATGCATGAGAGTTGTCACTAACAAACAAGCTCATAAAGTTGA
2611  49_HRV47       CAATCGCATGGGTGCATTGTGTATGAGAGTTGTAACAAACAAGCAACTCCATAAAGTTGA
2612  50_HRV47a|     CAATCGCATGGGTGCATTGTGTATGAGAGTTGTAACAAACAAGCAACTCCATAAAGTTGA
2613  51_HRV47b|     CAATCGCATGGGTGCATTGTGTATGAGAGTTGTAACAAACAAGCAACTCCATAAAGTTGA
2614  52_HRV11       CAATGATATGGGCACTCTGTGTTATAGAATAGTAACTGATGACCATAGACACAAAATTGA
2615  53_HRV11b|     CAATGATATGGGCACTCTGTGTTATAGAATAGTAACTGATGACCATAGACACAAAATTGA
2616  54_HRV11a|     CAATGATATGGGCACTCTGTGTTATAGAATAGTAACTGATGACCATAGACACAAAATTGA
2617  55_HRV76       CAATGACATGGGCACCCTATGTTCCAGGATAGTAACTGATGATCATAAGCACAAGATTGA
2618  56_HRV76b|     CAATGACATGGGCACCCTATGTTCCAGGATAGTAACTGATGATCATAAGCACAAGATTGA
2619  57_HRV76a|     CAATGACATGGGCACCCTATGTTCCAGGATAGTAACTGATGATCATAAGCACAAGATTGA
2620  58_HRV33       CAATGACATGGGCACTTTATGCTCTAGAATAGTTACAGATAATCATAAGCATCCAATAGA
2621  59_HRV33b|     CAATGACATGGGCACTTTATGCTCTAGAATAGTTACAGATAATCATAAGCATCCAATAGA
2622  60_HRV33a|     CAATGACATGGGCACTTTATGCTCTAGAATAGTTACAGATAATCATAAGCATCCAATAGA
2623  61_HRV24a|     AAACGACATGGGAACTCTATGCTATAGAATAGTCACTGACAAGCATAATCACCAAATAGA
2624  62_HRV24b|     AAACGACATGGGAACTCTATGCTATAGAATAGTCACTGACAAGCATAATCACCAAATAGA
2625  63_HRV24       AAACGACATGGGAACTCTATGCTATAGAATAGTCACTGACAAGCATAATCACCAAATAGA
2626  64_HRV90       TAATGATATGGGAACCTTATGTTATAGAATAGTTACAGATGAACATGCCCACAAAATAGA
2627  65_HRV90a|     TAATGATATGGGAACCTTATGTTATAGAATAGTTACAGATGAACATGCCCACAAAATAGA
2628  66_HRV90b|     TAATGATATGGGAACCTTATGTTATAGAATAGTTACAGATGAACATGCCCACAAAATAGA
2629  67_HRV34       TAATGACATGGGTACTTTATGCTCCAGAATTGTAACTGATGAACACCAAAACAGAGTAGA
2630  68_HRV34b|     TAATGACATGGGTACTTTATGCTCCAGAATTGTAACTGATGAACACCAAAACAGAGTAGA
2631  69_HRV34a|     TAATGACATGGGTACTTTATGCTCCAGAATTGTAACTGATGAACACCAAAACAGAGTAGA
2632  70_HRV50a|     CAATGACATGGGCACTTTGTGTTCTAGGATTGTCACTGATGAGCACCAAAATAAAGTGGA
2633  71_HRV50b|     CAATGACATGGGCACTTTGTGTTCTAGGATTGTCACTGATGAGCACCAAAATAAAGTGGA
2634  72_HRV50       CAATGACATGGGCACTTTGTGTTCTAGGATTGTCACTGATGAGCACCAAAATAAAGTGGA
2635  73_HRV18a|     AAATGACATGGGTACCTTGTGCTCTAGAATAGTCACAGATAAACATAAGAATGAGGTGGA
2636  74_HRV18b|     AAATGACATGGGTACCTTGTGCTCTAGAATAGTCACAGATAAACATAAGAATGAGGTGGA
2637  75_HRV18       AAATGACATGGGTACCTTGTGCTCTAGAATAGTCACAGATAAACATAAGAATGAGGTGGA
2638  76_HRV55       TAATGACATGGGTACTTTATGTTCTAGAATAATAACTGATAACCATAAGCACCCAATTGA
2639  77_HRV55b|     TAATGACATGGGTACTTTATGTTCTAGAATAATAACTGATAACCATAAGCACCCAATTGA
2640  78_HRV55a|     TAATGACATGGGTACTTTATGTTCTAGAATAATAACTGATAACCATAAGCACCCAATTGA
2641  79_HRV57       TAATGACATGGGCACTTTATGTTCTAGAATTGTTACTGACCAGCACACACATCCCATAAA
2642  80_HRV57a|     TAATGACATGGGCACTTTATGTTCTAGAATTGTTACTGACCAGCACACACATCCCATAAA
2643  81_HRV57b|     TAATGACATGGGCACTTTATGTTCTAGAATTGTTACTGACCAGCACACACATCCCATAAA
2644  82_HRV21       TAATGATATGGGATCTCTATGCTACAGAATAGTAACTGGCCAGCATAAGCATAAGATAGA
2645  83_HRVHan      TAATGATATGGGATCTCTATGCTATAGAATAGTAACTGATCAGCATAAGCACAAGATAGA
2646  84_HRV43       CAACCACATGGGAACATTATGTTCTAGGATAGTTACAGAAGAACACCAAAATCAAATCGA
2647  85_HRV43b|     CAACCACATGGGAACATTATGTTCTAGGATAGTTACAGAAGAACACCAAAATCAAATCGA
2648  86_HRV43a|     CAACCACATGGGAACATTATGTTCTAGGATAGTTACAGAAGAACACCAAAATCAAATCGA
2649  87_HRV75       TAATCACATGGGGACACTGTGTTCTAGAATAGTTACAGAAGAACATCGAAATAAAGTTGA
2650  88_HRV75b|     TAATCACATGGGGACACTGTGTTCTAGAATAGTTACAGAAGAACATCGAAATAAAGTTGA
2651  89_HRV75a|     TAATCACATGGGGACACTGTGTTCTAGAATAGTTACAGAAGAACATCGAAATAAAGTTGA
2652  96_HRV9a|d     AAATGATATGGGATCTTTATGTTCCCGTGTAGTTACTGAAGAGCATGGACCCCGTGTCAA
2653  97_HRV9b|d     AAATGATATGGGATCTTTATGTTCCCGTGTAGTTACTGAAGAGCATGGACCCCGTGTCAA
2654  98_HRV9        AAATGATATGGGATCTTTATGTTCCCGTGTAGTTACTGAAGAGCATGGACCCCGTGTCAA
2655  99_HRV32       AAATGATATGGGTTCCCTGTGTTCTCGTATAGTCACCGAAGAGCACGGATCCCGTGTTGA
2656  100_HRV32a     AAATGATATGGGTTCCCTGTGTTCTCGTATAGTCACCGAAGAGCACGGATCCCGTGTTGA
2657  101_HRV32b     AAATGATATGGGTTCCCTGTGTTCTCGTATAGTCACCGAAGAGCACGGATCCCGTGTTGA
2658  102_HRV67      TAATGATATGGGTTCCTTGTGTTCGCGTATAGTTACTGAAGAACATGGTTCTCGCGTAAA
2659  103_HRV67a     TAATGATATGGGTTCCTTGTGTTCGCGTATAGTTACTGAAGAACATGGTTCTCGCGTAAA
2660  104_HRV67b     TAATGATATGGGTTCCTTGTGTTCGCGTATAGTTACTGAAGAACATGGTTCTCGCGTAAA
2661  105_HRV15      TAATGACATGGGGACACTGTGTTCTAGAATAGTAACTGAAGAGCATGGGACACGTGTAGA
2662  106_HRV15a     TAATGACATGGGGACACTGTGTTCTAGAATAGTAACTGAAGAGCATGGGACACGTGTAGA
2663  107_HRV15b     TAATGACATGGGGACACTGTGTTCTAGAATAGTAACTGAAGAGCATGGGACACGTGTAGA
2664  108_HRV74a     AAATGACATGGGAACTCTATGTTCTAGAATTGTGACTGAAGAACACGATGCACGTGTGGA
2665  109_HRV74b     AAATGACATGGGAACTCTATGTTCTAGAATTGTGACTGAAGAACACGATGCACGTGTGGA
```

FIG. D6 CONT'D 02.trace                                                                 9/20/2007 4:59 PM

```
2666 110_HRV74   AAATGACATGGGAACTCTATGTTCTAGAATTGTGACTGAAGAACACGATGCACGTGTGGA
2667 111_HRV38a  CAATGATATGGGGACACTTTGTTCAAGAATAGTCACTGAAAATCATGGGACCCAAGTGAA
2668 112_HRV38b  CAATGATATGGGGACACTTTGTTCAAGAATAGTCACTGAAAATCATGGGACCCAAGTGAA
2669 113_HRV38   CAATGATATGGGGACACTTTGTTCAAGAATAGTCACTGAAAATCATGGGACCCAAGTGAA
2670 114_HRV60   CAATGACATGGGAACGTTGTGCTCCAGAATAGTTACTGAACACCATGGTACACAGGTTCA
2671 115_HRV60a  CAATGACATGGGAACGTTGTGCTCCAGAATAGTTACTGAACACCATGGTACACAGGTTCA
2672 116_HRV60b  CAATGACATGGGAACGTTGTGCTCCAGAATAGTTACTGAACACCATGGTACACAGGTTCA
2673 117_HRV64a  AAATGATATGGGCACTTTGTGTTCTAGAATTGTGACTGAGGAACACACAACACAGGTCAA
2674 118_HRV64b  AAATGATATGGGCACTTTGTGTTCTAGAATTGTGACTGAGGAACACACAACACAGGTCAA
2675 119_HRV64   AAATGATATGGGCACTTTGTGTTCTAGAATTGTGACTGAGGAACACACAACACAGGTCAA
2676 120_HRV94a  AAATGACATGGGAACATTATGCTCCAGGATTGTGACTGAGGAGCACAAGACACAGGTTAA
2677 121_HRV94b  AAATGACATGGGAACATTATGCTCCAGGATTGTGACTGAGGAGCACAAGACACAGGTTAA
2678 122_HRV94   AAATGACATGGGAACATTATGCTCCAGGATTGTGACTGAGGAGCACAAGACACAGGTTAA
2679 123_HRV22   AAATGATATGGGCACACTGTGCTCTAGGATTGTGACTGAAGAACACCAGACACAAGTCAA
2680 124_HRV22a  AAATGATATGGGCACACTGTGCTCTAGGATTGTGACTGAAGAACACCAGACACAAGTCAA
2681 125_HRV22b  AAATGATATGGGCACACTGTGCTCTAGGATTGTGACTGAAGAACACCAGACACAAGTCAA
2682 126_HRV82   AAATGACATGGGTACACTGTGTTCTAGAATTGTAACTGAAGAACACCAGACTCAAGTCAG
2683 127_HRV82b  AAATGACATGGGTACACTGTGTTCTAGAATTGTAACTGAAGAACACCAGACTCAAGTCAG
2684 128_HRV82a  AAATGACATGGGTACACTGTGTTCTAGAATTGTAACTGAAGAACACCAGACTCAAGTCAG
2685 129_HRV19   TAATGATATGGGAACCTTATGCTCCAGAATAGTAACTGATGAACACCAAACACAGGTTGC
2686 130_HRV19a  TAATGATATGGGAACCTTATGCTCCAGAATAGTAACTGATGAACACCAAACACAGGTTGC
2687 131_HRV19b  TAATGATATGGGAACCTTATGCTCCAGAATAGTAACTGATGAACACCAAACACAGGTTGC
2688 132_HRV13   TAATGATATGGGCACACTTTGCTTCAGAATAGTAACTGAAGAACATACTAACAAGGTCAA
2689 133_HRV13a  TAATGATATGGGCACACTTTGCTTCAGAATAGTAACTGAAGAACATACTAACAAGGTCAA
2690 134_HRV13b  TAATGATATGGGCACACTTTGCTTCAGAATAGTAACTGAAGAACATACTAACAAGGTCAA
2691 135_HRV41   AAATGACATGGGTACATTATGCTTTAGAATAGTTACTGAAGAACACACCAACAAAGTTAA
2692 136_HRV41a  AAATGACATGGGTACATTATGCTTTAGAATAGTTACTGAAGAACACACCAACAAAGTTAA
2693 137_HRV41b  AAATGACATGGGTACATTATGCTTTAGAATAGTTACTGAAGAACACACCAACAAAGTTAA
2694 138_HRV73   TAATGACATGGGCACATTATGCTTTAGGATAGTGACTGAAGAACACACTAGCAGGGTAAA
2695 139_HRV73b  TAATGACATGGGCACATTATGCTTTAGGATAGTGACTGAAGAACACACTAGCAGGGTAAA
2696 140_HRV73a  TAATGACATGGGCACATTATGCTTTAGGATAGTGACTGAAGAACACACTAGCAGGGTAAA
2697 141_HRV61   AAATGATATGGGTGCATTGTGCTTTAGAATAGTAACTGAACAGCATACAAATCAAGTTAA
2698 142_HRV61a  AAATGATATGGGTGCATTGTGCTTTAGAATAGTAACTGAACAGCATACAAATCAAGTTAA
2699 143_HRV61b  AAATGATATGGGTGCATTGTGCTTTAGAATAGTAACTGAACAGCATACAAATCAAGTTAA
2700 144_HRV96   CAATGACATGGGCACTTTATGTTTTAGAATAGTGACAGAGGAACACACCAACAAGGTCAA
2701 145_HRV96b  CAATGACATGGGCACTTTATGTTTTAGAATAGTGACAGAGGAACACACCAACAAGGTCAA
2702 146_HRV96a  CAATGACATGGGCACTTTATGTTTTAGAATAGTGACAGAGGAACACACCAACAAGGTCAA
2703 90_HRV16a|  CAATGACATGGGAACTTTGTGTTCGCGTATTGTGACCAGTGAGCAATTACACAAAGTCAA
2704 91_HRV16b|  CAATGACATGGGAACTTTGTGTTCGCGTATTGTGACCAGTGAGCAATTACACAAAGTCAA
2705 92_1AYM_A   CAATGACATGGGAACTTTGTGTTCGCGTATTGTGACCAGTGAGCAATTACACAAAGTCAA
2706 93_HRV81a|  TAATGATATGGGAACATTATGCTCACGGATAGTGACAAGTGAGCAAGTGCACAAGGTGAA
2707 94_HRV81b|  TAATGATATGGGAACATTATGCTCACGGATAGTGACAAGTGAGCAAGTGCACAAGGTGAA
2708 95_HRV81    TAATGATATGGGAACATTATGCTCACGGATAGTGACAAGTGAGCAAGTGCACAAGGTGAA
2709 147_HRV2    AAATAACATGGGGTCACTATGCTCTAGGATAGTAACAGAGAAACACATTCATAAGGTACA
2710 148_HRV2a|  AAATAACATGGGGTCACTATGCTCTAGGATAGTAACAGAGAAACACATTCATAAGGTACA
2711 149_HRV2b|  AAATAACATGGGGTCACTATGCTCTAGGATAGTAACAGAGAAACACATTCATAAGGTACA
2712 150_HRV49a  AAACAACATGGGATCATTATGCTCTAGGATAGTAACAGAGAAACACATTCACAGTATGCA
2713 151_HRV49b  AAACAACATGGGATCATTATGCTCTAGGATAGTAACAGAGAAACACATTCACAGTATGCA
2714 152_HRV49   AAACAACATGGGATCATTATGCTCTAGGATAGTAACAGAGAAACACATTCACAGTATGCA
2715 153_HRV23a  AAACAACATGGGCACATTGTGCTCCAGAGTGGTAACAGAGAAACACATTCATGATATGCG
2716 154_HRV23b  AAACAACATGGGCACATTGTGCTCCAGAGTGGTAACAGAGAAACACATTCATGATATGCG
2717 155_HRV23   AAACAACATGGGCACATTGTGCTCCAGAGTGGTAACAGAGAAACACATTCATGATATGCG
2718 156_HRV30a  AAACAACATGGGCACACTGTGTTCCAGAGTGGTAACAGAAAAACACATTCATGATGTGCG
2719 157_HRV30b  AAACAACATGGGCACACTGTGTTCCAGAGTGGTAACAGAAAAACACATTCATGATGTGCG
2720 158_HRV30   AAACAACATGGGCACACTGTGTTCCAGAGTGGTAACAGAAAAACACATTCATGATGTGCG
2721 159_HRV7    CAATGACATGGGAACCATATGTGTTAGACTAGTTACATCTACACAAAAACACAATTTAAA
2722 160_HRV7b|  CAATGACATGGGAACCATATGTGTTAGACTAGTTACATCTACACAAAAACACAATTTAAA
2723 161_HRV7a|  CAATGACATGGGAACCATATGTGTTAGACTAGTTACATCTACACAAAAACACAATTTAAA
2724 162_HRV88   TAATGATATGGGAACTATATGTATTAGATTGGTCACCTCCACCCAAAAGCATAAACTGAA
2725 163_HRV88a  TAATGATATGGGAACTATATGTATTAGATTGGTCACCTCCACCCAAAAGCATAAACTGAA
2726 164_HRV88b  TAATGATATGGGAACTATATGTATTAGATTGGTCACCTCCACCCAAAAGCATAAACTGAA
2727 165_HRV36a  TAACGACATGGGAACCATATGTGTTAGAATAGTTACATCCAACCAAAAACATGATTTAAA
2728 166_HRV36b  TAACGACATGGGAACCATATGTGTTAGAATAGTTACATCCAACCAAAAACATGATTTAAA
2729 167_HRV36   TAACGACATGGGAACCATATGTGTTAGAATAGTTACATCCAACCAAAAACATGATTTAAA
2730 168_HRV89a  TAATGATATGGGAACCATATGTGTTAGAATAGTGACATCCAACCAAAAACATGATTTAAA
```

FIG. D6 CONT'D

```
02.trace                                                           9/20/2007 4:59 PM 2731 169_HRV89b    TAATGATATGGGAACCATATGTGTTAGAATAGTGACATCCAACCAAAAACATGATTTAAA
2732 170_HRV89     TAATGATATGGGAACCATATGTGTTAGAATAGTGACATCCAACCAAAAACATGATTTAAA
2733 171_HRV58     AAATGACATGGGAACTATATGTGTTAGAATAGTCACATCCAAACAAAGACACAATTTAAA
2734 172_HRV58a    AAATGACATGGGAACTATATGTGTTAGAATAGTCACATCCAAACAAAGACACAATTTAAA
2735 173_HRV58b    AAATGACATGGGAACTATATGTGTTAGAATAGTCACATCCAAACAAAGACACAATTTAAA
2736 174_HRV12a    CAATGACATGGGTTCACTGTGTGTCAGAATAGTTACAGACCAGCAAAAACATAAAGTTAA
2737 175_HRV12b    CAATGACATGGGTTCACTGTGTGTCAGAATAGTTACAGACCAGCAAAAACATAAAGTTAA
2738 176_HRV12     CAATGACATGGGTTCACTGTGTGTCAGAATAGTTACAGACCAGCAAAAACATAAAGTTAA
2739 177_HRV78a    CAATGACATGGGTACACTGTGTATGAGGATGGTTACAGATCAACAACAACATAAGGTCAC
2740 178_HRV78b    CAATGACATGGGTACACTGTGTATGAGGATGGTTACAGATCAACAACAACATAAGGTCAC
2741 179_HRV78     CAATGACATGGGTACACTGTGTATGAGGATGGTTACAGATCAACAACAACATAAGGTCAC
2742 180_HRV20     AAACGATATGGGCACATTGTGTGTTCGTATTGTGACTGAGCAGCAGACACATAAGGTTAA
2743 181_HRV20a    AAACGATATGGGCACATTGTGTGTTCGTATTGTGACTGAGCAGCAGACACATAAGGTTAA
2744 182_HRV20b    AAACGATATGGGCACATTGTGTGTTCGTATTGTGACTGAGCAGCAGACACATAAGGTTAA
2745 183_HRV68     AAATGATATGGGCACATTATGTGTCCGTATTGTGACTGAGCAGCAGACACATAGGGTCAA
2746 184_HRV68a    AAATGATATGGGCACATTATGTGTCCGTATTGTGACTGAGCAGCAGACACATAGGGTCAA
2747 185_HRV68b    AAATGATATGGGCACATTATGTGTCCGTATTGTGACTGAGCAGCAGACACATAGGGTCAA
2748 186_HRV28     AAATCATATGGGAACACTCTGTGCTCGCATAGTAACTGAACAACAGAAGCATGAAGTCAA
2749 187_HRV28a    AAATCATATGGGAACACTCTGTGCTCGCATAGTAACTGAACAACAGAAGCATGAAGTCAA
2750 188_HRV28b    AAATCATATGGGAACACTCTGTGCTCGCATAGTAACTGAACAACAGAAGCATGAAGTCAA
2751 189_HRV53a    TAATGATATGGGAACACTTTGTGTGCGCATAGTGACTGAGCAACAGAAAAATGAGGTCAA
2752 190_HRV53b    TAATGATATGGGAACACTTTGTGTGCGCATAGTGACTGAGCAACAGAAAAATGAGGTCAA
2753 191_HRV53     TAATGATATGGGAACACTTTGTGTGCGCATAGTGACTGAGCAACAGAAAAATGAGGTCAA
2754 192_HRV46a    CAATGATATGGGAACTATATGTGTCAGAATTGTTACCGAACAACAAAAACATAAGGTTCT
2755 193_HRV46b    CAATGATATGGGAACTATATGTGTCAGAATTGTTACCGAACAACAAAAACATAAGGTTCT
2756 194_HRV46     CAATGATATGGGAACTATATGTGTCAGAATTGTTACCGAACAACAAAAACATAAGGTTCT
2757 195_HRV80a    CAATGATATGGGAACCCTGTGTGCTAGAATTGTTACAGAACAACAGAAACATAAAGTCCT
2758 196_HRV80b    CAATGATATGGGAACCCTGTGTGCTAGAATTGTTACAGAACAACAGAAACATAAAGTCCT
2759 197_HRV80     CAATGATATGGGAACCCTGTGTGCTAGAATTGTTACAGAACAACAGAAACATAAAGTCCT
2760 198_HRV51     AAATGCTATGGGGACACTATGTGTTCGTGTGGTCACAGAGCAACAAAAACATGAGGTTAA
2761 199_HRV51a    AAATGCTATGGGGACACTATGTGTTCGTGTGGTCACAGAGCAACAAAAACATGAGGTTAA
2762 200_HRV51b    AAATGCTATGGGGACACTATGTGTTCGTGTGGTCACAGAGCAACAAAAACATGAGGTTAA
2763 201_HRV65a    TAATGCTATGGGCACACTATATGTGCGTGTGGTTACAGAAAGGCAAAAACATGAAGTCAA
2764 202_HRV65b    TAATGCTATGGGCACACTATATGTGCGTGTGGTTACAGAAAGGCAAAAACATGAAGTCAA
2765 203_HRV65     TAATGCTATGGGCACACTATATGTGCGTGTGGTTACAGAAAGGCAAAAACATGAAGTCAA
2766 204_HRV71a    TAATGCCATGGGCACCTTATGTGTTCGTGTGGTTACAGAACAGCAAAGCAACACAGTCAA
2767 205_HRV71b    TAATGCCATGGGCACCTTATGTGTTCGTGTGGTTACAGAACAGCAAAGCAACACAGTCAA
2768 206_HRV71     TAATGCCATGGGCACCTTATGTGTTCGTGTGGTTACAGAACAGCAAAGCAACACAGTCAA
2769 207_HRV8      AAATCACATGGGCACAATATGTGTGAGAATGGTGACAGATAAACAGAAAATTAAAACTAA
2770 208_HRV95     AAATCACATGGGCACAATATGTGTGAGAATGGTGACAGATAAACAGAAAATTAAAACTAA
2771 209_HRV45     TAACCATATGGGGACTATATGTGTTAGAATTGTTACAGACCAACAACAACATAGAGTTAA
2772 210_HRV45a    TAACCATATGGGGACTATATGTGTTAGAATTGTTACAGACCAACAACAACATAGAGTTAA
2773 211_HRV45b    TAACCATATGGGGACTATATGTGTTAGAATTGTTACAGACCAACAACAACATAGAGTTAA
2774 GROUP_1       -AA----ATGGG--C--T-T------G--T--T-AC-------CA--------------
2775
2776 1_HRV1A1|d    CATCACAACACACATATATCATAAAGCTAAACACACAAAAGCTTGGTGTCCTAGGCCCCC
2777 2_HRV1A2|d    CATCACAACACACATATATCATAAAGCTAAACACACAAAAGCTTGGTGTCCTAGGCCCCC
2778 3_HRV1A|cD    CATCACAACACACATATATCATAAAGCTAAACACACAAAAGCTTGGTGTCCTAGGCCCCC
2779 4_HRV1B1|d    TATTACAACACACATATATCACAAAGCTAAACACACAAAAGCTTGGTGTCCTAGACCTCC
2780 5_HRV1B2|d    TATTACAACACACATATATCACAAAGCTAAACACACAAAAGCTTGGTGTCCTAGACCTCC
2781 6_HRV1B       TATTACAACACACATATATCACAAAGCTAAACACACAAAAGCTTGGTGTCCTAGACCTCC
2782 7_HRV40a|d    GATTACCACACGTATATATCACAAGGCCAAGCATATTAAAGCATGGTGTCCAAGGGCCCC
2783 8_HRV40b|d    GATTACCACACGTATATATCACAAGGCCAAGCATATTAAAGCATGGTGTCCAAGGGCCCC
2784 9_HRV40       GATTACCACACGTATATATCACAAGGCCAAGCATATTAAAGCATGGTGTCCAAGGGCCCC
2785 10_HRV85      AATCACCACGCGTGTGTATCATAAGGCCAAGCATGTAAAGGCTTGGTGTCCAAGAGCACC
2786 11_HRV85a|    AATCACCACGCGTGTGTATCATAAGGCCAAGCATGTAAAGGCTTGGTGTCCAAGAGCACC
2787 12_HRV85b|    AATCACCACGCGTGTGTATCATAAGGCCAAGCATGTAAAGGCTTGGTGTCCAAGAGCACC
2788 13_HRV56a|    AGTCACAACTCGTGTATATCATAAGGCAAAGCATATTCGAGCATGGTGTCCTAGAGCACC
2789 14_HRV56b|    AGTCACAACTCGTGTATATCATAAGGCAAAGCATATTCGAGCATGGTGTCCTAGAGCACC
2790 15_HRV56      AGTCACAACTCGTGTATATCATAAGGCAAAGCATATTCGAGCATGGTGTCCTAGAGCACC
2791 16_HRV54      AATCACCACGGGTGTATCACAAGGCAAAACACATTAGAGCATGGTGTCCACGTGCACC
2792 17_HRV98      AATCACTACACGTGTACCACAAAGCAAAACACATTAGAGCATGGTGTCCACGTGCACC
2793 18_HRV59a|    GGTTGTCACACGTGTGTATCACAAAGCTAAACACGTCAAAGCCTGGTGCCCTAGAGCTCC
2794 19_HRV59b|    GGTTGTCACACGTGTGTATCACAAAGCTAAACACGTCAAAGCCTGGTGCCCTAGAGCTCC
2795 20_HRV59      GGTTGTCACACGTGTGTATCACAAAGCTAAACACGTCAAAGCCTGGTGCCCTAGAGCTCC
```

FIG. D6 CONT'D

```
02.trace                                                                9/20/2007 4:59 PM 2796 21_HRV63    GGTGACTACACGTGTATATCATAAAGCTAAACACATCAGAGCCTGGTGCCCAAGAGCTCC
2797 22_HRV63b|  GGTGACTACACGTGTATATCATAAAGCTAAACACATCAGAGCCTGGTGCCCAAGAGCTCC
2798 23_HRV63a|  GGTGACTACACGTGTATATCATAAAGCTAAACACATCAGAGCCTGGTGCCCAAGAGCTCC
2799 24_HRV39    GGTTACAACCAGAGTTTACCATAAAGCCAAGCATGTTAAAGCATGGTGCCCTAGGGCTCC
2800 25_HRV39a|  GGTTACAACCAGAGTTTACCATAAAGCCAAGCATGTTAAAGCATGGTGCCCTAGGGCTCC
2801 26_HRV39b|  GGTTACAACCAGAGTTTACCATAAAGCCAAGCATGTTAAAGCATGGTGCCCTAGGGCTCC
2802 27_HRV10a|  AATTACCACCAGTGTTTATCACAAAGCCAAGCATGTCAAAGCATGGTGTCCAAGACCACC
2803 28_HRV10b|  AATTACCACCAGTGTTTATCACAAAGCCAAGCATGTCAAAGCATGGTGTCCAAGACCACC
2804 29_HRV10    AATTACCACCAGTGTTTATCACAAAGCCAAGCATGTCAAAGCATGGTGTCCAAGACCACC
2805 30_HRV100a  AATTACTACTAATATCTATCACAAGGCCAAACATGTTAAAGCTTGGTGCCCAAGACCACC
2806 31_HRV100b  AATTACTACTAATATCTATCACAAGGCCAAACATGTTAAAGCTTGGTGCCCAAGACCACC
2807 32_HRV100   AATTACTACTAATATCTATCACAAGGCCAAACATGTTAAAGCTTGGTGCCCAAGACCACC
2808 33_HRV66    AATTACTACTAGAGTATACCATAAGGCTAAGCATGTTAAAGCCTGGTGTCCTAGACCACT
2809 34_HRV66b|  AATTACTACTAGAGTATACCATAAGGCTAAGCATGTTAAAGCCTGGTGTCCTAGACCACT
2810 35_HRV66a|  AATTACTACTAGAGTATACCATAAGGCTAAGCATGTTAAAGCCTGGTGTCCTAGACCACT
2811 36_HRV77a|  AATCACCACTAGAGTATACCACAAGGCTAAACATATTAAAGCTTGGTGTCCCAGACCACC
2812 37_HRV77b|  AATCACCACTAGAGTATACCACAAGGCTAAACATATTAAAGCTTGGTGTCCCAGACCACC
2813 38_HRV77    AATCACCACTAGAGTATACCACAAGGCTAAACATATTAAAGCTTGGTGTCCCAGACCACC
2814 39_HRV62a   GGTCACAACTAATATTTACCACAAGGCTAAGCATGTAAAAGCGTGGTGCCCGCGGCCGCC
2815 40_HRV62b   GGTCACAACTAATATTTACCACAAGGCTAAGCATGTAAAAGCGTGGTGCCCTAGACCACC
2816 41_HRV25    GGTTACAACTAACATTTACCATAAAGCTAAGCATGTAAAAGCATGGTGCCCTAGACCACC
2817 42_HRV29a   AGTTACAACAAGTATCTATCATAAAGCTAAACATGTAAAGGCGTGGTGTCCTAGACCACC
2818 43_HRV29b   AGTTACAACAAGTATCTATCATAAAGCTAAACATGTAAAGGCGTGGTGTCCTAGACCACC
2819 44_HRV44a   AGTTACAACAAGCATTTACCAAAAGCTAAACATGTAAAAGCATGGTGCCCTAGACCACC
2820 45_HRV44b   AGTTACAACAAGCATTTACCATAAAGCTAAACATGTAAAAGCATGGTGCCCTAGACCACC
2821 46_HRV31    AATCACAACCAATATTTACCATAAGGCCAAACATGTTAAGGCATGGTGTCCTAGGCCCCC
2822 47_HRV31a|  AATCACAACCAATATTTACCATAAGGCCAAACATGTTAAGGCATGGTGTCCTAGGCCCCC
2823 48_HRV31b|  AATCACAACCAATATTTACCATAAGCCAAACATGTAAAGGCATGGTGTCCTAGGCCCCC
2824 49_HRV47    AATCACAACTAACATCTACCATAAAGCCAAGCATGTGAAAGCATGGTGTCCTAGACCACC
2825 50_HRV47a|  AATCACAACTAACATCTACCATAAAGCCAAGCATGTGAAAGCATGGTGTCCTAGACCACC
2826 51_HRV47b|  AATCACAACTAACATCTACCATAAAGCCAAGCATGTGAAAGCATGGTGTCCTAGACCACC
2827 52_HRV11    AGTCACAACTAGGGTGTATCATAAAGCAAAGCATGTGAAGGTGTGGTGTCCAAGACCACC
2828 53_HRV11b|  AGTCACAACTAGGGTGTATCATAAAGCAAAGCATGTGAAGGTGTGGTGTCCAAGACCACC
2829 54_HRV11a|  AGTCACAACTAGGGTGTATCATAAAGCAAAGCATGTGAAGGTGTGGTGTCCAAGACCACC
2830 55_HRV76    AGTTACAACAAGAATATATCACAAAGCAAAGCATGTTAAGGTATGGTGCCCGAGACCACC
2831 56_HRV76b|  AGTTACAACAAGAATATATCACAAAGCAAAGCATGTTAAGGTATGGTGCCCGAGACCACC
2832 57_HRV76a|  AGTTACAACAAGAATATATCACAAAGCAAAGCATGTTAAGGTATGGTGCCCGAGACCACC
2833 58_HRV33    AGTTACAACAAGAGTATACCATAAAGCAAAACATGTCAAAGTCTGGTGCCCAAGACCACC
2834 59_HRV33b|  AGTTACAACAAGAGTATACCATAAAGCAAAACATGTCAAAGTCTGGTGCCCAAGACCACC
2835 60_HRV33a|  AGTTACAACAAGAGTATACCATAAAGCAAAACATGTCAAAGTCTGGTGCCCAAGACCACC
2836 61_HRV24a|  AATTACAACAAGAATATACCACAAAGCAAAGCACATTAAGGTCTGGTGTCCAAGGCCACC
2837 62_HRV24b|  AATTACAACAAGAATATACCACAAAGCAAAGCACATTAAGGTCTGGTGTCCAAGGCCACC
2838 63_HRV24    AATTACAACAAGAATATACCACAAAGCAAAGCACATTAAGGTCTGGTGTCCAAGGCCACC
2839 64_HRV90    GATCACTACAAGAATATACCATAAAGCAAAACACATTAAGGTTTGGTGTCCAAGACCACC
2840 65_HRV90a|  GATCACTACAAGAATATACCATAAAGCAAAACACATTAAGGTTTGGTGTCCAAGACCACC
2841 66_HRV90b|  GATCACTACAAGAATATACCATAAAGCAAAACACATTAAGGTTTGGTGTCCAAGACCACC
2842 67_HRV34    AATAACAACTAGAGTTTATCACAAAGCTAAACATGTAAAAACCTGGTGTCCAAGACCACC
2843 68_HRV34b|  AATAACAACTAGAGTTTATCACAAAGCTAAACATGTAAAAACCTGGTGTCCAAGACCACC
2844 69_HRV34a|  AATAACAACTAGAGTTTATCACAAAGCTAAACATGTAAAAACCTGGTGTCCAAGACCACC
2845 70_HRV50a|  AATCACAACCAGAGTATACCATAAAGCCAAACACATAAAAGTCTGGTGTCCAAGACCACC
2846 71_HRV50b|  AATCACAACCAGAGTATACCATAAAGCCAAACACATAAAAGTCTGGTGTCCAAGACCACC
2847 72_HRV50    AATCACAACCAGAGTATACCATAAAGCCAAACACATAAAAGTCTGGTGTCCAAGACCACC
2848 73_HRV18a|  AATAACAACCAGAATATACCACAAGGCAAAACATGTTAAAGCATGGTGCCCAAGGCCACC
2849 74_HRV18b|  AATAACAACCAGAATATACCACAAGGCAAAACATGTTAAAGCATGGTGCCCAAGGCCACC
2850 75_HRV18    AATAACAACCAGAATATACCACAAGGCAAAACATGTTAAAGCATGGTGCCCAAGGCCACC
2851 76_HRV55    AGTGACGACAAGAGTCTATCATAAAGCTAAACACATCAAAGCATGGTGCCCCACGACCACC
2852 77_HRV55b|  AGTGACGACAAGAGTCTATCATAAAGCTAAACACATCAAAGCATGGTGCCCACGACCACC
2853 78_HRV55a|  AGTGACGACAAGAGTCTATCATAAAGCTAAACACATCAAAGCATGGTGCCCACGACCACC
2854 79_HRV57    AATAACAACCAGAGTGTATCACAAAGCCAAACATGTCAAAGCCTGGTGCCCTAGACCACC
2855 80_HRV57a|  AATAACAACCAGAGTATCACAAAGCCAAACATGTCAAAGCCTGGTGCCCTAGACCACC
2856 81_HRV57b|  AATAACAACCAGAGTGTATCACAAAGCCAAACATGTCAAAGCCTGGTGCCCTAGACCACC
2857 82_HRV21    AGTGACCACAAGAATATACCATAAGGCAAAGCATGTTAAAGCTTGGTGCCCCAGACCACC
2858 83_HRVHan   AGTGACCACAAGAATATACCATAAAGCAAAGCATGTTAAAGCTTGGTGCCCTAGACCACC
2859 84_HRV43    GATAACTACCAGGATATATCATAAAGCCAAGCATATCAAAGCTTGGTGCCCAAGACCACC
2860 85_HRV43b|  GATAACTACCAGGATATATCATAAAGCCAAGCATATCAAAGCTTGGTGCCCAAGACCACC
```

FIG. D6 CONT'D

```
02.trace                                                                    9/20/2007 4:59 PM 2861  86_HRV43a|    GATAACTACCAGGATATATCATAAAGCCAAGCATATCAAAGCTTGGTGCCCAAGACCACC
2862  87_HRV75      AGTAACCACTAGAATATATCACAAAGCCAAACATATAAAAGCTTGGTGTCCGAGGCCGCC
2863  88_HRV75b|    AGTAACCACTAGAATATATCACAAAGCCAAACATATAAAAGCTTGGTGTCCGAGGCCGCC
2864  89_HRV75a|    AGTAACCACTAGAATATATCACAAAGCCAAACATATAAAAGCTTGGTGTCCGAGGCCGCC
2865  96_HRV9a|d    AATTTCAACCAGAATATATCACAAAGCCAAACATGTTAAAGCCTGGTGCCCAAGACCTCC
2866  97_HRV9b|d    AATTTCAACCAGAATATATCACAAAGCCAAACATGTTAAAGCCTGGTGCCCAAGACCTCC
2867  98_HRV9       AATTTCAACCAGAATATATCACAAAGCCAAACATGTTAAAGCCTGGTGCCCAAGACCTCC
2868  99_HRV32      TATTTCAACTAGGGTATATCACAAAGCTAAACACGTCAAAGCTTGGTGCCCACGACCACC
2869  100_HRV32a    TATTTCAACTAGGGTATATCACAAAGCTAAACACGTCAAAGCTTGGTGCCCACGACCACC
2870  101_HRV32b    TATTTCAACTAGGGTATATCACAAAGCTAAACACGTCAAAGCTTGGTGCCCACGACCACC
2871  102_HRV67     AATTGCAACGCGGGTGTATCATAAGGCTAAACATGTAAAAGCTTGGTGCCCAAGGCCCCC
2872  103_HRV67a    AATTGCAACGCGGGTGTATCATAAGGCTAAACATGTAAAAGCTTGGTGCCCAAGGCCCCC
2873  104_HRV67b    AATTGCAACGCGGGTGTATCATAAGGCTAAACATGTAAAAGCTTGGTGCCCAAGGCCCCC
2874  105_HRV15     GATTACAACTAGAGTGTATCACAAAGCTAAACATGTAAAGGCTTGGTGCCCCAGACCCCC
2875  106_HRV15a    GATTACAACTAGAGTGTATCACAAAGCTAAACATGTAAAGGCTTGGTGCCCCAGACCCCC
2876  107_HRV15b    GATTACAACTAGAGTGTATCACAAAGCTAAACATGTAAAGGCTTGGTGCCCCAGACCCCC
2877  108_HRV74a    AATTACAACTAGAGTGTACCATAAAGCAAAGCATGTGAAGGCATGGTGTCCTAGACCCCC
2878  109_HRV74b    AATTACAACTAGAGTGTACCATAAAGCAAAGCATGTGAAGGCATGGTGTCCTAGACCCCC
2879  110_HRV74     AATTACAACTAGAGTGTACCATAAAGCAAAGCATGTGAAGGCATGGTGTCCTAGACCCCC
2880  111_HRV38a    GATAACAACTAGAATTTATCATAAGGCAAAACATGTAAAAGCCTGGTGTCCAAGACCCCC
2881  112_HRV38b    GATAACAACTAGAATTTATCATAAGGCAAAACATGTAAAAGCCTGGTGTCCAAGACCCCC
2882  113_HRV38     GATAACAACTAGAATTTATCATAAGGCAAAACATGTAAAAGCCTGGTGTCCAAGACCCCC
2883  114_HRV60     CGTCGCAACAAGAATATATCATAAAGCAAAGCATGTTAAGGCTTGGTGTCCAAGACCTCC
2884  115_HRV60a    CGTCGCAACAAGAATATATCATAAAGCAAAGCATGTTAAGGCTTGGTGTCCAAGACCTCC
2885  116_HRV60b    CGTCGCAACAAGAATATATCATAAAGCAAAGCATGTTAAGGCTTGGTGTCCAAGACCTCC
2886  117_HRV64a    CATCACTACTAGGGTTTATCACAAAGCAAAACATGTCAAGGCATGGTGTCCACGGCCCCC
2887  118_HRV64b    CATCACTACTAGGGTTTATCACAAAGCAAAACATGTCAAGGCATGGTGTCCACGGCCCCC
2888  119_HRV64     CATCACTACTAGGGTTTATCACAAAGCAAAACATGTCAAGGCATGGTGTCCACGGCCCCC
2889  120_HRV94a    CATCACTACTAGAGTGTACCACAAAGCAAAACATGTGAAAGCGTGGTGCCCGCGCCCTCC
2890  121_HRV94b    CATCACTACTAGAGTGTACCACAAAGCAAAACATGTGAAAGCGTGGTGCCCGCGCCCTCC
2891  122_HRV94     CATCACTACTAGAGTGTACCACAAAGCAAAACATGTGAAAGCGTGGTGCCCGCGCCCTCC
2892  123_HRV22     AATTACAACTAGAGTGTACCACAAAGCAAAACATGTAAAGGCATGGTGCCCACGTCCTCC
2893  124_HRV22a    AATTACAACTAGAGTGTACCACAAAGCAAAACATGTAAAGGCATGGTGCCCACGTCCTCC
2894  125_HRV22b    AATTACAACTAGAGTGTACCACAAAGCAAAACATGTAAAGGCATGGTGCCCACGTCCTCC
2895  126_HRV82     CATTACCACAAGAATATATCACAAAGCAAAACATGTGAAAGCGTGGTGTCCACGACCCCC
2896  127_HRV82b    CATTACCACAAGAATATATCACAAAGCAAAACATGTGAAAGCGTGGTGTCCACGACCCCC
2897  128_HRV82a    CATTACCACAAGAATATATCACAAAGCAAAACATGTGAAAGCGTGGTGTCCACGACCCCC
2898  129_HRV19     AATCACAACTAGAGTATATCATAAAGCTAAACATATAAAAGCTTGGTGCCCACGACCACC
2899  130_HRV19a    AATCACAACTAGAGTATATCATAAAGCTAAACATATAAAAGCTTGGTGCCCACGACCACC
2900  131_HRV19b    AATCACAACTAGAGTATATCATAAAGCTAAACATATAAAAGCTTGGTGCCCACGACCACC
2901  132_HRV13     GGTTACAACTAGAATCTATCATAAAGCTAAACATGTCAAAGCATGGTGTCCTAGACCTCC
2902  133_HRV13a    GGTTACAACTAGAATCTATCATAAAGCTAAACATGTCAAAGCATGGTGTCCTAGACCTCC
2903  134_HRV13b    GGTTACAACTAGAATCTATCATAAAGCTAAACATGTCAAAGCATGGTGTCCTAGACCTCC
2904  135_HRV41     GGTCACAACTAGAGTTTACCACAAAGCTAAACATGTTAAAGCATGGTGTCCTAGACCTCC
2905  136_HRV41a    GGTCACAACTAGAGTTTACCACAAAGCTAAACATGTTAAAGCATGGTGTCCTAGACCTCC
2906  137_HRV41b    GGTCACAACTAGAGTTTACCACAAAGCTAAACATGTTAAAGCATGGTGTCCTAGACCTCC
2907  138_HRV73     GGTTACTACTAGAATCTATCATAAAGCTAAACATGTTAAAGCTTGGTGTCCAAGACCTCC
2908  139_HRV73b    GGTTACTACTAGAATCTATCATAAGGCTAAACATGTTAAAGCTTGGTGTCCAAGACCTCC
2909  140_HRV73a    GGTTACTACTAGAATCTATCATAAGGCTAAACATGTTAAAGCTTGGTGTCCAAGACCTCC
2910  141_HRV61     AATCACAACTAGGATTTACCATAAAGCTAAACATGTTAAAGTCTGGTGTCCTAGACCCCC
2911  142_HRV61a    AATCACAACTAGGATTTACCATAAAGCTAAACATGTTAAAGTCTGGTGTCCTAGACCCCC
2912  143_HRV61b    AATCACAACTAGGATTTACCATAAAGCTAAACATGTTAAAGTCTGGTGTCCTAGACCCCC
2913  144_HRV96     AATTACAACCAGAGTTTACCACAAAGCTAAACATGTTAAGGTGTGGTGCCCGAGACCCCC
2914  145_HRV96b    AATTACAACCAGAGTTTACCACAAAGCTAAACATGTTAAGGTGTGGTGCCCGAGACCCCC
2915  146_HRV96a    AATTACAACCAGAGTTTACCACAAAGCTAAACATGTTAAGGTGTGGTGCCCGAGACCCCC
2916  90_HRV16a|    AGTGGTAACAAGGATATATCACAAAGCCAAACACACCAAAGCTTGGTGCCCAAGACCACC
2917  91_HRV16b|    AGTGGTAACAAGGATATATCACAAAGCCAAACACACCAAAGCTTGGTGCCCAAGACCACC
2918  92_1AYM_A     AGTGGTAACAAGGATATATCACAAAGCCAAACACACCAAAGCTTGGTGCCCAAGACCACC
2919  93_HRV81a|    AATAGTAACAAGAATATATCACAAAGCTAAGCACACCAAAGCTTGGTGTCCAAGACCACC
2920  94_HRV81b|    AATAGTAACAAGAATATATCACAAAGCTAAGCACACCAAAGCTTGGTGTCCAAGACCACC
2921  95_HRV81      AATAGTAACAAGAATATATCACAAAGCTAAGCACACCAAAGCTTGGTGTCCAAGACCACC
2922  147_HRV2      TATAATGACAAGAATCTATCACAAGGCTAAACATGTCAAGGCATGGTGTCCACGCCCACC
2923  148_HRV2a|    TATAATGACAAGAATCTATCACAAGGCTAAACATGTCAAGGCATGGTGTCCACGCCCACC
2924  149_HRV2b|    TATAATGACAAGAATCTATCACAAGGCTAAACATGTCAAGGCATGGTGTCCACGCCCACC
2925  150_HRV49a    TATCATGACAAGAATCTATCATAAAGCTAAACACGTCAAAGCATGGTGTCCGCGCCCACC
```

FIG. D6 CONT'D 02.trace                                                                                    9/20/2007 4:59 PM

```
2926 151_HRV49b     TATCATGACAAGAATCTATCATAAAGCTAAACACGTCAAAGCATGGTGTCCGCGCCCACC
2927 152_HRV49      TATCATGACAAGAATCTATCATAAAGCTAAACACGTCAAAGCATGGTGTCCGCGCCCACC
2928 153_HRV23a     GATAATGACAAGGGTCTACCACAAAGCTAAACATGTCAAAGCATGGTGTCCGCGGCCACC
2929 154_HRV23b     GATAATGACAAGGGTCTACCACAAAGCTAAACATGTCAAAGCATGGTGTCCGCGGCCACC
2930 155_HRV23      GATAATGACAAGGGTCTACCACAAAGCTAAACATGTCAAAGCATGGTGTCCGCGGCCACC
2931 156_HRV30a     CATAATGACAAGGGTCTACCACAAGGCTAAACATGTCAAAGCGTGGTGTCCACGGCCACC
2932 157_HRV30b     CATAATGACAAGGGTCTACCACAAGGCTAAACATGTCAAAGCGTGGTGTCCACGGCCACC
2933 158_HRV30      CATAATGACAAGGGTCTACCACAAGGCTAAACATGTCAAAGCGTGGTGTCCACGGCCACC
2934 159_HRV7       GATTGTGAGTCGCATTTACCACAAAGCCAAACATATAAAAGCATGGTGCCCACGCCCACC
2935 160_HRV7b|     GATTGTGAGTCGCATTTACCACAAAGCCAAACATATAAAAGCATGGTGCCCACGCCCACC
2936 161_HRV7a|     GATTGTGAGTCGCATTTACCACAAAGCCAAACATATAAAAGCATGGTGCCCACGCCCACC
2937 162_HRV88      TATCATTAGCCGTATATATCACAAGGCTAAACATATAAAGGCATGGTGTCCACGCCCACC
2938 163_HRV88a     TATCATTAGCCGTATATATCACAAGGCTAAACATATAAAGGCATGGTGTCCACGCCCACC
2939 164_HRV88b     TATCATTAGCCGTATATATCACAAGGCTAAACATATAAAGGCATGGTGTCCACGCCCACC
2940 165_HRV36a     TATTGTATGCCGCATTTATCATAAAGCTAAACACATAAAGGCCTGGTGCCCGCGTCCACC
2941 166_HRV36b     TATTGTATGCCGCATTTATCATAAAGCTAAACACATAAAGGCCTGGTGCCCGCGTCCACC
2942 167_HRV36      TATTGTATGCCGCATTTATCATAAAGCTAAACACATAAAGGCCTGGTGCCCGCGTCCACC
2943 168_HRV89a     TATTGTGTGCCGCATTTACCACAAGGCCAAACATATAAAAGCATGGTGTCCTCGCCCACC
2944 169_HRV89b     TATTGTGTGCCGCATTTACCACAAGGCCAAACATATAAAAGCATGGTGTCCTCGCCCACC
2945 170_HRV89      TATTGTGTGCCGCATTTACCACAAGGCCAAACATATAAAAGCATGGTGTCCTCGCCCACC
2946 171_HRV58      CATTGTCTGTCGCATTTACCACAAAGCCAAGCATATAAAAGCATGGTGTCCACGCCCACC
2947 172_HRV58a     CATTGTCTGTCGCATTTACCACAAAGCCAAGCATATAAAAGCATGGTGTCCACGCCCACC
2948 173_HRV58b     CATTGTCTGTCGCATTTACCACAAAGCCAAGCATATAAAAGCATGGTGTCCACGCCCACC
2949 174_HRV12a     GATTACCAGTAGAATATACCATAAAGCAAAACATATCAGTGCCTGGGGCCCTAGACCACC
2950 175_HRV12b     GATTACCAGTAGAATATACCATAAAGCAAAACATATCAGTGCCTGGGGCCCTAGACCACC
2951 176_HRV12      GATTACCAGTAGAATATACCATAAAGCAAAACATATCAGTGCCTGGGGCCCTAGACCACC
2952 177_HRV78a     AATTACAGCTAGAGTCTACCACAAGGCCAAACATATTAGTGCATGGGGCCCAAGACCTCC
2953 178_HRV78b     AATTACAGCTAGAGTCTACCACAAGGCCAAACATATTAGTGCATGGGGCCCAAGACCTCC
2954 179_HRV78      AATTACAGCTAGAGTCTACCACAAGGCCAAACATATTAGTGCATGGGGCCCAAGACCTCC
2955 180_HRV20      GATAACCAGTAGGATATTCCACAAGGCAAAGCATATTAGTGCATGGTGTCCAAGGGCCCC
2956 181_HRV20a     GATAACCAGTAGGATATTCCACAAGGCAAAGCATATTAGTGCATGGTGTCCAAGGGCCCC
2957 182_HRV20b     GATAACCAGTAGGATATTCCACAAGGCAAAGCATATTAGTGCATGGTGTCCAAGGGCCCC
2958 183_HRV68      AATAACCAGCAGAATATTCCATAAAGCAAAACATATTAGTGCGTGGTGTCCAAGAGCTCC
2959 184_HRV68a     AATAACCAGCAGAATATTCCATAAAGCAAAACATATTAGTGCGTGGTGTCCAAGAGCTCC
2960 185_HRV68b     AATAACCAGCAGAATATTCCATAAAGCAAAACATATTAGTGCGTGGTGTCCAAGAGCTCC
2961 186_HRV28      AATAACCAGCATAATATTCCACAAAGCTAAACATGTCAGTGCATGGTGCCCCAGACCTCC
2962 187_HRV28a     AATAACCAGCATAATATTCCACAAAGCTAAACATGTCAGTGCATGGTGCCCCAGACCTCC
2963 188_HRV28b     AATAACCAGCATAATATTCCACAAAGCTAAACATGTCAGTGCATGGTGCCCCAGACCTCC
2964 189_HRV53a     GATAACCAGTAGGATTTATCACAAGGCTAAACATATCAGTGCATGGTGTCCAAGACCACC
2965 190_HRV53b     GATAACCAGTAGGATTTATCACAAGGCTAAACATATCAGTGCATGGTGTCCAAGACCACC
2966 191_HRV53      GATAACCAGTAGGATTTATCACAAGGCTAAACATATCAGTGCATGGTGTCCAAGACCACC
2967 192_HRV46a     TATAACTAGCAGAATATATCACAAGGCTAAACACATTAAAGCATGGTGCCCCAGGGCACC
2968 193_HRV46b     TATAACTAGCAGAATATATCACAAGGCTAAACACATTAAAGCATGGTGCCCCAGGGCACC
2969 194_HRV46      TATAACTAGCAGAATATATCACAAGGCTAAACACATTAAAGCATGGTGCCCCAGGGCACC
2970 195_HRV80a     AATCACCAGCAGAATATATCACAAAGCTAAACACATCAAAGCATGGTGTCCAAGAGCACC
2971 196_HRV80b     AATCACCAGCAGAATATATCACAAAGCTAAACACATCAAAGCATGGTGTCCAAGAGCACC
2972 197_HRV80      AATCACCAGCAGAATATATCACAAAGCTAAACACATCAAAGCATGGTGTCCAAGAGCACC
2973 198_HRV51      CATAACTAGCAGGATTTACCACAAAGCCAAACATGTCAGTGCATGGTGCCCTCGTCCTCC
2974 199_HRV51a     CATAACTAGCAGGATTTACCACAAAGCCAAACATGTCAGTGCATGGTGCCCTCGTCCTCC
2975 200_HRV51b     CATAACTAGCAGGATTTACCACAAAGCCAAACATGTCAGTGCATGGTGCCCTCGTCCTCC
2976 201_HRV65a     CATAACCAGTAGAATATATCATAAAGCTAAACACATCAGTGCTTGGTGTCCACGACCTCC
2977 202_HRV65b     CATAACCAGTAGAATATATCATAAAGCTAAACACATCAGTGCTTGGTGTCCACGACCTCC
2978 203_HRV65      CATAACCAGTAGAATATATCATAAAGCTAAACACATCAGTGCTTGGTGTCCACGACCTCC
2979 204_HRV71a     CATAACAAGTAGGATTTATCACAAAGCCAAACATGTCAGAGCATGGTGTCCTAGACCCCC
2980 205_HRV71b     CATAACAAGTAGGATTTATCACAAAGCCAAACATGTCAGAGCATGGTGTCCTAGACCCCC
2981 206_HRV71      CATAACAAGTAGGATTTATCACAAAGCCAAACATGTCAGAGCATGGTGTCCTAGACCCCC
2982 207_HRV8       AATTGATTCAAGAATACCTGAAAGCAAAGCACATTAAAGCTTGGTGTCCTAGACCCCC
2983 208_HRV95      AATTGATTCAAGAATATACCTGAAAGCAAAGCATATTAAAGCTTGGTGTCCTAGACCCCC
2984 209_HRV45      GATCGACTCCATGGTATATCTAAAAGCTAAACACATCAAGGCATGGTGTCCCAGACCTCC
2985 210_HRV45a     GATCGACTCCATGGTATATCTAAAAGCTAAACACATCAAGGCATGGTGTCCCAGACCTCC
2986 211_HRV45b     GATCGACTCCATGGTATATCTAAAAGCTAAACACATCAAGGCATGGTGTCCCAGACCTCC
2987 GROUP_1        --T----------T-T--C--AA-GC-AA-CA---------TGG-G-CC--G--C-C-
2988
2989 1_HRV1A1|d     TAGAGCTGTCCCTTACACA-CATAGTCATGTGACTAATTATATGC-CAGAAA---CAGGT
2990 2_HRV1A2|d     TAGAGCTGTCCCTTACACA-CATAGTCATGTGACTAATTATATGC-CAGAAA---CAGGT
```

FIG. D6 CONT'D

```
02.trace                                                                    9/20/2007 4:59 PM 2991  3_HRV1A|cD    TAGAGCTGTCCCTTACACA-CATAGTCATGTGACTAATTATATGC-CAGAAA---CAGGT
2992  4_HRV1B1|d    TAGAGCTGTTCCTTACACA-CATAGTCGTGTAACTAATTATGTAC-CAAAAA---CAGGT
2993  5_HRV1B2|d    TAGAGCTGTTCCTTACACA-CATAGTCGTGTAACTAATTATGTAC-CAAAAA---CAGGT
2994  6_HRV1B       TAGAGCTGTTCCTTACACA-CATAGTCGTGTAACTAATTATGTAC-CAAAAA---CAGGT
2995  7_HRV40a|d    AAGAGCAGTACCTTACACA-CATACACACTCAACAAATTATAAAC-CTCAAG---AAGGT
2996  8_HRV40b|d    AAGAGCAGTACCTTACACA-CATACACACTCAACAAATTATAAAC-CTCAAG---AAGGT
2997  9_HRV40       AAGAGCAGTACCTTACACA-CATACACACTCAACAAATTATAAAC-CTCAAG---AAGGT
2998  10_HRV85      AAGAGCGGTGCCTTATACA-CACACACGCTCAACCAACTATGTGC-CACAAG---ATGGT
2999  11_HRV85a|    AAGAGCGGTGCCTTATACA-CACACACGCTCAACCAACTATGTGC-CACAAG---ATGGT
3000  12_HRV85b|    AAGAGCGGTGCCTTATACA-CACACACGCTCAACCAACTATGTGC-CACAAG---ATGGT
3001  13_HRV56a|    AAGGGCTGTGCCTTATACA-CATGCTCACGTCACCAATTATAAAC-CACAAG---ATGGT
3002  14_HRV56b|    AAGGGCTGTGCCTTATACA-CATGCTCACGTCACCAATTATAAAC-CACAAG---ATGGT
3003  15_HRV56      AAGGGCTGTGCCTTATACA-CATGCTCACGTCACCAATTATAAAC-CACAAG---ATGGT
3004  16_HRV54      TAGGGCTGTCCCATACACA-CATACTAGATCAACAAATTACATGC-CACGGG---AGGGT
3005  17_HRV98      TAGAGCTGTTCCATACACA-CACACTAGATCAACTAATTACATGC-CTCAAG---ATGGT
3006  18_HRV59a|    TAGAGCAGTCCCTTACACA-CACAGCTACGTAACTAACTACAAGATTGCTGG---AAAA-
3007  19_HRV59b|    TAGAGCAGTCCCTTACACA-CACAGCTACGTAACTAACTACAAGATTGCTGG---AAAA-
3008  20_HRV59      TAGAGCAGTCCCTTACACA-CACAGCTACGTAACTAACTACAAGATTGCTGG---AAAA-
3009  21_HRV63      TAGGGCTGTTCCATACACA-CATAGTTATGTCACTAACTATAAAATTACAGG---ACAG-
3010  22_HRV63b|    TAGGGCTGTTCCATACACA-CATAGTTATGTCACTAACTATAAAATTACAGG---ACAG-
3011  23_HRV63a|    TAGGGCTGTTCCATACACA-CATAGTTATGTCACTAACTATAAAATTACAGG---ACAG-
3012  24_HRV39      CAGAGCAGTCCCTTACACA-CACAGCAATGTTACAAATTACAAAG-TACGGG---ACGGT
3013  25_HRV39a|    CAGAGCAGTCCCTTACACA-CACAGCAATGTTACAAATTACAAAG-TACGGG---ACGGT
3014  26_HRV39b|    CAGAGCAGTCCCTTACACA-CACAGCAATGTTACAAATTACAAAG-TACGGG---ACGGT
3015  27_HRV10a|    CAGAGCTGTACCATATACA-CATGCCCATTCCACAAATTACAAAC-CACATG---GCAAA
3016  28_HRV10b|    CAGAGCTGTACCATATACA-CATGCCCATTCCACAAATTACAAAC-CACATG---GCAAA
3017  29_HRV10      CAGAGCTGTACCATATACA-CATGCCCATTCCACAAATTACAAAC-CACATG---GCAAA
3018  30_HRV100a    TCGGGCTGTGCCGTACACA-CATAGTCACTCTACAAATTACAAAC-CACATG---AGGGT
3019  31_HRV100b    TCGGGCTGTGCCGTACACA-CATAGTCACTCTACAAATTACAAAC-CACATG---AGGGT
3020  32_HRV100     TCGGGCTGTGCCGTACACA-CATAGTCACTCTACAAATTACAAAC-CACATG---AGGGT
3021  33_HRV66      TAGAGCTGTACCATACACA-ACTGTAAACTCAACCAATTATATGC-CTCATA---CTGGT
3022  34_HRV66b|    TAGAGCTGTACCATACACA-ACTGTAAACTCAACCAATTATATGC-CTCATA---CTGGT
3023  35_HRV66a|    TAGAGCTGTACCATACACA-ACTGTAAACTCAACCAATTATATGC-CTCATA---CTGGT
3024  36_HRV77a|    TAGAGCTGTACCATACACA-GCAGTAGATTCAACAAATTACAAAC-CTATGA---GAGGG
3025  37_HRV77b|    TAGAGCTGTACCATACACA-GCAGTAGATTCAACAAATTACAAAC-CTATGA---GAGGG
3026  38_HRV77      TAGAGCTGTACCATACACA-GCAGTAGATTCAACAAATTACAAAC-CTATGA---GAGGG
3027  39_HRV62a     CAGAGCTGTTCCATATAAA-TATGTTGATTTCAATAATTATGCAG-CCAGTG---ATAGT
3028  40_HRV62b     TAGAGCTGTTCCATATAAA-TATGTTGATTTCAATAATTATGCAG-CCAGTG---ATAGT
3029  41_HRV25      TAGAGCTGTCCCATATAAA-TATGTTGACTTCAATAATTATGCAG-CCAGTG---ATAAT
3030  42_HRV29a     AAGAGTTGTCCCATACAAG-TATGTTGGCCTAACTAATTACACAC-TTAAAG---AAGAA
3031  43_HRV29b     AAGAGTTGTCCCATACAAG-TATGTTGGCCTAACTAATTACACAC-TTAAAG---AAGAA
3032  44_HRV44a     AAGGGTTGTCCCATACAAG-TATGTTGGCCTAACTAATTACACAC-TTAAAG---AAACA
3033  45_HRV44b     AAGGGTTGTCCCATACAAG-TATGTTGGCCTAACTAATTACACAC-TTAAAG---AAACA
3034  46_HRV31      TAGAGCAGTTCCATACAGGGTATG-TGGATCAACAAACTACAAAC-CTGATG---AAAAT
3035  47_HRV31a|    TAGAGCAGTTCCATACAGGGTATG-TGGATCAACAAACTACAAAC-CTGATG---AAAAT
3036  48_HRV31b|    TAGAGCAGTTCCATACAGG-TATGTTGGATCAACAAACTACAAAC-CTGATG---AAAAT
3037  49_HRV47      TAGAGCTGTTCCATATAGA-TATGTTGGATCAACAAATTACAAAC-CTGATC---AAGGA
3038  50_HRV47a|    TAGAGCTGTTCCATATAGA-TATGTTGGATCAACAAATTACAAAC-CTGATC---AAGGA
3039  51_HRV47b|    TAGAGCTGTTCCATATAGA-TATGTTGGATCAACAAATTACAAAC-CTGATC---AAGGA
3040  52_HRV11      TAGAGCTGTAGAATATACT-CACACTCATGTAACCAATTACAAAC-CACAGG---AAGGA
3041  53_HRV11b|    TAGAGCTGTAGAATATACT-CACACTCATGTAACCAATTACAAAC-CACAGG---AAGGA
3042  54_HRV11a|    TAGAGCTGTAGAATATACT-CACACTCATGTAACCAATTACAAAC-CACAGG---AAGGA
3043  55_HRV76      TAGAGCTGTAGAGTATACA-TACACCCATGTAACAAACTACAAAC-CACATT---CTGGT
3044  56_HRV76b|    TAGAGCTGTAGAGTATACA-TACACCCATGTAACAAACTACAAAC-CACATT---CTGGT
3045  57_HRV76a|    TAGAGCTGTAGAGTATACA-TACACCCATGTAACAAACTACAAAC-CACATT---CTGGT
3046  58_HRV33      TAGAGCTGTGGAATACACC-CATACTCATGTTACAAATTATAAAT-CAACAA---CTCGT
3047  59_HRV33b|    TAGAGCTGTGGAATACACC-CATACTCATGTTACAAATTATAAAT-CAACAA---CTCGT
3048  60_HRV33a|    TAGAGCTGTGGAATACACC-CATACTCATGTTACAAATTATAAAT-CAACAA---CTCGT
3049  61_HRV24a|    CAGAGCTGTTGAGTATACA-CATACTCACGTGACCAATTATAAGC-ATCAGA---CTCGT
3050  62_HRV24b|    CAGAGCTGTTGAGTATACA-CATACTCACGTGACCAATTATAAGC-ATCAGA---CTCGT
3051  63_HRV24      CAGAGCTGTTGAGTATACA-CATACTCACGTGACCAATTATAAGC-ATCAGA---CTCGT
3052  64_HRV90      TAGGGCAGTTGAATACACA-CACACTCATGTAACAAACTACAAAC-ATGCAA---CACGT
3053  65_HRV90a|    TAGGGCAGTTGAATACACA-CACACTCATGTAACAAACTACAAAC-ATGCAA---CACGT
3054  66_HRV90b|    TAGGGCAGTTGAATACACA-CACACTCATGTAACAAACTACAAAC-ATGCAA---CACGT
3055  67_HRV34      AAGAGCTGTTGAGTACACA-CACACACATGTTACTAACTACAAAG-TTAGGG---GTAAA
```

FIG. D6 CONT'D 02.trace						9/20/2007 4:59 PM

```
3056  68_HRV34b|   AAGAGCTGTTGAGTACACA-CACACACATGTTACTAACTACAAAG-TTAGGG---GTAAA
3057  69_HRV34a|   AAGAGCTGTTGAGTACACA-CACACACATGTTACTAACTACAAAG-TTAGGG---GTAAA
3058  70_HRV50a|   AAGAGCTGTTGAATACACA-CACACCCATGTCACTAACTACAAGA-AAAGTG---ATGCT
3059  71_HRV50b|   AAGAGCTGTTGAATACACA-CACACCCATGTCACTAACTACAAGA-AAAGTG---ATGCT
3060  72_HRV50    AAGAGCTGTTGAATACACA-CACACCCATGTCACTAACTACAAGA-AAAGTG---ATGCT
3061  73_HRV18a|   GAGAGCTGTGGAGTACACA-CATACACATGTAACTAACTACAAGC-CTAAGG---AAGGA
3062  74_HRV18b|   GAGAGCTGTGGAGTACACA-CATACACATGTAACTAACTACAAGC-CTAAGG---AAGGA
3063  75_HRV18    GAGAGCTGTGGAGTACACA-CATACACATGTAACTAACTACAAGC-CTAAGG---AAGGA
3064  76_HRV55    TAGGGCTGTTGAATACACA-CACACACATGTCACAAATTACAAGA-AGACTG---ATGGC
3065  77_HRV55b|   TAGGGCTGTTGAATACACA-CACACACATGTCACAAATTACAAGA-AGACTG---ATGGC
3066  78_HRV55a|   TAGGGCTGTTGAATACACA-CACACACATGTCACAAATTACAAGA-AGACTG---ATGGC
3067  79_HRV57    ACGGGCTATCGAGTACACA-CATACACATGTTACTAATTATAAAA-TAAAAG---ATAGA
3068  80_HRV57a|   ACGGGCTATCGAGTACACA-CATACACATGTTACTAATTATAAAA-TAAAAG---ATAGA
3069  81_HRV57b|   ACGGGCTATCGAGTACACA-CATACACATGTTACTAATTATAAAA-TAAAAG---ATAGA
3070  82_HRV21    GAGGGCCGTTGAATACACA-CATACACACGTAACCAATTACAAAA-TTGCAA---ATCAT
3071  83_HRVHan   GAGGGCCGTTGAATACACA-CATACACATGTAACCAATTACAAAA-TTGCAA---ATAAA
3072  84_HRV43    CAGAGCTGTTGAATACACA-CACACACATGTCACAAATTATAAAA-GAGAAG---GAAAG
3073  85_HRV43b|   CAGAGCTGTTGAATACACA-CACACACATGTCACAAATTATAAAA-GAGAAG---GAAAG
3074  86_HRV43a|   CAGAGCTGTTGAATACACA-CACACACATGTCACAAATTATAAAA-GAGAAG---GAAAG
3075  87_HRV75    CAGGGCTGTTGAATACACA-TTTAGACGTGTAACAAATTACAAAA-GAGATG---GACAA
3076  88_HRV75b|   CAGGGCTGTTGAATACACA-TTTAGACGTGTAACAAATTACAAAA-GAGATG---GACAA
3077  89_HRV75a|   CAGGGCTGTTGAATACACA-TTTAGACGTGTAACAAATTACAAAA-GAGATG---GACAA
3078  96_HRV9a|d   TAGGGCAGTTGAGTATATA-CATACACATGTCACAAATTACAAGC-CAAGCA---CAGGC
3079  97_HRV9b|d   TAGGGCAGTTGAGTATATA-CATACACATGTCACAAATTACAAGC-CAAGCA---CAGGC
3080  98_HRV9     TAGGGCAGTTGAGTATATA-CATACACATGTCACAAATTACAAGC-CAAGCA---CAGGC
3081  99_HRV32    TAGGGCAGTTGAATATACA-CATACACATGTTACAAATTACAAAC-CAAGCA---CAGGT
3082 100_HRV32a   TAGGGCAGTTGAATATACA-CATACACATGTTACAAATTACAAAC-CAAGCA---CAGGT
3083 101_HRV32b   TAGGGCAGTTGAATATACA-CATACACATGTTACAAATTACAAAC-CAAGCA---CAGGT
3084 102_HRV67    TAGAGCAGTTGAATACATA-CACACACATGTTACAAACTATAGAC-CAGAAA---CAGGT
3085 103_HRV67a   TAGAGCAGTTGAATACATA-CACACACATGTTACAAACTATAGAC-CAGAAA---CAGGT
3086 104_HRV67b   TAGAGCAGTTGAATACATA-CACACACATGTTACAAACTATAGAC-CAGAAA---CAGGT
3087 105_HRV15    TAGAGCAGTGGAATATACA-CACACACATGTCACAAATTACAAAC-CACAAG---ATGGT
3088 106_HRV15a   TAGAGCAGTGGAATATACA-CACACACATGTCACAAATTACAAAC-CACAAG---ATGGT
3089 107_HRV15b   TAGAGCAGTGGAATATACA-CACACACATGTCACAAATTACAAAC-CACAAG---ATGGT
3090 108_HRV74a   TAGAGCAGTTGAATATACT-CACACACATGTCACAAATTACAAAC-CACAAG---AAGGT
3091 109_HRV74b   TAGAGCAGTTGAATATACT-CACACACATGTCACAAATTACAAAC-CACAAG---AAGGT
3092 110_HRV74    TAGAGCAGTTGAATATACT-CACACACATGTCACAAATTACAAAC-CACAAG---AAGGT
3093 111_HRV38a   AAGGGCAGTTGAATATAGA-CATACACATGTTAACAATTACAAAC-CAGACC---AAGGG
3094 112_HRV38b   AAGGGCAGTTGAATATAGA-CATACACATGTTAACAATTACAAAC-CAGACC---AAGGG
3095 113_HRV38    AAGGGCAGTTGAATATAGA-CATACACATGTTAACAATTACAAAC-CAGACC---AAGGG
3096 114_HRV60    AAGGGCAGTTGAATATAGA-CACACACATGTAAACAACTATAGAC-CAGATG---ATGGA
3097 115_HRV60a   AAGGGCAGTTGAATATAGA-CACACACATGTAAACAACTATAGAC-CAGATG---ATGGA
3098 116_HRV60b   AAGGGCAGTTGAATATAGA-CACACACATGTAAACAACTATAGAC-CAGATG---ATGGA
3099 117_HRV64a   AAGAGCTGTTGGATATACA-CATACAAATGTCACCAATTATAAAC-CATCCA---AAGGA
3100 118_HRV64b   AAGAGCTGTTGGATATACA-CATACAAATGTCACCAATTATAAAC-CATCCA---AAGGA
3101 119_HRV64    AAGAGCTGTTGGATATACA-CATACAAATGTCACCAATTATAAAC-CATCCA---AAGGA
3102 120_HRV94a   AAGAGCTGTTGGATACACA-CATACGCATGTCACTAATTACAAAC-CATCTG---AAGGG
3103 121_HRV94b   AAGAGCTGTTGGATACACA-CATACGCATGTCACTAATTACAAAC-CATCTG---AAGGG
3104 122_HRV94    AAGAGCTGTTGGATACACA-CATACGCATGTCACTAATTACAAAC-CATCTG---AAGGG
3105 123_HRV22    AAGAGCTGTTGGATATACA-CACACACATGTGACAAACTACAAAC-CATCTG---TAGGG
3106 124_HRV22a   AAGAGCTGTTGGATATACA-CACACACATGTGACAAACTACAAAC-CATCTG---TAGGG
3107 125_HRV22b   AAGAGCTGTTGGATATACA-CACACACATGTGACAAACTACAAAC-CATCTG---TAGGG
3108 126_HRV82    GAGGGCTGTGGGTTATACA-CACACACATGTTACCAACTACAAGC-CATCAC---AGGGA
3109 127_HRV82b   GAGGGCTGTGGGTTATACA-CACACACATGTTACCAACTACAAGC-CATCAC---AGGGA
3110 128_HRV82a   GAGGGCTGTGGGTTATACA-CACACACATGTTACCAACTACAAGC-CATCAC---AGGGA
3111 129_HRV19    CAGAGCCGTGGAATATACC-CACACTCATGTGACTAATTATAAAC-CCCAGA---CAGGT
3112 130_HRV19a   CAGAGCCGTGGAATATACC-CACACTCATGTGACTAATTATAAAC-CCCAGA---CAGGT
3113 131_HRV19b   CAGAGCCGTGGAATATACC-CACACTCATGTGACTAATTATAAAC-CCCAGA---CAGGT
3114 132_HRV13    CAGAGCTGTTGAATATACT-AATGTGCATGTTACAAACTACAAAC-CAGGGA---CAGGA
3115 133_HRV13a   CAGAGCTGTTGAATATACT-AATGTGCATGTTACAAACTACAAAC-CAGGGA---CAGGA
3116 134_HRV13b   CAGAGCTGTTGAATATACT-AATGTGCATGTTACAAACTACAAAC-CAGGGA---CAGGA
3117 135_HRV41    CAGGGCTGTGGAGTACACC-AATGTGCATGTCACAAATTACAAAC-CAAAAG---CAGGA
3118 136_HRV41a   CAGGGCTGTGGAGTACACC-AATGTGCATGTCACAAATTACAAAC-CAAAAG---CAGGA
3119 137_HRV41b   CAGGGCTGTGGAGTACACC-AATGTGCATGTCACAAATTACAAAC-CAAAAG---CAGGA
3120 138_HRV73    TAGGGCAGTAGAATATACA-AATGCACATGTGACCAATTATAAAC-CCACTG---ATGGA
```

FIG. D6 CONT'D 02.trace                                                              9/20/2007 4:59 PM

```
3121  139_HRV73b    TAGGGCAGTAGAATATACA-AATGCACATGTGACCAATTATAAAC-CCACTG---ATGGA
3122  140_HRV73a    TAGGGCAGTAGAATATACA-AATGCACATGTGACCAATTATAAAC-CCACTG---ATGGA
3123  141_HRV61     CAGAGCAGTGGAATATACT-AATGTGCATTTGACCAATTACAAGC-CCAAAG---ATAGT
3124  142_HRV61a    CAGAGCAGTGGAATATACT-AATGTGCATTTGACCAATTACAAGC-CCAAAG---ATAGT
3125  143_HRV61b    CAGAGCAGTGGAATATACT-AATGTGCATTTGACCAATTACAAGC-CCAAAG---ATAGT
3126  144_HRV96     TAGAGCAGTTGAATACACA-AATGTGCATCTCACAAATTATAAAC-CCAACA---ATG--
3127  145_HRV96b    TAGAGCAGTTGAATACACA-AATGTGCATCTCACAAATTATAAAC-CCAACA---ATG--
3128  146_HRV96a    TAGAGCAGTTGAATACACA-AATGTGCATCTCACAAATTATAAAC-CCAACA---ATG--
3129   90_HRV16a|   CAGAGCTGTTCAATACTCA-CATACACATACCACCAACTACAAAT-TGAGTT---CAGAA
3130   91_HRV16b|   CAGAGCTGTTCAATACTCA-CATACACATACCACCAACTACAAAT-TGAGTT---CAGAA
3131   92_1AYM_A    CAGAGCTGTTCAATACTCA-CATACACATACCACCAACTACAAAT-TGAGTT---CAGAA
3132   93_HRV81a|   CAGGGCTGTTCAGTACACA-CATACACATGTAACTAATTATAAAT-TAGAAA---CAGAT
3133   94_HRV81b|   CAGGGCTGTTCAGTACACA-CATACACATGTAACTAATTATAAAT-TAGAAA---CAGAT
3134   95_HRV81     CAGGGCTGTTCAGTACACA-CATACACATGTAACTAATTATAAAT-TAGAAA---CAGAT
3135  147_HRV2      CAGAGCGCTTGAGTATACT-CGTGCTCACCGCACTAATTTTAAAA-TTGAGG---ATAGG
3136  148_HRV2a|    CAGAGCGCTTGAGTATACT-CGTGCTCACCGCACTAATTTTAAAA-TTGAGG---ATAGG
3137  149_HRV2b|    CAGAGCGCTTGAGTATACT-CGTGCTCACCGCACTAATTTTAAAA-TTGAGG---ATAGG
3138  150_HRV49a    CAGAGCACTTGAATATACT-CGCGCTCACCGTACTAATTTCAAAG-TTGAAG---ACAGA
3139  151_HRV49b    CAGAGCACTTGAATATACT-CGCGCTCACCGTACTAATTTCAAAG-TTGAAG---ACAGA
3140  152_HRV49     CAGAGCACTTGAATATACT-CGCGCTCACCGTACTAATTTCAAAG-TTGAAG---ACAGA
3141  153_HRV23a    CAGAGCACTTGAATACACA-CGCGCTCACCGTACTAATTTCAAAA-TTGAAG---GTGAA
3142  154_HRV23b    CAGAGCACTTGAATACACA-CGCGCTCACCGTACTAATTTCAAAA-TTGAAG---GTGAA
3143  155_HRV23     CAGAGCACTTGAATACACA-CGCGCTCACCGTACTAATTTCAAAA-TTGAAG---GTGAA
3144  156_HRV30a    TAGGGCGCTTGAGTATACC-CGTGCTCATCGCACCAATTTTAAAA-TTGATG---GCAGG
3145  157_HRV30b    TAGGGCGCTTGAGTATACC-CGTGCTCATCGCACCAATTTTAAAA-TTGATG---GCAGG
3146  158_HRV30     TAGGGCGCTTGAGTATACC-CGTGCTCATCGCACCAATTTTAAAA-TTGATG---GCAGG
3147  159_HRV7      ACGAGCTGTGCCTTATCAA-CACACTCACTCCACCAACTATGTGC-CACAAA---ATGGA
3148  160_HRV7b|    ACGAGCTGTGCCTTATCAA-CACACTCACTCCACCAACTATGTGC-CACAAA---ATGGA
3149  161_HRV7a|    ACGAGCTGTGCCTTATCAA-CACACTCACTCCACCAACTATGTGC-CACAAA---ATGGA
3150  162_HRV88     AAGAGCCGTACCTTATCAG-CACACACACTCCACCAATTATGTAC-CAACAG---ATGGG
3151  163_HRV88a    AAGAGCCGTACCTTATCAG-CACACACACTCCACCAATTATGTAC-CAACAG---ATGGG
3152  164_HRV88b    AAGAGCCGTACCTTATCAG-CACACACACTCCACCAATTATGTAC-CAACAG---ATGGG
3153  165_HRV36a    AAGGGCCGTTCCTTACCAA-CACACACATTCCACTAATTATATAC-CATACA---AAGGT
3154  166_HRV36b    AAGGGCCGTTCCTTACCAA-CACACACATTCCACTAATTATATAC-CATACA---AAGGT
3155  167_HRV36     AAGGGCCGTTCCTTACCAA-CACACACATTCCACTAATTATATAC-CATACA---AAGGT
3156  168_HRV89a    AAGGGCTGTTGCCTATCAA-CACACACACTCAACCAATTACATAC-CATCCA---ATGGT
3157  169_HRV89b    AAGGGCTGTTGCCTATCAA-CACACACACTCAACCAATTACATAC-CATCCA---ATGGT
3158  170_HRV89     AAGGGCTGTTGCCTATCAA-CACACACACTCAACCAATTACATAC-CATCCA---ATGGT
3159  171_HRV58     AAGGGCTGTTCCTTATCAA-TTCACACATTCTACTAATTACATAC-CAGATA---GTGGT
3160  172_HRV58a    AAGGGCTGTTCCTTATCAA-TTCACACATTCTACTAATTACATAC-CAGATA---GTGGT
3161  173_HRV58b    AAGGGCTGTTCCTTATCAA-TTCACACATTCTACTAATTACATAC-CAGATA---GTGGT
3162  174_HRV12a    AAGAGCTGTACCATACCAG-CATATACACAATCCAAATTACAAGA-CAAGTA------AT
3163  175_HRV12b    AAGAGCTGTACCATACCAG-CATATACACAATCCAAATTACAAGA-CAAGTA------AT
3164  176_HRV12     AAGAGCTGTACCATACCAG-CATATACACAATCCAAATTACAAGA-CAAGTA------AT
3165  177_HRV78a    TAGAGCTGTACCTTATCAG-CACATATATAACCCTAATTATAAAA-CTGAAG------AA
3166  178_HRV78b    TAGAGCTGTACCTTATCAG-CACATATATAACCCTAATTATAAAA-CTGAAG------AA
3167  179_HRV78     TAGAGCTGTACCTTATCAG-CACATATATAACCCTAATTATAAAA-CTGAAG------AA
3168  180_HRV20     AAGAGCAGTGCCTTATCAA-CACACTAAGAGCACAAACTTAGTGC-CAAGGA---CAGGT
3169  181_HRV20a    AAGAGCAGTGCCTTATCAA-CACACTAAGAGCACAAACTTAGTGC-CAAGGA---CAGGT
3170  182_HRV20b    AAGAGCAGTGCCTTATCAA-CACACTAAGAGCACAAACTTAGTGC-CAAGGA---CAGGT
3171  183_HRV68     AAGAGCAGTGCCCTACCAG-CACACCAGAAGTACAAACTTAGTAC-CAAAGG---AAGGT
3172  184_HRV68a    AACAGCAGTGCCCTACCAG-CACACCAGAAGTACAAACTTAGTAC-CAAAGG---AAGGT
3173  185_HRV68b    AAGAGCAGTGCCCTACCAG-CACACCAGAAGTACAAACTTAGTAC-CAAAGG---AAGGT
3174  186_HRV28     ACGCGCTGTAGCTTATCAA-CATACATACAGTCCAAACTTTGTGC-CTCAGG---AAGGT
3175  187_HRV28a    ACGCGCTGTAGCTTATCAA-CATACATACAGTCCAAACTTTGTGC-CTCAGG---AAGGT
3176  188_HRV28b    ACGCGCTGTAGCTTATCAA-CATACATACAGTCCAAACTTTGTGC-CTCAGG---AAGGT
3177  189_HRV53a    AAGAGCAGTTGCATATCAA-CACACATATAGCCCAAATTTTGTAC-CGCAAA---CAGGA
3178  190_HRV53b    AAGAGCAGTTGCATATCAA-CACACATATAGCCCAAATTTTGTAC-CGCAAA---CAGGA
3179  191_HRV53     AAGAGCAGTTGCATATCAA-CACACATATAGCCCAAATTTTGTAC-CGCAAA---CAGGA
3180  192_HRV46a    CAGAGCAGTCCCATATCAA-CATATTTATAATCCAAATTTCAAGA-CTACTCAACCTGAG
3181  193_HRV46b    CAGAGCAGTCCCATATCAA-CATATTTATAATCCAAATTTCAAGA-CTACTCAACCTGAG
3182  194_HRV46     CAGAGCAGTCCCATATCAA-CATATTTATAATCCAAATTTCAAGA-CTACTCAACCTGAG
3183  195_HRV80a    TAGAGCAGTCCCATACCAA-CATACCTACAGCCCAAATTTCAAAA-ACACTG---ATGAA
3184  196_HRV80b    TAGAGCAGTCCCATACCAA-CATACCTACAGCCCAAATTTCAAAA-ACACTG---ATGAA
3185  197_HRV80     TAGAGCAGTCCCATACCAA-CATACCTACAGCCCAAATTTCAAAA-ACACTG---ATGAA
```

FIG. D6 CONT'D

```
02.trace                                                              9/20/2007 4:59 PM 3186 198_HRV51    TCGTGCTGTAGCCTACCAA-CACACATACAGTACAAACTTCGTTC-CAAAAGAGGGATTT
3187 199_HRV51a   TCGTGCTGTAGCCTACCAA-CACACATACAGTACAAACTTCGTTC-CAAAAGAGGGATTT
3188 200_HRV51b   TCGTGCTGTAGCCTACCAA-CACACATACAGTACAAACTTCGTTC-CAAAAGAGGGATTT
3189 201_HRV65a   CCGAGCAGTAGCTTACCAA-CACACATACAGTACAAATTTTGTTC-CTAGCGGAGGTCTT
3190 202_HRV65b   CCGAGCAGTAGCTTACCAA-CACACATACAGTACAAATTTTGTTC-CTAGCGGAGGTCTT
3191 203_HRV65    CCGAGCAGTAGCTTACCAA-CACACATACAGTACAAATTTTGTTC-CTAGCGGAGGTCTT
3192 204_HRV71a   CAGAGCAGTAGCCTACCAA-TCAACATATACCACAAATTTTGTTC-CACAAGACGGGATC
3193 205_HRV71b   CAGAGCAGTAGCCTACCAA-TCAACATATACCACAAATTTTGTTC-CACAAGACGGGATC
3194 206_HRV71    CAGAGCAGTAGCCTACCAA-TCAACATATACCACAAATTTTGTTC-CACAAGACGGGATC
3195 207_HRV8     CAGAGCAGTTACGTATAAC-CATATATACAACCCCAATTATGTTA-GAGAGG------GA
3196 208_HRV95    CAGAGCAGTTACGTATAAC-CATATATACAACCCCAATTATGTTA-GAGAGG------GA
3197 209_HRV45    AAGAGCAGTCACATATAAC-CATACATATAATCCAAATTATGTTA-GGGCTG------AT
3198 210_HRV45a   AAGAGCAGTCACATATAAC-CATACATATAATCCAAATTATGTTA-GGGCTG------AT
3199 211_HRV45b   AAGAGCAGTCACATATAAC-CATACATATAATCCAAATTATGTTA-GGGCTG------AT
3200 GROUP_1      --G-G---T----TA------------------AA-T-----------------------
3201
3202 1_HRV1A1|d   GACG------TGACAACAG---CCATAGTCCGCAGAA------ACACTATAACAACTG--
3203 2_HRV1A2|d   GACG------TGACAACAG---CCATAGTCCGCAGAA------ACACTATAACAACTG--
3204 3_HRV1A|cD   GACG------TGACAACAG---CCATAGTCCGCAGAA------ACACTATAACAACTG--
3205 4_HRV1B1|d   GATG------TGACAACAG---CTATAGTTCCTAGAG------CTAGCATGAAAACTG--
3206 5_HRV1B2|d   GATG------TGACAACAG---CTATAGTTCCTAGAG------CTAGCATGAAAACTG--
3207 6_HRV1B      GATG------TGACAACAG---CTATAGTTCCTAGAG------CTAGCATGAAAACTG--
3208 7_HRV40a|d   GAAG------TCCAGATTT---TCCTCAAAGAGAGAG------CCAGCCTAACAACAG--
3209 8_HRV40b|d   GAAG------TCCAGATTT---TCCTCAAAGAGAGAG------CCAGCCTAACAACAG--
3210 9_HRV40      GAAG------TCCAGATTT---TCCTCAAAGAGAGAG------CCAGCCTAACAACAG--
3211 10_HRV85     GAAG------TTAAGATCT---TCCTCAAAGAGAGAG------CTAGTTTAACCACAG--
3212 11_HRV85a|   GAAG------TTAAGATCT---TCCTCAAAGAGAGAG------CTAGTTTAACCACAG--
3213 12_HRV85b|   GAAG------TTAAGATCT---TCCTCAAAGAGAGAG------CTAGTTTAACCACAG--
3214 13_HRV56a|   GATG------TACAGATCT---TCTTAAAACCCAGAC------CCAGCCTAACAACAT--
3215 14_HRV56b|   GATG------TACAGATCT---TCTTAAAACCCAGAC------CCAGCCTAACAACAT--
3216 15_HRV56     GATG------TACAGATCT---TCTTAAAACCCAGAC------CCAGCCTAACAACAT--
3217 16_HRV54     GATC------CAACAATTT---TCCTTAAACACAGGA------CAAACCTTGTAACAG--
3218 17_HRV98     GAAC------CAACAATCT---TTCTTAAGCATAGAA------AAGATCTTGTAACAG--
3219 18_HRV59a|   GAAC------CTGAAATTT---TCTTAAAACCAAGAA------TGAATATTACAACAG--
3220 19_HRV59b|   GAAC------CTGAAATTT---TCTTAAAACCAAGAA------TGAATATTACAACAG--
3221 20_HRV59     GAAC------CTGAAATTT---TCTTAAAACCAAGAA------TGAATATTACAACAG--
3222 21_HRV63     GAGA------CTGAAATTT---TCTTAAAACCTAGAG------CAACTATCAAGACAG--
3223 22_HRV63b|   GAGA------CTGAAATTT---TCTTAAAACCTAGAG------CAACTATCAAGACAG--
3224 23_HRV63a|   GAGA------CTGAAATTT---TCTTAAAACCTAGAG------CAACTATCAAGACAG--
3225 24_HRV39     GAAC------CAACACTCT---TTATAAAATCAAGAG------AGAATCTTACCACAG--
3226 25_HRV39a|   GAAC------CAACACTCT---TTATAAAATCAAGAG------AGAATCTTACCACAG--
3227 26_HRV39b|   GAAC------CAACACTCT---TTATAAAACCAAGAG------AGAATCTTACCACAG--
3228 27_HRV10a|   GAAT------TACAAATAT---TTATTAGGTCTAGAGATGATCCCAAAGTAGTAACTG--
3229 28_HRV10b|   GAAT------TACAAATAT---TTATTAGGTCTAGAGATGATCCCAAAGTAGTAACTG--
3230 29_HRV10     GAAT------TACAAATAT---TTATTAGGTCTAGAGATGATCCCAAAGTAGTAACTG--
3231 30_HRV100a   GATG------TAAAGATTT---TCATTAGACCCAGAGATGATCCAAAGTTGTAACTG--
3232 31_HRV100b   GATG------TAAAGATTT---TCATTAGACCCAGAGATGATCCAAAGTTGTAACTG--
3233 32_HRV100    GATG------TAAAGATTT---TCATTAGACCCAGAGATGATCCAAAGTTGTAACTG--
3234 33_HRV66     GATC------TGCAAATTT---TCATTAAACCTAGAACAGATCCAAAGTAGTCAATG--
3235 34_HRV66b|   GATC------TGCAAATTT---TCATTAAACCTAGAACAGATCCAAAGTAGTCAATG--
3236 35_HRV66a|   GATC------TGCAAATTT---TCATTAAACCTAGAACAGATCCAAAGTAGTCAATG--
3237 36_HRV77a|   GATG------TACAAATCT---TTATTAAAGAGAGAGCAAGCCCAAAGTAGTTACTT--
3238 37_HRV77b|   GATG------TACAAATCT---TTATTAAAGAGAGAGCAAGCCCAAAGTAGTTACTT--
3239 38_HRV77     GATG------TACAAATCT---TTATTAAAGAGAGAGCAAGCCCAAAGTAGTTACTT--
3240 39_HRV62a    ---G------TTGACATTT---TTATAAAATCAAGG------CAAAACTTGCAAACAG--
3241 40_HRV62b    ---G------TTGACATTT---TTATAAAATCAAGG------CAAAACTTGCAAACAG--
3242 41_HRV25     ---G------TTGACATCT---TTATACAACCAAGA------AACAGTTTAAAAACAG--
3243 42_HRV29a    ---G------AT-CCAG-----TTGTGGAATCCAGA------CCAAGCTTAATGACAG--
3244 43_HRV29b    ---G------AT-ACAG-----TTGTGGAATCCAGA------CCAAGCTTAATGACAG--
3245 44_HRV44a    ---G------AT-ACAG-----TTGTGGAACCTAGA------CACAGCATAATGACAG--
3246 45_HRV44b    ---G------AT-ACAG-----TTGTGGAACCTAGA------CACAGCATAATGACAG--
3247 46_HRV31     GAAG------TTACAATCT---TTGTTAAACACAGGGATAATCCAAAGATTATCACAG--
3248 47_HRV31a|   GAAG------TTACAATCT---TTGTTAAACACAGGGATAATCCAAAGATTATCACAG--
3249 48_HRV31b|   GAAG------TTACAATCT---TTGTTAAACACAGGGATAATCCAAAGATTATCACAG--
3250 49_HRV47     GAAG------TTGCAATTT---TCATTGAGCATAGAGAAAATCCAAAATTCATTACAG--
```

FIG. D6 CONT'D

```
02.trace                                                                    9/20/2007 4:59 PM 3251  50_HRV47a|    GAAG------TTGCAATTT---TCATTGAGCATAGAGAAAATCCAAAATTCATTACAG--
3252  51_HRV47b|    GAAG------TTGCAATTT---TCATTGAGCATAGAGAAAATCCAAAATTCATTACAG--
3253  52_HRV11      CAGG------TGAAAACAG---CTGTCAAGGCTAGGAAAACAATTAAAACAGCA------
3254  53_HRV11b|    CAGG------TGAAAACAG---CTGTCAAGGCTAGGAAAACAATTAAAACAGCG------
3255  54_HRV11a|    CAGG------TGAAAACAG---CTGTCAAGGCTAGGAAAACAATTAAAACAGCT------
3256  55_HRV76      GATG------TGCAAACAG---CTATTAGACCAAGAGCAACAATTAAGACTGCA------
3257  56_HRV76b|    GATG------TGCAAACAG---CTATTAGACCAAGAGCAACAATTAAGACTGCG------
3258  57_HRV76a|    GATG------TGCAAACAG---CTATTAGACCAAGAGCAACAATTAAGACTGCT------
3259  58_HRV33      GAAG------TGAAGACAG---CTATTAGACCAAGAGCAACAATCAAGACTGCA------
3260  59_HRV33b|    GAAG------TGAAGACAG---CTATTAGACCAAGAGCAACAATCAAGACTGCG------
3261  60_HRV33a|    GAAG------TGAAGACAG---CTATTAGACCAAGAGCAACAATCAAGACTGCT------
3262  61_HRV24a|    GAAG------TCAAGACAG---CAATTGAACCTAGAAGAGGAATTAAAACAGTG------
3263  62_HRV24b|    GAAG------TCAAGACAG---CAATTGAACCTAGAAGAGGAATTAAAACAGTC------
3264  63_HRV24      GAAG------TCAAGACAG---CAATTGAACCTAGAAGAGGAATTAAAACAGTT------
3265  64_HRV90      GAAC------TTAAGACTG---CAATTAGGCCCAGGAAAACAATCACAACAGCA------
3266  65_HRV90a|    GAAC------TTAAGACTG---CAATTAGGCCCAGGAAAACAATCACAACAGCG------
3267  66_HRV90b|    GAAC------TTAAGACTG---CAATTAGGCCCAGGAAAACAATCACAACAGCT------
3268  67_HRV34      ACTG------AGAAGACTG---CAATCAAACACAGAGCAAAGATCACAATGCCC------
3269  68_HRV34b|    ACTG------AGAAGACTG---CAATCAAACACAGAGCAAAGATCACAATGGCA------
3270  69_HRV34a|    ACTG------AGAAGACTG---CAATCAAACACAGAGCAAAGATCACAATGGCT------
3271  70_HRV50a|    ACTG------AGAAGACTG---CAATTGCAACTAGACCAAAGATCACAGTGGCA------
3272  71_HRV50b|    ACTG------AGAAGACTG---CAATTGCAACTAGACCAAAGATCACAGTGGCG------
3273  72_HRV50      ACTG------AGAAGACTG---CAATTGCAACTAGACCAAAGATCACAGTGGCT------
3274  73_HRV18a|    AGAG------AGAAAACTG---CCATAGTACCCAGAGCAAGGATTACAATGGCA------
3275  74_HRV18b|    AGAG------AGAAAACTG---CCATAGTACCCAGAGCAAGGATTACAATGGCG------
3276  75_HRV18      AGAG------AGAAAACTG---CCATAGTACCCAGAGCAAGGATTACAATGGCT------
3277  76_HRV55      ACAG------AAAAGACAG---CAATTGAATACAGAAGGGACATTAAAACAGTG------
3278  77_HRV55b|    ACAG------AAAAGACAG---CAATTGAATACAGAAGGGACATTAAAACAGTC------
3279  78_HRV55a|    ACAG------AAAAGACAG---CAATTGAATACAGAAGGGACATTAAAACAGTA------
3280  79_HRV57      CAAG------AAGAAACAG---CAATTAAATATAGAAGGGACATTAAAATTGTTAAGA--
3281  80_HRV57a|    CAAG------AAGAAACAG---CAATTAAATATAGAAGGGACATTAAAATTGTTAAGA--
3282  81_HRV57b|    CAAG------AAGAAACAG---CAATTAAATATAGAAGGGACATTAAAATTGTTAAGA--
3283  82_HRV21      GAAG------TCACTTCTG---CAGTTGAGTCCAGAAGAACAATTGTCACAGTT------
3284  83_HRVHan     GATG------TCACTTCTG---CAGTTGAGTCCAGAAGAACAATTGTCACAGTT-----
3285  84_HRV43      GAGG------TAGAAACAG---CCATAGTATCTAGGAGGGATATCAAAATTGTCAATG--
3286  85_HRV43b|    GAGG------TAGAAACAG---CCATAGTATCTAGGAGGGATATCAAAATTGTCAATG--
3287  86_HRV43a|    GAGG------TAGAAACAG---CCATAGTATCTAGGAGGGATATCAAAATTGTCAATG--
3288  87_HRV75      CAAG------TTGAGATTG---CTATTGAGCCCAGAAGAGATGTTAAGTTTGTAAATG--
3289  88_HRV75b|    CAAG------TTGAGCCCAG---CTATTGAGCCCAGAAGAGATGTTAAGTTTGTAAATG--
3290  89_HRV75a|    CAAG------TTGAGATTG---CTATTGAGCCCAGAAGAGATGTTAAGTTTGTAAATG--
3291  96_HRV9a|d    GATT------ATGCCACAG---TTATACCAGTTAGAGACAATGTTAGGGCAGTAAAGA--
3292  97_HRV9b|d    GATT------ATGCCACAG---TTATACCAGTTAGAGACAATGTTAGGGCAGTAAAGA--
3293  98_HRV9       GATT------ATGCCACAG---TTATACCAGTTAGAGACAATGTTAGGGCAGTAAAGA--
3294  99_HRV32      GATT------ACACCACAG---CCATACAAACCAGAGAGCATGTTAGAGCAGTCAAAA--
3295  100_HRV32a    GATT------ACACCACAG---CCATACAAACCAGAGAGCATGTTAGAGCAGTCAAAA--
3296  101_HRV32b    GATT------ACACCACAG---CCATACAAACCAGAGAGCATGTTAGAGCAGTCAAAA--
3297  102_HRV67     GAGG------CTCAAACGG---TTATACCTGTTAGAGCAGATGTTAGAACAATTAGAA--
3298  103_HRV67a    GAGG------CTCAAACGG---TTATACCTGTTAGAGCAGATGTTAGAACAATTAGAA--
3299  104_HRV67b    GAGG------CTCAAACGG---TTATACCTGTTAGAGCAGATGTTAGAACAATTAGAA--
3300  105_HRV15     GATG------TAACTACAG---TTATTCCAACTAGAGAAAATGTTAGAGCTATAGTAA--
3301  106_HRV15a    GATG------TAATTACAG---TTATTCCAACTAGAGAAAATGTTAGAGCTATAGTAA--
3302  107_HRV15b    GATG------TAACTACAG---TTATTCCAACTAGAGAAAATGTTAGAGCTATAGTAA--
3303  108_HRV74a    GACG------TAACTACAG---TCATCCCAACTAGG---------AGATCAATAGTGA--
3304  109_HRV74b    GACG------TAACTACAG---TCATCCCAACTAGG---------AGATCAATAGTGA--
3305  110_HRV74     GACG------TAACTACAG---TCATCCCAACTAGG---------AGATCAATAGTGA--
3306  111_HRV38a    GAAG------TAACCACTA---TGATTCCAACTAGAACCAACATAAGAACCATCGTAA--
3307  112_HRV38b    GAAG------TAACCACTA---TGATTCCAACTAGAACCAACATAAGAACCATCGTAA--
3308  113_HRV38     GAAG------TAACCACTA---TGATTCCAACTAGAACCAACATAAGAACCATCGTAA--
3309  114_HRV60     GAAG------CAGCCATAA---CAATCCCCATTAGAACTGATATACGAGCAATCAGAA--
3310  115_HRV60a    GAAG------CAGCCATAA---CAATCCCCATTAGAACTGATATACGAGCAATCAGAA--
3311  116_HRV60b    GAAG------CAGCCATAA---CAATCCCCATTAGAACTGATATACGAGCAATCAGAA--
3312  117_HRV64a    GAAT------ACACACCAC---CCGTTCCGTCACGTAACAGCCCCAGAGATATTGTCA--
3313  118_HRV64b    GAAT------ACACACCAC---CCGTTCCGTCACGTAACAGCCCCAGAGATATTGTCA--
3314  119_HRV64     GAAT------ACACACCAC---CCGTTCCGTCACGTAACAGCCCCAGAGATATTGTCA--
3315  120_HRV94a    GAGT------ACAAGCCAC---CTGTCCCAGTTAGGAATAGCCCCAGAGACATTGTCA--
```

FIG. D6 CONT'D 02.trace                                                                                    9/20/2007 4:59 PM

```
3316 121_HRV94b    GAGT------ACAAGCCAC---CTGTCCCAGTTAGGAATAGCCCCAGAGACATTGTCA--
3317 122_HRV94     GAGT------ACAAGCCAC---CTGTCCCAGTTAGGAATAGCCCCAGAGACATTGTCA--
3318 123_HRV22     GATT------ACACACTAC---CTATCCCAACAAGAGCCAACCCTAGACAAATTTTGA--
3319 124_HRV22a    GATT------ACACACTAC---CTATCCCAACAAGAGCCAACCCTAGACAAATTTTGA--
3320 125_HRV22b    GATT------ACACACTAC---CTATCCCAACAAGAGCCAACCCTAGACAAATTTTGA--
3321 126_HRV82     GATT------ACAGTGTTG---TTATTCCAGTTAGAGAGAGTCCCAGACAGATTCTTA--
3322 127_HRV82b    GATT------ACAGTGTTG---TTATTCCAGTTAGAGAGAGTCCCAGACAGATTCTTA--
3323 128_HRV82a    GATT------ACAGTGTTG---TTATTCCAGTTAGAGAGAGTCCCAGACAGATTCTTA--
3324 129_HRV19     GAAG------TCACTCTTC---CAATTGAAATAAGAGATAACCCTAGACATATAAAGA--
3325 130_HRV19a    GAAG------TCACTCTTC---CAATTGAAATAAGAGATAACCCTAGACATATAAAGA--
3326 131_HRV19b    GAAG------TCACTCTTC---CAATTGAAATAAGAGATAACCCTAGACATATAAAGA--
3327 132_HRV13     GATG------TTGCAGTCT---CCATTGTACCTAGAGCAAATGTTAGGGAAATTAGAA--
3328 133_HRV13a    GATG------TTGCAGTCT---CCATTGTACCTAGAGCAAATGTTAGGGAAATTAGAA--
3329 134_HRV13b    GATG------TTGCAGTCT---CCATTGTACCTAGAGCAAATGTTAGGGAAATTAGAA--
3330 135_HRV41     GCAGA---GATTGTGGCTT---CTGTCAGACCTAGAGACAATGTTAGACAAGTAAGAA--
3331 136_HRV41a    GCAGA---GATTGTGGCTT---CTGTCAGACCTAGAGACAATGTTAGACAAGTAAGAA--
3332 137_HRV41b    GCAGA---GATTGTGGCTT---CTGTCAGACCTAGAGACAATGTTAGACAAGTAAGAA--
3333 138_HRV73     GAAG------TTACTACTG---CCATTAGGCATAGAGATAATGTTAGAGCCATCCAAA--
3334 139_HRV73b    GAAG------TTACTACTG---CCATTAGGCATAGAGATAATGTTAGAGCCATCCAAA--
3335 140_HRV73a    GAAG------TTACTACTG---CCATTAGGCATAGAGATAATGTTAGAGCCATCCAAA--
3336 141_HRV61     GAAAAACAAGTTACCACTT---TCATCAAACCTAGAGCTAACTTAAGAGAGATTAGAA--
3337 142_HRV61a    GAAAAACAAGTTACCACTT---TCATCAAACCTAGAGCTAACTTAAGAGAGATTAGAA--
3338 143_HRV61b    GAAAAACAAGTTACCACTT---TCATCAAACCTAGAGCTAACTTAAGAGAGATTAGAA--
3339 144_HRV96     -------AGGTTACCACTT---TTATCAAACCTAGAGAAAATCTAAGGGATATTAGAA--
3340 145_HRV96b    -------AGGTTACCACTT---TTATCAAACCTAGAGAAAATCTAAGGGATATTAGAA--
3341 146_HRV96a    -------AGGTTACCACTT---TTATCAAACCTAGAGAAAATCTAAGGGATATTAGAA--
3342  90_HRV16a|   GTAC------ACAATGATGTGGCTATAAGACCTAGAACAAATCTAACAACTGTA------
3343  91_HRV16b|   GTAC------ACAATGATGTGGCTATAAGACCTAGAACAAATCTAACAACTGTC------
3344  92_1AYM_A    GTAC------ACAATGATGTGGCTATAAGACCTAGAACAAATCTAACAACTGTT------
3345  93_HRV81a|   GTCC------ACACTAGTGTAGCCATAAAACCTAGAACAAGTCTAACAAATGTG------
3346  94_HRV81b|   GTCC------ACACTAGTGTAGCCATAAAACCTAGAACAAGTCTAACAAATGTC------
3347  95_HRV81     GTCC------ACACTAGTGTAGCCATAAAACCTAGAACAAGTCTAACAAATGTT------
3348 147_HRV2      AGTA------TTCAGACAG---CAATTGTGACCAGACCAATTATCACTACAGCT------
3349 148_HRV2a|    AGTA------TTCAGACAG---CAATTGTGACCAGACCAATTATCACTACAGCA------
3350 149_HRV2b|    AGTA------TTCAGACAG---CAATTGTGACCAGACCAATTATCACTACAGCG------
3351 150_HRV49a    GACA------TTAAAACAG---GAATCACATCCAGAGCAATTATTACAACAGCG------
3352 151_HRV49b    GACA------TTAAAACAG---GAATCACATCCAGAGCAATTATTACAACAGCA------
3353 152_HRV49     GACA------TTAAAACAG---GAATCACATCCAGAGCAATTATTACAACAGCT------
3354 153_HRV23a    AATG------TCAAATCAA---GGGTTGCACATAGACCTGCAGTGATAACAGCG------
3355 154_HRV23b    AATG------TCAAATCAA---GGGTTGCACATAGACCTGCAGTGATAACAGCA------
3356 155_HRV23     AATG------TCAAATCAA---GGGTTGCACATAGACCTGCAGTGATAACAGCT------
3357 156_HRV30a    GAAG------TTAAATCAA---GGGTTGAACACAGAGCTAGGGTGACGACAGCG------
3358 157_HRV30b    GAAG------TTAAATCAA---GGGTTGAACACAGAGCTAGGGTGACGACAGCG------
3359 158_HRV30     GAAG------TTAAATCAA---GGGTTGAACACAGAGCTAGGGTGACGACAGCT------
3360 159_HRV7      GAGG------TCGCA---ACTCAAATCAAAACCAGAGCCAATCTTTTCACCCTCAAAT--
3361 160_HRV7b|    GAGG------TCGCA---ACTCAAATCAAAACCAGAGCCAATCTTTTCACCCTCAAAT--
3362 161_HRV7a|    GAGG------TCGCA---ACTCAAATCAAAACCAGAGCCAATCTTTTCACCCTCAAAT--
3363 162_HRV88     GAAG------TAGCA---ACTCAAATCAAAACCAGACGAGATGTTTACACTGTTACCA--
3364 163_HRV88a    GAAG------TAGCA---ACTCAAATCAAAACCAGACGAGATGTTTACACTGTTACCA--
3365 164_HRV88b    GAAG------TAGCA---ACTCAAATCAAAACCAGACGAGATGTTTACACTGTTACCA--
3366 165_HRV36a    GAGA------TCACA---ACCCAAATTAAAACCAGACCTAATGTCTTCACTGTA------
3367 166_HRV36b    GAGA------TCACA---ACCCAAATTAAAACCAGACCTAATGTCTTCACTGTG------
3368 167_HRV36     GAGA------TCACA---ACCCAAATTAAAACCAGACCTAATGTCTTCACTGTT------
3369 168_HRV89a    GAGG------CCACA---ACTCAGATTAAAACCAGACCTGATGTTTTTACCGTTACAA--
3370 169_HRV89b    GAGG------CCACA---ACTCAGATTAAAACCAGACCTGATGTTTTTACCGTTACAA--
3371 170_HRV89     GAGG------CCACA---ACTCAGATTAAAACCAGACCTGATGTTTTTACCGTTACAA--
3372 171_HRV58     GAGG------TAACA---ACACAAATCAAACCCAGAACCAATGTTTTTACTATTACAT--
3373 172_HRV58a    GAGG------TAACA---ACACAAATCAAACCCAGAACCAATGTTTTTACTATTACAT--
3374 173_HRV58b    GAGG------TAACA---ACACAAATCAAACCCAGAACCAATGTTTTTACTATTACAT--
3375 174_HRV12a    GGAG------TTCCAGACAATAGAGTCAAACTCAGAGAGACACTCACCACAGTA------
3376 175_HRV12b    GGAG------TTCCAGACAATAGAGTCAAACTCAGAGAGACACTCACCACAGTG------
3377 176_HRV12     GGAG------TTCCAGACAATAGAGTCAAACTCAGAGAGACACTCACCACAGTT------
3378 177_HRV78a    GGAA------CTCCAGACACCAAAGTGGCAATTAGAGCTAATATTAAAACTGTA------
3379 178_HRV78b    GGAA------CTCCAGACACCAAAGTGGCAATTAGAGCTAATATTAAAACTGTG------
3380 179_HRV78     GGAA------CTCCAGACACCAAAGTGGCAATTAGAGCTAATATTAAAACTGTT------
```

FIG. D6 CONT'D

```
02.trace                                                            9/20/2007 4:59 PM 3381 180_HRV20      GAAA------TTACA---ACTCATATCAGATTCAGAAACACTGTCAAAGATCTAACATAC
3382 181_HRV20a     GAAA------TTACA---ACTCATATCAGATTCAGAAACACTGTCAAAGATCTAACATAC
3383 182_HRV20b     GAAA------TTACA---ACTCATATCAGATTCAGAAACACTGTCAAAGATCTAACATAC
3384 183_HRV68      GATA------TTAAA---ACTCATATTAAATTTAGGAATACTGTTAAAGATTTGGCATAT
3385 184_HRV68a     GATA------TTAAA---ACTCATATTAAATTTAGGAATACTGTTAAAGATTTGGCATAT
3386 185_HRV68b     GATA------TTAAA---ACTCATATTAAATTTAGGAATACTGTTAAAGATTTGGCATAT
3387 186_HRV28      GATG------TTGAG---ACTCATATTAAATTTAGAACAGATGTTAAACAGATCACAA--
3388 187_HRV28a     GATG------TTGAG---ACTCATATTAAATTTAGAACAGATGTTAAACAGATCACAA--
3389 188_HRV28b     GATG------TTGAG---ACTCATATTAAATTTAGAACAGATGTTAAACAGATCACAA--
3390 189_HRV53a     ACAG------TTGAA---ACTCACATTAAGTTCAGACCTGATGTTAAAGATGTAACAT--
3391 190_HRV53b     ACAG------TTGAA---ACTCACATTAAGTTCAGACCTGATGTTAAAGATGTAACAT--
3392 191_HRV53      ACAG------TTGAA---ACTCACATTAAGTTCAGACCTGATGTTAAAGATGTAACAT--
3393 192_HRV46a     ACTA------TACCAGATACTCATATTGGAATTAGAAGGGATATAAAGTACATTAAAA--
3394 193_HRV46b     ACTA------TACCAGATACTCATATTGGAATTAGAAGGGATATAAAGTACATTAAAA--
3395 194_HRV46      ACTA------TACCAGATACTCATATTGGAATTAGAAGGGATATAAAGTACATTAAAA--
3396 195_HRV80a     TCTA------TACCAGATACACAAATTAAAATCAGAGATAATATCAGGCAGGTTAGAA--
3397 196_HRV80b     TCTA------TACCAGATACACAAATTAAAATCAGAGATAATATCAGGCAGGTTAGAA--
3398 197_HRV80      TCTA------TACCAGATACACAAATTAAAATCAGAGATAATATCAGGCAGGTTAGAA--
3399 198_HRV51      GAAG------GCTTGAAAACTCAGATTAAAACTAGGGCAGACATCAAACTTGTGAACT--
3400 199_HRV51a     GAAG------GCTTGAAAACTCAGATTAAAACTAGGGCAGACATCAAACTTGTGAACT--
3401 200_HRV51b     GAAG------GCTTGAAAACTCAGATTAAAACTAGGGCAGACATCAAACTTGTGAACT--
3402 201_HRV65a     ACAA------ACCTAAGAACCCAAATTAAAACCAGAGATAACATTAAAATTGTAAACT--
3403 202_HRV65b     ACAA------ACCTAAGAACCCAAATTAAAACCAGAGATAACATTAAAATTGTAAACT--
3404 203_HRV65      ACAA------ACCTAAGAACCCAAATTAAAACCAGAGATAACATTAAAATTGTAAACT--
3405 204_HRV71a     AATT------CCATTAAAACCAAAATCAAAATCAGAAGAGACATTAAAGAGGTCAGCA--
3406 205_HRV71b     AATT------CCATTAAAACCAAAATCAAAATCAGAAGAGACATTAAAGAGGTCAGCA--
3407 206_HRV71      AATT------CCATTAAAACCAAAATCAAAATCAGAAGAGACATTAAAGAGGTCAGCA--
3408 207_HRV8       GTAA------CACCAGAAACTAAGGTTAAATATAGAGCTGAAGTCACAACCATT------
3409 208_HRV95      GTAA------CACCAGAAACTAAGGTCAAATATAGAGCTGAAGTCACAACCATT------
3410 209_HRV45      GAAA------CAGCC---ACAAAAGTCCAAACTAGAGCAAATGTCACAACAGTA------
3411 210_HRV45a     GAAA------CAGCC---ACAAAAGTCCAAACTAGAGCAAATGTCACAACAGTG------
3412 211_HRV45b     GAAA------CAGCC---ACAAAAGTCCAAACTAGAGCAAATGTCACAACAGTT------
3413 GROUP_1        ------------------------T--------G--------------------------
3414
3415 1_HRV1A1|d     ----CA---------------
3416 2_HRV1A2|d     ----CG---------------
3417 3_HRV1A|cD     ----CT---------------
3418 4_HRV1B1|d     ----TA---------------
3419 5_HRV1B2|d     ----TC---------------
3420 6_HRV1B        ----TT---------------
3421 7_HRV40a|d     ----TA---------------
3422 8_HRV40b|d     ----TC---------------
3423 9_HRV40        ----TT---------------
3424 10_HRV85       ----CA---------------
3425 11_HRV85a|     ----CG---------------
3426 12_HRV85b|     ----CT---------------
3427 13_HRV56a|     ----TA---------------
3428 14_HRV56b|     ----TG---------------
3429 15_HRV56|      ----TT---------------
3430 16_HRV54       ----CT---------------
3431 17_HRV98       ----CT---------------
3432 18_HRV59a|     ----CA---------------
3433 19_HRV59b|     ----CG---------------
3434 20_HRV59       ----CT---------------
3435 21_HRV63       ----CA---------------
3436 22_HRV63b|     ----CG---------------
3437 23_HRV63a|     ----CT---------------
3438 24_HRV39       ----CT---------------
3439 25_HRV39a|     ----CA---------------
3440 26_HRV39b|     ----CT---------------
3441 27_HRV10a|     ----CA---------------
3442 28_HRV10b|     ----CC---------------
3443 29_HRV10       ----CT---------------
3444 30_HRV100a     ----CA---------------
3445 31_HRV100b     ----CG---------------
```

FIG. D6 CONT'D

02.trace                                                          9/20/2007 4:59 PM

```
3446  32_HRV100     ----CT---------------
3447  33_HRV66      ----TA---------------
3448  34_HRV66b|    ----TG---------------
3449  35_HRV66a|    ----TC---------------
3450  36_HRV77a|    ----TG---------------
3451  37_HRV77b|    ----TA---------------
3452  38_HRV77      ----TT---------------
3453  39_HRV62a     ----CT---------------
3454  40_HRV62b     ----C----------------
3455  41_HRV25      ----CT---------------
3456  42_HRV29a     ----CT---------------
3457  43_HRV29b     ----CT---------------
3458  44_HRV44a     ----CT---------------
3459  45_HRV44b     ----CT---------------
3460  46_HRV31      ----CA---------------
3461  47_HRV31a|    ----CT---------------
3462  48_HRV31b|    ----CA---------------
3463  49_HRV47      ----CA---------------
3464  50_HRV47a|    ----CT---------------
3465  51_HRV47b|    ----CA---------------
3466  52_HRV11      ---------------------
3467  53_HRV11b|    ---------------------
3468  54_HRV11a|    ---------------------
3469  55_HRV76      ---------------------
3470  56_HRV76b|    ---------------------
3471  57_HRV76a|    ---------------------
3472  58_HRV33      ---------------------
3473  59_HRV33b|    ---------------------
3474  60_HRV33a|    ---------------------
3475  61_HRV24a|    ---------------------
3476  62_HRV24b|    ---------------------
3477  63_HRV24      ---------------------
3478  64_HRV90      ---------------------
3479  65_HRV90a|    ---------------------
3480  66_HRV90b|    ---------------------
3481  67_HRV34      ---------------------
3482  68_HRV34b|    ---------------------
3483  69_HRV34a|    ---------------------
3484  70_HRV50a|    ---------------------
3485  71_HRV50b|    ---------------------
3486  72_HRV50      ---------------------
3487  73_HRV18a|    ---------------------
3488  74_HRV18b|    ---------------------
3489  75_HRV18      ---------------------
3490  76_HRV55      ---------------------
3491  77_HRV55b|    ---------------------
3492  78_HRV55a|    ---------------------
3493  79_HRV57      ----ATGTG------------
3494  80_HRV57a|    ----ATGTA------------
3495  81_HRV57b|    ----ATGTC------------
3496  82_HRV21      ---------------------
3497  83_HRVHan     ---------------------
3498  84_HRV43      ----CA---------------
3499  85_HRV43b|    ----CG---------------
3500  86_HRV43a|    ----CT---------------
3501  87_HRV75      ----CA---------------
3502  88_HRV75b|    ----CG---------------
3503  89_HRV75a|    ----CT---------------
3504  96_HRV9a|d    ----ATGTC------------
3505  97_HRV9b|d    ----ATGTG------------
3506  98_HRV9       ----ATGTA------------
3507  99_HRV32      ----ATGTA------------
3508  100_HRV32a    ----ATGTG------------
3509  101_HRV32b    ----ATGTC------------
3510  102_HRV67     ----ATGTA------------
```

FIG. D6 CONT'D 02.trace                                                                9/20/2007 4:59 PM

```
3511 103_HRV67a     ----ATGTC-----------
3512 104_HRV67b     ----ATGTT-----------
3513 105_HRV15      ----ATGTT-----------
3514 106_HRV15a     ----ATGTA-----------
3515 107_HRV15b     ----ATGTC-----------
3516 108_HRV74a     ----ATGTA-----------
3517 109_HRV74b     ----ATGTC-----------
3518 110_HRV74      ----ATGTT-----------
3519 111_HRV38a     ----ATGTA-----------
3520 112_HRV38b     ----ATGTC-----------
3521 113_HRV38      ----ATGTT-----------
3522 114_HRV60      ----CAGTT-----------
3523 115_HRV60a     ----CAGTA-----------
3524 116_HRV60b     ----CAGTG-----------
3525 117_HRV64a     ----CAGTG-----------
3526 118_HRV64b     ----CAGTG-----------
3527 119_HRV64      ----CAGTA-----------
3528 120_HRV94a     ----CAGTG-----------
3529 121_HRV94b     ----CAGTC-----------
3530 122_HRV94      ----CAGTA-----------
3531 123_HRV22      ----ATGTA-----------
3532 124_HRV22a     ----ATGTG-----------
3533 125_HRV22b     ----ATGTC-----------
3534 126_HRV82      ----ATGTA-----------
3535 127_HRV82b     ----ATGTT-----------
3536 128_HRV82a     ----ATGTC-----------
3537 129_HRV19      ----ATGTA-----------
3538 130_HRV19a     ----ATGTG-----------
3539 131_HRV19b     ----ATGTC-----------
3540 132_HRV13      ----ACTTT-----------
3541 133_HRV13a     ----ACTTG-----------
3542 134_HRV13b     ----ACTTA-----------
3543 135_HRV41      ----ATTAT-----------
3544 136_HRV41a     ----ATTAG-----------
3545 137_HRV41b     ----ATTAC-----------
3546 138_HRV73      ----ATTTT-----------
3547 139_HRV73b     ----ATTTG-----------
3548 140_HRV73a     ----ATTTC-----------
3549 141_HRV61      ----CATTT-----------
3550 142_HRV61a     ----CATTT-----------
3551 143_HRV61b     ----CATTT-----------
3552 144_HRV96      ----ATTTT-----------
3553 145_HRV96b     ----ATTTA-----------
3554 146_HRV96a     ----ATTTC-----------
3555  90_HRV16a|    --------------------
3556  91_HRV16b|    --------------------
3557  92_1AYM_A     --------------------
3558  93_HRV81a|    --------------------
3559  94_HRV81b|    --------------------
3560  95_HRV81      --------------------
3561 147_HRV2       --------------------
3562 148_HRV2a|     --------------------
3563 149_HRV2b|     --------------------
3564 150_HRV49a     --------------------
3565 151_HRV49b     --------------------
3566 152_HRV49      --------------------
3567 153_HRV23a     --------------------
3568 154_HRV23b     --------------------
3569 155_HRV23      --------------------
3570 156_HRV30a     --------------------
3571 157_HRV30b     --------------------
3572 158_HRV30      --------------------
3573 159_HRV7       ----CAGCT-----------
3574 160_HRV7b|     ----CAGCA-----------
3575 161_HRV7a|     ----CAGCG-----------
```

FIG. D6 CONT'D 02.trace                                                                 9/20/2007 4:59 PM

```
3576  162_HRV88       ----CTGCT-----------
3577  163_HRV88a      ----CTGCA-----------
3578  164_HRV88b      ----CTGCG-----------
3579  165_HRV36a      --------------------
3580  166_HRV36b      --------------------
3581  167_HRV36       --------------------
3582  168_HRV89a      ----ACGTG-----------
3583  169_HRV89b      ----ACGTA-----------
3584  170_HRV89       ----ACGTC-----------
3585  171_HRV58       ----CTGCT-----------
3586  172_HRV58a      ----CTGCA-----------
3587  173_HRV58b      ----CTGCC-----------
3588  174_HRV12a      --------------------
3589  175_HRV12b      --------------------
3590  176_HRV12       --------------------
3591  177_HRV78a      --------------------
3592  178_HRV78b      --------------------
3593  179_HRV78       --------------------
3594  180_HRV20       CCCACAGAAATGACGAATGTT
3595  181_HRV20a      CCCACAGAAATGACGAATGTA
3596  182_HRV20b      CCCACAGAAATGACGAATGTG
3597  183_HRV68       CCTCCAGAATTAGCAAACCTT
3598  184_HRV68a      CCTCCAGAATTAGCAAACCTT
3599  185_HRV68b      CCTCCAGAATTAGCAAACCTT
3600  186_HRV28       ----CAGTT-----------
3601  187_HRV28a      ----CAGTA-----------
3602  188_HRV28b      ----CAGTC-----------
3603  189_HRV53a      ----CAGTAATGACAGCT---
3604  190_HRV53b      ----CAGTAATGACAGCT---
3605  191_HRV53       ----CAGTAATGACAGCA---
3606  192_HRV46a      ----CAGCA-----------
3607  193_HRV46b      ----CAGCC-----------
3608  194_HRV46       ----CAGCT-----------
3609  195_HRV80a      ----CAGTA-----------
3610  196_HRV80b      ----CAGTC-----------
3611  197_HRV80       ----CAGTT-----------
3612  198_HRV51       -----TT-------------
3613  199_HRV51a      -----TA-------------
3614  200_HRV51b      -----TG-------------
3615  201_HRV65a      -----TG-------------
3616  202_HRV65b      -----TA-------------
3617  203_HRV65       -----TT-------------
3618  204_HRV71a      -----ACTAA----------
3619  205_HRV71b      -----ACTAG----------
3620  206_HRV71       -----ACTAT----------
3621  207_HRV8        --------------------
3622  208_HRV95       --------------------
3623  209_HRV45       --------------------
3624  210_HRV45a      --------------------
3625  211_HRV45b      --------------------
3626  GROUP_1         --------------------
3627
3628
3629
3630  Summary:
3631
3632  GROUP_1    AA-CC--T-GA----T------A-----T--T-----A-GT--T--T-GT-CC--A----
3633  SUMMARY    AA-CC--T-GA----T------A-----T--T-----A-GT--T--T-GT-CC--A----
3634
3635  GROUP_1    ------AG-----------------A--C-G---C-----T-GA-GC-GC-GA-AC-GG
3636  SUMMARY    ------AG-----------------A--C-G---C-----T-GA-GC-GC-GA-AC-GG
3637
3638  GROUP_1    CA-AC-A--------CA-CC-GA-GA-----T-GA-AC--G----GT----------A
3639  SUMMARY    CA-AC-A--------CA-CC-GA-GA-----T-GA-AC--G----GT----------A
3640
```

FIG. D6 CONT'D

```
02.trace                                                                9/20/2007 4:59 PM 3641 GROUP_1    AC-----ATGA-A------T-GA----TT--T-GG--G--C----TG-------------
3642 SUMMARY    AC-----ATGA-A------T-GA----TT--T-GG--G--C----TG-------------
3643
3644 GROUP_1    ------------------------------------------------------------
3645 SUMMARY    ------------------------------------------------------------
3646
3647 GROUP_1    -----------TGG----T-A---T----GA-ATG-C-CA--T--G--G-AA----GA
3648 SUMMARY    -----------TGG----T-A---T----GA-ATG-C-CA--T--G--G-AA----GA
3649
3650 GROUP_1    -T-TT-AC-TA-----G-TT--A-TC-GA--T-AC--T-G-T-----------C------
3651 SUMMARY    -T-TT-AC-TA-----G-TT--A-TC-GA--T-AC--T-G-T-----------C------
3652
3653 GROUP_1    -------------GG-CA--T-----T-CA-T--ATGT---T-CC-CC-GG-G--CC---
3654 SUMMARY    -------------GG-CA--T-----T-CA-T--ATGT---T-CC-CC-GG-G--CC---
3655
3656 GROUP_1    -CC--------G-------------TGG-A--C--G-A--AA----TC----TT-TGGCA
3657 SUMMARY    -CC--------G-------------TGG-A--C--G-A--AA----TC----TT-TGGCA
3658
3659 GROUP_1    ----GG-CA----T--CC--G--T--C--T-CC-TT-----G--T-GC-TC-G--TA-TA
3660 SUMMARY    ----GG-CA----T--CC--G--T--C--T-CC-TT-----G--T-GC-TC-G--TA-TA
3661
3662 GROUP_1    -ATGTT-TA-GA-GG-TA-----------------------TA-GG------------
3663 SUMMARY    -ATGTT-TA-GA-GG-TA-----------------------TA-GG------------
3664
3665 GROUP_1    -AA----ATGGG--C--T-T------G--T--T-AC-------CA---------------
3666 SUMMARY    -AA----ATGGG--C--T-T------G--T--T-AC-------CA---------------
3667
3668 GROUP_1    --T-----------T-T--C--AA-GC-AA-CA---------TGG-G-CC--G--C-C
3669 SUMMARY    --T-----------T-T--C--AA-GC-AA-CA---------TGG-G-CC--G--C-C
3670
3671 GROUP_1    --G-G---T----TA--------------------AA-T---------------------
3672 SUMMARY    --G-G---T----TA--------------------AA-T---------------------
3673
3674 GROUP_1    ----------------------T--------G----------------------------
3675 SUMMARY    ----------------------T--------G----------------------------
3676
3677 GROUP_1    --------------------
3678 SUMMARY    --------------------
3679
3680
```

FIG. D6 CONT'D

```
03.trace                                                              9/20/2007 5:03 PM 1  Group 1:   1_HRV1A1|d
   2  Group 1:   2_HRV1A2|d
   3  Group 1:   3_HRV1A|cD
   4  Group 1:   4_HRV1B1|d
   5  Group 1:   5_HRV1B2|d
   6  Group 1:   6_HRV1B
   7  Group 1:   7_HRV40a|d
   8  Group 1:   8_HRV40b|d
   9  Group 1:   9_HRV40
  10  Group 1:  10_HRV85
  11  Group 1:  11_HRV85a|
  12  Group 1:  12_HRV85b|
  13  Group 1:  13_HRV56a|
  14  Group 1:  14_HRV56b|
  15  Group 1:  15_HRV56
  16  Group 1:  16_HRV54
  17  Group 1:  17_HRV98
  18  Group 1:  18_HRV59a|
  19  Group 1:  19_HRV59b|
  20  Group 1:  20_HRV59
  21  Group 1:  21_HRV63
  22  Group 1:  22_HRV63b|
  23  Group 1:  23_HRV63a|
  24  Group 1:  24_HRV39
  25  Group 1:  25_HRV39a|
  26  Group 1:  26_HRV39b|
  27  Group 1:  27_HRV10a|
  28  Group 1:  28_HRV10b|
  29  Group 1:  29_HRV10
  30  Group 1:  30_HRV100a
  31  Group 1:  31_HRV100b
  32  Group 1:  32_HRV100
  33  Group 1:  33_HRV66
  34  Group 1:  34_HRV66b|
  35  Group 1:  35_HRV66a|
  36  Group 1:  36_HRV77a|
  37  Group 1:  37_HRV77b|
  38  Group 1:  38_HRV77
  39  Group 1:  39_HRV62a
  40  Group 1:  40_HRV62b
  41  Group 1:  41_HRV25
  42  Group 1:  42_HRV29a
  43  Group 1:  43_HRV29b
  44  Group 1:  44_HRV44a
  45  Group 1:  45_HRV44b
  46  Group 1:  46_HRV31
  47  Group 1:  47_HRV31a|
  48  Group 1:  48_HRV31b|
  49  Group 1:  49_HRV47
  50  Group 1:  50_HRV47a|
  51  Group 1:  51_HRV47b|
  52  Group 1:  52_HRV11
  53  Group 1:  53_HRV11b|
  54  Group 1:  54_HRV11a|
  55  Group 1:  55_HRV76
  56  Group 1:  56_HRV76b|
  57  Group 1:  57_HRV76a|
  58  Group 1:  58_HRV33
  59  Group 1:  59_HRV33b|
  60  Group 1:  60_HRV33a|
  61  Group 1:  61_HRV24a|
  62  Group 1:  62_HRV24b|
  63  Group 1:  63_HRV24
  64  Group 1:  64_HRV90
  65  Group 1:  65_HRV90a|
```

FIG. D7

03.trace                                                                9/20/2007 5:03 PM

```
 66 Group 1:  66_HRV90b|
 67 Group 1:  67_HRV34
 68 Group 1:  68_HRV34b|
 69 Group 1:  69_HRV34a|
 70 Group 1:  70_HRV50a|
 71 Group 1:  71_HRV50b|
 72 Group 1:  72_HRV50
 73 Group 1:  73_HRV18a|
 74 Group 1:  74_HRV18b|
 75 Group 1:  75_HRV18
 76 Group 1:  76_HRV55
 77 Group 1:  77_HRV55b|
 78 Group 1:  78_HRV55a|
 79 Group 1:  79_HRV57
 80 Group 1:  80_HRV57a|
 81 Group 1:  81_HRV57b|
 82 Group 1:  82_HRV21
 83 Group 1:  83_HRVHan
 84 Group 1:  84_HRV43
 85 Group 1:  85_HRV43b|
 86 Group 1:  86_HRV43a|
 87 Group 1:  87_HRV75
 88 Group 1:  88_HRV75b|
 89 Group 1:  89_HRV75a|
 90 Group 1:  96_HRV9a|d
 91 Group 1:  97_HRV9b|d
 92 Group 1:  98_HRV9
 93 Group 1:  99_HRV32
 94 Group 1: 100_HRV32a
 95 Group 1: 101_HRV32b
 96 Group 1: 102_HRV67
 97 Group 1: 103_HRV67a
 98 Group 1: 104_HRV67b
 99 Group 1: 105_HRV15
100 Group 1: 106_HRV15a
101 Group 1: 107_HRV15b
102 Group 1: 108_HRV74a
103 Group 1: 109_HRV74b
104 Group 1: 110_HRV74
105 Group 1: 111_HRV38a
106 Group 1: 112_HRV38b
107 Group 1: 113_HRV38
108 Group 1: 114_HRV60
109 Group 1: 115_HRV60a
110 Group 1: 116_HRV60b
111 Group 1: 117_HRV64a
112 Group 1: 118_HRV64b
113 Group 1: 119_HRV64
114 Group 1: 120_HRV94a
115 Group 1: 121_HRV94b
116 Group 1: 122_HRV94
117 Group 1: 123_HRV22
118 Group 1: 124_HRV22a
119 Group 1: 125_HRV22b
120 Group 1: 126_HRV82
121 Group 1: 127_HRV82b
122 Group 1: 128_HRV82a
123 Group 1: 129_HRV19
124 Group 1: 130_HRV19a
125 Group 1: 131_HRV19b
126 Group 1: 132_HRV13
127 Group 1: 133_HRV13a
128 Group 1: 134_HRV13b
129 Group 1: 135_HRV41
130 Group 1: 136_HRV41a
```

FIG. D7 CONT'D

```
03.trace                                                         9/20/2007 5:03 PM 131 Group 1: 137_HRV41b
   132 Group 1: 138_HRV73
   133 Group 1: 139_HRV73b
   134 Group 1: 140_HRV73a
   135 Group 1: 141_HRV61
   136 Group 1: 142_HRV61a
   137 Group 1: 143_HRV61b
   138 Group 1: 144_HRV96
   139 Group 1: 145_HRV96b
   140 Group 1: 146_HRV96a
   141 Group 1: 90_HRV16a|
   142 Group 1: 91_HRV16b|
   143 Group 1: 92_1AYM_A
   144 Group 1: 93_HRV81a|
   145 Group 1: 94_HRV81b|
   146 Group 1: 95_HRV81
   147 Group 1: 147_HRV2
   148 Group 1: 148_HRV2a|
   149 Group 1: 149_HRV2b|
   150 Group 1: 150_HRV49a
   151 Group 1: 151_HRV49b
   152 Group 1: 152_HRV49
   153 Group 1: 153_HRV23a
   154 Group 1: 154_HRV23b
   155 Group 1: 155_HRV23
   156 Group 1: 156_HRV30a
   157 Group 1: 157_HRV30b
   158 Group 1: 158_HRV30
   159 Group 1: 159_HRV7
   160 Group 1: 160_HRV7b|
   161 Group 1: 161_HRV7a|
   162 Group 1: 162_HRV88
   163 Group 1: 163_HRV88a
   164 Group 1: 164_HRV88b
   165 Group 1: 165_HRV36a
   166 Group 1: 166_HRV36b
   167 Group 1: 167_HRV36
   168 Group 1: 168_HRV89a
   169 Group 1: 169_HRV89b
   170 Group 1: 170_HRV89
   171 Group 1: 171_HRV58
   172 Group 1: 172_HRV58a
   173 Group 1: 173_HRV58b
   174 Group 1: 174_HRV12a
   175 Group 1: 175_HRV12b
   176 Group 1: 176_HRV12
   177 Group 1: 177_HRV78a
   178 Group 1: 178_HRV78b
   179 Group 1: 179_HRV78
   180 Group 1: 180_HRV20
   181 Group 1: 181_HRV20a
   182 Group 1: 182_HRV20b
   183 Group 1: 183_HRV68
   184 Group 1: 184_HRV68a
   185 Group 1: 185_HRV68b
   186 Group 1: 186_HRV28
   187 Group 1: 187_HRV28a
   188 Group 1: 188_HRV28b
   189 Group 1: 189_HRV53a
   190 Group 1: 190_HRV53b
   191 Group 1: 191_HRV53
   192 Group 1: 192_HRV46a
   193 Group 1: 193_HRV46b
   194 Group 1: 194_HRV46
   195 Group 1: 195_HRV80a
```

FIG. D7 CONT'D

```
03.trace                                                           9/20/2007 5:03 PM 196 Group 1: 196_HRV80b
197 Group 1: 197_HRV80
198 Group 1: 198_HRV51
199 Group 1: 199_HRV51a
200 Group 1: 200_HRV51b
201 Group 1: 201_HRV65a
202 Group 1: 202_HRV65b
203 Group 1: 203_HRV65
204 Group 1: 204_HRV71a
205 Group 1: 205_HRV71b
206 Group 1: 206_HRV71
207 Group 1: 207_HRV8
208 Group 1: 208_HRV95
209 Group 1: 209_HRV45
210 Group 1: 210_HRV45a
211 Group 1: 211_HRV45b
212
213
214 >>>>>
215
216
217
218 Group 1:
219
220  1_HRV1A1|d    AATCCAGTAGAAAACTACATTGATGAAGTTTTAAATGAAGTTTTAGTAGTGCCGAATATA
221  2_HRV1A2|d    AATCCAGTAGAAAACTACATTGATGAAGTTTTAAATGAAGTTTTAGTAGTGCCGAATATA
222  3_HRV1A|cD    AATCCAGTAGAAAACTACATTGATGAAGTTTTAAATGAAGTTTTAGTAGTGCCGAATATA
223  4_HRV1B1|d    AATCCAGTGGAAAATTACATTGATGAAGTTTTAAATGAAGTTCTAGTAGTACCAAATATA
224  5_HRV1B2|d    AATCCAGTGGAAAATTACATTGATGAAGTTTTAAATGAAGTTCTAGTAGTACCAAATATA
225  6_HRV1B       AATCCAGTGGAAAATTACATTGATGAAGTTTTAAATGAAGTTCTAGTAGTACCAAATATA
226  7_HRV40a|d    AACCCCGTTGAAAGGTATGTTGATGAGGTTCTTAATGAAGTTCTGGTAGTTCCAAATATC
227  8_HRV40b|d    AACCCCGTTGAAAGGTATGTTGATGAGGTTCTTAATGAAGTTCTGGTAGTTCCAAATATC
228  9_HRV40       AACCCCGTTGAAAGGTATGTTGATGAGGTTCTTAATGAAGTTCTGGTAGTTCCAAATATC
229 10_HRV85       AATCCTGTTGAAAAATACGTTGATGAAGTCCTTAATGAGGTTCTAGTGGTTCCAAATATC
230 11_HRV85a|     AATCCTGTTGAAAAATACGTTGATGAAGTCCTTAATGAGGTTCTAGTGGTTCCAAATATC
231 12_HRV85b|     AATCCTGTTGAAAAATACGTTGATGAAGTCCTTAATGAGGTTCTAGTGGTTCCAAATATC
232 13_HRV56a|     AACCCAGTTGAGAGATATGTAGATGATGTTTTAAATGAAGTTTTAGTTGTTCCAAATATT
233 14_HRV56b|     AACCCAGTTGAGAGATATGTAGATGATGTTTTAAATGAAGTTTTAGTTGTTCCAAATATT
234 15_HRV56       AACCCAGTTGAGAGATATGTAGATGATGTTTTAAATGAAGTTTTAGTTGTTCCAAATATT
235 16_HRV54       AATCCTGTAGAAAGATATGTTGATGAAGTGTTAAATGAAGTGTTAGTTGTCCCAAACATT
236 17_HRV98       AATCCTGTAGAGAGATATGTTGATGAAGTATTAAATGAAGTGTTAGTTGTTCCAAACATT
237 18_HRV59a|     AACCCAGTGGAAAACTATGTTAATGATGTACTTAATGAGGTTTTAGTAGTACCAAATATA
238 19_HRV59b|     AACCCAGTGGAAAACTATGTTAATGATGTACTTAATGAGGTTTTAGTAGTACCAAATATA
239 20_HRV59       AACCCAGTGGAAAACTATGTTAATGATGTACTTAATGAGGTTTTAGTAGTACCAAATATA
240 21_HRV63       AATCCAGTAGAGAATTATGTAAATGATGTTCTTAATGAAGTGTTAGTTGTTCCAAACATA
241 22_HRV63b|     AATCCAGTAGAGAATTATGTAAATGATGTTCTTAATGAAGTGTTAGTTGTTCCAAACATA
242 23_HRV63a|     AATCCAGTAGAGAATTATGTAAATGATGTTCTTAATGAAGTGTTAGTTGTTCCAAACATA
243 24_HRV39       AATCCAGTAGAAAATTATATAGATGAAGTATTAAATGAGGTATTAGTTGTTCCTAATATA
244 25_HRV39a|     AATCCAGTAGAAAATTATATAGATGAAGTATTAAATGAGGTATTAGTTGTTCCTAATATA
245 26_HRV39b|     AATCCAGTAGAAAATTATATAGATGGAGTATTAAATGAGGTATTAGTTGTTCCTAATATA
246 27_HRV10a|     AATCCAGTTGAAAATTACATTGATAATGTACTTAATGAAGTCCTAGTGGTACCCAACATC
247 28_HRV10b|     AATCCAGTTGAAAATTACATTGATAATGTACTTAATGAAGTCCTAGTGGTACCCAACATC
248 29_HRV10       AATCCAGTTGAAAATTACATTGATAATGTACTTAATGAAGTCCTAGTGGTACCCAACATC
249 30_HRV100a     AATCCAGTAGAAAATTATGTTGAAGGTGTGCTGAATGAAGTACTAGTGGTACCTAATATT
250 31_HRV100b     AATCCAGTAGAAAATTATGTTGAAGGTGTGCTGAATGAAGTACTAGTGGTACCTAATATT
251 32_HRV100      AATCCAGTAGAAAATTATGTTGAAGGTGTGCTGAATGAAGTACTAGTGGTACCTAATATT
252 33_HRV66       AATCCAGTTGAAGATTATGTTGAGGGTGTTTTAAATGAAGTTTTAGTAGTACCAAACATC
253 34_HRV66b|     AATCCAGTTGAAGATTATGTTGAGGGTGTTTTAAATGAAGTTTTAGTAGTACCAAACATC
254 35_HRV66a|     AATCCAGTTGAAGATTATGTTGAGGGTGTTTTAAATGAAGTTTTAGTAGTACCAAACATC
255 36_HRV77a|     AATCCAGTTGAGGACTATATCGATAATGTACTTAATGAAGTCTTAGTAGTACCAAATACC
256 37_HRV77b|     AATCCAGTTGAGGACTATATCGATAATGTACTTAATGAAGTCTTAGTAGTACCAAATACC
257 38_HRV77       AATCCAGTTGAGGACTATATCGATAATGTACTTAATGAAGTCTTAGTAGTACCAAATACC
258 39_HRV62a      AATCCAATTGAAAATTATGTAGATCAAGTACTTAATGAAGTTTTAGTTGTACCAAATATT
259 40_HRV62b      AATCCAATTGAAAATTATGTAGATCAAGTACTTAATGAAGTTTTAGTTGTACCAAATATT
260 41_HRV25       AATCCAATTGAAAATTATGTAGATCAAGTACTTAATGAGGTTCTAGTCGTACCAAATATT
```

FIG. D7 CONT'D

```
03.trace                                                                    9/20/2007 5:03 PM 261  42_HRV29a     AACCCAGTTGAAAACTATGTGGATGAGGTGCTTAATGAAGTTTTAGTTGTGCCTAACATC
262  43_HRV29b     AACCCAGTTGAAAACTATGTGGATGAGGTGCTTAATGAAGTTTTAGTTGTGCCTAACATC
263  44_HRV44a     AACCCAGTTGAAAATTATGTGGATGAAGTACTTAATGAAGTCTTAGTTGTGCCTAATATC
264  45_HRV44b     AACCCAGTTGAAAATTATGTGGATGAAGTACTTAATGAAGTCTTAGTTGTGCCTAATATC
265  46_HRV31      AATCCAGTTGAAAACTATGTGGAAGAGGTTCTTAATGAAGTCTTAGTAGTACCTAATATC
266  47_HRV31a|    AATCCAGTTGAAAACTATGTGGAAGAGGTTCTTAATGAAGTCTTAGTAGTACCTAATATC
267  48_HRV31b|    AATCCAGTTGAAAACTATGTGGAAGAGGTTCTTAATGAAGTCTTAGTAGTACCTAATATC
268  49_HRV47      AACCCAGTCGAAAATTATGTGGAAGAGGTACTTAATGAGGTCTTAGTTGTACCAAATATC
269  50_HRV47a|    AACCCAGTCGAAAATTATGTGGAAGAGGTACTTAATGAGGTCTTAGTTGTACCAAATATC
270  51_HRV47b|    AACCCAGTCGAAAATTATGTGGAAGAGGTACTTAATGAGGTCTTAGTTGTACCAAATATC
271  52_HRV11      AACCCAGTGGAGGATTATGTTGATGGAATTCTAAATGAGGTTTTAGTTGTACCTAATATA
272  53_HRV11b|    AACCCAGTGGAGGATTATGTTGATGGAATTCTAAATGAGGTTTTAGTTGTACCTAATATA
273  54_HRV11a|    AACCCAGTGGAGGATTATGTTGATGGAATTCTAAATGAGGTTTTAGTTGTACCTAATATA
274  55_HRV76      AACCCAGTTGAAAATTACGTGGATGAGATATTAAATGAGGTTCTTGTAGTACCAAACATC
275  56_HRV76b|    AACCCAGTTGAAAATTACGTGGATGAGATATTAAATGAGGTTCTTGTAGTACCAAACATC
276  57_HRV76a|    AACCCAGTTGAAAATTACGTGGATGAGATATTAAATGAGGTTCTTGTAGTACCAAACATC
277  58_HRV33      AATCCAGTAGAGAATTATATAGAAGAGGTGTTGAATGAGGTTTTAGTAGTGCCTAATATC
278  59_HRV33b|    AATCCAGTAGAGAATTATATAGAAGAGGTGTTGAATGAGGTTTTAGTAGTGCCTAATATC
279  60_HRV33a|    AATCCAGTAGAGAATTATATAGAAGAGGTGTTGAATGAGGTTTTAGTAGTGCCTAATATC
280  61_HRV24a|    AACCCAGTAGAAAATTATATAGATGAGGTTTTGAATGAAGTACTGGTTGTGCCTAATATT
281  62_HRV24b|    AACCCAGTAGAAAATTATATAGATGAGGTTTTGAATGAAGTACTGGTTGTGCCTAATATT
282  63_HRV24      AACCCAGTAGAAAATTATATAGATGAGGTTTTGAATGAAGTACTGGTTGTGCCTAATATT
283  64_HRV90      AATCCAGTGGAAAATTATATAGATGAAGTCCTAAATGAGGTATTGGTTGTCCCTAATATT
284  65_HRV90a|    AATCCAGTGGAAAATTATATAGATGAAGTCCTAAATGAGGTATTGGTTGTCCCTAATATT
285  66_HRV90b|    AATCCAGTGGAAAATTATATAGATGAAGTCCTAAATGAGGTATTGGTTGTCCCTAATATT
286  67_HRV34      AATCCAGTTGAAAATTACATAGATGAGGTACTAAATGAGGTATTGGTTGTACCAAACATT
287  68_HRV34b|    AATCCAGTTGAAAATTACATAGATGAGGTACTAAATGAGGTATTGGTTGTACCAAACATT
288  69_HRV34a|    AATCCAGTTGAAAATTACATAGATGAGGTACTAAATGAGGTATTGGTTGTACCAAACATT
289  70_HRV50a|    AATCCAGTGGAGAATTACATAGATGAAGTATTAAATGAGGTATTAGTTGTCCCAAATATC
290  71_HRV50b|    AATCCAGTGGAGAATTACATAGATGAAGTATTAAATGAGGTATTAGTTGTCCCAAATATC
291  72_HRV50      AATCCAGTGGAGAATTACATAGATGAAGTATTAAATGAGGTATTACTTGTCCCAAATATC
292  73_HRV18a|    AATCCAGTAGAGAATTATATAGATGAAGTACTTAATGAAGTGTTAGTGGTCCCAAATGTG
293  74_HRV18b|    AATCCAGTAGAGAATTATATAGATGAAGTACTTAATGAAGTGTTAGTGGTCCCAAATGTG
294  75_HRV18      AATCCAGTAGAGAATTATATAGATGAAGTACTTAATGAAGTGTTAGTGGTCCCAAATGTG
295  76_HRV55      AATCCTGTAGAGAGATATGTTGATGAAGTCCTGAATGAAGTGCTAGTAGTTCCAAATATT
296  77_HRV55b|    AATCCTGTAGAGAGATATGTTGATGAAGTCCTGAATGAAGTGCTAGTAGTTCCAAATATT
297  78_HRV55a|    AATCCTGTAGAGAGATATGTTGATGAAGTCCTGAATGAAGTGCTAGTAGTTCCAAATATT
298  79_HRV57      AACCCAGTAGAAAATTTTGTGGATGAGATCTTGAATGAAGTTTTGGTGGTTCCAGATATC
299  80_HRV57a|    AACCCAGTAGAAAATTTTGTGGATGAGATCTTGAATGAAGTTTTGGTGGTTCCAGATATC
300  81_HRV57b|    AACCCAGTAGAAAATTTTGTGGATGAGATCTTGAATGAAGTTTTGGTGGTTCCAGATATC
301  82_HRV21      AATCCTGTAGAGAATTATATAGATGAAGTCCTAAATGAAGTCTTAGTAGTGCCAAATATC
302  83_HRVHan     AATCCTGTAGAGAATTACGTAGATGAAGTTCTAAATGAGGTCTTAGTAGTGCCAAATATC
303  84_HRV43      AATCCTGTTGAAAATTATGTTGATGAAATTTTAAATCAAGTTCTTGTAGTCCCAAACACT
304  85_HRV43b|    AATCCTGTTGAAAATTATGTTGATGAAATTTTAAATCAAGTTCTTGTAGTCCCAAACACT
305  86_HRV43a|    AATCCTGTTGAAAATTATGTTGATGAAATTTTAAATCAAGTTCTTGTAGTCCCAAACACT
306  87_HRV75      AATCCAGTTGAAAATTATGTGGATGAAATTTTAAACCAAGTTCTGGTAGTTCCAAACACC
307  88_HRV75b|    AATCCAGTTGAAAATTATGTGGATGAAATTTTAAACCAAGTTCTGGTAGTTCCAAACACC
308  89_HRV75a|    AATCCAGTTGAAAATTATGTGGATGAAATTTTAAACCAAGTTCTGGTAGTTCCAAACACC
309  96_HRV9a|d    AATCCAGTGGAGAATTACATAGATCAGGTGCTTAATGAGGTTTTGGTAGTCCCAAACATT
310  97_HRV9b|d    AATCCAGTGGAGAATTACATAGATCAGGTGCTTAATGAGGTTTTGGTAGTCCCAAACATT
311  98_HRV9       AATCCAGTGGAGAATTACATAGATCAGGTGCTTAATGAGGTTTTGGTAGTCCCAAACATT
312  99_HRV32      AATCCTGTGGAGAATTACATAGATCAAGTTTTAAATGAAGTTTTGGTAGTTCCAAACATC
313  100_HRV32a    AATCCTGTGGAGAATTACATAGATCAAGTTTTAAATGAAGTTTTGGTAGTTCCAAACATC
314  101_HRV32b    AATCCTGTGGAGAATTACATAGATCAAGTTTTAAATGAAGTTTTGGTAGTTCCAAACATC
315  102_HRV67     AACCCAGTAGAAGATTATGTAGATCAGGTATTGAATGAGGTCCTGGTGGTGCCAAATATA
316  103_HRV67a    AACCCAGTAGAAGATTATGTAGATCAGGTATTGAATGAGGTCCTGGTGGTGCCAAATATA
317  104_HRV67b    AACCCAGTAGAAGATTATGTAGATCAGGTATTGAATGAGGTCCTGGTGGTGCCAAATATA
318  105_HRV15     AACCCAGTGGAGAATTACATAGATGAAGTGTTAAATGAGGTTCTAGTAGTTCCAAACATT
319  106_HRV15a    AACCCAGTGGAGAATTACATAGATGAAGTGTTAAATGAGGTTCTAGTAGTTCCAAACATT
320  107_HRV15b    AACCCAGTGGAGAATTACATAGATGAAGTGTTAAATGAGGTTCTAGTAGTTCCAAACATT
321  108_HRV74a    AACCCAGTGGAGAATTACATAGATGAAGTGTTAGTTGAAGTGTTAGTTGTTCCAAATATT
322  109_HRV74b    AACCCAGTGGAGAATTACATAGATGAAGTGTTGAATGAAGTGTTAGTTGTTCCAAATATT
323  110_HRV74     AACCCAGTGGAGAATTACATAGATGAAGTGTTGAATGAAGTGTTAGTTGTTCCAAATATT
324  111_HRV38a    AACCCAGTAGAGGAATACATAGATGGAGTCTTGAATGAGGTTCTTGTGGTTCCGAACATT
325  112_HRV38b    AACCCAGTAGAGGAATACATAGATGGAGTCTTGAATGAGGTTCTTGTGGTTCCGAACATT
```

FIG. D7 CONT'D

```
03.trace                                                                                            9/20/2007 5:03 PM 326  113_HRV38    AACCCAGTAGAGGAATACATAGATGGAGTCTTGAATGAGGTTCTTGTGGTTCCGAACATT
327  114_HRV60    AATCCAGTAGAAAGCTACATAGATGGGGTCTTAAACGAAGTCCTTGTGGTTCCAAACATT
328  115_HRV60a   AATCCAGTAGAAAGCTACATAGATGGGGTCTTAAACGAAGTCCTTGTGGTTCCAAACATT
329  116_HRV60b   AATCCAGTAGAAAGCTACATAGATGGGGTCTTAAACGAAGTCCTTGTGGTTCCAAACATT
330  117_HRV64a   AACCCAGTTGAACAATACATTGATGGTGTGTTGAATGAAGTTTTGATTGTCCCAAACATC
331  118_HRV64b   AACCCAGTTGAACAATACATTGATGGTGTGTTGAATGAAGTTTTGATTGTCCCAAACATC
332  119_HRV64    AACCCAGTTGAACAATACATTGATGGTGTGTTGAATGAAGTTTTGATTGTCCCAAACATC
333  120_HRV94a   AATCCAGTTGAGAAATACATTGATGGTGTATTGAATGAAGTTTTAGTTGTTCCAAATATC
334  121_HRV94b   AATCCAGTTGAGAAATACATTGATGGTGTATTGAATGAAGTTTTAGTTGTTCCAAATATC
335  122_HRV94    AATCCAGTTGAGAAATACATTGATGGTGTATTGAATGAAGTTTTAGTTGTTCCAAATATC
336  123_HRV22    AACCCTGTAGAGAAATACATTGATGGTGTATTGAATGAAGTATTGGTTGTTCCAAACACA
337  124_HRV22a   AACCCTGTAGAGAAATACATTGATGGTGTATTGAATGAAGTATTGGTTGTTCCAAACACA
338  125_HRV22b   AACCCTGTAGAGAAATACATTGATGGTGTATTGAATGAAGTATTGGTTGTTCCAAACACA
339  126_HRV82    AATCCAGTTGAAAAGTATGTTGATAGTGTTTTAAACGAGGTATTAGTTGTTCCTAACATT
340  127_HRV82b   AATCCAGTTGAAAAGTATGTTGATAGTGTTTTAAACGAGGTATTAGTTGTTCCTAACATT
341  128_HRV82a   AATCCAGTTGAAAAGTATGTTGATAGTGTTTTAAACGAGGTATTAGTTGTTCCTAACATT
342  129_HRV19    AATCCTGTAGAGAAATATGTGGACACCATTCTGAATGAGGTGCTAGTTGTCCCAAATATC
343  130_HRV19a   AATCCTGTAGAGAAATATGTGGACACCATTCTGAATGAGGTGCTAGTTGTCCCAAATATC
344  131_HRV19b   AATCCTGTAGAGAAATATGTGGACACCATTCTGAATGAGGTGCTAGTTGTCCCAAATATC
345  132_HRV13    AATCCTGTTGAAAGGTATGTAGATGAAGTCTTGAATGAAGTTCTTGTAGTACCAAATATC
346  133_HRV13a   AATCCTGTTGAAAGGTATGTAGATGAAGTCTTGAATGAAGTTCTTGTAGTACCAAATATC
347  134_HRV13b   AATCCTGTTGAAAGGTATGTAGATGAAGTCTTGAATGAAGTTCTTGTAGTACCAAATATC
348  135_HRV41    AATCCTGTAGAAAGGTATGTGGATGAGGTCCTGAATGAGGTTCTTGTGGTACCAAATATT
349  136_HRV41a   AATCCTGTAGAAAGGTATGTGGATGAGGTCCTGAATGAGGTTCTTGTGGTACCAAATATT
350  137_HRV41b   AATCCTGTAGAAAGGTATGTGGATGAGGTCCTGAATGAGGTTCTTGTGGTACCAAATATT
351  138_HRV73    AATCCTGTAGAAAGATATGTAGATGAAGTTTTGAATGAAGTCCTTGTAGTACCCAATATC
352  139_HRV73b   AATCCTGTAGAAAGATATGTAGATGAAGTTTTGAATGAAGTCCTTGTAGTACCCAATATC
353  140_HRV73a   AATCCTGTAGAAAGATATGTAGATGAAGTTTTGAATGAAGTCCTTGTAGTACCCAATATC
354  141_HRV61    AACCCTGTGGAAAGATATGTAGATGAAGTTTTAAATGAAGTGCTTGTAGTCCCAAACATT
355  142_HRV61a   AACCCTGTGGAAAGATATGTAGATGAAGTTTTAAATGAAGTGCTTGTAGTCCCAAACATT
356  143_HRV61b   AACCCTGTGGAAAGATATGTAGATGAAGTTTTAAATGAAGTGCTTGTAGTCCCAAACATT
357  144_HRV96    AACCCTGTAGAGAGATATGTAGATGAAGTCTTGAATGAGGTTCTTGTAGTCCCTAATATT
358  145_HRV96b   AACCCTGTAGAGAGATATGTAGATGAAGTCTTGAATGAGGTTCTTGTAGTCCCTAATATT
359  146_HRV96a   AACCCTGTAGAGAGATATGTAGATGAAGTCTTGAATGAGGTTCTTGTAGTCCCTAATATT
360  90_HRV16a|   AATCCAGTGGAAAGATATGTAGATGAAGTCTTAAATGAAGTGTTAGTAGTGCCCAATATT
361  91_HRV16b|   AATCCAGTGGAAAGATATGTAGATGAAGTCTTAAATGAAGTGTTAGTAGTGCCCAATATT
362  92_1AYM_A    AATCCAGTGGAAAGATATGTAGATGAAGTCTTAAATGAAGTGTTAGTAGTGCCCAATATT
363  93_HRV81a|   AACCCAGTGGAGCGGTATGTGGATGAAGTCTTAAATGAAGTATTGGTAGTCCCTAATATT
364  94_HRV81b|   AACCCAGTGGAGCGGTATGTGGATGAAGTCTTAAATGAGGTATTGGTAGTCCCTAATATT
365  95_HRV81     AACCCAGTGGAGCGGTATGTGGATGAAGTCTTAAATGAGGTATTGGTAGTCCCTAATATT
366  147_HRV2     AACCCTGTTGAGAATTATATAGATGAAGTTCTTAATGAAGTTTTAGTTGTCCCAAATATT
367  148_HRV2a|   AACCCTGTTGAGAATTATATAGATGAAGTTCTTAATGAAGTTTTAGTTGTCCCAAATATT
368  149_HRV2b|   AACCCTGTTGAGAATTATATAGATGAAGTTCTTAATGAAGTTTTAGTTGTCCCAAATATT
369  150_HRV49a   AATCCTGTTGAACACTACATAGATGAGGTCCTTAATGAGGTTTTAGTTGTTCCAAATATT
370  151_HRV49b   AATCCTGTTGAACACTACATAGATGAGGTCCTTAATGAGGTTTTAGTTGTTCCAAATATT
371  152_HRV49    AATCCTGTTGAACACTACATAGATGAGGTCCTTAATGAGGTTTTAGTTGTTCCAAATATT
372  153_HRV23a   AATCCAATTGAGAACTATGTAGATGAAGTTCTTAATGAAGTCTTAGTTGTTCCCAATATC
373  154_HRV23b   AATCCAATTGAGAACTATGTAGATGAAGTTCTTAATGAAGTCTTAGTTGTTCCCAATATC
374  155_HRV23    AATCCAATTGAGAACTATGTAGATGAAGTTCTTAATGAAGTCTTAGTTGTTCCCAATATC
375  156_HRV30a   AACCCGGTTGAAAATTTTGTAGATGAAGTTCTTAGTGAAGTTTTAGTTGTTCCAAACATT
376  157_HRV30b   AACCCGGTTGAAAATTTTGTAGATGAAGTTCTTAGTGAAGTTTTAGTTGTTCCAAACATT
377  158_HRV30    AACCCGGTTGAAAATTTTGTAGATGAAGTTCTTAGTGAAGTTTTAGTTGTTCCAAACATT
378  159_HRV7     AACCCGGTAGAGAATTATGTAGATAGCTTACTAAATGAAGTATTAGTGGTACCTAATATT
379  160_HRV7b|   AACCCGGTAGAGAATTATGTAGATAGCTTACTAAATGAAGTATTAGTGGTACCTAATATT
380  161_HRV7a|   AACCCGGTAGAGAATTATGTAGATAGCTTACTAAATGAAGTATTAGTGGTACCTAATATT
381  162_HRV88    AATCCAGTAGAAAACTATGTAGATAACTTGTTAAACGAAGTGCTAGTAGTTCCTAACATT
382  163_HRV88a   AATCCAGTAGAAAACTATGTAGATAACTTGTTAAACGAAGTGCTAGTAGTTCCTAACATT
383  164_HRV88b   AATCCAGTAGAAAACTATGTAGATAACTTGTTAAACGAAGTGCTAGTAGTTCCTAACATT
384  165_HRV36a   AATCCAGTTGAAAATTACATAGATAATGTATTAAATGAAGTACTTGTAGTGCCAAACATC
385  166_HRV36b   AATCCAGTTGAAAATTACATAGATAATGTATTAAATGAAGTACTTGTAGTGCCAAACATC
386  167_HRV36    AATCCAGTTGAAAATTACATAGATAATGTATTAAATGAAGTACTTGTAGTGCCAAACATC
387  168_HRV89a   AACCCAGTTGAAAATTATATAGATAGTGTATTAAATGAAGTTCTTGTGGTGCCAAATATC
388  169_HRV89b   AACCCAGTTGAAAATTATATAGATAGTGTATTAAATGAAGTTCTTGTGGTGCCAAATATC
389  170_HRV89    AACCCAGTTGAAAATTATATAGATAGTGTATTAAATGAAGTTCTTGTGGTGCCAAATATC
390  171_HRV58    AATCCAGTAGAAAATTACATAGATAATGTGTTAAATGAAGTACTTGTAGTTCCAAATATC
```

FIG. D7 CONT'D

03.trace                                                                    9/20/2007 5:03 PM

```
391 172_HRV58a    AATCCAGTAGAAAATTACATAGATAATGTGTTAAATGAAGTACTTGTAGTTCCAAATATC
392 173_HRV58b    AATCCAGTAGAAAATTACATAGATAATGTGTTAAATGAAGTACTTGTAGTTCCAAATATC
393 174_HRV12a    AATCCAGTAGAGAGATATGTTGATGAGGTGCTAAATGAAGTTCTAGTTGTTCCAAACATA
394 175_HRV12b    AATCCAGTAGAGAGATATGTTGATGAGGTGCTAAATGAAGTTCTAGTTGTTCCAAACATA
395 176_HRV12     AATCCAGTAGAGAGATATGTTGATGAGGTGCTAAATGAAGTTCTAGTTGTTCCAAACATA
396 177_HRV78a    AATCCAGTGGAAGAATATGTTGATCAGGTTTTAAATGAGGTTTTAGTTGTTCCAAACATA
397 178_HRV78b    AATCCAGTGGAAGAATATGTTGATCAGGTTTTAAATGAGGTTTTAGTTGTTCCAAACATA
398 179_HRV78     AATCCAGTGGAAGAATATGTTGATCAGGTTTTAAATGAGGTTTTAGTTGTTCCAAACATA
399 180_HRV20     AACCCAGTGGAAAGGTACACAGAAGCTATTTTAAATGAAGTTCTTGTAGTTCCAAATATC
400 181_HRV20a    AACCCAGTGGAAAGGTACACAGAAGCTATTTTAAATGAAGTTCTTGTAGTTCCAAATATC
401 182_HRV20b    AACCCAGTGGAAAGGTACACAGAAGCTATTTTAAATGAAGTTCTTGTAGTTCCAAATATC
402 183_HRV68     AACCCAGTTGAAAAATACACAGAAGCCGTTCTTAATGAGGTCCTTGTGGTTCCAAACATA
403 184_HRV68a    AACCCAGTTGAAAAATACACAGAAGCCGTTCTTAATGAGGTCCTTGTGGTTCCAAACATA
404 185_HRV68b    AACCCAGTTGAAAAATACACAGAAGCCGTTCTTAATGAGGTCCTTGTGGTTCCAAACATA
405 186_HRV28     AATCCAGTTGAAAAATATACTGAAGCACTACTTAATGAAGTGCTTGTTGTGCCAAACATC
406 187_HRV28a    AATCCAGTTGAAAAATATACTGAAGCACTACTTAATGAAGTGCTTGTTGTGCCAAACATC
407 188_HRV28b    AATCCAGTTGAAAAATATACTGAAGCACTACTTAATGAAGTGCTTGTTGTGCCAAACATC
408 189_HRV53a    AACCCGGTAGAGAAATACACAGAGGCTATCTTAAATGAAGTATTAGTAGTCCCAAACATT
409 190_HRV53b    AACCCGGTAGAGAAATACACAGAGGCTATCTTAAATGAAGTATTAGTAGTCCCAAACATT
410 191_HRV53     AACCCGGTAGAGAAATACACAGAGGCTATCTTAAATGAAGTATTAGTAGTCCCAAACATT
411 192_HRV46a    AATCCAGTGGAAAAATATACAGAAGCTGTTCTTAATGAGGTCCTTGTAGTACCTAACATC
412 193_HRV46b    AATCCAGTGGAAAAATATACAGAAGCTGTTCTTAATGAGGTCCTTGTAGTACCTAACATC
413 194_HRV46     AATCCAGTGGAAAAATATACAGAAGCTGTTCTTAATGAGGTCCTTGTAGTACCTAACATC
414 195_HRV80a    AATCCAGTCGAAAAATACACAGAAGCAATCCTCAATGAAGTTCTTGTTGTACCAAACATC
415 196_HRV80b    AATCCAGTCGAAAAATACACAGAAGCAATCCTCAATGAAGTTCTTGTTGTACCAAACATC
416 197_HRV80     AATCCAGTCGAAAAATACACAGAAGCAATCCTCAATGAAGTTCTTGTTGTACCAAACATC
417 198_HRV51     AACCCTGTTGAAAAATATACAGAGGCTTTACTCAATGAAGTGTTGGTGGTTCCCAACATA
418 199_HRV51a    AACCCTGTTGAAAAATATACAGAGGCTTTACTCAATGAAGTGTTGGTGGTTCCCAACATA
419 200_HRV51b    AACCCTGTTGAAAAATATACAGAGGCTTTACTCAATGAAGTGTTGGTGGTTCCCAACATA
420 201_HRV65a    AATCCAATTGAGAAGTATACAGAAGCTCTACTTAATGAAGTGTTGGTGGTCCCAAATATA
421 202_HRV65b    AATCCAATTGAGAAGTATACAGAAGCTCTACTTAATGAAGTGTTGGTGGTCCCAAATATA
422 203_HRV65     AATCCAATTGAGAAGTATACAGAAGCTCTACTTAATGAAGTGTTGGTGGTCCCAAATATA
423 204_HRV71a    AATCCTGTAGAAAAATATACAGAAGCAATACTCAATGAGGTTCTAGTTGTGCCAAATATA
424 205_HRV71b    AATCCTGTAGAAAAATATACAGAAGCAATACTCAATGAGGTTCTAGTTGTGCCAAATATA
425 206_HRV71     AATCCTGTAGAAAAATATACAGAAGCAATACTCAATGAGGTTCTAGTTGTGCCAAATATA
426 207_HRV8      AACCCTATTGAACAATTCACAGAGGCAGTATTAAACGAGGTTCTTGTAGTTCCAAACACA
427 208_HRV95     AACCCTATTGAACAATTCACAGAGGCAGTATTAAACGAGGTTCTTGTAGTTCCAAATACA
428 209_HRV45     AACCCTGTTGAACAATTTGCAGAAGCAGTCCTTGATCAAGTATTAGTAGTTCCAAACACT
429 210_HRV45a    AACCCTGTTGAACAATTTGCAGAAGCAGTCCTTGATCAAGTATTAGTAGTTCCAAACACT
430 211_HRV45b    AACCCTGTTGAACAATTTGCAGAAGCAGTCCTTGATCAAGTATTAGTAGTTCCAAACACT
431 GROUP_1       AA-CC--T-GA----T------A-----T--T-----A-GT--T--T-GT-CC--A----
432
433 1_HRV1A1|d    AAAGAAAGTCATCACACTACATCAAACTCTGCCCCACTTTTAGATGCTGCAGAGACGGGA
434 2_HRV1A2|d    AAAGAAAGTCATCACACTACATCAAACTCTGCCCCACTTTTAGATGCTGCAGAGACGGGA
435 3_HRV1A|cD    AAAGAAAGTCATCACACTACATCAAACTCTGCCCCACTTTTAGATGCTGCAGAGACGGGA
436 4_HRV1B1|d    AAAGAAAGCCATCACACTACATCAAATTCTGCTCCACTCTTGGATGCTGCAGAGACAGGA
437 5_HRV1B2|d    AAAGAAAGCCATCACACTACATCAAATTCTGCTCCACTCTTGGATGCTGCAGAGACAGGA
438 6_HRV1B       AAAGAAAGCCATCACACTACATCAAATTCTGCTCCACTCTTGGATGCTGCAGAGACAGGA
439 7_HRV40a|d    AGAGAGAGCCATCCAACTACATCAAATTCGGCCCCTGCCTTGGATGCAGCAGAGACTGGA
440 8_HRV40b|d    AGAGAGAGCCATCCAACTACATCAAATTCGGCCCCTGCCTTGGATGCAGCAGAGACTGGA
441 9_HRV40       AGAGAGAGCCATCCAACTACATCAAATTCGGCCCCTGCCTTGGATGCAGCAGAGACTGGA
442 10_HRV85      AAAGAGAGTCACCCAACTATATCAAATTCAGCTCCTGCTTTGGATGCAGCAGAGACTGGC
443 11_HRV85a|    AAAGAGAGTCACCCAACTATATCAAATTCAGCTCCTGCTTTGGATGCAGCAGAGACTGGC
444 12_HRV85b|    AAAGAGAGTCACCCAACTATATCAAATTCAGCTCCTGCTTTGGATGCAGCAGAGACTGGC
445 13_HRV56a|    AGGGAGAGCCATCCATCCACATCAAATTCTGCCCCTGCATTAGATGCTGCTGAAACTGGC
446 14_HRV56b|    AGGGAGAGCCATCCATCCACATCAAATTCTGCCCCTGCATTAGATGCTGCTGAAACTGGC
447 15_HRV56      AGGGAGAGCCATCCATCCACATCAAATTCTGCCCCTGCATTAGATGCTGCTGAAACTGGC
448 16_HRV54      AGAGAAAGTCATCCAGCTACATCTAATTCAGCCCCTGCGCTAGATGCGGCAGAAACTGGA
449 17_HRV98      AAAGAAAGTCATCCAGCTACATCTAATTCGGCCCCTACACTAGATGCAGCAGAAACTGGG
450 18_HRV59a|    CAGGAAAGCCACCCAACCACCTCAAATGCTGCTCCAGCATTAGATGCAGCAGAGACTGGA
451 19_HRV59b|    CAGGAAAGCCACCCAACCACCTCAAATGCTGCTCCAGCATTAGATGCAGCAGAGACTGGA
452 20_HRV59      CAGGAAAGCCACCCAACCACCTCAAATGCTGCTCCAGCATTAGATGCAGCAGAGACTGGA
453 21_HRV63      CAAGAAAGCCATCCAACCACATCAAACGCTGCTCCTGTACTTGATGCTGCGGAAACAGGA
454 22_HRV63b|    CAAGAAAGCCATCCAACCACATCAAACGCTGCTCCTGTACTTGATGCTGCGGAAACAGGA
455 23_HRV63a|    CAAGAAAGCCATCCAACCACATCAAACGCTGCTCCTGTACTTGATGCTGCGGAAACAGGA
```

FIG. D7 CONT'D

```
03.trace                                                          9/20/2007 5:03 PM 456  24_HRV39      AGAGAGAGCCATCCAACTACATCTAATGCAGCTACAGCTTTGGATGCTGCTGAAACTGGA
457  25_HRV39a|    AGAGAGAGCCATCCAACTACATCTAATGCAGCTACAGCTTTGGATGCTGCTGAAACTGGA
458  26_HRV39b|    AGAGAGAGCCATCCAACTACATCTAATGCAGCTCCAGCTTTGGATGCTGCTGAAACTGGA
459  27_HRV10a|    AGAGAAAGTCATCCAAGCACCTCTAACTCTGCCCCAATTCTCGATGCAGCTGAGACTGGT
460  28_HRV10b|    AGAGAAAGTCATCCAAGCACCTCTAACTCTGCCCCAATTCTCGATGCAGCTGAGACTGGT
461  29_HRV10      AGAGAAAGTCATCCAAGCACCTCTAACTCTGCCCCAATTCTCGATGCAGCTGAGACTGGT
462  30_HRV100a    AGAGAGAGCCATCCAAGCACCTCAAACTCTGCTCCAATCCTTGATGCTGCTGAAACTGGC
463  31_HRV100b    AGAGAGAGCCATCCAAGCACCTCAAACTCTGCTCCAATCCTTGATGCTGCTGAAACTGGC
464  32_HRV100     AGAGAGAGCCATCCAAGCACCTCAAACTCTGCTCCAATCCTTGATGCTGCTGAAACTGGC
465  33_HRV66      AAGGAAAGCCATCCAAGCACATCAAATGCTGCCCCAATACTAGATGCAGCTGAAACAGGT
466  34_HRV66b|    AAGGAAAGCCATCCAAGCACATCAAATGCTGCCCCAATACTAGATGCAGCTGAAACAGGT
467  35_HRV66a|    AAGGAAAGCCATCCAAGCACATCAAATGCTGCCCCAATACTAGATGCAGCTGAAACAGGT
468  36_HRV77a|    AAGGAGAGTCATCCAAGCACTTCTAACTCTGCTCCTATACTAGATGCAGCTGAAACAGGC
469  37_HRV77b|    AAGGAGAGTCATCCAAGCACTTCTAACTCTGCTCCTATACTAGATGCAGCTGAAACAGGC
470  38_HRV77      AAGGAGAGTCATCCAAGCACTTCTAACTCTGCTCCTATACTAGATGCAGCTGAAACAGGC
471  39_HRV62a     AAAGAAAGTCACCCTAGTACGTCAAACTCTGCCCCAATTCTAGATGCTGCTGAAACCGGA
472  40_HRV62b     AAAGAAAGTCACCCTAGTACGTCAAACTCTGCCCCAATTCTAGATGCTGCTGAAACCGGA
473  41_HRV25      AAAGAAAGTCACCCAAGCACATCAAATTCTGCCCCAATTCTAGATGCTGCTGAAACTGGA
474  42_HRV29a     AGGGAGAGCCACCCAAGCACGTCCAACTCTGCACCAATCTTGGATGCTGCTGAGACTGGA
475  43_HRV29b     AGGGAGAGCCACCCAAGCACGTCCAACTCTGCACCAATCTTGGATGCTGCTGAGACTGGA
476  44_HRV44a     AGAGAGAGCCACCCAAGCACATCTAACTCTGCTCCAATTTTGGATGCTGCTGAAACTGGA
477  45_HRV44b     AGAGAGAGCCACCCAAGCATATCTAACTCTGCTCCAATTTTGGATGCTGCTGAAACTGGA
478  46_HRV31      AAAGAAAGCCATCCAAGCACATCTAATTCTGCCCCAATCCTGGACGCTGCTGAAACTGGA
479  47_HRV31a|    AAAGAAAGCCATCCAAGCACATCTAATTCTGCCCCAATCCTGGACGCTGCTGAAACTGGA
480  48_HRV31b|    AAAGAAAGCCATCCAAGCACATCTAATTCTGCCCCAATCCTGGACGCTGCTGAAACTGGA
481  49_HRV47      AAAGAAAGTCATCCAAGTACATCCAACTCTGCCCCGATTTTAGATGCTGCTGAAACTGGA
482  50_HRV47a|    AAAGAAAGTCATCCAAGTACATCCAACTCTGCCCCGATTTTAGATGCTGCTGAAACTGGA
483  51_HRV47b|    AAAGAAAGTCATCCAAGTACATCCAACTCTGCCCCGATTTTAGATGCTGCTGAAACTGGA
484  52_HRV11      AAGGAGAGCCAAGCTACCACATCAAACTCAGCACCTGCTCTAGATGCAGCTGAAACCGGA
485  53_HRV11b|    AAGGAGAGCCAAGCTACCACATCAAACTCAGCACCTGCTCTAGATGCAGCTGAAACCGGA
486  54_HRV11a|    AAGGAGAGCCAAGCTACCACATCAAACTCAGCACCTGCTCTAGATGCAGCTGAAACCGGA
487  55_HRV76      AAAGAGAGTCAGGCTACCACATCAAATGCAGCACCTGCTTTGGATGCAGCTGAGACTGGG
488  56_HRV76b|    AAAGAGAGTCAGGCTACCACATCAAATGCAGCACCTGCTTTGGATGCAGCTGAGACTGGG
489  57_HRV76a|    AAAGAGAGTCAGGCTACCACATCAAATGCAGCACCTGCTTTGGATGCAGCTGAGACTGGG
490  58_HRV33      AGAGAGAGTCAAGCAACCACATCAAATTCAGCACCTGCCTTAGATGCAGCTGAGACTGGA
491  59_HRV33b|    AGAGAGAGTCAAGCAACCACATCAAATTCAGCACCTGCCTTAGATGCAGCTGAGACTGGA
492  60_HRV33a|    AGAGAGAGTCAAGCAACCACATCAAATTCAGCACCTGCCTTAGATGCAGCTGAGACTGGA
493  61_HRV24a|    AAGGAAAGTAAACCATCAACATCAAACTCAGCACCAGCTTTGGATGCAGCAGAAACTGGA
494  62_HRV24b|    AAGGAAAGTAAACCATCAACATCAAACTCAGCACCAGCTTTGGATGCAGCAGAAACTGGA
495  63_HRV24      AAGGAAAGTAAACCATCAACATCAAACTCAGCACCAGCTTTGGATGCAGCAGAAACTGGA
496  64_HRV90      AAGGAAAGTAAACCTTCAACTTCAAACTCAGCGCCAGCTTTAGATGCAGCAGAAACCGGA
497  65_HRV90a|    AAGGAAAGTAAACCTTCAACTTCAAACTCAGCGCCAGCTTTAGATGCAGCAGAAACCGGA
498  66_HRV90b|    AAGGAAAGTAAACCTTCAACTTCAAACTCAGCGCCAGCTTTAGATGCAGCAGAAACCGGA
499  67_HRV34      AAAGAAAGCCAAGCCACCACATCAAACTCTGCCCCCGCACTGGATGCAGCTGAGACTGGT
500  68_HRV34b|    AAAGAAAGCCAAGCCACCACATCAAACTCTGCCCCCGCACTGGATGCAGCTGAGACTGGT
501  69_HRV34a|    AAAGAAAGCCAAGCCACCACATCAAACTCTGCCCCCGCACTGGATGCAGCTGAGACTGGT
502  70_HRV50a|    AAGGAGAGTCAAGCCACTACATCAAACTCTGCCCCTGCTTTAGATGCAGCTGAAACTGGA
503  71_HRV50b|    AAGGAGAGTCAAGCCACTACATCAAACTCTGCCCCTGCTTTAGATGCAGCTGAAACTGGA
504  72_HRV50      AAGGAGAGTCAAGCCACTACATCAAACTCTGCCCCTGCTTTAGATGCAGCTGAAACTGGA
505  73_HRV18a|    AATGAAAGTCACGCAATTACATCAAATTCAGCCCCTGCTTTAGATGCCGCTGAAACTGGT
506  74_HRV18b|    AATGAAAGTCACGCAATTACATCAAATTCAGCCCCTGCTTTAGATGCCGCTGAAACTGGT
507  75_HRV18      AATGAAAGTCACGCAATTACATCAAATTCAGCCCCTGCTTTAGATGCCGCTGAAACTGGT
508  76_HRV55      AGGGAGAGTCAAGCAGCAACATCAAATTCAGCTCCAGTACTAGATGCAGCAGAAACTGGG
509  77_HRV55b|    AGGGAGAGTCAAGCAGCAACATCAAATTCAGCTCCAGTACTAGATGCAGCAGAAACTGGG
510  78_HRV55a|    AGGGAGAGTCAAGCAGCAACATCAAATTCAGCTCCAGTACTAGATGCAGCAGAAACTGGG
511  79_HRV57      AAACAAAGTCAAGCAACAACATCAAACTCAGCACCTGCATTGGATGCAGCTGAAACTGGA
512  80_HRV57a|    AAACAAAGTCAAGCAACAACATCAAACTCAGCACCTGCATTGGATGCAGCTGAAACTGGA
513  81_HRV57b|    AAACAAAGTCAAGCAACAACATCAAACTCAGCACCTGCATTGGATGCAGCTGAAACTGGA
514  82_HRV21      AGAGAGAGTCATGGAACAACATCAAACTCTGCTCCCGCACTTGATGCTGCAGAAACTGGA
515  83_HRVHan     AGAGAGAGTCATGGAACAACATCAAACTCTGCTCCCGCACTTGATGCTGCAGAAACTGGA
516  84_HRV43      GTAGAAAGTCATTCAACAACATCCAATGCAGCCCCTGCACTTGATGCAGCTGAAACTGGG
517  85_HRV43b|    GTAGAAAGTCATTCAACAACATCCAATGCAGCCCCTGCACTTGATGCAGCTGAAACTGGG
518  86_HRV43a|    GTAGAAAGTCATTCAACAACATCCAATGCAGCCCCTGCACTTGATGCAGCTGAAACTGGG
519  87_HRV75      ATGGAGAGCCATCCAACAACGTCTAATGCTGCTCCAGCTTTAGATGCAGCTGAAACTGGC
520  88_HRV75b|    ATGGAGAGCCATCCAACAACGTCTAATGCTGCTCCAGCTTTAGATGCAGCTGAAACTGGC
```

FIG. D7 CONT'D 03.trace                                                                 9/20/2007 5:03 PM

```
521  89_HRV75a|    ATGGAGAGCCATCCAACAACGTCTAATGCTGCTCCAGCTTTAGATGCAGCTGAAACTGGC
522  96_HRV9a|d    AAAGAGAGCCAACCCTACAACCTCTAACTCAGCTCCAGCTCTAGATGCTGCTGAGACAGGC
523  97_HRV9b|d    AAAGAGAGCAACCCTACAACCTCTAACTCAGCTCCAGCTCTAGATGCTGCTGAGACAGGC
524  98_HRV9       AAAGAGAGCAACCCTACAACCTCTAACTCAGCTCCAGCTCTAGATGCTGCTGAGACAGGC
525  99_HRV32      AAAGAAAGCAATCCCACAACCTCTAATTCAGCCCCAGCCTTAGATGCTGCCGAAACAGGT
526  100_HRV32a    AAAGAAAGCAATCCCACAACCTCTAATTCAGCCCCAGCCTTAGATGCTGCCGAAACAGGT
527  101_HRV32b    AAAGAAAGCAATCCCACAACCTCTAATTCAGCCCCAGCCTTAGATGCTGCCGAAACAGGT
528  102_HRV67     AAGCAAAGTGAACCCACGACTTCCAATTCAGCCCCAGCTCTAGATGCTGCTGAGACAGGT
529  103_HRV67a    AAGCAAAGTGAACCCACGACTTCCAATTCAGCCCCAGCTCTAGATGCTGCTGAGACAGGT
530  104_HRV67b    AAGCAAAGTGAACCCACGACTTCCAATTCAGCCCCAGCTCTAGATGCTGCTGAGACAGGT
531  105_HRV15     AAGGAGAGTCACTCAAGCACATCCAACTCAGCACCAGCACTAGATGCAGCTGAGACCGGC
532  106_HRV15a    AAGGAGAGTCACTCAAGCACATCCAACTCAGCACCAGCACTAGATGCAGCTGAGACCGGC
533  107_HRV15b    AAGGAGAGTCACTCAAGCACATCCAACTCAGCACCAGCACTAGATGCAGCTGAGACCGGC
534  108_HRV74a    AGAGAAAGCCATTCAAGTACTTCAAACTCAGCACCAGCACTGGATGCAGCTGAAACTGGC
535  109_HRV74b    AGAGAAAGCCATTCAAGTACTTCAAACTCAGCACCAGCACTGGATGCAGCTGAAACTGGC
536  110_HRV74     AGAGAAAGCCATTCAAGTACTTCAAACTCAGCACCAGCACTGGATGCAGCTGAAACTGGC
537  111_HRV38a    AAGGAAAGCCACTCCAGCACATCAAATTCAGCACCAGCATTAGATGCTGCTGAGACTGGA
538  112_HRV38b    AAGGAAAGCCACTCCAGCACATCAAATTCAGCACCAGCATTAGATGCTGCTGAGACTGGA
539  113_HRV38     AAGGAAAGCCACTCCAGCACATCAAATTCAGCACCAGCATTAGATGCTGCTGAGACTGGA
540  114_HRV60     AGGGAGAGCCAACCCACTACTTCTAATTCTGCTCCAGCATTGGATGCTGCTGAGACTGGT
541  115_HRV60a    AGGGAGAGCCAACCCACTACTTCTAATTCTGCTCCAGCATTGGATGCTGCTGAGACTGGT
542  116_HRV60b    AGGGAGAGCCAACCCACTACTTCTAATTCTGCTCCAGCATTGGATGCTGCTGAGACTGGT
543  117_HRV64a    AATGAGAGCCATCCCAGCACTTCCAATGCAGCGCCAGCTTTAGATGCAGCTGAGACCGGA
544  118_HRV64b    AATGAGAGCCATCCCAGCACTTCCAATGCAGCGCCAGCTTTAGATGCAGCTGAGACCGGA
545  119_HRV64     AATGAGAGCCATCCCAGCACTTCCAATGCAGCGCCAGCTTTAGATGCAGCTGAGACCGGA
546  120_HRV94a    AATGAGAGTCACCCTAGCACATCCAATGCAGCGCCAGCCTTAGATGCTGCCGAAACTGGA
547  121_HRV94b    AATGAGAGTCACCCTAGCACATCCAATGCAGCGCCAGCCTTAGATGCTGCCGAAACTGGA
548  122_HRV94     AATGAGAGTCACCCTAGCACATCCAATGCAGCGCCAGCCTTAGATGCTGCCGAAACTGGA
549  123_HRV22     AATGAAAGTCACCCCAGTACATCAAATGCTGCACCAGCACTAGATGCTGCTGAAACTGGA
550  124_HRV22a    AATGAAAGTCACCCCAGTACATCAAATGCTGCACCAGCACTAGATGCTGCTGAAACTGGA
551  125_HRV22b    AATGAAAGTCACCCCAGTACATCAAATGCTGCACCAGCACTAGATGCTGCTGAAACTGGA
552  126_HRV82     AATGAAAGTCATCCTAGTACTTCAAATTCAGCTCCTGCCTTGGACGCTGCAGAGACAGGA
553  127_HRV82b    AATGAAAGTCATCCTAGTACTTCAAATTCAGCTCCTGCCTTGGACGCTGCAGAGACAGGA
554  128_HRV82a    AATGAAAGTCATCCTAGTACTTCAAATTCAGCTCCTGCCTTGGACGCTGCAGAGACAGGA
555  129_HRV19     AATGAAAGTCATCCAAGTACATCAAATGCTGCTCCTGCCTTAGATGCAGCCGAGACAGGA
556  130_HRV19a    AATGAAAGTCATCCAAGTACATCAAATGCTGCTCCTGCCTTAGATGCAGCCGAGACAGGA
557  131_HRV19b    AATGAAAGTCATCCAAGTACATCAAATGCTGCTCCTGCCTTAGATGCAGCCGAGACAGGA
558  132_HRV13     AGTGAAAGTAGCTCAACTACATCTAATTCAGCTCCAGCCTTAGATGCTGCAGAAACTGGC
559  133_HRV13a    AGTGAAAGTAGCTCAACTACATCTAATTCAGCTCCAGCCTTAGATGCTGCAGAAACTGGC
560  134_HRV13b    AGTGAAAGTAGCTCAACTACATCTAATTCAGCTCCAGCCTTAGATGCTGCAGAAACTGGC
561  135_HRV41     AGTGAAAGCAGTCCAACTACTTCTAATTCAGCTCCAGCCCTAGATGCAGCAGAGACTGGT
562  136_HRV41a    AGTGAAAGCAGTCCAACTACTTCTAATTCAGCTCCAGCCCTAGATGCAGCAGAGACTGGT
563  137_HRV41b    AGTGAAAGCAGTCCAACTACTTCTAATTCAGCTCCAGCCCTAGATGCAGCAGAGACTGGT
564  138_HRV73     AATGAAAGTAATCCAACTACATCCAACTCAGCACCTGCACTGGACGCTGCAGAAACTGGC
565  139_HRV73b    AATGAAAGTAATCCAACTACATCCAACTCAGCACCTGCACTGGACGCTGCAGAAACTGGC
566  140_HRV73a    AATGAAAGTAATCCAACTACATCCAACTCAGCACCTGCACTGGACGCTGCAGAAACTGGC
567  141_HRV61     AATCAGAGCAACCCTACAACATCCAACTCAGCACCAGTCTTAGACGCTGCTGAAACAGGT
568  142_HRV61a    AATCAGAGCAACCCTACAACATCCAACTCAGCACCAGTCTTAGACGCTGCTGAAACAGGT
569  143_HRV61b    AATCAGAGCAACCCTACAACATCCAACTCAGCACCAGTCTTAGACGCTGCTGAAACAGGT
570  144_HRV96     AATGAAAGTTACCCAACAACTTCCAATTCAGCCCCAGTGCTAGATGCCGCTGAAACAGGT
571  145_HRV96b    AATGAAAGTTACCCAACAACTTCCAATTCAGCCCCAGTGCTAGATGCCGCTGAAACAGGT
572  146_HRV96a    AATGAAAGTTACCCAACAACTTCCAATTCAGCCCCAGTGCTAGATGCCGCTGAAACAGGT
573  90_HRV16a|    AATGAGAGCCACCCTACCACATCAAATGCGGCCCCAGTTTTGGATGCTGCTGAAACAGGA
574  91_HRV16b|    AATGAGAGCCACCCTACCACATCAAATGCGGCCCCAGTTTTGGATGCTGCTGAAACAGGA
575  92_1AYM_A     AATGAGAGCCACCCTACCACATCAAATGCGGCCCCAGTTTTGGATGCTGCTGAAACAGGA
576  93_HRV81a|    AATGAAAGCCACCCTACAACATCTAATTCAGCTCCTGTTTTAGATGCAGCTGAAACTGGA
577  94_HRV81b|    AATGAAAGCCACCCTACAACATCTAATTCAGCTCCTGTTTTAGATGCAGCTGAAACTGGA
578  95_HRV81      AATGAAAGCCACCCTACAACATCTAATTCAGCTCCTGTTTTAGATGCAGCTGAAACTGGA
579  147_HRV2      AATAGTAGTAACCCCACAACATCAAATTCTGCCCCAGCATTAGATGCTGCAGAAACAGGG
580  148_HRV2a|    AATAGTAGTAACCCCACAACATCAAATTCTGCCCCAGCATTAGATGCTGCAGAAACAGGG
581  149_HRV2b|    AATAGTAGTAACCCCACAACATCAAATTCTGCCCCAGCATTAGATGCTGCAGAAACAGGG
582  150_HRV49a    AATAGTAGTCACCCCACGACATCAAATCTCTGCTCCAGCATTAGATGCTGCAGAAACAGGG
583  151_HRV49b    AATAGTAGTCACCCCACGACATCAAATCTCTGCTCCAGCATTAGATGCTGCAGAAACAGGG
584  152_HRV49     AATAGTAGTCACCCCACGACATCAAATCTCTGCTCCAGCATTAGATGCTGCAGAAACAGGG
585  153_HRV23a    AATAGTAGTCATCCCACAACATCAAACTCTGCTCCAGCATTAGACGCTGCGGAAACGGGT
```

FIG. D7 CONT'D 03.trace                                                              9/20/2007 5:03 PM

```
586 154_HRV23b    AATAGTAGTCATCCCACAACATCAAACTCTGCTCCAGCATTAGACGCTGCGGAAACGGGT
587 155_HRV23     AATAGTAGTCATCCCACAACATCAAACTCTGCTCCAGCATTAGACGCTGCGGAAACGGGT
588 156_HRV30a    AACAGTAGTCACCCTACTACATCAAACTCTGCTCCGGCATTAGATGCTGCAGAAACAGGA
589 157_HRV30b    AACAGTAGTCACCCTACTACATCAAACTCTGCTCCGGCATTAGATGCTGCAGAAACAGGA
590 158_HRV30     AACAGTAGTCACCCTACTACATCAAACTCTGCTCCGGCATTAGATGCTGCAGAAACAGGA
591 159_HRV7      CAGCCAAGTACATCTGTTTCAAGTCACTCTGTACCAGCATTGGATGCTGCAGAGACTGGA
592 160_HRV7b|    CAGCCAAGTACATCTGTTTCAAGTCACTCTGTACCAGCATTGGATGCTGCAGAGACTGGA
593 161_HRV7a|    CAGCCAAGTACATCTGTTTCAAGTCACTCTGTACCAGCATTGGATGCTGCAGAGACTGGA
594 162_HRV88     CAACCTAGCACATCCGTTTCAAGTCACTCTGTGCCAGCTCTGGATGCTGCGGAAACAGGG
595 163_HRV88a    CAACCTAGCACATCCGTTTCAAGTCACTCTGTGCCAGCTCTGGATGCTGCGGAAACAGGG
596 164_HRV88b    CAACCTAGCACATCCGTTTCAAGTCACTCTGTGCCAGCTCTGGATGCTGCGGAAACAGGG
597 165_HRV36a    CAACCTAGTTCATCTGTGTCAAGTCATTCAGCTCCCGCCTTAGACGCTGCGGAAACTGGA
598 166_HRV36b    CAACCTAGTTCATCTGTGTCAAGTCATTCAGCTCCCGCCTTAGACGCTGCGGAAACTGGA
599 167_HRV36     CAACCTAGTTCATCTGTGTCAAGTCATTCAGCTCCCGCCTTAGACGCTGCGGAAACTGGA
600 168_HRV89a    CAACCTAGCACATCTGTGTCAAGTCATGCAGCGCCTGCATTGGATGCTGCGGAAACCGGA
601 169_HRV89b    CAACCTAGCACATCTGTGTCAAGTCATGCAGCACCAGCGTTGGATGCTGCGGAAACCGGA
602 170_HRV89     CAACCTAGCACATCTGTGTCAAGTCATGCAGCGCCTGCATTGGATGCTGCGGAAACCGGA
603 171_HRV58     CAACCTAGTACATCTGTATCAAGTCATTCTGTGCCTGCCTTGGATGCTGCAGAAACGGGA
604 172_HRV58a    CAACCTAGTACATCTGTATCAAGTCATTCTGTGCCTGCCTTGGATGCTGCAGAAACGGGA
605 173_HRV58b    CAACCTAGTACATCTGTATCAAGTCATTCTGTGCCTGCCTTGGATGCTGCAGAAACGGGA
606 174_HRV12a    AACAAAAGTAATGGGCAGTTATCAAACGCAGCACCAGCGTTGGACGCTGCAGAAACTGGT
607 175_HRV12b    AACAAAAGTAATGGGCAGTTATCAAACGCAGCACCAGCGTTGGACGCTGCAGAAACTGGT
608 176_HRV12     AACAAAAGTAATGGGCAGTTATCAAACGCAGCACCAGCGTTGGACGCTGCAGAAACTGGT
609 177_HRV78a    AAAGAAAGTAAACCCCAGTCTAGCAACTCCGCTCCAGTTTTGGACGCTGCAGAAACAGGT
610 178_HRV78b    AAAGAAAGTAAACCCCAGTCTAGCAACTCCGCTCCAGTTTTGGACGCTGCAGAAACAGGT
611 179_HRV78     AAAGAAAGTAAACCCCAGTCTAGCAACTCCGCTCCAGTTTTGGACGCTGCAGAAACAGGT
612 180_HRV20     ACATCTAGTAACTCCCAAACATCAAATGCAGCACCAGCACTAGATGCTGCTGAGACAGGA
613 181_HRV20a    ACATCTAGTAACTCCCAAACATCAAATGCAGCACCAGCACTAGATGCTGCTGAGACAGGA
614 182_HRV20b    ACATCTAGTAACTCCCAAACATCAAATGCAGCACCAGCACTAGATGCTGCTGAGACAGGA
615 183_HRV68     CCAGCAAGTAATACCCAAACTTCAAATGCAGCCCCAGCCTTAGATGCTGCTGAGACTGGA
616 184_HRV68a    CCAGCAAGTAATACCCAAACTTCAAATGCAGCCCCAGCCTTAGATGCTGCTGAGACTGGA
617 185_HRV68b    CCAGCAAGTAATACCCAAACTTCAAATGCAGCCCCAGCCTTAGATGCTGCTGAGACTGGA
618 186_HRV28     AATCCTAGCAACGCACAAACTACAAATGCAGCTCCCGCTCTCGATGCCGCTGAGACGGGG
619 187_HRV28a    AATCCTAGCAACGCACAAACTACAAATGCAGCTCCCGCTCTCGATGCCGCTGAGACGGGG
620 188_HRV28b    AATCCTAGCAACGCACAAACTACAAATGCAGCTCCCGCTCTCGATGCCGCTGAGACGGGG
621 189_HRV53a    AATGCAAGCAATCCACAAACTTCAAATTCAGCACCAGCACTAGATGCTGCAGAAACGGGT
622 190_HRV53b    AATGCAAGCAATCCACAAACTTCAAATTCAGCACCAGCACTAGATGCTGCAGAAACGGGT
623 191_HRV53     AATGCAAGCAATCCACAAACTTCAAATTCAGCACCAGCACTAGATGCTGCAGAAACGGGT
624 192_HRV46a    AATGCCAGTAGTGGACATACATCTAATTCAGCTCCAGCACTTGATGCAGCAGAAACTGGA
625 193_HRV46b    AATGCCAGTAGTGGACATACATCTAATTCAGCTCCAGCACTTGATGCAGCAGAAACTGGA
626 194_HRV46     AATGCCAGTAGTGGACATACATCTAATTCAGCTCCAGCACTTGATGCAGCAGAAACTGGA
627 195_HRV80a    AGTGCTAGCAATGGACATACATCAAACTCAGCTCCAACACTTGATGCAGCAGAAACTGGT
628 196_HRV80b    AGTGCTAGCAATGGACATACATCAAACTCAGCTCCAACACTTGATGCAGCAGAAACTGGT
629 197_HRV80     AGTGCTAGCAATGGACATACATCAAACTCAGCTCCAACACTTGATGCAGCAGAAACTGGT
630 198_HRV51     CAACCTAGCAGTGGGCACACATCTAATGCTGCACCAGCTCTAGATGCTGCTGAGACAGGA
631 199_HRV51a    CAACCTAGCAGTGGGCACACATCTAATGCTGCACCAGCTCTAGATGCTGCTGAGACAGGA
632 200_HRV51b    CAACCTAGCAGTGGGCACACATCTAATGCTGCACCAGCTCTAGATGCTGCTGAGACAGGA
633 201_HRV65a    CAAGCTAGTAATGGGCATACATCTAATGCTGCACCAGCTTTAGATGCTGCTGAAACAGGA
634 202_HRV65b    CAAGCTAGTAATGGGCATACATCTAATGCTGCACCAGCTTTAGATGCTGCTGAAACAGGA
635 203_HRV65     CAAGCTAGTAATGGGCATACATCTAATGCTGCACCAGCTTTAGATGCTGCTGAAACAGGA
636 204_HRV71a    CAACCTAGTAATGGACATACCTCAAACTCAGCACCAGCCTTAGATGCAGCAGAAACTGGG
637 205_HRV71b    CAACCTAGTAATGGACATACCTCAAACTCAGCACCAGCCTTAGATGCAGCAGAAACTGGG
638 206_HRV71     CAACCTAGTAATGGACATACCTCAAACTCAGCACCAGCCTTAGATGCAGCAGAAACTGGG
639 207_HRV8      CAAGCTAGTAATGGATCTATAGCAAATTCAGCACCAGCATTAGATGCAGCAGAGACTGGA
640 208_HRV95     CAAGCCAGTAATGGATCTATAGCAAATTCAGCACCAGCATTAGATGCAGCAGAGACTGGA
641 209_HRV45     CGACCCAGCGATGGGTTGATTGCAAACTCAGCCCCAGCTTTGGATGCAGCTGAAACTGGA
642 210_HRV45a    CGACCCAGCGATGGGTTGATTGCAAACTCAGCCCCAGCTTTGGATGCAGCTGAAACTGGA
643 211_HRV45b    CGACCCAGCGATGGGTTGATTGCAAACTCAGCCCCAGCTTTGGATGCAGCTGAAACTGGA
644 GROUP_1       ------AG---------------A--C-G---C-----T-GA-GC-GC-GA-AC-GG-
645
646 1_HRV1A1|d    CACACCAGTAATGTTCAACCAGAAGATGCTATAGAGACAAGGTATGTTATAACATCACAA
647 2_HRV1A2|d    CACACCAGTAATGTTCAACCAGAAGATGCTATAGAGACAAGGTATGTTATAACATCACAA
648 3_HRV1A|cD    CACACCAGTAATGTTCAACCAGAAGATGCTATAGAGACAAGGTATGTTATAACATCACAA
649 4_HRV1B1|d    CACACCAGTAATGTACAACCAGAGGATGCTATAGAAACAAGATATGTTATGACATCACAA
650 5_HRV1B2|d    CACACCAGTAATGTACAACCAGAGGATGCTATAGAAACAAGATATGTTATGACATCACAA
```

FIG. D7 CONT'D

```
03.trace                                                        9/20/2007 5:03 PM 651  6_HRV1B      CACACCAGTAATGTACAACCAGAGGATGCTATAGAAACAAGATATGTTATGACATCACAA
652  7_HRV40a|d   CATACAAGCAACATACAACCTGAAGATACAATAGAAACAAGATTTGTGCAGACATCACAA
653  8_HRV40b|d   CATACAAGCAACATACAACCTGAAGATACAATAGAAACAAGATTTGTGCAGACATCACAA
654  9_HRV40      CATACAAGCAACATACAACCTGAAGATACAATAGAAACAAGATTTGTGCAGACATCACAA
655  10_HRV85     CATACAAGTAGTACACAGCCCGAGGATACAATAGAGACCAGGTTTGTTCAAACTTCACAG
656  11_HRV85a|   CATACAAGTAGTACACAGCCCGAGGATACAATAGAGACCAGGTTTGTTCAAACTTCACAG
657  12_HRV85b|   CATACAAGTAGTACACAGCCCGAGGATACAATAGAGACCAGGTTTGTTCAAACTTCACAG
658  13_HRV56a|   CATACTAGTGCAATCCAACCAGAAGACACTATAGAAACCAGATATGTACAGACATCACAA
659  14_HRV56b|   CATACTAGTGCAATCCAACCAGAAGACACTATAGAAACCAGATATGTACAGACATCACAA
660  15_HRV56     CATACTAGTGCAATCCAACCAGAAGACACTATAGAAACCAGATATGTACAGACATCACAA
661  16_HRV54     CACACTAGTGGAGTACAACCCGAGGACACCATAGAAACAAGATTTGTGCAGACATCACAA
662  17_HRV98     CACACTAGTGGAATACAACCTGAGGATACTATAGAAACAAGATATGTGCAGACATCACAA
663  18_HRV59a|   CATACAAGCAGTATACAACCTGAGGATACCATAGAAACAAGATATGTTCAGACATCACAA
664  19_HRV59b|   CATACAAGCAGTATACAACCTGAGGATACCATAGAAACAAGATATGTTCAGACATCACAA
665  20_HRV59     CATACAAGCAGTATACAACCTGAGGATACCATAGAAACAAGATATGTTCAGACATCACAA
666  21_HRV63     CACACAAGCAGTATACAACCTGAGGATACTGTAGAAACTAGATATGTGCAAACGTCTCAA
667  22_HRV63b|   CACACAAGCAGTATACAACCTGAGGATACTGTAGAAACTAGATATGTGCAAACGTCTCAA
668  23_HRV63a|   CACACAAGCAGTATACAACCTGAGGATACTGTAGAAACTAGATATGTGCAAACGTCTCAA
669  24_HRV39     CACACAAGTAGCACCCAGCCTGAAGACACAATTGAAACAAGATATGTGCAAACCTCACAT
670  25_HRV39a|   CACACAAGTAGCACCCAGCCTGAAGACACAATTGAAACAAGATATGTGCAAACCTCACAT
671  26_HRV39b|   CACACAAGTAGCATCCAACCTGAAGACACAATTGAAACAAGATATGTGCAAACCTCACAT
672  27_HRV10a|   CATACCAGTAGTGTACAACCAGAAGATACGGTTGAAACACGATATGTGCAAACATCCCAG
673  28_HRV10b|   CATACCAGTAGTGTACAACCAGAAGATACGGTTGAAACACGATATGTGCAAACATCCCAG
674  29_HRV10     CATACCAGTAGTGTACAACCAGAAGATACGGTTGAAACACGATATGTGCAAACATCCCAG
675  30_HRV100a   CACACTAGTAATGTGCAACCTGAAGATACAGTTGAAACTCGATATGTGCAGACATCACAG
676  31_HRV100b   CACACTAGTAATGTGCAACCTGAAGATACAGTTGAAACTCGATATGTGCAGACATCACAG
677  32_HRV100    CACACTAGTAATGTGCAACCTGAAGATACAGTTGAAACTCGATATGTGCAGACATCACAG
678  33_HRV66     CACACTAGTAAAGTACAACCAGAAGATACAGTTGAGACTCGTTACGTGCAAACATCACAG
679  34_HRV66b|   CACACTAGTAAAGTACAACCAGAAGATACAGTTGAGACTCGTTACGTGCAAACATCACAG
680  35_HRV66a|   CACACTAGTAAAGTACAACCAGAAGATACAGTTGAGACTCGTTACGTGCAAACATCACAG
681  36_HRV77a|   CATACTAGTAGTGTGCAACCAGAAGATACAGTTGAGACCCGCTATGTACAAACTTCCCAG
682  37_HRV77b|   CATACTAGTAGTGTGCAACCAGAAGATACAGTTGAGACCCGCTATGTACAAACTTCCCAG
683  38_HRV77     CATACTAGTAGTGTGCAACCAGAAGATACAGTTGAGACCCGCTATGTACAAACTTCCCAG
684  39_HRV62a    CACACTAGTAATGTACAACCAGAAGACACTATTGAAACCCGTCATGTTCAAACCACACAA
685  40_HRV62b    CACACTAGTAATGTACAACCAGAAGACACTATTGAAACCCGTTATGTTCAAACCACACAA
686  41_HRV25     CACACTAGCAATGTGCAACCAGAGGATACCATTGAAACTCGTTATGTTCAAACCACACAA
687  42_HRV29a    CATACTAGTAATGTACAACCAGAAGATACCATTGAGACTCGTTATGTACAAACCTCACAT
688  43_HRV29b    CATACTAGTAATGTACAACCAGAAGATACCATTGAGACTCGTTATGTACAAACCTCACAT
689  44_HRV44a    CATACTAGTAATGTACAACCAGAAGATACCATTGAGACTCGATATGTACAACCTCACAA
690  45_HRV44b    CATACTAGTAATGTACAACCAGAAGATACCATTGAGACTCGATATGTACAAACCTCACAA
691  46_HRV31     CACACTAGTAATGTACAACCAGAAGATACAATTGAAACTCGCTACGTGCAAACATCACAA
692  47_HRV31a|   CACACTAGTAATGTACAACCAGAAGATACAATTGAAACTCGCTACGTGCAAACATCACAA
693  48_HRV31b|   CACACTAGTAATGTACAACCAGAAGATACAATTGAAACTCGCTACGTGCAAACATCACAA
694  49_HRV47     CACACTAGCAATGTACAGCCAGAAGATACAATTGAAACTCGATATGTACAAACAGCACAA
695  50_HRV47a|   CACACTAGCAATGTACAGCCAGAAGATACAATTGAAACTCGATATGTACAAACAGCACAA
696  51_HRV47b|   CACACTAGCAATGTACAGCCAGAAGATACAATTGAAACTCGATATGTACAAACAGCACAA
697  52_HRV11     CATACTAGCAAAGTGCAGCCAGAGGATATGATTGAGACTAGATATGTGCAGACTTCACAG
698  53_HRV11b|   CATACTAGCAAAGTGCAGCCAGAGGATATGATTGAGACTAGATATGTGCAGACTTCACAG
699  54_HRV11a|   CATACTAGCAAAGTGCAGCCAGAGGATATGATTGAGACTAGATATGTGCAGACTTCACAG
700  55_HRV76     CACACAAGCAGCGTTCAACCAGAGGACATGGTTGAGACTAGGTATGTGCAAACATCACAA
701  56_HRV76b|   CACAAGCAGCGTTCAACCAGAGGACATGGTTGAGACTAGGTATGTGCAAACATCACAA
702  57_HRV76a|   CACACAAGCAGCGTTCAACCAGAGGACATGGTTGAGACTAGGTATGTGCAAACATCACAA
703  58_HRV33     CACACTAATAATGTACAACCAGAAGATATGATTGAAACAAGATATGTACAAACATCACAA
704  59_HRV33b|   CACACTAATAATGTACAACCAGAAGATATGATTGAAACAAGATATGTACAAACATCACAA
705  60_HRV33a|   CACACTAATAATGTACAACCAGAAGATATGATTGAAACAAGATATGTACAAACATCACAA
706  61_HRV24a|   CATACGAGTAGCGTGCAGCCAGAAGATATGGTTGAAACTAGATATGTCCAAACATCACAA
707  62_HRV24b|   CATACGAGTAGCGTGCAGCCAGAAGATATGGTTGAAACTAGATATGTCCAAACATCACAA
708  63_HRV24     CATACGAGTAGCGTGCAGCCAGAAGATATGGTTGAAACTAGATATGTCCAAACATCACAA
709  64_HRV90     CATACTAGTGATGTCCAGCCAGAAGATGTGGTAGAGACCAGATACGTGCAAACATCACAA
710  65_HRV90a|   CATACTAGTGATGTCCAGCCAGAAGATGTGGTAGAGACCAGATACGTGCAAACATCACAA
711  66_HRV90b|   CATACTAGTGATGTCCAGCCAGAAGATGTGGTAGAGACCAGATACGTGCAAACATCACAA
712  67_HRV34     CACACTAGCAGTGTACAACCTGAAGATATGATTGAGACCAGGTACGTACAAACATCACAA
713  68_HRV34b|   CACACTAGCAGTGTACAACCTGAAGATATGATTGAGACCAGGTACGTACAAACATCACAA
714  69_HRV34a|   CACACTAGCAGTGTACAACCTGAAGATATGATTGAGACCAGGTACGTACAAACATCACAA
715  70_HRV50a|   CACACAAGTAATGTGCAGCCTGAAGATATGCTTGAAACTAGATATGTGCAAACATCGCAT
```

FIG. D7 CONT'D

```
03.trace                                                              9/20/2007 5:03 PM 716  71_HRV50b|   CACACAAGTAATGTGCAGCCTGAAGATATGCTTGAAACTAGATATGTGCAAACATCGCAT
717  72_HRV50    CACACAAGTAATGTGCAGCCTGAAGATATGCTTGAAACTAGATATGTGCAAACATCGCAT
718  73_HRV18a|  CACACCAGCAATGTGCAACCTGAAGATATGATTGAGACTAGGTATGTACAAACATCACAA
719  74_HRV18b|  CACACCAGCAATGTGCAACCTGAAGATATGATTGAGACTAGGTATGTACAAACATCACAA
720  75_HRV18    CACACCAGCAATGTGCAACCTGAAGATATGATTGAGACTAGGTATGTACAAACATCACAA
721  76_HRV55    CATACAAGCAATGTACAACCAGAAGATGTAATTGAGACAAGATATGTTCAGACATCACAA
722  77_HRV55b|  CATACAAGCAATGTACAACCAGAAGATGTAATTGAGACAAGATATGTTCAGACATCACAA
723  78_HRV55a|  CATACAAGCAATGTACAACCAGAAGATGTAATTGAGACAAGATATGTTCAGACATCACAA
724  79_HRV57    CACACTAGTAATGTACAACCGGAAGACATGATTGAAACTAGATATGTCCAGACATCACAA
725  80_HRV57a|  CACACTAGTAATGTACAACCGGAAGACATGATTGAAACTAGATATGTCCAGACATCACAA
726  81_HRV57b|  CACACTAGTAATGTACAACCGGAAGACATGATTGAAACTAGATATGTCCAGACATCACAA
727  82_HRV21    CACACTAGTAATGTACAGCCGGAGGATATGGTTGAAACAAGGTATGTTCAGACATCACAA
728  83_HRVHan   CACACTAGTAATGTACAACCAGAGGATATGGTTGAAACAAGGTATGTTCAGACATCACAA
729  84_HRV43    CATACTAGCCAGGTGCAACCTGAAGACATGGTAGAGACAAGGTCAGTACATAATTTCCAA
730  85_HRV43b|  CATACTAGCCAGGTGCAACCTGAAGACATGGTAGAGACAAGGTCAGTACATAATTTCCAA
731  86_HRV43a|  CATACTAGCCAGGTGCAACCTGAAGACATGGTAGAGACAAGGTCAGTACATAATTTCCAA
732  87_HRV75    CATACCAGCCATGTTCAACCAGAAGACATGTTAGAAACAAGGCAAGTACAAAATTTCCAA
733  88_HRV75b|  CATACCAGCCATGTTCAACCAGAAGACATGTTAGAAACAAGGCAAGTACAAAATTTCCAA
734  89_HRV75a|  CATACCAGCCATGTTCAACCAGAAGACATGTTAGAAACAAGGCAAGTACAAAATTTCCAA
735  96_HRV9a|d  CATACTAGCAATGTTCAACCTGAAGACATGATTGAAACACGTTATGTGCAGACATCACAA
736  97_HRV9b|d  CATACTAGCAATGTTCAACCTGAAGACATGATTGAAACACGTTATGTGCAGACATCACAA
737  98_HRV9     CATACTAGCAATGTTCAACCTGAAGACATGATTGAAACACGTTATGTGCAGACATCACAA
738  99_HRV32    CACACTAGTAATGTTCAACCTGAAGACATGATTGAAACACGTTATGTGCAAACAACACAC
739  100_HRV32a  CATACCAGTAATGTTCAACCTGAAGACATGATTGAAACACGTTATGTGCAAACAACACAC
740  101_HRV32b  CATACCAGTAATGTTCAACCTGAAGACATGATTGAAACACGTTATGTGCAAACAACACAC
741  102_HRV67   CACACTAGCAGTGTACAACCTGAAGATATGATCGAGACTCGTTATGTACAGGCATCAAAT
742  103_HRV67a  CACACTAGCAGTGTACAACCTGAAGATATGATCGAGACTCGTTATGTACAGGCATCAAAT
743  104_HRV67b  CACACTAGCAGTGTACAACCTGAAGATATGATCGAGACTCGTTATGTACAGGCATCAAAT
744  105_HRV15   CATACTAGCAGTGTTCAACCTGAGGATATGATTGAAACTCGTTACGTCCAAACATCACAG
745  106_HRV15a  CATACTAGCAGTGTTCAACCTGAGGATATGATTGAAACTCGTTACGTCCAAACATCACAG
746  107_HRV15b  CATACTAGCAGTGTTCAACCTGAGGATATGATTGAAACTCGTTACGTCCAAACATCACAG
747  108_HRV74a  CATACCAGTAATGTGCAACCAGAAGATATGGTTGAGACACGCTATGTGCAAACCTCACAG
748  109_HRV74b  CATACCAGTAATGTGCAACCAGAAGATATGGTTGAGACACGCTATGTGCAAACCTCACAG
749  110_HRV74   CATACCAGTAATGTGCAACCAGAAGATATGGTTGAGACACGCTATGTGCAAACCTCACAG
750  111_HRV38a  CACACCAGTAATGTGCAGCCTGAGGATATGATTGAAACTCGCTATGTACAGACATCACAA
751  112_HRV38b  CACACCAGTAATGTGCAGCCTGAGGATATGATTGAAACTCGCTATGTACAGACATCACAA
752  113_HRV38   CACACCAGTAATGTGCAGCCTGAGGATATGATTGAAACTCGCTATGTACAGACATCACAA
753  114_HRV60   CACACTAGTAATGTACAGCCTGAGGTTGAAACACGTTATGTGCAGATTACACAA
754  115_HRV60a  CACACTAGTAATGTACAGCCTGAGGACGTGATTGAAACACGTTATGTGCAGATTACACAA
755  116_HRV60b  CACACTAGTAATGTACAGCCTGAGGACGTGATTGAAACACGTTATGTGCAGATTACACAA
756  117_HRV64a  CACACCAGTAATGTACAGCCTGAAGATATGATTGAAACGCGCTATGTACAAAACACTCAA
757  118_HRV64b  CACACCAGTAATGTACAGCCTGAAGATATGATTGAAACGCGCTATGTACAAAACACTCAA
758  119_HRV64   CACACCAGTAATGTACAGCCTGAAGATATGATTGAAACGCGCTATGTACAAAACACTCAA
759  120_HRV94a  CACACAAGCAATGTACAACCTGAGGATATGATTGAAACACGCTATGTACAAAACACTCAA
760  121_HRV94b  CACACAAGCAATGTACAACCTGAGGATATGATTGAAACACGCTATGTACAAAACACTCAA
761  122_HRV94   CACACAAGCAATGTACAACCTGAGGATATGATTGAAACACGCTATGTACAAAACACTCAA
762  123_HRV22   CACACAAGCAATGTGCAGCCAGAAGACATGATAGAAACACGCTATGTGTTAAATTCACAA
763  124_HRV22a  CACACAAGCAATGTGCAGCCAGAAGACATGATAGAAACACGCTATGTGTTAAATTCACAA
764  125_HRV22b  CACACAAGCAATGTGCAGCCAGAAGACATGATAGAAACACGCTATGTGTTAAATTCACAA
765  126_HRV82   CATACAAGTACTGTTCAACCTGAGGACATGATTGAAACACGGTATGTTCAAACATCACAA
766  127_HRV82b  CATACAAGTACTGTTCAACCTGAGGACATGATTGAAACACGGTATGTTCAAACATCACAA
767  128_HRV82a  CATACAAGTACTGTTCAACCTGAGGACATGATTGAAACACGGTATGTTCAAACATCACAA
768  129_HRV19   CATACTAGCAATGTACAGCCTGAGGACATGATCGAAACACGCTATGTTCAAACGTCCCAG
769  130_HRV19a  CATACTAGCAATGTACAGCCTGAGGACATGATCGAAACACGCTATGTTCAAACGTCCCAG
770  131_HRV19b  CATACTAGCAATGTACAGCCTGAGGACATGATCGAAACACGCTATGTTCAAACGTCCCAG
771  132_HRV13   CACACAAGCAGTGTACAACCAGAAGACATGGTTGAAACACGTTATGTCCAAACTTCACAA
772  133_HRV13a  CACACAAGCAGTGTACAACCAGAAGACATGGTTGAAACACGTTATGTCCAAACTTCACAA
773  134_HRV13b  CACACAAGCAGTGTACAACCAGAAGACATGGTTGAAACACGTTATGTCCAAACTTCACAA
774  135_HRV41   CATACCAGTAATGTACAACCAGAGGACATGATTGAAACACGATATGTCCAAACCTCACAA
775  136_HRV41a  CATACCAGTAATGTACAACCAGAGGACATGATTGAAACACGATATGTCCAAACCTCACAA
776  137_HRV41b  CATACCAGTAATGTACAACCAGAGGACATGATTGAAACACGATATGTCCAAACCTCACAA
777  138_HRV73   CATACCAGTGGTGTACAACCAGAAGACATGATTGAGACCCGTTATGTCCAAACATCACAG
778  139_HRV73b  CATACCAGTGGTGTACAACCAGAAGACATGATTGAGACCCGTTATGTCCAAACATCACAG
779  140_HRV73a  CATACCAGTGGTGTACAACCAGAAGACATGATTGAGACCCGTTATGTCCAAACATCACAG
780  141_HRV61   CATACCAGCAATGTTCAACCGGAGGACACGATTGAAACACGATATGTTCAAACCCTCACAG
```

FIG. D7 CONT'D

03.trace                                                                                    9/20/2007 5:03 PM

```
781  142_HRV61a   CATACCAGCAATGTTCAACCGGAGGACACGATTGAAACACGATATGTTCAAACCTCACAG
782  143_HRV61b   CATACCAGCAATGTTCAACCGGAGGACACGATTGAAACACGATATGTTCAAACCTCACAG
783  144_HRV96    CATACTAGCAATGTCCAACCAGAGGATATGATTGAGACTCGATATGTTCAGACATCGCAG
784  145_HRV96b   CATACTAGCAATGTCCAACCAGAGGATATGATTGAGACTCGATATGTTCAGACATCGCAG
785  146_HRV96a   CATACTAGCAATGTCCAACCAGAGGATATGATTGAGACTCGATATGTTCAGACATCGCAG
786  90_HRV16a|   CATACCAATAAGATACAGCCAGAAGACACTATAGAAACCAGATATGTGCAATCTTCACAG
787  91_HRV16b|   CATACCAATAAGATACAGCCAGAAGACACTATAGAAACCAGATATGTGCAATCTTCACAG
788  92_1AYM_A    CATACCAATAAGATACAGCCAGAAGACACTATAGAAACCAGATATGTGCAATCTTCACAG
789  93_HRV81a|   CACACCAGTAATATACAACCTGAGGATACTATTGAGACCAGATATGTACAATCTTCACAG
790  94_HRV81b|   CACACCAGTAATATACAACCTGAGGATACTATTGAGACCAGATATGTACAATCTTCACAG
791  95_HRV81     CACACCAGTAATATACAACCTGAGGATACTATTGAGACCAGATATGTACAATCTTCACAG
792  147_HRV2     CACACTAGTAGTGTTCAACCAGAGGATGTCATTGAAACTAGGTATGTGCAGACATCACAA
793  148_HRV2a|   CACACTAGTAGTGTTCAACCAGAGGATGTCATTGAAACTAGGTATGTGCAGACATCACAA
794  149_HRV2b|   CACACTAGTAGTGTTCAACCAGAGGATGTCATTGAAACTAGGTATGTGCAGACATCACAA
795  150_HRV49a   CACACTAGCAATGTGCAACCTGAAGATGTCATTGAAACCAGATATGTACAGACATCACAA
796  151_HRV49b   CACACTAGCAATGTGCAACCTGAAGATGTCATTGAAACCAGATATGTACAGACATCACAA
797  152_HRV49    CACACTAGCAATGTGCAACCTGAAGATGTCATTGAAACCAGATATGTACAGACATCACAA
798  153_HRV23a   CACACTAGTAATGTTCAACCAGAAGATGTCATTGAAACCAGGTACGTTCAAACATCACAA
799  154_HRV23b   CACACTAGTAATGTTCAACCAGAAGATGTCATTGAAACCAGGTACGTTCAAACATCACAA
800  155_HRV23    CACACTAGTAATGTTCAACCAGAAGATGTCATTGAAACCAGGTACGTTCAAACATCACAA
801  156_HRV30a   CATACTAGTAATGTTCAACCTGAAGATGTCATTGAAACTAGATATGTTCAAACATCACAA
802  157_HRV30b   CATACTAGTAATGTTCAACCTGAAGATGTCATTGAAACTAGATATGTTCAAACATCACAA
803  158_HRV30    CATACTAGTAATGTTCAACCTGAAGATGTCATTGAAACTAGATATGTTCAAACATCACAA
804  159_HRV7     CATACTAGTTCTGTTCAACCTGAAGATATGATCGAGACAAGGTATGTCATAACAGACCAA
805  160_HRV7b|   CATACTAGTTCTGTTCAACCTGAAGATATGATCGAGACAAGGTATGTCATAACAGACCAA
806  161_HRV7a|   CATACTAGTTCTGTTCAACCTGAAGATATGATCGAGACAAGGTATGTCATAACAGACCAA
807  162_HRV88    CATACTAGTTCTGTTCAACCTGAAGATATGATAGAAACTAGATATGTTATAACAGATCAA
808  163_HRV88a   CATACTAGTTCTGTTCAACCTGAAGATATGATAGAAACTAGATATGTTATAACAGATCAA
809  164_HRV88b   CATACTAGTTCTGTTCAACCTGAAGATATGATAGAAACTAGATATGTTATAACAGATCAA
810  165_HRV36a   CATACCAGCTCTGTCCAACCAGAGGACATGATCGAGACCAGATATGTCATAACTGATCAA
811  166_HRV36b   CATACCAGCTCTGTCCAACCAGAGGACATGATCGAGACCAGATATGTCATAACTGATCAA
812  167_HRV36    CATACCAGCTCTGTCCAACCAGAGGACATGATCGAGACCAGATATGTCATAACTGATCAA
813  168_HRV89a   CACACCAGCTCTGTTCAACCTGAAGATATGATTGAAACTAGATATGTTATAACTGATCAA
814  169_HRV89b   CACACCAGCTCTGTTCAACCTGAAGATATGATTGAAACTAGATATGTTATAACTGATCAA
815  170_HRV89    CACACCAGCTCTGTTCAACCTGAAGATATGATTGAAACTAGATATGTTATAACTGATCAA
816  171_HRV58    CACACAAGTTCTGTTCAGCCTGAGGATATGATTGAAACTAGATATGTTATCACAGATCAA
817  172_HRV58a   CACACAAGTTCTGTTCAGCCTGAGGATATGATTGAAACTAGATATGTTATCACAGATCAA
818  173_HRV58b   CACACAAGTTCTGTTCAGCCTGAGGATATGATTGAAACTAGATATGTTATCACAGATCAA
819  174_HRV12a   CATACCAGCCAAACACAACCAGAAGATGTGATTGAAACCAGGTATGTGATTACAGACCAG
820  175_HRV12b   CATACCAGCCAAACACAACCAGAAGATGTGATTGAAACCAGGTATGTGATTACAGACCAG
821  176_HRV12    CATACCAGCCAAACACAACCAGAAGATGTGATTGAAACCAGGTATGTGATTACAGACCAG
822  177_HRV78a   CATACGAACCAAGTACAGCCTGAAGACACCATAGAAACTAGATATGTTATAACTGACCAA
823  178_HRV78b   CATACGAACCAAGTACAGCCTGAAGACACCATAGAAACTAGATATGTTATAACTGACCAA
824  179_HRV78    CATACGAACCAAGTACAGCCTGAAGACACCATAGAAACTAGATATGTTATAACTGACCAA
825  180_HRV20    CACACAAACCAGGTCCAGCCAGAAGATATGGTCGAGACACGGTATGTAATTACTGATCAG
826  181_HRV20a   CACACAAACCAGGTCCAGCCAGAAGATATGGTCGAGACACGGTATGTAATTACTGATCAG
827  182_HRV20b   CACACAAACCAGGTCCAGCCAGAAGATATGGTCGAGACACGGTATGTAATTACTGATCAG
828  183_HRV68    CATACAAACCAAGTCCAACCAGAAGATGTGGTTGAAACACGCTATGTCATAACAGACCAG
829  184_HRV68a   CATACAAACCAAGTCCAACCAGAAGATGTGGTTGAAACACGCTATGTCATAACAGACCAG
830  185_HRV68b   CATACAAACCAAGTCCAACCAGAAGATGTGGTTGAAACACGCTATGTCATAACAGACCAG
831  186_HRV28    CACACAAGCCAAACACAACCTGAAGACATGGTTGAGACTAGGTATGTAATCACAGATCAG
832  187_HRV28a   CACACAAGCCAAACACAACCTGAAGACATGGTTGAGACTAGGTATGTAATCACAGATCAG
833  188_HRV28b   CACACAAGCCAAACACAACCTGAAGACATGGTTGAGACTAGGTATGTAATCACAGATCAG
834  189_HRV53a   CATACAAGTCAGACACAACCTGAGGACATGCTGGAAACTAGATATGTCATCACAGACCAA
835  190_HRV53b   CATACAAGTCAGACACAACCTGAGGACATGCTGGAAACTAGATATGTCATCACAGACCAA
836  191_HRV53    CATACAAGTCAGACACAACCTGAGGACATGCTGGAAACTAGATATGTCATCACAGACCAA
837  192_HRV46a   CACACTAGCCAGATACAACCAGAAGACATGATAGAAACCAGATATGTTATCACAGACCAA
838  193_HRV46b   CACACTAGCCAGATACAACCAGAAGACATGATAGAAACCAGATATGTTATCACAGACCAA
839  194_HRV46    CACACTAGCCAGATACAACCAGAAGACATGATAGAAACCAGATATGTTATCACAGACCAA
840  195_HRV80a   CACACTAGCCAGGTGCAACCAGAAGACATGATAGAAACTAGATATGTTATTACTGATCAG
841  196_HRV80b   CACACTAGCCAGGTGCAACCAGAAGACATGATAGAAACTAGATATGTTATTACTGATCAG
842  197_HRV80    CACACTAGCCAGGTGCAACCAGAAGACATGATAGAAACTAGATATGTTATTACTGATCAG
843  198_HRV51    CATACTAGTCAAGTTCAACCAGAAGATATGGTAGAGACCAGGTATGTTGTCACAGACCAA
844  199_HRV51a   CATACTAGTCAAGTTCAACCAGAAGATATGGTAGAGACCAGGTATGTTGTCACAGACCAA
845  200_HRV51b   CATACTAGTCAAGTTCAACCAGAAGATATGGTAGAGACCAGGTATGTTGTCACAGACCAA
```

FIG. D7 CONT'D

```
03.trace                                                                    9/20/2007 5:03 PM 846  201_HRV65a    CACACTAGTCAAGTTCAACCAGAGGATGTGATAGAAACCAGATATGTCATCACAGATCAA
847  202_HRV65b    CACACTAGTCAAGTTCAACCAGAGGATGTGATAGAAACCAGATATGTCATCACAGATCAA
848  203_HRV65     CACACTAGTCAAGTTCAACCAGAGGATGTGATAGAAACCAGATATGTCATCACAGATCAA
849  204_HRV71a    CATACCAACCAAGTACAACCAGAAGATGTTATGGAAACCAGATATGTGATCACTGATCAA
850  205_HRV71b    CATACCAACCAAGTACAACCAGAAGATGTTATGGAAACCAGATATGTGATCACTGATCAA
851  206_HRV71     CATACCAACCAAGTACAACCAGAAGATGTTATGGAAACCAGATATGTGATCACTGATCAA
852  207_HRV8      CACACAAGTTCAGTGCAACCTGAAGATCTTATAGAGACTAGGTATGTAATTACAGATCAA
853  208_HRV95     CACACAAGTTCAGTGCAACCTGAAGATCTTATAGAGACTAGGTATGTAATTACAGATCAA
854  209_HRV45     CACACCAGTTCAGTGCAGCCTGAGGACCTTATAGAGACTAGATATGTGATTGCAGACCAA
855  210_HRV45a    CACACCAGTTCAGTGCAGCCTGAGGACCTTATAGAGACTAGATATGTGATTGCAGACCAA
856  211_HRV45b    CACACCAGTTCAGTGCAGCCTGAGGACCTTATAGAGACTAGATATGTGATTGCAGACCAA
857  GROUP_1       CA-AC-A--------CA-CC-GA-GA-----T-GA-AC--G----GT-----------A-
858
859  1_HRV1A1|d    ACAAGAGATGAGATGAGTATAGAAAGTTTCCTTGGTAGATCTGGTTGTGTCCACATCTCA
860  2_HRV1A2|d    ACAAGAGATGAGATGAGTATAGAAAGTTTCCTTGGTAGATCTGGTTGTGTCCACATCTCA
861  3_HRV1A|cD    ACAAGAGATGAGATGAGTATAGAAAGTTTCCTTGGTAGATCTGGTTGTGTCCACATCTCA
862  4_HRV1B1|d    ACAAGAGATGAGATGAGTATAGAAAGTTTTCTTGGTAGATCTGGCTGTGTGCATATTTCA
863  5_HRV1B2|d    ACAAGAGATGAGATGAGTATAGAAAGTTTTCTTGGTAGATCTGGCTGTGTGCATATTTCA
864  6_HRV1B       ACAAGAGATGAGATGAGTATAGAAAGTTTTCTTGGTAGATCTGGCTGTGTGCATATTTCA
865  7_HRV40a|d    ACTAGAGATGAAATGAGCATAGAGAGTTTCTTGGGAAGATCTGGGTGCATTCATATATCC
866  8_HRV40b|d    ACTAGAGATGAAATGAGCATAGAGAGTTTCTTGGGAAGATCTGGGTGCATTCATATATCC
867  9_HRV40       ACTAGAGATGAAATGAGCATAGAGAGTTTCTTGGGAAGATCTGGGTGCATTCATATATCC
868  10_HRV85      ACTAGGGATTTAGAAAGTTTCTTGGGAAGATCTGGATGTATCCATATATCT
869  11_HRV85a|    ACTAGGGATGAAATGAGTTTAGAAAGTTTCTTGGGAAGATCTGGATGTATCCATATATCT
870  12_HRV85b|    ACTAGGGATGAAATGAGTTTAGAAAGTTTCTTGGGAAGATCTGGATGTATCCATATATCT
871  13_HRV56a|    ACTAGGGATGAAATGAGTATAGAGAGTTTTCTAGGTAGATCAGGTTGTATACATATATCA
872  14_HRV56b|    ACTAGGGATGAAATGAGTATAGAGAGTTTTCTAGGTAGATCAGGTTGTATACATATATCA
873  15_HRV56      ACTAGGGATGAAATGAGTATAGAGAGTTTTCTAGGTAGATCAGGTTGTATACATATATCA
874  16_HRV54      ACTAGAGATGAAATGAGCATAGAAAGTTTTCTAGGCAGGGCTGGTTGCATACATGAATCC
875  17_HRV98      ACCAGAGATGAAATGAGTATAGAAAGTTTTCTAGGTAGGGCCGGTTGTATACATGAATCT
876  18_HRV59a|    ACTAGAGATGAGATGAGTGTAGAAAGTTTCTTAGGTAGATCTGGGTGTATACATATTTCA
877  19_HRV59b|    ACTAGAGATGAGATGAGTGTAGAAAGTTTCTTAGGTAGATCTGGGTGTATACATATTTCA
878  20_HRV59      ACTAGAGATGAGATGAGTGTAGAAAGTTTCTTAGGTAGATCTGGGTGTATACATATTTCA
879  21_HRV63      ACAAGGGATGAAATGAGTGTAGAGAGCTTTCTTGGTAGATCAGGATGCATACACATATCA
880  22_HRV63b|    ACAAGGGATGAAATGAGTGTAGAGAGCTTTCTTGGTAGATCAGGATGCATACACATATCA
881  23_HRV63a|    ACAAGGGATGAAATGAGTGTAGAGAGCTTTCTTGGTAGATCAGGATGCATACACATATCA
882  24_HRV39      ACTAGGGATGAAATGAGCGTTGAAAGTTTCTTAGGCAGATCTGGCTGTATTCACATTTCC
883  25_HRV39a|    ACTAGGGATGAAATGAGCGTTGAAAGTTTCTTAGGCAGATCTGGCTGTATTCACATTTCC
884  26_HRV39b|    ACTAGGGATGAAATGAGTGTTGAAAGTTTCTTAGGCAGATCTGGCTGTATTCACATTTCC
885  27_HRV10a|    ACGAGAGATGAAATGAGTATTGAAAGTTTTCTTGGCAGGTCAGGTTGTATACACACCTCA
886  28_HRV10b|    ACGAGAGATGAAATGAGTATTGAAAGTTTTCTTGGCAGGTCAGGTTGTATACACACCTCA
887  29_HRV10      ACGAGAGATGAAATGAGTATTGAAAGTTTTCTTGGCAGGTCAGGTTGTATACACACCTCA
888  30_HRV100a    ACCAGGGATGAAATGAGTATTGAGAGCTTTCTTGGAAGATCTGGTTGTATACACACCTCA
889  31_HRV100b    ACCAGGGATGAAATGAGTATTGAGAGCTTTCTTGGAAGATCTGGTTGTATACACACCTCA
890  32_HRV100     ACCAGGGATGAAATGAGTATTGAGAGCTTTCTTGGAAGATCTGGTTGTATACACACCTCA
891  33_HRV66      ACTAGAGATGAAATGAGCATAGAAAGTTTTCTAGGTAGGTCAGGATGTATCCATATATCA
892  34_HRV66b|    ACTAGAGATGAAATGAGCATAGAAAGTTTTCTAGGTAGGTCAGGATGTATCCATATATCA
893  35_HRV66a|    ACTAGAGATGAAATGAGCATAGAAAGTTTTCTAGGTAGGTCAGGATGTATCCATATATCA
894  36_HRV77a|    ACAAGGGATGAGATGAGTATTGAGAGCTTTCTGGGTAGGTCTGGTTGTATTCACATTTCA
895  37_HRV77b|    ACAAGGGATGAGATGAGTATTGAGAGCTTTCTGGGTAGGTCTGGTTGTATTCACATTTCA
896  38_HRV77      ACAAGGGATGAGATGAGTATTGAGAGCTTTCTGGGTAGGTCTGGTTGTATTCACATTTCA
897  39_HRV62a     ACTAGAGATGAAATGAGCATTGAGAGCTTTCTTGGTAGGTCAGGGTGCGTACACACTTCA
898  40_HRV62b     ACTAGAGATGAAATGAGCATTGAGAGCTTTCTTGGTAGGTCAGGGTGCGTACACACTTCA
899  41_HRV25      ACTAGAGATGAAATGAGTATTGAAAGTTTTCTTGGTAGGTCAGGGTGTACATACTTCA
900  42_HRV29a     ACTAGAGATGAAATGAGCATTGAAAGTTTCTTGGGTAGATCAGGATGTATACATGTTTCA
901  43_HRV29b     ACTAGAGATGAAATGAGCATTGAAAGTTTTCTTGGTAGATCAGGATGTATACATGTTTCA
902  44_HRV44a     ACTAGAGATGAAATGAGCATTGAAAGTTTTCTTGGCAGATCAGGGTGTATACATGTTTCA
903  45_HRV44b     ACTAGAGATGAAATGAGCATTGAAAGTTTCTTCTTGGCAGATCAGGGTGTATACATGTTTCA
904  46_HRV31      ACAAGGATGAAATGAGCATTGAAAGTTTCCTTGGTAGGTCAGGATGTGTACATACTTCA
905  47_HRV31a|    ACAAGGAGATGAAATGAGCATTGAAAGTTTCCTTGGTAGGTCAGGATGTGTACATACTTCA
906  48_HRV31b|    ACAAGAGATGAAATGAGCATTGAAAGTTTCCTTGGTAGGTCAGGATGTGTACATACTTCA
907  49_HRV47      ACAAGAGATGAAATGAGCATTGAGAGCTTCCTTGGCAGGTCAGGATGTGTGCATTCCTCA
908  50_HRV47a|    ACAAGAGATGAAATGAGCATTGAGAGCTTCCTTGGCAGGTCAGGATGTGTGCATTCCTCA
909  51_HRV47b|    ACAAGAGATGAAATGAGCATTGAGAGCTTCCTTGGCAGGTCAGGATGTGTGCATTCCTCA
910  52_HRV11      ACTCTTGATGAAATGAGCATTGAGAGCTTCCTAGGTAGATCTGGTTGTATTCACATGTCC
```

FIG. D7 CONT'D

03.trace                                                                    9/20/2007 5:03 PM

```
911  53_HRV11b|   ACTCTTGATGAAATGAGCATTGAGAGCTTCCTAGGTAGATCTGGTTGTATTCACATGTCC
912  54_HRV11a|   ACTCTTGATGAAATGAGCATTGAGAGCTTCCTAGGTAGATCTGGTTGTATTCACATGTCC
913  55_HRV76    ACTCTTGATGAGATGTGTATGGAGAGTTTCTTAGGGAGATCTGGTTGTATTCATATTTCA
914  56_HRV76b|   ACTCTTGATGAGATGTGTATGGAGAGTTTCTTAGGGAGATCTGGTTGTATTCATATTTCA
915  57_HRV76a|   ACTCTTGATGAGATGTGTATGGAGAGTTTCTTAGGGAGATCTGGTTGTATTCATATTTCA
916  58_HRV33    ACTCTTGATGAGATGAGTGTGGAAAGCTTCTTAGGGAGATCTGGTTGCATTCACATGTCA
917  59_HRV33b|   ACTCTTGATGAGATGAGTGTGGAAAGCTTCTTAGGAAGGTCTGGTTGCATTCACATGTCA
918  60_HRV33a|   ACTCTTGATGAGATGAGTGTGGAAAGCTTCTTAGGAAGGTCTGGTTGCATTCACATGTCA
919  61_HRV24a|   ACATTACATGAGATGAGTGTTGAAAGTTTCTTGGGTAGATCAGGTTGCATACACATGTCC
920  62_HRV24b|   ACATTACATGAGATGAGTGTTGAAAGTTTCTTGGGTAGATCAGGTTGCATACACATGTCC
921  63_HRV24    ACATTACATGAGATGAGTGTTGAAAGTTTCTTGGGTAGATCAGGTTGCATACACATGTCC
922  64_HRV90    ACAAGAGATGAAATGAGTGTTGAAAGTTTTCTAGGGAGATCAGGTTGCATTCATATGTCA
923  65_HRV90a|   ACAAGAGATGAAATGAGTGTTGAAAGTTTTCTAGGGAGATCAGGTTGCATTCATATGTCA
924  66_HRV90b|   ACAAGAGATGAGATGAGTGTTGAAAGTTTTCTAGGGAGATCAGGTTGCATTCATATGTCA
925  67_HRV34    ACAAGAGATGAAATGAGCATTGAGAGTTTCCTGGGTAGGTCTGGCTGTATACACATGTCC
926  68_HRV34b|   ACAAGAGATGAAATGAGCATTGAGAGTTTCCTGGGTAGGTCTGGCTGTATACACATGTCC
927  69_HRV34a|   ACAAGAGATGAAATGAGCATTGAGAGTTTCCTGGGTAGGTCTGGCTGTATACACATGTCC
928  70_HRV50a|   ACAAGAGATGAAATGAGCATTGAAAGTTTCCTAGGTAGATCTGGTTGTATACATATATCT
929  71_HRV50b|   ACAAGAGATGAAATGAGCATTGAAAGTTTCCTAGGTAGATCTGGTTGTATACATATATCT
930  72_HRV50    ACAAGAGATGAAATGAGCATTGAAAGTTTCCTAGGTAGATCTGGTTGTATACATATATCT
931  73_HRV18a|   ACAAGAGATGAAATGAGTATAGAGTGTTTTCTAGGCAGATCAGGGTGTATACATATCTCC
932  74_HRV18b|   ACAAGAGATGAAATGAGTATAGAGTGTTTTCTAGGCAGATCAGGGTGTATACATATCTCC
933  75_HRV18    ACAAGAGATGAAATGAGTATAGAGTGTTTTCTAGGCAGATCAGGGTGTATACATATCTCC
934  76_HRV55    ACTCGTGATGAGATGAGCATTGAAAGTTTTCTAGGTAGATCAGGATGTGTACATATATCA
935  77_HRV55b|   ACTCGTGATGAGATGAGCATTGAAAGTTTTCTAGGTAGATCAGGATGTGTACATATATCA
936  78_HRV55a|   ACTCGTGATGAGATGAGCATTGAAAGTTTTCTAGGTAGATCAGGATGTGTACATATATCA
937  79_HRV57    ACACGTGATGAAATGAGTCTTGAGAGCTTCTTAGGAAGATCTGGCTGCATTCATATTTCA
938  80_HRV57a|   ACACGTGATGAAATGAGTCTTGAGAGCTTCTTAGGAAGATCTGGCTGCATTCATATTTCA
939  81_HRV57b|   ACACGTGATGAAATGAGTCTTGAGAGCTTCTTAGGAAGATCTGGCTGCATTCATATTTCA
940  82_HRV21    ACACGTGATGAAATGAGTTTGAAAGTTTCCTGGGCAGATCAGGGTGCATTCACATGTCA
941  83_HRVHan   ACACGTGATGAAATGAGTATTGAAAGTTTTCTAGGCAGATCAGGGTGTATCCACATGTCA
942  84_HRV43    ACCAGAGATGAAATGAGTATTGAAAGTTTCTTGGGCAGATCTGGTTGCATACATATTTCA
943  85_HRV43b|   ACCAGAGATGAAATGAGTATTGAAAGTTTCTTGGGCAGATCTGGTTGCATACATATTTCA
944  86_HRV43a|   ACCAGAGATGAAATGAGTATTGAAAGTTTCTTGGGCAGATCTGGTTGCATACATATTTCA
945  87_HRV75    ACTAGAGATGAGATGAGTATTGAGAGTTTCCTAGGCAGATCTGGATGTATTCATATTTCA
946  88_HRV75b|   ACTAGAGATGAGATGAGTATTGAGAGTTTCCTAGGCAGATCTGGATGTATTCATATTTCA
947  89_HRV75a|   ACTAGAGATGAGATGAGTATTGAGAGTTTCCTAGGCAGATCTGGATGTATTCATATTTCA
948  96_HRV9a|d  ACCAGAGATGAAATGAGTCTTGAAAGCTTCTTAGGGAGATCAGGTTGTATACACATATCT
949  97_HRV9b|d  ACCAGAGATGAAATGAGTCTTGAAAGCTTCTTAGGGAGATCAGGTTGTATACACATATCT
950  98_HRV9     ACCAGAGATGAAATGAGTCTTGAAAGCTTCTTAGGGAGATCAGGTTGTATACACATATCT
951  99_HRV32    ACTAGAGATGAGATGAGTCTTGAGAGCTTCTTAGGGAGGTCAGGATGTGTACATATATCC
952  100_HRV32a   ACTAGAGATGAGATGAGTCTTGAGAGCTTCTTAGGGAGGTCAGGATGTGTACATATATCC
953  101_HRV32b   ACTAGAGATGAGATGAGTCTTGAGAGCTTCTTAGGGAGGTCAGGATGTGTACATATATCC
954  102_HRV67    ACCAGAGATGAAATGAGTCTCGAGAGCTTTCTTGGAAGGTCAGGCTGTATTCATATATCA
955  103_HRV67a   ACCAGAGATGAAATGAGTCTCGAGAGCTTTCTTGGAAGGTCAGGCTGTATTCATATATCA
956  104_HRV67b   ACCAGAGATGAAATGAGTCTCGAGAGCTTTCTTGGAAGGTCAGGCTGTATTCATATATCA
957  105_HRV15    ACCAGAGATGAAATGAGTATTGAGAGCTTCCTTGGTAGATCAGGGTGTGTCCATATTTCT
958  106_HRV15a   ACCAGAGATGAAATGAGTATTGAGAGCTTCCTTGGTAGATCAGGGTGTGTCCATATTTCT
959  107_HRV15b   ACCAGAGATGAAATGAGTATTGAGAGCTTCCTTGGTAGATCAGGGTGTGTCCATATTTCT
960  108_HRV74a   ACAAGAGATGAGATGAGTGTAGAAAGTTTTCTTGGAAGATCAGGATGCATCCATATCTCA
961  109_HRV74b   ACAAGAGATGAGATGAGTGTAGAAAGTTTTCTTGGAAGATCAGGATGCATCCATATCTCA
962  110_HRV74    ACAAGAGATGAGATGAGTGTAGAAAGTTTTCTTGGAAGATCAGGATGCATCCATATCTCA
963  111_HRV38a   ACTAGAGATGAAATGAGTGTAGAAAGTTTTCTAGGAAGATCAGGTTGTGTACATATATCC
964  112_HRV38b   ACTAGAGATGAAATGAGTGTAGAAAGTTTTCTAGGAAGATCAGGTTGTGTACATATATCC
965  113_HRV38    ACTAGAGATGAAATGAGTGTAGAAAGTTTTCTAGGAAGATCAGGTTGTGTACATATATCC
966  114_HRV60    ACTAGAGATGAGATGAGTGTTGAGAGCTTCCTCGGCAGATCTGGATGTATTCATATTTCC
967  115_HRV60a   ACTAGAGATGAGATGAGTGTTGAGAGCTTCCTCGGCAGATCTGGATGTATTCATATTTCC
968  116_HRV60b   ACTAGAGATGAGATGAGTGTTGAGAGCTTCCTCGGCAGATCTGGATGTATTCATATTTCC
969  117_HRV64a   ACTAGAGATGAAATGAGCATTGAGAGTTTCTTGGGCAGGTCTGGTTGTATACACATATCA
970  118_HRV64b   ACTAGAGATGAAATGAGCATTGAGAGTTTCTTGGGCAGGTCTGGTTGTATACACATATCA
971  119_HRV64    ACTAGAGATGAAATGAGCATTGAGAGTTTCTTGGGCAGGTCTGGTTGTATACACATATCA
972  120_HRV94a   ACAAGGGATGAAATGAGCATTGAAAGCTTCTTGGGAAGATCTGGCTGTATACACATAGCA
973  121_HRV94b   ACAAGGGATGAAATGAGCATTGAAAGCTTCTTGGGAAGATCTGGCTGTATACACATAGCA
974  122_HRV94    ACAAGGGATGAAATGAGCATTGAAAGCTTCTTGGGAAGATCTGGCTGTATACACATAGCA
975  123_HRV22    ACTAGAGATGAAATGAGTATTGAGAGCTTCCTGGGAAGATCTGGTTGCATACATATATCA
```

FIG. D7 CONT'D 03.trace                                                              9/20/2007 5:03 PM

```
 976 124_HRV22a   ACTAGAGATGAAATGAGTATTGAGAGCTTCCTGGGAAGATCTGGTTGCATACATATATCA
 977 125_HRV22b   ACTAGAGATGAAATGAGTATTGAGAGCTTCCTGGGAAGATCTGGTTGCATACATATATCA
 978 126_HRV82    ACTAGAGATGAGATGAGCCTTGAGAGTTTCCTAGGGAGATCTGGCTGCATACACATATCA
 979 127_HRV82b   ACTAGAGATGAGATGAGCCTTGAGAGTTTCCTAGGGAGATCTGGCTGCATACACATATCA
 980 128_HRV82a   ACTAGAGATGAGATGAGCCTTGAGAGTTTCCTAGGGAGATCTGGCTGCATACACATATCA
 981 129_HRV19    ACTAGGGATGAAATGAGCATAGAAAGTTTTCTTGGCAGATCCGGTTGTGTACATGTTTCA
 982 130_HRV19a   ACTAGGGATGAAATGAGCATAGAAAGTTTTCTTGGCAGATCCGGTTGTGTACATGTTTCA
 983 131_HRV19b   ACTAGGGATGAAATGAGCATAGAAAGTTTTCTTGGCAGATCCGGTTGTGTACATGTTTCA
 984 132_HRV13    ACTAGGGATGAAATGAGTGTTGAGAGCTTTTTAGGCAGATCTGGTTGTATACACATGTCT
 985 133_HRV13a   ACTAGGGATGAAATGAGTGTTGAGAGCTTTTTAGGCAGATCTGGTTGTATACACATGTCT
 986 134_HRV13b   ACTAGGGATGAAATGAGTGTTGAGAGCTTTTTAGGCAGATCTGGTTGTATACACATGTCT
 987 135_HRV41    ACTAGAGATGAAATGAGCATAGAAAGCTTTTTAGGTAGATCAGGCTGTGTACATAAGTCC
 988 136_HRV41a   ACTAGAGATGAAATGAGCATAGAAAGCTTTTTAGGTAGATCAGGCTGTGTACATAAGTCC
 989 137_HRV41b   ACTAGAGATGAAATGAGCATAGAAAGCTTTTTAGGTAGATCAGGCTGTGTACATAAGTCC
 990 138_HRV73    ACTAGAGATGAAATGAGCATTGAAAGCTTCCTTGGCAGGTCAGGTTGTATACACATGTCA
 991 139_HRV73b   ACTAGAGATGAAATGAGCATTGAAAGCTTCCTTGGCAGGTCAGGTTGTATACACATGTCA
 992 140_HRV73a   ACTAGAGATGAAATGAGCATTGAAAGCTTCCTTGGCAGGTCAGGTTGTATACACATGTCA
 993 141_HRV61    ACAAGAGATGAAATGAGTGTAGAAAGTTTCTTGGTAGATCAGGGTGCATACATATGTCA
 994 142_HRV61a   ACAAGAGATGAAATGAGTGTAGAAAGTTTCTTGGGTAGATCAGGGTGCATACATATGTCA
 995 143_HRV61b   ACAAGAGATGAAATGAGTGTAGAAAGTTTCTTGGGTAGATCAGGGTGCATACATATGTCA
 996 144_HRV96    ACGAGAGATGAAATGAGCATTGAGAGCTTTTGGGTAGATCAGGGTGTATACACATGTCA
 997 145_HRV96b   ACGAGAGATGAAATGAGCATTGAGAGCTTTTTGGGTAGATCAGGGTGTATACACATGTCA
 998 146_HRV96a   ACGAGAGATGAAATGAGCATTGAGAGCTTTTTGGGTAGATCAGGGTGTATACACATGTCA
 999  90_HRV16|   ACATTGGATGAAATGAGTGTGGAAAGCTTCCTAGGCAGATCGGGGTGCATCCATGAATCA
1000  91_HRV16b|  ACATTGGATGAAATGAGTGTGGAAAGCTTCCTAGGCAGATCGGGGTGCATCCATGAATCA
1001  92_1AYM_A   ACATTGGATGAAATGAGTGTGGAAAGCTTCCTAGGCAGATCGGGGTGCATCCATGAATCA
1002  93_HRV81a|  ACACTGGATGAAATGAGTGTAGAAAGTTTTTTAGGCAGATCAGGTTGCATTCATGAATCC
1003  94_HRV81b|  ACACTGGATGAAATGAGTGTAGAAAGTTTTTTAGGCAGATCAGGTTGCATTCATGAATCC
1004  95_HRV81    ACACTGGATGAAATGAGTGTAGAAAGTTTTTTAGGCAGATCAGGTTGCATTCATGAATCC
1005 147_HRV2     ACAAGAGATGAAATGAGTTTAGAGAGTTTTCTTGGCAGATCAGGATGCATACATGAATCT
1006 148_HRV2a|   ACAAGAGATGAAATGAGTTTAGAGAGTTTTCTTGGCAGATCAGGATGCATACATGAATCT
1007 149_HRV2b|   ACAAGAGATGAAATGAGTTTAGAGAGTTTTCTTGGCAGATCAGGATGCATACATGAATCT
1008 150_HRV49a   ACAAGAGATGAAATGAGTTTAGAGAGTTTTCTTGGTAGGTCAGGGTGTATACATGAATCC
1009 151_HRV49b   ACAAGAGATGAAATGAGTTTAGAGAGTTTTCTTGGTAGGTCAGGGTGTATACATGAATCC
1010 152_HRV49    ACAAGAGATGAAATGAGTTTTCTTGGTAGGTCAGGGTGTATACATGAATCC
1011 153_HRV23a   ACAAGAGATGAAATGAGTTTAGAAAGTTTCCTTGGTAGGTCAGGGTGTATACATGAATCT
1012 154_HRV23b   ACAAGAGATGAAATGAGTTTAGAAAGTTTCCTTGGTAGGTCAGGGTGTATACATGAATCT
1013 155_HRV23    ACAAGAGATGAAATGAGTTTAGAAAGTTTCCTTGGTAGGTCAGGGTGTATACATGAATCT
1014 156_HRV30a   ACAAGGGATGAAATGAGTTTAGAAAGCTTTCTTGGTAGATCAGGATGTATACACGAGTCT
1015 157_HRV30b   ACAAGGGATGAAATGAGTTTAGAAAGCTTTCTTGGTAGATCAGGATGTATACACGAGTCT
1016 158_HRV30    ACAAGGGATGAAATGAGTTTAGAAAGCTTTCTTGGTAGATCAGGATGTATACACGAGTCT
1017 159_HRV7     ACAAGGGATGAAACTAGTATAGAGAGTTTCTTAGGTAGATCTGGATGTATTGCTAAAGTT
1018 160_HRV7b|   ACAAGGGATGAAACTAGTATAGAGAGTTTCTTAGGTAGATCTGGATGTATTGCTAAAGTT
1019 161_HRV7a|   ACAAGGGATGAAACTAGTATAGAGAGTTTCTTAGGTAGATCTGGATGTATTGCTAAAGTT
1020 162_HRV88    ACAAGGGATGAAACCAGCATTGAAAGCTTTCTGGGTAGGTCTGGATGCATAGCAAAAATT
1021 163_HRV88a   ACAAGGGATGAAACCAGCATTGAAAGCTTTCTGGGTAGGTCTGGATGCATAGCAAAAATT
1022 164_HRV88b   ACAAGGGATGAAACCAGCATTGAAAGCTTTCTGGGTAGGTCTGGATGCATAGCAAAAATT
1023 165_HRV36a   ACAAGAGATGAGACAAGTATTGAAAGCTTCTTAGGTAGGTCAGGGTGCATAGCTATGATA
1024 166_HRV36b   ACAAGAGATGAGACAAGTATTGAAAGCTTCTTAGGTAGGTCAGGGTGCATAGCTATGATA
1025 167_HRV36    ACAAGAGATGAGACAAGTATTGAAAGCTTCTTAGGTAGGTCAGGGTGCATAGCTATGATA
1026 168_HRV89a   ACAAGGGATGAAACAAGTATTGAGAGTTTCTTAGGTAGGTCAGGGTGTATCGCTATGATA
1027 169_HRV89b   ACAAGGGATGAAACAAGTATTGAGAGTTTCTTAGGTAGGTCAGGGTGTATCGCTATGATA
1028 170_HRV89    ACAAGGGATGAAACAAGTATTGAGAGTTTCTTAGGTAGGTCAGGGTGTATCGCTATGATA
1029 171_HRV58    ACAAGAGATGAAACTAGCATTGAAAGCTTTTTAGGTAGATCTGGTTGCATTGCTATCATA
1030 172_HRV58a   ACAAGAGATGAAACTAGCATTGAAAGCTTTTTAGGTAGATCTGGTTGCATTGCTATCATA
1031 173_HRV58b   ACAAGAGATGAAACTAGCATTGAAAGCTTTTTAGGTAGATCTGGTTGCATTGCTATCATA
1032 174_HRV12a   ACTAGAGATGAGATGTCAATTGAATCTTCCTTGGTCGGTCCGGATGCATTTCAATTATC
1033 175_HRV12b   ACTAGAGATGAGATGTCAATTGAATCTTCCTTGGTCGGTCCGGATGCATTTCAATTATC
1034 176_HRV12    ACTAGAGATGAGATGTCAATTGAATCTTCCTTGGTCGGTCCGGATGCATTTCAATTATC
1035 177_HRV78a   ACAAGAGATGAAATGAGCATTGAAAGTTTCCTCGGAAGATCAGGTTGTGCAACAATTATG
1036 178_HRV78b   ACAAGAGATGAAATGAGCATTGAAAGTTTCCTCGGAAGATCAGGTTGTGCAACAATTATG
1037 179_HRV78    ACAAGAGATGAAATGAGCATTGAAAGTTTCCTCGGAAGATCAGGTTGTGCAACAATTATG
1038 180_HRV20    ACCCGTGATGAAATGAGTGTGGAAAGTTTTCTTGGTAGATCTGGTTGCATTGCTATCATA
1039 181_HRV20a   ACCCGTGATGAAATGAGTGTGGAAAGTTTTCTTGGTAGATCTGGTTGCATTGCTATCATA
1040 182_HRV20b   ACCCGTGATGAAATGAGTGTGGAAAGTTTTCTTGGTAGATCTGGTTGCATTGCTATCATA
```

FIG. D7 CONT'D

```
03.trace                                                                    9/20/2007 5:03 PM 1041  183_HRV68    ACAAGGGATGAAATGAGCATAGAGAGCTTCCTCGGTAGGTCAGGTTGCATTGCAATCATA
1042  184_HRV68a   ACAAGGGATGAAATGAGCATAGAGAGCTTCCTCGGTAGGTCAGGTTGCATTGCAATCATA
1043  185_HRV68b   ACAAGGGATGAAATGAGCATAGAGAGCTTCCTCGGTAGGTCAGGTTGCATTGCAATCATA
1044  186_HRV28    ACCCGTGATGAAATGAGTATAGAGAGTTTCTTAGGTAGGTCTAGTTGCATTGCAATAATC
1045  187_HRV28a   ACCCGTGATGAAATGAGTATAGAGAGTTTCTTAGGTAGGTCTAGTTGCATTGCAATAATC
1046  188_HRV28b   ACCCGTGATGAAATGAGTATAGAGAGTTTCTTAGGTAGGTCTAGTTGCATTGCAATAATC
1047  189_HRV53a   ACCCGGGATGAAATGAGCATTGAAAGTTTCTTAGGCAGATCAAGTTGCATTGCTGAGATC
1048  190_HRV53b   ACCCGGGATGAAATGAGCATTGAAAGTTTCTTAGGCAGATCAAGTTGCATTGCTGAGATC
1049  191_HRV53    ACCCGGGATGAAATGAGCATTGAAAGTTTCTTAGGCAGATCAAGTTGCATTGCTGAGATC
1050  192_HRV46a   ACAAAAGATGAAATGAGTATAGAAAGTTTTCTAGGAAGGTCAGGCTGCATTGCCATTATT
1051  193_HRV46b   ACAAAAGATGAAATGAGTATAGAAAGTTTTCTAGGAAGGTCAGGCTGCATTGCCATTATT
1052  194_HRV46    ACAAAAGATGAAATGAGTATAGAAAGTTTTCTAGGAAGGTCAGGCTGCATTGCCATTATT
1053  195_HRV80a   ACAAAGGATGAGATGAGCATTGAAAGTTTCTTAGGAAGATCTGGTTGTGTTGCTATCATT
1054  196_HRV80b   ACAAAGGATGAGATGAGCATTGAAAGTTTCTTAGGAAGATCTGGTTGTGTTGCTATCATT
1055  197_HRV80    ACAAAGGATGAGATGAGCATTGAAAGTTTCTTAGGAAGATCTGGTTGTGTTGCTATCATT
1056  198_HRV51    ACTAGAGATGAAATGAGTATAGAGAGTTTCTTGGGTAGATCTGCTTGCGTAGCAATCATC
1057  199_HRV51a   ACTAGAGATGAAATGAGTATAGAGAGTTTCTTGGGTAGATCTGCTTGCGTAGCAATCATC
1058  200_HRV51b   ACTAGAGATGAAATGAGTATAGAGAGTTTCTTGGGTAGATCTGCTTGCGTAGCAATCATC
1059  201_HRV65a   ACCAGAGATGAGATGAGCGTAGAGAGTTTCCTGGGCAGATCTGCCTGCATAGCAGTCATT
1060  202_HRV65b   ACCAGAGATGAGATGAGCGTAGAGAGTTTCCTGGGCAGATCTGCCTGCATAGCAGTCATT
1061  203_HRV65    ACCAGAGATGAGATGAGCGTAGAGAGTTTCCTGGGCAGATCTGCCTGCATAGCAGTCATT
1062  204_HRV71a   ACTAGGGATGAAATGAGCATTGAGAGCTTCTTGGGCAGATCTGCATGCATAGCTACCATA
1063  205_HRV71b   ACTAGGGATGAAATGAGCATTGAGAGCTTCTTGGGCAGATCTGCATGCATAGCTACCATA
1064  206_HRV71    ACTAGGGATGAAATGAGCATTGAGAGCTTCTTGGGCAGATCTGCATGCATAGCTACCATA
1065  207_HRV8     ACTAGGCATGAGACATCACTGGAATCTTTCTTGGGTAGAGCAGGATGCATTAAAATCATT
1066  208_HRV95    ACTAGGTATGAGACATCACTGGAATCTTTCTTGGGTAGAGCAGGATGCATTAAAATTATT
1067  209_HRV45    ACCAGACATGAAACCTCCATTGAATCTTTTTGGGTAGGGCTGGATGTGTGGCCAATATT
1068  210_HRV45a   ACCAGACATGAAACCTCCATTGAATCTTTTTGGGTAGGGCTGGATGTGTGGCCAATATT
1069  211_HRV45b   ACCAGACATGAAACCTCCATTGAATCTTTTTGGGTAGGGCTGGATGTGTGGCCAATATT
1070  GROUP_1      AC-----ATGA-A------T-GA----TT--T-GG--G--C----TG------------
1071
1072  1_HRV1A1|d   AGAATAAAGGTTGATTACACTGAC---------------TATAATGGA---CAGGACATA
1073  2_HRV1A2|d   AGAATAAAGGTTGATTACACTGAC---------------TATAATGGA---CAGGACATA
1074  3_HRV1A|cD   AGAATAAAGGTTGATTACACTGAC---------------TATAATGGA---CAGGACATA
1075  4_HRV1B1|d   AGAATAAAGGTTGATTACAATGAC---------------TACAATGGA---GTGAACAAA
1076  5_HRV1B2|d   AGAATAAAGGTTGATTACAATGAC---------------TACAATGGA---GTGAACAAA
1077  6_HRV1B      AGAATAAAGGTTGATTACAATGAC---------------TACAATGGA---GTGAACAAA
1078  7_HRV40a|d   ACAATTACAGTGGATAACAGTTTG---------------GAATATG------ATGACCAC
1079  8_HRV40b|d   ACAATTACAGTGGATAACAGTTTG---------------GAATATG------ATGACCAC
1080  9_HRV40      ACAATTACAGTGGATAACAGTTTG---------------GAATATG------ATGACCAC
1081  10_HRV85     ACAATTACTGTGAATAACAACCTA---------------GATTATG------ATGAAAAT
1082  11_HRV85a|   ACAATTACTGTGAATAACAACCTA---------------GATTATG------ATGAAAAT
1083  12_HRV85b|   ACAATTACTGTGAATAACAACCTA---------------GATTATG------ATGAAAAT
1084  13_HRV56a|   ACTATAACTGTGGATAATGATGTA---------------GATTATA------ATTCAAAG
1085  14_HRV56b|   ACTATAACTGTGGATAATGATGTA---------------GATTATA------ATTCAAAG
1086  15_HRV56     ACTATAACTGTGGATAATGATGTA---------------GATTATA------ATTCAAAG
1087  16_HRV54     ACCATTACAATTCAAAATGATGTA---------------GAATACA------ATGATCAC
1088  17_HRV98     ACTATCACTATTCAAAATGATGTA---------------GAATATA------ACGATCAT
1089  18_HRV59a|   ACTATTACTGTCAATAAAGACATA---------------AAATATG------ATGATGGA
1090  19_HRV59b|   ACTATTACTGTCAATAAAGACATA---------------AAATATG------ATGATGGA
1091  20_HRV59     ACTATTACTGTCAATAAAGACATA---------------AAATATG------ATGATGGA
1092  21_HRV63     ACTATCACTGTTGACAAAACCATT---------------GACTATG------ACACTGGA
1093  22_HRV63b|   ACTATCACTGTTGACAAAACCATT---------------GACTATG------ACACTGGA
1094  23_HRV63a|   ACTATCACTGTTGACAAAACCATT---------------GACTATG------ACACTGGA
1095  24_HRV39     ACAATTACTATGAAGAAGGAG------------------AACTATA------ATGATCAT
1096  25_HRV39a|   ACAATTACTATGAAGAAGGAG------------------AACTATA------ATGATCAT
1097  26_HRV39b|   ACAATTACTATGAAGAAGGAG------------------AACTATA------ATGAACAT
1098  27_HRV10a|   ACAATAACTGTTAATAATACAAGA---------------CCCTACA------ATGAACAC
1099  28_HRV10b|   ACAATAACTGTTAATAATACAAGA---------------CCCTACA------ATGAACAC
1100  29_HRV10     ACAATAACTGTTAATAATACAAGA---------------CCCTACA------ATGAACAC
1101  30_HRV100a   ACAATTACTGTAAGTAAAATGAAA---------------AATTATA------ATGAGCAC
1102  31_HRV100b   ACAATTACTGTAAGTAAAATGAAA---------------AATTATA------ATGAGCAC
1103  32_HRV100    ACAATTACTGTAAGTAAAATGAAA---------------AATTATA------ATGAGCAC
1104  33_HRV66     ACAATTAATGTGGATAGCACAAAA---------------ACATATG------ATGAATCC
1105  34_HRV66b|   ACAATTAATGTGGATAGCACAAAA---------------ACATATG------ATGAATCC
```

FIG. D7 CONT'D 03.trace                                                          9/20/2007 5:03 PM

```
1106  35_HRV66a|    ACAATTAATGTGGATAGCACAAAA---------------ACATATG------ATGAATCC
1107  36_HRV77a|    ACAATAAATGTAGAAGATGGTAAA---------------ACTTATG------ATGAATCT
1108  37_HRV77b|    ACAATAAATGTAGAAGATGGTAAA---------------ACTTATG------ATGAATCT
1109  38_HRV77     ACAATAAATGTAGAAGATGGTAAA---------------ACTTATG------ATGAATCT
1110  39_HRV62a    ACAATTGAA---------ACAACG---------------CTTAGTC------ATAAAGAT
1111  40_HRV62b    ACAATTGAA---------ACAACG---------------CTTAGTC------ATAAAGAT
1112  41_HRV25     ACAATTGAA---------ACAAAA---------------CTTAAAC------ATGATGAA
1113  42_HRV29a    ACAATAAAA---------GCAAAT---------------CAGGCAC------ATGACGCC
1114  43_HRV29b    ACAATAAAA---------GCAAAT---------------CAGGCAC------ATGACGCC
1115  44_HRV44a    ACAATAAAG---------ACAAAT---------------CAGGCAC------ACAATACC
1116  45_HRV44b    ACAATAAAG---------ACAAAT---------------CAGGCAC------ACAATACC
1117  46_HRV31     ATAATAGAA---------CCAGAT---------------GGACTCC------ATGATAGC
1118  47_HRV31a|    ATAATAGAA---------CCAGAT---------------GGACTCC------ATGATAGC
1119  48_HRV31b|    ATAATAGAA---------CCAGAT---------------GGACTCC------ATGATAGC
1120  49_HRV47     ACAATAAAA---------TCAGAT---------------GAGCAAC------ACATTAAT
1121  50_HRV47a|    ACAATAAAA---------TCAGAT---------------GAGCAAC------ACATTAAT
1122  51_HRV47b|    ACAATACAA---------TCAAAT---------------GAGCAAC------ACATTAAT
1123  52_HRV11     AAGTTAATTGTGCAGTATGAAGAC---------------TATAAT------GGAAAGAAA
1124  53_HRV11b|    AAGTTAATTGTGCAGTATGAAGAC---------------TATAAT------GGAAAGAAA
1125  54_HRV11a|    AAGTTAATTGTGCAGTATGAAGAC---------------TATAAT------GGAAAGAAA
1126  55_HRV76     AAGCTAGTTGTAGAATATGAGGGA---------------TATGAT------GATACAAAA
1127  56_HRV76b|    AAGCTAGTTGTAGAATATGAGGGA---------------TATGAT------GATACAAAA
1128  57_HRV76a|    AAGCTAGTTGTAGAATATGAGGGA---------------TATGAT------GATACAAAA
1129  58_HRV33     AAATTAGTAGTGAAATATGAAGAC---------------TATAAT------GAGAAAAAG
1130  59_HRV33b|    AAATTAGTAGTGAAATATGAAGAC---------------TATAAT------GAGAAAAAG
1131  60_HRV33a|    AAATTAGTAGTGAAATATGAAGAC---------------TATAAT------GAGAAAAAG
1132  61_HRV24a|    AAGTTGACTGTGGATTAT---GAC---------------AATTAT------GATACAAAA
1133  62_HRV24b|    AAGTTGACTGTGGATTAT---GAC---------------AATTAT------GATACAAAA
1134  63_HRV24     AAGTTGACTGTGGATTAT---GAC---------------AATTAT------GATACAAAA
1135  64_HRV90     AAATTAGTTGTAAACTAT---GAT---------------AATTAT------GATGAAAAC
1136  65_HRV90a|    AAATTAGTTGTAAACTAT---GAT---------------AATTAT------GATGAAAAC
1137  66_HRV90b|    AAATTAGTTGTAAACTAT---GAT---------------AATTAT------GATGAAAAC
1138  67_HRV34     AAACTTGTTGTAGATTATGAAAAT---------------TACAATGCA---AAAACAAAG
1139  68_HRV34b|    AAACTTGTTGTAGATTATGAAAAT---------------TACAATGCA---AAAACAAAG
1140  69_HRV34a|    AAACTTGTTGTAGATTATGAAAAT---------------TACAATGCA---AAAACAAAG
1141  70_HRV50a|    AAATTAGTTGTTGATTATGATGGT---------------TACAATGAG---GAAACAAAG
1142  71_HRV50b|    AAATTAGTTGTTGATTATGATGGT---------------TACAATGAG---GAAACAAAG
1143  72_HRV50     AAATTAGTTGTTGATTATGATGGT---------------TACAATGAG---GAAACAAAG
1144  73_HRV18a|    AAGTTAGTTGTACATTATGAAGAT---------------TATAATGCA---GAAACAAGG
1145  74_HRV18b|    AAGTTAGTTGTACATTATGAAGAT---------------TATAATGCA---GAAACAAGG
1146  75_HRV18     AAGTTAGTTGTACATTATGAAGAT---------------TATAATGCA---GAAACAAGG
1147  76_HRV55     GAGTTAGTTGTTCATTATGAAGAA---------------TATAACAAA---GAGGGAAAA
1148  77_HRV55b|    GAGTTAGTTGTTCATTATGAAGAA---------------TATAACAAA---GAGGGAAAA
1149  78_HRV55a|    GAGTTAGTTGTTCATTATGAAGAA---------------TATAACAAA---GAGGGAAAA
1150  79_HRV57     GAGCTTAAGGTAAAATATGAAAAT---------------TACAACACA---GAG------
1151  80_HRV57a|    GAGCTTAAGGTAAAATATGAAAAT---------------TACAACACA---GAG------
1152  81_HRV57b|    GAGCTTAAGGTAAAATATGAAAAT---------------TACAACACA---GAG------
1153  82_HRV21     AAATTAGTAGTTAACTATGATAAT---------------TACAATACT---GGAGAAAAT
1154  83_HRVHan    AAATTAATAGTTAACTATGACAAC---------------TACAATACT---GGAGAAAAT
1155  84_HRV43     ACACTTGAAGTAAATTATGATGAT---------------TATAATGGG---ACAGGCATA
1156  85_HRV43b|    ACACTTGAAGTAAATTATGATGAT---------------TATAATGGG---ACAGGCATA
1157  86_HRV43a|    ACACTTGAAGTAAATTATGATGAT---------------TATAATGGG---ACAGGCATA
1158  87_HRV75     ACACTTGAGATGGATTATACAAAC---------------TATAATGGA---GAAGGCAAA
1159  88_HRV75b|    ACACTTGAGATGGATTATACAAAC---------------TATAATGGA---GAAGGCAAA
1160  89_HRV75a|    ACACTTGAGATGGATTATACAAAC---------------TATAATGGA---GAAGGCAAA
1161  96_HRV9a|d   AAATTGAATATTGATTACAGTGAC---------------TATGATAAG---AGTGTTGAA
1162  97_HRV9b|d   AAATTGAATATTGATTACAGTGAC---------------TATGATAAG---AGTGTTGAA
1163  98_HRV9      AAATTGAATATTGATTACAGTGAC---------------TATGATAAG---AGTGTTGAA
1164  99_HRV32     AAATTAGATATTGATTATACCAAT---------------TACAATAAA---AGTGTTAAG
1165  100_HRV32a   AAATTAGATATTGATTATACCAAT---------------TACAATAAA---AGTGTTAAG
1166  101_HRV32b   AAATTAGATATTGATTATACCAAT---------------TACAATAAA---AGTGTTAAG
1167  102_HRV67    AAATTGAATATTGATTATAATGCA---------------TATGATGAA---AGTAGGGAC
1168  103_HRV67a   AAATTGAATATTGATTATAATGCA---------------TATGATGAA---AGTAGGGAC
1169  104_HRV67b   AAATTGAATATTGATTATAATGCA---------------TATGATGAA---AGTAGGGAC
1170  105_HRV15    GATTTGAAAATACATTATGAAGAT---------------TATAATAAA---GATGGGAAA
```

FIG. D7 CONT'D 03.trace                                                                                       9/20/2007 5:03 PM

```
1171  106_HRV15a    GATTTGAAAATACATTATGAAGAT---------------TATAATAAA---GATGGGAAA
1172  107_HRV15b    GATTTGAAAATACATTATGAAGAT---------------TATAATAAA---GATGGGAAA
1173  108_HRV74a    CATCTAAAAATTGATTATACAAAC---------------TATAATGTT---AAAGGGAAG
1174  109_HRV74b    CATCTAAAAATTGATTATACAAAC---------------TATAATGTT---AAAGGGAAG
1175  110_HRV74     CATCTAAAAATTGATTATACAAAC---------------TATAATGTT---AAAGGGAAG
1176  111_HRV38a    AATCTTGACATAGATTACATTAAT---------------TACAACTCT---GAAGACAAA
1177  112_HRV38b    AATCTTGACATAGATTACATTAAT---------------TACAACTCT---GAAGACAAA
1178  113_HRV38     AATCTTGACATAGATTACATTAAT---------------TACAACTCT---GAAGACAAA
1179  114_HRV60     AAATTAGAAATTGACTATAGTAAC---------------TACAATGAG---GAGAATAAA
1180  115_HRV60a    AAATTAGAAATTGACTATAGTAAC---------------TACAATGAG---GAGAATAAA
1181  116_HRV60b    AAATTAGAAATTGACTATAGTAAC---------------TACAATGAG---GAGAATAAA
1182  117_HRV64a    GATTTAAAAGTAAATTATACTGGG---------------TATAATGAT---GAAGGTAAC
1183  118_HRV64b    GATTTAAAAGTAAATTATACTGGG---------------TATAATGAT---GAAGGTAAC
1184  119_HRV64     GATTTAAAAGTAAATTATACTGGG---------------TATAATGAT---GAAGGTAAC
1185  120_HRV94a    CATCTAGAGATCAAGTATGATGGT---------------TACAATGAT---GCTGGCAAC
1186  121_HRV94b    CATCTAGAGATCAAGTATGATGGT---------------TACAATGAT---GCTGGCAAC
1187  122_HRV94     CATCTAGAGATCAAGTATGATGGT---------------TACAATGAT---GCTGGCAAC
1188  123_HRV22     CACTTGAAGTAAAATACACAGGG----------------TATAATGAA---GAGGGTAAT
1189  124_HRV22a    CACTTAGAAGTAAAATACACAGGG---------------TATAATGAA---GAGGGTAAT
1190  125_HRV22b    CACTTAGAAGTAAAATACACAGGG---------------TATAATGAA---GAGGGTAAT
1191  126_HRV82     CACCTAAATGTCAGATACACTG-----------------ATTATAAT---GAAGGTAAT
1192  127_HRV82b    CACCTAAATGTCAGATACACTG-----------------ATTATAAT---GAAGGTAAT
1193  128_HRV82a    CACCTAAATGTCAGATACACTG-----------------ATTATAAT---GAAGGTAAT
1194  129_HRV19     GAGCTCCAATTAGATTATACCAAT---------------TACAATCAA---GAAAATAAT
1195  130_HRV19a    GAGCTCCAATTAGATTATACCAAT---------------TACAATCAA---GAAAATAAT
1196  131_HRV19b    GAGCTCCAATTAGATTATACCAAT---------------TACAATCAA---GAAAATAAT
1197  132_HRV13     ACCATGAACATAGATTATACTAAT---------------TATGATGAT---TCTGTTAAT
1198  133_HRV13a    ACCATGAACATAGATTATACTAAT---------------TATGATGAT---TCTGTTAAT
1199  134_HRV13b    ACCATGAACATAGATTATACTAAT---------------TATGATGAT---TCTGTTAAT
1200  135_HRV41     ACTTTGAATATAGATTATACTGAT---------------TATGATGAT---TCTATCCAG
1201  136_HRV41a    ACTTTGAATATAGATTATACTGAT---------------TATGATGAT---TCTATCCAG
1202  137_HRV41b    ACTTTGAATATAGATTATACTGAT---------------TATGATGAT---TCTATCCAG
1203  138_HRV73     ACTATGAATATAAATTATGAAAAT---------------TATGATGAT---GCTCCTGAA
1204  139_HRV73b    ACTATGAATATAAATTATGAAAAT---------------TATGATGAT---GCTCCTGAA
1205  140_HRV73a    ACTATGAATATAAATTATGAAAAT---------------TATGATGAT---GCTCCTGAA
1206  141_HRV61     ACATTAAATATAAACTATGATAAC---------------TATGATGAT---TCTATTGAA
1207  142_HRV61a    ACATTAAATATAAACTATGATAAC---------------TATGATGAT---TCTATTGAA
1208  143_HRV61b    ACATTAAATATAAACTATGATAAC---------------TATGATGAT---TCTATTGAA
1209  144_HRV96     ACATTAAACATAGATTATGACAAT---------------TATGATGAC---TCCCCTAAG
1210  145_HRV96b    ACATTAAACATAGATTATGACAAT---------------TATGATGAC---TCCCCTAAG
1211  146_HRV96a    ACATTAAACATAGATTATGACAAT---------------TATGATGAC---TCCCCTAAG
1212   90_HRV16a|   GTGTTGGATATTGTGGACAATTAC---------------AATGAT------------CAA
1213   91_HRV16b|   GTGTTGGATATTGTGGACAATTAC---------------AATGAT------------CAA
1214   92_1AYM_A    GTGTTGGATATTGTGGACAATTAC---------------AATGAT------------CAA
1215   93_HRV81a|   ATATTGGACATTAAAGAGGATTAC---------------AATACC------------CAG
1216   94_HRV81b|   ATATTGGACATTAAAGAGGATTAC---------------AATACC------------CAG
1217   95_HRV81     ATATTGGACATTAAAGAGGATTAC---------------AATACC------------CAG
1218  147_HRV2      AAATTAGAGGTTACACTTGCAAAT---------------TATAACA---------AGGAG
1219  148_HRV2a|    AAATTAGAGGTTACACTTGCAAAT---------------TATAACA---------AGGAG
1220  149_HRV2b|    AAATTAGAGGTTACACTTGCAAAT---------------TATAACA---------AGGAG
1221  150_HRV49a    AAACTAGAGGTCACACTTACAAAT---------------TACAATG---------AAAAT
1222  151_HRV49b    AAACTAGAGGTCACACTTACAAAT---------------TACAATG---------AAAAT
1223  152_HRV49     AAACTAGAGGTCACACTTACAAAT---------------TACAATG---------AAAAT
1224  153_HRV23a    AAATTAAAAGTTGAGATCGGAAAC---------------TATGATG---------AAAAC
1225  154_HRV23b    AAATTAAAAGTTGAGATCGGAAAC---------------TATGATG---------AAAAC
1226  155_HRV23     AAATTAAAAGTTGAGATCGGAAAC---------------TATGATG---------AAAAC
1227  156_HRV30a    AAATTAGAACTTGAGCTTGCACAC---------------TATGATA---------AAAAG
1228  157_HRV30b    AAATTAGAACTTGAGCTTGCACAC---------------TATGATA---------AAAAG
1229  158_HRV30     AAATTAGAACTTGAGCTTGCACAC---------------TATGATA---------AAAAG
1230  159_HRV7      AAACTTGACACAA------CACAGGGT---------GACTATGACACAGGCAAAGGTGTT
1231  160_HRV7b|    AAACTTGACACAA------CACAGGGT---------GACTATGACACAGGCAAAGGTGTT
1232  161_HRV7a|    AAACTTGACACAA------CACAGGGT---------GACTATGACACAGGCAAAGGTGTT
1233  162_HRV88     AAACTTGACACAA------ATGAAGGT---------GATTACGACACA---ATAGGTGTT
1234  163_HRV88a    AAACTTGACACAA------ATGAAGGT---------GATTACGACACA---ATAGGTGTT
1235  164_HRV88b    AAACTTGACACAA------ATGAAGGT---------GATTACGACACA---ATAGGTGTT
```

FIG. D7 CONT'D

```
03.trace                                                                            9/20/2007 5:03 PM 1236 165_HRV36a    GAATTTAGCACAAGTAGTGATAAAGAT---------GAACATGATGAA---ATTGGCAAG
1237 166_HRV36b    GAATTTAGCACAAGTAGTGATAAAGAT---------GAACATGATGAA---ATTGGCAAG
1238 167_HRV36     GAATTTAGCACAAGTAGTGATAAAGAT---------GAACATGATGAA---ATTGGCAAG
1239 168_HRV89a    GAATTTAATACAAGTAGTGATAAAACT---------GAACATGATAAA---ATTGGTAAA
1240 169_HRV89b    GAATTTAATACAAGTAGTGATAAAACT---------GAACATGATAAA---ATTGGTAAA
1241 170_HRV89     GAATTTAATACAAGTAGTGATAAAACT---------GAACATGATAAA---ATTGGTAAA
1242 171_HRV58     AAATTTAACACAA------ATAAGACT---------AATTATGATGAC---ATAGGTGTA
1243 172_HRV58a    AAATTTAACACAA------ATAAGACT---------AATTATGATGAC---ATAGGTGTA
1244 173_HRV58b    AAATTTAACACAA------ATAAGACT---------AATTATGATGAC---ATAGGTGTA
1245 174_HRV12a    GAATTGGATTTAGACCATGAAGGT--------------TATTCAGCA---GAAGGGAAA
1246 175_HRV12b    GAATTGGATTTAGACCATGAAGGT--------------TATTCAGCA---GAAGGGAAA
1247 176_HRV12     GAATTGGATTTAGACCATGAAGGT--------------TATTCAGCA---GAAGGGAAA
1248 177_HRV78a    AGACTAGAATTGGACCACACTGAT--------------TACAATGCT---GAAGGGAAA
1249 178_HRV78b    AGACTAGAATTGGACCACACTGAT--------------TACAATGCT---GAAGGGAAA
1250 179_HRV78     AGACTAGAATTGGACCACACTGAT--------------TACAATGCT---GAAGGGAAA
1251 180_HRV20     CATACTGACTTAGATCATGAAGCACAA---------CAATATAATGCA---CCCGGAAAA
1252 181_HRV20a    CATACTGACTTAGATCATGAAGCACAA---------CAATATAATGCA---CCCGGAAAA
1253 182_HRV20b    CATACTGACTTAGATCATGAAGCACAA---------CAATATAATGCA---CCCGGAAAA
1254 183_HRV68     CATACTGACTTAGATCACAATGAGGAT---------CAGTACAATGCA---CCTGGAAAA
1255 184_HRV68a    CATACTGACTTAGATCACAATGAGGAT---------CAGTACAATGCA---CCTGGAAAA
1256 185_HRV68b    CATACTGACTTAGATCACAATGAGGAT---------CAGTACAATGCA---CCTGGAAAA
1257 186_HRV28     CATACTGATGTTGTGCATGAAACAGAC---------AAGTACAACCAC---CCAGGGAAG
1258 187_HRV28a    CATACTGATGTTGTGCATGAAACAGAC---------AAGTACAACCAC---CCAGGGAAG
1259 188_HRV28b    CATACTGATGTTGTGCATGAAACAGAC---------AAGTACAACCAC---CCAGGGAAG
1260 189_HRV53a    CATACCAATTTAGACCAT---ACTG-----------GATACAATGAG---CCTGGGAAA
1261 190_HRV53b    CATACCAATTTAGACCAT---ACTG-----------GATACAATGAG---CCTGGGAAA
1262 191_HRV53     CATACCAATTTAGACCAT---ACTG-----------GATACAATGAG---CCTGGGAAA
1263 192_HRV46a    GAGACAGAATTGAATCATGAAGAAGGG---------AAATACAATGCA---GAAGATCAA
1264 193_HRV46b    GAGACAGAATTGAATCATGAAGAAGGG---------AAATACAATGCA---GAAGATCAA
1265 194_HRV46     GAGACAGAATTGAATCATGAAGAAGGG---------AAATACAATGCA---GAAGATCAA
1266 195_HRV80a    GAAACCAAATTAAACCATGAAACAGAC---------ATGTACAATGCT---GATGGTCAG
1267 196_HRV80b    GAAACCAAATTAAACCATGAAACAGAC---------ATGTACAATGCT---GATGGTCAG
1268 197_HRV80     GAAACCAAATTAAACCATGAAACAGAC---------ATGTACAATGCT---GATGGTCAG
1269 198_HRV51     CATACAAACCTTGAGCATGTTGAAGCAGACAGACAAGCCTACAATGCA---AAAGGGAAA
1270 199_HRV51a    CATACAAACCTTGAGCATGTTGAAGCAGACAGACAAGCCTACAATGCA---AAAGGGAAA
1271 200_HRV51b    CATACAAACCTTGAGCATGTTGAAGCAGACAGACAAGCCTACAATGCA---AAAGGGAAA
1272 201_HRV65a    CACACAGATCTTAAACATGACCATGAAGGCCAAAATGTTTACAATGAC---GAAGGCAGA
1273 202_HRV65b    CACACAGATCTTAAACATGACCATGAAGGCCAAAATGTTTACAATGAC---GAAGGCAGA
1274 203_HRV65     CACACAGATCTTAAACATGACCATGAAGGCCAAAATGTTTACAATGAC---GAAGGCAGA
1275 204_HRV71a    CACACTAAATTAGTACATGGAGAGGAGGG------TGTTTATAATATG---AAAGGTAAC
1276 205_HRV71b    CACACTAAATTAGTACATGGAGAGGAGGG------TGTTTATAATATG---AAAGGTAAC
1277 206_HRV71     CACACTAAATTAGTACATGGAGAGGAGGG------TGTTTATAATATG---AAAGGTAAC
1278 207_HRV8      GCATTAGAACTAGATCATGACAAC--------------TATGATGAA------------
1279 208_HRV95     GCATTAGAACTAGATCATGACAAC--------------TATGATAAA------------
1280 209_HRV45     AGTTTAGACATTAACCATGATGAC--------------TACCAAAAG------------
1281 210_HRV45a    AGTTTAGACATTAACCATGATGAC--------------TACCAAAAG------------
1282 211_HRV45b    AGTTTAGACATTAACCATGATGAC--------------TACCAAAAG------------
1283 GROUP_1       ------------------------------------------------------------
1284
1285 1_HRV1A1|d    AATTTCACAAAATGGAAAATCACACTACAGGAAATGGCACAGATTAGGAGAAAATTTGAA
1286 2_HRV1A2|d    AATTTCACAAAATGGAAAATCACACTACAGGAAATGGCACAGATTAGGAGAAAATTTGAA
1287 3_HRV1A|cD    AATTTCACAAAATGGAAAATCACACTACAGGAAATGGCACAGATTAGGAGAAAATTTGAA
1288 4_HRV1B1|d    AACTTTACAACATGGAAAATCACACTGCAGGAGATGGCACAAATTAGAAGAAAATTCGAA
1289 5_HRV1B2|d    AACTTTACAACATGGAAAATCACACTGCAGGAGATGGCACAAATTAGAAGAAAATTCGAA
1290 6_HRV1B       AACTTTACAACATGGAAAATCACACTGCAGGAGATGGCACAAATTAGAAGAAAATTCGAA
1291 7_HRV40a|d    CACTTTGATAAGTGGCAGATAACCATACAAGAGATGTCACAAATTAGGAGAAAATTTGAA
1292 8_HRV40b|d    CACTTTGATAAGTGGCAGATAACCATACAAGAGATGTCACAAATTAGGAGAAAATTTGAA
1293 9_HRV40       CACTTTGATAAGTGGCAGATAACCATACAAGAGATGTCACAAATTAGGAGAAAATTTGAA
1294 10_HRV85      CACTTTGATCAGTGGCAGATAACTATACAGGAAATGGCACAAATTAGAAGGAAGTTTGAG
1295 11_HRV85a|    CACTTTGATCAGTGGCAGATAACTATACAGGAAATGGCACAAATTAGAAGGAAGTTTGAG
1296 12_HRV85b|    CACTTTGATCAGTGGCAGATAACTATACAGGAAATGGCACAAATTAGAAGGAAGTTTGAG
1297 13_HRV56a|    CATTATAATAAATGGCAAATAACTTACAAGAAATGGCTCAAGTTAGGCGTAAATTTGAA
1298 14_HRV56b|    CATTATAATAAATGGCAAATAACCTTACAAGAAATGGCTCAAGTTAGGCGTAAATTTGAA
1299 15_HRV56      CATTATAATAAATGGCAAATAACCTTACAAGAAATGGCTCAAGTTAGGCGTAAATTTGAA
1300 16_HRV54      CATTTTAAGAAATGGGATATAACATTACAAGAGATGGCACAAATACGAAGGAAATTTGAA
```

FIG. D7 CONT'D

03.trace                                                                                                        9/20/2007 5:03 PM

```
1301  17_HRV98      CATTTTAGACAATGGGATATAACATTACAAGAAATGGCACAAATTCGAAGAAAATTTGAA
1302  18_HRV59a|    CACTTTCTTAAATGGCCTATAACATTACAAGAGATGGCACAAATTAGGAGAAAATTTGAA
1303  19_HRV59b|    CACTTTCTTAAATGGCCTATAACATTACAAGAGATGGCACAAATTAGGAGAAAATTTGAA
1304  20_HRV59      CACTTTCTTAAATGGCCTATAACATTACAAGAGATGGCACAAATTAGGAGAAAATTTGAA
1305  21_HRV63      CATTTTAATAAATGGCAAATAACATTACAAGAGATGGCACAAATTAGAAGGAAATTTGAA
1306  22_HRV63b|    CATTTTAATAAATGGCAAATAACATTACAAGAGATGGCACAAATTAGAAGGAAATTTGAA
1307  23_HRV63a|    CATTTTAATAAATGGCAAATAACATTACAAGAGATGGCACAAATTAGAAGGAAATTTGAA
1308  24_HRV39      AATTTTGTGGATTGGAAAATTACTTTGCAGGAGATGGCACAGGTTAGAAGGAAATTTGAA
1309  25_HRV39a|    AATTTTGTGGATTGGAAAATTACTTTGCAGGAGATGGCACAGGTTAGAAGGAAATTTGAA
1310  26_HRV39b|    AATTTTGTGGATTGGAAAATTACTTTGCAGGAGATGGCACAGGTTAGAAGGAAATTTGAA
1311  27_HRV10a|    ACTTTTGACACATGGCAAATAACTCTACAAGAAATGGCCCAAATTAGAAGGAAATTTGAA
1312  28_HRV10b|    ACTTTTGACACATGGCAAATAACTCTACAAGAAATGGCCCAAATTAGAAGGAAATTTGAA
1313  29_HRV10      ACTTTTGACACATGGCAAATAACTCTACAAGAAATGGCCCAAATTAGAAGGAAATTTGAA
1314  30_HRV100a    ACTTTTGACAAATGGCAAATAACCCTACAGGAAATGGCCCAAATTAGAAGGAAATTTGAA
1315  31_HRV100b    ACTTTTGACAAATGGCAAATAACCCTACAGGAAATGGCCCAAATTAGAAGGAAATTTGAA
1316  32_HRV100     ACTTTTGACAAATGGCAAATAACCCTACAGGAAATGGCCCAAATTAGAAGGAAATTTGAA
1317  33_HRV66      AAATTTAGAACATGGCAAATTACATTGCAAGAAATGGCTCAAATCAGACGCAAATTTGAG
1318  34_HRV66b|    AAATTTAGAACATGGCAAATTACATTGCAAGAAATGGCTCAAATCAGACGCAAATTTGAG
1319  35_HRV66a|    AAATTTAGAACATGGCAAATTACATTGCAAGAAATGGCTCAAATCAGACGCAAATTTGAG
1320  36_HRV77a|    AAATTTAGAAAATGGCAAATTACACTACAAGAAATGGCTCAAATTAGGCGCAAATTTGAA
1321  37_HRV77b|    AAATTTAGAAAATGGCAAATTACACTACAAGAAATGGCTCAAATTAGGCGCAAATTTGAA
1322  38_HRV77      AAATTTAGAAAATGGCAAATTACACTACAAGAAATGGCTCAAATTAGGCGCAAATTTGAA
1323  39_HRV62a     AGATTCAAAACATGGAATATTAACTTACAAGAGATGGCTCAAATCAGGAGAAAGTTTGAA
1324  40_HRV62b     AGATTCAAAACATGGAATATTAACTTACAAGAGATGGCTCAAATCAGGAGAAAGTTTGAA
1325  41_HRV25      AGATTTAAAATATGGAATATCAATTTACAAGAAATGGCTCAAATTAGGAGAAAGTTTGAG
1326  42_HRV29a     AAGTTCGATAAATGGAATGTTAACTTACAAGAAATGGCTCAAATTAGGCGCAAATTTGAA
1327  43_HRV29b     AAGTTCGATAAATGGAATGTTAACTTACAAGAAATGGCTCAAATTAGGCGCAAATTTGAA
1328  44_HRV44a     AAGTTTGATAAATGGAATATCAACTTACAAGAAATGGCTCAAATTAGACGCAAATTTGAA
1329  45_HRV44b     AAGTTTGATAAATGGAATATCAACTTACAAGAAATGGCTCAAATTAGACGCAAATTTGAA
1330  46_HRV31      AAATATAAAGTATGGCACATTAATTTACAAGAGATGGCCCAGATTAGGCGAAAATTTGAA
1331  47_HRV31a|    AAATATAAAGTATGGCACATTAATTTACAAGAGATGGCCCAGATTAGGCGAAAATTTGAA
1332  48_HRV31b|    AAATATAAAGTATGGCACATTAATTTACAAGAGATGGCCCAGATTAGGCGAAAATTTGAA
1333  49_HRV47      AAATTTAAAGTATGGCACATTAATTTACAAGAAATGGCCCAGATCAGGCGTAAATATGAA
1334  50_HRV47a|    AAATTTAAAGTATGGCACATTAATTTACAAGAAATGGCCCAGATCAGGCGTAAATATGAA
1335  51_HRV47b|    AAATTTAAAGTATGGCACATTAATTTACAAGAAATGGCCCAGATCAGGCGTAAATATGAA
1336  52_HRV11      AACTTTAACACATGGAAAATAAACTTGCAAGAGATGGCACAAATTAGAAGGAAATTTGAA
1337  53_HRV11b|    AACTTTAACACATGGAAAATAAACTTGCAAGAGATGGCACAAATTAGAAGGAAATTTGAA
1338  54_HRV11a|    AACTTTAACACATGGAAAATAAACTTGCAAGAGATGGCACAAATTAGAAGGAAATTTGAA
1339  55_HRV76      AACTTTAAGACATGGAAAATAAACCTACAAGAAATGGCACAAGTTAGAAGAAAATTTGAA
1340  56_HRV76b|    AACTTTAAGACATGGAAAATAAACCTACAAGAAATGGCACAAGTTAGAAGAAAATTTGAG
1341  57_HRV76a|    AACTTTAAGACATGGAAAATAAACCTACAAGAAATGGCACAAGTTAGAAGAAAATTTGAG
1342  58_HRV33      AATTTTATGACATGGAAAATAAATCTACAAGAGATGGCACAGATTAGGACGAAATTTGAA
1343  59_HRV33b|    AATTTTATGACATGGAAAATAAATCTACAAGAGATGGCACAGATTAGGAGGAAATTTGAA
1344  60_HRV33a|    AATTTTATGACATGGAAAATAAATCTACAAGAGATGGCACAGATTAGGAGGAAATTTGAA
1345  61_HRV24a|    AATTTTTTCAAATGGCAAATAAATCTACAAGAAATGGCCCAAGTCAGAAGAAAATTTGAA
1346  62_HRV24b|    AATTTTTTCAAATGGCAAATAAATCTACAAGAAATGGCCCAAGTCAGAAGAAAATTTGAA
1347  63_HRV24      AATTTTTTCAAATGGCAAATAAATCTACAAGAAATGGCCCAAGTCAGAAGAAAATTTGAA
1348  64_HRV90      AACTTCCATAAATGGCAAATTAACCTGCAAGAGATGGCACAGATTAGAAGAAAATTTGAA
1349  65_HRV90a|    AACTTCCATAAATGGCAAATTAACCTGCAAGAGATGGCACAGATTAGAAGAAAATTTGAA
1350  66_HRV90b|    AACTTCCATAAATGGCAAATTAACCTGCAAGAGATGGCACAGATTAGAAGAAAATTTGAA
1351  67_HRV34      AACTTTATGACATGGCAAATTAATTTACAGGAAATGGCACAGATTAGAAGGAAATTTGAA
1352  68_HRV34b|    AACTTTATGACATGGCAAATTAATTTACAGGAAATGGCACAGATTAGAAGGAAATTTGAA
1353  69_HRV34a|    AACTTTATGACATGGCAAATTAATTTACAGGAAATGGCACAGATTAGAAGGAAATTTGAA
1354  70_HRV50a|    AACTTCAAGAAATGGCAAATCAACCTACAAGAAATGGCACAGATCAGAAGGAAATTTGAG
1355  71_HRV50b|    AACTTCAAGAAATGGCAAATCAACCTACAAGAAATGGCACAGATCAGAAGGAAATTTGAG
1356  72_HRV50      AACTTCAAGAAATGGCAAATCAACCTACAAGAAATGGCACAGATCAGAAGGAAATTTGAG
1357  73_HRV18a|    AACTTTGTAAAATGGCAAATAAATCTACAGGGAAATGGCACAGATTAGGAGAAAATTTGAG
1358  74_HRV18b|    AACTTTGTAAAATGGCAAATAAATCTACAGGAAATGGCCCAGATTAGGAGAAAATTTGAG
1359  75_HRV18      AACTTTGTAAAATGGCAAATAAATCTACAGGAAATGGCCCAGATTAGGAGAAAATTTGAG
1360  76_HRV55      AATTTTACTAAGTGGCAAGTAAACATCCAAGAGATGGCTCAGATTAGAAGAAAATTTGAA
1361  77_HRV55b|    AATTTTACTAAGTGGCAAGTAAACATCCAAGAGATGGCTCAGATTAGAAGAAAATTTGAA
1362  78_HRV55a|    AATTTTACTAAGTGGCAAGTAAACATCCAAGAGATGGCTCAGATTAGAAGAAAATTTGAA
1363  79_HRV57      AATTTCACTAAATGGGAAATAAATCTACAAGAAATGGCACAAATCAGAAGAAAATTTGAA
1364  80_HRV57a|    AATTTCACTAAATGGGAAATAAATCTACAAGAAATGGCACAAATCAGAAGAAAATTTGAA
1365  81_HRV57b|    AATTTCACTAAATGGGAAATAAATCTACAAGAAATGGCACAAATCAGAAGAAAATTTGAA
```

FIG. D7 CONT'D 03.trace                                                                9/20/2007 5:03 PM

```
1366  82_HRV21     AACATTAGTACATGGCAAATAAATATTAAAGAGATGGCACAAATTAGGAGAAAATTTGAA
1367  83_HRVHan    AACATTAATACATGGCAAATAAATATTAAAGAGATGGCACAAATTAGGAGAAAATTTGAA
1368  84_HRV43     AATTTTACCCAATGGCCAATCAACTTGCAAGAAATGGCACAAATTAGAAGAAAGTATGAA
1369  85_HRV43bl   AATTTTACCCAATGGCCAATCAACTTGCAAGAAATGGCACAAATTAGAAGAAAGTATGAA
1370  86_HRV43al   AATTTTACCCAATGGCCAATCAACTTGCAAGAAATGGCACAAATTAGAAGAAAGTATGAA
1371  87_HRV75     AACTTCACTCAGTGGCCAATCAATCTACAGGAAATGGCTCAAATTAGAAGGAAATATGAA
1372  88_HRV75bl   AACTTCACTCAGTGGCCAATCAATCTACAGGAAATGGCTCAAATTAGAAGGAAATATGAA
1373  89_HRV75al   AACTTCACTCAGTGGCCAATCAATCTACAGGAAATGGCTCAAATTAGAAGGAAATATGAA
1374  96_HRV9ald   AATTTCACAATCTGGAAAATAAATATAAAGGAAATGGCCCAGATCAGGAGGAAATTTGAA
1375  97_HRV9bld   AATTTCACAATCTGGAAAATAAATATAAAGGAAATGGCCCAGATCAGGAGGAAATTTGAA
1376  98_HRV9      AATTTCACAATCTGGAAAATAAATATAAAGGAAATGGCCCAGATCAGGAGGAAATTTGAA
1377  99_HRV32     AATTTCACAATTTGGAAGATAAATATAAAAGAAATGGCCCAGATTAGGAGAAAATTTGAG
1378  100_HRV32a   AATTTCACAATTTGGAAGATAAATATAAAAGAAATGGCCCAGATTAGGAGAAAATTTGAG
1379  101_HRV32b   AATTTCACAATTTGGAAGATAAATATAAAAGAAATGGCCCAGATTAGGAGAAAATTTGAG
1380  102_HRV67    AATTTCACAATTTGGAAAATAAATATAAAAGAAATGGCCCAGATTAGGAGGAAATTTGAA
1381  103_HRV67a   AATTTCACAATTTGGAAAATAAATATAAAAGAAATGGCCCAGATTAGGAGGAAATTTGAA
1382  104_HRV67b   AATTTCACAATTTGGAAAATAAATATAAAAGAAATGGCCCAGATTAGGAGGAAATTTGAA
1383  105_HRV15    AACTTTACTAAATGGCAAATTAATCTCAAAGAAATGGCCCAGATTAGAAGGAAATTTGAG
1384  106_HRV15a   AACTTTACTAAATGGCAAATTAATCTCAAAGAAATGGCCCAGATTAGAAGGAAATTTGAG
1385  107_HRV15b   AACTTTACTAAATGGCAAATTAATCTCAAAGAAATGGCCCAGATTAGAAGGAAATTTGAG
1386  108_HRV74a   AATTTTACTAAATGGCAAATAAATCTTAAAGAAATGGCACAGATTAGGAGAAAATTTGAG
1387  109_HRV74b   AATTTTACTAAATGGCAAATAAATCTTAAAGAAATGGCACAGATTAGGAGAAAATTTGAG
1388  110_HRV74    AATTTTACTAAATGGCAAATAAATCTTAAAGAAATGGCACAGATTAGGAGAAAATTTGAG
1389  111_HRV38a   AACTTTACAACATGGCAAATCAATCTCAAAGAAATGGCTCAAATCAGAAGAAAGTTTGAA
1390  112_HRV38b   AACTTTACAACATGGCAAATCAATCTCAAAGAAATGGCTCAAATCAGAAGAAAGTTTGAA
1391  113_HRV38    AACTTTACAACATGGCAAATCAATCTCAAAGAAATGGCTCAAATCAGAAGAAAGTTTGAA
1392  114_HRV60    AATTTCACAACTTGGCAAATTAACCTAAAGGAAATGGCACAAATAAGAAGAAAGTTTGAA
1393  115_HRV60a   AATTTCACAACTTGGCAAATTAACCTAAAGGAAATGGCACAAATAAGAAGAAAGTTTGAA
1394  116_HRV60b   AATTTCACAACTTGGCAAATTAACCTAAAGGAAATGGCACAAATAAGAAGAAAGTTTGAA
1395  117_HRV64a   AATTTTAACAAATGGCAGATCACCTTGAAAGAAATGGCTCAGATAAGAAGGAAGTATGAA
1396  118_HRV64b   AATTTTAACAAATGGCAGATCACCTTGAAAGAAATGGCTCAGATAAGAAGGAAGTATGAA
1397  119_HRV64    AATTTTAACAAATGGCAGATCACCTTGAAAGAAATGGCTCAGATAAGAAGGAAGTATGAA
1398  120_HRV94a   AATTTCCAATCATGGCAAATTACCCTAAAAGAAATGGCACAAATAAGAAGGAAATTTGAA
1399  121_HRV94b   AATTTCCAATCATGGCAAATTACCCTAAAAGAAATGGCACAAATAAGAAGGAAATTTGAA
1400  122_HRV94    AATTTCCAATCATGGCAAATTACCCTAAAAGAAATGGCACAAATAAGAAGGAAATTTGAA
1401  123_HRV22    AACTTTAACATATGGCAAATTAACCTTAAAGAGATGGCTCAGATAAGAAGGAAGTTTGAG
1402  124_HRV22a   AACTTTAACATATGGCAAATTAACCTTAAAGAGATGGCTCAGATAAGAAGGAAGTTTGAG
1403  125_HRV22b   AACTTTAACATATGGCAAATTAACCTTAAAGAGATGGCTCAGATAAGAAGGAAGTTTGAG
1404  126_HRV82    AACTTTAGATCATGGCAAATAAGGAAATGGCACAAATTAGAAGGAAGTTTGAA
1405  127_HRV82b   AACTTTAGATCATGGCAAATAAGCATAAAGGAAATGGCACAAATTAGAAGGAAGTTTGAA
1406  128_HRV82a   AACTTTAGATCATGGCAAATAAGCATAAAGGAAATGGCACAAATTAGAAGGAAGTTTGAA
1407  129_HRV19    AATTTCAAAACTTGGCAAATAAACTTGAAAGAAATGGCACAGATTAGAAGAAAATTTGAA
1408  130_HRV19a   AATTTCAAAACTTGGCAAATAAACTTGAAAGAAATGGCACAGATTAGAAGAAAATTTGAA
1409  131_HRV19b   AATTTCAAAACTTGGCAAATAAACTTGAAAGAAATGGCACAGATTAGAAGAAAATTTGAA
1410  132_HRV13    AATTTTGTGAAATGGAAAATAAGTTTGCAAGAAATGGCCCAAGTGCGCAGAAAATTTGAG
1411  133_HRV13a   AATTTTGTGAAATGGAAAATAAGTTTGCAAGAAATGGCCCAAGTGCGCAGAAAATTTGAG
1412  134_HRV13b   AATTTTGTGAAATGGAAAATAAGTTTGCAAGAAATGGCCCAAGTGCGCAGAAAATTTGAG
1413  135_HRV41    AACTTCAAGAAGTGGAAAATTAGCTTACAGGAGATGGCCCAAGTACGTAGAAAGTTTGAG
1414  136_HRV41a   AACTTCAAGAAGTGGAAAATTAGCTTACAGGAGATGGCCCAAGTACGTAGAAAGTTTGAG
1415  137_HRV41b   AACTTCAAGAAGTGGAAAATTAGCTTACAGGAGATGGCCCAAGTACGTAGAAAGTTTGAG
1416  138_HRV73    AATTTTACCAAATGGAAAATAAGTTTACAAGAGATGGCTCAAATACGTAGGAAATTTGAA
1417  139_HRV73b   AATTTTACCAAATGGAAAATAAGTTTACAAGAGATGGCTCAAATACGTAGGAAATTTGAA
1418  140_HRV73a   AATTTTACCAAATGGAAAATAAGTTTACAAGAGATGGCTCAAATACGTAGGAAATTTGAA
1419  141_HRV61    AACTTCAAGGTGTGGAAAATAAACCTGCAAGAGATGGCACAAATACGTAGAAAATTTGAG
1420  142_HRV61a   AACTTCAAGGTGTGGAAAATAAACCTGCAAGAGATGGCACAAATACGTAGAAAATTTGAG
1421  143_HRV61b   AACTTCAAGGTGTGGAAAATAAACCTGCAAGAGATGGCACAAATACGTAGAAAATTTGAG
1422  144_HRV96    AATTTTAAGGTGTGGAAAATAAATCTACAAGAAATGGCTCAAATTCGCAGGAAGTTTGAA
1423  145_HRV96b   AATTTTAAGGTGTGGAAAATAAATCTACAAGAAATGGCTCAAATTCGCAGGAAGTTTGAA
1424  146_HRV96a   AATTTTAAGGTGTGGAAAATAAATCTACAAGAAATGGCTCAAATTCGCAGGAAGTTTGAA
1425  90_HRV16al   AGTTTCACTAAATGGAAGATAAACCTGCAAGAAATGGCACAAATTAGAAGAAAATTTGAA
1426  91_HRV16bl   AGTTTCACTAAATGGAAGATAAACCTGCAAGAAATGGCACAAATTAGAAGAAAATTTGAA
1427  92_1AYM_A    AGTTTCACTAAATGGAAGATAAACCTGCAAGAAATGGCACAAATTAGAAGAAAATTTGAA
1428  93_HRV81al   AGCTTTACTAAATGGAAAATTAACTTACAAGAGATGGCACAGATTAGGAGAAGTTTGAA
1429  94_HRV81bl   AGCTTTACTAAATGGAAAATTAACTTACAAGAGATGGCACAGATTAGGAGAAAGTTTGAA
1430  95_HRV81     AGCTTTACTAAATGGAAAATTAACTTACAAGAGATGGCACAGATTAGGAGAAAGTTTGAA
```

FIG. D7 CONT'D

```
03.trace                                                              9/20/2007 5:03 PM 1431  147_HRV2     AATTTTACAGTGTGGGCTATTAATATACAAGAAATGGCTCAAATTAGAAGGAAATTTGAA
1432  148_HRV2a|   AATTTTACAGTGTGGGCTATTAATATACAAGAAATGGCTCAAATTAGAAGGAAATTTGAA
1433  149_HRV2b|   AATTTTACAGTGTGGGCTATTAATATACAAGAAATGGCTCAAATTAGAAGGAAATTTGAA
1434  150_HRV49a   AATTTCAAAGTATGGAACATCAATTTGCAAGAAATGGCCCAGATCAGAAGAAAATTTGAA
1435  151_HRV49b   AATTTCAAAGTATGGAACATCAATTTGCAAGAAATGGCCCAGATCAGAAGAAAATTTGAA
1436  152_HRV49    AATTTCAAAGTATGGAACATCAATTTGCAAGAAATGGCCCAGATCAGAAGAAAATTTGAA
1437  153_HRV23a   AATTTTAATACTTGGAATATTAATTTACAGGAAATGGCCCAAATCAGAAGAAAGTTTGAA
1438  154_HRV23b   AATTTTAATACTTGGAATATTAATTTACAGGAAATGGCCCAAATCAGAAGAAAGTTTGAA
1439  155_HRV23    AATTTTAATACTTGGAATATTAATTTACAGGAAATGGCCCAAATCAGAAGAAAGTTTGAA
1440  156_HRV30a   AACTTTACCACATGGAATATTAATCTTCAAGAAATGGCCCAAATTAGAAGAAAATTTGAG
1441  157_HRV30b   AACTTTACCACATGGAATATTAATCTTCAAGAAATGGCCCAAATTAGAAGAAAATTTGAG
1442  158_HRV30    AACTTTACCACATGGAATATTAATCTTCAAGAAATGGCCCAAATTAGAAGAAAATTTGAG
1443  159_HRV7     GGTTTCACTACATGGAAAATCAGCTTACAAGAAATGGCACAAATCAGAAGAAAGTTTGAA
1444  160_HRV7b|   GGTTTCACTACATGGAAAATCAGCTTACAAGAAATGGCACAAATCAGAAGAAAGTTTGAA
1445  161_HRV7a|   GGTTTCACTACATGGAAAATCAGCTTACAAGAAATGGCACAAATCAGAAGAAAGTTTGAA
1446  162_HRV88    GGATTTGTAACATGGAAGATTAGCTTGCAAGAAATGGCACAAATCAGGAGAAATTTGAA
1447  163_HRV88a   GGATTTGTAACATGGAAGATTAGCTTGCAAGAAATGGCACAAATCAGGAGAAAATTTGAA
1448  164_HRV88b   GGATTTGTAACATGGAAGATTAGCTTGCAAGAAATGGCACAAATCAGGAGAAAATTTGAA
1449  165_HRV36a   GGATTCAAAACATGGAAGATTAGTCTTCAAGAAATGGCACAAATTAGAAGGAAATATGAA
1450  166_HRV36b   GGATTCAAAACATGGAAGATTAGTCTTCAAGAAATGGCACAAATTAGAAGGAAATATGAA
1451  167_HRV36    GGATTCAAAACATGGAAGATTAGTCTTCAAGAAATGGCACAAATTAGAAGGAAATATGAA
1452  168_HRV89a   GGATTCAAAACATGGAAGGTTAGTCTTCAAGAAATGGCACAAATCAGAAGAAAATATGAA
1453  169_HRV89b   GGATTCAAAACATGGAAGGTTAGTCTTCAAGAAATGGCACAAATCAGAAGAAAATATGAA
1454  170_HRV89    GGATTCAAAACATGGAAGGTTAGTCTTCAAGAAATGGCACAAATCAGAAGAAAATATGAA
1455  171_HRV58    GGATACAAAACATGGAAAATTAGCCTTCAAGAGATGGCACAAATTAGAAGGAAATTTGAG
1456  172_HRV58a   GGATACAAAACATGGAAAATTAGCCTTCAAGAGATGGCACAAATTAGAAGGAAATTTGAG
1457  173_HRV58b   GGATACAAAACATGGAAAATTAGCCTTCAAGAGATGGCACAAATTAGAAGGAAATTTGAG
1458  174_HRV12a   AACTTTAAAACATGGAAGATAAATCTTAAGGAAATGGCCCAGATTAGAAGGAAAAATGAA
1459  175_HRV12b   AACTTTAAAACATGGAAGATAAATCTTAAGGAAATGGCCCAGATTAGAAGGAAAAATGAG
1460  176_HRV12    AACTTTAAAACATGGAAGATAAATCTTAAGGAAATGGCCCAGATTAGAAGGAAAAATGAG
1461  177_HRV78a   AATTTTACAACGTGGAAAATCAACTTACAGGAGATGGCCCAGATTAGAAGAAAAGAATGAG
1462  178_HRV78b   AATTTTACAACGTGGAAAATCAACTTACAGGAGATGGCCCAGATTAGAAGAAAAGAATGAG
1463  179_HRV78    AATTTTACAACGTGGAAAATCAACTTACAGGAGATGGCCCAGATTAGAAGAAAAGAATGAG
1464  180_HRV20    AATTTCTCTCAGTGGAAGATCACAATCAAGGAAATGGCTCAAATCAGAAGAAAATGTGAG
1465  181_HRV20a   AATTTCTCTCAGTGGAAGATCACAATCAAGGAAATGGCTCAAATCAGAAGAAAATGTGAG
1466  182_HRV20b   AATTTCTCTCAGTGGAAGATCACAATCAAGGAAATGGCTCAAATCAGAAGAAAATGTGAG
1467  183_HRV68    AACTTCTCCCAATGGAAAATTACAATTAAGGAAATGGCTCAAATTAGAAGAAAGTGTGAA
1468  184_HRV68a   AACTTCTCCCAATGGAAAATTACAATTAAGGAAATGGCTCAAATTAGAAGAAAGTGTGAA
1469  185_HRV68b   AACTTCTCCCAATGGAAAATTACAATTAAGGAAATGGCTCAAATTAGAAGAAAGTGTGAA
1470  186_HRV28    AATTTTAGTAAATGGAATATCACTCTCAAAGAAATGGCCCAAATCAGAAGAAAGTGTGAA
1471  187_HRV28a   AATTTTAGTAAATGGAATATCACTCTCAAAGAAATGGCCCAAATCAGAAGAAAGTGTGAA
1472  188_HRV28b   AATTTTAGTAAATGGAATATCACTCTCAAAGAAATGGCCCAAATCAGAAGAAAGTGTGAA
1473  189_HRV53a   AACCACTCAGAATGGAAGATTACACTCAAAGAAATGGCCCAGATTAGAAGGAAATGTGAG
1474  190_HRV53b   AACCACTCAGAATGGAAGATTACACTCAAAGAAATGGCCCAGATTAGAAGGAAATGTGAG
1475  191_HRV53    AACCACTCAGAATGGAAGATTACACTCAAAGAAATGGCCCAGATTAGAAGGAAATGTGAG
1476  192_HRV46a   AACTTCTCAAAATGGAAAATAACACTGTTGGAAATGGCACAAATCAGAAGAAAGTGTGAA
1477  193_HRV46b   AACTTCTCAAAATGGAAAATAACACTGTTGGAAATGGCACAAATCAGAAGAAAGTGTGAA
1478  194_HRV46    AACTTCTCAAAATGGAAAATAACACTGTTGGAAATGGCACAAATCAGAAGAAAGTGTGAA
1479  195_HRV80a   AATTTTTCAAAGTGGAAAATAACATTAATGGAAATGGCACAAATTAGAAGAAAGTGTGAG
1480  196_HRV80b   AATTTTTCAAAGTGGAAAATAACATTAATGGAAATGGCACAAATTAGAAGAAAGTGTGAG
1481  197_HRV80    AATTTTTCAAAGTGGAAAATAACATTAATGGAAATGGCACAAATTAGAAGAAAGTGTGAG
1482  198_HRV51    AATTTCTCTACATGGAAAATTACACTCAAAGAAATGGCTCAAATTAGAAGAAAGTGTGAA
1483  199_HRV51a   AATTTCTCTACATGGAAAATTACACTCAAAGAAATGGCTCAAATTAGAAGAAAGTGTGAA
1484  200_HRV51b   AATTTCTCTACATGGAAAATTACACTCAAAGAAATGGCTCAAATTAGAAGAAAGTGTGAA
1485  201_HRV65a   AATTTCTCTGCTTGGGAAATTACACTCAAGGAAATGGCTCAAATTAGGAGAAAGTGTGAA
1486  202_HRV65b   AATTTCTCTGCTTGGGAAATTACACTCAAGGAAATGGCTCAAATTAGGAGAAAGTGTGAA
1487  203_HRV65    AATTTCTCTGCTTGGGAAATTACACTCAAGGAAATGGCTCAAATTAGGAGAAAGTGTGAA
1488  204_HRV71a   AATCTCTCAAAGTGGCAGATTACACTCAAAGAAATGGCTCAGATCAGGAGGAAATGTGAA
1489  205_HRV71b   AATCTCTCAAAGTGGCAGATTACACTCAAAGAAATGGCTCAGATCAGGAGGAAATGTGAA
1490  206_HRV71    AATCTCTCAAAGTGGCAGATTACACTCAAAGAAATGGCTCAGATCAGGAGGAAATGTGAA
1491  207_HRV8     AGTTTCAGGACCTGGGGAATAAACATACAAGAGATGTCACAAATTAGAAGGAAATTTGAG
1492  208_HRV95    AATTTCAGGACCTGGGGAATAAACATCAAGAGATGTCACAAATTGAAGGAAATTTGAA
1493  209_HRV45    AATTACAAAAATTGGGCAATTAGTTTACAAGAAATGTCACAAATTAGGAGGAAATTTGAA
1494  210_HRV45a   AATTACAAAAATTGGGCAATTAGTTTACAAGAAATGTCACAAATTAGGAGGAAATTTGAA
1495  211_HRV45b   AATTACAAAAATTGGGCAATTAGTTTACAAGAAATGTCACAAATTAGGAGGAAATTTGAA
```

FIG. D7 CONT'D

```
03.trace                                                          9/20/2007 5:03 PM 1496  GROUP_1        ------------TGG----T-A---T----GA-ATG-C-CA--T--G--G-AA----GA-
1497
1498   1_HRV1A1|d    TTGTTTACATATGTCAGGTTTGACTCAGAAATAACCTTGG-TGCCTTGTATTGCTGGTAG
1499   2_HRV1A2|d    TTGTTTACATATGTCAGGTTTGACTCAGAAATAACCTTGG-TGCCTTGTATTGCTGGTAG
1500   3_HRV1A|cD    TTGTTTACATATGTCAGGTTTGACTCAGAAATAACCTTGG-TGCCTTGTATTGCTGGTAG
1501   4_HRV1B1|d    CTATTTACTTATGTTAGGTTTGATTCAGAAGTAACTTTAG-TACCCTGTATTGCTGGTAG
1502   5_HRV1B2|d    CTATTTACTTATGTTAGGTTTGATTCAGAAGTAACTTTAG-TACCCTGTATTGCTGGTAG
1503   6_HRV1B       CTATTTACTTATGTTAGGTTTGATTCAGAAGTAACTTTAG-TACCCTGTATTGCTGGTAG
1504   7_HRV40a|d    TTCTTTACATATGCTAGGTTTGATTCAGAAATTACCTTAG-TTCCTTGTATAGCCGGTAA
1505   8_HRV40b|d    TTCTTTACATATGCTAGGTTTGATTCAGAAATTACCTTAG-TTCCTTGTATAGCCGGTAA
1506   9_HRV40       TTCTTTACATATGCTAGGTTTGATTCAGAAATTACCTTAG-TTCCTTGTATAGCCGGTAA
1507  10_HRV85       TTCTTTACTTACACTAGATTTGATTCAGAAATCACTTTAG-TCCCTTGTATAGCTGGAAA
1508  11_HRV85a|     TTCTTTACTTACACTAGATTTGATTCAGAAATCACTTTAG-TCCCTTGTATAGCTGGAAA
1509  12_HRV85b|     TTCTTACTTACACTAGATTTGATTCAGAAATCACTTTAG-TCCCTTGTATAGCTGGAAA
1510  13_HRV56a|     TTCTTTACTTATGTCAGATTTGATTCAGAAGGTTACTTTGG-TACCTTGCTAGCCGGCAA
1511  14_HRV56b|     TTCTTTACTTATGTCAGATTTGATTCAGAGGTTACTTTGG-TACCTTGTGTAGCCGGCAA
1512  15_HRV56       TTCTTTACTTATGTCAGATTTGATTCAGAGGTTACTTTGG-TACCTTGTGTAGCCGGCAA
1513  16_HRV54       TCTTTACTTATGTTAGGTTTGATTCAGAAATTACTCTAG-TCCCCTGTATAGCTGGTAA
1514  17_HRV98       TTCTTTACTTATGTTAGATTTGATTCAGAAGGTTACTTTAG-TTCCTTGCATAGCTGGCAA
1515  18_HRV59a|     TTCTTCACATATGTTAGATTTGACTCAGAAATCACTTTGG-TGCCTTGCATAGCTGGAAA
1516  19_HRV59b|     TTCTTCACATATGTTAGATTTGACTCAGAAATCACTTTGG-TGCCTTGCATAGCTGGAAA
1517  20_HRV59       TTCTTCACATATGTTAGATTTGACTCAGAAATCACTTTGG-TGCCTTGCATAGCTGGAAA
1518  21_HRV63       TTCTTCACATATGTCAGATTTGATTCAGAAGTCACTCTTG-TACCATGTATAGCAGGAAA
1519  22_HRV63b|     TTCTTCACATATGTCAGATTTGATTCAGAAGTCACTCTTG-TACCATGTATAGCAGGAAA
1520  23_HRV63a|     TTCTTCACATATGTCAGATTTGATTCAGAAGTCACTCTTG-TACCATGTATAGCAGGAAA
1521  24_HRV39       ATGTTCACCTATGTTAGATTTGACTCAGAGATTACTTTAG-TCCCATGCATAGCTGGAAG
1522  25_HRV39a|     ATGTTCACCTATGTTAGATTTGACTCAGAGATTACTTTAG-TCCCATGCATAGCTGGAAG
1523  26_HRV39b|     ATGTTCACCTACGTTAGATTTGACTCAGAGATTACTTTAG-TCCCATGCATAGCTGGAAG
1524  27_HRV10a|     ATGTTTACATATGTTAGATTTGACTCAGAAGTCACTTTAG-TACCTTGCATCGCAGGCAA
1525  28_HRV10b|     ATGTTTACATATGTTAGATTTGACTCAGAAGTCACTTTAG-TACCTTGCATCGCAGGCAA
1526  29_HRV10       ATGTTTACATATGTTAGATTTGACTCAGAAGTCACTTTAG-TACCTTGCATCGCAGGCAA
1527  30_HRV100a     ATGTTTACATATGTCAGATTTGACTCAGAAATCACATTGG-TACCCTGTATTGCAGGAAA
1528  31_HRV100b     ATGTTTACATATGTCAGATTTGACTCAGAAATCACATTGG-TACCCTGTATTGCAGGAAA
1529  32_HRV100      ATGTTTACATATGTCAGATTTGACTCAGAAATCACATTGG-TACCCTGTATTGCAGGAAA
1530  33_HRV66       ATGTTCACATATGTTAGGTTTGATTCTGAAATTACATTAG-TCCCATGCATTGCAGGAAA
1531  34_HRV66b|     ATGTTCACATATGTTAGGTTTGATTCTGAAATTACATTAG-TCCCATGCATTGCAGGAAA
1532  35_HRV66a|     ATGTTCACATATGTTAGGTTTGATTCTGAAATTACATTAG-TCCCATGCATTGCAGGAAA
1533  36_HRV77a|     ATGTTTACATATGTAAGATTTGATTCAGAAATTACATTGG-TCCCATGTATTGCTGGAAA
1534  37_HRV77b|     ATGTTTACATATGTAAGATTTGATTCAGAAATTACATTGG-TCCCATGTATTGCTGGAAA
1535  38_HRV77       ATGTTTACATATGTAAGATTTGATTCAGAAATTACATTGG-TCCCATGTATTGCTGGAAA
1536  39_HRV62a      ATGTTTACATATGTAAGATTTGATTCAGAAAATAACCCTGG-TTCCATCTATTGCAGGACG
1537  40_HRV62b      ATGTTTACATATGTAAGATTTGATTCAGAAAATAACCCTGG-TTCCATCTATTGCAGGACG
1538  41_HRV25       ATGTTTACATATGTGAGATTTGATTCAGAGATAACCTAG-TTCCATCTATTGCAGGACG
1539  42_HRV29a      ATGTTCACATATGTGAGATTTGACTCAGAAATAACTCTGG-TTCTTTGCATTGCAGGACG
1540  43_HRV29b      ATGTTCACATATGTGAGATTTGACTCAGAAATAACTCTGG-TTCCATGCATTGCAGGACG
1541  44_HRV44a      ATGTTCACATATGTAAGATTTCGGAAATAACTCTAG-TTCCATGCATTGCAGGACA
1542  45_HRV44b      ATGTTCACATATGTGAGATTTGATTCAGAAATAACTCTAG-TTCCATGCATTGCAGGACG
1543  46_HRV31       ATGTTCACATATGTAAGATTTGATTCAGAAGTGACCATAG-TTCCATGCATTGCAGGACA
1544  47_HRV31a|     ATGTTCACATATGTAAGATTTGATTCAGAAGTGACCATAG-TTCCATGCATTGCAGGACA
1545  48_HRV31b|     ATGTTCACATATGTAAGATTTGATTCAGAAGTGACCATAG-TTCCATGCATTGCAGGACA
1546  49_HRV47       ATGTTTACATATGTAAGATTTGATTCAGAAGTAACCATGG-TTCCATGTATTGCAGGGTA
1547  50_HRV47a|     ATGTTTACATATGTAAGATTTGATTCAGAAGTAACCATGG-TTCCATGTATTGCAGGGTA
1548  51_HRV47b|     ATGTTTACATATGTAAGATTTGATTCAGAAGTAACCATGG-TTCCATGTATTGCAGGGTA
1549  52_HRV11       ATGTTCACATACACTAGATTTGATTCAGAGATCACATTGG-TGCCTTGTATAGCTGCAAA
1550  53_HRV11b|     ATGTTCACATACACTAGATTTGATTCAGAGATCACATTGG-TGCCTTGTATAGCTGCAAA
1551  54_HRV11a|     ATGTTCACATACACTAGATTTGATTCAGAGATCACATTGG-TGCCTTGTATAGCTGCAAA
1552  55_HRV76       ATGTTTACATATACTAGATTTGATTCAGAAGTTACTCTAG-TTCCTTCTATAGCTGCCAA
1553  56_HRV76b|     ATGTTTACATATACTAGATTTGATTCAGAAGTTACTCTAG-TTCCTTCTATAGCTGCCAA
1554  57_HRV76a|     ATGTTTACATATACTAGATTTGATTCAGAAGTTACTCTAG-TTCCTTCTATAGCTGCCAA
1555  58_HRV33       ATGTTTACATATGCCAGATTTGATTCAGAGATCACCCTAG-TCCCTTCTATAGCTGCCCA
1556  59_HRV33b|     ATGTTTACATATGCCAGATTTGATTCAGAGATCACCCTAG-TCCCTTCTATAGCTGCCCA
1557  60_HRV33a|     ATGTTTACATATGCCAGATTTGATTCAGAGATCACCCTAG-TCCCTTCTATAGCTGCCCA
1558  61_HRV24a|     TTATTCACATATACTAGATTTGACTCTGAGATTACAATAG-TTCCATCCATAGCTGGCAA
1559  62_HRV24b|     TTATTCACATATACTAGATTTGACTCTGAGATTACAATAG-TTCCATCCATAGCTGGCAA
1560  63_HRV24       TTATTCACATATACTAGATTTGACTCTGAGATTACAATAG-TTCCATCCATAGCTGGCAA
```

FIG. D7 CONT'D 03.trace                                                                9/20/2007 5:03 PM

```
1561  64_HRV90      TTGTTTACATATGCTAGATTTGATTCTGAAATTACAATAG-TACCATCTATAGCTGGCAA
1562  65_HRV90a|    TTGTTTACATATGCTAGATTTGATTCTGAAATTACAATAG-TACCATCTATAGCTGGCAA
1563  66_HRV90b|    TTGTTTACATATGCTAGATTTGATTCTGAAATTACAATAG-TACCATCTATAGCTGGCAA
1564  67_HRV34      ATGTTCACCTACGTCAGATTTGATTCTGAAGTCACCCTAG-TACCATCAATAGCGGCCAA
1565  68_HRV34b|    ATGTTCACCTACGTCAGATTTGATTCTGAAGTCACCCTAG-TACCATCAATAGCGGCCAA
1566  69_HRV34a|    ATGTTCACCTACGTCAGATTTGATTCTGAAGTCACCCTAG-TACCATCAATAGCGGCCAA
1567  70_HRV50a|    ATGTTCACCTATGTGAGGTTTAATTCTGAGGTCACATTAG-TACCATCCATAGCTGCCAA
1568  71_HRV50b|    ATGTTCACCTATGTGAGGTTTAATTCTGAGGTCACATTAG-TACCATCCATAGCTGCCAA
1569  72_HRV50      ATGTTCACCTATGTGAGGTTTAATTCTGAGGTCACATTAG-TACCATCCATAGCTGCCAA
1570  73_HRV18a|    ATGTTTACATATGTTAGATTTGATTCAGAAATTACACTAG-TACCATCTGTAGCTGCTAA
1571  74_HRV18b|    ATGTTTACATATGTTAGATTTGATTCAGAAATTACACTAG-TACCATCTGTAGCTGCTAA
1572  75_HRV18      ATGTTTACATATGTTAGATTTGATTCAGAAATTACACTAG-TACCATCTGTAGCTGCTAA
1573  76_HRV55      ATGTTCACCTATACTAGATTTGATTCAGAAGTTACATTAG-TACCCTCTATTGCTGCAAA
1574  77_HRV55b|    ATGTTCACCTATACTAGATTTGATTCAGAAGTTACATTAG-TACCCTCTATTGCTGCAAA
1575  78_HRV55a|    ATGTTCACCTATACTAGATTTGATTCAGAAGTTACATTAG-TACCCTCTATTGCTGCAAA
1576  79_HRV57      CTATTTACATATGTTAGGTTTGATTCTGAAGTTACATTAG-TTCCCTCCATAGCTGCTCA
1577  80_HRV57a|    CTATTTACATATGTTAGGTTTGATTCTGAAGTTACATTAG-TTCCCTCCATAGCTGCTCA
1578  81_HRV57b|    CTATTTACATATGTTAGGTTTGATTCTGAAGTTACATTAG-TTCCCTCCATAGCTGCTCA
1579  82_HRV21      ATGTTCACCTATACTAGATTTGATTCAGAAATAACTTTGG-TGCCGTCAATTGCAGCTAG
1580  83_HRVHan     ATGTTCACCTATACTAGATTTGATTCAGAAATAACTTTGG-TACCGTCAATTGCAGCTAA
1581  84_HRV43      TTGTTCACATACTTAAGGTTTGATTCTGAAATTACCCTTG-TTCCTTGCATTGCAGCAAA
1582  85_HRV43b|    TTGTTCACATACTTAAGGTTTGATTCTGAAATTACCCTTG-TTCCTTGCATTGCAGCAAA
1583  86_HRV43a|    TTGTTCACATACTTAAGGTTTGATTCTGAAATTACCCTTG-TTCCTTGCATTGCAGCAAA
1584  87_HRV75      TTATTTACATATCTTAGATTTGATTCAGAGGTTACTCTGG-TGCCATGCATTGCAGCTAA
1585  88_HRV75b|    TTATTTACATATCTTAGATTTGATTCAGAGGTTACTCTGG-TGCCATGCATTGCAGCTAA
1586  89_HRV75a|    TTATTTACATATCTTAGATTTGATTCAGAGGTTACTCTGG-TGCCATGCATTGCAGCTAA
1587  96_HRV9a|d    TTGTTTACATATGCAAGATTTGACTCTGAAATAACATTGG-TCCCGTGTATAGCAGCAGA
1588  97_HRV9b|d    TTGTTTACATATGCAAGATTTGACTCTGAAATAACATTGG-TCCCGTGTATAGCAGCAGA
1589  98_HRV9       TTGTTTACATATGCAAGATTTGACTCTGAAATAACATTGG-TCCCGTGTATAGCAGCAGA
1590  99_HRV32      TTGTTTACATACACAAGGTTTGATTCTGAAATAACATTAG-TACCTTGTATAGCTGCAGA
1591  100_HRV32a    TTGTTTACATACACAAGGTTTGATTCTGAAATAACATTAG-TACCTTGTATAGCTGCAGA
1592  101_HRV32b    TTGTTTACATACACAAGGTTTGATTCTGAAATAACATTAG-TACCTTGTATAGCTGCAGA
1593  102_HRV67     CTATTCACATATACAAGATTTGATTCTGAGATAACACTGG-TACCATGCATAGCTGCAGA
1594  103_HRV67a    CTATTCACATATACAAGATTTGATTCTGAGATAACACTGG-TACCATGCATAGCTGCAGA
1595  104_HRV67b    CTATTCACATATACAAGATTTGATTCTGAGATAACACTGG-TACCATGCATAGCTGCAGA
1596  105_HRV15     TTATTCACATATGTAAGGTTTGATTCAGAAATAACACTTG-TACCATGCATTGCAGCAAA
1597  106_HRV15a    TTATTCACATATGTAAGGTTTGATTCAGAAATAACACTTG-TACCATGCATTGCAGCAAA
1598  107_HRV15b    TTATTCACATATGTAAGGTTTGATTCAGAAATAACACTTG-TACCATGCATTGCAGCAAA
1599  108_HRV74a    TTGTTCACATATGTTAGATTTGACTCAGAAGTGACATTAG-TTCCATGCATTGCTGCTAA
1600  109_HRV74b    TTGTTCACATATGTTAGATTTGACTCAGAAGTGACATTAG-TTCCATGCATTGCTGCTAA
1601  110_HRV74     TTGTTCACATATGTTAGATTTGACTCAGAAGTGACATTAG-TTCCATGCATTGCTGCTAA
1602  111_HRV38a    ATGTTTACATATGTGAGATTTGATTCAGAAGTTACATTAG-TCCCATGTATAGCAGCACA
1603  112_HRV38b    ATGTTTACATATGTGAGATTTGATTCAGAAGTTACATTAG-TCCCATGTATAGCAGCACA
1604  113_HRV38     ATGTTTACATATGTGAGATTTGATTCAGAAGTTACATTAG-TCCCATGTATAGCAGCACA
1605  114_HRV60     TTATTCACATATGTAAGATTTGATTCAGAATTGACTCTGG-TCCCATGCATAGCAGCAAA
1606  115_HRV60a    TTATTCACATATGTAAGATTTGATTCAGAATTGACTCTGG-TCCCATGCATAGCAGCAAA
1607  116_HRV60b    TTATTCACATATGTAAGATTTGATTCAGAATTGACTCTGG-TCCCATGCATAGCAGCAAA
1608  117_HRV64a    TTATTTACATATGTTAGATTTGATTCTGAAATAACCTTAG-TGCCTTGCATATCTTCTCA
1609  118_HRV64b    TTATTTACATATGTTAGATTTGATTCTGAAATAACCTTAG-TGCCTTGCATATCTTCTCA
1610  119_HRV64     TTATTTACATATGTTAGATTTGATTCTGAAATAACCTTAG-TGCCTTGCATATCTTCTCA
1611  120_HRV94a    CTATTTACTTATGTTAGATTTGATTCAGAAATAACTTTAG-TACCTTGCATATCATCTCA
1612  121_HRV94b    CTATTTACTTATGTTAGATTTGATTCAGAAATAACTTTAG-TACCTTGCATATCATCTCA
1613  122_HRV94     CTATTTACTTATGTTAGATTTGATTCAGAAATAACTTTAG-TACCTTGCATATCATCTCA
1614  123_HRV22     CTATTTACATATCTCAGGTTTGATTCTGAAATCACTTTGG-TACCATGCATTGCTTCACA
1615  124_HRV22a    CTATTTACATATCTCAGGTTTGATTCTGAAATCACTTTGG-TACCATGCATTGCTTCACA
1616  125_HRV22b    CTATTTACATATCTCAGGTTTGATTCTGAAATCACTTTGG-TACCATGCATTGCTTCACA
1617  126_HRV82     CTTTTCACATATGTGAGATTTGATTCAGAAATTACTTTAG-TGCCTTGCATAGCCTCTCA
1618  127_HRV82b    CTTTTCACATATGTGAGATTTGATTCAGAAATTACTTTAG-TGCCTTGCATAGCCTCTCA
1619  128_HRV82a    CTTTTCACATATGTGAGATTTGATTCAGAAATTACTTTAG-TGCCTTGCATAGCCTCTCA
1620  129_HRV19     CTTTTCACTTACCTCAGATTTGATTCAGAGGTAACATTAG-TCCCTTGCATAGCTGCTAA
1621  130_HRV19a    CTTTTCACTTACCTCAGATTTGATTCAGAGGTAACATTAG-TCCCTTGCATAGCTGCTAA
1622  131_HRV19b    CTTTTCACTTACCTCAGATTTGATTCAGAGGTAACATTAG-TCCCTTGCATAGCTGCTAA
1623  132_HRV13     TTGTTCACCTATGTAAGATTTGATTCAGAAATAACAATTG-TGCCGTGTATAGCCGGGCA
1624  133_HRV13a    TTGTTCACCTATGTAAGATTTGATTCAGAAATAACAATTG-TGCCATGTATAGCCGGGCA
1625  134_HRV13b    TTGTTCACCTATGTAAGATTTGATTCAGAAATAACAATTG-TGCCATGTATAGCCGGGCA
```

FIG. D7 CONT'D

```
03.trace                                                                              9/20/2007 5:03 PM 1626 135_HRV41    TTTTTTACGTATGTTAGATTTGACTCAGAAATAACAATTG-TGCCAAGTATAGCTGGACA
1627 136_HRV41a   TTTTTTACGTATGTTAGATTTGACTCAGAAATAACAATTG-TGCCAAGTATAGCTGGACA
1628 137_HRV41b   TTTTTTACGTATGTTAGATTTGACTCAGAAATAACAATTG-TGCCAAGTATAGCTGGACA
1629 138_HRV73    TTATTCACCTATGTAAGATTTGATTCAGAAGTGACAATTG-TACCATGTATAGCTGGTCA
1630 139_HRV73b   TTATTCACCTATGTAAGATTTGATTCAGAAGTGACAATTG-TACCATGTATAGCTGGTCA
1631 140_HRV73a   TTATTCACCTATGTAAGATTTGATTCAGAAGTGACAATTG-TACCATGTATAGCTGGTCA
1632 141_HRV61    TTGTTCACATATGCTAGATTTGATTCAGAGATTACAATTG-TACCTTGTGTTGCTGGGCA
1633 142_HRV61a   TTGTTCACATATGCTAGATTTGATTCAGAGATTACAATTG-TACCTTGTGTTGCTGGGCA
1634 143_HRV61b   TTGTTCACATATGCTAGATTTGATTCAGAGATTACAATTG-TACCTTGTGTTGCTGGGCA
1635 144_HRV96    CTGTTCACTTATGCTAGATTTGATTCAGAGATAACAATTG-TTCCATGTGTTGCTGTGCA
1636 145_HRV96b   CTGTTCACTTATGCTAGATTTGATTCAGAGATAACAATTG-TTCCATGTGTTGCTGTGCA
1637 146_HRV96a   CTGTTCACTTATGCTAGATTTGATTCAGAGATAACAATTG-TTCCATGTGTTGCTGTGCA
1638 90_HRV16a|   ATGTTTACTTATGCAAGATTTGACTCTGAAATTACTATGG-TACCAAGTGTAGCAGCCAA
1639 91_HRV16b|   ATGTTTACTTATGCAAGATTTGACTCTGAAATTACTATGG-TACCAAGTGTAGCAGCCAA
1640 92_1AYM_A    ATGTTTACTTATGCAAGATTTGACTCTGAAATTACTATGG-TACCAAGTGTAGCAGCCAA
1641 93_HRV81a|   ATGTTCACATACACTAGATTTAACTCTGAGATTACACTGG-TACCAAGTATTGCAAACAA
1642 94_HRV81b|   ATGTTCACATACACTAGATTTAACTCTGAGATTACACTGG-TACCAAGTATTGCAAACAA
1643 95_HRV81     ATGTTCACATACACTAGATTTAACTCTGAGATTACACTGG-TACCAAGTATTGCAAACAA
1644 147_HRV2     TTGTTCACCTATACTAGGTTTGATTCTGAAATAACCCTAG-TTCCATGCATTTCCGCCCT
1645 148_HRV2a|   TTGTTCACCTATACTAGGTTTGATTCTGAAATAACCCTAG-TTCCATGCATTTCCGCCCT
1646 149_HRV2b|   TTGTTCACCTATACTAGGTTTGATTCTGAAATAACCCTAG-TTCCATGCATTTCCGCCCT
1647 150_HRV49a   CTGTTTACTTACACTAGATTCGATTCTGAAATAACCTTGG-TTCCATGCATTTCTGCACT
1648 151_HRV49b   CTGTTTACTTACACTAGATTCGATTCTGAAATAACCTTGG-TTCCATGCATTTCTGCACT
1649 152_HRV49    CTGTTTACTTACACTAGATTCGATTCTGAAATAACCTTGG-TTCCATGCATTTCTGCACT
1650 153_HRV23a   CTGTTTACTTACACTAGATTTGATTCTGAAATTACTTTGG-TTCCATGCATTTCTGCTCT
1651 154_HRV23b   CTGTTTACTTACACTAGATTTGATTCTGAAATTACTTTGG-TTCCATGCATTTCTGCTCT
1652 155_HRV23    CTGTTTACTTACACTAGATTTGATTCTGAAATTACTTTGG-TTCCATGCATTTCTGCTCT
1653 156_HRV30a   CTATTCACTTACACTAGATTTGATTCTGAGATAACCTTGG-TTCCGTGTATTTCAGCTCT
1654 157_HRV30b   CTATTCACTTACACTAGATTTGATTCTGAGATAACCTTGG-TTCCGTGTATTTCAGCTCT
1655 158_HRV30    CTATTCACTTACACTAGATTTGATTCTGAGATAACCTTGG-TTCCGTGTATTTCAGCTCT
1656 159_HRV7     CTATTCACATACACTAGATTTGATTCTGAGATAACAATAG-TCACAGCAGCAGCAGCACA
1657 160_HRV7b|   CTATTCACATACACTAGATTTGATTCTGAGATAACAATAG-TCACAGCAGCAGCAGCACA
1658 161_HRV7a|   CTATTCACATACACTAGATTTGATTCTGAGATAACAATAG-TCACAGCAGCAGCAGCACA
1659 162_HRV88    TTGTTTACATACACTAGATTTGACTCAGAAATAACAATAG-TCACAGCAGCTGCAGCACA
1660 163_HRV88a   TTGTTTACATACACTAGATTTGACTCAGAAATAACAATAG-TCACAGCAGCTGCAGCACA
1661 164_HRV88b   TTGTTTACATACACTAGATTTGACTCAGAAATAACAATAG-TCACAGCAGCTGCAGCACA
1662 165_HRV36a   TTGTTTACATACACAAGATTTGACTCAGAAATAACAATAG-TCACCGCAGCTGCAGTGCA
1663 166_HRV36b   TTGTTTACATACACAAGATTTGACTCAGAAATAACAATAG-TCACCGCAGCTGCAGTGCA
1664 167_HRV36    TTGTTTACATACACAAGATTTGACTCAGAAATAACAATAG-TCACCGCAGCTGCAGTGCA
1665 168_HRV89a   TTATTCACATATACAAGATTTGATTCAGAGATAACAATAG-TCACTGCAGCCGCAGCTCA
1666 169_HRV89b   TTATTCACATATACAAGATTTGATTCAGAGATAACAATAG-TCACTGCAGCCGCAGCTCA
1667 170_HRV89    TTATTCACATATACAAGATTTGATTCAGAGATAACAATAG-TCACTGCAGCCGCAGCTCA
1668 171_HRV58    TTGTTTACATATACAAGATTTGACTCAGAGATTACAATAG-TCACTGCAGCAGCTGCTCA
1669 172_HRV58a   TTGTTTACATATACAAGATTTGACTCAGAGATTACAATAG-TCACTGCAGCAGCTGCTCA
1670 173_HRV58b   TTGTTTACATATACAAGATTTGACTCAGAGATTACAATAG-TCACTGCAGCAGCTGCTCA
1671 174_HRV12a   CTTTTCACCTACTTAAGGTTTGATTCTGAAATCACCATTGTTCCAAGCAATG-CAGCAAT
1672 175_HRV12b   CTTTTCACCTACTTAAGGTTTGATTCTGAAATCACCATTGTTCCAAGCAATG-CAGCAAT
1673 176_HRV12    CTTTTCACCTACTTAAGGTTTGATTCTGAAATCACCATTGTTCCAAGCAATG-CAGCAAT
1674 177_HRV78a   ATGTTCACATATCTCAGATTTGATTCAGAAATCACTCTTG-TGTGTGCAGTGGCCTCACA
1675 178_HRV78b   ATGTTCACATATCTCAGATTTGATTCAGAAATCACTCTTG-TGTGTGCAGTGGCCTCACA
1676 179_HRV78    ATGTTCACATATCTCAGATTTGATTCAGAAATCACTCTTG-TGTGTGCAGTGGCCTCACA
1677 180_HRV20    CTCTTTACATACCTCAGATTTGATTCTGAGATTACAATAG-TAGCAACAGTAGCTGCACT
1678 181_HRV20a   CTCTTTACATACCTCAGATTTGATTCTGAGATTACAATAG-TAGCAACAGTAGCTGCACT
1679 182_HRV20b   CTCTTTACATACCTCAGATTTGATTCTGAGATTACAATAG-TAGCAACAGTAGCTGCACT
1680 183_HRV68    CTATTCACATACCTTAGGTTTGACTCTGAGATTACAATAG-TAGCAACAATAGCTGCTCT
1681 184_HRV68a   CTATTCACATACCTTAGGTTTGACTCTGAGATTACAATAG-TAGCAACAATAGCTGCTCT
1682 185_HRV68b   CTATTCACATACCTTAGGTTTGACTCTGAGATTACAATAG-TAGCAACAATAGCTGCTCT
1683 186_HRV28    ATGTTTACATATCTCAGATTTGATTCTGAAATTACTATAG-TGGTGTCAGTTGCAAGTAA
1684 187_HRV28a   ATGTTTACATATCTCAGATTTGATTCTGAAATTACTATAG-TGGTGTCAGTTGCAAGTAA
1685 188_HRV28b   ATGTTTACATATCTCAGATTTGATTCTGAAATTACTATAG-TGGTGTCAGTTGCAAGTAA
1686 189_HRV53a   ATGTTCACATATCTTAGATTTGATTCAGAAATAACTATAG-TGGTATCAGTGGCTAGTAA
1687 190_HRV53b   ATGTTCACATATCTTAGATTTGATTCAGAAATAACTATAG-TGGTATCAGTGGCTAGTAA
1688 191_HRV53    ATGTTCACATATCTTAGATTTGATTCAGAAATAACTATAG-TGGTATCAGTGGCTAGTAA
1689 192_HRV46a   CTTTTTACATATCTCAGATTTGATTCAGAAATAACAATAG-TCACCACATTGGCAGGCCA
1690 193_HRV46b   CTTTTTACATATCTCAGATTTGATTCAGAAATAACAATAG-TCACCACATTGGCAGGCCA
```

FIG. D7 CONT'D

03.trace                                                                 9/20/2007 5:03 PM

```
1691 194_HRV46    CTTTTTACATATCTCAGATTTGATTCAGAAATAACAATAG-TCACCACATTGGCAGGCCA
1692 195_HRV80a   CTTTTCACTTACCTCAGATTTGACTCAGAAATAACAATAG-TAACTACCTTAGCAGGACA
1693 196_HRV80b   CTTTTCACTTACCTCAGATTTGACTCAGAAATAACAATAG-TAACTACCTTAGCAGGACA
1694 197_HRV80    CTTTTCACTTACCTCAGATTTGACTCAGAAATAACAATAG-TAACTACCTTAGCAGGACA
1695 198_HRV51    CTTTTCACATACTTAAGATTTGATTCAGAGATCACTATAG-TTGCTACCATTGCTGGACA
1696 199_HRV51a   CTTTTCACATACTTAAGATTTGATTCAGAGATCACTATAG-TTGCTACCATTGCTGGACA
1697 200_HRV51b   CTTTTCACATACTTAAGATTTGATTCAGAGATCACTATAG-TTGCTACCATTGCTGGACA
1698 201_HRV65a   CTCTTCACCTATTTGCGCTTTGACTCAGAAATTACCATAG-TGGCTACTATAGCTGGACA
1699 202_HRV65b   CTCTTCACCTATTTGCGCTTTGACTCAGAAATTACCATAG-TGGCTACTATAGCTGGACA
1700 203_HRV65    CTCTTCACCTATTTGCGCTTTGACTCAGAAATTACCATAG-TGGCTACTATAGCTGGACA
1701 204_HRV71a   CTCTTCACATACCTGCGCTTTGATTCAGAGATAACAATTG-TAGCTACACTAGCAGGGCA
1702 205_HRV71b   CTCTTCACATACCTGCGCTTTGATTCAGAGATAACAATTG-TAGCTACACTAGCAGGGCA
1703 206_HRV71    CTCTTCACATACCTGCGCTTTGATTCAGAGATAACAATTG-TAGCTACACTAGCAGGGCA
1704 207_HRV8     ATGTTCACTTATGTAAGATTTGATTCAGAGATAACAATTG-TACCATGTATTGCAGCTAT
1705 208_HRV95    ATGTTCACTTATGTAAGATTTGATTCAGAGATAACAATTG-TACCATGTATTGCAGCTAT
1706 209_HRV45    ATGTTTACATATGTCAGATTTGATTCCGAAATAACAATAG-TACCATGTGTTGCTGCCAC
1707 210_HRV45a   ATGTTTACATATGTCAGATTTGATTCCGAAATAACAATAG-TACCATGTGTTGCTGCCAC
1708 211_HRV45b   ATGTTTACATATGTCAGATTTGATTCCGAAATAACAATAG-TACCATGTGTTGCTGCCAC
1709 GROUP_1      -T-TT-AC-TA-----G-TT--A-TC-GA--T-AC--T-G-T-----------C------
1710
1711 1_HRV1A1|d   AGGAGACGACATTGGACATATTGTAATGCAATATATGTATGTTCCTCCAGGAGCTCCAAT
1712 2_HRV1A2|d   AGGAGACGACATTGGACATATTGTAATGCAATATATGTATGTTCCTCCAGGAGCTCCAAT
1713 3_HRV1A|cD   AGGAGACGACATTGGACATATTGTAATGCAATATATGTATGTTCCTCCAGGAGCTCCAAT
1714 4_HRV1B1|d   AGGAGATGACATTGGTCATGTTGTAATGCAGTATATGTATGTTCCCCCAGGAGCTCCAAT
1715 5_HRV1B2|d   AGGAGATGACATTGGTCATGTTGTAATGCAGTATATGTATGTTCCCCCAGGAGCTCCAAT
1716 6_HRV1B      AGGAGATGACATTGGTCATGTTGTAATGCAGTATATGTATGTTCCCCCAGGAGCTCCAAT
1717 7_HRV40a|d   GGGTGAAGACATTGGTCATCAATATATGTATGTACCCCCTGGCGCACCCAT
1718 8_HRV40b|d   GGGTGAAGACATTGGACACATTGTGATGCAATATATGTATGTACCCCCTGGCGCACCCAT
1719 9_HRV40      GGGTGAAGACATTGGACACATTGTGATGCAATATATGTATGTACCCCCTGGCGCACCCAT
1720 10_HRV85     GGGTGATGATATTGGACACATTGTAATGCAGTATATGTATGTGCCCCCCGGAGCACCAAT
1721 11_HRV85a|   GGGTGATGATATTGGACACATTGTAATGCAGTATATGTATGTGCCCCCCGGAGCACCAAT
1722 12_HRV85b|   GGGTGATGATATTGGACACATTGTAATGCAGTATATGTATGTGCCCCCCGGAGCACCAAT
1723 13_HRV56a|   GGGAGATGATATTGGACACATTGTAATGCAATACATGTATGTGCCTCCTGGTGCACCACT
1724 14_HRV56b|   GGGAGATGATATTGGACACATTGTAATGCAATACATGTATGTGCCTCCTGGTGCACCACT
1725 15_HRV56     GGGAGATGATATTGGACACATTGTAATGCAATACATGTATGTGCCTCCTGGTGCACCACT
1726 16_HRV54     GGGAGTTGATATTGGACACATTGTCATGCAATTCATGTATGTACCGCCTGGTGCACCAAA
1727 17_HRV98     GGGAGCTGACATTGGACACATTGTCATGCAATTCATGTATGTTCCACCTGGTGCACCTAA
1728 18_HRV59a|   AGGGGATGACATTGGTCATATAGTCATGCAATATATGTATGTTCCACCAGGTGCTCCACT
1729 19_HRV59b|   AGGGGATGACATTGGTCATATAGTCATGCAATATATGTATGTTCCACCAGGTGCTCCACT
1730 20_HRV59     AGGGGATGACATTGGTCATATAGTCATGCAATATATGTATGTTCCACCAGGTGCTCCACT
1731 21_HRV63     AGGTGATGACATTGGTCATATAGTTATGCAGTACATGTACGTTCCACCCGGTGCCCCTCT
1732 22_HRV63b|   AGGTGATGACATTGGTCATATAGTTATGCAGTACATGTACGTTCCACCCGGTGCCCCTCT
1733 23_HRV63a|   AGGTGATGACATTGGTCATATAGTTATGCAGTACATGTACGTTCCACCCGGTGCCCCTCT
1734 24_HRV39     AGGTGAAGATATTGGACACATAGTAATGCAATACATGTATGTCCCACCTGGTGCACCTGT
1735 25_HRV39a|   AGGTGAAGATATTGGACACATAGTAATGCAATACATGTATGTCCCACCTGGTGCACCTGT
1736 26_HRV39b|   AGGTGAAGATATTGGACACATAGTAATGCAATACATGTATGTCCCACCTGGTGCACCTGT
1737 27_HRV10a|   GGGCGATGACATAGGTCACATAGTTATGCAATATATGTATGTGCCACCTGGGGCTCCAGT
1738 28_HRV10b|   GGGCGATGACATAGGTCACATAGTTATGCAATATATGTATGTGCCACCTGGGGCTCCAGT
1739 29_HRV10|    GGGCGATGACATAGGTCACATAGTTATGCAATATATGTATGTGCCACCTGGGGCTCCAGT
1740 30_HRV100a   AGGAGATGACATAGGGCATATCGTAATGCAGTACATGTATGTGCCACCTGGAGCTCCAGT
1741 31_HRV100b   AGGAGATGACATAGGGCATATCGTAATGCAGTACATGTATGTGCCACCTGGAGCTCCAGT
1742 32_HRV100    AGGAGATGACATAGGGCATATCGTAATGCAGTACATGTATGTGCCACCTGGAGCTCCAGT
1743 33_HRV66     GGGTGATGATATAGGACATATTGTGATGCAATACATGTATGTACCACCTGGAGCCCCAAT
1744 34_HRV66b|   GGGTGATGATATAGGACATATTGTGATGCAATACATGTATGTACCACCTGGAGCCCCAAT
1745 35_HRV66a|   GGGTGATGATATAGGACATATTGTGATGCAATACATGTATGTACCACCTGGAGCCCCAAT
1746 36_HRV77a|   AGGTGATGACATAGGACATGTTGTCATGCAATACATGTATGTACCACCAGGGGCACCCAT
1747 37_HRV77b|   AGGTGATGACATAGGACATGTTGTCATGCAATACATGTATGTACCACCAGGGGCACCCAT
1748 38_HRV77     AGGTGATGACATAGGACATGTTGTCATGCAATACATGTATGTACCACCAGGGGCACCCAT
1749 39_HRV62a    TGGTGCAGATATAGGTCACATAGTTATGCAATATATGTATGTACCACCTGGGGCTCCACT
1750 40_HRV62b    TGGTGCAGATATAGGTCACATAGTTATGCAATATATGTATGTACCACCTGGGGCTCCACT
1751 41_HRV25     TGGTGCAGATATAGGTCACATAGTTATGCAATACATGTATGTACCACCTGGAGCCCCATT
1752 42_HRV29a    TGGTAATGATATAGGTCACATAGTTATGCAGTACATGTATGTACCACCTGGAGCTCCAGT
1753 43_HRV29b    TGGTAATGATATAGGTCACATAGTTATGCAGTACATGTATGTACCACCTGGAGCTCCAGT
1754 44_HRV44a    TGGTGATGATATAGGCCACATAGTTATGCAGTACATGTATGTACCACCTGGAGCTCCAGT
1755 45_HRV44b    TGGTGATGATATAGGCCACATAGTTATGCAGTACATGTATGTACCACCTGGAGCTCCAGT
```

FIG. D7 CONT'D

```
03.trace                                                                 9/20/2007 5:03 PM 1756  46_HRV31     TGGTAGTGACATAGGCCATATAGTCATGCAATACATGTATGTACCACCTGGGGCCCCAGT
1757  47_HRV31a|   TGGTAGTGACATAGGCCATATAGTCATGCAATACATGTATGTACCACCTGGGGCCCCAGT
1758  48_HRV31b|   TGGTAGTGACATAGGCCATATAGTCATGCAATACATGTATGTACCACCTGGGGCCCCAGT
1759  49_HRV47     TGGTGATGACATAGGTCACATAGTTATGCAATACATGTATGTGCCGCCTGGGGCTCCAGT
1760  50_HRV47a|   TGGTGATGACATAGGTCACATAGTTATGCAATACATGTATGTGCCGCCTGGGGCTCCAGT
1761  51_HRV47b|   TGGTGATGACATAGGTCACATAGTTATGCAATACATGTATGTGCCGCCTGGGGCTCCAGT
1762  52_HRV11     AGGAAATGATATTGGTCATGTTGTAATGCAATATATGTATGTCCCACCAGGTGCTCCAGT
1763  53_HRV11b|   AGGAAATGATATTGGTCATGTTGTAATGCAATATATGTATGTCCCACCAGGTGCTCCAGT
1764  54_HRV11a|   AGGAAATGATATTGGTCATGTTGTAATGCAATATATGTATGTCCCACCAGGTGCTCCAGT
1765  55_HRV76     AGGGGATGACATTGGTCATGTAGTGATGCAATACATGTATGTCCCACCAGGCGCTCCAGT
1766  56_HRV76b|   AGGGGATGACATTGGTCATGTAGTGATGCAATACATGTATGTCCCACCAGGCGCTCCAGT
1767  57_HRV76a|   AGGGGATGACATTGGTCATGTAGTGATGCAATACATGTATGTCCCACCAGGCGCTCCAGT
1768  58_HRV33     GGGAGATGATGTTGGTCATGTTGTAATGCAGTACATGTATGTCCCACCAGGTGCACCAGC
1769  59_HRV33b|   GGGAGATGATGTTGGTCATGTTGTAATGCAGTACATGTATGTCCCACCAGGTGCACCAGC
1770  60_HRV33a|   GGGAGATGATGTTGGTCATGTTGTAATGCAGTACATGTATGTCCCACCAGGTGCACCAGC
1771  61_HRV24a|   GGGAGATGACATTGGACATGTTGTAATGCAGTACATGTATATACCACCTGGAGCACCAGT
1772  62_HRV24b|   GGGAGATGACATTGGACATGTTGTAATGCAGTACATGTATATACCACCTGGAGCACCAGT
1773  63_HRV24     GGGAGATGACATTGGACATGTTGTAATGCAGTACATGTATATACCACCTGGAGCACCAGT
1774  64_HRV90     GGGCAATGATATTGGTCATGTTGTGATGCAATACATGTATATACCACCTGGGGCACCAGT
1775  65_HRV90a|   GGGCAATGATATTGGACATGTTGTGATGCAATACATGTATATACCACCTGGGGCACCAGT
1776  66_HRV90b|   GGGCAATGATATTGGACATGTTGTGATGCAATACATGTATATACCACCTGGGGCACCAGT
1777  67_HRV34     AGGTGATGATATTGGACATGTTGTGATGCAATACATGTATGTACCACCAGGTGCACCAAT
1778  68_HRV34b|   AGGTGATGATATTGGACATGTTGTGATGCAATACATGTATGTACCACCAGGTGCACCAAT
1779  69_HRV34a|   AGGTGATGATATTGGACATGTTGTGATGCAATACATGTATGTACCACCAGGTGCACCAAT
1780  70_HRV50a|   GGGTGTTGATATTGGACATGTTGTCATGCAATACATGTATGTCCCACCAGGTGCACCAAT
1781  71_HRV50b|   GGGTGTTGATATTGGACATGTTGTCATGCAATACATGTATGTCCCACCAGGTGCACCAAT
1782  72_HRV50     GGGTGTTGATATTGGACATGTTGTCATGCAATACATGTATGTCCCACCAGGTGCACCAAT
1783  73_HRV18a|   GGGTGATGACATAGGACATATTGTTATGCAGTACATGTATGTTCCTCCAGGAGCACCAAT
1784  74_HRV18b|   GGGTGATGACATAGGACATATTGTTATGCAGTACATGTATGTTCCTCCAGGAGCACCAAT
1785  75_HRV18     GGGTGATGACATAGGACATATTGTTATGCAGTACATGTATGTTCCTCCAGGAGCACCAAT
1786  76_HRV55     GGGAGATGACATTGGACATGTAGTCATGCAATACATGTATGTTCCACCTGGAGCACCAAT
1787  77_HRV55b|   GGGAGATGACATTGGACATGTAGTCATGCAATACATGTATGTTCCACCTGGAGCACCAAT
1788  78_HRV55a|   GGGAGATGACATTGGACATGTAGTCATGCAATACATGTATGTTCCACCTGGAGCACCAAT
1789  79_HRV57     AGGTGAGGATATAGGCCATGTTGTAATGCAATACATGTATGTCCCTCCTGGGGCACCAAT
1790  80_HRV57a|   AGGTGAGGATATAGGCCATGTTGTAATGCAATACATGTATGTCCCTCCTGGGGCACCAAT
1791  81_HRV57b|   AGGTGAGGATATAGGCCATGTTGTAATGCAATACATGTATGTCCCTCCTGGGGCACCAAT
1792  82_HRV21     AACGGGTGACATAGGACATGTTGTAATGCAATATATGTATGTCCCACCAGGTGCTCCAAT
1793  83_HRVHan    AGCGGGTGACATAGGACATGTTGTCAATATATGTATGTCCCACCAGGTGCTCCAAT
1794  84_HRV43     AAGCAATGATATAGGCCATGTGGTAATGCAGTACATGTATGTACCACCAGGTGCGCCAAT
1795  85_HRV43b|   AAGCAATGATATAGGCCATGTGGTAATGCAGTACATGTATGTACCACCAGGTGCGCCAAT
1796  86_HRV43a|   AAGCAATGATATAGGCCATGTGGTAATGCAGTACATGTATGTACCACCAGGTGCGCCAAT
1797  87_HRV75     AGGGAATGACATAGGCCATGTAGTAATGCAATATATGTATGTACCACCAGGAGCACCAAT
1798  88_HRV75b|   AGGGAATGACATAGGCCATGTAGTAATGCAATATATGTATGTACCACCAGGAGCACCAAT
1799  89_HRV75a|   AGGGAATGACATAGGCCATGTAGTAATGCAATATATGTATGTACCACCAGGAGCACCAAT
1800  96_HRV9a|d   AAGTGATAGCGTTGGCCATGTTGTTATGCAGTACATGTATGTACCACCAGGGGCACCTTT
1801  97_HRV9b|d   AAGTGATAGCGTTGGCCATGTTGTTATGCAGTACATGTATGTACCACCAGGGGCACCTTT
1802  98_HRV9      AAGTGATAGCGTTGGCCATGTTGTTATGCAGTACATGTATGTACCACCAGGGGCACCTTT
1803  99_HRV32     AAGTGACAGCATTGGTCATGTTGTTATGCAGTACATGTATGTACCACCAGGGGCTCCTCT
1804  100_HRV32a   AAGTGACAGCATTGGTCATGTTGTTATGCAGTACATGTATGTACCACCAGGGGCTCCTCT
1805  101_HRV32b   AAGTGACAGCATTGGTCATGTTGTTATGCAGTACATGTATGTACCACCAGGGGCTCCTCT
1806  102_HRV67    GAGTGACAGCATTGGGCATGTTGTAATGCAATATATGTATGTACCTCCAGGAGCACCATT
1807  103_HRV67a   GAGTGACAGCATTGGGCATGTTGTAATGCAATATATGTATGTACCTCCAGGAGCACCATT
1808  104_HRV67b   GAGTGACAGCATTGGGCATGTTGTAATGCAATATATGTATGTACCTCCAGGAGCACCATT
1809  105_HRV15    GAGTGATAACATCGGTCATGTTGTCATGCAATATATGTATGTTCCTCCGGGAGCCCCTTT
1810  106_HRV15a   GAGTGATAACATCGGTCATGTTGTCATGCAATATATGTATGTTCCTCCGGGAGCCCCTTT
1811  107_HRV15b   GAGTGATAACATCGGTCATGTTGTCATGCAATATATGTATGTTCCTCCGGGAGCCCCTTT
1812  108_HRV74a   AAGTGACAACATTGGCCATGTTGTTATGCAATACATGTATGTCCCCCCAGGAGCACCTTT
1813  109_HRV74b   AAGTGACAACATTGGCCATGTTGTTATGCAATACATGTATGTCCCCCCAGGAGCACCTTT
1814  110_HRV74    AAGTGACAACATTGGCCATGTTGTTATGCAATACATGTATGTCCCCCCAGGAGCACCTTT
1815  111_HRV38a   AAATGAAGGTGTGGGGCATGTTGTTATGCAGTATATGTATGTCCCTCCAGGGGCACCATT
1816  112_HRV38b   AAATGAAGGTGTGGGGCATGTTGTTATGCAGTATATGTATGTCCCTCCAGGGGCACCATT
1817  113_HRV38    AAATGAAGGTGTGGGGCATGTTGTTATGCAGTATATGTATGTCCCTCCAGGGGCACCATT
1818  114_HRV60    AAATGATGGCATAGGTCATGTTGTCATGCAATACATGTATGTCCCCCCAGGAGCACCATT
1819  115_HRV60a   AAATGATGGCATAGGTCATGTTGTCATGCAATACATGTATGTCCCCCCAGGAGCACCATT
1820  116_HRV60b   AAATGATGGCATAGGTCATGTTGTCATGCAATACATGTATGTCCCCCCAGGAGCACCATT
```

FIG. D7 CONT'D

03.trace                                                                                      9/20/2007 5:03 PM

```
1821 117_HRV64a    GAGTGCTAACATTGGTCATGTTGTTATGCAATATATGTATGTCCCTCCTGGAGCTCCAAT
1822 118_HRV64b    GAGTGCTAACATTGGTCATGTTGTTATGCAATATATGTATGTCCCTCCTGGAGCTCCAAT
1823 119_HRV64     GAGTGCTAACATTGGTCATGTTGTTATGCAATATATGTATGTCCCTCCTGGAGCTCCAAT
1824 120_HRV94a    AAGTGCTAATATTGGTCATGTTGTCATGCAGTACATGTATGTTCCTCCTGGAGCTCCAAA
1825 121_HRV94b    AAGTGCTAATATTGGTCATGTTGTCATGCAGTACATGTATGTTCCTCCTGGAGCTCCAAA
1826 122_HRV94     AAGTGCTAATATTGGTCATGTTGTCATGCAGTACATGTATGTTCCTCCTGGAGCTCCAAA
1827 123_HRV22     AAGTAAAAACATTGGTCATGTGGTCATGCAATACATGTATGTTCCGCCTGGAGCTCCTAA
1828 124_HRV22a    AAGTAAAAACATTGGTCATGTGGTCATGCAATACATGTATGTTCCGCCTGGAGCTCCTAA
1829 125_HRV22b    AAGTAAAAACATTGGTCATGTGGTCATGCAATACATGTATGTTCCGCCTGGAGCTCCTAA
1830 126_HRV82     AAGTAATGATATTGGGCATGTAGTGATGCAATACATGTATGTCCCACCAGGTGCTCCTAA
1831 127_HRV82b    AAGTAATGATATTGGGCATGTAGTGATGCAATACATGTATGTCCCACCAGGTGCTCCTAA
1832 128_HRV82a    AAGTAATGATATTGGGCATGTAGTGATGCAATACATGTATGTCCCACCAGGTGCTCCTAA
1833 129_HRV19     AAGTAAAAACATTGGACATGTTGTTATGCAATACATGTATGTGCCTCCTGGTGCTCCTAT
1834 130_HRV19a    AAGTAAAAACATTGGACATGTTGTTATGCAATACATGTATGTGCCTCCTGGTGCTCCTAT
1835 131_HRV19b    AAGTAAAAACATTGGACATGTTGTTATGCAATACATGTATGTGCCTCCTGGTGCTCCTAT
1836 132_HRV13     AGGTGGTGATGTCGGACATGTTGTTATGCAATACATGTATGTACCGCCCGGTGCACCCCT
1837 133_HRV13a    AGGTGGTGATGTCGGACATGTTGTTATGCAATACATGTATGTACCGCCCGGTGCACCCCT
1838 134_HRV13b    AGGTGGTGATGTCGGACATGTTGTTATGCAATACATGTATGTACCGCCCGGTGCACCCCT
1839 135_HRV41     GGGTAGTGATGTCGGACATGTTGTCATGCAATACATGTTCGTACCACCTGGCGCACCCCT
1840 136_HRV41a    GGGTAGTGATGTCGGACATGTTGTCATGCAATACATGTTCGTACCACCTGGCGCACCCCT
1841 137_HRV41b    GGGTAGTGATGTCGGACATGTTGTCATGCAATACATGTTCGTACCACCTGGCGCACCCCT
1842 138_HRV73     AAGTGGAGATGTGGGACATGTAGTTATGCAGTATATGTATGTCCCACCTGGAGCCCCTCT
1843 139_HRV73b    AAGTGGAGATGTGGGACATGTAGTTATGCAGTATATGTATGTCCCACCTGGAGCCCCTCT
1844 140_HRV73a    AAGTGGAGATGTGGGACATGTAGTTATGCAGTATATGTATGTCCCACCTGGAGCCCCTCT
1845 141_HRV61     AGGTGGTGACATTGGACACGTGGTCATGCAATACATGTATGTTCCACCTGGTGCACCTAC
1846 142_HRV61a    AGGTGGTGACATTGGACACGTGGTCATGCAATACATGTATGTTCCACCTGGTGCACCTAC
1847 143_HRV61b    AGGTGGTGACATTGGACACGTGGTCATGCAATACATGTATGTTCCACCTGGTGCACCTAC
1848 144_HRV96     GAGTGGTGATATTGGTCATGTGGTCATGCAATATATGTATGTTCCACCAGGTGCCCCCAC
1849 145_HRV96b    GAGTGGTGATATTGGTCATGTGGTCATGCAATATATGTATGTTCCACCAGGTGCCCCCAC
1850 146_HRV96a    GAGTGGTGATATTGGTCATGTGGTCATGCAATATATGTATGTTCCACCAGGTGCCCCCAC
1851  90_HRV16a|   AGATGGTCACATTGGTCATATAGTCATGCAATATATGTATGTACCACCAGGAGCACCTAT
1852  91_HRV16b|   AGATGGTCACATTGGTCATATAGTCATGCAATATATGTATGTACCACCAGGAGCACCTAT
1853  92_1AYM_A    AGATGGTCACATTGGTCATATAGTCATGCAATATATGTATGTACCACCAGGAGCACCTAT
1854  93_HRV81a|   GGAAGGTCATATTGGTCATATAGTAATGCAATACATGTATGTACCACCAGGAGCACCCAT
1855  94_HRV81b|   GGAAGGTCATATTGGTCATATAGTAATGCAATACATGTATGTACCACCAGGAGCACCCAT
1856  95_HRV81     GGAAGGTCATATTGGTCATATAGTAATGCAATACATGTATGTACCACCAGGAGCACCCAT
1857 147_HRV2      TAGTCAGGACATTGGACACATCACAATGCAATACATGTATGTTCCACCTGGTGCACCGGT
1858 148_HRV2a|    TAGTCAGGACATTGGACACATCACAATGCAATACATGTATGTTCCACCTGGTGCACCGGT
1859 149_HRV2b|    TAGTCAGGACATTGGACACATCACAATGCAATACATGTATGTTCCACCTGGTGCACCGGT
1860 150_HRV49a    TAGCAAGGATATTGGACACATTACAATGCAATACATGTATGTGCCGCCAGGTGCACCTGT
1861 151_HRV49b    TAGCAAGGATATTGGACACATTACAATGCAATACATGTATGTGCCGCCAGGTGCACCTGT
1862 152_HRV49     TAGCAAGGATATTGGACACATTACAATGCAATACATGTATGTGCCGCCAGGTGCACCTGT
1863 153_HRV23a    TAGTCAAGATATTGGTCACATCACAATGCAGTATATGTATGTCCCACCAGGTGCTCCAAT
1864 154_HRV23b    TAGTCAAGATATTGGTCACATCACAATGCAGTATATGTATGTCCCACCAGGTGCTCCAAT
1865 155_HRV23     TAGTCAAGATATTGGTCACATCACAATGCAGTATATGTATGTCCCACCAGGTGCTCCAAT
1866 156_HRV30a    CAGCCAAGATATCGGACACATTACAATGCAGTATATGTATGTTCCACCTGGCGCTCCAAT
1867 157_HRV30b    CAGCCAAGATATCGGACACATTACAATGCAGTATATGTATGTTCCACCTGGCGCTCCAAT
1868 158_HRV30     CAGCCAAGATATCGGACACATTACAATGCAGTATATGTATGTTCCACCTGGCGCTCCAAT
1869 159_HRV7      AGGTAATGATATTGGACATATAGTTATGCAATTTATGTATGTACCTCCAGGGGCCCCAGT
1870 160_HRV7b|    AGGTAATGATATTGGACATATAGTTATGCAATTTATGTATGTACCTCCAGGGGCCCCAGT
1871 161_HRV7a|    AGGTAATGATATTGGACATATAGTTATGCAATTTATGTATGTACCTCCAGGGGCCCCAGT
1872 162_HRV88     AGGTGATGATACTGGACATATAGTACTGCAATTCATGTATGTGCCTCCAGGTGCACCAAT
1873 163_HRV88a    AGGTGATGATACTGGACATATAGTACTGCAATTCATGTATGTGCCTCCAGGTGCACCAAT
1874 164_HRV88b    AGGTGATGATACTGGACATATAGTACTGCAATTCATGTATGTGCCTCCAGGTGCACCAAT
1875 165_HRV36a    GGGAGATGATAGTGGGCATGTAGTATTACAATTCATGTATGTACCTCCAGGAGCGCCTGT
1876 166_HRV36b    GGGAGATGATAGTGGGCATGTAGTATTACAATTCATGTATGTACCTCCAGGAGCGCCTGT
1877 167_HRV36     GGGAGATGATAGTGGGCATGTAGTATTACAATTCATGTATGTACCTCCAGGAGCGCCTGT
1878 168_HRV89a    AGGAAATGATAGTGGACATATAGTATTGCAATTTATGTATGTACCCCCAGGAGCACCTGT
1879 169_HRV89b    AGGAAATGATAGTGGACATATAGTATTGCAATTTATGTATGTACCCCCAGGAGCACCTGT
1880 170_HRV89     AGGAAATGATAGTGGACATATAGTATTGCAATTTATGTATGTACCCCCAGGAGCACCTGT
1881 171_HRV58     AGGAGAAGATAATGGACATATTGTTACAATTTATGTATGTACCCCCAGGAGCACCTGT
1882 172_HRV58a    AGGAGAAGATAATGGACATATTGTGTTACAATTTATGTATGTACCCCCAGGAGCACCTGT
1883 173_HRV58b    AGGAGAAGATAATGGACATATTGTGTTACAATTTATGTATGTACCCCCAGGAGCACCTGT
1884 174_HRV12a    AGAAGGAAGCAATGGTCACGTGGTGGTCCAATACATGTATGTACCTCCTGGTGCCCCACT
1885 175_HRV12b    AGAAGGAAGCAATGGTCACGTGGTGGTCCAATACATGTATGTACCTCCTGGTGCCCCACT
```

FIG. D7 CONT'D

```
03.trace                                                                    9/20/2007 5:03 PM 1886 176_HRV12     AGAAGGAAGCAATGGTCACGTGGTGGTCCAATACATGTATGTACCTCCTGGTGCCCCACT
1887 177_HRV78a    AGGAGACAATAATGGACATGTGGTGCTTCAATTTATGTTTGTTCCACCTGGAGCCCCTAT
1888 178_HRV78b    AGGAGACAATAATGGACATGTGGTGCTTCAATTTATGTTTGTTCCACCTGGAGCCCCTAT
1889 179_HRV78     AGGAGACAATAATGGACATGTGGTGCTTCAATTTATGTTTGTTCCACCTGGAGCCCCTAT
1890 180_HRV20     AGGTCGGGATAATGGGCATGTTGTTTTACAGTATATGTATGTACCACCAGGGGCACCAAT
1891 181_HRV20a    AGGTCGGGATAATGGGCATGTTGTTTTACAGTATATGTATGTACCACCAGGGGCACCAAT
1892 182_HRV20b    AGGTCGGGATAATGGGCATGTTGTTTTACAGTATATGTATGTACCACCAGGGGCACCAAT
1893 183_HRV68     TGGAAAAGATAATGGCCATGTGGTTTTACAGTACATGTATGTGCCGCCAGGGGCACCCAT
1894 184_HRV68a    TGGAAAAGATAATGGCCATGTGGTTTTACAGTACATGTATGTGCCGCCAGGGGCACCCAT
1895 185_HRV68b    TGGAAAAGATAATGGCCATGTGGTTTTACAGTACATGTATGTGCCGCCAGGGGCACCCAT
1896 186_HRV28     AGGTGATGATAATGGGCATGTAGTTATGCAATATATGTATGTACCTCCAGGAGCCCCCAT
1897 187_HRV28a    AGGTGATGATAATGGGCATGTAGTTATGCAATATATGTATGTACCTCCAGGAGCCCCCAT
1898 188_HRV28b    AGGTGATGATAATGGGCATGTAGTTATGCAATATATGTATGTACCTCCAGGAGCCCCCAT
1899 189_HRV53a    ACAAGGGAATAACGGGCACGTGGTGATACAATACATGTATGTACCACCGGGTGCTCCAAT
1900 190_HRV53b    ACAAGGGAATAACGGGCACGTGGTGATACAATACATGTATGTACCACCGGGTGCTCCAAT
1901 191_HRV53     ACAAGGGAATAACGGGCACGTGGTGATACAATACATGTATGTACCACCGGGTGCTCCAAT
1902 192_HRV46a    AGGGGATGATATTGGACATGTGGTCATACAATATATGTATGTGCCTCCTGGTGCTCCATT
1903 193_HRV46b    AGGGGATGATATTGGACATGTGGTCATACAATATATGTATGTGCCTCCTGGTGCTCCATT
1904 194_HRV46     AGGGGATGATATTGGACATGTGGTCATACAATATATGTATGTGCCTCCTGGTGCTCCATT
1905 195_HRV80a    AGGGGAGGACATTGGTCATGTAGTTATTCAATACATGTACGTACCACCAGGGGCCCCGTT
1906 196_HRV80b    AGGGGAGGACATTGGTCATGTAGTTATTCAATACATGTACGTACCACCAGGGGCCCCGTT
1907 197_HRV80     AGGGGAGGACATTGGTCATGTAGTTATTCAATACATGTACGTACCACCAGGGGCCCCGTT
1908 198_HRV51     GGGTGATGACATAGGGCACATTGTACTTCAATACATGTATGTACCCCCTGGAGGACCAGT
1909 199_HRV51a    GGGTGATGACATAGGGCACATTGTACTTCAATACATGTATGTACCCCCTGGAGGACCAGT
1910 200_HRV51b    GGGTGATGACATAGGGCACATTGTACTTCAATACATGTATGTACCCCCTGGAGGACCAGT
1911 201_HRV65a    AGGTGATGACATAGGGCACATAGTGCTTCAATATATGTATGTGCCTCCTGGTGGTCCTGT
1912 202_HRV65b    AGGTGATGACATAGGGCACATAGTGCTTCAATATATGTATGTGCCTCCTGGTGGTCCTGT
1913 203_HRV65     AGGTGATGACATAGGGCACATAGTGCTTCAATATATGTATGTGCCTCCTGGTGGTCCTGT
1914 204_HRV71a    AGGAGATGATTTAGGACATATTGTACTCCAGTACATGTATGTTCCCCCAGGTGGTCCAAT
1915 205_HRV71b    AGGAGATGATTTAGGACATATTGTACTCCAGTACATGTATGTTCCCCCAGGTGGTCCAAT
1916 206_HRV71     AGGAGATGATTTAGGACATATTGTACTCCAGTACATGTATGTTCCCCCAGGTGGTCCAAT
1917 207_HRV8      AAAAGGTGACCTTGGACACATAGTCCTTCAATACATGTATGTTCCCCCGGGTGCACCTCT
1918 208_HRV95     AGAAGGTGACCTTGGACACATAGTCCTCCAATACATGTATGTTCCCCCGGGTGCACCTCT
1919 209_HRV45     AGAAGGTAACTTGGGACACATTGTTGTGCAATACATGTTTGTACCACCAGGAGCACCTCT
1920 210_HRV45a    AGAAGGTAACTTGGGACACATTGTTGTGCAATACATGTTTGTACCACCAGGAGCACCTCT
1921 211_HRV45b    AGAAGGTAACTTGGGACACATTGTTGTGCAATACATGTTTGTACCACCAGGAGCACCTCT
1922 GROUP_1       ------------GG-CA--T-----T-CA-T--ATGT---T-CC-CC-GG-G--CC---
1923
1924 1_HRV1A1|d    TCCTTCAAAAAGAAACGATTTCTCATGGCAATCAGGCACCAATATGTCAATATTCTGGCA
1925 2_HRV1A2|d    TCCTTCAAAAAGAAACGATTTCTCATGGCAATCAGGCACCAATATGTCAATATTCTGGCA
1926 3_HRV1A|cD    TCCTTCAAAAAGAAACGATTTCTCATGGCAATCAGGCACCAATATGTCAATATTCTGGCA
1927 4_HRV1B1|d    TCCAAAAACAAGAAATGATTTCTCATGGCAATCAGGCACTAATATGTCAATATTCTGGCA
1928 5_HRV1B2|d    TCCAAAAACAAGAAATGATTTCTCATGGCAATCAGGCACTAATATGTCAATATTCTGGCA
1929 6_HRV1B       TCCAAAAACAAGAAATGATTTCTCATGGCAATCAGGCACTAATATGTCAATATTCTGGCA
1930 7_HRV40a|d    ACCAAAGAAAAGAAATGATTACACATGGCAGTCAGGCACTAATGCTTCTGTATTCTGGCA
1931 8_HRV40b|d    ACCAAAGAAAAGAAATGATTACACATGGCAGTCAGGCACTAATGCTTCTGTATTCTGGCA
1932 9_HRV40       ACCAAAGAAAAGAAATGATTACACATGGCAGTCAGGCACTAATGCTTCTGTATTCTGGCA
1933 10_HRV85      ACCAAGGAAAAGAGATGATTACACATGGCAATCAGGTACTAATGCTTCCGTGTTTTGGCA
1934 11_HRV85a|    ACCAAGGAAAAGAGATGATTACACATGGCAATCAGGTACTAATGCTTCCGTGTTTTGGCA
1935 12_HRV85b|    ACCAAGGAAAAGAGATGATTACACATGGCAATCAGGTACTAATGCTTCCGTGTTTTGGCA
1936 13_HRV56a|    TCCAAACTCAAGAGATGATTTTACATGGCAATCTGGCACCAATGCTTCTGTCTTTTGGCA
1937 14_HRV56b|    TCCAAACTCAAGAGATGATTTTACATGGCAATCTGGCACCAATGCTTCTGTCTTTTGGCA
1938 15_HRV56      TCCAAACTCAAGAGATGATTTTACATGGCAATCTGGCACCAATGCTTCTGTCTTTTGGCA
1939 16_HRV54      ACCAGAAAAAGGAATGATTACACCTGGGCAGTCAAGCACAAACCCTTCTATATTTTGGCA
1940 17_HRV98      ACCTAAAAGAGGAATGATTATACTTGGGAATCAAGCACAAACCCTTCTATATTCTGGCA
1941 18_HRV59a|    GCCCACAAGAGAGATGATTACACATGGCAATCTGGTACTAATGCTTCAATATTCTGGCA
1942 19_HRV59b|    GCCCACAAGAGAGATGATTACACATGGCAATCTGGTACTAATGCTTCAATATTCTGGCA
1943 20_HRV59      GCCCACAAGAGAGATGATTACACATGGCAATCTGGTACTAATGCTTCAATATTCTGGCA
1944 21_HRV63      ACCCACCCGAAGAGAAGATTACACATGGCAATCTGGCACTAATGCTTCAATATTCTGGCA
1945 22_HRV63b|    ACCCACCCGAAGAGAAGATTACACATGGCAATCTGGCACTAATGCTTCAATATTCTGGCA
1946 23_HRV63a|    ACCCACCCGAAGAGAAGATTACACATGGCAATCTGGCACTAATGCTTCAATATTCTGGCA
1947 24_HRV39      ACCTAAGAAGAGAGATGATTACACATGGCAATCTGGAAAAATGCCTCAGTTTTCTGGCA
1948 25_HRV39a|    ACCTAAGAAGAGAGATGATTACACATGGCAATCTGGAACAAATGCCTCAGTTTTCTGGCA
1949 26_HRV39b|    ACCTAAGAAGAGAGATGATTACACATGGCAATCTGGAACAAATGCCTCAGTTTTCTGGCA
1950 27_HRV10a|    ACCAACTAAGAGAGATGATTTTGCTTGGCAGTCGGGAACAAATGCATCAGTCTTCTGGCA
```

FIG. D7 CONT'D 03.trace                                                                 9/20/2007 5:03 PM

```
1951 28_HRV10b|     ACCAACTAAGAGAGATGATTTTGCTTGGCAGTCGGGAACAAATGCATCAGTCTTCTGGCA
1952 29_HRV10      ACCAACTAAGAGAGATGATTTTGCTTGGCAGTCGGGAACAAATGCATCAGTCTTCTGGCA
1953 30_HRV100a    TCCAACAAAAAGGGATGATTTTGCATGGCAATCAGGCACAAATGCATCAGTTTTTGGCA
1954 31_HRV100b    TCCAACAAAAAGGGATGATTTTGCATGGCAATCAGGCACAAATGCATCAGTTTTTTGGCA
1955 32_HRV100     TCCAACAAAAAGGGATGATTTTGCATGGCAATCAGGCACAAATGCATCAGTTTTTTGGCA
1956 33_HRV66      TCCAGATAATAGAACACACTTTGCTTGGCAATCAGGAACAAATGCATCTATATTCTGGCA
1957 34_HRV66b|    TCCAGATAATAGAACACACTTTGCTTGGCAATCAGGAACAAATGCATCTATATTCTGGCA
1958 35_HRV66a|    TCCAGATAATAGAACACACTTTGCTTGGCAATCAGGAACAAATGCATCTATATTCTGGCA
1959 36_HRV77a|    ACCAGATAGCAGGACTCATTTTGCATGGCAGTCAGGGACTAATGCATCAATATTCTGGCA
1960 37_HRV77b|    ACCAGATAGCAGGACTCATTTTGCATGGCAGTCAGGGACTAATGCATCAATATTCTGGCA
1961 38_HRV77      ACCAGATAGCAGGACTCATTTTGCATGGCAGTCAGGGACTAATGCATCAATATTCTGGCA
1962 39_HRV62a     ACCAACAGACAGAAAGCATTTTGCCTGGCAATCAAGTACTAATGCATCAATATTTTGGCA
1963 40_HRV62b     ACCAACAGACAGAAAGCATTTTGCCTGGCAATCAAGTACTAATGCATCAATATTTTGGCA
1964 41_HRV25      ACCAACAGACAGAAAACACTTTGCATGGCAATCAAGTACTAATGCATCAATATTTTGGCA
1965 42_HRV29a     ACCAAATGACAGAAATCATTTTGCATGGCAATCAGGGACTAATGCATCAATATTCTGGCA
1966 43_HRV29b     ACCAAATGACAGAAATCATTTTGCATGGCAATCAGGGACTAATGCATCAATATTCTGGCA
1967 44_HRV44a     ACCAGATGACAGAAACCACTTTGCATGGCAATCGGGGACTAATGCATCAATATTCTGGCA
1968 45_HRV44b     ACCAGATGACAGAATCCACTTTGCATGGCAATCGGGGAATAATGCATCAATATTCTGGCA
1969 46_HRV31      ACCAACAAATAGAAAACATTTTGCATGGCAATCAGGTACTAATGCATCGATTTTCTGGCA
1970 47_HRV31a|    ACCAACAAATAGAAAACATTTTGCATGGCAATCAGGTACTAATGCATCGATTTTCTGGCA
1971 48_HRV31b|    ACCAACAAATAGAAAACATTTTGCATGGCAATCAGGTACTAATGCATCGATTTTCTGGCA
1972 49_HRV47      GCCAACAAGTAGAGAGCACTTTGCATGGCAGTCAGGTACCAATGCATCAACTTTCTGGCA
1973 50_HRV47a|    GCCAACAAGTAGAGAGCACTTTGCATGGCAGTCAGGTACCAATGCATCAACTTTCTGGCA
1974 51_HRV47b|    GCCAACAAGTAGAGAGCACTTTGCATGGCAGTCAGGTACCAATGCATCAATTTTCTGGCA
1975 52_HRV11      TCCAGAGAAAAGAGATGATTATACATGGCAATCAGGAACAAATGCATCTATTTTCTGGCA
1976 53_HRV11b|    TCCAGAGAAAAGAGATGATTATACATGGCAATCAGGAACAAATGCATCTATTTTCTGGCA
1977 54_HRV11a|    TCCAGAGAAAAGAGATGATTATACATGGCAATCAGGAACAAATGCATCTATTTTCTGGCA
1978 55_HRV76      TCCAAAGAAGAGAGATGACTACACATGGCAGTCAGGAACCAATGCATCTATTTTCTGGCA
1979 56_HRV76b|    TCCAAAGAAGAGAGATGACTACACATGGCAGTCAGGAACCAATGCATCTATTTTCTGGCA
1980 57_HRV76a|    TCCAAAGAAGAGAGATGACTACACATGGCAGTCAGGAACCAATGCATCTATTTTCTGGCA
1981 58_HRV33      TCCAGAAAAGAGAGATGATTACACATGGCAATCAGGAACAAATGCATCTGTCTTTTGGCA
1982 59_HRV33b|    TCCAGAAAAGAGAGATGATTACACATGGCAATCAGGAACAAATGCATCTGTCTTTTGGCA
1983 60_HRV33a|    TCCAGAAAAGAGAGATGATTACACATGGCAATCAGGAACAAATGCATCTGTCTTTTGGCA
1984 61_HRV24a|    CCCAACAAAGAGAGATGATTATACATGGCAATCAGGAACAAATGCATCTGTCTTTTGGCA
1985 62_HRV24b|    CCCAACAAAGAGAGATGATTATACATGGCAATCAGGAACAAATGCATCTGTCTTTTGGCA
1986 63_HRV24      CCCAACAAAGAGAGATGATTATACATGGCAATCAGGAACAAATGCATCTGTCTTTTGGCA
1987 64_HRV90      ACCTGAGAAGAGGGATGATTATGCATGGCAATCAGGCACTAATGCATCTATCTTTTGGCA
1988 65_HRV90a|    ACCTGAGAAGAGGGATGATTATGCATGGCAATCAGGCACTAATGCATCTATCTTTTGGCA
1989 66_HRV90b|    ACCTGAGAAGAGGGATGATTATGCATGGCAATCAGGCACTAATGCATCTATCTTTTGGCA
1990 67_HRV34      ACCTAAAACTAGAGATGATTTTGCATGGCAATCTGGAACAAATGCCTCAATATTTTGGCA
1991 68_HRV34b|    ACCTAAAACTAGAGATGATTTTGCATGGCAATCTGGAACAAATGCCTCAATATTTTGGCA
1992 69_HRV34a|    ACCTAAAACTAGAGATGATTTTGCATGGCAATCTGGAACAAATGCCTCAATATTTTGGCA
1993 70_HRV50a|    ACCCAAGACTAGGGATGATTTTGCCTGGCAATCTGGAACTAATGCTTCAATCTTTTGGCA
1994 71_HRV50b|    ACCCAAGACTAGGGATGATTTTGCCTGGCAATCTGGAACTAATGCTTCAATCTTTTGGCA
1995 72_HRV50      ACCCAAGACTAGGGATGATTTTGCCTGGCAATCTGGAACTAATGCTTCAATCTTTTGGCA
1996 73_HRV18a|    ACCAAAACCAGAGATGATTTTGCCTGGCAATCTGGAACAAATGCATCAATCTTCTGGCA
1997 74_HRV18b|    ACCAAAACCAGAGATGATTTTGCCTGGCAATCTGGAACAAATGCATCAATCTTCTGGCA
1998 75_HRV18      ACCAAAACCAGAGATGATTTTGCCTGGCAATCTGGAACAAATGCATCAATCTTCTGGCA
1999 76_HRV55      TCCAAAGACAAGAGAAGATTATGCTTGGCAATCAGGGACCAATGCATCTATCTTTTGGCA
2000 77_HRV55b|    TCCAAAGACAAGAGAAGATTATGCTTGGCAATCAGGGACCAATGCATCTATCTTTTGGCA
2001 78_HRV55a|    TCCAAAGACAAGAGAAGATTATGCTTGGCAATCAGGGACCAATGCATCTATCTTTTGGCA
2002 79_HRV57      TCCAAAAACAAGAGAGGATTATACATGGCAATCTGGTACCAATGCTTCAATATTTTGGCA
2003 80_HRV57a|    TCCAAAAACAAGAGAGGATTATACATGGCAATCTGGTACCAATGCTTCAATATTTTGGCA
2004 81_HRV57b|    TCCAAAAACAAGAGAGGATTATACATGGCAATCTGGTACCAATGCTTCAATATTTTGGCA
2005 82_HRV21      TCCAAAAACTAGGGAAGATTTTGCTTGGCAGTCAGGCACTAATGCATCCATTTTCTGGCA
2006 83_HRVHan     TCCAAAAACTAGGGAAGATTTTGCTTGGCAATCAGGTACCAATGCATCCATTTTCTGGCA
2007 84_HRV43      TCCAAAAACTAGGAAAGATTATGCATGGCAATCTGGCACAAATGCATCTGTTTTCTGGCA
2008 85_HRV43b|    TCCAAAAACTAGGAAAGATTATGCATGGCAATCTGGCACAAATGCATCTGTTTTCTGGCA
2009 86_HRV43a|    TCCAAAAACTAGGAAAGATTATGCATGGCAATCTGGCACAAATGCATCTGTTTTCTGGCA
2010 87_HRV75      ACCAACAACTAGAAAAGATTATGCATGGCAATCTGGAACAAATGCATCTGTATTTTGGCA
2011 88_HRV75b|    ACCAACAACTAGAAAAGATTATGCATGGCAATCTGGAACAAATGCATCTGTATTTTGGCA
2012 89_HRV75a|    ACCAACAACTAGAAAAGATTATGCATGGCAATCTGGAACAAATGCATCTGTATTTTGGCA
2013 96_HRV9a|d    ACCAAGGACTAGAGATGATTATGCATGGCAATCAGGCACAAATGCTTCCATCTTTTGGCA
2014 97_HRV9b|d    ACCAAGGACTAGAGATGATTATGCATGGCAATCAGGCACAAATGCTTCCATCTTTTGGCA
2015 98_HRV9       ACCAAGGACTAGAGATGATTATGCATGGCAATCAGGCACAAATGCTTCCATCTTTTGGCA
```

FIG. D7 CONT'D 03.trace                                                                    9/20/2007 5:03 PM

```
2016  99_HRV32    ACCACAAGCAAGAGATGACTACACATGGCAATCTGGCACGAATGCATCTATCTTTTGGCA
2017 100_HRV32a   ACCACAAGCAAGAGATGACTACACATGGCAATCTGGCACGAATGCATCTATCTTTTGGCA
2018 101_HRV32b   ACCACAAGCAAGAGATGACTACACATGGCAATCTGGCACGAATGCATCTATCTTTTGGCA
2019 102_HRV67    ACCAACAAAAGAGATGACTACACATGGCAATCAGGTACAAATGCATCCATCTTTTGGCA
2020 103_HRV67a   ACCAACAAAAGAGATGACTACACATGGCAATCAGGTACAAATGCATCCATCTTTTGGCA
2021 104_HRV67b   ACCAACAAAAGAGATGACTACACATGGCAATCAGGTACAAATGCATCCATCTTTTGGCA
2022 105_HRV15    ACCCAATAAAAGGAATGATTACACATGGCAATCAGGTACAAATGCCTCTGTTTTCTGGCA
2023 106_HRV15a   ACCCAATAAAAGGAATGATTACACATGGCAATCAGGTACAAATGCCTCTGTTTTCTGGCA
2024 107_HRV15b   ACCCAATAAAAGGAATGATTACACATGGCAATCAGGTACAAATGCCTCTGTTTTCTGGCA
2025 108_HRV74a   ACCCAAGAAAAGAGATGATTACACATGGCAATCTGGCACAAATGCATCTGTGTTTTGGCA
2026 109_HRV74b   ACCCAAGAAAAGAGATGATTACACATGGCAATCTGGCACAAATGCATCTGTGTTTTGGCA
2027 110_HRV74    ACCCAAGAAAAGAGATGATTACACATGGCAATCTGGCACAAATGCATCTGTGTTTTGGCA
2028 111_HRV38a   ACCCAGGAAGAGAGATGATTACACTTGGCAATCTGGTACAAATGCCTCTGTTTTCTGGCA
2029 112_HRV38b   ACCCAGGAAGAGAGATGATTACACTTGGCAATCTGGTACAAATGCCTCTGTTTTCTGGCA
2030 113_HRV38    ACCCAGGAAGAGAGATGATTACACTTGGCAATCTGGTACAAATGCCTCTGTTTTCTGGCA
2031 114_HRV60    ACCTACTAAAAGAGACGATTACACATGGCAATCTGGCACAAATGCTTCTGTATTTTGGCA
2032 115_HRV60a   ACCTACTAAAAGAGACGATTACACATGGCAATCTGGCACAAATGCTTCTGTATTTTGGCA
2033 116_HRV60b   ACCTACTAAAAGAGACGATTACACATGGCAATCTGGCACAAATGCTTCTGTATTTTGGCA
2034 117_HRV64a   ACCAACCAAAAGAAATGATTACGTCTGGCAGTCAGGCACCAATGCATCCATCTTTTGGCA
2035 118_HRV64b   ACCAACCAAAAGAAATGATTACGTCTGGCAGTCAGGCACCAATGCATCCATCTTTTGGCA
2036 119_HRV64    ACCAACCAAAAGAAATGATTACGTCTGGCAGTCAGGCACCAATGCATCCATCTTTTGGCA
2037 120_HRV94a   ACCAGACAAAAGAGATGATTATGTTTGGCAATCAGGAACTAATGCATCTATATTCTGGCA
2038 121_HRV94b   ACCAGACAAAAGAGATGATTATGTTTGGCAATCAGGAACTAATGCATCTATATTCTGGCA
2039 122_HRV94    ACCAGACAAAAGAGATGATTATGTTTGGCAATCAGGAACTAATGCATCTATATTCTGGCA
2040 123_HRV22    ACCTGAAAAGAGAGATGACTACACATGGCAATCTGGCACTAATGCATCTGTTTTCTGGCA
2041 124_HRV22a   ACCTGAAAAGAGAGATGACTACACATGGCAATCTGGCACTAATGCATCTGTTTTCTGGCA
2042 125_HRV22b   ACCTGAAAAGAGAGATGACTACACATGGCAATCTGGCACTAATGCATCTGTTTTCTGGCA
2043 126_HRV82    ACCAGAAAAGAGAGACGACTACACTTGGCAATCTGGAACTAATGCTTCAATTTTCTGGCA
2044 127_HRV82b   ACCAGAAAAGAGAGACGACTACACTTGGCAATCTGGAACTAATGCTTCAATTTTCTGGCA
2045 128_HRV82a   ACCAGAAAAGAGAGACGACTACACTTGGCAATCTGGAACTAATGCTTCAATTTTCTGGCA
2046 129_HRV19    CCCAAAAACTAGAAATGATTACACATGGCAATCAGGTACTAATGCATCTATATTTTGGCA
2047 130_HRV19a   CCCAAAAACTAGAAATGATTACACATGGCAATCAGGTACTAATGCATCTATATTTTGGCA
2048 131_HRV19b   CCCAAAAACTAGAAATGATTACACATGGCAATCAGGTACTAATGCATCTATATTTTGGCA
2049 132_HRV13    TCCAACGAAGAGAAATGATTACACATGGCAATCTGGCACCAATGCATCTGTTTTCTGGCA
2050 133_HRV13a   TCCAACGAAGAGAAATGATTACACATGGCAATCTGGCACCAATGCATCTGTTTTCTGGCA
2051 134_HRV13b   TCCAACGAAGAGAAATGATTACACATGGCAATCTGGCACCAATGCATCTGTTTTCTGGCA
2052 135_HRV41    CCCAGAAAAGAGAGATGATTACACATGGCAATCTGGCACCAATGCATCTGTATTCTGGCA
2053 136_HRV41a   CCCAGAAAAGAGAGATGATTACACATGGCAATCTGGCACCAATGCATCTGTATTCTGGCA
2054 137_HRV41b   CCCAGAAAAGAGAGATGATTACACATGGCAATCTGGCACCAATGCATCTGTATTCTGGCA
2055 138_HRV73    ACCCACAAAAAGAAATGACTACACATGGCAGTCCGGCACTAATGCATCAGTATTCTGGCA
2056 139_HRV73b   ACCCACAAAAAGAAATGACTACACATGGCAGTCCGGCACTAATGCATCAGTATTCTGGCA
2057 140_HRV73a   ACCCACAAAAAGAAATGACTACACATGGCAGTCCGGCACTAATGCATCAGTATTCTGGCA
2058 141_HRV61    ACCTGAGAAAGAAATGATTTCACATGGCAATCAGGCACAAATGCATCTGTTTTCTGGCA
2059 142_HRV61a   ACCTGAGAAAAGAAATGATTTCACATGGCAATCAGGCACAAATGCATCTGTTTTCTGGCA
2060 143_HRV61b   ACCTGAGAAAAGAAATGATTTCACATGGCAATCAGGCACAAATGCATCTGTTTTCTGGCA
2061 144_HRV96    ACCTGAGAAGAGAGATGACTTTACATGGCAATCAGGCACAAATGCATCTGTGTTTTGGCA
2062 145_HRV96b   ACCTGAGAAGAGAGATGACTTTACATGGCAATCAGGCACAAATGCATCTGTGTTTTGGCA
2063 146_HRV96a   ACCTGAGAAGAGAGATGACTTTACATGGCAATCAGGCACAAATGCATCTGTGTTTTGGCA
2064  90_HRV16a|  ACCAACAACTAGAAATGACTATGCTTGGCAATCTGGAACAAATGCATCTGTATTTTGGCA
2065  91_HRV16b|  ACCAACAACTAGAAATGACTATGCTTGGCAATCTGGAACAAATGCATCTGTATTTTGGCA
2066  92_1AYM_A|  ACCAACAACTAGAAATGACTATGCTTGGCAATCTGGAACAAATGCATCTGTATTTTGGCA
2067  93_HRV81a|  TCCAACAACTAGAGAAGACTATGCTTGGCAATCTGGAACAAATGCATCTATATTCTGGCA
2068  94_HRV81b|  TCCAACAACTAGAGAAGACTATGCTTGGCAATCTGGAACAAATGCATCTATATTCTGGCA
2069  95_HRV81    TCCAACAACTAGAGAAGACTATGCTTGGCAATCTGGAACAAATGCATCTATATTCTGGCA
2070 147_HRV2     TCCAATAGTAGGGACGATTATGCATGGCAGTCTGGCACTAATGCCTCTGTTTTCTGGCA
2071 148_HRV2a|   GCCCAATAGTAGGGACGATTATGCATGGCAGTCTGGCACTAATGCCTCTGTTTTCTGGCA
2072 149_HRV2b|   GCCCAATAGTAGGGACGATTATGCATGGCAGTCTGGCACTAATGCCTCTGTTTTCTGGCA
2073 150_HRV49a   ACCAAAGAGCAGAGATGATTATGCATGGCAGTCTGGCACTAATGCATCTGTTTTCTGGCA
2074 151_HRV49b   ACCAAAGAGCAGAGATGATTATGCATGGCAGTCTGGCACTAATGCATCTGTTTTTCTGGCA
2075 152_HRV49    ACCAAAGAGCAGAGATGATTATGCATGGCAGTCTGGCACTAATGCATCTGTTTTCTGGCA
2076 153_HRV23a   ACCGGAAAGTAGAAATGACTATGCATGGCAATCTGGAACAAATGCGTCCATTTTTTGGCA
2077 154_HRV23b   ACCGGAAAGTAGAAATGACTATGCATGGCAATCTGGAACAAATGCGTCCATTTTTTGGCA
2078 155_HRV23    ACCGGAAAGTAGAAATGACTATGCATGGCAATCTGGAACAAATGCGTCCATTTTTTGGCA
2079 156_HRV30a   TCCCGAGAGCAGAAATGACTATGCATGGCAGTCTGGAACAAATGCATCTGTTTTTTGGCA
2080 157_HRV30b   TCCCGAGAGCAGAAATGACTATGCATGGCAGTCTGGAACAAATGCATCTGTTTTTTGGCA
```

FIG. D7 CONT'D

```
03.trace                                                                        9/20/2007 5:03 PM 2081 158_HRV30    TCCCGAGAGCAGAAATGACTATGCATGGCAGTCTGGAACAAATGCATCTGTTTTTTGGCA
2082 159_HRV7     TCCAATAAAACGCGAAGATTATACATGGCAATCAGGAACAAATGCTTCTATATTTTGGCA
2083 160_HRV7b|   TCCAATAAAACGCGAAGATTATACATGGCAATCAGGAACAAATGCTTCTATATTTTGGCA
2084 161_HRV7a|   TCCAATAAAACGCGAAGATTATACATGGCAATCAGGAACAAATGCTTCTATATTTTGGCA
2085 162_HRV88    TCCCAAGAAACGTGATGATTACACATGGCAGTCAGGAACAAATGCATCTGTGTTCTGGCA
2086 163_HRV88a   TCCCAAGAAACGTGATGATTACACATGGCAGTCAGGAACAAATGCATCTGTGTTCTGGCA
2087 164_HRV88b   TCCCAAGAAACGTGATGATTACACATGGCAGTCAGGAACAAATGCATCTGTGTTCTGGCA
2088 165_HRV36a   TCCTGTGAAGCGTGATGACTACACATGGCAATCAGGGACAAATGCATCTGTGTTCTGGCA
2089 166_HRV36b   TCCTGTGAAGCGTGATGACTACACATGGCAATCAGGGACAAATGCATCTGTGTTCTGGCA
2090 167_HRV36    TCCTGTGAAGCGTGATGACTACACATGGCAATCAGGGACAAATGCATCTGTGTTCTGGCA
2091 168_HRV89a   CCCCGAAAAACGTGATGATTACACATGGCAATCAGGAACAAATGCATCTGTGTTCTGGCA
2092 169_HRV89b   CCCCGAAAAACGTGATGATTACACATGGCAATCAGGAACAAATGCATCTGTGTTCTGGCA
2093 170_HRV89    CCCCGAAAAACGTGATGATTACACATGGCAATCAGGAACAAATGCATCTGTGTTCTGGCA
2094 171_HRV58    ACCCAAGAATCGTGATGACTTTACATGGCAATCAGGCACAAATGCATCTGTTTTCTGGCA
2095 172_HRV58a   ACCCAAGAATCGTGATGACTTTACATGGCAATCAGGCACAAATGCATCTGTTTTCTGGCA
2096 173_HRV58b   ACCCAAGAATCGTGATGACTTTACATGGCAATCAGGCACAAATGCATCTGTTTTCTGGCA
2097 174_HRV12a   ACCCAAAAAACGTGATGATTACACATGGCAATCTGGCACCAACGCCTCAGTTTTTTGGCA
2098 175_HRV12b   ACCCAAAAAACGTGATGATTACACATGGCAATCTGGCACCAACGCCTCAGTTTTTTGGCA
2099 176_HRV12    ACCCAAAAAACGTGATGATTACACATGGCAATCTGGCACCAACGCCTCAGTTTTTTGGCA
2100 177_HRV78a   ACCAAAGAAGAGAGATGACTATACTTGGCAGTCAGGCACCAATGCATCTGTGTTTTGGCA
2101 178_HRV78b   ACCAAAGAAGAGAGATGACTATACTTGGCAGGCACCAATGCATCTGTGTTTTGGCA
2102 179_HRV78    ACCAAAGAAGAGAGATGACTATACTTGGCAGTCAGGCACCAATGCATCTGTGTTTTGGCA
2103 180_HRV20    ACCAAAGACTAGAGATGACTACACATGGCAATCAGGGACAAATGCATCAGTATTTTGGCA
2104 181_HRV20a   ACCAAAGACTAGAGATGACTACACATGGCAATCAGGGACAAATGCATCAGTATTTTGGCA
2105 182_HRV20b   ACCAAAGACTAGAGATGACTACACATGGCAATCAGGGACAAATGCATCAGTATTTTGGCA
2106 183_HRV68    ACCAAAAACTAGAGATGATTACACATGGCAGTCAGGCACTAATGCATCAGTGTTTTGGCA
2107 184_HRV68a   ACCAAAAACTAGAGATGATTACACATGGCAGTCAGGCACTAATGCATCAGTGTTTTGGCA
2108 185_HRV68b   ACCAAAAACTAGAGATGATTACACATGGCAGTCAGGCACTAATGCATCAGTGTTTTGGCA
2109 186_HRV28    CCCCACTACCAGAAATGATTACACATGGCAATCCAGTACCAATGCCTCTGTTTTCTGGCA
2110 187_HRV28a   CCCCACTACCAGAAATGATTACACATGGCAATCCAGTACCAATGCCTCTGTTTTCTGGCA
2111 188_HRV28b   CCCCACTACCAGAAATGATTACACATGGCAATCCAGTACCAATGCCTCTGTTTTCTGGCA
2112 189_HRV53a   ACCCAAAACCAGAGATGACTATACCTGGCAATCTGGAACTAATGCTTCAGTCTTTTGGCA
2113 190_HRV53b   ACCCAAAACCAGAGATGACTATACCTGGCAATCTGGAACTAATGCTTCAGTCTTTTGGCA
2114 191_HRV53    ACCCAAAACCAGAGATGACTATACCTGGCAATCTGGAACTAATGCTTCAGTCTTTTGGCA
2115 192_HRV46a   ACCGAGATATCGGAATGATTATACTTGGCAGTCTGGTACTAATGCTTCAGTGTTCTGGCA
2116 193_HRV46b   ACCGAGATATCGGAATGATTATACTTGGCAGTCTGGTACTAATGCTTCAGTGTTCTGGCA
2117 194_HRV46    ACCGAGATATCGGAATGATTATACTTGGCAGTCTGGTACTAATGCTTCAGTGTTCTGGCA
2118 195_HRV80a   GCCAAACAAACGCAATGATTATACTTGGCAGTCTGGCACGAATGCTTCAGTCTTCTGGCA
2119 196_HRV80b   GCCAAACAAACGCAATGATTATACTTGGCAGTCTGGCACGAATGCTTCAGTCTTCTGGCA
2120 197_HRV80    GCCAAACAAACGCAATGATTATACTTGGCAGTCTGGCACGAATGCTTCAGTCTTCTGGCA
2121 198_HRV51    TCCACTTACTAGGAAAGATGATGAGTGGCAATCAGGAACTAATGCTTCAGTATTCTGGCA
2122 199_HRV51a   TCCACTTACTAGGAAAGATGATGAGTGGCAATCAGGAACTAATGCTTCAGTATTCTGGCA
2123 200_HRV51b   TCCACTTACTAGGAAAGATGATGAGTGGCAATCAGGAACTAATGCTTCAGTATTCTGGCA
2124 201_HRV65a   TCCAAAAACTAGAAAAGATGAAGAGTGGCAGACAGGAACTAATGCTTCAGTCTTTTGGCA
2125 202_HRV65b   TCCAAAAACTAGAAAAGATGAAGAGTGGCAGACAGGAACTAATGCTTCAGTCTTTTGGCA
2126 203_HRV65    TCCAAAAACTAGAAAAGATGAAGAGTGGCAGACAGGAACTAATGCTTCAGTCTTTTGGCA
2127 204_HRV71a   ACCAGAGACCAGGGATGCCGATGAATGGCAGTCTGGAACTAATGCATCAGTCTTTTGGCA
2128 205_HRV71b   ACCAGAGACCAGGGATGCCGATGAATGGCAGTCTGGAACTAATGCATCAGTCTTTTGGCA
2129 206_HRV71    ACCAGAGACCAGGGATGCCGATGAATGGCAGTCTGGAACTAATGCATCAGTCTTTTGGCA
2130 207_HRV8     TCCAGATAAAAGGATGCACGATGCCTGGCAAACCAGTACAAATGCCTCAGTCTTCTGGCA
2131 208_HRV95    TCCAGATAAAAGGATGCACGATGCCTGGCAAACCAGTACAAATGCCTCAGTCTTCTGGCA
2132 209_HRV45    CCCTGTTAGTAGAACTGACAACACTTGGCAATCTAGCACAAATGCATCAGTCTTTTGGCA
2133 210_HRV45a   CCCTGTTAGTAGAACTGACAACACTTGGCAATCTAGCACAAATGCATCAGTCTTTTGGCA
2134 211_HRV45b   CCCTGTTAGTAGAACTGACAACACTTGGCAATCTAGCACAAATGCATCAGTCTTTTGGCA
2135 GROUP_1      -CC--------G-------------TGG-A--C--G-A--AA----TC----TT-TGGCA
2136
2137 1_HRV1A1|d   ACATGGACAGCCATTTCCTAGATTTTCTTTACCATTTCTTAGCATTGCATCAGCTTATTA
2138 2_HRV1A2|d   ACATGGACAGCCATTTCCTAGATTTTCTTTACCATTTCTTAGCATTGCATCAGCTTATTA
2139 3_HRV1A|cD   ACATGGACAGCCATTTCCTAGATTTTCTTTACCATTTCTTAGCATTGCATCAGCTTATTA
2140 4_HRV1B1|d   ACATGGACAACCGTTCCCTAGATTCTCTTTACCATTTCTTAGCATTGCATCAGCTTATTA
2141 5_HRV1B2|d   ACATGGACAACCGTTCCCTAGATTCTCTTTACCATTTCTTAGCATTGCATCAGCTTATTA
2142 6_HRV1B      ACATGGACAACCGTTCCCTAGATTCTCTTTACCATTTCTTAGCATTGCATCAGCTTATTA
2143 7_HRV40a|d   ACATGGTCAAACTTTCCCTAGATTTTCTTTACCTTTCCTAAGCATAGCTTCAGCATACTA
2144 8_HRV40b|d   ACATGGTCAAACTTTCCCTAGATTTTCTTTACCTTTCCTAAGCATAGCTTCAGCATACTA
2145 9_HRV40      ACATGGTCAAACTTTCCCTAGATTTTCTTTACCTTTCCTAAGCATAGCTTCAGCATACTA
```

FIG. D7 CONT'D 03.trace                                                                    9/20/2007 5:03 PM

```
2146 10_HRV85     ACATGGGCAAACTTTCCCCAGATTTTCCTTACCTTTCTTGAGTGTTGCTTCAGCATATTA
2147 11_HRV85a|   ACATGGGCAAACTTTCCCCAGATTTTCCTTACCTTTCTTGAGTGTTGCTTCAGCATATTA
2148 12_HRV85b|   ACATGGGCAAACTTTCCCCAGATTTTCCTTACCTTTCTTGAGTGTTGCTTCAGCATATTA
2149 13_HRV56a|   ACATGGCCAAGCTTTCCCCAGATTCTCTCTACCTTTCTTAAGTATTGCTTCTGCTTATTA
2150 14_HRV56b|   ACATGGCCAAGCTTTCCCCAGATTCTCTCTACCTTTCTTAAGTATTGCTTCTGCTTATTA
2151 15_HRV56     ACATGGCCAAGCTTTCCCCAGATTCTCTCTACCTTTCTTAAGTATTGCTTCTGCTTATTA
2152 16_HRV54     ACATGGCCAAGCTTATCCAAGATTCTCTTTACCATTTTTAAGTATTGCATCTGCTTACTA
2153 17_HRV98     GCATGGTCAGGCCTATCCAAGATTCTCTACCATTCTTGAGCATTGCATCTGCTTACTA
2154 18_HRV59a|   ACATGGACAAACATTCCCAAGATTTTCATTGCCCTTCCTGAGCATAGCATCAGCTTATTA
2155 19_HRV59b|   ACATGGACAAACATTCCCAAGATTTTCATTGCCCTTCCTGAGCATAGCATCAGCTTATTA
2156 20_HRV59     ACATGGACAAACATTCCCAAGATTTTCATTGCCCTTCCTGAGCATAGCATCAGCTTATTA
2157 21_HRV63     ACATGGACAAGCTTTTCCAAGGTTTTCTCTACCTTTCTTGAGTATTGCATCAGCATATTA
2158 22_HRV63b|   ACATGGACAAGCTTTTCCAAGGTTTTCTCTACCTTTCTTGAGTATTGCATCAGCATATTA
2159 23_HRV63a|   ACATGGACAAGCTTTTCCAAGGTTTTCTCTACCTTTCTTGAGTATTGCATCAGCATATTA
2160 24_HRV39     ACACGGACAGCCTTACCCTAGATTTTCATTACCATTTCTAAGCATAGCCTCAGCATATTA
2161 25_HRV39a|   ACACGGACAGCCTTACCCTAGATTTTCATTACCATTTCTAAGCATAGCCTCAGCATATTA
2162 26_HRV39b|   ACACGGACAGCCTTACCCTAGATTTTCATTACCATTTCTAAGCATAGCCTCAGCATATTA
2163 27_HRV10a|   ACATGGACAACCTTTCCCTAGATTTTCTTTACCCTTCTTAAGCATTGCATCTGCTTACTA
2164 28_HRV10b|   ACATGGACAACCTTTCCCTAGATTTTCTTTACCCTTCTTAAGCATTGCATCTGCTTACTA
2165 29_HRV10     ACATGGACAACCTTTCCCTAGATTTTCTTTACCCTTCTTAAGCATTGCATCTGCTTACTA
2166 30_HRV100a   GCATGGGCAGCCATTCCCTAGAATTTCTTTACCTTTCTTGAGCATTGCTTCTGCATACTA
2167 31_HRV100b   GCATGGGCAGCCATTCCCTAGAATTTCTTTACCTTTCTTGAGCATTGCTTCTGCATACTA
2168 32_HRV100    GCATGGGCAGCCATTCCCTAGAATTTCTTTACCTTTCTTGAGCATTGCTTCTGCATACTA
2169 33_HRV66     ACTTGGACAACCATTCTCGCTACCTTTCTAGGCATAGCTTCAGCATATTA
2170 34_HRV66b|   ACTTGGACAACCATTCCCAAGATTCTCGCTACCTTTTCTAGGCATAGCTTCAGCATATTA
2171 35_HRV66a|   ACTTGGACAACCATTCCCAAGATTCTCGCTACCTTTTCTAGGCATAGCTTCAGCATATTA
2172 36_HRV77a|   ACATGGACAACCATTCCCAAGATTTTCACTACCTTTTCTGAGTATTGCTTCAGCTTACTA
2173 37_HRV77b|   ACATGGACAACCATTCCCAAGATTTTCACTACCTTTTCTGAGTATTGCTTCAGCTTACTA
2174 38_HRV77     ACATGGACAACCATTCCCAAGATTTTCACTACCTTTTCTGAGTATTGCTTCAGCTTACTA
2175 39_HRV62a    ACATGGGCAACCCTTTCCTAGATTTTCATTACCTTTTTTGAGTGTTGCATCTGCTTATTA
2176 40_HRV62b    ACATGGGCAACCCTTTCCTAGATTTTCATTACCTTTTTTGAGTGTTGCATCTGCTTATTA
2177 41_HRV25     ACATGGACAACCCTTCCCAAGATTTTCATTGCCATTTCTGAGTGTTGCATCTGCTTATTA
2178 42_HRV29a    ACATGGTCAGCCTTTCCCAAGATTTTCATTACCATTCCTAAGTGTTGCATCTGCTTATTA
2179 43_HRV29b    ACATGGTCAGCCTTTCCCAAGATTTTCATTACCATTCCTAAGTGTTGCATCTGCTTATTA
2180 44_HRV44a    ACATGGTCAACCTTTCCCAAGATTTTCATTACCATTTCTAAGTGTTGCATCTGCCTATTA
2181 45_HRV44b    ACATGGTCAACCTTTCCCAAGATTTTCATTGCCATTTCTAAGTGTTGCATCTGCATATTA
2182 46_HRV31     ACATGGACAACCCTTTCCAAGATTTACATTACCCTTTTTGAGTGTCGCATCCGCTTATTA
2183 47_HRV31a|   ACATGGACAACCCTTTCCAAGATTTACATTACCCTTTTTGAGTGTCGCATCCGCTTATTA
2184 48_HRV31b|   ACATGGACAACCCTTTCCAAGATTTACATTACCCTTTTTGAGTGTCGCATCCGCTTATTA
2185 49_HRV47     ACAAGGGCAACCCTTTCCAAGATTTTCATTACCATTTTTGAGTGTTGCATCTGCTTATTA
2186 50_HRV47a|   ACAAGGGCAACCCTTTCCAAGATTTTCATTACCATTTTTGAGTGTTGCATCTGCTTATTA
2187 51_HRV47b|   ACAAGGGCAACCCTTTCCAAGATTTTCATTACCATTTTTGAGTGTTGCATCTGCTTATTA
2188 52_HRV11     ATATGGTCAAACATACCCAAGATTTTCTCTACCTTTCATGAGTATAGCACAGCATATTA
2189 53_HRV11b|   ATATGGTCAAACATACCCAAGATTTTCTCTACCTTTCATGAGTATAGCCTCAGCATATTA
2190 54_HRV11a|   ATATGGTCAAACATACCCAAGATTTTCTCTACCTTTCATGAGTATAGCCTCAGCATATTA
2191 55_HRV76     ATATGGACAAACATACCCTAGGTTTTCATTACCCTTTCTAAGTATAGCTTCAGCTTATTA
2192 56_HRV76b|   ATATGGACAAACATACCCTAGGTTTTCATTACCCTTTCTAAGTATAGCTTCAGCTTATTA
2193 57_HRV76a|   ATATGGACAAACATACCCTAGGTTTTCATTACCCTTTCTAAGTATAGCTTCAGCTTATTA
2194 58_HRV33     ATATGGACAAACATATCCTAGGTTCTCATTACCTTTCCTTAGCATAGCTTCAGCATATTA
2195 59_HRV33b|   ATATGGACAAACATATCCTAGGTTCTCATTACCTTTCCTTAGCATAGCTTCAGCATATTA
2196 60_HRV33a|   ATATGGACAAACATATCCTAGGTTCTCATTACCTTTCCTTAGCATAGCTTCAGCATATTA
2197 61_HRV24a|   ACATGGACAAACCTATCCTAGATTTTCCCTTCCTTTTCTGAGTGTAGCCTCTGCATATTA
2198 62_HRV24b|   ACATGGACAAACCTATCCTAGATTTTCCCTTCCTTTTCTGAGTGTAGCCTCTGCATATTA
2199 63_HRV24     ACATGGACAAACCTATCCTAGATTTTCCCTTCCTTTTCTGAGTGTAGCCTCTGCATATTA
2200 64_HRV90     ACATGGACAAACATACCCTAGATTTCACTTCCTTTCTTAAGTATAGCTTCTGCATACTA
2201 65_HRV90a|   ACATGGACAAACATACCCAGATTTTCACTTCCTTTCTTAAGTATAGCTTCTGCATACTA
2202 66_HRV90b|   ACATGGACAAACATACCCAGATTTTCACTTCCTTTCTTAAGTATAGCTTCTGCATACTA
2203 67_HRV34     ACATGGTCAAACATACCCAGATTTTCCCTCCCTTTCTTAAGCATAGCCTCAGCATACTA
2204 68_HRV34b|   ACATGGTCAAACATACCCAGATTTTCCCTCCCTTTCTTAAGCATAGCCTCAGCATACTA
2205 69_HRV34a|   ACATGGTCAAACATACCCAGATTTTCCCTCCCTTTCTTAAGCATAGCCTCAGCATACTA
2206 70_HRV50a|   ACATGGTCAAACATACCCTAGATTCTCTCTACCATTCTTGAGTATAGCATCTGCATATTA
2207 71_HRV50b|   ACATGGTCAAACATACCCTAGATTCTCTCTACCATTCTTGAGTATAGCATCTGCATATTA
2208 72_HRV50     ACATGGTCAAACATACCCTAGATTCTCTCTACCATTCTTGAGTATAGCATCTGCATATTA
2209 73_HRV18a|   ACATGGTCAAACATACCCCAGATTTTCACTTCCTTTCCTCAGTATAGCATCAGCTTATTA
2210 74_HRV18b|   ACATGGTCAAACATACCCCAGATTTTCACTTCCTTTCCTCAGTATAGCATCAGCTTATTA
```

FIG. D7 CONT'D

03.trace                                                                    9/20/2007 5:03 PM

```
2211  75_HRV18     ACATGGTCAAACATACCCCAGATTTTCACTTCCTTTCCTCAGTATAGCATCAGCTTATTA
2212  76_HRV55     ACATGGGCAAACATACCCTAGATTTTCACTTCCTTTCCTAAGTATAGCTTCTGCTTATTA
2213  77_HRV55b|   ACATGGGCAAACATACCCTAGATTTTCACTTCCTTTCCTAAGTATAGCTTCTGCTTATTA
2214  78_HRV55a|   ACATGGGCAAACATACCCTAGATTTTCACTTCCTTTCCTAAGTATAGCTTCTGCTTATTA
2215  79_HRV57     ACATGGTCAAACATACCCTAGATTTTCCTTGCCTTTCTTAAGTATAGCCTCAGCATATTA
2216  80_HRV57a|   ACATGGTCAAACATACCCTAGATTTTCCTTGCCTTTCTTAAGTATAGCCTCAGCATATTA
2217  81_HRV57b|   ACATGGTCAAACATACCCTAGATTTTCCTTGCCTTTCTTAAGTATAGCCTCAGCATATTA
2218  82_HRV21     GCATGGCCAGACTTATCCTAGATTTTCATTACCCTTCCTTAGTATAGCATCAGCATACTA
2219  83_HRVHan    GCATGGTCAAACTTATCCTAGATTTTCACTACCCTTCCTTAGTATAGCATCAGCATATTA
2220  84_HRV43     ACATGGTCAAACATTTCCAAGATTTTCCTTACCTTTTCTGAGCATAGCATCAGCATATTA
2221  85_HRV43b|   ACATGGTCAAACATTTCCAAGATTTTCCTTACCTTTTCTGAGCATAGCATCAGCATATTA
2222  86_HRV43a|   ACATGGTCAAACATTTCCAAGATTTTCCTTACCTTTTCTGAGCATAGCATCAGCATATTA
2223  87_HRV75     ACATGGACAAACATTTCCAAGATTTTCACTACCATTTCTGAGCATTGCATCAGCATATTA
2224  88_HRV75b|   ACATGGACAAACATTTCCAAGATTTTCACTACCATTTCTGAGCATTGCATCAGCATATTA
2225  89_HRV75a|   ACATGGACAAACATTTCCAAGATTTTCACTACCATTTCTGAGCATTGCATCAGCATATTA
2226  96_HRV9a|d   ACATGGACAATCATATCCCAGATTTTCACTTCCGTTTTTGAGCATTGCCTCTGCATATTA
2227  97_HRV9b|d   ACATGGACAATCATATCCCAGATTTTCACTTCCGTTTTTGAGCATTGCCTCTGCATATTA
2228  98_HRV9      ACATGGACAATCATATCCCAGATTTTCACTTCCGTTTTTGAGCATTGCCTCTGCATATTA
2229  99_HRV32     GCATGGACAGGCATATCCCAGGTTTTCACTTCCATTTCTAAGTATTGCCTCTGCATACTA
2230  100_HRV32a   GCATGGACAGGCATATCCCAGGTTTTCACTTCCATTTCTAAGTATTGCCTCTGCATACTA
2231  101_HRV32b   GCATGGACAGGCATATCCCAGGTTTTCACTTCCATTTCTAAGTATTGCCTCTGCATACTA
2232  102_HRV67    ACATGGACAATCATACCCCAGATTCTCACTACCATTCTTAAGTATTGCCTCTGCTTATTA
2233  103_HRV67a   ACATGGACAATCATACCCCAGATTCTCACTACCATTCTTAAGTATTGCCTCTGCTTATTA
2234  104_HRV67b   ACATGGACAATCATACCCCAGATTCTCACTACCATTCTTAAGTATTGCCTCTGCTTATTA
2235  105_HRV15    ACATGGTCAACCTTACCCCAGATTTTCTTTGCCTTTTCTCAGCATTGCATCTGCTTACTA
2236  106_HRV15a   ACATGGTCAACCTTACCCCAGATTTTCTTTGCCTTTTCTCAGCATTGCATCTGCTTACTA
2237  107_HRV15b   ACATGGTCAACCTTACCCCAGATTTTCTTTGCCTTTTCTCAGCATTGCATCTGCTTACTA
2238  108_HRV74a   GCATGGACAGCCATACCCTAGATTCTCATTACCTTTCCTTAGCATAGCATCTGCTTATTA
2239  109_HRV74b   GCATGGACAGCCATACCCTAGATTCTCATTACCTTTCCTTAGCATAGCATCTGCTTATTA
2240  110_HRV74    GCATGGACAGCCATACCCTAGATTCTCATTACCTTTCCTTAGCATAGCATCTGCTTATTA
2241  111_HRV38a   ATATGGTCAGACATATCCTCGATTTTCCTTACCTTTCTTAAGCATTGCATCTGTCTATTA
2242  112_HRV38b   ATATGGTCAGACATATCCTCGATTTTCCTTACCTTTCTTAAGCATTGCATCTGTCTATTA
2243  113_HRV38    ATATGGTCAGACATATCCTCGATTTTCCTTACCTTTCTTAAGCATTGCATCTGTCTATTA
2244  114_HRV60    GCATGGACAAACATACCCTAGATTTTCACTTCCATTTCTAAGTATTGCATCTGCCTACTA
2245  115_HRV60a   GCATGGACAAACATACCCTAGATTTTCACTTCCATTTCTAAGTATTGCATCTGCCTACTA
2246  116_HRV60b   GCATGGACAAACATACCCTAGATTTTCACTTCCATTTCTAAGTATTGCATCTGCCTACTA
2247  117_HRV64a   ACACGGTCAACCATACCCTCGATTTTCTCTCCCTTTCCTTAGCATAGCCTCAGCATATTA
2248  118_HRV64b   ACACGGTCAACCATACCCTCGATTTTCTCTCCCTTTCCTTAGCATAGCCTCAGCATATTA
2249  119_HRV64    ACACGGTCAACCATACCCTCGATTTTCTCTCCCTTTCCTTAGCATAGCCTCAGCATATTA
2250  120_HRV94a   ACATGGTCAACCCTACCCTCGATTCTCACTTCCATTCTTAGTATAGCCTCAGCATATTA
2251  121_HRV94b   ACATGGTCAACCCTACCCTCGATTCTCACTTCCATTTCTTAGTATAGCCTCAGCATATTA
2252  122_HRV94    ACATGGTCAACCCTACCCTCGATTCTCACTTCCATTTCTTAGTATAGCCTCAGCATATTA
2253  123_HRV22    GCATGGTCAACCTTATCCCCGATTCTCACTCCCTTTCCTCAGTGTAGCTTCAGCATATTA
2254  124_HRV22a   GCATGGTCAACCTTATCCCCGATTCTCACTCCCTTTCCTCAGTGTAGCTTCAGCATATTA
2255  125_HRV22b   GCATGGTCAACCTTATCCCCGATTCTCACTCCCTTTCCTCAGTGTAGCTTCAGCATATTA
2256  126_HRV82    ACATGGACAACCTTACCCTCGCTTCTCACTTCCTTTCTTGAGTATAGCCTCAGCTTACTA
2257  127_HRV82b   ACATGGACAACCTTACCCTCGCTTCTCACTTCCTTTCTTGAGTATAGCCTCAGCTTACTA
2258  128_HRV82a   ACATGGACAACCTTACCCTCGCTTCTCACTTCCTTTCTTGAGTATAGCCTCAGCTTACTA
2259  129_HRV19    ACATGGTCAACCATACCCAAGATTTTCATTACCTTTTCTAAGTATAGCTTCTGCATATTA
2260  130_HRV19a   ACATGGTCAACCATACCCAAGATTTTCATTACCTTTTCTAAGTATAGCTTCTGCATATTA
2261  131_HRV19b   ACATGGTCAACCATACCCAAGATTTTCATTACCTTTTCTAAGTATAGCTTCTGCATATTA
2262  132_HRV13    ACATGGTCAAATTTACCCCCGATTCTCTTTACCATTTCTTAGTATTGCATCTGCATATTA
2263  133_HRV13a   ACATGGTCAAATTTACCCCCGATTCTCTTTACCATTTCTTAGTATTGCATCTGCATATTA
2264  134_HRV13b   ACATGGTCAAATTTACCCCCGATTCTCTTTACCATTTCTTAGTATTGCATCTGCATATTA
2265  135_HRV41    GTATGGTCAAGTTTACCCTAGGTTTTCTCTACCATTTCTTAGCATTGCTTCCGCATATTA
2266  136_HRV41a   GTATGGTCAAGTTTACCCTAGGTTTTCTCTACCATTTCTTAGCATTGCTTCCGCATATTA
2267  137_HRV41b   GTATGGTCAAGTTTACCCTAGGTTTTCTCTACCATTTCTTAGCATTGCTTCCGCATATTA
2268  138_HRV73    ACATGGTCAAACTTACCCCAGATTCTCATTACCATTCCTTAGTATAGCATCCGCATATTA
2269  139_HRV73b   ACATGGTCAAACTTACCCCAGATTCTCATTACCATTCCTTAGTATAGCATCCGCATATTA
2270  140_HRV73a   ACATGGTCAAACTTACCCCAGATTCTCATTACCATTCCTTAGTATAGCATCCGCATATTA
2271  141_HRV61    ACATGGTCAAGCTTATCCCAGATTTTCATTACCATTCCTTAAGTATTGCATCTGCATATTA
2272  142_HRV61a   ACATGGTCAAGCTTATCCCAGATTTTCATTACCATTCCTAAGTATTGCATCTGCATATTA
2273  143_HRV61b   ACATGGTCAAGCTTATCCCAGATTTTCATTACCATTCCTAAGTATTGCATCTGCATATTA
2274  144_HRV96    GCACGGGCAAGCATATCCTAGATTTTCACTGCCTTTCCTTAGTATTGCCTCTGCATATTA
2275  145_HRV96b   GCACGGGCAAGCATATCCTAGATTTTCACTGCCTTTCCTTAGTATTGCCTCTGCATATTA
```

FIG. D7 CONT'D

03.trace                                                                    9/20/2007 5:03 PM

```
2276  146_HRV96a   GCACGGGCAAGCATATCCTAGATTTTCACTGCCTTTCCTTAGTATTGCCTCTGCATATTA
2277   90_HRV16a|  GCATGGGCAACCTTTCCCTCGCTTTTCACTTCCCTTTTTGAGTATTGCATCAGCATATTA
2278   91_HRV16b|  GCATGGGCAACCTTTCCCTCGCTTTTCACTTCCCTTTTTGAGTATTGCATCAGCATATTA
2279   92_1AYM_A   GCATGGGCAACCTTTCCCTCGCTTTTCACTTCCCTTTTTGAGTATTGCATCAGCATATTA
2280   93_HRV81a|  ACATGGGCAACCCTTTCCCCGGTTTTCACTCCCTTTTCTAAGTGTAGCATCAGCATATTA
2281   94_HRV81b|  ACATGGGCAACCCTTTCCCCGGTTTTCACTCCCTTTTCTAAGTGTAGCATCAGCATATTA
2282   95_HRV81    ACATGGGCAACCCTTTCCCCGGTTTTCACTCCCTTTTCTAAGTGTAGCATCAGCATATTA
2283  147_HRV2     ACATGGACAGGCTTATCCAAGATTTTCCTTACCTTTCCTAAGTGTGGCATCTGCTTATTA
2284  148_HRV2a|   ACATGGACAGGCTTATCCAAGATTTTCCTTACCTTTCCTAAGTGTGGCATCTGCTTATTA
2285  149_HRV2b|   ACATGGACAGGCTTATCCAAGATTTTCCTTACCTTTCCTAAGTGTGGCATCTGCTTATTA
2286  150_HRV49a   ACATGGGCAAGCATACCCAAGATTTTCTCTACCCTTTTTGAGTGTAGCTTCAGCTTACTA
2287  151_HRV49b   ACATGGGCAAGCATACCCAAGATTTTCTCTACCCTTTTTGAGTGTAGCTTCAGCTTACTA
2288  152_HRV49    ACATGGGCAAGCATACCCAAGATTTTCTCTACCCTTTTTGAGTGTAGCTTCAGCTTACTA
2289  153_HRV23a   ACATGGACAAACATATCCAAGGTTCTCCTTACCCTTTTTGAGTGTGGCATCTGCTTATTA
2290  154_HRV23b   ACATGGACAAACATATCCAAGGTTCTCCTTACCCTTTTTGAGTGTGGCATCTGCTTATTA
2291  155_HRV23    ACATGGACAAACATATCCAAGGTTCTCCTTACCCTTTTTGAGTGTGGCATCTGCTTATTA
2292  156_HRV30a   ACACGGACAAACATACCCAAGATTCTCCCTACCATTTTTGAGTGTAGCATCTGCTTATTA
2293  157_HRV30b   ACACGGACAAACATACCCAAGATTCTCCCTACCATTTTTGAGTGTAGCATCTGCTTATTA
2294  158_HRV30    ACACGGACAAACATACCCAAGATTCTCCCTACCATTTTTGAGTGTAGCATCTGCTTATTA
2295  159_HRV7     GGAGGGTCAACCATACCCTAGATTCACAATTCCTTTTATGAGTATTGCATCAGCTTATTA
2296  160_HRV7b|   GGAGGGTCAACCATACCCTAGATTCACAATTCCTTTTATGAGTATTGCATCAGCTTATTA
2297  161_HRV7a|   GGAGGGTCAACCATACCCTAGATTCACAATTCCTTTTATGAGTATTGCATCAGCTTATTA
2298  162_HRV88    AGAAGGACAACCATACCCAAGATTTACCATTCCCTTTATGAGTATTGCATCAGCTTACTA
2299  163_HRV88a   AGAAGGACAACCATACCCAAGATTTACCATTCCCTTTATGAGTATTGCATCAGCTTACTA
2300  164_HRV88b   AGAAGGACAACCATACCCAAGATTTACCATTCCCTTTATGAGTATTGCATCAGCTTACTA
2301  165_HRV36a   AGAAGGGCAACCATATCCTAGATTTACAATCCCCTTTATGAGTATTGCATCAGCTTATTA
2302  166_HRV36b   AGAAGGGCAACCATATCCTAGATTTACAATCCCCTTTATGAGTATTGCATCAGCTTATTA
2303  167_HRV36    AGAAGGGCAACCATATCCTAGATTTACAATCCCCTTTATGAGTATTGCATCAGCTTATTA
2304  168_HRV89a   AGAAGGACAACCATACCCCAGATTCACAATCCCTTTTATGAGCATTGCATCAGCCTATTA
2305  169_HRV89b   AGAAGGACAACCATACCCCAGATTCACAATCCCTTTTATGAGCATTGCATCAGCCTATTA
2306  170_HRV89    AGAAGGACAACCATACCCCAGATTCACAATCCCTTTTATGAGCATTGCATCAGCCTATTA
2307  171_HRV58    GGAAGGACAACCATACCCTAGATTTACAATCCCTTTTATGAGCATTGCATCAGCTTACTA
2308  172_HRV58a   GGAAGGACAACCATACCCTAGATTTACAATCCCTTTTATGAGCATTGCATCAGCTTACTA
2309  173_HRV58b   GGAAGGACAACCATACCCTAGATTTACAATCCCTTTTATGAGCATTGCATCAGCTTACTA
2310  174_HRV12a   GGAAGGTCAACCTTACCCCAGATTCACAATCCCTTTATTAGTATTGCCTCAGCATATTA
2311  175_HRV12b   GGAAGGTCAACCTTACCCCAGATTCACAATCCCTTTTATTAGTATTGCCTCAGCATATTA
2312  176_HRV12    GGAAGGTCAACCTTACCCCAGATTCACAATCCCTTTTATTAGTATTGCCTCAGCATATTA
2313  177_HRV78a   ACAAGGTCAAACATACCCCAGGTTCTCTATACCATTTTCTAGTATTGCCTCAGCTTATTA
2314  178_HRV78b   ACAAGGTCAAACATACCCCAGGTTCTCTATACCATTTTCTAGTATTGCCTCAGCTTATTA
2315  179_HRV78    ACAAGGTCAAACATACCCCAGGTTCTCTATACCATTTTCTAGTATTGCCTCAGCTTATTA
2316  180_HRV20    GCAGGGCCAACCTTACCCCAGATTTACCATTCCATTTATGAGTATAGCTTCAGCATATTA
2317  181_HRV20a   GCAGGGCCAACCTTACCCCAGATTTACCATTCCATTTATGAGTATAGCTTCAGCATATTA
2318  182_HRV20b   GCAGGGCCAACCTTACCCCAGATTTACCATTCCATTTATGAGTATAGCTTCAGCATATTA
2319  183_HRV68    ACAAGGACAACCTTACCCCAGATTTACCATTCCATTTATGAGTATAGCTTCAGCATATTA
2320  184_HRV68a   ACAAGGACAACCTTACCCCAGATTTACCATTCCATTTATGAGTATAGCTTCAGCATATTA
2321  185_HRV68b   ACAAGGACAACCTTACCCCAGATTTACCATTCCATTTATGAGTATAGCTTCAGCATATTA
2322  186_HRV28    ACAAGGACAACCATATCCCAGATTCACTATACCTTTTATGAGTATTGCCTCAGCTTATTA
2323  187_HRV28a   ACAAGGACAACCATATCCCAGATTCACTATACCTTTTATGAGTATTGCCTCAGCTTATTA
2324  188_HRV28b   ACAAGGACAACCATATCCCAGATTCACTATACCTTTTATGAGTATTGCCTCAGCTTATTA
2325  189_HRV53a   ACAAGGACAACCATACCCTAGATTCACAATCCCTTTCATGAGTATTGCGTCAGCATATTA
2326  190_HRV53b   ACAAGGACAACCATACCCTAGATTCACAATCCCTTTCATGAGTATTGCGTCAGCATATTA
2327  191_HRV53    ACAAGGACAACCATACCCTAGATTCACAATCCCTTTCATGAGTATTGCGTCAGCATATTA
2328  192_HRV46a   GCAAGGGCAGCCATACCCTAGATTCACTATCCCGTTCATGAGTATAGCCTCAGCATATTA
2329  193_HRV46b   GCAAGGGCAGCCATACCCTAGATTCACTATCCCGTTCATGAGTATAGCCTCAGCATATTA
2330  194_HRV46    GCAAGGGCAGCCATACCCTAGATTCACTATCCCGTTCATGAGTATAGCCTCAGCATATTA
2331  195_HRV80a   ACAGGGTCAGCCATACCCCAGATTCACTATTCCATTCATGAGTATAGCCTCAGCTTATTA
2332  196_HRV80b   ACAGGGTCAGCCATACCCCAGATTCACTATTCCATTCATGAGTATAGCCTCAGCTTATTA
2333  197_HRV80    ACAGGGTCAGCCATACCCCAGATTCACTATTCCATTCATGAGTATAGCCTCAGCTTATTA
2334  198_HRV51    ACATGGACAACCATACCCTAGATTTACAATCCCTTTTGTAAGCATAGCCTCAGCATACTA
2335  199_HRV51a   ACATGGACAACCATACCCTAGATTTACAATCCCTTTTGTAAGCATAGCCTCAGCATACTA
2336  200_HRV51b   ACATGGACAACCATACCCTAGATTTACAATCCCTTTTGTAAGCATAGCCTCAGCATACTA
2337  201_HRV65a   GCATGGTCAACCATACCCCAGATTTACAATTCCTTTTGTGAGTATTGCCTCAGCATATTA
2338  202_HRV65b   GCATGGTCAACCATACCCCAGATTTACAATTCCTTTTGTGAGTATTGCCTCAGCATATTA
2339  203_HRV65    GCATGGTCAACCATACCCCAGATTTACAATTCCTTTTGTGAGTATTGCCTCAGCATATTA
2340  204_HRV71a   GCACGGCCAACCATACCCAAGGTTTACAATCCCCTTCATAAGCATTGCATCAGCATATTA
```

FIG. D7 CONT'D

```
03.trace                                                                    9/20/2007 5:03 PM 2341 205_HRV71b    GCACGGCCAACCATACCCAAGGTTTACAATCCCCTTCATAAGCATTGCATCAGCATATTA
2342 206_HRV71     GCACGGCCAACCATACCCAAGGTTTACAATCCCCTTCATAAGCATTGCATCAGCATATTA
2343 207_HRV8      AGTTGGACAAACTTATCCCAGATTCACCATACCTTTCTCCAGCATAGCATCAGCTTATTA
2344 208_HRV95     AGTTGGACAGACTTATCCCAGATTCACCATACCTTTCTCCAGTATAGCATCAGCTTATTA
2345 209_HRV45     GGTTGGTCAAACTTATCCCAGATTTTCTATACCTTTCTCAAGTATAGCTTCAGCTTACTA
2346 210_HRV45a    GGTTGGTCAAACTTATCCCAGATTTTCTATACCTTTCTCAAGTATAGCTTCAGCTTACTA
2347 211_HRV45b    GGTTGGTCAAACTTATCCCAGATTTTCTATACCTTTCTCAAGTATAGCTTCAGCTTACTA
2348 GROUP_1       ----GG-CA----T--CC--G--T--C--T-CC-TT-----G--T-GC-TC-G--TA-TA
2349
2350 1_HRV1A1|d    TATGTTTTATGATGGATATGATGGAGACAACACTTCTTCCAAGTATGGTAGCGTAGTTAC
2351 2_HRV1A2|d    TATGTTTTATGATGGATATGATGGAGACAACACTTCTTCCAAGTATGGTAGCGTAGTTAC
2352 3_HRV1A|cD    TATGTTTTATGATGGATATGATGGAGACAACACTTCTTCCAAGTATGGTAGCGTAGTTAC
2353 4_HRV1B1|d    CATGTTTTATGATGGATATGATGGAGATAATTCCTCTTCCAAATATGGTAGTATAGTCAC
2354 5_HRV1B2|d    CATGTTTTATGATGGATATGATGGAGATAATTCCTCTTCCAAATATGGTAGTATAGTCAC
2355 6_HRV1B       CATGTTTTATGATGGATATGATGGAGATAATTCCTCTTCCAAATATGGTAGTATAGTCAC
2356 7_HRV40a|d    CATGTTTTATGATGGATACGATGGTGATACATCGACCTCAAGATATGGCACATCAGTCAC
2357 8_HRV40b|d    CATGTTTTATGATGGATACGATGGTGATACATCGACCTCAAGATATGGCACATCAGTCAC
2358 9_HRV40       CATGTTTTATGATGGATACGATGGTGATACATCGACCTCAAGATATGGCACATCAGTCAC
2359 10_HRV85      CATGTTTTATGATGGTTATGATGGTGATACACCAGGCTCAATGTATGGGACGTCAGTCAC
2360 11_HRV85a|    CATGTTTTATGATGGTTATGATGGTGATACACCAGGCTCAATGTATGGGACGTCAGTCAC
2361 12_HRV85b|    CATGTTTTATGATGGTTATGATGGTGATACACCAGGCTCAATGTATGGGACGTCAGTCAC
2362 13_HRV56a|    CATGTTTTATGATGGTTATGATGGAGACACTTCAAGCTCCAGATATGGTACATCAGTTAC
2363 14_HRV56b|    CATGTTTTATGATGGTTATGATGGAGACACTTCAAGCTCCAGATATGGTACATCAGTTAC
2364 15_HRV56      CATGTTTTATGATGGTTATGATGGAGACACTTCAAGCTCCAGATATGGTACATCAGTTAC
2365 16_HRV54      CATGTTTTATGATGGGTATGATGGTGACGCACCTGGATCAAGATATGGGACTTCAGTTAC
2366 17_HRV98      CATGTTTACGATGGGTATGATGGTGATGCACCTGGATCAAGATATGGGAACCTCAGTCAC
2367 18_HRV59a|    CATGTTTTATGATGGTTATGATGGAGATAAATCTGAATCTAGGTATGGTGTGTCTGTAAC
2368 19_HRV59b|    CATGTTTTATGATGGTTATGATGGAGATAAATCTGAATCTAGGTATGGTGTGTCTGTAAC
2369 20_HRV59      CATGTTTTATGATGGTTATGATGGAGATAAATCTGAATCTAGGTATGGTGTGTCTGTAAC
2370 21_HRV63      CATGTTTTATGATGGATATGATGGAGATAAATCAAGCTCTAGGTATGGTGTTTCAGTTAC
2371 22_HRV63b|    CATGTTTTATGATGGATATGATGGAGATAAATCAAGCTCTAGGTATGGTGTTTCAGTTAC
2372 23_HRV63a|    CATGTTTTATGATGGATATGATGGAGATAAATCAAGCTCTAGGTATGGTGTTTCAGTTAC
2373 24_HRV39      TATGTTCTATGATGGATATGATGGTGATAAATCGTCATCTAGGTATGGTGTTTCTGTCAC
2374 25_HRV39a|    TATGTTCTATGATGGATATGATGGTGATAAATCGTCATCTAGGTATGGTGTTTCTGTCAC
2375 26_HRV39b|    TATGTTCTATGATGGATATGATGGTGATAAATCGTCATCTAGGTATGGTGTTTCTGTCAC
2376 27_HRV10a|    CATGTTCTATGATGGTTATGATGGTGATACACATGACTCACGTTATGGCACAACAGTGAT
2377 28_HRV10b|    CATGTTCTATGATGGTTATGATGGTGATACACATGACTCACGTTATGGCACAACAGTGAT
2378 29_HRV10      CATGTTCTATGATGGTTATGATGGTGATACACATGACTCACGTTATGGCACAACAGTGAT
2379 30_HRV100a    CATGTTTTATGATGGATATGATGGTGATACACATGATTCACACTATGGTACTACTGTAAT
2380 31_HRV100b    CATGTTTTATGATGGATATGATGGTGATACACATGATTCACACTATGGTACTACTGTAAT
2381 32_HRV100     CATGTTTTATGATGGATATGATGGTGATACACATGATTCACACTATGGTACTACTGTAAT
2382 33_HRV66      CATGTTCTATGATGGTTATGATGGAGATACTCCTGGGTCTCGTTATGGAACCACAGTAGT
2383 34_HRV66b|    CATGTTCTATGATGGTTATGATGGAGATACTCCTGGGTCTCGTTATGGAACCACAGTAGT
2384 35_HRV66a|    CATGTTCTATGATGGTTATGATGGAGATACTCCTGGGTCTCGTTATGGAACCACAGTAGT
2385 36_HRV77a|    CATGTTTTATGATGGCTATGATGGGGATACCTATGAATCACGTTATGGTACTACAGTGGT
2386 37_HRV77b|    CATGTTTTATGATGGCTATGATGGGGATACCTATGAATCACGTTATGGTACTACAGTGGT
2387 38_HRV77      CATGTTTTATGATGGCTATGATGGGGATACCTATGAATCACGTTATGGTACTACAGTGGT
2388 39_HRV62a     CATGTTTTATGATGGCTATAATGGTGATGACTATACAGCAAAATACGGTACCACCGTGGT
2389 40_HRV62b     CATGTTTTATGATGGCTATAATGGTGATGACTATACAGCAAAATACGGTACCACCGTGGT
2390 41_HRV25      CATGTTTTATGATGGCTATAATGGTGATGATCACACAGCGAGATATGGTACCACTGTGGT
2391 42_HRV29a     CATGTTTTATGATGGTTACAATGGAGGTGATCATACAGCAACTTATGGCACCACAGTGGT
2392 43_HRV29b     CATGTTTTATGATGGTTACAATGGAGGTGATCATACAGCAACTTATGGCACCACAGTGGT
2393 44_HRV44a     CATGTTTTATGATGGTTATAATGGTGATCATACAGCAACTTATGGCACCACAGTGGT
2394 45_HRV44b     CATGTTTTATGACGGTTATAATGGAGGTGATCATACAGCAACTTATGGCACCACAGTGGT
2395 46_HRV31      CATGTTTTATGATGGTTATGATGGAGACAAAAGTGGAGCCAAGTATGGTACTACAGTAGT
2396 47_HRV31a|    CATGTTTTATGATGGTTATGATGGAGACAAAAGTGGAGCCAAGTATGGTACTACAGTAGT
2397 48_HRV31b|    CATGTTTTATGATGGTTATGATGGAGACAAAAGTGGAGCCAAGTATGGTACTACAGTAGT
2398 49_HRV47      CATGTTTTATGATGGCTATAATGGTGACAGAAGTGGAGCCAAGTATGGCACCACAGTGGT
2399 50_HRV47a|    CATGTTTTATGATGGCTATAATGGTGACAGAAGTGGAGCCAAGTATGGCACCACAGTGGT
2400 51_HRV47b|    CATGTTTTATGATGGCTATAATGGTGACAGAAGTGGAGCCAAGTATGGCACCACAGTGGT
2401 52_HRV11      CATGTTTTATGATGGATATGATGGAGATCAACCAAACTCCAGATATGGTAATATAGTTAC
2402 53_HRV11b|    CATGTTTTATGATGGATATGATGGAGATCAACCAAACTCCAGATATGGTAATATAGTTAC
2403 54_HRV11a|    CATGTTTTATGATGGATATGATGGAGATCAACCAAACTCCAGATATGGTAATATAGTTAC
2404 55_HRV76      CATGTTTTATGATGGATATGATGGAGACCAACCTAGTTCTAGGTATGGTAATATAGTTAC
2405 56_HRV76b|    CATGTTTTATGATGGATATGATGGAGACCAACCTAGTTCTAGGTATGGTAATATAGTTAC
```

FIG. D7 CONT'D

03.trace                                                         9/20/2007 5:03 PM

```
2406  57_HRV76a|   CATGTTTTATGATGGATATGATGGAGACCAACCTAGTTCTAGGTATGGTAATATAGTTAC
2407  58_HRV33     CATGTTCTATGATGGATATGATGGGGACCAACCCAATTCCAGGTATGGTAATATGGTTAC
2408  59_HRV33b|   CATGTTCTATGATGGATATGATGATGGGGACCAACCCAATTCCAGGTATGGTAATATGGTTAC
2409  60_HRV33a|   CATGTTCTATGATGGATATGATGGGGACCAACCCAATTCCAGGTATGGTAATATGGTTAC
2410  61_HRV24a|   CATGTTTTATGATGGATATGATGGTGATCAACACGACTCAGTGTATGGTTCAGTTGTTAC
2411  62_HRV24b|   CATGTTTTATGATGGATATGATGGTGATCAACACGACTCAGTGTATGGTTCAGTTGTTAC
2412  63_HRV24     CATGTTTTATGATGGATATGATGGTGATCAACACGACTCAGTGTATGGTTCAGTTGTTAC
2413  64_HRV90     TATGTTTTATGATGGATATGATGGTGACCAAACTGATTCGAGATATGGTACCATTGTTAC
2414  65_HRV90a|   TATGTTTTATGATGGATATGATGGTGACCAAACTGATTCGAGATATGGTACCATTGTTAC
2415  66_HRV90b|   TATGTTTTATGATGGATATGATGGTGACCAAACTGATTCGAGATATGGTACCATTGTTAC
2416  67_HRV34     CATGTTTTATGATGGATATGATGGTGATCAACATGATTCAAGATATGGTACAGTAGTGAC
2417  68_HRV34b|   CATGTTTTATGATGGATATGATGGTGATCAACATGATTCAAGATATGGTACAGTAGTGAC
2418  69_HRV34a|   CATGTTTTATGATGGATATGATGGTGATCAACATGATTCAAGATATGGTACAGTAGTGAC
2419  70_HRV50a|   CATGTTTTATGATGGTTATGATGGTGATAAATCTACATCCAGGTATGGTACAGTAGTTAC
2420  71_HRV50b|   CATGTTTTATGATGGTTATGATGGTGATAAATCTACATCCAGGTATGGTACAGTAGTTAC
2421  72_HRV50     CATGTTTTATGATGGTTATGATGGTGATAAATCTACATCCAGGTATGGTACAGTAGTTAC
2422  73_HRV18a|   CATGTTCTATGATGGCTACGACGGTGACCAGACCTCATCGCGGTATGGCACAGTTGCAAC
2423  74_HRV18b|   CATGTTCTATGATGGCTACGACGGTGACCAGACCTCATCGCGGTATGGCACAGTTGCAAC
2424  75_HRV18     CATGTTCTATGATGGCTACGACGGTGACCAGACCTCATCGCGGTATGGCACAGTTGCAAC
2425  76_HRV55     CATGTTCTATGATGGATATGATGGTGACCAAACTGAGTCACGCTATGGCACTGTAGTCAC
2426  77_HRV55b|   CATGTTCTATGATGGATATGATGGTGACCAAACTGAGTCACGCTATGGCACTGTAGTCAC
2427  78_HRV55a|   CATGTTCTATGATGGATATGATGGTGACCAAACTGAGTCACGCTATGGCACTGTAGTCAC
2428  79_HRV57     CATGTTTTATGATGGATATGATGGTGACCAAACTGAATCAAGATATGGTACTGTAGTCAC
2429  80_HRV57a|   CATGTTTTATGATGGATATGATGGTGACCAAACTGAATCAAGATATGGTACTGTAGTCAC
2430  81_HRV57b|   CATGTTTTATGATGGATATGATGGTGACCAAACTGAATCAAGATATGGTACTGTAGTCAC
2431  82_HRV21     CATGTTTTATGATGGTTATGATGGTGACCAGACTGACTCACAATATGGTGCAGTAGTAAC
2432  83_HRVHan    CATGTTTTATGATGGTTATGATGGTGATCAGACTGACTCACAATATGGTGCAGTGGTGAC
2433  84_HRV43     CATGTTTTATGATGGATATGAAGGTGACCAAAAAACATCCCGTTATGGCACAATTGCAAG
2434  85_HRV43b|   CATGTTTTATGATGGATATGAAGGTGACCAAAAAACATCCCGTTATGGCACAATTGCAAG
2435  86_HRV43a|   CATGTTTTATGATGGATATGAAGGTGACCAAAAAACATCCCGTTATGGCACAATTGCAAG
2436  87_HRV75     CATGTTTTATGATGGATATGAAGGGGATCAAAATACATCCCGTTATGGCACCATTGCTAG
2437  88_HRV75b|   CATGTTTTATGATGGATATGAAGGGGATCAAAATACATCCCGTTATGGCACCATTGCTAG
2438  89_HRV75a|   CATGTTTTATGATGGATATGAAGGGGATCAAAATACATCCCGTTATGGCACCATTGCTAG
2439  96_HRV9a|d   CATGTTCTATGATGGTTATGATGGTGG---ACCAGATTCTCTGTATGGAACAATTGTAAC
2440  97_HRV9b|d   CATGTTCTATGATGGTTATGATGGTGG---ACCAGATTCTCTGTATGGAACAATTGTAAC
2441  98_HRV9      CATGTTCTATGATGGTTATGATGGTGG---ACCAGATTCTCTGTATGGAACAATTGTAAC
2442  99_HRV32     CATGTTTTATGATGGTTATGATGGTGG---GCCAGATTCACAATATGGAACAATTGTAAC
2443  100_HRV32a   CATGTTTTATGATGGTTATGATGGTGG---GCCAGATTCACAATATGGAACAATTGTAAC
2444  101_HRV32b   CATGTTTTATGATGGTTATGATGGTGG---GCCAGATTCACAATATGGAACAATTGTAAC
2445  102_HRV67    CATGTTTTATGATGGCTATGATGGTGG---ACCAGATTCACTATATGGCACCATAGTAAC
2446  103_HRV67a   CATGTTTTATGATGGCTATGATGGTGG---ACCAGATTCACTATATGGCACCATAGTAAC
2447  104_HRV67b   CATGTTTTATGATGGCTATGATGGTGG---ACCAGATTCACTATATGGCACCATAGTAAC
2448  105_HRV15    CATGTTCTATGATGGATATGATGGAGATTCCACTGAATCACATTATGGTACAGTGGTCAC
2449  106_HRV15a   CATGTTCTATGATGGATATGATGGAGATTCCACTGAATCACATTATGGTACAGTGGTCAC
2450  107_HRV15b   CATGTTCTATGATGGATATGATGGAGATTCCACTGAATCACATTATGGTACAGTGGTCAC
2451  108_HRV74a   CATGTTTTATGATGGATATGATGGAGACTCTACTGAATCACATTATGGTACAGTAGTAAC
2452  109_HRV74b   CATGTTTTATGATGGATATGATGGAGACTCTACTGAATCACATTATGGTACAGTAGTAAC
2453  110_HRV74    CATGTTTTATGATGGATATGATGGAGACTCTACTGAATCACATTATGGTACAGTAGTAAC
2454  111_HRV38a   TATGTTTTATGATGGATATGATGGGGACTCAACAGAATCACATTATGGGACAGCGGTGAC
2455  112_HRV38b   TATGTTTTATGATGGATATGATGGGGACTCAACAGAATCACATTATGGGACAGCGGTGAC
2456  113_HRV38    TATGTTTTATGATGGATATGATGGGGACTCAACAGAATCACATTATGGGACAGCGGTGAC
2457  114_HRV60    CATGTTTTATGATGGTTATGATGGTCACTCAACTGAATCACATTATGGGACGGTTGTGAC
2458  115_HRV60a   CATGTTTTATGATGGATATGATGGTCACTCAACTGAATCACATTATGGGACGGTTGTGAC
2459  116_HRV60b   CATGTTTTATGATGGTTATGATGGTCACTCAACTGAATCACATTATGGGACGGTTGTGAC
2460  117_HRV64a   CATGTTTTATGATGGTTATGACGGTGG---ACCTGGTTCCCGTTATGGCGCAGTGGTGAC
2461  118_HRV64b   CATGTTTTATGATGGTTATGACGGTGG---ACCTGGTTCCCGTTATGGCGCAGTGGTGAC
2462  119_HRV64    CATGTTTTATGATGGTTATGATGGTGG---ACCTGGTTCCCGTTATGGCGCAGTGGTGAC
2463  120_HRV94a   CATGTTCTATGATGGTTATGATGGTGG---ACCTGGCTCACGCTATGGCACAGTGGTGAC
2464  121_HRV94b   CATGTTCTATGATGGTTATGATGGTGG---ACCTGGCTCACGCTATGGCACAGTGGTGAC
2465  122_HRV94    CATGTTCTATGATGGTTATGATGGTGG---ACCTGGCTCACGCTATGGCACAGTGGTGAC
2466  123_HRV22    CATGTTTTATGATGGGTATGATGGAGG---TCCCGGATCACGTTATGGAGCAGTGGTAAC
2467  124_HRV22a   CATGTTTTATGATGGGTATGATGGAGG---TCCCGGATCACGTTATGGAGCAGTGGTAAC
2468  125_HRV22b   CATGTTTTATGATGGGTATGATGGAGG---TCCCGGATCACGTTATGGAGCAGTGGTAAC
2469  126_HRV82    TATGTTCTATGATGGCTATGATGGTGATGCTCCCGGATCGCGATACGGGACCATAGTGAC
2470  127_HRV82b   TATGTTCTATGATGGCTATGATGGTGATGCTCCCGGATCGCGATACGGGACCATAGTGAC
```

FIG. D7 CONT'D

```
03.trace                                                             9/20/2007 5:03 PM 2471  128_HRV82a   TATGTTCTATGATGGCTATGATGGTGATGCTCCCGGATCGCGATACGGGACCATAGTGAC
2472  129_HRV19    CATGTTTTATGATGGGTATGATGGAGATTCACCAGGATCCCGCTATGGAACAATAGTAAC
2473  130_HRV19a   CATGTTTTATGATGGGTATGATGGAGATTCACCAGGATCCCGCTATGGAACAATAGTAAC
2474  131_HRV19b   CATGTTTTATGATGGGTATGATGGAGATTCACCAGGATCCCGCTATGGAACAATAGTAAC
2475  132_HRV13    TATGTTTTATGATGGATATAATGGAGATTCCTCAGATGCACGCTATGGGACAACAATCAC
2476  133_HRV13a   TATGTTTTATGATGGATATAATGGAGATTCCTCAGATGCACGCTATGGGACAACAATCAC
2477  134_HRV13b   TATGTTTTATGATGGATATAATGGAGATTCCTCAGATGCACGCTATGGGACAACAATCAC
2478  135_HRV41    CATGTTTTATGATGGTTATGAAGAAGGCTCTACAAATGCACGCTATGGAACAACAGTCAC
2479  136_HRV41a   CATGTTTTATGATGGTTATGAAGAAGGCTCTACAAATGCACGCTATGGAACAACAGTCAC
2480  137_HRV41b   CATGTTTTATGATGGTTATGAAGAAGGCTCTACAAATGCACGCTATGGAACAACAGTCAC
2481  138_HRV73    TATGTTTTATGATGGATATGATGGTGACTCCACACAATCACATTATGGCACCACAGTAGT
2482  139_HRV73b   TATGTTTTATGATGGATATGATGGTGACTCCACACAATCACATTATGGCACCACAGTAGT
2483  140_HRV73a   TATGTTTTATGATGGATATGATGGTGACTCCACACAATCACATTATGGCACCACAGTAGT
2484  141_HRV61    TATGTTTTATGATGGTTATGATGGAGATTCTGAAATAACGCGCTATGGAACATCAGTGAC
2485  142_HRV61a   TATGTTTTATGATGGTTATGATGGAGATTCTGAAATAACGCGCTATGGAACATCAGTGAC
2486  143_HRV61b   TATGTTTTATGATGGTTATGATGGAGATTCTGAAATAACGCGCTATGGAACATCAGTGAC
2487  144_HRV96    CATGTTTTATGATGGATATGATGGTGACTCTGAATCAACACGCTATGGAACATCTGTTAC
2488  145_HRV96b   CATGTTTTATGATGGATATGATGGTGACTCTGAATCAACACGCTATGGAACATCTGTTAC
2489  146_HRV96a   CATGTTTTATGATGGATATGATGGTGACTCTGAATCAACACGCTATGGAACATCTGTTAC
2490  90_HRV16a|   CATGTTTTATGATGGTTATGATGGAGACACATATAAATCCAGATATGGAACTGTAGTCAC
2491  91_HRV16b|   CATGTTTTATGATGGTTATGATGGAGACACATATAAATCCAGATATGGAACTGTAGTCAC
2492  92_1AYM_A    CATGTTTTATGATGGTTATGATGGAGACACATATAAATCCAGATATGGAACTGTAGTCAC
2493  93_HRV81a|   CATGTTCTATGATGGATATGATGGTGATACTTATCACTCCAGATACGGGACTGTAGTCAC
2494  94_HRV81b|   CATGTTCTATGATGGATATGATGGTGATACTTATCACTCCAGATACGGGACTGTAGTCAC
2495  95_HRV81     CATGTTCTATGATGGATATGATGGTGATACTTATCACTCCAGATACGGGACTGTAGTCAC
2496  147_HRV2     CATGTTTTATGATGGGTATGATG------AACAAGATCAAAACTATGGTACAGCAAGCAC
2497  148_HRV2a|   CATGTTTTATGATGGGTATGATG------AACAAGATCAAAACTATGGTACAGCAAGCAC
2498  149_HRV2b|   CATGTTTTATGATGGGTATGATG------AACAAGATCAAAACTATGGTACAGCAAGCAC
2499  150_HRV49a   CATGTTTTATGATGGATATAATG------AACAGGGCCAAAATTATGGTACGGTAAGTAC
2500  151_HRV49b   CATGTTTTATGATGGATATAATG------AACAGGGCCAAAATTATGGTACGGTAAGTAC
2501  152_HRV49    CATGTTTTATGATGGATATAATG------AACAGGGCCAAAATTATGGTACGGTAAGTAC
2502  153_HRV23a   CATGTTTTATGATGGATACAATG------AGAAAGGCACGCATTATGGAACAGTTAGCAC
2503  154_HRV23b   CATGTTTTATGATGGATACAATG------AGAAAGGCACGCATTATGGAACAGTTAGCAC
2504  155_HRV23    CATGTTTTATGATGGATACAATG------AGAAAGGCACGCATTATGGAACAGTTAGCAC
2505  156_HRV30a   CATGTTCTATGATGGATACAATG------AGGGAGGCACAAATTATGGTACAGTGAGCAC
2506  157_HRV30b   CATGTTCTATGATGGATACAATG------AGGGAGGCACAAATTATGGTACAGTGAGCAC
2507  158_HRV30    CATGTTCTATGATGGATACAATG------AGGGAGGCACAAATTATGGTACAGTGAGCAC
2508  159_HRV7     TATGTTCTATGATGGATATGATGGTGATGATGCGTCATCCAAATATGGTTCCGTAGTAAC
2509  160_HRV7b|   TATGTTCTATGATGGATATGATGGTGATGATGCGTCATCCAAATATGGTTCCGTAGTAAC
2510  161_HRV7a|   TATGTTCTATGATGGATATGATGGTGATGATGCGTCATCCAAATATGGTTCCGTAGTAAC
2511  162_HRV88    TATGTTTTATGATGGATATGATGGTGATGATGCATCATCTAGGTATGGCTCAGTGGTAAC
2512  163_HRV88a   TATGTTTTATGATGGATATGATGGTGATGATGCATCATCTAGGTATGGCTCAGTGGTAAC
2513  164_HRV88b   TATGTTTTATGATGGATATGATGGTGATGATGCATCATCTAGGTATGGCTCAGTGGTAAC
2514  165_HRV36a   TATGTTTTATGATGGTTATGATGGTGATAATGCCGCATCAAAATATGGATCTGTGGTTAC
2515  166_HRV36b   TATGTTTTATGATGGTTATGATGGTGATAATGCCGCATCAAAATATGGATCTGTGGTTAC
2516  167_HRV36    TATGTTTTATGATGGTTATGATGGTGATAATGCCGCATCAAAATATGGATCTGTGGTTAC
2517  168_HRV89a   CATGTTTTATGATGGTTATGATGGTGATAGTGCAGCATCAAAATACGGTTCTGTAGTCAC
2518  169_HRV89b   CATGTTTTATGATGGTTATGATGGTGATAGTGCAGCATCAAAATACGGTTCTGTAGTCAC
2519  170_HRV89    CATGTTTTATGATGGTTATGATGGTGATAGTGCAGCATCAAAATACGGTTCTGTAGTCAC
2520  171_HRV58    TATGTTTTATGATGGCTATGATGGTGATGATGCTAAATCAATATATGGTTCTGTGGTAAC
2521  172_HRV58a   TATGTTTTATGATGGCTATGATGGTGATGATGCTAAATCAATATATGGTTCTGTGGTAAC
2522  173_HRV58b   TATGTTTTATGATGGCTATGATGGTGATGATGCTAAATCAATATATGGTTCTGTGGTAAC
2523  174_HRV12a   CATGTTTTATGATGGTTATGCTGATGACAACCCAAGTGCACCTTATGGAACTGTAGTTAC
2524  175_HRV12b   CATGTTTTATGATGGTTATGCTGATGACAACCCAAGTGCACCTTATGGAACTGTAGTTAC
2525  176_HRV12    CATGTTTTATGATGGTTATGCTGATGACAACCCAAGTGCACCTTATGGAACTGTAGTTAC
2526  177_HRV78a   CATGTTTTATGATGGATACTCGGATGACAGCACATCCTCTCCATATGGCACTGTAGTTAC
2527  178_HRV78b   CATGTTTTATGATGGATACTCGGATGACAGCACATCCTCTCCATATGGCACTGTAGTTAC
2528  179_HRV78    CATGTTTTATGATGGATACTCGGATGACAGCACATCCTCTCCATATGGCACTGTAGTTAC
2529  180_HRV20    TATGTTTTATGATGGTTATGAAGATGATAAGG---GAAGTGTGTATGGGTCTGTTGTCAC
2530  181_HRV20a   TATGTTTTATGATGGTTATGAAGATGATAAGG---GAAGTGTGTATGGGTCTGTTGTCAC
2531  182_HRV20b   TATGTTTTATGATGGTTATGAAGATGATAAGG---GAAGTGTGTATGGGTCTGTTGTCAC
2532  183_HRV68    TATGTTTTATGATGGATATGAGGATGACAAAG---GAAGTGTGTATGGATCTGTTGTTAC
2533  184_HRV68a   TATGTTTTATGATGGATATGAGGATGACAAAG---GAAGTGTGTATGGATCTGTTGTTAC
2534  185_HRV68b   TATGTTTTATGATGGATATGAGGATGACAAAG---GAAGTGTGTATGGATCTGTTGTTAC
2535  186_HRV28    CATGTTTTATGATGGTTATGAAGATGACAATG---GAACTACCTATGGTGCAGTGGTTAC
```

FIG. D7 CONT'D

```
03.trace                                                                9/20/2007 5:03 PM 2536 187_HRV28a    CATGTTTTATGATGGTTATGAAGATGACAATG---GAACTACCTATGGTGCAGTGGTTAC
2537 188_HRV28b    CATGTTTTATGATGGTTATGAAGATGACAATG---GAACTACCTATGGTGCAGTGGTTAC
2538 189_HRV53a    TATGTTCTATGATGGGTATGAAGATGACAATG---GCACCACTTATGGGGCTGTTGTTAC
2539 190_HRV53b    TATGTTCTATGATGGGTATGAAGATGACAATG---GCACCACTTATGGGGCTGTTGTTAC
2540 191_HRV53     TATGTTCTATGATGGGTATGAAGATGACAATG---GCACCACTTATGGGGCTGTTGTTAC
2541 192_HRV46a    CATGTTTTATGATGGCTACGAAAGTGATAAAG---GCAAGATCTATGGAACTGCAGTCAC
2542 193_HRV46b    CATGTTTTATGATGGCTACGAAAGTGATAAAG---GCAAGATCTATGGAACTGCAGTCAC
2543 194_HRV46     CATGTTTTATGATGGCTACGAAAGTGATAAAG---GCAAGATCTATGGAACTGCAGTCAC
2544 195_HRV80a    CATGTTCTATGATGGGTATGAGAGTGATAAAG---GCAACATTTATGGAACAGCAGTTAC
2545 196_HRV80b    CATGTTCTATGATGGGTATGAGAGTGATAAAG---GCAACATTTATGGAACAGCAGTTAC
2546 197_HRV80     CATGTTCTATGATGGGTATGAGAGTGATAAAG---GCAACATTTATGGAACAGCAGTTAC
2547 198_HRV51     CATGTTTTATGATGGGTATGAAGGTGATAGTTTGACCTCACAGTACGGTTCAGTAGTCAC
2548 199_HRV51a    CATGTTTTATGATGGGTATGAAGGTGATAGTTTGACCTCACAGTACGGTTCAGTAGTCAC
2549 200_HRV51b    CATGTTTTATGATGGGTATGAAGGTGATAGTTTGACCTCACAGTACGGTTCAGTAGTCAC
2550 201_HRV65a    CATGTTCTATGATGGTTATGAGGGTGATGACCCAAATTCAAAATATGGTTCAGTGGTTAC
2551 202_HRV65b    CATGTTCTATGATGGTTATGAGGGTGATGACCCAAATTCAAAATATGGTTCAGTGGTTAC
2552 203_HRV65     CATGTTCTATGATGGTTATGAGGGTGATGACCCAAATTCAAAATATGGTTCAGTGGTTAC
2553 204_HRV71a    CATGTTCTATGATGGGTATGAAGGTGATGCCCTCAGTTCTAAATATGGCTCAGTAGTTAC
2554 205_HRV71b    CATGTTCTATGATGGGTATGAAGGTGATGCCCTCAGTTCTAAATATGGCTCAGTAGTTAC
2555 206_HRV71     CATGTTCTATGATGGGTATGAAGGTGATGCCCTCAGTTCTAAATATGGCTCAGTAGTTAC
2556 207_HRV8      CATGTTCTATGATGGTTATGATTCAGATGGTTTAGATGCTATTTATGGTATTCCTGTTAC
2557 208_HRV95     CATGTTCTATGATGGTTATGATTCAGATGGTTTAGATGCTATTTATGGTATTCCTGTTAC
2558 209_HRV45     CATGTTTTATGATGGATACGACACTGATGGCACAGATGCAGTGTATGGTGTTAGTGTGAC
2559 210_HRV45a    CATGTTTTATGATGGATACGACACTGATGGCACAGATGCAGTGTATGGTTAGTGTGAC
2560 211_HRV45b    CATGTTTTATGATGGATACGACACTGATGGCACAGATGCAGTGTATGGTGTTAGTGTGAC
2561 GROUP_1       -ATGTT-TA-GA-GG-TA----------------------TA-GG------------
2562
2563 1_HRV1A1|d    TAATGATATGGGTACTATATGCTCAAGAATAGTTACAGAAAAACAGAAACATTCTGTTGT
2564 2_HRV1A2|d    TAATGATATGGGTACTATATGCTCAAGAATAGTTACAGAAAAACAGAAACATTCTGTTGT
2565 3_HRV1A|cD    TAATGATATGGGTACTATATGCTCAAGAATAGTTACAGAAAAACAGAAACATTCTGTTGT
2566 4_HRV1B1|d    CAATGATATGGGAACCATATGTTCAAGAATAGTTACAGAGAAGCAGGAACACCCTGTCGT
2567 5_HRV1B2|d    CAATGATATGGGAACCATATGTTCAAGAATAGTTACAGAGAAGCAGGAACACCCTGTCGT
2568 6_HRV1B       CAATGATATGGGAACCATATGTTCAAGAATAGTTACAGAGAAGCAGGAACACCCTGTCGT
2569 7_HRV40a|d    TAACCATATGGGAACGCTATGCTCAAGAATAGTCACCAACAAGCAGCAGCATGAAGTTGA
2570 8_HRV40b|d    TAACCATATGGGAACGCTATGCTCAAGAATAGTCACCAACAAGCAGCAGCATGAAGTTGA
2571 9_HRV40       TAACCATATGGGAACGCTATGCTCAAGAATAGTCACCAACAAGCAGCAGCATGAAGTTGA
2572 10_HRV85      CAACCACATGGGAACACTGTGCTCGAGGATAGTTACCAACAAACAGCAGCATGAGGTTGA
2573 11_HRV85a|    CAACCACATGGGAACACTGTGCTCGAGGATAGTTACCAACAAACAGCAGCATGAGGTTGA
2574 12_HRV85b|    CAACCACATGGGAACACTGTGCTCGAGGATAGTTACCAACAAACAGCAGCATGAGGTTGA
2575 13_HRV56a|    AAACCACATGGGGACACTCTGTTCAAGAATTGTGACAAATAAACAACTTCATCCTGTTGA
2576 14_HRV56b|    AAACCACATGGGGACACTCTGTTCAAGAATTGTGACAAATAAACAACTTCATCCTGTTGA
2577 15_HRV56      AAACCACATGGGGACACTCTGTTCAAGAATTGTGACAAATAAACAACTTCATCCTGTTGA
2578 16_HRV54      CAATCATATGGGTACTTTGTGTTCAAGAGTGGTTACTGATAAACAAAAACCCAGTTGA
2579 17_HRV98      TAATCACATGGGCACTTTGTGTTCAAGAGTAGTTACTGGCAAACAAGAACACCCAGTTGA
2580 18_HRV59a|    CAACCACATGGGCACTTTATGTTCTAGAATAGTTACAAACAGTCAGGAGCATCCAGTGGA
2581 19_HRV59b|    CAACCACATGGGCACTTTATGTTCTAGAATAGTTACAAACAGTCAGGAGCATCCAGTGGA
2582 20_HRV59      CAACCACATGGGCACTTTATGTTCTAGAATAGTTACAAACAGTCAGGAGCATCCAGTGGA
2583 21_HRV63      TAACCACATGGGGACTTTATGTTCTAGAATTGTAACAAACAGCCAAGAACATCCAGTTGA
2584 22_HRV63b|    TAACCACATGGGGACTTTATGTTCTAGAATTGTAACAAACAGCCAAGAACATCCAGTTGA
2585 23_HRV63a|    TAACCACATGGGGACTTTATGTTCTAGAATTGTAACAAACAGCCAAGAACATCCAGTTGA
2586 24_HRV39      TAATGATATGGGTACACTTTGCACTAGAATTGTAACAAACCAACAGGAACACCTAGTGGA
2587 25_HRV39a|    TAATGATATGGGTACACTTTGCACTAGAATTGTAACAAACCAACAGGAACACCTAGTGGA
2588 26_HRV39b|    TAATGATATGGGTACACTTTGCACTAGAATTGTAACAAACCAACAGAAACACCTAGTGGA
2589 27_HRV10a|    AAATCACATGGGCACTTTGTGCATGCGAATAGTCACAAACCAGCAAGCACATGAGGTGGA
2590 28_HRV10b|    AAATCACATGGGCACTTTGTGCATGCGAATAGTCACAAACCAGCAAGCACATGAGGTGGA
2591 29_HRV10      AAATCACATGGGCACTTTGTGCATGCGAATAGTCACAAACCAGCAAGCACATGAGGTGGA
2592 30_HRV100a    TAACCACATGGGTACACTTTGTATGAGGATAGTTACAAATCAGCAAGCACATGAGGTGGA
2593 31_HRV100b    TAACCACATGGGTACACTTTGTATGAGGATAGTTACAAATCAGCAAGCACATGAGGTGGA
2594 32_HRV100     TAACCACATGGGTACACTTTGTATGAGGATAGTTACAAATCAGCAAGCACATGAGGTGGA
2595 33_HRV66      TAATCATATGGGTACATTATGTATTAGGATTGTTACAAATGAACAGCACCATAATGTTGA
2596 34_HRV66b|    TAATCATATGGGTACATTATGTATTAGGATTGTTACAAATGAACAGCACCATAATGTTGA
2597 35_HRV66a|    TAATCATATGGGTACATTATGTATTAGGATTGTTACAAATGAACAGCACCATAATGTTGA
2598 36_HRV77a|    TAATCACATGGGCACACTGTGCATTAGAATAGTCACTAATCAGCAAAATCATGAGGTTGA
2599 37_HRV77b|    TAATCACATGGGCACACTGTGCATTAGAATAGTCACTAATCAGCAAAATCATGAGGTTGA
2600 38_HRV77      TAATCACATGGGCACACTGTGCATTAGAATAGTCACTAATCAGCAAAATCATGAGGTTGA
```

FIG. D7 CONT'D

03.trace                                                               9/20/2007 5:03 PM

```
2601  39_HRV62a    TAATCGTATGGGGGCACTGTGTATGAGGATTGTCACAAACAAACAAGTTCATGATGTTGA
2602  40_HRV62b    TAATCGTATGGGGGCACTGTGTATGAGGATTGTCACAAACAAACAAGTTCATGATGTTGA
2603  41_HRV25     TAACCGTATGGGAGCACTGTGCATGAGAATTGTCACAAATAAACAAGTCCATGATGTTGA
2604  42_HRV29a    TAACCGGATGGGGACGCTTTGTGTCAGAATTGTTACAGGCAAACAAGCTCATGATGTTCA
2605  43_HRV29b    TAACCGGATGGGGACGCTTTGTGTCAGAATTGTTACAGGCAAACAAGCTCATGATGTTCA
2606  44_HRV44a    TAACCGGATGGGGACGCTTTGCGTCAGGATCGTTACGGGCAAACAGGCTCATGATGTCCA
2607  45_HRV44b    TAACCGGATGGGGACGCTTTGCGTCAGGATCGTTACGGGCAAACAGGCTCATGATGTCCA
2608  46_HRV31     TAATCGCATGGGTGCACTATGCATGAGAGTTGTCACTAACAAACAAGCTCATGATAAGTTGA
2609  47_HRV31a|   TAATCGCATGGGTGCACTATGCATGAGAGTTGTCACTAACAAACAAGCTCATAAAGTTGA
2610  48_HRV31b|   TAATCGCATGGGTGCACTATGCATGAGAGTTGTCACTAACAAACAAGCTCATAAAGTTGA
2611  49_HRV47     CAATCGCATGGGTGCATTGTGTATGAGAGTTGTAACAAACAAGCAACTCCATAAAGTTGA
2612  50_HRV47a|   CAATCGCATGGGTGCATTGTGTATGAGAGTTGTAACAAACAAGCAACTCCATAAAGTTGA
2613  51_HRV47b|   CAATCGCATGGGTGCATTGTGTATGAGAGTTGTAACAAACAAGCAACTCCATAAAGTTGA
2614  52_HRV11     CAATGATATGGGCACTCTGTGTTATAGAATAGTAACTGATGACCATAGACACAAAATTGA
2615  53_HRV11b|   CAATGATATGGGCACTCTGTGTTATAGAATAGTAACTGATGACCATAGACACAAAATTGA
2616  54_HRV11a|   CAATGATATGGGCACTCTGTGTTATAGAATAGTAACTGATGACCATAGACACAAAATTGA
2617  55_HRV76     CAATGACATGGGCACCCTATGTTCCAGGATAGTAACTGATGATCATAAGCACAAGATTGA
2618  56_HRV76b|   CAATGACATGGGCACCCTATGTTCCAGGATAGTAACTGATGATCATAAGCACAAGATTGA
2619  57_HRV76a|   CAATGACATGGGCACCCTATGTTCCAGGATAGTAACTGATGATCATAAGCACAAGATTGA
2620  58_HRV33     CAATGACATGGGCACTTTATGCTCTAGAATAGTTACAGATAATCATAAGCATCCAATAGA
2621  59_HRV33b|   CAATGACATGGGCACTTTATGCTCTAGAATAGTTACAGATAATCATAAGCATCCAATAGA
2622  60_HRV33a|   CAATGACATGGGCACTTTATGCTCTAGAATAGTTACAGATAATCATAAGCATCCAATAGA
2623  61_HRV24a|   AAACGACATGGGAACTCTATGCTATAGAATAGTCACTGACAAGCATAATCACCAAATAGA
2624  62_HRV24b|   AAACGACATGGGAACTCTATGCTATAGAATAGTCACTGACAAGCATAATCACCAAATAGA
2625  63_HRV24     AAACGACATGGGAACTCTATGCTATAGAATAGTCACTGACAAGCATAATCACCAAATAGA
2626  64_HRV90     TAATGATATGGGAACCTTATGTTATAGAATAGTTACAGATGAACATGCCCACAAAATAGA
2627  65_HRV90a|   TAATGATATGGGAACCTTATGTTATAGAATAGTTACAGATGAACATGCCCACAAAATAGA
2628  66_HRV90b|   TAATGATATGGGAACCTTATGTTATAGAATAGTTACAGATGAACATGCCCACAAAATAGA
2629  67_HRV34     TAATGACATGGGTACTTTATGCTCCAGAATTGTAACTGATGAACACCAAAACAGAGTAGA
2630  68_HRV34b|   TAATGACATGGGTACTTTATGCTCCAGAATTGTAACTGATGAACACCAAAACAGAGTAGA
2631  69_HRV34a|   TAATGACATGGGTACTTTATGCTCCAGAATTGTAACTGATGAACACCAAAACAGAGTAGA
2632  70_HRV50a|   CAATGACATGGGCACTTTGTGTTCTAGGATTGTCACTGATGAGCACCAAAATAAAGTGGA
2633  71_HRV50b|   CAATGACATGGGCACTTTGTGTTCTAGGATTGTCACTGATGAGCACCAAAATAAAGTGGA
2634  72_HRV50     CAATGACATGGGCACTTTGTGTTCTAGGATTGTCACTGATGAGCACCAAAATAAAGTGGA
2635  73_HRV18a|   AAATGACATGGGTACCTTGTGCTCTAGAATAGTCACAGATAAACATAAGAATGAGGTGGA
2636  74_HRV18b|   AAATGACATGGGTACCTTGTGCTCTAGAATAGTCACAGATAAACATAAGAATGAGGTGGA
2637  75_HRV18     AAATGACATGGGTACCTTGTGCTCTAGAATAGTCACAGATAAACATAAGAATGAGGTGGA
2638  76_HRV55     TAATGACATGGGTACTTTATGTTCTAGAATAATAACTGATAACCATAAGCACCCAATTGA
2639  77_HRV55b|   TAATGACATGGGTACTTTATGTTCTAGAATAATAACTGATAACCATAAGCACCCAATTGA
2640  78_HRV55a|   TAATGACATGGGTACTTTATGTTCTAGAATAATAACTGATAACCATAAGCACCCAATTGA
2641  79_HRV57     TAATGACATGGGCACTTTATGTTCTAGAATTGTTACTGACCAGCACACACATCCCATAAA
2642  80_HRV57a|   TAATGACATGGGCACTTTATGTTCTAGAATTGTTACTGACCAGCACACACATCCCATAAA
2643  81_HRV57b|   TAATGACATGGGCACTTTATGTTCTAGAATTGTTACTGACCAGCACACACATCCCATAAA
2644  82_HRV21     TAATGATATGGGATCTCTATGCTACAGAATAGTAACTGGCCAGCATAAGCATAAGATAGA
2645  83_HRVHan    TAATGATATGGGATCTCTATGCTATAGAATAGTAACTGATCAGCATAAGCACAAGATAGA
2646  84_HRV43     CAACCACATGGGAACATTATGTTCTAGGATAGTTACAGAAGAACACCAAAATCAAATCGA
2647  85_HRV43b|   CAACCACATGGGAACATTATGTTCTAGGATAGTTACAGAAGAACACCAAAATCAAATCGA
2648  86_HRV43a|   CAACCACATGGGAACATTATGTTCTAGGATAGTTACAGAAGAACACCAAAATCAAATCGA
2649  87_HRV75     TAATCACATGGGGACACTGTGTTCTAGAATAGTTACAGAAGAACATCGAAATAAAGTTGA
2650  88_HRV75b|   TAATCACATGGGGACACTGTGTTCTAGAATAGTTACAGAAGAACATCGAAATAAAGTTGA
2651  89_HRV75a|   TAATCACATGGGGACACTGTGTTCTAGAATAGTTACAGAAGAACATCGAAATAAAGTTGA
2652  96_HRV9a|d   AAATGATATGGGATCTTTATGTTCCCGTGTAGTTACTGAAGAGCATGGACCCCGTGTCAA
2653  97_HRV9b|d   AAATGATATGGGATCTTTATGTTCCCGTGTAGTTACTGAAGAGCATGGACCCCGTGTCAA
2654  98_HRV9      AAATGATATGGGATCTTTATGTTCCCGTGTAGTTACTGAAGAGCATGGACCCCGTGTCAA
2655  99_HRV32     AAATGATATGGGTTCCCTGTGTTCTCGTACCGAAGAGCACGGATCCCGTGTTGA
2656  100_HRV32a   AAATGATATGGGTTCCCTGTGTTCTCGTATAGTCACCGAAGAGCACGGATCCCGTGTTGA
2657  101_HRV32b   AAATGATATGGGTTCCCTGTGTTCTCGTATAGTCACCGAAGAGCACGGATCCCGTGTTGA
2658  102_HRV67    TAATGATATGGGTTCCTTGTGTTCGCGTATAGTTACTGAAGAACATGGTTCTCGCGTAAA
2659  103_HRV67a   TAATGATATGGGTTCCTTGTGTTCGCGTATAGTTACTGAAGAACATGGTTCTCGCGTAAA
2660  104_HRV67b   TAATGATATGGGTTCCTTGTGTTCGCGTATAGTTACTGAAGAACATGGTTCTCGCGTAAA
2661  105_HRV15    TAATGACATGGGGACACTGTGTTCTAGAATAGTAACTGAAGAGCATGGGACACGTGTAGA
2662  106_HRV15a   TAATGACATGGGGACACTGTGTTCTAGAATAGTAACTGAAGAGCATGGGACACGTGTAGA
2663  107_HRV15b   TAATGACATGGGGACACTGTGTTCTAGAATAGTAACTGAAGAGCATGGGACACGTGTAGA
2664  108_HRV74a   AAATGACATGGGAACTCTATGTTCTAGAATTGTGACTGAAGAACACGATCACGTGTGGA
2665  109_HRV74b   AAATGACATGGGAACTCTATGTTCTAGAATTGTGACTGAAGAACACGATCACGTGTGGA
```

FIG. D7 CONT'D

```
03.trace                                                                                         9/20/2007 5:03 PM 2666 110_HRV74    AAATGACATGGGAACTCTATGTTCTAGAATTGTGACTGAAGAACACGATGCACGTGTGGA
2667 111_HRV38a   CAATGATATGGGGACACTTTGTTCAAGAATAGTCACTGAAAATCATGGGACCCAAGTGAA
2668 112_HRV38b   CAATGATATGGGGACACTTTGTTCAAGAATAGTCACTGAAAATCATGGGACCCAAGTGAA
2669 113_HRV38    CAATGATATGGGGACACTTTGTTCAAGAATAGTCACTGAAAATCATGGGACCCAAGTGAA
2670 114_HRV60    CAATGACATGGGAACGTTGTGCTCCAGAATAGTTACTGAACACCATGGTACACAGGTTCA
2671 115_HRV60a   CAATGACATGGGAACGTTGTGCTCCAGAATAGTTACTGAACACCATGGTACACAGGTTCA
2672 116_HRV60b   CAATGACATGGGAACGTTGTGCTCCAGAATAGTTACTGAACACCATGGTACACAGGTTCA
2673 117_HRV64a   AAATGATATGGGCACTTTGTGTTCTAGAATTGTGACTGAGGAACACACAACACAGGTCAA
2674 118_HRV64b   AAATGATATGGGCACTTTGTGTTCTAGAATTGTGACTGAGGAACACACAACACAGGTCAA
2675 119_HRV64    AAATGATATGGGCACTTTGTGTTCTAGAATTGTGACTGAGGAACACACAACACAGGTCAA
2676 120_HRV94a   AAATGACATGGGAACATTATGCTCCAGGATTGTGACTGAGGAGCACAAGACACAGGTTAA
2677 121_HRV94b   AAATGACATGGGAACATTATGCTCCAGGATTGTGACTGAGGAGCACAAGACACAGGTTAA
2678 122_HRV94    AAATGACATGGGAACATTATGCTCCAGGATTGTGACTGAGGAGCACAAGACACAGGTTAA
2679 123_HRV22    AAATGATATGGGCACACTGTGCTCTAGGATTGTGACTGAAGAACACCAGACACAAGTCAA
2680 124_HRV22a   AAATGATATGGGCACACTGTGCTCTAGGATTGTGACTGAAGAACACCAGACACAAGTCAA
2681 125_HRV22b   AAATGATATGGGCACACTGTGCTCTAGGATTGTGACTGAAGAACACCAGACACAAGTCAA
2682 126_HRV82    AAATGACATGGGTACACTGTGTTCTAGAATTGTAACTGAAGAACACCAGACTCAAGTCAG
2683 127_HRV82b   AAATGACATGGGTACACTGTGTTCTAGAATTGTAACTGAAGAACACCAGACTCAAGTCAG
2684 128_HRV82a   AAATGACATGGGTACACTGTGTTCTAGAATTGTAACTGAAGAACACCAGACTCAAGTCAG
2685 129_HRV19    TAATGATATGGGAACCTTATGCTCCAGAATAGTAACTGATGAACACCAAACACAGGTTGC
2686 130_HRV19a   TAATGATATGGGAACCTTATGCTCCAGAATAGTAACTGATGAACACCAAACACAGGTTGC
2687 131_HRV19b   TAATGATATGGGAACCTTATGCTCCAGAATAGTAACTGATGAACACCAAACACAGGTTGC
2688 132_HRV13    TAATGATATGGGCACACTTTGCTTCAGAATAGTAACTGAAGAACATACTAACAAGGTCAA
2689 133_HRV13a   TAATGATATGGGCACACTTTGCTTCAGAATAGTAACTGAAGAACATACTAACAAGGTCAA
2690 134_HRV13b   TAATGATATGGGCACACTTTGCTTCAGAATAGTAACTGAAGAACATACTAACAAGGTCAA
2691 135_HRV41    AAATGACATGGGTACATTATGCTTTAGAATAGTTACTGAAGAACACACCAACAAAGTTAA
2692 136_HRV41a   AAATGACATGGGTACATTATGCTTTAGAATAGTTACTGAAGAACACACCAACAAAGTTAA
2693 137_HRV41b   AAATGACATGGGTACATTATGCTTTAGAATAGTTACTGAAGAACACACCAACAAAGTTAA
2694 138_HRV73    TAATGACATGGGCACATTATGCTTTAGGATAGTGACTGAAGAACACACTAGCAGGGTAAA
2695 139_HRV73b   TAATGACATGGGCACATTATGCTTTAGGATAGTGACTGAAGAACACACTAGCAGGGTAAA
2696 140_HRV73a   TAATGACATGGGCACATTATGCTTTAGGATAGTGACTGAAGAACACACTAGCAGGGTAAA
2697 141_HRV61    AAATGATATGGGTGCATTGTGCTTTAGAATAGTAACTGAACAGCATACAAATCAAGTTAA
2698 142_HRV61a   AAATGATATGGGTGCATTGTGCTTTAGAATAGTAACTGAACAGCATACAAATCAAGTTAA
2699 143_HRV61b   AAATGATATGGGTGCATTGTGCTTTAGAATAGTAACTGAACAGCATACAAATCAAGTTAA
2700 144_HRV96    CAATGACATGGGCACTTTATGTTTTAGAATAGTGACAGAGGAACACACCAACAAGGTCAA
2701 145_HRV96b   CAATGACATGGGCACTTTATGTTTTAGAATAGTGACAGAGGAACACACCAACAAGGTCAA
2702 146_HRV96a   CAATGACATGGGCACTTTATGTTTTAGAATAGTGACAGAGGAACACACCAACAAGGTCAA
2703 90_HRV16a|   CAATGACATGGGAACTTTGTGTTGACCAGTGAGCAATTACACAAAGTCAA
2704 91_HRV16b|   CAATGACATGGGAACTTTGTGTTCGCGTATTGTGACCAGTGAGCAATTACACAAAGTCAA
2705 92_1AYM_A    CAATGACATGGGAACTTTGTGTTCGCGTATTGTGACCAGTGAGCAATTACACAAAGTCAA
2706 93_HRV81a|   TAATGATATGGGAACATTATGCTCACGGATAGTGACAAGTGAGCAAGTGCACAAGGTGAA
2707 94_HRV81b|   TAATGATATGGGAACATTATGCTCACGGATAGTGACAAGTGAGCAAGTGCACAAGGTGAA
2708 95_HRV81     TAATGATATGGGAACATTATGCTCACGGATAGTGACAAGTGAGCAAGTGCACAAGGTGAA
2709 147_HRV2     AAATAACATGGGGTCACTATGCTCTAGGATAGTAACAGAGAAACACATTCATAAGGTACA
2710 148_HRV2a|   AAATAACATGGGGTCACTATGCTCTAGGATAGTAACAGAGAAACACATTCATAAGGTACA
2711 149_HRV2b|   AAATAACATGGGGTCACTATGCTCTAGGATAGTAACAGAGAAACACATTCATAAGGTACA
2712 150_HRV49a   AAACAACATGGGATCATTATGCTCTAGGATAGTAACAGAGAAACACATTCACAGTATGCA
2713 151_HRV49b   AAACAACATGGGATCATTATGCTCTAGGATAGTAACAGAGAAACACATTCACAGTATGCA
2714 152_HRV49    AAACAACATGGGATCATTATGCTCTAGGATAGTAACAGAGAAACACATTCACAGTATGCA
2715 153_HRV23a   AAACAACATGGGCACATTGTGCTCCAGAGTGGTAACAGAGAAACACATTCATGATATGCG
2716 154_HRV23b   AAACAACATGGGCACATTGTGCTCCAGAGTGGTAACAGAGAAACACATTCATGATATGCG
2717 155_HRV23    AAACAACATGGGCACATTGTGCTCCAGAGTGGTAACAGAGAAACACATTCATGATATGCG
2718 156_HRV30a   AAACAACATGGGCACACTGTGTTCCAGAGTGGTAACAGAAAAACACATTCATGATGTGCG
2719 157_HRV30b   AAACAACATGGGCACACTGTGTTCCAGAGTGGTAACAGAAAAACACATTCATGATGTGCG
2720 158_HRV30    AAACAACATGGGCACACTGTGTTCCAGAGTGGTAACAGAAAAACACATTCATGATGTGCG
2721 159_HRV7     CAATGACATGGGAACCATATGTGTTACATCTACACAAAAACACAATTTAAA
2722 160_HRV7b|   CAATGACATGGGAACCATATGTGTTAGACTAGTTACATCTACACAAAAACACAATTTAAA
2723 161_HRV7a|   CAATGACATGGGAACCATATGTGTTAGACTAGTTACATCTACACAAAAACACAATTTAAA
2724 162_HRV88    TAATGATATGGGAACTATATGTATTAGATTGGTCACCTCCACCCAAAAGCATAAACTGAA
2725 163_HRV88a   TAATGATATGGGAACTATATGTATTAGATTGGTCACCTCCACCCAAAAGCATAAACTGAA
2726 164_HRV88b   TAATGATATGGGAACTATATGTATTAGATTGGTCACCTCCACCCAAAAGCATAAACTGAA
2727 165_HRV36a   TAACGACATGGGAACCATATGTGTTAGAATAGTTACATCCAACCAAAAACATGATTTAAA
2728 166_HRV36b   TAACGACATGGGAACCATATGTGTTAGAATAGTTACATCCAACCAAAAACATGATTTAAA
2729 167_HRV36    TAACGACATGGGAACCATATGTGTTAGAATAGTTACATCCAACCAAAAACATGATTTAAA
2730 168_HRV89a   TAATGATATGGGAACCATATGTGTTAGAATAGTGACATCCAACCAAAAACATGATTTAAA
```

FIG. D7 CONT'D

```
03.trace                                                          9/20/2007 5:03 PM 2731 169_HRV89b    TAATGATATGGGAACCATATGTGTTAGAATAGTGACATCCAACCAAAAACATGATTTAAA
2732 170_HRV89     TAATGATATGGGAACCATATGTGTTAGAATAGTGACATCCAACCAAAAACATGATTTAAA
2733 171_HRV58     AAATGACATGGGAACTATATGTGTTAGAATAGTCACATCCAAACAAAGACACAATTTAAA
2734 172_HRV58a    AAATGACATGGGAACTATATGTGTTAGAATAGTCACATCCAAACAAAGACACAATTTAAA
2735 173_HRV58b    AAATGACATGGGAACTATATGTGTTAGAATAGTCACATCCAAACAAAGACACAATTTAAA
2736 174_HRV12a    CAATGACATGGGTTCACTGTGTGTCAGAATAGTTACAGACCAGCAAAAACATAAAGTTAA
2737 175_HRV12b    CAATGACATGGGTTCACTGTGTGTCAGAATAGTTACAGACCAGCAAAAACATAAAGTTAA
2738 176_HRV12     CAATGACATGGGTTCACTGTGTGTCAGAATAGTTACAGACCAGCAAAAACATAAAGTTAA
2739 177_HRV78a    CAATGACATGGGTACACTGTGTATGAGGATGGTTACAGATCAACAACAACATAAGGTCAC
2740 178_HRV78b    CAATGACATGGGTACACTGTGTATGAGGATGGTTACAGATCAACAACAACATAAGGTCAC
2741 179_HRV78     CAATGACATGGGTACACTGTGTATGAGGATGGTTACAGATCAACAACAACATAAGGTCAC
2742 180_HRV20     AAACGATATGGGCACATTGTGTGTTCGTATTGTGACTGAGCAGCAGACACATAAGGTTAA
2743 181_HRV20a    AAACGATATGGGCACATTGTGTGTTCGTATTGTGACTGAGCAGCAGACACATAAGGTTAA
2744 182_HRV20b    AAACGATATGGGCACATTGTGTGTTCGTATTGTGACTGAGCAGCAGACACATAAGGTTAA
2745 183_HRV68     AAATGATATGGGCACATTATGTGTCCGTATTGTGACTGAGCAGCAGACACATAGGGTCAA
2746 184_HRV68a    AAATGATATGGGCACATTATGTGTCCGTATTGTGACTGAGCAGCAGACACATAGGGTCAA
2747 185_HRV68b    AAATGATATGGGCACATTATGTGTCCGTATTGTGACTGAGCAGCAGACACATAGGGTCAA
2748 186_HRV28     AAATCATATGGGAACACTCTGTGCTCGCATAGTAACTGAACAACAGAAGCATGAAGTCAA
2749 187_HRV28a    AAATCATATGGGAACACTCTGTGCTCGCATAGTAACTGAACAACAGAAGCATGAAGTCAA
2750 188_HRV28b    AAATCATATGGGAACACTCTGTGCTCGCATAGTAACTGAACAACAGAAGCATGAAGTCAA
2751 189_HRV53a    TAATGATATGGGAACACTTTGTGTGCGCATAGTGACTGAGCAACAGAAAAATGAGGTCAA
2752 190_HRV53b    TAATGATATGGGAACACTTTGTGTGCGCATAGTGACTGAGCAACAGAAAAATGAGGTCAA
2753 191_HRV53     TAATGATATGGGAACACTTTGTGTGCGCATAGTGACTGAGCAACAGAAAAATGAGGTCAA
2754 192_HRV46a    CAATGATATGGGAACTATATGTGTCAGAATTGTTACCGAACAACAAAAACATAAGGTTCT
2755 193_HRV46b    CAATGATATGGGAACTATATGTGTCAGAATTGTTACCGAACAACAAAAACATAAGGTTCT
2756 194_HRV46     CAATGATATGGGAACTATATGTGTCAGAATTGTTACCGAACAACAAAAACATAAGGTTCT
2757 195_HRV80a    CAATGATATGGGAACCCTGTGTGCTAGAATTGTTACAGAACAACAGAAAACATAAAGTCCT
2758 196_HRV80b    CAATGATATGGGAACCCTGTGTGCTAGAATTGTTACAGAACAACAGAAACATAAAGTCCT
2759 197_HRV80     CAATGATATGGGAACCCTGTGTGCTAGAATTGTTACAGAACAACAGAAACATAAAGTCCT
2760 198_HRV51     AAATGCTATGGGGACACTATGTGTTCGTGTGGTCACAGAGCAACAAAAACATGAGGTTAA
2761 199_HRV51a    AAATGCTATGGGGACACTATGTGTTCGTGTGGTCACAGAGCAACAAAAACATGAGGTTAA
2762 200_HRV51b    AAATGCTATGGGGACACTATGTGTTCGTGTGGTCACAGAGCAACAAAAACATGAGGTTAA
2763 201_HRV65a    TAATGCTATGGGCACACTATATGTGCGTGTGGTTACAGAAAGGCAAAAACATGAAGTCAA
2764 202_HRV65b    TAATGCTATGGGCACACTATATGTGCGTGTGGTTACAGAAAGGCAAAAACATGAAGTCAA
2765 203_HRV65     TAATGCTATGGGCACACTATATGTGCGTGTGGTTACAGAAAGGCAAAAACATGAAGTCAA
2766 204_HRV71a    TAATGCCATGGGCACCTTATGTGTTCGTGTGGTTACAGAACAGCAAAGCAACACAGTCAA
2767 205_HRV71b    TAATGCCATGGGCACCTTATGTGTTCGTGTGGTTACAGAACAGCAAAGCAACACAGTCAA
2768 206_HRV71     TAATGCCATGGGCACCTTATGTGTTCGTGTGGTTACAGAACAGCAAAGCAACACAGTCAA
2769 207_HRV8      AAATCACATGGGCACAATATGTGTGAGAATGGTGACAGATAAACAGAAAATTAAAACTAA
2770 208_HRV95     AAATCACATGGGCACAATATGTGTGAGAATGGTGACAGATAAACAGAAAATTAAAACTAA
2771 209_HRV45     TAACCATATGGGGACTATATGTGTTAGAATTGTTACAGACCAACAACAACATAGAGTTAA
2772 210_HRV45a    TAACCATATGGGGACTATATGTGTTAGAATTGTTACAGACCAACAACAACATAGAGTTAA
2773 211_HRV45b    TAACCATATGGGGACTATATGTGTTAGAATTGTTACAGACCAACAACAACATAGAGTTAA
2774 GROUP_1       -AA----ATGGG--C--T-T------G--T--T-AC-------CA--------------
2775
2776 1_HRV1A1|d    CATCACAACACACATATATCATAAAGCTAAACACACAAAAGCTTGGTGTCCTAGGCCCCC
2777 2_HRV1A2|d    CATCACAACACACATATATCATAAAGCTAAACACACAAAAGCTTGGTGTCCTAGGCCCCC
2778 3_HRV1A|cD    CATCACAACACACATATATCATAAAGCTAAACACACAAAAGCTTGGTGTCCTAGGCCCCC
2779 4_HRV1B1|d    TATTACAACACACATATATCACAAAGCTAAACACACAAAAGCTTGGTGTCCTAGACCTCC
2780 5_HRV1B2|d    TATTACAACACACATATATCACAAAGCTAAACACACAAAAGCTTGGTGTCCTAGACCTCC
2781 6_HRV1B       TATTACAACACACATATATCACAAAGCTAAACACACAAAAGCTTGGTGTCCTAGACCTCC
2782 7_HRV40a|d    GATTACCACACGTATATATCACAAGGCCAAGCATATTAAAGCATGGTGTCCAAGGGCCCC
2783 8_HRV40b|d    GATTACCACACGTATATATCACAAGGCCAAGCATATTAAAGCATGGTGTCCAAGGGCCCC
2784 9_HRV40       GATTACCACACGTATATATCACAAGGCCAAGCATATTAAAGCATGGTGTCCAAGGGCCCC
2785 10_HRV85      AATCACCACGCGTGTGTATCATAAGGCCAAGCATGTAAAGGCTTGGTGTCCAAGAGCACC
2786 11_HRV85a|    AATCACCACGCGTGTGTATCATAAGGCCAAGCATGTAAAGGCTTGGTGTCCAAGAGCACC
2787 12_HRV85b|    AATCACCACGCGTGTGTATCATAAGGCCAAGCATGTAAAGGCTTGGTGTCCAAGAGCACC
2788 13_HRV56a|    AGTCACAACTCGTGTATATCATAAGGCAAAGCATATTCGAGCATGGTGTCCTAGAGCACC
2789 14_HRV56b|    AGTCACAACTCGTGTATATCATAAGGCAAAGCATATTCGAGCATGGTGTCCTAGAGCACC
2790 15_HRV56      AGTCACAACTCGTGTATATCATAAGGCAAAGCATATTCGAGCATGGTGTCCTAGAGCACC
2791 16_HRV54      AATCACCACGGGTGTATCACAAGGCAAAACATTAGAGCATGGTGTCCACGTGCACC
2792 17_HRV98      AATCACTACACGTGTGTACCACAAAGCAAAACACATTAGAGCATGGTGTCCACGTGCACC
2793 18_HRV59a|    GGTTGTCACACGTGTGTATCACAAAGCTAAACACGTCAAAGCCTGGTGCCCTAGAGCTCC
2794 19_HRV59b|    GGTTGTCACACGTGTGTATCACAAAGCTAAACACGTCAAAGCCTGGTGCCCTAGAGCTCC
2795 20_HRV59      GGTTGTCACACGTGTGTATCACAAAGCTAAACACGTCAAAGCCTGGTGCCCTAGAGCTCC
```

FIG. D7 CONT'D

03.trace                                                          9/20/2007 5:03 PM

```
2796  21_HRV63      GGTGACTACACGTGTATATCATAAAGCTAAACACATCAGAGCCTGGTGCCCAAGAGCTCC
2797  22_HRV63b|    GGTGACTACACGTGTATATCATAAAGCTAAACACATCAGAGCCTGGTGCCCAAGAGCTCC
2798  23_HRV63a|    GGTGACTACACGTGTATATCATAAAGCTAAACACATCAGAGCCTGGTGCCCAAGAGCTCC
2799  24_HRV39      GGTTACAACCAGAGTTTACCATAAAGCCAAGCATGTTAAAGCATGGTGCCCTAGGGCTCC
2800  25_HRV39a|    GGTTACAACCAGAGTTTACCATAAAGCCAAGCATGTTAAAGCATGGTGCCCTAGGGCTCC
2801  26_HRV39b|    GGTTACAACCAGAGTTTACCATAAAGCCAAGCATGTTAAAGCATGGTGCCCTAGGGCTCC
2802  27_HRV10a|    AATTACCACCAGTGTTTATCACAAAGCCAAGCATGTCAAAGCATGGTGTCCAAGACCACC
2803  28_HRV10b|    AATTACCACCAGTGTTTATCACAAAGCCAAGCATGTCAAAGCATGGTGTCCAAGACCACC
2804  29_HRV10      AATTACCACCAGTGTTTATCACAAAGCCAAGCATGTCAAAGCATGGTGTCCAAGACCACC
2805  30_HRV100a    AATTACTACTAATATCTATCACAAGGCCAAACATGTTAAAGCTTGGTGCCCAAGACCACC
2806  31_HRV100b    AATTACTACTAATATCTATCACAAGGCCAAACATGTTAAAGCTTGGTGCCCAAGACCACC
2807  32_HRV100     AATTACTACTAATATCTATCACAAGGCCAAACATGTTAAAGCTTGGTGCCCAAGACCACC
2808  33_HRV66      AATTACTACTAGAGTATACCATAAGGCTAAGCATGTTAAAGCCTGGTGTCCTAGACCACT
2809  34_HRV66b|    AATTACTACTAGAGTATACCATAAGGCTAAGCATGTTAAAGCCTGGTGTCCTAGACCACT
2810  35_HRV66a|    AATTACTACTAGAGTATACCATAAGGCTAAGCATGTTAAAGCCTGGTGTCCTAGACCACT
2811  36_HRV77a|    AATCACCACTAGAGTATACCACAAGGCTAAACATATTAAAGCTTGGTGTCCCAGACCACC
2812  37_HRV77b|    AATCACCACTAGAGTATACCACAAGGCTAAACATATTAAAGCTTGGTGTCCCAGACCACC
2813  38_HRV77      AATCACCACTAGAGTATACCACAAGGCTAAACATATTAAAGCTTGGTGTCCCAGACCACC
2814  39_HRV62a     GGTCACAACTAATATTTACCACAAGGCTAAGCATGTAAAACCGTGGTGCCCGCGGCCGCC
2815  40_HRV62b     GGTCACAACTAATATTTACCACAAGGCTAAGCATGTAAAAGCGTGGTGCCCTAGACCACC
2816  41_HRV25      GGTTACAACTAACATTTACCATAAAGCTAAGCATGTAAAAGCATGGTGCCCTAGACCACC
2817  42_HRV29a     AGTTACAACAAGTATCTATCATAAAGCTAAACATGTAAAGGCGTGGTGTCCTAGACCACC
2818  43_HRV29b     AGTTACAACAAGTATCTATCATAAAGCTAAACATGTAAAGGCGTGGTGTCCTAGACCACC
2819  44_HRV44a     AGTTACAACAAGCATTTATCACAAAGCTAAACATGTAAAAGCATGGTGCCCTAGACCACC
2820  45_HRV44b     AGTTACAACAAGCATTTATCACAAAGCTAAACATGTAAAAGCATGGTGCCCTAGACCACC
2821  46_HRV31      AATCACAACCAATATTTACCATAAGGCCAAACATGTTAAGGCATGGTGTCCTAGGCCCCC
2822  47_HRV31a|    AATCACAACCAATATTTACCATAAGGCCAAACATGTTAAAGGCATGGTGTCCTAGGCCCCC
2823  48_HRV31b|    AATCACAACCAATATTTACCATAAGGCCAAACATGTAAAGGCATGGTGTCCTAGGCCCCC
2824  49_HRV47      AATCACAACTAACATCTACCATAAAGCCAAGCATGTGAAAGCATGGTGTCCTAGACCACC
2825  50_HRV47a|    AATCACAACTAACATCTACCATAAAGCCAAGCATGTGAAAGCATGGTGTCCTAGACCACC
2826  51_HRV47b|    AATCACAACTAACATCTACCATAAAGCCAAGCATGTGAAAGCATGGTGTCCTAGACCACC
2827  52_HRV11      AGTCACAACTAGGGTGTATCATAAAGCAAAGCATGTGAAGGTGTGGTGTCCAAGACCACC
2828  53_HRV11b|    AGTCACAACTAGGGTGTATCATAAAGCAAAGCATGTGAAGGTGTGGTGTCCAAGACCACC
2829  54_HRV11a|    AGTCACAACTAGGGTGTATCATAAAGCAAAGCATGTGAAGGTGTGGTGTCCAAGACCACC
2830  55_HRV76      AGTTACAACAAGAATATATCACAAAGCAAAGCATGTTAAGGTATGGTGCCCGAGACCACC
2831  56_HRV76b|    AGTTACAACAAGAATATATCACAAAGCAAAGCATGTTAAGGTATGGTGCCCGAGACCACC
2832  57_HRV76a|    AGTTACAACAAGAATATATCACAAAGCAAAGCATGTTAAGGTGTGGTGCCCGAGACCACC
2833  58_HRV33      AGTTACAACAAGAGTATACCACAAAGCAAATCATGTCAAAGTCTGGTGCCCAAGACCACC
2834  59_HRV33b|    AGTTACAACAAGAGTATACCATAAAGCAAAACATGTCAAAGTCTGGTGCCCAAGACCACC
2835  60_HRV33a|    AGTTACAACAAGAGTATACCATAAAGCAAAACATGTCAAAGTCTGGTGCCCAAGACCACC
2836  61_HRV24a     AATTACAACAAGAATATACCACAAAGCAAAGCACATTAAGGTCTGGTGTCCAAGGCCACC
2837  62_HRV24b     AATTACAACAAGAATATACCACAAAGCAAAGCACATTAAGGTCTGGTGTCCAAGGCCACC
2838  63_HRV24      AATTACAACAAGAATATACCACAAAGCAAAGCACATTAAGGTCTGGTGTCCAAGGCCACC
2839  64_HRV90      GATCACTACAAGAATATACCATAAAGCAAAACACATTAAGGTTTGGTGTCCAAGACCACC
2840  65_HRV90a|    GATCACTACAAGAATATACCATAAAGCAAAACACATTAAGGTTTGGTGTCCAAGACCACC
2841  66_HRV90b|    GATCACTACAAGAATATACCATAAAGCAAAACACATTAAGGTTTGGTGTCCAAGACCACC
2842  67_HRV34      AATAACAACTAGAGTTTATCACAAAGCTAAACATGTAAAAACCTGGTGTCCAAGACCACC
2843  68_HRV34b|    AATAACAACTAGAGTTTATCACAAAGCTAAACATGTAAAAACCTGGTGTCCAAGACCACC
2844  69_HRV34a|    AATAACAACTAGAGTTTATCACAAAGCTAAACATGTAAAAACCTGGTGTCCAAGACCACC
2845  70_HRV50a|    AATCACAACCAGAGTATACCATAAAGCCAAACACATAAAAGTCTGGTGTCCAAGACCACC
2846  71_HRV50b|    AATCACAACCAGAGTATACCATAAAGCCAAACACATAAAAGTCTGGTGTCCAAGACCACC
2847  72_HRV50      AATCACAACCAGAGTATACCATAAAGCCAAACACATAAAAGTCTGGTGTCCAAGACCACC
2848  73_HRV18a|    AATAACAACCAGAATATACCACAAGGCAAAACATGTTAAAGCATGGTGCCCAAGGCCACC
2849  74_HRV18b|    AATAACAACCAGAATATACCACAAGGCAAAACATGTTAAAGCATGGTGCCCAAGGCCACC
2850  75_HRV18      AATAACAACCAGAATATACCACAAGGCAAAACATGTTAAAGCATGGTGCCCAAGGCCACC
2851  76_HRV55      AGTGACGACAAGAGTCTATCATAAAGCTAAACACATCAAAGCATGGTGCCCACGACCACC
2852  77_HRV55b|    AGTGACGACAAGAGTCTATCATAAAGCTAAACACATCAAAGCATGGTGCCCACGACCACC
2853  78_HRV55a|    AGTGACGACAAGAGTCTATCATAAAGCTAAACACATCAAAGCATGGTGCCCACGACCACC
2854  79_HRV57      AATAACAACCAGAGTGTATCACAAAGCCAAACATGTCAAAGCCTGGTGCCCTAGACCACC
2855  80_HRV57a|    AATAACAACCAGAGTGTATCACAAAGCCAAACATGTCAAAGCCTGGTGCCCTAGACCACC
2856  81_HRV57b|    AATAACAACCAGAGTGTATCACAAAGCCAAACATGTCAAAGCCTGGTGCCCTAGACCACC
2857  82_HRV21      AGTGACCACAAGAATATACCATAAGGCAAAGCATGTTAAAGCTTGGTGCCCCAGACCACC
2858  83_HRVHan     AGTGACCACAAGAATATACCATAAGGCAAAGCATGTTAAAGCTTGGTGCCCTAGACCACC
2859  84_HRV43      GATAACTACCAGGATATATCATAAAGCCAAGCATATCAAAGCTTGGTGCCCAAGACCACC
2860  85_HRV43b|    GATAACTACCAGGATATATCATAAAGCCAAGCATATCAAAGCTTGGTGCCCAAGACCACC
```

FIG. D7 CONT'D

03.trace                                                              9/20/2007 5:03 PM

```
2861  86_HRV43a|    GATAACTACCAGGATATATCATAAAGCCAAGCATATCAAAGCTTGGTGCCCAAGACCACC
2862  87_HRV75      AGTAACCACTAGAATATATCACAAAGCCAAACATATAAAAGCTTGGTGTCCGAGGCCGCC
2863  88_HRV75b|    AGTAACCACTAGAATATATCACAAAGCCAAACATATAAAAGCTTGGTGTCCGAGGCCGCC
2864  89_HRV75a|    AGTAACCACTAGAATATATCACAAAGCCAAACATATAAAAGCTTGGTGTCCGAGGCCGCC
2865  96_HRV9a|d    AATTTCAACCAGAATATATCACAAAGCCAAACATGTTAAAGCCTGGTGCCCAAGACCTCC
2866  97_HRV9b|d    AATTTCAACCAGAATATATCACAAAGCCAAACATGTTAAAGCCTGGTGCCCAAGACCTCC
2867  98_HRV9       AATTTCAACCAGAATATATCACAAAGCCAAACATGTTAAAGCCTGGTGCCCAAGACCTCC
2868  99_HRV32      TATTTCAACTAGGGTATATCACAAAGCTAAACACGTCAAAGCTTGGTGCCCAGGACCACC
2869  100_HRV32a    TATTTCAACTAGGGTATATCACAAAGCTAAACACGTCAAAGCTTGGTGCCCACGACCACC
2870  101_HRV32b    TATTTCAACTAGGGTATATCACAAAGCTAAACACGTCAAAGCTTGGTGCCCACGACCACC
2871  102_HRV67     AATTGCAACGCGGGTGTATCATAAGGCTAAACATGTAAAAGCTTGGTGCCCAAGGCCCCC
2872  103_HRV67a    AATTGCAACGCGGGTGTATCATAAGGCTAAACATGTAAAAGCTTGGTGCCCAAGGCCCCC
2873  104_HRV67b    AATTGCAACGCGGGTGTATCATAAGGCTAAACATGTAAAAGCTTGGTGCCCAAGGCCCCC
2874  105_HRV15     GATTACAACTAGAGTGTATCACAAAGCTAAACATGTAAAGGCTTGGTGCCCCAGACCCCC
2875  106_HRV15a    GATTACAACTAGAGTGTATCACAAAGCTAAACATGTAAAGGCTTGGTGCCCCAGACCCCC
2876  107_HRV15b    GATTACAACTAGAGTGTATCACAAAGCTAAACATGTAAAGGCTTGGTGCCCCAGACCCCC
2877  108_HRV74a    AATTACAACTAGAGTGTACCATAAAGCAAAGCATGTGAAGGCATGGTGTCCTAGACCCCC
2878  109_HRV74b    AATTACAACTAGAGTGTACCATAAAGCAAAGCATGTGAAGGCATGGTGTCCTAGACCCCC
2879  110_HRV74     AATTACAACTAGAGTGTACCATAAAGCAAAGCATGTGAAGGCATGGTGTCCTAGACCCCC
2880  111_HRV38a    GATAACAACTAGAATTTATCATAAGGCAAAACATGTAAAAGCCTGGTGTCCCAAGACCCCC
2881  112_HRV38b    GATAACAACTAGAATTTATCATAAGGCAAAACATGTAAAAGCCTGGTGTCCAAGACCCCC
2882  113_HRV38     GATAACAACTAGAATTTATCATAAGGCAAAACATGTAAAAGCCTGGTGTCCAAGACCCCC
2883  114_HRV60     CGTCGCAACAAGAATATATCATAAAGCAAAGCATGTTAAGGCTTGGTGTCCAAGACCTCC
2884  115_HRV60a    CGTCGCAACAAGAATATATCATAAAGCAAAGCATGTTAAGGCTTGGTGTCCAAGACCTCC
2885  116_HRV60b    CGTCGCAACAAGAATATATCATAAAGCAAAGCATGTTAAGGCTTGGTGTCCAAGACCTCC
2886  117_HRV64a    CATCACTACTAGGGTTTATCACAAAGCAAAACATGTCAAGGCATGGTGTCCACGGCCCCC
2887  118_HRV64b    CATCACTACTAGGGTTTATCACAAAGCAAAACATGTCAAGGCATGGTGTCCACGGCCCCC
2888  119_HRV64     CATCACTACTAGGGTTTATCACAAAGCAAAACATGTCAAGGCATGGTGTCCACGGCCCCC
2889  120_HRV94a    CATCACTACTAGAGTGTACCACAAAGCAAAACATGTGAAAGCGTGGTGCCCGCGCCCTCC
2890  121_HRV94b    CATCACTACTAGAGTGTACCACAAAGCAAAACATGTGAAAGCGTGGTGCCCGCGCCCTCC
2891  122_HRV94     CATCACTACTAGAGTGTACCACAAAGCAAAACATGTGAAAGCGTGGTGCCCGCGCCCTCC
2892  123_HRV22     AATTACAACTAGAGTGTACCACAAAGCAAAACATGTAAAGGCATGGTGCCCACGTCCTCC
2893  124_HRV22a    AATTACAACTAGAGTGTACCACAAAGCAAAACATGTAAAGGCATGGTGCCCACGTCCTCC
2894  125_HRV22b    AATTACAACTAGAGTGTACCACAAAGCAAAACATGTAAAGGCATGGTGCCCACGTCCTCC
2895  126_HRV82     CATTACCACAAGAATATATCACAAAGCAAAACATGTGAAAGCGTGGTGTCCACGACCCCC
2896  127_HRV82b    CATTACCACAAGAATATATCACAAAGCAAAACATGTGAAAGCGTGGTGTCCACGACCCCC
2897  128_HRV82a    CATTACCACAAGAATATATCACAAAGCAAAACATGTGAAAGCGTGGTGTCCACGACCCCC
2898  129_HRV19     AATCACAACTAGAGTATATCATAAAGCTAAACATATAAAAGCTTGGTGCCCACGACCACC
2899  130_HRV19a    AATCACAACTAGAGTATATCATAAAGCTAAACATATAAAAGCTTGGTGCCCACGACCACC
2900  131_HRV19b    AATCACAACTAGAGTATATCATAAAGCTAAACATATAAAAGCTTGGTGCCCACGACCACC
2901  132_HRV13     GGTTACAACTAGAATCTATCATAAAGCTAAACATGTCAAAGCATGGTGTCCTAGACCTCC
2902  133_HRV13a    GGTTACAACTAGAATCTATCATAAAGCTAAACATGTCAAAGCATGGTGTCCTAGACCTCC
2903  134_HRV13b    GGTTACAACTAGAATCTATCATAAAGCTAAACATGTCAAAGCATGGTGTCCTAGACCTCC
2904  135_HRV41     GGTCACAACTAGAGTTTACCACAAAGCTAAACATGTCAAAGCATGGTGTCCTAGACCTCC
2905  136_HRV41a    GGTCACAACTAGAGTTTACCACAAAGCTAAACATGTTAAAGCATGGTGTCCTAGACCTCC
2906  137_HRV41b    GGTCACAACTAGAGTTTACCACAAAGCTAAACATGTTAAAGCATGGTGTCCTAGACCTCC
2907  138_HRV73     GGTTACTACTAGAATCTATCATAAAGCTAAACATGTTAAAGCTTGGTGTCCAAGACCTCC
2908  139_HRV73b    GGTTACTACTAGAATCTATCATAAGGCTAAACATGTTAAAGCTTGGTGTCCAAGACCTCC
2909  140_HRV73a    GGTTACTACTAGAATCTATCATAAGGCTAAACATGTTAAAGCTTGGTGTCCAAGACCTCC
2910  141_HRV61     AATCACAACTAGGATTTACCATAAAGCTAAACATGTTAAAGTCTGGTGTCCTAGACCCCC
2911  142_HRV61a    AATCACAACTAGGATTTACCATAAAGCTAAACATGTTAAAGTCTGGTGTCCTAGACCCCC
2912  143_HRV61b    AATCACAACTAGGATTTACCATAAAGCTAAACATGTTAAAGTCTGGTGTCCTAGACCCCC
2913  144_HRV96     AATTACAACCAGAGTTTACCACAAAGCTAAACATGTTAAGGTGTGGTGCCCGAGACCCCC
2914  145_HRV96b    AATTACAACCAGAGTTTACCACAAAGCTAAACATGTTAAGGTGTGGTGCCCGAGACCCCC
2915  146_HRV96a    AATTACAACCAGAGTTTACCACAAAGCTAAACATGTTAAGGTGTGGTGCCCGAGACCCCC
2916  90_HRV16a|    AGTGGTAACAAGGATATATCACAAAGCCAAACACACCAAAGCTTGGTGCCCAAGACCACC
2917  91_HRV16b|    AGTGGTAACAAGGATATATCACAAAGCCAAACACACCAAAGCTTGGTGCCCAAGACCACC
2918  92_1AYM_A     AGTGGTAACAAGGATATATCACAAAGCCAAACACACCAAAGCTTGGTGCCCAAGACCACC
2919  93_HRV81a|    AATAGTAACAAGAATATATCACAAAGCTAAGCACACCAAAGCTTGGTGTCCAAGACCACC
2920  94_HRV81b|    AATAGTAACAAGAATATATCACAAAGCTAAGCACACCAAAGCTTGGTGTCCAAGACCACC
2921  95_HRV81      AATAGTAACAAGAATATATCACAAAGCTAAGCACACCAAAGCTTGGTGTCCAAGACCACC
2922  147_HRV2      TATAATGACAAGAATCTATCACAAGGCTAAACATGTCAAGGCATGGTGTCCACGCCCACC
2923  148_HRV2a|    TATAATGACAAGAATCTATCACAAGGCTAAACATGTCAAGGCATGGTGTCCACGCCCACC
2924  149_HRV2b|    TATAATGACAAGAATCTATCACAAGGCTAAACATGTCAAGGCATGGTGTCCACGCCCACC
2925  150_HRV49a    TATCATGACAAGAATCTATCACAAAGCTAAACACGTCAAAGCATGGTGTCCGCGCCCACC
```

FIG. D7 CONT'D

```
03.trace                                                                         9/20/2007 5:03 PM 2926 151_HRV49b    TATCATGACAAGAATCTATCATAAAGCTAAACACGTCAAAGCATGGTGTCCGCGCCCACC
2927 152_HRV49     TATCATGACAAGAATCTATCATAAAGCTAAACACGTCAAAGCATGGTGTCCGCGCCCACC
2928 153_HRV23a    GATAATGACAAGGGTCTACCACAAAGCTAAACATGTCAAAGCATGGTGTCCGCGGCCACC
2929 154_HRV23b    GATAATGACAAGGGTCTACCACAAAGCTAAACATGTCAAAGCATGGTGTCCGCGGCCACC
2930 155_HRV23     GATAATGACAAGGGTCTACCACAAAGCTAAACATGTCAAAGCATGGTGTCCGCGGCCACC
2931 156_HRV30a    CATAATGACAAGGGTCTACCACAAGGCTAAACATGTCAAAGCGTGGTGTCCACGGCCACC
2932 157_HRV30b    CATAATGACAAGGGTCTACCACAAGGCTAAACATGTCAAAGCGTGGTGTCCACGGCCACC
2933 158_HRV30     CATAATGACAAGGGTCTACCACAAGGCTAAACATGTCAAAGCGTGGTGTCCACGGCCACC
2934 159_HRV7      GATTGTGAGTCGCATTTACCACAAAGCCAAACATATAAAAGCATGGTGCCCACGCCCACC
2935 160_HRV7b|    GATTGTGAGTCGCATTTACCACAAAGCCAAACATATAAAAGCATGGTGCCCACGCCCACC
2936 161_HRV7a|    GATTGTGAGTCGCATTTACCACAAAGCCAAACATATAAAAGCATGGTGCCCACGCCCACC
2937 162_HRV88     TATCATTAGCCGTATATATCACAAGGCTAAACATATAAAGGCATGGTGTCCACGCCCACC
2938 163_HRV88a    TATCATTAGCCGTATATATCACAAGGCTAAACATATAAAGGCATGGTGTCCACGCCCACC
2939 164_HRV88b    TATCATTAGCCGTATATATCACAAGGCTAAACATATAAAGGCATGGTGTCCACGCCCACC
2940 165_HRV36a    TATTGTATGCCGCATTTATCATAAAGCTAAACACATAAAGGCCTGGTGCCCGCGTCCACC
2941 166_HRV36b    TATTGTATGCCGCATTTATCATAAAGCTAAACACATAAAGGCCTGGTGCCCGCGTCCACC
2942 167_HRV36     TATTGTATGCCGCATTTATCATAAAGCTAAACACATAAAGGCCTGGTGCCCGCGTCCACC
2943 168_HRV89a    TATTGTGTGCCGCATTTACCACAAGGCCAAACATATAAAAGCATGGTGTCCTCGCCCACC
2944 169_HRV89b    TATTGTGTGCCGCATTTACCACAAGGCCAAACATATAAAAGCATGGTGTCCTCGCCCACC
2945 170_HRV89     TATTGTGTGCCGCATTTACCACAAGGCCAAACATATAAAAGCATGGTGTCCTCGCCCACC
2946 171_HRV58     CATTGTCTGTCGCATTTACCACAAAGCCAAGCATATAAAAGCATGGTGTCCACGCCCACC
2947 172_HRV58a    CATTGTCTGTCGCATTTACCACAAAGCCAAGCATATAAAAGCATGGTGTCCACGCCCACC
2948 173_HRV58b    CATTGTCTGTCGCATTTACCACAAAGCCAAGCATATAAAAGCATGGTGTCCACGCCCACC
2949 174_HRV12a    GATTACCAGTAGAATATACCATAAAGCAAAACATATCAGTGCCTGGGGCCCTAGACCACC
2950 175_HRV12b    GATTACCAGTAGAATATACCATAAAGCAAAACATATCAGTGCCTGGGGCCCTAGACCACC
2951 176_HRV12     GATTACCAGTAGAATATACCATAAAGCAAAACATATCAGTGCCTGGGGCCCTAGACCACC
2952 177_HRV78a    AATTACAGCTAGAGTCTACCACAAGGCCAAACATATTAGTGCATGGGGCCCAAGACCTCC
2953 178_HRV78b    AATTACAGCTAGAGTCTACCACAAGGCCAAACATATTAGTGCATGGGGCCCAAGACCTCC
2954 179_HRV78     AATTACAGCTAGAGTCTACCACAAGGCCAAACATATTAGTGCATGGGGCCCAAGACCTCC
2955 180_HRV20     GATAACCAGTAGGATATTCCACAAGGCAAAGCATATTAGTGCATGGTGTCCAAGGGCCCC
2956 181_HRV20a    GATAACCAGTAGGATATTCCACAAGGCAAAGCATATTAGTGCATGGTGTCCAAGGGCCCC
2957 182_HRV20b    GATAACCAGTAGGATATTCCACAAGGCAAAGCATATTAGTGCATGGTGTCCAAGGGCCCC
2958 183_HRV68     AATAACCAGCAGAATATTCCATAAAGCAAAACATATTAGTGCGTGGTGTCCAAGAGCTCC
2959 184_HRV68a    AATAACCAGCAGAATATTCCATAAAGCAAAACATATTAGTGCGTGGTGTCCAAGAGCTCC
2960 185_HRV68b    AATAACCAGCAGAATATTCCATAAAGCAAAACATATTAGTGCGTGGTGTCCAAGAGCTCC
2961 186_HRV28     AATAACCAGCATAATATTCCACAAAGCTAAACATGTCAGTGCATGGTGCCCCAGACCTCC
2962 187_HRV28a    AATAACCAGCATAATATTCCACAAAGCTAAACATGTCAGTGCATGGTGCCCCAGACCTCC
2963 188_HRV28b    AATAACCAGCATAATATTCCACAAAGCTAAACATGTCAGTGCATGGTGCCCCAGACCTCC
2964 189_HRV53a    GATAACCAGTAGGATTTATCACAAGGCTAAACATATCAGTGCATGGTGTCCAAGACCACC
2965 190_HRV53b    GATAACCAGTAGGATTTATCACAAGGCTAAACATATCAGTGCATGGTGTCCAAGACCACC
2966 191_HRV53     GATAACCAGTAGGATTTATCACAAGGCTAAACATATCAGTGCATGGTGTCCAAGACCACC
2967 192_HRV46a    TATAACTAGCAGAATATATCACAAGGCTAAACACATTAAAGCATGGTGCCCCAGGGCACC
2968 193_HRV46b    TATAACTAGCAGAATATATCACAAGGCTAAACACATTAAAGCATGGTGCCCCAGGGCACC
2969 194_HRV46     TATAACTAGCAGAATATATCACAAGGCTAAACACATTAAAGCATGGTGCCCCAGGGCACC
2970 195_HRV80a    AATCACCAGCAGAATATATCACAAAGCTAAACACATCAAAGCATGGTGTCCAAGAGCACC
2971 196_HRV80b    AATCACCAGCAGAATATATCACAAAGCTAAACACATCAAAGCATGGTGTCCAAGAGCACC
2972 197_HRV80     AATCACCAGCAGAATATATCACAAAGCTAAACACATCAAAGCATGGTGTCCAAGAGCACC
2973 198_HRV51     CATAACTAGCAGGATTTACCACAAAGCCAAACATGTCAGTGCATGGTGCCCTCGTCCTCC
2974 199_HRV51a    CATAACTAGCAGGATTTACCACAAAGCCAAACATGTCAGTGCATGGTGCCCTCGTCCTCC
2975 200_HRV51b    CATAACTAGCAGGATTTACCACAAAGCCAAACATGTCAGTGCATGGTGCCCTCGTCCTCC
2976 201_HRV65a    CATAACCAGTAGAATATATCATAAAGCTAAACACATCAGTGCTTGGTGTCCACGACCTCC
2977 202_HRV65b    CATAACCAGTAGAATATATCATAAAGCTAAACACATCAGTGCTTGGTGTCCACGACCTCC
2978 203_HRV65     CATAACCAGTAGAATATATCATAAAGCTAAACACATCAGTGCTTGGTGTCCACGACCTCC
2979 204_HRV71a    CATAACAAGTAGGATTTATCACAAAGCCAAACATGTCAGAGCATGGTGTCCTAGACCCCC
2980 205_HRV71b    CATAACAAGTAGGATTTATCACAAAGCCAAACATGTCAGAGCATGGTGTCCTAGACCCCC
2981 206_HRV71     CATAACAAGTAGGATTTATCACAAAGCCAAACATGTCAGAGCATGGTGTCCTAGACCCCC
2982 207_HRV8      AATTGATTCAAGAATATACCTGAAAGCAAAGCACATTAAAGCTTGGTGTCCTAGACCCCC
2983 208_HRV95     AATTGATTCAAGAATATACCTGAAAGCAAAGCATATTAAAGCTTGGTGTCCTAGACCCCC
2984 209_HRV45     GATCGACTCCATGGTATATCTAAAAGCTAAACACATCAAGGCATGGTGTCCCAGACCTCC
2985 210_HRV45a    GATCGACTCCATGGTATATCTAAAAGCTAAACACATCAAGGCATGGTGTCCCAGACCTCC
2986 211_HRV45b    GATCGACTCCATGGTATATCTAAAAGCTAAACACATCAAGGCATGGTGTCCCAGACCTCC
2987 GROUP_1       --T-----------T-T--C--AA-GC-AA-CA----------TGG-G-CC--G--C-C-
2988
2989 1_HRV1A1|d    TAGAGCTGTCCCTTACACA-CATAGTCATGTGACTAATTATATGC-CAGAAA---CAGGT
2990 2_HRV1A2|d    TAGAGCTGTCCCTTACACA-CATAGTCATGTGACTAATTATATGC-CAGAAA---CAGGT
```

FIG. D7 CONT'D 03.trace                                                                                                9/20/2007 5:03 PM

```
2991  3_HRV1A|cD    TAGAGCTGTCCCTTACACA-CATAGTCATGTGACTAATTATATGC-CAGAAA---CAGGT
2992  4_HRV1B1|d    TAGAGCTGTTCCTTACACA-CATAGTCGTGTAACTAATTATGTAC-CAAAAA---CAGGT
2993  5_HRV1B2|d    TAGAGCTGTTCCTTACACA-CATAGTCGTGTAACTAATTATGTAC-CAAAAA---CAGGT
2994  6_HRV1B       TAGAGCTGTTCCTTACACA-CATAGTCGTGTAACTAATTATGTAC-CAAAAA---CAGGT
2995  7_HRV40a|d    AAGAGCAGTACCTTACACA-CATACACACTCAACAAATTATAAAC-CTCAAG---AAGGT
2996  8_HRV40b|d    AAGAGCAGTACCTTACACA-CATACACACTCAACAAATTATAAAC-CTCAAG---AAGGT
2997  9_HRV40       AAGAGCAGTACCTTACACA-CATACACACTCAACAAATTATAAAC-CTCAAG---AAGGT
2998  10_HRV85      AAGAGCGGTGCCTTATACA-CACACACGCTCAACCAACTATGTGC-CACAAG---ATGGT
2999  11_HRV85a|    AAGAGCGGTGCCTTATACA-CACACACGCTCAACCAACTATGTGC-CACAAG---ATGGT
3000  12_HRV85b|    AAGAGCGGTGCCTTATACA-CACACACGCTCAACCAACTATGTGC-CACAAG---ATGGT
3001  13_HRV56a|    AAGGGCTGTGCCTTATACA-CATGCTCACGTCACCAATTATAAAC-CACAAG---ATGGT
3002  14_HRV56b|    AAGGGCTGTGCCTTATACA-CATGCTCACGTCACCAATTATAAAC-CACAAG---ATGGT
3003  15_HRV56      AAGGGCTGTGCCTTATACA-CATGCTCACGTCACCAATTATAAAC-CACAAG---ATGGT
3004  16_HRV54      TAGGGCTGTCCCATACACA-CATACTAGATCAACAAATTACATGC-CACGGG---AGGGT
3005  17_HRV98      TAGAGCTGTTCCATACACA-CACACTAGATCAACTAATTACATGC-CTCAAG---ATGGT
3006  18_HRV59a|    TAGAGCAGTCCCTTACACA-CACAGCTACGTAACTAACTACAAGATTGCTGG---AAAA-
3007  19_HRV59b|    TAGAGCAGTCCCTTACACA-CACAGCTACGTAACTAACTACAAGATTGCTGG---AAAA-
3008  20_HRV59      TAGAGCAGTCCCTTACACA-CACAGCTACGTAACTAACTACAAGATTGCTGG---AAAA-
3009  21_HRV63      TAGGGCTGTTCCATACACA-CATAGTTATGTCACTAACTATAAAATTACAGG---ACAG-
3010  22_HRV63b|    TAGGGCTGTTCCATACACA-CATAGTTATGTCACTAACTATAAAATTACAGG---ACAG-
3011  23_HRV63a|    TAGGGCTGTTCCATACACA-CATAGTTATGTCACTAACTATAAAATTACAGG---ACAG-
3012  24_HRV39      CAGAGCAGTCCCTTACACA-CACAGCAATGTTACAAATTACAAAG-TACGGG---ACGGT
3013  25_HRV39a|    CAGAGCAGTCCCTTACACA-CACAGCAATGTTACAAATTACAAAG-TACGGG---ACGGT
3014  26_HRV39b|    CAGAGCAGTCCCTTACACA-CACAGCAATGTTACAAATTACAAAG-TACGGG---ACGGT
3015  27_HRV10a|    CAGAGCTGTACCATATACA-CATGCCCATTCCACAAATTACAAAC-CACATG---GCAAA
3016  28_HRV10b|    CAGAGCTGTACCATATACA-CATGCCCATTCCACAAATTACAAAC-CACATG---GCAAA
3017  29_HRV10      CAGAGCTGTACCATATACA-CATGCCCATTCCACAAATTACAAAC-CACATG---GCAAA
3018  30_HRV100a    TCGGGCTGTGCCGTACACA-CATAGTCACTCTACAAATTACAAAC-CACATG---AGGGT
3019  31_HRV100b    TCGGGCTGTGCCGTACACA-CATAGTCACTCTACAAATTACAAAC-CACATG---AGGGT
3020  32_HRV100     TCGGGCTGTGCCGTACACA-CATAGTCACTCTACAAATTACAAAC-CACATG---AGGGT
3021  33_HRV66      TAGAGCTGTACCATACACA-ACTGTAAACTCAACCAATTATATGC-CTCATA---CTGGT
3022  34_HRV66b|    TAGAGCTGTACCATACACA-ACTGTAAACTCAACCAATTATATGC-CTCATA---CTGGT
3023  35_HRV66a|    TAGAGCTGTACCATACACA-ACTGTAAACTCAACCAATTATATGC-CTCATA---CTGGT
3024  36_HRV77a|    TAGAGCTGTACCATACACA-GCAGTAGATTCAACAAATTACAAAC-CTATGA---GAGGG
3025  37_HRV77b|    TAGAGCTGTACCATACACA-GCAGTAGATTCAACAAATTACAAAC-CTATGA---GAGGG
3026  38_HRV77      TAGAGCTGTACCATACACA-GCAGTAGATTCAACAAATTACAAAC-CTATGA---GAGGG
3027  39_HRV62a     CAGAGCTGTTCCATATAAA-TATGTTGATTTCAATAATTATGCAG-CCAGTG---ATAGT
3028  40_HRV62b     TAGAGCTGTTCCATATAAA-TATGTTGATTTCAATAATTATGCAG-CCAGTG---ATAGT
3029  41_HRV25      TAGAGCTGTCCCATATAAA-TATGTTGACTTCAATAATTATGCAG-CCAGTG---ATAAT
3030  42_HRV29a     AAGAGTTGTCCCATACAAG-TATGTTGGCCTAACTAATTACACAC-TTAAAG---AAGAA
3031  43_HRV29b     AAGAGTTGTCCCATACAAG-TATGTTGGCCTAACTAATTACACAC-TTAAAG---AAGAA
3032  44_HRV44a     AAGGGTTGTCCCATACAAG-TATGTTGGCCTAACTAATTACACAC-TTAAAG---AAACA
3033  45_HRV44b     AAGGGTTGTCCCATACAAG-TATGTTGGCCTAACTAATTACACAC-TTAAAG---AAACA
3034  46_HRV31      TAGAGCAGTTCCATACAGGGTATG-TGGATCAACAAACTACAAAC-CTGATG---AAAAT
3035  47_HRV31a|    TAGAGCAGTTCCATACAGGGTATG-TGGATCAACAAACTACAAAC-CTGATG---AAAAT
3036  48_HRV31b|    TAGAGCAGTTCCATACAGG-TATGTTGGATCAACAAACTACAAAC-CTGATG---AAAAT
3037  49_HRV47      TAGAGCTGTTCCATATAGA-TATGTTGGATCAACAAATTACAAAC-CTGATC---AAGGA
3038  50_HRV47a|    TAGAGCTGTTCCATATAGA-TATGTTGGATCAACAAATTACAAAC-CTGATC---AAGGA
3039  51_HRV47b|    TAGAGCTGTTCCATATAGA-TATGTTGGATCAACAAATTACAAAC-CTGATC---AAGGA
3040  52_HRV11      TAGAGCTGTAGAATATACT-CACACTCATGTAACCAATTACAAAC-CACAGG---AAGGA
3041  53_HRV11b|    TAGAGCTGTAGAATATACT-CACACTCATGTAACCAATTACAAAC-CACAGG---AAGGA
3042  54_HRV11a|    TAGAGCTGTAGAATATACT-CACACTCATGTAACCAATTACAAAC-CACAGG---AAGGA
3043  55_HRV76      TAGAGCTGTAGAGTATACA-TACACCCATGTAACAAACTACAAAC-CACATT---CTGGT
3044  56_HRV76b|    TAGAGCTGTAGAGTATACA-TACACCCATGTAACAAACTACAAAC-CACATT---CTGGT
3045  57_HRV76a|    TAGAGCTGTAGAGTATACA-TACACCCATGTAACAAACTACAAAC-CACATT---CTGGT
3046  58_HRV33      TAGAGCTGTGGAATACACC-CATACTCATGTTACAAATTATAAAT-CAACAA---CTCGT
3047  59_HRV33b|    TAGAGCTGTGGAATACACC-CATACTCATGTTACAAATTATAAAT-CAACAA---CTCGT
3048  60_HRV33a|    TAGAGCTGTGGAATACACC-CATACTCATGTTACAAATTATAAAT-CAACAA---CTCGT
3049  61_HRV24a|    CAGAGCTGTTGAGTATACA-CATACTCACGTGACCAATTATAAGC-ATCAGA---CTCGT
3050  62_HRV24b|    CAGAGCTGTTGAGTATACA-CATACTCACGTGACCAATTATAAGC-ATCAGA---CTCGT
3051  63_HRV24      CAGAGCTGTTGAGTATACA-CATACTCACGTGACCAATTATAAGC-ATCAGA---CTCGT
3052  64_HRV90      TAGGGCAGTTGAATACACA-CACACTCATGTAACAAACTACAAAC-ATGCAA---CACGT
3053  65_HRV90a|    TAGGGCAGTTGAATACACA-CACACTCATGTAACAAACTACAAAC-ATGCAA---CACGT
3054  66_HRV90b|    TAGGGCAGTTGAATACACA-CACACTCATGTAACAAACTACAAAC-ATGCAA---CACGT
3055  67_HRV34      AAGAGCTGTTGAGTACACA-CACACACATGTTACTAACTACAAAG-TTAGGG---GTAAA
```

FIG. D7 CONT'D 03.trace                                                                9/20/2007 5:03 PM

```
3056  68_HRV34b|    AAGAGCTGTTGAGTACACA-CACACACATGTTACTAACTACAAAG-TTAGGG---GTAAA
3057  69_HRV34a|    AAGAGCTGTTGAGTACACA-CACACACATGTTACTAACTACAAAG-TTAGGG---GTAAA
3058  70_HRV50a|    AAGAGCTGTTGAATACACA-CACACCCATGTCACTAACTACAAGA-AAAGTG---ATGCT
3059  71_HRV50b|    AAGAGCTGTTGAATACACA-CACACCCATGTCACTAACTACAAGA-AAAGTG---ATGCT
3060  72_HRV50     AAGAGCTGTTGAATACACA-CACACCCATGTCACTAACTACAAGA-AAAGTG---ATGCT
3061  73_HRV18a|    GAGAGCTGTGGAGTACACA-CATACACATGTAACTAACTACAAGC-CTAAGG---AAGGA
3062  74_HRV18b|    GAGAGCTGTGGAGTACACA-CATACACATGTAACTAACTACAAGC-CTAAGG---AAGGA
3063  75_HRV18     GAGAGCTGTGGAGTACACA-CATACACATGTAACTAACTACAAGC-CTAAGG---AAGGA
3064  76_HRV55     TAGGGCTGTTGAATACACA-CACACACATGTCACAAATTACAAGA-AGACTG---ATGGC
3065  77_HRV55b|    TAGGGCTGTTGAATACACA-CACACACATGTCACAAATTACAAGA-AGACTG---ATGGC
3066  78_HRV55a|    TAGGGCTGTTGAATACACA-CACACACATGTCACAAATTACAAGA-AGACTG---ATGGC
3067  79_HRV57     ACGGGCTATCGAGTACACA-CATACACATGTTACTAATTATAAAA-TAAAAG---ATAGA
3068  80_HRV57a|    ACGGGCTATCGAGTACACA-CATACACATGTTACTAATTATAAAA-TAAAAG---ATAGA
3069  81_HRV57b|    ACGGGCTATCGAGTACACA-CATACACATGTTACTAATTATAAAA-TAAAAG---ATAGA
3070  82_HRV21     GAGGGCCGTTGAATACACA-CATACACACGTAACCAATTACAAAA-TTGCAA---ATCAT
3071  83_HRVHan    GAGGGCCGTTGAATACACA-CATACACATGTAACCAATTACAAAA-TTGCAA---ATAAA
3072  84_HRV43     CAGAGCTGTTGAATACACA-CACACACATGTCACAAATTATAAAA-GAGAAG---GAAAG
3073  85_HRV43b|    CAGAGCTGTTGAATACACA-CACACACATGTCACAAATTATAAAA-GAGAAG---GAAAG
3074  86_HRV43a|    CAGAGCTGTTGAATACACA-CACACACATGTCACAAATTATAAAA-GAGAAG---GAAAG
3075  87_HRV75     CAGGGCTGTTGAATACACA-TTTAGACGTGTAACAAATTACAAAA-GAGATG---GACAA
3076  88_HRV75b|    CAGGGCTGTTGAATACACA-TTTAGACGTGTAACAAATTACAAAA-GAGATG---GACAA
3077  89_HRV75a|    CAGGGCTGTTGAATACACA-TTTAGACGTGTAACAAATTACAAAA-GAGATG---GACAA
3078  96_HRV9a|d    TAGGGCAGTTGAGTATATA-CATACACATGTCACAAATTACAAGC-CAAGCA---CAGGC
3079  97_HRV9b|d    TAGGGCAGTTGAGTATATA-CATACACATGTCACAAATTACAAGC-CAAGCA---CAGGC
3080  98_HRV9      TAGGGCAGTTGAGTATATA-CATACACATGTCACAAATTACAAGC-CAAGCA---CAGGC
3081  99_HRV32     TAGGGCAGTTGAATATACA-CATACACATGTTACAAATTACAAAC-CAAGCA---CAGGT
3082  100_HRV32a    TAGGGCAGTTGAATATACA-CATACACATGTTACAAATTACAAAC-CAAGCA---CAGGT
3083  101_HRV32b    TAGGGCAGTTGAATATACA-CATACACATGTTACAAATTACAAAC-CAAGCA---CAGGT
3084  102_HRV67     TAGAGCAGTTGAATACATA-CACACACATGTTACAAACTATAGAC-CAGAAA---CAGGT
3085  103_HRV67a    TAGAGCAGTTGAATACATA-CACACACATGTTACAAACTATAGAC-CAGAAA---CAGGT
3086  104_HRV67b    TAGAGCAGTTGAATACATA-CACACACATGTTACAAACTATAGAC-CAGAAA---CAGGT
3087  105_HRV15     TAGAGCAGTGGAATATACA-CACACACATGTCACAAATTACAAAC-CACAAG---ATGGT
3088  106_HRV15a    TAGAGCAGTGGAATATACA-CACACACATGTCACAAATTACAAAC-CACAAG---ATGGT
3089  107_HRV15b    TAGAGCAGTGGAATATACA-CACACACATGTCACAAATTACAAAC-CACAAG---ATGGT
3090  108_HRV74a    TAGAGCAGTTGAATATACT-CACACACATGTCACAAATTACAAAC-CACAAG---AAGGT
3091  109_HRV74b    TAGAGCAGTTGAATATACT-CACACACATGTCACAAATTACAAAC-CACAAG---AAGGT
3092  110_HRV74    TAGAGCAGTTGAATATACT-CACACACATGTCACAAATTACAAAC-CACAAG---AAGGT
3093  111_HRV38a    AAGGGCAGTTGAATATAGA-CATACACATGTTAACAATTACAAAC-CAGACC---AAGGG
3094  112_HRV38b    AAGGGCAGTTGAATATAGA-CATACACATGTTAACAATTACAAAC-CAGACC---AAGGG
3095  113_HRV38    AAGGGCAGTTGAATATAGA-CATACACATGTTAACAATTACAAAC-CAGACC---AAGGG
3096  114_HRV60     AAGGGCAGTTGAATATAGA-CACACACATGTAAACAACTATAGAC-CAGATG---ATGGA
3097  115_HRV60a    AAGGGCAGTTGAATATAGA-CACACACATGTAAACAACTATAGAC-CAGATG---ATGGA
3098  116_HRV60b    AAGGGCAGTTGAATATAGA-CACACACATGTAAACAACTATAGAC-CAGATG---ATGGA
3099  117_HRV64a    AAGAGCTGTTGGATATACA-CATACAAATGTCACCAATTATAAAC-CATCCA---AAGGA
3100  118_HRV64b    AAGAGCTGTTGGATATACA-CATACAAATGTCACCAATTATAAAC-CATCCA---AAGGA
3101  119_HRV64    AAGAGCTGTTGGATATACA-CATACAAATGTCACCAATTATAAAC-CATCCA---AAGGA
3102  120_HRV94a    AAGAGCTGTTGGATACACA-CATACGCATGTCACTAATTACAAAC-CATCTG---AAGGG
3103  121_HRV94b    AAGAGCTGTTGGATACACA-CATACGCATGTCACTAATTACAAAC-CATCTG---AAGGG
3104  122_HRV94    AAGAGCTGTTGGATACACA-CATACGCATGTCACTAATTACAAAC-CATCTG---AAGGG
3105  123_HRV22    AAGAGCTGTTGGATATACA-CACACACATGTGACAAACTACAAAC-CATCTG---TAGGG
3106  124_HRV22a    AAGAGCTGTTGGATATACA-CACACACATGTGACAAACTACAAAC-CATCTG---TAGGG
3107  125_HRV22b    AAGAGCTGTTGGATATACA-CACACACATGTGACAAACTACAAAC-CATCTG---TAGGG
3108  126_HRV82    GAGGGCTGTGGGTTATACA-CACACACATGTTACCAACTACAAGC-CATCAC---AGGGA
3109  127_HRV82b    GAGGGCTGTGGGTTATACA-CACACACATGTTACCAACTACAAGC-CATCAC---AGGGA
3110  128_HRV82a    GAGGGCTGTGGGTTATACA-CACACACATGTTACCAACTACAAGC-CATCAC---AGGGA
3111  129_HRV19    CAGAGCCGTGGAATATACC-CACACTCATGTGACTAATTATAAAC-CCCAGA---CAGGT
3112  130_HRV19a    CAGAGCCGTGGAATATACC-CACACTCATGTGACTAATTATAAAC-CCCAGA---CAGGT
3113  131_HRV19b    CAGAGCCGTGGAATATACC-CACACTCATGTGACTAATTATAAAC-CCCAGA---CAGGT
3114  132_HRV13    CAGAGCTGTTGAATATACT-AATGTGCATGTTACAAACTACAAAC-CAGGGA---CAGGA
3115  133_HRV13a    CAGAGCTGTTGAATATACT-AATGTGCATGTTACAAACTACAAAC-CAGGGA---CAGGA
3116  134_HRV13b    CAGAGCTGTTGAATATACT-AATGTGCATGTTACAAACTACAAAC-CAGGGA---CAGGA
3117  135_HRV41    CAGGGCTGTGGAGTACACC-AATGTGCATGTCACAAATTACAAAC-CAAAAG---CAGGA
3118  136_HRV41a    CAGGGCTGTGGAGTACACC-AATGTGCATGTCACAAATTACAAAC-CAAAAG---CAGGA
3119  137_HRV41b    CAGGGCTGTGGAGTACACC-AATGTGCATGTCACAAATTACAAAC-CAAAAG---CAGGA
3120  138_HRV73    TAGGGCAGTAGAATATACA-AATGCACATGTGACCAATTATAAAC-CCACTG---ATGGA
```

FIG. D7 CONT'D 03.trace                                                                9/20/2007 5:03 PM

```
3121  139_HRV73b   TAGGGCAGTAGAATATACA-AATGCACATGTGACCAATTATAAAC-CCACTG---ATGGA
3122  140_HRV73a   TAGGGCAGTAGAATATACA-AATGCACATGTGACCAATTATAAAC-CCACTG---ATGGA
3123  141_HRV61    CAGAGCAGTGGAATATACT-AATGTGCATTTGACCAATTACAAGC-CCAAAG---ATAGT
3124  142_HRV61a   CAGAGCAGTGGAATATACT-AATGTGCATTTGACCAATTACAAGC-CCAAAG---ATAGT
3125  143_HRV61b   CAGAGCAGTGGAATATACT-AATGTGCATTTGACCAATTACAAGC-CCAAAG---ATAGT
3126  144_HRV96    TAGAGCAGTTGAATACACA-AATGTGCATCTCACAAATTATAAAC-CCAACA---ATG--
3127  145_HRV96b   TAGAGCAGTTGAATACACA-AATGTGCATCTCACAAATTATAAAC-CCAACA---ATG--
3128  146_HRV96a   TAGAGCAGTTGAATACACA-AATGTGCATCTCACAAATTATAAAC-CCAACA---ATG--
3129   90_HRV16a|  CAGAGCTGTTCAATACTCA-CATACACATACCACCAACTACAAAT-TGAGTT---CAGAA
3130   91_HRV16b|  CAGAGCTGTTCAATACTCA-CATACACATACCACCAACTACAAAT-TGAGTT---CAGAA
3131   92_1AYM_A   CAGAGCTGTTCAATACTCA-CATACACATACCACCAACTACAAAT-TGAGTT---CAGAA
3132   93_HRV81a|  CAGGGCTGTTCAGTACACA-CATACACATGTAACTAATTATAAAT-TAGAAA---CAGAT
3133   94_HRV81b|  CAGGGCTGTTCAGTACACA-CATACACATGTAACTAATTATAAAT-TAGAAA---CAGAT
3134   95_HRV81    CAGGGCTGTTCAGTACACA-CATACACATGTAACTAATTATAAAT-TAGAAA---CAGAT
3135  147_HRV2     CAGAGCGCTTGAGTATACT-CGTGCTCACCGCACTAATTTTAAAA-TTGAGG---ATAGG
3136  148_HRV2a|   CAGAGCGCTTGAGTATACT-CGTGCTCACCGCACTAATTTTAAAA-TTGAGG---ATAGG
3137  149_HRV2b|   CAGAGCGCTTGAGTATACT-CGTGCTCACCGCACTAATTTTAAAA-TTGAGG---ATAGG
3138  150_HRV49a   CAGAGCACTTGAATATACT-CGCGCTCACCGTACTAATTTCAAAG-TTGAAG---ACAGA
3139  151_HRV49b   CAGAGCACTTGAATATACT-CGCGCTCACCGTACTAATTTCAAAG-TTGAAG---ACAGA
3140  152_HRV49    CAGAGCACTTGAATATACT-CGCGCTCACCGTACTAATTTCAAAG-TTGAAG---ACAGA
3141  153_HRV23a   CAGAGCACTTGAATACACA-CGCGCTCACCGTACTAATTTCAAAA-TTGAAG---GTGAA
3142  154_HRV23b   CAGAGCACTTGAATACACA-CGCGCTCACCGTACTAATTTCAAAA-TTGAAG---GTGAA
3143  155_HRV23    CAGAGCACTTGAATACACA-CGCGCTCACCGTACTAATTTCAAAA-TTGAAG---GTGAA
3144  156_HRV30a   TAGGGCGCTTGAGTATACC-CGTGCTCATCGCACCAATTTTAAAA-TTGATG---GCAGG
3145  157_HRV30b   TAGGGCGCTTGAGTATACC-CGTGCTCATCGCACCAATTTTAAAA-TTGATG---GCAGG
3146  158_HRV30    TAGGGCGCTTGAGTATACC-CGTGCTCATCGCACCAATTTTAAAA-TTGATG---GCAGG
3147  159_HRV7     ACGAGCTGTGCCTTATCAA-CACACTCACTCCACCAACTATGTGC-CACAAA---ATGGA
3148  160_HRV7b|   ACGAGCTGTGCCTTATCAA-CACACTCACTCCACCAACTATGTGC-CACAAA---ATGGA
3149  161_HRV7a|   ACGAGCTGTGCCTTATCAA-CACACTCACTCCACCAACTATGTGC-CACAAA---ATGGA
3150  162_HRV88    AAGAGCCGTACCTTATCAG-CACACACACTCCACCAATTATGTAC-CAACAG---ATGGG
3151  163_HRV88a   AAGAGCCGTACCTTATCAG-CACACACACTCCACCAATTATGTAC-CAACAG---ATGGG
3152  164_HRV88b   AAGAGCCGTACCTTATCAG-CACACACACTCCACCAATTATGTAC-CAACAG---ATGGG
3153  165_HRV36a   AAGGGCCGTTCCTTACCAA-CACACACATTCCACTAATTATATAC-CATACA---AAGGT
3154  166_HRV36b   AAGGGCCGTTCCTTACCAA-CACACACATTCCACTAATTATATAC-CATACA---AAGGT
3155  167_HRV36    AAGGGCCGTTCCTTACCAA-CACACACATTCCACTAATTATATAC-CATACA---AAGGT
3156  168_HRV89a   AAGGGCTGTTGCCTATCAA-CACACACTCAACCAATTACATAC-CATCCA---ATGGT
3157  169_HRV89b   AAGGGCTGTTGCCTATCAA-CACACACACTCAACCAATTACATAC-CATCCA---ATGGT
3158  170_HRV89    AAGGGCTGTTGCCTATCAA-CACACACACTCAACCAATTACATAC-CATCCA---ATGGT
3159  171_HRV58    AAGGGCTGTTCCTTATCAA-TTCACACATTCTACTAATTACATAC-CAGATA---GTGGT
3160  172_HRV58a   AAGGGCTGTTCCTTATCAA-TTCACACATTCTACTAATTACATAC-CAGATA---GTGGT
3161  173_HRV58b   AAGGGCTGTTCCTTATCAA-TTCACACATTCTACTAATTACATAC-CAGATA---GTGGT
3162  174_HRV12a   AAGAGCTGTACCATACCAG-CATATACACAATCCAAATTACAAGA-CAAGTA------AT
3163  175_HRV12b   AAGAGCTGTACCATACCAG-CATATACACAATCCAAATTACAAGA-CAAGTA------AT
3164  176_HRV12    AAGAGCTGTACCATACCAG-CATATACACAATCCAAATTACAAGA-CAAGTA------AT
3165  177_HRV78a   TAGAGCTGTACCTTATCAG-CACATATATAACCCTAATTATAAAA-CTGAAG------AA
3166  178_HRV78b   TAGAGCTGTACCTTATCAG-CACATATATAACCCTAATTATAAAA-CTGAAG------AA
3167  179_HRV78    TAGAGCTGTACCTTATCAG-CACATATATAACCCTAATTATAAAA-CTGAAG------AA
3168  180_HRV20    AAGAGCAGTGCCTTATCAA-CACACTAAGAGCACAAACTTAGTGC-CAAGGA---CAGGT
3169  181_HRV20a   AAGAGCAGTGCCTTATCAA-CACACTAAGAGCACAAACTTAGTGC-CAAGGA---CAGGT
3170  182_HRV20b   AAGAGCAGTGCCTTATCAA-CACACTAAGAGCACAAACTTAGTGC-CAAGGA---CAGGT
3171  183_HRV68    AAGAGCAGTGCCCTACCAG-CACACCAGAAGTACAAACTTAGTAC-CAAAGG---AAGGT
3172  184_HRV68a   AAGAGCAGTGCCCTACCAG-CACACCAGAAGTACAAACTTAGTAC-CAAAGG---AAGGT
3173  185_HRV68b   AAGAGCAGTGCCCTACCAG-CACACCAGAAGTACAAACTTAGTAC-CAAAGG---AAGGT
3174  186_HRV28    ACGCGCTGTAGCTTATCAA-CATACATACAGTCCAAACTTTGTGC-CTCAGG---AAGGT
3175  187_HRV28a   ACGCGCTGTAGCTTATCAA-CATACATACAGTCCAAACTTTGTGC-CTCAGG---AAGGT
3176  188_HRV28b   ACGCGCTGTAGCTTATCAA-CATACATACAGTCCAAACTTTGTGC-CTCAGG---AAGGT
3177  189_HRV53a   AAGAGCAGTTGCATATCAA-CACACATATAGCCCAAATTTTGTAC-CGCAAA---CAGGA
3178  190_HRV53b   AAGAGCAGTTGCATATCAA-CACACATATAGCCCAAATTTTGTAC-CGCAAA---CAGGA
3179  191_HRV53    AAGAGCAGTTGCATATCAA-CACACATATAGCCCAAATTTTGTAC-CGCAAA---CAGGA
3180  192_HRV46a   CAGAGCAGTCCCATATCAA-CATATTTATAATCCAAATTTCAAGA-CTACTCAACCTGAG
3181  193_HRV46b   CAGAGCAGTCCCATATCAA-CATATTTATAATCCAAATTTCAAGA-CTACTCAACCTGAG
3182  194_HRV46    CAGAGCAGTCCCATATCAA-CATATTTATAATCCAAATTTCAAGA-CTACTCAACCTGAG
3183  195_HRV80a   TAGAGCAGTCCCATACCAA-CATACCTACAGCCCAAATTTCAAAA-ACACTG---ATGAA
3184  196_HRV80b   TAGAGCAGTCCCATACCAA-CATACCTACAGCCCAAATTTCAAAA-ACACTG---ATGAA
3185  197_HRV80    TAGAGCAGTCCCATACCAA-CATACCTACAGCCCAAATTTCAAAA-ACACTG---ATGAA
```

FIG. D7 CONT'D 03.trace                                                                9/20/2007 5:03 PM

```
3186 198_HRV51     TCGTGCTGTAGCCTACCAA-CACACATACAGTACAAACTTCGTTC-CAAAAGAGGGATTT
3187 199_HRV51a    TCGTGCTGTAGCCTACCAA-CACACATACAGTACAAACTTCGTTC-CAAAAGAGGGATTT
3188 200_HRV51b    TCGTGCTGTAGCCTACCAA-CACACATACAGTACAAACTTCGTTC-CAAAAGAGGGATTT
3189 201_HRV65a    CCGAGCAGTAGCTTACCAA-CACACATACAGTACAAATTTTGTTC-CTAGCGGAGGTCTT
3190 202_HRV65b    CCGAGCAGTAGCTTACCAA-CACACATACAGTACAAATTTTGTTC-CTAGCGGAGGTCTT
3191 203_HRV65     CCGAGCAGTAGCTTACCAA-CACACATACAGTACAAATTTTGTTC-CTAGCGGAGGTCTT
3192 204_HRV71a    CAGAGCAGTAGCCTACCAA-TCAACATATACCACAAATTTTGTTC-CACAAGACGGGATC
3193 205_HRV71b    CAGAGCAGTAGCCTACCAA-TCAACATATACCACAAATTTTGTTC-CACAAGACGGGATC
3194 206_HRV71     CAGAGCAGTAGCCTACCAA-TCAACATATACCACAAATTTTGTTC-CACAAGACGGGATC
3195 207_HRV8      CAGAGCAGTTACGTATAAC-CATATATACAACCCCAATTATGTTA-GAGAGG------GA
3196 208_HRV95     CAGAGCAGTTACGTATAAC-CATATATACAACCCCAATTATGTTA-GAGAGG------GA
3197 209_HRV45     AAGAGCAGTCACATATAAC-CATACATATAATCCAAATTATGTTA-GGGCTG------AT
3198 210_HRV45a    AAGAGCAGTCACATATAAC-CATACATATAATCCAAATTATGTTA-GGGCTG------AT
3199 211_HRV45b    AAGAGCAGTCACATATAAC-CATACATATAATCCAAATTATGTTA-GGGCTG------AT
3200 GROUP_1       --G-G---T----TA-------------------AA-T----------------------
3201
3202 1_HRV1A1|d    GACG------TGACAACAG---CCATAGTCCGCAGAA------ACACTATAACAACTG--
3203 2_HRV1A2|d    GACG------TGACAACAG---CCATAGTCCGCAGAA------ACACTATAACAACTG--
3204 3_HRV1A|cD    GACG------TGACAACAG---CCATAGTCCGCAGAA------ACACTATAACAACTG--
3205 4_HRV1B1|d    GATG------TGACAACAG---CTATAGTTCCTAGAG------CTAGCATGAAAACTG--
3206 5_HRV1B2|d    GATG------TGACAACAG---CTATAGTTCCTAGAG------CTAGCATGAAAACTG--
3207 6_HRV1B       GATG------TGACAACAG---CTATAGTTCCTAGAG------CTAGCATGAAAACTG--
3208 7_HRV40a|d    GAAG------TCCAGATTT---TCCTCAAAGAGAGAG------CCAGCCTAACAACAG--
3209 8_HRV40b|d    GAAG------TCCAGATTT---TCCTCAAAGAGAGAG------CCAGCCTAACAACAG--
3210 9_HRV40       GAAG------TCCAGATTT---TCCTCAAAGAGAGAG------CCAGCCTAACAACAG--
3211 10_HRV85      GAAG------TTAAGATCT---TCCTCAAAGAGAGAG------CTAGTTTAACCACAG--
3212 11_HRV85a|    GAAG------TTAAGATCT---TCCTCAAAGAGAGAG------CTAGTTTAACCACAG--
3213 12_HRV85b|    GAAG------TTAAGATCT---TCCTCAAAGAGAGAG------CTAGTTTAACCACAG--
3214 13_HRV56a|    GATG------TACAGATCT---TCTTAAAACCCAGAC------CCAGCCTAACAACAT--
3215 14_HRV56b|    GATG------TACAGATCT---TCTTAAAACCCAGAC------CCAGCCTAACAACAT--
3216 15_HRV56      GATG------TACAGATCT---TCTTAAAACCCAGAC------CCAGCCTAACAACAT--
3217 16_HRV54      GATC------CAACAATTT---TCCTTAAACACAGGA------CAAACCTTGTAACAG--
3218 17_HRV98      GAAC------CAACAATCT---TTCTTAAGCATAGAA------AAGATCTTGTAACAG--
3219 18_HRV59a|    GAAC------CTGAAATTT---TCTTAAAACCAAGAA------TGAATATTACAACAG--
3220 19_HRV59b|    GAAC------CTGAAATTT---TCTTAAAACCAAGAA------TGAATATTACAACAG--
3221 20_HRV59      GAAC------CTGAAATTT---TCTTAAAACCAAGAA------TGAATATTACAACAG--
3222 21_HRV63      GAGA------CTGAAATTT---TCTTAAAACCTAGAG------CAACTATCAAGACAG--
3223 22_HRV63b|    GAGA------CTGAAATTT---TCTTAAAACCTAGAG------CAACTATCAAGACAG--
3224 23_HRV63a|    GAGA------CTGAAATTT---TCTTAAAACCTAGAG------CAACTATCAAGACAG--
3225 24_HRV39      GAAC------CAACACTCT---TTATAAAATCAAGAG------AGAATCTTACCACAG--
3226 25_HRV39a|    GAAC------CAACACTCT---TTATAAAATCAAGAG------AGAATCTTACCACAG--
3227 26_HRV39b|    GAAC------CAACACTCT---TTATAAAACCAAGAG------AGAATCTTACCACAG--
3228 27_HRV10a|    GAAT------TACAAATAT---TTATTAGGTCTAGAGATGATCCCAAAGTAGTAACTG--
3229 28_HRV10b|    GAAT------TACAAATAT---TTATTAGGTCTAGAGATGATCCCAAAGTAGTAACTG--
3230 29_HRV10      GAAT------TACAAATAT---TTATTAGGTCTAGAGATGATCCCAAAGTAGTAACTG--
3231 30_HRV100a    GATG------TAAAGATTT---TCATTAGACCCAGAGATGATCCCAAAGTTTGTAACTG--
3232 31_HRV100b    GATG------TAAAGATTT---TCATTAGACCCAGAGATGATCCCAAAGTTTGTAACTG--
3233 32_HRV100     GATG------TAAAGATTT---TCATTAGACCCAGAGATGATCCCAAAGTTTGTAACTG--
3234 33_HRV66      GATC------TGCAAATTT---TCATTAAACCTAGAACAGATCCAAAGTAGTCAATG--
3235 34_HRV66b|    GATC------TGCAAATTT---TCATTAAACCTAGAACAGATCCAAAGTAGTCAATG--
3236 35_HRV66a|    GATC------TGCAAATTT---TCATTAAACCTAGAACAGATCCAAAGTAGTCAATG--
3237 36_HRV77a|    GATG------TACAAATCT---TTATTAAAGAGAGAGCAAGCCCAAAGTAGTTACTT--
3238 37_HRV77b|    GATG------TACAAATCT---TTATTAAAGAGAGAGCAAGCCCAAAGTAGTTACTT--
3239 38_HRV77      GATG------TACAAATCT---TTATTAAAGAGAGAGCAAGCCCAAAGTAGTTACTT--
3240 39_HRV62a     ---G------TTGACATTT---TTATAAAATCAAGG------CAAAACTTGCAAACAG--
3241 40_HRV62b     ---G------TTGACATTT---TTATAAAATCAAGG------CAAAACTTGCAAACAG--
3242 41_HRV25      ---G------TTGACATCT---TTATACAACCAAGA------AACAGTTTAAAAACAG--
3243 42_HRV29a     ---G------AT-CCAG-----TTGTGGAATCCAGA------CCAAGCTTAATGACAG--
3244 43_HRV29b     ---G------AT-ACAG-----TTGTGGAATCCAGA------CCAAGCTTAATGACAG--
3245 44_HRV44a     ---G------AT-ACAG-----TTGTGGAACCTAGA------CACAGCATAATGACAG--
3246 45_HRV44b     ---G------AT-ACAG-----TTGTGGAACCTAGA------CACAGCATAATGACAG--
3247 46_HRV31      GAAG------TTACAATTT---TTGTTAAACACAGGGATAATCCAAAGATTATCACAG--
3248 47_HRV31a|    GAAG------TTACAATCT---TTGTTAAACACAGGGATAATCCAAAGATTATCACAG--
3249 48_HRV31b|    GAAG------TTACAATCT---TTGTTAAACACAGGGATAATCCAAAGATTATCACAG--
3250 49_HRV47      GAAG------TTGCAATTT---TCATTGAGCATAGAGAAAATCCAAAATTCATTACAG--
```

FIG. D7 CONT'D

```
03.trace                                                                         9/20/2007 5:03 PM 3251  50_HRV47a|    GAAG------TTGCAATTT---TCATTGAGCATAGAGAAAATCCAAAATTCATTACAG--
3252  51_HRV47b|    GAAG------TTGCAATTT---TCATTGAGCATAGAGAAAATCCAAAATTCATTACAG--
3253  52_HRV11      CAGG------TGAAAACAG---CTGTCAAGGCTAGGAAAACAATTAAAACAGCA------
3254  53_HRV11b|    CAGG------TGAAAACAG---CTGTCAAGGCTAGGAAAACAATTAAAACAGCG------
3255  54_HRV11a|    CAGG------TGAAAACAG---CTGTCAAGGCTAGGAAAACAATTAAAACAGCT------
3256  55_HRV76      GATG------TGCAAACAG---CTATTAGACCAAGAGCAACAATTAAGACTGCA------
3257  56_HRV76b|    GATG------TGCAAACAG---CTATTAGACCAAGAGCAACAATTAAGACTGCG------
3258  57_HRV76a|    GATG------TGCAAACAG---CTATTAGACCAAGAGCAACAATTAAGACTGCT------
3259  58_HRV33      GAAG------TGAAGACAG---CTATTAGACCAAGAGCAACAATCAAGACTGCA------
3260  59_HRV33b|    GAAG------TGAAGACAG---CTATTAGACCAAGAGCAACAATCAAGACTGCG------
3261  60_HRV33a|    GAAG------TGAAGACAG---CTATTAGACCAAGAGCAACAATCAAGACTGCT------
3262  61_HRV24a|    GAAG------TCAAGACAG---CAATTGAACCTAGAAGAGGAATTAAAACAGTG------
3263  62_HRV24b|    GAAG------TCAAGACAG---CAATTGAACCTAGAAGAGGAATTAAAACAGTC------
3264  63_HRV24      GAAG------TCAAGACAG---CAATTGAACCTAGAAGAGGAATTAAAACAGTT------
3265  64_HRV90      GAAC------TTAAGACTG---CAATTAGGCCCAGGAAAACAATCACAACAGCA------
3266  65_HRV90a|    GAAC------TTAAGACTG---CAATTAGGCCCAGGAAAACAATCACAACAGCG------
3267  66_HRV90b|    GAAC------TTAAGACTG---CAATTAGGCCCAGGAAAACAATCACAACAGCT------
3268  67_HRV34      ACTG------AGAAGACTG---CAATCAAACACAGAGCAAAGATCACAATGGCC------
3269  68_HRV34b|    ACTG------AGAAGACTG---CAATCAAACACAGAGCAAAGATCACAATGGCA------
3270  69_HRV34a|    ACTG------AGAAGACTG---CAATCAAACACAGAGCAAAGATCACAATGGCT------
3271  70_HRV50a|    ACTG------AGAAGACTG---CAATTGCAACTAGACCAAAGATCACAGTGGCA------
3272  71_HRV50b|    ACTG------AGAAGACTG---CAATTGCAACTAGACCAAAGATCACAGTGGCG------
3273  72_HRV50      ACTG------AGAAGACTG---CAATTGCAACTAGACCAAAGATCACAGTGGCT------
3274  73_HRV18a|    AGAG------AGAAAACTG---CCATAGTACCCAGAGCAAGGATTACAATGGCA------
3275  74_HRV18b|    AGAG------AGAAAACTG---CCATAGTACCCAGAGCAAGGATTACAATGGCG------
3276  75_HRV18      AGAG------AGAAAACTG---CCATAGTACCCAGAGCAAGGATTACAATGGCT------
3277  76_HRV55      ACAG------AAAAGACAG---CAATTGAATACAGAAGGGACATTAAAACAGTG------
3278  77_HRV55b|    ACAG------AAAAGACAG---CAATTGAATACAGAAGGGACATTAAAACAGTC------
3279  78_HRV55a|    ACAG------AAAAGACAG---CAATTGAATACAGAAGGGACATTAAAACAGTA------
3280  79_HRV57      CAAG------AAGAAACAG---CAATTAAATATAGAAGGGACATTAAAATTGTTAAGA--
3281  80_HRV57a|    CAAG------AAGAAACAG---CAATTAAATATAGAAGGGACATTAAAATTGTTAAGA--
3282  81_HRV57b|    CAAG------AAGAAACAG---CAATTAAATATAGAAGGGACATTAAAATTGTTAAGA--
3283  82_HRV21      GAAG------TCACTTCTG---CAGTTGAGTCCAGAAGAACAATTGTCACAGTT------
3284  83_HRVHan     GATG------TCACTTCTG---CAGTTGAGTCCAGAAGAACAATTGTCACAGTT------
3285  84_HRV43      GAGG------TAGAAACAG---CCATAGTATCTAGGAGGGATATCAAAATTGTCAATG--
3286  85_HRV43b|    GAGG------TAGAAACAG---CCATAGTATCTAGGAGGGATATCAAAATTGTCAATG--
3287  86_HRV43a|    GAGG------TAGAAACAG---CCATAGTATCTAGGAGGGATATCAAAATTGTCAATG--
3288  87_HRV75      CAAG------TTGAGATTG---CTATTGAGCCCAGAAGAGATGTTAAGTTTGTAAATG--
3289  88_HRV75b|    CAAG------TTGAGATTG---CTATTGAGCCCAGAAGAGATGTTAAGTTTGTAAATG--
3290  89_HRV75a|    CAAG------TTGAGATTG---CTATTGAGCCCAGAAGAGATGTTAAGTTTGTAAATG--
3291  96_HRV9a|d    GATT------ATGCCACAG---TTATACCAGTTAGAGACAATGTTAGGGCAGTAAAGA--
3292  97_HRV9b|d    GATT------ATGCCACAG---TTATACCAGTTAGAGACAATGTTAGGGCAGTAAAGA--
3293  98_HRV9       GATT------ATGCCACAG---TTATACCAGTTAGAGACAATGTTAGGGCAGTAAAGA--
3294  99_HRV32      GATT------ACACCACAG---CCATACAAACCAGAGAGCATGTTAGAGCAGTCAAAA--
3295  100_HRV32a    GATT------ACACCACAG---CCATACAAACCAGAGAGCATGTTAGAGCAGTCAAAA--
3296  101_HRV32b    GATT------ACACCACAG---CCATACAAACCAGAGAGCATGTTAGAGCAGTCAAAA--
3297  102_HRV67     GAGG------CTCAAACGG---TTATACCTGTTAGAGCAGATGTTAGAACAATTAGAA--
3298  103_HRV67a    GAGG------CTCAAACGG---TTATACCTGTTAGAGCAGATGTTAGAACAATTAGAA--
3299  104_HRV67b    GAGG------CTCAAACGG---TTATACCTGTTAGAGCAGATGTTAGAACAATTAGAA--
3300  105_HRV15     GATG------TAACTACAG---TTATTCCAACTAGAGAAAATGTTAGAGCTATAGTAA--
3301  106_HRV15a    GATG------TAACTACAG---TTATTCCAACTAGAGAAAATGTTAGAGCTATAGTAA--
3302  107_HRV15b    GATG------TAACTACAG---TTATTCCAACTAGAGAAAATGTTAGAGCTATAGTAA--
3303  108_HRV74a    GACG------TAACTACAG---TCATCCCAACTAGG--------AGATCAATAGTGA--
3304  109_HRV74b    GACG------TAACTACAG---TCATCCCAACTAGG--------AGATCAATAGTGA--
3305  110_HRV74     GACG------TAACTACAG---TCATCCCAACTAGG--------AGATCAATAGTGA--
3306  111_HRV38a    GAAG------TAACCACTA---TGATTCCAACTAGAACCAACATAAGAACCATCGTAA--
3307  112_HRV38b    GAAG------TAACCACTA---TGATTCCAACTAGAACCAACATAAGAACCATCGTAA--
3308  113_HRV38     GAAG------TAACCACTA---TGATTCCAACTAGAACCAACATAAGAACCATCGTAA--
3309  114_HRV60     GAAG------CAGCCATAA---CAATCCCCATTAGAACTGATATACGAGCAATCAGAA--
3310  115_HRV60a    GAAG------CAGCCATAA---CAATCCCCATTAGAACTGATATACGAGCAATCAGAA--
3311  116_HRV60b    GAAG------CAGCCATAA---CAATCCCCATTAGAACTGATATACGAGCAATCAGAA--
3312  117_HRV64a    GAAT------ACACACCAC---CCGTTCCGTCACGTAACAGCCCCAGAGATATTGTCA--
3313  118_HRV64b    GAAT------ACACACCAC---CCGTTCCGTCACGTAACAGCCCCAGAGATATTGTCA--
3314  119_HRV64     GAAT------ACACACCAC---CCGTTCCGTCACGTAACAGCCCCAGAGATATTGTCA--
3315  120_HRV94a    GAGT------ACAAGCCAC---CTGTCCCAGTTAGGAATAGCCCCAGAGACATTGTCA--
```

FIG. D7 CONT'D

```
03.trace                                                              9/20/2007 5:03 PM 3316 121_HRV94b   GAGT------ACAAGCCAC---CTGTCCCAGTTAGGAATAGCCCCAGAGACATTGTCA--
3317 122_HRV94    GAGT------ACAAGCCAC---CTGTCCCAGTTAGGAATAGCCCCAGAGACATTGTCA--
3318 123_HRV22    GATT------ACACACTAC---CTATCCCAACAAGAGCCAACCCTAGACAAATTTTGA--
3319 124_HRV22a   GATT------ACACACTAC---CTATCCCAACAAGAGCCAACCCTAGACAAATTTTGA--
3320 125_HRV22b   GATT------ACACACTAC---CTATCCCAACAAGAGCCAACCCTAGACAAATTTTGA--
3321 126_HRV82    GATT------ACAGTGTTG---TTATTCCAGTTAGAGAGAGTCCCAGACAGATTCTTA--
3322 127_HRV82b   GATT------ACAGTGTTG---TTATTCCAGTTAGAGAGAGTCCCAGACAGATTCTTA--
3323 128_HRV82a   GATT------ACAGTGTTG---TTATTCCAGTTAGAGAGAGTCCCAGACAGATTCTTA--
3324 129_HRV19    GAAG------TCACTCTTC---CAATTGAAATAAGAGATAACCCTAGACATATAAAGA--
3325 130_HRV19a   GAAG------TCACTCTTC---CAATTGAAATAAGAGATAACCCTAGACATATAAAGA--
3326 131_HRV19b   GAAG------TCACTCTTC---CAATTGAAATAAGAGATAACCCTAGACATATAAAGA--
3327 132_HRV13    GATG------TTGCAGTCT---CCATTGTACCTAGAGCAAATGTTAGGGAAATTAGAA--
3328 133_HRV13a   GATG------TTGCAGTCT---CCATTGTACCTAGAGCAAATGTTAGGGAAATTAGAA--
3329 134_HRV13b   GATG------TTGCAGTCT---CCATTGTACCTAGAGCAAATGTTAGGGAAATTAGAA--
3330 135_HRV41    GCAGA---GATTGTGGCTT---CTGTCAGACCTAGAGACAATGTTAGACAAGTAAGAA--
3331 136_HRV41a   GCAGA---GATTGTGGCTT---CTGTCAGACCTAGAGACAATGTTAGACAAGTAAGAA--
3332 137_HRV41b   GCAGA---GATTGTGGCTT---CTGTCAGACCTAGAGACAATGTTAGACAAGTAAGAA--
3333 138_HRV73    GAAG------TTACTACTG---CCATTAGGCATAGAGATAATGTTAGAGCCATCCAAA--
3334 139_HRV73b   GAAG------TTACTACTG---CCATTAGGCATAGAGATAATGTTAGAGCCATCCAAA--
3335 140_HRV73a   GAAG------TTACTACTG---CCATTAGGCATAGAGATAATGTTAGAGCCATCCAAA--
3336 141_HRV61    GAAAAACAAGTTACCACTT---TCATCAAACCTAGAGCTAACTTAAGAGAGATTAGAA--
3337 142_HRV61a   GAAAAACAAGTTACCACTT---TCATCAAACCTAGAGCTAACTTAAGAGAGATTAGAA--
3338 143_HRV61b   GAAAAACAAGTTACCACTT---TCATCAAACCTAGAGCTAACTTAAGAGAGATTAGAA--
3339 144_HRV96    -------AGGTTACCACTT---TTATCAAACCTAGAGAAAATCTAAGGGATATTAGAA--
3340 145_HRV96b   -------AGGTTACCACTT---TTATCAAACCTAGAGAAAATCTAAGGGATATTAGAA--
3341 146_HRV96a   -------AGGTTACCACTT---TTATCAAACCTAGAGAAAATCTAAGGGATATTAGAA--
3342  90_HRV16a|  GTAC------ACAATGATGTGGCTATAAGACCTAGAACAAATCTAACAACTGTA------
3343  91_HRV16b|  GTAC------ACAATGATGTGGCTATAAGACCTAGAACAAATCTAACAACTGTC------
3344  92_1AYM_A    GTAC------ACAATGATGTGGCTATAAGACCTAGAACAAATCTAACAACTGTT------
3345  93_HRV81a|  GTCC------ACACTAGTGTAGCCATAAAACCTAGAACAAGTCTAACAAATGTG------
3346  94_HRV81b|  GTCC------ACACTAGTGTAGCCATAAAACCTAGAACAAGTCTAACAAATGTC------
3347  95_HRV81    GTCC------ACACTAGTGTAGCCATAAAACCTAGAACAAGTCTAACAAATGTT------
3348 147_HRV2     AGTA------TTCAGACAG---CAATTGTGACCAGACCAATTATCACTACAGCT------
3349 148_HRV2a|   AGTA------TTCAGACAG---CAATTGTGACCAGACCAATTATCACTACAGCA------
3350 149_HRV2b|   AGTA------TTCAGACAG---CAATTGTGACCAGACCAATTATCACTACAGCG------
3351 150_HRV49a   GACA------TTAAAACAG---GAATCACATCCAGAGCAATTATTACAACAGCG------
3352 151_HRV49b   GACA------TTAAAACAG---GAATCACATCCAGAGCAATTATTACAACAGCA------
3353 152_HRV49    GACA------TTAAAACAG---GAATCACATCCAGAGCAATTATTACAACAGCT------
3354 153_HRV23a   AATG------TCAAATCAA---GGGTTGCACATAGACCTGCAGTGATAACAGCG------
3355 154_HRV23b   AATG------TCAAATCAA---GGGTTGCACATAGACCTGCAGTGATAACAGCC------
3356 155_HRV23    AATG------TCAAATCAA---GGGTTGCACATAGACCTGCAGTGATAACAGCT------
3357 156_HRV30a   GAAG------TTAAATCAA---GGGTTGAACACAGAGCTAGGGTGACGACAGCA------
3358 157_HRV30b   GAAG------TTAAATCAA---GGGTTGAACACAGAGCTAGGGTGACGACAGCG------
3359 158_HRV30    GAAG------TTAAATCAA---GGGTTGAACACAGAGCTAGGGTGACGACAGCT------
3360 159_HRV7     GAGG------TCGCA---ACTCAAATCAAACCAGAGCCAATCTTTTCACCCTCAAAT--
3361 160_HRV7b|   GAGG------TCGCA---ACTCAAATCAAACCAGAGCCAATCTTTTCACCCTCAAAT--
3362 161_HRV7a|   GAGG------TCGCA---ACTCAAATCAAACCAGAGCCAATCTTTTCACCCTCAAAT--
3363 162_HRV88    GAAG------TAGCA---ACTCAAATCAAACCAGACGAGATGTTTACACTGTTACCA--
3364 163_HRV88a   GAAG------TAGCA---ACTCAAATCAAACCAGACGAGATGTTTACACTGTTACCA--
3365 164_HRV88b   GAAG------TAGCA---ACTCAAATCAAACCAGACGAGATGTTTACACTGTTACCA--
3366 165_HRV36a   GAGA------TCACA---ACCCAAATTAAAACCAGACCTAATGTCTTCACTGTA-----
3367 166_HRV36b   GAGA------TCACA---ACCCAAATTAAAACCAGACCTAATGTCTTCACTGTG-----
3368 167_HRV36    GAGA------TCACA---ACCCAAATTAAAACCAGACCTAATGTCTTCACTGTT-----
3369 168_HRV89a   GAGG------CCACA---ACTCAGATTAAAACCAGACCTGATGTTTTTACCGTTACAA--
3370 169_HRV89b   GAGG------CCACA---ACTCAGATTAAAACCAGACCTGATGTTTTTACCGTTACAA--
3371 170_HRV89    GAGG------CCACA---ACTCAGATTAAAACCAGACCTGATGTTTTTACCGTTACAA--
3372 171_HRV58    GAGG------TAACA---ACACAAATCAAACCCAGAACCAATGTTTTTACTATTACAT--
3373 172_HRV58a   GAGG------TAACA---ACACAAATCAAACCCAGAACCAATGTTTTTACTATTACAT--
3374 173_HRV58b   GAGG------TAACA---ACACAAATCAAACCCAGAACCAATGTTTTTACTATTACAT--
3375 174_HRV12a   GGAG------TTCCAGACAATAGAGTCAAACTCAGAGAGACACTCACCACAGTA-----
3376 175_HRV12b   GGAG------TTCCAGACAATAGAGTCAAACTCAGAGAGACACTCACCACAGTG-----
3377 176_HRV12    GGAG------TTCCAGACAATAGAGTCAAACTCAGAGAGACACTCACCACAGTT-----
3378 177_HRV78a   GGAA------CTCCAGACACCAAAGTGGCAATTAGAGCTAATATTAAAACTGTA-----
3379 178_HRV78b   GGAA------CTCCAGACACCAAAGTGGCAATTAGAGCTAATATTAAAACTGTG-----
3380 179_HRV78    GGAA------CTCCAGACACCAAAGTGGCAATTAGAGCTAATATTAAAACTGTT-----
```

FIG. D7 CONT'D

```
03.trace                                                                  9/20/2007 5:03 PM 3381 180_HRV20     GAAA------TTACA---ACTCATATCAGATTCAGAAACACTGTCAAAGATCTAACATAC
3382 181_HRV20a    GAAA------TTACA---ACTCATATCAGATTCAGAAACACTGTCAAAGATCTAACATAC
3383 182_HRV20b    GAAA------TTACA---ACTCATATCAGATTCAGAAACACTGTCAAAGATCTAACATAC
3384 183_HRV68     GATA------TTAAA---ACTCATATTAAATTTAGGAATACTGTTAAAGATTTGGCATAT
3385 184_HRV68a    GATA------TTAAA---ACTCATATTAAATTTAGGAATACTGTTAAAGATTTGGCATAT
3386 185_HRV68b    GATA------TTAAA---ACTCATATTAAATTTAGGAATACTGTTAAAGATTTGGCATAT
3387 186_HRV28     GATG------TTGAG---ACTCATATTAAATTTAGAACAGATGTTAAACAGATCACAA--
3388 187_HRV28a    GATG------TTGAG---ACTCATATTAAATTTAGAACAGATGTTAAACAGATCACAA--
3389 188_HRV28b    GATG------TTGAG---ACTCATATTAAATTTAGAACAGATGTTAAACAGATCACAA--
3390 189_HRV53a    ACAG------TTGAA---ACTCACATTAAGTTCAGACCTGATGTTAAAGATGTAACAT--
3391 190_HRV53b    ACAG------TTGAA---ACTCACATTAAGTTCAGACCTGATGTTAAAGATGTAACAT--
3392 191_HRV53     ACAG------TTGAA---ACTCACATTAAGTTCAGACCTGATGTTAAAGATGTAACAT--
3393 192_HRV46a    ACTA------TACCAGATACTCATATTGGAATTAGAAGGGATATAAAGTACATTAAAA--
3394 193_HRV46b    ACTA------TACCAGATACTCATATTGGAATTAGAAGGGATATAAAGTACATTAAAA--
3395 194_HRV46     ACTA------TACCAGATACTCATATTGGAATTAGAAGGGATATAAAGTACATTAAAA--
3396 195_HRV80a    TCTA------TACCAGATACACAAATTAAAATCAGAGATAATATCAGGCAGGTTAGAA--
3397 196_HRV80b    TCTA------TACCAGATACACAAATTAAAATCAGAGATAATATCAGGCAGGTTAGAA--
3398 197_HRV80     TCTA------TACCAGATACACAAATTAAAATCAGAGATAATATCAGGCAGGTTAGAA--
3399 198_HRV51     GAAG------GCTTGAAAACTCAGATTAAAACTAGGGCAGACATCAAACTTGTGAACT--
3400 199_HRV51a    GAAG------GCTTGAAAACTCAGATTAAAACTAGGGCAGACATCAAACTTGTGAACT--
3401 200_HRV51b    GAAG------GCTTGAAAACTCAGATTAAAACTAGGGCAGACATCAAACTTGTGAACT--
3402 201_HRV65a    ACAA------ACCTAAGAACCCAAATTAAAACCAGAGATAACATTAAAATTGTAAACT--
3403 202_HRV65b    ACAA------ACCTAAGAACCCAAATTAAAACCAGAGATAACATTAAAATTGTAAACT--
3404 203_HRV65     ACAA------ACCTAAGAACCCAAATTAAAACCAGAGATAACATTAAAATTGTAAACT--
3405 204_HRV71a    AATT------CCATTAAAACCAAAATCAAAATCAGAAGAGACATTAAAGAGGTCAGCA--
3406 205_HRV71b    AATT------CCATTAAAACCAAAATCAAAATCAGAAGAGACATTAAAGAGGTCAGCA--
3407 206_HRV71     AATT------CCATTAAAACCAAAATCAAAATCAGAAGAGACATTAAAGAGGTCAGCA--
3408 207_HRV8      GTAA------CACCAGAAACTAAGGTTAAATATAGAGCTGAAGTCACAACCATT------
3409 208_HRV95     GTAA------CACCAGAAACTAAGGTCAAATATAGAGCTGAAGTCACAACCATT------
3410 209_HRV45     GAAA------CAGCC---ACAAAAGTCCAAACTAGAGCAAATGTCACAACAGTA------
3411 210_HRV45a    GAAA------CAGCC---ACAAAAGTCCAAACTAGAGCAAATGTCACAACAGTG------
3412 211_HRV45b    GAAA------CAGCC---ACAAAAGTCCAAACTAGAGCAAATGTCACAACAGTT------
3413 GROUP_1       --------------------T--------G------------------------------
3414
3415 1_HRV1A1|d    ----CA---------------
3416 2_HRV1A2|d    ----CG---------------
3417 3_HRV1A|cD    ----CT---------------
3418 4_HRV1B1|d    ----TA---------------
3419 5_HRV1B2|d    ----TC---------------
3420 6_HRV1B       ----TT---------------
3421 7_HRV40a|d    ----TA---------------
3422 8_HRV40b|d    ----TC---------------
3423 9_HRV40       ----TT---------------
3424 10_HRV85      ----CA---------------
3425 11_HRV85a|    ----CG---------------
3426 12_HRV85b|    ----CT---------------
3427 13_HRV56a|    ----TA---------------
3428 14_HRV56b|    ----TG---------------
3429 15_HRV56      ----TT---------------
3430 16_HRV54      ----CT---------------
3431 17_HRV98      ----CT---------------
3432 18_HRV59a|    ----CA---------------
3433 19_HRV59b|    ----CG---------------
3434 20_HRV59      ----CT---------------
3435 21_HRV63      ----CA---------------
3436 22_HRV63b|    ----CG---------------
3437 23_HRV63a|    ----CT---------------
3438 24_HRV39      ----CT---------------
3439 25_HRV39a|    ----CA---------------
3440 26_HRV39b|    ----CT---------------
3441 27_HRV10a|    ----CA---------------
3442 28_HRV10b|    ----CC---------------
3443 29_HRV10      ----CT---------------
3444 30_HRV100a    ----CA---------------
3445 31_HRV100b    ----CG---------------
```

FIG. D7 CONT'D 03.trace                                                                9/20/2007 5:03 PM

```
3446  32_HRV100    ----CT--------------
3447  33_HRV66     ----TA--------------
3448  34_HRV66b|   ----TG--------------
3449  35_HRV66a|   ----TC--------------
3450  36_HRV77a|   ----TG--------------
3451  37_HRV77b|   ----TA--------------
3452  38_HRV77     ----TT--------------
3453  39_HRV62a    ----CT--------------
3454  40_HRV62b    ----C---------------
3455  41_HRV25     ----CT--------------
3456  42_HRV29a    ----CT--------------
3457  43_HRV29b    ----CT--------------
3458  44_HRV44a    ----CT--------------
3459  45_HRV44b    ----CT--------------
3460  46_HRV31     ----CA--------------
3461  47_HRV31a|   ----CT--------------
3462  48_HRV31b|   ----CA--------------
3463  49_HRV47     ----CA--------------
3464  50_HRV47a|   ----CT--------------
3465  51_HRV47b|   ----CA--------------
3466  52_HRV11     --------------------
3467  53_HRV11b|   --------------------
3468  54_HRV11a|   --------------------
3469  55_HRV76     --------------------
3470  56_HRV76b|   --------------------
3471  57_HRV76a|   --------------------
3472  58_HRV33     --------------------
3473  59_HRV33b|   --------------------
3474  60_HRV33a|   --------------------
3475  61_HRV24a|   --------------------
3476  62_HRV24b|   --------------------
3477  63_HRV24     --------------------
3478  64_HRV90     --------------------
3479  65_HRV90a|   --------------------
3480  66_HRV90b|   --------------------
3481  67_HRV34     --------------------
3482  68_HRV34b|   --------------------
3483  69_HRV34a|   --------------------
3484  70_HRV50a|   --------------------
3485  71_HRV50b|   --------------------
3486  72_HRV50     --------------------
3487  73_HRV18a|   --------------------
3488  74_HRV18b|   --------------------
3489  75_HRV18     --------------------
3490  76_HRV55     --------------------
3491  77_HRV55b|   --------------------
3492  78_HRV55a|   --------------------
3493  79_HRV57     ----ATGTG-----------
3494  80_HRV57a|   ----ATGTA-----------
3495  81_HRV57b|   ----ATGTC-----------
3496  82_HRV21     --------------------
3497  83_HRVHan    --------------------
3498  84_HRV43     ----CA--------------
3499  85_HRV43b|   ----CG--------------
3500  86_HRV43a|   ----CT--------------
3501  87_HRV75     ----CA--------------
3502  88_HRV75b|   ----CG--------------
3503  89_HRV75a|   ----CT--------------
3504  96_HRV9a|d   ----ATGTC-----------
3505  97_HRV9b|d   ----ATGTG-----------
3506  98_HRV9      ----ATGTA-----------
3507  99_HRV32     ----ATGTA-----------
3508  100_HRV32a   ----ATGTG-----------
3509  101_HRV32b   ----ATGTC-----------
3510  102_HRV67    ----ATGTA-----------
```

FIG. D7 CONT'D

```
03.trace                                                             9/20/2007 5:03 PM 3511  103_HRV67a     ----ATGTC------------
        3512  104_HRV67b     ----ATGTT------------
        3513  105_HRV15      ----ATGTT------------
        3514  106_HRV15a     ----ATGTA------------
        3515  107_HRV15b     ----ATGTC------------
        3516  108_HRV74a     ----ATGTA------------
        3517  109_HRV74b     ----ATGTC------------
        3518  110_HRV74      ----ATGTT------------
        3519  111_HRV38a     ----ATGTA------------
        3520  112_HRV38b     ----ATGTC------------
        3521  113_HRV38      ----ATGTT------------
        3522  114_HRV60      ----CAGTT------------
        3523  115_HRV60a     ----CAGTA------------
        3524  116_HRV60b     ----CAGTG------------
        3525  117_HRV64a     ----CAGTG------------
        3526  118_HRV64b     ----CAGTG------------
        3527  119_HRV64      ----CAGTA------------
        3528  120_HRV94a     ----CAGTG------------
        3529  121_HRV94b     ----CAGTC------------
        3530  122_HRV94      ----CAGTA------------
        3531  123_HRV22      ----ATGTA------------
        3532  124_HRV22a     ----ATGTG------------
        3533  125_HRV22b     ----ATGTC------------
        3534  126_HRV82      ----ATGTA------------
        3535  127_HRV82b     ----ATGTT------------
        3536  128_HRV82a     ----ATGTC------------
        3537  129_HRV19      ----ATGTA------------
        3538  130_HRV19a     ----ATGTG------------
        3539  131_HRV19b     ----ATGTC------------
        3540  132_HRV13      ----ACTTT------------
        3541  133_HRV13a     ----ACTTG------------
        3542  134_HRV13b     ----ACTTA------------
        3543  135_HRV41      ----ATTAT------------
        3544  136_HRV41a     ----ATTAG------------
        3545  137_HRV41b     ----ATTAC------------
        3546  138_HRV73      ----ATTTT------------
        3547  139_HRV73b     ----ATTTG------------
        3548  140_HRV73a     ----ATTTC------------
        3549  141_HRV61      ----CATTT------------
        3550  142_HRV61a     ----CATTT------------
        3551  143_HRV61b     ----CATTT------------
        3552  144_HRV96      ----ATTTT------------
        3553  145_HRV96b     ----ATTTA------------
        3554  146_HRV96a     ----ATTTC------------
        3555  90_HRV16a|     ---------------------
        3556  91_HRV16b|     ---------------------
        3557  92_1AYM_A      ---------------------
        3558  93_HRV81a|     ---------------------
        3559  94_HRV81b|     ---------------------
        3560  95_HRV81       ---------------------
        3561  147_HRV2       ---------------------
        3562  148_HRV2a|     ---------------------
        3563  149_HRV2b|     ---------------------
        3564  150_HRV49a     ---------------------
        3565  151_HRV49b     ---------------------
        3566  152_HRV49      ---------------------
        3567  153_HRV23a     ---------------------
        3568  154_HRV23b     ---------------------
        3569  155_HRV23      ---------------------
        3570  156_HRV30a     ---------------------
        3571  157_HRV30b     ---------------------
        3572  158_HRV30      ---------------------
        3573  159_HRV7       ----CAGCT------------
        3574  160_HRV7b|     ----CAGCA------------
        3575  161_HRV7a|     ----CAGCG------------
```

FIG. D7 CONT'D

```
03.trace                                                           9/20/2007 5:03 PM 3576  162_HRV88       ----CTGCT------------
3577  163_HRV88a      ----CTGCA------------
3578  164_HRV88b      ----CTGCG------------
3579  165_HRV36a      ---------------------
3580  166_HRV36b      ---------------------
3581  167_HRV36       ---------------------
3582  168_HRV89a      ----ACGTG------------
3583  169_HRV89b      ----ACGTA------------
3584  170_HRV89       ----ACGTC------------
3585  171_HRV58       ----CTGCT------------
3586  172_HRV58a      ----CTGCA------------
3587  173_HRV58b      ----CTGCC------------
3588  174_HRV12a      ---------------------
3589  175_HRV12b      ---------------------
3590  176_HRV12       ---------------------
3591  177_HRV78a      ---------------------
3592  178_HRV78b      ---------------------
3593  179_HRV78       ---------------------
3594  180_HRV20       CCCACAGAAATGACGAATGTT
3595  181_HRV20a      CCCACAGAAATGACGAATGTA
3596  182_HRV20b      CCCACAGAAATGACGAATGTG
3597  183_HRV68       CCTCCAGAATTAGCAAACCTT
3598  184_HRV68a      CCTCCAGAATTAGCAAACCTT
3599  185_HRV68b      CCTCCAGAATTAGCAAACCTT
3600  186_HRV28       ----CAGTT------------
3601  187_HRV28a      ----CAGTA------------
3602  188_HRV28b      ----CAGTC------------
3603  189_HRV53a      ----CAGTAATGACAGCT---
3604  190_HRV53b      ----CAGTAATGACAGCT---
3605  191_HRV53       ----CAGTAATGACAGCA---
3606  192_HRV46a      ----CAGCA------------
3607  193_HRV46b      ----CAGCC------------
3608  194_HRV46       ----CAGCT------------
3609  195_HRV80a      ----CAGTA------------
3610  196_HRV80b      ----CAGTC------------
3611  197_HRV80       ----CAGTT------------
3612  198_HRV51       -----TT--------------
3613  199_HRV51a      -----TA--------------
3614  200_HRV51b      -----TG--------------
3615  201_HRV65a      -----TG--------------
3616  202_HRV65b      -----TA--------------
3617  203_HRV65       -----TT--------------
3618  204_HRV71a      -----ACTAA-----------
3619  205_HRV71b      -----ACTAG-----------
3620  206_HRV71       -----ACTAT-----------
3621  207_HRV8        ---------------------
3622  208_HRV95       ---------------------
3623  209_HRV45       ---------------------
3624  210_HRV45a      ---------------------
3625  211_HRV45b      ---------------------
3626  GROUP_1         ---------------------
3627
3628
3629
3630  Summary:
3631
3632  GROUP_1         AA-CC--T-GA----T------A-----T--T-----A-GT--T--T-GT-CC--A----
3633  SUMMARY         AA-CC--T-GA----T------A-----T--T-----A-GT--T--T-GT-CC--A----
3634
3635  GROUP_1         ------AG----------------A--C-G---C-----T-GA-GC-GC-GA-AC-GG
3636  SUMMARY         ------AG----------------A--C-G---C-----T-GA-GC-GC-GA-AC-GG
3637
3638  GROUP_1         CA-AC-A--------CA-CC-GA-GA-----T-GA-AC--G----GT----------A
3639  SUMMARY         CA-AC-A--------CA-CC-GA-GA-----T-GA-AC--G----GT----------A
3640
```

FIG. D7 CONT'D

```
03.trace                                                          9/20/2007 5:03 PM 3641 GROUP_1    AC-----ATGA-A------T-GA----TT--T-GG--G--C----TG-------------
3642 SUMMARY    AC-----ATGA-A------T-GA----TT--T-GG--G--C----TG-------------
3643
3644 GROUP_1    ------------------------------------------------------------
3645 SUMMARY    ------------------------------------------------------------
3646 GROUP_1    ------------TGG----T-A---T----GA-ATG-C-CA--T--G--G-AA----GA
3647
3648 SUMMARY    ------------TGG----T-A---T----GA-ATG-C-CA--T--G--G-AA----GA
3649
3650 GROUP_1    -T-TT-AC-TA-----G-TT--A-TC-GA--T-AC--T-G-T-----------C------
3651 SUMMARY    -T-TT-AC-TA-----G-TT--A-TC-GA--T-AC--T-G-T-----------C------
3652
3653 GROUP_1    --------------GG-CA--T-----T-CA-T--ATGT---T-CC-CC-GG-G--CC---
3654 SUMMARY    --------------GG-CA--T-----T-CA-T--ATGT---T-CC-CC-GG-G--CC---
3655
3656 GROUP_1    -CC--------G-------------TGG-A--C--G-A--AA----TC----TT-TGGCA
3657 SUMMARY    -CC--------G-------------TGG-A--C--G-A--AA----TC----TT-TGGCA
3658
3659 GROUP_1    ----GG-CA----T--CC--G--T--C--T-CC-TT-----G--T-GC-TC-G--TA-TA
3660 SUMMARY    ----GG-CA----T--CC--G--T--C--T-CC-TT-----G--T-GC-TC-G--TA-TA
3661
3662 GROUP_1    -ATGTT-TA-GA-GG-TA------------------------TA-GG------------
3663 SUMMARY    -ATGTT-TA-GA-GG-TA------------------------TA-GG------------
3664
3665 GROUP_1    -AA----ATGGG--C--T-T------G--T--T-AC-------CA---------------
3666 SUMMARY    -AA----ATGGG--C--T-T------G--T--T-AC-------CA---------------
3667
3668 GROUP_1    --T-----------T-T--C--AA-GC-AA-CA---------TGG-G-CC--G--C-C
3669 SUMMARY    --T-----------T-T--C--AA-GC-AA-CA---------TGG-G-CC--G--C-C
3670
3671 GROUP_1    --G-G---T----TA-------------------AA-T---------------------
3672 SUMMARY    --G-G---T----TA-------------------AA-T---------------------
3673
3674 GROUP_1    ------------------------------T--------G-------------------
3675 SUMMARY    ------------------------------T--------G-------------------
3676
3677 GROUP_1    --------------------
3678 SUMMARY    --------------------
3679
3680
```

FIG. D7 CONT'D

```
04-2.trace                                                                    9/20/2007 5:04 PM 1 Group 1:  1_HRV1A1|d
 2 Group 1:  2_HRV1A2|d
 3 Group 1:  3_HRV1A|cD
 4 Group 1:  4_HRV1B1|d
 5 Group 1:  5_HRV1B2|d
 6 Group 1:  6_HRV1B
 7 Group 1:  7_HRV40a|d
 8 Group 1:  8_HRV40b|d
 9 Group 1:  9_HRV40
10 Group 1: 10_HRV85
11 Group 1: 11_HRV85a|
12 Group 1: 12_HRV85b|
13 Group 1: 13_HRV56a|
14 Group 1: 14_HRV56b|
15 Group 1: 15_HRV56
16 Group 1: 16_HRV54
17 Group 1: 17_HRV98
18 Group 1: 18_HRV59a|
19 Group 1: 19_HRV59b|
20 Group 1: 20_HRV59
21 Group 1: 21_HRV63
22 Group 1: 22_HRV63b|
23 Group 1: 23_HRV63a|
24 Group 1: 24_HRV39
25 Group 1: 25_HRV39a|
26 Group 1: 26_HRV39b|
27 Group 1: 27_HRV10a|
28 Group 1: 28_HRV10b|
29 Group 1: 29_HRV10
30 Group 1: 30_HRV100a
31 Group 1: 31_HRV100b
32 Group 1: 32_HRV100
33 Group 1: 33_HRV66
34 Group 1: 34_HRV66b|
35 Group 1: 35_HRV66a|
36 Group 1: 36_HRV77a|
37 Group 1: 37_HRV77b|
38 Group 1: 38_HRV77
39 Group 1: 39_HRV62a
40 Group 1: 40_HRV62b
41 Group 1: 41_HRV25
42 Group 1: 42_HRV29a
43 Group 1: 43_HRV29b
44 Group 1: 44_HRV44a
45 Group 1: 45_HRV44b
46 Group 1: 46_HRV31
47 Group 1: 47_HRV31a|
48 Group 1: 48_HRV31b|
49 Group 1: 49_HRV47
50 Group 1: 50_HRV47a|
51 Group 1: 51_HRV47b|
52 Group 1: 52_HRV11
53 Group 1: 53_HRV11b|
54 Group 1: 54_HRV11a|
55 Group 1: 55_HRV76
56 Group 1: 56_HRV76b|
57 Group 1: 57_HRV76a|
58 Group 1: 58_HRV33
59 Group 1: 59_HRV33b|
60 Group 1: 60_HRV33a|
61 Group 1: 61_HRV24a|
62 Group 1: 62_HRV24b|
```

FIG. D8

```
04-2.trace                                                         9/20/2007 5:04 PM
         63 Group 1:  63_HRV24
         64 Group 1:  64_HRV90
         65 Group 1:  65_HRV90a|
         66 Group 1:  66_HRV90b|
         67 Group 1:  67_HRV34
         68 Group 1:  68_HRV34b|
         69 Group 1:  69_HRV34a|
         70 Group 1:  70_HRV50a|
         71 Group 1:  71_HRV50b|
         72 Group 1:  72_HRV50
         73 Group 1:  73_HRV18a|
         74 Group 1:  74_HRV18b|
         75 Group 1:  75_HRV18
         76 Group 1:  76_HRV55
         77 Group 1:  77_HRV55b|
         78 Group 1:  78_HRV55a|
         79 Group 1:  79_HRV57
         80 Group 1:  80_HRV57a|
         81 Group 1:  81_HRV57b|
         82 Group 1:  82_HRV21
         83 Group 1:  83_HRVHan
         84 Group 1:  84_HRV43
         85 Group 1:  85_HRV43b|
         86 Group 1:  86_HRV43a|
         87 Group 1:  87_HRV75
         88 Group 1:  88_HRV75b|
         89 Group 1:  89_HRV75a|
         90 Group 1:  96_HRV9a|d
         91 Group 1:  97_HRV9b|d
         92 Group 1:  98_HRV9
         93 Group 1:  99_HRV32
         94 Group 1:  100_HRV32a
         95 Group 1:  101_HRV32b
         96 Group 1:  102_HRV67
         97 Group 1:  103_HRV67a
         98 Group 1:  104_HRV67b
         99 Group 1:  105_HRV15
        100 Group 1:  106_HRV15a
        101 Group 1:  107_HRV15b
        102 Group 1:  108_HRV74a
        103 Group 1:  109_HRV74b
        104 Group 1:  110_HRV74
        105 Group 1:  111_HRV38a
        106 Group 1:  112_HRV38b
        107 Group 1:  113_HRV38
        108 Group 1:  114_HRV60
        109 Group 1:  115_HRV60a
        110 Group 1:  116_HRV60b
        111 Group 1:  117_HRV64a
        112 Group 1:  118_HRV64b
        113 Group 1:  119_HRV64
        114 Group 1:  120_HRV94a
        115 Group 1:  121_HRV94b
        116 Group 1:  122_HRV94
        117 Group 1:  123_HRV22
        118 Group 1:  124_HRV22a
        119 Group 1:  125_HRV22b
        120 Group 1:  126_HRV82
        121 Group 1:  127_HRV82b
        122 Group 1:  128_HRV82a
        123 Group 1:  129_HRV19
        124 Group 1:  130_HRV19a
        125 Group 1:  131_HRV19b
        126 Group 1:  132_HRV13
        127 Group 1:  133_HRV13a
```

FIG. D8 CONT'D

```
04-2.trace                                                      9/20/2007 5:04 PM 128 Group 1: 134_HRV13b
    129 Group 1: 135_HRV41
    130 Group 1: 136_HRV41a
    131 Group 1: 137_HRV41b
    132 Group 1: 138_HRV73
    133 Group 1: 139_HRV73b
    134 Group 1: 140_HRV73a
    135 Group 1: 141_HRV61
    136 Group 1: 142_HRV61a
    137 Group 1: 143_HRV61b
    138 Group 1: 144_HRV96
    139 Group 1: 145_HRV96b
    140 Group 1: 146_HRV96a
    141 Group 1: 90_HRV16a|
    142 Group 1: 91_HRV16b|
    143 Group 1: 92_1AYM_A
    144 Group 1: 93_HRV81a|
    145 Group 1: 94_HRV81b|
    146 Group 1: 95_HRV81
    147 Group 1: 147_HRV2
    148 Group 1: 148_HRV2a|
    149 Group 1: 149_HRV2b|
    150 Group 1: 150_HRV49a
    151 Group 1: 151_HRV49b
    152 Group 1: 152_HRV49
    153 Group 1: 153_HRV23a
    154 Group 1: 154_HRV23b
    155 Group 1: 155_HRV23
    156 Group 1: 156_HRV30a
    157 Group 1: 157_HRV30b
    158 Group 1: 158_HRV30
    159 Group 1: 159_HRV7
    160 Group 1: 160_HRV7b|
    161 Group 1: 161_HRV7a|
    162 Group 1: 162_HRV88
    163 Group 1: 163_HRV88a
    164 Group 1: 164_HRV88b
    165 Group 1: 165_HRV36a
    166 Group 1: 166_HRV36b
    167 Group 1: 167_HRV36
    168 Group 1: 168_HRV89a
    169 Group 1: 169_HRV89b
    170 Group 1: 170_HRV89
    171 Group 1: 171_HRV58
    172 Group 1: 172_HRV58a
    173 Group 1: 173_HRV58b
    174 Group 1: 174_HRV12a
    175 Group 1: 175_HRV12b
    176 Group 1: 176_HRV12
    177 Group 1: 177_HRV78a
    178 Group 1: 178_HRV78b
    179 Group 1: 179_HRV78
    180 Group 1: 180_HRV20
    181 Group 1: 181_HRV20a
    182 Group 1: 182_HRV20b
    183 Group 1: 183_HRV68
    184 Group 1: 184_HRV68a
    185 Group 1: 185_HRV68b
    186 Group 1: 186_HRV28
    187 Group 1: 187_HRV28a
    188 Group 1: 188_HRV28b
    189 Group 1: 189_HRV53a
    190 Group 1: 190_HRV53b
    191 Group 1: 191_HRV53
    192 Group 1: 192_HRV46a
```

FIG. D8 CONT'D

```
04-2.trace                                                               9/20/2007 5:04 PM 193 Group 1: 193_HRV46b
194 Group 1: 194_HRV46
195 Group 1: 195_HRV80a
196 Group 1: 196_HRV80b
197 Group 1: 197_HRV80
198 Group 1: 198_HRV51
199 Group 1: 199_HRV51a
200 Group 1: 200_HRV51b
201 Group 1: 201_HRV65a
202 Group 1: 202_HRV65b
203 Group 1: 203_HRV65
204 Group 1: 204_HRV71a
205 Group 1: 205_HRV71b
206 Group 1: 206_HRV71
207 Group 1: 207_HRV8
208 Group 1: 208_HRV95
209 Group 1: 209_HRV45
210 Group 1: 210_HRV45a
211 Group 1: 211_HRV45b
212
213
214 >>>>>
215
216
217
218 Group 1:
219
220  1_HRV1A1|d      AATCCAGTAGAAAACTACATTGATGAAGTTTTAAATGAAGTTTTAGTAGTGCCGAATATA
221  2_HRV1A2|d      AATCCAGTAGAAAACTACATTGATGAAGTTTTAAATGAAGTTTTAGTAGTGCCGAATATA
222  3_HRV1A|cD      AATCCAGTAGAAAACTACATTGATGAAGTTTTAAATGAAGTTTTAGTAGTGCCGAATATA
223  4_HRV1B1|d      AATCCAGTGGAAAATTACATTGATGAAGTTTTAAATGAAGTTCTAGTAGTACCAAATATA
224  5_HRV1B2|d      AATCCAGTGGAAAATTACATTGATGAAGTTTTAAATGAAGTTCTAGTAGTACCAAATATA
225  6_HRV1B         AATCCAGTGGAAAATTACATTGATGAAGTTTTAAATGAAGTTCTAGTAGTACCAAATATA
226  7_HRV40a|d      AACCCCGTTGAAAGGTATGTTGATGAGGTTCTTAATGAAGTTCTGGTAGTTCCAAATATC
227  8_HRV40b|d      AACCCCGTTGAAAGGTATGTTGATGAGGTTCTTAATGAAGTTCTGGTAGTTCCAAATATC
228  9_HRV40         AACCCCGTTGAAAGGTATGTTGATGAGGTTCTTAATGAAGTTCTGGTAGTACCAAATATC
229 10_HRV85         AATCCTGTTGAAAAATACGTTGATGAAGTCCTTAATGAGGTTCTAGTGGTTCCAAATATC
230 11_HRV85a|       AATCCTGTTGAAAAATACGTTGATGAAGTCCTTAATGAGGTTCTAGTGGTTCCAAATATC
231 12_HRV85b|       AATCCTGTTGAAAAATACGTTGATGAAGTCCTTAATGAGGTTCTAGTGGTTCCAAATATC
232 13_HRV56a|       AACCCCAGTTGAGAGATATGTAGATGATGTTTTAAATGAAGTTTTAGTTGTTCCAAATATT
233 14_HRV56b|       AACCCAGTTGAGAGATATGTAGATGATGTTTTAAATGAAGTTTTAGTTGTTCCAAATATT
234 15_HRV56         AACCCAGTTGAGAGATATGTAGATGATGTTTTAAATGAAGTTTTAGTTGTTCCAAATATT
235 16_HRV54         AATCCTGTAGAAAGATATGTTGATGAAGTGTTAAATGAAGTGTTAGTTGTCCCAAACATT
236 17_HRV98         AATCCTGTAGAGAGATATGTTGATGAAGTATTAAATGAAGTGTTAGTTGTTCCAAACATT
237 18_HRV59a|       AACCCAGTGGAAAACTATGTTAATGATGTACTTAATGAGGTTTTAGTAGTACCAAATATA
238 19_HRV59b|       AACCCAGTGGAAAACTATGTTAATGATGTACTTAATGAGGTTTTAGTAGTACCAAATATA
239 20_HRV59         AACCCAGTGGAAAACTATGTTAATGATGTACTTAATGAGGTTTTAGTAGTACCAAATATA
240 21_HRV63         AATCCAGTAGAGAATTATGTAAATGATGTTCTTAATGAAGTGTTAGTTGTTCCAAACATA
241 22_HRV63b|       AATCCAGTAGAGAATTATGTAAATGATGTTCTTAATGAAGTGTTAGTTGTTCCAAACATA
242 23_HRV63a|       AATCCAGTAGAGAATTATGTAAATGATGTTCTTAATGAAGTGTTAGTTGTTCCAAACATA
243 24_HRV39         AATCCAGTAGAAAATTATATAGATGAAGTATTAAATGAAGTGTTAGTTGTTCCTAATATA
244 25_HRV39a|       AATCCAGTAGAAAATTATATAGATGAAGTATTAAATGAGGTATTAGTTGTTCCTAATATA
245 26_HRV39b|       AATCCAGTAGAAAATTATATAGATGGAGTATTAAATGAGGTATTAGTTGTTCCTAATATA
246 27_HRV10a|       AATCCAGTTGAAAATTACATTGATAATGTACTTAATGAAGTCCTAGTGGTACCCAACATC
247 28_HRV10b|       AATCCAGTTGAAAATTACATTGATAATGTACTTAATGAAGTCCTAGTGGTACCCAACATC
248 29_HRV10         AATCCAGTTGAAAATTACATTGATAATGTACTTAATGAAGTCCTAGTGGTACCCAACATC
249 30_HRV100a       AATCCAGTAGAAAATTATGTTGAAGGTGTGCTGAATGAAGTACTAGTGGTACCTAATATT
250 31_HRV100b       AATCCAGTAGAAAATTATGTTGAAGGTGTGCTGAATGAAGTACTAGTGGTACCTAATATT
251 32_HRV100        AATCCAGTAGAAAATTATGTTGAAGGTGTGCTGAATGAAGTACTAGTGGTACCTAATATT
252 33_HRV66         AATCCAGTTGAAGATTATGTTGAGGGTGTTTAAATGAAGTTTTAGTAGTACCAAACATC
253 34_HRV66b|       AATCCAGTTGAAGATTATGTTGAGGGTGTTTTAAATGAAGTTTTAGTAGTACCAAACATC
254 35_HRV66a|       AATCCAGTTGAAGATTATGTTGAGGGTGTTTTAAATGAAGTTTTAGTAGTACCAAACATC
255 36_HRV77a|       AATCCAGTTGAGGACTATATCGATAATGTACTTAATGAAGTCTTAGTAGTACCAAATACC
```

FIG. D8 CONT'D

04-2.trace                                                                                        9/20/2007 5:04 PM

```
256  37_HRV77b|    AATCCAGTTGAGGACTATATCGATAATGTACTTAATGAAGTCTTAGTAGTACCAAATACC
257  38_HRV77     AATCCAGTTGAGGACTATATCGATAATGTACTTAATGAAGTCTTAGTAGTACCAAATACC
258  39_HRV62a    AATCCAATTGAAAATTATGTAGATCAAGTACTTAATGAAGTTTTAGTTGTACCAAATATT
259  40_HRV62b    AATCCAATTGAAAATTATGTAGATCAAGTACTTAATGAAGTTTTAGTTGTACCAAATATT
260  41_HRV25     AATCCAATTGAAAATTATGTAGATCAAGTACTTAATGAGGTTCTAGTCGTACCAAATATT
261  42_HRV29a    AACCCAGTTGAAAACTATGTGGATGAGGTGCTTAATGAAGTTTTAGTTGTGCCTAACATC
262  43_HRV29b    AACCCAGTTGAAAACTATGTGGATGAGGTGCTTAATGAAGTTTTAGTTGTGCCTAACATC
263  44_HRV44a    AACCCAGTTGAAAATTATGTGGATGAAGTACTTAATGAAGTCTTAGTTGTGCCTAATATC
264  45_HRV44b    AACCCAGTTGAAAATTATGTGGATGAAGTACTTAATGAAGTCTTAGTTGTGCCTAATATC
265  46_HRV31     AATCCAGTTGAAAACTATGTGGAAGAGGTTCTTAATGAAGTCTTAGTAGTACCTAATATC
266  47_HRV31a|   AATCCAGTTGAAAACTATGTGGAAGAGGTTCTTAATGAAGTCTTAGTAGTACCTAATATC
267  48_HRV31b|   AATCCAGTTGAAAACTATGTGGAAGAGGTTCTTAATGAAGTCTTAGTAGTACCTAATATC
268  49_HRV47     AACCCAGTCGAAAATTATGTGGAAGAGGTACTTAATGAGGTCTTAGTTGTACCAAATATC
269  50_HRV47a|   AACCCAGTCGAAAATTATGTGGAAGAGGTACTTAATGAGGTCTTAGTTGTACCAAATATC
270  51_HRV47b|   AACCCAGTCGAAAATTATGTGGAAGAGGTACTTAATGAGGTCTTAGTTGTACCAAATATC
271  52_HRV11     AACCCAGTGGAGGATTATGTTGATGGAATTCTAAATGAGGTTTTAGTTGTACCTAATATA
272  53_HRV11b|   AACCCAGTGGAGGATTATGTTGATGGAATTCTAAATGAGGTTTTAGTTGTACCTAATATA
273  54_HRV11a|   AACCCAGTGGAGGATTATGTTGATGGAATTCTAAATGAGGTTTTAGTTGTACCTAATATA
274  55_HRV76     AACCCAGTTGAAAATTACGTGGATGAGATATTAAATGAGGTTCTTGTAGTACCAAACATC
275  56_HRV76b|   AACCCAGTTGAAAATTACGTGGATGAGATATTAAATGAGGTTCTTGTAGTACCAAACATC
276  57_HRV76a|   AACCCAGTTGAAAATTACGTGGATGAGATATTAAATGAGGTTCTTGTAGTACCAAACATC
277  58_HRV33     AATCCAGTAGAGAATTATATAGAAGAGGTGTTGAATGAGGTTTTAGTAGTGCCTAATATC
278  59_HRV33b|   AATCCAGTAGAGAATTATATAGAAGAGGTGTTGAATGAGGTTTTAGTAGTGCCTAATATC
279  60_HRV33a|   AATCCAGTAGAGAATTATATAGAAGAGGTGTTGAATGAGGTTTTAGTAGTGCCTAATATC
280  61_HRV24a|   AACCCAGTAGAAAATTATATAGATGAGGTTTTGAATGAAGTACTGGTTGTGCCTAATATT
281  62_HRV24b|   AACCCAGTAGAAAATTATATAGATGAGGTTTTGAATGAAGTACTGGTTGTGCCTAATATT
282  63_HRV24     AACCCAGTAGAAAATTATATAGATGAGGTTTTGAATGAAGTACTGGTTGTGCCTAATATT
283  64_HRV90     AATCCAGTGGAAAATTATATAGATGAAGTCCTAAATGAGGTATTGGTTGTCCCTAATATT
284  65_HRV90a|   AATCCAGTGGAAAATTATATAGATGAAGTCCTAAATGAGGTATTGGTTGTCCCTAATATT
285  66_HRV90b|   AATCCAGTGGAAAATTATATAGATGAAGTCCTAAATGAGGTATTGGTTGTCCCTAATATT
286  67_HRV34     AATCCAGTTGAAAATTACATAGATGAGGTACTAAATGAGGTATTGGTTGTACCAAACATT
287  68_HRV34b|   AATCCAGTTGAAAATTACATAGATGAGGTACTAAATGAGGTATTGGTTGTACCAAACATT
288  69_HRV34a|   AATCCAGTTGAAAATTACATAGATGAGGTACTAAATGAGGTATTGGTTGTACCAAACATT
289  70_HRV50a|   AATCCAGTGGAGAATTACATAGATGAAGTATTAAATGAGGTATTAGTTGTCCCAAATATC
290  71_HRV50b|   AATCCAGTGGAGAATTACATAGATGAAGTATTAAATGAGGTATTAGTTGTCCCAAATATC
291  72_HRV50     AATCCAGTGGAGAATTACATAGATGAAGTATTAAATGAGGTATTAGTTGTCCCAAATATC
292  73_HRV18a|   AATCCAGTAGAGAATTATATAGATGAAGTACTTAATGAAGTGTTAGTGGTCCCAAATGTG
293  74_HRV18b|   AATCCAGTAGAGAATTATATAGATGAAGTACTTAATGAAGTGTTAGTGGTCCCAAATGTG
294  75_HRV18     AATCCAGTAGAGAATTATATAGATGAAGTACTTAATGAAGTGTTAGTGGTCCCAAATGTG
295  76_HRV55     AATCCTGTAGAGAGATATGTTGATGAAGTCCTGAATGAAGTGCTAGTAGTTCCAAATATT
296  77_HRV55b|   AATCCTGTAGAGAGATATGTTGATGAAGTCCTGAATGAAGTGCTAGTAGTTCCAAATATT
297  78_HRV55a|   AATCCTGTAGAGAGATATGTTGATGAAGTCCTGAATGAAGTGCTAGTAGTTCCAAATATT
298  79_HRV57     AACCCAGTAGAAAATTTTGTGGATGAGATCTTGAATGAAGTTTTGGTGGTTCCAGATATC
299  80_HRV57a|   AACCCAGTAGAAAATTTTGTGGATGAGATCTTGAATGAAGTTTTGGTGGTTCCAGATATC
300  81_HRV57b|   AACCCAGTAGAAAATTTTGTGGATGAGATCTTGAATGAAGTTTTGGTGGTTCCAGATATC
301  82_HRV21     AATCCTGTAGAGAATTATATAGATGAAGTCCTAAATGAAGTCTTAGTAGTGCCAAATATC
302  83_HRVHan    AATCCTGTAGAGAATTATATAGATGAAGTTCTAAATGAGGTCTTAGTAGTGCCAAATATC
303  84_HRV43     AATCCTGTTGAAAATTATGTTGATGAAATTTTAAATCAAGTTCTTGTAGTCCCAAACACT
304  85_HRV43b|   AATCCTGTTGAAAATTATGTTGATGAAATTTTAAATCAAGTTCTTGTAGTCCCAAACACT
305  86_HRV43a|   AATCCTGTTGAAAATTATGTTGATGAAATTTTAAATCAAGTTCTTGTAGTCCCAAACACT
306  87_HRV75     AATCCAGTTGAAAATTATGTGGATGAAATTTTAAACCAAGTTCTGGTAGTTCCAAACACC
307  88_HRV75b|   AATCCAGTTGAAAATTATGTGGATGAAATTTTAAACCAAGTTCTGGTAGTTCCAAACACC
308  89_HRV75a|   AATCCAGTTGAAAATTATGTGGATGAAATTTTAAACCAAGTTCTGGTAGTTCCAAACACC
309  96_HRV9a|d   AATCCAGTGGAGAATTACATAGATCAGGTGCTTAATGAGGTTTTGGTAGTCCCAAACATT
310  97_HRV9b|d   AATCCAGTGGAGAATTACATAGATCAGGTGCTTAATGAGGTTTTGGTAGTCCCAAACATT
311  98_HRV9      AATCCAGTGGAGAATTACATAGATCAGGTGCTTAATGAGGTTTTGGTAGTCCCAAACATT
312  99_HRV32     AATCCTGTGGAGAATTACATAGATCAAGTTTTAAATGAAGTTTTGGTAGTTCCAAACATC
313  100_HRV32a   AATCCTGTGGAGAATTACATAGATCAAGTTTTAAATGAAGTTTTGGTAGTTCCAAACATC
314  101_HRV32b   AATCCTGTGGAGAATTACATAGATCAAGTTTTAAATGAAGTTTTGGTAGTTCCAAACATC
315  102_HRV67    AACCCAGTAGAAGATTATGTAGATCAGGTATTGAATGAGGTCCTGGTGGTGCCAAATATA
316  103_HRV67a   AACCCAGTAGAAGATTATGTAGATCAGGTATTGAATGAGGTCCTGGTGGTGCCAAATATA
317  104_HRV67b   AACCCAGTAGAAGATTATGTAGATCAGGTATTGAATGAGGTCCTGGTGGTGCCAAATATA
318  105_HRV15    AACCCAGTGGAGAATTACATAGATGAAGTGTAAATGAGGTTCTAGTAGTTCCAAACATT
319  106_HRV15a   AACCCAGTGGAGAATTACATAGATGAAGTGTAAATGAGGTTCTAGTAGTTCCAAACATT
320  107_HRV15b   AACCCAGTGGAGAATTACATAGATGAAGTGTAAATGAGGTTCTAGTAGTTCCAAACATT
```

FIG. D8 CONT'D

04-2.trace                                                                  9/20/2007 5:04 PM

```
321 108_HRV74a      AACCCAGTGGAGAATTACATAGATGAAGTGTTGAATGAAGTGTTAGTTGTTCCAAATATT
322 109_HRV74b      AACCCAGTGGAGAATTACATAGATGAAGTGTTGAATGAAGTGTTAGTTGTTCCAAATATT
323 110_HRV74       AACCCAGTGGAGAATTACATAGATGAAGTGTTGAATGAAGTGTTAGTTGTTCCAAATATT
324 111_HRV38a      AACCCAGTAGAGGAATACATAGATGGAGTCTTGAATGAGGTTCTTGTGGTTCCGAACATT
325 112_HRV38b      AACCCAGTAGAGGAATACATAGATGGAGTCTTGAATGAGGTTCTTGTGGTTCCGAACATT
326 113_HRV38       AACCCAGTAGAGGAATACATAGATGGAGTCTTGAATGAGGTTCTTGTGGTTCCGAACATT
327 114_HRV60       AATCCAGTAGAAAGCTACATAGATGGGGTCTTAAACGAAGTCCTTGTGGTTCCAAACATT
328 115_HRV60a      AATCCAGTAGAAAGCTACATAGATGGGGTCTTAAACGAAGTCCTTGTGGTTCCAAACATT
329 116_HRV60b      AATCCAGTAGAAAGCTACATAGATGGGGTCTTAAACCAAGTCCTTGTGGTTCCAAACATT
330 117_HRV64a      AACCCAGTTGAACAATACATTGATGGTGTGTTGAATGAAGTTTTGATTGTCCCAAACATC
331 118_HRV64b      AACCCAGTTGAACAATACATTGATGGTGTGTTGAATGAAGTTTTGATTGTCCCAAACATC
332 119_HRV64       AACCCAGTTGAACAATACATTGATGGTGTGTTGAATGAAGTTTTGATTGTCCCAAACATC
333 120_HRV94a      AATCCAGTTGAGAAATACATTGATGGTGTATTGAATGAAGTTTTAGTTGTTCCAAATATC
334 121_HRV94b      AATCCAGTTGAGAAATACATTGATGGTGTATTGAATGAAGTTTTAGTTGTTCCAAATATC
335 122_HRV94       AATCCAGTTGAGAAATACATTGATGGTGTATTGAATGAAGTTTTAGTTGTTCCAAATATC
336 123_HRV22       AACCCTGTAGAGAAATACATTGATGGTGTCTATTGAATGAAGTATTGGTTGTTCCAAACACA
337 124_HRV22a      AACCCTGTAGAGAAATACATTGATGGTGTATTGAATGAAGTATTGGTTGTTCCAAACACA
338 125_HRV22b      AACCCTGTAGAGAAATACATTGATGGTGTATTGAATGAAGTATTGGTTGTTCCAAACACA
339 126_HRV82       AATCCAGTTGAAAAGTATGTTGATAGTGTTTTAAACGAGGTATTAGTTGTTCCTAACATT
340 127_HRV82b      AATCCAGTTGAAAAGTATGTTGATAGTGTTTTAAACGAGGTATTAGTTGTTCCTAACATT
341 128_HRV82a      AATCCAGTTGAAAAGTATGTTGATAGTGTTTTAAACGAGGTATTAGTTGTTCCTAACATT
342 129_HRV19       AATCCTGTAGAGAAATATGTGGACACCATTCTGAATGAGGTGCTAGTTGTCCCAAATATC
343 130_HRV19a      AATCCTGTAGAGAAATATGTGGACACCATTCTGAATGAGGTGCTAGTTGTCCCAAATATC
344 131_HRV19b      AATCCTGTAGAGAAATATGTGGACACCATTCTGAATGAGGTGCTAGTTGTCCCAAATATC
345 132_HRV13       AATCCTGTTGAAAGGTATGTAGATGAAGTCTTGAATGAAGTTCTTGTAGTACCAAATATC
346 133_HRV13a      AATCCTGTTGAAAGGTATGTAGATGAAGTCTTGAATGAAGTTCTTGTAGTACCAAATATC
347 134_HRV13b      AATCCTGTTGAAAGGTATGTAGATGAAGTCTTGAATGAAGTTCTTGTAGTACCAAATATC
348 135_HRV41       AATCCTGTAGAAAGGTATGTGGATGAGGTCCTGAATGAGGTTCTTGTGGTACCAAATATT
349 136_HRV41a      AATCCTGTAGAAAGGTATGTGGATGAGGTCCTGAATGAGGTTCTTGTGGTACCAAATATT
350 137_HRV41b      AATCCTGTAGAAAGGTATGTGGATGAGGTCCTGAATGAGGTTCTTGTGGTACCAAATATT
351 138_HRV73       AATCCTGTAAAGATATGTAGATGAAGTTTTGAATGAAGTCCTTGTAGTACCCAATATC
352 139_HRV73b      AATCCTGTAGAAAGATATGTAGATGAAGTTTTGAATGAAGTCCTTGTAGTACCCAATATC
353 140_HRV73a      AATCCTGTAGAAAGATATGTAGATGAAGTTTTGAATGAAGTCCTTGTAGTACCCAATATC
354 141_HRV61       AACCCTGTGGAAAGATATGTAGATGAAGTTTTAAATGAAGTGCTTGTAGTCCCAAACATT
355 142_HRV61a      AACCCTGTGGAAAGATATGTAGATGAAGTTTTAAATGAAGTGCTTGTAGTCCCAAACATT
356 143_HRV61b      AACCCTGTGGAAAGATATGTAGATGAAGTTTTAAATGAAGTGCTTGTAGTCCCAAACATT
357 144_HRV96       AACCCTGTAGAGAGATATGTAGATGAAGTCTTGAATGAGGTTCTTGTAGTCCCTAATATT
358 145_HRV96b      AACCCTGTAGAGAGATATGTAGATGAAGTCTTGAATGAGGTTCTTGTAGTCCCTAATATT
359 146_HRV96a      AACCCTGTAGAGAGATATGTAGATGAAGTCTTGAATGAGGTTCTTGTAGTCCCTAATATT
360  90_HRV16a|     AATCCAGTGGAAAGATATGTAGATGAAGTCTTAAATGAAGTGTTAGTAGTGCCCAATATT
361  91_HRV16b|     AATCCAGTGGAAAGATATGTAGATGAAGTCTTAAATGAAGTGTTAGTAGTGCCCAATATT
362  92_1AYM_A      AATCCAGTGGAAAGATATGTAGATGAAGTCTTAAATGAAGTGTTAGTAGTGCCCAATATT
363  93_HRV81a|     AACCCAGTGGAGCGGTATGTGGATGAAGTCTTAAATGAGGTATTGGTAGTCCCTAATATT
364  94_HRV81b|     AACCCAGTGGAGCGGTATGTGGATGAAGTCTTAAATGAGGTATTGGTAGTCCCTAATATT
365  95_HRV81       AACCCAGTGGAGCGGTATGTGGATGAAGTCTTAAATGAGGTATTGGTAGTCCCTAATATT
366 147_HRV2        AACCCTGTTGAGAATTATATAGATGAAGTTCTTAATGAAGTTTTAGTTGTCCCAAATATT
367 148_HRV2a|      AACCCTGTTGAGAATTATATAGATGAAGTTCTTAATGAAGTTTTAGTTGTCCCAAATATT
368 149_HRV2b|      AACCCTGTTGAGAATTATATAGATGAAGTTCTTAATGAAGTTTTAGTTGTCCCAAATATT
369 150_HRV49a      AATCCTGTTGAACACTACATAGATGAGGTCCTTAATGAGGTTTTAGTTGTTCCAAATATT
370 151_HRV49b      AATCCTGTTGAACACTACATAGATGAGGTCCTTAATGAGGTTTTAGTTGTTCCAAATATT
371 152_HRV49       AATCCTGTTGAACACTACATAGATGAGGTCCTTAATGAGGTTTTAGTTGTTCCAAATATT
372 153_HRV23a      AATCCAATTGAGAACTATGTAGATGAAGTTCTTAATGAAGTCTTAGTTGTTCCCAATATC
373 154_HRV23b      AATCCAATTGAGAACTATGTAGATGAAGTTCTTAATGAAGTCTTAGTTGTTCCCAATATC
374 155_HRV23       AATCCAATTGAGAACTATGTAGATGAAGTTCTTAATGAAGTCTTAGTTGTTCCCAATATC
375 156_HRV30a      AACCCGGTTGAAAATTTTGTAGATGAAGTTCTTAGTGAAGTTTAGTTGTTCCAAACATT
376 157_HRV30b      AACCCGGTTGAAAATTTTGTAGATGAAGTTCTTAGTGAAGTTTTAGTTGTTCCAAACATT
377 158_HRV30       AACCCGGTTGAAAATTTTGTAGATGAAGTTCTTAGTGAAGTTTTAGTTGTTCCAAACATT
378 159_HRV7        AACCCGGTAGAGAATTATGTAGATAGCTTACTAAATGAAGTATTAGTGGTACCTAATATT
379 160_HRV7b|      AACCCGGTAGAGAATTATGTAGATAGCTTACTAAATGAAGTATTAGTGGTACCTAATATT
380 161_HRV7a|      AACCCGGTAGAGAATTATGTAGATAGCTTACTAAATGAAGTATTAGTGGTACCTAATATT
381 162_HRV88       AATCCAGTAGAAAACTATGTAGATAACTTGTTAAACGAAGTGCTAGTAGTTCCTAACATT
382 163_HRV88a      AATCCAGTAGAAAACTATGTAGATAACTTGTTAAACGAAGTGCTAGTAGTTCCTAACATT
383 164_HRV88b      AATCCAGTAGAAAACTATGTAGATAACTTGTTAAACGAAGTGCTAGTAGTTCCTAACATT
384 165_HRV36a      AATCCAGTTGAAAATTACATAGATAATGTATTAAATGAAGTACTTGTAGTGCCAAACATC
385 166_HRV36b      AATCCAGTTGAAAATTACATAGATAATGTATTAAATGAAGTACTTGTAGTGCCAAACATC
```

FIG. D8 CONT'D

04-2.trace                                                                 9/20/2007 5:04 PM

```
386  167_HRV36      AATCCAGTTGAAAATTACATAGATAATGTATTAAATGAAGTACTTGTAGTGCCAAACATC
387  168_HRV89a     AACCCAGTTGAAAATTATATAGATAGTGTATTAAATGAAGTTCTTGTGGTGCCAAATATC
388  169_HRV89b     AACCCAGTTGAAAATTATATAGATAGTGTATTAAATGAAGTTCTTGTGGTGCCAAATATC
389  170_HRV89      AACCCAGTTGAAAATTATATAGATAGTGTATTAAATGAAGTTCTTGTGGTGCCAAATATC
390  171_HRV58      AATCCAGTAGAAAATTACATAGATAATGTGTTAAATGAAGTACTTGTAGTTCCAAATATC
391  172_HRV58a     AATCCAGTAGAAAATTACATAGATAATGTGTTAAATGAAGTACTTGTAGTTCCAAATATC
392  173_HRV58b     AATCCAGTAGAAAATTACATAGATAATGTGTTAAATGAAGTACTTGTAGTTCCAAATATC
393  174_HRV12a     AATCCAGTAGAGAGATATGTTGATGAGGTGCTAAATGAAGTTCTAGTTGTTCCAAACATA
394  175_HRV12b     AATCCAGTAGAGAGATATGTTGATGAGGTGCTAAATGAAGTTCTAGTTGTTCCAAACATA
395  176_HRV12      AATCCAGTAGAGAGATATGTTGATGAGGTGCTAAATGAAGTTCTAGTTGTTCCAAACATA
396  177_HRV78a     AATCCAGTGGAAGAATATGTTGATCAGGTTTTAAATGAGGTTTTAGTTGTTCCAAACATA
397  178_HRV78b     AATCCAGTGGAAGAATATGTTGATCAGGTTTTAAATGAGGTTTTAGTTGTTCCAAACATA
398  179_HRV78      AATCCAGTGGAAGAATATGTTGATCAGGTTTTAAATGAGGTTTTAGTTGTTCCAAACATA
399  180_HRV20      AACCCAGTGGAAAGGTACACAGAAGCTATTTTAAATGAAGTTCTTGTAGTTCCAAATATC
400  181_HRV20a     AACCCAGTGGAAAGGTACACAGAAGCTATTTTAAATGAAGTTCTTGTAGTTCCAAATATC
401  182_HRV20b     AACCCAGTGGAAAGGTACACAGAAGCTATTTTAAATGAAGTTCTTGTAGTTCCAAATATC
402  183_HRV68      AACCCAGTTGAAAATACACAGAAGCCGTTCTTAATGAGGTCCTTGTGGTTCCAAACATA
403  184_HRV68a     AACCCAGTTGAAAATACACAGAAGCCGTTCTTAATGAGGTCCTTGTGGTTCCAAACATA
404  185_HRV68b     AACCCAGTTGAAAATACACAGAAGCCGTTCTTAATGAGGTCCTTGTGGTTCCAAACATA
405  186_HRV28      AATCCAGTTGAAAAATATACTGAAGCACTACTTAATGAAGTGCTTGTTGTGCCAAACATC
406  187_HRV28a     AATCCAGTTGAAAAATATACTGAAGCACTACTTAATGAAGTGCTTGTTGTGCCAAACATC
407  188_HRV28b     AATCCAGTTGAAAAATATACTGAAGCACTACTTAATGAAGTGCTTGTTGTGCCAAACATC
408  189_HRV53a     AACCCGGTAGAGAAATACACAGAGGCTATCTTAAATGAAGTATTAGTAGTCCCAAACATT
409  190_HRV53b     AACCCGGTAGAGAAATACACAGAGGCTATCTTAAATGAAGTATTAGTAGTCCCAAACATT
410  191_HRV53      AACCCGGTAGAGAAATACACAGAGGCTATCTTAAATGAAGTATTAGTAGTCCCAAACATT
411  192_HRV46a     AATCCAGTGGAAAAATATACAGAAGCTGTTCTTAATGAGGTCCTTGTAGTACCTAACATC
412  193_HRV46b     AATCCAGTGGAAAAATATACAGAAGCTGTTCTTAATGAGGTCCTTGTAGTACCTAACATC
413  194_HRV46      AATCCAGTGGAAAAATATACAGAAGCTGTTCTTAATGAGGTCCTTGTAGTACCTAACATC
414  195_HRV80a     AATCCAGTCGAAAAATACACAGAAGCAATCCTCAATGAAGTTCTTGTTGTACCAAACATC
415  196_HRV80b     AATCCAGTCGAAAAATACACAGAAGCAATCCTCAATGAAGTTCTTGTTGTACCAAACATC
416  197_HRV80      AATCCAGTCGAAAAATACACAGAAGCAATCCTCAATGAAGTTCTTGTTGTACCAAACATC
417  198_HRV51      AACCCTGTTGAAAAATATACAGAGGCTTTACTCAATGAAGTGTTGGTGGTTCCCAACATA
418  199_HRV51a     AACCCTGTTGAAAAATATACAGAGGCTTTACTCAATGAAGTGTTGGTGGTTCCCAACATA
419  200_HRV51b     AACCCTGTTGAAAAATATACAGAGGCTTTACTCAATGAAGTGTTGGTGGTTCCCAACATA
420  201_HRV65a     AATCCAATTGAGAAGTATACAGAAGCTCTACTTAATGAAGTGTTGGTGGTCCCAAATATA
421  202_HRV65b     AATCCAATTGAGAAGTATACAGAAGCTCTACTTAATGAAGTGTTGGTGGTCCCAAATATA
422  203_HRV65      AATCCAATTGAGAAGTATACAGAAGCTCTACTTAATGAAGTGTTGGTGGTCCCAAATATA
423  204_HRV71a     AATCCTGTAGAAAAATATACAGAAGCAATACTCAATGAGGTTCTAGTTGTGCCAAATATA
424  205_HRV71b     AATCCTGTAGAAAAATATACAGAAGCAATACTCAATGAGGTTCTAGTTGTGCCAAATATA
425  206_HRV71      AATCCTGTAGAAAAATATACAGAAGCAATACTCAATGAGGTTCTAGTTGTGCCAAATATA
426  207_HRV8       AACCCTATTGAACAATTCACAGAGGCAGTATTAAACGAGGTTCTTGTAGTTCCAAACACA
427  208_HRV95      AACCCTATTGAACAATTCACAGAGGCAGTATTAAACGAGGTTCTTGTAGTTCCAAATACA
428  209_HRV45      AACCCTGTTGAACAATTTGCAGAAGCAGTCCTTGATCAAGTATTAGTAGTTCCAAACACT
429  210_HRV45a     AACCCTGTTGAACAATTTGCAGAAGCAGTCCTTGATCAAGTATTAGTAGTTCCAAACACT
430  211_HRV45b     AACCCTGTTGAACAATTTGCAGAAGCAGTCCTTGATCAAGTATTAGTAGTTCCAAACACT
431  GROUP_1        AA-CC--T-GA----T------A-----T--T-----A-GT--T--T-GT-CC--A----
432
433  1_HRV1A1|d     AAAGAAAGTCATCACACTACATCAAACTCTGCCCCACTTTTAGATGCTGCAGAGACGGGA
434  2_HRV1A2|d     AAAGAAAGTCATCACACTACATCAAACTCTGCCCCACTTTTAGATGCTGCAGAGACGGGA
435  3_HRV1A|cD     AAAGAAAGTCATCACACTACATCAAACTCTGCCCCACTTTTAGATGCTGCAGAGACGGGA
436  4_HRV1B1|d     AAAGAAAGCCATCACACTACATCAAATTCTGCTCCACTCTTGGATGCTGCAGAGACAGGA
437  5_HRV1B2|d     AAAGAAAGCCATCACACTACATCAAATTCTGCTCCACTCTTGGATGCTGCAGAGACAGGA
438  6_HRV1B        AAAGAAAGCCATCACACTACATCAAATTCTGCTCCACTCTTGGATGCTGCAGAGACAGGA
439  7_HRV40a|d     AGAGAGAGCCATCCAACTACATCAAATTCGGCCCCTGCCTTGGATGCAGCAGAGACTGGA
440  8_HRV40b|d     AGAGAGAGCCATCCAACTACATCAAATTCGGCCCCTGCCTTGGATGCAGCAGAGACTGGA
441  9_HRV40        AGAGAGAGCCATCCAACTACATCAAATTCGGCCCCTGCCTTGGATGCAGCAGAGACTGGA
442  10_HRV85       AAAGAGAGTCACCCAACTATATCAAATTCAGCTCCTGCTTTGGATGCAGCAGAGACTGGC
443  11_HRV85a|     AAAGAGAGTCACCCAACTATATCAAATTCAGCTCCTGCTTTGGATGCAGCAGAGACTGGC
444  12_HRV85b|     AAAGAGAGTCACCCAACTATATCAAATTCAGCTCCTGCTTTGGATGCAGCAGAGACTGGC
445  13_HRV56a|     AGGGAGAGCCATCCATCCACATCAAATTCTGCCCCTGCATTAGATGCTGCTGAAACTGGC
446  14_HRV56b|     AGGGAGAGCCATCCATCCACATCAAATTCTGCCCCTGCATTAGATGCTGCTGAAACTGGC
447  15_HRV56       AGGGAGAGCCATCCATCCACATCAAATTCTGCCCCTGCATTAGATGCTGCTGAAACTGGC
448  16_HRV54       AGAGAAAGTCATCCAGCTACATCTAATTCAGCCCCTGCGCTAGATGCGGCAGAAACTGGA
449  17_HRV98       AAAGAAAGTCATCCAGCTACATCTAATTCGGCCCCTACACTAGATGCAGCAGAAACTGGG
450  18_HRV59a|     CAGGAAAGCCACCCAACCACCTCAAATGCTGCTCCAGCATTAGATGCAGCAGAGACTGGA
```

FIG. D8 CONT'D

04-2.trace                                                                    9/20/2007 5:04 PM

```
451  19_HRV59b|   CAGGAAAGCCACCCAACCACCTCAAATGCTGCTCCAGCATTAGATGCAGCAGAGACTGGA
452  20_HRV59     CAGGAAAGCCACCCAACCACCTCAAATGCTGCTCCAGCATTAGATGCAGCAGAGACTGGA
453  21_HRV63     CAAGAAAGCCATCCAACCACATCAAACGCTGCTCCTGTACTTGATGCTGCGGAAACAGGA
454  22_HRV63b|   CAAGAAAGCCATCCAACCACATCAAACGCTGCTCCTGTACTTGATGCTGCGGAAACAGGA
455  23_HRV63a|   CAAGAAAGCCATCCAACCACATCAAACGCTGCTCCTGTACTTGATGCTGCGGAAACAGGA
456  24_HRV39     AGAGAGAGCCATCCAACTACATCTAATGCAGCTACAGCTTTGGATGCTGCTGAAACTGGA
457  25_HRV39a|   AGAGAGAGCCATCCAACTACATCTAATGCAGCTACAGCTTTGGATGCTGCTGAAACTGGA
458  26_HRV39b|   AGAGAGAGCCATCCAACTACATCTAATGCAGCTCCAGCTTTGGATGCTGCTGAAACTGGA
459  27_HRV10a|   AGAGAAAGTCATCCAAGCACCTCTAACTCTGCCCCAATTCTCGATGCAGCTGAGACTGGT
460  28_HRV10b|   AGAGAAAGTCATCCAAGCACCTCTAACTCTGCCCCAATTCTCGATGCAGCTGAGACTGGT
461  29_HRV10     AGAGAAAGTCATCCAAGCACCTCTAACTCTGCCCCAATTCTCGATGCAGCTGAGACTGGT
462  30_HRV100a   AGAGAGAGCCATCCAAGCACCTCAAACTCTGCTCCAATCCTTGATGCTGCTGAAACTGGC
463  31_HRV100b   AGAGAGAGCCATCCAAGCACCTCAAACTCTGCTCCAATCCTTGATGCTGCTGAAACTGGC
464  32_HRV100    AGAGAGAGCCATCCAAGCACCTCAAACTCTGCTCCAATCCTTGATGCTGCTGAAACTGGC
465  33_HRV66     AAGGAAAGCCATCCAAGCACATCAAATGCTGCCCCAATACTAGATGCAGCTGAAACAGGT
466  34_HRV66b|   AAGGAAAGCCATCCAAGCACATCAAATGCTGCCCCAATACTAGATGCAGCTGAAACAGGT
467  35_HRV66a|   AAGGAAAGCCATCCAAGCACATCAAATGCTGCCCCAATACTAGATGCAGCTGAAACAGGT
468  36_HRV77a|   AAGGAGAGTCATCCAAGCACTTCTAACTCTGCTCCTATACTAGATGCAGCTGAAACAGGC
469  37_HRV77b|   AAGGAGAGTCATCCAAGCACTTCTAACTCTGCTCCTATACTAGATGCAGCTGAAACAGGC
470  38_HRV77     AAGGAGAGTCATCCAAGCACTTCTAACTCTGCTCCTATACTAGATGCAGCTGAAACAGGC
471  39_HRV62a    AAAGAAAGTCACCCTAGTACGTCAAACTCTGCCCCAATTCTAGATGCTGCTGAAACCGGA
472  40_HRV62b    AAAGAAAGTCACCCTAGTACGTCAAACTCTGCCCCAATTCTAGATGCTGCTGAAACCGGA
473  41_HRV25     AAAGAAAGTCACCCAAGCACATCAAATTCTGCCCCAATTCTAGATGCTGCTGAAACTGGA
474  42_HRV29a    AGGGAGAGCCACCCAAGCACGTCCAACTCTGCACCAATCTTGGATGCTGCTGAGACTGGA
475  43_HRV29b    AGGGAGAGCCACCCAAGCACGTCCAACTCTGCACCAATCTTGGATGCTGCTGAGACTGGA
476  44_HRV44a    AGAGAGAGCCACACATCTAACTCTGCTCCAATTTTGGATGCTGCTGAAACTGGA
477  45_HRV44b    AGAGAGAGCCACCCAAGCATATCTAACTCTGCTCCAATTTTGGATGCTGCTGAAACTGGA
478  46_HRV31     AAAGAAAGCCATCCAAGCACATCTAATTCTGCCCCAATCCTGGACGCTGCTGAAACTGGA
479  47_HRV31a|   AAAGAAAGCCATCCAAGCACATCTAATTCTGCCCCAATCCTGGACGCTGCTGAAACTGGA
480  48_HRV31b|   AAAGAAAGCCATCCAAGCACATCTAATTCTGCCCCAATCCTGGACGCTGCTGAAACTGGA
481  49_HRV47     AAAGAAAGTCATCCAAGTACATCCAACTCTGCCCCGATTTTAGATGCTGCTGAAACTGGA
482  50_HRV47a|   AAAGAAAGTCATCCAAGTACATCCAACTCTGCCCCGATTTTAGATGCTGCTGAAACTGGA
483  51_HRV47b|   AAAGAAAGTCATCCAAGTACATCCAACTCTGCCCCGATTTTAGATGCTGCTGAAACTGGA
484  52_HRV11     AAGGAGAGCCAAGCTACCACATCAAACTCAGCACCTGTCTAGATGCAGCTGAAACCGGA
485  53_HRV11b|   AAGGAGAGCCAAGCTACCACATCAAACTCAGCACCTGCTCTAGATGCAGCTGAAACCGGA
486  54_HRV11a|   AAGGAGAGCCAAGCTACCACATCAAACTCAGCACCTGCTCTAGATGCAGCTGAAACCGGA
487  55_HRV76     AAAGAGAGTCAGGCTACCACATCAAATGCAGCACCTGCTTTGGATGCAGCTGAGACTGGG
488  56_HRV76b|   AAAGAGAGTCAGGCTACCACATCAAATGCAGCACCTGCTTTGGATGCAGCTGAGACTGGG
489  57_HRV76a|   AAAGAGAGTCAGGCTACCACATCAAATGCAGCACCTGCTTTGGATGCAGCTGAGACTGGG
490  58_HRV33     AGAGAGAGTCAAGCAACCACATCAAATTCAGCACCTGCCTTAGATGCAGCTGAGACTGGA
491  59_HRV33b|   AGAGAGAGTCAAGCAACCACATCAAATTCAGCACCTGCCTTAGATGCAGCTGAGACTGGA
492  60_HRV33a|   AGAGAGAGTCAAGCAACCACATCAAATTCAGCACCTGCCTTAGATGCAGCTGAGACTGGA
493  61_HRV24a|   AAGGAAAGTAAACCATCAACATCAAACTCAGCACCAGCTTTGGATGCAGCAGAAACTGGA
494  62_HRV24b|   AAGGAAAGTAAACCATCAACATCAAACTCAGCACCAGCTTTGGATGCAGCAGAAACTGGA
495  63_HRV24     AAGGAAAGTAAACCATCAACATCAAACTCAGCACCAGCTTTGGATGCAGCAGAAACTGGA
496  64_HRV90     AAGGAAAGTAAACCTTCAACTTCAAACTCAGCGCCAGCTTTAGATGCAGCAGAAACCGGA
497  65_HRV90a|   AAGGAAAGTAAACCTTCAACTTCAAACTCAGCGCCAGCTTTAGATGCAGCAGAAACCGGA
498  66_HRV90b|   AAGGAAAGTAAACCTTCAACTTCAAACTCAGCGCCAGCTTTAGATGCAGCAGAAACCGGA
499  67_HRV34     AAAGAAAGCCAAGCCACCACATCAAACTCTGCCCCCGCACTGGATGCAGCTGAGACTGGT
500  68_HRV34b|   AAAGAAAGCCAAGCCACCACATCAAACTCTGCCCCCGCACTGGATGCAGCTGAGACTGGT
501  69_HRV34a|   AAAGAAAGCCAAGCCACCACATCAAACTCTGCCCCCGCACTGGATGCAGCTGAGACTGGT
502  70_HRV50a|   AAGGAGAGTCAAGCCACTACATCAAACTCTGCCCCTGCTTTAGATGCAGCTGAAACTGGA
503  71_HRV50b|   AAGGAGAGTCAAGCCACTACATCAAACTCTGCCCCTGCTTTAGATGCAGCTGAAACTGGA
504  72_HRV50     AAGGAGAGTCAAGCCACTACATCAAACTCTGCCCCTGCTTTAGATGCAGCTGAAACTGGA
505  73_HRV18a|   AATGAAAGTCACGCAATTACATCAAATTCAGCCCCTGCTTTAGATGCCGCTGAAACTGGT
506  74_HRV18b|   AATGAAAGTCACGCAATTACATCAAATTCAGCCCCTGCTTTAGATGCCGCTGAAACTGGT
507  75_HRV18     AATGAAAGTCACGCAATTACATCAAATTCAGCCCCTGCTTTAGATGCCGCTGAAACTGGT
508  76_HRV55     AGGGAGAGTCAAGCAGCAACATCAAATTCAGCTCCAGTACTAGATGCAGCAGAAACTGGG
509  77_HRV55b|   AGGGAGAGTCAAGCAGCAACATCAAATTCAGCTCCAGTACTAGATGCAGCAGAAACTGGG
510  78_HRV55a|   AGGGAGAGTCAAGCAGCAACATCAAATTCAGCTCCAGTACTAGATGCAGCAGAAACTGGG
511  79_HRV57     AAACAAAGTCAAGCAACAACATCAAACTCAGCACCTGCTTTGGATGCAGCTGAAACTGGA
512  80_HRV57a|   AAACAAAGTCAAGCAACAACATCAAACTCAGCACCTGCATTGGATGCAGCTGAAACTGGA
513  81_HRV57b|   AAACAAAGTCAAGCAACAACATCAAACTCAGCACCTGCATTGGATGCAGCTGAAACTGGA
514  82_HRV21     AGAGAGAGTCATGGAACAACATCAAACTCTGCTCCCGCACTTGATGCTGCAGAAACTGGA
515  83_HRVHan    AGAGAGAGTCATGGAACAACATCAAACTCTGCTCCCGCACTTGATGCTGCAGAAACTGGG
```

FIG. D8 CONT'D 04-2.trace                                                                                      9/20/2007 5:04 PM

```
516  84_HRV43     GTAGAAAGTCATTCAACAACATCCAATGCAGCCCCTGCACTTGATGCAGCTGAAACTGGG
517  85_HRV43b|   GTAGAAAGTCATTCAACAACATCCAATGCAGCCCCTGCACTTGATGCAGCTGAAACTGGG
518  86_HRV43a|   GTAGAAAGTCATTCAACAACATCCAATGCAGCCCCTGCACTTGATGCAGCTGAAACTGGG
519  87_HRV75     ATGGAGAGCCATCCAACAACGTCTAATGCTGCTCCAGCTTTAGATGCAGCTGAAACTGGC
520  88_HRV75b|   ATGGAGAGCCATCCAACAACGTCTAATGCTGCTCCAGCTTTAGATGCAGCTGAAACTGGC
521  89_HRV75a|   ATGGAGAGCCATCCAACAACGTCTAATGCTGCTCCAGCTTTAGATGCAGCTGAAACTGGC
522  96_HRV9a|d   AAAGAGAGCAACCCTACAACCTCTAACTCAGCTCCAGCTCTAGATGCTGCTGAGACAGGC
523  97_HRV9b|d   AAAGAGAGCAACCCTACAACCTCTAACTCAGCTCCAGCTCTAGATGCTGCTGAGACAGGC
524  98_HRV9      AAAGAGAGCAACCCTACAACCTCTAACTCAGCTCCAGCTCTAGATGCTGCTGAGACAGGC
525  99_HRV32     AAAGAAAGCAATCCCACAACCTCTAATTCAGCCCCAGCCTTAGATGCTGCCGAAACAGGT
526  100_HRV32a   AAAGAAAGCAATCCCACAACCTCTAATTCAGCCCCAGCCTTAGATGCTGCCGAAACAGGT
527  101_HRV32b   AAAGAAAGCAATCCCACAACCTCTAATTCAGCCCCAGCCTTAGATGCTGCCGAAACAGGT
528  102_HRV67    AAGCAAAGTGAACCCACGACTTCCAATTCAGCCCCAGCTCTAGATGCTGCTGAGACAGGT
529  103_HRV67a   AAGCAAAGTGAACCCACGACTTCCAATTCAGCCCCAGCTCTAGATGCTGCTGAGACAGGT
530  104_HRV67b   AAGCAAAGTGAACCCACGACTTCCAATTCAGCCCCAGCTCTAGATGCTGCTGAGACAGGT
531  105_HRV15    AAGGAGAGTCACTCAAGCACATCCAACTCAGCACCAGCACTAGATGCAGCTGAGACCGGC
532  106_HRV15a   AAGGAGAGTCACTCAAGCACATCCAACTCAGCACCAGCACTAGATGCAGCTGAGACCGGC
533  107_HRV15b   AAGGAGAGTCACTCAAGCACATCCAACTCAGCACCAGCACTAGATGCAGCTGAGACCGGC
534  108_HRV74a   AGAGAAAGCCATTCAAGTACTTCAAACTCAGCACCAGCACTGGATGCAGCTGAAACTGGC
535  109_HRV74b   AGAGAAAGCCATTCAAGTACTTCAAACTCAGCACCAGCACTGGATGCAGCTGAAACTGGC
536  110_HRV74    AGAGAAAGCCATTCAAGTACTTCAAACTCAGCACCAGCACTGGATGCAGCTGAAACTGGC
537  111_HRV38a   AAGGAAAGCCACTCCAGCACATCAAATTCAGCACCAGCATTAGATGCTGCTGAGACTGGA
538  112_HRV38b   AAGGAAAGCCACTCCAGCACATCAAATTCAGCACCAGCATTAGATGCTGCTGAGACTGGA
539  113_HRV38    AAGGAAAGCCACTCCAGCACATCAAATTCAGCACCAGCATTAGATGCTGCTGAGACTGGA
540  114_HRV60    AGGGAGAGCCAACCCACTACTTCTGCTCCAGCATTGGATGCTGCTGAGACTGGT
541  115_HRV60a   AGGGAGAGCCAACCCACTACTTCTAATTCTGCTCCAGCATTGGATGCTGCTGAGACTGGT
542  116_HRV60b   AGGGAGAGCCAACCCACTACTTCTAATTCTGCTCCAGCATTGGATGCTGCTGAGACTGGT
543  117_HRV64a   AATGAGAGCCATCCCAGCACTTCCAATGCAGCGCCAGCTTTAGATGCAGCTGAGACCGGA
544  118_HRV64b   AATGAGAGCCATCCCAGCACTTCCAATGCAGCGCCAGCTTTAGATGCAGCTGAGACCGGA
545  119_HRV64    AATGAGAGCCATCCCAGCACTTCCAATGCAGCGCCAGCTTTAGATGCAGCTGAGACCGGA
546  120_HRV94a   AATGAGAGTCACCCTAGCACATCCAATGCAGCGCCAGCCTTAGATGCTGCCGAAACTGGA
547  121_HRV94b   AATGAGAGTCACCCTAGCACATCCAATGCAGCGCCAGCCTTAGATGCTGCCGAAACTGGA
548  122_HRV94    AATGAGAGTCACCCTAGCACATCCAATGCAGCGCCAGCCTTAGATGCTGCCGAAACTGGA
549  123_HRV22    AATGAAAGTCACCCCAGTACATCAAATGCTGCACCAGCACTAGATGCTGCTGAAACTGGA
550  124_HRV22a   AATGAAAGTCACCCCAGTACATCAAATGCTGCACCAGCACTAGATGCTGCTGAAACTGGA
551  125_HRV22b   AATGAAAGTCACCCCAGTACATCAAATGCTGCACCAGCACTAGATGCTGCTGAAACTGGA
552  126_HRV82    AATGAAAGTCATCCTAGTACTTCAAATTCAGCTCCTGCCTTGGACGCTGCAGAGACAGGA
553  127_HRV82b   AATGAAAGTCATCCTAGTACTTCAAATTCAGCTCCTGCCTTGGACGCTGCAGAGACAGGA
554  128_HRV82a   AATGAAAGTCATCCTAGTACTTCAAATTCAGCTCCTGCCTTGGACGCTGCAGAGACAGGA
555  129_HRV19    AATGAAAGTCATCCAAGTACATCAAATGCTGCTCCTGCCTTAGATGCAGCCGAGACAGGA
556  130_HRV19a   AATGAAAGTCATCCAAGTACATCAAATGCTGCTCCTGCCTTAGATGCAGCCGAGACAGGA
557  131_HRV19b   AATGAAAGTCATCCAAGTACATCAAATGCTGCTCCTGCCTTAGATGCAGCCGAGACAGGA
558  132_HRV13    AGTGAAAGTAGCTCAACTACATCTAATTCAGCTCCAGCCTTAGATGCTGCAGAAACTGGC
559  133_HRV13a   AGTGAAAGTAGCTCAACTACATCTAATTCAGCTCCAGCCTTAGATGCTGCAGAAACTGGC
560  134_HRV13b   AGTGAAAGTAGCTCAACTACATCTAATTCAGCTCCAGCCTTAGATGCTGCAGAAACTGGC
561  135_HRV41    AGTGAAAGCCAACTACTTCTAATTCAGCTCCAGCCCTAGATGCAGCAGAGACTGGT
562  136_HRV41a   AGTGAAAGCAGTCCAACTACTTCTAATTCAGCTCCAGCCCTAGATGCAGCAGAGACTGGT
563  137_HRV41b   AGTGAAAGCAGTCCAACTACTTCTAATTCAGCTCCAGCCCTAGATGCAGCAGAGACTGGT
564  138_HRV73    AATGAAAGTAATCCAACTACATCCAACTCAGCACCTGCACTGGACGCTGCAGAAACTGGC
565  139_HRV73b   AATGAAAGTAATCCAACTACATCCAACTCAGCACCTGCACTGGACGCTGCAGAAACTGGC
566  140_HRV73a   AATGAAAGTAATCCAACTACATCCAACTCAGCACCTGCACTGGACGCTGCAGAAACTGGC
567  141_HRV61    AATCAGAGCAACCCTACAACATCCAACTCAGCACCAGTCTTAGACGCTGCTGAAACAGGT
568  142_HRV61a   AATCAGAGCAACCCTACAACATCCAACTCAGCACCAGTCTTAGACGCTGCTGAAACAGGT
569  143_HRV61b   AATCAGAGCAACCCTACAACATCCAACTCAGCACCAGTCTTAGACGCTGCTGAAACAGGT
570  144_HRV96    AATGAAAGTTACCCAACAACTTCCAATTCAGCCCCAGTGCTAGATGCCGCTGAAACAGGT
571  145_HRV96b   AATGAAAGTTACCCAACAACTTCCAATTCAGCCCCAGTGCTAGATGCCGCTGAAACAGGT
572  146_HRV96a   AATGAAAGTTACCCAACAACTTCCAATTCAGCCCCAGTGCTAGATGCCGCTGAAACAGGT
573  90_HRV16a|   AATGAGAGCCACCCTACCACATCAAATGCGGCCCCAGTTTTGGATGCTGCTGAAACAGGA
574  91_HRV16b|   AATGAGAGCCACCCTACCACATCAAATGCGGCCCCAGTTTTGGATGCTGCTGAAACAGGA
575  92_1AYM_A    AATGAGAGCCACCCTACCACATCAAATGCGGCCCCAGTTTTGGATGCTGCTGAAACAGGA
576  93_HRV81a|   AATGAAAGCCACCCTACAACATCTAATTCAGCTCCTGTTTTAGATGCTGCAGAAACTGGA
577  94_HRV81b|   AATGAAAGCCACCCTACAACATCTAATTCAGCTCCTGTTTTAGATGCTGCAGAAACTGGA
578  95_HRV81     AATGAAAGCCACCCTACAACATCTAATTCAGCTCCTGTTTTAGATGCAGCTGAAACTGGA
579  147_HRV2     AATAGTAGTAACCCCACAACATCAAATTCTGCCCCAGCATTAGATGCTGCAGAAACAGGG
580  148_HRV2a|   AATAGTAGTAACCCCACAACATCAAATTCTGCCCCAGCATTAGATGCTGCAGAAACAGGG
```

FIG. D8 CONT'D

```
04-2.trace                                                                                                        9/20/2007 5:04 PM 581 149_HRV2b|     AATAGTAGTAACCCCACAACATCAAATTCTGCCCCAGCATTAGATGCTGCAGAAACAGGG
582 150_HRV49a     AATAGTAGTCACCCCACGACATCAAACTCTGCTCCAGCATTAGATGCTGCAGAAACAGGG
583 151_HRV49b     AATAGTAGTCACCCCACGACATCAAACTCTGCTCCAGCATTAGATGCTGCAGAAACAGGG
584 152_HRV49      AATAGTAGTCACCCCACGACATCAAACTCTGCTCCAGCATTAGATGCTGCAGAAACAGGG
585 153_HRV23a     AATAGTAGTCATCCCACAACATCAAACTCTGCTCCAGCATTAGACGCTGCGGAAACGGGT
586 154_HRV23b     AATAGTAGTCATCCCACAACATCAAACTCTGCTCCAGCATTAGACGCTGCGGAAACGGGT
587 155_HRV23      AATAGTAGTCATCCCACAACATCAAACTCTGCTCCAGCATTAGACGCTGCGGAAACGGGT
588 156_HRV30a     AACAGTAGTCACCCTACTACATCAAACTCTGCTCCGGCATTAGATGCTGCAGAAACAGGA
589 157_HRV30b     AACAGTAGTCACCCTACTACATCAAACTCTGCTCCGGCATTAGATGCTGCAGAAACAGGA
590 158_HRV30      AACAGTAGTCACCCTACTACATCAAACTCTGCTCCGGCATTAGATGCTGCAGAAACAGGA
591 159_HRV7       CAGCCAAGTACATCTGTTTCAAGTCACTCTGTACCAGCATTGGATGCTGCAGAGACTGGA
592 160_HRV7b|     CAGCCAAGTACATCTGTTTCAAGTCACTCTGTACCAGCATTGGATGCTGCAGAGACTGGA
593 161_HRV7a|     CAGCCAAGTACATCTGTTTCAAGTCACTCTGTACCAGCATTGGATGCTGCAGAGACTGGA
594 162_HRV88      CAACCTAGCACATCCGTTTCAAGTCACTCTGTGCCAGCTCTGGATGCTGCGGAAACAGGG
595 163_HRV88a     CAACCTAGCACATCCGTTTCAAGTCACTCTGTGCCAGCTCTGGATGCTGCGGAAACAGGG
596 164_HRV88b     CAACCTAGCACATCCGTTTCAAGTCACTCTGTGCCAGCTCTGGATGCTGCGGAAACAGGG
597 165_HRV36a     CAACCTAGTTCATCTGTGTCAAGTCATTCAGCTCCCGCCTTAGACGCTGCGGAAACTGGA
598 166_HRV36b     CAACCTAGTTCATCTGTGTCAAGTCATTCAGCTCCCGCCTTAGACGCTGCGGAAACTGGA
599 167_HRV36      CAACCTAGTTCATCTGTGTCAAGTCATTCAGCTCCCGCCTTAGACGCTGCGGAAACTGGA
600 168_HRV89a     CAACCTAGCACATCTGTGTCAAGTCATGCAGCGCCTGCATTGGATGCTGCGGAAACCGGA
601 169_HRV89b     CAACCTAGCACATCTGTGTCAAGTCATGCAGCGCCTGCATTGGATGCTGCGGAAACCGGA
602 170_HRV89      CAACCTAGCACATCTGTGTCAAGTCATGCAGCGCCTGCATTGGATGCTGCGGAAACCGGA
603 171_HRV58      CAACCTAGTACATCTGTATCAAGTCATTCTGTGCCTGCCTTGGATGCTGCAGAAACGGGA
604 172_HRV58a     CAACCTAGTACATCTGTATCAAGTCATTCTGTGCCTGCCTTGGATGCTGCAGAAACGGGA
605 173_HRV58b     CAACCTAGTACATCTGTATCAAGTCATTCTGTGCCTGCCTTGGATGCTGCAGAAACGGGA
606 174_HRV12a     AACAAAAGTAATGGGCAGTTATCAAACGCAGCACCAGCGTTGGACGCTGCAGAAACTGGT
607 175_HRV12b     AACAAAAGTAATGGGCAGTTATCAAACGCAGCACCAGCGTTGGACGCTGCAGAAACTGGT
608 176_HRV12      AACAAAAGTAATGGGCAGTTATCAAACGCAGCACCAGCGTTGGACGCTGCAGAAACTGGT
609 177_HRV78a     AAAGAAAGTAAACCCCAGTCTAGCAACTCCGCTCCAGTTTTGGACGCTGCAGAAACAGGT
610 178_HRV78b     AAAGAAAGTAAACCCCAGTCTAGCAACTCCGCTCCAGTTTTGGACGCTGCAGAAACAGGT
611 179_HRV78      AAAGAAAGTAAACCCCAGTCTAGCAACTCCGCTCCAGTTTTGGACGCTGCAGAAACAGGT
612 180_HRV20      ACATCTAGTAACTCCCAAACATCAAATGCAGCACCAGCACTAGATGCTGCTGAGACAGGA
613 181_HRV20a     ACATCTAGTAACTCCCAAACATCAAATGCAGCACCAGCACTAGATGCTGCTGAGACAGGA
614 182_HRV20b     ACATCTAGTAACTCCCAAACATCAAATGCAGCACCAGCACTAGATGCTGCTGAGACAGGA
615 183_HRV68      CCAGCAAGTAATACCCAAACTTCAAATGCAGCCCCAGCCTTAGATGCTGCTGAGACTGGA
616 184_HRV68a     CCAGCAAGTAATACCCAAACTTCAAATGCAGCCCCAGCCTTAGATGCTGCTGAGACTGGA
617 185_HRV68b     CCAGCAAGTAATACCCAAACTTCAAATGCAGCCCCAGCCTTAGATGCTGCTGAGACTGGA
618 186_HRV28      AATCCTAGCAACGCACAAACTACAAATGCAGCTCCCGCTCTCGATGCCGCTGAGACGGGG
619 187_HRV28a     AATCCTAGCAACGCACAAACTACAAATGCAGCTCCCGCTCTCGATGCCGCTGAGACGGGG
620 188_HRV28b     AATCCTAGCAACGCACAAACTACAAATGCAGCTCCCGCTCTCGATGCCGCTGAGACGGGG
621 189_HRV53a     AATGCAAGCAATCCACAAACTTCAAATTCAGCACCAGCACTAGATGCTGCAGAAACGGGT
622 190_HRV53b     AATGCAAGCAATCCACAAACTTCAAATTCAGCACCAGCACTAGATGCTGCAGAAACGGGT
623 191_HRV53      AATGCAAGCAATCCACAAACTTCAAATTCAGCACCAGCACTAGATGCTGCAGAAACGGGT
624 192_HRV46a     AATGCCAGTAGTGGACATACATCTAATTCAGCTCCAGCACTTGATGCAGCAGAAACTGGA
625 193_HRV46b     AATGCCAGTAGTGGACATACATCTAATTCAGCTCCAGCACTTGATGCAGCAGAAACTGGA
626 194_HRV46      AATGCCAGTAGTGGACATACATCTAATTCAGCTCCAGCACTTGATGCAGCAGAAACTGGA
627 195_HRV80a     AGTGCTAGCAATGGACATACATCAAACTCAGCTCCAACACTTGATGCAGCAGAAACTGGT
628 196_HRV80b     AGTGCTAGCAATGGACATACATCAAACTCAGCTCCAACACTTGATGCAGCAGAAACTGGT
629 197_HRV80      AGTGCTAGCAATGGACATACATCAAACTCAGCTCCAACACTTGATGCAGCAGAAACTGGT
630 198_HRV51      CAACCTAGCAGTGGGCACACATCTAATGCTGCACCAGCTCTAGATGCTGCTGAGACAGGA
631 199_HRV51a     CAACCTAGCAGTGGGCACACATCTAATGCTGCACCAGCTCTAGATGCTGCTGAGACAGGA
632 200_HRV51b     CAACCTAGCAGTGGGCACACATCTAATGCTGCACCAGCTCTAGATGCTGCTGAGACAGGA
633 201_HRV65a     CAAGCTAGTAATGGGCATACATCTAATGCTGCACCAGCTTTAGATGCTGCTGAAACAGGA
634 202_HRV65b     CAAGCTAGTAATGGGCATACATCTAATGCTGCACCAGCTTTAGATGCTGCTGAAACAGGA
635 203_HRV65      CAAGCTAGTAATGGGCATACATCTAATGCTGCACCAGCTTTAGATGCTGCTGAAACAGGA
636 204_HRV71a     CAACCTAGTAATGGACATACCTCAAACTCAGCACCAGCCTTAGATGCAGCAGAAACTGGG
637 205_HRV71b     CAACCTAGTAATGGACATACCTCAAACTCAGCACCAGCCTTAGATGCAGCAGAAACTGGG
638 206_HRV71      CAACCTAGTAATGGACATACCTCAAACTCAGCACCAGCCTTAGATGCAGCAGAAACTGGG
639 207_HRV8       CAAGCTAGTAATGGATCTATAGCAAATTCAGCACCAGCATTAGATGCAGCAGAGACTGGA
640 208_HRV95      CAAGCCAGTAATGGATCTATAGCAAATTCAGCACCAGCATTAGATGCAGCAGAGACTGGA
641 209_HRV45      CGACCCAGCGATGGGTTGATTGCAAACTCAGCCCCAGCTTTGGATGCAGCTGAAACTGGA
642 210_HRV45a     CGACCCAGCGATGGGTTGATTGCAAACTCAGCCCCAGCTTTGGATGCAGCTGAAACTGGA
643 211_HRV45b     CGACCCAGCGATGGGTTGATTGCAAACTCAGCCCCAGCTTTGGATGCAGCTGAAACTGGA
644 GROUP_1        ------AG----------------A--C-G---C-----T-GA-GC-GC-GA-AC-GG-
645
```

FIG. D8 CONT'D

04-2.trace                                                                                          9/20/2007 5:04 PM

```
646  1_HRV1A1|d    CACACCAGTAATGTTCAACCAGAAGATGCTATAGAGACAAGGTATGTTATAACATCACAA
647  2_HRV1A2|d    CACACCAGTAATGTTCAACCAGAAGATGCTATAGAGACAAGGTATGTTATAACATCACAA
648  3_HRV1A|cD    CACACCAGTAATGTTCAACCAGAAGATGCTATAGAGACAAGGTATGTTATAACATCACAA
649  4_HRV1B1|d    CACACCAGTAATGTACAACCAGAGGATGCTATAGAAACAAGATATGTTATGACATCACAA
650  5_HRV1B2|d    CACACCAGTAATGTACAACCAGAGGATGCTATAGAAACAAGATATGTTATGACATCACAA
651  6_HRV1B       CACACCAGTAATGTACAACCAGAGGATGCTATAGAAACAAGATATGTTATGACATCACAA
652  7_HRV40a|d    CATACAAGCAACATACAACCTGAAGATACAATAGAAACAAGATTTGTGCAGACATCACAA
653  8_HRV40b|d    CATACAAGCAACATACAACCTGAAGATACAATAGAAACAAGATTTGTGCAGACATCACAA
654  9_HRV40       CACAAGCAACATACAACCTGAAGATACAATAGAAACAAGATTTGTGCAGACATCACAA
655  10_HRV85      CATACAAGTAGTACACAGCCCGAGGATACAATAGAGACCAGGTTTGTTCAAACTTCACAG
656  11_HRV85a|    CATACAAGTAGTACACAGCCCGAGGATACAATAGAGACCAGGTTTGTTCAAACTTCACAG
657  12_HRV85b|    CATACAAGTAGTACACAGCCCGAGGATACAATAGAGACCAGGTTTGTTCAAACTTCACAG
658  13_HRV56a|    CATACTAGTGCAATCCAACCAGAAGACACTATAGAAACCAGATATGTACAGACATCACAA
659  14_HRV56b|    CATACTAGTGCAATCCAACCAGAAGACACTATAGAAACCAGATATGTACAGACATCACAA
660  15_HRV56      CATACTAGTGCAATCCAACCAGAAGACACTATAGAAACCAGATATGTACAGACATCACAA
661  16_HRV54      CACACTAGTGGAGTACAACCCGAGGACACCATAGAAACAAGATATGTGCAGACATCACAA
662  17_HRV98      CACACTAGTGGAATACAACCTGAGGATACTATAGAAACAAGATATGTGCAGACATCACAA
663  18_HRV59a|    CATACAAGCAGTATACAACCTGAGGATACCATAGAAACAAGATATGTTCAGACATCACAA
664  19_HRV59b|    CATACAAGCAGTATACAACCTGAGGATACCATAGAAACAAGATATGTTCAGACATCACAA
665  20_HRV59      CATACAAGCAGTATACAACCTGAGGATACCATAGAAACAAGATATGTTCAGACATCACAA
666  21_HRV63      CACACAAGCAGTATACAACCTGAGGATACTGTAGAAACTAGATATGTGCAAACGTCTCAA
667  22_HRV63b|    CACACAAGCAGTATACAACCTGAGGATACTGTAGAAACTAGATATGTGCAAACGTCTCAA
668  23_HRV63a|    CACACAAGCAGTATACAACCTGAGGATACTGTAGAAACTAGATATGTGCAAACGTCTCAA
669  24_HRV39      CACACAAGTAGCACCCAGCCTGAAGACACAATTGAAACAAGATATGTGCAAACCTCACAT
670  25_HRV39a|    CACACAAGTAGCACCCAGCCTGAAGACACAATTGAAACAAGATATGTGCAAACCTCACAT
671  26_HRV39b|    CACACAAGTAGCATCCAACCTGAAGACACAATTGAAACAAGATATGTGCAAACCTCACAT
672  27_HRV10a|    CATACCAGTAGTGTACAACCAGAAGATACGGTTGAAACACGATATGTGCAAACATCCCAG
673  28_HRV10b|    CATACCAGTAGTGTACAACCAGAAGATACGGTTGAAACACGATATGTGCAAACATCCCAG
674  29_HRV10      CATACCAGTAGTGTACAACCAGAAGATACGGTTGAAACACGATATGTGCAAACATCCCAG
675  30_HRV100a    CACACTAGTAATGTGCAACCTGAAGATACAGTTGAAACTCGATATGTGCAGACATCACAG
676  31_HRV100b    CACACTAGTAATGTGCAACCTGAAGATACAGTTGAAACTCGATATGTGCAGACATCACAG
677  32_HRV100     CACACTAGTAATGTGCAACCTGAAGATACAGTTGAAACTCGATATGTGCAGACATCACAG
678  33_HRV66      CACACTAGTAAAGTACAACCAGAAGATACAGTTGAGACTCGTTACGTGCAAACATCACAG
679  34_HRV66b|    CACACTAGTAAAGTACAACCAGAAGATACAGTTGAGACTCGTTACGTGCAAACATCACAG
680  35_HRV66a|    CACACTAGTAAAGTACAACCAGAAGATACAGTTGAGACTCGTTACGTGCAAACATCACAG
681  36_HRV77a|    CATACTAGTAGTGTGCAACCAGAAGATACAGTTGAGACCCGCTATGTACAAACTTCCCAG
682  37_HRV77b|    CATACTAGTAGTGTGCAACCAGAAGATACAGTTGAGACCCGCTATGTACAAACTTCCCAG
683  38_HRV77      CATACTAGTAGTGTGCAACCAGAAGATACAGTTGAGACCCGCTATGTACAAACTTCCCAG
684  39_HRV62a     CACACTAGTAATGTACAACCAAGACACTATTGAAACCCGTCATGTTCAAACCACACAA
685  40_HRV62b     CACACTAGTAATGTACAACCAGAAGACACTATTGAAACCCGTTATGTTCAAACCACACAA
686  41_HRV25      CACACTAGCAATGTGCAACCAGAGGATACCATTGAAACTCGTTATGTTCAAACCACACAA
687  42_HRV29a     CATACTAGTAGTACAACCAGAAGATACCATTGAGACTCGTTATGTACAAACCTCACAT
688  43_HRV29b     CATACTAGTAATGTACAACCAGAAGATACCATTGAGACTCGTTATGTACAAACCTCACAT
689  44_HRV44a     CATACTAGTAATGTACAACCAGAAGATACCATTGAGACTCGATATGTACAAACCTCACAA
690  45_HRV44b     CATACTAGTAATGTACAACCAGAAGATACCATTGAGACTCGATATGTACAAACCTCACAA
691  46_HRV31      CACACTAGTATACAACCAGAAGATACAATTCGCTACGTGCAAACATCACAA
692  47_HRV31a|    CACACTAGTAATGTACAACCAGAAGATACAATTGAAACTCGCTACGTGCAAACATCACAA
693  48_HRV31b|    CACACTAGTAATGTACAACCAGAAGATACAATTGAAACTCGCTACGTGCAAACATCACAA
694  49_HRV47      CACACTAGCAATGTACAGCCAGAAGATACAATTGAAACTCGATATGTACAAACAGCACAA
695  50_HRV47a|    CACACTAGCAATGTACAGCCAGAAGATACAATTGAAACTCGATATGTACAAACAGCACAA
696  51_HRV47b|    CACACTAGCAATGTACAGCCAGAAGATACAATTGAAACTCGATATGTACAAACAGCACAA
697  52_HRV11      CATACTAGCAAAGTGCAGCCAGAGGATATGATTGAGACTAGATATGTGCAGACTTCACAG
698  53_HRV11b|    CATACTAGCAAAGTGCAGCCAGAGGATATGATTGAGACTAGATATGTGCAGACTTCACAG
699  54_HRV11a|    CATACTAGCAAAGTGCAGCCAGAGGATATGATTGAGACTAGATATGTGCAGACTTCACAG
700  55_HRV76      CACACAAGCAGCGTTCAACCAGAGGACATGGTTGAGACTAGGTATGTGCAAACATCACAA
701  56_HRV76b|    CACACAAGCAGCGTTCAACCAGAGGACATGGTTGAGACTAGGTATGTGCAAACATCACAA
702  57_HRV76a|    CACAAGCAGCGTTCAACCAGAGGACATGGTTGAGACTAGGTATGTGCAAACATCACAA
703  58_HRV33      CACACTAATAATGTACAACCAGAAGATATGATTGAAACAAGATATGTACAAACATCACAA
704  59_HRV33b|    CACACTAATAATGTACAACCAGAAGATATGATTGAAACAAGATATGTACAAACATCACAA
705  60_HRV33a|    CACACTAATAATGTACAACCAGAAGATATGATTGAAACAAGATATGTACAAACATCACAA
706  61_HRV24a|    CATACGAGTAGCGTGCAGCCAGAAGATATGGTTGAAACTAGATATGTCCAAACATCACAA
707  62_HRV24b|    CATACGAGTAGCGTGCAGCCAGAAGATATGGTTGAAACTAGATATGTCCAAACATCACAA
708  63_HRV24      CATACGAGTAGCGTGCAGCCAGAAGATATGGTTGAAACTAGATATGTCCAAACATCACAA
709  64_HRV90      CATACTAGTGATGTCCAGCCAGAAGATGTGGTAGAGACCAGATACGTGCAAACATCACAA
710  65_HRV90a|    CATACTAGTGATGTCCAGCCAGAAGATGTGGTAGAGACCAGATACGTGCAAACATCACAA
```

FIG. D8 CONT'D 04-2.trace                                                                9/20/2007 5:04 PM

```
711  66_HRV90b|    CATACTAGTGATGTCCAGCCAGAAGATGTGGTAGAGACCAGATACGTGCAAACATCACAA
712  67_HRV34      CACACTAGCAGTGTACAACCTGAAGATATGATTGAGACCAGGTACGTACAAACATCACAA
713  68_HRV34b|    CACACTAGCAGTGTACAACCTGAAGATATGATTGAGACCAGGTACGTACAAACATCACAA
714  69_HRV34a|    CACACTAGCAGTGTACAACCTGAAGATATGATTGAGACCAGGTACGTACAAACATCACAA
715  70_HRV50a|    CACACAAGTAATGTGCAGCCTGAAGATATGCTTGAAACTAGATATGTGCAAACATCGCAT
716  71_HRV50b|    CACACAAGTAATGTGCAGCCTGAAGATATGCTTGAAACTAGATATGTGCAAACATCGCAT
717  72_HRV50      CACACAAGTAATGTGCAGCCTGAAGATATGCTTGAAACTAGATATGTGCAAACATCGCAT
718  73_HRV18a|    CACACCAGCAATGTGCAACCTGAAGATATGATTGAGACTAGGTATGTACAAACATCACAA
719  74_HRV18b|    CACACCAGCAATGTGCAACCTGAAGATATGATTGAGACTAGGTATGTACAAACATCACAA
720  75_HRV18      CACACCAGCAATGTGCAACCTGAAGATATGATTGAGACTAGGTATGTACAAACATCACAA
721  76_HRV55      CATACAAGCAATGTACAACCAGAAGATGTAATTGAGACAAGATATGTTCAGACATCACAA
722  77_HRV55b|    CATACAAGCAATGTACAACCAGAAGATGTAATTGAGACAAGATATGTTCAGACATCACAA
723  78_HRV55a|    CATACAAGCAATGTACAACCAGAAGATGTAATTGAGACAAGATATGTTCAGACATCACAA
724  79_HRV57      CACACTAGTAATGTACAACCGGAAGACATGATTGAAACTAGATATGTCCAGACATCACAA
725  80_HRV57a|    CACACTAGTAATGTACAACCGGAAGACATGATTGAAACTAGATATGTCCAGACATCACAA
726  81_HRV57b|    CACACTAGTAATGTACAACCGGAAGACATGATTGAAACTAGATATGTCCAGACATCACAA
727  82_HRV21      CACACTAGTAATGTACGGAGGATATGGTTGAAACAAGGTATGTTCAGACATCACAA
728  83_HRVHan     CACACTAGTAATGTCAACCAGAAGATATGGTTGAAACAAGGTATGTTCAGACATCACAA
729  84_HRV43      CATACTAGCCAGGTGCAACCTGAAGCATGGTAGAGACAAGGTCAGTACATAATTTCCAA
730  85_HRV43b|    CATACTAGCCAGGTGCAACCTGAAGACATGGTAGAGACAAGGTCAGTACATAATTTCCAA
731  86_HRV43a|    CATACTAGCCAGGTGCAACCTGAAGACATGGTAGAGACAAGGTCAGTACATAATTTCCAA
732  87_HRV75      CATACCAGCCATGTTCAACCAGAAGACATGTTAGAAACAAGGCAAGTACAAAATTTCCAA
733  88_HRV75b|    CATACCAGCCATGTTCAACCAGAAGACATGTTAGAAACAAGGCAAGTACAAAATTTCCAA
734  89_HRV75a|    CATACCAGCCATGTTCAACCAGAAGACATGTTAGAAACAAGGCAAGTACAAAATTTCCAA
735  96_HRV9a|d    CATACTAGCAATGTTCAACCTGAAGACATGATTGAAACACGTTATGTGCAGACATCACAA
736  97_HRV9b|d    CATACTAGCAATGTTCAACCTGAAGACATGATTGAAACACGTTATGTGCAGACATCACAA
737  98_HRV9       CATACTAGCAATGTTCAACCTGAAGACATGATTGAAACACGTTATGTGCAGACATCACAA
738  99_HRV32      CATACCAGTAATGTTCAACCTGAAGACATGATTGAAACACGTTATGTGCAAACAACACAC
739  100_HRV32a    CATACCAGTAATGTTCAACCTGAAGACATGATTGAAACACGTTATGTGCAAACAACACAC
740  101_HRV32b    CATACCAGTAATGTTCAACCTGAAGACATGATTGAAACACGTTATGTGCAAACAACACAC
741  102_HRV67     CACACTAGCAGTGTACAACCTGAAGATATGATCGAGACTCGTTATGTACAGGCATCAAAT
742  103_HRV67a    CACACTAGCAGTGTACAACCTGAAGATATGATCGAGACTCGTTATGTACAGGCATCAAAT
743  104_HRV67b    CACACTAGCAGTGTACAACCTGAAGATATGATCGAGACTCGTTATGTACAGGCATCAAAT
744  105_HRV15     CATACTAGCAGTGTTCAACCTGAGGATATGATTGAAACTCGTTACGTCCAAACATCACAG
745  106_HRV15a    CATACTAGCAGTGTTCAACCTGAGGATATGATTGAAACTCGTTACGTCCAAACATCACAG
746  107_HRV15b    CATACTAGCAGTGTTCAACCTGAGGATATGATTGAAACTCGTTACGTCCAAACATCACAG
747  108_HRV74a    CATACCAGTAATGTGCAACCAGAAGATATGGTTGAGACACGCTATGTGCAAACCTCACAG
748  109_HRV74b    CATACCAGTAATGTGCAACCAGAAGATATGGTTGAGACACGCTATGTGCAAACCTCACAG
749  110_HRV74     CATACCAGTAATGTGCAACCAGAAGATATGGTTGAGACACGCTATGTGCAAACCTCACAG
750  111_HRV38a    CACACCAGTAATGTGCAGCCTGAGGATATGATTGAAACTCGCTATGTACAGACATCACAA
751  112_HRV38b    CACACCAGTAATGTGCAGCCTGAGGATATGATTGAAACTCGCTATGTACAGACATCACAA
752  113_HRV38     CACACCAGTAATGTGCAGCCTGAGGATATGATTGAAACTCGCTATGTACAGACATCACAA
753  114_HRV60     CACACTAGTAATGTACAGCCTGAGGACGTGATTGAAACACGTTATGTGCAGATTACACAA
754  115_HRV60a    CACACTAGTAATGTACAGCCTGAGGACGTGATTGAAACACGTTATGTGCAGATTACACAA
755  116_HRV60b    CACACTAGTAATGTACAGCCTGAGGACGTGATTGAAACACGTTATGTGCAGATTACACAA
756  117_HRV64a    CACACCAGTAATGTACAGCCTGAAGATATGATTGAAACGCGCTATGTACAAAACACTCAA
757  118_HRV64b    CACACCAGTAATGTACAGCCTGAAGATATGATTGAAACGCGCTATGTACAAAACACTCAA
758  119_HRV64     CACACCAGTAATGTACAGCCTGAAGATATGATTGAAACGCGCTATGTACAAAACACTCAA
759  120_HRV94a    CACACAAGCAATGTACAACCTGAGGATATGATTGAAACACGCTATGTACAAAACACTCAA
760  121_HRV94b    CACACAAGCAATGTACAACCTGAGGATATGATTGAAACACGCTATGTACAAAACACTCAA
761  122_HRV94     CACACAAGCAATGTACAACCTGAGGATATGATTGAAACACGCTATGTACAAAACACTCAA
762  123_HRV22     CACACAAGCAATGTGCAGCCAGAAGACATGATAGAAACACGCTATGTGTTAAATTCACAA
763  124_HRV22a    CACACAAGCAATGTGCAGCCAGAAGACATGATAGAAACACGCTATGTGTTAAATTCACAA
764  125_HRV22b    CACACAAGCAATGTGCAGCCAGAAGACATGATAGAAACACGCTATGTGTTAAATTCACAA
765  126_HRV82     CATACAAGTACTGTTCAACCTGAGGACATGATTGAAACACGGTATGTTCAAACATCACAA
766  127_HRV82b    CATACAAGTACTGTTCAACCTGAGGACATGATTGAAACACGGTATGTTCAAACATCACAA
767  128_HRV82a    CATACAAGTACTGTTCAACCTGAGGACATGATTGAAACACGGTATGTTCAAACATCACAA
768  129_HRV19     CATACTAGCAATGTACAGCCTGAGGACATGATCGAAACACGCTATGTTCAAACGTCCAG
769  130_HRV19a    CATACTAGCAATGTACAGCCTGAGGACATGATCGAAACACGCTATGTTCAAACGTCCAG
770  131_HRV19b    CATACTAGCAATGTACAGCCTGAGGACATGATCGAAACACGCTATGTTCAAACGTCCAG
771  132_HRV13     CACACAAGTAGTACAACCAGAAGACATGGTTGAAACACGTTATGTCCAAACTTCACAA
772  133_HRV13a    CACACAAGCAGTGTACAACCAGAAGACATGGTTGAAACACGTTATGTCCAAACTTCACAA
773  134_HRV13b    CACACAAGCAGTGTACAACCAGAAGACATGGTTGAAACACGTTATGTCCAAACTTCACAA
774  135_HRV41     CATACCAGTAATGTACAACCAGAGGACATGATTGAAACACGATATGTCCAAACCTCACAA
775  136_HRV41a    CATACCAGTAATGTACAACCAGAGGACATGATTGAAACACGATATGTCCAAACCTCACAA
```

FIG. D8 CONT'D

```
04-2.trace                                                                                                    9/20/2007 5:04 PM 776  137_HRV41b    CATACCAGTAATGTACAACCAGAGGACATGATTGAAACACGATATGTCCAAACCTCACAA
777  138_HRV73     CATACCAGTGGTGTACAACCAGAAGACATGATTGAGACCCGTTATGTCCAAACATCACAG
778  139_HRV73b    CATACCAGTGGTGTACAACCAGAAGACATGATTGAGACCCGTTATGTCCAAACATCACAG
779  140_HRV73a    CATACCAGTGGTGTACAACCAGAAGACATGATTGAGACCCGTTATGTCCAAACATCACAG
780  141_HRV61     CATACCAGCAATGTTCAACCGGAGGACACGATTGAAACACGATATGTTCAAACCTCACAG
781  142_HRV61a    CATACCAGCAATGTTCAACCGGAGGACACGATTGAAACACGATATGTTCAAACCTCACAG
782  143_HRV61b    CATACCAGCAATGTTCAACCGGAGGACACGATTGAAACACGATATGTTCAAACCTCACAG
783  144_HRV96     CATACTAGCAATGTCCAACCAGAGGATATGATTGAGACTCGATATGTTCAGACATCGCAG
784  145_HRV96b    CATACTAGCAATGTCCAACCAGAGGATATGATTGAGACTCGATATGTTCAGACATCGCAG
785  146_HRV96a    CATACTAGCAATGTCCAACCAGAGGATATGATTGAGACTCGATATGTTCAGACATCGCAG
786  90_HRV16a|    CATACCAATAAGATACAGCCAGAAGACACTATAGAAACCAGATATGTGCAATCTTCACAG
787  91_HRV16b|    CATACCAATAAGATACAGCCAGAAGACACTATAGAAACCAGATATGTGCAATCTTCACAG
788  92_1AYM_A     CATACCAATAAGATACAGCCAGAAGACACTATAGAAACCAGATATGTGCAATCTTCACAG
789  93_HRV81a|    CACACCAGTAATATACAACCTGAGGATACTATTGAGACCAGATATGTACAATCTTCACAG
790  94_HRV81b|    CACACCAGTAATATACAACCTGAGGATACTATTGAGACCAGATATGTACAATCTTCACAG
791  95_HRV81      CACACCAGTAATATACAACCTGAGGATACTATTGAGACCAGATATGTACAATCTTCACAG
792  147_HRV2      CACACTAGTAGTGTTCAACCAGAGGATGTCATTGAAACTAGGTATGTGCAGACATCACAA
793  148_HRV2a|    CACACTAGTAGTGTTCAACCAGAGGATGTCATTGAAACTAGGTATGTGCAGACATCACAA
794  149_HRV2b|    CACACTAGTAGTGTTCAACCAGAGGATGTCATTGAAACTAGGTATGTGCAGACATCACAA
795  150_HRV49a    CACACTAGCAATGTGCAACCTGAAGATGTCATTGAAACCAGATATGTACAGACATCACAA
796  151_HRV49b    CACACTAGCAATGTGCAACCTGAAGATGTCATTGAAACCAGATATGTACAGACATCACAA
797  152_HRV49     CACACTAGCAATGTGCAACCTGAAGATGTCATTGAAACCAGATATGTACAGACATCACAA
798  153_HRV23a    CACACTAGTAATGTTCAACCAGAAGATGTCATTGAAACCAGGTACGTTCAAACATCACAA
799  154_HRV23b    CACACTAGTAATGTTCAACCAGAAGATGTCATTGAAACCAGGTACGTTCAAACATCACAA
800  155_HRV23     CACACTAGTAATGTTCAACCAGAAGATGTCATTGAAACCAGGTACGTTCAAACATCACAA
801  156_HRV30a    CATACTAGTAATGTTCAACCTGAAGATGTCATTGAAACTAGATATGTTCAAACATCACAA
802  157_HRV30b    CATACTAGTAATGTTCAACCTGAAGATGTCATTGAAACTAGATATGTTCAAACATCACAA
803  158_HRV30     CATACTAGTAATGTTCAACCTGAAGATGTCATTGAAACTAGATATGTTCAAACATCACAA
804  159_HRV7      CATACTAGTTCTGTTCAACCTGAAGTATGATCGAGACAAGGTATGTCATAACAGACCAA
805  160_HRV7b|    CATACTAGTTCTGTTCAACCTGAAGTATGATCGAGACAAGGTATGTCATAACAGACCAA
806  161_HRV7a|    CATACTAGTTCTGTTCAACCTGAAGTATGATCGAGACAAGGTATGTCATAACAGACCAA
807  162_HRV88     CATACTAGTTCTGTTCAACCTGAAGTATGATAGAAACTAGATATGTTATAACAGATCAA
808  163_HRV88a    CATACTAGTTCTGTTCAACCTGAAGTATGATAGAAACTAGATATGTTATAACAGATCAA
809  164_HRV88b    CATACTAGTTCTGTTCAACCTGAAGTATGATAGAAACTAGATATGTTATAACAGATCAA
810  165_HRV36a    CATACCAGCTCTGTCCAACCAGAGGACATGATCGAGACCAGATATGTCATAACTGATCAA
811  166_HRV36b    CATACCAGCTCTGTCCAACCAGAGGACATGATCGAGACCAGATATGTCATAACTGATCAA
812  167_HRV36     CATACCAGCTCTGTCCAACCAGAGGACATGATCGAGACCAGATATGTCATAACTGATCAA
813  168_HRV89a    CACACCAGCTCTGTTCAACCTGAAGATATGATTGAAACTAGATATGTTATAACTGATCAA
814  169_HRV89b    CACACCAGCTCTGTTCAACCTGAAGATATGATTGAAACTAGATATGTTATAACTGATCAA
815  170_HRV89     CACACCAGCTCTGTTCAACCTGAAGATATGATTGAAACTAGATATGTTATAACTGATCAA
816  171_HRV58     CACACAAGTTCTGTTCAGCCTGAGGATATGATTGAAACTAGATATGTTATCACAGATCAA
817  172_HRV58a    CACACAAGTTCTGTTCAGCCTGAGGATATGATTGAAACTAGATATGTTATCACAGATCAA
818  173_HRV58b    CACACAAGTTCTGTTCAGCCTGAGGATATGATTGAAACTAGATATGTTATCACAGATCAA
819  174_HRV12a    CATACCAGCCAAACACAACCAGAAGATGTGATTGAAACCAGGTATGTGATTACAGACCAG
820  175_HRV12b    CATACCAGCCAAACACAACCAGAAGATGTGATTGAAACCAGGTATGTGATTACAGACCAG
821  176_HRV12     CATACCAGCCAAACACAACCAGAAGATGTGATTGAAACCAGGTATGTGATTACAGACCAG
822  177_HRV78a    CATACGAACCAAGTACAGCCTGAAGACACCATAGAAACTAGATATGTTATAACTGACCAA
823  178_HRV78b    CATACGAACCAAGTACAGCCTGAAGACACCATAGAAACTAGATATGTTATAACTGACCAA
824  179_HRV78     CATACGAACCAAGTACAGCCTGAAGACACCATAGAAACTAGATATGTTATAACTGACCAA
825  180_HRV20     CACACAAACCAGGTCCAGCCAGAAGATATGGTCGAGACACGGTATGTAATTACTGATCAG
826  181_HRV20a    CACACAAACCAGGTCCAGCCAGAAGATATGGTCGAGACACGGTATGTAATTACTGATCAG
827  182_HRV20b    CACACAAACCAGGTCCAGCCAGAAGATATGGTCGAGACACGGTATGTAATTACTGATCAG
828  183_HRV68     CATACAAACCAAGTCCAACCAGAAGATGTGGTTGAAACACGCTATGTCATAACAGACCAG
829  184_HRV68a    CATACAAACCAAGTCCAACCAGAAGATGTGGTTGAAACACGCTATGTCATAACAGACCAG
830  185_HRV68b    CATACAAACCAAGTCCAACCAGAAGATGTGGTTGAAACACGCTATGTCATAACAGACCAG
831  186_HRV28     CACACAAGCCAAACACAACCTGAAGACATGGTTGAGACTAGGTATGTAATCACAGATCAG
832  187_HRV28a    CACACAAGCCAAACACAACCTGAAGACATGGTTGAGACTAGGTATGTAATCACAGATCAG
833  188_HRV28b    CACACAAGCCAAACACAACCTGAAGACATGGTTGAGACTAGGTATGTAATCACAGATCAG
834  189_HRV53a    CATACAAGTCAGACACAACCTGAGGACATGCTGGAAACTAGATATGTCATCACAGACCAA
835  190_HRV53b    CATACAAGTCAGACACAACCTGAGGACATGCTGGAAACTAGATATGTCATCACAGACCAA
836  191_HRV53     CATACAAGTCAGACACAACCTGAGGACATGCTGGAAACTAGATATGTCATCACAGACCAA
837  192_HRV46a    CACACTAGCCAGATACAACCAGAAGACATGATAGAAACCAGATATGTTATCACAGACCAA
838  193_HRV46b    CACACTAGCCAGATACAACCAGAAGACATGATAGAAACCAGATATGTTATCACAGACCAA
839  194_HRV46     CACACTAGCCAGATACAACCAGAAGACATGATAGAAACCAGATATGTTATCACAGACCAA
840  195_HRV80a    CACACTAGCCAGGTGCAACCAGAAGACATGATAGAAACTAGATATGTTATTACTGATCAG
```

FIG. D8 CONT'D

```
04-2.trace                                                                                              9/20/2007 5:04 PM 841  196_HRV80b       CACACTAGCCAGGTGCAACCAGAAGACATGATAGAAACTAGATATGTTATTACTGATCAG
842  197_HRV80        CACACTAGCCAGGTGCAACCAGAAGACATGATAGAAACTAGATATGTTATTACTGATCAG
843  198_HRV51        CATACTAGTCAAGTTCAACCAGAAGATATGGTAGAGACCAGGTATGTTGTCACAGACCAA
844  199_HRV51a       CATACTAGTCAAGTTCAACCAGAAGATATGGTAGAGACCAGGTATGTTGTCACAGACCAA
845  200_HRV51b       CATACTAGTCAAGTTCAACCAGAAGATATGGTAGAGACCAGGTATGTTGTCACAGACCAA
846  201_HRV65a       CACACTAGTCAAGTTCAACCAGAGGATGTGATAGAAACCAGATATGTCATCACAGATCAA
847  202_HRV65b       CACACTAGTCAAGTTCAACCAGAGGATGTGATAGAAACCAGATATGTCATCACAGATCAA
848  203_HRV65        CACACTAGTCAAGTTCAACCAGAGGATGTGATAGAAACCAGATATGTCATCACAGATCAA
849  204_HRV71a       CATACCAACCAAGTACAACCAGAAGATGTTATGGAAACCAGATATGTGATCACTGATCAA
850  205_HRV71b       CATACCAACCAAGTACAACCAGAAGATGTTATGGAAACCAGATATGTGATCACTGATCAA
851  206_HRV71        CATACCAACCAAGTACAACCAGAAGATGTTATGGAAACCAGATATGTGATCACTGATCAA
852  207_HRV8         CACACAAGTTCAGTGCAACCTGAAGATCTTATAGAGACTAGGTATGTAATTACAGATCAA
853  208_HRV95        CACACAAGTTCAGTGCAACCTGAAGATCTTATAGAGACTAGGTATGTAATTACAGATCAA
854  209_HRV45        CACACCAGTTCAGTGCAGCCTGAGGACCTTATAGAGACTAGATATGTGATTGCAGACCAA
855  210_HRV45a       CACACCAGTTCAGTGCAGCCTGAGGACCTTATAGAGACTAGATATGTGATTGCAGACCAA
856  211_HRV45b       CACACCAGTTCAGTGCAGCCTGAGGACCTTATAGAGACTAGATATGTGATTGCAGACCAA
857  GROUP_1          CA-AC-A--------CA-CC-GA-GA-----T-GA-AC--G----GT-----------A-
858

859  1_HRV1A1|d       ACAAGAGATGAGATGAGTATAGAAAGTTTCCTTGGTAGATCTGGTTGTGTCCACATCTCA
860  2_HRV1A2|d       ACAAGAGATGAGATGAGTATAGAAAGTTTCCTTGGTAGATCTGGTTGTGTCCACATCTCA
861  3_HRV1A|cD       ACAAGAGATGAGATGAGTATAGAAAGTTTCCTTGGTAGATCTGGTTGTGTCCACATCTCA
862  4_HRV1B1|d       ACAAGAGATGAGATGAGTATAGAAAGTTTCTTGGTAGATCTGGCTGTGTGCATATTTCA
863  5_HRV1B2|d       ACAAGAGATGAGATGAGTATAGAAAGTTTCTTGGTAGATCTGGCTGTGTGCATATTTCA
864  6_HRV1B          ACAAGAGATGAGATGAGTATAGAAAGTTTCTTGGTAGATCTGGCTGTGTGCATATTTCA
865  7_HRV40a|d       ACTAGAGATGAAATGAGCAGAGAGTTTCTTGGGAAGATCTGGGTGCATTCATATATCC
866  8_HRV40b|d       ACTAGAGATGAAATGAGCATAGAGAGTTTCTTGGGAAGATCTGGGTGCATTCATATATCC
867  9_HRV40          ACTAGAGATGAAATGAGCATAGAGAGTTTCTTGGGAAGATCTGGGTGCATTCATATATCC
868  10_HRV85         ACTAGGGATGAAATGAGTTTAGAAAGTTTCTTGGGAAGATCTGGATGTATCCATATATCT
869  11_HRV85a|       ACTAGGGATGAAATGAGTTTAGAAAGTTTCTTGGGAAGATCTGGATGTATCCATATATCT
870  12_HRV85b|       ACTAGGGATGAAATGAGTTTAGAAAGTTTCTTGGGAAGATCTGGATGTATCCATATATCT
871  13_HRV56a|       ACTAGGGATGAAATGAGTATAGAGAGTTTTCTAGGTAGATCAGGTTGTATACATATATCA
872  14_HRV56b|       ACTAGGGATGAAATGAGTATAGAGAGTTTTCTAGGTAGATCAGGTTGTATACATATATCA
873  15_HRV56         ACTAGGGATGAAATGAGTATAGAGAGTTTTCTAGGTAGATCAGGTTGTATACATATATCA
874  16_HRV54         ACTAGAGATGAAATGAGCATAGAAAGTTTTCTAGGCAGGGCTGGTTGCATACATGAATCC
875  17_HRV98         ACCAGAGATGAAATGAGTATAGAAAGTTTTCTAGGTAGGGCCGGTTGTATACATGAATCT
876  18_HRV59a|       ACTAGAGATGAGATGAGTGTAGAAAGTTTCTTAGGTAGATCTGGGTGTATACATATTTCA
877  19_HRV59b|       ACTAGAGATGAGATGAGTGTAGAAAGTTTCTTAGGTAGATCTGGGTGTATACATATTTCA
878  20_HRV59         ACTAGAGATGAGATGAGTGTAGAAAGTTTCTTAGGTAGATCTGGGTGTATACATATTTCA
879  21_HRV63         ACAAGGGATGAAATGAGTGTAGAGAGCTTTCTTGGTAGATCAGGATGCATACACATATCA
880  22_HRV63b|       ACAAGGGATGAAATGAGTGTAGAGAGCTTTCTTGGTAGATCAGGATGCATACACATATCA
881  23_HRV63a|       ACAAGGGATGAAATGAGTGTAGAGAGCTTTCTTGGTAGATCAGGATGCATACACATATCA
882  24_HRV39         ACTAGGGATGAAATGAGCGTTGAAAGTTTCTTAGGCAGATCTGGCTGTATTCACATTTCC
883  25_HRV39a|       ACTAGGGATGAAATGAGCGTTGAAAGTTTCTTAGGCAGATCTGGCTGTATTCACATTTCC
884  26_HRV39b|       ACTAGGGATGAAATGAGTGTTGAAAGTTTCTTAGGCAGATCTGGCTGTATTCACATTTCC
885  27_HRV10a|       ACGAGAGATGAAATGAGTATTGAAAGTTTTCTTGGCAGGTCAGGTTGTATACACACCTCA
886  28_HRV10b|       ACGAGAGATGAAATGAGTATTGAAAGTTTTCTTGGCAGGTCAGGTTGTATACACACCTCA
887  29_HRV10         ACGAGAGATGAAATGAGTATTGAAAGTTTTCTTGGCAGGTCAGGTTGTATACACACCTCA
888  30_HRV100a       ACCAGGGATGAAATGAGTATTGAGAGCTTTCTTGGAAGATCTGGTTGTATACACACCTCA
889  31_HRV100b       ACCAGGGATGAAATGAGTATTGAGAGCTTTCTTGGAAGATCTGGTTGTATACACACCTCA
890  32_HRV100        ACCAGGGATGAAATGAGTATTGAGAGCTTTCTTGGAAGATCTGGTTGTATACACACCTCA
891  33_HRV66         ACTAGAGATGAAATGAGCATAGAAAGTTTCTAGGTAGGTCAGGATGTATCCATATATCA
892  34_HRV66b|       ACTAGAGATGAAATGAGCATAGAAAGTTTTCTAGGTAGGTCAGGATGTATCCATATATCA
893  35_HRV66a|       ACTAGAGATGAAATGAGCATAGAAAGTTTTCTAGGTAGGTCAGGATGTATCCATATATCA
894  36_HRV77a|       ACAAGGGATGAGATGAGTATTGAGAGCTTTCTGGGTAGGTCTGGTTGTATTCACATTTCA
895  37_HRV77b|       ACAAGGGATGAGATGAGTATTGAGAGCTTTCTGGGTAGGTCTGGTTGTATTCACATTTCA
896  38_HRV77         ACAAGGGATGAGATGAGTATTGAGAGCTTTCTGGGTAGGTCTGGTTGTATTCACATTTCA
897  39_HRV62a        ACTAGAGATGAAATGAGCATTGAGAGCTTTCTTGGTAGGTCAGGGTGCGTACACACTTCA
898  40_HRV62b        ACTAGAGATGAAATGAGCATTGAGAGCTTTCTTGGTAGGTCAGGGTGCGTACACACTTCA
899  41_HRV25         ACTAGAGATGAAATGAGTATTGAAAGTTTCTTGGTAGGTCAGGGTGTGTACATACTTCA
900  42_HRV29a        ACTAGAGATGAAATGAGCATTGAAAGTTTCTTGGGTAGATCAGGATGTATACATGTTTCA
901  43_HRV29b        ACTAGAGATGAAATGAGCATTGAAAGTTTCTTGGTAGATCAGGATGTATACATGTTTCA
902  44_HRV44a        ACTAGAGATGAAATGAGCATTGAAAGTTTCTTGGCAGATCAGGTGTATACATGTTTCA
903  45_HRV44b        ACTAGAGATGAAATGAGCATTGAAAGTTTCTTGGCAGATCAGGGTGTATACATGTTTCA
904  46_HRV31         ACAAGAGATGAAATGAGCATTGAAAGTTTCCTTGGTAGGTCAGGATGTGTACATACTTCA
905  47_HRV31a|       ACAAGAGATGAAATGAGCATTGAAAGTTTCCTTGGTAGGTCAGGATGTGTACATACTTCA
```

FIG. D8 CONT'D

04-2.trace                                                                                                9/20/2007 5:04 PM

```
906  48_HRV31b|     ACAAGAGATGAAATGAGCATTGAAAGTTTCCTTGGTAGGTCAGGATGTGTACATACTTCA
907  49_HRV47      ACAAGAGATGAAATGAGCATTGAGAGCTTCCTTGGCAGGTCAGGATGTGTGCATTCCTCA
908  50_HRV47a|    ACAAGAGATGAAATGAGCATTGAGAGCTTCCTTGGCAGGTCAGGATGTGTGCATTCCTCA
909  51_HRV47b|    ACAAGAGATGAAATGAGCATTGAGAGCTTCCTTGGCAGGTCAGGATGTGTGCATTCCTCA
910  52_HRV11      ACTCTTGATGAAATGAGCATTGAGAGCTTCCTAGGTAGATCTGGTTGTATTCACATGTCC
911  53_HRV11b|    ACTCTTGATGAAATGAGCATTGAGAGCTTCCTAGGTAGATCTGGTTGTATTCACATGTCC
912  54_HRV11a|    ACTCTTGATGAAATGAGCATTGAGAGCTTCCTAGGTAGATCTGGTTGTATTCACATGTCC
913  55_HRV76      ACTCTTGATGAGATGTGTATGGAGAGTTTCTTAGGGAGATCTGGTTGTATTCATATTTCA
914  56_HRV76b|    ACTCTTGATGAGATGTGTATGGAGAGTTTCTTAGGGAGATCTGGTTGTATTCATATTTCA
915  57_HRV76a|    ACTCTTGATGAGATGTGTATGGAGAGTTTCTTAGGGAGATCTGGTTGTATTCATATTTCA
916  58_HRV33      ACTCTTGATGAGATGAGTGTGGAAAGCTTCTTAGGAAGGTCTGGTTGCATTCACATGTCA
917  59_HRV33b|    ACTCTTGATGAGATGAGTGTGGAAAGCTTCTTAGGAAGGTCTGGTTGCATTCACATGTCA
918  60_HRV33a|    ACTCTTGATGAGATGAGTGTGGAAAGCTTCTTAGGAAGGTCTGGTTGCATTCACATGTCA
919  61_HRV24a|    ACATTACATGAGATGAGTGTTGAAAGTTTCTTGGGTAGATCAGGTTGCATACACATGTCC
920  62_HRV24b|    ACATTACATGAGATGAGTGTTGAAAGTTTCTTGGGTAGATCAGGTTGCATACACATGTCC
921  63_HRV24      ACATTACATGAGATGAGTGTTGAAAGTTTCTTGGGTAGATCAGGTTGCATACACATGTCC
922  64_HRV90      ACAAGAGATGAAATGAGTGTTGAAAGTTTTCTAGGGAGATCAGGTTGCATTCATATGTCA
923  65_HRV90a|    ACAAGAGATGAAATGAGTGTTGAAAGTTTTCTAGGGAGATCAGGTTGCATTCATATGTCA
924  66_HRV90b|    ACAAGAGATGAAATGAGTGTTGAAAGTTTTCTAGGGAGATCAGGTTGCATTCATATGTCA
925  67_HRV34      ACAAGAGATGAAATGAGCATTGAGAGTTTCCTGGGTAGGTCTGGCTGTATACACATGTCC
926  68_HRV34b|    ACAAGAGATGAAATGAGCATTGAGAGTTTCCTGGGTAGGTCTGGCTGTATACACATGTCC
927  69_HRV34a|    ACAAGAGATGAAATGAGCATTGAGAGTTTCCTGGGTAGGTCTGGCTGTATACACATGTCC
928  70_HRV50a|    ACAAGAGATGAAATGAGCATTGAAAGTTTCCTAGGTAGATCTGGTTGTATACATATATCT
929  71_HRV50b|    ACAAGAGATGAAATGAGCATTGAAAGTTTCCTAGGTAGATCTGGTTGTATACATATATCT
930  72_HRV50      ACAAGAGATGAAATGAGCATTGAAAGTTTCCTAGGTAGATCTGGTTGTATACATATATCT
931  73_HRV18a|    ACAAGAGATGAAATGAGTATAGAGTGTTTTCTAGGCAGATCAGGGTGTATACATATCTCC
932  74_HRV18b|    ACAAGAGATGAAATGAGTATAGAGTGTTTTCTAGGCAGATCAGGGTGTATACATATCTCC
933  75_HRV18      ACAAGAGATGAAATGAGTATAGAGTGTTTTCTACGCAGATCAGGGTGTATACATATCTCC
934  76_HRV55      ACTCGTGATGAGATGAGCATTGAAAGTTTCTAGGTAGATCAGGATGTGTACATATATCA
935  77_HRV55b|    ACTCGTGATGAGATGAGCATTGAAAGTTTCTAGGTAGATCAGGATGTGTACATATATCA
936  78_HRV55a|    ACTCGTGATGAGATGAGCATTGAAAGTTTTCTAGGTAGATCAGGATGTGTACATATATCA
937  79_HRV57      ACACGTGATGAAATGAGTCTTGAGAGCTTCTTAGGAAGATCTGGCTGCATTCATATTTCA
938  80_HRV57a|    ACACGTGATGAAATGAGTCTTGAGAGCTTCTTAGGAAGATCTGGCTGCATTCATATTTCA
939  81_HRV57b|    ACACGTGATGAAATGAGTCTTGAGAGCTTCTTAGGAAGATCTGGCTGCATTCATATTTCA
940  82_HRV21      ACACGTGATGAAATGAGTATTGAAAGTTTTCTGGGCAGATCAGGTTGCATTCACATGTCA
941  83_HRVHan     ACACGTGATGAAATGAGTATTGAAAGTTTCCTAGGCAGATCAGGGTGTATCCACATGTCA
942  84_HRV43      ACCAGAGATGAAATGAGTATTGAAAGTTTCTTGGGCAGATCTGGTTGCATACATATTTCA
943  85_HRV43b|    ACCAGAGATGAAATGAGTATTGAAAGTTTCTTGGGCAGATCTGGTTGCATACATATTTCA
944  86_HRV43a|    ACCAGAGATGAAATGAGTATTGAAAGTTTCTTGGGCAGATCTGGTTGCATACATATTTCA
945  87_HRV75      ACTAGAGATGAGATGAGTATTGAGAGTTTCCTAGGCAGATCTGGATGTATTCATATTTCA
946  88_HRV75b|    ACTAGAGATGAGATGAGTATTGAGAGTTTCCTAGGCAGATCTGGATGTATTCATATTTCA
947  89_HRV75a|    ACTAGAGATGAGATGAGTATTGAGAGTTTCCTAGGCAGATCTGGATGTATTCATATTTCA
948  96_HRV9a|d    ACCAGAGATGAAATGAGTCTTGAAAGCTTCTTAGGGAGATCAGGTTGTATACACATATCT
949  97_HRV9b|d    ACCAGAGATGAAATGAGTCTTGAAAGCTTCTTAGGGAGATCAGGTTGTATACACATATCT
950  98_HRV9       ACCAGAGATGAAATGAGTCTTGAAAGCTTCTTAGGGAGATCAGGTTGTATACACATATCT
951  99_HRV32      ACTAGAGATGAGATGAGTCTTGAGAGCTTCTTAGGGAGGTCAGGATGTGTACATATATCC
952  100_HRV32a    ACTAGAGATGAGATGAGTCTTGAGAGCTTCTTAGGGAGGTCAGGATGTGTACATATATCC
953  101_HRV32b    ACTAGAGATGAGATGAGTCTTGAGAGCTTCTTAGGGAGGTCAGGATGTGTACATATATCC
954  102_HRV67     ACCAGAGATGAAATGAGTCTCGAGAGCTTTCTTGGAAGGTCAGGCTGTATTCATATCA
955  103_HRV67a    ACCAGAGATGAAATGAGTCTCGAGAGCTTTCTTGGAAGGTCAGGCTGTATTCATATCA
956  104_HRV67b    ACCAGAGATGAAATGAGTCTCGAGAGCTTTCTTGGAAGGTCAGGCTGTATTCATATCA
957  105_HRV15     ACCAGAGATGAAATGAGTATTGAGAGCTTCCTTGGTAGATCAGGGTGTGTCCATATTTCT
958  106_HRV15a    ACCAGAGATGAAATGAGTATTGAGAGCTTCCTTGGTAGATCAGGGTGTGTCCATATTTCT
959  107_HRV15b    ACCAGAGATGAAATGAGTATTGAGAGCTTCCTTGGTAGATCAGGGTGTGTCCATATTTCT
960  108_HRV74a    ACAAGAGATGAGATGAGTGTAGAAAGTTTTCTTGGAAGATCAGGATGCATCCATATCTCA
961  109_HRV74b    ACAAGAGATGAGATGAGTGTAGAAAGTTTTCTTGGAAGATCAGGATGCATCCATATCTCA
962  110_HRV74     ACAAGAGATGAGATGAGTGTAGAAAGTTTTCTTGGAAGATCAGGATGCATCCATATCTCA
963  111_HRV38a    ACTAGAGATGAAATGAGTGTAGAAAGTTTTCTAGGAAGATCAGGTTGTGTACATATATCC
964  112_HRV38b    ACTAGAGATGAAATGAGTGTAGAAAGTTTTCTAGGAAGATCAGGTTGTGTACATATATCC
965  113_HRV38     ACTAGAGATGAAATGAGTGTAGAAAGTTTTCTAGGAAGATCAGGTTGTGTACATATATCC
966  114_HRV60     ACTAGAGATGAGATGAGTGTTGAGAGCTTCCTCGGCAGATCTGGATGTATTCATATTTCC
967  115_HRV60a    ACTAGAGATGAGATGAGTGTTGAGAGCTTCCTCGGCAGATCTGGATGTATTCATATTTCC
968  116_HRV60b    ACTAGAGATGAGATGAGTGTTGAGAGCTTCCTCGGCAGATCTGGATGTATTCATATTTCC
969  117_HRV64a    ACTAGAGATGAAATGAGCATTGAGAGTTTCTTGGGCAGGTCTGGTTGTATACACATATCA
970  118_HRV64b    ACTAGAGATGAAATGAGCATTGAGAGTTTCTTGGGCAGGTCTGGTTGTATACACATATCA
```

FIG. D8 CONT'D 04-2.trace                                                                                                    9/20/2007 5:04 PM

```
 971 119_HRV64      ACTAGAGATGAAATGAGCATTGAGAGTTTCTTGGGCAGGTCTGGTTGTATACACATATCA
 972 120_HRV94a     ACAAGGGATGAAATGAGCATTGAAAGCTTCTTGGGAAGATCTGGCTGTATACACATAGCA
 973 121_HRV94b     ACAAGGGATGAAATGAGCATTGAAAGCTTCTTGGGAAGATCTGGCTGTATACACATAGCA
 974 122_HRV94      ACAAGGGATGAAATGAGCATTGAAAGCTTCTTGGGAAGATCTGGCTGTATACACATAGCA
 975 123_HRV22      ACTAGAGATGAAATGAGTATTGAGAGCTTCCTGGGAAGATCTGGTTGCATACATATATCA
 976 124_HRV22a     ACTAGAGATGAAATGAGTATTGAGAGCTTCCTGGGAAGATCTGGTTGCATACATATATCA
 977 125_HRV22b     ACTAGAGATGAAATGAGTATTGAGAGCTTCCTGGGAAGATCTGGTTGCATACATATATCA
 978 126_HRV82      ACTAGAGATGAGATGAGCCTTGAGAGTTTCCTAGGGAGATCTGGCTGCATACACATATCA
 979 127_HRV82b     ACTAGAGATGAGATGAGCCTTGAGAGTTTCCTAGGGAGATCTGGCTGCATACACATATCA
 980 128_HRV82a     ACTAGAGATGAGATGAGCCTTGAGAGTTTCCTAGGGAGATCTGGCTGCATACACATATCA
 981 129_HRV19      ACTAGGGATGAAATGAGCATAGAAAGTTTTCTTGGCAGATCCGGTTGTGTACATGTTTCA
 982 130_HRV19a     ACTAGGGATGAAATGAGCATAGAAAGTTTTCTTGGCAGATCCGGTTGTGTACATGTTTCA
 983 131_HRV19b     ACTAGGGATGAAATGAGCATAGAAAGTTTTCTTGGCAGATCCGGTTGTGTACATGTTTCA
 984 132_HRV13      ACTAGGGATGAAATGAGTGTTGAGAGCTTTTAGGCAGATCTGGTTGTATACACATGTCT
 985 133_HRV13a     ACTAGGGATGAAATGAGTGTTGAGAGCTTTTAGGCAGATCTGGTTGTATACACATGTCT
 986 134_HRV13b     ACTAGGGATGAAATGAGTGTTGAGAGCTTTTAGGCAGATCTGGTTGTATACACATGTCT
 987 135_HRV41      ACTAGAGATGAAATGAGCATAGAAAGCTTTTAGGTAGATCAGGCTGTGTACATAAGTCC
 988 136_HRV41a     ACTAGAGATGAAATGAGCATAGAAAGCTTTTAGGTAGATCAGGCTGTGTACATAAGTCC
 989 137_HRV41b     ACTAGAGATGAAATGAGCATAGAAAGCTTTTAGGTAGATCAGGCTGTGTACATAAGTCC
 990 138_HRV73      ACTAGAGATGAAATGAGCATTGAAAGCTTCCTTGGCAGGTCAGGTTGTATACACATGTCA
 991 139_HRV73b     ACTAGAGATGAAATGAGCATTGAAAGCTTCCTTGGCAGGTCAGGTTGTATACACATGTCA
 992 140_HRV73a     ACTAGAGATGAAATGAGCATTGAAAGCTTCCTTGGCAGGTCAGGTTGTATACACATGTCA
 993 141_HRV61      ACAAGAGATGAAATGAGTGTAGAAAGTTTCTTGGGTAGATCAGGGTGCATACATATGTCA
 994 142_HRV61a     ACAAGAGATGAAATGAGTGTAGAAAGTTTCTTGGGTAGATCAGGGTGCATACATATGTCA
 995 143_HRV61b     ACAAGAGATGAAATGAGTGTAGAAAGTTTCTTGGGTAGATCAGGGTGCATACATATGTCA
 996 144_HRV96      ACGAGAGATGAAATGAGCATTGAGAGCTTTTTGGGTAGATCAGGGTGTATACACATGTCA
 997 145_HRV96b     ACGAGAGATGAAATGAGCATTGAGAGCTTTTTGGGTAGATCAGGGTGTATACACATGTCA
 998 146_HRV96a     ACGAGAGATGAAATGAGCATTGAGAGCTTTTTGGGTAGATCAGGGTGTATACACATGTCA
 999 90_HRV16a|     ACATTGGATGAAATGAGTGTGGAAAGCTTCCTAGGCAGATCGGGGTGCATCCATGAATCA
1000 91_HRV16b|     ACATTGGATGAAATGAGTGTGGAAAGCTTCCTAGGCAGATCGGGGTGCATCCATGAATCA
1001 92_1AYM_A      ACATTGGATGAAATGAGTGTGGAAAGCTTCCTAGGCAGATCGGGGTGCATCCATGAATCA
1002 93_HRV81a|     ACACTGGATGAAATGAGTGTAGAAAGTTTTTAGGCAGATCAGGTTGCATTCATGAATCC
1003 94_HRV81b|     ACACTGGATGAAATGAGTGTAGAAAGTTTTTAGGCAGATCAGGTTGCATTCATGAATCC
1004 95_HRV81       ACACTGGATGAAATGAGTGTAGAAAGTTTTTAGGCAGATCAGGTTGCATTCATGAATCC
1005 147_HRV2       ACAAGAGATGAAATGAGTTTCTTGGCAGATCAGGATGCATACATGAATCT
1006 148_HRV2a|     ACAAGAGATGAAATGAGTTTAGAGAGTTTTCTTGGCAGATCAGGATGCATACATGAATCT
1007 149_HRV2b|     ACAAGAGATGAAATGAGTTTAGAGAGTTTTCTTGGCAGATCAGGATGCATACATGAATCT
1008 150_HRV49a     ACAAGAGATGAAATGAGTTTAGAGAGTTTTCTTGGTAGGTCAGGGTGTATACATGAATCC
1009 151_HRV49b     ACAAGAGATGAAATGAGTTTAGAGAGTTTTCTTGGTAGGTCAGGGTGTATACATGAATCC
1010 152_HRV49      ACAAGAGATGAAATGAGTTTAGAGAGTTTTCTTGGTAGGTCAGGGTGTATACATGAATCC
1011 153_HRV23a     ACAAGAGATGAAATGAGTTTAGAAAGTTTCCTTGGTAGGTCAGGGTGTATACATGAATCT
1012 154_HRV23b     ACAAGAGATGAAATGAGTTTAGAAAGTTTCCTTGGTAGGTCAGGGTGTATACATGAATCT
1013 155_HRV23      ACAAGAGATGAAATGAGTTTAGAAAGTTTCCTTGGTAGGTCAGGGTGTATACATGAATCT
1014 156_HRV30a     ACAAGGGATGAAATGAGTTTAGAAAGCTTTCTTGGTAGATCAGGATGTATACACGAGTCT
1015 157_HRV30b     ACAAGGGATGAAATGAGTTTAGAAAGCTTTCTTGGTAGATCAGGATGTATACACGAGTCT
1016 158_HRV30      ACAAGGGATGAAATGAGTTTAGAAAGCTTTCTTGGTAGATCAGGATGTATACACGAGTCT
1017 159_HRV7       ACAAGGGATGAAACTAGTATAGAGAGTTTCTTAGGTAGATCTGGATGTATTGCTAAAGTT
1018 160_HRV7b|     ACAAGGGATGAAACTAGTATAGAGAGTTTCTTAGGTAGATCTGGATGTATTGCTAAAGTT
1019 161_HRV7a|     ACAAGGGATGAAACTAGTATAGAGAGTTTCTTAGGTAGATCTGGATGTATTGCTAAAGTT
1020 162_HRV88      ACAAGGGATGAAACCAGCATTGAAAGCTTTCTGGGTAGGTCTGGATGCATAGCAAAAATT
1021 163_HRV88a     ACAAGGGATGAAACCAGCATTGAAAGCTTTCTGGGTAGGTCTGGATGCATAGCAAAAATT
1022 164_HRV88b     ACAAGGGATGAAACCAGCATTGAAAGCTTTCTGGGTAGGTCTGGATGCATAGCAAAAATT
1023 165_HRV36a     ACAAGAGATGAGACAAGTATTGAAAGCTTCTTAGGTAGGTCAGGGTGCATAGCTATGATA
1024 166_HRV36b     ACAAGAGATGAGACAAGTATTGAAAGCTTCTTAGGTAGGTCAGGGTGCATAGCTATGATA
1025 167_HRV36      ACAAGAGATGAGACAAGTATTGAAAGCTTCTTAGGTAGGTCAGGGTGCATAGCTATGATA
1026 168_HRV89a     ACAAGGGATGAAACAAGTATTGAGAGTTTCTTAGGTAGGTCAGGGTGTATCGCTATGATA
1027 169_HRV89b     ACAAGGGATGAAACAAGTATTGAGAGTTTCTTAGGTAGGTCAGGGTGTATCGCTATGATA
1028 170_HRV89      ACAAGGGATGAAACAAGTATTGAGAGTTTCTTAGGTAGGTCAGGGTGTATCGCTATGATA
1029 171_HRV58      ACAAGAGATGAAACTAGCATTGAAAGCTTTTAGGTAGATCTGGTTGCATTGCTATCATA
1030 172_HRV58a     ACAAGAGATGAAACTAGCATTGAAAGCTTTTAGGTAGATCTGGTTGCATTGCTATCATA
1031 173_HRV58b     ACAAGAGATGAAACTAGCATTGAAAGCTTTTAGGTAGATCTGGTTGCATTGCTATCATA
1032 174_HRV12a     ACTAGAGATGAGATGTCAATTGAATCTTTCCTTGGTCGGTCCGGATGCATTTCAATTATC
1033 175_HRV12b     ACTAGAGATGAGATGTCAATTGAATCTTTCCTTGGTCGGTCCGGATGCATTTCAATTATC
1034 176_HRV12      ACTAGAGATGAGATGTCAATTGAATCTTTCCTTGGTCGGTCCGGATGCATTTCAATTATC
1035 177_HRV78a     ACAAGAGATGAAATGAGCATTGAAAGTTTCCTCGGAAGATCAGGTTGTGCAACAATTATG
```

FIG. D8 CONT'D

```
04-2.trace                                                                                    9/20/2007 5:04 PM 1036 178_HRV78b      ACAAGAGATGAAATGAGCATTGAAAGTTTCCTCGGAAGATCAGGTTGTGCAACAATTATG
1037 179_HRV78       ACAAGAGATGAAATGAGCATTGAAAGTTTCCTCGGAAGATCAGGTTGTGCAACAATTATG
1038 180_HRV20       ACCCGTGATGAAATGAGTGTGGAAAGTTTTCTTGGTAGATCTGGTTGCATTGCTATCATA
1039 181_HRV20a      ACCCGTGATGAAATGAGTGTGGAAAGTTTTCTTGGTAGATCTGGTTGCATTGCTATCATA
1040 182_HRV20b      ACCCGTGATGAAATGAGTGTGGAAAGTTTTCTTGGTAGATCTGGTTGCATTGCTATCATA
1041 183_HRV68       ACAAGGGATGAAATGAGCATAGAGAGCTTCCTCGGTAGGTCAGGTTGCATTGCAATCATA
1042 184_HRV68a      ACAAGGGATGAAATGAGCATAGAGAGCTTCCTCGGTAGGTCAGGTTGCATTGCAATCATA
1043 185_HRV68b      ACAAGGGATGAAATGAGCATAGAGAGCTTCCTCGGTAGGTCAGGTTGCATTGCAATCATA
1044 186_HRV28       ACCCGTGATGAAATGAGTATAGAGAGTTTCTTAGGTAGGTCTAGTTGCATTGCAATAATC
1045 187_HRV28a      ACCCGTGATGAAATGAGTATAGAGAGTTTCTTAGGTAGGTCTAGTTGCATTGCAATAATC
1046 188_HRV28b      ACCCGTGATGAAATGAGTATAGAGAGTTTCTTAGGTAGGTCTAGTTGCATTGCAATAATC
1047 189_HRV53a      ACCCGGGATGAAATGAGCATTGAAAGTTTCTTAGGCAGATCAAGTTGCATTGCTGAGATC
1048 190_HRV53b      ACCCGGGATGAAATGAGCATTGAAAGTTTCTTAGGCAGATCAAGTTGCATTGCTGAGATC
1049 191_HRV53       ACCCGGGATGAAATGAGCATTGAAAGTTTCTTAGGCAGATCAAGTTGCATTGCTGAGATC
1050 192_HRV46a      ACAAAAGATGAAATGAGTATAGAAAGTTTTCTAGGAAGGTCAGGCTGCATTGCCATTATT
1051 193_HRV46b      ACAAAAGATGAAATGAGTATAGAAAGTTTTCTAGGAAGGTCAGGCTGCATTGCCATTATT
1052 194_HRV46       ACAAAAGATGAAATGAGTATAGAAAGTTTTCTAGGAAGGTCAGGCTGCATTGCCATTATT
1053 195_HRV80a      ACAAAGGATGAGATGAGCATTGAAAGTTTCTTAGGAAGATCTGGTTGTGTTGCTATCATT
1054 196_HRV80b      ACAAAGGATGAGATGAGCATTGAAAGTTTCTTAGGAAGATCTGGTTGTGTTGCTATCATT
1055 197_HRV80       ACAAAGGATGAGATGAGCATTGAAAGTTTCTTAGGAAGATCTGGTTGTGTTGCTATCATT
1056 198_HRV51       ACTAGAGATGAAATGAGTATAGAGAGTTTCTTGGGTAGATCTGCTTGCGTAGCAATCATC
1057 199_HRV51a      ACTAGAGATGAAATGAGTATAGAGAGTTTCTTGGGTAGATCTGCTTGCGTAGCAATCATC
1058 200_HRV51b      ACTAGAGATGAAATGAGTATAGAGAGTTTCTTGGGTAGATCTGCTTGCGTAGCAATCATC
1059 201_HRV65a      ACCAGAGATGAGATGAGCGTAGAGAGTTTCCTGGGCAGATCTGCCTGCATAGCAGTCATT
1060 202_HRV65b      ACCAGAGATGAGATGAGCGTAGAGAGTTTCCTGGGCAGATCTGCCTGCATAGCAGTCATT
1061 203_HRV65       ACCAGAGATGAGATGAGCGTAGAGAGTTTCCTGGGCAGATCTGCCTGCATAGCAGTCATT
1062 204_HRV71a      ACTAGGGATGAAATGAGCATTGAGAGCTTCTTGGGCAGATCTGCATGCATAGCTACCATA
1063 205_HRV71b      ACTAGGGATGAAATGAGCATTGAGAGCTTCTTGGGCAGATCTGCATGCATAGCTACCATA
1064 206_HRV71       ACTAGGGATGAAATGAGCATTGAGAGCTTCTTGGGCAGATCTGCATGCATAGCTACCATA
1065 207_HRV8        ACTAGGCATGAGACATCACTGGAATCTTTCTTGGGTAGAGCAGGATGCATTAAAATCATT
1066 208_HRV95       ACTAGGTATGAGACATCACTGGAATCTTTCTTGGGTAGAGCAGGATGCATTAAAATTATT
1067 209_HRV45       ACCAGACATGAAACCTCCATTGAATCTTTTTGGGTAGGGCTGGATGTGTGGCCAATATT
1068 210_HRV45a      ACCAGACATGAAACCTCCATTGAATCTTTTTGGGTAGGGCTGGATGTGTGGCCAATATT
1069 211_HRV45b      ACCAGACATGAAACCTCCATTGAATCTTTTTGGGTAGGGCTGGATGTGTGGCCAATATT
1070 GROUP_1         AC-----ATGA-A------T-GA----TT--T-GG--G--C----TG-------------
1071
1072 1_HRV1A1|d     AGAATAAAGGTTGATTACACTGAC--------------TATAATGGA---CAGGACATA
1073 2_HRV1A2|d     AGAATAAAGGTTGATTACACTGAC--------------TATAATGGA---CAGGACATA
1074 3_HRV1A|cD     AGAATAAAGGTTGATTACACTGAC--------------TATAATGGA---CAGGACATA
1075 4_HRV1B1|d     AGAATAAAGGTTGATTACAATGAC--------------TACAATGGA---GTGAACAAA
1076 5_HRV1B2|d     AGAATAAAGGTTGATTACAATGAC--------------TACAATGGA---GTGAACAAA
1077 6_HRV1B        AGAATAAAGGTTGATTACAATGAC--------------TACAATGGA---GTGAACAAA
1078 7_HRV40a|d     ACAATTACAGTGGATAACAGTTTG--------------GAATATG------ATGACCAC
1079 8_HRV40b|d     ACAATTACAGTGGATAACAGTTTG--------------GAATATG------ATGACCAC
1080 9_HRV40        ACAATTACAGTGGATAACAGTTTG--------------GAATATG------ATGACCAC
1081 10_HRV85       ACAATTACTGTGAATAACAACCTA--------------GATTATG------ATGAAAAT
1082 11_HRV85a|     ACAATTACTGTGAATAACAACCTA--------------GATTATG------ATGAAAAT
1083 12_HRV85b|     ACAATTACTGTGAATAACAACCTA--------------GATTATG------ATGAAAAT
1084 13_HRV56a|     ACTATAACTGTGGATAATGATGTA--------------GATTATA------ATTCAAAG
1085 14_HRV56b|     ACTATAACTGTGGATAATGATGTA--------------GATTATA------ATTCAAAG
1086 15_HRV56       ACTATAACTGTGGATAATGATGTA--------------GATTATA------ATTCAAAG
1087 16_HRV54       ACCATTACAATTCAAAATGATGTA--------------GAATACA------ATGATCAC
1088 17_HRV98       ACTATCACTATTCAAAATGATGTA--------------GAATATA------ACGATCAT
1089 18_HRV59a|     ACTATTACTGTCAATAAAGACATA--------------AAATATG------ATGATGGA
1090 19_HRV59b|     ACTATTACTGTCAATAAAGACATA--------------AAATATG------ATGATGGA
1091 20_HRV59       ACTATTACTGTCAATAAAGACATA--------------AAATATG------ATGATGGA
1092 21_HRV63       ACTATCACTGTTGACAAAACCATT--------------GACTATG------ACACTGGA
1093 22_HRV63b|     ACTATCACTGTTGACAAAACCATT--------------GACTATG------ACACTGGA
1094 23_HRV63a|     ACTATCACTGTTGACAAAACCATT--------------GACTATG------ACACTGGA
1095 24_HRV39       ACAATTACTATGAAGAAGGAG-----------------AACTATA------ATGATCAT
1096 25_HRV39a|     ACAATTACTATGAAGAAGGAG-----------------AACTATA------ATGATCAT
1097 26_HRV39b|     ACAATTACTATGAAGAAGGAG-----------------AACTATA------ATGAACAT
1098 27_HRV10a|     ACAATAACTGTTAATAATACAAGA--------------CCCTACA------ATGAACAC
1099 28_HRV10b|     ACAATAACTGTTAATAATACAAGA--------------CCCTACA------ATGAACAC
1100 29_HRV10       ACAATAACTGTTAATAATACAAGA--------------CCCTACA------ATGAACAC
```

FIG. D8 CONT'D

04-2.trace                                                                 9/20/2007 5:04 PM

```
1101  30_HRV100a    ACAATTACTGTAAGTAAAATGAAA---------------AATTATA------ATGAGCAC
1102  31_HRV100b    ACAATTACTGTAAGTAAAATGAAA---------------AATTATA------ATGAGCAC
1103  32_HRV100     ACAATTACTGTAAGTAAAATGAAA---------------AATTATA------ATGAGCAC
1104  33_HRV66      ACAATTAATGTGGATAGCACAAAA---------------ACATATG------ATGAATCC
1105  34_HRV66b|    ACAATTAATGTGGATAGCACAAAA---------------ACATATG------ATGAATCC
1106  35_HRV66a|    ACAATTAATGTGGATAGCACAAAA---------------ACATATG------ATGAATCC
1107  36_HRV77a|    ACAATAAATGTAGAAGATGGTAAA---------------ACTTATG------ATGAATCT
1108  37_HRV77b|    ACAATAAATGTAGAAGATGGTAAA---------------ACTTATG------ATGAATCT
1109  38_HRV77      ACAATAAATGTAGAAGATGGTAAA---------------ACTTATG------ATGAATCT
1110  39_HRV62a     ACAATTGAA---------ACAACG---------------CTTAGTC------ATAAAGAT
1111  40_HRV62b     ACAATTGAA---------ACAACG---------------CTTAGTC------ATAAAGAT
1112  41_HRV25      ACAATTGAA---------ACAAAA---------------CTTAAAC------ATGATGAA
1113  42_HRV29a     ACAATAAAA---------GCAAAT---------------CAGGCAC------ATGACGCC
1114  43_HRV29b     ACAATAAAA---------GCAAAT---------------CAGGCAC------ATGACGCC
1115  44_HRV44a     ACAATAAAG---------ACAAAT---------------CAGGCAC------ACAATACC
1116  45_HRV44b     ACAATAAAG---------ACAAAT---------------CAGGCAC------ACAATACC
1117  46_HRV31      ATAATAGAA---------CCAGAT---------------GGACTCC------ATGATAGC
1118  47_HRV31a|    ATAATAGAA---------CCAGAT---------------GGACTCC------ATGATAGC
1119  48_HRV31b|    ATAATAGAA---------CCAGAT---------------GGACTCC------ATGATAGC
1120  49_HRV47      ACAATAAAA---------TCAGAT---------------GAGCAAC------ACATTAAT
1121  50_HRV47a|    ACAATAAAA---------TCAGAT---------------GAGCAAC------ACATTAAT
1122  51_HRV47b|    ACAATACAA---------TCAAAT---------------GAGCAAC------ACATTAAT
1123  52_HRV11      AAGTTAATTGTGCAGTATGAAGAC---------------TATAAT------GGAAAGAAA
1124  53_HRV11b|    AAGTTAATTGTGCAGTATGAAGAC---------------TATAAT------GGAAAGAAA
1125  54_HRV11a|    AAGTTAATTGTGCAGTATGAAGAC---------------TATAAT------GGAAAGAAA
1126  55_HRV76      AAGCTAGTTGTAGAATATGAGGGA---------------TATGAT------GATACAAAA
1127  56_HRV76b|    AAGCTAGTTGTAGAATATGAGGGA---------------TATGAT------GATACAAAA
1128  57_HRV76a|    AAGCTAGTTGTAGAATATGAGGGA---------------TATGAT------GATACAAAA
1129  58_HRV33      AAATTAGTAGTGAAATATGAAGAC---------------TATAAT------GAGAAAAAG
1130  59_HRV33b|    AAATTAGTAGTGAAATATGAAGAC---------------TATAAT------GAGAAAAAG
1131  60_HRV33a|    AAATTAGTAGTGAAATATGAAGAC---------------TATAAT------GAGAAAAAG
1132  61_HRV24a|    AAGTTGACTGTGGATTAT---GAC---------------AATTAT------GATACAAAA
1133  62_HRV24b|    AAGTTGACTGTGGATTAT---GAC---------------AATTAT------GATACAAAA
1134  63_HRV24      AAGTTGACTGTGGATTAT---GAC---------------AATTAT------GATACAAAA
1135  64_HRV90      AAATTAGTTGTAAACTAT---GAT---------------AATTAT------GATGAAAAC
1136  65_HRV90a|    AAATTAGTTGTAAACTAT---GAT---------------AATTAT------GATGAAAAC
1137  66_HRV90b|    AAATTAGTTGTAAACTAT---GAT---------------AATTAT------GATGAAAAC
1138  67_HRV34      AAACTTGTTGTAGATTATGAAAAT---------------TACAATGCA---AAAACAAAG
1139  68_HRV34b|    AAACTTGTTGTAGATTATGAAAAT---------------TACAATGCA---AAAACAAAG
1140  69_HRV34a|    AAACTTGTTGTAGATTATGAAAAT---------------TACAATGCA---AAAACAAAG
1141  70_HRV50a|    AAATTAGTTGTTGATTATGATGGT---------------TACAATGAG---GAAACAAAG
1142  71_HRV50b|    AAATTAGTTGTTGATTATGATGGT---------------TACAATGAG---GAAACAAAG
1143  72_HRV50      AAATTAGTTGTTGATTATGATGGT---------------TACAATGAG---GAAACAAAG
1144  73_HRV18a|    AAGTTAGTTGTACATTATGAAGAT---------------TATAATGCA---GAAACAAGG
1145  74_HRV18b|    AAGTTAGTTGTACATTATGAAGAT---------------TATAATGCA---GAAACAAGG
1146  75_HRV18      AAGTTAGTTGTACATTATGAAGAT---------------TATAATGCA---GAAACAGG
1147  76_HRV55      GAGTTAGTTGTTCATTATGAAGAA---------------TATAACAAA---GAGGGAAAA
1148  77_HRV55b|    GAGTTAGTTGTTCATTATGAAGAA---------------TATAACAAA---GAGGGAAAA
1149  78_HRV55a|    GAGTTAGTTGTTCATTATGAAGAA---------------TATAACAAA---GAGGGAAAA
1150  79_HRV57      GAGCTTAAGGTAAAATATGAAAAT---------------TACAACACA---GAG------
1151  80_HRV57a|    GAGCTTAAGGTAAAATATGAAAAT---------------TACAACACA---GAG------
1152  81_HRV57b|    GAGCTTAAGGTAAAATATGAAAAT---------------TACAACACA---GAG------
1153  82_HRV21      AAATTAGTAGTTAACTATGATAAT---------------TACAATACT---GGAGAAAAT
1154  83_HRVHan     AAATTAATAGTTAACTATGACAAC---------------TACAATACT---GGAGAAAAT
1155  84_HRV43      ACACTTGAAGTAAATTATGATGAT---------------TATAATGGG---ACAGGCATA
1156  85_HRV43b|    ACACTTGAAGTAAATTATGATGAT---------------TATAATGGG---ACAGGCATA
1157  86_HRV43a|    ACACTTGAAGTAAATTATGATGAT---------------TATAATGGG---ACAGGCATA
1158  87_HRV75      ACACTTGAGATGGATTATACAAAC---------------TATAATGGA---GAAGGCAAA
1159  88_HRV75b|    ACACTTGAGATGGATTATACAAAC---------------TATAATGGA---GAAGGCAAA
1160  89_HRV75a|    ACACTTGAGATGGATTATACAAAC---------------TATAATGGA---GAAGGCAAA
1161  96_HRV9a|d    AAATTGAATATTGATTACAGTGAC---------------TATGATAAG---AGTGTTGAA
1162  97_HRV9b|d    AAATTGAATATTGATTACAGTGAC---------------TATGATAAG---AGTGTTGAA
1163  98_HRV9       AAATTGAATATTGATTACAGTGAC---------------TATGATAAG---AGTGTTGAA
1164  99_HRV32      AAATTAGATATTGATTATACCAAT---------------TACAATAAA---AGTGTTAAG
1165  100_HRV32a    AAATTAGATATTGATTATACCAAT---------------TACAATAAA---AGTGTTAAG
```

FIG. D8 CONT'D

```
04-2.trace                                                                      9/20/2007 5:04 PM 1166 101_HRV32b       AAAATTAGATATTGATTATACCAAT---------------TACAATAAA---AGTGTTAAG
1167 102_HRV67        AAATTGAATATTGATTATAATGCA---------------TATGATGAA---AGTAGGGAC
1168 103_HRV67a       AAATTGAATATTGATTATAATGCA---------------TATGATGAA---AGTAGGGAC
1169 104_HRV67b       AAATTGAATATTGATTATAATGCA---------------TATGATGAA---AGTAGGGAC
1170 105_HRV15        GATTTGAAAATACATTATGAAGAT---------------TATAATAAA---GATGGGAAA
1171 106_HRV15a       GATTTGAAAATACATTATGAAGAT---------------TATAATAAA---GATGGGAAA
1172 107_HRV15b       GATTTGAAAATACATTATGAAGAT---------------TATAATAAA---GATGGGAAA
1173 108_HRV74a       CATCTAAAAATTGATTATACAAAC---------------TATAATGTT---AAAGGGAAG
1174 109_HRV74b       CATCTAAAAATTGATTATACAAAC---------------TATAATGTT---AAAGGGAAG
1175 110_HRV74        CATCTAAAAATTGATTATACAAAC---------------TATAATGTT---AAAGGGAAG
1176 111_HRV38a       AATCTTGACATAGATTACATTAAT---------------TACAACTCT---GAAGACAAA
1177 112_HRV38b       AATCTTGACATAGATTACATTAAT---------------TACAACTCT---GAAGACAAA
1178 113_HRV38        AATCTTGACATAGATTACATTAAT---------------TACAACTCT---GAAGACAAA
1179 114_HRV60        AAATTAGAAATTGACTATAGTAAC---------------TACAATGAG---GAGAATAAA
1180 115_HRV60a       AAATTAGAAATTGACTATAGTAAC---------------TACAATGAG---GAGAATAAA
1181 116_HRV60b       AAATTAGAAATTGACTATAGTAAC---------------TACAATGAG---GAGAATAAA
1182 117_HRV64a       GATTTAAAAGTAAATTATACTGGG---------------TATAATGAT---GAAGGTAAC
1183 118_HRV64b       GATTTAAAAGTAAATTATACTGGG---------------TATAATGAT---GAAGGTAAC
1184 119_HRV64        GATTTAAAAGTAAATTATACTGGG---------------TATAATGAT---GAAGGTAAC
1185 120_HRV94a       CATCTAGAGATCAAGTATGATGGT---------------TACAATGAT---GCTGGCAAC
1186 121_HRV94b       CATCTAGAGATCAAGTATGATGGT---------------TACAATGAT---GCTGGCAAC
1187 122_HRV94        CATCTAGAGATCAAGTATGATGGT---------------TACAATGAT---GCTGGCAAC
1188 123_HRV22        CACTTAGAAGTAAAATACACAGGG---------------TATAATGAA---GAGGGTAAT
1189 124_HRV22a       CACTTAGAAGTAAAATACACAGGG---------------TATAATGAA---GAGGGTAAT
1190 125_HRV22b       CACTTAGAAGTAAAATACACAGGG---------------TATAATGAA---GAGGGTAAT
1191 126_HRV82        CACCTAAATGTCAGATACACTG-----------------ATTATAAT---GAAGGTAAT
1192 127_HRV82b       CACCTAAATGTCAGATACACTG------------------ATTATAAT---GAAGGTAAT
1193 128_HRV82a       CACCTAAATGTCAGATACACTG------------------ATTATAAT---GAAGGTAAT
1194 129_HRV19        GAGCTCCAATTAGATTATACCAAT---------------TACAATCAA---GAAAATAAT
1195 130_HRV19a       GAGCTCCAATTAGATTATACCAAT---------------TACAATCAA---GAAAATAAT
1196 131_HRV19b       GAGCTCCAATTAGATTATACCAAT---------------TACAATCAA---GAAAATAAT
1197 132_HRV13        ACCATGAACATAGATTATACTAAT---------------TATGATGAT---TCTGTTAAT
1198 133_HRV13a       ACCATGAACATAGATTATACTAAT---------------TATGATGAT---TCTGTTAAT
1199 134_HRV13b       ACCATGAACATAGATTATACTAAT---------------TATGATGAT---TCTGTTAAT
1200 135_HRV41        ACTTTGAATATAGATTATACTGAT---------------TATGATGAT---TCTATCCAG
1201 136_HRV41a       ACTTTGAATATAGATTATACTGAT---------------TATGATGAT---TCTATCCAG
1202 137_HRV41b       ACTTTGAATATAGATTATACTGAT---------------TATGATGAT---TCTATCCAG
1203 138_HRV73        ACTATGAATATAAATTATGAAAAT---------------TATGATGAT---GCTCCTGAA
1204 139_HRV73b       ACTATGAATATAAATTATGAAAAT---------------TATGATGAT---GCTCCTGAA
1205 140_HRV73a       ACTATGAATATAAATTATGAAAAT---------------TATGATGAT---GCTCCTGAA
1206 141_HRV61        ACATTAAATATAAACTATGATAAC---------------TATGATGAT---TCTATTGAA
1207 142_HRV61a       ACATTAAATATAAACTATGATAAC---------------TATGATGAT---TCTATTGAA
1208 143_HRV61b       ACATTAAATATAAACTATGATAAC---------------TATGATGAT---TCTATTGAA
1209 144_HRV96        ACATTAAACATAGATTATGACAAT---------------TATGATGAC---TCCCCTAAG
1210 145_HRV96b       ACATTAAACATAGATTATGACAAT---------------TATGATGAC---TCCCCTAAG
1211 146_HRV96a       ACATTAAACATAGATTATGACAAT---------------TATGATGAC---TCCCCTAAG
1212  90_HRV16a|      GTGTTGGATATTGTGGACAATTAC---------------AATGAT-----------CAA
1213  91_HRV16b|      GTGTTGGATATTGTGGACAATTAC---------------AATGAT-----------CAA
1214  92_1AYM_A       GTGTTGGATATTGTGGACAATTAC---------------AATGAT-----------CAA
1215  93_HRV81a|      ATATTGGACATTAAAGAGGATTAC---------------AATACC-----------CAG
1216  94_HRV81b|      ATATTGGACATTAAAGAGGATTAC---------------AATACC-----------CAG
1217  95_HRV81        ATATTGGACATTAAAGAGGATTAC---------------AATACC-----------CAG
1218 147_HRV2         AAATTAGAGGTTACACTTGCAAAT---------------TATAACA--------AGGAG
1219 148_HRV2a|       AAATTAGAGGTTACACTTGCAAAT---------------TATAACA--------AGGAG
1220 149_HRV2b|       AAATTAGAGGTTACACTTGCAAAT---------------TATAACA--------AGGAG
1221 150_HRV49a       AAACTAGAGGTCACACTTACAAAT---------------TACAATG--------AAAAT
1222 151_HRV49b       AAACTAGAGGTCACACTTACAAAT---------------TACAATG--------AAAAT
1223 152_HRV49        AAACTAGAGGTCACACTTACAAAT---------------TACAATG--------AAAAT
1224 153_HRV23a       AAATTAAAAGTTGAGATCGGAAAC---------------TATGATG--------AAAAC
1225 154_HRV23b       AAATTAAAAGTTGAGATCGGAAAC---------------TATGATG--------AAAAC
1226 155_HRV23        AAATTAAAAGTTGAGATCGGAAAC---------------TATGATG--------AAAAC
1227 156_HRV30a       AAATTAGAACTTGAGCTTGCACAC---------------TATGATA--------AAAAG
1228 157_HRV30b       AAATTAGAACTTGAGCTTGCACAC---------------TATGATA--------AAAAG
1229 158_HRV30        AAATTAGAACTTGAGCTTGCACAC---------------TATGATA--------AAAAG
1230 159_HRV7         AAACTTGACACAA------CACAGGGT---------GACTATGACACAGGCAAAGGTGTT
```

FIG. D8 CONT'D

04-2.trace                                                                                          9/20/2007 5:04 PM

```
1231 160_HRV7b|      AAACTTGACACAA------CACAGGGT---------GACTATGACACAGGCAAAGGTGTT
1232 161_HRV7a|      AAACTTGACACAA------CACAGGGT---------GACTATGACACAGGCAAAGGTGTT
1233 162_HRV88       AAACTTGACACAA------ATGAAGGT---------GATTACGACACA---ATAGGTGTT
1234 163_HRV88a      AAACTTGACACAA------ATGAAGGT---------GATTACGACACA---ATAGGTGTT
1235 164_HRV88b      AAACTTGACACAA------ATGAAGGT---------GATTACGACACA---ATAGGTGTT
1236 165_HRV36a      GAATTTAGCACAAGTAGTGATAAAGAT---------GAACATGATGAA---ATTGGCAAG
1237 166_HRV36b      GAATTTAGCACAAGTAGTGATAAAGAT---------GAACATGATGAA---ATTGGCAAG
1238 167_HRV36       GAATTTAGCACAAGTAGTGATAAAGAT---------GAACATGATGAA---ATTGGCAAG
1239 168_HRV89a      GAATTTAATACAAGTAGTGATAAAACT---------GAACATGATAAA---ATTGGTAAA
1240 169_HRV89b      GAATTTAATACAAGTAGTGATAAAACT---------GAACATGATAAA---ATTGGTAAA
1241 170_HRV89       GAATTTAATACAAGTAGTGATAAAACT---------GAACATGATAAA---ATTGGTAAA
1242 171_HRV58       AAATTTAACACAA------ATAAGACT---------AATTATGATGAC---ATAGGTGTA
1243 172_HRV58a      AAATTTAACACAA------ATAAGACT---------AATTATGATGAC---ATAGGTGTA
1244 173_HRV58b      AAATTTAACACAA------ATAAGACT---------AATTATGATGAC---ATAGGTGTA
1245 174_HRV12a      GAATTGGATTTAGACCATGAAGGT---------------TATTCAGCA---GAAGGGAAA
1246 175_HRV12b      GAATTGGATTTAGACCATGAAGGT---------------TATTCAGCA---GAAGGGAAA
1247 176_HRV12       GAATTGGATTTAGACCATGAAGGT---------------TATTCAGCA---GAAGGGAAA
1248 177_HRV78a      AGACTAGAATTGGACCACACTGAT---------------TACAATGCT---GAAGGGAAA
1249 178_HRV78b      AGACTAGAATTGGACCACACTGAT---------------TACAATGCT---GAAGGGAAA
1250 179_HRV78       AGACTAGAATTGGACCACACTGAT---------------TACAATGCT---GAAGGGAAA
1251 180_HRV20       CATACTGACTTAGATCATGAAGCACAA---------CAATATAATGCA---CCCGGAAAA
1252 181_HRV20a      CATACTGACTTAGATCATGAAGCACAA---------CAATATAATGCA---CCCGGAAAA
1253 182_HRV20b      CATACTGACTTAGATCATGAAGCACAA---------CAATATAATGCA---CCCGGAAAA
1254 183_HRV68       CATACTGACTTAGATCAATGAGGAT---------CAGTACAATGCA---CCTGGAAAA
1255 184_HRV68a      CATACTGACTTAGATCACAATGAGGAT---------CAGTACAATGCA---CCTGGAAAA
1256 185_HRV68b      CATACTGACTTAGATCACAATGAGGAT---------CAGTACAATGCA---CCTGGAAAA
1257 186_HRV28       CATACTGATGTTGTGCATGAAACAGAC---------AAGTACAACCAC---CCAGGGAAG
1258 187_HRV28a      CATACTGATGTTGTGCATGAAACAGAC---------AAGTACAACCAC---CCAGGGAAG
1259 188_HRV28b      CATACTGATGTTGTGCATGAAACAGAC---------AAGTACAACCAC---CCAGGGAAG
1260 189_HRV53a      CATACCAATTTAGACCAT---ACTG-----------GATACAATGAG---CCTGGGAAA
1261 190_HRV53b      CATACCAATTTAGACCAT---ACTG-----------GATACAATGAG---CCTGGGAAA
1262 191_HRV53       CATACCAATTTAGACCAT---ACTG-----------GATACAATGAG---CCTGGGAAA
1263 192_HRV46a      GAGACAGAATTGAATCATGAAGAAGGG---------AAATACAATGCA---GAAGATCAA
1264 193_HRV46b      GAGACAGAATTGAATCATGAAGAAGGG---------AAATACAATGCA---GAAGATCAA
1265 194_HRV46       GAGACAGAATTGAATCATGAAGAAGGG---------AAATACAATGCA---GAAGATCAA
1266 195_HRV80a      GAAACCAAATTAAACCATGAAACAGAC---------ATGTACAATGCT---GATGGTCAG
1267 196_HRV80b      GAAACCAAATTAAACCATGAAACAGAC---------ATGTACAATGCT---GATGGTCAG
1268 197_HRV80       GAAACCAAATTAAACCATGAAACAGAC---------ATGTACAATGCT---GATGGTCAG
1269 198_HRV51       CATACAAACCTTGAGCATGTTGAAGCAGACAGACAAGCCTACAATGCA---AAAGGGAAA
1270 199_HRV51a      CATACAAACCTTGAGCATGTTGAAGCAGACAGACAAGCCTACAATGCA---AAAGGGAAA
1271 200_HRV51b      CATACAAACCTTGAGCATGTTGAAGCAGACAGACAAGCCTACAATGCA---AAAGGGAAA
1272 201_HRV65a      CACACAGATCTTAAACATGACCATGAAGGCCAAAATGTTTACAATGAC---GAAGGCAGA
1273 202_HRV65b      CACACAGATCTTAAACATGACCATGAAGGCCAAAATGTTTACAATGAC---GAAGGCAGA
1274 203_HRV65       CACACAGATCTTAAACATGACCATGAAGGCCAAAATGTTTACAATGAC---GAAGGCAGA
1275 204_HRV71a      CACACTAAATTAGTACATGGAGAGGAGGG------TGTTTATAATATG---AAAGGTAAC
1276 205_HRV71b      CACACTAAATTAGTACATGGAGAGGAGGG------TGTTTATAATATG---AAAGGTAAC
1277 206_HRV71       CACACTAAATTAGTACATGGAGAGGAGGG------TGTTTATAATATG---AAAGGTAAC
1278 207_HRV8        GCATTAGAACTAGATCATGACAAC---------------TATGATGAA-----------
1279 208_HRV95       GCATTAGAACTAGATCATGACAAC---------------TATGATAAA-----------
1280 209_HRV45       AGTTTAGACATTAACCATGATGAC---------------TACCAAAAG-----------
1281 210_HRV45a      AGTTTAGACATTAACCATGATGAC---------------TACCAAAAG-----------
1282 211_HRV45b      AGTTTAGACATTAACCATGATGAC---------------TACCAAAAG-----------
1283 GROUP_1         ------------------------------------------------------------
1284
1285 1_HRV1A1|d      AATTTCACAAAATGGAAAATCACACTACAGGAAATGGCACAGATTAGGAGAAAATTTGAA
1286 2_HRV1A2|d      AATTTCACAAAATGGAAAATCACACTACAGGAAATGGCACAGATTAGGAGAAAATTTGAA
1287 3_HRV1A|cD      AATTTCACAAAATGGAAAATCACACTACAGGAAATGGCACAGATTAGGAGAAAATTTGAA
1288 4_HRV1B1|d      AACTTTACAACATGGAAAATCACACTGCAGGAGATGGCACAAATTAGAAGAAAATTCGAA
1289 5_HRV1B2|d      AACTTTACAACATGGAAAATCACACTGCAGGAGATGGCACAAATTAGAAGAAAATTCGAA
1290 6_HRV1B         AACTTTACAACATGGAAAATCACACTGCAGGAGATGGCACAAATTAGAAGAAAATTCGAA
1291 7_HRV40a|d      CACTTTGATAAGTGGCAGATAACCATAAGAGATGTCACAAATTAGGAGAAAATTTGAA
1292 8_HRV40b|d      CACTTTGATAAGTGGCAGATAACCATAAGAGATGTCACAAATTAGGAGAAAATTTGAA
1293 9_HRV40         CACTTTGATAAGTGGCAGATAACCATACAAGAGATGTCACAAATTAGGAGAAAATTTGAA
1294 10_HRV85        CACTTTGATCAGTGGCAGATAACTATACAGGAAATGGCACAAATTAGAAGGAAGTTTGAG
1295 11_HRV85a|      CACTTTGATCAGTGGCAGATAACTATACAGGAAATGGCACAAATTAGAAGGAAGTTTGAG
```

FIG. D8 CONT'D 04-2.trace                                                                 9/20/2007 5:04 PM

```
1296 12_HRV85b|     CACTTTGATCAGTGGCAGATAACTATACAGGAAATGGCACAAATTAGAAGGAAGTTTGAG
1297 13_HRV56a|     CATTATAATAAATGGCAAATAACCTTACAAGAAATGGCTCAAGTTAGGCGTAAATTTGAA
1298 14_HRV56b|     CATTATAATAAATGGCAAATAACCTTACAAGAAATGGCTCAAGTTAGGCGTAAATTTGAA
1299 15_HRV56      CATTATAATAAATGGCAAATAACCTTACAAGAAATGGCTCAAGTTAGGCGTAAATTTGAA
1300 16_HRV54      CATTTTAAGAAATGGGATATAACATTACAAGAGATGGCACAAATACGAAGGAAATTTGAA
1301 17_HRV98      CATTTTAGACAATGGGATATAACATTACAAGAAATGGCACAAATTCGAAGAAATTTGAA
1302 18_HRV59a|     CACTTTCTTAAATGGCCTATAACATTACAAGAGATGGCACAAATTAGGAGAAATTTGAA
1303 19_HRV59b|     CACTTTCTTAAATGGCCTATAACATTACAAGAGATGGCACAAATTAGGAGAAATTTGAA
1304 20_HRV59      CACTTTCTTAAATGGCCTATAACATTACAAGAGATGGCACAAATTAGGAGAAAATTTGAA
1305 21_HRV63      CATTTTAATAAATGGCAAATAACATTACAAGAGATGGCACAAATTAGAAGGAAATTTGAA
1306 22_HRV63b|     CATTTTAATAAATGGCAAATAACATTACAAGAGATGGCACAAATTAGAAGGAAATTTGAA
1307 23_HRV63a|     CATTTTAATAAATGGCAAATAACATTACAAGAGATGGCACAAATTAGAAGGAAATTTGAA
1308 24_HRV39      AATTTTGTGGATTGGAAAATTACTTTGCAGGAGATGGCACAGGTTAGAAGGAAATTTGAA
1309 25_HRV39a|     AATTTTGTGGATTGGAAAATTACTTTGCAGGAGATGGCACAGGTTAGAAGGAAATTTGAA
1310 26_HRV39b|     AATTTTGTGGATTGGAAAATTACTTTGCAGGAGATGGCACAGGTTAGAAGGAAATTTGAA
1311 27_HRV10a|     ACTTTTGACACATGGCAAATAACTCTACAAGAAATGGCCCAAATTAGAAGGAAATTTGAA
1312 28_HRV10b|     ACTTTTGACACATGGCAAATAACTCTACAAGAAATGGCCCAAATTAGAAGGAAATTTGAA
1313 29_HRV10      ACTTTTGACACATGGCAAATAACTCTACAAGAAATGGCCCAAATTAGAAGGAAATTTGAA
1314 30_HRV100a    ACTTTTGACAAATGGCAAATAACCCTACAGGAAATGGCCCAAATTAGAAGGAAATTTGAA
1315 31_HRV100b    ACTTTTGACAAATGGCAAATAACCCTACAGGAAATGGCCCAAATTAGAAGGAAATTTGAA
1316 32_HRV100     ACTTTTGACAAATGGCAAATAACCCTACAGGAAATGGCCCAAATTAGAAGGAAATTTGAA
1317 33_HRV66      AAATTTAGAACATGGCAAATTACATTGCAAGAAATGGCTCAAATCAGACGCAAATTTGAG
1318 34_HRV66b|     AAATTTAGAACATGGCAAATTACATTGCAAGAAATGGCTCAAATCAGACGCAAATTTGAG
1319 35_HRV66a|     AAATTTAGAACATGGCAAATTACATTGCAAGAAATGGCTCAAATCAGACGCAAATTTGAG
1320 36_HRV77a|     AAATTTAGAAAATGGCAAATTACACTACAAGAAATGGCTCAAATTAGGCGCAAATTTGAA
1321 37_HRV77b|     AAATTTAGAAAATGGCAAATTACACTACAAGAAATGGCTCAAATTAGGCGCAAATTTGAA
1322 38_HRV77      AAATTTAGAAAATGGCAAATTACACTACAAGAAATGGCTCAAATTAGGCGCAAATTTGAA
1323 39_HRV62a     AGATTCAAAACATGGAATATTAACTTACAAGAGATGGCTCAAATCAGGAGAAAGTTTGAA
1324 40_HRV62b     AGATTCAAAACATGGAATATTAACTTACAAGAAATGGCTCAAATCAGGAGAAAGTTTGAA
1325 41_HRV25      AGATTTAAAATATGGAATATCAATTTACAAGAAATGGCTCAAATTAGGAGAAAGTTTGAG
1326 42_HRV29a     AAGTTCGATAAATGGAATGTTAACTTACAAGAAATGGCTCAAATTAGGCGCAAATTTGAA
1327 43_HRV29b     AAGTTCGATAAATGGAATGTTAACTTACAAGAAATGGCTCAAATTAGGCGCAAATTTGAA
1328 44_HRV44a     AAGTTTGATAAATGGAATATCAACTTACAAGAAATGGCTCAAATTAGACGCAAATTTGAA
1329 45_HRV44b     AAGTTTGATAAATGGAATATCAACTTACAAGAAATGGCTCAAATTAGACGCAAATTTGAA
1330 46_HRV31      AAAATATAAAGTATGGCACATTAATTTACAAGAGATGGCCCAGATTAGGCGCAAATTTGAA
1331 47_HRV31a|     AAAATATAAAGTATGGCACATTAATTTACAAGAGATGGCCCAGATTAGGCGAAAATTTGAA
1332 48_HRV31b|     AAAATATAAAGTATGGCACATTAATTTACAAGAGATGGCCCAGATTAGGCGAAAATTTGAA
1333 49_HRV47      AAATTTAAAGTATGGCACATTAATTTACAAGAAATGGCCCAGATCAGGCGTAAATATGAA
1334 50_HRV47a|     AAATTTAAAGTATGGCACATTAATTTACAAGAAATGGCCCAGATCAGGCGTAAATATGAA
1335 51_HRV47b|     AAATTTAAAGTATGGCACATTAATTTACAAGAAATGGCCCAGATCAGGCGTAAATATGAA
1336 52_HRV11      AACTTTAACACATGGAAAATAAACTTGCAAGAGATGGCACAAATTAGAAGGAAATTTGAA
1337 53_HRV11b|     AACTTTAACACATGGAAAATAAACTTGCAAGAGATGGCACAAATTAGAAGGAAATTTGAA
1338 54_HRV11a|     AACTTTAACACATGGAAAATAAACTTGCAAGAGATGGCACAAATTAGAAGGAAATTTGAA
1339 55_HRV76      AACTTTAAGACATGGAAAATAAACCTACAAGAAATGGCACAAGTTAGAAGAAAATTTGAG
1340 56_HRV76b|     AACTTTAAGACATGGAAAATAAACCTACAAGAAATGGCACAAGTTAGAAGAAAATTTGAG
1341 57_HRV76a|     AACTTTAAGACATGGAAAATAAACCTACAAGAAATGGCACAAGTTAGAAGAAAATTTGAG
1342 58_HRV33      AATTTTATGACATGGAAAATAAATCTACAAGAGATGGCACAGATTAGGAGGAAATTTGAA
1343 59_HRV33b|     AATTTTATGACATGGAAAATAAATCTACAAGAGATGGCACAGATTAGGAGGAAATTTGAA
1344 60_HRV33a|     AATTTTATGACATGGAAAATAAATCTACAAGAGATGGCACAGATTAGGAGGAAATTTGAA
1345 61_HRV24a|     AATTTTTTCAAATGGCAAATAAATCTACAAGAAATGGCCCAAGTCAGAAGAAAATTTGAA
1346 62_HRV24b|     AATTTTTTCAAATGGCAAATAAATCTACAAGAAATGGCCCAAGTCAGAAGAAAATTTGAA
1347 63_HRV24      AATTTTTTCAAATGGCAAATAAATCTACAAGAAATGGCCCAAGTCAGAAGAAAATTTGAA
1348 64_HRV90      AACTTCCATAAATGGCAAATTAACCTGCAAGAGATGGCACAGATTAGAAGAAAATTTGAA
1349 65_HRV90a|     AACTTCCATAAATGGCAAATTAACCTGCAAGAGATGGCACAGATTAGAAGAAAATTTGAA
1350 66_HRV90b|     AACTTCCATAAATGGCAAATTAACCTGCAAGAGATGGCACAGATTAGAAGAAAATTTGAA
1351 67_HRV34      AACTTTATGACATGGCAAATTAATTTACAGGAAATGGCACAGATTAGAAGGAAATTTGAA
1352 68_HRV34b|     AACTTTTATGACATGGCAAATTAATTTACAGGAAATGGCACAGATTAGAAGGAAATTTGAA
1353 69_HRV34a|     AACTTTATGACATGGCAAATTAATTTACAGGAAATGGCACAGATTAGAAGGAAATTTGAA
1354 70_HRV50a|     AACTTCAAGAAATGGCAAATCAACCTACAAGAAATGGCACAGATCAGAAGGAAATTTGAG
1355 71_HRV50b|     AACTTCAAGAAATGGCAAATCAACCTACAAGAAATGGCACAGATCAGAAGGAAATTTGAG
1356 72_HRV50      AACTTCAAGAAATGGCAAATCAACCTACAAGAAATGGCACAGATCAGAAGGAAATTTGAG
1357 73_HRV18a|     AACTTTGTAAAATGGCAAATAAATCTACAGGAAATGGCCCAGATTAGGAGAAAATTTGAG
1358 74_HRV18b|     AACTTTGTAAAATGGCAAATAAATCTACAGGAAATGGCCCAGATTAGGAGAAAATTTGAG
1359 75_HRV18      AACTTTGTAAAATGGCAAATAAATCTACAGGAAATGGCCCAGATTAGGAGAAAATTTGAG
1360 76_HRV55      AATTTTACTAAGTGGCAAGTAAACATCCAAGAGATGGCTCAGATTAGAAGAAAATTTGAA
```

FIG. D8 CONT'D

04-2.trace                                                                                              9/20/2007 5:04 PM

```
1361  77_HRV55b|     AATTTTACTAAGTGGCAAGTAAACATCCAAGAGATGGCTCAGATTAGAAGAAAATTTGAA
1362  78_HRV55a|     AATTTTACTAAGTGGCAAGTAAACATCCAAGAGATGGCTCAGATTAGAAGAAAATTTGAA
1363  79_HRV57      AATTTCACTAAATGGGAAATAAATCTACAAGAAATGGCACAAATCAGAAGAAAATTTGAA
1364  80_HRV57a|    AATTTCACTAAATGGGAAATAAATCTACAAGAAATGGCACAAATCAGAAGAAAATTTGAA
1365  81_HRV57b|    AATTTCACTAAATGGGAAATAAATCTACAAGAAATGGCACAAATCAGAAGAAAATTTGAA
1366  82_HRV21      AACATTAGTACATGGCAAATAAATATTAAAGAGATGGCACAAATTAGGAGAAAATTTGAA
1367  83_HRVHan     AACATTAATACATGGCAAATAAATATTAAAGAGATGGCACAAATTAGGAGAAAATTTGAA
1368  84_HRV43      AATTTTACCCAATGGCCAATCAACTTGCAAGAAATGGCACAAATTAGAAGAAAGTATGAA
1369  85_HRV43b|    AATTTTACCCAATGGCCAATCAACTTGCAAGAAATGGCACAAATTAGAAGAAAGTATGAA
1370  86_HRV43a|    AATTTTACCCAATGGCCAATCAACTTGCAAGAAATGGCACAAATTAGAAGAAAGTATGAA
1371  87_HRV75      AACTTCACTCAGTGGCCAATCAATCTACAGGAAATGGCTCAAATTAGAAGGAAATATGAA
1372  88_HRV75b|    AACTTCACTCAGTGGCCAATCAATCTACAGGAAATGGCTCAAATTAGAAGGAAATATGAA
1373  89_HRV75a|    AACTTCACTCAGTGGCCAATCAATCTACAGGAAATGGCTCAAATTAGAAGGAAATATGAA
1374  96_HRV9a|d    AATTTCACAATCTGGAAAATAAATATAAAGGAAATGGCCCAGATCAGGAGGAAATTTGAA
1375  97_HRV9b|d    AATTTCACAATCTGGAAAATAAATATAAAGGAAATGGCCCAGATCAGGAGGAAATTTGAA
1376  98_HRV9       AATTTCACAATCTGGAAAATAAATATAAAGGAAATGGCCCAGATCAGGAGGAAATTTGAA
1377  99_HRV32      AATTTCACAATTTGGAAGATAAATATAAAAGAAATGGCCCAGATTAGGAGAAAATTTGAG
1378  100_HRV32a    AATTTCACAATTTGGAAGATAAATATAAAAGAAATGGCCCAGATTAGGAGAAAATTTGAG
1379  101_HRV32b    AATTTCACAATTTGGAAGATAAATATAAAAGAAATGGCCCAGATTAGGAGAAAATTTGAG
1380  102_HRV67     AATTTCACAATTTGGAAAATAAATATAAAAGAAATGGCCCAGATTAGGAGGAAATTTGAA
1381  103_HRV67a    AATTTCACAATTTGGAAAATAAATATAAAAGAAATGGCCCAGATTAGGAGGAAATTTGAA
1382  104_HRV67b    AATTTCACAATTTGGAAAATAAATATAAAAGAAATGGCCCAGATTAGGAGGAAATTTGAA
1383  105_HRV15     AACTTTACTAAATGGCAAATTAATCTCAAAGAAATGGCCCAGATTAGAAGGAAATTTGAG
1384  106_HRV15a    AACTTTACTAAATGGCAAATTAATCTCAAAGAAATGGCCCAGATTAGAAGGAAATTTGAG
1385  107_HRV15b    AACTTTACTAAATGGCAAATTAATCTCAAAGAAATGGCCCAGATTAGAAGGAAATTTGAG
1386  108_HRV74a    AATTTTACTAAATGGCAAATAAATCTTAAAGAAATGGCACAGATTAGGAGAAAATTTGAG
1387  109_HRV74b    AATTTTACTAAATGGCAAATAAATCTTAAAGAAATGGCACAGATTAGGAGAAAATTTGAG
1388  110_HRV74     AATTTTACTAAATGGCAAATAAATCTTAAAGAAATGGCACAGATTAGGAGAAAATTTGAG
1389  111_HRV38a    AACTTTACAACATGGCAAATCAATCTCAAAGAAATGGCTCAAATCAGAAGAAAGTTTGAA
1390  112_HRV38b    AACTTTACAACATGGCAAATCAATCTCAAAGAAATGGCTCAAATCAGAAGAAAGTTTGAA
1391  113_HRV38     AACTTTACAACATGGCAAATCAATCTCAAAGAAATGGCTCAAATCAGAAGAAAGTTTGAA
1392  114_HRV60     AATTTCACAACTTGGCAAATTAACCTAAAGGAAATGGCACAAATAAGAAGAAAGTTTGAA
1393  115_HRV60a    AATTTCACAACTTGGCAAATTAACCTAAAGGAAATGGCACAAATAAGAAGAAAGTTTGAA
1394  116_HRV60b    AATTTCACAACTTGGCAAATTAACCTAAAGGAAATGGCACAAATAAGAAGAAAGTTTGAA
1395  117_HRV64a    AATTTTAACAAATGGCAGATCACCTTGAAAGAAATGGCTCAGATAAGAAGGAAGTATGAA
1396  118_HRV64b    AATTTTAACAAATGGCAGATCACCTTGAAAGAAATGGCTCAGATAAGAAGGAAGTATGAA
1397  119_HRV64     AATTTTAACAAATGGCAGATCACCTTGAAAGAAATGGCTCAGATAAGAAGGAAGTATGAA
1398  120_HRV94a    AATTTCCAATCATGGCAAATTACCCTAAAAGAAATGGCACAAATAAGAAGGAAATTTGAA
1399  121_HRV94b    AATTTCCAATCATGGCAAATTACCCTAAAAGAAATGGCACAAATAAGAAGGAAATTTGAA
1400  122_HRV94     AATTTCCAATCATGGCAAATTACCCTAAAAGAAATGGCACAAATAAGAAGGAAATTTGAA
1401  123_HRV22     AACTTTAACATATGGCAAATTAACCTTAAAGAGATGGCTCAGATAAGAAGGAAGTTTGAG
1402  124_HRV22a    AACTTTAACATATGGCAAATTAACCTTAAAGAGATGGCTCAGATAAGAAGGAAGTTTGAG
1403  125_HRV22b    AACTTTAACATATGGCAAATTAACCTTAAAGAGATGGCTCAGATAAGAAGGAAGTTTGAG
1404  126_HRV82     AACTTTAGATCATGGCAAATAAGCATAAAGGAAATGGCACAAATTAGAAGGAAGTTTGAA
1405  127_HRV82b    AACTTTAGATCATGGCAAATAAGCATAAAGGAAATGGCACAAATTAGAAGGAAGTTTGAA
1406  128_HRV82a    AACTTTAGATCATGGCAAATAAGCATAAAGGAAATGGCACAAATTAGAAGGAAGTTTGAA
1407  129_HRV19     AATTTCAAAACTTGGCAAATAAACTTGAAAGAAATGGCACAGATTAGAAGAAAATTTGAA
1408  130_HRV19a    AATTTCAAAACTTGGCAAATAAACTTGAAAGAAATGGCACAGATTAGAAGAAAATTTGAA
1409  131_HRV19b    AATTTCAAAACTTGGCAAATAAACTTGAAAGAAATGGCACAGATTAGAAGAAAATTTGAA
1410  132_HRV13     AATTTTGTGAAATGGAAAATAAGTTTGCAAGAAATGGCCCAAGTGCGCAGAAAATTTGAG
1411  133_HRV13a    AATTTTGTGAAATGGAAAATAAGTTTGCAAGAAATGGCCCAAGTGCGCAGAAAATTTGAG
1412  134_HRV13b    AATTTTGTGAAATGGAAAATAAGTTTGCAAGAAATGGCCCAAGTGCGCAGAAAATTTGAG
1413  135_HRV41     AACTTCAAGAAGTGGAAAATTAGCTTACAGGAGATGGCCCAAGTACGTAGAAAGTTTGAG
1414  136_HRV41a    AACTTCAAGAAGTGGAAAATTAGCTTACAGGAGATGGCCCAAGTACGTAGAAAGTTTGAG
1415  137_HRV41b    AACTTCAAGAAGTGGAAAATTAGCTTACAGGAGATGGCCCAAGTACGTAGAAAGTTTGAG
1416  138_HRV73     AATTTTACCAAATGGAAAATAAGTTTACAAGAGATGGCTCAAATACGTAGGAAATTTGAA
1417  139_HRV73b    AATTTTACCAAATGGAAAATAAGTTTACAAGAGATGGCTCAAATACGTAGGAAATTTGAA
1418  140_HRV73a    AATTTTACCAAATGGAAAATAAGTTTACAAGAGATGGCTCAAATACGTAGGAAATTTGAA
1419  141_HRV61     AACTTCAAGGTGTGGAAAATAAACCTGCAAGAGATGGCACAAATACGTAGAAAATTTGAG
1420  142_HRV61a    AACTTCAAGGTGTGGAAAATAAACCTGCAAGAGATGGCACAAATACGTAGAAAATTTGAG
1421  143_HRV61b    AACTTCAAGGTGTGGAAAATAAACCTGCAAGAGATGGCACAAATACGTAGAAAATTTGAG
1422  144_HRV96     AATTTTAAGGTGTGGAAATAAATCTACAAGAAATGGCTCAAATTCGCAGGAAGTTTGAA
1423  145_HRV96b    AATTTTAAGGTGTGGAAATAAATCTACAAGAAATGGCTCAAATTCGCAGGAAGTTTGAA
1424  146_HRV96a    AATTTTAAGGTGTGGAAATAAATCTACAAGAAATGGCTCAAATTCGCAGGAAGTTTGAA
1425  90_HRV16a|    AGTTTCACTAAATGGAAGATAAACCTGCAAGAAATGGCACAAATTAGAAGAAAATTTGAA
```

FIG. D8 CONT'D 04-2.trace                                                                 9/20/2007 5:04 PM

```
1426  91_HRV16b|     AGTTTCACTAAATGGAAGATAAACCTGCAAGAAATGGCACAAATTAGAAGAAAATTTGAA
1427  92_1AYM_A      AGTTTCACTAAATGGAAGATAAACCTGCAAGAAATGGCACAAATTAGAAGAAAATTTGAA
1428  93_HRV81a|     AGCTTTACTAAATGGAAAATTAACTTACAAGAGATGGCACAGATTAGGAGAAAGTTTGAA
1429  94_HRV81b|     AGCTTTACTAAATGGAAAATTAACTTACAAGAGATGGCACAGATTAGGAGAAAGTTTGAA
1430  95_HRV81       AGCTTTACTAAATGGAAAATTAACTTACAAGAGATGGCACAGATTAGGAGAAAGTTTGAA
1431 147_HRV2        AATTTTACAGTGTGGGCTATTAATATACAAGAAATGGCTCAAATTAGAAGGAAATTTGAA
1432 148_HRV2a|      AATTTTACAGTGTGGGCTATTAATATACAAGAAATGGCTCAAATTAGAAGGAAATTTGAA
1433 149_HRV2b|      AATTTTACAGTGTGGGCTATTAATATACAAGAAATGGCTCAAATTAGAAGGAAATTTGAA
1434 150_HRV49a      AATTTCAAAGTATGGAACATCAATTTGCAAGAAATGGCCCAGATCAGAAGAAAATTTGAA
1435 151_HRV49b      AATTTCAAAGTATGGAACATCAATTTGCAAGAAATGGCCCAGATCAGAAGAAAATTTGAA
1436 152_HRV49       AATTTCAAAGTATGGAACATCAATTTGCAAGAAATGGCCCAGATCAGAAGAAAATTTGAA
1437 153_HRV23a      AATTTTAATACTTGGAATATTAATTTACAGGAAATGGCCCAAATCAGAAGAAAGTTTGAA
1438 154_HRV23b      AATTTTAATACTTGGAATATTAATTTACAGGAAATGGCCCAAATCAGAAGAAAGTTTGAA
1439 155_HRV23       AATTTTAATACTTGGAATATTAATTTACAGGAAATGGCCCAAATCAGAAGAAAGTTTGAA
1440 156_HRV30a      AACTTTACCACATGGAATATTAATCTTCAAGAAATGGCCCAAATTAGAAGAAAATTTGAG
1441 157_HRV30b      AACTTTACCACATGGAATATTAATCTTCAAGAAATGGCCCAAATTAGAAGAAAATTTGAG
1442 158_HRV30       AACTTTACCACATGGAATATTAATCTTCAAGAAATGGCCCAAATTAGAAGAAAATTTGAG
1443 159_HRV7        GGTTTCACTACATGGAAAATCAGCTTACAAGAAATGGCACAAATCAGAAGAAAGTTTGAA
1444 160_HRV7b|      GGTTTCACTACATGGAAAATCAGCTTACAAGAAATGGCACAAATCAGAAGAAAGTTTGAA
1445 161_HRV7a|      GGTTTCACTACATGGAAAATCAGCTTACAAGAAATGGCACAAATCAGAAGAAAGTTTGAA
1446 162_HRV88       GGATTTGTAACATGGAAGATTAGCTTGCAAGAAATGGCACAAATCAGGAGAAAATTTGAA
1447 163_HRV88a      GGATTTGTAACATGGAAGATTAGCTTGCAAGAAATGGCACAAATCAGGAGAAAATTTGAA
1448 164_HRV88b      GGATTTGTAACATGGAAGATTAGCTTGCAAGAAATGGCACAAATCAGGAGAAAATTTGAA
1449 165_HRV36a      GGATTCAAAACATGGAAGATTAGTCTTCAAGAAATGGCACAAATTAGAAGGAAATATGAA
1450 166_HRV36b      GGATTCAAAACATGGAAGATTAGTCTTCAAGAAATGGCACAAATTAGAAGGAAATATGAA
1451 167_HRV36       GGATTCAAAACATGGAAGATTAGTCTTCAAGAAATGGCACAAATTAGAAGGAAATATGAA
1452 168_HRV89a      GGATTCAAAACATGGAAGGTTAGTCTTCAAGAAATGGCACAAATCAGAAGAAAAATATGAA
1453 169_HRV89b      GGATTCAAAACATGGAAGGTTAGTCTTCAAGAAATGGCACAAATCAGAAGAAAATATGAA
1454 170_HRV89       GGATTCAAAACATGGAAGGTTAGTCTTCAAGAAATGGCACAAATCAGAAGAAAATATGAA
1455 171_HRV58       GGATACAAAACATGGAAAATTAGCCTTCAAGAGATGGCACAAATTAGAAGGAAATTTGAG
1456 172_HRV58a      GGATACAAAACATGGAAAATTAGCCTTCAAGAGATGGCACAAATTAGAAGGAAATTTGAG
1457 173_HRV58b      GGATACAAAACATGGAAAATTAGCCTTCAAGAGATGGCACAAATTAGAAGGAAATTTGAG
1458 174_HRV12a      AACTTTAAAACATGGAAGATAAATCTTAAGGAAATGGCCCAGATTAGAAGGAAAAATGAG
1459 175_HRV12b      AACTTTAAAACATGGAAGATAAATCTTAAGGAAATGGCCCAGATTAGAAGGAAAAATGAG
1460 176_HRV12       AACTTTAAAACATGGAAGATAAATCTTAAGGAAATGGCCCAGATTAGAAGGAAAAATGAG
1461 177_HRV78a      AATTTTACAACGTGGAAAATCAACTTACAGGAGATGGCCCAGATTAGAAGAAAGAATGAG
1462 178_HRV78b      AATTTTACAACGTGGAAAATCAACTTACAGGAGATGGCCCAGATTAGAAGAAAGAATGAG
1463 179_HRV78       AATTTTACAACGTGGAAAATCAACTTACAGGAGATGGCCCAGATTAGAAGAAAGAATGAG
1464 180_HRV20       AATTTCTCTCAGTGGAAGATCACAATCAAGGAAATGGCTCAAATCAGAAGAAAATGTGAG
1465 181_HRV20a      AATTTCTCTCAGTGGAAGATCACAATCAAGGAAATGGCTCAAATCAGAAGAAAATGTGAG
1466 182_HRV20b      AATTTCTCTCAGTGGAAGATCACAATCAAGGAAATGGCTCAAATCAGAAGAAAATGTGAG
1467 183_HRV68       AACTTCTCCCAATGGAAAATTACAATTAAGGAAATGGCTCAAATTAGAAGAAAGTGTGAA
1468 184_HRV68a      AACTTCTCCCAATGGAAAATTACAATTAAGGAAATGGCTCAAATTAGAAGAAAGTGTGAA
1469 185_HRV68b      AACTTCTCCCAATGGAAAATTACAATTAAGGAAATGGCTCAAATTAGAAGAAAGTGTGAA
1470 186_HRV28       AATTTTAGTAAATGGAATATCACTCTCAAAGAAATGGCCCAAATCAGAAGAAAGTGTGAA
1471 187_HRV28a      AATTTTAGTAAATGGAATATCACTCTCAAAGAAATGGCCCAAATCAGAAGAAAGTGTGAA
1472 188_HRV28b      AATTTTAGTAAATGGAATATCACTCTCAAAGAAATGGCCCAAATCAGAAGAAAGTGTGAA
1473 189_HRV53a      AACCACTCAGAATGGAAGATTACACTCAAAGAAATGGCCCAGATTAGAAGGAAATGTGAG
1474 190_HRV53b      AACCACTCAGAATGGAAGATTACACTCAAAGAAATGGCCCAGATTAGAAGGAAATGTGAG
1475 191_HRV53       AACCACTCAGAATGGAAGATTACACTCAAAGAAATGGCCCAGATTAGAAGGAAATGTGAG
1476 192_HRV46a      AACTTCTCAAAATGGAAAATAACACTGTTGGAAATGGCACAAATCAGAAGAAAGTGTGAA
1477 193_HRV46b      AACTTCTCAAAATGGAAAATAACACTGTTGGAAATGGCACAAATCAGAAGAAAGTGTGAA
1478 194_HRV46       AACTTCTCAAAATGGAAAATAACACTGTTGGAAATGGCACAAATCAGAAGAAAGTGTGAA
1479 195_HRV80a      AATTTTTCAAAGTGGAAAATAACATTAATGGAAATGGCACAAATTAGAAGAAAGTGTGAG
1480 196_HRV80b      AATTTTTCAAAGTGGAAAATAACATTAATGGAAATGGCACAAATTAGAAGAAAGTGTGAG
1481 197_HRV80       AATTTTTCAAAGTGGAAAATAACATTAATGGAAATGGCACAAATTAGAAGAAAGTGTGAG
1482 198_HRV51       AATTTCTCTACATGGAAAATTACACTCAAAGAAATGGCTCAAATTAGAAGAAAGTGTGAA
1483 199_HRV51a      AATTTCTCTACATGGAAAATTACACTCAAAGAAATGGCTCAAATTAGAAGAAAGTGTGAA
1484 200_HRV51b      AATTTCTCTACATGGAAAATTACACTCAAAGAAATGGCTCAAATTAGAAGAAAGTGTGAA
1485 201_HRV65a      AATTTCTCTGCTTGGGAAATTACACTCAAGGAAATGGCTCAAATTAGGAGAAAGTGTGAA
1486 202_HRV65b      AATTTCTCTGCTTGGGAAATTACACTCAAGGAAATGGCTCAAATTAGGAGAAAGTGTGAA
1487 203_HRV65       AATTTCTCTGCTTGGGAAATTACACTCAAGGAAATGGCTCAAATTAGGAGAAAGTGTGAA
1488 204_HRV71a      AATCTCTCAAAGTGGCAGATTACACTCAAAGAAATGGCTCAGATCAGGAGGAAATGTGAA
1489 205_HRV71b      AATCTCTCAAAGTGGCAGATTACACTCAAAGAAATGGCTCAGATCAGGAGGAAATGTGAA
1490 206_HRV71       AATCTCTCAAAGTGGCAGATTACACTCAAAGAAATGGCTCAGATCAGGAGGAAATGTGAA
```

FIG. D8 CONT'D

04-2.trace                                                                9/20/2007 5:04 PM

```
1491 207_HRV8     AGTTTCAGGACCTGGGGAATAAACATACAAGAGATGTCACAAATTAGAAGGAAATTTGAG
1492 208_HRV95    AATTTCAGGACCTGGGGAATAAACATACAAGAGATGTCACAAATTAGAAGGAAATTTGAA
1493 209_HRV45    AATTACAAAAATTGGGCAATTAGTTTACAAGAAATGTCACAAATTAGGAGGAAATTTGAA
1494 210_HRV45a   AATTACAAAAATTGGGCAATTAGTTTACAAGAAATGTCACAAATTAGGAGGAAATTTGAA
1495 211_HRV45b   AATTACAAAAATTGGGCAATTAGTTTACAAGAAATGTCACAAATTAGGAGGAAATTTGAA
1496 GROUP_1      ------------TGG----T-A---T----GA-ATG-C-CA--T--G--G-AA----GA-
1497
1498 1_HRV1A1|d   TTGTTTACATATGTCAGGTTTGACTCAGAAATAACCTTGG-TGCCTTGTATTGCTGGTAG
1499 2_HRV1A2|d   TTGTTTACATATGTCAGGTTTGACTCAGAAATAACCTTGG-TGCCTTGTATTGCTGGTAG
1500 3_HRV1A|cD   TTGTTTACATATGTCAGGTTTGACTCAGAAATAACCTTGG-TGCCTTGTATTGCTGGTAG
1501 4_HRV1B1|d   CTATTTACTTATGTTAGGTTTGATTCAGAAGTAACTTTAG-TACCCTGTATTGCTGGTAG
1502 5_HRV1B2|d   CTATTTACTTATGTTAGGTTTGATTCAGAAGTAACTTTAG-TACCCTGTATTGCTGGTAG
1503 6_HRV1B      CTATTTACTTATGTTAGGTTTGATTCAGAAGTAACTTTAG-TACCCTGTATTGCTGGTAG
1504 7_HRV40a|d   TTCTTTACATATGCTAGGTTTGATTCAGAAATTACCTTAG-TTCCTTGTATAGCCGGTAA
1505 8_HRV40b|d   TTCTTTACATATGCTAGGTTTGATTCAGAAATTACCTTAG-TTCCTTGTATAGCCGGTAA
1506 9_HRV40      TTCTTTACATATGCTAGGTTTGATTCAGAAATTACCTTAG-TTCCTTGTATAGCCGGTAA
1507 10_HRV85     TTCTTTACTTACACTAGATTTGATTCAGAAATCACTTTAG-TCCCTTGTATAGCTGGAAA
1508 11_HRV85a|   TTCTTTACTTACACTAGATTTGATTCAGAAATCACTTTAG-TCCCTTGTATAGCTGGAAA
1509 12_HRV85b|   TTCTTTACTTACACTAGATTTGATTCAGAAATCACTTTAG-TCCCTTGTATAGCTGGAAA
1510 13_HRV56a|   TTCTTTACTTATGTCAGATTTGATTCAGAGGTTACTTTGG-TACCTTGTGTAGCCGGCAA
1511 14_HRV56b|   TTCTTTACTTATGTCAGATTTGATTCAGAGGTTACTTTGG-TACCTTGTGTAGCCGGCAA
1512 15_HRV56     TTCTTTACTTATGTCAGATTTGATTCAGAGGTTACTTTGG-TACCTTGTGTAGCCGGCAA
1513 16_HRV54     TTCTTTACTTATGTTAGGTTTGATTCAGAAATTACTCTAG-TCCCCTGTATAGCTGGTAA
1514 17_HRV98     TTCTTTACTTATGTTAGATTTCAGAAGTTACCTTAG-TTCCTTGCATAGCTGGCAA
1515 18_HRV59a|   TTCTTCACATATGTTAGATTTGACTCAGAAATCACTTTGG-TGCCTTGCATAGCTGGAAA
1516 19_HRV59b|   TTCTTCACATATGTTAGATTTGACTCAGAAATCACTTTGG-TGCCTTGCATAGCTGGAAA
1517 20_HRV59     TTCTTCACATATGTTAGATTTGACTCAGAAATCACTTTGG-TGCCTTGCATAGCTGGAAA
1518 21_HRV63     TTCTTCACATATGTCAGATTTGATTCAGAAGTCACTCTTG-TACCATGTATAGCAGGAAA
1519 22_HRV63b|   TTCTTCACATATGTCAGATTTGATTCAGAAGTCACTCTTG-TACCATGTATAGCAGGAAA
1520 23_HRV63a|   TTCTTCACATATGTCAGATTTGATTCAGAAGTCACTCTTG-TACCATGTATAGCAGGAAA
1521 24_HRV39     ATGTTCACCTATGTTAGATTTGACTCAGAGATTACTTTAG-TCCCATGCATAGCTGGAAG
1522 25_HRV39a|   ATGTTCACCTATGTTAGATTTGACTCAGAGATTACTTTAG-TCCCATGCATAGCTGGAAG
1523 26_HRV39b|   ATGTTCACCTACGTTAGATTTGACTCAGAGATTACTTTAG-TCCCATGCATAGCTGGAAG
1524 27_HRV10a|   ATGTTTACATATGTTAGATTTGACTCAGAAGTCACTTTAG-TACCTTGCATCGCAGGCAA
1525 28_HRV10b|   ATGTTTACATATGTTAGATTTGACTCAGAAGTCACTTTAG-TACCTTGCATCGCAGGCAA
1526 29_HRV10     ATGTTTACATATGTTAGATTTGACTCAGAAGTCACTTTAG-TACCTTGCATCGCAGGCAA
1527 30_HRV100a   ATGTTTACATATGTCAGATTTGACTCAGAAATCACATTGG-TACCCTGTATTGCAGGAAA
1528 31_HRV100b   ATGTTTACATATGTCAGATTTGACTCAGAAATCACATTGG-TACCCTGTATTGCAGGAAA
1529 32_HRV100    ATGTTTACATATGTCAGATTTGACTCAGAAATCACATTGG-TACCCTGTATTGCAGGAAA
1530 33_HRV66     ATGTTCACATATGTTAGGTTTGATTCTGAAATTACATTAG-TCCCATGCATTGCAGGAAA
1531 34_HRV66b|   ATGTTCACATATGTTAGGTTTGATTCTGAAATTACATTAG-TCCCATGCATTGCAGGAAA
1532 35_HRV66a|   ATGTTCACATATGTTAGGTTTGATTCTGAAATTACATTAG-TCCCATGCATTGCAGGAAA
1533 36_HRV77a|   ATGTTTACATATGTAAGATTTGATTCAGAAATTACATTGG-TCCCATGTATTGCTGGAAA
1534 37_HRV77b|   ATGTTTACATATGTAAGATTTGATTCAGAAATTACATTGG-TCCCATGTATTGCTGGAAA
1535 38_HRV77     ATGTTTACATATGTAAGATTTGATTCAGAAATTACATTGG-TCCCATGTATTGCTGGAAA
1536 39_HRV62a    ATGTTTACATATGTAAGATTTGATTCAGAAATAACCCTGG-TTCCATCTATTGCAGGACG
1537 40_HRV62b    ATGTTTACATATGTAAGATTTGATTCAGAAATAACCCTGG-TTCCATCTATTGCAGGACG
1538 41_HRV25     ATGTTTACATATGTGAGATTTCAGAGATAACCCTAG-TTCCATCTATTGCAGGACG
1539 42_HRV29a    ATGTTCACATATGTGAGATTTGACTCAGAAATAACCCTCTG-TTCTTTGCATTGCAGGACG
1540 43_HRV29b    ATGTTCACATATGTGAGATTTGACTCAGAAATAACCCTGG-TTCCATGCATTGCAGGACG
1541 44_HRV44a    ATGTTCACATATGTGAGATTTGATTCGGAAATAACTCTAG-TTCCATGCATTGCAGGACA
1542 45_HRV44b    ATGTTCACATATGTGAGATTTGATTCAGAAATAACTCTAG-TTCCATGCATTGCAGGACG
1543 46_HRV31     ATGTTCACATATGTAAGATTTGATTCAGAAGTCACCATAG-TTCCATGCATTGCAGGACA
1544 47_HRV31a|   ATGTTCACATATGTAAGATTTGATTCAGAAGTGACCATAG-TTCCATGCATTGCAGGACA
1545 48_HRV31b|   ATGTTCACATATGTAAGATTTGATTCAGAAGTGACCATAG-TTCCATGCATTGCAGGACA
1546 49_HRV47     ATGTTCACATATGTAAGATTTGATTCAGAAGTAACCATGG-TTCCATGTATTGCAGGGTA
1547 50_HRV47a|   ATGTTTACATATGTAAGATTTGATTCAGAAGTAACCATGG-TTCCATGTATTGCAGGGTA
1548 51_HRV47b|   ATGTTTACATATGTAAGATTTGATTCAGAAGTAACCATGG-TTCCATGTATTGCAGGGTA
1549 52_HRV11     ATGTTCACATACACTAGATTTGATTCAGAGATCACATTGG-TGCCTTGTATAGCTGCAAA
1550 53_HRV11b|   ATGTTCACATACACTAGATTTGATTCAGAGATCACATTGG-TGCCTTGTATAGCTGCAAA
1551 54_HRV11a|   ATGTTCACATACACTAGATTTGATTCAGAGATCACATTGG-TGCCTTGTATAGCTGCAAA
1552 55_HRV76     ATGTTTACATATACTAGATTTGATTCAGAAGTTACTCTAG-TTCCTTCTATAGCTGCCAA
1553 56_HRV76b|   ATGTTTACATATACTAGATTTGATTCAGAAGTTACTCTAG-TTCCTTCTATAGCTGCCAA
1554 57_HRV76a|   ATGTTTACATATACTAGATTTGATTCAGAAGTTACTCTAG-TTCCTTCTATAGCTGCCAA
1555 58_HRV33     ATGTTTACATATGCCAGATTTGATTCAGAGATCACCCTAG-TCCCTTCTATAGCTGCCCA
```

FIG. D8 CONT'D

```
04-2.trace                                                                                    9/20/2007 5:04 PM 1556  59_HRV33b|      ATGTTTACATATGCCAGATTTGATTCAGAGATCACCCTAG-TCCCTTCTATAGCTGCCCA
1557  60_HRV33a|      ATGTTTACATATGCCAGATTTGATTCAGAGATCACCCTAG-TCCCTTCTATAGCTGCCCA
1558  61_HRV24a|      TTATTCACATATACTAGATTTGACTCTGAGATTACAATAG-TTCCATCCATAGCTGGCAA
1559  62_HRV24b|      TTATTCACATATACTAGATTTGACTCTGAGATTACAATAG-TTCCATCCATAGCTGGCAA
1560  63_HRV24       TTATTCACATATACTAGATTTGACTCTGAGATTACAATAG-TTCCATCCATAGCTGGCAA
1561  64_HRV90       TTGTTTACATATGCTAGATTTGATTCTGAAATTACAATAG-TACCATCTATAGCTGGCAA
1562  65_HRV90a|     TTGTTTACATATGCTAGATTTGATTCTGAAATTACAATAG-TACCATCTATAGCTGGCAA
1563  66_HRV90b|     TTGTTTACATATGCTAGATTTGATTCTGAAATTACAATAG-TACCATCTATAGCTGGCAA
1564  67_HRV34       ATGTTCACCTACGTCAGATTTGATTCTGAAGTCACCCTAG-TACCATCAATAGCGGCCAA
1565  68_HRV34b|     ATGTTCACCTACGTCAGATTTGATTCTGAAGTCACCCTAG-TACCATCAATAGCGGCCAA
1566  69_HRV34a|     ATGTTCACCTACGTCAGATTTGATTCTGAAGTCACCCTAG-TACCATCAATAGCGGCCAA
1567  70_HRV50a|     ATGTTCACCTATGTGAGGTTTAATTCTGAGGTCACATTAG-TACCATCCATAGCTGCCAA
1568  71_HRV50b|     ATGTTCACCTATGTGAGGTTTAATTCTGAGGTCACATTAG-TACCATCCATAGCTGCCAA
1569  72_HRV50       ATGTTCACCTATGTGAGGTTTAATTCTGAGGTCACATTAG-TACCATCCATAGCTGCCAA
1570  73_HRV18a|     ATGTTTACATATGTTAGATTTGATTCAGAAATTACACTAG-TACCATCTGTAGCTGCTAA
1571  74_HRV18b|     ATGTTTACATATGTTAGATTTGATTCAGAAATTACACTAG-TACCATCTGTAGCTGCTAA
1572  75_HRV18       ATGTTTACATATGTTAGATTTGATTCAGAAATTACACTAG-TACCATCTGTAGCTGCTAA
1573  76_HRV55       ATGTTCACCTATACTAGATTTGATTCAGAAGTTACATTAG-TACCCTCTATTGCTGCAAA
1574  77_HRV55b|     ATGTTCACCTATACTAGATTTGATTCAGAAGTTACATTAG-TACCCTCTATTGCTGCAAA
1575  78_HRV55a|     ATGTTCACCTATACTAGATTTGATTCAGAAGTTACATTAG-TACCCTCTATTGCTGCAAA
1576  79_HRV57       CTATTTACATATGTTAGGTTTGATTCTGAAGTTACATTAG-TTCCCTCCATAGCTGCTCA
1577  80_HRV57a|     CTATTTACATATGTTAGGTTTGATTCTGAAGTTACATTAG-TTCCCTCCATAGCTGCTCA
1578  81_HRV57b|     CTATTTACATATGTTAGGTTTGATTCTGAAGTTACATTAG-TTCCCTCCATAGCTGCTCA
1579  82_HRV21       ATGTTCACCTATACTAGATTTGATTCAGAAATAACTTTGG-TGCCGTCAATTGCAGCTAG
1580  83_HRVHan      ATGTTCACCTATACTAGATTTGATTCAGAAATAACTTTGG-TACCGTCAATTGCAGCTAA
1581  84_HRV43       TTGTTCACATACTTAAGGTTTGATTCTGAAATTACCCTTG-TTCCTTGCATTGCAGCAAA
1582  85_HRV43b|     TTGTTCACATACTTAAGGTTTGATTCTGAAATTACCCTTG-TTCCTTGCATTGCAGCAAA
1583  86_HRV43a|     TTGTTCACATACTTAAGGTTTGATTCTGAAATTACCCTTG-TTCCTTGCATTGCAGCAAA
1584  87_HRV75       TTATTTACATATCTTAGATTTGATTCAGAGGTTACTCTGG-TGCCATGCATTGCAGCTAA
1585  88_HRV75b|     TTATTTACATATCTTAGATTTGATTCAGAGGTTACTCTGG-TGCCATGCATTGCAGCTAA
1586  89_HRV75a|     TTATTTACATATCTTAGATTTGATTCAGAGGTTACTCTGG-TGCCATGCATTGCAGCTAA
1587  96_HRV9a|d     TTGTTTACATATGCAAGATTTGACTCTGAAATAACATTGG-TCCCGTGTATAGCAGCAGA
1588  97_HRV9b|d     TTGTTTACATATGCAAGATTTGACTCTGAAATAACATTGG-TCCCGTGTATAGCAGCAGA
1589  98_HRV9        TTGTTTACATATGCAAGATTTGACTCTGAAATAACATTGG-TCCCGTGTATAGCAGCAGA
1590  99_HRV32       TTGTTTACATACACAAGGTTTGATTCTGAAATAACATTAG-TACCTTGTATAGCTGCAGA
1591  100_HRV32a     TTGTTTACATACACAAGGTTTGATTCTGAAATAACATTAG-TACCTTGTATAGCTGCAGA
1592  101_HRV32b     TTGTTTACATACACAAGGTTTGATTCTGAAATAACATTAG-TACCTTGTATAGCTGCAGA
1593  102_HRV67      CTACTCACATACAAGATTTGATTCTGAAATAACTGG-TACCATGCATAGCTGCAGA
1594  103_HRV67a     CTATTCACATATACAAGATTTGATTCTGAGATAACACTGG-TACCATGCATAGCTGCAGA
1595  104_HRV67b     CTATTCACATATACAAGATTTGATTCTGAGATAACACTGG-TACCATGCATAGCTGCAGA
1596  105_HRV15      TTATTCACATATGTAAGGTTTGATTCAGAAATAACACTTG-TACCATGCATTGCAGCAAA
1597  106_HRV15a     TTATTCACATATGTAAGGTTTGATTCAGAAATAACACTTG-TACCATGCATTGCAGCAAA
1598  107_HRV15b     TTATTCACATATGTAAGGTTTGATTCAGAAATAACACTTG-TACCATGCATTGCAGCAAA
1599  108_HRV74a     TTGTTCACATATGTTAGATTTGACTCAGAAGTGACATTAG-TTCCATGCATTGCTGCTAA
1600  109_HRV74b     TTGTTCACATATGTTAGATTTGACTCAGAAGTGACATTAG-TTCCATGCATTGCTGCTAA
1601  110_HRV74      TTGTTCACATATGTTAGATTTGACTCAGAAGTGACATTAG-TTCCATGCATTGCTGCTAA
1602  111_HRV38a     ATGTTTACATATGTGAGATTTGATTCAGAAGTTACATTAG-TCCCATGTATAGCAGCACA
1603  112_HRV38b     ATGTTTACATATGTGAGATTTGATTCAGAAGTTACATTAG-TCCCATGTATAGCAGCACA
1604  113_HRV38      ATGTTTACATATGTGAGATTTGATTCAGAAGTTACATTAG-TCCCATGTATAGCAGCACA
1605  114_HRV60      TTATTTACATATGTAAGATTTGATTCAGAATTGACTCTGG-TCCCATGCATAGCAGCAAA
1606  115_HRV60a     TTATTTACATATGTAAGATTTGATTCAGAATTGACTCTGG-TCCCATGCATAGCAGCAAA
1607  116_HRV60b     TTATTTACATATGTAAGATTTGATTCAGAATTGACTCTGG-TCCCATGCATAGCAGCAAA
1608  117_HRV64a     TTATTTACATATGTTAGATTTGATTCTGAAATAACCTTAG-TGCCTTGCATATCTTCTCA
1609  118_HRV64b     TTATTTACATATGTTAGATTTGATTCTGAAATAACCTTAG-TGCCTTGCATATCTTCTCA
1610  119_HRV64      TTATTTACATATGTTAGATTTGATTCTGAAATAACCTTAG-TGCCTTGCATATCTTCTCA
1611  120_HRV94a     CTATTTACTTATGTTAGATTTGATTCAGAAATAACTTTAG-TACCTTGCATATCATCTCA
1612  121_HRV94b     CTATTTACTTATGTTAGATTTGATTCAGAAATAACTTTAG-TACCTTGCATATCATCTCA
1613  122_HRV94      CTATTTACTTATGTTAGATTTGATTCAGAAATAACTTTAG-TACCTTGCATATCATCTCA
1614  123_HRV22      CTATTTACATATCTCAGGTTTGATTCTGAAATCACTTTGG-TACCATGCATTGCTTCACA
1615  124_HRV22a     CTATTTACATATCTCAGGTTTGATTCTGAAATCACTTTGG-TACCATGCATTGCTTCACA
1616  125_HRV22b     CTATTTACATATCTCAGGTTTGATTCTGAAATCACTTTGG-TACCATGCATTGCTTCACA
1617  126_HRV82      CTTTTCACATATGTGAGATTTGATTCAGAAATTACTTTAG-TGCCTTGCATAGCCTCTCA
1618  127_HRV82b     CTTTTCACATATGTGAGATTTGATTCAGAAATTACTTTAG-TGCCTTGCATAGCCTCTCA
1619  128_HRV82a     CTTTTCACATATGTGAGATTTGATTCAGAAATTACTTTAG-TGCCTTGCATAGCCTCTCA
1620  129_HRV19      CTTTTCACTTACCTCAGATTTGATTCAGAGGTAACATTAG-TCCCTTGCATAGCTGCTAA
```

FIG. D8 CONT'D 04-2.trace                                                                                              9/20/2007 5:04 PM

```
1621  130_HRV19a      CTTTTCACTTACCTCAGATTTGATTCAGAGGTAACATTAG-TCCCTTGCATAGCTGCTAA
1622  131_HRV19b      CTTTTCACTTACCTCAGATTTGATTCAGAGGTAACATTAG-TCCCTTGCATAGCTGCTAA
1623  132_HRV13       TTGTTCACCTATGTAAGATTTGATTCAGAAATAACAATTG-TGCCATGTATAGCCGGGCA
1624  133_HRV13a      TTGTTCACCTATGTAAGATTTGATTCAGAAATAACAATTG-TGCCATGTATAGCCGGGCA
1625  134_HRV13b      TTGTTCACCTATGTAAGATTTGATTCAGAAATAACAATTG-TGCCATGTATAGCCGGGCA
1626  135_HRV41       TTTTTTACGTATGTTAGATTTGACTCAGAAATAACAATTG-TGCCAAGTATAGCTGGACA
1627  136_HRV41a      TTTTTTACGTATGTTAGATTTGACTCAGAAATAACAATTG-TGCCAAGTATAGCTGGACA
1628  137_HRV41b      TTTTTTACGTATGTTAGATTTGACTCAGAAATAACAATTG-TGCCAAGTATAGCTGGACA
1629  138_HRV73       TTATTCACCTATGTAAGATTTGATTCAGAAGTGACAATTG-TACCATGTATAGCTGGTCA
1630  139_HRV73b      TTATTCACCTATGTAAGATTTGATTCAGAAGTGACAATTG-TACCATGTATAGCTGGTCA
1631  140_HRV73a      TTATTCACCTATGTAAGATTTGATTCAGAAGTGACAATTG-TACCATGTATAGCTGGTCA
1632  141_HRV61       TTGTTCACATATGCTAGATTTGATTCAGAGATTACAATTG-TACCTTGTGTTGCTGGGCA
1633  142_HRV61a      TTGTTCACATATGCTAGATTTGATTCAGAGATTACAATTG-TACCTTGTGTTGCTGGGCA
1634  143_HRV61b      TTGTTCACATATGCTAGATTTGATTCAGAGATTACAATTG-TACCTTGTGTTGCTGGGCA
1635  144_HRV96       CTGTTCACTTATGCTAGATTTGATTCAGAGATAACAATTG-TTCCATGTGTTGCTGTGCA
1636  145_HRV96b      CTGTTCACTTATGCTAGATTTGATTCAGAGATAACAATTG-TTCCATGTGTTGCTGTGCA
1637  146_HRV96a      CTGTTCACTTATGCTAGATTTGATTCAGAGATAACAATTG-TTCCATGTGTTGCTGTGCA
1638  90_HRV16a|      ATGTTTACTTATGCAAGATTTGACTCTGAAATTACTATGG-TACCAAGTGTAGCAGCCAA
1639  91_HRV16b|      ATGTTTACTTATGCAAGATTTGACTCTGAAATTACTATGG-TACCAAGTGTAGCAGCCAA
1640  92_1AYM_A       ATGTTTACTTATGCAAGATTTGACTCTGAAATTACTATGG-TACCAAGTGTAGCAGCCAA
1641  93_HRV81a|      ATGTTCACATACACTAGATTTAACTCTGAGATTACACTGG-TACCAAGTATTGCAAACAA
1642  94_HRV81b|      ATGTTCACATACACTAGATTTAACTCTGAGATTACACTGG-TACCAAGTATTGCAAACAA
1643  95_HRV81        ATGTTCACATACACTAGATTTAACTCTGAGATTACACTGG-TACCAAGTATTGCAAACAA
1644  147_HRV2        TTGTTCACCTATACTAGGTTTGATTCTGAAATAACCCTAG-TTCCATGCATTTCCGCCCT
1645  148_HRV2a|      TTGTTCACCTATACTAGGTTTGATTCTGAAATAACCCTAG-TTCCATGCATTTCCGCCCT
1646  149_HRV2b|      TTGTTCACCTATACTAGGTTTGATTCTGAAATAACCCTAG-TTCCATGCATTTCCGCCCT
1647  150_HRV49a      CTGTTTACTTACACTAGATTCGATTCTGAAATAACCTTGG-TTCCATGCATTTCTGCACT
1648  151_HRV49b      CTGTTTACTTACACTAGATTCGATTCTGAAATAACCTTGG-TTCCATGCATTTCTGCACT
1649  152_HRV49       CTGTTTACTTACACTAGATTCGATTCTGAAATAACCTTGG-TTCCATGCATTTCTGCACT
1650  153_HRV23a      CTGTTTACTTACACTAGATTTGATTCTGAAATTACTTTGG-TTCCATGCATTTCTGCTCT
1651  154_HRV23b      CTGTTTACTTACACTAGATTTGATTCTGAAATTACTTTGG-TTCCATGCATTTCTGCTCT
1652  155_HRV23       CTGTTTACTTACACTAGATTTGATTCTGAAATTACTTTGG-TTCCATGCATTTCTGCTCT
1653  156_HRV30a      CTATTCACTTACACTAGATTTGATTCTGAGATAACCTTGG-TTCCGTGTATTTCAGCTCT
1654  157_HRV30b      CTATTCACTTACACTAGATTTGATTCTGAGATAACCTTGG-TTCCGTGTATTTCAGCTCT
1655  158_HRV30       CTATTCACTTACACTAGATTTGATTCTGAGATAACCTTGG-TTCCGTGTATTTCAGCTCT
1656  159_HRV7        CTATTCACATACACTAGATTTGATTCTGAGATAACAATAG-TCACAGCAGCAGCAGCACA
1657  160_HRV7b|      CTATTCACATACACTAGATTTGATTCTGAGATAACAATAG-TCACAGCAGCAGCAGCACA
1658  161_HRV7a|      CTATTCACATACACTAGATTTGATTCTGAGATAACAATAG-TCACAGCAGCAGCAGCACA
1659  162_HRV88       TTGTTTACATACACTAGATTTGACTCAGAAATAACAATAG-TCACAGCAGCTGCAGCACA
1660  163_HRV88a      TTGTTTACATACACTAGATTTGACTCAGAAATAACAATAG-TCACAGCAGCTGCAGCACA
1661  164_HRV88b      TTGTTTACATACACTAGATTTGACTCAGAAATAACAATAG-TCACAGCAGCTGCAGCACA
1662  165_HRV36a      TTGTTTACATACACAAGATTTGACTCAGAAATAACAATAG-TCACCGCAGCTGCAGTGCA
1663  166_HRV36b      TTGTTTACATACACAAGATTTGACTCAGAAATAACAATAG-TCACCGCAGCTGCAGTGCA
1664  167_HRV36       TTGTTTACATACACAAGATTTGACTCAGAAATAACAATAG-TCACCGCAGCTGCAGTGCA
1665  168_HRV89a      TTATTCACATATACAAGATTTGATTCAGAGATAACAATAG-TCACTGCAGCCGCAGCTCA
1666  169_HRV89b      TTATTCACATATACAAGATTTGATTCAGAGATAACAATAG-TCACTGCAGCCGCAGCTCA
1667  170_HRV89       TTATTCACATATACAAGATTTGATTCAGAGATAACAATAG-TCACTGCAGCCGCAGCTCA
1668  171_HRV58       TTGTTTACATATACAAGATTTGACTCAGAGATTACAATAG-TCACTGCAGCAGCTGCTCA
1669  172_HRV58a      TTGTTTACATATACAAGATTTGACTCAGAGATTACAATAG-TCACTGCAGCAGCTGCTCA
1670  173_HRV58b      TTGTTTACATATACAAGATTTGACTCAGAGATTACAATAG-TCACTGCAGCAGCTGCTCA
1671  174_HRV12a      CTTTTCACCTACTTAAGGTTTGATTCTGAAATCACCATTGTTCCAAGCAATG-CAGCAAT
1672  175_HRV12b      CTTTTCACCTACTTAAGGTTTGATTCTGAAATCACCATTGTTCCAAGCAATG-CAGCAAT
1673  176_HRV12       CTTTTCACCTACTTAAGGTTTGATTCTGAAATCACCATTGTTCCAAGCAATG-CAGCAAT
1674  177_HRV78a      ATGTTCACATATCTCAGATTTGATTCAGAAATCACTCTTG-TGTGTGCAGTGGCCTCACA
1675  178_HRV78b      ATGTTCACATATCTCAGATTTGATTCAGAAATCACTCTTG-TGTGTGCAGTGGCCTCACA
1676  179_HRV78       ATGTTCACATATCTCAGATTTGATTCAGAAATCACTCTTG-TGTGTGCAGTGGCCTCACA
1677  180_HRV20       CTCTTTACATACCTCAGATTTGATTCTGAGATTACAATAG-TAGCAACAGTAGCTGCACT
1678  181_HRV20a      CTCTTTACATACCTCAGATTTGATTCTGAGATTACAATAG-TAGCAACAGTAGCTGCACT
1679  182_HRV20b      CTCTTTACATACCTCAGATTTGATTCTGAGATTACAATAG-TAGCAACAGTAGCTGCACT
1680  183_HRV68       CTATTCACATACCTTAGGTTTGACTCTGAGATTACAATAG-TAGCAACAATAGCTGCTCT
1681  184_HRV68a      CTATTCACATACCTTAGGTTTGACTCTGAGATTACAATAG-TAGCAACAATAGCTGCTCT
1682  185_HRV68b      CTATTCACATACCTTAGGTTTGACTCTGAGATTACAATAG-TAGCAACAATAGCTGCTCT
1683  186_HRV28       ATGTTTACATATCTCAGATTTGATTCTGAAATTACTATAG-TGGTGTCAGTTGCAAGTAA
1684  187_HRV28a      ATGTTTACATATCTCAGATTTGATTCTGAAATTACTATAG-TGGTGTCAGTTGCAAGTAA
1685  188_HRV28b      ATGTTTACATATCTCAGATTTGATTCTGAAATTACTATAG-TGGTGTCAGTTGCAAGTAA
```

FIG. D8 CONT'D 04-2.trace                                                                9/20/2007 5:04 PM

```
1686 189_HRV53a     ATGTTCACATATCTTAGATTTGATTCAGAAATAACTATAG-TGGTATCAGTGGCTAGTAA
1687 190_HRV53b     ATGTTCACATATCTTAGATTTGATTCAGAAATAACTATAG-TGGTATCAGTGGCTAGTAA
1688 191_HRV53      ATGTTCACATATCTTAGATTTGATTCAGAAATAACTATAG-TGGTATCAGTGGCTAGTAA
1689 192_HRV46a     CTTTTTACATATCTCAGATTTGATTCAGAAATAACAATAG-TCACCACATTGGCAGGCCA
1690 193_HRV46b     CTTTTTACATATCTCAGATTTGATTCAGAAATAACAATAG-TCACCACATTGGCAGGCCA
1691 194_HRV46      CTTTTTACATATCTCAGATTTGATTCAGAAATAACAATAG-TCACCACATTGGCAGGCCA
1692 195_HRV80a     CTTTTCACTTACCTCAGATTTGACTCAGAAATAACAATAG-TAACTACCTTAGCAGGACA
1693 196_HRV80b     CTTTTCACTTACCTCAGATTTGACTCAGAAATAACAATAG-TAACTACCTTAGCAGGACA
1694 197_HRV80      CTTTTCACTTACCTCAGATTTGACTCAGAAATAACAATAG-TAACTACCTTAGCAGGACA
1695 198_HRV51      CTTTTCACATACTTAAGATTTGATTCAGAGATCACTATAG-TTGCTACCATTGCTGGACA
1696 199_HRV51a     CTTTTCACATACTTAAGATTTGATTCAGAGATCACTATAG-TTGCTACCATTGCTGGACA
1697 200_HRV51b     CTTTTCACATACTTAAGATTTGATTCAGAGATCACTATAG-TTGCTACCATTGCTGGACA
1698 201_HRV65a     CTCTTCACCTATTTGCGCTTTGACTCAGAAATTACCATAG-TGGCTACTATAGCTGGACA
1699 202_HRV65b     CTCTTCACCTATTTGCGCTTTGACTCAGAAATTACCATAG-TGGCTACTATAGCTGGACA
1700 203_HRV65      CTCTTCACCTATTTGCGCTTTGACTCAGAAATTACCATAG-TGGCTACTATAGCTGGACA
1701 204_HRV71a     CTCTTCACATACCTGCGCTTTGACTCAGAAATTG-TAGCTACACTAGCAGGGCA
1702 205_HRV71b     CTCTTCACATACCTGCGCTTTGATTCAGAGATAACAATTG-TAGCTACACTAGCAGGGCA
1703 206_HRV71      CTCTTCACATACCTGCGCTTTGATTCAGAGATAACAATTG-TAGCTACACTAGCAGGGCA
1704 207_HRV8       ATGTTCACTTATGTAAGATTTGATTCAGAGATAACAATTG-TACCATGTATTGCAGCTAT
1705 208_HRV95      ATGTTCACTTATGTAAGATTTGATTCAGAGATAACAATTG-TACCATGTATTGCAGCTAT
1706 209_HRV45      ATGTTTACATATGTCAGATTTGATTCCGAAATAACAATAG-TACCATGTGTTGCTGCCAC
1707 210_HRV45a     ATGTTTACATATGTCAGATTTGATTCCGAAATAACAATAG-TACCATGTGTTGCTGCCAC
1708 211_HRV45b     ATGTTTACATATGTCAGATTTGATTCCGAAATAACAATAG-TACCATGTGTTGCTGCCAC
1709 GROUP_1        -T-TT-AC-TA-----G-TT--A-TC-GA--T-AC--T-G-T----------C------
1710
1711 1_HRV1A1|d     AGGAGACGACATTGGACATATTGTAATGCAATATATGTATGTTCCTCCAGGAGCTCCAAT
1712 2_HRV1A2|d     AGGAGACGACATTGGACATATTGTAATGCAATATATGTATGTTCCTCCAGGAGCTCCAAT
1713 3_HRV1A|cD     AGGAGACGACATTGGACATATTGTAATGCAATATATGTATGTTCCTCCAGGAGCTCCAAT
1714 4_HRV1B1|d     AGGAGATGACATTGGTCATGTTGTAATGCAGTATATGTATGTTCCCCAGGAGCTCCAAT
1715 5_HRV1B2|d     AGGAGATGACATTGGTCATGTTGTAATGCAGTATATGTATGTTCCCCAGGAGCTCCAAT
1716 6_HRV1B        AGGAGATGACATTGGTCATGTTGTAATGCAGTATATGTATGTTCCCCAGGAGCTCCAAT
1717 7_HRV40a|d     GGGTGAAGACATTGGACACATTGTGATGCAATATATGTATGTACCCCCTGGCGCACCCAT
1718 8_HRV40b|d     GGGTGAAGACATTGGACACATTGTGATGCAATATATGTATGTACCCCCTGGCGCACCCAT
1719 9_HRV40        GGGTGAAGACATTGGACACATTGTGATGCAATATATGTATGTACCCCCTGGCGCACCCAT
1720 10_HRV85       GGGTGATGATATTGGACACATTGTAATGCAGTATATGTATGTGCCCCCCGGAGCACCAAT
1721 11_HRV85a|     GGGTGATGATATTGGACACATTGTAATGCAGTATATGTATGTGCCCCCCGGAGCACCAAT
1722 12_HRV85b|     GGGTGATGATATTGGACACATTGTAATGCAGTATATGTATGTGCCCCCCGGAGCACCAAT
1723 13_HRV56a|     GGGAGATGATATTGGACACATTGTAATGCAATACATGTATGTGCCTCCTGGTGCACCACT
1724 14_HRV56b|     GGGAGATGATATTGGACACATTGTAATGCAATACATGTATGTGCCTCCTGGTGCACCACT
1725 15_HRV56       GGGAGATGATATTGGACACATTGTAATGCAATACATGTATGTGCCTCCTGGTGCACCACT
1726 16_HRV54       GGGAGTTGATATTGGACACATTGTCATGCAATTCATGTATGTACCGCCTGGTGCACCAAA
1727 17_HRV98       GGGAGCTGACATTGGACACATTGTCATGCAATTCATGTATGTTCCACCTGGTGCACCTAA
1728 18_HRV59a|     AGGGGATGACATTGGTCATATAGTCATGCAATATATGTATGTTCCACCAGGTGCTCCACT
1729 19_HRV59b|     AGGGGATGACATTGGTCATATAGTCATGCAATATATGTATGTTCCACCAGGTGCTCCACT
1730 20_HRV59       AGGGGATGACATTGGTCATATAGTCATGCAATATATGTATGTTCCACCAGGTGCTCCACT
1731 21_HRV63       AGGTGATGACATTGGTCATATAGTTATGCAGTACATGTACGTTCCACCCGGTGCCCCTCT
1732 22_HRV63b|     AGGTGATGACATTGGTCATATAGTTATGCAGTACATGTACGTTCCACCCGGTGCCCCTCT
1733 23_HRV63a|     AGGTGATGACATTGGTCATATAGTTATGCAGTACATGTACGTTCCACCCGGTGCCCCTCT
1734 24_HRV39       AGGTGAAGATATTGGACACATAGTAATGCAATACATGTATGTCCCACCTGGTGCACCTGT
1735 25_HRV39a|     AGGTGAAGATATTGGACACATAGTAATGCAATACATGTATGTCCCACCTGGTGCACCTGT
1736 26_HRV39b|     AGGTGAAGATATTGGACACATAGTAATGCAATACATGTATGTCCCACCCGGTGCACCTGT
1737 27_HRV10a|     GGGCGATGACATAGGTCACATAGTTATGCAATATATGTATGTGCCACCTGGGGCTCCAGT
1738 28_HRV10b|     GGGCGATGACATAGGTCACATAGTTATGCAATATATGTATGTGCCACCTGGGGCTCCAGT
1739 29_HRV10       GGGCGATGACATAGGTCACATAGTTATGCAATATATGTATGTGCCACCTGGGGCTCCAGT
1740 30_HRV100a     AGGAGATGACATAGGGCATATCGTAATGCAGTACATGTATGTGCCACCTGGAGCTCCAGT
1741 31_HRV100b     AGGAGATGACATAGGGCATATCGTAATGCAGTACATGTATGTGCCACCTGGAGCTCCAGT
1742 32_HRV100      AGGAGATGACATAGGGCATATCGTAATGCAGTACATGTATGTGCCACCTGGAGCTCCAGT
1743 33_HRV66       GGGTGATGATATAGGACACATTGTGATGCAATACATGTATGTACCACCTGGAGCCCCAAT
1744 34_HRV66b|     GGGTGATGATATAGGACACATTGTGATGCAATACATGTATGTACCACCTGGAGCCCCAAT
1745 35_HRV66a|     GGGTGATGATATAGGACACATTGTGATGCAATACATGTATGTACCACCTGGAGCCCCAAT
1746 36_HRV77a|     AGGTGATGACATAGGACACATGTTGTCATGCAATACATGTATGTACCACCAGGGGCACCCAT
1747 37_HRV77b|     AGGTGATGACATAGGACACATGTTGTCATGCAATACATGTATGTACCACCAGGGGCACCCAT
1748 38_HRV77       AGGTGATGACATAGGACACATGTTGTCATGCAATACATGTATGTACCACCAGGGGCACCCAT
1749 39_HRV62a      TGGTGCAGATATAGGTCACATAGTTATGCAATATATGTATGTACCACCTGGGGCTCCACT
1750 40_HRV62b      TGGTGCAGATATAGGTCACATAGTTATGCAATATATGTATGTACCACCTGGGGCTCCACT
```

FIG. D8 CONT'D

04-2.trace                                                                                          9/20/2007 5:04 PM

```
1751  41_HRV25     TGGTGCAGATATAGGTCACATAGTTATGCAATATATGTATGTGCCACCTGGAGCCCCATT
1752  42_HRV29a    TGGTAATGATATAGGTCACATAGTTATGCAGTACATGTATGTACCACCTGGAGCTCCAGT
1753  43_HRV29b    TGGTAATGATATAGGTCACATAGTTATGCAGTACATGTATGTACCACCTGGAGCTCCAGT
1754  44_HRV44a    TGGTGATGATATAGGCCACATAGTTATGCAGTACATGTATGTACCACCTGGAGCTCCAGT
1755  45_HRV44b    TGGTGATGATATAGGCCACATAGTTATGCAGTACATGTATGTACCACCTGGAGCTCCAGT
1756  46_HRV31     TGGTAGTGACATAGGCCATATAGTCATGCAATACATGTATGTACCACCTGGGGCCCCAGT
1757  47_HRV31a|   TGGTAGTGACATAGGCCATATAGTCATGCAATACATGTATGTACCACCTGGGGCCCCAGT
1758  48_HRV31b|   TGGTAGTGACATAGGCCATATAGTCATGCAATACATGTATGTACCACCTGGGGCCCCAGT
1759  49_HRV47     TGGTGATGACATAGGTCACATAGTTATGCAATACATGTATGTGCCGCCTGGGGCTCCAGT
1760  50_HRV47a|   TGGTGATGACATAGGTCACATAGTTATGCAATACATGTATGTGCCGCCTGGGGCTCCAGT
1761  51_HRV47b|   TGGTGATGACATAGGTCACATAGTTATGCAATACATGTATGTGCCGCCTGGGGCTCCAGT
1762  52_HRV11     AGGAAATGATATTGGTCATGTTGTAATGCAATATATGTATGTCCCACCAGGTGCTCCAGT
1763  53_HRV11b|   AGGAAATGATATTGGTCATGTTGTAATGCAATATATGTATGTCCCACCAGGTGCTCCAGT
1764  54_HRV11a|   AGGAAATGATATTGGTCATGTTGTAATGCAATATATGTATGTCCCACCAGGTGCTCCAGT
1765  55_HRV76     AGGGGATGACATTGGTCATGTAGTGATGCAATACATGTATGTCCCACCAGGCGCTCCAGT
1766  56_HRV76b|   AGGGGATGACATTGGTCATGTGATGCAATACATGTATGTCCCACCAGGCGCTCCAGT
1767  57_HRV76a|   AGGGGATGACATTGGTCATGTAGTGATGCAATACATGTATGTCCCACCAGGCGCTCCAGT
1768  58_HRV33     GGGAGATGATGTTGGTCATGTTGTAATGCAGTACATGTATGTCCCACCAGGTGCACCAGC
1769  59_HRV33b|   GGGAGATGATGTTGGTCATGTTGTAATGCAGTACATGTATGTCCCACCAGGTGCACCAGC
1770  60_HRV33a|   GGGAGATGATGTTGGTCATGTTGTAATGCAGTACATGTATGTCCCACCAGGTGCACCAGC
1771  61_HRV24a|   GGGAGATGACATTGGACATGTTGTAATGCAGTACATGTATATACCACCTGGAGCACCAGT
1772  62_HRV24b|   GGGAGATGACATTGGACATGTTGTAATGCAGTACATGTATATACCACCTGGAGCACCAGT
1773  63_HRV24     GGGAGATGACATTGGACATGTTGTAATGCAGTACATGTATATACCACCTGGAGCACCAGT
1774  64_HRV90     GGGCAATGATATTGGACATGTTGTGATGCAATACATGTATATACCACCTGGGGCACCAGT
1775  65_HRV90a|   GGGCAATGATATTGGACATGTTGTGATGCAATACATGTATATACCACCTGGGGCACCAGT
1776  66_HRV90b|   GGGCAATGATATTGGACATGTTGTGATGCAATACATGTATATACCACCTGGGGCACCAGT
1777  67_HRV34     AGGTGATGATATTGGACATGTTGTGATGCAATACATGTATGTACCACCAGGTGCACCAAT
1778  68_HRV34b|   AGGTGATGATATTGGACATGTTGTGATGCAATACATGTATGTACCACCAGGTGCACCAAT
1779  69_HRV34a|   AGGTGATGATATTGGACATGTTGTGATGCAATACATGTATGTACCACCAGGTGCACCAAT
1780  70_HRV50a|   GGGTGTTGATATTGGACATGTTGTCATGCAATACATGTATGTCCCACCAGGTGCACCAAT
1781  71_HRV50b|   GGGTGTTGATATTGGACATGTTGTCATGCAATACATGTATGTCCCACCAGGTGCACCAAT
1782  72_HRV50     GGGTGTTGATATTGGACATGTTGTCATGCAATACATGTATGTCCCACCAGGTGCACCAAT
1783  73_HRV18a|   GGGTGATGACATAGGACATATTGTTATGCAGTACATGTATGTTCCTCCAGGAGCACCAAT
1784  74_HRV18b|   GGGTGATGACATAGGACATATTGTTATGCAGTACATGTATGTTCCTCCAGGAGCACCAAT
1785  75_HRV18     GGGTGATGACATAGGACATATTGTTATGCAGTACATGTATGTTCCTCCAGGAGCACCAAT
1786  76_HRV55     GGGAGATGACATTGGACATGTAGTCATGCAATACATGTATGTTCCACCTGGAGCACCAAT
1787  77_HRV55b|   GGGAGATGACATTGGACATGTAGTCATGCAATACATGTATGTTCCACCTGGAGCACCAAT
1788  78_HRV55a|   GGGAGATGACATTGGACATGTAGTCATGCAATACATGTATGTTCCACCTGGAGCACCAAT
1789  79_HRV57     AGGTGAGGATATAGGCCATGTTGTAATGCAATACATGTATGTCCCTCCTGGGGCACCAAT
1790  80_HRV57a|   AGGTGAGGATATAGGCCATGTTGTAATGCAATACATGTATGTCCCTCCTGGGGCACCAAT
1791  81_HRV57b|   AGGTGAGGATATAGGCCATGTTGTAATGCAATACATGTATGTCCCTCCTGGGGCACCAAT
1792  82_HRV21     AACGGGTGACATAGGACATGTTGTAATGCAATATATGTATGTCCCACCAGGTGCTCCAAT
1793  83_HRVHan    AGCGGGTGACATAGGACATGTTGTGATGCAATATATGTATGTCCCACCAGGTGCTCCAAT
1794  84_HRV43     AAGCAATGATATAGGCCATGTGGTAATGCAGTACATGTATGTACCACCAGGTGCGCCAAT
1795  85_HRV43b|   AAGCAATGATATAGGCCATGTGGTAATGCAGTACATGTATGTACCACCAGGTGCGCCAAT
1796  86_HRV43a|   AAGCAATGATATAGGCCATGTGGTAATGCAGTACATGTATGTACCACCAGGTGCGCCAAT
1797  87_HRV75     AGGGAATGACATAGGCCATGTAGTAATGCAATACATGTATGTACCACCAGGAGCACCAAT
1798  88_HRV75b|   AGGGAATGACATAGGCCATGTAGTAATGCAATATATGTATGTACCACCAGGAGCACCAAT
1799  89_HRV75a|   AGGGAATGACATAGGCCATGTAGTAATGCAATATATGTATGTACCACCAGGAGCACCAAT
1800  96_HRV9a|d   AAGTGATAGCGTTGGCCATGTTGTTATGCAGTACATGTATGTACCACCAGGGGCACCTTT
1801  97_HRV9b|d   AAGTGATAGCGTTGGCCATGTTGTTATGCAGTACATGTATGTACCACCAGGGGCACCTTT
1802  98_HRV9      AAGTGATAGCGTTGGCCATGTTGTTATGCAGTACATGTATGTACCACCAGGGGCACCTTT
1803  99_HRV32     AAGTGACAGCATTGGTCATGTTGTTATGCAGTACATGTATGTACCACCAGGGGCTCCTCT
1804  100_HRV32a   AAGTGACAGCATTGGTCATGTTGTTATGCAGTACATGTATGTACCACCAGGGGCTCCTCT
1805  101_HRV32b   AAGTGACAGCATTGGTCATGTTGTTATGCAGTACATGTATGTACCACCAGGGGCTCCTCT
1806  102_HRV67    GAGTGACAGCATTGGGCATGTTGTAATGCAATATATGTATGTACCTCCAGGAGCACCATT
1807  103_HRV67a   GAGTGACAGCATTGGGCATGTTGTAATGCAATATATGTATGTACCTCCAGGAGCACCATT
1808  104_HRV67b   GAGTGACAGCATTGGGCATGTTGTAATGCAATATATGTATGTACCTCCAGGAGCACCATT
1809  105_HRV15    GAGTGATAACATCGGTCATGTTGTCATGCAATATATGTATGTTCCTCCGGGAGCCCCTTT
1810  106_HRV15a   GAGTGATAACATCGGTCATGTTGTCATGCAATATATGTATGTTCCTCCGGGAGCCCCTTT
1811  107_HRV15b   GAGTGATAACATCGGTCATGTTGTCATGCAATATATGTATGTTCCTCCGGGAGCCCCTTT
1812  108_HRV74a   AAGTGACAACATTGGCCATGTTGTTATGCAATACATGTATGTCCCCCCAGGAGCACCTTT
1813  109_HRV74b   AAGTGACAACATTGGCCATGTTGTTATGCAATACATGTATGTCCCCCCAGGAGCACCTTT
1814  110_HRV74    AAGTGACAACATTGGCCATGTTGTTATGCAATACATGTATGTCCCCCCAGGAGCACCTTT
1815  111_HRV38a   AAATGAAGGTGTGGGGCATGTTGTTATGCAGTATATGTATGTCCCTCCAGGGGCACCATT
```

FIG. D8 CONT'D

```
04-2.trace                                                                 9/20/2007 5:04 PM 1816  112_HRV38b    AAATGAAGGTGTGGGGCATGTTGTTATGCAGTATATGTATGTCCCTCCAGGGGCACCATT
1817  113_HRV38     AAATGAAGGTGTGGGGCATGTTGTTATGCAGTATATGTATGTCCCTCCAGGGGCACCATT
1818  114_HRV60     AAATGATGGCATAGGTCATGTTGTCATGCAATACATGTATGTCCCCCCAGGAGCACCATT
1819  115_HRV60a    AAATGATGGCATAGGTCATGTTGTCATGCAATACATGTATGTCCCCCCAGGAGCACCATT
1820  116_HRV60b    AAATGATGGCATAGGTCATGTTGTCATGCAATACATGTATGTCCCCCCAGGAGCACCATT
1821  117_HRV64a    GAGTGCTAACATTGGTCATGTTGTTATGCAATATATGTATGTCCCTCCTGGAGCTCCAAT
1822  118_HRV64b    GAGTGCTAACATTGGTCATGTTGTTATGCAATATATGTATGTCCCTCCTGGAGCTCCAAT
1823  119_HRV64     GAGTGCTAACATTGGTCATGTTGTTATGCAATATATGTATGTCCCTCCTGGAGCTCCAAT
1824  120_HRV94a    AAGTGCTAATATTGGTCATGTTGTCAGTACATGTATGTCCTCCTGGAGCTCCAAA
1825  121_HRV94b    AAGTGCTAATATTGGTCATGTTGTCATGCAGTACATGTATGTTCCTCCTGGAGCTCCAAA
1826  122_HRV94     AAGTGCTAATATTGGTCATGTTGTCATGCAGTACATGTATGTTCCTCCTGGAGCTCCAAA
1827  123_HRV22     AAGTAAAAACATTGGTCATGTGGTCATGCAATACATGTATGTTCCGCCTGGAGCTCCTAA
1828  124_HRV22a    AAGTAAAAACATTGGTCATGTGGTCATGCAATACATGTATGTTCCGCCTGGAGCTCCTAA
1829  125_HRV22b    AAGTAAAAACATTGGTCATGTGGTCATGCAATACATGTATGTTCCGCCTGGAGCTCCTAA
1830  126_HRV82     AAGTAATGATATTGGGCATGTAGTGATGCAATACATGTATGTCCCACCAGGTGCTCCTAA
1831  127_HRV82b    AAGTAATGATATTGGGCATGTAGTGATGCAATACATGTATGTCCCACCAGGTGCTCCTAA
1832  128_HRV82a    AAGTAATGATATTGGGCATGTAGTGATGCAATACATGTATGTCCCACCAGGTGCTCCTAA
1833  129_HRV19     AAGTAAAAACATTGGACATGTTGTTATGCAATACATGTATGTGCCTCCTGGTGCTCCTAT
1834  130_HRV19a    AAGTAAAAACATTGGACATGTTGTTATGCAATACATGTATGTGCCTCCTGGTGCTCCTAT
1835  131_HRV19b    AAGTAAAAACATTGGACATGTTGTTATGCAATACATGTATGTGCCTCCTGGTGCTCCTAT
1836  132_HRV13     AGGTGGTGATGTCGGACATGTTGTTATGCAATACATGTATGTACCGCCCGGTGCACCCCT
1837  133_HRV13a    AGGTGGTGATGTCGGACATGTTGTTATGCAATACATGTATGTACCGCCCGGTGCACCCCT
1838  134_HRV13b    AGGTGGTGATGTCGGACATGTTGTTATGCAATACATGTATGTACCGCCCGGTGCACCCCT
1839  135_HRV41     GGGTAGTGATGTCGGACATGTTGTCATGCAATACATGTTCGTACCACCTGGCGCACCCCT
1840  136_HRV41a    GGGTAGTGATGTCGGACATGTTGTCATGCAATACATGTTCGTACCACCTGGCGCACCCCT
1841  137_HRV41b    GGGTAGTGATGTCGGACATGTTGTCATGCAATACATGTTCGTACCACCTGGCGCACCCCT
1842  138_HRV73     AAGTGGAGATGTGGGACATGTAGTTATGCAGTATATGTATGTCCCACCTGGAGCCCCTCT
1843  139_HRV73b    AAGTGGAGATGTGGGACATGTAGTTATGCAGTATATGTATGTCCCACCTGGAGCCCCTCT
1844  140_HRV73a    AAGTGGAGATGTGGGACATGTAGTTATGCAGTATATGTATGTCCCACCTGGAGCCCCTCT
1845  141_HRV61     AGGTGGTGACATTGGACACGTGGTCATGCAATACATGTATGTTCCACCTGGTGCACCTAC
1846  142_HRV61a    AGGTGGTGACATTGGACACGTGGTCATGCAATACATGTATGTTCCACCTGGTGCACCTAC
1847  143_HRV61b    AGGTGGTGACATTGGACACGTGGTCATGCAATACATGTATGTTCCACCTGGTGCACCTAC
1848  144_HRV96     GAGTGGTGATATTGGTCATGTGGTCATGCAATATATGTATGTTCCACCAGGTGCCCCCAC
1849  145_HRV96b    GAGTGGTGATATTGGTCATGTGGTCATGCAATATATGTATGTTCCACCAGGTGCCCCCAC
1850  146_HRV96a    GAGTGGTGATATTGGTCATGTGGTCATGCAATATATGTATGTTCCACCAGGTGCCCCCAC
1851  90_HRV16a|    AGATGGTCACATTGGTCATATAGTCATGCAATATATGTATGTACCACCAGGAGCACCTAT
1852  91_HRV16b|    AGATGGTCACATTGGTCATATAGTCATGCAATATATGTATGTACCACCAGGAGCACCTAT
1853  92_1AYM_A     AGATGGTCACATTGGTCATATAGTCATGCAATATATGTATGTACCACCAGGAGCACCTAT
1854  93_HRV81a|    GGAAGGTCATATTGGTCATATAGTAATGCAATACATGTATGTACCACCAGGAGCACCCAT
1855  94_HRV81b|    GGAAGGTCATATTGGTCATATAGTAATGCAATACATGTATGTACCACCAGGAGCACCCAT
1856  95_HRV81      GGAAGGTCATATTGGTCATATAGTAATGCAATACATGTATGTACCACCAGGAGCACCCAT
1857  147_HRV2      TAGTCAGGACATTGGACACATCACAATGCAATACATGTATGTTCCACCTGGTGCACCGGT
1858  148_HRV2a|    TAGTCAGGACATTGGACACATCACAATGCAATACATGTATGTTCCACCTGGTGCACCGGT
1859  149_HRV2b|    TAGTCAGGACATTGGACACATCACAATGCAATACATGTATGTTCCACCTGGTGCACCGGT
1860  150_HRV49a    TAGCAAGGATATTGGACACATTACAATGCAATACATGTATGTGCCGCCAGGTGCACCTGT
1861  151_HRV49b    TAGCAAGGATATTGGACACATTACAATGCAATACATGTATGTGCCGCCAGGTGCACCTGT
1862  152_HRV49     TAGCAAGGATATTGGACACATTACAATGCAATACATGTATGTGCCGCCAGGTGCACCTGT
1863  153_HRV23a    TAGTCAAGATATTGGTCACATCACAATGCAGTATATGTATGTCCCACCAGGTGCTCCAAT
1864  154_HRV23b    TAGTCAAGATATTGGTCACATCACAATGCAGTATATGTATGTCCCACCAGGTGCTCCAAT
1865  155_HRV23     TAGTCAAGATATTGGTCACATCACAATGCAGTATATGTATGTCCCACCAGGTGCTCCAAT
1866  156_HRV30a    CAGCCAAGATATCGGACACATTACAATGCAGTATATGTATGTTCCACCTGGCGCTCCAAT
1867  157_HRV30b    CAGCCAAGATATCGGACACATTACAATGCAGTATATGTATGTTCCACCTGGCGCTCCAAT
1868  158_HRV30     CAGCCAAGATATCGGACACATTACAATGCAGTATATGTATGTTCCACCTGGCGCTCCAAT
1869  159_HRV7      AGGTAATGATATTGGACATATAGTTATGCAATTTATGTATGTACCTCCAGGGGCCCCAGT
1870  160_HRV7b|    AGGTAATGATATTGGACATATAGTTATGCAATTTATGTATGTACCTCCAGGGGCCCCAGT
1871  161_HRV7a|    AGGTAATGATATTGGACATATAGTTATGCAATTTATGTATGTACCTCCAGGGGCCCCAGT
1872  162_HRV88     AGGTGATGATACTGGACATATAGTACTGCAATTCATGTATGTGCCTCCAGGTGCACCAAT
1873  163_HRV88a    AGGTGATGATACTGGACATATAGTACTGCAATTCATGTATGTGCCTCCAGGTGCACCAAT
1874  164_HRV88b    AGGTGATGATACTGGACATATAGTACTGCAATTCATGTATGTGCCTCCAGGTGCACCAAT
1875  165_HRV36a    GGGAGATGATAGTGGGCATGTAGTATTACAATTCATGTATGTACCTCCAGGAGCGCCTGT
1876  166_HRV36b    GGGAGATGATAGTGGGCATGTAGTATTACAATTCATGTATGTACCTCCAGGAGCGCCTGT
1877  167_HRV36     GGGAGATGATAGTGGGCATGTAGTATTACAATTCATGTATGTACCTCCAGGAGCGCCTGT
1878  168_HRV89a    AGGAAATGATAGTGGACATATAGTATTGCAATTTATGTATGTACCCCCAGGAGCACCTGT
1879  169_HRV89b    AGGAAATGATAGTGGACATATAGTATTGCAATTTATGTATGTACCCCCAGGAGCACCTGT
1880  170_HRV89     AGGAAATGATAGTGGACATATAGTATTGCAATTTATGTATGTACCCCCAGGAGCACCTGT
```

FIG. D8 CONT'D

04-2.trace                                                                                                    9/20/2007 5:04 PM

```
1881  171_HRV58     AGGAGAAGATAATGGACATATTGTGTTACAATTTATGTATGTACCCCCAGGAGCACCTGT
1882  172_HRV58a    AGGAGAAGATAATGGACATATTGTGTTACAATTTATGTATGTACCCCCAGGAGCACCTGT
1883  173_HRV58b    AGGAGAAGATAATGGACATATTGTGTTACAATTTATGTATGTACCCCCAGGAGCACCTGT
1884  174_HRV12a    AGAAGGAAGCAATGGTCACGTGGTGGTCCAATACATGTATGTACCTCCTGGTGCCCCACT
1885  175_HRV12b    AGAAGGAAGCAATGGTCACGTGGTGGTCCAATACATGTATGTACCTCCTGGTGCCCCACT
1886  176_HRV12     AGAAGGAAGCAATGGTCACGTGGTGGTCCAATACATGTATGTACCTCCTGGTGCCCCACT
1887  177_HRV78a    AGGAGACAATAATGGACATGTGGTGCTTCAATTTATGTTTGTTCCACCTGGAGCCCCTAT
1888  178_HRV78b    AGGAGACAATAATGGACATGTGGTGCTTCAATTTATGTTTGTTCCACCTGGAGCCCCTAT
1889  179_HRV78     AGGAGACAATAATGGACATGTGGTGCTTCAATTTATGTTTGTTCCACCTGGAGCCCCTAT
1890  180_HRV20     AGGTCGGGATAATGGGCATGTTGTTTACAGTATATGTATGTACCACCAGGGGCACCAAT
1891  181_HRV20a    AGGTCGGGATAATGGGCATGTTGTTTTACAGTATATGTATGTACCACCAGGGGCACCAAT
1892  182_HRV20b    AGGTCGGGATAATGGGCATGTTGTTTTACAGTATATGTATGTACCACCAGGGGCACCAAT
1893  183_HRV68     TGGAAAAGATAATGGCCATGTGGTTTTACAGTACATGTATGTGCCCGCCAGGGGCACCCAT
1894  184_HRV68a    TGGAAAAGATAATGGCCATGTGGTTTTACAGTACATGTATGTGCCCGCCAGGGGCACCCAT
1895  185_HRV68b    TGGAAAAGATAATGGCCATGTGGTTTTACAGTACATGTATGTGCCCGCCAGGGGCACCCAT
1896  186_HRV28     AGGTGATGATAATGGGCATGTAGTTATGCAATATATGTATGTACCTCCAGGAGCCCCCAT
1897  187_HRV28a    AGGTGATGATAATGGGCATGTAGTTATGCAATATATGTATGTACCTCCAGGAGCCCCCAT
1898  188_HRV28b    AGGTGATGATAATGGGCATGTAGTTATGCAATATATGTATGTACCTCCAGGAGCCCCCAT
1899  189_HRV53a    ACAAGGGAATAACGGGCACGTGGTGATACAATACATGTATGTACCACCGGGTGCTCCAAT
1900  190_HRV53b    ACAAGGGAATAACGGGCACGTGGTGATACAATACATGTATGTACCACCGGGTGCTCCAAT
1901  191_HRV53     ACAAGGGAATAACGGGCACGTGGTGATACAATACATGTATGTACCACCGGGTGCTCCAAT
1902  192_HRV46a    AGGGGATGATATTGGACATGTGGTCATACAATATATGTATGTGCCTCCTGGTGCTCCATT
1903  193_HRV46b    AGGGGATGATATTGGACATGTGGTCATACAATATATGTATGTGCCTCCTGGTGCTCCATT
1904  194_HRV46     AGGGGATGATATTGGACATGTGGTCATACAATATATGTATGTGCCTCCTGGTGCTCCATT
1905  195_HRV80a    AGGGGAGGACATTGGTCATGTAGTTATTCAATACATGTACGTACCACCAGGGGCCCCGTT
1906  196_HRV80b    AGGGGAGGACATTGGTCATGTAGTTATTCAATACATGTACGTACCACCAGGGGCCCCGTT
1907  197_HRV80     AGGGGAGGACATTGGTCATGTAGTTATTCAATACATGTACGTACCACCAGGGGCCCCGTT
1908  198_HRV51     GGGTGATGACATAGGGCACATTGTACTTCAATACATGTATGTACCCCCTGGAGGACCAGT
1909  199_HRV51a    GGGTGATGACATAGGGCACATTGTACTTCAATACATGTATGTACCCCCTGGAGGACCAGT
1910  200_HRV51b    GGGTGATGACATAGGGCACATTGTACTTCAATACATGTATGTACCCCCTGGAGGACCAGT
1911  201_HRV65a    AGGTGATGACATAGGGCACATAGTGCTTCAATATATGTATGTGCCTCCTGGTGGTCCTGT
1912  202_HRV65b    AGGTGATGACATAGGGCACATAGTGCTTCAATATATGTATGTGCCTCCTGGTGGTCCTGT
1913  203_HRV65     AGGTGATGACATAGGGCACATAGTGCTTCAATATATGTATGTGCCTCCTGGTGGTCCTGT
1914  204_HRV71a    AGGAGATGATTTAGGACATATTGTACTCCAGTACATGTATGTTCCCCCAGGTGGTCCAAT
1915  205_HRV71b    AGGAGATGATTTAGGACATATTGTACTCCAGTACATGTATGTTCCCCCAGGTGGTCCAAT
1916  206_HRV71     AGGAGATGATTTAGGACATATTGTACTCCAGTACATGTATGTTCCCCCAGGTGGTCCAAT
1917  207_HRV8      AAAAGGTGACCTTGGACACATAGTCCTTCAATACATGTATGTTCCCCGGGTGCACCTCT
1918  208_HRV95     AGAAGGTGACCTTGGACACATAGTCCTCCAATACATGTATGTTCCCCGGGTGCACCTCT
1919  209_HRV45     AGAAGGTAACTTGGGACACATTGTTGTGCAATACATGTTTGTACCACCAGGAGCACCTCT
1920  210_HRV45a    AGAAGGTAACTTGGGACACATTGTTGTGCAATACATGTTTGTACCACCAGGAGCACCTCT
1921  211_HRV45b    AGAAGGTAACTTGGGACACATTGTTGTGCAATACATGTTTGTACCACCAGGAGCACCTCT
1922  GROUP_1       -------------GG-CA--T-----T-CA-T---ATGT---T-CC-CC-GG-G--CC---
1923
1924  1_HRV1A1|d    TCCTTCAAAAAGAAACGATTTCTCATGGCAATCAGGCACCAATATGTCAATATTCTGGCA
1925  2_HRV1A2|d    TCCTTCAAAAAGAAACGATTTCTCATGGCAATCAGGCACCAATATGTCAATATTCTGGCA
1926  3_HRV1A|cD    TCCTTCAAAAAGAAACGATTTCTCATGGCAATCAGGCACCAATATGTCAATATTCTGGCA
1927  4_HRV1B1|d    TCCAAAAACAAGAAATGATTTCTCATGGCAATCAGGCACTAATATGTCAATATTCTGGCA
1928  5_HRV1B2|d    TCCAAAAACAAGAAATGATTTCTCATGGCAATCAGGCACTAATATGTCAATATTCTGGCA
1929  6_HRV1B       TCCAAAAACAAGAAATGATTTCTCATGGCAATCAGGCACTAATATGTCAATATTCTGGCA
1930  7_HRV40a|d    ACCAAAGAAAAGAAATGATTACACATGGCAGTCAGGCACTAATAGCTTCTGTATTCTGGCA
1931  8_HRV40b|d    ACCAAAGAAAAGAAATGATTACACATGGCAGTCAGGCACTAATGCTTCTGTATTCTGGCA
1932  9_HRV40       ACCAAAGAAAAGAAATGATTACACATGGCAGTCAGGCACTAATGCTTCTGTATTCTGGCA
1933  10_HRV85      ACCAAGGAAAAGAGATGATTACACATGGCAATCAGGTACTAATGCTTCCGTGTTTTGGCA
1934  11_HRV85a|    ACCAAGGAAAAGAGATGATTACACATGGCAATCAGGTACTAATGCTTCCGTGTTTTGGCA
1935  12_HRV85b|    ACCAAGGAAAAGAGATGATTACACATGGCAATCAGGTACTAATGCTTCCGTGTTTTGGCA
1936  13_HRV56a|    TCCAAACTCAAGAGATGATTTTACATGGCAATCTGGCACCAATGCTTCTGTCTTTTGGCA
1937  14_HRV56b|    TCCAAACTCAAGAGATGATTTTACATGGCAATCTGGCACCAATGCTTCTGTCTTTTGGCA
1938  15_HRV56      TCCAAACTCAAGAGATGATTTTACATGGCAATCTGGCACCAATGCTTCTGTCTTTTGGCA
1939  16_HRV54      ACCAGAAAAAGGAATGATTACACCTGGGAGTCAAGCACAAACCCTTCTATATTTTGGCA
1940  17_HRV98      ACCTAAAAAGAGGAATGATTATACTTGGGAATCAAGCACAAACCCTTCTATATTTTGGCA
1941  18_HRV59a|    GCCCACAAAGAGAGATGATTACACATGGCAATCTGGTACTAATGCTTCAATATTCTGGCA
1942  19_HRV59b|    GCCCACAAAGAGAGATGATTACACATGGCAATCTGGTACTAATGCTTCAATATTCTGGCA
1943  20_HRV59      GCCCACAAAGAGAGATGATTACACATGGCAATCTGGTACTAATGCTTCAATATTCTGGCA
1944  21_HRV63      ACCCACCCGAAGAGAAGATTACACATGGCAATCTGGCACTAATGCTTCAATATTCTGGCA
1945  22_HRV63b|    ACCCACCCGAAGAGAAGATTACACATGGCAATCTGGCACTAATGCTTCAATATTCTGGCA
```

FIG. D8 CONT'D 04-2.trace                                                                                        9/20/2007 5:04 PM

```
1946  23_HRV63a|   ACCCACCCGAAGAGAAGATTACACATGGCAATCTGGCACTAATGCTTCAATATTCTGGCA
1947  24_HRV39     ACCTAAGAAGAGAGATGATTACACATGGCAATCTGGAACAAATGCCTCAGTTTTCTGGCA
1948  25_HRV39a|   ACCTAAGAAGAGAGATGATTACACATGGCAATCTGGAACAAATGCCTCAGTTTTCTGGCA
1949  26_HRV39b|   ACCTAAGAAGAGAGATGATTACACATGGCAATCTGGAACAAATGCCTCAGTTTTCTGGCA
1950  27_HRV10a|   ACCAACTAAGAGAGATGATTTTGCTTGGCAGTCGGGAACAAATGCATCAGTCTTCTGGCA
1951  28_HRV10b|   ACCAACTAAGAGAGATGATTTTGCTTGGCAGTCGGGAACAAATGCATCAGTCTTCTGGCA
1952  29_HRV10     ACCAACTAAGAGAGATGATTTTGCTTGGCAGTCGGGAACAAATGCATCAGTCTTCTGGCA
1953  30_HRV100a   TCCAACAAAAAGGGATGATTTTGCATGGCAATCAGGCACAAATGCATCAGTTTTTTGGCA
1954  31_HRV100b   TCCAACAAAAAGGGATGATTTTGCATGGCAATCAGGCACAAATGCATCAGTTTTTTGGCA
1955  32_HRV100    TCCAACAAAAAGGGATGATTTTGCATGGCAATCAGGCACAAATGCATCAGTTTTTTGGCA
1956  33_HRV66     TCCAGATAATAGAACACACTTTGCTTGGCAATCAGGAACAAATGCATCTATATTCTGGCA
1957  34_HRV66b|   TCCAGATAATAGAACACACTTTGCTTGGCAATCAGGAACAAATGCATCTATATTCTGGCA
1958  35_HRV66a|   TCCAGATAATAGAACACACTTTGCTTGGCAATCAGGAACAAATGCATCTATATTCTGGCA
1959  36_HRV77a|   ACCAGATAGCAGGACTCATTTTGCATGGCAGTCAGGGACTAATGCATCAATATTCTGGCA
1960  37_HRV77b|   ACCAGATAGCAGGACTCATTTTGCATGGCAGTCAGGGACTAATGCATCAATATTCTGGCA
1961  38_HRV77     ACCAGATAGCAGGACTCATTTTGCATGGCAGTCAGGGACTAATGCATCAATATTCTGGCA
1962  39_HRV62a    ACCAACAGACAGAAAGCATTTTGCCTGGCAATCAAGTACTAATGCATCAATATTTTGGCA
1963  40_HRV62b    ACCAACAGACAGAAAGCATTTTGCCTGGCAATCAAGTACTAATGCATCAATATTTTGGCA
1964  41_HRV25     ACCAACAGACAGAAAACACTTTTGCATGGCAATCAAGTACTAATGCATCAATATTTTGGCA
1965  42_HRV29a    ACCAAATGACAGAAATCATTTTGCATGGCAATCAGGGACTAATGCATCAATATTCTGGCA
1966  43_HRV29b    ACCAAATGACAGAAATCATTTTGCATGGCAATCAGGGACTAATGCATCAATATTCTGGCA
1967  44_HRV44a    ACCAGATGACAGAAACCACTTTGCATGGCAATCGGGGACTAATGCATCAATATTCTGGCA
1968  45_HRV44b    ACCAGATGACAGAATCCACTTTGCATGGCAATCGGGGAATAATGCATCAATATTCTGGCA
1969  46_HRV31     ACCAACAAATAGAAAACATTTTGCATGGCAATCAGGGTACTAATGCATCGATTTCTGGCA
1970  47_HRV31a|   ACCAACAAATAGAAAACATTTTGCATGGCAATCAGGTACTAATGCATCGATTTTCTGGCA
1971  48_HRV31b|   ACCAACAAATAGAAAACATTTTGCATGGCAATCAGGTACTAATGCATCGATTTTCTGGCA
1972  49_HRV47     GCCAACAAGTAGAGAGCACTTTGCATGGCAGTCAGGTACCAATGCATCAACTTTCTGGCA
1973  50_HRV47a|   GCCAACAAGTAGAGAGCACTTTGCATGGCAGTCAGGTACCAATGCATCAACTTTCTGGCA
1974  51_HRV47b|   GCCAACAAGTAGAGAGCACTTTGCATGGCAGTCAGGTACCAATGCATCAATTTTCTGGCA
1975  52_HRV11     TCCAGAGAAAAGAGATGATTATACATGGCAATCAGGAACAAATGCATCTATTTTCTGGCA
1976  53_HRV11b|   TCCAGAGAAAAGAGATGATTATACATGGCAATCAGGAACAAATGCATCTATTTTCTGGCA
1977  54_HRV11a|   TCCAGAGAAAAGAGATGATTATACATGGCAATCAGGAACAAATGCATCTATTTTCTGGCA
1978  55_HRV76     TCCAAAGAAGAGAGATGACTACACATGGCAGTCAGGAACCAATGCATCTATTTTCTGGCA
1979  56_HRV76b|   TCCAAAGAAGAGAGATGACTACACATGGCAGTCAGGAACCAATGCATCTATTTTCTGGCA
1980  57_HRV76a|   TCCAAAGAAGAGAGATGACTACACATGGCAGTCAGGAACCAATGCATCTATTTTCTGGCA
1981  58_HRV33     TCCAGAAAAGAGAGATGATTACACATGGCAATCAGGAACAAATGCATCTGTCTTTTGGCA
1982  59_HRV33b|   TCCAGAAAAGAGAGATGATTACACATGGCAATCAGGAACAAATGCATCTGTCTTTTGGCA
1983  60_HRV33a|   TCCAGAAAAGAGAGATGATTACACATGGCAATCAGGAACAAATGCATCTGTCTTTTGGCA
1984  61_HRV24a|   CCCAACAAAGAGAGATGATTATACATGGCAATCAGGAACAAATGCATCTGTCTTTTGGCA
1985  62_HRV24b|   CCCAACAAAGAGAGATGATTATACATGGCAATCAGGAACAAATGCATCTGTCTTTTGGCA
1986  63_HRV24     CCCAACAAAGAGAGATGATTATACATGGCAATCAGGAACAAATGCATCTGTCTTTTGGCA
1987  64_HRV90     ACCTGAGAAGAGGGATGATTATGCATGGCAATCAGGCACTAATGCATCTATCTTTTGGCA
1988  65_HRV90a|   ACCTGAGAAGAGGGATGATTATGCATGGCAATCAGGCACTAATGCATCTATCTTTTGGCA
1989  66_HRV90b|   ACCTGAGAAGAGGGATGATTATGCATGGCAATCAGGCACTAATGCATCTATCTTTTGGCA
1990  67_HRV34     ACCTAAAACTAGAGATGATTTTGCATGGCAATCTGGAACAAATGCCTCAATATTTTGGCA
1991  68_HRV34b|   ACCTAAAACTAGAGATGATTTTGCATGGCAATCTGGAACAAATGCCTCAATATTTTGGCA
1992  69_HRV34a|   ACCTAAAACTAGAGATGATTTTGCATGGCAATCTGGAACAAATGCCTCAATATTTTGGCA
1993  70_HRV50a|   ACCCAAGACTAGGGATGATTTTGCCTGGCAATCTGGAACTAATGCTTCAATCTTTTGGCA
1994  71_HRV50b|   ACCCAAGACTAGGGATGATTTTGCCTGGCAATCTGGAACTAATGCTTCAATCTTTTGGCA
1995  72_HRV50     ACCCAAGACTAGGGATGATTTTGCCTGGCAATCTGGAACTAATGCTTCAATCTTTTGGCA
1996  73_HRV18a|   ACCAAAAACCAGAGATGATTTTGCCTGGCAATCTGGAACAAATGCATCAATCTTCTGGCA
1997  74_HRV18b|   ACCAAAAACCAGAGATGATTTTGCCTGGCAATCTGGAACAAATGCATCAATCTTCTGGCA
1998  75_HRV18     ACCAAAAACCAGAGATGATTTTGCCTGGCAATCTGGAACAAATGCATCAATCTTCTGGCA
1999  76_HRV55     TCCAAAGACAAGAGAAGATTATGCTTGGCAATCAGGGACCAATGCATCTATCTTTTGGCA
2000  77_HRV55b|   TCCAAAGACAAGAGAAGATTATGCTTGGCAATCAGGGACCAATGCATCTATCTTTTGGCA
2001  78_HRV55a|   TCCAAAGACAAGAGAAGATTATGCTTGGCAATCAGGGACCAATGCATCTATCTTTTGGCA
2002  79_HRV57     TCCAAAAACAAGAGAGGATTATACATGGCAATCTGGTACCAATGCTTCAATATTTTGGCA
2003  80_HRV57a|   TCCAAAAACAAGAGAGGATTATACATGGCAATCTGGTACCAATGCTTCAATATTTTGGCA
2004  81_HRV57b|   TCCAAAAACAAGAGAGGATTATACATGGCAATCTGGTACCAATGCTTCAATATTTTGGCA
2005  82_HRV21     TCCAAAAACTAGGGAAGATTTTGCTTGGCAGTCAGGCACTAATGCATCCATTTTCTGGCA
2006  83_HRVHan    TCCAAAAACTAGGGAAGATTTTGCTTGGCAATCAGGTACCAATGCATCCATTTTCTGGCA
2007  84_HRV43     TCCAAAAACTAGGAAAGATTATGCATGGCAATCTGGCACAAATGCATCTGTTTTCTGGCA
2008  85_HRV43b|   TCCAAAAACTAGGAAAGATTATGCATGGCAATCTGGCACAAATGCATCTGTTTTCTGGCA
2009  86_HRV43a|   TCCAAAAACTAGGAAAGATTATGCATGGCAATCTGGCACAAATGCATCTGTTTTCTGGCA
2010  87_HRV75     ACCAACAACTAGAAAAGATTATGCATGGCAATCTGGAACAAATGCATCTGTATTTTGGCA
```

FIG. D8 CONT'D

04-2.trace 9/20/2007 5:04 PM

```
2011  88_HRV75b|    ACCAACAACTAGAAAAGATTATGCATGGCAATCTGGAACAAATGCATCTGTATTTTGGCA
2012  89_HRV75a|    ACCAACAACTAGAAAAGATTATGCATGGCAATCTGGAACAAATGCATCTGTATTTTGGCA
2013  96_HRV9a|d    ACCAAGGACTAGAGATGATTATGCATGGCAATCAGGCACAAATGCTTCCATCTTTTGGCA
2014  97_HRV9b|d    ACCAAGGACTAGAGATGATTATGCATGGCAATCAGGCACAAATGCTTCCATCTTTTGGCA
2015  98_HRV9       ACCAAGGACTAGAGATGATTATGCATGGCAATCAGGCACAAATGCTTCCATCTTTTGGCA
2016  99_HRV32      ACCACAAGCAAGAGATGACTACACATGGCAATCTGGCACGAATGCATCTATCTTTTGGCA
2017  100_HRV32a    ACCACAAGCAAGAGATGACTACACATGGCAATCTGGCACGAATGCATCTATCTTTTGGCA
2018  101_HRV32b    ACCACAAGCAAGAGATGACTACACATGGCAATCTGGCACGAATGCATCTATCTTTTGGCA
2019  102_HRV67     ACCAACAAAAGAGATGACTACACATGGCAATCAGGTACAAATGCATCCATCTTTTGGCA
2020  103_HRV67a    ACCAACAAAAGAGATGACTACACATGGCAATCAGGTACAAATGCATCCATCTTTTGGCA
2021  104_HRV67b    ACCAACAAAAGAGATGACTACACATGGCAATCAGGTACAAATGCATCCATCTTTTGGCA
2022  105_HRV15     ACCCAATAAAAGGAATGATTACACATGGCAATCAGGTACAAATGCCTCTGTTTTCTGGCA
2023  106_HRV15a    ACCCAATAAAAGGAATGATTACACATGGCAATCAGGTACAAATGCCTCTGTTTTCTGGCA
2024  107_HRV15b    ACCCAATAAAAGGAATGATTACACATGGCAATCAGGTACAAATGCCTCTGTTTTCTGGCA
2025  108_HRV74a    ACCCAAGAAAAGAGATGATTACACATGGCAATCTGGCACAAATGCATCTGTGTTTTGGCA
2026  109_HRV74b    ACCCAAGAAAAGAGATGATTACACATGGCAATCTGGCACAAATGCATCTGTGTTTTGGCA
2027  110_HRV74     ACCCAAGAAAAGAGATGATTACACATGGCAATCTGGCACAAATGCATCTGTGTTTTGGCA
2028  111_HRV38a    ACCCAGGAAGAGAGATGATTACACTTGGCAATCTGGTACAAATGCCTCTGTTTTCTGGCA
2029  112_HRV38b    ACCCAGGAAGAGAGATGATTACACTTGGCAATCTGGTACAAATGCCTCTGTTTTCTGGCA
2030  113_HRV38     ACCCAGGAAGAGAGATGATTACACTTGGCAATCTGGTACAAATGCCTCTGTTTTCTGGCA
2031  114_HRV60     ACCTACTAAAAGAGACGATTACACATGGCAATCTGGCACAAATGCTTCTGTATTTTGGCA
2032  115_HRV60a    ACCTACTAAAAGAGACGATTACACATGGCAATCTGGCACAAATGCTTCTGTATTTTGGCA
2033  116_HRV60b    ACCTACTAAAAGAGACGATTACACATGGCAATCTGGCACAAATGCTTCTGTATTTTGGCA
2034  117_HRV64a    ACCAACCAAAAGAAATGATTACGTCTGGCAGTCAGGCACCAATGCATCCATCTTTTGGCA
2035  118_HRV64b    ACCAACCAAAAGAAATGATTACGTCTGGCAGTCAGGCACCAATGCATCCATCTTTTGGCA
2036  119_HRV64     ACCAACCAAAAGAAATGATTACGTCTGGCAGTCAGGCACCAATGCATCCATCTTTTGGCA
2037  120_HRV94a    ACCAGACAAAAGAGATGATTATGTTTGGCAATCAGGAACTAATGCATCTATATTCTGGCA
2038  121_HRV94b    ACCAGACAAAAGAGATGATTATGTTTGGCAATCAGGAACTAATGCATCTATATTCTGGCA
2039  122_HRV94     ACCAGACAAAAGAGATGATTATGTTTGGCAATCAGGAACTAATGCATCTATATTCTGGCA
2040  123_HRV22     ACCTGAAAAGAGAGATGACTACACATGGCAATCTGGCACTAATGCATCTGTTTTCTGGCA
2041  124_HRV22a    ACCTGAAAAGAGAGATGACTACACATGGCAATCTGGCACTAATGCATCTGTTTTCTGGCA
2042  125_HRV22b    ACCTGAAAAGAGAGATGACTACACATGGCAATCTGGCACTAATGCATCTGTTTTCTGGCA
2043  126_HRV82     ACCAGAAAAGAGAGACGACTACACTTGGCAATCTGGAACTAATGCTTCAATTTTCTGGCA
2044  127_HRV82b    ACCAGAAAAGAGAGACGACTACACTTGGCAATCTGGAACTAATGCTTCAATTTTCTGGCA
2045  128_HRV82a    ACCAGAAAAGAGAGACGACTACACTTGGCAATCTGGAACTAATGCTTCAATTTTCTGGCA
2046  129_HRV19     CCCAAAAACTAGAAATGATTACACATGGCAATCAGGTACTAATGCATCTATATTTTGGCA
2047  130_HRV19a    CCCAAAAACTAGAAATGATTACACATGGCAATCAGGTACTAATGCATCTATATTTTGGCA
2048  131_HRV19b    CCCAAAAACTAGAAATGATTACACATGGCAATCAGGTACTAATGCATCTATATTTTGGCA
2049  132_HRV13     TCCAACGAAGAAATGATTACACATGGCAATCTGGCACCAATGCATCGTCTGTTTTCTGGCA
2050  133_HRV13a    TCCAACGAAGAGAAATGATTACACATGGCAATCTGGCACCAATGCATCTGTTTTCTGGCA
2051  134_HRV13b    TCCAACGAAGAGAAATGATTACACATGGCAATCTGGCACCAATGCATCTGTTTTCTGGCA
2052  135_HRV41     CCCAGAAAAGAGAGATGATTACACATGGCAATCTGGCACCAATGCATCTGTATTCTGGCA
2053  136_HRV41a    CCCAGAAAAGAGAGATGATTACACATGGCAATCTGGCACCAATGCATCTGTATTCTGGCA
2054  137_HRV41b    CCCAGAAAAGAGAGATGATTACACATGGCAATCTGGCACCAATGCATCTGTATTCTGGCA
2055  138_HRV73     ACCCACAAAAAGAAATGACTACACATGGCAGTCCGGCACTAATGCATCAGTATTCTGGCA
2056  139_HRV73b    ACCCACAAAAAGAAATGACTACACATGGCAGTCCGGCACTAATGCATCAGTATTCTGGCA
2057  140_HRV73a    ACCCACAAAAAGAAATGACTACACATGGCAGTCCGGCACTAATGCATCAGTATTCTGGCA
2058  141_HRV61     ACCTGAGAAAAGAAATGATTTCACATGGCAATCAGGCACAAATGCATCTGTTTTCTGGCA
2059  142_HRV61a    ACCTGAGAAAAGAAATGATTTCACATGGCAATCAGGCACAAATGCATCTGTTTTCTGGCA
2060  143_HRV61b    ACCTGAGAAAAGAAATGATTTCACATGGCAATCAGGCACAAATGCATCTGTTTTCTGGCA
2061  144_HRV96     ACCTGAGAAGAGAGATGACTTTACATGGCAATCAGGCACAAATGCATCTGTGTTTTGGCA
2062  145_HRV96b    ACCTGAGAAGAGAGATGACTTTACATGGCAATCAGGCACAAATGCATCTGTGTTTTGGCA
2063  146_HRV96a    ACCTGAGAAGAGAGATGACTTTACATGGCAATCAGGCACAAATGCATCTGTGTTTTGGCA
2064  90_HRV16a|    ACCAACAACTAGAAATGACTGCTTGGCAATCTGGAACAAATGCATCTGTATTTTGGCA
2065  91_HRV16b|    ACCAACAACTAGAAATGACTATGCTTGGCAATCTGGAACAAATGCATCTGTATTTTGGCA
2066  92_1AYM_A     ACCAACAACTAGAAATGACTATGCTTGGCAATCTGGAACAAATGCATCTGTATTTTGGCA
2067  93_HRV81a|    TCCAACAACTAGAGAAGACTATGCTTGGCAATCTGGAACAAATGCATCTATATTCTGGCA
2068  94_HRV81b|    TCCAACAACTAGAGAAGACTATGCTTGGCAATCTGGAACAAATGCATCTATATTCTGGCA
2069  95_HRV81      TCCAACAACTAGAGAAGACTATGCTTGGCAATCTGGAACAAATGCATCTATATTCTGGCA
2070  147_HRV2      GCCCAATAGTAGGGACGATTATGCATGGCAGTCTGGCACTAATGCCTCTGTTTTCTGGCA
2071  148_HRV2a|    GCCCAATAGTAGGGACGATTATGCATGGCAGTCTGGCACTAATGCCTCTGTTTTCTGGCA
2072  149_HRV2b|    GCCCAATAGTAGGGACGATTATGCATGGCAGTCTGGCACTAATGCCTCTGTTTTCTGGCA
2073  150_HRV49a    ACCAAAGAGCAGAGATGATTATGCATGGCAGTCTGGCACTAATGCATCTGTTTTCTGGCA
2074  151_HRV49b    ACCAAAGAGCAGAGATGATTATGCATGGCAGTCTGGCACTAATGCATCTGTTTTCTGGCA
2075  152_HRV49     ACCAAAGAGCAGAGATGATTATGCATGGCAGTCTGGCACTAATGCATCTGTTTTCTGGCA
```

FIG. D8 CONT'D 04-2.trace                                                                  9/20/2007 5:04 PM

```
2076  153_HRV23a    ACCGGAAAGTAGAAATGACTATGCATGGCAATCTGGAACAAATGCGTCCATTTTTTGGCA
2077  154_HRV23b    ACCGGAAAGTAGAAATGACTATGCATGGCAATCTGGAACAAATGCGTCCATTTTTTGGCA
2078  155_HRV23     ACCGGAAAGTAGAAATGACTATGCATGGCAATCTGGAACAAATGCGTCCATTTTTTGGCA
2079  156_HRV30a    TCCCGAGAGCAGAAATGACTATGCATGGCAGTCTGGAACAAATGCATCTGTTTTTTGGCA
2080  157_HRV30b    TCCCGAGAGCAGAAATGACTATGCATGGCAGTCTGGAACAAATGCATCTGTTTTTTGGCA
2081  158_HRV30     TCCCGAGAGCAGAAATGACTATGCATGGCAGTCTGGAACAAATGCATCTGTTTTTTGGCA
2082  159_HRV7      TCCAATAAAACGCGAAGATTATACATGGCAATCAGGAACAAATGCTTCTATATTTTGGCA
2083  160_HRV7b|    TCCAATAAAACGCGAAGATTATACATGGCAATCAGGAACAAATGCTTCTATATTTTGGCA
2084  161_HRV7a|    TCCAATAAAACGCGAAGATTATACATGGCAATCAGGAACAAATGCTTCTATATTTTGGCA
2085  162_HRV88     TCCCAAGAAACGTGATGATTACACATGGCAGTCAGGAACAAATGCATCTGTGTTCTGGCA
2086  163_HRV88a    TCCCAAGAAACGTGATGATTACACATGGCAGTCAGGAACAAATGCATCTGTGTTCTGGCA
2087  164_HRV88b    TCCCAAGAAACGTGATGATTACACATGGCAGTCAGGAACAAATGCATCTGTGTTCTGGCA
2088  165_HRV36a    TCCTGTGAAGCGTGATGACTACACATGGCAATCAGGGACAAATGCATCTGTGTTCTGGCA
2089  166_HRV36b    TCCTGTGAAGCGTGATGACTACACATGGCAATCAGGGACAAATGCATCTGTGTTCTGGCA
2090  167_HRV36     TCCTGTGAAGCGTGATGACTACACATGGCAATCAGGGACAAATGCATCTGTGTTCTGGCA
2091  168_HRV89a    CCCCGAAAAACGTGATGATTACACATGGCAATCAGGAACAAATGCATCTGTGTTCTGGCA
2092  169_HRV89b    CCCCGAAAAACGTGATGATTACACATGGCAATCAGGAACAAATGCATCTGTGTTCTGGCA
2093  170_HRV89     CCCCGAAAAACGTGATGATTACACATGGCAATCAGGAACAAATGCATCTGTGTTCTGGCA
2094  171_HRV58     ACCCAAGAATCGTGATGACTTTACATGGCAATCAGGCACAAATGCATCTGTTTTCTGGCA
2095  172_HRV58a    ACCCAAGAATCGTGATGACTTTACATGGCAATCAGGCACAAATGCATCTGTTTTCTGGCA
2096  173_HRV58b    ACCCAAGAATCGTGATGACTTTACATGGCAATCAGGCACAAATGCATCTGTTTTCTGGCA
2097  174_HRV12a    ACCCAAAAAACGTGATGATTACACATGGCAATCTGGCACCAACGCCTCAGTTTTTTGGCA
2098  175_HRV12b    ACCCAAAAAACGTGATGATTACACATGGCAATCTGGCACCAACGCCTCAGTTTTTTGGCA
2099  176_HRV12     ACCCAAAAAACGTGATGATTACACATGGCAATCTGGCACCAACGCCTCAGTTTTTTGGCA
2100  177_HRV78a    ACCAAAGAAGAGAGATGACTATACTTGGCAGTCAGGCACCAATGCATCTGTGTTTTGGCA
2101  178_HRV78b    ACCAAAGAAGAGAGATGACTATACTTGGCAGTCAGGCACCAATGCATCTGTGTTTTGGCA
2102  179_HRV78     ACCAAAGAAGAGAGATGACTATACTTGGCAGTCAGGCACCAATGCATCTGTGTTTTGGCA
2103  180_HRV20     ACCAAAGACTAGAGATGACTACACATGGCAATCAGGGACAAATGCATCAGTATTTTGGCA
2104  181_HRV20a    ACCAAAGACTAGAGATGACTACACATGGCAATCAGGGACAAATGCATCAGTATTTTGGCA
2105  182_HRV20b    ACCAAAGACTAGAGATGACTACACATGGCAATCAGGGACAAATGCATCAGTATTTTGGCA
2106  183_HRV68     ACCAAAAACTAGAGATGACTACACATGGCAGTCAGGCACTAATGCATCAGTGTTTGGCA
2107  184_HRV68a    ACCAAAAACTAGAGATGATTACACATGGCAGTCAGGCACTAATGCATCAGTGTTTTGGCA
2108  185_HRV68b    ACCAAAAACTAGAGATGATTACACATGGCAGTCAGGCACTAATGCATCAGTGTTTTGGCA
2109  186_HRV28     CCCCACTACCAGAAATGATTACACATGGCAATCCAGTACCAATGCCTCTGTTTTCTGGCA
2110  187_HRV28a    CCCCACTACCAGAAATGATTACACATGGCAATCCAGTACCAATGCCTCTGTTTTCTGGCA
2111  188_HRV28b    CCCCACTACCAGAAATGATTACACATGGCAATCCAGTACCAATGCCTCTGTTTTCTGGCA
2112  189_HRV53a    ACCCAAAACCAGAGATGACTATACCTGGCAATCTGGAACTAATGCTTCAGTCTTTTGGCA
2113  190_HRV53b    ACCCAAAACCAGAGATGACTATACCTGGCAATCTGGAACTAATGCTTCAGTCTTTTGGCA
2114  191_HRV53     ACCCAAAACCAGAGATGACTATACCTGGCAATCTGGAACTAATGCTTCAGTCTTTTGGCA
2115  192_HRV46a    ACCGAGATATCGGAATGATTATACTTGGCAGTCTGGTACTAATGCTTCAGTGTTCTGGCA
2116  193_HRV46b    ACCGAGATATCGGAATGATTATACTTGGCAGTCTGGTACTAATGCTTCAGTGTTCTGGCA
2117  194_HRV46     ACCGAGATATCGGAATGATTATACTTGGCAGTCTGGTACTAATGCTTCAGTGTTCTGGCA
2118  195_HRV80a    GCCAAACAAACGCAATGATTATACTTGGCAGTCTGGCACGAATGCTTCAGTCTTCTGGCA
2119  196_HRV80b    GCCAAACAAACGCAATGATTATACTTGGCAGTCTGGCACGAATGCTTCAGTCTTCTGGCA
2120  197_HRV80     GCCAAACAAACGCAATGATTATACTTGGCAGTCTGGCACGAATGCTTCAGTCTTCTGGCA
2121  198_HRV51     TCCACTTACTAGGAAAGATGATGAGTGGCAATCAGGAACTAATGCTTCAGTATTCTGGCA
2122  199_HRV51a    TCCACTTACTAGGAAAGATGATGAGTGGCAATCAGGAACTAATGCTTCAGTATTCTGGCA
2123  200_HRV51b    TCCACTTACTAGGAAAGATGATGAGTGGCAATCAGGAACTAATGCTTCAGTATTCTGGCA
2124  201_HRV65a    TCCAAAAACTAGAAAAGATGAAGAGTGGCAGACAGGAACTAATGCTTCAGTCTTTTGGCA
2125  202_HRV65b    TCCAAAAACTAGAAAAGATGAAGAGTGGCAGACAGGAACTAATGCTTCAGTCTTTTGGCA
2126  203_HRV65     TCCAAAAACTAGAAAAGATGAAGAGTGGCAGACAGGAACTAATGCTTCAGTCTTTTGGCA
2127  204_HRV71a    ACCAGAGACCAGGGATGCCGATGAATGGCAGTCTGGAACTAATGCATCAGTCTTTTGGCA
2128  205_HRV71b    ACCAGAGACCAGGGATGCCGATGAATGGCAGTCTGGAACTAATGCATCAGTCTTTTGGCA
2129  206_HRV71     ACCAGAGACCAGGGATGCCGATGAATGGCAGTCTGGAACTAATGCATCAGTCTTTTGGCA
2130  207_HRV8      TCCAGATAAAAGGATGCACGATGCCTGGCAAACCAGTACAAATGCCTCAGTCTTCTGGCA
2131  208_HRV95     TCCAGATAAAAGGATGCACGATGCCTGGCAAACCAGTACAAATGCCTCAGTCTTCTGGCA
2132  209_HRV45     CCCTGTTAGTAGAACTGACAACACTTGGCAATCTAGCACAAATGCATCAGTCTTTTGGCA
2133  210_HRV45a    CCCTGTTAGTAGAACTGACAACACTTGGCAATCTAGCACAAATGCATCAGTCTTTTGGCA
2134  211_HRV45b    CCCTGTTAGTAGAACTGACAACACTTGGCAATCTAGCACAAATGCATCAGTCTTTTGGCA
2135  GROUP_1       -CC--------G-------------TGG-A--C--G-A--AA----TC----TT-TGGCA
2136
2137  1_HRV1A1|d    ACATGGACAGCCATTTCCTAGATTTTCTTTACCATTTCTTAGCATTGCATCAGCTTATTA
2138  2_HRV1A2|d    ACATGGACAGCCATTTCCTAGATTTTCTTTACCATTTCTTAGCATTGCATCAGCTTATTA
2139  3_HRV1A|cD    ACATGGACAGCCATTTCCTAGATTTTCTTTACCATTTCTTAGCATTGCATCAGCTTATTA
2140  4_HRV1B1|d    ACATGGACAACCGTTCCCTAGATTCTCTTTACCATTTCTTAGCATTGCATCAGCTTATTA
```

FIG. D8 CONT'D 04-2.trace                                                                                      9/20/2007 5:04 PM

```
2141  5_HRV1B2|d       ACATGGACAACCGTTCCCTAGATTCTCTTTACCATTTCTTAGCATTGCATCAGCTTATTA
2142  6_HRV1B          ACATGGACAACCGTTCCCTAGATTCTCTTTACCATTTCTTAGCATTGCATCAGCTTATTA
2143  7_HRV40a|d       ACATGGTCAAACTTTCCCTAGATTTTCTTTACCTTTCCTAAGCATAGCTTCAGCATACTA
2144  8_HRV40b|d       ACATGGTCAAACTTTCCCTAGATTTTCTTTACCTTTCCTAAGCATAGCTTCAGCATACTA
2145  9_HRV40          ACATGGTCAAACTTTCCCTAGATTTTCTTTACCTTTCCTAAGCATAGCTTCAGCATACTA
2146  10_HRV85         ACATGGGCAAACTTTCCCCAGATTTTCCTTACCTTTCTTGAGTGTTGCTTCAGCATATTA
2147  11_HRV85a|       ACATGGGCAAACTTTCCCCAGATTTTCCTTACCTTTCTTGAGTGTTGCTTCAGCATATTA
2148  12_HRV85b|       ACATGGGCAAACTTTCCCTACCTTTCTTGAGTGTTGCTTCAGCATATTA
2149  13_HRV56a|       ACATGGCCAAGCTTTCCCCAGATTCTCTCTACCTTTCTTAAGTATTGCTTCTGCTTATTA
2150  14_HRV56b|       ACATGGCCAAGCTTTCCCCAGATTCTCTCTACCTTTCTTAAGTATTGCTTCTGCTTATTA
2151  15_HRV56         ACATGGCCAAGCTTTCCCCAGATTCTCTCTACCTTTCTTAAGTATTGCTTCTGCTTATTA
2152  16_HRV54         ACATGGCCAAGCTTATCCAAGATTCTCTTTACCATTTTGCATCTGCTTATTA
2153  17_HRV98         GCATGGTCAGGCCTATCCAAGATTTTCTCTACCATTCTTGAGCATTGCATCTGCTTACTA
2154  18_HRV59a|       ACATGGACAAACATTCCCAAGATTTTCATTGCCCTTCCTGAGCATAGCATCAGCTTATTA
2155  19_HRV59b|       ACATGGACAAACATTCCCAAGATTTTCATTGCCCTTCCTGAGCATAGCATCAGCTTATTA
2156  20_HRV59         ACATGGACAAACATTCCCAAGATTTTCATTGCCCTTCCTGAGCATAGCATCAGCTTATTA
2157  21_HRV63         ACATGGACAAGCTTTTCCAAGGTTTTCTCTACCTTTCTTGAGTATTGCATCAGCATATTA
2158  22_HRV63b|       ACATGGACAAGCTTTTCCAAGGTTTTCTCTACCTTTCTTGAGTATTGCATCAGCATATTA
2159  23_HRV63a|       ACATGGACAAGCTTTCCCAAGGTTTTCTCTACCTTTCTTGAGTATTGCATCAGCATATTA
2160  24_HRV39         ACACGGACAGCCTTACCCTAGATTTTCATTACCATTTCTAAGCATAGCCTCAGCATATTA
2161  25_HRV39a|       ACACGGACAGCCTTACCCTAGATTTTCATTACCATTTCTAAGCATAGCCTCAGCATATTA
2162  26_HRV39b|       ACACGGACAGCCTTACCCTAGATTTTCATTACCATTTCTAAGCATAGCCTCAGCATATTA
2163  27_HRV10a|       ACATGGACAACCTTTCCTTTACCTTCTTAAGCATTGCATCTGCTTACTA
2164  28_HRV10b|       ACATGGACAACCTTTCCCTAGATTTTCTTTACCCTTCTTAAGCATTGCATCTGCTTACTA
2165  29_HRV10         ACATGGACAACCTTTCCCTAGATTTTCTTTACCCTTCTTAAGCATTGCATCTGCTTACTA
2166  30_HRV100a       GCATGGGCAGCCATTCCCTAGAATTTCTTTACCTTTCTTGAGCATTGCTTCTGCATACTA
2167  31_HRV100b       GCATGGGCAGCCATTCCCTAGAATTTCTTTACCTTTCTTGAGCATTGCTTCTGCATACTA
2168  32_HRV100        GCATGGGCAGCCATTCCCTAGAATTTCTTTACCTTTCTTGAGCATTGCTTCTGCATACTA
2169  33_HRV66         ACTTGGACAACCATTCCCAAGATTCTCGCTACCTTTTCTAGGCATAGCTTCAGCATATTA
2170  34_HRV66b|       ACTTGGACAACCATTCCCAAGATTCTCGCTACCTTTTCTAGGCATAGCTTCAGCATATTA
2171  35_HRV66a|       ACTTGGACAACCATTCCCAAGATTCTCGCTACCTTTTCTAGGCATAGCTTCAGCATATTA
2172  36_HRV77a|       ACATGGACAACCATTCCCAAGATTTTCACTACCTTTTCTGAGTATTGCTTCAGCTTACTA
2173  37_HRV77b|       ACATGGACAACCATTCCCAAGATTTTCACTACCTTTTCTGAGTATTGCTTCAGCTTACTA
2174  38_HRV77         ACATGGACAACCATTCCCAAGATTTTCACTACCTTTTCTGAGTATTGCTTCAGCTTACTA
2175  39_HRV62a        ACATGGGCAACCCTTTCCTAGATTTTCATTACCTTTTTTGAGTGTTGCATCTGCTTATTA
2176  40_HRV62b        ACATGGGCAACCCTTTCCTAGATTTTCATTACCTTTTTTGAGTGTTGCATCTGCTTATTA
2177  41_HRV25         ACATGGACAACCCTTCCCTAGATTTTCATTGCCATTTCTGAGTGTTGCATCTGCTTATTA
2178  42_HRV29a        ACATGGTCAGCCTTTCCCAAGATTTTCATTACCATTCCTAAGTGTTGCATCTGCTTATTA
2179  43_HRV29b        ACATGGTCAGCCTTTCCCAAGATTTTCATTACCATTCCTAAGTGTTGCATCTGCTTATTA
2180  44_HRV44a        ACATGGTCAACCTTTCCCAAGATTTTCATTGCCATTTCTAAGTGTTGCATCTGCCTATTA
2181  45_HRV44b        ACATGGTCAACCTTTCCCAAGATTTTCATTGCCATTTCTAAGTGTTGCATCTGCCTATTA
2182  46_HRV31         ACATGGACAACCCTTTACATTACCCTTTTGAGTGTCGCATCCGCTTATTA
2183  47_HRV31a|       ACATGGACAACCCTTTCCAAGATTTACATTACCCTTTTGAGTGTCGCATCCGCTTATTA
2184  48_HRV31b|       ACATGGACAACCCTTTCCAAGATTTACATTACCCTTTTGAGTGTCGCATCCGCTTATTA
2185  49_HRV47         ACAAGGGCAACCCTTTCCAAGATTTTCATTACCATTTTTGAGTGTTGCATCTGCTTATTA
2186  50_HRV47a|       ACAAGGGCAACCCTTTCCAAGATTTTCATTACCATTTTTGAGTGTTGCATCTGCTTATTA
2187  51_HRV47b|       ACAAGGGCAACCCTTTCCAAGATTTTCATTACCATTTTTGAGTGTTGCATCTGCTTATTA
2188  52_HRV11         ATATGGTCAAACATACCCAAGATTTTCTCTACCTTTCATGAGTATAGCCTCAGCATATTA
2189  53_HRV11b|       ATATGGTCAAACATACCCAAGATTTTCTCTACCTTTCATGAGTATAGCCTCAGCATATTA
2190  54_HRV11a|       ATATGGTCAAACATACCCAAGATTTTCTCTACCTTTCATGAGTATAGCCTCAGCATATTA
2191  55_HRV76         ATATGGACAAACATACCCTAGGTTTTCATTACCCTTTCTAAGTATAGCTTCAGCTTATTA
2192  56_HRV76b|       ATATGGACAAACATACCCTAGGTTTTCATTACCCTTTCTAAGTATAGCTTCAGCTTATTA
2193  57_HRV76a|       ATATGGACAAACATACCCTAGGTTTTCATTACCCTTTCTAAGTATAGCTTCAGCTTATTA
2194  58_HRV33         ATATGGACAAACATATCCTAGGTTCTCATTACCTTTCCTTAGCATAGCTTCAGCATATTA
2195  59_HRV33b|       ATATGGACAAACATATCCTAGGTTCTCATTACCTTTCCTTAGCATAGCTTCAGCATATTA
2196  60_HRV33a|       ATATGGACAAACATATCCTAGGTTCTCATTACCTTTCCTTAGCATAGCTTCAGCATATTA
2197  61_HRV24a|       ACATGGACAAACCTATCCTAGATTTCCCTTCCTTTTCTGAGTGTAGCCTCTGCATATTA
2198  62_HRV24b|       ACATGGACAAACCTATCCTAGATTTTCCCTTCCTTTTCTGAGTGTAGCCTCTGCATATTA
2199  63_HRV24         ACATGGACAAACCTATCCTAGATTTTCCCTTCCTTTTCTGAGTGTAGCCTCTGCATATTA
2200  64_HRV90         ACATGGACAAACATACCCTAGATTTTCACTTCCTTTCTTAAGTATAGCTTCTGCATACTA
2201  65_HRV90a|       ACATGGACAAACATACCCTAGATTTTCACTTCCTTTCTTAAGTATAGCTTCTGCATACTA
2202  66_HRV90b|       ACATGGACAAACATACCCTAGATTTTCACTTCCTTTCTTAAGTATAGCTTCTGCATACTA
2203  67_HRV34         ACATGGTCAAACATACCCTAGATTTTCCCTCCCTTTCTTAAGCATAGCCTCAGCATACTA
2204  68_HRV34b|       ACATGGTCAAACATACCCTAGATTTTCCCTCCCTTTCTTAAGCATAGCCTCAGCATACTA
2205  69_HRV34a|       ACATGGTCAAACATACCCTAGATTTTCCCTCCCTTTCTTAAGCATAGCCTCAGCATACTA
```

FIG. D8 CONT'D

04-2.trace                                                                                          9/20/2007 5:04 PM

```
2206  70_HRV50a|    ACATGGTCAAACATACCCTAGATTCTCTCTACCATTCTTGAGTATAGCATCTGCATATTA
2207  71_HRV50b|    ACATGGTCAAACATACCCTAGATTCTCTCTACCATTCTTGAGTATAGCATCTGCATATTA
2208  72_HRV50     ACATGGTCAAACATACCCTAGATTCTCTCTACCATTCTTGAGTATAGCATCTGCATATTA
2209  73_HRV18a|   ACATGGTCAAACATACCCCAGATTTTCACTTCCTTTCCTCAGTATAGCATCAGCTTATTA
2210  74_HRV18b|   ACATGGTCAAACATACCCCAGATTTTCACTTCCTTTCCTCAGTATAGCATCAGCTTATTA
2211  75_HRV18     ACATGGTCAAACATACCCCAGATTTTCACTTCCTTTCCTCAGTATAGCATCAGCTTATTA
2212  76_HRV55     ACATGGGCAAACATACCCTAGATTTTCACTTCCTTTCCTAAGTATAGCTTCTGCTTATTA
2213  77_HRV55b|   ACATGGGCAAACATACCCTAGATTTCCACTTCCTTTCCTAAGTATAGCTTCTGCTTATTA
2214  78_HRV55a|   ACATGGGCAAACATACCCTAGATTTTCACTTCCTTTCCTAAGTATAGCTTCTGCTTATTA
2215  79_HRV57     ACATGGTCAAACATACCCTAGATTTTCCTTGCCTTTCTTAAGTATAGCCTCAGCATATTA
2216  80_HRV57a|   ACATGGTCAAACATACCCTAGATTTTCCTTGCCTTTCTTAAGTATAGCCTCAGCATATTA
2217  81_HRV57b|   ACATGGTCAAACATACCCTAGATTTTCCTTGCCTTTCTTAAGTATAGCCTCAGCATATTA
2218  82_HRV21     GCATGGCCAGACTTATCCTAGATTTTCATTACCCTTCCTTAGTATAGCATCAGCATACTA
2219  83_HRVHan    GCATGGCCAAACTTATCCTAGATTTTCACTACCCTTCCTTAGTATAGCATCAGCATATTA
2220  84_HRV43     ACATGGTCAAACATTTCCAAGATTTTCCTTACCTTTTCTGAGCATAGCATCAGCATATTA
2221  85_HRV43b|   ACATGGTCAAACATTTCCAAGATTTTCCTTACCTTTTCTGAGCATAGCATCAGCATATTA
2222  86_HRV43a|   ACATGGTCAAACATTTCCAAGATTTTCCTTACCTTTTCTGAGCATAGCATCAGCATATTA
2223  87_HRV75     ACATGGACAAACATTTCCAAGATTTTCACTACCATTTCTGAGCATTGCATCAGCATATTA
2224  88_HRV75b|   ACATGGACAAACATTTCCAAGATTTTCACTACCATTTCTGAGCATTGCATCAGCATATTA
2225  89_HRV75a|   ACATGGACAAACATTTCCAAGATTTTCACTACCATTTCTGAGCATTGCATCAGCATATTA
2226  96_HRV9a|d   ACATGGACAATCATATCCCAGATTTTCACTTCCGTTTTGAGCATTGCCTCTGCATATTA
2227  97_HRV9b|d   ACATGGACAATCATATCCCAGATTTTCACTTCCGTTTTTGAGCATTGCCTCTGCATATTA
2228  98_HRV9      ACATGGACAATCATATCCCAGATTTTCACTTCCGTTTTGAGCATTGCCTCTGCATATTA
2229  99_HRV32     GCATGGACAGGCATATCCCAGGTTTTCACTTCCATTTCTAAGTATTGCCTCTGCATACTA
2230  100_HRV32a   GCATGGACAGGCATATCCCAGGTTTTCACTTCCATTTCTAAGTATTGCCTCTGCATACTA
2231  101_HRV32b   GCATGGACAGGCATATCCCAGGTTTTCACTTCCATTTCTAAGTATTGCCTCTGCATACTA
2232  102_HRV67    ACATGGACAATCATACCCCAGATTCTCACTACCATTCTTAAGTATTGCCTCTGCTTATTA
2233  103_HRV67a   ACATGGACAATCATACCCCAGATTCTCACTACCATTCTTAAGTATTGCCTCTGCTTATTA
2234  104_HRV67b   ACATGGACAATCATACCCCAGATTCTCACTACCATTCTTAAGTATTGCCTCTGCTTATTA
2235  105_HRV15    ACATGGTCAACCTTACCCCAGATTTTCTTTGCCTTTTCTCAGCATTGCATCTGCTTACTA
2236  106_HRV15a   ACATGGTCAACCTTACCCCAGATTTTCTTTGCCTTTTCTCAGCATTGCATCTGCTTACTA
2237  107_HRV15b   ACATGGTCAACCTTACCCCAGATTTTCTTTGCCTTTTCTCAGCATTGCATCTGCTTACTA
2238  108_HRV74a   GCATGGACAGCCATACCCTAGATTCTCATTACCTTTCCTTAGCATAGCATCTGCTTATTA
2239  109_HRV74b   GCATGGACAGCCATACCCTAGATTCTCATTACCTTTCCTTAGCATAGCATCTGCTTATTA
2240  110_HRV74    GCATGGACAGCCATACCCTAGATTCTCATTACCTTTCCTTAGCATAGCATCTGCTTATTA
2241  111_HRV38a   ATATGGTCAGACATATCCTCGATTTTCCTTACCTTTCTTAAGCATTGCATCTGTCTATTA
2242  112_HRV38b   ATATGGTCAGACATATCCTCGATTTTCCTTACCTTTCTTAAGCATTGCATCTGTCTATTA
2243  113_HRV38    ATATGGTCAGACATATCCTCGATTTTCCTTACCTTTCTTAAGCATTGCATCTGTCTATTA
2244  114_HRV60    GCATGGACAAACATACCCTAGATTTTCACTTCCATTTCTAAGTATTGCATCTGCCTACTA
2245  115_HRV60a   GCATGGACAAACATACCCTAGATTTTCACTTCCATTTCTAAGTATTGCATCTGCCTACTA
2246  116_HRV60b   GCATGGACAAACATACCCTAGATTTTCACTTCCATTTCTAAGTATTGCATCTGCCTACTA
2247  117_HRV64a   ACACGGTCAACCATACCCTCGATTTCTCTCCCTTTCCTTAGCATAGCCTCAGCATATTA
2248  118_HRV64b   ACACGGTCAACCATACCCTCGATTTTCTCTCCCTTTCCTTAGCATAGCCTCAGCATATTA
2249  119_HRV64    ACACGGTCAACCATACCCTCGATTTTCTCTCCCTTTCCTTAGCATAGCCTCAGCATATTA
2250  120_HRV94a   ACATGGTCAACCCTACCCTCGATTCTCACTTCCATTTCTTAGTATAGCCTCAGCATATTA
2251  121_HRV94b   ACATGGTCAACCCTACCCTCGATTCTCACTTCCATTTCTTAGTATAGCCTCAGCATATTA
2252  122_HRV94    ACATGGTCAACCCTACCCTCGATTCTCACTTCCATTTCTTAGTATAGCCTCAGCATATTA
2253  123_HRV22    GCATGGTCAACCTTATCCCCGATTCTCACTCCCTTTCCTCAGTGTAGCTTCAGCATATTA
2254  124_HRV22a   GCATGGTCAACCTTATCCCCGATTCTCACTCCCTTTCCTCAGTGTAGCTTCAGCATATTA
2255  125_HRV22b   GCATGGTCAACCTTATCCCCGATTCTCACTCCCTTTCCTCAGTGTAGCTTCAGCATATTA
2256  126_HRV82    ACATGGACAACCTTACCCCGCTTCTCACTTCCTTTCTTGAGTATAGCCTCAGCTTACTA
2257  127_HRV82b   ACATGGACAACCTTACCCTCGCTTCTCACTTCCTTTCTTGAGTATAGCCTCAGCTTACTA
2258  128_HRV82a   ACATGGACAACCTTACCCTCGCTTCTCACTTCCTTTCTTGAGTATAGCCTCAGCTTACTA
2259  129_HRV19    ACATGGTCAACCATACCCAAGATTTTCATTACCTTTTCTAAGTATAGCCTTCTGCATATTA
2260  130_HRV19a   ACATGGTCAACCATACCCAAGATTTTCATTACCTTTTCTAAGTATAGCTTCTGCATATTA
2261  131_HRV19b   ACATGGTCAACCATACCCAAGATTTTCATTACCTTTTCTAAGTATAGCTTCTGCATATTA
2262  132_HRV13    ACATGGTCAAATTTACCCCCGATTCTCTTTACCATTTCTTAGTATTGCATCTGCATATTA
2263  133_HRV13a   ACATGGTCAAATTTACCCCCGATTCTCTTTACCATTTCTTAGTATTGCATCTGCATATTA
2264  134_HRV13b   ACATGGTCAAATTTACCCCCGATTCTCTTTACCATTTCTTAGTATTGCATCTGCATATTA
2265  135_HRV41    GTATGGTCAAGTTTACCCTAGGTTTTCTCTACCATTTCTTAGCATTGCTTCCGCATATTA
2266  136_HRV41a   GTATGGTCAAGTTTACCCTAGGTTTTCTCTACCATTTCTTAGCATTGCTTCCGCATATTA
2267  137_HRV41b   GTATGGTCAAGTTTACCCTAGGTTTTCTCTACCATTTCTTAGCATTGCTTCCGCATATTA
2268  138_HRV73    ACATGGTCAAACTTACCCCAGATTCTCATTACCATTCTTAGTATAGCATCCGCATATTA
2269  139_HRV73b   ACATGGTCAAACTTACCCCAGATTCTCATTACCATTCTTAGTATAGCATCCGCATATTA
2270  140_HRV73a   ACATGGTCAAACTTACCCCAGATTCTCATTACCATTCTTAGTATAGCATCCGCATATTA
```

FIG. D8 CONT'D 04-2.trace                                                                9/20/2007 5:04 PM

```
2271 141_HRV61     ACATGGTCAAGCTTATCCCAGATTTTCATTACCATTCCTAAGTATTGCATCTGCATATTA
2272 142_HRV61a    ACATGGTCAAGCTTATCCCAGATTTTCATTACCATTCCTAAGTATTGCATCTGCATATTA
2273 143_HRV61b    ACATGGTCAAGCTTATCCCAGATTTTCATTACCATTCCTAAGTATTGCATCTGCATATTA
2274 144_HRV96     GCACGGGCAAGCATATCCTAGATTTTCACTGCCTTTCCTTAGTATTGCCTCTGCATATTA
2275 145_HRV96b    GCACGGGCAAGCATATCCTAGATTTTCACTGCCTTTCCTTAGTATTGCCTCTGCATATTA
2276 146_HRV96a    GCACGGGCAAGCATATCCTAGATTTTCACTGCCTTTCCTTAGTATTGCCTCTGCATATTA
2277 90_HRV16a|    GCATGGGCAACCTTTCCCTCGCTTTTCACTTCCCTTTTTGAGTATTGCATCAGCATATTA
2278 91_HRV16b|    GCATGGGCAACCTTTCCCTCGCTTTTCACTTCCCTTTTTGAGTATTGCATCAGCATATTA
2279 92_1AYM_A     GCATGGGCAACCTTTCCCTCGCTTTTCACTTCCCTTTTTGAGTATTGCATCAGCATATTA
2280 93_HRV81a|    ACATGGGCAACCCTTTCCCCGGTTTTCACTCCCTTTTCTAAGTGTAGCATCAGCATATTA
2281 94_HRV81b|    ACATGGGCAACCCTTTCCCCGGTTTTCACTCCCTTTTCTAAGTGTAGCATCAGCATATTA
2282 95_HRV81      ACATGGGCAACCCTTTCCCCGGTTTTCACTCCCTTTTCTAAGTGTAGCATCAGCATATTA
2283 147_HRV2      ACATGGACAGGCTTATCCAAGATTTTCCTTACCTTTCCTAAGTGTGGCATCTGCTTATTA
2284 148_HRV2a|    ACATGGACAGGCTTATCCAAGATTTTCCTTACCTTTCCTAAGTGTGGCATCTGCTTATTA
2285 149_HRV2b|    ACATGGACAGGCTTATCCAAGATTTTCCTTACCTTTCCTAAGTGTGGCATCTGCTTATTA
2286 150_HRV49a    ACATGGGCAAGCATACCCAAGATTTTCTCTACCCTTTTTGAGTGTAGCTTCAGCTTACTA
2287 151_HRV49b    ACATGGGCAAGCATACCCAAGATTTTCTCTACCCTTTTTGAGTGTAGCTTCAGCTTACTA
2288 152_HRV49     ACATGGGCAAGCATACCCAAGATTTTCTCTACCCTTTTTGAGTGTAGCTTCAGCTTACTA
2289 153_HRV23a    ACATGGACAAACATATCCAAGGTTCTCCTTACCCTTTTTGAGTGTGGCATCTGCTTATTA
2290 154_HRV23b    ACATGGACAAACATATCCAAGGTTCTCCTTACCCTTTTTGAGTGTGGCATCTGCTTATTA
2291 155_HRV23     ACATGGACAAACATATCCAAGGTTCTCCTTACCCTTTTTGAGTGTGGCATCTGCTTATTA
2292 156_HRV30a    ACACGGACAAACATACCCAAGATTCTCCCTACCATTTTTGAGTGTAGCATCTGCTTATTA
2293 157_HRV30b    ACACGGACAAACATACCCAAGATTCTCCCTACCATTTTTGAGTGTAGCATCTGCTTATTA
2294 158_HRV30     ACACGGACAAACATACCCAAGATTCTCCCTACCATTTTTGAGTGTAGCATCTGCTTATTA
2295 159_HRV7      GGAGGGTCAACCATACCCTAGATTCACAATTCCTTTTATGAGTATTGCATCAGCTTATTA
2296 160_HRV7b|    GGAGGGTCAACCATACCCTAGATTCACAATTCCTTTTATGAGTATTGCATCAGCTTATTA
2297 161_HRV7a|    GGAGGGTCAACCATACCCTAGATTCACAATTCCTTTTATGAGTATTGCATCAGCTTATTA
2298 162_HRV88     AGAAGGACAACCATACCCAAGATTTACCATTCCCTTTATGAGTATTGCATCAGCTTACTA
2299 163_HRV88a    AGAAGGACAACCATACCCAAGATTTACCATTCCCTTTATGAGTATTGCATCAGCTTACTA
2300 164_HRV88b    AGAAGGACAACCATACCCAAGATTTACCATTCCCTTTATGAGTATTGCATCAGCTTACTA
2301 165_HRV36a    AGAAGGGCAACCATATCCTAGATTTACAATCCCCTTTATGAGTATTGCATCAGCTTATTA
2302 166_HRV36b    AGAAGGGCAACCATATCCTAGATTTACAATCCCCTTTATGAGTATTGCATCAGCTTATTA
2303 167_HRV36     AGAAGGGCAACCATATCCTAGATTTACAATCCCCTTTATGAGTATTGCATCAGCTTATTA
2304 168_HRV89a    AGAAGGACAACCATACCCCAGATTCACAATCCCTTTTATGAGCATTGCATCAGCCTATTA
2305 169_HRV89b    AGAAGGACAACCATACCCCAGATTCACAATCCCTTTTATGAGCATTGCATCAGCCTATTA
2306 170_HRV89     AGAAGGACAACCATACCCCAGATTCACAATCCCTTTTATGAGCATTGCATCAGCCTATTA
2307 171_HRV58     GGAAGGACAACCATACCCTAGATTTACAATCCCTTTTATGAGCATTGCATCAGCTTACTA
2308 172_HRV58a    GGAAGGACAACCATACCCTAGATTTACAATCCCTTTTATGAGCATTGCATCAGCTTACTA
2309 173_HRV58b    GGAAGGACAACCATACCCTAGATTTACAATCCCTTTTATGAGCATTGCATCAGCTTACTA
2310 174_HRV12a    GGAAGGTCAACCTTACCCCAGATTCACAATCCCTTTTATTAGTATTGCCTCAGCATATTA
2311 175_HRV12b    GGAAGGTCAACCTTACCCCAGATTCACAATCCCTTTTATTAGTATTGCCTCAGCATATTA
2312 176_HRV12     GGAAGGTCAACCTTACCCCAGATTCACAATCCCTTTTATTAGTATTGCCTCAGCATATTA
2313 177_HRV78a    ACAAGGTCAAACATACCCCAGGTTCTCTATACCATTTTCTAGTATTGCCTCAGCTTATTA
2314 178_HRV78b    ACAAGGTCAAACATACCCCAGGTTCTCTATACCATTTTCTAGTATTGCCTCAGCTTATTA
2315 179_HRV78     ACAAGGTCAAACATACCCCAGGTTCTCTATACCATTTTCTAGTATTGCCTCAGCTTATTA
2316 180_HRV20     GCAGGGCCAACCTTACCCCAGATTTACCATTCCATTTATGAGTATAGCTTCAGCATATTA
2317 181_HRV20a    GCAGGGCCAACCTTACCCCAGATTTACCATTCCATTTATGAGTATAGCTTCAGCATATTA
2318 182_HRV20b    GCAGGGCCAACCTTACCCCAGATTTACCATTCCATTTATGAGTATAGCTTCAGCATATTA
2319 183_HRV68     ACAAGGACAACCTTACCCCAGATTTACCATTCCATTTATGAGTATAGCTTCAGCATATTA
2320 184_HRV68a    ACAAGGACAACCTTACCCCAGATTTACCATTCCATTTATGAGTATAGCTTCAGCATATTA
2321 185_HRV68b    ACAAGGACAACCTTACCCCAGATTTACCATTCCATTTATGAGTATAGCTTCAGCATATTA
2322 186_HRV28     ACAAGGACAACCATATCCCAGATTCACTATACCTTTTATGAGTATTGCCTCAGCTTATTA
2323 187_HRV28a    ACAAGGACAACCATATCCCAGATTCACTATACCTTTTATGAGTATTGCCTCAGCTTATTA
2324 188_HRV28b    ACAAGGACAACCATATCCCAGATTCACTATACCTTTTATGAGTATTGCCTCAGCTTATTA
2325 189_HRV53a    ACAAGGACAACCATACCCTAGATTCACAATCCCTTTCATGAGTATTGCGTCAGCATATTA
2326 190_HRV53b    ACAAGGACAACCATACCCTAGATTCACAATCCCTTTCATGAGTATTGCGTCAGCATATTA
2327 191_HRV53     ACAAGGACAACCATACCCTAGATTCACAATCCCTTTCATGAGTATTGCGTCAGCATATTA
2328 192_HRV46a    GCAAGGGCAGCCATACCCTAGATTCACTATCCCGTTCATGAGTATAGCCTCAGCATATTA
2329 193_HRV46b    GCAAGGGCAGCCATACCCTAGATTCACTATCCCGTTCATGAGTATAGCCTCAGCATATTA
2330 194_HRV46     GCAAGGGCAGCCATACCCTAGATTCACTATCCCGTTCATGAGTATAGCCTCAGCATATTA
2331 195_HRV80a    ACAGGGTCAGCCATACCCCAGATTCACAATTCCATTCATGAGTATAGCCTCAGCTTATTA
2332 196_HRV80b    ACAGGGTCAGCCATACCCCAGATTCACTATTCCATTCATGAGTATAGCCTCAGCTTATTA
2333 197_HRV80     ACAGGGTCAGCCATACCCCAGATTCACTATTCCATTCATGAGTATAGCCTCAGCTTATTA
2334 198_HRV51     ACATGGACAACCATACCCTAGATTTACAATCCCTTTTGTAAGCATAGCCTCAGCATACTA
2335 199_HRV51a    ACATGGACAACCATACCCTAGATTTACAATCCCTTTTGTAAGCATAGCCTCAGCATACTA
```

FIG. D8 CONT'D

```
04-2.trace                                                              9/20/2007 5:04 PM 2336  200_HRV51b      ACATGGACAACCATACCCTAGATTTACAATCCCTTTTGTAAGCATAGCCCTCAGCATACTA
2337  201_HRV65a      GCATGGTCAACCATACCCCAGATTTACAATTCCTTTTGTGAGTATTGCCTCAGCATATTA
2338  202_HRV65b      GCATGGTCAACCATACCCCAGATTTACAATTCCTTTTGTGAGTATTGCCTCAGCATATTA
2339  203_HRV65       GCATGGTCAACCATACCCCAGATTTACAATTCCTTTTGTGAGTATTGCCTCAGCATATTA
2340  204_HRV71a      GCACGGCCAACCATACCCAAGGTTTACAATCCCCTTCATAAGCATTGCATCAGCATATTA
2341  205_HRV71b      GCACGGCCAACCATACCCAAGGTTTACAATCCCCTTCATAAGCATTGCATCAGCATATTA
2342  206_HRV71       GCACGGCCAACCATACCCAAGGTTTACAATCCCCTTCATAAGCATTGCATCAGCATATTA
2343  207_HRV8        AGTTGGACAAACTTATCCCAGATTCACCATACCTTTCTCCAGCATAGCATCAGCTTATTA
2344  208_HRV95       AGTTGGACAGACTTATCCCAGATTCACCATACCTTTCTCCAGTATAGCATCAGCTTATTA
2345  209_HRV45       GGTTGGTCAAACTTATCCCAGATTTTCTATACCTTTCTCAAGTATAGCTTCAGCTTACTA
2346  210_HRV45a      GGTTGGTCAAACTTATCCCAGATTTTCTATACCTTTCTCAAGTATAGCTTCAGCTTACTA
2347  211_HRV45b      GGTTGGTCAAACTTATCCCAGATTTTCTATACCTTTCTCAAGTATAGCTTCAGCTTACTA
2348  GROUP_1         ----GG-CA----T--CC--G--T--C--T-CC--TT-----G--T-GC-TC-G--TA-TA
2349
2350  1_HRV1A1|d      TATGTTTTATGATGGATATGATGGAGACAACACTTCTTCCAAGTATGGTAGCGTAGTTAC
2351  2_HRV1A2|d      TATGTTTTATGATGGATATGATGGAGACAACACTTCTTCCAAGTATGGTAGCGTAGTTAC
2352  3_HRV1A|cD      TATGTTTTATGATGGATATGATGGAGACAACACTTCTTCCAAGTATGGTAGCGTAGTTAC
2353  4_HRV1B1|d      CATGTTTTATGATGGATATGATGGAGATAATTCCTCTTCCAAATATGGTAGTATAGTCAC
2354  5_HRV1B2|d      CATGTTTTATGATGGATATGATGGAGATAATTCCTCTTCCAAATATGGTAGTATAGTCAC
2355  6_HRV1B         CATGTTTTATGATGGATATGATGGAGATAATTCCTCTTCCAAATATGGTAGTATAGTCAC
2356  7_HRV40a|d      CATGTTTTATGATGGATACGATGGTGATACATCGACCTCAAGATATGGCACATCAGTCAC
2357  8_HRV40b|d      CATGTTTTATGATGGATACGATGGTGATACATCGACCTCAAGATATGGCACATCAGTCAC
2358  9_HRV40         CATGTTTTATGATGGATACGATGGTGATACATCGACCTCAAGATATGGCACATCAGTCAC
2359  10_HRV85        CATGTTTTATGATGGTTATGATGGTGATACACCAGGCTCAATGTATGGGACGTCAGTCAC
2360  11_HRV85a|      CATGTTTTATGATGGTTATGATGGTGATACACCAGGCTCAATGTATGGGACGTCAGTCAC
2361  12_HRV85b|      CATGTTTTATGATGGTTATGATGGTGATACACCAGGCTCAATGTATGGGACGTCAGTCAC
2362  13_HRV56a|      CATGTTTTATGATGGTTATGATGGAGACACTTCAAGCTCCAGATATGGTACATCAGTTAC
2363  14_HRV56b|      CATGTTTTATGATGGTTATGATGGAGACACTTCAAGCTCCAGATATGGTACATCAGTTAC
2364  15_HRV56        CATGTTTTATGATGGTTATGATGGAGACACTTCAAGCTCCAGATATGGTACATCAGTTAC
2365  16_HRV54        CATGTTTTATGATGGGTATGATGGTGACGCACCTGGATCAAGATATGGGACTTCAGTTAC
2366  17_HRV98        CATGTTTTACGATGGGTATGATGGTGACCTGGATCAAGATATGGAACCTCAGTCAC
2367  18_HRV59a|      CATGTTTTATGATGGTTATGATGGAGATAAATCTGAATCTAGGTATGGTGTGTCTGTAAC
2368  19_HRV59b|      CATGTTTTATGATGGTTATGATGGAGATAAATCTGAATCTAGGTATGGTGTGTCTGTAAC
2369  20_HRV59        CATGTTTTATGATGGTTATGATGGAGATAAATCTGAATCTAGGTATGGTGTGTCTGTAAC
2370  21_HRV63        CATGTTTTATGATGGATATGATGGAGATAAATCAAGCTCTAGGTATGGTGTTTCAGTTAC
2371  22_HRV63b|      CATGTTTTATGATGGATATGATGGAGATAAATCAAGCTCTAGGTATGGTGTTTCAGTTAC
2372  23_HRV63a|      CATGTTTTATGATGGATATGATGGAGATAAATCAAGCTCTAGGTATGGTGTTTCAGTTAC
2373  24_HRV39        TATGTTCTATGATGGATATGATGGTGATAAATCGTCATCTAGGTATGGTGTTTCTGTCAC
2374  25_HRV39a|      TATGTTCTATGATGGATATGATGGTGATAAATCGTCATCTAGGTATGGTGTTTCTGTCAC
2375  26_HRV39b|      TATGTTCTATGATGGATATGATGGTGATAAATCGTCATCTAGGTATGGTGTTTCTGTCAC
2376  27_HRV10a|      CATGTTCTATGATGGTTATGATGGTGATACACATGACTCACGTTATGGCACAACAGTGAT
2377  28_HRV10b|      CATGTTCTATGATGGTTATGATGGTGATACACATGACTCACGTTATGGCACAACAGTGAT
2378  29_HRV10        CATGTTCTATGATGGTTATGATGGTGATACACATGACTCACGTTATGGCACAACAGTGAT
2379  30_HRV100a      CATGTTTTATGATGGATATGATGGTGATACACATGATTCACACTATGGTACTACTGTAAT
2380  31_HRV100b      CATGTTTTATGATGGATATGATGGTGATACACATGATTCACACTATGGTACTACTGTAAT
2381  32_HRV100       CATGTTTTATGATGGATATGATGGTGATACACATGATTCACACTATGGTACTACTGTAAT
2382  33_HRV66        CATGTTCTATGATGGTTATGATGGAGATACTCCTGGGTCTCGTTATGGAACCACAGTAGT
2383  34_HRV66b|      CATGTTCTATGATGGTTATGATGGAGATACTCCTGGGTCTCGTTATGGAACCACAGTAGT
2384  35_HRV66a|      CATGTTCTATGATGGTTATGATGGAGATACTCCTGGGTCTCGTTATGGAACCACAGTAGT
2385  36_HRV77a|      CATGTTTTATGATGGCTATGATGGGGATACCTATGAATCACGTTATGGTACTACAGTGGT
2386  37_HRV77b|      CATGTTTTATGATGGCTATGATGGGGATACCTATGAATCACGTTATGGTACTACAGTGGT
2387  38_HRV77        CATGTTTTATGATGGCTATGATGGGGATACCTATGAATCACGTTATGGTACTACAGTGGT
2388  39_HRV62a       CATGTTTTATGATGGCTATAATGGTGATGACTATACAGCAAAATACGGTACCACCGTGGT
2389  40_HRV62b       CATGTTTTATGATGGCTATAATGGTGATGACTATACAGCAAAATACGGTACCACCGTGGT
2390  41_HRV25        CATGTTTTATGATGGCTATAATGGTGATGATCACACAGCGAGATATGGTACCACTGTGGT
2391  42_HRV29a       CATGTTTTATGATGGTTACAATGGAGGTGATCATACAGCAACTTATGGCACCACAGTGGT
2392  43_HRV29b       CATGTTTTATGATGGTTACAATGGAGGTGATCATACAGCAACTTATGGCACCACAGTGGT
2393  44_HRV44a       CATGTTTTATGACGGTTATAATGGAGGTGATCATACAGCAACTTATGGCACCACAGTGGT
2394  45_HRV44b       CATGTTTTATGACGGTTATAATGGAGGTGATCATACAGCAACTTATGGCACCACAGTGGT
2395  46_HRV31        CATGTTTTATGATGGTTATGATGGAGACAAAAGTGGAGCCAAGTATGGTACTACAGTAGT
2396  47_HRV31a|      CATGTTTTATGATGGTTATGATGGAGACAAAAGTGGAGCCAAGTATGGTACTACAGTAGT
2397  48_HRV31b|      CATGTTTTATGATGGTTATGATGGAGACAAAAGTGGAGCCAAGTATGGTACTACAGTAGT
2398  49_HRV47        CATGTTTTATGATGGCTATAATGGTGACAGAAGTGGAGCCAAGTATGGCACCACAGTGGT
2399  50_HRV47a|      CATGTTTTATGATGGCTATAATGGTGACAGAAGTGGAGCCAAGTATGGCACCACAGTGGT
2400  51_HRV47b|      CATGTTTTATGATGGCTATAATGGTGACAGAAGTGGAGCCAAGTATGGCACCACAGTGGT
```

FIG. D8 CONT'D

```
04-2.trace                                                                                    9/20/2007 5:04 PM 2401  52_HRV11      CATGTTTTATGATGGATATGATGGAGATCAACCAAACTCCAGATATGGTAATATAGTTAC
2402  53_HRV11b|    CATGTTTTATGATGGATATGATGGAGATCAACCAAACTCCAGATATGGTAATATAGTTAC
2403  54_HRV11a|    CATGTTTTATGATGGATATGATGGAGATCAACCAAACTCCAGATATGGTAATATAGTTAC
2404  55_HRV76      CATGTTTTATGATGGATATGATGGAGACCAACCTAGTTCTAGGTATGGTAATATAGTTAC
2405  56_HRV76b|    CATGTTTTATGATGGATATGATGGAGACCAACCTAGTTCTAGGTATGGTAATATAGTTAC
2406  57_HRV76a|    CATGTTTTATGATGGATATGATGGAGACCAACCTAGTTCTAGGTATGGTAATATAGTTAC
2407  58_HRV33      CATGTTCTATGATGGATATGATGGGGACCAACCCAATTCCAGGTATGGTAATATGGTTAC
2408  59_HRV33b|    CATGTTCTATGATGGATATGATGGGGACCAACCCAATTCCAGGTATGGTAATATGGTTAC
2409  60_HRV33a|    CATGTTCTATGATGGATATGATGGGGACCAACCCAATTCCAGGTATGGTAATATGGTTAC
2410  61_HRV24a|    CATGTTTTATGATGGATATGATGGTGATCAACACGACTCAGTGTATGGTTCAGTTGTTAC
2411  62_HRV24b|    CATGTTTTATGATGGATATGATGGTGATCAACACGACTCAGTGTATGGTTCAGTTGTTAC
2412  63_HRV24      CATGTTTTATGATGGATATGATGGTGATCAACACGACTCAGTGTATGGTTCAGTTGTTAC
2413  64_HRV90      TATGTTTTATGATGGATATGATGGTGACCAAACTGATTCGAGATATGGTACCATTGTTAC
2414  65_HRV90a|    TATGTTTTATGATGGATATGATGGTGACCAAACTGATTCGAGATATGGTACCATTGTTAC
2415  66_HRV90b|    TATGTTTTATGATGGATATGATGGTGACCAAACTGATTCGAGATATGGTACCATTGTTAC
2416  67_HRV34      CATGTTTTATGATGGATATGATGGTGATCAACATGATTCAAGATATGGTACAGTAGTGAC
2417  68_HRV34b|    CATGTTTTATGATGGATATGATGGTGATCAACATGATTCAAGATATGGTACAGTAGTGAC
2418  69_HRV34a|    CATGTTTTATGATGGATATGATGGTGATCAACATGATTCAAGATATGGTACAGTAGTGAC
2419  70_HRV50a|    CATGTTTTATGATGGTTATGATGGTGATAAATCTACATCCAGGTATGGTACAGTAGTTAC
2420  71_HRV50b|    CATGTTTTATGATGGTTATGATGGTGATAAATCTACATCCAGGTATGGTACAGTAGTTAC
2421  72_HRV50      CATGTTTTATGATGGTTATGATGGTGATAAATCTACATCCAGGTATGGTACAGTAGTTAC
2422  73_HRV18a|    CATGTTCTATGATGGCTACGACGGTGACCAGACCTCATCGCGGTATGGCACAGTTGCAAC
2423  74_HRV18b|    CATGTTCTATGATGGCTACGACGGTGACCAGACCTCATCGCGGTATGGCACAGTTGCAAC
2424  75_HRV18      CATGTTCTATGATGGCTACGACGGTGACCAGACCTCATCGCGGTATGGCACAGTTGCAAC
2425  76_HRV55      CATGTTCTATGATGGATATGATGGTGACCAAACTGAGTCACGCTATGGCACTGTAGTCAC
2426  77_HRV55b|    CATGTTCTATGATGGATATGATGGTGACCAAACTGAGTCACGCTATGGCACTGTAGTCAC
2427  78_HRV55a|    CATGTTCTATGATGGATATGATGGTGACCAAACTGAGTCACGCTATGGCACTGTAGTCAC
2428  79_HRV57      CATGTTTTATGATGGATATGATGGTGACCAAACTGAATCAAGATATGGTACTGTAGTCAC
2429  80_HRV57a|    CATGTTTTATGATGGATATGATGGTGACCAAACTGAATCAAGATATGGTACTGTAGTCAC
2430  81_HRV57b|    CATGTTTTATGATGGATATGATGGTGACCAAACTGAATCAAGATATGGTACTGTAGTCAC
2431  82_HRV21      CATGTTTTATGATGGTTATGATGGTGACCAGACTGACTCACAATATGGTGCAGTAGTAAC
2432  83_HRVHan     CATGTTTTATGATGGTTATGATGGTGATCAGACTGACTCACAATATGGTGCAGTGGTGAC
2433  84_HRV43      CATGTTTTATGATGGATATGAAGGTGACCAAAAAACATCCCGTTATGGCACAATTGCAAG
2434  85_HRV43b|    CATGTTTTATGATGGATATGAAGGTGACCAAAAAACATCCCGTTATGGCACAATTGCAAG
2435  86_HRV43a|    CATGTTTTATGATGGATATGAAGGTGACCAAAAAACATCCCGTTATGGCACAATTGCAAG
2436  87_HRV75      CATGTTTTATGATGGATATGAAGGGGATCAAAATACATCCCGTTATGGCACCATTGCTAG
2437  88_HRV75b|    CATGTTTTATGATGGATATGAAGGGGATCAAAATACATCCCGTTATGGCACCATTGCTAG
2438  89_HRV75a|    CATGTTTTATGATGGATATGAAGGGGATCAAAATACATCCCGTTATGGCACCATTGCTAG
2439  96_HRV9a|d    CATGTTCTATGATGGTTATGATGGTGG---ACCAGATTCTCTGTATGGAACAATTGTAAC
2440  97_HRV9b|d    CATGTTCTATGATGGTTATGATGGTGG---ACCAGATTCTCTGTATGGAACAATTGTAAC
2441  98_HRV9       CATGTTCTATGATGGTTATGATGGTGG---ACCAGATTCTCTGTATGGAACAATTGTAAC
2442  99_HRV32      CATGTTTTATGATGGTTATGATGGTGG---GCCAGATTCACAATATGGAACAATTGTAAC
2443  100_HRV32a    CATGTTTTATGATGGTTATGATGGTGG---GCCAGATTCACAATATGGAACAATTGTAAC
2444  101_HRV32b    CATGTTTTATGATGGTTATGATGGTGG---GCCAGATTCACAATATGGAACAATTGTAAC
2445  102_HRV67     CATGTTCTATGATGGCTATGATGGTGG---ACCAGATTCACTATATGGCACCATAGTAAC
2446  103_HRV67a    CATGTTTTATGATGGCTATGATGGTGG---ACCAGATTCACTATATGGCACCATAGTAAC
2447  104_HRV67b    CATGTTTTATGATGGCTATGATGGTGG---ACCAGATTCACTATATGGCACCATAGTAAC
2448  105_HRV15     CATGTTCTATGATGGATATGATGGAGATTCCACTGAATCACATTATGGTACAGTGGTCAC
2449  106_HRV15a    CATGTTCTATGATGGATATGATGGAGATTCCACTGAATCACATTATGGTACAGTGGTCAC
2450  107_HRV15b    CATGTTCTATGATGGATATGATGGAGATTCCACTGAATCACATTATGGTACAGTGGTCAC
2451  108_HRV74a    CATGTTTTATGATGGATATGATGGAGACTCTACTGAATCACATTATGGTACAGTAGTAAC
2452  109_HRV74b    CATGTTTTATGATGGATATGATGGAGACTCTACTGAATCACATTATGGTACAGTAGTAAC
2453  110_HRV74     CATGTTTTATGATGGATATGATGGAGACTCTACTGAATCACATTATGGTACAGTAGTAAC
2454  111_HRV38a    TATGTTTTATGATGGATATGATGGGGACTCAACAGAATCACATTATGGGACAGCGGTGAC
2455  112_HRV38b    TATGTTTTATGATGGATATGATGGGGACTCAACAGAATCACATTATGGGACAGCGGTGAC
2456  113_HRV38     TATGTTTTATGATGGATATGATGGGGACTCAACAGAATCACATTATGGGACAGCGGTGAC
2457  114_HRV60     CATGTTTTATGATGGTTATGATGGTCACTCAACTGAATCACATTATGGGACGGTTGTGAC
2458  115_HRV60a    CATGTTTTATGATGGTTATGATGGTCACTCAACTGAATCACATTATGGGACGGTTGTGAC
2459  116_HRV60b    CATGTTTTATGATGGTTATGATGGTCACTCAACTGAATCACATTATGGGACGGTTGTGAC
2460  117_HRV64a    CATGTTTTATGATGGTTATGACGGTGG---ACCTGGTTCCCGTTATGGCGCAGTGGTGAC
2461  118_HRV64b    CATGTTTTATGATGGTTATGACGGTGG---ACCTGGTTCCCGTTATGGCGCAGTGGTGAC
2462  119_HRV64     CATGTTTTATGATGGTTATGACGGTGG---ACCTGGTTCCCGTTATGGCGCAGTGGTGAC
2463  120_HRV94a    CATGTTCTATGATGGTTATGATGGTGG---ACCTGGCTCACGCTATGGCACAGTGGTGAC
2464  121_HRV94b    CATGTTCTATGATGGTTATGATGGTGG---ACCTGGCTCACGCTATGGCACAGTGGTGAC
2465  122_HRV94     CATGTTCTATGATGGTTATGATGGTGG---ACCTGGCTCACGCTATGGCACAGTGGTGAC
```

FIG. D8 CONT'D

04-2.trace                                                                                        9/20/2007 5:04 PM

```
2466  123_HRV22     CATGTTTTATGATGGGTATGATGGAGG---TCCCGGATCACGTTATGGAGCAGTGGTAAC
2467  124_HRV22a    CATGTTTTATGATGGGTATGATGGAGG---TCCCGGATCACGTTATGGAGCAGTGGTAAC
2468  125_HRV22b    CATGTTTTATGATGGGTATGATGGAGG---TCCCGGATCACGTTATGGAGCAGTGGTAAC
2469  126_HRV82     TATGTTCTATGATGGCTATGATGGTGATGCTCCCGGATCGCGATACGGGACCATAGTGAC
2470  127_HRV82b    TATGTTCTATGATGGCTATGATGGTGATGCTCCCGGATCGCGATACGGGACCATAGTGAC
2471  128_HRV82a    TATGTTCTATGATGGCTATGATGGTGATGCTCCCGGATCGCGATACGGGACCATAGTGAC
2472  129_HRV19     CATGTTTTATGATGGGTATGATGGAGATTCACCAGGATCCCGCTATGGAACAATAGTAAC
2473  130_HRV19a    CATGTTTTATGATGGGTATGATGGAGATTCACCAGGATCCCGCTATGGAACAATAGTAAC
2474  131_HRV19b    CATGTTTTATGATGGGTATGATGGAGATTCACCAGGATCCCGCTATGGAACAATAGTAAC
2475  132_HRV13     TATGTTTTATGATGGATATAATGGAGATTCCTCAGATGCACGCTATGGGACAACAATCAC
2476  133_HRV13a    TATGTTTTATGATGGATATAATGGAGATTCCTCAGATGCACGCTATGGGACAACAATCAC
2477  134_HRV13b    TATGTTTTATGATGGATATAATGGAGATTCCTCAGATGCACGCTATGGGACAACAATCAC
2478  135_HRV41     CATGTTTTATGATGGTTATGAAGAAGGCTCTACAAATGCACGCTATGGAACAACAGTCAC
2479  136_HRV41a    CATGTTTTATGATGGTTATGAAGAAGGCTCTACAAATGCACGCTATGGAACAACAGTCAC
2480  137_HRV41b    CATGTTTTATGATGGTTATGAAGAAGGCTCTACAAATGCACGCTATGGAACAACAGTCAC
2481  138_HRV73     TATGTTTTATGATGGATATGATGGTGACTCCACACAATCACATTATGGCACCACAGTAGT
2482  139_HRV73b    TATGTTTTATGATGGATATGATGGTGACTCCACACAATCACATTATGGCACCACAGTAGT
2483  140_HRV73a    TATGTTTTATGATGGATATGATGGTGACTCCACACAATCACATTATGGCACCACAGTAGT
2484  141_HRV61     TATGTTTTATGATGGTTATGATGGAGATTCTGAAATAACGCGCTATGGAACATCAGTGAC
2485  142_HRV61a    TATGTTTTATGATGGTTATGATGGAGATTCTGAAATAACGCGCTATGGAACATCAGTGAC
2486  143_HRV61b    TATGTTTTATGATGGTTATGATGGAGATTCTGAAATAACGCGCTATGGAACATCAGTGAC
2487  144_HRV96     CATGTTTTATGATGGATATGATGGTGACTCTGAATCAACACGCTATGGAACATCTGTTAC
2488  145_HRV96b    CATGTTTTATGATGGATATGATGGTGACTCTGAATCAACACGCTATGGAACATCTGTTAC
2489  146_HRV96a    CATGTTTTATGATGGATATGATGGTGACTCTGAATCAACACGCTATGGAACATCTGTTAC
2490  90_HRV16a|    CATGTTTTATGATGGTTATGATGGAGACACATATAAATCCAGATATGGAACTGTAGTCAC
2491  91_HRV16b|    CATGTTTTATGATGGTTATGATGGAGACACATATAAATCCAGATATGGAACTGTAGTCAC
2492  92_1AYM_A     CATGTTTTATGATGGTTATGATGGAGACACATATAAATCCAGATATGGAACTGTAGTCAC
2493  93_HRV81a|    CATGTTCTATGATGGATATGATGGTGATACTTATCACTCCAGATACGGGACTGTAGTCAC
2494  94_HRV81b|    CATGTTCTATGATGGATATGATGGTGATACTTATCACTCCAGATACGGGACTGTAGTCAC
2495  95_HRV81      CATGTTCTATGATGGATATGATGGTGATACTTATCACTCCAGATACGGGACTGTAGTCAC
2496  147_HRV2      CATGTTTTATGATGGGTATGATG------AACAAGATCAAAACTATGGTACAGCAAGCAC
2497  148_HRV2a|    CATGTTTTATGATGGGTATGATG------AACAAGATCAAAACTATGGTACAGCAAGCAC
2498  149_HRV2b|    CATGTTTTATGATGGGTATGATG------AACAAGATCAAAACTATGGTACAGCAAGCAC
2499  150_HRV49a    CATGTTTTATGATGGATATAATG------AACAGGGCCAAAATTATGGTACGGTAAGTAC
2500  151_HRV49b    CATGTTTTATGATGGATATAATG------AACAGGGCCAAAATTATGGTACGGTAAGTAC
2501  152_HRV49     CATGTTTTATGATGGATATAATG------AACAGGGCCAAAATTATGGTACGGTAAGTAC
2502  153_HRV23a    CATGTTTTATGATGGATACAATG------AGAAAGGCACGCATTATGGAACAGTTAGCAC
2503  154_HRV23b    CATGTTTTATGATGGATACAATG------AGAAAGGCACGCATTATGGAACAGTTAGCAC
2504  155_HRV23     CATGTTTTATGATGGATACAATG------AGAAAGGCACGCATTATGGAACAGTTAGCAC
2505  156_HRV30a    CATGTTCTATGATGGATACAATG------AGGGAGGCACAAATTATGGTACAGTGAGCAC
2506  157_HRV30b    CATGTTCTATGATGGATACAATG------AGGGAGGCACAAATTATGGTACAGTGAGCAC
2507  158_HRV30     CATGTTCTATGATGGATACAATG------AGGGAGGCACAAATTATGGTACAGTGAGCAC
2508  159_HRV7      TATGTTCTATGATGGATATGATGGTGATGATGCGTCATCCAAATATGGTTCCGTAGTAAC
2509  160_HRV7b|    TATGTTCTATGATGGATATGATGGTGATGATGCGTCATCCAAATATGGTTCCGTAGTAAC
2510  161_HRV7a|    TATGTTCTATGATGGATATGATGGTGATGATGCGTCATCCAAATATGGTTCCGTAGTAAC
2511  162_HRV88     TATGTTTTATGATGGATATGATGGTGATCATCATCTAGGTATGGCTCAGTGGTAAC
2512  163_HRV88a    TATGTTTTATGATGGATATGATGGTGATGATGCATCATCTAGGTATGGCTCAGTGGTAAC
2513  164_HRV88b    TATGTTTTATGATGGATATGATGGTGATGATGCATCATCTAGGTATGGCTCAGTGGTAAC
2514  165_HRV36a    TATGTTTTATGATGGTTATGATGGTGATAATGCCGCATCAAAATATGGATCTGTGGTTAC
2515  166_HRV36b    TATGTTTTATGATGGTTATGATGGTGATAATGCCGCATCAAAATATGGATCTGTGGTTAC
2516  167_HRV36     TATGTTTTATGATGGTTATGATGGTGATAATGCCGCATCAAAATATGGATCTGTGGTTAC
2517  168_HRV89a    CATGTTTTATGATGGTTATGATGGTGATAGTGCAGCATCAAAATACGGTTCTGTAGTCAC
2518  169_HRV89b    CATGTTTTATGATGGTTATGATGGTGATAGTGCAGCATCAAAATACGGTTCTGTAGTCAC
2519  170_HRV89     CATGTTTTATGATGGTTATGATGGTGATAGTGCAGCATCAAAATACGGTTCTGTAGTCAC
2520  171_HRV58     TATGTTTTATGATGGCTATGATGGTGATGATGCTAAATCAATATATGGTTCTGTGGTAAC
2521  172_HRV58a    TATGTTTTATGATGGCTATGATGGTGATGATGCTAAATCAATATATGGTTCTGTGGTAAC
2522  173_HRV58b    TATGTTTTATGATGGCTATGATGGTGATGATGCTAAATCAATATATGGTTCTGTGGTAAC
2523  174_HRV12a    CATGTTTTATGATGGTTATGCTGATGACAACCCAAGTGCACCTTATGGAACTGTAGTTAC
2524  175_HRV12b    CATGTTTTATGATGGTTATGCTGATGACAACCCAAGTGCACCTTATGGAACTGTAGTTAC
2525  176_HRV12     CATGTTTTATGATGGTTATGCTGATGACAACCCAAGTGCACCTTATGGAACTGTAGTTAC
2526  177_HRV78a    CATGTTTTATGGATACTCGGATGACAGCACATCCTCTCCATATGGCACTGTAGTTAC
2527  178_HRV78b    CATGTTTTATGATGGATACTCGGATGACAGCACATCCTCTCCATATGGCACTGTAGTTAC
2528  179_HRV78     CATGTTTTATGATGGATACTCGGATGACAGCACATCCTCTCCATATGGCACTGTAGTTAC
2529  180_HRV20     TATGTTTTATGATGGTTATGAAGATGATAAGG---GAAGTGTGTATGGGTCTGTTGTCAC
2530  181_HRV20a    TATGTTTTATGATGGTTATGAAGATGATAAGG---GAAGTGTGTATGGGTCTGTTGTCAC
```

FIG. D8 CONT'D

04-2.trace								9/20/2007 5:04 PM

```
2531 182_HRV20b       TATGTTTTATGATGGTTATGAAGATGATAAGG---GAAGTGTGTATGGGTCTGTTGTCAC
2532 183_HRV68        TATGTTTTATGATGGATATGAGGATGACAAAG---GAAGTGTGTATGGATCTGTTGTTAC
2533 184_HRV68a       TATGTTTTATGATGGATATGAGGATGACAAAG---GAAGTGTGTATGGATCTGTTTGTTAC
2534 185_HRV68b       TATGTTTTATGATGGATATGAGGATGACAAAG---GAAGTGTGTATGGATCTGTTGTTAC
2535 186_HRV28        CATGTTTTATGATGGTTATGAAGATGACAATG---GAACTACCTATGGTGCAGTGGTTAC
2536 187_HRV28a       CATGTTTTATGATGGTTATGAAGATGACAATG---GAACTACCTATGGTGCAGTGGTTAC
2537 188_HRV28b       CATGTTTTATGATGGTTATGAAGATGACAATG---GAACTACCTATGGTGCAGTGGTTAC
2538 189_HRV53a       TATGTTCTATGATGGGTATGAAGATGACAATG---GCACCACTTATGGGGCTGTTGTTAC
2539 190_HRV53b       TATGTTCTATGATGGGTATGAAGATGACAATG---GCACCACTTATGGGGCTGTTGTTAC
2540 191_HRV53        TATGTTCTATGATGGGTATGAAGATGACAATG---GCACCACTTATGGGGCTGTTGTTAC
2541 192_HRV46a       CATGTTTTATGATGGCTACGAAAGTGATAAAG---GCAAGATCTATGGAACTGCAGTCAC
2542 193_HRV46b       CATGTTTTATGATGGCTACGAAAGTGATAAAG---GCAAGATCTATGGAACTGCAGTCAC
2543 194_HRV46        CATGTTTTATGATGGCTACGAAAGTGATAAAG---GCAAGATCTATGGAACTGCAGTCAC
2544 195_HRV80a       CATGTTCTATGATGGGTATGAGAGTGATAAAG---GCAACATTTATGGAACAGCAGTTAC
2545 196_HRV80b       CATGTTCTATGATGGGTATGAGAGTGATAAAG---GCAACATTTATGGAACAGCAGTTAC
2546 197_HRV80        CATGTTCTATGATGGGTATGAGAGTGATAAAG---GCAACATTTATGGAACAGCAGTTAC
2547 198_HRV51        CATGTTTTATGATGGGTATGAAGGTGATAGTTTGACCTCACAGTACGGTTCAGTAGTCAC
2548 199_HRV51a       CATGTTTTATGATGGGTATGAAGGTGATAGTTTGACCTCACAGTACGGTTCAGTAGTCAC
2549 200_HRV51b       CATGTTTTATGATGGGTATGAAGGTGATAGTTTGACCTCACAGTACGGTTCAGTAGTCAC
2550 201_HRV65a       CATGTTCTATGATGGTTATGAGGGTGATGACCCAAATTCAAAATATGGTTCAGTGGTTAC
2551 202_HRV65b       CATGTTCTATGATGGTTATGAGGGTGATGACCCAAATTCAAAATATGGTTCAGTGGTTAC
2552 203_HRV65        CATGTTCTATGATGGTTATGAGGGTGATGACCCAAATTCAAAATATGGTTCAGTGGTTAC
2553 204_HRV71a       CATGTTCTATGATGGGTATGAAGGTGATGCCCTCAGTTCTAAATATGGCTCAGTAGTTAC
2554 205_HRV71b       CATGTTCTATGATGGGTATGAAGGTGATGCCCTCAGTTCTAAATATGGCTCAGTAGTTAC
2555 206_HRV71        CATGTTCTATGATGGGTATGAAGGTGATGCCCTCAGTTCTAAATATGGCTCAGTAGTTAC
2556 207_HRV8         CATGTTCTATGATGGTTATCAGATGGTTTAGATGCTATTTATGGTATTCCTGTTAC
2557 208_HRV95        CATGTTCTATGATGGTTATGATTCAGATGGTTTAGATGCTATTTATGGTATTCCTGTTAC
2558 209_HRV45        CATGTTTTATGATGGATACGACACTGATGGCACAGATGCAGTGTATGGTGTTAGTGTGAC
2559 210_HRV45a       CATGTTTTATGATGGATACGACACTGATGGCACAGATGCAGTGTATGGTGTTAGTGTGAC
2560 211_HRV45b       CATGTTTTATGATGGATACGACACTGATGGCACAGATGCAGTGTATGGTGTTAGTGTGAC
2561 GROUP_1          -ATGTT-TA-GA-GG-TA----------------------TA-GG------------
2562
2563  1_HRV1A1|d      TAATGATATGGGTACTATATGCTCAAGAATAGTTACAGAAAAACAGAAACATTCTGTTGT
2564  2_HRV1A2|d      TAATGATATGGGTACTATATGCTCAAGAATAGTTACAGAAAAACAGAAACATTCTGTTGT
2565  3_HRV1A|cD      TAATGATATGGGTACTATATGCTCAAGAATAGTTACAGAAAAACAGAAACATTCTGTTGT
2566  4_HRV1B1|d      CAATGATATGGGAACCATATGTTCAAGAATAGTTACAGAGAAGCAGGAACACCCTGTCGT
2567  5_HRV1B2|d      CAATGATATGGGAACCATATGTTCAAGAATAGTTACAGAGAAGCAGGAACACCCTGTCGT
2568  6_HRV1B         CAATGATATGGGAACCATATGTTCAAGAATAGTTACAGAGAAGCAGGAACACCCTGTCGT
2569  7_HRV40a|d      TAACCATATGGGACGCTATGCTCAAGAATAGTCACCAACAAGCAGCAGCATGAAGTTGA
2570  8_HRV40b|d      TAACCATATGGGAACGCTATGCTCAAGAATAGTCACCAACAAGCAGCAGCATGAAGTTGA
2571  9_HRV40         TAACCATATGGGAACGCTATGCTCAAGAATAGTCACCAACAAGCAGCAGCATGAAGTTGA
2572 10_HRV85         CAACCACATGGGAACACTGTGCTCGAGGATAGTTACCAACAAACAGCAGCATGAGGTTGA
2573 11_HRV85a|       CAACCACATGGGAACACTGTGCTCGAGGATAGTTACCAACAAACAGCAGCATGAGGTTGA
2574 12_HRV85b|       CAACCACATGGGAACACTGTGCTCGAGGATAGTTACCAACAAACAGCAGCATGAGGTTGA
2575 13_HRV56a|       AAACCACATGGGGACACTCTGTTCAAGAATTGTGACAAATAAACAACTTCATCCTGTTGA
2576 14_HRV56b|       AAACCACATGGGGACACTCTGTTCAAGAATTGTGACAAATAAACAACTTCATCCTGTTGA
2577 15_HRV56         AAACCACATGGGGACACTCTGTTCAAGAATTGTGACAAATAAACAACTTCATCCTGTTGA
2578 16_HRV54         CAATCATATGGGTACTTTGTGTTCAAGAGTGGTTACTGATAAACAAAAACACCCAGTTGA
2579 17_HRV98         TAATCACATGGGCACTTTGTGTTCAAGAGTAGTTACTGGCAAACAAGAACACCCAGTTGA
2580 18_HRV59a|       CAACCACATGGGCACTTTATTGTCTAGAATAGTTACAAACAGTCAGGAGCATCCAGTGGA
2581 19_HRV59b|       CAACCACATGGGCACTTTATTGTCTAGAATAGTTACAAACAGTCAGGAGCATCCAGTGGA
2582 20_HRV59         CAACCACATGGGCACTTTATTGTCTAGAATAGTTACAAACAGTCAGGAGCATCCAGTGGA
2583 21_HRV63         TAACCACATGGGGACTTTATGTTCTAGAATTGTAACAAACAGCCAAGAACATCCAGTTGA
2584 22_HRV63b|       TAACCACATGGGGACTTTATGTTCTAGAATTGTAACAAACAGCCAAGAACATCCAGTTGA
2585 23_HRV63a|       TAACCACATGGGGACTTTATGTTCTAGAATTGTAACAAACAGCCAAGAACATCCAGTTGA
2586 24_HRV39         TAATGATATGGGTACACTTTGCACTAGAATTGTAACAAACCAACAGGAACACCTAGTGGA
2587 25_HRV39a|       TAATGATATGGGTACACTTTGCACTAGAATTGTAACAAACCAACAGGAACACCTAGTGGA
2588 26_HRV39b|       TAATGATATGGGTACACTTTGCACTAGAATTGTAACAAACCAACAGAAACACCTAGTGGA
2589 27_HRV10a|       AAATCACATGGGCACTTTGTGCATGCGAATAGTCACAAACCAGCAAGCACATGAGGTGGA
2590 28_HRV10b|       AAATCACATGGGCACTTTGTGCATGCGAATAGTCACAAACCAGCAAGCACATGAGGTGGA
2591 29_HRV10         AAATCACATGGGCACTTTGTGCATGCGAATAGTCACAAACCAGCAAGCACATGAGGTGGA
2592 30_HRV100a       TAACCACATGGGTACACTTTGTATGAGGATAGTTACAAATCAGCAAGCACATGAGGTGGA
2593 31_HRV100b       TAACCACATGGGTACACTTTGTATGAGGATAGTTACAAATCAGCAAGCACATGAGGTGGA
2594 32_HRV100        TAACCACATGGGTACACTTTGTATGAGGATAGTTACAAATCAGCAAGCACATGAGGTGGA
2595 33_HRV66         TAATCATATGGGTACATTATGTATTAGGATTGTTACAAATGAACAGCACCATAATGTTGA
```

FIG. D8 CONT'D

```
04-2.trace                                                                  9/20/2007 5:04 PM 2596  34_HRV66b|    TAATCATATGGGTACATTATGTATTAGGATTGTTACAAATGAACAGCACCATAATGTTGA
2597  35_HRV66a|    TAATCATATGGGTACATTATGTATTAGGATTGTTACAAATGAACAGCACCATAATGTTGA
2598  36_HRV77a|    TAATCACATGGGCACACTGTGCATTAGAATAGTCACTAATCAGCAAAATCATGAGGTTGA
2599  37_HRV77b|    TAATCACATGGGCACACTGTGCATTAGAATAGTCACTAATCAGCAAAATCATGAGGTTGA
2600  38_HRV77     TAATCACATGGGCACACTGTGCATTAGAATAGTCACTAATCAGCAAAATCATGAGGTTGA
2601  39_HRV62a    TAATCGTATGGGGGCACTGTGTATGAGGATTGTCACAAACAAACAAGTTCATGATGTTGA
2602  40_HRV62b    TAATCGTATGGGGGCACTGTGTATGAGGATTGTCACAAACAAACAAGTTCATGATGTTGA
2603  41_HRV25     TAACCGTATGGGAGCACTGTGCATGAGAATTGTCACAAATAAACAAGTCCATGATGTTGA
2604  42_HRV29a    TAACCGGATGGGGACGCTTTGTGTCAGAATTGTTACAGGCAAACAAGCTCATGATGTTCA
2605  43_HRV29b    TAACCGGATGGGGACGCTTTGTGTCAGAATTGTTACAGGCAAACAAGCTCATGATGTTCA
2606  44_HRV44a    TAACCGGATGGGGACGCTTTGCGTCAGGATCGTTACGGGCAAACAGGCTCATGATGTCCA
2607  45_HRV44b    TAACCGGATGGGGACGCTTTGCGTCAGGATCGTTACGGGCAAACAGGCTCATGATGTCCA
2608  46_HRV31     TAATCGCATGGGTGCACTATGCATGAGAGTTGTCACTAACAAACAAGCTCATAAAGTTGA
2609  47_HRV31a|   TAATCGCATGGGTGCACTATGCATGAGAGTTGTCACTAACAAACAAGCTCATAAAGTTGA
2610  48_HRV31b|   TAATCGCATGGGTGCACTATGCATGAGAGTTGTCACTAACAAACAAGCTCATAAAGTTGA
2611  49_HRV47     CAATCGCATGGGTGCATTGTGTATGAGAGTTGTAACAAACAAGCAACTCCATAAAGTTGA
2612  50_HRV47a|   CAATCGCATGGGTGCATTGTGTATGAGAGTTGTAACAAACAAGCAACTCCATAAAGTTGA
2613  51_HRV47b|   CAATCGCATGGGTGCATTGTGTATGAGAGTTGTAACAAACAAGCAACTCCATAAAGTTGA
2614  52_HRV11     CAATGATATGGGCACTCTGTGTTATAGAATAGTAACTGATGACCATAGACACAAAATTGA
2615  53_HRV11b|   CAATGATATGGGCACTCTGTGTTATAGAATAGTAACTGATGACCATAGACACAAAATTGA
2616  54_HRV11a|   CAATGATATGGGCACTCTGTGTTATAGAATAGTAACTGATGACCATAGACACAAAATTGA
2617  55_HRV76     CAATGACATGGGCACCCTATGTTCCAGGATAGTAACTGATGATCATAAGCACAAGATTGA
2618  56_HRV76b|   CAATGACATGGGCACCCTATGTTCCAGGATAGTAACTGATGATCATAAGCACAAGATTGA
2619  57_HRV76a|   CAATGACATGGGCACCCTATGTTCCAGGATAGTAACTGATGATCATAAGCACAAGATTGA
2620  58_HRV33     CAATGACATGGGCACTTTATGCTCTAGAATAGTTACAGATAATCATAAGCATCCAATAGA
2621  59_HRV33b|   CAATGACATGGGCACTTTATGCTCTAGAATAGTTACAGATAATCATAAGCATCCAATAGA
2622  60_HRV33a|   CAATGACATGGGCACTTTATGCTCTAGAATAGTTACAGATAATCATAAGCATCCAATAGA
2623  61_HRV24a|   AAACGACATGGGAACTCTATGCTATAGAATAGTCACTGACAAGCATAATCACCAAATAGA
2624  62_HRV24b|   AAACGACATGGGAACTCTATGCTATAGAATAGTCACTGACAAGCATAATCACCAAATAGA
2625  63_HRV24     AAACGACATGGGAACTCTATGCTATAGAATAGTCACTGACAAGCATAATCACCAAATAGA
2626  64_HRV90     TAATGATATGGGAACCTTATGTTATAGAATAGTTACAGATGAACATGCCCACAAAATAGA
2627  65_HRV90a|   TAATGATATGGGAACCTTATGTTATAGAATAGTTACAGATGAACATGCCCACAAAATAGA
2628  66_HRV90b|   TAATGATATGGGAACCTTATGTTATAGAATAGTTACAGATGAACATGCCCACAAAATAGA
2629  67_HRV34     TAATGACATGGGTACTTTATGCTCCAGAATTGTAACTGATGAACACCAAAACAGAGTAGA
2630  68_HRV34b|   TAATGACATGGGTACTTTATGCTCCAGAATTGTAACTGATGAACACCAAAACAGAGTAGA
2631  69_HRV34a|   TAATGACATGGGTACTTTATGCTCCAGAATTGTAACTGATGAACACCAAAACAGAGTAGA
2632  70_HRV50a|   CAATGACATGGGCACTTTGTGTTCTAGGATTGTCACTGATGAGCACCAAAATAAAGTGGA
2633  71_HRV50b|   CAATGACATGGGCACTTTGTGTTCTAGGATTGTCACTGATGAGCACCAAAATAAAGTGGA
2634  72_HRV50     CAATGACATGGGCACTTTGTGTTCTAGGATTGTCACTGATGAGCACCAAAATAAAGTGGA
2635  73_HRV18a|   AAATGACATGGGTACCTTGTGCTCTAGAATAGTCACAGATAAACATAAGAATGAGGTGGA
2636  74_HRV18b|   AAATGACATGGGTACCTTGTGCTCTAGAATAGTCACAGATAAACATAAGAATGAGGTGGA
2637  75_HRV18     AAATGACATGGGTACCTTGTGCTCTAGAATAGTCACAGATAAACATAAGAATGAGGTGGA
2638  76_HRV55     TAATGACATGGGTACTTTATGTTCTAGAATAATAACTGATAACCATAAGCACCCAATTGA
2639  77_HRV55b|   TAATGACATGGGTACTTTATGTTCTAGAATAATAACTGATAACCATAAGCACCCAATTGA
2640  78_HRV55a|   TAATGACATGGGTACTTTATGTTCTAGAATAATAACTGATAACCATAAGCACCCAATTGA
2641  79_HRV57     TAATGACATGGGCACTTTATGTTCTAGAATTGTTACTGACCAGCACACACATCCCATAAA
2642  80_HRV57a|   TAATGACATGGGCACTTTATGTTCTAGAATTGTTACTGACCAGCACACACATCCCATAAA
2643  81_HRV57b|   TAATGACATGGGCACTTTATGTTCTAGAATTGTTACTGACCAGCACACACATCCCATAAA
2644  82_HRV21     TAATGATATGGGATCTCTATGCTACAGAATAGTAACTGGCCAGCATAAGCATAAGATAGA
2645  83_HRVHan    TAATGATATGGGATCTCTATGCTACAGAATAGTAACTGATCAGCATAAGCACAAGATAGA
2646  84_HRV43     CAACCACATGGGAACATTATGTTCTAGGATAGTTACAGAAGAACACCAAAATCAAATCGA
2647  85_HRV43b|   CAACCACATGGGAACATTATGTTCTAGGATAGTTACAGAAGAACACCAAAATCAAATCGA
2648  86_HRV43a|   CAACCACATGGGAACATTATGTTCTAGGATAGTTACAGAAGAACACCAAAATCAAATCGA
2649  87_HRV75     TAATCACATGGGGACACTGTGTTCTAGAATAGTTACAGAAGAACATCGAAATAAAGTTGA
2650  88_HRV75b|   TAATCACATGGGGACACTGTGTTCTAGAATAGTTACAGAAGAACATCGAAATAAAGTTGA
2651  89_HRV75a|   TAATCACATGGGGACACTGTGTTCTAGAATAGTTACAGAAGAACATCGAAATAAAGTTGA
2652  96_HRV9a|d   AAATGATATCTTTATGTTCCCGTGTAGTTACTGAAGAGCATGGACCCCGTGTCAA
2653  97_HRV9b|d   AAATGATATGGGATCTTTATGTTCCCGTGTAGTTACTGAAGAGCATGGACCCCGTGTCAA
2654  98_HRV9      AAATGATATGGGATCTTTATGTTCCCGTGTAGTTACTGAAGAGCATGGACCCCGTGTCAA
2655  99_HRV32     AAATGATATGGGTTCCCTGTGTTCTCGTATAGTCACCGAAGAGCACGGATCCCGTGTTGA
2656  100_HRV32a   AAATGATATGGGTTCCCTGTGTTCTCGTATAGTCACCGAAGAGCACGGATCCCGTGTTGA
2657  101_HRV32b   AAATGATATGGGTTCCCTGTGTTCTCGTATAGTCACCGAAGAGCACGGATCCCGTGTTGA
2658  102_HRV67    TAATGATATGGGTTCCTTGTGTTCGCGTATAGTTACTGAAGAACATGGTTCTCGCGTAAA
2659  103_HRV67a   TAATGATATGGGTTCCTTGTGTTCGCGTATAGTTACTGAAGAACATGGTTCTCGCGTAAA
2660  104_HRV67b   TAATGATATGGGTTCCTTGTGTTCGCGTATAGTTACTGAAGAACATGGTTCTCGCGTAAA
```

FIG. D8 CONT'D

```
04-2.trace                                                                                                   9/20/2007 5:04 PM 2661  105_HRV15       TAATGACATGGGGACACTGTGTTCTAGAATAGTAACTGAAGAGCATGGGACACGTGTAGA
2662  106_HRV15a      TAATGACATGGGGACACTGTGTTCTAGAATAGTAACTGAAGAGCATGGGACACGTGTAGA
2663  107_HRV15b      TAATGACATGGGGACACTGTGTTCTAGAATAGTAACTGAAGAGCATGGGACACGTGTAGA
2664  108_HRV74a      AAATGACATGGGAACTCTATGTTCTAGAATTGTGACTGAAGAACACGATGCACGTGTGGA
2665  109_HRV74b      AAATGACATGGGAACTCTATGTTCTAGAATTGTGACTGAAGAACACGATGCACGTGTGGA
2666  110_HRV74       AAATGACATGGGAACTCTATGTTCTAGAATTGTGACTGAAGAACACGATGCACGTGTGGA
2667  111_HRV38a      CAATGATATGGGGACACTTTGTTCAAGAATAGTCACTGAAAATCATGGGACCCAAGTGAA
2668  112_HRV38b      CAATGATATGGGGACACTTTGTTCAAGAATAGTCACTGAAAATCATGGGACCCAAGTGAA
2669  113_HRV38       CAATGATATGGGGACACTTTGTTCAAGAATAGTCACTGAAAATCATGGGACCCAAGTGAA
2670  114_HRV60       CAATGACATGGGAACGTTGTGCTCCAGAATAGTTACTGAACACCATGGTACACAGGTTCA
2671  115_HRV60a      CAATGACATGGGAACGTTGTGCTCCAGAATAGTTACTGAACACCATGGTACACAGGTTCA
2672  116_HRV60b      CAATGACATGGGAACGTTGTGCTCCAGAATAGTTACTGAACACCATGGTACACAGGTTCA
2673  117_HRV64a      AAATGATATGGGCACTTTGTGTTCTAGAATTGTGACTGAGGAACACACAACACAGGTCAA
2674  118_HRV64b      AAATGATATGGGCACTTTGTGTTCTAGAATTGTGACTGAGGAACACACAACACAGGTCAA
2675  119_HRV64       AAATGATATGGGCACTTTGTGTTCTAGAATTGTGACTGAGGAACACACAACACAGGTCAA
2676  120_HRV94a      AAATGACATGGGAACATTATGCTCCAGGATTGTGACTGAGGAGCACAAGACACAGGTTAA
2677  121_HRV94b      AAATGACATGGGAACATTATGCTCCAGGATTGTGACTGAGGAGCACAAGACACAGGTTAA
2678  122_HRV94       AAATGACATGGGAACATTATGCTCCAGGATTGTGACTGAGGAGCACAAGACACAGGTTAA
2679  123_HRV22       AAATGATATGGGCACACTGTGCTCTAGGATTGTGACTGAAGAACACCAGACACAAGTCAA
2680  124_HRV22a      AAATGATATGGGCACACTGTGCTCTAGGATTGTGACTGAAGAACACCAGACACAAGTCAA
2681  125_HRV22b      AAATGATATGGGCACACTGTGCTCTAGGATTGTGACTGAAGAACACCAGACACAAGTCAA
2682  126_HRV82       AAATGACATGGGTACACTGTGTTCTAGAATTGTAACTGAAGAACACCAGACTCAAGTCAG
2683  127_HRV82b      AAATGACATGGGTACACTGTGTTCTAGAATTGTAACTGAAGAACACCAGACTCAAGTCAG
2684  128_HRV82a      AAATGACATGGGTACACTGTGTTCTAGAATTGTAACTGAAGAACACCAGACTCAAGTCAG
2685  129_HRV19       TAATGATATGGGAACCTTATGCTCCAGAATAGTAACTGATGAACACAAACACAGGTTGC
2686  130_HRV19a      TAATGATATGGGAACCTTATGCTCCAGAATAGTAACTGATGAACACAAACACAGGTTGC
2687  131_HRV19b      TAATGATATGGGAACCTTATGCTCCAGAATAGTAACTGATGAACACAAACACAGGTTGC
2688  132_HRV13       TAATGATATGGGCACACTTTGCTTCAGAATAGTAACTGAAGAACATACTAACAAGGTCAA
2689  133_HRV13a      TAATGATATGGGCACACTTTGCTTCAGAATAGTAACTGAAGAACATACTAACAAGGTCAA
2690  134_HRV13b      TAATGATATGGGCACACTTTGCTTCAGAATAGTAACTGAAGAACATACTAACAAGGTCAA
2691  135_HRV41       AAATGACATGGGTACATTATGCTTTAGAATAGTTACTGAAGAACACACCAACAAAGTTAA
2692  136_HRV41a      AAATGACATGGGTACATTATGCTTTAGAATAGTTACTGAAGAACACACCAACAAAGTTAA
2693  137_HRV41b      AAATGACATGGGTACATTATGCTTTAGAATAGTTACTGAAGAACACACCAACAAAGTTAA
2694  138_HRV73       TAATGACATGGGCACATTATGCTTTAGGATAGTGACTGAAGAACACACTAGCAGGGTAAA
2695  139_HRV73b      TAATGACATGGGCACATTATGCTTTAGGATAGTGACTGAAGAACACACTAGCAGGGTAAA
2696  140_HRV73a      TAATGACATGGGCACATTATGCTTTAGGATAGTGACTGAAGAACACACTAGCAGGGTAAA
2697  141_HRV61       AAATGATATGGGTGCATTGTGCTTTAGAATAGTAACTGAACAGCATACAAATCAAGTTAA
2698  142_HRV61a      AAATGATATGGGTGCATTGTGCTTTAGAATAGTAACTGAACAGCATACAAATCAAGTTAA
2699  143_HRV61b      AAATGATATGGGTGCATTGTGCTTTAGAATAGTAACTGAACAGCATACAAATCAAGTTAA
2700  144_HRV96       CAATGACATGGGCACTTTATGTTTTAGAATAGTGACAGAGGAACACACCAACAAGGTCAA
2701  145_HRV96b      CAATGACATGGGCACTTTATGTTTTAGAATAGTGACAGAGGAACACACCAACAAGGTCAA
2702  146_HRV96a      CAATGACATGGGCACTTTATGTTTTAGAATAGTGACAGAGGAACACACCAACAAGGTCAA
2703  90_HRV16a|      CAATGACATGGGAACTTTGTGTTCGCGTATTGTGACCAGTGAGCAATTACACAAAGTCAA
2704  91_HRV16b|      CAATGACATGGGAACTTTGTGTTCGCGTATTGTGACCAGTGAGCAATTACACAAAGTCAA
2705  92_1AYM_A       CAATGACATGGGAACTTTGTGTTCGCGTATTGTGACCAGTGAGCAATTACACAAAGTCAA
2706  93_HRV81a|      TAATGATATGGGAACATTATGCTCACGGATAGTGACAAGTGAGCAAGTGCACAAGGTGAA
2707  94_HRV81b|      TAATGATATGGGAACATTATGCTCACGGATAGTGACAAGTGAGCAAGTGCACAAGGTGAA
2708  95_HRV81        TAATGATATGGGAACATTATGCTCACGGATAGTGACAAGTGAGCAAGTGCACAAGGTGAA
2709  147_HRV2        AAATAACATGGGGTCACTATGCTCTAGGATAGTAACAGAGAAACACATTCATAAGGTACA
2710  148_HRV2a|      AAATAACATGGGGTCACTATGCTCTAGGATAGTAACAGAGAAACACATTCATAAGGTACA
2711  149_HRV2b|      AAATAACATGGGGTCACTATGCTCTAGGATAGTAACAGAGAAACACATTCATAAGGTACA
2712  150_HRV49a      AAACAACATGGGATCATTATGCTCTAGGATAGTAACAGAGAAACACATTCACAGTATGCA
2713  151_HRV49b      AAACAACATGGGATCATTATGCTCTAGGATAGTAACAGAGAAACACATTCACAGTATGCA
2714  152_HRV49       AAACAACATGGGATCATTATGCTCTAGGATAGTAACAGAGAAACACATTCACAGTATGCA
2715  153_HRV23a      AAACAACATGGGCACATTGTGCTCCAGAGTGGTAACAGAGAAACACATTCATGATATGCG
2716  154_HRV23b      AAACAACATGGGCACATTGTGCTCCAGAGTGGTAACAGAGAAACACATTCATGATATGCG
2717  155_HRV23       AAACAACATGGGCACATTGTGCTCCAGAGTGGTAACAGAGAAACACATTCATGATATGCG
2718  156_HRV30a      AAACAACATGGGCACACTGTGTTCCAGAGTGGTAACAGAAAACACATTCATGATGTGCG
2719  157_HRV30b      AAACAACATGGGCACACTGTGTTCCAGAGTGGTAACAGAAAACACATTCATGATGTGCG
2720  158_HRV30       AAACAACATGGGCACACTGTGTTCCAGAGTGGTAACAGAAAACACATTCATGATGTGCG
2721  159_HRV7        CAATGACATGGGAACCATATGTGTTAGACTAGTTACATCTACACAAAAACACAATTTAAA
2722  160_HRV7b|      CAATGACATGGGAACCATATGTGTTAGACTAGTTACATCTACACAAAAACACAATTTAAA
2723  161_HRV7a|      CAATGACATGGGAACCATATGTGTTAGACTAGTTACATCTACACAAAAACACAATTTAAA
2724  162_HRV88       TAATGATATGGGAACTATATGTATTAGATTGGTCACCTCCACCCAAAAGCATAAACTGAA
2725  163_HRV88a      TAATGATATGGGAACTATATGTATTAGATTGGTCACCTCCACCCAAAAGCATAAACTGAA
```

FIG. D8 CONT'D

```
04-2.trace                                                                                    9/20/2007 5:04 PM 2726  164_HRV88b    TAATGATATGGGAACTATATGTATTAGATTGGTCACCTCCACCCAAAAGCATAAACTGAA
2727  165_HRV36a    TAACGACATGGGAACCATATGTGTTAGAATAGTTACATCCAACCAAAAACATGATTTAAA
2728  166_HRV36b    TAACGACATGGGAACCATATGTGTTAGAATAGTTACATCCAACCAAAAACATGATTTAAA
2729  167_HRV36     TAACGACATGGGAACCATATGTGTTAGAATAGTTACATCCAACCAAAAACATGATTTAAA
2730  168_HRV89a    TAATGATATGGGAACCATATGTGTTAGAATAGTGACATCCAACCAAAAACATGATTTAAA
2731  169_HRV89b    TAATGATATGGGAACCATATGTGTTAGAATAGTGACATCCAACCAAAAACATGATTTAAA
2732  170_HRV89     TAATGATATGGGAACCATATGTGTTAGAATAGTGACATCCAACCAAAAACATGATTTAAA
2733  171_HRV58     AAATGACATGGGAACTATATGTGTTAGAATAGTCACATCCAAACAAAGACACAATTTAAA
2734  172_HRV58a    AAATGACATGGGAACTATATGTGTTAGAATAGTCACATCCAAACAAAGACACAATTTAAA
2735  173_HRV58b    AAATGACATGGGAACTATATGTGTTAGAATAGTCACATCCAAACAAAGACACAATTTAAA
2736  174_HRV12a    CAATGACATGGGTTCACTGTGTGTCAGAATAGTTACAGACCAGCAAAAACATAAAGTTAA
2737  175_HRV12b    CAATGACATGGGTTCACTGTGTGTCAGAATAGTTACAGACCAGCAAAAACATAAAGTTAA
2738  176_HRV12     CAATGACATGGGTTCACTGTGTGTCAGAATAGTTACAGACCAGCAAAAACATAAAGTTAA
2739  177_HRV78a    CAATGACATGGGTACACTGTGTATGAGGATGGTTACAGATCAACAACAACATAAGGTCAC
2740  178_HRV78b    CAATGACATGGGTACACTGTGTATGAGGATGGTTACAGATCAACAACAACATAAGGTCAC
2741  179_HRV78     CAATGACATGGGTACACTGTGTATGAGGATGGTTACAGATCAACAACAACATAAGGTCAC
2742  180_HRV20     AAACGATATGGGCACATTGTGTGTTCGTATTGTGACTGAGCAGCAGACACATAAGGTTAA
2743  181_HRV20a    AAACGATATGGGCACATTGTGTGTTCGTATTGTGACTGAGCAGCAGACACATAAGGTTAA
2744  182_HRV20b    AAACGATATGGGCACATTGTGTGTTCGTATTGTGACTGAGCAGCAGACACATAAGGTTAA
2745  183_HRV68     AAATGATATGGGCACATTATGTGTCCGTATTGTGACTGAGCAGCAGACACATAGGGTCAA
2746  184_HRV68a    AAATGATATGGGCACATTATGTGTCCGTATTGTGACTGAGCAGCAGACACATAGGGTCAA
2747  185_HRV68b    AAATGATATGGGCACATTATGTGTCCGTATTGTGACTGAGCAGCAGACACATAGGGTCAA
2748  186_HRV28     AAATCATATGGGAACACTCTGTGCTCGCATAGTAACTGAACAACAGAAGCATGAAGTCAA
2749  187_HRV28a    AAATCATATGGGAACACTCTGTGCTCGCATAGTAACTGAACAACAGAAGCATGAAGTCAA
2750  188_HRV28b    AAATCATATGGGAACACTCTGTGCTCGCATAGTAACTGAACAACAGAAGCATGAAGTCAA
2751  189_HRV53a    TAATGATATGGGAACACTTTGTGTGCGCATAGTGACTGAGCAACAGAAAAATGAGGTCAA
2752  190_HRV53b    TAATGATATGGGAACACTTTGTGTGCGCATAGTGACTGAGCAACAGAAAAATGAGGTCAA
2753  191_HRV53     TAATGATATGGGAACACTTTGTGTGCGCATAGTGACTGAGCAACAGAAAAATGAGGTCAA
2754  192_HRV46a    CAATGATATGGGAACTATATGTGTCAGAATTGTTACCGAACAACAAAAACATAAGGTTCT
2755  193_HRV46b    CAATGATATGGGAACTATATGTGTCAGAATTGTTACCGAACAACAAAAACATAAGGTTCT
2756  194_HRV46     CAATGATATGGGAACTATATGTGTCAGAATTGTTACCGAACAACAAAAACATAAGGTTCT
2757  195_HRV80a    CAATGATATGGGAACCCGTGTGCTAGAATTGTTACAGAACAACAGAAACATAAAGTCCT
2758  196_HRV80b    CAATGATATGGGAACCCTGTGTGCTAGAATTGTTACAGAACAACAGAAACATAAAGTCCT
2759  197_HRV80     CAATGATATGGGAACCCTGTGTGCTAGAATTGTTACAGAACAACAGAAACATAAAGTCCT
2760  198_HRV51     AAATGCTATGGGACACTATGTGTTCGTGTGGTCACAGAGCAACAAAAACATGAGGTTAA
2761  199_HRV51a    AAATGCTATGGGGACACTATGTGTTCGTGTGGTCACAGAGCAACAAAAACATGAGGTTAA
2762  200_HRV51b    AAATGCTATGGGGACACTATGTGTTCGTGTGGTCACAGAGCAACAAAAACATGAGGTTAA
2763  201_HRV65a    TAATGCTATGGGCACACTATATGTGCGTGTGGTTACAGAAAGGCAAAAACATGAAGTCAA
2764  202_HRV65b    TAATGCTATGGGCACACTATATGTGCGTGTGGTTACAGAAAGGCAAAAACATGAAGTCAA
2765  203_HRV65     TAATGCTATGGGCACACTATATGTGCGTGTGGTTACAGAAAGGCAAAAACATGAAGTCAA
2766  204_HRV71a    TAATGCCATGGGCACCTTATGTGTTCGTGTGGTTACAGAACAGCAAAGCAACACAGTCAA
2767  205_HRV71b    TAATGCCATGGGCACCTTATGTGTTCGTGTGGTTACAGAACAGCAAAGCAACACAGTCAA
2768  206_HRV71     TAATGCCATGGGCACCTTATGTGTTCGTGTGGTTACAGAACAGCAAAGCAACACAGTCAA
2769  207_HRV8      AAATCACATGGGCACAATATGTGTGAGAATGGTGACAGATAAACAGAAAATTAAAACTAA
2770  208_HRV95     AAATCACATGGGCACAATATGTGTGAGAATGGTGACAGATAAACAGAAAATTAAAACTAA
2771  209_HRV45     TAACCATATGGGGACTATATGTGTTAGAATTGTTACAGACCAACAACAACATAGAGTTAA
2772  210_HRV45a    TAACCATATGGGGACTATATGTGTTAGAATTGTTACAGACCAACAACAACATAGAGTTAA
2773  211_HRV45b    TAACCATATGGGGACTATATGTGTTAGAATTGTTACAGACCAACAACAACATAGAGTTAA
2774  GROUP_1       -AA----ATGGG--C--T-T------G--T--T-AC-------CA---------------
2775

2776  1_HRV1A1|d    CATCACAACACACATATATCATAAAGCTAAACACACAAAAGCTTGGTGTCCTAGGCCCCC
2777  2_HRV1A2|d    CATCACAACACACATATATCATAAAGCTAAACACACAAAAGCTTGGTGTCCTAGGCCCCC
2778  3_HRV1A|cD    CATCACAACACACATATATCATAAAGCTAAACACACAAAAGCTTGGTGTCCTAGGCCCCC
2779  4_HRV1B1|d    TATTACAACACACATATATCACAAAGCTAAACACACAAAAGCTTGGTGTCCTAGACCTCC
2780  5_HRV1B2|d    TATTACAACACACATATATCACAAAGCTAAACACACAAAAGCTTGGTGTCCTAGACCTCC
2781  6_HRV1B       TATTACAACACACATATATCACAAAGCTAAACACACAAAAGCTTGGTGTCCTAGACCTCC
2782  7_HRV40a|d    GATTACCACACGTATATATCACAAGGCCAAGCATATTAAAGCATGGTGTCCAAGGGCCCC
2783  8_HRV40b|d    GATTACCACACGTATATATCACAAGGCCAAGCATATTAAAGCATGGTGTCCAAGGGCCCC
2784  9_HRV40       GATTACCACACGTATATATCACAAGGCCAAGCATATTAAAGCATGGTGTCCAAGGGCCCC
2785  10_HRV85      AATCACCACGCGTGTGTATCATAAGGCCAAGCATGTAAAGGCTTGGTGTCCAAGAGCACC
2786  11_HRV85a|    AATCACCACGCGTGTGTATCATAAGGCCAAGCATGTAAAGGCTTGGTGTCCAAGAGCACC
2787  12_HRV85b|    AATCACCACGCGTGTGTATCATAAGGCCAAGCATGTAAAGGCTTGGTGTCCAAGAGCACC
2788  13_HRV56a|    AGTCACAACTCGTGTATATCATAAGGCAAAGCATATTCGAGCATGGTGTCCTAGAGCACC
2789  14_HRV56b|    AGTCACAACTCGTGTATATCATAAGGCAAAGCATATTCGAGCATGGTGTCCTAGAGCACC
2790  15_HRV56      AGTCACAACTCGTGTATATCATAAGGCAAAGCATATTCGAGCATGGTGTCCTAGAGCACC
```

FIG. D8 CONT'D

```
04-2.trace                                                                              9/20/2007 5:04 PM 2791  16_HRV54       AATCACCACACGGGTGTATCACAAGGCAAAACACATTAGAGCATGGTGTCCACGTGCACC
2792  17_HRV98       AATCACTACACGTGTGTACCACAAAGCAAAACACATTAGAGCATGGTGTCCACGTGCACC
2793  18_HRV59a|     GGTTGTCACACGTGTGTATCACAAAGCTAAACACGTCAAAGCCTGGTGCCCTAGAGCTCC
2794  19_HRV59b|     GGTTGTCACACGTGTGTATCACAAAGCTAAACACGTCAAAGCCTGGTGCCCTAGAGCTCC
2795  20_HRV59       GGTTGTCACACGTGTGTATCACAAAGCTAAACACGTCAAAGCCTGGTGCCCTAGAGCTCC
2796  21_HRV63       GGTGACTACACGTGTATATCATAAAGCTAAACACATCAGAGCCTGGTGCCCAAGAGCTCC
2797  22_HRV63b|     GGTGACTACACGTGTATATCATAAAGCTAAACACATCAGAGCCTGGTGCCCAAGAGCTCC
2798  23_HRV63a|     GGTGACTACACGTGTATATCATAAAGCTAAACACATCAGAGCCTGGTGCCCAAGAGCTCC
2799  24_HRV39       GGTTACAACCAGAGTTTACCATAAAGCCAAGCATGTTAAAGCATGGTGCCCTAGGGCTCC
2800  25_HRV39a|     GGTTACAACCAGAGTTTACCATAAAGCCAAGCATGTTAAAGCATGGTGCCCTAGGGCTCC
2801  26_HRV39b|     GGTTACAACCAGAGTTTACCATAAAGCCAAGCATGTTAAAGCATGGTGCCCTAGGGCTCC
2802  27_HRV10a|     AATTACCACCAGTGTTTATCACAAAGCCAAGCATGTCAAAGCATGGTGTCCAAGACCACC
2803  28_HRV10b|     AATTACCACCAGTGTTTATCACAAAGCCAAGCATGTCAAAGCATGGTGTCCAAGACCACC
2804  29_HRV10       AATTACCACCAGTGTTTATCACAAAGCCAAGCATGTCAAAGCATGGTGTCCAAGACCACC
2805  30_HRV100a     AATTACTACTAATATCTATCACAAGGCCAAACATGTTAAAGCTTGGTGCCCAAGACCACC
2806  31_HRV100b     AATTACTACTAATATCTATCACAAGGCCAAACATGTTAAAGCTTGGTGCCCAAGACCACC
2807  32_HRV100      AATTACTACTAATATCTATCACAAGGCCAAACATGTTAAAGCTTGGTGCCCAAGACCACC
2808  33_HRV66       AATTACTACTAGAGTATACCATAAGGCTAAGCATGTTAAAGCCTGGTGTCCTAGACCACT
2809  34_HRV66b|     AATTACTACTAGAGTATACCATAAGGCTAAGCATGTTAAAGCCTGGTGTCCTAGACCACT
2810  35_HRV66a|     AATTACTACTAGAGTATACCATAAGGCTAAGCATGTTAAAGCCTGGTGTCCTAGACCACT
2811  36_HRV77a|     AATCACCACTAGAGTATACCACAAGGCTAAACATATTAAAGCTTGGTGTCCCAGACCACC
2812  37_HRV77b|     AATCACCACTAGAGTATACCACAAGGCTAAACATATTAAAGCTTGGTGTCCCAGACCACC
2813  38_HRV77       AATCACCACTAGAGTATACCACAAGGCTAAACATATTAAAGCTTGGTGTCCCAGACCACC
2814  39_HRV62a      GGTCACAACTAATATTTACCACAAGGCTAAGCATGTAAAAGCGTGGTGCCCGCGGCCGCC
2815  40_HRV62b      GGTCACAACTAATATTTACCACAAGGCTAAGCATGTAAAAGCGTGGTGCCCTAGACCACC
2816  41_HRV25       GGTTACAACTAACATTTACCATAAAGCTAAGCATGTAAAAGCATGGTGCCCTAGACCACC
2817  42_HRV29a      AGTTACAACAAGTATCTATCATAAAGCTAAACATGTAAAGGCGTGGTGTCCTAGACCACC
2818  43_HRV29b      AGTTACAACAAGTATCTATCATAAAGCTAAACATGTAAAGGCGTGGTGTCCTAGACCACC
2819  44_HRV44a      AGTTACAACAAGCATTTATCACAAAGCTAAACATGTAAAAGCATGGTGCCCTAGACCACC
2820  45_HRV44b      AGTTACAACAAGCATTTATCACAAAGCTAAACATGTAAAAGCATGGTGCCCTAGACCACC
2821  46_HRV31       AATCACAACCAATATTTACCATAAGGCCAAACATGTTAAGGCATGGTGTCCTAGGCCCCC
2822  47_HRV31a|     AATCACAACCAATATTTACCATAAGGCCAAACATGTTAAGGCATGGTGTCCTAGGCCCCC
2823  48_HRV31b|     AATCACAACCAATATTTACCATAAGGCCAAACATGTAAAGGCATGGTGTCCTAGGCCACC
2824  49_HRV47       AATCACAACTAACATCTACCATAAAGCCAAGCATGTGAAAGCATGGTGTCCTAGACCACC
2825  50_HRV47a|     AATCACAACTAACATCTACCATAAAGCCAAGCATGTGAAAGCATGGTGTCCTAGACCACC
2826  51_HRV47b|     AATCACAACTAACATCTACCATAAAGCCAAGCATGTGAAAGCATGGTGTCCTAGACCACC
2827  52_HRV11       AGTCACAACTAGGGTGTATCATAAAGCAAAGCATGTGAAGGTGTGGTGTCCAAGACCACC
2828  53_HRV11b|     AGTCACAACTAGGGTGTATCATAAAGCAAAGCATGTGAAGGTGTGGTGTCCAAGACCACC
2829  54_HRV11a|     AGTCACAACTAGGGTGTATCATAAAGCAAAGCATGTGAAGGTGTGGTGTCCAAGACCACC
2830  55_HRV76       AGTTACAACAAGAATATATCACAAAGCAAAGCATGTTAAGGTATGGTGCCCGAGACCACC
2831  56_HRV76b|     AGTTACAACAAGAATATATCACAAAGCAAAGCATGTTAAGGTATGGTGCCCGAGACCACC
2832  57_HRV76a|     AGTTACAACAAGAATATATCACAAAGCAAAGCATGTTAAGGTATGGTGCCCGAGACCACC
2833  58_HRV33       AGTTACAACAAGAGTATACCATAAAGCAAAACATGTCAAAGTCTGGTGCCCAAGACCACC
2834  59_HRV33b|     AGTTACAACAAGAGTATACCATAAAGCAAAACATGTCAAAGTCTGGTGCCCAAGACCACC
2835  60_HRV33a|     AGTTACAACAAGAGTATACCATAAAGCAAAACATGTCAAAGTCTGGTGCCCAAGACCACC
2836  61_HRV24a|     AATTACAACAAGAATATACCACAAAGCAAAGCACATTAAGGTCTGGTGTCCAAGGCCACC
2837  62_HRV24b|     AATTACAACAAGAATATACCACAAAGCAAAGCACATTAAGGTCTGGTGTCCAAGGCCACC
2838  63_HRV24       AATTACAACAAGAATATACCACAAAGCAAAGCACATTAAGGTCTGGTGTCCAAGGCCACC
2839  64_HRV90       GATCACTACAAGAATATACCATAAAGCAAAACACATTAAGGTTTGGTGTCCAAGACCACC
2840  65_HRV90a|     GATCACTACAAGAATATACCATAAAGCAAAACACATTAAGGTTTGGTGTCCAAGACCACC
2841  66_HRV90b|     GATCACTACAAGAATATACCATAAAGCAAAACACATTAAGGTTTGGTGTCCAAGACCACC
2842  67_HRV34       AATAACAACTAGAGTTTATCACAAAGCTAAACATGTAAAAACCTGGTGTCCAAGACCACC
2843  68_HRV34b|     AATAACAACTAGAGTTTATCACAAAGCTAAACATGTAAAAACCTGGTGTCCAAGACCACC
2844  69_HRV34a|     AATAACAACTAGAGTTTATCACAAAGCTAAACATGTAAAAACCTGGTGTCCAAGACCACC
2845  70_HRV50a|     AATCACAACCAGAGTATACCATAAAGCCAAACATAAAAGTCTGGTGTCCAAGACCACC
2846  71_HRV50b|     AATCACAACCAGAGTATACCATAAAGCCAAACACATAAAAGTCTGGTGTCCAAGACCACC
2847  72_HRV50       AATCACAACCAGAGTATACCATAAAGCCAAACACATAAAAGTCTGGTGTCCAAGACCACC
2848  73_HRV18a|     AATAACAACCAGAATATACCACAAGGCAAAACATGTTAAAGCATGCCCCAAGGCCACC
2849  74_HRV18b|     AATAACAACCAGAATATACCACAAGGCAAAACATGTTAAAGCATGGTGCCCAAGGCCACC
2850  75_HRV18       AATAACAACCAGAATATACCACAAGGCAAAACATGTTAAAGCATGGTGCCCAAGGCCACC
2851  76_HRV55       AGTGACGACAAGAGTCTATCATAAAGCTAAACACATCAAAGCATGGTGCCCACGACCACC
2852  77_HRV55b|     AGTGACGACAAGAGTCTATCATAAAGCTAAACACATCAAAGCATGGTGCCCACGACCACC
2853  78_HRV55a|     AGTGACGACAAGAGTCTATCATAAAGCTAAACACATCAAAGCATGGTGCCCACGACCACC
2854  79_HRV57       AATAACAACCAGAGTGTATCACAAAGCCAAACATGTCAAAGCCTGGTGCCCTAGACCACC
2855  80_HRV57a|     AATAACAACCAGAGTGTATCACAAAGCCAAACATGTCAAAGCCTGGTGCCCTAGACCACC
```

FIG. D8 CONT'D 04-2.trace                                                              9/20/2007 5:04 PM

| | | |
|---|---|---|
| 2856 | 81_HRV57b| | AATAACAACCAGAGTGTATCACAAAGCCAAACATGTCAAAGCCTGGTGCCCTAGACCACC |
| 2857 | 82_HRV21 | AGTGACCACAAGAATATACCATAAGGCAAAGCATGTTAAAGCTTGGTGCCCCAGACCACC |
| 2858 | 83_HRVHan | AGTGACCACAAGAATATACCATAAGGCAAAGCATGTTAAAGCTTGGTGCCCTAGACCACC |
| 2859 | 84_HRV43 | GATAACTACCAGGATATATCATAAAGCCAAGCATATCAAAGCTTGGTGCCCAAGACCACC |
| 2860 | 85_HRV43b| | GATAACTACCAGGATATATCATAAAGCCAAGCATATCAAAGCTTGGTGCCCAAGACCACC |
| 2861 | 86_HRV43a| | GATAACTACCAGGATATATCATAAAGCCAAGCATATCAAAGCTTGGTGCCCAAGACCACC |
| 2862 | 87_HRV75 | AGTAACCACTAGAATATATCACAAAGCCAAACATATAAAAGCTTGGTGTCCGAGGCCGCC |
| 2863 | 88_HRV75b| | AGTAACCACTAGAATATATCACAAAGCCAAACATATAAAAGCTTGGTGTCCGAGGCCGCC |
| 2864 | 89_HRV75a| | AGTAACCACTAGAATATATCACAAAGCCAAACATATAAAAGCTTGGTGTCCGAGGCCGCC |
| 2865 | 96_HRV9a|d | AATTTCAACCAGAATATATCACAAAGCCAAACATGTTAAAGCCTGGTGCCCAAGACCTCC |
| 2866 | 97_HRV9b|d | AATTTCAACCAGAATATATCACAAAGCCAAACATGTTAAAGCCTGGTGCCCAAGACCTCC |
| 2867 | 98_HRV9 | AATTTCAACCAGAATATATCACAAAGCCAAACATGTTAAAGCCTGGTGCCCAAGACCTCC |
| 2868 | 99_HRV32 | TATTTCAACTAGGGTATATCACAAAGCTAAACACGTCAAAGCTTGGTGCCCACGACCACC |
| 2869 | 100_HRV32a | TATTTCAACTAGGGTATATCACAAAGCTAAACACGTCAAAGCTTGGTGCCCACGACCACC |
| 2870 | 101_HRV32b | TATTTCAACTAGGGTATATCACAAAGCTAAACACGTCAAAGCTTGGTGCCCACGACCACC |
| 2871 | 102_HRV67 | AATTGCAACGCGGGTGTATCATAAGGCTAAACATGTAAAAGCTTGGTGCCCAAGGCCCCC |
| 2872 | 103_HRV67a | AATTGCAACGCGGGTGTATCATAAGGCTAAACATGTAAAAGCTTGGTGCCCAAGGCCCCC |
| 2873 | 104_HRV67b | AATTGCAACGCGGGTGTATCATAAGGCTAAACATGTAAAAGCTTGGTGCCCAAGGCCCCC |
| 2874 | 105_HRV15 | GATTACAACTAGAGTGTATCACAAAGCTAAACATGTAAAGGCTTGGTGCCCCAGACCCCC |
| 2875 | 106_HRV15a | GATTACAACTAGAGTGTATCACAAAGCTAAACATGTAAAGGCTTGGTGCCCCAGACCCCC |
| 2876 | 107_HRV15b | GATTACAACTAGAGTGTATCACAAAGCTAAACATGTAAAGGCTTGGTGCCCCAGACCCCC |
| 2877 | 108_HRV74a | AATTACAACTAGAGTGTACCATAAAGCAAAGCATGTGAAGGCATGGTGTCCTAGACCCCC |
| 2878 | 109_HRV74b | AATTACAACTAGAGTGTACCATAAAGCAAAGCATGTGAAGGCATGGTGTCCTAGACCCCC |
| 2879 | 110_HRV74 | AATTACAACTAGAGTGTACCATAAAGCAAAGCATGTGAAGGCATGGTGTCCTAGACCCCC |
| 2880 | 111_HRV38a | GATAACAACTAGAATTTATCATAAGGCAAAACATGTAAAAGCCTGGTGTCCAAGACCCCC |
| 2881 | 112_HRV38b | GATAACAACTAGAATTTATCATAAGGCAAAACATGTAAAAGCCTGGTGTCCAAGACCCCC |
| 2882 | 113_HRV38 | GATAACAACTAGAATTTATCATAAGCAAAACATGTAAAAGCCTGGTGTCCAAGACCCCC |
| 2883 | 114_HRV60 | CGTCGCAACAAGAATATATCATAAAGCAAAGCATGTTAAGGCTTGGTGTCCAAGACCTCC |
| 2884 | 115_HRV60a | CGTCGCAACAAGAATATATCATAAAGCAAAGCATGTTAAGGCTTGGTGTCCAAGACCTCC |
| 2885 | 116_HRV60b | CGTCGCAACAAGAATATATCATAAAGCAAAGCATGTTAAGGCTTGGTGTCCAAGACCTCC |
| 2886 | 117_HRV64a | CATCACTACTAGGGTTTATCACAAACAAAACATGTCAAGGCATGGTGTCCACGGCCCCC |
| 2887 | 118_HRV64b | CATCACTACTAGGGTTTATCACAAAGCAAAACATGTCAAGGCATGGTGTCCACGGCCCCC |
| 2888 | 119_HRV64 | CATCACTACTAGGGTTTATCACAAAGCAAAACATGTCAAGGCATGGTGTCCACGGCCCCC |
| 2889 | 120_HRV94a | CATCACTACTAGAGTGTACCACAAAGCAAAACATGTGAAAGCGTGGTGCCCGCGCCCTCC |
| 2890 | 121_HRV94b | CATCACTACTAGAGTGTACCACAAAGCAAAACATGTGAAAGCGTGGTGCCCGCGCCCTCC |
| 2891 | 122_HRV94 | CATCACTACTAGAGTGTACCACAAAGCAAAACATGTGAAAGCGTGGTGCCCGCGCCCTCC |
| 2892 | 123_HRV22 | AATTACAACTAGAGTGTACCACAAAGCAAAACATGTAAAGGCATGGTGCCCACGTCCTCC |
| 2893 | 124_HRV22a | AATTACAACTAGAGTGTACCACAAAGCAAAACATGTAAAGGCATGGTGCCCACGTCCTCC |
| 2894 | 125_HRV22b | AATTACAACTAGAGTGTACCACAAAGCAAAACATGTAAAGGCATGGTGCCCACGTCCTCC |
| 2895 | 126_HRV82 | CATTACCACAAGAATATATCACAAAGCAAAACATGTGAAAGCGTGGTGTCCACGACCCCC |
| 2896 | 127_HRV82b | CATTACCACAAGAATATATCACAAAGCAAAACATGTGAAAGCGTGGTGTCCACGACCCCC |
| 2897 | 128_HRV82a | CATTACCACAAGAATATATCACAAAGCAAAACATGTGAAAGCGTGGTGTCCACGACCCCC |
| 2898 | 129_HRV19 | AATCACAACTAGAGTATATCATAAAGCTAAACATATAAAAGCTTGGTGCCCCACGACCACC |
| 2899 | 130_HRV19a | AATCACAACTAGAGTATATCATAAAGCTAAACATATAAAAGCTTGGTGCCCACGACCACC |
| 2900 | 131_HRV19b | AATCACAACTAGAGTATATCATAAAGCTAAACATATAAAAGCTTGGTGCCCACGACCACC |
| 2901 | 132_HRV13 | GGTTACAACTAGAATCTATCATAAAGCTAAACATGTCAAAGCATGGTGTCCTAGACCTCC |
| 2902 | 133_HRV13a | GGTTACAACTAGAATCTATCATAAAGCTAAACATGTCAAAGCATGGTGTCCTAGACCTCC |
| 2903 | 134_HRV13b | GGTTACAACTAGAATCTATCATAAAGCTAAACATGTCAAAGCATGGTGTCCTAGACCTCC |
| 2904 | 135_HRV41 | GGTCACAACTAGAGTTTACCACAAAGCTAAACATGTTAAAGCATGGTGTCCTAGACCTCC |
| 2905 | 136_HRV41a | GGTCACAACTAGAGTTTACCACAAAGCTAAACATGTTAAAGCATGGTGTCCTAGACCTCC |
| 2906 | 137_HRV41b | GGTCACAACTAGAGTTTACCACAAAGCTAAACATGTTAAAGCATGGTGTCCTAGACCTCC |
| 2907 | 138_HRV73 | GGTTACTACTAGAATCTATCATAAGGCTAAACATGTTAAAGCTTGGTGTCCAAGACCTCC |
| 2908 | 139_HRV73b | GGTTACTACTAGAATCTATCATAAGGCTAAACATGTTAAAGCTTGGTGTCCAAGACCTCC |
| 2909 | 140_HRV73a | GGTTACTACTAGAATCTATCATAAGGCTAAACATGTTAAAGCTTGGTGTCCAAGACCTCC |
| 2910 | 141_HRV61 | AATCACAACTAGGATTTACCATAAAGCTAAACATGTTAAAGTCTGGTGTCCTAGACCCCC |
| 2911 | 142_HRV61a | AATCACAACTAGGATTTACCATAAAGCTAAACATGTTAAAGTCTGGTGTCCTAGACCCCC |
| 2912 | 143_HRV61b | AATCACAACTAGGATTTACCATAAAGCTAAACATGTTAAAGTCTGGTGTCCTAGACCCCC |
| 2913 | 144_HRV96 | AATTACAACCAGAGTTTACCACAAAGCTAAACATGTGTGGTGCCCGAGACCCCC |
| 2914 | 145_HRV96b | AATTACAACCAGAGTTTACCACAAAGCTAAACATGTTAAGGTGTGGTGCCCGAGACCCCC |
| 2915 | 146_HRV96a | AATTACAACCAGAGTTTACCACAAAGCTAAACATGTTAAGGTGTGGTGCCCGAGACCCCC |
| 2916 | 90_HRV16a| | AGTGGTAACAAGGATATATCACAAAGCCAAACACCAAAGCTTGGTGCCCAAGACCACC |
| 2917 | 91_HRV16b| | AGTGGTAACAAGGATATATCACAAAGCCAAACACCAAAGCTTGGTGCCCAAGACCACC |
| 2918 | 92_1AYM_A | AGTGGTAACAAGGATATATCACAAAGCCAAACACCAAAGCTTGGTGCCCAAGACCACC |
| 2919 | 93_HRV81a| | AATAGTAACAAGAATATATCACAAAGCTAAGCACACCAAAGCTTGGTGTCCAAGACCACC |
| 2920 | 94_HRV81b| | AATAGTAACAAGAATATATCACAAAGCTAAGCACACCAAAGCTTGGTGTCCAAGACCACC |

FIG. D8 CONT'D

```
04-2.trace                                                           9/20/2007 5:04 PM 2921  95_HRV81    AATAGTAACAAGAATATATCACAAAGCTAAGCACACCAAAGCTTGGTGTCCAAGACCACC
2922 147_HRV2     TATAATGACAAGAATCTATCACAAGGCTAAACATGTCAAGGCATGGTGTCCACGCCCACC
2923 148_HRV2a|   TATAATGACAAGAATCTATCACAAGGCTAAACATGTCAAGGCATGGTGTCCACGCCCACC
2924 149_HRV2b|   TATAATGACAAGAATCTATCACAAGGCTAAACATGTCAAGGCATGGTGTCCACGCCCACC
2925 150_HRV49a   TATCATGACAAGAATCTATCATAAAGCTAAACACGTCAAAGCATGGTGTCCGCGCCCACC
2926 151_HRV49b   TATCATGACAAGAATCTATCATAAAGCTAAACACGTCAAAGCATGGTGTCCGCGCCCACC
2927 152_HRV49    TATCATGACAAGAATCTATCATAAAGCTAAACACGTCAAAGCATGGTGTCCGCGCCCACC
2928 153_HRV23a   GATAATGACAAGGGTCTACCACAAAGCTAAACATGTCAAAGCATGGTGTCCGCGGCCACC
2929 154_HRV23b   GATAATGACAAGGGTCTACCACAAAGCTAAACATGTCAAAGCATGGTGTCCGCGGCCACC
2930 155_HRV23    GATAATGACAAGGGTCTACCACAAAGCTAAACATGTCAAAGCATGGTGTCCGCGGCCACC
2931 156_HRV30a   CATAATGACAAGGGTCTACCACAAGGCTAAACATGTCAAAGCGTGGTGTCCACGGCCACC
2932 157_HRV30b   CATAATGACAAGGGTCTACCACAAGGCTAAACATGTCAAAGCGTGGTGTCCACGGCCACC
2933 158_HRV30    CATAATGACAAGGGTCTACCACAAGGCTAAACATGTCAAAGCGTGGTGTCCACGGCCACC
2934 159_HRV7     GATTGTGAGTCGCATTTACCACAAAGCCAAACATATAAAAGCATGGTGCCCACGCCCACC
2935 160_HRV7b|   GATTGTGAGTCGCATTTACCACAAAGCCAAACATATAAAAGCATGGTGCCCACGCCCACC
2936 161_HRV7a|   GATTGTGAGTCGCATTTACCACAAAGCCAAACATATAAAAGCATGGTGCCCACGCCCACC
2937 162_HRV88    TATCATTAGCCGTATATATCACAAGGCTAAACATATAAAGGCATGGTGTCCACGCCCACC
2938 163_HRV88a   TATCATTAGCCGTATATATCACAAGGCTAAACATATAAAGGCATGGTGTCCACGCCCACC
2939 164_HRV88b   TATCATTAGCCGTATATATCACAAGGCTAAACATATAAAAGCATGGTGTCCACGCCCACC
2940 165_HRV36a   TATTGTATGCCGCATTTATCATAAAGCTAAACACATAAAGGCCTGGTGCCCGCGTCCACC
2941 166_HRV36b   TATTGTATGCCGCATTTATCATAAAGCTAAACACATAAAGGCCTGGTGCCCGCGTCCACC
2942 167_HRV36    TATTGTATGCCGCATTTATCATAAAGCTAAACACATAAAGGCCTGGTGCCCGCGTCCACC
2943 168_HRV89a   TATTGTGTGCCGCATTTACCACAAGGCCAAACATATAAAAGCATGGTGTCCTCTCGCCCACC
2944 169_HRV89b   TATTGTGTGCCGCATTTACCACAAGGCCAAACATATAAAAGCATGGTGTCCTCGCCCACC
2945 170_HRV89    TATTGTGTGCCGCATTTACCACAAGGCCAAACATATAAAAGCATGGTGTCCTCGCCCACC
2946 171_HRV58    CATTGTCTGTCGCATTTACCACAAAGCCAAGCATATAAAAGCATGGTGTCCACGCCCACC
2947 172_HRV58a   CATTGTCTGTCGCATTTACCACAAAGCCAAGCATATAAAAGCATGGTGTCCACGCCCACC
2948 173_HRV58b   CATTGTCTGTCGCATTTACCACAAAGCCAAGCATATAAAAGCATGGTGTCCACGCCCACC
2949 174_HRV12a   GATTACCAGTAGAATATACCATAAAGCAAAACATATCAGTGCCTGGGGCCCTAGACCACC
2950 175_HRV12b   GATTACCAGTAGAATATACCATAAAGCAAAACATATCAGTGCCTGGGGCCCTAGACCACC
2951 176_HRV12    GATTACCAGTAGAATATACCATAAAGCAAAACATATCAGTGCCTGGGGCCCTAGACCACC
2952 177_HRV78a   AATTACAGCTAGAGTCTACCACAAGGCCAAACATATTAGTGCATGGGGCCCAAGACCTCC
2953 178_HRV78b   AATTACAGCTAGAGTCTACCACAAGGCCAAACATATTAGTGCATGGGGCCCAAGACCTCC
2954 179_HRV78    AATTACAGCTAGAGTCTACCACAAGGCCAAACATATTAGTGCATGGGGCCCAAGACCTCC
2955 180_HRV20    GATAACCAGTAGGATATTCCACAAGGCAAAGCATATTAGTGCATGGTGTCCAAGGGCCCC
2956 181_HRV20a   GATAACCAGTAGGATATTCCACAAGGCAAAGCATATTAGTGCATGGTGTCCAAGGGCCCC
2957 182_HRV20b   GATAACCAGTAGGATATTCCACAAGGCAAAGCATATTAGTGCATGGTGTCCAAGGGCCCC
2958 183_HRV68    AATAACCAGCAGAATATTCACAAAACAAAACATATTAGTGCGTGGTGTCCAAGAGCTCC
2959 184_HRV68a   AATAACCAGCAGAATATTCCATAAAGCAAAACATATTAGTGCGTGGTGTCCAAGAGCTCC
2960 185_HRV68b   AATAACCAGCAGAATATTCCATAAAGCAAAACATATTAGTGCGTGGTGTCCAAGAGCTCC
2961 186_HRV28    AATAACCAGCATAATATTCCACAAAGCTAAACATGTCAGTGCATGGTGCCCCAGACCTCC
2962 187_HRV28a   AATAACCAGCATAATATTCCACAAAGCTAAACATGTCAGTGCATGGTGCCCCAGACCTCC
2963 188_HRV28b   AATAACCAGCATAATATTCCACAAAGCTAAACATGTCAGTGCATGGTGCCCCAGACCTCC
2964 189_HRV53a   GATAACCAGTAGGATTTATCACAAGGCTAAACATATCAGTGCATGGTGTCCAAGACCACC
2965 190_HRV53b   GATAACCAGTAGGATTTATCACAAGGCTAAACATATCAGTGCATGGTGTCCAAGACCACC
2966 191_HRV53    GATAACCAGTAGGATTTATCACAAGGCTAAACATATCAGTGCATGGTGTCCAAGACCACC
2967 192_HRV46a   TATAACTAGCAGAATATATCACAAGGCTAAACACATTAAAGCATGGTGCCCCAGGGCACC
2968 193_HRV46b   TATAACTAGCAGAATATATCACAAGGCTAAACACATTAAAGCATGGTGCCCCAGGGCACC
2969 194_HRV46    TATAACTAGCAGAATATATCACAAGGCTAAACACATTAAAGCATGGTGCCCCAGGGCACC
2970 195_HRV80a   AATCACCAGCAGAATATATCACAAAGCTAAACACATCAAAGCATGGTGTCCAAGAGCACC
2971 196_HRV80b   AATCACCAGCAGAATATATCACAAAGCTAAACACATCAAAGCATGGTGTCCAAGAGCACC
2972 197_HRV80    AATCACCAGCAGAATATATCACAAAGCTAAACACATCAAAGCATGGTGTCCAAGAGCACC
2973 198_HRV51    CATAACTAGCAGGATTTACCACAAAGCCAAACATGTCAGTGCATGGTGCCCTCGTCCTCC
2974 199_HRV51a   CATAACTAGCAGGATTTACCACAAAGCCAAACATGTCAGTGCATGGTGCCCTCGTCCTCC
2975 200_HRV51b   CATAACTAGCAGGATTTACCACAAAGCCAAACATGTCAGTGCATGGTGCCCTCGTCCTCC
2976 201_HRV65a   CATAACCAGTAGAATATATCATAAAGCTAAACACATCAGTGCTTGGTGTCCACGACCTCC
2977 202_HRV65b   CATAACCAGTAGAATATATCATAAAGCTAAACACATCAGTGCTTGGTGTCCACGACCTCC
2978 203_HRV65    CATAACCAGTAGAATATATCATAAAGCTAAACACATCAGTGCTTGGTGTCCACGACCTCC
2979 204_HRV71a   CATAACAAGTAGGATTTATCACAAAGCCAAACATGTCAGAGCATGGTGTCCTAGACCCCC
2980 205_HRV71b   CATAACAAGTAGGATTTATCACAAAGCCAAACATGTCAGAGCATGGTGTCCTAGACCCCC
2981 206_HRV71    CATAACAAGTAGGATTTATCACAAAGCCAAACATGTCAGAGCATGGTGTCCTAGACCCCC
2982 207_HRV8     AATTGATTCAAGAATATACCTGAAAGCAAAGCACATTAAAGCTTGGTGTCCTAGACCCCC
2983 208_HRV95    AATTGATTCAAGAATATACCTGAAAGCAAAGCATATTAAAGCTTGGTGTCCTAGACCCCC
2984 209_HRV45    GATCGACTCCATGGTATATCTAAAAGCTAAACACATCAAGGCATGGTGTCCCAGACCTCC
2985 210_HRV45a   GATCGACTCCATGGTATATCTAAAAGCTAAACACATCAAGGCATGGTGTCCCAGACCTCC
```

FIG. D8 CONT'D

04-2.trace                                                                      9/20/2007 5:04 PM

```
2986  211_HRV45b      GATCGACTCCATGGTATATCTAAAAGCTAAACACATCAAGGCATGGTGTCCCAGACCTCC
2987  GROUP_1         --T----------T-T--C--AA-GC-AA-CA----------TGG-G-CC--G--C-C-
2988
2989  1_HRV1A1|d      TAGAGCTGTCCCTTACACA-CATAGTCATGTGACTAATTATATGC-CAGAAA---CAGGT
2990  2_HRV1A2|d      TAGAGCTGTCCCTTACACA-CATAGTCATGTGACTAATTATATGC-CAGAAA---CAGGT
2991  3_HRV1A|cD      TAGAGCTGTCCCTTACACA-CATAGTCATGTGACTAATTATATGC-CAGAAA---CAGGT
2992  4_HRV1B1|d      TAGAGCTGTTCCTTACACA-CATAGTCGTGTAACTAATTATGTAC-CAAAAA---CAGGT
2993  5_HRV1B2|d      TAGAGCTGTTCCTTACACA-CATAGTCGTGTAACTAATTATGTAC-CAAAAA---CAGGT
2994  6_HRV1B         TAGAGCTGTTCCTTACACA-CATAGTCGTGTAACTAATTATGTAC-CAAAAA---CAGGT
2995  7_HRV40a|d      AAGAGCAGTACCTTACACA-CATACACACTCAACAAATTATAAAC-CTCAAG---AAGGT
2996  8_HRV40b|d      AAGAGCAGTACCTTACACA-CATACACACTCAACAAATTATAAAC-CTCAAG---AAGGT
2997  9_HRV40         AAGAGCAGTACCTTACACA-CATACACACTCAACAAATTATAAAC-CTCAAG---AAGGT
2998  10_HRV85        AAGAGCGGTGCCTTATACA-CACACACGCTCAACCAACTATGTGC-CACAAG---ATGGT
2999  11_HRV85a|      AAGAGCGGTGCCTTATACA-CACACACGCTCAACCAACTATGTGC-CACAAG---ATGGT
3000  12_HRV85b|      AAGAGCGGTGCCTTATACA-CACACACGCTCAACCAACTATGTGC-CACAAG---ATGGT
3001  13_HRV56a|      AAGGGCTGTGCCTTATACA-CATGCTCACGTCACCAATTATAAAC-CACAAG---ATGGT
3002  14_HRV56b|      AAGGGCTGTGCCTTATACA-CATGCTCACGTCACCAATTATAAAC-CACAAG---ATGGT
3003  15_HRV56        AAGGGCTGTGCCTTATACA-CATGCTCACGTCACCAATTATAAAC-CACAAG---ATGGT
3004  16_HRV54        TAGGGCTGTCCCATACACA-CATACTAGATCAACAAATTACATGC-CACGGG---AGGGT
3005  17_HRV98        TAGAGCTGTTCCATACACA-CACACTAGATCAACTAATTACATGC-CTCAAG---ATGGT
3006  18_HRV59a|      TAGAGCAGTCCCTTACACA-CACAGCTACGTAACTAACTACAAGATTGCTGG---AAAA-
3007  19_HRV59b|      TAGAGCAGTCCCTTACACA-CACAGCTACGTAACTAACTACAAGATTGCTGG---AAAA-
3008  20_HRV59        TAGAGCAGTCCCTTACACA-CACAGCTACGTAACTAACTACAAGATTGCTGG---AAAA-
3009  21_HRV63        TAGGGCTGTTCCATACACA-CATAGTTATGTCACTAACTATAAAATTACAGG---ACAG-
3010  22_HRV63b|      TAGGGCTGTTCCATACACA-CATAGTTATGTCACTAACTATAAAATTACAGG---ACAG-
3011  23_HRV63a|      TAGGGCTGTTCCATACACA-CATAGTTATGTCACTAACTATAAAATTACAGG---ACAG-
3012  24_HRV39        CAGAGCAGTCCCTTACACA-CACAGCAATGTTACAAATTACAAAG-TACGGG---ACGGT
3013  25_HRV39a|      CAGAGCAGTCCCTTACACA-CACAGCAATGTTACAAATTACAAAG-TACGGG---ACGGT
3014  26_HRV39b|      CAGAGCAGTCCCTTACACA-CACAGCAATGTTACAAATTACAAAG-TACGGG---ACGGT
3015  27_HRV10a|      CAGAGCTGTACCATATACA-CATGCCCATTCCACAAATTACAAAC-CACATG---GCAAA
3016  28_HRV10b|      CAGAGCTGTACCATATACA-CATGCCCATTCCACAAATTACAAAC-CACATG---GCAAA
3017  29_HRV10        CAGAGCTGTACCATATACA-CATGCCCATTCCACAAATTACAAAC-CACATG---GCAAA
3018  30_HRV100a      TCGGGCTGTGCCGTACACA-CATAGTCACTCTACAAATTACAAAC-CACATG---AGGGT
3019  31_HRV100b      TCGGGCTGTGCCGTACACA-CATAGTCACTCTACAAATTACAAAC-CACATG---AGGGT
3020  32_HRV100       TCGGGCTGTGCCGTACACA-CATAGTCACTCTACAAATTACAAAC-CACATG---AGGGT
3021  33_HRV66        TAGAGCTGTACCATACACA-ACTGTAAACTCAACCAATTATATGC-CTCATA---CTGGT
3022  34_HRV66b|      TAGAGCTGTACCATACACA-ACTGTAAACTCAACCAATTATATGC-CTCATA---CTGGT
3023  35_HRV66a|      TAGAGCTGTACCATACACA-ACTGTAAACTCAACCAATTATATGC-CTCATA---CTGGT
3024  36_HRV77a|      TAGAGCTGTACCATACACA-GCAGTAGATTCAACAAATTACAAAC-CTATGA---GAGGG
3025  37_HRV77b|      TAGAGCTGTACCATACACA-GCAGTAGATTCAACAAATTACAAAC-CTATGA---GAGGG
3026  38_HRV77        TAGAGCTGTACCATACACA-GCAGTAGATTCAACAAATTACAAAC-CTATGA---GAGGG
3027  39_HRV62a       CAGAGCTGTTCCATATAAA-TATGTTGATTTCAATAATTATGCAG-CCAGTG---ATAGT
3028  40_HRV62b       TAGAGCTGTTCCATATAAA-TATGTTGATTTCAATAATTATGCAG-CCAGTG---ATAGT
3029  41_HRV25        TAGAGCTGTCCCATATAAA-TATGTTGACTTCAATAATTATGCAG-CCAGTG---ATAAT
3030  42_HRV29a       AAGAGTTGTCCCATACAAG-TATGTTGGCCTAACTAATTACACAC-TTAAAG---AAGAA
3031  43_HRV29b       AAGAGTTGTCCCATACAAG-TATGTTGGCCTAACTAATTACACAC-TTAAAG---AAGAA
3032  44_HRV44a       AAGGGTTGTCCCATACAAG-TATGTTGGCCTAACTAATTACACAC-TTAAAG---AAACA
3033  45_HRV44b       AAGGGTTGTCCCATACAAG-TATGTTGGCCTAACTAATTACACAC-TTAAAG---AAACA
3034  46_HRV31        TAGAGCAGTTCCATACAGGGTATG-TGGATCAACAAACTACAAAC-CTGATG---AAAAT
3035  47_HRV31a|      TAGAGCAGTTCCATACAGGGTATG-TGGATCAACAAACTACAAAC-CTGATG---AAAAT
3036  48_HRV31b|      TAGAGCAGTTCCATACAGG-TATGTTGGATCAACAAACTACAAAC-CTGATG---AAAAT
3037  49_HRV47        TAGAGCTGTTCCATATAGA-TATGTTGGATCAACAAACTACAAAC-CTGATC---AAGGA
3038  50_HRV47a|      TAGAGCTGTTCCATATAGA-TATGTTGGATCAACAAATTACAAAC-CTGATC---AAGGA
3039  51_HRV47b|      TAGAGCTGTTCCATATAGA-TATGTTGGATCAACAAATTACAAAC-CTGATC---AAGGA
3040  52_HRV11        TAGAGCTGTAGAATATACT-CACACTCATGTAACCAATTACAAAC-CACAGG---AAGGA
3041  53_HRV11b|      TAGAGCTGTAGAATATACT-CACACTCATGTAACCAATTACAAAC-CACAGG---AAGGA
3042  54_HRV11a|      TAGAGCTGTAGAATATACT-CACACTCATGTAACCAATTACAAAC-CACAGG---AAGGA
3043  55_HRV76        TAGAGCTGTAGAGTATACA-TACACCCATGTAACAAACTACAAAC-CACATT---CTGGT
3044  56_HRV76b|      TAGAGCTGTAGAGTATACA-TACACCCATGTAACAAACTACAAAC-CACATT---CTGGT
3045  57_HRV76a|      TAGAGCTGTAGAGTATACA-TACACCCATGTAACAAACTACAAAC-CACATT---CTGGT
3046  58_HRV33        TAGAGCTGTGGAATACACC-CATACTCATGTTACAAATTATAAAT-CAACAA---CTCGT
3047  59_HRV33b|      TAGAGCTGTGGAATACACC-CATACTCATGTTACAAATTATAAAT-CAACAA---CTCGT
3048  60_HRV33a|      TAGAGCTGTGGAATACACC-CATACTCATGTTACAAATTATAAAT-CAACAA---CTCGT
3049  61_HRV24a|      CAGAGCTGTTGAGTATACA-CATACTCACGTGACCAATTATAAGC-ATCAGA---CTCGT
3050  62_HRV24b|      CAGAGCTGTTGAGTATACA-CATACTCACGTGACCAATTATAAGC-ATCAGA---CTCGT
```

FIG. D8 CONT'D

04-2.trace                                                                      9/20/2007 5:04 PM

```
3051  63_HRV24       CAGAGCTGTTGAGTATACA-CATACTCACGTGACCAATTATAAGC-ATCAGA---CTCGT
3052  64_HRV90       TAGGGCAGTTGAATACACA-CACACTCATGTAACAAACTACAAAC-ATGCAA---CACGT
3053  65_HRV90a|     TAGGGCAGTTGAATACACA-CACACTCATGTAACAAACTACAAAC-ATGCAA---CACGT
3054  66_HRV90b|     TAGGGCAGTTGAATACACA-CACACTCATGTAACAAACTACAAAC-ATGCAA---CACGT
3055  67_HRV34       AAGAGCTGTTGAGTACACA-CACACACATGTTACTAACTACAAAG-TTAGGG---GTAAA
3056  68_HRV34b|     AAGAGCTGTTGAGTACACA-CACACACATGTTACTAACTACAAAG-TTAGGG---GTAAA
3057  69_HRV34a|     AAGAGCTGTTGAGTACACA-CACACACATGTTACTAACTACAAAG-TTAGGG---GTAAA
3058  70_HRV50a|     AAGAGCTGTTGAATACACA-CACACCCATGTCACTAACTACAAGA-AAAGTG---ATGCT
3059  71_HRV50b|     AAGAGCTGTTGAATACACA-CACACCCATGTCACTAACTACAAGA-AAAGTG---ATGCT
3060  72_HRV50       AAGAGCTGTTGAATACACA-CACACCCATGTCACTAACTACAAGA-AAAGTG---ATGCT
3061  73_HRV18a|     GAGAGCTGTGGAGTACACA-CATACACATGTAACTAACTACAAGC-CTAAGG---AAGGA
3062  74_HRV18b|     GAGAGCTGTGGAGTACACA-CATACACATGTAACTAACTACAAGC-CTAAGG---AAGGA
3063  75_HRV18       GAGAGCTGTGGAGTACACA-CATACACATGTAACTAACTACAAGC-CTAAGG---AAGGA
3064  76_HRV55       TAGGGCTGTTGAATACACA-CACACACATGTCACAAATTACAAGA-AGACTG---ATGGC
3065  77_HRV55b|     TAGGGCTGTTGAATACACA-CACACACATGTCACAAATTACAAGA-AGACTG---ATGGC
3066  78_HRV55a|     TAGGGCTGTTGAATACACA-CACACACATGTCACAAATTACAAGA-AGACTG---ATGGC
3067  79_HRV57       ACGGGCTATCGAGTACACA-CATACACATGTTACTAATTATAAAA-TAAAAG---ATAGA
3068  80_HRV57a|     ACGGGCTATCGAGTACACA-CATACACATGTTACTAATTATAAAA-TAAAAG---ATAGA
3069  81_HRV57b|     ACGGGCTATCGAGTACACA-CATACACATGTTACTAATTATAAAA-TAAAAG---ATAGA
3070  82_HRV21       GAGGGCCGTTGAATACACA-CATACACACGTAACCAATTACAAAA-TTGCAA---ATCAT
3071  83_HRVHan      GAGGGCCGTTGAATACACA-CATACACATGTAACCAATTACAAAA-TTGCAA---ATAAA
3072  84_HRV43       CAGAGCTGTTGAATACACA-CACACACATGTCACAAATTATAAAA-GAGAAG---GAAAG
3073  85_HRV43b|     CAGAGCTGTTGAATACACA-CACACACATGTCACAAATTATAAAA-GAGAAG---GAAAG
3074  86_HRV43a|     CAGAGCTGTTGAATACACA-CACACACATGTCACAAATTATAAAA-GAGAAG---GAAAG
3075  87_HRV75       CAGGGCTGTTGAATACACA-TTTAGACGTGTAACAAATTACAAAA-GAGATG---GACAA
3076  88_HRV75b|     CAGGGCTGTTGAATACACA-TTTAGACGTGTAACAAATTACAAAA-GAGATG---GACAA
3077  89_HRV75a|     CAGGGCTGTTGAATACACA-TTTAGACGTGTAACAAATTACAAAA-GAGATG---GACAA
3078  96_HRV9a|d     TAGGGCAGTTGAGTATATA-CATACACATGTCACAAATTACAAGC-CAAGCA---CAGGC
3079  97_HRV9b|d     TAGGGCAGTTGAGTATATA-CATACACATGTCACAAATTACAAGC-CAAGCA---CAGGC
3080  98_HRV9        TAGGGCAGTTGAGTATATA-CATACACATGTCACAAATTACAAGC-CAAGCA---CAGGC
3081  99_HRV32       TAGGGCAGTTGAATATACA-CATACACATGTTAACAATTACAAAC-CAAGCA---CAGGT
3082  100_HRV32a     TAGGGCAGTTGAATATACA-CATACACATGTTACAAATTACAAAC-CAAGCA---CAGGT
3083  101_HRV32b     TAGGGCAGTTGAATATACA-CATACACATGTTACAAATTACAAAC-CAAGCA---CAGGT
3084  102_HRV67      TAGAGCAGTTGAATACATA-CACACACATGTTACAAACTATAGAC-CAGAAA---CAGGT
3085  103_HRV67a     TAGAGCAGTTGAATACATA-CACACACATGTTACAAACTATAGAC-CAGAAA---CAGGT
3086  104_HRV67b     TAGAGCAGTTGAATACATA-CACACACATGTTACAAACTATAGAC-CAGAAA---CAGGT
3087  105_HRV15      TAGAGCAGTGGAATATACA-CACACACATGTCACAAATTACAAAC-CACAAG---ATGGT
3088  106_HRV15a     TAGAGCAGTGGAATATACA-CACACACATGTCACAAATTACAAAC-CACAAG---ATGGT
3089  107_HRV15b     TAGAGCAGTGGAATATACA-CACACACATGTCACAAATTACAAAC-CACAAG---ATGGT
3090  108_HRV74a     TAGAGCAGTTGAATATACT-CACACACATGTCACAAATTACAAAC-CACAAG---AAGGT
3091  109_HRV74b     TAGAGCAGTTGAATATACT-CACACACATGTCACAAATTACAAAC-CACAAG---AAGGT
3092  110_HRV74      TAGAGCAGTTGAATATACT-CACACACATGTCACAAATTACAAAC-CACAAG---AAGGT
3093  111_HRV38a     AAGGGCAGTTGAATATAGA-CATACACATGTTAACAATTACAAAC-CAGACC---AAGGG
3094  112_HRV38b     AAGGGCAGTTGAATATAGA-CATACACATGTTAACAATTACAAAC-CAGACC---AAGGG
3095  113_HRV38      AAGGGCAGTTGAATATAGA-CATACACATGTTAACAATTACAAAC-CAGACC---AAGGG
3096  114_HRV60      AAGGGCAGTTGAATATAGA-CACACACATGTAAACAATTATAGAC-CAGATG---ATGGA
3097  115_HRV60a     AAGGGCAGTTGAATATAGA-CACACACATGTAAACAATTATAGAC-CAGATG---ATGGA
3098  116_HRV60b     AAGGGCAGTTGAATATAGA-CACACACATGTAAACAATTATAGAC-CAGATG---ATGGA
3099  117_HRV64a     AAGAGCTGTTGGATATACA-CATACAAATGTCACCAATTATAAAC-CATCCA---AAGGA
3100  118_HRV64b     AAGAGCTGTTGGATATACA-CATACAAATGTCACCAATTATAAAC-CATCCA---AAGGA
3101  119_HRV64      AAGAGCTGTTGGATATACA-CATACAAATGTCACCAATTATAAAC-CATCCA---AAGGA
3102  120_HRV94a     AAGAGCTGTTGGATACACA-CATACGCATGTCACTAATTACAAAC-CATCTG---AAGGG
3103  121_HRV94b     AAGAGCTGTTGGATACACA-CATACGCATGTCACTAATTACAAAC-CATCTG---AAGGG
3104  122_HRV94      AAGAGCTGTTGGATACACA-CATACGCATGTCACTAATTACAAAC-CATCTG---AAGGG
3105  123_HRV22      AAGAGCTGTTGGATATACA-CACACACATGTGACAAACTACAAAC-CATCTG---TAGGG
3106  124_HRV22a     AAGAGCTGTTGGATATACA-CACACACATGTGACAAACTACAAAC-CATCTG---TAGGG
3107  125_HRV22b     AAGAGCTGTTGGATATACA-CACACACATGTGACAAACTACAAAC-CATCTG---TAGGG
3108  126_HRV82      GAGGGCTGTGGGTTATACA-CACACACATGTTACCAACTACAAGC-CATCAC---AGGGA
3109  127_HRV82b     GAGGGCTGTGGGTTATACA-CACACACATGTTACCAACTACAAGC-CATCAC---AGGGA
3110  128_HRV82a     GAGGGCTGTGGGTTATACA-CACACACATGTTACCAACTACAAGC-CATCAC---AGGGA
3111  129_HRV19      CAGAGCCGTGGAATATACC-CACACTCATGTGACTAATTATAAAC-CCCAGA---CAGGT
3112  130_HRV19a     CAGAGCCGTGGAATATACC-CACACTCATGTGACTAATTATAAAC-CCCAGA---CAGGT
3113  131_HRV19b     CAGAGCCGTGGAATATACC-CACACTCATGTGACTAATTATAAAC-CCCAGA---CAGGT
3114  132_HRV13      CAGAGCTGTTGAATATACT-AATGTGCATGTTACAAACTACAAAC-CAGGGA---CAGGA
3115  133_HRV13a     CAGAGCTGTTGAATATACT-AATGTGCATGTTACAAACTACAAAC-CAGGGA---CAGGA
```

FIG. D8 CONT'D 04-2.trace                                                                                        9/20/2007 5:04 PM

```
3116  134_HRV13b    CAGAGCTGTTGAATATACT-AATGTGCATGTTACAAACTACAAAC-CAGGGA---CAGGA
3117  135_HRV41     CAGGGCTGTGGAGTACACC-AATGTGCATGTCACAAATTACAAAC-CAAAAG---CAGGA
3118  136_HRV41a    CAGGGCTGTGGAGTACACA-AATGTGCATGTCACAAATTACAAAC-CAAAAG---CAGGA
3119  137_HRV41b    CAGGGCTGTGGAGTACACC-AATGTGCATGTCACAAATTACAAAC-CAAAAG---CAGGA
3120  138_HRV73     TAGGGCAGTAGAATATACA-AATGCACATGTGACCAATTATAAAC-CCACTG---ATGGA
3121  139_HRV73b    TAGGGCAGTAGAATATACA-AATGCACATGTGACCAATTATAAAC-CCACTG---ATGGA
3122  140_HRV73a    TAGGGCAGTAGAATATACA-AATGCACATGTGACCAATTATAAAC-CCACTG---ATGGA
3123  141_HRV61     CAGAGCAGTGGAATATACT-AATGTGCATTTGACCAATTACAAGC-CCAAAG---ATAGT
3124  142_HRV61a    CAGAGCAGTGGAATATACT-AATGTGCATTTGACCAATTACAAGC-CCAAAG---ATAGT
3125  143_HRV61b    CAGAGCAGTGGAATATACT-AATGTGCATTTGACCAATTACAAGC-CCAAAG---ATAGT
3126  144_HRV96     TAGAGCAGTTGAATACACA-AATGTGCATCTCACAAATTATAAAC-CCAACA---ATG--
3127  145_HRV96b    TAGAGCAGTTGAATACACA-AATGTGCATCTCACAAATTATAAAC-CCAACA---ATG--
3128  146_HRV96a    TAGAGCAGTTGAATACACA-AATGTGCATCTCACAAATTATAAAC-CCAACA---ATG--
3129  90_HRV16a|    CAGAGCTGTTCAATACTCA-CATACACATACCACCAACTACAAAT-TGAGTT---CAGAA
3130  91_HRV16b|    CAGAGCTGTTCAATACTCA-CATACACATACCACCAACTACAAAT-TGAGTT---CAGAA
3131  92_1AYM_A     CAGAGCTGTTCAATACTCA-CATACACATACCACCAACTACAAAT-TGAGTT---CAGAA
3132  93_HRV81a|    CAGGGCTGTTCAGTACACA-CATACACATGTAACTAATTATAAAT-TAGAAA---CAGAT
3133  94_HRV81b|    CAGGGCTGTTCAGTACACA-CATACACATGTAACTAATTATAAAT-TAGAAA---CAGAT
3134  95_HRV81      CAGGGCTGTTCAGTACACA-CATACACATGTAACTAATTATAAAT-TAGAAA---CAGAT
3135  147_HRV2      CAGAGCGCTTGAGTATACT-CGTGCTCACCGCACTAATTTTAAAA-TTGAGG---ATAGG
3136  148_HRV2a|    CAGAGCGCTTGAGTATACT-CGTGCTCACCGCACTAATTTTAAAA-TTGAGG---ATAGG
3137  149_HRV2b|    CAGAGCGCTTGAGTATACT-CGTGCTCACCGCACTAATTTTAAAA-TTGAGG---ATAGG
3138  150_HRV49a    CAGAGCACTTGAATATACT-CGCGCTCACCGTACTAATTTCAAAG-TTGAAG---ACAGA
3139  151_HRV49b    CAGAGCACTTGAATATACT-CGCGCTCACCGTACTAATTTCAAAG-TTGAAG---ACAGA
3140  152_HRV49     CAGAGCACTTGAATATACT-CGCGCTCACCGTACTAATTTCAAAG-TTGAAG---ACAGA
3141  153_HRV23a    CAGAGCACTTGAATACACA-CGCGCTCACCGTACTAATTTCAAAA-TTGAAG---GTGAA
3142  154_HRV23b    CAGAGCACTTGAATACACA-CGCGCTCACCGTACTAATTTCAAAA-TTGAAG---GTGAA
3143  155_HRV23     CAGAGCACTTGAATACACA-CGCGCTCACCGTACTAATTTCAAAA-TTGAAG---GTGAA
3144  156_HRV30a    TAGGGCGCTTGAGTATACC-CGTGCTCATCGCACCAATTTTAAAA-TTGATG---GCAGG
3145  157_HRV30b    TAGGGCGCTTGAGTATACC-CGTGCTCATCGCACCAATTTTAAAA-TTGATG---GCAGG
3146  158_HRV30     TAGGGCGCTTGAGTATACC-CGTGCTCATCGCACCAATTTTAAAA-TTGATG---GCAGG
3147  159_HRV7      ACGAGCTGTGCCTTATCAA-CACACTCACTCCACCAACTATGTGC-CACAAA---ATGGA
3148  160_HRV7b|    ACGAGCTGTGCCTTATCAA-CACACTCACTCCACCAACTATGTGC-CACAAA---ATGGA
3149  161_HRV7a|    ACGAGCTGTGCCTTATCAA-CACACTCACTCCACCAACTATGTGC-CACAAA---ATGGA
3150  162_HRV88     AAGAGCCGTACCTTATCAG-CACACTCACTCCACCAATTATGTAC-CAACAG---ATGGG
3151  163_HRV88a    AAGAGCCGTACCTTATCAG-CACACACACTCCACCAATTATGTAC-CAACAG---ATGGG
3152  164_HRV88b    AAGAGCCGTACCTTATCAG-CACACACACTCCACCAATTATGTAC-CAACAG---ATGGG
3153  165_HRV36a    AAGGGCCGTTCCTTACCAA-CACACACATTCCACTAATTATATAC-CATACA---AAGGT
3154  166_HRV36b    AAGGGCCGTTCCTTACCAA-CACACACATTCCACTAATTATATAC-CATACA---AAGGT
3155  167_HRV36     AAGGGCCGTTCCTTACCAA-CACACACATTCCACTAATTATATAC-CATACA---AAGGT
3156  168_HRV89a    AAGGGCTGTTGCCTATCAA-CACACACACTCAACCAATTACATAC-CATCCA---ATGGT
3157  169_HRV89b    AAGGGCTGTTGCCTATCAA-CACACACACTCAACCAATTACATAC-CATCCA---ATGGT
3158  170_HRV89     AAGGGCTGTTGCCTATCAA-CACACACACTCAACCAATTACATAC-CATCCA---ATGGT
3159  171_HRV58     AAGGGCTGTTCCTTATCAA-TTCACACATTCTACTAATTACATAC-CAGATA---GTGGT
3160  172_HRV58a    AAGGGCTGTTCCTTATCAA-TTCACACATTCTACTAATTACATAC-CAGATA---GTGGT
3161  173_HRV58b    AAGGGCTGTTCCTTATCAA-TTCACACATTCTACTAATTACATAC-CAGATA---GTGGT
3162  174_HRV12a    AAGAGCTGTACCATACCAG-CATATACACAATCCAAATTACAAGA-CAAGTA------AT
3163  175_HRV12b    AAGAGCTGTACCATACCAG-CATATACACAATCCAAATTACAAGA-CAAGTA------AT
3164  176_HRV12     AAGAGCTGTACCATACCAG-CATATACACAATCCAAATTACAAGA-CAAGTA------AT
3165  177_HRV78a    TAGAGCTGTACCTTATCAG-CACATATATAACCCTAATTATAAAA-CTGAAG------AA
3166  178_HRV78b    TAGAGCTGTACCTTATCAG-CACATATATAACCCTAATTATAAAA-CTGAAG------AA
3167  179_HRV78     TAGAGCTGTACCTTATCAG-CACATATATAACCCTAATTATAAAA-CTGAAG------AA
3168  180_HRV20     AAGAGCAGTGCCTTATCAA-CACACTAAGAGCACAAACTTAGTGC-CAAGGA---CAGGT
3169  181_HRV20a    AAGAGCAGTGCCTTATCAA-CACACTAAGAGCACAAACTTAGTGC-CAAGGA---CAGGT
3170  182_HRV20b    AAGAGCAGTGCCTTATCAA-CACACTAAGAGCACAAACTTAGTGC-CAAGGA---CAGGT
3171  183_HRV68     AAGAGCAGTGCCCTACCAG-CACACCAGAAGTACAAACTTAGTAC-CAAAGG---AAGGT
3172  184_HRV68a    AAGAGCAGTGCCCTACCAG-CACACCAGAAGTACAAACTTAGTAC-CAAAGG---AAGGT
3173  185_HRV68b    AAGAGCAGTGCCCTACCAG-CACACCAGAAGTACAAACTTAGTAC-CAAAGG---AAGGT
3174  186_HRV28     ACGCGCTGTAGCTTATCAA-CATACATACAGTCCAAACTTTGTGC-CTCAGG---AAGGT
3175  187_HRV28a    ACGCGCTGTAGCTTATCAA-CATACATACAGTCCAAACTTTGTGC-CTCAGG---AAGGT
3176  188_HRV28b    ACGCGCTGTAGCTTATCAA-CATACATACAGTCCAAACTTTGTGC-CTCAGG---AAGGT
3177  189_HRV53a    AAGAGCAGTTGCATATCAA-CACACATATAGCCCAAATTTTGTAC-CGCAAA---CAGGA
3178  190_HRV53b    AAGAGCAGTTGCATATCAA-CACACATATAGCCCAAATTTTGTAC-CGCAAA---CAGGA
3179  191_HRV53     AAGAGCAGTTGCATATCAA-CACACATATAGCCCAAATTTTGTAC-CGCAAA---CAGGA
3180  192_HRV46a    CAGAGCAGTCCCATATCAA-CATATTTATAATCCAAATTTCAAGA-CTACTCAACCTGAG
```

FIG. D8 CONT'D

```
04-2.trace                                                                  9/20/2007 5:04 PM 3181 193_HRV46b    CAGAGCAGTCCCATATCAA-CATATTTATAATCCAAATTTCAAGA-CTACTCAACCTGAG
3182 194_HRV46     CAGAGCAGTCCCATATCAA-CATATTTATAATCCAAATTTCAAGA-CTACTCAACCTGAG
3183 195_HRV80a    TAGAGCAGTCCCATACCAA-CATACCTACAGCCCAAATTTCAAAA-ACACTG---ATGAA
3184 196_HRV80b    TAGAGCAGTCCCATACCAA-CATACCTACAGCCCAAATTTCAAAA-ACACTG---ATGAA
3185 197_HRV80     TAGAGCAGTCCCATACCAA-CATACCTACAGCCCAAATTTCAAAA-ACACTG---ATGAA
3186 198_HRV51     TCGTGCTGTAGCCTACCAA-CACACATACAGTACAAACTTCGTTC-CAAAAGAGGGATTT
3187 199_HRV51a    TCGTGCTGTAGCCTACCAA-CACACATACAGTACAAACTTCGTTC-CAAAAGAGGGATTT
3188 200_HRV51b    TCGTGCTGTAGCCTACCAA-CACACATACAGTACAAACTTCGTTC-CAAAAGAGGGATTT
3189 201_HRV65a    CCGAGCAGTAGCTTACCAA-CACACATACAGTACAAATTTGTTC-CTAGCGGAGGTCTT
3190 202_HRV65b    CCGAGCAGTAGCTTACCAA-CACACATACAGTACAAATTTGTTC-CTAGCGGAGGTCTT
3191 203_HRV65     CCGAGCAGTAGCTTACCAA-CACACATACAGTACAAATTTGTTC-CTAGCGGAGGTCTT
3192 204_HRV71a    CAGAGCAGTAGCCTACCAA-TCAACATATACCACAAATTTTGTTC-CACAAGACGGGATC
3193 205_HRV71b    CAGAGCAGTAGCCTACCAA-TCAACATATACCACAAATTTGTTC-CACAAGACGGGATC
3194 206_HRV71     CAGAGCAGTAGCCTACCAA-TCAACATATACCACAAATTTGTTC-CACAAGACGGGATC
3195 207_HRV8      CAGAGCAGTTACGTATAAC-CATATATACAACCCCAATTATGTTA-GAGAGG------GA
3196 208_HRV95     CAGAGCAGTTACGTATAAC-CATATATACAACCCCAATTATGTTA-GAGAGG------GA
3197 209_HRV45     AAGAGCAGTCACATATAAC-CATACATATAATCCAAATTATGTTA-GGGCTG------AT
3198 210_HRV45a    AAGAGCAGTCACATATAAC-CATACATATAATCCAAATTATGTTA-GGGCTG------AT
3199 211_HRV45b    AAGAGCAGTCACATATAAC-CATACATATAATCCAAATTATGTTA-GGGCTG------AT
3200 GROUP_1       --G-G---T----TA-------------------AA-T----------------------
3201
3202  1_HRV1A1|d   GACG------TGACAACAG---CCATAGTCCGCAGAA------ACACTATAACAACTG--
3203  2_HRV1A2|d   GACG------TGACAACAG---CCATAGTCCGCAGAA------ACACTATAACAACTG--
3204  3_HRV1A|cD   GACG------TGACAACAG---CCATAGTCCGCAGAA------ACACTATAACAACTG--
3205  4_HRV1B1|d   GATG------TGACAACAG---CTATAGTTCCTAGAG------CTAGCATGAAAACTG--
3206  5_HRV1B2|d   GATG------TGACAACAG---CTATAGTTCCTAGAG------CTAGCATGAAAACTG--
3207  6_HRV1B      GATG------TGACAACAG---CTATAGTTCCTAGAG------CTAGCATGAAAACTG--
3208  7_HRV40a|d   GAAG------TCCAGATTT---TCCTCAAAGAGAGAG------CCAGCCTAACAACAG--
3209  8_HRV40b|d   GAAG------TCCAGATTT---TCCTCAAAGAGAGAG------CCAGCCTAACAACAG--
3210  9_HRV40      GAAG------TCCAGATTT---TCCTCAAAGAGAGAG------CCAGCCTAACAACAG--
3211 10_HRV85      GAAG------TTAAGATCT---TCCTCAAAGAGAGAG------CTAGTTTAACCACAG--
3212 11_HRV85a|    GAAG------TTAAGATCT---TCCTCAAAGAGAGAG------CTAGTTTAACCACAG--
3213 12_HRV85b|    GAAG------TTAAGATCT---TCCTCAAAGAGAGAG------CTAGTTTAACCACAG--
3214 13_HRV56a|    GATG------TACAGATCT---TCTTAAAACCCAGAC------CCAGCCTAACAACAT--
3215 14_HRV56b|    GATG------TACAGATCT---TCTTAAAACCCAGAC------CCAGCCTAACAACAT--
3216 15_HRV56      GATG------TACAGATCT---TCTTAAAACCCAGAC------CCAGCCTAACAACAT--
3217 16_HRV54      GATC------CAACAATTT---TCCTTAAACACAGGA------CAAACCTTGTAACAG--
3218 17_HRV98      GAAC------CAACAATCT---TTCTTAAGCATAGAA------AAGATCTTGTAACAG--
3219 18_HRV59a|    GAAC------CTGAAATTT---TCTTAAAACCAAGAA------TGAATATTACAACAG--
3220 19_HRV59b|    GAAC------CTGAAATTT---TCTTAAAACCAAGAA------TGAATATTACAACAG--
3221 20_HRV59      GAAC------CTGAAATTT---TCTTAAAACCAAGAA------TGAATATTACAACAG--
3222 21_HRV63      GAGA------CTGAAATTT---TCTTAAAACCTAGAG------CAACTATCAAGACAG--
3223 22_HRV63b|    GAGA------CTGAAATTT---TCTTAAAACCTAGAG------CAACTATCAAGACAG--
3224 23_HRV63a|    GAGA------CTGAAATTT---TCTTAAAACCTAGAG------CAACTATCAAGACAG--
3225 24_HRV39      GAAC------CAACACTCT---TTTATAAAATCAAGAG------AGAATCTTACCACAG--
3226 25_HRV39a|    GAAC------CAACACTCT---TTTATAAAATCAAGAG------AGAATCTTACCACAG--
3227 26_HRV39b|    GAAC------CAACACTCT---TTTATAAAACCAAGAG------AGAATCTTACCACAG--
3228 27_HRV10a|    GAAT------TACAAATAT---TTATTAGGTCTAGAGATGATCCCAAAGTAGTAACTG--
3229 28_HRV10b|    GAAT------TACAAATAT---TTATTAGGTCTAGAGATGATCCCAAAGTAGTAACTG--
3230 29_HRV10      GAAT------TACAAATAT---TTATTAGGTCTAGAGATGATCCCAAAGTAGTAACTG--
3231 30_HRV100a    GATG------TAAAGATTT---TCATTAGACCCAGAGATGATCCAAAGTTTGTAACTG--
3232 31_HRV100b    GATG------TAAAGATTT---TCATTAGACCCAGAGATGATCCAAAGTTTGTAACTG--
3233 32_HRV100     GATG------TAAAGATTT---TCATTAGACCCAGAGATGATCCAAAGTTTGTAACTG--
3234 33_HRV66      GATC------TGCAAATTT---TCATTAAACCTAGAACAGATCCAAAGTAGTCAATG--
3235 34_HRV66b|    GATC------TGCAAATTT---TCATTAAACCTAGAACAGATCCAAAGTAGTCAATG--
3236 35_HRV66a|    GATC------TGCAAATTT---TCATTAAACCTAGAACAGATCCAAAGTAGTCAATG--
3237 36_HRV77a|    GATG------TACAAATCT---TTATTAAAGAGAGAGCAAGCCCAAAAGTAGTTACTT--
3238 37_HRV77b|    GATG------TACAAATCT---TTATTAAAGAGAGAGCAAGCCCAAAAGTAGTTACTT--
3239 38_HRV77      GATG------TACAAATCT---TTATTAAAGAGAGAGCAAGCCCAAAAGTAGTTACTT--
3240 39_HRV62a     ---G------TTGACATTT---TTATAAAATCAAGG------CAAAACTTGCAAACAG--
3241 40_HRV62b     ---G------TTGACATTT---TTATAAAATCAAGG------CAAAACTTGCAAACAG--
3242 41_HRV25      ---G------TTGACATCT---TTATACAACCAAGA------AACAGTTTAAAAACAG--
3243 42_HRV29a     ---G------AT-CCAG-----TTGTGGAATCCAGA------CCAAGCTTAATGACAG--
3244 43_HRV29b     ---G------AT-ACAG-----TTGTGGAATCCAGA------CCAAGCTTAATGACAG--
3245 44_HRV44a     ---G------AT-ACAG-----TTGTGGAACCTAGA------CACAGCATAATGACAG--
```

FIG. D8 CONT'D

```
04-2.trace                                                                      9/20/2007 5:04 PM 3246  45_HRV44b      ---G------AT-ACAG-----TTGTGGAACCTAGA------CACAGCATAATGACAG--
3247  46_HRV31       GAAG------TTACAATCT---TTGTTAAACACAGGGATAATCCAAAGATTATCACAG--
3248  47_HRV31a|     GAAG------TTACAATCT---TTGTTAAACACAGGGATAATCCAAAGATTATCACAG--
3249  48_HRV31b|     GAAG------TTACAATCT---TTGTTAAACACAGGGATAATCCAAAGATTATCACAG--
3250  49_HRV47       GAAG------TTGCAATTT---TCATTGAGCATAGAGAAAATCCAAAATTCATTACAG--
3251  50_HRV47a|     GAAG------TTGCAATTT---TCATTGAGCATAGAGAAAATCCAAAATTCATTACAG--
3252  51_HRV47b|     GAAG------TTGCAATTT---TCATTGAGCATAGAGAAAATCCAAAATTCATTACAG--
3253  52_HRV11       CAGG------TGAAAACAG---CTGTCAAGGCTAGGAAAACAATTAAAACAGCA------
3254  53_HRV11b|     CAGG------TGAAAACAG---CTGTCAAGGCTAGGAAAACAATTAAAACAGCG------
3255  54_HRV11a|     CAGG------TGAAAACAG---CTGTCAAGGCTAGGAAAACAATTAAAACAGCT------
3256  55_HRV76       GATG------TGCAAACAG---CTATTAGACCAAGAGCAACAATTAAGACTGCA------
3257  56_HRV76b|     GATG------TGCAAACAG---CTATTAGACCAAGAGCAACAATTAAGACTGCG------
3258  57_HRV76a|     GATG------TGCAAACAG---CTATTAGACCAAGAGCAACAATTAAGACTGCT------
3259  58_HRV33       GAAG------TGAAGACAG---CTATTAGACCAAGAGCAACAATCAAGACTGCA------
3260  59_HRV33b|     GAAG------TGAAGACAG---CTATTAGACCAAGAGCAACAATCAAGACTGCG------
3261  60_HRV33a|     GAAG------TGAAGACAG---CTATTAGACCAAGAGCAACAATCAAGACTGCT------
3262  61_HRV24a|     GAAG------TCAAGACAG---CAATTGAACCTAGAAGAGGAATTAAAACAGTG------
3263  62_HRV24b|     GAAG------TCAAGACAG---CAATTGAACCTAGAAGAGGAATTAAAACAGTC------
3264  63_HRV24       GAAG------TCAAGACAG---CAATTGAACCTAGAAGAGGAATTAAAACAGTT------
3265  64_HRV90       GAAC------TTAAGACTG---CAATTAGGCCCAGGAAAACAATCACAACAGCA------
3266  65_HRV90a|     GAAC------TTAAGACTG---CAATTAGGCCCAGGAAAACAATCACAACAGCG------
3267  66_HRV90b|     GAAC------TTAAGACTG---CAATTAGGCCCAGGAAAACAATCACAACAGCT------
3268  67_HRV34       ACTG------AGAAGACTG---CAATCAAACACAGAGCAAAGATCACAATGGCC------
3269  68_HRV34b|     ACTG------AGAAGACTG---CAATCAAACACAGAGCAAAGATCACAATGGCA------
3270  69_HRV34a|     ACTG------AGAAGACTG---CAATCAAACACAGAGCAAAGATCACAATGGCT------
3271  70_HRV50a|     ACTG------AGAAGACTG---CAATTGCAACTAGACCAAAGATCACAGTGGCA------
3272  71_HRV50b|     ACTG------AGAAGACTG---CAATTGCAACTAGACCAAAGATCACAGTGGCG------
3273  72_HRV50       ACTG------AGAAGACTG---CAATTGCAACTAGACCAAAGATCACAGTGGCT------
3274  73_HRV18a|     AGAG------AGAAAACTG---CCATAGTACCCAGAGCAAGGATTACAATGGCA------
3275  74_HRV18b|     AGAG------AGAAAACTG---CCATAGTACCCAGAGCAAGGATTACAATGGCG------
3276  75_HRV18       AGAG------AGAAAACTG---CCATAGTACCCAGAGCAAGGATTACAATGGCT------
3277  76_HRV55       ACAG------AAAAGACAG---CAATTGAATACAGAAGGGACATTAAAACAGTG------
3278  77_HRV55b|     ACAG------AAAAGACAG---CAATTGAATACAGAAGGGACATTAAAACAGTC------
3279  78_HRV55a|     ACAG------AAAAGACAG---CAATTGAATACAGAAGGGACATTAAAACAGTA------
3280  79_HRV57       CAAG------AAGAAACAG---CAATTAAATATAGAAGGGACATTAAAATTGTTAAGA--
3281  80_HRV57a|     CAAG------AAGAAACAG---CAATTAAATATAGAAGGGACATTAAAATTGTTAAGA--
3282  81_HRV57b|     CAAG------AAGAAACAG---CAATTAAATATAGAAGGGACATTAAAATTGTTAAGA--
3283  82_HRV21       GAAG------TCACTTCTG---CAGTTGAGTCCAGAAGAACAATTGTCACAGTT------
3284  83_HRVHan      GATG------TCACTTCTG---CAGTTGAGTCCAGAAGAACAATTGTCACAGTT------
3285  84_HRV43       GAGG------TAGAAACAG---CCATAGTATCTAGGAGGGATATCAAAATTGTCAATG--
3286  85_HRV43b|     GAGG------TAGAAACAG---CCATAGTATCTAGGAGGGATATCAAAATTGTCAATG--
3287  86_HRV43a|     GAGG------TAGAAACAG---CCATAGTATCTAGGAGGGATATCAAAATTGTCAATG--
3288  87_HRV75       CAAG------TTGAGATTG---CTATTGAGCCCAGAAGAGATGTTAAGTTTGTAAATG--
3289  88_HRV75b|     CAAG------TTGAGATTG---CTATTGAGCCCAGAAGAGATGTTAAGTTTGTAAATG--
3290  89_HRV75a|     CAAG------TTGAGATTG---CTATTGAGCCCAGAAGAGATGTTAAGTTTGTAAATG--
3291  96_HRV9a|d     GATT------ATGCCACAG---TTATACCAGTTAGAGACAATGTTAGGGCAGTAAAGA--
3292  97_HRV9b|d     GATT------ATGCCACAG---TTATACCAGTTAGAGACAATGTTAGGGCAGTAAAGA--
3293  98_HRV9        GATT------ATGCCACAG---TTATACCAGTTAGAGACAATGTTAGGGCAGTAAAGA--
3294  99_HRV32       GATT------ACACCACAG---CCATACAAACCAGAGAGCATGTTAGAGCAGTCAAAA--
3295  100_HRV32a     GATT------ACACCACAG---CCATACAAACCAGAGAGCATGTTAGAGCAGTCAAAA--
3296  101_HRV32b     GATT------ACACCACAG---CCATACAAACCAGAGAGCATGTTAGAGCAGTCAAAA--
3297  102_HRV67      GAGG------CTCAAACGG---TTATACCTGTTAGAGCAGATGTTAGAACAATTAGAA--
3298  103_HRV67a     GAGG------CTCAAACGG---TTATACCTGTTAGAGCAGATGTTAGAACAATTAGAA--
3299  104_HRV67b     GAGG------CTCAAACGG---TTATACCTGTTAGAGCAGATGTTAGAACAATTAGAA--
3300  105_HRV15      GATG------TAACTACAG---TTATTCCAACTAGAGAAAATGTTAGAGCTATAGTAA--
3301  106_HRV15a     GATG------TAACTACAG---TTATTCCAACTAGAGAAAATGTTAGAGCTATAGTAA--
3302  107_HRV15b     GATG------TAACTACAG---TTATTCCAACTAGAGAAAATGTTAGAGCTATAGTAA--
3303  108_HRV74a     GACG------TAACTACAG---TCATCCCAACTAGG---------AGATCAATAGTGA--
3304  109_HRV74b     GACG------TAACTACAG---TCATCCCAACTAGG---------AGATCAATAGTGA--
3305  110_HRV74      GACG------TAACTACAG---TCATCCCAACTAGG---------AGATCAATAGTGA--
3306  111_HRV38a     GAAG------TAACCACTA---TGATTCCAACTAGAACCAACATAAGAACCATCGTAA--
3307  112_HRV38b     GAAG------TAACCACTA---TGATTCCAACTAGAACCAACATAAGAACCATCGTAA--
3308  113_HRV38      GAAG------TAACCACTA---TGATTCCAACTAGAACCAACATAAGAACCATCGTAA--
3309  114_HRV60      GAAG------CAGCCATAA---CAATCCCCATTAGAACTGATATACGAGCAATCAGAA--
3310  115_HRV60a     GAAG------CAGCCATAA---CAATCCCCATTAGAACTGATATACGAGCAATCAGAA--
```

FIG. D8 CONT'D

04-2.trace                                                                                          9/20/2007 5:04 PM

```
3311  116_HRV60b    GAAG------CAGCCATAA---CAATCCCCATTAGAACTGATATACGAGCAATCAGAA--
3312  117_HRV64a    GAAT------ACACACCAC---CCGTTCCGTCACGTAACAGCCCCAGAGATATTGTCA--
3313  118_HRV64b    GAAT------ACACACCAC---CCGTTCCGTCACGTAACAGCCCCAGAGATATTGTCA--
3314  119_HRV64     GAAT------ACACACCAC---CCGTTCCGTCACGTAACAGCCCCAGAGATATTGTCA--
3315  120_HRV94a    GAGT------ACAAGCCAC---CTGTCCCAGTTAGGAATAGCCCCAGAGACATTGTCA--
3316  121_HRV94b    GAGT------ACAAGCCAC---CTGTCCCAGTTAGGAATAGCCCCAGAGACATTGTCA--
3317  122_HRV94     GAGT------ACAAGCCAC---CTGTCCCAGTTAGGAATAGCCCCAGAGACATTGTCA--
3318  123_HRV22     GATT------ACACACTAC---CTATCCCAACAAGAGCCAACCCTAGACAAATTTTGA--
3319  124_HRV22a    GATT------ACACACTAC---CTATCCCAACAAGAGCCAACCCTAGACAAATTTTGA--
3320  125_HRV22b    GATT------ACACACTAC---CTATCCCAACAAGAGCCAACCCTAGACAAATTTTGA--
3321  126_HRV82     GATT------ACAGTGTTG---TTATTCCAGTTAGAGAGAGTCCCAGACAGATTCTTA--
3322  127_HRV82b    GATT------ACAGTGTTG---TTATTCCAGTTAGAGAGAGTCCCAGACAGATTCTTA--
3323  128_HRV82a    GATT------ACAGTGTTG---TTATTCCAGTTAGAGAGAGTCCCAGACAGATTCTTA--
3324  129_HRV19     GAAG------TCACTCTTC---CAATTGAAATAAGAGATAACCCTAGACATATAAAGA--
3325  130_HRV19a    GAAG------TCACTCTTC---CAATTGAAATAAGAGATAACCCTAGACATATAAAGA--
3326  131_HRV19b    GAAG------TCACTCTTC---CAATTGAAATAAGAGATAACCCTAGACATATAAAGA--
3327  132_HRV13     GATG------TTGCAGTCT---CCATTGTACCTAGAGCAAATGTTAGGGAAATTAGAA--
3328  133_HRV13a    GATG------TTGCAGTCT---CCATTGTACCTAGAGCAAATGTTAGGGAAATTAGAA--
3329  134_HRV13b    GATG------TTGCAGTCT---CCATTGTACCTAGAGCAAATGTTAGGGAAATTAGAA--
3330  135_HRV41     GCAGA---GATTGTGGCTT---CTGTCAGACCTAGAGACAATGTTAGACAAGTAAGAA--
3331  136_HRV41a    GCAGA---GATTGTGGCTT---CTGTCAGACCTAGAGACAATGTTAGACAAGTAAGAA--
3332  137_HRV41b    GCAGA---GATTGTGGCTT---CTGTCAGACCTAGAGACAATGTTAGACAAGTAAGAA--
3333  138_HRV73     GAAG------TTACTACTG---CCATTAGGCATAGAGATAATGTTAGAGCCATCCAAA--
3334  139_HRV73b    GAAG------TTACTACTG---CCATTAGGCATAGAGATAATGTTAGAGCCATCCAAA--
3335  140_HRV73a    GAAG------TTACTACTG---CCATTAGGCATAGAGATAATGTTAGAGCCATCCAAA--
3336  141_HRV61     GAAAAACAAGTTACCACTT---TCATCAAACCTAGAGCTAACTTAAGAGAGATTAGAA--
3337  142_HRV61a    GAAAAACAAGTTACCACTT---TCATCAAACCTAGAGCTAACTTAAGAGAGATTAGAA--
3338  143_HRV61b    GAAAAACAAGTTACCACTT---TCATCAAACCTAGAGCTAACTTAAGAGAGATTAGAA--
3339  144_HRV96     -------AGGTTACCACTT---TTATCAAACCTAGAGAAAATCTAAGGGATATTAGAA--
3340  145_HRV96b    -------AGGTTACCACTT---TTATCAAACCTAGAGAAAATCTAAGGGATATTAGAA--
3341  146_HRV96a    -------AGGTTACCACTT---TTATCAAACCTAGAGAAAATCTAAGGGATATTAGAA--
3342   90_HRV16a|   GTAC------ACAATGATGTGGCTATAAGACCTAGAACAAATCTAACAACTGTA------
3343   91_HRV16b|   GTAC------ACAATGATGTGGCTATAAGACCTAGAACAAATCTAACAACTGTC------
3344   92_1AYM_A    GTAC------ACAATGATGTGGCTATAAGACCTAGAACAAATCTAACAACTGTT------
3345   93_HRV81a|   GTCC------ACACTAGTGTAGCCATAAAACCTAGAACAAGTCTAACAAATGTG------
3346   94_HRV81b|   GTCC------ACACTAGTGTAGCCATAAAACCTAGAACAAGTCTAACAAATGTC------
3347   95_HRV81     GTCC------ACACTAGTGTAGCCATAAAACCTAGAACAAGTCTAACAAATGTT------
3348  147_HRV2      AGTA------TTCAGACAG---CAATTGTGACCAGACCAATTATCACTACAGCT------
3349  148_HRV2a|    AGTA------TTCAGACAG---CAATTGTGACCAGACCAATTATCACTACAGCA------
3350  149_HRV2b|    AGTA------TTCAGACAG---CAATTGTGACCAGACCAATTATCACTACAGCG------
3351  150_HRV49a    GACA------TTAAAACAG---GAATCACATCCAGAGCAATTATTACAACAGCG------
3352  151_HRV49b    GACA------TTAAAACAG---GAATCACATCCAGAGCAATTATTACAACAGCA------
3353  152_HRV49     GACA------TTAAAACAG---GAATCACATCCAGAGCAATTATTACAACAGCT------
3354  153_HRV23a    AATG------TCAAATCAA---GGGTTGCACATAGACCTGCAGTGATAACAGCG------
3355  154_HRV23b    AATG------TCAAATCAA---GGGTTGCACATAGACCTGCAGTGATAACAGCA------
3356  155_HRV23     AATG------TCAAATCAA---GGGTTGCACATAGACCTGCAGTGATAACAGCT------
3357  156_HRV30a    GAAG------TTAAATCAA---GGGTTGAACACAGAGCTAGGGTGACGACAGCA------
3358  157_HRV30b    GAAG------TTAAATCAA---GGGTTGAACACAGAGCTAGGGTGACGACAGCG------
3359  158_HRV30     GAAG------TTAAATCAA---GGGTTGAACACAGAGCTAGGGTGACGACAGCT------
3360  159_HRV7      GAGG------TCGCA---ACTCAAATCAAAACCAGAGCCAATCTTTTCACCCTCAAAT--
3361  160_HRV7b|    GAGG------TCGCA---ACTCAAATCAAAACCAGAGCCAATCTTTTCACCCTCAAAT--
3362  161_HRV7a|    GAGG------TCGCA---ACTCAAATCAAAACCAGAGCCAATCTTTTCACCCTCAAAT--
3363  162_HRV88     GAAG------TAGCA---ACTCAAATCAAAACCAGACGAGATGTTTACACTGTTACCA--
3364  163_HRV88a    GAAG------TAGCA---ACTCAAATCAAAACCAGACGAGATGTTTACACTGTTACCA--
3365  164_HRV88b    GAAG------TAGCA---ACTCAAATCAAAACCAGACGAGATGTTTACACTGTTACCA--
3366  165_HRV36a    GAGA------TCACA---ACCCAAATTAAAACCAGACCTAATGTCTTCACTGTA------
3367  166_HRV36b    GAGA------TCACA---ACCCAAATTAAAACCAGACCTAATGTCTTCACTGTG------
3368  167_HRV36     GAGA------TCACA---ACCCAAATTAAAACCAGACCTAATGTCTTCACTGTT------
3369  168_HRV89a    GAGG------CCACA---ACTCAGATTAAAACCAGACCTGATGTTTTTACCGTTACAA--
3370  169_HRV89b    GAGG------CCACA---ACTCAGATTAAAACCAGACCTGATGTTTTTACCGTTACAA--
3371  170_HRV89     GAGG------CCACA---ACTCAGATTAAAACCAGACCTGATGTTTTTACCGTTACAA--
3372  171_HRV58     GAGG------TAACA---ACACAAATCAAACCCAGAACCAATGTTTTTACTATTACAT--
3373  172_HRV58a    GAGG------TAACA---ACACAAATCAAACCCAGAACCAATGTTTTTACTATTACAT--
3374  173_HRV58b    GAGG------TAACA---ACACAAATCAAACCCAGAACCAATGTTTTTACTATTACAT--
3375  174_HRV12a    GGAG------TTCCAGACAATAGAGTCAAACTCAGAGAGACACTCACCACAGTA------
```

FIG. D8 CONT'D

```
04-2.trace                                                                  9/20/2007 5:04 PM 3376 175_HRV12b         GGAG------TTCCAGACAATAGAGTCAAACTCAGAGAGACACTCACCACAGTG------
3377 176_HRV12          GGAG------TTCCAGACAATAGAGTCAAACTCAGAGAGACACTCACCACAGTT------
3378 177_HRV78a         GGAA------CTCCAGACACCAAAGTGGCAATTAGAGCTAATATTAAAACTGTA------
3379 178_HRV78b         GGAA------CTCCAGACACCAAAGTGGCAATTAGAGCTAATATTAAAACTGTG------
3380 179_HRV78          GGAA------CTCCAGACACCAAAGTGGCAATTAGAGCTAATATTAAAACTGTT------
3381 180_HRV20          GAAA------TTACA---ACTCATATCAGATTCAGAAACACTGTCAAAGATCTAACATAC
3382 181_HRV20a         GAAA------TTACA---ACTCATATCAGATTCAGAAACACTGTCAAAGATCTAACATAC
3383 182_HRV20b         GAAA------TTACA---ACTCATATCAGATTCAGAAACACTGTCAAAGATCTAACATAC
3384 183_HRV68          GATA------TTAAA---ACTCATATTAAATTTAGGAATACTGTTAAAGATTTGGCATAT
3385 184_HRV68a         GATA------TTAAA---ACTCATATTAAATTTAGGAATACTGTTAAAGATTTGGCATAT
3386 185_HRV68b         GATA------TTAAA---ACTCATATTAAATTTAGGAATACTGTTAAAGATTTGGCATAT
3387 186_HRV28          GATG------TTGAG---ACTCATATTAAATTTAGAACAGATGTTAAACAGATCACAA--
3388 187_HRV28a         GATG------TTGAG---ACTCATATTAAATTTAGAACAGATGTTAAACAGATCACAA--
3389 188_HRV28b         GATG------TTGAG---ACTCATATTAAATTTAGAACAGATGTTAAACAGATCACAA--
3390 189_HRV53a         ACAG------TTGAA---ACTCACATTAAGTTCAGACCTGATGTTAAAGATGTAACAT--
3391 190_HRV53b         ACAG------TTGAA---ACTCACATTAAGTTCAGACCTGATGTTAAAGATGTAACAT--
3392 191_HRV53          ACAG------TTGAA---ACTCACATTAAGTTCAGACCTGATGTTAAAGATGTAACAT--
3393 192_HRV46a         ACTA------TACCAGATACTCATATTGGAATTAGAAGGGATATAAAGTACATTAAAA--
3394 193_HRV46b         ACTA------TACCAGATACTCATATTGGAATTAGAAGGGATATAAAGTACATTAAAA--
3395 194_HRV46          ACTA------TACCAGATACTCATATTGGAATTAGAAGGGATATAAAGTACATTAAAA--
3396 195_HRV80a         TCTA------TACCAGATACACAAATTAAAATCAGAGATAATATCAGGCAGGTTAGAA--
3397 196_HRV80b         TCTA------TACCAGATACACAAATTAAAATCAGAGATAATATCAGGCAGGTTAGAA--
3398 197_HRV80          TCTA------TACCAGATACACAAATTAAAATCAGAGATAATATCAGGCAGGTTAGAA--
3399 198_HRV51          GAAG------GCTTGAAAACTCAGATTAAAACTAGGGCAGACATCAAACTTGTGAACT--
3400 199_HRV51a         GAAG------GCTTGAAAACTCAGATTAAAACTAGGGCAGACATCAAACTTGTGAACT--
3401 200_HRV51b         GAAG------GCTTGAAAACTCAGATTAAAACTAGGGCAGACATCAAACTTGTGAACT--
3402 201_HRV65a         ACAA------ACCTAAGAACCCAAATTAAAACCAGAGATAACATTAAAATTGTAAACT--
3403 202_HRV65b         ACAA------ACCTAAGAACCCAAATTAAAACCAGAGATAACATTAAAATTGTAAACT--
3404 203_HRV65          ACAA------ACCTAAGAACCCAAATTAAAACCAGAGATAACATTAAAATTGTAAACT--
3405 204_HRV71a         AATT------CCATTAAAACCAAAATCAAAATCAGAAGAGACATTAAAGAGGTCAGCA--
3406 205_HRV71b         AATT------CCATTAAAACCAAAATCAAAATCAGAAGAGACATTAAAGAGGTCAGCA--
3407 206_HRV71          AATT------CCATTAAAACCAAAATCAAAATCAGAAGAGACATTAAAGAGGTCAGCA--
3408 207_HRV8           GTAA------CACCAGAAACTAAGGTTAAATATAGAGCTGAAGTCACAACCATT------
3409 208_HRV95          GTAA------CACCAGAAACTAAGGTCAAATATAGAGCTGAAGTCACAACCATT------
3410 209_HRV45          GAAA------CAGCC---ACAAAAGTCCAAACTAGAGCAAATGTCACAACAGTA------
3411 210_HRV45a         GAAA------CAGCC---ACAAAAGTCCAAACTAGAGCAAATGTCACAACAGTG------
3412 211_HRV45b         GAAA------CAGCC---ACAAAAGTCCAAACTAGAGCAAATGTCACAACAGTT------
3413 GROUP_1            ------------------------T--------G--------------------------
3414
3415  1_HRV1A1|d        ----CA----------------
3416  2_HRV1A2|d        ----CG----------------
3417  3_HRV1A|cD        ----CT----------------
3418  4_HRV1B1|d        ----TA----------------
3419  5_HRV1B2|d        ----TC----------------
3420  6_HRV1B           ----TT----------------
3421  7_HRV40a|d        ----TA----------------
3422  8_HRV40b|d        ----TC----------------
3423  9_HRV40           ----TT----------------
3424 10_HRV85           ----CA----------------
3425 11_HRV85a|         ----CG----------------
3426 12_HRV85b|         ----CT----------------
3427 13_HRV56a|         ----TA----------------
3428 14_HRV56b|         ----TG----------------
3429 15_HRV56           ----TT----------------
3430 16_HRV54           ----CT----------------
3431 17_HRV98           ----CT----------------
3432 18_HRV59a|         ----CA----------------
3433 19_HRV59b|         ----CG----------------
3434 20_HRV59           ----CT----------------
3435 21_HRV63           ----CA----------------
3436 22_HRV63b|         ----CG----------------
3437 23_HRV63a|         ----CT----------------
3438 24_HRV39           ----CT----------------
3439 25_HRV39a|         ----CA----------------
3440 26_HRV39b|         ----CT----------------
```

FIG. D8 CONT'D

04-2.trace                                                                 9/20/2007 5:04 PM

```
3441  27_HRV10a|      ----CA---------------
3442  28_HRV10b|      ----CC---------------
3443  29_HRV10       ----CT---------------
3444  30_HRV100a     ----CA---------------
3445  31_HRV100b     ----CG---------------
3446  32_HRV100      ----CT---------------
3447  33_HRV66       ----TA---------------
3448  34_HRV66b|     ----TG---------------
3449  35_HRV66a|     ----TC---------------
3450  36_HRV77a|     ----TG---------------
3451  37_HRV77b|     ----TA---------------
3452  38_HRV77       ----TT---------------
3453  39_HRV62a      ----CT---------------
3454  40_HRV62b      ----C----------------
3455  41_HRV25       ----CT---------------
3456  42_HRV29a      ----CT---------------
3457  43_HRV29b      ----CT---------------
3458  44_HRV44a      ----CT---------------
3459  45_HRV44b      ----CT---------------
3460  46_HRV31       ----CA---------------
3461  47_HRV31a|     ----CT---------------
3462  48_HRV31b|     ----CA---------------
3463  49_HRV47       ----CA---------------
3464  50_HRV47a|     ----CT---------------
3465  51_HRV47b|     ----CA---------------
3466  52_HRV11       ---------------------
3467  53_HRV11b|     ---------------------
3468  54_HRV11a|     ---------------------
3469  55_HRV76       ---------------------
3470  56_HRV76b|     ---------------------
3471  57_HRV76a|     ---------------------
3472  58_HRV33       ---------------------
3473  59_HRV33b|     ---------------------
3474  60_HRV33a|     ---------------------
3475  61_HRV24a|     ---------------------
3476  62_HRV24b|     ---------------------
3477  63_HRV24       ---------------------
3478  64_HRV90       ---------------------
3479  65_HRV90a|     ---------------------
3480  66_HRV90b|     ---------------------
3481  67_HRV34       ---------------------
3482  68_HRV34b|     ---------------------
3483  69_HRV34a|     ---------------------
3484  70_HRV50a|     ---------------------
3485  71_HRV50b|     ---------------------
3486  72_HRV50       ---------------------
3487  73_HRV18a|     ---------------------
3488  74_HRV18b|     ---------------------
3489  75_HRV18       ---------------------
3490  76_HRV55       ---------------------
3491  77_HRV55b|     ---------------------
3492  78_HRV55a|     ---------------------
3493  79_HRV57       ----ATGTG------------
3494  80_HRV57a|     ----ATGTA------------
3495  81_HRV57b|     ----ATGTC------------
3496  82_HRV21       ---------------------
3497  83_HRVHan      ---------------------
3498  84_HRV43       ----CA---------------
3499  85_HRV43b|     ----CG---------------
3500  86_HRV43a|     ----CT---------------
3501  87_HRV75       ----CA---------------
3502  88_HRV75b|     ----CG---------------
3503  89_HRV75a|     ----CT---------------
3504  96_HRV9a|d     ----ATGTC------------
3505  97_HRV9b|d     ----ATGTG------------
```

FIG. D8 CONT'D 04-2.trace                                                                9/20/2007 5:04 PM

```
3506  98_HRV9        ----ATGTA-----------
3507  99_HRV32       ----ATGTA-----------
3508  100_HRV32a     ----ATGTG-----------
3509  101_HRV32b     ----ATGTC-----------
3510  102_HRV67      ----ATGTA-----------
3511  103_HRV67a     ----ATGTC-----------
3512  104_HRV67b     ----ATGTT-----------
3513  105_HRV15      ----ATGTT-----------
3514  106_HRV15a     ----ATGTA-----------
3515  107_HRV15b     ----ATGTC-----------
3516  108_HRV74a     ----ATGTA-----------
3517  109_HRV74b     ----ATGTC-----------
3518  110_HRV74      ----ATGTT-----------
3519  111_HRV38a     ----ATGTA-----------
3520  112_HRV38b     ----ATGTC-----------
3521  113_HRV38      ----ATGTT-----------
3522  114_HRV60      ----CAGTT-----------
3523  115_HRV60a     ----CAGTA-----------
3524  116_HRV60b     ----CAGTG-----------
3525  117_HRV64a     ----CAGTG-----------
3526  118_HRV64b     ----CAGTG-----------
3527  119_HRV64      ----CAGTA-----------
3528  120_HRV94a     ----CAGTG-----------
3529  121_HRV94b     ----CAGTC-----------
3530  122_HRV94      ----CAGTA-----------
3531  123_HRV22      ----ATGTA-----------
3532  124_HRV22a     ----ATGTG-----------
3533  125_HRV22b     ----ATGTC-----------
3534  126_HRV82      ----ATGTA-----------
3535  127_HRV82b     ----ATGTT-----------
3536  128_HRV82a     ----ATGTC-----------
3537  129_HRV19      ----ATGTA-----------
3538  130_HRV19a     ----ATGTG-----------
3539  131_HRV19b     ----ATGTC-----------
3540  132_HRV13      ----ACTTT-----------
3541  133_HRV13a     ----ACTTG-----------
3542  134_HRV13b     ----ACTTA-----------
3543  135_HRV41      ----ATTAT-----------
3544  136_HRV41a     ----ATTAG-----------
3545  137_HRV41b     ----ATTAC-----------
3546  138_HRV73      ----ATTTT-----------
3547  139_HRV73b     ----ATTTG-----------
3548  140_HRV73a     ----ATTTC-----------
3549  141_HRV61      ----CATTT-----------
3550  142_HRV61a     ----CATTT-----------
3551  143_HRV61b     ----CATTT-----------
3552  144_HRV96      ----ATTTT-----------
3553  145_HRV96b     ----ATTTA-----------
3554  146_HRV96a     ----ATTTC-----------
3555  90_HRV16a|     --------------------
3556  91_HRV16b|     --------------------
3557  92_1AYM_A      --------------------
3558  93_HRV81a|     --------------------
3559  94_HRV81b|     --------------------
3560  95_HRV81       --------------------
3561  147_HRV2       --------------------
3562  148_HRV2a|     --------------------
3563  149_HRV2b|     --------------------
3564  150_HRV49a     --------------------
3565  151_HRV49b     --------------------
3566  152_HRV49      --------------------
3567  153_HRV23a     --------------------
3568  154_HRV23b     --------------------
3569  155_HRV23      --------------------
3570  156_HRV30a     --------------------
```

FIG. D8 CONT'D

```
04-2.trace                                                                              9/20/2007 5:04 PM 3571  157_HRV30b              --------------------
3572  158_HRV30               --------------------
3573  159_HRV7                ----CAGCT-----------
3574  160_HRV7b|              ----CAGCA-----------
3575  161_HRV7a|              ----CAGCG-----------
3576  162_HRV88               ----CTGCT-----------
3577  163_HRV88a              ----CTGCA-----------
3578  164_HRV88b              ----CTGCG-----------
3579  165_HRV36a              --------------------
3580  166_HRV36b              --------------------
3581  167_HRV36               --------------------
3582  168_HRV89a              ----ACGTG-----------
3583  169_HRV89b              ----ACGTA-----------
3584  170_HRV89               ----ACGTC-----------
3585  171_HRV58               ----CTGCT-----------
3586  172_HRV58a              ----CTGCA-----------
3587  173_HRV58b              ----CTGCC-----------
3588  174_HRV12a              --------------------
3589  175_HRV12b              --------------------
3590  176_HRV12               --------------------
3591  177_HRV78a              --------------------
3592  178_HRV78b              --------------------
3593  179_HRV78               --------------------
3594  180_HRV20               CCCACAGAAATGACGAATGTT
3595  181_HRV20a              CCCACAGAAATGACGAATGTA
3596  182_HRV20b              CCCACAGAAATGACGAATGTG
3597  183_HRV68               CCTCCAGAATTAGCAAACCTT
3598  184_HRV68a              CCTCCAGAATTAGCAAACCTT
3599  185_HRV68b              CCTCCAGAATTAGCAAACCTT
3600  186_HRV28               ----CAGTT-----------
3601  187_HRV28a              ----CAGTA-----------
3602  188_HRV28b              ----CAGTC-----------
3603  189_HRV53a              ----CAGTAATGACAGCT---
3604  190_HRV53b              ----CAGTAATGACAGCT---
3605  191_HRV53               ----CAGTAATGACAGCA---
3606  192_HRV46a              ----CAGCA-----------
3607  193_HRV46b              ----CAGCC-----------
3608  194_HRV46               ----CAGCT-----------
3609  195_HRV80a              ----CAGTA-----------
3610  196_HRV80b              ----CAGTC-----------
3611  197_HRV80               ----CAGTT-----------
3612  198_HRV51               -----TT-------------
3613  199_HRV51a              ------TA------------
3614  200_HRV51b              ------TG------------
3615  201_HRV65a              ------TG------------
3616  202_HRV65b              ------TA------------
3617  203_HRV65               -----TT-------------
3618  204_HRV71a              -----ACTAA----------
3619  205_HRV71b              -----ACTAG----------
3620  206_HRV71               -----ACTAT----------
3621  207_HRV8                --------------------
3622  208_HRV95               --------------------
3623  209_HRV45               --------------------
3624  210_HRV45a              --------------------
3625  211_HRV45b              --------------------
3626  GROUP_1                 --------------------
3627
3628
3629
3630  Summary:
3631
3632  GROUP_1                 AA-CC--T-GA----T------A-----T--T-----A-GT--T--T-GT-CC--A----
3633  SUMMARY                 AA-CC--T-GA----T------A-----T--T-----A-GT--T--T-GT-CC--A----
3634
```

FIG. D8 CONT'D

04-2.trace                                                                  9/20/2007 5:04 PM

```
3635 GROUP_1      ------AG-----------------A--C-G---C-----T-GA-GC-GC-GA-AC-GG-
3636 SUMMARY      ------AG-----------------A--C-G---C-----T-GA-GC-GC-GA-AC-GG-
3637
3638 GROUP_1      CA-AC-A--------CA-CC-GA-GA-----T-GA-AC--G----GT-----------A-
3639 SUMMARY      CA-AC-A--------CA-CC-GA-GA-----T-GA-AC--G----GT-----------A-
3640
3641 GROUP_1      AC-----ATGA-A------T-GA----TT--T-GG--G--C----TG-------------
3642 SUMMARY      AC-----ATGA-A------T-GA----TT--T-GG--G--C----TG-------------
3643
3644 GROUP_1      ------------------------------------------------------------
3645 SUMMARY      ------------------------------------------------------------
3646
3647 GROUP_1      ------------TGG----T-A---T----GA-ATG-C-CA--T--G--G-AA----GA-
3648 SUMMARY      ------------TGG----T-A---T----GA-ATG-C-CA--T--G--G-AA----GA-
3649
3650 GROUP_1      -T-TT-AC-TA-----G-TT--A-TC-GA--T-AC--T-G-T-----------C------
3651 SUMMARY      -T-TT-AC-TA-----G-TT--A-TC-GA--T-AC--T-G-T-----------C------
3652
3653 GROUP_1      -------------GG-CA--T-----T-CA-T--ATGT---T-CC-CC-GG-G--CC---
3654 SUMMARY      -------------GG-CA--T-----T-CA-T--ATGT---T-CC-CC-GG-G--CC---
3655
3656 GROUP_1      -CC--------G-------------TGG-A--C--G-A--AA----TC----TT-TGGCA
3657 SUMMARY      -CC--------G-------------TGG-A--C--G-A--AA----TC----TT-TGGCA
3658
3659 GROUP_1      ----GG-CA----T--CC--G--T--C--T-CC-TT-----G--T-GC-TC-G--TA-TA
3660 SUMMARY      ----GG-CA----T--CC--G--T--C--T-CC-TT-----G--T-GC-TC-G--TA-TA
3661
3662 GROUP_1      -ATGTT-TA-GA-GG-TA-----------------------TA-GG-------------
3663 SUMMARY      -ATGTT-TA-GA-GG-TA-----------------------TA-GG-------------
3664
3665 GROUP_1      -AA----ATGGG--C--T-T------G--T--T-AC-------CA---------------
3666 SUMMARY      -AA----ATGGG--C--T-T------G--T--T-AC-------CA---------------
3667
3668 GROUP_1      --T-----------T-T--C--AA-GC-AA-CA---------TGG-G-CC--G--C-C-
3669 SUMMARY      --T-----------T-T--C--AA-GC-AA-CA---------TGG-G-CC--G--C-C-
3670
3671 GROUP_1      --G-G---T----TA--------------------AA-T---------------------
3672 SUMMARY      --G-G---T----TA--------------------AA-T---------------------
3673
3674 GROUP_1      ---------------------T--------G-----------------------------
3675 SUMMARY      ---------------------T--------G-----------------------------
3676
3677 GROUP_1      --------------------
3678 SUMMARY      --------------------
3679
3680
```

FIG. D8 CONT'D 05.trace                                                          9/20/2007 5:04 PM

```
 1 Group 1:  1_HRV1A1|d
 2 Group 1:  2_HRV1A2|d
 3 Group 1:  3_HRV1A|cD
 4 Group 1:  4_HRV1B1|d
 5 Group 1:  5_HRV1B2|d
 6 Group 1:  6_HRV1B
 7 Group 1:  7_HRV40a|d
 8 Group 1:  8_HRV40b|d
 9 Group 1:  9_HRV40
10 Group 1: 10_HRV85
11 Group 1: 11_HRV85a|
12 Group 1: 12_HRV85b|
13 Group 1: 13_HRV56a|
14 Group 1: 14_HRV56b|
15 Group 1: 15_HRV56
16 Group 1: 16_HRV54
17 Group 1: 17_HRV98
18 Group 1: 18_HRV59a|
19 Group 1: 19_HRV59b|
20 Group 1: 20_HRV59
21 Group 1: 21_HRV63
22 Group 1: 22_HRV63b|
23 Group 1: 23_HRV63a|
24 Group 1: 24_HRV39
25 Group 1: 25_HRV39a|
26 Group 1: 26_HRV39b|
27 Group 1: 27_HRV10a|
28 Group 1: 28_HRV10b|
29 Group 1: 29_HRV10
30 Group 1: 30_HRV100a
31 Group 1: 31_HRV100b
32 Group 1: 32_HRV100
33 Group 1: 33_HRV66
34 Group 1: 34_HRV66b|
35 Group 1: 35_HRV66a|
36 Group 1: 36_HRV77a|
37 Group 1: 37_HRV77b|
38 Group 1: 38_HRV77
39 Group 1: 39_HRV62a
40 Group 1: 40_HRV62b
41 Group 1: 41_HRV25
42 Group 1: 42_HRV29a
43 Group 1: 43_HRV29b
44 Group 1: 44_HRV44a
45 Group 1: 45_HRV44b
46 Group 1: 46_HRV31
47 Group 1: 47_HRV31a|
48 Group 1: 48_HRV31b|
49 Group 1: 49_HRV47
50 Group 1: 50_HRV47a|
51 Group 1: 51_HRV47b|
52 Group 1: 52_HRV11
53 Group 1: 53_HRV11b|
54 Group 1: 54_HRV11a|
55 Group 1: 55_HRV76
56 Group 1: 56_HRV76b|
57 Group 1: 57_HRV76a|
58 Group 1: 58_HRV33
59 Group 1: 59_HRV33b|
60 Group 1: 60_HRV33a|
61 Group 1: 61_HRV24a|
62 Group 1: 62_HRV24b|
```

FIG. D9

05.trace								9/20/2007 5:04 PM

```
 63 Group 1:  63_HRV24
 64 Group 1:  64_HRV90
 65 Group 1:  65_HRV90a|
 66 Group 1:  66_HRV90b|
 67 Group 1:  67_HRV34
 68 Group 1:  68_HRV34b|
 69 Group 1:  69_HRV34a|
 70 Group 1:  70_HRV50a|
 71 Group 1:  71_HRV50b|
 72 Group 1:  72_HRV50
 73 Group 1:  73_HRV18a|
 74 Group 1:  74_HRV18b|
 75 Group 1:  75_HRV18
 76 Group 1:  76_HRV55
 77 Group 1:  77_HRV55b|
 78 Group 1:  78_HRV55a|
 79 Group 1:  79_HRV57
 80 Group 1:  80_HRV57a|
 81 Group 1:  81_HRV57b|
 82 Group 1:  82_HRV21
 83 Group 1:  83_HRVHan
 84 Group 1:  84_HRV43
 85 Group 1:  85_HRV43b|
 86 Group 1:  86_HRV43a|
 87 Group 1:  87_HRV75
 88 Group 1:  88_HRV75b|
 89 Group 1:  89_HRV75a|
 90 Group 1:  96_HRV9a|d
 91 Group 1:  97_HRV9b|d
 92 Group 1:  98_HRV9
 93 Group 1:  99_HRV32
 94 Group 1:  100_HRV32a
 95 Group 1:  101_HRV32b
 96 Group 1:  102_HRV67
 97 Group 1:  103_HRV67a
 98 Group 1:  104_HRV67b
 99 Group 1:  105_HRV15
100 Group 1:  106_HRV15a
101 Group 1:  107_HRV15b
102 Group 1:  108_HRV74a
103 Group 1:  109_HRV74b
104 Group 1:  110_HRV74
105 Group 1:  111_HRV38a
106 Group 1:  112_HRV38b
107 Group 1:  113_HRV38
108 Group 1:  114_HRV60
109 Group 1:  115_HRV60a
110 Group 1:  116_HRV60b
111 Group 1:  117_HRV64a
112 Group 1:  118_HRV64b
113 Group 1:  119_HRV64
114 Group 1:  120_HRV94a
115 Group 1:  121_HRV94b
116 Group 1:  122_HRV94
117 Group 1:  123_HRV22
118 Group 1:  124_HRV22a
119 Group 1:  125_HRV22b
120 Group 1:  126_HRV82
121 Group 1:  127_HRV82b
122 Group 1:  128_HRV82a
123 Group 1:  129_HRV19
124 Group 1:  130_HRV19a
125 Group 1:  131_HRV19b
126 Group 1:  132_HRV13
127 Group 1:  133_HRV13a
```

FIG. D9 CONT'D

```
05.trace                                                          9/20/2007 5:04 PM
    128 Group 1: 134_HRV13b
    129 Group 1: 135_HRV41
    130 Group 1: 136_HRV41a
    131 Group 1: 137_HRV41b
    132 Group 1: 138_HRV73
    133 Group 1: 139_HRV73b
    134 Group 1: 140_HRV73a
    135 Group 1: 141_HRV61
    136 Group 1: 142_HRV61a
    137 Group 1: 143_HRV61b
    138 Group 1: 144_HRV96
    139 Group 1: 145_HRV96b
    140 Group 1: 146_HRV96a
    141 Group 1: 90_HRV16a|
    142 Group 1: 91_HRV16b|
    143 Group 1: 92_1AYM_A
    144 Group 1: 93_HRV81a|
    145 Group 1: 94_HRV81b|
    146 Group 1: 95_HRV81
    147 Group 1: 147_HRV2
    148 Group 1: 148_HRV2a|
    149 Group 1: 149_HRV2b|
    150 Group 1: 150_HRV49a
    151 Group 1: 151_HRV49b
    152 Group 1: 152_HRV49
    153 Group 1: 153_HRV23a
    154 Group 1: 154_HRV23b
    155 Group 1: 155_HRV23
    156 Group 1: 156_HRV30a
    157 Group 1: 157_HRV30b
    158 Group 1: 158_HRV30
    159 Group 1: 159_HRV7
    160 Group 1: 160_HRV7b|
    161 Group 1: 161_HRV7a|
    162 Group 1: 162_HRV88
    163 Group 1: 163_HRV88a
    164 Group 1: 164_HRV88b
    165 Group 1: 165_HRV36a
    166 Group 1: 166_HRV36b
    167 Group 1: 167_HRV36
    168 Group 1: 168_HRV89a
    169 Group 1: 169_HRV89b
    170 Group 1: 170_HRV89
    171 Group 1: 171_HRV58
    172 Group 1: 172_HRV58a
    173 Group 1: 173_HRV58b
    174 Group 1: 174_HRV12a
    175 Group 1: 175_HRV12b
    176 Group 1: 176_HRV12
    177 Group 1: 177_HRV78a
    178 Group 1: 178_HRV78b
    179 Group 1: 179_HRV78
    180 Group 1: 180_HRV20
    181 Group 1: 181_HRV20a
    182 Group 1: 182_HRV20b
    183 Group 1: 183_HRV68
    184 Group 1: 184_HRV68a
    185 Group 1: 185_HRV68b
    186 Group 1: 186_HRV28
    187 Group 1: 187_HRV28a
    188 Group 1: 188_HRV28b
    189 Group 1: 189_HRV53a
    190 Group 1: 190_HRV53b
    191 Group 1: 191_HRV53
    192 Group 1: 192_HRV46a
```

FIG. D9 CONT'D

05.trace                                                                      9/20/2007 5:04 PM

```
193 Group 1: 193_HRV46b
194 Group 1: 194_HRV46
195 Group 1: 195_HRV80a
196 Group 1: 196_HRV80b
197 Group 1: 197_HRV80
198 Group 1: 198_HRV51
199 Group 1: 199_HRV51a
200 Group 1: 200_HRV51b
201 Group 1: 201_HRV65a
202 Group 1: 202_HRV65b
203 Group 1: 203_HRV65
204 Group 1: 204_HRV71a
205 Group 1: 205_HRV71b
206 Group 1: 206_HRV71
207 Group 1: 207_HRV8
208 Group 1: 208_HRV95
209 Group 1: 209_HRV45
210 Group 1: 210_HRV45a
211 Group 1: 211_HRV45b
212
213
214 >>>>>
215
216
217
218 Group 1:
219
220  1_HRV1A1|d    AATCCAGTAGAAAACTACATTGATGAAGTTTTAAATGAAGTTTTAGTAGTGCCGAATATA
221  2_HRV1A2|d    AATCCAGTAGAAAACTACATTGATGAAGTTTTAAATGAAGTTTTAGTAGTGCCGAATATA
222  3_HRV1A|cD    AATCCAGTAGAAAACTACATTGATGAAGTTTTAAATGAAGTTTTAGTAGTGCCGAATATA
223  4_HRV1B1|d    AATCCAGTGGAAAATTACATTGATGAAGTTTTAAATGAAGTTCTAGTAGTACCAAATATA
224  5_HRV1B2|d    AATCCAGTGGAAAATTACATTGATGAAGTTTTAAATGAAGTTCTAGTAGTACCAAATATA
225  6_HRV1B       AATCCAGTGGAAAATTACATTGATGAAGTTTTAAATGAAGTTCTAGTAGTACCAAATATA
226  7_HRV40a|d    AACCCCGTTGAAAGGTATGTTGATGAGGTTCTTAATGAAGTTCTGGTAGTTCCAAATATC
227  8_HRV40b|d    AACCCCGTTGAAAGGTATGTTGATGAGGTTCTTAATGAAGTTCTGGTAGTTCCAAATATC
228  9_HRV40       AACCCCGTTGAAAGGTATGTTGATGAGGTTCTTAATGAAGTTCTGGTAGTTCCAAATATC
229 10_HRV85       AATCCTGTTGAAAAATACGTTGATGAAGTCCTTAATGAGGTTCTAGTGGTTCCAAATATC
230 11_HRV85a|     AATCCTGTTGAAAAATACGTTGATGAAGTCCTTAATGAGGTTCTAGTGGTTCCAAATATC
231 12_HRV85b|     AATCCTGTTGAAAAATACGTTGATGAAGTCCTTAATGAGGTTCTAGTGGTTCCAAATATC
232 13_HRV56a|     AACCCAGTTGAGAGATATGTAGATGATGTTTTAAATGAAGTTTTAGTTGTTCCAAATATT
233 14_HRV56b|     AACCCAGTTGAGAGATATGTAGATGATGTTTTAAATGAAGTTTTAGTTGTTCCAAATATT
234 15_HRV56       AACCCAGTTGAGAGATATGTAGATGATGTTTTAAATGAAGTTTTAGTTGTTCCAAATATT
235 16_HRV54       AATCCTGTAGAAAGATATGTTGATGAAGTGTTAAATGAAGTGTTAGTTGTCCCAAACATT
236 17_HRV98       AATCCTGTAGAGAGATATGTTGATGAAGTATTAAATGAAGTGTTAGTTGTCCCAAACATT
237 18_HRV59a|     AACCCAGTGGAAAACTATGTTAATGATGTACTTAATGAGGTTTTAGTAGTACCAAATATA
238 19_HRV59b|     AACCCAGTGGAAAACTATGTTAATGATGTACTTAATGAGGTTTTAGTAGTACCAAATATA
239 20_HRV59       AACCCAGTGGAAAACTATGTTAATGATGTACTTAATGAGGTTTTAGTAGTACCAAATATA
240 21_HRV63       AATCCAGTAGAGAATTATGTAAATGATGTTCTTAATGAAGTGTTAGTTGTTCCAAACATA
241 22_HRV63b|     AATCCAGTAGAGAATTATGTAAATGATGTTCTTAATGAAGTGTTAGTTGTTCCAAACATA
242 23_HRV63a|     AATCCAGTAGAGAATTATGTAAATGATGTTCTTAATGAAGTGTTAGTTGTTCCAAACATA
243 24_HRV39       AATCCAGTAGAAAATTATATAGATGAAGTATTAAATGAGGTATTAGTTGTTCCTAATATA
244 25_HRV39a|     AATCCAGTAGAAAATTATATAGATGAAGTATTAAATGAGGTATTAGTTGTTCCTAATATA
245 26_HRV39b|     AATCCAGTAGAAAATTATATAGATGGAGTATTAAATGAGGTATTAGTTGTTCCTAATATA
246 27_HRV10a|     AATCCAGTTGAAAATTACATTGATAATGTACTTAATGAAGTCCTAGTGGTACCCAACATC
247 28_HRV10b|     AATCCAGTTGAAAATTACATTGATAATGTACTTAATGAAGTCCTAGTGGTACCCAACATC
248 29_HRV10       AATCCAGTTGAAAATTACATTGATAATGTACTTAATGAAGTCCTAGTGGTACCCAACATC
249 30_HRV100a     AATCCAGTAGAAAATTATGTTGAAGGTGTGCTGAATGAAGTACTAGTGGTACCTAATATT
250 31_HRV100b     AATCCAGTAGAAAATTATGTTGAAGGTGTGCTGAATGAAGTACTAGTGGTACCTAATATT
251 32_HRV100      AATCCAGTAGAAAATTATGTTGAAGGTGTGCTGAATGAAGTACTAGTGGTACCTAATATT
252 33_HRV66       AATCCAGTTGAAGATTATGTTGAGGGTGTTTTAAATGAAGTTTTAGTAGTACCAAACATC
253 34_HRV66b|     AATCCAGTTGAAGATTATGTTGAGGGTGTTTTAAATGAAGTTTTAGTAGTACCAAACATC
254 35_HRV66a|     AATCCAGTTGAAGATTATGTTGAGGGTGTTTTAAATGAAGTTTTAGTAGTACCAAACATC
255 36_HRV77a|     AATCCAGTTGAGGACTATATCGATAATGTACTTAATGAAGTCTTAGTAGTACCAAATACC
```

FIG. D9 CONT'D

05.trace                                                                9/20/2007 5:04 PM

```
256  37_HRV77b|    AATCCAGTTGAGGACTATATCGATAATGTACTTAATGAAGTCTTAGTAGTACCAAATACC
257  38_HRV77     AATCCAGTTGAGGACTATATCGATAATGTACTTAATGAAGTCTTAGTAGTACCAAATACC
258  39_HRV62a    AATCCAATTGAAAATTATGTAGATCAAGTACTTAATGAAGTTTTAGTTGTACCAAATATT
259  40_HRV62b    AATCCAATTGAAAATTATGTAGATCAAGTACTTAATGAAGTTTTAGTTGTACCAAATATT
260  41_HRV25     AATCCAATTGAAAATTATGTAGATCAAGTACTTAATGAGGTTCTAGTCGTACCAAATATT
261  42_HRV29a    AACCCAGTTGAAAACTATGTGGATGAGGTGCTTAATGAAGTTTTAGTTGTGCCTAACATC
262  43_HRV29b    AACCCAGTTGAAAACTATGTGGATGAGGTGCTTAATGAAGTTTTAGTTGTGCCTAACATC
263  44_HRV44a    AACCCAGTTGAAAATTATGTGGATGAAGTACTTAATGAAGTCTTAGTTGTGCCTAATATC
264  45_HRV44b    AACCCAGTTGAAAATTATGTGGATGAAGTACTTAATGAAGTCTTAGTTGTGCCTAATATC
265  46_HRV31     AATCCAGTTGAAAACTATGTGGAAGAGGTTCTTAATGAAGTCTTAGTAGTACCTAATATC
266  47_HRV31a|   AATCCAGTTGAAAACTATGTGGAAGAGGTTCTTAATGAAGTCTTAGTAGTACCTAATATC
267  48_HRV31b|   AATCCAGTTGAAAACTATGTGGAAGAGGTTCTTAATGAAGTCTTAGTAGTACCTAATATC
268  49_HRV47     AACCCAGTCGAAAATTATGTGGAAGAGGTACTTAATGAGGTCTTAGTTGTACCAAATATC
269  50_HRV47a|   AACCCAGTCGAAAATTATGTGGAAGAGGTACTTAATGAGGTCTTAGTTGTACCAAATATC
270  51_HRV47b|   AACCCAGTCGAAAATTATGTGGAAGAGGTACTTAATGAGGTCTTAGTTGTACCAAATATC
271  52_HRV11     AACCCAGTGGAGGATTATGTTGATGGAATTCTAAATGAGGTTTTAGTTGTACCTAATATA
272  53_HRV11b|   AACCCAGTGGAGGATTATGTTGATGGAATTCTAAATGAGGTTTTAGTTGTACCTAATATA
273  54_HRV11a|   AACCCAGTGGAGGATTATGTTGATGGAATTCTAAATGAGGTTTTAGTTGTACCTAATATA
274  55_HRV76     AACCCAGTTGAAAATTACGTGGATGAGATATTAAATGAGGTTCTTGTAGTACCAAACATC
275  56_HRV76b|   AACCCAGTTGAAAATTACGTGGATGAGATATTAAATGAGGTTCTTGTAGTACCAAACATC
276  57_HRV76a|   AACCCAGTTGAAAATTACGTGGATGAGATATTAAATGAGGTTCTTGTAGTACCAAACATC
277  58_HRV33     AATCCAGTAGAGAATTATATAGAAGAGGTGTTGAATGAGGTTTTAGTAGTGCCTAATATC
278  59_HRV33b|   AATCCAGTAGAGAATTATATAGAAGAGGTGTTGAATGAGGTTTTAGTAGTGCCTAATATC
279  60_HRV33a|   AATCCAGTAGAGAATTATATAGAAGAGGTGTTGAATGAGGTTTTAGTAGTGCCTAATATC
280  61_HRV24a|   AACCCAGTAGAAAATTATATAGATGAGGTTTTGAATGAAGTACTGGTTGTGCCTAATATT
281  62_HRV24b|   AACCCAGTAGAAAATTATATAGATGAGGTTTTGAATGAAGTACTGGTTGTGCCTAATATT
282  63_HRV24     AACCCAGTAGAAAATTATATAGATGAGGTTTTGAATGAAGTACTGGTTGTGCCTAATATT
283  64_HRV90     AATCCAGTGGAAAATTATATAGATGAAGTCCTAAATGAGGTATTGGTTGTCCCTAATATT
284  65_HRV90a|   AATCCAGTGGAAAATTATATAGATGAAGTCCTAAATGAGGTATTGGTTGTCCCTAATATT
285  66_HRV90b|   AATCCAGTGGAAAATTATATAGATGAAGTCCTAAATGAGGTATTGGTTGTCCCTAATATT
286  67_HRV34     AATCCAGTTGAAAATTACATAGAGAGGTACTAAATGAGGTATTGGTTGTACCAAACATT
287  68_HRV34b|   AATCCAGTTGAAAATTACATAGAGAGGTACTAAATGAGGTATTGGTTGTACCAAACATT
288  69_HRV34a|   AATCCAGTTGAAAATTACATAGAGAGGTACTAAATGAGGTATTGGTTGTACCAAACATT
289  70_HRV50a|   AATCCAGTGGAGAATTACATAGATGAAGTATTAAATGAGGTATTAGTTGTCCCAAATATC
290  71_HRV50b|   AATCCAGTGGAGAATTACATAGATGAAGTATTAAATGAGGTATTAGTTGTCCCAAATATC
291  72_HRV50     AATCCAGTGGAGAATTACATAGATGAAGTATTAAATGAGGTATTAGTTGTCCCAAATATC
292  73_HRV18a|   AATCCAGTAGAGAATTATATAGATGAAGTACTTAATGAAGTGTTAGTGGTCCCAAATGTG
293  74_HRV18b|   AATCCAGTAGAGAATTATATAGATGAAGTACTTAATGAAGTGTTAGTGGTCCCAAATGTG
294  75_HRV18     AATCCAGTAGAGAATTATATAGATGAAGTACTTAATGAAGTGTTAGTGGTCCCAAATGTG
295  76_HRV55     AATCCTGTAGAGAGATATGTTGATGAAGTCCTGAATGAAGTGCTAGTAGTTCCAAATATT
296  77_HRV55b|   AATCCTGTAGAGAGATATGTTGATGAAGTCCTGAATGAAGTGCTAGTAGTTCCAAATATT
297  78_HRV55a|   AATCCTGTAGAGAGATATGTTGATGAAGTCCTGAATGAAGTGCTAGTAGTTCCAAATATT
298  79_HRV57     AACCCAGTAGAAAATTTTGTGGATGAGATCTTGAATGAAGTTTTGGTGGTTCCAGATATC
299  80_HRV57a|   AACCCAGTAGAAAATTTTGTGGATGAGATCTTGAATGAAGTTTTGGTGGTTCCAGATATC
300  81_HRV57b|   AACCCAGTAGAAAATTTTGTGGATGAGATCTTGAATGAAGTTTTGGTGGTTCCAGATATC
301  82_HRV21     AATCCTGTAGAGAATTATATAGAAGTCCTAAATGAAGTCTTAGTAGTGCCAAATATC
302  83_HRVHan    AATCCTGTAGAGAATTACGTAGATGAAGTTCTAAATGAGGTCTTAGTAGTGCCAAATATC
303  84_HRV43     AATCCTGTTGAAAATTATGTTGATGAAATTTAAATCAAGTTCTTGTAGTCCCAAACACT
304  85_HRV43b|   AATCCTGTTGAAAATTATGTTGATGAAATTTAAATCAAGTTCTTGTAGTCCCAAACACT
305  86_HRV43a|   AATCCTGTTGAAAATTATGTTGATGAAATTTAAATCAAGTTCTTGTAGTCCCAAACACT
306  87_HRV75     AATCCAGTTGAAAATTATGTGGATGAAATTTAAACCAAGTTCTGGTAGTTCCAAACACC
307  88_HRV75b|   AATCCAGTTGAAAATTATGTGGATGAAATTTAAACCAAGTTCTGGTAGTTCCAAACACC
308  89_HRV75a|   AATCCAGTTGAAAATTATGTGGATGAAATTTAAACCAAGTTCTGGTAGTTCCAAACACC
309  96_HRV9a|d   AATCCAGTGGAGAATTACATAGATCAGGTGCTTAATGAGGTTTTGGTAGTCCCAAACATT
310  97_HRV9b|d   AATCCAGTGGAGAATTACATAGATCAGGTGCTTAATGAGGTTTTGGTAGTCCCAAACATT
311  98_HRV9      AATCCAGTGGAGAATTACATAGATCAGGTGCTTAATGAGGTTTTGGTAGTCCCAAACATT
312  99_HRV32     AATCCTGTGGAGAATTACATAGATCAAGTTTAAATGAAGTTTTGGTAGTTCCAAACATC
313  100_HRV32a   AATCCTGTGGAGAATTACATAGATCAAGTTTTAAATGAAGTTTTGGTAGTTCCAAACATC
314  101_HRV32b   AATCCTGTGGAGAATTACATAGATCAAGTTTTAAATGAAGTTTTGGTAGTTCCAAACATC
315  102_HRV67    AACCCAGTAGAAGATTATGTAGATCAGGTATTGAATGAGGTCCTGGTGGTGCCAAATATA
316  103_HRV67a   AACCCAGTAGAAGATTATGTAGATCAGGTATTGAATGAGGTCCTGGTGGTGCCAAATATA
317  104_HRV67b   AACCCAGTAGAAGATTATGTAGATCAGGTATTGAATGAGGTCCTGGTGGTGCCAAATATA
318  105_HRV15    AACCCAGTGGAGAATTACATAGATGAAGTGTTAAATGAGGTTCTAGTAGTTCCAAACATT
319  106_HRV15a   AACCCAGTGGAGAATTACATAGATGAAGTGTTAAATGAGGTTCTAGTAGTTCCAAACATT
320  107_HRV15b   AACCCAGTGGAGAATTACATAGATGAAGTGTTAAATGAGGTTCTAGTAGTTCCAAACATT
```

FIG. D9 CONT'D

```
05.trace                                                                          9/20/2007 5:04 PM 321 108_HRV74a   AACCCAGTGGAGAATTACATAGATGAAGTGTTGAATGAAGTGTTAGTTGTTCCAAATATT
322 109_HRV74b   AACCCAGTGGAGAATTACATAGATGAAGTGTTGAATGAAGTGTTAGTTGTTCCAAATATT
323 110_HRV74    AACCCAGTGGAGAATTACATAGATGAAGTGTTGAATGAAGTGTTAGTTGTTCCAAATATT
324 111_HRV38a   AACCCAGTAGAGGAATACATAGATGGAGTCTTGAATGAGGTTCTTGTGGTTCCGAACATT
325 112_HRV38b   AACCCAGTAGAGGAATACATAGATGGAGTCTTGAATGAGGTTCTTGTGGTTCCGAACATT
326 113_HRV38    AACCCAGTAGAGGAATACATAGATGGAGTCTTGAATGAGGTTCTTGTGGTTCCGAACATT
327 114_HRV60    AATCCAGTAGAAAGCTACATAGATGGGGTCTTAAACGAAGTCCTTGTGGTTCCAAACATT
328 115_HRV60a   AATCCAGTAGAAAGCTACATAGATGGGGTCTTAAACGAAGTCCTTGTGGTTCCAAACATT
329 116_HRV60b   AATCCAGTAGAAAGCTACATAGATGGGGTCTTAAACGAAGTCCTTGTGGTTCCAAACATT
330 117_HRV64a   AACCCAGTTGAACAATACATTGATGGTGTGTTGAATGAAGTTTTGATTGTCCCAAACATC
331 118_HRV64b   AACCCAGTTGAACAATACATTGATGGTGTGTTGAATGAAGTTTTGATTGTCCCAAACATC
332 119_HRV64    AACCCAGTTGAACAATACATTGATGGTGTGTTGAATGAAGTTTTGATTGTCCCAAACATC
333 120_HRV94a   AATCCAGTTGAGAAATACATTGATGGTGTATTGAATGAAGTTTTAGTTGTTCCAAATATT
334 121_HRV94b   AATCCAGTTGAGAAATACATTGATGGTGTATTGAATGAAGTTTTAGTTGTTCCAAATATT
335 122_HRV94    AATCCAGTTGAGAAATACATTGATGGTGTATTGAATGAAGTATTAGTTGTTCCAAATATT
336 123_HRV22    AACCCTGTAGAGAAATACATTGATGGTGTATTGAATGAAGTATTGGTTGTTCCAAACACA
337 124_HRV22a   AACCCTGTAGAGAAATACATTGATGGTGTATTGAATGAAGTATTGGTTGTTCCAAACACA
338 125_HRV22b   AACCCTGTAGAGAAATACATTGATGGTGTATTGAATGAAGTATTAGTTGTTCCAAACACA
339 126_HRV82    AATCCAGTTGAAAAGTATGTTGATAGTGTTTTAAACGAGGTATTAGTTGTTCCTAACATT
340 127_HRV82b   AATCCAGTTGAAAAGTATGTTGATAGTGTTTTAAACGAGGTATTAGTTGTTCCTAACATT
341 128_HRV82a   AATCCAGTTGAAAAGTATGTTGATAGTGTTTTAAACGAGGTATTAGTTGTTCCTAACATT
342 129_HRV19    AATCCTGTAGAGAAATATGTGGACACCATTCTGAATGAGGTGCTAGTTGTCCCAAATATC
343 130_HRV19a   AATCCTGTAGAGAAATATGTGGACACCATTCTGAATGAGGTGCTAGTTGTCCCAAATATC
344 131_HRV19b   AATCCTGTAGAGAAATATGTGGACACCATTCTGAATGAGGTGCTAGTTGTCCCAAATATC
345 132_HRV13    AATCCTGTTGAAAGGTATGTAGATGAAGTCTTGAATGAAGTTCTTGTAGTACCAAATATC
346 133_HRV13a   AATCCTGTTGAAAGGTATGTAGATGAAGTCTTGAATGAAGTTCTTGTAGTACCAAATATC
347 134_HRV13b   AATCCTGTTGAAAGGTATGTAGATGAAGTCTTGAATGAAGTTCTTGTAGTACCAAATATC
348 135_HRV41    AATCCTGTAGAAAGGTATGTGGATGAGGTCCTGAATGAGGTTCTTGTGGTACCAAATATT
349 136_HRV41a   AATCCTGTAGAAAGGTATGTGGATGAGGTCCTGAATGAGGTTCTTGTGGTACCAAATATT
350 137_HRV41b   AATCCTGTAGAAAGGTATGTGGATGAGGTCCTGAATGAGGTTCTTGTGGTACCAAATATT
351 138_HRV73    AATCCTGTAGAAAGATATGTAGATGAAGTTTTGAATGAAGTCCTTGTAGTACCCAATATC
352 139_HRV73b   AATCCTGTAGAAAGATATGTAGATGAAGTTTTGAATGAAGTCCTTGTAGTACCCAATATC
353 140_HRV73a   AATCCTGTAGAAAGATATGTAGATGAAGTTTTGAATGAAGTCCTTGTAGTACCCAATATC
354 141_HRV61    AACCCTGTGGAAAGATATGTAGATGAAGTTTTAAATGAAGTGCTTGTAGTCCCAAACATT
355 142_HRV61a   AACCCTGTGGAAAGATATGTAGATGAAGTTTTAAATGAAGTGCTTGTAGTCCCAAACATT
356 143_HRV61b   AACCCTGTGGAAAGATATGTAGATGAAGTTTTAAATGAAGTGCTTGTAGTCCCAAACATT
357 144_HRV96    AACCCTGTAGAGAGATATGTAGATGAAGTCTTGAATGAGGTTCTTGTAGTCCCTAATATT
358 145_HRV96b   AACCCTGTAGAGAGATATGTAGATGAAGTCTTGAATGAGGTTCTTGTAGTCCCTAATATT
359 146_HRV96a   AACCCTGTAGAGAGATATGTAGATGAAGTCTTGAATGAGGTTCTTGTAGTCCCTAATATT
360  90_HRV16a|  AATCCAGTGGAAAGATATGTAGATGAAGTCTTAAATGAAGTGTTAGTAGTGCCCAATATT
361  91_HRV16b|  AATCCAGTGGAAAGATATGTAGATGAAGTCTTAAATGAAGTGTTAGTAGTGCCCAATATT
362  92_1AYM_A   AATCCAGTGGAAAGATATGTAGATGAAGTCTTAAATGAAGTGTTAGTAGTGCCCAATATT
363  93_HRV81a|  AACCCAGTGGAGCGGTATGTGGATGAAGTCTTAAATGAGGTATTGGTAGTCCCTAATATT
364  94_HRV81b|  AACCCAGTGGAGCGGTATGTGGATGAAGTCTTAAATGAGGTATTGGTAGTCCCTAATATT
365  95_HRV81    AACCCAGTGGAGCGGTATGTGGATGAAGTCTTAAATGAGGTATTGGTAGTCCCTAATATT
366 147_HRV2     AACCCTGTTGAGAATTATATAGATGAAGTTCTTAATGAAGTTTTAGTTGTCCCAAATATT
367 148_HRV2a|   AACCCTGTTGAGAATTATATAGATGAAGTTCTTAATGAAGTTTTAGTTGTCCCAAATATT
368 149_HRV2b|   AACCCTGTTGAGAATTATATAGATGAAGTTCTTAATGAAGTTTTAGTTGTCCCAAATATT
369 150_HRV49a   AATCCTGTTGAACACTACATAGATGAGGTCCTTAATGAGGTTTTAGTTGTTCCAAATATT
370 151_HRV49b   AATCCTGTTGAACACTACATAGATGAGGTCCTTAATGAGGTTTTAGTTGTTCCAAATATT
371 152_HRV49    AATCCTGTTGAACACTACATAGATGAGGTCCTTAATGAGGTTTTAGTTGTTCCAAATATT
372 153_HRV23a   AATCCAATTGAGAACTATGTAGATGAAGTTCTTAATGAAGTCTTAGTTGTTCCCAATATC
373 154_HRV23b   AATCCAATTGAGAACTATGTAGATGAAGTTCTTAATGAAGTCTTAGTTGTTCCCAATATC
374 155_HRV23    AATCCAATTGAGAACTATGTAGATGAAGTTCTTAATGAAGTCTTAGTTGTTCCCAATATC
375 156_HRV30a   AACCCGGTTGAAAATTTTGTAGATGAAGTTCTTAGTGAAGTTTTAGTTGTTCCAAACATT
376 157_HRV30b   AACCCGGTTGAAAATTTTGTAGATGAAGTTCTTAGTGAAGTTTTAGTTGTTCCAAACATT
377 158_HRV30    AACCCGGTTGAAAATTTTGTAGATGAAGTTCTTAGTGAAGTTTTAGTTGTTCCAAACATT
378 159_HRV7     AACCCGGTAGAGAATTATGTAGATAGCTTACTAAATGAAGTATTAGTGGTACCTAATATT
379 160_HRV7b|   AACCCGGTAGAGAATTATGTAGATAGCTTACTAAATGAAGTATTAGTGGTACCTAATATT
380 161_HRV7a|   AACCCGGTAGAGAATTATGTAGATAGCTTACTAAATGAAGTATTAGTGGTACCTAATATT
381 162_HRV88    AATCCAGTAGAAACTATGTAGATAACTTGTTAAACGAAGTGCTAGTAGTTCCTAACATT
382 163_HRV88a   AATCCAGTAGAAACTATGTAGATAACTTGTTAAACGAAGTGCTAGTAGTTCCTAACATT
383 164_HRV88b   AATCCAGTAGAAACTATGTAGATAACTTGTTAAACGAAGTGCTAGTAGTTCCTAACATT
384 165_HRV36a   AATCCAGTTGAAAATTACATAGATAATGTATTAAATGAAGTACTTGTAGTGCCAAACATC
385 166_HRV36b   AATCCAGTTGAAAATTACATAGATAATGTATTAAATGAAGTACTTGTAGTGCCAAACATC
```

FIG. D9 CONT'D

05.trace                                                                                       9/20/2007 5:04 PM

```
386  167_HRV36     AATCCAGTTGAAAATTACATAGATAATGTATTAAATGAAGTACTTGTAGTGCCAAACATC
387  168_HRV89a    AACCCAGTTGAAAATTATATAGATAGTGTATTAAATGAAGTTCTTGTGGTGCCAAATATC
388  169_HRV89b    AACCCAGTTGAAAATTATATAGATAGTGTATTAAATGAAGTTCTTGTGGTGCCAAATATC
389  170_HRV89     AACCCAGTTGAAAATTATATAGATAGTGTATTAAATGAAGTTCTTGTGGTGCCAAATATC
390  171_HRV58     AATCCAGTAGAAAATTACATAGATAATGTGTTAAATGAAGTACTTGTAGTTCCAAATATC
391  172_HRV58a    AATCCAGTAGAAAATTACATAGATAATGTGTTAAATGAAGTACTTGTAGTTCCAAATATC
392  173_HRV58b    AATCCAGTAGAAAATTACATAGATAATGTGTTAAATGAAGTACTTGTAGTTCCAAATATC
393  174_HRV12a    AATCCAGTAGAGAGATATGTTGATGAGGTGCTAAATGAAGTTCTAGTTGTTCCAAACATA
394  175_HRV12b    AATCCAGTAGAGAGATATGTTGATGAGGTGCTAAATGAAGTTCTAGTTGTTCCAAACATA
395  176_HRV12     AATCCAGTAGAGAGATATGTTGATGAGGTGCTAAATGAAGTTCTAGTTGTTCCAAACATA
396  177_HRV78a    AATCCAGTGGAAGAATATGTTGATCAGGTTTTAAATGAGGTTTTAGTTGTTCCAAACATA
397  178_HRV78b    AATCCAGTGGAAGAATATGTTGATCAGGTTTTAAATGAGGTTTTAGTTGTTCCAAACATA
398  179_HRV78     AATCCAGTGGAAGAATATGTTGATCAGGTTTTAAATGAGGTTTTAGTTGTTCCAAACATA
399  180_HRV20     AACCCAGTGGAAAGGTACACAGAAGCTATTTTAAATGAAGTTCTTGTAGTTCCAAATATC
400  181_HRV20a    AACCCAGTGGAAAGGTACACAGAAGCTATTTTAAATGAAGTTCTTGTAGTTCCAAATATC
401  182_HRV20b    AACCCAGTGGAAAGGTACACAGAAGCTATTTTAAATGAAGTTCTTGTAGTTCCAAATATC
402  183_HRV68     AACCCAGTTGAAAAATACACAGAAGCCGTTCTTAATGAGGTCCTTGTGGTTCCAAACATA
403  184_HRV68a    AACCCAGTTGAAAATACACAGAAGCCGTTCTTAATGAGGTCCTTGTGGTTCCAAACATA
404  185_HRV68b    AACCCAGTTGAAAATACACAGAAGCCGTTCTTAATGAGGTCCTTGTGGTTCCAAACATA
405  186_HRV28     AATCCAGTTGAAAATATACTGAAGCACTACTTAATGAAGTGCTTGTTGTGCCAAACATC
406  187_HRV28a    AATCCAGTTGAAAAATATACTGAAGCACTACTTAATGAAGTGCTTGTTGTGCCAAACATC
407  188_HRV28b    AATCCAGTTGAAAATATACTGAAGCACTACTTAATGAAGTGCTTGTTGTGCCAAACATC
408  189_HRV53a    AACCCGGTAGAGAAATACACAGAGGCTATCTTAAATGAAGTATTAGTAGTCCCAAACATT
409  190_HRV53b    AACCCGGTAGAGAAATACACAGAGGCTATCTTAAATGAAGTATTAGTAGTCCCAAACATT
410  191_HRV53     AACCCGGTAGAGAAATACACAGAGGCTATCTTAAATGAAGTATTAGTAGTCCCAAACATT
411  192_HRV46a    AATCCAGTGGAAAATATACAGAAGCTGTTCTTAATGAGGTCCTTGTAGTACCTAACATC
412  193_HRV46b    AATCCAGTGGAAAAATATACAGAAGCTGTTCTTAATGAGGTCCTTGTAGTACCTAACATC
413  194_HRV46     AATCCAGTGGAAAAATATACAGAAGCTGTTCTTAATGAGGTCCTTGTAGTACCTAACATC
414  195_HRV80a    AATCCAGTCGAAAATATACACAGAAGCAATCCTCAATGAAGTTCTTGTTGTACCAAACATC
415  196_HRV80b    AATCCAGTCGAAAATATACACAGAAGCAATCCTCAATGAAGTTCTTGTTGTACCAAACATC
416  197_HRV80     AATCCAGTCGAAAATATACACAGAAGCAATCCTCAATGAAGTTCTTGTTGTACCAAACATC
417  198_HRV51     AACCCTGTTGAAAAATATACAGAGGCTTTACTCAATGAAGTGTTGGTGGTTCCCAACATA
418  199_HRV51a    AACCCTGTTGAAAAATATACAGAGGCTTTACTCAATGAAGTGTTGGTGGTTCCCAACATA
419  200_HRV51b    AACCCTGTTGAAAAATATACAGAGGCTTTTACTCAATGAAGTGTTGGTGGTTCCCAACATA
420  201_HRV65a    AATCCAATTGAGAAGTATACAGAAGCTCTACTTAATGAAGTGTTGGTGGTCCCAAATATA
421  202_HRV65b    AATCCAATTGAGAAGTATACAGAAGCTCTACTTAATGAAGTGTTGGTGGTCCCAAATATA
422  203_HRV65     AATCCAATTGAGAAGTATACAGAAGCTCTACTTAATGAAGTGTTGGTGGTCCCAAATATA
423  204_HRV71a    AATCCTGTAGAAAAAATATACAGAAGCAATACTCAATGAGGTTCTAGTTGTGCCAAATATA
424  205_HRV71b    AATCCTGTAGAAAAAATATACAGAAGCAATACTCAATGAGGTTCTAGTTGTGCCAAATATA
425  206_HRV71     AATCCTGTAGAAAAAATATACAGAAGCAATACTCAATGAGGTTCTAGTTGTGCCAAATATA
426  207_HRV8      AACCCTATTGAACAATTCACAGAGGCAGTATTAAACGAGGTTCTTGTAGTTCCAAACACA
427  208_HRV95     AACCCTATTGAACAATTCACAGAGGCAGTATTAAACGAGGTTCTTGTAGTTCCAAACACA
428  209_HRV45     AACCCTGTTGAACAATTTGCAGAAGCAGTCCTTGATCAAGTATTAGTAGTTCCAAACACT
429  210_HRV45a    AACCCTGTTGAACAATTTGCAGAAGCAGTCCTTGATCAAGTATTAGTAGTTCCAAACACT
430  211_HRV45b    AACCCTGTTGAACAATTTGCAGAAGCAGTCCTTGATCAAGTATTAGTAGTTCCAAACACT
431  GROUP_1       AA-CC--T-GA----T------A-----T--T-----A-GT--T--T-GT-CC--A----
432
433  1_HRV1A1|d    AAAGAAAGTCATCACACTACATCAAACTCTGCCCCACTTTTAGATGCTGCAGAGACGGGA
434  2_HRV1A2|d    AAAGAAAGTCATCACACTACATCAAACTCTGCCCCACTTTTAGATGCTGCAGAGACGGGA
435  3_HRV1A|cD    AAAGAAAGTCATCACACTACATCAAACTCTGCCCCACTTTTAGATGCTGCAGAGACGGGA
436  4_HRV1B1|d    AAAGAAAGCCATCACACTACATCAAATTCTGCTCCACTCTTGGATGCTGCAGAGACAGGA
437  5_HRV1B2|d    AAAGAAAGCCATCACACTACATCAAATTCTGCTCCACTCTTGGATGCTGCAGAGACAGGA
438  6_HRV1B       AAAGAAAGCCATCACACTACATCAAATTCTGCTCCACTCTTGGATGCTGCAGAGACAGGA
439  7_HRV40a|d    AGAGAGAGCCATCCAACTACATCAAATTCGGCCCCTGCCTTGGATGCAGCAGAGACTGGA
440  8_HRV40b|d    AGAGAGAGCCATCCAACTACATCAAATTCGGCCCCTGCCTTGGATGCAGCAGAGACTGGA
441  9_HRV40       AGAGAGAGCCATCCAACTACATCAAATTCGGCCCCTGCCTTGGATGCAGCAGAGACTGGA
442  10_HRV85      AAAGAGAGTCACCCAACTATATCAAATTCAGCTCCTGCTTTGGATGCAGCAGAGACTGGC
443  11_HRV85a|    AAAGAGAGTCACCCAACTATATCAAATTCAGCTCCTGCTTTGGATGCAGCAGAGACTGGC
444  12_HRV85b|    AAAGAGAGTCACCCAACTATATCAAATTCAGCTCCTGCTTTGGATGCAGCAGAGACTGGC
445  13_HRV56a|    AGGGAGAGCCATCCATCCACATCAAATTCTGCCCCTGCATTAGATGCTGCTGAAACTGGC
446  14_HRV56b|    AGGGAGAGCCATCCATCCACATCAAATCTGCCCCTGCATTAGATGCTGCTGAAACTGGC
447  15_HRV56      AGGGAGAGCCATCCATCCACATCAAATCTGCCCCTGCATTAGATGCTGCTGAAACTGGC
448  16_HRV54      AGAGAGAGTCATCCAGCTACATCAAATTCAGCCCCTGCGCTAGATGCGGCAGAAACTGGA
449  17_HRV98      AAAGAAAGTCATCCAGCTACATCTAATTCGGCCCCTACACTAGATGCAGCAGAAACTGGG
450  18_HRV59a|    CAGGAAAGCCACCCAACCACCTCAAATGCTGCTCCAGCATTAGATGCAGCAGAGACTGGA
```

FIG. D9 CONT'D

```
05.trace                                                                  9/20/2007 5:04 PM 451  19_HRV59b|   CAGGAAAGCCACCCAACCACCTCAAATGCTGCTCCAGCATTAGATGCAGCAGAGACTGGA
452  20_HRV59     CAGGAAAGCCACCCAACCACCTCAAATGCTGCTCCAGCATTAGATGCAGCAGAGACTGGA
453  21_HRV63     CAAGAAAGCCATCCAACCACATCAAACGCTGCTCCTGTACTTGATGCTGCGGAAACAGGA
454  22_HRV63b|   CAAGAAAGCCATCCAACCACATCAAACGCTGCTCCTGTACTTGATGCTGCGGAAACAGGA
455  23_HRV63a|   CAAGAAAGCCATCCAACCACATCAAACGCTGCTCCTGTACTTGATGCTGCGGAAACAGGA
456  24_HRV39     AGAGAGAGCCATCCAACTACATCTAATGCAGCTACAGCTTTGGATGCTGCTGAAACTGGA
457  25_HRV39a|   AGAGAGAGCCATCCAACTACATCTAATGCAGCTACAGCTTTGGATGCTGCTGAAACTGGA
458  26_HRV39b|   AGAGAGAGCCATCCAACTACATCTAATGCAGCTCCAGCTTTGGATGCTGCTGAAACTGGA
459  27_HRV10a|   AGAGAAAGTCATCCAAGCACCTCTAACTCTGCCCCAATTCTCGATGCAGCTGAGACTGGT
460  28_HRV10b|   AGAGAAAGTCATCCAAGCACCTCTAACTCTGCCCCAATTCTCGATGCAGCTGAGACTGGT
461  29_HRV10     AGAGAAAGTCATCCAAGCACCTCTAACTCTGCCCCAATTCTCGATGCAGCTGAGACTGGT
462  30_HRV100a   AGAGAGAGCCATCCAAGCACCTCAAACTCTGCTCCAATCCTTGATGCTGCTGAAACTGGC
463  31_HRV100b   AGAGAGAGCCATCCAAGCACCTCAAACTCTGCTCCAATCCTTGATGCTGCTGAAACTGGC
464  32_HRV100    AGAGAGAGCCATCCAAGCACCTCAAACTCTGCTCCAATCCTTGATGCTGCTGAAACTGGC
465  33_HRV66     AAGGAAAGCCATCCAAGCACATCAAATGCTGCCCCAATACTAGATGCAGCTGAAACAGGT
466  34_HRV66b|   AAGGAAAGCCATCCAAGCACATCAAATGCTGCCCCAATACTAGATGCAGCTGAAACAGGT
467  35_HRV66a|   AAGGAAAGCCATCCAAGCACATCAAATGCTGCCCCAATACTAGATGCAGCTGAAACAGGT
468  36_HRV77a|   AAGGAGAGTCATCCAAGCACTTCTAACTCTGCTCCTATACTAGATGCAGCTGAAACAGGC
469  37_HRV77b|   AAGGAGAGTCATCCAAGCACTTCTAACTCTGCTCCTATACTAGATGCAGCTGAAACAGGC
470  38_HRV77     AAGGAGAGTCATCCAAGCACTTCTAACTCTGCTCCTATACTAGATGCAGCTGAAACAGGC
471  39_HRV62a    AAAGAAAGTCACCCTAGTACGTCAAACTCTGCCCCAATTCTAGATGCTGCTGAAACCGGA
472  40_HRV62b    AAAGAAAGTCACCCTAGTACGTCAAATTCTGCCCCAATTCTAGATGCTGCTGAAACCGGA
473  41_HRV25     AAAGAAAGTCACCCAAGCACATCAAACTCTGCCCCAATTCTAGATGCTGCTGAAACTGGA
474  42_HRV29a    AGGGAGAGCCACCCAAGCACGTCCAACTCTGCACCAATCTTGGATGCTGCTGAGACTGGA
475  43_HRV29b    AGGGAGAGCCACCCAAGCACGTCCAACTCTGCACCAATCTTGGATGCTGCTGAGACTGGA
476  44_HRV44a    AGAGAGAGCCACCCAAGCACATCTAACTCTGCTCCAATTTTGGATGCTGCTGAAACTGGA
477  45_HRV44b    AGAGAGAGCCACCCAAGCATATCTAACTCTGCTCCAATTTTGGATGCTGCTGAAACTGGA
478  46_HRV31     AAAGAAAGCCATCCAAGCACATCTAATTCTGCCCCAATCCTGGACGCTGCTGAAACTGGA
479  47_HRV31a|   AAAGAAAGCCATCCAAGCACATCTAATTCTGCCCCAATCCTGGACGCTGCTGAAACTGGA
480  48_HRV31b|   AAAGAAAGCCATCCAAGCACATCTAATTCTGCCCCAATCCTGGACGCTGCTGAAACTGGA
481  49_HRV47     AAAGAAAGTCATCCAAGTACATCCAACTCTGCCCCGATTTTAGATGCTGCTGAAACTGGA
482  50_HRV47a|   AAAGAAAGTCATCCAAGTACATCCAACTCTGCCCCGATTTTAGATGCTGCTGAAACTGGA
483  51_HRV47b|   AAAGAAAGTCATCCAAGTACATCCAACTCTGCCCCGATTTTAGATGCTGCTGAAACTGGA
484  52_HRV11     AAGGAGAGCCAAGCTACCACATCAAACTCAGCACCTGCTCTAGATGCAGCTGAAACCGGA
485  53_HRV11b|   AAGGAGAGCCAAGCTACCACATCAAACTCAGCACCTGCTCTAGATGCAGCTGAAACCGGA
486  54_HRV11a|   AAGGAGAGCCAAGCTACCACATCAAACTCAGCACCTGCTCTAGATGCAGCTGAAACCGGA
487  55_HRV76     AAAGAGAGTCAGGCTACCACATCAAATGCAGCACCTGCTTTGGATGCAGCTGAGACTGGG
488  56_HRV76b|   AAAGAGAGTCAGGCTACCACATCAAATGCAGCACCTGCTTTGGATGCAGCTGAGACTGGG
489  57_HRV76a|   AAAGAGAGTCAGGCTACCACATCAAATGCAGCACCTGCTTTGGATGCAGCTGAGACTGGG
490  58_HRV33     AGAGAGAGTCAAGCAACCACATCAAATTCAGCACCTGCCTTAGATGCAGCTGAGACTGGA
491  59_HRV33b|   AGAGAGAGTCAAGCAACCACATCAAATTCAGCACCTGCCTTTAGATGCAGCTGAGACTGGA
492  60_HRV33a|   AGAGAGAGTCAAGCAACCACATCAAATTCAGCACCTGCCTTAGATGCAGCTGAGACTGGA
493  61_HRV24a|   AAGGAAAGTAAACCATCAACATCAAACTCAGCACCAGCTTTGGATGCAGCAGAAACTGGA
494  62_HRV24b|   AAGGAAAGTAAACCATCAACATCAAACTCAGCACCAGCTTTGGATGCAGCAGAAACTGGA
495  63_HRV24     AAGGAAAGTAAACCATCAACATCAAACTCAGCACCAGCTTTGGATGCAGCAGAAACTGGA
496  64_HRV90     AAGGAAAGTAAACCTTCAACTTCAAACTCAGCGCCAGCTTTAGATGCAGCAGAAACCGGA
497  65_HRV90a|   AAGGAAAGTAAACCTTCAACTTCAAACTCAGCGCCAGCTTTAGATGCAGCAGAAACCGGA
498  66_HRV90b|   AAGGAAAGTAAACCTTCAACTTCAAACTCAGCGCCAGCTTTAGATGCAGCAGAAACCGGA
499  67_HRV34     AAAGAAAGCCAAGCCACCACATCAAACTCTGCCCCCGCACTGGATGCAGCTGAGACTGGT
500  68_HRV34b|   AAAGAAAGCCAAGCCACCACATCAAACTCTGCCCCCGCACTGGATGCAGCTGAGACTGGT
501  69_HRV34a|   AAAGAAAGCCAAGCCACCACATCAAACTCTGCCCCCGCACTGGATGCAGCTGAGACTGGT
502  70_HRV50a|   AAGGAGAGTCAAGCCACTACATCAAACTCTGCCCCTGCTTTAGATGCAGCTGAAACTGGA
503  71_HRV50b|   AAGGAGAGTCAAGCCACTACATCAAACTCTGCCCCTGCTTTAGATGCAGCTGAAACTGGA
504  72_HRV50     AAGGAGAGTCAAGCCACTACATCAAACTCTGCCCCTGCTTTAGATGCAGCTGAAACTGGA
505  73_HRV18a|   AATGAAAGTCACGCAATTACATCAAATTCAGCCCCTGCTTTAGATGCCGCTGAAACTGGT
506  74_HRV18b|   AATGAAAGTCACGCAATTACATCAAATTCAGCCCCTGCTTTAGATGCCGCTGAAACTGGT
507  75_HRV18     AATGAAAGTCACGCAATTACATCAAATTCAGCCCCTGCTTTAGATGCCGCTGAAACTGGT
508  76_HRV55     AGGGAGAGTCAAGCAGCAACATCAAATTCAGCTCCAGTACTAGATGCAGCAGAAACTGGG
509  77_HRV55b|   AGGGAGAGTCAAGCAGCAACATCAAATTCAGCTCCAGTACTAGATGCAGCAGAAACTGGG
510  78_HRV55a|   AGGGAGAGTCAAGCAGCAACATCAAATTCAGCTCCAGTACTAGATGCAGCAGAAACTGGG
511  79_HRV57     AAACAAAGTCAAGCAACAACATCAAACTCAGCACCTGCATTGGATGCAGCTGAAACTGGA
512  80_HRV57a|   AAACAAAGTCAAGCAACAACATCAAACTCAGCACCTGCATTGGATGCAGCTGAAACTGGA
513  81_HRV57b|   AAACAAAGTCAAGCAACAACATCAAACTCAGCACCTGCATTGGATGCAGCTGAAACTGGA
514  82_HRV21     AGAGAGAGTCATGGAACAACATCAAACTCTGCTCCCGCACTTGATGCTGCAGAAACTGGA
515  83_HRVHan    AGAGAGAGTCATGGAACAACATCAAACTCTGCTCCCGCACTTGATGCTGCAGAAACTGGG
```

FIG. D9 CONT'D

05.trace                                                                 9/20/2007 5:04 PM

```
516  84_HRV43     GTAGAAAGTCATTCAACAACATCCAATGCAGCCCCTGCACTTGATGCAGCTGAAACTGGG
517  85_HRV43b|   GTAGAAAGTCATTCAACAACATCCAATGCAGCCCCTGCACTTGATGCAGCTGAAACTGGG
518  86_HRV43a|   GTAGAAAGTCATTCAACAACATCCAATGCAGCCCCTGCACTTGATGCAGCTGAAACTGGG
519  87_HRV75     ATGGAGAGCCATCCAACAACGTCTAATGCTGCTCCAGCTTTAGATGCAGCTGAAACTGGC
520  88_HRV75b|   ATGGAGAGCCATCCAACAACGTCTAATGCTGCTCCAGCTTTAGATGCAGCTGAAACTGGC
521  89_HRV75a|   ATGGAGAGCCATCCAACAACGTCTAATGCTGCTCCAGCTTTAGATGCAGCTGAAACTGGC
522  96_HRV9a|d   AAAGAGAGCAACCCTACAACCTCTAACTCAGCTCCAGCTCTAGATGCTGCTGAGACAGGC
523  97_HRV9b|d   AAAGAGAGCAACCCTACAACCTCTAACTCAGCTCCAGCTCTAGATGCTGCTGAGACAGGC
524  98_HRV9      AAAGAGAGCAACCCTACAACCTCTAACTCAGCTCCAGCTCTAGATGCTGCTGAGACAGGC
525  99_HRV32     AAAGAAAGCAATCCCACAACCTCTAATTCAGCCCCAGCCTTAGATGCTGCCGAAACAGGT
526  100_HRV32a   AAAGAAAGCAATCCCACAACCTCTAATTCAGCCCCAGCCTTAGATGCTGCCGAAACAGGT
527  101_HRV32b   AAAGAAAGCAATCCCACAACCTCTAATTCAGCCCCAGCCTTAGATGCTGCCGAAACAGGT
528  102_HRV67    AAGCAAAGTGAACCCACGACTTCCAATTCAGCCCCAGCTCTAGATGCTGCTGAGACAGGT
529  103_HRV67a   AAGCAAAGTGAACCCACGACTTCCAATTCAGCCCCAGCTCTAGATGCTGCTGAGACAGGT
530  104_HRV67b   AAGCAAAGTGAACCCACGACTTCCAATTCAGCCCCAGCTCTAGATGCTGCTGAGACAGGT
531  105_HRV15    AAGGAGAGTCACTCAAGCACATCCAACTCAGCACCAGCACTAGATGCAGCTGAGACCGGC
532  106_HRV15a   AAGGAGAGTCACTCAAGCACATCCAACTCAGCACCAGCACTAGATGCAGCTGAGACCGGC
533  107_HRV15b   AAGGAGAGTCACTCAAGCACATCCAACTCAGCACCAGCACTAGATGCAGCTGAGACCGGC
534  108_HRV74a   AGAGAAAGCCATTCAAGTACTTCAAACTCAGCACCAGCACTGGATGCAGCTGAAACTGGC
535  109_HRV74b   AGAGAAAGCCATTCAAGTACTTCAAACTCAGCACCAGCACTGGATGCAGCTGAAACTGGC
536  110_HRV74    AGAGAAAGCCATTCAAGTACTTCAAACTCAGCACCAGCACTGGATGCAGCTGAAACTGGC
537  111_HRV38a   AAGGAAAGCCACTCCAGCACATCAAATTCAGCACCAGCATTAGATGCTGCTGAGACTGGA
538  112_HRV38b   AAGGAAAGCCACTCCAGCACATCAAATTCAGCACCAGCATTAGATGCTGCTGAGACTGGA
539  113_HRV38    AAGGAAAGCCACTCCAGCACATCAAATTCAGCACCAGCATTAGATGCTGCTGAGACTGGA
540  114_HRV60    AGGGAGAGCCAACCCACTACTTCTAATTCTGCTCCAGCATTGGATGCTGCTGAGACTGGT
541  115_HRV60a   AGGGAGAGCCAACCCACTACTTCTAATTCTGCTCCAGCATTGGATGCTGCTGAGACTGGT
542  116_HRV60b   AGGGAGAGCCAACCCACTACTTCTAATTCTGCTCCAGCATTGGATGCTGCTGAGACTGGT
543  117_HRV64a   AATGAGAGCCATCCCAGCACTTCCAATGCAGCGCCAGCTTTAGATGCAGCTGAGACCGGA
544  118_HRV64b   AATGAGAGCCATCCCAGCACTTCCAATGCAGCGCCAGCTTTAGATGCAGCTGAGACCGGA
545  119_HRV64    AATGAGAGCCATCCCAGCACTTCCAATGCAGCGCCAGCTTTAGATGCAGCTGAGACCGGA
546  120_HRV94a   AATGAGAGTCACCCTAGCACATCCAATGCAGCGCCAGCCTTAGATGCTGCCGAAACTGGA
547  121_HRV94b   AATGAGAGTCACCCTAGCACATCCAATGCAGCGCCAGCCTTAGATGCTGCCGAAACTGGA
548  122_HRV94    AATGAGAGTCACCCTAGCACATCCAATGCAGCGCCAGCCTTAGATGCTGCCGAAACTGGA
549  123_HRV22    AATGAAAGTCACCCCAGTACATCAAATGCTGCACCAGCACTAGATGCTGCTGAAACTGGA
550  124_HRV22a   AATGAAAGTCACCCCAGTACATCAAATGCTGCACCAGCACTAGATGCTGCTGAAACTGGA
551  125_HRV22b   AATGAAAGTCACCCCAGTACATCAAATGCTGCACCAGCACTAGATGCTGCTGAAACTGGA
552  126_HRV82    AATGAAAGTCATCCTAGTACTTCAAATTCAGCTCCTGCCTTGGACGCTGCAGAGACAGGA
553  127_HRV82b   AATGAAAGTCATCCTAGTACTTCAAATTCAGCTCCTGCCTTGGACGCTGCAGAGACAGGA
554  128_HRV82a   AATGAAAGTCATCCTAGTACTTCAAATTCAGCTCCTGCCTTGGACGCTGCAGAGACAGGA
555  129_HRV19    AATGAAAGTCATCCAAGTACATCAAATGCTGCTCCTGCCTTAGATGCAGCCGAGACAGGA
556  130_HRV19a   AATGAAAGTCATCCAAGTACATCAAATGCTGCTCCTGCCTTAGATGCAGCCGAGACAGGA
557  131_HRV19b   AATGAAAGTCATCCAAGTACATCAAATGCTGCTCCTGCCTTAGATGCAGCCGAGACAGGA
558  132_HRV13    AGTGAAAGTAGCTCAACTACATCTAATTCAGCTCCAGCCTTAGATGCTGCAGAAACTGGC
559  133_HRV13a   AGTGAAAGTAGCTCAACTACATCTAATTCAGCTCCAGCCTTAGATGCTGCAGAAACTGGC
560  134_HRV13b   AGTGAAAGTAGCTCAACTACATCTAATTCAGCTCCAGCCTTAGATGCTGCAGAAACTGGC
561  135_HRV41    AGTGAAAGCAGTCCAACTACTTCTAATTCAGCTCCAGCCCTAGATGCAGCAGAGACTGGT
562  136_HRV41a   AGTGAAAGCAGTCCAACTACTTCTAATTCAGCTCCAGCCCTAGATGCAGCAGAGACTGGT
563  137_HRV41b   AGTGAAAGCAGTCCAACTACTTCTAATTCAGCTCCAGCCCTAGATGCAGCAGAGACTGGT
564  138_HRV73    AATGAAAGTAATCCAACTACATCCAACTCAGCACCTGCACTGGACGCTGCAGAAACTGGC
565  139_HRV73b   AATGAAAGTAATCCAACTACATCCAACTCAGCACCTGCACTGGACGCTGCAGAAACTGGC
566  140_HRV73a   AATGAAAGTAATCCAACTACATCCAACTCAGCACCTGCACTGGACGCTGCAGAAACTGGC
567  141_HRV61    AATCAGAGCAACCCTACAACATCCAACTCAGCACCAGTCTTAGACGCTGCTGAAACAGGT
568  142_HRV61a   AATCAGAGCAACCCTACAACATCCAACTCAGCACCAGTCTTAGACGCTGCTGAAACAGGT
569  143_HRV61b   AATCAGAGCAACCCTACAACATCCAACTCAGCACCAGTCTTAGACGCTGCTGAAACAGGT
570  144_HRV96    AATGAAAGTTACCCAACAACTTCCAATTCAGCCCCAGTGCTAGATGCCGCTGAAACAGGT
571  145_HRV96b   AATGAAAGTTACCCAACAACTTCCAATTCAGCCCCAGTGCTAGATGCCGCTGAAACAGGT
572  146_HRV96a   AATGAAAGTTACCCAACAACTTCCAATTCAGCCCCAGTGCTAGATGCCGCTGAAACAGGT
573  90_HRV16a|   AATGAGAGCCACCCTACCACATCAAATGCGGCCCCAGTTTTGGATGCTGCTGAAACAGGA
574  91_HRV16b|   AATGAGAGCCACCCTACCACATCAAATGCGGCCCCAGTTTTGGATGCTGCTGAAACAGGA
575  92_1AYM_A    AATGAGAGCCACCCTACCACATCAAATGCGGCCCCAGTTTTGGATGCTGCTGAAACAGGA
576  93_HRV81a|   ATGAAAGCCACCCTACAACATCTAATTCAGCTCCTGTTTTAGATGCAGCTGAAACTGGA
577  94_HRV81b|   ATGAAAGCCACCCTACAACATCTAATTCAGCTCCTGTTTTAGATGCAGCTGAAACTGGA
578  95_HRV81     ATGAAAGCCACCCTACAACATCTAATTCAGCTCCTGTTTTAGATGCAGCTGAAACTGGA
579  147_HRV2     AATAGTAGTAACCCCACAACATCAAATTCTGCCCCAGCATTAGATGCTGCAGAAACAGGG
580  148_HRV2a|   AATAGTAGTAACCCCACAACATCAAATTCTGCCCCAGCATTAGATGCTGCAGAAACAGGG
```

FIG. D9 CONT'D 05.trace                                                                                                    9/20/2007 5:04 PM

```
581 149_HRV2b|    AATAGTAGTAACCCCACAACATCAAATTCTGCCCCAGCATTAGATGCTGCAGAAACAGGG
582 150_HRV49a    AATAGTAGTCACCCCACGACATCAAACTCTGCTCCAGCATTAGATGCTGCAGAAACAGGG
583 151_HRV49b    AATAGTAGTCACCCCACGACATCAAACTCTGCTCCAGCATTAGATGCTGCAGAAACAGGG
584 152_HRV49     AATAGTAGTCACCCCACGACATCAAACTCTGCTCCAGCATTAGATGCTGCAGAAACAGGG
585 153_HRV23a    AATAGTAGTCATCCCACAACATCAAACTCTGCTCCAGCATTAGACGCTGCGGAAACGGGT
586 154_HRV23b    AATAGTAGTCATCCCACAACATCAAACTCTGCTCCAGCATTAGACGCTGCGGAAACGGGT
587 155_HRV23     AATAGTAGTCATCCCACAACATCAAACTCTGCTCCAGCATTAGACGCTGCGGAAACGGGT
588 156_HRV30a    AACAGTAGTCACCCTACTACATCAAACTCTGCTCCGGCATTAGATGCTGCAGAAACAGGA
589 157_HRV30b    AACAGTAGTCACCCTACTACATCAAACTCTGCTCCGGCATTAGATGCTGCAGAAACAGGA
590 158_HRV30     AACAGTAGTCACCCTACTACATCAAACTCTGCTCCGGCATTAGATGCTGCAGAAACAGGA
591 159_HRV7      CAGCCAAGTACATCTGTTTCAAGTCACTCTGTACCAGCATTGGATGCTGCAGAGACTGGA
592 160_HRV7b|    CAGCCAAGTACATCTGTTTCAAGTCACTCTGTACCAGCATTGGATGCTGCAGAGACTGGA
593 161_HRV7a|    CAGCCAAGTACATCTGTTTCAAGTCACTCTGTACCAGCATTGGATGCTGCAGAGACTGGA
594 162_HRV88     CAACCTAGCACATCCGTTTCAAGTCACTCTGTGCCAGCTCTGGATGCTGCGGAAACAGGG
595 163_HRV88a    CAACCTAGCACATCCGTTTCAAGTCACTCTGTGCCAGCTCTGGATGCTGCGGAAACAGGG
596 164_HRV88b    CAACCTAGCACATCCGTTTCAAGTCACTCTGTGCCAGCTCTGGATGCTGCGGAAACAGGG
597 165_HRV36a    CAACCTAGTTCATCTGTGTCAAGTCATTCAGCTCCCGCCTTAGACGCTGCGGAAACTGGA
598 166_HRV36b    CAACCTAGTTCATCTGTGTCAAGTCATTCAGCTCCCGCCTTAGACGCTGCGGAAACTGGA
599 167_HRV36     CAACCTAGTTCATCTGTGTCAAGTCATTCAGCTCCCGCCTTAGACGCTGCGGAAACTGGA
600 168_HRV89a    CAACCTAGCACATCTGTGTCAAGTCATGCAGCGCCTGCATTGGATGCTGCGGAAACCGGA
601 169_HRV89b    CAACCTAGCACATCTGTGTCAAGTCATGCAGCGCCTGCATTGGATGCTGCGGAAACCGGA
602 170_HRV89     CAACCTAGCACATCTGTGTCAAGTCATGCAGCGCCTGCATTGGATGCTGCGGAAACCGGA
603 171_HRV58     CAACCTAGTACATCTGTATCAAGTCATTCTGTGCCTGCCTTGGATGCTGCAGAAACGGGA
604 172_HRV58a    CAACCTAGTACATCTGTATCAAGTCATTCTGTGCCTGCCTTGGATGCTGCAGAAACGGGA
605 173_HRV58b    CAACCTAGTACATCTGTATCAAGTCATTCTGTGCCTGCCTTGGATGCTGCAGAAACGGGA
606 174_HRV12a    AACAAAAGTAATGGGCAGTTATCAAACGCAGCACCAGCGTTGGACGCTGCAGAAACTGGT
607 175_HRV12b    AACAAAAGTAATGGGCAGTTATCAAACGCAGCACCAGCGTTGGACGCTGCAGAAACTGGT
608 176_HRV12     AACAAAAGTAATGGGCAGTTATCAAACGCAGCACCAGCGTTGGACGCTGCAGAAACTGGT
609 177_HRV78a    AAAGAAAGTAAACCCCAGTCTAGCAACTCCGCTCCAGTTTTGGACGCTGCAGAAACAGGT
610 178_HRV78b    AAAGAAAGTAAACCCCAGTCTAGCAACTCCGCTCCAGTTTTGGACGCTGCAGAAACAGGT
611 179_HRV78     AAAGAAAGTAAACCCCAGTCTAGCAACTCCGCTCCAGTTTTGGACGCTGCAGAAACAGGT
612 180_HRV20     ACATCTAGTAACTCCCAAACATCAAATGCAGCACCAGCACTAGATGCTGCTGAGACAGGA
613 181_HRV20a    ACATCTAGTAACTCCCAAACATCAAATGCAGCACCAGCACTAGATGCTGCTGAGACAGGA
614 182_HRV20b    ACATCTAGTAACTCCCAAACATCAAATGCAGCACCAGCACTAGATGCTGCTGAGACAGGA
615 183_HRV68     CCAGCAAGTAATACCCAAACTTCAAATGCAGCCCCAGCCTTAGATGCTGCTGAGACTGGA
616 184_HRV68a    CCAGCAAGTAATACCCAAACTTCAAATGCAGCCCCAGCCTTAGATGCTGCTGAGACTGGA
617 185_HRV68b    CCAGCAAGTAATACCCAAACTTCAAATGCAGCCCCAGCCTTAGATGCTGCTGAGACTGGA
618 186_HRV28     AATCCTAGCAACGCACAAACTACAAATGCAGCTCCCGCTCTCGATGCCGCTGAGACGGGG
619 187_HRV28a    AATCCTAGCAACGCACAAACTACAAATGCAGCTCCCGCTCTCGATGCCGCTGAGACGGGG
620 188_HRV28b    AATCCTAGCAACGCACAAACTACAAATGCAGCTCCCGCTCTCGATGCCGCTGAGACGGGG
621 189_HRV53a    AATGCAAGCAATCCACAAACTTCAAATTCAGCACCAGCACTAGATGCTGCAGAAACGGGT
622 190_HRV53b    AATGCAAGCAATCCACAAACTTCAAATTCAGCACCAGCACTAGATGCTGCAGAAACGGGT
623 191_HRV53     AATGCAAGCAATCCACAAACTTCAAATTCAGCACCAGCACTAGATGCTGCAGAAACGGGT
624 192_HRV46a    AATGCCAGTAGTGGACATACATCTAATTCAGCTCCAGCACTTGATGCAGCAGAAACTGGA
625 193_HRV46b    AATGCCAGTAGTGGACATACATCTAATTCAGCTCCAGCACTTGATGCAGCAGAAACTGGA
626 194_HRV46     AATGCCAGTAGTGGACATACATCTAATTCAGCTCCAGCACTTGATGCAGCAGAAACTGGA
627 195_HRV80a    AGTGCTAGCAATGGACATACATCAAACTCAGCTCCAACACTTGATGCAGCAGAAACTGGT
628 196_HRV80b    AGTGCTAGCAATGGACATACATCAAACTCAGCTCCAACACTTGATGCAGCAGAAACTGGT
629 197_HRV80     AGTGCTAGCAATGGACATACATCAAACTCAGCTCCAACACTTGATGCAGCAGAAACTGGT
630 198_HRV51     CAACCTAGCAGTGGGCACACATCTAATGCTGCACCAGCTCTAGATGCTGCTGAGACAGGA
631 199_HRV51a    CAACCTAGCAGTGGGCACACATCTAATGCTGCACCAGCTCTAGATGCTGCTGAGACAGGA
632 200_HRV51b    CAACCTAGCAGTGGGCACACATCTAATGCTGCACCAGCTCTAGATGCTGCTGAGACAGGA
633 201_HRV65a    CAAGCTAGTAATGGGCATACATCTAATGCTGCACCAGCTTTAGATGCTGCTGAAACAGGA
634 202_HRV65b    CAAGCTAGTAATGGGCATACATCTAATGCTGCACCAGCTTTAGATGCTGCTGAAACAGGA
635 203_HRV65     CAAGCTAGTAATGGGCATACATCTAATGCTGCACCAGCTTTAGATGCTGCTGAAACAGGA
636 204_HRV71a    CAACCTAGTAATGGACATACCTCAAACTCAGCACCAGCCTTAGATGCAGCAGAAACTGGG
637 205_HRV71b    CAACCTAGTAATGGACATACCTCAAACTCAGCACCAGCCTTAGATGCAGCAGAAACTGGG
638 206_HRV71     CAACCTAGTAATGGACATACCTCAAACTCAGCACCAGCCTTAGATGCAGCAGAAACTGGG
639 207_HRV8      CAAGCTAGTAATGGATCTATAGCAAATTCAGCACCAGCATTAGATGCAGCAGAGACTGGA
640 208_HRV95     CAAGCCAGTAATGGATCTATAGCAAATTCAGCACCAGCATTAGATGCAGCAGAGACTGGA
641 209_HRV45     CGACCCAGCGATGGGTTGATTGCAAACTCAGCCCCAGCTTTGGATGCAGCTGAAACTGGA
642 210_HRV45a    CGACCCAGCGATGGGTTGATTGCAAACTCAGCCCCAGCTTTGGATGCAGCTGAAACTGGA
643 211_HRV45b    CGACCCAGCGATGGGTTGATTGCAAACTCAGCCCCAGCTTTGGATGCAGCTGAAACTGGA
644 GROUP_1       ------AG---------------A--C-G---C-----T-GA-GC-GC-GA-AC-GG-
645
```

FIG. D9 CONT'D

```
05.trace                                                                9/20/2007 5:04 PM 646   1_HRV1A1|d    CACACCAGTAATGTTCAACCAGAAGATGCTATAGAGACAAGGTATGTTATAACATCACAA
647   2_HRV1A2|d    CACACCAGTAATGTTCAACCAGAAGATGCTATAGAGACAAGGTATGTTATAACATCACAA
648   3_HRV1A|cD    CACACCAGTAATGTTCAACCAGAAGATGCTATAGAGACAAGGTATGTTATAACATCACAA
649   4_HRV1B1|d    CACACCAGTAATGTACAACCAGAGGATGCTATAGAAACAAGATATGTTATGACATCACAA
650   5_HRV1B2|d    CACACCAGTAATGTACAACCAGAGGATGCTATAGAAACAAGATATGTTATGACATCACAA
651   6_HRV1B       CACACCAGTAATGTACAACCAGAGGATGCTATAGAAACAAGATATGTTATGACATCACAA
652   7_HRV40a|d    CATACAAGCAACATACAACCTGAAGATACAATAGAAACAAGATTTGTGCAGACATCACAA
653   8_HRV40b|d    CATACAAGCAACATACAACCTGAAGATACAATAGAAACAAGATTTGTGCAGACATCACAA
654   9_HRV40       CATACAAGCAACATACAACCTGAAGATACAATAGAAACAAGATTTGTGCAGACATCACAA
655  10_HRV85       CATACAAGTAGTACACAGCCCGAGGATACAATAGAGACCAGGTTTGTTCAAACTTCACAG
656  11_HRV85a|     CATACAAGTAGTACACAGCCCGAGGATACAATAGAGACCAGGTTTGTTCAAACTTCACAG
657  12_HRV85b|     CATACAAGTAGTACACAGCCCGAGGATACAATAGAGACCAGGTTTGTTCAAACTTCACAG
658  13_HRV56a|     CATACTAGTGCAATCCAACCAGAAGACACTATAGAAACCAGATATGTACAGACATCACAA
659  14_HRV56b|     CATACTAGTGCAATCCAACCAGAAGACACTATAGAAACCAGATATGTACAGACATCACAA
660  15_HRV56       CATACTAGTGCAATCCAACCAGAAGACACTATAGAAACCAGATATGTACAGACATCACAA
661  16_HRV54       CACACTAGTGGAGTACAACCCGAGGACACCATAGAAACAAGATTTGTGCAGACATCACAA
662  17_HRV98       CACACTAGTGGAATACAACCTGAGGATACTATAGAAACAAGATATGTGCAGACATCACAA
663  18_HRV59a|     CATACAAGCAGTATACAACCTGAGGATACCATAGAAACAAGATATGTTCAGACATCACAA
664  19_HRV59b|     CATACAAGCAGTATACAACCTGAGGATACCATAGAAACAAGATATGTTCAGACATCACAA
665  20_HRV59       CATACAAGCAGTATACAACCTGAGGATACCATAGAAACAAGATATGTTCAGACATCACAA
666  21_HRV63       CACACAAGCAGTATACAACCTGAGGATACTGTAGAAACTAGATATGTGCAAACGTCTCAA
667  22_HRV63b|     CACACAAGCAGTATACAACCTGAGGATACTGTAGAAACTAGATATGTGCAAACGTCTCAA
668  23_HRV63a|     CACACAAGCAGTATACAACCTGAGGATACTGTAGAAACTAGATATGTGCAAACGTCTCAA
669  24_HRV39       CACACAAGTAGCACCCAGCCTGAAGACACAATTGAAACAAGATATGTGCAAACCTCACAT
670  25_HRV39a|     CACACAAGTAGCACCCAGCCTGAAGACACAATTGAAACAAGATATGTGCAAACCTCACAT
671  26_HRV39b|     CACACAAGTAGCATCCAACCTGAAGACACAATTGAAACAAGATATGTGCAAACCTCACAT
672  27_HRV10a|     CATACCAGTAGTGTACAACCAGAAGATACGGTTGAAACACGATATGTGCAAACATCCCAG
673  28_HRV10b|     CATACCAGTAGTGTACAACCAGAAGATACGGTTGAAACACGATATGTGCAAACATCCCAG
674  29_HRV10       CATACCAGTAGTGTACAACCAGAAGATACGGTTGAAACACGATATGTGCAAACATCCCAG
675  30_HRV100a     CACACTAGTAATGTGCAACCTGAAGATACAGTTGAAACTCGATATGTGCAGACATCACAG
676  31_HRV100b     CACACTAGTAATGTGCAACCTGAAGATACAGTTGAAACTCGATATGTGCAGACATCACAG
677  32_HRV100      CACACTAGTAATGTGCAACCTGAAGATACAGTTGAAACTCGATATGTGCAGACATCACAG
678  33_HRV66       CACACTAGTAAAGTACAACCAGAAGATACAGTTGAGACTCGTTACGTGCAAACATCACAG
679  34_HRV66b|     CACACTAGTAAAGTACAACCAGAAGATACAGTTGAGACTCGTTACGTGCAAACATCACAG
680  35_HRV66a|     CACACTAGTAAAGTACAACCAGAAGATACAGTTGAGACTCGTTACGTGCAAACATCACAG
681  36_HRV77a|     CATACTAGTAGTGTGCAACCAGAAGATACAGTTGAGACCCGCTATGTACAAACTTCCCAG
682  37_HRV77b|     CATACTAGTAGTGTGCAACCAGAAGATACAGTTGAGACCCGCTATGTACAAACTTCCCAG
683  38_HRV77       CATACTAGTAGTGTGCAACCAGAAGATACAGTTGAGACCCGCTATGTACAAACTTCCCAG
684  39_HRV62a      CACACTAGTAATGTACAACCAAGAGACACTATTGAAACCCGTCATGTTCAAACCACACAA
685  40_HRV62b      CACACTAGTAATGTACAACCAGAAGACACTATTGAAACCCGTTATGTTCAAACCACACAA
686  41_HRV25       CACACTAGCAATGTGCAACCAGAGGATACCATTGAAACTCGTTATGTTCAAACCACACAA
687  42_HRV29a      CATACTAGTAATGTACAACCAGAAGATACCATTGAGACTCGTTATGTACAAACCTCACAT
688  43_HRV29b      CATACTAGTAATGTACAACCAGAAGATACCATTGAGACTCGTTATGTACAAACCTCACAT
689  44_HRV44a      CATACTAGTAATGTACAACCAGAAGATACCATTGAGACTCGATATGTACAAACCTCACAA
690  45_HRV44b      CATACTAGTAATGTACAACCAGAAGATACCATTGAGACTCGATATGTACAAACCTCACAA
691  46_HRV31       CACACTAGTAATGTACAACCAGAAGATACAATTGAAACTCGCTACGTGCAAACATCACAA
692  47_HRV31a|     CACACTAGTAATGTACAACCAGAAGATACAATTGAAACTCGCTACGTGCAAACATCACAA
693  48_HRV31b|     CACACTAGTAATGTACAACCAGAAGATACAATTGAAACTCGCTACGTGCAAACATCACAA
694  49_HRV47       CACACTAGCAATGTACAGCCAGAAGATACAATTGAAACTCGATATGTACAAACAGCACAA
695  50_HRV47a|     CACACTAGCAATGTACAGCCAGAAGATACAATTGAAACTCGATATGTACAAACAGCACAA
696  51_HRV47b|     CACACTAGCAATGTACAGCCAGAAGATACAATTGAAACTCGATATGTACAAACAGCACAA
697  52_HRV11       CATACTAGCAAAGTGCAGCCAGAGGATATGATTGAGACTAGATATGTGCAGACTTCACAG
698  53_HRV11b|     CATACTAGCAAAGTGCAGCCAGAGGATATGATTGAGACTAGATATGTGCAGACTTCACAG
699  54_HRV11a|     CATACTAGCAAAGTGCAGCCAGAGGATATGATTGAGACTAGATATGTGCAGACTTCACAG
700  55_HRV76       CACACAAGCAGCGTTCAACCAGAGGACATGGTTGAGACTAGGTATGTGCAAACATCACAA
701  56_HRV76b|     CACACAAGCAGCGTTCAACCAGAGGACATGGTTGAGACTAGGTATGTGCAAACATCACAA
702  57_HRV76a|     CACACAAGCAGCGTTCAACCAGAGGACATGGTTGAGACTAGGTATGTGCAAACATCACAA
703  58_HRV33       CACACTAATAATGTACAACCAGAAGATATGATTGAAACAAGATATGTACAAACATCACAA
704  59_HRV33b|     CACACTAATAATGTACAACCAGAAGATATGATTGAAACAAGATATGTACAAACATCACAA
705  60_HRV33a|     CACACTAATAATGTACAACCAGAAGATATGATTGAAACAAGATATGTACAAACATCACAA
706  61_HRV24a|     CATACGAGTAGCGTGCAGCCAGAAGATATGGTTGAAACTAGATATGTCCAAACATCACAA
707  62_HRV24b|     CATACGAGTAGCGTGCAGCCAGAAGATATGGTTGAAACTAGATATGTCCAAACATCACAA
708  63_HRV24       CATACGAGTAGCGTGCAGCCAGAAGATATGGTTGAAACTAGATATGTCCAAACATCACAA
709  64_HRV90       CATACTAGTGATGTCCAGCCAGAAGATGTGGTAGAGACCAGATACGTGCAAACATCACAA
710  65_HRV90a|     CATACTAGTGATGTCCAGCCAGAAGATGTGGTAGAGACCAGATACGTGCAAACATCACAA
```

FIG. D9 CONT'D

05.trace                                                                   9/20/2007 5:04 PM

```
711  66_HRV90b|    CATACTAGTGATGTCCAGCCAGAAGATGTGGTAGAGACCAGATACGTGCAAACATCACAA
712  67_HRV34      CACACTAGCAGTGTACAACCTGAAGATATGATTGAGACCAGGTACGTACAAACATCACAA
713  68_HRV34b|    CACACTAGCAGTGTACAACCTGAAGATATGATTGAGACCAGGTACGTACAAACATCACAA
714  69_HRV34a|    CACACTAGCAGTGTACAACCTGAAGATATGATTGAGACCAGGTACGTACAAACATCACAA
715  70_HRV50a|    CACACAAGTAATGTGCAGCCTGAAGATATGCTTGAAACTAGATATGTGCAAACATCGCAT
716  71_HRV50b|    CACACAAGTAATGTGCAGCCTGAAGATATGCTTGAAACTAGATATGTGCAAACATCGCAT
717  72_HRV50      CACACAAGTAATGTGCAGCCTGAAGATATGCTTGAAACTAGATATGTGCAAACATCGCAT
718  73_HRV18a|    CACACCAGCAATGTGCAACCTGAAGATATGATTGAGACTAGGTATGTACAAACATCACAA
719  74_HRV18b|    CACACCAGCAATGTGCAACCTGAAGATATGATTGAGACTAGGTATGTACAAACATCACAA
720  75_HRV18      CACACCAGCAATGTGCAACCTGAAGATATGATTGAGACTAGGTATGTACAAACATCACAA
721  76_HRV55      CATACAAGCAATGTACAACCAGAAGATGTAATTGAGACAAGATATGTTCAGACATCACAA
722  77_HRV55b|    CATACAAGCAATGTACAACCAGAAGATGTAATTGAGACAAGATATGTTCAGACATCACAA
723  78_HRV55a|    CATACAAGCAATGTACAACCAGAAGATGTAATTGAGACAAGATATGTTCAGACATCACAA
724  79_HRV57      CACACTAGTAATGTACAACCGGAAGACATGATTGAAACTAGATATGTCCAGACATCACAA
725  80_HRV57a|    CACACTAGTAATGTACAACCGGAAGACATGATTGAAACTAGATATGTCCAGACATCACAA
726  81_HRV57b|    CACACTAGTAATGTACAACCGGAAGACATGATTGAAACTAGATATGTCCAGACATCACAA
727  82_HRV21      CACACTAGTAATGTACAGCCGGAGGATATGGTTGAAACAAGGTATGTTCAGACATCACAA
728  83_HRVHan     CACACTAGTAATGTACAACCAGAGGATATGGTTGAAACAAGGTATGTTCAGACATCACAA
729  84_HRV43      CATACTAGCCAGGTGCAACCTGAAGACATGGTAGAGACAAGGTCAGTACATAATTTCCAA
730  85_HRV43b|    CATACTAGCCAGGTGCAACCTGAAGACATGGTAGAGACAAGGTCAGTACATAATTTCCAA
731  86_HRV43a|    CATACTAGCCAGGTGCAACCTGAAGACATGGTAGAGACAAGGTCAGTACATAATTTCCAA
732  87_HRV75      CATACCAGCCATGTTCAACCAGAAGACATGTTAGAAACAAGGCAAGTACAAAATTTCCAA
733  88_HRV75b|    CATACCAGCCATGTTCAACCAGAAGACATGTTAGAAACAAGGCAAGTACAAAATTTCCAA
734  89_HRV75a|    CATACCAGCCATGTTCAACCAGAAGACATGTTAGAAACAAGGCAAGTACAAAATTTCCAA
735  96_HRV9a|d    CATACTAGCAATGTTCAACCTGAAGACATGATTGAAACACGTTATGTGCAGACATCACAA
736  97_HRV9b|d    CATACTAGCAATGTTCAACCTGAAGACATGATTGAAACACGTTATGTGCAGACATCACAA
737  98_HRV9       CATACTAGCAATGTTCAACCTGAAGACATGATTGAAACACGTTATGTGCAGACATCACAA
738  99_HRV32      CATACCAGTAATGTTCAACCTGAAGACATGATTGAAACACGTTATGTGCAAACAACACAC
739  100_HRV32a    CATACCAGTAATGTTCAACCTGAAGACATGATTGAAACACGTTATGTGCAAACAACACAC
740  101_HRV32b    CATACCAGTAATGTTCAACCTGAAGACATGATTGAAACACGTTATGTGCAAACAACACAC
741  102_HRV67     CACACTAGCAGTGTACAACCTGAAGATATGATCGAGACTCGTTATGTACAGGCATCAAAT
742  103_HRV67a    CACACTAGCAGTGTACAACCTGAAGATATGATCGAGACTCGTTATGTACAGGCATCAAAT
743  104_HRV67b    CACACTAGCAGTGTACAACCTGAAGATATGATCGAGACTCGTTATGTACAGGCATCAAAT
744  105_HRV15     CATACTAGCAGTGTTCAACCTGAGGATATGATTGAAACTCGTTACGTCCAAACATCACAG
745  106_HRV15a    CATACTAGCAGTGTTCAACCTGAGGATATGATTGAAACTCGTTACGTCCAAACATCACAG
746  107_HRV15b    CATACTAGCAGTGTTCAACCTGAGGATATGATTGAAACTCGTTACGTCCAAACATCACAG
747  108_HRV74a    CACACCAGTAATGTGCAACCAGAAGATATGGTTGAGACACGCTATGTGCAAACCTCACAG
748  109_HRV74b    CACACCAGTAATGTGCAACCAGAAGATATGGTTGAGACACGCTATGTGCAAACCTCACAG
749  110_HRV74     CACACCAGTAATGTGCAACCAGAAGATATGGTTGAGACACGCTATGTGCAAACCTCACAG
750  111_HRV38a    CACACCAGTAATGTGCAGCCTGAGGATATGATTGAAACTCGCTATGTACAGACATCACAA
751  112_HRV38b    CACACCAGTAATGTGCAGCCTGAGGATATGATTGAAACTCGCTATGTACAGACATCACAA
752  113_HRV38     CACACCAGTAATGTGCAGCCTGAGGATATGATTGAAACTCGCTATGTACAGACATCACAA
753  114_HRV60     CACACTAGTAATGTACAGCCTGAGGACGTGATTGAAACACGTTATGTGCAGATTACACAA
754  115_HRV60a    CACACTAGTAATGTACAGCCTGAGGACGTGATTGAAACACGTTATGTGCAGATTACACAA
755  116_HRV60b    CACACTAGTAATGTACAGCCTGAGGACGTGATTGAAACACGTTATGTGCAGATTACACAA
756  117_HRV64a    CACACCAGTAATGTACAGCCTGAAGATATGATTGAAACGCGCTATGTACAAAACACTCAA
757  118_HRV64b    CACACCAGTAATGTACAGCCTGAAGATATGATTGAAACGCGCTATGTACAAAACACTCAA
758  119_HRV64     CACACCAGTAATGTACAGCCTGAAGATATGATTGAAACGCGCTATGTACAAAACACTCAA
759  120_HRV94a    CACACAAGCAATGTACAACCTGAGGATATGATTGAAACACGCTATGTACAAAACACTCAA
760  121_HRV94b    CACACAAGCAATGTACAACCTGAGGATATGATTGAAACACGCTATGTACAAAACACTCAA
761  122_HRV94     CACACAAGCAATGTACAACCTGAGGATATGATTGAAACACGCTATGTACAAAACACTCAA
762  123_HRV22     CACACAAGCAATGTGCAGCCAGAAGACATAGAAACACGCTATGTGTTAAATTCACAA
763  124_HRV22a    CACACAAGCAATGTGCAGCCAGAAGACATGATAGAAACACGCTATGTGTTAAATTCACAA
764  125_HRV22b    CACACAAGCAATGTGCAGCCAGAAGACATGATAGAAACACGCTATGTGTTAAATTCACAA
765  126_HRV82     CATACAAGTACTGTTCAACCTGAGGACATGATTGAAACACGGTATGTTCAAACATCACAA
766  127_HRV82b    CATACAAGTACTGTTCAACCTGAGGACATGATTGAAACACGGTATGTTCAAACATCACAA
767  128_HRV82a    CATACAAGTACTGTTCAACCTGAGGACATGATTGAAACACGGTATGTTCAAACATCACAA
768  129_HRV19     CATACTAGCAATGTACAGCCTGAGGACATGATCGAAACACGCTATGTTCAAACGTCCCAG
769  130_HRV19a    CATACTAGCAATGTACAGCCTGAGGACATGATCGAAACACGCTATGTTCAAACGTCCCAG
770  131_HRV19b    CATACTAGCAATGTACAGCCTGAGGACATGATCGAAACACGCTATGTTCAAACGTCCCAG
771  132_HRV13     CACACAAGCAGTGTACAACCAGAAGACATGGTTGAAACACGTTATGTCCAAACTTCACAA
772  133_HRV13a    CACACAAGCAGTGTACAACCAGAAGACATGGTTGAAACACGTTATGTCCAAACTTCACAA
773  134_HRV13b    CACACAAGCAGTGTACAACCAGAAGACATGGTTGAAACACGTTATGTCCAAACTTCACAA
774  135_HRV41     CATACCAGTAATGTACAACCAGAGGACATGATTGAAACACGATATGTCCAAACCTCACAA
775  136_HRV41a    CATACCAGTAATGTACAACCAGAGGACATGATTGAAACACGATATGTCCAAACCTCACAA
```

FIG. D9 CONT'D

```
05.trace                                                                          9/20/2007 5:04 PM 776 137_HRV41b   CATACCAGTAATGTACAACCAGAGGACATGATTGAAACACGATATGTCCAAACCTCACAA
777 138_HRV73    CATACCAGTGGTGTACAACCAGAAGACATGATTGAGACCCGTTATGTCCAAACATCACAG
778 139_HRV73b   CATACCAGTGGTGTACAACCAGAAGACATGATTGAGACCCGTTATGTCCAAACATCACAG
779 140_HRV73a   CATACCAGTGGTGTACAACCAGAAGACATGATTGAGACCCGTTATGTCCAAACATCACAG
780 141_HRV61    CATACCAGCAATGTTCAACCGGAGGACACGATTGAAACACGATATGTTCAAACCTCACAG
781 142_HRV61a   CATACCAGCAATGTTCAACCGGAGGACACGATTGAAACACGATATGTTCAAACCTCACAG
782 143_HRV61b   CATACCAGCAATGTTCAACCGGAGGACACGATTGAAACACGATATGTTCAAACCTCACAG
783 144_HRV96    CATACTAGCAATGTCCAACCAGAGGATATGATTGAGACTCGATATGTTCAGACATCGCAG
784 145_HRV96b   CATACTAGCAATGTCCAACCAGAGGATATGATTGAGACTCGATATGTTCAGACATCGCAG
785 146_HRV96a   CATACTAGCAATGTCCAACCAGAGGATATGATTGAGACTCGATATGTTCAGACATCGCAG
786 90_HRV16a|   CATACCAATAAGATACAGCCAGAAGACACTATAGAAACCAGATATGTGCAATCTTCACAG
787 91_HRV16b|   CATACCAATAAGATACAGCCAGAAGACACTATAGAAACCAGATATGTGCAATCTTCACAG
788 92_1AYM_A    CATACCAATAAGATACAGCCAGAAGACACTATAGAAACCAGATATGTGCAATCTTCACAG
789 93_HRV81a|   CACACCAGTAATATACAACCTGAGGATACTATTGAGACCAGATATGTACAATCTTCACAG
790 94_HRV81b|   CACACCAGTAATATACAACCTGAGGATACTATTGAGACCAGATATGTACAATCTTCACAG
791 95_HRV81     CACACCAGTAATATACAACCTGAGGATACTATTGAGACCAGATATGTACAATCTTCACAG
792 147_HRV2     CACACTAGTAGTGTTCAACCAGAGGATGTCATTGAAACTAGGTATGTGCAGACATCACAA
793 148_HRV2a|   CACACTAGTAGTGTTCAACCAGAGGATGTCATTGAAACTAGGTATGTGCAGACATCACAA
794 149_HRV2b|   CACACTAGTAGTGTTCAACCAGAGGATGTCATTGAAACTAGGTATGTGCAGACATCACAA
795 150_HRV49a   CACACTAGCAATGTGCAACCTGAAGATGTCATTGAAACCAGATATGTACAGACATCACAA
796 151_HRV49b   CACACTAGCAATGTGCAACCTGAAGATGTCATTGAAACCAGATATGTACAGACATCACAA
797 152_HRV49    CACACTAGCAATGTGCAACCTGAAGATGTCATTGAAACCAGATATGTACAGACATCACAA
798 153_HRV23a   CACACTAGTAATGTTCAACCAGAAGATGTCATTGAAACCAGGTACGTTCAAACATCACAA
799 154_HRV23b   CACACTAGTAATGTTCAACCAGAAGATGTCATTGAAACCAGGTACGTTCAAACATCACAA
800 155_HRV23    CACACTAGTAATGTTCAACCAGAAGATGTCATTGAAACCAGGTACGTTCAAACATCACAA
801 156_HRV30a   CATACTAGTAATGTTCAACCTGAAGATGTCATTGAAACTAGATATGTTCAAACATCACAA
802 157_HRV30b   CATACTAGTAATGTTCAACCTGAAGATGTCATTGAAACTAGATATGTTCAAACATCACAA
803 158_HRV30    CATACTAGTAATGTTCAACCTGAAGATGTCATTGAAACTAGATATGTTCAAACATCACAA
804 159_HRV7     CATACTAGTTCTGTTCAACCTGAAGATATGATCGAGACAAGGTATGTCATAACAGACCAA
805 160_HRV7b|   CATACTAGTTCTGTTCAACCTGAAGATATGATCGAGACAAGGTATGTCATAACAGACCAA
806 161_HRV7a|   CATACTAGTTCTGTTCAACCTGAAGATATGATCGAGACAAGGTATGTCATAACAGACCAA
807 162_HRV88    CATACTAGTTCTGTTCAACCTGAAGATATGATAGAAACTAGATATGTTATAACAGATCAA
808 163_HRV88a   CATACTAGTTCTGTTCAACCTGAAGATATGATAGAAACTAGATATGTTATAACAGATCAA
809 164_HRV88b   CATACTAGTTCTGTTCAACCTGAAGATATGATAGAAACTAGATATGTTATAACAGATCAA
810 165_HRV36a   CATACCAGCTCTGTCCAACCAGAGGACATGATCGAGACCAGATATGTCATAACTGATCAA
811 166_HRV36b   CATACCAGCTCTGTCCAACCAGAGGACATGATCGAGACCAGATATGTCATAACTGATCAA
812 167_HRV36    CATACCAGCTCTGTCCAACCAGAGGACATGATCGAGACCAGATATGTCATAACTGATCAA
813 168_HRV89a   CACACCAGCTCTGTTCAACCTGAAGATATGATTGAAACTAGATATGTTATAACTGATCAA
814 169_HRV89b   CACACCAGCTCTGTTCAACCTGAAGATATGATTGAAACTAGATATGTTATAACTGATCAA
815 170_HRV89    CACACCAGCTCTGTTCAACCTGAAGATATGATTGAAACTAGATATGTTATAACTGATCAA
816 171_HRV58    CACACAAGTTCTGTTCAGCCTGAGGATATGATTGAAACTAGATATGTTATCACAGATCAA
817 172_HRV58a   CACACAAGTTCTGTTCAGCCTGAGGATATGATTGAAACTAGATATGTTATCACAGATCAA
818 173_HRV58b   CACACAAGTTCTGTTCAGCCTGAGGATATGATTGAAACTAGATATGTTATCACAGATCAA
819 174_HRV12a   CATACCAGCCAAACACAACCAGAAGATGTGATTGAAACCAGGTATGTGATTACAGACCAG
820 175_HRV12b   CATACCAGCCAAACACAACCAGAAGATGTGATTGAAACCAGGTATGTGATTACAGACCAG
821 176_HRV12    CATACCAGCCAAACACAACCAGAAGATGTGATTGAAACCAGGTATGTGATTACAGACCAG
822 177_HRV78a   CATACGAACCAAGTACAGCCTGAAGACACCATAGAAACTAGATATGTTATAACTGACCAA
823 178_HRV78b   CATACGAACCAAGTACAGCCTGAAGACACCATAGAAACTAGATATGTTATAACTGACCAA
824 179_HRV78    CATACGAACCAAGTACAGCCTGAAGACACCATAGAAACTAGATATGTTATAACTGACCAA
825 180_HRV20    CACACAAAACCAGGTCCAGCCAGAAGATATGGTCGAGACACGGTATGTAATTACTGATCAG
826 181_HRV20a   CACACAAAACCAGGTCCAGCCAGAAGATATGGTCGAGACACGGTATGTAATTACTGATCAG
827 182_HRV20b   CACACAAAACCAGGTCCAGCCAGAAGATATGGTCGAGACACGGTATGTAATTACTGATCAG
828 183_HRV68    CATACAAAACCAAGTCCAACCAGAAGATGTGGTTGAAACACGCTATGTCATAACAGACCAG
829 184_HRV68a   CATACAAAACCAAGTCCAACCAGAAGATGTGGTTGAAACACGCTATGTCATAACAGACCAG
830 185_HRV68b   CATACAAAACCAAGTCCAACCAGAAGATGTGGTTGAAACACGCTATGTCATAACAGACCAG
831 186_HRV28    CACACAAGCCAAACACAACCTGAAGACATGGTTGAGACTAGGTATGTAATCACAGATCAG
832 187_HRV28a   CACACAAGCCAAACACAACCTGAAGACATGGTTGAGACTAGGTATGTAATCACAGATCAG
833 188_HRV28b   CACACAAGCCAAACACAACCTGAAGACATGGTTGAGACTAGGTATGTAATCACAGATCAG
834 189_HRV53a   CATACAAGTCAGACACAACCTGAGGACATGCTGGAAACTAGATATGTCATCACAGACCAA
835 190_HRV53b   CATACAAGTCAGACACAACCTGAGGACATGCTGGAAACTAGATATGTCATCACAGACCAA
836 191_HRV53    CATACAAGTCAGACACAACCTGAGGACATGCTGGAAACTAGATATGTCATCACAGACCAA
837 192_HRV46a   CACACTAGCCAGATACAACCAGAAGACATGATAGAAACCAGATATGTTATCACAGACCAA
838 193_HRV46b   CACACTAGCCAGATACAACCAGAAGACATGATAGAAACCAGATATGTTATCACAGACCAA
839 194_HRV46    CACACTAGCCAGATACAACCAGAAGACATGATAGAAACCAGATATGTTATCACAGACCAA
840 195_HRV80a   CACACTAGCCAGGTGCAACCAGAAGACATGATAGAAACTAGATATGTTATTACTGATCAG
```

FIG. D9 CONT'D 05.trace                                                                 9/20/2007 5:04 PM

```
841  196_HRV80b    CACACTAGCCAGGTGCAACCAGAAGACATGATAGAAACTAGATATGTTATTACTGATCAG
842  197_HRV80     CACACTAGCCAGGTGCAACCAGAAGACATGATAGAAACTAGATATGTTATTACTGATCAG
843  198_HRV51     CATACTAGTCAAGTTCAACCAGAAGATATGGTAGAGACCAGGTATGTTGTCACAGACCAA
844  199_HRV51a    CATACTAGTCAAGTTCAACCAGAAGATATGGTAGAGACCAGGTATGTTGTCACAGACCAA
845  200_HRV51b    CATACTAGTCAAGTTCAACCAGAAGATATGGTAGAGACCAGGTATGTTGTCACAGACCAA
846  201_HRV65a    CACACTAGTCAAGTTCAACCAGAGGATGTGATAGAAACCAGATATGTCATCACAGATCAA
847  202_HRV65b    CACACTAGTCAAGTTCAACCAGAGGATGTGATAGAAACCAGATATGTCATCACAGATCAA
848  203_HRV65     CACACTAGTCAAGTTCAACCAGAGGATGTGATAGAAACCAGATATGTCATCACAGATCAA
849  204_HRV71a    CATACCAACCAAGTACAACCAGAAGATGTTATGGAAACCAGATATGTGATCACTGATCAA
850  205_HRV71b    CATACCAACCAAGTACAACCAGAAGATGTTATGGAAACCAGATATGTGATCACTGATCAA
851  206_HRV71     CATACCAACCAAGTACAACCAGAAGATGTTATGGAAACCAGATATGTGATCACTGATCAA
852  207_HRV8      CACACAAGTTCAGTGCAACCTGAAGATCTTATAGAGACTAGGTATGTAATTACAGATCAA
853  208_HRV95     CACACAAGTTCAGTGCAACCTGAAGATCTTATAGAGACTAGGTATGTAATTACAGATCAA
854  209_HRV45     CACACCAGTTCAGTGCAGCCTGAGGACCTTATAGAGACTAGATATGTGATTGCAGACCAA
855  210_HRV45a    CACACCAGTTCAGTGCAGCCTGAGGACCTTATAGAGACTAGATATGTGATTGCAGACCAA
856  211_HRV45b    CACACCAGTTCAGTGCAGCCTGAGGACCTTATAGAGACTAGATATGTGATTGCAGACCAA
857  GROUP_1       CA-AC-A--------CA-CC-GA-GA-----T-GA-AC--G----GT-----------A-
858
859   1_HRV1A1|d   ACAAGAGATGAGATGAGTATAGAAAGTTTCCTTGGTAGATCTGGTTGTGTCCACATCTCA
860   2_HRV1A2|d   ACAAGAGATGAGATGAGTATAGAAAGTTTCCTTGGTAGATCTGGTTGTGTCCACATCTCA
861   3_HRV1A|cD   ACAAGAGATGAGATGAGTATAGAAAGTTTCCTTGGTAGATCTGGTTGTGTCCACATCTCA
862   4_HRV1B1|d   ACAAGAGATGAGATGAGTATAGAAAGTTTCTTGGTAGATCTGGCTGTGTGCATATTTCA
863   5_HRV1B2|d   ACAAGAGATGAGATGAGTATAGAAAGTTTTCTTGGTAGATCTGGCTGTGTGCATATTTCA
864   6_HRV1B      ACAAGAGATGAGATGAGTATAGAAAGTTTCTTGGTAGATCTGGCTGTGTGCATATTTCA
865   7_HRV40a|d   ACTAGAGATGAAATGAGCATAGAGAGTTTCTTGGGAAGATCTGGGTGCATTCATATATCC
866   8_HRV40b|d   ACTAGAGATGAAATGAGCATAGAGAGTTTCTTGGGAAGATCTGGGTGCATTCATATATCC
867   9_HRV40      ACTAGAGATGAAATGAGCATAGAGAGTTTCTTGGGAAGATCTGGGTGCATTCATATATCC
868  10_HRV85      ACTAGGGATGAAATGAGTTTAGAAAGTTTCTTGGGAAGATCTGGATGTATCCATATATCT
869  11_HRV85a|    ACTAGGGATGAAATGAGTTTAGAAAGTTTCTTGGGAAGATCTGGATGTATCCATATATCT
870  12_HRV85b|    ACTAGGGATGAAATGAGTTTAGAAAGTTTCTTGGGAAGATCTGGATGTATCCATATATCT
871  13_HRV56a|    ACTAGGGATGAAATGAGTATAGAGAGTTTTCTAGGTAGATCAGGTTGTATACATATATCA
872  14_HRV56b|    ACTAGGGATGAAATGAGTATAGAGAGTTTTCTAGGTAGATCAGGTTGTATACATATATCA
873  15_HRV56      ACTAGGGATGAAATGAGTATAGAGAGTTTTCTAGGTAGATCAGGTTGTATACATATATCA
874  16_HRV54      ACTAGAGATGAAATGAGCATAGAAAGTTTTCTAGGCAGGGCTGGTTGCATACATGAATCC
875  17_HRV98      ACCAGAGATGAAATGAGTATAGAAAGTTTTCTAGGTAGGGCCGGTTGTATACATGAATCT
876  18_HRV59a|    ACTAGAGATGAGATGAGTGTAGAAAGTTTCTAGGTAGATCAGGATGTATATATATCA
877  19_HRV59b|    ACTAGAGATGAGATGAGTGTAGAAAGTTTCTTAGGTAGATCTGGGTGTATACATATTTCA
878  20_HRV59      ACTAGAGATGAGATGAGTGTAGAAAGTTTCTTAGGTAGATCTGGCTGTATACATATTTCA
879  21_HRV63      ACAAGGGATGAAATGAGTGTAGAGAGCTTTCTTGGTAGATCAGGATGCATACACATATCA
880  22_HRV63b|    ACAAGGGATGAAATGAGTGTAGAGAGCTTTCTTGGTAGATCAGGATGCATACACATATCA
881  23_HRV63a|    ACAAGGGATGAAATGAGTGTAGAGAGCTTTCTTGGTAGATCAGGATGCATACACATATCA
882  24_HRV39      ACTAGGGATGAAATGAGCGTTGAAAGTTTCTTAGGCAGATCTGGCTGTATTCACATTTCC
883  25_HRV39a|    ACTAGGGATGAAATGAGCGTTGAAAGTTTCTTAGGCAGATCTGGCTGTATTCACATTTCC
884  26_HRV39b|    ACTAGGGATGAAATGAGTGTTGAAAGTTTCTTAGGCAGATCTGGCTGTATTCACATTTCC
885  27_HRV10a|    ACGAGAGATGAAATGAGTATTGAAAGTTTTCTTGGCAGGTCAGGTTGTATACACACCTCA
886  28_HRV10b|    ACGAGAGATGAAATGAGTATTGAAAGTTTTCTTGGCAGGTCAGGTTGTATACACACCTCA
887  29_HRV10      ACGAGAGATGAAATGAGTATTGAAAGTTTTCTTGGCAGGTCAGGTTGTATACACACCTCA
888  30_HRV100a    ACCAGGGATGAAATGAGTATTGAGAGCTTTCTTGGAAGATCTGGTTGTATACACACCTCA
889  31_HRV100b    ACCAGGGATGAAATGAGTATTGAGAGCTTTCTTGGAAGATCTGGTTGTATACACACCTCA
890  32_HRV100     ACCAGGGATGAAATGAGTATTGAGAGCTTTCTTGGAAGATCTGGTTGTATACACACCTCA
891  33_HRV66      ACTAGAGATGAAATGAGCATAGAAAGTTTTCTAGGTAGGTCAGGATGTATCCATATATCA
892  34_HRV66b|    ACTAGAGATGAAATGAGCATAGAAAGTTTTCTAGGTAGGTCAGGATGTATCCATATATCA
893  35_HRV66a|    ACTAGAGATGAAATGAGCATAGAAAGTTTTCTAGGTAGGTCAGGATGTATCCATATATCA
894  36_HRV77a|    ACAAGGGATGAGATGAGTATTGAGAGCTTTCTGGGTAGGTCTGGTTGTATTCACATTTCA
895  37_HRV77b|    ACAAGGGATGAGATGAGTATTGAGAGCTTTCTGGGTAGGTCTGGTTGTATTCACATTTCA
896  38_HRV77      ACAAGGGATGAGATGAGTATTGAGAGCTTTCTGGGTAGGTCTGGTTGTATTCACATTTCA
897  39_HRV62a     ACTAGAGATGAAATGAGCTTTGAGAGCTTTCTGGAGGTCAGGGTGCGTACACACTTCA
898  40_HRV62b     ACTAGAGATGAAATGAGCATTGAGAGCTTTCTTGGTAGGTCAGGGTGCGTACACACTTCA
899  41_HRV25      ACTAGAGATGAAATGAGTATTGAAAGTTTTCTTGGTAGGTCAGGGTGTGTACATACTTCA
900  42_HRV29a     ACTAGAGATGAAATGAGCATTGAAAGTTTCTTGGGTAGATCAGGATGTATACATGTTTCA
901  43_HRV29b     ACTAGAGATGAAATGAGCATTGAAAGTTTCTTGGTAGATCAGGATGTATACATGTTTCA
902  44_HRV44a     ACTAGAGATGAAATGAGCATTGAAAGTTTCTTGGCAGATCAGGGTGTATACATGTTTCA
903  45_HRV44b     ACTAGAGATGAAATGAGCATTGAAAGTTTCTTGGCAGATCAGGGTGTATACATGTTTCA
904  46_HRV31      ACAAGAGATGAAATGAGCATTGAAAGTTTCCTTGGTAGGTCAGGATGTGTACATACTTCA
905  47_HRV31a|    ACAAGAGATGAAATGAGCATTGAAAGTTTCCTTGGTAGGTCAGGATGTGTACATACTTCA
```

FIG. D9 CONT'D 05.trace                                                                 9/20/2007 5:04 PM

```
906  48_HRV31b|   ACAAGAGATGAAATGAGCATTGAAAGTTTCCTTGGTAGGTCAGGATGTGTACATACTTCA
907  49_HRV47     ACAAGAGATGAAATGAGCATTGAGAGCTTCCTTGGCAGGTCAGGATGTGTGCATTCCTCA
908  50_HRV47a|   ACAAGAGATGAAATGAGCATTGAGAGCTTCCTTGGCAGGTCAGGATGTGTGCATTCCTCA
909  51_HRV47b|   ACAAGAGATGAAATGAGCATTGAGAGCTTCCTTGGCAGGTCAGGATGTGTGCATTCCTCA
910  52_HRV11     ACTCTTGATGAAATGAGCATTGAGAGCTTCCTAGGTAGATCTGGTTGTATTCACATGTCC
911  53_HRV11b|   ACTCTTGATGAAATGAGCATTGAGAGCTTCCTAGGTAGATCTGGTTGTATTCACATGTCC
912  54_HRV11a|   ACTCTTGATGAAATGAGCATTGAGAGCTTCCTAGGTAGATCTGGTTGTATTCACATGTCC
913  55_HRV76     ACTCTTGATGAGATGTGTATGGAGAGTTTCTTAGGGAGATCTGGTTGTATTCATATTTCA
914  56_HRV76b|   ACTCTTGATGAGATGTGTATGGAGAGTTTCTTAGGGAGATCTGGTTGTATTCATATTTCA
915  57_HRV76a|   ACTCTTGATGAGATGTGTATGGAGAGTTTCTTAGGGAGATCTGGTTGTATTCATATTTCA
916  58_HRV33     ACTCTTGATGAGATGAGTGTGGAAAGCTTCTTAGGAAGGTCTGGTTGCATTCACATGTCA
917  59_HRV33b|   ACTCTTGATGAGATGAGTGTGGAAAGCTTCTTAGGAAGGTCTGGTTGCATTCACATGTCA
918  60_HRV33a|   ACTCTTGATGAGATGAGTGTGGAAAGCTTCTTAGGAAGGTCTGGTTGCATTCACATGTCA
919  61_HRV24a|   ACATTACATGAGATGAGTGTTGAAAGTTTCTTGGGTAGATCAGGTTGCATACACATGTCC
920  62_HRV24b|   ACATTACATGAGATGAGTGTTGAAAGTTTCTTGGGTAGATCAGGTTGCATACACATGTCC
921  63_HRV24     ACATTACATGAGATGAGTGTTGAAAGTTTCTTGGGTAGATCAGGTTGCATACACATGTCC
922  64_HRV90     ACAAGAGATGAGTGAGTGTTGAAAGTTTTCTAGGGAGATCAGGTTGCATTCATATGTCA
923  65_HRV90a|   ACAAGAGATGAAATGAGTGTTGAAAGTTTTCTAGGGAGATCAGGTTGCATTCATATGTCA
924  66_HRV90b|   ACAAGAGATGAAATGAGTGTTGAAAGTTTTCTAGGGAGATCAGGTTGCATTCATATGTCA
925  67_HRV34     ACAAGAGATGAAATGAGCATTGAGAGTTTCCTGGGTAGGTCTGGCTGTATACACATGTCC
926  68_HRV34b|   ACAAGAGATGAAATGAGCATTGAGAGTTTCCTGGGTAGGTCTGGCTGTATACACATGTCC
927  69_HRV34a|   ACAAGAGATGAAATGAGCATTGAGAGTTTCCTGGGTAGGTCTGGCTGTATACACATGTCC
928  70_HRV50a|   ACAAGAGATGAAATGAGCATTGAAAGTTTCCTAGGTAGATCTGGTTGTATACATATATCT
929  71_HRV50b|   ACAAGAGATGAAATGAGCATTGAAAGTTTCCTAGGTAGATCTGGTTGTATACATATATCT
930  72_HRV50     ACAAGAGATGAAATGAGCATTGAAAGTTTCCTAGGTAGATCTGGTTGTATACATATATCT
931  73_HRV18a|   ACAAGAGATGAAATGAGTATAGAGTGTTTTCTAGGCAGATCAGGGTGTATACATATCTCC
932  74_HRV18b|   ACAAGAGATGAAATGAGTATAGAGTGTTTTCTAGGCAGATCAGGGTGTATACATATCTCC
933  75_HRV18     ACAAGAGATGAAATGAGTATAGAGTGTTTTCTAGGCAGATCAGGGTGTATACATATCTCC
934  76_HRV55     ACTCGTGATGAGATGAGCATTGAAAGTTTTCTAGGTAGATCAGGATGTGTACATATATCA
935  77_HRV55b|   ACTCGTGATGAGATGAGCATTGAAAGTTTTCTAGGTAGATCAGGATGTGTACATATATCA
936  78_HRV55a|   ACTCGTGATGAGATGAGCATTGAAAGTTTTCTAGGTAGATCAGGATGTGTACATATATCA
937  79_HRV57     ACACGTGATGAAATGAGTCTTGAGAGCTTCTTAGGAAGATCTGGCTGCATTCATATTTCA
938  80_HRV57a|   ACACGTGATGAAATGAGTCTTGAGAGCTTCTTAGGAAGATCTGGCTGCATTCATATTTCA
939  81_HRV57b|   ACACGTGATGAAATGAGTCTTGAGAGCTTCTTAGGAAGATCTGGCTGCATTCATATTTCA
940  82_HRV21     ACACGTGATGAAATGAGTATTGAGAGCTCTGGGCAGATCAGGGTGCATTCACATGTCA
941  83_HRVHan    ACACGTGATGAAATGAGTATTGAAAGTTTTCTAGGCAGATCAGGGTGTATCCACATGTCA
942  84_HRV43     ACCAGAGATGAAATGAGTATTGAAAGTTTCTTGGGCAGATCTGGTTGCATACATATTTCA
943  85_HRV43b|   ACCAGAGATGAAATGAGTATTGAAAGTTTCTTGGGCAGATCTGGTTGCATACATATTTCA
944  86_HRV43a|   ACCAGAGATGAAATGAGTATTGAAAGTTTCTTGGGCAGATCTGGTTGCATACATATTTCA
945  87_HRV75     ACTAGAGATGAGATGAGTATTGAGAGTTTCCTAGGCAGATCTGGATGTATTCATATTTCA
946  88_HRV75b|   ACTAGAGATGAGATGAGTATTGAGAGTTTCCTAGGCAGATCTGGATGTATTCATATTTCA
947  89_HRV75a|   ACTAGAGATGAGATGAGTATTGAGAGTTTCCTAGGCAGATCTGGATGTATTCATATTTCA
948  96_HRV9a|d   ACCAGAGATGAAATGAGTCTTGAAAGCTTCTTAGGGAGATCAGGTTGTATACACATATCT
949  97_HRV9b|d   ACCAGAGATGAAATGAGTCTTGAAAGCTTCTTAGGGAGATCAGGTTGTATACACATATCT
950  98_HRV9      ACCAGAGATGAAATGAGTCTTGAAAGCTTCTTAGGGAGATCAGGTTGTATACACATATCT
951  99_HRV32     ACTAGAGATGAGATGAGTCTTGAGAGCTTCTTAGGGAGGTCAGGATGTGTACATATATCC
952  100_HRV32a   ACTAGAGATGAGATGAGTCTTGAGAGCTTCTTAGGGAGGTCAGGATGTGTACATATATCC
953  101_HRV32b   ACTAGAGATGAGATGAGTCTTGAGAGCTTCTTAGGGAGGTCAGGATGTGTACATATATCC
954  102_HRV67    ACCAGAGATGAAATGAGTCTCGAGAGCTTTCTTGGGAAGGTCAGGCTGTGTATTCATATCA
955  103_HRV67a   ACCAGAGATGAAATGAGTCTCGAGAGCTTTCTTGGAAGGTCAGGCTGTATTCATATCA
956  104_HRV67b   ACCAGAGATGAAATGAGTCTCGAGAGCTTTCTTGGAAGGTCAGGCTGTATTCATATCA
957  105_HRV15    ACCAGAGATGAAATGAGTATTGAGAGCTTCCTTGGTAGATCAGGGTGTGTCCATATTTCT
958  106_HRV15a   ACCAGAGATGAAATGAGTATTGAGAGCTTCCTTGGTAGATCAGGGTGTGTCCATATTTCT
959  107_HRV15b   ACCAGAGATGAAATGAGTATTGAGAGCTTCCTTGGTAGATCAGGGTGTGTCCATATTTCT
960  108_HRV74a   ACAAGAGATGAGATGAGTGTAGAAAGTTTTCTTGGAAGATCAGGATGCATCCATATCTCA
961  109_HRV74b   ACAAGAGATGAGATGAGTGTAGAAAGTTTTCTTGGAAGATCAGGATGCATCCATATCTCA
962  110_HRV74    ACAAGAGATGAGATGAGTGTAGAAAGTTTTCTTGGAAGATCAGGATGCATCCATATCTCA
963  111_HRV38a   ACTAGAGATGAAATGAGTGTAGAAAGTTTTCTAGGAAGATCAGGTTGTGTACATATATCC
964  112_HRV38b   ACTAGAGATGAAATGAGTGTAGAAAGTTTTCTAGGAAGATCAGGTTGTGTACATATATCC
965  113_HRV38    ACTAGAGATGAAATGAGTGTAGAAAGTTTTCTAGGAAGATCAGGTTGTGTACATATATCC
966  114_HRV60    ACTAGAGATGAGATGAGTGTTGAGAGCTTCCTCGGCAGATCTGGATGTATTCATATTTCC
967  115_HRV60a   ACTAGAGATGAGATGAGTGTTGAGAGCTTCCTCGGCAGATCTGGATGTATTCATATTTCC
968  116_HRV60b   ACTAGAGATGAGATGAGTGTTGAGAGCTTCCTCGGCAGATCTGGATGTATTCATATTTCC
969  117_HRV64a   ACTAGAGATGAAATGAGCATTGAGAGTTTCTTGGGCAGGTCTGGTTGTATACACATATCA
970  118_HRV64b   ACTAGAGATGAAATGAGCATTGAGAGTTTCTTGGGCAGGTCTGGTTGTATACACATATCA
```

FIG. D9 CONT'D 05.trace                                                                    9/20/2007 5:04 PM

```
 971  119_HRV64    ACTAGAGATGAAATGAGCATTGAGAGTTTCTTGGGCAGGTCTGGTTGTATACACATATCA
 972  120_HRV94a   ACAAGGGATGAAATGAGCATTGAAAGCTTCTTGGGAAGATCTGGCTGTATACACATAGCA
 973  121_HRV94b   ACAAGGGATGAAATGAGCATTGAAAGCTTCTTGGGAAGATCTGGCTGTATACACATAGCA
 974  122_HRV94    ACAAGGGATGAAATGAGCATTGAAAGCTTCTTGGGAAGATCTGGCTGTATACACATAGCA
 975  123_HRV22    ACTAGAGATGAAATGAGTATTGAGAGCTTCCTGGGAAGATCTGGTTGCATACATATATCA
 976  124_HRV22a   ACTAGAGATGAAATGAGTATTGAGAGCTTCCTGGGAAGATCTGGTTGCATACATATATCA
 977  125_HRV22b   ACTAGAGATGAAATGAGTATTGAGAGCTTCCTGGGAAGATCTGGTTGCATACATATATCA
 978  126_HRV82    ACTAGAGATGAGATGAGCCTTGAGAGTTTCCTAGGGAGATCTGGCTGCATACACATATCA
 979  127_HRV82b   ACTAGAGATGAGATGAGCCTTGAGAGTTTCCTAGGGAGATCTGGCTGCATACACATATCA
 980  128_HRV82a   ACTAGAGATGAGATGAGCCTTGAGAGTTTCCTAGGGAGATCTGGCTGCATACACATATCA
 981  129_HRV19    ACTAGGGATGAAATGAGCATAGAAAGTTTCTTGGCAGATCCGGTTGTGTACATGTTTCA
 982  130_HRV19a   ACTAGGGATGAAATGAGCATAGAAAGTTTCTTGGCAGATCCGGTTGTGTACATGTTTCA
 983  131_HRV19b   ACTAGGGATGAAATGAGCATAGAAAGTTTCTTGGCAGATCCGGTTGTGTACATGTTTCA
 984  132_HRV13    ACTAGGGATGAAATGAGTGTTGAGAGCTTTTAGGCAGATCTGGTTGTATACACATGTCT
 985  133_HRV13a   ACTAGGGATGAAATGAGTGTTGAGAGCTTTTAGGCAGATCTGGTTGTATACACATGTCT
 986  134_HRV13b   ACTAGGGATGAAATGAGTGTTGAGAGCTTTTAGGCAGATCTGGTTGTATACACATGTCT
 987  135_HRV41    ACTAGAGATGAAATGAGCATAGAAAGCTTTTTAGGTAGATCAGGCTGTGTACATAAGTCC
 988  136_HRV41a   ACTAGAGATGAAATGAGCATAGAAAGCTTTTTAGGTAGATCAGGCTGTGTACATAAGTCC
 989  137_HRV41b   ACTAGAGATGAAATGAGCATAGAAAGCTTTTTAGGTAGATCAGGCTGTGTACATAAGTCC
 990  138_HRV73    ACTAGAGATGAAATGAGCATTGAAAGCTTCCTTGGCAGGTCAGGTTGTATACACATGTCA
 991  139_HRV73b   ACTAGAGATGAAATGAGCATTGAAAGCTTCCTTGGCAGGTCAGGTTGTATACACATGTCA
 992  140_HRV73a   ACTAGAGATGAAATGAGCATTGAAAGCTTCCTTGGCAGGTCAGGTTGTATACACATGTCA
 993  141_HRV61    ACAAGAGATGAAATGAGTGTAGAAAGTTTCTTGGGTAGATCAGGGTGCATACATATGTCA
 994  142_HRV61a   ACAAGAGATGAAATGAGTGTAGAAAGTTTCTTGGGTAGATCAGGGTGCATACATATGTCA
 995  143_HRV61b   ACAAGAGATGAAATGAGTGTAGAAAGTTTCTTGGGTAGATCAGGGTGCATACATATGTCA
 996  144_HRV96    ACGAGAGATGAAATGAGCATTGAGAGCTTTTGGGTAGATCAGGGTGTATACACATGTCA
 997  145_HRV96b   ACGAGAGATGAAATGAGCATTGAGAGCTTTTGGGTAGATCAGGGTGTATACACATGTCA
 998  146_HRV96a   ACGAGAGATGAAATGAGCATTGAGAGCTTTTGGGTAGATCAGGGTGTATACACATGTCA
 999   90_HRV16a|  ACATTGGATGAAATGAGTGTGGAAAGCTTCCTAGGCAGATCGGGGTGCATCCATGAATCA
1000   91_HRV16b|  ACATTGGATGAAATGAGTGTGGAAAGCTTCCTAGGCAGATCGGGGTGCATCCATGAATCA
1001   92_1AYM_A   ACATTGGATGAAATGAGTGTGGAAAGCTTCCTAGGCAGATCGGGGTGCATCCATGAATCA
1002   93_HRV81a|  ACACTGGATGAAATGAGTGTAGAAAGTTTTTAGGCAGATCAGGTTGCATTCATGAATCC
1003   94_HRV81b|  ACACTGGATGAAATGAGTGTAGAAAGTTTTTAGGCAGATCAGGTTGCATTCATGAATCC
1004   95_HRV81    ACACTGGATGAAATGAGTGTAGAAAGTTTTTAGGCAGATCAGGTTGCATTCATGAATCC
1005  147_HRV2     ACAAGAGATGAAATGAGTTTAGAGAGTTTCTTGGCAGATCAGGATGCATACATGAATCT
1006  148_HRV2a|   ACAAGAGATGAAATGAGTTTAGAGAGTTTTCTTGGCAGATCAGGATGCATACATGAATCT
1007  149_HRV2b|   ACAAGAGATGAAATGAGTTTAGAGAGTTTCTTGGCAGATCAGGATGCATACATGAATCT
1008  150_HRV49a   ACAAGAGATGAAATGAGTTTAGAGAGTTTTCTTGGTAGGTCAGGGTGTATACATGAATCC
1009  151_HRV49b   ACAAGAGATGAAATGAGTTTAGAGAGTTTCTTGGTAGGTCAGGGTGTATACATGAATCC
1010  152_HRV49    ACAAGAGATGAAATGAGTTTAGAGAGTTTCTTGGTAGGTCAGGGTGTATACATGAATCC
1011  153_HRV23a   ACAAGAGATGAAATGAGTTTAGAAAGTTTCCTTGGTAGGTCAGGGTGTATACATGAATCT
1012  154_HRV23b   ACAAGAGATGAAATGAGTTTAGAAAGTTTCCTTGGTAGGTCAGGGTGTATACATGAATCT
1013  155_HRV23    ACAAGAGATGAAATGAGTTTAGAAAGTTTCCTTGGTAGGGTCAGGGTGTATACATGAATCT
1014  156_HRV30a   ACAAGGGATGAAATGAGTTTAGAAAGCTTTCTTGGTAGATCAGGATGTATACACGAGTCT
1015  157_HRV30b   ACAAGGGATGAAATGAGTTTAGAAAGCTTTCTTGGTAGATCAGGATGTATACACGAGTCT
1016  158_HRV30    ACAAGGGATGAAATGAGTTTAGAAAGCTTTCTTGGTAGATCAGGATGTATACACGAGTCT
1017  159_HRV7     ACAAGGGATGAAACTAGTATAGAGAGTTTCTTAGGTAGATCTGGATGTATTGCTAAAGTT
1018  160_HRV7b|   ACAAGGGATGAAACTAGTATAGAGAGTTTCTTAGGTAGATCTGGATGTATTGCTAAAGTT
1019  161_HRV7a|   ACAAGGGATGAAACTAGTATAGAGAGTTTCTTAGGTAGATCTGGATGTATTGCTAAAGTT
1020  162_HRV88    ACAAGGGATGAAACCAGCATTGAAAGCTTTCTGGGTAGGTCTGGATGCATAGCAAAAATT
1021  163_HRV88a   ACAAGGGATGAAACCAGCATTGAAAGCTTTCTGGGTAGGTCTGGATGCATAGCAAAAATT
1022  164_HRV88b   ACAAGGGATGAAACCAGCATTGAAAGCTTTCTGGGTAGGTCTGGATGCATAGCAAAAATT
1023  165_HRV36    ACAAGAGATGAGACAAGTATTGAAAGCTTCTTAGGTAGGTCAGGGTGCATAGCTATGATA
1024  166_HRV36b   ACAAGAGATGAGACAAGTATTGAAAGCTTCTTAGGTAGGTCAGGGTGCATAGCTATGATA
1025  167_HRV36    ACAAGAGATGAGACAAGTATTGAAAGCTTCTTAGGTAGGTCAGGGTGCATAGCTATGATA
1026  168_HRV89a   ACAAGGGATGAAACAAGTATTGAGAGTTTCTTAGGTAGGTCAGGGTGTATCGCTATGATA
1027  169_HRV89b   ACAAGGGATGAAACAAGTATTGAGAGTTTCTTAGGTAGGTCAGGGTGTATCGCTATGATA
1028  170_HRV89    ACAAGGGATGAAACAAGTATTGAGAGTTTCTTAGGTAGGTCAGGGTGTATCGCTATGATA
1029  171_HRV58    ACAAGAGATGAAACTAGCATTGAAAGCTTTTAGGTAGATCTGGTTGCATTGCTATCATA
1030  172_HRV58a   ACAAGAGATGAAACTAGCATTGAAAGCTTTTTAGGTAGATCTGGTTGCATTGCTATCATA
1031  173_HRV58b   ACAAGAGATGAAACTAGCATTGAAAGCTTTTTAGGTAGATCTGGTTGCATTGCTATCATA
1032  174_HRV12a   ACTAGAGATGAGATGTCAATTGAATCTTTCCTTGGTCGGTCCGGATGCATTTCAATTATC
1033  175_HRV12b   ACTAGAGATGAGATGTCAATTGAATCTTTCCTTGGTCGGTCCGGATGCATTTCAATTATC
1034  176_HRV12    ACTAGAGATGAGATGTCAATTGAATCTTTCCTTGGTCGGTCCGGATGCATTTCAATTATC
1035  177_HRV78a   ACAAGAGATGAAATGAGCATTGAAAGTTTCCTCGGAAGATCAGGTTGTGCAACAATTATG
```

FIG. D9 CONT'D 05.trace                                                                 9/20/2007 5:04 PM

```
1036 178_HRV78b    ACAAGAGATGAAATGAGCATTGAAAGTTTCCTCGGAAGATCAGGTTGTGCAACAATTATG
1037 179_HRV78     ACAAGAGATGAAATGAGCATTGAAAGTTTCCTCGGAAGATCAGGTTGTGCAACAATTATG
1038 180_HRV20     ACCCGTGATGAAATGAGTGTGGAAAGTTTTCTTGGTAGATCTGGTTGCATTGCTATCATA
1039 181_HRV20a    ACCCGTGATGAAATGAGTGTGGAAAGTTTTCTTGGTAGATCTGGTTGCATTGCTATCATA
1040 182_HRV20b    ACCCGTGATGAAATGAGTGTGGAAAGTTTTCTTGGTAGATCTGGTTGCATTGCTATCATA
1041 183_HRV68     ACAAGGGATGAAATGAGCATAGAGAGCTTCCTCGGTAGGTCAGGTTGCATTGCAATCATA
1042 184_HRV68a    ACAAGGGATGAAATGAGCATAGAGAGCTTCCTCGGTAGGTCAGGTTGCATTGCAATCATA
1043 185_HRV68b    ACAAGGGATGAAATGAGCATAGAGAGCTTCCTCGGTAGGTCAGGTTGCATTGCAATCATA
1044 186_HRV28     ACCCGTGATGAAATGAGTATAGAGAGTTTCTTAGGTAGGTCTAGTTGCATTGCAATAATC
1045 187_HRV28a    ACCCGTGATGAAATGAGTATAGAGAGTTTCTTAGGTAGGTCTAGTTGCATTGCAATAATC
1046 188_HRV28b    ACCCGTGATGAAATGAGTATAGAGAGTTTCTTAGGTAGGTCTAGTTGCATTGCAATAATC
1047 189_HRV53a    ACCCGGGATGAAATGAGCATTGAAAGTTTCTTAGGCAGATCAAGTTGCATTGCTGAGATC
1048 190_HRV53b    ACCCGGGATGAAATGAGCATTGAAAGTTTCTTAGGCAGATCAAGTTGCATTGCTGAGATC
1049 191_HRV53     ACCCGGGATGAAATGAGCATTGAAAGTTTCTTAGGCAGATCAAGTTGCATTGCTGAGATC
1050 192_HRV46a    ACAAAAGATGAAATGAGTATAGAAAGTTTTCTAGGAAGGTCAGGCTGCATTGCCATTATT
1051 193_HRV46b    ACAAAAGAAATGAGTATAGAAAGTTTTCTTAGGAAGGTCAGGCTGCATTGCCATTATT
1052 194_HRV46     ACAAAAGATGAAATGAGTATAGAAAGTTTTCTAGGAAGGTCAGGCTGCATTGCCATTATT
1053 195_HRV80a    ACAAAGGATGAGATGAGCATTGAAAGTTTCTTAGGAAGATCTGGTTGTGTTGCTATCATT
1054 196_HRV80b    ACAAAGGATGAGATGAGCATTGAAAGTTTCTTAGGAAGATCTGGTTGTGTTGCTATCATT
1055 197_HRV80     ACAAAGGATGAGATGAGCATTGAAAGTTTCTTAGGAAGATCTGGTTGTGTTGCTATCATT
1056 198_HRV51     ACTAGAGATGAAATGAGTATAGAGAGTTTCTTGGGTAGATCTGCTTGCGTAGCAATCATC
1057 199_HRV51a    ACTAGAGATGAAATGAGTATAGAGAGTTTCTTGGGTAGATCTGCTTGCGTAGCAATCATC
1058 200_HRV51b    ACTAGAGATGAAATGAGTATAGAGAGTTTCTTGGGTAGATCTGCTTGCGTAGCAATCATC
1059 201_HRV65a    ACCAGAGATGAGATGAGCGTAGAGAGTTTCCTGGGCAGATCTGCCTGCATAGCAGTCATT
1060 202_HRV65b    ACCAGAGATGAGATGAGCGTAGAGAGTTTCCTGGGCAGATCTGCCTGCATAGCAGTCATT
1061 203_HRV65     ACCAGAGATGAGATGAGCGTAGAGAGTTTCCTGGGCAGATCTGCCTGCATAGCAGTCATT
1062 204_HRV71a    ACTAGGGATGAAATGAGCATTGAGAGCTTCTTGGGCAGATCTGCATGCATAGCTACCATA
1063 205_HRV71b    ACTAGGGATGAAATGAGCATTGAGAGCTTCTTGGGCAGATCTGCATGCATAGCTACCATA
1064 206_HRV71     ACTAGGGATGAAATGAGCATTGAGAGCTTCTTGGGCAGATCTGCATGCATAGCTACCATA
1065 207_HRV8      ACTAGGCATGAGACATCACTGGAATCTTTCTTGGGTAGAGCAGGATGCATTAAAATCATT
1066 208_HRV95     ACTAGGTATGAGACATCACTGGAATCTTTCTTGGGTAGAGCAGGATGCATTAAAATTATT
1067 209_HRV45     ACCAGACATGAAACCTCCATTGAATCTTTTTGGGTAGGGCTGGATGTGTGGCCAATATT
1068 210_HRV45a    ACCAGACATGAAACCTCCATTGAATCTTTTTGGGTAGGGCTGGATGTGTGGCCAATATT
1069 211_HRV45b    ACCAGACATGAAACCTCCATTGAATCTTTTTGGGTAGGGCTGGATGTGTGGCCAATATT
1070 GROUP_1       AC-----ATGA-A------T-GA----TT--T-GG--G---C----TG------------
1071
1072 1_HRV1A1|d    AGAATAAAGGTTGATTACACTGAC---------------TATAATGGA---CAGGACATA
1073 2_HRV1A2|d    AGAATAAAGGTTGATTACACTGAC---------------TATAATGGA---CAGGACATA
1074 3_HRV1A|cD    AGAATAAAGGTTGATTACACTGAC---------------TATAATGGA---CAGGACATA
1075 4_HRV1B1|d    AGAATAAAGGTTGATTACAATGAC---------------TACAATGGA---GTGAACAAA
1076 5_HRV1B2|d    AGAATAAAGGTTGATTACAATGAC---------------TACAATGGA---GTGAACAAA
1077 6_HRV1B       AGAATAAAGGTTGATTACAATGAC---------------TACAATGGA---GTGAACAAA
1078 7_HRV40a|d    ACAATTACAGTGGATAACAGTTTG---------------GAATATG------ATGACCAC
1079 8_HRV40b|d    ACAATTACAGTGGATAACAGTTTG---------------GAATATG------ATGACCAC
1080 9_HRV40       ACAATTACAGTGGATAACAGTTTG---------------GAATATG------ATGACCAC
1081 10_HRV85      ACAATTACTGTGAATAACAACCTA---------------GATTATG------ATGAAAAT
1082 11_HRV85a|    ACAATTACTGTGAATAACAACCTA---------------GATTATG------ATGAAAAT
1083 12_HRV85b|    ACAATTACTGTGAATAACAACCTA---------------GATTATG------ATGAAAAT
1084 13_HRV56a|    ACTATAACTGTGGATAATGATGTA---------------GATTATA------ATTCAAAG
1085 14_HRV56b|    ACTATAACTGTGGATAATGATGTA---------------GATTATA------ATTCAAAG
1086 15_HRV56      ACTATAACTGTGGATAATGATGTA---------------GATTATA------ATTCAAAG
1087 16_HRV54      ACCATTACAATTCAAAATGATGTA---------------GAATACA------ATGATCAC
1088 17_HRV98      ACTATCACTATTCAAAATGATGTA---------------GAATATA------ACGATCAT
1089 18_HRV59a|    ACTATTACTGTCAATAAAGACATA---------------AAATATG------ATGATGGA
1090 19_HRV59b|    ACTATTACTGTCAATAAAGACATA---------------AAATATG------ATGATGGA
1091 20_HRV59      ACTATTACTGTCAATAAAGACATA---------------AAATATG------ATGATGGA
1092 21_HRV63      ACTATCACTGTTGACAAAACCATT---------------GACTATG------ACACTGGA
1093 22_HRV63b|    ACTATCACTGTTGACAAAACCATT---------------GACTATG------ACACTGGA
1094 23_HRV63a|    ACTATCACTGTTGACAAAACCATT---------------GACTATG------ACACTGGA
1095 24_HRV39      ACAATTACTATGAAGAAGGAG------------------AACTATA------ATGATCAT
1096 25_HRV39a|    ACAATTACTATGAAGAAGGAG------------------AACTATA------ATGATCAT
1097 26_HRV39b|    ACAATTACTATGAAGAAGGAG------------------AACTATA------ATGAACAT
1098 27_HRV10a|    ACAATAACTGTTAATAATACAAGA---------------CCCTACA------ATGAACAC
1099 28_HRV10b|    ACAATAACTGTTAATAATACAAGA---------------CCCTACA------ATGAACAC
1100 29_HRV10      ACAATAACTGTTAATAATACAAGA---------------CCCTACA------ATGAACAC
```

FIG. D9 CONT'D

```
05.trace                                                                                         9/20/2007 5:04 PM 1101  30_HRV100a   ACAATTACTGTAAGTAAAATGAAA---------------AATTATA------ATGAGCAC
1102  31_HRV100b   ACAATTACTGTAAGTAAAATGAAA---------------AATTATA------ATGAGCAC
1103  32_HRV100    ACAATTACTGTAAGTAAAATGAAA---------------AATTATA------ATGAGCAC
1104  33_HRV66     ACAATTAATGTGGATAGCACAAAA---------------ACATATG------ATGAATCC
1105  34_HRV66b|   ACAATTAATGTGGATAGCACAAAA---------------ACATATG------ATGAATCC
1106  35_HRV66a|   ACAATTAATGTGGATAGCACAAAA---------------ACATATG------ATGAATCC
1107  36_HRV77a|   ACAATAAATGTAGAAGATGGTAAA---------------ACTTATG------ATGAATCT
1108  37_HRV77b|   ACAATAAATGTAGAAGATGGTAAA---------------ACTTATG------ATGAATCT
1109  38_HRV77     ACAATAAATGTAGAAGATGGTAAA---------------ACTTATG------ATGAATCT
1110  39_HRV62a    ACAATTGAA--------ACAACG----------------CTTAGTC------ATAAAGAT
1111  40_HRV62b    ACAATTGAA--------ACAACG----------------CTTAGTC------ATAAAGAT
1112  41_HRV25     ACAATTGAA--------ACAAAA----------------CTTAAAC------ATGATGAA
1113  42_HRV29a    ACAATAAAA--------GCAAAT----------------CAGGCAC------ATGACGCC
1114  43_HRV29b    ACAATAAAA--------GCAAAT----------------CAGGCAC------ATGACGCC
1115  44_HRV44a    ACAATAAAG--------ACAAAT----------------CAGGCAC------ACAATACC
1116  45_HRV44b    ACAATAAAG--------ACAAAT----------------CAGGCAC------ACAATACC
1117  46_HRV31     ATAATAGAA--------CCAGAT----------------GGACTCC------ATGATAGC
1118  47_HRV31a|   ATAATAGAA--------CCAGAT----------------GGACTCC------ATGATAGC
1119  48_HRV31b|   ATAATAGAA--------CCAGAT----------------GGACTCC------ATGATAGC
1120  49_HRV47     ACAATAAAA--------TCAGAT----------------GAGCAAC------ACATTAAT
1121  50_HRV47a|   ACAATAAAA--------TCAGAT----------------GAGCAAC------ACATTAAT
1122  51_HRV47b|   ACAATACAA--------TCAAAT----------------GAGCAAC------ACATTAAT
1123  52_HRV11     AAGTTAATTGTGCAGTATGAAGAC---------------TATAAT------GGAAAGAAA
1124  53_HRV11b|   AAGTTAATTGTGCAGTATGAAGAC---------------TATAAT------GGAAAGAAA
1125  54_HRV11a|   AAGTTAATTGTGCAGTATGAAGAC---------------TATAAT------GGAAAGAAA
1126  55_HRV76     AAGCTAGTTGTAGAATATGAGGGA---------------TATGAT------GATACAAAA
1127  56_HRV76b|   AAGCTAGTTGTAGAATATGAGGGA---------------TATGAT------GATACAAAA
1128  57_HRV76a|   AAGCTAGTTGTAGAATATGAGGGA---------------TATGAT------GATACAAAA
1129  58_HRV33     AAATTAGTAGTGAAATATGAAGAC---------------TATAAT------GAGAAAAAG
1130  59_HRV33b|   AAATTAGTAGTGAAATATGAAGAC---------------TATAAT------GAGAAAAAG
1131  60_HRV33a|   AAATTAGTAGTGAAATATGAAGAC---------------TATAAT------GAGAAAAAG
1132  61_HRV24a|   AAGTTGACTGTGGATTAT---GAC---------------AATTAT------GATACAAAA
1133  62_HRV24b|   AAGTTGACTGTGGATTAT---GAC---------------AATTAT------GATACAAAA
1134  63_HRV24     AAGTTGACTGTGGATTAT---GAC---------------AATTAT------GATACAAAA
1135  64_HRV90     AAATTAGTTGTAAACTAT---GAT---------------AATTAT------GATGAAAAC
1136  65_HRV90a|   AAATTAGTTGTAAACTAT---GAT---------------AATTAT------GATGAAAAC
1137  66_HRV90b|   AAATTAGTTGTAAACTAT---GAT---------------AATTAT------GATGAAAAC
1138  67_HRV34     AAACTTGTTGTAGATTATGAAAAT---------------TACAATGCA---AAAACAAAG
1139  68_HRV34b|   AAACTTGTTGTAGATTATGAAAAT---------------TACAATGCA---AAAACAAAG
1140  69_HRV34a|   AAACTTGTTGTAGATTATGAAAAT---------------TACAATGCA---AAAACAAAG
1141  70_HRV50a|   AAATTAGTTGTTGATTATGATGGT---------------TACAATGAG---GAAACAAAG
1142  71_HRV50b|   AAATTAGTTGTTGATTATGATGGT---------------TACAATGAG---GAAACAAAG
1143  72_HRV50     AAATTAGTTGTTGATTATGATGGT---------------TACAATGAG---GAAACAAAG
1144  73_HRV18a|   AAGTTAGTTGTACATTATGAAGAT---------------TATAATGCA---GAAACAAGG
1145  74_HRV18b|   AAGTTAGTTGTACATTATGAAGAT---------------TATAATGCA---GAAACAAGG
1146  75_HRV18     AAGTTAGTTGTACATTATGAAGAT---------------TATAATGCA---GAAACAAGG
1147  76_HRV55     GAGTTAGTTGTTCATTATGAAGAA---------------TATAACAAA---GAGGGAAAA
1148  77_HRV55b|   GAGTTAGTTGTTCATTATGAAGAA---------------TATAACAAA---GAGGGAAAA
1149  78_HRV55a|   GAGTTAGTTGTTCATTATGAAGAA---------------TATAACAAA---GAGGGAAAA
1150  79_HRV57     GAGCTTAAGGTAAAATATGAAAAT---------------TACAACACA---GAG------
1151  80_HRV57a|   GAGCTTAAGGTAAAATATGAAAAT---------------TACAACACA---GAG------
1152  81_HRV57b|   GAGCTTAAGGTAAAATATGAAAAT---------------TACAACACA---GAG------
1153  82_HRV21     AAATTAGTAGTTAACTATGATAAT---------------TACAATACT---GGAGAAAAT
1154  83_HRVHan    AAATTAATAGTTAACTATGACAAC---------------TACAATACT---GGAGAAAAT
1155  84_HRV43     ACACTTGAAGTAAATTATGATGAT---------------TATAATGGG---ACAGGCATA
1156  85_HRV43b|   ACACTTGAAGTAAATTATGATGAT---------------TATAATGGG---ACAGGCATA
1157  86_HRV43a|   ACACTTGAAGTAAATTATGATGAT---------------TATAATGGG---ACAGGCATA
1158  87_HRV75     ACACTTGAGATGGATTATACAAAC---------------TATAATGGA---GAAGGCAAA
1159  88_HRV75b|   ACACTTGAGATGGATTATACAAAC---------------TATAATGGA---GAAGGCAAA
1160  89_HRV75a|   ACACTTGAGATGGATTATACAAAC---------------TATAATGGA---GAAGGCAAA
1161  96_HRV9a|d   AAATTGAATATTGATTACAGTGAC---------------TATGATAAG---AGTGTTGAA
1162  97_HRV9b|d   AAATTGAATATTGATTACAGTGAC---------------TATGATAAG---AGTGTTGAA
1163  98_HRV9      AAATTGAATATTGATTACAGTGAC---------------TATGATAAG---AGTGTTGAA
1164  99_HRV32     AAATTAGATATTGATTATACCAAT---------------TACAATAAA---AGTGTTAAG
1165  100_HRV32a   AAATTAGATATTGATTATACCAAT---------------TACAATAAA---AGTGTTAAG
```

FIG. D9 CONT'D

```
05.trace                                                                              9/20/2007 5:04 PM 1166 101_HRV32b   AAATTAGATATTGATTATACCAAT---------------TACAATAAA---AGTGTTAAG
1167 102_HRV67    AAATTGAATATTGATTATAATGCA---------------TATGATGAA---AGTAGGGAC
1168 103_HRV67a   AAATTGAATATTGATTATAATGCA---------------TATGATGAA---AGTAGGGAC
1169 104_HRV67b   AAATTGAATATTGATTATAATGCA---------------TATGATGAA---AGTAGGGAC
1170 105_HRV15    GATTTGAAAATACATTATGAAGAT---------------TATAATAAA---GATGGGAAA
1171 106_HRV15a   GATTTGAAAATACATTATGAAGAT---------------TATAATAAA---GATGGGAAA
1172 107_HRV15b   GATTTGAAAATACATTATGAAGAT---------------TATAATAAA---GATGGGAAA
1173 108_HRV74a   CATCTAAAAATTGATTATACAAAC---------------TATAATGTT---AAAGGGAAG
1174 109_HRV74b   CATCTAAAAATTGATTATACAAAC---------------TATAATGTT---AAAGGGAAG
1175 110_HRV74    CATCTAAAAATTGATTATACAAAC---------------TATAATGTT---AAAGGGAAG
1176 111_HRV38a   AATCTTGACATAGATTACATTAAT---------------TACAACTCT---GAAGACAAA
1177 112_HRV38b   AATCTTGACATAGATTACATTAAT---------------TACAACTCT---GAAGACAAA
1178 113_HRV38    AATCTTGACATAGATTACATTAAT---------------TACAACTCT---GAAGACAAA
1179 114_HRV60    AAATTAGAAATTGACTATAGTAAC---------------TACAATGAG---GAGAATAAA
1180 115_HRV60a   AAATTAGAAATTGACTATAGTAAC---------------TACAATGAG---GAGAATAAA
1181 116_HRV60b   AAATTAGAAATTGACTATAGTAAC---------------TACAATGAG---GAGAATAAA
1182 117_HRV64a   GATTTAAAAGTAAATTATACTGGG---------------TATAATGAT---GAAGGTAAC
1183 118_HRV64b   GATTTAAAAGTAAATTATACTGGG---------------TATAATGAT---GAAGGTAAC
1184 119_HRV64    GATTTAAAAGTAAATTATACTGGG---------------TATAATGAT---GAAGGTAAC
1185 120_HRV94a   CATCTAGAGATCAAGTATGATGGT---------------TACAATGAT---GCTGGCAAC
1186 121_HRV94b   CATCTAGAGATCAAGTATGATGGT---------------TACAATGAT---GCTGGCAAC
1187 122_HRV94    CATCTAGAGATCAAGTATGATGGT---------------TACAATGAT---GCTGGCAAC
1188 123_HRV22    CACTTAGAAGTAAAATACACAGGG---------------TATAATGAA---GAGGGTAAT
1189 124_HRV22a   CACTTAGAAGTAAAATACACAGGG---------------TATAATGAA---GAGGGTAAT
1190 125_HRV22b   CACTTAGAAGTAAAATACACAGGG---------------TATAATGAA---GAGGGTAAT
1191 126_HRV82    CACCTAAATGTCAGATACACTG-----------------ATTATAAT---GAAGGTAAT
1192 127_HRV82b   CACCTAAATGTCAGATACACTG-----------------ATTATAAT---GAAGGTAAT
1193 128_HRV82a   CACCTAAATGTCAGATACACTG-----------------ATTATAAT---GAAGGTAAT
1194 129_HRV19    GAGCTCCAATTAGATTATACCAAT---------------TACAATCAA---GAAAATAAT
1195 130_HRV19a   GAGCTCCAATTAGATTATACCAAT---------------TACAATCAA---GAAAATAAT
1196 131_HRV19b   GAGCTCCAATTAGATTATACCAAT---------------TACAATCAA---GAAAATAAT
1197 132_HRV13    ACCATGAACATAGATTATACTAAT---------------TATGATGAT---TCTGTTAAT
1198 133_HRV13a   ACCATGAACATAGATTATACTAAT---------------TATGATGAT---TCTGTTAAT
1199 134_HRV13b   ACCATGAACATAGATTATACTAAT---------------TATGATGAT---TCTGTTAAT
1200 135_HRV41    ACTTTGAATATAGATTATACTGAT---------------TATGATGAT---TCTATCCAG
1201 136_HRV41a   ACTTTGAATATAGATTATACTGAT---------------TATGATGAT---TCTATCCAG
1202 137_HRV41b   ACTTTGAATATAGATTATACTGAT---------------TATGATGAT---TCTATCCAG
1203 138_HRV73    ACTATGAATATAAATTATGAAAAT---------------TATGATGAT---GCTCCTGAA
1204 139_HRV73b   ACTATGAATATAAATTATGAAAAT---------------TATGATGAT---GCTCCTGAA
1205 140_HRV73a   ACTATGAATATAAATTATGAAAAT---------------TATGATGAT---GCTCCTGAA
1206 141_HRV61    ACATTAAATATAAACTATGATAAC---------------TATGATGAT---TCTATTGAA
1207 142_HRV61a   ACATTAAATATAAACTATGATAAC---------------TATGATGAT---TCTATTGAA
1208 143_HRV61b   ACATTAAATATAAACTATGATAAC---------------TATGATGAT---TCTATTGAA
1209 144_HRV96    ACATTAAACATAGATTATGACAAT---------------TATGATGAC---TCCCCTAAG
1210 145_HRV96b   ACATTAAACATAGATTATGACAAT---------------TATGATGAC---TCCCCTAAG
1211 146_HRV96a   ACATTAAACATAGATTATGACAAT---------------TATGATGAC---TCCCCTAAG
1212  90_HRV16a|  GTGTTGGATATTGTGGACAATTAC---------------AATGAT-----------CAA
1213  91_HRV16b|  GTGTTGGATATTGTGGACAATTAC---------------AATGAT-----------CAA
1214  92_1AYM_A    GTGTTGGATATTGTGGACAATTAC---------------AATGAT-----------CAA
1215  93_HRV81a|  ATATTGGACATTAAAGAGGATTAC---------------AATACC-----------CAG
1216  94_HRV81b|  ATATTGGACATTAAAGAGGATTAC---------------AATACC-----------CAG
1217  95_HRV81     ATATTGGACATTAAAGAGGATTAC---------------AATACC-----------CAG
1218 147_HRV2     AAATTAGAGGTTACACTTGCAAAT---------------TATAACA--------AGGAG
1219 148_HRV2a|  AAATTAGAGGTTACACTTGCAAAT---------------TATAACA--------AGGAG
1220 149_HRV2b|  AAATTAGAGGTTACACTTGCAAAT---------------TATAACA--------AGGAG
1221 150_HRV49a   AAACTAGAGGTCACACTTACAAAT---------------TACAATG--------AAAAT
1222 151_HRV49b   AAACTAGAGGTCACACTTACAAAT---------------TACAATG--------AAAAT
1223 152_HRV49    AAACTAGAGGTCACACTTACAAAT---------------TACAATG--------AAAAT
1224 153_HRV23a   AAATTAAAAGTTGAGATCGGAAAC---------------TATGATG--------AAAAC
1225 154_HRV23b   AAATTAAAAGTTGAGATCGGAAAC---------------TATGATG--------AAAAC
1226 155_HRV23    AAATTAAAAGTTGAGATCGGAAAC---------------TATGATG--------AAAAC
1227 156_HRV30a   AAATTAGAACTTGAGCTTGCACAC---------------TATGATA--------AAAAG
1228 157_HRV30b   AAATTAGAACTTGAGCTTGCACAC---------------TATGATA--------AAAAG
1229 158_HRV30    AAATTAGAACTTGAGCTTGCACAC---------------TATGATA--------AAAAG
1230 159_HRV7     AAACTTGACACAA------CACAGGGT---------GACTATGACACAGGCAAAGGTGTT
```

FIG. D9 CONT'D

```
05.trace                                                              9/20/2007 5:04 PM 1231 160_HRV7b|    AAACTTGACACAA------CACAGGGT---------GACTATGACACAGGCAAAGGTGTT
1232 161_HRV7a|    AAACTTGACACAA------CACAGGGT---------GACTATGACACAGGCAAAGGTGTT
1233 162_HRV88     AAACTTGACACAA------ATGAAGGT---------GATTACGACACA---ATAGGTGTT
1234 163_HRV88a    AAACTTGACACAA------ATGAAGGT---------GATTACGACACA---ATAGGTGTT
1235 164_HRV88b    AAACTTGACACAA------ATGAAGGT---------GATTACGACACA---ATAGGTGTT
1236 165_HRV36a    GAATTTAGCACAAGTAGTGATAAAGAT---------GAACATGATGAA---ATTGGCAAG
1237 166_HRV36b    GAATTTAGCACAAGTAGTGATAAAGAT---------GAACATGATGAA---ATTGGCAAG
1238 167_HRV36     GAATTTAGCACAAGTAGTGATAAAGAT---------GAACATGATGAA---ATTGGCAAG
1239 168_HRV89a    GAATTTAATACAAGTAGTGATAAAACT---------GAACATGATAAA---ATTGGTAAA
1240 169_HRV89b    GAATTTAATACAAGTAGTGATAAAACT---------GAACATGATAAA---ATTGGTAAA
1241 170_HRV89     GAATTTAATACAAGTAGTGATAAAACT---------GAACATGATGAC---ATAGGTGTA
1242 171_HRV58     AAATTTAACACAA------ATAAGACT---------AATTATGATGAC---ATAGGTGTA
1243 172_HRV58a    AAATTTAACACAA------ATAAGACT---------AATTATGATGAC---ATAGGTGTA
1244 173_HRV58b    AAATTTAACACAA------ATAAGACT---------AATTATGATGAC---ATAGGTGTA
1245 174_HRV12a    GAATTGGATTTAGACCATGAAGGT---------------TATTCAGCA---GAAGGGAAA
1246 175_HRV12b    GAATTGGATTTAGACCATGAAGGT---------------TATTCAGCA---GAAGGGAAA
1247 176_HRV12     GAATTGGATTTAGACCATGAAGGT---------------TATTCAGCA---GAAGGGAAA
1248 177_HRV78a    AGACTAGAATTGGACCACACTGAT---------------TACAATGCT---GAAGGGAAA
1249 178_HRV78b    AGACTAGAATTGGACCACACTGAT---------------TACAATGCT---GAAGGGAAA
1250 179_HRV78     AGACTAGAATTGGACCACACTGAT---------------TACAATGCT---GAAGGGAAA
1251 180_HRV20     CATACTGACTTAGATCATGAAGCACAA---------CAATATAATGCA---CCCGGAAAA
1252 181_HRV20a    CATACTGACTTAGATCATGAAGCACAA---------CAATATAATGCA---CCCGGAAAA
1253 182_HRV20b    CATACTGACTTAGATCATGAAGCACAA---------CAATATAATGCA---CCCGGAAAA
1254 183_HRV68     CATACTGACTTAGATCACAATGAGGAT---------CAGTACAATGCA---CCTGGAAAA
1255 184_HRV68a    CATACTGACTTAGATCACAATGAGGAT---------CAGTACAATGCA---CCTGGAAAA
1256 185_HRV68b    CATACTGACTTAGATCACAATGAGGAT---------CAGTACAATGCA---CCTGGAAAA
1257 186_HRV28     CATACTGATGTTGTGCATGAAACAGAC---------AAGTACAACCAC---CCAGGGAAG
1258 187_HRV28a    CATACTGATGTTGTGCATGAAACAGAC---------AAGTACAACCAC---CCAGGGAAG
1259 188_HRV28b    CATACTGATGTTGTGCATGAAACAGAC---------AAGTACAACCAC---CCAGGGAAG
1260 189_HRV53a    CATACCAATTTAGACCAT---ACTG-----------GATACAATGAG---CCTGGGAAA
1261 190_HRV53b    CATACCAATTTAGACCAT---ACTG-----------GATACAATGAG---CCTGGGAAA
1262 191_HRV53     CATACCAATTTAGACCAT---ACTG-----------GATACAATGAG---CCTGGGAAA
1263 192_HRV46a    GAGACAGAATTGAATCATGAAGAAGGG---------AAATACAATGCA---GAAGATCAA
1264 193_HRV46b    GAGACAGAATTGAATCATGAAGAAGGG---------AAATACAATGCA---GAAGATCAA
1265 194_HRV46     GAGACAGAATTGAATCATGAAGAAGGG---------AAATACAATGCA---GAAGATCAA
1266 195_HRV80a    GAAACCAAATTAAACCATGAAACAGAC---------ATGTACAATGCT---GATGGTCAG
1267 196_HRV80b    GAAACCAAATTAAACCATGAAACAGAC---------ATGTACAATGCT---GATGGTCAG
1268 197_HRV80     GAAACCAAATTAAACCATGAAACAGAC---------ATGTACAATGCT---GATGGTCAG
1269 198_HRV51     CATACAAACCTTGAGCATGTTGAAGCAGACAGACAAGCCTACAATGCA---AAAGGGAAA
1270 199_HRV51a    CATACAAACCTTGAGCATGTTGAAGCAGACAGACAAGCCTACAATGCA---AAAGGGAAA
1271 200_HRV51b    CATACAAACCTTGAGCATGTTGAAGCAGACAGACAAGCCTACAATGCA---AAAGGGAAA
1272 201_HRV65a    CACACAGATCTTAAACATGACCATGAAGGCCAAAATGTTTACAATGAC---GAAGGCAGA
1273 202_HRV65b    CACACAGATCTTAAACATGACCATGAAGGCCAAAATGTTTACAATGAC---GAAGGCAGA
1274 203_HRV65     CACACAGATCTTAAACATGACCATGAAGGCCAAAATGTTTACAATGAC---GAAGGCAGA
1275 204_HRV71a    CACACTAAATTAGTACATGGAGAGGAGGG------TGTTTATAATATG---AAAGGTAAC
1276 205_HRV71b    CACACTAAATTAGTACATGGAGAGGAGGG------TGTTTATAATATG---AAAGGTAAC
1277 206_HRV71     CACACTAAATTAGTACATGGAGAGGAGGG------TGTTTATAATATG---AAAGGTAAC
1278 207_HRV8      GCATTAGAACTAGATCATGACAAC---------------TATGATGAA------------
1279 208_HRV95     GCATTAGAACTAGATCATGACAAC---------------TATGATAAA------------
1280 209_HRV45     AGTTTAGACATTAACCATGATGAC---------------TACCAAAAG------------
1281 210_HRV45a    AGTTTAGACATTAACCATGATGAC---------------TACCAAAAG------------
1282 211_HRV45b    AGTTTAGACATTAACCATGATGAC---------------TACCAAAAG------------
1283 GROUP_1       ------------------------------------------------------------
1284
1285 1_HRV1A1|d    AATTTCACAAAATGGAAAATCACACTACAGGAAATGGCACAGATTAGGAGAAAATTTGAA
1286 2_HRV1A2|d    AATTTCACAAAATGGAAAATCACACTACAGGAAATGGCACAGATTAGGAGAAAATTTGAA
1287 3_HRV1A|cD    AATTTCACAAAATGGAAAATCACACTACAGGAAATGGCACAGATTAGGAGAAAATTTGAA
1288 4_HRV1B1|d    AACTTTACAACATGGAAAATCACACTGCAGGAGATGGCACAAATTAGAAGAAAATTCGAA
1289 5_HRV1B2|d    AACTTTACAACATGGAAAATCACACTGCAGGAGATGGCACAAATTAGAAGAAAATTCGAA
1290 6_HRV1B       AACTTTACAACATGGAAAATCACACTGCAGGAGATGGCACAAATTAGAAGAAAATTCGAA
1291 7_HRV40a|d    CACTTTGATAAGTGGCAGATAACCATACAAGAGATGTCACAAATTAGGAGAAAATTTGAA
1292 8_HRV40b|d    CACTTTGATAAGTGGCAGATAACCATACAAGAGATGTCACAAATTAGGAGAAAATTTGAA
1293 9_HRV40       CACTTTGATAAGTGGCAGATAACCATACAAGAGATGTCACAAATTAGGAGAAAATTTGAA
1294 10_HRV85      CACTTTGATCAGTGGCAGATAACTATACAGGAAATGGCACAAATTAGAAGGAAGTTTGAG
1295 11_HRV85a|    CACTTTGATCAGTGGCAGATAACTATACAGGAAATGGCACAAATTAGAAGGAAGTTTGAG
```

FIG. D9 CONT'D

05.trace                                                                 9/20/2007 5:04 PM

```
1296  12_HRV85b|   CACTTTGATCAGTGGCAGATAACTATACAGGAAATGGCACAAATTAGAAGGAAGTTTGAG
1297  13_HRV56a|   CATTATAATAAATGGCAAATAACCTTACAAGAAATGGCTCAAGTTAGGCGTAAATTTGAA
1298  14_HRV56b|   CATTATAATAAATGGCAAATAACCTTACAAGAAATGGCTCAAGTTAGGCGTAAATTTGAA
1299  15_HRV56    CATTATAATAAATGGCAAATAACCTTACAAGAAATGGCTCAAGTTAGGCGTAAATTTGAA
1300  16_HRV54    CATTTTAAGAAATGGGATATAACATTACAAGAGATGGCACAAATACGAAGGAAATTTGAA
1301  17_HRV98    CATTTTAGACAATGGGATATAACATTACAAGAAATGGCACAAATTCGAAGAAAATTTGAA
1302  18_HRV59a|   CACTTTCTTAAATGGCCTATAACATTACAAGAGATGGCACAAATTAGGAGAAAATTTGAA
1303  19_HRV59b|   CACTTTCTTAAATGGCCTATAACATTACAAGAGATGGCACAAATTAGGAGAAAATTTGAA
1304  20_HRV59    CACTTTCTTAAATGGCCTATAACATTACAAGAGATGGCACAAATTAGGAGAAAATTTGAA
1305  21_HRV63    CATTTTAATAAATGGCAAATAACATTACAAGAGATGGCACAAATTAGAAGGAAATTTGAA
1306  22_HRV63b|   CATTTTAATAAATGGCAAATAACATTACAAGAGATGGCACAAATTAGAAGGAAATTTGAA
1307  23_HRV63a|   CATTTTAATAAATGGCAAATAACATTACAAGAGATGGCACAAATTAGAAGGAAATTTGAA
1308  24_HRV39    AATTTTGTGGATTGGAAAATTACTTTGCAGGAGATGGCACAGGTTAGAAGGAAATTTGAA
1309  25_HRV39a|   AATTTTGTGGATTGGAAAATTACTTTGCAGGAGATGGCACAGGTTAGAAGGAAATTTGAA
1310  26_HRV39b|   AATTTTGTGGATTGGAAAATTACTTTGCAGGAGATGGCACAGGTTAGAAGGAAATTTGAA
1311  27_HRV10a|   ACTTTTGACACATGGCAAATAACTCTACAAGAAATGGCCCAAATTAGAAGGAAATTTGAA
1312  28_HRV10b|   ACTTTTGACACATGGCAAATAACTCTACAAGAAATGGCCCAAATTAGAAGGAAATTTGAA
1313  29_HRV10    ACTTTTGACACATGGCAAATAACTCTACAAGAAATGGCCCAAATTAGAAGGAAATTTGAA
1314  30_HRV100a   ACTTTTGACAAATGGCAAATAACCCTACAGGAAATGGCCCAAATTAGAAGGAAATTTGAA
1315  31_HRV100b   ACTTTTGACAAATGGCAAATAACCCTACAGGAAATGGCCCAAATTAGAAGGAAATTTGAA
1316  32_HRV100   ACTTTTGACAAATGGCAAATAACCCTACAGGAAATGGCCCAAATTAGAAGGAAATTTGAA
1317  33_HRV66    AAATTTAGAACATGGCAAATTACATTGCAAGAAATGGCTCAAATCAGACGCAAATTTGAG
1318  34_HRV66b|   AAATTTAGAACATGGCAAATTACATTGCAAGAAATGGCTCAAATCAGACGCAAATTTGAG
1319  35_HRV66a|   AAATTTAGAACATGGCAAATTACATTGCAAGAAATGGCTCAAATCAGACGCAAATTTGAG
1320  36_HRV77a|   AAATTTAGAAAATGGCAAATTACACTACAAGAAATGGCTCAAATTAGGCGCAAATTTGAA
1321  37_HRV77b|   AAATTTAGAAAATGGCAAATTACACTACAAGAAATGGCTCAAATTAGGCGCAAATTTGAA
1322  38_HRV77    AAATTTAGAAAATGGCAAATTACACTACAAGAAATGGCTCAAATTAGGCGCAAATTTGAA
1323  39_HRV62a   AGATTCAAAACATGGAATATTAACTTACAAGAGATGGCTCAAATCAGGAGAAAGTTTGAA
1324  40_HRV62b   AGATTCAAAACATGGAATATTAACTTACAAGAGATGGCTCAAATCAGGAGAAAGTTTGAA
1325  41_HRV25    AGATTTAAAATATGGAATATCAATTTACAAGAAATGGCTCAAATTAGGAGAAAGTTTGAG
1326  42_HRV29a   AAGTTCGATAAATGGAATGTTAACTTACAAGAAATGGCTCAAATTAGGCGCAAATTTGAA
1327  43_HRV29b   AAGTTCGATAAATGGAATGTTAACTTACAAGAAATGGCTCAAATTAGGCGCAAATTTGAA
1328  44_HRV44a   AAGTTTGATAAATGGAATATCAACTTACAAGAAATGGCTCAAATTAGACGCAAATTTGAA
1329  45_HRV44b   AAGTTTGATAAATGGAATATCAACTTACAAGAAATGGCTCAAATTAGACGCAAATTTGAA
1330  46_HRV31    AAATAAAAGTATGGCACATTAATTTACAAGAGATGGCCCAGATTAGGCGAAAATTTGAA
1331  47_HRV31a|   AAATATAAAGTATGGCACATTAATTTACAAGAGATGGCCCAGATTAGGCGAAAATTTGAA
1332  48_HRV31b|   AAATATAAAGTATGGCACATTAATTTACAAGAGATGGCCCAGATTAGGCGAAAATTTGAA
1333  49_HRV47    AAATTTAAAGTATGGCACATTAATTTACAAGAAATGGCCCAGATCAGGCGTAAATATGAA
1334  50_HRV47a|   AAATTTAAAGTATGGCACATTAATTTACAAGAAATGGCCCAGATCAGGCGTAAATATGAA
1335  51_HRV47b|   AAATTTAAAGTATGGCACATTAATTTACAAGAAATGGCCCAGATCAGGCGTAAATATGAA
1336  52_HRV11    AACTTTAACACATGGAAAATAAACTTGCAAGAGATGGCACAAATTAGAAGGAAATTTGAA
1337  53_HRV11b|   AACTTTAACACATGGAAAATAAACTTGCAAGAGATGGCACAAATTAGAAGGAAATTTGAA
1338  54_HRV11a|   AACTTTAACACATGGAAAATAAACTTGCAAGAGATGGCACAAATTAGAAGGAAATTTGAA
1339  55_HRV76    AACTTTAAGACATGGAAAATAAACCTACAAGAAATGGCACAAGTTAGAAGAAAATTTGAG
1340  56_HRV76b|   AACTTTAAGACATGGAAAATAAACCTACAAGAAATGGCACAAGTTAGAAGAAAATTTGAG
1341  57_HRV76a|   AACTTTAAGACATGGAAAATAAACCTACAAGAAATGGCACAAGTTAGAAGAAAATTTGAG
1342  58_HRV33    AATTTTATGACATGGAAAATAAATCTACAAGAGATGGCACAGATTAGGAGGAAATTTGAA
1343  59_HRV33b|   AATTTTATGACATGGAAAATAAATCTACAAGAGATGGCACAGATTAGGAGGAAATTTGAA
1344  60_HRV33a|   AATTTTATGACATGGAAAATAAATCTACAAGAGATGGCACAGATTAGGAGGAAATTTGAA
1345  61_HRV24a|   AATTTTTTCAAATGGCAAATAAATCTACAAGAAATGGCCCAAGTCAGAAGAAAATTTGAA
1346  62_HRV24b|   AATTTTTTCAAATGGCAAATAAATCTACAAGAAATGGCCCAAGTCAGAAGAAAATTTGAA
1347  63_HRV24    AATTTTTTCAAATGGCAAATAAATCTACAAGAAATGGCCCAAGTCAGAAGAAAATTTGAA
1348  64_HRV90    AACTTCCATAAATGGCAAATTAACCTGCAAGAGATGGCACAGATTAGAAGAAAATTTGAA
1349  65_HRV90a|   AACTTCCATAAATGGCAAATTAACCTGCAAGAGATGGCACAGATTAGAAGAAAATTTGAA
1350  66_HRV90b|   AACTTCCATAAATGGCAAATTAACCTGCAAGAGATGGCACAGATTAGAAGAAAATTTGAA
1351  67_HRV34    AACTTTATGACATGGCAAATTAATTTACAGGAAATGGCACAGATTAGAAGGAAATTTGAA
1352  68_HRV34b|   AACTTTATGACATGGCAAATTAATTTACAGGAAATGGCACAGATTAGAAGGAAATTTGAA
1353  69_HRV34a|   AACTTTATGACATGGCAAATTAATTTACAGGAAATGGCACAGATTAGAAGGAAATTTGAA
1354  70_HRV50a|   AACTTCAAGAAATGGCAAATCAACCTACAAGAAATGGCACAGATCAGAAGGAAATTTGAG
1355  71_HRV50b|   AACTTCAAGAAATGGCAAATCAACCTACAAGAAATGGCACAGATCAGAAGGAAATTTGAG
1356  72_HRV50    AACTTCAAGAAATGGCAAATCAACCTACAAGAAATGGCACAGATCAGAAGGAAATTTGAG
1357  73_HRV18a|   AACTTTGTAAAATGGCAAATAAATCTACAGGAAATGGCACAGATTAGGAGGAAATTTGAG
1358  74_HRV18b|   AACTTTGTAAAATGGCAAATAAATCTACAGGAAATGGCCCAGATTAGGAGAAAATTTGAG
1359  75_HRV18    AACTTTGTAAAATGGCAAATAAATCTACAGGAAATGGCCCAGATTAGGAGAAAATTTGAG
1360  76_HRV55    AATTTTACTAAGTGGCAAGTAAACATCCAAGAGATGGCTCAGATTAGAAGAAAATTTGAA
```

FIG. D9 CONT'D

```
05.trace                                                                    9/20/2007 5:04 PM 1361  77_HRV55b|   AATTTTACTAAGTGGCAAGTAAACATCCAAGAGATGGCTCAGATTAGAAGAAAATTTGAA
1362  78_HRV55a|   AATTTTACTAAGTGGCAAGTAAACATCCAAGAGATGGCTCAGATTAGAAGAAAATTTGAA
1363  79_HRV57    AATTTCACTAAATGGGAAATAAATCTACAAGAAATGGCACAAATCAGAAGAAAATTTGAA
1364  80_HRV57a|   AATTTCACTAAATGGGAAATAAATCTACAAGAAATGGCACAAATCAGAAGAAAATTTGAA
1365  81_HRV57b|   AATTTCACTAAATGGGAAATAAATCTACAAGAAATGGCACAAATCAGAAGAAAATTTGAA
1366  82_HRV21    AACATTAGTACATGGCAAATAAATATTAAAGAGATGGCACAAATTAGGAGAAAATTTGAA
1367  83_HRVHan   AACATTAATACATGGCAAATAAATATTAAAGAGATGGCACAAATTAGGAGAAAATTTGAA
1368  84_HRV43    AATTTTACCCAATGGCCAATCAACTTGCAAGAAATGGCACAAATTAGAAGAAAGTATGAA
1369  85_HRV43b|   AATTTTACCCAATGGCCAATCAACTTGCAAGAAATGGCACAAATTAGAAGAAAGTATGAA
1370  86_HRV43a|   AATTTTACCCAATGGCCAATCAACTTGCAAGAAATGGCACAAATTAGAAGAAAGTATGAA
1371  87_HRV75    AACTTCACTCAGTGGCCAATCAATCTACAGGAAATGGCTCAAATTAGAAGGAAATATGAA
1372  88_HRV75b|   AACTTCACTCAGTGGCCAATCAATCTACAGGAAATGGCTCAAATTAGAAGGAAATATGAA
1373  89_HRV75a|   AACTTCACTCAGTGGCCAATCAATCTACAGGAAATGGCTCAAATTAGAAGGAAATATGAA
1374  96_HRV9a|d   AATTTCACAATCTGGAAAATAAATATAAAGGAAATGGCCCAGATCAGGAGGAAATTTGAA
1375  97_HRV9b|d   AATTTCACAATCTGGAAAATAAATATAAAGGAAATGGCCCAGATCAGGAGGAAATTTGAA
1376  98_HRV9     AATTTCACAATCTGGAAAATAAATATAAAGGAAATGGCCCAGATCAGGAGGAAATTTGAA
1377  99_HRV32    AATTTCACAATTTGGAAGATAAATATAAAAGAAATGGCCCAGATTAGGAGAAAATTTGAG
1378  100_HRV32a   AATTTCACAATTTGGAAGATAAATATAAAAGAAATGGCCCAGATTAGGAGAAAATTTGAG
1379  101_HRV32b   AATTTCACAATTTGGAAGATAAATATAAAAGAAATGGCCCAGATTAGGAGAAAATTTGAG
1380  102_HRV67   AATTTCACAATTTGGAAATAAATATAAAAGAAATGGCCCAGATTAGGAGGAAATTTGAA
1381  103_HRV67a   AATTTCACAATTTGGAAATAAATATAAAAGAAATGGCCCAGATTAGGAGGAAATTTGAA
1382  104_HRV67b   AATTTCACAATTTGGAAATAAATATAAAAGAAATGGCCCAGATTAGGAGGAAATTTGAA
1383  105_HRV15   AACTTTACTAAATGGCAAATTAATCTCAAAGAAATGGCCCAGATTAGAAGGAAATTTGAG
1384  106_HRV15a   AACTTTACTAAATGGCAAATTAATCTCAAAGAAATGGCCCAGATTAGAAGGAAATTTGAG
1385  107_HRV15b   AACTTTACTAAATGGCAAATTAATCTCAAAGAAATGGCCCAGATTAGAAGGAAATTTGAG
1386  108_HRV74a   AATTTTACTAAATGGCAAATAAATCTTAAAGAAATGGCACAGATTAGGAGAAAATTTGAG
1387  109_HRV74b   AATTTTACTAAATGGCAAATAAATCTTAAAGAAATGGCACAGATTAGGAGAAAATTTGAG
1388  110_HRV74   AATTTTACTAAATGGCAAATAAATCTTAAAGAAATGGCACAGATTAGGAGAAAATTTGAG
1389  111_HRV38a   AACTTTACAACATGGCAAATCAATCTCAAAGAAATGGCTCAAATCAGAAGAAAGTTTGAA
1390  112_HRV38b   AACTTTACAACATGGCAAATCAATCTCAAAGAAATGGCTCAAATCAGAAGAAAGTTTGAA
1391  113_HRV38   AACTTTACAACATGGCAAATCAATCTCAAAGAAATGGCTCAAATCAGAAGAAAGTTTGAA
1392  114_HRV60   AATTTCACAACTTGGCAAATTAACCTAAAGGAAATGGCACAAATAAGAAGAAAGTTTGAA
1393  115_HRV60a   AATTTCACAACTTGGCAAATTAACCTAAAGGAAATGGCACAAATAAGAAGAAAGTTTGAA
1394  116_HRV60b   AATTTCACAACTTGGCAAATTAACCTAAAGGAAATGGCACAAATAAGAAGAAAGTTTGAA
1395  117_HRV64a   AATTTTAACAAATGGCAGATCACCTTGAAAGAAATGGCTCAGATAAGAAGGAAGTATGAA
1396  118_HRV64b   AATTTTAACAAATGGCAGATCACCTTGAAAGAAATGGCTCAGATAAGAAGGAAGTATGAA
1397  119_HRV64   AATTTTAACAAATGGCAGATCACCTTGAAAGAAATGGCTCAGATAAGAAGGAAGTATGAA
1398  120_HRV94a   AATTTCCAATCATGGCAAATTACCCTAAAAGAAATGGCACAAATAAGGAAGGAAATTTGAA
1399  121_HRV94b   AATTTCCAATCATGGCAAATTACCCTAAAAGAAATGGCACAAATAAGAAGGAAATTTGAA
1400  122_HRV94   AATTTCCAATCATGGCAAATTACCCTAAAAGAAATGGCACAAATAAGAAGGAAATTTGAA
1401  123_HRV22   AACTTTAACATATGGCAAATTAACCTTAAAGAGATGGCTCAGATAAGAAGGAAGTTTGAG
1402  124_HRV22a   AACTTTAACATATGGCAAATTAACCTTAAAGAGATGGCTCAGATAAGAAGGAAGTTTGAG
1403  125_HRV22b   AACTTTAACATATGGCAAATTAACCTTAAAGAGATGGCTCAGATAAGAAGGAAGTTTGAG
1404  126_HRV82   AACTTTAGATCATGGCAAATAAGCATAAAGGAAATGGCACAAATTAGAAGGAAGTTTGAA
1405  127_HRV82b   AACTTTAGATCATGGCAAATAAGCATAAAGGAAATGGCACAAATTAGAAGGAAGTTTGAA
1406  128_HRV82a   AACTTTAGATCATGGCAAATAAGCATAAAGGAAATGGCACAAATTAGAAGGAAGTTTGAA
1407  129_HRV19   AATTTCAAACTTGGCAAATAAACTTGAAAGAAATGGCACAGATTAGAAGAAAATTTGAA
1408  130_HRV19a   AATTTCAAAACTTGGCAAATAAACTTGAAAGAAATGGCACAGATTAGAAGAAAATTTGAA
1409  131_HRV19b   AATTTCAAAACTTGGCAAATAAACTTGAAAGAAATGGCACAGATTAGAAGAAAATTTGAA
1410  132_HRV13   AATTTTGTGAAATGGAAATAAGTTTGCAAGAAATGGCCCAAGTGCGCAGAAAATTTGAG
1411  133_HRV13a   AATTTTGTGAAATGGAAATAAGTTTGCAAGAAATGGCCCAAGTGCGCAGAAAATTTGAG
1412  134_HRV13b   AATTTTGTGAAATGGAAATAAGTTTGCAAGAAATGGCCCAAGTGCGCAGAAAATTTGAG
1413  135_HRV41   AACTTCAAGAAGTGGAAAATTAGCTTACAGGAGATGGCCCAAGTACGTAGAAAGTTTGAA
1414  136_HRV41a   AACTTCAAGAAGTGGAAAATTAGCTTACAGGAGATGGCCCAAGTACGTAGAAAGTTTGAA
1415  137_HRV41b   AACTTCAAGAAGTGGAAAATTAGCTTACAGGAGATGGCCCAAGTACGTAGAAAGTTTGAA
1416  138_HRV73   AATTTTACCAAATGGAAAATAAGTTTACAAGAGATGGCTCAAATACGTAGGAAATTTGAA
1417  139_HRV73b   AATTTTACCAAATGGAAAATAAGTTTACAAGAGATGGCTCAAATACGTAGGAAATTTGAA
1418  140_HRV73a   AATTTTACCAAATGGAAAATAAGTTTACAAGAGATGGCTCAAATACGTAGGAAATTTGAA
1419  141_HRV61   AACTTCAAGGTGTGGAAAATAAACCTGCAAGAGATGGCACAAATACGTAGAAAATTTGAG
1420  142_HRV61a   AACTTCAAGGTGTGGAAAATAAACCTGCAAGAGATGGCACAAATACGTAGAAAATTTGAG
1421  143_HRV61b   AACTTCAAGGTGTGGAAAATAAACCTGCAAGAGATGGCACAAATACGTAGAAAATTTGAG
1422  144_HRV96   AATTTAAGGTGTGGAAAATAAACCTACAAGAAATGGCTCAAATTCGCAGGAAGTTTGAA
1423  145_HRV96b   AATTTTAAGGTGTGGAAAATAAACCTACAAGAAATGGCTCAAATTCGCAGGAAGTTTGAA
1424  146_HRV96a   AATTTTAAGGTGTGGAAAATAAATCTACAAGAAATGGCTCAAATTCGCAGGAAGTTTGAA
1425  90_HRV16a|   AGTTTCACTAAATGGAAGATAAACCTGCAAGAAATGGCACAAATTAGAAGAAAATTTGAA
```

FIG. D9 CONT'D

```
05.trace                                                                         9/20/2007 5:04 PM 1426  91_HRV16b|   AGTTTCACTAAATGGAAGATAAACCTGCAAGAAATGGCACAAATTAGAAGAAAATTTGAA
1427  92_1AYM_A    AGTTTCACTAAATGGAAGATAAACCTGCAAGAAATGGCACAAATTAGAAGAAAATTTGAA
1428  93_HRV81a|   AGCTTTACTAAATGGAAAATTAACTTACAAGAGATGGCACAGATTAGGAGAAAGTTTGAA
1429  94_HRV81b|   AGCTTTACTAAATGGAAAATTAACTTACAAGAGATGGCACAGATTAGGAGAAAGTTTGAA
1430  95_HRV81     AGCTTTACTAAATGGAAAATTAACTTACAAGAGATGGCACAGATTAGGAGAAAGTTTGAA
1431  147_HRV2     AATTTTACAGTGTGGGCTATTAATATACAAGAAATGGCTCAAATTAGAAGGAAATTTGAA
1432  148_HRV2a|   AATTTTACAGTGTGGGCTATTAATATACAAGAAATGGCTCAAATTAGAAGGAAATTTGAA
1433  149_HRV2b|   AATTTTACAGTGTGGGCTATTAATATACAAGAAATGGCTCAAATTAGAAGGAAATTTGAA
1434  150_HRV49a   AATTTCAAAGTATGGAACATCAATTTGCAAGAAATGGCCCAGATCAGAAGAAAATTTGAA
1435  151_HRV49b   AATTTCAAAGTATGGAACATCAATTTGCAAGAAATGGCCCAGATCAGAAGAAAATTTGAA
1436  152_HRV49    AATTTCAAAGTATGGAACATCAATTTGCAAGAAATGGCCCAGATCAGAAGAAAATTTGAA
1437  153_HRV23a   AATTTTAATACTTGGAATATTAATTTACAGGAAATGGCCCAAATCAGAAGAAAGTTTGAA
1438  154_HRV23b   AATTTTAATACTTGGAATATTAATTTACAGGAAATGGCCCAAATCAGAAGAAAGTTTGAA
1439  155_HRV23    AATTTTAATACTTGGAATATTAATTTACAGGAAATGGCCCAAATCAGAAGAAAGTTTGAA
1440  156_HRV30a   AACTTTACCACATGGAATATTAATCTTCAAGAAATGGCCCAAATTAGAAGAAAATTTGAG
1441  157_HRV30b   AACTTTACCACATGGAATATTAATCTTCAAGAAATGGCCCAAATTAGAAGAAAATTTGAG
1442  158_HRV30    AACTTTACCACATGGAATATTAATCTTCAAGAAATGGCCCAAATTAGAAGAAAATTTGAG
1443  159_HRV7     GGTTTCACTACATGGAAAATCAGCTTACAAGAAATGGCACAAATCAGAAGAAAGTTTGAA
1444  160_HRV7b|   GGTTTCACTACATGGAAAATCAGCTTACAAGAAATGGCACAAATCAGAAGAAAGTTTGAA
1445  161_HRV7a|   GGTTTCACTACATGGAAAATCAGCTTACAAGAAATGGCACAAATCAGAAGAAAGTTTGAA
1446  162_HRV88    GGATTTGTAACATGGAAGATTAGCTTGCAAGAAATGGCACAAATCAGGAGAAAATTTGAA
1447  163_HRV88a   GGATTTGTAACATGGAAGATTAGCTTGCAAGAAATGGCACAAATCAGGAGAAAATTTGAA
1448  164_HRV88b   GGATTTGTAACATGGAAGATTAGCTTGCAAGAAATGGCACAAATCAGGAGAAAATTTGAA
1449  165_HRV36a   GGATTCAAAACATGGAAGATTAGTCTTCAAGAAATGGCACAAATTAGAAGGAAATATGAA
1450  166_HRV36b   GGATTCAAAACATGGAAGATTAGTCTTCAAGAAATGGCACAAATTAGAAGGAAATATGAA
1451  167_HRV36    GGATTCAAAACATGGAAGATTAGTCTTCAAGAAATGGCACAAATTAGAAGGAAATATGAA
1452  168_HRV89a   GGATTCAAAACATGGAAGGTTAGTCTTCAAGAAATGGCACAAATCAGAAGAAAATATGAA
1453  169_HRV89b   GGATTCAAAACATGGAAGGTTAGTCTTCAAGAAATGGCACAAATCAGAAGAAAATATGAA
1454  170_HRV89    GGATTCAAAACATGGAAGGTTAGTCTTCAAGAAATGGCACAAATCAGAAGAAAATATGAA
1455  171_HRV58    GGATACAAAACATGGAAAATTAGCCTTCAAGAGATGGCACAAATTAGAAGGAAATTTGAG
1456  172_HRV58a   GGATACAAAACATGGAAAATTAGCCTTCAAGAGATGGCACAAATTAGAAGGAAATTTGAG
1457  173_HRV58b   GGATACAAAACATGGAAAATTAGCCTTCAAGAGATGGCACAAATTAGAAGGAAATTTGAG
1458  174_HRV12a   AACTTTAAAACATGGAAGATAAATCTTAAGGAAATGGCCCAGATTAGAAGGAAAAATGAG
1459  175_HRV12b   AACTTTAAAACATGGAAGATAAATCTTAAGGAAATGGCCCAGATTAGAAGGAAAAATGAG
1460  176_HRV12    AACTTTAAAACATGGAAGATAAATCTTAAGGAAATGGCCCAGATTAGAAGGAAAAATGAG
1461  177_HRV78a   AATTTTACAACGTGGAAAATCAACTTACAGGAGATGGCCCAGATTAGAAGAAAAGAATGAG
1462  178_HRV78b   AATTTTACAACGTGGAAAATCAACTTACAGGAGATGGCCCAGATTAGAAGAAAAGAATGAG
1463  179_HRV78    AATTTTACAACGTGGAAAATCAACTTACAGGAGATGGCCCAGATTAGAAGAAAAGAATGAG
1464  180_HRV20    AATTTCTCTCAGTGGAAGATCACAATCAAGGAAATGGCTCAAATCAGAAGAAAATGTGAG
1465  181_HRV20a   AATTTCTCTCAGTGGAAGATCACAATCAAGGAAATGGCTCAAATCAGAAGAAAATGTGAG
1466  182_HRV20b   AATTTCTCTCAGTGGAAGATCACAATCAAGGAAATGGCTCAAATCAGAAGAAAATGTGAG
1467  183_HRV68    AACTTCTCCCAATGGAAAATTACAATTAAGGAAATGGCTCAAATTAGAAGAAAGTGTGAA
1468  184_HRV68a   AACTTCTCCCAATGGAAAATTACAATTAAGGAAATGGCTCAAATTAGAAGAAAGTGTGAA
1469  185_HRV68b   AACTTCTCCCAATGGAAAATTACAATTAAGGAAATGGCTCAAATTAGAAGAAAGTGTGAA
1470  186_HRV28    AATTTTAGTAAATGGAATATCACTCTCAAAGAAATGGCCCAAATCAGAAGAAAGTGTGAA
1471  187_HRV28a   AATTTTAGTAAATGGAATATCACTCTCAAAGAAATGGCCCAAATCAGAAGAAAGTGTGAA
1472  188_HRV28b   AATTTTAGTAAATGGAATATCACTCTCAAAGAAATGGCCCAAATCAGAAGAAAGTGTGAA
1473  189_HRV53a   AACCACTCAGAATGGAAGATTACACTCAAAGAAATGGCCCAGATTAGAAGGAAATGTGAG
1474  190_HRV53b   AACCACTCAGAATGGAAGATTACACTCAAAGAAATGGCCCAGATTAGAAGGAAATGTGAG
1475  191_HRV53    AACCACTCAGAATGGAAGATTACACTCAAAGAAATGGCCCAGATTAGAAGGAAATGTGAG
1476  192_HRV46a   AACTTCTCAAAATGGAAAATAACACTGTTGGAAATGGCACAAATCAGAAGGAAGTGTGAA
1477  193_HRV46b   AACTTCTCAAAATGGAAAATAACACTGTTGGAAATGGCACAAATCAGAAGAAAGTGTGAA
1478  194_HRV46    AACTTCTCAAAATGGAAAATAACACTGTTGGAAATGGCACAAATCAGAAGAAAGTGTGAA
1479  195_HRV80a   AATTTTTCAAAGTGGAAAATAACATTAATGGAAATGGCACAAATTAGAAGAAAGTGTGAG
1480  196_HRV80b   AATTTTTCAAAGTGGAAAATAACATTAATGGAAATGGCACAAATTAGAAGAAAGTGTGAG
1481  197_HRV80    AATTTTTCAAAGTGGAAAATAACATTAATGGAAATGGCACAAATTAGAAGAAAGTGTGAG
1482  198_HRV51    AATTTCTCTACATGGAAAATTACACTCAAAGAAATGGCTCAAATTAGAAGAAAGTGTGAA
1483  199_HRV51a   AATTTCTCTACATGGAAAATTACACTCAAAGAAATGGCTCAAATTAGAAGAAAGTGTGAA
1484  200_HRV51b   AATTTCTCTACATGGAAAATTACACTCAAAGAAATGGCTCAAATTAGAAGAAAGTGTGAA
1485  201_HRV65a   AATTTCTCTGCTTGGGAAATTACACTCAAGGAAATGGCTCAAATTAGGAGAAAGTGTGAA
1486  202_HRV65b   AATTTCTCTGCTTGGGAAATTACACTCAAGGAAATGGCTCAAATTAGGAGAAAGTGTGAA
1487  203_HRV65    AATTTCTCTGCTTGGGAAATTACACTCAAGGAAATGGCTCAAATTAGGAGAAAGTGTGAA
1488  204_HRV71a   AATCTCTCAAAGTGGCAGATTACACTCAAAGAAATGGCTCAGATCAGGAGGAAATGTGAA
1489  205_HRV71b   AATCTCTCAAAGTGGCAGATTACACTCAAAGAAATGGCTCAGATCAGGAGGAAATGTGAA
1490  206_HRV71    AATCTCTCAAAGTGGCAGATTACACTCAAAGAAATGGCTCAGATCAGGAGGAAATGTGAA
```

FIG. D9 CONT'D 05.trace                                                                      9/20/2007 5:04 PM

```
1491 207_HRV8     AGTTTCAGGACCTGGGGAATAAACATACAAGAGATGTCACAAATTAGAAGGAAATTTGAG
1492 208_HRV95    AATTTCAGGACCTGGGGAATAAACATACAAGAGATGTCACAAATTAGAAGGAAATTTGAA
1493 209_HRV45    AATTACAAAAATTGGGCAATTAGTTTACAAGAAATGTCACAAATTAGGAGGAAATTTGAA
1494 210_HRV45a   AATTACAAAAATTGGGCAATTAGTTTACAAGAAATGTCACAAATTAGGAGGAAATTTGAA
1495 211_HRV45b   AATTACAAAAATTGGGCAATTAGTTTACAAGAAATGTCACAAATTAGGAGGAAATTTGAA
1496 GROUP_1      -----------TGG----T-A---T----GA-ATG-C-CA--T--G--G-AA----GA-
1497
1498  1_HRV1A1|d  TTGTTTACATATGTCAGGTTTGACTCAGAAATAACCTTGG-TGCCTTGTATTGCTGGTAG
1499  2_HRV1A2|d  TTGTTTACATATGTCAGGTTTGACTCAGAAATAACCTTGG-TGCCTTGTATTGCTGGTAG
1500  3_HRV1A|cD  TTGTTTACATATGTCAGGTTTGACTCAGAAATAACCTTGG-TGCCTTGTATTGCTGGTAG
1501  4_HRV1B1|d  CTATTTACTTATGTTAGGTTTGATTCAGAAGTAACTTTAG-TACCCTGTATTGCTGGTAG
1502  5_HRV1B2|d  CTATTTACTTATGTTAGGTTTGATTCAGAAGTAACTTTAG-TACCCTGTATTGCTGGTAG
1503  6_HRV1B     CTATTTACTTATGTTAGGTTTGATTCAGAAGTAACTTTAG-TACCCTGTATTGCTGGTAG
1504  7_HRV40a|d  TTCTTTACATATGCTAGGTTTGATTCAGAAATTACCTTAG-TTCCTTGTATAGCCGGTAA
1505  8_HRV40b|d  TTCTTTACATATGCTAGGTTTGATTCAGAAATTACCTTAG-TTCCTTGTATAGCCGGTAA
1506  9_HRV40     TTCTTTACATATGCTAGGTTTGATTCAGAAATTACCTTAG-TTCCTTGTATAGCCGGTAA
1507 10_HRV85     TTCTTTACTTACACTAGATTTGATTCAGAAATCACTTTAG-TCCCTTGTATAGCTGGAAA
1508 11_HRV85a|   TTCTTTACTTACACTAGATTTGATTCAGAAATCACTTTAG-TCCCTTGTATAGCTGGAAA
1509 12_HRV85b|   TTCTTTACTTACACTAGATTTGATTCAGAAATCACTTTAG-TCCCTTGTATAGCTGGAAA
1510 13_HRV56a|   TTCTTTACTTATGTCAGATTTGATTCAGAGGTTACTTTGG-TACCTTGTGTAGCCGGCAA
1511 14_HRV56b|   TTCTTTACTTATGTCAGATTTGATTCAGAGGTTACTTTGG-TACCTTGTGTAGCCGGCAA
1512 15_HRV56     TTCTTTACTTATGTCAGATTTGATTCAGAGGTTACTTTGG-TACCTTGTGTAGCCGGCAA
1513 16_HRV54     TTCTTTACTTATGTTAGGTTTGATTCAGAAATTACTCTAG-TCCCCTGTATAGCTGGTAA
1514 17_HRV98     TTCTTTACTTATGTTAGATTTGATTCAGAAGTTACCTTAG-TTCCTTGCATAGCTGGCAA
1515 18_HRV59a|   TTCTTCACATATGTTAGATTTGACTCAGAAATCACTTTGG-TGCCTTGCATAGCTGGAAA
1516 19_HRV59b|   TTCTTCACATATGTTAGATTTGACTCAGAAATCACTTTGG-TGCCTTGCATAGCTGGAAA
1517 20_HRV59     TTCTTCACATATGTTAGATTTGACTCAGAAATCACTTTGG-TGCCTTGCATAGCTGGAAA
1518 21_HRV63     TTCTTCACATATGTCAGATTTGATTCAGAAGTCACTCTTG-TACCATGTATAGCAGGAAA
1519 22_HRV63b|   TTCTTCACATATGTCAGATTTGATTCAGAAGTCACTCTTG-TACCATGTATAGCAGGAAA
1520 23_HRV63a|   TTCTTCACATATGTCAGATTTGATTCAGAAGTCACTCTTG-TACCATGTATAGCAGGAAA
1521 24_HRV39     ATGTTCACCTATGTTAGATTTGACTCAGAGATTACTTTAG-TCCCATGCATAGCTGGAAG
1522 25_HRV39a|   ATGTTCACCTATGTTAGATTTGACTCAGAGATTACTTTAG-TCCCATGCATAGCTGGAAG
1523 26_HRV39b|   ATGTTCACCTACGTTAGATTTGACTCAGAGATTACTTTAG-TCCCATGCATAGCTGGAAG
1524 27_HRV10a|   ATGTTTACATATGTTAGATTTGACTCAGAAGTCACTTTAG-TACCTTGCATCGCAGGCAA
1525 28_HRV10b|   ATGTTTACATATGTTAGATTTGACTCAGAAGTCACTTTAG-TACCTTGCATCGCAGGCAA
1526 29_HRV10     ATGTTTACATATGTTAGATTTGACTCAGAAGTCACTTTAG-TACCTTGCATCGCAGGCAA
1527 30_HRV100a   ATGTTTACATATGTCAGATTTGACTCAGAAATCACATTGG-TACCCTGTATTGCAGGAAA
1528 31_HRV100b   ATGTTTACATATGTCAGATTTGACTCAGAAATCACATTGG-TACCCTGTATTGCAGGAAA
1529 32_HRV100    ATGTTTACATATGTCAGATTTGACTCAGAAATCACATTGG-TACCCTGTATTGCAGGAAA
1530 33_HRV66     ATGTTCACATATGTTAGGTTTGATTCTGAAATTACATTAG-TCCCATGCATTGCAGGAAA
1531 34_HRV66b|   ATGTTCACATATGTTAGGTTTGATTCTGAAATTACATTAG-TCCCATGCATTGCAGGAAA
1532 35_HRV66a|   ATGTTCACATATGTTAGGTTTGATTCTGAAATTACATTAG-TCCCATGCATTGCAGGAAA
1533 36_HRV77a|   ATGTTTACATATGTAAGATTTGATTCAGAAATTACATTGG-TCCCATGTATTGCTGGAAA
1534 37_HRV77b|   ATGTTTACATATGTAAGATTTGATTCAGAAATTACATTAG-TCCCATGTATTGCTGGAAA
1535 38_HRV77     ATGTTTACATATGTAAGATTTGATTCAGAAATTACATTGG-TCCCATGTATTGCTGGAAA
1536 39_HRV62a    ATGTTTACATATGTAAGATTTGATTCAGAAATAACCCTGG-TTCCATCTATTGCAGGACG
1537 40_HRV62b    ATGTTTACATATGTAAGATTTGATTCAGAAATAACCCTGG-TTCCATCTATTGCAGGACG
1538 41_HRV25     ATGTTTACATATGTGAGATTTGATTCAGAGATAACCCTAG-TTCCATCTATTGCAGGACG
1539 42_HRV29a    ATGTTCACATATGTGAGATTTGACTCAGAAATAACTCTGG-TTCCTTTGCATTGCAGGACG
1540 43_HRV29b    ATGTTCACATATGTGAGATTTGACTCAGAAATAACTCTGG-TTCCATGCATTGCAGGACG
1541 44_HRV44a    ATGTTCACATATGTGAGATTTGATTCGGAAATAACTCTAG-TTCCATGCATTGCAGGACA
1542 45_HRV44b    ATGTTCACATATGTGAGATTTGATTCAGAAATAACTCTAG-TTCCATGCATTGCAGGACG
1543 46_HRV31     ATGTTCACATATGTAAGATTTGATTCAGAAGTGACCATAG-TTCCATGCATTGCAGGACA
1544 47_HRV31a|   ATGTTCACATATGTAAGATTTGATTCAGAAGTGACCATAG-TTCCATGCATTGCAGGACA
1545 48_HRV31b|   ATGTTCACATATGTAAGATTTGATTCAGAAGTGACCATAG-TTCCATGCATTGCAGGACA
1546 49_HRV47     ATGTTTACATATGTAAGATTTGATTCAGAAGTAACCATGG-TTCCATGTATTGCAGGGTA
1547 50_HRV47a|   ATGTTTACATATGTAAGATTTGATTCAGAAGTAACCATGG-TTCCATGCATTGCAGGGTA
1548 51_HRV47b|   ATGTTTACATATGTAAGATTTGATTCAGAAGTAACCATGG-TTCCATGTATTGCAGGGTA
1549 52_HRV11     ATGTTCACATACACTAGATTTGATTCAGAGATCACATTGG-TGCCTTGTATAGCTGCAAA
1550 53_HRV11b|   ATGTTCACATACACTAGATTTGATTCAGAGATCACATTGG-TGCCTTGTATAGCTGCAAA
1551 54_HRV11a|   ATGTTCACATACACTAGATTTGATTCAGAGATCACATTGG-TGCCTTGTATAGCTGCAAA
1552 55_HRV76     ATGTTTACATATACTAGATTTGATTCAGAAGTTACTCTAG-TTCCTTCTATAGCTGCCAA
1553 56_HRV76b|   ATGTTTACATATACTAGATTTGATTCAGAAGTTACTCTAG-TTCCTTCTATAGCTGCCAA
1554 57_HRV76a|   ATGTTTACATATACTAGATTTGATTCAGAAGTTACTCTAG-TTCCTTCTATAGCTGCCAA
1555 58_HRV33     ATGTTTACATATGCCAGATTTGATTCAGAGATCACCCTAG-TCCCTTCTATAGCTGCCCA
```

FIG. D9 CONT'D 05.trace                                                                                    9/20/2007 5:04 PM

```
1556  59_HRV33b|   ATGTTTACATATGCCAGATTTGATTCAGAGATCACCCTAG-TCCCTTCTATAGCTGCCCA
1557  60_HRV33a|   ATGTTTACATATGCCAGATTTGATTCAGAGATCACCCTAG-TCCCTTCTATAGCTGCCCA
1558  61_HRV24a|   TTATTCACATATACTAGATTTGACTCTGAGATTACAATAG-TTCCATCCATAGCTGGCAA
1559  62_HRV24b|   TTATTCACATATACTAGATTTGACTCTGAGATTACAATAG-TTCCATCCATAGCTGGCAA
1560  63_HRV24     TTATTCACATATACTAGATTTGACTCTGAGATTACAATAG-TTCCATCCATAGCTGGCAA
1561  64_HRV90     TTGTTTACATATGCTAGATTTGATTCTGAAATTACAATAG-TACCATCTATAGCTGGCAA
1562  65_HRV90a|   TTGTTTACATATGCTAGATTTGATTCTGAAATTACAATAG-TACCATCTATAGCTGGCAA
1563  66_HRV90b|   TTGTTTACATATGCTAGATTTGATTCTGAAATTACAATAG-TACCATCTATAGCTGGCAA
1564  67_HRV34     ATGTTCACCTACGTCAGATTTGATTCTGAAGTCACCCTAG-TACCATCAATAGCGGCCAA
1565  68_HRV34b|   ATGTTCACCTACGTCAGATTTGATTCTGAAGTCACCCTAG-TACCATCAATAGCGGCCAA
1566  69_HRV34a|   ATGTTCACCTACGTCAGATTTGATTCTGAAGTCACCCTAG-TACCATCAATAGCGGCCAA
1567  70_HRV50a|   ATGTTCACCTATGTGAGGTTTAATTCTGAGGTCACATTAG-TACCATCCATAGCTGCCAA
1568  71_HRV50b|   ATGTTCACCTATGTGAGGTTTAATTCTGAGGTCACATTAG-TACCATCCATAGCTGCCAA
1569  72_HRV50     ATGTTCACCTATGTGAGGTTTAATTCTGAGGTCACATTAG-TACCATCCATAGCTGCCAA
1570  73_HRV18a|   ATGTTTACATATGTTAGATTTGATTCAGAAATTACACTAG-TACCATCTGTAGCTGCTAA
1571  74_HRV18b|   ATGTTTACATATGTTAGATTTGATTCAGAAATTACACTAG-TACCATCTGTAGCTGCTAA
1572  75_HRV18     ATGTTTACATATGTTAGATTTGATTCAGAAATTACACTAG-TACCATCTGTAGCTGCTAA
1573  76_HRV55     ATGTTCACCTATACTAGATTTGATTCAGAAGTTACATTAG-TACCCTCTATTGCTGCAAA
1574  77_HRV55b|   ATGTTCACCTATACTAGATTTGATTCAGAAGTTACATTAG-TACCCTCTATTGCTGCAAA
1575  78_HRV55a|   ATGTTCACCTATACTAGATTTGATTCAGAAGTTACATTAG-TACCCTCTATTGCTGCAAA
1576  79_HRV57     CTATTTACATATGTTAGGTTTGATTCTGAAGTTACATTAG-TTCCCTCCATAGCTGCTCA
1577  80_HRV57a|   CTATTTACATATGTTAGGTTTGATTCTGAAGTTACATTAG-TTCCCTCCATAGCTGCTCA
1578  81_HRV57b|   CTATTTACATATGTTAGGTTTGATTCTGAAGTTACATTAG-TTCCCTCCATAGCTGCTCA
1579  82_HRV21     ATGTTCACCTATACTAGATTTGATTCAGAAATAACTTTGG-TGCCGTCAATTGCAGCTAG
1580  83_HRVHan    ATGTTCACCTATACTAGATTTGATTCAGAAATAACTTTGG-TACCGTCAATTGCAGCTAG
1581  84_HRV43     TTGTTCACATACTTAAGGTTTGATTCTGAAATTACCCTTG-TTCCTTGCATTGCAGCAAA
1582  85_HRV43b|   TTGTTCACATACTTAAGGTTTGATTCTGAAATTACCCTTG-TTCCTTGCATTGCAGCAAA
1583  86_HRV43a|   TTGTTCACATACTTAAGGTTTGATTCTGAAATTACCCTTG-TTCCTTGCATTGCAGCAAA
1584  87_HRV75     TTATTTACATATCTTAGATTTGATTCAGAGGTTACTCTGG-TGCCATGCATTGCAGCTAA
1585  88_HRV75b|   TTATTTACATATCTTAGATTTGATTCAGAGGTTACTCTGG-TGCCATGCATTGCAGCTAA
1586  89_HRV75a|   TTATTTACATATCTTAGATTTGATTCAGAGGTTACTCTGG-TGCCATGCATTGCAGCTAA
1587  96_HRV9a|d   TTGTTTACATATGCAAGATTTGACTCTGAAATAACATTGG-TCCCGTGTATAGCAGCAGA
1588  97_HRV9b|d   TTGTTTACATATGCAAGATTTGACTCTGAAATAACATTGG-TCCCGTGTATAGCAGCAGA
1589  98_HRV9      TTGTTTACATATGCAAGATTTGACTCTGAAATAACATTGG-TCCCGTGTATAGCAGCAGA
1590  99_HRV32     TTGTTTACACACAAGGTTTGATTCTGAAATAACATTAG-TACCTTGTATAGCTGCAGA
1591  100_HRV32a   TTGTTTACACACAAGGTTTGATTCTGAAATAACATTAG-TACCTTGTATAGCTGCAGA
1592  101_HRV32b   TTGTTTACACACAAGGTTTGATTCTGAAATAACATTAG-TACCTTGTATAGCTGCAGA
1593  102_HRV67    CTATTCACATATACAAGATTTGATTCTGAGATAACACTGG-TACCATGCATAGCTGCAGA
1594  103_HRV67a   CTATTCACATATACAAGATTTGATTCTGAGATAACACTGG-TACCATGCATAGCTGCAGA
1595  104_HRV67b   CTATTCACATATACAAGATTTGATTCTGAGATAACACTGG-TACCATGCATAGCTGCAGA
1596  105_HRV15    TTATTCACATATGTAAGGTTTGATTCAGAAATAACACTTG-TACCATGCATTGCAGCAAA
1597  106_HRV15a   TTATTCACATATGTAAGGTTTGATTCAGAAATAACACTTG-TACCATGCATTGCAGCAAA
1598  107_HRV15b   TTATTCACATATGTAAGGTTTGATTCAGAAATAACACTTG-TACCATGCATTGCAGCAAA
1599  108_HRV74a   TTGTTCACATATGTTAGATTTGACTCAGAAGTGACATTAG-TTCCATGCATTGCTGCTAA
1600  109_HRV74b   TTGTTCACATATGTTAGATTTGACTCAGAAGTGACATTAG-TTCCATGCATTGCTGCTAA
1601  110_HRV74    TTGTTCACATATGTTAGATTTGACTCAGAAGTGACATTAG-TTCCATGCATTGCTGCTAA
1602  111_HRV38a   ATGTTTACATATGTGAGATTTGATTCAGAAGTTACATTAG-TCCCATGTATAGCAGCACA
1603  112_HRV38b   ATGTTTACATATGTGAGATTTGATTCAGAAGTTACATTAG-TCCCATGTATAGCAGCACA
1604  113_HRV38    ATGTTTACATATGTGAGATTTGATTCAGAAGTTACATTAG-TCCCATGTATAGCAGCACA
1605  114_HRV60    TTATTTACATATGTAAGATTTGATTCAGAATTGACTCTGG-TCCCATGCATAGCAGCAAA
1606  115_HRV60a   TTATTTACATATGTAAGATTTGATTCAGAATTGACTCTGG-TCCCATGCATAGCAGCAAA
1607  116_HRV60b   TTATTTACATATGTAAGATTTGATTCAGAATTGACTCTGG-TCCCATGCATAGCAGCAAA
1608  117_HRV64a   TTATTTACATATGTTAGATTTGATTCTGAAATAACCTTAG-TGCCTTGCATATCTTCTCA
1609  118_HRV64b   TTATTTACATATGTTAGATTTGATTCTGAAATAACCTTAG-TGCCTTGCATATCTTCTCA
1610  119_HRV64    TTATTTACATATGTTAGATTTGATTCTGAAATAACCTTAG-TGCCTTGCATATCTTCTCA
1611  120_HRV94a   CTATTTACTTATGTTAGATTTGATTCAGAAATAACTTTAG-TACCTTGCATATCATCTCA
1612  121_HRV94b   CTATTTACTTATGTTAGATTTGATTCAGAAATAACTTTAG-TACCTTGCATATCATCTCA
1613  122_HRV94    CTATTTACTTATGTTAGATTTGATTCAGAAATAACTTTAG-TACCTTGCATATCATCTCA
1614  123_HRV22    CTATTTACATATCTCAGGTTTGATTCTGAAATCACTTTGG-TACCATGCATTGCTTCACA
1615  124_HRV22a   CTATTTACATATCTCAGGTTTGATTCTGAAATCACTTTGG-TACCATGCATTGCTTCACA
1616  125_HRV22b   CTATTTACATATCTCAGGTTTGATTCTGAAATCACTTTGG-TACCATGCATTGCTTCACA
1617  126_HRV82    CTTTTCACATATGTGAGATTTGATTCAGAAATTACTTTAG-TGCCTTGCATAGCCTCTCA
1618  127_HRV82b   CTTTTCACATATGTGAGATTTGATTCAGAAATTACTTTAG-TGCCTTGCATAGCCTCTCA
1619  128_HRV82a   CTTTTCACATATGTGAGATTTGATTCAGAAATTACTTTAG-TGCCTTGCATAGCCTCTCA
1620  129_HRV19    CTTTTCACTTACCTCAGATTTGATTCAGAGGTAACATTAG-TCCCTTGCATAGCTGCTAA
```

FIG. D9 CONT'D

```
05.trace                                                                            9/20/2007 5:04 PM 1621 130_HRV19a    CTTTTCACTTACCTCAGATTTGATTCAGAGGTAACATTAG-TCCCTTGCATAGCTGCTAA
1622 131_HRV19b    CTTTTCACTTACCTCAGATTTGATTCAGAGGTAACATTAG-TCCCTTGCATAGCTGCTAA
1623 132_HRV13     TTGTTCACCTATGTAAGATTTGATTCAGAAATAACAATTG-TGCCATGTATAGCCGGGCA
1624 133_HRV13a    TTGTTCACCTATGTAAGATTTGATTCAGAAATAACAATTG-TGCCATGTATAGCCGGGCA
1625 134_HRV13b    TTGTTCACCTATGTAAGATTTGATTCAGAAATAACAATTG-TGCCATGTATAGCCGGGCA
1626 135_HRV41     TTTTTTACGTATGTTAGATTTGACTCAGAAATAACAATTG-TGCCAAGTATAGCTGGACA
1627 136_HRV41a    TTTTTTACGTATGTTAGATTTGACTCAGAAATAACAATTG-TGCCAAGTATAGCTGGACA
1628 137_HRV41b    TTTTTTACGTATGTTAGATTTGACTCAGAAATAACAATTG-TGCCAAGTATAGCTGGACA
1629 138_HRV73     TTATTCACCTATGTAAGATTTCAGAAGTGACAATTG-TACCATGTATAGCTGGTCA
1630 139_HRV73b    TTATTCACCTATGTAAGATTTGATTCAGAAGTGACAATTG-TACCATGTATAGCTGGTCA
1631 140_HRV73a    TTATTCACCTATGTAAGATTTGATTCAGAAGTGACAATTG-TACCATGTATAGCTGGTCA
1632 141_HRV61     TTGTTCACATATGCTAGATTTGATTCAGAGATTACAATTG-TACCTTGTGTTGCTGGGCA
1633 142_HRV61a    TTGTTCACATATGCTAGATTTGATTCAGAGATTACAATTG-TACCTTGTGTTGCTGGGCA
1634 143_HRV61b    TTGTTCACATATGCTAGATTTGATTCAGAGATTACAATTG-TACCTTGTGTTGCTGGGCA
1635 144_HRV96     CTGTTCACTTATGCTAGATTTGATTCAGAGATAACAATTG-TTCCATGTGTTGCTGTGCA
1636 145_HRV96b    CTGTTCACTTATGCTAGATTTGATTCAGAGATAACAATTG-TTCCATGTGTTGCTGTGCA
1637 146_HRV96a    CTGTTCACTTATGCTAGATTTGATTCAGAGATAACAATTG-TTCCATGTGTTGCTGTGCA
1638 90_HRV16a|    ATGTTTACTTATGCAAGATTTGACTCTGAAATTACTATGG-TACCAAGTGTAGCAGCCAA
1639 91_HRV16b|    ATGTTTACTTATGCAAGATTTGACTCTGAAATTACTATGG-TACCAAGTGTAGCAGCCAA
1640 92_1AYM_A     ATGTTTACTTATGCAAGATTTGACTCTGAAATTACTATGG-TACCAAGTGTAGCAGCCAA
1641 93_HRV81a|    ATGTTCACATACACTAGATTTAACTCTGAGATTACACTGG-TACCAAGTATTGCAAACAA
1642 94_HRV81b|    ATGTTCACATACACTAGATTTAACTCTGAGATTACACTGG-TACCAAGTATTGCAAACAA
1643 95_HRV81      ATGTTCACATACACTAGATTTAACTCTGAGATTACACTGG-TACCAAGTATTGCAAACAA
1644 147_HRV2      TTGTTCACCTATACTAGGTTTGATTCTGAAATAACCCTAG-TTCCATGCATTTCCGCCCT
1645 148_HRV2a|    TTGTTCACCTATACTAGGTTTGATTCTGAAATAACCCTAG-TTCCATGCATTTCCGCCCT
1646 149_HRV2b|    TTGTTCACCTATACTAGGTTTGATTCTGAAATAACCCTAG-TTCCATGCATTTCCGCCCT
1647 150_HRV49a    CTGTTTACTTACACTAGATTCGATTCTGAAATAACCTTGG-TTCCATGCATTTCTGCACT
1648 151_HRV49b    CTGTTTACTTACACTAGATTCGATTCTGAAATAACCTTGG-TTCCATGCATTTCTGCACT
1649 152_HRV49     CTGTTTACTTACACTAGATTCGATTCTGAAATAACCTTGG-TTCCATGCATTTCTGCACT
1650 153_HRV23a    CTGTTTACTTACACTAGATTTGATTCTGAAATTACTTTGG-TTCCATGCATTTCTGCTCT
1651 154_HRV23b    CTGTTTACTTACACTAGATTTGATTCTGAAATTACTTTGG-TTCCATGCATTTCTGCTCT
1652 155_HRV23     CTGTTTACTTACACTAGATTTGATTCTGAAATTACTTTGG-TTCCATGCATTTCTGCTCT
1653 156_HRV30a    CTATTCACTTACACTAGATTTGATTCTGAGATAACCTTGG-TTCCGTGTATTTCAGCTCT
1654 157_HRV30b    CTATTCACTTACACTAGATTTGATTCTGAGATAACCTTGG-TTCCGTGTATTTCAGCTCT
1655 158_HRV30     CTATTCACTTACACTAGATTTGATTCTGAGATAACCTTGG-TTCCGTGTATTTCAGCTCT
1656 159_HRV7      CTATTCACATACACTAGATTTGATTCTGAGATAACAATAG-TCACAGCAGCAGCAGCACA
1657 160_HRV7b|    CTATTCACATACACTAGATTTGATTCTGAGATAACAATAG-TCACAGCAGCAGCAGCACA
1658 161_HRV7a|    CTATTCACATACACTAGATTTGATTCTGAGATAACAATAG-TCACAGCAGCAGCAGCACA
1659 162_HRV88     TTGTTTACATACACTAGATTTGACTCAGAAATAACAATAG-TCACAGCAGCTGCAGCACA
1660 163_HRV88a    TTGTTTACATACACTAGATTTGACTCAGAAATAACAATAG-TCACAGCAGCTGCAGCACA
1661 164_HRV88b    TTGTTTACATACACTAGATTTGACTCAGAAATAACAATAG-TCACAGCAGCTGCAGCACA
1662 165_HRV36a    TTGTTTACATACACAAGATTTGACTCAGAAATAACAATAG-TCACCGCAGCTGCAGTGCA
1663 166_HRV36b    TTGTTTACATACACAAGATTTGACTCAGAAATAACAATAG-TCACCGCAGCTGCAGTGCA
1664 167_HRV36     TTGTTTACATACACAAGATTTGACTCAGAAATAACAATAG-TCACCGCAGCTGCAGTGCA
1665 168_HRV89a    TTATTCACATATACAAGATTTGATTCAGAGATAACAATAG-TCACTGCAGCCCGCAGCTCA
1666 169_HRV89b    TTATTCACATATACAAGATTTGATTCAGAGATAACAATAG-TCACTGCAGCCCGCAGCTCA
1667 170_HRV89     TTATTCACATATACAAGATTTGATTCAGAGATAACAATAG-TCACTGCAGCCCGCAGCTCA
1668 171_HRV58     TTGTTTACATATACAAGATTTGACTCAGAGATTACAATAG-TCACTGCAGCAGCTGCTCA
1669 172_HRV58a    TTGTTTACATATACAAGATTTGACTCAGAGATTACAATAG-TCACTGCAGCAGCTGCTCA
1670 173_HRV58b    TTGTTTACATATACAAGATTTGACTCAGAGATTACAATAG-TCACTGCAGCAGCTGCTCA
1671 174_HRV12a    CTTTTCACCTACTTAAGGTTTGATTCTGAAATCACCATTGTTCCAAGCAATG-CAGCAAT
1672 175_HRV12b    CTTTTCACCTACTTAAGGTTTGATTCTGAAATCACCATTGTTCCAAGCAATG-CAGCAAT
1673 176_HRV12     CTTTTCACCTACTTAAGGTTTGATTCTGAAATCACCATTGTTCCAAGCAATG-CAGCAAT
1674 177_HRV78a    ATGTTCACATATCTCAGATTTGATTCAGAAATCACTCTTG-TGTGTGCAGTGGCCTCACA
1675 178_HRV78b    ATGTTCACATATCTCAGATTTGATTCAGAAATCACTCTTG-TGTGTGCAGTGGCCTCACA
1676 179_HRV78     ATGTTCACATATCTCAGATTTGATTCAGAAATCACTCTTG-TGTGTGCAGTGGCCTCACA
1677 180_HRV20     CTCTTTACATACCTCAGATTTGATTCTGAGATTACAATAG-TAGCAACAGTAGCTGCACT
1678 181_HRV20a    CTCTTTACATACCTCAGATTTGATTCTGAGATTACAATAG-TAGCAACAGTAGCTGCACT
1679 182_HRV20b    CTCTTTACATACCTCAGATTTGATTCTGAGATTACAATAG-TAGCAACAGTAGCTGCACT
1680 183_HRV68     CTATTCACATACCTTAGGTTTGACTCTGAGATTACAATAG-TAGCAACAATAGCTGCTCT
1681 184_HRV68a    CTATTCACATACCTTAGGTTTGACTCTGAGATTACAATAG-TAGCAACAATAGCTGCTCT
1682 185_HRV68b    CTATTCACATACCTTAGGTTTGACTCTGAGATTACAATAG-TAGCAACAATAGCTGCTCT
1683 186_HRV28     ATGTTTACATATCTCAGATTTGATTCTGAAATTACTATAG-TGGTGTCAGTTGCAAGTAA
1684 187_HRV28a    ATGTTTACATATCTCAGATTTGATTCTGAAATTACTATAG-TGGTGTCAGTTGCAAGTAA
1685 188_HRV28b    ATGTTTACATATCTCAGATTTGATTCTGAAATTACTATAG-TGGTGTCAGTTGCAAGTAA
```

FIG. D9 CONT'D 05.trace                                                                    9/20/2007 5:04 PM

```
1686 189_HRV53a    ATGTTCACATATCTTAGATTTGATTCAGAAATAACTATAG-TGGTATCAGTGGCTAGTAA
1687 190_HRV53b    ATGTTCACATATCTTAGATTTGATTCAGAAATAACTATAG-TGGTATCAGTGGCTAGTAA
1688 191_HRV53     ATGTTCACATATCTTAGATTTGATTCAGAAATAACTATAG-TGGTATCAGTGGCTAGTAA
1689 192_HRV46a    CTTTTTACATATCTCAGATTTGATTCAGAAATAACAATAG-TCACCACATTGGCAGGCCA
1690 193_HRV46b    CTTTTTACATATCTCAGATTTGATTCAGAAATAACAATAG-TCACCACATTGGCAGGCCA
1691 194_HRV46     CTTTTTACATATCTCAGATTTGATTCAGAAATAACAATAG-TCACCACATTGGCAGGCCA
1692 195_HRV80a    CTTTTCACTTACCTCAGATTTGACTCAGAAATAACAATAG-TAACTACCTTAGCAGGACA
1693 196_HRV80b    CTTTTCACTTACCTCAGATTTGACTCAGAAATAACAATAG-TAACTACCTTAGCAGGACA
1694 197_HRV80     CTTTTCACTTACCTCAGATTTGACTCAGAAATAACAATAG-TAACTACCTTAGCAGGACA
1695 198_HRV51     CTTTTCACATACTTAAGATTTGATTCAGAGATCACTATAG-TTGCTACCATTGCTGGACA
1696 199_HRV51a    CTTTTCACATACTTAAGATTTGATTCAGAGATCACTATAG-TTGCTACCATTGCTGGACA
1697 200_HRV51b    CTTTTCACATACTTAAGATTTGATTCAGAGATCACTATAG-TTGCTACCATTGCTGGACA
1698 201_HRV65a    CTCTTCACCTATTTGCGCTTTGACTCAGAAATTACCATAG-TGGCTACTATAGCTGGACA
1699 202_HRV65b    CTCTTCACCTATTTGCGCTTTGACTCAGAAATTACCATAG-TGGCTACTATAGCTGGACA
1700 203_HRV65     CTCTTCACCTATTTGCGCTTTGACTCAGAAATTACCATAG-TGGCTACTATAGCTGGACA
1701 204_HRV71a    CTCTTCACATACCTGCGCTTTGATTCAGAGATAACAATTG-TAGCTACACTAGCAGGGCA
1702 205_HRV71b    CTCTTCACATACCTGCGCTTTGATTCAGAGATAACAATTG-TAGCTACACTAGCAGGGCA
1703 206_HRV71     CTCTTCACATACCTGCGCTTTGATTCAGAGATAACAATTG-TAGCTACACTAGCAGGGCA
1704 207_HRV8      ATGTTCACTTATGTAAGATTTGATTCAGAGATAACAATTG-TACCATGTATTGCAGCTAT
1705 208_HRV95     ATGTTCACTTATGTAAGATTTGATTCAGAGATAACAATTG-TACCATGTATTGCAGCTAT
1706 209_HRV45     ATGTTTACATATGTCAGATTTGATTCCGAAATAACAATAG-TACCATGTGTTGCTGCCAC
1707 210_HRV45a    ATGTTTACATATGTCAGATTTGATTCCGAAATAACAATAG-TACCATGTGTTGCTGCCAC
1708 211_HRV45b    ATGTTTACATATGTCAGATTTGATTCCGAAATAACAATAG-TACCATGTGTTGCTGCCAC
1709 GROUP_1       -T-TT-AC-TA-----G-TT--A-TC-GA--T-AC--T-G-T-----------C------
1710
1711  1_HRV1A1|d   AGGAGACGACATTGGACATATTGTAATGCAATATATGTATGTTCCTCCAGGAGCTCCAAT
1712  2_HRV1A2|d   AGGAGACGACATTGGACATATTGTAATGCAATATATGTATGTTCCTCCAGGAGCTCCAAT
1713  3_HRV1A|cD   AGGAGACGACATTGGACATATTGTAATGCAATATATGTATGTTCCTCCAGGAGCTCCAAT
1714  4_HRV1B1|d   AGGAGATGACATTGGTCATGTTGTAATGCAGTATATGTATGTTCCCCAGGAGCTCCAAT
1715  5_HRV1B2|d   AGGAGATGACATTGGTCATGTTGTAATGCAGTATATGTATGTTCCCCCAGGAGCTCCAAT
1716  6_HRV1B      AGGAGATGACATTGGTCATGTTGTAATGCAGTATATGTATGTTCCCCCAGGAGCTCCAAT
1717  7_HRV40a|d   GGGTGAAGACATTGGACACATTGTGATGCAATATATGTATGTACCCCCTGGCGCACCCAT
1718  8_HRV40b|d   GGGTGAAGACATTGGACACATTGTGATGCAATATATGTATGTACCCCCTGGCGCACCCAT
1719  9_HRV40      GGGTGAAGACATTGGACACATTGTGATGCAATATATGTATGTACCCCCTGGCGCACCCAT
1720 10_HRV85      GGGTGATGATATTGGACACATTGTAATGCAGTATATGTATGTGCCCCCCGGAGCACCAAT
1721 11_HRV85a|    GGGTGATGATATTGGACACATTGTAATGCAGTATATGTATGTGCCCCCCGGAGCACCAAT
1722 12_HRV85b|    GGGTGATGATATTGGACACATTGTAATGCAGTATATGTATGTGCCCCCCGGAGCACCAAT
1723 13_HRV56a|    GGGAGATGATATTGGACACATTGTAATGCAATACATGTATGTGCCTCCTGGTGCACCACT
1724 14_HRV56b|    GGGAGATGATATTGGACACATTGTAATGCAATACATGTATGTGCCTCCTGGTGCACCACT
1725 15_HRV56      GGGAGATGATATTGGACACATTGTAATGCAATACATGTATGTGCCTCCTGGTGCACCACT
1726 16_HRV54      GGGAGTTGATATTGGACACATTGTCATGCAATTCATGTATGTACCGCCTGGTGCACCAAA
1727 17_HRV98      GGGAGCTGACATTGGACACATTGTCATGCAATTCATGTATGTTCCACCTGGCACCCAAT
1728 18_HRV59a|    AGGGGATGACATTGGTCATATAGTCATGCAATATATGTATGTTCCACCAGGTGCTCCACT
1729 19_HRV59b|    AGGGGATGACATTGGTCATATAGTCATGCAATATATGTATGTTCCACCAGGTGCTCCACT
1730 20_HRV59      AGGGGATGACATTGGTCATATAGTCATGCAATATATGTATGTTCCACCAGGTGCTCCACT
1731 21_HRV63      AGGTGATGACATTGGTCATATAGTTATGCAGTACATGTACGTTCCACCCGGTGCCCCTCT
1732 22_HRV63b|    AGGTGATGACATTGGTCATATAGTTATGCAGTACATGTACGTTCCACCCGGTGCCCCTCT
1733 23_HRV63a|    AGGTGATGACATTGGTCATATAGTTATGCAGTACATGTACGTTCCACCCGGTGCCCCTCT
1734 24_HRV39      AGGTGAAGATATTGGACACATAGTAATGCAATACATGTATGTCCCACCTGGTGCACCTGT
1735 25_HRV39a|    AGGTGAAGATATTGGACACATAGTAATGCAATACATGTATGTCCCACCTGGTGCACCTGT
1736 26_HRV39b|    AGGTGAAGATATTGGACACATAGTAATGCAATACATGTATGTCCCACCCGGTGCACCTGT
1737 27_HRV10a|    GGGCGATGACATAGGTCACATAGTTATGCAATATATGTATGTGCCACCTGGGGCTCCAGT
1738 28_HRV10b|    GGGCGATGACATAGGTCACATAGTTATGCAATATATGTATGTGCCACCTGGGGCTCCAGT
1739 29_HRV10      GGGCGATGACATAGGTCACATAGTTATGCAATATATGTATGTGCCACCTGGGGCTCCAGT
1740 30_HRV100a    AGGAGATGACATAGGGCATATCGTAATGCAGTACATGTATGTGCCACCTGGAGCTCCAGT
1741 31_HRV100b    AGGAGATGACATAGGGCATATCGTAATGCAGTACATGTATGTGCCACCTGGAGCTCCAGT
1742 32_HRV100     AGGAGATGACATAGGGCATATCGTAATGCAGTACATGTATGTGCCACCTGGAGCTCCAGT
1743 33_HRV66      GGGTGATGATATAGGACATATTGTGATGCAATACATGTATGTACCACCTGGAGCCCCAAT
1744 34_HRV66b|    GGGTGATGATATAGGACATATTGTGATGCAATACATGTATGTACCACCTGGAGCCCCAAT
1745 35_HRV66a|    GGGTGATGATATAGGACATATTGTGATGCAATACATGTATGTACCACCTGGAGCCCCAAT
1746 36_HRV77a|    AGGTGATGACATAGGACATGTTGTCATGCAATACATGTATGTACCACCAGGGGCACCCAT
1747 37_HRV77b|    AGGTGATGACATAGGACATGTTGTCATGCAATACATGTATGTACCACCAGGGGCACCCAT
1748 38_HRV77      AGGTGATGACATAGGACATGTTGTCATGCAATACATGTATGTACCACCAGGGGCACCCAT
1749 39_HRV62a     TGGTGCAGATATAGGTCACATAGTTATGCAATATATGTATGTACCACCTGGGGCTCCACT
1750 40_HRV62b     TGGTGCAGATATAGGTCACATAGTTATGCAATATATGTATGTACCACCTGGGGCTCCACT
```

FIG. D9 CONT'D

```
05.trace                                                                                         9/20/2007  5:04 PM 1751  41_HRV25      TGGTGCAGATATAGGTCACATAGTTATGCAATATATGTATGTGCCACCTGGAGCCCCATT
1752  42_HRV29a     TGGTAATGATATAGGTCACATAGTTATGCAGTACATGTATGTACCACCTGGAGCTCCAGT
1753  43_HRV29b     TGGTAATGATATAGGTCACATAGTTATGCAGTACATGTATGTACCACCTGGAGCTCCAGT
1754  44_HRV44a     TGGTGATGATATAGGCCACATAGTTATGCAGTACATGTATGTACCACCTGGAGCTCCAGT
1755  45_HRV44b     TGGTGATGATATAGGCCACATAGTTATGCAGTACATGTATGTACCACCTGGAGCTCCAGT
1756  46_HRV31      TGGTAGTGACATAGGCCATATAGTCATGCAATACATGTATGTACCACCTGGGGCCCCAGT
1757  47_HRV31a|    TGGTAGTGACATAGGCCATATAGTCATGCAATACATGTATGTACCACCTGGGGCCCCAGT
1758  48_HRV31b|    TGGTAGTGACATAGGCCATATAGTCATGCAATACATGTATGTACCACCTGGGGCCCCAGT
1759  49_HRV47      TGGTGATGACATAGGTCACATAGTTATGCAATACATGTATGTGCCGCCTGGGGCTCCAGT
1760  50_HRV47a|    TGGTGATGACATAGGTCACATAGTTATGCAATACATGTATGTGCCGCCTGGGGCTCCAGT
1761  51_HRV47b|    TGGTGATGACATAGGTCACATAGTTATGCAATACATGTATGTGCCGCCTGGGGCTCCAGT
1762  52_HRV11      AGGAAATGATATTGGTCATGTTGTAATGCAATATATGTATGTCCCACCAGGTGCTCCAGT
1763  53_HRV11b|    AGGAAATGATATTGGTCATGTTGTAATGCAATATATGTATGTCCCACCAGGTGCTCCAGT
1764  54_HRV11a|    AGGAAATGATATTGGTCATGTTGTAATGCAATATATGTATGTCCCACCAGGTGCTCCAGT
1765  55_HRV76      AGGGGATGACATTGGTCATGTAGTGATGCAATACATGTATGTCCCACCAGGCGCTCCAGT
1766  56_HRV76b|    AGGGGATGACATTGGTCATGTAGTGATGCAATACATGTATGTCCCACCAGGCGCTCCAGT
1767  57_HRV76a|    AGGGGATGACATTGGTCATGTAGTGATGCAATACATGTATGTCCCACCAGGCGCTCCAGT
1768  58_HRV33      GGGAGATGATGTTGGTCATGTTGTAATGCAGTACATGTATGTCCCACCAGGTGCACCAGC
1769  59_HRV33b|    GGGAGATGATGTTGGTCATGTTGTAATGCAGTACATGTATGTCCCACCAGGTGCACCAGC
1770  60_HRV33a|    GGGAGATGATGTTGGTCATGTTGTAATGCAGTACATGTATGTCCCACCAGGTGCACCAGC
1771  61_HRV24a|    GGGAGATGACATTGGACATGTTGTAATGCAGTACATGTATATACCACCTGGAGCACCAGT
1772  62_HRV24b|    GGGAGATGACATTGGACATGTTGTAATGCAGTACATGTATATACCACCTGGAGCACCAGT
1773  63_HRV24      GGGAGATGACATTGGACATGTTGTAATGCAGTACATGTATATACCACCTGGAGCACCAGT
1774  64_HRV90      GGGCAATGATATTGGACATGTTGTGATGCAATACATGTATATACCACCTGGGGCACCAGT
1775  65_HRV90a|    GGGCAATGATATTGGACATGTTGTGATGCAATACATGTATATACCACCTGGGGCACCAGT
1776  66_HRV90b|    GGGCAATGATATTGGACATGTTGTGATGCAATACATGTATATACCACCTGGGGCACCAGT
1777  67_HRV34      AGGTGATGATATTGGACATGTTGTGATGCAATACATGTATGTACCACCAGGTGCACCAAT
1778  68_HRV34b|    AGGTGATGATATTGGACATGTTGTGATGCAATACATGTATGTACCACCAGGTGCACCAAT
1779  69_HRV34a|    AGGTGATGATATTGGACATGTTGTGATGCAATACATGTATGTACCACCAGGTGCACCAAT
1780  70_HRV50a|    GGGTGTTGATATTGGACATGTTGTCATGCAATACATGTATGTCCCACCAGGTGCACCAAT
1781  71_HRV50b|    GGGTGTTGATATTGGACATGTTGTCATGCAATACATGTATGTCCCACCAGGTGCACCAAT
1782  72_HRV50      GGGTGTTGATATTGGACATGTTGTCATGCAATACATGTATGTCCCACCAGGTGCACCAAT
1783  73_HRV18a|    GGGTGATGACATAGGACATATTGTTATGCAGTACATGTATGTTCCTCCAGGAGCACCAAT
1784  74_HRV18b|    GGGTGATGACATAGGACATATTGTTATGCAGTACATGTATGTTCCTCCAGGAGCACCAAT
1785  75_HRV18      GGGTGATGACATAGGACATATTGTTATGCAGTACATGTATGTTCCTCCAGGAGCACCAAT
1786  76_HRV55      GGGAGATGACATTGGACATGTAGTCATGCAATACATGTATGTTCCACCTGGAGCACCAAT
1787  77_HRV55b|    GGGAGATGACATTGGACATGTAGTCATGCAATACATGTATGTTCCACCTGGAGCACCAAT
1788  78_HRV55a|    GGGAGATGACATTGGACATGTAGTCATGCAATACATGTATGTTCCACCTGGAGCACCAAT
1789  79_HRV57      AGGTGAGGATATAGGCCATGTTGTAATGCAATACATGTATGTCCCTCCTGGGGCACCAAT
1790  80_HRV57a|    AGGTGAGGATATAGGCCATGTTGTAATGCAATACATGTATGTCCCTCCTGGGGCACCAAT
1791  81_HRV57b|    AGGTGAGGATATAGGCCATGTTGTAATGCAATACATGTATGTCCCTCCTGGGGCACCAAT
1792  82_HRV21      AACGGGTGACATAGGACATGTTGTAATGCAATATATGTATGTCCCACCAGGTGCTCCAAT
1793  83_HRVHan     AGCGGGTGACATAGGACATGTTGTGATGCAATATATGTATGTCCCACCAGGTGCTCCAAT
1794  84_HRV43      AAGCAATGATATAGGCCATGTGGTAATGCAGTACATGTATGTACCACCAGGTGCGCCAAT
1795  85_HRV43b|    AAGCAATGATATAGGCCATGTGGTAATGCAGTACATGTATGTACCACCAGGTGCGCCAAT
1796  86_HRV43a|    AAGCAATGATATAGGCCATGTGGTAATGCAGTACATGTATGTACCACCAGGTGCGCCAAT
1797  87_HRV75      AGGGAATGACATAGGCCATGTAGTAATGCAATATATGTATGTACCACCAGGAGCACCAAT
1798  88_HRV75b|    AGGGAATGACATAGGCCATGTAGTAATGCAATATATGTATGTACCACCAGGAGCACCAAT
1799  89_HRV75a|    AGGGAATGACATAGGCCATGTAGTAATGCAATATATGTATGTACCACCAGGAGCACCAAT
1800  96_HRV9a|d    AAGTGATAGCGTTGGCCATGTTGTTATGCAGTACATGTATGTACCACCAGGGGCACCTTT
1801  97_HRV9b|d    AAGTGATAGCGTTGGCCATGTTGTTATGCAGTACATGTATGTACCACCAGGGGCACCTTT
1802  98_HRV9       AAGTGATAGCGTTGGCCATGTTGTTATGCAGTACATGTATGTACCACCAGGGGCACCTTT
1803  99_HRV32      AAGTGACAGCATTGGTCATGTTGTTATGCAGTACATGTATGTACCACCAGGGGCTCCTCT
1804  100_HRV32a    AAGTGACAGCATTGGTCATGTTGTTATGCAGTACATGTATGTACCACCAGGGGCTCCTCT
1805  101_HRV32b    AAGTGACAGCATTGGTCATGTTGTTATGCAGTACATGTATGTACCACCAGGGGCTCCTCT
1806  102_HRV67     GAGTGACAGCATTGGGCATGTTGTAATGCAATATATGTATGTACCTCCAGGAGCACCATT
1807  103_HRV67a    GAGTGACAGCATTGGGCATGTTGTAATGCAATATATGTATGTACCTCCAGGAGCACCATT
1808  104_HRV67b    GAGTGACAGCATTGGGCATGTTGTAATGCAATATATGTATGTACCTCCAGGAGCACCATT
1809  105_HRV15     GAGTGATAACATCGGTCATGTTGTCATGCAATATATGTATGTTCCTCCGGGAGCCCCTTT
1810  106_HRV15a    GAGTGATAACATCGGTCATGTTGTCATGCAATATATGTATGTTCCTCCGGGAGCCCCTTT
1811  107_HRV15b    GAGTGATAACATCGGTCATGTTGTCATGCAATATATGTATGTTCCTCCGGGAGCCCCTTT
1812  108_HRV74a    AAGTGACAACATTGGCCATGTTGTTATGCAATACATGTATGTCCCCCCAGGAGCACCTTT
1813  109_HRV74b    AAGTGACAACATTGGCCATGTTGTTATGCAATACATGTATGTCCCCCCAGGAGCACCTTT
1814  110_HRV74     AAGTGACAACATTGGCCATGTTGTTATGCAATACATGTATGTCCCCCCAGGAGCACCTTT
1815  111_HRV38a    AAATGAAGGTGTGGGGCATGTTGTTATGCAGTATATGTATGTCCCTCCAGGGGCACCATT
```

FIG. D9 CONT'D 05.trace                                                                 9/20/2007 5:04 PM

```
1816 112_HRV38b   AAATGAAGGTGTGGGGCATGTTGTTATGCAGTATATGTATGTCCCTCCAGGGGCACCATT
1817 113_HRV38    AAATGAAGGTGTGGGGCATGTTGTTATGCAGTATATGTATGTCCCTCCAGGGGCACCATT
1818 114_HRV60    AAATGATGGCATAGGTCATGTTGTCATGCAATACATGTATGTCCCCCCAGGAGCACCATT
1819 115_HRV60a   AAATGATGGCATAGGTCATGTTGTCATGCAATACATGTATGTCCCCCCAGGAGCACCATT
1820 116_HRV60b   AAATGATGGCATAGGTCATGTTGTCATGCAATACATGTATGTCCCCCCAGGAGCACCATT
1821 117_HRV64a   GAGTGCTAACATTGGTCATGTTGTTATGCAATATATGTATGTCCCTCCTGGAGCTCCAAT
1822 118_HRV64b   GAGTGCTAACATTGGTCATGTTGTTATGCAATATATGTATGTCCCTCCTGGAGCTCCAAT
1823 119_HRV64    GAGTGCTAACATTGGTCATGTTGTTATGCAATATATGTATGTCCCTCCTGGAGCTCCAAT
1824 120_HRV94a   AAGTGCTAATATTGGTCATGTTGTCATGCAGTACATGTATGTTCCTCCTGGAGCTCCAAA
1825 121_HRV94b   AAGTGCTAATATTGGTCATGTTGTCATGCAGTACATGTATGTTCCTCCTGGAGCTCCAAA
1826 122_HRV94    AAGTGCTAATATTGGTCATGTTGTCATGCAGTACATGTATGTTCCTCCTGGAGCTCCAAA
1827 123_HRV22    AAGTAAAAACATTGGTCATGTGGTCATGCAATACATGTATGTTCCGCCTGGAGCTCCTAA
1828 124_HRV22a   AAGTAAAAACATTGGTCATGTGGTCATGCAATACATGTATGTTCCGCCTGGAGCTCCTAA
1829 125_HRV22b   AAGTAAAAACATTGGTCATGTGGTCATGCAATACATGTATGTTCCGCCTGGAGCTCCTAA
1830 126_HRV82    AAGTAATGATATTGGGCATGTAGTGATGCAATACATGTATGTCCCACCAGGTGCTCCTAA
1831 127_HRV82b   AAGTAATGATATTGGGCATGTAGTGATGCAATACATGTATGTCCCACCAGGTGCTCCTAA
1832 128_HRV82a   AAGTAATGATATTGGGCATGTAGTGATGCAATACATGTATGTCCCACCAGGTGCTCCTAA
1833 129_HRV19    AAGTAAAAACATTGGACATGTTGTTATGCAATACATGTATGTGCCTCCTGGTGCTCCTAT
1834 130_HRV19a   AAGTAAAAACATTGGACATGTTGTTATGCAATACATGTATGTGCCTCCTGGTGCTCCTAT
1835 131_HRV19b   AAGTAAAAACATTGGACATGTTGTTATGCAATACATGTATGTGCCTCCTGGTGCTCCTAT
1836 132_HRV13    AGGTGGTGATGTCGGACATGTTGTTATGCAATACATGTATGTACCGCCCGGTGCACCCCT
1837 133_HRV13a   AGGTGGTGATGTCGGACATGTTGTTATGCAATACATGTATGTACCGCCCGGTGCACCCCT
1838 134_HRV13b   AGGTGGTGATGTCGGACATGTTGTTATGCAATACATGTATGTACCGCCCGGTGCACCCCT
1839 135_HRV41    GGGTAGTGATGTCGGACATGTTGTCATGCAATACATGTTCGTACCACCTGGCGCACCCCT
1840 136_HRV41a   GGGTAGTGATGTCGGACATGTTGTCATGCAATACATGTTCGTACCACCTGGCGCACCCCT
1841 137_HRV41b   GGGTAGTGATGTCGGACATGTTGTCATGCAATACATGTTCGTACCACCTGGCGCACCCCT
1842 138_HRV73    AAGTGGAGATGTGGGACATGTAGTTATGCAGTATATGTATGTCCCACCTGGAGCCCCTCT
1843 139_HRV73b   AAGTGGAGATGTGGGACATGTAGTTATGCAGTATATGTATGTCCCACCTGGAGCCCCTCT
1844 140_HRV73a   AAGTGGAGATGTGGGACATGTAGTTATGCAGTATATGTATGTCCCACCTGGAGCCCCTCT
1845 141_HRV61    AGGTGGTGACATTGGACACGTGGTCATGCAATACATGTATGTTCCACCTGGTGCACCTAC
1846 142_HRV61a   AGGTGGTGACATTGGACACGTGGTCATGCAATACATGTATGTTCCACCTGGTGCACCTAC
1847 143_HRV61b   AGGTGGTGACATTGGACACGTGGTCATGCAATACATGTATGTTCCACCTGGTGCACCTAC
1848 144_HRV96    GAGTGGTGATATTGGTCATGTGGTCATGCAATATATGTATGTTCCACCAGGTGCCCCCAC
1849 145_HRV96b   GAGTGGTGATATTGGTCATGTGGTCATGCAATATATGTATGTTCCACCAGGTGCCCCCAC
1850 146_HRV96a   GAGTGGTGATATTGGTCATGTGGTCATGCAATATATGTATGTTCCACCAGGTGCCCCCAC
1851  90_HRV16a|  AGATGGTCACATTGGTCATATAGTCATGCAATATATGTATGTACCACCAGGAGCACCTAT
1852  91_HRV16b|  AGATGGTCACATTGGTCATATAGTCATGCAATATATGTATGTACCACCAGGAGCACCTAT
1853  92_1AYM_A   AGATGGTCACATTGGTCATATAGTCATGCAATATATGTATGTACCACCAGGAGCACCTAT
1854  93_HRV81a|  GGAAGGTCATATTGGTCATATAGTAATGCAATACATGTATGTACCACCAGGAGCACCCAT
1855  94_HRV81b|  GGAAGGTCATATTGGTCATATAGTAATGCAATACATGTATGTACCACCAGGAGCACCCAT
1856  95_HRV81    GGAAGGTCATATTGGTCATATAGTAATGCAATACATGTATGTACCACCAGGAGCACCCAT
1857 147_HRV2     TAGTCAGGACATTGGACACATCACAATGCAATACATGTATGTTCCACCTGGTGCACCGGT
1858 148_HRV2a|   TAGTCAGGACATTGGACACATCACAATGCAATACATGTATGTTCCACCTGGTGCACCGGT
1859 149_HRV2b|   TAGTCAGGACATTGGACACATCACAATGCAATACATGTATGTTCCACCTGGTGCACCGGT
1860 150_HRV49a   TAGCAAGGATATTGGACACATTACAATGCAATACATGTATGTGCCGCCAGGTGCACCTGT
1861 151_HRV49b   TAGCAAGGATATTGGACACATTACAATGCAATACATGTATGTGCCGCCAGGTGCACCTGT
1862 152_HRV49    TAGCAAGGATATTGGACACATTACAATGCAATACATGTATGTGCCGCCAGGTGCACCTGT
1863 153_HRV23a   TAGTCAAGATTGGTCACATCACAATGCAGTATATGTATGTCCCACCAGGTGCTCCAAT
1864 154_HRV23b   TAGTCAAGATATTGGTCACATCACAATGCAGTATATGTATGTCCCACCAGGTGCTCCAAT
1865 155_HRV23    TAGTCAAGATATTGGTCACATCACAATGCAGTATATGTATGTCCCACCAGGTGCTCCAAT
1866 156_HRV30a   CAGCCAAGATATCGGACACATTACAATGCAGTATATGTATGTTCCACCTGGCGCTCCAAT
1867 157_HRV30b   CAGCCAAGATATCGGACACATTACAATGCAGTATATGTATGTCCCACCTGGCGCTCCAAT
1868 158_HRV30    CAGCCAAGATATCGGACACATTACAATGCAGTATATGTATGTTCCACCTGGCGCTCCAAT
1869 159_HRV7     AGGTAATGATATTGGACATATAGTTATGCAATTTATGTATGTACCTCCAGGGGCCCCAGT
1870 160_HRV7b|   AGGTAATGATATTGGACATATAGTTATGCAATTTATGTATGTACCTCCAGGGGCCCCAGT
1871 161_HRV7a|   AGGTAATGATATTGGACATATAGTTATGCAATTTATGTATGTACCTCCAGGGGCCCCAGT
1872 162_HRV88    AGGTGATGATACTGGACATATAGTACTGCAATTCATGTATGTGCCTCCAGGTGCACCAAT
1873 163_HRV88a   AGGTGATGATACTGGACATATAGTACTGCAATTCATGTATGTGCCTCCAGGTGCACCAAT
1874 164_HRV88b   AGGTGATGATACTGGACATATAGTACTGCAATTCATGTATGTGCCTCCAGGTGCACCAAT
1875 165_HRV36a   GGGAGATGATAGTGGGCATGTAGTATTACAATTCATGTATGTACCTCCAGGAGCGCCTGT
1876 166_HRV36b   GGGAGATGATAGTGGGCATGTAGTATTACAATTCATGTATGTACCTCCAGGAGCGCCTGT
1877 167_HRV36    GGGAGATGATAGTGGGCATGTAGTATTACAATTCATGTATGTACCTCCAGGAGCGCCTGT
1878 168_HRV89a   AGGAAATGATAGTGGACATATAGTATTGCAATTTATGTATGTACCCCCAGGAGCACCTGT
1879 169_HRV89b   AGGAAATGATAGTGGACATATAGTATTGCAATTTATGTATGTACCCCCAGGAGCACCTGT
1880 170_HRV89    AGGAAATGATAGTGGACATATAGTATTGCAATTTATGTATGTACCCCCAGGAGCACCTGT
```

FIG. D9 CONT'D

```
05.trace                                                                                  9/20/2007 5:04 PM 1881 171_HRV58     AGGAGAAGATAATGGACATATTGTGTTACAATTTATGTATGTACCCCCAGGAGCACCTGT
1882 172_HRV58a    AGGAGAAGATAATGGACATATTGTGTTACAATTTATGTATGTACCCCCAGGAGCACCTGT
1883 173_HRV58b    AGGAGAAGATAATGGACATATTGTGTTACAATTTATGTATGTACCCCCAGGAGCACCTGT
1884 174_HRV12a    AGAAGGAAGCAATGGTCACGTGGTGGTCCAATACATGTATGTACCTCCTGGTGCCCCACT
1885 175_HRV12b    AGAAGGAAGCAATGGTCACGTGGTGGTCCAATACATGTATGTACCTCCTGGTGCCCCACT
1886 176_HRV12     AGAAGGAAGCAATGGTCACGTGGTGGTCCAATACATGTATGTACCTCCTGGTGCCCCACT
1887 177_HRV78a    AGGAGACAATAATGGACATGTGGTGCTTCAATTTATGTTTGTTCCACCTGGAGCCCCTAT
1888 178_HRV78b    AGGAGACAATAATGGACATGTGGTGCTTCAATTTATGTTTGTTCCACCTGGAGCCCCTAT
1889 179_HRV78     AGGAGACAATAATGGACATGTGGTGCTTCAATTTATGTTTGTTCCACCTGGAGCCCCTAT
1890 180_HRV20     AGGTCGGGATAATGGGCATGTTGTTTTACAGTATATGTATGTACCACCAGGGGCACCAAT
1891 181_HRV20a    AGGTCGGGATAATGGGCATGTTGTTTTACAGTATATGTATGTACCACCAGGGGCACCAAT
1892 182_HRV20b    AGGTCGGGATAATGGGCATGTTGTTTTACAGTATATGTATGTACCACCAGGGGCACCAAT
1893 183_HRV68     TGGAAAAGATAATGGCCATGTGGTTTACAGTACATGTATGTGCCGCCAGGGGCACCCAT
1894 184_HRV68a    TGGAAAAGATAATGGCCATGTGGTTTTACAGTACATGTATGTGCCGCCAGGGGCACCCAT
1895 185_HRV68b    TGGAAAAGATAATGGCCATGTGGTTTTACAGTACATGTATGTGCCGCCAGGGGCACCCAT
1896 186_HRV28     AGGTGATGATAATGGGCATGTAGTTATGCAATATATGTATGTACCTCCAGGAGCCCCCAT
1897 187_HRV28a    AGGTGATGATAATGGGCATGTAGTTATGCAATATATGTATGTACCTCCAGGAGCCCCCAT
1898 188_HRV28b    AGGTGATGATAATGGGCATGTAGTTATGCAATATATGTATGTACCTCCAGGAGCCCCCAT
1899 189_HRV53a    ACAAGGGAATAACGGGCACGTGGTGATACAATACATGTATGTACCACCGGGTGCTCCAAT
1900 190_HRV53b    ACAAGGGAATAACGGGCACGTGGTGATACAATACATGTATGTACCACCGGGTGCTCCAAT
1901 191_HRV53     ACAAGGGAATAACGGGCACGTGGTGATACAATACATGTATGTACCACCGGGTGCTCCAAT
1902 192_HRV46a    AGGGGATGATATTGGACATGTGGTCATACAATATATGTATGTGCCTCCTGGTGCTCCATT
1903 193_HRV46b    AGGGGATGATATTGGACATGTGGTCATACAATATATGTATGTGCCTCCTGGTGCTCCATT
1904 194_HRV46     AGGGGATGATATTGGACATGTGGTCATACAATATATGTATGTGCCTCCTGGTGCTCCATT
1905 195_HRV80a    AGGGGAGGACATTGGTCATGTAGTTATTCAATACATGTACGTACCACCAGGGGCCCCGTT
1906 196_HRV80b    AGGGGAGGACATTGGTCATGTAGTTATTCAATACATGTACGTACCACCAGGGGCCCCGTT
1907 197_HRV80     AGGGGAGGACATTGGTCATGTAGTTATTCAATACATGTACGTACCACCAGGGGCCCCGTT
1908 198_HRV51     GGGTGATGACATAGGGCACATTGTACTTCAATACATGTATGTACCCCCTGGAGGACCAGT
1909 199_HRV51a    GGGTGATGACATAGGGCACATTGTACTTCAATACATGTATGTACCCCCTGGAGGACCAGT
1910 200_HRV51b    GGGTGATGACATAGGGCACATTGTACTTCAATACATGTATGTACCCCCTGGAGGACCAGT
1911 201_HRV65a    AGGTGATGACATAGGGCACATAGTGCTTCAATATATGTATGTGCCTCCTGGTGGTCCTGT
1912 202_HRV65b    AGGTGATGACATAGGGCACATAGTGCTTCAATATATGTATGTGCCTCCTGGTGGTCCTGT
1913 203_HRV65     AGGTGATGACATAGGGCACATAGTGCTTCAATATATGTATGTGCCTCCTGGTGGTCCTGT
1914 204_HRV71a    AGGAGATGATTTAGGACATATTGTACTCCAGTACATGTATGTTCCCCCAGGTGGTCCAAT
1915 205_HRV71b    AGGAGATGATTTAGGACATATTGTACTCCAGTACATGTATGTTCCCCCAGGTGGTCCAAT
1916 206_HRV71     AGGAGATGATTTAGGACATATTGTACTCCAGTACATGTATGTTCCCCCAGGTGGTCCAAT
1917 207_HRV8      AAAAGGTGACCTTGGACACATAGTCCTTCAATACATGTATGTTCCCCGGGTGCACCTCT
1918 208_HRV95     AGAAGGTGACCTTGGACACATAGTCCTCCAATACATGTATGTCCCCCGGGTGCACCTCT
1919 209_HRV45     AGAAGGTAACTTGGGACACATTGTTGTGCAATACATGTTTGTACCACCAGGAGCACCTCT
1920 210_HRV45a    AGAAGGTAACTTGGGACACATTGTTGTGCAATACATGTTTGTACCACCAGGAGCACCTCT
1921 211_HRV45b    AGAAGGTAACTTGGGACACATTGTTGTGCAATACATGTTTGTACCACCAGGAGCACCTCT
1922 GROUP_1       ------------GG-CA--T-----T-CA-T---ATGT---T-CC-CC-GG-G--CC---
1923
1924 1_HRV1A1|d    TCCTTCAAAAAGAAACGATTTCTCATGGCAATCAGGCACCAATATGTCAATATTCTGGCA
1925 2_HRV1A2|d    TCCTTCAAAAAGAAACGATTTCTCATGGCAATCAGGCACCAATATGTCAATATTCTGGCA
1926 3_HRV1A|cD    TCCTTCAAAAAGAAACGATTTCTCATGGCAATCAGGCACCAATATGTCAATATTCTGGCA
1927 4_HRV1B1|d    TCCAAAAACAAGAAATGATTTCTCATGGCAATCAGGCACTAATATGTCAATATTCTGGCA
1928 5_HRV1B2|d    TCCAAAAACAAGAAATGATTTCTCATGGCAATCAGGCACTAATATGTCAATATTCTGGCA
1929 6_HRV1B       TCCAAAAACAAGAAATGATTTCTCATGGCAATCAGGCACTAATATGTCAATATTCTGGCA
1930 7_HRV40a|d    ACCAAAGAAAAGAAATGATTACACATGGCAGTCAGGCACTAATGCTTCTGTATTCTGGCA
1931 8_HRV40b|d    ACCAAAGAAAAGAAATGATTACACATGGCAGTCAGGCACTAATGCTTCTGTATTCTGGCA
1932 9_HRV40       ACCAAAGAAAAGAAATGATTACACATGGCAGTCAGGCACTAATGCTTCTGTATTCTGGCA
1933 10_HRV85      ACCAAGGAAAAGAGATGATTACACATGGCAATCAGGTACTAATGCTTCCGTGTTTTGGCA
1934 11_HRV85a|    ACCAAGGAAAAGAGATGATTACACATGGCAATCAGGTACTAATGCTTCCGTGTTTTGGCA
1935 12_HRV85b|    ACCAAGGAAAAGAGATGATTACACATGGCAATCAGGTACTAATGCTTCCGTGTTTTGGCA
1936 13_HRV56a|    TCCAAACTCAAGAGATGATTTTACATGGCAATCTGGCACCAATGCTTCTGTCTTTTGGCA
1937 14_HRV56b|    TCCAAACTCAAGAGATGATTTTACATGGCAATCTGGCACCAATGCTTCTGTCTTTTGGCA
1938 15_HRV56      TCCAAACTCAAGAGATGATTTTACATGGCAATCTGGCACCAATGCTTCTGTCTTTTGGCA
1939 16_HRV54      ACCAGAAAAAGGAATGATTACACCTGGGAGTCAAGCACAAACCCTTCTATATTTTGGCA
1940 17_HRV98      ACCTAAAAGAGGAATGATTATACTTGGGAATCAAGCACAAACCCTTCTATATTCTGGCA
1941 18_HRV59a|    GCCCACAAAGAGAGATGATTACACATGGCAATCTGGTACTAATGCTTCAATATTCTGGCA
1942 19_HRV59b|    GCCCACAAAGAGAGATGATTACACATGGCAATCTGGTACTAATGCTTCAATATTCTGGCA
1943 20_HRV59      GCCCACAAAGAGAGATGATTACACATGGCAATCTGGTACTAATGCTTCAATATTCTGGCA
1944 21_HRV63      ACCCACCCGAAGAGAAGATTACACATGGCAATCTGGCACTAATGCTTCAATATTCTGGCA
1945 22_HRV63b|    ACCCACCCGAAGAGAAGATTACACATGGCAATCTGGCACTAATGCTTCAATATTCTGGCA
```

FIG. D9 CONT'D

05.trace                                                                                                                    9/20/2007 5:04 PM

```
1946  23_HRV63a|   ACCCACCCGAAGAGAAGATTACACATGGCAATCTGGCACTAATGCTTCAATATTCTGGCA
1947  24_HRV39     ACCTAAGAAGAGAGATGATTACACATGGCAATCTGGAACAAATGCCTCAGTTTTCTGGCA
1948  25_HRV39a|   ACCTAAGAAGAGAGATGATTACACATGGCAATCTGGAACAAATGCCTCAGTTTTCTGGCA
1949  26_HRV39b|   ACCTAAGAAGAGAGATGATTACACATGGCAATCTGGAACAAATGCCTCAGTTTTCTGGCA
1950  27_HRV10a|   ACCAACTAAGAGAGATGATTTTGCTTGGCAGTCGGGAACAAATGCATCAGTCTTCTGGCA
1951  28_HRV10b|   ACCAACTAAGAGAGATGATTTTGCTTGGCAGTCGGGAACAAATGCATCAGTCTTCTGGCA
1952  29_HRV10     ACCAACTAAGAGAGATGATTTTGCTTGGCAGTCGGGAACAAATGCATCAGTCTTCTGGCA
1953  30_HRV100a   TCCAACAAAAAGGGATGATTTTGCATGGCAATCAGGCACAAATGCATCAGTTTTTTGGCA
1954  31_HRV100b   TCCAACAAAAAGGGATGATTTTGCATGGCAATCAGGCACAAATGCATCAGTTTTTTGGCA
1955  32_HRV100    TCCAACAAAAAGGGATGATTTTGCATGGCAATCAGGCACAAATGCATCAGTTTTTTGGCA
1956  33_HRV66     TCCAGATAATAGAACACACTTTGCTTGGCAATCAGGAACAAATGCATCTATATTCTGGCA
1957  34_HRV66b|   TCCAGATAATAGAACACACTTTGCTTGGCAATCAGGAACAAATGCATCTATATTCTGGCA
1958  35_HRV66a|   TCCAGATAATAGAACACACTTTGCTTGGCAATCAGGAACAAATGCATCTATATTCTGGCA
1959  36_HRV77a|   ACCAGATAGCAGGACTCATTTTGCATGGCAGTCAGGGACTAATGCATCAATATTCTGGCA
1960  37_HRV77b|   ACCAGATAGCAGGACTCATTTTGCATGGCAGTCAGGGACTAATGCATCAATATTCTGGCA
1961  38_HRV77     ACCAGATAGCAGGACTCATTTTGCATGGCAGTCAGGGACTAATGCATCAATATTCTGGCA
1962  39_HRV62a    ACCAACAGACAGAAAGCATTTTGCCTGGCAATCAAGTACTAATGCATCAATATTTTGGCA
1963  40_HRV62b    ACCAACAGACAGAAAGCATTTTGCCTGGCAATCAAGTACTAATGCATCAATATTTTGGCA
1964  41_HRV25     ACCAACAGACAGAAAACACTTTGCCTGGCAATCAAGTACTAATGCATCAATATTTTGGCA
1965  42_HRV29a    ACCAAATGACAGAAATCATTTTGCATGGCAATCAGGGACTAATGCATCAATATTCTGGCA
1966  43_HRV29b    ACCAAATGACAGAAATCATTTTGCATGGCAATCAGGGACTAATGCATCAATATTCTGGCA
1967  44_HRV44a    ACCAGATGACAGAAACCACTTTGCATGGCAATCGGGGACTAATGCATCAATATTCTGGCA
1968  45_HRV44b    ACCAGATGACAGAAATCCACTTTGCATGGCAATCGGGGAATAATGCATCAATATTCTGGCA
1969  46_HRV31     ACCAACAAATAGAAAACATTTTGCATGGCAATCAGGTACTAATGCATCGATTTTCTGGCA
1970  47_HRV31a|   ACCAACAAATAGAAAACATTTTGCATGGCAATCAGGTACTAATGCATCGATTTTCTGGCA
1971  48_HRV31b|   ACCAACAAATAGAAAACATTTTGCATGGCAATCAGGTACTAATGCATCGATTTTCTGGCA
1972  49_HRV47     GCCAACAAGTAGAGAGCACTTTGCATGGCAGTCAGGTACCAATGCATCAACTTTCTGGCA
1973  50_HRV47a|   GCCAACAAGTAGAGAGCACTTTGCATGGCAGTCAGGTACCAATGCATCAACTTTCTGGCA
1974  51_HRV47b|   GCCAACAAGTAGAGAGCACTTTGCATGGCAGTCAGGTACCAATGCATCAATTTTCTGGCA
1975  52_HRV11     TCCAGAGAAAAGAGATGATTATACATGGCAATCAGGAACAAATGCATCTATTTTCTGGCA
1976  53_HRV11b|   TCCAGAGAAAAGAGATGATTATACATGGCAATCAGGAACAAATGCATCTATTTTCTGGCA
1977  54_HRV11a|   TCCAGAGAAAAGAGATGATTATACATGGCAATCAGGAACAAATGCATCTATTTTCTGGCA
1978  55_HRV76     TCCAAAGAAGAGAGATGACTACACATGGCAGTCAGGAACCAATGCATCTATTTTCTGGCA
1979  56_HRV76b|   TCCAAAGAAGAGAGATGACTACACATGGCAGTCAGGAACCAATGCATCTATTTTCTGGCA
1980  57_HRV76a|   TCCAAAGAAGAGAGATGACTACACATGGCAGTCAGGAACCAATGCATCTATTTTCTGGCA
1981  58_HRV33     TCCAGAAAAGAGAGATGATTACACATGGCAATCAGGAACAAATGCATCTGTCTTTTGGCA
1982  59_HRV33b|   TCCAGAAAAGAGAGATGATTACACATGGCAATCAGGAACAAATGCATCTGTCTTTTGGCA
1983  60_HRV33a|   TCCAGAAAAGAGAGATGATTACACATGGCAATCAGGAACAAATGCATCTGTCTTTTGGCA
1984  61_HRV24a|   CCCAACAAAGAGAGATGATTATACATGGCAATCAGGAACAAATGCATCTGTCTTTTGGCA
1985  62_HRV24b|   CCCAACAAAGAGAGATGATTATACATGGCAATCAGGAACAAATGCATCTGTCTTTTGGCA
1986  63_HRV24     CCCAACAAAGAGAGATGATTATACATGGCAATCAGGAACAAATGCATCTGTCTTTTGGCA
1987  64_HRV90     ACCTGAGAAGAGGGATGATTATGCATGGCAATCAGGCACTAATGCATCTATCTTTTGGCA
1988  65_HRV90a|   ACCTGAGAAGAGGGATGATTATGCATGGCAATCAGGCACTAATGCATCTATCTTTTGGCA
1989  66_HRV90b|   ACCTGAGAAGAGGGATGATTATGCATGGCAATCAGGCACTAATGCATCTATCTTTTGGCA
1990  67_HRV34     ACCTAAAACTAGAGATGATTTTGCATGGCAATCTGGAACAAATGCCTCAATATTTTGGCA
1991  68_HRV34b|   ACCTAAAACTAGAGATGATTTTGCATGGCAATCTGGAACAAATGCCTCAATATTTTGGCA
1992  69_HRV34a|   ACCTAAAACTAGAGATGATTTTGCATGGCAATCTGGAACAAATGCCTCAATATTTTGGCA
1993  70_HRV50a|   ACCCAAGACTAGGGATGATTTTGCCTGGCAATCTGGAACTAATGCTTCAATCTTTTGGCA
1994  71_HRV50b|   ACCCAAGACTAGGGATGATTTTGCCTGGCAATCTGGAACTAATGCTTCAATCTTTTGGCA
1995  72_HRV50     ACCCAAGACTAGGGATGATTTTGCCTGGCAATCTGGAACTAATGCTTCAATCTTTTGGCA
1996  73_HRV18a|   ACCAAAAACCAGAGATGATTTTGCCTGGCAATCTGGAACAAATGCATCAATCTTCTGGCA
1997  74_HRV18b|   ACCAAAAACCAGAGATGATTTTGCCTGGCAATCTGGAACAAATGCATCAATCTTCTGGCA
1998  75_HRV18     ACCAAAAACCAGAGATGATTTTGCCTGGCAATCTGGAACAAATGCATCAATCTTCTGGCA
1999  76_HRV55     TCCAAAGACAAGAGAAGATTATGCTTGGCAATCAGGGACCAATGCATCTATCTTTTGGCA
2000  77_HRV55b|   TCCAAAGACAAGAGAAGATTATGCTTGGCAATCAGGGACCAATGCATCTATCTTTTGGCA
2001  78_HRV55a|   TCCAAAGACAAGAGAAGATTATGCTTGGCAATCAGGGACCAATGCATCTATCTTTTGGCA
2002  79_HRV57     TCCAAAAACAAGAGAGGATTATACATGGCAATCTGGTACCAATGCTTCAATATTTTGGCA
2003  80_HRV57a|   TCCAAAAACAAGAGAGGATTATACATGGCAATCTGGTACCAATGCTTCAATATTTTGGCA
2004  81_HRV57b|   TCCAAAAACAAGAGAGGATTATACATGGCAATCTGGTACCAATGCTTCAATATTTTGGCA
2005  82_HRV21     TCCAAAAACTAGGGAAGATTTTGCTTGGCAGTCAGGCACTAATGCATCCATTTTCTGGCA
2006  83_HRVHan    TCCAAAAACTAGGGAAGATTTTGCTTGGCAGTCAGGGACTAATGCATCCATTTTCTGGCA
2007  84_HRV43     TCCAAAAACTAGGAAAGATTATGCATGGCAATCTGGCACAAATGCATCTGTTTTCTGGCA
2008  85_HRV43b|   TCCAAAAACTAGGAAAGATTATGCATGGCAATCTGGCACAAATGCATCTGTTTTCTGGCA
2009  86_HRV43a|   TCCAAAAACTAGGAAAGATTATGCATGGCAATCTGGCACAAATGCATCTGTTTTCTGGCA
2010  87_HRV75     ACCAACAACTAGAAAAGATTATGCATGGCAATCTGGAACAAATGCATCTGTATTTTGGCA
```

FIG. D9 CONT'D

```
05.trace                                                                          9/20/2007 5:04 PM 2011 88_HRV75b|   ACCAACAACTAGAAAAGATTATGCATGGCAATCTGGAACAAATGCATCTGTATTTTGGCA
2012 89_HRV75a|   ACCAACAACTAGAAAAGATTATGCATGGCAATCTGGAACAAATGCATCTGTATTTTGGCA
2013 96_HRV9a|d  ACCAAGGACTAGAGATGATTATGCATGGCAATCAGGCACAAATGCTTCCATCTTTTGGCA
2014 97_HRV9b|d  ACCAAGGACTAGAGATGATTATGCATGGCAATCAGGCACAAATGCTTCCATCTTTTGGCA
2015 98_HRV9     ACCAAGGACTAGAGATGATTATGCATGGCAATCAGGCACAAATGCTTCCATCTTTTGGCA
2016 99_HRV32    ACCACAAGCAAGAGATGACTACACATGGCAATCTGGCACGAATGCATCTATCTTTTGGCA
2017 100_HRV32a  ACCACAAGCAAGAGATGACTACACATGGCAATCTGGCACGAATGCATCTATCTTTTGGCA
2018 101_HRV32b  ACCACAAGCAAGAGATGACTACACATGGCAATCTGGCACGAATGCATCTATCTTTTGGCA
2019 102_HRV67   ACCAACAAAAGAGATGACTACACATGGCAATCAGGTACAAATGCATCCATCTTTTGGCA
2020 103_HRV67a  ACCAACAAAAGAGATGACTACACATGGCAATCAGGTACAAATGCATCCATCTTTTGGCA
2021 104_HRV67b  ACCAACAAAAGAGATGACTACACATGGCAATCAGGTACAAATGCATCCATCTTTTGGCA
2022 105_HRV15   ACCCAATAAAAGGAATGATTACACATGGCAATCAGGTACAAATGCCTCTGTTTTCTGGCA
2023 106_HRV15a  ACCCAATAAAAGGAATGATTACACATGGCAATCAGGTACAAATGCCTCTGTTTTCTGGCA
2024 107_HRV15b  ACCCAATAAAAGGAATGATTACACATGGCAATCAGGTACAAATGCCTCTGTTTTCTGGCA
2025 108_HRV74a  ACCCAAGAAAAGAGATGATTACACATGGCAATCTGGCACAAATGCATCTGTGTTTTGGCA
2026 109_HRV74b  ACCCAAGAAAAGAGATGATTACACATGGCAATCTGGCACAAATGCATCTGTGTTTTGGCA
2027 110_HRV74   ACCCAAGAAAAGAGATGATTACACATGGCAATCTGGCACAAATGCATCTGTGTTTTGGCA
2028 111_HRV38a  ACCCAGGAAGAGAGATGATTACACTTGGCAATCTGGTACAAATGCCTCTGTTTTCTGGCA
2029 112_HRV38b  ACCCAGGAAGAGAGATGATTACACTTGGCAATCTGGTACAAATGCCTCTGTTTTCTGGCA
2030 113_HRV38   ACCCAGGAAGAGAGATGATTACACTTGGCAATCTGGTACAAATGCCTCTGTTTTCTGGCA
2031 114_HRV60   ACCTACTAAAAGAGACGATTACACATGGCAATCTGGCACAAATGCTTCTGTATTTTGGCA
2032 115_HRV60a  ACCTACTAAAAGAGACGATTACACATGGCAATCTGGCACAAATGCTTCTGTATTTTGGCA
2033 116_HRV60b  ACCTACTAAAAGAGACGATTACACATGGCAATCTGGCACAAATGCTTCTGTATTTTGGCA
2034 117_HRV64a  ACCAACCAAAAGAAATGATGTCTGGCAGTCAGGCACCAATGCATCCATCTTTTGGCA
2035 118_HRV64b  ACCAACCAAAAGAAATGATTACGTCTGGCAGTCAGGCACCAATGCATCCATCTTTTGGCA
2036 119_HRV64   ACCAACCAAAAGAAATGATTACGTCTGGCAGTCAGGCACCAATGCATCCATCTTTTGGCA
2037 120_HRV94a  ACCAGACAAAAGAGATGATTATGTTTGGCAATCAGGAACTAATGCATCTATATTCTGGCA
2038 121_HRV94b  ACCAGACAAAAGAGATGATTATGTTTGGCAATCAGGAACTAATGCATCTATATTCTGGCA
2039 122_HRV94   ACCAGACAAAAGAGATGATTATGTTTGGCAATCAGGAACTAATGCATCTATATTCTGGCA
2040 123_HRV22   ACCTGAAAAGAGAGATGACTACACATGGCAATCTGGCACTAATGCATCTGTTTTCTGGCA
2041 124_HRV22a  ACCTGAAAAGAGAGATGACTACACATGGCAATCTGGCACTAATGCATCTGTTTTCTGGCA
2042 125_HRV22b  ACCTGAAAAGAGAGATGACTACACATGGCAATCTGGCACTAATGCATCTGTTTTCTGGCA
2043 126_HRV82   ACCAGAAAAGAGAGACGACTACACTTGGCAATCTGGAACTAATGCTTCAATTTTCTGGCA
2044 127_HRV82b  ACCAGAAAAGAGAGACGACTACACTTGGCAATCTGGAACTAATGCTTCAATTTTCTGGCA
2045 128_HRV82a  ACCAGAAAAGAGAGACGACTACACTTGGCAATCTGGAACTAATGCTTCAATTTTCTGGCA
2046 129_HRV19   CCCAAAAACTAGAAATGATTACACATGGCAATCAGGTACTAATGCATCTATATTTTGGCA
2047 130_HRV19a  CCCAAAAACTAGAAATGATTACACATGGCAATCAGGTACTAATGCATCTATATTTTGGCA
2048 131_HRV19b  CCCAAAAACTAGAAATGATTACACATGGCAATCAGGTACTAATGCATCTATATTTTGGCA
2049 132_HRV13   TCCAACGAAGAGAAATGATTACACATGGCAATCTGGCACCAATGCATCTGTTTTCTGGCA
2050 133_HRV13a  TCCAACGAAGAGAAATGATTACACATGGCAATCTGGCACCAATGCATCTGTTTTCTGGCA
2051 134_HRV13b  TCCAACGAAGAGAAATGATTACACATGGCAATCTGGCACCAATGCATCTGTTTTCTGGCA
2052 135_HRV41   CCCAGAAAAGAGAGATGATTACACATGGCAATCTGGCACCAATGCATCTGTATTCTGGCA
2053 136_HRV41a  CCCAGAAAAGAGAGATGATTACACATGGCAATCTGGCACCAATGCATCTGTATTCTGGCA
2054 137_HRV41b  CCCAGAAAAGAGAGATGATTACACATGGCAATCTGGCACCAATGCATCTGTATTCTGGCA
2055 138_HRV73   ACCCACAAAAAGAAATGACTACACATGGCAGTCCGGCACTAATGCATCAGTATTCTGGCA
2056 139_HRV73b  ACCCACAAAAAGAAATGACTACACATGGCAGTCCGGCACTAATGCATCAGTATTCTGGCA
2057 140_HRV73a  ACCCACAAAAAGAAATGACTACACATGGCAGTCCGGCACTAATGCATCAGTATTCTGGCA
2058 141_HRV61   ACCTGAGAAAAGAAATGATTTCACATGGCAATCAGGCACAAATGCATCTGTTTTCTGGCA
2059 142_HRV61a  ACCTGAGAAAAGAAATGATTTCACATGGCAATCAGGCACAAATGCATCTGTTTTCTGGCA
2060 143_HRV61b  ACCTGAGAAAAGAAATGATTTCACATGGCAATCAGGCACAAATGCATCTGTTTTCTGGCA
2061 144_HRV96   ACCTGAGAAGAGAGATGACTTTACATGGCAATCAGGCACAAATGCATCTGTGTTTTGGCA
2062 145_HRV96b  ACCTGAGAAGAGAGATGACTTTACATGGCAATCAGGCACAAATGCATCTGTGTTTTGGCA
2063 146_HRV96a  ACCTGAGAAGAGAGATGACTTTACATGGCAATCAGGCACAAATGCATCTGTGTTTTGGCA
2064 90_HRV16a|  ACCAACAACTAGAAATGACTATGCTTGGCAATCTGGAACAAATGCATCTGTATTTTGGCA
2065 91_HRV16b|  ACCAACAACTAGAAATGACTATGCTTGGCAATCTGGAACAAATGCATCTGTATTTTGGCA
2066 92_1AYM_A   ACCAACAACTAGAAATGACTATGCTTGGCAATCTGGAACAAATGCATCTGTATTTTGGCA
2067 93_HRV81a|  TCCAACAACTAGAGAAGACTATGCTTGGCAATCTGGAACAAATGCATCTATATTCTGGCA
2068 94_HRV81b|  TCCAACAACTAGAGAAGACTATGCTTGGCAATCTGGAACAAATGCATCTATATTCTGGCA
2069 95_HRV81    TCCAACAACTAGAGAAGACTATGCTTGGCAATCTGGAACAAATGCATCTATATTCTGGCA
2070 147_HRV2    GCCCAATAGTAGGGACGATTATGCATGGCAGTCTGGCACTAATGCCTCTGTTTTCTGGCA
2071 148_HRV2a|  GCCCAATAGTAGGGACGATTATGCATGGCAGTCTGGCACTAATGCCTCTGTTTTCTGGCA
2072 149_HRV2b|  GCCCAATAGTAGGGACGATTATGCATGGCAGTCTGGCACTAATGCCTCTGTTTTCTGGCA
2073 150_HRV49a  ACCAAAGAGCAGAGATGATTATGCATGGCAGTCTGGCACTAATGCATCTGTTTTCTGGCA
2074 151_HRV49b  ACCAAAGAGCAGAGATGATTATGCATGGCAGTCTGGCACTAATGCATCTGTTTTCTGGCA
2075 152_HRV49   ACCAAAGAGCAGAGATGATTATGCATGGCAGTCTGGCACTAATGCATCTGTTTTCTGGCA
```

FIG. D9 CONT'D

```
05.trace                                                              9/20/2007 5:04 PM 2076 153_HRV23a    ACCGGAAAGTAGAAATGACTATGCATGGCAATCTGGAACAAATGCGTCCATTTTTTGGCA
2077 154_HRV23b    ACCGGAAAGTAGAAATGACTATGCATGGCAATCTGGAACAAATGCGTCCATTTTTTGGCA
2078 155_HRV23     ACCGGAAAGTAGAAATGACTATGCATGGCAATCTGGAACAAATGCGTCCATTTTTTGGCA
2079 156_HRV30a    TCCCGAGAGCAGAAATGACTATGCATGGCAGTCTGGAACAAATGCATCTGTTTTTTGGCA
2080 157_HRV30b    TCCCGAGAGCAGAAATGACTATGCATGGCAGTCTGGAACAAATGCATCTGTTTTTTGGCA
2081 158_HRV30     TCCCGAGAGCAGAAATGACTATGCATGGCAGTCTGGAACAAATGCATCTGTTTTTTGGCA
2082 159_HRV7      TCCAATAAAACGCGAAGATTATACATGGCAATCAGGAACAAATGCTTCTATATTTTGGCA
2083 160_HRV7b|    TCCAATAAAACGCGAAGATTATACATGGCAATCAGGAACAAATGCTTCTATATTTTGGCA
2084 161_HRV7a|    TCCAATAAAACGCGAAGATTATACATGGCAATCAGGAACAAATGCTTCTATATTTTGGCA
2085 162_HRV88     TCCCAAGAAACGTGATGATTACACATGGCAGTCAGGAACAAATGCATCTGTGTTCTGGCA
2086 163_HRV88a    TCCCAAGAAACGTGATGATTACACATGGCAGTCAGGAACAAATGCATCTGTGTTCTGGCA
2087 164_HRV88b    TCCCAAGAAACGTGATGATTACACATGGCAGTCAGGAACAAATGCATCTGTGTTCTGGCA
2088 165_HRV36a    TCCTGTGAAGCGTGATGACTACACATGGCAATCAGGGACAAATGCATCTGTGTTCTGGCA
2089 166_HRV36b    TCCTGTGAAGCGTGATGACTACACATGGCAATCAGGGACAAATGCATCTGTGTTCTGGCA
2090 167_HRV36     TCCTGTGAAGCGTGATGACTACACATGGCAATCAGGGACAAATGCATCTGTGTTCTGGCA
2091 168_HRV89a    CCCCGAAAAACGTGATGATTACACATGGCAATCAGGAACAAATGCATCTGTGTTCTGGCA
2092 169_HRV89b    CCCCGAAAAACGTGATGATTACACATGGCAATCAGGAACAAATGCATCTGTGTTCTGGCA
2093 170_HRV89     CCCCGAAAAACGTGATGATTACACATGGCAATCAGGAACAAATGCATCTGTGTTCTGGCA
2094 171_HRV58     ACCCAAGAATCGTGATGACTTTACATGGCAATCAGGCACAAATGCATCTGTTTTCTGGCA
2095 172_HRV58a    ACCCAAGAATCGTGATGACTTTACATGGCAATCAGGCACAAATGCATCTGTTTTCTGGCA
2096 173_HRV58b    ACCCAAGAATCGTGATGACTTTACATGGCAATCAGGCACAAATGCATCTGTTTTCTGGCA
2097 174_HRV12a    ACCCAAAAAACGTGATGATTACACATGGCAATCTGGCACCAACGCCTCAGTTTTTTGGCA
2098 175_HRV12b    ACCCAAAAAACGTGATGATTACACATGGCAATCTGGCACCAACGCCTCAGTTTTTTGGCA
2099 176_HRV12     ACCCAAAAAACGTGATGATTACACATGGCAATCTGGCACCAACGCCTCAGTTTTTTGGCA
2100 177_HRV78a    ACCAAAGAAGAGAGATGACTATACTTGGCAGTCAGGCACCAATGCATCTGTGTTTTGGCA
2101 178_HRV78b    ACCAAAGAAGAGAGATGACTATACTTGGCAGTCAGGCACCAATGCATCTGTGTTTTGGCA
2102 179_HRV78     ACCAAAGAAGAGAGATGACTATACTTGGCAGTCAGGCACCAATGCATCTGTGTTTTGGCA
2103 180_HRV20     ACCAAAGACTAGAGATGACTACACATGGCAATCAGGGACAAATGCATCAGTATTTTGGCA
2104 181_HRV20a    ACCAAAGACTAGAGATGACTACACATGGCAATCAGGGACAAATGCATCAGTATTTTGGCA
2105 182_HRV20b    ACCAAAGACTAGAGATGACTACACATGGCAATCAGGGACAAATGCATCAGTATTTTGGCA
2106 183_HRV68     ACCAAAAACTAGAGATGATTACACATGGCAGTCAGGCACTAATGCATCAGTGTTTTGGCA
2107 184_HRV68a    ACCAAAAACTAGAGATGATTACACATGGCAGTCAGGCACTAATGCATCAGTGTTTTGGCA
2108 185_HRV68b    ACCAAAAACTAGAGATGATTACACATGGCAGTCAGGCACTAATGCATCAGTGTTTTGGCA
2109 186_HRV28     CCCCACTACCAGAGATGATTACACATGGCAATCCAGTACCAATGCCTCTGTTTTCTGGCA
2110 187_HRV28a    CCCCACTACCAGAAATGATTACACATGGCAATCCAGTACCAATGCCTCTGTTTTCTGGCA
2111 188_HRV28b    CCCCACTACCAGAAATGATTACACATGGCAATCCAGTACCAATGCCTCTGTTTTCTGGCA
2112 189_HRV53a    ACCCAAAACCAGAGATGACTATACCTGGCAATCTGGAACTAATGCTTCAGTCTTTTGGCA
2113 190_HRV53b    ACCAAAACCAGAGATGACTATACCTGGCAATCTGGAACTAATGCTTCAGTCTTTTGGCA
2114 191_HRV53     ACCCAAAACCAGAGATGACTATACCTGGCAATCTGGAACTAATGCTTCAGTCTTTTGGCA
2115 192_HRV46a    ACCGAGATATCGGAATGATTATACTTGGCAGTCTGGTACTAATGCTTCAGTGTTCTGGCA
2116 193_HRV46b    ACCGAGATATCGGAATGATTATACTTGGCAGTCTGGTACTAATGCTTCAGTGTTCTGGCA
2117 194_HRV46     ACCGAGATATCGGAATGATTATACTTGGCAGTCTGGTACTAATGCTTCAGTGTTCTGGCA
2118 195_HRV80a    GCCAAACAAACGCAATGATTATACTTGGCAGTCTGGCACGAATGCTTCAGTCTTCTGGCA
2119 196_HRV80b    GCCAAACAAACGCAATGATTATACTTGGCAGTCTGGCACGAATGCTTCAGTCTTCTGGCA
2120 197_HRV80     GCCAAACAAACGCAATGATTATACTTGGCAGTCTGGCACGAATGCTTCAGTCTTCTGGCA
2121 198_HRV51     TCCACTTACTAGGAAAGATGATGAGTGGCAATCAGGAACTAATGCTTCAGTATTCTGGCA
2122 199_HRV51a    TCCACTTACTAGGAAAGATGATGAGTGGCAATCAGGAACTAATGCTTCAGTATTCTGGCA
2123 200_HRV51b    TCCACTTACTAGGAAAGATGATGAGTGGCAATCAGGAACTAATGCTTCAGTATTCTGGCA
2124 201_HRV65a    TCCAAAAACTAGAAAAGATGAAGAGTGGCAGACAGGAACTAATGCTTCAGTCTTTTGGCA
2125 202_HRV65b    TCCAAAAACTAGAAAAGATGAAGAGTGGCAGACAGGAACTAATGCTTCAGTCTTTTGGCA
2126 203_HRV65     TCCAAAAACTAGAAAAGATGAAGAGTGGCAGACAGGAACTAATGCTTCAGTCTTTTGGCA
2127 204_HRV71a    ACCAGAGACCAGGGATGCCGATGAATGGCAGTCTGGAACTAATGCATCAGTCTTTTGGCA
2128 205_HRV71b    ACCAGAGACCAGGGATGCCGATGAATGGCAGTCTGGAACTAATGCATCAGTCTTTTGGCA
2129 206_HRV71     ACCAGAGACCAGGGATGCCGATGAATGGCAGTCTGGAACTAATGCATCAGTCTTTTGGCA
2130 207_HRV8      TCCAGATAAAAGGATGCACGATGCCTGGCAAACCAGTACAAATGCCTCAGTCTTCTGGCA
2131 208_HRV95     TCCAGATAAAAGGATGCACGATGCCTGGCAAACCAGTACAAATGCCTCAGTCTTCTGGCA
2132 209_HRV45     CCCTGTTAGTAGAACTGACAACACTTGGCAATCTAGCACAAATGCATCAGTCTTTTGGCA
2133 210_HRV45a    CCCTGTTAGTAGAACTGACAACACTTGGCAATCTAGCACAAATGCATCAGTCTTTTGGCA
2134 211_HRV45b    CCCTGTTAGTAGAACTGACAACACTTGGCAATCTAGCACAAATGCATCAGTCTTTTGGCA
2135 GROUP_1       -CC--------G-------------TGG-A--C--G-A--AA----TC----TT-TGGCA
2136
2137 1_HRV1A1|d    ACATGGACAGCCATTTCCTAGATTTTCTTTACCATTTCTTAGCATTGCATCAGCTTATTA
2138 2_HRV1A2|d    ACATGGACAGCCATTTCCTAGATTTTCTTTACCATTTCTTAGCATTGCATCAGCTTATTA
2139 3_HRV1A|cD    ACATGGACAGCCATTTCCTAGATTTTCTTTACCATTTCTTAGCATTGCATCAGCTTATTA
2140 4_HRV1B1|d    ACATGGACAACCGTTCCCTAGATTCTCTTTACCATTTCTTAGCATTGCATCAGCTTATTA
```

FIG. D9 CONT'D

05.trace                                                                                    9/20/2007 5:04 PM

```
2141  5_HRV1B2|d   ACATGGACAACCGTTCCCTAGATTCTCTTTACCATTTCTTAGCATTGCATCAGCTTATTA
2142  6_HRV1B      ACATGGACAACCGTTCCCTAGATTCTCTTTACCATTTCTTAGCATTGCATCAGCTTATTA
2143  7_HRV40a|d   ACATGGTCAAACTTTCCCTAGATTTTCTTTACCTTTCCTAAGCATAGCTTCAGCATACTA
2144  8_HRV40b|d   ACATGGTCAAACTTTCCCTAGATTTTCTTTACCTTTCCTAAGCATAGCTTCAGCATACTA
2145  9_HRV40      ACATGGTCAAACTTTCCCTAGATTTTCTTTACCTTTCCTAAGCATAGCTTCAGCATACTA
2146  10_HRV85     ACATGGGCAAACTTTCCCCAGATTTTCCTTACCTTTCTTGAGTGTTGCTTCAGCATATTA
2147  11_HRV85a|   ACATGGGCAAACTTTCCCCAGATTTTCCTTACCTTTCTTGAGTGTTGCTTCAGCATATTA
2148  12_HRV85b|   ACATGGGCAAACTTTCCCCAGATTTTCCTTACCTTTCTTGAGTGTTGCTTCAGCATATTA
2149  13_HRV56a|   ACATGGCCAAGCTTTCCCCAGATTCTCTCTACCTTTCTTAAGTATTGCTTCTGCTTATTA
2150  14_HRV56b|   ACATGGCCAAGCTTTCCCCAGATTCTCTCTACCTTTCTTAAGTATTGCTTCTGCTTATTA
2151  15_HRV56     ACATGGCCAAGCTTTCCCCAGATTCTCTCTACCTTTCTTAAGTATTGCTTCTGCTTATTA
2152  16_HRV54     ACATGGCCAAGCTTATCCAAGATTCTCTTTACCATTCTTGAGCATTGCATCTGCTTACTA
2153  17_HRV98     GCATGGTCAGGCCTATCCAAGATTTTCTCTACCATTCTTGAGCATTGCATCTGCTTACTA
2154  18_HRV59a|   ACATGGACAAACATTCCCAAGATTTTCATTGCCCTTCCTGAGCATAGCCATCAGCTTATTA
2155  19_HRV59b|   ACATGGACAAACATTCCCAAGATTTTCATTGCCCTTCCTGAGCATAGCATCAGCTTATTA
2156  20_HRV59     ACATGGACAAACATTCCCAAGATTTTCATTGCCCTTCCTGAGCATAGCATCAGCTTATTA
2157  21_HRV63     ACATGGACAAGCTTTTCCAAGGTTTTCTCTACCTTTCTTGAGTATTGCATCAGCATATTA
2158  22_HRV63b|   ACATGGACAAGCTTTTCCAAGGTTTTCTCTACCTTTCTTGAGTATTGCATCAGCATATTA
2159  23_HRV63a|   ACATGGACAAGCTTTTCCAAGGTTTTCTCTACCTTTCTTGAGTATTGCATCAGCATATTA
2160  24_HRV39     ACACGGACAGCCTTACCCTAGATTTTCATTACCATTTCTAAGCATAGCCTCAGCATATTA
2161  25_HRV39a|   ACACGGACAGCCTTACCCTAGATTTTCATTACCATTTCTAAGCATAGCCTCAGCATATTA
2162  26_HRV39b|   ACACGGACAGCCTTACCCTAGATTTTCATTACCATTTCTAAGCATAGCCTCAGCATATTA
2163  27_HRV10a|   ACATGGACAACCTTTCCCTAGATTTTCTTTACCCTTCTTAAGCATAGCCATCTGCTTACTA
2164  28_HRV10b|   ACATGGACAACCTTTCCCTAGATTTTCTTTACCCTTCTTAAGCATTGCATCTGCTTACTA
2165  29_HRV10     ACATGGACAACCTTTCCCTAGATTTTCTTTACCCTTCTTAAGCATTGCATCTGCTTACTA
2166  30_HRV100a   GCATGGGCAGCCATTCCCTAGATTTCTTTACCTTTCTTGAGCATTGCTTCTGCATACTA
2167  31_HRV100b   GCATGGGCAGCCATTCCCTAGAATTTCTTTACCTTTCTTGAGCATTGCTTCTGCATACTA
2168  32_HRV100    GCATGGGCAGCCATTCCCTAGAATTTCTTTACCTTTCTTGAGCATTGCTTCTGCATACTA
2169  33_HRV66     ACTTGGACAACCATTCCCAAGATTCTCGCTACCTTTTCTAGGCATAGCTTCAGCATATTA
2170  34_HRV66b|   ACTTGGACAACCATTCCCAAGATTCTCGCTACCTTTTCTAGGCATAGCTTCAGCATATTA
2171  35_HRV66a|   ACTTGGACAACCATTCCCAAGATTCTCGCTACCTTTTCTAGGCATAGCTTCAGCATATTA
2172  36_HRV77a|   ACATGGACAACCATTCCCAAGATTTTCACTACCTTTTCTGAGTATTGCTTCAGCTTACTA
2173  37_HRV77b|   ACATGGACAACCATTCCCAAGATTTTCACTACCTTTTCTGAGTATTGCTTCAGCTTACTA
2174  38_HRV77     ACATGGACAACCATTCCCAAGATTTTCACTACCTTTTCTGAGTATTGCTTCAGCTTACTA
2175  39_HRV62a    ACATGGGCAACCCTTTCCTAGATTTTCATTACCTTTTTGAGTGTTGCATCTGCTTATTA
2176  40_HRV62b    ACATGGGCAACCCTTTCCTAGATTTTCATTACCTTTTTGAGTGTTGCATCTGCTTATTA
2177  41_HRV25     ACATGGACAACCCTTCCCAAGATTTTCATTGCCATTTCTGAGTGTTGCATCTGCTTATTA
2178  42_HRV29a    ACATGGTCAGCCTTTCCCAAGATTTTCATTACCATTCCTAAGTGTTGCATCTGCTTATTA
2179  43_HRV29b    ACATGGTCAGCCTTTCCCAAGATTTTCATTACCATTCCTAAGTGTTGCATCTGCTTATTA
2180  44_HRV44a    ACATGGTCAACCTTTCCCAAGATTTTCATTGCCATTTCTAAGTGTTGCATCTGCCTATTA
2181  45_HRV44b    ACATGGTCAACCTTTCCCAAGATTTTCATTGCCATTTCTAAGTGTTGCATCTGCCTATTA
2182  46_HRV31     ACATGGACAACCCTTTCCAAGATTTACATTACCCTTTTTGAGTGTCGCATCCGCTTATTA
2183  47_HRV31a|   ACATGGACAACCCTTTCCAAGATTTACATTACCCTTTTTGAGTGTCGCATCCGCTTATTA
2184  48_HRV31b|   ACATGGACAACCCTTTCCAAGATTTACATTACCCTTTTTGAGTGTCGCATCCGCTTATTA
2185  49_HRV47     ACAAGGGCAACCCTTTCCAAGATTTTCATTACCATTTTTGAGTGTTGCATCTGCTTATTA
2186  50_HRV47a|   ACAAGGGCAACCCTTTCCAAGATTTTCATTACCATTTTTGAGTGTTGCATCTGCTTATTA
2187  51_HRV47b|   ACAAGGGCAACCCTTTCCAAGATTTTCATTACCATTTTTGAGTGTTGCATCTGCTTATTA
2188  52_HRV11     ATATGGTCAAACATACCCAAGATTTTCTCTACCTTTCATGAGTATAGCCTCAGCATATTA
2189  53_HRV11b|   ATATGGTCAAACATACCCAAGATTTTCTCTACCTTTCATGAGTATAGCCTCAGCATATTA
2190  54_HRV11a|   ATATGGTCAAACATACCCAAGATTTTCTCTACCTTTCATGAGTATAGCCTCAGCATATTA
2191  55_HRV76     ATATGGACAAACATACCCTAGGTTTTCATTACCCTTTCTAAGTATAGCTTCAGCTTATTA
2192  56_HRV76b|   ATATGGACAAACATACCCTAGGTTTTCATTACCCTTTCTAAGTATAGCTTCAGCTTATTA
2193  57_HRV76a|   ATATGGACAAACATACCCTAGGTTTTCATTACCCTTTCTAAGTATAGCTTCAGCTTATTA
2194  58_HRV33     ATATGGACAAACATATCCTAGGTTCTCATTACCTTTCCTTAGCATAGCTTCAGCATATTA
2195  59_HRV33b|   ATATGGACAAACATATCCTAGGTTCTCATTACCTTTCCTTAGCATAGCTTCAGCATATTA
2196  60_HRV33a|   ATATGGACAAACATATCCTAGGTTCTCATTACCTTTCCTTAGCATAGCTTCAGCATATTA
2197  61_HRV24a|   ACATGGACAAACCTATCCTAGATTTTCCCTTCCTTTTCTGAGTGTAGCCTCTGCATATTA
2198  62_HRV24b|   ACATGGACAAACCTATCCTAGATTTTCCCTTCCTTTTCTGAGTGTAGCCTCTGCATATTA
2199  63_HRV24     ACATGGACAAACCTATCCTAGATTTTCCCTTCCTTTTCTGAGTGTAGCCTCTGCATATTA
2200  64_HRV90     ACATGGACAAACATACCCTAGATTTTCACTTCCTTTCTTAAGTATAGCTTCTGCATACTA
2201  65_HRV90a|   ACATGGACAAACATACCCTAGATTTTCACTTCCTTTCTTAAGTATAGCTTCTGCATACTA
2202  66_HRV90b|   ACATGGACAAACATACCCTAGATTTTCACTTCCTTTCTTAAGTATAGCTTCTGCATACTA
2203  67_HRV34     ACATGGTCAAACATACCCTAGATTTTCCCTCCCTTTCTTAAGCATAGCCTCAGCATACTA
2204  68_HRV34b|   ACATGGTCAAACATACCCTAGATTTTCCCTCCCTTTCTTAAGCATAGCCTCAGCATACTA
2205  69_HRV34a|   ACATGGTCAAACATACCCTAGATTTTCCCTCCCTTTCTTAAGCATAGCCTCAGCATACTA
```

FIG. D9 CONT'D 05.trace                                                                9/20/2007 5:04 PM

```
2206  70_HRV50a|    ACATGGTCAAACATACCCTAGATTCTCTCTACCATTCTTGAGTATAGCATCTGCATATTA
2207  71_HRV50b|    ACATGGTCAAACATACCCTAGATTCTCTCTACCATTCTTGAGTATAGCATCTGCATATTA
2208  72_HRV50     ACATGGTCAAACATACCCTAGATTCTCTCTACCATTCTTGAGTATAGCATCTGCATATTA
2209  73_HRV18a|    ACATGGTCAAACATACCCCAGATTTTCACTTCCTTTCCTCAGTATAGCATCAGCTTATTA
2210  74_HRV18b|    ACATGGTCAAACATACCCCAGATTTTCACTTCCTTTCCTCAGTATAGCATCAGCTTATTA
2211  75_HRV18     ACATGGTCAAACATACCCCAGATTTTCACTTCCTTTCCTCAGTATAGCATCAGCTTATTA
2212  76_HRV55     ACATGGGCAAACATACCCTAGATTTTCACTTCCTTTCCTAAGTATAGCTTCTGCTTATTA
2213  77_HRV55b|    ACATGGGCAAACATACCCTAGATTTTCACTTCCTTTCCTAAGTATAGCTTCTGCTTATTA
2214  78_HRV55a|    ACATGGGCAAACATACCCTAGATTTTCACTTCCTTTCCTAAGTATAGCTTCTGCTTATTA
2215  79_HRV57     ACATGGTCAAACATACCCTAGATTTTCCTTGCCTTTCTTAAGTATAGCCTCAGCATATTA
2216  80_HRV57a|    ACATGGTCAAACATACCCTAGATTTTCCTTGCCTTTCTTAAGTATAGCCTCAGCATACTA
2217  81_HRV57b|    ACATGGTCAAACATACCCTAGATTTTCCTTGCCTTTCTTAAGTATAGCCTCAGCATATTA
2218  82_HRV21     GCATGGCCAGACTTATCCTAGATTTTCATTACCCTTCCTTAGTATAGCATCAGCATACTA
2219  83_HRVHan    GCATGGTCAAACTTATCCTAGATTTTCACTACCCTTCCTTAGTATAGCATCAGCATATTA
2220  84_HRV43     ACATGGTCAAACATTTCCAAGATTTTCCTTACCTTTTCTGAGCATAGCATCAGCATATTA
2221  85_HRV43b|    ACATGGTCAAACATTTCCAAGATTTTCCTTACCTTTTCTGAGCATAGCATCAGCATATTA
2222  86_HRV43a|    ACATGGTCAAACATTTCCAAGATTTTCCTTACCTTTTCTGAGCATAGCATCAGCATATTA
2223  87_HRV75     ACATGGACAAACATTTCCAAGATTTTCACTACCATTTCTGAGCATTGCATCAGCATATTA
2224  88_HRV75b|    ACATGGACAAACATTTCCAAGATTTTCACTACCATTTCTGAGCATTGCATCAGCATATTA
2225  89_HRV75a|    ACATGGACAAACATTTCCAAGATTTTCACTACCATTTCTGAGCATTGCATCAGCATATTA
2226  96_HRV9a|d   ACATGGACAATCATATCCCAGATTTTCACTTCCGTTTTTGAGCATTGCCTCTGCATATTA
2227  97_HRV9b|d   ACATGGACAATCATATCCCAGATTTTCACTTCCGTTTTTGAGCATTGCCTCTGCATATTA
2228  98_HRV9      ACATGGACAATCATATCCCAGATTTTCACTTCCGTTTTTGAGCATTGCCTCTGCATATTA
2229  99_HRV32     GCATGGACAGGCATATCCCAGGTTTTCACTTCCATTTCTAAGTATTGCCTCTGCATACTA
2230  100_HRV32a   GCATGGACAGGCATATCCCAGGTTTTCACTTCCATTTCTAAGTATTGCCTCTGCATACTA
2231  101_HRV32b   GCATGGACAGGCATATCCCAGGTTTTCACTTCCATTTCTAAGTATTGCCTCTGCATACTA
2232  102_HRV67    ACATGGACAATCATACCCCAGATTCTCACTACCATTCTTAAGTATTGCCTCTGCTTATTA
2233  103_HRV67a   ACATGGACAATCATACCCCAGATTCTCACTACCATTCTTAAGTATTGCCTCTGCTTATTA
2234  104_HRV67b   ACATGGACAATCATACCCCAGATTCTCACTACCATTCTTAAGTATTGCCTCTGCTTATTA
2235  105_HRV15    ACATGGTCAACCTTACCCCAGATTTTCTTTGCCTTTTCTCAGCATTGCATCTGCTTACTA
2236  106_HRV15a   ACATGGTCAACCTTACCCCAGATTTTCTTTGCCTTTTCTCAGCATTGCATCTGCTTACTA
2237  107_HRV15b   ACATGGTCAACCTTACCCCAGATTTTCTTTGCCTTTTCTCAGCATTGCATCTGCTTACTA
2238  108_HRV74a   GCATGGACAGCCATACCCTAGATTCTCATTACCTTTCCTTAGCATAGCATCTGCTTATTA
2239  109_HRV74b   GCATGGACAGCCATACCCTAGATTCTCATTACCTTTCCTTAGCATAGCATCTGCTTATTA
2240  110_HRV74    GCATGGACAGCCATACCCTAGATTCTCATTACCTTTCCTTAGCATAGCATCTGCTTATTA
2241  111_HRV38a   ATATGGTCAGACATATCCTCGATTTTCCTTACCTTTCTTAAGCATTGCATCTGTCTATTA
2242  112_HRV38b   ATATGGTCAGACATATCCTCGATTTTCCTTACCTTTCTTAAGCATTGCATCTGTCTATTA
2243  113_HRV38    ATATGGTCAGACATATCCTCGATTTTCTTACCTTTCTTAAGCATTGCATCTGTCTATTA
2244  114_HRV60    GCATGGACAAACATACCCTAGATTTTCACTTCCATTTCTAAGTATTGCCATCTGCCTACTA
2245  115_HRV60a   GCATGGACAAACATACCCTAGATTTTCACTTCCATTTCTAAGTATTGCATCTGCCTACTA
2246  116_HRV60b   GCATGGACAAACATACCCTAGATTTTCACTTCCATTTCTAAGTATTGCATCTGCCTACTA
2247  117_HRV64a   ACACGGTCAACCATACCCTCGATTTTCTCTCCCTTTCCTTAGCATAGCCTCAGCATATTA
2248  118_HRV64b   ACACGGTCAACCATACCCTCGATTTTCTCTCCCTTTCCTTAGCATAGCCTCAGCATATTA
2249  119_HRV64    ACACGGTCAACCATACCCTCGATTTTCTCTCCCTTTCCTTAGCATAGCCTCAGCATATTA
2250  120_HRV94a   ACATGGTCAACCCTACCCTCGATTCTCACTTCCATTTCTTAGTATAGCCTCAGCATATTA
2251  121_HRV94b   ACATGGTCAACCCTACCCTCGATTCTCACTTCCATTTCTTAGTATAGCCTCAGCATATTA
2252  122_HRV94    ACATGGTCAACCCTACCCTCGATTCTCACTTCCATTTCTTAGTATAGCCTCAGCATATTA
2253  123_HRV22    GCATGGTCAACCTTATCCCCGATTCTCACTCCCTTTCCTCAGTGTAGCTTCAGCATTA
2254  124_HRV22a   GCATGGTCAACCTTATCCCCGATTCTCACTCCCTTTCCTCAGTGTAGCTTCAGCATATTA
2255  125_HRV22b   GCATGGTCAACCTTATCCCCGATTCTCACTCCCTTTCCTCAGTGTAGCTTCAGCATATTA
2256  126_HRV82    ACATGGACAACCTTACCCTCGCTTCTCACTTCCTTTCTTGAGTATAGCCTCAGCTTACTA
2257  127_HRV82b   ACATGGACAACCTTACCCTCGCTTCTCACTTCCTTTCTTGAGTATAGCCTCAGCTTACTA
2258  128_HRV82a   ACATGGACAACCTTACCCTCGCTTCTCACTTCCTTTCTTGAGTATAGCCTCAGCTTACTA
2259  129_HRV19    ACATGGTCAACCATACCCAAGATTTTCATTACCTTTTCTAAGTATAGCCTTCTGCATATTA
2260  130_HRV19a   ACATGGTCAACCATACCCAAGATTTTCATTACCTTTTCTAAGTATAGCTTCTGCATATTA
2261  131_HRV19b   ACATGGTCAACCATACCCAAGATTTTCATTACCTTTTCTAAGTATAGCTTCTGCATATTA
2262  132_HRV13    ACATGGTCAAATTTACCCCCGATTCTCTTTACCATTTCTTAGTATTGCATCTGCATATTA
2263  133_HRV13a   ACATGGTCAAATTTACCCCCGATTCTCTTTACCATTTCTTAGTATTGCATCTGCATATTA
2264  134_HRV13b   ACATGGTCAAATTTACCCCCGATTCTCTTTACCATTTCTTAGTATTGCATCTGCATATTA
2265  135_HRV41    GTATGGTCAAGTTTACCCTAGGTTTTCTCTACCATTTCTTAGCATTGCTTCCGCATATTA
2266  136_HRV41a   GTATGGTCAAGTTTACCCTAGGTTTTCTCTACCATTGCTTAGCATTGCTTCCGCATATTA
2267  137_HRV41b   GTATGGTCAAGTTTACCCTAGGTTTTCTCTACCATTTCTTAGCATTGCTTCCGCATATTA
2268  138_HRV73    ACATGGTCAAACTTACCCCAGATTCTCATTACCATTCCTTAGTATAGCATCCGCATATTA
2269  139_HRV73b   ACATGGTCAAACTTACCCCAGATTCTCATTACCATTCCTTAGTATAGCATCCGCATATTA
2270  140_HRV73a   ACATGGTCAAACTTACCCCAGATTCTCATTACCATTCCTTAGTATAGCATCCGCATATTA
```

FIG. D9 CONT'D

```
05.trace                                                                      9/20/2007 5:04 PM 2271 141_HRV61    ACATGGTCAAGCTTATCCCAGATTTTCATTACCATTCCTAAGTATTGCATCTGCATATTA
2272 142_HRV61a   ACATGGTCAAGCTTATCCCAGATTTTCATTACCATTCCTAAGTATTGCATCTGCATATTA
2273 143_HRV61b   ACATGGTCAAGCTTATCCCAGATTTTCATTACCATTCCTAAGTATTGCATCTGCATATTA
2274 144_HRV96    GCACGGGCAAGCATATCCTAGATTTTCACTGCCTTTCCTTAGTATTGCCTCTGCATATTA
2275 145_HRV96b   GCACGGGCAAGCATATCCTAGATTTTCACTGCCTTTCCTTAGTATTGCCTCTGCATATTA
2276 146_HRV96a   GCACGGGCAAGCATATCCTAGATTTTCACTGCCTTTCCTTAGTATTGCCTCTGCATATTA
2277 90_HRV16a|   GCATGGGCAACCTTTCCCTCGCTTTTCACTTCCCTTTTTGAGTATTGCATCAGCATATTA
2278 91_HRV16b|   GCATGGGCAACCTTTCCCTCGCTTTTCACTTCCCTTTTTGAGTATTGCATCAGCATATTA
2279 92_1AYM_A    GCATGGGCAACCTTTCCCTCGCTTTTCACTTCCCTTTTTGAGTATTGCATCAGCATATTA
2280 93_HRV81a|   ACATGGGCAACCCTTTCCCCGGTTTTCACTCCCTTTTCTAAGTGTAGCATCAGCATATTA
2281 94_HRV81b|   ACATGGGCAACCCTTTCCCCGGTTTTCTCTACCTTTTCTAAGTGTAGCATCAGCATATTA
2282 95_HRV81     ACATGGGCAACCCTTTCCCCGGTTTTCACTCCCTTTTCTAAGTGTAGCATCAGCATATTA
2283 147_HRV2     ACATGGACAGGCTTATCCAAGATTTTCCTTACCTTTCCTAAGTGTGGCATCTGCTTATTA
2284 148_HRV2a|   ACATGGACAGGCTTATCCAAGATTTTCCTTACCTTTCCTAAGTGTGGCATCTGCTTATTA
2285 149_HRV2b|   ACATGGACAGGCTTATCCAAGATTTTCCTTACCTTTCCTAAGTGTGGCATCTGCTTATTA
2286 150_HRV49a   ACATGGGCAAGCATACCCAAGATTTTCTCTACCCTTTTGAGTGTAGCTTCAGCTTACTA
2287 151_HRV49b   ACATGGGCAAGCATACCCAAGATTTTCTCTACCCTTTTGAGTGTAGCTTCAGCTTACTA
2288 152_HRV49    ACATGGGCAAGCATACCCAAGATTTTCTCTACCCTTTTGAGTGTAGCTTCAGCTTACTA
2289 153_HRV23a   ACATGGACAAACATATCCAAGGTTCTCCTTACCCTTTTTGAGTGTGGCATCTGCTTATTA
2290 154_HRV23b   ACATGGACAAACATATCCAAGGTTCTCCTTACCCTTTTTGAGTGTGGCATCTGCTTATTA
2291 155_HRV23    ACATGGACAAACATATCCAAGGTTCTCCTTACCCTTTTTGAGTGTGGCATCTGCTTATTA
2292 156_HRV30a   ACACGGACAAACATACCCAAGATTCTCCTACCATTTTGAGTGTAGCATCTGCTTATTA
2293 157_HRV30b   ACACGGACAAACATACCCAAGATTCTCCCTACCATTTTGAGTGTAGCATCTGCTTATTA
2294 158_HRV30    ACACGGACAAACATACCCAAGATTCTCCCTACCATTTTGAGTGTAGCATCTGCTTATTA
2295 159_HRV7     GGAGGGTCAACCATACCCTAGATTCACAATTCCTTTATGAGTATTGCATCAGCTTATTA
2296 160_HRV7b|   GGAGGGTCAACCATACCCTAGATTCACAATTCCTTTATGAGTATTGCATCAGCTTATTA
2297 161_HRV7a|   GGAGGGTCAACCATACCCTAGATTCACAATTCCTTTATGAGTATTGCATCAGCTTATTA
2298 162_HRV88    AGAAGGACAACCATACCCAAGATTTACCATTCCCTTTATGAGTATTGCATCAGCTTACTA
2299 163_HRV88a   AGAAGGACAACCATACCCAAGATTTACCATTCCCTTTATGAGTATTGCATCAGCTTACTA
2300 164_HRV88b   AGAAGGACAACCATACCCAAGATTTACCATTCCCTTTATGAGTATTGCATCAGCTTACTA
2301 165_HRV36a   AGAAGGGCAACCATATCCTAGATTTACAATCCCCTTTATGAGTATTGCATCAGCTTATTA
2302 166_HRV36b   AGAAGGGCAACCATATCCTAGATTTACAATCCCCTTTATGAGTATTGCATCAGCTTATTA
2303 167_HRV36    AGAAGGGCAACCATATCCTAGATTTACAATCCCCTTTATGAGTATTGCATCAGCTTATTA
2304 168_HRV89a   AGAAGGACAACCATACCCCAGATTCACAATCCCTTTATGAGCATTGCATCAGCAGCCTATTA
2305 169_HRV89b   AGAAGGACAACCATACCCCAGATTCACAATCCCTTTTATGAGCATTGCATCAGCCTATTA
2306 170_HRV89    AGAAGGACAACCATACCCCAGATTCACAATCCCTTTTATGAGCATTGCATCAGCCTATTA
2307 171_HRV58    GGAAGGACAACCATACCCTAGATTTACAATCCCTTTATGAGCATTGCATCAGCTTACTA
2308 172_HRV58a   GGAAGGACAACCATACCCTAGATTTACAATCCCTTTTATGAGCATTGCATCAGCTTACTA
2309 173_HRV58b   GGAAGGACAACCATACCCTAGATTTACAATCCCTTTTATGAGCATTGCATCAGCTTACTA
2310 174_HRV12a   GGAAGGTCAACCTTACCCCAGATTCACAATCCCTTTTATTAGTATTGCCTCAGCATATTA
2311 175_HRV12b   GGAAGGTCAACCTTACCCCAGATTCACAATCCCTTTTATTAGTATTGCCTCAGCATATTA
2312 176_HRV12    GGAAGGTCAACCTTACCCCAGATTCACAATCCCTTTTATTAGTATTGCCTCAGCATATTA
2313 177_HRV78a   ACAAGGTCAAACATACCCCAGGTTCTCTATACCATTTTCTAGTATTGCCTCAGCTTATTA
2314 178_HRV78b   ACAAGGTCAAACATACCCCAGGTTCTCTATACCATTTTCTAGTATTGCCTCAGCTTATTA
2315 179_HRV78    ACAAGGTCAAACATACCCCAGGTTCTCTATACCATTTTCTAGTATTGCCTCAGCTTATTA
2316 180_HRV20    GCAGGGCCAACCTTACCCCAGATTTACCATTCCATTTATGAGTATAGCTTCAGCATATTA
2317 181_HRV20a   GCAGGGCCAACCTTACCCCAGATTTACCATTCCATTTATGAGTATAGCTTCAGCATATTA
2318 182_HRV20b   GCAGGGCCAACCTTACCCCAGATTTACCATTCCATTTATGAGTATAGCTTCAGCATATTA
2319 183_HRV68    ACAAGGACAACCTTACCCCAGATTTACCATTCCATTTATGAGTATAGCTTCAGCATATTA
2320 184_HRV68a   ACAAGGACAACCTTACCCCAGATTTACCATTCCATTTATGAGTATAGCTTCAGCATATTA
2321 185_HRV68b   ACAAGGACAACCTTACCCCAGATTTACCATTCCATTTATGAGTATAGCTTCAGCATATTA
2322 186_HRV28    ACAAGGACAACCATATCCCAGATTCACTATACCTTTTATGAGTATTGCCTCAGCTTATTA
2323 187_HRV28a   ACAAGGACAACCATATCCCAGATTCACTATACCTTTTATGAGTATTGCCTCAGCTTATTA
2324 188_HRV28b   ACAAGGACAACCATATCCCAGATTCACTATACCTTTTATGAGTATTGCCTCAGCTTATTA
2325 189_HRV53a   ACAAGGACAACCATACCCTAGATTCACAATCCCTTTCATGAGTATTGCGTCAGCATATTA
2326 190_HRV53b   ACAAGGACAACCATACCCTAGATTCACAATCCCTTTCATGAGTATTGCGTCAGCATATTA
2327 191_HRV53    ACAAGGACAACCATACCCTAGATTCACAATCCCTTTCATGAGTATTGCGTCAGCATATTA
2328 192_HRV46a   GCAAGGGCAGCCATACCCTAGATTCACTATCCCGTTCATGAGTATAGCCTCAGCATATTA
2329 193_HRV46b   GCAAGGGCAGCCATACCCTAGATTCACTATCCCGTTCATGAGTATAGCCTCAGCATATTA
2330 194_HRV46    GCAAGGGCAGCCATACCCTAGATTCACTATCCCGTTCATGAGTATAGCCTCAGCATATTA
2331 195_HRV80a   ACAGGGTCAGCCATACCCCAGATTCACTATTCCATTCATGAGTATAGCCTCAGCTTATTA
2332 196_HRV80b   ACAGGGTCAGCCATACCCCAGATTCACTCATTCATGAGTATAGCCTCAGCTTATTA
2333 197_HRV80    ACAGGGTCAGCCATACCCCAGATTCACTATTCCATTCATGAGTATAGCCTCAGCTTATTA
2334 198_HRV51    ACATGGACAACCATACCCTAGATTTACAATCCCTTTTGTAAGCATAGCCTCAGCATACTA
2335 199_HRV51a   ACATGGACAACCATACCCTAGATTTACAATCCCTTTTGTAAGCATAGCCTCAGCATACTA
```

FIG. D9 CONT'D

```
05.trace                                                            9/20/2007 5:04 PM 2336 200_HRV51b   ACATGGACAACCATACCCTAGATTTACAATCCCTTTTGTAAGCATAGCCTCAGCATACTA
2337 201_HRV65a   GCATGGTCAACCATACCCCAGATTTACAATTCCTTTTGTGAGTATTGCCTCAGCATATTA
2338 202_HRV65b   GCATGGTCAACCATACCCCAGATTTACAATTCCTTTTGTGAGTATTGCCTCAGCATATTA
2339 203_HRV65    GCATGGTCAACCATACCCCAGATTTACAATTCCTTTTGTGAGTATTGCCTCAGCATATTA
2340 204_HRV71a   GCACGGCCAACCATACCCAAGGTTTACAATCCCCTTCATAAGCATTGCATCAGCATATTA
2341 205_HRV71b   GCACGGCCAACCATACCCAAGGTTTACAATCCCCTTCATAAGCATTGCATCAGCATATTA
2342 206_HRV71    GCACGGCCAACCATACCCAAGGTTTACAATCCCCTTCATAAGCATTGCATCAGCATATTA
2343 207_HRV8     AGTTGGACAAACTTATCCCAGATTCACCATACCTTTCTCCAGCATAGCATCAGCTTATTA
2344 208_HRV95    AGTTGGACAGACTTATCCCAGATTCACCATACCTTTCTCCAGTATAGCATCAGCTTATTA
2345 209_HRV45    GGTTGGTCAAACTTATCCCAGATTTTCTATACCTTTCTCAAGTATAGCTTCAGCTTACTA
2346 210_HRV45a   GGTTGGTCAAACTTATCCCAGATTTTCTATACCTTTCTCAAGTATAGCTTCAGCTTACTA
2347 211_HRV45b   GGTTGGTCAAACTTATCCCAGATTTTCTATACCTTTCTCAAGTATAGCTTCAGCTTACTA
2348 GROUP_1      ----GG-CA----T--CC--G--T--C--T-CC-TT-----G--T-GC-TC-G--TA-TA
2349
2350 1_HRV1A1|d   TATGTTTTATGATGGATATGATGGAGACAACACTTCTTCCAAGTATGGTAGCGTAGTTAC
2351 2_HRV1A2|d   TATGTTTTATGATGGATATGATGGAGACAACACTTCTTCCAAGTATGGTAGCGTAGTTAC
2352 3_HRV1A|cD   TATGTTTTATGATGGATATGATGGAGACAACACTTCTTCCAAGTATGGTAGCGTAGTTAC
2353 4_HRV1B1|d   CATGTTTTATGATGGATATGATGGAGATAATTCCTCTTCCAAATATGGTAGTATAGTCAC
2354 5_HRV1B2|d   CATGTTTTATGATGGATATGATGGAGATAATTCCTCTTCCAAATATGGTAGTATAGTCAC
2355 6_HRV1B      CATGTTTTATGATGGATATGATGGAGATAATTCCTCTTCCAAATATGGTAGTATAGTCAC
2356 7_HRV40a|d   CATGTTTTATGATGGATACGATGGTGATACATCGACCTCAAGATATGGCACATCAGTCAC
2357 8_HRV40b|d   CATGTTTTATGATGGATACGATGGTGATACATCGACCTCAAGATATGGCACATCAGTCAC
2358 9_HRV40      CATGTTTTATGATGGATACGATGGTGATACATCGACCTCAAGATATGGCACATCAGTCAC
2359 10_HRV85     CATGTTTTATGATGGTTATGATGGTGATACACCAGGCTCAATGTATGGGACGTCAGTCAC
2360 11_HRV85a|   CATGTTTTATGATGGTTATGATGGTGATACACCAGGCTCAATGTATGGGACGTCAGTCAC
2361 12_HRV85b|   CATGTTTTATGATGGTTATGATGGTGATACACCAGGCTCAATGTATGGGACGTCAGTCAC
2362 13_HRV56a|   CATGTTTTATGATGGTTATGATGGAGACACTTCAAGCTCCAGATATGGTACATCAGTTAC
2363 14_HRV56b|   CATGTTTTATGATGGTTATGATGGAGACACTTCAAGCTCCAGATATGGTACATCAGTTAC
2364 15_HRV56     CATGTTTTATGATGGTTATGATGGAGACACTTCAAGCTCCAGATATGGTACATCAGTTAC
2365 16_HRV54     CATGTTTTATGATGGGTATGATGGTGACGCACCTGGATCAAGATATGGGACTTCAGTTAC
2366 17_HRV98     CATGTTTTACGATGGGTATGATGGTGATGCACCTGGATCAAGATATGGAACCTCAGTCAC
2367 18_HRV59a|   CATGTTTTATGATGGTTATGATGGAGATAAATCTGAATCTAGGTATGGTGTGTCTGTAAC
2368 19_HRV59b|   CATGTTTTATGATGGTTATGATGGAGATAAATCTGAATCTAGGTATGGTGTGTCTGTAAC
2369 20_HRV59     CATGTTTTATGATGGTTATGATGGAGATAAATCTGAATCTAGGTATGGTGTGTCTGTAAC
2370 21_HRV63     CATGTTTTATGATGGATATGATGGAGATAAATCAAGCTCTAGGTATGGTGTTTCAGTTAC
2371 22_HRV63b|   CATGTTTTATGATGGATATGATGGAGATAAATCAAGCTCTAGGTATGGTGTTTCAGTTAC
2372 23_HRV63a|   CATGTTTTATGATGGATATGATGGAGATAAATCAAGCTCTAGGTATGGTGTTTCAGTTAC
2373 24_HRV39     TATGTTCTATGATGGATATGATGGTGATAAATCGTCATCTAGGTATGGTGTTTCTGTCAC
2374 25_HRV39a|   TATGTTCTATGATGGATATGATGGTGATAAATCGTCATCTAGGTATGGTGTTTCTGTCAC
2375 26_HRV39b|   TATGTTCTATGATGGATATGATGGTGATAAATCGTCATCTAGGTATGGTGTTTCTGTCAC
2376 27_HRV10a|   CATGTTCTATGATGGTTATGATGGTGATACACATGACTCACGTTATGGCACAACAGTGAT
2377 28_HRV10b|   CATGTTCTATGATGGTTATGATGGTGATACACATGACTCACGTTATGGCACAACAGTGAT
2378 29_HRV10     CATGTTCTATGATGGTTATGATGGTGATACACATGACTCACGTTATGGCACAACAGTGAT
2379 30_HRV100a   CATGTTTTATGATGGATATGATGGTGATACACATGATTCACACTATGGTACTACTGTAAT
2380 31_HRV100b   CATGTTTTATGATGGATATGATGGTGATACACATGATTCACACTATGGTACTACTGTAAT
2381 32_HRV100    CATGTTTTATGATGGATATGATGGTGATACACATGATTCACACTATGGTACTACTGTAAT
2382 33_HRV66     CATGTTCTATGATGGTTATGATGGAGATACTCCTGGGTCTCGTTATGGAACCACAGTAGT
2383 34_HRV66b|   CATGTTCTATGATGGTTATGATGGAGATACTCCTGGGTCTCGTTATGGAACCACAGTAGT
2384 35_HRV66a|   CATGTTCTATGATGGTTATGATGGAGATACTCCTGGGTCTCGTTATGGAACCACAGTAGT
2385 36_HRV77a|   CATGTTTTATGATGGCTATGATGGGGATACCTATGAATCACGTTATGGTACTACAGTGGT
2386 37_HRV77b|   CATGTTTTATGATGGCTATGATGGGGATACCTATGAATCACGTTATGGTACTACAGTGGT
2387 38_HRV77     CATGTTTTATGATGGCTATGATGGGGATACCTATGAATCACGTTATGGTACTACAGTGGT
2388 39_HRV62a    CATGTTTTATGATGGCTATAATGGTGATGACTATACAGCAAAATACGGTACCACCGTGGT
2389 40_HRV62b    CATGTTTTATGATGGCTATAATGGTGATGACTATACAGCAAAATACGGTACCACCGTGGT
2390 41_HRV25     CATGTTTTATGATGGCTATAATGGTGATGATCACACAGCGAGATATGGTACCACTGTGGT
2391 42_HRV29a    CATGTTTTATGATGGTTACAATGGAGGTGATCATACAGCAACTTATGGCACCACAGTGGT
2392 43_HRV29b    CATGTTTTATGATGGTTACAATGGAGGTGATCATACAGCAACTTATGGCACCACAGTGGT
2393 44_HRV44a    CATGTTTTATGACGGTTATAATGGAGGTGATCATACAGCAACTTATGGCACCACAGTGGT
2394 45_HRV44b    CATGTTTTATGACGGTTATAATGGAGGTGATCATACAGCAACTTATGGCACCACAGTGGT
2395 46_HRV31     CATGTTTTATGATGGTTATGATGGAGACAAAAGTGGAGCCAAGTATGGTACTACAGTAGT
2396 47_HRV31a|   CATGTTTTATGATGGTTATGATGGAGACAAAAGTGGAGCCAAGTATGGTACTACAGTAGT
2397 48_HRV31b|   CATGTTTTATGATGGTTATGATGGAGACAAAAGTGGAGCCAAGTATGGTACTACAGTAGT
2398 49_HRV47     CATGTTTTATGATGGCTATAATGGAGACAGAAGTGGAGCCAAGTATGGCACCACAGTGGT
2399 50_HRV47a|   CATGTTTTATGATGGCTATAATGGTGACAGAAGTGGAGCCAAGTATGGCACCACAGTGGT
2400 51_HRV47b|   CATGTTTTATGATGGCTATAATGGTGACAGAAGTGGAGCCAAGTATGGCACCACAGTGGT
```

FIG. D9 CONT'D

05.trace                                                                                           9/20/2007 5:04 PM

| | | |
|---|---|---|
| 2401 | 52_HRV11 | CATGTTTTATGATGGATATGATGGAGATCAACCAAACTCCAGATATGGTAATATAGTTAC |
| 2402 | 53_HRV11b\| | CATGTTTTATGATGGATATGATGGAGATCAACCAAACTCCAGATATGGTAATATAGTTAC |
| 2403 | 54_HRV11a\| | CATGTTTTATGATGGATATGATGGAGATCAACCAAACTCCAGATATGGTAATATAGTTAC |
| 2404 | 55_HRV76 | CATGTTTTATGATGGATATGATGGAGACCAACCTAGTTCTAGGTATGGTAATATAGTTAC |
| 2405 | 56_HRV76b\| | CATGTTTTATGATGGATATGATGGAGACCAACCTAGTTCTAGGTATGGTAATATAGTTAC |
| 2406 | 57_HRV76a\| | CATGTTTTATGATGGATATGATGGAGACCAACCTAGTTCTAGGTATGGTAATATAGTTAC |
| 2407 | 58_HRV33 | CATGTTCTATGATGGATATGATGGGGACCAACCCAATTCCAGGTATGGTAATATGGTTAC |
| 2408 | 59_HRV33b\| | CATGTTCTATGATGGATATGATGGGGACCAACCCAATTCCAGGTATGGTAATATGGTTAC |
| 2409 | 60_HRV33a\| | CATGTTCTATGATGGATATGATGGGGACCAACCCAATTCCAGGTATGGTAATATGGTTAC |
| 2410 | 61_HRV24a\| | CATGTTTTATGATGGATATGATGGTGATCAACACGACTCAGTGTATGGTTCAGTTGTTAC |
| 2411 | 62_HRV24b\| | CATGTTTTATGATGGATATGATGGTGATCAACACGACTCAGTGTATGGTTCAGTTGTTAC |
| 2412 | 63_HRV24 | CATGTTTTATGATGGATATGATGGTGATCAACACGACTCAGTGTATGGTTCAGTTGTTAC |
| 2413 | 64_HRV90 | TATGTTTTATGATGGATATGATGGTGACCAAACTGATTCGAGATATGGTACCATTGTTAC |
| 2414 | 65_HRV90a\| | TATGTTTTATGATGGATATGATGGTGACCAAACTGATTCGAGATATGGTACCATTGTTAC |
| 2415 | 66_HRV90b\| | TATGTTTTATGATGGATATGATGGTGACCAAACTGATTCGAGATATGGTACCATTGTTAC |
| 2416 | 67_HRV34 | CATGTTTTATGATGGATATGATGGTGATCAACATGATTCAAGATATGGTACAGTAGTGAC |
| 2417 | 68_HRV34b\| | CATGTTTTATGATGGATATGATGGTGATCAACATGATTCAAGATATGGTACAGTAGTGAC |
| 2418 | 69_HRV34a\| | CATGTTTTATGATGGATATGATGGTGATCAACATGATTCAAGATATGGTACAGTAGTGAC |
| 2419 | 70_HRV50a\| | CATGTTTTATGATGGTTATGATGGTGATAAATCTACATCCAGGTATGGTACAGTAGTTAC |
| 2420 | 71_HRV50b\| | CATGTTTTATGATGGTTATGATGGTGATAAATCTACATCCAGGTATGGTACAGTAGTTAC |
| 2421 | 72_HRV50 | CATGTTTTATGATGGTTATGATGGTGATAAATCTACATCCAGGTATGGTACAGTAGTTAC |
| 2422 | 73_HRV18a\| | CATGTTCTATGATGGCTACGACGGTGACCAGACCTCATCGCGGTATGGCACAGTTGCAAC |
| 2423 | 74_HRV18b\| | CATGTTCTATGATGGCTACGACGGTGACCAGACCTCATCGCGGTATGGCACAGTTGCAAC |
| 2424 | 75_HRV18 | CATGTTCTATGATGGCTACGACGGTGACCAGACCTCATCGCGGTATGGCACAGTTGCAAC |
| 2425 | 76_HRV55 | CATGTTCTATGATGGATATGATGGTGACCAAACTGAGTCACGCTATGGCACTGTAGTCAC |
| 2426 | 77_HRV55b\| | CATGTTCTATGATGGATATGATGGTGACCAAACTGAGTCACGCTATGGCACTGTAGTCAC |
| 2427 | 78_HRV55a\| | CATGTTCTATGATGGATATGATGGTGACCAAACTGAGTCACGCTATGGCACTGTAGTCAC |
| 2428 | 79_HRV57 | CATGTTTTATGATGGATATGATGGTGACCAAACTGAATCAAGATATGGTACTGTAGTCAC |
| 2429 | 80_HRV57a\| | CATGTTTTATGATGGATATGATGGTGACCAAACTGAATCAAGATATGGTACTGTAGTCAC |
| 2430 | 81_HRV57b\| | CATGTTTTATGATGGATATGATGGTGACCAAACTGAATCAAGATATGGTACTGTAGTCAC |
| 2431 | 82_HRV21 | CATGTTTTATGATGGTTATGATGGTGACCGACTGACTCACAATATGGTGCAGTAGTAAC |
| 2432 | 83_HRVHan | CATGTTTTATGATGGTTATGATGGTGATCAGACTGACTCACAATATGGTGCAGTGGTGAC |
| 2433 | 84_HRV43 | CATGTTTTATGATGGATATGAAGGTGACCAAAAAACATCCCGTTATGGCACAATTGCAAG |
| 2434 | 85_HRV43b\| | CATGTTTTATGATGGATATGAAGGTGACCAAAAAACATCCCGTTATGGCACAATTGCAAG |
| 2435 | 86_HRV43a\| | CATGTTTTATGATGGATATGAAGGTGACCAAAAAACATCCCGTTATGGCACAATTGCAAG |
| 2436 | 87_HRV75 | CATGTTTTATGATGGATATGAAGGGGATCAAAATACATCCCGTTATGGCACCATTGCTAG |
| 2437 | 88_HRV75b\| | CATGTTTTATGATGGATATGAAGGGGATCAAAATACATCCCGTTATGGCACCATTGCTAG |
| 2438 | 89_HRV75a\| | CATGTTTTATGATGGATATGAAGGGGATCAAAATACATCCCGTTATGGCACCATTGCTAG |
| 2439 | 96_HRV9a\|d | CATGTTCTATGATGGTTATGATGGTGG---ACCAGATTCTCTGTATGGAACAATTGTAAC |
| 2440 | 97_HRV9b\|d | CATGTTCTATGATGGTTATGATGGTGG---ACCAGATTCTCTGTATGGAACAATTGTAAC |
| 2441 | 98_HRV9 | CATGTTCTATGATGGTTATGATGGTGG---ACCAGATTCTCTGTATGGAACAATTGTAAC |
| 2442 | 99_HRV32 | CATGTTTTATGATGGTTATGATGGTGG---GCCAGATTCACAATATGGAACAATTGTAAC |
| 2443 | 100_HRV32a | CATGTTTTATGATGGTTATGATGGTGG---GCCAGATTCACAATATGGAACAATTGTAAC |
| 2444 | 101_HRV32b | CATGTTTTATGATGGTTATGATGGTGG---GCCAGATTCACAATATGGAACAATTGTAAC |
| 2445 | 102_HRV67 | CATGTTTTATGATGGCTATGATGGTGG---ACCAGATTCACTATATGGCACCATAGTAAC |
| 2446 | 103_HRV67a | CATGTTTTATGATGGCTATGATGGTGG---ACCAGATTCACTATATGGCACCATAGTAAC |
| 2447 | 104_HRV67b | CATGTTTTATGATGGCTATGATGGTGG---ACCAGATTCACTATATGGCACCATAGTAAC |
| 2448 | 105_HRV15 | CATGTTCTATGATGGATATGATGGAGATTCCACTGAATCACATTATGGTACAGTGGTCAC |
| 2449 | 106_HRV15a | CATGTTCTATGATGGATATGATGGAGATTCCACTGAATCACATTATGGTACAGTGGTCAC |
| 2450 | 107_HRV15b | CATGTTCTATGATGGATATGATGGAGATTCCACTGAATCACATTATGGTACAGTGGTCAC |
| 2451 | 108_HRV74a | CATGTTTTATGATGGATATGATGGAGACTCTACTGAATCACATTATGGTACAGTAGTAAC |
| 2452 | 109_HRV74b | CATGTTTTATGATGGATATGATGGAGACTCTACTGAATCACATTATGGTACAGTAGTAAC |
| 2453 | 110_HRV74 | CATGTTTTATGATGGATATGATGGAGACTCTACTGAATCACATTATGGTACAGTAGTAAC |
| 2454 | 111_HRV38a | TATGTTTTATGATGGATATGATGGGGACTCAACAGAATCACATTATGGGACAGCGGTGAC |
| 2455 | 112_HRV38b | TATGTTTTATGATGGATATGATGGGGACTCAACAGAATCACATTATGGGACAGCGGTGAC |
| 2456 | 113_HRV38 | TATGTTTTATGATGGATATGATGGGGACTCAACAGAATCACATTATGGGACAGCGGTGAC |
| 2457 | 114_HRV60 | CATGTTTTATGATGGTTATGATGGTCACTCAACTGAATCACATTATGGGACGGTTGTGAC |
| 2458 | 115_HRV60a | CATGTTTTATGATGGTTATGATGGTCACTCAACTGAATCACATTATGGGACGGTTGTGAC |
| 2459 | 116_HRV60b | CATGTTTTATGATGGTTATGATGGTCACTCAACTGAATCACATTATGGGACGGTTGTGAC |
| 2460 | 117_HRV64a | CATGTTTTATGATGGTTATGACGGTGG---ACCTGGTTCCCGTTATGGCGCAGTGGTGAC |
| 2461 | 118_HRV64b | CATGTTTTATGATGGTTATGACGGTGG---ACCTGGTTCCCGTTATGGCGCAGTGGTGAC |
| 2462 | 119_HRV64 | CATGTTTTATGATGGTTATGACGGTGG---ACCTGGTTCCCGTTATGGCGCAGTGGTGAC |
| 2463 | 120_HRV94a | CATGTTCTATGATGGTTATGATGGTGG---ACCTGGCTCACGCTATGGCACAGTGGTGAC |
| 2464 | 121_HRV94b | CATGTTCTATGATGGTTATGATGGTGG---ACCTGGCTCACGCTATGGCACAGTGGTGAC |
| 2465 | 122_HRV94 | CATGTTCTATGATGGTTATGATGGTGG---ACCTGGCTCACGCTATGGCACAGTGGTGAC |

FIG. D9 CONT'D 05.trace  9/20/2007 5:04 PM

```
2466 123_HRV22   CATGTTTTATGATGGGTATGATGGAGG---TCCCGGATCACGTTATGGAGCAGTGGTAAC
2467 124_HRV22a  CATGTTTTATGATGGGTATGATGGAGG---TCCCGGATCACGTTATGGAGCAGTGGTAAC
2468 125_HRV22b  CATGTTTTATGATGGGTATGATGGAGG---TCCCGGATCACGTTATGGAGCAGTGGTAAC
2469 126_HRV82   TATGTTCTATGATGGCTATGATGGTGATGCTCCCGGATCGCGATACGGGACCATAGTGAC
2470 127_HRV82b  TATGTTCTATGATGGCTATGATGGTGATGCTCCCGGATCGCGATACGGGACCATAGTGAC
2471 128_HRV82a  TATGTTCTATGATGGCTATGATGGTGATGCTCCCGGATCGCGATACGGGACCATAGTGAC
2472 129_HRV19   CATGTTTTATGATGGGTATGATGGAGATTCACCAGGATCCCGCTATGGAACAATAGTAAC
2473 130_HRV19a  CATGTTTTATGATGGGTATGATGGAGATTCACCAGGATCCCGCTATGGAACAATAGTAAC
2474 131_HRV19b  CATGTTTTATGATGGGTATGATGGAGATTCACCAGGATCCCGCTATGGAACAATAGTAAC
2475 132_HRV13   TATGTTTTATGATGGATATAATGGAGATTCCTCAGATGCACGCTATGGGACAACAATCAC
2476 133_HRV13a  TATGTTTTATGATGGATATAATGGAGATTCCTCAGATGCACGCTATGGGACAACAATCAC
2477 134_HRV13b  TATGTTTTATGATGGATATAATGGAGATTCCTCAGATGCACGCTATGGGACAACAATCAC
2478 135_HRV41   CATGTTTTATGATGGTTATGAAGAAGGCTCTACAAATGCACGCTATGGAACAACAGTCAC
2479 136_HRV41a  CATGTTTTATGATGGTTATGAAGAAGGCTCTACAAATGCACGCTATGGAACAACAGTCAC
2480 137_HRV41b  CATGTTTTATGATGGTTATGAAGAAGGCTCTACAAATGCACGCTATGGAACAACAGTCAC
2481 138_HRV73   TATGTTTTATGATGGATATGATGGTGACTCCACACAATCACATTATGGCACCACAGTAGT
2482 139_HRV73b  TATGTTTTATGATGGATATGATGGTGACTCCACACAATCACATTATGGCACCACAGTAGT
2483 140_HRV73a  TATGTTTTATGATGGATATGATGGTGACTCCACACAATCACATTATGGCACCACAGTAGT
2484 141_HRV61   TATGTTTTATGATGGTTATGATGGAGATTCTGAAATAACGCGCTATGGAACATCAGTGAC
2485 142_HRV61a  TATGTTTTATGATGGTTATGATGGAGATTCTGAAATAACGCGCTATGGAACATCAGTGAC
2486 143_HRV61b  TATGTTTTATGATGGTTATGATGGAGATTCTGAAATAACGCGCTATGGAACATCAGTGAC
2487 144_HRV96   CATGTTTTATGATGGATATGATGGTGACTCTGAATCAACACGCTATGGAACATCTGTTAC
2488 145_HRV96b  CATGTTTTATGATGGATATGATGGTGACTCTGAATCAACACGCTATGGAACATCTGTTAC
2489 146_HRV96a  CATGTTTTATGATGGATATGATGGTGACTCTGAATCAACACGCTATGGAACATCTGTTAC
2490  90_HRV16a|  CATGTTTTATGATGGTTATGATGGAGACACATATAAATCCAGATATGGAACTGTAGTCAC
2491  91_HRV16b|  CATGTTTTATGATGGTTATGATGGAGACACATATAAATCCAGATATGGAACTGTAGTCAC
2492  92_1AYM_A   CATGTTTTATGATGGTTATGATGGAGACACATATAAATCCAGATATGGAACTGTAGTCAC
2493  93_HRV81a|  CATGTTCTATGATGGATATGATGGTGATACTTATCACTCCAGATACGGGACTGTAGTCAC
2494  94_HRV81b|  CATGTTCTATGATGGATATGATGGTGATACTTATCACTCCAGATACGGGACTGTAGTCAC
2495  95_HRV81|   CATGTTCTATGATGGATATGATGGTGATACTTATCACTCCAGATACGGGACTGTAGTCAC
2496 147_HRV2    CATGTTTTATGATGGGTATGATG------AACAAGATCAAAACTATGGTACAGCAAGCAC
2497 148_HRV2a|  CATGTTTTATGATGGGTATGATG------AACAAGATCAAAACTATGGTACAGCAAGCAC
2498 149_HRV2b|  CATGTTTTATGATGGGTATGATG------AACAAGATCAAAACTATGGTACAGCAAGCAC
2499 150_HRV49a  CATGTTTTATGATGGATATAATG------AACAGGGCCAAAATTATGGTACGGTAAGTAC
2500 151_HRV49b  CATGTTTTATGATGGATATAATG------AACAGGGCCAAAATTATGGTACGGTAAGTAC
2501 152_HRV49   CATGTTTTATGATGGATATAATG------AACAGGGCCAAAATTATGGTACGGTAAGTAC
2502 153_HRV23a  CATGTTTTATGATGGATACAATG------AGAAAGGCACGCATTATGGAACAGTTAGCAC
2503 154_HRV23b  CATGTTTTATGATGGATACAATG------AGAAAGGCACGCATTATGGAACAGTTAGCAC
2504 155_HRV23   CATGTTTTATGATGGATACAATG------AGAAAGGCACGCATTATGGAACAGTTAGCAC
2505 156_HRV30a  CATGTTCTATGATGGATACAATG------AGGGAGGCACAAATTATGGTACAGTGAGCAC
2506 157_HRV30b  CATGTTCTATGATGGATACAATG------AGGGAGGCACAAATTATGGTACAGTGAGCAC
2507 158_HRV30   CATGTTCTATGATGGATACAATG------AGGGAGGCACAAATTATGGTACAGTGAGCAC
2508 159_HRV7    TATGTTCTATGATGGATATGATGGTGATGCGTCATCCAAATATGGTTCCGTAGTAAC
2509 160_HRV7b|  TATGTTCTATGATGGATATGATGGTGATGATGCGTCATCCAAATATGGTTCCGTAGTAAC
2510 161_HRV7a|  TATGTTCTATGATGGATATGATGGTGATGATGCGTCATCCAAATATGGTTCCGTAGTAAC
2511 162_HRV88   TATGTTTTATGATGGATATGATGGTGATGATGCATCATCTAGGTATGGCTCAGTGGTAAC
2512 163_HRV88a  TATGTTTTATGATGGATATGATGGTGATGATGCATCATCTAGGTATGGCTCAGTGGTAAC
2513 164_HRV88b  TATGTTTTATGATGGATATGATGGTGATGATGCATCATCTAGGTATGGCTCAGTGGTAAC
2514 165_HRV36a  TATGTTTTATGATGGTTATGATGGTGATAATGCCGCATCAAAATATGGATCTGTGGTTAC
2515 166_HRV36b  TATGTTTTATGATGGTTATGATGGTGATAATGCCGCATCAAAATATGGATCTGTGGTTAC
2516 167_HRV36   TATGTTTTATGATGGTTATGATGGTGATAATGCCGCATCAAAATATGGATCTGTGGTTAC
2517 168_HRV89a  CATGTTTTATGATGGTTATGATGGTGATAGTGCAGCATCAAAATACGGTTCTGTAGTCAC
2518 169_HRV89b  CATGTTTTATGATGGTTATGATGGTGATAGTGCAGCATCAAAATACGGTTCTGTAGTCAC
2519 170_HRV89   CATGTTTTATGATGGTTATGATGGTGATAGTGCAGCATCAAAATACGGTTCTGTAGTCAC
2520 171_HRV58   TATGTTTTATGATGGCTATGATGGTGATGATGCTAAATCAATATATGGTTCTGTGGTAAC
2521 172_HRV58a  TATGTTTTATGATGGCTATGATGGTGATGATGCTAAATCAATATATGGTTCTGTGGTAAC
2522 173_HRV58b  TATGTTTTATGATGGCTATGATGGTGATGATGCTAAATCAATATATGGTTCTGTGGTAAC
2523 174_HRV12a  CATGTTTTATGATGGTTATGCTGATGACAACCCAAGTGCACCTTATGGAACTGTAGTTAC
2524 175_HRV12b  CATGTTTTATGATGGTTATGCTGATGACAACCCAAGTGCACCTTATGGAACTGTAGTTAC
2525 176_HRV12   CATGTTTTATGATGGTTATGCTGATGACAACCCAAGTGCACCTTATGGAACTGTAGTTAC
2526 177_HRV78a  CATGTTTTATGATGGATACTCGGATGACAGCACATCCTCTCCATATGGCACTGTAGTTAC
2527 178_HRV78b  CATGTTTTATGATGGATACTCGGATGACAGCACATCCTCTCCATATGGCACTGTAGTTAC
2528 179_HRV78   CATGTTTTATGATGGATACTCGGATGACAGCACATCCTCTCCATATGGCACTGTAGTTAC
2529 180_HRV20   TATGTTTTATGATGGTTATGAAGATGATAAGG---GAAGTGTGTATGGGTCTGTTGTCAC
2530 181_HRV20a  TATGTTTTATGATGGTTATGAAGATGATAAGG---GAAGTGTGTATGGGTCTGTTGTCAC
```

FIG. D9 CONT'D

```
05.trace                                                                     9/20/2007 5:04 PM 2531  182_HRV20b   TATGTTTTATGATGGTTATGAAGATGATAAGG---GAAGTGTGTATGGGTCTGTTGTCAC
2532  183_HRV68    TATGTTTTATGATGGATATGAGGATGACAAAG---GAAGTGTGTATGGATCTGTTGTTAC
2533  184_HRV68a   TATGTTTTATGATGGATATGAGGATGACAAAG---GAAGTGTGTATGGATCTGTTGTTAC
2534  185_HRV68b   TATGTTTTATGATGGATATGAGGATGACAAAG---GAAGTGTGTATGGATCTGTTGTTAC
2535  186_HRV28    CATGTTTTATGATGGTTATGAAGATGACAATG---GAACTACCTATGGTGCAGTGGTTAC
2536  187_HRV28a   CATGTTTTATGATGGTTATGAAGATGACAATG---GAACTACCTATGGTGCAGTGGTTAC
2537  188_HRV28b   CATGTTTTATGATGGTTATGAAGATGACAATG---GAACTACCTATGGTGCAGTGGTTAC
2538  189_HRV53a   TATGTTCTATGATGGGTATGAAGATGACAATG---GCACCACTTATGGGGCTGTTGTTAC
2539  190_HRV53b   TATGTTCTATGATGGGTATGAAGATGACAATG---GCACCACTTATGGGGCTGTTGTTAC
2540  191_HRV53    TATGTTCTATGATGGGTATGAAGATGACAATG---GCACCACTTATGGGGCTGTTGTTAC
2541  192_HRV46a   CATGTTTTATGATGGCTACGAAAGTGATAAAG---GCAAGATCTATGGAACTGCAGTCAC
2542  193_HRV46b   CATGTTTTATGATGGCTACGAAAGTGATAAAG---GCAAGATCTATGGAACTGCAGTCAC
2543  194_HRV46    CATGTTTTATGATGGCTACGAAAGTGATAAAG---GCAAGATCTATGGAACTGCAGTCAC
2544  195_HRV80a   CATGTTCTATGATGGGTATGAGAGTGATAAAG---GCAACATTTATGGAACAGCAGTTAC
2545  196_HRV80b   CATGTTCTATGATGGGTATGAGAGTGATAAAG---GCAACATTTATGGAACAGCAGTTAC
2546  197_HRV80    CATGTTCTATGATGGGTATGAGAGTGATAAAG---GCAACATTTATGGAACAGCAGTTAC
2547  198_HRV51    CATGTTTTATGATGGGTATGAAGGTGATAGTTTGACCTCACAGTACGGTTCAGTAGTCAC
2548  199_HRV51a   CATGTTTTATGATGGGTATGAAGGTGATAGTTTGACCTCACAGTACGGTTCAGTAGTCAC
2549  200_HRV51b   CATGTTTTATGATGGGTATGAAGGTGATAGTTTGACCTCACAGTACGGTTCAGTAGTCAC
2550  201_HRV65a   CATGTTCTATGATGGTTATGAGGGTGATGACCCAAATTCAAAATATGGTTCAGTGGTTAC
2551  202_HRV65b   CATGTTCTATGATGGTTATGAGGGTGATGACCCAAATTCAAAATATGGTTCAGTGGTTAC
2552  203_HRV65    CATGTTCTATGATGGTTATGAGGGTGATGACCCAAATTCAAAATATGGTTCAGTGGTTAC
2553  204_HRV71a   CATGTTCTATGATGGGTATGAAGGTGATGCCCTCAGTTCTAAATATGGCTCAGTAGTTAC
2554  205_HRV71b   CATGTTCTATGATGGGTATGAAGGTGATGCCCTCAGTTCTAAATATGGCTCAGTAGTTAC
2555  206_HRV71    CATGTTCTATGATGGGTATGAAGGTGATGCCCTCAGTTCTAAATATGGCTCAGTAGTTAC
2556  207_HRV8     CATGTTCTATGATGGTTATGATTCAGATGGTTTAGATGCTATTTATGGTATTCCTGTTAC
2557  208_HRV95    CATGTTCTATGATGGTTATGATTCAGATGGTTTAGATGCTATTTATGGTATTCCTGTTAC
2558  209_HRV45    CATGTTTTATGATGGATACGACACTGATGGCACAGATGCAGTGTATGGTGTTAGTGTGAC
2559  210_HRV45a   CATGTTTTATGATGGATACGACACTGATGGCACAGATGCAGTGTATGGTGTTAGTGTGAC
2560  211_HRV45b   CATGTTTTATGATGGATACGACACTGATGGCACAGATGCAGTGTATGGTGTTAGTGTGAC
2561  GROUP_1      -ATGTT-TA-GA-GG-TA----------------------TA-GG------------
2562
2563  1_HRV1A1|d   TAATGATATGGGTACTATATGCTCAAGAATAGTTACAGAAAAACAGAAACATTCTGTTGT
2564  2_HRV1A2|d   TAATGATATGGGTACTATATGCTCAAGAATAGTTACAGAAAAACAGAAACATTCTGTTGT
2565  3_HRV1A|cD   TAATGATATGGGTACTATATGCTCAAGAATAGTTACAGAAAAACAGAAACATTCTGTTGT
2566  4_HRV1B1|d   CAATGATATGGGAACCATATGTTCAAGAATAGTTACAGAGAAGCAGGAACACCCTGTCGT
2567  5_HRV1B2|d   CAATGATATGGGAACCATATGTTCAAGAATAGTTACAGAGAAGCAGGAACACCCTGTCGT
2568  6_HRV1B      CAATGATATGGGAACCATATGTTCAAGAATAGTTACAGAGAAGCAGGAACACCCTGTCGT
2569  7_HRV40a|d   TAACCATATGGGAACGCTATGCTCAAGAATAGTCACCAACAAGCAGCAGCATGAAGTTGA
2570  8_HRV40b|d   TAACCATATGGGAACGCTATGCTCAAGAATAGTCACCAACAAGCAGCAGCATGAAGTTGA
2571  9_HRV40      TAACCATATGGGAACGCTATGCTCAAGAATAGTCACCAACAAGCAGCAGCATGAAGTTGA
2572  10_HRV85     CAACCACATGGGAACACTGTGCTCGAGGATAGTTACCAACAAACAGCAGCATGAGGTTGA
2573  11_HRV85a|   CAACCACATGGGAACACTGTGCTCGAGGATAGTTACCAACAAACAGCAGCATGAGGTTGA
2574  12_HRV85b|   CAACCACATGGGAACACTGTGCTCGAGGATAGTTACCAACAAACAGCAGCATGAGGTTGA
2575  13_HRV56a|   AAACCACATGGGGACACTCTGTTCAAGAATTGTGACAAATAAACAACTTCATCCTGTTGA
2576  14_HRV56b|   AAACCACATGGGGACACTCTGTTCAAGAATTGTGACAAATAAACAACTTCATCCTGTTGA
2577  15_HRV56     AAACCACATGGGGACACTCTGTTCAAGAATTGTGACAAATAAACAACTTCATCCTGTTGA
2578  16_HRV54     CAATCATATGGGTACTTTGTGTTCAAGAGTGGTTACTGATAAACAAAAACACCCAGTTGA
2579  17_HRV98     TAATGATATGGGCACTTTGTGTTCAAGAATAGTTACTGGCAAACAAGAACACCCAGTTGA
2580  18_HRV59a|   CAACCACATGGGCACTTTATGTTCTAGAATAGTTACAAACAGTCAGGAGCATCCAGTGGA
2581  19_HRV59b|   CAACCACATGGGCACTTTATGTTCTAGAATAGTTACAAACAGTCAGGAGCATCCAGTGGA
2582  20_HRV59     CAACCACATGGGCACTTTATGTTCTAGAATAGTTACAAACAGTCAGGAGCATCCAGTGGA
2583  21_HRV63     TAACCACATGGGGACTTTATGTTCTAGAATTGTAACAAACAGCCAAGAACATCCAGTTGA
2584  22_HRV63b|   TAACCACATGGGGACTTTATGTTCTAGAATTGTAACAAACAGCCAAGAACATCCAGTTGA
2585  23_HRV63a|   TAACCACATGGGGACTTTATGTTCTAGAATTGTAACAAACAGCCAAGAACATCCAGTTGA
2586  24_HRV39     TAATGATATGGGTACACTTTGCACTAGAATTGTAACAAACCAACAGGAACACCTAGTGGA
2587  25_HRV39a|   TAATGATATGGGTACACTTTGCACTAGAATTGTAACAAACCAACAGGAACACCTAGTGGA
2588  26_HRV39b|   TAATGATATGGGTACACTTTGCACTAGAATTGTAACAAACCAACAGAAACACCTAGTGGA
2589  27_HRV10a|   AAATCACATGGGCACTTTGTGCATGCGAATAGTCACAAACCAGCAAGCACATGAGGTGGA
2590  28_HRV10b|   AAATCACATGGGCACTTTGTGCATGCGAATAGTCACAAACCAGCAAGCACATGAGGTGGA
2591  29_HRV10     AAATCACATGGGCACTTTGTGCATGCGAATAGTCACAAACCAGCAAGCACATGAGGTGGA
2592  30_HRV100a   TAACCACATGGGTACACTTTGTATGAGGATAGTTACAAATCAGCAAGCACATGAGGTGGA
2593  31_HRV100b   TAACCACATGGGTACACTTTGTATGAGGATAGTTACAAATCAGCAAGCACATGAGGTGGA
2594  32_HRV100    TAACCACATGGGTACACTTTGTATGAGGATAGTTACAAATCAGCAAGCACATGAGGTGGA
2595  33_HRV66     TAATCATATGGGTACATTATGTATTAGGATTGTTACAAATGAACAGCACCATAATGTTGA
```

FIG. D9 CONT'D

```
05.trace                                                                               9/20/2007 5:04 PM 2596  34_HRV66b|    TAATCATATGGGTACATTATGTATTAGGATTGTTACAAATGAACAGCACCATAATGTTGA
2597  35_HRV66a|    TAATCATATGGGTACATTATGTATTAGGATTGTTACAAATGAACAGCACCATAATGTTGA
2598  36_HRV77a|    TAATCACATGGGCACACTGTGCATTAGAATAGTCACTAATCAGCAAAATCATGAGGTTGA
2599  37_HRV77b|    TAATCACATGGGCACACTGTGCATTAGAATAGTCACTAATCAGCAAAATCATGAGGTTGA
2600  38_HRV77     TAATCACATGGGCACACTGTGCATTAGAATAGTCACTAATCAGCAAAATCATGAGGTTGA
2601  39_HRV62a    TAATCGTATGGGGCACTGTGTATGAGGATTGTCACAAACAAACAAGTTCATGATGTTGA
2602  40_HRV62b    TAATCGTATGGGGGCACTGTGTATGAGGATTGTCACAAACAAACAAGTTCATGATGTTGA
2603  41_HRV25     TAACCGTATGGGAGCACTGTGCATGAGAATTGTCACAAATAAACAAGTCCATGATGTTGA
2604  42_HRV29a    TAACCGGATGGGGACGCTTTGTGTCAGAATTGTTACAGGCAAACAAGCTCATGATGTTCA
2605  43_HRV29b    TAACCGGATGGGGACGCTTTGTGTCAGAATTGTTACAGGCAAACAAGCTCATGATGTTCA
2606  44_HRV44a    TAACCGGATGGGGACGCTTTGCGTCAGGATCGTTACGGGCAAACAGGCTCATGATGTCCA
2607  45_HRV44b    TAACCGGATGGGGACGCTTTGCGTCAGGATCGTTACGGGCAAACAGGCTCATGATGTCCA
2608  46_HRV31     TAATCGCATGGGTGCACTATGCATGAGAGTTGTCACTAACAAACAAGCTCATAAAGTTGA
2609  47_HRV31a|   TAATCGCATGGGTGCACTATGCATGAGAGTTGTCACTAACAAACAAGCTCATAAAGTTGA
2610  48_HRV31b|   TAATCGCATGGGTGCACTATGCATGAGAGTTGTCACTAACAAACAAGCTCATAAAGTTGA
2611  49_HRV47     CAATCGCATGGGTGCATTGTGTATGAGAGTTGTAACAAACAAGCAACTCCATAAAGTTGA
2612  50_HRV47a|   CAATCGCATGGGTGCACTATGCATGAGAGTTGTAACAAACAAGCAACTCCATAAAGTTGA
2613  51_HRV47b|   CAATCGCATGGGTGCATTGTGTATGAGAGTTGTAACAAACAAGCAACTCCATAAAGTTGA
2614  52_HRV11     CAATGATATGGGCACTCTGTGTTATAGAATAGTAACTGATGACCATAGACACAAAATTGA
2615  53_HRV11b|   CAATGATATGGGCACTCTGTGTTATAGAATAGTAACTGATGACCATAGACACAAAATTGA
2616  54_HRV11a|   CAATGATATGGGCACTCTGTGTTATAGAATAGTAACTGATGACCATAGACACAAAATTGA
2617  55_HRV76     CAATGACATGGGCACCCTATGTTCCAGGATAGTAACTGATGATCATAAGCACAAGATTGA
2618  56_HRV76b|   CAATGACATGGGCACCCTATGTTCCAGGATAGTAACTGATGATCATAAGCACAAGATTGA
2619  57_HRV76a|   CAATGACATGGGCACCCTATGTTCCAGGATAGTAACTGATGATCATAAGCACAAGATTGA
2620  58_HRV33     CAATGACATGGGCACTTTATGCTCTAGAATAGTTACAGATAATCATAAGCATCCAATAGA
2621  59_HRV33b|   CAATGACATGGGCACTTTATGCTCTAGAATAGTTACAGATAATCATAAGCATCCAATAGA
2622  60_HRV33a|   CAATGACATGGGCACTTTATGCTCTAGAATAGTTACAGATAATCATAAGCATCCAATAGA
2623  61_HRV24a|   AAACGACATGGGAACTCTATGCTATAGAATAGTCACTGACAAGCATAATCACCAAATAGA
2624  62_HRV24b|   AAACGACATGGGAACTCTATGCTATAGAATAGTCACTGACAAGCATAATCACCAAATAGA
2625  63_HRV24     AAACGACATGGGAACTCTATGCTATAGAATAGTCACTGACAAGCATAATCACCAAATAGA
2626  64_HRV90     TAATGATATGGGAACCTTATGTTATAGAATAGTTACAGATGAACATGCCCACAAAATAGA
2627  65_HRV90a|   TAATGATATGGGAACCTTATGTTATAGAATAGTTACAGATGAACATGCCCACAAAATAGA
2628  66_HRV90b|   TAATGATATGGGAACCTTATGTTATAGAATAGTTACAGATGAACATGCCCACAAAATAGA
2629  67_HRV34     TAATGACATGGGTACTTTATGCTCCAGAATTGTAACTGATGAACACCAAAACAGAGTAGA
2630  68_HRV34b|   TAATGACATGGGTACTTTATGCTCCAGAATTGTAACTGATGAACACCAAAACAGAGTAGA
2631  69_HRV34a|   TAATGACATGGGTACTTTATGCTCCAGAATTGTAACTGATGAACACCAAAACAGAGTAGA
2632  70_HRV50a|   CAATGACATGGGCACTTTGTGTTCTAGGATTGTCACTGATGAGCACCAAAATAAAGTGGA
2633  71_HRV50b|   CAATGACATGGGCACTTTGTGTTCTAGGATTGTCACTGATGAGCACCAAAATAAAGTGGA
2634  72_HRV50     CAATGACATGGGCACTTTGTGTTCTAGGATTGTCACTGATGAGCACCAAAATAAAGTGGA
2635  73_HRV18a|   AAATGACATGGGTACCTTGTGCTCTAGAATAGTCACAGATAAACATAAGAATGAGGTGGA
2636  74_HRV18b|   AAATGACATGGGTACCTTGTGCTCTAGAATAGTCACAGATAAACATAAGAATGAGGTGGA
2637  75_HRV18     AAATGACATGGGTACCTTGTGCTCTAGAATAGTCACAGATAAACATAAGAATGAGGTGGA
2638  76_HRV55     TAATGACATGGGTACTTTATGTTCTAGAATAATAACTGATAACCATAAGCACCCAATTGA
2639  77_HRV55b|   TAATGACATGGGTACTTTATGTTCTAGAATAATAACTGATAACCATAAGCACCCAATTGA
2640  78_HRV55a|   TAATGACATGGGTACTTTATGTTCTAGAATAATAACTGATAACCATAAGCACCCAATTGA
2641  79_HRV57     TAATGACATGGGCACTTTATGTTCTAGAATTGTTACTGACCAGCACACACATCCCATAAA
2642  80_HRV57a|   TAATGACATGGGCACTTTATGTTCTAGAATTGTTACTGACCAGCACACACATCCCATAAA
2643  81_HRV57b|   TAATGACATGGGCACTTTATGTTCTAGAATTGTTACTGACCAGCACACACATCCCATAAA
2644  82_HRV21     TAATGATATGGGATCTCTATGCTACAGAATAGTAACTGGCCAGCATAAGCATAAGATAGA
2645  83_HRVHan    TAATGATATGGGATCTCTATGCTATAGAATAGTAACTGATCAGCATAAGCACAAGATAGA
2646  84_HRV43     CAACCACATGGGAACATTATGTTCTAGGATAGTTACAGAAGAACACCAAAATCAAATCGA
2647  85_HRV43b|   CAACCACATGGGAACATTATGTTCTAGGATAGTTACAGAAGAACACCAAAATCAAATCGA
2648  86_HRV43a|   CAACCACATGGGAACATTATGTTCTAGGATAGTTACAGAAGAACACCAAAATCAAATCGA
2649  87_HRV75     TAATCACATGGGGACACTGTGTTCTAGAATAGTTACAGAAGAACATCGAAATAAAGTTGA
2650  88_HRV75b|   TAATCACATGGGGACACTGTGTTCTAGAATAGTTACAGAAGAACATCGAAATAAAGTTGA
2651  89_HRV75a|   TAATCACATGGGGACACTGTGTTCTAGAATAGTTACAGAAGAACATCGAAATAAAGTTGA
2652  96_HRV9a|d   AAATGATATGGGATCTTTATGTTCCCGTGTAGTTACTGAAGAGCATGGACCCCGTGTCAA
2653  97_HRV9b|d   AAATGATATGGGATCTTTATGTTCCCGTGTAGTTACTGAAGAGCATGGACCCCGTGTCAA
2654  98_HRV9      AAATGATATGGGATCTTTATGTTCCCGTGTAGTTACTGAAGAGCATGGACCCCGTGTCAA
2655  99_HRV32     AAATGATATGGGTTCCCTGTGTTCTCGTATAGTCACCGAAGAGCACGGATCCCGTGTTGA
2656  100_HRV32a   AAATGATATGGGTTCCCTGTGTTCTCGTATAGTCACCGAAGAGCACGGATCCCGTGTTGA
2657  101_HRV32b   AAATGATATGGGTTCCCTGTGTTCTCGTATAGTCACCGAAGAGCACGGATCCCGTGTTGA
2658  102_HRV67    TAATGATATGGGTTCCTTGTGTTCGCGTATAGTTACTGAAGAACATGGTTCTCGCGTAAA
2659  103_HRV67a   TAATGATATGGGTTCCTTGTGTTCGCGTATAGTTACTGAAGAACATGGTTCTCGCGTAAA
2660  104_HRV67b   TAATGATATGGGTTCCTTGTGTTCGCGTATAGTTACTGAAGAACATGGTTCTCGCGTAAA
```

FIG. D9 CONT'D 05.trace                                                                9/20/2007 5:04 PM

```
2661  105_HRV15     TAATGACATGGGGACACTGTGTTCTAGAATAGTAACTGAAGAGCATGGGACACGTGTAGA
2662  106_HRV15a    TAATGACATGGGGACACTGTGTTCTAGAATAGTAACTGAAGAGCATGGGACACGTGTAGA
2663  107_HRV15b    TAATGACATGGGGACACTGTGTTCTAGAATAGTAACTGAAGAGCATGGGACACGTGTAGA
2664  108_HRV74a    AAATGACATGGGAACTCTATGTTCTAGAATTGTGACTGAAGAACACGATGCACGTGTGGA
2665  109_HRV74b    AAATGACATGGGAACTCTATGTTCTAGAATTGTGACTGAAGAACACGATGCACGTGTGGA
2666  110_HRV74     AAATGACATGGGAACTCTATGTTCTAGAATTGTGACTGAAGAACACGATGCACGTGTGGA
2667  111_HRV38a    CAATGATATGGGGACACTTTGTTCAAGAATAGTCACTGAAAATCATGGGACCCAAGTGAA
2668  112_HRV38b    CAATGATATGGGGACACTTTGTTCAAGAATAGTCACTGAAAATCATGGGACCCAAGTGAA
2669  113_HRV38     CAATGATATGGGGACACTTTGTTCAAGAATAGTCACTGAAAATCATGGGACCCAAGTGAA
2670  114_HRV60     CAATGACATGGGAACGTTGTGCTCCAGAATAGTTACTGAACACCATGGTACACAGGTTCA
2671  115_HRV60a    CAATGACATGGGAACGTTGTGCTCCAGAATAGTTACTGAACACCATGGTACACAGGTTCA
2672  116_HRV60b    CAATGACATGGGAACGTTGTGCTCCAGAATAGTTACTGAACACCATGGTACACAGGTTCA
2673  117_HRV64a    AAATGATATGGGCACTTTGTGTTCTAGAATTGTGACTGAGGAACACACAACACAGGTCAA
2674  118_HRV64b    AAATGATATGGGCACTTTGTGTTCTAGAATTGTGACTGAGGAACACACAACACAGGTCAA
2675  119_HRV64     AAATGATATGGGCACTTTGTGTTCTAGAATTGTGACTGAGGAACACACAACACAGGTCAA
2676  120_HRV94a    AAATGACATGGGAACATTATGCTCCAGGATTGTGACTGAGGAGCACAAGACACAGGTTAA
2677  121_HRV94b    AAATGACATGGGAACATTATGCTCCAGGATTGTGACTGAGGAGCACAAGACACAGGTTAA
2678  122_HRV94     AAATGACATGGGAACATTATGCTCCAGGATTGTGACTGAGGAGCACAAGACACAGGTTAA
2679  123_HRV22     AAATGATATGGGCACACTGTGCTCTAGGATTGTGACTGAAGAACACCAGACACAAGTCAA
2680  124_HRV22a    AAATGATATGGGCACACTGTGCTCTAGGATTGTGACTGAAGAACACCAGACACAAGTCAA
2681  125_HRV22b    AAATGATATGGGCACACTGTGCTCTAGGATTGTGACTGAAGAACACCAGACACAAGTCAA
2682  126_HRV82     AAATGACATGGGTACACTGTGTTCTAGAATTGTAACTGAAGAACACCAGACTCAAGTCAG
2683  127_HRV82b    AAATGACATGGGTACACTGTGTTCTAGAATTGTAACTGAAGAACACCAGACTCAAGTCAG
2684  128_HRV82a    AAATGACATGGGTACACTGTGTTCTAGAATTGTAACTGAAGAACACCAGACTCAAGTCAG
2685  129_HRV19     TAATGATATGGGAACCTTATGCTCCAGAATAGTAACTGATGAACACCAAACACAGGTTGC
2686  130_HRV19a    TAATGATATGGGAACCTTATGCTCCAGAATAGTAACTGATGAACACCAAACACAGGTTGC
2687  131_HRV19b    TAATGATATGGGAACCTTATGCTCCAGAATAGTAACTGATGAACACCAAACACAGGTTGC
2688  132_HRV13     TAATGATATGGGCACACTTTGCTTCAGAATAGTAACTGAAGAACATACTAACAAGGTCAA
2689  133_HRV13a    TAATGATATGGGCACACTTTGCTTCAGAATAGTAACTGAAGAACATACTAACAAGGTCAA
2690  134_HRV13b    TAATGATATGGGCACACTTTGCTTCAGAATAGTAACTGAAGAACATACTAACAAGGTCAA
2691  135_HRV41     AAATGACATGGGTACATTATGCTTTAGAATAGTTACTGAAGAACACACCAACAAAGTTAA
2692  136_HRV41a    AAATGACATGGGTACATTATGCTTTAGAATAGTTACTGAAGAACACACCAACAAAGTTAA
2693  137_HRV41b    AAATGACATGGGTACATTATGCTTTAGAATAGTTACTGAAGAACACACCAACAAAGTTAA
2694  138_HRV73     TAATGACATGGGCACATTATGCTTTAGGATAGTGACTGAAGAACACACTAGCAGGGTAAA
2695  139_HRV73b    TAATGACATGGGCACATTATGCTTTAGGATAGTGACTGAAGAACACACTAGCAGGGTAAA
2696  140_HRV73a    TAATGACATGGGCACATTATGCTTTAGGATAGTGACTGAAGAACACACTAGCAGGGTAAA
2697  141_HRV61     AAATGATATGGGTGCATTGTGCTTTAGAATAGTAACTGAACAGCATACAAATCAAGTTAA
2698  142_HRV61a    AAATGATATGGGTGCATTGTGCTTTAGAATAGTAACTGAACAGCATACAAATCAAGTTAA
2699  143_HRV61b    AAATGATATGGGTGCATTGTGCTTTAGAATAGTAACTGAACAGCATACAAATCAAGTTAA
2700  144_HRV96     CAATGACATGGGCACTTTATGTTTTAGAATAGTGACAGAGGAACACACCAACAAGGTCAA
2701  145_HRV96b    CAATGACATGGGCACTTTATGTTTTAGAATAGTGACAGAGGAACACACCAACAAGGTCAA
2702  146_HRV96a    CAATGACATGGGCACTTTATGTTTTAGAATAGTGACAGAGGAACACACCAACAAGGTCAA
2703  90_HRV16a|    CAATGACATGGGAACTTTGTGTTCGCGTATTGTGACCAGTGAGCAATTACACAAAGTCAA
2704  91_HRV16b|    CAATGACATGGGAACTTTGTGTTCGCGTATTGTGACCAGTGAGCAATTACACAAAGTCAA
2705  92_1AYM_A     CAATGACATGGGAACTTTGTGTTCGCGTATTGTGACCAGTGAGCAATTACACAAAGTCAA
2706  93_HRV81a|    TAATGACATGGGAACATTATGCTCACGGATAGTGACAAGTGCACAAGGTGAA
2707  94_HRV81b|    TAATGATATGGGAACATTATGCTCACGGATAGTGACAAGTGAGCAAGTGCACAAGGTGAA
2708  95_HRV81      TAATGATATGGGAACATTATGCTCACGGATAGTGACAAGTGAGCAAGTGCACAAGGTGAA
2709  147_HRV2      AAATAACATGGGGTCACTATGCTCTAGGATAGTAACAGAGAAACACATTCATAAGGTACA
2710  148_HRV2a|    AAATAACATGGGGTCACTATGCTCTAGGATAGTAACAGAGAAACACATTCATAAGGTACA
2711  149_HRV2b|    AAATAACATGGGGTCACTATGCTCTAGGATAGTAACAGAGAAACACATTCATAAGGTACA
2712  150_HRV49a    AAACAACATGGGATCATTATGCTCTAGGATAGTAACAGAGAAACACATTCACAGTATGCA
2713  151_HRV49b    AAACAACATGGGATCATTATGCTCTAGGATAGTAACAGAGAAACACATTCACAGTATGCA
2714  152_HRV49     AAACAACATGGGATCATTATGCTCTAGGATAGTAACAGAGAAACACATTCACAGTATGCA
2715  153_HRV23a    AAACAACATGGGCACATTGTGCTCCAGAGTGGTAACAGAGAAACACATTCATGATATGCG
2716  154_HRV23b    AAACAACATGGGCACATTGTGCTCCAGAGTGGTAACAGAGAAACACATTCATGATATGCG
2717  155_HRV23     AAACAACATGGGCACATTGTGCTCCAGAGTGGTAACAGAGAAACACATTCATGATATGCG
2718  156_HRV30a    AAACAACATGGGCACACTGTGTTCCAGAGTGGTAACAGAAAAACACATTCATGATGTGCG
2719  157_HRV30b    AAACAACATGGGCACACTGTGTTCCAGAGTGGTAACAGAAAAACACATTCATGATGTGCG
2720  158_HRV30     AAACAACATGGGCACACTGTGTTCCAGAGTGGTAACAGAAAAACACATTCATGATGTGCG
2721  159_HRV7      CAATGACATGGGAACCATATGTGTTAGACTAGTTACATCTACACAAAAACACAATTTAAA
2722  160_HRV7b|    CAATGACATGGGAACCATATGTGTTAGACTAGTTACATCTACACAAAAACACAATTTAAA
2723  161_HRV7a|    CAATGACATGGGAACCATATGTGTTAGACTAGTTACATCTACACAAAAACACAATTTAAA
2724  162_HRV88     TAATGATATGGGAACTATATGTATTAGATTGGTCACCTCCACCCAAAAGCATAAACTGAA
2725  163_HRV88a    TAATGATATGGGAACTATATGTATTAGATTGGTCACCTCCACCCAAAAGCATAAACTGAA
```

FIG. D9 CONT'D

```
05.trace                                                                                          9/20/2007 5:04 PM 2726  164_HRV88b   TAATGATATGGGAACTATATGTATTAGATTGGTCACCTCCACCCAAAAGCATAAACTGAA
2727  165_HRV36a   TAACGACATGGGAACCATATGTGTTAGAATAGTTACATCCAACCAAAAACATGATTTAAA
2728  166_HRV36b   TAACGACATGGGAACCATATGTGTTAGAATAGTTACATCCAACCAAAAACATGATTTAAA
2729  167_HRV36    TAACGACATGGGAACCATATGTGTTAGAATAGTTACATCCAACCAAAAACATGATTTAAA
2730  168_HRV89a   TAATGATATGGGAACCATATGTGTTAGAATAGTGACATCCAACCAAAAACATGATTTAAA
2731  169_HRV89b   TAATGATATGGGAACCATATGTGTTAGAATAGTGACATCCAACCAAAAACATGATTTAAA
2732  170_HRV89    TAATGATATGGGAACCATATGTGTTAGAATAGTGACATCCAACCAAAAACATGATTTAAA
2733  171_HRV58    AAATGACATGGGAACTATATGTGTTAGAATAGTCACATCCAAACAAAGACACAATTTAAA
2734  172_HRV58a   AAATGACATGGGAACTATATGTGTTAGAATAGTCACATCCAAACAAAGACACAATTTAAA
2735  173_HRV58b   AAATGACATGGGAACTATATGTGTTAGAATAGTCACATCCAAACAAAGACACAATTTAAA
2736  174_HRV12a   CAATGACATGGGTTCACTGTGTGTCAGAATAGTTACAGACCAGCAAAAACATAAAGTTAA
2737  175_HRV12b   CAATGACATGGGTTCACTGTGTGTCAGAATAGTTACAGACCAGCAAAAACATAAAGTTAA
2738  176_HRV12    CAATGACATGGGTTCACTGTGTGTCAGAATAGTTACAGACCAGCAAAAACATAAAGTTAA
2739  177_HRV78a   CAATGACATGGGTACACTGTGTATGAGGATGGTTACAGATCAACAACAACATAAGGTCAC
2740  178_HRV78b   CAATGACATGGGTACACTGTGTATGAGGATGGTTACAGATCAACAACAACATAAGGTCAC
2741  179_HRV78    CAATGACATGGGTACACTGTGTATGAGGATGGTTACAGATCAACAACAACATAAGGTCAC
2742  180_HRV20    AAACGATATGGGCACATTGTGTGTTCGTATTGTGACTGAGCAGCAGACACATAAGGTTAA
2743  181_HRV20a   AAACGATATGGGCACATTGTGTGTTCGTATTGTGACTGAGCAGCAGACACATAAGGTTAA
2744  182_HRV20b   AAACGATATGGGCACATTGTGTGTTCGTATTGTGACTGAGCAGCAGACACATAAGGTTAA
2745  183_HRV68    AAATGATATGGGCACATTATGTGTCCGTATTGTGACTGAGCAGCAGACACATAGGGTCAA
2746  184_HRV68a   AAATGATATGGGCACATTATGTGTCCGTATTGTGACTGAGCAGCAGACACATAGGGTCAA
2747  185_HRV68b   AAATGATATGGGCACATTATGTGTCCGTATTGTGACTGAGCAGCAGACACATAGGGTCAA
2748  186_HRV28    AAATCATATGGGAACACTCTGTGCTCGCATAGTAACTGAACAACAGAAGCATGAAGTCAA
2749  187_HRV28a   AAATCATATGGGAACACTCTGTGCTCGCATAGTAACTGAACAACAGAAGCATGAAGTCAA
2750  188_HRV28b   AAATCATATGGGAACACTCTGTGCTCGCATAGTAACTGAACAACAGAAGCATGAAGTCAA
2751  189_HRV53a   TAATGATATGGGAACACTTTGTGTGCGCATAGTGACTGAGCAACAGAAAAATGAGGTCAA
2752  190_HRV53b   TAATGATATGGGAACACTTTGTGTGCGCATAGTGACTGAGCAACAGAAAAATGAGGTCAA
2753  191_HRV53    TAATGATATGGGAACACTTTGTGTGCGCATAGTGACTGAGCAACAGAAAAATGAGGTCAA
2754  192_HRV46a   CAATGATATGGGAACTATATGTGTCAGAATTGTTACCGAACAACAAAAACATAAGGTTCT
2755  193_HRV46b   CAATGATATGGGAACTATATGTGTCAGAATTGTTACCGAACAACAAAAACATAAGGTTCT
2756  194_HRV46    CAATGATATGGGAACTATATGTGTCAGAATTGTTACCGAACAACAAAAACATAAGGTTCT
2757  195_HRV80a   CAATGATATGGGAACCCTGTGTGCTAGAATTGTTACAGAACAACAGAAACATAAAGTCCT
2758  196_HRV80b   CAATGATATGGGAACCCTGTGTGCTAGAATTGTTACAGAACAACAGAAACATAAAGTCCT
2759  197_HRV80    CAATGATATGGGAACCCTGTGTGCTAGAATTGTTACAGAACAACAGAAACATAAAGTCCT
2760  198_HRV51    AAATGCTATGGGGACACTATGTGTTCGTGTGGTCACAGAGCAACAAAAACATGAGGTTAA
2761  199_HRV51a   AAATGCTATGGGGACACTATGTGTTCGTGTGGTCACAGAGCAACAAAAACATGAGGTTAA
2762  200_HRV51b   AAATGCTATGGGGACACTATGTGTTCGTGTGGTCACAGAGCAACAAAAACATGAGGTTAA
2763  201_HRV65a   TAATGCTATGGGCACACTATATGTGCGTGTGGTTACAGAAAGGCAAAAACATGAAGTCAA
2764  202_HRV65b   TAATGCTATGGGCACACTATATGTGCGTGTGGTTACAGAAAGGCAAAAACATGAAGTCAA
2765  203_HRV65    TAATGCTATGGGCACACTATATGTGCGTGTGGTTACAGAAAGGCAAAAACATGAAGTCAA
2766  204_HRV71a   TAATGCCATGGGCACCTTATGTGTTCGTGTGGTTACAGAACAGCAAAGCAACACAGTCAA
2767  205_HRV71b   TAATGCCATGGGCACCTTATGTGTTCGTGTGGTTACAGAACAGCAAAGCAACACAGTCAA
2768  206_HRV71    TAATGCCATGGGCACCTTATGTGTTCGTGTGGTTACAGAACAGCAAAGCAACACAGTCAA
2769  207_HRV8     AAATCACATGGGCACAATATGTGTGAGAATGGTGACAGATAAACAGAAAATTAAAACTAA
2770  208_HRV95    AAATCACATGGGCACAATATGTGTGAGAATGGTGACAGATAAACAGAAAATTAAAACTAA
2771  209_HRV45    TAACCATATGGGGACTATATGTGTTAGAATTGTTACAGACCAACAACAACATAGAGTTAA
2772  210_HRV45a   TAACCATATGGGGACTATATGTGTTAGAATTGTTACAGACCAACAACAACATAGAGTTAA
2773  211_HRV45b   TAACCATATGGGGACTATATGTGTTAGAATTGTTACAGACCAACAACAACATAGAGTTAA
2774  GROUP_1      -AA----ATGGG--C--T-T------G--T---T-AC-------CA--------------
2775
2776  1_HRV1A1|d   CATCACAACACACATATATCATAAAGCTAAACACACAAAAGCTTGGTGTCCTAGGCCCCC
2777  2_HRV1A2|d   CATCACAACACACATATATCATAAAGCTAAACACACAAAAGCTTGGTGTCCTAGGCCCCC
2778  3_HRV1A|cD   CATCACAACACACATATATCATAAAGCTAAACACACAAAAGCTTGGTGTCCTAGGCCCCC
2779  4_HRV1B1|d   TATTACAACACACATATATCACAAAGCTAAACACACAAAAGCTTGGTGTCCTAGACCTCC
2780  5_HRV1B2|d   TATTACAACACACATATATCACAAAGCTAAACACACAAAAGCTTGGTGTCCTAGACCTCC
2781  6_HRV1B      TATTACAACACACATATATCACAAAGCTAAACACACAAAAGCTTGGTGTCCTAGACCTCC
2782  7_HRV40a|d   GATTACCACACGTATATATCACAAGGCCAAGCATATTAAAGCATGGTGTCCAAGGGCCCC
2783  8_HRV40b|d   GATTACCACACGTATATATCACAAGGCCAAGCATATTAAAGCATGGTGTCCAAGGGCCCC
2784  9_HRV40      GATTACCACACGTATATATCACAAGGCCAAGCATATTAAAGCATGGTGTCCAAGGGCCCC
2785  10_HRV85     AATCACCACGCGTGTGTATCATAAGGCCAAGCATGTAAAGCTTGGTGTCCAAGAGCACC
2786  11_HRV85a|   AATCACCACGCGTGTGTATCATAAGGCCAAGCATGTAAAGCTTGGTGTCCAAGAGCACC
2787  12_HRV85b|   AATCACCACGCGTGTGTATCATAAGGCCAAGCATGTAAAGCTTGGTGTCCAAGAGCACC
2788  13_HRV56a|   AGTCACAACTCGTGTATATCATAAGGCAAAGCATATTCGAGCATGGTGTCCTAGAGCACC
2789  14_HRV56b|   AGTCACAACTCGTGTATATCATAAGGCAAAGCATATTCGAGCATGGTGTCCTAGAGCACC
2790  15_HRV56     AGTCACAACTCGTGTATATCATAAGGCAAAGCATATTCGAGCATGGTGTCCTAGAGCACC
```

FIG. D9 CONT'D

05.trace                                                                 9/20/2007 5:04 PM

```
2791 16_HRV54    AATCACCACACGGGTGTATCACAAGGCAAAACACATTAGAGCATGGTGTCCACGTGCACC
2792 17_HRV98    AATCACTACACGTGTGTACCACAAAGCAAAACACATTAGAGCATGGTGTCCACGTGCACC
2793 18_HRV59a|  GGTTGTCACACGTGTGTATCACAAAGCTAAACACGTCAAAGCCTGGTGCCCTAGAGCTCC
2794 19_HRV59b|  GGTTGTCACACGTGTGTATCACAAAGCTAAACACGTCAAAGCCTGGTGCCCTACAGCTCC
2795 20_HRV59    GGTTGTCACACGTGTGTATCACAAAGCTAAACACGTCAAAGCCTGGTGCCCTAGAGCTCC
2796 21_HRV63    GGTGACTACACGTGTATATCATAAAGCTAAACACATCAGAGCCTGGTGCCCAAGCAGCTCC
2797 22_HRV63b|  GGTGACTACACGTGTATATCATAAAGCTAAACACATCAGAGCCTGGTGCCCAAGCAGCTCC
2798 23_HRV63a|  GGTGACTACACGTGTATATCATAAAGCTAAACACATCAGAGCCTGGTGCCCAAGCAGCTCC
2799 24_HRV39    GGTTACAACCAGAGTTTACCATAAAGCCAAGCATGTTAAAGCATGGTGCCCTAGGGCTCC
2800 25_HRV39a|  GGTTACAACCAGAGTTTACCATAAAGCCAAGCATGTTAAAGCATGGTGCCCTAGGGCTCC
2801 26_HRV39b|  GGTTACAACCAGAGTTTACCATAAAGCCAAGCATGTTAAAGCATGGTGCCCTAGGGCTCC
2802 27_HRV10a|  AATTACCACCAGTGTTTATCACAAAGCCAAGCATGTCAAAGCATGGTGTCCAAGACCACC
2803 28_HRV10b|  AATTACCACCAGTGTTTATCACAAAGCCAAGCATGTCAAAGCATGGTGTCCAAGACCACC
2804 29_HRV10    AATTACCACCAGTGTTTATCACAAAGCCAAGCATGTCAAAGCATGGTGTCCAAGACCACC
2805 30_HRV100a  AATTACTACTAATATCTATCACAAGGCCAAACATGTTAAAGCTTGGTGCCCAAGACCACC
2806 31_HRV100b  AATTACTACTAATATCTATCACAAGGCCAAACATGTTAAAGCTTGGTGCCCAAGACCACC
2807 32_HRV100   AATTACTACTAATATCTATCACAAGGCCAAACATGTTAAAGCTTGGTGCCCAAGACCACC
2808 33_HRV66    AATTACTACTAGAGTATACCATAAGGCTAAGCATGTTAAAGCCTGGTGTCCTAGACCACT
2809 34_HRV66b|  AATTACTACTAGAGTATACCATAAGGCTAAGCATGTTAAAGCCTGGTGTCCTAGACCACT
2810 35_HRV66a|  AATTACTACTAGAGTATACCATAAGGCTAAGCATGTTAAAGCCTGGTGTCCTAGACCACT
2811 36_HRV77a|  AATCACCACTAGAGTATACCACAAGGCTAAACATATTAAAGCTTGGTGTCCCAGACCACC
2812 37_HRV77b|  AATCACCACTAGAGTATACCACAAGGCTAAACATATTAAAGCTTGGTGTCCCAGACCACC
2813 38_HRV77    AATCACCACTAGAGTATACCACAAGGCTAAACATATTAAAGCTTGGTGTCCCAGACCACC
2814 39_HRV62a   GGTCACAACTAATATTTACCACAAGGCTAAGCATGTAAAAGCGTGGTGCCCGCGGCCGCC
2815 40_HRV62b   GGTCACAACTAATATTTACCACAAGGCTAAGCATGTAAAAGCGTGGTGCCCTAGACCACC
2816 41_HRV25    GGTTACAACTAACATTTACCATAAAGCTAAGCATGTAAAAGCATGGTGCCCTAGACCACC
2817 42_HRV29a   AGTTACAACAAGTATCTATCATAAAGCTAAACATGTAAAGGCGTGGTGTCCTAGACCACC
2818 43_HRV29b   AGTTACAACAAGTATCTATCATAAAGCTAAACATGTAAAGGCGTGGTGTCCTAGACCACC
2819 44_HRV44a   AGTTACAACAAGCATTTATCACAAAGCTAAACATGTAAAAGCATGGTGCCCTAGACCACC
2820 45_HRV44b   AGTTACAACAAGCATTTATCACAAAGCTAAACATGTAAAAGCATGGTGCCCTAGACCACC
2821 46_HRV31    AATCACAACCAATATTTACCATAAAGCCAAACATGTTAAGGCATGGTGTCCTAGGCCCCC
2822 47_HRV31a|  AATCACAACCAATATTTACCATAAGGCCAAACATGTTAAGGCATGGTGTCCTAGGCCCCC
2823 48_HRV31b|  AATCACAACCAATATTTACCATAAGGCCAAACATGTAAAGGCATGGTGTCCTAGGCCACC
2824 49_HRV47    AATCACAACTAACATCTACCATAAAGCCAAGCATGTGAAAGCATGGTGTCCTAGACCACC
2825 50_HRV47a|  AATCACAACTAACATCTACCATAAAGCCAAGCATGTGAAAGCATGGTGTCCTAGACCACC
2826 51_HRV47b|  AATCACAACTAACATCTACCATAAAGCCAAGCATGTGAAAGCATGGTGTCCTAGACCACC
2827 52_HRV11    AGTCACAACTAGGGTGTATCATAAAGCAAAGCATGTGAAGGTGTGGTGTCCAAGACCACC
2828 53_HRV11b|  AGTCACAACTAGGGTGTATCATAAAGCAAAGCATGTGAAGGTGTGGTGTCCAAGACCACC
2829 54_HRV11a|  AGTCACAACTAGGGTGTATCATAAAGCAAAGCATGTGAAGGTGTGGTGTCCAAGACCACC
2830 55_HRV76    AGTTACAACAAGAATATATCACAAAGCAAAGCATGTTAAGGTATGGTGCCCGAGACCACC
2831 56_HRV76b|  AGTTACAACAAGAATATATCACAAAGCAAAGCATGTTAAGGTATGGTGCCCGAGACCACC
2832 57_HRV76a|  AGTTACAACAAGAATATATCACAAAGCAAAGCATGTTAAGGTATGGTGCCCGAGACCACC
2833 58_HRV33    AGTTACAACAAGAGTATACCATAAAGCAAAACATGTCAAAGTCTGGTGCCCAAGACCACC
2834 59_HRV33b|  AGTTACAACAAGAGTATACCATAAAGCAAAACATGTCAAAGTCTGGTGCCCAAGACCACC
2835 60_HRV33a|  AGTTACAACAAGAGTATACCATAAAGCAAAACATGTCAAAGTCTGGTGCCCAAGACCACC
2836 61_HRV24a|  AATTACAACAAGAATATACCACAAAGCAAAGCACATTAAGGTCTGGTGTCCAAGGCCACC
2837 62_HRV24b|  AATTACAACAAGAATATACCACAAAGCAAAGCACATTAAGGTCTGGTGTCCAAGGCCACC
2838 63_HRV24    AATTACAACAAGAATATACCACAAAGCAAAGCACATTAAGGTCTGGTGTCCAAGGCCACC
2839 64_HRV90    GATCACTACAAGAATATACCACAAAGCAAAACACATTAAGGTTTGGTGTCCAAGACCACC
2840 65_HRV90a|  GATCACTACAAGAATATACCATAAAGCAAAACACATTAAGGTTTGGTGTCCAAGACCACC
2841 66_HRV90b|  GATCACTACAAGAATATACCATAAAGCAAAACACATTAAGGTTTGGTGTCCAAGACCACC
2842 67_HRV34    AATAACAACTAGAGTTTATCACAAAGCTAAACATGTAAAAACCTGGTGTCCAAGACCACC
2843 68_HRV34b|  AATAACAACTAGAGTTTATCACAAAGCTAAACATGTAAAAACCTGGTGTCCAAGACCACC
2844 69_HRV34a|  AATAACAACTAGAGTTTATCACAAAGCTAAACATGTAAAAACCTGGTGTCCAAGACCACC
2845 70_HRV50a|  AATCACAACCAGAGTATACCATAAAGCCAAACACATAAAAGTCTGGTGTCCAAGACCACC
2846 71_HRV50b|  AATCACAACCAGAGTATACCATAAAGCCAAACACATAAAAGTCTGGTGTCCAAGACCACC
2847 72_HRV50    AATCACAACCAGAGTATACCATAAAGCCAAACACATAAAAGTCTGGTGTCCAAGACCACC
2848 73_HRV18a|  AATAACAACCAGAATATACCACAAGGCAAAACATGTTAAAGCATGGTGCCCAAGGCCACC
2849 74_HRV18b|  AATAACAACCAGAATATACCACAAGGCAAAACATGTTAAAGCATGGTGCCCAAGGCCACC
2850 75_HRV18    AATAACAACCAGAATATACCACAAGGCAAAACATGTTAAAGCATGGTGCCCAAGGCCACC
2851 76_HRV55    AGTGACGACAAGAGTCTATCATAAAGCTAAACATCAAAGCATGGTGCCCACGACCACC
2852 77_HRV55b|  AGTGACGACAAGAGTCTATCATAAAGCTAAACATCAAAGCATGGTGCCCACGACCACC
2853 78_HRV55a|  AGTGACGACAAGAGTCTATCATAAAGCTAAACATCAAAGCATGGTGCCCACGACCACC
2854 79_HRV57    AATAACAACCAGAGTGTATCACAAAGCCAAACATGTCAAAGCCTGGTGCCCTAGACCACC
2855 80_HRV57a|  AATAACAACCAGAGTGTATCACAAAGCCAAACATGTCAAAGCCTGGTGCCCTAGACCACC
```

FIG. D9 CONT'D 05.trace                                                                  9/20/2007 5:04 PM

```
2856  81_HRV57b|    AATAACAACCAGAGTGTATCACAAAGCCAAACATGTCAAAGCCTGGTGCCCTAGACCACC
2857  82_HRV21      AGTGACCACAAGAATATACCATAAGGCAAAGCATGTTAAAGCTTGGTGCCCCAGACCACC
2858  83_HRVHan     AGTGACCACAAGAATATACCATAAGGCAAAGCATGTTAAAGCTTGGTGCCCTAGACCACC
2859  84_HRV43      GATAACTACCAGGATATATCATAAAGCCAAGCATATCAAAGCTTGGTGCCCAAGACCACC
2860  85_HRV43b|    GATAACTACCAGGATATATCATAAAGCCAAGCATATCAAAGCTTGGTGCCCAAGACCACC
2861  86_HRV43a|    GATAACTACCAGGATATATCATAAAGCCAAGCATATCAAAGCTTGGTGCCCAAGACCACC
2862  87_HRV75      AGTAACCACTAGAATATATCACAAAGCCAAACATATAAAAGCTTGGTGTCCGAGGCCGCC
2863  88_HRV75b|    AGTAACCACTAGAATATATCACAAAGCCAAACATATAAAAGCTTGGTGTCCGAGGCCGCC
2864  89_HRV75a|    AGTAACCACTAGAATATATCACAAAGCCAAACATATAAAAGCTTGGTGTCCGAGGCCGCC
2865  96_HRV9a|d    AATTTCAACCAGAATATATCACAAAGCCAAACATGTTAAAGCCTGGTGCCCAAGACCTCC
2866  97_HRV9b|d    AATTTCAACCAGAATATATCACAAAGCCAAACATGTTAAAGCCTGGTGCCCAAGACCTCC
2867  98_HRV9       AATTTCAACCAGAATATATCACAAAGCCAAACATGTTAAAGCCTGGTGCCCAAGACCTCC
2868  99_HRV32      TATTTCAACTAGGGTATATCACAAAGCTAAACACGTCAAAGCTTGGTGCCCACGACCACC
2869  100_HRV32a    TATTTCAACTAGGGTATATCACAAAGCTAAACACGTCAAAGCTTGGTGCCCACGACCACC
2870  101_HRV32b    TATTTCAACTAGGGTATATCACAAAGCTAAACACGTCAAAGCTTGGTGCCCACGACCACC
2871  102_HRV67     AATTGCAACGCGGGTGTATCATAAGGCTAAACATGTAAAAGCTTGGTGCCCAAGGCCCCC
2872  103_HRV67a    AATTGCAACGCGGGTGTATCATAAGGCTAAACATGTAAAAGCTTGGTGCCCAAGGCCCCC
2873  104_HRV67b    AATTGCAACGCGGGTGTATCATAAGGCTAAACATGTAAAAGCTTGGTGCCCAAGGCCCCC
2874  105_HRV15     GATTACAACTAGAGTGTATCACAAAGCTAAACATGTAAAGGCTTGGTGCCCCAGACCCCC
2875  106_HRV15a    GATTACAACTAGAGTGTATCACAAAGCTAAACATGTAAAGGCTTGGTGCCCCAGACCCCC
2876  107_HRV15b    GATTACAACTAGAGTGTATCACAAAGCTAAACATGTAAAGGCTTGGTGCCCCAGACCCCC
2877  108_HRV74a    AATTACAACTAGAGTGTACCATAAAGCAAAGCATGTGAAGGCATGGTGTCCTAGACCCCC
2878  109_HRV74b    AATTACAACTAGAGTGTACCATAAAGCAAAGCATGTGAAGGCATGGTGTCCTAGACCCCC
2879  110_HRV74     AATTACAACTAGAGTGTACCATAAAGCAAAGCATGTGAAGGCATGGTGTCCTAGACCCCC
2880  111_HRV38a    GATAACAACTAGAATTTATCATAAGGCAAAACATGTAAAAGCCTGGTGTCCAAGACCCCC
2881  112_HRV38b    GATAACAACTAGAATTTATCATAAGGCAAAACATGTAAAAGCCTGGTGTCCAAGACCCCC
2882  113_HRV38     GATAACAACTAGAATTTATCATAAGGCAAAACATGTAAAAGCCTGGTGTCCAAGACCCCC
2883  114_HRV60     CGTCGCAACAAGAATATATCATAAAGCAAAGCATGTTAAGGCTTGGTGTCCAAGACCTCC
2884  115_HRV60a    CGTCGCAACAAGAATATATCATAAAGCAAAGCATGTTAAGGCTTGGTGTCCAAGACCTCC
2885  116_HRV60b    CGTCGCAACAAGAATATATCATAAAGCAAAGCATGTTAAGGCTTGGTGTCCAAGACCTCC
2886  117_HRV64a    CATCACTACTAGGGTTTATCACAAAGCAAAACATGTCAAGGCATGGTGTCCACGGCCCCC
2887  118_HRV64b    CATCACTACTAGGGTTTATCACAAAGCAAAACATGTCAAGGCATGGTGTCCACGGCCCCC
2888  119_HRV64     CATCACTACTAGGGTTTATCACAAAGCAAAACATGTCAAGGCATGGTGTCCACGGCCCCC
2889  120_HRV94a    CATCACTACTAGAGTGTACCACAAAGCAAAACATGTGAAAGCGTGGTGCCCGCCCCTCC
2890  121_HRV94b    CATCACTACTAGAGTGTACCACAAAGCAAAACATGTGAAAGCGTGGTGCCCGCGCCCTCC
2891  122_HRV94     CATCACTACTAGAGTGTACCACAAAGCAAAACATGTGAAAGCGTGGTGCCCGCGCCCTCC
2892  123_HRV22     AATTACAACTAGAGTGTACCACAAAGCAAAACATGTAAAGGCATGGTGCCCACGTCCTCC
2893  124_HRV22a    AATTACAACTAGAGTGTACCACAAAGCAAAACATGTAAAGGCATGGTGCCCACGTCCTCC
2894  125_HRV22b    AATTACAACTAGAGTGTACCACAAAGCAAAACATGTAAAGGCATGGTGCCCACGTCCTCC
2895  126_HRV82     CATTACCACAAGAATATATCACAAAGCAAAACATGTGAAAGCGTGGTGTCCACGACCCCC
2896  127_HRV82b    CATTACCACAAGAATATATCACAAAGCAAAACATGTGAAAGCGTGGTGTCCACGACCCCC
2897  128_HRV82a    CATTACCACAAGAATATATCACAAAGCAAAACATGTGAAAGCGTGGTGTCCACGACCCCC
2898  129_HRV19     AATCACAACTAGAGTATATCATAAAGCTAAACATATAAAAGCTTGGTGCCCACGACCACC
2899  130_HRV19a    AATCACAACTAGAGTATATCATAAAGCTAAACATATAAAAGCTTGGTGCCCACGACCACC
2900  131_HRV19b    AATCACAACTAGAGTATATCATAAAGCTAAACATATAAAAGCTTGGTGCCCACGACCACC
2901  132_HRV13     GGTTACAACTAGAATCTATCATAAAGCTAAACATGTCAAAGCATGGTGTCCTAGACCTCC
2902  133_HRV13a    GGTTACAACTAGAATCTATCATAAAGCTAAACATGTCAAAGCATGGTGTCCTAGACCTCC
2903  134_HRV13b    GGTTACAACTAGAATCTATCATAAAGCTAAACATGTCAAAGCATGGTGTCCTAGACCTCC
2904  135_HRV41     GGTCACAACTAGAGTTTACCACAAAGCTAAACATGTTAAAGCATGGTGTCCTAGACCTCC
2905  136_HRV41a    GGTCACAACTAGAGTTTACCACAAAGCTAAACATGTTAAAGCATGGTGTCCTAGACCTCC
2906  137_HRV41b    GGTCACAACTAGAGTTTACCACAAAGCTAAACATGTTAAAGCATGGTGTCCTAGACCTCC
2907  138_HRV73     GGTTACTACTAGAATCTATCAAAGGCTAAACATGTTAAAGCTTGGTGTCCAAGACCTCC
2908  139_HRV73b    GGTTACTACTAGAATCTATCATAAGGCTAAACATGTTAAAGCTTGGTGTCCAAGACCTCC
2909  140_HRV73a    GGTTACTACTAGAATCTATCATAAGGCTAAACATGTTAAAGCTTGGTGTCCAAGACCTCC
2910  141_HRV61     AATCACAACTAGGATTTACCATAAAGCTAAACATGTTAAAGTCTGGTGTCCTAGACCCCC
2911  142_HRV61a    AATCACAACTAGGATTTACCATAAAGCTAAACATGTTAAAGTCTGGTGTCCTAGACCCCC
2912  143_HRV61b    AATCACAACTAGGATTTACCATAAAGCTAAACATGTTAAAGTCTGGTGTCCTAGACCCCC
2913  144_HRV96     AATTACAACCAGAGTTTACCACAAAGCTAAACATGTTAAGGTGTGGTGCCCGAGACCCCC
2914  145_HRV96b    AATTACAACCAGAGTTTACCACAAAGCTAAACATGTTAAGGTGTGGTGCCCGAGACCCCC
2915  146_HRV96a    AATTACAACCAGAGTTTACCACAAAGCTAAACATGTTAAGGTGTGGTGCCCGAGACCCCC
2916  90_HRV16a|    AGTGGTAACAAGGATATATCACAAAGCCAAACACACCAAAGCTTGGTGCCCAAGACCACC
2917  91_HRV16b|    AGTGGTAACAAGGATATATCACAAAGCCAAACACACCAAAGCTTGGTGCCCAAGACCACC
2918  92_1AYM_A|    AGTGGTAACAAGGATATATCACAAAGCCAAACACACCAAAGCTTGGTGCCCAAGACCACC
2919  93_HRV81a|    AATAGTAACAAGAATATATCACAAAGCTAAGCACACCAAAGCTTGGTGTCCAAGACCACC
2920  94_HRV81b|    AATAGTAACAAGAATATATCACAAAGCTAAGCACACCAAAGCTTGGTGTCCAAGACCACC
```

FIG. D9 CONT'D 05.trace                                                                 9/20/2007 5:04 PM

```
2921  95_HRV81    AATAGTAACAAGAATATATCACAAAGCTAAGCACACCAAAGCTTGGTGTCCAAGACCACC
2922 147_HRV2     TATAATGACAAGAATCTATCACAAGGCTAAACATGTCAAGGCATGGTGTCCACGCCCACC
2923 148_HRV2a|   TATAATGACAAGAATCTATCACAAGGCTAAACATGTCAAGGCATGGTGTCCACGCCCACC
2924 149_HRV2b|   TATAATGACAAGAATCTATCACAAGGCTAAACATGTCAAGGCATGGTGTCCACGCCCACC
2925 150_HRV49a   TATCATGACAAGAATCTATCATAAAGCTAAACACGTCAAAGCATGGTGTCCGCGCCCACC
2926 151_HRV49b   TATCATGACAAGAATCTATCATAAAGCTAAACACGTCAAAGCATGGTGTCCGCGCCCACC
2927 152_HRV49    TATCATGACAAGAATCTATCATAAAGCTAAACACGTCAAAGCATGGTGTCCGCGCCCACC
2928 153_HRV23a   GATAATGACAAGGGTCTACCACAAGGCTAAACATGTCAAAGCATGGTGTCCGCGGCCACC
2929 154_HRV23b   GATAATGACAAGGGTCTACCACAAAGCTAAACATGTCAAAGCATGGTGTCCGCGGCCACC
2930 155_HRV23    GATAATGACAAGGGTCTACCACAAAGCTAAACATGTCAAAGCATGGTGTCCGCGGCCACC
2931 156_HRV30a   CATAATGACAAGGGTCTACCACAAGGCTAAACATGTCAAAGCGTGGTGTCCACGGCCACC
2932 157_HRV30b   CATAATGACAAGGGTCTACCACAAGGCTAAACATGTCAAAGCGTGGTGTCCACGGCCACC
2933 158_HRV30    CATAATGACAAGGGTCTACCACAAGGCTAAACATGTCAAAGCGTGGTGTCCACGGCCACC
2934 159_HRV7     GATTGTGAGTCGCATTTACCACAAAGCCAAACATATAAAAGCATGGTGCCCACGCCCACC
2935 160_HRV7b|   GATTGTGAGTCGCATTTACCACAAAGCCAAACATATAAAAGCATGGTGCCCACGCCCACC
2936 161_HRV7a|   GATTGTGAGTCGCATTTACCACAAAGCCAAACATATAAAAGCATGGTGCCCACGCCCACC
2937 162_HRV88    TATCATTAGCCGTATATATCACAAGGCTAAACATATAAAGGCATGGTGTCCACGCCCACC
2938 163_HRV88a   TATCATTAGCCGTATATATCACAAGGCTAAACATATAAAGGCATGGTGTCCACGCCCACC
2939 164_HRV88b   TATCATTAGCCGTATATATCACAAGGCTAAACATATAAAGGCATGGTGTCCACGCCCACC
2940 165_HRV36a   TATTGTATGCCGCATTTATCATAAAGCTAAACACATAAAGGCCTGGTGCCCGCGTCCACC
2941 166_HRV36b   TATTGTATGCCGCATTTATCATAAAGCTAAACACATAAAGGCCTGGTGCCCGCGTCCACC
2942 167_HRV36    TATTGTATGCCGCATTTATCATAAAGCTAAACACATAAAGGCCTGGTGCCCGCGTCCACC
2943 168_HRV89a   TATTGTGTGCCGCATTTACCACAAGGCCAAACATATAAAAGCATGGTGTCCTCGCCCACC
2944 169_HRV89b   TATTGTGTGCCGCATTTACCACAAGGCCAAACATATAAAAGCATGGTGTCCTCGCCCACC
2945 170_HRV89    TATTGTGTGCCGCATTTACCACAAGGCCAAACATATAAAAGCATGGTGTCCTCGCCCACC
2946 171_HRV58    CATTGTCTGTCGCATTTACCACAAAGCCAAGCATATAAAAGCATGGTGTCCACGCCCACC
2947 172_HRV58a   CATTGTCTGTCGCATTTACCACAAAGCCAAGCATATAAAAGCATGGTGTCCACGCCCACC
2948 173_HRV58b   CATTGTCTGTCGCATTTACCACAAAGCCAAGCATATAAAAGCATGGTGTCCACGCCCACC
2949 174_HRV12a   GATTACCAGTAGAATATACCATAAAGCAAAACATATCAGTGCCTGGGGCCCTAGACCACC
2950 175_HRV12b   GATTACCAGTAGAATATACCATAAAGCAAAACATATCAGTGCCTGGGGCCCTAGACCACC
2951 176_HRV12    GATTACCAGTAGAATATACCATAAAGCAAAACATATCAGTGCCTGGGGCCCTAGACCACC
2952 177_HRV78a   AATTACAGCTAGAGTCTACCACAAGGCCAAACATATTAGTGCATGGGGCCCAAGACCTCC
2953 178_HRV78b   AATTACAGCTAGAGTCTACCACAAGGCCAAACATATTAGTGCATGGGGCCCAAGACCTCC
2954 179_HRV78    AATTACAGCTAGAGTCTACCACAAGGCCAAACATATTAGTGCATGGGGCCCAAGACCTCC
2955 180_HRV20    GATAACCAGTAGGATATTCCACAAGGCAAAGCATATTAGTGCATGGTGTCCAAGGGCCCC
2956 181_HRV20a   GATAACCAGTAGGATATTCCACAAGGCAAAGCATATTAGTGCATGGTGTCCAAGGGCCCC
2957 182_HRV20b   GATAACCAGTAGGATATTCCACAAGGCAAAGCATATTAGTGCATGGTGTCCAAGGGCCCC
2958 183_HRV68    AATAACCAGCAGAATATTCCATAAAGCAAAACATATTAGTGCGTGGTGTCCAAGAGCTCC
2959 184_HRV68a   AATAACCAGCAGAATATTCCATAAAGCAAAACATATTAGTGCGTGGTGTCCAAGAGCTCC
2960 185_HRV68b   AATAACCAGCAGAATATTCCATAAAGCAAAACATATTAGTGCGTGGTGTCCAAGAGCTCC
2961 186_HRV28    AATAACCAGCATAATATTCCACAAAGCTAAACATGTCAGTGCATGGTGCCCCAGACCTCC
2962 187_HRV28a   AATAACCAGCATAATATTCCACAAAGCTAAACATGTCAGTGCATGGTGCCCCAGAGCTCC
2963 188_HRV28b   AATAACCAGCATAATATTCCACAAAGCTAAACATGTCAGTGCATGGTGCCCCAGACCTCC
2964 189_HRV53a   GATAACCAGTAGGATTTATCACAAGGCTAAACATATCAGTGCATGGTGTCCAAGACCACC
2965 190_HRV53b   GATAACCAGTAGGATTTATCACAAGGCTAAACATATCAGTGCATGGTGTCCAAGACCACC
2966 191_HRV53    GATAACCAGTAGGATTTATCACAAGGCTAAACATATCAGTGCATGGTGTCCAAGACCACC
2967 192_HRV46a   TATAACTAGCAGAATATATCACAAGGCTAAACACATTAAAGCATGGTGCCCCAGGGCACC
2968 193_HRV46b   TATAACTAGCAGAATATATCACAAGGCTAAACACATTAAAGCATGGTGCCCCAGGGCACC
2969 194_HRV46    TATAACTAGCAGAATATATCACAAGGCTAAACACATTAAAGCATGGTGCCCCAGGGCACC
2970 195_HRV80a   AATCACCAGCAGAATATATCACAAAGCTAAACACATCAAAGCATGGTGTCCAAGAGCACC
2971 196_HRV80b   AATCACCAGCAGAATATATCACAAAGCTAAACACATCAAAGCATGGTGTCCAAGAGCACC
2972 197_HRV80    AATCACCAGCAGAATATATCACAAAGCTAAACACATCAAAGCATGGTGTCCAAGAGCACC
2973 198_HRV51    CATAACTAGCAGGATTTACCACAAAGCCAAACATGTCAGTGCATGGTGCCCTCGTCCTCC
2974 199_HRV51a   CATAACTAGCAGGATTTACCACAAAGCCAAACATGTCAGTGCATGGTGCCCTCGTCCTCC
2975 200_HRV51b   CATAACTAGCAGGATTTACCACAAAGCCAAACATGTCAGTGCATGGTGCCCTCGTCCTCC
2976 201_HRV65a   CATAACCAGTAGAATATATCATAAAGCTAAACACATCAGTGCTTGGTGTCCACGACCTCC
2977 202_HRV65b   CATAACCAGTAGAATATATCATAAAGCTAAACACATCAGTGCTTGGTGTCCACGACCTCC
2978 203_HRV65    CATAACCAGTAGAATATATCATAAAGCTAAACACATCAGTGCTTGGTGTCCACGACCTCC
2979 204_HRV71a   CATAACAAGTAGGATTTATCAAAAGCCAAACATGTCAGAGCATGGTGTCCTAGACCCCC
2980 205_HRV71b   CATAACAAGTAGGATTTATCACAAAGCCAAACATGTCAGAGCATGGTGTCCTAGACCCCC
2981 206_HRV71    CATAACAAGTAGGATTTATCACAAAGCCAAACATGTCAGAGCATGGTGTCCTAGACCCCC
2982 207_HRV8     AATTGATTCAAGAATATACCTGAAAGCAAAGCAACATTAAAGCTTGGTGTCCTAGACCCCC
2983 208_HRV95    AATTGATTCAAGAATATACCTGAAAGCAAAGCATATTAAAGCTTGGTGTCCTAGACCCCC
2984 209_HRV45    GATCGACTCCATGGTATATCTAAAAGCTAAACACATCAAGGCATGGTGTCCCAGACCTCC
2985 210_HRV45a   GATCGACTCCATGGTATATCTAAAAGCTAAACACATCAAGGCATGGTGTCCCAGACCTCC
```

FIG. D9 CONT'D

```
05.trace                                                                    9/20/2007 5:04 PM 2986  211_HRV45b    GATCGACTCCATGGTATATCTAAAAGCTAAACACATCAAGGCATGGTGTCCCAGACCTCC
2987  GROUP_1       --T-----------T-T--C--AA-GC-AA-CA---------TGG-G-CC--G--C-C-
2988
2989  1_HRV1A1|d    TAGAGCTGTCCCTTACACA-CATAGTCATGTGACTAATTATATGC-CAGAAA---CAGGT
2990  2_HRV1A2|d    TAGAGCTGTCCCTTACACA-CATAGTCATGTGACTAATTATATGC-CAGAAA---CAGGT
2991  3_HRV1A|cD    TAGAGCTGTCCCTTACACA-CATAGTCATGTGACTAATTATATGC-CAGAAA---CAGGT
2992  4_HRV1B1|d    TAGAGCTGTTCCTTACACA-CATAGTCGTGTAACTAATTATGTAC-CAAAAA---CAGGT
2993  5_HRV1B2|d    TAGAGCTGTTCCTTACACA-CATAGTCGTGTAACTAATTATGTAC-CAAAAA---CAGGT
2994  6_HRV1B       TAGAGCTGTTCCTTACACA-CATAGTCGTGTAACTAATTATGTAC-CAAAAA---CAGGT
2995  7_HRV40a|d    AAGAGCAGTACCTTACACA-CATACACACTCAACAAATTATAAAC-CTCAAG---AAGGT
2996  8_HRV40b|d    AAGAGCAGTACCTTACACA-CATACACACTCAACAAATTATAAAC-CTCAAG---AAGGT
2997  9_HRV40       AAGAGCAGTACCTTACACA-CATACACACTCAACAAATTATAAAC-CTCAAG---AAGGT
2998  10_HRV85      AAGAGCGGTGCCTTATACA-CACACACGCTCAACCAACTATGTGC-CACAAG---ATGGT
2999  11_HRV85a|    AAGAGCGGTGCCTTATACA-CACACACGCTCAACCAACTATGTGC-CACAAG---ATGGT
3000  12_HRV85b|    AAGAGCGGTGCCTTATACA-CACACACGCTCAACCAACTATGTGC-CACAAG---ATGGT
3001  13_HRV56a|    AAGGGCTGTGCCTTATACA-CATGCTCACGTCACCAATTATAAAC-CACAAG---ATGGT
3002  14_HRV56b|    AAGGGCTGTGCCTTATACA-CATGCTCACGTCACCAATTATAAAC-CACAAG---ATGGT
3003  15_HRV56      AAGGGCTGTGCCTTATACA-CATGCTCACGTCACCAATTATAAAC-CACAAG---ATGGT
3004  16_HRV54      TAGGGCTGTCCCATACACA-CATACTAGATCAACAAATTACATGC-CACGGG---AGGGT
3005  17_HRV98      TAGAGCTGTTCCATACACA-CACACTAGATCAACTAATTACATGC-CTCAAG---ATGGT
3006  18_HRV59a|    TAGAGCAGTCCCTTACACA-CACAGCTACGTAACTAACTACAAGATTGCTGG---AAAA-
3007  19_HRV59b|    TAGAGCAGTCCCTTACACA-CACAGCTACGTAACTAACTACAAGATTGCTGG---AAAA-
3008  20_HRV59      TAGAGCAGTCCCTTACACA-CACAGCTACGTAACTAACTACAAGATTGCTGG---AAAA-
3009  21_HRV63      TAGGGCTGTTCCATACACA-CATAGTTATGTCACTAACTATAAAATTACAGG---ACAG-
3010  22_HRV63b|    TAGGGCTGTTCCATACACA-CATAGTTATGTCACTAACTATAAAATTACAGG---ACAG-
3011  23_HRV63a|    TAGGGCTGTTCCATACACA-CATAGTTATGTCACTAACTATAAAATTACAGG---ACAG-
3012  24_HRV39      CAGAGCAGTCCCTTACACA-CACAGCAATGTTACAAATTACAAAG-TACGGG---ACGGT
3013  25_HRV39a|    CAGAGCAGTCCCTTACACA-CACAGCAATGTTACAAATTACAAAG-TACGGG---ACGGT
3014  26_HRV39b|    CAGAGCAGTCCCTTACACA-CACAGCAATGTTACAAATTACAAAG-TACGGG---ACGGT
3015  27_HRV10a|    CAGAGCTGTACCATATACA-CATGCCCATTCCACAAATTACAAAC-CACATG---GCAAA
3016  28_HRV10b|    CAGAGCTGTACCATATACA-CATGCCCATTCCACAAATTACAAAC-CACATG---GCAAA
3017  29_HRV10      CAGAGCTGTACCATATACA-CATGCCCATTCCACAAATTACAAAC-CACATG---GCAAA
3018  30_HRV100a    TCGGGCTGTGCCGTACACA-CATAGTCACTCTACAAATTACAAAC-CACATG---AGGGT
3019  31_HRV100b    TCGGGCTGTGCCGTACACA-CATAGTCACTCTACAAATTACAAAC-CACATG---AGGGT
3020  32_HRV100     TCGGGCTGTGCCGTACACA-CATAGTCACTCTACAAATTACAAAC-CACATG---AGGGT
3021  33_HRV66      TAGAGCTGTACCATACACA-ACTGTAAACTCAACCAATTATATGC-CTCATA---CTGGT
3022  34_HRV66b|    TAGAGCTGTACCATACACA-ACTGTAAACTCAACCAATTATATGC-CTCATA---CTGGT
3023  35_HRV66a|    TAGAGCTGTACCATACACA-ACTGTAAACTCAACCAATTATATGC-CTCATA---CTGGT
3024  36_HRV77a|    TAGAGCTGTACCATACACA-GCAGTAGATTCAACAAATTACAAAC-CTATGA---GAGGG
3025  37_HRV77b|    TAGAGCTGTACCATACACA-GCAGTAGATTCAACAAATTACAAAC-CTATGA---GAGGG
3026  38_HRV77      TAGAGCTGTACCATACACA-GCAGTAGATTCAACAAATTACAAAC-CTATGA---GAGGG
3027  39_HRV62a     CAGAGCTGTTCCATATAAA-TATGTTGATTTCAATAATTATGCAG-CCAGTG---ATAGT
3028  40_HRV62b     TAGAGCTGTTCCATATAAA-TATGTTGATTTCAATAATTATGCAG-CCAGTG---ATAGT
3029  41_HRV25      TAGAGCTGTCCCATATAAA-TATGTTGACTTCAATAATTATGCAG-CCAGTG---ATAAT
3030  42_HRV29a     AAGAGTTGTCCCATACAAG-TATGTTGGCCTAACTAATTACACAC-TTAAAG---AAGAA
3031  43_HRV29b     AAGAGTTGTCCCATACAAG-TATGTTGGCCTAACTAATTACACAC-TTAAAG---AAGAA
3032  44_HRV44a     AAGGGTTGTCCCATACAAG-TATGTTGGCCTAACTAATTACACAC-TTAAAG---AAACA
3033  45_HRV44b     AAGGGTTGTCCCATACAAG-TATGTTGGCCTAACTAATTACACAC-TTAAAG---AAACA
3034  46_HRV31      TAGAGCAGTTCCATACAGGGTATG-TGGATCAACAAACTACAAAC-CTGATG---AAAAT
3035  47_HRV31a|    TAGAGCAGTTCCATACAGGGTATG-TGGATCAACAAACTACAAAC-CTGATG---AAAAT
3036  48_HRV31b|    TAGAGCAGTTCCATACAGG-TATGTTGGATCAACAAACTACAAAC-CTGATG---AAAAT
3037  49_HRV47      TAGAGCTGTTCCATATAGA-TATGTTGGATCAACAAATTACAAAC-CTGATC---AAGGA
3038  50_HRV47a|    TAGAGCTGTTCCATATAGA-TATGTTGGATCAACAAATTACAAAC-CTGATC---AAGGA
3039  51_HRV47b|    TAGAGCTGTTCCATATAGA-TATGTTGGATCAACAAATTACAAAC-CTGATC---AAGGA
3040  52_HRV11      TAGAGCTGTAGAATATACT-CACACTCATGTAACCAATTACAAAC-CACAGG---AAGGA
3041  53_HRV11b|    TAGAGCTGTAGAATATACT-CACACTCATGTAACCAATTACAAAC-CACAGG---AAGGA
3042  54_HRV11a|    TAGAGCTGTAGAATATACT-CACACTCATGTAACCAATTACAAAC-CACAGG---AAGGA
3043  55_HRV76      TAGAGCTGTAGAGTATACA-TACACCCATGTAACAAACTACAAAC-CACATT---CTGGT
3044  56_HRV76b|    TAGAGCTGTAGAGTATACA-TACACCCATGTAACAAACTACAAAC-CACATT---CTGGT
3045  57_HRV76a|    TAGAGCTGTAGAGTATACA-TACACCCATGTAACAAACTACAAAC-CACATT---CTGGT
3046  58_HRV33      TAGAGCTGTGGAATACACC-CATACTCATGTTACAAATTATAAAT-CAACAA---CTCGT
3047  59_HRV33b|    TAGAGCTGTGGAATACACC-CATACTCATGTTACAAATTATAAAT-CAACAA---CTCGT
3048  60_HRV33a|    TAGAGCTGTGGAATACACC-CATACTCATGTTACAAATTATAAAT-CAACAA---CTCGT
3049  61_HRV24a|    CAGAGCTGTTGAGTATACA-CATACTCACGTGACCAATTATAAGC-ATCAGA---CTCGT
3050  62_HRV24b|    CAGAGCTGTTGAGTATACA-CATACTCACGTGACCAATTATAAGC-ATCAGA---CTCGT
```

FIG. D9 CONT'D

05.trace                                                                                                       9/20/2007 5:04 PM

```
3051  63_HRV24     CAGAGCTGTTGAGTATACA-CATACTCACGTGACCAATTATAAGC-ATCAGA---CTCGT
3052  64_HRV90     TAGGGCAGTTGAATACACA-CACACTCATGTAACAAACTACAAAC-ATGCAA---CACGT
3053  65_HRV90a|   TAGGGCAGTTGAATACACA-CACACTCATGTAACAAACTACAAAC-ATGCAA---CACGT
3054  66_HRV90b|   TAGGGCAGTTGAATACACA-CACACTCATGTAACAAACTACAAAC-ATGCAA---CACGT
3055  67_HRV34     AAGAGCTGTTGAGTACACA-CACACACATGTTACTAACTACAAAG-TTAGGG---GTAAA
3056  68_HRV34b|   AAGAGCTGTTGAGTACACA-CACACACATGTTACTAACTACAAAG-TTAGGG---GTAAA
3057  69_HRV34a|   AAGAGCTGTTGAGTACACA-CACACACATGTTACTAACTACAAAG-TTAGGG---GTAAA
3058  70_HRV50a|   AAGAGCTGTTGAATACACA-CACACCCATGTCACTAACTACAAGA-AAAGTG---ATGCT
3059  71_HRV50b|   AAGAGCTGTTGAATACACA-CACACCCATGTCACTAACTACAAGA-AAAGTG---ATGCT
3060  72_HRV50     AAGAGCTGTTGAATACACA-CACACCCATGTCACTAACTACAAGA-AAAGTG---ATGCT
3061  73_HRV18a|   GAGAGCTGTGGAGTACACA-CATACACATGTAACTAACTACAAGC-CTAAGG---AAGGA
3062  74_HRV18b|   GAGAGCTGTGGAGTACACA-CATACACATGTAACTAACTACAAGC-CTAAGG---AAGGA
3063  75_HRV18     GAGAGCTGTGGAGTACACA-CATACACATGTAACTAACTACAAGC-CTAAGG---AAGGA
3064  76_HRV55     TAGGGCTGTTGAATACACA-CACACACATGTCACAAATTACAAGA-AGACTG---ATGGC
3065  77_HRV55b|   TAGGGCTGTTGAATACACA-CACACACATGTCACAAATTACAAGA-AGACTG---ATGGC
3066  78_HRV55a|   TAGGGCTGTTGAATACACA-CACACACATGTCACAAATTACAAGA-AGACTG---ATGGC
3067  79_HRV57     ACGGGCTATCGAGTACACA-CATACACATGTTACTAATTATAAAA-TAAAAG---ATAGA
3068  80_HRV57a|   ACGGGCTATCGAGTACACA-CATACACATGTTACTAATTATAAAA-TAAAAG---ATAGA
3069  81_HRV57b|   ACGGGCTATCGAGTACACA-CATACACATGTTACTAATTATAAAA-TAAAAG---ATAGA
3070  82_HRV21     GAGGGCCGTTGAATACACA-CATACACACGTAACCAATTACAAAA-TTGCAA---ATCAT
3071  83_HRVHan    GAGGGCCGTTGAATACACA-CATACACATGTAACCAATTACAAAA-TTGCAA---ATAAA
3072  84_HRV43     CAGAGCTGTTGAATACACA-CACACACATGTCACAAATTATAAAA-GAGAAG---GAAAG
3073  85_HRV43b|   CAGAGCTGTTGAATACACA-CACACACATGTCACAAATTATAAAA-GAGAAG---GAAAG
3074  86_HRV43a|   CAGAGCTGTTGAATACACA-CACACACATGTCACAAATTATAAAA-GAGAAG---GAAAG
3075  87_HRV75     CAGGGCTGTTGAATACACA-TTTAGACGTGTAACAAATTACAAAA-GAGATG---GACAA
3076  88_HRV75b|   CAGGGCTGTTGAATACACA-TTTAGACGTGTAACAAATTACAAAA-GAGATG---GACAA
3077  89_HRV75a|   CAGGGCTGTTGAATACACA-TTTAGACGTGTAACAAATTACAAAA-GAGATG---GACAA
3078  96_HRV9a|d   TAGGGCAGTTGAGTATATA-CATACACATGTCACAAATTACAAGC-CAAGCA---CAGGC
3079  97_HRV9b|d   TAGGGCAGTTGAGTATATA-CATACACATGTCACAAATTACAAGC-CAAGCA---CAGGC
3080  98_HRV9      TAGGGCAGTTGAGTATATA-CATACACATGTCACAAATTACAAGC-CAAGCA---CAGGC
3081  99_HRV32     TAGGGCAGTTGAATATACA-CATACACATGTTACAAATTACAAAC-CAAGCA---CAGGT
3082  100_HRV32a   TAGGGCAGTTGAATATACA-CATACACATGTTACAAATTACAAAC-CAAGCA---CAGGT
3083  101_HRV32b   TAGGGCAGTTGAATATACA-CATACACATGTTACAAATTACAAAC-CAAGCA---CAGGT
3084  102_HRV67    TAGAGCAGTTGAATACATA-CACACACATGTTACAAACTATAGAC-CAGAAA---CAGGT
3085  103_HRV67a   TAGAGCAGTTGAATACATA-CACACACATGTTACAAACTATAGAC-CAGAAA---CAGGT
3086  104_HRV67b   TAGAGCAGTTGAATACATA-CACACACATGTTACAAACTATAGAC-CAGAAA---CAGGT
3087  105_HRV15    TAGAGCAGTGGAATATACA-CACACACATGTCACAAATTACAAAC-CACAAG---ATGGT
3088  106_HRV15a   TAGAGCAGTGGAATATACA-CACACACATGTCACAAATTACAAAC-CACAAG---ATGGT
3089  107_HRV15b   TAGAGCAGTGGAATATACA-CACACACATGTCACAAATTACAAAC-CACAAG---ATGGT
3090  108_HRV74a   TAGAGCAGTTGAATATACT-CACACACATGTCACAAATTACAAAC-CACAAG---AAGGT
3091  109_HRV74b   TAGAGCAGTTGAATATACT-CACACACATGTCACAAATTACAAAC-CACAAG---AAGGT
3092  110_HRV74    TAGAGCAGTTGAATATACT-CACACACATGTCACAAATTACAAAC-CACAAG---AAGGT
3093  111_HRV38a   AAGGGCAGTTGAATATAGA-CATACACATGTTAACAATTACAAAC-CAGACC---AAGGG
3094  112_HRV38b   AAGGGCAGTTGAATATAGA-CATACACATGTTAACAATTACAAAC-CAGACC---AAGGG
3095  113_HRV38    AAGGGCAGTTGAATATAGA-CATACACATGTTAACAATTACAAAC-CAGACC---AAGGG
3096  114_HRV60    AAGGGCAGTTGAATATAGA-CACACACATGTAAACAACTATAGAC-CAGATG---ATGGA
3097  115_HRV60a   AAGGGCAGTTGAATATAGA-CACACACATGTAAACAACTATAGAC-CAGATG---ATGGA
3098  116_HRV60b   AAGGGCAGTTGAATATAGA-CACACACATGTAAACAACTATAGAC-CAGATG---ATGGA
3099  117_HRV64a   AAGAGCTGTTGGATATACA-CATACAAATGTCACCAATTATAAAC-CATCCA---AAGGA
3100  118_HRV64b   AAGAGCTGTTGGATATACA-CATACAAATGTCACCAATTATAAAC-CATCCA---AAGGA
3101  119_HRV64    AAGAGCTGTTGGATATACA-CATACAAATGTCACCAATTATAAAC-CATCCA---AAGGA
3102  120_HRV94a   AAGAGCTGTTGGATACACA-CATACGCATGTCACTAATTACAAAC-CATCTG---AAGGG
3103  121_HRV94b   AAGAGCTGTTGGATACACA-CATACGCATGTCACTAATTACAAAC-CATCTG---AAGGG
3104  122_HRV94    AAGAGCTGTTGGATACACA-CATACGCATGTCACTAATTACAAAC-CATCTG---AAGGG
3105  123_HRV22    AAGAGCTGTTGGATATACA-CACACACATGTGACAAACTACAAAC-CATCTG---TAGGG
3106  124_HRV22a   AAGAGCTGTTGGATATACA-CACACACATGTGACAAACTACAAAC-CATCTG---TAGGG
3107  125_HRV22b   AAGAGCTGTTGGATATACA-CACACACATGTGACAAACTACAAAC-CATCTG---TAGGG
3108  126_HRV82    GAGGGCTGTGGGTTATACA-CACACACATGTTACCAACTACAAGC-CATCAC---AGGGA
3109  127_HRV82b   GAGGGCTGTGGGTTATACA-CACACACATGTTACCAACTACAAGC-CATCAC---AGGGA
3110  128_HRV82a   GAGGGCTGTGGGTTATACA-CACACACATGTTACCAACTACAAGC-CATCAC---AGGGA
3111  129_HRV19    CAGAGCCGTGGAATATACC-CACACTCATGTGACTAATTATAAAC-CCCAGA---CAGGT
3112  130_HRV19a   CAGAGCCGTGGAATATACC-CACACTCATGTGACTAATTATAAAC-CCCAGA---CAGGT
3113  131_HRV19b   CAGAGCCGTGGAATATACC-CACACTCATGTGACTAATTATAAAC-CCCAGA---CAGGT
3114  132_HRV13    CAGAGCTGTTGAATATACT-AATGTGCATGTTACAAACTACAAAC-CAGGGA---CAGGA
3115  133_HRV13a   CAGAGCTGTTGAATATACT-AATGTGCATGTTACAAACTACAAAC-CAGGGA---CAGGA
```

FIG. D9 CONT'D 05.trace                                                                                         9/20/2007 5:04 PM

```
3116 134_HRV13b    CAGAGCTGTTGAATATACT-AATGTGCATGTTACAAACTACAAAC-CAGGGA---CAGGA
3117 135_HRV41     CAGGGCTGTGGAGTACACC-AATGTGCATGTCACAAATTACAAAC-CAAAAG---CAGGA
3118 136_HRV41a    CAGGGCTGTGGAGTACACC-AATGTGCATGTCACAAATTACAAAC-CAAAAG---CAGGA
3119 137_HRV41b    CAGGGCTGTGGAGTACACC-AATGTGCATGTCACAAATTACAAAC-CAAAAG---CAGGA
3120 138_HRV73     TAGGGCAGTAGAATATACA-AATGCACATGTGACCAATTATAAAC-CCACTG---ATGGA
3121 139_HRV73b    TAGGGCAGTAGAATATACA-AATGCACATGTGACCAATTATAAAC-CCACTG---ATGGA
3122 140_HRV73a    TAGGGCAGTAGAATATACA-AATGCACATGTGACCAATTATAAAC-CCACTG---ATGGA
3123 141_HRV61     CAGAGCAGTGGAATATACT-AATGTGCATTTGACCAATTACAAGC-CCAAAG---ATAGT
3124 142_HRV61a    CAGAGCAGTGGAATATACT-AATGTGCATTTGACCAATTACAAGC-CCAAAG---ATAGT
3125 143_HRV61b    CAGAGCAGTGGAATATACT-AATGTGCATTTGACCAATTACAAGC-CCAAAG---ATAGT
3126 144_HRV96     TAGAGCAGTTGAATACACA-AATGTGCATCTCACAAATTATAAAC-CCAACA---ATG--
3127 145_HRV96b    TAGAGCAGTTGAATACACA-AATGTGCATCTCACAAATTATAAAC-CCAACA---ATG--
3128 146_HRV96a    TAGAGCAGTTGAATACACA-AATGTGCATCTCACAAATTATAAAC-CCAACA---ATG--
3129 90_HRV16a|    CAGAGCTGTTCAATACTCA-CATACACATACCACCAACTACAAAT-TGAGTT---CAGAA
3130 91_HRV16b|    CAGAGCTGTTCAATACTCA-CATACACATACCACCAACTACAAAT-TGAGTT---CAGAA
3131 92_1AYM_A     CAGAGCTGTTCAATACTCA-CATACACATACCACCAACTACAAAT-TGAGTT---CAGAA
3132 93_HRV81a|    CAGGGCTGTTCAGTACACA-CATACACATGTAACTAATTATAAAT-TAGAAA---CAGAT
3133 94_HRV81b|    CAGGGCTGTTCAGTACACA-CATACACATGTAACTAATTATAAAT-TAGAAA---CAGAT
3134 95_HRV81      CAGGGCTGTTCAGTACACA-CATACACATGTAACTAATTATAAAT-TAGAAA---CAGAT
3135 147_HRV2      CAGAGCGCTTGAGTATACT-CGTGCTCACCGCACTAATTTTAAAA-TTGAGG---ATAGG
3136 148_HRV2a|    CAGAGCGCTTGAGTATACT-CGTGCTCACCGCACTAATTTTAAAA-TTGAGG---ATAGG
3137 149_HRV2b|    CAGAGCGCTTGAGTATACT-CGTGCTCACCGCACTAATTTTAAAA-TTGAGG---ATAGG
3138 150_HRV49a    CAGAGCACTTGAATATACT-CGCGCTCACCGTACTAATTTCAAAG-TTGAAG---ACAGA
3139 151_HRV49b    CAGAGCACTTGAATATACT-CGCGCTCACCGTACTAATTTCAAAG-TTGAAG---ACAGA
3140 152_HRV49     CAGAGCACTTGAATATACT-CGCGCTCACCGTACTAATTTCAAAG-TTGAAG---ACAGA
3141 153_HRV23a    CAGAGCACTTGAATACACA-CGCGCTCACCGTACTAATTTCAAAA-TTGAAG---GTGAA
3142 154_HRV23b    CAGAGCACTTGAATACACA-CGCGCTCACCGTACTAATTTCAAAA-TTGAAG---GTGAA
3143 155_HRV23     CAGAGCACTTGAATACACA-CGCGCTCACCGTACTAATTTCAAAA-TTGAAG---GTGAA
3144 156_HRV30a    TAGGGCGCTTGAGTATACC-CGTGCTCATCGCACCAATTTTAAAA-TTGATG---GCAGG
3145 157_HRV30b    TAGGGCGCTTGAGTATACC-CGTGCTCATCGCACCAATTTTAAAA-TTGATG---GCAGG
3146 158_HRV30     TAGGGCGCTTGAGTATACC-CGTGCTCATCGCACCAATTTTAAAA-TTGATG---GCAGG
3147 159_HRV7      ACGAGCTGTGCCTTATCAA-CACACTCACTCCACCAACTATGTGC-CACAAA---ATGGA
3148 160_HRV7b|    ACGAGCTGTGCCTTATCAA-CACACTCACTCCACCAACTATGTGC-CACAAA---ATGGA
3149 161_HRV7a|    ACGAGCTGTGCCTTATCAA-CACACTCACTCCACCAACTATGTGC-CACAAA---ATGGA
3150 162_HRV88     AAGAGCCGTACCTTATCAG-CACACACACTCCACCAATTATGTAC-CAACAG---ATGGG
3151 163_HRV88a    AAGAGCCGTACCTTATCAG-CACACACACTCCACCAATTATGTAC-CAACAG---ATGGG
3152 164_HRV88b    AAGAGCCGTACCTTATCAG-CACACACACTCCACCAATTATGTAC-CAACAG---ATGGG
3153 165_HRV36a    AAGGGCCGTTCCTTACCAA-CACACACATTCCACTAATTATATAC-CATACA---AAGGT
3154 166_HRV36b    AAGGGCCGTTCCTTACCAA-CACACACATTCCACTAATTATATAC-CATACA---AAGGT
3155 167_HRV36     AAGGGCCGTTCCTTACCAA-CACACACATTCCACTAATTATATAC-CATACA---AAGGT
3156 168_HRV89a    AAGGGCTGTTGCCTATCAA-CACACACACTCAACCAATTACATAC-CATCCA---ATGGT
3157 169_HRV89b    AAGGGCTGTTGCCTATCAA-CACACACACTCAACCAATTACATAC-CATCCA---ATGGT
3158 170_HRV89     AAGGGCTGTTGCCTATCAA-CACACACACTCAACCAATTACATAC-CATCCA---ATGGT
3159 171_HRV58     AAGGGCTGTTCCTTATCAA-TTCACACATTCTACTAATTACATAC-CAGATA---GTGGT
3160 172_HRV58a    AAGGGCTGTTCCTTATCAA-TTCACACATTCTACTAATTACATAC-CAGATA---GTGGT
3161 173_HRV58b    AAGGGCTGTTCCTTATCAA-TTCACACATTCTACTAATTACATAC-CAGATA---GTGGT
3162 174_HRV12a    AAGAGCTGTACCATACCAG-CATATACACAATCCAAATTACAAGA-CAAGTA------AT
3163 175_HRV12b    AAGAGCTGTACCATACCAG-CATATACACAATCCAAATTACAAGA-CAAGTA------AT
3164 176_HRV12     AAGAGCTGTACCATACCAG-CATATACACAATTACAAATTACAAGA-CAAGTA------AT
3165 177_HRV78a    TAGAGCTGTACCTTATCAG-CACATATATAACCCTAATTATAAAA-CTGAAG------AA
3166 178_HRV78b    TAGAGCTGTACCTTATCAG-CACATATATAACCCTAATTATAAAA-CTGAAG------AA
3167 179_HRV78     TAGAGCTGTACCTTATCAG-CACATATATAACCCTAATTATAAAA-CTGAAG------AA
3168 180_HRV20     AAGAGCAGTGCCTTATCAA-CACACTAAGAGCACAAACTTAGTGC-CAAGGA---CAGGT
3169 181_HRV20a    AAGAGCAGTGCCTTATCAA-CACACTAAGAGCACAAACTTAGTGC-CAAGGA---CAGGT
3170 182_HRV20b    AAGAGCAGTGCCTTATCAA-CACACTAAGAGCACAAACTTAGTGC-CAAGGA---CAGGT
3171 183_HRV68     AAGAGCAGTGCCCTACCAG-CACACCAGAAGTACAAACTTAGTAC-CAAAGG---AAGGT
3172 184_HRV68a    AAGAGCAGTGCCCTACCAG-CACACCAGAAGTACAAACTTAGTAC-CAAAGG---AAGGT
3173 185_HRV68b    AAGAGCAGTGCCCTACCAG-CACACCAGAAGTACAAACTTAGTAC-CAAAGG---AAGGT
3174 186_HRV28     ACGCGCTGTAGCTTATCAA-CATACATACAGTCCAAACTTTGTGC-CTCAGG---AAGGT
3175 187_HRV28a    ACGCGCTGTAGCTTATCAA-CATACATACAGTCCAAACTTTGTGC-CTCAGG---AAGGT
3176 188_HRV28b    ACGCGCTGTAGCTTATCAA-CATACATACAGTCCAAACTTTGTGC-CTCAGG---AAGGT
3177 189_HRV53a    AAGAGCAGTTGCATATCAA-CACACATATAGCCCAAATTTTGTAC-CGCAAA---CAGGA
3178 190_HRV53b    AAGAGCAGTTGCATATCAA-CACACATATAGCCCAAATTTTGTAC-CGCAAA---CAGGA
3179 191_HRV53     AAGAGCAGTTGCATATCAA-CACACATATAGCCCAAATTTTGTAC-CGCAAA---CAGGA
3180 192_HRV46a    CAGAGCAGTCCCATATCAA-CATATTTATAATCCAAATTTCAAGA-CTACTCAACCTGAG
```

FIG. D9 CONT'D

| | | |
|---|---|---|
| 05.trace | | 9/20/2007 5:04 PM |

| | | |
|---|---|---|
| 3181 | 193_HRV46b | CAGAGCAGTCCCATATCAA-CATATTTATAATCCAAATTTCAAGA-CTACTCAACCTGAG |
| 3182 | 194_HRV46 | CAGAGCAGTCCCATATCAA-CATATTTATAATCCAAATTTCAAGA-CTACTCAACCTGAG |
| 3183 | 195_HRV80a | TAGAGCAGTCCCATACCAA-CATACCTACAGCCCAAATTTCAAAA-ACACTG---ATGAA |
| 3184 | 196_HRV80b | TAGAGCAGTCCCATACCAA-CATACCTACAGCCCAAATTTCAAAA-ACACTG---ATGAA |
| 3185 | 197_HRV80 | TAGAGCAGTCCCATACCAA-CATACCTACAGCCCAAATTTCAAAA-ACACTG---ATGAA |
| 3186 | 198_HRV51 | TCGTGCTGTAGCCTACCAA-CACACATACAGTACAAACTTCGTTC-CAAAAGAGGGATTT |
| 3187 | 199_HRV51a | TCGTGCTGTAGCCTACCAA-CACACATACAGTACAAACTTCGTTC-CAAAAGAGGGATTT |
| 3188 | 200_HRV51b | TCGTGCTGTAGCCTACCAA-CACACATACAGTACAAACTTCGTTC-CAAAAGAGGGATTT |
| 3189 | 201_HRV65a | CCGAGCAGTAGCTTACCAA-CACACATACAGTACAAATTTTGTTC-CTAGCGGAGGTCTT |
| 3190 | 202_HRV65b | CCGAGCAGTAGCTTACCAA-CACACATACAGTACAAATTTTGTTC-CTAGCGGAGGTCTT |
| 3191 | 203_HRV65 | CCGAGCAGTAGCTTACCAA-CACACATACAGTACAAATTTTGTTC-CTAGCGGAGGTCTT |
| 3192 | 204_HRV71a | CAGAGCAGTAGCCTACCAA-TCAACATATACCACAAATTTTGTTC-CACAAGACGGGATC |
| 3193 | 205_HRV71b | CAGAGCAGTAGCCTACCAA-TCAACATATACCACAAATTTTGTTC-CACAAGACGGGATC |
| 3194 | 206_HRV71 | CAGAGCAGTAGCCTACCAA-TCAACATATACCACAAATTTTGTTC-CACAAGACGGGATC |
| 3195 | 207_HRV8 | CAGAGCAGTTACGTATAAC-CATATATACAACCCCAATTATGTTA-GAGAGG------GA |
| 3196 | 208_HRV95 | CAGAGCAGTTACGTATAAC-CATATATACAACCCCAATTATGTTA-GAGAGG------GA |
| 3197 | 209_HRV45 | AAGAGCAGTCACATATAAC-CATACATATAATCCAAATTATGTTA-GGGCTG------AT |
| 3198 | 210_HRV45a | AAGAGCAGTCACATATAAC-CATACATATAATCCAAATTATGTTA-GGGCTG------AT |
| 3199 | 211_HRV45b | AAGAGCAGTCACATATAAC-CATACATATAATCCAAATTATGTTA-GGGCTG------AT |
| 3200 | GROUP_1 | --G-G---T----TA------------------AA-T-------------------- |
| 3201 | | |
| 3202 | 1_HRV1A1\|d | GACG------TGACAACAG---CCATAGTCCGCAGAA------ACACTATAACAACTG-- |
| 3203 | 2_HRV1A2\|d | GACG------TGACAACAG---CCATAGTCCGCAGAA------ACACTATAACAACTG-- |
| 3204 | 3_HRV1A\|cD | GACG------TGACAACAG---CCATAGTCCGCAGAA------ACACTATAACAACTG-- |
| 3205 | 4_HRV1B1\|d | GATG------TGACAACAG---CTATAGTTCCTAGAG------CTAGCATGAAAACTG-- |
| 3206 | 5_HRV1B2\|d | GATG------TGACAACAG---CTATAGTTCCTAGAG------CTAGCATGAAAACTG-- |
| 3207 | 6_HRV1B | GATG------TGACAACAG---CTATAGTTCCTAGAG------CTAGCATGAAAACTG-- |
| 3208 | 7_HRV40a\|d | GAAG------TCCAGATTT---TCCTCAAAGAGAG------CCAGCCTAACAACAG-- |
| 3209 | 8_HRV40b\|d | GAAG------TCCAGATTT---TCCTCAAAGAGAGAG------CCAGCCTAACAACAG-- |
| 3210 | 9_HRV40 | GAAG------TCCAGATTT---TCCTCAAAGAGAGAG------CCAGCCTAACAACAG-- |
| 3211 | 10_HRV85 | GAAG------TTAAGATCT---TCCTCAAAGAGAGAG------CTAGTTTAACCACAG-- |
| 3212 | 11_HRV85a\| | GAAG------TTAAGATCT---TCCTCAAAGAGAGAG------CTAGTTTAACCACAG-- |
| 3213 | 12_HRV85b\| | GAAG------TTAAGATCT---TCCTCAAAGAGAGAG------CTAGTTTAACCACAG-- |
| 3214 | 13_HRV56a\| | GATG------TACAGATCT---TCTTAAAACCCAGAC------CCAGCCTAACAACAT-- |
| 3215 | 14_HRV56b\| | GATG------TACAGATCT---TCTTAAAACCCAGAC------CCAGCCTAACAACAT-- |
| 3216 | 15_HRV56 | GATG------TACAGATCT---TCTTAAAACCCAGAC------CCAGCCTAACAACAT-- |
| 3217 | 16_HRV54 | GATC------CAACAATTT---TCCTTAAACACAGGA------CAAACCTTGTAACAG-- |
| 3218 | 17_HRV98 | GAAC------CAACAATCT---TTCTTAAGCATAGAA------AAGATCTTGTAACAG-- |
| 3219 | 18_HRV59a\| | GAAC------CTGAAATTT---TCTTAAAACCAAGAA------TGAATATTACAACAG-- |
| 3220 | 19_HRV59b\| | GAAC------CTGAAATTT---TCTTAAAACCAAGAA------TGAATATTACAACAG-- |
| 3221 | 20_HRV59 | GAAC------CTGAAATTT---TCTTAAAACCAAGAA------TGAATATTACAACAG-- |
| 3222 | 21_HRV63 | GAGA------CTGAAATTT---TCTTAAAACCTAGAG------CAACTATCAAGACAG-- |
| 3223 | 22_HRV63b\| | GAGA------CTGAAATTT---TCTTAAAACCTAGAG------CAACTATCAAGACAG-- |
| 3224 | 23_HRV63a\| | GAGA------CTGAAATTT---TCTTAAAACCTAGAG------CAACTATCAAGACAG-- |
| 3225 | 24_HRV39 | GAAC------CAACACTCT---TTATAAAATCAAGAG------AGAATCTTACCACAG-- |
| 3226 | 25_HRV39a\| | GAAC------CAACACTCT---TTATAAAATCAAGAG------AGAATCTTACCACAG-- |
| 3227 | 26_HRV39b\| | GAAC------CAACACTCT---TTATAAAACCAAGAG------AGAATCTTACCACAG-- |
| 3228 | 27_HRV10a\| | GAAT------TACAAATAT---TTATTAGGTCTAGAGATGATCCCAAAGTAGTAACTG-- |
| 3229 | 28_HRV10b\| | GAAT------TACAAATAT---TTATTAGGTCTAGAGATGATCCCAAAGTAGTAACTG-- |
| 3230 | 29_HRV10 | GAAT------TACAAATAT---TTATTAGGTCTAGAGATGATCCCAAAGTAGTAACTG-- |
| 3231 | 30_HRV100a | GATG------TAAAGATTT---TCATTAGACCCAGAGATGATCCAAAGTTTGTAACTG-- |
| 3232 | 31_HRV100b | GATG------TAAAGATTT---TCATTAGACCCAGAGATGATCCAAAGTTTGTAACTG-- |
| 3233 | 32_HRV100 | GATG------TAAAGATTT---TCATTAGACCCAGAGATGATCCAAAGTTTGTAACTG-- |
| 3234 | 33_HRV66 | GATC------TGCAAATTT---TCATTAAACCTAGAACAGATCCAAAAGTAGTCAATG-- |
| 3235 | 34_HRV66b\| | GATC------TGCAAATTT---TCATTAAACCTAGAACAGATCCAAAAGTAGTCAATG-- |
| 3236 | 35_HRV66a\| | GATC------TGCAAATTT---TCATTAAACCTAGAACAGATCCAAAAGTAGTCAATG-- |
| 3237 | 36_HRV77a\| | GATG------TACAAATCT---TTATTAAAGAGAGAGCAAGCCCAAAAGTAGTTACTT-- |
| 3238 | 37_HRV77b\| | GATG------TACAAATCT---TTATTAAAGAGAGAGCAAGCCCAAAAGTAGTTACTT-- |
| 3239 | 38_HRV77 | GATG------TACAAATCT---TTATTAAAGAGAGAGCAAGCCCAAAAGTAGTTACTT-- |
| 3240 | 39_HRV62a | ---G------TTGACATTT---TTATAAAATCAAGG------CAAAACTTGCAAACAG-- |
| 3241 | 40_HRV62b | ---G------TTGACATTT---TTATAAAATCAAGG------CAAAACTTGCAAACAG-- |
| 3242 | 41_HRV25 | ---G------TTGACATCT---TTATACAACCAAGA------AACAGTTTAAAAACAG-- |
| 3243 | 42_HRV29a | ---G------AT-CCAG-----TTGTGGAATCCAGA------CCAAGCTTAATGACAG-- |
| 3244 | 43_HRV29b | ---G------AT-ACAG-----TTGTGGAATCCAGA------CCAAGCTTAATGACAG-- |
| 3245 | 44_HRV44a | ---G------AT-ACAG-----TTGTGGAACCTAGA------CACAGCATAATGACAG-- |

FIG. D9 CONT'D

```
05.trace                                                                        9/20/2007 5:04 PM 3246  45_HRV44b     ---G------AT-ACAG-----TTGTGGAACCTAGA------CACAGCATAATGACAG--
3247  46_HRV31      GAAG------TTACAATCT---TTGTTAAACACAGGGATAATCCAAAGATTATCACAG--
3248  47_HRV31a|    GAAG------TTACAATCT---TTGTTAAACACAGGGATAATCCAAAGATTATCACAG--
3249  48_HRV31b|    GAAG------TTACAATCT---TTGTTAAACACAGGGATAATCCAAAGATTATCACAG--
3250  49_HRV47      GAAG------TTGCAATTT---TCATTGAGCATAGAGAAAATCCAAAATTCATTACAG--
3251  50_HRV47a|    GAAG------TTGCAATTT---TCATTGAGCATAGAGAAAATCCAAAATTCATTACAG--
3252  51_HRV47b|    GAAG------TTGCAATTT---TCATTGAGCATAGAGAAAATCCAAAATTCATTACAG--
3253  52_HRV11      CAGG------TGAAAACAG---CTGTCAAGGCTAGGAAAACAATTAAAACAGCA------
3254  53_HRV11b|    CAGG------TGAAAACAG---CTGTCAAGGCTAGGAAAACAATTAAAACAGCG------
3255  54_HRV11a|    CAGG------TGAAAACAG---CTGTCAAGGCTAGGAAAACAATTAAAACAGCT------
3256  55_HRV76      GATG------TGCAAACAG---CTATTAGACCAAGAGCAACAATTAAGACTGCA------
3257  56_HRV76b|    GATG------TGCAAACAG---CTATTAGACCAAGAGCAACAATTAAGACTGCG------
3258  57_HRV76a|    GATG------TGCAAACAG---CTATTAGACCAAGAGCAACAATTAAGACTGCT------
3259  58_HRV33      GAAG------TGAAGACAG---CTATTAGACCAAGAGCAACAATCAAGACTGCA------
3260  59_HRV33b|    GAAG------TGAAGACAG---CTATTAGACCAAGAGCAACAATCAAGACTGCG------
3261  60_HRV33a|    GAAG------TGAAGACAG---CTATTAGACCAAGAGCAACAATCAAGACTGCT------
3262  61_HRV24a|    GAAG------TCAAGACAG---CAATTGAACCTAGAAGAGGAATTAAAACAGTG------
3263  62_HRV24b|    GAAG------TCAAGACAG---CAATTGAACCTAGAAGAGGAATTAAAACAGTC------
3264  63_HRV24      GAAG------TCAAGACAG---CAATTGAACCTAGAAGAGGAATTAAAACAGTT------
3265  64_HRV90      GAAC------TTAAGACTG---CAATTAGGCCCAGGAAAACAATCACAACAGCA------
3266  65_HRV90a|    GAAC------TTAAGACTG---CAATTAGGCCCAGGAAAACAATCACAACAGCG------
3267  66_HRV90b|    GAAC------TTAAGACTG---CAATTAGGCCCAGGAAAACAATCACAACAGCT------
3268  67_HRV34      ACTG------AGAAGACTG---CAATCAAACACAGAGCAAAGATCACAATGGCC------
3269  68_HRV34b|    ACTG------AGAAGACTG---CAATCAAACACAGAGCAAAGATCACAATGGCA------
3270  69_HRV34a|    ACTG------AGAAGACTG---CAATCAAACACAGAGCAAAGATCACAATGGCT------
3271  70_HRV50a|    ACTG------AGAAGACTG---CAATTGCAACTAGACCAAAGATCACAGTGGCA------
3272  71_HRV50b|    ACTG------AGAAGACTG---CAATTGCAACTAGACCAAAGATCACAGTGGCG------
3273  72_HRV50      ACTG------AGAAGACTG---CAATTGCAACTAGACCAAAGATCACAGTGGCT------
3274  73_HRV18a|    AGAG------AGAAAACTG---CCATAGTACCCAGAGCAAGGATTACAATGGCA------
3275  74_HRV18b|    AGAG------AGAAAACTG---CCATAGTACCCAGAGCAAGGATTACAATGGCG------
3276  75_HRV18      AGAG------AGAAAACTG---CCATAGTACCCAGAGCAAGGATTACAATGGCT------
3277  76_HRV55      ACAG------AAAAGACAG---CAATTGAATACAGAAGGGACATTAAAACAGTG------
3278  77_HRV55b|    ACAG------AAAAGACAG---CAATTGAATACAGAAGGGACATTAAAACAGTC------
3279  78_HRV55a|    ACAG------AAAAGACAG---CAATTGAATACAGAAGGGACATTAAAACAGTA------
3280  79_HRV57      CAAG------AAGAAACAG---CAATTAAATATAGAAGGGACATTAAAATTGTTAAGA--
3281  80_HRV57a|    CAAG------AAGAAACAG---CAATTAAATATAGAAGGGACATTAAAATTGTTAAGA--
3282  81_HRV57b|    CAAG------AAGAAACAG---CAATTAAATATAGAAGGGACATTAAAATTGTTAAGA--
3283  82_HRV21      GAAG------TCACTTCTG---CAGTTGAGTCCAGAAGAACAATTGTCACAGTT------
3284  83_HRVHan     GATG------TCACTTCTG---CAGTTGAGTCCAGAAGAACAATTGTCACAGTT------
3285  84_HRV43      GAGG------TAGAAACAG---CCATAGTATCTAGGAGGGATATCAAAATTGTCAATG--
3286  85_HRV43b|    GAGG------TAGAAACAG---CCATAGTATCTAGGAGGGATATCAAAATTGTCAATG--
3287  86_HRV43a|    GAGG------TAGAAACAG---CCATAGTATCTAGGAGGGATATCAAAATTGTCAATG--
3288  87_HRV75      CAAG------TTGAGATTG---CTATTGAGCCCAGAAGAGATGTTAAGTTTGTAAATG--
3289  88_HRV75b|    CAAG------TTGAGATTG---CTATTGAGCCCAGAAGAGATGTTAAGTTTGTAAATG--
3290  89_HRV75a|    CAAG------TTGAGATTG---CTATTGAGCCCAGAAGAGATGTTAAGTTTGTAAATG--
3291  96_HRV9a|d    GATT------ATGCCACAG---TTATACCAGTTAGAGACAATGTTAGGGCAGTAAAGA--
3292  97_HRV9b|d    GATT------ATGCCACAG---TTATACCAGTTAGAGACAATGTTAGGGCAGTAAAGA--
3293  98_HRV9       GATT------ATGCCACAG---TTATACCAGTTAGAGACAATGTTAGGGCAGTAAAGA--
3294  99_HRV32      GATT------ACACCACAG---CCATACAAACCAGAGAGCATGTTAGAGCAGTCAAAA--
3295  100_HRV32a    GATT------ACACCACAG---CCATACAAACCAGAGAGCATGTTAGAGCAGTCAAAA--
3296  101_HRV32b    GATT------ACACCACAG---CCATACAAACCAGAGAGCATGTTAGAGCAGTCAAAA--
3297  102_HRV67     GAGG------CTCAAACGG---TTATACCTGTTAGAGCAGATGTTAGAACAATTAGAA--
3298  103_HRV67a    GAGG------CTCAAACGG---TTATACCTGTTAGAGCAGATGTTAGAACAATTAGAA--
3299  104_HRV67b    GAGG------CTCAAACGG---TTATACCTGTTAGAGCAGATGTTAGAACAATTAGAA--
3300  105_HRV15     GATG------TAACTACAG---TTATTCCAACTAGAGAAAATGTTAGAGCTATAGTAA--
3301  106_HRV15a    GATG------TAACTACAG---TTATTCCAACTAGAGAAAATGTTAGAGCTATAGTAA--
3302  107_HRV15b    GATG------TAACTACAG---TTATTCCAACTAGAGAAAATGTTAGAGCTATAGTAA--
3303  108_HRV74a    GACG------TAACTACAG---TCATCCCAACTAGG---------AGATCAATAGTGA--
3304  109_HRV74b    GACG------TAACTACAG---TCATCCCAACTAGG---------AGATCAATAGTGA--
3305  110_HRV74     GACG------TAACTACAG---TCATCCCAACTAGG---------AGATCAATAGTGA--
3306  111_HRV38a    GAAG------TAACCACTA---TGATTCCAACTAGAACCAACATAAGAACCATCGTAA--
3307  112_HRV38b    GAAG------TAACCACTA---TGATTCCAACTAGAACCAACATAAGAACCATCGTAA--
3308  113_HRV38     GAAG------TAACCACTA---TGATTCCAACTAGAACCAACATAAGAACCATCGTAA--
3309  114_HRV60     GAAG------CAGCCATAA---CAATCCCCATTAGAACTGATATACGAGCAATCAGAA--
3310  115_HRV60a    GAAG------CAGCCATAA---CAATCCCCATTAGAACTGATATACGAGCAATCAGAA--
```

FIG. D9 CONT'D 05.trace                                                                                    9/20/2007 5:04 PM

```
3311 116_HRV60b   GAAG------CAGCCATAA---CAATCCCCATTAGAACTGATATACGAGCAATCAGAA--
3312 117_HRV64a   GAAT------ACACACCAC---CCGTTCCGTCACGTAACAGCCCCAGAGATATTGTCA--
3313 118_HRV64b   GAAT------ACACACCAC---CCGTTCCGTCACGTAACAGCCCCAGAGATATTGTCA--
3314 119_HRV64    GAAT------ACACACCAC---CCGTTCCGTCACGTAACAGCCCCAGAGATATTGTCA--
3315 120_HRV94a   GAGT------ACAAGCCAC---CTGTCCCAGTTAGGAATAGCCCCAGAGACATTGTCA--
3316 121_HRV94b   GAGT------ACAAGCCAC---CTGTCCCAGTTAGGAATAGCCCCAGAGACATTGTCA--
3317 122_HRV94    GAGT------ACAAGCCAC---CTGTCCCAGTTAGGAATAGCCCCAGAGACATTGTCA--
3318 123_HRV22    GATT------ACACACTAC---CTATCCCAACAAGAGCCAACCCTAGACAAATTTTGA--
3319 124_HRV22a   GATT------ACACACTAC---CTATCCCAACAAGAGCCAACCCTAGACAAATTTTGA--
3320 125_HRV22b   GATT------ACACACTAC---CTATCCCAACAAGAGCCAACCCTAGACAAATTTTGA--
3321 126_HRV82    GATT------ACAGTGTTG---TTATTCCAGTTAGAGAGAGTCCCAGACAGATTCTTA--
3322 127_HRV82b   GATT------ACAGTGTTG---TTATTCCAGTTAGAGAGAGTCCCAGACAGATTCTTA--
3323 128_HRV82a   GATT------ACAGTGTTG---TTATTCCAGTTAGAGAGAGTCCCAGACAGATTCTTA--
3324 129_HRV19    GAAG------TCACTCTTC---CAATTGAAATAAGAGATAACCCTAGACATATAAAGA--
3325 130_HRV19a   GAAG------TCACTCTTC---CAATTGAAATAAGAGATAACCCTAGACATATAAAGA--
3326 131_HRV19b   GAAG------TCACTCTTC---CAATTGAAATAAGAGATAACCCTAAGACATATAAAGA--
3327 132_HRV13    GATG------TTGCAGTCT---CCATTGTACCTAGAGCAAATGTTAGGGAAATTAGAA--
3328 133_HRV13a   GATG------TTGCAGTCT---CCATTGTACCTAGAGCAAATGTTAGGGAAATTAGAA--
3329 134_HRV13b   GATG------TTGCAGTCT---CCATTGTACCTAGAGCAAATGTTAGGGAAATTAGAA--
3330 135_HRV41    GCAGA---GATTGTGGCTT---CTGTCAGACCTAGAGACAATGTTAGACAAGTAAGAA--
3331 136_HRV41a   GCAGA---GATTGTGGCTT---CTGTCAGACCTAGAGACAATGTTAGACAAGTAAGAA--
3332 137_HRV41b   GCAGA---GATTGTGGCTT---CTGTCAGACCTAGAGACAATGTTAGACAAGTAAGAA--
3333 138_HRV73    GAAG------TTACTACTG---CCATTAGGCATAGAGATAATGTTAGAGCCATCCAAA--
3334 139_HRV73b   GAAG------TTACTACTG---CCATTAGGCATAGAGATAATGTTAGAGCCATCCAAA--
3335 140_HRV73a   GAAG------TTACTACTG---CCATTAGGCATAGAGATAATGTTAGAGCCATCCAAA--
3336 141_HRV61    GAAAAACAAGTTACCACTT---TCATCAAACCTAGAGCTAACTTAAGAGAGATTAGAA--
3337 142_HRV61a   GAAAAACAAGTTACCACTT---TCATCAAACCTAGAGCTAACTTAAGAGAGATTAGAA--
3338 143_HRV61b   GAAAAACAAGTTACCACTT---TCATCAAACCTAGAGCTAACTTAAGAGAGATTAGAA--
3339 144_HRV96    -------AGGTTACCACTT---TTATCAAACCTAGAGAAAATCTAAGGGATATTAGAA--
3340 145_HRV96b   -------AGGTTACCACTT---TTATCAAACCTAGAGAAAATCTAAGGGATATTAGAA--
3341 146_HRV96a   -------AGGTTACCACTT---TTATCAAACCTAGAGAAAATCTAAGGGATATTAGAA--
3342  90_HRV16a|  GTAC------ACAATGATGTGGCTATAAGACCTAGAACAAATCTAACAACTGTA------
3343  91_HRV16b|  GTAC------ACAATGATGTGGCTATAAGACCTAGAACAAATCTAACAACTGTC------
3344  92_1AYM_A   GTAC------ACAATGATGTGGCTATAAGACCTAGAACAAATCTAACAACTGTT------
3345  93_HRV81a|  GTCC------ACACTAGTGTAGCCATAAAACCTAGAACAAGTCTAACAAATGTG------
3346  94_HRV81b|  GTCC------ACACTAGTGTAGCCATAAAACCTAGAACAAGTCTAACAAATGTC------
3347  95_HRV81    GTCC------ACACTAGTGTAGCCATAAAACCTAGAACAAGTCTAACAAATGTT------
3348 147_HRV2     AGTA------TTCAGACAG---CAATTGTGACCAGACCAATTATCACTACAGCT------
3349 148_HRV2a|   AGTA------TTCAGACAG---CAATTGTGACCAGACCAATTATCACTACAGCA------
3350 149_HRV2b|   AGTA------TTCAGACAG---CAATTGTGACCAGACCAATTATCACTACAGCG------
3351 150_HRV49a   GACA------TTAAAACAG---GAATCACATCCAGAGCAATTATTACAACAGCG------
3352 151_HRV49b   GACA------TTAAAACAG---GAATCACATCCAGAGCAATTATTACAACAGCA------
3353 152_HRV49    GACA------TTAAAACAG---GAATCACATCCAGAGCAATTATTACAACAGCT------
3354 153_HRV23a   AATG------TCAAATCAA---GGGTTGCACATAGACCTGCAGTGATAACAGCG------
3355 154_HRV23b   AATG------TCAAATCAA---GGGTTGCACATAGACCTGCAGTGATAACAGCA------
3356 155_HRV23    AATG------TCAAATCAA---GGGTTGCACATAGACCTGCAGTGATAACAGCT------
3357 156_HRV30a   GAAG------TTAAATCAA---GGGTTGAACACAGAGCTAGGGTGACGACAGCA------
3358 157_HRV30b   GAAG------TTAAATCAA---GGGTTGAACACAGAGCTAGGGTGACGACAGCG------
3359 158_HRV30    GAAG------TTAAATCAA---GGGTTGAACACAGAGCTAGGGTGACGACAGCT------
3360 159_HRV7     GAGG------TCGCA---ACTCAAATCAAAACCAGAGCCAATCTTTTCACCCTCAAAT--
3361 160_HRV7b|   GAGG------TCGCA---ACTCAAATCAAAACCAGAGCCAATCTTTTCACCCTCAAAT--
3362 161_HRV7a|   GAGG------TCGCA---ACTCAAATCAAAACCAGAGCCAATCTTTTCACCCTCAAAT--
3363 162_HRV88    GAAG------TAGCA---ACTCAAATCAAAACCAGACGAGATGTTTACACTGTTACCA--
3364 163_HRV88a   GAAG------TAGCA---ACTCAAATCAAAACCAGACGAGATGTTTACACTGTTACCA--
3365 164_HRV88b   GAAG------TAGCA---ACTCAAATCAAAACCAGACGAGATGTTTACACTGTTACCA--
3366 165_HRV36a   GAGA------TCACA---ACCCAAATTAAAACCAGACCTAATGTCTTCACTGTA------
3367 166_HRV36b   GAGA------TCACA---ACCCAAATTAAAACCAGACCTAATGTCTTCACTGTG------
3368 167_HRV36    GAGA------TCACA---ACCAAATTAAAACCAGACCTAATGTCTTCACTGTT------
3369 168_HRV89a   GAGG------CCACA---ACTCAGATTAAAACCAGACCTGATGTTTTTACCGTTACAA--
3370 169_HRV89b   GAGG------CCACA---ACTCAGATTAAAACCAGACCTGATGTTTTTACCGTTACAA--
3371 170_HRV89    GAGG------CCACA---ACTCAGATTAAAACCAGACCTGATGTTTTTACCGTTACAA--
3372 171_HRV58    GAGG------TAACA---ACACAAATCAAACCCAGAACCAATGTTTTTACTATTACAT--
3373 172_HRV58a   GAGG------TAACA---ACACAAATCAAACCCAGAACCAATGTTTTTACTATTACAT--
3374 173_HRV58b   GAGG------TAACA---ACACAAATCAAACCCAGAACCAATGTTTTTACTATTACAT--
3375 174_HRV12a   GGAG------TTCCAGACAATAGAGTCAAACTCAGAGAGACACTCACCACAGTA------
```

FIG. D9 CONT'D

05.trace                                                                    9/20/2007 5:04 PM

```
3376 175_HRV12b     GGAG------TTCCAGACAATAGAGTCAAACTCAGAGAGACACTCACCACAGTG------
3377 176_HRV12      GGAG------TTCCAGACAATAGAGTCAAACTCAGAGAGACACTCACCACAGTT------
3378 177_HRV78a     GGAA------CTCCAGACACCAAAGTGGCAATTAGAGCTAATATTAAAACTGTA------
3379 178_HRV78b     GGAA------CTCCAGACACCAAAGTGGCAATTAGAGCTAATATTAAAACTGTG------
3380 179_HRV78      GGAA------CTCCAGACACCAAAGTGGCAATTAGAGCTAATATTAAAACTGTT------
3381 180_HRV20      GAAA------TTACA---ACTCATATCAGATTCAGAAACACTGTCAAAGATCTAACATAC
3382 181_HRV20a     GAAA------TTACA---ACTCATATCAGATTCAGAAACACTGTCAAAGATCTAACATAC
3383 182_HRV20b     GAAA------TTACA---ACTCATATCAGATTCAGAAACACTGTCAAAGATCTAACATAC
3384 183_HRV68      GATA------TTAAA---ACTCATATTAAATTTAGGAATACTGTTAAAGATTTGGCATAT
3385 184_HRV68a     GATA------TTAAA---ACTCATATTAAATTTAGGAATACTGTTAAAGATTTGGCATAT
3386 185_HRV68b     GATA------TTAAA---ACTCATATTAAATTTAGGAATACTGTTAAAGATTTGGCATAT
3387 186_HRV28      GATG------TTGAG---ACTCATATTAAATTTAGAACAGATGTTAAACAGATCACAA--
3388 187_HRV28a     GATG------TTGAG---ACTCATATTAAATTTAGAACAGATGTTAAACAGATCACAA--
3389 188_HRV28b     GATG------TTGAG---ACTCATATTAAATTTAGAACAGATGTTAAACAGATCACAA--
3390 189_HRV53a     ACAG------TTGAA---ACTCACATTAAGTTCAGACCTGATGTTAAAGATGTAACAT--
3391 190_HRV53b     ACAG------TTGAA---ACTCACATTAAGTTCAGACCTGATGTTAAAGATGTAACAT--
3392 191_HRV53      ACAG------TTGAA---ACTCACATTAAGTTCAGACCTGATGTTAAAGATGTAACAT--
3393 192_HRV46a     ACTA------TACCAGATACTCATATTGGAATTAGAAGGGATATAAAGTACATTAAAA--
3394 193_HRV46b     ACTA------TACCAGATACTCATATTGGAATTAGAAGGGATATAAAGTACATTAAAA--
3395 194_HRV46      ACTA------TACCAGATACTCATATTGGAATTAGAAGGGATATAAAGTACATTAAAA--
3396 195_HRV80a     TCTA------TACCAGATACACAAATTAAAATCAGAGATAATATCAGGCAGGTTAGAA--
3397 196_HRV80b     TCTA------TACCAGATACACAAATTAAAATCAGAGATAATATCAGGCAGGTTAGAA--
3398 197_HRV80      TCTA------TACCAGATACACAAATTAAAATCAGAGATAATATCAGGCAGGTTAGAA--
3399 198_HRV51      GAAG------GCTTGAAAACTCAGATTAAAACTAGGGCAGACATCAAACTTGTGAACT--
3400 199_HRV51a     GAAG------GCTTGAAAACTCAGATTAAAACTAGGGCAGACATCAAACTTGTGAACT--
3401 200_HRV51b     GAAG------GCTTGAAAACTCAGATTAAAACTAGGGCAGACATCAAACTTGTGAACT--
3402 201_HRV65a     ACAA------ACCTAAGAACCCAAATTAAAACCAGAGATAACATTAAAATTGTAAACT--
3403 202_HRV65b     ACAA------ACCTAAGAACCCAAATTAAAACCAGAGATAACATTAAAATTGTAAACT--
3404 203_HRV65      ACAA------ACCTAAGAACCCAAATTAAAACCAGAGATAACATTAAAATTGTAAACT--
3405 204_HRV71a     AATT------CCATTAAAACCAAAATCAAAATCAGAAGAGACATTAAAGAGGTCAGCA--
3406 205_HRV71b     AATT------CCATTAAAACCAAAATCAAAATCAGAAGAGACATTAAAGAGGTCAGCA--
3407 206_HRV71      AATT------CCATTAAAACCAAAATCAAAATCAGAAGAGACATTAAAGAGGTCAGCA--
3408 207_HRV8       GTAA------CACCAGAAACTAAGGTTAAATATAGAGCTGAAGTCACAACCATT------
3409 208_HRV95      GTAA------CACCAGAAACTAAGGTCAAATATAGAGCTGAAGTCACAACCATT------
3410 209_HRV45      GAAA------CAGCC---ACAAAAGTCCAAACTAGAGCAAATGTCACAACAGTA------
3411 210_HRV45a     GAAA------CAGCC---ACAAAAGTCCAAACTAGAGCAAATGTCACAACAGTG------
3412 211_HRV45b     GAAA------CAGCC---ACAAAAGTCCAAACTAGAGCAAATGTCACAACAGTT------
3413 GROUP_1        ------------------------T--------G--------------------------
3414
3415 1_HRV1A1|d     ----CA---------------
3416 2_HRV1A2|d     ----CG---------------
3417 3_HRV1A|cD     ----CT---------------
3418 4_HRV1B1|d     ----TA---------------
3419 5_HRV1B2|d     ----TC---------------
3420 6_HRV1B        ----TT---------------
3421 7_HRV40a|d     ----TA---------------
3422 8_HRV40b|d     ----TC---------------
3423 9_HRV40        ----TT---------------
3424 10_HRV85       ----CA---------------
3425 11_HRV85a|     ----CG---------------
3426 12_HRV85b|     ----CT---------------
3427 13_HRV56a|     ----TA---------------
3428 14_HRV56b|     ----TG---------------
3429 15_HRV56       ----TT---------------
3430 16_HRV54       ----CT---------------
3431 17_HRV98       ----CT---------------
3432 18_HRV59a|     ----CA---------------
3433 19_HRV59b|     ----CG---------------
3434 20_HRV59       ----CT---------------
3435 21_HRV63       ----CA---------------
3436 22_HRV63b|     ----CG---------------
3437 23_HRV63a|     ----CT---------------
3438 24_HRV39       ----CT---------------
3439 25_HRV39a|     ----CA---------------
3440 26_HRV39b|     ----CT---------------
```

FIG. D9 CONT'D 05.trace                                                                 9/20/2007 5:04 PM

```
3441  27_HRV10a|     ----CA---------------
3442  28_HRV10b|     ----CC---------------
3443  29_HRV10      ----CT---------------
3444  30_HRV100a    ----CA---------------
3445  31_HRV100b    ----CG---------------
3446  32_HRV100     ----CT---------------
3447  33_HRV66      ----TA---------------
3448  34_HRV66b|    ----TG---------------
3449  35_HRV66a|    ----TC---------------
3450  36_HRV77a|    ----TG---------------
3451  37_HRV77b|    ----TA---------------
3452  38_HRV77      ----TT---------------
3453  39_HRV62a     ----CT---------------
3454  40_HRV62b     ----C----------------
3455  41_HRV25      ----CT---------------
3456  42_HRV29a     ----CT---------------
3457  43_HRV29b     ----CT---------------
3458  44_HRV44a     ----CT---------------
3459  45_HRV44b     ----CT---------------
3460  46_HRV31      ----CA---------------
3461  47_HRV31a|    ----CT---------------
3462  48_HRV31b|    ----CA---------------
3463  49_HRV47      ----CA---------------
3464  50_HRV47a|    ----CT---------------
3465  51_HRV47b|    ----CA---------------
3466  52_HRV11      ---------------------
3467  53_HRV11b|    ---------------------
3468  54_HRV11a|    ---------------------
3469  55_HRV76      ---------------------
3470  56_HRV76b|    ---------------------
3471  57_HRV76a|    ---------------------
3472  58_HRV33      ---------------------
3473  59_HRV33b|    ---------------------
3474  60_HRV33a|    ---------------------
3475  61_HRV24a|    ---------------------
3476  62_HRV24b|    ---------------------
3477  63_HRV24      ---------------------
3478  64_HRV90      ---------------------
3479  65_HRV90a|    ---------------------
3480  66_HRV90b|    ---------------------
3481  67_HRV34      ---------------------
3482  68_HRV34b|    ---------------------
3483  69_HRV34a|    ---------------------
3484  70_HRV50a|    ---------------------
3485  71_HRV50b|    ---------------------
3486  72_HRV50      ---------------------
3487  73_HRV18a|    ---------------------
3488  74_HRV18b|    ---------------------
3489  75_HRV18      ---------------------
3490  76_HRV55      ---------------------
3491  77_HRV55b|    ---------------------
3492  78_HRV55a|    ---------------------
3493  79_HRV57      ----ATGTG------------
3494  80_HRV57a|    ----ATGTA------------
3495  81_HRV57b|    ----ATGTC------------
3496  82_HRV21      ---------------------
3497  83_HRVHan     ---------------------
3498  84_HRV43      ----CA---------------
3499  85_HRV43b|    ----CG---------------
3500  86_HRV43a|    ----CT---------------
3501  87_HRV75      ----CA---------------
3502  88_HRV75b|    ----CG---------------
3503  89_HRV75a|    ----CT---------------
3504  96_HRV9a|d    ----ATGTC------------
3505  97_HRV9b|d    ----ATGTG------------
```

FIG. D9 CONT'D 05.trace                                                              9/20/2007 5:04 PM

```
3506  98_HRV9       ----ATGTA------------
3507  99_HRV32      ----ATGTA------------
3508  100_HRV32a    ----ATGTG------------
3509  101_HRV32b    ----ATGTC------------
3510  102_HRV67     ----ATGTA------------
3511  103_HRV67a    ----ATGTC------------
3512  104_HRV67b    ----ATGTT------------
3513  105_HRV15     ----ATGTT------------
3514  106_HRV15a    ----ATGTA------------
3515  107_HRV15b    ----ATGTC------------
3516  108_HRV74a    ----ATGTA------------
3517  109_HRV74b    ----ATGTC------------
3518  110_HRV74     ----ATGTT------------
3519  111_HRV38a    ----ATGTA------------
3520  112_HRV38b    ----ATGTC------------
3521  113_HRV38     ----ATGTT------------
3522  114_HRV60     ----CAGTT------------
3523  115_HRV60a    ----CAGTA------------
3524  116_HRV60b    ----CAGTG------------
3525  117_HRV64a    ----CAGTG------------
3526  118_HRV64b    ----CAGTG------------
3527  119_HRV64     ----CAGTA------------
3528  120_HRV94a    ----CAGTG------------
3529  121_HRV94b    ----CAGTC------------
3530  122_HRV94     ----CAGTA------------
3531  123_HRV22     ----ATGTA------------
3532  124_HRV22a    ----ATGTG------------
3533  125_HRV22b    ----ATGTC------------
3534  126_HRV82     ----ATGTA------------
3535  127_HRV82b    ----ATGTT------------
3536  128_HRV82a    ----ATGTC------------
3537  129_HRV19     ----ATGTA------------
3538  130_HRV19a    ----ATGTG------------
3539  131_HRV19b    ----ATGTC------------
3540  132_HRV13     ----ACTTT------------
3541  133_HRV13a    ----ACTTG------------
3542  134_HRV13b    ----ACTTA------------
3543  135_HRV41     ----ATTAT------------
3544  136_HRV41a    ----ATTAG------------
3545  137_HRV41b    ----ATTAC------------
3546  138_HRV73     ----ATTTT------------
3547  139_HRV73b    ----ATTTG------------
3548  140_HRV73a    ----ATTTC------------
3549  141_HRV61     ----CATTT------------
3550  142_HRV61a    ----CATTT------------
3551  143_HRV61b    ----CATTT------------
3552  144_HRV96     ----ATTTT------------
3553  145_HRV96b    ----ATTTA------------
3554  146_HRV96a    ----ATTTC------------
3555  90_HRV16a|    ---------------------
3556  91_HRV16b|    ---------------------
3557  92_1AYM_A     ---------------------
3558  93_HRV81a|    ---------------------
3559  94_HRV81b|    ---------------------
3560  95_HRV81      ---------------------
3561  147_HRV2      ---------------------
3562  148_HRV2a|    ---------------------
3563  149_HRV2b|    ---------------------
3564  150_HRV49a    ---------------------
3565  151_HRV49b    ---------------------
3566  152_HRV49     ---------------------
3567  153_HRV23a    ---------------------
3568  154_HRV23b    ---------------------
3569  155_HRV23     ---------------------
3570  156_HRV30a    ---------------------
```

FIG. D9 CONT'D

```
05.trace                                                              9/20/2007 5:04 PM 3571  157_HRV30b     --------------------
3572  158_HRV30      --------------------
3573  159_HRV7       ----CAGCT-----------
3574  160_HRV7b|     ----CAGCA-----------
3575  161_HRV7a|     ----CAGCG-----------
3576  162_HRV88      ----CTGCT-----------
3577  163_HRV88a     ----CTGCA-----------
3578  164_HRV88b     ----CTGCG-----------
3579  165_HRV36a     --------------------
3580  166_HRV36b     --------------------
3581  167_HRV36      --------------------
3582  168_HRV89a     ----ACGTG-----------
3583  169_HRV89b     ----ACGTA-----------
3584  170_HRV89      ----ACGTC-----------
3585  171_HRV58      ----CTGCT-----------
3586  172_HRV58a     ----CTGCA-----------
3587  173_HRV58b     ----CTGCC-----------
3588  174_HRV12a     --------------------
3589  175_HRV12b     --------------------
3590  176_HRV12      --------------------
3591  177_HRV78a     --------------------
3592  178_HRV78b     --------------------
3593  179_HRV78      --------------------
3594  180_HRV20      CCCACAGAAATGACGAATGTT
3595  181_HRV20a     CCCACAGAAATGACGAATGTA
3596  182_HRV20b     CCCACAGAAATGACGAATGTG
3597  183_HRV68      CCTCCAGAATTAGCAAACCTT
3598  184_HRV68a     CCTCCAGAATTAGCAAACCTT
3599  185_HRV68b     CCTCCAGAATTAGCAAACCTT
3600  186_HRV28      ----CAGTT-----------
3601  187_HRV28a     ----CAGTA-----------
3602  188_HRV28b     ----CAGTC-----------
3603  189_HRV53a     ----CAGTAATGACAGCT---
3604  190_HRV53b     ----CAGTAATGACAGCT---
3605  191_HRV53      ----CAGTAATGACAGCA---
3606  192_HRV46a     ----CAGCA-----------
3607  193_HRV46b     ----CAGCC-----------
3608  194_HRV46      ----CAGCT-----------
3609  195_HRV80a     ----CAGTA-----------
3610  196_HRV80b     ----CAGTC-----------
3611  197_HRV80      ----CAGTT-----------
3612  198_HRV51      -----TT-------------
3613  199_HRV51a     -----TA-------------
3614  200_HRV51b     -----TG-------------
3615  201_HRV65a     -----TG-------------
3616  202_HRV65b     -----TA-------------
3617  203_HRV65      -----TT-------------
3618  204_HRV71a     -----ACTAA----------
3619  205_HRV71b     -----ACTAG----------
3620  206_HRV71      -----ACTAT----------
3621  207_HRV8       --------------------
3622  208_HRV95      --------------------
3623  209_HRV45      --------------------
3624  210_HRV45a     --------------------
3625  211_HRV45b     --------------------
3626  GROUP_1        --------------------
3627
3628
3629
3630  Summary:
3631
3632  GROUP_1        AA-CC--T-GA----T------A-----T--T-----A-GT--T--T-GT-CC--A----
3633  SUMMARY        AA-CC--T-GA----T------A-----T--T-----A-GT--T--T-GT-CC--A----
3634
3635  GROUP_1        ------AG---------------A--C-G---C-----T-GA-GC-GC-GA-AC-GG-
```

FIG. D9 CONT'D

```
05.trace                                                                      9/20/2007 5:04 PM 3636 SUMMARY      ------AG----------------A--C-G---C-----T-GA-GC-GC-GA-AC-GG-
3637
3638 GROUP_1     CA-AC-A--------CA-CC-GA-GA-----T-GA-AC--G----GT----------A-
3639 SUMMARY     CA-AC-A--------CA-CC-GA-GA-----T-GA-AC--G----GT----------A-
3640
3641 GROUP_1     AC-----ATGA-A------T-GA----TT--T-GG--G--C----TG-------------
3642 SUMMARY     AC-----ATGA-A------T-GA----TT--T-GG--G--C----TG-------------
3643
3644 GROUP_1     ------------------------------------------------------------
3645 SUMMARY     ------------------------------------------------------------
3646
3647 GROUP_1     ------------TGG----T-A---T----GA-ATG-C-CA--T--G--G-AA----GA-
3648 SUMMARY     ------------TGG----T-A---T----GA-ATG-C-CA--T--G--G-AA----GA-
3649
3650 GROUP_1     -T-TT-AC-TA-----G-TT--A-TC-GA--T-AC--T-G-T-----------C------
3651 SUMMARY     -T-TT-AC-TA-----G-TT--A-TC-GA--T-AC--T-G-T-----------C------
3652
3653 GROUP_1     -------------GG-CA--T-----T-CA-T--ATGT---T-CC-CC-GG-G--CC---
3654 SUMMARY     -------------GG-CA--T-----T-CA-T--ATGT---T-CC-CC-GG-G--CC---
3655
3656 GROUP_1     -CC--------G-------------TGG-A--C--G-A--AA----TC----TT-TGGCA
3657 SUMMARY     -CC--------G-------------TGG-A--C--G-A--AA----TC----TT-TGGCA
3658
3659 GROUP_1     ----GG-CA----T--CC--G--T--C--T-CC-TT-----G--T-GC-TC-G--TA-TA
3660 SUMMARY     ----GG-CA----T--CC--G--T--C--T-CC-TT-----G--T-GC-TC-G--TA-TA
3661
3662 GROUP_1     -ATGTT-TA-GA-GG-TA-----------------------TA-GG-------------
3663 SUMMARY     -ATGTT-TA-GA-GG-TA-----------------------TA-GG-------------
3664
3665 GROUP_1     -AA----ATGGG--C--T-T------G--T--T-AC-------CA---------------
3666 SUMMARY     -AA----ATGGG--C--T-T------G--T--T-AC-------CA---------------
3667
3668 GROUP_1     --T----------T-T--C--AA-GC-AA-CA---------TGG-G-CC--G--C-C-
3669 SUMMARY     --T----------T-T--C--AA-GC-AA-CA---------TGG-G-CC--G--C-C-
3670
3671 GROUP_1     --G-G---T----TA--------------------AA-T---------------------
3672 SUMMARY     --G-G---T----TA--------------------AA-T---------------------
3673
3674 GROUP_1     -------------------------T--------G-------------------------
3675 SUMMARY     -------------------------T--------G-------------------------
3676
3677 GROUP_1     --------------------
3678 SUMMARY     --------------------
3679
3680
```

FIG. D9 CONT'D

```
06.trace                                                            9/20/2007 5:04 PM 1 Group 1:  1_HRV1A1|d
 2 Group 1:  2_HRV1A2|d
 3 Group 1:  3_HRV1A|cD
 4 Group 1:  4_HRV1B1|d
 5 Group 1:  5_HRV1B2|d
 6 Group 1:  6_HRV1B
 7 Group 1:  7_HRV40a|d
 8 Group 1:  8_HRV40b|d
 9 Group 1:  9_HRV40
10 Group 1: 10_HRV85
11 Group 1: 11_HRV85a|
12 Group 1: 12_HRV85b|
13 Group 1: 13_HRV56a|
14 Group 1: 14_HRV56b|
15 Group 1: 15_HRV56
16 Group 1: 16_HRV54
17 Group 1: 17_HRV98
18 Group 1: 18_HRV59a|
19 Group 1: 19_HRV59b|
20 Group 1: 20_HRV59
21 Group 1: 21_HRV63
22 Group 1: 22_HRV63b|
23 Group 1: 23_HRV63a|
24 Group 1: 24_HRV39
25 Group 1: 25_HRV39a|
26 Group 1: 26_HRV39b|
27 Group 1: 27_HRV10a|
28 Group 1: 28_HRV10b|
29 Group 1: 29_HRV10
30 Group 1: 30_HRV100a
31 Group 1: 31_HRV100b
32 Group 1: 32_HRV100
33 Group 1: 33_HRV66
34 Group 1: 34_HRV66b|
35 Group 1: 35_HRV66a|
36 Group 1: 36_HRV77a|
37 Group 1: 37_HRV77b|
38 Group 1: 38_HRV77
39 Group 1: 39_HRV62a
40 Group 1: 40_HRV62b
41 Group 1: 41_HRV25
42 Group 1: 42_HRV29a
43 Group 1: 43_HRV29b
44 Group 1: 44_HRV44a
45 Group 1: 45_HRV44b
46 Group 1: 46_HRV31
47 Group 1: 47_HRV31a|
48 Group 1: 48_HRV31b|
49 Group 1: 49_HRV47
50 Group 1: 50_HRV47a|
51 Group 1: 51_HRV47b|
52 Group 1: 52_HRV11
53 Group 1: 53_HRV11b|
54 Group 1: 54_HRV11a|
55 Group 1: 55_HRV76
56 Group 1: 56_HRV76b|
57 Group 1: 57_HRV76a|
58 Group 1: 58_HRV33
59 Group 1: 59_HRV33b|
60 Group 1: 60_HRV33a|
61 Group 1: 61_HRV24a|
62 Group 1: 62_HRV24b|
63 Group 1: 63_HRV24
64 Group 1: 64_HRV90
65 Group 1: 65_HRV90a|
```

FIG. D10

06.trace                                                                    9/20/2007 5:04 PM

```
 66 Group 1:  66_HRV90b|
 67 Group 1:  67_HRV34
 68 Group 1:  68_HRV34b|
 69 Group 1:  69_HRV34a|
 70 Group 1:  70_HRV50a|
 71 Group 1:  71_HRV50b|
 72 Group 1:  72_HRV50
 73 Group 1:  73_HRV18a|
 74 Group 1:  74_HRV18b|
 75 Group 1:  75_HRV18
 76 Group 1:  76_HRV55
 77 Group 1:  77_HRV55b|
 78 Group 1:  78_HRV55a|
 79 Group 1:  79_HRV57
 80 Group 1:  80_HRV57a|
 81 Group 1:  81_HRV57b|
 82 Group 1:  82_HRV21
 83 Group 1:  83_HRVHan
 84 Group 1:  84_HRV43
 85 Group 1:  85_HRV43b|
 86 Group 1:  86_HRV43a|
 87 Group 1:  87_HRV75
 88 Group 1:  88_HRV75b|
 89 Group 1:  89_HRV75a|
 90 Group 1:  96_HRV9a|d
 91 Group 1:  97_HRV9b|d
 92 Group 1:  98_HRV9
 93 Group 1:  99_HRV32
 94 Group 1: 100_HRV32a
 95 Group 1: 101_HRV32b
 96 Group 1: 102_HRV67
 97 Group 1: 103_HRV67a
 98 Group 1: 104_HRV67b
 99 Group 1: 105_HRV15
100 Group 1: 106_HRV15a
101 Group 1: 107_HRV15b
102 Group 1: 108_HRV74a
103 Group 1: 109_HRV74b
104 Group 1: 110_HRV74
105 Group 1: 111_HRV38a
106 Group 1: 112_HRV38b
107 Group 1: 113_HRV38
108 Group 1: 114_HRV60
109 Group 1: 115_HRV60a
110 Group 1: 116_HRV60b
111 Group 1: 117_HRV64a
112 Group 1: 118_HRV64b
113 Group 1: 119_HRV64
114 Group 1: 120_HRV94a
115 Group 1: 121_HRV94b
116 Group 1: 122_HRV94
117 Group 1: 123_HRV22
118 Group 1: 124_HRV22a
119 Group 1: 125_HRV22b
120 Group 1: 126_HRV82
121 Group 1: 127_HRV82b
122 Group 1: 128_HRV82a
123 Group 1: 129_HRV19
124 Group 1: 130_HRV19a
125 Group 1: 131_HRV19b
126 Group 1: 132_HRV13
127 Group 1: 133_HRV13a
128 Group 1: 134_HRV13b
129 Group 1: 135_HRV41
130 Group 1: 136_HRV41a
```

FIG. D10 CONT'D

```
06.trace                                                      9/20/2007 5:04 PM
    131 Group 1: 137_HRV41b
    132 Group 1: 138_HRV73
    133 Group 1: 139_HRV73b
    134 Group 1: 140_HRV73a
    135 Group 1: 141_HRV61
    136 Group 1: 142_HRV61a
    137 Group 1: 143_HRV61b
    138 Group 1: 144_HRV96
    139 Group 1: 145_HRV96b
    140 Group 1: 146_HRV96a
    141 Group 1: 90_HRV16a|
    142 Group 1: 91_HRV16b|
    143 Group 1: 92_1AYM_A
    144 Group 1: 93_HRV81a|
    145 Group 1: 94_HRV81b|
    146 Group 1: 95_HRV81
    147 Group 1: 147_HRV2
    148 Group 1: 148_HRV2a|
    149 Group 1: 149_HRV2b|
    150 Group 1: 150_HRV49a
    151 Group 1: 151_HRV49b
    152 Group 1: 152_HRV49
    153 Group 1: 153_HRV23a
    154 Group 1: 154_HRV23b
    155 Group 1: 155_HRV23
    156 Group 1: 156_HRV30a
    157 Group 1: 157_HRV30b
    158 Group 1: 158_HRV30
    159 Group 1: 159_HRV7
    160 Group 1: 160_HRV7b|
    161 Group 1: 161_HRV7a|
    162 Group 1: 162_HRV88
    163 Group 1: 163_HRV88a
    164 Group 1: 164_HRV88b
    165 Group 1: 165_HRV36a
    166 Group 1: 166_HRV36b
    167 Group 1: 167_HRV36
    168 Group 1: 168_HRV89a
    169 Group 1: 169_HRV89b
    170 Group 1: 170_HRV89
    171 Group 1: 171_HRV58
    172 Group 1: 172_HRV58a
    173 Group 1: 173_HRV58b
    174 Group 1: 174_HRV12a
    175 Group 1: 175_HRV12b
    176 Group 1: 176_HRV12
    177 Group 1: 177_HRV78a
    178 Group 1: 178_HRV78b
    179 Group 1: 179_HRV78
    180 Group 1: 180_HRV20
    181 Group 1: 181_HRV20a
    182 Group 1: 182_HRV20b
    183 Group 1: 183_HRV68
    184 Group 1: 184_HRV68a
    185 Group 1: 185_HRV68b
    186 Group 1: 186_HRV28
    187 Group 1: 187_HRV28a
    188 Group 1: 188_HRV28b
    189 Group 1: 189_HRV53a
    190 Group 1: 190_HRV53b
    191 Group 1: 191_HRV53
    192 Group 1: 192_HRV46a
    193 Group 1: 193_HRV46b
    194 Group 1: 194_HRV46
    195 Group 1: 195_HRV80a
```

FIG. D10 CONT'D

```
06.trace                                                                  9/20/2007 5:04 PM 196 Group 1: 196_HRV80b
197 Group 1: 197_HRV80
198 Group 1: 198_HRV51
199 Group 1: 199_HRV51a
200 Group 1: 200_HRV51b
201 Group 1: 201_HRV65a
202 Group 1: 202_HRV65b
203 Group 1: 203_HRV65
204 Group 1: 204_HRV71a
205 Group 1: 205_HRV71b
206 Group 1: 206_HRV71
207 Group 1: 207_HRV8
208 Group 1: 208_HRV95
209 Group 1: 209_HRV45
210 Group 1: 210_HRV45a
211 Group 1: 211_HRV45b
212
213
214 >>>>>
215
216
217
218 Group 1:
219
220  1_HRV1A1|d     AATCCAGTAGAAAACTACATTGATGAAGTTTTAAATGAAGTTTTAGTAGTGCCGAATATA
221  2_HRV1A2|d     AATCCAGTAGAAAACTACATTGATGAAGTTTTAAATGAAGTTTTAGTAGTGCCGAATATA
222  3_HRV1A|cD     AATCCAGTAGAAAACTACATTGATGAAGTTTTAAATGAAGTTTTAGTAGTGCCGAATATA
223  4_HRV1B1|d     AATCCAGTGGAAAATTACATTGATGAAGTTTTAAATGAAGTTCTAGTAGTACCAAATATA
224  5_HRV1B2|d     AATCCAGTGGAAAATTACATTGATGAAGTTTTAAATGAAGTTCTAGTAGTACCAAATATA
225  6_HRV1B        AATCCAGTGGAAAATTACATTGATGAAGTTTTAAATGAAGTTCTAGTAGTACCAAATATA
226  7_HRV40a|d     AACCCCGTTGAAAGGTATGTTGATGAGGTTCTTAATGAAGTTCTGGTAGTTCCAAATATC
227  8_HRV40b|d     AACCCCGTTGAAAGGTATGTTGATGAGGTTCTTAATGAAGTTCTGGTAGTTCCAAATATC
228  9_HRV40        AACCCCGTTGAAAGGTATGTTGATGAGGTTCTTAATGAAGTTCTGGTAGTTCCAAATATC
229 10_HRV85        AATCCTGTTGAAAAATACGTTGATGAAGTCCTTAATGAGGTTCTAGTGGTTCCAAATATC
230 11_HRV85a|      AATCCTGTTGAAAAATACGTTGATGAAGTCCTTAATGAGGTTCTAGTGGTTCCAAATATC
231 12_HRV85b|      AATCCTGTTGAAAAATACGTTGATGAAGTCCTTAATGAGGTTCTAGTGGTTCCAAATATC
232 13_HRV56a|      AACCCAGTTGAGAGATATGTAGATGATGTTTTAAATGAAGTTTTAGTTGTTCCAAATATT
233 14_HRV56b|      AACCCAGTTGAGAGATATGTAGATGATGTTTTAAATGAAGTTTTAGTTGTTCCAAATATT
234 15_HRV56        AACCCAGTTGAGAGATATGTAGATGATGTTTTAAATGAAGTTTTAGTTGTTCCAAATATT
235 16_HRV54        AATCCTGTAGAAAGATATGTTGATGAAGTGTTAAATGAAGTGTTAGTTGTCCCAAACATT
236 17_HRV98        AATCCTGTAGAGAGATATGTTGATGAAGTATTAAATGAAGTGTTAGTTGTTCCAAACATT
237 18_HRV59a|      AACCCAGTGGAAAACTATGTTAATGATGTACTTAATGAGGTTTTAGTAGTACCAAATATA
238 19_HRV59b|      AACCCAGTGGAAAACTATGTTAATGATGTACTTAATGAGGTTTTAGTAGTACCAAATATA
239 20_HRV59        AACCCAGTGGAAAACTATGTTAATGATGTACTTAATGAGGTTTTAGTAGTACCAAATATA
240 21_HRV63        AATCCAGTAGAATTATGTAAATGATGTTCTTAATGAAGTGTTAGTTGTTCCAAACATA
241 22_HRV63b|      AATCCAGTAGAGAATTATGTAAATGATGTTCTTAATGAAGTGTTAGTTGTTCCAAACATA
242 23_HRV63a|      AATCCAGTAGAGAATTATGTAAATGATGTTCTTAATGAAGTGTTAGTTGTTCCAAACATA
243 24_HRV39        AATCCAGTAGAAAATTATATAGATGAAGTATTAAATGAGGTATTAGTTGTTCCTAATATA
244 25_HRV39a|      AATCCAGTAGAAAATTATATAGATGAAGTATTAAATGAGGTATTAGTTGTTCCTAATATA
245 26_HRV39b|      AATCCAGTAGAAAATTATATAGATGGAGTATTAAATGAGGTATTAGTTGTTCCTAATATA
246 27_HRV10a|      AATCCAGTTGAAAATTACATTGATAATGTACTTAATGAAGTCCTAGTGGTACCCAACATC
247 28_HRV10b|      AATCCAGTTGAAAATTACATTGATAATGTACTTAATGAAGTCCTAGTGGTACCCAACATC
248 29_HRV10        AATCCAGTTGAAAATTACATTGATAATGTACTTAATGAAGTCCTAGTGGTACCCAACATC
249 30_HRV100a      AATCCAGTAGAAAATTATGTTGAAGGTGTGCTGAATGAAGTACTAGTGGTACCTAATATT
250 31_HRV100b      AATCCAGTAGAAAATTATGTTGAAGGTGTGCTGAATGAAGTACTAGTGGTACCTAATATT
251 32_HRV100       AATCCAGTAGAAAATTATGTTGAAGGTGTGCTGAATGAAGTACTAGTGGTACCTAATATT
252 33_HRV66        AATCCAGTTGAAGATTATGTTGAGGGTGTTTTAAATGAAGTTTTAGTAGTACCAAACATC
253 34_HRV66b|      AATCCAGTTGAAGATTATGTTGAGGGTGTTTTAAATGAAGTTTTAGTAGTACCAAACATC
254 35_HRV66a|      AATCCAGTTGAAGATTATGTTGAGGGTGTTTTAAATGAAGTTTTAGTAGTACCAAACATC
255 36_HRV77a|      AATCCAGTTGAGGACTATATCGATAATGTACTTAATGAAGTCTTAGTAGTACCAAATACC
256 37_HRV77b|      AATCCAGTTGAGGACTATATCGATAATGTACTTAATGAAGTCTTAGTAGTACCAAATACC
257 38_HRV77        AATCCAGTTGAGGACTATATCGATAATGTACTTAATGAAGTCTTAGTAGTACCAAATACC
258 39_HRV62a       AATCCAATTGAAAATTATGTAGATCAAGTACTTAATGAAGTTTTAGTTGTACCAAATATT
259 40_HRV62b       AATCCAATTGAAAATTATGTAGATCAAGTACTTAATGAAGTTTTAGTTGTACCAAATATT
260 41_HRV25        AATCCAATTGAAAAATTATGTAGATCAAGTACTTAATGAGGTTCTAGTCGTACCAAATATT
```

FIG. D10 CONT'D

06.trace                                                                                       9/20/2007 5:04 PM

```
261  42_HRV29a    AACCCAGTTGAAAACTATGTGGATGAGGTGCTTAATGAAGTTTTAGTTGTGCCTAACATC
262  43_HRV29b    AACCCAGTTGAAAACTATGTGGATGAGGTGCTTAATGAAGTTTTAGTTGTGCCTAACATC
263  44_HRV44a    AACCCAGTTGAAAATTATGTGGATGAAGTACTTAATGAAGTCTTAGTTGTGCCTAATATC
264  45_HRV44b    AACCCAGTTGAAAATTATGTGGATGAAGTACTTAATGAAGTCTTAGTTGTGCCTAATATC
265  46_HRV31     AATCCAGTTGAAAACTATGTGGAAGAGGTTCTTAATGAAGTCTTAGTAGTACCTAATATC
266  47_HRV31a|   AATCCAGTTGAAAACTATGTGGAAGAGGTTCTTAATGAAGTCTTAGTAGTACCTAATATC
267  48_HRV31b|   AATCCAGTTGAAAACTATGTGGAAGAGGTTCTTAATGAAGTCTTAGTAGTACCTAATATC
268  49_HRV47     AACCCAGTCGAAAATTATGTGGAAGAGGTACTTAATGAGGTCTTAGTTGTACCAAATATC
269  50_HRV47a|   AACCCAGTCGAAAATTATGTGGAAGAGGTACTTAATGAGGTCTTAGTTGTACCAAATATC
270  51_HRV47b|   AACCCAGTCGAAAATTATGTGGAAGAGGTACTTAATGAGGTCTTAGTTGTACCAAATATC
271  52_HRV11     AACCCAGTGGAGGATTATGTTGATGGAATTCTAAATGAGGTTTTAGTTGTACCTAATATA
272  53_HRV11b|   AACCCAGTGGAGGATTATGTTGATGGAATTCTAAATGAGGTTTTAGTTGTACCTAATATA
273  54_HRV11a|   AACCCAGTGGAGGATTATGTTGATGGAATTCTAAATGAGGTTTTAGTTGTACCTAATATA
274  55_HRV76     AACCCAGTTGAAAATTACGTGGATGAGATATTAAATGAGGTTCTTGTAGTACCAAACATC
275  56_HRV76b|   AACCCAGTTGAAAATTACGTGGATGAGATATTAAATGAGGTTCTTGTAGTACCAAACATC
276  57_HRV76a|   AACCCAGTTGAAAATTACGTGGATGAGATATTAAATGAGGTTCTTGTAGTACCAAACATC
277  58_HRV33     AATCCAGTAGAGAATTATATAGAAGAGGTGTTGAATGAGGTTTTAGTAGTGCCTAATATC
278  59_HRV33b|   AATCCAGTAGAGAATTATATAGAAGAGGTGTTGAATGAGGTTTTAGTAGTGCCTAATATC
279  60_HRV33a|   AATCCAGTAGAGAATTATATAGAAGAGGTGTTGAATGAGGTTTTAGTAGTGCCTAATATC
280  61_HRV24a|   AACCCAGTAGAAAATTATATAGATGAGGTTTTGAATGAAGTACTGGTTGTGCCTAATATT
281  62_HRV24b|   AACCCAGTAGAAAATTATATAGATGAGGTTTTGAATGAAGTACTGGTTGTGCCTAATATT
282  63_HRV24     AACCCAGTAGAAAATTATATAGATGAGGTTTTGAATGAAGTACTGGTTGTGCCTAATATT
283  64_HRV90     AATCCAGTGGAAAATTATATAGATGAAGTCCTAAATGAGGTATTGGTTGTCCCTAATATT
284  65_HRV90a|   AATCCAGTGGAAAATTATATAGATGAAGTCCTAAATGAGGTATTGGTTGTCCCTAATATT
285  66_HRV90b|   AATCCAGTGGAAAATTATATAGATGAAGTCCTAAATGAGGTATTGGTTGTCCCTAATATT
286  67_HRV34     AATCCAGTTGAAAATTACATAGATGAGGTACTAAATGAGGTATTGGTTGTACCAAACATT
287  68_HRV34b|   AATCCAGTTGAAAATTACATAGATGAGGTACTAAATGAGGTATTGGTTGTACCAAACATT
288  69_HRV34a|   AATCCAGTTGAAAATTACATAGATGAGGTACTAAATGAGGTATTGGTTGTACCAAACATT
289  70_HRV50a|   AATCCAGTGGAGAATTACATAGATGAAGTATTAAATGAGGTATTAGTTGTCCCAAATATC
290  71_HRV50b|   AATCCAGTGGAGAATTACATAGATGAAGTATTAAATGAGGTATTAGTTGTCCCAAATATC
291  72_HRV50     AATCCAGTGGAGAATTACATAGATGAAGTATTAAATGAGGTATTAGTTGTCCCAAATATC
292  73_HRV18a|   AATCCAGTAGAGAATTATATAGATGAAGTACTTAATGAAGTGTTAGTGGTCCCAAATGTG
293  74_HRV18b|   AATCCAGTAGAGAATTATATAGATGAAGTACTTAATGAAGTGTTAGTGGTCCCAAATGTG
294  75_HRV18     AATCCAGTAGAGAATTATATAGATGAAGTACTTAATGAAGTGTTAGTGGTCCCAAATGTG
295  76_HRV55     AATCCTGTAGAGAGATATGTTGATGAAGTCCTGAATGAAGTGCTAGTAGTTCCAAATATT
296  77_HRV55b|   AATCCTGTAGAGAGATATGTTGATGAAGTCCTGAATGAAGTGCTAGTAGTTCCAAATATT
297  78_HRV55a|   AATCCTGTAGAGAGATATGTTGATGAAGTCCTGAATGAAGTGCTAGTAGTTCCAAATATT
298  79_HRV57     AACCCAGTAGAAAATTTTGTGGATGAGATCTTGAATGAAGTTTTGGTGGTTCCAGATATC
299  80_HRV57a|   AACCCAGTAGAAAATTTTGTGGATGAGATCTTGAATGAAGTTTTGGTGGTTCCAGATATC
300  81_HRV57b|   AACCCAGTAGAAAATTTTGTGGATGAGATCTTGAATGAAGTTTTGGTGGTTCCAGATATC
301  82_HRV21     AATCCTGTAGAGAATTATATAGATGAAGTCCTAAATGAAGTCTTAGTAGTGCCAAATATC
302  83_HRVHan    AATCCAGTAGAGAATTACGTAGATGAAGTCCTAAATGAGGTCTTAGTAGTGCCAAATATC
303  84_HRV43     AATCCTGTTGAAAATTATGTTGATGAAATTTTAAATCAAGTTCTTGTAGTCCCAAACACT
304  85_HRV43b|   AATCCTGTTGAAAATTATGTTGATGAAATTTTAAATCAAGTTCTTGTAGTCCCAAACACT
305  86_HRV43a|   AATCCTGTTGAAAATTATGTTGATGAAATTTTAAATCAAGTTCTTGTAGTCCCAAACACT
306  87_HRV75     AATCCAGTTGAAAATTATGTGGATGAAATTTTAAACCAAGTTCTGGTAGTTCCAAACACC
307  88_HRV75b|   AATCCAGTTGAAAATTATGTGGATGAAATTTTAAACCAAGTTCTGGTAGTTCCAAACACC
308  89_HRV75a|   AATCCAGTTGAAAATTATGTGGATGAAATTTTAAACCAAGTTCTGGTAGTTCCAAACACC
309  96_HRV9a|d   AATCCAGTGGAGAATTACATAGATCAGGTGCTTAATGAGGTTTTGGTAGTCCCAAACATT
310  97_HRV9b|d   AATCCAGTGGAGAATTACATAGATCAGGTGCTTAATGAGGTTTTGGTAGTCCCAAACATT
311  98_HRV9      AATCCAGTGGAGAATTACATAGATCAGGTGCTTAATGAGGTTTTGGTAGTCCCAAACATT
312  99_HRV32     AATCCTGTGGAGAATTACATAGATCAAGTTTTAAATGAAGTTTTGGTAGTTCCAAACATC
313  100_HRV32a   AATCCTGTGGAGAATTACATAGATCAAGTTTTAAATGAAGTTTTGGTAGTTCCAAACATC
314  101_HRV32b   AATCCTGTGGAGAATTACATAGATCAAGTTTTAAATGAAGTTTTGGTAGTTCCAAACATC
315  102_HRV67    AACCCAGTAGAAGATTATGTAGATCAGGTATTGAATGAGGTCCTGGTGGTGCCAAATATA
316  103_HRV67a   AACCCAGTAGAAGATTATGTAGATCAGGTATTGAATGAGGTCCTGGTGGTGCCAAATATA
317  104_HRV67b   AACCCAGTAGAAGATTATGTAGATCAGGTATTGAATGAGGTCCTGGTGGTGCCAAATATA
318  105_HRV15    AACCCAGTGGAGAATTACATAGATGAAGTGTTAAATGAGGTTCTAGTAGTTCCAAACATT
319  106_HRV15a   AACCCAGTGGAGAATTACATAGATGAAGTGTTAAATGAGGTTCTAGTAGTTCCAAACATT
320  107_HRV15b   AACCCAGTGGAGAATTACATAGATGAAGTGTTAAATGAGGTTCTAGTAGTTCCAAACATT
321  108_HRV74a   AACCCAGTGGAGAATTACATAGATGAAGTGTTGAATGAAGTGTTAGTTGTTCCAAATATT
322  109_HRV74b   AACCCAGTGGAGAATTACATAGATGAAGTGTTGAATGAAGTGTTAGTTGTTCCAAATATT
323  110_HRV74    AACCCAGTGGAGAATTACATAGATGAAGTGTTGAATGAAGTGTTAGTTGTTCCAAATATT
324  111_HRV38a   AACCCAGTAGAGGAATACATAGATGGAGTCTTGAATGAGGTTCTTGTGGTTCCGAACATT
325  112_HRV38b   AACCCAGTAGAGGAATACATAGATGGAGTCTTGAATGAGGTTCTTGTGGTTCCGAACATT
```

FIG. D10 CONT'D 06.trace                                                                9/20/2007 5:04 PM

```
326 113_HRV38   AACCCAGTAGAGGAATACATAGATGGAGTCTTGAATGAGGTTCTTGTGGTTCCGAACATT
327 114_HRV60   AATCCAGTAGAAAGCTACATAGATGGGGTCTTAAACGAAGTCCTTGTGGTTCCAAACATT
328 115_HRV60a  AATCCAGTAGAAAGCTACATAGATGGGGTCTTAAACGAAGTCCTTGTGGTTCCAAACATT
329 116_HRV60b  AATCCAGTAGAAAGCTACATAGATGGGGTCTTAAACGAAGTCCTTGTGGTTCCAAACATT
330 117_HRV64a  AACCCAGTTGAACAATACATTGATGGTGTGTTGAATGAAGTTTTGATTGTCCCAAACATC
331 118_HRV64b  AACCCAGTTGAACAATACATTGATGGTGTGTTGAATGAAGTTTTGATTGTCCCAAACATC
332 119_HRV64   AACCCAGTTGAACAATACATTGATGGTGTGTTGAATGAAGTTTTGATTGTCCCAAACATC
333 120_HRV94a  AATCCAGTTGAGAAATACATTGATGGTGTATTGAATGAAGTTTTAGTTGTTCCAAATATC
334 121_HRV94b  AATCCAGTTGAGAAATACATTGATGGTGTATTGAATGAAGTTTTAGTTGTTCCAAATATC
335 122_HRV94   AATCCAGTTGAGAAATACATTGATGGTGTATTGAATGAAGTTTTAGTTGTTCCAAATATC
336 123_HRV22   AACCCTGTAGAGAAATACATTGATGGTGTATTGAATGAAGTATTGGTTGTTCCAAACACA
337 124_HRV22a  AACCCTGTAGAGAAATACATTGATGGTGTATTGAATGAAGTATTGGTTGTTCCAAACACA
338 125_HRV22b  AACCCTGTAGAGAAATACATTGATGGTGTATTGAATGAAGTATTGGTTGTTCCAAACACA
339 126_HRV82   AATCCAGTTGAAAAGTATGTTGATAGTGTTTTAAACGAGGTATTAGTTGTTCCTAACATT
340 127_HRV82b  AATCCAGTTGAAAAGTATGTTGATAGTGTTTTAAACGAGGTATTAGTTGTTCCTAACATT
341 128_HRV82a  AATCCAGTTGAAAAGTATGTTGATAGTGTTTTAAACGAGGTATTAGTTGTTCCTAACATT
342 129_HRV19   AATCCTGTAGAGAAATATGTGGACACCATTCTGAATGAGGTGCTAGTTGTCCCAAATATC
343 130_HRV19a  AATCCTGTAGAGAAATATGTGGACACCATTCTGAATGAGGTGCTAGTTGTCCCAAATATC
344 131_HRV19b  AATCCTGTAGAGAAATATGTGGACACCATTCTGAATGAGGTGCTAGTTGTCCCAAATATC
345 132_HRV13   AATCCTGTTGAAAGGTATGTAGATGAAGTCTTGAATGAAGTTCTTGTAGTACCAAATATC
346 133_HRV13a  AATCCTGTTGAAAGGTATGTAGATGAAGTCTTGAATGAAGTTCTTGTAGTACCAAATATC
347 134_HRV13b  AATCCTGTTGAAAGGTATGTAGATGAAGTCTTGAATGAAGTTCTTGTAGTACCAAATATC
348 135_HRV41   AATCCTGTAGAAAGGTATGTGGATGAGGTCCTGAATGAGGTTCTTGTGGTACCAAATATT
349 136_HRV41a  AATCCTGTAGAAAGGTATGTGGATGAGGTCCTGAATGAGGTTCTTGTGGTACCAAATATT
350 137_HRV41b  AATCCTGTAGAAAGGTATGTGGATGAGGTCCTGAATGAGGTTCTTGTGGTACCAAATATT
351 138_HRV73   AATCCTGTAGAAAGATATGTAGATGAAGTTTTGAATGAAGTCCTTGTAGTACCCAATATC
352 139_HRV73b  AATCCTGTAGAAAGATATGTAGATGAAGTTTTGAATGAAGTCCTTGTAGTACCCAATATC
353 140_HRV73a  AATCCTGTAGAAAGATATGTAGATGAAGTTTTGAATGAAGTCCTTGTAGTACCCAATATC
354 141_HRV61   AACCCTGTGGAAAGATATGTAGATGAAGTTTTAAATGAAGTGCTTGTAGTCCCAAACATT
355 142_HRV61a  AACCCTGTGGAAAGATATGTAGATGAAGTTTTAAATGAAGTGCTTGTAGTCCCAAACATT
356 143_HRV61b  AACCCTGTGGAAAGATATGTAGATGAAGTTTTAAATGAAGTGCTTGTAGTCCCAAACATT
357 144_HRV96   AACCCTGTAGAGAGATATGTAGATGAAGTCTTGAATGAGGTTCTTGTAGTCCCTAATATT
358 145_HRV96b  AACCCTGTAGAGAGATATGTAGATGAAGTCTTGAATGAGGTTCTTGTAGTCCCTAATATT
359 146_HRV96a  AACCCTGTAGAGAGATATGTAGATGAAGTCTTGAATGAGGTTCTTGTAGTCCCTAATATT
360  90_HRV16a|  AATCCAGTGGAAAGATATGTAGATGAAGTCTTAAATGAAGTGTTAGTAGTGCCCAATATT
361  91_HRV16b|  AATCCAGTGGAAAGATATGTAGATGAAGTCTTAAATGAAGTGTTAGTAGTGCCCAATATT
362  92_1AYM_A   AATCCAGTGGAAAGATATGTAGATGAAGTCTTAAATGAAGTGTTAGTAGTGCCCAATATT
363  93_HRV81a|  AACCCAGTGGAGCGGTATGTGGATGAAGTCTTAAATGAGGTATTGGTAGTCCCTAATATT
364  94_HRV81b|  AACCCAGTGGAGCGGTATGTGGATGAAGTCTTAAATGAGGTATTGGTAGTCCCTAATATT
365  95_HRV81   AACCCAGTGGAGCGGTATGTGGATGAAGTCTTAAATGAGGTATTGGTAGTCCCTAATATT
366 147_HRV2    AACCCTGTTGAGAATTATATAGATGAAGTTCTTAATGAAGTTTTAGTTGTCCCAAATATT
367 148_HRV2a|  AACCCTGTTGAGAATTATATAGATGAAGTTCTTAATGAAGTTTTAGTTGTCCCAAATATT
368 149_HRV2b|  AACCCTGTTGAGAATTATATAGATGAAGTTCTTAATGAAGTTTTAGTTGTCCCAAATATT
369 150_HRV49a  AATCCTGTTGAACACTACATAGATGAGGTCCTTAATGAGGTTTTAGTTGTTCCAAATATT
370 151_HRV49b  AATCCTGTTGAACACTACATAGATGAGGTCCTTAATGAGGTTTTAGTTGTTCCAAATATT
371 152_HRV49   AATCCTGTTGAACACTACATAGATGAGGTCCTTAATGAGGTTTTAGTTGTTCCAAATATT
372 153_HRV23a  AATCCAATTGAGAACTATGTAGATGAAGTTCTTAATGAAGTCTTAGTTGTTCCCAATATC
373 154_HRV23b  AATCCAATTGAGAACTATGTAGATGAAGTTCTTAATGAAGTCTTAGTTGTTCCCAATATC
374 155_HRV23   AATCCAATTGAGAACTATGTAGATGAAGTTCTTAATGAAGTCTTAGTTGTTCCCAATATC
375 156_HRV30a  AACCCGGTTGAAAATTTTGTAGATGAAGTTCTTAGTGAAGTTTTAGTTGTTCCAAACATT
376 157_HRV30b  AACCCGGTTGAAAATTTTGTAGATGAAGTTCTTAGTGAAGTTTTAGTTGTTCCAAACATT
377 158_HRV30   AACCCGGTTGAAAATTTTGTAGATGAAGTTCTTAGTGAAGTTTTAGTTGTTCCAAACATT
378 159_HRV7    AACCCGGTAGAGAATTATGTAGATAGCTTACTAAATGAAGTATTAGTGGTACCTAATATT
379 160_HRV7b|  AACCCGGTAGAGAATTATGTAGATAGCTTACTAAATGAAGTATTAGTGGTACCTAATATT
380 161_HRV7a|  AACCCGGTAGAGAATTATGTAGATAGCTTACTAAATGAAGTATTAGTGGTACCTAATATT
381 162_HRV88   AATCCAGTAGAAAACTATGTAGATAACTTGTTAAACGAAGTGCTAGTAGTTCCTAACATT
382 163_HRV88a  AATCCAGTAGAAAACTATGTAGATAACTTGTTAAACGAAGTGCTAGTAGTTCCTAACATT
383 164_HRV88b  AATCCAGTAGAAAACTATGTAGATAACTTGTTAAACGAAGTGCTAGTAGTTCCTAACATT
384 165_HRV36a  AATCCAGTTGAAAATTACATAGATAATGTATTTAAAGAAGTACTTGTAGTGCCAAACATC
385 166_HRV36b  AATCCAGTTGAAAATTACATAGATAATGTATTTAAAGAAGTACTTGTAGTGCCAAACATC
386 167_HRV36   AATCCAGTTGAAAATTACATAGATAATGTATTTAAAGAAGTACTTGTAGTGCCAAACATC
387 168_HRV89a  AACCCAGTTGAAAATTATATAGATAGTGTATTTAAATGAAGTTCTTGTGGTGCCAAATATC
388 169_HRV89b  AACCCAGTTGAAAATTATATAGATAGTGTATTTAAATGAAGTTCTTGTGGTGCCAAATATC
389 170_HRV89   AACCCAGTTGAAAATTATATAGATAGTGTATTTAAATGAAGTTCTTGTGGTGCCAAATATC
390 171_HRV58   AATCCAGTAGAAAATTACATAGATAATGTGTTAAATGAAGTACTTGTAGTTCCAAATATC
```

FIG. D10 CONT'D

06.trace                                                                 9/20/2007 5:04 PM

```
391 172_HRV58a       AATCCAGTAGAAAATTACATAGATAATGTGTTAAATGAAGTACTTGTAGTTCCAAATATC
392 173_HRV58b       AATCCAGTAGAAAATTACATAGATAATGTGTTAAATGAAGTACTTGTAGTTCCAAATATC
393 174_HRV12a       AATCCAGTAGAGAGATATGTTGATGAGGTGCTAAATGAAGTTCTAGTTGTTCCAAACATA
394 175_HRV12b       AATCCAGTAGAGAGATATGTTGATGAGGTGCTAAATGAAGTTCTAGTTGTTCCAAACATA
395 176_HRV12        AATCCAGTAGAGAGATATGTTGATGAGGTGCTAAATGAAGTTCTAGTTGTTCCAAACATA
396 177_HRV78a       AATCCAGTGGAAGAATATGTTGATCAGGTTTTAAATGAGGTTTTAGTTGTTCCAAACATA
397 178_HRV78b       AATCCAGTGGAAGAATATGTTGATCAGGTTTTAAATGAGGTTTTAGTTGTTCCAAACATA
398 179_HRV78        AATCCAGTGGAAGAATATGTTGATCAGGTTTTAAATGAGGTTTTAGTTGTTCCAAACATA
399 180_HRV20        AACCCAGTGGAAAGGTACACAGAAGCTATTTTAAATGAAGTTCTTGTAGTTCCAAATATC
400 181_HRV20a       AACCCAGTGGAAAGGTACACAGAAGCTATTTTAAATGAAGTTCTTGTAGTTCCAAATATC
401 182_HRV20b       AACCCAGTGGAAAGGTACACAGAAGCTATTTTAAATGAAGTTCTTGTAGTTCCAAATATC
402 183_HRV68        AACCCAGTTGAAAAATACACAGAAGCCGTTCTTAATGAGGTCCTTGTGGTTCCAAACATA
403 184_HRV68a       AACCCAGTTGAAAAATACACAGAAGCCGTTCTTAATGAGGTCCTTGTGGTTCCAAACATA
404 185_HRV68b       AACCCAGTTGAAAAATACACAGAAGCCGTTCTTAATGAGGTCCTTGTGGTTCCAAACATA
405 186_HRV28        AATCCAGTTGAAAAATATACTGAAGCACTACTTAATGAAGTGCTTGTTGTGCCAAACATC
406 187_HRV28a       AATCCAGTTGAAAAATATACTGAAGCACTACTTAATGAAGTGCTTGTTGTGCCAAACATC
407 188_HRV28b       AATCCAGTTGAAAAATATACTGAAGCACTACTTAATGAAGTGCTTGTTGTGCCAAACATC
408 189_HRV53a       AACCCGGTAGAGAAATACACAGAGGCTATCTTAAATGAAGTATTAGTAGTCCCAAACATT
409 190_HRV53b       AACCCGGTAGAGAAATACACAGAGGCTATCTTAAATGAAGTATTAGTAGTCCCAAACATT
410 191_HRV53        AACCCGGTAGAGAAATACACAGAGGCTATCTTAAATGAAGTATTAGTAGTCCCAAACATT
411 192_HRV46a       AATCCAGTGGAAAAATATACAGAAGCTGTTCTTAATGAGGTCCTTGTAGTACCTAACATC
412 193_HRV46b       AATCCAGTGGAAAAATATACAGAAGCTGTTCTTAATGAGGTCCTTGTAGTACCTAACATC
413 194_HRV46        AATCCAGTGGAAAAATATACAGAAGCTGTTCTTAATGAGGTCCTTGTAGTACCTAACATC
414 195_HRV80a       AATCCAGTCGAAAAATACACAGAAGCAATCCTCAATGAAGTTCTTGTTGTACCAAACATC
415 196_HRV80b       AATCCAGTCGAAAAATACACAGAAGCAATCCTCAATGAAGTTCTTGTTGTACCAAACATC
416 197_HRV80        AATCCAGTCGAAAAATACACAGAAGCAATCCTCAATGAAGTTCTTGTTGTACCAAACATC
417 198_HRV51        AACCCTGTTGAAAAATATACAGAGGCTTTACTCAATGAAGTGTTGGTGGTTCCCAACATA
418 199_HRV51a       AACCCTGTTGAAAAATATACAGAGGCTTTACTCAATGAAGTGTTGGTGGTTCCCAACATA
419 200_HRV51b       AACCCTGTTGAAAAATATACAGAGGCTTTACTCAATGAAGTGTTGGTGGTTCCCAACATA
420 201_HRV65a       AATCCAATTGAGAAGTATACAGAAGCTCTACTTAATGAAGTGTTGGTGGTCCCAAATATA
421 202_HRV65b       AATCCAATTGAGAAGTATACAGAAGCTCTACTTAATGAAGTGTTGGTGGTCCCAAATATA
422 203_HRV65        AATCCAATTGAGAAGTATACAGAAGCTCTACTTAATGAAGTGTTGGTGGTCCCAAATATA
423 204_HRV71a       AATCCTGTAGAAAAATATACAGAAGCAATACTCAATGAGGTTCTAGTTGTGCCAAATATA
424 205_HRV71b       AATCCTGTAGAAAAATATACAGAAGCAATACTCAATGAGGTTCTAGTTGTGCCAAATATA
425 206_HRV71        AATCCTGTAGAAAAATATACAGAAGCAATACTCAATGAGGTTCTAGTTGTGCCAAATATA
426 207_HRV8         AACCCTATTGAACAATTCACAGAGGCAGTATTAAACGAGGTTCTTGTAGTTCCAAACACA
427 208_HRV95        AACCCTATTGAACAATTCACAGAGGCAGTATTAAACGAGGTTCTTGTAGTTCCAAATACA
428 209_HRV45        AACCCTGTTGAACAATTTGCAGAAGCAGTCCTTGATCAAGTATTAGTAGTTCCAAACACT
429 210_HRV45a       AACCCTGTTGAACAATTTGCAGAAGCAGTCCTTGATCAAGTATTAGTAGTTCCAAACACT
430 211_HRV45b       AACCCTGTTGAACAATTTGCAGAAGCAGTCCTTGATCAAGTATTAGTAGTTCCAAACACT
431 GROUP_1          AA-CC--T-GA----T------A-----T--T------A-GT--T--T-GT-CC--A----
432
433 1_HRV1A1|d       AAAGAAAGTCATCACACTACATCAAACTCTGCCCCACTTTTAGATGCTGCAGAGACGGGA
434 2_HRV1A2|d       AAAGAAAGTCATCACACTACATCAAACTCTGCCCCACTTTTAGATGCTGCAGAGACGGGA
435 3_HRV1A|cD       AAAGAAAGTCATCACACTACATCAAACTCTGCCCCACTTTTAGATGCTGCAGAGACGGGA
436 4_HRV1B1|d       AAAGAAAGCCATCACACTACATCAAATTCTGCTCCACTCTTGGATGCTGCAGAGACAGGA
437 5_HRV1B2|d       AAAGAAAGCCATCACACTACATCAAATTCTGCTCCACTCTTGGATGCTGCAGAGACAGGA
438 6_HRV1B          AAAGAAAGCCATCACACTACATCAAATTCTGCTCCACTCTTGGATGCTGCAGAGACAGGA
439 7_HRV40a|d       AGAGAGAGCCATCCAACTACATCAAATTCGGCCCCTGCCTTGGATGCAGCAGAGACTGGA
440 8_HRV40b|d       AGAGAGAGCCATCCAACTACATCAAATTCGGCCCCTGCCTTGGATGCAGCAGAGACTGGA
441 9_HRV40          AGAGAGAGCCATCCAACTACATCAAATTCGGCCCCTGCCTTGGATGCAGCAGAGACTGGA
442 10_HRV85         AAAGAGAGTCACCCAACTATATCAAATTCAGCTCCTGCTTTGGATGCAGCAGAGACTGGC
443 11_HRV85a|       AAAGAGAGTCACCCAACTATATCAAATTCAGCTCCTGCTTTGGATGCAGCAGAGACTGGC
444 12_HRV85b|       AAAGAGAGTCACCCAACTATATCAAATTCAGCTCCTGCTTTGGATGCAGCAGAGACTGGC
445 13_HRV56a|       AGGGAGAGCCATCCATCCACATCAAATTCTGCCCCTGCATTAGATGCTGCTGAAACTGGC
446 14_HRV56b|       AGGGAGAGCCATCCATCCACATCAAATTCTGCCCCTGCATTAGATGCTGCTGAAACTGGC
447 15_HRV56         AGGGAGAGCCATCCATCCACATCAAATTCTGCCCCTGCATTAGATGCTGCTGAAACTGGC
448 16_HRV54         AGAGAAAGTCATCCAGCTACATCTAATTCAGCCCCTGCGCTAGATGCGGCAGAAACTGGA
449 17_HRV98         AAAGAAAGTCATCCAGCTACATCTAATTCGGCCCCTACACTAGATGCAGCAGAAACTGGG
450 18_HRV59a|       CAGGAAAGCCACCCAACCACCTCAAATGCTGCTCCAGCATTAGATGCAGCAGAGACTGGA
451 19_HRV59b|       CAGGAAAGCCACCCAACCACCTCAAATGCTGCTCCAGCATTAGATGCAGCAGAGACTGGA
452 20_HRV59         CAGGAAAGCCACCCAACCACCTCAAATGCTGCTCCAGCATTAGATGCAGCAGAGACTGGA
453 21_HRV63         CAAGAAAGCCATCCAACCACATCAAACGCTGCTCCTGTACTTGATGCTGCGGAAACAGGA
454 22_HRV63b|       CAAGAAAGCCATCCAACCACATCAAACGCTGCTCCTGTACTTGATGCTGCGGAAACAGGA
455 23_HRV63a|       CAAGAAAGCCATCCAACCACATCAAACGCTGCTCCTGTACTTGATGCTGCGGAAACAGGA
```

FIG. D10 CONT'D 06.trace                                                                                               9/20/2007 5:04 PM

```
456  24_HRV39     AGAGAGAGCCATCCAACTACATCTAATGCAGCTACAGCTTTGGATGCTGCTGAAACTGGA
457  25_HRV39a|   AGAGAGAGCCATCCAACTACATCTAATGCAGCTACAGCTTTGGATGCTGCTGAAACTGGA
458  26_HRV39b|   AGAGAGAGCCATCCAACTACATCTAATGCAGCTCCAGCTTTGGATGCTGCTGAAACTGGA
459  27_HRV10a|   AGAGAAAGTCATCCAAGCACCTCTAACTCTGCCCCAATTCTCGATGCAGCTGAGACTGGT
460  28_HRV10b|   AGAGAAAGTCATCCAAGCACCTCTAACTCTGCCCCAATTCTCGATGCAGCTGAGACTGGT
461  29_HRV10     AGAGAAAGTCATCCAAGCACCTCTAACTCTGCCCCAATTCTCGATGCAGCTGAGACTGGT
462  30_HRV100a   AGAGAGAGCCATCCAAGCACCTCAAACTCTGCTCCAATCCTTGATGCTGCTGAAACTGGC
463  31_HRV100b   AGAGAGAGCCATCCAAGCACCTCAAACTCTGCTCCAATCCTTGATGCTGCTGAAACTGGC
464  32_HRV100    AGAGAGAGCCATCCAAGCACCTCTGCTCCAATCCTTGATGCTGCTGAAACTGGC
465  33_HRV66     AAGGAAAGCCATCCAAGCACATCAAATGCTGCCCCAATACTAGATGCAGCTGAAACAGGT
466  34_HRV66b|   AAGGAAAGCCATCCAAGCACATCAAATGCTGCCCCAATACTAGATGCAGCTGAAACAGGT
467  35_HRV66a|   AAGGAAAGCCATCCAAGCACATCAAATGCTGCCCCAATACTAGATGCAGCTGAAACAGGT
468  36_HRV77a|   AAGGAGAGTCATCCAAGCACTTCTAACTCTGCTCCTATACTAGATGCAGCTGAAACAGGC
469  37_HRV77b|   AAGGAGAGTCATCCAAGCACTTCTAACTCTGCTCCTATACTAGATGCAGCTGAAACAGGC
470  38_HRV77     AAGGAGAGTCATCCAAGCACTTCTAACTCTGCTCCTATACTAGATGCAGCTGAAACAGGC
471  39_HRV62a    AAAGAAAGTCACCCTAGTACGTCAAACTCTGCCCCAATTCTAGATGCTGCTGAAACCGGA
472  40_HRV62b    AAAGAAAGTCACCCTAGTACGTCAAACTCTGCCCCAATTCTAGATGCTGCTGAAACCGGA
473  41_HRV25     AAAGAAAGTCACCCAAGCACATCAAATTCTGCCCCAATTCTAGATGCTGCTGAAACTGGA
474  42_HRV29a    AGGGAGAGCCACCCAAGCACGTCCAACTCTGCACCAATCTTGGATGCTGCTGAGACTGGA
475  43_HRV29b    AGGGAGAGCCACCCAAGCACGTCCAACTCTGCACCAATCTTGGATGCTGCTGAGACTGGA
476  44_HRV44a    AGAGAGAGCCACCCAAGCACATCTAACTCTGCTCCAATTTTGGATGCTGCTGAGACTGGA
477  45_HRV44b    AGAGAGAGCCACCCAAGCATATCTAACTCTGCTCCAATTTTGGATGCTGCTGAAACTGGA
478  46_HRV31     AAAGAAAGCCATCCAAGCACATCTAATTCTGCCCCAATCCTGGACGCTGCTGAAACTGGA
479  47_HRV31a|   AAAGAAAGCCATCCAAGCACATCTAATTCTGCCCCAATCCTGGACGCTGCTGAAACTGGA
480  48_HRV31b|   AAAGAAAGCCATCCAAGCACATCTAATTCTGCCCCAATCCTGGACGCTGCTGAAACTGGA
481  49_HRV47     AAAGAAAGTCATCCAAGTACATCCAACTCTGCCCCGATTTTAGATGCTGCTGAAACTGGA
482  50_HRV47a|   AAAGAAAGTCATCCAAGTACATCCAACTCTGCCCCGATTTTAGATGCTGCTGAAACTGGA
483  51_HRV47b|   AAAGAAAGTCATCCAAGTACATCCAACTCTGCCCCGATTTTAGATGCTGCTGAAACTGGA
484  52_HRV11     AAGGAGAGCCAAGCTACCACATCAAACTCAGCACCTGCTCTAGATGCAGCTGAAACCGGA
485  53_HRV11b|   AAGGAGAGCCAAGCTACCACATCAAACTCAGCACCTGCTCTAGATGCAGCTGAAACCGGA
486  54_HRV11a|   AAGGAGAGCCAAGCTACCACATCAAACTCAGCACCTGCTCTAGATGCAGCTGAAACCGGA
487  55_HRV76     AAAGAGAGTCAGGCTACCACATCAAATGCAGCACCTGCTTTGGATGCAGCTGAGACTGGG
488  56_HRV76b|   AAAGAGAGTCAGGCTACCACATCAAATGCAGCACCTGCTTTGGATGCAGCTGAGACTGGG
489  57_HRV76a|   AAAGAGAGTCAGGCTACCACATCAAATGCAGCACCTGCTTTGGATGCAGCTGAGACTGGG
490  58_HRV33     AGAGAGAGTCAAGCAACCACATCAAATTCAGCACCTGCCCTTAGATGCAGCTGAGACTGGA
491  59_HRV33b|   AGAGAGAGTCAAGCAACCACATCAAATTCAGCACCTGCCTTAGATGCAGCTGAGACTGGA
492  60_HRV33a|   AGAGAGAGTCAAGCAACCACATCAAATTCAGCACCTGCCTTAGATGCAGCTGAGACTGGA
493  61_HRV24a|   AAGGAAAGTAAACCATCAACATCAAACTCAGCACCAGCTTTGGATGCAGCAGAAACTGGA
494  62_HRV24b|   AAGGAAAGTAAACCATCAACATCAAACTCAGCACCAGCTTTGGATGCAGCAGAAACTGGA
495  63_HRV24     AAGGAAAGTAAACCATCAACATCAAACTCAGCACCAGCTTTGGATGCAGCAGAAACTGGA
496  64_HRV90     AAGGAAAGTAAACCTTCAACTTCAAACTCAGCGCCAGCTTTAGATGCAGCAGAAACCGGA
497  65_HRV90a|   AAGGAAAGTAAACCTTCAACTTCAAACTCAGCGCCAGCTTTAGATGCAGCAGAAACCGGA
498  66_HRV90b|   AAGGAAAGTAAACCTTCAACTTCAAACTCAGCGCCAGCTTTAGATGCAGCAGAAACCGGA
499  67_HRV34     AAAGAAAGCCAAGCCACCACATCAAACTCTGCCCCCGCACTGGATGCAGCTGAGACTGGT
500  68_HRV34b|   AAAGAAAGCCAAGCCACCACATCAAACTCTGCCCCCGCACTGGATGCAGCTGAGACTGGT
501  69_HRV34a|   AAAGAAAGCCAAGCCACCACATCAAACTCTGCCCCCGCACTGGATGCAGCTGAGACTGGT
502  70_HRV50a|   AAGGAGAGTCAAGCCACTACATCAAACTCTGCCCCTGCTTTAGATGCAGCTGAAACTGGA
503  71_HRV50b|   AAGGAGAGTCAAGCCACTACATCAAACTCTGCCCCTGCTTTAGATGCAGCTGAAACTGGA
504  72_HRV50     AAGGAGAGTCAAGCCACTACATCAAACTCTGCCCCTGCTTTAGATGCAGCTGAAACTGGA
505  73_HRV18a|   AATGAAAGTCACGCAATTACATCAAATTCAGCCCCTGCTTTAGATGCCGCTGAAACTGGT
506  74_HRV18b|   AATGAAAGTCACGCAATTACATCAAATTCAGCCCCTGCTTTAGATGCCGCTGAAACTGGT
507  75_HRV18     AATGAAAGTCACGCAATTACATCAAATTCAGCCCCTGCTTTAGATGCCGCTGAAACTGGT
508  76_HRV55     AGGGAGAGTCAAGCAGCAACATCAAATTCAGCTCCAGTACTAGATGCAGCAGAAACTGGG
509  77_HRV55b|   AGGGAGAGTCAAGCAGCAACATCAAATTCAGCTCCAGTACTAGATGCAGCAGAAACTGGG
510  78_HRV55a|   AGGGAGAGTCAAGCAGCAACATCAAATTCAGCTCCAGTACTAGATGCAGCAGAAACTGGG
511  79_HRV57     AAACAAAGTCAAGCAACAACATCAAACTCAGCACCTGCATTGGATGCAGCTGAAACTGGA
512  80_HRV57a|   AAACAAAGTCAAGCAACAACATCAAACTCAGCACCTGCATTGGATGCAGCTGAAACTGGA
513  81_HRV57b|   AAACAAAGTCAAGCAACAACATCAAACTCAGCACCTGCATTGGATGCAGCTGAAACTGGA
514  82_HRV21     AGAGAGAGTCATGGAACAACATCAAACTCTGCTCCCGCACTTGATGCTGCAGAAACTGGA
515  83_HRVHan    AGAGAGAGTCATGGAACAACATCAAACTCTGCTCCCGCACTTGATGCTGCAGAAACTGGG
516  84_HRV43     GTAGAAAGTCATTCAACAACATCCAATGCAGCCCCTGCACTTGATGCAGCTGAAACTGGG
517  85_HRV43b|   GTAGAAAGTCATTCAACAACATCCAATGCAGCCCCTGCACTTGATGCAGCTGAAACTGGG
518  86_HRV43a|   GTAGAAAGTCATTCAACAACATCCAATGCAGCCCCTGCACTTGATGCAGCTGAAACTGGG
519  87_HRV75     ATGGAGAGCCATCCAACAACGTCTAATGCTGCTCCAGCTTTAGATGCAGCTGAAACTGGC
520  88_HRV75b|   ATGGAGAGCCATCCAACAACGTCTAATGCTGCTCCAGCTTTAGATGCAGCTGAAACTGGC
```

FIG. D10 CONT'D 06.trace                                                                9/20/2007 5:04 PM

```
521   89_HRV75a|    ATGGAGAGCCATCCAACAACGTCTAATGCTGCTCCAGCTTTAGATGCAGCTGAAACTGGC
522   96_HRV9a|d    AAAGAGAGCAACCCTACAACCTCTAACTCAGCTCCAGCTCTAGATGCTGCTGAGACAGGC
523   97_HRV9b|d    AAAGAGAGCAACCCTACAACCTCTAACTCAGCTCCAGCTCTAGATGCTGCTGAGACAGGC
524   98_HRV9       AAAGAGAGCAACCCTACAACCTCTAACTCAGCTCCAGCTCTAGATGCTGCTGAGACAGGC
525   99_HRV32      AAAGAAAGCAATCCCACAACCTCTAATTCAGCCCCAGCCTTAGATGCTGCCGAAACAGGT
526  100_HRV32a     AAAGAAAGCAATCCCACAACCTCTAATTCAGCCCCAGCCTTAGATGCTGCCGAAACAGGT
527  101_HRV32b     AAAGAAAGCAATCCCACAACCTCTAATTCAGCCCCAGCCTTAGATGCTGCCGAAACAGGT
528  102_HRV67      AAGCAAAGTGAACCCACGACTTCCAATTCAGCCCCAGCTCTAGATGCTGCTGAGACAGGT
529  103_HRV67a     AAGCAAAGTGAACCCACGACTTCCAATTCAGCCCCAGCTCTAGATGCTGCTGAGACAGGT
530  104_HRV67b     AAGCAAAGTGAACCCACGACTTCCAATTCAGCCCCAGCTCTAGATGCTGCTGAGACAGGT
531  105_HRV15      AAGGAGAGTCACTCAAGCACATCCAACTCAGCACCAGCACTAGATGCAGCTGAGACCGGC
532  106_HRV15a     AAGGAGAGTCACTCAAGCACATCCAACTCAGCACCAGCACTAGATGCAGCTGAGACCGGC
533  107_HRV15b     AAGGAGAGTCACTCAAGCACATCCAACTCAGCACCAGCACTAGATGCAGCTGAGACCGGC
534  108_HRV74a     AGAGAAAGCCATTCAAGTACTTCAAACTCAGCACCAGCACTGGATGCAGCTGAAACTGGC
535  109_HRV74b     AGAGAAAGCCATTCAAGTACTTCAAACTCAGCACCAGCACTGGATGCAGCTGAAACTGGC
536  110_HRV74      AGAGAAAGCCATTCAAGTACTTCAAACTCAGCACCAGCACTGGATGCAGCTGAAACTGGC
537  111_HRV38a     AAGGAAAGCCACTCCAGCACATCAAATTCAGCACCAGCATTAGATGCTGCTGAGACTGGA
538  112_HRV38b     AAGGAAAGCCACTCCAGCACATCAAATTCAGCACCAGCATTAGATGCTGCTGAGACTGGA
539  113_HRV38      AAGGAAAGCCACTCCAGCACATCAAATTCAGCACCAGCATTAGATGCTGCTGAGACTGGA
540  114_HRV60      AGGGAGAGCCAACCCACTACTTCTAATTCTGCTCCAGCATTGGATGCTGCTGAGACTGGT
541  115_HRV60a     AGGGAGAGCCAACCCACTACTTCTAATTCTGCTCCAGCATTGGATGCTGCTGAGACTGGT
542  116_HRV60b     AGGGAGAGCCAACCCACTACTTCTAATTCTGCTCCAGCATTGGATGCTGCTGAGACTGGT
543  117_HRV64a     AATGAGAGCCATCCCAGCACTTCCAATGCAGCGCCAGCTTTAGATGCAGCTGAGACCGGA
544  118_HRV64b     AATGAGAGCCATCCCAGCACTTCCAATGCAGCGCCAGCTTTAGATGCAGCTGAGACCGGA
545  119_HRV64      AATGAGAGCCATCCCAGCACTTCCAATGCAGCGCCAGCTTTAGATGCAGCTGAGACCGGA
546  120_HRV94a     AATGAGAGTCACCCTAGCACATCCAATGCAGCGCCAGCCTTAGATGCTGCCGAAACTGGA
547  121_HRV94b     AATGAGAGTCACCCTAGCACATCCAATGCAGCGCCAGCCTTAGATGCTGCCGAAACTGGA
548  122_HRV94      AATGAGAGTCACCCTAGCACATCCAATGCAGCGCCAGCCTTAGATGCTGCCGAAACTGGA
549  123_HRV22      AATGAAAGTCACCCCAGTACATCAAATGCTGCACCAGCACTAGATGCTGCTGAAACTGGA
550  124_HRV22a     AATGAAAGTCACCCCAGTACATCAAATGCTGCACCAGCACTAGATGCTGCTGAAACTGGA
551  125_HRV22b     AATAAAAGTCACCCCAGTACATCAAATGCTGCACCAGCACTAGATGCTGCTGAAACTGGA
552  126_HRV82      AATGAAAGTCATCCTAGTACTTCAAATTCAGCTCCTGCCTTGGACGCTGCAGAGACAGGA
553  127_HRV82b     AATGAAAGTCATCCTAGTACTTCAAATTCAGCTCCTGCCTTGGACGCTGCAGAGACAGGA
554  128_HRV82a     AATAAAAGTCATCCTAGTACTTCAAATTCAGCTCCTGCCTTGGACGCTGCAGAGACAGGA
555  129_HRV19      AATGAAAGTCATCCAAGTACATCAAATGCTGCTCCTGCCTTAGATGCAGCCGAGACAGGA
556  130_HRV19a     AATGAAAGTCATCCAAGTACATCAAATGCTGCTCCTGCCTTAGATGCAGCCGAGACAGGA
557  131_HRV19b     AATGAAAGTCATCCAAGTACATCAAATGCTGCTCCTGCCTTAGATGCAGCCGAGACAGGA
558  132_HRV13      AGTGAAAGTAGCTCAACTACATCTAATTCAGCTCCAGCCTTAGATGCTGCAGAAACTGGC
559  133_HRV13a     AGTGAAAGTAGCTCAACTACATCTAATTCAGCTCCAGCCTTAGATGCTGCAGAAACTGGC
560  134_HRV13b     AGTGAAAGTAGCTCAACTACATCTAATTCAGCTCCAGCCTTAGATGCTGCAGAAACTGGC
561  135_HRV41      AGTGAAAGCAGTCCAACTACTTCTAATTCAGCTCCAGCCCTAGATGCAGCAGAGACTGGT
562  136_HRV41a     AGTGAAAGCAGTCCAACTACTTCTAATTCAGCTCCAGCCCTAGATGCAGCAGAGACTGGT
563  137_HRV41b     AGTGAAAGCAGTCCAACTACTTCTAATTCAGCTCCAGCCCTAGATGCAGCAGAGACTGGT
564  138_HRV73      AATGAAAGTAATCCAACTACATCCAACTCAGCACCTGCACTGGACGCTGCAGAAACTGGC
565  139_HRV73b     AATGAAAGTAATCCAACTACATCCAACTCAGCACCTGCACTGGACGCTGCAGAAACTGGC
566  140_HRV73a     AATGAAAGTAATCCAACTACATCCAACTCAGCACCTGCACTGGACGCTGCAGAAACTGGC
567  141_HRV61      AATCAGAGCAACCCTACAACATCCAACTCAGCACCAGTCTTAGACGCTGCTGAAACAGGT
568  142_HRV61a     AATCAGAGCAACCCTACAACATCCAACTCAGCACCAGTCTTAGACGCTGCTGAAACAGGT
569  143_HRV61b     AATCAGAGCAACCCTACAACATCCAACTCAGCACCAGTCTTAGACGCTGCTGAAACAGGT
570  144_HRV96      AATGAAAGTTACCCAACAACTTCCAATTCAGCCCCAGTGCTAGATGCCGCTGAAACAGGT
571  145_HRV96b     AATGAAAGTTACCCAACAACTTCCAATTCAGCCCCAGTGCTAGATGCCGCTGAAACAGGT
572  146_HRV96a     AATAAAAGTTACCCAACAACTTCCAATTCAGCCCCAGTGCTAGATGCCGCTGAAACAGGT
573   90_HRV16a|    AATGAGAGCCACCCTACCACATCAAATGCGGCCCCAGTTTTGGATGCTGCTGAAACAGGA
574   91_HRV16b|    AATGAGAGCCACCCTACCACATCAAATGCGGCCCCAGTTTTGGATGCTGCTGAAACAGGA
575   92_1AYM_A     AATGAGAGCCACCCTACCACATCAAATGCGGCCCCAGTTTTGGATGCTGCTGAAACAGGA
576   93_HRV81a|    AATGAAAGCCACCCTACAACATCTAATCAGCTCCTCCTGTTTTAGATGCAGCTGAAACTGGA
577   94_HRV81b|    AATGAAAGCCACCCTACAACATCTAATTCAGCTCCTGTTTTAGATGCAGCTGAAACTGGA
578   95_HRV81      AATGAAAGCCACCCTACAACATCTAATTCAGCTCCTGTTTTAGATGCAGCTGAAACTGGA
579  147_HRV2       AATAGTAGTAACCCCACAACATCAAATTCTGCCCCAGCATTAGATGCTGCAGAAACAGGG
580  148_HRV2a|     AATAGTAGTAACCCCACAACATCAAATTCTGCCCCAGCATTAGATGCTGCAGAAACAGGG
581  149_HRV2b|     AATAGTAGTAACCCCACAACATCAAATTCTGCCCCAGCATTAGATGCTGCAGAAACAGGG
582  150_HRV49a     AATAGTAGTCACCCCACGACATCAAACTCTGCTCCAGCATTAGATGCTGCAGAAACAGGG
583  151_HRV49b     AATAGTAGTCACCCCACGACATCAAACTCTGCTCCAGCATTAGATGCTGCAGAAACAGGG
584  152_HRV49      AATAGTAGTCACCCCACGACATCAAACTCTGCTCCAGCATTAGATGCTGCAGAAACAGGG
585  153_HRV23a     AATAGTAGTCATCCCACAACATCAAACTCTGCTCCAGCATTAGACGCTGCGGAAACGGGT
```

FIG. D10 CONT'D

```
06.trace                                                                9/20/2007 5:04 PM 586  154_HRV23b    AATAGTAGTCATCCCACAACATCAAACTCTGCTCCAGCATTAGACGCTGCGGAAACGGGT
587  155_HRV23     AATAGTAGTCATCCCACAACATCAAACTCTGCTCCAGCATTAGACGCTGCGGAAACGGGT
588  156_HRV30a    AACAGTAGTCACCCTACTACATCAAACTCTGCTCCGGCATTAGATGCTGCAGAAACAGGA
589  157_HRV30b    AACAGTAGTCACCCTACTACATCAAACTCTGCTCCGGCATTAGATGCTGCAGAAACAGGA
590  158_HRV30     AACAGTAGTCACCCTACTACATCAAACTCTGCTCCGGCATTAGATGCTGCAGAAACAGGA
591  159_HRV7      CAGCCAAGTACATCTGTTTCAAGTCACTCTGTACCAGCATTGGATGCTGCAGAGACTGGA
592  160_HRV7b|    CAGCCAAGTACATCTGTTTCAAGTCACTCTGTACCAGCATTGGATGCTGCAGAGACTGGA
593  161_HRV7a|    CAGCCAAGTACATCTGTTTCAAGTCACTCTGTACCAGCATTGGATGCTGCAGAGACTGGA
594  162_HRV88     CAACCTAGCACATCCGTTTCAAGTCACTCTGTGCCAGCTCTGGATGCTGCGGAAACAGGG
595  163_HRV88a    CAACCTAGCACATCCGTTTCAAGTCACTCTGTGCCAGCTCTGGATGCTGCGGAAACAGGG
596  164_HRV88b    CAACCTAGCACATCCGTTTCAAGTCACTCTGTGCCAGCTCTGGATGCTGCGGAAACAGGG
597  165_HRV36a    CAACCTAGTTCATCTGTGTCAAGTCATTCAGCTCCCGCCTTAGACGCTGCGGAAACTGGA
598  166_HRV36b    CAACCTAGTTCATCTGTGTCAAGTCATTCAGCTCCCGCCTTAGACGCTGCGGAAACTGGA
599  167_HRV36     CAACCTAGTTCATCTGTGTCAAGTCATTCAGCTCCCGCCTTAGACGCTGCGGAAACTGGA
600  168_HRV89a    CAACCTAGCACATCTGTGTCAAGTCATGCAGCGCCTGCATTGGATGCTGCGGAAACCGGA
601  169_HRV89b    CAACCTAGCACATCTGTGTCAAGTCATGCAGCGCCTGCATTGGATGCTGCGGAAACCGGA
602  170_HRV89     CAACCTAGCACATCTGTGTCAAGTCATGCAGCGCCTGCATTGGATGCTGCGGAAACCGGA
603  171_HRV58     CAACCTAGTACATCTGTATCAAGTCATTCTGTGCCTGCCTTGGATGCTGCAGAAACGGGA
604  172_HRV58a    CAACCTAGTACATCTGTATCAAGTCATTCTGTGCCTGCCTTGGATGCTGCAGAAACGGGA
605  173_HRV58b    CAACCTAGTACATCTGTATCAAGTCATTCTGTGCCTGCCTTGGATGCTGCAGAAACGGGA
606  174_HRV12a    AACAAAAGTAATGGGCAGTTATCAAACGCAGCACCAGCGTTGGACGCTGCAGAAACTGGT
607  175_HRV12b    AACAAAAGTAATGGGCAGTTATCAAACGCAGCACCAGCGTTGGACGCTGCAGAAACTGGT
608  176_HRV12     AACAAAAGTAATGGGCAGTTATCAAACGCAGCACCAGCGTTGGACGCTGCAGAAACTGGT
609  177_HRV78a    AAAGAAAGTAAACCCCAGTCTAGCAACTCCCGCTCCAGTTTTGGACGCTGCAGAAACAGGT
610  178_HRV78b    AAAGAAAGTAAACCCCAGTCTAGCAACTCCGCTCCAGTTTTGGACGCTGCAGAAACAGGT
611  179_HRV78     AAAGAAAGTAAACCCCAGTCTAGCAACTCCGCTCCAGTTTTGGACGCTGCAGAAACAGGT
612  180_HRV20     ACATCTAGTAACTCCCAAACATCAAATGCAGCACCAGCACTAGATGCTGCTGAGACAGGA
613  181_HRV20a    ACATCTAGTAACTCCCAAACATCAAATGCAGCACCAGCACTAGATGCTGCTGAGACAGGA
614  182_HRV20b    ACATCTAGTAACTCCCAAACATCAAATGCAGCACCAGCACTAGATGCTGCTGAGACAGGA
615  183_HRV68     CCAGCAAGTAATACCCAAACTTCAAATGCAGCCCCAGCCTTAGATGCTGCTGAGACTGGA
616  184_HRV68a    CCAGCAAGTAATACCCAAACTTCAAATGCAGCCCCAGCCTCTAGATGCTGCTGAGACTGGA
617  185_HRV68b    CCAGCAAGTAATACCCAAACTTCAAATGCAGCCCCAGCCTTAGATGCTGCTGAGACTGGA
618  186_HRV28     AATCCTAGCAACGCACAAACTACAAATGCAGCTCCCGCTCTCGATGCCGCTGAGACGGGG
619  187_HRV28a    AATCCTAGCAACGCACAAACTACAAATGCAGCTCCCGCTCTCGATGCCGCTGAGACGGGG
620  188_HRV28b    AATCCTAGCAACGCACAAACTACAAATGCAGCTCCCGCTCTCGATGCCGCTGAGACGGGG
621  189_HRV53a    AATGCAAGCAATCCACAAACTTCAAATTCAGCACCAGCACTAGATGCTGCAGAAACGGGT
622  190_HRV53b    AATGCAAGCAATCCACAAACTTCAAATTCAGCACCAGCACTAGATGCTGCAGAAACGGGT
623  191_HRV53     AATGCAAGCAATCCACAAACTTCAAATTCAGCACCAGCACTAGATGCTGCAGAAACGGGT
624  192_HRV46a    AATGCCAGTAGTGGACATACATCTAATTCAGCTCCAGCACTTGATGCAGCAGAAACTGGA
625  193_HRV46b    AATGCCAGTAGTGGACATACATCTAATTCAGCTCCAGCACTTGATGCAGCAGAAACTGGA
626  194_HRV46     AATGCCAGTAGTGGACATACATCTAATTCAGCTCCAGCACTTGATGCAGCAGAAACTGGA
627  195_HRV80a    AGTGCTAGCAATGGACATACATCAAACTCAGCTCCAACACTTGATGCAGCAGAAACTGGT
628  196_HRV80b    AGTGCTAGCAATGGACATACATCAAACTCAGCTCCAACACTTGATGCAGCAGAAACTGGT
629  197_HRV80     AGTGCTAGCAATGGACATACATCAAACTCAGCTCCAACACTTGATGCAGCAGAAACTGGT
630  198_HRV51     CAACCTAGCAGTGGGCACACATCTAATGCTGCACCAGCTCTAGATGCTGCTGAGACAGGA
631  199_HRV51a    CAACCTAGCAGTGGGCACACATCTAATGCTGCACCAGCTCTAGATGCTGCTGAGACAGGA
632  200_HRV51b    CAACCTAGCAGTGGGCACACATCTAATGCTGCACCAGCTCTAGATGCTGCTGAGACAGGA
633  201_HRV65a    CAAGCTAGTAATGGGCATACATCTAATGCTGCACCAGCTTTAGATGCTGCTGAAACAGGA
634  202_HRV65b    CAAGCTAGTAATGGGCATACATCTAATGCTGCACCAGCTTTAGATGCTGCTGAAACAGGA
635  203_HRV65     CAAGCTAGTAATGGGCATACATCTAATGCTGCACCAGCTTTAGATGCTGCTGAAACAGGA
636  204_HRV71a    CAACCTAGTAATGGACATACCTCAAACTCAGCACCAGCCTTAGATGCAGCAGAAACTGGG
637  205_HRV71b    CAACCTAGTAATGGACATACCTCAAACTCAGCACCAGCCTTAGATGCAGCAGAAACTGGG
638  206_HRV71     CAACCTAGTAATGGACATACCTCAAACTCAGCACCAGCCTTAGATGCAGCAGAAACTGGG
639  207_HRV8      CAAGCTAGTAATGGATCTATAGCAAATTCAGCACCAGCATTAGATGCAGCAGAGACTGGA
640  208_HRV95     CAAGCCAGTAATGGATCTATAGCAAATTCAGCACCAGCATTAGATGCAGCAGAGACTGGA
641  209_HRV45     CGACCCAGCGATGGGTTGATTGCAAACTCAGCCCCAGCTTTGGATGCAGCTGAAACTGGA
642  210_HRV45a    CGACCCAGCGATGGGTTGATTGCAAACTCAGCCCCAGCTTTGGATGCAGCTGAAACTGGA
643  211_HRV45b    CGACCCAGCGATGGGTTGATTGCAAACTCAGCCCCAGCTTTGGATGCAGCTGAAACTGGA
644  GROUP_1       ------AG---------------A--C-G---C-----T-GA-GC-GC-GA-AC-GG-
645
646  1_HRV1A1|d    CACACCAGTAATGTTCAACCAGAAGATGCTATAGAGACAAGGTATGTTATAACATCACAA
647  2_HRV1A2|d    CACACCAGTAATGTTCAACCAGAAGATGCTATAGAGACAAGGTATGTTATAACATCACAA
648  3_HRV1A|cD    CACACCAGTAATGTTCAACCAGAAGATGCTATAGAGACAAGGTATGTTATAACATCACAA
649  4_HRV1B1|d    CACACCAGTAATGTACAACCAGAGGATGCTATAGAAACAAGATATGTTATGACATCACAA
650  5_HRV1B2|d    CACACCAGTAATGTACAACCAGAGGATGCTATAGAAACAAGATATGTTATGACATCACAA
```

FIG. D10 CONT'D

```
06.trace                                                                                    9/20/2007 5:04 PM 651  6_HRV1B      CACACCAGTAATGTACAACCAGAGGATGCTATAGAAACAAGATATGTTATGACATCACAA
652  7_HRV40a|d   CATACAAGCAACATACAACCTGAAGATACAATAGAAACAAGATTTGTGCAGACATCACAA
653  8_HRV40b|d   CATACAAGCAACATACAACCTGAAGATACAATAGAAACAAGATTTGTGCAGACATCACAA
654  9_HRV40      CATACAAGCAACATACAACCTGAAGATACAATAGAAACAAGATTTGTGCAGACATCACAA
655  10_HRV85     CATACAAGTAGTACACAGCCCGAGGATACAATAGAGACCAGGTTTGTTCAAACTTCACAG
656  11_HRV85a|   CATACAAGTAGTACACAGCCCGAGGATACAATAGAGACCAGGTTTGTTCAAACTTCACAG
657  12_HRV85b|   CATACAAGTAGTACACAGCCCGAGGATACAATAGAGACCAGGTTTGTTCAAACTTCACAG
658  13_HRV56a|   CATACTAGTGCAATCCAACCAGAAGACACTATAGAAACCAGATATGTACAGACATCACAA
659  14_HRV56b|   CATACTAGTGCAATCCAACCAGAAGACACTATAGAAACCAGATATGTACAGACATCACAA
660  15_HRV56     CATACTAGTGCAATCCAACCAGAAGACACTATAGAAACCAGATATGTACAGACATCACAA
661  16_HRV54     CACACTAGTGGAGTACAACCCGAGGACACCATAGAAACAAGATTTGTGCAGACATCACAA
662  17_HRV98     CACACTAGTGGAATACAACCTGAGGATACTATAGAAACAAGATATGTGCAGACATCACAA
663  18_HRV59a|   CATACAAGCAGTATACAACCTGAGGATACCATAGAAACAAGATATGTTCAGACATCACAA
664  19_HRV59b|   CATACAAGCAGTATACAACCTGAGGATACCATAGAAACAAGATATGTTCAGACATCACAA
665  20_HRV59     CATACAAGCAGTATACAACCTGAGGATACCATAGAAACAAGATATGTTCAGACATCACAA
666  21_HRV63     CACACAAGCAGTATACAACCTGAGGATACTGTAGAAACTAGATATGTGCAAACGTCTCAA
667  22_HRV63b|   CACACAAGCAGTATACAACCTGAGGATACTGTAGAAACTAGATATGTGCAAACGTCTCAA
668  23_HRV63a|   CACACAAGCAGTATACAACCTGAGGATACTGTAGAAACTAGATATGTGCAAACGTCTCAA
669  24_HRV39     CACACAAGTAGCACCCAGCCTGAAGACACAATTGAAACAAGATATGTGCAAACCTCACAT
670  25_HRV39a|   CACACAAGTAGCACCCAGCCTGAAGACACAATTGAAACAAGATATGTGCAAACCTCACAT
671  26_HRV39b|   CACACAAGTAGCATCCAACCTGAAGACACAATTGAAACAAGATATGTGCAAACCTCACAT
672  27_HRV10a|   CATACCAGTAGTGTACAACCAGAAGATACGGTTGAAACACGATATGTGCAAACATCCCAG
673  28_HRV10b|   CATACCAGTAGTGTACAACCAGAAGATACGGTTGAAACACGATATGTGCAAACATCCCAG
674  29_HRV10     CATACCAGTAGTGTACAACCAGAAGATACGGTTGAAACACGATATGTGCAAACATCCCAG
675  30_HRV100a   CACACTAGTAATGTGCAACCTGAAGATACAGTTGAAACTCGATATGTGCAGACATCACAG
676  31_HRV100b   CACACTAGTAATGTGCAACCTGAAGATACAGTTGAAACTCGATATGTGCAGACATCACAG
677  32_HRV100    CACACTAGTAATGTGCAACCTGAAGATACAGTTGAAACTCGATATGTGCAGACATCACAG
678  33_HRV66     CACACTAGTAAAGTACAACCAGAAGATACAGTTGAGACTCGTTACGTGCAAACATCACAG
679  34_HRV66b|   CACACTAGTAAAGTACAACCAGAAGATACAGTTGAGACTCGTTACGTGCAAACATCACAG
680  35_HRV66a|   CACACTAGTAAAGTACAACCAGAAGATACAGTTGAGACTCGTTACGTGCAAACATCACAG
681  36_HRV77a|   CATACTAGTAGTGTGCAACCAGAAGATACAGTTGAGACCCGCTATGTACAAACTTCCCAG
682  37_HRV77b|   CATACTAGTAGTGTGCAACCAGAAGATACAGTTGAGACCCGCTATGTACAAACTTCCCAG
683  38_HRV77     CATACTAGTAGTGTGCAACCAGAAGATACAGTTGAGACCCGCTATGTACAAACTTCCCAG
684  39_HRV62a    CACACTAGTAATGTACAACCAGAAGCACTATTGAAACCCGTCATGTTCAAACCACACAA
685  40_HRV62b    CACACTAGTAATGTACAACCAGAAGACACTATTGAAACCCGTTATGTTCAAACCACACAA
686  41_HRV25     CACACTAGCAATGTGCAACCAGAGGATACCATTGAAACTCGTTATGTTCAAACCACACAA
687  42_HRV29a    CATACTAGTAATGTACAACCAGAAGATACCATTGAGACTCGTTATGTACAAACCTCACAT
688  43_HRV29b    CATACTAGTAATGTACAACCAGAAGATACCATTGAGACTCGTTATGTACAAACCTCACAT
689  44_HRV44a    CATACTAGTAATGTACAACCAGAAGATACCATTGAGACTCGATATGTACAAACCTCACAA
690  45_HRV44b    CATACTAGTAATGTACAACCAGAAGATACCATTGAGACTCGATATGTACAAACCTCACAA
691  46_HRV31     CACACTAGTAATGTACAACCAGAAGATACAATTGAAACTCGCTACGTGCAAACATCACAA
692  47_HRV31a|   CACACTAGTAATGTACAACCAGAAGATACAATTGAAACTCGCTACGTGCAAACATCACAA
693  48_HRV31b|   CACACTAGTAATGTACAACCAGAAGATACAATTGAAACTCGCTACGTGCAAACATCACAA
694  49_HRV47     CACACTAGCAATGTACAGCCAGAAGATACAATTGAAACTCGATATGTACAAACAGCACAA
695  50_HRV47a|   CACACTAGCAATGTACAGCCAGAAGATACAATTGAAACTCGATATGTACAAACAGCACAA
696  51_HRV47b|   CACACTAGCAATGTACAGCCAGAAGATACAATTGAAACTCGATATGTACAAACAGCACAA
697  52_HRV11     CATACTAGCAAAGTGCAGCCAGAGGATATGATTGAGACTAGATATGTGCAGACTTCACAG
698  53_HRV11b|   CATACTAGCAAAGTGCAGCCAGAGGATATGATTGAGACTAGATATGTGCAGACTTCACAG
699  54_HRV11a|   CATACTAGCAAAGTGCAGCCAGAGGATATGATTGAGACTAGATATGTGCAGACTTCACAG
700  55_HRV76     CACACAAGCAGCGTTCAACCAGAGGACATGGTTGAGACTAGGTATGTGCAAACATCACAA
701  56_HRV76b|   CACACAAGCAGCGTTCAACCAGAGGACATGGTTGAGACTAGGTATGTGCAAACATCACAA
702  57_HRV76a|   CACACAAGCAGCGTTCAACCAGAGGACATGGTTGAGACTAGGTATGTGCAAACATCACAA
703  58_HRV33     CACACTAATAATGTACAACCAGAAGATATGATTGAAACAAGATATGTACAAACATCACAA
704  59_HRV33b|   CACACTAATAATGTACAACCAGAAGATATGATTGAAACAAGATATGTACAAACATCACAA
705  60_HRV33a|   CACACTAATAATGTACAACCAGAAGATATGATTGAAACAAGATATGTACAAACATCACAA
706  61_HRV24a|   CATACGAGTAGCGTGCAGCCAGAAGATATGGTTGAAACTAGATATGTCCAAACATCACAA
707  62_HRV24b|   CATACGAGTAGCGTGCAGCCAGAAGATATGGTTGAAACTAGATATGTCCAAACATCACAA
708  63_HRV24     CATACGAGTAGCGTGCAGCCAGAAGATATGGTTGAAACTAGATATGTCCAAACATCACAA
709  64_HRV90     CATACTAGTGATGTCCAGCCAGAAGATGTGGTAGAGACCAGATACGTGCAAACATCACAA
710  65_HRV90a|   CATACTAGTGATGTCCAGCCAGAAGATGTGGTAGAGACCAGATACGTGCAAACATCACAA
711  66_HRV90b|   CATACTAGTGATGTCCAGCCAGAAGATGTGGTAGAGACCAGATACGTGCAAACATCACAA
712  67_HRV34     CACACTAGCAGTGTACAACCTGAAGATATGATTGAGACCAGGTACGTACAAACATCACAA
713  68_HRV34b|   CACACTAGCAGTGTACAACCTGAAGATATGATTGAGACCAGGTACGTACAAACATCACAA
714  69_HRV34a|   CACACTAGCAGTGTACAACCTGAAGATATGATTGAGACCAGGTACGTACAAACATCACAA
715  70_HRV50a|   CACACAAGTAATGTGCAGCCTGAAGATATGCTTGAAACTAGATATGTGCAAACATCGCAT
```

FIG. D10 CONT'D 06.trace                                                                                    9/20/2007 5:04 PM

```
716  71_HRV50b|    CACACAAGTAATGTGCAGCCTGAAGATATGCTTGAAACTAGATATGTGCAAACATCGCAT
717  72_HRV50     CACACAAGTAATGTGCAGCCTGAAGATATGCTTGAAACTAGATATGTGCAAACATCGCAT
718  73_HRV18a|   CACACCAGCAATGTGCAACCTGAAGATATGATTGAGACTAGGTATGTACAAACATCACAA
719  74_HRV18b|   CACACCAGCAATGTGCAACCTGAAGATATGATTGAGACTAGGTATGTACAAACATCACAA
720  75_HRV18     CACACCAGCAATGTGCAACCTGAAGATATGATTGAGACTAGGTATGTACAAACATCACAA
721  76_HRV55     CATACAAGCAATGTACAACCAGAAGATGTAATTGAGACAAGATATGTTCAGACATCACAA
722  77_HRV55b|   CATACAAGCAATGTACAACCAGAAGATGTAATTGAGACAAGATATGTTCAGACATCACAA
723  78_HRV55a|   CATACAAGCAATGTACAACCAGAAGATGTAATTGAGACAAGATATGTTCAGACATCACAA
724  79_HRV57     CACACTAGTAATGTACAACCGGAAGACATGATTGAAACTAGATATGTCCAGACATCACAA
725  80_HRV57a|   CACACTAGTAATGTACAACCGGAAGACATGATTGAAACTAGATATGTCCAGACATCACAA
726  81_HRV57b|   CACACTAGTAATGTACAACCGGAAGACATGATTGAAACTAGATATGTCCAGACATCACAA
727  82_HRV21     CACACTAGTAATGTACAGCCGGAGGATATGGTTGAAACAAGGTATGTTCAGACATCACAA
728  83_HRVHan    CACACTAGTAATGTACAACCAGAGGATATGGTTGAAACAAGGTATGTTCAGACATCACAA
729  84_HRV43     CATACTAGCCAGGTGCAACCTGAAGACATGGTAGAGACAAGGTCAGTACATAATTTCCAA
730  85_HRV43b|   CATACTAGCCAGGTGCAACCTGAAGACATGGTAGAGACAAGGTCAGTACATAATTTCCAA
731  86_HRV43a|   CATACTAGCCAGGTGCAACCTGAAGACATGGTAGAGACAAGGTCAGTACATAATTTCCAA
732  87_HRV75     CATACCAGCCATGTTCAACCAGAAGACATGTTAGAAACAAGGCAAGTACAAAATTTCCAA
733  88_HRV75b|   CATACCAGCCATGTTCAACCAGAAGACATGTTAGAAACAAGGCAAGTACAAAATTTCCAA
734  89_HRV75a|   CATACCAGCCATGTTCAACCAGAAGACATGTTAGAAACAAGGCAAGTACAAAATTTCCAA
735  96_HRV9a|d   CATACTAGCAATGTTCAACCTGAAGACATGATTGAAACACGTTATGTGCAGACATCACAA
736  97_HRV9b|d   CATACTAGCAATGTTCAACCTGAAGACATGATTGAAACACGTTATGTGCAGACATCACAA
737  98_HRV9      CATACTAGCAATGTTCAACCTGAAGACATGATTGAAACACGTTATGTGCAGACATCACAA
738  99_HRV32     CATACCAGTAATGTTCAACCTGAAGACATGATTGAAACACGTTATGTGCAAACAACACAC
739  100_HRV32a   CATACCAGTAATGTTCAACCTGAAGACATGATTGAAACACGTTATGTGCAAACAACACAC
740  101_HRV32b   CATACCAGTAATGTTCAACCTGAAGACATGATTGAAACACGTTATGTGCAAACAACACAC
741  102_HRV67    CACACTAGCAGTGTACAACCTGAAGATATGATCGAGACTCGTTATGTACAGGCATCAAAT
742  103_HRV67a   CACACTAGCAGTGTACAACCTGAAGATATGATCGAGACTCGTTATGTACAGGCATCAAAT
743  104_HRV67b   CACACTAGCAGTGTACAACCTGAAGATATGATCGAGACTCGTTATGTACAGGCATCAAAT
744  105_HRV15    CATACTAGCAGTGTTCAACCTGAGGATATGATTGAAACTCGTTACGTCCAAACATCACAG
745  106_HRV15a   CATACTAGCAGTGTTCAACCTGAGGATATGATTGAAACTCGTTACGTCCAAACATCACAG
746  107_HRV15b   CATACTAGCAGTGTTCAACCTGAAGATATGATTGAAACTCGTTACGTCCAAACATCACAG
747  108_HRV74a   CATACCAGTAATGTGCAACCAGAAGATATGGTTGAGACACGCTATGTGCAAACCTCACAG
748  109_HRV74b   CATACCAGTAATGTGCAACCAGAAGATATGGTTGAGACACGCTATGTGCAAACCTCACAG
749  110_HRV74    CATACCAGTAATGTGCAACCAGAAGATATGGTTGAGACACGCTATGTGCAAACCTCACAG
750  111_HRV38a   CACACCAGTAATGTGCAGCCTGAGGATATGATTGAAACTCGCTATGTACAGACATCACAA
751  112_HRV38b   CACACCAGTAATGTGCAGCCTGAGGATATGATTGAAACTCGCTATGTACAGACATCACAA
752  113_HRV38    CACACCAGTAATGTGCAGCCTGAGGATATGATTGAAACTCGCTATGTACAGACATCACAA
753  114_HRV60    CACTAGTAATGTACAGCCTGAGGACGTGATTGAAACACGTTATGTGCAGATTACACAA
754  115_HRV60a   CACACTAGTAATGTACAGCCTGAGGACGTGATTGAAACACGTTATGTGCAGATTACACAA
755  116_HRV60b   CACACTAGTAATGTACAGCCTGAGGACGTGATTGAAACACGTTATGTGCAGATTACACAA
756  117_HRV64a   CACACCAGTAATGTACAGCCTGAAGATATGATTGAAACGCGCTATGTACAAAACACTCAA
757  118_HRV64b   CACACCAGTAATGTACAGCCTGAAGATATGATTGAAACGCGCTATGTACAAAACACTCAA
758  119_HRV64    CACACCAGTAATGTACAGCCTGAAGATATGATTGAAACGCGCTATGTACAAAACACTCAA
759  120_HRV94a   CACACAAGCAATGTACAACCTGAGGATATGATTGAAACACGCTATGTACAAAACACTCAA
760  121_HRV94b   CACACAAGCAATGTACAACCTGAGGATATGATTGAAACACGCTATGTACAAAACACTCAA
761  122_HRV94    CACACAAGCAATGTACAACCTGAGGATATGATTGAAACACGCTATGTACAAAACACTCAA
762  123_HRV22    CACACAAGCAATGTGCAGCCAGAAGACATGATAGAAACACGCTATGTGTTAAATTCACAA
763  124_HRV22a   CACACAAGCAATGTGCAGCCAGAAGACATGATAGAAACACGCTATGTGTTAAATTCACAA
764  125_HRV22b   CACACAAGCAATGTGCAGCCAGAAGACATGATAGAAACACGCTATGTGTTAAATTCACAA
765  126_HRV82    CATACAAGTACTGTTCAACCTGAGGACATGATTGAAACACGGTATGTTCAAACATCACAA
766  127_HRV82b   CATACAAGTACTGTTCAACCTGAGGACATGATTGAAACACGGTATGTTCAAACATCACAA
767  128_HRV82a   CATACAAGTACTGTTCAACCTGAGGACATGATTGAAACACGGTATGTTCAAACATCACAA
768  129_HRV19    CATACTAGCAATGTACAGCCTGAGGACATGATCGAAACACGCTATGTTCAAACGTCCCAG
769  130_HRV19a   CATACTAGCAATGTACAGCCTGAGGACATGATCGAAACACGCTATGTTCAAACGTCCCAG
770  131_HRV19b   CATACTAGCAATGTACAGCCTGAGGACATGATCGAAACACGCTATGTTCAAACGTCCCAG
771  132_HRV13    CACACAAGCAGTGTACAACCAGAAGACATGGTTGAAACACGTTATGTCCAAACTTCACAA
772  133_HRV13a   CACACAAGCAGTGTACAACCAGAAGACATGGTTGAAACACGTTATGTCCAAACTTCACAA
773  134_HRV13b   CACACAAGCAGTGTACAACCAGAAGACATGGTTGAAACACGTTATGTCCAAACTTCACAA
774  135_HRV41    CATACCAGTAATGTACAACCAGAAGACATGATTGAAACACGATATGTCCAAACCTCACAA
775  136_HRV41a   CATACCAGTAATGTACAACCAGAGGACATGATTGAAACACGATATGTCCAAACCTCACAA
776  137_HRV41b   CATACCAGTAATGTACAACCAGAGGACATGATTGAAACACGATATGTCCAAACCTCACAA
777  138_HRV73    CATACCAGTGGTGTACAACCAGAAGACATGATTGAGACCCGTTATGTCCAAACATCACAG
778  139_HRV73b   CATACCAGTGGTGTACAACCAGAAGACATGATTGAGACCCGTTATGTCCAAACATCACAG
779  140_HRV73a   CATACCAGTGGTGTACAACCAGAAGACATGATTGAGACCCGTTATGTCCAAACATCACAG
780  141_HRV61    CATACCAGCAATGTTCAACCGGAGGACACGATTGAAACACGATATGTTCAAACCTCACAG
```

FIG. D10 CONT'D 06.trace                                                                 9/20/2007 5:04 PM

```
781  142_HRV61a   CATACCAGCAATGTTCAACCGGAGGACACGATTGAAACACGATATGTTCAAACCTCACAG
782  143_HRV61b   CATACCAGCAATGTTCAACCGGAGGACACGATTGAAACACGATATGTTCAAACCTCACAG
783  144_HRV96    CATACTAGCAATGTCCAACCAGAGGATATGATTGAGACTCGATATGTTCAGACATCGCAG
784  145_HRV96b   CATACTAGCAATGTCCAACCAGAGGATATGATTGAGACTCGATATGTTCAGACATCGCAG
785  146_HRV96a   CATACTAGCAATGTCCAACCAGAGGATATGATTGAGACTCGATATGTTCAGACATCGCAG
786  90_HRV16a|   CATACCAATAAGATACAGCCAGAAGACACTATAGAAACCAGATATGTGCAATCTTCACAG
787  91_HRV16b|   CATACCAATAAGATACAGCCAGAAGACACTATAGAAACCAGATATGTGCAATCTTCACAG
788  92_1AYM_A    CATACCAATAAGATACAGCCAGAAGACACTATAGAAACCAGATATGTGCAATCTTCACAG
789  93_HRV81a|   CACACCAGTAATATACAACCTGAGGATACTATTGAGACCAGATATGTACAATCTTCACAG
790  94_HRV81b|   CACACCAGTAATATACAACCTGAGGATACTATTGAGACCAGATATGTACAATCTTCACAG
791  95_HRV81     CACACCAGTAATATACAACCTGAGGATACTATTGAGACCAGATATGTACAATCTTCACAG
792  147_HRV2     CACACTAGTAGTGTTCAACCAGAGGATGTCATTGAAACTAGGTATGTGCAGACATCACAA
793  148_HRV2a|   CACACTAGTAGTGTTCAACCAGAGGATGTCATTGAAACTAGGTATGTGCAGACATCACAA
794  149_HRV2b|   CACACTAGTAGTGTTCAACCAGAGGATGTCATTGAAACTAGGTATGTGCAGACATCACAA
795  150_HRV49a   CACACTAGCAATGTGCAACCTGAAGATGTCATTGAAACCAGATATGTACAGACATCACAA
796  151_HRV49b   CACACTAGCAATGTGCAACCTGAAGATGTCATTGAAACCAGATATGTACAGACATCACAA
797  152_HRV49    CACACTAGCAATGTGCAACCTGAAGATGTCATTGAAACCAGATATGTACAGACATCACAA
798  153_HRV23a   CACACTAGTAATGTTCAACCAGAAGATGTCATTGAAACCAGGTACGTTCAAACATCACAA
799  154_HRV23b   CACACTAGTAATGTTCAACCAGAAGATGTCATTGAAACCAGGTACGTTCAAACATCACAA
800  155_HRV23    CACACTAGTAATGTTCAACCAGAAGATGTCATTGAAACCAGGTACGTTCAAACATCACAA
801  156_HRV30a   CATACTAGTAATGTTCAACCTGAAGATGTCATTGAAACTAGATATGTTCAAACATCACAA
802  157_HRV30b   CATACTAGTAATGTTCAACCTGAAGATGTCATTGAAACTAGATATGTTCAAACATCACAA
803  158_HRV30    CACACTAGTAATGTTCAACCTGAAGATGTCATTGAAACTAGATATGTTCAAACATCACAA
804  159_HRV7     CATACTAGTTCTGTTCAACCTGAAGATATGATCGAGACAAGGTATGTCATAACAGACCAA
805  160_HRV7b|   CATACTAGTTCTGTTCAACCTGAAGATATGATCGAGACAAGGTATGTCATAACAGACCAA
806  161_HRV7a|   CATACTAGTTCTGTTCAACCTGAAGATATGATCGAGACAAGGTATGTCATAACAGACCAA
807  162_HRV88    CATACTAGTTCTGTTCAACCTGAAGATATGATAGAAACTAGATATGTTATAACAGATCAA
808  163_HRV88a   CATACTAGTTCTGTTCAACCTGAAGATATGATAGAAACTAGATATGTTATAACAGATCAA
809  164_HRV88b   CATACTAGTTCTGTTCAACCTGAAGATATGATAGAAACTAGATATGTTATAACAGATCAA
810  165_HRV36a   CATACCAGCTCTGTCCAACCAGAGGACATGATCGAGACCAGATATGTCATAACTGATCAA
811  166_HRV36b   CATACCAGCTCTGTCCAACCAGAGGACATGATCGAGACCAGATATGTCATAACTGATCAA
812  167_HRV36    CATACCAGCTCTGTCCAACCAGAGGACATGATCGAGACCAGATATGTCATAACTGATCAA
813  168_HRV89a   CACACCAGCTCTGTTCAACCTGAAGATATGATTGAAACTAGATATGTTATAACTGATCAA
814  169_HRV89b   CACACCAGCTCTGTTCAACCTGAAGATATGATTGAAACTAGATATGTTATAACTGATCAA
815  170_HRV89    CACACCAGCTCTGTTCAACCTGAAGATATGATTGAAACTAGATATGTTATAACTGATCAA
816  171_HRV58    CACACAAGTTCTGTTCAGCCTGAGGATATGATTGAAACTAGATATGTTATCACAGATCAA
817  172_HRV58a   CACACAAGTTCTGTTCAGCCTGAGGATATGATTGAAACTAGATATGTTATCACAGATCAA
818  173_HRV58b   CACACAAGTTCTGTTCAGCCTGAGGATATGATTGAAACTAGATATGTTATCACAGATCAA
819  174_HRV12a   CATACCAGCCAAACACAACCAGAAGATGTGATTGAAACCAGGTATGTGATTACAGACCAG
820  175_HRV12b   CATACCAGCCAAACACAACCAGAAGATGTGATTGAAACCAGGTATGTGATTACAGACCAG
821  176_HRV12    CATACCAGCCAAACACAACCAGAAGATGTGATTGAAACCAGGTATGTGATTACAGACCAG
822  177_HRV78a   CATACGAACCAAGTACAGCCTGAAGACACCATAGAAACTAGATATGTTATAACTGACCAA
823  178_HRV78b   CATACGAACCAAGTACAGCCTGAAGACACCATAGAAACTAGATATGTTATAACTGACCAA
824  179_HRV78    CATACGAACCAAGTACAGCCTGAAGACACCATAGAAACTAGATATGTTATAACTGACCAA
825  180_HRV20    CACACAAACCAGGTCCAGCCAGAAGATATGGTCGAGACACGGTATGTAATTACTGATCAG
826  181_HRV20a   CACACAAACCAGGTCCAGCCAGAAGATATGGTCGAGACACGGTATGTAATTACTGATCAG
827  182_HRV20b   CACACAAACCAGGTCCAGCCAGAAGATATGGTCGAGACACGGTATGTAATTACTGATCAG
828  183_HRV68    CATACAAACCAAGTCCAACCAGAAGATGTGGTTGAAACACGCTATGTCATAACAGACCAG
829  184_HRV68a   CATACAAACCAAGTCCAACCAGAAGATGTGGTTGAAACACGCTATGTCATAACAGACCAG
830  185_HRV68b   CATACAAACCAAGTCCAACCAGAAGATGTGGTTGAAACACGCTATGTCATAACAGACCAG
831  186_HRV28    CACACAAGCCAAACACAACCTGAAGACATGGTTGAGACTAGGTATGTAATCACAGATCAG
832  187_HRV28a   CACACAAGCCAAACACAACCTGAAGACATGGTTGAGACTAGGTATGTAATCACAGATCAG
833  188_HRV28b   CACACAAGCCAAACACAACCTGAAGACATGGTTGAGACTAGGTATGTAATCACAGATCAG
834  189_HRV53a   CATACAAGTCAGACACAACCTGAGGACATGCTGGAAACTAGATATGTCATCACAGACCAA
835  190_HRV53b   CATACAAGTCAGACACAACCTGAGGACATGCTGGAAACTAGATATGTCATCACAGACCAA
836  191_HRV53    CATACAAGTCAGACACAACCTGAGGACATGCTGGAAACTAGATATGTCATCACAGACCAA
837  192_HRV46a   CACACTAGCCAGATACAACCAGAAGACATGATAGAAACCAGATATGTTATCACAGACCAA
838  193_HRV46b   CACACTAGCCAGATACAACCAGAAGACATGATAGAAACCAGATATGTTATCACAGACCAA
839  194_HRV46    CACACTAGCCAGATACAACCAGAAGACATGATAGAAACCAGATATGTTATCACAGACCAA
840  195_HRV80a   CACACTAGCCAGGTGCAACCAGAAGACATGATAGAAACTAGATATGTTATTACTGATCAG
841  196_HRV80b   CACACTAGCCAGGTGCAACCAGAAGACATGATAGAAACTAGATATGTTATTACTGATCAG
842  197_HRV80    CACACTAGCCAGGTGCAACCAGAAGACATGATAGAAACTAGATATGTTATTACTGATCAG
843  198_HRV51    CATACTAGTCAAGTTCAACCAGAAGATATGGTAGAGACCAGGTATGTTGTCACAGACCAA
844  199_HRV51a   CATACTAGTCAAGTTCAACCAGAAGATATGGTAGAGACCAGGTATGTTGTCACAGACCAA
845  200_HRV51b   CATACTAGTCAAGTTCAACCAGAAGATATGGTAGAGACCAGGTATGTTGTCACAGACCAA
```

FIG. D10 CONT'D

```
06.trace                                                                                                9/20/2007 5:04 PM 846 201_HRV65a    CACACTAGTCAAGTTCAACCAGAGGATGTGATAGAAACCAGATATGTCATCACAGATCAA
847 202_HRV65b    CACACTAGTCAAGTTCAACCAGAGGATGTGATAGAAACCAGATATGTCATCACAGATCAA
848 203_HRV65     CACACTAGTCAAGTTCAACCAGAGGATGTGATAGAAACCAGATATGTCATCACAGATCAA
849 204_HRV71a    CATACCAACCAAGTACAACCAGAAGATGTTATGGAAACCAGATATGTGATCACTGATCAA
850 205_HRV71b    CATACCAACCAAGTACAACCAGAAGATGTTATGGAAACCAGATATGTGATCACTGATCAA
851 206_HRV71     CATACCAACCAAGTACAACCAGAAGATGTTATGGAAACCAGATATGTGATCACTGATCAA
852 207_HRV8      CACACAAGTTCAGTGCAACCTGAAGATCTTATAGAGACTAGGTATGTAATTACAGATCAA
853 208_HRV95     CACACAAGTTCAGTGCAACCTGAAGATCTTATAGAGACTAGGTATGTAATTACAGATCAA
854 209_HRV45     CACACCAGTTCAGTGCAGCCTGAGGACCTTATAGAGACTAGATATGTGATTGCAGACCAA
855 210_HRV45a    CACACCAGTTCAGTGCAGCCTGAGGACCTTATAGAGACTAGATATGTGATTGCAGACCAA
856 211_HRV45b    CACACCAGTTCAGTGCAGCCTGAGGACCTTATAGAGACTAGATATGTGATTGCAGACCAA
857 GROUP_1       CA-AC-A--------CA-CC-GA-GA-----T-GA-AC--G----GT-----------A-
858
859 1_HRV1A1|d    ACAAGAGATGAGATGAGTATAGAAAGTTTCCTTGGTAGATCTGGTTGTGTCCACATCTCA
860 2_HRV1A2|d    ACAAGAGATGAGATGAGTATAGAAAGTTTCCTTGGTAGATCTGGTTGTGTCCACATCTCA
861 3_HRV1A|cD    ACAAGAGATGAGATGAGTATAGAAAGTTTCCTTGGTAGATCTGGTTGTGTCCACATCTCA
862 4_HRV1B1|d    ACAAGAGATGAGATGAGTATAGAAAGTTTTCTTGGTAGATCTGGCTGTGTGCATATTTCA
863 5_HRV1B2|d    ACAAGAGATGAGATGAGTATAGAAAGTTTTCTTGGTAGATCTGGCTGTGTGCATATTTCA
864 6_HRV1B       ACAAGAGATGAGATGAGTATAGAAAGTTTTCTTGGTAGATCTGGCTGTGTGCATATTTCA
865 7_HRV40a|d    ACTAGAGATGAAATGAGCATAGAGAGTTTCTTGGGAAGATCTGGGTGCATTCATATATCC
866 8_HRV40b|d    ACTAGAGATGAAATGAGCATAGAGAGTTTCTTGGGAAGATCTGGGTGCATTCATATATCC
867 9_HRV40       ACTAGAGATGAAATGAGCATAGAGAGTTTCTTGGGAAGATCTGGGTGCATTCATATATCC
868 10_HRV85      ACTAGGGATGAAATGAGTTTAGAAAGTTTCTTGGGAAGATCTGGATGTATCCATATATCT
869 11_HRV85a|    ACTAGGGATGAAATGAGTTTAGAAAGTTTCTTGGGAAGATCTGGATGTATCCATATATCT
870 12_HRV85b|    ACTAGGGATGAAATGAGTTTAGAAAGTTTCTTGGGAAGATCTGGATGTATCCATATATCT
871 13_HRV56a|    ACTAGGGATGAAATGAGTATAGAGAGTTTTCTAGGTAGATCAGGTTGTATACATATATCA
872 14_HRV56b|    ACTAGGGATGAAATGAGTATAGAGAGTTTTCTAGGTAGATCAGGTTGTATACATATATCA
873 15_HRV56      ACTAGGGATGAAATGAGTATAGAGAGTTTTCTAGGTAGATCAGGTTGTATACATATATCA
874 16_HRV54      ACTAGAGATGAAATGAGCATAGAAAGTTTTCTAGGCAGGGCTGGTTGCATACATGAATCC
875 17_HRV98      ACCAGAGATGAAATGAGTATAGAAAGTTTTCTAGGTAGGGCCGGTTGTATACATGAATCT
876 18_HRV59a|    ACTAGAGATGAGATGAGTGTAGAAAGTTTCTTAGGTAGATCTGGGTGTATACATATTTCA
877 19_HRV59b|    ACTAGAGATGAGATGAGTGTAGAAAGTTTCTTAGGTAGATCTGGGTGTATACATATTTCA
878 20_HRV59      ACTAGAGATGAGATGAGTGTAGAAAGTTTCTTAGGTAGATCTGGGTGTATACATATTTCA
879 21_HRV63      ACAAGGGATGAAATGAGTGTTCTTGGTAGACAGGATGCATACACATATCA
880 22_HRV63b|    ACAAGGGATGAAATGAGTGTAGAGAGCTTTCTTGGTAGATCAGGATGCATACACATATCA
881 23_HRV63a|    ACAAGGGATGAAATGAGTGTAGAGAGCTTTCTTGGTAGATCAGGATGCATACACATATCA
882 24_HRV39      ACTAGGGATGAAATGAGCGTTGAAAGTTTCTTAGGCAGATCTGGCTGTATTCACATTTCC
883 25_HRV39a|    ACTAGGGATGAAATGAGCGTTGAAAGTTTCTTAGGCAGATCTGGCTGTATTCACATTTCC
884 26_HRV39b|    ACTAGGGATGAAATGAGTGTTGAAAGTTTCTTAGGCAGATCTGGCTGTATTCACATTTCC
885 27_HRV10a|    ACGAGAGATGAAATGAGTATTGAAAGTTTTCTTGGCAGGTCAGGTTGTATACACACCTCA
886 28_HRV10b|    ACGAGAGATGAAATGAGTATTGAAAGTTTTCTTGGCAGGTCAGGTTGTATACACACCTCA
887 29_HRV10      ACGAGAGATGAAATGAGTATTGAAAGTTTTCTTGGCAGGTCAGGTTGTATACACACCTCA
888 30_HRV100a    ACCAGGGATGAAATGAGTATTGAGAGCTTTCTTGGAAGATCTGGTTGTATACACACCTCA
889 31_HRV100b    ACCAGGGATGAAATGAGTATTGAGAGCTTTCTTGGAAGATCTGGTTGTATACACACCTCA
890 32_HRV100     ACCAGGGATGAAATGAGTATTGAGAGCTTTCTTGGAAGATCTGGTTGTATACACACCTCA
891 33_HRV66      ACTAGAGATGAAATGAGCATAGAAAGTTTTCTAGGTAGGTCAGGATGTATCCATATATCA
892 34_HRV66b|    ACTAGAGATGAAATGAGCATAGAAAGTTTTCTAGGTAGGTCAGGATGTATCCATATATCA
893 35_HRV66a|    ACTAGAGATGAAATGAGCATAGAAAGTTTTCTAGGTAGGTCAGGATGTATCCATATATCA
894 36_HRV77a|    ACAAGGGATGAGATGAGTATTGAGAGCTTTCTGGGGTAGGTCTGGTTGTATTCACATTCA
895 37_HRV77b|    ACAAGGGATGAGATGAGTATTGAGAGCTTTCTGGGTAGGTCTGGTTGTATTCACATTTCA
896 38_HRV77      ACAAGGGATGAGATGAGTATTGAGAGCTTTCTGGGTAGGTCTGGTTGTATTCACATTTCA
897 39_HRV62a     ACTAGAGATGAAATGAGCATTGAGAGCTTTCTTGGTAGGTCAGGGTGCGTACACACTTCA
898 40_HRV62b     ACTAGAGATGAAATGAGCATTGAGAGCTTTCTTGGTAGGTCAGGGTGCGTACACACTTCA
899 41_HRV25      ACTAGAGATGAAATGAGTATTGAAAGTTTCTTGGTAGGTCAGGGTGTGTACATACTTCA
900 42_HRV29a     ACTAGAGATGAAATGAGCATTGAAAGTTTCTTGGGTAGATCAGGATGTATACATGTTTCA
901 43_HRV29b     ACTAGAGATGAAATGAGCATTGAAAGTTTTCTTGGTAGATCAGGATGTATACATGTTTCA
902 44_HRV44a     ACTAGAGATGAAATGAGCATTGAAAGTTTCTTGGCACAGATCAGGGTGTATACATGTTTCA
903 45_HRV44b     ACTAGAGATGAAATGAGCATTGAAAGTTTCTTGGCAGATCAGGGTGTATACATGTTTCA
904 46_HRV31      ACAAGAGATGAAATGAGCATTGAAAGTTTCCTTGGTAGGTCAGGATGTGTACATACTTCA
905 47_HRV31a|    ACAAGAGATGAAATGAGCATTGAAAGTTTCCTTGGTAGGTCAGGATGTGTACATACTTCA
906 48_HRV31b|    ACAAGAGATGAAATGAGCATTGAAAGTTTCCTTGGTAGGTCAGGATGTGTACATACTTCA
907 49_HRV47      ACAAGAGATGAAATGAGCATTGAGAGCTTCCTTGGCAGGTCAGGATGTGTGCATTCCTCA
908 50_HRV47a|    ACAAGAGATGAAATGAGCATTGAGAGCTTCCTTGGCAGGTCAGGATGTGTGCATTCCTCA
909 51_HRV47b|    ACAAGAGATGAAATGAGCATTGAGAGCTTCCTTGGCAGGTCAGGATGTGTGCATTCCTCA
910 52_HRV11      ACTCTTGATGAAATGAGCATTGAGAGCTTCCTAGGTAGATCTGGTTGTATTCACATGTCC
```

FIG. D10 CONT'D

06.trace                                                                                        9/20/2007 5:04 PM

```
911  53_HRV11b|    ACTCTTGATGAAATGAGCATTGAGAGCTTCCTAGGTAGATCTGGTTGTATTCACATGTCC
912  54_HRV11a|    ACTCTTGATGAAATGAGCATTGAGAGCTTCCTAGGTAGATCTGGTTGTATTCACATGTCC
913  55_HRV76     ACTCTTGATGAGATGTGTATGGAGAGTTTCTTAGGGAGATCTGGTTGTATTCATATTTCA
914  56_HRV76b|    ACTCTTGATGAGATGTGTATGGAGAGTTTCTTAGGGAGATCTGGTTGTATTCATATTTCA
915  57_HRV76a|    ACTCTTGATGAGATGTGTATGGAGAGTTTCTTAGGGAGATCTGGTTGTATTCATATTTCA
916  58_HRV33     ACTCTTGATGAGATGAGTGTGGAAAGCTTCTTAGGAAGGTCTGGTTGCATTCACATGTCA
917  59_HRV33b|    ACTCTTGATGAGATGAGTGTGGAAAGCTTCTTAGGAAGGTCTGGTTGCATTCACATGTCA
918  60_HRV33a|    ACTCTTGATGAGATGAGTGTGGAAAGCTTCTTAGGAAGGTCTGGTTGCATTCACATGTCA
919  61_HRV24a|    ACATTACATGAGATGAGTGTTGAAAGTTTCTTGGGTAGATCAGGTTGCATACACATGTCC
920  62_HRV24b|    ACATTACATGAGATGAGTGTTGAAAGTTTCTTGGGTAGATCAGGTTGCATACACATGTCC
921  63_HRV24     ACATTACATGAGATGAGTGTTGAAAGTTTCTTGGGTAGATCAGGTTGCATACACATGTCC
922  64_HRV90     ACAAGAGATGAAATGAGTGTTGAAAGTTTTCTAGGGAGATCAGGTTGCATTCATATGTCA
923  65_HRV90a|    ACAAGAGATGAAATGAGTGTTGAAAGTTTTCTAGGGAGATCAGGTTGCATTCATATGTCA
924  66_HRV90b|    ACAAGAGATGAAATGAGTGTTGAAAGTTTTCTAGGGAGATCAGGTTGCATTCATATGTCA
925  67_HRV34     ACAAGAGATGAAATGAGCATTGAGAGTTTCCTGGGTAGGTCTGGCTGTATACACATGTCC
926  68_HRV34b|    ACAAGAGATGAAATGAGCATTGAGAGTTTCCTGGGTAGGTCTGGCTGTATACACATGTCC
927  69_HRV34a|    ACAAGAGATGAAATGAGCATTGAGAGTTTCCTGGGTAGGTCTGGCTGTATACACATGTCC
928  70_HRV50a|    ACAAGAGATGAAATGAGCATTGAAAGTTTCCTAGGTAGATCTGGTTGTATACATATATCT
929  71_HRV50b|    ACAAGAGATGAAATGAGCATTGAAAGTTTCCTAGGTAGATCTGGTTGTATACATATATCT
930  72_HRV50     ACAAGAGATGAAATGAGCATTGAAAGTTTCCTAGGTAGATCTGGTTGTATACATATATCT
931  73_HRV18a|    ACAAGAGATGAAATGAGTATAGAGTGTTTCTAGGCAGATCAGGGTGTATACATATCTCC
932  74_HRV18b|    ACAAGAGATGAAATGAGTATAGAGTGTTTTCTAGGCAGATCAGGGTGTATACATATCTCC
933  75_HRV18     ACAAGAGATGAAATGAGTATAGAGTGTTTTCTAGGCAGATCAGGGTGTATACATATCTCC
934  76_HRV55     ACTCGTGATGAGATGAGCATTGAAAGTTTTCTAGGTAGATCAGGATGTGTACATATATCA
935  77_HRV55b|    ACTCGTGATGAGATGAGCATTGAAAGTTTTCTAGGTAGATCAGGATGTGTACATATATCA
936  78_HRV55a|    ACTCGTGATGAGATGAGCATTGAAAGTTTTCTAGGTAGATCAGGATGTGTACATATATCA
937  79_HRV57     ACACGTGATGAAATGAGTCTTGAGAGCTTCTTAGGAAGATCTGGCTGCATTCATATTTCA
938  80_HRV57a|    ACACGTGATGAAATGAGTCTTGAGAGCTTCTTAGGAAGATCTGGCTGCATTCATATTTCA
939  81_HRV57b|    ACACGTGATGAAATGAGTCTTGAGAGCTTCTTAGGAAGATCTGGCTGCATTCATATTTCA
940  82_HRV21     ACACGTGATGAAATGAGTATTGAAAGTTTTCTGGGCAGATCAGGGTGCATTCACATGTCA
941  83_HRVHan    ACACGTGATGAAATGAGTATTGAAAGTTTTCTAGGCAGATCAGGGTGTATCCACATGTCA
942  84_HRV43     ACCAGAGATGAAATGAGTATTGAAAGTTTCTTGGGCAGATCTGGTTGCATACATATTTCA
943  85_HRV43b|    ACCAGAGATGAAATGAGTATTGAAAGTTTCTTGGGCAGATCTGGTTGCATACATATTTCA
944  86_HRV43a|    ACCAGAGATGAAATGAGTATTGAAAGTTTCTTGGGCAGATCTGGTTGCATACATATTTCA
945  87_HRV75     ACTAGAGATGAGATGAGTATTGAGAGTTTCCTAGGCAGATCTGGATGTATTCATATTTCA
946  88_HRV75b|    ACTAGAGATGAGATGAGTATTGAGAGTTTCCTAGGCAGATCTGGATGTATTCATATTTCA
947  89_HRV75a|    ACTAGAGATGAGATGAGTATTGAGAGTTTCCTAGGCAGATCTGGATGTATTCATATTTCA
948  96_HRV9a|d    ACCAGAGATGAAATGAGTCTTGAAAGCTTCTTAGGGAGATCAGGTTGTATACACATATCT
949  97_HRV9b|d    ACCAGAGATGAAATGAGTCTTGAAAGCTTCTTAGGGAGATCAGGTTGTATACACATATCT
950  98_HRV9      ACCAGAGATGAAATGAGTCTTGAAAGCTTCTTAGGGAGATCAGGTTGTATACACATATCT
951  99_HRV32     ACTAGAGATGAGATGAGTCTTGAGAGCTTCTTAGGGAGGTCAGGATGTGTACATATATCC
952  100_HRV32a    ACTAGAGATGAGATGAGTCTTGAGAGCTTCTTAGGGAGGTCAGGATGTGTACATATATCC
953  101_HRV32b    ACTAGAGATGAGATGAGTCTTGAGAGCTTCTTAGGGAGGTCAGGATGTGTACATATATCC
954  102_HRV67     ACCAGAGATGAAATGAGTCTCGAGAGCTTTCTTGGAAGGTCAGGCTGTATTCATATATCA
955  103_HRV67a    ACCAGAGATGAAATGAGTCTCGAGAGCTTTCTTGGAAGGTCAGGCTGTATTCATATATCA
956  104_HRV67b    ACCAGAGATGAAATGAGTCTCGAGAGCTTTCTTGGAAGGTCAGGCTGTATTCATATATCA
957  105_HRV15     ACCAGAGATGAAATGAGTATTGAGAGCTTCCTTGGTAGATCAGGGTGTGTCCATATTTCT
958  106_HRV15a    ACCAGAGATGAAATGAGTATTGAGAGCTTCCTTGGTAGATCAGGGTGTGTCCATATTTCT
959  107_HRV15b    ACCAGAGATGAAATGAGTATTGAGAGCTTCCTTGGTAGATCAGGGTGTGTCCATATTTCT
960  108_HRV74a    ACAAGAGATGAGATGAGTGTAGAAAGTTTTCTTGGAAGATCAGGATGCATCCATATCTCA
961  109_HRV74b    ACAAGAGATGAGATGAGTGTAGAAAGTTTTCTTGGAAGATCAGGATGCATCCATATCTCA
962  110_HRV74     ACAAGAGATGAGATGAGTGTAGAAAGTTTTCTTGGAAGATCAGGATGCATCCATATCTCA
963  111_HRV38a    ACTAGAGATGAAATGAGTGTAGAAAGTTTTCTAGGAAGATCAGGTTGTGTACATATATCC
964  112_HRV38b    ACTAGAGATGAAATGAGTGTAGAAAGTTTTCTAGGAAGATCAGGTTGTGTACATATATCC
965  113_HRV38     ACTAGAGATGAAATGAGTGTAGAAAGTTTTCTAGGAAGATCAGGTTGTGTACATATATCC
966  114_HRV60     ACTAGAGATGAGAGTGTTGAGAGCTTCCTCCGGCAGATCTGGATGTATTCATATTTCC
967  115_HRV60a    ACTAGAGATGAGAGTGTTGAGAGCTTCCTCCGGCAGATCTGGATGTATTCATATTTCC
968  116_HRV60b    ACTAGAGATGAGAGTGTTGAGAGCTTCCTCCGGCAGATCTGGATGTATTCATATTTCC
969  117_HRV64a    ACTAGAGATGAAATGAGCATTGAGAGTTTCTTGGGCAGGTCTGGTTGTATACACATATCA
970  118_HRV64b    ACTAGAGATGAAATGAGCATTGAGAGTTTCTTGGGCAGGTCTGGTTGTATACACATATCA
971  119_HRV64     ACTAGAGATGAAATGAGCATTGAGAGTTTCTTGGGCAGGTCTGGTTGTATACACATATCA
972  120_HRV94a    ACAAGGGATGAAATGAGCATTGAAAGCTTCTTGGGAAGATCTGGCTGTATACACATAGCA
973  121_HRV94b    ACAAGGGATGAAATGAGCATTGAAAGCTTCTTGGGAAGATCTGGCTGTATACACATAGCA
974  122_HRV94     ACAAGGGATGAAATGAGCATTGAAAGCTTCTTGGGAAGATCTGGCTGTATACACATAGCA
975  123_HRV22     ACTAGAGATGAAATGAGTATTGAGAGCTTCCTGGGAAGATCTGGTTGCATACATATATCA
```

FIG. D10 CONT'D 06.trace                                                                9/20/2007 5:04 PM

```
 976  124_HRV22a    ACTAGAGATGAAATGAGTATTGAGAGCTTCCTGGGAAGATCTGGTTGCATACATATATCA
 977  125_HRV22b    ACTAGAGATGAAATGAGTATTGAGAGCTTCCTGGGAAGATCTGGTTGCATACATATATCA
 978  126_HRV82     ACTAGAGATGAGATGAGCCTTGAGAGTTTCCTAGGGAGATCTGGCTGCATACACATATCA
 979  127_HRV82b    ACTAGAGATGAGATGAGCCTTGAGAGTTTCCTAGGGAGATCTGGCTGCATACACATATCA
 980  128_HRV82a    ACTAGAGATGAGATGAGCCTTGAGAGTTTCCTAGGGAGATCTGGCTGCATACACATATCA
 981  129_HRV19     ACTAGGGATGAAATGAGCATAGAAAGTTTTCTTGGCAGATCCGGTTGTGTACATGTTTCA
 982  130_HRV19a    ACTAGGGATGAAATGAGCATAGAAAGTTTTCTTGGCAGATCCGGTTGTGTACATGTTTCA
 983  131_HRV19b    ACTAGGGATGAAATGAGCATAGAAAGTTTTCTTGGCAGATCCGGTTGTGTACATGTTTCA
 984  132_HRV13     ACTAGGGATGAAATGAGTGTTGAGAGCTTTTAGGCAGATCTGGTTGTATACACATGTCT
 985  133_HRV13a    ACTAGGGATGAAATGAGTGTTGAGAGCTTTTTAGGCAGATCTGGTTGTATACACATGTCT
 986  134_HRV13b    ACTAGGGATGAAATGAGTGTTGAGAGCTTTTTAGGCAGATCTGGTTGTATACACATGTCT
 987  135_HRV41     ACTAGAGATGAAATGAGCATAGAAAGCTTTTTAGGTAGATCAGGCTGTGTACATAAGTCC
 988  136_HRV41a    ACTAGAGATGAAATGAGCATAGAAAGCTTTTTAGGTAGATCAGGCTGTGTACATAAGTCC
 989  137_HRV41b    ACTAGAGATGAAATGAGCATAGAAAGCTTTTTAGGTAGATCAGGCTGTGTACATAAGTCC
 990  138_HRV73     ACTAGAGATGAAATGAGCATTGAAAGCTTCCTTGGCAGGTCAGGTTGTATACACATGTCA
 991  139_HRV73b    ACTAGAGATGAAATGAGCATTGAAAGCTTCCTTGGCAGGTCAGGTTGTATACACATGTCA
 992  140_HRV73a    ACTAGAGATGAAATGAGCATTGAAAGCTTCCTTGGCAGGTCAGGTTGTATACACATGTCA
 993  141_HRV61     ACAAGAGATGAAATGAGTGTAGAAAGTTTCTTGGGTAGATCAGGGTGCATACATATGTCA
 994  142_HRV61a    ACAAGAGATGAAATGAGTGTAGAAAGTTTCTTGGGTAGATCAGGGTGCATACATATGTCA
 995  143_HRV61b    ACAAGAGATGAAATGAGTGTAGAAAGTTTCTTGGGTAGATCAGGGTGCATACATATGTCA
 996  144_HRV96     ACGAGAGATGAAATGAGCATTGAGAGCTTTTTGGGTAGATCAGGGTGTATACACATGTCA
 997  145_HRV96b    ACGAGAGATGAAATGAGCATTGAGAGCTTTTTGGGTAGATCAGGGTGTATACACATGTCA
 998  146_HRV96a    ACGAGAGATGAAATGAGCATTGAGAGCTTTTTGGGTAGATCAGGGTGTATACACATGTCA
 999   90_HRV16a|   ACATTGGATGAAATGAGTGTGGAAAGCTTCCTAGGCAGATCGGGGTGCATCCATGAATCA
1000   91_HRV16b|   ACATTGGATGAAATGAGTGTGGAAAGCTTCCTAGGCAGATCGGGGTGCATCCATGAATCA
1001   92_1AYM_A    ACATTGGATGAAATGAGTGTGGAAAGCTTCCTAGGCAGATCGGGGTGCATCCATGAATCA
1002   93_HRV81a|   ACACTGGATGAAATGAGTGTAGAAAGTTTTTTAGGCAGATCAGGTTGCATTCATGAATCC
1003   94_HRV81b|   ACACTGGATGAAATGAGTGTAGAAAGTTTTTTAGGCAGATCAGGTTGCATTCATGAATCC
1004   95_HRV81     ACACTGGATGAAATGAGTGTAGAAAGTTTTTTAGGCAGATCAGGTTGCATTCATGAATCC
1005  147_HRV2      ACAAGAGATGAAATGAGTTTAGAGAGTTTTCTTGGCAGATCAGGATGCATACATGAATCT
1006  148_HRV2a|    ACAAGAGATGAAATGAGTTTAGAGAGTTTTCTTGGCAGATCAGGATGCATACATGAATCT
1007  149_HRV2b|    ACAAGAGATGAAATGAGTTTAGAGAGTTTTCTTGGCAGATCAGGATGCATACATGAATCT
1008  150_HRV49a    ACAAGAGATGAAATGAGTTTAGAGAGTTTTCTTGGTAGGTCAGGGTGTATACATGAATCC
1009  151_HRV49b    ACAAGAGATGAAATGAGTTTAGAGAGTTTTCTTGGTAGGTCAGGGTGTATACATGAATCC
1010  152_HRV49     ACAAGAGATGAAATGAGTTTAGAGAGTTTTCTTGGTAGGTCAGGGTGTATACATGAATCC
1011  153_HRV23a    ACAAGAGATGAAATGAGTTTAGAAAGTTTCCTTGGTAGGTCAGGGTGTATACATGAATCT
1012  154_HRV23b    ACAAGAGATGAAATGAGTTTAGAAAGTTTCCTTGGTAGGTCAGGGTGTATACATGAATCT
1013  155_HRV23     ACAAGAGATGAAATGAGTTTAGAAAGTTTCCTTGGTAGGTCAGGGTGTATACATGAATCT
1014  156_HRV30a    ACAAGGGATGAAATGAGTTTAGAAAGCTTTCTTGGTAGATCAGGATGTATACACGAGTCT
1015  157_HRV30b    ACAAGGGATGAAATGAGTTTAGAAAGCTTTCTTGGTAGATCAGGATGTATACACGAGTCT
1016  158_HRV30     ACAAGGGATGAAATGAGTTTAGAAAGCTTTCTTGGTAGATCAGGATGTATACACGAGTCT
1017  159_HRV7      ACAAGGGATGAAACTAGTATAGAGAGTTTCTTAGGTAGATCTGGATGTATTGCTAAAGTT
1018  160_HRV7b|    ACAAGGGATGAAACTAGTATAGAGAGTTTCTTAGGTAGATCTGGATGTATTGCTAAAGTT
1019  161_HRV7a|    ACAAGGGATGAAACTAGTATAGAGAGTTTCTTAGGTAGATCTGGATGTATTGCTAAAGTT
1020  162_HRV88     ACAAGGGATGAAACCAGCATTGAAAGCTTTCTGGGTAGGTCTGGATGCATAGCAAAAATT
1021  163_HRV88a    ACAAGGGATGAAACCAGCATTGAAAGCTTTCTGGGTAGGTCTGGATGCATAGCAAAAATT
1022  164_HRV88b    ACAAGGGATGAAACCAGCATTGAAAGCTTTCTGGGTAGGTCTGGATGCATAGCAAAAATT
1023  165_HRV36a    ACAAGAGATGAGACAAGTATTGAAAGCTTCTTAGGTAGGTCAGGGTGCATAGCTATGATA
1024  166_HRV36b    ACAAGAGATGAGACAAGTATTGAAAGCTTCTTAGGTAGGTCAGGGTGCATAGCTATGATA
1025  167_HRV36     ACAAGAGATGAGACAAGTATTGAAAGCTTCTTAGGTAGGTCAGGGTGCATAGCTATGATA
1026  168_HRV89a    ACAAGGGATGAAACAAGTATTGAGAGTTTCTTAGGTAGGTCAGGGTGTATCGCTATGATA
1027  169_HRV89b    ACAAGGGATGAAACAAGTATTGAGAGTTTCTTAGGTAGGTCAGGGTGTATCGCTATGATA
1028  170_HRV89     ACAAGGGATGAAACAAGTATTGAGAGTTTCTTAGGTAGGTCAGGGTGTATCGCTATGATA
1029  171_HRV58     ACAAGAGATGAAACTAGCATTGAAAGCTTTTTAGGTAGATCTGGTTGCATTGCTATCATA
1030  172_HRV58a    ACAAGAGATGAAACTAGCATTGAAAGCTTTTTAGGTAGATCTGGTTGCATTGCTATCATA
1031  173_HRV58b    ACAAGAGATGAAACTAGCATTGAAAGCTTTTTAGGTAGATCTGGTTGCATTGCTATCATA
1032  174_HRV12a    ACTAGAGATGAGATGTCAATTGAATCTTTCCTTGGTCGGTCCGGATGCATTTCAATTATC
1033  175_HRV12b    ACTAGAGATGAGATGTCAATTGAATCTTTCCTTGGTCGGTCCGGATGCATTTCAATTATC
1034  176_HRV12     ACTAGAGATGAGATGTCAATTGAATCTTTCCTTGGTCGGTCCGGATGCATTTCAATTATC
1035  177_HRV78a    ACAAGAGATGAAATGAGCATTGAAAGTTTCCTCGGAAGATCAGGTTGTGCAACAATTATG
1036  178_HRV78b    ACAAGAGATGAAATGAGCATTGAAAGTTTCCTCGGAAGATCAGGTTGTGCAACAATTATG
1037  179_HRV78     ACAAGAGATGAAATGAGCATTGAAAGTTTCCTCGGAAGATCAGGTTGTGCAACAATTATG
1038  180_HRV20     ACCCGTGATGAAATGAGTGTGGAAAGTTTTCTTGGTAGATCTGGTTGCATTGCTATCATA
1039  181_HRV20a    ACCCGTGATGAAATGAGTGTGGAAAGTTTTCTTGGTAGATCTGGTTGCATTGCTATCATA
1040  182_HRV20b    ACCCGTGATGAAATGAGTGTGGAAAGTTTTCTTGGTAGATCTGGTTGCATTGCTATCATA
```

FIG. D10 CONT'D 06.trace                                                                                          9/20/2007 5:04 PM

```
1041 183_HRV68      ACAAGGGATGAAATGAGCATAGAGAGCTTCCTCGGTAGGTCAGGTTGCATTGCAATCATA
1042 184_HRV68a     ACAAGGGATGAAATGAGCATAGAGAGCTTCCTCGGTAGGTCAGGTTGCATTGCAATCATA
1043 185_HRV68b     ACAAGGGATGAAATGAGCATAGAGAGCTTCCTCGGTAGGTCAGGTTGCATTGCAATCATA
1044 186_HRV28      ACCCGTGATGAAATGAGTATAGAGAGTTTCTTAGGTAGGTCTAGTTGCATTGCAATAATC
1045 187_HRV28a     ACCCGTGATGAAATGAGTATAGAGAGTTTCTTAGGTAGGTCTAGTTGCATTGCAATAATC
1046 188_HRV28b     ACCCGTGATGAAATGAGTATAGAGAGTTTCTTAGGTAGGTCTAGTTGCATTGCAATAATC
1047 189_HRV53a     ACCCGGGATGAAATGAGCATTGAAAGTTTCTTAGGCAGATCAAGTTGCATTGCTGAGATC
1048 190_HRV53b     ACCCGGGAAATGAAATGAGCATTGAAAGTTTCTTAGGCAGATCAAGTTGCATTGCTGAGATC
1049 191_HRV53      ACCCGGGATGAAATGAGCATTGAAAGTTTCTTAGGCAGATCAAGTTGCATTGCTGAGATC
1050 192_HRV46a     ACAAAAGATGAAATGAGTATAGAAAGTTTTCTAGGAAGGTCAGGCTGCATTGCCATTATT
1051 193_HRV46b     ACAAAAGATGAAATGAGTATAGAAAGTTTTCTAGGAAGGTCAGGCTGCATTGCCATTATT
1052 194_HRV46      ACAAAAGATGAAATGAGTATAGAAAGTTTTCTAGGAAGGTCAGGCTGCATTGCCATTATT
1053 195_HRV80a     ACAAAGGATGAGATGAGCATTGAAAGTTTCTTAGGAAGATCTGGTTGTGTTGCTATCATT
1054 196_HRV80b     ACAAAGGATGAGATGAGCATTGAAAGTTTCTTAGGAAGATCTGGTTGTGTTGCTATCATT
1055 197_HRV80      ACAAAGGATGAGATGAGCATTGAAAGTTTCTTAGGAAGATCTGGTTGTGTTGCTATCATT
1056 198_HRV51      ACTAGAGATGAAATGAGTATAGAGAGTTTCTTGGGTAGATCTGCTTGCGTAGCAATCATC
1057 199_HRV51a     ACTAGAGATGAAATGAGTATAGAGAGTTTCTTGGGTAGATCTGCTTGCGTAGCAATCATC
1058 200_HRV51b     ACTAGAGATGAAATGAGTATAGAGAGTTTCTTGGGTAGATCTGCTTGCGTAGCAATCATC
1059 201_HRV65a     ACCAGAGATGAGATGAGCGTAGAGAGTTTCCTGGGCAGATCTGCCTGCATAGCAGTCATT
1060 202_HRV65b     ACCAGAGATGAGATGAGCGTAGAGAGTTTCCTGGGCAGATCTGCCTGCATAGCAGTCATT
1061 203_HRV65      ACCAGAGATGAGATGAGCGTAGAGAGTTTCCTGGGCAGATCTGCCTGCATAGCAGTCATT
1062 204_HRV71a     ACTAGGGATGAAATGAGCATTGAGAGCTTCTTGGGCAGATCTGCATGCATAGCTACCATA
1063 205_HRV71b     ACTAGGGAAATGAAATGAGCATTGAGAGCTTCTTGGGCAGATCTGCATGCATAGCTACCATA
1064 206_HRV71      ACTAGGGATGAAATGAGCATTGAGAGCTTCTTGGGCAGATCTGCATGCATAGCTACCATA
1065 207_HRV8       ACTAGGCATGAGACATCACTGGAATCTTTCTTGGGTAGAGCAGGATGCATTAAAATCATT
1066 208_HRV95      ACTAGGTATGAGACATCACTGGAATCTTTCTTGGGTAGAGCAGGATGCATTAAAATTATT
1067 209_HRV45      ACCAGACATGAAACCTCCATTGAATCTTTTTGGGTAGGGCTGGATGTGTGGCCAATATT
1068 210_HRV45a     ACCAGACATGAAACCTCCATTGAATCTTTTTGGGTAGGGCTGGATGTGTGGCCAATATT
1069 211_HRV45b     ACCAGACATGAAACCTCCATTGAATCTTTTTGGGTAGGGCTGGATGTGTGGCCAATATT
1070 GROUP_1        AC-----ATGA-A------T-GA----TT--T-GG--G--C----TG-------------
1071
1072  1_HRV1A1|d    AGAATAAAGGTTGATTACACTGAC---------------TATAATGGA---CAGGACATA
1073  2_HRV1A2|d    AGAATAAAGGTTGATTACACTGAC---------------TATAATGGA---CAGGACATA
1074  3_HRV1A|cD    AGAATAAAGGTTGATTACACTGAC---------------TATAATGGA---CAGGACATA
1075  4_HRV1B1|d    AGAATAAAGGTTGATTACAATGAC---------------TACAATGGA---GTGAACAAA
1076  5_HRV1B2|d    AGAATAAAGGTTGATTACAATGAC---------------TACAATGGA---GTGAACAAA
1077  6_HRV1B       AGAATAAAGGTTGATTACAATGAC---------------TACAATGGA---GTGAACAAA
1078  7_HRV40a|d    ACAATTACAGTGGATAACAGTTTG---------------GAATATG------ATGACCAC
1079  8_HRV40b|d    ACAATTACAGTGGATAACAGTTTG---------------GAATATG------ATGACCAC
1080  9_HRV40       ACAATTACAGTGGATAACAGTTTG---------------GAATATG------ATGACCAC
1081 10_HRV85       ACAATTACTGTGAATAACAACCTA---------------GATTATG------ATGAAAAT
1082 11_HRV85a|     ACAATTACTGTGAATAACAACCTA---------------GATTATG------ATGAAAAT
1083 12_HRV85b|     ACAATTACTGTGAATAACAACCTA---------------GATTATG------ATGAAAAT
1084 13_HRV56a|     ACTATAACTGTGGATAATGATGTA---------------GATTATA------ATTCAAAG
1085 14_HRV56b|     ACTATAACTGTGGATAATGATGTA---------------GATTATA------ATTCAAAG
1086 15_HRV56       ACTATAACTGTGGATAATGATGTA---------------GATTATA------ATTCAAAG
1087 16_HRV54       ACCATTACAATTCAAAATGATGTA---------------GAATACA------ATGATCAC
1088 17_HRV98       ACTATCACTATTCAAAATGATGTA---------------GAATATA------ACGATCAT
1089 18_HRV59a|     ACTATTACTGTCAATAAAGACATA---------------AAATATG------ATGATGGA
1090 19_HRV59b|     ACTATTACTGTCAATAAAGACATA---------------AAATATG------ATGATGGA
1091 20_HRV59       ACTATTACTGTCAATAAAGACATA---------------AAATATG------ATGATGGA
1092 21_HRV63       ACTATCACTGTTGACAAAACCATT---------------GACTATG------ACACTGGA
1093 22_HRV63b|     ACTATCACTGTTGACAAAACCATT---------------GACTATG------ACACTGGA
1094 23_HRV63a|     ACTATCACTGTTGACAAAACCATT---------------GACTATG------ACACTGGA
1095 24_HRV39       ACAATTACTATGAAGAAGGAG------------------AACTATA------ATGATCAT
1096 25_HRV39a|     ACAATTACTATGAAGAAGGAG------------------AACTATA------ATGATCAT
1097 26_HRV39b|     ACAATTACTATGAAGAAGGAG------------------AACTATA------ATGACACAT
1098 27_HRV10a|     ACAATAACTGTTAATAATACAAGA---------------CCCTACA------ATGAACAC
1099 28_HRV10b|     ACAATAACTGTTAATAATACAAGA---------------CCCTACA------ATGAACAC
1100 29_HRV10       ACAATAACTGTTAATAATACAAGA---------------CCCTACA------ATGAACAC
1101 30_HRV100a     ACAATTACTGTAAGTAAAATGAAA---------------AATTATA------ATGAGCAC
1102 31_HRV100b     ACAATTACTGTAAGTAAAATGAAA---------------AATTATA------ATGAGCAC
1103 32_HRV100      ACAATTACTGTAAGTAAAATGAAA---------------AATTATA------ATGAGCAC
1104 33_HRV66       ACAATTAATGTGGATAGCACAAAA---------------ACATATG------ATGAATCC
1105 34_HRV66b|     ACAATTAATGTGGATAGCACAAAA---------------ACATATG------ATGAATCC
```

FIG. D10 CONT'D

```
06.trace                                                                        9/20/2007 5:04 PM 1106  35_HRV66a|   ACAATTAATGTGGATAGCACAAAA---------------ACATATG------ATGAATCC
1107  36_HRV77a|   ACAATAAATGTAGAAGATGGTAAA---------------ACTTATG------ATGAATCT
1108  37_HRV77b|   ACAATAAATGTAGAAGATGGTAAA---------------ACTTATG------ATGAATCT
1109  38_HRV77    ACAATAAATGTAGAAGATGGTAAA---------------ACTTATG------ATGAATCT
1110  39_HRV62a   ACAATTGAA---------ACAACG---------------CTTAGTC------ATAAAGAT
1111  40_HRV62b   ACAATTGAA---------ACAACG---------------CTTAGTC------ATAAAGAT
1112  41_HRV25    ACAATTGAA---------ACAAAA---------------CTTAAAC------ATGATGAA
1113  42_HRV29a   ACAATAAAA---------GCAAAT---------------CAGGCAC------ATGACGCC
1114  43_HRV29b   ACAATAAAA---------GCAAAT---------------CAGGCAC------ATGACGCC
1115  44_HRV44a   ACAATAAAG---------ACAAAT---------------CAGGCAC------ACAATACC
1116  45_HRV44b   ACAATAAAG---------ACAAAT---------------CAGGCAC------ACAATACC
1117  46_HRV31    ATAATAGAA---------CCAGAT---------------GGACTCC------ATGATAGC
1118  47_HRV31a|   ATAATAGAA---------CCAGAT---------------GGACTCC------ATGATAGC
1119  48_HRV31b|   ATAATAGAA---------CCAGAT---------------GGACTCC------ATGATAGC
1120  49_HRV47    ACAATAAAA---------TCAGAT---------------GAGCAAC------ACATTAAT
1121  50_HRV47a|   ACAATAAAA---------TCAAAT---------------GAGCAAC------ACATTAAT
1122  51_HRV47b|   ACAATACAA---------TCAAAT---------------GAGCAAC------ACATTAAT
1123  52_HRV11    AAGTTAATTGTGCAGTATGAAGAC---------------TATAAT------GGAAAGAAA
1124  53_HRV11b|   AAGTTAATTGTGCAGTATGAAGAC---------------TATAAT------GGAAAGAAA
1125  54_HRV11a|   AAGTTAATTGTGCAGTATGAAGAC---------------TATAAT------GGAAAGAAA
1126  55_HRV76    AAGCTAGTTGTAGAATATGAGGGA---------------TATGAT------GATACAAAA
1127  56_HRV76b|   AAGCTAGTTGTAGAATATGAGGGA---------------TATGAT------GATACAAAA
1128  57_HRV76a|   AAGCTAGTTGTAGAATATGAGGGA---------------TATGAT------GATACAAAA
1129  58_HRV33    AAATTAGTAGTGAAATATGAAGAC---------------TATAAT------GAGAAAAAG
1130  59_HRV33b|   AAATTAGTAGTGAAATATGAAGAC---------------TATAAT------GAGAAAAAG
1131  60_HRV33a|   AAATTAGTAGTGAAATATGAAGAC---------------TATAAT------GAGAAAAAG
1132  61_HRV24a|   AAGTTGACTGTGGATTAT---GAC---------------AATTAT------GATACAAAA
1133  62_HRV24b|   AAGTTGACTGTGGATTAT---GAC---------------AATTAT------GATACAAAA
1134  63_HRV24    AAGTTGACTGTGGATTAT---GAC---------------AATTAT------GATACAAAA
1135  64_HRV90    AAATTAGTTGTAAACTAT---GAT---------------AATTAT------GATGAAAAC
1136  65_HRV90a|   AAATTAGTTGTAAACTAT---GAT---------------AATTAT------GATGAAAAC
1137  66_HRV90b|   AAATTAGTTGTAAACTAT---GAT---------------AATTAT------GATGAAAAC
1138  67_HRV34    AAACTTGTTGTAGATTATGAAAAT---------------TACAATGCA---AAAACAAAG
1139  68_HRV34b|   AAACTTGTTGTAGATTATGAAAAT---------------TACAATGCA---AAAACAAAG
1140  69_HRV34a|   AAACTTGTTGTAGATTATGAAAAT---------------TACAATGCA---AAAACAAAG
1141  70_HRV50a|   AAATTAGTTGTTGATTATGATGGT---------------TACAATGAG---GAAACAAAG
1142  71_HRV50b|   AAATTAGTTGTTGATTATGATGGT---------------TACAATGAG---GAAACAAAG
1143  72_HRV50    AAATTAGTTGTTGATTATGATGGT---------------TACAATGAG---GAAACAAAG
1144  73_HRV18a|   AAGTTAGTTGTACATTATGAAGAT---------------TATAATGCA---GAAACAAGG
1145  74_HRV18b|   AAGTTAGTTGTACATTATGAAGAT---------------TATAATGCA---GAAACAAGG
1146  75_HRV18    AAGTTAGTTGTACATTATGAAGAT---------------TATAATGCA---GAAACAAGG
1147  76_HRV55    GAGTTAGTTGTTCATTATGAAGAA---------------TATAACAAA---GAGGGAAAA
1148  77_HRV55b|   GAGTTAGTTGTTCATTATGAAGAA---------------TATAACAAA---GAGGGAAAA
1149  78_HRV55a|   GAGTTAGTTGTTCATTATGAAGAA---------------TATAACAAA---GAGGGAAAA
1150  79_HRV57    GAGCTTAAGGTAAAATATGAAAAT---------------TACAACACA---GAG------
1151  80_HRV57a|   GAGCTTAAGGTAAAATATGAAAAT---------------TACAACACA---GAG------
1152  81_HRV57b|   GAGCTTAAGGTAAAATATGAAAAT---------------TACAACACA---GAG------
1153  82_HRV21    AAATTAGTAGTTAACTATGATAAT---------------TACAATACT---GGAGAAAAT
1154  83_HRVHan   AAATTAATAGTTAACTATGACAAC---------------TACAATACT---GGAGAAAAT
1155  84_HRV43    ACACTTGAAGTAAATTATGATGAT---------------TATAATGGG---ACAGGCATA
1156  85_HRV43b|   ACACTTGAAGTAAATTATGATGAT---------------TATAATGGG---ACAGGCATA
1157  86_HRV43a|   ACACTTGAAGTAAATTATGATGAT---------------TATAATGGG---ACAGGCATA
1158  87_HRV75    ACACTTGAGATGGATTATACAAAC---------------TATAATGGA---GAAGGCAAA
1159  88_HRV75b|   ACACTTGAGATGGATTATACAAAC---------------TATAATGGA---GAAGGCAAA
1160  89_HRV75a|   ACACTTGAGATGGATTATACAAAC---------------TATAATGGA---GAAGGCAAA
1161  96_HRV9a|d   AAATTGAATATTGATTACAGTGAC---------------TATGATAAG---AGTGTTGAA
1162  97_HRV9b|d   AAATTGAATATTGATTACAGTGAC---------------TATGATAAG---AGTGTTGAA
1163  98_HRV9     AAATTGAATATTGATTACAGTGAC---------------TATGATAAG---AGTGTTGAA
1164  99_HRV32    AAATTAGATATTGATTATACCAAT---------------TACAATAAA---AGTGTTAAG
1165 100_HRV32a   AAATTAGATATTGATTATACCAAT---------------TACAATAAA---AGTGTTAAG
1166 101_HRV32b   AAATTAGATATTGATTATACCAAT---------------TACAATAAA---AGTGTTAAG
1167 102_HRV67    AAATTGAATATTGATTATAATGCA---------------TATGATGAA---AGTAGGGAC
1168 103_HRV67a   AAATTGAATATTGATTATAATGCA---------------TATGATGAA---AGTAGGGAC
1169 104_HRV67b   AAATTGAATATTGATTATAATGCA---------------TATGATGAA---AGTAGGGAC
1170 105_HRV15    GATTTGAAAATACATTATGAAGAT---------------TATAATAAA---GATGGGAAA
```

FIG. D10 CONT'D 06.trace                                                                9/20/2007 5:04 PM

```
1171 106_HRV15a   GATTTGAAAATACATTATGAAGAT---------------TATAATAAA---GATGGGAAA
1172 107_HRV15b   GATTTGAAAATACATTATGAAGAT---------------TATAATAAA---GATGGGAAA
1173 108_HRV74a   CATCTAAAAATTGATTATACAAAC---------------TATAATGTT---AAAGGGAAG
1174 109_HRV74b   CATCTAAAAATTGATTATACAAAC---------------TATAATGTT---AAAGGGAAG
1175 110_HRV74    CATCTAAAAATTGATTATACAAAC---------------TATAATGTT---AAAGGGAAG
1176 111_HRV38a   AATCTTGACATAGATTACATTAAT---------------TACAACTCT---GAAGACAAA
1177 112_HRV38b   AATCTTGACATAGATTACATTAAT---------------TACAACTCT---GAAGACAAA
1178 113_HRV38    AATCTTGACATAGATTACATTAAT---------------TACAACTCT---GAAGACAAA
1179 114_HRV60    AAAATTAGAAATTGACTATAGTAAC---------------TACAATGAG---GAGAATAAA
1180 115_HRV60a   AAAATTAGAAATTGACTATAGTAAC---------------TACAATGAG---GAGAATAAA
1181 116_HRV60b   AAAATTAGAAATTGACTATAGTAAC---------------TACAATGAG---GAGAATAAA
1182 117_HRV64a   GATTTAAAAGTAAATTATACTGGG---------------TATAATGAT---GAAGGTAAC
1183 118_HRV64b   GATTTAAAAGTAAATTATACTGGG---------------TATAATGAT---GAAGGTAAC
1184 119_HRV64    GATTTAAAAGTAAATTATACTGGG---------------TATAATGAT---GAAGGTAAC
1185 120_HRV94a   CATCTAGAGATCAAGTATGATGGT---------------TACAATGAT---GCTGGCAAC
1186 121_HRV94b   CATCTAGAGATCAAGTATGATGGT---------------TACAATGAT---GCTGGCAAC
1187 122_HRV94    CATCTAGAGATCAAGTATGATGGT---------------TACAATGAT---GCTGGCAAC
1188 123_HRV22    CACTTAGAAGTAAAATACACAGGG---------------TATAATGAA---GAGGGTAAT
1189 124_HRV22a   CACTTAGAAGTAAAATACACAGGG---------------TATAATGAA---GAGGGTAAT
1190 125_HRV22b   CACTTAGAAGTAAAATACACAGGG---------------TATAATGAA---GAGGGTAAT
1191 126_HRV82    CACCTAAATGTCAGATACACTG------------------ATTATAAT---GAAGGTAAT
1192 127_HRV82b   CACCTAAATGTCAGATACACTG------------------ATTATAAT---GAAGGTAAT
1193 128_HRV82a   CACCTAAATGTCAGATACACTG------------------ATTATAAT---GAAGGTAAT
1194 129_HRV19    GAGCTCCAATTAGATTATACCAAT---------------TACAATCAA---GAAAATAAT
1195 130_HRV19a   GAGCTCCAATTAGATTATACCAAT---------------TACAATCAA---GAAAATAAT
1196 131_HRV19b   GAGCTCCAATTAGATTATACCAAT---------------TACAATCAA---GAAAATAAT
1197 132_HRV13    ACCATGAACATAGATTATACTAAT---------------TATGATGAT---TCTGTTAAT
1198 133_HRV13a   ACCATGAACATAGATTATACTAAT---------------TATGATGAT---TCTGTTAAT
1199 134_HRV13b   ACCATGAACATAGATTATACTAAT---------------TATGATGAT---TCTGTTAAT
1200 135_HRV41    ACTTTGAATATAGATTATACTGAT---------------TATGATGAT---TCTATCCAG
1201 136_HRV41a   ACTTTGAATATAGATTATACTGAT---------------TATGATGAT---TCTATCCAG
1202 137_HRV41b   ACTTTGAATATAGATTATACTGAT---------------TATGATGAT---TCTATCCAG
1203 138_HRV73    ACTATGAATATAAATTATGAAAAT---------------TATGATGAT---GCTCCTGAA
1204 139_HRV73b   ACTATGAATATAAATTATGAAAAT---------------TATGATGAT---GCTCCTGAA
1205 140_HRV73a   ACTATGAATATAAATTATGAAAAT---------------TATGATGAT---GCTCCTGAA
1206 141_HRV61    ACATTAAATATAAACTATGATAAC---------------TATGATGAT---TCTATTGAA
1207 142_HRV61a   ACATTAAATATAAACTATGATAAC---------------TATGATGAT---TCTATTGAA
1208 143_HRV61b   ACATTAAATATAAACTATGATAAC---------------TATGATGAT---TCTATTGAA
1209 144_HRV96    ACATTAAACATAGATTATGACAAT---------------TATGATGAC---TCCCCTAAG
1210 145_HRV96b   ACATTAAACATAGATTATGACAAT---------------TATGATGAC---TCCCCTAAG
1211 146_HRV96a   ACATTAAACATAGATTATGACAAT---------------TATGATGAC---TCCCCTAAG
1212 90_HRV16a|   GTGTTGGATATTGTGGACAATTAC---------------AATGAT-----------CAA
1213 91_HRV16b|   GTGTTGGATATTGTGGACAATTAC---------------AATGAT-----------CAA
1214 92_1AYM_A    GTGTTGGATATTGTGGACAATTAC---------------AATGAT-----------CAA
1215 93_HRV81a|   ATATTGGACATTAAAGAGGATTAC---------------AATACC-----------CAG
1216 94_HRV81b|   ATATTGGACATTAAAGAGGATTAC---------------AATACC-----------CAG
1217 95_HRV81     ATATTGGACATTAAAGAGGATTAC---------------AATACC-----------CAG
1218 147_HRV2     AAATTAGAGGTTACACTTGCAAAT---------------TATAACA--------AGGAG
1219 148_HRV2a|   AAATTAGAGGTTACACTTGCAAAT---------------TATAACA--------AGGAG
1220 149_HRV2b|   AAATTAGAGGTTACACTTGCAAAT---------------TATAACA--------AGGAG
1221 150_HRV49a   AAACTAGAGGTCACACTTACAAAT---------------TACAATG--------AAAAT
1222 151_HRV49b   AAACTAGAGGTCACACTTACAAAT---------------TACAATG--------AAAAT
1223 152_HRV49    AAACTAGAGGTCACACTTACAAAT---------------TACAATG--------AAAAT
1224 153_HRV23a   AAATTAAAAGTTGAGATCGGAAAC---------------TATGATG--------AAAAC
1225 154_HRV23b   AAATTAAAAGTTGAGATCGGAAAC---------------TATGATG--------AAAAC
1226 155_HRV23    AAATTAAAAGTTGAGATCGGAAAC---------------TATGATG--------AAAAC
1227 156_HRV30a   AAATTAGAACTTGAGCTTGCACAC---------------TATGATA--------AAAAG
1228 157_HRV30b   AAATTAGAACTTGAGCTTGCACAC---------------TATGATA--------AAAAG
1229 158_HRV30    AAATTAGAACTTGAGCTTGCACAC---------------TATGATA--------AAAAG
1230 159_HRV7     AAACTTGACACAA------CACAGGGT---------GACTATGACACAGGCAAAGGTGTT
1231 160_HRV7b|   AAACTTGACACAA------CACAGGGT---------GACTATGACACAGGCAAAGGTGTT
1232 161_HRV7a|   AAACTTGACACAA------CACAGGGT---------GACTATGACACAGGCAAAGGTGTT
1233 162_HRV88    AAACTTGACACAA------ATGAAGGT---------GATTACGACACA---ATAGGTGTT
1234 163_HRV88a   AAACTTGACACAA------ATGAAGGT---------GATTACGACACA---ATAGGTGTT
1235 164_HRV88b   AAACTTGACACAA------ATGAAGGT---------GATTACGACACA---ATAGGTGTT
```

FIG. D10 CONT'D 06.trace                                                                9/20/2007 5:04 PM

```
1236 165_HRV36a    GAATTTAGCACAAGTAGTGATAAAGAT---------GAACATGATGAA---ATTGGCAAG
1237 166_HRV36b    GAATTTAGCACAAGTAGTGATAAAGAT---------GAACATGATGAA---ATTGGCAAG
1238 167_HRV36     GAATTTAGCACAAGTAGTGATAAAGAT---------GAACATGATGAA---ATTGGCAAG
1239 168_HRV89a    GAATTTAATACAAGTAGTGATAAAACT---------GAACATGATAAA---ATTGGTAAA
1240 169_HRV89b    GAATTTAATACAAGTAGTGATAAAACT---------GAACATGATAAA---ATTGGTAAA
1241 170_HRV89     GAATTTAATACAAGTAGTGATAAAACT---------GAACATGATAAA---ATTGGTAAA
1242 171_HRV58     AAATTTAACACAA------ATAAGACT---------AATTATGATGAC---ATAGGTGTA
1243 172_HRV58a    AAATTTAACACAA------ATAAGACT---------AATTATGATGAC---ATAGGTGTA
1244 173_HRV58b    AAATTTAACACAA------ATAAGACT---------AATTATGATGAC---ATAGGTGTA
1245 174_HRV12a    GAATTGGATTTAGACCATGAAGGT---------------TATTCAGCA---GAAGGGAAA
1246 175_HRV12b    GAATTGGATTTAGACCATGAAGGT---------------TATTCAGCA---GAAGGGAAA
1247 176_HRV12     GAATTGGATTTAGACCATGAAGGT---------------TATTCAGCA---GAAGGGAAA
1248 177_HRV78     AGACTAGAATTGGACCACACTGAT---------------TACAATGCT---GAAGGGAAA
1249 178_HRV78b    AGACTAGAATTGGACCACACTGAT---------------TACAATGCT---GAAGGGAAA
1250 179_HRV78     AGACTAGAATTGGACCACACTGAT---------------TACAATGCT---GAAGGGAAA
1251 180_HRV20     CATACTGACTTAGATCATGAAGCACAA---------CAATATAATGCA---CCCGGAAAA
1252 181_HRV20a    CATACTGACTTAGATCATGAAGCACAA---------CAATATAATGCA---CCCGGAAAA
1253 182_HRV20b    CATACTGACTTAGATCATGAAGCACAA---------CAATATAATGCA---CCCGGAAAA
1254 183_HRV68     CATACTGACTTAGATCACAATGAGGAT---------CAGTACAATGCA---CCTGGAAAA
1255 184_HRV68a    CATACTGACTTAGATCACAATGAGGAT---------CAGTACAATGCA---CCTGGAAAA
1256 185_HRV68b    CATACTGACTTAGATCACAATGAGGAT---------CAGTACAATGCA---CCTGGAAAA
1257 186_HRV28     CATACTGATGTTGTGCATGAAACAGAC---------AAGTACAACCAC---CCAGGGAAG
1258 187_HRV28a    CATACTGATGTTGTGCATGAAACAGAC---------AAGTACAACCAC---CCAGGGAAG
1259 188_HRV28b    CATACTGATGTTGTGCATGAAACAGAC---------AAGTACAACCAC---CCAGGGAAG
1260 189_HRV53a    CATACCAATTTAGACCAT---ACTG-----------GATACAATGAG---CCTGGGAAA
1261 190_HRV53b    CATACCAATTTAGACCAT---ACTG-----------GATACAATGAG---CCTGGGAAA
1262 191_HRV53     CATACCAATTTAGACCAT---ACTG-----------GATACAATGAG---CCTGGGAAA
1263 192_HRV46a    GAGACAGAATTGAATCATGAAGAAGGG---------AAATACAATGCA---GAAGATCAA
1264 193_HRV46b    GAGACAGAATTGAATCATGAAGAAGGG---------AAATACAATGCA---GAAGATCAA
1265 194_HRV46     GAGACAGAATTGAATCATGAAGAAGGG---------AAATACAATGCA---GAAGATCAA
1266 195_HRV80a    GAAACCAAATTAAACCATGAAACAGAC---------ATGTACAATGCT---GATGGTCAG
1267 196_HRV80b    GAAACCAAATTAAACCATGAAACAGAC---------ATGTACAATGCT---GATGGTCAG
1268 197_HRV80     GAAACCAAATTAAACCATGAAACAGAC---------ATGTACAATGCT---GATGGTCAG
1269 198_HRV51     CATACAAACCTTGAGCATGTTGAAGCAGACAGAAGCCTACAATGCA---AAAGGGAAA
1270 199_HRV51a    CATACAAACCTTGAGCATGTTGAAGCAGACAGAAGCCTACAATGCA---AAAGGGAAA
1271 200_HRV51b    CATACAAACCTTGAGCATGTTGAAGCAGACAGAAGCCTACAATGCA---AAAGGGAAA
1272 201_HRV65a    CACACAGATCTTAAACATGACCATGAAGGCCAAAATGTTTACAATGAC---GAAGGCAGA
1273 202_HRV65b    CACACAGATCTTAAACATGACCATGAAGGCCAAAATGTTTACAATGAC---GAAGGCAGA
1274 203_HRV65     CACACAGATCTTAAACATGACCATGAAGGCCAAAATGTTTACAATGAC---GAAGGCAGA
1275 204_HRV71a    CACACTAAATTAGTACATGGAGAGGAGGG------TGTTTATAATATG---AAAGGTAAC
1276 205_HRV71b    CACACTAAATTAGTACATGGAGAGGAGGG------TGTTTATAATATG---AAAGGTAAC
1277 206_HRV71     CACACTAAATTAGTACATGGAGAGGAGGG------TGTTTATAATATG---AAAGGTAAC
1278 207_HRV8      GCATTAGAACTAGATCATGACAAC---------------TATGATGAA------------
1279 208_HRV95     GCATTGAACTAGATCATGACAAC---------------TATGATAAA------------
1280 209_HRV45     AGTTTAGACATTAACCATGATGAC---------------TACCAAAAG------------
1281 210_HRV45a    AGTTTAGACATTAACCATGATGAC---------------TACCAAAAG------------
1282 211_HRV45b    AGTTTAGACATTAACCATGATGAC---------------TACCAAAAG------------
1283 GROUP_1       ------------------------------------------------------------
1284
1285 1_HRV1A1|d    AATTTCACAAAATGGAAAATCACACTACAGGAAATGGCACAGATTAGGAGAAAATTTGAA
1286 2_HRV1A2|d    AATTTCACAAAATGGAAAATCACACTACAGGAAATGGCACAGATTAGGAGAAAATTTGAA
1287 3_HRV1A|cD    AATTTCACAAAATGGAAAATCACACTACAGGAAATGGCACAGATTAGGAGAAAATTTGAA
1288 4_HRV1B1|d    AACTTTACAACATGGAAAATCACACTGCAGGAGATGGCACAAATTAGAAGAAAATTCGAA
1289 5_HRV1B2|d    AACTTTACAACATGGAAAATCACACTGCAGGAGATGGCACAAATTAGAAGAAAATTCGAA
1290 6_HRV1B       AACTTTACAACATGGAAAATCACACTGCAGGAGATGGCACAAATTAGAAGAAAATTCGAA
1291 7_HRV40a|d    CACTTTGATAAGTGGCAGATAACCATACAAGAGATGTCACAAATTAGGAGAAAATTTGAA
1292 8_HRV40b|d    CACTTTGATAAGTGGCAGATAACCATACAAGAGATGTCACAAATTAGGAGAAAATTTGAA
1293 9_HRV40       CACTTTGATAAGTGGCAGATAACCATACAAGAGATGTCACAAATTAGGAGAAAATTTGAA
1294 10_HRV85      CACTTTGATCAGTGGCAGATAACTATACAGGAAATGGCACAAATTAGAAGGAAGTTTGAG
1295 11_HRV85a|    CACTTTGATCAGTGGCAGATAACTATACAGGAAATGGCACAAATTAGAAGGAAGTTTGAG
1296 12_HRV85b|    CACTTTGATCAGTGGCAGATAACTATACAGGAAATGGCACAAATTAGAAGGAAGTTTGAG
1297 13_HRV56a|    CATTATAATAAATGGCAAATAACCTTACAAGAAATGGCTCAAGTTAGGCGTAAATTTGAA
1298 14_HRV56b|    CATTATAATAAATGGCAAATAACCTTACAAGAAATGGCTCAAGTTAGGCGTAAATTTGAA
1299 15_HRV56     CATTATAATAAATGGCAAATAACCTTACAAGAAATGGCTCAAGTTAGGCGTAAATTTGAA
1300 16_HRV54     CATTTTAAGAAATGGGATATAACATTACAAGAGATGGCACAAATACGAAGGAAATTTGAA
```

FIG. D10 CONT'D 06.trace                                                                9/20/2007 5:04 PM

```
1301  17_HRV98     CATTTTAGACAATGGGATATAACATTACAAGAAATGGCACAAATTCGAAGAAAATTTGAA
1302  18_HRV59a|   CACTTTCTTAAATGGCCTATAACATTACAAGAGATGGCACAAATTAGGAGAAAATTTGAA
1303  19_HRV59b|   CACTTTCTTAAATGGCCTATAACATTACAAGAGATGGCACAAATTAGGAGAAAATTTGAA
1304  20_HRV59     CACTTTCTTAAATGGCCTATAACATTACAAGAGATGGCACAAATTAGGAGAAAATTTGAA
1305  21_HRV63     CATTTTAATAAATGGCAAATAACATTACAAGAGATGGCACAAATTAGAAGGAAATTTGAA
1306  22_HRV63b|   CATTTTAATAAATGGCAAATAACATTACAAGAGATGGCACAAATTAGAAGGAAATTTGAA
1307  23_HRV63a|   CATTTTAATAAATGGCAAATAACATTACAAGAGATGGCACAAATTAGACGGAAATTTGAA
1308  24_HRV39     AATTTTGTGGATTGGAAAATTACTTTGCAGGAGATGGCACAGGTTAGAAGGAAATTTGAA
1309  25_HRV39a|   AATTTTGTGGATTGGAAAATTACTTTGCAGGAGATGGCACAGGTTAGAAGGAAATTTGAA
1310  26_HRV39b|   AATTTTGTGGATTGGAAAATTACTTTGCAGGAGATGGCACAGGTTAGAAGGAAATTTGAA
1311  27_HRV10a|   ACTTTTGACACATGGCAAATAACTCTACAAGAAATGGCCCAAATTAGAAGGAAATTTGAA
1312  28_HRV10b|   ACTTTTGACACATGGCAAATAACTCTACAAGAAATGGCCCAAATTAGAAGGAAATTTGAA
1313  29_HRV10     ACTTTTGACACATGGCAAATAACTCTACAAGAAATGGCCCAAATTAGAAGGAAATTTGAA
1314  30_HRV100a   ACTTTTGACAAATGGCAAATAACCCTACAGGAAATGGCCCAAATTAGAAGGAAATTTGAA
1315  31_HRV100b   ACTTTTGACAAATGGCAAATAACCCTACAGGAAATGGCCCAAATTAGAAGGAAATTTGAA
1316  32_HRV100    ACTTTTGACAAATGGCAAATAACCCTACAGGAAATGGCCCAAATTAGAAGGAAATTTGAA
1317  33_HRV66     AAATTTAGAACATGGCAAATTACATTGCAAGAAATGGCTCAAATCAGACGCAAATTTGAG
1318  34_HRV66b|   AAATTTAGAACATGGCAAATTACATTGCAAGAAATGGCTCAAATCAGACGCAAATTTGAG
1319  35_HRV66a|   AAATTTAGAACATGGCAAATTACATTGCAAGAAATGGCTCAAATCAGACGCAAATTTGAG
1320  36_HRV77a|   AAATTTAGAAAATGGCAAATTACACTACAAGAAATGGCTCAAATTAGGCGCAAATTTGAA
1321  37_HRV77b|   AAATTTAGAAAATGGCAAATTACACTACAAGAAATGGCTCAAATTAGGCGCAAATTTGAA
1322  38_HRV77     AAATTTAGAAAATGGCAAATTACACTACAAGAAATGGCTCAAATTAGGCGCAAATTTGAA
1323  39_HRV62a    AGATTCAAAACATGGAATATTAACTTACAAGAGATGGCTCAAATCAGGAGAAAGTTTGAA
1324  40_HRV62b    AGATTCAAAACATGGAATATTAACTTACAAGAGATGGCTCAAATCAGGAGAAAGTTTGAA
1325  41_HRV25     AGATTTAAAATATGGAATATCAATTTACAAGAAATGGCTCAAATTAGGAGAAAGTTTGAG
1326  42_HRV29a    AAGTTCGATAAATGGAATGTTAACTTACAAGAAATGGCTCAAATTAGGCGCAAATTTGAA
1327  43_HRV29b    AAGTTCGATAAATGGAATGTTAACTTACAAGAAATGGCTCAAATTAGGCGCAAATTTGAA
1328  44_HRV44a    AAGTTTGATAAATGGAATATCAACTTACAAGAAATGGCTCAAATTAGACGCAAATTTGAA
1329  45_HRV44b    AAGTTTGATAAATGGAATATCAACTTACAAGAAATGGCTCAAATTAGACGCAAATTTGAA
1330  46_HRV31     AAATATAAAGTATGGCACATTAATTTACAAGAGATGGCCCAGATTAGGCGAAAATTTGAA
1331  47_HRV31a|   AAATATAAAGTATGGCACATTAATTTACAAGAGATGGCCCAGATTAGGCGAAAATTTGAA
1332  48_HRV31b|   AAATATAAAGTATGGCACATTAATTTACAAGAGATGGCCCAGATTAGGCGAAAATTTGAA
1333  49_HRV47     AAATTTAAAGTATGGCACATTAATTTACAAGAAATGGCCCAGATCAGGCGTAAATATGAA
1334  50_HRV47a|   AAATTTAAAGTATGGCACATTAATTTACAAGAAATGGCCCAGATCAGGCGTAAATATGAA
1335  51_HRV47b|   AAATTTAAAGTATGGCACATTAATTTTACAAGAAATGGCCCAGATCAGGCGTAAATATGAA
1336  52_HRV11     AACTTTAACACATGGAAAATAAACTTGCAAGAGATGGCACAAATTAGAAGGAAATTTGAA
1337  53_HRV11b|   AACTTTAACACATGGAAAATAAACTTGCAAGAGATGGCACAAATTAGAAGGAAATTTGAA
1338  54_HRV11a|   AACTTTAACACATGGAAAATAAACTTGCAAGAGATGGCACAAATTAGAAGGAAATTTGAA
1339  55_HRV76     AACTTTAAGACATGGAAAATAAACCTACAAGAAATGGCACAAGTTAGAAGAAAATTTGAG
1340  56_HRV76b|   AACTTTAAGACATGGAAAATAAACCTACAAGAAATGGCACAAGTTAGAAGAAAATTTGAG
1341  57_HRV76a|   AACTTTAAGACATGGAAAATAAACCTACAAGAAATGGCACAAGTTAGAAGAAAATTTGAG
1342  58_HRV33     AATTTTATGACATGGAAAATAAACTCTACAAGAGATGGCACAGATTAGGAGGAAATTTGAA
1343  59_HRV33b|   AATTTTATGACATGGAAAATAAACTCTACAAGAGATGGCACAGATTAGGAGGAAATTTGAA
1344  60_HRV33a|   AATTTTATGACATGGAAAATAAACTCTACAAGAGATGGCACAGATTAGGAGGAAATTTGAA
1345  61_HRV24a|   AATTTTTTCAAATGGCAAATAAATCTACAAGAAATGGCCCAAGTCAGAAGAAAATTTGAA
1346  62_HRV24b|   AATTTTTTCAAATGGCAAATAAATCTACAAGAAATGGCCCAAGTCAGAAGAAAATTTGAA
1347  63_HRV24     AATTTTTTCAAATGGCAAATAAATCTACAAGAAATGGCCCAAGTCAGAAGAAAATTTGAA
1348  64_HRV90     AACTTCCATAAATGGCAAATTAACCTGCAAGAGATGGCACAGATTAGAAGAAAATTTGAA
1349  65_HRV90a|   AACTTCCATAAATGGCAAATTAACCTGCAAGAGATGGCACAGATTAGAAGAAAATTTGAA
1350  66_HRV90b|   AACTTCCATAAATGGCAAATTAACCTGCAAGAGATGGCACAGATTAGAAGAAAATTTGAA
1351  67_HRV34     AACTTTATGACATGGCAAATTAATTTACAGGAAATGGCACAGATTAGAAGGAAATTTGAA
1352  68_HRV34b|   AACTTTATGACATGGCAAATTAATTTACAGGAAATGGCACAGATTAGAAGGAAATTTGAA
1353  69_HRV34a|   AACTTTATGACATGGCAAATTAATTTACAGGAAATGGCACAGATTAGAAGGAAATTTGAA
1354  70_HRV50a|   AACTTCAAGAAATGGCAAATCAACCTACAAGAAATGGCACAGATCAGAAGGAAATTTGAG
1355  71_HRV50b|   AACTTCAAGAAATGGCAAATCAACCTACAAGAAATGGCACAGATCAGAAGGAAATTTGAG
1356  72_HRV50     AACTTCAAGAAATGGCAAATCAACCTACAAGAAATGGCACAGATCAGAAGGAAATTTGAG
1357  73_HRV18a|   AACTTTGTAAAATGGCAAATAAATCTACAGGAAATGGCCCAGATTAGGAGAAAATTTGAG
1358  74_HRV18b|   AACTTTGTAAAATGGCAAATAAATCTACAGGAAATGGCCCAGATTAGGAGAAAATTTGAG
1359  75_HRV18     AACTTTGTAAAATGGCAAATAAATCTACAGGAAATGGCCCAGATTAGGAGAAAATTTGAG
1360  76_HRV55     AATTTTACTAAGTGGCAAGTAAACATCCAAGAGATGGCTCAGATTAGAAGAAAATTTGAA
1361  77_HRV55b|   AATTTTACTAAGTGGCAAGTAAACATCCAAGAGATGGCTCAGATTAGAAGAAAATTTGAA
1362  78_HRV55a|   AATTTTACTAAGTGGCAAGTAAACATCCAAGAGATGGCTCAGATTAGAAGAAAATTTGAA
1363  79_HRV57     AATTTCACTAAATGGAAATAAATCTACAAGAAATGGCACAAATCAGAAGAAAATTTGAA
1364  80_HRV57a|   AATTTCACTAAATGGGAAATAAATCTACAAGAAATGGCACAAATCAGAAGAAAATTTGAA
1365  81_HRV57b|   AATTTCACTAAATGGGAAATAAATCTACAAGAAATGGCACAAATCAGAAGAAAATTTGAA
```

FIG. D10 CONT'D 06.trace                                                                                        9/20/2007 5:04 PM

```
1366  82_HRV21      AACATTAGTACATGGCAAATAAATATTAAAGAGATGGCACAAATTAGGAGAAAATTTGAA
1367  83_HRVHan     AACATTAATACATGGCAAATAAATATTAAAGAGATGGCACAAATTAGGAGAAAATTTGAA
1368  84_HRV43      AATTTTACCCAATGGCCAATCAACTTGCAAGAAATGGCACAAATTAGAAGAAAGTATGAA
1369  85_HRV43b|    AATTTTACCCAATGGCCAATCAACTTGCAAGAAATGGCACAAATTAGAAGAAAGTATGAA
1370  86_HRV43a|    AATTTTACCCAATGGCCAATCAACTTGCAAGAAATGGCACAAATTAGAAGAAAGTATGAA
1371  87_HRV75      AACTTCACTCAGTGGCCAATCAATCTACAGGAAATGGCTCAAATTAGAAGGAAATATGAA
1372  88_HRV75b|    AACTTCACTCAGTGGCCAATCAATCTACAGGAAATGGCTCAAATTAGAAGGAAATATGAA
1373  89_HRV75a|    AACTTCACTCAGTGGCCAATCAATCTACAGGAAATGGCTCAAATTAGAAGGAAATATGAA
1374  96_HRV9a|d    AATTTCACAATCTGGAAAATAAATATAAAGGAAATGGCCCAGATCAGGAGGAAATTTGAA
1375  97_HRV9b|d    AATTTCACAATCTGGAAAATAAATATAAAGGAAATGGCCCAGATCAGGAGGAAATTTGAA
1376  98_HRV9       AATTTCACAATCTGGAAAATAAATATAAAGGAAATGGCCCAGATCAGGAGGAAATTTGAA
1377  99_HRV32      AATTTCACAATTTGGAAGATAAATATAAAAGAAATGGCCCAGATTAGGAGAAAATTTGAG
1378  100_HRV32a    AATTTCACAATTTGGAAGATAAATATAAAAGAAATGGCCCAGATTAGGAGAAAATTTGAG
1379  101_HRV32b    AATTTCACAATTTGGAAGATAAATATAAAAGAAATGGCCCAGATTAGGAGAAAATTTGAG
1380  102_HRV67     AATTTCACAATTTGGAAAATAAATATAAAAGAAATGGCCCAGATTAGGAGGAAATTTGAA
1381  103_HRV67a    AATTTCACAATTTGGAAAATAAATATAAAAGAAATGGCCCAGATTAGGAGGAAATTTGAA
1382  104_HRV67b    AATTTCACAATTTGGAAAATAAATATAAAAGAAATGGCCCAGATTAGGAGAAAATTTGAA
1383  105_HRV15     AACTTTACTAAATGGCAAATTAATCTCAAAGAAATGGCCCAGATTAGAAGGAAATTTGAG
1384  106_HRV15a    AACTTTACTAAATGGCAAATTAATCTCAAAGAAATGGCCCAGATTAGAAGGAAATTTGAG
1385  107_HRV15b    AACTTTACTAAATGGCAAATTAATCTCAAAGAAATGGCCCAGATTAGAAGGAAATTTGAG
1386  108_HRV74a    AATTTTACTAAATGGCAAATAAATCTTAAAGAAATGGCACAGATTAGGAGAAAATTTGAG
1387  109_HRV74b    AATTTTACTAAATGGCAAATAAATCTTAAAGAAATGGCACAGATTAGGAGAAAATTTGAG
1388  110_HRV74     AATTTTACTAAATGGCAAATAAATCTTAAAGAAATGGCACAGATTAGGAGAAAATTTGAG
1389  111_HRV38a    AACTTTACAACATGGCAAATCAATCTCAAAGAAATGGCTCAAATCAGAAGAAAGTTTGAA
1390  112_HRV38b    AACTTTACAACATGGCAAATCAATCTCAAAGAAATGGCTCAAATCAGAAGAAAGTTTGAA
1391  113_HRV38     AACTTTACAACATGGCAAATCAATCTCAAAGAAATGGCTCAAATCAGAAGAAAGTTTGAA
1392  114_HRV60     AATTTCACAACTTGGCAAATTAACCTAAAGGAAATGGCACAAATAAGAAGAAAGTTTGAA
1393  115_HRV60a    AATTTCACAACTTGGCAAATTAACCTAAAGGAAATGGCACAAATAAGAAGAAAGTTTGAA
1394  116_HRV60b    AATTTCACAACTTGGCAAATTAACCTAAAGGAAATGGCACAAATAAGAAGAAAGTTTGAA
1395  117_HRV64a    AATTTTAACAAATGGCAGATCACCTTGAAAGAAATGGCTCAGATAAGAAGGAAGTATGAA
1396  118_HRV64b    AATTTTAACAAATGGCAGATCACCTTGAAAGAAATGGCTCAGATAAGAAGGAAGTATGAA
1397  119_HRV64     AATTTTAACAAATGGCAGATCACCTTGAAAGAAATGGCTCAGATAAGAAGGAAGTATGAA
1398  120_HRV94a    AATTTCCAATCATGGCAAATTACCCTAAAAGAAATGGCACAAATAAGAAGGAAATTTGAA
1399  121_HRV94b    AATTTCCAATCATGGCAAATTACCCTAAAAGAAATGGCACAAATAAGAAGGAAATTTGAA
1400  122_HRV94     AATTTCCAATCATGGCAAATTACCCTAAAAGAAATGGCACAAATAAGAAGGAAATTTGAA
1401  123_HRV22     AACTTTAACATATGGCAAATTAACCTTAAAGAGATGGCTCAGATAAGAAGGAAGTTTGAG
1402  124_HRV22a    AACTTTAACATATGGCAAATTAACCTTAAAGAGATGGCTCAGATAAGAAGGAAGTTTGAG
1403  125_HRV22b    AACTTTAACATATGGCAAATTAACCTTAAAGAGATGGCTCAGATAAGAAGGAAGTTTGAG
1404  126_HRV82     AACTTTAGATCATGGCAAATAAGCATAAAGGAAATGGCACAAATTAGAAGGAAGTTTGAA
1405  127_HRV82b    AACTTTAGATCATGGCAAATAAGCATAAAGGAAATGGCACAAATTAGAAGGAAGTTTGAA
1406  128_HRV82a    AACTTTAGATCATGGCAAATAAGCATAAAGGAAATGGCACAAATTAGAAGGAAGTTTGAA
1407  129_HRV19     AATTTCAAAACTTGGCAAATAAACTTGAAAGAAATGGCACAGATTAGAAGAAAATTTGAA
1408  130_HRV19a    AATTTCAAAACTTGGCAAATAAACTTGAAAGAAATGGCACAGATTAGAAGAAAATTTGAA
1409  131_HRV19b    AATTTCAAAACTTGGCAAATAAACTTGAAAGAAATGGCACAGATTAGAAGAAAATTTGAA
1410  132_HRV13     AATTTTGTGAAATGGAAAATAAGTTTGCAAGAAATGGCCCAAGTGCGCAGAAAATTTGAG
1411  133_HRV13a    AATTTTGTGAAATGGAAAATAAGTTTGCAAGAAATGGCCCAAGTGCGCAGAAAATTTGAG
1412  134_HRV13b    AATTTTGTGAAATGGAAAATAAGTTTGCAAGAAATGGCCCAAGTGCGCAGAAAATTTGAG
1413  135_HRV41     AACTTCAAGAAGTGGAAAATTAGCTTACAGGAGATGGCCCAAGTACGTAGAAAGTTTGAG
1414  136_HRV41a    AACTTCAAGAAGTGGAAAATTAGCTTACAGGAGATGGCCCAAGTACGTAGAAAGTTTGAG
1415  137_HRV41b    AACTTCAAGAAGTGGAAAATTAGCTTACAGGAGATGGCCCAAGTACGTAGAAAGTTTGAG
1416  138_HRV73     AATTTTACCAAATGGAAAATAAGTTTACAGGAGATGGCTCAAATACGTAGGAAATTTGAA
1417  139_HRV73b    AATTTTACCAAATGGAAAATAAGTTTACAAGAGATGGCTCAAATACGTAGGAAATTTGAA
1418  140_HRV73a    AATTTTACCAAATGGAAAATAAGTTTACAGGAGATGGCTCAAATACGTAGGAAATTTGAA
1419  141_HRV61     AACTTCAAGGTGTGGAAAATAAACCTGCAAGAGATGGCACAAATACGTAGAAAATTTGAG
1420  142_HRV61a    AACTTCAAGGTGTGGAAAATAAACCTGCAAGAGATGGCACAAATACGTAGAAAATTTGAG
1421  143_HRV61b    AACTTCAAGGTGTGGAAAATAAACCTGCAAGAGATGGCACAAATACGTAGAAAATTTGAG
1422  144_HRV96     AATTTTAAGGTGTGGAAAATAAATCTACAAGAAATGGCTCAAATTCGCAGGAAGTTTGAA
1423  145_HRV96b    AATTTTAAGGTGTGGAAAATAAATCTACAAGAAATGGCTCAAATTCGCAGGAAGTTTGAA
1424  146_HRV96a    AATTTTAAGGTGTGGAAAATAAATCTACAAGAAATGGCTCAAATTCGCAGGAAGTTTGAA
1425  90_HRV16a|    AGTTTCACTAAATGGAAGATAAACCTGCAAGAAATGGCACAAATTAGAAGAAAATTTGAA
1426  91_HRV16b|    AGTTTCACTAAATGGAAGATAAACCTGCAAGAAATGGCACAAATTAGAAGAAAATTTGAA
1427  92_1AYM_A     AGTTTCACTAAATGGAAGATAAACCTGCAAGAAATGGCACAAATTAGAAGAAAATTTGAA
1428  93_HRV81a|    AGCTTTACTAAATGGAAAATTAACTTACAAGAGATGGCACAGATTAGGAGAAAGTTTGAA
1429  94_HRV81b|    AGCTTTACTAAATGGAAAATTAACTTACAAGAGATGGCACAGATTAGGAGAAAGTTTGAA
1430  95_HRV81      AGCTTTACTAAATGGAAAATTAACTTACAAGAGATGGCACAGATTAGGAGAAAGTTTGAA
```

FIG. D10 CONT'D 06.trace                                                                9/20/2007 5:04 PM

```
1431 147_HRV2     AATTTTACAGTGTGGGCTATTAATATACAAGAAATGGCTCAAATTAGAAGGAAATTTGAA
1432 148_HRV2a|   AATTTTACAGTGTGGGCTATTAATATACAAGAAATGGCTCAAATTAGAAGGAAATTTGAA
1433 149_HRV2b|   AATTTTACAGTGTGGGCTATTAATATACAAGAAATGGCTCAAATTAGAAGGAAATTTGAA
1434 150_HRV49a   AATTTCAAAGTATGGAACATCAATTTGCAAGAAATGGCCCAGATCAGAAGAAAATTTGAA
1435 151_HRV49b   AATTTCAAAGTATGGAACATCAATTTGCAAGAAATGGCCCAGATCAGAAGAAAATTTGAA
1436 152_HRV49    AATTTCAAAGTATGGAACATCAATTTGCAAGAAATGGCCCAGATCAGAAGAAAATTTGAA
1437 153_HRV23a   AATTTTAATACTTGGAATATTAATTTACAGGAAATGGCCCAAATCAGAAGAAAGTTTGAA
1438 154_HRV23b   AATTTTAATACTTGGAATATTAATTTACAGGAAATGGCCCAAATCAGAAGAAAGTTTGAA
1439 155_HRV23    AATTTTAATACTTGGAATATTAATTTACAGGAAATGGCCCAAATCAGAAGAAAGTTTGAA
1440 156_HRV30a   AACTTTACCACATGGAATATTAATCTTCAAGAAATGGCCCAAATTAGAAGAAAATTTGAG
1441 157_HRV30b   AACTTTACCACATGGAATATTAATCTTCAAGAAATGGCCCAAATTAGAAGAAAATTTGAG
1442 158_HRV30    AACTTTACCACATGGAATATTAATCTTCAAGAAATGGCCCAAATTAGAAGAAAATTTGAG
1443 159_HRV7     GGTTTCACTACATGGAAAATCAGCTTACAAGAAATGGCACAAATCAGAAGAAAGTTTGAA
1444 160_HRV7b|   GGTTTCACTACATGGAAAATCAGCTTACAAGAAATGGCACAAATCAGAAGAAAGTTTGAA
1445 161_HRV7a|   GGTTTCACTACATGGAAAATCAGCTTACAAGAAATGGCACAAATCAGAAGAAAGTTTGAA
1446 162_HRV88    GGATTTGTAACATGGAAGATTAGCTTGCAAGAAATGGCACAAATCAGGAGAAAATTTGAA
1447 163_HRV88a   GGATTTGTAACATGGAAGATTAGCTTGCAAGAAATGGCACAAATCAGGAGAAAATTTGAA
1448 164_HRV88b   GGATTTGTAACATGGAAGATTAGCTTGCAAGAAATGGCACAAATCAGGAGAAAATTTGAA
1449 165_HRV36a   GGATTCAAAACATGGAAGATTAGTCTTCAAGAAATGGCACAAATTAGAAGGAAATATGAA
1450 166_HRV36b   GGATTCAAAACATGGAAGATTAGTCTTCAAGAAATGGCACAAATTAGAAGGAAATATGAA
1451 167_HRV36    GGATTCAAAACATGGAAGATTAGTCTTCAAGAAATGGCACAAATTAGAAGGAAATATGAA
1452 168_HRV89a   GGATTCAAAACATGGAAGGTTAGTCTTCAAGAAATGGCACAAATCAGAAGAAAATATGAA
1453 169_HRV89b   GGATTCAAAACATGGAAGGTTAGTCTTCAAGAAATGGCACAAATCAGAAGAAAATATGAA
1454 170_HRV89    GGATTCAAAACATGGAAGGTTAGTCTTCAAGAAATGGCACAAATCAGAAGAAAATATGAA
1455 171_HRV58    GGATACAAAACATGGAAAATTAGCCTTCAAGAGATGGCACAAATTAGAAGGAAATTTGAG
1456 172_HRV58a   GGATACAAAACATGGAAAATTAGCCTTCAAGAGATGGCACAAATTAGAAGGAAATTTGAG
1457 173_HRV58b   GGATACAAAACATGGAAAATTAGCCTTCAAGAGATGGCACAAATTAGAAGGAAATTTGAG
1458 174_HRV12a   AACTTTAAAACATGGAAGATAAATCTTAAGGAAATGGCCCAGATTAGAAGGAAAAATGAG
1459 175_HRV12b   AACTTTAAAACATGGAAGATAAATCTTAAGGAAATGGCCCAGATTAGAAGGAAAAATGAG
1460 176_HRV12    AACTTTAAAACATGGAAGATAAATCTTAAGGAAATGGCCCAGATTAGAAGGAAAAATGAG
1461 177_HRV78a   AATTTTACAACGTGGAAAATCAACTTACAGGAGATGGCCCAGATTAGAAGAAAGAATGAG
1462 178_HRV78b   AATTTTACAACGTGGAAAATCAACTTACAGGAGATGGCCCAGATTAGAAGAAAGAATGAG
1463 179_HRV78    AATTTTACAACGTGGAAAATCAACTTACAGGAGATGGCCCAGATTAGAAGAAAGAATGAG
1464 180_HRV20    AATTTCTCTCAGTGGAAGATCACAATCAAGGAAATGGCTCAAATCAGAAGAAAATGTGAG
1465 181_HRV20a   AATTTCTCTCAGTGGAAGATCACAATCAAGGAAATGGCTCAAATCAGAAGAAAATGTGAG
1466 182_HRV20b   AATTTCTCTCAGTGGAAGATCACAATCAAGGAAATGGCTCAAATCAGAAGAAAATGTGAG
1467 183_HRV68    AACTTCTCCCAATGGAAAATTACAATTAAGGAAATGGCTCAAATTAGAAGAAAGTGTGAA
1468 184_HRV68a   AACTTCTCCCAATGGAAAATTACAATTAAGGAAATGGCTCAAATTAGAAGAAAGTGTGAA
1469 185_HRV68b   AACTTCTCCCAATGGAAAATTACAATTAAGGAAATGGCTCAAATTAGAAGAAAGTGTGAA
1470 186_HRV28    AATTTTAGTAAATGGAATATCACTCTCAAAGAAATGGCCCAAATCAGAAGAAAGTGTGAA
1471 187_HRV28a   AATTTTAGTAAATGGAATATCACTCTCAAAGAAATGGCCCAAATCAGAAGAAAGTGTGAA
1472 188_HRV28b   AATTTTAGTAAATGGAATATCACTCTCAAAGAAATGGCCCAAATCAGAAGAAAGTGTGAA
1473 189_HRV53a   AACCACTCAGAATGGAAGATTACACTCAAAGAAATGGCCCAGATTAGAAGGAAATGTGAG
1474 190_HRV53b   AACCACTCAGAATGGAAGATTACACTCAAAGAAATGGCCCAGATTAGAAGGAAATGTGAG
1475 191_HRV53    AACCACTCAGAATGGAAGATTACACTCAAAGAAATGGCCCAGATTAGAAGGAAATGTGAG
1476 192_HRV46a   AACTTCTCAAAATGGAAAATAACACTGTTGGAAATGGCACAAATCAGAAGAAAGTGTGAA
1477 193_HRV46b   AACTTCTCAAAATGGAAAATAACACTGTTGGAAATGGCACAAATCAGAAGAAAGTGTGAA
1478 194_HRV46    AACTTCTCAAAATGGAAAATAACACTGTTGGAAATGGCACAAATCAGAAGAAAGTGTGAA
1479 195_HRV80a   AATTTTTCAAAGTGGAAAATAACATTAATGGAAATGGCACAAATTAGAAGAAAGTGTGAG
1480 196_HRV80b   AATTTTTCAAAGTGGAAAATAACATTAATGGAAATGGCACAAATTAGAAGAAAGTGTGAG
1481 197_HRV80    AATTTTTCAAAGTGGAAAATAACATTAATGGAAATGGCACAAATTAGAAGAAAGTGTGAG
1482 198_HRV51    AATTTCTCTACATGGAAAATTACACTCAAAGAAATGGCTCAAATTAGAAGAAAGTGTGAA
1483 199_HRV51a   AATTTCTCTACATGGAAAATTACACTCAAAGAAATGGCTCAAATTAGAAGAAAGTGTGAA
1484 200_HRV51b   AATTTCTCTACATGGAAAATTACACTCAAAGAAATGGCTCAAATTAGAAGAAAGTGTGAA
1485 201_HRV65a   AATTTCTCTGCTTGGGAAATTACACTCAAGGAAATGGCTCAAATTAGGAGAAAGTGTGAA
1486 202_HRV65b   AATTTCTCTGCTTGGGAAATTACACTCAAGGAAATGGCTCAAATTAGGAGAAAGTGTGAA
1487 203_HRV65    AATTTCTCTGCTTGGGAAATTACACTCAAGGAAATGGCTCAAATTAGGAGAAAGTGTGAA
1488 204_HRV71a   AATCTCTCAAAGTGGCAGATTACACTCAAAGAAATGGCTCAGATCAGGAGGAAATGTGAA
1489 205_HRV71b   AATCTCTCAAAGTGGCAGATTACACTCAAAGAAATGGCTCAGATCAGGAGGAAATGTGAA
1490 206_HRV71    AATCTCTCAAAGTGGCAGATTACACTCAAAGAAATGGCTCAGATCAGGAGGAAATGTGAA
1491 207_HRV8     AGTTTCAGGACCTGGGGAATAAACATACAAGAGATGTCACAAATTAGAAGGAAATTTGAG
1492 208_HRV95    AATTTCAGGACCTGGGGAATAAACATACAAGAGATGTCACAAATTAGAAGGAAATTTGAA
1493 209_HRV45    AATTACAAAAATTGGGCAATTAGTTTACAAGAAATGTCACAAATTAGGAGGAAATTTGAA
1494 210_HRV45a   AATTACAAAAATTGGGCAATTAGTTTACAAGAAATGTCACAAATTAGGAGGAAATTTGAA
1495 211_HRV45b   AATTACAAAAATTGGGCAATTAGTTTACAAGAAATGTCACAAATTAGGAGGAAATTTGAA
```

FIG. D10 CONT'D 06.trace                                                              9/20/2007 5:04 PM

```
1496 GROUP_1       ------------TGG----T-A---T----GA-ATG-C-CA--T--G--G-AA----GA-
1497
1498  1_HRV1A1|d   TTGTTTACATATGTCAGGTTTGACTCAGAAATAACCTTGG-TGCCTTGTATTGCTGGTAG
1499  2_HRV1A2|d   TTGTTTACATATGTCAGGTTTGACTCAGAAATAACCTTGG-TGCCTTGTATTGCTGGTAG
1500  3_HRV1A|cD   TTGTTTACATATGTCAGGTTTGACTCAGAAATAACCTTGG-TGCCTTGTATTGCTGGTAG
1501  4_HRV1B1|d   CTATTTACTTATGTTAGGTTTGATTCAGAAGTAACTTTAG-TACCCTGTATTGCTGGTAG
1502  5_HRV1B2|d   CTATTTACTTATGTTAGGTTTGATTCAGAAGTAACTTTAG-TACCCTGTATTGCTGGTAG
1503  6_HRV1B      CTATTTACTTATGTTAGGTTTGATTCAGAAGTAACTTTAG-TACCCTGTATTGCTGGTAG
1504  7_HRV40a|d   TTCTTTACATATGCTAGGTTTGATTCAGAAATTACCTTAG-TTCCTTGTATAGCCGGTAA
1505  8_HRV40b|d   TTCTTTACATATGCTAGGTTTGATTCAGAAATTACCTTAG-TTCCTTGTATAGCCGGTAA
1506  9_HRV40      TTCTTTACATATGCTAGGTTTGATTCAGAAATTACCTTAG-TTCCTTGTATAGCCGGTAA
1507 10_HRV85      TTCTTTACTTACACTAGATTTGATTCAGAAATCACTTTAG-TCCCTTGTATAGCTGGAAA
1508 11_HRV85a|    TTCTTTACTTACACTAGATTTGATTCAGAAATCACTTTAG-TCCCTTGTATAGCTGGAAA
1509 12_HRV85b|    TTCTTTACTTACACTAGATTTGATTCAGAAATCACTTTAG-TCCCTTGTATAGCTGGAAA
1510 13_HRV56a|    TTCTTTACTTATGTCAGATTTGATTCAGAGGTTACTTTGG-TACCTTGTGTAGCCGGCAA
1511 14_HRV56b|    TTCTTTACTTATGTCAGATTTGATTCAGAGGTTACTTTGG-TACCTTGTGTAGCCGGCAA
1512 15_HRV56      TTCTTTACTTATGTCAGATTTGATTCAGAGGTTACTTTGG-TACCTTGTGTAGCCGGCAA
1513 16_HRV54      TTCTTTACTTATGTTAGGTTTGATTCAGAAATTACTCTAG-TCCCCTGTATAGCTGGTAA
1514 17_HRV98      TTCTTTACTTATGTTAGATTTGATTCAGAAGTTACCTTAG-TTCCTTGCATAGCTGGCAA
1515 18_HRV59a|    TTCTTCACATATGTTAGATTTGACTCAGAAATCACTTTGG-TGCCTTGCATAGCTGGAAA
1516 19_HRV59b|    TTCTTCACATATGTTAGATTTGACTCAGAAATCACTTTGG-TGCCTTGCATAGCTGGAAA
1517 20_HRV59      TTCTTCACATATGTTAGATTTGACTCAGAAATCACTTTGG-TGCCTTGCATAGCTGGAAA
1518 21_HRV63      TTCTTCACATATGTCAGATTTGATTCAGAAGTCACTCTTG-TACCATGTATAGCAGGAAA
1519 22_HRV63b|    TTCTTCACATATGTCAGATTTGATTCAGAAGTCACTCTTG-TACCATGTATAGCAGGAAA
1520 23_HRV63a|    TTCTTCACATATGTCAGATTTGATTCAGAAGTCACTCTTG-TACCATGTATAGCAGGAAA
1521 24_HRV39      ATGTTCACCTATGTTAGATTTGACTCAGAGATTACTTTAG-TCCCATGCATAGCTGGAAG
1522 25_HRV39a|    ATGTTCACCTATGTTAGATTTGACTCAGAGATTACTTTAG-TCCCATGCATAGCTGGAAG
1523 26_HRV39b|    ATGTTCACCTACGTTAGATTTGACTCAGAGATTACTTTAG-TCCCATGCATAGCTGGAAG
1524 27_HRV10a|    ATGTTTACATATGTTAGATTTGACTCAGAAGTCACTTTAG-TACCTTGCATCGCAGGCAA
1525 28_HRV10b|    ATGTTTACATATGTTAGATTTGACTCAGAAGTCACTTTAG-TACCTTGCATCGCAGGCAA
1526 29_HRV10      ATGTTTACATATGTTAGATTTGACTCAGAAGTCACTTTAG-TACCTTGCATCGCAGGCAA
1527 30_HRV100a    ATGTTTACATATGTCAGATTTGACTCAGAAATCACATTGG-TACCCTGTATTGCAGGAAA
1528 31_HRV100b    ATGTTTACATATGTCAGATTTGACTCAGAAATCACATTGG-TACCCTGTATTGCAGGAAA
1529 32_HRV100     ATGTTTACATATGTCAGATTTGACTCAGAAATCACATTGG-TACCCTGTATTGCAGGAAA
1530 33_HRV66      ATGTTCACATATGTTAGGTTTGATTCTGAAATTACATTAG-TCCCATGCATTGCAGGAAA
1531 34_HRV66b|    ATGTTCACATATGTTAGGTTTGATTCTGAAATTACATTAG-TCCCATGCATTGCAGGAAA
1532 35_HRV66a|    ATGTTCACATATGTTAGGTTTGATTCTGAAATTACATTAG-TCCCATGCATTGCAGGAAA
1533 36_HRV77a|    ATGTTTACATATGTAAGATTTGATTCAGAAATTACATTGG-TCCCATGTATTGCTGGAAA
1534 37_HRV77b|    ATGTTTACATATGTAAGATTTGATTCAGAAATTACATTGG-TCCCATGTATTGCTGGAAA
1535 38_HRV77      ATGTTTACATATGTAAGATTTGATTCAGAAATTACATTGG-TCCCATGTATTGCTGGAAA
1536 39_HRV62a     ATGTTTACATATGTAAGATTTGATTCAGAAATAACCCTGG-TTCCATCTATTGCAGGACG
1537 40_HRV62b     ATGTTTACATATGTAAGATTTGATTCAGAAATAACCCTGG-TTCCATCTATTGCAGGACG
1538 41_HRV25      ATGTTTACATATGTGAGATTTGATTCAGAAATAACCCTAG-TTCCATCTATTGCAGGACG
1539 42_HRV29a     ATGTTCACATATGTGAGATTTGACTCAGAAATAACTCTGG-TTCTTTGCATTGCAGGACG
1540 43_HRV29b     ATGTTCACATATGTGAGATTTGACTCAGAAATAACTCTGG-TTCCATGCATTGCAGGACG
1541 44_HRV44a     ATGTTCACATATGTGAGATTTGACTCAGAAATAACTCTAG-TTCCATGCATTGCAGGACA
1542 45_HRV44b     ATGTTCACATATGTGAGATTTGATTCAGAAATAACTCTAG-TTCCATGCATTGCAGGACG
1543 46_HRV31      ATGTTCACATATGTAAGATTTGATTCAGAAGTGACCATAG-TTCCATGCATTGCAGGACA
1544 47_HRV31a|    ATGTTCACATATGTAAGATTTGATTCAGAAGTGACCATAG-TTCCATGCATTGCAGGACA
1545 48_HRV31b|    ATGTTCACATATGTAAGATTTGATTCAGAAGTGACCATAG-TTCCATGCATTGCAGGACA
1546 49_HRV47      ATGTTTACATATGTAAGATTTGATTCAGAAGTAACCATGG-TTCCATGTATTGCAGGGTA
1547 50_HRV47a|    ATGTTTACATATGTAAGATTTGATTCAGAAGTAACCATGG-TTCCATGTATTGCAGGGTA
1548 51_HRV47b|    ATGTTTACATATGTAAGATTTGATTCAGAAGTAACCATGG-TTCCATGTATTGCAGGGTA
1549 52_HRV11      ATGTTCACATACACTAGATTTGATTCAGAGTCACATTGG--TGCCTTGTATAGCTGCAAA
1550 53_HRV11b|    ATGTTCACATACACTAGATTTGATTCAGAGATCACATTGG-TGCCTTGTATAGCTGCAAA
1551 54_HRV11a|    ATGTTCACATACACTAGATTTGATTCAGAGATCACATTGG-TGCCTTGTATAGCTGCAAA
1552 55_HRV76      ATGTTTACATATACTAGATTTGATTCAGAAGTTACTCTAG-TTCCTTCTATAGCTGCCAA
1553 56_HRV76b|    ATGTTTACATATACTAGATTTGATTCAGAAGTTACTCTAG-TTCCTTCTATAGCTGCCAA
1554 57_HRV76a|    ATGTTTACATATACTAGATTTGATTCAGAAGTTACTCTAG-TTCCTTCTATAGCTGCCAA
1555 58_HRV33      ATGTTTACATATGCCAGATTTGATTCAGAGATCACCCTAG-TCCCTTCTATAGCTGCCCA
1556 59_HRV33b|    ATGTTTACATATGCCAGATTTGATTCAGAGATCACCCTAG-TCCCTTCTATAGCTGCCCA
1557 60_HRV33a|    ATGTTTACATATGCCAGATTTGATTCAGAGATCACCCTAG-TCCCTTCTATAGCTGCCCA
1558 61_HRV24a|    TTATTCACATATACTAGATTTGACTCTGAGATTACAATAG-TTCCATCCATAGCTGGCAA
1559 62_HRV24b|    TTATTCACATATACTAGATTTGACTCTGAGATTACAATAG-TTCCATCCATAGCTGGCAA
1560 63_HRV24      TTATTCACATATACTAGATTTGACTCTGAGATTACAATAG-TTCCATCCATAGCTGGCAA
```

FIG. D10 CONT'D 06.trace                                                                                           9/20/2007 5:04 PM

```
1561  64_HRV90      TTGTTTACATATGCTAGATTTGATTCTGAAATTACAATAG-TACCATCTATAGCTGGCAA
1562  65_HRV90a|    TTGTTTACATATGCTAGATTTGATTCTGAAATTACAATAG-TACCATCTATAGCTGGCAA
1563  66_HRV90b|    TTGTTTACATATGCTAGATTTGATTCTGAAATTACAATAG-TACCATCTATAGCTGGCAA
1564  67_HRV34      ATGTTCACCTACGTCAGATTTGATTCTGAAGTCACCCTAG-TACCATCAATAGCGGCCAA
1565  68_HRV34b|    ATGTTCACCTACGTCAGATTTGATTCTGAAGTCACCCTAG-TACCATCAATAGCGGCCAA
1566  69_HRV34a|    ATGTTCACCTACGTCAGATTTGATTCTGAAGTCACCCTAG-TACCATCAATAGCGGCCAA
1567  70_HRV50a|    ATGTTCACCTATGTGAGGTTTAATTCTGAGGTCACATTAG-TACCATCCATAGCTGCCAA
1568  71_HRV50b|    ATGTTCACCTATGTGAGGTTTAATTCTGAGGTCACATTAG-TACCATCCATAGCTGCCAA
1569  72_HRV50      ATGTTCACCTATGTGAGGTTTAATTCTGAGGTCACATTAG-TACCATCCATAGCTGCCAA
1570  73_HRV18a|    ATGTTTACATATGTTAGATTTGATTCAGAAATTACACTAG-TACCATCTGTAGCTGCTAA
1571  74_HRV18b|    ATGTTTACATATGTTAGATTTGATTCAGAAATTACACTAG-TACCATCTGTAGCTGCTAA
1572  75_HRV18      ATGTTTACATATGTTAGATTTGATTCAGAAATTACACTAG-TACCATCTGTAGCTGCTAA
1573  76_HRV55      ATGTTCACCTACTAGATTTGATTCAGAAGTTACATTAG-TACCCTCTATTGCTGCAAA
1574  77_HRV55b|    ATGTTCACCTACTAGATTTGATTCAGAAGTTACATTAG-TACCCTCTATTGCTGCAAA
1575  78_HRV55a|    ATGTTCACCTACTAGATTTGATTCAGAAGTTACATTAG-TACCCTCTATTGCTGCAAA
1576  79_HRV57      CTATTTACATATGTTAGGTTTGATTCTGAAGTTACATTAG-TTCCCTCCATAGCTGCTCA
1577  80_HRV57a|    CTATTTACATATGTTAGGTTTGATTCTGAAGTTACATTAG-TTCCCTCCATAGCTGCTCA
1578  81_HRV57b|    CTATTTACATATGTTAGGTTTGATTCTGAAGTTACATTAG-TTCCCTCCATAGCTGCTCA
1579  82_HRV21      ATGTTCACCTATACTAGATTTGATTCAGAAATAACTTTGG-TGCCGTCAATTGCAGCTAG
1580  83_HRVHan     ATGTTCACCTACTAGATTTGATTCAGAAATAACTTTGG-TACCGTCAATTGCAGCTAA
1581  84_HRV43      TTGTTCACATACTTAAGGTTTGATTCTGAAATTACCCTTG-TTCCTTGCATTGCAGCAAA
1582  85_HRV43b|    TTGTTCACATACTTAAGGTTTGATTCTGAAATTACCCTTG-TTCCTTGCATTGCAGCAAA
1583  86_HRV43a|    TTGTTCACATACTTAAGGTTTGATTCTGAAATTACCCTTG-TTCCTTGCATTGCAGCAAA
1584  87_HRV75      TTATTTACATATCTTAGATTTGATTCAGAGGTTACTCTGG-TGCCATGCATTGCAGCTAA
1585  88_HRV75b|    TTATTTACATATCTTAGATTTGATTCAGAGGTTACTCTGG-TGCCATGCATTGCAGCTAA
1586  89_HRV75a|    TTATTTACATATCTTAGATTTGATTCAGAGGTTACTCTGG-TGCCATGCATTGCAGCTAA
1587  96_HRV9a|d    TTGTTTACATATGCAAGATTTGACTCTGAAATAACATTGG-TCCCGTGTATAGCAGCAGA
1588  97_HRV9b|d    TTGTTTACATATGCAAGATTTGACTCTGAAATAACATTGG-TCCCGTGTATAGCAGCAGA
1589  98_HRV9       TTGTTTACATATGCAAGATTTGACTCTGAAATAACATTGG-TCCCGTGTATAGCAGCAGA
1590  99_HRV32      TTGTTTACATACACAAGGTTTGATTCTGAAATAACATTAG-TACCTTGTATAGCTGCAGA
1591  100_HRV32a    TTGTTTACATACACAAGGTTTGATTCTGAAATAACATTAG-TACCTTGTATAGCTGCAGA
1592  101_HRV32b    TTGTTTACATACACAAGGTTTGATTCTGAAATAACATTAG-TACCTTGTATAGCTGCAGA
1593  102_HRV67     CTATTCACATATACAAGATTTGATTCTGAGATAACACTGG-TACCATGCATAGCTGCAGA
1594  103_HRV67a    CTATTCACATATACAAGATTTGATTCTGAGATAACACTGG-TACCATGCATAGCTGCAGA
1595  104_HRV67b    CTATTCACATATACAAGATTTGATTCTGAGATAACACTGG-TACCATGCATAGCTGCAGA
1596  105_HRV15     TTATTCACATATGTAAGGTTTGATTCAGAAATAACACTTG-TACCATGCATTGCAGCAAA
1597  106_HRV15a    TTATTCACATATGTAAGGTTTGATTCAGAAATAACACTTG-TACCATGCATTGCAGCAAA
1598  107_HRV15b    TTATTCACATATGTAAGGTTTGATTCAGAAATAACACTTG-TACCATGCATTGCAGCAAA
1599  108_HRV74a    TTGTTCACATATGTTAGATTTGACTCAGAAGTGACATTAG-TTCCATGCATTGCTGCTAA
1600  109_HRV74b    TTGTTCACATATGTTAGATTTGACTCAGAAGTGACATTAG-TTCCATGCATTGCTGCTAA
1601  110_HRV74     TTGTTCACATATGTTAGATTTGACTCAGAAGTGACATTAG-TTCCATGCATTGCTGCTAA
1602  111_HRV38a    ATGTTTACATATGTGAGATTTGATTCAGAAGTTACATTAG-TCCCATGTATAGCAGCACA
1603  112_HRV38b    ATGTTTACATATGTGAGATTTGATTCAGAAGTTACATTAG-TCCCATGTATAGCAGCACA
1604  113_HRV38     ATGTTTACATATGTGAGATTTGATTCAGAAGTTACATTAG-TCCCATGTATAGCAGCACA
1605  114_HRV60     TTATTTACATATGTAAGATTTGATTCAGAATTGACTCTGG-TCCCATGCATAGCAGCAAA
1606  115_HRV60a    TTATTTACATATGTAAGATTTGATTCAGAATTGACTCTGG-TCCCATGCATAGCAGCAAA
1607  116_HRV60b    TTATTTACATATGTAAGATTTGATTCAGAATTGACTCTGG-TCCCATGCATAGCAGCAAA
1608  117_HRV64a    TTATTTACATATGTTAGATTTGATTCTGAAATAACCTTAG-TGCCTTGCATATCTTCTCA
1609  118_HRV64b    TTATTTACATATGTTAGATTTGATTCTGAAATAACCTTAG-TGCCTTGCATATCTTCTCA
1610  119_HRV64     TTATTTACATATGTTAGATTTGATTCTGAAATAACCTTAG-TGCCTTGCATATCTTCTCA
1611  120_HRV94a    CTATTTACTTATGTTAGATTTGATTCAGAAATAACTTTAG-TACCTTGCATATCATCTCA
1612  121_HRV94b    CTATTTACTTATGTTAGATTTGATTCAGAAATAACTTTAG-TACCTTGCATATCATCTCA
1613  122_HRV94     CTATTTACTTATGTTAGATTTGATTCAGAAATAACTTTAG-TACCTTGCATATCATCTCA
1614  123_HRV22     CTATTTACATATCTCAGGTTTGATTCTGAAATCACTTTGG-TACCATGCATTGCTTCACA
1615  124_HRV22a    CTATTTACATATCTCAGGTTTGATTCTGAAATCACTTTGG-TACCATGCATTGCTTCACA
1616  125_HRV22b    CTATTTACATATCTCAGGTTTGATTCTGAAATCACTTTGG-TACCATGCATTGCTTCACA
1617  126_HRV82     CTTTTCACATATGTGAGATTTGATTCAGAAATTACTTTAG-TGCCTTGCATAGCCTCTCA
1618  127_HRV82b    CTTTTCACATATGTGAGATTTGATTCAGAAATTACTTTAG-TGCCTTGCATAGCCTCTCA
1619  128_HRV82a    CTTTTCACATATGTGAGATTTGATTCAGAAATTACTTTAG-TGCCTTGCATAGCCTCTCA
1620  129_HRV19     CTTTTCACTTACCTCAGATTTGATTCAGAGGTAACATTAG-TCCCTTGCATAGCTGCTAA
1621  130_HRV19a    CTTTTCACTTACCTCAGATTTGATTCAGAGGTAACATTAG-TCCCTTGCATAGCTGCTAA
1622  131_HRV19b    CTTTTCACTTACCTCAGATTTGATTCAGAGGTAACATTAG-TCCCTTGCATAGCTGCTAA
1623  132_HRV13     TTGTTCACCTATGTAAGATTTGATTCAGAAATAACAATTG-TGCCATGTATAGCCGGGCA
1624  133_HRV13a    TTGTTCACCTATGTAAGATTTGATTCAGAAATAACAATTG-TGCCATGTATAGCCGGGCA
1625  134_HRV13b    TTGTTCACCTATGTAAGATTTGATTCAGAAATAACAATTG-TGCCATGTATAGCCGGGCA
```

FIG. D10 CONT'D

```
06.trace                                                                              9/20/2007 5:04 PM 1626 135_HRV41    TTTTTTACGTATGTTAGATTTGACTCAGAAATAACAATTG-TGCCAAGTATAGCTGGACA
1627 136_HRV41a   TTTTTTACGTATGTTAGATTTGACTCAGAAATAACAATTG-TGCCAAGTATAGCTGGACA
1628 137_HRV41b   TTTTTTACGTATGTTAGATTTGACTCAGAAATAACAATTG-TGCCAAGTATAGCTGGACA
1629 138_HRV73    TTATTCACCTATGTAAGATTTGATTCAGAAGTGACAATTG-TACCATGTATAGCTGGTCA
1630 139_HRV73b   TTATTCACCTATGTAAGATTTGATTCAGAAGTGACAATTG-TACCATGTATAGCTGGTCA
1631 140_HRV73a   TTATTCACCTATGTAAGATTTGATTCAGAAGTGACAATTG-TACCATGTATAGCTGGTCA
1632 141_HRV61    TTGTTCACATATGCTAGATTTGATTCAGAGATTACAATTG-TACCTTGTGTTGCTGGGCA
1633 142_HRV61a   TTGTTCACATATGCTAGATTTGATTCAGAGATTACAATTG-TACCTTGTGTTGCTGGGCA
1634 143_HRV61b   TTGTTCACATATGCTAGATTTGATTCAGAGATTACAATTG-TACCTTGTGTTGCTGGGCA
1635 144_HRV96    CTGTTCACTTATGCTAGATTTGATTCAGAGATAACAATTG-TTCCATGTGTTGCTGTGCA
1636 145_HRV96b   CTGTTCACTTATGCTAGATTTGATTCAGAGATAACAATTG-TTCCATGTGTTGCTGTGCA
1637 146_HRV96a   CTGTTCACTTATGCTAGATTTGATTCAGAGATAACAATTG-TTCCATGTGTTGCTGTGCA
1638 90_HRV16a|   ATGTTTACTTATGCAAGATTTGACTCTGAAATTACTATGG-TACCAAGTGTAGCAGCCAA
1639 91_HRV16b|   ATGTTTACTTATGCAAGATTTGACTCTGAAATTACTATGG-TACCAAGTGTAGCAGCCAA
1640 92_1AYM_A    ATGTTTACTTATGCAAGATTTGACTCTGAAATTACTATGG-TACCAAGTGTAGCAGCCAA
1641 93_HRV81a|   ATGTTCACATACACTAGATTTAACTCTGAGATTACACTGG-TACCAAGTATTGCAAACAA
1642 94_HRV81b|   ATGTTCACATACACTAGATTTAACTCTGAGATTACACTGG-TACCAAGTATTGCAAACAA
1643 95_HRV81     ATGTTCACATACACTAGATTTAACTCTGAGATTACACTGG-TACCAAGTATTGCAAACAA
1644 147_HRV2     TTGTTCACCTATACTAGGTTTGATTCTGAAATAACCCTAG-TTCCATGCATTTCCGCCCT
1645 148_HRV2a|   TTGTTCACCTATACTAGGTTTGATTCTGAAATAACCCTAG-TTCCATGCATTTCCGCCCT
1646 149_HRV2b|   TTGTTCACCTATACTAGGTTTGATTCTGAAATAACCCTAG-TTCCATGCATTTCCGCCCT
1647 150_HRV49a   CTGTTTACTTACACTAGATTCGATTCTGAAATAACCTTGG-TTCCATGCATTTCTGCACT
1648 151_HRV49b   CTGTTTACTTACACTAGATTCGATTCTGAAATAACCTTGG-TTCCATGCATTTCTGCACT
1649 152_HRV49    CTGTTTACTTACACTAGATTCGATTCTGAAATAACCTTGG-TTCCATGCATTTCTGCACT
1650 153_HRV23a   CTGTTTACTTACACTAGATTTGATTCTGAAATTACTTTGG-TTCCATGCATTTCTGCTCT
1651 154_HRV23b   CTGTTTACTTACACTAGATTTGATTCTGAAATTACTTTGG-TTCCATGCATTTCTGCTCT
1652 155_HRV23    CTGTTTACTTACACTAGATTTGATTCTGAAATTACTTTGG-TTCCATGCATTTCTGCTCT
1653 156_HRV30a   CTATTCACTTACACTAGATTTGATTCTGAGATAACCTTGG-TTCCGTGTATTTCAGCTCT
1654 157_HRV30b   CTATTCACTTACACTAGATTTGATTCTGAGATAACCTTGG-TTCCGTGTATTTCAGCTCT
1655 158_HRV30    CTATTCACTTACACTAGATTTGATTCTGAGATAACCTTGG-TTCCGTGTATTTCAGCTCT
1656 159_HRV7     CTATTCACACACACTAGATTTGATTCTGAGATAACAATAG-TCACAGCAGCAGCAGCACA
1657 160_HRV7b|   CTATTCACATACACTAGATTTGATTCTGAGATAACAATAG-TCACAGCAGCAGCAGCACA
1658 161_HRV7a|   CTATTCACATACACTAGATTTGATTCTGAGATAACAATAG-TCACAGCAGCAGCAGCACA
1659 162_HRV88    TTGTTTACATACACTAGATTTGACTCAGAAATAACAATAG-TCACAGCAGCTGCAGCACA
1660 163_HRV88a   TTGTTTACATACACTAGATTTGACTCAGAAATAACAATAG-TCACAGCAGCTGCAGCACA
1661 164_HRV88b   TTGTTTACATACACTAGATTTGACTCAGAAATAACAATAG-TCACAGCAGCTGCAGCACA
1662 165_HRV36a   TTGTTTACATACACAAGATTTGACTCAGAAATAACAATAG-TCACCGCAGCTGCAGTGCA
1663 166_HRV36b   TTGTTTACATACACAAGATTTGACTCAGAAATAACAATAG-TCACCGCAGCTGCAGTGCA
1664 167_HRV36    TTGTTTACATACACAAGATTTGACTCAGAAATAACAATAG-TCACCGCAGCTGCAGTGCA
1665 168_HRV89a   TTATTCACATATACAAGATTTGATTCAGAGATAACAATAG-TCACTGCAGCCGCAGCTCA
1666 169_HRV89b   TTATTCACATATACAAGATTTGATTCAGAGATAACAATAG-TCACTGCAGCCGCAGCTCA
1667 170_HRV89    TTATTCACATATACAAGATTTGATTCAGAGATAACAATAG-TCACTGCAGCCGCAGCTCA
1668 171_HRV58    TTGTTCACATATACAAGATTTGACTCAGAGATTACAATAG-TCACTGCAGCAGCTGCTCA
1669 172_HRV58a   TTGTTTACATATACAAGATTTGACTCAGAGATTACAATAG-TCACTGCAGCAGCTGCTCA
1670 173_HRV58b   TTGTTTACATATACAAGATTTGACTCAGAGATTACAATAG-TCACTGCAGCAGCTGCTCA
1671 174_HRV12a   CTTTTCACCTACTTAAGGTTTGATTCTGAAATCACCATTGTTCCAAGCAATG-CAGCAAT
1672 175_HRV12b   CTTTTCACCTACTTAAGGTTTGATTCTGAAATCACCATTGTTCCAAGCAATG-CAGCAAT
1673 176_HRV12    CTTTTCACCTACTTAAGGTTTGATTCTGAAATCACCATTGTTCCAAGCAATG-CAGCAAT
1674 177_HRV78a   ATGTTCACATATCTCAGATTTGATTCAGAAATCACTCTTG-TGTGTGCAGTGGCCTCACA
1675 178_HRV78b   ATGTTCACATATCTCAGATTTGATTCAGAAATCACTCTTG-TGTGTGCAGTGGCCTCACA
1676 179_HRV78    ATGTTCACATATCTCAGATTTGATTCAGAAATCACTCTTG-TGTGTGCAGTGGCCTCACA
1677 180_HRV20    CTCTTTACATACCTCAGATTTGATTCTGAGATTACAATAG-TAGCAACAGTAGCTGCACT
1678 181_HRV20a   CTCTTTACATACCTCAGATTTGATTCTGAGATTACAATAG-TAGCAACAGTAGCTGCACT
1679 182_HRV20b   CTCTTTACATACCTCAGATTTGATTCTGAGATTACAATAG-TAGCAACAGTAGCTGCACT
1680 183_HRV68    CTATTCACATACCTTAGGTTTGACTCTGAGATTACAATAG-TAGCAACAATAGCTGCTCT
1681 184_HRV68a   CTATTCACATACCTTAGGTTTGACTCTGAGATTACAATAG-TAGCAACAATAGCTGCTCT
1682 185_HRV68b   CTATTCACATACCTTAGGTTTGACTCTGAGATTACAATAG-TAGCAACAATAGCTGCTCT
1683 186_HRV28    ATGTTTACATATCTCAGATTTGATTCTGAAATTACTATAG-TGGTGTCAGTTGCAAGTAA
1684 187_HRV28a   ATGTTTACATATCTCAGATTTGATTCTGAAATTACTATAG-TGGTGTCAGTTGCAAGTAA
1685 188_HRV28b   ATGTTTACATATCTCAGATTTGATTCTGAAATTACTATAG-TGGTGTCAGTTGCAAGTAA
1686 189_HRV53a   ATGTTCACATATCTTAGATTTGATTCAGAAATAACTATAG-TGGTATCAGTGGCTAGTAA
1687 190_HRV53b   ATGTTCACATATCTTAGATTTGATTCAGAAATAACTATAG-TGGTATCAGTGGCTAGTAA
1688 191_HRV53    ATGTTCACATATCTTAGATTTGATTCAGAAATAACTATAG-TGGTATCAGTGGCTAGTAA
1689 192_HRV46a   CTTTTTACATATCTCAGATTTGATTCAGAAATAACAATAG-TCACCACATTGGCAGGCCA
1690 193_HRV46b   CTTTTTACATATCTCAGATTTGATTCAGAAATAACAATAG-TCACCACATTGGCAGGCCA
```

FIG. D10 CONT'D 06.trace                                                                                                9/20/2007 5:04 PM

```
1691  194_HRV46     CTTTTTACATATCTCAGATTTGATTCAGAAATAACAATAG-TCACCACATTGGCAGGCCA
1692  195_HRV80a    CTTTTCACTTACCTCAGATTTGACTCAGAAATAACAATAG-TAACTACCTTAGCAGGACA
1693  196_HRV80b    CTTTTCACTTACCTCAGATTTGACTCAGAAATAACAATAG-TAACTACCTTAGCAGGACA
1694  197_HRV80     CTTTTCACTTACCTCAGATTTGACTCAGAAATAACAATAG-TAACTACCTTAGCAGGACA
1695  198_HRV51     CTTTTCACATACTTAAGATTTGATTCAGAGATCACTATAG-TTGCTACCATTGCTGGACA
1696  199_HRV51a    CTTTTCACATACTTAAGATTTGATTCAGAGATCACTATAG-TTGCTACCATTGCTGGACA
1697  200_HRV51b    CTTTTCACATACTTAAGATTTGATTCAGAGATCACTATAG-TTGCTACCATTGCTGGACA
1698  201_HRV65a    CTCTTCACCTATTTGCGCTTTGACTCAGAAATTACCATAG-TGGCTACTATAGCTGGACA
1699  202_HRV65b    CTCTTCACCTATTTGCGCTTTGACTCAGAAATTACCATAG-TGGCTACTATAGCTGGACA
1700  203_HRV65     CTCTTCACCTATTTGCGCTTTGACTCAGAAATTACCATAG-TGGCTACTATAGCTGGACA
1701  204_HRV71a    CTCTTCACATACCTGCGCTTTGATTCAGAGATAACAATTG-TAGCTACACTAGCAGGGCA
1702  205_HRV71b    CTCTTCACATACCTGCGCTTTGATTCAGAGATAACAATTG-TAGCTACACTAGCAGGGCA
1703  206_HRV71     CTCTTCACATACCTGCGCTTTGATTCAGAGATAACAATTG-TAGCTACACTAGCAGGGCA
1704  207_HRV8      ATGTTCACTTATGTAAGATTTGATTCAGAGATAACAATTG-TACCATGTATTGCAGCTAT
1705  208_HRV95     ATGTTCACTTATGTAAGATTTGATTCAGAGATAACAATTG-TACCATGTATTGCAGCTAT
1706  209_HRV45     ATGTTTACATATGTCAGATTTGATTCCGAAATAACAATAG-TACCATGTGTTGCTGCCAC
1707  210_HRV45a    ATGTTTACATATGTCAGATTTGATTCCGAAATAACAATAG-TACCATGTGTTGCTGCCAC
1708  211_HRV45b    ATGTTTACATATGTCAGATTTGATTCCGAAATAACAATAG-TACCATGTGTTGCTGCCAC
1709  GROUP_1       -T-TT-AC-TA-----G-TT--A-TC-GA--T-AC--T-G-T-----------C------
1710
1711  1_HRV1A1|d    AGGAGACGACATTGGACATATTGTAATGCAATATATGTATGTTCCTCCAGGAGCTCCAAT
1712  2_HRV1A2|d    AGGAGACGACATTGGACATATTGTAATGCAATATATGTATGTTCCTCCAGGAGCTCCAAT
1713  3_HRV1A|cD    AGGAGACGACATTGGACATATTGTAATGCAATATATGTATGTTCCTCCAGGAGCTCCAAT
1714  4_HRV1B1|d    AGGAGATGACATTGGTCATGTTGTAATGCAGTATATGTATGTTCCCCCAGGAGCTCCAAT
1715  5_HRV1B2|d    AGGAGATGACATTGGTCATGTTGTAATGCAGTATATGTATGTTCCCCCAGGAGCTCCAAT
1716  6_HRV1B       AGGAGATGACATTGGTCATGTTGTAATGCAGTATATGTATGTTCCCCCAGGAGCTCCAAT
1717  7_HRV40a|d    GGGTGAAGACATTGGACACATTGTGATGCAATATATGTATGTACCCCCTGGCGCACCCAT
1718  8_HRV40b|d    GGGTGAAGACATTGGACACATTGTGATGCAATATATGTATGTACCCCCTGGCGCACCCAT
1719  9_HRV40       GGGTGAAGACATTGGACACATTGTGATGCAATATATGTATGTACCCCCTGGCGCACCCAT
1720  10_HRV85      GGGTGATGATATTGGACACATTGTAATGCAGTATATGTATGTGCCCCCCGGAGCACCAAT
1721  11_HRV85a|    GGGTGATGATATTGGACACATTGTAATGCAGTATATGTATGTGCCCCCCGGAGCACCAAT
1722  12_HRV85b|    GGGTGATGATATTGGACACATTGTAATGCAGTATATGTATGTGCCCCCCGGAGCACCAAT
1723  13_HRV56a|    GGGAGATGATATTGGACACATTGTAATGCAATACATGTATGTGCCTCCTGGTGCACCACT
1724  14_HRV56b|    GGGAGATGATATTGGACACATTGTAATGCAATACATGTATGTGCCTCCTGGTGCACCACT
1725  15_HRV56      GGGAGATGATATTGGACACATTGTAATGCAATACATGTATGTGCCTCCTGGTGCACCACT
1726  16_HRV54      GGGAGTTGATATTGGACACATTGTCATGCAATTCATGTATGTACCGCCTGGTGCACCAAA
1727  17_HRV98      GGGAGCTGACATTGGACACATTGTCATGCAATTCATGTATGTTCCACCTGGTGCACCTAA
1728  18_HRV59a|    AGGGGATGACATTGGTCATATAGTCATGCAATATATGTATGTTCCACCAGGTGCTCCACT
1729  19_HRV59b|    AGGGGATGACATTGGTCATATAGTCATGCAATATATGTATGTTCCACCAGGTGCTCCACT
1730  20_HRV59      AGGGGATGACATTGGTCATATAGTCATGCAATATATGTATGTTCCACCAGGTGCTCCACT
1731  21_HRV63      AGGTGATGACATTGGTCATATAGTTATGCAGTACATGTACGTTCCACCCGGTGCCCCTCT
1732  22_HRV63b|    AGGTGATGACATTGGTCATATAGTTATGCAGTACATGTACGTTCCACCCGGTGCCCCTCT
1733  23_HRV63a|    AGGTGATGACATTGGTCATATAGTTATGCAGTACATGTACGTTCCACCCGGTGCCCCTCT
1734  24_HRV39      AGGTGAAGATATTGGACACATAGTAATGCAATACATGTATGTCCCACCTGGTGCACCTGT
1735  25_HRV39a|    AGGTGAAGATATTGGACACATAGTAATGCAATACATGTATGTCCCACCTGGTGCACCTGT
1736  26_HRV39b|    AGGTGAAGATATTGGACACATAGTAATGCAATACATGTATGTCCCACCTGGTGCACCTGT
1737  27_HRV10a|    GGGCGATGACATAGGTCACATAGTTATGCAATATATGTATGTGCCACCTGGGGCTCCAGT
1738  28_HRV10b|    GGGCGATGACATAGGTCACATAGTTATGCAATATATGTATGTGCCACCTGGGGCTCCAGT
1739  29_HRV10      GGGCGATGACATAGGTCACATAGTTATGCAATATATGTATGTGCCACCTGGGGCTCCAGT
1740  30_HRV100a    AGGAGATGACATAGGGCATATCGTAATGCAGTACATGTATGTGCCACCTGGAGCTCCAGT
1741  31_HRV100b    AGGAGATGACATAGGGCATATCGTAATGCAGTACATGTATGTGCCACCTGGAGCTCCAGT
1742  32_HRV100     AGGAGATGACATAGGGCATATCGTAATGCAGTACATGTATGTGCCACCTGGAGCTCCAGT
1743  33_HRV66      GGGTGATGATATAGGACATATTGTGATGCAATACATGTATGTACCACCTGGAGCCCCAAT
1744  34_HRV66b|    GGGTGATGATATAGGACATATTGTGATGCAATACATGTATGTACCACCTGGAGCCCCAAT
1745  35_HRV66a|    GGGTGATGATATAGGACATATTGTGATGCAATACATGTATGTACCACCTGGAGCCCCAAT
1746  36_HRV77a|    AGGTGATGACATAGGACATGTTGTCATGCAATACATGTATGTACCACCAGGGGCACCCAT
1747  37_HRV77b|    AGGTGATGACATAGGACATGTTGTCATGCAATACATGTATGTACCACCAGGGGCACCCAT
1748  38_HRV77      AGGTGATGACATAGGACATGTTGTCATGCAATACATGTATGTACCACCAGGGGCACCCAT
1749  39_HRV62a     TGGTGCAGATATAGGTCACATAGTTATGCAATATATGTATGTACCACCTGGGGCTCCACT
1750  40_HRV62b     TGGTGCAGATATAGGTCACATAGTTATGCAATATATGTATGTACCACCTGGGGCTCCACT
1751  41_HRV25      TGGTGCAGATATAGGTCACATAGTTATGCAGTACATGTATGTGCCACCTGGAGCCCCATT
1752  42_HRV29a     TGGTAATGATATAGGTCACATAGTTATGCAGTACATGTATGTACCACCTGGAGCTCCAGT
1753  43_HRV29b     TGGTAATGATATAGGTCACATAGTTATGCAGTACATGTATGTACCACCTGGAGCTCCAGT
1754  44_HRV44a     TGGTGATGATATAGGCCACATAGTTATGCAGTACATGTATGTACCACCTGGAGCTCCAGT
1755  45_HRV44b     TGGTGATGATATAGGCCACATAGTTATGCAGTACATGTATGTACCACCTGGAGCTCCAGT
```

FIG. D10 CONT'D

```
06.trace                                                                        9/20/2007 5:04 PM 1756  46_HRV31    TGGTAGTGACATAGGCCATATAGTCATGCAATACATGTATGTACCACCTGGGGCCCCAGT
1757  47_HRV31a|  TGGTAGTGACATAGGCCATATAGTCATGCAATACATGTATGTACCACCTGGGGCCCCAGT
1758  48_HRV31b|  TGGTAGTGACATAGGCCATATAGTCATGCAATACATGTATGTACCACCTGGGGCCCCAGT
1759  49_HRV47    TGGTGATGACATAGGTCACATAGTTATGCAATACATGTATGTGCCGCCTGGGGCTCCAGT
1760  50_HRV47a|  TGGTGATGACATAGGTCACATAGTTATGCAATACATGTATGTGCCGCCTGGGGCTCCAGT
1761  51_HRV47b|  TGGTGATGACATAGGTCACATAGTTATGCAATACATGTATGTGCCGCCTGGGGCTCCAGT
1762  52_HRV11    AGGAAATGATATTGGTCATGTTGTAATGCAATATATGTATGTCCCACCAGGTGCTCCAGT
1763  53_HRV11b|  AGGAAATGATATTGGTCATGTTGTAATGCAATATATGTATGTCCCACCAGGTGCTCCAGT
1764  54_HRV11a|  AGGAAATGATATTGGTCATGTTGTAATGCAATATATGTATGTCCCACCAGGTGCTCCAGT
1765  55_HRV76    AGGGGATGACATTGGTCATGTAGTGATGCAATACATGTATGTCCCACCAGGCGCTCCAGT
1766  56_HRV76b|  AGGGGATGACATTGGTCATGTAGTGATGCAATACATGTATGTCCCACCAGGCGCTCCAGT
1767  57_HRV76a|  AGGGGATGACATTGGTCATGTAGTGATGCAATACATGTATGTCCCACCAGGCGCTCCAGT
1768  58_HRV33    GGGAGATGATGTTGGTCATGTTGTAATGCAGTACATGTATGTCCCACCAGGTGCACCAGC
1769  59_HRV33b|  GGGAGATGATGTTGGTCATGTTGTAATGCAGTACATGTATGTCCCACCAGGTGCACCAGC
1770  60_HRV33a|  GGGAGATGATGTTGGTCATGTTGTAATGCAGTACATGTATGTCCCACCAGGTGCACCAGC
1771  61_HRV24a|  GGGAGATGACATTGGACATGTTGTAATGCAGTACATGTATATACCACCTGGAGCACCAGT
1772  62_HRV24b|  GGGAGATGACATTGGACATGTTGTAATGCAGTACATGTATATACCACCTGGAGCACCAGT
1773  63_HRV24    GGGAGATGACATTGGACATGTTGTAATGCAGTACATGTATATACCACCTGGAGCACCAGT
1774  64_HRV90    GGGCAATGATATTGGACATGTTGTGATGCAATACATGTATATACCACCTGGGGCACCAGT
1775  65_HRV90a|  GGGCAATGATATTGGACATGTTGTGATGCAATACATGTATATACCACCTGGGGCACCAGT
1776  66_HRV90b|  GGGCAATGATATTGGACATGTTGTGATGCAATACATGTATATACCACCTGGGGCACCAGT
1777  67_HRV34    AGGTGATGATATTGGACATGTTGTGATGCAATACATGTATGTACCACCAGGTGCACCAAT
1778  68_HRV34b|  AGGTGATGATATTGGACATGTTGTGATGCAATACATGTATGTACCACCAGGTGCACCAAT
1779  69_HRV34a|  AGGTGATGATATTGGACATGTTGTGATGCAATACATGTATGTACCACCAGGTGCACCAAT
1780  70_HRV50a|  GGGTGTTGATATTGGACATGTTGTCATGCAATACATGTATGTCCCACCAGGTGCACCAAT
1781  71_HRV50b|  GGGTGTTGATATTGGACATGTTGTCATGCAATACATGTATGTCCCACCAGGTGCACCAAT
1782  72_HRV50    GGGTGTTGATATTGGACATGTTGTCATGCAATACATGTATGTCCCACCAGGTGCACCAAT
1783  73_HRV18a|  GGGTGATGACATAGGACATATTGTTATGCAGTACATGTATGTTCCTCCAGGAGCACCAAT
1784  74_HRV18b|  GGGTGATGACATAGGACATATTGTTATGCAGTACATGTATGTTCCTCCAGGAGCACCAAT
1785  75_HRV18    GGGTGATGACATAGGACATATTGTTATGCAGTACATGTATGTTCCTCCAGGAGCACCAAT
1786  76_HRV55    GGGAGATGACATTGGACATGTAGTCATGCAATACATGTATGTTCCACCTGGAGCACCAAT
1787  77_HRV55b|  GGGAGATGACATTGGACATGTAGTCATGCAATACATGTATGTTCCACCTGGAGCACCAAT
1788  78_HRV55a|  GGGAGATGACATTGGACATGTAGTCATGCAATACATGTATGTTCCACCTGGAGCACCAAT
1789  79_HRV57    AGGTGAGGATATAGGCCATGTTGTAATGCAATACATGTATGTCCCTCCTGGGGCACCAAT
1790  80_HRV57a|  AGGTGAGGATATAGGCCATGTTGTAATGCAATACATGTATGTCCCTCCTGGGGCACCAAT
1791  81_HRV57b|  AGGTGAGGATATAGGCCATGTTGTAATGCAATACATGTATGTCCCTCCTGGGGCACCAAT
1792  82_HRV21    AACGGGTGACATAGGACATGTTGTAATGCAATATATGTATGTCCCACCAGGTGCTCCAAT
1793  83_HRVHan   AGCGGGTGACATAGGACATGTTGTGATGCAATATATGTATGTCCCACCAGGTGCTCCAAT
1794  84_HRV43    AAGCAATGATATAGGCCATGTGGTAATGCAGTACATGTATGTACCACCAGGTGCGCCAAT
1795  85_HRV43b|  AAGCAATGATATAGGCCATGTGGTAATGCAGTACATGTATGTACCACCAGGTGCGCCAAT
1796  86_HRV43a|  AAGCAATGATATAGGCCATGTGGTAATGCAGTACATGTATGTACCACCAGGTGCGCCAAT
1797  87_HRV75    AGGGAATGACATAGGCCATGTAGTAATGCAATATATGTATGTACCACCAGGAGCACCAAT
1798  88_HRV75b|  AGGGAATGACATAGGCCATGTAGTAATGCAATATATGTATGTACCACCAGGAGCACCAAT
1799  89_HRV75a|  AGGGAATGACATAGGCCATGTAGTAATGCAATATATGTATGTACCACCAGGAGCACCAAT
1800  96_HRV9a|d  AAGTGATAGCGTTGGCCATGTTGTTATGCAGTACATGTATGTACCACCAGGGGCACCTTT
1801  97_HRV9b|d  AAGTGATAGCGTTGGCCATGTTGTTATGCAGTACATGTATGTACCACCAGGGGCACCTTT
1802  98_HRV9     AAGTGATAGCGTTGGCCATGTTGTTATGCAGTACATGTATGTACCACCAGGGGCACCTTT
1803  99_HRV32    AAGTGACAGCATTGGTCATGTTGTTATGCAGTACATGTATGTACCACCAGGGGCTCCTCT
1804  100_HRV32a  AAGTGACAGCATTGGTCATGTTGTTATGCAGTACATGTATGTACCACCAGGGGCTCCTCT
1805  101_HRV32b  AAGTGACAGCATTGGTCATGTTGTTATGCAGTACATGTATGTACCACCAGGGGCTCCTCT
1806  102_HRV67   GAGTGACAGCATTGGGCATGTTGTAATGCAATATATGTATGTACCTCCAGGAGCACCATT
1807  103_HRV67a  GAGTGACAGCATTGGGCATGTTGTAATGCAATATATGTATGTACCTCCAGGAGCACCATT
1808  104_HRV67b  GAGTGACAGCATTGGGCATGTTGTAATGCAATATATGTATGTACCTCCAGGAGCACCATT
1809  105_HRV15   GAGTGATAACATCGGTCATGTTGTCATGCAATATATGTATGTTCCTCCGGGAGCCCCTTT
1810  106_HRV15a  GAGTGATAACATCGGTCATGTTGTCATGCAATATATGTATGTTCCTCCGGGAGCCCCTTT
1811  107_HRV15b  GAGTGATAACATCGGTCATGTTGTCATGCAATATATGTATGTTCCTCCGGGAGCCCCTTT
1812  108_HRV74a  AAGTGACAACATTGGCCATGTTGTTATGCAATACATGTATGTCCCCCCAGGAGCACCTTT
1813  109_HRV74b  AAGTGACAACATTGGCCATGTTGTTATGCAATACATGTATGTCCCCCCAGGAGCACCTTT
1814  110_HRV74   AAGTGACAACATTGGCCATGTTGTTATGCAATACATGTATGTCCCCCCAGGAGCACCTTT
1815  111_HRV38a  AAATGAAGGTGTGGGGCATGTTGTTATGCAGTATATGTATGTCCCTCCAGGGGCACCATT
1816  112_HRV38b  AAATGAAGGTGTGGGGCATGTTGTTATGCAGTATATGTATGTCCCTCCAGGGGCACCATT
1817  113_HRV38   AAATGAAGGTGTGGGGCATGTTGTTATGCAGTATATGTATGTCCCTCCAGGGGCACCATT
1818  114_HRV60   AAATGATGGCATAGGTCATGTTGTCATGCAATACATGTATGTCCCCCCAGGAGCACCATT
1819  115_HRV60a  AAATGATGGCATAGGTCATGTTGTCATGCAATACATGTATGTCCCCCCAGGAGCACCATT
1820  116_HRV60b  AAATGATGGCATAGGTCATGTTGTCATGCAATACATGTATGTCCCCCCAGGAGCACCATT
```

FIG. D10 CONT'D 06.trace                                                                9/20/2007 5:04 PM

```
1821  117_HRV64a    GAGTGCTAACATTGGTCATGTTGTTATGCAATATATGTATGTCCCTCCTGGAGCTCCAAT
1822  118_HRV64b    GAGTGCTAACATTGGTCATGTTGTTATGCAATATATGTATGTCCCTCCTGGAGCTCCAAT
1823  119_HRV64     GAGTGCTAACATTGGTCATGTTGTTATGCAATATATGTATGTCCCTCCTGGAGCTCCAAT
1824  120_HRV94a    AAGTGCTAATATTGGTCATGTTGTCATGCAGTACATGTATGTTCCTCCTGGAGCTCCAAA
1825  121_HRV94b    AAGTGCTAATATTGGTCATGTTGTCATGCAGTACATGTATGTTCCTCCTGGAGCTCCAAA
1826  122_HRV94     AAGTGCTAATATTGGTCATGTTGTCATGCAGTACATGTATGTTCCTCCTGGAGCTCCAAA
1827  123_HRV22     AAGTAAAAACATTGGTCATGTGGTCATGCAATACATGTATGTTCCGCCTGGAGCTCCTAA
1828  124_HRV22a    AAGTAAAAACATTGGTCATGTGGTCATGCAATACATGTATGTTCCGCCTGGAGCTCCTAA
1829  125_HRV22b    AAGTAAAAACATTGGTCATGTGGTCATGCAATACATGTATGTTCCGCCTGGAGCTCCTAA
1830  126_HRV82     AAGTAATGATATTGGGCATGTAGTGATGCAATACATGTATGTCCCACCAGGTGCTCCTAA
1831  127_HRV82b    AAGTAATGATATTGGGCATGTAGTGATGCAATACATGTATGTCCCACCAGGTGCTCCTAA
1832  128_HRV82a    AAGTAATGATATTGGGCATGTAGTGATGCAATACATGTATGTCCCACCAGGTGCTCCTAA
1833  129_HRV19     AAGTAAAAACATTGGACATGTTGTTATGCAATACATGTATGTGCCTCCTGGTGCTCCTAT
1834  130_HRV19a    AAGTAAAAACATTGGACATGTTGTTATGCAATACATGTATGTGCCTCCTGGTGCTCCTAT
1835  131_HRV19b    AAGTAAAAACATTGGACATGTTGTTATGCAATACATGTATGTGCCTCCTGGTGCTCCTAT
1836  132_HRV13     AGGTGGTGATGTCGGACATGTTGTTATGCAATACATGTATGTACCGCCCGGTGCACCCCT
1837  133_HRV13a    AGGTGGTGATGTCGGACATGTTGTTATGCAATACATGTATGTACCGCCCGGTGCACCCCT
1838  134_HRV13b    AGGTGGTGATGTCGGACATGTTGTTATGCAATACATGTATGTACCGCCCGGTGCACCCCT
1839  135_HRV41     GGGTAGTGATGTCGGACATGTTGTCATGCAATACATGTTCGTACCACCTGGCGCACCCCT
1840  136_HRV41a    GGGTAGTGATGTCGGACATGTTGTCATGCAATACATGTTCGTACCACCTGGCGCACCCCT
1841  137_HRV41b    GGGTAGTGATGTCGGACATGTTGTCATGCAATACATGTTCGTACCACCTGGCGCACCCCT
1842  138_HRV73     AAGTGGAGATGTGGGACATGTAGTTATGCAGTATATGTATGTCCCACCTGGAGCCCCTCT
1843  139_HRV73b    AAGTGGAGATGTGGGACATGTAGTTATGCAGTATATGTATGTCCCACCTGGAGCCCCTCT
1844  140_HRV73a    AAGTGGAGATGTGGGACATGTAGTTATGCAGTATATGTATGTCCCACCTGGAGCCCCTCT
1845  141_HRV61     AGGTGGTGACATTGGACACGTGGTCATGCAATACATGTATGTTCCACCTGGTGCACCTAC
1846  142_HRV61a    AGGTGGTGACATTGGACACGTGGTCATGCAATACATGTATGTTCCACCTGGTGCACCTAC
1847  143_HRV61b    AGGTGGTGACATTGGACACGTGGTCATGCAATACATGTATGTTCCACCTGGTGCACCTAC
1848  144_HRV96     GAGTGGTGATATTGGTCATGTGGTCATGCAATATATGTATGTTCCACCAGGTGCCCCCAC
1849  145_HRV96b    GAGTGGTGATATTGGTCATGTGGTCATGCAATATATGTATGTTCCACCAGGTGCCCCCAC
1850  146_HRV96a    GAGTGGTGATATTGGTCATGTGGTCATGCAATATATGTATGTTCCACCAGGTGCCCCCAC
1851   90_HRV16a|   AGATGGTCACATTGGTCATATAGTCATGCAATATATGTATGTACCACCAGGAGCACCTAT
1852   91_HRV16b|   AGATGGTCACATTGGTCATATAGTCATGCAATATATGTATGTACCACCAGGAGCACCTAT
1853   92_1AYM_A    AGATGGTCACATTGGTCATATAGTCATGCAATATATGTATGTACCACCAGGAGCACCTAT
1854   93_HRV81a|   GGAAGGTCATATTGGTCATATAGTAATGCAATACATGTATGTACCACCAGGAGCACCCAT
1855   94_HRV81b|   GGAAGGTCATATTGGTCATATAGTAATGCAATACATGTATGTACCACCAGGAGCACCCAT
1856   95_HRV81     GGAAGGTCATATTGGTCATATAGTAATGCAATACATGTATGTACCACCAGGAGCACCCAT
1857  147_HRV2      TAGTCAGGACATTGGACACATCACAATGCAATACATGTATGTTCCACCTGGTGCACCGGT
1858  148_HRV2a|    TAGTCAGGACATTGGACACATCACAATGCAATACATGTATGTTCCACCTGGTGCACCGGT
1859  149_HRV2b|    TAGTCAGGACATTGGACACATCACAATGCAATACATGTATGTTCCACCTGGTGCACCGGT
1860  150_HRV49a    TAGCAAGGATATTGGACACATTACAATGCAATACATGTATGTGCCCGCCAGGTGCACCTGT
1861  151_HRV49b    TAGCAAGGATATTGGACACATTACAATGCAATACATGTATGTGCCCGCCAGGTGCACCTGT
1862  152_HRV49     TAGCAAGGATATTGGACACATTACAATGCAATACATGTATGTGCCCGCCAGGTGCACCTGT
1863  153_HRV23a    TAGTCAAGATATTGGTCACATCACAATGCAGTATATGTATGTCCCACCAGGTGCTCCAAT
1864  154_HRV23b    TAGTCAAGATATTGGTCACATCACAATGCAGTATATGTATGTCCCACCAGGTGCTCCAAT
1865  155_HRV23     TAGTCAAGATATTGGTCACATCACAATGCAGTATATGTATGTCCCACCAGGTGCTCCAAT
1866  156_HRV30a    CAGCCAAGATATCGGACACATTACAATGCAGTATATGTATGTTCCACCTGGCGCTCCAAT
1867  157_HRV30b    CAGCCAAGATATCGGACACATTACAATGCAGTATATGTATGTTCCACCTGGCGCTCCAAT
1868  158_HRV30     CAGCCAAGATATCGGACACATTACAATGCAGTATATGTATGTTCCACCTGGCGCTCCAAT
1869  159_HRV7      AGGTAATGATATTGGACATATAGTTATGCAATTTATGTATGTACCTCCAGGGGCCCCAGT
1870  160_HRV7b|    AGGTAATGATATTGGACATATAGTTATGCAATTTATGTATGTACCTCCAGGGGCCCCAGT
1871  161_HRV7a|    AGGTAATGATATTGGACATATAGTTATGCAATTTATGTATGTACCTCCAGGGGCCCCAGT
1872  162_HRV88     AGGTGATGATACTGGACATATAGTACTGCAATTCATGTATGTGCCTCCAGGTGCACCAAT
1873  163_HRV88a    AGGTGATGATACTGGACATATAGTACTGCAATTCATGTATGTGCCTCCAGGTGCACCAAT
1874  164_HRV88b    AGGTGATGATACTGGACATATAGTACTGCAATTCATGTATGTGCCTCCAGGTGCACCAAT
1875  165_HRV36a    GGGAGATGATAGTGGGCATGTAGTATTACAATTCATGTATGTACCTCCAGGAGCGCCTGT
1876  166_HRV36b    GGGAGATGATAGTGGGCATGTAGTATTACAATTCATGTATGTACCTCCAGGAGCGCCTGT
1877  167_HRV36     GGGAGATGATAGTGGGCATGTAGTATTACAATTCATGTATGTACCTCCAGGAGCGCCTGT
1878  168_HRV89a    AGGAAATGATAGTTGGACATATAGTATTGCAATTTATGTATGTACCCCCAGGAGCACCTGT
1879  169_HRV89b    AGGAAATGATAGTTGGACATATAGTATTGCAATTTATGTATGTACCCCCAGGAGCACCTGT
1880  170_HRV89     AGGAAATGATAGTTGGACATATAGTATTGCAATTTATGTATGTACCCCCAGGAGCACCTGT
1881  171_HRV58     AGGAGAAGATAATGGACATATTTATGTATGTACCCCCAGGAGCACCTGT
1882  172_HRV58a    AGGAGAAGATAATGGACATATTGTGTTACAATTTATGTATGTACCCCCAGGAGCACCTGT
1883  173_HRV58b    AGGAGAAGATAATGGACATATTGTGTTACAATTTATGTATGTACCCCCAGGAGCACCTGT
1884  174_HRV12a    AGAAGGAAGCAATGGTCACGTGGTGGTCCAATACATGTATGTACCTCCTGGTGCCCCACT
1885  175_HRV12b    AGAAGGAAGCAATGGTCACGTGGTGGTCCAATACATGTATGTACCTCCTGGTGCCCCACT
```

FIG. D10 CONT'D 06.trace                                                              9/20/2007 5:04 PM

```
1886  176_HRV12     AGAAGGAAGCAATGGTCACGTGGTGGTCCAATACATGTATGTACCTCCTGGTGCCCCACT
1887  177_HRV78a    AGGAGACAATAATGGACATGTGGTGCTTCAATTTATGTTTGTTCCACCTGGAGCCCCTAT
1888  178_HRV78b    AGGAGACAATAATGGACATGTGGTGCTTCAATTTATGTTTGTTCCACCTGGAGCCCCTAT
1889  179_HRV78     AGGAGACAATAATGGACATGTGGTGCTTCAATTTATGTTTGTTCCACCTGGAGCCCCTAT
1890  180_HRV20     AGGTCGGGATAATGGGCATGTTGTTTTACAGTATATGTATGTACCACCAGGGGCACCAAT
1891  181_HRV20a    AGGTCGGGATAATGGGCATGTTGTTTTACAGTATATGTATGTACCACCAGGGGCACCAAT
1892  182_HRV20b    AGGTCGGGATAATGGGCATGTTGTTTTACAGTATATGTATGTACCACCAGGGGCACCAAT
1893  183_HRV68     TGGAAAAGATAATGGCCATGTGGTTTTACAGTACATGTATGTGCCGCCAGGGGCACCCAT
1894  184_HRV68a    TGGAAAAGATAATGGCCATGTGGTTTTACAGTACATGTATGTGCCGCCAGGGGCACCCAT
1895  185_HRV68b    TGGAAAAGATAATGGCCATGTGGTTTTACAGTACATGTATGTGCCGCCAGGGGCACCCAT
1896  186_HRV28     AGGTGATGATAATGGGCATGTAGTTATGCAATATATGTATGTACCTCCAGGAGCCCCCAT
1897  187_HRV28a    AGGTGATGATAATGGGCATGTAGTTATGCAATATATGTATGTACCTCCAGGAGCCCCCAT
1898  188_HRV28b    AGGTGATGATAATGGGCATGTAGTTATGCAATATATGTATGTACCTCCAGGAGCCCCCAT
1899  189_HRV53a    ACAAGGGAATAACGGGCACGTGGTGATACAATACATGTATGTACCACCGGGTGCTCCAAT
1900  190_HRV53b    ACAAGGGAATAACGGGCACGTGGTGATACAATACATGTATGTACCACCGGGTGCTCCAAT
1901  191_HRV53     ACAAGGGAATAACGGGCACGTGGTGATACAATACATGTATGTACCACCGGGTGCTCCAAT
1902  192_HRV46a    AGGGGATGATATTGGACATGTGGTCATACAATATATGTATGTGCCTCCTGGTGCTCCATT
1903  193_HRV46b    AGGGGATGATATTGGACATGTGGTCATACAATATATGTATGTGCCTCCTGGTGCTCCATT
1904  194_HRV46     AGGGGATGATATTGGACATGTGGTCATACAATATATGTATGTGCCTCCTGGTGCTCCATT
1905  195_HRV80a    AGGGGAGGACATTGGTCATGTAGTTATTCAATACATGTACGTACCACCAGGGGCCCCGTT
1906  196_HRV80b    AGGGGAGGACATTGGTCATGTAGTTATTCAATACATGTACGTACCACCAGGGGCCCCGTT
1907  197_HRV80     AGGGGAGGACATTGGTCATGTAGTTATTCAATACATGTACGTACCACCAGGGGCCCCGTT
1908  198_HRV51     GGGTGATGACATAGGGCACATTGTACTTCAATACATGTATGTACCCCCTGGAGGACCAGT
1909  199_HRV51a    GGGTGATGACATAGGGCACATTGTACTTCAATACATGTATGTACCCCCTGGAGGACCAGT
1910  200_HRV51b    GGGTGATGACATAGGGCACATTGTACTTCAATACATGTATGTACCCCCTGGAGGACCAGT
1911  201_HRV65a    AGGTGATGACATAGGGCACATAGTGCTTCAATATATGTATGTGCCTCCTGGTGGTCCTGT
1912  202_HRV65b    AGGTGATGACATAGGGCACATAGTGCTTCAATATATGTATGTGCCTCCTGGTGGTCCTGT
1913  203_HRV65     AGGTGATGACATAGGGCACATAGTGCTTCAATATATGTATGTGCCTCCTGGTGGTCCTGT
1914  204_HRV71a    AGGAGATGATTTAGGACATATTGTACTCCAGTACATGTATGTTCCCCCAGGTGGTCCAAT
1915  205_HRV71b    AGGAGATGATTTAGGACATATTGTACTCCAGTACATGTATGTTCCCCCAGGTGGTCCAAT
1916  206_HRV71     AGGAGATGATTTAGGACATATTGTACTCCAGTACATGTATGTTCCCCCAGGTGGTCCAAT
1917  207_HRV8      AAAAGGTGACCTTGGACACATAGTCCTTCAATACATGTATGTTCCCCCGGGTGCACCTCT
1918  208_HRV95     AGAAGGTGACCTTGGACACATAGTCCTCCAATACATGTATGTTCCCCCGGGTGCACCTCT
1919  209_HRV45     AGAAGGTAACTTGGGACACATTGTTGTGCAATACATGTTTGTACCACCAGGAGCACCTCT
1920  210_HRV45a    AGAAGGTAACTTGGGACACATTGTTGTGCAATACATGTTTGTACCACCAGGAGCACCTCT
1921  211_HRV45b    AGAAGGTAACTTGGGACACATTGTTGTGCAATACATGTTTGTACCACCAGGAGCACCTCT
1922  GROUP_1       -------------GG-CA--T-----T-CA-T---ATGT---T-CC-CC-GG-G--CC---
1923
1924  1_HRV1A1|d    TCCTTCAAAAAGAAACGATTTCTCATGGCAATCAGGCACCAATATGTCAATATTCTGGCA
1925  2_HRV1A2|d    TCCTTCAAAAAGAAACGATTTCTCATGGCAATCAGGCACCAATATGTCAATATTCTGGCA
1926  3_HRV1A|cD    TCCTTCAAAAAGAAACGATTTCTCATGGCAATCAGGCACCAATATGTCAATATTCTGGCA
1927  4_HRV1B1|d    TCCAAAAACAAGAAATGATTTCTCATGGCAATCAGGCACTAATATGTCAATATTCTGGCA
1928  5_HRV1B2|d    TCCAAAAACAAGAAATGATTTCTCATGGCAATCAGGCACTAATATGTCAATATTCTGGCA
1929  6_HRV1B       TCCAAAAACAAGAAATGATTTCTCATGGCAATCAGGCACTAATATGTCAATATTCTGGCA
1930  7_HRV40a|d    ACCAAAGAAAAGAAATGATTACACATGGCAGTCAGGCACTAATGCTTCTGTATTCTGGCA
1931  8_HRV40b|d    ACCAAAGAAAAGAAATGATTACACATGGCAGTCAGGCACTAATGCTTCTGTATTCTGGCA
1932  9_HRV40       ACCAAAGAAAAGAAATGATTACACATGGCAGTCAGGCACTAATGCTTCTGTATTCTGGCA
1933  10_HRV85      ACCAAGGAAAAGAGATGATTACACATGGCAATCAGGTACTAATGCTTCCGTGTTTTGGCA
1934  11_HRV85a     ACCAAGGAAAAGAGATGATTACACATGGCAATCAGGTACTAATGCTTCCGTGTTTTGGCA
1935  12_HRV85b|    ACCAAGGAAAAGAGATGATTACACATGGCAATCAGGTACTAATGCTTCCGTGTTTTGGCA
1936  13_HRV56a|    TCCAAACTCAAGAGATGATTTTACATGGCAATCTGGCACCAATGCTTCTGTCTTTTGGCA
1937  14_HRV56b|    TCCAAACTCAAGAGATGATTTTACATGGCAATCTGGCACCAATGCTTCTGTCTTTTGGCA
1938  15_HRV56      TCCAAACTCAAGAGATGATTTTACATGGCAATCTGGCACCAATGCTTCTGTCTTTTGGCA
1939  16_HRV54      ACCAGAAAAAAGGAATGATTACACCTGGGAGTCAAGCACAAACCCTTCTATATTTTGGCA
1940  17_HRV98      ACCTAAAAGAGGAATGATTATACTTGGGAATCAAGCACAAACCCTTCTATATTCTGGCA
1941  18_HRV59a|    GCCCACAAAGAGAGATGATTACACATGGCAATCTGGTACTAATGCTTCAATATTCTGGCA
1942  19_HRV59b|    GCCCACAAAGAGAGATGATTACACATGGCAATCTGGTACTAATGCTTCAATATTCTGGCA
1943  20_HRV59      GCCCACAAAGAGAGATGATTACACATGGCAATCTGGTACTAATGCTTCAATATTCTGGCA
1944  21_HRV63      ACCCACCCGAAGAAGATTACACATGGCAATCTGGCACTAATGCTTCAATATTCTGGCA
1945  22_HRV63b|    ACCCACCCGAAGAAGATTACACATGGCAATCTGGCACTAATGCTTCAATATTCTGGCA
1946  23_HRV63a|    ACCCACCCGAAGAAGATTACACATGGCAATCTGGCACTAATGCTTCAATATTCTGGCA
1947  24_HRV39      ACCTAAGAAGAGAGATGATTACACATGGCAATCTGGAACAAATGCCTCAGTTTTCTGGCA
1948  25_HRV39a|    ACCTAAGAAGAGAGATGATTACACATGGCAATCTGGAACAAATGCCTCAGTTTTCTGGCA
1949  26_HRV39b|    ACCTAAGAAGAGAGATGATTACACATGGCAATCTGGAACAAATGCCTCAGTTTTCTGGCA
1950  27_HRV10a|    ACCAACTAAGAGAGATGATTTTGCTTGGCAGTCGGGAACAAATGCATCAGTCTTCTGGCA
```

FIG. D10 CONT'D 06.trace                                                                              9/20/2007 5:04 PM

```
1951  28_HRV10b|    ACCAACTAAGAGAGATGATTTTGCTTGGCAGTCGGGAACAAATGCATCAGTCTTCTGGCA
1952  29_HRV10     ACCAACTAAGAGAGATGATTTTGCTTGGCAGTCGGGAACAAATGCATCAGTCTTCTGGCA
1953  30_HRV100a   TCCAACAAAAAGGGATGATTTTGCATGGCAATCAGGCACAAATGCATCAGTTTTTTGGCA
1954  31_HRV100b   TCCAACAAAAAGGGATGATTTTGCATGGCAATCAGGCACAAATGCATCAGTTTTTTGGCA
1955  32_HRV100    TCCAACAAAAAGGGATGATTTTGCATGGCAATCAGGCACAAATGCATCAGTTTTTTGGCA
1956  33_HRV66     TCCAGATAATAGAACACACTTTGCTTGGCAATCAGGAACAAATGCATCTATATTCTGGCA
1957  34_HRV66b|   TCCAGATAATAGAACACACTTTGCTTGGCAATCAGGAACAAATGCATCTATATTCTGGCA
1958  35_HRV66a|   TCCAGATAATAGAACACACTTTGCTTGGCAATCAGGAACAAATGCATCTATATTCTGGCA
1959  36_HRV77a|   ACCAGATAGCAGGACTCATTTTGCATGGCAGTCAGGGACTAATGCATCAATATTCTGGCA
1960  37_HRV77b|   ACCAGATAGCAGGACTCATTTTGCATGGCAGTCAGGGACTAATGCATCAATATTCTGGCA
1961  38_HRV77     ACCAGATAGCAGGACTCATTTTGCATGGCAGTCAGGGACTAATGCATCAATATTCTGGCA
1962  39_HRV62a    ACCAACAGACAGAAAGCATTTTGCCTGGCAATCAAGTACTAATGCATCAATATTTTGGCA
1963  40_HRV62b    ACCAACAGACAGAAAGCATTTTGCCTGGCAATCAAGTACTAATGCATCAATATTTTGGCA
1964  41_HRV25     ACCAACAGACAGAAAACACTTTGCATGGCAATCAAGTACTAATGCATCAATATTTTGGCA
1965  42_HRV29a    ACCAAATGACAGAAATCATTTTGCATGGCAATCAGGGACTAATGCATCAATATTCTGGCA
1966  43_HRV29b    ACCAAATGACAGAAATCATTTTGCATGGCAATCAGGGACTAATGCATCAATATTCTGGCA
1967  44_HRV44a    ACCAGATGACAGAAACCACTTTGCATGGCAATCGGGGACTAATGCATCAATATTCTGGCA
1968  45_HRV44b    ACCAGATGACAGAATCCACTTTGCATGGCAATCGGGGAATAATGCATCAATATTCTGGCA
1969  46_HRV31     ACCAACAAATAGAAAACATTTTGCATGGCAATCAGGTACTAATGCATCGATTTTCTGGCA
1970  47_HRV31a|   ACCAACAAATAGAAAACATTTTGCATGGCAATCAGGTACTAATGCATCGATTTTCTGGCA
1971  48_HRV31b|   ACCAACAAATAGAAAACATTTTGCATGGCAATCAGGTACTAATGCATCGATTTTCTGGCA
1972  49_HRV47     GCCAACAAGTAGAGAGCACTTTGCATGGCAGTCAGGTACCAATGCATCAACTTTCTGGCA
1973  50_HRV47a|   GCCAACAAGTAGAGAGCACTTTGCATGGCAGTCAGGTACCAATGCATCAACTTTCTGGCA
1974  51_HRV47b|   GCCAACAAGTAGAGAGCACTTTGCATGGCAGTCAGGTACCAATGCATCAATTTTCTGGCA
1975  52_HRV11     TCCAGAGAAAAGAGATGATTATACATGGCAATCAGGAACAAATGCATCTATTTTCTGGCA
1976  53_HRV11b|   TCCAGAGAAAAGAGATGATTATACATGGCAATCAGGAACAAATGCATCTATTTTCTGGCA
1977  54_HRV11a|   TCCAGAGAAAAGAGATGATTATACATGGCAATCAGGAACAAATGCATCTATTTTCTGGCA
1978  55_HRV76     TCCAAAGAAGAGAGATGACTACACATGGCAGTCAGGAACCAATGCATCTATTTTCTGGCA
1979  56_HRV76b|   TCCAAAGAAGAGAGATGACTACACATGGCAGTCAGGAACCAATGCATCTATTTTCTGGCA
1980  57_HRV76a|   TCCAAAGAAGAGAGATGACTACACATGGCAGTCAGGAACCAATGCATCTATTTTCTGGCA
1981  58_HRV33     TCCAGAAAAGAGAGATGATTACACATGGCAATCAGGAACAAATGCATCTGTCTTTTGGCA
1982  59_HRV33b|   TCCAGAAAAGAGAGATGATTACACATGGCAATCAGGAACAAATGCATCTGTCTTTTGGCA
1983  60_HRV33a|   TCCAGAAAAGAGAGATGATTACACATGGCAATCAGGAACAAATGCATCTGTCTTTTGGCA
1984  61_HRV24a|   CCCAACAAAGAGAGATGATTATACATGGCAATCAGGAACAAATGCATCTGTCTTTTGGCA
1985  62_HRV24b|   CCCAACAAAGAGAGATGATTATACATGGCAATCAGGAACAAATGCATCTGTCTTTTGGCA
1986  63_HRV24     CCCAACAAAGAGAGATGATTATACATGGCAATCAGGAACAAATGCATCTGTCTTTTGGCA
1987  64_HRV90     ACCTGAGAAGAGGGATGATTATGCATGGCAATCAGGCACTAATGCATCTATCTTTTGGCA
1988  65_HRV90a|   ACCTGAGAAGAGGGATGATTATGCATGGCAATCAGGCACTAATGCATCTATCTTTTGGCA
1989  66_HRV90b|   ACCTGAGAAGAGGGATGATTATGCATGGCAATCAGGCACTAATGCATCTATCTTTTGGCA
1990  67_HRV34     ACCTAAAACTAGAGATGATTTTGCATGGCAATCTGGAACAAATGCCTCAATATTTTGGCA
1991  68_HRV34b|   ACCTAAAACTAGAGATGATTTTGCATGGCAATCTGGAACAAATGCCTCAATATTTTGGCA
1992  69_HRV34a|   ACCTAAAACTAGAGATGATTTTGCATGGCAATCTGGAACAAATGCCTCAATATTTTGGCA
1993  70_HRV50a|   ACCCAAGACTAGGGATGATTTTGCCTGGCAATCTGGAACTAATGCTTCAATCTTTTGGCA
1994  71_HRV50b|   ACCCAAGACTAGGGATGATTTTGCCTGGCAATCTGGAACTAATGCTTCAATCTTTTGGCA
1995  72_HRV50     ACCCAAGACTAGGGATGATTTTGCCTGGCAATCTGGAACTAATGCTTCAATCTTTTGGCA
1996  73_HRV18a|   ACCAAAAACCAGAGATGATTTTGCCTGGCAATCTGGAACAAATGCATCAATCTTCTGGCA
1997  74_HRV18b|   ACCAAAAACCAGAGATGATTTTGCCTGGCAATCTGGAACAAATGCATCAATCTTCTGGCA
1998  75_HRV18     ACCAAAAACCAGAGATGATTTTGCCTGGCAATCTGGAACAAATGCATCAATCTTCTGGCA
1999  76_HRV55     TCCAAAGACAAGAGAAGATTATGCTTGGCAATCAGGGACCAATGCATCTATCTTTTGGCA
2000  77_HRV55b|   TCCAAAGACAAGAGAAGATTATGCTTGGCAATCAGGGACCAATGCATCTATCTTTTGGCA
2001  78_HRV55a|   TCCAAAGACAAGAGAAGATTATGCTTGGCAATCAGGGACCAATGCATCTATCTTTTGGCA
2002  79_HRV57     TCCAAAACAAGAGAGGATTATACATGGCAATCTGGTACCAATGCTTCAATATTTTGGCA
2003  80_HRV57a|   TCCAAAAACAAGAGAGGATTATACATGGCAATCTGGTACCAATGCTTCAATATTTTGGCA
2004  81_HRV57b|   TCCAAAAACAAGAGAGGATTATACATGGCAATCTGGTACCAATGCTTCAATATTTTGGCA
2005  82_HRV21     TCCAAAAACTAGGGAAGATTTTGCTTGGCAGTCAGGCACTAATGCATCCATTTTCTGGCA
2006  83_HRVHan    TCCAAAAACTAGGGAAGATTTTGCTTGGCAGTCAGGTACCAATGCATCCATTTTCTGGCA
2007  84_HRV43     TCCAAAAACTAGGGAAGATTATGCATGGCAATCTGGCACAAATGCATCTGTTTTCTGGCA
2008  85_HRV43b|   TCCAAAAACTAGGAAAGATTATGCATGGCAATCTGGCACAAATGCATCTGTTTTCTGGCA
2009  86_HRV43a|   TCCAAAAACTAGGAAAGATTATGCATGGCAATCTGGCACAAATGCATCTGTTTTCTGGCA
2010  87_HRV75     ACCAACAACTAGAAAAGATTATGCATGGCAATCTGGAACAAATGCATCTGTATTTTGGCA
2011  88_HRV75b|   ACCAACAACTAGAAAAGATTATGCATGGCAATCTGGAACAAATGCATCTGTATTTTGGCA
2012  89_HRV75a|   ACCAACAACTAGAAAAGATTATGCATGGCAATCTGGAACAAATGCATCTGTATTTTGGCA
2013  96_HRV9a|d   ACCAAGGACTAGAGATGATTATGCATGGCAATCAGGCACAAATGCATCCATCTTTTGGCA
2014  97_HRV9b|d   ACCAAGGACTAGAGATGATTATGCATGGCAATCAGGCACAAATGCTTCCATCTTTTGGCA
2015  98_HRV9      ACCAAGGACTAGAGATGATTATGCATGGCAATCAGGCACAAATGCTTCCATCTTTTGGCA
```

FIG. D10 CONT'D 06.trace                                                                                                        9/20/2007 5:04 PM

```
2016  99_HRV32      ACCACAAGCAAGAGATGACTACACATGGCAATCTGGCACGAATGCATCTATCTTTTGGCA
2017 100_HRV32a     ACCACAAGCAAGAGATGACTACACATGGCAATCTGGCACGAATGCATCTATCTTTTGGCA
2018 101_HRV32b     ACCACAAGCAAGAGATGACTACACATGGCAATCTGGCACGAATGCATCTATCTTTTGGCA
2019 102_HRV67      ACCAACAAAAGAGATGACTACACATGGCAATCAGGTACAAATGCATCCATCTTTTGGCA
2020 103_HRV67a     ACCAACAAAAGAGATGACTACACATGGCAATCAGGTACAAATGCATCCATCTTTTGGCA
2021 104_HRV67b     ACCAACAAAAGAGATGACTACACATGGCAATCAGGTACAAATGCATCCATCTTTTGGCA
2022 105_HRV15      ACCCAATAAAAGGAATGATTACACATGGCAATCAGGTACAAATGCCTCTGTTTTCTGGCA
2023 106_HRV15a     ACCCAATAAAAGGAATGATTACACATGGCAATCAGGTACAAATGCCTCTGTTTTCTGGCA
2024 107_HRV15b     ACCCAATAAAAGGAATGATTACACATGGCAATCAGGTACAAATGCCTCTGTTTTCTGGCA
2025 108_HRV74a     ACCCAAGAAAAGAGATGATTACACATGGCAATCTGGCACAAATGCATCTGTGTTTTGGCA
2026 109_HRV74b     ACCCAAGAAAAGAGATGATTACACATGGCAATCTGGCACAAATGCATCTGTGTTTTGGCA
2027 110_HRV74      ACCCAAGAAAAGAGATGATTACACATGGCAATCTGGCACAAATGCATCTGTGTTTTGGCA
2028 111_HRV38a     ACCCAGGAAGAGAGATGATTACACTTGGCAATCTGGTACAAATGCCTCTGTTTTCTGGCA
2029 112_HRV38b     ACCCAGGAAGAGAGATGATTACACTTGGCAATCTGGTACAAATGCCTCTGTTTTCTGGCA
2030 113_HRV38      ACCCAGGAAGAGAGATGATTACACTTGGCAATCTGGTACAAATGCCTCTGTTTTCTGGCA
2031 114_HRV60      ACCTACTAAAAGAGACGATTACACATGGCAATCTGGCACAAATGCTTCTGTATTTTGGCA
2032 115_HRV60a     ACCTACTAAAAGAGACGATTACACATGGCAATCTGGCACAAATGCTTCTGTATTTTGGCA
2033 116_HRV60b     ACCTACTAAAAGAGACGATTACACATGGCAATCTGGCACAAATGCTTCTGTATTTTGGCA
2034 117_HRV64a     ACCAACCAAAAGAAATTACGTCTGGCAGTCAGGCACCAATGCATCCATCTTTTGGCA
2035 118_HRV64b     ACCAACCAAAAGAAATGATTACGTCTGGCAGTCAGGCACCAATGCATCCATCTTTTGGCA
2036 119_HRV64      ACCAACCAAAAGAAATGATTACGTCTGGCAGTCAGGCACCAATGCATCCATCTTTTGGCA
2037 120_HRV94a     ACCAGACAAAAGAGATGATTATGTTTGGCAATCAGGAACTAATGCATCTATATTCTGGCA
2038 121_HRV94b     ACCAGACAAAAGAGATGATTATGTTTGGCAATCAGGAACTAATGCATCTATATTCTGGCA
2039 122_HRV94      ACCAGACAAAAGAGATGATTATGTTTGGCAATCAGGAACTAATGCATCTATATTCTGGCA
2040 123_HRV22      ACCTGAAAAGAGAGATGACTACACATGGCAATCTGGCACTAATGCATCTGTTTTCTGGCA
2041 124_HRV22a     ACCTGAAAAGAGAGATGACTACACATGGCAATCTGGCACTAATGCATCTGTTTTCTGGCA
2042 125_HRV22b     ACCTGAAAAGAGAGATGACTACACATGGCAATCTGGCACTAATGCATCTGTTTTCTGGCA
2043 126_HRV82      ACCAGAAAAGAGAGACGACTACACTTGGCAATCTGGAACTAATGCTTCAATTTTCTGGCA
2044 127_HRV82b     ACCAGAAAAGAGAGACGACTACACTTGGCAATCTGGAACTAATGCTTCAATTTTCTGGCA
2045 128_HRV82a     ACCAGAAAAGAGAGACGACTACACTTGGCAATCTGGAACTAATGCTTCAATTTTCTGGCA
2046 129_HRV19      CCCAAAAACTAGAAATGATTACACATGGCAATCAGGTACTAATGCATCTATATTTTGGCA
2047 130_HRV19a     CCCAAAAACTAGAAATGATTACACATGGCAATCAGGTACTAATGCATCTATATTTTGGCA
2048 131_HRV19b     CCCAAAAACTAGAAATGATTACACATGGCAATCAGGTACTAATGCATCTATATTTTGGCA
2049 132_HRV13      TCCAACGAAGAGAAATGATTACACATGGCAATCTGGCACCAATGCATCTGTTTTCTGGCA
2050 133_HRV13a     TCCAACGAAGAGAAATGATTACACATGGCAATCTGGCACCAATGCATCTGTTTTCTGGCA
2051 134_HRV13b     TCCAACGAAGAGAAATGATTACACATGGCAATCTGGCACCAATGCATCTGTTTTCTGGCA
2052 135_HRV41      CCCAGAAAAGAGAGATGATTACACATGGCAATCTGGCACCAATGCATCTGTATTCTGGCA
2053 136_HRV41a     CCCAGAAAAGAGAGATGATTACACATGGCAATCTGGCACCAATGCATCTGTATTCTGGCA
2054 137_HRV41b     CCCAGAAAAGAGAGATGATTACACATGGCAATCTGGCACCAATGCATCTGTATTCTGGCA
2055 138_HRV73      ACCCACAAAAGAAATGACTACACATGGCAGTCCGGCACTAATGCATCAGTATTCTGGCA
2056 139_HRV73b     ACCCACAAAAGAAATGACTACACATGGCAGTCCGGCACTAATGCATCAGTATTCTGGCA
2057 140_HRV73a     ACCCACAAAAGAAATGACTACACATGGCAGTCCGGCACTAATGCATCAGTATTCTGGCA
2058 141_HRV61      ACCTGAGAAAAGAAATGATTTCACATGGCAATCAGGCACAAATGCATCTGTTTTCTGGCA
2059 142_HRV61a     ACCTGAGAAAAGAAATGATTTCACATGGCAATCAGGCACAAATGCATCTGTTTTCTGGCA
2060 143_HRV61b     ACCTGAGAAAAGAAATGATTTCACATGGCAATCAGGCACAAATGCATCTGTTTTCTGGCA
2061 144_HRV96      ACCTGAGAAGAGAGATGACTTTACATGGCAATCAGGCACAAATGCATCTGTGTTTTGGCA
2062 145_HRV96b     ACCTGAGAAGAGAGATGACTTTACATGGCAATCAGGCACAAATGCATCTGTGTTTTGGCA
2063 146_HRV96a     ACCTGAGAAGAGAGATGACTTTACATGGCAATCAGGCACAAATGCATCTGTGTTTTGGCA
2064  90_HRV16a|    ACCAACAACTAGAAATGACTATGCTTGGCAATCTGGAACAAATGCATCTGTATTTTGGCA
2065  91_HRV16b|    ACCAACAACTAGAAATGACTATGCTTGGCAATCTGGAACAAATGCATCTGTATTTTGGCA
2066  92_1AYM_A     ACCAACAACTAGAAATGACTATGCTTGGCAATCTGGAACAAATGCATCTGTATTTTGGCA
2067  93_HRV81a|    TCCAACAACTAGAGAAGACTATGCTTGGCAATCTGGAACAAATGCATCTATATTCTGGCA
2068  94_HRV81b|    TCCAACAACTAGAGAAGACTATGCTTGGCAATCTGGAACAAATGCATCTATATTCTGGCA
2069  95_HRV81      TCCAACAACTAGAGAAGACTATGCTTGGCAATCTGGAACAAATGCATCTATATTCTGGCA
2070 147_HRV2       GCCCAATAGTAGGGACGATTATGCATGGCAGTCTGGCACTAATGCCTCTGTTTTCTGGCA
2071 148_HRV2a|     GCCCAATAGTAGGGACGATTATGCATGGCAGTCTGGCACTAATGCCTCTGTTTTCTGGCA
2072 149_HRV2b|     GCCCAATAGTAGGGACGATTATGCATGGCAGTCTGGCACTAATGCCTCTGTTTTCTGGCA
2073 150_HRV49a     ACCAAAGAGCAGAGATGATTATGCATGGCAGTCTGGCACTAATGCATCTGTTTTCTGGCA
2074 151_HRV49b     ACCAAAGAGCAGAGATGATTATGCATGGCAGTCTGGCACTAATGCATCTGTTTTCTGGCA
2075 152_HRV49      ACCAAAGAGCAGAGATGATTATGCATGGCAGTCTGGCACTAATGCATCTGTTTTCTGGCA
2076 153_HRV23a     ACCGGAAAGTAGAAATGACTATGCATGGCAATCTGGAACAAATGCGTCCATTTTTTGGCA
2077 154_HRV23b     ACCGGAAAGTAGAAATGACTATGCATGGCAATCTGGAACAAATGCGTCCATTTTTTGGCA
2078 155_HRV23      ACCGGAAAGTAGAAATGACTATGCATGGCAATCTGGAACAAATGCGTCCATTTTTTGGCA
2079 156_HRV30a     TCCCGAGAGCAGAAATGACTATGCATGGCAGTCTGGAACAAATGCATCTGTTTTTGGCA
2080 157_HRV30b     TCCCGAGAGCAGAAATGACTATGCATGGCAGTCTGGAACAAATGCATCTGTTTTTGGCA
```

FIG. D10 CONT'D

```
06.trace                                                                      9/20/2007 5:04 PM 2081 158_HRV30    TCCCGAGAGCAGAAATGACTATGCATGGCAGTCTGGAACAAATGCATCTGTTTTTTGGCA
2082 159_HRV7     TCCAATAAAACGCGAAGATTATACATGGCAATCAGGAACAAATGCTTCTATATTTTGGCA
2083 160_HRV7b|   TCCAATAAAACGCGAAGATTATACATGGCAATCAGGAACAAATGCTTCTATATTTTGGCA
2084 161_HRV7a|   TCCAATAAAACGCGAAGATTATACATGGCAATCAGGAACAAATGCTTCTATATTTTGGCA
2085 162_HRV88    TCCCAAGAAACGTGATGATTACACATGGCAGTCAGGAACAAATGCATCTGTGTTCTGGCA
2086 163_HRV88a   TCCCAAGAAACGTGATGATTACACATGGCAGTCAGGAACAAATGCATCTGTGTTCTGGCA
2087 164_HRV88b   TCCCAAGAAACGTGATGATTACACATGGCAGTCAGGAACAAATGCATCTGTGTTCTGGCA
2088 165_HRV36a   TCCTGTGAAGCGTGATGACTACACATGGCAATCAGGGACAAATGCATCTGTGTTCTGGCA
2089 166_HRV36b   TCCTGTGAAGCGTGATGACTACACATGGCAATCAGGGACAAATGCATCTGTGTTCTGGCA
2090 167_HRV36    TCCTGTGAAGCGTGATGACTACACATGGCAATCAGGGACAAATGCATCTGTGTTCTGGCA
2091 168_HRV89a   CCCCGAAAAACGTGATGATTACACATGGCAATCAGGAACAAATGCATCTGTGTTCTGGCA
2092 169_HRV89b   CCCCGAAAAACGTGATGATTACACATGGCAATCAGGAACAAATGCATCTGTGTTCTGGCA
2093 170_HRV89    CCCCGAAAAACGTGATGATTACACATGGCAATCAGGAACAAATGCATCTGTGTTCTGGCA
2094 171_HRV58    ACCCAAGAATCGTGATGACTTTACATGGCAATCAGGCACAAATGCATCTGTTTTCTGGCA
2095 172_HRV58a   ACCCAAGAATCGTGATGACTTTACATGGCAATCAGGCACAAATGCATCTGTTTTCTGGCA
2096 173_HRV58b   ACCCAAGAATCGTGATGACTTTACATGGCAATCAGGCACAAATGCATCTGTTTTCTGGCA
2097 174_HRV12a   ACCCAAAAAACGTGATGATTACACATGGCAATCTGGCACCAACGCCTCAGTTTTTTGGCA
2098 175_HRV12b   ACCCAAAAAACGTGATGATTACACATGGCAATCTGGCACCAACGCCTCAGTTTTTTGGCA
2099 176_HRV12    ACCCAAAAAACGTGATGATTACACATGGCAATCTGGCACCAACGCCTCAGTTTTTTGGCA
2100 177_HRV78a   ACCAAAGAAGAGAGATGACTATACTTGGCAGTCAGGCACCAATGCATCTGTGTTTTGGCA
2101 178_HRV78b   ACCAAAGAAGAGAGATGACTATACTTGGCAGTCAGGCACCAATGCATCTGTGTTTTGGCA
2102 179_HRV78    ACCAAAGAAGAGAGATGACTATACTTGGCAGTCAGGCACCAATGCATCTGTGTTTTGGCA
2103 180_HRV20    ACCAAAGACTAGAGATGACTACACATGGCAATCAGGGACAAATGCATCAGTATTTTGGCA
2104 181_HRV20a   ACCAAAGACTAGAGATGACTACACATGGCAATCAGGGACAAATGCATCAGTATTTTGGCA
2105 182_HRV20b   ACCAAAGACTAGAGATGACTACACATGGCAATCAGGGACAAATGCATCAGTATTTTGGCA
2106 183_HRV68    ACCAAAAACTAGAGATGATTACACATGGCAGTCAGGCACTAATGCATCAGTGTTTTGGCA
2107 184_HRV68a   ACCAAAAACTAGAGATGATTACACATGGCAGTCAGGCACTAATGCATCAGTGTTTTGGCA
2108 185_HRV68b   ACCAAAAACTAGAGATGATTACACATGGCAGTCAGGCACTAATGCATCAGTGTTTTGGCA
2109 186_HRV28    CCCCACTACCAGAAATGATTACACATGGCAATCCAGTACCAATGCCTCTGTTTTCTGGCA
2110 187_HRV28a   CCCCACTACCAGAAATGATTACACATGGCAATCCAGTACCAATGCCTCTGTTTTCTGGCA
2111 188_HRV28b   CCCCACTACCAGAAATGATTACACATGGCAATCCAGTACCAATGCCTCTGTTTTCTGGCA
2112 189_HRV53a   ACCCAAAACCAGAGATGACTATACCTGGCAATCTGGAACTAATGCTTCAGTCTTTTGGCA
2113 190_HRV53b   ACCCAAAACCAGAGATGACTATACCTGGCAATCTGGAACTAATGCTTCAGTCTTTTGGCA
2114 191_HRV53    ACCCAAAACCAGAGATGACTATACCTGGCAATCTGGAACTAATGCTTCAGTCTTTTGGCA
2115 192_HRV46a   ACCGAGATATCGGAATGATTATACTTGGCAGTCTGGTACTAATGCTTCAGTGTTCTGGCA
2116 193_HRV46b   ACCGAGATATCGGAATGATTATACTTGGCAGTCTGGTACTAATGCTTCAGTTCTGGCA
2117 194_HRV46    ACCGAGATATCGGAATGATTATACTTGGCAGTCTGGTACTAATGCTTCAGTGTTCTGGCA
2118 195_HRV80a   GCCAAACAAACGCAATGATTATACTTGGCAGTCTGGCACGAATGCTTCAGTCTTCTGGCA
2119 196_HRV80b   GCCAAACAAACGCAATGATTATACTTGGCAGTCTGGCACGAATGCTTCAGTCTTCTGGCA
2120 197_HRV80    GCCAAACAAACGCAATGATTATACTTGGCAGTCTGGCACGAATGCTTCAGTCTTCTGGCA
2121 198_HRV51    TCCACTTACTAGGAAAGATGATGAGTGGCAATCAGGAACTAATGCTTCAGTATTCTGGCA
2122 199_HRV51a   TCCACTTACTAGGAAAGATGATGAGTGGCAATCAGGAACTAATGCTTCAGTATTCTGGCA
2123 200_HRV51b   TCCACTTACTAGGAAAGATGATGAGTGGCAATCAGGAACTAATGCTTCAGTATTCTGGCA
2124 201_HRV65a   TCCAAAAACTAGAAAAGATGAAGAGTGGCAGACAGGAACTAATGCTTCAGTCTTTTGGCA
2125 202_HRV65b   TCCAAAAACTAGAAAAGATGAAGAGTGGCAGACAGGAACTAATGCTTCAGTCTTTTGGCA
2126 203_HRV65    TCCAAAAACTAGAAAAGATGAAGAGTGGCAGACAGGAACTAATGCTTCAGTCTTTTGGCA
2127 204_HRV71a   ACCAGAGACCAGGGATGCCGATGAATGGCAGTCTGGAACTAATGCATCAGTCTTTTGGCA
2128 205_HRV71b   ACCAGAGACCAGGGATGCCGATGAATGGCAGTCTGGAACTAATGCATCAGTCTTTTGGCA
2129 206_HRV71    ACCAGAGACCAGGGATGCCGATGAATGGCAGTCTGGAACTAATGCATCAGTCTTTTGGCA
2130 207_HRV8     TCCAGATAAAAGGATGCACGATGCCTGGCAAACCAGTACAAATGCCTCAGTCTTCTGGCA
2131 208_HRV95    TCCAGATAAAAGGATGCACGATGCCTGGCAAACCAGTACAAATGCCTCAGTCTTCTGGCA
2132 209_HRV45    CCCTGTTAGTAGAACTGACAACACTTGGCAATCTAGCACAAATGCATCAGTCTTTTGGCA
2133 210_HRV45a   CCCTGTTAGTAGAACTGACAACACTTGGCAATCTAGCACAAATGCATCAGTCTTTTGGCA
2134 211_HRV45b   CCCTGTTAGTAGAACTGACAACACTTGGCAATCTAGCACAAATGCATCAGTCTTTTGGCA
2135 GROUP_1      -CC--------G-------------TGG-A--C--G-A--AA----TC----TT-TGGCA
2136
2137 1_HRV1A1|d   ACATGGACAGCCATTTCCTAGATTTTCTTTACCATTTCTTAGCATTGCATCAGCTTATTA
2138 2_HRV1A2|d   ACATGGACAGCCATTTCCTAGATTTTCTTTACCATTTCTTAGCATTGCATCAGCTTATTA
2139 3_HRV1A|cD   ACATGGACAGCCATTTCCTAGATTTTCTTTACCATTTCTTAGCATTGCATCAGCTTATTA
2140 4_HRV1B1|d   ACATGGACAACCGTTCCCTAGATTTTCTTTACCATTTCTTAGCATTGCATCAGCTTATTA
2141 5_HRV1B2|d   ACATGGACAACCGTTCCCTAGATTCTCTTTACCATTTCTTAGCATTGCATCAGCTTATTA
2142 6_HRV1B      ACATGGACAACCGTTCCCTAGATTCTCTTTACCATTTCTTAGCATTGCATCAGCTTATTA
2143 7_HRV40a|d   ACATGGTCAAACTTTCCCTAGATTTTCTTTACCTTTCCTAAGCATAGCTTCAGCATACTA
2144 8_HRV40b|d   ACATGGTCAAACTTTCCCTAGATTTTCTTTACCTTTCCTAAGCATAGCTTCAGCATACTA
2145 9_HRV40      ACATGGTCAAACTTTCCCTAGATTTTCTTTACCTTTCCTAAGCATAGCTTCAGCATACTA
```

FIG. D10 CONT'D

```
06.trace                                                                                    9/20/2007 5:04 PM 2146  10_HRV85      ACATGGGCAAACTTTCCCCAGATTTTCCTTACCTTTCTTGAGTGTTGCTTCAGCATATTA
2147  11_HRV85a|    ACATGGGCAAACTTTCCCCAGATTTTCCTTACCTTTCTTGAGTGTTGCTTCAGCATATTA
2148  12_HRV85b|    ACATGGGCAAACTTTCCCCAGATTTTCCTTACCTTTCTTGAGTGTTGCTTCAGCATATTA
2149  13_HRV56a|    ACATGGCCAAGCTTTCCCCAGATTCTCTCTACCTTTCTTAAGTATTGCTTCTGCTTATTA
2150  14_HRV56b|    ACATGGCCAAGCTTTCCCCAGATTCTCTCTACCTTTCTTAAGTATTGCTTCTGCTTATTA
2151  15_HRV56      ACATGGCCAAGCTTTCCCCAGATTCTCTCTACCTTTCTTAAGTATTGCTTCTGCTTATTA
2152  16_HRV54      ACATGGCCAAGCTTATCCAAGATTCTCTTTACCATTTTTAAGTATTGCATCTGCTTACTA
2153  17_HRV98      GCATGGTCAGGCCTATCCAAGATTTTCTCTACCATTCTTGAGCATTGCATCTGCTTACTA
2154  18_HRV59a|    ACATGGACAAACATTCCCAAGATTTTCATTGCCCTTCCTGAGCATAGCATCAGCTTATTA
2155  19_HRV59b|    ACATGGACAAACATTCCCAAGATTTTCATTGCCCTTCCTGAGCATAGCATCAGCTTATTA
2156  20_HRV59      ACATGGACAAACATTCCCAAGATTTTCATTGCCCTTCCTGAGCATAGCATCAGCTTATTA
2157  21_HRV63      ACATGGACAAGCTTTTCCAAGGTTTTCTCTACCTTTCTTGAGTATTGCATCAGCATATTA
2158  22_HRV63b|    ACATGGACAAGCTTTTCCAAGGTTTTCTCTACCTTTCTTGAGTATTGCATCAGCATATTA
2159  23_HRV63a|    ACATGGACAAGCTTTTCCAAGGTTTCTCTACCTTTCTTGAGTATTGCATCAGCATATTA
2160  24_HRV39      ACACGGACAGCCTTACCCTAGATTTTCATTACCATTTCTAAGCATAGCCTCAGCATATTA
2161  25_HRV39a|    ACACGGACAGCCTTACCCTAGATTTTCATTACCATTTCTAAGCATAGCCTCAGCATATTA
2162  26_HRV39b|    ACACGGACAGCCTTACCCTAGATTTTCATTACCATTTCTAAGCATAGCCTCAGCATATTA
2163  27_HRV10a|    ACATGGACAACCTTTCCCTAGATTTTCTTTACCCTTCTTAAGCATTGCATCTGCTTACTA
2164  28_HRV10b|    ACATGGACAACCTTTCCCTAGATTTTCTTTACCCTTCTTAAGCATTGCATCTGCTTACTA
2165  29_HRV10      ACATGGACAACCTTTCCCTAGATTTTCTTTACCCTTCTTAAGCATTGCATCTGCTTACTA
2166  30_HRV100a    GCATGGGCAGCCATTCCCTAGAATTTCTTTACCTTTCTTGAGCATTGCTTCTGCATACTA
2167  31_HRV100b    GCATGGGCAGCCATTCCCTAGAATTTCTTTACCTTTCTTGAGCATTGCTTCTGCATACTA
2168  32_HRV100     GCATGGGCAGCCATTCCCTAGAATTTCTTTACCTTTCTTGAGCATTGCTTCTGCATACTA
2169  33_HRV66      ACTTGGACAACCATTCCCAAGATTCTCGCTACCTTTTCTAGGCATAGCTTCAGCATATTA
2170  34_HRV66b|    ACTTGGACAACCATTCCCAAGATTCTCGCTACCTTTTCTAGGCATAGCTTCAGCATATTA
2171  35_HRV66a|    ACTTGGACAACCATTCCCAAGATTCTCGCTACCTTTTCTAGGCATAGCTTCAGCATATTA
2172  36_HRV77a|    ACATGGACAACCATTCCCAAGATTTTCACTACCTTTTCTGAGTATTGCTTCAGCTTACTA
2173  37_HRV77b|    ACATGGACAACCATTCCCAAGATTTTCACTACCTTTTCTGAGTATTGCTTCAGCTTACTA
2174  38_HRV77      ACATGGACAACCATTCCCAAGATTTTCACTACCTTTTCTGAGTATTGCTTCAGCTTACTA
2175  39_HRV62a     ACATGGGCAACCCTTTCCTAGATTTTCATTACCTTTTTTGAGTGTTGCATCTGCTTATTA
2176  40_HRV62b     ACATGGGCAACCCTTTCCTAGATTTTCATTACCTTTTTTGAGTGTTGCATCTGCTTATTA
2177  41_HRV25      ACATGGACAACCCTTCCCTAGATTTTCATTGCCATTTCTGAGTGTTGCATCTGCTTATTA
2178  42_HRV29a     ACATGGTCAGCCTTTCCCAAGATTTTCATTACCATTCCTAAGTGTTGCATCTGCTTATTA
2179  43_HRV29b     ACATGGTCAGCCTTTCCCAAGATTTTCATTACCATTCCTAAGTGTTGCATCTGCTTATTA
2180  44_HRV44a     ACATGGTCAACCTTTCCCAAGATTTTCATTGCCATTTCTAAGTGTTGCATCTGCCTATTA
2181  45_HRV44b     ACATGGTCAACCTTTCCCAAGATTTTCATTGCCATTTCTAAGTGTTGCATCTGCCTATTA
2182  46_HRV31      ACATGGACAACCCTTTCCAAGATTTACATTACCCTTTTTGAGTGTCGCATCCGCTTATTA
2183  47_HRV31a|    ACATGGACAACCCTTTCCAAGATTTACATTACCCTTTTTGAGTGTCGCATCCGCTTATTA
2184  48_HRV31b|    ACATGGACAACCCTTTCCAAGATTTACATTACCCTTTTTGAGTGTCGCATCCGCTTATTA
2185  49_HRV47      ACAAGGGCAACCCTTTCCAAGATTTTCATTACCATTTTTGAGTGTTGCATCTGCTTATTA
2186  50_HRV47a|    ACAAGGGCAACCCTTTCCAAGATTTTCATTACCATTTTTGAGTGTTGCATCTGCTTATTA
2187  51_HRV47b|    ACAAGGGCAACCCTTTCCAAGATTTTCATTACCATTTTTGAGTGTTGCATCTGCTTATTA
2188  52_HRV11      ATATGGTCAAACATACCCAAGATTTTCTCTACCTTTCATGAGTATAGCCTCAGCATATTA
2189  53_HRV11b|    ATATGGTCAAACATACCCAAGATTTTCTCTACCTTTCATGAGTATAGCCTCAGCATATTA
2190  54_HRV11a|    ATATGGTCAAACATACCCAAGATTTTCTCTACCTTTCATGAGTATAGCCTCAGCATATTA
2191  55_HRV76      ATATGGACAAACATACCCTAGGTTTTCATTACCCTTTCTAAGTATAGCTTCAGCTTATTA
2192  56_HRV76b|    ATATGGACAAACATACCCTAGGTTTTCATTACCCTTTCTAAGTATAGCTTCAGCTTATTA
2193  57_HRV76a|    ATATGGACAAACATACCCTAGGTTTTCATTACCCTTTCTAAGTATAGCTTCAGCTTATTA
2194  58_HRV33      ATATGGACAAACATATCCTAGGTCTCATTACCTTTCCTTAGCATAGCTTCAGCATATTA
2195  59_HRV33b|    ATATGGACAAACATATCCTAGGTCTCATTACCTTTCCTTAGCATAGCTTCAGCATATTA
2196  60_HRV33a|    ATATGGACAAACATATCCTAGGTCTCATTACCTTTCCTTAGCATAGCTTCAGCATATTA
2197  61_HRV24a|    ACATGGACAAACCTATCCTAGATTTTCCCTTCCTTTTCTGAGTGTAGCCTCTGCATATTA
2198  62_HRV24b|    ACATGGACAAACCTATCCTAGATTTTCCCTTCCTTTTCTGAGTGTAGCCTCTGCATATTA
2199  63_HRV24      ACATGGACAAACCTATCCTAGATTTTCCCTTCCTTTTCTGAGTGTAGCCTCTGCATATTA
2200  64_HRV90      ACATGGACAAACATACCCTAGATTTTCACTTCCTTTCTTAAGTATAGCTTCTGCATACTA
2201  65_HRV90a|    ACATGGACAAACATACCCTAGATTTTCACTTCCTTTCTTAAGTATAGCTTCTGCATACTA
2202  66_HRV90b|    ACATGGACAAACATACCCTAGATTTTCACTTCCTTTCTTAAGTATAGCTTCTGCATACTA
2203  67_HRV34      ACATGGTCAAACATACCCTAGATTTTCCCTCCCTTTCTTAAGCATAGCCTCAGCATACTA
2204  68_HRV34b|    ACATGGTCAAACATACCCTAGATTTTCCCTCCCTTTCTTAAGCATAGCCTCAGCATACTA
2205  69_HRV34a|    ACATGGTCAAACATACCCTAGATTTTCCCTCCCTTTCTTAAGCATAGCCTCAGCATACTA
2206  70_HRV50a|    ACATGGTCAAACATACCCTAGATCTCTCTACCATTCTTGAGTATAGCATCTGCATATTA
2207  71_HRV50b|    ACATGGTCAAACATACCCTAGATTCTCTCTACCATTCTTGAGTATAGCATCTGCATATTA
2208  72_HRV50      ACATGGTCAAACATACCCTAGATCTCTCTACCATTCTTGAGTATAGCATCTGCATATTA
2209  73_HRV18a|    ACATGGTCAAACATACCCCAGATTTTCACTTCCTTTCCTCAGTATAGCATCAGCTTATTA
2210  74_HRV18b|    ACATGGTCAAACATACCCCAGATTTTCACTTCCTTTCCTCAGTATAGCATCAGCTTATTA
```

FIG. D10 CONT'D

06.trace                                                                                                    9/20/2007 5:04 PM

```
2211  75_HRV18      ACATGGTCAAACATACCCCAGATTTTCACTTCCTTTCCTCAGTATAGCATCAGCTTATTA
2212  76_HRV55      ACATGGGCAAACATACCCTAGATTTTCACTTCCTTTCCTAAGTATAGCTTCTGCTTATTA
2213  77_HRV55b|    ACATGGGCAAACATACCCTAGATTTTCACTTCCTTTCCTAAGTATAGCTTCTGCTTATTA
2214  78_HRV55a|    ACATGGGCAAACATACCCTAGATTTTCACTTCCTTTCCTAAGTATAGCTTCTGCTTATTA
2215  79_HRV57      ACATGGTCAAACATACCCTAGATTTTCCTTGCCTTTCTTAAGTATAGCCTCAGCATATTA
2216  80_HRV57a|    ACATGGTCAAACATACCCTAGATTTTCCTTGCCTTTCTTAAGTATAGCCTCAGCATATTA
2217  81_HRV57b|    ACATGGTCAAACATACCCTAGATTTTCCTTGCCTTTCTTAAGTATAGCCTCAGCATATTA
2218  82_HRV21      GCATGGCCAGACTTATCCTAGATTTTCATTACCCTTCCTTAGTATAGCATCAGCATACTA
2219  83_HRVHan     GCATGGTCAAACTTATCCTAGATTTTCACTACCCTTCCTTAGTATAGCATCAGCATATTA
2220  84_HRV43      ACATGGTCAAACATTTCCAAGATTTTCCTTACCTTTTCTGAGCATAGCATCAGCATATTA
2221  85_HRV43b|    ACATGGTCAAACATTTCCAAGATTTTCCTTACCTTTCTGAGCATAGCATCAGCATATTA
2222  86_HRV43a|    ACATGGTCAAACATTTCCAAGATTTTCCTTACCTTTTCTGAGCATAGCATCAGCATATTA
2223  87_HRV75      ACATGGACAAACATTTCCAAGATTTTCACTACCATTTCTGAGCATTGCATCAGCATATTA
2224  88_HRV75b|    ACATGGACAAACATTTCCAAGATTTTCACTACCATTTCTGAGCATTGCATCAGCATATTA
2225  89_HRV75a|    ACATGGACAAACATTTCCAAGATTTTCACTACCATTTCTGAGCATTGCATCAGCATATTA
2226  96_HRV9a|d    ACATGGACAATCATATCCCAGATTTTCACTTCCGTTTTTGAGCATTGCCTCTGCATATTA
2227  97_HRV9b|d    ACATGGACAATCATATCCCAGATTTTCACTTCCGTTTTTGAGCATTGCCTCTGCATATTA
2228  98_HRV9       ACATGGACAATCATATCCCAGATTTTCACTTCCGTTTTTGAGCATTGCCTCTGCATATTA
2229  99_HRV32      GCATGGACAGGCATATCCCAGGTTTTCACTTCCATTTCTAAGTATTGCCTCTGCATACTA
2230  100_HRV32a    GCATGGACAGGCATATCCCAGGTTTTCACTTCCATTTCTAAGTATTGCCTCTGCATACTA
2231  101_HRV32b    GCATGGACAGGCATATCCCAGGTTTTCACTTCCATTTCTAAGTATTGCCTCTGCATACTA
2232  102_HRV67     ACATGGACAATCATACCCCAGATTCTCACTACCATTCTTAAGTATTGCCTCTGCTTATTA
2233  103_HRV67a    ACATGGACAATCATACCCCAGATTCTCACTACCATTCTTAAGTATTGCCTCTGCTTATTA
2234  104_HRV67b    ACATGGACAATCATACCCCAGATTCTCACTACCATTCTTAAGTATTGCCTCTGCTTATTA
2235  105_HRV15     ACATGGTCAACCTTACCCCAGATTTTCTTTGCCTTTTCTCAGCATTGCATCTGCTTACTA
2236  106_HRV15a    ACATGGTCAACCTTACCCCAGATTTTCTTTGCCTTTTCTCAGCATTGCATCTGCTTACTA
2237  107_HRV15b    ACATGGTCAACCTTACCCCAGATTTTCTTTGCCTTTTCTCAGCATTGCATCTGCTTACTA
2238  108_HRV74a    GCATGGACAGCCATACCCTAGATTCTCATTACCTTTCCTTAGCATAGCATCTGCTTATTA
2239  109_HRV74b    GCATGGACAGCCATACCCTAGATTCTCATTACCTTTCCTTAGCATAGCATCTGCTTATTA
2240  110_HRV74     GCATGGACAGCCATACCCTAGATTCTCATTACCTTTCCTTAGCATAGCATCTGCTTATTA
2241  111_HRV38a    ATATGGTCAGACATATCCTCGATTTCCTTACCTTTCTTAAGCATTGCATCATCTGTCTATTA
2242  112_HRV38b    ATATGGTCAGACATATCCTCGATTTTCCTTACCTTTCTTAAGCATTGCATCTGTCTATTA
2243  113_HRV38     ATATGGTCAGACATATCCTCGATTTTCCTTACCTTTCTTAAGCATTGCATCTGTCTATTA
2244  114_HRV60     GCATGGACAAACATACCCTAGATTTTCACTTCCATTTCTAAGTATTGCATCTGCCTACTA
2245  115_HRV60a    GCATGGACAAACATACCCTAGATTTTCACTTCCATTTCTAAGTATTGCATCTGCCTACTA
2246  116_HRV60b    GCATGGACAAACATACCCTAGATTTTCACTTCCATTTCTAAGTATTGCATCTGCCTACTA
2247  117_HRV64a    ACACGGTCAACCATACCCTCGATTTTCTCTCCCTTTCCTTAGCATAGCCTCAGCATATTA
2248  118_HRV64b    ACACGGTCAACCATACCCTCGATTTTCTCTCCCTTTCCTTAGCATAGCCTCAGCATATTA
2249  119_HRV64     ACACGGTCAACCATACCCTCGATTTTCTCTCCCTTTCCTTAGCATAGCCTCAGCATATTA
2250  120_HRV94a    ACATGGTCAACCCTACCCTCGATTCTCACTTCCATTCTTAGTATAGCCTCAGCATATTA
2251  121_HRV94b    ACATGGTCAACCCTACCCTCGATTCTCACTTCCATTCTTAGTATAGCCTCAGCATATTA
2252  122_HRV94     ACATGGTCAACCCTACCCTCGATTCTCACTTCCATTCTTAGTATAGCCTCAGCATATTA
2253  123_HRV22     GCATGGTCAACCTTATCCCCGATTCTCACTCCCTTTCCTCAGTGTAGCTTCAGCATATTA
2254  124_HRV22a    GCATGGTCAACCTTATCCCCGATTCTCACTCCCTTTCCTCAGTGTAGCTTCAGCATATTA
2255  125_HRV22b    GCATGGTCAACCTTATCCCCGATTCTCACTCCCTTTCCTCAGTGTAGCTTCAGCATATTA
2256  126_HRV82     ACATGGACAACCTTACCCTCGCTTCTCACTTCCTTTCTTGAGTATAGCCTCAGCTTACTA
2257  127_HRV82b    ACATGGACAACCTTACCCTCGCTTCTCACTTCCTTTCTTGAGTATAGCCTCAGCTTACTA
2258  128_HRV82a    ACATGGACAACCTTACCCTCGCTTCTCACTTCCTTTCTTGAGTATAGCCTCAGCTTACTA
2259  129_HRV19     ACATGGTCAACCATACCCAAGATTTTCATTACCTTTTCTAAGTATAGCTTCTGCATATTA
2260  130_HRV19a    ACATGGTCAACCATACCCAAGATTTTCATTACCTTTTCTAAGTATAGCTTCTGCATATTA
2261  131_HRV19b    ACATGGTCAACCATACCCAAGATTTTCATTACCTTTCTCTAAGTATAGCTTCTGCATATTA
2262  132_HRV13     ACATGGTCAAATTTACCCCCGATTCTCTTTACCATTTCTTAGTATTGCATCTGCATATTA
2263  133_HRV13a    ACATGGTCAAATTTACCCCCGATTCTCTTTACCATTTCTTAGTATTGCATCTGCATATTA
2264  134_HRV13b    ACATGGTCAAATTTACCCCCGATTCTCTTTACCATTTCTTAGTATTGCATCTGCATATTA
2265  135_HRV41     GTATGGTCAAGTTTACCCTAGGTTTTCTCTACCATTTCTTAGCATTGCTTCCGCATATTA
2266  136_HRV41a    GTATGGTCAAGTTTACCCTAGGTTTTCTCTACCATTTCTTAGCATTGCTTCCGCATATTA
2267  137_HRV41b    GTATGGTCAAGTTTACCCTAGGTTTTCTCTACCATTTCTTAGCATTGCTTCCGCATATTA
2268  138_HRV73     ACATGGTCAAACTTACCCCAGATTCTCATTACCATTCCTTAGTATAGCATCCGCATATTA
2269  139_HRV73b    ACATGGTCAAACTTACCCCAGATTCTCATTACCATTCCTTAGTATAGCATCCGCATATTA
2270  140_HRV73a    ACATGGTCAAACTTACCCCAGATTCTCATTACCATTCCTTAGTATAGCATCCGCATATTA
2271  141_HRV61     ACATGGTCAAGCTTATCCCAGATTTTCATTACCATTCCTAAGTATTGCATCTGCATATTA
2272  142_HRV61a    ACATGGTCAAGCTTATCCCAGATTTTCATTACCATTCCTAAGTATTGCATCTGCATATTA
2273  143_HRV61b    ACATGGTCAAGCTTATCCCAGATTTTCATTACCATTCCTAAGTATTGCATCTGCATATTA
2274  144_HRV96     GCACGGGCAAGCATATCCTAGATTTTCACTGCCTTTCCTTAGTATTGCCTCTGCATATTA
2275  145_HRV96b    GCACGGGCAAGCATATCCTAGATTTTCACTGCCTTTCCTTAGTATTGCCTCTGCATATTA
```

FIG. D10 CONT'D

```
06.trace                                                                    9/20/2007 5:04 PM 2276 146_HRV96a    GCACGGGCAAGCATATCCTAGATTTTCACTGCCTTTCCTTAGTATTGCCTCTGCATATTA
2277  90_HRV16a|   GCATGGGCAACCTTTCCCTCGCTTTTCACTTCCCTTTTTGAGTATTGCATCAGCATATTA
2278  91_HRV16b|   GCATGGGCAACCTTTCCCTCGCTTTTCACTTCCCTTTTTGAGTATTGCATCAGCATATTA
2279  92_1AYM_A    GCATGGGCAACCTTTCCCTCGCTTTTCACTTCCCTTTTTGAGTATTGCATCAGCATATTA
2280  93_HRV81a|   ACATGGGCAACCCTTTCCCCGGTTTTCACTCCCTTTTCTAAGTGTAGCATCAGCATATTA
2281  94_HRV81b|   ACATGGGCAACCCTTTCCCCGGTTTTCACTCCCTTTTCTAAGTGTAGCATCAGCATATTA
2282  95_HRV81     ACATGGGCAACCCTTTCCCCGGTTTTCACTCCCTTTTCTAAGTGTAGCATCAGCATATTA
2283 147_HRV2      ACATGGACAGGCTTATCCAAGATTTTCCTTACCTTTCCTAAGTGTGGCATCTGCTTATTA
2284 148_HRV2a|    ACATGGACAGGCTTATCCAAGATTTTCCTTACCTTTCCTAAGTGTGGCATCTGCTTATTA
2285 149_HRV2b|    ACATGGACAGGCTTATCCAAGATTTTCCTTACCTTTCCTAAGTGTGGCATCTGCTTATTA
2286 150_HRV49a    ACATGGGCAAGCATACCCAAGATTTTCTCTACCCTTTTGAGTGTAGCTTCAGCTTACTA
2287 151_HRV49b    ACATGGGCAAGCATACCCAAGATTTTCTCTACCCTTTTTGAGTGTAGCTTCAGCTTACTA
2288 152_HRV49     ACATGGGCAAGCATACCCAAGATTTTCTCTACCCTTTTTGAGTGTAGCTTCAGCTTACTA
2289 153_HRV23a    ACATGGACAAACATATCCAAGGTTCTCCTTACCCTTTTTGAGTGTGGCATCTGCTTATTA
2290 154_HRV23b    ACATGGACAAACATATCCAAGGTTCTCCTTACCCTTTTTGAGTGTGGCATCTGCTTATTA
2291 155_HRV23     ACATGGACAAACATATCCAAGGTTCTCCTTACCCTTTTTGAGTGTGGCATCTGCTTATTA
2292 156_HRV30a    ACACGGACAAACATACCCAAGATTCTCCCTACCATTTTGAGTGTAGCATCTGCTTATTA
2293 157_HRV30b    ACACGGACAAACATACCCAAGATTCTCCCTACCATTTTGAGTGTAGCATCTGCTTATTA
2294 158_HRV30     ACACGGACAAACATACCCAAGATTCTCCCTACCATTTTGAGTGTAGCATCTGCTTATTA
2295 159_HRV7      GGAGGGTCAACCATACCCTAGATTCACAATTCCTTTTATGAGTATTGCATCAGCTTATTA
2296 160_HRV7b|    GGAGGGTCAACCATACCCTAGATTCACAATTCCTTTTATGAGTATTGCATCAGCTTATTA
2297 161_HRV7a|    GGAGGGTCAACCATACCCTAGATTCACAATTCCTTTTATGAGTATTGCATCAGCTTATTA
2298 162_HRV88     AGAAGGACAACCATACCCAAGATTTACCATTCCCTTTATGAGTATTGCATCAGCTTACTA
2299 163_HRV88a    AGAAGGACAACCATACCCAAGATTTACCATTCCCTTTATGAGTATTGCATCAGCTTACTA
2300 164_HRV88b    AGAAGGACAACCATACCCAAGATTTACCATTCCCTTTATGAGTATTGCATCAGCTTACTA
2301 165_HRV36a    AGAAGGGCAACCATATCCTAGATTTACAATCCCCTTTATGAGTATTGCATCAGCTTATTA
2302 166_HRV36b    AGAAGGGCAACCATATCCTAGATTTACAATCCCCTTTATGAGTATTGCATCAGCTTATTA
2303 167_HRV36     AGAAGGGCAACCATATCCTAGATTTACAATCCCCTTTATGAGTATTGCATCAGCTTATTA
2304 168_HRV89a    AGAAGGACAACCATACCCCAGATTCACAATCCCTTTTATGAGCATTGCATCAGCCTATTA
2305 169_HRV89b    AGAAGGACAACCATACCCCAGATTCACAATCCCTTTTATGAGCATTGCATCAGCCTATTA
2306 170_HRV89     AGAAGGACAACCATACCCCAGATTCACAATCCCTTTTATGAGCATTGCATCAGCCTATTA
2307 171_HRV58     GGAAGGACAACCATACCCTAGATTTACAATCCCTTTTATGAGCATTGCATCAGCTTACTA
2308 172_HRV58a    GGAAGGACAACCATACCCTAGATTTACAATCCCTTTTATGAGCATTGCATCAGCTTACTA
2309 173_HRV58b    GGAAGGACAACCATACCCTAGATTTACAATCCCTTTTATGAGCATTGCATCAGCTTACTA
2310 174_HRV12a    GGAAGGTCAACCTTACCCCAGATTCACAATCCCTTTTATTAGTATTGCCTCAGCATATTA
2311 175_HRV12b    GGAAGGTCAACCTTACCCCAGATTCACAATCCCTTTTATTAGTATTGCCTCAGCATATTA
2312 176_HRV12     GGAAGGTCAACCTTACCCCAGATTCACAATCCCTTTTATTAGTATTGCCTCAGCATATTA
2313 177_HRV78a    ACAAGGTCAAACATACCCCAGGTTCTCTATACCATTTTCTAGTATTGCCTCAGCTTATTA
2314 178_HRV78b    ACAAGGTCAAACATACCCCAGGTTCTCTATACCATTTTCTAGTATTGCCTCAGCTTATTA
2315 179_HRV78     ACAAGGTCAAACATACCCCAGGTTCTCTATACCATTTTCTAGTATTGCCTCAGCTTATTA
2316 180_HRV20     GCAGGGCCAACCTTACCCCAGATTTACCATTCCATTTATGAGTATAGCTTCAGCATATTA
2317 181_HRV20a    GCAGGGCCAACCTTACCCCAGATTTACCATTCCATTTATGAGTATAGCTTCAGCATATTA
2318 182_HRV20b    GCAGGGCCAACCTTACCCCAGATTTACCATTCCATTTATGAGTATAGCTTCAGCATATTA
2319 183_HRV68     ACAAGGACAACCTTACCCCAGATTTACCATTCCATTTATGAGTATAGCTTCAGCATATTA
2320 184_HRV68a    ACAAGGACAACCTTACCCCAGATTTACCATTCCATTTATGAGTATAGCTTCAGCATATTA
2321 185_HRV68b    ACAAGGACAACCTTACCCCAGATTTACCATTCCATTTATGAGTATAGCTTCAGCATATTA
2322 186_HRV28     ACAAGGACAACCATATCCCAGATTCACTATACCTTTTATGAGTATTGCCTCAGCTTATTA
2323 187_HRV28a    ACAAGGACAACCATATCCCAGATTCACTATACCTTTTATGAGTATTGCCTCAGCTTATTA
2324 188_HRV28b    ACAAGGACAACCATATCCCAGATTCACTATACCTTTTATGAGTATAGCCTCAGCTTATTA
2325 189_HRV53a    ACAAGGACAACCATACCCTAGATTCACAATCCCTTTCATGAGTATTGCGTCAGCATATTA
2326 190_HRV53b    ACAAGGACAACCATACCCTAGATTCACAATCCCTTTCATGAGTATTGCGTCAGCATATTA
2327 191_HRV53     ACAAGGACAACCATACCCTAGATTCACAATCCCTTTCATGAGTATTGCGTCAGCATATTA
2328 192_HRV46a    GCAAGGGCAGCCATACCCTAGATTCACTATCCGTTCATGAGTATAGCCTCAGCATATTA
2329 193_HRV46b    GCAAGGGCAGCCATACCCTAGATTCACTATCCCGTTCATGAGTATAGCCTCAGCTTATTA
2330 194_HRV46     GCAAGGGCAGCCATACCCTAGATTCACTATCCCGTTCATGAGTATAGCCTCAGCATATTA
2331 195_HRV80a    ACAGGGTCAGCCATACCCCAGATTCACTATTCCATTCATGAGTATAGCCTCAGCTTATTA
2332 196_HRV80b    ACAGGGTCAGCCATACCCCAGATTCACTATTCCATTCATGAGTATAGCCTCAGCTTATTA
2333 197_HRV80     ACAGGGTCAGCCATACCCCAGATTCACTATTCCATTCATGAGTATAGCCTCAGCTTATTA
2334 198_HRV51     ACATGGACAACCATACCCTAGATTTACAATCCCTTTTGTAAGCATAGCCTCAGCATACTA
2335 199_HRV51a    ACATGGACAACCATACCCTAGATTTACAATCCCTTTTGTAAGCATAGCCTCAGCATACTA
2336 200_HRV51b    ACATGGACAACCATACCCTAGATTTACAATCCCTTTTGTAAGCATAGCCTCAGCATACTA
2337 201_HRV65a    GCATGGTCAACCATACCCCAGATTTACAATTCCTTTTGTGAGTATTGCCTCAGCATATTA
2338 202_HRV65b    GCATGGTCAACCATACCCCAGATTTACAATTCCTTTTGTGAGTATTGCCTCAGCATATTA
2339 203_HRV65     GCATGGTCAACCATACCCCAGATTTACAATTCCTTTTGTGAGTATTGCCTCAGCATATTA
2340 204_HRV71a    GCACGGCCAACCATACCCAAGGTTTACAATCCCCTTCATAAGCATTGCATCAGCATATTA
```

FIG. D10 CONT'D

```
06.trace                                                                    9/20/2007 5:04 PM 2341 205_HRV71b    GCACGGCCAACCATACCCAAGGTTTACAATCCCCTTCATAAGCATTGCATCAGCATATTA
2342 206_HRV71     GCACGGCCAACCATACCCAAGGTTTACAATCCCCTTCATAAGCATTGCATCAGCATATTA
2343 207_HRV8      AGTTGGACAAACTTATCCCAGATTCACCATACCTTTCTCCAGCATAGCATCAGCTTATTA
2344 208_HRV95     AGTTGGACAGACTTATCCCAGATTCACCATACCTTTCTCCAGTATAGCATCAGCTTATTA
2345 209_HRV45     GGTTGGTCAAACTTATCCCAGATTTTCTATACCTTTCTCAAGTATAGCTTCAGCTTACTA
2346 210_HRV45a    GGTTGGTCAAACTTATCCCAGATTTTCTATACCTTTCTCAAGTATAGCTTCAGCTTACTA
2347 211_HRV45b    GGTTGGTCAAACTTATCCCAGATTTTCTATACCTTTCTCAAGTATAGCTTCAGCTTACTA
2348 GROUP_1       ----GG-CA----T--CC--G--T--C--T-CC-TT-----G--T-GC-TC-G--TA-TA
2349
2350 1_HRV1A1|d   TATGTTTTATGATGGATATGATGGAGACAACACTTCTTCCAAGTATGGTAGCGTAGTTAC
2351 2_HRV1A2|d   TATGTTTTATGATGGATATGATGGAGACAACACTTCTTCCAAGTATGGTAGCGTAGTTAC
2352 3_HRV1A|cD   TATGTTTTATGATGGATATGATGGAGACAACACTTCTTCCAAGTATGGTAGCGTAGTTAC
2353 4_HRV1B1|d   CATGTTTTATGATGGATATGATGGAGATAATTCCTCTTCCAAATATGGTAGTATAGTCAC
2354 5_HRV1B2|d   CATGTTTTATGATGGATATGATGGAGATAATTCCTCTTCCAAATATGGTAGTATAGTCAC
2355 6_HRV1B      CATGTTTTATGATGGATATGATGGAGATAATTCCTCTTCCAAATATGGTAGTATAGTCAC
2356 7_HRV40a|d   CATGTTTTATGATGGATACGATGGTGATACATCGACCTCAAGATATGGCACATCAGTCAC
2357 8_HRV40b|d   CATGTTTTATGATGGATACGATGGTGATACATCGACCTCAAGATATGGCACATCAGTCAC
2358 9_HRV40      CATGTTTTATGATGGATACGATGGTGATACATCGACCTCAAGATATGGCACATCAGTCAC
2359 10_HRV85     CATGTTTTATGATGGTTATGATGGTGATACACCAGGCTCAATGTATGGGACGTCAGTCAC
2360 11_HRV85a|   CATGTTTTATGATGGTTATGATGGTGATACACCAGGCTCAATGTATGGGACGTCAGTCAC
2361 12_HRV85b|   CATGTTTTATGATGGTTATGATGGTGATACACCAGGCTCAATGTATGGGACGTCAGTCAC
2362 13_HRV56a|   CATGTTTTATGATGGTTATGATGGAGACACTTCAAGCTCCAGATATGGTACATCAGTTAC
2363 14_HRV56b|   CATGTTTTATGATGGTTATGATGGAGACACTTCAAGCTCCAGATATGGTACATCAGTTAC
2364 15_HRV56     CATGTTTTATGATGGTTATGATGGAGACACTTCAAGCTCCAGATATGGTACATCAGTTAC
2365 16_HRV54     CATGTTTTATGATGGGTATGATGGTGACGCACCTGGATCAAGATATGGGACTTCAGTTAC
2366 17_HRV98     CATGTTTTACGATGGGTATGATGGTGATGCACCTGGATCAAGATATGGAACCTCAGTCAC
2367 18_HRV59a|   CATGTTTTATGATGGTTATGATGGAGATAAATCTGAATCTAGGTATGGTGTGTCTGTAAC
2368 19_HRV59b|   CATGTTTTATGATGGTTATGATGGAGATAAATCTGAATCTAGGTATGGTGTGTCTGTAAC
2369 20_HRV59     CATGTTTTATGATGGTTATGATGGAGATAAATCTGAATCTAGGTATGGTGTGTCTGTAAC
2370 21_HRV63     CATGTTTTATGGATATGATGGAGATAAATCAAGCTCTAGGTATGGTGTTTCAGTTAC
2371 22_HRV63b|   CATGTTTTATGATGGATATGATGGAGATAAATCAAGCTCTAGGTATGGTGTTTCAGTTAC
2372 23_HRV63a|   CATGTTTTATGATGGATATGATGGAGATAAATCAAGCTCTAGGTATGGTGTTTCAGTTAC
2373 24_HRV39     TATGTTCTATGATGGATATGATGGTGATAAATCGTCATCTAGGTATGGTGTTTCTGTCAC
2374 25_HRV39a|   TATGTTCTATGATGGATATGATGGTGATAAATCGTCATCTAGGTATGGTGTTTCTGTCAC
2375 26_HRV39b|   TATGTTCTATGATGGATATGATGGTGATAAATCGTCATCTAGGTATGGTGTTTCTGTCAC
2376 27_HRV10a|   CATGTTCTATGATGGTTATGATGGTGATACACATGACTCACGTTATGGCACAACAGTGAT
2377 28_HRV10b|   CATGTTCTATGATGGTTATGATGGTGATACACATGACTCACGTTATGGCACAACAGTGAT
2378 29_HRV10     CATGTTCTATGATGGTTATGATGGTGATACACATGACTCACGTTATGGCACAACAGTGAT
2379 30_HRV100a   CATGTTTTATGATGGATATGATGGTGATACACATGATTCACACTATGGTACTACTGTAAT
2380 31_HRV100b   CATGTTTTATGATGGATATGATGGTGATACACATGATTCACACTATGGTACTACTGTAAT
2381 32_HRV100    CATGTTTTATGATGGATATGATGGTGATACACATGATTCACACTATGGTACTACTGTAAT
2382 33_HRV66     CATGTTCTATGATGGTTATGATGGAGATACTCCTGGGTCTCGTTATGGAACCACAGTAGT
2383 34_HRV66b|   CATGTTCTATGATGGTTATGATGGAGATACTCCTGGGTCTCGTTATGGAACCACAGTAGT
2384 35_HRV66a|   CATGTTCTATGATGGTTATGATGGAGATACTCCTGGGTCTCGTTATGGAACCACAGTAGT
2385 36_HRV77a|   CATGTTTTATGATGGCTATGATGGGGATACCTATGAATCACGTTATGGTACTACAGTGGT
2386 37_HRV77b|   CATGTTTTATGATGGCTATGATGGGGATACCTATGAATCACGTTATGGTACTACAGTGGT
2387 38_HRV77     CATGTTTTATGATGGCTATGATGGGGATACCTATGAATCACGTTATGGTACTACAGTGGT
2388 39_HRV62a    CATGTTTTATGATGGCTATAATGGTGATGACTATACAGCAAAATACGGTACCACCGTGGT
2389 40_HRV62b    CATGTTTTATGATGGCTATAATGGTGATGACTATACAGCAAAATACGGTACCACCGTGGT
2390 41_HRV25     CATGTTTTATGATGGCTATAATGGTGATGATCACACAGCGAGATATGGTACCACTGTGGT
2391 42_HRV29a    CATGTTTTATGATGGTTACAATGGAGGTGATCATACAGCAACTTATGGCACCACAGTGGT
2392 43_HRV29b    CATGTTTTATGATGGTTACAATGGAGGTGATCATACAGCAACTTATGGCACCACAGTGGT
2393 44_HRV44a    CATGTTTTATGACGGTTATAATGGAGGTGATCATACAGCAACTTATGGCACCACAGTGGT
2394 45_HRV44b    CATGTTTTATGACGGTTATAATGGAGGTGATCATACAGCAACTTATGGCACCACAGTGGT
2395 46_HRV31     CATGTTTTATGATGGTTATGATGGAGACAAAAGTGGAGCCAAGTATGGTACTACAGTAGT
2396 47_HRV31a|   CATGTTTTATGATGGTTATGATGGAGACAAAAGTGGAGCCAAGTATGGTACTACAGTAGT
2397 48_HRV31b|   CATGTTTTATGATGGTTATGATGGAGACAAAAGTGGAGCCAAGTATGGTACTACAGTAGT
2398 49_HRV47     CATGTTTTATGATGGCTATAATGGTGACAGAAGTGGAGCCAAGTATGGCACCACAGTGGT
2399 50_HRV47a|   CATGTTTTATGATGGCTATAATGGTGACAGAAGTGGAGCCAAGTATGGCACCACAGTGGT
2400 51_HRV47b|   CATGTTTTATGATGGCTATAATGGTGACAGAAGTGGAGCCAAGTATGGCACCACAGTGGT
2401 52_HRV11     CATGTTTTATGATGGATATGATGGAGATCAACCAAACTCCAGATATGGTAATATAGTTAC
2402 53_HRV11b|   CATGTTTTATGATGGATATGATGGAGATCAACCAAACTCCAGATATGGTAATATAGTTAC
2403 54_HRV11a|   CATGTTTTATGATGGATATGATGGAGATCAACCAAACTCCAGATATGGTAATATAGTTAC
2404 55_HRV76     CATGTTTTATGATGGATATGATGGAGACCAACCTAGTTCTAGGTATGGTAATATAGTTAC
2405 56_HRV76b|   CATGTTTTATGATGGATATGATGGAGACCAACCTAGTTCTAGGTATGGTAATATAGTTAC
```

FIG. D10 CONT'D

06.trace                                                                                    9/20/2007 5:04 PM

```
2406  57_HRV76a|   CATGTTTTATGATGGATATGATGGAGACCAACCTAGTTCTAGGTATGGTAATATAGTTAC
2407  58_HRV33     CATGTTCTATGATGGATATGATGGGACCAACCCAATTCCAGGTATGGTAATATGGTTAC
2408  59_HRV33b|   CATGTTCTATGATGGATATGATGGGACCAACCCAATTCCAGGTATGGTAATATGGTTAC
2409  60_HRV33a|   CATGTTCTATGATGGATATGATGGGACCAACCCAATTCCAGGTATGGTAATATGGTTAC
2410  61_HRV24a|   CATGTTTTATGATGGATATGATGGTGATCAACACGACTCAGTGTATGGTTCAGTTGTTAC
2411  62_HRV24b|   CATGTTTTATGATGGATATGATGGTGATCAACACGACTCAGTGTATGGTTCAGTTGTTAC
2412  63_HRV24     CATGTTTTATGATGGATATGATGGTGATCAACACGACTCAGTGTATGGTTCAGTTGTTAC
2413  64_HRV90     TATGTTTTATGATGGATATGATGGTGACCAAACTGATTCGAGATATGGTACCATTGTTAC
2414  65_HRV90a|   TATGTTTTATGATGGATATGATGGTGACCAAACTGATTCGAGATATGGTACCATTGTTAC
2415  66_HRV90b|   TATGTTTTATGATGGATATGATGGTGACCAAACTGATTCGAGATATGGTACCATTGTTAC
2416  67_HRV34     CATGTTTTATGATGGATATGATGGTGATCAACATGATTCAAGATATGGTACAGTAGTGAC
2417  68_HRV34b|   CATGTTTTATGATGGATATGATGGTGATCAACATGATTCAAGATATGGTACAGTAGTGAC
2418  69_HRV34a|   CATGTTTTATGATGGATATGATGGTGATCAACATGATTCAAGATATGGTACAGTAGTGAC
2419  70_HRV50a|   CATGTTTTATGATGGTTATGATGGTGATAAATCTACATCCAGGTATGGTACAGTAGTTAC
2420  71_HRV50b|   CATGTTTTATGATGGTTATGATGGTGATAAATCTACATCCAGGTATGGTACAGTAGTTAC
2421  72_HRV50     CATGTTTTATGATGGTTATGATGGTGATAAATCTACATCCAGGTATGGTACAGTAGTTAC
2422  73_HRV18a|   CATGTTCTATGATGGCTACGACGGTGACCAGACCTCATCGCGGTATGGCACAGTTGCAAC
2423  74_HRV18b|   CATGTTCTATGATGGCTACGACGGTGACCAGACCTCATCGCGGTATGGCACAGTTGCAAC
2424  75_HRV18     CATGTTCTATGATGGCTACGACGGTGACCAGACCTCATCGCGGTATGGCACAGTTGCAAC
2425  76_HRV55     CATGTTCTATGATGGATATGATGGTGACCAAACTGAGTCACGCTATGGCACTGTAGTCAC
2426  77_HRV55b|   CATGTTCTATGATGGATATGATGGTGACCAAACTGAGTCACGCTATGGCACTGTAGTCAC
2427  78_HRV55a|   CATGTTCTATGATGGATATGATGGTGACCAAACTGAGTCACGCTATGGCACTGTAGTCAC
2428  79_HRV57     CATGTTTTATGATGGATATGATGGTGACCAAACTGAATCAAGATATGGTACTGTAGTCAC
2429  80_HRV57a|   CATGTTTTATGATGGATATGATGGTGACCAAACTGAATCAAGATATGGTACTGTAGTCAC
2430  81_HRV57b|   CATGTTTTATGATGGATATGATGGTGACCAAACTGAATCAAGATATGGTACTGTAGTCAC
2431  82_HRV21     CATGTTTTATGATGGTTATGATGGTGACCAGACTGACTCACAATATGGTGCAGTAGTAAC
2432  83_HRVHan    CATGTTTTATGATGGTTATGATGGTGACCAGACTGACTCACAATATGGTGCAGTGGTGAC
2433  84_HRV43     CATGTTTTATGATGGATATGAAGGTGACCAAAAAACATCCCGTTATGGCACAATTGCAAG
2434  85_HRV43b|   CATGTTTTATGATGGATATGAAGGTGACCAAAAAACATCCCGTTATGGCACAATTGCAAG
2435  86_HRV43a|   CATGTTTTATGATGGATATGAAGGTGACCAAAAAACATCCCGTTATGGCACAATTGCAAG
2436  87_HRV75     CATGTTTTATGATGGATATGAAGGGGATCAAAATACATCCCGTTATGGCACCATTGCTAG
2437  88_HRV75b|   CATGTTTTATGATGGATATGAAGGGGATCAAAATACATCCCGTTATGGCACCATTGCTAG
2438  89_HRV75a|   CATGTTTTATGATGGATATGAAGGGGATCAAAATACATCCCGTTATGGCACCATTGCTAG
2439  96_HRV9a|d   CATGTTCTATGATGGTTATGATGGTGG---ACCAGATTCTCTGTATGGAACAATTGTAAC
2440  97_HRV9b|d   CATGTTCTATGATGGTTATGATGGTGG---ACCAGATTCTCTGTATGGAACAATTGTAAC
2441  98_HRV9      CATGTTCTATGATGGTTATGATGGTGG---ACCAGATTCTCTGTATGGAACAATTGTAAC
2442  99_HRV32     CATGTTTTATGATGGTTATGATGGTGG---GCCAGATTCACAATATGGAACAATTGTAAC
2443  100_HRV32a   CATGTTTTATGATGGTTATGATGGTGG---GCCAGATTCACAATATGGAACAATTGTAAC
2444  101_HRV32b   CATGTTTTATGATGGTTATGATGGTGG---GCCAGATTCACAATATGGAACAATTGTAAC
2445  102_HRV67    CATGTTCTATGATGGCTATGATGGTGG---ACCAGATTCACTATATGGCACCATAGTAAC
2446  103_HRV67a   CATGTTTTATGATGGCTATGATGGTGG---ACCAGATTCACTATATGGCACCATAGTAAC
2447  104_HRV67b   CATGTTTTATGATGGCTATGATGGTGG---ACCAGATTCACTATATGGCACCATAGTAAC
2448  105_HRV15    CATGTTCTATGATGGATATGATGGAGATTCCACTGAATCACATTATGGTACAGTGGTCAC
2449  106_HRV15a   CATGTTCTATGATGGATATGATGGAGATTCCACTGAATCACATTATGGTACAGTGGTCAC
2450  107_HRV15b   CATGTTCTATGATGGATATGATGGAGATTCCACTGAATCACATTATGGTACAGTGGTCAC
2451  108_HRV74a   CATGTTTTATGATGGATATGATGGAGACTCTACTGAATCACATTATGGTACAGTAGTAAC
2452  109_HRV74b   CATGTTTTATGATGGATATGATGGAGACTCTACTGAATCACATTATGGTACAGTAGTAAC
2453  110_HRV74    CATGTTTTATGATGGATATGATGGAGACTCTACTGAATCACATTATGGTACAGTAGTAAC
2454  111_HRV38a   TATGTTTTATGATGGATATGATGGGGACTCAACAGAATCACATTATGGGACAGCGGTGAC
2455  112_HRV38b   TATGTTTTATGATGGATATGATGGGGACTCAACAGAATCACATTATGGGACAGCGGTGAC
2456  113_HRV38    TATGTTTTATGATGGATATGATGGGGACTCAACAGAATCACATTATGGGACAGCGGTGAC
2457  114_HRV60    CATGTTTTATGATGGTTATGATGGTCACTCAACTGAATCACATTATGGGACGGTTGTGAC
2458  115_HRV60a   CATGTTTTATGATGGTTATGATGGTCACTCAACTGAATCACATTATGGGACGGTTGTGAC
2459  116_HRV60b   CATGTTTTATGATGGTTATGATGGTCACTCAACTGAATCACATTATGGGACGGTTGTGAC
2460  117_HRV64a   CATGTTTTATGATGGTTATGACGGTGG---ACCTGGTTCCCGTTATGGCGCAGTGGTGAC
2461  118_HRV64b   CATGTTTTATGATGGTTATGACGGTGG---ACCTGGTTCCCGTTATGGCGCAGTGGTGAC
2462  119_HRV64    CATGTTTTATGATGGTTATGACGGTGG---ACCTGGTTCCCGTTATGGCGCAGTGGTGAC
2463  120_HRV94a   CATGTTCTATGATGGTTATGATGGTGG---ACCTGGCTCACGCTATGGCACAGTGGTGAC
2464  121_HRV94b   CATGTTCTATGATGGTTATGATGGTGG---ACCTGGCTCACGCTATGGCACAGTGGTGAC
2465  122_HRV94    CATGTTCTATGATGGTTATGATGGTGG---ACCTGGCTCACGCTATGGCACAGTGGTGAC
2466  123_HRV22    CATGTTTTATGATGGGTATGATGGAGG---TCCCGGATCACGTTATGGAGCAGTGGTAAC
2467  124_HRV22a   CATGTTTTATGATGGGTATGATGGAGG---TCCCGGATCACGTTATGGAGCAGTGGTAAC
2468  125_HRV22b   CATGTTTTATGATGGGTATGATGGAGG---TCCCGGATCACGTTATGGAGCAGTGGTAAC
2469  126_HRV82    TATGTTCTATGATGGCTATGATGGTGATGCTCCCGGATCGCGATACGGGACCATAGTGAC
2470  127_HRV82b   TATGTTCTATGATGGCTATGATGGTGATGCTCCCGGATCGCGATACGGGACCATAGTGAC
```

FIG. D10 CONT'D 06.trace                                                                9/20/2007 5:04 PM

```
2471  128_HRV82a    TATGTTCTATGATGGCTATGATGGTGATGCTCCCGGATCGCGATACGGGACCATAGTGAC
2472  129_HRV19     CATGTTTTATGATGGGTATGATGGAGATTCACCAGGATCCCGCTATGGAACAATAGTAAC
2473  130_HRV19a    CATGTTTTATGATGGGTATGATGGAGATTCACCAGGATCCCGCTATGGAACAATAGTAAC
2474  131_HRV19b    CATGTTTTATGATGGGTATGATGGAGATTCACCAGGATCCCGCTATGGAACAATAGTAAC
2475  132_HRV13     TATGTTTTATGATGGATATAATGGAGATTCCTCAGATGCACGCTATGGGACAACAATCAC
2476  133_HRV13a    CATGTTTTATGATGGATATAATGGAGATTCCTCAGATGCACGCTATGGGACAACAATCAC
2477  134_HRV13b    TATGTTTTATGATGGATATAATGGAGATTCCTCAGATGCACGCTATGGGACAACAATCAC
2478  135_HRV41     CATGTTTTATGATGGTTATGAAGAAGGCTCTACAAATGCACGCTATGGAACAACAGTCAC
2479  136_HRV41a    CATGTTTTATGATGGTTATGAAGAAGGCTCTACAAATGCACGCTATGGAACAACAGTCAC
2480  137_HRV41b    CATGTTTTATGATGGTTATGAAGAAGGCTCTACAAATGCACGCTATGGAACAACAGTCAC
2481  138_HRV73     TATGTTTTATGATGGATATGATGGTGACTCCACACAATCACATTATGGCACCACAGTAGT
2482  139_HRV73b    TATGTTTTATGATGGATATGATGGTGACTCCACACAATCACATTATGGCACCACAGTAGT
2483  140_HRV73a    TATGTTTTATGATGGATATGATGGTGACTCCACACAATCACATTATGGCACCACAGTAGT
2484  141_HRV61     TATGTTTTATGATGGTTATGATGGAGATTCTGAAATAACGCGCTATGGAACATCAGTGAC
2485  142_HRV61a    TATGTTTTATGATGGTTATGATGGAGATTCTGAAATAACGCGCTATGGAACATCAGTGAC
2486  143_HRV61b    TATGTTTTATGATGGTTATGATGGAGATTCTGAAATAACGCGCTATGGAACATCAGTGAC
2487  144_HRV96     CATGTTTTATGATGGATATGATGGTGACTCTGAATCAACACGCTATGGAACATCTGTTAC
2488  145_HRV96b    CATGTTTTATGATGGATATGATGGTGACTCTGAATCAACACGCTATGGAACATCTGTTAC
2489  146_HRV96a    CATGTTTTATGATGGATATGATGGTGACTCTGAATCAACACGCTATGGAACATCTGTTAC
2490   90_HRV16a|   CATGTTTTATGATGGTTATGATGGAGACACATATAAATCCAGATATGGAACTGTAGTCAC
2491   91_HRV16b|   CATGTTTTATGATGGTTATGATGGAGACACATATAAATCCAGATATGGAACTGTAGTCAC
2492   92_1AYM_A    CATGTTTTATGATGGTTATGATGGAGACACATATAAATCCAGATATGGAACTGTAGTCAC
2493   93_HRV81a|   CATGTTCTATGATGGATATGATGGTGATACTTATCACTCCAGATACGGGACTGTAGTCAC
2494   94_HRV81b|   CATGTTCTATGATGGATATGATGGTGATACTTATCACTCCAGATACGGGACTGTAGTCAC
2495   95_HRV81     CATGTTCTATGATGGATATGATGGTGATACTTATCACTCCAGATACGGGACTGTAGTCAC
2496  147_HRV2      CATGTTTTATGATGGGTATGATG------AACAAGATCAAAACTATGGTACAGCAAGCAC
2497  148_HRV2a|    CATGTTTTATGATGGGTATGATG------AACAAGATCAAAACTATGGTACAGCAAGCAC
2498  149_HRV2b|    CATGTTTTATGATGGGTATGATG------AACAAGATCAAAACTATGGTACAGCAAGCAC
2499  150_HRV49a    CATGTTTTATGATGGATATAATG------AACAGGGCCAAAATTATGGTACGGTAAGTAC
2500  151_HRV49b    CATGTTTTATGATGGATATAATG------AACAGGGCCAAAATTATGGTACGGTAAGTAC
2501  152_HRV49     CATGTTTTATGATGGATATAATG------AACAGGGCCAAAATTATGGTACGGTAAGTAC
2502  153_HRV23a    CATGTTTTATGATGGATACAATG------AGAAAGGCACGCATTATGGAACAGTTAGCAC
2503  154_HRV23b    CATGTTTTATGATGGATACAATG------AGAAAGGCACGCATTATGGAACAGTTAGCAC
2504  155_HRV23     CATGTTTTATGATGGATACAATG------AGAAAGGCACGCATTATGGAACAGTTAGCAC
2505  156_HRV30a    CATGTTCTATGATGGATACAATG------AGGGAGGCACAAATTATGGTACAGTGAGCAC
2506  157_HRV30b    CATGTTCTATGATGGATACAATG------AGGGAGGCACAAATTATGGTACAGTGAGCAC
2507  158_HRV30     CATGTTCTATGATGGATACAATG------AGGGAGGCACAAATTATGGTACAGTGAGCAC
2508  159_HRV7      TATGTTCTATGATGGATATGATGGTGATGCGTCATCCAAATATGGTTCCGTAGTAAC
2509  160_HRV7b|    TATGTTCTATGATGGATATGATGGTGATGATGCGTCATCCAAATATGGTTCCGTAGTAAC
2510  161_HRV7a|    TATGTTCTATGATGGATATGATGGTGATGATGCGTCATCCAAATATGGTTCCGTAGTAAC
2511  162_HRV88     TATGTTTTATGATGGATATGATGGTGATGATGCATCATCTAGGTATGGCTCAGTGGTAAC
2512  163_HRV88a    TATGTTTTATGATGGATATGATGGTGATGATGCATCATCTAGGTATGGCTCAGTGGTAAC
2513  164_HRV88b    TATGTTTTATGATGGATATGATGGTGATGATGCATCATCTAGGTATGGCTCAGTGGTAAC
2514  165_HRV36a    TATGTTTTATGATGGTTATGATGGTGATAATGCCGCATCAAAATATGGATCTGTGGTTAC
2515  166_HRV36b    TATGTTTTATGATGGTTATGATGGTGATAATGCCGCATCAAAATATGGATCTGTGGTTAC
2516  167_HRV36     TATGTTTTATGATGGTTATGATGGTGATAATGCCGCATCAAAATATGGATCTGTGGTTAC
2517  168_HRV89a    CATGTTTTATGATGGTTATGATGGTGATAGTGCAGCATCAAAATACGGTTCTGTAGTCAC
2518  169_HRV89b    CATGTTTTATGATGGTTATGATGGTGATAGTGCAGCATCAAAATACGGTTCTGTAGTCAC
2519  170_HRV89     CATGTTTTATGATGGTTATGATGGTGATAGTGCAGCATCAAAATACGGTTCTGTAGTCAC
2520  171_HRV58     TATGTTTTATGATGGCTATGATGGTGATGATGCTAAATCAATATATGGTTCTGTGGTAAC
2521  172_HRV58a    CATGTTTTATGATGGCTATGATGGTGATGATGCTAAATCAATATATGGTTCTGTGGTAAC
2522  173_HRV58b    TATGTTTTATGATGGCTATGATGGTGATGATGCTAAATCAATATATGGTTCTGTGGTAAC
2523  174_HRV12a    CATGTTTTATGATGGTTATGCTGATGACAACCCAAGTGCACCTTATGGAACTGTAGTTAC
2524  175_HRV12b    CATGTTTTATGATGGTTATGCTGATGACAACCCAAGTGCACCTTATGGAACTGTAGTTAC
2525  176_HRV12     CATGTTTTATGATGGTTATGCTGATGACAACCCAAGTGCACCTTATGGAACTGTAGTTAC
2526  177_HRV78a    CATGTTTTATGATGGATACTCGGATGACAGCACATCCTCTCCATATGGCACTGTAGTTAC
2527  178_HRV78b    CATGTTTTATGATGGATACTCGGATGACAGCACATCCTCTCCATATGGCACTGTAGTTAC
2528  179_HRV78     CATGTTTTATGATGGATACTCGGATGACAGCACATCCTCTCCATATGGCACTGTAGTTAC
2529  180_HRV20     TATGTTTTATGATGGTTATGAAGATGATAAGG---GAAGTGTGTATGGGTCTGTTGTCAC
2530  181_HRV20a    TATGTTTTATGATGGTTATGAAGATGATAAGG---GAAGTGTGTATGGGTCTGTTGTCAC
2531  182_HRV20b    TATGTTTTATGATGGTTATGAAGATGATAAGG---GAAGTGTGTATGGGTCTGTTGTCAC
2532  183_HRV68     TATGTTTTATGATGGATATGAGGATGACAAAG---GAAGTGTGTATGGATCTGTTGTTAC
2533  184_HRV68a    TATGTTTTATGATGGATATGATGGAGACAAAG---GAAGTGTGTATGGATCTGTTGTTAC
2534  185_HRV68b    TATGTTTTATGATGGATATGAGGATGACAAAG---GAAGTGTGTATGGATCTGTTGTTAC
2535  186_HRV28     CATGTTTTATGATGGTTATGAAGATGACAATG---GAACTACCTATGGTGCAGTGGTTAC
```

FIG. D10 CONT'D 06.trace                                                                  9/20/2007 5:04 PM

```
2536  187_HRV28a   CATGTTTTATGATGGTTATGAAGATGACAATG---GAACTACCTATGGTGCAGTGGTTAC
2537  188_HRV28b   CATGTTTTATGATGGTTATGAAGATGACAATG---GAACTACCTATGGTGCAGTGGTTAC
2538  189_HRV53a   TATGTTCTATGATGGGTATGAAGATGACAATG---GCACCACTTATGGGGCTGTTGTTAC
2539  190_HRV53b   TATGTTCTATGATGGGTATGAAGATGACAATG---GCACCACTTATGGGGCTGTTGTTAC
2540  191_HRV53    TATGTTCTATGATGGGTATGAAGATGACAATG---GCACCACTTATGGGGCTGTTGTTAC
2541  192_HRV46a   CATGTTTTATGATGGCTACGAAAGTGATAAAG---GCAAGATCTATGGAACTGCAGTCAC
2542  193_HRV46b   CATGTTTTATGATGGCTACGAAAGTGATAAAG---GCAAGATCTATGGAACTGCAGTCAC
2543  194_HRV46    CATGTTTTATGATGGCTACGAAAGTGATAAAG---GCAAGATCTATGGAACTGCAGTCAC
2544  195_HRV80a   CATGTTCTATGATGGGTATGAGAGTGATAAAG---GCAACATTTATGGAACAGCAGTTAC
2545  196_HRV80b   CATGTTCTATGATGGGTATGAGAGTGATAAAG---GCAACATTTATGGAACAGCAGTTAC
2546  197_HRV80    CATGTTCTATGATGGGTATGAGAGTGATAAAG---GCAACATTTATGGAACAGCAGTTAC
2547  198_HRV51    CATGTTTTATGATGGGTATGAAGGTGATAGTTTGACCTCACAGTACGGTTCAGTAGTCAC
2548  199_HRV51a   CATGTTTTATGATGGGTATGAAGGTGATAGTTTGACCTCACAGTACGGTTCAGTAGTCAC
2549  200_HRV51b   CATGTTTTATGATGGGTATGAAGGTGATAGTTTGACCTCACAGTACGGTTCAGTAGTCAC
2550  201_HRV65a   CATGTTCTATGATGGTTATGAGGGTGATGACCCAAATTCAAAATATGGTTCAGTGGTTAC
2551  202_HRV65b   CATGTTCTATGATGGTTATGAGGGTGATGACCCAAATTCAAAATATGGTTCAGTGGTTAC
2552  203_HRV65    CATGTTCTATGATGGTTATGAGGGTGATGACCCAAATTCAAAATATGGTTCAGTGGTTAC
2553  204_HRV71a   CATGTTCTATGATGGGTATGAAGGTGATGCCCTCAGTTCTAAATATGGCTCAGTAGTTAC
2554  205_HRV71b   CATGTTCTATGATGGGTATGAAGGTGATGCCCTCAGTTCTAAATATGGCTCAGTAGTTAC
2555  206_HRV71    CATGTTCTATGATGGGTATGAAGGTGATGCCCTCAGTTCTAAATATGGCTCAGTAGTTAC
2556  207_HRV8     CATGTTCTATGATGGTTATGATTCAGATGGTTTAGATGCTATTTATGGTATTCCTGTTAC
2557  208_HRV95    CATGTTCTATGATGGTTATGATTCAGATGGTTTAGATGCTATTTATGGTATTCCTGTTAC
2558  209_HRV45    CATGTTTTATGGATACGACACTGATGGCACAGATGCAGTGTATGGTGTTAGTGTGAC
2559  210_HRV45a   CATGTTTTATGATGGATACGACACTGATGGCACAGATGCAGTGTATGGTGTTAGTGTGAC
2560  211_HRV45b   CATGTTTTATGATGGATACGACACTGATGGCACAGATGCAGTGTATGGTGTTAGTGTGAC
2561  GROUP_1      -ATGTT-TA-GA-GG-TA----------------------TA-GG------------
2562
2563  1_HRV1A1|d   TAATGATATGGGTACTATATGCTCAAGAATAGTTACAGAAAAACAGAAACATTCTGTTGT
2564  2_HRV1A2|d   TAATGATATGGGTACTATATGCTCAAGAATAGTTACAGAAAAACAGAAACATTCTGTTGT
2565  3_HRV1A|cD   TAATGATATGGGTACTATATGCTCAAGAATAGTTACAGAAAAACAGAAACATTCTGTTGT
2566  4_HRV1B1|d   CAATGATATGGGAACCATATGTTCAAGAATAGTTACAGAGAAGCAGGAACACCCTGTCGT
2567  5_HRV1B2|d   CAATGATATGGGAACCATATGTTCAAGAATAGTTACAGAGAAGCAGGAACACCCTGTCGT
2568  6_HRV1B      CAATGATATGGGAACCATATGTTCAAGAATAGTTACAGAGAAGCAGGAACACCCTGTCGT
2569  7_HRV40a|d   TAACCATATGGGAACGCTATGCTCAAGAATAGTCACCAACAAGCAGCAGCATGAAGTTGA
2570  8_HRV40b|d   TAACCATATGGGAACGCTATGCTCAAGAATAGTCACCAACAAGCAGCAGCATGAAGTTGA
2571  9_HRV40      TAACCATATGGGAACGCTATGCTCAAGAATAGTCACCAACAAGCAGCAGCATGAAGTTGA
2572  10_HRV85     CAACCACATGGGAACACTGTGCTCGAGGATAGTTACCAACAAACAGCAGCATGAGGTTGA
2573  11_HRV85a|   CAACCACATGGGAACACTGTGCTCGAGGATAGTTACCAACAAACAGCAGCATGAGGTTGA
2574  12_HRV85b|   CAACCACATGGGAACACTGTGCTCGAGGATAGTTACCAACAAACAGCAGCATGAGGTTGA
2575  13_HRV56a|   AAACCACATGGGGACACTCTGTTCAAGAATTGTGACAAATAAACAACTTCATCCTGTTGA
2576  14_HRV56b|   AAACCACATGGGGACACTCTGTTCAAGAATTGTGACAAATAAACAACTTCATCCTGTTGA
2577  15_HRV56     AAACCACATGGGGACACTCTGTTCAAGAATTGTGACAAATAAACAACTTCATCCTGTTGA
2578  16_HRV54     CAATCATATGGGTACTTTGTGTTCAAGAGTGGTTACTGATAAACAAAAACACCCAGTTGA
2579  17_HRV98     TAATCACATGGGCACTTTGTGTTCAAGAGTAGTTACTGGCAAACAAGAACACCCAGTTGA
2580  18_HRV59a|   CAACCACATGGGCACTTTATGTTCTAGAATAGTTACAAACAGTCAGGAGCATCCAGTGGA
2581  19_HRV59b|   CAACCACATGGGCACTTTATGTTCTAGAATAGTTACAAACAGTCAGGAGCATCCAGTGGA
2582  20_HRV59     CAACCACATGGGCACTTTATGTTCTAGAATAGTTACAAACAGTCAGGAGCATCCAGTGGA
2583  21_HRV63     TAACCACATGGGGACTTTATGTTCTAGAATTGTAACAAACAGCCAAGAACATCCAGTTGA
2584  22_HRV63b|   TAACCACATGGGGACTTTATGTTCTAGAATTGTAACAAACAGCCAAGAACATCCAGTTGA
2585  23_HRV63a|   TAACCACATGGGGACTTTATGTTCTAGAATTGTAACAAACAGCCAAGAACATCCAGTTGA
2586  24_HRV39     TAATGATATGGGTACACTTTGCACTAGAATTGTAACAAACCAACAGGAACACCTAGTGGA
2587  25_HRV39a|   TAATGATATGGGTACACTTTGCACTAGAATTGTAACAAACCAACAGGAACACCTAGTGGA
2588  26_HRV39b|   TAATGATATGGGTACACTTTGCACTAGAATTGTAACAAACCAACAGGAACACCTAGTGGA
2589  27_HRV10a|   AAATCACATGGGCACTTTGTGCATGCGAATAGTCACAAACCAGCAAGCACATGAGGTGGA
2590  28_HRV10b|   AAATCACATGGGCACTTTGTGCATGCGAATAGTCACAAACCAGCAAGCACATGAGGTGGA
2591  29_HRV10     AAATCACATGGGCACTTTGTGCATGCGAATAGTCACAAACCAGCAAGCACATGAGGTGGA
2592  30_HRV100a   TAACCACATGGGTACACTTTGTATGAGGATAGTTACAAATCAGCAAGCACATGAGGTGGA
2593  31_HRV100b   TAACCACATGGGTACACTTTGTATGAGGATAGTTACAAATCAGCAAGCACATGAGGTGGA
2594  32_HRV100    TAACCACATGGGTACACTTTGTATGAGGATAGTTACAAATCAGCAAGCACATGAGGTGGA
2595  33_HRV66     TAATCATATGGGTACATTATTGTATTAGGATTGTTACAAATGAACAGCACCATAATGTTGA
2596  34_HRV66b|   TAATCATATGGGTACATTATGTATTAGGATTGTTACAAATGAACAGCACCATAATGTTGA
2597  35_HRV66a|   TAATCATATGGGTACATTATGTATTAGGATTGTTACAAATGAACAGCACCATAATGTTGA
2598  36_HRV77a|   TAATCACATGGGCACACTGTGCATTAGAATAGTCACTAATCAGCAAAATCATGAGGTTGA
2599  37_HRV77b|   TAATCACATGGGCACACTGTGCATTAGAATAGTCACTAATCAGCAAAATCATGAGGTTGA
2600  38_HRV77     TAATCACATGGGCACACTGTGCATTAGAATAGTCACTAATCAGCAAAATCATGAGGTTGA
```

FIG. D10 CONT'D

```
06.trace                                                                    9/20/2007 5:04 PM 2601  39_HRV62a    TAATCGTATGGGGGCACTGTGTATGAGGATTGTCACAAACAAACAAGTTCATGATGTTGA
2602  40_HRV62b    TAATCGTATGGGGGCACTGTGTATGAGGATTGTCACAAACAAACAAGTTCATGATGTTGA
2603  41_HRV25     TAACCGTATGGGAGCACTGTGCATGAGAATTGTCACAAATAAACAAGTCCATGATGTTGA
2604  42_HRV29a    TAACCGGATGGGGACGCTTTGTGTCAGAATTGTTACAGGCAAACAAGCTCATGATGTTCA
2605  43_HRV29b    TAACCGGATGGGGACGCTTTGTGTCAGAATTGTTACAGGCAAACAAGCTCATGATGTTCA
2606  44_HRV44a    TAACCGGATGGGGACGCTTTGCGTCAGGATCGTTACGGGCAAACAGGCTCATGATGTCCA
2607  45_HRV44b    TAACCGGATGGGGACGCTTTGCGTCAGGATCGTTACGGGCAAACAGGCTCATGATGTCCA
2608  46_HRV31     TAATCGCATGGGTGCACTATGCATGAGAGTTGTCACTAACAAACAAGCTCATAAAGTTGA
2609  47_HRV31a|   TAATCGCATGGGTGCACTATGCATGAGAGTTGTCACTAACAAACAAGCTCATAAAGTTGA
2610  48_HRV31b|   TAATCGCATGGGTGCACTATGCATGAGAGTTGTCACTAACAAACAAGCTCATAAAGTTGA
2611  49_HRV47     CAATCGCATGGGTGCATTGTGTATGAGAGTTGTAACAAACAAGCAACTCCATAAAGTTGA
2612  50_HRV47a|   CAATCGCATGGGTGCATTGTGTATGAGAGTTGTAACAAACAAGCAACTCCATAAAGTTGA
2613  51_HRV47b|   CAATCGCATGGGTGCATTGTGTATGAGAGTTGTAACAAACAAGCAACTCCATAAAGTTGA
2614  52_HRV11     CAATGATATGGGCACTCTGTGTTATAGAATAGTAACTGATGACCATAGACACAAAATTGA
2615  53_HRV11b|   CAATGATATGGGCACTCTGTGTTATAGAATAGTAACTGATGACCATAGACACAAAATTGA
2616  54_HRV11a|   CAATGATATGGGCACTCTGTGTTATAGAATAGTAACTGATGACCATAGACACAAAATTGA
2617  55_HRV76     CAATGACATGGGCACCCTATGTTCCAGGATAGTAACTGATGATCATAAGCACAAGATTGA
2618  56_HRV76b|   CAATGACATGGGCACCCTATGTTCCAGGATAGTAACTGATGATCATAAGCACAAGATTGA
2619  57_HRV76a|   CAATGACATGGGCACCCTATGTTCCAGGATAGTAACTGATGATCATAAGCACAAGATTGA
2620  58_HRV33     CAATGACATGGGCACTTTATGCTCTAGAATAGTTACAGATAATCATAAGCATCCAATAGA
2621  59_HRV33b|   CAATGACATGGGCACTTTATGCTCTAGAATAGTTACAGATAATCATAAGCATCCAATAGA
2622  60_HRV33a|   CAATGACATGGGCACTTTATGCTCTAGAATAGTTACAGATAATCATAAGCATCCAATAGA
2623  61_HRV24a|   AAACGACATGGGAACTCTATGCTATAGAATAGTCACTGACAAGCATAATCACCAAATAGA
2624  62_HRV24b|   AAACGACATGGGAACTCTATGCTATAGAATAGTCACTGACAAGCATAATCACCAAATAGA
2625  63_HRV24     AAACGACATGGGAACTCTATGCTATAGAATAGTCACTGACAAGCATAATCACCAAATAGA
2626  64_HRV90     TAATGATATGGGAACCTTATGTTATAGAATAGTTACAGATGAACATGCCCACAAAATAGA
2627  65_HRV90a|   TAATGATATGGGAACCTTATGTTATAGAATAGTTACAGATGAACATGCCCACAAAATAGA
2628  66_HRV90b|   TAATGATATGGGAACCTTATGTTATAGAATAGTTACAGATGAACATGCCCACAAAATAGA
2629  67_HRV34     TAATGACATGGGTACTTTATGCTCCAGAATTGTAACTGATGAACACCAAAACAGAGTAGA
2630  68_HRV34b|   TAATGACATGGGTACTTTATGCTCCAGAATTGTAACTGATGAACACCAAAACAGAGTAGA
2631  69_HRV34a|   TAATGACATGGGTACTTTATGCTCCAGAATTGTAACTGATGAACACCAAAACAGAGTAGA
2632  70_HRV50a|   CAATGACATGGGCACTTTGTGTTCTAGGATTGTCACTGATGAGCACCAAAATAAAGTGGA
2633  71_HRV50b|   CAATGACATGGGCACTTTGTGTTCTAGGATTGTCACTGATGAGCACCAAAATAAAGTGGA
2634  72_HRV50     CAATGACATGGGCACTTTGTGTTCTAGGATTGTCACTGATGAGCACCAAAATAAAGTGGA
2635  73_HRV18a|   AAATGACATGGGTACCTTGTGCTCTAGAATAGTCACAGATAAACATAAGAATGAGGTGGA
2636  74_HRV18b|   AAATGACATGGGTACCTTGTGCTCTAGAATAGTCACAGATAAACATAAGAATGAGGTGGA
2637  75_HRV18     AAATGACATGGGTACCTTGTGCTCTAGAATAGTCACAGATAAACATAAGAATGAGGTGGA
2638  76_HRV55     TAATGACATGGGTACTTTATGTTCTAGAATAATAACTGATAACCATAAGCACCCAATTGA
2639  77_HRV55b|   TAATGACATGGGTACTTTATGTTCTAGAATAATAACTGATAACCATAAGCACCCAATTGA
2640  78_HRV55a|   TAATGACATGGGTACTTTATGTTCTAGAATAATAACTGATAACCATAAGCACCCAATTGA
2641  79_HRV57     TAATGACATGGGCACTTTATGTTCTAGAATTGTTACTGACCAGCACACACATCCCATAAA
2642  80_HRV57a|   TAATGACATGGGCACTTTATGTTCTAGAATTGTTACTGACCAGCACACACATCCCATAAA
2643  81_HRV57b|   TAATGACATGGGCACTTTATGTTCTAGAATTGTTACTGACCAGCACACACATCCCATAAA
2644  82_HRV21     TAATGATATGGGATCTCTATGCTACAATAGTAACTGGCCAGCATAAGCATAAGATAGA
2645  83_HRVHan    TAATGATATGGGATCTCTATGCTATAGAATAGTAACTGATCAGCATAAGCACAAGATAGA
2646  84_HRV43     CAACCACATGGGAACATTATGTTCTAGGATAGTTACAGAAGAACACCAAAATCAAATCGA
2647  85_HRV43b|   CAACCACATGGGAACATTATGTTCTAGGATAGTTACAGAAGAACACCAAAATCAAATCGA
2648  86_HRV43a|   CAACCACATGGGAACATTATGTTCTAGGATAGTTACAGAAGAACACCAAAATCAAATCGA
2649  87_HRV75     TAATCACATGGGGACACTGTGTTCTAGAATAGTTACAGAAGAACATCGAAATAAAGTTGA
2650  88_HRV75b|   TAATCACATGGGGACACTGTGTTCTAGAATAGTTACAGAAGAACATCGAAATAAAGTTGA
2651  89_HRV75a|   TAATCACATGGGGACACTGTGTTCTAGAATAGTTACAGAAGAACATCGAAATAAAGTTGA
2652  96_HRV9a|d   AAATGATATGGGATCTTTATGTTCCCGTGTAGTTACTGAAGAGCATGGACCCCGTGTCAA
2653  97_HRV9b|d   AAATGATATGGGATCTTTATGTTCCCGTGTAGTTACTGAAGAGCATGGACCCCGTGTCAA
2654  98_HRV9      AAATGATATGGGATCTTTATGTTCCCGTGTAGTTACTGAAGAGCATGGACCCCGTGTCAA
2655  99_HRV32     AAATGATATGGGTTCCCTGTGTTCTCGTATAGTCACCGAAGAGCACGGATCCCGTGTTGA
2656  100_HRV32a   AAATGATATGGGTTCCCTGTGTTCTCGTATAGTCACCGAAGAGCACGGATCCCGTGTTGA
2657  101_HRV32b   AAATGATATGGGTTCCCTGTGTTCTCGTATAGTCACCGAAGAGCACGGATCCCGTGTTGA
2658  102_HRV67    TAATGATATGGGTTCCTTGTGTTCGCGTATAGTTACTGAAGAACATGGTTCTCGCGTAAA
2659  103_HRV67a   TAATGATATGGGTTCCTTGTGTTCGCGTATAGTTACTGAAGAACATGGTTCTCGCGTAAA
2660  104_HRV67b   TAATGATATGGGTTCCTTGTGTTCGCGTATAGTTACTGAAGAACATGGTTCTCGCGTAAA
2661  105_HRV15    TAATGACATGGGGACACTGTGTTCTAGAATAGTAACTGAAGAGCATGGGACACGTGTAGA
2662  106_HRV15a   TAATGACATGGGGACACTGTGTTCTAGAATAGTAACTGAAGAGCATGGGACACGTGTAGA
2663  107_HRV15b   TAATGACATGGGGACACTGTGTTCTAGAATAGTAACTGAAGAGCATGGGACACGTGTAGA
2664  108_HRV74a   AAATGACATGGGAACTCTATGTTCTAGAATTGTGACTGAAGAACACGATGCACGTGTGGA
2665  109_HRV74b   AAATGACATGGGAACTCTATGTTCTAGAATTGTGACTGAAGAACACGATGCACGTGTGGA
```

FIG. D10 CONT'D

```
06.trace                                                                                    9/20/2007 5:04 PM 2666 110_HRV74   AAATGACATGGGAACTCTATGTTCTAGAATTGTGACTGAAGAACACGATGCACGTGTGGA
2667 111_HRV38a  CAATGATATGGGGACACTTTGTTCAAGAATAGTCACTGAAAATCATGGGACCCAAGTGAA
2668 112_HRV38b  CAATGATATGGGGACACTTTGTTCAAGAATAGTCACTGAAAATCATGGGACCCAAGTGAA
2669 113_HRV38   CAATGATATGGGGACACTTTGTTCAAGAATAGTCACTGAAAATCATGGGACCCAAGTGAA
2670 114_HRV60   CAATGACATGGGAACGTTGTGCTCCAGAATAGTTACTGAACACCATGGTACACAGGTTCA
2671 115_HRV60a  CAATGACATGGGAACGTTGTGCTCCAGAATAGTTACTGAACACCATGGTACACAGGTTCA
2672 116_HRV60b  CAATGACATGGGAACGTTGTGCTCCAGAATAGTTACTGAACACCATGGTACACAGGTTCA
2673 117_HRV64a  AAATGATATGGGCACTTTGTGTTCTAGAATTGTGACTGAGGAACACACAACACAGGTCAA
2674 118_HRV64b  AAATGATATGGGCACTTTGTGTTCTAGAATTGTGACTGAGGAACACACAACACAGGTCAA
2675 119_HRV64   AAATGATATGGGCACTTTGTGTTCTAGAATTGTGACTGAGGAACACACAACACAGGTCAA
2676 120_HRV94a  AAATGACATGGGAACATTATGCTCCAGGATTGTGACTGAGGAGCACAAGACACAGGTTAA
2677 121_HRV94b  AAATGACATGGGAACATTATGCTCCAGGATTGTGACTGAGGAGCACAAGACACAGGTTAA
2678 122_HRV94   AAATGACATGGGAACATTATGCTCCAGGATTGTGACTGAGGAGCACAAGACACAGGTTAA
2679 123_HRV22   AAATGATATGGGCACACTGTGCTCTAGGATTGTGACTGAAGAACACCAGACACAAGTCAA
2680 124_HRV22a  AAATGATATGGGCACACTGTGCTCTAGGATTGTGACTGAAGAACACCAGACACAAGTCAA
2681 125_HRV22b  AAATGATATGGGCACACTGTGCTCTAGGATTGTGACTGAAGAACACCAGACACAAGTCAA
2682 126_HRV82   AAATGACATGGGTACACTGTGTTCTAGAATTGTAACTGAAGAACACCAGACTCAAGTCAG
2683 127_HRV82b  AAATGACATGGGTACACTGTGTTCTAGAATTGTAACTGAAGAACACCAGACTCAAGTCAG
2684 128_HRV82a  AAATGACATGGGTACACTGTGTTCTAGAATTGTAACTGAAGAACACCAGACTCAAGTCAG
2685 129_HRV19   TAATGATATGGGAACCTTATGCTCCAGAATAGTAACTGATGAACACCAAACACAGGTTGC
2686 130_HRV19a  TAATGATATGGGAACCTTATGCTCCAGAATAGTAACTGATGAACACCAAACACAGGTTGC
2687 131_HRV19b  TAATGATATGGGAACCTTATGCTCCAGAATAGTAACTGATGAACACCAAACACAGGTTGC
2688 132_HRV13   TAATGATATGGGCACACTTTGCTTCAGAATAGTAACTGAAGAACATACTAACAAGGTCAA
2689 133_HRV13a  TAATGATATGGGCACACTTTGCTTCAGAATAGTAACTGAAGAACATACTAACAAGGTCAA
2690 134_HRV13b  TAATGATATGGGCACACTTTGCTTCAGAATAGTAACTGAAGAACATACTAACAAGGTCAA
2691 135_HRV41   AAATGACATGGGTACATTATGCTTTAGAATAGTTACTGAAGAACACACCAACAAAGTTAA
2692 136_HRV41a  AAATGACATGGGTACATTATGCTTTAGAATAGTTACTGAAGAACACACCAACAAAGTTAA
2693 137_HRV41b  AAATGACATGGGTACATTATGCTTTAGAATAGTTACTGAAGAACACACCAACAAAGTTAA
2694 138_HRV73   TAATGATATGGGCACATTATGCTTTAGGATAGTGACTGAAGAACACACTAGCAGGGTAAA
2695 139_HRV73b  TAATGATATGGGCACATTATGCTTTAGGATAGTGACTGAAGAACACACTAGCAGGGTAAA
2696 140_HRV73a  TAATGATATGGGCACATTATGCTTTAGGATAGTGACTGAAGAACACACTAGCAGGGTAAA
2697 141_HRV61   AAATGATATGGGTGCATTGTGCTTTAGAATAGTAACTGAACAGCATACAAATCAAGTTAA
2698 142_HRV61a  AAATGATATGGGTGCATTGTGCTTTAGAATAGTAACTGAACAGCATACAAATCAAGTTAA
2699 143_HRV61b  AAATGATATGGGTGCATTGTGCTTTAGAATAGTAACTGAACAGCATACAAATCAAGTTAA
2700 144_HRV96   CAATGACATGGGCACTTTATGTTTTAGAATAGTGACAGAGGAACACACCAACAAGGTCAA
2701 145_HRV96b  CAATGACATGGGCACTTTATGTTTTAGAATAGTGACAGAGGAACACACCAACAAGGTCAA
2702 146_HRV96a  CAATGACATGGGCACTTTATGTTTTAGAATAGTGACAGAGGAACACACCAACAAGGTCAA
2703 90_HRV16|   CAATGACATGGGAACTTTGTGTTCGCGTATTGTGACCAGTGAGCAATTACACAAAGTCAA
2704 91_HRV16b|  CAATGACATGGGAACTTTGTGTTCGCGTATTGTGACCAGTGAGCAATTACACAAAGTCAA
2705 92_1AYM_A   CAATGACATGGGAACTTTGTGTTCGCGTATTGTGACCAGTGAGCAATTACACAAAGTCAA
2706 93_HRV81a|  TAATGATATGGGAACATTATGCTCACGGATAGTGACAAGTGAGCAAGTGCACAAGGTGAA
2707 94_HRV81b|  TAATGATATGGGAACATTATGCTCACGGATAGTGACAAGTGAGCAAGTGCACAAGGTGAA
2708 95_HRV81    TAATGATATGGGAACATTATGCTCACGGATAGTGACAAGTGAGCAAGTGCACAAGGTGAA
2709 147_HRV2    AAATAACATGGGGTCACTATGCTCTAGGATAGTAACAGAGAAACACATTCATAAGGTACA
2710 148_HRV2a|  AAATAACATGGGGTCACTATGCTCTAGGATAGTAACAGAGAAACACATTCATAAGGTACA
2711 149_HRV2b|  AAATAACATGGGGTCACTATGCTCTAGGATAGTAACAGAGAAACACATTCATAAGGTACA
2712 150_HRV49a  AAACAACATGGGATCATTATGCTCTAGGATAGTAACAGAGAAACACATTCACAGTATGCA
2713 151_HRV49b  AAACAACATGGGATCATTATGCTCTAGGATAGTAACAGAGAAACACATTCACAGTATGCA
2714 152_HRV49   AAACAACATGGGATCATTATGCTCTAGGATAGTAACAGAGAAACACATTCACAGTATGCA
2715 153_HRV23a  AAACAACATGGGCACATTGTGCTCCAGAGTGGTAACAGAGAAACACATTCATGATATGCG
2716 154_HRV23b  AAACAACATGGGCACATTGTGCTCCAGAGTGGTAACAGAGAAACACATTCATGATATGCG
2717 155_HRV23   AAACAACATGGGCACATTGTGCTCCAGAGTGGTAACAGAGAAACACATTCATGATATGCG
2718 156_HRV30a  AAACAACATGGGCACACTGTGTTCCAGAGTGGTAACAGAAAAACACATTCATGATGTGCG
2719 157_HRV30b  AAACAACATGGGCACACTGTGTTCCAGAGTGGTAACAGAAAAACACATTCATGATGTGCG
2720 158_HRV30   AAACAACATGGGCACACTGTGTTCCAGAGTGGTAACAGAAAAACACATTCATGATGTGCG
2721 159_HRV7    CAATGACATGGGAACCATATGTGTTAGACTAGTTACATCTACACAAAAACACAATTTAAA
2722 160_HRV7b|  CAATGACATGGGAACCATATGTGTTAGACTAGTTACATCTACACAAAAACACAATTTAAA
2723 161_HRV7a|  CAATGACATGGGAACCATATGTGTTAGACTAGTTACATCTACACAAAAACACAATTTAAA
2724 162_HRV88   TAATGATATGGGAACTATATGTATTAGATTGGTCACCTCCACCCAAAAGCATAAACTGAA
2725 163_HRV88a  TAATGATATGGGAACTATATGTATTAGATTGGTCACCTCCACCCAAAAGCATAAACTGAA
2726 164_HRV88b  TAATGATATGGGAACTATATGTATTAGATTGGTCACCTCCACCCAAAAGCATAAACTGAA
2727 165_HRV36a  TAACGACATGGGAACCATATGTGTTAGAATAGTTACATCCAACCAAAAACATGATTTAAA
2728 166_HRV36b  TAACGACATGGGAACCATATGTGTTAGAATAGTTACATCCAACCAAAAACATGATTTAAA
2729 167_HRV36   TAACGACATGGGAACCATATGTGTTAGAATAGTTACATCCAACCAAAAACATGATTTAAA
2730 168_HRV89a  TAATGATATGGGAACCATATGTGTTAGAATAGTGACATCCAACCAAAAACATGATTTAAA
```

FIG. D10 CONT'D

```
06.trace                                                                   9/20/2007 5:04 PM 2731 169_HRV89b   TAATGATATGGGAACCATATGTGTTAGAATAGTGACATCCAACCAAAAACATGATTTAAA
2732 170_HRV89    TAATGATATGGGAACCATATGTGTTAGAATAGTGACATCCAACCAAAAACATGATTTAAA
2733 171_HRV58    AAATGACATGGGAACTATATGTGTTAGAATAGTCACATCCAAACAAAGACACAATTTAAA
2734 172_HRV58a   AAATGACATGGGAACTATATGTGTTAGAATAGTCACATCCAAACAAAGACACAATTTAAA
2735 173_HRV58b   AAATGACATGGGAACTATATGTGTTAGAATAGTCACATCCAAACAAAGACACAATTTAAA
2736 174_HRV12a   CAATGACATGGGTTCACTGTGTGTCAGAATAGTTACAGACCAGCAAAAACATAAAGTTAA
2737 175_HRV12b   CAATGACATGGGTTCACTGTGTGTCAGAATAGTTACAGACCAGCAAAAACATAAAGTTAA
2738 176_HRV12    CAATGACATGGGTTCACTGTGTGTCAGAATAGTTACAGACCAGCAAAAACATAAAGTTAA
2739 177_HRV78a   CAATGACATGGGTACACTGTGTATGAGGATGGTTACAGATCAACAACAACATAAGGTCAC
2740 178_HRV78b   CAATGACATGGGTACACTGTGTATGAGGATGGTTACAGATCAACAACAACATAAGGTCAC
2741 179_HRV78    CAATGACATGGGTACACTGTGTATGAGGATGGTTACAGATCAACAACAACATAAGGTCAC
2742 180_HRV20    AAACGATATGGGCACATTGTGTGTTCGTATTGTGACTGAGCAGCAGACACATAAGGTTAA
2743 181_HRV20a   AAACGATATGGGCACATTGTGTGTTCGTATTGTGACTGAGCAGCAGACACATAAGGTTAA
2744 182_HRV20b   AAACGATATGGGCACATTGTGTGTTCGTATTGTGACTGAGCAGCAGACACATAAGGTTAA
2745 183_HRV68    AAATGATATGGGCACATTATGTGTCCGTATTGTGACTGAGCAGCAGACACATAGGGTCAA
2746 184_HRV68a   AAATGATATGGGCACATTATGTGTCCGTATTGTGACTGAGCAGCAGACACATAGGGTCAA
2747 185_HRV68b   AAATGATATGGGCACATTATGTGTCCGTATTGTGACTGAGCAGCAGACACATAGGGTCAA
2748 186_HRV28    AAATCATATGGGAACACTCTGTGCTCGCATAGTAACTGAACAACAGAAGCATGAAGTCAA
2749 187_HRV28a   AAATCATATGGGAACACTCTGTGCTCGCATAGTAACTGAACAACAGAAGCATGAAGTCAA
2750 188_HRV28b   AAATCATATGGGAACACTCTGTGCTCGCATAGTAACTGAACAACAGAAGCATGAAGTCAA
2751 189_HRV53a   TAATGATATGGGAACACTTTGTGTGCGCATAGTGACTGAGCAACAGAAAAATGAGGTCAA
2752 190_HRV53b   TAATGATATGGGAACACTTTGTGTGCGCATAGTGACTGAGCAACAGAAAAATGAGGTCAA
2753 191_HRV53    TAATGATATGGGAACACTTTGTGTGCGCATAGTGACTGAGCAACAGAAAAATGAGGTCAA
2754 192_HRV46a   CAATGATATGGGAACTATATGTGTCAGAATTGTTACCGAACAACAAAAACATAAGGTTCT
2755 193_HRV46b   CAATGATATGGGAACTATATGTGTCAGAATTGTTACCGAACAACAAAAACATAAGGTTCT
2756 194_HRV46    CAATGATATGGGAACTATATGTGTCAGAATTGTTACCGAACAACAAAAACATAAGGTTCT
2757 195_HRV80a   CAATGATATGGGAACCCTGTGTGCTAGAATTGTTACAGAACAACAGAAACATAAAGTCCT
2758 196_HRV80b   CAATGATATGGGAACCCTGTGTGCTAGAATTGTTACAGAACAACAGAAACATAAAGTCCT
2759 197_HRV80    CAATGATATGGGAACCCTGTGTGCTAGAATTGTTACAGAACAACAGAAACATAAAGTCCT
2760 198_HRV51    AAATGCTATGGGGACACTATGTGTTCGTGTGGTCACAGAGCAACAAAAACATGAGGTTAA
2761 199_HRV51a   AAATGCTATGGGGACACTATGTGTTCGTGTGGTCACAGAGCAACAAAAACATGAGGTTAA
2762 200_HRV51b   AAATGCTATGGGGACACTATGTGTTCGTGTGGTCACAGAGCAACAAAAACATGAGGTTAA
2763 201_HRV65a   TAATGCTATGGGCACACTATATGTGCGTGTGGTTACAGAAAGGCAAAAACATGAAGTCAA
2764 202_HRV65b   TAATGCTATGGGCACACTATATGTGCGTGTGGTTACAGAAAGGCAAAAACATGAAGTCAA
2765 203_HRV65    TAATGCTATGGGCACACTATATGTGCGTGTGGTTACAGAAAGGCAAAAACATGAAGTCAA
2766 204_HRV71a   TAATGCCATGGGCACCTTATGTGTTCGTGTGGTTACAGAACAGCAAAGCAACACAGTCAA
2767 205_HRV71b   TAATGCCATGGGCACCTTATGTGTTCGTGTGGTTACAGAACAGCAAAGCAACACAGTCAA
2768 206_HRV71    TAATGCCATGGGCACCTTATGTGTTCGTGTGGTTACAGAACAGCAAAGCAACACAGTCAA
2769 207_HRV8     AAATCACATGGGCACAATATGTGTGAGAATGGTGACAGATAAACAGAAAATTAAAACTAA
2770 208_HRV95    AAATCACATGGGCACAATATGTGTGAGAATGGTGACAGATAAACAGAAAATTAAAACTAA
2771 209_HRV45    TAACCATATGGGGACTATATGTGTTAGAATTGTTACAGACCAACAACAACATAGAGTTAA
2772 210_HRV45a   TAACCATATGGGGACTATATGTGTTAGAATTGTTACAGACCAACAACAACATAGAGTTAA
2773 211_HRV45b   TAACCATATGGGGACTATATGTGTTAGAATTGTTACAGACCAACAACAACATAGAGTTAA
2774 GROUP_1      -AA----ATGGG--C--T-T------G--T--T-AC-------CA--------------
2775
2776  1_HRV1A1|d  CATCACAACACACATATATCATAAAGCTAAACACACAAAAGCTTGGTGTCCTAGGCCCCC
2777  2_HRV1A2|d  CATCACAACACACATATATCATAAAGCTAAACACACAAAAGCTTGGTGTCCTAGGCCCCC
2778  3_HRV1A|cD  CATCACAACACACATATATCATAAAGCTAAACACACAAAAGCTTGGTGTCCTAGGCCCCC
2779  4_HRV1B1|d  TATTCAACACACATATATCACAAAGCTAAACACACAAAAGCTTGGTGTCCTAGGCCCTCC
2780  5_HRV1B2|d  TATTACAACACACATATATCACAAAGCTAAACACACAAAAGCTTGGTGTCCTAGGCCCTCC
2781  6_HRV1B     TATTACAACACACATATATCACAAAGCTAAACACACAAAAGCTTGGTGTCCTAGGCCCTCC
2782  7_HRV40a|d  GATTACCACACGTATATATCACAAGGCCAAGCATATTAAAGCATGGTGTCCAAGGGCCCC
2783  8_HRV40b|d  GATTACCACACGTATATATCACAAGGCCAAGCATATTAAAGCATGGTGTCCAAGGGCCCC
2784  9_HRV40     GATTACCACACGTATATATCACAAGGCCAAGCATATTAAAGCATGGTGTCCAAGGGCCCC
2785 10_HRV85     AATCACCACGCGTGTGTATCATAAGGCCAAGCATGTAAAGGCTTGGTGTCCAAGAGCACC
2786 11_HRV85a|   AATCACCACGCGTGTGTATCATAAGGCCAAGCATGTAAAGGCTTGGTGTCCAAGAGCACC
2787 12_HRV85b|   AATCACCACGCGTGTGTATCATAAGGCCAAGCATGTAAAGGCTTGGTGTCCAAGAGCACC
2788 13_HRV56a|   AGTCACAACTCGTGTATATCATAAGGCAAAGCATATTCGAGCATGGTGTCCTAGAGCACC
2789 14_HRV56b|   AGTCACAACTCGTGTATATCATAAGGCAAAGCATATTCGAGCATGGTGTCCTAGAGCACC
2790 15_HRV56     AGTCACAACTCGTGTATATCATAAGGCAAAGCATATTCGAGCATGGTGTCCTAGAGCACC
2791 16_HRV54     AATCACCACACGGGTGTATCACAAGGCAAAACACATTAGAGCATGGTGTCCACGTGCACC
2792 17_HRV98     AATCACTACACGTGTGTACCACAAAGCAAAACACATTAGAGCATGGTGTCCACGTGCACC
2793 18_HRV59a|   GGTTGTCACACGTGTGTATCACAAAGCTAAACACGTCAAAGCCTGGTGCCCTAGAGCTCC
2794 19_HRV59b|   GGTTGTCACACGTGTGTATCACAAAGCTAAACACGTCAAAGCCTGGTGCCCTAGAGCTCC
2795 20_HRV59     GGTTGTCACACGTGTGTATCACAAAGCTAAACACGTCAAAGCCTGGTGCCCTAGAGCTCC
```

FIG. D10 CONT'D 06.trace                                                                  9/20/2007 5:04 PM

```
2796  21_HRV63     GGTGACTACACGTGTATATCATAAAGCTAAACACATCAGAGCCTGGTGCCCAAGAGCTCC
2797  22_HRV63b|   GGTGACTACACGTGTATATCATAAAGCTAAACACATCAGAGCCTGGTGCCCAAGAGCTCC
2798  23_HRV63a|   GGTGACTACACGTGTATATCATAAAGCTAAACACATCAGAGCCTGGTGCCCAAGAGCTCC
2799  24_HRV39     GGTTACAACCAGAGTTTACCATAAAGCCAAGCATGTTAAAGCATGGTGCCCTAGGGCTCC
2800  25_HRV39a|   GGTTACAACCAGAGTTTACCATAAAGCCAAGCATGTTAAAGCATGGTGCCCTAGGGCTCC
2801  26_HRV39b|   GGTTACAACCAGAGTTTACCATAAAGCCAAGCATGTTAAAGCATGGTGCCCTAGGGCTCC
2802  27_HRV10a|   AATTACCACCAGTGTTTATCACAAAGCCAAGCATGTCAAAGCATGGTGTCCAAGACCACC
2803  28_HRV10b|   AATTACCACCAGTGTTTATCACAAAGCCAAGCATGTCAAAGCATGGTGTCCAAGACCACC
2804  29_HRV10     AATTACCACCAGTGTTTATCACAAAGCCAAGCATGTCAAAGCATGGTGTCCAAGACCACC
2805  30_HRV100a   AATTACTACTAATATCTATCACAAGGCCAAACATGTTAAAGCTTGGTGCCCAAGACCACC
2806  31_HRV100b   AATTACTACTAATATCTATCACAAGGCCAAACATGTTAAAGCTTGGTGCCCAAGACCACC
2807  32_HRV100    AATTACTACTAATATCTATCACAAGGCCAAACATGTTAAAGCTTGGTGCCCAAGACCACC
2808  33_HRV66     AATTACTACTAGAGTATACCATAAGGCTAAGCATGTTAAAGCCTGGTGTCCTAGACCACT
2809  34_HRV66b|   AATTACTACTAGAGTATACCATAAGGCTAAGCATGTTAAAGCCTGGTGTCCTAGACCACT
2810  35_HRV66a|   AATTACTACTAGAGTATACCATAAGGCTAAGCATGTTAAAGCCTGGTGTCCTAGACCACT
2811  36_HRV77a|   AATCACCACTAGAGTATACCACAAGGCTAAACATATTAAAGCTTGGTGTCCCAGACCACC
2812  37_HRV77b|   AATCACCACTAGAGTATACCACAAGGCTAAACATATTAAAGCTTGGTGTCCCAGACCACC
2813  38_HRV77     AATCACCACTAGAGTATACCACAAGGCTAAACATATTAAAGCTTGGTGTCCCAGACCACC
2814  39_HRV62a    GGTCACAACTAATATTTACCACAAGGCTAAGCATGTAAAAGCGTGGTGCCCGCGGCCGCC
2815  40_HRV62b    GGTCACAACTAATATTTACCACAAGGCTAAGCATGTAAAAGCGTGGTGCCCTAGACCACC
2816  41_HRV25     GGTTACAACTAACATTTACCATAAAGCTAAGCATGTAAAAGCATGGTGCCCTAGACCACC
2817  42_HRV29a    AGTTACAACAAGTATCTATCATAAAGCTAAACATGTAAAGGCGTGGTGTCCTAGACCACC
2818  43_HRV29b    AGTTACAACAAGTATCTATCATAAAGCTAAACATGTAAAGGCGTGGTGTCCTAGACCACC
2819  44_HRV44a    AGTTACAACAAGCATTTATCACAAAGCTAAACATGTAAAAGCATGGTGCCCTAGACCACC
2820  45_HRV44b    AGTTACAACAAGCATTTATCACAAAGCTAAACATGTAAAAGCATGGTGCCCTAGACCACC
2821  46_HRV31     AATCACAACCAATATTTACCATAAGGCCAAACATGTTAAGGCATGGTGTCCTAGGCCCCC
2822  47_HRV31a|   AATCACAACCAATATTTACCATAAGGCCAAACATGTTAAGGCATGGTGTCCTAGGCCACC
2823  48_HRV31b|   AATCACAACCAATATTTACCATAAGGCCAAACATGTAAAAGCATGGTGTCCTAGGCCACC
2824  49_HRV47     AATCACAACTAACATCTACCATAAAGCCAAGCATGTGAAAGCATGGTGTCCTAGACCACC
2825  50_HRV47a|   AATCACAACTAACATCTACCATAAAGCCAAGCATGTGAAAGCATGGTGTCCTAGACCACC
2826  51_HRV47b|   AATCACAACTAACATCTACCATAAAGCCAAGCATGTGAAAGCATGGTGTCCTAGACCACC
2827  52_HRV11     AGTCACAACTAGGGTGTATCATAAAGCAAAGCATGTGAAGGTGTGGTGTCCAAGACCACC
2828  53_HRV11b|   AGTCACAACTAGGGTGTATCATAAAGCAAAGCATGTGAAGGTGTGGTGTCCAAGACCACC
2829  54_HRV11a|   AGTCACAACTAGGGTGTATCATAAAGCAAAGCATGTGAAGGTGTGGTGTCCAAGACCACC
2830  55_HRV76     AGTTACAACAAGAATATATCACAAAGCAAAGCATGTTAAGGTATGGTGCCCGAGACCACC
2831  56_HRV76b|   AGTTACAACAAGAATATATCACAAAGCAAAGCATGTTAAGGTATGGTGCCCGAGACCACC
2832  57_HRV76a|   AGTTACAACAAGAATATATCACAAAGCAAAGCATGTTAAGGTATGGTGCCCGAGACCACC
2833  58_HRV33     AGTTACAACAAGAGTATACCATAAAGCAAACATGTCAAAGTCTGGTGCCCAAGACCACC
2834  59_HRV33b|   AGTTACAACAAGAGTATACCATAAAGCAAACATGTCAAAGTCTGGTGCCCAAGACCACC
2835  60_HRV33a|   AGTTACAACAAGAGTATACCATAAAGCAAACATGTCAAAGTCTGGTGCCCAAGACCACC
2836  61_HRV24a|   AATTACAACAAGAATATACCACAAAGCAAAGCACATTAAGGTCTGGTGTCCAAGGCCACC
2837  62_HRV24b|   AATTACAACAAGAATATACCACAAAGCAAAGCACATTAAGGTCTGGTGTCCAAGGCCACC
2838  63_HRV24     AATTACAACAAGAATATACCACAAAGCAAAGCACATTAAGGTCTGGTGTCCAAGGCCACC
2839  64_HRV90     GATCACTACAAGAATATACCACAAAACACATTAAGGTTTGGTGTCCAAGACCACC
2840  65_HRV90a|   GATCACTACAAGAATATACCATAAAGCAAAACACATTAAGGTTTGGTGTCCAAGACCACC
2841  66_HRV90b|   GATCACTACAAGAATATACCATAAAGCAAAACACATTAAGGTTTGGTGTCCAAGACCACC
2842  67_HRV34     AATAACAACTAGAGTTTATCACAAAGCTAAACATGTAAAAACCTGGTGTCCAAGACCACC
2843  68_HRV34b|   AATAACAACTAGAGTTTATCACAAAGCTAAACATGTAAAAACCTGGTGTCCAAGACCACC
2844  69_HRV34a|   AATAACAACTAGAGTTTATCACAAAGCTAAACATGTAAAAACCTGGTGTCCAAGACCACC
2845  70_HRV50a|   AATCACAACCAGAGTATACCATAAAGCCAAACACATAAAAGTCTGGTGTCCAAGACCACC
2846  71_HRV50b|   AATCACAACCAGAGTATACCATAAAGCCAAACACATAAAAGTCTGGTGTCCAAGACCACC
2847  72_HRV50     AATCACAACCAGAGTATACCATAAAGCCAAACACATAAAAGTCTGGTGTCCAAGACCACC
2848  73_HRV18a|   AATAACAACCAGAATATACCACAAGGCAAAACATGTTAAAGCATGGTGCCCAAGGCCACC
2849  74_HRV18b|   AATAACAACCAGAATATACCACAAAGCAAAACATGTTAAAGCATGGTGCCCAAGGCCACC
2850  75_HRV18     AATAACAACCAGAATATACCACAAGGCAAAACATGTTAAAGCATGGTGCCCAAGGCCACC
2851  76_HRV55     AGTGACGACAAGAGTCTATCATAAAGCTAAACACATCAAAGCATGGTGCCCACGACCACC
2852  77_HRV55b|   AGTGACGACAAGAGTCTATCATAAAGCTAAACACATCAAAGCATGGTGCCCACGACCACC
2853  78_HRV55a|   AGTGACGACAAGAGTCTATCATAAAGCTAAACACATCAAAGCATGGTGCCCACGACCACC
2854  79_HRV57     AATAACAACCAGAGTGTATCACAAAGCCAAACATGTCAAAGCCTGGTGCCCTAGACCACC
2855  80_HRV57a|   AATAACAACCAGAGTGTATCACAAAGCCAAACATGTCAAAGCCTGGTGCCCTAGACCACC
2856  81_HRV57b|   AATAACAACCAGAGTGTATCACAAAGCCAAACATGTCAAAGCCTGGTGCCCTAGACCACC
2857  82_HRV21     AGTGACCACAAGAATATACCATAAGGCAAAGCATGTTAAAGCTTGGTGCCCCAGACCACC
2858  83_HRVHan    AGTGACCACAAGAATATACCATAAGGCAAAGCATGTTAAAGCTTGGTGCCCTAGACCACC
2859  84_HRV43     GATAACTACCAGGATATATCATAAAGCCAAGCATATCAAAGCTTGGTGCCCAAGACCACC
2860  85_HRV43b|   GATAACTACCAGGATATATCATAAAGCCAAGCATATCAAAGCTTGGTGCCCAAGACCACC
```

FIG. D10 CONT'D 06.trace                                                                9/20/2007 5:04 PM

```
2861  86_HRV43a|    GATAACTACCAGGATATATCATAAAGCCAAGCATATCAAAGCTTGGTGCCCAAGACCACC
2862  87_HRV75      AGTAACCACTAGAATATATCACAAAGCCAAACATATAAAAGCTTGGTGTCCGAGGCCGCC
2863  88_HRV75b|    AGTAACCACTAGAATATATCACAAAGCCAAACATATAAAAGCTTGGTGTCCGAGGCCGCC
2864  89_HRV75a|    AGTAACCACTAGAATATATCACAAAGCCAAACATATAAAAGCTTGGTGTCCGAGGCCGCC
2865  96_HRV9a|d    AATTTCAACCAGAATATATCACAAAGCCAAACATGTTAAAGCCTGGTGCCCAAGACCTCC
2866  97_HRV9b|d    AATTTCAACCAGAATATATCACAAAGCCAAACATGTTAAAGCCTGGTGCCCAAGACCTCC
2867  98_HRV9       AATTTCAACCAGAATATATCACAAAGCCAAACATGTTAAAGCCTGGTGCCCAAGACCTCC
2868  99_HRV32      TATTTCAACTAGGGTATATCACAAAGCTAAACACGTCAAAGCTTGGTGCCCACGACCACC
2869  100_HRV32a    TATTTCAACTAGGGTATATCACAAAGCTAAACACGTCAAAGCTTGGTGCCCACGACCACC
2870  101_HRV32b    TATTTCAACTAGGGTATATCACAAAGCTAAACACGTCAAAGCTTGGTGCCCACGACCACC
2871  102_HRV67     AATTGCAACGCGGGTGTATCATAAGGCTAAACATGTAAAAGCTTGGTGCCCAAGGCCCCC
2872  103_HRV67a    AATTGCAACGCGGGTGTATCATAAGGCTAAACATGTAAAAGCTTGGTGCCCAAGGCCCCC
2873  104_HRV67b    AATTGCAACGCGGGTGTATCATAAGGCTAAACATGTAAAAGCTTGGTGCCCAAGGCCCCC
2874  105_HRV15     GATTACAACTAGAGTGTATCACAAAGCTAAACATGTAAAGGCTTGGTGCCCCAGACCCCC
2875  106_HRV15a    GATTACAACTAGAGTGTATCACAAAGCTAAACATGTAAAGGCTTGGTGCCCCAGACCCCC
2876  107_HRV15b    GATTACAACTAGAGTGTATCACAAAGCTAAACATGTAAAGGCTTGGTGCCCCAGACCCCC
2877  108_HRV74a    AATTACAACTAGAGTGTACCATAAAGCAAAGCATGTGAAGGCATGGTGTCCTAGACCCCC
2878  109_HRV74b    AATTACAACTAGAGTGTACCATAAAGCAAAGCATGTGAAGGCATGGTGTCCTAGACCCCC
2879  110_HRV74     AATTACAACTAGAGTGTACCATAAAGCAAAGCATGTGAAGGCATGGTGTCCTAGACCCCC
2880  111_HRV38a    GATAACAACTAGAATTTATCATAAGGCAAAACATGTAAAAGCCTGGTGTCCAAGACCCCC
2881  112_HRV38b    GATAACAACTAGAATTTATCATAAAGCAAAACATGTAAAAGCCTGGTGTCCAAGACCCCC
2882  113_HRV38     GATAACAACTAGAATTTATCATAAGGCAAAACATGTAAAAGCCTGGTGTCCAAGACCCCC
2883  114_HRV60     CGTCGCAACAAGAATATATCATAAAGCAAAGCATGTTAAGGCTTGGTGTCCAAGACCTCC
2884  115_HRV60a    CGTCGCAACAAGAATATATCATAAAGCAAAGCATGTTAAGGCTTGGTGTCCAAGACCTCC
2885  116_HRV60b    CGTCGCAACAAGAATATATCATAAAGCAAAGCATGTTAAGGCTTGGTGTCCAAGACCTCC
2886  117_HRV64a    CATCACTACTAGGGTTTATCACAAAGCAAAACATGTCAAGGCATGGTGTCCACGGCCCCC
2887  118_HRV64b    CATCACTACTAGGGTTTATCACAAAGCAAAACATGTCAAGGCATGGTGTCCACGGCCCCC
2888  119_HRV64     CATCACTACTAGGGTTTATCACAAAGCAAAACATGTCAAGGCATGGTGTCCACGGCCCCC
2889  120_HRV94a    CATCACTACTAGAGTGTACCACAAAGCAAAACATGTGAAAGCGTGGTGCCCGCGCCCTCC
2890  121_HRV94b    CATCACTACTAGAGTGTACCACAAAGCAAAACATGTGAAAGCGTGGTGCCCGCGCCCTCC
2891  122_HRV94     CATCACTACTAGAGTGTACCACAAAGCAAAACATGTGAAAGCGTGGTGCCCGCGCCCTCC
2892  123_HRV22     AATTACAACTAGAGTGTACCACAAAGCAAAACATGTAAAGGCATGGTGCCCACGTCCTCC
2893  124_HRV22a    AATTACAACTAGAGTGTACCACAAAGCAAAACATGTAAAGGCATGGTGCCCACGTCCTCC
2894  125_HRV22b    AATTACAACTAGAGTGTACCACAAAGCAAAACATGTAAAGGCATGGTGCCCACGTCCTCC
2895  126_HRV82     CATTACCACAAGAATATCACAAAGCAAAACATGTGAAAGCGTGGTGTCCACGACCCCC
2896  127_HRV82b    CATTACCACAAGAATATATCACAAAGCAAAACATGTGAAAGCGTGGTGTCCACGACCCCC
2897  128_HRV82a    CATTACCACAAGAATATATCACAAAGCAAAACATGTGAAAGCGTGGTGTCCACGACCCCC
2898  129_HRV19     AATCACAACTAGAGTATATCATAAAGCTAAACATATAAAAGCCTGGTGCCCACGACCACC
2899  130_HRV19a    AATCACAACTAGAGTATATCATAAAGCTAAACATATAAAAGCTTGGTGCCCACGACCACC
2900  131_HRV19b    AATCACAACTAGAGTATATCATAAAGCTAAACATATAAAAGCTTGGTGCCCACGACCACC
2901  132_HRV13     GGTTACAACTAGAATCTATCATAAAGCTAAACATGTCAAAGCATGGTGTCCTAGACCTCC
2902  133_HRV13a    GGTTACAACTAGAATCTATCATAAAGCTAAACATGTCAAAGCATGGTGTCCTAGACCTCC
2903  134_HRV13b    GGTTACAACTAGAATCTATCATAAAGCTAAACATGTCAAAGCATGGTGTCCTAGACCTCC
2904  135_HRV41     GGTCACAACTAGAGTTTACCACAAAGCTAAACATGTTAAAGCATGGTGTCCTAGACCTCC
2905  136_HRV41a    GGTCACAACTAGAGTTTACCACAAAGCTAAACATGTTAAAGCATGGTGTCCTAGACCTCC
2906  137_HRV41b    GGTCACAACTAGAGTTTACCACAAAGCTAAACATGTTAAAGCATGGTGTCCTAGACCTCC
2907  138_HRV73     GGTTACTACTAGAATCTATCATAAGGCTAAACATGTTAAAGCTTGGTGTCCAAGACCTCC
2908  139_HRV73b    GGTTACTACTAGAATCTATCATAAGGCTAAACATGTTAAAGCTTGGTGTCCAAGACCTCC
2909  140_HRV73a    GGTTACTACTAGAATCTATCATAAGGCTAAACATGTTAAAGCTTGGTGTCCAAGACCTCC
2910  141_HRV61     AATCACAACTAGGATTTACCATAAAGCTAAACATGTTAAAGTCTGGTGTCCTAGACCCCC
2911  142_HRV61a    AATCACAACTAGGATTTACCATAAAGCTAAACATGTTAAAGTCTGGTGTCCTAGACCCCC
2912  143_HRV61b    AATCACAACTAGGATTTACCATAAAGCTAAACATGTTAAAGTCTGGTGTCCTAGACCCCC
2913  144_HRV96     AATTACAACCAGAGTTTACCACAAAGCTAAACATGTTAAGGTGTGGTGCCCGAGACCCCC
2914  145_HRV96b    AATTACAACCAGAGTTTACCACAAAGCTAAACATGTTAAGGTGTGGTGCCCGAGACCCCC
2915  146_HRV96a    AATTACAACCAGAGTTTACCACAAAGCTAAACATGTTAAGGTGTGGTGCCCGAGACCCCC
2916  90_HRV16a|    AGTGGTAACAAGGATATATCACAAAGCCAAACACACCAAAGCTTGGTGCCCAAGACCACC
2917  91_HRV16b|    AGTGGTAACAAGGATATATCACAAAGCCAAACACACCAAAGCTTGGTGCCCAAGACCACC
2918  92_1AYM_A     AGTGGTAACAAGGATATATCACAAAGCCAAACACACCAAAGCTTGGTGCCCAAGACCACC
2919  93_HRV81a|    AATAGTAACAAGAATATATCACAAAGCTAAGCACACCAAAGCTTGGTGTCCAAGACCACC
2920  94_HRV81b|    AATAGTAACAAGAATATATCACAAAGCTAAGCACACCAAAGCTTGGTGTCCAAGACCACC
2921  95_HRV81      AATAGTAACAAGAATATATCACAAAGCTAAGCACACCAAAGCTTGGTGTCCAAGACCACC
2922  147_HRV2      TATAATGACAAGAATCTATCACAAGGCTAAACATGTCAAGGCATGGTGTCCACGCCCACC
2923  148_HRV2a|    TATAATGACAAGAATCTATCACAAGGCTAAACATGTCAAGGCATGGTGTCCACGCCCACC
2924  149_HRV2b|    TATAATGACAAGAATCTATCACAAGGCTAAACATGTCAAGGCATGGTGTCCACGCCCACC
2925  150_HRV49a    TATCATGACAAGAATCTATCATAAAGCTAAACACGTCAAAGCATGGTGTCCGCGCCCACC
```

FIG. D10 CONT'D

```
06.trace                                                                  9/20/2007 5:04 PM 2926 151_HRV49b    TATCATGACAAGAATCTATCATAAAGCTAAACACGTCAAAGCATGGTGTCCGCGCCCACC
2927 152_HRV49     TATCATGACAAGAATCTATCATAAAGCTAAACACGTCAAAGCATGGTGTCCGCGCCCACC
2928 153_HRV23a    GATAATGACAAGGGTCTACCACAAAGCTAAACATGTCAAAGCATGGTGTCCGCGGCCACC
2929 154_HRV23b    GATAATGACAAGGGTCTACCACAAAGCTAAACATGTCAAAGCATGGTGTCCGCGGCCACC
2930 155_HRV23     GATAATGACAAGGGTCTACCACAAAGCTAAACATGTCAAAGCATGGTGTCCGCGGCCACC
2931 156_HRV30a    CATAATGACAAGGGTCTACCACAAGGCTAAACATGTCAAAGCGTGGTGTCCACGGCCACC
2932 157_HRV30b    CATAATGACAAGGGTCTACCACAAGGCTAAACATGTCAAAGCGTGGTGTCCACGGCCACC
2933 158_HRV30     CATAATGACAAGGGTCTACCACAAGGCTAAACATGTCAAAGCGTGGTGTCCACGGCCACC
2934 159_HRV7      GATTGTGAGTCGCATTTACCACAAAGCCAAACATATAAAAGCATGGTGCCCACGCCCACC
2935 160_HRV7b|    GATTGTGAGTCGCATTTACCACAAAGCCAAACATATAAAAGCATGGTGCCCACGCCCACC
2936 161_HRV7a|    GATTGTGAGTCGCATTTACCACAAAGCCAAACATATAAAAGCATGGTGCCCACGCCCACC
2937 162_HRV88     TATCATTAGCCGTATATATCACAAGGCTAAACATATAAAGGCATGGTGTCCACGCCCACC
2938 163_HRV88a    TATCATTAGCCGTATATATCACAAGGCTAAACATATAAAGGCATGGTGTCCACGCCCACC
2939 164_HRV88b    TATCATTAGCCGTATATATCACAAGGCTAAACATATAAAGGCATGGTGTCCACGCCCACC
2940 165_HRV36a    TATTGTATGCCGCATTTATCATAAAGCTAAACACATAAAGGCCTGGTGCCCGCGTCCACC
2941 166_HRV36b    TATTGTATGCCGCATTTATCATAAAGCTAAACACATAAAGGCCTGGTGCCCCGCGTCCACC
2942 167_HRV36     TATTGTATGCCGCATTTATCATAAAGCTAAACACATAAAGGCCTGGTGCCCCGCGTCCACC
2943 168_HRV89a    TATTGTGTGCCGCATTTACCACAAGGCCAAACATATAAAAGCATGGTGTCCTCGCCCACC
2944 169_HRV89b    TATTGTGTGCCGCATTTACCACAAGGCCAAACATATAAAAGCATGGTGTCCTCGCCCACC
2945 170_HRV89     TATTGTGTGCCGCATTTACCACAAGGCCAAACATATAAAAGCATGGTGTCCTCGCCCACC
2946 171_HRV58     CATTGTCTGTCGCATTTACCACAAAGCCAAGATATAAAAGCATGGTGTCCACGCCCACC
2947 172_HRV58a    CATTGTCTGTCGCATTTACCACAAAGCCAAGCATATAAAAGCATGGTGTCCACGCCCACC
2948 173_HRV58b    CATTGTCTGTCGCATTTACCACAAAGCCAAGCATATAAAAGCATGGTGTCCACGCCCACC
2949 174_HRV12a    GATTACCAGTAGAATATACCATAAAGCAAAACATATCAGTGCCTGGGGCCCTAGACCACC
2950 175_HRV12b    GATTACCAGTAGAATATACCATAAAGCAAAACATATCAGTGCCTGGGGCCCTAGACCACC
2951 176_HRV12     GATTACCAGTAGAATATACCATAAAGCAAAACATATCAGTGCCTGGGGCCCTAGACCACC
2952 177_HRV78a    AATTACAGCTAGAGTCTACCACAAGGCCAAACATATTAGTGCATGGGGCCCAAGACCTCC
2953 178_HRV78b    AATTACAGCTAGAGTCTACCACAAGGCCAAACATATTAGTGCATGGGGCCCAAGACCTCC
2954 179_HRV78     AATTACAGCTAGAGTCTACCACAAGGCCAAACATATTAGTGCATGGGGCCCAAGACCTCC
2955 180_HRV20     GATAACCAGTAGGATATTCCACAAGGCAAAGCATATTAGTGCATGGTGTCCAAGGGCCCC
2956 181_HRV20a    GATAACCAGTAGGATATTCCACAAGGCAAAGCATATTAGTGCATGGTGTCCAAGGGCCCC
2957 182_HRV20b    GATAACCAGTAGGATATTCCACAAGGCAAAGCATATTAGTGCATGGTGTCCAAGGGCCCC
2958 183_HRV68     AATAACCAGCAGAATATTCCATAAAGCAAAACATATTAGTGCGTGGTGTCCAAGAGCTCC
2959 184_HRV68a    AATAACCAGCAGAATATTCCATAAAGCAAAACATATTAGTGCGTGGTGTCCAAGAGCTCC
2960 185_HRV68b    AATAACCAGCAGAATATTCCATAAAGCAAAACATATTAGTGCGTGGTGTCCAAGAGCTCC
2961 186_HRV28     AATAACCAGCATAATATTCCACAAAGCTAAACATGTCAGTGCATGGTGCCCCAGACCTCC
2962 187_HRV28a    AATAACCAGCATAATATTCCACAAAGCTAAACATGTCAGTGCATGGTGCCCCAGACCTCC
2963 188_HRV28b    AATAACCAGCATAATATTCCACAAAGCTAAACATGTCAGTGCATGGTGCCCCAGACCTCC
2964 189_HRV53a    GATAACCAGTAGGATTTATCACAAGGCTAAACATATCAGTGCATGGTGTCCAAGACCACC
2965 190_HRV53b    GATAACCAGTAGGATTTATCACAAGGCTAAACATATCAGTGCATGGTGTCCAAGACCACC
2966 191_HRV53     GATAACCAGTAGGATTTATCACAAGGCTAAACATATCAGTGCATGGTGTCCAAGACCACC
2967 192_HRV46a    TATAACTAGCAGAATATATCACAAGGCTAAACACATTAAAGCATGGTGCCCAGGGCACC
2968 193_HRV46b    TATAACTAGCAGAATATATCACAAGGCTAAACACATTAAAGCATGGTGCCCCAGGGCACC
2969 194_HRV46     TATAACTAGCAGAATATATCACAAGGCTAAACACATTAAAGCATGGTGCCCCAGGGCACC
2970 195_HRV80a    AATCACCAGCAGAATATATCACAAAGCTAAACACATCAAAGCATGGTGTCCAAGAGCACC
2971 196_HRV80b    AATCACCAGCAGAATATATCACAAAGCTAAACACATCAAAGCATGGTGTCCAAGAGCACC
2972 197_HRV80     AATCACCAGCAGAATATATCACAAAGCTAAACACATCAAAGCATGGTGTCCAAGAGCACC
2973 198_HRV51     CATAACTAGCAGGATTTACCACAAAGCCAAACATGTCAGTGCATGGTGCCCTCGTCCTCC
2974 199_HRV51a    CATAACTAGCAGGATTTACCACAAAGCCAAACATGTCAGTGCATGGTGCCCTCGTCCTCC
2975 200_HRV51b    CATAACTAGCAGGATTTACCACAAAGCCAAACATGTCAGTGCATGGTGCCCTCGTCCTCC
2976 201_HRV65a    CATAACCAGTAGAATATATCATAAAGCTAAACACATCAGTGCTTGGTGTCCACGACCTCC
2977 202_HRV65b    CATAACCAGTAGAATATATCATAAAGCTAAACACATCAGTGCTTGGTGTCCACGACCTCC
2978 203_HRV65     CATAACCAGTAGAATATATCATAAAGCTAAACACATCAGTGCTTGGTGTCCACGACCTCC
2979 204_HRV71a    CATAACAAGTAGGATTTATCACAAAGCCAAACATGTCAGAGCATGGTGTCCTAGACCCCC
2980 205_HRV71b    CATAACAAGTAGGATTTATCACAAAGCCAAACATGTCAGAGCATGGTGTCCTAGACCCCC
2981 206_HRV71     CATAACAAGTAGGATTTATCACAAAGCCAAACATGTCAGAGCATGGTGTCCTAGACCCCC
2982 207_HRV8      AATTGATTCAAGAATATACCTGAAAGCAAAGCACATTAAAGCTTGGTGTCCTAGACCCCC
2983 208_HRV95     AATTGATTCAAGAATATACCTGAAAGCAAAGCATATTAAAGCTTGGTGTCCTAGACCCCC
2984 209_HRV45     GATCGACTCCATGGTATATCTAAAAGCTAAACATCAAGGCATGGTGTCCCAGACCTCC
2985 210_HRV45a    GATCGACTCCATGGTATATCTAAAAGCTAAACACATCAAGGCATGGTGTCCCAGACCTCC
2986 211_HRV45b    GATCGACTCCATGGTATATCTAAAAGCTAAACACATCAAGGCATGGTGTCCCAGACCTCC
2987 GROUP_1       --T-----------T-T--C--AA-GC-AA-CA---------TGG-G-CC--G--C-C-
2988
2989 1_HRV1A1|d    TAGAGCTGTCCCTTACACA-CATAGTCATGTGACTAATTATATGC-CAGAAA---CAGGT
2990 2_HRV1A2|d    TAGAGCTGTCCCTTACACA-CATAGTCATGTGACTAATTATATGC-CAGAAA---CAGGT
```

FIG. D10 CONT'D 06.trace                                                                      9/20/2007 5:04 PM

```
2991  3_HRV1A|cD    TAGAGCTGTCCCTTACACA-CATAGTCATGTGACTAATTATATGC-CAGAAA---CAGGT
2992  4_HRV1B1|d    TAGAGCTGTTCCTTACACA-CATAGTCGTGTAACTAATTATGTAC-CAAAAA---CAGGT
2993  5_HRV1B2|d    TAGAGCTGTTCCTTACACA-CATAGTCGTGTAACTAATTATGTAC-CAAAAA---CAGGT
2994  6_HRV1B       TAGAGCTGTTCCTTACACA-CATAGTCGTGTAACTAATTATGTAC-CAAAAA---CAGGT
2995  7_HRV40a|d    AAGAGCAGTACCTTACACA-CATACACACTCAACAAATTATAAAC-CTCAAG---AAGGT
2996  8_HRV40b|d    AAGAGCAGTACCTTACACA-CATACACACTCAACAAATTATAAAC-CTCAAG---AAGGT
2997  9_HRV40       AAGAGCAGTACCTTACACA-CATACACACTCAACAAATTATAAAC-CTCAAG---AAGGT
2998  10_HRV85      AAGAGCGGTGCCTTATACA-CACACACGCTCAACCAACTATGTGC-CACAAG---ATGGT
2999  11_HRV85a|    AAGAGCGGTGCCTTATACA-CACACACGCTCAACCAACTATGTGC-CACAAG---ATGGT
3000  12_HRV85b|    AAGAGCGGTGCCTTATACA-CACACACGCTCAACCAACTATGTGC-CACAAG---ATGGT
3001  13_HRV56a|    AAGGGCTGTGCCTTATACA-CATGCTCACGTCACCAATTATAAAC-CACAAG---ATGGT
3002  14_HRV56b|    AAGGGCTGTGCCTTATACA-CATGCTCACGTCACCAATTATAAAC-CACAAG---ATGGT
3003  15_HRV56      AAGGGCTGTGCCTTATACA-CATGCTCACGTCACCAATTATAAAC-CACAAG---ATGGT
3004  16_HRV54      TAGGGCTGTCCCATACACA-CATACTAGATCAACAAATTACATGC-CACGGG---AGGGT
3005  17_HRV98      TAGAGCTGTTCCATACACA-CACACTAGATCAACTAATTACATGC-CTCAAG---ATGGT
3006  18_HRV59a|    TAGAGCAGTCCCTTACACA-CACAGCTACGTAACTAACTACAAGATTGCTGG---AAAA-
3007  19_HRV59b|    TAGAGCAGTCCCTTACACA-CACAGCTACGTAACTAACTACAAGATTGCTGG---AAAA-
3008  20_HRV59      TAGAGCAGTCCCTTACACA-CACAGCTACGTAACTAACTACAAGATTGCTGG---AAAA-
3009  21_HRV63      TAGGGCTGTTCCATACACA-CATAGTTATGTCACTAACTATAAAATTACAGG---ACAG-
3010  22_HRV63b|    TAGGGCTGTTCCATACACA-CATAGTTATGTCACTAACTATAAAATTACAGG---ACAG-
3011  23_HRV63a|    TAGGGCTGTTCCATACACA-CATAGTTATGTCACTAACTATAAAATTACAGG---ACAG-
3012  24_HRV39      CAGAGCAGTCCCTTACACA-CACAGCAATGTTACAAATTACAAAG-TACGGG---ACGGT
3013  25_HRV39a|    CAGAGCAGTCCCTTACACA-CACAGCAATGTTACAAATTACAAAG-TACGGG---ACGGT
3014  26_HRV39b|    CAGAGCAGTCCCTTACACA-CACAGCAATGTTACAAATTACAAAG-TACGGG---ACGGT
3015  27_HRV10a|    CAGAGCTGTACCATATACA-CATGCCCATTCCACAAATTACAAAC-CACATG---GCAAA
3016  28_HRV10b|    CAGAGCTGTACCATATACA-CATGCCCATTCCACAAATTACAAAC-CACATG---GCAAA
3017  29_HRV10      CAGAGCTGTACCATATACA-CATGCCCATTCCACAAATTACAAAC-CACATG---GCAAA
3018  30_HRV100a    TCGGGCTGTGCCGTACACA-CATAGTCACTCTACAAATTACAAAC-CACATG---AGGGT
3019  31_HRV100b    TCGGGCTGTGCCGTACACA-CATAGTCACTCTACAAATTACAAAC-CACATG---AGGGT
3020  32_HRV100     TCGGGCTGTGCCGTACACA-CATAGTCACTCTACAAATTACAAAC-CACATG---AGGGT
3021  33_HRV66      TAGAGCTGTACCATACACA-ACTGTAAACTCAACCAATTATATGC-CTCATA---CTGGT
3022  34_HRV66b|    TAGAGCTGTACCATACACA-ACTGTAAACTCAACCAATTATATGC-CTCATA---CTGGT
3023  35_HRV66a|    TAGAGCTGTACCATACACA-ACTGTAAACTCAACCAATTATATGC-CTCATA---CTGGT
3024  36_HRV77a|    TAGAGCTGTACCATACACA-GCAGTAGATTCAACAAATTACAAAC-CTATGA---GAGGG
3025  37_HRV77b|    TAGAGCTGTACCATACACA-GCAGTAGATTCAACAAATTACAAAC-CTATGA---GAGGG
3026  38_HRV77      TAGAGCTGTACCATACACA-GCAGTAGATTCAACAAATTACAAAC-CTATGA---GAGGG
3027  39_HRV62a     CAGAGCTGTTCCATATAAA-TATGTTGATTTCAATAATTATGCAG-CCAGTG---ATAGT
3028  40_HRV62b     CAGAGCTGTTCCATATAAA-TATGTTGATTTCAATAATTATGCAG-CCAGTG---ATAGT
3029  41_HRV25      TAGAGCTGTCCCATATAAA-TATGTTGACTTCAATAATTATGCAG-CCAGTG---ATAAT
3030  42_HRV29a     AAGAGTTGTCCCATACAAG-TATGTTGGCCTAACTAATTACACAC-TTAAAG---AAGAA
3031  43_HRV29b     AAGAGTTGTCCCATACAAG-TATGTTGGCCTAACTAATTACACAC-TTAAAG---AAGAA
3032  44_HRV44a     AAGGGTTGTCCCATACAAG-TATGTTGGCCTAACTAATTACACAC-TTAAAG---AAACA
3033  45_HRV44b     AAGGGTTGTCCCATACAAG-TATGTTGGCCTAACTAATTACACAC-TTAAAG---AAACA
3034  46_HRV31      TAGAGCAGTTCCATACAGGGTATG-TGGATCAACAAACTACAAAC-CTGATG---AAAAT
3035  47_HRV31a|    TAGAGCAGTTCCATACAGGGTATG-TGGATCAACAAACTACAAAC-CTGATG---AAAAT
3036  48_HRV31b|    TAGAGCAGTTCCATACAGG-TATGTTGGATCAACAAACTACAAAC-CTGATG---AAAAT
3037  49_HRV47      TAGAGCTGTTCCATATAGA-TATGTTGGATCAACAAATTACAAAC-CTGATC---AAGGA
3038  50_HRV47a|    TAGAGCTGTTCCATATAGA-TATGTTGGATCAACAAATTACAAAC-CTGATC---AAGGA
3039  51_HRV47b|    TAGAGCTGTTCCATATAGA-TATGTTGGATCAACAAATTACAAAC-CTGATC---AAGGA
3040  52_HRV11      TAGAGCTGTAGAATATACT-CACACTCATGTAACCAATTACAAAC-CACAGG---AAGGA
3041  53_HRV11b|    TAGAGCTGTAGAATATACT-CACACTCATGTAACCAATTACAAAC-CACAGG---AAGGA
3042  54_HRV11a|    TAGAGCTGTAGAATATACT-CACACTCATGTAACCAATTACAAAC-CACAGG---AAGGA
3043  55_HRV76      TAGAGCTGTAGAGTATACA-TACACCCATGTAACAAACTACAAAC-CACATT---CTGGT
3044  56_HRV76b|    TAGAGCTGTAGAGTATACA-TACACCCATGTAACAAACTACAAAC-CACATT---CTGGT
3045  57_HRV76a|    TAGAGCTGTAGAGTATACA-TACACCCATGTAACAAACTACAAAC-CACATT---CTGGT
3046  58_HRV33      TAGAGCTGTGGAATACACC-CATACTCATGTTACAAATTATAAAT-CAACAA---CTCGT
3047  59_HRV33b|    TAGAGCTGTGGAATACACC-CATACTCATGTTACAAATTATAAAT-CAACAA---CTCGT
3048  60_HRV33a|    TAGAGCTGTGGAATACACC-CATACTCATGTTACAAATTATAAAT-CAACAA---CTCGT
3049  61_HRV24a|    CAGAGCTGTTGAGTATACA-CATACTCACGTGACCAATTATAAGC-ATCAGA---CTCGT
3050  62_HRV24b|    CAGAGCTGTTGAGTATACA-CATACTCACGTGACCAATTATAAGC-ATCAGA---CTCGT
3051  63_HRV24      CAGAGCTGTTGAGTATACA-CATACTCACGTGACCAATTATAAGC-ATCAGA---CTCGT
3052  64_HRV90      TAGGGCAGTTGAATACACA-CACACTCATGTAACAAACTACAAAC-ATGCAA---CACGT
3053  65_HRV90a|    TAGGGCAGTTGAATACACA-CACACTCATGTAACAAACTACAAAC-ATGCAA---CACGT
3054  66_HRV90b|    TAGGGCAGTTGAATACACA-CACACTCATGTAACAAACTACAAAC-ATGCAA---CACGT
3055  67_HRV34      AAGAGCTGTTGAGTACACA-CACACACATGTTACTAACTACAAAG-TTAGGG---GTAAA
```

FIG. D10 CONT'D

06.trace                                                              9/20/2007 5:04 PM

```
3056  68_HRV34b|    AAGAGCTGTTGAGTACACA-CACACACATGTTACTAACTACAAAG-TTAGGG---GTAAA
3057  69_HRV34a|    AAGAGCTGTTGAGTACACA-CACACACATGTTACTAACTACAAAG-TTAGGG---GTAAA
3058  70_HRV50a|    AAGAGCTGTTGAATACACA-CACACCCATGTCACTAACTACAAGA-AAAGTG---ATGCT
3059  71_HRV50b|    AAGAGCTGTTGAATACACA-CACACCCATGTCACTAACTACAAGA-AAAGTG---ATGCT
3060  72_HRV50     AAGAGCTGTTGAATACACA-CACACCCATGTCACTAACTACAAGA-AAAGTG---ATGCT
3061  73_HRV18a|    GAGAGCTGTGGAGTACACA-CATACACATGTAACTAACTACAAGC-CTAAGG---AAGGA
3062  74_HRV18b|    GAGAGCTGTGGAGTACACA-CATACACATGTAACTAACTACAAGC-CTAAGG---AAGGA
3063  75_HRV18     GAGAGCTGTGGAGTACACA-CATACACATGTAACTAACTACAAGC-CTAAGG---AAGGA
3064  76_HRV55     TAGGGCTGTTGAATACACA-CACACACATGTCACAAATTACAAGA-AGACTG---ATGGC
3065  77_HRV55b|    TAGGGCTGTTGAATACACA-CACACACATGTCACAAATTACAAGA-AGACTG---ATGGC
3066  78_HRV55a|    TAGGGCTGTTGAATACACA-CACACACATGTCACAAATTACAAGA-AGACTG---ATGGC
3067  79_HRV57     ACGGGCTATCGAGTACACA-CATACACATGTTACTAATTATAAAA-TAAAAG---ATAGA
3068  80_HRV57a|    ACGGGCTATCGAGTACACA-CATACACATGTTACTAATTATAAAA-TAAAAG---ATAGA
3069  81_HRV57b|    ACGGGCTATCGAGTACACA-CATACACATGTTACTAATTATAAAA-TAAAAG---ATAGA
3070  82_HRV21     GAGGGCCGTTGAATACACA-CATACACACGTAACCAATTACAAAA-TTGCAA---ATCAT
3071  83_HRVHan    GAGGGCCGTTGAATACACA-CATACACATGTAACCAATTACAAAA-TTGCAA---ATAAA
3072  84_HRV43     CAGAGCTGTTGAATACACA-CACACACATGTCACAAATTATAAAA-GAGAAG---GAAAG
3073  85_HRV43b|    CAGAGCTGTTGAATACACA-CACACACATGTCACAAATTATAAAA-GAGAAG---GAAAG
3074  86_HRV43a|    CAGAGCTGTTGAATACACA-CACACACATGTCACAAATTATAAAA-GAGAAG---GAAAG
3075  87_HRV75     CAGGGCTGTTGAATACACA-TTTAGACGTGTAACAAATTACAAAA-GAGATG---GACAA
3076  88_HRV75b|    CAGGGCTGTTGAATACACA-TTTAGACGTGTAACAAATTACAAAA-GAGATG---GACAA
3077  89_HRV75a|    CAGGGCTGTTGAATACACA-TTTAGACGTGTAACAAATTACAAAA-GAGATG---GACAA
3078  96_HRV9a|d    TAGGGCAGTTGAGTATATA-CATACACATGTCACAAATTACAAGC-CAAGCA---CAGGC
3079  97_HRV9b|d    TAGGGCAGTTGAGTATATA-CATACACATGTCACAAATTACAAGC-CAAGCA---CAGGC
3080  98_HRV9      TAGGGCAGTTGAGTATATA-CATACACATGTCACAAATTACAAGC-CAAGCA---CAGGC
3081  99_HRV32     TAGGGCAGTTGAATATACA-CATACACATGTTACAAATTACAAAC-CAAGCA---CAGGT
3082  100_HRV32a    TAGGGCAGTTGAATATACA-CATACACATGTTACAAATTACAAAC-CAAGCA---CAGGT
3083  101_HRV32b    TAGGGCAGTTGAATATACA-CATACACATGTTACAAATTACAAAC-CAAGCA---CAGGT
3084  102_HRV67    TAGAGCAGTTGAATACATA-CACACACATGTTACAAACTATAGAC-CAGAAA---CAGGT
3085  103_HRV67a   TAGAGCAGTTGAATACATA-CACACACATGTTACAAACTATAGAC-CAGAAA---CAGGT
3086  104_HRV67b   TAGAGCAGTTGAATACATA-CACACACATGTTACAAACTATAGAC-CAGAAA---CAGGT
3087  105_HRV15    TAGAGCAGTGGAATATACA-CACACACATGTCACAAATTACAAAC-CACAAG---ATGGT
3088  106_HRV15a   TAGAGCAGTGGAATATACA-CACACACATGTCACAAATTACAAAC-CACAAG---ATGGT
3089  107_HRV15b   TAGAGCAGTGGAATATACA-CACACACATGTCACAAATTACAAAC-CACAAG---ATGGT
3090  108_HRV74a   TAGAGCAGTTGAATATACT-CACACACATGTCACAAATTACAAAC-CACAAG---AAGGT
3091  109_HRV74b   TAGAGCAGTTGAATATACT-CACACACATGTCACAAATTACAAAC-CACAAG---AAGGT
3092  110_HRV74    TAGAGCAGTTGAATATACT-CACACACATGTCACAAATTACAAAC-CACAAG---AAGGT
3093  111_HRV38a   AAGGGCAGTTGAATATAGA-CATACACATGTTAACAATTACAAAC-CAGACC---AAGGG
3094  112_HRV38b   AAGGGCAGTTGAATATAGA-CATACACATGTTAACAATTACAAAC-CAGACC---AAGGG
3095  113_HRV38    AAGGGCAGTTGAATATAGA-CATACACATGTTAACAATTACAAAC-CAGACC---AAGGG
3096  114_HRV60    AAGGGCAGTTGAATATAGA-CACACACATGTAAACAACTATAGAC-CAGATG---ATGGA
3097  115_HRV60a   AAGGGCAGTTGAATATAGA-CACACACATGTAAACAACTATAGAC-CAGATG---ATGGA
3098  116_HRV60b   AAGGGCAGTTGAATATAGA-CACACACATGTAAACAACTATAGAC-CAGATG---ATGGA
3099  117_HRV64a   AAGAGCTGTTGGATATACA-CATACAAATGTCACCAATTATAAAC-CATCCA---AAGGA
3100  118_HRV64b   AAGAGCTGTTGGATATACA-CATACAAATGTCACCAATTATAAAC-CATCCA---AAGGA
3101  119_HRV64    AAGAGCTGTTGGATATACA-CATACAAATGTCACCAATTATAAAC-CATCCA---AAGGA
3102  120_HRV94a   AAGAGCTGTTGGATACACA-CATACGCATGTCACTAATTACAAAC-CATCTG---AAGGG
3103  121_HRV94b   AAGAGCTGTTGGATACACA-CATACGCATGTCACTAATTACAAAC-CATCTG---AAGGG
3104  122_HRV94    AAGAGCTGTTGGATACACA-CATACGCATGTCACTAATTACAAAC-CATCTG---AAGGG
3105  123_HRV22    AAGAGCTGTTGGATATACA-CACACACATGTGACAAACTACAAAC-CATCTG---TAGGG
3106  124_HRV22a   AAGAGCTGTTGGATATACA-CACACACATGTGACAAACTACAAAC-CATCTG---TAGGG
3107  125_HRV22b   AAGAGCTGTTGGATATACA-CACACACATGTGACAAACTACAAAC-CATCTG---TAGGG
3108  126_HRV82    GAGGGCTGTGGGTTATACA-CACACACATGTTACCAACTACAAGC-CATCAC---AGGGA
3109  127_HRV82b   GAGGGCTGTGGGTTATACA-CACACACATGTTACCAACTACAAGC-CATCAC---AGGGA
3110  128_HRV82a   GAGGGCTGTGGGTTATACA-CACACACATGTTACCAACTACAAGC-CATCAC---AGGGA
3111  129_HRV19    CAGAGCCGTGGAATATACC-CACACTCATGTGACTAATTATAAAC-CCCAGA---CAGGT
3112  130_HRV19a   CAGAGCCGTGGAATATACC-CACACTCATGTGACTAATTATAAAC-CCCAGA---CAGGT
3113  131_HRV19b   CAGAGCCGTGGAATATACC-CACACTCATGTGACTAATTATAAAC-CCCAGA---CAGGT
3114  132_HRV13    CAGAGCTGTTGAATATACT-AATGTGCATGTTACAAATACAAAC-CAGGGA---CAGGA
3115  133_HRV13a   CAGAGCTGTTGAATATACT-AATGTGCATGTTACAAATACAAAC-CAGGGA---CAGGA
3116  134_HRV13b   CAGAGCTGTTGAATATACT-AATGTGCATGTTACAAATACAAAC-CAGGGA---CAGGA
3117  135_HRV41    CAGGGCTGTGGAGTACACC-AATGTGCATGTCACAAATTACAAAC-CAAAAG---CAGGA
3118  136_HRV41a   CAGGGCTGTGGAGTACACC-AATGTGCATGTCACAAATTACAAAC-CAAAAG---CAGGA
3119  137_HRV41b   CAGGGCTGTGGAGTACACC-AATGTGCATGTCACAAATTACAAAC-CAAAAG---CAGGA
3120  138_HRV73    TAGGGCAGTAGAATATACA-AATGCACATGTGACCAATTATAAAC-CCACTG---ATGGA
```

FIG. D10 CONT'D 06.trace                                                                9/20/2007 5:04 PM

```
3121 139_HRV73b  TAGGGCAGTAGAATATACA-AATGCACATGTGACCAATTATAAAC-CCACTG---ATGGA
3122 140_HRV73a  TAGGGCAGTAGAATATACA-AATGCACATGTGACCAATTATAAAC-CCACTG---ATGGA
3123 141_HRV61   CAGAGCAGTGGAATATACT-AATGTGCATTTGACCAATTACAAGC-CCAAAG---ATAGT
3124 142_HRV61a  CAGAGCAGTGGAATATACT-AATGTGCATTTGACCAATTACAAGC-CCAAAG---ATAGT
3125 143_HRV61b  CAGAGCAGTGGAATATACT-AATGTGCATTTGACCAATTACAAGC-CCAAAG---ATAGT
3126 144_HRV96   TAGAGCAGTTGAATACACA-AATGTGCATCTCACAAATTATAAAC-CCAACA---ATG--
3127 145_HRV96b  TAGAGCAGTTGAATACACA-AATGTGCATCTCACAAATTATAAAC-CCAACA---ATG--
3128 146_HRV96a  TAGAGCAGTTGAATACACA-AATGTGCATCTCACAAATTATAAAC-CCAACA---ATG--
3129  90_HRV16a| CAGAGCTGTTCAATACTCA-CATACACATACCACCAACTACAAAT-TGAGTT---CAGAA
3130  91_HRV16b| CAGAGCTGTTCAATACTCA-CATACACATACCACCAACTACAAAT-TGAGTT---CAGAA
3131  92_1AYM_A  CAGAGCTGTTCAATACTCA-CATACACATACCACCAACTACAAAT-TGAGTT---CAGAA
3132  93_HRV81a| CAGGGCTGTTCAGTACACA-CATACACATGTAACTAATTATAAAT-TAGAAA---CAGAT
3133  94_HRV81b| CAGGGCTGTTCAGTACACA-CATACACATGTAACTAATTATAAAT-TAGAAA---CAGAT
3134  95_HRV81   CAGGGCTGTTCAGTACACA-CATACACATGTAACTAATTATAAAT-TAGAAA---CAGAT
3135 147_HRV2    CAGAGCGCTTGAGTATACT-CGTGCTCACCGCACTAATTTTAAAA-TTGAGG---ATAGG
3136 148_HRV2a|  CAGAGCGCTTGAGTATACT-CGTGCTCACCGCACTAATTTTAAAA-TTGAGG---ATAGG
3137 149_HRV2b|  CAGAGCGCTTGAGTATACT-CGTGCTCACCGCACTAATTTTAAAA-TTGAGG---ATAGG
3138 150_HRV49a  CAGAGCACTTGAATATACT-CGCGCTCACCGTACTAATTTCAAAG-TTGAAG---ACAGA
3139 151_HRV49b  CAGAGCACTTGAATATACT-CGCGCTCACCGTACTAATTTCAAAG-TTGAAG---ACAGA
3140 152_HRV49   CAGAGCACTTGAATATACT-CGCGCTCACCGTACTAATTTCAAAG-TTGAAG---ACAGA
3141 153_HRV23a  CAGAGCACTTGAATACACA-CGCGCTCACCGTACTAATTTCAAAA-TTGAAG---GTGAA
3142 154_HRV23b  CAGAGCACTTGAATACACA-CGCGCTCACCGTACTAATTTCAAAA-TTGAAG---GTGAA
3143 155_HRV23   CAGAGCACTTGAATACACA-CGCGCTCACCGTACTAATTTCAAAA-TTGAAG---GTGAA
3144 156_HRV30a  TAGGGCGCTTGAGTATACC-CGTGCTCATCGCACCAATTTTAAAA-TTGATG---GCAGG
3145 157_HRV30b  TAGGGCGCTTGAGTATACC-CGTGCTCATCGCACCAATTTTAAAA-TTGATG---GCAGG
3146 158_HRV30   TAGGGCGCTTGAGTATACC-CGTGCTCATCGCACCAATTTTAAAA-TTGATG---GCAGG
3147 159_HRV7    ACGAGCTGTGCCTTATCAA-CACACTCACTCCACCAACTATGTGC-CACAAA---ATGGA
3148 160_HRV7b|  ACGAGCTGTGCCTTATCAA-CACACTCACTCCACCAACTATGTGC-CACAAA---ATGGA
3149 161_HRV7a|  ACGAGCTGTGCCTTATCAA-CACACTCACTCCACCAACTATGTGC-CACAAA---ATGGA
3150 162_HRV88   AAGAGCCGTACCTTATCAG-CACACACACTCCACCAATTATGTAC-CAACAG---ATGGG
3151 163_HRV88a  AAGAGCCGTACCTTATCAG-CACACACACTCCACCAATTATGTAC-CAACAG---ATGGG
3152 164_HRV88b  AAGAGCCGTACCTTATCAG-CACACACACTCCACCAATTATGTAC-CAACAG---ATGGG
3153 165_HRV36a  AAGGGCCGTTCCTTACCAA-CACACACATTCCACTAATTATATAC-CATACA---AAGGT
3154 166_HRV36b  AAGGGCCGTTCCTTACCAA-CACACACATTCCACTAATTATATAC-CATACA---AAGGT
3155 167_HRV36   AAGGGCCGTTCCTTACCAA-CACACACATTCCACTAATTATATAC-CATACA---AAGGT
3156 168_HRV89a  AAGGGCTGTTGCCTATCAA-CACACACACTCAACCAATTACATAC-CATCCA---ATGGT
3157 169_HRV89b  AAGGGCTGTTGCCTATCAA-CACACACACTCAACCAATTACATAC-CATCCA---ATGGT
3158 170_HRV89   AAGGGCTGTTGCCTATCAA-CACACACACTCAACCAATTACATAC-CATCCA---ATGGT
3159 171_HRV58   AAGGGCTGTTCCTTATCAA-TTCACACATTCTACTAATTACATAC-CAGATA---GTGGT
3160 172_HRV58a  AAGGGCTGTTCCTTATCAA-TTCACACATTCTACTAATTACATAC-CAGATA---GTGGT
3161 173_HRV58b  AAGGGCTGTTCCTTATCAA-TTCACACATTCTACTAATTACATAC-CAGATA---GTGGT
3162 174_HRV12a  AAGAGCTGTACCATACCAG-CATATACACAATCCAAATTACAAGA-CAAGTA------AT
3163 175_HRV12b  AAGAGCTGTACCATACCAG-CATATACACAATCCAAATTACAAGA-CAAGTA------AT
3164 176_HRV12   AAGAGCTGTACCATACCAG-CATATACACAATCCAAATTACAAGA-CAAGTA------AT
3165 177_HRV78a  TAGAGCTGTACCTTATCAG-CACATATATAACCCTAATTATAAAA-CTGAAG------AA
3166 178_HRV78b  TAGAGCTGTACCTTATCAG-CACATATATAACCCTAATTATAAAA-CTGAAG------AA
3167 179_HRV78   TAGAGCTGTACCTTATCAG-CACATATATAACCCTAATTATAAAA-CTGAAG------AA
3168 180_HRV20   AAGAGCAGTGCCTTATCAA-CACACTAAGAGCACAAACTTAGTGC-CAAGGA---CAGGT
3169 181_HRV20a  AAGAGCAGTGCCTTATCAA-CACACTAAGAGCACAAACTTAGTGC-CAAGGA---CAGGT
3170 182_HRV20b  AAGAGCAGTGCCTTATCAA-CACACTAAGAGCACAAACTTAGTGC-CAAGGA---CAGGT
3171 183_HRV68   AAGAGCAGTGCCCTACCAG-CACACCAGAAGTACAAACTTAGTAC-CAAAGG---AAGGT
3172 184_HRV68a  AAGAGCAGTGCCCTACCAG-CACACCAGAAGTACAAACTTAGTAC-CAAAGG---AAGGT
3173 185_HRV68b  AAGAGCAGTGCCCTACCAG-CACACCAGAAGTACAAACTTAGTAC-CAAAGG---AAGGT
3174 186_HRV28   ACGCGCTGTAGCTTATCAA-CATACATACAGTCCAAACTTTGTGC-CTCAGG---AAGGT
3175 187_HRV28a  ACGCGCTGTAGCTTATCAA-CATACATACAGTCCAAACTTTGTGC-CTCAGG---AAGGT
3176 188_HRV28b  ACGCGCTGTAGCTTATCAA-CATACATACAGTCCAAACTTTGTGC-CTCAGG---AAGGT
3177 189_HRV53a  AAGAGCAGTTGCATATCAA-CACACATATAGCCCAAATTTTGTAC-CGCAAA---CAGGA
3178 190_HRV53b  AAGAGCAGTTGCATATCAA-CACACATATAGCCCAAATTTTGTAC-CGCAAA---CAGGA
3179 191_HRV53   AAGAGCAGTTGCATATCAA-CACACATATAGCCCAAATTTTGTAC-CGCAAA---CAGGA
3180 192_HRV46a  CAGAGCAGTCCCATATCAA-CATATTTATAATCCAAATTTCAAGA-CTACTCAACCTGAG
3181 193_HRV46b  CAGAGCAGTCCCATATCAA-CATATTTATAATCCAAATTTCAAGA-CTACTCAACCTGAG
3182 194_HRV46   CAGAGCAGTCCCATATCAA-CATATTTATAATCCAAATTTCAAGA-CTACTCAACCTGAG
3183 195_HRV80a  TAGAGCAGTCCCATACCAA-CATACCTACAGCCCAAATTTCAAAA-ACACTG---ATGAA
3184 196_HRV80b  TAGAGCAGTCCCATACCAA-CATACCTACAGCCCAAATTTCAAAA-ACACTG---ATGAA
3185 197_HRV80   TAGAGCAGTCCCATACCAA-CATACCTACAGCCCAAATTTCAAAA-ACACTG---ATGAA
```

FIG. D10 CONT'D

06.trace                                                                  9/20/2007 5:04 PM

```
3186 198_HRV51    TCGTGCTGTAGCCTACCAA-CACACATACAGTACAAACTTCGTTC-CAAAAGAGGGATTT
3187 199_HRV51a   TCGTGCTGTAGCCTACCAA-CACACATACAGTACAAACTTCGTTC-CAAAAGAGGGATTT
3188 200_HRV51b   TCGTGCTGTAGCCTACCAA-CACACATACAGTACAAACTTCGTTC-CAAAAGAGGGATTT
3189 201_HRV65a   CCGAGCAGTAGCTTACCAA-CACACATACAGTACAAATTTTGTTC-CTAGCGGAGGTCTT
3190 202_HRV65b   CCGAGCAGTAGCTTACCAA-CACACATACAGTACAAATTTTGTTC-CTAGCGGAGGTCTT
3191 203_HRV65    CCGAGCAGTAGCTTACCAA-CACACATACAGTACAAATTTTGTTC-CTAGCGGAGGTCTT
3192 204_HRV71a   CAGAGCAGTAGCCTACCAA-TCAACATATACCACAAATTTTGTTC-CACAAGACGGGATC
3193 205_HRV71b   CAGAGCAGTAGCCTACCAA-TCAACATATACCACAAATTTTGTTC-CACAAGACGGGATC
3194 206_HRV71    CAGAGCAGTAGCCTACCAA-TCAACATATACCACAAATTTTGTTC-CACAAGACGGGATC
3195 207_HRV8     CAGAGCAGTTACGTATAAC-CATATATACAACCCCAATTATGTTA-GAGAGG------GA
3196 208_HRV95    CAGAGCAGTTACGTATAAC-CATATATACAACCCCAATTATGTTA-GAGAGG------GA
3197 209_HRV45    AAGAGCAGTCACATATAAC-CATACATATAATCCAAATTATGTTA-GGGCTG------AT
3198 210_HRV45a   AAGAGCAGTCACATATAAC-CATACATATAATCCAAATTATGTTA-GGGCTG------AT
3199 211_HRV45b   AAGAGCAGTCACATATAAC-CATACATATAATCCAAATTATGTTA-GGGCTG------AT
3200 GROUP_1      --G-G---T----TA------------------AA-T-----------------------
3201
3202 1_HRV1A1|d   GACG------TGACAACAG---CCATAGTCCGCAGAA------ACACTATAACAACTG--
3203 2_HRV1A2|d   GACG------TGACAACAG---CCATAGTCCGCAGAA------ACACTATAACAACTG--
3204 3_HRV1A|cD   GACG------TGACAACAG---CCATAGTCCGCAGAA------ACACTATAACAACTG--
3205 4_HRV1B1|d   GATG------TGACAACAG---CTATAGTTCCTAGAG------CTAGCATGAAAACTG--
3206 5_HRV1B2|d   GATG------TGACAACAG---CTATAGTTCCTAGAG------CTAGCATGAAAACTG--
3207 6_HRV1B      GATG------TGACAACAG---CTATAGTTCCTAGAG------CTAGCATGAAAACTG--
3208 7_HRV40a|d   GAAG------TCCAGATTT---TCCTCAAAGAGAGAG------CCAGCCTAACAACAG--
3209 8_HRV40b|d   GAAG------TCCAGATTT---TCCTCAAAGAGAGAG------CCAGCCTAACAACAG--
3210 9_HRV40      GAAG------TCCAGATTT---TCCTCAAAGAGAGAG------CCAGCCTAACAACAG--
3211 10_HRV85     GAAG------TTAAGATCT---TCCTCAAAGAGAGAG------CTAGTTTAACCACAG--
3212 11_HRV85a|   GAAG------TTAAGATCT---TCCTCAAAGAGAGAG------CTAGTTTAACCACAG--
3213 12_HRV85b|   GAAG------TTAAGATCT---TCCTCAAAGAGAGAG------CTAGTTTAACCACAG--
3214 13_HRV56a|   GATG------TACAGATCT---TCTTAAAACCCAGAC------CCAGCCTAACAACAT--
3215 14_HRV56b|   GATG------TACAGATCT---TCTTAAAACCCAGAC------CCAGCCTAACAACAT--
3216 15_HRV56     GATG------TACAGATCT---TCTTAAAACCCAGAC------CCAGCCTAACAACAT--
3217 16_HRV54     GATC------CAACAATTT---TCCTTAAACACAGGA------CAAACCTTGTAACAG--
3218 17_HRV98     GAAC------CAACAATCT---TTCTTAAGCATAGAA------AAGATCTTGTAACAG--
3219 18_HRV59a|   GAAC------CTGAAATTT---TCTTAAAACCAAGAA------TGAATATTACAACAG--
3220 19_HRV59b|   GAAC------CTGAAATTT---TCTTAAAACCAAGAA------TGAATATTACAACAG--
3221 20_HRV59     GAAC------CTGAAATTT---TCTTAAAACCAAGAA------TGAATATTACAACAG--
3222 21_HRV63     GAGA------CTGAAATTT---TCTTAAAACCTAGAG------CAACTATCAAGACAG--
3223 22_HRV63b|   GAGA------CTGAAATTT---TCTTAAAACCTAGAG------CAACTATCAAGACAG--
3224 23_HRV63a|   GAGA------CTGAAATTT---TCTTAAAACCTAGAG------CAACTATCAAGACAG--
3225 24_HRV39     GAAC------CAACACTCT---TTATAAAATCAAGAG------AGAATCTTACCACAG--
3226 25_HRV39a|   GAAC------CAACACTCT---TTATAAAATCAAGAG------AGAATCTTACCACAG--
3227 26_HRV39b|   GAAC------CAACACTCT---TTATAAACCAAGAG-------AGAATCTTACCACAG--
3228 27_HRV10a|   GAAT------TACAAATAT---TTATTAGGTCTAGAGATGATCCCAAAGTAGTAACTG--
3229 28_HRV10b|   GAAT------TACAAATAT---TTATTAGGTCTAGAGATGATCCCAAAGTAGTAACTG--
3230 29_HRV10     GAAT------TACAAATAT---TTATTAGGTCTAGAGATGATCCCAAAGTAGTAACTG--
3231 30_HRV100a   GATG------TAAAGATTT---TCATTAGACCCAGAGATGATCCAAAGTTTGTAACTG--
3232 31_HRV100b   GATG------TAAAGATTT---TCATTAGACCCAGAGATGATCCAAAGTTTGTAACTG--
3233 32_HRV100    GATG------TAAAGATTT---TCATTAGACCCAGAGATGATCCAAAGTTTGTAACTG--
3234 33_HRV66     GATC------TGCAAATTT---TCATTAAACCTAGAACAGATCCAAAAGTAGTCAATG--
3235 34_HRV66b|   GATC------TGCAAATTT---TCATTAAACCTAGAACAGATCCAAAAGTAGTCAATG--
3236 35_HRV66a|   GATC------TGCAAATTT---TCATTAAACCTAGAACAGATCCAAAAGTAGTCAATG--
3237 36_HRV77a|   GATG------TACAAATCT---TTATTAAAGAGAGAGCAAGCCCAAAAGTAGTTACTT--
3238 37_HRV77b|   GATG------TACAAATCT---TTATTAAAGAGAGAGCAAGCCCAAAAGTAGTTACTT--
3239 38_HRV77     GATG------TACAAATCT---TTATTAAAGAGAGAGCAAGCCCAAAAGTAGTTACTT--
3240 39_HRV62a    ---G------TTGACATTT---TTATAAAATCAAGG------CAAAACTTGCAAACAG--
3241 40_HRV62b    ---G------TTGACATTT---TTATAAAATCAAGG------CAAAACTTGCAAACAG--
3242 41_HRV25     ---G------TTGACATCT---TTATACAACCAAGA------AACAGTTTAAAAACAG--
3243 42_HRV29a    ---G------AT-CCAG-----TTGTGGAATCCAGA------CCAAGCTTAATGACAG--
3244 43_HRV29b    ---G------AT-ACAG-----TTGTGGAATCCAGA------CCAAGCTTAATGACAG--
3245 44_HRV44a    ---G------AT-ACAG-----TTGTGGAACCTAGA------CACAGCATAATGACAG--
3246 45_HRV44b    ---G------AT-ACAG-----TTGTGGAACCTAGA------CACAGCATAATGACAG--
3247 46_HRV31     GAAG------TTACAATCT---TTGTTAAACACAGGGATAATCCAAAGATTATCACAG--
3248 47_HRV31a|   GAAG------TTACAATCT---TTGTTAAACACAGGGATAATCCAAAGATTATCACAG--
3249 48_HRV31b|   GAAG------TTACAATCT---TTGTTAAACACAGGGATAATCCAAAGATTATCACAG--
3250 49_HRV47     GAAG------TTGCAATTT---TCATTGAGCATAGAGAAAATCCAAAATTCATTACAG--
```

FIG. D10 CONT'D

06.trace                                                                    9/20/2007 5:04 PM

```
3251  50_HRV47a|   GAAG------TTGCAATTT---TCATTGAGCATAGAGAAAATCCAAAATTCATTACAG--
3252  51_HRV47b|   GAAG------TTGCAATTT---TCATTGAGCATAGAGAAAATCCAAAATTCATTACAG--
3253  52_HRV11     CAGG------TGAAAACAG---CTGTCAAGGCTAGGAAAACAATTAAAACAGCA------
3254  53_HRV11b|   CAGG------TGAAAACAG---CTGTCAAGGCTAGGAAAACAATTAAAACAGCG------
3255  54_HRV11a|   CAGG------TGAAAACAG---CTGTCAAGGCTAGGAAAACAATTAAAACAGCT------
3256  55_HRV76     GATG------TGCAAACAG---CTATTAGACCAAGAGCAACAATTAAGACTGCA------
3257  56_HRV76b|   GATG------TGCAAACAG---CTATTAGACCAAGAGCAACAATTAAGACTGCG------
3258  57_HRV76a|   GATG------TGCAAACAG---CTATTAGACCAAGAGCAACAATTAAGACTGCT------
3259  58_HRV33     GAAG------TGAAGACAG---CTATTAGACCAAGAGCAACAATCAAGACTGCA------
3260  59_HRV33b|   GAAG------TGAAGACAG---CTATTAGACCAAGAGCAACAATCAAGACTGCG------
3261  60_HRV33a|   GAAG------TGAAGACAG---CTATTAGACCAAGAGCAACAATCAAGACTGCT------
3262  61_HRV24a|   GAAG------TCAAGACAG---CAATTGAACCTAGAAGAGGAATTAAAACAGTG------
3263  62_HRV24b|   GAAG------TCAAGACAG---CAATTGAACCTAGAAGAGGAATTAAAACAGTC------
3264  63_HRV24     GAAG------TCAAGACAG---CAATTGAACCTAGAAGAGGAATTAAAACAGTT------
3265  64_HRV90     GAAC------TTAAGACTG---CAATTAGGCCCAGGAAAACAATCACAACAGCA------
3266  65_HRV90a|   GAAC------TTAAGACTG---CAATTAGGCCCAGGAAAACAATCACAACAGCG------
3267  66_HRV90b|   GAAC------TTAAGACTG---CAATTAGGCCCAGGAAAACAATCACAACAGCT------
3268  67_HRV34     ACTG------AGAAGACTG---CAATCAAACACAGAGCAAAGATCACAATGGCC------
3269  68_HRV34b|   ACTG------AGAAGACTG---CAATCAAACACAGAGCAAAGATCACAATGGCA------
3270  69_HRV34a|   ACTG------AGAAGACTG---CAATCAAACACAGAGCAAAGATCACAATGGCT------
3271  70_HRV50a|   ACTG------AGAAGACTG---CAATTGCAACTAGACCAAAGATCACAGTGGCA------
3272  71_HRV50b|   ACTG------AGAAGACTG---CAATTGCAACTAGACCAAAGATCACAGTGGCG------
3273  72_HRV50     ACTG------AGAAGACTG---CAATTGCAACTAGACCAAAGATCACAGTGGCT------
3274  73_HRV18a|   AGAG------AGAAAACTG---CCATAGTACCCAGAGCAAGGATTACAATGGCA------
3275  74_HRV18b|   AGAG------AGAAAACTG---CCATAGTACCCAGAGCAAGGATTACAATGGCG------
3276  75_HRV18     AGAG------AGAAAACTG---CCATAGTACCCAGAGCAAGGATTACAATGGCT------
3277  76_HRV55     ACAG------AAAAGACAG---CAATTGAATACAGAAGGGACATTAAAACAGTG------
3278  77_HRV55b|   ACAG------AAAAGACAG---CAATTGAATACAGAAGGGACATTAAAACAGTC------
3279  78_HRV55a|   ACAG------AAAAGACAG---CAATTGAATACAGAAGGGACATTAAAACAGTA------
3280  79_HRV57     CAAG------AAGAAACAG---CAATTAAATATAGAAGGGACATTAAAATTGTTAAGA--
3281  80_HRV57a|   CAAG------AAGAAACAG---CAATTAAATATAGAAGGGACATTAAAATTGTTAAGA--
3282  81_HRV57b|   CAAG------AAGAAACAG---CAATTAAATATAGAAGGGACATTAAAATTGTTAAGA--
3283  82_HRV21     GAAG------TCACTTCTG---CAGTTGAGTCCAGAAGAACAATTGTCACAGTT------
3284  83_HRVHan    GATG------TCACTTCTG---CAGTTGAGTCCAGAAGAACAATTGTCACAGTT------
3285  84_HRV43     GAGG------TAGAAACAG---CCATAGTATCTAGGAGGGATATCAAAATTGTCAATG--
3286  85_HRV43b|   GAGG------TAGAAACAG---CCATAGTATCTAGGAGGGATATCAAAATTGTCAATG--
3287  86_HRV43a|   GAGG------TAGAAACAG---CCATAGTATCTAGGAGGGATATCAAAATTGTCAATG--
3288  87_HRV75     CAAG------TTGAGATTG---CTATTGAGCCCAGAAGAGATGTTAAGTTTGTAAATG--
3289  88_HRV75b|   CAAG------TTGAGATTG---CTATTGAGCCCAGAAGAGATGTTAAGTTTGTAAATG--
3290  89_HRV75a|   CAAG------TTGAGATTG---CTATTGAGCCCAGAAGAGATGTTAAGTTTGTAAATG--
3291  96_HRV9a|d   GATT------ATGCCACAG---TTATACCAGTTAGAGACAATGTTAGGGCAGTAAAGA--
3292  97_HRV9b|d   GATT------ATGCCACAG---TTATACCAGTTAGAGACAATGTTAGGGCAGTAAAGA--
3293  98_HRV9      GATT------ATGCCACAG---TTATACCAGTTAGAGACAATGTTAGGGCAGTAAAGA--
3294  99_HRV32     GATT------ACACCACAG---CCATACAAACCAGAGAGCATGTTAGAGCAGTCAAAA--
3295 100_HRV32a    GATT------ACACCACAG---CCATACAAACCAGAGAGCATGTTAGAGCAGTCAAAA--
3296 101_HRV32b    GATT------ACACCACAG---CCATACAAACCAGAGAGCATGTTAGAGCAGTCAAAA--
3297 102_HRV67     GAGG------CTCAAACGG---TTATACCTGTTAGAGCAGATGTTAGAACAATTAGAA--
3298 103_HRV67a    GAGG------CTCAAACGG---TTATACCTGTTAGAGCAGATGTTAGAACAATTAGAA--
3299 104_HRV67b    GAGG------CTCAAACGG---TTATACCTGTTAGAGCAGATGTTAGAACAATTAGAA--
3300 105_HRV15     GATG------TAACTACAG---TTATTCCAACTAGAGAAAATGTTAGAGCTATAGTAA--
3301 106_HRV15a    GATG------TAACTACAG---TTATTCCAACTAGAGAAAATGTTAGAGCTATAGTAA--
3302 107_HRV15b    GATG------TAACTACAG---TTATTCCAACTAGAGAAAATGTTAGAGCTATAGTAA--
3303 108_HRV74a    GACG------TAACTACAG---TCATCCCAACTAGG--------AGATCAATAGTGA--
3304 109_HRV74b    GACG------TAACTACAG---TCATCCCAACTAGG--------AGATCAATAGTGA--
3305 110_HRV74     GACG------TAACTACAG---TCATCCCAACTAGG--------AGATCAATAGTGA--
3306 111_HRV38a    GAAG------TAACCACTA---TGATTCCAACTAGAACCAACATAAGAACCATCGTAA--
3307 112_HRV38b    GAAG------TAACCACTA---TGATTCCAACTAGAACCAACATAAGAACCATCGTAA--
3308 113_HRV38     GAAG------TAACCACTA---TGATTCCAACTAGAACCAACATAAGAACCATCGTAA--
3309 114_HRV60     GAAG------CAGCCATAA---CAATCCCCATTAGAACTGATATACGAGCAATCAGAA--
3310 115_HRV60a    GAAG------CAGCCATAA---CAATCCCCATTAGAACTGATATACGAGCAATCAGAA--
3311 116_HRV60b    GAAG------CAGCCATAA---CAATCCCCATTAGAACTGATATACGAGCAATCAGAA--
3312 117_HRV64a    GAAT------ACACACCAC---CCGTTCCGTCACGTAACAGCCCCAGAGATATTGTCA--
3313 118_HRV64b    GAAT------ACACACCAC---CCGTTCCGTCACGTAACAGCCCCAGAGATATTGTCA--
3314 119_HRV64     GAAT------ACACACCAC---CCGTTCCGTCACGTAACAGCCCCAGAGATATTGTCA--
3315 120_HRV94a    GAGT------ACAAGCCAC---CTGTCCCAGTTAGGAATAGCCCCAGAGACATTGTCA--
```

FIG. D10 CONT'D 06.trace                                                                                          9/20/2007 5:04 PM

```
3316  121_HRV94b  GAGT------ACAAGCCAC---CTGTCCCAGTTAGGAATAGCCCCAGAGACATTGTCA--
3317  122_HRV94   GAGT------ACAAGCCAC---CTGTCCCAGTTAGGAATAGCCCCAGAGACATTGTCA--
3318  123_HRV22   GATT------ACACACTAC---CTATCCCAACAAGAGCCAACCCTAGACAAATTTTGA--
3319  124_HRV22a  GATT------ACACACTAC---CTATCCCAACAAGAGCCAACCCTAGACAAATTTTGA--
3320  125_HRV22b  GATT------ACACACTAC---CTATCCCAACAAGAGCCAACCCTAGACAAATTTTGA--
3321  126_HRV82   GATT------ACAGTGTTG---TTATTCCAGTTAGAGAGAGTCCCAGACAGATTCTTA--
3322  127_HRV82b  GATT------ACAGTGTTG---TTATTCCAGTTAGAGAGAGTCCCAGACAGATTCTTA--
3323  128_HRV82a  GATT------ACAGTGTTG---TTATTCCAGTTAGAGAGAGTCCCAGACAGATTCTTA--
3324  129_HRV19   GAAG------TCACTCTTC---CAATTGAAATAAGAGATAACCCTAGACATATAAAGA--
3325  130_HRV19a  GAAG------TCACTCTTC---CAATTGAAATAAGAGATAACCCTAGACATATAAAGA--
3326  131_HRV19b  GAAG------TCACTCTTC---CAATTGAAATAAGAGATAACCCTAGACATATAAAGA--
3327  132_HRV13   GATG------TTGCAGTCT---CCATTGTACCTAGAGCAAATGTTAGGGAAATTAGAA--
3328  133_HRV13a  GATG------TTGCAGTCT---CCATTGTACCTAGAGCAAATGTTAGGGAAATTAGAA--
3329  134_HRV13b  GATG------TTGCAGTCT---CCATTGTACCTAGAGCAAATGTTAGGGAAATTAGAA--
3330  135_HRV41   GCAGA---GATTGTGGCTT---CTGTCAGACCTAGAGACAATGTTAGACAAGTAAGAA--
3331  136_HRV41a  GCAGA---GATTGTGGCTT---CTGTCAGACCTAGAGACAATGTTAGACAAGTAAGAA--
3332  137_HRV41b  GCAGA---GATTGTGGCTT---CTGTCAGACCTAGAGACAATGTTAGACAAGTAAGAA--
3333  138_HRV73   GAAG------TTACTACTG---CCATTAGGCATAGAGATAATGTTAGAGCCATCCAAA--
3334  139_HRV73b  GAAG------TTACTACTG---CCATTAGGCATAGAGATAATGTTAGAGCCATCCAAA--
3335  140_HRV73a  GAAG------TTACTACTG---CCATTAGGCATAGAGATAATGTTAGAGCCATCCAAA--
3336  141_HRV61   GAAAAACAAGTTACCACTT---TCATCAAACCTAGAGCTAACTTAAGAGAGATTAGAA--
3337  142_HRV61a  GAAAAACAAGTTACCACTT---TCATCAAACCTAGAGCTAACTTAAGAGAGATTAGAA--
3338  143_HRV61b  GAAAAACAAGTTACCACTT---TCATCAAACCTAGAGCTAACTTAAGAGAGATTAGAA--
3339  144_HRV96   -------AGGTTACCACTT---TTATCAAACCTAGAGAAAATCTAAGGGATATTAGAA--
3340  145_HRV96b  -------AGGTTACCACTT---TTATCAAACCTAGAGAAAATCTAAGGGATATTAGAA--
3341  146_HRV96a  -------AGGTTACCACTT---TTATCAAACCTAGAGAAAATCTAAGGGATATTAGAA--
3342   90_HRV16a|  GTAC------ACAATGATGTGGCTATAAGACCTAGAACAAATCTAACAACTGTA-----
3343   91_HRV16b|  GTAC------ACAATGATGTGGCTATAAGACCTAGAACAAATCTAACAACTGTC-----
3344   92_1AYM_A   GTAC------ACAATGATGTGGCTATAAGACCTAGAACAAATCTAACAACTGTT-----
3345   93_HRV81a|  GTCC------ACACTAGTGTAGCCATAAAACCTAGAACAAGTCTAACAAATGTG-----
3346   94_HRV81b|  GTCC------ACACTAGTGTAGCCATAAAACCTAGAACAAGTCTAACAAATGTC-----
3347   95_HRV81    GTCC------ACACTAGTGTAGCCATAAAACCTAGAACAAGTCTAACAAATGTT-----
3348  147_HRV2    AGTA------TTCAGACAG---CAATTGTGACCAGACCAATTATCACTACAGCT-----
3349  148_HRV2a|  AGTA------TTCAGACAG---CAATTGTGACCAGACCAATTATCACTACAGCA-----
3350  149_HRV2b|  AGTA------TTCAGACAG---CAATTGTGACCAGACCAATTATCACTACAGCG-----
3351  150_HRV49a  GACA------TTAAAACAG---GAATCACATCCAGAGCAATTATTACAACAGCG-----
3352  151_HRV49b  GACA------TTAAAACAG---GAATCACATCCAGAGCAATTATTACAACAGCA-----
3353  152_HRV49   GACA------TTAAAACAG---GAATCACATCCAGAGCAATTATTACAACAGCT-----
3354  153_HRV23a  AATG------TCAAATCAA---GGGTTGCACATAGACCTGCAGTGATAACAGCG-----
3355  154_HRV23b  AATG------TCAAATCAA---GGGTTGCACATAGACCTGCAGTGATAACAGCA-----
3356  155_HRV23   AATG------TCAAATCAA---GGGTTGCACATAGACCTGCAGTGATAACAGCT-----
3357  156_HRV30a  GAAG------TTAAATCAA---GGGTTGAACACAGAGCTAGGTGACGACAGCG-----
3358  157_HRV30b  GAAG------TTAAATCAA---GGGTTGAACACAGAGCTAGGGTGACGACAGCG-----
3359  158_HRV30   GAAG------TTAAATCAA---GGGTTGAACACAGAGCTAGGGTGACGACAGCT-----
3360  159_HRV7    GAGG------TCGCA---ACTCAAATCAAAACCAGAGCCAATCTTTTCACCCTCAAAT--
3361  160_HRV7b|  GAGG------TCGCA---ACTCAAATCAAAACCAGAGCCAATCTTTTCACCCTCAAAT--
3362  161_HRV7a|  GAGG------TCGCA---ACTCAAATCAAAACCAGAGCCAATCTTTTCACCCTCAAAT--
3363  162_HRV88   GAAG------TAGCA---ACTCAAATCAAAACCAGACGAGATGTTTACACTGTTACCA--
3364  163_HRV88a  GAAG------TAGCA---ACTCAAATCAAAACCAGACGAGATGTTTACACTGTTACCA--
3365  164_HRV88b  GAAG------TAGCA---ACTCAAATCAAAACCAGACGAGATGTTTACACTGTTACCA--
3366  165_HRV36a  GAGA------TCACA---ACCCAAATTAAAACCAGACCTAATGTCTTCACTGTA-----
3367  166_HRV36b  GAGA------TCACA---ACCCAAATTAAAACCAGACCTAATGTCTTCACTGTG-----
3368  167_HRV36   GAGA------TCACA---ACCCAAATTAAAACCAGACCTAATGTCTTCACTGTT-----
3369  168_HRV89a  GAGG------CCACA---ACTCAGATTAAAACCAGACCTGATGTTTTTACCGTTACAA--
3370  169_HRV89b  GAGG------CCACA---ACTCAGATTAAAACCAGACCTGATGTTTTTACCGTTACAA--
3371  170_HRV89   GAGG------CCACA---ACTCAGATTAAAACCAGACCTGATGTTTTTACCGTTACAA--
3372  171_HRV58   GAGG------TAACA---ACACAAATCAAACCCAGAACCAATGTTTTTACTATTACAT--
3373  172_HRV58a  GAGG------TAACA---ACACAAATCAAACCCAGAACCAATGTTTTTACTATTACAT--
3374  173_HRV58b  GAGG------TAACA---ACACAAATCAAACCCAGAACCAATGTTTTTACTATTACAT--
3375  174_HRV12a  GGAG------TTCCAGACAATAGAGTCAAACTCAGAGAGACACTCACCACAGTA-----
3376  175_HRV12b  GGAG------TTCCAGACAATAGAGTCAAACTCAGAGAGACACTCACCACAGTG-----
3377  176_HRV12   GGAG------TTCCAGACAATAGAGTCAAACTCAGAGAGACACTCACCACAGTT-----
3378  177_HRV78a  GGAA------CTCCAGACACCAAAGTGGCAATTAGAGCTAATATTAAAACTGTA-----
3379  178_HRV78b  GGAA------CTCCAGACACCAAAGTGGCAATTAGAGCTAATATTAAAACTGTG-----
3380  179_HRV78   GGAA------CTCCAGACACCAAAGTGGCAATTAGAGCTAATATTAAAACTGTT-----
```

FIG. D10 CONT'D

```
06.trace                                                                 9/20/2007 5:04 PM 3381  180_HRV20    GAAA------TTACA---ACTCATATCAGATTCAGAAACACTGTCAAAGATCTAACATAC
3382  181_HRV20a   GAAA------TTACA---ACTCATATCAGATTCAGAAACACTGTCAAAGATCTAACATAC
3383  182_HRV20b   GAAA------TTACA---ACTCATATCAGATTCAGAAACACTGTCAAAGATCTAACATAC
3384  183_HRV68    GATA------TTAAA---ACTCATATTAAATTTAGGAATACTGTTAAAGATTTGGCATAT
3385  184_HRV68a   GATA------TTAAA---ACTCATATTAAATTTAGGAATACTGTTAAAGATTTGGCATAT
3386  185_HRV68b   GATA------TTAAA---ACTCATATTAAATTTAGGAATACTGTTAAAGATTTGGCATAT
3387  186_HRV28    GATG------TTGAG---ACTCATATTAAATTTAGAACAGATGTTAAACAGATCACAA--
3388  187_HRV28a   GATG------TTGAG---ACTCATATTAAATTTAGAACAGATGTTAAACAGATCACAA--
3389  188_HRV28b   GATG------TTGAG---ACTCATATTAAATTTAGAACAGATGTTAAACAGATCACAA--
3390  189_HRV53a   ACAG------TTGAA---ACTCACATTAAGTTCAGACCTGATGTTAAAGATGTAACAT--
3391  190_HRV53b   ACAG------TTGAA---ACTCACATTAAGTTCAGACCTGATGTTAAAGATGTAACAT--
3392  191_HRV53    ACAG------TTGAA---ACTCACATTAAGTTCAGACCTGATGTTAAAGATGTAACAT--
3393  192_HRV46a   ACTA------TACCAGATACTCATATTGGAATTAGAAGGGATATAAAGTACATTAAAA--
3394  193_HRV46b   ACTA------TACCAGATACTCATATTGGAATTAGAAGGGATATAAAGTACATTAAAA--
3395  194_HRV46    ACTA------TACCAGATACTCATATTGGAATTAGAAGGGATATAAAGTACATTAAAA--
3396  195_HRV80a   TCTA------TACCAGATACACAAATTAAAATCAGAGATAATATCAGGCAGGTTAGAA--
3397  196_HRV80b   TCTA------TACCAGATACACAAATTAAAATCAGAGATAATATCAGGCAGGTTAGAA--
3398  197_HRV80    TCTA------TACCAGATACACAAATTAAAATCAGAGATAATATCAGGCAGGTTAGAA--
3399  198_HRV51    GAAG------GCTTGAAAACTCAGATTAAAACTAGGGCAGACATCAAACTTGTGAACT--
3400  199_HRV51a   GAAG------GCTTGAAAACTCAGATTAAAACTAGGGCAGACATCAAACTTGTGAACT--
3401  200_HRV51b   GAAG------GCTTGAAAACTCAGATTAAAACTAGGGCAGACATCAAACTTGTGAACT--
3402  201_HRV65a   ACAA------ACCTAAGAACCCAAATTAAAACCAGAGATAACATTAAAATTGTAAACT--
3403  202_HRV65b   ACAA------ACCTAAGAACCCAAATTAAAACCAGAGATAACATTAAAATTGTAAACT--
3404  203_HRV65    ACAA------ACCTAAGAACCCAAATTAAAACCAGAGATAACATTAAAATTGTAAACT--
3405  204_HRV71a   AATT------CCATTAAAACCAAAATCAAAATCAGAAGAGACATTAAAGAGGTCAGCA--
3406  205_HRV71b   AATT------CCATTAAAACCAAAATCAAAATCAGAAGAGACATTAAAGAGGTCAGCA--
3407  206_HRV71    AATT------CCATTAAAACCAAAATCAAAATCAGAAGAGACATTAAAGAGGTCAGCA--
3408  207_HRV8     GTAA------CACCAGAAACTAAGGTTAAATATAGAGCTGAAGTCACAACCATT------
3409  208_HRV95    GTAA------CACCAGAAACTAAGGTCAAATATAGAGCTGAAGTCACAACCATT------
3410  209_HRV45    GAAA------CAGCC---ACAAAAGTCCAAACTAGAGCAAATGTCACAACAGTA------
3411  210_HRV45a   GAAA------CAGCC---ACAAAAGTCCAAACTAGAGCAAATGTCACAACAGTG------
3412  211_HRV45b   GAAA------CAGCC---ACAAAAGTCCAAACTAGAGCAAATGTCACAACAGTT------
3413  GROUP_1      -----------------------T--------G---------------------------
3414
3415  1_HRV1A1|d   ----CA---------------
3416  2_HRV1A2|d   ----CG---------------
3417  3_HRV1A|cD   ----CT---------------
3418  4_HRV1B1|d   ----TA---------------
3419  5_HRV1B2|d   ----TC---------------
3420  6_HRV1B      ----TT---------------
3421  7_HRV40a|d   ----TA---------------
3422  8_HRV40b|d   ----TC---------------
3423  9_HRV40      ----TT---------------
3424  10_HRV85     ----CA---------------
3425  11_HRV85a|   ----CG---------------
3426  12_HRV85b|   ----CT---------------
3427  13_HRV56a|   ----TA---------------
3428  14_HRV56b|   ----TG---------------
3429  15_HRV56     ----TT---------------
3430  16_HRV54     ----CT---------------
3431  17_HRV98     ----CT---------------
3432  18_HRV59a|   ----CA---------------
3433  19_HRV59b|   ----CG---------------
3434  20_HRV59     ----CT---------------
3435  21_HRV63     ----CA---------------
3436  22_HRV63b|   ----CG---------------
3437  23_HRV63a|   ----CT---------------
3438  24_HRV39     ----CT---------------
3439  25_HRV39a|   ----CA---------------
3440  26_HRV39b|   ----CT---------------
3441  27_HRV10a|   ----CA---------------
3442  28_HRV10b|   ----CC---------------
3443  29_HRV10     ----CT---------------
3444  30_HRV100a   ----CA---------------
3445  31_HRV100b   ----CG---------------
```

FIG. D10 CONT'D 06.trace                                                                9/20/2007 5:04 PM

```
3446  32_HRV100     ----CT---------------
3447  33_HRV66      ----TA---------------
3448  34_HRV66b|    ----TG---------------
3449  35_HRV66a|    ----TC---------------
3450  36_HRV77a|    ----TG---------------
3451  37_HRV77b|    ----TA---------------
3452  38_HRV77      ----TT---------------
3453  39_HRV62a     ----CT---------------
3454  40_HRV62b     ----C----------------
3455  41_HRV25      ----CT---------------
3456  42_HRV29a     ----CT---------------
3457  43_HRV29b     ----CT---------------
3458  44_HRV44a     ----CT---------------
3459  45_HRV44b     ----CT---------------
3460  46_HRV31      ----CA---------------
3461  47_HRV31a|    ----CT---------------
3462  48_HRV31b|    ----CA---------------
3463  49_HRV47      ----CA---------------
3464  50_HRV47a|    ----CT---------------
3465  51_HRV47b|    ----CA---------------
3466  52_HRV11      ---------------------
3467  53_HRV11b|    ---------------------
3468  54_HRV11a|    ---------------------
3469  55_HRV76      ---------------------
3470  56_HRV76b|    ---------------------
3471  57_HRV76a|    ---------------------
3472  58_HRV33      ---------------------
3473  59_HRV33b|    ---------------------
3474  60_HRV33a|    ---------------------
3475  61_HRV24a|    ---------------------
3476  62_HRV24b|    ---------------------
3477  63_HRV24      ---------------------
3478  64_HRV90      ---------------------
3479  65_HRV90a|    ---------------------
3480  66_HRV90b|    ---------------------
3481  67_HRV34      ---------------------
3482  68_HRV34b|    ---------------------
3483  69_HRV34a|    ---------------------
3484  70_HRV50a|    ---------------------
3485  71_HRV50b|    ---------------------
3486  72_HRV50      ---------------------
3487  73_HRV18a|    ---------------------
3488  74_HRV18b|    ---------------------
3489  75_HRV18      ---------------------
3490  76_HRV55      ---------------------
3491  77_HRV55b|    ---------------------
3492  78_HRV55a|    ---------------------
3493  79_HRV57      ----ATGTG------------
3494  80_HRV57a|    ----ATGTA------------
3495  81_HRV57b|    ----ATGTC------------
3496  82_HRV21      ---------------------
3497  83_HRVHan     ---------------------
3498  84_HRV43      ----CA---------------
3499  85_HRV43b|    ----CG---------------
3500  86_HRV43a|    ----CT---------------
3501  87_HRV75      ----CA---------------
3502  88_HRV75b|    ----CG---------------
3503  89_HRV75a|    ----CT---------------
3504  96_HRV9a|d    ----ATGTC------------
3505  97_HRV9b|d    ----ATGTG------------
3506  98_HRV9       ----ATGTA------------
3507  99_HRV32      ----ATGTA------------
3508  100_HRV32a    ----ATGTG------------
3509  101_HRV32b    ----ATGTC------------
3510  102_HRV67     ----ATGTA------------
```

FIG. D10 CONT'D

```
06.trace                                                                  9/20/2007 5:04 PM 3511  103_HRV67a      ----ATGTC-----------
3512  104_HRV67b      ----ATGTT-----------
3513  105_HRV15       ----ATGTT-----------
3514  106_HRV15a      ----ATGTA-----------
3515  107_HRV15b      ----ATGTC-----------
3516  108_HRV74a      ----ATGTA-----------
3517  109_HRV74b      ----ATGTC-----------
3518  110_HRV74       ----ATGTT-----------
3519  111_HRV38a      ----ATGTA-----------
3520  112_HRV38b      ----ATGTC-----------
3521  113_HRV38       ----ATGTT-----------
3522  114_HRV60       ----CAGTT-----------
3523  115_HRV60a      ----CAGTA-----------
3524  116_HRV60b      ----CAGTG-----------
3525  117_HRV64a      ----CAGTG-----------
3526  118_HRV64b      ----CAGTG-----------
3527  119_HRV64       ----CAGTA-----------
3528  120_HRV94a      ----CAGTG-----------
3529  121_HRV94b      ----CAGTC-----------
3530  122_HRV94       ----CAGTA-----------
3531  123_HRV22       ----ATGTA-----------
3532  124_HRV22a      ----ATGTG-----------
3533  125_HRV22b      ----ATGTC-----------
3534  126_HRV82       ----ATGTA-----------
3535  127_HRV82b      ----ATGTT-----------
3536  128_HRV82a      ----ATGTC-----------
3537  129_HRV19       ----ATGTA-----------
3538  130_HRV19a      ----ATGTG-----------
3539  131_HRV19b      ----ATGTC-----------
3540  132_HRV13       ----ACTTT-----------
3541  133_HRV13a      ----ACTTG-----------
3542  134_HRV13b      ----ACTTA-----------
3543  135_HRV41       ----ATTAT-----------
3544  136_HRV41a      ----ATTAG-----------
3545  137_HRV41b      ----ATTAC-----------
3546  138_HRV73       ----ATTTT-----------
3547  139_HRV73b      ----ATTTG-----------
3548  140_HRV73a      ----ATTTC-----------
3549  141_HRV61       ----CATTT-----------
3550  142_HRV61a      ----CATTT-----------
3551  143_HRV61b      ----CATTT-----------
3552  144_HRV96       ----ATTTT-----------
3553  145_HRV96b      ----ATTTA-----------
3554  146_HRV96a      ----ATTTC-----------
3555  90_HRV16a|      --------------------
3556  91_HRV16b|      --------------------
3557  92_1AYM_A       --------------------
3558  93_HRV81a|      --------------------
3559  94_HRV81b|      --------------------
3560  95_HRV81        --------------------
3561  147_HRV2        --------------------
3562  148_HRV2a|      --------------------
3563  149_HRV2b|      --------------------
3564  150_HRV49a      --------------------
3565  151_HRV49b      --------------------
3566  152_HRV49       --------------------
3567  153_HRV23a      --------------------
3568  154_HRV23b      --------------------
3569  155_HRV23       --------------------
3570  156_HRV30a      --------------------
3571  157_HRV30b      --------------------
3572  158_HRV30       --------------------
3573  159_HRV7        ----CAGCT-----------
3574  160_HRV7b|      ----CAGCA-----------
3575  161_HRV7a|      ----CAGCG-----------
```

FIG. D10 CONT'D 06.trace                                                                                              9/20/2007 5:04 PM

```
3576 162_HRV88      ----CTGCT-----------
3577 163_HRV88a     ----CTGCA-----------
3578 164_HRV88b     ----CTGCG-----------
3579 165_HRV36a     --------------------
3580 166_HRV36b     --------------------
3581 167_HRV36      --------------------
3582 168_HRV89a     ----ACGTG-----------
3583 169_HRV89b     ----ACGTA-----------
3584 170_HRV89      ----ACGTC-----------
3585 171_HRV58      ----CTGCT-----------
3586 172_HRV58a     ----CTGCA-----------
3587 173_HRV58b     ----CTGCC-----------
3588 174_HRV12a     --------------------
3589 175_HRV12b     --------------------
3590 176_HRV12      --------------------
3591 177_HRV78a     --------------------
3592 178_HRV78b     --------------------
3593 179_HRV78      --------------------
3594 180_HRV20      CCCACAGAAATGACGAATGTT
3595 181_HRV20a     CCCACAGAAATGACGAATGTA
3596 182_HRV20b     CCCACAGAAATGACGAATGTG
3597 183_HRV68      CCTCCAGAATTAGCAAACCTT
3598 184_HRV68a     CCTCCAGAATTAGCAAACCTT
3599 185_HRV68b     CCTCCAGAATTAGCAAACCTT
3600 186_HRV28      ----CAGTT-----------
3601 187_HRV28a     ----CAGTA-----------
3602 188_HRV28b     ----CAGTC-----------
3603 189_HRV53a     ----CAGTAATGACAGCT---
3604 190_HRV53b     ----CAGTAATGACAGCT---
3605 191_HRV53      ----CAGTAATGACAGCA---
3606 192_HRV46a     ----CAGCA-----------
3607 193_HRV46b     ----CAGCC-----------
3608 194_HRV46      ----CAGCT-----------
3609 195_HRV80a     ----CAGTA-----------
3610 196_HRV80b     ----CAGTC-----------
3611 197_HRV80      ----CAGTT-----------
3612 198_HRV51      -----TT-------------
3613 199_HRV51a     -----TA-------------
3614 200_HRV51b     -----TG-------------
3615 201_HRV65a     -----TG-------------
3616 202_HRV65b     -----TA-------------
3617 203_HRV65      -----TT-------------
3618 204_HRV71a     -----ACTAA----------
3619 205_HRV71b     -----ACTAG----------
3620 206_HRV71      -----ACTAT----------
3621 207_HRV8       --------------------
3622 208_HRV95      --------------------
3623 209_HRV45      --------------------
3624 210_HRV45a     --------------------
3625 211_HRV45b     --------------------
3626 GROUP_1        --------------------
3627
3628
3629
3630 Summary:
3631
3632 GROUP_1        AA-CC--T-GA----T------A-----T--T-----A-GT--T--T-GT-CC--A----
3633 SUMMARY        AA-CC--T-GA----T------A-----T--T-----A-GT--T--T-GT-CC--A----
3634
3635 GROUP_1        ------AG----------------A--C-G---C-----T-GA-GC-GC-GA-AC-GG-
3636 SUMMARY        ------AG----------------A--C-G---C-----T-GA-GC-GC-GA-AC-GG-
3637
3638 GROUP_1        CA-AC-A--------CA-CC-GA-GA-----T-GA-AC--G----GT----------A-
3639 SUMMARY        CA-AC-A--------CA-CC-GA-GA-----T-GA-AC--G----GT----------A-
3640
```

FIG. D10 CONT'D

```
06.trace                                                          9/20/2007 5:04 PM 3641 GROUP_1      AC-----ATGA-A------T-GA----TT--T-GG--G--C----TG-------------
3642 SUMMARY      AC-----ATGA-A------T-GA----TT--T-GG--G--C----TG-------------
3643
3644 GROUP_1      ------------------------------------------------------------
3645 SUMMARY      ------------------------------------------------------------
3646
3647 GROUP_1      ------------TGG----T-A---T----GA-ATG-C-CA--T--G--G-AA----GA-
3648 SUMMARY      ------------TGG----T-A---T----GA-ATG-C-CA--T--G--G-AA----GA-
3649
3650 GROUP_1      -T-TT-AC-TA-----G-TT--A-TC-GA--T-AC--T-G-T----------C------
3651 SUMMARY      -T-TT-AC-TA-----G-TT--A-TC-GA--T-AC--T-G-T----------C------
3652
3653 GROUP_1      -------------GG-CA--T-----T-CA-T--ATGT---T-CC-CC-GG-G--CC---
3654 SUMMARY      -------------GG-CA--T-----T-CA-T--ATGT---T-CC-CC-GG-G--CC---
3655
3656 GROUP_1      -CC--------G-------------TGG-A--C--G-A--AA----TC----TT-TGGCA
3657 SUMMARY      -CC--------G-------------TGG-A--C--G-A--AA----TC----TT-TGGCA
3658
3659 GROUP_1      ----GG-CA----T--CC--G--T--C--T-CC-TT-----G--T-GC-TC-G--TA-TA
3660 SUMMARY      ----GG-CA----T--CC--G--T--C--T-CC-TT-----G--T-GC-TC-G--TA-TA
3661
3662 GROUP_1      -ATGTT-TA-GA-GG-TA-----------------------TA-GG------------
3663 SUMMARY      -ATGTT-TA-GA-GG-TA-----------------------TA-GG------------
3664
3665 GROUP_1      -AA----ATGGG--C--T-T------G--T--T-AC-------CA---------------
3666 SUMMARY      -AA----ATGGG--C--T-T------G--T--T-AC-------CA---------------
3667
3668 GROUP_1      --T----------T-T--C--AA-GC-AA-CA---------TGG-G-CC--G--C-C-
3669 SUMMARY      --T----------T-T--C--AA-GC-AA-CA---------TGG-G-CC--G--C-C-
3670
3671 GROUP_1      --G-G---T----TA------------------AA-T---------------------
3672 SUMMARY      --G-G---T----TA------------------AA-T---------------------
3673
3674 GROUP_1      -------------------------T--------G------------------------
3675 SUMMARY      -------------------------T--------G------------------------
3676
3677 GROUP_1      ---------------------
3678 SUMMARY      ---------------------
3679
3680
```

FIG. D10 CONT'D

```
07.trace                                                        9/20/2007 5:04 PM 1 Group 1:  1_HRV1A1|d
 2 Group 1:  2_HRV1A2|d
 3 Group 1:  3_HRV1A|cD
 4 Group 1:  4_HRV1B1|d
 5 Group 1:  5_HRV1B2|d
 6 Group 1:  6_HRV1B
 7 Group 1:  7_HRV40a|d
 8 Group 1:  8_HRV40b|d
 9 Group 1:  9_HRV40
10 Group 1: 10_HRV85
11 Group 1: 11_HRV85a|
12 Group 1: 12_HRV85b|
13 Group 1: 13_HRV56a|
14 Group 1: 14_HRV56b|
15 Group 1: 15_HRV56
16 Group 1: 16_HRV54
17 Group 1: 17_HRV98
18 Group 1: 18_HRV59a|
19 Group 1: 19_HRV59b|
20 Group 1: 20_HRV59
21 Group 1: 21_HRV63
22 Group 1: 22_HRV63b|
23 Group 1: 23_HRV63a|
24 Group 1: 24_HRV39
25 Group 1: 25_HRV39a|
26 Group 1: 26_HRV39b|
27 Group 1: 27_HRV10a|
28 Group 1: 28_HRV10b|
29 Group 1: 29_HRV10
30 Group 1: 30_HRV100a
31 Group 1: 31_HRV100b
32 Group 1: 32_HRV100
33 Group 1: 33_HRV66
34 Group 1: 34_HRV66b|
35 Group 1: 35_HRV66a|
36 Group 1: 36_HRV77a|
37 Group 1: 37_HRV77b|
38 Group 1: 38_HRV77
39 Group 1: 39_HRV62a
40 Group 1: 40_HRV62b
41 Group 1: 41_HRV25
42 Group 1: 42_HRV29a
43 Group 1: 43_HRV29b
44 Group 1: 44_HRV44a
45 Group 1: 45_HRV44b
46 Group 1: 46_HRV31
47 Group 1: 47_HRV31a|
48 Group 1: 48_HRV31b|
49 Group 1: 49_HRV47
50 Group 1: 50_HRV47a|
51 Group 1: 51_HRV47b|
52 Group 1: 52_HRV11
53 Group 1: 53_HRV11b|
54 Group 1: 54_HRV11a|
55 Group 1: 55_HRV76
56 Group 1: 56_HRV76b|
57 Group 1: 57_HRV76a|
58 Group 1: 58_HRV33
59 Group 1: 59_HRV33b|
60 Group 1: 60_HRV33a|
61 Group 1: 61_HRV24a|
62 Group 1: 62_HRV24b|
```

FIG. D11

```
07.trace                                                        9/20/2007 5:04 PM
     63 Group 1:  63_HRV24
     64 Group 1:  64_HRV90
     65 Group 1:  65_HRV90a|
     66 Group 1:  66_HRV90b|
     67 Group 1:  67_HRV34
     68 Group 1:  68_HRV34b|
     69 Group 1:  69_HRV34a|
     70 Group 1:  70_HRV50a|
     71 Group 1:  71_HRV50b|
     72 Group 1:  72_HRV50
     73 Group 1:  73_HRV18a|
     74 Group 1:  74_HRV18b|
     75 Group 1:  75_HRV18
     76 Group 1:  76_HRV55
     77 Group 1:  77_HRV55b|
     78 Group 1:  78_HRV55a|
     79 Group 1:  79_HRV57
     80 Group 1:  80_HRV57a|
     81 Group 1:  81_HRV57b|
     82 Group 1:  82_HRV21
     83 Group 1:  83_HRVHan
     84 Group 1:  84_HRV43
     85 Group 1:  85_HRV43b|
     86 Group 1:  86_HRV43a|
     87 Group 1:  87_HRV75
     88 Group 1:  88_HRV75b|
     89 Group 1:  89_HRV75a|
     90 Group 1:  96_HRV9a|d
     91 Group 1:  97_HRV9b|d
     92 Group 1:  98_HRV9
     93 Group 1:  99_HRV32
     94 Group 1: 100_HRV32a
     95 Group 1: 101_HRV32b
     96 Group 1: 102_HRV67
     97 Group 1: 103_HRV67a
     98 Group 1: 104_HRV67b
     99 Group 1: 105_HRV15
    100 Group 1: 106_HRV15a
    101 Group 1: 107_HRV15b
    102 Group 1: 108_HRV74a
    103 Group 1: 109_HRV74b
    104 Group 1: 110_HRV74
    105 Group 1: 111_HRV38a
    106 Group 1: 112_HRV38b
    107 Group 1: 113_HRV38
    108 Group 1: 114_HRV60
    109 Group 1: 115_HRV60a
    110 Group 1: 116_HRV60b
    111 Group 1: 117_HRV64a
    112 Group 1: 118_HRV64b
    113 Group 1: 119_HRV64
    114 Group 1: 120_HRV94a
    115 Group 1: 121_HRV94b
    116 Group 1: 122_HRV94
    117 Group 1: 123_HRV22
    118 Group 1: 124_HRV22a
    119 Group 1: 125_HRV22b
    120 Group 1: 126_HRV82
    121 Group 1: 127_HRV82b
    122 Group 1: 128_HRV82a
    123 Group 1: 129_HRV19
    124 Group 1: 130_HRV19a
    125 Group 1: 131_HRV19b
    126 Group 1: 132_HRV13
    127 Group 1: 133_HRV13a
```

FIG. D11 CONT'D 07.trace                                                                    9/20/2007  5:04 PM

```
128 Group 1: 134_HRV13b
129 Group 1: 135_HRV41
130 Group 1: 136_HRV41a
131 Group 1: 137_HRV41b
132 Group 1: 138_HRV73
133 Group 1: 139_HRV73b
134 Group 1: 140_HRV73a
135 Group 1: 141_HRV61
136 Group 1: 142_HRV61a
137 Group 1: 143_HRV61b
138 Group 1: 144_HRV96
139 Group 1: 145_HRV96b
140 Group 1: 146_HRV96a
141 Group 1: 90_HRV16a|
142 Group 1: 91_HRV16b|
143 Group 1: 92_1AYM_A
144 Group 1: 93_HRV81a|
145 Group 1: 94_HRV81b|
146 Group 1: 95_HRV81
147 Group 1: 147_HRV2
148 Group 1: 148_HRV2a|
149 Group 1: 149_HRV2b|
150 Group 1: 150_HRV49a
151 Group 1: 151_HRV49b
152 Group 1: 152_HRV49
153 Group 1: 153_HRV23a
154 Group 1: 154_HRV23b
155 Group 1: 155_HRV23
156 Group 1: 156_HRV30a
157 Group 1: 157_HRV30b
158 Group 1: 158_HRV30
159 Group 1: 159_HRV7
160 Group 1: 160_HRV7b|
161 Group 1: 161_HRV7a|
162 Group 1: 162_HRV88
163 Group 1: 163_HRV88a
164 Group 1: 164_HRV88b
165 Group 1: 165_HRV36a
166 Group 1: 166_HRV36b
167 Group 1: 167_HRV36
168 Group 1: 168_HRV89a
169 Group 1: 169_HRV89b
170 Group 1: 170_HRV89
171 Group 1: 171_HRV58
172 Group 1: 172_HRV58a
173 Group 1: 173_HRV58b
174 Group 1: 174_HRV12a
175 Group 1: 175_HRV12b
176 Group 1: 176_HRV12
177 Group 1: 177_HRV78a
178 Group 1: 178_HRV78b
179 Group 1: 179_HRV78
180 Group 1: 180_HRV20
181 Group 1: 181_HRV20a
182 Group 1: 182_HRV20b
183 Group 1: 183_HRV68
184 Group 1: 184_HRV68a
185 Group 1: 185_HRV68b
186 Group 1: 186_HRV28
187 Group 1: 187_HRV28a
188 Group 1: 188_HRV28b
189 Group 1: 189_HRV53a
190 Group 1: 190_HRV53b
191 Group 1: 191_HRV53
192 Group 1: 192_HRV46a
```

FIG. D11 CONT'D 07.trace                                                          9/20/2007 5:04 PM

```
193 Group 1: 193_HRV46b
194 Group 1: 194_HRV46
195 Group 1: 195_HRV80a
196 Group 1: 196_HRV80b
197 Group 1: 197_HRV80
198 Group 1: 198_HRV51
199 Group 1: 199_HRV51a
200 Group 1: 200_HRV51b
201 Group 1: 201_HRV65a
202 Group 1: 202_HRV65b
203 Group 1: 203_HRV65
204 Group 1: 204_HRV71a
205 Group 1: 205_HRV71b
206 Group 1: 206_HRV71
207 Group 1: 207_HRV8
208 Group 1: 208_HRV95
209 Group 1: 209_HRV45
210 Group 1: 210_HRV45a
211 Group 1: 211_HRV45b
212
213
214 >>>>>
215
216
217
218 Group 1:
219
220  1_HRV1A1|d    AATCCAGTAGAAAACTACATTGATGAAGTTTTAAATGAAGTTTTAGTAGTGCCGAATATA
221  2_HRV1A2|d    AATCCAGTAGAAAACTACATTGATGAAGTTTTAAATGAAGTTTTAGTAGTGCCGAATATA
222  3_HRV1A|cD    AATCCAGTAGAAAACTACATTGATGAAGTTTTAAATGAAGTTTTAGTAGTGCCGAATATA
223  4_HRV1B1|d    AATCCAGTGGAAAATTACATTGATGAAGTTTTAAATGAAGTTCTAGTAGTACCAAATATA
224  5_HRV1B2|d    AATCCAGTGGAAAATTACATTGATGAAGTTTTAAATGAAGTTCTAGTAGTACCAAATATA
225  6_HRV1B       AATCCAGTGGAAAATTACATTGATGAAGTTTTAAATGAAGTTCTAGTAGTACCAAATATA
226  7_HRV40a|d    AACCCCGTTGAAAGGTATGTTGATGAGGTTCTTAATGAAGTTCTGGTAGTTCCAAATATC
227  8_HRV40b|d    AACCCCGTTGAAAGGTATGTTGATGAGGTTCTTAATGAAGTTCTGGTAGTTCCAAATATC
228  9_HRV40       AACCCCGTTGAAAGGTATGTTGATGAGGTTCTTAATGAAGTTCTGGTAGTTCCAAATATC
229 10_HRV85       AATCCTGTTGAAAAATACGTTGATGAAGTCCTTAATGAGGTTCTAGTGGTTCCAAATATC
230 11_HRV85a|     AATCCTGTTGAAAAATACGTTGATGAAGTCCTTAATGAGGTTCTAGTGGTTCCAAATATC
231 12_HRV85b|     AATCCTGTTGAAAAATACGTTGATGAAGTCCTTAATGAGGTTCTAGTGGTTCCAAATATC
232 13_HRV56a|     AACCCAGTTGAGAGATATGTAGATGATGTTTTAAATGAAGTTTTAGTTGTTCCAAATATT
233 14_HRV56b|     AACCCAGTTGAGAGATATGTAGATGATGTTTTAAATGAAGTTTTAGTTGTTCCAAATATT
234 15_HRV56       AACCCAGTTGAGAGATATGTAGATGATGTTTTAAATGAAGTTTTAGTTGTTCCAAATATT
235 16_HRV54       AATCCTGTAGAAAGATATGTTGATGAAGTGTTAAATGAAGTGTTAGTTGTCCCAAACATT
236 17_HRV98       AATCCTGTAGAGAGATATGTTGATGAAGTGTTAAATGAAGTGTTAGTTGTCCCAAACATT
237 18_HRV59a|     AACCCAGTGGAAAACTATGTTAATGATGTACTTAATGAGGTTTTAGTAGTACCAAATATA
238 19_HRV59b|     AACCCAGTGGAAAACTATGTTAATGATGTACTTAATGAGGTTTTAGTAGTACCAAATATA
239 20_HRV59       AACCCAGTGGAAAACTATGTTAATGATGTACTTAATGAGGTTTTAGTAGTACCAAATATA
240 21_HRV63       AATCCAGTAGAGAATTATGTAAATGATGTTCTTAATGAAGTGTTAGTTGTTCCAAACATA
241 22_HRV63b|     AATCCAGTAGAGAATTATGTAAATGATGTTCTTAATGAAGTGTTAGTTGTTCCAAACATA
242 23_HRV63a|     AATCCAGTAGAGAATTATGTAAATGATGTTCTTAATGAAGTGTTAGTTGTTCCAAACATA
243 24_HRV39       AATCCAGTAGAAAATTATATAGATGAAGTATTAAATGAGGTATTAGTTGTTCCTAATATA
244 25_HRV39a|     AATCCAGTAGAAAATTATATAGATGAAGTATTAAATGAGGTATTAGTTGTTCCTAATATA
245 26_HRV39b|     AATCCAGTAGAAAATTATATAGATGGAGTATTAAATGAGGTATTAGTTGTTCCTAATATA
246 27_HRV10a|     AATCCAGTTGAAAATTACATTGATAATGTACTTAATGAAGTCCTAGTGGTACCCAACATC
247 28_HRV10b|     AATCCAGTTGAAAATTACATTGATAATGTACTTAATGAAGTCCTAGTGGTACCCAACATC
248 29_HRV10       AATCCAGTTGAAAATTACATTGATAATGTACTTAATGAAGTCCTAGTGGTACCCAACATC
249 30_HRV100a     AATCCAGTAGAAAATTATGTTGAAGGTGTGCTGAATGAAGTACTAGTGGTACCTAATATT
250 31_HRV100b     AATCCAGTAGAAAATTATGTTGAAGGTGTGCTGAATGAAGTACTAGTGGTACCTAATATT
251 32_HRV100      AATCCAGTAGAAAATTATGTTGAAGGTGTGCTGAATGAAGTACTAGTGGTACCTAATATT
252 33_HRV66       AATCCAGTTGAAGATTATGTTGAGGGTGTTTTAAATGAAGTTTTAGTAGTACCAAACATC
253 34_HRV66b|     AATCCAGTTGAAGATTATGTTGAGGGTGTTTTAAATGAAGTTTTAGTAGTACCAAACATC
254 35_HRV66a|     AATCCAGTTGAAGATTATGTTGAGGGTGTTTTAAATGAAGTTTTAGTAGTACCAAACATC
255 36_HRV77a|     AATCCAGTTGAGGACTATATCGATAATGTACTTAATGAAGTCTTAGTAGTACCAAATACC
```

FIG. D11 CONT'D

07.trace                                                                 9/20/2007 5:04 PM

```
256  37_HRV77b|   AATCCAGTTGAGGACTATATCGATAATGTACTTAATGAAGTCTTAGTAGTACCAAATACC
257  38_HRV77    AATCCAGTTGAGGACTATATCGATAATGTACTTAATGAAGTCTTAGTAGTACCAAATACC
258  39_HRV62a   AATCCAATTGAAAATTATGTAGATCAAGTACTTAATGAAGTTTTAGTTGTACCAAATATT
259  40_HRV62b   AATCCAATTGAAAATTATGTAGATCAAGTACTTAATGAAGTTTTAGTTGTACCAAATATT
260  41_HRV25    AATCCAATTGAAAATTATGTAGATCAAGTACTTAATGAGGTTCTAGTCGTACCAAATATT
261  42_HRV29a   AACCCAGTTGAAAACTATGTGGATGAGGTGCTTAATGAAGTTTTAGTTGTGCCTAACATC
262  43_HRV29b   AACCCAGTTGAAAACTATGTGGATGAGGTGCTTAATGAAGTTTTAGTTGTGCCTAACATC
263  44_HRV44a   AACCCAGTTGAAAATTATGTGGATGAAGTACTTAATGAAGTCTTAGTTGTGCCTAATATC
264  45_HRV44b   AACCCAGTTGAAAATTATGTGGATGAAGTACTTAATGAAGTCTTAGTTGTGCCTAATATC
265  46_HRV31    AATCCAGTTGAAAACTATGTGGAAGAGGTTCTTAATGAAGTCTTAGTAGTACCTAATATC
266  47_HRV31a|  AATCCAGTTGAAAACTATGTGGAAGAGGTTCTTAATGAAGTCTTAGTAGTACCTAATATC
267  48_HRV31b|  AATCCAGTTGAAAACTATGTGGAAGAGGTTCTTAATGAAGTCTTAGTAGTACCTAATATC
268  49_HRV47    AACCCAGTCGAAAATTATGTGGAAGAGGTACTTAATGAGGTCTTAGTTGTACCAAATATC
269  50_HRV47a|  AACCCAGTCGAAAATTATGTGGAAGAGGTACTTAATGAGGTCTTAGTTGTACCAAATATC
270  51_HRV47b|  AACCCAGTCGAAAATTATGTGGAAGAGGTACTTAATGAGGTCTTAGTTGTACCAAATATC
271  52_HRV11    AACCCAGTGGAGGATTATGTTGATGGAATTCTAAATGAGGTTTTAGTTGTACCTAATATA
272  53_HRV11b|  AACCCAGTGGAGGATTATGTTGATGGAATTCTAAATGAGGTTTTAGTTGTACCTAATATA
273  54_HRV11a|  AACCCAGTGGAGGATTATGTTGATGGAATTCTAAATGAGGTTTTAGTTGTACCTAATATA
274  55_HRV76    AACCCAGTTGAAAATTACGTGGATGAGATATTAAATGAGGTTCTTGTAGTACCAAACATC
275  56_HRV76b|  AACCCAGTTGAAAATTACGTGGATGAGATATTAAATGAGGTTCTTGTAGTACCAAACATC
276  57_HRV76a|  AACCCAGTTGAAAATTACGTGGATGAGATATTAAATGAGGTTCTTGTAGTACCAAACATC
277  58_HRV33    AATCCAGTAGAGAATTATATAGAAGAGGTGTTGAATGAGGTTTTAGTAGTGCCTAATATC
278  59_HRV33b|  AATCCAGTAGAGAATTATATAGAAGAGGTGTTGAATGAGGTTTTAGTAGTGCCTAATATC
279  60_HRV33a|  AATCCAGTAGAGAATTATATAGAAGAGGTGTTGAATGAGGTTTTAGTAGTGCCTAATATC
280  61_HRV24a|  AACCCAGTAGAAAATTATATAGATGAGGTTTTGAATGAAGTACTGGTTGTGCCTAATATT
281  62_HRV24b|  AACCCAGTAGAAAATTATATAGATGAGGTTTTGAATGAAGTACTGGTTGTGCCTAATATT
282  63_HRV24    AACCCAGTAGAAAATTATATAGATGAGGTTTTGAATGAAGTACTGGTTGTGCCTAATATT
283  64_HRV90    AATCCAGTGGAAAATTATATAGATGAAGTCCTAAATGAGGTATTGGTTGTCCCTAATATT
284  65_HRV90a|  AATCCAGTGGAAAATTATATAGATGAAGTCCTAAATGAGGTATTGGTTGTCCCTAATATT
285  66_HRV90b|  AATCCAGTGGAAAATTATATAGATGAAGTCCTAAATGAGGTATTGGTTGTCCCTAATATT
286  67_HRV34    AATCCAGTTGAAAATTACATAGATGAGGTACTAAATGAGGTATTGGTTGTACCAAACATT
287  68_HRV34b|  AATCCAGTTGAAAATTACATAGATGAGGTACTAAATGAGGTATTGGTTGTACCAAACATT
288  69_HRV34a|  AATCCAGTTGAAAATTACATAGATGAGGTACTAAATGAGGTATTGGTTGTACCAAACATT
289  70_HRV50a|  AATCCAGTGGAGAATTACATAGATGAAGTATTAAATGAGGTATTAGTTGTCCCAAATATC
290  71_HRV50b|  AATCCAGTGGAGAATTACATAGATGAAGTATTAAATGAGGTATTAGTTGTCCCAAATATC
291  72_HRV50    AATCCAGTGGAGAATTACATAGATGAAGTATTAAATGAGGTATTAGTTGTCCCAAATATC
292  73_HRV18a|  AATCCAGTAGAGAATTATATAGATGAAGTACTTAATGAAGTGTTAGTGGTCCCAAATGTG
293  74_HRV18b|  AATCCAGTAGAGAATTATATAGATGAAGTACTTAATGAAGTGTTAGTGGTCCCAAATGTG
294  75_HRV18    AATCCAGTAGAGAATTATATAGATGAAGTACTTAATGAAGTGTTAGTGGTCCCAAATGTG
295  76_HRV55    AATCCTGTAGAGAGATATGTTGATGAAGTCCTGAATGAAGTGCTAGTAGTTCCAAATATT
296  77_HRV55b|  AATCCTGTAGAGAGATATGTTGATGAAGTCCTGAATGAAGTGCTAGTAGTTCCAAATATT
297  78_HRV55a|  AATCCTGTAGAGAGATATGTTGATGAAGTCCTGAATGAAGTGCTAGTAGTTCCAAATATT
298  79_HRV57    AACCCAGTAGAAAATTTTGTGGATGAGATCTTGAATGAAGTTTTGGTGGTTCCAGATATC
299  80_HRV57a|  AACCCAGTAGAAAATTTTGTGGATGAGATCTTGAATGAAGTTTTGGTGGTTCCAGATATC
300  81_HRV57b|  AACCCAGTAGAAAATTTTGTGGATGAGATCTTGAATGAAGTTTTGGTGGTTCCAGATATC
301  82_HRV21    AATCCTGTAGAGAATTATATAGATGAGGTCCTAAATGAAGTCTTAGTAGTGCCAAATATC
302  83_HRVHan   AATCCTGTAGAGAATTACGTAGATGAAGTTCTAAATGAGGTCTTAGTAGTGCCAAATATC
303  84_HRV43    AATCCTGTTGAAAATTATGTTGATGAAATTTAAATCAAGTTCTTGTAGTCCCAAACACT
304  85_HRV43b|  AATCCTGTTGAAAATTATGTTGATGAAATTTAAATCAAGTTCTTGTAGTCCCAAACACT
305  86_HRV43a|  AATCCTGTTGAAAATTATGTTGATGAAATTTAAATCAAGTTCTTGTAGTCCCAAACACT
306  87_HRV75    AATCCAGTTGAAAATTATGTGGATGAAATTTTAAACCAAGTTCTGGTAGTTCCAAACACC
307  88_HRV75b|  AATCCAGTTGAAAATTATGTGGATGAAATTTTAAACCAAGTTCTGGTAGTTCCAAACACC
308  89_HRV75a|  AATCCAGTTGAAAATTATGTGGATGAAATTTTAAACCAAGTTCTGGTAGTTCCAAACACC
309  96_HRV9a|d  AATCCAGTGGAGAATTACATAGATCAGGTGCTTAATGAGGTTTTGGTAGTCCCAAACATT
310  97_HRV9b|d  AATCCAGTGGAGAATTACATAGATCAGGTGCTTAATGAGGTTTTGGTAGTCCCAAACATT
311  98_HRV9     AATCCAGTGGAGAATTACATAGATCAGGTGCTTAATGAGGTTTTGGTAGTCCCAAACATT
312  99_HRV32    AATCCTGTGGAGAATTACATAGATCAAGTTTTAAATGAAGTTTTGGTAGTTCCAAACATC
313  100_HRV32a  AATCCTGTGGAGAATTACATAGATCAAGTTTTAAATGAAGTTTTGGTAGTTCCAAACATC
314  101_HRV32b  AATCCTGTGGAGAATTACATAGATCAAGTTTTAAATGAAGTTTTGGTAGTTCCAAACATC
315  102_HRV67   AACCCAGTAGAAGATTATGTAGATCAGGTATTGAATGAGGTCCTGGTGGTGCCAAATATA
316  103_HRV67a  AACCCAGTAGAAGATTATGTAGATCAGGTATTGAATGAGGTCCTGGTGGTGCCAAATATA
317  104_HRV67b  AACCCAGTAGAAGATTATGTAGATCAGGTATTGAATGAGGTCCTGGTGGTGCCAAATATA
318  105_HRV15   AACCCAGTGGAGAATTACATAGATGAAGTGTTAAATGAGGTTCTAGTAGTTCCAAACATT
319  106_HRV15a  AACCCAGTGGAGAATTACATAGATGAAGTGTTAAATGAGGTTCTAGTAGTTCCAAACATT
320  107_HRV15b  AACCCAGTGGAGAATTACATAGATGAAGTGTTAAATGAGGTTCTAGTAGTTCCAAACATT
```

FIG. D11 CONT'D 07.trace                                                                                    9/20/2007 5:04 PM

```
321  108_HRV74a     AACCCAGTGGAGAATTACATAGATGAAGTGTTGAATGAAGTGTTAGTTGTTCCAAATATT
322  109_HRV74b     AACCCAGTGGAGAATTACATAGATGAAGTGTTGAATGAAGTGTTAGTTGTTCCAAATATT
323  110_HRV74      AACCCAGTGGAGAATTACATAGATGAAGTGTTGAATGAAGTGTTAGTTGTTCCAAATATT
324  111_HRV38a     AACCCAGTAGAGGAATACATAGATGGAGTCTTGAATGAGGTTCTTGTGGTTCCGAACATT
325  112_HRV38b     AACCCAGTAGAGGAATACATAGATGGAGTCTTGAATGAGGTTCTTGTGGTTCCGAACATT
326  113_HRV38      AACCCAGTAGAGGAATACATAGATGGAGTCTTGAATGAGGTTCTTGTGGTTCCGAACATT
327  114_HRV60      AATCCAGTAGAAAGCTACATAGATGGGGTCTTAAACGAAGTCCTTGTGGTTCCAAACATT
328  115_HRV60a     AATCCAGTAGAAAGCTACATAGATGGGGTCTTAAACGAAGTCCTTGTGGTTCCAAACATT
329  116_HRV60b     AATCCAGTAGAAAGCTACATAGATGGGGTCTTAAACGAAGTCCTTGTGGTTCCAAACATT
330  117_HRV64a     AACCCAGTTGAACAATACATTGATGGTGTGTTGAATGAAGTTTTGATTGTCCCAAACATC
331  118_HRV64b     AACCCAGTTGAACAATACATTGATGGTGTGTTGAATGAAGTTTTGATTGTCCCAAACATC
332  119_HRV64      AACCCAGTTGAACAATACATTGATGGTGTGTTGAATGAAGTTTTGATTGTCCCAAACATC
333  120_HRV94a     AATCCAGTTGAGAAATACATTGATGGTGTATTGAATGAAGTTTTAGTTGTTCCAAATATC
334  121_HRV94b     AATCCAGTTGAGAAATACATTGATGGTGTATTGAATGAAGTTTTAGTTGTTCCAAATATC
335  122_HRV94      AATCCAGTTGAGAAATACATTGATGGTGTATTGAATGAAGTTTTAGTTGTTCCAAATATC
336  123_HRV22      AACCCTGTAGAGAAATACATTGATGGTGTATTGAATGAAGTATTGGTTGTTCCAAACACA
337  124_HRV22a     AACCCTGTAGAGAAATACATTGATGGTGTATTGAATGAAGTATTGGTTGTTCCAAACACA
338  125_HRV22b     AACCCTGTAGAGAAATACATTGATGGTGTATTGAATGAAGTATTGGTTGTTCCAAACACA
339  126_HRV82      AATCCAGTTGAAAAGTATGTTGATAGTGTTTTAAACGAGGTATTAGTTGTTCCTAACATT
340  127_HRV82b     AATCCAGTTGAAAAGTATGTTGATAGTGTTTTAAACGAGGTATTAGTTGTTCCTAACATT
341  128_HRV82a     AATCCAGTTGAAAAGTATGTTGATAGTGTTTTAAACGAGGTATTAGTTGTTCCTAACATT
342  129_HRV19      AATCCTGTAGAGAAATATGTGGACACCATTCTGAATGAGGTGCTAGTTGTCCCAAATATC
343  130_HRV19a     AATCCTGTAGAGAAATATGTGGACACCATTCTGAATGAGGTGCTAGTTGTCCCAAATATC
344  131_HRV19b     AATCCTGTAGAGAAATATGTGGACACCATTCTGAATGAGGTGCTAGTTGTCCCAAATATC
345  132_HRV13      AATCCTGTTGAAAGGTATGTAGATGAAGTCTTGAATGAAGTTCTTGTAGTACCAAATATC
346  133_HRV13a     AATCCTGTTGAAAGGTATGTAGATGAAGTCTTGAATGAAGTTCTTGTAGTACCAAATATC
347  134_HRV13b     AATCCTGTTGAAAGGTATGTAGATGAAGTCTTGAATGAAGTTCTTGTAGTACCAAATATC
348  135_HRV41      AATCCTGTAGAAAGGTATGTGGATGAGGTCCTGAATGAGGTTCTTGTGGTACCAAATATT
349  136_HRV41a     AATCCTGTAGAAAGGTATGTGGATGAGGTCCTGAATGAGGTTCTTGTGGTACCAAATATT
350  137_HRV41b     AATCCTGTAGAAAGGTATGTGGATGAGGTCCTGAATGAGGTTCTTGTGGTACCAAATATT
351  138_HRV73      AATCCTGTAGAAAGATATGTAGATGAAGTTTTGAATGAAGTCCTTGTAGTACCCAATATC
352  139_HRV73b     AATCCTGTAGAAAGATATGTAGATGAAGTTTTGAATGAAGTCCTTGTAGTACCCAATATC
353  140_HRV73a     AATCCTGTAGAAAGATATGTAGATGAAGTTTTGAATGAAGTCCTTGTAGTACCCAATATC
354  141_HRV61      AACCCTGTGGAAAGATATGTAGATGAAGTTTTAAATGAAGTGCTTGTAGTCCCAAACATT
355  142_HRV61a     AACCCTGTGGAAAGATATGTAGATGAAGTTTTAAATGAAGTGCTTGTAGTCCCAAACATT
356  143_HRV61b     AACCCTGTGGAAAGATATGTAGATGAAGTTTTAAATGAAGTGCTTGTAGTCCCAAACATT
357  144_HRV96      AACCCTGTAGAGAGATATGTAGATGAAGTCTTGAATGAGGTTCTTGTAGTCCCTAATATT
358  145_HRV96b     AACCCTGTAGAGAGATATGTAGATGAAGTCTTGTGTGAGGTTCTTGTAGTCCCTAATATT
359  146_HRV96a     AACCCTGTAGAGAGATATGTAGATGAAGTCTTGAATGAGGTTCTTGTAGTCCCTAATATT
360  90_HRV16a|     AATCCAGTGGAAAGATATGTAGATGAAGTCTTAAATGAAGTGTTAGTAGTGCCCAATATT
361  91_HRV16b|     AATCCAGTGGAAAGATATGTAGATGAAGTCTTAAATGAAGTGTTAGTAGTGCCCAATATT
362  92_1AYM_A      AATCCAGTGGAAAGATATGTAGATGAAGTCTTAAATGAAGTGTTAGTAGTGCCCAATATT
363  93_HRV81a|     AACCCAGTGGAGCGGTATGTGGATGAAGTCTTAAATGAGGTATTGGTAGTCCCTAATATT
364  94_HRV81b|     AACCCAGTGGAGCGGTATGTGGATGAAGTCTTAAATGAGGTATTGGTAGTCCCTAATATT
365  95_HRV81       AACCCAGTGGAGCGGTATGTGGATGAAGTCTTAAATGAGGTATTGGTAGTCCCTAATATT
366  147_HRV2       AACCCTGTTGAGAATTATATAGATGAAGTTCTTAATGAAGTTTTAGTTGTCCCAAATATT
367  148_HRV2a|     AACCCTGTTGAGAATTATATAGATGAAGTTCTTAATGAAGTTTTAGTTGTCCCAAATATT
368  149_HRV2b|     AACCCTGTTGAGAATTATATAGATGAAGTTCTTAATGAAGTTTTAGTTGTCCCAAATATT
369  150_HRV49a     AATCCTGTTGAACACTACATAGATGAGGTCCTTAATGAGGTTTTAGTTGTCCAAATATT
370  151_HRV49b     AATCCTGTTGAACACTACATAGATGAGGTCCTTAATGAGGTTTTAGTTGTTCCAAATATT
371  152_HRV49      AATCCTGTTGAACACTACATAGATGAGGTCCTTAATGAGGTTTTAGTTGTTCCAAATATT
372  153_HRV23a     AATCCAATTGAGAACTATGTAGATGAAGTTCTTAATGAAGTCTTAGTTGTTCCCAATATC
373  154_HRV23b     AATCCAATTGAGAACTATGTAGATGAAGTTCTTAATGAAGTCTTAGTTGTTCCCAATATC
374  155_HRV23      AATCCAATTGAGAACTATGTAGATGAAGTTCTTAATGAAGTCTTAGTTGTTCCCAATATC
375  156_HRV30a     AACCCGGTTGAAAATTTTGTAGATGAAGTTCTTAGTGAAGTTTTAGTTGTTCCAAACATT
376  157_HRV30b     AACCCGGTTGAAAATTTTGTAGATGAAGTTCTTAGTGAAGTTTTAGTTGTTCCAAACATT
377  158_HRV30      AACCCGGTTGAAAATTTTGTAGATGAAGTTCTTAGTGAAGTTTTAGTTGTTCCAAACATT
378  159_HRV7       AACCCGGTAGAGAATTATGTAGATAGCTTACTAAATGAAGTATTAGTGGTACCTAATATT
379  160_HRV7b|     AACCCGGTAGAGAATTATGTAGATAGCTTACTAAATGAAGTATTAGTGGTACCTAATATT
380  161_HRV7a|     AACCCGGTAGAGAATTATGTAGATAGCTTACTAAATGAAGTATTAGTGGTACCTAATATT
381  162_HRV88      AATCCAGTAGAAACTATGTAGATAACTTGTTAAACGAAGTGCTAGTAGTTCCTAACATT
382  163_HRV88a     AATCCAGTAGAAAACTATGTAGATAACTTGTTAAACGAAGTGCTAGTAGTTCCTAACATT
383  164_HRV88b     AATCCAGTAGAAAACTATGTAGATAACTTGTTAAACGAAGTGCTAGTAGTTCCTAACATT
384  165_HRV36a     AATCCAGTTGAAAATTACATAGATAATGTATTAAATGAAGTACTTGTAGTGCCAAACATC
385  166_HRV36b     AATCCAGTTGAAAATTACATAGATAATGTATTAAATGAAGTACTTGTAGTGCCAAACATC
```

FIG. D11 CONT'D

```
07.trace                                                                                          9/20/2007 5:04 PM 386 167_HRV36    AATCCAGTTGAAAATTACATAGATAATGTATTAAATGAAGTACTTGTAGTGCCAAACATC
387 168_HRV89a   AACCCAGTTGAAAATTATATAGATAGTGTATTAAATGAAGTTCTTGTGGTGCCAAATATC
388 169_HRV89b   AACCCAGTTGAAAATTATATAGATAGTGTATTAAATGAAGTTCTTGTGGTGCCAAATATC
389 170_HRV89    AACCCAGTTGAAAATTATATAGATAGTGTATTAAATGAAGTTCTTGTGGTGCCAAATATC
390 171_HRV58    AATCCAGTAGAAAATTACATAGATAATGTGTTAAATGAAGTACTTGTAGTTCCAAATATC
391 172_HRV58a   AATCCAGTAGAAAATTACATAGATAATGTGTTAAATGAAGTACTTGTAGTTCCAAATATC
392 173_HRV58b   AATCCAGTAGAAAATTACATAGATAATGTGTTAAATGAAGTACTTGTAGTTCCAAATATC
393 174_HRV12a   AATCCAGTAGAGAGATATGTTGATGAGGTGCTAAATGAAGTTCTAGTTGTTCCAAACATA
394 175_HRV12b   AATCCAGTAGAGAGATATGTTGATGAGGTGCTAAATGAAGTTCTAGTTGTTCCAAACATA
395 176_HRV12    AATCCAGTAGAGAGATATGTTGATGAGGTGCTAAATGAAGTTCTAGTTGTTCCAAACATA
396 177_HRV78a   AATCCAGTGGAAGAATATGTTGATCAGGTTTTAAATGAGGTTTTAGTTGTTCCAAACATA
397 178_HRV78b   AATCCAGTGGAAGAATATGTTGATCAGGTTTTAAATGAGGTTTTAGTTGTTCCAAACATA
398 179_HRV78    AATCCAGTGGAAGAATATGTTGATCAGGTTTTAAATGAGGTTTTAGTTGTTCCAAACATA
399 180_HRV20    AACCCAGTGGAAAGGTACACAGAAGCTATTTTAAATGAAGTTCTTGTAGTTCCAAATATC
400 181_HRV20a   AACCCAGTGGAAAGGTACACAGAAGCTATTTTAAATGAAGTTCTTGTAGTTCCAAATATC
401 182_HRV20b   AACCCAGTGGAAAGGTACACAGAAGCTATTTTAAATGAAGTTCTTGTAGTTCCAAATATC
402 183_HRV68    AACCCAGTTGAAAAATACACAGAAGCCGTTCTTAATGAGGTCCTTGTGGTTCCAAACATA
403 184_HRV68a   AACCCAGTTGAAAAATACACAGAAGCCGTTCTTAATGAGGTCCTTGTGGTTCCAAACATA
404 185_HRV68b   AACCCAGTTGAAAAATACACAGAAGCCGTTCTTAATGAGGTCCTTGTGGTTCCAAACATA
405 186_HRV28    AATCCAGTTGAAAATATACTGAAGCACTACTTAATGAAGTGCTTGTTGTGCCAAACATC
406 187_HRV28a   AATCCAGTTGAAAATATACTGAAGCACTACTTAATGAAGTGCTTGTTGTGCCAAACATC
407 188_HRV28b   AATCCAGTTGAAAATATACTGAAGCACTACTTAATGAAGTGCTTGTTGTGCCAAACATC
408 189_HRV53a   AACCCGGTAGAGAAATACACAGAGGCTATCTTAAATGAAGTATTAGTAGTCCCAAACATT
409 190_HRV53b   AACCCGGTAGAGAAATACACAGAGGCTATCTTAAATGAAGTATTAGTAGTCCCAAACATT
410 191_HRV53    AACCCGGTAGAGAAATACACAGAGGCTATCTTAAATGAAGTATTAGTAGTCCCAAACATT
411 192_HRV46a   AATCCAGTGGAAAATATACAGAAGCTGTTCTTAATGAGGTCCTTGTAGTACCTAACATC
412 193_HRV46b   AATCCAGTGGAAAATATACAGAAGCTGTTCTTAATGAGGTCCTTGTAGTACCTAACATC
413 194_HRV46    AATCCAGTGGAAAATATACAGAAGCTGTTCTTAATGAGGTCCTTGTAGTACCTAACATC
414 195_HRV80a   AATCCAGTCGAAAATACACAGAAGCAATCCTCAATGAAGTTCTTGTTGTACCAAACATC
415 196_HRV80b   AATCCAGTCGAAAATACACAGAAGCAATCCTCAATGAAGTTCTTGTTGTACCAAACATC
416 197_HRV80    AATCCAGTCGAAAATACACAGAAGCAATCCTCAATGAAGTTCTTGTTGTACCAAACATC
417 198_HRV51    AACCCTGTTGAAAAATATACAGAGGCTTTACTCAATGAAGTGTTGGTGGTTCCCAACATA
418 199_HRV51a   AACCCTGTTGAAAAATATACAGAGGCTTTACTCAATGAAGTGTTGGTGGTTCCCAACATA
419 200_HRV51b   AACCCTGTTGAAAAATATACAGAGGCTTTACTCAATGAAGTGTTGGTGGTTCCCAACATA
420 201_HRV65a   AATCCAATTGAGAAGTATACAGAAGCTCTACTTAATGAAGTGTTGGTGGTCCCAAATATA
421 202_HRV65b   AATCCAATTGAGAAGTATACAGAAGCTCTACTTAATGAAGTGTTGGTGGTCCCAAATATA
422 203_HRV65    AATCCAATTGAGAAGTATACAGAAGCTCTACTTAATGAAGTGTTGGTGGTCCCAAATATA
423 204_HRV71a   AATCCTGTAGAAAAATATACAGAAGCAATACTCAATGAGGTTCTAGTTGTGCCAAATATA
424 205_HRV71b   AATCCTGTAGAAAAATATACAGAAGCAATACTCAATGAGGTTCTAGTTGTGCCAAATATA
425 206_HRV71    AATCCTGTAGAAAAATATACAGAAGCAATACTCAATGAGGTTCTAGTTGTGCCAAATATA
426 207_HRV8     AACCCTATTGAACAATTCACAGAGGCAGTATTAAACGAGGTTCTTGTAGTTCCAAACACA
427 208_HRV95    AACCCTATTGAACAATTCACAGAGGCAGTATTAAACGAGGTTCTTGTAGTTCCAAATACA
428 209_HRV45    AACCCTGTTGAACAATTTGCAGAAGCAGTCCTTGATCAAGTATTAGTAGTTCCAAACACT
429 210_HRV45a   AACCCTGTTGAACAATTTGCAGAAGCAGTCCTTGATCAAGTATTAGTAGTTCCAAACACT
430 211_HRV45b   AACCCTGTTGAACAATTTGCAGAAGCAGTCCTTGATCAAGTATTAGTAGTTCCAAACACT
431 GROUP_1      AA-CC--T-GA----T------A-----T--T-----A-GT--T--T-GT-CC--A----
432
433 1_HRV1A1|d   AAAGAAAGTCATCACACTACATCAAACTCTGCCCCACTTTTAGATGCTGCAGAGACGGGA
434 2_HRV1A2|d   AAAGAAAGTCATCACACTACATCAAACTCTGCCCCACTTTTAGATGCTGCAGAGACGGGA
435 3_HRV1A|cD   AAAGAAAGTCATCACACTACATCAAACTCTGCCCCACTTTTAGATGCTGCAGAGACGGGA
436 4_HRV1B1|d   AAAGAAAGCCATCACACTACATCAAATTCTGCTCCACTCTTGGATGCTGCAGAGACAGGA
437 5_HRV1B2|d   AAAGAAAGCCATCACACTACATCAAATTCTGCTCCACTCTTGGATGCTGCAGAGACAGGA
438 6_HRV1B      AAAGAAAGCCATCACACTACATCAAATTCTGCTCCACTCTTGGATGCTGCAGAGACAGGA
439 7_HRV40a|d   AGAGAGAGCCATCCAACTACATCAAATTCGGCCCCTGCCTTGGATGCAGCAGAGACTGGA
440 8_HRV40b|d   AGAGAGAGCCATCCAACTACATCAAATTCGGCCCCTGCCTTGGATGCAGCAGAGACAGGA
441 9_HRV40      AGAGAGAGCCATCCAACTACATCAAATTCGGCCCCTGCCTTGGATGCAGCAGAGACTGGA
442 10_HRV85     AAAGAGAGTCACCCAACTATATCAAATTCAGCTCCTGCTTTGGATGCAGCAGAGACTGGC
443 11_HRV85a|   AAAGAGAGTCACCCAACTATATCAAATTCAGCTCCTGCTTTGGATGCAGCAGAGACTGGC
444 12_HRV85b|   AAAGAGAGTCACCCAACTATATCAAATTCAGCTCCTGCTTTGGATGCAGCAGAGACTGGC
445 13_HRV56a|   AGGGAGAGCCATCCATCCACATCAAATTCTGCCCCTGCATTAGATGCTGCTGAAACTGGC
446 14_HRV56b|   AGGGAGAGCCATCCATCCACATCAAATTCTGCCCCTGCATTAGATGCTGCTGAAACTGGC
447 15_HRV56     AGGGAGAGCCATCCATCCACATCAAATTCTGCCCCTGCATTAGATGCTGCTGAAACTGGC
448 16_HRV54     AGAGAAAGTCATCCAGCTACATCTAATTCAGCCCCTGCGCTAGATGCGGCAGAAACTGGA
449 17_HRV98     AAAGAAAGTCATCCAGCTACATCTAATTCGGCCCCTACACTAGATGCAGCAGAAACTGGG
450 18_HRV59a|   CAGGAAAGCCACCCAACCACCTCAAATGCTGCTCCAGCATTAGATGCAGCAGAGACTGGA
```

FIG. D11 CONT'D

07.trace                                                                              9/20/2007 5:04 PM

```
451  19_HRV59b|   CAGGAAAGCCACCCAACCACCTCAAATGCTGCTCCAGCATTAGATGCAGCAGAGACTGGA
452  20_HRV59    CAGGAAAGCCACCCAACCACCTCAAATGCTGCTCCAGCATTAGATGCAGCAGAGACTGGA
453  21_HRV63    CAAGAAAGCCATCCAACCACATCAAACGCTGCTCCTGTACTTGATGCTGCGGAAACAGGA
454  22_HRV63b|  CAAGAAAGCCATCCAACCACATCAAACGCTGCTCCTGTACTTGATGCTGCGGAAACAGGA
455  23_HRV63a|  CAAGAAAGCCATCCAACCACATCAAACGCTGCTCCTGTACTTGATGCTGCGGAAACAGGA
456  24_HRV39    AGAGAGAGCCATCCAACTACATCTAATGCAGCTACAGCTTTGGATGCTGCTGAAACTGGA
457  25_HRV39a|  AGAGAGAGCCATCCAACTACATCTAATGCAGCTACAGCTTTGGATGCTGCTGAAACTGGA
458  26_HRV39b|  AGAGAGAGCCATCCAACTACATCTAATGCAGCTCCAGCTTTGGATGCTGCTGAAACTGGA
459  27_HRV10a|  AGAGAAAGTCATCCAAGCACCTCTAACTCTGCCCCAATTCTCGATGCAGCTGAGACTGGT
460  28_HRV10b|  AGAGAAAGTCATCCAAGCACCTCTAACTCTGCCCCAATTCTCGATGCAGCTGAGACTGGT
461  29_HRV10    AGAGAAAGTCATCCAAGCACCTCTAACTCTGCCCCAATTCTCGATGCAGCTGAGACTGGT
462  30_HRV100a  AGAGAGAGCCATCCAAGCACCTCAAACTCTGCTCCAATCCTTGATGCTGCTGAAACTGGC
463  31_HRV100b  AGAGAGAGCCATCCAAGCACCTCAAACTCTGCTCCAATCCTTGATGCTGCTGAAACTGGC
464  32_HRV100   AGAGAGAGCCATCCAAGCACCTCAAACTCTGCTCCAATCCTTGATGCTGCTGAAACTGGC
465  33_HRV66    AAGGAAAGCCATCCAAGCACATCAAATGCTGCCCCAATACTAGATGCAGCTGAAACAGGT
466  34_HRV66b|  AAGGAAAGCCATCCAAGCACATCAAATGCTGCCCCAATACTAGATGCAGCTGAAACAGGT
467  35_HRV66a|  AAGGAAAGCCATCCAAGCACATCAAATGCTGCCCCAATACTAGATGCAGCTGAAACAGGT
468  36_HRV77a|  AAGGAGAGTCATCCAAGCACTTCTAACTCTGCTCCTATACTAGATGCAGCTGAAACAGGC
469  37_HRV77b|  AAGGAGAGTCATCCAAGCACTTCTAACTCTGCTCCTATACTAGATGCAGCTGAAACAGGC
470  38_HRV77    AAGGAGAGTCATCCAAGCACTTCTAACTCTGCTCCTATACTAGATGCAGCTGAAACAGGC
471  39_HRV62a   AAAGAAAGTCACCCTAGTACGTCAAACTCTGCCCCAATTCTAGATGCTGCTGAAACCGGA
472  40_HRV62b   AAAGAAAGTCACCCTAGTACGTCAAACTCTGCCCCAATTCTAGATGCTGCTGAAACCGGA
473  41_HRV25    AAAGAAAGTCACCCAAGCACATCAAATTCTGCCCCAATTCTAGATGCTGCTGAAACTGGA
474  42_HRV29a   AGGGAGAGCCACCCAAGCACGTCCAACTCTGCACCAATCTTGGATGCTGCTGAGACTGGA
475  43_HRV29b   AGGGAGAGCCACCCAAGCACGTCCAACTCTGCACCAATCTTGGATGCTGCTGAGACTGGA
476  44_HRV44a   AGAGAGAGCCACCCAAGCACATCTAACTCTGCTCCAATTTTGGATGCTGCTGAAACTGGA
477  45_HRV44b   AGAGAGAGCCACCCAAGCATATCTAACTCTGCTCCAATTTTGGATGCTGCTGAAACTGGA
478  46_HRV31    AAAGAAAGCCATCCAAGCACATCTAATTCTGCCCCAATCCTGGACGCTGCTGAAACTGGA
479  47_HRV31a|  AAAGAAAGCCATCCAAGCACATCTAATTCTGCCCCAATCCTGGACGCTGCTGAAACTGGA
480  48_HRV31b|  AAAGAAAGCCATCCAAGCACATCTAATTCTGCCCCAATCCTGGACGCTGCTGAAACTGGA
481  49_HRV47    AAAGAAAGTCATCCAAGCACATCCAACTCTGCCCCGATTTTAGATGCTGCTGAAACTGGA
482  50_HRV47a|  AAAGAAAGTCATCCAAGTACATCCAACTCTGCCCCGATTTTAGATGCTGCTGAAACTGGA
483  51_HRV47b|  AAAGAAAGTCATCCAAGTACATCCAACTCTGCCCCGATTTTAGATGCTGCTGAAACTGGA
484  52_HRV11    AAGGAGAGCCAAGCTACCACATCAAACTCAGCACCTGCTCTAGATGCAGCTGAAACCGGA
485  53_HRV11b|  AAGGAGAGCCAAGCTACCACATCAAACTCAGCACCTGCTCTAGATGCAGCTGAAACCGGA
486  54_HRV11a|  AAGGAGAGCCAAGCTACCACATCAAACTCAGCACCTGCTCTAGATGCAGCTGAAACCGGA
487  55_HRV76    AAAGAGAGTCAGGCTACCACATCAAATGCAGCACCTGCTTTGGATGCAGCTGAGACTGGG
488  56_HRV76b|  AAAGAGAGTCAGGCTACCACATCAAATGCAGCACCTGCTTTTGGATGCAGCTGAGACTGGG
489  57_HRV76a|  AAAGAGAGTCAGGCTACCACATCAAATGCAGCACCTGCTTTGGATGCAGCTGAGACTGGG
490  58_HRV33    AGAGAGAGTCAAGCAACCACATCAAATTCAGCACCTGCCTTAGATGCAGCTGAGACTGGA
491  59_HRV33b|  AGAGAGAGTCAAGCAACCACATCAAATTCAGCACCTGCCTTAGATGCAGCTGAGACTGGA
492  60_HRV33a|  AGAGAGAGTCAAGCAACCACATCAAATTCAGCACCTGCCTTAGATGCAGCTGAGACTGGA
493  61_HRV24a|  AAGGAAAGTAAACCATCAACATCAAACTCAGCACCAGCTTTGGATGCAGCAGAAACTGGA
494  62_HRV24b|  AAGGAAAGTAAACCATCAACATCAAACTCAGCACCAGCTTTGGATGCAGCAGAAACTGGA
495  63_HRV24    AAGGAAAGTAAACCATCAACATCAAACTCAGCACCAGCTTTGGATGCAGCAGAAACTGGA
496  64_HRV90    AAGGAAAGTAAACCTTCAACTTCAAACTCAGCGCCAGCTTTAGATGCAGCAGAAACCGGA
497  65_HRV90a|  AAGGAAAGTAAACCTTCAACTTCAAACTCAGCGCCAGCTTTAGATGCAGCAGAAACCGGA
498  66_HRV90b|  AAGGAAAGTAAACCTTCAACTTCAAACTCAGCGCCAGCTTTAGATGCAGCAGAAACCGGA
499  67_HRV34    AAAGAAAGCCAAGCCACCACATCAAACTCTGCCCCCGCACTGGATGCAGCTGAGACTGGT
500  68_HRV34b|  AAAGAAAGCCAAGCCACCACATCAAACTCTGCCCCCGCACTGGATGCAGCTGAGACTGGT
501  69_HRV34a|  AAAGAAAGCCAAGCCACCACATCAAACTCTGCCCCCGCACTGGATGCAGCTGAGACTGGT
502  70_HRV50a|  AAGGAGAGTCAAGCCACTACATCAAACTCTGCCCCTGCTTTAGATGCAGCTGAAACTGGA
503  71_HRV50b|  AAGGAGAGTCAAGCCACTACATCAAACTCTGCCCCTGCTTTAGATGCAGCTGAAACTGGA
504  72_HRV50    AAGGAGAGTCAAGCCACTACATCAAACTCTGCCCCTGCTTTAGATGCAGCTGAAACTGGA
505  73_HRV18a|  AATGAAAGTCACGCAATTACATCAAATTCAGCCCCTGCTTTAGATGCCGCTGAAACTGGT
506  74_HRV18b|  AATGAAAGTCACGCAATTACATCAAATTCAGCCCCTGCTTTAGATGCCGCTGAAACTGGT
507  75_HRV18    AATGAAAGTCACGCAATTACATCAAATTCAGCCCCTGCTTTAGATGCCGCTGAAACTGGT
508  76_HRV55    AGGGAGAGTCAAGCAGCAACATCAAATTCAGCTCCAGTACTAGATGCAGCAGAACTGGG
509  77_HRV55b|  AGGGAGAGTCAAGCAGCAACATCAAATTCAGCTCCAGTACTAGATGCAGCAGAAACTGGG
510  78_HRV55a|  AGGGAGAGTCAAGCAGCAACATCAAATTCAGCTCCAGTACTAGATGCAGCAGAAACTGGG
511  79_HRV57    AAACAAAGTCAAGCAACAACATCAAACTCAGCACCTGCATTGGATGCAGCTGAAACTGGA
512  80_HRV57a|  AAACAAAGTCAAGCAACAACATCAAACTCAGCACCTGCATTGGATGCAGCTGAAACTGGA
513  81_HRV57b|  AAACAAAGTCAAGCAACAACATCAAACTCAGCACCTGCATTGGATGCAGCTGAAACTGGA
514  82_HRV21    AGAGAGAGTCATGGAACAACATCAAACTCTGCTCCCGCACTTGATGCTGCAGAAACTGGA
515  83_HRVHan   AGAGAGAGTCATGGAACAACATCAAACTCTGCTCCCGCACTTGATGCTGCAGAAACTGGG
```

FIG. D11 CONT'D

```
07.trace                                                              9/20/2007 5:04 PM 516  84_HRV43     GTAGAAAGTCATTCAACAACATCCAATGCAGCCCCTGCACTTGATGCAGCTGAAACTGGG
517  85_HRV43b|   GTAGAAAGTCATTCAACAACATCCAATGCAGCCCCTGCACTTGATGCAGCTGAAACTGGG
518  86_HRV43a|   GTAGAAAGTCATTCAACAACATCCAATGCAGCCCCTGCACTTGATGCAGCTGAAACTGGG
519  87_HRV75     ATGGAGAGCCATCCAACAACGTCTAATGCTGCTCCAGCTTTAGATGCAGCTGAAACTGGC
520  88_HRV75b|   ATGGAGAGCCATCCAACAACGTCTAATGCTGCTCCAGCTTTAGATGCAGCTGAAACTGGC
521  89_HRV75a|   ATGGAGAGCCATCCAACAACGTCTAATGCTGCTCCAGCTTTAGATGCAGCTGAAACTGGC
522  96_HRV9a|d   AAAGAGAGCAACCCTACAACCTCTAACTCAGCTCCAGCTCTAGATGCTGCTGAGACAGGC
523  97_HRV9b|d   AAAGAGAGCAACCCTACAACCTCTAACTCAGCTCCAGCTCTAGATGCTGCTGAGACAGGC
524  98_HRV9      AAAGAGAGCAACCCTACAACCTCTAACTCAGCTCCAGCTCTAGATGCTGCTGAGACAGGC
525  99_HRV32     AAAGAAAGCAATCCCACAACCTCTAATTCAGCCCCAGCCTTAGATGCTGCCGAAACAGGT
526  100_HRV32a   AAAGAAAGCAATCCCACAACCTCTAATTCAGCCCCAGCCTTAGATGCTGCCGAAACAGGT
527  101_HRV32b   AAAGAAAGCAATCCCACAACCTCTAATTCAGCCCCAGCCTTAGATGCTGCCGAAACAGGT
528  102_HRV67    AAGCAAAGTGAACCCACGACTTCCAATTCAGCCCCAGCTCTAGATGCTGCTGAGACAGGT
529  103_HRV67a   AAGCAAAGTGAACCCACGACTTCCAATTCAGCCCCAGCTCTAGATGCTGCTGAGACAGGT
530  104_HRV67b   AAGCAAAGTGAACCCACGACTTCCAATTCAGCCCCAGCTCTAGATGCTGCTGAGACAGGT
531  105_HRV15    AAGGAGAGTCACTCAAGCACATCCAACTCAGCACCAGCACTAGATGCAGCTGAGACCGGC
532  106_HRV15a   AAGGAGAGTCACTCAAGCACATCCAACTCAGCACCAGCACTAGATGCAGCTGAGACCGGC
533  107_HRV15b   AAGGAGAGTCACTCAAGCACATCCAACTCAGCACCAGCACTAGATGCAGCTGAGACCGGC
534  108_HRV74a   AGAGAAAGCCATTCAAGTACTTCAAACTCAGCACCAGCACTGGATGCAGCTGAAACTGGC
535  109_HRV74b   AGAGAAAGCCATTCAAGTACTTCAAACTCAGCACCAGCACTGGATGCAGCTGAAACTGGC
536  110_HRV74    AGAGAAAGCCATTCAAGTACTTCAAACTCAGCACCAGCACTGGATGCAGCTGAAACTGGC
537  111_HRV38a   AAGGAAAGCCACTCCAGCACATCAAATTCAGCACCAGCATTAGATGCTGCTGAGACTGGA
538  112_HRV38b   AAGGAAAGCCACTCCAGCACATCAAATTCAGCACCAGCATTAGATGCTGCTGAGACTGGA
539  113_HRV38    AAGGAAAGCCACTCCAGCACATCAAATTCAGCACCAGCATTAGATGCTGCTGAGACTGGA
540  114_HRV60    AGGGAGAGCCAACCCACTACTTCTAATTCTGCTCCAGCATTGGATGCTGCTGAGACTGGT
541  115_HRV60a   AGGGAGAGCCAACCCACTACTTCTAATTCTGCTCCAGCATTGGATGCTGCTGAGACTGGT
542  116_HRV60b   AGGGAGAGCCAACCCACTACTTCTAATTCTGCTCCAGCATTGGATGCTGCTGAGACTGGT
543  117_HRV64a   AATGAGAGCCATCCCAGCACTTCCAATGCAGCCAGCTTTAGATGCAGCTGAGACCGGA
544  118_HRV64b   AATGAGAGCCATCCCAGCACTTCCAATGCAGCGCCAGCTTTAGATGCAGCTGAGACCGGA
545  119_HRV64    AATGAGAGCCATCCCAGCACTTCCAATGCAGCGCCAGCTTTAGATGCAGCTGAGACCGGA
546  120_HRV94a   AATGAGAGTCACCCTAGCACATCCAATGCAGCGCCAGCCTTAGATGCTGCCGAAACTGGA
547  121_HRV94b   AATGAGAGTCACCCTAGCACATCCAATGCAGCGCCAGCCTTAGATGCTGCCGAAACTGGA
548  122_HRV94    AATGAGAGTCACCCTAGCACATCCAATGCAGCGCCAGCCTTAGATGCTGCCGAAACTGGA
549  123_HRV22    AATGAAAGTCACCCCAGTACATCAAATGCTGCACCAGCACTAGATGCTGCTGAAACTGGA
550  124_HRV22a   AATGAAAGTCACCCCAGTACATCAAATGCTGCACCAGCACTAGATGCTGCTGAAACTGGA
551  125_HRV22b   AATGAAAGTCACCCCAGTACATCAAATGCTGCACCAGCACTAGATGCTGCTGAAACTGGA
552  126_HRV82    AATGAAAGTCATCCTAGTACTTCAAATTCAGCTCCTGCCTTGGACGCTGCAGAGACAGGA
553  127_HRV82b   AATGAAAGTCATCCTAGTACTTCAAATTCAGCTCCTGCCTTGGACGCTGCAGAGACAGGA
554  128_HRV82a   AATGAAAGTCATCCTAGTACTTCAAATTCAGCTCCTGCCTTGGACGCTGCAGAGACAGGA
555  129_HRV19    AATGAAAGTCATCCAAGTACATCAAATGCTGCTCCTGCCTTAGATGCAGCCGAGACAGGA
556  130_HRV19a   AATGAAAGTCATCCAAGTACATCAAATGCTGCTCCTGCCTTAGATGCAGCCGAGACAGGA
557  131_HRV19b   AATGAAAGTCATCCAAGTACATCAAATGCTGCTCCTGCCTTAGATGCAGCCGAGACAGGA
558  132_HRV13    AGTGAAAGTAGCTCAACTACATCTAATTCAGCTCCAGCCTTAGATGCTGCAGAAACTGGC
559  133_HRV13a   AGTGAAAGTAGCTCAACTACATCTAATTCAGCTCCAGCCTTAGATGCTGCAGAAACTGGC
560  134_HRV13b   AGTGAAAGTAGCTCAACTACATCTAATTCAGCTCCAGCCTTAGATGCTGCAGAAACTGGC
561  135_HRV41    AGTGAAAGCAGTCCAACTACTTCTAATTCAGCTCCAGCCCCTAGATGCAGCAGAGACTGGT
562  136_HRV41a   AGTGAAAGCAGTCCAACTACTTCTAATTCAGCTCCAGCCCCTAGATGCAGCAGAGACTGGT
563  137_HRV41b   AGTGAAAGCAGTCCAACTACTTCTAATTCAGCTCCAGCCCCTAGATGCAGCAGAGACTGGT
564  138_HRV73    AATGAAAGTAATCCAACTACATCCAACTCAGCACCTGCACTGGACGCTGCAGAAACTGGC
565  139_HRV73b   AATGAAAGTAATCCAACTACATCCAACTCAGCACCTGCACTGGACGCTGCAGAAACTGGC
566  140_HRV73a   AATGAAAGTAATCCAACTACATCCAACTCAGCACCTGCACTGGACGCTGCAGAAACTGGC
567  141_HRV61    AATCAGAGCAACCCTACAACATCCAACTCAGCACCAGTCTTAGACGCTGCTGAAACAGGT
568  142_HRV61a   AATCAGAGCAACCCTACAACATCCAACTCAGCACCAGTCTTAGACGCTGCTGAAACAGGT
569  143_HRV61b   AATCAGAGCAACCCTACAACATCCAACTCAGCACCAGTCTTAGACGCTGCTGAAACAGGT
570  144_HRV96    AATGAAAGTTACCCAACAACTTCCAATTCAGCCCCAGTGCTAGATGCCGCTGAAACAGGT
571  145_HRV96b   AATGAAAGTTACCCAACAACTTCCAATTCAGCCCCAGTGCTAGATGCCGCTGAAACAGGT
572  146_HRV96a   AATGAAAGTTACCCAACAACTTCCAATTCAGCCCCAGTGCTAGATGCCGCTGAAACAGGT
573  90_HRV16a|   AATGAGAGCCACCCTACCACATCAAATGCGGCCCCAGTTTTGGATGCTGCTGAAACAGGA
574  91_HRV16b|   AATGAGAGCCACCCTACCACATCAAATGCGGCCCCAGTTTTGGATGCTGCTGAAACAGGA
575  92_1AYM_A    AATGAGAGCCACCCTACCACATCAAATGCGGCCCCAGTTTTGGATGCTGCTGAAACAGGA
576  93_HRV81a|   AATGAAAGCCACCCTACAACATCTAATTCAGCTCCTGTTTTAGATGCAGCTGAAACTGGA
577  94_HRV81b|   AATGAAAGCCACCCTACAACATCTAATTCAGCTCCTGTTTTAGATGCAGCTGAAACTGGA
578  95_HRV81     AATGAAAGCCACCCTACAACATCTAATTCAGCTCCTGTTTTAGATGCAGCTGAAACTGGA
579  147_HRV2     AATAGTAGTAACCCCACAACATCAAATTCTGCCCCAGCATTAGATGCTGCAGAAACAGGG
580  148_HRV2a|   AATAGTAGTAACCCCACAACATCAAATTCTGCCCCAGCATTAGATGCTGCAGAAACAGGG
```

FIG. D11 CONT'D

07.trace                                                                9/20/2007 5:04 PM

```
581  149_HRV2b|    AATAGTAGTAACCCCACAACATCAAATTCTGCCCCAGCATTAGATGCTGCAGAAACAGGG
582  150_HRV49a    AATAGTAGTCACCCCACGACATCAAACTCTGCTCCAGCATTAGATGCTGCAGAAACAGGG
583  151_HRV49b    AATAGTAGTCACCCCACGACATCAAACTCTGCTCCAGCATTAGATGCTGCAGAAACAGGG
584  152_HRV49     AATAGTAGTCACCCCACGACATCAAACTCTGCTCCAGCATTAGATGCTGCAGAAACAGGG
585  153_HRV23a    AATAGTAGTCATCCCACAACATCAAACTCTGCTCCAGCATTAGACGCTGCGGAAACGGGT
586  154_HRV23b    AATAGTAGTCATCCCACAACATCAAACTCTGCTCCAGCATTAGACGCTGCGGAAACGGGT
587  155_HRV23     AATAGTAGTCATCCCACAACATCAAACTCTGCTCCAGCATTAGACGCTGCGGAAACGGGT
588  156_HRV30a    AACAGTAGTCACCCTACTACATCAAACTCTGCTCCGGCATTAGATGCTGCAGAAACAGGA
589  157_HRV30b    AACAGTAGTCACCCTACTACATCAAACTCTGCTCCGGCATTAGATGCTGCAGAAACAGGA
590  158_HRV30     AACAGTAGTCACCCTACTACATCAAACTCTGCTCCGGCATTAGATGCTGCAGAAACAGGA
591  159_HRV7      CAGCCAAGTACATCTGTTTCAAGTCACTCTGTACCAGCATTGGATGCTGCAGAGACTGGA
592  160_HRV7b|    CAGCCAAGTACATCTGTTTCAAGTCACTCTGTACCAGCATTGGATGCTGCAGAGACTGGA
593  161_HRV7a|    CAGCCAAGTACATCTGTTTCAAGTCACTCTGTACCAGCATTGGATGCTGCAGAGACTGGA
594  162_HRV88     CAACCTAGCACATCCGTTTCAAGTCACTCTGTGCCAGCTCTGGATGCTGCGGAAACAGGG
595  163_HRV88a    CAACCTAGCACATCCGTTTCAAGTCACTCTGTGCCAGCTCTGGATGCTGCGGAAACAGGG
596  164_HRV88b    CAACCTAGCACATCCGTTTCAAGTCACTCTGTGCCAGCTCTGGATGCTGCGGAAACAGGG
597  165_HRV36a    CAACCTAGTTCATCTGTGTCAAGTCATTCAGCTCCCGCCTTAGACGCTGCGGAAACTGGA
598  166_HRV36b    CAACCTAGTTCATCTGTGTCAAGTCATTCAGCTCCCGCCTTAGACGCTGCGGAAACTGGA
599  167_HRV36     CAACCTAGTTCATCTGTGTCAAGTCATTCAGCTCCCGCCTTAGACGCTGCGGAAACTGGA
600  168_HRV89a    CAACCTAGCACATCTGTGTCAAGTCATGCAGCGCCTGCATTGGATGCTGCGGAAACCGGA
601  169_HRV89b    CAACCTAGCACATCTGTGTCAAGTCATGCAGCGCCTGCATTGGATGCTGCGGAAACCGGA
602  170_HRV89     CAACCTAGCACATCTGTGTCAAGTCATGCAGCGCCTGCATTGGATGCTGCGGAAACCGGA
603  171_HRV58     CAACCTAGTACATCTGTATCAAGTCATTCTGTGCCTGCCTTGGATGCTGCAGAAACGGGA
604  172_HRV58a    CAACCTAGTACATCTGTATCAAGTCATTCTGTGCCTGCCTTGGATGCTGCAGAAACGGGA
605  173_HRV58b    CAACCTAGTACATCTGTATCAAGTCATTCTGTGCCTGCCTTGGATGCTGCAGAAACGGGA
606  174_HRV12a    AACAAAAGTAATGGGCAGTTATCAAACGCAGCACCAGCGTTGGACGCTGCAGAAACTGGT
607  175_HRV12b    AACAAAAGTAATGGGCAGTTATCAAACGCAGCACCAGCGTTGGACGCTGCAGAAACTGGT
608  176_HRV12     AACAAAAGTAATGGGCAGTTATCAAACGCAGCACCAGCGTTGGACGCTGCAGAAACTGGT
609  177_HRV78a    AAAGAAAGTAAACCCCAGTCTAGCAACTCCGCTCCAGTTTTGGACGCTGCAGAAACAGGT
610  178_HRV78b    AAAGAAAGTAAACCCCAGTCTAGCAACTCCGCTCCAGTTTTGGACGCTGCAGAAACAGGT
611  179_HRV78     AAAGAAAGTAAACCCCAGTCTAGCAACTCCGCTCCAGTTTTGGACGCTGCAGAAACAGGT
612  180_HRV20     ACATCTAGTAACTCCCAAACATCAAATGCAGCACCAGCACTAGATGCTGCTGAGACAGGA
613  181_HRV20a    ACATCTAGTAACTCCCAAACATCAAATGCAGCACCAGCACTAGATGCTGCTGAGACAGGA
614  182_HRV20b    ACATCTAGTAACTCCCAAACATCAAATGCAGCACCAGCACTAGATGCTGCTGAGACAGGA
615  183_HRV68     CCAGCAAGTAATACCCAAACTTCAAATGCAGCCCCAGCCTTAGATGCTGCTGAGACTGGA
616  184_HRV68a    CCAGCAAGTAATACCCAAACTTCAAATGCAGCCCCAGCCTTAGATGCTGCTGAGACTGGA
617  185_HRV68b    CCAGCAAGTAATACCCAAACTTCAAATGCAGCCCCAGCCTTAGATGCTGCTGAGACTGGA
618  186_HRV28     AATCCTAGCAACGCACAAACTACAAATGCAGCTCCCGCTCTCGATGCCGCTGAGACGGGG
619  187_HRV28a    AATCCTAGCAACGCACAAACTACAAATGCAGCTCCCGCTCTCGATGCCGCTGAGACGGGG
620  188_HRV28b    AATCCTAGCAACGCACAAACTACAAATGCAGCTCCCGCTCTCGATGCCGCTGAGACGGGG
621  189_HRV53a    AATGCAAGCAATCCACAAACTTCAAATTCAGCACCAGCACTAGATGCTGCAGAAACGGGT
622  190_HRV53b    AATGCAAGCAATCCACAAACTTCAAATTCAGCACCAGCACTAGATGCTGCAGAAACGGGT
623  191_HRV53     AATGCAAGCAATCCACAAACTTCAAATTCAGCACCAGCACTAGATGCTGCAGAAACGGGT
624  192_HRV46a    AATGCCAGTAGTGGACATACATCTAATTCAGCTCCAGCACTTGATGCAGCAGAAACTGGA
625  193_HRV46b    AATGCCAGTAGTGGACATACATCTAATTCAGCTCCAGCACTTGATGCAGCAGAAACTGGA
626  194_HRV46     AATGCCAGTAGTGGACATACATCTAATTCAGCTCCAGCACTTGATGCAGCAGAAACTGGA
627  195_HRV80a    AGTGCTAGCAATGGACATACATCAAACTCAGCTCCAACACTTGATGCAGCAGAAACTGGT
628  196_HRV80b    AGTGCTAGCAATGGACATACATCAAACTCAGCTCCAACACTTGATGCAGCAGAAACTGGT
629  197_HRV80     AGTGCTAGCAATGGACATACATCAAACTCAGCTCCAACACTTGATGCAGCAGAAACTGGT
630  198_HRV51     CAACCTAGCAGTGGGCACACATCTAATGCTGCACCAGCTCTAGATGCTGCTGAGACAGGA
631  199_HRV51a    CAACCTAGCAGTGGGCACACATCTAATGCTGCACCAGCTCTAGATGCTGCTGAGACAGGA
632  200_HRV51b    CAACCTAGCAGTGGGCACACATCTAATGCTGCACCAGCTCTAGATGCTGCTGAGACAGGA
633  201_HRV65a    CAAGCTAGTAATGGGCATACATCTAATGCTGCACCAGCTTTAGATGCTGCTGAAACAGGA
634  202_HRV65b    CAAGCTAGTAATGGGCATACATCTAATGCTGCACCAGCTTTAGATGCTGCTGAAACAGGA
635  203_HRV65     CAAGCTAGTAATGGGCATACATCTAATGCTGCACCAGCTTTAGATGCTGCTGAAACAGGA
636  204_HRV71a    CAACCTAGTAATGGACATACCTCAAACTCAGCACCAGCCTTAGATGCAGCAGAAACTGGG
637  205_HRV71b    CAACCTAGTAATGGACATACCTCAAACTCAGCACCAGCCTTAGATGCAGCAGAAACTGGG
638  206_HRV71     CAACCTAGTAATGGACATACCTCAAACTCAGCACCAGCCTTAGATGCAGCAGAAACTGGG
639  207_HRV8      CAAGCTAGTAATGGATCTATAGCAAATTCAGCACCAGCATTAGATGCAGCAGAGACTGGA
640  208_HRV95     CAAGCAGTAATGGATCTATAGCAAATTCAGCACCAGCATTAGATGCAGCAGAGACTGGA
641  209_HRV45     CGACCCAGCGATGGGTTGATTGCAAACTCAGCCCCAGCTTTGGATGCAGCTGAAACTGGA
642  210_HRV45a    CGACCCAGCGATGGGTTGATTGCAAACTCAGCCCCAGCTTTGGATGCAGCTGAAACTGGA
643  211_HRV45b    CGACCCAGCGATGGGTTGATTGCAAACTCAGCCCCAGCTTTGGATGCAGCTGAAACTGGA
644  GROUP_1       ------AG---------------A--C-G---C-----T-GA-GC-GC-GA-AC-GG-
645
```

FIG. D11 CONT'D 07.trace                                                                    9/20/2007 5:04 PM

```
646  1_HRV1A1|d    CACACCAGTAATGTTCAACCAGAAGATGCTATAGAGACAAGGTATGTTATAACATCACAA
647  2_HRV1A2|d    CACACCAGTAATGTTCAACCAGAAGATGCTATAGAGACAAGGTATGTTATAACATCACAA
648  3_HRV1A|cD    CACACCAGTAATGTTCAACCAGAAGATGCTATAGAGACAAGGTATGTTATAACATCACAA
649  4_HRV1B1|d    CACACCAGTAATGTACAACCAGAGGATGCTATAGAAACAAGATATGTTATGACATCACAA
650  5_HRV1B2|d    CACACCAGTAATGTACAACCAGAGGATGCTATAGAAACAAGATATGTTATGACATCACAA
651  6_HRV1B       CACACCAGTAATGTACAACCAGAGGATGCTATAGAAACAAGATATGTTATGACATCACAA
652  7_HRV40a|d    CATACAAGCAACATACAACCTGAAGATACAATAGAAACAAGATTTGTGCAGACATCACAA
653  8_HRV40b|d    CATACAAGCAACATACAACCTGAAGATACAATAGAAACAAGATTTGTGCAGACATCACAA
654  9_HRV40       CATACAAGCAACATACAACCTGAAGATACAATAGAAACAAGATTTGTGCAGACATCACAA
655 10_HRV85       CATACAAGTAGTACACAGCCCGAGGATACAATAGAGACCAGGTTTGTTCAAACTTCACAG
656 11_HRV85a|     CATACAAGTAGTACACAGCCCGAGGATACAATAGAGACCAGGTTTGTTCAAACTTCACAG
657 12_HRV85b|     CATACAAGTAGTACACAGCCCGAGGATACAATAGAGACCAGGTTTGTTCAAACTTCACAG
658 13_HRV56a|     CATACTAGTGCAATCCAACCAGAAGACACTATAGAAACCAGATATGTACAGACATCACAA
659 14_HRV56b|     CATACTAGTGCAATCCAACCAGAAGACACTATAGAAACCAGATATGTACAGACATCACAA
660 15_HRV56       CATACTAGTGCAATCCAACCAGAAGACACTATAGAAACCAGATATGTACAGACATCACAA
661 16_HRV54       CACACTAGTGGAGTACAACCCGAGGACACCATAGAAACAAGATTTGTGCAGACATCACAA
662 17_HRV98       CACACTAGTGGAATACAACCTGAGGATACTATAGAAACAAGATATGTGCAGACATCACAA
663 18_HRV59a|     CATACAAGCAGTATACAACCTGAGGATACCATAGAAACAAGATATGTTCAGACATCACAA
664 19_HRV59b|     CATACAAGCAGTATACAACCTGAGGATACCATAGAAACAAGATATGTTCAGACATCACAA
665 20_HRV59       CATACAAGCAGTATACAACCTGAGGATACCATAGAAACAAGATATGTTCAGACATCACAA
666 21_HRV63       CACACAAGCAGTATACAACCTGAGGATACTGTAGAAACTAGATATGTGCAAACGTCTCAA
667 22_HRV63b|     CACACAAGCAGTATACAACCTGAGGATACTGTAGAAACTAGATATGTGCAAACGTCTCAA
668 23_HRV63a|     CACACAAGCAGTATACAACCTGAGGATACTGTAGAAACTAGATATGTGCAAACGTCTCAA
669 24_HRV39       CACACAAGTAGCACCCAGCCTGAAGACACAATTGAAACAAGATATGTGCAAACCTCACAT
670 25_HRV39a|     CACACAAGTAGCACCCAGCCTGAAGCACAATTGAAACAAGATATGTGCAAACCTCACAT
671 26_HRV39b|     CACACAAGTAGCATCCAACCTGAAGACACAATTGAAACAAGATATGTGCAAACCTCACAT
672 27_HRV10a|     CATACCAGTAGTGTACAACCAGAAGATACGGTTGAAACACGATATGTGCAAACATCCCAG
673 28_HRV10b|     CATACCAGTAGTGTACAACCAGAAGATACGGTTGAAACACGATATGTGCAAACATCCCAG
674 29_HRV10       CATACCAGTAGTGTACAACCAGAAGATACGGTTGAAACACGATATGTGCAAACATCCCAG
675 30_HRV100a     CACACTAGTAATGTGCAACCTGAAGATACAGTTGAAACTCGATATGTGCAGACATCACAG
676 31_HRV100b     CACACTAGTAATGTGCAACCTGAAGATACAGTTGAAACTCGATATGTGCAGACATCACAG
677 32_HRV100      CACACTAGTAATGTGCAACCTGAAGATACAGTTGAAACTCGATATGTGCAGACATCACAG
678 33_HRV66       CACACTAGTAAAGTACAACCAGAAGATACAGTTGAGACTCGTTACGTGCAAACATCACAG
679 34_HRV66b|     CACACTAGTAAAGTACAACCAGAAGATACAGTTGAGACTCGTTACGTGCAAACATCACAG
680 35_HRV66a|     CACACTAGTAAAGTACAACCAGAAGATACAGTTGAGACTCGTTACGTGCAAACATCACAG
681 36_HRV77a|     CATACTAGTAGTGTGCAACCAGAAGATACAGTTGAGACCCGCTATGTACAAACTTCCCAG
682 37_HRV77b|     CATACTAGTAGTGTGCAACCAGAAGATACAGTTGAGACCCGCTATGTACAAACTTCCCAG
683 38_HRV77       CATACTAGTAGTGTGCAACCAGAAGATACAGTTGAGACCCGCTATGTACAAACTTCCCAG
684 39_HRV62a      CACACTAGTAATGTACAACCAGAAGACACTATTGAAACCCGTCATGTTCAAACCACACAA
685 40_HRV62b      CACACTAGTAATGTACAACCAGAAGACACTATTGAAACCCGTTATGTTCAAACCACACAA
686 41_HRV25       CACACTAGCAATGTGCAACCAGAGGATACCATTGAAACTCGTTATGTTCAAACCACACAA
687 42_HRV29a      CATACTAGTAATGTACAACCAGAAGATACCATTGAGACTCGTTATGTACAAACCTCACAT
688 43_HRV29b      CATACTAGTAATGTACAACCAGAAGATACCATTGAGACTCGTTATGTACAAACCTCACAT
689 44_HRV44a      CATACTAGTAATGTACAACCAGAAGATACCATTGAGACTCGATATGTACAAACCTCACAA
690 45_HRV44b      CATACTAGTAATGTACAACCAGAAGATACCATTGAGACTCGATATGTACAAACCTCACAA
691 46_HRV31       CACACTAGTAATGTACAACCAGAAGATACAATTGAAACTCGCTACGTGCAAACATCACAA
692 47_HRV31a|     CACACTAGTAATGTACAACCAGAAGATACAATTGAAACTCGCTACGTGCAAACATCACAA
693 48_HRV31b|     CACACTAGTAATGTACAACCAGAAGATACAATTGAAACTCGCTACGTGCAAACATCACAA
694 49_HRV47       CACACTAGCAATGTACAGCCAGAAGATACAATTGAAACTCGATATGTACAAACAGCACAA
695 50_HRV47a|     CACACTAGCAATGTACAGCCAGAAGATACAATTGAAACTCGATATGTACAAACAGCACAA
696 51_HRV47b|     CACACTAGCAATGTACAGCCAGAAGATACAATTGAAACTCGATATGTACAAACAGCACAA
697 52_HRV11       CATACTAGCAAAGTGCAGCCAGAGGATATGATTGAGACTAGATATGTGCAGACTTCACAG
698 53_HRV11b|     CATACTAGCAAAGTGCAGCCAGAGGATATGATTGAGACTAGATATGTGCAGACTTCACAG
699 54_HRV11a|     CATACTAGCAAAGTGCAGCCAGAGGATATGATTGAGACTAGATATGTGCAGACTTCACAG
700 55_HRV76       CACACAAGCAGCGTTCAACCAGAGGACATGGTTGAGACTAGGTATGTGCAAACATCACAA
701 56_HRV76b|     CACACAAGCAGCGTTCAACCAGAGGACATGGTTGAGACTAGGTATGTGCAAACATCACAA
702 57_HRV76a|     CACACAAGCAGCGTTCAACCAGAGGACATGGTTGAGACTAGGTATGTGCAAACATCACAA
703 58_HRV33       CACACTAATAATGTACAACCAGAATATGATTGAAACAAGATATGTACAAACATCACAA
704 59_HRV33b|     CACACTAATAATGTACAACCAGAAGATATGATTGAAACAAGATATGTACAAACATCACAA
705 60_HRV33a|     CACACTAATAATGTACAACCAGAAGATATGATTGAAACAAGATATGTACAAACATCACAA
706 61_HRV24a|     CATACGAGTAGCGTGCAGCCAGAAGATATGGTTGAAACTAGATATGTCCAAACATCACAA
707 62_HRV24b|     CATACGAGTAGCGTGCAGCCAGAAGATATGGTTGAAACTAGATATGTCCAAACATCACAA
708 63_HRV24       CATACGAGTAGCGTGCAGCCAGAAGATATGGTTGAAACTAGATATGTCCAAACATCACAA
709 64_HRV90       CATACTAGTGATGTCCAGCCAGAAGATGTGGTAGAGACCAGATACGTGCAAACATCACAA
710 65_HRV90a|     CATACTAGTGATGTCCAGCCAGAAGATGTGGTAGAGACCAGATACGTGCAAACATCACAA
```

FIG. D11 CONT'D 07.trace                                                                    9/20/2007 5:04 PM

| | | |
|---|---|---|
| 711 | 66_HRV90b\| | CATACTAGTGATGTCCAGCCAGAAGATGTGGTAGAGACCAGATACGTGCAAACATCACAA |
| 712 | 67_HRV34 | CACACTAGCAGTGTACAACCTGAAGATATGATTGAGACCAGGTACGTACAAACATCACAA |
| 713 | 68_HRV34b\| | CACACTAGCAGTGTACAACCTGAAGATATGATTGAGACCAGGTACGTACAAACATCACAA |
| 714 | 69_HRV34a\| | CACACTAGCAGTGTACAACCTGAAGATATGATTGAGACCAGGTACGTACAAACATCACAA |
| 715 | 70_HRV50a\| | CACACAAGTAATGTGCAGCCTGAAGATATGCTTGAAACTAGATATGTGCAAACATCGCAT |
| 716 | 71_HRV50b\| | CACACAAGTAATGTGCAGCCTGAAGATATGCTTGAAACTAGATATGTGCAAACATCGCAT |
| 717 | 72_HRV50 | CACACAAGTAATGTGCAGCCTGAAGATATGCTTGAAACTAGATATGTGCAAACATCGCAT |
| 718 | 73_HRV18a\| | CACACCAGCAATGTGCAACCTGAAGATATGATTGAGACTAGGTATGTACAAACATCACAA |
| 719 | 74_HRV18b\| | CACACCAGCAATGTGCAACCTGAAGATATGATTGAGACTAGGTATGTACAAACATCACAA |
| 720 | 75_HRV18 | CACACCAGCAATGTGCAACCTGAAGATATGATTGAGACTAGGTATGTACAAACATCACAA |
| 721 | 76_HRV55 | CATACAAGCAATGTACAACCAGAAGATGTAATTGAGACAAGATATGTTCAGACATCACAA |
| 722 | 77_HRV55b\| | CATACAAGCAATGTACAACCAGAAGATGTAATTGAGACAAGATATGTTCAGACATCACAA |
| 723 | 78_HRV55a\| | CATACAAGCAATGTACAACCAGAAGATGTAATTGAGACAAGATATGTTCAGACATCACAA |
| 724 | 79_HRV57 | CACACTAGTAATGTACAACCGGAAGACATGATTGAAACTAGATATGTCCAGACATCACAA |
| 725 | 80_HRV57a\| | CACACTAGTAATGTACAACCGGAAGACATGATTGAAACTAGATATGTCCAGACATCACAA |
| 726 | 81_HRV57b\| | CACACTAGTAATGTACAACCGGAAGACATGATTGAAACTAGATATGTCCAGACATCACAA |
| 727 | 82_HRV21 | CACACTAGTAATGTACAGCCGGAGGATATGTTGAAACAAGGTATGTTCAGACATCACAA |
| 728 | 83_HRVHan | CACACTAGTAATGTACAACCAGAGGATATGGTTGAAACAAGGTATGTTCAGACATCACAA |
| 729 | 84_HRV43 | CATACTAGCCAGGTGCAACCTGAAGACATGGTAGAGACAAGGTCAGTACATAATTTCCAA |
| 730 | 85_HRV43b\| | CATACTAGCCAGGTGCAACCTGAAGACATGGTAGAGACAAGGTCAGTACATAATTTCCAA |
| 731 | 86_HRV43a\| | CATACTAGCCAGGTGCAACCTGAAGACATGGTAGAGACAAGGTCAGTACATAATTTCCAA |
| 732 | 87_HRV75 | CATACCAGCCATGTTCAACCAGAAGACATGTTAGAAACAAGGCAAGTACAAAATTTCCAA |
| 733 | 88_HRV75b\| | CATACCAGCCATGTTCAACCAGAAGACATGTTAGAAACAAGGCAAGTACAAAATTTCCAA |
| 734 | 89_HRV75a\| | CATACCAGCCATGTTCAACCAGAAGACATGTTAGAAACAAGGCAAGTACAAAATTTCCAA |
| 735 | 96_HRV9a\|d | CATACTAGCAATGTTCAACCTGAAGCATGATTGAAACACGTTATGTGCAGACATCACAA |
| 736 | 97_HRV9b\|d | CATACTAGCAATGTTCAACCTGAAGACATGATTGAAACACGTTATGTGCAGACATCACAA |
| 737 | 98_HRV9 | CATACTAGCAATGTTCAACCTGAAGACATGATTGAAACACGTTATGTGCAGACATCACAA |
| 738 | 99_HRV32 | CATACCAGTAATGTTCAACCTGAAGACATGATTGAAACACGTTATGTGCAAACAACACAC |
| 739 | 100_HRV32a | CATACCAGTAATGTTCAACCTGAAGACATGATTGAAACACGTTATGTGCAAACAACACAC |
| 740 | 101_HRV32b | CATACCAGTAATGTTCAACCTGAAGACATGATTGAAACACGTTATGTGCAAACAACACAC |
| 741 | 102_HRV67 | CACACTAGCAGTGTACAACCTGAAGATATGATCGAGACTCGTTATGTACAGGCATCAAAT |
| 742 | 103_HRV67a | CACACTAGCAGTGTACAACCTGAAGATATGATCGAGACTCGTTATGTACAGGCATCAAAT |
| 743 | 104_HRV67b | CACACTAGCAGTGTACAACCTGAAGATATGATCGAGACTCGTTATGTACAGGCATCAAAT |
| 744 | 105_HRV15 | CATACTAGCAGTGTTCAACCTGAGGATATGATTGAAACTCGTTACGTCCAAACATCACAG |
| 745 | 106_HRV15a | CATACTAGCAGTGTTCAACCTGAGGATATGATTGAAACTCGTTACGTCCAAACATCACAG |
| 746 | 107_HRV15b | CATACTAGCAGTGTTCAACCTGAGGATATGATTGAAACTCGTTACGTCCAAACATCACAG |
| 747 | 108_HRV74a | CATACCAGTAATGTGCAACCAGAAGATATGGTTGAGACACGCTATGTGCAAACCTCACAG |
| 748 | 109_HRV74b | CATACCAGTAATGTGCAACCAGAAGATATGGTTGAGACACGCTATGTGCAAACCTCACAG |
| 749 | 110_HRV74 | CATACCAGTAATGTGCAACCAGAAGATATGGTTGAGACACGCTATGTGCAAACCTCACAG |
| 750 | 111_HRV38a | CACACCAGTAATGTGCAGCCTGAGGATATGATTGAAACTCGCTATGTACAGACATCACAA |
| 751 | 112_HRV38b | CACACCAGTAATGTGCAGCCTGAGGATATGATTGAAACTCGCTATGTACAGACATCACAA |
| 752 | 113_HRV38 | CACACCAGTAATGTGCAGCCTGAGGATATGATTGAAACTCGCTATGTACAGACATCACAA |
| 753 | 114_HRV60 | CACACTAGTAATGTACAGCCTGAGGACGTGATTGAAACACGTTATGTGCAGATTACACAA |
| 754 | 115_HRV60a | CACACTAGTAATGTACAGCCTGAGGACGTGATTGAAACACGTTATGTGCAGATTACACAA |
| 755 | 116_HRV60b | CACACTAGTAATGTACAGCCTGAGGACGTGATTGAAACACGTTATGTGCAGATTACACAA |
| 756 | 117_HRV64a | CACACCAGTAATGTACAGCCTGAAGATATGATTGAAACGCGCTATGTACAAAACACTCAA |
| 757 | 118_HRV64b | CACACCAGTAATGTACAGCCTGAAGATATGATTGAAACGCGCTATGTACAAAACACTCAA |
| 758 | 119_HRV64 | CACACCAGTAATGTACAGCCTGAAGATATGATTGAAACGCGCTATGTACAAAACACTCAA |
| 759 | 120_HRV94a | CACACAAGCAATGTACAACCTGAGGATATGATTGAAACACGCTATGTACAAAACACTCAA |
| 760 | 121_HRV94b | CACACAAGCAATGTACAACCTGAGGATATGATTGAAACACGCTATGTACAAAACACTCAA |
| 761 | 122_HRV94 | CACACAAGCAATGTACAACCTGAGGATATGATTGAAACACGCTATGTACAAAACACTCAA |
| 762 | 123_HRV22 | CACACAAGCAATGTGCAGCCAGAAGACATGATAGAAACACGCTATGTGTTAAATTCACAA |
| 763 | 124_HRV22a | CACACAAGCAATGTGCAGCCAGAAGACATGATAGAAACACGCTATGTGTTAAATTCACAA |
| 764 | 125_HRV22b | CACACAAGCAATGTGCAGCCAGAAGACATGATAGAAACACGCTATGTGTTAAATTCACAA |
| 765 | 126_HRV82 | CATACAAGTACTGTTCAACCTGAGGACATGATTGAAACACGGTATGTTCAAACATCACAA |
| 766 | 127_HRV82b | CATACAAGTACTGTTCAACCTGAGGACATGATTGAAACACGGTATGTTCAAACATCACAA |
| 767 | 128_HRV82a | CATACAAGTACTGTTCAACCTGAGGACATGATTGAAACACGGTATGTTCAAACATCACAA |
| 768 | 129_HRV19 | CATACTAGCAATGTACAGCCTGAGGACATGATCGAAACACGCTATGTTCAAACGTCCCAG |
| 769 | 130_HRV19a | CATACTAGCAATGTACAGCCTGAGGACATGATCGAAACACGCTATGTTCAAACGTCCCAG |
| 770 | 131_HRV19b | CATACTAGCAATGTACAGCCTGAGGACATGATCGAAACACGCTATGTTCAAACGTCCCAG |
| 771 | 132_HRV13 | CACACAAGCAGTGTACAACCAGAAGACATGGTTGAAACACGTTATGTCCAAACTTCACAA |
| 772 | 133_HRV13a | CACACAAGCAGTGTACAACCAGAAGACATGGTTGAAACACGTTATGTCCAAACTTCACAA |
| 773 | 134_HRV13b | CACACAAGCAGTGTACAACCAGAAGACATGGTTGAAACACGTTATGTCCAAACTTCACAA |
| 774 | 135_HRV41 | CATACCAGTAATGTACAACCAGAGGACATGATTGAAACACGATATGTCCAAACCTCACAA |
| 775 | 136_HRV41a | CATACCAGTAATGTACAACCAGAGGACATGATTGAAACACGATATGTCCAAACCTCACAA |

FIG. D11 CONT'D 07.trace                                                                                          9/20/2007 5:04 PM

```
776  137_HRV41b    CATACCAGTAATGTACAACCAGAGGACATGATTGAAACACGATATGTCCAAACCTCACAA
777  138_HRV73     CATACCAGTGGTGTACAACCAGAAGACATGATTGAGACCCGTTATGTCCAAACATCACAG
778  139_HRV73b    CATACCAGTGGTGTACAACCAGAAGACATGATTGAGACCCGTTATGTCCAAACATCACAG
779  140_HRV73a    CATACCAGTGGTGTACAACCAGAAGACATGATTGAGACCCGTTATGTCCAAACATCACAG
780  141_HRV61     CATACCAGCAATGTTCAACCGGAGGACACGATTGAAACACGATATGTTCAAACCTCACAG
781  142_HRV61a    CATACCAGCAATGTTCAACCGGAGGACACGATTGAAACACGATATGTTCAAACCTCACAG
782  143_HRV61b    CATACCAGCAATGTTCAACCGGAGGACACGATTGAAACACGATATGTTCAAACCTCACAG
783  144_HRV96     CATACTAGCAATGTCCAACCAGAGGATATGATTGAGACTCGATATGTTCAGACATCGCAG
784  145_HRV96b    CATACTAGCAATGTCCAACCAGAGGATATGATTGAGACTCGATATGTTCAGACATCGCAG
785  146_HRV96a    CATACTAGCAATGTCCAACCAGAGGATATGATTGAGACTCGATATGTTCAGACATCGCAG
786  90_HRV16a|    CATACCAATAAGATACAGCCAGAAGACACTATAGAAACCAGATATGTGCAATCTTCACAG
787  91_HRV16b|    CATACCAATAAGATACAGCCAGAAGACACTATAGAAACCAGATATGTGCAATCTTCACAG
788  92_1AYM_A     CATACCAATAAGATACAGCCAGAAGACACTATAGAAACCAGATATGTGCAATCTTCACAG
789  93_HRV81a|    CACACCAGTAATATACAACCTGAGGATACTATTGAGACCAGATATGTACAATCTTCACAG
790  94_HRV81b|    CACACCAGTAATATACAACCTGAGGATACTATTGAGACCAGATATGTACAATCTTCACAG
791  95_HRV81      CACACCAGTAATATACAACCTGAGGATACTATTGAGACCAGATATGTACAATCTTCACAG
792  147_HRV2      CACACTAGTAGTGTTCAACCAGAGGATGTCATTGAAACTAGGTATGTGCAGACATCACAA
793  148_HRV2a|    CACACTAGTAGTGTTCAACCAGAGGATGTCATTGAAACTAGGTATGTGCAGACATCACAA
794  149_HRV2b|    CACACTAGTAGTGTTCAACCAGAGGATGTCATTGAAACTAGGTATGTGCAGACATCACAA
795  150_HRV49a    CACACTAGCAATGTGCAACCTGAAGATGTCATTGAAACCAGATATGTACAGACATCACAA
796  151_HRV49b    CACACTAGCAATGTGCAACCTGAAGATGTCATTGAAACCAGATATGTACAGACATCACAA
797  152_HRV49     CACACTAGCAATGTGCAACCTGAAGATGTCATTGAAACCAGATATGTACAGACATCACAA
798  153_HRV23a    CACACTAGTAATGTTCAACCAGAAGTGTCATTGAAACCAGGTACGTTCAAACATCACAA
799  154_HRV23b    CACACTAGTAATGTTCAACCAGAAGATGTCATTGAAACCAGGTACGTTCAAACATCACAA
800  155_HRV23     CACACTAGTAATGTTCAACCAGAAGATGTCATTGAAACCAGGTACGTTCAAACATCACAA
801  156_HRV30a    CATACTAGTAATGTTCAACCTGAAGATGTCATTGAAACTAGATATGTTCAAACATCACAA
802  157_HRV30b    CATACTAGTAATGTTCAACCTGAAGATGTCATTGAAACTAGATATGTTCAAACATCACAA
803  158_HRV30     CATACTAGTAATGTTCAACCTGAAGATGTCATTGAAACTAGATATGTTCAAACATCACAA
804  159_HRV7      CATACTAGTTCTGTTCAACCTGAAGTATGATCGAGACAAGGTATGTCATAACAGACCAA
805  160_HRV7b|    CATACTAGTTCTGTTCAACCTGAAGATATGATCGAGACAAGGTATGTCATAACAGACCAA
806  161_HRV7a|    CATACTAGTTCTGTTCAACCTGAAGATATGATCGAGACAAGGTATGTCATAACAGACCAA
807  162_HRV88     CATACTAGTTCTGTTCAACCTGAAGATATGATAGAAACTAGATATGTTATAACAGATCAA
808  163_HRV88a    CATACTAGTTCTGTTCAACCTGAAGATATGATAGAAACTAGATATGTTATAACAGATCAA
809  164_HRV88b    CATACTAGTTCTGTTCAACCTGAAGATATGATAGAAACTAGATATGTTATAACAGATCAA
810  165_HRV36     CATACCAGCTCTGTCCAACCAGAGGACATGATCGAGACCAGATATGTCATAACTGATCAA
811  166_HRV36b    CATACCAGCTCTGTCCAACCAGAGGACATGATCGAGACCAGATATGTCATAACTGATCAA
812  167_HRV36     CATACCAGCTCTGTCCAACCAGAGGACATGATCGAGACCAGATATGTCATAACTGATCAA
813  168_HRV89a    CACACCAGCTCTGTTCAACCTGAAGATATGATTGAAACTAGATATGTTATAACTGATCAA
814  169_HRV89b    CACACCAGCTCTGTTCAACCTGAAGATATGATTGAAACTAGATATGTTATAACTGATCAA
815  170_HRV89     CACACCAGCTCTGTTCAACCTGAAGATATGATTGAAACTAGATATGTTATAACTGATCAA
816  171_HRV58     CACACAAGTTCTGTTCAGCCTGAGGATATGATTGAAACTAGATATGTTATCACAGATCAA
817  172_HRV58a    CACACAAGTTCTGTTCAGCCTGAGGATATGATTGAAACTAGATATGTTATCACAGATCAA
818  173_HRV58b    CACACAAGTTCTGTTCAGCCTGAGGATATGATTGAAACTAGATATGTTATCACAGATCAA
819  174_HRV12a    CATACCAGCCAAACACAACCAGAAGATGTGATTGAAACCAGGTATGTGATTACAGACCAG
820  175_HRV12b    CATACCAGCCAAACACAACCAGAAGATGTGATTGAAACCAGGTATGTGATTACAGACCAG
821  176_HRV12     CATACCAGCCAAACACAACCAGAAGATGTGATTGAAACCAGGTATGTGATTACAGACCAG
822  177_HRV78a    CATACGAACCAAGTACAGCCTGAAGACACCATAGAAACTAGATATGTTATAACTGACCAA
823  178_HRV78b    CATACGAACCAAGTACAGCCTGAAGACACCATAGAAACTAGATATGTTATAACTGACCAA
824  179_HRV78     CATACGAACCAAGTACAGCCTGAAGACACCATAGAAACTAGATATGTTATAACTGACCAA
825  180_HRV20     CACACAAACCAGGTCCAGCCAGAAGATATGGTCGAGACACGGTATGTAATTACTGATCAG
826  181_HRV20a    CACACAAACCAGGTCCAGCCAGAAGATATGGTCGAGACACGGTATGTAATTACTGATCAG
827  182_HRV20b    CACACAAACCAGGTCCAGCCAGAAGATATGGTCGAGACACGGTATGTAATTACTGATCAG
828  183_HRV68     CATACAAACCAAGTCCAACCAGAAGATGTGGTTGAAACACGCTATGTCATAACAGACCAG
829  184_HRV68a    CATACAAACCAAGTCCAACCAGAAGATGTGGTTGAAACACGCTATGTCATAACAGACCAG
830  185_HRV68b    CATACAAACCAAGTCCAACCAGAAGATGTGGTTGAAACACGCTATGTCATAACAGACCAG
831  186_HRV28     CACACAAGCCAAACACAACCTGAAGACATGGTTGAGACTAGGTATGTAATCACAGATCAG
832  187_HRV28a    CACACAAGCCAAACACAACCTGAAGCATGGTTGAGACTAGGTATGTAATCACAGATCAG
833  188_HRV28b    CACACAAGCCAAACACAACCTGAAGCATGGTTGAGACTAGGTATGTAATCACAGATCAG
834  189_HRV53a    CATACAAGTCAGACACAACCTGAGGACATGCTGGAAACTAGATATGTCATCACAGACCAA
835  190_HRV53b    CATACAAGTCAGACACAACCTGAGGACATGCTGGAAACTAGATATGTCATCACAGACCAA
836  191_HRV53     CATACAAGTCAGACACAACCTGAGGACATGCTGGAAACTAGATATGTCATCACAGACCAA
837  192_HRV46a    CACACTAGCCAGATACAACCAGAAGACATGATAGAAACCAGATATGTTATCACAGACCAA
838  193_HRV46b    CACACTAGCCAGATACAACCAGAAGACATGATAGAAACCAGATATGTTATCACAGACCAA
839  194_HRV46     CACACTAGCCAGATACAACCAGAAGACATGATAGAAACCAGATATGTTATCACAGACCAA
840  195_HRV80a    CACACTAGCCAGGTGCAACCAGAAGACATGATAGAAACTAGATATGTTATTACTGATCAG
```

FIG. D11 CONT'D 07.trace                                                                                    9/20/2007 5:04 PM

```
841 196_HRV80b    CACACTAGCCAGGTGCAACCAGAAGACATGATAGAAACTAGATATGTTATTACTGATCAG
842 197_HRV80     CACACTAGCCAGGTGCAACCAGAAGACATGATAGAAACTAGATATGTTATTACTGATCAG
843 198_HRV51     CATACTAGTCAAGTTCAACCAGAAGATATGGTAGAGACCAGGTATGTTGTCACAGACCAA
844 199_HRV51a    CATACTAGTCAAGTTCAACCAGAAGATATGGTAGAGACCAGGTATGTTGTCACAGACCAA
845 200_HRV51b    CATACTAGTCAAGTTCAACCAGAAGATATGGTAGAGACCAGGTATGTTGTCACAGACCAA
846 201_HRV65a    CACACTAGTCAAGTTCAACCAGAGGATGTGATAGAAACCAGATATGTCATCACAGATCAA
847 202_HRV65b    CACACTAGTCAAGTTCAACCAGAGGATGTGATAGAAACCAGATATGTCATCACAGATCAA
848 203_HRV65     CACACTAGTCAAGTTCAACCAGAGGATGTGATAGAAACCAGATATGTCATCACAGATCAA
849 204_HRV71a    CATACCAACCAAGTACAACCAGAAGATGTTATGGAAACCAGATATGTGATCACTGATCAA
850 205_HRV71b    CATACCAACCAAGTACAACCAGAAGATGTTATGGAAACCAGATATGTGATCACTGATCAA
851 206_HRV71     CATACCAACCAAGTACAACCAGAAGATGTTATGGAAACCAGATATGTGATCACTGATCAA
852 207_HRV8      CACACAAGTTCAGTGCAACCTGAAGATCTTATAGAGACTAGGTATGTAATTACAGATCAA
853 208_HRV95     CACACAAGTTCAGTGCAACCTGAAGATCTTATAGAGACTAGGTATGTAATTACAGATCAA
854 209_HRV45     CACACCAGTTCAGTGCAGCCTGAGGACCTTATAGAGACTAGATATGTGATTGCAGACCAA
855 210_HRV45a    CACACCAGTTCAGTGCAGCCTGAGGACCTTATAGAGACTAGATATGTGATTGCAGACCAA
856 211_HRV45b    CACACCAGTTCAGTGCAGCCTGAGGACCTTATAGAGACTAGATATGTGATTGCAGACCAA
857 GROUP_1       CA-AC-A--------CA-CC-GA-GA-----T-GA-AC--G----GT-----------A-
858
859 1_HRV1A1|d    ACAAGAGATGAGATGAGTATAGAAAGTTTCCTTGGTAGATCTGGTTGTGTCCACATCTCA
860 2_HRV1A2|d    ACAAGAGATGAGATGAGTATAGAAAGTTTCCTTGGTAGATCTGGTTGTGTCCACATCTCA
861 3_HRV1A|cD    ACAAGAGATGAGATGAGTATAGAAAGTTTCCTTGGTAGATCTGGTTGTGTCCACATCTCA
862 4_HRV1B1|d    ACAAGAGATGAGATGAGTATAGAAAGTTTCTTGGTAGATCTGGCTGTGTGCATATTTCA
863 5_HRV1B2|d    ACAAGAGATGAGATGAGTATAGAAAGTTTCTTGGTAGATCTGGCTGTGTGCATATTTCA
864 6_HRV1B       ACAAGAGATGAGATGAGTATAGAAAGTTTCTTGGTAGATCTGGCTGTGTGCATATTTCA
865 7_HRV40a|d    ACTAGAGATGAAATGAGCATAGAGAGTTTCTTGGGAAGATCTGGGTGCATTCATATATCC
866 8_HRV40b|d    ACTAGAGATGAAATGAGCATAGAGAGTTTCTTGGGAAGATCTGGGTGCATTCATATATCC
867 9_HRV40       ACTAGAGATGAAATGAGCATAGAGAGTTTCTTGGGAAGATCTGGGTGCATTCATATATCC
868 10_HRV85      ACTAGGGATGAAATGAGTTTAGAAAGTTTCTTGGGAAGATCTGGATGTATCCATATATCT
869 11_HRV85a|    ACTAGGGATGAAATGAGTTTAGAAAGTTTCTTGGGAAGATCTGGATGTATCCATATATCT
870 12_HRV85b|    ACTAGGGATGAAATGAGTTTAGAAAGTTTCTTGGGAAGATCTGGATGTATCCATATATCT
871 13_HRV56a|    ACTAGGGATGAAATGAGTATAGAGAGTTTTCTAGGTAGATCAGGTTGTATACATATATCA
872 14_HRV56b|    ACTAGGGATGAAATGAGTATAGAGAGTTTTCTAGGTAGATCAGGTTGTATACATATATCA
873 15_HRV56      ACTAGGGATGAAATGAGTATAGAGAGTTTTCTAGGTAGATCAGGTTGTATACATATATCA
874 16_HRV54      ACTAGAGATGAAATGAGCATAGAAAGTTTTCTAGGCAGGGCTGGTTGCATACATGAATCC
875 17_HRV98      ACCAGAGATGAAATGAGTATACAAAGTTTCTAGGTAGGGCCGGTTGTATACATGAATCT
876 18_HRV59a|    ACTAGAGATGAGATGAGTGTAGAAAGTTTCTTAGGTAGATCTGGGTGTATACATATTTCA
877 19_HRV59b|    ACTAGAGATGAGATGAGTGTACAAAGTTTCTTAGGTAGATCTGGGTGTATACATATTTCA
878 20_HRV59      ACTAGAGATGAGATGAGTGTAGAAAGTTTCTTAGGTAGATCTGGGTGTATACATATTTCA
879 21_HRV63      ACAAGGGATGAAATGAGTGTAGAGAGCTTTCTTGGTAGATCAGGATGCATACACATATCA
880 22_HRV63b|    ACAAGGGATGAAATGAGTGTAGAGAGCTTTCTTGGTAGATCAGGATGCATACACATATCA
881 23_HRV63a|    ACAAGGGATGAAATGAGTGTAGAGAGCTTTCTTGGTAGATCAGGATGCATACACATATCA
882 24_HRV39      ACTAGGGATGAAATGAGCGTTGAAAGTTTCTTAGGCAGATCTGGCTGTATTCACATTTCC
883 25_HRV39a|    ACTAGGGATGAAATGAGCGTTGAAAGTTTCTTAGGCAGATCTGGCTGTATTCACATTTCC
884 26_HRV39b|    ACTAGGGATGAAATGAGTGTTGAAAGTTTCTTAGGCAGATCTGGCTGTATTCACATTTCC
885 27_HRV10a|    ACGAGAGATGAAATGAGTATTGAAAGTTTTCTTGGCAGGTCAGGTTGTATACACACCTCA
886 28_HRV10b|    ACGAGAGATGAAATGAGTATTGAAAGTTTTCTTGGCAGGTCAGGTTGTATACACACCTCA
887 29_HRV10      ACGAGAGATGAAATGAGTATTGAAAGTTTTCTTGGCAGGTCAGGTTGTATACACACCTCA
888 30_HRV100a    ACCAGGGATGAAATGAGTATTGAGAGCTTTCTTGGAAGATCTGGTTGTATACACACCTCA
889 31_HRV100b    ACCAGGGATGAAATGAGTATTGAGAGCTTTCTTGGAAGATCTGGTTGTATACACACCTCA
890 32_HRV100     ACCAGGGATGAAATGAGTATTGAGAGCTTTCTTGGAAGATCTGGTTGTATACACACCTCA
891 33_HRV66      ACTAGAGATGAAATGAGCATAGAAAGTTTTCTAGGTAGGTCAGGATGTATCCATATATCA
892 34_HRV66b|    ACTAGAGATGAAATGAGCATAGAAAGTTTTCTAGGTAGGTCAGGATGTATCCATATATCA
893 35_HRV66a|    ACTAGAGATGAAATGAGCATAGAAAGTTTTCTAGGTAGGTCAGGATGTATCCATATATCA
894 36_HRV77a|    ACAAGGGATGAGATGAGTATTGAGAGCTTTCTGGGTAGGTCTGGTTGTATTCACATTTCA
895 37_HRV77b|    ACAAGGGATGAGATGAGTATTGAGAGCTTTCTGGGTAGGTCTGGTTGTATTCACATTTCA
896 38_HRV77      ACAAGGGATGAGATGAGTATTGAGAGCTTTCTGGGTAGGTCTGGTTGTATTCACATTTCA
897 39_HRV62a     ACTAGAGATGAAATGAGCATTGAGAGCTTTCTTGGTAGGTCAGGGTGCGTACACACTTCA
898 40_HRV62b     ACTAGAGATGAAATGAGCATTGAGAGCTTTCTTGGTAGGTCAGGGTGCGTACACACTTCA
899 41_HRV25      ACTAGAGATGAAATGAGTATTGAAAGTTTCTTGGTAGGTCAGGGTGTGTACATACTTCA
900 42_HRV29a     ACTAGAGATGAAATGAGCATTGAAAGTTTCTTGGTAGATCAGGATGTATACATGTTTCA
901 43_HRV29b     ACTAGAGATGAAATGAGCATTGAAAGTTTCTTGGTAGATCAGGATGTATACATGTTTCA
902 44_HRV44a     ACTAGAGATGAAATGAGCATTGAAAGTTTCTTGGCAGATCAGGGTGTATACATGTTTCA
903 45_HRV44b     ACTAGAGATGAAATGAGCATTGAAAGTTTCTTGGCAGATCAGGGTGTATACATGTTTCA
904 46_HRV31      ACAAGAGATGAAATGAGCATTGAAAGTTTCCTTGGTAGGTCAGGATGTGTACATACTTCA
905 47_HRV31a|    ACAAGAGATGAAATGAGCATTGAAAGTTTCCTTGGTAGGTCAGGATGTGTACATACTTCA
```

FIG. D11 CONT'D 07.trace                                                                                       9/20/2007 5:04 PM

```
906  48_HRV31b|   ACAAGAGATGAAATGAGCATTGAAAGTTTCCTTGGTAGGTCAGGATGTGTACATACTTCA
907  49_HRV47    ACAAGAGATGAAATGAGCATTGAGAGCTTCCTTGGCAGGTCAGGATGTGTGCATTCCTCA
908  50_HRV47a|  ACAAGAGATGAAATGAGCATTGAGAGCTTCCTTGGCAGGTCAGGATGTGTGCATTCCTCA
909  51_HRV47b|  ACAAGAGATGAAATGAGCATTGAGAGCTTCCTTGGCAGGTCAGGATGTGTGCATTCCTCA
910  52_HRV11    ACTCTTGATGAAATGAGCATTGAGAGCTTCCTAGGTAGATCTGGTTGTATTCACATGTCC
911  53_HRV11b|  ACTCTTGATGAAATGAGCATTGAGAGCTTCCTAGGTAGATCTGGTTGTATTCACATGTCC
912  54_HRV11a|  ACTCTTGATGAAATGAGCATTGAGAGCTTCCTAGGTAGATCTGGTTGTATTCACATGTCC
913  55_HRV76    ACTCTTGATGAGATGTGTATGGAGAGTTTCTTAGGGAGATCTGGTTGTATTCATATTTCA
914  56_HRV76b|  ACTCTTGATGAGATGTGTATGGAGAGTTTCTTAGGGAGATCTGGTTGTATTCATATTTCA
915  57_HRV76a|  ACTCTTGATGAGATGTGTATGGAGAGTTTCTTAGGGAGATCTGGTTGTATTCATATTTCA
916  58_HRV33    ACTCTTGATGAGATGAGTGTGGAAAGCTTCTTAGGAAGGTCTGGTTGCATTCACATGTCA
917  59_HRV33b|  ACTCTTGATGAGATGAGTGTGGAAAGCTTCTTAGGAAGGTCTGGTTGCATTCACATGTCA
918  60_HRV33a|  ACTCTTGATGAGATGAGTGTGGAAAGCTTCTTAGGAAGGTCTGGTTGCATTCACATGTCA
919  61_HRV24a|  ACATTACATGAGATGAGTGTTGAAAGTTTCTTGGGTAGATCAGGTTGCATACACATGTCC
920  62_HRV24b|  ACATTACATGAGATGAGTGTTGAAAGTTTCTTGGGTAGATCAGGTTGCATACACATGTCC
921  63_HRV24    ACATTACATGAGATGAGTGTTGAAAGTTTCTTGGGTAGATCAGGTTGCATACACATGTCC
922  64_HRV90    ACAAGAGATGAAATGAGTGTTGAAAGTTTTCTAGGGAGATCAGGTTGCATTCATATGTCA
923  65_HRV90a|  ACAAGAGATGAAATGAGTGTTGAAAGTTTTCTAGGGAGATCAGGTTGCATTCATATGTCA
924  66_HRV90b|  ACAAGAGATGAAATGAGTGTTGAAAGTTTTCTAGGGAGATCAGGTTGCATTCATATGTCA
925  67_HRV34    ACAAGAGATGAAATGAGCATTGAAAGCTTCTGGGTAGGTCTGGCTGTATACACATGTCC
926  68_HRV34b|  ACAAGAGATGAAATGAGCATTGAGAGTTTCCTGGGTAGGTCTGGCTGTATACACATGTCC
927  69_HRV34a|  ACAAGAGATGAAATGAGCATTGAGAGTTTCCTGGGTAGGTCTGGCTGTATACACATGTCC
928  70_HRV50a|  ACAAGAGATGAAATGAGCATTGAAAGTTTCCTAGGTAGATCTGGTTGTATACATATATCT
929  71_HRV50b|  ACAAGAGATGAAATGAGCATTGAAAGTTTCCTAGGTAGATCTGGTTGTATACATATATCT
930  72_HRV50    ACAAGAGATGAAATGAGCATTGAAAGTTTCCTAGGTAGATCTGGTTGTATACATATATCT
931  73_HRV18a|  ACAAGAGATGAAATGAGTATAGAGTGTTTTCTAGGCAGATCAGGGTGTATACATATCTCC
932  74_HRV18b|  ACAAGAGATGAAATGAGTATAGAGTGTTTTCTAGGCAGATCAGGGTGTATACATATCTCC
933  75_HRV18    ACAAGAGATGAAATGAGTATAGAGTGTTTTCTAGGCAGATCAGGGTGTATACATATCTCC
934  76_HRV55    ACTCGTGATGAGATGAGCATTGAAAGTTTTCTAGGTAGATCAGGATGTGTACATATATCA
935  77_HRV55b|  ACTCGTGATGAGATGAGCATTGAAAGTTTTCTAGGTAGATCAGGATGTGTACATATATCA
936  78_HRV55a|  ACTCGTGATGAGATGAGCATTGAAAGTTTTCTAGGTAGATCAGGATGTGTACATATATCA
937  79_HRV57    ACACGTGATGAAATGAGTCTTGAGAGCTTCTTAGGAAGATCTGGCTGCATTCATATTTCA
938  80_HRV57a|  ACACGTGATGAAATGAGTCTTGAGAGCTTCTTAGGAAGATCTGGCTGCATTCATATTTCA
939  81_HRV57b|  ACACGTGATGAAATGAGTCTTGAGAGCTTCTTAGGAAGATCTGGCTGCATTCATATTTCA
940  82_HRV21    ACACGTGATGAAATGAGTATTGAAAGTTTTCTGGGCAGATCAGGGTGCATTCACATGTCA
941  83_HRVHan   ACACGTGATGAAATGAGTATTGAAAGTTTTCTAGGCAGATCAGGGTGTATCCACATGTCA
942  84_HRV43    ACCAGAGATGAAATGAGTATTGAAAGTTTCTTGGGCAGATCTGGTTGCATACATATTTCA
943  85_HRV43b|  ACCAGAGATGAAATGAGTATTGAAAGTTTCTTGGGCAGATCTGGTTGCATACATATTTCA
944  86_HRV43a|  ACCAGAGATGAAATGAGTATTGAAAGTTTCTTGGGCAGATCTGGTTGCATACATATTTCA
945  87_HRV75    ACTAGAGATGAGATGAGTATTGAGAGTTTCCTAGGCAGATCTGGATGTATTCATATTTCA
946  88_HRV75b|  ACTAGAGATGAGATGAGTATTGAGAGTTTCCTAGGCAGATCTGGATGTATTCATATTTCA
947  89_HRV75a|  ACTAGAGATGAGATGAGTATTGAGAGTTTCCTAGGCAGATCTGGATGTATTCATATTTCA
948  96_HRV9a|d  ACCAGAGATGAAATGAGTCTTGAAAGCTTCTTAGGGAGATCAGGTTGTATACACATATCT
949  97_HRV9b|d  ACCAGAGATGAAATGAGTCTTGAAAGCTTCTTAGGGAGATCAGGTTGTATACACATATCT
950  98_HRV9     ACCAGAGATGAAATGAGTCTTGAAAGCTTCTTAGGGAGATCAGGTTGTATACACATATCT
951  99_HRV32    ACTAGAGATGAGATGAGTCTTGAGAGCTTCTTAGGGAGGTCAGGATGTGTACATATATCC
952  100_HRV32a  ACTAGAGATGAGATGAGTCTTGAGAGCTTCTTAGGGAGGTCAGGATGTGTACATATATCC
953  101_HRV32b  ACTAGAGATGAGATGAGTCTTGAGAGCTTCTTAGGGAGGTCAGGATGTGTACATATATCC
954  102_HRV67   ACCAGAGATGAAATGAGTCTCGAGAGCTTTCTTGGAAGGTCAGGCTGTATTCATATATCA
955  103_HRV67a  ACCAGAGATGAAATGAGTCTCGAGAGCTTTCTTGGAAGGTCAGGCTGTATTCATATATCA
956  104_HRV67b  ACCAGAGATGAAATGAGTCTCGAGAGCTTTCTTGGAAGGTCAGGCTGTATTCATATATCA
957  105_HRV15   ACCAGAGATGAAATGAGTATTGAGAGCTTCCTTGGTAGATCAGGGTGTGTCCATATTTCT
958  106_HRV15a  ACCAGAGATGAAATGAGTATTGAGAGCTTCCTTGGTAGATCAGGGTGTGTCCATATTTCT
959  107_HRV15b  ACCAGAGATGAAATGAGTATTGAGAGCTTCCTTGGTAGATCAGGGTGTGTCCATATTTCT
960  108_HRV74a  ACAAGAGATGAGATGAGTGTAGAAAGTTTTCTTGGAAGATCAGGATGCATCCATATCTCA
961  109_HRV74b  ACAAGAGATGAGATGAGTGTAGAAAGTTTTCTTGGAAGATCAGGATGCATCCATATCTCA
962  110_HRV74   ACAAGAGATGAGATGAGTGTAGAAAGTTTTCTTGGAAGATCAGGATGCATCCATATCTCA
963  111_HRV38a  ACTAGAGATGAAATGAGTGTAGAAAGTTTTCTAGGAAGATCAGGTTGTGTACATATATCC
964  112_HRV38b  ACTAGAGATGAAATGAGTGTAGAAAGTTTTCTAGGAAGATCAGGTTGTGTACATATATCC
965  113_HRV38   ACTAGAGATGAAATGAGTGTAGAAAGTTTTCTAGGAAGATCAGGTTGTGTACATATATCC
966  114_HRV60   ACTAGAGATGAGATGAGTGTTGAGAGCTTCCTCGGCAGATCTGGATGTATTCATATTTCC
967  115_HRV60a  ACTAGAGATGAGATGAGTGTTGAGAGCTTCCTCGGCAGATCTGGATGTATTCATATTTCC
968  116_HRV60b  ACTAGAGATGAGATGAGTGTTGAGAGCTTCCTCGGCAGATCTGGATGTATTCATATTTCC
969  117_HRV64a  ACTAGAGATGAAATGAGCATTGAGAGTTTCTTGGGCAGGTCTGGTTGTATACACATATCA
970  118_HRV64b  ACTAGAGATGAAATGAGCATTGAGAGTTTCTTGGGCAGGTCTGGTTGTATACACATATCA
```

FIG. D11 CONT'D 07.trace                                                                9/20/2007 5:04 PM

```
 971 119_HRV64   ACTAGAGATGAAATGAGCATTGAGAGTTTCTTGGGCAGGTCTGGTTGTATACACATATCA
 972 120_HRV94a  ACAAGGGATGAAATGAGCATTGAAAGCTTCTTGGGAAGATCTGGCTGTATACACATAGCA
 973 121_HRV94b  ACAAGGGATGAAATGAGCATTGAAAGCTTCTTGGGAAGATCTGGCTGTATACACATAGCA
 974 122_HRV94   ACAAGGGATGAAATGAGCATTGAAAGCTTCTTGGGAAGATCTGGCTGTATACACATAGCA
 975 123_HRV22   ACTAGAGATGAAATGAGTATTGAGAGCTTCCTGGGAAGATCTGGTTGCATACATATATCA
 976 124_HRV22a  ACTAGAGATGAAATGAGTATTGAGAGCTTCCTGGGAAGATCTGGTTGCATACATATATCA
 977 125_HRV22b  ACTAGAGATGAAATGAGTATTGAGAGCTTCCTGGGAAGATCTGGTTGCATACATATATCA
 978 126_HRV82   ACTAGAGATGAGATGAGCCTTGAGAGTTTCCTAGGGAGATCTGGCTGCATACACATATCA
 979 127_HRV82b  ACTAGAGATGAGATGAGCCTTGAGAGTTTCCTAGGGAGATCTGGCTGCATACACATATCA
 980 128_HRV82a  ACTAGAGATGAGATGAGCCTTGAGAGTTTCCTAGGGAGATCTGGCTGCATACACATATCA
 981 129_HRV19   ACTAGGGATGAAATGAGCATAGAAAGTTTTCTTGGCAGATCCGGTTGTGTACATGTTTCA
 982 130_HRV19a  ACTAGGGATGAAATGAGCATAGAAAGTTTTCTTGGCAGATCCGGTTGTGTACATGTTTCA
 983 131_HRV19b  ACTAGGGATGAAATGAGCATAGAAAGTTTTCTTGGCAGATCCGGTTGTGTACATGTTTCA
 984 132_HRV13   ACTAGGGATGAAATGAGTGTTGAGAGCTTTTAGGCAGATCTGGTTGTATACACATGTCT
 985 133_HRV13a  ACTAGGGATGAAATGAGTGTTGAGAGCTTTTAGGCAGATCTGGTTGTATACACATGTCT
 986 134_HRV13b  ACTAGGGATGAAATGAGTGTTGAGAGCTTTTAGGCAGATCTGGTTGTATACACATGTCT
 987 135_HRV41   ACTAGAGATGAAATGAGCATAGAAAGCTTTTAGGTAGATCAGGCTGTGTACATAAGTCC
 988 136_HRV41a  ACTAGAGATGAAATGAGCATAGAAAGCTTTTAGGTAGATCAGGCTGTGTACATAAGTCC
 989 137_HRV41b  ACTAGAGATGAAATGAGCATAGAAAGCTTTTAGGTAGATCAGGCTGTGTACATAAGTCC
 990 138_HRV73   ACTAGAGATGAAATGAGCATTGAAAGCTTCCTTGGCAGGTCAGGTTGTATACACATGTCA
 991 139_HRV73b  ACTAGAGATGAAATGAGCATTGAAAGCTTCCTTGGCAGGTCAGGTTGTATACACATGTCA
 992 140_HRV73a  ACTAGAGATGAAATGAGCATTGAAAGCTTCCTTGGCAGGTCAGGTTGTATACACATGTCA
 993 141_HRV61   ACAAGAGATGAAATGAGTGTAGAAAGTTTCTTGGGTAGATCAGGGTGCATACATATGTCA
 994 142_HRV61a  ACAAGAGATGAAATGAGTGTAGAAAGTTTCTTGGGTAGATCAGGGTGCATACATATGTCA
 995 143_HRV61b  ACAAGAGATGAAATGAGTGTAGAAAGTTTCTTGGGTAGATCAGGGTGCATACATATGTCA
 996 144_HRV96   ACGAGAGATGAAATGAGCATTGAGAGCTTTTGGGTAGATCAGGGTGTATACACATGTCA
 997 145_HRV96b  ACGAGAGATGAAATGAGCATTGAGAGCTTTTGGGTAGATCAGGGTGTATACACATGTCA
 998 146_HRV96a  ACGAGAGATGAAATGAGCATTGAGAGCTTTTGGGTAGATCAGGGTGTATACACATGTCA
 999  90_HRV16a| ACATTGGATGAAATGAGTGTGGAAAGCTTCCTAGGCAGATCGGGGTGCATCCATGAATCA
1000  91_HRV16b| ACATTGGATGAAATGAGTGTGGAAAGCTTCCTAGGCAGATCGGGGTGCATCCATGAATCA
1001  92_1AYM_A  ACATTGGATGAAATGAGTGTGGAAAGCTTCCTAGGCAGATCGGGGTGCATCCATGAATCA
1002  93_HRV81a| ACACTGGATGAAATGAGTGTAGAAAGTTTTTAGGCAGATCAGGTTGCATTCATGAATCC
1003  94_HRV81b| ACACTGGATGAAATGAGTGTAGAAAGTTTTTAGGCAGATCAGGTTGCATTCATGAATCC
1004  95_HRV81   ACACTGGATGAAATGAGTGTAGAAAGTTTTTAGGCAGATCAGGTTGCATTCATGAATCC
1005 147_HRV2    ACAAGAGATGAAATGAGTTTAGAGAGTTTTCTTGGCAGATCAGGATGCATACATGAATCT
1006 148_HRV2a|  ACAAGAGATGAAATGAGTTTAGAGAGTTTTCTTGGCAGATCAGGATGCATACATGAATCT
1007 149_HRV2b|  ACAAGAGATGAAATGAGTTTAGAGAGTTTTCTTGGCAGATCAGGATGCATACATGAATCT
1008 150_HRV49a  ACAAGAGATGAAATGAGTTTTAGAGAGTTTCTTGGTAGGTCAGGGTGTATACATGAATCC
1009 151_HRV49b  ACAAGAGATGAAATGAGTTTAGAGAGTTTTCTTGGTAGGTCAGGGTGTATACATGAATCC
1010 152_HRV49   ACAAGAGATGAAATGAGTTTAGAGAGTTTTCTTGGTAGGTCAGGGTGTATACATGAATCC
1011 153_HRV23a  ACAAGAGATGAAATGAGTTTAGAAAGTTTTCTTGGTAGGTCAGGGTGTATACATGAATCT
1012 154_HRV23b  ACAAGAGATGAAATGAGTTTAGAAAGTTTCCTTGGTAGGTCAGGGTGTATACATGAATCT
1013 155_HRV23   ACAAGAGATGAAATGAGTTTAGAAAGTTTCCTTGGTAGGTCAGGGTGTATACATGAATCT
1014 156_HRV30a  ACAAGGGATGAAATGAGTTTAGAAAGCTTTCTTGGTAGATCAGGATGTATACACGAGTCT
1015 157_HRV30b  ACAAGGGATGAAATGAGTTTAGAAAGCTTTCTTGGTAGATCAGGATGTATACACGAGTCT
1016 158_HRV30   ACAAGGGATGAAATGAGTTTAGAAAGCTTTCTTGGTAGATCAGGATGTATACACGAGTCT
1017 159_HRV7    ACAAGGGATGAAACTAGTATAGAGAGTTTCTTAGGTAGATCTGGATGTATTGCTAAAGTT
1018 160_HRV7b|  ACAAGGGATGAAACTAGTATAGAGAGTTTCTTAGGTAGATCTGGATGTATTGCTAAAGTT
1019 161_HRV7a|  ACAAGGGATGAAACTAGTATAGAGAGTTTCTTAGGTAGATCTGGATGTATTGCTAAAGTT
1020 162_HRV88   ACAAGGGATGAAACCAGCATTGAAAGCTTTCTGGGTAGGTCTGGATGCATAGCAAAAATT
1021 163_HRV88a  ACAAGGGATGAAACCAGCATTGAAAGCTTTCTGGGTAGGTCTGGATGCATAGCAAAAATT
1022 164_HRV88b  ACAAGGGATGAAACCAGCATTGAAAGCTTTCTGGGTAGGTCTGGATGCATAGCAAAAATT
1023 165_HRV36a  ACAAGAGATGAGACAAGTATTGAAAGCTTCTTAGGTAGGTCAGGGTGCATAGCTATGATA
1024 166_HRV36b  ACAAGAGATGAGACAAGTATTGAAAGCTTCTTAGGTAGGTCAGGGTGCATAGCTATGATA
1025 167_HRV36   ACAAGAGATGAGACAAGTATTGAAAGCTTCTTAGGTAGGTCAGGGTGCATAGCTATGATA
1026 168_HRV89a  ACAAGGGATGAAACAAGTATTGAGAGTTTCTTAGGTAGGTCAGGGTGTATCGCTATGATA
1027 169_HRV89b  ACAAGGGATGAAACAAGTATTGAGAGTTTCTTAGGTAGGTCAGGGTGTATCGCTATGATA
1028 170_HRV89   ACAAGGGATGAAACAAGTATTGAGAGTTTCTTAGGTAGGTCAGGGTGTATCGCTATGATA
1029 171_HRV58   ACAAGAGATGAAACTAGCATTGAAAGCTTTTAGGTAGATCTGGTTGCATTGCTATCATA
1030 172_HRV58a  ACAAGAGATGAAACTAGCATTGAAAGCTTTTAGGTAGATCTGGTTGCATTGCTATCATA
1031 173_HRV58b  ACAAGAGATGAAACTAGCATTGAAAGCTTTTAGGTAGATCTGGTTGCATTGCTATCATA
1032 174_HRV12a  ACTAGAGATGAGATGTCAATTGAATCTTTCCTTGGTCGGTCCGGATGCATTTCAATTATC
1033 175_HRV12b  ACTAGAGATGAGATGTCAATTGAATCTTTCCTTGGTCGGTCCGGATGCATTTCAATTATC
1034 176_HRV12   ACTAGAGATGAGATGTCAATTGAATCTTTCCTTGGTCGGTCCGGATGCATTTCAATTATC
1035 177_HRV78a  ACAAGAGATGAAATGAGCATTGAAAGTTTCCTCGGAAGATCAGGTTGTGCAACAATTATG
```

FIG. D11 CONT'D

```
07.trace                                                                9/20/2007 5:04 PM 1036  178_HRV78b    ACAAGAGATGAAATGAGCATTGAAAGTTTCCTCGGAAGATCAGGTTGTGCAACAATTATG
1037  179_HRV78     ACAAGAGATGAAATGAGCATTGAAAGTTTCCTCGGAAGATCAGGTTGTGCAACAATTATG
1038  180_HRV20     ACCCGTGATGAAATGAGTGTGGAAAGTTTCTTGGTAGATCTGGTTGCATTGCTATCATA
1039  181_HRV20a    ACCCGTGATGAAATGAGTGTGGAAAGTTTCTTGGTAGATCTGGTTGCATTGCTATCATA
1040  182_HRV20b    ACCCGTGATGAAATGAGTGTGGAAAGTTTTCTTGGTAGATCTGGTTGCATTGCTATCATA
1041  183_HRV68     ACAAGGGATGAAATGAGCATAGAGAGCTTCCTCGGTAGGTCAGGTTGCATTGCAATCATA
1042  184_HRV68a    ACAAGGGATGAAATGAGCATAGAGAGCTTCCTCGGTAGGTCAGGTTGCATTGCAATCATA
1043  185_HRV68b    ACAAGGGATGAAATGAGCATAGAGAGCTTCCTCGGTAGGTCAGGTTGCATTGCAATCATA
1044  186_HRV28     ACCCGTGATGAAATGAGTATAGAGAGTTTCTTAGGTAGGTCTAGTTGCATTGCAATAATC
1045  187_HRV28a    ACCCGTGATGAAATGAGTATAGAGAGTTTCTTAGGTAGGTCTAGTTGCATTGCAATAATC
1046  188_HRV28b    ACCCGTGATGAAATGAGTATAGAGAGTTTCTTAGGTAGGTCTAGTTGCATTGCAATAATC
1047  189_HRV53a    ACCCGGGATGAAATGAGCATTGAAAGTTTCTTAGGCAGATCAAGTTGCATTGCTGAGATC
1048  190_HRV53b    ACCCGTGATGAAATGAGCATTGAAAGTTTCTTAGGCAGATCAAGTTGCATTGCTGAGATC
1049  191_HRV53     ACCCGGGATGAAATGAGCATTGAAAGTTTCTTAGGCAGATCAAGTTGCATTGCTGAGATC
1050  192_HRV46a    ACAAAAGATGAAATGAGTATAGAAAGTTTTCTAGGAAGGTCAGGCTGCATTGCCATTATT
1051  193_HRV46b    ACAAAAGATGAAATGAGTATAGAAAGTTTTCTAGGAAGGTCAGGCTGCATTGCCATTATT
1052  194_HRV46     ACAAAAGATGAAATGAGTATAGAAAGTTTTCTAGGAAGGTCAGGCTGCATTGCCATTATT
1053  195_HRV80a    ACAAAGGATGAGATGAGCATTGAAAGTTTCTTAGGAAGATCTGGTTGTGTTGCTATCATT
1054  196_HRV80b    ACAAAGGATGAGATGAGCATTGAAAGTTTCTTAGGAAGATCTGGTTGTGTTGCTATCATT
1055  197_HRV80     ACAAAGGATGAGATGAGCATTGAAAGTTTCTTAGGAAGATCTGGTTGTGTTGCTATCATT
1056  198_HRV51     ACTAGAGATGAAATGAGTATAGAGAGTTTCTTGGGTAGATCTGCTTGCGTAGCAATCATC
1057  199_HRV51a    ACTAGAGATGAAATGAGTATAGAGAGTTTCTTGGGTAGATCTGCTTGCGTAGCAATCATC
1058  200_HRV51b    ACTAGAGATGAAATGAGTATAGAGAGTTTCTTGGGTAGATCTGCTTGCGTAGCAATCATC
1059  201_HRV65a    ACCAGAGATGAGATGAGCGTAGAGAGTTTCCTGGGCAGATCTGCCTGCATAGCAGTCATT
1060  202_HRV65b    ACCAGAGATGAGATGAGCGTAGAGAGTTTCCTGGGCAGATCTGCCTGCATAGCAGTCATT
1061  203_HRV65     ACCAGAGATGAGATGAGCGTAGAGAGTTTCCTGGGCAGATCTGCCTGCATAGCAGTCATT
1062  204_HRV71a    ACTAGGGATGAAATGAGCATTGAGAGCTTCTTGGGCAGATCTGCATGCATAGCTACCATA
1063  205_HRV71b    ACTAGGTGATGAAATGAGCATTGAGAGCTTCTTGGGCAGATCTGCATGCATAGCTACCATA
1064  206_HRV71     ACTAGGGATGAAATGAGCATTGAGAGCTTCTTGGGCAGATCTGCATGCATAGCTACCATA
1065  207_HRV8      ACTAGGCATGAGACATCACTGGAATCTTTCTTGGGTAGAGCAGGATGCATTAAAATCATT
1066  208_HRV95     ACTAGGTATGAGACATCACTGGAATCTTTCTTGGGTAGAGCAGGATGCATTAAATTATT
1067  209_HRV45     ACCAGACATGAAACCTCCATTGAATCTTTTTGGGTAGGGCTGGATGTGTGGCCAATATT
1068  210_HRV45a    ACCAGACATGAAACCTCCATTGAATCTTTTTTGGGTAGGGCTGGATGTGTGGCCAATATT
1069  211_HRV45b    ACCAGACATGAAACCTCCATTGAATCTTTTTTGGGTAGGGCTGGATGTGTGGCCAATATT
1070  GROUP_1       AC-----ATGA-A------T-GA----TT--T-GG--G--C----TG-------------
1071
1072  1_HRV1A1|d    AGAATAAAGGTTGATTACACTGAC---------------TATAATGGA---CAGGACATA
1073  2_HRV1A2|d    AGAATAAAGGTTGATTACACTGAC---------------TATAATGGA---CAGGACATA
1074  3_HRV1A|cD    AGAATAAAGGTTGATTACACTGAC---------------TATAATGGA---CAGGACATA
1075  4_HRV1B1|d    AGAATAAAGGTTGATTACAATGAC---------------TACAATGGA---GTGAACAAA
1076  5_HRV1B2|d    AGAATAAAGGTTGATTACAATGAC---------------TACAATGGA---GTGAACAAA
1077  6_HRV1B       AGAATAAAGGTTGATTACAATGAC---------------TACAATGGA---GTGAACAAA
1078  7_HRV40a|d    ACAATTACAGTGGATAACAGTTTG---------------GAATATG------ATGACCAC
1079  8_HRV40b|d    ACAATTACAGTGGATAACAGTTTG---------------GAATATG------ATGACCAC
1080  9_HRV40       ACAATTACAGTGGATAACAGTTTG---------------GAATATG------ATGACCAC
1081  10_HRV85      ACAATTACTGTGAATAACAACCTA---------------GATTATG------ATGAAAAT
1082  11_HRV85a|    ACAATTACTGTGAATAACAACCTA---------------GATTATG------ATGAAAAT
1083  12_HRV85b|    ACAATTACTGTGAATAACAACCTA---------------GATTATG------ATGAAAAT
1084  13_HRV56a|    ACTATAACTGTGGATAATGATGTA---------------GATTATA------ATTCAAAG
1085  14_HRV56b|    ACTATAACTGTGGATAATGATGTA---------------GATTATA------ATTCAAAG
1086  15_HRV56      ACTATAACTGTGGATAATGATGTA---------------GATTATA------ATTCAAAG
1087  16_HRV54      ACCATTACAATTCAAAATGATGTA---------------GAATACA------ATGATCAC
1088  17_HRV98      ACTATCACTATTCAAAATGATGTA---------------GAATATA------ACGATCAT
1089  18_HRV59a|    ACTATTACTGTCAATAAAGACATA---------------AAATATG------ATGATGGA
1090  19_HRV59b|    ACTATTACTGTCAATAAAGACATA---------------AAATATG------ATGATGGA
1091  20_HRV59      ACTATTACTGTCAATAAAGACATA---------------AAATATG------ATGATGGA
1092  21_HRV63      ACTATCACTGTTGACAAAACCATT---------------GACTATG------ACACTGGA
1093  22_HRV63b|    ACTATCACTGTTGACAAAACCATT---------------GACTATG------ACACTGGA
1094  23_HRV63a|    ACTATCACTGTTGACAAAACCATT---------------GACTATG------ACACTGGA
1095  24_HRV39      ACAATTACTATGAAGAAGGAG------------------AACTATA------ATGATCAT
1096  25_HRV39a|    ACAATTACTATGAAGAAGGAG------------------AACTATA------ATGATCAT
1097  26_HRV39b|    ACAATTACTATGAAGAAGGAG------------------AACTATA------ATGAACAT
1098  27_HRV10a|    ACAATAACTGTTAATAATACAAGA---------------CCCTACA------ATGAACAC
1099  28_HRV10b|    ACAATAACTGTTAATAATACAAGA---------------CCCTACA------ATGAACAC
1100  29_HRV10      ACAATAACTGTTAATAATACAAGA---------------CCCTACA------ATGAACAC
```

FIG. D11 CONT'D

```
07.trace                                                                    9/20/2007 5:04 PM 1101  30_HRV100a   ACAATTACTGTAAGTAAAATGAAA---------------AATTATA------ATGAGCAC
1102  31_HRV100b   ACAATTACTGTAAGTAAAATGAAA---------------AATTATA------ATGAGCAC
1103  32_HRV100    ACAATTACTGTAAGTAAAATGAAA---------------AATTATA------ATGAGCAC
1104  33_HRV66     ACAATTAATGTGGATAGCACAAAA---------------ACATATG------ATGAATCC
1105  34_HRV66b|   ACAATTAATGTGGATAGCACAAAA---------------ACATATG------ATGAATCC
1106  35_HRV66a|   ACAATTAATGTGGATAGCACAAAA---------------ACATATG------ATGAATCC
1107  36_HRV77a|   ACAATAAATGTAGAAGATGGTAAA---------------ACTTATG------ATGAATCT
1108  37_HRV77b|   ACAATAAATGTAGAAGATGGTAAA---------------ACTTATG------ATGAATCT
1109  38_HRV77     ACAATAAATGTAGAAGATGGTAAA---------------ACTTATG------ATGAATCT
1110  39_HRV62a    ACAATTGAA--------ACAACG----------------CTTAGTC------ATAAAGAT
1111  40_HRV62b    ACAATTGAA--------ACAACG----------------CTTAGTC------ATAAAGAT
1112  41_HRV25     ACAATTGAA--------ACAAAA----------------CTTAAAC------ATGATGAA
1113  42_HRV29a    ACAATAAAA--------GCAAAT----------------CAGGCAC------ATGACGCC
1114  43_HRV29b    ACAATAAAA--------GCAAAT----------------CAGGCAC------ATGACGCC
1115  44_HRV44a    ACAATAAAG--------ACAAAT----------------CAGGCAC------ACAATACC
1116  45_HRV44b    ACAATAAAG--------ACAAAT----------------CAGGCAC------ACAATACC
1117  46_HRV31     ATAATAGAA--------CCAGAT----------------GGACTCC------ATGATAGC
1118  47_HRV31a|   ATAATAGAA--------CCAGAT----------------GGACTCC------ATGATAGC
1119  48_HRV31b|   ATAATAGAA--------CCAGAT----------------GGACTCC------ATGATAGC
1120  49_HRV47     ACAATAAAA--------TCAGAT----------------GAGCAAC------ACATTAAT
1121  50_HRV47a|   ACAATAAAA--------TCAGAT----------------GAGCAAC------ACATTAAT
1122  51_HRV47b|   ACAATACAA--------TCAAAT----------------GAGCAAC------ACATTAAT
1123  52_HRV11     AAGTTAATTGTGCAGTATGAAGAC---------------TATAAT------GGAAAGAAA
1124  53_HRV11b|   AAGTTAATTGTGCAGTATGAAGAC---------------TATAAT------GGAAAGAAA
1125  54_HRV11a|   AAGTTAATTGTGCAGTATGAAGAC---------------TATAAT------GGAAAGAAA
1126  55_HRV76     AAGCTAGTTGTAGAATATGAGGGA---------------TATGAT------GATACAAAA
1127  56_HRV76b|   AAGCTAGTTGTAGAATATGAGGGA---------------TATGAT------GATACAAAA
1128  57_HRV76a|   AAGCTAGTTGTAGAATATGAGGGA---------------TATGAT------GATACAAAA
1129  58_HRV33     AAATTAGTAGTGAAATATGAAGAC---------------TATAAT------GAGAAAAAG
1130  59_HRV33b|   AAATTAGTAGTGAAATATGAAGAC---------------TATAAT------GAGAAAAAG
1131  60_HRV33a|   AAATTAGTAGTGAAATATGAAGAC---------------TATAAT------GAGAAAAAG
1132  61_HRV24a|   AAGTTGACTGTGGATTAT---GAC---------------AATTAT------GATACAAAA
1133  62_HRV24b|   AAGTTGACTGTGGATTAT---GAC---------------AATTAT------GATACAAAA
1134  63_HRV24     AAGTTGACTGTGGATTAT---GAC---------------AATTAT------GATACAAAA
1135  64_HRV90     AAATTAGTTGTAAACTAT---GAT---------------AATTAT------GATGAAAAC
1136  65_HRV90a|   AAATTAGTTGTAAACTAT---GAT---------------AATTAT------GATGAAAAC
1137  66_HRV90b|   AAATTAGTTGTAAACTAT---GAT---------------AATTAT------GATGAAAAC
1138  67_HRV34     AAACTTGTTGTAGATTATGAAAAT---------------TACAATGCA---AAAACAAAG
1139  68_HRV34b|   AAACTTGTTGTAGATTATGAAAAT---------------TACAATGCA---AAAACAAAG
1140  69_HRV34a|   AAACTTGTTGTAGATTATGAAAAT---------------TACAATGCA---AAAACAAAG
1141  70_HRV50a|   AAATTAGTTGTTGATTATGATGGT---------------TACAATGAG---GAAACAAAG
1142  71_HRV50b|   AAATTAGTTGTTGATTATGATGGT---------------TACAATGAG---GAAACAAAG
1143  72_HRV50     AAATTAGTTGTTGATTATGATGGT---------------TACAATGAG---GAAACAAAG
1144  73_HRV18a|   AAGTTAGTTGTACATTATGAAGAT---------------TATAATGCA---GAAACAAGG
1145  74_HRV18b|   AAGTTAGTTGTACATTATGAAGAT---------------TATAATGCA---GAAACAAGG
1146  75_HRV18     AAGTTAGTTGTACATTATGAAGAT---------------TATAATGCA---GAAACAAGG
1147  76_HRV55     GAGTTAGTTGTTCATTATGAAGAA---------------TATAACAAA---GAGGGAAAA
1148  77_HRV55b|   GAGTTAGTTGTTCATTATGAAGAA---------------TATAACAAA---GAGGGAAAA
1149  78_HRV55a|   GAGTTAGTTGTTCATTATGAAGAA---------------TATAACAAA---GAGGGAAAA
1150  79_HRV57     GAGCTTAAGGTAAAATATGAAAAT---------------TACAACACA---GAG------
1151  80_HRV57a|   GAGCTTAAGGTAAAATATGAAAAT---------------TACAACACA---GAG------
1152  81_HRV57b|   GAGCTTAAGGTAAAATATGAAAAT---------------TACAACACA---GAG------
1153  82_HRV21     AAATTAGTAGTTAACTATGATAAT---------------TACAATACT---GGAGAAAAT
1154  83_HRVHan    AAATTAATAGTTAACTATGACAAC---------------TACAATACT---GGAGAAAAT
1155  84_HRV43     ACACTTGAAGTAAATTATGATGAT---------------TATAATGGG---ACAGGCATA
1156  85_HRV43b|   ACACTTGAAGTAAATTATGATGAT---------------TATAATGGG---ACAGGCATA
1157  86_HRV43a|   ACACTTGAAGTAAATTATGATGAT---------------TATAATGGG---ACAGGCATA
1158  87_HRV75     ACACTTGAGATGGATTATACAAAC---------------TATAATGGA---GAAGGCAAA
1159  88_HRV75b|   ACACTTGAGATGGATTATACAAAC---------------TATAATGGA---GAAGGCAAA
1160  89_HRV75a|   ACACTTGAGATGGATTATACAAAC---------------TATAATGGA---GAAGGCAAA
1161  96_HRV9a|d   AAATTGAATATTGATTACAGTGAC---------------TATGATAAG---AGTGTTGAA
1162  97_HRV9b|d   AAATTGAATATTGATTACAGTGAC---------------TATGATAAG---AGTGTTGAA
1163  98_HRV9      AAATTGAATATTGATTACAGTGAC---------------TATGATAAG---AGTGTTGAA
1164  99_HRV32     AAATTAGATATTGATTATACCAAT---------------TACAATAAA---AGTGTTAAG
1165  100_HRV32a   AAATTAGATATTGATTATACCAAT---------------TACAATAAA---AGTGTTAAG
```

FIG. D11 CONT'D

```
07.trace                                                                    9/20/2007 5:04 PM 1166  101_HRV32b    AAATTAGATATTGATTATACCAAT---------------TACAATAAA---AGTGTTAAG
1167  102_HRV67     AAATTGAATATTGATTATAATGCA---------------TATGATGAA---AGTAGGGAC
1168  103_HRV67a    AAATTGAATATTGATTATAATGCA---------------TATGATGAA---AGTAGGGAC
1169  104_HRV67b    AAATTGAATATTGATTATAATGCA---------------TATGATGAA---AGTAGGGAC
1170  105_HRV15     GATTTGAAAATACATTATGAAGAT---------------TATAATAAA---GATGGGAAA
1171  106_HRV15a    GATTTGAAAATACATTATGAAGAT---------------TATAATAAA---GATGGGAAA
1172  107_HRV15b    GATTTGAAAATACATTATGAAGAT---------------TATAATAAA---GATGGGAAA
1173  108_HRV74a    CATCTAAAAATTGATTATACAAAC---------------TATAATGTT---AAAGGGAAG
1174  109_HRV74b    CATCTAAAAATTGATTATACAAAC---------------TATAATGTT---AAAGGGAAG
1175  110_HRV74     CATCTAAAAATTGATTATACAAAC---------------TATAATGTT---AAAGGGAAG
1176  111_HRV38a    AATCTTGACATAGATTACATTAAT---------------TACAACTCT---GAAGACAAA
1177  112_HRV38b    AATCTTGACATAGATTACATTAAT---------------TACAACTCT---GAAGACAAA
1178  113_HRV38     AATCTTGACATAGATTACATTAAT---------------TACAACTCT---GAAGACAAA
1179  114_HRV60     AAATTAGAAATTGACTATAGTAAC---------------TACAATGAG---GAGAATAAA
1180  115_HRV60a    AAATTAGAAATTGACTATAGTAAC---------------TACAATGAG---GAGAATAAA
1181  116_HRV60b    AAATTAGAAATTGACTATAGTAAC---------------TACAATGAG---GAGAATAAA
1182  117_HRV64a    GATTTAAAAGTAAATTATACTGGG---------------TATAATGAT---GAAGGTAAC
1183  118_HRV64b    GATTTAAAAGTAAATTATACTGGG---------------TATAATGAT---GAAGGTAAC
1184  119_HRV64     GATTTAAAAGTAAATTATACTGGG---------------TATAATGAT---GAAGGTAAC
1185  120_HRV94a    CATCTAGAGATCAAGTATGATGGT---------------TACAATGAT---GCTGGCAAC
1186  121_HRV94b    CATCTAGAGATCAAGTATGATGGT---------------TACAATGAT---GCTGGCAAC
1187  122_HRV94     CATCTAGAGATCAAGTATGATGGT---------------TACAATGAT---GCTGGCAAC
1188  123_HRV22     CACTTAGAAGTAAAATACACAGGG---------------TATAATGAA---GAGGGTAAT
1189  124_HRV22a    CACTTAGAAGTAAAATACACAGGG---------------TATAATGAA---GAGGGTAAT
1190  125_HRV22b    CACTTAGAAGTAAAATACACAGGG---------------TATAATGAA---GAGGGTAAT
1191  126_HRV82     CACCTAAATGTCAGATACACTG-----------------ATTATAAT---GAAGGTAAT
1192  127_HRV82b    CACCTAAATGTCAGATACACTG-----------------ATTATAAT---GAAGGTAAT
1193  128_HRV82a    CACCTAAATGTCAGATACACTG-----------------ATTATAAT---GAAGGTAAT
1194  129_HRV19     GAGCTCCAATTAGATTATACCAAT---------------TACAATCAA---GAAAATAAT
1195  130_HRV19a    GAGCTCCAATTAGATTATACCAAT---------------TACAATCAA---GAAAATAAT
1196  131_HRV19b    GAGCTCCAATTAGATTATACCAAT---------------TACAATCAA---GAAAATAAT
1197  132_HRV13     ACCATGAACATAGATTATACTAAT---------------TATGATGAT---TCTGTTAAT
1198  133_HRV13a    ACCATGAACATAGATTATACTAAT---------------TATGATGAT---TCTGTTAAT
1199  134_HRV13b    ACCATGAACATAGATTATACTAAT---------------TATGATGAT---TCTGTTAAT
1200  135_HRV41     ACTTTGAATATAGATTATACTGAT---------------TATGATGAT---TCTATCCAG
1201  136_HRV41a    ACTTTGAATATAGATTATACTGAT---------------TATGATGAT---TCTATCCAG
1202  137_HRV41b    ACTTTGAATATAGATTATACTGAT---------------TATGATGAT---TCTATCCAG
1203  138_HRV73     ACTATGAATATAAATTATGAAAAT---------------TATGATGAT---GCTCCTGAA
1204  139_HRV73b    ACTATGAATATAAATTATGAAAAT---------------TATGATGAT---GCTCCTGAA
1205  140_HRV73a    ACTATGAATATAAATTATGAAAAT---------------TATGATGAT---GCTCCTGAA
1206  141_HRV61     ACATTAAATATAAACTATGATAAC---------------TATGATGAT---TCTATTGAA
1207  142_HRV61a    ACATTAAATATAAACTATGATAAC---------------TATGATGAT---TCTATTGAA
1208  143_HRV61b    ACATTAAATATAAACTATGATAAC---------------TATGATGAT---TCTATTGAA
1209  144_HRV96     ACATTAAACATAGATTATGACAAT---------------TATGATGAC---TCCCCTAAG
1210  145_HRV96b    ACATTAAACATAGATTATGACAAT---------------TATGATGAC---TCCCCTAAG
1211  146_HRV96a    ACATTAAACATAGATTATGACAAT---------------TATGATGAC---TCCCCTAAG
1212  90_HRV16a|    GTGTTGGATATTGTGGACAATTAC---------------AATGAT-----------CAA
1213  91_HRV16b|    GTGTTGGATATTGTGGACAATTAC---------------AATGAT-----------CAA
1214  92_1AYM_A     GTGTTGGATATTGTGGACAATTAC---------------AATGAT-----------CAA
1215  93_HRV81a|    ATATTGGACATTAAAGAGGATTAC---------------AATACC-----------CAG
1216  94_HRV81b|    ATATTGGACATTAAAGAGGATTAC---------------AATACC-----------CAG
1217  95_HRV81      ATATTGGACATTAAAGAGGATTAC---------------AATACC-----------CAG
1218  147_HRV2      AAATTAGAGGTTACACTTGCAAAT---------------TATAACA--------AGGAG
1219  148_HRV2a|    AAATTAGAGGTTACACTTGCAAAT---------------TATAACA--------AGGAG
1220  149_HRV2b|    AAATTAGAGGTTACACTTGCAAAT---------------TATAACA--------AGGAG
1221  150_HRV49a    AAACTAGAGGTCACACTTACAAAT---------------TACAATG--------AAAAT
1222  151_HRV49b    AAACTAGAGGTCACACTTACAAAT---------------TACAATG--------AAAAT
1223  152_HRV49     AAACTAGAGGTCACACTTACAAAT---------------TACAATG--------AAAAT
1224  153_HRV23a    AAATTAAAAGTTGAGATCGGAAAC---------------TATGATG--------AAAAC
1225  154_HRV23b    AAATTAAAAGTTGAGATCGGAAAC---------------TATGATG--------AAAAC
1226  155_HRV23     AAATTAAAAGTTGAGATCGGAAAC---------------TATGATG--------AAAAC
1227  156_HRV30a    AAATTAGAACTTGAGCTTGCACAC---------------TATGATA--------AAAAG
1228  157_HRV30b    AAATTAGAACTTGAGCTTGCACAC---------------TATGATA--------AAAAG
1229  158_HRV30     AAATTAGAACTTGAGCTTGCACAC---------------TATGATA--------AAAAG
1230  159_HRV7      AAACTTGACACAA------CACAGGGT---------GACTATGACACAGGCAAAGGTGTT
```

FIG. D11 CONT'D

07.trace                                                                                    9/20/2007 5:04 PM

```
1231 160_HRV7b|       AAACTTGACACAA------CACAGGGT---------GACTATGACACAGGCAAAGGTGTT
1232 161_HRV7a|       AAACTTGACACAA------CACAGGGT---------GACTATGACACAGGCAAAGGTGTT
1233 162_HRV88        AAACTTGACACAA------ATGAAGGT---------GATTACGACACA---ATAGGTGTT
1234 163_HRV88a       AAACTTGACACAA------ATGAAGGT---------GATTACGACACA---ATAGGTGTT
1235 164_HRV88b       AAACTTGACACAA------ATGAAGGT---------GATTACGACACA---ATAGGTGTT
1236 165_HRV36a       GAATTTAGCACAAGTAGTGATAAAGAT---------GAACATGATGAA---ATTGGCAAG
1237 166_HRV36b       GAATTTAGCACAAGTAGTGATAAAGAT---------GAACATGATGAA---ATTGGCAAG
1238 167_HRV36        GAATTTAGCACAAGTAGTGATAAAGAT---------GAACATGATGAA---ATTGGCAAG
1239 168_HRV89a       GAATTTAATACAAGTAGTGATAAAACT---------GAACATGATAAA---ATTGGTAAA
1240 169_HRV89b       GAATTTAATACAAGTAGTGATAAAACT---------GAACATGATAAA---ATTGGTAAA
1241 170_HRV89        GAATTTAATACAAGTAGTGATAAAACT---------GAACATGATAAA---ATTGGTAAA
1242 171_HRV58        AAATTTAACACAA------ATAAGACT---------AATTATGATGAC---ATAGGTGTA
1243 172_HRV58a       AAATTTAACACAA------ATAAGACT---------AATTATGATGAC---ATAGGTGTA
1244 173_HRV58b       AAATTTAACACAA------ATAAGACT---------AATTATGATGAC---ATAGGTGTA
1245 174_HRV12a       GAATTGGATTTAGACCATGAAGGT--------------TATTCAGCA---GAAGGGAAA
1246 175_HRV12b       GAATTGGATTTAGACCATGAAGGT--------------TATTCAGCA---GAAGGGAAA
1247 176_HRV12        GAATTGGATTTAGACCATGAAGGT--------------TATTCAGCA---GAAGGGAAA
1248 177_HRV78a       AGACTAGAATTGGACCACACTGAT--------------TACAATGCT---GAAGGGAAA
1249 178_HRV78b       AGACTAGAATTGGACCACACTGAT--------------TACAATGCT---GAAGGGAAA
1250 179_HRV78        AGACTAGAATTGGACCACACTGAT--------------TACAATGCT---GAAGGGAAA
1251 180_HRV20        CATACTGACTTAGATCATGAAGCACAA---------CAATATAATGCA---CCCGGAAAA
1252 181_HRV20a       CATACTGACTTAGATCATGAAGCACAA---------CAATATAATGCA---CCCGGAAAA
1253 182_HRV20b       CATACTGACTTAGATCATGAAGCACAA---------CAATATAATGCA---CCCGGAAAA
1254 183_HRV68        CATACTGACTTAGATCACAATGAGGAT---------CAGTACAATGCA---CCTGGAAAA
1255 184_HRV68a       CATACTGACTTAGATCACAATGAGGAT---------CAGTACAATGCA---CCTGGAAAA
1256 185_HRV68b       CATACTGACTTAGATCACAATGAGGAT---------CAGTACAATGCA---CCTGGAAAA
1257 186_HRV28        CATACTGATGTTGTGCATGAAACAGAC---------AAGTACAACCAC---CCAGGGAAG
1258 187_HRV28a       CATACTGATGTTGTGCATGAAACAGAC---------AAGTACAACCAC---CCAGGGAAG
1259 188_HRV28b       CATACTGATGTTGTGCATGAAACAGAC---------AAGTACAACCAC---CCAGGGAAG
1260 189_HRV53a       CATACCAATTTAGACCAT---ACTG-----------GATACAATGAG---CCTGGGAAA
1261 190_HRV53b       CATACCAATTTAGACCAT---ACTG-----------GATACAATGAG---CCTGGGAAA
1262 191_HRV53        CATACCAATTTAGACCAT---ACTG-----------GATACAATGAG---CCTGGGAAA
1263 192_HRV46a       GAGACAGAATTGAATCATGAAGAAGGG---------AAATACAATGCA---GAAGATCAA
1264 193_HRV46b       GAGACAGAATTGAATCATGAAGAAGGG---------AAATACAATGCA---GAAGATCAA
1265 194_HRV46        GAGACAGAATTGAATCATGAAGAAGGG---------AAATACAATGCA---GAAGATCAA
1266 195_HRV80a       GAAACCAAATTAAACCATGAAACAGAC---------ATGTACAATGCT---GATGGTCAG
1267 196_HRV80b       GAAACCAAATTAAACCATGAAACAGAC---------ATGTACAATGCT---GATGGTCAG
1268 197_HRV80        GAAACCAAATTAAACCATGAAACAGAC---------ATGTACAATGCT---GATGGTCAG
1269 198_HRV51        CATACAAACCTTGAGCATGTTGAAGCAGACAGACAAGCCTACAATGCA---AAAGGGAAA
1270 199_HRV51a       CATACAAACCTTGAGCATGTTGAAGCAGACAGACAAGCCTACAATGCA---AAAGGGAAA
1271 200_HRV51b       CATACAAACCTTGAGCATGTTGAAGCAGACAGACAAGCCTACAATGCA---AAAGGGAAA
1272 201_HRV65a       CACACAGATCTTAAACATGACCATGAAGGCCAAAATGTTTACAATGAC---GAAGGCAGA
1273 202_HRV65b       CACACAGATCTTAAACATGACCATGAAGGCCAAAATGTTTACAATGAC---GAAGGCAGA
1274 203_HRV65        CACACAGATCTTAAACATGACCATGAAGGCCAAAATGTTTACAATGAC---GAAGGCAGA
1275 204_HRV71a       CACACTAAATTAGTACATGGAGAGGAGG------TGTTTATAATATG---AAAGGTAAC
1276 205_HRV71b       CACACTAAATTAGTACATGGAGAGGAGG------TGTTTATAATATG---AAAGGTAAC
1277 206_HRV71        CACACTAAATTAGTACATGGAGAGGAGG------TGTTTATAATATG---AAAGGTAAC
1278 207_HRV8         GCATTAGAACTAGATCATGACAAC---------------TATGATGAA-----------
1279 208_HRV95        GCATTAGAACTAGATCATGACAAC---------------TATGATAAA-----------
1280 209_HRV45        AGTTTAGACATTAACCATGATGAC---------------TACCAAAAG-----------
1281 210_HRV45a       AGTTTAGACATTAACCATGATGAC---------------TACCAAAAG-----------
1282 211_HRV45b       AGTTTAGACATTAACCATGATGAC---------------TACCAAAAG-----------
1283 GROUP_1          ------------------------------------------------------------
1284
1285 1_HRV1A1|d       AATTTCACAAAATGGAAAATCACACTACAGGAAATGGCACAGATTAGGAGAAAATTTGAA
1286 2_HRV1A2|d       AATTTCACAAAATGGAAAATCACACTACAGGAAATGGCACAGATTAGGAGAAAATTTGAA
1287 3_HRV1A|cD       AATTTCACAAAATGGAAAATCACACTACAGGAAATGGCACAGATTAGGAGAAAATTTGAA
1288 4_HRV1B1|d       AACTTTACAACATGGAAAATCACACTGCAGGAGATGGCACAAATTAGAAGAAAATTCGAA
1289 5_HRV1B2|d       AACTTTACAACATGGAAAATCACACTGCAGGAGATGGCACAAATTAGAAGAAAATTCGAA
1290 6_HRV1B          AACTTTACAACATGGAAAATCACACTGCAGGAGATGGCACAAATTAGAAGAAAATTCGAA
1291 7_HRV40a|d       CACTTTGATAAGTGGCAGATAACCATACAAGAGATGTCACAAATTAGGAGAAAATTTGAA
1292 8_HRV40b|d       CACTTTGATAAGTGGCAGATAACCATACAAGAGATGTCACAAATTAGGAGAAAATTTGAA
1293 9_HRV40          CACTTTGATAAGTGGCAGATAACCATACAAGAGATGTCACAAATTAGGAGAAAATTTGAA
1294 10_HRV85         CACTTTGATCAGTGGCAGATAACTATACAGGAAATGGCACAAATTAGAAGGAAGTTTGAG
1295 11_HRV85a|       CACTTTGATCAGTGGCAGATAACTATACAGGAAATGGCACAAATTAGAAGGAAGTTTGAG
```

FIG. D11 CONT'D

```
07.trace                                                                        9/20/2007 5:04 PM 1296  12_HRV85b|    CACTTTGATCAGTGGCAGATAACTATACAGGAAATGGCACAAATTAGAAGGAAGTTTGAG
1297  13_HRV56a|    CATTATAATAAATGGCAAATAACCTTACAAGAAATGGCTCAAGTTAGGCGTAAATTTGAA
1298  14_HRV56b|    CATTATAATAAATGGCAAATAACCTTACAAGAAATGGCTCAAGTTAGGCGTAAATTTGAA
1299  15_HRV56     CATTATAATAAATGGCAAATAACCTTACAAGAAATGGCTCAAGTTAGGCGTAAATTTGAA
1300  16_HRV54     CATTTTAAGAAATGGGATATAACATTACAAGAGATGGCACAAATACGAAGGAAATTTGAA
1301  17_HRV98     CATTTTAGACAATGGGATATAACATTACAAGAAATGGCACAAATTCGAAGAAAATTTGAA
1302  18_HRV59a|    CACTTTCTTAAATGGCCTATAACATTACAAGAGATGGCACAAATTAGGAGAAAATTTGAA
1303  19_HRV59b|    CACTTTCTTAAATGGCCTATAACATTACAAGAGATGGCACAAATTAGGAGAAAATTTGAA
1304  20_HRV59     CACTTTCTTAAATGGCCTATAACATTACAAGAGATGGCACAAATTAGGAGAAAATTTGAA
1305  21_HRV63     CATTTTAATAAATGGCAAATAACATTACAAGAGATGGCACAAATTAGAAGGAAATTTGAA
1306  22_HRV63b|    CATTTTAATAAATGGCAAATAACATTACAAGAGATGGCACAAATTAGAAGGAAATTTGAA
1307  23_HRV63a|    CATTTTAATAAATGGCAAATAACATTACAAGAGATGGCACAAATTAGAAGGAAATTTGAA
1308  24_HRV39     AATTTTGTGGATTGGAAAATTACTTTGCAGGAGATGGCACAGGTTAGAAGGAAATTTGAA
1309  25_HRV39a|    AATTTTGTGGATTGGAAAATTACTTTGCAGGAGATGGCACAGGTTAGAAGGAAATTTGAA
1310  26_HRV39b|    AATTTTGTGGATTGGAAAATTACTTTGCAGGAGATGGCACAGGTTAGAAGGAAATTTGAA
1311  27_HRV10a|    ACTTTTGACACATGGCAAATAACTCTACAAGAAATGGCCCAAATTAGAAGGAAATTTGAA
1312  28_HRV10b|    ACTTTTGACACATGGCAAATAACTCTACAAGAAATGGCCCAAATTAGAAGGAAATTTGAA
1313  29_HRV10     ACTTTTGACACATGGCAAATAACTCTACAAGAAATGGCCCAAATTAGAAGGAAATTTGAA
1314  30_HRV100a   ACTTTTGACAAATGGCAAATAACCCTACAGGAAATGGCCCAAATTAGAAGGAAATTTGAA
1315  31_HRV100b   ACTTTTGACAAATGGCAAATAACCCTACAGGAAATGGCCCAAATTAGAAGGAAATTTGAA
1316  32_HRV100    ACTTTTGACAAATGGCAAATAACCCTACAGGAAATGGCCCAAATTAGAAGGAAATTTGAA
1317  33_HRV66     AAATTTAGAACATGGCAAATTACATTGCAAGAAATGGCTCAAATCAGACGCAAATTTGAG
1318  34_HRV66b|    AAATTTAGAACATGGCAAATTACATTGCAAGAAATGGCTCAAATCAGACGCAAATTTGAG
1319  35_HRV66a|    AAATTTAGAACATGGCAAATTACATTGCAAGAAATGGCTCAAATCAGACGCAAATTTGAG
1320  36_HRV77a|    AAATTTAGAAAATGGCAAATTACACTACAAGAAATGGCTCAAATTAGGCGCAAATTTGAA
1321  37_HRV77b|    AAATTTAGAAAATGGCAAATTACACTACAAGAAATGGCTCAAATTAGGCGCAAATTTGAA
1322  38_HRV77     AAATTTAGAAAATGGCAAATTACACTACAAGAAATGGCTCAAATTAGGCGCAAATTTGAA
1323  39_HRV62a    AGATTCAAAACATGGAATATTAACTTACAAGAGATGGCTCAAATCAGGAGAAAGTTTGAA
1324  40_HRV62b    AGATTCAAAACATGGAATATTAACTTACAAGAGATGGCTCAAATCAGGAGAAAGTTTGAA
1325  41_HRV25     AGATTTAAAATATGGAATATCAATTTACAAGAAATGGCTCAAATTAGGAGAAAGTTTGAG
1326  42_HRV29a    AAGTTCGATAAATGGAATGTTAACTTACAAGAAATGGCTCAAATTAGGCGCAAATTTGAA
1327  43_HRV29b    AAGTTCGATAAATGGAATGTTAACTTACAAGAAATGGCTCAAATTAGGCGCAAATTTGAA
1328  44_HRV44a    AAGTTTGATAAATGGAATATCAACTTACAAGAAATGGCTCAAATTAGACGCAAATTTGAA
1329  45_HRV44b    AAGTTTGATAAATGGAATATCAACTTACAAGAAATGGCTCAAATTAGACGCAAATTTGAA
1330  46_HRV31     AAATATAAAGTATGGCACATTAATTTACAAGAGATGGCCCAGATTAGGCGAAAATTTGAA
1331  47_HRV31a|    AAATATAAAGTATGGCACATTAATTTACAAGAGATGGCCCAGATTAGGCGAAAATTTGAA
1332  48_HRV31b|    AAATATAAAGTATGGCACATTAATTTACAAGAGATGGCCCAGATTAGGCGAAAATTTGAA
1333  49_HRV47     AAATTTAAAGTATGGCACATTAATTTACAAGAAATGGCCCAGATCAGGCGTAAATATGAA
1334  50_HRV47a|    AAATTTAAAGTATGGCACATTAATTTACAAGAAATGGCCCAGATCAGGCGTAAATATGAA
1335  51_HRV47b|    AAATTTAAAGTATGGCACATTAATTTACAAGAAATGGCCCAGATCAGGCGTAAATATGAA
1336  52_HRV11     AACTTTAACACATGGAAAATAAACTTGCAAGAGATGGCACAAATTAGAAGGAAATTTGAA
1337  53_HRV11b|    AACTTTAACACATGGAAAATAAACTTGCAAGAGATGGCACAAATTAGAAGGAAATTTGAA
1338  54_HRV11a|    AACTTTAACACATGGAAAATAAACTTGCAAGAGATGGCACAAATTAGAAGGAAATTTGAA
1339  55_HRV76     AACTTTAAGACATGGAAAATAAACCTACAAGAAATGGCACAAGTTAGAAGAAAATTTGAG
1340  56_HRV76b|    AACTTTAAGACATGGAAAATAAACCTACAAGAAATGGCACAAGTTAGAAGAAAATTTGAG
1341  57_HRV76a|    AACTTTAAGACATGGAAAATAAACCTACAAGAAATGGCACAAGTTAGAAGAAAATTTGAG
1342  58_HRV33     AATTTTATGACATGGAAAATAAACTTGCAAGAGATGGCACAATTAGGAGGAAATTTGAA
1343  59_HRV33b|    AATTTTATGACATGGAAAATAAATCTACAAGAGATGGCACAGATTAGGAGGAAATTTGAA
1344  60_HRV33a|    AATTTTATGACATGGAAAATAAATCTACAAGAGATGGCACAGATTAGGAGGAAATTTGAA
1345  61_HRV24a|    AATTTTTTCAAATGGCAAATAAATCTACAAGAAATGGCCCAAGTCAGAAGAAAATTTGAA
1346  62_HRV24b|    AATTTTTTCAAATGGCAAATAAATCTACAAGAAATGGCCCAAGTCAGAAGAAAATTTGAA
1347  63_HRV24     AATTTTTTCAAATGGCAAATAAATCTACAAGAAATGGCCCAAGTCAGAAGAAAATTTGAA
1348  64_HRV90     AACTTCCATAAATGGCAAATTAACCTGCAAGAGATGGCACAGATTAGAAGAAAATTTGAA
1349  65_HRV90a|    AACTTCCATAAATGGCAAATTAACCTGCAAGAGATGGCACAGATTAGAAGAAAATTTGAA
1350  66_HRV90b|    AACTTCCATAAATGGCAAATTAACCTGCAAGAGATGGCACAGATTAGAAGAAAATTTGAA
1351  67_HRV34     AACTTTATGACATGGCAAATTAATTTACAGGAAATGGCACAGATTAGAAGGAAATTTGAA
1352  68_HRV34b|    AACTTTATGACATGGCAAATTAATTTACAGGAAATGGCACAGATTAGAAGGAAATTTGAA
1353  69_HRV34a|    AACTTTATGACATGGCAAATTAATTTACAGGAAATGGCACAGATTAGAAGGAAATTTGAA
1354  70_HRV50a|    AACTTCAAGAAATGGCAAATCAACCTACAAGAAATGGCACAGATCAGAAGGAAATTTGAG
1355  71_HRV50b|    AACTTCAAGAAATGGCAAATCAACCTACAAGAAATGGCACAGATCAGAAGGAAATTTGAG
1356  72_HRV50     AACTTCAAGAAATGGCAAATCAACCTACAAGAAATGGCACAGATCAGAAGGAAATTTGAG
1357  73_HRV18a|    AACTTTGTAAAATGGCAAATAAATCTACAGGAAATGGCCCCAGATTAGGAGAAAATTTGAG
1358  74_HRV18b|    AACTTTGTAAAATGGCAAATAAATCTACAGGAAATGGCCCCAGATTAGGAGAAAATTTGAG
1359  75_HRV18     AACTTTGTAAAATGGCAAATAAATCTACAGGAAATGGCCCCAGATTAGGAGAAAATTTGAG
1360  76_HRV55     AATTTTACTAAGTGGCAAGTAAACATCCAAGAGATGGCTCAGATTAGAAGAAAATTTGAA
```

FIG. D11 CONT'D

07.trace                                                              9/20/2007 5:04 PM

```
1361  77_HRV55b|   AATTTTACTAAGTGGCAAGTAAACATCCAAGAGATGGCTCAGATTAGAAGAAAATTTGAA
1362  78_HRV55a|   AATTTTACTAAGTGGCAAGTAAACATCCAAGAGATGGCTCAGATTAGAAGAAAATTTGAA
1363  79_HRV57    AATTTCACTAAATGGGAAATAAATCTACAAGAAATGGCACAAATCAGAAGAAAATTTGAA
1364  80_HRV57a|   AATTTCACTAAATGGGAAATAAATCTACAAGAAATGGCACAAATCAGAAGAAAATTTGAA
1365  81_HRV57b|   AATTTCACTAAATGGGAAATAAATCTACAAGAAATGGCACAAATCAGAAGAAAATTTGAA
1366  82_HRV21    AACATTAGTACATGGCAAATAAATATTAAAGAGATGGCACAAATTAGGAGAAAATTTGAA
1367  83_HRVHan   AACATTAATACATGGCAAATAAATATTAAAGAGATGGCACAAATTAGGAGAAAATTTGAA
1368  84_HRV43    AATTTTACCCAATGGCCAATCAACTTGCAAGAAATGGCACAAATTAGAAGAAAGTATGAA
1369  85_HRV43b|   AATTTTACCCAATGGCCAATCAACTTGCAAGAAATGGCACAAATTAGAAGAAAGTATGAA
1370  86_HRV43a|   AATTTTACCCAATGGCCAATCAACTTGCAAGAAATGGCACAAATTAGAAGAAAGTATGAA
1371  87_HRV75    AACTTCACTCAGTGGCCAATCAATCTACAGGAAATGGCTCAAATTAGAAGGAAATATGAA
1372  88_HRV75b|   AACTTCACTCAGTGGCCAATCAATCTACAGGAAATGGCTCAAATTAGAAGGAAATATGAA
1373  89_HRV75a|   AACTTCACTCAGTGGCCAATCAATCTACAGGAAATGGCTCAAATTAGAAGGAAATATGAA
1374  96_HRV9a|d   AATTTCACAATCTGGAAAATAAATATAAAGGAAATGGCCCAGATCAGGAGGAAATTTGAA
1375  97_HRV9b|d   AATTTCACAATCTGGAAAATAAATATAAAGGAAATGGCCCAGATCAGGAGGAAATTTGAA
1376  98_HRV9     AATTTCACAATCTGGAAAATAAATATAAAGGAAATGGCCCAGATCAGGAGGAAATTTGAA
1377  99_HRV32    AATTTCACAATTTGGAAGATAAATATAAAAGAAATGGCCCAGATTAGGAGAAATTTGAG
1378  100_HRV32a   AATTTCACAATTTGGAAGATAAATATAAAAGAAATGGCCCAGATTAGGAGAAAATTTGAG
1379  101_HRV32b   AATTTCACAATTTGGAAGATAAATATAAAAGAAATGGCCCAGATTAGGAGAAAATTTGAG
1380  102_HRV67    AATTTCACAATTTGGAAAATAAATATAAAAGAAATGGCCCAGATTAGGAGGAAATTTGAA
1381  103_HRV67a   AATTTCACAATTTGGAAAATAAATATAAAAGAAATGGCCCAGATTAGGAGGAAATTTGAA
1382  104_HRV67b   AATTTCACAATTTGGAAAATAAATATAAAAGAAATGGCCCAGATTAGGAGGAAATTTGAA
1383  105_HRV15   AACTTTACTAAATGGCAAATTAATCTCAAAGAAATGGCCCAGATTAGAAGGAAATTTGAA
1384  106_HRV15a   AACTTTACTAAATGGCAAATTAATCTCAAAGAAATGGCCCAGATTAGAAGGAAATTTGAA
1385  107_HRV15b   AACTTTACTAAATGGCAAATTAATCTCAAAGAAATGGCCCAGATTAGAAGGAAATTTGAA
1386  108_HRV74a   AATTTTACTAAATGGCAAATAAATCTTAAAGAAATGGCACAGATTAGGAGAAAATTTGAG
1387  109_HRV74b   AATTTTACTAAATGGCAAATAAATCTTAAAGAAATGGCACAGATTAGGAGAAAATTTGAG
1388  110_HRV74   AATTTTACTAAATGGCAAATAAATCTTAAAGAAATGGCACAGATTAGGAGAAAATTTGAG
1389  111_HRV38a   AACTTTACAACATGGCAAATCAATCTCAAAGAAATGGCTCAAATCAGAAGAAAGTTTGAA
1390  112_HRV38b   AACTTTACAACATGGCAAATCAATCTCAAAGAAATGGCTCAAATCAGAAGAAAGTTTGAA
1391  113_HRV38   AACTTTACAACATGGCAAATCAATCTCAAAGAAATGGCTCAAATCAGAAGAAAGTTTGAA
1392  114_HRV60   AATTTCACAACTTGGCAAATTAACCTAAAGGAAATGGCACAAATAAGAAGAAAGTTTGAA
1393  115_HRV60a   AATTTCACAACTTGGCAAATTAACCTAAAGGAAATGGCACAAATAAGAAGAAAGTTTGAA
1394  116_HRV60b   AATTTCACAACTTGGCAAATTAACCTAAAGGAAATGGCACAAATAAGAAGAAAGTTTGAA
1395  117_HRV64a   AATTTTAACAAATGGCAGATCACCTTGAAAGAAATGGCTCAGATAAGAAGGGAAGTATGAA
1396  118_HRV64b   AATTTTAACAAATGGCAGATCACCTTGAAAGAAATGGCTCAGATAAGAAGGAAGTATGAA
1397  119_HRV64   AATTTTAACAAATGGCAGATCACCTTGAAAGAAATGGCTCAGATAAGAAGGAAGTATGAA
1398  120_HRV94a   AATTTCCAATCATGGCAAATTACCCTAAAAGAAATGGCACAAATAAGAAGGAAATTTGAA
1399  121_HRV94b   AATTTCCAATCATGGCAAATTACCCTAAAAGAAATGGCACAAATAAGAAGGAAATTTGAA
1400  122_HRV94   AATTTCCAATCATGGCAAATTACCCTAAAAGAAATGGCACAAATAAGAAGGAAATTTGAA
1401  123_HRV22   AACTTTAACATATGGCAAATTAACCTTAAAGAGATGGCTCAGATAAGAAGGAAGTTTGAG
1402  124_HRV22a   AACTTTAACATATGGCAAATTAACCTTAAAGAGATGGCTCAGATAAGAAGGAAGTTTGAG
1403  125_HRV22b   AACTTTAACATATGGCAAATTAACCTTAAAGAGATGGCTCAGATAAGAAGGAAGTTTGAG
1404  126_HRV82   AACTTTAGATCATGGCAAATAAGCATAAAGGAAATGGCACAAATTAGAAGGAAGTTTGAA
1405  127_HRV82b   AACTTTAGATCATGGCAAATAAGCATAAAGGAAATGGCACAAATTAGAAGGAAGTTTGAA
1406  128_HRV82a   AACTTTAGATCATGGCAAATAAGCATAAAGGAAATGGCACAAATTAGAAGGAAGTTTGAA
1407  129_HRV19   AATTTCAAAACTTGGCAAATAAACTTGAAAGAAATGGCACAGATTAGAAGAAAATTTGAA
1408  130_HRV19a   AATTTCAAAACTTGGCAAATAAACTTGAAAGAAATGGCACAGATTAGAAGAAAATTTGAA
1409  131_HRV19b   AATTTCAAAACTTGGCAAATAAACTTGAAAGAAATGGCACAGATTAGAAGAAAATTTGAA
1410  132_HRV13   AATTTTGTGAAATGGAAAATAAGTTTGCAAGAAATGGCCCAAGTGCGCAGAAAATTTGAG
1411  133_HRV13a   AATTTTGTGAAATGGAAAATAAGTTTGCAAGAAATGGCCCAAGTGCGCAGAAAATTTGAG
1412  134_HRV13b   AATTTTGTGAAATGGAAAATAAGTTTGCAAGAAATGGCCCAAGTGCGCAGAAAATTTGAG
1413  135_HRV41   AACTTCAAGAAGTGGAAAATTAGCTTACAGGAGATGGCCCAAGTACGTAGAAAGTTTGAG
1414  136_HRV41a   AACTTCAAGAAGTGGAAAATTAGCTTACAGGAGATGGCCCAAGTACGTAGAAAGTTTGAG
1415  137_HRV41b   AACTTCAAGAAGTGGAAAATTAGCTTACAGGAGATGGCCCAAGTACGTAGAAAGTTTGAG
1416  138_HRV73   AATTTTACCAAATGGAAAATAAGTTTACAAGAGATGGCTCAAATACGTAGGAAATTTGAA
1417  139_HRV73b   AATTTTACCAAATGGAAAATAAGTTTACAAGAGATGGCTCAAATACGTAGGAAATTTGAA
1418  140_HRV73a   AATTTTACCAAATGGAAAATAAGTTTACAAGAGATGGCTCAAATACGTAGGAAATTTGAA
1419  141_HRV61   AACTTCAAGGTGTGGAAAATAAACCTGCAAGAGATGGCACAAATACGTAGAAAATTTGAG
1420  142_HRV61a   AACTTCAAGGTGTGGAAAATAAACCTGCAAGAGATGGCACAAATACGTAGAAAATTTGAG
1421  143_HRV61b   AACTTCAAGGTGTGGAAAATAAACCTGCAAGAGATGGCACAAATACGTAGAAAATTTGAG
1422  144_HRV96   AATTTTAAGGTGTGGAAAATAAATCTACAAGAAATGGCTCAAATTCGCAGGAAGTTTGAA
1423  145_HRV96b   AATTTTAAGGTGTGGAAAATAAATCTACAAGAAATGGCTCAAATTCGCAGGAAGTTTGAA
1424  146_HRV96a   AATTTTAAGGTGTGGAAAATAAATCTACAAGAAATGGCTCAAATTCGCAGGAAGTTTGAA
1425  90_HRV16a|   AGTTTCACTAAATGGAAGATAAACCTGCAAGAAATGGCACAAATTAGAAGAAAATTTGAA
```

FIG. D11 CONT'D

```
07.trace                                                                                          9/20/2007 5:04 PM 1426  91_HRV16b|    AGTTTCACTAAATGGAAGATAAACCTGCAAGAAATGGCACAAATTAGAAGAAAATTTGAA
1427  92_1AYM_A     AGTTTCACTAAATGGAAGATAAACCTGCAAGAAATGGCACAAATTAGAAGAAAATTTGAA
1428  93_HRV81a|    AGCTTTACTAAATGGAAAATTAACTTACAAGAGATGGCACAGATTAGGAGAAAGTTTGAA
1429  94_HRV81b|    AGCTTTACTAAATGGAAAATTAACTTACAAGAGATGGCACAGATTAGGAGAAAGTTTGAA
1430  95_HRV81      AGCTTTACTAAATGGAAAATTAACTTACAAGAGATGGCACAGATTAGGAGAAAGTTTGAA
1431  147_HRV2      AATTTTACAGTGTGGGCTATTAATATACAAGAAATGGCTCAAATTAGAAGGAAATTTGAA
1432  148_HRV2a|    AATTTTACAGTGTGGGCTATTAATATACAAGAAATGGCTCAAATTAGAAGGAAATTTGAA
1433  149_HRV2b|    AATTTTACAGTGTGGGCTATTAATATACAAGAAATGGCTCAAATTAGAAGGAAATTTGAA
1434  150_HRV49a    AATTTCAAAGTATGGAACATCAATTTGCAAGAAATGGCCCAGATCAGAAGAAAATTTGAA
1435  151_HRV49b    AATTTCAAAGTATGGAACATCAATTTGCAAGAAATGGCCCAGATCAGAAGAAAATTTGAA
1436  152_HRV49     AATTTCAAAGTATGGAACATCAATTTGCAAGAAATGGCCCAGATCAGAAGAAAATTTGAA
1437  153_HRV23a    AATTTAATACTTGGAATATTAATTTACAGGAAATGGCCCAAATCAGAAGAAAGTTTGAA
1438  154_HRV23b    AATTTAATACTTGGAATATTAATTTACAGGAAATGGCCCAAATCAGAAGAAAGTTTGAA
1439  155_HRV23     AATTTAATACTTGGAATATTAATTTACAGGAAATGGCCCAAATCAGAAGAAAGTTTGAA
1440  156_HRV30a    AACTTTACCACATGGAATATTAATCTTCAAGAAATGGCCCAAATTAGAAGAAAATTTGAG
1441  157_HRV30b    AACTTTACCACATGGAATATTAATCTTCAAGAAATGGCCCAAATTAGAAGAAAATTTGAG
1442  158_HRV30     AACTTTACCACATGGAATATTAATCTTCAAGAAATGGCCCAAATTAGAAGAAAATTTGAG
1443  159_HRV7      GGTTTCACTACATGGAAAATCAGCTTACAAGAAATGGCACAAATCAGAAGAAAGTTTGAA
1444  160_HRV7b|    GGTTTCACTACATGGAAAATCAGCTTACAAGAAATGGCACAAATCAGAAGAAAGTTTGAA
1445  161_HRV7a|    GGTTTCACTACATGGAAAATCAGCTTACAAGAAATGGCACAAATCAGAAGAAAGTTTGAA
1446  162_HRV88     GGATTTGTAACATGGAAGATTAGCTTGCAAGAAATGGCACAAATCAGGAGAAAATTTGAA
1447  163_HRV88a    GGATTTGTAACATGGAAGATTAGCTTGCAAGAAATGGCACAAATCAGGAGAAAATTTGAA
1448  164_HRV88b    GGATTTGTAACATGGAAGATTAGCTTGCAAGAAATGGCACAAATCAGGAGAAAATTTGAA
1449  165_HRV36a    GGATTCAAAACATGGAAGATTAGTCTTCAAGAAATGGCACAAATTAGAAGGAAAATATGAA
1450  166_HRV36b    GGATTCAAAACATGGAAGATTAGTCTTCAAGAAATGGCACAAATTAGAAGGAAATATGAA
1451  167_HRV36     GGATTCAAAACATGGAAGATTAGTCTTCAAGAAATGGCACAAATTAGAAGGAAATATGAA
1452  168_HRV89a    GGATTCAAAACATGGAAGGTTAGTCTTCAAGAAATGGCACAAATCAGAAGAAAAATATGAA
1453  169_HRV89b    GGATTCAAAACATGGAAGGTTAGTCTTCAAGAAATGGCACAAATCAGAAGAAAAATATGAA
1454  170_HRV89     GGATTCAAAACATGGAAGGTTAGTCTTCAAGAAATGGCACAAATCAGAAGAAAATATGAA
1455  171_HRV58     GGATACAAAACATGGAAAATTAGCCTTCAAGAGATGGCACAAATTAGAAGGAAATTTGAG
1456  172_HRV58a    GGATACAAAACATGGAAAATTAGCCTTCAAGAGATGGCACAAATTAGAAGGAAATTTGAG
1457  173_HRV58b    GGATACAAAACATGGAAAATTAGCCTTCAAGAGATGGCACAAATTAGAAGGAAATTTGAG
1458  174_HRV12a    AACTTTAAAACATGGAAGATAAATCTTAAGGAAATGGCCCAGATTAGAAGGAAAAATGAG
1459  175_HRV12b    AACTTTAAAACATGGAAGATAAATCTTAAGGAAATGGCCCAGATTAGAAGGAAAAATGAG
1460  176_HRV12     AACTTTAAAACATGGAAGATAAATCTTAAGGAAATGGCCCAGATTAGAAGGAAAAATGAG
1461  177_HRV78a    AATTTTACAACGTGGAAAATCAACTTACAGGAGATGGCCCAGATTAGAAGAAAAGAATGAG
1462  178_HRV78b    AATTTTACAACGTGGAAAATCAACTTACAGGAGATGGCCCAGATTAGAAGAAAAGAATGAG
1463  179_HRV78     AATTTTACAACGTGGAAAATCAACTTACAGGAGATGGCCCAGATTAGAAGAAAAGAATGAG
1464  180_HRV20     AATTTCTCTCAGTGGAAGATCACAATCAAGGAAATGGCTCAAATCAGAAGAAAATGTGAG
1465  181_HRV20a    AATTTCTCTCAGTGGAAGATCACAATCAAGGAAATGGCTCAAATCAGAAGAAAATGTGAG
1466  182_HRV20b    AATTTCTCTCAGTGGAAGATCACAATCAAGGAAATGGCTCAAATCAGAAGAAAATGTGAG
1467  183_HRV68     AACTTCTCCCAATGGAAAATTACAATTAAGGAAATGGCTCAAATTAGAAGAAAAGTGTGAA
1468  184_HRV68a    AACTTCTCCCAATGGAAAATTACAATTAAGGAAATGGCTCAAATTAGAAGAAAAGTGTGAA
1469  185_HRV68b    AACTTCTCCCAATGGAAAATTACAATTAAGGAAATGGCTCAAATTAGAAGAAAAGTGTGAA
1470  186_HRV28     AATTTTAGTAAATGGAATATCACTCTCAAAGAAATGGCCCAAATCAGAAGAAAGTGTGAA
1471  187_HRV28a    AATTTTAGTAAATGGAATATCACTCTCAAAGAAATGGCCCAAATCAGAAGAAAGTGTGAA
1472  188_HRV28b    AATTTTAGTAAATGGAATATCACTCTCAAAGAAATGGCCCAAATCAGAAGAAAGTGTGAA
1473  189_HRV53a    AACCACTCAGAATGGAAGATTACACTCAAAGAAATGGCCCAGATTAGAAGGAAATGTGAG
1474  190_HRV53b    AACCACTCAGAATGGAAGATTACACTCAAAGAAATGGCCCAGATTAGAAGGAAATGTGAG
1475  191_HRV53     AACCACTCAGAATGGAAGATTACACTCAAAGAAATGGCCCAGATTAGAAGGAAATGTGAG
1476  192_HRV46a    AACTTCTCAAAATGGAAAATAACACTGTTGGAAATGGCACAAATCAGAAGAAAGTGTGAA
1477  193_HRV46b    AACTTCTCAAAATGGAAAATAACACTGTTGGAAATGGCACAAATCAGAAGAAAGTGTGAA
1478  194_HRV46     AACTTCTCAAAATGGAAAATAACACTGTTGGAAATGGCACAAATCAGAAGAAAGTGTGAA
1479  195_HRV80a    AATTTTTCAAAGTGGAAAATAACATTAATGGAAATGGCACAAATTAGAAGAAAGTGTGAG
1480  196_HRV80b    AATTTTTCAAAGTGGAAAATAACATTAATGGAAATGGCACAAATTAGAAGAAAGTGTGAG
1481  197_HRV80     AATTTTTCAAAGTGGAAAATAACATTAATGGAAATGGCACAAATTAGAAGAAAGTGTGAG
1482  198_HRV51     AATTTCTCTACATGGAAAATTACACTCAAAGAAATGGCTCAAATTAGAAGAAAGTGTGAA
1483  199_HRV51a    AATTTCTCTACATGGAAAATTACACTCAAAGAAATGGCTCAAATTAGAAGAAAGTGTGAA
1484  200_HRV51b    AATTTCTCTACATGGAAAATTACACTCAAAGAAATGGCTCAAATTAGAAGAAAGTGTGAA
1485  201_HRV65a    AATTTCTCTGCTTGGGAAATTACACTCAAGGAAATGGCTCAAATTAGGAGAAAGTGTGAA
1486  202_HRV65b    AATTTCTCTGCTTGGGAAATTACACTCAAGGAAATGGCTCAAATTAGGAGAAAGTGTGAA
1487  203_HRV65     AATTTCTCTGCTTGGGAAATTACACTCAAGGAAATGGCTCAAATTAGGAGAAAGTGTGAA
1488  204_HRV71a    AATCTCTCAAAGTGGCAGATTACACTCAAAGAAATGGCTCAGATCAGGAGGAAATGTGAA
1489  205_HRV71b    AATCTCTCAAAGTGGCAGATTACACTCAAAGAAATGGCTCAGATCAGGAGGAAATGTGAA
1490  206_HRV71     AATCTCTCAAAGTGGCAGATTACACTCAAAGAAATGGCTCAGATCAGGAGGAAATGTGAA
```

FIG. D11 CONT'D

```
07.trace                                                                                          9/20/2007 5:04 PM 1491 207_HRV8      AGTTTCAGGACCTGGGGAATAAACATACAAGAGATGTCACAAATTAGAAGGAAATTTGAG
1492 208_HRV95     AATTTCAGGACCTGGGGAATAAACATACAAGAGATGTCACAAATTAGAAGGAAATTTGAA
1493 209_HRV45     AATTACAAAAATTGGGCAATTAGTTTACAAGAAATGTCACAAATTAGGAGGAAATTTGAA
1494 210_HRV45a    AATTACAAAAATTGGGCAATTAGTTTACAAGAAATGTCACAAATTAGGAGGAAATTTGAA
1495 211_HRV45b    AATTACAAAAATTGGGCAATTAGTTTACAAGAAATGTCACAAATTAGGAGGAAATTTGAA
1496 GROUP_1       ------------TGG----T-A---T----GA-ATG-C-CA--T--G--G-AA----GA-
1497
1498  1_HRV1A1|d   TTGTTTACATATGTCAGGTTTGACTCAGAAATAACCTTGG-TGCCTTGTATTGCTGGTAG
1499  2_HRV1A2|d   TTGTTTACATATGTCAGGTTTGACTCAGAAATAACCTTGG-TGCCTTGTATTGCTGGTAG
1500  3_HRV1A|cD   TTGTTTACATATGTCAGGTTTGACTCAGAAATAACCTTGG-TGCCTTGTATTGCTGGTAG
1501  4_HRV1B1|d   CTATTTACTTATGTTAGGTTTGATTCAGAAGTAACTTTAG-TACCCTGTATTGCTGGTAG
1502  5_HRV1B2|d   CTATTTACTTATGTTAGGTTTGATTCAGAAGTAACTTTAG-TACCCTGTATTGCTGGTAG
1503  6_HRV1B      CTATTTACTTATGTTAGGTTTGATTCAGAAGTAACTTTAG-TACCCTGTATTGCTGGTAG
1504  7_HRV40a|d   TTCTTTACATATGCTAGGTTTGATTCAGAAATTACCTTAG-TTCCTTGTATAGCCGGTAA
1505  8_HRV40b|d   TTCTTTACATATGCTAGGTTTGATTCAGAAATTACCTTAG-TTCCTTGTATAGCCGGTAA
1506  9_HRV40      TTCTTTACATATGCTAGGTTTGATTCAGAAATTACCTTAG-TTCCTTGTATAGCCGGTAA
1507 10_HRV85      TTCTTTACTTACACTAGATTTGATTCAGAAATCACTTTAG-TCCCTTGTATAGCTGGAAA
1508 11_HRV85a|    TTCTTTACTTACACTAGATTTGATTCAGAAATCACTTTAG-TCCCTTGTATAGCTGGAAA
1509 12_HRV85b|    TTCTTTACTTACACTAGATTTGATTCAGAAATCACTTTAG-TCCCTTGTATAGCTGGAAA
1510 13_HRV56a|    TTCTTTACTTATGTCAGATTTGATTCAGAGGTTACTTTGG-TACCTTGTGTAGCCGGCAA
1511 14_HRV56b|    TTCTTTACTTATGTCAGATTTGATTCAGAGGTTACTTTGG-TACCTTGTGTAGCCGGCAA
1512 15_HRV56      TTCTTTACTTATGTCAGATTTGATTCAGAGGTTACTTTGG-TACCTTGTGTAGCCGGCAA
1513 16_HRV54      TTCTTTACTTATGTTAGGTTTGATTCAGAAATTACTCTAG-TCCCCTGTATAGCTGGTAA
1514 17_HRV98      TTCTTTACTTATGTTAGATTTGATTCAGAAGTTACCTTAG-TTCCTTGCATAGCTGGCAA
1515 18_HRV59a|    TTCTTCACATATGTTAGATTTGACTCAGAAATCACTTTGG-TGCCTTGCATAGCTGGAAA
1516 19_HRV59b|    TTCTTCACATATGTTAGATTTGACTCAGAAATCACTTTGG-TGCCTTGCATAGCTGGAAA
1517 20_HRV59      TTCTTCACATATGTTAGATTTGACTCAGAAATCACTTTGG-TGCCTTGCATAGCTGGAAA
1518 21_HRV63      TTCTTCACATATGTCAGATTTGATTCAGAAGTCACTCTTG-TACCATGTATAGCAGGAAA
1519 22_HRV63b|    TTCTTCACATATGTCAGATTTGATTCAGAAGTCACTCTTG-TACCATGTATAGCAGGAAA
1520 23_HRV63a|    TTCTTCACATATGTCAGATTTGATTCAGAAGTCACTCTTG-TACCATGTATAGCAGGAAA
1521 24_HRV39      ATGTTCACCTATGTTAGATTTGACTCAGAGATTACTTTAG-TCCCATGCATAGCTGGAAG
1522 25_HRV39a|    ATGTTCACCTATGTTAGATTTGACTCAGAGATTACTTTAG-TCCCATGCATAGCTGGAAG
1523 26_HRV39b|    ATGTTCACCTACGTTAGATTTGACTCAGAGATTACTTTAG-TCCCATGCATAGCTGGAAG
1524 27_HRV10a|    ATGTTTACATATGTTAGATTTGACTCAGAAGTCACTTTAG-TACCTTGCATCGCAGGCAA
1525 28_HRV10b|    ATGTTTACATATGTTAGATTTGACTCAGAAGTCACTTTAG-TACCTTGCATCGCAGGCAA
1526 29_HRV10      ATGTTTACATATGTTAGATTTGACTCAGAAGTCACTTTAG-TACCTTGCATCGCAGGCAA
1527 30_HRV100a    ATGTTTACATATGTCAGATTTGACTCAGAAATCACATTGG-TACCCTGTATTGCAGGAAA
1528 31_HRV100b    ATGTTTACATATGTCAGATTTGACTCAGAAATCACATTGG-TACCCTGTATTGCAGGAAA
1529 32_HRV100     ATGTTTACATATGTCAGATTTGACTCAGAAATCACATTGG-TACCCTGTATTGCAGGAAA
1530 33_HRV66      ATGTTCACATATGTTAGGTTTGATTCTGAAATTACATTAG-TCCCATGCATTGCAGGAAA
1531 34_HRV66b|    ATGTTCACATATGTTAGGTTTGATTCTGAAATTACATTAG-TCCCATGCATTGCAGGAAA
1532 35_HRV66a|    ATGTTCACATATGTTAGGTTTGATTCTGAAATTACATTAG-TCCCATGCATTGCAGGAAA
1533 36_HRV77a|    ATGTTCACATATGTAAGATTTGATTCAGAAATTACATTGG-TCCCATGTATTGCTGGAAA
1534 37_HRV77b|    ATGTTCACATATGTAAGATTTGATTCAGAAATTACATTGG-TCCCATGTATTGCTGGAAA
1535 38_HRV77      ATGTTCACATATGTAAGATTTGATTCAGAAATTACATTGG-TCCCATGTATTGCTGGAAA
1536 39_HRV62a     ATGTTTACATATGTAAGATTTGATTCAGAAATAACCCTGG-TTCCATCTATTGCAGGACG
1537 40_HRV62b     ATGTTTACATATGTAAGATTTGATTCAGAAATAACCCTGG-TTCCATCTATTGCAGGACG
1538 41_HRV25      ATGTTTACATATGTGAGATTTGATTCAGAGATAACCCTAG-TTCCATCTATTGCAGGACG
1539 42_HRV29a     ATGTTCACATATGTGAGATTTGACTCAGAAATAACTCTGG-TTCTTTGCATTGCAGGACG
1540 43_HRV29b     ATGTTCACATATGTGAGATTTGACTCAGAAATAACTCTGG-TTCCATGCATTGCAGGACG
1541 44_HRV44a     ATGTTCACATATGTGAGATTTGATTCGGAAATAACCCTAG-TTCCATGCATTGCAGGACA
1542 45_HRV44b     ATGTTCACATATGTGAGATTTGATTCAGAAATAACTCTAG-TTCCATGCATTGCAGGACG
1543 46_HRV31      ATGTTCACATATGTAAGATTTGATTCAGAAGTGACCATAG-TTCCATGCATTGCAGGACA
1544 47_HRV31a|    ATGTTCACATATGTAAGATTTGATTCAGAAGTGACCATAG-TTCCATGCATTGCAGGACA
1545 48_HRV31b|    ATGTTCACATATGTAAGATTTGATTCAGAAGTGACCATAG-TTCCATGCATTGCAGGACA
1546 49_HRV47      ATGTTTACATATGTAAGATTTGATTCAGAAGTAACCATGG-TTCCATGTATTGCAGGGTA
1547 50_HRV47a|    ATGTTTACATATGTAAGATTTGATTCAGAAGTAACCATGG-TTCCATGTATTGCAGGGTA
1548 51_HRV47b|    ATGTTTACATATGTAAGATTTGATTCAGAAGTAACCATGG-TTCCATGTATTGCAGGGTA
1549 52_HRV11      ATGTTCACATACACTAGATTTGATTCAGAGATCACATTGG-TGCCTTGTATAGCTGCAAA
1550 53_HRV11b|    ATGTTCACATACACTAGATTTGATTCAGAGATCACATTGG-TGCCTTGTATAGCTGCAAA
1551 54_HRV11a|    ATGTTCACATACACTAGATTTGATTCAGAGATCACATTGG-TGCCTTGTATAGCTGCAAA
1552 55_HRV76      ATGTTTACATATACTAGATTTGATTCAGAAGTTACTCTAG-TTCCTTCTATAGCTGCCAA
1553 56_HRV76b|    ATGTTTACATATACTAGATTTGATTCAGAAGTTACTCTAG-TTCCTTCTATAGCTGCCAA
1554 57_HRV76a|    ATGTTTACATATACTAGATTTGATTCAGAAGTTACTCTAG-TTCCTTCTATAGCTGCCAA
1555 58_HRV33      ATGTTTACATATGCCAGATTTGATTCAGAGATCACCCTAG-TCCCTTCTATAGCTGCCCA
```

FIG. D11 CONT'D

```
07.trace                                                                  9/20/2007 5:04 PM 1556  59_HRV33b|   ATGTTTACATATGCCAGATTTGATTCAGAGATCACCCTAG-TCCCTTCTATAGCTGCCCA
1557  60_HRV33a|   ATGTTTACATATGCCAGATTTGATTCAGAGATCACCCTAG-TCCCTTCTATAGCTGCCCA
1558  61_HRV24a|   TTATTCACATATACTAGATTTGACTCTGAGATTACAATAG-TTCCATCCATAGCTGGCAA
1559  62_HRV24b|   TTATTCACATATACTAGATTTGACTCTGAGATTACAATAG-TTCCATCCATAGCTGGCAA
1560  63_HRV24    TTATTCACATATACTAGATTTGACTCTGAGATTACAATAG-TTCCATCCATAGCTGGCAA
1561  64_HRV90    TTGTTTACATATGCTAGATTTGATTCTGAAATTACAATAG-TACCATCTATAGCTGGCAA
1562  65_HRV90a|   TTGTTTACATATGCTAGATTTGATTCTGAAATTACAATAG-TACCATCTATAGCTGGCAA
1563  66_HRV90b|   TTGTTTACATATGCTAGATTTGATTCTGAAATTACAATAG-TACCATCTATAGCTGGCAA
1564  67_HRV34    ATGTTCACCTACGTCAGATTTGATTCTGAAGTCACCCTAG-TACCATCAATAGCGGCCAA
1565  68_HRV34b|   ATGTTCACCTACGTCAGATTTGATTCTGAAGTCACCCTAG-TACCATCAATAGCGGCCAA
1566  69_HRV34a|   ATGTTCACCTACGTCAGATTTGATTCTGAAGTCACCCTAG-TACCATCAATAGCGGCCAA
1567  70_HRV50a|   ATGTTCACCTATGTGAGGTTTAATTCTGAGGTCACATTAG-TACCATCCATAGCTGCCAA
1568  71_HRV50b|   ATGTTCACCTATGTGAGGTTTAATTCTGAGGTCACATTAG-TACCATCCATAGCTGCCAA
1569  72_HRV50    ATGTTCACCTATGTGAGGTTTAATTCTGAGGTCACATTAG-TACCATCCATAGCTGCCAA
1570  73_HRV18a|   ATGTTTACATATGTTAGATTTGATTCAGAAATTACACTAG-TACCATCTGTAGCTGCTAA
1571  74_HRV18b|   ATGTTTACATATGTTAGATTTGATTCAGAAATTACACTAG-TACCATCTGTAGCTGCTAA
1572  75_HRV18    ATGTTTACATATGTTAGATTTGATTCAGAAATTACACTAG-TACCATCTGTAGCTGCTAA
1573  76_HRV55    ATGTTCACCTATACTAGATTTGATTCAGAAGTTACATTAG-TACCCTCTATTGCTGCAAA
1574  77_HRV55b|   ATGTTCACCTATACTAGATTTGATTCAGAAGTTACATTAG-TACCCTCTATTGCTGCAAA
1575  78_HRV55a|   ATGTTCACCTATACTAGATTTGATTCAGAAGTTACATTAG-TACCCTCTATTGCTGCAAA
1576  79_HRV57    CTATTTACATATGTTAGGTTTGATTCTGAAGTTACATTAG-TTCCCTCCATAGCTGCTCA
1577  80_HRV57a|   CTATTTACATATGTTAGGTTTGATTCTGAAGTTACATTAG-TTCCCTCCATAGCTGCTCA
1578  81_HRV57b|   CTATTTACATATGTTAGGTTTGATTCTGAAGTTACATTAG-TTCCCTCCATAGCTGCTCA
1579  82_HRV21    ATGTTCACCTATACTAGATTTGATTCAGAAATAACTTTGG-TGCCGTCAATTGCAGCTAG
1580  83_HRVHan   ATGTTCACCTATACTAGATTTGATTCAGAAATAACTTTGG-TACCGTCAATTGCAGCTAA
1581  84_HRV43    TTGTTCACATACTTAAGGTTTGATTCTGAAATTACCCTTG-TTCCTTGCATTGCAGCAAA
1582  85_HRV43b|   TTGTTCACATACTTAAGGTTTGATTCTGAAATTACCCTTG-TTCCTTGCATTGCAGCAAA
1583  86_HRV43a|   TTGTTCACATACTTAAGGTTTGATTCTGAAATTACCCTTG-TTCCTTGCATTGCAGCAAA
1584  87_HRV75    TTATTTACATATCTTAGATTTGATTCAGAGGTTACTCTGG-TGCCATGCATTGCAGCTAA
1585  88_HRV75b|   TTATTTACATATCTTAGATTTGATTCAGAGGTTACTCTGG-TGCCATGCATTGCAGCTAA
1586  89_HRV75a|   TTATTTACATATCTTAGATTTGATTCAGAGGTTACTCTGG-TGCCATGCATTGCAGCTAA
1587  96_HRV9a|d  TTGTTTACATATGCAAGATTTGACTCTGAAATAACATTGG-TCCCGTGTATAGCAGCAGA
1588  97_HRV9b|d  TTGTTTACATATGCAAGATTTGACTCTGAAATAACATTGG-TCCCGTGTATAGCAGCAGA
1589  98_HRV9     TTGTTTACATATGCAAGATTTGACTCTGAAATAACATTGG-TCCCGTGTATAGCAGCAGA
1590  99_HRV32    TTGTTTACATACACAAGGTTTGATTCTGAAATAACATTAG-TACCTTGTATAGCTGCAGA
1591  100_HRV32a  TTGTTTACATACACAAGGTTTGATTCTGAAATAACATTAG-TACCTTGTATAGCTGCAGA
1592  101_HRV32b  TTGTTTACATACACAAGGTTTGATTCTGAAATAACATTAG-TACCTTGTATAGCTGCAGA
1593  102_HRV67   CTATTCACATATACAAGATTTGATTCTGAGATAACACTGG-TACCATGCATAGCTGCAGA
1594  103_HRV67a  CTATTCACATATACAAGATTTGATTCTGAGATAACACTGG-TACCATGCATAGCTGCAGA
1595  104_HRV67b  CTATTCACATATACAAGATTTGATTCTGAGATAACACTGG-TACCATGCATAGCTGCAGA
1596  105_HRV15   TTATTCACATATGTAAGGTTTGATTCAGAAATAACACTTG-TACCATGCATTGCAGCAAA
1597  106_HRV15a  TTATTCACATATGTAAGGTTTGATTCAGAAATAACACTTG-TACCATGCATTGCAGCAAA
1598  107_HRV15b  TTATTCACATATGTAAGGTTTGATTCAGAAATAACACTTG-TACCATGCATTGCAGCAAA
1599  108_HRV74a  TTGTTCACATATGTTAGATTTGACTCAGAAGTGACATTAG-TTCCATGCATTGCTGCTAA
1600  109_HRV74b  TTGTTCACATATGTTAGATTTGACTCAGAAGTGACATTAG-TTCCATGCATTGCTGCTAA
1601  110_HRV74   TTGTTCACATATGTTAGATTTGACTCAGAAGTGACATTAG-TTCCATGCATTGCTGCTAA
1602  111_HRV38a  ATGTTTACATATGTGAGATTTGATTCAGAAGTTACATTAG-TCCCATGTATAGCAGCACA
1603  112_HRV38b  ATGTTTACATATGTGAGATTTGATTCAGAAGTTACATTAG-TCCCATGTATAGCAGCACA
1604  113_HRV38   ATGTTTACATATGTGAGATTTGATTCAGAAGTTACATTAG-TCCCATGTATAGCAGCACA
1605  114_HRV60   TTATTTACATATGTAAGATTTGATTCTCTGG-TCCCATGCATAGCAGCAAA
1606  115_HRV60a  TTATTTACATATGTAAGATTTGATTCAGAATTGACTCTGG-TCCCATGCATAGCAGCAAA
1607  116_HRV60b  TTATTTACATATGTAAGATTTGATTCAGAATTGACTCTGG-TCCCATGCATAGCAGCAAA
1608  117_HRV64a  TTATTTACATATGTTAGATTTGATTCTGAAATAACCTTAG-TGCCTTGCATATCTTCTCA
1609  118_HRV64b  TTATTTACATATGTTAGATTTGATTCTGAAATAACCTTAG-TGCCTTGCATATCTTCTCA
1610  119_HRV64   TTATTTACATATGTTAGATTTGATTCTGAAATAACCTTAG-TGCCTTGCATATCTTCTCA
1611  120_HRV94a  CTATTTACTTATGTTAGATTTGATTCAGAAATAACTTTAG-TACCTTGCATATCATCTCA
1612  121_HRV94b  CTATTTACTTATGTTAGATTTGATTCAGAAATAACTTTAG-TACCTTGCATATCATCTCA
1613  122_HRV94   CTATTTACTTATGTTAGATTTGATTCAGAAATAACTTTAG-TACCTTGCATATCATCTCA
1614  123_HRV22   CTATTTACATATCTCAGGTTTGATTCTGAAATCACTTTGG-TACCATGCATTGCTTCACA
1615  124_HRV22a  CTATTTACATATCTCAGGTTTGATTCTGAAATCACTTTGG-TACCATGCATTGCTTCACA
1616  125_HRV22b  CTATTTACATATCTCAGGTTTGATTCTGAAATCACTTTGG-TACCATGCATTGCTTCACA
1617  126_HRV82   CTTTTCACATATGTGAGATTTGATTCAGAAATTACTTTAG-TGCCTTGCATAGCCTCTCA
1618  127_HRV82b  CTTTTCACATATGTGAGATTTGATTCAGAAATTACTTTAG-TGCCTTGCATAGCCTCTCA
1619  128_HRV82a  CTTTTCACATATGTGAGATTTGATTCAGAAATTACTTTAG-TGCCTTGCATAGCCTCTCA
1620  129_HRV19   CTTTTCACTTACCTCAGATTTGATTCAGAGGTAACATTAG-TCCCTTGCATAGCTGCTAA
```

FIG. D11 CONT'D

```
07.trace                                                                                    9/20/2007 5:04 PM 1621 130_HRV19a     CTTTTCACTTACCTCAGATTTGATTCAGAGGTAACATTAG-TCCCTTGCATAGCTGCTAA
1622 131_HRV19b     CTTTTCACTTACCTCAGATTTGATTCAGAGGTAACATTAG-TCCCTTGCATAGCTGCTAA
1623 132_HRV13      TTGTTCACCTATGTAAGATTTGATTCAGAAATAACAATTG-TGCCATGTATAGCCGGGCA
1624 133_HRV13a     TTGTTCACCTATGTAAGATTTGATTCAGAAATAACAATTG-TGCCATGTATAGCCGGGCA
1625 134_HRV13b     TTGTTCACCTATGTAAGATTTGATTCAGAAATAACAATTG-TGCCATGTATAGCCGGGCA
1626 135_HRV41      TTTTTTACGTATGTTAGATTTGACTCAGAAATAACAATTG-TGCCAAGTATAGCTGGACA
1627 136_HRV41a     TTTTTTACGTATGTTAGATTTGACTCAGAAATAACAATTG-TGCCAAGTATAGCTGGACA
1628 137_HRV41b     TTTTTTACGTATGTTAGATTTGACTCAGAAATAACAATTG-TGCCAAGTATAGCTGGACA
1629 138_HRV73      TTATTCACCTATGTAAGATTTGATTCAGAAGTGACAATTG-TACCATGTATAGCTGGTCA
1630 139_HRV73b     TTATTCACCTATGTAAGATTTGATTCAGAAGTGACAATTG-TACCATGTATAGCTGGTCA
1631 140_HRV73a     TTATTCACCTATGTAAGATTTGATTCAGAAGTGACAATTG-TACCATGTATAGCTGGTCA
1632 141_HRV61      TTGTTCACATATGCTAGATTTGATTCAGAGATTACAATTG-TACCTTGTGTTGCTGGGCA
1633 142_HRV61a     TTGTTCACATATGCTAGATTTGATTCAGAGATTACAATTG-TACCTTGTGTTGCTGGGCA
1634 143_HRV61b     TTGTTCACATATGCTAGATTTGATTCAGAGATTACAATTG-TACCTTGTGTTGCTGGGCA
1635 144_HRV96      CTGTTCACTTATGCTAGATTTGATTCAGAGATAACAATTG-TTCCATGTGTTGCTGTGCA
1636 145_HRV96b     CTGTTCACTTATGCTAGATTTGATTCAGAGATAACAATTG-TTCCATGTGTTGCTGTGCA
1637 146_HRV96a     CTGTTCACTTATGCTAGATTTGATTCAGAGATAACAATTG-TTCCATGTGTTGCTGTGCA
1638 90_HRV16a|     ATGTTTACTTATGCAAGATTTGACTCTGAAATTACTATGG-TACCAAGTGTAGCAGCCAA
1639 91_HRV16b|     ATGTTTACTTATGCAAGATTTGACTCTGAAATTACTATGG-TACCAAGTGTAGCAGCCAA
1640 92_1AYM_A      ATGTTTACTTATGCAAGATTTGACTCTGAAATTACTATGG-TACCAAGTGTAGCAGCCAA
1641 93_HRV81a|     ATGTTCACATACACTAGATTTAACTCTGAGATTACACTGG-TACCAAGTGTTGCAAACAA
1642 94_HRV81b|     ATGTTCACATACACTAGATTTAACTCTGAGATTACACTGG-TACCAAGTATTGCAAACAA
1643 95_HRV81       ATGTTCACATACACTAGATTTAACTCTGAGATTACACTGG-TACCAAGTATTGCAAACAA
1644 147_HRV2       TTGTTCACCTATACTAGGTTTGATTCTGAAATAACCCTAG-TTCCATGCATTTCCGCCCT
1645 148_HRV2a|     TTGTTCACCTATACTAGGTTTGATTCTGAAATAACCCTAG-TTCCATGCATTTCCGCCCT
1646 149_HRV2b|     TTGTTCACCTATACTAGGTTTGATTCTGAAATAACCCTAG-TTCCATGCATTTCCGCCCT
1647 150_HRV49a     CTGTTTACTTACACTAGATTCGATTCTGAAATAACCTTGG-TTCCATGCATTTCTGCACT
1648 151_HRV49b     CTGTTTACTTACACTAGATTCGATTCTGAAATAACCTTGG-TTCCATGCATTTCTGCACT
1649 152_HRV49      CTGTTTACTTACACTAGATTCGATTCTGAAATAACCTTGG-TTCCATGCATTTCTGCACT
1650 153_HRV23a     CTGTTTACTTACACTAGATTTGATTCTGAAATTACTTTGG-TTCCATGCATTTCTGCTCT
1651 154_HRV23b     CTGTTTACTTACACTAGATTTGATTCTGAAATTACTTTGG-TTCCATGCATTTCTGCTCT
1652 155_HRV23      CTGTTTACTTACACTAGATTTGATTCTGAAATTACTTTGG-TTCCATGCATTTCTGCTCT
1653 156_HRV30a     CTATTCACTTACACTAGATTTGATTCTGAGATAACCTTGG-TTCCGTGTATTTCAGCTCT
1654 157_HRV30b     CTATTCACTTACACTAGATTTGATTCTGAGATAACCTTGG-TTCCGTGTATTTCAGCTCT
1655 158_HRV30      CTATTCACTTACACTAGATTTGATTCTGAGATAACCTTGG-TTCCGTGTATTTCAGCTCT
1656 159_HRV7       CTATTCACATACACTAGATTTGATTCTGAGATAACAATAG-TCACAGCAGCAATAGCACA
1657 160_HRV7b|     CTATTCACATACACTAGATTTGATTCTGAGATAACAATAG-TCACAGCAGCAGCAGCACA
1658 161_HRV7a|     CTATTCACATACACTAGATTTGATTCTGAGATAACAATAG-TCACAGCAGCAGCAGCACA
1659 162_HRV88      TTGTTTACATACACTAGATTTGACTCAGAAATAACAATAG-TCACAGCAGCTGCAGCACA
1660 163_HRV88a     TTGTTTACATACACTAGATTTGACTCAGAAATAACAATAG-TCACAGCAGCTGCAGCACA
1661 164_HRV88b     TTGTTTACATACACTAGATTTGACTCAGAAATAACAATAG-TCACAGCAGCTGCAGCACA
1662 165_HRV36a     TTGTTTACATACACAAGATTTGACTCAGAAATAACAATAG-TCACCGCAGCTGCAGTGCA
1663 166_HRV36b     TTGTTTACATACACAAGATTTGACTCAGAAATAACAATAG-TCACCGCAGCTGCAGTGCA
1664 167_HRV36      TTGTTTACATACACAAGATTTGACTCAGAAATAACAATAG-TCACCGCAGCTGCAGTGCA
1665 168_HRV89a     TTATTCACATATACAAGATTTGATTCAGAGATAACAATAG-TCACTGCAGCCGCAGCTCA
1666 169_HRV89b     TTATTCACATATACAAGATTTGATTCAGAGATAACAATAG-TCACTGCAGCCGCAGCTCA
1667 170_HRV89      TTATTCACATATACAAGATTTGATTCAGAGATAACAATAG-TCACTGCAGCCGCAGCTCA
1668 171_HRV58      TTGTTTACATATACAAGATTTGACTCAGAGATTACAATAG-TCACTGCAGCAGCTGCTCA
1669 172_HRV58a     TTGTTTACATATACAAGATTTGACTCAGAGATTACAATAG-TCACTGCAGCAGCTGCTCA
1670 173_HRV58b     TTGTTTACATATACAAGATTTGACTCAGAGATTACAATAG-TCACTGCAGCAGCTGCTCA
1671 174_HRV12a     CTTTTCACCTACTTAAGGTTTGATTCTGAAATCACCATTGTTCCAAGCAATG-CAGCAAT
1672 175_HRV12b     CTTTTCACCTACTTAAGGTTTGATTCTGAAATCACCATTGTTCCAAGCAATG-CAGCAAT
1673 176_HRV12      CTTTTCACCTACTTAAGGTTTGATTCTGAAATCACCATTGTTCCAAGCAATG-CAGCAAT
1674 177_HRV78a     ATGTTCACATATCTCAGATTTGATTCAGAAATCACTCTTG-TGTGTGCAGTGGCCTCACA
1675 178_HRV78b     ATGTTCACATATCTCAGATTTGATTCAGAAATCACTCTTG-TGTGTGCAGTGGCCTCACA
1676 179_HRV78      ATGTTCACATATCTCAGATTTGATTCAGAAATCACTCTTG-TGTGTGCAGTGGCCTCACA
1677 180_HRV20      CTCTTTACATACCTCAGATTTGATTCTGAGATTACAATAG-TAGCAACAGTAGCTGCACT
1678 181_HRV20a     CTCTTTACATACCTCAGATTTGATTCTGAGATTACAATAG-TAGCAACAGTAGCTGCACT
1679 182_HRV20b     CTCTTTACATACCTCAGATTTGATTCTGAGATTACAATAG-TAGCAACAGTAGCTGCACT
1680 183_HRV68      CTATTCACATACCTTAGGTTTGACTCTGAGATTACAATAG-TAGCAACAATAGCTGCTCT
1681 184_HRV68a     CTATTCACATACCTTAGGTTTGACTCTGAGATTACAATAG-TAGCAACAATAGCTGCTCT
1682 185_HRV68b     CTATTCACATACCTTAGGTTTGACTCTGAGATTACAATAG-TAGCAACAATAGCTGCTCT
1683 186_HRV28      ATGTTTACATATCTCAGATTTGATTCTGAAATTACTATAG-TGGTGTCAGTTGCAAGTAA
1684 187_HRV28a     ATGTTTACATATCTCAGATTTGATTCTGAAATTACTATAG-TGGTGTCAGTTGCAAGTAA
1685 188_HRV28b     ATGTTTACATATCTCAGATTTGATTCTGAAATTACTATAG-TGGTGTCAGTTGCAAGTAA
```

FIG. D11 CONT'D

```
07.trace                                                                              9/20/2007 5:04 PM 1686 189_HRV53a      ATGTTCACATATCTTAGATTTGATTCAGAAATAACTATAG-TGGTATCAGTGGCTAGTAA
1687 190_HRV53b      ATGTTCACATATCTTAGATTTGATTCAGAAATAACTATAG-TGGTATCAGTGGCTAGTAA
1688 191_HRV53       ATGTTCACATATCTTAGATTTGATTCAGAAATAACTATAG-TGGTATCAGTGGCTAGTAA
1689 192_HRV46a      CTTTTTACATATCTCAGATTTGATTCAGAAATAACAATAG-TCACCACATTGGCAGGCCA
1690 193_HRV46b      CTTTTTACATATCTCAGATTTGATTCAGAAATAACAATAG-TCACCACATTGGCAGGCCA
1691 194_HRV46       CTTTTTACATATCTCAGATTTGATTCAGAAATAACAATAG-TCACCACATTGGCAGGCCA
1692 195_HRV80a      CTTTTCACTTACCTCAGATTTGACTCAGAAATAACAATAG-TAACTACCTTAGCAGGACA
1693 196_HRV80b      CTTTTCACTTACCTCAGATTTGACTCAGAAATAACAATAG-TAACTACCTTAGCAGGACA
1694 197_HRV80       CTTTTCACTTACCTCAGATTTGACTCAGAAATAACAATAG-TAACTACCTTAGCAGGACA
1695 198_HRV51       CTTTTCACATACTTAAGATTTGATTCAGAGATCACTATAG-TTGCTACCATTGCTGGACA
1696 199_HRV51a      CTTTTCACATACTTAAGATTTGATTCAGAGATCACTATAG-TTGCTACCATTGCTGGACA
1697 200_HRV51b      CTTTTCACATACTTAAGATTTGATTCAGAGATCACTATAG-TTGCTACCATTGCTGGACA
1698 201_HRV65a      CTCTTCACCTATTTGCGCTTTGACTCAGAAATTACCATAG-TGGCTACTATAGCTGGACA
1699 202_HRV65b      CTCTTCACCTATTTGCGCTTTGACTCAGAAATTACCATAG-TGGCTACTATAGCTGGACA
1700 203_HRV65       CTCTTCACCTATTTGCGCTTTGACTCAGAAATTACCATAG-TGGCTACTATAGCTGGACA
1701 204_HRV71a      CTCTTCACATACCTGCGCTTTGATTCAGAGATAACAATTG-TAGCTACACTAGCAGGGCA
1702 205_HRV71b      CTCTTCACATACCTGCGCTTTGATTCAGAGATAACAATTG-TAGCTACACTAGCAGGGCA
1703 206_HRV71       CTCTTCACATACCTGCGCTTTGATTCAGAGATAACAATTG-TAGCTACACTAGCAGGGCA
1704 207_HRV8        ATGTTCACTTATGTAAGATTTGATTCAGAGATAACAATTG-TACCATGTATTGCAGCTAT
1705 208_HRV95       ATGTTCACTTATGTAAGATTTGATTCAGAGATAACAATTG-TACCATGTATTGCAGCTAT
1706 209_HRV45       ATGTTTACATATGTCAGATTTGATTCCGAAATAACAATAG-TACCATGTGTTGCTGCCAC
1707 210_HRV45a      ATGTTTACATATGTCAGATTTGATTCCGAAATAACAATAG-TACCATGTGTTGCTGCCAC
1708 211_HRV45b      ATGTTTACATATGTCAGATTTGATTCCGAAATAACAATAG-TACCATGTGTTGCTGCCAC
1709 GROUP_1         -T-TT-AC-TA-----G-TT--A-TC-GA--T-AC--T-G-T----------C------
1710
1711 1_HRV1A1|d      AGGAGACGACATTGGACATATTGTAATGCAATATATGTATGTTCCTCCAGGAGCTCCAAT
1712 2_HRV1A2|d      AGGAGACGACATTGGACATATTGTAATGCAATATATGTATGTTCCTCCAGGAGCTCCAAT
1713 3_HRV1A|cD      AGGAGACGACATTGGACATATTGTAATGCAATATATGTATGTTCCTCCAGGAGCTCCAAT
1714 4_HRV1B1|d      AGGAGATGACATTGGTCATGTTGTAATGCAGTATATGTATGTTCCCCCAGGAGCTCCAAT
1715 5_HRV1B2|d      AGGAGATGACATTGGTCATGTTGTAATGCAGTATATGTATGTTCCCCCAGGAGCTCCAAT
1716 6_HRV1B         AGGAGATGACATTGGTCATGTTGTAATGCAGTATATGTATGTTCCCCCAGGAGCTCCAAT
1717 7_HRV40a|d      GGGTGAAGACATTGGACACATTGTGATGCAATATATGTATGTACCCCCTGGCCGCACCCAT
1718 8_HRV40b|d      GGGTGAAGACATTGGACACATTGTGATGCAATATATGTATGTACCCCCTGGCCGCACCCAT
1719 9_HRV40         GGGTGAAGACATTGGACACATTGTGATGCAATATATGTATGTACCCCCTGGCCGCACCCAT
1720 10_HRV85        GGGTGATGATATTGGACACATTGTAATGCAGTATATGTATGTGCCCCCCGGAGCACCAAT
1721 11_HRV85a|      GGGTGATGATATTGGACACATTGTAATGCAGTATATGTATGTGCCCCCCGGAGCACCAAT
1722 12_HRV85b|      GGGTGATGATATTGGACACATTGTAATGCAGTATATGTATGTGCCCCCCGGAGCACCAAT
1723 13_HRV56a|      GGGAGATGATATTGGACACATTGTAATGCAATACATGTATGTGCCTCCTGGTGCACCACT
1724 14_HRV56b|      GGGAGATGATATTGGACACATTGTAATGCAATACATGTATGTGCCTCCTGGTGCACCACT
1725 15_HRV56        GGGAGATGATATTGGACACATTGTAATGCAATACATGTATGTGCCTCCTGGTGCACCACT
1726 16_HRV54        GGGAGTTGATATTGGACACATTGTCATGCAATTCATGTATGTACCGCCTGGTGCACCAAA
1727 17_HRV98        GGGAGCTGACATTGGACACATTGTCATGCAATTCATGTATGTTCCACCTGGTGCACCTAA
1728 18_HRV59a|      AGGGGATGATATTGGTCATATAGTCATGCAATATATGTATGTTCCACCAGGTGCTCCACT
1729 19_HRV59b|      AGGGGATGACATTGGTCATATAGTCATGCAATATATGTATGTTCCACCAGGTGCTCCACT
1730 20_HRV59        AGGGGATGACATTGGTCATATAGTCATGCAATATATGTATGTTCCACCAGGTGCTCCACT
1731 21_HRV63        AGGTGATGACATTGGTCATATAGTTATGCAGTACATGTACGTTCCACCCGGTGCCCCTCT
1732 22_HRV63b|      AGGTGATGACATTGGTCATATAGTTATGCAGTACATGTACGTTCCACCCGGTGCCCCTCT
1733 23_HRV63a|      AGGTGATGACATTGGTCATATAGTTATGCAGTACATGTACGTTCCACCCGGTGCCCCTCT
1734 24_HRV39        AGGTGAAGATATTGGACACATAGTAATGCAATACATGTATGTCCCCACCTGGTGCACCTGT
1735 25_HRV39a|      AGGTGAAGATATTGGACACATAGTAATGCAATACATGTATGTCCCCACCTGGTGCACCTGT
1736 26_HRV39b|      AGGTGAAGATATTGGACACATAGTAATGCAATACATGTATGTCCCCACCGGTGCACCTGT
1737 27_HRV10a|      GGGCGATGACATAGGTCACATAGTTATGCAATATATGTATGTGCCACCTGGGGCTCCAGT
1738 28_HRV10b|      GGGCGATGACATAGGTCACATAGTTATGCAATATATGTATGTGCCACCTGGGGCTCCAGT
1739 29_HRV10        GGGCGATGACATAGGTCACATAGTTATGCAATATATGTATGTGCCACCTGGGGCTCCAGT
1740 30_HRV100a      AGGAGATGACATAGGCCATATCGTAATGCAGTACATGTATGTGCCACCTGGAGCTCCAGT
1741 31_HRV100b      AGGAGATGACATAGGGCATATCGTAATGCAGTACATGTATGTGCCACCTGGAGCTCCAGT
1742 32_HRV100       AGGAGATGACATAGGGCATATCGTAATGCAGTACATGTATGTGCCACCTGGAGCTCCAGT
1743 33_HRV66        GGGTGATGATATAGGACATATTGTGATGCAATACATGTATGTACCACCTGGAGCCCCAAT
1744 34_HRV66b|      GGGTGATGATATAGGACATATTGTGATGCAATACATGTATGTACCACCTGGAGCCCCAAT
1745 35_HRV66a|      GGGTGATGATATAGGACATATTGTGATGCAATACATGTATGTACCACCTGGAGCCCCAAT
1746 36_HRV77a|      AGGTGATGACATAGGACATGTTGTCATGCAATACATGTATGTACCACCAGGGGCACCCAT
1747 37_HRV77b|      AGGTGATGACATAGGACATGTTGTCATGCAATACATGTATGTACCACCAGGGGCACCCAT
1748 38_HRV77        AGGTGATGACATAGGACATGTTGTCATGCAATACATGTATGTACCACCAGGGGCACCCAT
1749 39_HRV62a       TGGTGCAGATATAGGTCACATAGTTATGCAATATATGTATGTACCACCTGGGGCTCCACT
1750 40_HRV62b       TGGTGCAGATATAGGTCACATAGTTATGCAATATATGTATGTACCACCTGGGGCTCCACT
```

FIG. D11 CONT'D 07.trace                                                                                                                          9/20/2007 5:04 PM

```
1751  41_HRV25      TGGTGCAGATATAGGTCACATAGTTATGCAATATATGTATGTGCCACCTGGAGCCCCATT
1752  42_HRV29a     TGGTAATGATATAGGTCACATAGTTATGCAGTACATGTATGTACCACCTGGAGCTCCAGT
1753  43_HRV29b     TGGTAATGATATAGGTCACATAGTTATGCAGTACATGTATGTACCACCTGGAGCTCCAGT
1754  44_HRV44a     TGGTGATGATATAGGCCACATAGTTATGCAGTACATGTATGTACCACCTGGAGCTCCAGT
1755  45_HRV44b     TGGTGATGATATAGGCCACATAGTTATGCAGTACATGTATGTACCACCTGGAGCTCCAGT
1756  46_HRV31      TGGTAGTGACATAGGCCATATAGTCATGCAATACATGTATGTACCACCTGGGGCCCCAGT
1757  47_HRV31a|    TGGTAGTGACATAGGCCATATAGTCATGCAATACATGTATGTACCACCTGGGGCCCCAGT
1758  48_HRV31b|    TGGTAGTGACATAGGCCATATAGTCATGCAATACATGTATGTACCACCTGGGGCCCCAGT
1759  49_HRV47      TGGTGATGACATAGGTCACATAGTTATGCAATACATGTATGTGCCGCCTGGGGCTCCAGT
1760  50_HRV47a|    TGGTGATGACATAGGTCACATAGTTATGCAATACATGTATGTGCCGCCTGGGGCTCCAGT
1761  51_HRV47b|    TGGTGATGACATAGGTCACATAGTTATGCAATACATGTATGTGCCGCCTGGGGCTCCAGT
1762  52_HRV11      AGGAAATGATATTGGTCATGTTGTAATGCAATATATGTATGTCCCACCAGGTGCTCCAGT
1763  53_HRV11b|    AGGAAATGATATTGGTCATGTTGTAATGCAATATATGTATGTCCCACCAGGTGCTCCAGT
1764  54_HRV11a|    AGGAAATGATATTGGTCATGTTGTAATGCAATATATGTATGTCCCACCAGGTGCTCCAGT
1765  55_HRV76      AGGGGATGACATTGGTCATGTAGTGATGCAATACATGTATGTCCCACCAGGCGCTCCAGT
1766  56_HRV76b|    AGGGGATGACATTGGTCATGTAGTGATGCAATACATGTATGTCCCACCAGGCGCTCCAGT
1767  57_HRV76a|    AGGGGATGACATTGGTCATGTAGTGATGCAATACATGTATGTCCCACCAGGCGCTCCAGT
1768  58_HRV33      GGGAGATGATGTTGGTCATGTTGTAATGCAGTACATGTATGTCCCACCAGGTGCACCAGC
1769  59_HRV33b|    GGGAGATGATGTTGGTCATGTTGTAATGCAGTACATGTATGTCCCACCAGGTGCACCAGC
1770  60_HRV33a|    GGGAGATGATGTTGGTCATGTTGTAATGCAGTACATGTATGTCCCACCAGGTGCACCAGC
1771  61_HRV24a|    GGGAGATGACATTGGACATGTTGTAATGCAGTACATGTATATACCACCTGGAGCACCAGT
1772  62_HRV24b|    GGGAGATGACATTGGACATGTTGTAATGCAGTACATGTATATACCACCTGGAGCACCAGT
1773  63_HRV24      GGGAGATGACATTGGACATGTTGTAATGCAGTACATGTATATACCACCTGGAGCACCAGT
1774  64_HRV90      GGGCAATGATATTGGACATGTTGTGATGCAATACATGTATATACCACCTGGGGCACCAGT
1775  65_HRV90a|    GGGCAATGATATTGGACATGTTGTGATGCAATACATGTATATACCACCTGGGGCACCAGT
1776  66_HRV90b|    GGGCAATGATATTGGACATGTTGTGATGCAATACATGTATATACCACCTGGGGCACCAGT
1777  67_HRV34      AGGTGATGATATTGGACATGTTGTGATGCAATACATGTATGTACCACCAGGTGCACCAAT
1778  68_HRV34b|    AGGTGATGATATTGGACATGTTGTGATGCAATACATGTATGTACCACCAGGTGCACCAAT
1779  69_HRV34a|    AGGTGATGATATTGGACATGTTGTGATGCAATACATGTATGTACCACCAGGTGCACCAAT
1780  70_HRV50a|    GGGTGTTGATATTGGACATGTTGTCATGCAATACATGTATGTCCCACCAGGTGCACCAAT
1781  71_HRV50b|    GGGTGTTGATATTGGACATGTTGTCATGCAATACATGTATGTCCCACCAGGTGCACCAAT
1782  72_HRV50      GGGTGTTGATATTGGACATGTTGTCATGCAATACATGTATGTCCCACCAGGTGCACCAAT
1783  73_HRV18a|    GGGTGATGACATAGGACATATTGTTATGCAGTACATGTATGTTCCTCCAGGAGCACCAAT
1784  74_HRV18b|    GGGTGATGACATAGGACATATTGTTATGCAGTACATGTATGTTCCTCCAGGAGCACCAAT
1785  75_HRV18      GGGTGATGACATAGGACATATTGTTATGCAGTACATGTATGTTCCTCCAGGAGCACCAAT
1786  76_HRV55      GGGAGATGACATTGGACATGTAGTCATGCAATACATGTATGTTCCACCTGGAGCACCAAT
1787  77_HRV55b|    GGGAGATGACATTGGACATGTAGTCATGCAATACATGTATGTTCCACCTGGAGCACCAAT
1788  78_HRV55a|    GGGAGATGACATTGGACATGTAGTCATGCAATACATGTATGTTCCACCTGGAGCACCAAT
1789  79_HRV57      AGGTGAGGATATAGGCCATGTTGTAATGCAATACATGTATGTCCCTCCTGGGGCACCAAT
1790  80_HRV57a|    AGGTGAGGATATAGGCCATGTTGTAATGCAATACATGTATGTCCCTCCTGGGGCACCAAT
1791  81_HRV57b|    AGGTGAGGATATAGGCCATGTTGTAATGCAATACATGTATGTCCCTCCTGGGGCACCAAT
1792  82_HRV21      AACGGGTGACATAGGACATGTTGTAATGCAATATATGTATGTCCCACCAGGTGCTCCAAT
1793  83_HRVHan     AGCGGGTGACATAGGACATGTTGTGATGCAATATATGTATGTCCCACCAGGTGCTCCAAT
1794  84_HRV43      AAGCAATGATATAGGCCATGTGGTAATGCAGTACATGTATGTACCACCAGGTGCGCCAAT
1795  85_HRV43b|    AAGCAATGATATAGGCCATGTGGTAATGCAGTACATGTATGTACCACCAGGTGCGCCAAT
1796  86_HRV43a|    AAGCAATGATATAGGCCATGTGGTAATGCAGTACATGTATGTACCACCAGGTGCGCCAAT
1797  87_HRV75      AGGGAATGACATAGGCCATGTAGTAATGCAATATATGTATGTACCACCAGGAGCACCAAT
1798  88_HRV75b|    AGGGAATGACATAGGCCATGTAGTAATGCAATATATGTATGTACCACCAGGAGCACCAAT
1799  89_HRV75a|    AGGGAATGACATAGGCCATGTAGTAATGCAATATATGTATGTACCACCAGGAGCACCAAT
1800  96_HRV9a|d    AAGTGATAGCGTTGGCCATGTTGTTATGCAGTACATGTATGTACCACCAGGGGCACCTTT
1801  97_HRV9b|d    AAGTGATAGCGTTGGCCATGTTGTTATGCAGTACATGTATGTACCACCAGGGGCACCTTT
1802  98_HRV9       AAGTGATAGCGTTGGCCATGTTGTTATGCAGTACATGTATGTACCACCAGGGGCACCTTT
1803  99_HRV32      AAGTGACAGCATTGGTCATGTTGTTATGCAGTACATGTATGTACCACCAGGGGCTCCTCT
1804  100_HRV32a    AAGTGACAGCATTGGTCATGTTGTTATGCAGTACATGTATGTACCACCAGGGGCTCCTCT
1805  101_HRV32b    AAGTGACAGCATTGGTCATGTTGTTATGCAGTACATGTATGTACCACCAGGGGCTCCTCT
1806  102_HRV67     GAGTGACAGCATTGGTCATGTTGTAATGCAATATATGTATGTACCTCCAGGAGCACCATT
1807  103_HRV67a    GAGTGACAGCATTGGGCATGTTGTAATGCAATATATGTATGTACCTCCAGGAGCACCATT
1808  104_HRV67b    GAGTGACAGCATTGGGCATGTTGTAATGCAATATATGTATGTACCTCCAGGAGCACCATT
1809  105_HRV15     GAGTGATAACATCGGTCATGTTGTCATGCAATATATGTATGTTCCTCCGGGAGCCCCTTT
1810  106_HRV15a    GAGTGATAACATCGGTCATGTTGTCATGCAATATATGTATGTTCCTCCGGGAGCCCCTTT
1811  107_HRV15b    GAGTGATAACATCGGTCATGTTGTCATGCAATATATGTATGTTCCTCCGGGAGCCCCTTT
1812  108_HRV74a    AAGTGACAACATTGGCCATGTTGTTATGCAATACATGTATGTCCCCCCAGGAGCACCTTT
1813  109_HRV74b    AAGTGACAACATTGGCCATGTTGTTATGCAATACATGTATGTCCCCCCAGGAGCACCTTT
1814  110_HRV74     AAGTGACAACATTGGCCATGTTGTTATGCAATACATGTATGTCCCCCCAGGAGCACCTTT
1815  111_HRV38a    AAATGAAGGTGTGGGGCATGTTGTTATGCAGTATATGTATGTCCCTCCAGGGGCACCATT
```

FIG. D11 CONT'D

```
07.trace                                                                9/20/2007 5:04 PM 1816 112_HRV38b  AAATGAAGGTGTGGGGCATGTTGTTATGCAGTATATGTATGTCCCTCCAGGGGCACCATT
1817 113_HRV38   AAATGAAGGTGTGGGGCATGTTGTTATGCAGTATATGTATGTCCCTCCAGGGGCACCATT
1818 114_HRV60   AAATGATGGCATAGGTCATGTTGTCATGCAATACATGTATGTCCCCCCAGGAGCACCATT
1819 115_HRV60a  AAATGATGGCATAGGTCATGTTGTCATGCAATACATGTATGTCCCCCCAGGAGCACCATT
1820 116_HRV60b  AAATGATGGCATAGGTCATGTTGTCATGCAATACATGTATGTCCCCCCAGGAGCACCATT
1821 117_HRV64a  GAGTGCTAACATTGGTCATGTTGTTATGCAATATATGTATGTCCCTCCTGGAGCTCCAAT
1822 118_HRV64b  GAGTGCTAACATTGGTCATGTTGTTATGCAATATATGTATGTCCCTCCTGGAGCTCCAAT
1823 119_HRV64   GAGTGCTAACATTGGTCATGTTGTTATGCAATATATGTATGTCCCTCCTGGAGCTCCAAT
1824 120_HRV94a  AAGTGCTAATATTGGTCATGTTGTCATGCAGTACATGTATGTTCCTCCTGGAGCTCCAAA
1825 121_HRV94b  AAGTGCTAATATTGGTCATGTTGTCATGCAGTACATGTATGTTCCTCCTGGAGCTCCAAA
1826 122_HRV94   AAGTGCTAATATTGGTCATGTTGTCATGCAGTACATGTATGTTCCTCCTGGAGCTCCAAA
1827 123_HRV22   AAGTAAAAACATTGGTCATGTGGTCATGCAATACATGTATGTTCCGCCTGGAGCTCCTAA
1828 124_HRV22a  AAGTAAAAACATTGGTCATGTGGTCATGCAATACATGTATGTTCCGCCTGGAGCTCCTAA
1829 125_HRV22b  AAGTAAAAACATTGGTCATGTGGTCATGCAATACATGTATGTTCCGCCTGGAGCTCCTAA
1830 126_HRV82   AAGTAATGATATTGGGCATGTAGTGATGCAATACATGTATGTCCCACCAGGTGCTCCTAA
1831 127_HRV82b  AAGTAATGATATTGGGCATGTAGTGATGCAATACATGTATGTCCCACCAGGTGCTCCTAA
1832 128_HRV82a  AAGTAATGATATTGGGCATGTAGTGATGCAATACATGTATGTCCCACCAGGTGCTCCTAA
1833 129_HRV19   AAGTAAAAACATTGGACATGTTGTTATGCAATACATGTATGTGCCTCCTGGTGCTCCTAT
1834 130_HRV19a  AAGTAAAAACATTGGACATGTTGTTATGCAATACATGTATGTGCCTCCTGGTGCTCCTAT
1835 131_HRV19b  AAGTAAAAACATTGGACATGTTGTTATGCAATACATGTATGTGCCTCCTGGTGCTCCTAT
1836 132_HRV13   AGGTGGTGATGTCGGACATGTTGTTATGCAATACATGTATGTACCGCCCGGTGCACCCCT
1837 133_HRV13a  AGGTGGTGATGTCGGACATGTTGTTATGCAATACATGTATGTACCGCCCGGTGCACCCCT
1838 134_HRV13b  AGGTGGTGATGTCGGACATGTTGTTATGCAATACATGTATGTACCGCCCGGTGCACCCCT
1839 135_HRV41   GGGTAGTGATGTCGGACATGTTGTCATGCAATACATGTTCGTACCACCTGGCGCACCCCT
1840 136_HRV41a  GGGTAGTGATGTCGGACATGTTGTCATGCAATACATGTTCGTACCACCTGGCGCACCCCT
1841 137_HRV41b  GGGTAGTGATGTCGGACATGTTGTCATGCAATACATGTTCGTACCACCTGGCGCACCCCT
1842 138_HRV73   AAGTGGAGATGTGGGACATGTAGTTATGCAGTATATGTATGTCCCACCTGGAGCCCCTCT
1843 139_HRV73b  AAGTGGAGATGTGGGACATGTAGTTATGCAGTATATGTATGTCCCACCTGGAGCCCCTCT
1844 140_HRV73a  AAGTGGAGATGTGGGACATGTAGTTATGCAGTATATGTATGTCCCACCTGGAGCCCCTCT
1845 141_HRV61   AGGTGGTGACATTGGACACGTGGTCATGCAATACATGTATGTTCCACCTGGTGCACCTAC
1846 142_HRV61a  AGGTGGTGACATTGGACACGTGGTCATGCAATACATGTATGTTCCACCTGGTGCACCTAC
1847 143_HRV61b  AGGTGGTGACATTGGACACGTGGTCATGCAATACATGTATGTTCCACCTGGTGCACCTAC
1848 144_HRV96   GAGTGGTGATATTGGTCATGTGGTCATGCAATATATGTATGTTCCACCAGGTGCCCCCAC
1849 145_HRV96b  GAGTGGTGATATTGGTCATGTGGTCATGCAATATATGTATGTTCCACCAGGTGCCCCCAC
1850 146_HRV96a  GAGTGGTGATATTGGTCATGTGGTCATGCAATATATGTATGTTCCACCAGGTGCCCCCAC
1851 90_HRV16a|  AGATGGTCACATTGGTCATATAGTCATGCAATATATGTATGTACCACCAGGAGCACCTAT
1852 91_HRV16b|  AGATGGTCACATTGGTCATATAGTCATGCAATATATGTATGTACCACCAGGAGCACCTAT
1853 92_1AYM_A   AGATGGTCACATTGGTCATATAGTCATGCAATATATGTATGTACCACCAGGAGCACCTAT
1854 93_HRV81a|  GGAAGGTCATATTGGTCATATAGTAATGCAATACATGTATGTACCACCAGGAGCACCCAT
1855 94_HRV81b|  GGAAGGTCATATTGGTCATATAGTAATGCAATACATGTATGTACCACCAGGAGCACCCAT
1856 95_HRV81    GGAAGGTCATATTGGTCATATAGTAATGCAATACATGTATGTACCACCAGGAGCACCCAT
1857 147_HRV2    TAGTCAGGACATTGGACACATCACAATGCAATACATGTATGTTCCACCTGGTGCACCGGT
1858 148_HRV2a|  TAGTCAGGACATTGGACACATCACAATGCAATACATGTATGTTCCACCTGGTGCACCGGT
1859 149_HRV2b|  TAGTCAGGACATTGGACACATCACAATGCAATACATGTATGTTCCACCTGGTGCACCGGT
1860 150_HRV49a  TAGCAAGGATATTGGACACATTACAATGCAATACATGTATGTGCCGCCAGGTGCACCTGT
1861 151_HRV49b  TAGCAAGGATATTGGACACATTACAATGCAATACATGTATGTGCCGCCAGGTGCACCTGT
1862 152_HRV49   TAGCAAGGATATTGGACACATTACAATGCAATACATGTATGTGCCGCCAGGTGCACCTGT
1863 153_HRV23a  TAGTCAAGATATTGGTCACATCACAATGCAGTATATGTATGTCCCACCAGGTGCTCCAAT
1864 154_HRV23b  TAGTCAAGATATTGGTCACATCACAATGCAGTATATGTATGTCCCACCAGGTGCTCCAAT
1865 155_HRV23   TAGTCAAGATATTGGTCACATCACAATGCAGTATATGTATGTCCCACCAGGTGCTCCAAT
1866 156_HRV30a  CAGCCAAGATATCGGACACATTACAATGCAGTATATGTATGTTCCACCTGGCGCTCCAAT
1867 157_HRV30b  CAGCCAAGATATCGGACACATTACAATGCAGTATATGTATGTTCCACCTGGCGCTCCAAT
1868 158_HRV30   CAGCCAAGATATCGGACACATTACAATGCAGTATATGTATGTTCCACCTGGCGCTCCAAT
1869 159_HRV7    AGGTAATGATATTGGACATATAGTTATGCAATTTATGTATGTACCTCCAGGGGCCCCAGT
1870 160_HRV7b|  AGGTAATGATATTGGACATATAGTTATGCAATTTATGTATGTACCTCCAGGGGCCCCAGT
1871 161_HRV7a|  AGGTAATGATATTGGACATATAGTTATGCAATTTATGTATGTACCTCCAGGGGCCCCAGT
1872 162_HRV88   AGGTGATGATACTGGACATATAGTACTGCAATTCATGTATGTGCCTCCAGGTGCACCAAT
1873 163_HRV88a  AGGTGATGATACTGGACATATAGTACTGCAATTCATGTATGTGCCTCCAGGTGCACCAAT
1874 164_HRV88b  AGGTGATGATACTGGACATATAGTACTGCAATTCATGTATGTGCCTCCAGGTGCACCAAT
1875 165_HRV36a  GGGAGATGATAGTGGGCATGTAGTATTACAATTCATGTATGTACCTCCAGGAGCGCCTGT
1876 166_HRV36b  GGGAGATGATAGTGGGCATGTAGTATTACAATTCATGTATGTACCTCCAGGAGCGCCTGT
1877 167_HRV36   GGGAGATGATAGTGGGCATGTAGTATTACAATTCATGTATGTACCTCCAGGAGCGCCTGT
1878 168_HRV89a  AGGAAATGATAGTGGACATATAGTATTGCAATTTATGTATGTACCCCCAGGAGCACCTGT
1879 169_HRV89b  AGGAAATGATAGTGGACATATAGTATTGCAATTTATGTATGTACCCCCAGGAGCACCTGT
1880 170_HRV89   AGGAAATGATAGTGGACATATAGTATTGCAATTTATGTATGTACCCCCAGGAGCACCTGT
```

FIG. D11 CONT'D 07.trace                                                                  9/20/2007 5:04 PM

```
1881 171_HRV58     AGGAGAAGATAATGGACATATTGTGTTACAATTTATGTATGTACCCCCAGGAGCACCTGT
1882 172_HRV58a    AGGAGAAGATAATGGACATATTGTGTTACAATTTATGTATGTACCCCCAGGAGCACCTGT
1883 173_HRV58b    AGGAGAAGATAATGGACATATTGTGTTACAATTTATGTATGTACCCCCAGGAGCACCTGT
1884 174_HRV12a    AGAAGGAAGCAATGGTCACGTGGTGGTCCAATACATGTATGTACCTCCTGGTGCCCCACT
1885 175_HRV12b    AGAAGGAAGCAATGGTCACGTGGTGGTCCAATACATGTATGTACCTCCTGGTGCCCCACT
1886 176_HRV12     AGAAGGAAGCAATGGTCACGTGGTGGTCCAATACATGTATGTACCTCCTGGTGCCCCACT
1887 177_HRV78a    AGGAGACAATAATGGACATGTGGTGCTTCAATTTATGTTTGTTCCACCTGGAGCCCCTAT
1888 178_HRV78b    AGGAGACAATAATGGACATGTGGTGCTTCAATTTATGTTTGTTCCACCTGGAGCCCCTAT
1889 179_HRV78     AGGAGACAATAATGGACATGTGGTGCTTCAATTTATGTTTGTTCCACCTGGAGCCCCTAT
1890 180_HRV20     AGGTCGGGATAATGGGCATGTTGTTTTACAGTATATGTATGTACCACCAGGGGCACCAAT
1891 181_HRV20a    AGGTCGGGATAATGGGCATGTTGTTTTACAGTATATGTATGTACCACCAGGGGCACCAAT
1892 182_HRV20b    AGGTCGGGATAATGGGCATGTTGTTTTACAGTATATGTATGTACCACCAGGGGCACCAAT
1893 183_HRV68     TGGAAAAGATAATGGCCATGTGGTTTTACAGTACATGTATGTGCCGCCAGGGGCACCCAT
1894 184_HRV68a    TGGAAAAGATAATGGCCATGTGGTTTTACAGTACATGTATGTGCCGCCAGGGGCACCCAT
1895 185_HRV68b    TGGAAAAGATAATGGCCATGTGGTTTTACAGTACATGTATGTGCCCCCACGGGGCACCCAT
1896 186_HRV28     AGGTGATGATAATGGGCATGTAGTTATGCAATATATGTATGTACCTCCAGGAGCCCCCAT
1897 187_HRV28a    AGGTGATGATAATGGGCATGTAGTTATGCAATATATGTATGTACCTCCAGGAGCCCCCAT
1898 188_HRV28b    AGGTGATGATAATGGGCATGTAGTTATGCAATATATGTATGTACCTCCAGGAGCCCCCAT
1899 189_HRV53a    ACAAGGGAATAACGGGCACGTGGTGATACAATACATGTATGTACCACCGGGTGCTCCAAT
1900 190_HRV53b    ACAAGGGAATAACGGGCACGTGGTGATACAATACATGTATGTACCACCGGGTGCTCCAAT
1901 191_HRV53     ACAAGGGAATAACGGGCACGTGGTGATACAATACATGTATGTACCACCGGGTGCTCCAAT
1902 192_HRV46a    AGGGGATGATATTGGACATGTGGTCATACAATATATGTATGTGCCTCCTGGTGCTCCATT
1903 193_HRV46b    AGGGGATGATATTGGACATGTGGTCATACAATATATGTATGTGCCTCCTGGTGCTCCATT
1904 194_HRV46     AGGGGATGATATTGGACATGTGGTCATACAATATATGTATGTGCCTCCTGGTGCTCCATT
1905 195_HRV80a    AGGGGAGGACATTGGTCATGTAGTTATTCAATACATGTACGTACCACCAGGGGCCCCGTT
1906 196_HRV80b    AGGGGAGGACATTGGTCATGTAGTTATTCAATACATGTACGTACCACCAGGGGCCCCGTT
1907 197_HRV80     AGGGGAGGACATTGGTCATGTAGTTATTCAATACATGTACGTACCACCAGGGGCCCCGTT
1908 198_HRV51     GGGTGATGACATAGGGCACATTGTACTTCAATACATGTATGTACCCCCTGGAGGACCAGT
1909 199_HRV51a    GGGTGATGACATAGGGCACATTGTACTTCAATACATGTATGTACCCCCTGGAGGACCAGT
1910 200_HRV51b    GGGTGATGACATAGGGCACATTGTACTTCAATACATGTATGTACCCCCTGGAGGACCAGT
1911 201_HRV65a    AGGTGATGACATAGGGCACATAGTGCTTCAATATATGTATGTGCCTCCTGGTGGTCCTGT
1912 202_HRV65b    AGGTGATGACATAGGGCACATAGTGCTTCAATATATGTATGTGCCTCCTGGTGGTCCTGT
1913 203_HRV65     AGGTGATGACATAGGGCACATAGTGCTTCAATATATGTATGTGCCTCCTGGTGGTCCTGT
1914 204_HRV71a    AGGAGATGATTTAGGACATATTGTACTCCAGTACATGTATGTTCCCCCAGGTGGTCCAAT
1915 205_HRV71b    AGGAGATGATTTAGGACATATTGTACTCCAGTACATGTATGTTCCCCCAGGTGGTCCAAT
1916 206_HRV71     AGGAGATGATTTAGGACATATTGTACTCCAGTACATGTATGTTCCCCCAGGTGGTCCAAT
1917 207_HRV8      AAAAGGTGACCTTGGACACATAGTCCTTCAATACATGTATGTTCCCCCGGGTGCACCTCT
1918 208_HRV95     AGAAGGTGACCTTGGACACATAGTCCTCCAATACATGTATGTTCCCCCGGGTGCACCTCT
1919 209_HRV45     AGAAGGTAACTTGGGACACATTGTTGTGCAATACATGTTTGTACCACCAGGAGCACCTCT
1920 210_HRV45a    AGAAGGTAACTTGGGACACATTGTTGTGCAATACATGTTTGTACCACCAGGAGCACCTCT
1921 211_HRV45b    AGAAGGTAACTTGGGACACATTGTTGTGCAATACATGTTTGTACCACCAGGAGCACCTCT
1922 GROUP_1       -------------GG-CA--T-----T-CA-T--ATGT---T-CC-CC-GG-G--CC---
1923
1924 1_HRV1A1|d    TCCTTCAAAAAGAAACGATTTCTCATGGCAATCAGGCACCAATATGTCAATATTCTGGCA
1925 2_HRV1A2|d    TCCTTCAAAAAGAAACGATTTCTCATGGCAATCAGGCACCAATATGTCAATATTCTGGCA
1926 3_HRV1A|cD    TCCTTCAAAAAGAAACGATTTCTCATGGCAATCAGGCACCAATATGTCAATATTCTGGCA
1927 4_HRV1B1|d    TCCAAAAACAAGAAATGATTTCTCATGGCAATCAGGCACTAATATGTCAATATTCTGGCA
1928 5_HRV1B2|d    TCCAAAAACAAGAAATGATTTCTCATGGCAATCAGGCACTAATATGTCAATATTCTGGCA
1929 6_HRV1B       TCCAAAAACAAGAAATGATTTCTCATGGCAATCAGGCACTAATATGTCAATATTCTGGCA
1930 7_HRV40a|d    ACCAAAGAAAAGAAATGATTACACATGGCAGTCAGGCACTAATGCTTCTGTATTCTGGCA
1931 8_HRV40b|d    ACCAAAGAAAAGAAATGATTACACATGGCAGTCAGGCACTAATGCTTCTGTATTCTGGCA
1932 9_HRV40       ACCAAAGAAAAGAAATGATTACACATGGCAGTCAGGCACTAATGCTTCTGTATTCTGGCA
1933 10_HRV85      ACCAAGGAAAAGAGATGATTACACATGGCAATCAGGTACTAATGCTTCCGTGTTTTGGCA
1934 11_HRV85a|    ACCAAGGAAAAGAGATGATTACACATGGCAATCAGGTACTAATGCTTCCGTGTTTTGGCA
1935 12_HRV85b|    ACCAAGGAAAAGAGATGATTACACATGGCAATCAGGTACTAATGCTTCCGTGTTTTGGCA
1936 13_HRV56a|    TCCAAACTCAAGAGATGATTTACATGGCAATCTGGCACCAATGCTTCTGTCTTTTGGCA
1937 14_HRV56b|    TCCAAACTCAAGAGATGATTTACATGGCAATCTGGCACCAATGCTTCTGTCTTTTGGCA
1938 15_HRV56      TCCAAACTCAAGAGATGATTTACATGGCAATCTGGCACCAATGCTTCTGTCTTTTGGCA
1939 16_HRV54      ACCAGAAAAAGGAATGATTACACCTGGGAGTCAAGCACAAACCCTTCTATATTTTGGCA
1940 17_HRV98      ACCTAAAAGAGGAATGATTATACTTGGGAATCAAGCACAAACCCTTCTATATTCTGGCA
1941 18_HRV59a|    GCCCACAAAGAGAGATGATTACACATGGCAATCTGGTACTAATGCTTCAATATTCTGGCA
1942 19_HRV59b|    GCCCACAAAGAGAGATGATTACACATGGCAATCTGGTACTAATGCTTCAATATTCTGGCA
1943 20_HRV59      GCCCACAAAGAGAGATGATTACACATGGCAATCTGGTACTAATGCTTCAATATTCTGGCA
1944 21_HRV63      ACCCACCCGAAGAGAAGATTACACATGGCAATCTGGCACTAATGCTTCAATATTCTGGCA
1945 22_HRV63b|    ACCCACCCGAAGAGAAGATTACACATGGCAATCTGGCACTAATGCTTCAATATTCTGGCA
```

FIG. D11 CONT'D

07.trace                                                                 9/20/2007 5:04 PM

```
1946 23_HRV63a|  ACCCACCCGAAGAGAAGATTACACATGGCAATCTGGCACTAATGCTTCAATATTCTGGCA
1947 24_HRV39    ACCTAAGAAGAGAGATGATTACACATGGCAATCTGGAACAAATGCCTCAGTTTTCTGGCA
1948 25_HRV39a|  ACCTAAGAAGAGAGATGATTACACATGGCAATCTGGAACAAATGCCTCAGTTTTCTGGCA
1949 26_HRV39b|  ACCTAAGAAGAGAGATGATTACACATGGCAATCTGGAACAAATGCCTCAGTTTTCTGGCA
1950 27_HRV10a|  ACCAACTAAGAGAGATGATTTTGCTTGGCAGTCGGGAACAAATGCATCAGTCTTCTGGCA
1951 28_HRV10b|  ACCAACTAAGAGAGATGATTTTGCTTGGCAGTCGGGAACAAATGCATCAGTCTTCTGGCA
1952 29_HRV10    ACCAACTAAGAGAGATGATTTTGCTTGGCAGTCGGGAACAAATGCATCAGTCTTCTGGCA
1953 30_HRV100a  TCCAACAAAAAGGGATGATTTTGCATGGCAATCAGGCACAAATGCATCAGTTTTTTGGCA
1954 31_HRV100b  TCCAACAAAAAGGGATGATTTTGCATGGCAATCAGGCACAAATGCATCAGTTTTTTGGCA
1955 32_HRV100   TCCAACAAAAAGGGATGATTTTGCATGGCAATCAGGCACAAATGCATCAGTTTTTTGGCA
1956 33_HRV66    TCCAGATAATAGAACACACTTTGCTTGGCAATCAGGAACAAATGCATCTATATTCTGGCA
1957 34_HRV66b|  TCCAGATAATAGAACACACTTTGCTTGGCAATCAGGAACAAATGCATCTATATTCTGGCA
1958 35_HRV66a|  TCCAGATAATAGAACACACTTTGCTTGGCAATCAGGAACAAATGCATCTATATTCTGGCA
1959 36_HRV77a|  ACCAGATAGCAGGACTCATTTTGCATGGCAGTCAGGGACTAATGCATCAATATTCTGGCA
1960 37_HRV77b|  ACCAGATAGCAGGACTCATTTTGCATGGCAGTCAGGGACTAATGCATCAATATTCTGGCA
1961 38_HRV77    ACCAGATAGCAGGACTCATTTTGCATGGCAGTCAGGGACTAATGCATCAATATTCTGGCA
1962 39_HRV62a   ACCAACAGACAGAAAGCATTTTGCCTGGCAATCAAGTACTAATGCATCAATATTTTGGCA
1963 40_HRV62b   ACCAACAGACAGAAAGCATTTTGCCTGGCAATCAAGTACTAATGCATCAATATTTTGGCA
1964 41_HRV25    ACCAACAGACAGAAAACACTTTGCATGGCAATCAAGTACTAATGCATCAATATTTTGGCA
1965 42_HRV29a   ACCAAATGACAGAAATCATTTTGCATGGCAATCAGGGACTAATGCATCAATATTCTGGCA
1966 43_HRV29b   ACCAAATGACAGAAATCATTTTGCATGGCAATCAGGGACTAATGCATCAATATTCTGGCA
1967 44_HRV44a   ACCAGATGACAGAAACCACTTTGCATGGCAATCGGGGACTAATGCATCAATATTCTGGCA
1968 45_HRV44b   ACCAGATGACAGAATCCACTTTGCATGGCAATCGGGGAATAATGCATCAATATTCTGGCA
1969 46_HRV31    ACCAACAAATAGAAAACATTTTGCATGGCAATCAGGTACTAATGCATCGATTTCTGGCA
1970 47_HRV31a|  ACCAACAAATAGAAAACATTTTGCATGGCAATCAGGTACTAATGCATCGATTTTCTGGCA
1971 48_HRV31b|  ACCAACAAATAGAAAACATTTTGCATGGCAATCAGGTACTAATGCATCGATTTTCTGGCA
1972 49_HRV47    GCCAACAAGTAGAGAGCACTTTGCATGGCAGTCAGGTACCAATGCATCAACTTTCTGGCA
1973 50_HRV47a|  GCCAACAAGTAGAGAGCACTTGCATGGCAGTCAGGTACCAATGCATCAACTTTCTGGCA
1974 51_HRV47b|  GCCAACAAGTAGAGAGCACTTTGCATGGCAGTCAGGTACCAATGCATCAATTTTCTGGCA
1975 52_HRV11    TCCAGAGAAAAGAGATGATTATACATGGCAATCAGGAACAAATGCATCTATTTTCTGGCA
1976 53_HRV11b|  TCCAGAGAAAAGAGATGATTATACATGGCAATCAGGAACAAATGCATCTATTTTCTGGCA
1977 54_HRV11a|  TCCAGAGAAAAGAGATGATTATACATGGCAATCAGGAACAAATGCATCTATTTTCTGGCA
1978 55_HRV76    TCCAAAGAAGACAGAGATGACTACACATGGCAGTCAGGAACCAATGCATCTATTTTCTGGCA
1979 56_HRV76b|  TCCAAAGAAGACAGAGATGACTACACATGGCAGTCAGGAACCAATGCATCTATTTTCTGGCA
1980 57_HRV76a|  TCCAAAGAAGACAGAGATGACTACACATGGCAGTCAGGAACCAATGCATCTATTTTCTGGCA
1981 58_HRV33    TCCAGAAAGAGAGATGATTACACATGGCAATCAGGAACAAATGCATCTGTCTTTTGGCA
1982 59_HRV33b|  TCCAGAAAAGAGAGATGATTACACATGGCAATCAGGAACAAATGCATCTGTCTTTTGGCA
1983 60_HRV33a|  TCCAGAAAAGAGAGATGATTACACATGGCAATCAGGAACAAATGCATCTGTCTTTTGGCA
1984 61_HRV24a|  CCCAACAAAGAGAGATGATTATACATGGCAATCAGGAACAAATGCATCTGTCTTTTGGCA
1985 62_HRV24b|  CCCAACAAAGAGAGATGATTATACATGGCAATCAGGAACAAATGCATCTGTCTTTTGGCA
1986 63_HRV24    CCCAACAAAGAGAGATGATTATACATGGCAATCAGGAACAAATGCATCTGTCTTTTGGCA
1987 64_HRV90    ACCTGAGAAGAGGGGATGATTATGCATGGCAATCAGGCACTAATGCATCTCTTTTCTGGCA
1988 65_HRV90a|  ACCTGAGAAGAGGGATGATTATGCATGGCAATCAGGCACTAATGCATCTATCTTTTGGCA
1989 66_HRV90b|  ACCTGAGAAGAGGGATGATTATGCATGGCAATCAGGCACTAATGCATCTATCTTTTGGCA
1990 67_HRV34    ACCTAAAACTAGAGATGATTTTGCATGGCAATCTGGAACAAATGCCTCAATATTTTGGCA
1991 68_HRV34b|  ACCTAAAACTAGAGATGATTTTGCATGGCAATCTGGAACAAATGCCTCAATATTTTGGCA
1992 69_HRV34a|  ACCTAAAACTAGAGATGATTTTGCATGGCAATCTGGAACAAATGCCTCAATATTTTGGCA
1993 70_HRV50a|  ACCCAAGACTAGGGATGATTTTGCCTGGCAATCTGGAACTAATGCTTCAATCTTTTGGCA
1994 71_HRV50b|  ACCCAAGACTAGGGATGATTTTGCCTGGCAATCTGGAACTAATGCTTCAATCTTTTGGCA
1995 72_HRV50    ACCCAAGACTAGGGATGATTTTGCCTGGCAATCTGGAACTAATGCTTCAATCTTTTGGCA
1996 73_HRV18a|  ACCAAAAACCAGAGATGATTTTGCCTGGCAATCTGGAACAAATGCATCAATCTTCTGGCA
1997 74_HRV18b|  ACCAAAAACCAGAGATGATTTTGCCTGGCAATCTGGAACAAATGCATCAATCTTCTGGCA
1998 75_HRV18    ACCAAAAACCAGAGATGATTTTGCCTGGCAATCTGGAACAAATGCATCAATCTTCTGGCA
1999 76_HRV55    TCCAAAGACAAGAGAAGATTATGCTTGGCAATCAGGGACCAATGCATCTATCTTTTGGCA
2000 77_HRV55b|  TCCAAAGACAAGAGAAGATTATGCTTGGCAATCAGGGACCAATGCATCTATCTTTTGGCA
2001 78_HRV55a|  TCCAAAGACAAGAGAAGATTATGCTTGGCAATCAGGGACCAATGCATCTATCTTTTGGCA
2002 79_HRV57    TCCAAAAACAAGAGAGGATTATACATGGCAATCTGGTACCAATGCTTCAATATTTTGGCA
2003 80_HRV57a|  TCCAAAAACAAGAGAGGATTATACATGGCAATCTGGTACCAATGCTTCAATATTTTGGCA
2004 81_HRV57b|  TCCAAAAACAAGAGAGGATTATACATGGCAATCTGGTACCAATGCTTCAATATTTTGGCA
2005 82_HRV21    TCCAAAAACTAGGGAAGATTTTGCTTGGCAGTCAGGCACTAATGCATCATCCATTTCTGGCA
2006 83_HRVHan   TCCAAAAACTAGGGAAGATTTTGCTTGGCAATCAGGTACCAATGCATCCATTTTCTGGCA
2007 84_HRV43    TCCAAAAACTAGGAAAGATTATGCATGGCAATCTGGCACAAATGCATCTGTTTTCTGGCA
2008 85_HRV43b|  TCCAAAAACTAGGAAAGATTATGCATGGCAATCTGGCACAAATGCATCTGTTTTCTGGCA
2009 86_HRV43a|  TCCAAAAACTAGGAAAGATTATGCATGGCAATCTGGCACAAATGCATCTGTTTTCTGGCA
2010 87_HRV75    ACCAACAACTAGAAAAGATTATGCATGGCAATCTGGAACAAATGCATCTGTATTTTGGCA
```

FIG. D11 CONT'D 07.trace                                                                                                    9/20/2007 5:04 PM

```
2011  88_HRV75b|   ACCAACAACTAGAAAAGATTATGCATGGCAATCTGGAACAAATGCATCTGTATTTTGGCA
2012  89_HRV75a|   ACCAACAACTAGAAAAGATTATGCATGGCAATCTGGAACAAATGCATCTGTATTTTGGCA
2013  96_HRV9a|d   ACCAAGGACTAGAGATGATTATGCATGGCAATCAGGCACAAATGCTTCCATCTTTTGGCA
2014  97_HRV9b|d   ACCAAGGACTAGAGATGATTATGCATGGCAATCAGGCACAAATGCTTCCATCTTTTGGCA
2015  98_HRV9      ACCAAGGACTAGAGATGATTATGCATGGCAATCAGGCACAAATGCTTCCATCTTTTGGCA
2016  99_HRV32     ACCACAAGCAAGAGATGACTACACATGGCAATCTGGCACGAATGCATCTATCTTTTGGCA
2017 100_HRV32a    ACCACAAGCAAGAGATGACTACACATGGCAATCTGGCACGAATGCATCTATCTTTTGGCA
2018 101_HRV32b    ACCACAAGCAAGAGATGACTACACATGGCAATCTGGCACGAATGCATCTATCTTTTGGCA
2019 102_HRV67     ACCAACAAAAGAGATGACTACACATGGCAATCAGGTACAAATGCATCCATCTTTTGGCA
2020 103_HRV67a    ACCAACAAAAGAGATGACTACACATGGCAATCAGGTACAAATGCATCCATCTTTTGGCA
2021 104_HRV67b    ACCAACAAAAGAGATGACTACACATGGCAATCAGGTACAAATGCATCCATCTTTTGGCA
2022 105_HRV15     ACCCAATAAAAGGAATGATTACACATGGCAATCAGGTACAAATGCCTCTGTTTTCTGGCA
2023 106_HRV15a    ACCCAATAAAAGGAATGATTACACATGGCAATCAGGTACAAATGCCTCTGTTTTCTGGCA
2024 107_HRV15b    ACCCAATAAAAGGAATGATTACACATGGCAATCAGGTACAAATGCCTCTGTTTTCTGGCA
2025 108_HRV74a    ACCCAAGAAAAGAGATGATTACACATGGCAATCTGGCACAAATGCATCTGTGTTTTGGCA
2026 109_HRV74b    ACCCAAGAAAAGAGATGATTACACATGGCAATCTGGCACAAATGCATCTGTGTTTTGGCA
2027 110_HRV74     ACCCAAGAAAAGAGATGATTACACATGGCAATCTGGCACAAATGCATCTGTGTTTTGGCA
2028 111_HRV38a    ACCCAGGAAGAGAGATTACACTTGGCAATCTGGTACAAATGCCTCTGTTTTCTGGCA
2029 112_HRV38b    ACCCAGGAAGAGAGATGATTACACTTGGCAATCTGGTACAAATGCCTCTGTTTTCTGGCA
2030 113_HRV38     ACCCAGGAAGAGAGATGATTACACTTGGCAATCTGGTACAAATGCCTCTGTTTTCTGGCA
2031 114_HRV60     ACCTACTAAAAGAGACGATTACACATGGCAATCTGGCACAAATGCTTCTGTATTTTGGCA
2032 115_HRV60a    ACCTACTAAAAGAGACGATTACACATGGCAATCTGGCACAAATGCTTCTGTATTTTGGCA
2033 116_HRV60b    ACCTACTAAAAGAGACGATTACACATGGCAATCTGGCACAAATGCTTCTGTATTTTGGCA
2034 117_HRV64a    ACCAACCAAAAGAAATGATTACGTCTGGCAGTCAGGCACCAATGCATCCATCTTTTGGCA
2035 118_HRV64b    ACCAACCAAAAGAAATGATTACGTCTGGCAGTCAGGCACCAATGCATCCATCTTTTGGCA
2036 119_HRV64     ACCAACCAAAAGAAATGATTACGTCTGGCAGTCAGGCACCAATGCATCCATCTTTTGGCA
2037 120_HRV94a    ACCAGACAAAAGAGATGATTATGTTTGGCAATCAGGAACTAATGCATCTATATTCTGGCA
2038 121_HRV94b    ACCAGACAAAAGAGATGATTATGTTTGGCAATCAGGAACTAATGCATCTATATTCTGGCA
2039 122_HRV94     ACCAGACAAAAGAGATGATTATGTTTGGCAATCAGGAACTAATGCATCTATATTCTGGCA
2040 123_HRV22     ACCTGAAAAGAGAGATGACTACACATGGCAATCTGGCACTAATGCATCTGTTTTCTGGCA
2041 124_HRV22a    ACCTGAAAAGAGAGATGACTACACATGGCAATCTGGCACTAATGCATCTGTTTTCTGGCA
2042 125_HRV22b    ACCTGAAAAGAGAGATGACTACACATGGCAATCTGGCACTAATGCATCTGTTTTCTGGCA
2043 126_HRV82     ACCAGAAAAGAGAGACGACTACACTTGGCAATCTGGAACTAATGCTTCAATTTTCTGGCA
2044 127_HRV82b    ACCAGAAAAGAGAGACGACTACACTTGGCAATCTGGAACTAATGCTTCAATTTTCTGGCA
2045 128_HRV82a    ACCAGAAAAGAGAGACGACTACACTTGGCAATCTGGAACTAATGCTTCAATTTTCTGGCA
2046 129_HRV19     CCCAAAAACTAGAAATGATTACACATGGCAATCAGGTACTAATGCATCTATATTTTGGCA
2047 130_HRV19a    CCCAAAAACTAGAAATGATTACACATGGCAATCAGGTACTAATGCATCTATATTTTGGCA
2048 131_HRV19b    CCCAAAAACTAGAAATGATTACACATGGCAATCAGGTACTAATGCATCTATATTTTGGCA
2049 132_HRV13     TCCAACGAAGAGAAATGATTACACATGGCAATCTGGCACCAATGCATCTGTTTTCTGGCA
2050 133_HRV13a    TCCAACGAAGAGAAATGATTACACATGGCAATCTGGCACCAATGCATCTGTTTTCTGGCA
2051 134_HRV13b    TCCAACGAAGAGAAATGATTACACATGGCAATCTGGCACCAATGCATCTGTTTTCTGGCA
2052 135_HRV41     CCCAGAAAAGAGAGATGATTACACATGGCAATCTGGCACCAATGCATCTGTATTCTGGCA
2053 136_HRV41a    CCCAGAAAAGAGAGATGATTACACATGGCAATCTGGCACCAATGCATCTGTATTCTGGCA
2054 137_HRV41b    CCCAGAAAAGAGAGATGATTACACATGGCAATCTGGCACCAATGCATCTGTATTCTGGCA
2055 138_HRV73     ACCCACAAAAGAAATGACTACACATGGCAGTCCGGCACTAATGCATCAGTATTCTGGCA
2056 139_HRV73b    ACCCACAAAAGAAATGACTACACATGGCAGTCCGGCACTAATGCATCAGTATTCTGGCA
2057 140_HRV73a    ACCCACAAAAGAAATGACTACACATGGCAGTCCGGCACTAATGCATCAGTATTCTGGCA
2058 141_HRV61     ACCTGAGAAAAGAAATGATTTCACATGGCAATCAGGCACAAATGCATCTGTTTTCTGGCA
2059 142_HRV61a    ACCTGAGAAAAGAAATGATTTCACATGGCAATCAGGCACAAATGCATCTGTTTTCTGGCA
2060 143_HRV61b    ACCTGAGAAAAGAAATGATTTCACATGGCAATCAGGCACAAATGCATCTGTTTTCTGGCA
2061 144_HRV96     ACCTGAAGAGAGAGATGACTTTACATGGCAATCAGGCACAAATGCATCTGTGTTTTGGCA
2062 145_HRV96b    ACCTGAGAAGAGAGATGACTTTACATGGCAATCAGGCACAAATGCATCTGTGTTTTGGCA
2063 146_HRV96a    ACCTGAGAAGAGAGATGACTTTACATGGCAATCAGGCACAAATGCATCTGTGTTTTGGCA
2064  90_HRV16a|   ACCAACAACTAGAAATGACTATGCTTGGCAATCTGGAACAAATGCATCTGTATTTTGGCA
2065  91_HRV16b|   ACCAACAACTAGAAATGACTATGCTTGGCAATCTGGAACAAATGCATCTGTATTTTGGCA
2066  92_1AYM_A    ACCAACAACTAGAAATGACTATGCTTGGCAATCTGGAACAAATGCATCTGTATTTTGGCA
2067  93_HRV81a|   TCCAACAACTAGAGAAGACTATGCTTGGCAATCTGGAACAAATGCATCTATATTTGGCA
2068  94_HRV81b|   TCCAACAACTAGAGAAGACTATGCTTGGCAATCTGGAACAAATGCATCTATATTTGGCA
2069  95_HRV81     TCCAACAACTAGAGAAGACTATGCTTGGCAATCTGGAACAAATGCATCTATATTCTGGCA
2070 147_HRV2      GCCCAATAGTAGGGACGATTATGCATGGCAGTCTGGCACTAATGCCTCTGTTTTCTGGCA
2071 148_HRV2a|    GCCCAATAGTAGGGACGATTATGCATGGCAGTCTGGCACTAATGCCTCTGTTTTCTGGCA
2072 149_HRV2b|    GCCCAATAGTAGGGACGATTATGCATGGCAGTCTGGCACTAATGCCTCTGTTTTCTGGCA
2073 150_HRV49a    ACCAAAGAGCAGAGATGATTATGCATGGCAGTCTGGCACTAATGCATCTGTTTTCTGGCA
2074 151_HRV49b    ACCAAAGAGCAGAGATGATTATGCATGGCAGTCTGGCACTAATGCATCTGTTTTCTGGCA
2075 152_HRV49     ACCAAAGAGCAGAGATGATTATGCATGGCAGTCTGGCACTAATGCATCTGTTTTCTGGCA
```

FIG. D11 CONT'D

07.trace                                                              9/20/2007 5:04 PM

```
2076 153_HRV23a  ACCGGAAAGTAGAAATGACTATGCATGGCAATCTGGAACAAATGCGTCCATTTTTTGGCA
2077 154_HRV23b  ACCGGAAAGTAGAAATGACTATGCATGGCAATCTGGAACAAATGCGTCCATTTTTTGGCA
2078 155_HRV23   ACCGGAAAGTAGAAATGACTATGCATGGCAATCTGGAACAAATGCGTCCATTTTTTGGCA
2079 156_HRV30a  TCCCGAGAGCAGAAATGACTATGCATGGCAGTCTGGAACAAATGCATCTGTTTTTTGGCA
2080 157_HRV30b  TCCCGAGAGCAGAAATGACTATGCATGGCAGTCTGGAACAAATGCATCTGTTTTTTGGCA
2081 158_HRV30   TCCCGAGAGCAGAAATGACTATGCATGGCAGTCTGGAACAAATGCATCTGTTTTTTGGCA
2082 159_HRV7    TCCAATAAAACGCGAAGATTATACATGGCAATCAGGAACAAATGCTTCTATATTTTGGCA
2083 160_HRV7b|  TCCAATAAAACGCGAAGATTATACATGGCAATCAGGAACAAATGCTTCTATATTTTGGCA
2084 161_HRV7a|  TCCAATAAAACGCGAAGATTATACATGGCAATCAGGAACAAATGCTTCTATATTTTGGCA
2085 162_HRV88   TCCCAAGAAACGTGATGATTACACATGGCAGTCAGGAACAAATGCATCTGTGTTCTGGCA
2086 163_HRV88a  TCCCAAGAAACGTGATGATTACACATGGCAGTCAGGAACAAATGCATCTGTGTTCTGGCA
2087 164_HRV88b  TCCCAAGAAACGTGATGATTACACATGGCAGTCAGGAACAAATGCATCTGTGTTCTGGCA
2088 165_HRV36a  TCCTGTGAAGCGTGATGACTACACATGGCAATCAGGGACAAATGCATCTGTGTTCTGGCA
2089 166_HRV36b  TCCTGTGAAGCGTGATGACTACACATGGCAATCAGGGACAAATGCATCTGTGTTCTGGCA
2090 167_HRV36   TCCTGTGAAGCGTGATGACTACACATGGCAATCAGGGACAAATGCATCTGTGTTCTGGCA
2091 168_HRV89a  CCCCGAAAAACGTGATGATTACACATGGCAATCAGGAACAAATGCATCTGTGTTCTGGCA
2092 169_HRV89b  CCCCGAAAAACGTGATGATTACACATGGCAATCAGGAACAAATGCATCTGTGTTCTGGCA
2093 170_HRV89   CCCCGAAAAACGTGATGATTACACATGGCAATCAGGAACAAATGCATCTGTGTTCTGGCA
2094 171_HRV58   ACCCAAGAATCGTGATGACTTTACATGGCAATCAGGCACAAATGCATCTGTTTTCTGGCA
2095 172_HRV58a  ACCCAAGAATCGTGATGACTTTACATGGCAATCAGGCACAAATGCATCTGTTTTCTGGCA
2096 173_HRV58b  ACCCAAGAATCGTGATGACTTTACATGGCAATCAGGCACAAATGCATCTGTTTTCTGGCA
2097 174_HRV12a  ACCCAAAAAACGTGATGATTACACATGGCAATCTGGCACCAACGCCTCAGTTTTTTGGCA
2098 175_HRV12b  ACCCAAAAAACGTGATGATTACACATGGCAATCTGGCACCAACGCCTCAGTTTTTTGGCA
2099 176_HRV12   ACCCAAAAAACGTGATGATTACACATGGCAATCTGGCACCAACGCCTCAGTTTTTTGGCA
2100 177_HRV78a  ACCAAAGAAGAGAGATGACTATACTTGGCAGTCAGGCACCAATGCATCTGTGTTTTGGCA
2101 178_HRV78b  ACCAAAGAAGAGAGATGACTATACTTGGCAGTCAGGCACCAATGCATCTGTGTTTTGGCA
2102 179_HRV78   ACCAAAGAAGAGAGATGACTATACTTGGCAGTCAGGCACCAATGCATCTGTGTTTTGGCA
2103 180_HRV20   ACCAAAGACTAGAGATGACTACACATGGCAATCAGGGCACAAATGCATCAGTATTTTGGCA
2104 181_HRV20a  ACCAAAGACTAGAGATGACTACACATGGCAATCAGGGACAAATGCATCAGTATTTTGGCA
2105 182_HRV20b  ACCAAAGACTAGAGATGACTACACATGGCAATCAGGGACAAATGCATCAGTATTTTGGCA
2106 183_HRV68   ACCAAAAACTAGAGATGATTACACATGGCAGTCAGGCACTAATGCATCAGTGTTTTGGCA
2107 184_HRV68a  ACCAAAAACTAGAGATGATTACACATGGCAGTCAGGCACTAATGCATCAGTGTTTTGGCA
2108 185_HRV68b  ACCAAAAACTAGAGATGATTACACATGGCAGTCAGGCACTAATGCATCAGTGTTTTGGCA
2109 186_HRV28   CCCCACTACCAGAAATGATTACACATGGCAATCCAGTACCAATGCCTCTGTTTTCTGGCA
2110 187_HRV28a  CCCCACTACCAGAAATGATTACACATGGCAATCCAGTACCAATGCCTCTGTTTTCTGGCA
2111 188_HRV28b  CCCCACTACCAGAAATGATTACACATGGCAATCCAGTACCAATGCCTCTGTTTTCTGGCA
2112 189_HRV53a  ACCCAAAACCAGAGATGACTATACCTGGCAATCTGGAACTAATGCTTCAGTCTTTTGGCA
2113 190_HRV53b  ACCCAAAACCAGAGATGACTATACCTGGCAATCTGGAACTAATGCTTCAGTCTTTTGGCA
2114 191_HRV53   ACCCAAAACCAGAGATGACTATACCTGGCAATCTGGAACTAATGCTTCAGTCTTTTGGCA
2115 192_HRV46a  ACCGAGATATCGGAATGATTATACTTGGCAGTCTGGTACTAATGCTTCAGTGTTCTGGCA
2116 193_HRV46b  ACCGAGATATCGGAATGATTATACTTGGCAGTCTGGTACTAATGCTTCAGTGTTCTGGCA
2117 194_HRV46   ACCGAGATATCGGAATGATTATACTTGGCAGTCTGGTACTAATGCTTCAGTGTTCTGGCA
2118 195_HRV80a  GCCAAACAAACGCAATGATTATACTTGGCAGTCTGGCACGAATGCTTCAGTCTTCTGGCA
2119 196_HRV80b  GCCAAACAAACGCAATGATTATACTTGGCAGTCTGGCACGAATGCTTCAGTCTTCTGGCA
2120 197_HRV80   GCCAAACAAACGCAATGATTATACTTGGCAGTCTGGCACGAATGCTTCAGTCTTCTGGCA
2121 198_HRV51   TCCACTTACTAGGAAAGATGATGAGTGGCAATCAGGAACTAATGCTTCAGTATTCTGGCA
2122 199_HRV51a  TCCACTTACTAGGAAAGATGATGAGTGGCAATCAGGAACTAATGCTTCAGTATTCTGGCA
2123 200_HRV51b  TCCACTTACTAGGAAAGATGATGAGTGGCAATCAGGAACTAATGCTTCAGTATTCTGGCA
2124 201_HRV65a  TCCAAAAACTAGAAAAGATGAAGAGTGGCAGACAGGAACTAATGCTTCAGTCTTTTGGCA
2125 202_HRV65b  TCCAAAAACTAGAAAAGATGAAGAGTGGCAGACAGGAACTAATGCTTCAGTCTTTTGGCA
2126 203_HRV65   TCCAAAAACTAGAAAAGATGAAGAGTGGCAGACAGGAACTAATGCTTCAGTCTTTTGGCA
2127 204_HRV71a  ACCAGAGACCAGGGATGCCGATGAATGGCAGTCTGGAACTAATGCATCAGTCTTTTGGCA
2128 205_HRV71b  ACCAGAGACCAGGGATGCCGATGAATGGCAGTCTGGAACTAATGCATCAGTCTTTTGGCA
2129 206_HRV71   ACCAGAGACCAGGGATGCCGATGAATGGCAGTCTGGAACTAATGCATCAGTCTTTTGGCA
2130 207_HRV8    TCCAGATAAAAGGATGCACGATGCCTGGCAAACCAGTACAAATGCCTCAGTCTTCTGGCA
2131 208_HRV95   TCCAGATAAAAGGATGCACGATGCCTGGCAAACCAGTACAAATGCCTCAGTCTTCTGGCA
2132 209_HRV45   CCCTGTTAGTAGAACTGACAACACTTGGCAATCTAGCACAAATGCATCAGTCTTTTGGCA
2133 210_HRV45a  CCCTGTTAGTAGAACTGACAACACTTGGCAATCTAGCACAAATGCATCAGTCTTTTGGCA
2134 211_HRV45b  CCCTGTTAGTAGAACTGACAACACTTGGCAATCTAGCACAAATGCATCAGTCTTTTGGCA
2135 GROUP_1     -CC--------G-------------TGG-A--C--G-A--AA----TC----TT-TGGCA
2136
2137 1_HRV1A1|d  ACATGGACAGCCATTTCCTAGATTTTCTTTACCATTTCTTAGCATTGCATCAGCTTATTA
2138 2_HRV1A2|d  ACATGGACAGCCATTTCCTAGATTTTCTTTACCATTTCTTAGCATTGCATCAGCTTATTA
2139 3_HRV1A|cD  ACATGGACAGCCATTTCCTAGATTTTCTTTACCATTTCTTAGCATTGCATCAGCTTATTA
2140 4_HRV1B1|d  ACATGGACAACCGTTCCCTAGATTCTCTTTACCATTTCTTAGCATTGCATCAGCTTATTA
```

FIG. D11 CONT'D

07.trace                                                                                                                  9/20/2007 5:04 PM

```
2141  5_HRV1B2|d    ACATGGACAACCGTTCCCTAGATTCTCTTTACCATTTCTTAGCATTGCATCAGCTTATTA
2142  6_HRV1B       ACATGGACAACCGTTCCCTAGATTCTCTTTACCATTTCTTAGCATTGCATCAGCTTATTA
2143  7_HRV40a|d    ACATGGTCAAACTTTCCCTAGATTTTCTTTACCTTTCCTAAGCATAGCTTCAGCATACTA
2144  8_HRV40b|d    ACATGGTCAAACTTTCCCTAGATTTTCTTTACCTTTCCTAAGCATAGCTTCAGCATACTA
2145  9_HRV40       ACATGGTCAAACTTTCCCTGATTTTCTTTACCTTTCCTAAGCATAGCTTCAGCATACTA
2146  10_HRV85      ACATGGGCAAACTTTCCCCAGATTTTCCTTACCTTTCTTGAGTGTTGCTTCAGCATATTA
2147  11_HRV85a|    ACATGGGCAAACTTTCCCCAGATTTTCCTTACCTTTCTTGAGTGTTGCTTCAGCATATTA
2148  12_HRV85b|    ACATGGGCAAACTTTCCCCAGATTTTCCTTACCTTTCTTGAGTGTTGCTTCAGCATATTA
2149  13_HRV56a|    ACATGGCCAAGCTTTCCCCAGATTCTCTCTACCTTTCTTAAGTATTGCTTCTGCTTATTA
2150  14_HRV56b|    ACATGGCCAAGCTTTCCCCAGATTCTCTCTACCTTTCTTAAGTATTGCTTCTGCTTATTA
2151  15_HRV56      ACATGGCCAAGCTTTCCCCAGATTCTCTCTACCTTTCTTAAGTATTGCTTCTGCTTATTA
2152  16_HRV54      ACATGGCCAAGCTTATCCAAGATTCTCTTTACCATTTTTAAGTATTGCATCTGCTTACTA
2153  17_HRV98      GCATGGTCAGGCCTATCCAAGATTTTCTCTACCATTCTTGAGCATTGCATCTGCTTACTA
2154  18_HRV59a|    ACATGGACAAACATTCCCAAGATTTTCATTGCCCTTCCTGAGCATAGCATCAGCTTATTA
2155  19_HRV59b|    ACATGGACAAACATTCCCAAGATTTTCATTGCCCTTCCTGAGCATAGCATCAGCTTATTA
2156  20_HRV59      ACATGGACAAACATTCCCAAGATTTTCATTGCCCTTCCTGAGCATAGCATCAGCTTATTA
2157  21_HRV63      ACATGGACAAGCTTTTCCAAGGTTTTCTCTACCTTTCTTGAGTATTGCATCAGCATATTA
2158  22_HRV63b|    ACATGGACAAGCTTTTCCAAGGTTTTCTCTACCTTTCTTGAGTATTGCATCAGCATATTA
2159  23_HRV63a|    ACATGGACAAGCTTTTCCAAGGTTTTCTCTACCTTTCTTGAGTATTGCATCAGCATATTA
2160  24_HRV39      ACACGGACAGCCTTACCCTAGATTTTCATTACCATTTCTAAGCATAGCCTCAGCATATTA
2161  25_HRV39a|    ACACGGACAGCCTTACCCTAGATTTTCATTACCATTTCTAAGCATAGCCTCAGCATATTA
2162  26_HRV39b|    ACACGGACAGCCTTACCCTAGATTTTCATTACCATTTCTAAGCATAGCCTCAGCATATTA
2163  27_HRV10a|    ACATGGACAACCTTTCCCTAGATTTTCTTTACCCTTCTTAAGCATTGCATCTGCTTACTA
2164  28_HRV10b|    ACATGGACAACCTTTCCCTAGATTTTCTTTACCCTTCTTAAGCATTGCATCTGCTTACTA
2165  29_HRV10      ACATGGACAACCTTTCCCTAGATTTTCTTTACCCTTCTTAAGCATTGCATCTGCTTACTA
2166  30_HRV100a    GCATGGGCAGCCATTCCCTAGAATTTCTTTACCTTTCTTGAGCATTGCTTCTGCATACTA
2167  31_HRV100b    GCATGGGCAGCCATTCCCTAGAATTTCTTTACCTTTCTTGAGCATTGCTTCTGCATACTA
2168  32_HRV100     GCATGGGCAGCCATTCCCTAGAATTTCTTTACCTTTCTTGAGCATTGCTTCTGCATACTA
2169  33_HRV66      ACTTGGACAACCATTCCCAAGATTCTCGCTACCTTTTCTAGGCATAGCTTCAGCATATTA
2170  34_HRV66b|    ACTTGGACAACCATTCCCAAGATTCTCGCTACCTTTTCTAGGCATAGCTTCAGCATATTA
2171  35_HRV66a|    ACTTGGACAACCATTCCCAAGATTCTCGCTACCTTTTCTAGGCATAGCTTCAGCATATTA
2172  36_HRV77a|    ACATGGACAACCATTCCCAAGATTTTCACTACCTTTTCTGAGTATTGCTTCAGCTTACTA
2173  37_HRV77b|    ACATGGACAACCATTCCCAAGATTTTCACTACCTTTTCTGAGTATTGCTTCAGCTTACTA
2174  38_HRV77      ACATGGACAACCATTCCCAAGATTTTCACTACCTTTTCTGAGTATTGCTTCAGCTTACTA
2175  39_HRV62a     ACATGGGCAACCCTTTCCTAGATTTTCATTACCTTTTTTGAGTGTTGCATCTGCTTATTA
2176  40_HRV62b     ACATGGGCAACCCTTTCCTAGATTTTCATTACCTTTTTTGAGTGTTGCATCTGCTTATTA
2177  41_HRV25      ACATGGACAACCCTTCCCTAGATTTTCATTGCCATTTCTGAGTGTTGCATCTGCTTATTA
2178  42_HRV29a     ACATGGTCAGCCTTTCCCAAGATTTTCATTACCATTCCTAAGTGTTGCATCTGCTTATTA
2179  43_HRV29b     ACATGGTCAGCCTTTCCCAAGATTTTCATTACCATTCCTAAGTGTTGCATCTGCTTATTA
2180  44_HRV44a     ACATGGTCAACCTTTCCCAAGATTTTCATTGCCATTTCTAAGTGTTGCATCTGCCTATTA
2181  45_HRV44b     ACATGGTCAACCTTTCCCAAGATTTTCATTGCCATTTCTAAGTGTTGCATCTGCCTATTA
2182  46_HRV31      ACATGGACAACCCTTTCCAAGATTTACATTACCCTTTTTGAGTGTCGCATCCGCTTATTA
2183  47_HRV31a|    ACATGGACAACCCTTTCCAAGATTTACATTACCCTTTTTGAGTGTCGCATCCGCTTATTA
2184  48_HRV31b|    ACATGGACAACCCTTTCCAAGATTTACATTACCCTTTTTGAGTGTCGCATCCGCTTATTA
2185  49_HRV47      ACAAGGGCAACCCTTTCCAAGATTTTCATTACCATTTTTGAGTGTTGCATCTGCTTATTA
2186  50_HRV47a|    ACAAGGGCAACCCTTTCCAAGATTTTCATTACCATTTTTGAGTGTTGCATCTGCTTATTA
2187  51_HRV47b|    ACAAGGGCAACCCTTTCCAAGATTTTCATTACCATTTTTGAGTGTTGCATCTGCTTATTA
2188  52_HRV11      ATATGGTCAAACATACCCAAGATTTTCTCTACCTTTCATGAGTATAGCCTCAGCATATTA
2189  53_HRV11b|    ATATGGTCAAACATACCCAAGATTTTCTCTACCTTTCATGAGTATAGCCTCAGCATATTA
2190  54_HRV11a|    ATATGGTCAAACATACCCAAGATTTTCTCTACCTTTCATGAGTATAGCCTCAGCATATTA
2191  55_HRV76      ATATGGACAAACATACCCTAGGTTTTCATTACCCTTTCTAAGTATAGCTTCAGCTTATTA
2192  56_HRV76b|    ATATGGACAAACATACCCTAGGTTTTCATTACCCTTTCTAAGTATAGCTTCAGCTTATTA
2193  57_HRV76a|    ATATGGACAAACATACCCTAGGTTTTCATTACCCTTTCTAAGTATAGCTTCAGCTTATTA
2194  58_HRV33      ATATGGACAAACATATCCTAGGTTCTCATTACCTTTCCTTAGCATAGCTTCAGCATATTA
2195  59_HRV33b|    ATATGGACAAACATATCCTAGGTTCTCATTACCTTTCCTTAGCATAGCTTCAGCATATTA
2196  60_HRV33a|    ATATGGACAAACATATCCTAGGTTCTCATTACCTTTCCTTAGCATAGCTTCAGCATATTA
2197  61_HRV24a|    ACATGGACAAACCTATCCAGATTTTCCCTTCCTTTTCTGAGTGTAGCCTCTGCATATTA
2198  62_HRV24b|    ACATGGACAAACCTATCCTAGATTTTCCCTTCCTTTTCTGAGTGTAGCCTCTGCATATTA
2199  63_HRV24      ACATGGACAAACCTATCCTAGATTTTCCCTTCCTTTTCTGAGTGTAGCCTCTGCATATTA
2200  64_HRV90      ACATGGACAAACATACCCTAGATTTTCCTCTCCTTTCTTAAGTATAGCCTCTGCATATTA
2201  65_HRV90a|    ACATGGACAAACATACCCTAGATTTTCACTTCCTTTCTTAAGTATAGCTTCTGCATACTA
2202  66_HRV90b|    ACATGGACAAACATACCCTAGATTTTCACTTCCTTTCTTAAGTATAGCTTCTGCATACTA
2203  67_HRV34      ACATGGTCAAACATACCCTAGATTTTCCCTCCCTTTCTTAAGCATAGCCTCAGCATACTA
2204  68_HRV34b|    ACATGGTCAAACATACCCTAGATTTTCCCTCCCTTTCTTAAGCATAGCCTCAGCATACTA
2205  69_HRV34a|    ACATGGTCAAACATACCCTAGATTTTCCCTCCCTTTCTTAAGCATAGCCTCAGCATACTA
```

FIG. D11 CONT'D 07.trace                                                                                       9/20/2007 5:04 PM

```
2206  70_HRV50a|   ACATGGTCAAACATACCCTAGATTCTCTCTACCATTCTTGAGTATAGCATCTGCATATTA
2207  71_HRV50b|   ACATGGTCAAACATACCCTAGATTCTCTCTACCATTCTTGAGTATAGCATCTGCATATTA
2208  72_HRV50     ACATGGTCAAACATACCCTAGATTCTCTCTACCATTCTTGAGTATAGCATCTGCATATTA
2209  73_HRV18a|   ACATGGTCAAACATACCCCAGATTTTCACTTCCTTTCCTCAGTATAGCATCAGCTTATTA
2210  74_HRV18b|   ACATGGTCAAACATACCCCAGATTTTCACTTCCTTTCCTCAGTATAGCATCAGCTTATTA
2211  75_HRV18     ACATGGTCAAACATACCCCAGATTTTCACTTCCTTTCCTCAGTATAGCATCAGCTTATTA
2212  76_HRV55     ACATGGGCAAACATACCCTAGATTTTCACTTCCTTTCCTAAGTATAGCTTCTGCTTATTA
2213  77_HRV55b|   ACATGGGCAAACATACCCTAGATTTTCACTTCCTTTCCTAAGTATAGCTTCTGCTTATTA
2214  78_HRV55a|   ACATGGGCAAACATACCCTAGATTTTCACTTCCTTTCCTAAGTATAGCTTCTGCTTATTA
2215  79_HRV57     ACATGGTCAAACATACCCTAGATTTTCCTTGCCTTTCTTAAGTATAGCCTCAGCATATTA
2216  80_HRV57a|   ACATGGTCAAACATACCCTAGATTTTCCTTGCCTTTCTTAAGTATAGCCTCAGCATATTA
2217  81_HRV57b|   ACATGGTCAAACATACCCTAGATTTTCCTTGCCTTTCTTAAGTATAGCCTCAGCATATTA
2218  82_HRV21     GCATGGCCAGACTTATCCTAGATTTTCATTACCCTTCCTTAGTATAGCATCAGCATACTA
2219  83_HRVHan    GCATGGTCAAACTTATCCTAGATTTTCACTACCCTTCCTTAGTATAGCATCAGCATATTA
2220  84_HRV43     ACATGGTCAAACATTTCCAAGATTTTCCTTACCTTTTCTGAGCATAGCATCAGCATATTA
2221  85_HRV43b|   ACATGGTCAAACATTTCCAAGATTTTCCTTACCTTTTCTGAGCATAGCATCAGCATATTA
2222  86_HRV43a|   ACATGGTCAAACATTTCCAAGATTTTCCTTACCTTTTCTGAGCATAGCATCAGCATATTA
2223  87_HRV75     ACATGGACAAACATTTCCAAGATTTTCACTACCATTTCTGAGCATTGCATCAGCATATTA
2224  88_HRV75b|   ACATGGACAAACATTTCCAAGATTTTCACTACCATTTCTGAGCATTGCATCAGCATATTA
2225  89_HRV75a|   ACATGGACAAACATTTCCAAGATTTTCACTACCATTTCTGAGCATTGCATCAGCATATTA
2226  96_HRV9a|d   ACATGGACAATCATATCCCAGATTTTCACTTCCGTTTTGAGCATTGCCTCTGCATATTA
2227  97_HRV9b|d   ACATGGACAATCATATCCCAGATTTTCACTTCCGTTTTGAGCATTGCCTCTGCATATTA
2228  98_HRV9      ACATGGACAATCATATCCCAGATTTTCACTTCCGTTTTGAGCATTGCCTCTGCATATTA
2229  99_HRV32     GCATGGACAGGCATATCCCAGGTTTTCACTTCCATTTCTAAGTATTGCCTCTGCATACTA
2230 100_HRV32a    GCATGGACAGGCATATCCCAGGTTTTCACTTCCATTTCTAAGTATTGCCTCTGCATACTA
2231 101_HRV32b    GCATGGACAGGCATATCCCAGGTTTTCACTTCCATTTCTAAGTATTGCCTCTGCATACTA
2232 102_HRV67     ACATGGACAATCATACCCCAGATTCTCACTACCATTCTTAAGTATTGCCTCTGCTTATTA
2233 103_HRV67a    ACATGGACAATCATACCCCAGATTCTCACTACCATTCTTAAGTATTGCCTCTGCTTATTA
2234 104_HRV67b    ACATGGACAATCATACCCCAGATTCTCACTACCATTCTTAAGTATTGCCTCTGCTTATTA
2235 105_HRV15     ACATGGTCAACCTTACCCCAGATTTCTTTGCCTTTTCTCAGCATTGCATCTGCTTACTA
2236 106_HRV15a    ACATGGTCAACCTTACCCCAGATTTTCTTTGCCTTTTCTCAGCATTGCATCTGCTTACTA
2237 107_HRV15b    ACATGGTCAACCTTACCCCAGATTTTCTTTGCCTTTTCTCAGCATTGCATCTGCTTACTA
2238 108_HRV74a    GCATGGACAGCCATACCCTAGATTCTCATTACCTTTCCTTAGCATAGCATCTGCTTATTA
2239 109_HRV74b    GCATGGACAGCCATACCCTAGATTCTCATTACCTTTCCTTAGCATAGCATCTGCTTATTA
2240 110_HRV74     GCATGGACAGCCATACCCTAGATTCTCATTACCTTTCCTTAGCATAGCATCTGCTTATTA
2241 111_HRV38a    ATATGGTCAGACATATCCTCGATTTTCCTTACCTTTCTTAAGCATTGCATCTGTCTATTA
2242 112_HRV38b    ATATGGTCAGACATATCCTCGATTTTCCTTACCTTTCTTAAGCATTGCATCTGTCTATTA
2243 113_HRV38     ATATGGTCAGACATATCCTCGATTTTCCTTACCTTTCTTAAGCATTGCATCTGTCTATTA
2244 114_HRV60     GCATGGACAAACATACCCTAGATTTTCACTTCCATTTCTAAGTATTGCATCTGCCTACTA
2245 115_HRV60a    GCATGGACAAACATACCCTAGATTTTCACTTCCATTTCTAAGTATTGCATCTGCCTACTA
2246 116_HRV60b    GCATGGACAAACATACCCTAGATTTTCACTTCCATTTCTAAGTATTGCATCTGCCTACTA
2247 117_HRV64a    ACACGGTCAACCATACCCTCGATTTTCTCTCCCTTTCCTTAGCATAGCCTCAGCATATTA
2248 118_HRV64b    ACACGGTCAACCATACCCTCGATTTTCTCTCCCTTTCCTTAGCATAGCCTCAGCATATTA
2249 119_HRV64     ACACGGTCAACCATACCCTCGATTTTCTCTCCCTTTCCTTAGCATAGCCTCAGCATATTA
2250 120_HRV94a    ACATGGTCAACCCTACCCTCGATTCTCACTTCCATTTCTTAGTATAGCCTCAGCATATTA
2251 121_HRV94b    ACATGGTCAACCCTACCCTCGATTCTCACTTCCATTTCTTAGTATAGCCTCAGCATATTA
2252 122_HRV94     ACATGGTCAACCCTACCCTCGATTCTCACTTCCATTTCTTAGTATAGCCTCAGCATATTA
2253 123_HRV22     GCATGGTCAACCTTATCCCCGATTCTCACTCCCTTTCCTCAGTGTAGCTTCAGCATATTA
2254 124_HRV22a    GCATGGTCAACCTTATCCCCGATTCTCACTCCCTTTCCTCAGTGTAGCTTCAGCATATTA
2255 125_HRV22b    GCATGGTCAACCTTATCCCCGATTCTCACTCCCTTTCCTCAGTGTAGCTTCAGCATATTA
2256 126_HRV82     ACATGGACAACCTTACCCTCGCTTCTCACTTCCTTTCTTGAGTATAGCCTCAGCTTACTA
2257 127_HRV82b    ACATGGACAACCTTACCCTCGCTTCTCACTTCCTTTCTTGAGTATAGCCTCAGCTTACTA
2258 128_HRV82a    ACATGGACAACCTTACCCTCGCTTCTCACTTCCTTTCTTGAGTATAGCCTCAGCTTACTA
2259 129_HRV19     ACATGGTCAACCATACCCAAGATTTTCATTACCTTTTCTAAGTATAGCTTCTGCATATTA
2260 130_HRV19a    ACATGGTCAACCATACCCAAGATTTTCATTACCTTTTCTAAGTATAGCTTCTGCATATTA
2261 131_HRV19b    ACATGGTCAACCATACCCAAGATTTTCATTACCTTTTCTAAGTATAGCTTCTGCATATTA
2262 132_HRV13     ACATGGTCAAATTTACCCCCGATTCTCTTTACCATTTCTTAGTATTGCATCTGCATATTA
2263 133_HRV13a    ACATGGTCAAATTTACCCCCGATTCTCTTTACCATTTCTTAGTATTGCATCTGCATATTA
2264 134_HRV13b    ACATGGTCAAATTTACCCCCGATTCTCTTTACCATTTCTTAGTATTGCATCTGCATATTA
2265 135_HRV41     GTATGGTCAACGTTTACCCTAGGTTTTCTCTACCATTTCTTAGCATTGCTTCCGCATATTA
2266 136_HRV41a    GTATGGTCAAGTTTACCCTAGGTTTTCTCTACCATTTCTTAGCATTGCTTCCGCATATTA
2267 137_HRV41b    GTATGGTCAAGTTTACCCTAGGTTTTCTCTACCATTTCTTAGCATTGCTTCCGCATATTA
2268 138_HRV73     ACATGGTCAAACTTACCCCAGATTCTCATTACCATTCCTTAGTATAGCATCCGCATATTA
2269 139_HRV73b    ACATGGTCAAACTTACCCCAGATTCTCATTACCATTCCTTAGTATAGCATCCGCATATTA
2270 140_HRV73a    ACATGGTCAAACTTACCCCAGATTCTCATTACCATTCCTTAGTATAGCATCCGCATATTA
```

FIG. D11 CONT'D

```
07.trace                                                                    9/20/2007 5:04 PM 2271 141_HRV61     ACATGGTCAAGCTTATCCCAGATTTTCATTACCATTCCTAAGTATTGCATCTGCATATTA
2272 142_HRV61a    ACATGGTCAAGCTTATCCCAGATTTTCATTACCATTCCTAAGTATTGCATCTGCATATTA
2273 143_HRV61b    ACATGGTCAAGCTTATCCCAGATTTTCATTACCATTCCTAAGTATTGCATCTGCATATTA
2274 144_HRV96     GCACGGGCAAGCATATCCTAGATTTTCACTGCCTTTCCTTAGTATTGCCTCTGCATATTA
2275 145_HRV96b    GCACGGGCAAGCATATCCTAGATTTTCACTGCCTTTCCTTAGTATTGCCTCTGCATATTA
2276 146_HRV96a    GCACGGGCAAGCATATCCTAGATTTTCACTGCCTTTCCTTAGTATTGCCTCTGCATATTA
2277 90_HRV16a|    GCATGGGCAACCTTTCCCTCGCTTTTCACTTCCCTTTTTGAGTATTGCATCAGCATATTA
2278 91_HRV16b|    GCATGGGCAACCTTTCCCTCGCTTTTCACTTCCCTTTTTGAGTATTGCATCAGCATATTA
2279 92_1AYM_A     GCATGGGCAACCTTTCCCTCGCTTTTCACTTCCCTTTTTGAGTATTGCATCAGCATATTA
2280 93_HRV81a|    ACATGGGCAACCCTTTCCCCGGTTTTCACTCCCTTTTCTAAGTGTAGCATCAGCATATTA
2281 94_HRV81b|    ACATGGGCAACCCTTTCCCCGGTTTTCACTCCCTTTTCTAAGTGTAGCATCAGCATATTA
2282 95_HRV81      ACATGGGCAACCCTTTCCCCGGTTTTCACTCCCTTTTCTAAGTGTAGCATCAGCATATTA
2283 147_HRV2      ACATGGACAGGCTTATCCAAGATTTTCCTTACCTTTCCTAAGTGTGGCATCTGCTTATTA
2284 148_HRV2a|    ACATGGACAGGCTTATCCAAGATTTTCCTTACCTTTCCTAAGTGTGGCATCTGCTTATTA
2285 149_HRV2b|    ACATGGACAGGCTTATCCAAGATTTTCCTTACCTTTCCTAAGTGTGGCATCTGCTTATTA
2286 150_HRV49a    ACATGGGCAAGCATACCCAAGATTTTCTCTACCCTTTTTGAGTGTAGCTTCAGCTTACTA
2287 151_HRV49b    ACATGGGCAAGCATACCCAAGATTTTCTCTACCCTTTTTGAGTGTAGCTTCAGCTTACTA
2288 152_HRV49     ACATGGGCAAGCATACCCAAGATTTTCTCTACCCTTTTTGAGTGTAGCTTCAGCTTACTA
2289 153_HRV23a    ACATGGACAAACATATCCAAGGTTCTCCTTACCCTTTTTGAGTGTGGCATCTGCTTATTA
2290 154_HRV23b    ACATGGACAAACATATCCAAGGTTCTCCTTACCCTTTTTGAGTGTGGCATCTGCTTATTA
2291 155_HRV23     ACATGGACAAACATATCCAAGGTTCTCCTTACCCTTTTTGAGTGTGGCATCTGCTTATTA
2292 156_HRV30a    ACACGGACAAACATACCCAAGATTCTCCCTACCATTTTTGAGTGTAGCATCTGCTTATTA
2293 157_HRV30b    ACACGGACAAACATACCCAAGATTCTCCCTACCATTTTTGAGTGTAGCATCTGCTTATTA
2294 158_HRV30     ACACGGACAAACATACCCAAGATTCTCCCTACCATTTTTGAGTGTAGCATCTGCTTATTA
2295 159_HRV7      GGAGGGTCAACCATACCCTAGATTCACAATTCCTTTTATGAGTATTGCATCAGCTTATTA
2296 160_HRV7b|    GGAGGGTCAACCATACCCTAGATTCACAATTCCTTTTATGAGTATTGCATCAGCTTATTA
2297 161_HRV7a|    GGAGGGTCAACCATACCCTAGATTCACAATTCCTTTTATGAGTATTGCATCAGCTTATTA
2298 162_HRV88     AGAAGGACAACCATACCCAAGATTTACCATTCCCTTTATGAGTATTGCATCAGCTTACTA
2299 163_HRV88a    AGAAGGACAACCATACCCAAGATTTACCATTCCCTTTATGAGTATTGCATCAGCTTACTA
2300 164_HRV88b    AGAAGGACAACCATACCCAAGATTTACCATTCCCTTTATGAGTATTGCATCAGCTTACTA
2301 165_HRV36a    AGAAGGGCAACCATATCCTAGATTTACAATCCCCTTTATGAGTATTGCATCAGCTTATTA
2302 166_HRV36b    AGAAGGGCAACCATATCCTAGATTTACAATCCCCTTTATGAGTATTGCATCAGCTTATTA
2303 167_HRV36     AGAAGGGCAACCATATCCTAGATTTACAATCCCCTTTATGAGTATTGCATCAGCTTATTA
2304 168_HRV89a    AGAAGGACAACCATACCCCAGATTCACAATCCCTTTTATGAGCATTGCATCAGCCTATTA
2305 169_HRV89b    AGAAGGACAACCATACCCCAGATTCACAATCCCTTTTATGAGCATTGCATCAGCCTATTA
2306 170_HRV89     AGAAGGACAACCATACCCCAGATTCACAATCCCTTTTATGAGCATTGCATCAGCCTATTA
2307 171_HRV58     GGAAGGACAACCATACCCTAGATTTACAATCCCTTTTATGAGCATTGCATCAGCTTACTA
2308 172_HRV58a    GGAAGGACAACCATACCCTAGATTTACAATCCCTTTTATGAGCATTGCATCAGCTTACTA
2309 173_HRV58b    GGAAGGACAACCATACCCTAGATTTACAATCCCTTTTATGAGCATTGCATCAGCTTACTA
2310 174_HRV12a    GGAAGGTCAACCTTACCCCAGATTCACAATCCCTTTTATTAGTATTGCCTCAGCATATTA
2311 175_HRV12b    GGAAGGTCAACCTTACCCCAGATTCACAATCCCTTTTATTAGTATTGCCTCAGCATATTA
2312 176_HRV12     GGAAGGTCAACCTTACCCCAGATTCACAATCCCTTTTATTAGTATTGCCTCAGCATATTA
2313 177_HRV78a    ACAAGGTCAAACATACCCCAGGTTCTCTATACCATTTTCTAGTATTGCCTCAGCTTATTA
2314 178_HRV78b    ACAAGGTCAAACATACCCCAGGTTCTCTATACCATTTTCTAGTATTGCCTCAGCTTATTA
2315 179_HRV78     ACAAGGTCAAACATACCCCAGGTTCTCTATACCATTTTCTAGTATTGCCTCAGCTTATTA
2316 180_HRV20     GCAGGGCAACCTTACCCCAGATTTACCATTCCATTTATGAGTATAGCTTCAGCATATTA
2317 181_HRV20a    GCAGGGCCAACCTTACCCCAGATTTACCATTCCATTTATGAGTATAGCTTCAGCATATTA
2318 182_HRV20b    GCAGGGCCAACCTTACCCCAGATTTACCATTCCATTTATGAGTATAGCTTCAGCATATTA
2319 183_HRV68     ACAAGGACAACCTTACCCCAGATTTACCATTCCATTTATGAGTATAGCTTCAGCATATTA
2320 184_HRV68a    ACAAGGACAACCTTACCCCAGATTTACCATTCCATTTATGAGTATAGCTTCAGCATATTA
2321 185_HRV68b    ACAAGGACAACCTTACCCCAGATTTACCATTCCATTTATGAGTATAGCTTCAGCATATTA
2322 186_HRV28     ACAAGGACAACCATACCCCAGATTCACTATACCTTTTATGAGTATTGCCTCAGCTTATTA
2323 187_HRV28a    ACAAGGACAACCATATCCCAGATTCACTATACCTTTTATGAGTATTGCCTCAGCTTATTA
2324 188_HRV28b    ACAAGGACAACCATATCCCAGATTCACTATACCTTTTATGAGTATTGCCTCAGCTTATTA
2325 189_HRV53a    ACAAGGACAACCATACCCTAGATTCACAATCCCTTTCATGAGTATTGCGTCAGCATATTA
2326 190_HRV53b    ACAAGGACAACCATACCCTAGATTCACAATCCCTTTCATGAGTATTGCGTCAGCATATTA
2327 191_HRV53     ACAAGGACAACCATACCCTAGATTCACAATCCCTTTCATGAGTATTGCGTCAGCATATTA
2328 192_HRV46a    GCAAGGGCAGCCATACCCCAGATTCACTATCCCGTTCATGAGTATAGCCTCAGCATATTA
2329 193_HRV46b    GCAAGGGCAGCCATACCCCAGATTCACTATCCCGTTCATGAGTATAGCCTCAGCATATTA
2330 194_HRV46     GCAAGGGCAGCCATACCCCAGATTCACTATCCCGTTCATGAGTATAGCCTCAGCATATTA
2331 195_HRV80a    ACAGGGTCAGCCATACCCCAGATTCACTATTCCATTCATGAGTATAGCCTCAGCTTATTA
2332 196_HRV80b    ACAGGGTCAGCCATACCCCAGATTCACTATTCCATTCATGAGTATAGCCTCAGCTTATTA
2333 197_HRV80     ACAGGGTCAGCCATACCCCAGATTCACTATTCCATTCATGAGTATAGCCTCAGCTTATTA
2334 198_HRV51     ACATGGACAACCATACCCTAGATTTACAATCCCTTTTGTAAGCATAGCCTCAGCATACTA
2335 199_HRV51a    ACATGGACAACCATACCCTAGATTTACAATCCCTTTTGTAAGCATAGCCTCAGCATACTA
```

FIG. D11 CONT'D

```
07.trace                                                               9/20/2007 5:04 PM 2336 200_HRV51b    ACATGGACAACCATACCCTAGATTTACAATCCCTTTTGTAAGCATAGCCTCAGCATACTA
2337 201_HRV65a    GCATGGTCAACCATACCCCAGATTTACAATTCCTTTTGTGAGTATTGCCTCAGCATATTA
2338 202_HRV65b    GCATGGTCAACCATACCCCAGATTTACAATTCCTTTTGTGAGTATTGCCTCAGCATATTA
2339 203_HRV65     GCATGGTCAACCATACCCCAGATTTACAATTCCTTTTGTGAGTATTGCCTCAGCATATTA
2340 204_HRV71a    GCACGGCCAACCATACCCAAGGTTTACAATCCCCTTCATAAGCATTGCATCAGCATATTA
2341 205_HRV71b    GCACGGCCAACCATACCCAAGGTTTACAATCCCCTTCATAAGCATTGCATCAGCATATTA
2342 206_HRV71     GCACGGCCAACCATACCCAAGGTTTACAATCCCCTTCATAAGCATTGCATCAGCATATTA
2343 207_HRV8      AGTTGGACAAACTTATCCCAGATTCACCATACCTTTCTCCAGCATAGCATCAGCTTATTA
2344 208_HRV95     AGTTGGACAGACTTATCCCAGATTCACCATACCTTTCTCCAGTATAGCATCAGCTTATTA
2345 209_HRV45     GGTTGGTCAAACTTATCCCAGATTTTCTATACCTTTCTCAAGTATAGCTTCAGCTTACTA
2346 210_HRV45a    GGTTGGTCAAACTTATCCCAGATTTTCTATACCTTTCTCAAGTATAGCTTCAGCTTACTA
2347 211_HRV45b    GGTTGGTCAAACTTATCCCAGATTTTCTATACCTTTCTCAAGTATAGCTTCAGCTTACTA
2348 GROUP_1       ----GG-CA----T--CC--G--T--C--T-CC-TT-----G--T-GC-TC-G--TA-TA
2349
2350 1_HRV1A1|d    TATGTTTTATGATGGATATGATGGAGACAACACTTCTTCCAAGTATGGTAGCGTAGTTAC
2351 2_HRV1A2|d    TATGTTTTATGATGGATATGATGGAGACAACACTTCTTCCAAGTATGGTAGCGTAGTTAC
2352 3_HRV1A|cD    TATGTTTTATGATGGATATGATGGAGACAACACTTCTTCCAAGTATGGTAGCGTAGTTAC
2353 4_HRV1B1|d    CATGTTTTATGATGGATATGATGGAGATAATTCCTCTTCCAAATATGGTAGTATAGTCAC
2354 5_HRV1B2|d    CATGTTTTATGATGGATATGATGGAGATAATTCCTCTTCCAAATATGGTAGTATAGTCAC
2355 6_HRV1B       CATGTTTTATGATGGATATGATGGAGATAATTCCTCTTCCAAATATGGTAGTATAGTCAC
2356 7_HRV40a|d    CATGTTTTATGATGGATACGATGGTGATACATCGACCTCAAGATATGGCACATCAGTCAC
2357 8_HRV40b|d    CATGTTTTATGATGGATACGATGGTGATACATCGACCTCAAGATATGGCACATCAGTCAC
2358 9_HRV40       CATGTTTTATGATGGATACGATGGTGATACATCGACCTCAAGATATGGCACATCAGTCAC
2359 10_HRV85      CATGTTTTATGATGGTTATGATGGTGATACACCAGGCTCAATGTATGGGACGTCAGTCAC
2360 11_HRV85a|    CATGTTTTATGATGGTTATGATGGTGATACACCAGGCTCAATGTATGGGACGTCAGTCAC
2361 12_HRV85b|    CATGTTTTATGATGGTTATGATGGTGATACACCAGGCTCAATGTATGGGACGTCAGTCAC
2362 13_HRV56a|    CATGTTTTATGATGGTTATGATGGAGACACTTCAAGCTCCAGATATGGTACATCAGTTAC
2363 14_HRV56b|    CATGTTTTATGATGGTTATGATGGAGACACTTCAAGCTCCAGATATGGTACATCAGTTAC
2364 15_HRV56      CATGTTTTATGATGGTTATGATGGAGACACTTCAAGCTCCAGATATGGTACATCAGTTAC
2365 16_HRV54      CATGTTTTATGATGGGTATGATGGTGACGCACCTGGATCAAGATATGGGACTTCAGTTAC
2366 17_HRV98      CATGTTTTACGATGGGTATGATGGTGATGCACCTGGATCAAGATATGGAACCTCAGTCAC
2367 18_HRV59a|    CATGTTTTATGATGGTTATGATGGAGATAAATCTAGGTATGGTGTGTCTGTAAC
2368 19_HRV59b|    CATGTTTTATGATGGTTATGATGGAGATAAATCTGAATCTAGGTATGGTGTGTCTGTAAC
2369 20_HRV59      CATGTTTTATGATGGTTATGATGGAGATAAATCTGAATCTAGGTATGGTGTGTCTGTAAC
2370 21_HRV63      CATGTTTTATGATGGATATGATGGAGATAAATCAAGCTCTAGGTATGGTGTTTCAGTTAC
2371 22_HRV63b|    CATGTTTTATGATGGATATGATGGAGATAAATCAAGCTCTAGGTATGGTGTTTCAGTTAC
2372 23_HRV63a|    CATGTTTTATGATGGATATGATGGAGATAAATCAAGCTCTAGGTATGGTGTTTCAGTTAC
2373 24_HRV39      TATGTTCTATGATGGATATGATGGTGATAAATCGTCATCTAGGTATGGTGTTTCTGTCAC
2374 25_HRV39a|    TATGTTCTATGATGGATATGATGGTGATAAATCGTCATCTAGGTATGGTGTTTCTGTCAC
2375 26_HRV39b|    TATGTTCTATGATGGATATGATGGTGATAAATCGTCATCTAGGTATGGTGTTTCTGTCAC
2376 27_HRV10a|    CATGTTCTATGATGGTTATGATGGTGATACACATGACTCACGTTATGGCACAACAGTGAT
2377 28_HRV10b|    CATGTTCTATGATGGTTATGATGGTGATACACATGACTCACGTTATGGCACAACAGTGAT
2378 29_HRV10      CATGTTCTATGATGGTTATGATGGTGATACACATGACTCACGTTATGGCACAACAGTGAT
2379 30_HRV100a    CATGTTTTATGATGGATATGATGGTGATACACATGATTCACACTATGGTACTACTGTAAT
2380 31_HRV100b    CATGTTTTATGATGGATATGATGGTGATACACATGATTCACACTATGGTACTACTGTAAT
2381 32_HRV100     CATGTTTTATGATGGATATGATGGTGATACACATGATTCACACTATGGTACTACTGTAAT
2382 33_HRV66      CATGTTCTATGATGGTTATGATGGAGATACTCCTGGGTCTCGTTATGGAACCACAGTAGT
2383 34_HRV66b|    CATGTTCTATGATGGTTATGATGGAGATACTCCTGGGTCTCGTTATGGAACCACAGTAGT
2384 35_HRV66a|    CATGTTCTATGATGGTTATGATGGAGATACTCCTGGGTCTCGTTATGGAACCACAGTAGT
2385 36_HRV77a|    CATGTTTTATGATGGCTATGATGGGGATACCTATGAATCACGTTATGGTACTACAGTGGT
2386 37_HRV77b|    CATGTTTTATGATGGCTATGATGGGGATACCTATGAATCACGTTATGGTACTACAGTGGT
2387 38_HRV77      CATGTTTTATGATGGCTATGATGGGGATACCTATGAATCACGTTATGGTACTACAGTGGT
2388 39_HRV62a     CATGTTTTATGATGGCTATAATGGTGACTATACAGCAAAATACGGTACCACCGTGGT
2389 40_HRV62b     CATGTTTTATGATGGCTATAATGGTGATGACTATACAGCAAAATACGGTACCACCGTGGT
2390 41_HRV25      CATGTTTTATGATGGCTATAATGGTGATGATCACACAGCGAGATATGGTACCACTGTGGT
2391 42_HRV29a     CATGTTTTATGATGGTTACAATGGAGGTGATCATACAGCAACTTATGGCACCACAGTGGT
2392 43_HRV29b     CATGTTTTATGATGGTTACAATGGAGGTGATCATACAGCAACTTATGGCACCACAGTGGT
2393 44_HRV44a     CATGTTTTATGACGGTTATAATGGAGGTGATCATACAGCAACTTATGGCACCACAGTGGT
2394 45_HRV44b     CATGTTTTATGACGGTTATAATGGAGGTGATCATACAGCAACTTATGGCACCACAGTGGT
2395 46_HRV31      CATGTTTTATGATGGTTATGATGGAGACAAAAGTGGAGCCAAGTATGGTACTACAGTAGT
2396 47_HRV31a|    CATGTTTTATGATGGTTATGATGGAGACAAAAGTGGAGCCAAGTATGGTACTACAGTAGT
2397 48_HRV31b|    CATGTTTTATGATGGTTATGATGGAGACAAAAGTGGAGCCAAGTATGGTACTACAGTAGT
2398 49_HRV47      CATGTTTTATGATGGCTATAATGGTGACAGAAGTGGAGCCAAGTATGGCACCACAGTGGT
2399 50_HRV47a|    CATGTTTTATGATGGCTATAATGGTGACAGAAGTGGAGCCAAGTATGGCACCACAGTGGT
2400 51_HRV47b|    CATGTTTTATGATGGCTATAATGGTGACAGAAGTGGAGCCAAGTATGGCACCACAGTGGT
```

FIG. D11 CONT'D

07.trace                                                                                        9/20/2007 5:04 PM

```
2401  52_HRV11      CATGTTTTATGATGGATATGATGGAGATCAACCAAACTCCAGATATGGTAATATAGTTAC
2402  53_HRV11b|    CATGTTTTATGATGGATATGATGGAGATCAACCAAACTCCAGATATGGTAATATAGTTAC
2403  54_HRV11a|    CATGTTTTATGATGGATATGATGGAGATCAACCAAACTCCAGATATGGTAATATAGTTAC
2404  55_HRV76      CATGTTTTATGATGGATATGATGGAGACCAACCTAGTTCTAGGTATGGTAATATAGTTAC
2405  56_HRV76b|    CATGTTTTATGATGGATATGATGGAGACCAACCTAGTTCTAGGTATGGTAATATAGTTAC
2406  57_HRV76a|    CATGTTTTATGATGGATATGATGGAGACCAACCTAGTTCTAGGTATGGTAATATAGTTAC
2407  58_HRV33      CATGTTCTATGATGGATATGATGGGGACCAACCCAATTCCAGGTATGGTAATATGGTTAC
2408  59_HRV33b|    CATGTTCTATGATGGATATGATGGGGACCAACCCAATTCCAGGTATGGTAATATGGTTAC
2409  60_HRV33a|    CATGTTCTATGATGGATATGATGGGGACCAACCCAATTCCAGGTATGGTAATATGGTTAC
2410  61_HRV24a|    CATGTTTTATGATGGATATGATGGTGATCAACACGACTCAGTGTATGGTTCAGTTGTTAC
2411  62_HRV24b|    CATGTTTTATGATGGATATGATGGTGATCAACACGACTCAGTGTATGGTTCAGTTGTTAC
2412  63_HRV24      CATGTTTTATGATGGATATGATGGTGATCAACACGACTCAGTGTATGGTTCAGTTGTTAC
2413  64_HRV90      TATGTTTTATGATGGATATGATGGTGACCAAACTGATTCGAGATATGGTACCATTGTTAC
2414  65_HRV90a|    TATGTTTTATGATGGATATGATGGTGACCAAACTGATTCGAGATATGGTACCATTGTTAC
2415  66_HRV90b|    TATGTTTTATGATGGATATGATGGTGACCAAACTGATTCGAGATATGGTACCATTGTTAC
2416  67_HRV34      CATGTTTTATGATGGATATGATGGTGATCAACATGATTCAAGATATGGTACAGTAGTGAC
2417  68_HRV34b|    CATGTTTTATGATGGATATGATGGTGATCAACATGATTCAAGATATGGTACAGTAGTGAC
2418  69_HRV34a|    CATGTTTTATGATGGATATGATGGTGATCAACATGATTCAAGATATGGTACAGTAGTGAC
2419  70_HRV50a|    CATGTTTTATGATGGTTATGATGGTGATAAATCTACATCCAGGTATGGTACAGTAGTTAC
2420  71_HRV50b|    CATGTTTTATGATGGTTATGATGGTGATAAATCTACATCCAGGTATGGTACAGTAGTTAC
2421  72_HRV50      CATGTTTTATGATGGTTATGATGGTGATAAATCTACATCCAGGTATGGTACAGTAGTTAC
2422  73_HRV18a|    CATGTTCTATGATGGCTACGACGGTGACCAGACCTCATCGCGGTATGGCACAGTTGCAAC
2423  74_HRV18b|    CATGTTCTATGATGGCTACGACGGTGACCAGACCTCATCGCGGTATGGCACAGTTGCAAC
2424  75_HRV18      CATGTTCTATGATGGCTACGACGGTGACCAGACCTCATCGCGGTATGGCACAGTTGCAAC
2425  76_HRV55      CATGTTCTATGATGGATATGATGGTGACCAAACTGAGTCACGCTATGGCACTGTAGTCAC
2426  77_HRV55b|    CATGTTTTATGATGGATATGATGGTGACCAAACTGAGTCACGCTATGGCACTGTAGTCAC
2427  78_HRV55a|    CATGTTCTATGATGGATATGATGGTGACCAAACTGAGTCACGCTATGGCACTGTAGTCAC
2428  79_HRV57      CATGTTTTATGATGGATATGATGGTGACCAAACTGAATCAAGATATGGTACTGTAGTCAC
2429  80_HRV57a|    CATGTTTTATGATGGATATGATGGTGACCAAACTGAATCAAGATATGGTACTGTAGTCAC
2430  81_HRV57b|    CATGTTTTATGATGGATATGATGGTGACCAAACTGAATCAAGATATGGTACTGTAGTCAC
2431  82_HRV21      CATGTTCTATGATGGTTATGATGGTGACCAGACTGACTCACAATATGGTGCAGTAGTAAC
2432  83_HRVHan     CATGTTTTATGATGGTTATGATGGTGATCAGACTGACTCACAATATGGTGCAGTGGTGAC
2433  84_HRV43      CATGTTTTATGATGGATATGAAGGTGACCAAAAAACATCCCGTTATGGCACAATTGCAAG
2434  85_HRV43b|    CATGTTTTATGATGGATATGAAGGTGACCAAAAAACATCCCGTTATGGCACAATTGCAAG
2435  86_HRV43a|    CATGTTTTATGATGGATATGAAGGTGACCAAAAAACATCCCGTTATGGCACAATTGCAAG
2436  87_HRV75      CATGTTTTATGATGGATATGAAGGGGATCAAAATACATCCCGTTATGGCACCATTGCTAG
2437  88_HRV75b|    CATGTTTTATGATGGATATGAAGGGGATCAAAATACATCCCGTTATGGCACCATTGCTAG
2438  89_HRV75a|    CATGTTTTATGATGGATATGAAGGGGATCAAAATACATCCCGTTATGGCACCATTGCTAG
2439  96_HRV9a|d    CATGTTCTATGATGGTTATGATGGTGG---ACCAGATTCTCTGTATGGAACAATTGTAAC
2440  97_HRV9b|d    CATGTTCTATGATGGTTATGATGGTGG---ACCAGATTCTCTGTATGGAACAATTGTAAC
2441  98_HRV9       CATGTTCTATGATGGTTATGATGGTGG---ACCAGATTCTCTGTATGGAACAATTGTAAC
2442  99_HRV32      CATGTTTTATGATGGTTATGATGGTGG---GCCAGATTCACAATATGGAACAATTGTAAC
2443  100_HRV32a    CATGTTTTATGATGGTTATGATGGTGG---GCCAGATTCACAATATGGAACAATTGTAAC
2444  101_HRV32b    CATGTTTTATGATGGTTATGATGGTGG---GCCAGATTCACAATATGGAACAATTGTAAC
2445  102_HRV67     CATGTTTTATGATGGCTATGATGGTGG---ACCAGATTCACTATATGGCACCATAGTAAC
2446  103_HRV67a    CATGTTTTATGATGGCTATGATGGTGG---ACCAGATTCACTATATGGCACCATAGTAAC
2447  104_HRV67b    CATGTTTTATGATGGCTATGATGGTGG---ACCAGATTCACTATATGGCACCATAGTAAC
2448  105_HRV15     CATGTTCTATGATGGATATGATGGAGATTCCACTGAATCACATTATGGTACAGTGGTCAC
2449  106_HRV15a    CATGTTCTATGATGGATATGATGGAGATTCCACTGAATCACATTATGGTACAGTGGTCAC
2450  107_HRV15b    CATGTTCTATGATGGATATGATGGAGATTCCACTGAATCACATTATGGTACAGTGGTCAC
2451  108_HRV74a    CATGTTTTATGATGGATATGATGGAGACTCTACTGAATCACATTATGGTACAGTAGTAAC
2452  109_HRV74b    CATGTTTTATGATGGATATGATGGAGACTCTACTGAATCACATTATGGTACAGTAGTAAC
2453  110_HRV74     CATGTTTTATGATGGATATGATGGAGACTCTACTGAATCACATTATGGTACAGTAGTAAC
2454  111_HRV38a    TATGTTTTATGATGGATATGATGGGGACTCAACAGAATCACATTATGGGACAGCGGTGAC
2455  112_HRV38b    TATGTTTTATGATGGATATGATGGGGACTCAACAGAATCACATTATGGGACAGCGGTGAC
2456  113_HRV38     TATGTTTTATGATGGATATGATGGGGACTCAACAGAATCACATTATGGGACAGCGGTGAC
2457  114_HRV60     CATGTTTTATGATGGTTATGATGGTCACTCAACTGAATCACATTATGGGACGGTTGTGAC
2458  115_HRV60a    CATGTTTTATGATGGTTATGATGGTCACTCAACTGAATCACATTATGGGACGGTTGTGAC
2459  116_HRV60b    CATGTTTTATGATGGTTATGATGGTCACTCAACTGAATCACATTATGGGACGGTTGTGAC
2460  117_HRV64a    CATGTTTTATGATGGTTATGACGGTGG---ACCTGGTTCCCGTTATGGCGCAGTGGTGAC
2461  118_HRV64b    CATGTTTTATGATGGTTATGACGGTGG---ACCTGGTTCCCGTTATGGCGCAGTGGTGAC
2462  119_HRV64     CATGTTTTATGATGGTTATGACGGTGG---ACCTGGTTCCCGTTATGGCGCAGTGGTGAC
2463  120_HRV94a    CATGTTCTATGATGGTTATGATGGTGG---ACCTGGCTCACGCTATGGCACAGTGGTGAC
2464  121_HRV94b    CATGTTCTATGATGGTTATGATGGTGG---ACCTGGCTCACGCTATGGCACAGTGGTGAC
2465  122_HRV94     CATGTTCTATGATGGTTATGATGGTGG---ACCTGGCTCACGCTATGGCACAGTGGTGAC
```

FIG. D11 CONT'D

07.trace                                                                 9/20/2007 5:04 PM

```
2466  123_HRV22    CATGTTTTATGATGGGTATGATGGAGG---TCCCGGATCACGTTATGGAGCAGTGGTAAC
2467  124_HRV22a   CATGTTTTATGATGGGTATGATGGAGG---TCCCGGATCACGTTATGGAGCAGTGGTAAC
2468  125_HRV22b   CATGTTTTATGATGGGTATGATGGAGG---TCCCGGATCACGTTATGGAGCAGTGGTAAC
2469  126_HRV82    TATGTTCTATGATGGCTATGATGGTGATGCTCCCGGATCGCGATACGGGACCATAGTGAC
2470  127_HRV82b   TATGTTCTATGATGGCTATGATGGTGATGCTCCCGGATCGCGATACGGGACCATAGTGAC
2471  128_HRV82a   TATGTTCTATGATGGCTATGATGGTGATGCTCCCGGATCGCGATACGGGACCATAGTGAC
2472  129_HRV19    CATGTTTTATGATGGGTATGATGGAGATTCACCAGGATCCCGCTATGGAACAATAGTAAC
2473  130_HRV19a   CATGTTTTATGATGGGTATGATGGAGATTCACCAGGATCCCGCTATGGAACAATAGTAAC
2474  131_HRV19b   CATGTTTTATGATGGGTATGATGGAGATTCACCAGGATCCGCTATGGAACAATAGTAAC
2475  132_HRV13    TATGTTTTATGATGGATATAATGGAGATTCCTCAGATGCACGCTATGGGACAACAATCAC
2476  133_HRV13a   TATGTTTTATGATGGATATAATGGAGATTCCTCAGATGCACGCTATGGGACAACAATCAC
2477  134_HRV13b   TATGTTTTATGATGGATATAATGGAGATTCCTCAGATGCACGCTATGGGACAACAATCAC
2478  135_HRV41    CATGTTTTATGATGGTTATGAAGAAGGCTCTACAAATGCACGCTATGGAACAACAGTCAC
2479  136_HRV41a   CATGTTTTATGATGGTTATGAAGAAGGCTCTACAAATGCACGCTATGGAACAACAGTCAC
2480  137_HRV41b   CATGTTTTATGATGGTTATGAAGAAGGCTCTACAAATGCACGCTATGGAACAACAGTCAC
2481  138_HRV73    TATGTTTTATGATGGATATGATGGTGACTCCACACAATCACATTATGGCACCACAGTAGT
2482  139_HRV73b   TATGTTTTATGATGGATATGATGGTGACTCCACACAATCACATTATGGCACCACAGTAGT
2483  140_HRV73a   TATGTTTTATGATGGATATGATGGTGACTCCACACAATCACATTATGGCACCACAGTAGT
2484  141_HRV61    TATGTTTTATGATGGTTATGATGGAGATTCTGAAATAACGCGCTATGGAACATCAGTGAC
2485  142_HRV61a   TATGTTTTATGATGGTTATGATGGAGATTCTGAAATAACGCGCTATGGAACATCAGTGAC
2486  143_HRV61b   TATGTTTTATGATGGTTATGATGGAGATTCTGAAATAACGCGCTATGGAACATCAGTGAC
2487  144_HRV96    CATGTTTTATGATGGATATGATGGTGACTCTGAATCAACACGCTATGGAACATCTGTTAC
2488  145_HRV96b   CATGTTTTATGATGGATATGATGGTGACTCTGAATCAACACGCTATGGAACATCTGTTAC
2489  146_HRV96a   CATGTTTTATGATGGATATGATGGTGACTCTGAATCAACACGCTATGGAACATCTGTTAC
2490   90_HRV16a|  CATGTTTTATGATGGTTATGATGGAGACACATATAAATCCAGATATGGAACTGTAGTCAC
2491   91_HRV16b|  CATGTTTTATGATGGTTATGATGGAGACACATATAAATCCAGATATGGAACTGTAGTCAC
2492   92_1AYM_A   CATGTTTTATGATGGTTATGATGGAGACACATATAAATCCAGATATGGAACTGTAGTCAC
2493   93_HRV81a|  CATGTTCTATGATGGATATGATGGTGATACTTATCACTCCAGATACGGGACTGTAGTCAC
2494   94_HRV81b|  CATGTTCTATGATGGATATGATGGTGATACTTATCACTCCAGATACGGGACTGTAGTCAC
2495   95_HRV81    CATGTTCTATGATGGATATGATGGTGATACTTATCACTCCAGATACGGGACTGTAGTCAC
2496  147_HRV2     CATGTTTTATGATGGGTATGATG------AACAAGATCAAAACTATGGTACAGCAAGCAC
2497  148_HRV2a|   CATGTTTTATGATGGGTATGATG------AACAAGATCAAAACTATGGTACAGCAAGCAC
2498  149_HRV2b|   CATGTTTTATGATGGGTATGATG------AACAAGATCAAAACTATGGTACAGCAAGCAC
2499  150_HRV49a   CATGTTTTATGATGGATATAATG------AACAGGGCCAAAATTATGGTACGGTAAGTAC
2500  151_HRV49b   CATGTTTTATGATGGATATAATG------AACAGGGCCAAAATTATGGTACGGTAAGTAC
2501  152_HRV49    CATGTTTTATGATGGATATAATG------AACAGGGCCAAAATTATGGTACGGTAAGTAC
2502  153_HRV23a   CATGTTTTATGATGGATACAATG------AGAAAGGCACGCATTATGGAACAGTTAGCAC
2503  154_HRV23b   CATGTTTTATGATGGATACAATG------AGAAAGGCACGCATTATGGAACAGTTAGCAC
2504  155_HRV23    CATGTTTTATGATGGATACAATG------AGAAAGGCACGCATTATGGAACAGTTAGCAC
2505  156_HRV30a   CATGTTCTATGATGGATACAATG------AGGGAGGCACAAATTATGGTACAGTGAGCAC
2506  157_HRV30b   CATGTTCTATGATGGATACAATG------AGGGAGGCACAAATTATGGTACAGTGAGCAC
2507  158_HRV30    CATGTTCTATGATGGATACAATG------AGGGAGGCACAAATTATGGTACAGTGAGCAC
2508  159_HRV7     TATGTTCTATGATGGATATGATGGTGATGATGCGTCATCCAAATATGGTTCCGTAGTAAC
2509  160_HRV7b|   TATGTTCTATGATGGATATGATGGTGATGATGCGTCATCCAAATATGGTTCCGTAGTAAC
2510  161_HRV7a|   TATGTTCTATGATGGATATGATGGTGATGATGCGTCATCCAAATATGGTTCCGTAGTAAC
2511  162_HRV88    TATGTTTTATGATGGATATGATGGTGATGATGCATCATCTAGGTATGGCTCAGTGGTAAC
2512  163_HRV88a   TATGTTTTATGATGGATATGATGGTGATGATGCATCATCTAGGTATGGCTCAGTGGTAAC
2513  164_HRV88b   TATGTTTTATGATGGATATGATGGTGATGATGCATCATCTAGGTATGGCTCAGTGGTAAC
2514  165_HRV36a   TATGTTTTATGATGGTTATGATGGTGATAATGCCGCATCAAAATATGGATCTGTGGTTAC
2515  166_HRV36b   TATGTTTTATGATGGTTATGATGGTGATAATGCCGCATCAAAATATGGATCTGTGGTTAC
2516  167_HRV36    TATGTTTTATGATGGTTATGATGGTGATAATGCCGCATCAAAATATGGATCTGTGGTTAC
2517  168_HRV89a   CATGTTTTATGATGGTTATGATGGTGATAGTGCAGCATCAAAATACGGTTCTGTAGTCAC
2518  169_HRV89b   CATGTTTTATGATGGTTATGATGGTGATAGTGCAGCATCAAAATACGGTTCTGTAGTCAC
2519  170_HRV89    CATGTTTTATGATGGTTATGATGGTGATAGTGCAGCATCAAAATACGGTTCTGTAGTCAC
2520  171_HRV58    TATGTTTTATGATGGCTATGATGGTGATGATGCTAAATCAATATATGGTTCTGTGGTAAC
2521  172_HRV58a   TATGTTTTATGATGGCTATGATGGTGATGATGCTAAATCAATATATGGTTCTGTGGTAAC
2522  173_HRV58b   TATGTTTTATGATGGCTATGATGGTGATGATGCTAAATCAATATATGGTTCTGTGGTAAC
2523  174_HRV12a   CATGTTTTATGATGGTTATGCTGATGACAACCCAAGTGCACCTTATGGAACTGTAGTTAC
2524  175_HRV12b   CATGTTTTATGATGGTTATGCTGATGACAACCCAAGTGCACCTTATGGAACTGTAGTTAC
2525  176_HRV12    CATGTTTTATGATGGTTATGCTGATGACAACCCAAGTGCACCTTATGGAACTGTAGTTAC
2526  177_HRV78a   CATGTTTTATGATGGATACTCGGATGACAGCACATCCTCTCCATATGGCACTGTAGTTAC
2527  178_HRV78b   CATGTTTTATGATGGATACTCGGATGACAGCACATCCTCTCCATATGGCACTGTAGTTAC
2528  179_HRV78    CATGTTTTATGATGGATACTCGGATGACAGCACATCCTCTCCATATGGCACTGTAGTTAC
2529  180_HRV20    TATGTTTTATGATGGTTATGAAGATGATAAGG---GAAGTGTGTATGGGTCTGTTGTCAC
2530  181_HRV20a   TATGTTTTATGATGGTTATGAAGATGATAAGG---GAAGTGTGTATGGGTCTGTTGTCAC
```

FIG. D11 CONT'D

```
07.trace                                                                    9/20/2007 5:04 PM 2531 182_HRV20b   TATGTTTTATGATGGTTATGAAGATGATAAGG---GAAGTGTGTATGGGTCTGTTGTCAC
2532 183_HRV68    TATGTTTTATGATGGATATGAGGATGACAAAG---GAAGTGTGTATGGATCTGTTGTTAC
2533 184_HRV68a   TATGTTTTATGATGGATATGAGGATGACAAAG---GAAGTGTGTATGGATCTGTTGTTAC
2534 185_HRV68b   TATGTTTTATGATGGATATGAGGATGACAAAG---GAAGTGTGTATGGATCTGTTGTTAC
2535 186_HRV28    CATGTTTTATGATGGTTATGAAGATGACAATG---GAACTACCTATGGTGCAGTGGTTAC
2536 187_HRV28a   CATGTTTTATGATGGTTATGAAGATGACAATG---GAACTACCTATGGTGCAGTGGTTAC
2537 188_HRV28b   CATGTTTTATGATGGTTATGAAGATGACAATG---GAACTACCTATGGTGCAGTGGTTAC
2538 189_HRV53a   TATGTTCTATGATGGTGAAGATGACAATG---GCACCACTTATGGGGCTGTTGTTAC
2539 190_HRV53b   TATGTTCTATGATGGGTATGAAGATGACAATG---GCACCACTTATGGGGCTGTTGTTAC
2540 191_HRV53    TATGTTCTATGATGGGTATGAAGATGACAATG---GCACCACTTATGGGGCTGTTGTTAC
2541 192_HRV46a   CATGTTTTATGATGGCTACGAAAGTGATAAAG---GCAAGATCTATGGAACTGCAGTCAC
2542 193_HRV46b   CATGTTTTATGATGGCTACGAAAGTGATAAAG---GCAAGATCTATGGAACTGCAGTCAC
2543 194_HRV46    CATGTTTTATGATGGCTACGAAAGTGATAAAG---GCAAGATCTATGGAACTGCAGTCAC
2544 195_HRV80a   CATGTTCTATGATGGGTATGAGAGTGATAAAG---GCAACATTTATGGAACAGCAGTTAC
2545 196_HRV80b   CATGTTCTATGATGGGTATGAGAGTGATAAAG---GCAACATTTATGGAACAGCAGTTAC
2546 197_HRV80    CATGTTCTATGATGGGTATGAGAGTGATAAAG---GCAACATTTATGGAACAGCAGTTAC
2547 198_HRV51    CATGTTTTATGATGGGTATGAAGGTGATAGTTTGACCTCACAGTACGGTTCAGTAGTCAC
2548 199_HRV51a   CATGTTTTATGATGGGTATGAAGGTGATAGTTTGACCTCACAGTACGGTTCAGTAGTCAC
2549 200_HRV51b   CATGTTTTATGATGGGTATGAAGGTGATAGTTTGACCTCACAGTACGGTTCAGTAGTCAC
2550 201_HRV65a   CATGTTCTATGATGGTTATGAGGGTGATGACCCAAATTCAAAATATGGTTCAGTGGTTAC
2551 202_HRV65b   CATGTTCTATGATGGTTATGAGGGTGATGACCCAAATTCAAAATATGGTTCAGTGGTTAC
2552 203_HRV65    CATGTTCTATGATGGTTATGAGGGTGATGACCCAAATTCAAAATATGGTTCAGTGGTTAC
2553 204_HRV71a   CATGTTCTATGATGGGTATGAAGGTGATGCCCTCAGTTCTAAATATGGCTCAGTAGTTAC
2554 205_HRV71b   CATGTTCTATGATGGGTATGAAGGTGATGCCCTCAGTTCTAAATATGGCTCAGTAGTTAC
2555 206_HRV71    CATGTTCTATGATGGGTATGAAGGTGATGCCCTCAGTTCTAAATATGGCTCAGTAGTTAC
2556 207_HRV8     CATGTTCTATGATGGTTATGATTCAGATGGTTTAGATGCTATTTATGGTATTCCTGTTAC
2557 208_HRV95    CATGTTCTATGATGGTTATGATTCAGATGGTTTAGATGCTATTTATGGTATTCCTGTTAC
2558 209_HRV45    CATGTTTTATGATGGATACGACACTGATGGCACAGATGCAGTGTATGGTGTTAGTGTGAC
2559 210_HRV45a   CATGTTTTATGATGGATACGACACTGATGGCACAGATGCAGTGTATGGTGTTAGTGTGAC
2560 211_HRV45b   CATGTTTTATGATGGATACGACACTGATGGCACAGATGCAGTGTATGGTGTTAGTGTGAC
2561 GROUP_1      -ATGTT-TA-GA-GG-TA---------------------TA-GG------------
2562
2563 1_HRV1A1|d   TAATGATATGGGTACTATATGCTCAAGAATAGTTACAGAAAAACAGAAACATTCTGTTGT
2564 2_HRV1A2|d   TAATGATATGGGTACTATATGCTCAAGAATAGTTACAGAAAAACAGAAACATTCTGTTGT
2565 3_HRV1A|cD   TAATGATATGGGTACTATATGCTCAAGAATAGTTACAGAAAAACAGAAACATTCTGTTGT
2566 4_HRV1B1|d   CAATGATATGGGAACCATATGTTCAAGAATAGTTACAGAGAAGCAGGAACACCCTGTCGT
2567 5_HRV1B2|d   CAATGATATGGGAACCATATGTTCAAGAATAGTTACAGAGAAGCAGGAACACCCTGTCGT
2568 6_HRV1B      CAATGATATGGGAACCATATGTTCAAGAATAGTTACAGAGAAGCAGGAACACCCTGTCGT
2569 7_HRV40a|d   TAACCATATGGGAACGCTATGCTCAAGAATAGTCACCAACAAGCAGCAGCATGAAGTTGA
2570 8_HRV40b|d   TAACCATATGGGAACGCTATGCTCAAGAATAGTCACCAACAAGCAGCAGCATGAAGTTGA
2571 9_HRV40      TAACCATATGGGAACGCTATGCTCAAGAATAGTCACCAACAAGCAGCAGCATGAAGTTGA
2572 10_HRV85     CAACCACATGGGAACACTGTGCTCGAGGATAGTTACCAACAAACAGCAGCATGAGGTTGA
2573 11_HRV85a|   CAACCACATGGGAACACTGTGCTCGAGGATAGTTACCAACAAACAGCAGCATGAGGTTGA
2574 12_HRV85b|   CAACCACATGGGAACACTGTGCTCGAGGATAGTTACCAACAAACAGCAGCATGAGGTTGA
2575 13_HRV56a|   AAACCACATGGGGACACTCTGTTCAAGAATTGTGACAAATAAACAACTTCATCCTGTTGA
2576 14_HRV56b|   AAACCACATGGGGACACTCTGTTCAAGAATTGTGACAAATAAACAACTTCATCCTGTTGA
2577 15_HRV56     AAACCACATGGGGACACTCTGTTCAAGAATTGTGACAAATAAACAACTTCATCCTGTTGA
2578 16_HRV54     CAATCATATGGGTACTTTGTGTTCAAGAGTGGTTACTGATAAACAAAAACACCCAGTTGA
2579 17_HRV98     TAATCACATGGGCACTTTGTGTTCAAGAGTAGTTACTGGCAAACAAGAACACCCAGTTGA
2580 18_HRV59a|   CAACCACATGGGCACTTTATGTTCTAGAATAGTTACAAACAGTCAGGAGCATCCAGTGGA
2581 19_HRV59b|   CAACCACATGGGCACTTTATGTTCTAGAATAGTTACAAACAGTCAGGAGCATCCAGTGGA
2582 20_HRV59     CAACCACATGGGCACTTTATGTTCTAGAATAGTTACAAACAGTCAGGAGCATCCAGTGGA
2583 21_HRV63     TAACCACATGGGGACTTTATGTTCTAGAATTGTAACAAACAGCCAAGAACATCCAGTTGA
2584 22_HRV63b|   TAACCACATGGGGACTTTATGTTCTAGAATTGTAACAAACAGCCAAGAACATCCAGTTGA
2585 23_HRV63a|   TAACCACATGGGGACTTTATGTTCTAGAATTGTAACAAACAGCCAAGAACATCCAGTTGA
2586 24_HRV39     TAATGATATGGGTACACTTTGCACTAGAATTGTAACAAACCAACAGGAACACCTAGTGGA
2587 25_HRV39a|   TAATGATATGGGTACACTTTGCACTAGAATTGTAACAAACCAACAGGAACACCTAGTGGA
2588 26_HRV39b|   TAATGATATGGGTACACTTTGCACTAGAATTGTAACAAACCAACAGAAACACCTAGTGGA
2589 27_HRV10a|   AAATCACATGGGCACTTTGTGCATGCGAATAGTCACAAACCAGCAAGCACATGAGGTGGA
2590 28_HRV10b|   AAATCACATGGGCACTTTGTGCATGCGAATAGTCACAAACCAGCAAGCACATGAGGTGGA
2591 29_HRV10     AAATCACATGGGCACTTTGTGCATGCGAATAGTCACAAACCAGCAAGCACATGAGGTGGA
2592 30_HRV100a   TAACCACATGGGTACACTTTGTATGAGGATAGTTACAAATCAGCAAGCACATGAGGTGGA
2593 31_HRV100b   TAACCACATGGGTACACTTTGTATGAGGATAGTTACAAATCAGCAAGCACATGAGGTGGA
2594 32_HRV100    TAACCACATGGGTACACTTTGTATGAGGATAGTTACAAATCAGCAAGCACATGAGGTGGA
2595 33_HRV66     TAATCATATGGGTACATTATGTATTAGGATTGTTACAAATGAACAGCACCATAATGTTGA
```

FIG. D11 CONT'D

```
07.trace                                                                    9/20/2007 5:04 PM 2596  34_HRV66b|   TAATCATATGGGTACATTATGTATTAGGATTGTTACAAATGAACAGCACCATAATGTTGA
2597  35_HRV66a|   TAATCATATGGGTACATTATGTATTAGGATTGTTACAAATGAACAGCACCATAATGTTGA
2598  36_HRV77a|   TAATCACATGGGCACACTGTGCATTAGAATAGTCACTAATCAGCAAAATCATGAGGTTGA
2599  37_HRV77b|   TAATCACATGGGCACACTGTGCATTAGAATAGTCACTAATCAGCAAAATCATGAGGTTGA
2600  38_HRV77    TAATCACATGGGCACACTGTGCATTAGAATAGTCACTAATCAGCAAAATCATGAGGTTGA
2601  39_HRV62a   TAATCGTATGGGGGCACTGTGTATGAGGATTGTCACAAACAAACAAGTTCATGATGTTGA
2602  40_HRV62b   TAATCGTATGGGGGCACTGTGTATGAGGATTGTCACAAACAAACAAGTTCATGATGTTGA
2603  41_HRV25    TAACCGTATGGGAGCACTGTGCATGAGAATTGTCACAAATAAACAAGTCCATGATGTTGA
2604  42_HRV29a   TAACCGGATGGGGACGCTTTGTGTCAGAATTGTTACAGGCAAACAAGCTCATGATGTTCA
2605  43_HRV29b   TAACCGGATGGGGACGCTTTGTGTCAGAATTGTTACAGGCAAACAAGCTCATGATGTTCA
2606  44_HRV44a   TAACCGGATGGGGACGCTTTGCGTCAGGATCGTTACGGGCAAACAGGCTCATGATGTCCA
2607  45_HRV44b   TAACCGGATGGGGACGCTTTGCGTCAGGATCGTTACGGGCAAACAGGCTCATGATGTCCA
2608  46_HRV31    TAATCGCATGGGTGCACTATGCATGAGAGTTGTCACTAACAAACAAGCTCATAAAGTTGA
2609  47_HRV31a|  TAATCGCATGGGTGCACTATGCATGAGAGTTGTCACTAACAAACAAGCTCATAAAGTTGA
2610  48_HRV31b|  TAATCGCATGGGTGCACTATGCATGAGAGTTGTCACTAACAAACAAGCTCATAAAGTTGA
2611  49_HRV47    CAATCGCATGGGTGCATTGTGTATGAGAGTTGTAACAAACAAGCAACTCCATAAAGTTGA
2612  50_HRV47a|  CAATCGCATGGGTGCATTGTGTATGAGAGTTGTAACAAACAAGCAACTCCATAAAGTTGA
2613  51_HRV47b|  CAATCGCATGGGTGCATTGTGTATGAGAGTTGTAACAAACAAGCAACTCCATAAAGTTGA
2614  52_HRV11    CAATGATATGGGCACTCTGTGTTATAGAATAGTAACTGATGACCATAGACACAAAATTGA
2615  53_HRV11b|  CAATGATATGGGCACTCTGTGTTATAGAATAGTAACTGATGACCATAGACACAAAATTGA
2616  54_HRV11a|  CAATGATATGGGCACTCTGTGTTATAGAATAGTAACTGATGACCATAGACACAAAATTGA
2617  55_HRV76    CAATGACATGGGCACCCTATGTTCCAGGATAGTAACTGATGATCATAAGCACAAGATTGA
2618  56_HRV76b|  CAATGACATGGGCACCCTATGTTCCAGGATAGTAACTGATGATCATAAGCACAAGATTGA
2619  57_HRV76a|  CAATGACATGGGCACCCTATGTTCCAGGATAGTAACTGATGATCATAAGCACAAGATTGA
2620  58_HRV33    CAATGACATGGGCACTTTATGCTCTAGAATAGTTACAGATAATCATAAGCATCCAATAGA
2621  59_HRV33b|  CAATGACATGGGCACTTTATGCTCTAGAATAGTTACAGATAATCATAAGCATCCAATAGA
2622  60_HRV33a|  CAATGACATGGGCACTTTATGCTCTAGAATAGTTACAGATAATCATAAGCATCCAATAGA
2623  61_HRV24a|  AAACGACATGGGAACTCTATGCTATAGAATAGTCACTGACAAGCATAATCACCAAATAGA
2624  62_HRV24b|  AAACGACATGGGAACTCTATGCTATAGAATAGTCACTGACAAGCATAATCACCAAATAGA
2625  63_HRV24    AAACGACATGGGAACTCTATGCTATAGAATAGTCACTGACAAGCATAATCACCAAATAGA
2626  64_HRV90    TAATGATATGGGAACCTTATGTTATAGAATAGTTACAGATGAACATGCCCACAAAATAGA
2627  65_HRV90a|  TAATGATATGGGAACCTTATGTTATAGAATAGTTACAGATGAACATGCCCACAAAATAGA
2628  66_HRV90b|  TAATGATATGGGAACCTTATGTTATAGAATAGTTACAGATGAACATGCCCACAAAATAGA
2629  67_HRV34    TAATGACATGGGTACTTTATGCTCCAGAATTGTAACTGATGAACACCAAAACAGAGTAGA
2630  68_HRV34b|  TAATGACATGGGTACTTTATGCTCCAGAATTGTAACTGATGAACACCAAAACAGAGTAGA
2631  69_HRV34a|  TAATGACATGGGTACTTTATGCTCCAGAATTGTAACTGATGAACACCAAAACAGAGTAGA
2632  70_HRV50a|  CAATGACATGGGCACTTTGTGTTCTAGGATTGTCACTGATGAGCACCAAAATAAAGTGGA
2633  71_HRV50b|  CAATGACATGGGCACTTTGTGTTCTAGGATTGTCACTGATGAGCACCAAAATAAAGTGGA
2634  72_HRV50    CAATGACATGGGCACTTTGTGTTCTAGGATTGTCACTGATGAGCACCAAAATAAAGTGGA
2635  73_HRV18a|  AAATGACATGGGTACCTTGTGCTCTAGAATAGTCACAGATAAACATAAGAATGAGGTGGA
2636  74_HRV18b|  AAATGACATGGGTACCTTGTGCTCTAGAATAGTCACAGATAAACATAAGAATGAGGTGGA
2637  75_HRV18    AAATGACATGGGTACCTTGTGCTCTAGAATAGTCACAGATAAACATAAGAATGAGGTGGA
2638  76_HRV55    TAATGACATGGGTACTTTATGTTCTAGAATAATAACTGATAACCATAAGCACCCAATTGA
2639  77_HRV55b|  TAATGACATGGGTACTTTATGTTCTAGAATAATAACTGATAACCATAAGCACCCAATTGA
2640  78_HRV55a|  TAATGACATGGGTACTTTATGTTCTAGAATAATAACTGATAACCATAAGCACCCAATTGA
2641  79_HRV57    TAATGACATGGGCACTTTATGTTCTAGAATTGTTACTGACCAGCACACACATCCCATAAA
2642  80_HRV57a|  TAATGACATGGGCACTTTATGTTCTAGAATTGTTACTGACCAGCACACACATCCCATAAA
2643  81_HRV57b|  TAATGACATGGGCACTTTATGTTCTAGAATTGTTACTGACCAGCACACACATCCCATAAA
2644  82_HRV21    TAATGATATGGGATCTCTATGCTACAGAATAGTAACTGGCCAGCATAAGCATAAGATAGA
2645  83_HRVHan   TAATGATATGGGATCTCTATGCTATAGAATAGTAACTGATCAGCATAAGCACAAGATAGA
2646  84_HRV43    CAACCACATGGGAACATTATGTTCTAGGATAGTTACAGAAGAACACCAAAATCAAATCGA
2647  85_HRV43b|  CAACCACATGGGAACATTATGTTCTAGGATAGTTACAGAAGAACACCAAAATCAAATCGA
2648  86_HRV43a|  CAACCACATGGGAACATTATGTTCTAGGATAGTTACAGAAGAACACCAAAATCAAATCGA
2649  87_HRV75    TAATCACATGGGGACACTGTGTTCTAGAATTACAGAAGAACATCGAAATAAAGTTGA
2650  88_HRV75b|  TAATCACATGGGGACACTGTGTTCTAGAATAGTTACAGAAGAACATCGAAATAAAGTTGA
2651  89_HRV75a|  TAATCACATGGGGACACTGTGTTCTAGAATAGTTACAGAAGAACATCGAAATAAAGTTGA
2652  96_HRV9a|d  AAATGATATGGGATCTTTATGTTCCCGTGTAGTTACTGAAGAGCATGGACCCCGTGTCAA
2653  97_HRV9b|d  AAATGATATGGGATCTTTATGTTCCCGTGTAGTTACTGAAGAGCATGGACCCCGTGTCAA
2654  98_HRV9     AAATGATATGGGATCTTTATGTTCCCGTGTAGTTACTGAAGAGCATGGACCCCGTGTCAA
2655  99_HRV32    AAATGATATGGGTTCCCTGTGTTCTCGTATAGTCACCGAAGAGCACGGATCCCGTGTTGA
2656  100_HRV32a  AAATGATATGGGTTCCCTGTGTTCTCGTATAGTCACCGAAGAGCACGGATCCCGTGTTGA
2657  101_HRV32b  AAATGATATGGGTTCCCTGTGTTCTCGTATAGTCACCGAAGAGCACGGATCCCGTGTTGA
2658  102_HRV67   TAATGATATGGGTTCCTTGTGTTCGCGTATAGTTACTGAAGAACATGGTTCTCGCGTAAA
2659  103_HRV67a  TAATGATATGGGTTCCTTGTGTTCGCGTATAGTTACTGAAGAACATGGTTCTCGCGTAAA
2660  104_HRV67b  TAATGATATGGGTTCCTTGTGTTCGCGTATAGTTACTGAAGAACATGGTTCTCGCGTAAA
```

FIG. D11 CONT'D 07.trace 9/20/2007 5:04 PM

```
2661  105_HRV15    TAATGACATGGGGACACTGTGTTCTAGAATAGTAACTGAAGAGCATGGGACACGTGTAGA
2662  106_HRV15a   TAATGACATGGGGACACTGTGTTCTAGAATAGTAACTGAAGAGCATGGGACACGTGTAGA
2663  107_HRV15b   TAATGACATGGGGACACTGTGTTCTAGAATAGTAACTGAAGAGCATGGGACACGTGTAGA
2664  108_HRV74a   AAATGACATGGGAACTCTATGTTCTAGAATTGTGACTGAAGAACACGATGCACGTGTGGA
2665  109_HRV74b   AAATGACATGGGAACTCTATGTTCTAGAATTGTGACTGAAGAACACGATGCACGTGTGGA
2666  110_HRV74    AAATGACATGGGAACTCTATGTTCTAGAATTGTGACTGAAGAACACGATGCACGTGTGGA
2667  111_HRV38a   CAATGATATGGGGACACTTTGTTCAAGAATAGTCACTGAAAATCATGGGACCCAAGTGAA
2668  112_HRV38b   CAATGATATGGGGACACTTTGTTCAAGAATAGTCACTGAAAATCATGGGACCCAAGTGAA
2669  113_HRV38    CAATGATATGGGGACACTTTGTTCAAGAATAGTCACTGAAAATCATGGGACCCAAGTGAA
2670  114_HRV60    CAATGACATGGGAACGTTGTGCTCCAGAATAGTTACTGAACACCATGGTACACAGGTTCA
2671  115_HRV60a   CAATGACATGGGAACGTTGTGCTCCAGAATAGTTACTGAACACCATGGTACACAGGTTCA
2672  116_HRV60b   CAATGACATGGGAACGTTGTGCTCCAGAATAGTTACTGAACACCATGGTACACAGGTTCA
2673  117_HRV64a   AAATGATATGGGCACTTTGTGTTCTAGAATTGTGACTGAGGAACACACAACACAGGTCAA
2674  118_HRV64b   AAATGATATGGGCACTTTGTGTTCTAGAATTGTGACTGAGGAACACACAACACAGGTCAA
2675  119_HRV64    AAATGATATGGGCACTTTGTGTTCTAGAATTGTGACTGAGGAACACACAACACAGGTCAA
2676  120_HRV94a   AAATGACATGGGAACATTATGCTCCAGGATTGTGACTGAGGAGCACAAGACACAGGTTAA
2677  121_HRV94b   AAATGACATGGGAACATTATGCTCCAGGATTGTGACTGAGGAGCACAAGACACAGGTTAA
2678  122_HRV94    AAATGACATGGGAACATTATGCTCCAGGATTGTGACTGAGGAGCACAAGACACAGGTTAA
2679  123_HRV22    AAATGATATGGGCACACTGTGCTCTAGGATTGTGACTGAAGAACACCAGACACAAGTCAA
2680  124_HRV22a   AAATGATATGGGCACACTGTGCTCTAGGATTGTGACTGAAGAACACCAGACACAAGTCAA
2681  125_HRV22b   AAATGATATGGGCACACTGTGCTCTAGGATTGTGACTGAAGAACACCAGACACAAGTCAA
2682  126_HRV82    AAATGACATGGGTACACTGTGTTCTAGAATTGTAACTGAAGAACACCAGACTCAAGTCAG
2683  127_HRV82b   AAATGACATGGGTACACTGTGTTCTAGAATTGTAACTGAAGAACACCAGACTCAAGTCAG
2684  128_HRV82a   AAATGACATGGGTACACTGTGTTCTAGAATTGTAACTGAAGAACACCAGACTCAAGTCAG
2685  129_HRV19    TAATGATATGGGAACCTTATGCTCCAGAATAGTAACTGATGAACACCAAACACAGGTTGC
2686  130_HRV19a   TAATGATATGGGAACCTTATGCTCCAGAATAGTAACTGATGAACACCAAACACAGGTTGC
2687  131_HRV19b   TAATGATATGGGAACCTTATGCTCCAGAATAGTAACTGATGAACACCAAACACAGGTTGC
2688  132_HRV13    TAATGATATGGGCACACTTTGCTTCAGAATAGTAACTGAAGAACATACTAACAAGGTCAA
2689  133_HRV13a   TAATGATATGGGCACACTTTGCTTCAGAATAGTAACTGAAGAACATACTAACAAGGTCAA
2690  134_HRV13b   TAATGATATGGGCACACTTTGCTTCAGAATAGTAACTGAAGAACATACTAACAAGGTCAA
2691  135_HRV41    AAATGACATGGGTACATTATGCTTTAGAATAGTTACTGAAGAACACACCAACAAAGTTAA
2692  136_HRV41a   AAATGACATGGGTACATTATGCTTTAGAATAGTTACTGAAGAACACACCAACAAAGTTAA
2693  137_HRV41b   AAATGACATGGGTACATTATGCTTTAGAATAGTTACTGAAGAACACACCAACAAAGTTAA
2694  138_HRV73    TAATGACATGGGCACATTATGCTTTAGGATAGTGACTGAAGAACACACTAGCAGGGTAAA
2695  139_HRV73b   TAATGACATGGGCACATTATGCTTTAGGATAGTGACTGAAGAACACACTAGCAGGGTAAA
2696  140_HRV73a   TAATGACATGGGCACATTATGCTTTAGGATAGTGACTGAAGAACACACTAGCAGGGTAAA
2697  141_HRV61    AAATGATATGGGTGCATTGTGCTTTAGAATAGTAACTGAACAGCATACAAATCAAGTTAA
2698  142_HRV61a   AAATGATATGGGTGCATTGTGCTTTAGAATAGTAACTGAACAGCATACAAATCAAGTTAA
2699  143_HRV61b   AAATGATATGGGTGCATTGTGCTTTAGAATAGTAACTGAACAGCATACAAATCAAGTTAA
2700  144_HRV96    CAATGACATGGGCACTTTATGTTTTAGAATAGTGACAGAGGAACACACCAACAAGGTCAA
2701  145_HRV96b   CAATGACATGGGCACTTTATGTTTTAGAATAGTGACAGAGGAACACACCAACAAGGTCAA
2702  146_HRV96a   CAATGACATGGGCACTTTATGTTTTAGAATAGTGACAGAGGAACACACCAACAAGGTCAA
2703  90_HRV16a|   CAATGACATGGGAACTTTGTGTTCGCGTATTGTGACCAGTGAGCAATTACACAAAGTCAA
2704  91_HRV16b|   CAATGACATGGGAACTTTGTGTTCGCGTATTGTGACCAGTGAGCAATTACACAAAGTCAA
2705  92_1AYM_A    CAATGACATGGGAACTTTGTGTTCGCGTATTGTGACCAGTGAGCAATTACACAAAGTCAA
2706  93_HRV81a|   TAATGATATGGGAACATTATGCTCACGGATAGTGACAAGTGAGCAAGTGCACAAGGTGAA
2707  94_HRV81b|   TAATGATATGGGAACATTATGCTCACGGATAGTGACAAGTGAGCAAGTGCACAAGGTGAA
2708  95_HRV81     TAATGATATGGGAACATTATGCTCACGGATAGTGACAAGTGAGCAAGTGCACAAGGTGAA
2709  147_HRV2     AAATAACATGGGGTCACTATGCTCTAGGATAGTAACAGAGAAACACATTCATAAGGTACA
2710  148_HRV2a|   AAATAACATGGGGTCACTATGCTCTAGGATAGTAACAGAGAAACACATTCATAAGGTACA
2711  149_HRV2b|   AAATAACATGGGGTCACTATGCTCTAGGATAGTAACAGAGAAACACATTCATAAGGTACA
2712  150_HRV49a   AAACAACATGGGATCATTATGCTCTAGGATAGTAACAGAGAAACACATTCACAGTATGCA
2713  151_HRV49b   AAACAACATGGGATCATTATGCTCTAGGATAGTAACAGAGAAACACATTCACAGTATGCA
2714  152_HRV49    AAACAACATGGGATCATTATGCTCTAGGATAGTAACAGAGAAACACATTCACAGTATGCA
2715  153_HRV23a   AAACAACATGGGCACATTGTGCTCCAGAGTGGTAACAGAGAAACACATTCATGATATGCG
2716  154_HRV23b   AAACAACATGGGCACATTGTGCTCCAGAGTGGTAACAGAGAAACACATTCATGATATGCG
2717  155_HRV23    AAACAACATGGGCACATTGTGCTCCAGAGTGGTAACAGAGAAACACATTCATGATATGCG
2718  156_HRV30a   AAACAACATGGGCACACTGTGTTCCAGAGTGGTAACAGAGAAAAACACATTCATGATGTGCG
2719  157_HRV30b   AAACAACATGGGCACACTGTGTTCCAGAGTGGTAACAGAAAAACACATTCATGATGTGCG
2720  158_HRV30    AAACAACATGGGCACACTGTGTTCCAGAGTGGTAACAGAAAAACACATTCATGATGTGCG
2721  159_HRV7     CAATGACATGGGAACCATATGTGTTAGACTAGTTACATCTACACAAAAACACAATTTAAA
2722  160_HRV7b|   CAATGACATGGGAACCATATGTGTTAGACTAGTTACATCTACACAAAAACACAATTTAAA
2723  161_HRV7a|   CAATGACATGGGAACCATATGTGTTAGACTAGTTACATCTACACAAAAACACAATTTAAA
2724  162_HRV88    TAATGATATGGGAACTATATGTATTAGATTGGTCACCTCCACCCAAAAGCATAAACTGAA
2725  163_HRV88a   TAATGATATGGGAACTATATGTATTAGATTGGTCACCTCCACCCAAAAGCATAAACTGAA
```

FIG. D11 CONT'D 07.trace                                                          9/20/2007 5:04 PM

```
2726  164_HRV88b    TAATGATATGGGAACTATATGTATTAGATTGGTCACCTCCACCCAAAAGCATAAACTGAA
2727  165_HRV36a    TAACGACATGGGAACCATATGTGTTAGAATAGTTACATCCAACCAAAAACATGATTTAAA
2728  166_HRV36b    TAACGACATGGGAACCATATGTGTTAGAATAGTTACATCCAACCAAAAACATGATTTAAA
2729  167_HRV36     TAACGACATGGGAACCATATGTGTTAGAATAGTTACATCCAACCAAAAACATGATTTAAA
2730  168_HRV89a    TAATGATATGGGAACCATATGTGTTAGAATAGTGACATCCAACCAAAAACATGATTTAAA
2731  169_HRV89b    TAATGATATGGGAACCATATGTGTTAGAATAGTGACATCCAACCAAAAACATGATTTAAA
2732  170_HRV89     TAATGATATGGGAACCATATGTGTTAGAATAGTGACATCCAACCAAAAACATGATTTAAA
2733  171_HRV58     AAATGACATGGGAACTATATGTGTTAGAATAGTCACATCCAAACAAAGACACAATTTAAA
2734  172_HRV58a    AAATGACATGGGAACTATATGTGTTAGAATAGTCACATCCAAACAAAGACACAATTTAAA
2735  173_HRV58b    AAATGACATGGGAACTATATGTGTTAGAATAGTCACATCCAAACAAAGACACAATTTAAA
2736  174_HRV12a    CAATGACATGGGTTCACTGTGTGTCAGAATAGTTACAGACCAGCAAAAACATAAAGTTAA
2737  175_HRV12b    CAATGACATGGGTTCACTGTGTGTCAGAATAGTTACAGACCAGCAAAAACATAAAGTTAA
2738  176_HRV12     CAATGACATGGGTTCACTGTGTGTCAGAATAGTTACAGACCAGCAAAAACATAAAGTTAA
2739  177_HRV78a    CAATGACATGGGTACACTGTGTATGAGGATGGTTACAGATCAACAACAACATAAGGTCAC
2740  178_HRV78b    CAATGACATGGGTACACTGTGTATGAGGATGGTTACAGATCAACAACAACATAAGGTCAC
2741  179_HRV78     CAATGACATGGGTACACTGTGTATGAGGATGGTTACAGATCAACAACAACATAAGGTCAC
2742  180_HRV20     AAACGATATGGGCACATTGTGTGTTCGTATTGTGACTGAGCAGCAGACACATAAGGTTAA
2743  181_HRV20a    AAACGATATGGGCACATTGTGTGTTCGTATTGTGACTGAGCAGCAGACACATAAGGTTAA
2744  182_HRV20b    AAACGATATGGGCACATTGTGTGTTCGTATTGTGACTGAGCAGCAGACACATAAGGTTAA
2745  183_HRV68     AAATGATATGGGCACATTATGTGTCCGTATTGTGACTGAGCAGCAGACACATAGGGTCAA
2746  184_HRV68a    AAATGATATGGGCACATTATGTGTCCGTATTGTGACTGAGCAGCAGACACATAGGGTCAA
2747  185_HRV68b    AAATGATATGGGCACATTATGTGTCCGTATTGTGACTGAGCAGCAGACACATAGGGTCAA
2748  186_HRV28     AAATCATATGGGAACACTCTGTGCTCGCATAGTAACTGAACAACAGAAGCATGAAGTCAA
2749  187_HRV28a    AAATCATATGGGAACACTCTGTGCTCGCATAGTAACTGAACAACAGAAGCATGAAGTCAA
2750  188_HRV28b    AAATCATATGGGAACACTCTGTGCTCGCATAGTAACTGAACAACAGAAGCATGAAGTCAA
2751  189_HRV53a    TAATGATATGGGAACACTTTGTGTGCGCATAGTGACTGAGCAACAGAAAAATGAGGTCAA
2752  190_HRV53b    TAATGATATGGGAACACTTTGTGTGCGCATAGTGACTGAGCAACAGAAAAATGAGGTCAA
2753  191_HRV53     TAATGATATGGGAACACTTTGTGTGCGCATAGTGACTGAGCAACAGAAAAATGAGGTCAA
2754  192_HRV46a    CAATGATATGGGAACTATATGTGTCAGAATTGTTACCGAACAACAAAAACATAAGGTTCT
2755  193_HRV46b    CAATGATATGGGAACTATATGTGTCAGAATTGTTACCGAACAACAAAAACATAAGGTTCT
2756  194_HRV46     CAATGATATGGGAACTATATGTGTCAGAATTGTTACCGAACAACAAAAACATAAGGTTCT
2757  195_HRV80a    CAATGATATGGGAACCCTGTGTGCTAGAATTGTTACAGAACAACAGAAACATAAAGTCCT
2758  196_HRV80b    CAATGATATGGGAACCCTGTGTGCTAGAATTGTTACAGAACAACAGAAACATAAAGTCCT
2759  197_HRV80     CAATGATATGGGAACCCTGTGTGCTAGAATTGTTACAGAACAACAGAAACATAAAGTCCT
2760  198_HRV51     AAATGCTATGGGGACACTATGTGTTCGTGTGGTCACAGAGCAACAAAAACATGAGGTTAA
2761  199_HRV51a    AAATGCTATGGGGACACTATGTGTTCGTGTGGTCACAGAGCAACAAAAACATGAGGTTAA
2762  200_HRV51b    AAATGCTATGGGGACACTATGTGTTCGTGTGGTCACAGAGCAACAAAAACATGAGGTTAA
2763  201_HRV65a    TAATGCTATGGGCACACTATATGTGCCGTGTGGTTACAGAAAGGCAAAAACATGAAGTCAA
2764  202_HRV65b    TAATGCTATGGGCACACTATATGTGCCGTGTGGTTACAGAAAGGCAAAAACATGAAGTCAA
2765  203_HRV65     TAATGCTATGGGCACACTATATGTGCCGTGTGGTTACAGAAAGGCAAAAACATGAAGTCAA
2766  204_HRV71a    TAATGCCATGGGCACCTTATGTGTTCGTGTGGTTACAGAACAGCAAAGCAACACAGTCAA
2767  205_HRV71b    TAATGCCATGGGCACCTTATGTGTTCGTGTGGTTACAGAACAGCAAAGCAACACAGTCAA
2768  206_HRV71     TAATGCCATGGGCACCTTATGTGTTCGTGTGGTTACAGAACAGCAAAGCAACACAGTCAA
2769  207_HRV8      AAATCACATGGGCACAATATGTGTGAGAATGGTGACAGATAAACAGAAAATTAAAACTAA
2770  208_HRV95     AAATCACATGGGCACAATATGTGTGAGAATGGTGACAGATAAACAGAAAATTAAAACTAA
2771  209_HRV45     TAACCATATGGGGACTATATGTGTTAGAATTGTTACAGACCAACAACAACATAGAGTTAA
2772  210_HRV45a    TAACCATATGGGGACTATATGTGTTAGAATTGTTACAGACCAACAACAACATAGAGTTAA
2773  211_HRV45b    TAACCATATGGGGACTATATGTGTTAGAATTGTTACAGACCAACAACAACATAGAGTTAA
2774  GROUP_1       -AA----ATGGG--C--T-T------G--T--T-AC-------CA--------------
2775
2776  1_HRV1A1|d    CATCACAACACACATATATCATAAAGCTAAACACACAAAAGCTTGGTGTCCTAGGCCCCC
2777  2_HRV1A2|d    CATCACAACACACATATATCATAAAGCTAAACACACAAAAGCTTGGTGTCCTAGGCCCCC
2778  3_HRV1A|cD    CATCACAACACACATATATCATAAAGCTAAACACACAAAAGCTTGGTGTCCTAGGCCCCC
2779  4_HRV1B1|d    TATTACAACACACATATATCACAAAGCTAAACACACAAAAGCTTGGTGTCCTAGACCTCC
2780  5_HRV1B2|d    TATTACAACACACATATATCACAAAGCTAAACACACAAAAGCTTGGTGTCCTAGACCTCC
2781  6_HRV1B       TATTACAACACACATATATCACAAAGCTAAACACACAAAAGCTTGGTGTCCTAGACCTCC
2782  7_HRV40a|d    GATTACCACACGTATATATCACAAGGCCAAGCATATTAAAGCATGGTGTCCAAGGGCCCC
2783  8_HRV40b|d    GATTACCACACGTATATATCACAAGGCCAAGCATATTAAAGCATGGTGTCCAAGGGCCCC
2784  9_HRV40       GATTACCACACGTATATATCACAAGGCCAAGCATATTAAAGCATGGTGTCCAAGGGCCCC
2785  10_HRV85      AATCACCACGCGTGTGTATCATAAGGCCAAGCATGTAAAGGCTTGGTGTCCAAGAGCACC
2786  11_HRV85a|    AATCACCACGCGTGTGTATCATAAGGCCAAGCATGTAAAGGCTTGGTGTCCAAGAGCACC
2787  12_HRV85b|    AATCACCACGCGTGTGTATCATAAGGCCAAGCATGTAAAGGCTTGGTGTCCAAGAGCACC
2788  13_HRV56a|    AGTCACAACTCGTGTATATCATAAGGCAAAGCATATTCGAGCATGGTGTCCTAGAGCACC
2789  14_HRV56b|    AGTCACAACTCGTGTATATCATAAGGCAAAGCATATTCGAGCATGGTGTCCTAGAGCACC
2790  15_HRV56      AGTCACAACTCGTGTATATCATAAGGCAAAGCATATTCGAGCATGGTGTCCTAGAGCACC
```

FIG. D11 CONT'D 07.trace                                                                                    9/20/2007 5:04 PM

```
2791  16_HRV54    AATCACCACACGGGTGTATCACAAGGCAAAACACATTAGAGCATGGTGTCCACGTGCACC
2792  17_HRV98    AATCACTACACGTGTGTACCACAAAGCAAAACACATTAGAGCATGGTGTCCACGTGCACC
2793  18_HRV59a|  GGTTGTCACACGTGTGTATCACAAAGCTAAACACGTCAAAGCCTGGTGCCCTAGAGCTCC
2794  19_HRV59b|  GGTTGTCACACGTGTGTATCACAAAGCTAAACACGTCAAAGCCTGGTGCCCTAGAGCTCC
2795  20_HRV59    GGTTGTCACACGTGTGTATCACAAAGCTAAACACGTCAAAGCCTGGTGCCCTAGAGCTCC
2796  21_HRV63    GGTGACTACACGTGTATATCATAAAGCTAAACACATCAGAGCCTGGTGCCCAAGAGCTCC
2797  22_HRV63b|  GGTGACTACACGTGTATATCATAAAGCTAAACACATCAGAGCCTGGTGCCCAAGAGCTCC
2798  23_HRV63a|  GGTGACTACACGTGTATATCATAAAGCTAAACACATCAGAGCCTGGTGCCCAAGAGCTCC
2799  24_HRV39    GGTTACAACCAGAGTTTACCATAAAGCCAAGCATGTTAAAGCATGGTGCCCTAGGGCTCC
2800  25_HRV39a|  GGTTACAACCAGAGTTTACCATAAAGCCAAGCATGTTAAAGCATGGTGCCCTAGGGCTCC
2801  26_HRV39b|  GGTTACAACCAGAGTTTACCATAAAGCCAAGCATGTTAAAGCATGGTGCCCTAGGGCTCC
2802  27_HRV10a|  AATTACCACCAGTGTTTATCACAAAGCCAAGCATGTCAAAGCATGGTGTCCAAGACCACC
2803  28_HRV10b|  AATTACCACCAGTGTTTATCACAAAGCCAAGCATGTCAAAGCATGGTGTCCAAGACCACC
2804  29_HRV10    AATTACCACCAGTGTTTATCACAAAGCCAAGCATGTCAAAGCATGGTGTCCAAGACCACC
2805  30_HRV100a  AATTACTACTAATATCTATCACAAGGCCAAACATGTTAAAGCTTGGTGCCCAAGACCACC
2806  31_HRV100b  AATTACTACTAATATCTATCACAAGGCCAAACATGTTAAAGCTTGGTGCCCAAGACCACC
2807  32_HRV100   AATTACTACTAATATCTATCACAAGGCCAAACATGTTAAAGCTTGGTGCCCAAGACCACC
2808  33_HRV66    AATTACTACTAGAGTATACCATAAGGCTAAGCATGTTAAAGCCTGGTGTCCTAGACCACT
2809  34_HRV66b|  AATTACTACTAGAGTATACCATAAGGCTAAGCATGTTAAAGCCTGGTGTCCTAGACCACT
2810  35_HRV66a|  AATTACTACTAGAGTATACCATAAGGCTAAGCATGTTAAAGCCTGGTGTCCTAGACCACT
2811  36_HRV77a|  AATCACCACTAGAGTATACCACAAGGCTAAACATATTAAAGCTTGGTGTCCCAGACCACC
2812  37_HRV77b|  AATCACCACTAGAGTATACCACAAGGCTAAACATATTAAAGCTTGGTGTCCCAGACCACC
2813  38_HRV77    AATCACCACTAGAGTATACCACAAGGCTAAACATATTAAAGCTTGGTGTCCCAGACCACC
2814  39_HRV62a   GGTCACAACTAATATTTACCACAAGGCTAAGCATGTAAAAGCGTGGTGCCCGCGGCCGCC
2815  40_HRV62b   GGTCACAACTAATATTTACCACAAGGCTAAGCATGTAAAAGCGTGGTGCCCTAGACCACC
2816  41_HRV25    GGTTACAACTAACATTTACCATAAAGCTAAGCATGTAAAAGCATGGTGCCCTAGACCACC
2817  42_HRV29a   AGTTACAACAAGTATCTATCACAAAGCTAAACATGTAAAGGCGTGGTGTCCTAGACCACC
2818  43_HRV29b   AGTTACAACAAGTATCTATCACAAAGCTAAACATGTAAAGGCGTGGTGTCCTAGACCACC
2819  44_HRV44a   AGTTACAACAAGCATTTATCACAAAGCTAAACATGTAAAAGCATGGTGCCCTAGACCACC
2820  45_HRV44b   AGTTACAACAAGCATTTATCACAAAGCTAAACATGTAAAAGCATGGTGCCCTAGACCACC
2821  46_HRV31    AATCACAACCAATATTTACCATAAGGCCAAACATGTTAAGGCATGGTGTCCTAGGCCCCC
2822  47_HRV31a|  AATCACAACCAATATTTACCATAAGGCCAAACATGTTAAGGCATGGTGTCCTAGGCCCCC
2823  48_HRV31b|  AATCACAACCAATATTTACCATAAGGCCAAACATGTAAAGGCATGGTGTCCTAGGCCACC
2824  49_HRV47    AATCACAACTAACATCTACCATAAAGCCAAGCATGTGAAAGCATGGTGTCCTAGACCACC
2825  50_HRV47a|  AATCACAACTAACATCTACCATAAAGCCAAGCATGTGAAAGCATGGTGTCCTAGACCACC
2826  51_HRV47b|  AATCACAACTAACATCTACCATAAAGCCAAGCATGTGAAAGCATGGTGTCCTAGACCACC
2827  52_HRV11    AGTCACAACTAGGGTGTATCATAAAGCAAAGCATGTGAAGGTGTGGTGTCCAAGACCACC
2828  53_HRV11b   AGTCACAACTAGGGTGTATCATAAAGCAAAGCATGTGAAGGTGTGGTGTCCAAGACCACC
2829  54_HRV11a|  AGTCACAACTAGGGTGTATCATAAAGCAAAGCATGTGAAGGTGTGGTGTCCAAGACCACC
2830  55_HRV76    AGTTACAACAAGAATATATCACAAAGCAAAGCATGTTAAGGTATGGTGCCCGAGACCACC
2831  56_HRV76b|  AGTTACAACAAGAATATATCACAAAGCAAAGCATGTTAAGGTATGGTGCCCGAGACCACC
2832  57_HRV76a|  AGTTACAACAAGAATATATCACAAAGCAAAGCATGTTAAGGTATGGTGCCCGAGACCACC
2833  58_HRV33    AGTTACAACAAGAGTATACCACAAAGCAAACATGTCAAAGTCTGGTGCCCAAGACCACC
2834  59_HRV33b|  AGTTACAACAAGAGTATACCATAAAGCAAAACATGTCAAAGTCTGGTGCCCAAGACCACC
2835  60_HRV33a|  AGTTACAACAAGAGTATACCATAAAGCAAAACATGTCAAAGTCTGGTGCCCAAGACCACC
2836  61_HRV24a   AATTACAACAAGAATATACCACAAAGCAAAGCACATTAAGGTCTGGTGTCCAAGGCCACC
2837  62_HRV24b|  AATTACAACAAGAATATACCACAAAGCAAAGCACATTAAGGTCTGGTGTCCAAGGCCACC
2838  63_HRV24    AATTACAACAAGAATATACCACAAAGCAAAGCACATTAAGGTCTGGTGTCCAAGGCCACC
2839  64_HRV90    GATCACTACAAGAATATACCATAAAGCAAAACACATTAAGGTTTGGTGTCCAAGACCACC
2840  65_HRV90a|  GATCACTACAAGAATATACCATAAAGCAAAACACATTAAGGTTTGGTGTCCAAGACCACC
2841  66_HRV90b|  GATCACTACAAGAATATACCATAAAGCAAAACACATTAAGGTTTGGTGTCCAAGACCACC
2842  67_HRV34    AATAACAACTAGAGTTTATCACAAAGCTAAACATGTAAAAACCTGGTGTCCAAGACCACC
2843  68_HRV34b|  AATAACAACTAGAGTTTATCACAAAGCTAAACATGTAAAAACCTGGTGTCCAAGACCACC
2844  69_HRV34a|  AATAACAACTAGAGTTTATCACAAAGCTAAACATGTAAAAACCTGGTGTCCAAGACCACC
2845  70_HRV50a|  AATCACAACCAGAGTATACCATAAAGCCAAACACATAAAAGTCTGGTGTCCAAGACCACC
2846  71_HRV50b|  AATCACAACCAGAGTATACCATAAAGCCAAACACATAAAAGTCTGGTGTCCAAGACCACC
2847  72_HRV50    AATCACAACCAGAGTATACCATAAAGCCAAACACATAAAAGTCTGGTGTCCAAGACCACC
2848  73_HRV18a   AATAACAACTAGAATACCACAAGGCAAAACATGTTAAAGCATGGTGCCCAAGGCCACC
2849  74_HRV18b|  AATAACAACCAGAATATACCACAAGGCAAAACATGTTAAAGCATGGTGCCCAAGGCCACC
2850  75_HRV18    AATAACAACCAGAATATACCACAAGGCAAAACATGTTAAAGCATGGTGCCCAAGGCCACC
2851  76_HRV55    AGTGACGACAAGAGTCTATCATAAAGCTAAACATCAAAGCATGGTGCCCACGACCACC
2852  77_HRV55b|  AGTGACGACAAGAGTCTATCATAAAGCTAAACATCAAAGCATGGTGCCCACGACCACC
2853  78_HRV55a|  AGTGACGACAAGAGTCTATCATAAAGCTAAACATCAAAGCATGGTGCCCACGACCACC
2854  79_HRV57    AATAACAACCAGAGTGTATCACAAAGCCAAACATGTCAAAGCCTGGTGCCCTAGACCACC
2855  80_HRV57a|  AATAACAACCAGAGTGTATCACAAAGCCAAACATGTCAAAGCCTGGTGCCCTAGACCACC
```

FIG. D11 CONT'D

07.trace                                                                 9/20/2007 5:04 PM

```
2856  81_HRV57b|  AATAACAACCAGAGTGTATCACAAAGCCAAACATGTCAAAGCCTGGTGCCCTAGACCACC
2857  82_HRV21    AGTGACCACAAGAATATACCATAAGGCAAAGCATGTTAAAGCTTGGTGCCCCAGACCACC
2858  83_HRVHan   AGTGACCACAAGAATATACCATAAGGCAAAGCATGTTAAAGCTTGGTGCCCTAGACCACC
2859  84_HRV43    GATAACTACCAGGATATATCATAAAGCCAAGCATATCAAAGCTTGGTGCCCAAGACCACC
2860  85_HRV43b|  GATAACTACCAGGATATATCATAAAGCCAAGCATATCAAAGCTTGGTGCCCAAGACCACC
2861  86_HRV43a|  GATAACTACCAGGATATATCATAAAGCCAAGCATATCAAAGCTTGGTGCCCAAGACCACC
2862  87_HRV75    AGTAACCACTAGAATATATCACAAAGCCAAACATATAAAAGCTTGGTGTCCGAGGCCGCC
2863  88_HRV75b|  AGTAACCACTAGAATATATCACAAAGCCAAACATATAAAAGCTTGGTGTCCGAGGCCGCC
2864  89_HRV75a|  AGTAACCACTAGAATATATCACAAAGCCAAACATATAAAAGCTTGGTGTCCGAGGCCGCC
2865  96_HRV9a|d  AATTTCAACCAGAATATATCACAAAGCCAAACATGTTAAAGCCTGGTGCCCAAGACCTCC
2866  97_HRV9b|d  AATTTCAACCAGAATATATCACAAAGCCAAACATGTTAAAGCCTGGTGCCCAAGACCTCC
2867  98_HRV9     AATTTCAACCAGAATATATCACAAAGCCAAACATGTTAAAGCCTGGTGCCCAAGACCTCC
2868  99_HRV32    TATTTCAACTAGGGTATATCACAAAGCTAAACACGTCAAAGCTTGGTGCCCACGACCACC
2869  100_HRV32a  TATTTCAACTAGGGTATATCACAAAGCTAAACACGTCAAAGCTTGGTGCCCACGACCACC
2870  101_HRV32b  TATTTCAACTAGGGTATATCACAAAGCTAAACACGTCAAAGCTTGGTGCCCACGACCACC
2871  102_HRV67   AATTGCAACGCGGGTGTATCATAAGGCTAAACATGTAAAAGCTTGGTGCCCAAGGCCCCC
2872  103_HRV67a  AATTGCAACGCGGGTGTATCATAAGGCTAAACATGTAAAAGCTTGGTGCCCAAGGCCCCC
2873  104_HRV67b  AATTGCAACGCGGGTGTATCATAAGGCTAAACATGTAAAAGCTTGGTGCCCAAGGCCCCC
2874  105_HRV15   GATTACAACTAGAGTGTATCACAAAGCTAAACATGTAAAGGCTTGGTGCCCCAGACCCCC
2875  106_HRV15a  GATTACAACTAGAGTGTATCACAAAGCTAAACATGTAAAGGCTTGGTGCCCCAGACCCCC
2876  107_HRV15b  GATTACAACTAGAGTGTATCACAAAGCTAAACATGTAAAGGCTTGGTGCCCCAGACCCCC
2877  108_HRV74a  AATTACAACTAGAGTGTACCATAAAGCAAAGCATGTGAAGGCATGGTGTCCTAGACCCCC
2878  109_HRV74b  AATTACAACTAGAGTGTACCATAAAGCAAAGCATGTGAAGGCATGGTGTCCTAGACCCCC
2879  110_HRV74   AATTACAACTAGAGTGTACCATAAAGCAAAGCATGTGAAGGCATGGTGTCCTAGACCCCC
2880  111_HRV38a  GATAACAACTAGAATTTATCATAAGGCAAAACATGTAAAAGCCTGGTGTCCAAGACCCCC
2881  112_HRV38b  GATAACAACTAGAATTTATCATAAGGCAAAACATGTAAAAGCCTGGTGTCCAAGACCCCC
2882  113_HRV38   GATAACAACTAGAATTTATCATAAGGCAAAACATGTAAAAGCCTGGTGTCCAAGACCCCC
2883  114_HRV60   CGTCGCAACAAGAATATATCATAAAGCAAAGCATGTTAAGGCTTGGTGTCCAAGACCTCC
2884  115_HRV60a  CGTCGCAACAAGAATATATCATAAAGCAAAGCATGTTAAGGCTTGGTGTCCAAGACCTCC
2885  116_HRV60b  CGTCGCAACAAGAATATATCATAAAGCAAAGCATGTTAAGGCTTGGTGTCCAAGACCTCC
2886  117_HRV64a  CATCACTACTAGGGTTTATCACAAAGCAAAACATGTCAAGGCATGGTGTCCACGGCCCCC
2887  118_HRV64b  CATCACTACTAGGGTTTATCACAAAGCAAAACATGTCAAGGCATGGTGTCCACGGCCCCC
2888  119_HRV64   CATCACTACTAGGGTTTATCACAAAGCAAAACATGTCAAGGCATGGTGTCCACGGCCCCC
2889  120_HRV94a  CATCACTACTAGAGTGTACCACAAAGCAAAACATGTGAAAGCGTGGTGCCCGCGCCCTCC
2890  121_HRV94b  CATCACTACTAGAGTGTACCACAAAGCAAAACATGTGAAAGCGTGGTGCCCGCGCCCTCC
2891  122_HRV94   CATCACTACTAGAGTGTACCACAAAGCAAAACATGTGAAAGCGTGGTGCCCGCGCCCTCC
2892  123_HRV22   AATTACAACTAGAGTGTACCACAAAGCAAAACATGTAAAGGCATGGTGCCCACGTCCTCC
2893  124_HRV22a  AATTACAACTAGAGTGTACCACAAAGCAAAACATGTAAAGGCATGGTGCCCACGTCCTCC
2894  125_HRV22b  AATTACAACTAGAGTGTACCACAAAGCAAAACATGTAAAGGCATGGTGCCCACGTCCTCC
2895  126_HRV82   CATTACCACAAGAATATATCACAAAGCAAAACATGTGAAAGCGTGGTGTCCACGACCCCC
2896  127_HRV82b  CATTACCACAAGAATATATCACAAAGCAAAACATGTGAAAGCGTGGTGTCCACGACCCCC
2897  128_HRV82a  CATTACCACAAGAATATATCACAAAGCAAAACATGTGAAAGCGTGGTGTCCACGACCCCC
2898  129_HRV19   AATCACAACTAGAGTATATCATAAAGCTAAACATATAAAAGCTTGGTGCCCACGACCACC
2899  130_HRV19a  AATCACAACTAGAGTATATCATAAAGCTAAACATATAAAAGCTTGGTGCCCACGACCACC
2900  131_HRV19b  AATCACAACTAGAGTATATCATAAAGCTAAACATATAAAAGCTTGGTGCCCACGACCACC
2901  132_HRV13   GGTTACAACTAGAATCTATCATAAAGCTAAACATGTCAAAGCATGGTGTCCTAGACCTCC
2902  133_HRV13a  GGTTACAACTAGAATCTATCATAAAGCTAAACATGTCAAAGCATGGTGTCCTAGACCTCC
2903  134_HRV13b  GGTTACAACTAGAATCTATCATAAAGCTAAACATGTCAAAGCATGGTGTCCTAGACCTCC
2904  135_HRV41   GGTCACAACTAGAGTTTACCACAAAGCTAAACATGTAAAGCATGGTGTCCTAGACCTCC
2905  136_HRV41a  GGTCACAACTAGAGTTTACCACAAAGCTAAACATGTTAAAGCATGGTGTCCTAGACCTCC
2906  137_HRV41b  GGTCACAACTAGAGTTTACCACAAAGCTAAACATGTTAAAGCATGGTGTCCTAGACCTCC
2907  138_HRV73   GGTTACTACTAGAATCTATCATAAGGCTAAACATGTTAAAGCTTGGTGTCCAAGACCTCC
2908  139_HRV73b  GGTTACTACTAGAATCTATCAAAGGCTAAACATGTTAAAGCTTGGTGTCCAAGACCTCC
2909  140_HRV73a  GGTTACTACTAGAATCTATCATAAGGCTAAACATGTTAAAGCTTGGTGTCCAAGACCTCC
2910  141_HRV61   AATCACAACTAGGATTTACCATAAAGCTAAACATGTTAAAGTCTGGTGTCCTAGACCCCC
2911  142_HRV61a  AATCACAACTAGGATTTACCATAAAGCTAAACATGTTAAAGTCTGGTGTCCTAGACCCCC
2912  143_HRV61b  AATCACAACTAGGATTTACCATAAAGCTAAACATGTTGGTGTCCTAGACCCCC
2913  144_HRV96   AATTACAACCAGAGTTTACCACAAAGCTAAACATGTTAAGGTGTGGTGCCCGAGACCCCC
2914  145_HRV96b  AATTACAACCAGAGTTTACCACAAAGCTAAACATGTTAAGGTGTGGTGCCCGAGACCCCC
2915  146_HRV96a  AATTACAACCAGAGTTTACCACAAAGCTAAACATGTTAAGGTGTGGTGCCCGAGACCCCC
2916  90_HRV16a|  AGTGGTAACAAGGATATATCACAAAGCCAAACACACCAAAGCTTGGTGCCCAAGACCACC
2917  91_HRV16b|  AGTGGTAACAAGGATATATCACAAAGCCAAACACACCAAAGCTTGGTGCCCAAGACCACC
2918  92_1AYM_A   AGTGGTAACAAGGATATATCACAAAGCCAAACACACCAAAGCTTGGTGCCCAAGACCACC
2919  93_HRV81a|  AATAGTAACAAGAATATATCACAAAGCTAAGCACACCAAAGCTTGGTGTCCAAGACCACC
2920  94_HRV81b|  AATAGTAACAAGAATATATCACAAAGCTAAGCACACCAAAGCTTGGTGTCCAAGACCACC
```

FIG. D11 CONT'D 07.trace                                                                  9/20/2007 5:04 PM

```
2921  95_HRV81    AATAGTAACAAGAATATATCACAAAGCTAAGCACACCAAAGCTTGGTGTCCAAGACCACC
2922 147_HRV2     TATAATGACAAGAATCTATCACAAGGCTAAACATGTCAAGGCATGGTGTCCACGCCCACC
2923 148_HRV2a|   TATAATGACAAGAATCTATCACAAGGCTAAACATGTCAAGGCATGGTGTCCACGCCCACC
2924 149_HRV2b|   TATAATGACAAGAATCTATCACAAGGCTAAACATGTCAAGGCATGGTGTCCACGCCCACC
2925 150_HRV49a   TATCATGACAAGAATCTATCATAAAGCTAAACACGTCAAAGCATGGTGTCCGCGCCCACC
2926 151_HRV49b   TATCATGACAAGAATCTATCATAAAGCTAAACACGTCAAAGCATGGTGTCCGCGCCCACC
2927 152_HRV49    TATCATGACAAGAATCTATCATAAAGCTAAACACGTCAAAGCATGGTGTCCGCGCCCACC
2928 153_HRV23a   GATAATGACAAGGGTCTACCACAAAGCTAAACATGTCAAAGCATGGTGTCCGCGGCCACC
2929 154_HRV23b   GATAATGACAAGGGTCTACCACAAAGCTAAACATGTCAAAGCATGGTGTCCGCGGCCACC
2930 155_HRV23    GATAATGACAAGGGTCTACCACAAAGCTAAACATGTCAAAGCATGGTGTCCGCGGCCACC
2931 156_HRV30a   CATAATGACAAGGGTCTACCACAAGGCTAAACATGTCAAAGCGTGGTGTCCACGGCCACC
2932 157_HRV30b   CATAATGACAAGGGTCTACCACAAGGCTAAACATGTCAAAGCGTGGTGTCCACGGCCACC
2933 158_HRV30    CATAATGACAAGGGTCTACCACAAGGCTAAACATGTCAAAGCGTGGTGTCCACGGCCACC
2934 159_HRV7     GATTGTGAGTCGCATTTACCACAAAGCCAAACATATAAAAGCATGGTGCCCACGCCCACC
2935 160_HRV7b|   GATTGTGAGTCGCATTTACCACAAAGCCAAACATATAAAAGCATGGTGCCCACGCCCACC
2936 161_HRV7a|   GATTGTGAGTCGCATTTACCACAAAGCCAAACATATAAAAGCATGGTGCCCACGCCCACC
2937 162_HRV88    TATCATTAGCCGTATATATCACAAGGCTAAACATATAAAAGCATGGTGTCCACGCCCACC
2938 163_HRV88a   TATCATTAGCCGTATATATCACAAGGCTAAACATATAAAGGCATGGTGTCCACGCCCACC
2939 164_HRV88b   TATCATTAGCCGTATATATCACAAGGCTAAACATATAAAGGCATGGTGTCCACGCCCACC
2940 165_HRV36a   TATTGTATGCCGCATTTATCATAAAGCTAAACACATAAAGGCCTGGTGCCCGCGTCCACC
2941 166_HRV36b   TATTGTATGCCGCATTTATCATAAAGCTAAACACATAAAGGCCTGGTGCCCGCGTCCACC
2942 167_HRV36    TATTGTATGCCGCATTTATCATAAAGCTAAACACATAAAGGCCTGGTGCCCGCGTCCACC
2943 168_HRV89a   TATTGTGTGCCGCATTTACCACAAGGCCAAACATATAAAAGCATGGTGTCCTCGCCCACC
2944 169_HRV89b   TATTGTGTGCCGCATTTACCACAAGGCCAAACATATAAAAGCATGGTGTCCTCGCCCACC
2945 170_HRV89    TATTGTGTGCCGCATTTACCACAAGGCCAAACATATAAAAGCATGGTGTCCTCGCCCACC
2946 171_HRV58    CATTGTCTGTCGCATTTACCACAAAGCCAAGCATATAAAGCATGGTGTCCACGCCCACC
2947 172_HRV58a   CATTGTCTGTCGCATTTACCACAAAGCCAAGCATATAAAGCATGGTGTCCACGCCCACC
2948 173_HRV58b   CATTGTCTGTCGCATTTACCACAAAGCCAAGCATATAAAGCATGGTGTCCACGCCCACC
2949 174_HRV12a   GATTACCAGTAGAATATACCATAAAGCAAAACATATCAGTGCCTGGGGCCCTAGACCACC
2950 175_HRV12b   GATTACCAGTAGAATATACCATAAAGCAAAACATATCAGTGCCTGGGGCCCTAGACCACC
2951 176_HRV12    GATTACCAGTAGAATATACCATAAAGCAAAACATATCAGTGCCTGGGGCCCTAGACCACC
2952 177_HRV78a   AATTACAGCTAGAGTCTACCACAAGGCCAAACATATTAGTGCATGGGGCCCAAGACCTCC
2953 178_HRV78b   AATTACAGCTAGAGTCTACCACAAGGCCAAACATATTAGTGCATGGGGCCCAAGACCTCC
2954 179_HRV78    AATTACAGCTAGAGTCTACCACAAGGCCAAACATATTAGTGCATGGGGCCCAAGACCTCC
2955 180_HRV20    GATAACCAGTAGGATATTCCACAAGGCAAAGCATATTAGTGCATGGTGTCCAAGGGCCCC
2956 181_HRV20a   GATAACCAGTAGGATATTCCACAAGGCAAAGCATATTAGTGCATGGTGTCCAAGGGCCCC
2957 182_HRV20b   GATAACCAGTAGGATATTCCACAAGGCAAAGCATATTAGTGCATGGTGTCCAAGGGCCCC
2958 183_HRV68    AATAACCAGCAGAATATTCCATAAAGCAAAACATATTAGTGCGTGGTGTCCAAGAGCTCC
2959 184_HRV68a   AATAACCAGCAGAATATTCCATAAAGCAAAACATATTAGTGCGTGGTGTCCAAGAGCTCC
2960 185_HRV68b   AATAACCAGCAGAATATTCCATAAAGCAAAACATATTAGTGCGTGGTGTCCAAGAGCTCC
2961 186_HRV28    AATAACCAGCATAATATTCCACAAAGCTAAACATGTCAGTGCATGGTGCCCCAGACCTCC
2962 187_HRV28a   AATAACCAGCATAATATTCCACAAAGCTAAACATGTCAGTGCATGGTGCCCCAGACCTCC
2963 188_HRV28b   AATAACCAGCATAATATTCCACAAAGCTAAACATGTCAGTGCATGGTGCCCCAGACCTCC
2964 189_HRV53a   GATAACCAGTAGGATTTATCACAAGGCTAAACATATCAGTGCATGGTGTCCAAGACCACC
2965 190_HRV53b   GATAACCAGTAGGATTTATCACAAGGCTAAACATATCAGTGCATGGTGTCCAAGACCACC
2966 191_HRV53    GATAACCAGTAGGATTTATCACAAGGCTAAACATATCAGTGCATGGTGTCCAAGACCACC
2967 192_HRV46a   TATAACTAGCAGAATATATCACAAGGCTAAACACATTAAAGCATGGTGCCCCAGGGCACC
2968 193_HRV46b   TATAACTAGCAGAATATATCACAAGGCTAAACACATTAAAGCATGGTGCCCCAGGGCACC
2969 194_HRV46    TATAACTAGCAGAATATATCACAAGGCTAAACACATTAAAGCATGGTGCCCCAGGGCACC
2970 195_HRV80a   AATCACCAGCAGAATATATCACAAAGCTAAACATCAAAGCATGGTGTCCAAGAGCACC
2971 196_HRV80b   AATCACCAGCAGAATATATCACAAAGCTAAACATCAAAGCATGGTGTCCAAGAGCACC
2972 197_HRV80    AATCACCAGCAGAATATATCACAAAGCTAAACATCAAAGCATGGTGTCCAAGAGCACC
2973 198_HRV51    CATAACTAGCAGGATTTACCACAAAGCCAAACATGTCAGTGCATGGTGCCCTCGTCCTCC
2974 199_HRV51a   CATAACTAGCAGGATTTACCACAAAGCCAAACATGTCAGTGCATGGTGCCCTCGTCCTCC
2975 200_HRV51b   CATAACTAGCAGGATTTACCACAAAGCCAAACATGTCAGTGCATGGTGCCCTCGTCCTCC
2976 201_HRV65a   CATAACCAGTAGAATATATCATAAAGCTAAACACATCAGTGCTTGGTGTCCACGACCTCC
2977 202_HRV65b   CATAACCAGTAGAATATATCATAAAGCTAAACACATCAGTGCTTGGTGTCCACGACCTCC
2978 203_HRV65    CATAACCAGTAGAATATATCATAAAGCTAAACACATCAGTGCTTGGTGTCCACGACCTCC
2979 204_HRV71a   CATAACAAGTAGGATTTATCACAAAGCCAAACATGTCAGAGCATGGTGTCCTAGACCCCC
2980 205_HRV71b   CATAACAAGTAGGATTTATCACAAAGCCAAACATGTCAGAGCATGGTGTCCTAGACCCCC
2981 206_HRV71    CATAACAAGTAGGATTTATCACAAAGCCAAACATGTCAGAGCATGGTGTCCTAGACCCCC
2982 207_HRV8     AATTGATTCAAGAATATACCTGAAAGCAAAGCACATTAAAGCTTGGTGTCCTAGACCCCC
2983 208_HRV95    AATTGATTCAAGAATATACCTGAAAGCAAAGCATATTAAAGCTTGGTGTCCTAGACCCCC
2984 209_HRV45    GATCGACTCCATGGTATATCTAAAAGCTAAACACATCAAGGCATGGTGTCCCAGACCTCC
2985 210_HRV45a   GATCGACTCCATGGTATATCTAAAAGCTAAACACATCAAGGCATGGTGTCCCAGACCTCC
```

FIG. D11 CONT'D

```
07.trace                                                                        9/20/2007 5:04 PM 2986 211_HRV45b   GATCGACTCCATGGTATATCTAAAAGCTAAACACATCAAGGCATGGTGTCCCAGACCTCC
2987 GROUP_1     --T-----------T-T--C--AA-GC-AA-CA---------TGG-G-CC--G--C-C-
2988
2989  1_HRV1A1|d    TAGAGCTGTCCCTTACACA-CATAGTCATGTGACTAATTATATGC-CAGAAA---CAGGT
2990  2_HRV1A2|d    TAGAGCTGTCCCTTACACA-CATAGTCATGTGACTAATTATATGC-CAGAAA---CAGGT
2991  3_HRV1A|cD    TAGAGCTGTCCCTTACACA-CATAGTCATGTGACTAATTATATGC-CAGAAA---CAGGT
2992  4_HRV1B1|d    TAGAGCTGTTCCTTACACA-CATAGTCGTGTAACTAATTATGTAC-CAAAAA---CAGGT
2993  5_HRV1B2|d    TAGAGCTGTTCCTTACACA-CATAGTCGTGTAACTAATTATGTAC-CAAAAA---CAGGT
2994  6_HRV1B       TAGAGCTGTTCCTTACACA-CATAGTCGTGTAACTAATTATGTAC-CAAAAA---CAGGT
2995  7_HRV40a|d    AAGAGCAGTACCTTACACA-CATACACACTCAACAAATTATAAAC-CTCAAG---AAGGT
2996  8_HRV40b|d    AAGAGCAGTACCTTACACA-CATACACACTCAACAAATTATAAAC-CTCAAG---AAGGT
2997  9_HRV40       AAGAGCAGTACCTTACACA-CATACACACTCAACAAATTATAAAC-CTCAAG---AAGGT
2998 10_HRV85       AAGAGCGGTGCCTTATACA-CACACACGCTCAACCAACTATGTGC-CACAAG---ATGGT
2999 11_HRV85a|     AAGAGCGGTGCCTTATACA-CACACACGCTCAACCAACTATGTGC-CACAAG---ATGGT
3000 12_HRV85b|     AAGAGCGGTGCCTTATACA-CACACACGCTCAACCAACTATGTGC-CACAAG---ATGGT
3001 13_HRV56a|     AAGGGCTGTGCCTTATACA-CATGCTCACGTCACCAATTATAAAC-CACAAG---ATGGT
3002 14_HRV56b|     AAGGGCTGTGCCTTATACA-CATGCTCACGTCACCAATTATAAAC-CACAAG---ATGGT
3003 15_HRV56       AAGGGCTGTGCCTTATACA-CATGCTCACGTCACCAATTATAAAC-CACAAG---ATGGT
3004 16_HRV54       TAGGGCTGTCCCATACACA-CATACTAGATCAACAAATTACATGC-CACGGG---AGGGT
3005 17_HRV98       TAGAGCTGTTCCATACACA-CACACTAGATCAACTAATTACATGC-CTCAAG---ATGGT
3006 18_HRV59a|     TAGAGCAGTCCCTTACACA-CACAGCTACGTAACTAACTACAAGATTGCTGG---AAAA-
3007 19_HRV59b|     TAGAGCAGTCCCTTACACA-CACAGCTACGTAACTAACTACAAGATTGCTGG---AAAA-
3008 20_HRV59       TAGAGCAGTCCCTTACACA-CACAGCTACGTAACTAACTACAAGATTGCTGG---AAAA-
3009 21_HRV63       TAGGGCTGTTCCATACACA-CATAGTTATGTCACTAACTATAAAATTACAGG---ACAG-
3010 22_HRV63b|     TAGGGCTGTTCCATACACA-CATAGTTATGTCACTAACTATAAAATTACAGG---ACAG-
3011 23_HRV63a|     TAGGGCTGTTCCATACACA-CATAGTTATGTCACTAACTATAAAATTACAGG---ACAG-
3012 24_HRV39       CAGAGCAGTCCCTTACACA-CACAGCAATGTTACAAATTACAAAG-TACGGG---ACGGT
3013 25_HRV39a|     CAGAGCAGTCCCTTACACA-CACAGCAATGTTACAAATTACAAAG-TACGGG---ACGGT
3014 26_HRV39b|     CAGAGCAGTCCCTTACACA-CACAGCAATGTTACAAATTACAAAG-TACGGG---ACGGT
3015 27_HRV10a|     CAGAGCTGTACCATATACA-CATGCCCATTCCACAAATTACAAAC-CACATG---GCAAA
3016 28_HRV10b|     CAGAGCTGTACCATATACA-CATGCCCATTCCACAAATTACAAAC-CACATG---GCAAA
3017 29_HRV10       CAGAGCTGTACCATATACA-CATGCCCATTCCACAAATTACAAAC-CACATG---GCAAA
3018 30_HRV100a     TCGGGCTGTGCCGTACACA-CATAGTCACTCTACAAATTACAAAC-CACATG---AGGGT
3019 31_HRV100b     TCGGGCTGTGCCGTACACA-CATAGTCACTCTACAAATTACAAAC-CACATG---AGGGT
3020 32_HRV100      TCGGGCTGTGCCGTACACA-CATAGTCACTCTACAAATTACAAAC-CACATG---AGGGT
3021 33_HRV66       TAGAGCTGTACCATACACA-ACTGTAAACTCAACCAATTATATGC-CTCATA---CTGGT
3022 34_HRV66b|     TAGAGCTGTACCATACACA-ACTGTAAACTCAACCAATTATATGC-CTCATA---CTGGT
3023 35_HRV66a|     TAGAGCTGTACCATACACA-ACTGTAAACTCAACCAATTATATGC-CTCATA---CTGGT
3024 36_HRV77a|     TAGAGCTGTACCATACACA-GCAGTAGATTCAACAAATTACAAAC-CTATGA---GAGGG
3025 37_HRV77b|     TAGAGCTGTACCATACACA-GCAGTAGATTCAACAAATTACAAAC-CTATGA---GAGGG
3026 38_HRV77       TAGAGCTGTACCATACACA-GCAGTAGATTCAACAAATTACAAAC-CTATGA---GAGGG
3027 39_HRV62a      CAGAGCTGTTCCATATAAA-TATGTTGATTTCAATAATTATGCAG-CCAGTG---ATAGT
3028 40_HRV62b      TAGAGCTGTTCCATATAAA-TATGTTGATTTCAATAATTATGCAG-CCAGTG---ATAGT
3029 41_HRV25       TAGAGCTGTCCCATATAAA-TATGTTGACTTCAATAATTATGCAG-CCAGTG---ATAAT
3030 42_HRV29a      AAGAGTTGTCCCATACAAG-TATGTTGGCCTAACTAATTACACAC-TTAAAG---AAGAA
3031 43_HRV29b      AAGAGTTGTCCCATACAAG-TATGTTGGCCTAACTAATTACACAC-TTAAAG---AAGAA
3032 44_HRV44a      AAGGGTTGTCCCATACAAG-TATGTTGGCCTAACTAATTACACAC-TTAAAG---AAACA
3033 45_HRV44b      AAGGGTTGTCCCATACAAG-TATGTTGGCCTAACTAATTACACAC-TTAAAG---AAACA
3034 46_HRV31       TAGAGCAGTTCCATACAGGGTATG-TGGATCAACAAACTACAAAC-CTGATG---AAAAT
3035 47_HRV31a|     TAGAGCAGTTCCATACAGGGTATG-TGGATCAACAAACTACAAAC-CTGATG---AAAAT
3036 48_HRV31b|     TAGAGCAGTTCCATACAGG-TATGTTGGATCAACAAACTACAAAC-CTGATG---AAAAT
3037 49_HRV47       TAGAGCTGTTCCATATAGA-TATGTTGGATCAACAAATTACAAAC-CTGATC---AAGGA
3038 50_HRV47a|     TAGAGCTGTTCCATATAGA-TATGTTGGATCAACAAATTACAAAC-CTGATC---AAGGA
3039 51_HRV47b|     TAGAGCTGTTCCATATAGA-TATGTTGGATCAACAAATTACAAAC-CTGATC---AAGGA
3040 52_HRV11       TAGAGCTGTAGAATATACT-CACACTCATGTAACCAATTACAAAC-CACAGG---AAGGA
3041 53_HRV11b|     TAGAGCTGTAGAATATACT-CACACTCATGTAACCAATTACAAAC-CACAGG---AAGGA
3042 54_HRV11a|     TAGAGCTGTAGAATATACT-CACACTCATGTAACCAATTACAAAC-CACAGG---AAGGA
3043 55_HRV76       TAGAGCTGTAGAGTATACA-TACACCCATGTAACAAACTACAAAC-CACATT---CTGGT
3044 56_HRV76b|     TAGAGCTGTAGAGTATACA-TACACCCATGTAACAAACTACAAAC-CACATT---CTGGT
3045 57_HRV76a|     TAGAGCTGTAGAGTATACA-TACACCCATGTAACAAACTACAAAC-CACATT---CTGGT
3046 58_HRV33       TAGAGCTGTGGAATACACC-CATACTCATGTTACAAATTACAAAT-CAACAA---CTCGT
3047 59_HRV33b|     TAGAGCTGTGGAATACACC-CATACTCATGTTACAAATTATAAAT-CAACAA---CTCGT
3048 60_HRV33a|     TAGAGCTGTGGAATACACC-CATACTCATGTTACAAATTATAAAT-CAACAA---CTCGT
3049 61_HRV24a|     CAGAGCTGTTGAGTATACA-CATACTCACGTGACCAATTATAAGC-ATCAGA---CTCGT
3050 62_HRV24b|     CAGAGCTGTTGAGTATACA-CATACTCACGTGACCAATTATAAGC-ATCAGA---CTCGT
```

FIG. D11 CONT'D

```
07.trace                                                               9/20/2007 5:04 PM 3051  63_HRV24     CAGAGCTGTTGAGTATACA-CATACTCACGTGACCAATTATAAGC-ATCAGA---CTCGT
3052  64_HRV90     TAGGGCAGTTGAATACACA-CACACTCATGTAACAAACTACAAAC-ATGCAA---CACGT
3053  65_HRV90a|   TAGGGCAGTTGAATACACA-CACACTCATGTAACAAACTACAAAC-ATGCAA---CACGT
3054  66_HRV90b|   TAGGGCAGTTGAATACACA-CACACTCATGTAACAAACTACAAAC-ATGCAA---CACGT
3055  67_HRV34     AAGAGCTGTTGAGTACACA-CACACACATGTTACTAACTACAAAG-TTAGGG---GTAAA
3056  68_HRV34b|   AAGAGCTGTTGAGTACACA-CACACACATGTTACTAACTACAAAG-TTAGGG---GTAAA
3057  69_HRV34a|   AAGAGCTGTTGAGTACACA-CACACACATGTTACTAACTACAAAG-TTAGGG---GTAAA
3058  70_HRV50a|   AAGAGCTGTTGAATACACA-CACACCCATGTCACTAACTACAAGA-AAAGTG---ATGCT
3059  71_HRV50b|   AAGAGCTGTTGAATACACA-CACACCCATGTCACTAACTACAAGA-AAAGTG---ATGCT
3060  72_HRV50     AAGAGCTGTTGAATACACA-CACACCCATGTCACTAACTACAAGA-AAAGTG---ATGCT
3061  73_HRV18a|   GAGAGCTGTGGAGTACACA-CATACACATGTAACTAACTACAAGC-CTAAGG---AAGGA
3062  74_HRV18b|   GAGAGCTGTGGAGTACACA-CATACACATGTAACTAACTACAAGC-CTAAGG---AAGGA
3063  75_HRV18     GAGAGCTGTGGAGTACACA-CATACACATGTAACTAACTACAAGC-CTAAGG---AAGGA
3064  76_HRV55     TAGGGCTGTTGAATACACA-CACACACATGTCACAAATTACAAGA-AGACTG---ATGGC
3065  77_HRV55b|   TAGGGCTGTTGAATACACA-CACACACATGTCACAAATTACAAGA-AGACTG---ATGGC
3066  78_HRV55a|   TAGGGCTGTTGAATACACA-CACACACATGTCACAAATTACAAGA-AGACTG---ATGGC
3067  79_HRV57     ACGGGCTATCGAGTACACA-CATACACATGTTACTAATTATAAAA-TAAAAG---ATAGA
3068  80_HRV57a|   ACGGGCTATCGAGTACACA-CATACACATGTTACTAATTATAAAA-TAAAAG---ATAGA
3069  81_HRV57b|   ACGGGCTATCGAGTACACA-CATACACATGTTACTAATTATAAAA-TAAAAG---ATAGA
3070  82_HRV21     GAGGGCCGTTGAATACACA-CATACACACGTAACCAATTACAAAA-TTGCAA---ATCAT
3071  83_HRVHan    GAGGGCCGTTGAATACACA-CATACACATGTAACCAATTACAAAA-TTGCAA---ATAAA
3072  84_HRV43     CAGAGCTGTTGAATACACA-CACACACATGTCACAAATTATAAAA-GAGAAG---GAAAG
3073  85_HRV43b|   CAGAGCTGTTGAATACACA-CACACACATGTCACAAATTATAAAA-GAGAAG---GAAAG
3074  86_HRV43a|   CAGAGCTGTTGAATACACA-CACACACATGTCACAAATTATAAAA-GAGAAG---GAAAG
3075  87_HRV75     CAGGGCTGTTGAATACACA-TTTAGACGTGTAACAAATTACAAAA-GAGATG---GACAA
3076  88_HRV75b|   CAGGGCTGTTGAATACACA-TTTAGACGTGTAACAAATTACAAAA-GAGATG---GACAA
3077  89_HRV75a|   CAGGGCTGTTGAATACACA-TTTAGACGTGTAACAAATTACAAAA-GAGATG---GACAA
3078  96_HRV9a|d   TAGGGCAGTTGAGTATATA-CATACACATGTCACAAATTACAAGC-CAAGCA---CAGGC
3079  97_HRV9b|d   TAGGGCAGTTGAGTATATA-CATACACATGTCACAAATTACAAGC-CAAGCA---CAGGC
3080  98_HRV9      TAGGGCAGTTGAGTATATA-CATACACATGTCACAAATTACAAGC-CAAGCA---CAGGC
3081  99_HRV32     TAGGGCAGTTGAATATACA-CATACACATGTTACAAATTACAAAC-CAAGCA---CAGGT
3082  100_HRV32a   TAGGGCAGTTGAATATACA-CATACACATGTTACAAATTACAAAC-CAAGCA---CAGGT
3083  101_HRV32b   TAGGGCAGTTGAATATACA-CATACACATGTTACAAATTACAAAC-CAAGCA---CAGGT
3084  102_HRV67    TAGAGCAGTTGAATACATA-CACACACATGTTACAAACTATAGAC-CAGAAA---CAGGT
3085  103_HRV67a   TAGAGCAGTTGAATACACA-CACACACATGTTACAAACTATAGAC-CAGAAA---CAGGT
3086  104_HRV67b   TAGAGCAGTTGAATACATA-CACACACATGTTACAAACTATAGAC-CAGAAA---CAGGT
3087  105_HRV15    TAGAGCAGTGGAATATACA-CACACACATGTCACAAATTACAAAC-CACAAG---ATGGT
3088  106_HRV15a   TAGAGCAGTGGAATATACA-CACACACATGTCACAAATTACAAAC-CACAAG---ATGGT
3089  107_HRV15b   TAGAGCAGTGGAATATACA-CACACACATGTCACAAATTACAAAC-CACAAG---ATGGT
3090  108_HRV74a   TAGAGCAGTTGAATATACT-CACACACATGTCACAAATTACAAAC-CACAAG---AAGGT
3091  109_HRV74b   TAGAGCAGTTGAATATACT-CACACACATGTCACAAATTACAAAC-CACAAG---AAGGT
3092  110_HRV74    TAGAGCAGTTGAATATACT-CACACACATGTCACAAATTACAAAC-CACAAG---AAGGT
3093  111_HRV38a   AAGGGCAGTTGAATATAGA-CATACACATGTTAACAATTACAAAC-CAGACC---AAGGG
3094  112_HRV38b   AAGGGCAGTTGAATATAGA-CATACACATGTTAACAATTACAAAC-CAGACC---AAGGG
3095  113_HRV38    AAGGGCAGTTGAATATAGA-CATACACATGTTAACAATTACAAAC-CAGACC---AAGGG
3096  114_HRV60    AAGGGCAGTTGAATATAGA-CACACACATGTAAACAACTATAGAC-CAGATG---ATGGA
3097  115_HRV60a   AAGGGCAGTTGAATATAGA-CACACACATGTAAACAACTATAGAC-CAGATG---ATGGA
3098  116_HRV60b   AAGGGCAGTTGAATATAGA-CACACACATGTAAACAACTATAGAC-CAGATG---ATGGA
3099  117_HRV64a   AAGAGCTGTTGGATATACA-CATACAAATGTCACCAATTATAAAC-CATCCA---AAGGA
3100  118_HRV64b   AAGAGCTGTTGGATATACA-CATACAAATGTCACCAATTATAAAC-CATCCA---AAGGA
3101  119_HRV64    AAGAGCTGTTGGATATACA-CATACAAATGTCACCAATTATAAAC-CATCCA---AAGGA
3102  120_HRV94a   AAGAGCTGTTGGATACACA-CATACGCATGTCACTAATTACAAAC-CATCTG---AAGGG
3103  121_HRV94b   AAGAGCTGTTGGATACACA-CATACGCATGTCACTAATTACAAAC-CATCTG---AAGGG
3104  122_HRV94    AAGAGCTGTTGGATACACA-CATACGCATGTCACTAATTACAAAC-CATCTG---AAGGG
3105  123_HRV22    AAGAGCTGTTGGATATACA-CACACACATGTGACAAACTACAAAC-CATCTG---TAGGG
3106  124_HRV22a   AAGAGCTGTTGGATATACA-CACACACATGTGACAAACTACAAAC-CATCTG---TAGGG
3107  125_HRV22b   AAGAGCTGTTGGATATACA-CACACACATGTGACAAACTACAAAC-CATCTG---TAGGG
3108  126_HRV82    GAGGGCTGTGGGTTATACA-CACACACATGTTACCAACTACAAGC-CATCAC---AGGGA
3109  127_HRV82b   GAGGGCTGTGGGTTATACA-CACACACATGTTACCAACTACAAGC-CATCAC---AGGGA
3110  128_HRV82a   GAGGGCTGTGGGTTATACA-CACACACATGTTACCAACTACAAGC-CATCAC---AGGGA
3111  129_HRV19    CAGAGCCGTGGAATATACC-CACACTCATGTGACTAATTATAAAC-CCCAGA---CAGGT
3112  130_HRV19a   CAGAGCCGTGGAATATACC-CACACTCATGTGACTAATTATAAAC-CCCAGA---CAGGT
3113  131_HRV19b   CAGAGCCGTGGAATATACC-CACACTCATGTGACTAATTATAAAC-CCCAGA---CAGGT
3114  132_HRV13    CAGAGCTGTTGAATATACT-AATGTGCATGTTACAAACTACAAAC-CAGGGA---CAGGA
3115  133_HRV13a   CAGAGCTGTTGAATATACT-AATGTGCATGTTACAAACTACAAAC-CAGGGA---CAGGA
```

FIG. D11 CONT'D 07.trace 9/20/2007 5:04 PM

```
3116 134_HRV13b    CAGAGCTGTTGAATATACT-AATGTGCATGTTACAAACTACAAAC-CAGGGA---CAGGA
3117 135_HRV41     CAGGGCTGTGGAGTACACC-AATGTGCATGTCACAAATTACAAAC-CAAAAG---CAGGA
3118 136_HRV41a    CAGGGCTGTGGAGTACACC-AATGTGCATGTCACAAATTACAAAC-CAAAAG---CAGGA
3119 137_HRV41b    CAGGGCTGTGGAGTACACC-AATGTGCATGTCACAAATTACAAAC-CAAAAG---CAGGA
3120 138_HRV73     TAGGGCAGTAGAATATACA-AATGCACATGTGACCAATTATAAAC-CCACTG---ATGGA
3121 139_HRV73b    TAGGGCAGTAGAATATACA-AATGCACATGTGACCAATTATAAAC-CCACTG---ATGGA
3122 140_HRV73a    TAGGGCAGTAGAATATACA-AATGCACATGTGACCAATTATAAAC-CCACTG---ATGGA
3123 141_HRV61     CAGAGCAGTGGAATATACT-AATGTGCATTTGACCAATTACAAGC-CCAAAG---ATAGT
3124 142_HRV61a    CAGAGCAGTGGAATATACT-AATGTGCATTTGACCAATTACAAGC-CCAAAG---ATAGT
3125 143_HRV61b    CAGAGCAGTGGAATATACT-AATGTGCATTTGACCAATTACAAGC-CCAAAG---ATAGT
3126 144_HRV96     TAGAGCAGTTGAATACACA-AATGTGCATCTCACAAATTATAAAC-CCAACA---ATG--
3127 145_HRV96b    TAGAGCAGTTGAATACACA-AATGTGCATCTCACAAATTATAAAC-CCAACA---ATG--
3128 146_HRV96a    TAGAGCAGTTGAATACACA-AATGTGCATCTCACAAATTATAAAC-CCAACA---ATG--
3129 90_HRV16a|    CAGAGCTGTTCAATACTCA-CATACACATACCACCAACTACAAAT-TGAGTT---CAGAA
3130 91_HRV16b|    CAGAGCTGTTCAATACTCA-CATACACATACCACCAACTACAAAT-TGAGTT---CAGAA
3131 92_1AYM_A     CAGAGCTGTTCAATACTCA-CATACACATACCACCAACTACAAAT-TGAGTT---CAGAA
3132 93_HRV81a|    CAGGGCTGTCAGTACACA-CATACACATGTAACTAATTATAAAT-TAGAAA---CAGAT
3133 94_HRV81b|    CAGGGCTGTTCAGTACACA-CATACACATGTAACTAATTATAAAT-TAGAAA---CAGAT
3134 95_HRV81      CAGGGCTGTTCAGTACACA-CATACACATGTAACTAATTATAAAT-TAGAAA---CAGAT
3135 147_HRV2      CAGAGCGCTTGAGTATACT-CGTGCTCACCGCACTAATTTTAAAA-TTGAGG---ATAGG
3136 148_HRV2a|    CAGAGCGCTTGAGTATACT-CGTGCTCACCGCACTAATTTTAAAA-TTGAGG---ATAGG
3137 149_HRV2b|    CAGAGCGCTTGAGTATACT-CGTGCTCACCGCACTAATTTTAAAA-TTGAGG---ATAGG
3138 150_HRV49a    CAGAGCACTTGAATATACT-CGCGCTCACCGTACTAATTTCAAAG-TTGAAG---ACAGA
3139 151_HRV49b    CAGAGCACTTGAATATACT-CGCGCTCACCGTACTAATTTCAAAG-TTGAAG---ACAGA
3140 152_HRV49     CAGAGCACTTGAATATACT-CGCGCTCACCGTACTAATTTCAAAG-TTGAAG---ACAGA
3141 153_HRV23a    CAGAGCACTTGAATACACA-CGCGCTCACCGTACTAATTTCAAAA-TTGAAG---GTGAA
3142 154_HRV23b    CAGAGCACTTGAATACACA-CGCGCTCACCGTACTAATTTCAAAA-TTGAAG---GTGAA
3143 155_HRV23     CAGAGCACTTGAATACACA-CGCGCTCACCGTACTAATTTCAAAA-TTGAAG---GTGAA
3144 156_HRV30a    TAGGGCGCTTGAGTATACC-CGTGCTCATCGCACCAATTTTAAAA-TTGATG---GCAGG
3145 157_HRV30b    TAGGGCGCTTGAGTATACC-CGTGCTCATCGCACCAATTTTAAAA-TTGATG---GCAGG
3146 158_HRV30     TAGGGCGCTTGAGTATACC-CGTGCTCATCGCACCAATTTTAAAA-TTGATG---GCAGG
3147 159_HRV7      ACGAGCTGTGCCTTATCAA-CACACTCACTCCACCAACTATGTGC-CACAAA---ATGGA
3148 160_HRV7b|    ACGAGCTGTGCCTTATCAA-CACACTCACTCCACCAACTATGTGC-CACAAA---ATGGA
3149 161_HRV7a|    ACGAGCTGTGCCTTATCAA-CACACTCACTCCACCAACTATGTGC-CACAAA---ATGGA
3150 162_HRV88     AAGAGCCGTACCTTATCAG-CACACACACTCCACCAATTATGTAC-CAACAG---ATGGG
3151 163_HRV88a    AAGAGCCGTACCTTATCAG-CACACACACTCCACCAATTATGTAC-CAACAG---ATGGG
3152 164_HRV88b    AAGAGCCGTACCTTATCAG-CACACACACTCCACCAATTATGTAC-CAACAG---ATGGG
3153 165_HRV36a    AAGGGCCGTTCCTTACCAA-CACACACATTCCACTAATTATATAC-CATACA---AAGGT
3154 166_HRV36b    AAGGGCCGTTCCTTACCAA-CACACACATTCCACTAATTATATAC-CATACA---AAGGT
3155 167_HRV36     AAGGGCCGTTCCTTACCAA-CACACACATTCCACTAATTATATAC-CATACA---AAGGT
3156 168_HRV89a    AAGGGCTGTTGCCTATCAA-CACACACACTCAACCAATTACATAC-CATCCA---ATGGT
3157 169_HRV89b    AAGGGCTGTTGCCTATCAA-CACACACACTCAACCAATTACATAC-CATCCA---ATGGT
3158 170_HRV89     AAGGGCTGTTGCCTATCAA-CACACACACTCAACCAATTACATAC-CATCCA---ATGGT
3159 171_HRV58     AAGGGCTGTTCCTTATCAA-TTCACACATTCTACTAATTACATAC-CAGATA---GTGGT
3160 172_HRV58a    AAGGGCTGTTCCTTATCAA-TTCACACATTCTACTAATTACATAC-CAGATA---GTGGT
3161 173_HRV58b    AAGGGCTGTTCCTTATCAA-TTCACACATTCTACTAATTACATAC-CAGATA---GTGGT
3162 174_HRV12a    AAGAGCTGTACCATACCAG-CATATACACAATCCAAATTACAAGA-CAAGTA------AT
3163 175_HRV12b    AAGAGCTGTACCATACCAG-CATATACACAATCCAAATTACAAGA-CAAGTA------AT
3164 176_HRV12     AAGAGCTGTACCATACCAG-CATATACACAATCCAAATTACAAGA-CAAGTA------AT
3165 177_HRV78a    TAGAGCTGTACCTTATCAG-CACATATATAACCCTAATTATAAAA-CTGAAG------AA
3166 178_HRV78b    TAGAGCTGTACCTTATCAG-CACATATATAACCCTAATTATAAAA-CTGAAG------AA
3167 179_HRV78     TAGAGCTGTACCTTATCAG-CACATATATAACCCTAATTATAAAA-CTGAAG------AA
3168 180_HRV20     AAGAGCAGTGCCTTATCAA-CACACTAAGAGCACAAACTTAGTGC-CAAGGA---CAGGT
3169 181_HRV20a    AAGAGCAGTGCCTTATCAA-CACACTAAGAGCACAAACTTAGTGC-CAAGGA---CAGGT
3170 182_HRV20b    AAGAGCAGTGCCTTATCAA-CACACTAAGAGCACAAACTTAGTGC-CAAGGA---CAGGT
3171 183_HRV68     AAGAGCAGTGCCCTACCAG-CACACCAGAAGTACAAACTTAGTAC-CAAAGG---AAGGT
3172 184_HRV68a    AAGAGCAGTGCCCTACCAG-CACACCAGAAGTACAAACTTAGTAC-CAAAGG---AAGGT
3173 185_HRV68b    AAGAGCAGTGCCCTACCAG-CACACCAGAAGTACAAACTTAGTAC-CAAAGG---AAGGT
3174 186_HRV28     ACGCGCTGTAGCTTATCAA-CATACATACAGTCCAAACTTTGTGC-CTCAGG---AAGGT
3175 187_HRV28a    ACGCGCTGTAGCTTATCAA-CATACATACAGTCCAAACTTTGTGC-CTCAGG---AAGGT
3176 188_HRV28b    ACGCGCTGTAGCTTATCAA-CATACATACAGTCCAAACTTTGTGC-CTCAGG---AAGGT
3177 189_HRV53a    AAGAGCAGTTGCATATCAA-CACACATATAGCCCAAATTTTGTAC-CGCAAA---CAGGA
3178 190_HRV53b    AAGAGCAGTTGCATATCAA-CACACATATAGCCCAAATTTTGTAC-CGCAAA---CAGGA
3179 191_HRV53     AAGAGCAGTTGCATATCAA-CACACATATAGCCCAAATTTTGTAC-CGCAAA---CAGGA
3180 192_HRV46a    CAGAGCAGTCCCATATCAA-CATATTTATAATCCAAATTTCAAGA-CTACTCAACCTGAG
```

FIG. D11 CONT'D

```
07.trace                                                            9/20/2007 5:04 PM 3181  193_HRV46b    CAGAGCAGTCCCATATCAA-CATATTTATAATCCAAATTTCAAGA-CTACTCAACCTGAG
3182  194_HRV46     CAGAGCAGTCCCATATCAA-CATATTTATAATCCAAATTTCAAGA-CTACTCAACCTGAG
3183  195_HRV80a    TAGAGCAGTCCCATACCAA-CATACCTACAGCCCAAATTTCAAAA-ACACTG---ATGAA
3184  196_HRV80b    TAGAGCAGTCCCATACCAA-CATACCTACAGCCCAAATTTCAAAA-ACACTG---ATGAA
3185  197_HRV80     TAGAGCAGTCCCATACCAA-CATACCTACAGCCCAAATTTCAAAA-ACACTG---ATGAA
3186  198_HRV51     TCGTGCTGTAGCCTACCAA-CACACATACAGTACAAACTTCGTTC-CAAAAGAGGGATTT
3187  199_HRV51a    TCGTGCTGTAGCCTACCAA-CACACATACAGTACAAACTTCGTTC-CAAAAGAGGGATTT
3188  200_HRV51b    TCGTGCTGTAGCCTACCAA-CACACATACAGTACAAACTTCGTTC-CAAAAGAGGGATTT
3189  201_HRV65a    CCGAGCAGTAGCTTACCAA-CACACATACAGTACAAATTTTGTTC-CTAGCGGAGGTCTT
3190  202_HRV65b    CCGAGCAGTAGCTTACCAA-CACACATACAGTACAAATTTTGTTC-CTAGCGGAGGTCTT
3191  203_HRV65     CCGAGCAGTAGCTTACCAA-CACACATACAGTACAAATTTTGTTC-CTAGCGGAGGTCTT
3192  204_HRV71a    CAGAGCAGTAGCCTACCAA-TCAACATATACCACAAATTTTGTTC-CACAAGACGGGATC
3193  205_HRV71b    CAGAGCAGTAGCCTACCAA-TCAACATATACCACAAATTTTGTTC-CACAAGACGGGATC
3194  206_HRV71     CAGAGCAGTAGCCTACCAA-TCAACATATACCACAAATTTTGTTC-CACAAGACGGGATC
3195  207_HRV8      CAGAGCAGTTACGTATAAC-CATATATACAACCCCAATTATGTTA-GAGAGG------GA
3196  208_HRV95     CAGAGCAGTTACGTATAAC-CATATATACAACCCCAATTATGTTA-GAGAGG------GA
3197  209_HRV45     AAGAGCAGTCACATATAAC-CATACATATAATCCAAATTATGTTA-GGGCTG------AT
3198  210_HRV45a    AAGAGCAGTCACATATAAC-CATACATATAATCCAAATTATGTTA-GGGCTG------AT
3199  211_HRV45b    AAGAGCAGTCACATATAAC-CATACATATAATCCAAATTATGTTA-GGGCTG------AT
3200  GROUP_1       --G-G---T----TA-----------------AA-T------------------------
3201
3202  1_HRV1A1|d    GACG------TGACAACAG---CCATAGTCCGCAGAA------ACACTATAACAACTG--
3203  2_HRV1A2|d    GACG------TGACAACAG---CCATAGTCCGCAGAA------ACACTATAACAACTG--
3204  3_HRV1A|cD    GACG------TGACAACAG---CCATAGTCCGCAGAA------ACACTATAACAACTG--
3205  4_HRV1B1|d    GATG------TGACAACAG---CTATAGTTCCTAGAG------CTAGCATGAAAACTG--
3206  5_HRV1B2|d    GATG------TGACAACAG---CTATAGTTCCTAGAG------CTAGCATGAAAACTG--
3207  6_HRV1B      GATG------TGACAACAG---CTATAGTTCCTAGAG------CTAGCATGAAAACTG--
3208  7_HRV40a|d    GAAG------TCCAGATTT---TCCTCAAAGAGAGAG------CCAGCCTAACAACAG--
3209  8_HRV40b|d    GAAG------TCCAGATTT---TCCTCAAAGAGAGAG------CCAGCCTAACAACAG--
3210  9_HRV40      GAAG------TCCAGATTT---TCCTCAAAGAGAGAG------CCAGCCTAACAACAG--
3211  10_HRV85     GAAG------TTAAGATCT---TCCTCAAAGAGAGAG------CTAGTTTAACCACAG--
3212  11_HRV85a|   GAAG------TTAAGATCT---TCCTCAAAGAGAGAG------CTAGTTTAACCACAG--
3213  12_HRV85b|   GAAG------TTAAGATCT---TCCTCAAAGAGAGAG------CTAGTTTAACCACAG--
3214  13_HRV56a|   GATG------TACAGATCT---TCTTAAAACCCAGAC------CCAGCCTAACAACAT--
3215  14_HRV56b|   GATG------TACAGATCT---TCTTAAAACCCAGAC------CCAGCCTAACAACAT--
3216  15_HRV56     GATG------TACAGATCT---TCTTAAAACCCAGAC------CCAGCCTAACAACAT--
3217  16_HRV54     GATC------CAACAATTT---TCCTTAAACACAGGA------CAAACCTTGTAACAG--
3218  17_HRV98     GAAC------CAACAATCT---TTCTTAAGCATAGAA------AAGATCTTGTAACAG--
3219  18_HRV59a|   GAAC------CTGAAATTT---TCTTAAAACCAAGAA------TGAATATTACAACAG--
3220  19_HRV59b|   GAAC------CTGAAATTT---TCTTAAAACCAAGAA------TGAATATTACAACAG--
3221  20_HRV59     GAAC------CTGAAATTT---TCTTAAAACCAAGAA------TGAATATTACAACAG--
3222  21_HRV63     GAGA------CTGAAATTT---TCTTAAAACCTAGAG------CAACTATCAAGACAG--
3223  22_HRV63b|   GAGA------CTGAAATTT---TCTTAAAACCTAGAG------CAACTATCAAGACAG--
3224  23_HRV63a|   GAGA------CTGAAATTT---TCTTAAAACCTAGAG------CAACTATCAAGACAG--
3225  24_HRV39     GAAC------CAACACTCT---TTATAAAATCAAGAG------AGAATCTTACCACAG--
3226  25_HRV39a|   GAAC------CAACACTCT---TTATAAAATCAAGAG------AGAATCTTACCACAG--
3227  26_HRV39b|   GAAC------CAACACTCT---TTATAAAACCAAGAG------AGAATCTTACCACAG--
3228  27_HRV10a|   GAAT------TACAAATAT---TTATTAGGTCTAGAGATGATCCCAAAGTAGTAACTG--
3229  28_HRV10b|   GAAT------TACAAATAT---TTATTAGGTCTAGAGATGATCCCAAAGTAGTAACTG--
3230  29_HRV10     GAAT------TACAAATAT---TTATTAGGTCTAGAGATGATCCCAAAGTAGTAACTG--
3231  30_HRV100a   GATG------TAAAGATTT---TCATTAGACCCAGAGATGATCCAAAGTTGTAACTG--
3232  31_HRV100b   GATG------TAAAGATTT---TCATTAGACCCAGAGATGATCCAAAGTTGTAACTG--
3233  32_HRV100    GATG------TAAAGATTT---TCATTAGACCCAGAGATGATCCAAAGTTGTAACTG--
3234  33_HRV66     GATC------TGCAAATTT---TCATTAAACCTAGAACAGATCCAAAGTAGTCAATG--
3235  34_HRV66b|   GATC------TGCAAATTT---TCATTAAACCTAGAACAGATCCAAAGTAGTCAATG--
3236  35_HRV66a|   GATC------TGCAAATTT---TCATTAAACCTAGAACAGATCCAAAGTAGTCAATG--
3237  36_HRV77a|   GATG------TACAAATCT---TTATTAAAGAGAGCAAGCCCAAAAGTAGTTACTT--
3238  37_HRV77b|   GATG------TACAAATCT---TTATTAAAGAGAGCAAGCCCAAAAGTAGTTACTT--
3239  38_HRV77     GATG------TACAAATCT---TTATTAAAGAGAGCAAGCCCAAAAGTAGTTACTT--
3240  39_HRV62a    ---G------TTGACATTT---TTATAAAATCAAGG------CAAAACTTGCAAACAG--
3241  40_HRV62b    ---G------TTGACATTT---TTATAAAATCAAGG------CAAAACTTGCAAACAG--
3242  41_HRV25     ---G------TTGACATCT---TTATACAACCAAGA------AACAGTTTAAAAACAG--
3243  42_HRV29a    ---G------AT-CCAG-----TTGTGGAATCCAGA------CCAAGCTTAATGACAG--
3244  43_HRV29b    ---G------AT-ACAG-----TTGTGGAATCCAGA------CCAAGCTTAATGACAG--
3245  44_HRV44a    ---G------AT-ACAG-----TTGTGGAACCTAGA------CACAGCATAATGACAG--
```

FIG. D11 CONT'D 07.trace                                                                                      9/20/2007 5:04 PM

```
3246  45_HRV44b    ---G------AT-ACAG-----TTGTGGAACCTAGA------CACAGCATAATGACAG--
3247  46_HRV31     GAAG------TTACAATCT---TTGTTAAACACAGGGATAATCCAAAGATTATCACAG--
3248  47_HRV31a|   GAAG------TTACAATCT---TTGTTAAACACAGGGATAATCCAAAGATTATCACAG--
3249  48_HRV31b|   GAAG------TTACAATCT---TTGTTAAACACAGGGATAATCCAAAGATTATCACAG--
3250  49_HRV47     GAAG------TTGCAATTT---TCATTGAGCATAGAGAAAATCCAAAATTCATTACAG--
3251  50_HRV47a|   GAAG------TTGCAATTT---TCATTGAGCATAGAGAAAATCCAAAATTCATTACAG--
3252  51_HRV47b|   GAAG------TTGCAATTT---TCATTGAGCATAGAGAAAATCCAAAATTCATTACAG--
3253  52_HRV11     CAGG------TGAAAACAG---CTGTCAAGGCTAGGAAAACAATTAAAACAGCA------
3254  53_HRV11b|   CAGG------TGAAAACAG---CTGTCAAGGCTAGGAAAACAATTAAAACAGCG------
3255  54_HRV11a|   CAGG------TGAAAACAG---CTGTCAAGGCTAGGAAAACAATTAAAACAGCT------
3256  55_HRV76     GATG------TGCAAACAG---CTATTAGACCAAGAGCAACAATTAAGACTGCA------
3257  56_HRV76b|   GATG------TGCAAACAG---CTATTAGACCAAGAGCAACAATTAAGACTGCG------
3258  57_HRV76a|   GATG------TGCAAACAG---CTATTAGACCAAGAGCAACAATTAAGACTGCT------
3259  58_HRV33     GAAG------TGAAGACAG---CTATTAGACCAAGAGCAACAATCAAGACTGCA------
3260  59_HRV33b|   GAAG------TGAAGACAG---CTATTAGACCAAGAGCAACAATCAAGACTGCG------
3261  60_HRV33a|   GAAG------TGAAGACAG---CTATTAGACCAAGAGCAACAATCAAGACTGCT------
3262  61_HRV24a|   GAAG------TCAAGACAG---CAATTGAACCTAGAAGAGGAATTAAAACAGTG------
3263  62_HRV24b|   GAAG------TCAAGACAG---CAATTGAACCTAGAAGAGGAATTAAAACAGTC------
3264  63_HRV24     GAAG------TCAAGACAG---CAATTGAACCTAGAAGAGGAATTAAAACAGTT------
3265  64_HRV90     GAAC------TTAAGACTG---CAATTAGGCCCAGGAAAACAATCACAACAGCA------
3266  65_HRV90a|   GAAC------TTAAGACTG---CAATTAGGCCCAGGAAAACAATCACAACAGCG------
3267  66_HRV90b|   GAAC------TTAAGACTG---CAATTAGGCCCAGGAAAACAATCACAACAGCT------
3268  67_HRV34     ACTG------AGAAGACTG---CAATCAAACACAGAGCAAAGATCACAATGGCC------
3269  68_HRV34b|   ACTG------AGAAGACTG---CAATCAAACACAGAGCAAAGATCACAATGGCA------
3270  69_HRV34a|   ACTG------AGAAGACTG---CAATCAAACACAGAGCAAAGATCACAATGGCT------
3271  70_HRV50a|   ACTG------AGAAGACTG---CAATTGCAACTAGACCAAAGATCACAGTGGCA------
3272  71_HRV50b|   ACTG------AGAAGACTG---CAATTGCAACTAGACCAAAGATCACAGTGGCG------
3273  72_HRV50     ACTG------AGAAGACTG---CAATTGCAACTAGACCAAAGATCACAGTGGCT------
3274  73_HRV18a|   AGAG------AGAAAACTG---CCATAGTACCCAGAGCAAGGATTACAATGGCA------
3275  74_HRV18b|   AGAG------AGAAAACTG---CCATAGTACCCAGAGCAAGGATTACAATGGCG------
3276  75_HRV18     AGAG------AGAAAACTG---CCATAGTACCCAGAGCAAGGATTACAATGGCT------
3277  76_HRV55     ACAG------AAAAGACAG---CAATTGAATACAGAAGGGACATTAAAACAGTG------
3278  77_HRV55b|   ACAG------AAAAGACAG---CAATTGAATACAGAAGGGACATTAAAACAGTC------
3279  78_HRV55a|   ACAG------AAAAGACAG---CAATTGAATACAGAAGGGACATTAAAACAGTA------
3280  79_HRV57     CAAG------AAGAAACAG---CAATTAAATATAGAAGGGACATTAAAATTGTTAAGA--
3281  80_HRV57a|   CAAG------AAGAAACAG---CAATTAAATATAGAAGGGACATTAAAATTGTTAAGA--
3282  81_HRV57b|   CAAG------AAGAAACAG---CAATTAAATATAGAAGGGACATTAAAATTGTTAAGA--
3283  82_HRV21     GAAG------TCACTTCTG---CAGTTGAGTCCAGAAGAACAATTGTCACAGTT------
3284  83_HRVHan    GATG------TCACTTCTG---CAGTTGAGTCCAGAAGAACAATTGTCACAGTT------
3285  84_HRV43     GAGG------TAGAAACAG---CCATAGTATCTAGGAGGGATATCAAAGTTGTCAATG--
3286  85_HRV43b|   GAGG------TAGAAACAG---CCATAGTATCTAGGAGGGATATCAAAATTGTCAATG--
3287  86_HRV43a|   GAGG------TAGAAACAG---CCATAGTATCTAGGAGGGATATCAAAATTGTCAATG--
3288  87_HRV75     CAAG------TTGAGATTG---CTATTGAGCCCAGAAGAGATGTTAAGTTTGTAAATG--
3289  88_HRV75b|   CAAG------TTGAGATTG---CTATTGAGCCCAGAAGAGATGTTAAGTTTGTAAATG--
3290  89_HRV75a|   CAAG------TTGAGATTG---CTATTGAGCCCAGAAGAGATGTTAAGTTTGTAAATG--
3291  96_HRV9a|d   GATT------ATGCCACAG---TTATACCAGTTAGAGACAATGTTAGGGCAGTAAAGA--
3292  97_HRV9b|d   GATT------ATGCCACAG---TTATACCAGTTAGAGACAATGTTAGGGCAGTAAAGA--
3293  98_HRV9      GATT------ATGCCACAG---TTATACCAGTTAGAGACAATGTTAGGGCAGTAAAGA--
3294  99_HRV32     GATT------ACACCACAG---CCATACAAACCAGAGAGCATGTTAGAGCAGTCAAAA--
3295  100_HRV32a   GATT------ACACCACAG---CCATACAAACCAGAGAGCATGTTAGAGCAGTCAAAA--
3296  101_HRV32b   GATT------ACACCACAG---CCATACAAACCAGAGAGCATGTTAGAGCAGTCAAAA--
3297  102_HRV67    GAGG------CTCAAACGG---TTATACCTGTTAGAGCAGATGTTAGAACAATTAGAA--
3298  103_HRV67a   GAGG------CTCAAACGG---TTATACCTGTTAGAGCAGATGTTAGAACAATTAGAA--
3299  104_HRV67b   GAGG------CTCAAACGG---TTATACCTGTTAGAGCAGATGTTAGAACAATTAGAA--
3300  105_HRV15    GATG------TAACTACAG---TTATTCCAACTAGAGAAATGTTAGAGCTATAGTAA--
3301  106_HRV15a   GATG------TAACTACAG---TTATTCCAACTAGAGAAAATGTTAGAGCTATAGTAA--
3302  107_HRV15b   GATG------TAACTACAG---TTATTCCAACTAGAGAAAATGTTAGAGCTATAGTAA--
3303  108_HRV74a   GACG------TAACTACAG---TCATCCCAACTAGG---------AGATCAATAGTGA--
3304  109_HRV74b   GACG------TAACTACAG---TCATCCCAACTAGG---------AGATCAATAGTGA--
3305  110_HRV74    GACG------TAACTACAG---TCATCCCAACTAGG---------AGATCAATAGTGA--
3306  111_HRV38a   GAAG------TAACCACTA---TGATTCCAACTAGAACCAACATAAGAACCATCGTAA--
3307  112_HRV38b   GAAG------TAACCACTA---TGATTCCAACTAGAACCAACATAAGAACCATCGTAA--
3308  113_HRV38    GAAG------TAACCACTA---TGATTCCAACTAGAACCAACATAAGAACCATCGTAA--
3309  114_HRV60    GAAG------CAGCCATAA---CAATCCCCATTAGAACTGATATACGAGCAATCAGAA--
3310  115_HRV60a   GAAG------CAGCCATAA---CAATCCCCATTAGAACTGATATACGAGCAATCAGAA--
```

FIG. D11 CONT'D

07.trace                                                                9/20/2007 5:04 PM

```
3311 116_HRV60b    GAAG------CAGCCATAA---CAATCCCCATTAGAACTGATATACGAGCAATCAGAA--
3312 117_HRV64a    GAAT------ACACACCAC---CCGTTCCGTCACGTAACAGCCCCAGAGATATTGTCA--
3313 118_HRV64b    GAAT------ACACACCAC---CCGTTCCGTCACGTAACAGCCCCAGAGATATTGTCA--
3314 119_HRV64     GAAT------ACACACCAC---CCGTTCCGTCACGTAACAGCCCCAGAGATATTGTCA--
3315 120_HRV94a    GAGT------ACAAGCCAC---CTGTCCCAGTTAGGAATAGCCCCAGAGACATTGTCA--
3316 121_HRV94b    GAGT------ACAAGCCAC---CTGTCCCAGTTAGGAATAGCCCCAGAGACATTGTCA--
3317 122_HRV94     GAGT------ACAAGCCAC---CTGTCCCAGTTAGGAATAGCCCCAGAGACATTGTCA--
3318 123_HRV22     GATT------ACACACTAC---CTATCCCAACAAGAGCCAACCCTAGACAAATTTTGA--
3319 124_HRV22a    GATT------ACACACTAC---CTATCCCAACAAGAGCCAACCCTAGACAAATTTTGA--
3320 125_HRV22b    GATT------ACACACTAC---CTATCCCAACAAGAGCCAACCCTAGACAAATTTTGA--
3321 126_HRV82     GATT------ACAGTGTTG---TTATTCCAGTTAGAGAGAGTCCCAGACAGATTCTTA--
3322 127_HRV82b    GATT------ACAGTGTTG---TTATTCCAGTTAGAGAGAGTCCCAGACAGATTCTTA--
3323 128_HRV82a    GATT------ACAGTGTTG---TTATTCCAGTTAGAGAGAGTCCCAGACAGATTCTTA--
3324 129_HRV19     GAAG------TCACTCTTC---CAATTGAAATAAGAGATAACCTAGACATATAAAGA--
3325 130_HRV19a    GAAG------TCACTCTTC---CAATTGAAATAAGAGATAACCCTAGACATATAAAGA--
3326 131_HRV19b    GAAG------TCACTCTTC---CAATTGAAATAAGAGATAACCCTAGACATATAAAGA--
3327 132_HRV13     GATG------TTGCAGTCT---CCATTGTACCTAGAGCAAATGTTAGGGAAATTAGAA--
3328 133_HRV13a    GATG------TTGCAGTCT---CCATTGTACCTAGAGCAAATGTTAGGGAAATTAGAA--
3329 134_HRV13b    GATG------TTGCAGTCT---CCATTGTACCTAGAGCAAATGTTAGGGAAATTAGAA--
3330 135_HRV41     GCAGA---GATTGTGGCTT---CTGTCAGACCTAGAGACAATGTTAGACAAGTAAGAA--
3331 136_HRV41a    GCAGA---GATTGTGGCTT---CTGTCAGACCTAGAGACAATGTTAGACAAGTAAGAA--
3332 137_HRV41b    GCAGA---GATTGTGGCTT---CTGTCAGACCTAGAGACAATGTTAGACAAGTAAGAA--
3333 138_HRV73     GAAG------TTACTACTG---CCATTAGGCATAGAGATAATGTTAGAGCCATCCAAA--
3334 139_HRV73b    GAAG------TTACTACTG---CCATTAGGCATAGAGATAATGTTAGAGCCATCCAAA--
3335 140_HRV73a    GAAG------TTACTACTG---CCATTAGGCATAGAGATAATGTTAGAGCCATCCAAA--
3336 141_HRV61     GAAAAACAAGTTACCACTT---TCATCAAACCTAGAGCTAACTTAAGAGAGATTAGAA--
3337 142_HRV61a    GAAAAACAAGTTACCACTT---TCATCAAACCTAGAGCTAACTTAAGAGAGATTAGAA--
3338 143_HRV61b    GAAAAACAAGTTACCACTT---TCATCAAACCTAGAGCTAACTTAAGAGAGATTAGAA--
3339 144_HRV96     -------AGGTTACCACTT---TTATCAAACCTAGAGAAAATCTAAGGGATATTAGAA--
3340 145_HRV96b    -------AGGTTACCACTT---TTATCAAACCTAGAGAAAATCTAAGGGATATTAGAA--
3341 146_HRV96a    -------AGGTTACCACTT---TTATCAAACCTAGAGAAAATCTAAGGGATATTAGAA--
3342 90_HRV16a|    GTAC------ACAATGATGTGGCTATAAGACCTAGAACAAATCTAACAACTGTA------
3343 91_HRV16b|    GTAC------ACAATGATGTGGCTATAAGACCTAGAACAAATCTAACAACTGTC------
3344 92_1AYM_A     GTAC------ACAATGATGTGGCTATAAGACCTAGAACAAATCTAACAACTGTT------
3345 93_HRV81a|    GTCC------ACACTAGTGTAGCCATAAAACCTAGAACAAGTCTAACAAGTG------
3346 94_HRV81b|    GTCC------ACACTAGTGTAGCCATAAAACCTAGAACAAGTCTAACAAATGTC------
3347 95_HRV81      GTCC------ACACTAGTGTAGCCATAAAACCTAGAACAAGTCTAACAAATGTT------
3348 147_HRV2      AGTA------TTCAGACAG---CAATTGTGACCAGACCAATTATCACTACAGCT------
3349 148_HRV2a|    AGTA------TTCAGACAG---CAATTGTGACCAGACCAATTATCACTACAGCA------
3350 149_HRV2b|    AGTA------TTCAGACAG---CAATTGTGACCAGACCAATTATCACTACAGCG------
3351 150_HRV49a    GACA------TTAAAACAG---GAATCACATCCAGAGCAATTATTACAACAGCG------
3352 151_HRV49b    GACA------TTAAAACAG---GAATCACATCCAGAGCAATTATTACAACAGCA------
3353 152_HRV49     GACA------TTAAAACAG---GAATCACATCCAGAGCAATTATTACAACAGCT------
3354 153_HRV23a    AATG------TCAAATCAA---GGGTTGCACATAGACCTGCAGTGATAACAGCG------
3355 154_HRV23b    AATG------TCAAATCAA---GGGTTGCACATAGACCTGCAGTGATAACAGCA------
3356 155_HRV23     AATG------TCAAATCAA---GGGTTGCACATAGACCTGCAGTGATAACAGCT------
3357 156_HRV30a    GAAG------TTAAATCAA---GGGTTGAACACAGAGCTAGGGTGACGACAGCA------
3358 157_HRV30b    GAAG------TTAAATCAA---GGGTTGAACACAGAGCTAGGGTGACGACAGCG------
3359 158_HRV30     GAAG------TTAAATCAA---GGGTTGAACACAGAGCTAGGGTGACGACAGCT------
3360 159_HRV7      GAGG------TCGCA---ACTCAAATCAAAACCAGAGCCAATCTTTTCACCCTCAAAT--
3361 160_HRV7b|    GAGG------TCGCA---ACTCAAATCAAAACCAGAGCCAATCTTTTCACCCTCAAAT--
3362 161_HRV7a|    GAGG------TCGCA---ACTCAAATCAAAACCAGAGCCAATCTTTTCACCCTCAAAT--
3363 162_HRV88     GAAG------TAGCA---ACTCAAATCAAAACCAGACGAGATGTTTACACTGTTACCA--
3364 163_HRV88a    GAAG------TAGCA---ACTCAAATCAAAACCAGACGAGATGTTTACACTGTTACCA--
3365 164_HRV88b    GAAG------TAGCA---ACTCAAATCAAAACCAGACGAGATGTTTACACTGTTACCA--
3366 165_HRV36a    GAGA------TCACA---ACCCAAATTAAAACCAGACCTAATGTCTTCACTGTA------
3367 166_HRV36b    GAGA------TCACA---ACCCAAATTAAAACCAGACCTAATGTCTTCACTGTG------
3368 167_HRV36     GAGA------TCACA---ACCCAAATTAAAACCAGACCTAATGTCTTCACTGTT------
3369 168_HRV89a    GAGG------CCACA---ACTCAGATTAAAACCAGACCTGATGTTTTACCGTTACAA--
3370 169_HRV89b    GAGG------CCACA---ACTCAGATTAAAACCAGACCTGATGTTTTACCGTTACAA--
3371 170_HRV89     GAGG------CCACA---ACTCAGATTAAAACCAGACCTGATGTTTTACCGTTACAA--
3372 171_HRV58     GAGG------TAACA---ACACAAATCAAACCCAGAACCAATGTTTTACTATTACAT--
3373 172_HRV58a    GAGG------TAACA---ACACAAATCAAACCCAGAACCAATGTTTTACTATTACAT--
3374 173_HRV58b    GAGG------TAACA---ACACAAATCAAACCCAGAACCAATGTTTTACTATTACAT--
3375 174_HRV12a    GGAG------TTCCAGACAATAGAGTCAAACTCAGAGAGACACTCACCACAGTA------
```

FIG. D11 CONT'D 07.trace                                                                9/20/2007 5:04 PM

```
3376 175_HRV12b    GGAG------TTCCAGACAATAGAGTCAAACTCAGAGAGACACTCACCACAGTG------
3377 176_HRV12     GGAG------TTCCAGACAATAGAGTCAAACTCAGAGAGACACTCACCACAGTT------
3378 177_HRV78a    GGAA------CTCCAGACACCAAAGTGGCAATTAGAGCTAATATTAAAACTGTA------
3379 178_HRV78b    GGAA------CTCCAGACACCAAAGTGGCAATTAGAGCTAATATTAAAACTGTG------
3380 179_HRV78     GGAA------CTCCAGACACCAAAGTGGCAATTAGAGCTAATATTAAAACTGTT------
3381 180_HRV20     GAAA------TTACA---ACTCATATCAGATTCAGAAACACTGTCAAAGATCTAACATAC
3382 181_HRV20a    GAAA------TTACA---ACTCATATCAGATTCAGAAACACTGTCAAAGATCTAACATAC
3383 182_HRV20b    GAAA------TTACA---ACTCATATCAGATTCAGAAACACTGTCAAAGATCTAACATAC
3384 183_HRV68     GATA------TTAAA---ACTCATATTAAATTTAGGAATACTGTTAAAGATTTGGCATAT
3385 184_HRV68a    GATA------TTAAA---ACTCATATTAAATTTAGGAATACTGTTAAAGATTTGGCATAT
3386 185_HRV68b    GATA------TTAAA---ACTCATATTAAATTTAGGAATACTGTTAAAGATTTGGCATAT
3387 186_HRV28     GATG------TTGAG---ACTCATATTAAATTTAGAACAGATGTTAAACAGATCACAA--
3388 187_HRV28a    GATG------TTGAG---ACTCATATTAAATTTAGAACAGATGTTAAACAGATCACAA--
3389 188_HRV28b    GATG------TTGAG---ACTCATATTAAATTTAGAACAGATGTTAAACAGATCACAA--
3390 189_HRV53a    ACAG------TTGAA---ACTCACATTAAGTTCAGACCTGATGTTAAAGATGTAACAT--
3391 190_HRV53b    ACAG------TTGAA---ACTCACATTAAGTTCAGACCTGATGTTAAAGATGTAACAT--
3392 191_HRV53     ACAG------TTGAA---ACTCACATTAAGTTCAGACCTGATGTTAAAGATGTAACAT--
3393 192_HRV46a    ACTA------TACCAGATACTCATATTGGAATTAGAAGGGATATAAAGTACATTAAAA--
3394 193_HRV46b    ACTA------TACCAGATACTCATATTGGAATTAGAAGGGATATAAAGTACATTAAAA--
3395 194_HRV46     ACTA------TACCAGATACTCATATTGGAATTAGAAGGGATATAAAGTACATTAAAA--
3396 195_HRV80a    TCTA------TACCAGATACACAAATTAAAATCAGAGATAATATCAGGCAGGTTAGAA--
3397 196_HRV80b    TCTA------TACCAGATACACAAATTAAAATCAGAGATAATATCAGGCAGGTTAGAA--
3398 197_HRV80     TCTA------TACCAGATACACAAATTAAAATCAGAGATAATATCAGGCAGGTTAGAA--
3399 198_HRV51     GAAG------GCTTGAAAACTCAGATTAAAACTAGGGCAGACATCAAACTTGTGAACT--
3400 199_HRV51a    GAAG------GCTTGAAAACTCAGATTAAAACTAGGGCAGACATCAAACTTGTGAACT--
3401 200_HRV51b    GAAG------GCTTGAAAACTCAGATTAAAACTAGGGCAGACATCAAACTTGTGAACT--
3402 201_HRV65a    ACAA------ACCTAAGAACCCAAATTAAAACCAGAGATAACATTAAAATTGTAAACT--
3403 202_HRV65b    ACAA------ACCTAAGAACCCAAATTAAAACCAGAGATAACATTAAAATTGTAAACT--
3404 203_HRV65     ACAA------ACCTAAGAACCCAAATTAAAACCAGAGATAACATTAAAATTGTAAACT--
3405 204_HRV71a    AATT------CCATTAAAACCAAAATCAAAATCAGAAGAGACATTAAAGAGGTCAGCA--
3406 205_HRV71b    AATT------CCATTAAAACCAAAATCAAAATCAGAAGAGACATTAAAGAGGTCAGCA--
3407 206_HRV71     AATT------CCATTAAAACCAAAATCAAAATCAGAAGAGACATTAAAGAGGTCAGCA--
3408 207_HRV8      GTAA------CACCAGAAACTAAGGTTAAATATAGAGCTGAAGTCACAACCATT------
3409 208_HRV95     GTAA------CACCAGAAACTAAGGTCAAATATAGAGCTGAAGTCACAACCATT------
3410 209_HRV45     GAAA------CAGCC---ACAAAAGTCCAAACTAGAGCAAATGTCACAACAGTA------
3411 210_HRV45a    GAAA------CAGCC---ACAAAAGTCCAAACTAGAGCAAATGTCACAACAGTG------
3412 211_HRV45b    GAAA------CAGCC---ACAAAAGTCCAAACTAGAGCAAATGTCACAACAGTT------
3413 GROUP_1       ------------------------T--------G--------------------------
3414
3415 1_HRV1A1|d    ----CA---------------
3416 2_HRV1A2|d    ----CG---------------
3417 3_HRV1A|cD    ----CT---------------
3418 4_HRV1B1|d    ----TA---------------
3419 5_HRV1B2|d    ----TC---------------
3420 6_HRV1B       ----TT---------------
3421 7_HRV40a|d    ----TA---------------
3422 8_HRV40b|d    ----TC---------------
3423 9_HRV40       ----TT---------------
3424 10_HRV85      ----CA---------------
3425 11_HRV85a|    ----CG---------------
3426 12_HRV85b|    ----CT---------------
3427 13_HRV56a|    ----TA---------------
3428 14_HRV56b|    ----TG---------------
3429 15_HRV56      ----TT---------------
3430 16_HRV54      ----CT---------------
3431 17_HRV98      ----CT---------------
3432 18_HRV59a|    ----CA---------------
3433 19_HRV59b|    ----CG---------------
3434 20_HRV59      ----CT---------------
3435 21_HRV63      ----CA---------------
3436 22_HRV63b|    ----CG---------------
3437 23_HRV63a|    ----CT---------------
3438 24_HRV39      ----CT---------------
3439 25_HRV39a|    ----CA---------------
3440 26_HRV39b|    ----CT---------------
```

FIG. D11 CONT'D 07.trace                                                                9/20/2007 5:04 PM

```
3441 27_HRV10a|     ----CA---------------
3442 28_HRV10b|     ----CC---------------
3443 29_HRV10       ----CT---------------
3444 30_HRV100a     ----CA---------------
3445 31_HRV100b     ----CG---------------
3446 32_HRV100      ----CT---------------
3447 33_HRV66       ----TA---------------
3448 34_HRV66b|     ----TG---------------
3449 35_HRV66a|     ----TC---------------
3450 36_HRV77a|     ----TG---------------
3451 37_HRV77b|     ----TA---------------
3452 38_HRV77       ----TT---------------
3453 39_HRV62a      ----CT---------------
3454 40_HRV62b      ----C----------------
3455 41_HRV25       ----CT---------------
3456 42_HRV29a      ----CT---------------
3457 43_HRV29b      ----CT---------------
3458 44_HRV44a      ----CT---------------
3459 45_HRV44b      ----CT---------------
3460 46_HRV31       ----CA---------------
3461 47_HRV31a|     ----CT---------------
3462 48_HRV31b|     ----CA---------------
3463 49_HRV47       ----CA---------------
3464 50_HRV47a|     ----CT---------------
3465 51_HRV47b|     ----CA---------------
3466 52_HRV11       ---------------------
3467 53_HRV11b|     ---------------------
3468 54_HRV11a|     ---------------------
3469 55_HRV76       ---------------------
3470 56_HRV76b|     ---------------------
3471 57_HRV76a|     ---------------------
3472 58_HRV33       ---------------------
3473 59_HRV33b|     ---------------------
3474 60_HRV33a|     ---------------------
3475 61_HRV24a|     ---------------------
3476 62_HRV24b|     ---------------------
3477 63_HRV24       ---------------------
3478 64_HRV90       ---------------------
3479 65_HRV90a|     ---------------------
3480 66_HRV90b|     ---------------------
3481 67_HRV34       ---------------------
3482 68_HRV34b|     ---------------------
3483 69_HRV34a|     ---------------------
3484 70_HRV50a|     ---------------------
3485 71_HRV50b|     ---------------------
3486 72_HRV50       ---------------------
3487 73_HRV18a|     ---------------------
3488 74_HRV18b|     ---------------------
3489 75_HRV18       ---------------------
3490 76_HRV55       ---------------------
3491 77_HRV55b|     ---------------------
3492 78_HRV55a|     ---------------------
3493 79_HRV57       ----ATGTG------------
3494 80_HRV57a|     ----ATGTA------------
3495 81_HRV57b|     ----ATGTC------------
3496 82_HRV21       ---------------------
3497 83_HRVHan      ---------------------
3498 84_HRV43       ----CA---------------
3499 85_HRV43b|     ----CG---------------
3500 86_HRV43a|     ----CT---------------
3501 87_HRV75       ----CA---------------
3502 88_HRV75b|     ----CG---------------
3503 89_HRV75a|     ----CT---------------
3504 96_HRV9a|d     ----ATGTC------------
3505 97_HRV9b|d     ----ATGTG------------
```

FIG. D11 CONT'D 07.trace                                                                9/20/2007 5:04 PM

```
3506  98_HRV9       ----ATGTA------------
3507  99_HRV32      ----ATGTA------------
3508  100_HRV32a    ----ATGTG------------
3509  101_HRV32b    ----ATGTC------------
3510  102_HRV67     ----ATGTA------------
3511  103_HRV67a    ----ATGTC------------
3512  104_HRV67b    ----ATGTT------------
3513  105_HRV15     ----ATGTT------------
3514  106_HRV15a    ----ATGTA------------
3515  107_HRV15b    ----ATGTC------------
3516  108_HRV74a    ----ATGTA------------
3517  109_HRV74b    ----ATGTC------------
3518  110_HRV74     ----ATGTT------------
3519  111_HRV38a    ----ATGTA------------
3520  112_HRV38b    ----ATGTC------------
3521  113_HRV38     ----ATGTT------------
3522  114_HRV60     ----CAGTT------------
3523  115_HRV60a    ----CAGTA------------
3524  116_HRV60b    ----CAGTG------------
3525  117_HRV64a    ----CAGTG------------
3526  118_HRV64b    ----CAGTG------------
3527  119_HRV64     ----CAGTA------------
3528  120_HRV94a    ----CAGTG------------
3529  121_HRV94b    ----CAGTC------------
3530  122_HRV94     ----CAGTA------------
3531  123_HRV22     ----ATGTA------------
3532  124_HRV22a    ----ATGTG------------
3533  125_HRV22b    ----ATGTC------------
3534  126_HRV82     ----ATGTA------------
3535  127_HRV82b    ----ATGTT------------
3536  128_HRV82a    ----ATGTC------------
3537  129_HRV19     ----ATGTA------------
3538  130_HRV19a    ----ATGTG------------
3539  131_HRV19b    ----ATGTC------------
3540  132_HRV13     ----ACTTT------------
3541  133_HRV13a    ----ACTTG------------
3542  134_HRV13b    ----ACTTA------------
3543  135_HRV41     ----ATTAT------------
3544  136_HRV41a    ----ATTAG------------
3545  137_HRV41b    ----ATTAC------------
3546  138_HRV73     ----ATTTT------------
3547  139_HRV73b    ----ATTTG------------
3548  140_HRV73a    ----ATTTC------------
3549  141_HRV61     ----CATTT------------
3550  142_HRV61a    ----CATTT------------
3551  143_HRV61b    ----CATTT------------
3552  144_HRV96     ----ATTTT------------
3553  145_HRV96b    ----ATTTA------------
3554  146_HRV96a    ----ATTTC------------
3555  90_HRV16a|    ---------------------
3556  91_HRV16b|    ---------------------
3557  92_1AYM_A     ---------------------
3558  93_HRV81a|    ---------------------
3559  94_HRV81b|    ---------------------
3560  95_HRV81      ---------------------
3561  147_HRV2      ---------------------
3562  148_HRV2a|    ---------------------
3563  149_HRV2b|    ---------------------
3564  150_HRV49a    ---------------------
3565  151_HRV49b    ---------------------
3566  152_HRV49     ---------------------
3567  153_HRV23a    ---------------------
3568  154_HRV23b    ---------------------
3569  155_HRV23     ---------------------
3570  156_HRV30a    ---------------------
```

FIG. D11 CONT'D

```
07.trace                                                                  9/20/2007 5:04 PM 3571  157_HRV30b    --------------------
3572  158_HRV30     --------------------
3573  159_HRV7      ----CAGCT-----------
3574  160_HRV7b|    ----CAGCA-----------
3575  161_HRV7a|    ----CAGCG-----------
3576  162_HRV88     ----CTGCT-----------
3577  163_HRV88a    ----CTGCA-----------
3578  164_HRV88b    ----CTGCG-----------
3579  165_HRV36a    --------------------
3580  166_HRV36b    --------------------
3581  167_HRV36     --------------------
3582  168_HRV89a    ----ACGTG-----------
3583  169_HRV89b    ----ACGTA-----------
3584  170_HRV89     ----ACGTC-----------
3585  171_HRV58     ----CTGCT-----------
3586  172_HRV58a    ----CTGCA-----------
3587  173_HRV58b    ----CTGCC-----------
3588  174_HRV12a    --------------------
3589  175_HRV12b    --------------------
3590  176_HRV12     --------------------
3591  177_HRV78a    --------------------
3592  178_HRV78b    --------------------
3593  179_HRV78     --------------------
3594  180_HRV20     CCCACAGAAATGACGAATGTT
3595  181_HRV20a    CCCACAGAAATGACGAATGTA
3596  182_HRV20b    CCCACAGAAATGACGAATGTG
3597  183_HRV68     CCTCCAGAATTAGCAAACCTT
3598  184_HRV68a    CCTCCAGAATTAGCAAACCTT
3599  185_HRV68b    CCTCCAGAATTAGCAAACCTT
3600  186_HRV28     ----CAGTT-----------
3601  187_HRV28a    ----CAGTA-----------
3602  188_HRV28b    ----CAGTC-----------
3603  189_HRV53a    ----CAGTAATGACAGCT---
3604  190_HRV53b    ----CAGTAATGACAGCT---
3605  191_HRV53     ----CAGTAATGACAGCA---
3606  192_HRV46a    ----CAGCA-----------
3607  193_HRV46b    ----CAGCC-----------
3608  194_HRV46     ----CAGCT-----------
3609  195_HRV80a    ----CAGTA-----------
3610  196_HRV80b    ----CAGTC-----------
3611  197_HRV80     ----CAGTT-----------
3612  198_HRV51     -----TT-------------
3613  199_HRV51a    -----TA-------------
3614  200_HRV51b    -----TG-------------
3615  201_HRV65a    -----TG-------------
3616  202_HRV65b    -----TA-------------
3617  203_HRV65     -----TT-------------
3618  204_HRV71a    -----ACTAA----------
3619  205_HRV71b    -----ACTAG----------
3620  206_HRV71     -----ACTAT----------
3621  207_HRV8      --------------------
3622  208_HRV95     --------------------
3623  209_HRV45     --------------------
3624  210_HRV45a    --------------------
3625  211_HRV45b    --------------------
3626  GROUP_1       --------------------
3627
3628
3629
3630  Summary:
3631
3632  GROUP_1       AA-CC--T-GA----T------A-----T--T-----A-GT--T--T-GT-CC--A----
3633  SUMMARY       AA-CC--T-GA----T------A-----T--T-----A-GT--T--T-GT-CC--A----
```

FIG. D11 CONT'D

```
07.trace                                                                  9/20/2007 5:04 PM
3634
3635 GROUP_1      ------AG----------------A--C-G---C-----T-GA-GC-GC-GA-AC-GG-
3636 SUMMARY      ------AG----------------A--C-G---C-----T-GA-GC-GC-GA-AC-GG-
3637
3638 GROUP_1      CA-AC-A--------CA-CC-GA-GA-----T-GA-AC--G----GT-----------A-
3639 SUMMARY      CA-AC-A--------CA-CC-GA-GA-----T-GA-AC--G----GT-----------A-
3640
3641 GROUP_1      AC-----ATGA-A------T-GA----TT--T-GG--G--C----TG-------------
3642 SUMMARY      AC-----ATGA-A------T-GA----TT--T-GG--G--C----TG-------------
3643
3644 GROUP_1      ------------------------------------------------------------
3645 SUMMARY      ------------------------------------------------------------
3646
3647 GROUP_1      ------------TGG----T-A---T----GA-ATG-C-CA--T--G--G-AA----GA-
3648 SUMMARY      ------------TGG----T-A---T----GA-ATG-C-CA--T--G--G-AA----GA-
3649
3650 GROUP_1      -T-TT-AC-TA-----G-TT--A-TC-GA--T-AC--T-G-T-----------C------
3651 SUMMARY      -T-TT-AC-TA-----G-TT--A-TC-GA--T-AC--T-G-T-----------C------
3652
3653 GROUP_1      --------------GG-CA--T-----T-CA-T--ATGT---T-CC-CC-GG-G--CC---
3654 SUMMARY      --------------GG-CA--T-----T-CA-T--ATGT---T-CC-CC-GG-G--CC---
3655
3656 GROUP_1      -CC--------G--------------TGG-A--C--G-A--AA----TC----TT-TGGCA
3657 SUMMARY      -CC--------G--------------TGG-A--C--G-A--AA----TC----TT-TGGCA
3658
3659 GROUP_1      ----GG-CA----T--CC--G--T--C--T-CC-TT-----G--T-GC-TC-G--TA-TA
3660 SUMMARY      ----GG-CA----T--CC--G--T--C--T-CC-TT-----G--T-GC-TC-G--TA-TA
3661
3662 GROUP_1      -ATGTT-TA-GA-GG-TA-----------------------TA-GG-------------
3663 SUMMARY      -ATGTT-TA-GA-GG-TA-----------------------TA-GG-------------
3664
3665 GROUP_1      -AA----ATGGG--C--T-T------G--T--T-AC-------CA---------------
3666 SUMMARY      -AA----ATGGG--C--T-T------G--T--T-AC-------CA---------------
3667
3668 GROUP_1      --T-----------T-T--C--AA-GC-AA-CA----------TGG-G-CC--G--C-C-
3669 SUMMARY      --T-----------T-T--C--AA-GC-AA-CA----------TGG-G-CC--G--C-C-
3670
3671 GROUP_1      --G-G---T----TA--------------------AA-T---------------------
3672 SUMMARY      --G-G---T----TA--------------------AA-T---------------------
3673
3674 GROUP_1      -----------------------T--------G---------------------------
3675 SUMMARY      -----------------------T--------G---------------------------
3676
3677 GROUP_1      --------------------
3678 SUMMARY      --------------------
3679
3680
```

FIG. D11 CONT'D

```
08.trace                                                            9/20/2007 5:05 PM
     1  Group  1:   1_HRV1A1|d
     2  Group  1:   2_HRV1A2|d
     3  Group  1:   3_HRV1A|cD
     4  Group  1:   4_HRV1B1|d
     5  Group  1:   5_HRV1B2|d
     6  Group  1:   6_HRV1B
     7  Group  1:   7_HRV40a|d
     8  Group  1:   8_HRV40b|d
     9  Group  1:   9_HRV40
    10  Group  1:  10_HRV85
    11  Group  1:  11_HRV85a|
    12  Group  1:  12_HRV85b|
    13  Group  1:  13_HRV56a|
    14  Group  1:  14_HRV56b|
    15  Group  1:  15_HRV56
    16  Group  1:  16_HRV54
    17  Group  1:  17_HRV98
    18  Group  1:  18_HRV59a|
    19  Group  1:  19_HRV59b|
    20  Group  1:  20_HRV59
    21  Group  1:  21_HRV63
    22  Group  1:  22_HRV63b|
    23  Group  1:  23_HRV63a|
    24  Group  1:  24_HRV39
    25  Group  1:  25_HRV39a|
    26  Group  1:  26_HRV39b|
    27  Group  1:  27_HRV10a|
    28  Group  1:  28_HRV10b|
    29  Group  1:  29_HRV10
    30  Group  1:  30_HRV100a
    31  Group  1:  31_HRV100b
    32  Group  1:  32_HRV100
    33  Group  1:  33_HRV66
    34  Group  1:  34_HRV66b|
    35  Group  1:  35_HRV66a|
    36  Group  1:  36_HRV77a|
    37  Group  1:  37_HRV77b|
    38  Group  1:  38_HRV77
    39  Group  1:  39_HRV62a
    40  Group  1:  40_HRV62b
    41  Group  1:  41_HRV25
    42  Group  1:  42_HRV29a
    43  Group  1:  43_HRV29b
    44  Group  1:  44_HRV44a
    45  Group  1:  45_HRV44b
    46  Group  1:  46_HRV31
    47  Group  1:  47_HRV31a|
    48  Group  1:  48_HRV31b|
    49  Group  1:  49_HRV47
    50  Group  1:  50_HRV47a|
    51  Group  1:  51_HRV47b|
    52  Group  1:  52_HRV11
    53  Group  1:  53_HRV11b|
    54  Group  1:  54_HRV11a|
    55  Group  1:  55_HRV76
    56  Group  1:  56_HRV76b|
    57  Group  1:  57_HRV76a|
    58  Group  1:  58_HRV33
    59  Group  1:  59_HRV33b|
    60  Group  1:  60_HRV33a|
    61  Group  1:  61_HRV24a|
    62  Group  1:  62_HRV24b|
    63  Group  1:  63_HRV24
    64  Group  1:  64_HRV90
    65  Group  1:  65_HRV90a|
```

FIG. D12

08.trace                                                              9/20/2007 5:05 PM

```
 66 Group 1:  66_HRV90b|
 67 Group 1:  67_HRV34
 68 Group 1:  68_HRV34b|
 69 Group 1:  69_HRV34a|
 70 Group 1:  70_HRV50a|
 71 Group 1:  71_HRV50b|
 72 Group 1:  72_HRV50
 73 Group 1:  73_HRV18a|
 74 Group 1:  74_HRV18b|
 75 Group 1:  75_HRV18
 76 Group 1:  76_HRV55
 77 Group 1:  77_HRV55b|
 78 Group 1:  78_HRV55a|
 79 Group 1:  79_HRV57
 80 Group 1:  80_HRV57a|
 81 Group 1:  81_HRV57b|
 82 Group 1:  82_HRV21
 83 Group 1:  83_HRVHan
 84 Group 1:  84_HRV43
 85 Group 1:  85_HRV43b|
 86 Group 1:  86_HRV43a|
 87 Group 1:  87_HRV75
 88 Group 1:  88_HRV75b|
 89 Group 1:  89_HRV75a|
 90 Group 1:  96_HRV9a|d
 91 Group 1:  97_HRV9b|d
 92 Group 1:  98_HRV9
 93 Group 1:  99_HRV32
 94 Group 1: 100_HRV32a
 95 Group 1: 101_HRV32b
 96 Group 1: 102_HRV67
 97 Group 1: 103_HRV67a
 98 Group 1: 104_HRV67b
 99 Group 1: 105_HRV15
100 Group 1: 106_HRV15a
101 Group 1: 107_HRV15b
102 Group 1: 108_HRV74a
103 Group 1: 109_HRV74b
104 Group 1: 110_HRV74
105 Group 1: 111_HRV38a
106 Group 1: 112_HRV38b
107 Group 1: 113_HRV38
108 Group 1: 114_HRV60
109 Group 1: 115_HRV60a
110 Group 1: 116_HRV60b
111 Group 1: 117_HRV64a
112 Group 1: 118_HRV64b
113 Group 1: 119_HRV64
114 Group 1: 120_HRV94a
115 Group 1: 121_HRV94b
116 Group 1: 122_HRV94
117 Group 1: 123_HRV22
118 Group 1: 124_HRV22a
119 Group 1: 125_HRV22b
120 Group 1: 126_HRV82
121 Group 1: 127_HRV82b
122 Group 1: 128_HRV82a
123 Group 1: 129_HRV19
124 Group 1: 130_HRV19a
125 Group 1: 131_HRV19b
126 Group 1: 132_HRV13
127 Group 1: 133_HRV13a
128 Group 1: 134_HRV13b
129 Group 1: 135_HRV41
130 Group 1: 136_HRV41a
```

FIG. D12 CONT'D 08.trace                                                                                    9/20/2007 5:05 PM

```
131 Group 1: 137_HRV41b
132 Group 1: 138_HRV73
133 Group 1: 139_HRV73b
134 Group 1: 140_HRV73a
135 Group 1: 141_HRV61
136 Group 1: 142_HRV61a
137 Group 1: 143_HRV61b
138 Group 1: 144_HRV96
139 Group 1: 145_HRV96b
140 Group 1: 146_HRV96a
141 Group 1: 90_HRV16a|
142 Group 1: 91_HRV16b|
143 Group 1: 92_1AYM_A
144 Group 1: 93_HRV81a|
145 Group 1: 94_HRV81b|
146 Group 1: 95_HRV81
147
148 Group 2: 147_HRV2
149 Group 2: 148_HRV2a|
150 Group 2: 149_HRV2b|
151 Group 2: 150_HRV49a
152 Group 2: 151_HRV49b
153 Group 2: 152_HRV49
154 Group 2: 153_HRV23a
155 Group 2: 154_HRV23b
156 Group 2: 155_HRV23
157 Group 2: 156_HRV30a
158 Group 2: 157_HRV30b
159 Group 2: 158_HRV30
160
161 Group 3: 159_HRV7
162 Group 3: 160_HRV7b|
163 Group 3: 161_HRV7a|
164 Group 3: 162_HRV88
165 Group 3: 163_HRV88a
166 Group 3: 164_HRV88b
167 Group 3: 165_HRV36a
168 Group 3: 166_HRV36b
169 Group 3: 167_HRV36
170 Group 3: 168_HRV89a
171 Group 3: 169_HRV89b
172 Group 3: 170_HRV89
173 Group 3: 171_HRV58
174 Group 3: 172_HRV58a
175 Group 3: 173_HRV58b
176
177 Group 4: 174_HRV12a
178 Group 4: 175_HRV12b
179 Group 4: 176_HRV12
180 Group 4: 177_HRV78a
181 Group 4: 178_HRV78b
182 Group 4: 179_HRV78
183
184 Group 5: 180_HRV20
185 Group 5: 181_HRV20a
186 Group 5: 182_HRV20b
187 Group 5: 183_HRV68
188 Group 5: 184_HRV68a
189 Group 5: 185_HRV68b
190 Group 5: 186_HRV28
191 Group 5: 187_HRV28a
192 Group 5: 188_HRV28b
193 Group 5: 189_HRV53a
194 Group 5: 190_HRV53b
195 Group 5: 191_HRV53
```

FIG. D12 CONT'D

```
08.trace                                                               9/20/2007 5:05 PM 196 Group 5: 192_HRV46a
197 Group 5: 193_HRV46b
198 Group 5: 194_HRV46
199 Group 5: 195_HRV80a
200 Group 5: 196_HRV80b
201 Group 5: 197_HRV80
202 Group 5: 198_HRV51
203 Group 5: 199_HRV51a
204 Group 5: 200_HRV51b
205 Group 5: 201_HRV65a
206 Group 5: 202_HRV65b
207 Group 5: 203_HRV65
208 Group 5: 204_HRV71a
209 Group 5: 205_HRV71b
210 Group 5: 206_HRV71
211
212 Group 6: 207_HRV8
213 Group 6: 208_HRV95
214 Group 6: 209_HRV45
215 Group 6: 210_HRV45a
216 Group 6: 211_HRV45b
217
218
219 >>>>>
220
221
222
223 Group 1:
224
225  1_HRV1A1|d    AATCCAGTAGAAAACTACATTGATGAAGTTTTAAATGAAGTTTTAGTAGTGCCGAATATA
226  2_HRV1A2|d    AATCCAGTAGAAAACTACATTGATGAAGTTTTAAATGAAGTTTTAGTAGTGCCGAATATA
227  3_HRV1A|cD    AATCCAGTAGAAAACTACATTGATGAAGTTTTAAATGAAGTTTTAGTAGTGCCGAATATA
228  4_HRV1B1|d    AATCCAGTGGAAAATTACATTGATGAAGTTTTAAATGAAGTTCTAGTAGTACCAAATATA
229  5_HRV1B2|d    AATCCAGTGGAAAATTACATTGATGAAGTTTTAAATGAAGTTCTAGTAGTACCAAATATA
230  6_HRV1B       AATCCAGTGGAAAATTACATTGATGAAGTTTTAAATGAAGTTCTAGTAGTACCAAATATA
231  7_HRV40a|d    AACCCCGTTGAAAGGTATGTTGATGAGGTTCTTAATGAAGTTCTGGTAGTTCCAAATATC
232  8_HRV40b|d    AACCCCGTTGAAAGGTATGTTGATGAGGTTCTTAATGAAGTTCTGGTAGTTCCAAATATC
233  9_HRV40       AACCCCGTTGAAAGGTATGTTGATGAGGTTCTTAATGAAGTTCTGGTAGTTCCAAATATC
234 10_HRV85       AATCCTGTTGAAAAATACGTTGATGAAGTCCTTAATGAGGTTCTAGTGGTTCCAAATATC
235 11_HRV85a|     AATCCTGTTGAAAAATACGTTGATGAAGTCCTTAATGAGGTTCTAGTGGTTCCAAATATC
236 12_HRV85b|     AATCCTGTTGAAAAATACGTTGATGAAGTCCTTAATGAGGTTCTAGTGGTTCCAAATATC
237 13_HRV56a|     AACCCAGTTGAGAGATATGTAGATGATGTTTTAAATGAAGTTTTAGTTGTTCCAAATATT
238 14_HRV56b|     AACCCAGTTGAGAGATATGTAGATGATGTTTTAAATGAAGTTTTAGTTGTTCCAAATATT
239 15_HRV56       AACCCAGTTGAGAGATATGTAGATGATGTTTTAAATGAAGTTTTAGTTGTTCCAAATATT
240 16_HRV54       AATCCTGTAGAAAGATATGTTGATGAAGTGTTAAATGAAGTGTTAGTTGTCCCAAACATT
241 17_HRV98       AATCCTGTAGAGAGATATGTTGATGAAGTATTAAATGAAGTGTTAGTTGTTCCAAACATT
242 18_HRV59a|     AACCCAGTGGAAAACTATGTTAATGATGTACTTAATGAGGTTTTAGTAGTACCAAATATA
243 19_HRV59b|     AACCCAGTGGAAAACTATGTTAATGATGTACTTAATGAGGTTTTAGTAGTACCAAATATA
244 20_HRV59       AACCCAGTGGAAAACTATGTTAATGATGTACTTAATGAGGTTTTAGTAGTACCAAATATA
245 21_HRV63       AATCCAGTAGAGAATTATGTAAATGATGTTCTTAATGAAGTGTTAGTTGTTCCAAACATA
246 22_HRV63b|     AATCCAGTAGAGAATTATGTAAATGATGTTCTTAATGAAGTGTTAGTTGTTCCAAACATA
247 23_HRV63a|     AATCCAGTAGAGAATTATGTAAATGATGTTCTTAATGAAGTGTTAGTTGTTCCAAACATA
248 24_HRV39       AATCCAGTAGAAAATTATATAGATGAAGTATTAAATGAGGTATTAGTTGTTCCTAATATA
249 25_HRV39a|     AATCCAGTAGAAAATTATATAGATGAAGTATTAAATGAGGTATTAGTTGTTCCTAATATA
250 26_HRV39b|     AATCCAGTAGAAAATTATATAGATGGAGTATTAAATGAGGTATTAGTTGTTCCTAATATA
251 27_HRV10a|     AATCCAGTTGAAAATTACATTGATAATGTACTTAATGAAGTCCTAGTGGTACCCAACATC
252 28_HRV10b|     AATCCAGTTGAAAATTACATTGATAATGTACTTAATGAAGTCCTAGTGGTACCCAACATC
253 29_HRV10       AATCCAGTTGAAAATTACATTGATAATGTACTTAATGAAGTCCTAGTGGTACCCAACATC
254 30_HRV100a     AATCCAGTAGAAAATTATGTTGAAGGTGTGCTGAATGAAGTACTAGTGGTACCTAATATT
255 31_HRV100b     AATCCAGTAGAAAATTATGTTGAAGGTGTGCTGAATGAAGTACTAGTGGTACCTAATATT
256 32_HRV100      AATCCAGTAGAAAATTATGTTGAAGGTGTGCTGAATGAAGTACTAGTGGTACCTAATATT
257 33_HRV66       AATCCAGTTGAAGATTATGTTGAGGGTGTTTTAAATGAAGTTTAGTAGTACCAAACATC
258 34_HRV66b|     AATCCAGTTGAAGATTATGTTGAGGGTGTTTTAAATGAAGTTTTAGTAGTACCAAACATC
259 35_HRV66a|     AATCCAGTTGAAGATTATGTTGAGGGTGTTTTAAATGAAGTTTTAGTAGTACCAAACATC
260 36_HRV77a|     AATCCAGTTGAGGACTATATCGATAATGTACTTAATGAAGTCTTAGTAGTACCAAATACC
```

```
08.trace                                                              9/20/2007 5:05 PM 261  37_HRV77b|    AATCCAGTTGAGGACTATATCGATAATGTACTTAATGAAGTCTTAGTAGTACCAAATACC
262  38_HRV77     AATCCAGTTGAGGACTATATCGATAATGTACTTAATGAAGTCTTAGTAGTACCAAATACC
263  39_HRV62a    AATCCAATTGAAAATTATGTAGATCAAGTACTTAATGAAGTTTTAGTTGTACCAAATATT
264  40_HRV62b    AATCCAATTGAAAATTATGTAGATCAAGTACTTAATGAAGTTTTAGTTGTACCAAATATT
265  41_HRV25     AATCCAATTGAAAATTATGTAGATCAAGTACTTAATGAGGTTCTAGTCGTACCAAATATT
266  42_HRV29a    AACCCAGTTGAAAACTATGTGGATGAGGTGCTTAATGAAGTTTTAGTTGTGCCTAACATC
267  43_HRV29b    AACCCAGTTGAAAACTATGTGGATGAGGTGCTTAATGAAGTTTTAGTTGTGCCTAACATC
268  44_HRV44a    AACCCAGTTGAAAATTATGTGGATGAAGTACTTAATGAAGTCTTAGTTGTGCCTAATATC
269  45_HRV44b    AACCCAGTTGAAAATTATGTGGATGAAGTACTTAATGAAGTCTTAGTTGTGCCTAATATC
270  46_HRV31     AATCCAGTTGAAAACTATGTGGAAGAGGTTCTTAATGAAGTCTTAGTAGTACCTAATATC
271  47_HRV31a|   AATCCAGTTGAAAACTATGTGGAAGAGGTTCTTAATGAAGTCTTAGTAGTACCTAATATC
272  48_HRV31b|   AATCCAGTTGAAAACTATGTGGAAGAGGTTCTTAATGAAGTCTTAGTAGTACCTAATATC
273  49_HRV47     AACCCAGTCGAAAATTATGTGGAAGAGGTACTTAATGAGGTCTTAGTTGTACCAAATATC
274  50_HRV47a|   AACCCAGTCGAAAATTATGTGGAAGAGGTACTTAATGAGGTCTTAGTTGTACCAAATATC
275  51_HRV47b|   AACCCAGTCGAAAATTATGTGGAAGAGGTACTTAATGAGGTCTTAGTTGTACCAAATATC
276  52_HRV11     AACCCAGTGGAGGATTATGTTGATGGAATTCTAAATGAGGTTTTAGTGTACCTAATATA
277  53_HRV11b|   AACCCAGTGGAGGATTATGTTGATGGAATTCTAAATGAGGTTTTAGTTGTACCTAATATA
278  54_HRV11a|   AACCCAGTGGAGGATTATGTTGATGGAATTCTAAATGAGGTTTTAGTTGTACCTAATATA
279  55_HRV76     AACCCAGTTGAAAATTACGTGGATGAGATATTAAATGAGGTTCTTGTAGTACCAAACATC
280  56_HRV76b|   AACCCAGTTGAAAATTACGTGGATGAGATATTAAATGAGGTTCTTGTAGTACCAAACATC
281  57_HRV76a|   AACCCAGTTGAAAATTACGTGGATGAGATATTAAATGAGGTTCTTGTAGTACCAAACATC
282  58_HRV33     AATCCAGTAGAGAATTATATAGAAGAGGTGTTGAATGAGGTTTTAGTAGTGCCTAATATC
283  59_HRV33b|   AATCCAGTAGAGAATTATATAGAAGAGGTGTTGAATGAGGTTTTAGTAGTGCCTAATATC
284  60_HRV33a|   AATCCAGTAGAGAATTATATAGAAGAGGTGTTGAATGAGGTTTTAGTAGTGCCTAATATC
285  61_HRV24a|   AACCCAGTAGAAAATTATATAGATGAGGTTTTGAATGAAGTACTGGTTGTGCCTAATATT
286  62_HRV24b|   AACCCAGTAGAAAATTATATAGATGAGGTTTTGAATGAAGTACTGGTTGTGCCTAATATT
287  63_HRV24     AACCCAGTAGAAAATTATATAGATGAGGTTTTGAATGAAGTACTGGTTGTGCCTAATATT
288  64_HRV90     AATCCAGTGGAAAATTATATAGATGAAGTCCTAAATGAGGTATTGGTTGTCCCTAATATT
289  65_HRV90a|   AATCCAGTGGAAAATTATATAGATGAAGTCCTAAATGAGGTATTGGTTGTCCCTAATATT
290  66_HRV90b|   AATCCAGTGGAAAATTATATAGATGAAGTCCTAAATGAGGTATTGGTTGTCCCTAATATT
291  67_HRV34     AATCCAGTTGAAAATTACATAGATGAGGTACTAAATGAGGTATTGGTTGTACCAAACATT
292  68_HRV34b|   AATCCAGTTGAAAATTACATAGATGAGGTACTAAATGAGGTATTGGTTGTACCAAACATT
293  69_HRV34a|   AATCCAGTTGAAAATTACATAGATGAGGTACTAAATGAGGTATTGGTTGTACCAAACATT
294  70_HRV50a|   AATCCAGTGGAGAATTACATAGATGAAGTATTAAATGAGGTATTAGTTGTCCCAAATATC
295  71_HRV50b|   AATCCAGTGGAGAATTACATAGATGAAGTATTAAATGAGGTATTAGTTGTCCCAAATATC
296  72_HRV50     AATCCAGTGGAGAATTACATAGATGAAGTATTAAATGAGGTATTAGTTGTCCCAAATATC
297  73_HRV18a|   AATCCAGTAGAGAATTATATAGATGAAGTACTTAATGAAGTGTTAGTGGTCCCAAATGTG
298  74_HRV18b|   AATCCAGTAGAGAATTATATAGATGAAGTACTTAATGAAGTGTTAGTGGTCCCAAATGTG
299  75_HRV18     AATCCAGTAGAGAATTATATAGATGAAGTACTTAATGAAGTGTTAGTGGTCCCAAATGTG
300  76_HRV55     AATCCTGTAGAGAGATATGTTGATGAAGTCCTGAATGAAGTGCTAGTAGTTCCAAATATT
301  77_HRV55b|   AATCCTGTAGAGAGATATGTTGATGAAGTCCTGAATGAAGTGCTAGTAGTTCCAAATATT
302  78_HRV55a|   AATCCTGTAGAGAGATATGTTGATGAAGTCCTGAATGAAGTGCTAGTAGTTCCAAATATT
303  79_HRV57     AACCCAGTAGAAAATTTTGTGGATGAGATCTTGAATGAAGTTTTGGTGGTTCCAGATATC
304  80_HRV57a|   AACCCAGTAGAAAATTTTGTGGATGAGATCTTGAATGAAGTTTTGGTGGTTCCAGATATC
305  81_HRV57b|   AACCCAGTAGAAAATTTTGTGGATGAGATCTTGAATGAAGTTTTGGTGGTTCCAGATATC
306  82_HRV21     AATCCTGTAGAGAATTATATAGATGAAGTACTTAATGAAGTCTTAGTAGTGCCAAATATC
307  83_HRVHan    AATCCTGTAGAGAATTACGTAGATGAAGTTCTAAATGAGGTCTTAGTAGTGCCAAATATC
308  84_HRV43     AATCCTGTTGAAAATTATGTTGATGAAATTTAAATCAAGTTCTTGTAGTCCCAAACACT
309  85_HRV43b|   AATCCTGTTGAAAATTATGTTGATGAAATTTTAAATCAAGTTCTTGTAGTCCCAAACACT
310  86_HRV43a|   AATCCTGTTGAAAATTATGTTGATGAAATTTTAAATCAAGTTCTTGTAGTCCCAAACACT
311  87_HRV75     AATCCAGTTGAAAATTATGTGGATGAAATTTTAAACCAAGTTCTGGTAGTTCCAAACACC
312  88_HRV75b|   AATCCAGTTGAAAATTATGTGGATGAAATTTTAAACCAAGTTCTGGTAGTTCCAAACACC
313  89_HRV75a|   AATCCAGTTGAAAATTATGTGGATGAAATTTTAAACCAAGTTCTGGTAGTTCCAAACACC
314  96_HRV9a|d   AACCCAGTGGAGAATTACATAGATCAGGTGCTTAATGAGGTTTTGGTAGTCCCAAACATT
315  97_HRV9b|d   AACCCAGTGGAGAATTACATAGATCAGGTGCTTAATGAGGTTTTGGTAGTCCCAAACATT
316  98_HRV9      AATCCAGTGGAGAATTACATAGATCAGGTGCTTAATGAGGTTTTGGTAGTCCCAAACATT
317  99_HRV32     AATCCTGTGGAGAATTACATAGATCAAGTTTTAAATGAAGTTTTGGTAGTTCCAAACATC
318  100_HRV32a   AATCCTGTGGAGAATTACATAGATCAAGTTTTAAATGAAGTTTTGGTAGTTCCAAACATC
319  101_HRV32b   AATCCTGTGGAGAATTACATAGATCAAGTTTTAAATGAAGTTTTGGTAGTTCCAAACATC
320  102_HRV67    AACCCAGTAGAAGATTATGTAGATCAGGTATTGAATGAGGTCCTGGTGGTGCCAAATATA
321  103_HRV67a   AACCCAGTAGAAGATTATGTAGATCAGGTATTGAATGAGGTCCTGGTGGTGCCAAATATA
322  104_HRV67b   AACCCAGTAGAAGATTATGTAGATCAGGTATTGAATGAGGTCCTGGTGGTGCCAAATATA
323  105_HRV15    AACCCAGTGGAGAATTACATAGATGAAGTGTTAAATGAGGTTCTAGTAGTTCCAAACATT
324  106_HRV15a   AACCCAGTGGAGAATTACATAGATGAAGTGTTAAATGAGGTTCTAGTAGTTCCAAACATT
325  107_HRV15b   AACCCAGTGGAGAATTACATAGATGAAGTGTTAAATGAGGTTCTAGTAGTTCCAAACATT
```

FIG. D12 CONT'D

```
08.trace                                                                                          9/20/2007 5:05 PM 326  108_HRV74a   AACCCAGTGGAGAATTACATAGATGAAGTGTTGAATGAAGTGTTAGTTGTTCCAAATATT
327  109_HRV74b   AACCCAGTGGAGAATTACATAGATGAAGTGTTGAATGAAGTGTTAGTTGTTCCAAATATT
328  110_HRV74    AACCCAGTGGAGAATTACATAGATGAAGTGTTGAATGAAGTGTTAGTTGTTCCAAATATT
329  111_HRV38a   AACCCAGTAGAGGAATACATAGATGGAGTCTTGAATGAGGTTCTTGTGGTTCCGAACATT
330  112_HRV38b   AACCCAGTAGAGGAATACATAGATGGAGTCTTGAATGAGGTTCTTGTGGTTCCGAACATT
331  113_HRV38    AACCCAGTAGAGGAATACATAGATGGAGTCTTGAATGAGGTTCTTGTGGTTCCGAACATT
332  114_HRV60    AATCCAGTAGAAAGCTACATAGATGGGGTCTTAAACGAAGTCCTTGTGGTTCCAAACATT
333  115_HRV60a   AATCCAGTAGAAAGCTACATAGATGGGGTCTTAAACGAAGTCCTTGTGGTTCCAAACATT
334  116_HRV60b   AATCCAGTAGAAAGCTACATAGATGGGGTCTTAAACGAAGTCCTTGTGGTTCCAAACATT
335  117_HRV64a   AACCCAGTTGAACAATACATTGATGGTGTGTTGAATGAAGTTTTGATTGTCCCAAACATC
336  118_HRV64b   AACCCAGTTGAACAATACATTGATGGTGTGTTGAATGAAGTTTTGATTGTCCCAAACATC
337  119_HRV64    AACCCAGTTGAACAATACATTGATGGTGTGTTGAATGAAGTTTTGATTGTCCCAAACATC
338  120_HRV94a   AATCCAGTTGAGAAATACATTGATGGTGTATTGAATGAAGTTTTAGTTGTTCCAAATATC
339  121_HRV94b   AATCCAGTTGAGAAATACATTGATGGTGTATTGAATGAAGTTTTAGTTGTTCCAAATATC
340  122_HRV94    AATCCAGTTGAGAAATACATTGATGGTGTATTGAATGAAGTTTTAGTTGTTCCAAATATC
341  123_HRV22    AACCCTGTAGAGAAATACATTGATGGTGTATTGAATGAAGTATTGGTTGTTCCAAACACA
342  124_HRV22a   AACCCTGTAGAGAAATACATTGATGGTGTATTGAATGAAGTATTGGTTGTTCCAAACACA
343  125_HRV22b   AACCCTGTAGAGAAATACATTGATGGTGTATTGAATGAAGTATTGGTTGTTCCAAACACA
344  126_HRV82    AATCCAGTTGAAAAGTATGTTGATAGTGTTTTAAACGAGGTATTAGTTGTTCCTAACATT
345  127_HRV82b   AATCCAGTTGAAAAGTATGTTGATAGTGTTTTAAACGAGGTATTAGTTGTTCCTAACATT
346  128_HRV82a   AATCCAGTTGAAAAGTATGTTGATAGTGTTTTAAACGAGGTATTAGTTGTTCCTAACATT
347  129_HRV19    AATCCTGTAGAGAAATATGTGGACACCATTCTGAATGAGGTGCTAGTTGTCCCAAATATC
348  130_HRV19a   AATCCTGTAGAGAAATATGTGGACACCATTCTGAATGAGGTGCTAGTTGTCCCAAATATC
349  131_HRV19b   AATCCTGTAGAGAAATATGTGGACACCATTCTGAATGAGGTGCTAGTTGTCCCAAATATC
350  132_HRV13    AATCCTGTTGAAAGGTATGTAGATGAAGTCTTGAATGAAGTTCTTGTAGTACCAAATATC
351  133_HRV13a   AATCCTGTTGAAAGGTATGTAGATGAAGTCTTGAATGAAGTTCTTGTAGTACCAAATATC
352  134_HRV13b   AATCCTGTTGAAAGGTATGTAGATGAAGTCTTGAATGAAGTTCTTGTAGTACCAAATATC
353  135_HRV41    AATCCTGTAGAAAGGTATGTGGATGAGGTCCTGAATGAGGTTCTTGTGGTACCAAATATT
354  136_HRV41a   AATCCTGTAGAAAGGTATGTGGATGAGGTCCTGAATGAGGTTCTTGTGGTACCAAATATT
355  137_HRV41b   AATCCTGTAGAAAGGTATGTGGATGAGGTCCTGAATGAGGTTCTTGTGGTACCAAATATT
356  138_HRV73    AATCCTGTAGAAAGATATGTAGATGAAGTTTTGAATGAAGTCCTTGTAGTACCCAATATC
357  139_HRV73b   AATCCTGTAGAAAGATATGTAGATGAAGTTTTGAATGAAGTCCTTGTAGTACCCAATATC
358  140_HRV73a   AATCCTGTAGAAAGATATGTAGATGAAGTTTTGAATGAAGTCCTTGTAGTACCCAATATC
359  141_HRV61    AACCCTGTGGAAAGATATGTAGATGAAGTTTTAAATGAAGTGCTTGTAGTCCCAAACATT
360  142_HRV61a   AACCCTGTGGAAAGATATGTAGATGAAGTTTTAAATGAAGTGCTTGTAGTCCCAAACATT
361  143_HRV61b   AACCCTGTGGAAAGATATGTAGATGAAGTTTTAAATGAAGTGCTTGTAGTCCCAAACATT
362  144_HRV96    AACCCTGTAGAGAGATATGTAGATGAAGTCTTGAATGAGGTTCTTGTAGTCCCTAATATT
363  145_HRV96b   AACCCTGTAGAGAGATATGTAGATGAAGTCTTGAATGAGGTTCTTGTAGTCCCTAATATT
364  146_HRV96a   AACCCTGTAGAGAGATATGTAGATGAAGTCTTGAATGAGGTTCTTGTAGTCCCTAATATT
365  90_HRV16a|   AATCCAGTGGAAAGATATGTAGATGAAGTCTTAAATGAAGTGTTAGTAGTGCCCAATATT
366  91_HRV16b|   AATCCAGTGGAAAGATATGTAGATGAAGTCTTAAATGAAGTGTTAGTAGTGCCCAATATT
367  92_1AYM_A    AATCCAGTGGAAAGATATGTAGATGAAGTCTTAAATGAAGTGTTAGTAGTGCCCAATATT
368  93_HRV81a|   AACCCAGTGGAGCGGTATGTGGATGAAGTCTTAAATGAGGTATTGGTACTCCCTAATATT
369  94_HRV81b|   AACCCAGTGGAGCGGTATGTGGATGAAGTCTTAAATGAGGTATTGGTACTCCCTAATATT
370  95_HRV81     AACCCAGTGGAGCGGTATGTGGATGAAGTCTTAAATGAGGTATTGGTACTCCCTAATATT
371  GROUP_1      AA--CC--T-GA----T---T--A-----T--T-AA--A-GT--T--T-GT-CC--A----
372
373  1_HRV1A1|d   AAAGAAAGTCATCACACTACATCAAACTCTGCCCCACTTTTAGATGCTGCAGAGACGGGA
374  2_HRV1A2|d   AAAGAAAGTCATCACACTACATCAAACTCTGCCCCACTTTTAGATGCTGCAGAGACGGGA
375  3_HRV1A|cD   AAAGAAAGTCATCACACTACATCAAACTCTGCCCCACTTTTAGATGCTGCAGAGACGGGA
376  4_HRV1B1|d   AAAGAAAGCCATCACACTACATCAAATTCTGCTCCACTCTTGGATGCTGCAGAGACAGGA
377  5_HRV1B2|d   AAAGAAAGCCATCACACTACATCAAATTCTGCTCCACTCTTGGATGCTGCAGAGACAGGA
378  6_HRV1B      AAAGAAAGCCATCACACTACATCAAATTCTGCTCCACTCTTGGATGCTGCAGAGACAGGA
379  7_HRV40a|d   AGAGAGAGCCATCCAACTACATCAAATTCGGCCCCTGCCTTGGATGCAGCAGAGACTGGA
380  8_HRV40b|d   AGAGAGAGCCATCCAACTACATCAAATTCGGCCCCTGCCTTGGATGCAGCAGAGACTGGA
381  9_HRV40      AGAGAGAGCCATCCAACTACATCAAATTCGGCCCCTGCCTTGGATGCAGCAGAGACTGGA
382  10_HRV85     AAAGAGAGTCACCCAACTATATCAAATTCAGCTCCTGCTTTGGATGCAGCAGAGACTGGC
383  11_HRV85a|   AAAGAGAGTCACCCAACTATATCAAATTCAGCTCCTGCTTTGGATGCAGCAGAGACTGGC
384  12_HRV85b|   AAAGAGAGTCACCCAACTATATCAAATTCAGCTCCTGCTTTGGATGCAGCAGAGACTGGC
385  13_HRV56a|   AGGGAGAGCCATCCATCCACATCAAATTCTGCCCCTGCATTAGATGCTGCTGAAACTGGC
386  14_HRV56b|   AGGGAGAGCCATCCATCCACATCAAATTCTGCCCCTGCATTAGATGCTGCTGAAACTGGC
387  15_HRV56     AGGGAGAGCCATCCATCCACATCAAATTCTGCCCCTGCATTAGATGCTGCTGAAACTGGC
388  16_HRV54     AGAGAAAGTCATCCAGCTACATCTAATTCAGCCCCTGCGCTAGATGCGGCAGAAACTGGA
389  17_HRV98     AAAGAAAGTCATCCACTACATCTCAAATTCGGCCCCTACACTAGATGCAGCAGAAACTGGG
390  18_HRV59a|   CAGGAAAGCCACCCAACCACCTCAAATGCTGCTCCAGCATTAGATGCAGCAGAGACTGGA
```

FIG. D12 CONT'D

08.trace                                                                                    9/20/2007 5:05 PM

```
391 19_HRV59b|   CAGGAAAGCCACCCAACCACCTCAAATGCTGCTCCAGCATTAGATGCAGCAGAGACTGGA
392 20_HRV59     CAGGAAAGCCACCCAACCACCTCAAATGCTGCTCCAGCATTAGATGCAGCAGAGACTGGA
393 21_HRV63     CAAGAAAGCCATCCAACCACATCAAACGCTGCTCCTGTACTTGATGCTGCGGAAACAGGA
394 22_HRV63b|   CAAGAAAGCCATCCAACCACATCAAACGCTGCTCCTGTACTTGATGCTGCGGAAACAGGA
395 23_HRV63a|   CAAGAAAGCCATCCAACCACATCAAACGCTGCTCCTGTACTTGATGCTGCGGAAACAGGA
396 24_HRV39     AGAGAGAGCCATCCAACTACATCTAATGCAGCTACAGCTTTGGATGCTGCTGAAACTGGA
397 25_HRV39a|   AGAGAGAGCCATCCAACTACATCTAATGCAGCTACAGCTTTGGATGCTGCTGAAACTGGA
398 26_HRV39b|   AGAGAGAGCCATCCAACTACATCTAATGCAGCTCCAGCTTTGGATGCTGCTGAAACTGGA
399 27_HRV10a|   AGAGAAAGTCATCCAAGCACCTCTAACTCTGCCCCAATTCTCGATGCAGCTGAGACTGGT
400 28_HRV10b|   AGAGAAAGTCATCCAAGCACCTCTAACTCTGCCCCAATTCTCGATGCAGCTGAGACTGGT
401 29_HRV10     AGAGAAAGTCATCCAAGCACCTCTAACTCTGCCCCAATTCTCGATGCAGCTGAGACTGGT
402 30_HRV100a   AGAGAGAGCCATCCAAGCACCTCAAACTCTGCTCCAATCCTTGATGCTGCTGAAACTGGC
403 31_HRV100b   AGAGAGAGCCATCCAAGCACCTCAAACTCTGCTCCAATCCTTGATGCTGCTGAAACTGGC
404 32_HRV100    AGAGAGAGCCATCCAAGCACCTCAAACTCTGCTCCAATCCTTGATGCTGCTGAAACTGGC
405 33_HRV66     AAGGAAAGCCATCCAAGCACATCAAATGCTGCCCCAATACTAGATGCAGCTGAAACAGGT
406 34_HRV66b|   AAGGAAAGCCATCCAAGCACATCAAATGCTGCCCCAATACTAGATGCAGCTGAAACAGGT
407 35_HRV66a|   AAGGAAAGCCATCCAAGCACATCAAATGCTGCCCCAATACTAGATGCAGCTGAAACAGGT
408 36_HRV77a|   AAGGAGAGTCATCCAAGCACTTCTAACTCTGCTCCTATACTAGATGCAGCTGAAACAGGC
409 37_HRV77b|   AAGGAGAGTCATCCAAGCACTTCTAACTCTGCTCCTATACTAGATGCAGCTGAAACAGGC
410 38_HRV77     AAGGAGAGTCATCCAAGCACTTCTAACTCTGCTCCTATACTAGATGCAGCTGAAACAGGC
411 39_HRV62a    AAAGAAAGTCACCCTAGTACGTCAAACTCTGCCCCAATTCTAGATGCTGCTGAAACCGGA
412 40_HRV62b    AAAGAAAGTCACCCTAGTACGTCAAACTCTGCCCCAATTCTAGATGCTGCTGAAACCGGA
413 41_HRV25     AAAGAAAGTCACCCAAGCACATCAAATTCTGCCCCAATTCTAGATGCTGCTGAAACTGGA
414 42_HRV29a    AGGGAGAGCCACCCAAGCACGTCCAACTCTGCACCAATCTTGGATGCTGCTGAGACTGGA
415 43_HRV29b    AGGGAGAGCCACCCAAGCACGTCCAACTCTGCACCAATCTTGGATGCTGCTGAGACTGGA
416 44_HRV44a    AGAGAGAGCCACCCAAGCACATCTAACTCTGCTCCAATTTTGGATGCTGCTGAAACTGGA
417 45_HRV44b    AGAGAGAGCCACCCAAGCATATCTAACTCTGCTCCAATTTTGGATGCTGCTGAAACTGGA
418 46_HRV31     AAAGAAAGCCATCCAAGCACATCTAATTCTGCCCCAATCCTGGACGCTGCTGAAACTGGA
419 47_HRV31a|   AAAGAAAGCCATCCAAGCACATCTAATTCTGCCCCAATCCTGGACGCTGCTGAAACTGGA
420 48_HRV31b|   AAAGAAAGCCATCCAAGCACATCTAATTCTGCCCCAATCCTGGACGCTGCTGAAACTGGA
421 49_HRV47     AAAGAAAGTCATCCAAGTACATCCAACTCTGCCCCGATTTTAGATGCTGCTGAAACTGGA
422 50_HRV47a|   AAAGAAAGTCATCCAAGTACATCCAACTCTGCCCCGATTTTAGATGCTGCTGAAACTGGA
423 51_HRV47b|   AAAGAAAGTCATCCAAGTACATCCAACTCTGCCCCGATTTTAGATGCTGCTGAAACTGGA
424 52_HRV11     AAGGAGAGCCAAGCTACCACATCAAACTCAGCACCTGCTCTAGATGCAGCTGAAACCGGA
425 53_HRV11b|   AAGGAGAGCCAAGCTACCACATCAAACTCAGCACCTGCTCTAGATGCAGCTGAAACCGGA
426 54_HRV11a|   AAGGAGAGCCAAGCTACCACATCAAACTCAGCACCTGCTCTAGATGCAGCTGAAACCGGA
427 55_HRV76     AAAGAGAGTCAGGCTACCACATCAAATGCAGCACCTGCTTTGGATGCAGCTGAGACTGGG
428 56_HRV76b|   AAAGAGAGTCAGGCTACCACATCAAATGCAGCACCTGCTTTGGATGCAGCTGAGACTGGG
429 57_HRV76a|   AAAGAGAGTCAGGCTACCACATCAAATGCAGCACCTGCTTTGGATGCAGCTGAGACTGGG
430 58_HRV33     AGAGAGAGTCAAGCAACCACATCAAATTCAGCACCTGCCTTAGATGCAGCTGAGACTGGA
431 59_HRV33b|   AGAGAGAGTCAAGCAACCACATCAAATTCAGCACCTGCCTTAGATGCAGCTGAGACTGGA
432 60_HRV33a|   AGAGAGAGTCAAGCAACCACATCAAATTCAGCACCTGCCTTAGATGCAGCTGAGACTGGA
433 61_HRV24a|   AAGGAAAGTAAACCATCAACATCAAACTCAGCACCAGCTTTGGATGCAGCAGAAACTGGA
434 62_HRV24b|   AAGGAAAGTAAACCATCAACATCAAACTCAGCACCAGCTTTGGATGCAGCAGAAACTGGA
435 63_HRV24     AAGGAAAGTAAACCATCAACATCAAACTCAGCACCAGCTTTGGATGCAGCAGAAACTGGA
436 64_HRV90     AAGGAAAGTAAACCTTCAACTTCAAACTCAGCGCCAGCTTTAGATGCAGCAGAAACCGGA
437 65_HRV90a|   AAGGAAAGTAAACCTTCAACTTCAAACTCAGCGCCAGCTTTAGATGCAGCAGAAACCGGA
438 66_HRV90b|   AAGGAAAGTAAACCTTCAACTTCAAACTCAGCGCCAGCTTTAGATGCAGCAGAAACCGGA
439 67_HRV34     AAAGAAAGCCAAGCCACCACATCAAACTCTGCCCCCGCACTGGATGCAGCTGAGACTGGT
440 68_HRV34b|   AAAGAAAGCCAAGCCACCACATCAAACTCTGCCCCCGCACTGGATGCAGCTGAGACTGGT
441 69_HRV34a|   AAAGAAAGCCAAGCCACCACATCAAACTCTGCCCCCGCACTGGATGCAGCTGAGACTGGT
442 70_HRV50a|   AAGGAGAGTCAAGCCACTACATCAAACTCTGCCCCTGCTTTAGATGCAGCTGAAACTGGA
443 71_HRV50b|   AAGGAGAGTCAAGCCACTACATCAAACTCTGCCCCTGCTTTAGATGCAGCTGAAACTGGA
444 72_HRV50     AAGGAGAGTCAAGCCACTACATCAAACTCTGCCCCTGCTTTAGATGCAGCTGAAACTGGA
445 73_HRV18a|   AATGAAAGTCACGCAATTACATCAAATTCAGCCCCTGCTTTAGATGCCGCTGAAACTGGT
446 74_HRV18b|   AATGAAAGTCACGCAATTACATCAAATTCAGCCCCTGCTTTAGATGCCGCTGAAACTGGT
447 75_HRV18     AATGAAAGTCACGCAATTACATCAAATTCAGCCCCTGCTTTAGATGCCGCTGAAACTGGT
448 76_HRV55     AGGGAGAGTCAAGCAGCAACATCAAATTCAGCTCCAGTACTAGATGCAGCAGAAACTGGG
449 77_HRV55b|   AGGGAGAGTCAAGCAGCAACATCAAATTCAGCTCCAGTACTAGATGCAGCAGAAACTGGG
450 78_HRV55a|   AGGGAGAGTCAAGCAGCAACATCAAATTCAGCTCCAGTACTAGATGCAGCAGAAACTGGG
451 79_HRV57     AAACAAAGTCAAGCAACAACATCAAACTCAGCACCTGCATTGGATGCAGCTGAAACTGGA
452 80_HRV57a|   AAACAAAGTCAAGCAACAACATCAAACTCAGCACCTGCATTGGATGCAGCTGAAACTGGA
453 81_HRV57b|   AAACAAAGTCAAGCAACAACATCAAACTCAGCACCTGCATTGGATGCAGCTGAAACTGGA
454 82_HRV21     AGAGAGAGTCATGGAACAACATCAAACTCTGCTCCCGCACTTGATGCTGCAGAAACTGGA
455 83_HRVHan    AGAGAGAGTCATGGAACAACATCAAACTCTGCTCCCGCACTTGATGCTGCAGAAACTGGG
```

FIG. D12 CONT'D

08.trace                                                                      9/20/2007 5:05 PM

```
456  84_HRV43      GTAGAAAGTCATTCAACAACATCCAATGCAGCCCCTGCACTTGATGCAGCTGAAACTGGG
457  85_HRV43b|    GTAGAAAGTCATTCAACAACATCCAATGCAGCCCCTGCACTTGATGCAGCTGAAACTGGG
458  86_HRV43a|    GTAGAAAGTCATTCAACAACATCCAATGCAGCCCCTGCACTTGATGCAGCTGAAACTGGG
459  87_HRV75      ATGGAGAGCCATCCAACAACGTCTAATGCTGCTCCAGCTTTAGATGCAGCTGAAACTGGC
460  88_HRV75b|    ATGGAGAGCCATCCAACAACGTCTAATGCTGCTCCAGCTTTAGATGCAGCTGAAACTGGC
461  89_HRV75a|    ATGGAGAGCCATCCAACAACGTCTAATGCTGCTCCAGCTTTAGATGCAGCTGAAACTGGC
462  96_HRV9a|d    AAAGAGAGCAACCCTACAACCTCTAACTCAGCTCCAGCTCTAGATGCTGCTGAGACAGGC
463  97_HRV9b|d    AAAGAGAGCAACCCTACAACCTCTAACTCAGCTCCAGCTCTAGATGCTGCTGAGACAGGC
464  98_HRV9       AAAGAGAGCAACCCTACAACCTCTAACTCAGCTCCAGCTCTAGATGCTGCTGAGACAGGC
465  99_HRV32      AAAGAAAGCAATCCCACAACCTCTAATTCAGCCCCAGCCTTAGATGCTGCCGAAACAGGT
466  100_HRV32a    AAAGAAAGCAATCCCACAACCTCTAATTCAGCCCCAGCCTTAGATGCTGCCGAAACAGGT
467  101_HRV32b    AAAGAAAGCAATCCCACAACCTCTAATTCAGCCCCAGCCTTAGATGCTGCCGAAACAGGT
468  102_HRV67     AAGCAAAGTGAACCCACGACTTCCAATTCAGCCCCAGCTCTAGATGCTGCTGAGACAGGT
469  103_HRV67a    AAGCAAAGTGAACCCACGACTTCCAATTCAGCCCCAGCTCTAGATGCTGCTGAGACAGGT
470  104_HRV67b    AAGCAAAGTGAACCCACGACTTCCAATTCAGCCCCAGCTCTAGATGCTGCTGAGACAGGT
471  105_HRV15     AAGGAGAGTCACTCAAGCACATCCAACTCAGCACCAGCACTAGATGCAGCTGAGACCGGC
472  106_HRV15a    AAGGAGAGTCACTCAAGCACATCCAACTCAGCACCAGCACTAGATGCAGCTGAGACCGGC
473  107_HRV15b    AAGGAGAGTCACTCAAGCACATCCAACTCAGCACCAGCACTAGATGCAGCTGAGACCGGC
474  108_HRV74a    AGAGAAAGCCATTCAAGTACTTCAAACTCAGCACCAGCACTGGATGCAGCTGAAACTGGC
475  109_HRV74b    AGAGAAAGCCATTCAAGTACTTCAAACTCAGCACCAGCACTGGATGCAGCTGAAACTGGC
476  110_HRV74     AGAGAAAGCCATTCAAGTACTTCAAACTCAGCACCAGCACTGGATGCAGCTGAAACTGGC
477  111_HRV38a    AAGGAAAGCCACTCCAGCACATCAAATTCAGCACCAGCATTAGATGCTGCTGAGACTGGA
478  112_HRV38b    AAGGAAAGCCACTCCAGCACATCAAATTCAGCACCAGCATTAGATGCTGCTGAGACTGGA
479  113_HRV38     AAGGAAAGCCACTCCAGCACATCAAATTCAGCACCAGCATTAGATGCTGCTGAGACTGGA
480  114_HRV60     AGGGAGAGCCAACCCACTACTTCTAATTCTGCTCCAGCATTGGATGCTGCTGAGACTGGT
481  115_HRV60a    AGGGAGAGCCAACCCACTACTTCTAATTCTGCTCCAGCATTGGATGCTGCTGAGACTGGT
482  116_HRV60b    AGGGAGAGCCAACCCACTACTTCTAATTCTGCTCCAGCATTGGATGCTGCTGAGACTGGT
483  117_HRV64a    AATGAGAGCCATCCCAGCACTTCCAATGCAGCGCCAGCTTTAGATGCAGCTGAGACCGGA
484  118_HRV64b    AATGAGAGCCATCCCAGCACTTCCAATGCAGCGCCAGCTTTAGATGCAGCTGAGACCGGA
485  119_HRV64     AATGAGAGCCATCCCAGCACTTCCAATGCAGCGCCAGCTTTAGATGCAGCTGAGACCGGA
486  120_HRV94a    AATGAGAGTCACCCTAGCACATCCAATGCAGCGCCAGCCTTAGATGCTGCCGAAACTGGA
487  121_HRV94b    AATGAGAGTCACCCTAGCACATCCAATGCAGCGCCAGCCTTAGATGCTGCCGAAACTGGA
488  122_HRV94     AATGAGAGTCACCCTAGCACATCCAATGCAGCGCCAGCCTTAGATGCTGCCGAAACTGGA
489  123_HRV22     AATGAAAGTCACCCCAGTACATCAAATGCTGCACCAGCACTAGATGCTGCTGAAACTGGA
490  124_HRV22a    AATGAAAGTCACCCCAGTACATCAAATGCTGCACCAGCACTAGATGCTGCTGAAACTGGA
491  125_HRV22b    AATGAAAGTCACCCCAGTACATCAAATGCTGCACCAGCACTAGATGCTGCTGAAACTGGA
492  126_HRV82     AATGAAAGTCATCCTAGTACTTCAAATTCAGCTCCTGCCTTGGACGCTGCAGAGACAGGA
493  127_HRV82b    AATGAAAGTCATCCTAGTACTTCAAATTCAGCTCCTGCCTTGGACGCTGCAGAGACAGGA
494  128_HRV82a    AATGAAAGTCATCCTAGTACTTCAAATTCAGCTCCTGCCTTGGACGCTGCAGAGACAGGA
495  129_HRV19     AATGAAAGTCATCCAAGTACATCAAATGCTGCTCCTGCCTTAGATGCAGCCGAGACAGGA
496  130_HRV19a    AATGAAAGTCATCCAAGTACATCAAATGCTGCTCCTGCCTTAGATGCAGCCGAGACAGGA
497  131_HRV19b    AATGAAAGTCATCCAAGTACATCAAATGCTGCTCCTGCCTTAGATGCAGCCGAGACAGGA
498  132_HRV13     AGTGAAAGTAGCTCAACTACATCTAATTCAGCTCCAGCCTTAGATGCTGCAGAAACTGGC
499  133_HRV13a    AGTGAAAGTAGCTCAACTACATCTAATTCAGCTCCAGCCTTAGATGCTGCAGAAACTGGC
500  134_HRV13b    AGTGAAAGTAGCTCAACTACATCTAATTCAGCTCCAGCCTTAGATGCTGCAGAAACTGGC
501  135_HRV41     AGTGAAAGCAGTCCAACTACTTCAGCTCCAGCCCTAGATGCAGCAGAGACTGGT
502  136_HRV41a    AGTGAAAGCAGTCCAACTACTTCTAATTCAGCTCCAGCCCTAGATGCAGCAGAGACTGGT
503  137_HRV41b    AGTGAAAGCAGTCCAACTACTTCTAATTCAGCTCCAGCCCTAGATGCAGCAGAGACTGGT
504  138_HRV73     AATGAAAGTAATCCAACTACATCCAACTCAGCACCTGCACTGGACGCTGCAGAAACTGGC
505  139_HRV73b    AATGAAAGTAATCCAACTACATCCAACTCAGCACCTGCACTGGACGCTGCAGAAACTGGC
506  140_HRV73a    AATGAAAGTAATCCAACTACATCCAACTCAGCACCTGCACTGGACGCTGCAGAAACTGGC
507  141_HRV61     AATCAGAGCAACCCTACAACATCCAACTCAGCACCAGTCTTAGACGCTGCTGAAACAGGT
508  142_HRV61a    AATCAGAGCAACCCTACAACATCCAACTCAGCACCAGTCTTAGACGCTGCTGAAACAGGT
509  143_HRV61b    AATCAGAGCAACCCTACAACATCCAACTCAGCACCAGTCTTAGACGCTGCTGAAACAGGT
510  144_HRV96     AATGAAAGTTACCCAACAACTTCCAATTCAGCCCCAGTGCTAGATGCCGCTGAAACAGGT
511  145_HRV96b    AATGAAAGTTACCCAACAACTTCCAATTCAGCCCCAGTGCTAGATGCCGCTGAAACAGGT
512  146_HRV96a    AATGAAAGTTACCCAACAACTTCCAATTCAGCCCCAGTGCTAGATGCCGCTGAAACAGGT
513  90_HRV16a|    AATGAGAGCCACCCTACCACATCAAATGCGGCCCCAGTTTTGGATGCTGCTGAAACAGGA
514  91_HRV16b|    AATGAGAGCCACCCTACCACATCAAATGCGGCCCCAGTTTTGGATGCTGCTGAAACAGGA
515  92_1AYM_A     AATGAGAGCCACCCTACCACATCAAATGCGGCCCCAGTTTTGGATGCTGCTGAAACAGGA
516  93_HRV81a|    AATGAAAGCCACCCTACAACATCTAATTCAGCTCCTGTTTTAGATGCAGCTGAAACTGGA
517  94_HRV81b|    AATGAAAGCCACCCTACAACATCTAATTCAGCTCCTGTTTTAGATGCAGCTGAAACTGGA
518  95_HRV81      AATGAAAGCCACCCTACAACATCTAATTCAGCTCCTGTTTTAGATGCAGCTGAAACTGGA
519  GROUP_1       ----A-AG----------A--TC-AA--C-GC--C-----T-GA-GC-GC-GA-AC-GG-
520
```

FIG. D12 CONT'D 08.trace                                                                                    9/20/2007 5:05 PM

```
521  1_HRV1A1|d     CACACCAGTAATGTTCAACCAGAAGATGCTATAGAGACAAGGTATGTTATAACATCACAA
522  2_HRV1A2|d     CACACCAGTAATGTTCAACCAGAAGATGCTATAGAGACAAGGTATGTTATAACATCACAA
523  3_HRV1A|cD     CACACCAGTAATGTTCAACCAGAAGATGCTATAGAGACAAGGTATGTTATAACATCACAA
524  4_HRV1B1|d     CACACCAGTAATGTACAACCAGAGGATGCTATAGAAACAAGATATGTTATGACATCACAA
525  5_HRV1B2|d     CACACCAGTAATGTACAACCAGAGGATGCTATAGAAACAAGATATGTTATGACATCACAA
526  6_HRV1B        CACACCAGTAATGTACAACCAGAGGATGCTATAGAAACAAGATATGTTATGACATCACAA
527  7_HRV40a|d     CATACAAGCAACATACAACCTGAAGATACAATAGAAACAAGATTTGTGCAGACATCACAA
528  8_HRV40b|d     CATACAAGCAACATACAACCTGAAGATACAATAGAAACAAGATTTGTGCAGACATCACAA
529  9_HRV40        CATACAAGCAACATACAACCTGAAGATACAATAGAAACAAGATTTGTGCAGACATCACAA
530  10_HRV85       CATACAAGTAGTACACAGCCCGAGGATACAATAGAGACCAGGTTTGTTCAAACTTCACAG
531  11_HRV85a|     CATACAAGTAGTACACAGCCCGAGGATACAATAGAGACCAGGTTTGTTCAAACTTCACAG
532  12_HRV85b|     CATACAAGTAGTACACAGCCCGAGGATACAATAGAGACCAGGTTTGTTCAAACTTCACAG
533  13_HRV56a|     CATACTAGTGCAATCCAACCAGAAGACACTATAGAAACCAGATATGTACAGACATCACAA
534  14_HRV56b|     CATACTAGTGCAATCCAACCAGAAGACACTATAGAAACCAGATATGTACAGACATCACAA
535  15_HRV56       CATACTAGTGCAATCCAACCAGAAGACACTATAGAAACCAGATATGTACAGACATCACAA
536  16_HRV54       CACACTAGTGGAGTACAACCCGAGGACACCATAGAAACAAGATTTGTGCAGACATCACAA
537  17_HRV98       CACACTAGTGGAATACAACCTGAGGATACTATAGAAACAAGATATGTGCAGACATCACAA
538  18_HRV59a|     CATACAAGCAGTATACAACCTGAGGATACCATAGAAACAAGATATGTTCAGACATCACAA
539  19_HRV59b|     CATACAAGCAGTATACAACCTGAGGATACCATAGAAACAAGATATGTTCAGACATCACAA
540  20_HRV59       CATACAAGCAGTATACAACCTGAGGATACCATAGAAACAAGATATGTTCAGACATCACAA
541  21_HRV63       CACACAAGCAGTATACAACCTGAGGATACTGTAGAAACTAGATATGTGCAAACGTCTCAA
542  22_HRV63b|     CACACAAGCAGTATACAACCTGAGGATACTGTAGAAACTAGATATGTGCAAACGTCTCAA
543  23_HRV63a|     CACACAAGCAGTATACAACCTGAGGATACTGTAGAAACTAGATATGTGCAAACGTCTCAA
544  24_HRV39       CACACAAGTAGCACCCAGCCTGAAGACACAATTGAAACAAGATATGTGCAAACCTCACAT
545  25_HRV39a|     CACACAAGTAGCACCCAGCCTGAAGACACAATTGAAACAAGATATGTGCAAACCTCACAT
546  26_HRV39b|     CACACAAGTAGCATCCAACCTGAAGACACAATTGAAACAAGATATGTGCAAACCTCACAT
547  27_HRV10a|     CATACCAGTAGTGTACAACCAGAAGATACGGTTGAAACACGATATGTGCAAACATCCCAG
548  28_HRV10b|     CATACCAGTAGTGTACAACCAGAAGATACGGTTGAAACACGATATGTGCAAACATCCCAG
549  29_HRV10       CATACCAGTAGTGTACAACCAGAAGATACGGTTGAAACACGATATGTGCAAACATCCCAG
550  30_HRV100a     CACACTAGTAATGTGCAACCTGAAGATACAGTTGAAACTCGATATGTGCAGACATCACAG
551  31_HRV100b     CACACTAGTAATGTGCAACCTGAAGATACAGTTGAAACTCGATATGTGCAGACATCACAG
552  32_HRV100      CACACTAGTAATGTGCAACCTGAAGATACAGTTGAAACTCGATATGTGCAGACATCACAG
553  33_HRV66       CACACTAGTAAAGTACAACCAGAAGATACAGTTGAGACTCGTTACGTGCAAACATCACAG
554  34_HRV66b|     CACACTAGTAAAGTACAACCAGAAGATACAGTTGAGACTCGTTACGTGCAAACATCACAG
555  35_HRV66a|     CACACTAGTAAAGTACAACCAGAAGATACAGTTGAGACTCGTTACGTGCAAACATCACAG
556  36_HRV77a|     CATACTAGTAGTGTGCAACCAGAAGATACAGTTGAGACCCGCTATGTACAAACTTCCCAG
557  37_HRV77b|     CATACTAGTAGTGTGCAACCAGAAGATACAGTTGAGACCCGCTATGTACAAACTTCCCAG
558  38_HRV77       CATACTAGTAGTGTGCAACCAGAAGATACAGTTGAGACCCGCTATGTACAAACTTCCCAG
559  39_HRV62a      CACACTAGTAATGTACAACCAGAAGACACTATTGAAACCCGTCATGTTCAAACCACACAA
560  40_HRV62b      CACACTAGTAATGTACAACCAGAAGACACTATTGAAACCCGTTATGTTCAAACCACACAA
561  41_HRV25       CACACTAGCAATGTGCAACCAGAGGATACCATTGAAACTCGTTATGTTCAAACCACACAA
562  42_HRV29a      CATACTAGTAATGTACAACCAGAAGATACCATTGAGACTCGTTATGTACAAACCTCACAT
563  43_HRV29b      CATACTAGTAATGTACAACCAGAAGATACCATTGAGACTCGTTATGTACAAACCTCACAT
564  44_HRV44a      CATACTAGTAATGTACAACCAGAAGATACCATTGAGACTCGATATGTACAAACCTCACAA
565  45_HRV44b      CATACTAGTAATGTACAACCAGAAGATACCATTGAGACTCGATATGTACAAACCTCACAA
566  46_HRV31       CACACTAGTAATGTACAACCAGAAGATACAATTGAAACTCGCTACGTGCAAACATCACAA
567  47_HRV31a|     CACACTAGTAATGTACAACCAGAAGATACAATTGAAACTCGCTACGTGCAAACATCACAA
568  48_HRV31b|     CACACTAGTAATGTACAACCAGAAGATACAATTGAAACTCGCTACGTGCAAACATCACAA
569  49_HRV47       CACACTAGCAATGTACAGCCAGAAGATACAATTGAAACTCGATATGTACAAACAGCACAA
570  50_HRV47a|     CACACTAGCAATGTACAGCCAGAAGATACAATTGAAACTCGATATGTACAAACAGCACAA
571  51_HRV47b|     CACACTAGCAATGTACAGCCAGAAGATACAATTGAAACTCGATATGTACAAACAGCACAA
572  52_HRV11       CATACTAGCAAAGTGCAGCCAGAGGATATGATTGAGACTAGATATGTGCAGACTTCACAG
573  53_HRV11b|     CATACTAGCAAAGTGCAGCCAGAGGATATGATTGAGACTAGATATGTGCAGACTTCACAG
574  54_HRV11a|     CATACTAGCAAAGTGCAGCCAGAGGATATGATTGAGACTAGATATGTGCAGACTTCACAG
575  55_HRV76       CACACAAGCAGCGTTCAACCAGAGGACATGGTTGAGACTAGGTATGTGCAAACATCACAA
576  56_HRV76b|     CACACAAGCAGCGTTCAACCAGAGGACATGGTTGAGACTAGGTATGTGCAAACATCACAA
577  57_HRV76a|     CACACAAGCAGCGTTCAACCAGAGGACATGGTTGAGACTAGGTATGTGCAAACATCACAA
578  58_HRV33       CACACTAATAATGTACAACCAGAAGATATGTGAACAAGATATGTACAAACATCACAA
579  59_HRV33b|     CACACTAATAATGTACAACCAGAAGATATGATTGAAACAAGATATGTACAAACATCACAA
580  60_HRV33a|     CACACTAATAATGTACAACCAGAAGATATGATTGAAACAAGATATGTACAAACATCACAA
581  61_HRV24a|     CATACGAGTAGCGTGCAGCCAGAAGATATGGTTGAAACTAGATATGTCCAAACATCACAA
582  62_HRV24b|     CATACGAGTAGCGTGCAGCCAGAAGATATGGTTGAAACTAGATATGTCCAAACATCACAA
583  63_HRV24       CATACGAGTAGCGTGCAGCCAGAAGATATGGTTGAAACTAGATATGTCCAAACATCACAA
584  64_HRV90       CATACTAGTGATGTCCAGCCAGAAGATGTGGTAGAGACCAGATACGTGCAAACATCACAA
585  65_HRV90a|     CATACTAGTGATGTCCAGCCAGAAGATGTGGTAGAGACCAGATACGTGCAAACATCACAA
```

FIG. D12 CONT'D

```
08.trace                                                              9/20/2007 5:05 PM 586  66_HRV90b|    CATACTAGTGATGTCCAGCCAGAAGATGTGGTAGAGACCAGATACGTGCAAACATCACAA
587  67_HRV34      CACACTAGCAGTGTACAACCTGAAGATATGATTGAGACCAGGTACGTACAAACATCACAA
588  68_HRV34b|    CACACTAGCAGTGTACAACCTGAAGATATGATTGAGACCAGGTACGTACAAACATCACAA
589  69_HRV34a|    CACACTAGCAGTGTACAACCTGAAGATATGATTGAGACCAGGTACGTACAAACATCACAA
590  70_HRV50a|    CACACAAGTAATGTGCAGCCTGAAGATATGCTTGAAACTAGATATGTGCAAACATCGCAT
591  71_HRV50b|    CACACAAGTAATGTGCAGCCTGAAGATATGCTTGAAACTAGATATGTGCAAACATCGCAT
592  72_HRV50      CACACAAGTAATGTGCAGCCTGAAGATATGCTTGAAACTAGATATGTGCAAACATCGCAT
593  73_HRV18a|    CACACCAGCAATGTGCAACCTGAAGATATGATTGAGACTAGGTATGTACAAACATCACAA
594  74_HRV18b|    CACACCAGCAATGTGCAACCTGAAGATATGATTGAGACTAGGTATGTACAAACATCACAA
595  75_HRV18      CACACCAGCAATGTGCAACCTGAAGATATGATTGAGACTAGGTATGTACAAACATCACAA
596  76_HRV55      CATACAAGCAATGTACAACCAGAAGATGTAATTGAGACAAGATATGTTCAGACATCACAA
597  77_HRV55b|    CATACAAGCAATGTACAACCAGAAGATGTAATTGAGACAAGATATGTTCAGACATCACAA
598  78_HRV55a|    CATACAAGCAATGTACAACCAGAAGATGTAATTGAGACAAGATATGTTCAGACATCACAA
599  79_HRV57      CACACTAGTAATGTACAACCGGAAGACATGATTGAAACTAGATATGTCCAGACATCACAA
600  80_HRV57a|    CACACTAGTAATGTACAACCGGAAGACATGATTGAAACTAGATATGTCCAGACATCACAA
601  81_HRV57b|    CACACTAGTAATGTACAACCGGAAGACATGATTGAAACTAGATATGTCCAGACATCACAA
602  82_HRV21      CACACTAGTAATGTACAGCCGGAGGATATGGTTGAAACAAGGTATGTTCAGACATCACAA
603  83_HRVHan     CACACTAGTAATGTACAACCAGAGGATATGGTTGAAACAAGGTATGTTCAGACATCACAA
604  84_HRV43      CATACTAGCCAGGTGCAACCTGAAGACATGGTAGAGACAAGGTCAGTACATAATTTCCAA
605  85_HRV43b|    CATACTAGCCAGGTGCAACCTGAAGACATGGTAGAGACAAGGTCAGTACATAATTTCCAA
606  86_HRV43a|    CATACTAGCCAGGTGCAACCTGAAGACATGGTAGAGACAAGGTCAGTACATAATTTCCAA
607  87_HRV75      CATACCAGCCATGTTCAACCAGAAGACATGTTAGAAACAAGGCAAGTACAAAATTTCCAA
608  88_HRV75b|    CATACCAGCCATGTTCAACCAGAAGACATGTTAGAAACAAGGCAAGTACAAAATTTCCAA
609  89_HRV75a|    CATACCAGCCATGTTCAACCAGAAGACATGTTAGAAACAAGGCAAGTACAAAATTTCCAA
610  96_HRV9a|d    CATACTAGCAATGTTCAACCTGAAGACATGATTGAAACACGTTATGTGCAGACATCACAA
611  97_HRV9b|d    CATACTAGCAATGTTCAACCTGAAGACATGATTGAAACACGTTATGTGCAGACATCACAA
612  98_HRV9       CATACTAGCAATGTTCAACCTGAAGACATGATTGAAACACGTTATGTGCAGACATCACAA
613  99_HRV32      CATACCAGTAATGTTCAACCTGAAGACATGATTGAAACACGTTATGTGCAAACAACACAC
614  100_HRV32a    CATACCAGTAATGTTCAACCTGAAGACATGATTGAAACACGTTATGTGCAAACAACACAC
615  101_HRV32b    CATACCAGTAATGTTCAACCTGAAGACATGATTGAAACACGTTATGTGCAAACAACACAC
616  102_HRV67     CACACTAGCAGTGTACAACCTGAAGATATGATCGAGACTCGTTATGTACAGGCATCAAAT
617  103_HRV67a    CACACTAGCAGTGTACAACCTGAAGATATGATCGAGACTCGTTATGTACAGGCATCAAAT
618  104_HRV67b    CACACTAGCAGTGTACAACCTGAAGATATGATCGAGACTCGTTATGTACAGGCATCAAAT
619  105_HRV15     CATACTAGCAGTGTTCAACCTGAGGATATGATTGAAACTCGTTACGTCCAAACATCACAG
620  106_HRV15a    CATACTAGCAGTGTTCAACCTGAGGATATGATTGAAACTCGTTACGTCCAAACATCACAG
621  107_HRV15b    CATACTAGCAGTGTTCAACCTGAGGATATGATTGAAACTCGTTACGTCCAAACATCACAG
622  108_HRV74a    CATACCAGTAATGTGCAACCAGAAGATATGGTTGAGACACGCTATGTGCAAACCTCACAG
623  109_HRV74b    CATACCAGTAATGTGCAACCAGAAGATATGGTTGAGACACGCTATGTGCAAACCTCACAG
624  110_HRV74     CATACCAGTAATGTGCAACCAGAAGATATGGTTGAGACACGCTATGTGCAAACCTCACAG
625  111_HRV38a    CACACCAGTAATGTGCAGCCTGAGGATATGATTGAAACTCGCTATGTACAGACATCACAA
626  112_HRV38b    CACACCAGTAATGTGCAGCCTGAGGATATGATTGAAACTCGCTATGTACAGACATCACAA
627  113_HRV38     CACACCAGTAATGTGCAGCCTGAGGATATGATTGAAACTCGCTATGTACAGACATCACAA
628  114_HRV60     CACACTAGTAATGTACAGCCTGAGGATGTGATTGAAACACGTTATGTGCAGATTACACAA
629  115_HRV60a    CACACTAGTAATGTACAGCCTGAGGACGTGATTGAAACACGTTATGTGCAGATTACACAA
630  116_HRV60b    CACACTAGTAATGTACAGCCTGAGGACGTGATTGAAACACGTTATGTGCAGATTACACAA
631  117_HRV64a    CACACCAGTAATGTACAGCCTGAAGATATGATTGAAACGCGCTATGTACAAAACACTCAA
632  118_HRV64b    CACACTAGTAATGTACAGCCTGAAGATATGATTGAAACGCGCTATGTACAAAACACTCAA
633  119_HRV64     CACACCAGTAATGTACAGCCTGAAGATATGATTGAAACGCGCTATGTACAAAACACTCAA
634  120_HRV94a    CACACAAGCAATGTACAACCTGAGGATATGATTGAAACACGCTATGTACAAAACACTCAA
635  121_HRV94b    CACACAAGCAATGTACAACCTGAGGATATGATTGAAACACGCTATGTACAAAACACTCAA
636  122_HRV94     CACACAAGCAATGTACAACCTGAGGATATGATTGAAACACGCTATGTACAAAACACTCAA
637  123_HRV22     CACACAAGCAATGTGCAGCCAGAAGACATGATAGAAACACGCTATGTGTTAAATTCACAA
638  124_HRV22a    CACACAAGCAATGTGCAGCCAGAAGACATGATAGAAACACGCTATGTGTTAAATTCACAA
639  125_HRV22b    CACACAAGCAATGTGCAGCCAGAAGACATGATAGAAACACGCTATGTGTTAAATTCACAA
640  126_HRV82     CATACAAGTACTGTTCAACCTGAGGACATGATTGAAACACGGTATGTTCAAACATCACAA
641  127_HRV82b    CATACAAGTACTGTTCAACCTGAGGACATGATTGAAACACGGTATGTTCAAACATCACAA
642  128_HRV82a    CATACAAGTACTGTTCAACCTGAGGACATGATTGAAACACGGTATGTTCAAACATCACAA
643  129_HRV19     CATACTAGCAATGTACAGCCTGAGGACATGATCGAAACACGCTATGTTCAAACGTCCCAG
644  130_HRV19a    CATACTAGCAATGTACAGCCTGAGGACATGATCGAAACACGCTATGTTCAAACGTCCCAG
645  131_HRV19b    CATACTAGCAATGTACAGCCTGAGGACATGATCGAAACACGCTATGTTCAAACGTCCCAG
646  132_HRV13     CACACAAGCAGTGTACAACCAGAAGACATGGTTGAAACACGTTATGTCCAAACTTCACAA
647  133_HRV13a    CACACAAGCAGTGTACAACCAGAAGACATGGTTGAAACACGTTATGTCCAAACTTCACAA
648  134_HRV13b    CACACAAGCAGTGTACAACCAGAAGACATGGTTGAAACACGTTATGTCCAAACTTCACAA
649  135_HRV41     CATACCAGTAATGTACAACCAGAGGACATGATTGAAACACGATATGTCCAAACCTCACAA
650  136_HRV41a    CATACCAGTAATGTACAACCAGAGGACATGATTGAAACACGATATGTCCAAACCTCACAA
```

FIG. D12 CONT'D

08.trace                                                                 9/20/2007 5:05 PM

```
651  137_HRV41b    CATACCAGTAATGTACAACCAGAGGACATGATTGAAACACGATATGTCCAAACCTCACAA
652  138_HRV73     CATACCAGTGGTGTACAACCAGAAGACATGATTGAGACCCGTTATGTCCAAACATCACAG
653  139_HRV73b    CATACCAGTGGTGTACAACCAGAAGACATGATTGAGACCCGTTATGTCCAAACATCACAG
654  140_HRV73a    CATACCAGTGGTGTACAACCAGAAGACATGATTGAGACCCGTTATGTCCAAACATCACAG
655  141_HRV61     CATACCAGCAATGTTCAACCGGAGGACACGATTGAAACACGATATGTTCAAACCTCACAG
656  142_HRV61a    CATACCAGCAATGTTCAACCGGAGGACACGATTGAAACACGATATGTTCAAACCTCACAG
657  143_HRV61b    CATACCAGCAATGTTCAACCGGAGGACACGATTGAAACACGATATGTTCAAACCTCACAG
658  144_HRV96     CATACTAGCAATGTCCAACCAGAGGATATGATTGAGACTCGATATGTTCAGACATCGCAG
659  145_HRV96b    CATACTAGCAATGTCCAACCAGAGGATATGATTGAGACTCGATATGTTCAGACATCGCAG
660  146_HRV96a    CATACTAGCAATGTCCAACCAGAGGATATGATTGAGACTCGATATGTTCAGACATCGCAG
661  90_HRV16a|    CATACCAATAAGATACAGCCAGAAGACACTATAGAAACCAGATATGTGCAATCTTCACAG
662  91_HRV16b|    CATACCAATAAGATACAGCCAGAAGACACTATAGAAACCAGATATGTGCAATCTTCACAG
663  92_1AYM_A     CATACCAATAAGATACAGCCAGAAGACACTATAGAAACCAGATATGTGCAATCTTCACAG
664  93_HRV81a|    CACACCAGTAATATACAACCTGAGGATACTATTGAGACCAGATATGTACAATCTTCACAG
665  94_HRV81b|    CACACCAGTAATATACAACCTGAGGATACTATTGAGACCAGATATGTACAATCTTCACAG
666  95_HRV81      CACACCAGTAATATACAACCTGAGGATACTATTGAGACCAGATATGTACAATCTTCACAG
667  GROUP_1       CA-AC-A--------CA-CC-GA-GA-----T-GA-AC--G----GT----------A-
668
669  1_HRV1A1|d    ACAAGAGATGAGATGAGTATAGAAAGTTTCCTTGGTAGATCTGGTTGTGTCCACATCTCA
670  2_HRV1A2|d    ACAAGAGATGAGATGAGTATAGAAAGTTTCCTTGGTAGATCTGGTTGTGTCCACATCTCA
671  3_HRV1A|cD    ACAAGAGATGAGATGAGTATAGAAAGTTTCCTTGGTAGATCTGGTTGTGTCCACATCTCA
672  4_HRV1B1|d    ACAAGAGATGAGATGAGTATAGAAAGTTTTCTTGGTAGATCTGGCTGTGTGCATATTTCA
673  5_HRV1B2|d    ACAAGAGATGAGATGAGTATAGAAAGTTTTCTTGGTAGATCTGGCTGTGTGCATATTTCA
674  6_HRV1B       ACAAGAGATGAGATGAGTATAGAAAGTTTTCTTGGTAGATCTGGCTGTGTGCATATTTCA
675  7_HRV40a|d    ACTAGAGATGAAATGAGCATAGAGAGTTTCTTGGGAAGATCTGGGTGCATTCATATATCC
676  8_HRV40b|d    ACTAGAGATGAAATGAGCATAGAGAGTTTCTTGGGAAGATCTGGGTGCATTCATATATCC
677  9_HRV40       ACTAGAGATGAAATGAGCATAGAGAGTTTCTTGGGAAGATCTGGGTGCATTCATATATCC
678  10_HRV85      ACTAGGGATGAAATGAGTTTAGAAAGTTTCTTGGGAAGATCTGGATGTATCCATATATCT
679  11_HRV85a|    ACTAGGGATGAAATGAGTTTAGAAAGTTTCTTGGGAAGATCTGGATGTATCCATATATCT
680  12_HRV85b|    ACTAGGGATGAAATGAGTTTAGAAAGTTTCTTGGGAAGATCTGGATGTATCCATATATCT
681  13_HRV56a|    ACTAGGGATGAAATGAGTATAGAGAGTTTCTAGGTAGATCAGGTTGTATACATATATCA
682  14_HRV56b|    ACTAGGGATGAAATGAGTATAGAGAGTTTTCTAGGTAGATCAGGTTGTATACATATATCA
683  15_HRV56      ACTAGGGATGAAATGAGTATAGAGAGTTTCTAGGTAGATCAGGTTGTATACATATATCA
684  16_HRV54      ACTAGAGATGAAATGAGCATAGAAAGTTTTCTAGGCAGGGCTGGTTGCATACATGAATCC
685  17_HRV98      ACCAGAGATGAAATGAGTATAGAAAGTTTTCTAGGTAGGGCCGGTTGTATACATGAATCT
686  18_HRV59a|    ACTAGAGATGAGATGAGTGTAGAAAGTTTCTTAGGTAGATCTGGGTGTATACATATTTCA
687  19_HRV59b|    ACTAGAGATGAGATGAGTGTAGAAAGTTTCTTAGGTAGATCTGGGTGTATACATATTTCA
688  20_HRV59      ACTAGAGATGAGATGAGTGTAGAAAGTTTCTTAGGTAGATCTGGGTGTATACATATTTCA
689  21_HRV63      ACAAGGGATGAAATGAGTGTAGAGAGCTTTCTTGGTAGATCAGGATGCATACACATATCA
690  22_HRV63b|    ACAAGGGATGAAATGAGTGTAGAGAGCTTTCTTGGTAGATCAGGATGCATACACATATCA
691  23_HRV63a|    ACAAGGGATGAAATGAGTGTAGAGAGCTTTCTTGGTAGATCAGGATGCATACACATATCA
692  24_HRV39      ACTAGGGATGAAATGAGCGTTGAAAGTTTCTTAGGCAGATCTGGCTGTATTCACATTTCC
693  25_HRV39a|    ACTAGGGATGAAATGAGCGTTGAAAGTTTCTTAGGCAGATCTGGCTGTATTCACATTTCC
694  26_HRV39b|    ACTAGGGATGAAATGAGTGTTGAAAGTTTCTTAGGCAGATCTGGCTGTATTCACATTTCC
695  27_HRV10a|    ACGAGAGATGAAATGAGTATTGAAAGTTTTCTTGGCAGGTCAGGTTGTATACACACCTCA
696  28_HRV10b|    ACGAGAGATGAAATGAGTATTGAAAGTTTTCTTGGCAGGTCAGGTTGTATACACACCTCA
697  29_HRV10      ACGAGAGATGAAATGAGTATTGAAAGTTTTCTTGGCAGGTCAGGTTGTATACACACCTCA
698  30_HRV100a    ACCAGGGATGAAATGAGTATTGAGAGCTTTCTTGGAAGATCTGGTTGTATACACACCTCA
699  31_HRV100b    ACCAGGGATGAAATGAGTATTGAGAGCTTTCTTGGAAGATCTGGTTGTATACACACCTCA
700  32_HRV100     ACCAGGGATGAAATGAGTATTGAGAGCTTTCTTGGAAGATCTGGTTGTATACACACCTCA
701  33_HRV66      ACTAGAGATGAAATGAGCATAGAAAGTTTTCTAGGTAGGTCAGGATGTATCCATATATCA
702  34_HRV66b|    ACTAGAGATGAAATGAGCATAGAAAGTTTTCTAGGTAGGTCAGGATGTATCCATATATCA
703  35_HRV66a|    ACTAGAGATGAAATGAGCATAGAAAGTTTTCTAGGTAGGTCAGGATGTATCCATATATCA
704  36_HRV77a|    ACAAGGGATGAGATGAGTATTGAGAGCTTTCTGGGTAGGTCTGGTTGTATTCACATTTCA
705  37_HRV77b|    ACAAGGGATGAGATGAGTATTGAGAGCTTTCTGGGTAGGTCTGGTTGTATTCACATTTCA
706  38_HRV77      ACAAGGGATGAGATGAGTATTGAGAGCTTTCTGGGTAGGTCTGGTTGTATTCACATTTCA
707  39_HRV62a     ACTAGAGATGAAATGAGCATTGAGAGCTTTCTTGGTAGGTCAGGGTGCGTACACACTTCA
708  40_HRV62b     ACTAGAGATGAAATGAGCATTGAGAGCTTTCTTGGTAGGTCAGGGTGCGTACACACTTCA
709  41_HRV25      ACTAGAGATGAAATGAGTATTGAAAGTTTTCTTGGTAGGTCAGGGTGTGTACATACTTCA
710  42_HRV29a     ACTAGAGATGAAATGAGCATTGAAAGTTTCTTGGGTAGATCAGGATGTATACATGTTTCA
711  43_HRV29b     ACTAGAGATGAAATGAGCATTGAAAGTTTCTTGGGTAGATCAGGATGTATACATGTTTCA
712  44_HRV44a     ACTAGAGATGAAATGAGCATTGAAAGTTTCTTGGCAGATCAGGGTGTATACATGTTTCA
713  45_HRV44b     ACTAGAGATGAAATGAGCATTGAAAGTTTCTTGGCAGATCAGGGTGTATACATGTTTCA
714  46_HRV31      ACAAGAGATGAAATGAGCATTGAAAGTTTCCTTGGTAGGTCAGGATGTGTACATACTTCA
715  47_HRV31a|    ACAAGAGATGAAATGAGCATTGAAAGTTTCCTTGGTAGGTCAGGATGTGTACATACTTCA
```

FIG. D12 CONT'D

08.trace												9/20/2007 5:05 PM

| | | |
|---|---|---|
| 716 | 48_HRV31b| | ACAAGAGATGAAATGAGCATTGAAAGTTTCCTTGGTAGGTCAGGATGTGTACATACTTCA |
| 717 | 49_HRV47 | ACAAGAGATGAAATGAGCATTGAGAGCTTCCTTGGCAGGTCAGGATGTGTGCATTCCTCA |
| 718 | 50_HRV47a| | ACAAGAGATGAAATGAGCATTGAGAGCTTCCTTGGCAGGTCAGGATGTGTGCATTCCTCA |
| 719 | 51_HRV47b| | ACAAGAGATGAAATGAGCATTGAGAGCTTCCTTGGCAGGTCAGGATGTGTGCATTCCTCA |
| 720 | 52_HRV11 | ACTCTTGATGAAATGAGCATTGAGAGCTTCCTAGGTAGATCTGGTTGTATTCACATGTCC |
| 721 | 53_HRV11b| | ACTCTTGATGAAATGAGCATTGAGAGCTTCCTAGGTAGATCTGGTTGTATTCACATGTCC |
| 722 | 54_HRV11a| | ACTCTTGATGAAATGAGCATTGAGAGCTTCCTAGGTAGATCTGGTTGTATTCACATGTCC |
| 723 | 55_HRV76 | ACTCTTGATGAGATGTGTATGGAGAGTTTCTTAGGGAGATCTGGTTGTATTCATATTTCA |
| 724 | 56_HRV76b| | ACTCTTGATGAGATGTGTATGGAGAGTTTCTTAGGGAGATCTGGTTGTATTCATATTTCA |
| 725 | 57_HRV76a| | ACTCTTGATGAGATGTGTATGGAGAGTTTCTTAGGGAGATCTGGTTGTATTCATATTTCA |
| 726 | 58_HRV33 | ACTCTTGATGAGATGAGTGTGGAAAGCTTCTTAGGAAGGTCTGGTTGCATTCACATGTCA |
| 727 | 59_HRV33b| | ACTCTTGATGAGATGAGTGTGGAAAGCTTCTTAGGAAGGTCTGGTTGCATTCACATGTCA |
| 728 | 60_HRV33a| | ACTCTTGATGAGATGAGTGTGGAAAGCTTCTTAGGAAGGTCTGGTTGCATTCACATGTCA |
| 729 | 61_HRV24a| | ACATTACATGAGATGAGTGTTGAAAGTTTCTTGGGTAGATCAGGTTGCATACACATGTCC |
| 730 | 62_HRV24b| | ACATTACATGAGATGAGTGTTGAAAGTTTCTTGGGTAGATCAGGTTGCATACACATGTCC |
| 731 | 63_HRV24 | ACATTACATGAGATGAGTGTTGAAAGTTTCTTGGGTAGATCAGGTTGCATACACATGTCC |
| 732 | 64_HRV90 | ACAAGAGATGAAATGAGTGTTGAAAGTTTTCTAGGGAGATCAGGTTGCATTCATATGTCA |
| 733 | 65_HRV90a| | ACAAGAGATGAAATGAGTGTTGAAAGTTTTCTAGGGAGATCAGGTTGCATTCATATGTCA |
| 734 | 66_HRV90b| | ACAAGAGATGAAATGAGTGTTGAAAGTTTTCTAGGGAGATCAGGTTGCATTCATATGTCA |
| 735 | 67_HRV34 | ACAAGAGATGAAATGAGCATTGAGAGTTTCCTGGGTAGGTCTGGCTGTATACACATGTCC |
| 736 | 68_HRV34b| | ACAAGAGATGAAATGAGCATTGAGAGTTTCCTGGGTAGGTCTGGCTGTATACACATGTCC |
| 737 | 69_HRV34a| | ACAAGAGATGAAATGAGCATTGAGAGTTTCCTGGGTAGGTCTGGCTGTATACACATGTCC |
| 738 | 70_HRV50a| | ACAAGAGATGAAATGAGCATTGAAAGTTTCCTAGGTAGATCTGGTTGTATACATATATCT |
| 739 | 71_HRV50b| | ACAAGAGATGAAATGAGCATTGAAAGTTTCCTAGGTAGATCTGGTTGTATACATATATCT |
| 740 | 72_HRV50 | ACAAGAGATGAAATGAGCATTGAAAGTTTCCTAGGTAGATCTGGTTGTATACATATATCT |
| 741 | 73_HRV18a| | ACAAGAGATGAAATGAGTATAGAGTGTTTTCTAGGCAGATCAGGGTGTATACATATCTCC |
| 742 | 74_HRV18b| | ACAAGAGATGAAATGAGTATAGAGTGTTTTCTAGGCAGATCAGGGTGTATACATATCTCC |
| 743 | 75_HRV18 | ACAAGAGATGAAATGAGTATAGAGTGTTTTCTAGGCAGATCAGGGTGTATACATATCTCC |
| 744 | 76_HRV55 | ACTCGTGATGAGATGAGCATTGAAAGTTTCTAGGTAGATCAGGATGTGTACATATATCA |
| 745 | 77_HRV55b| | ACTCGTGATGAGATGAGCATTGAAAGTTTTCTAGGTAGATCAGGATGTGTACATATATCA |
| 746 | 78_HRV55a| | ACTCGTGATGAGATGAGCATTGAAAGTTTCTAGGTAGATCAGGATGTGTACATATATCA |
| 747 | 79_HRV57 | ACACGTGATGAAATGAGTCTTGAGAGCTTCTTAGGAAGATCTGGCTGCATTCATATTTCA |
| 748 | 80_HRV57a| | ACACGTGATGAAATGAGTCTTGAGAGCTTCTTAGGAAGATCTGGCTGCATTCATATTTCA |
| 749 | 81_HRV57b| | ACACGTGATGAAATGAGTCTTGAGAGCTTCTTAGGAAGATCTGGCTGCATTCATATTTCA |
| 750 | 82_HRV21 | ACACGTGATGAAATGAGTATTGAAAGTTTTCTGGGCAGATCAGGCTGCATTCACATGTCA |
| 751 | 83_HRVHan | ACACGTGATGAAATGAGTATTGAAAGTTTTCTAGGCAGATCAGGGTGTATCCACATGTCA |
| 752 | 84_HRV43 | ACCAGAGATGAAATGAGTATTGAAAGTTTCTTGGGCAGATCTGGTTGCATACATATTTCA |
| 753 | 85_HRV43b| | ACCAGAGATGAAATGAGTATTGAAAGTTTCTTGGGCAGATCTGGTTGCATACATATTTCA |
| 754 | 86_HRV43a| | ACCAGAGATGAAATGAGTATTGAAAGTTTCTTGGGCAGATCTGGTTGCATACATATTTCA |
| 755 | 87_HRV75 | ACTAGAGATGAGATGAGTATTGAGAGTTTCCTAGGCAGATCTGGATGTATTCATATTTCA |
| 756 | 88_HRV75b| | ACTAGAGATGAGATGAGTATTGAGAGTTTCCTAGGCAGATCTGGATGTATTCATATTTCA |
| 757 | 89_HRV75a| | ACTAGAGATGAGATGAGTATTGAGAGTTTCCTAGGCAGATCTGGATGTATTCATATTTCA |
| 758 | 96_HRV9a|d | ACCAGAGATGAAATGAGTCTTGAAAGCTTCTTAGGGAGATCAGGTTGTATACACATATCT |
| 759 | 97_HRV9b|d | ACCAGAGATGAAATGAGTCTTGAAAGCTTCTTAGGGAGATCAGGTTGTATACACATATCT |
| 760 | 98_HRV9 | ACCAGAGATGAAATGAGTCTTGAAAGCTTCTTAGGGAGATCAGGTTGTATACACATATCT |
| 761 | 99_HRV32 | ACTAGAGATGAGATGAGTCTTGAGAGCTTCTTAGGGAGGTCAGGATGTGTACATATATCC |
| 762 | 100_HRV32a | ACTAGAGATGAGATGAGTCTTGAGAGCTTCTTAGGGAGGTCAGGATGTGTACATATATCC |
| 763 | 101_HRV32b | ACTAGAGATGAGATGAGTCTTGAGAGCTTCTTAGGGAGGTCAGGATGTGTACATATATCC |
| 764 | 102_HRV67 | ACCAGAGATGAAATGAGTCTCGAGAGCTTTCTTGGAAGGTCAGGCTGTATTCATATATCA |
| 765 | 103_HRV67a | ACCAGAGATGAAATGAGTCTCGAGAGCTTTCTTGGAAGGTCAGGCTGTATTCATATATCA |
| 766 | 104_HRV67b | ACCAGAGATGAAATGAGTCTCGAGAGCTTTCTTGGAAGGTCAGGCTGTATTCATATATCA |
| 767 | 105_HRV15 | ACCAGAGATGAAATGAGTATTGAGAGCTTCCTTGGTAGATCAGGGTGTGTCCATATTTCT |
| 768 | 106_HRV15a | ACCAGAGATGAAATGAGTATTGAGAGCTTCCTTGGTAGATCAGGGTGTGTCCATATTTCT |
| 769 | 107_HRV15b | ACCAGAGATGAAATGAGTATTGAGAGCTTCCTTGGTAGATCAGGGTGTGTCCATATTTCT |
| 770 | 108_HRV74a | ACAAGAGATGAGATGAGTGTAGAAAGTTTTCTTGGAAGATCAGGATGCATCCATATCTCA |
| 771 | 109_HRV74b | ACAAGAGATGAGATGAGTGTAGAAAGTTTCTTGGAAGATCAGGATGCATCCATATCTCA |
| 772 | 110_HRV74 | ACAAGAGATGAGATGAGTGTAGAAAGTTTCTTGGAAGATCAGGATGCATCCATATCTCA |
| 773 | 111_HRV38a | ACTAGAGATGAAATGAGTGTAGAAAGTTTTCTAGGAAGATCAGGTTGTGTACATATATCC |
| 774 | 112_HRV38b | ACTAGAGATGAAATGAGTGTAGAAAGTTTTCTAGGAAGATCAGGTTGTGTACATATATCC |
| 775 | 113_HRV38 | ACTAGAGATGAAATGAGTGTAGAAAGTTTTCTAGGAAGATCAGGTTGTGTACATATATCC |
| 776 | 114_HRV60 | ACTAGAGATGAGATGAGTGTTGAGAGCTTCCTCGGCAGATCTGGATGTATTCATATTTCC |
| 777 | 115_HRV60a | ACTAGAGATGAGATGAGTGTTGAGAGCTTCCTCGGCAGATCTGGATGTATTCATATTTCC |
| 778 | 116_HRV60b | ACTAGAGATGAGATGAGTGTTGAGAGCTTCCTCGGCAGATCTGGATGTATTCATATTTCC |
| 779 | 117_HRV64a | ACTAGAGATGAAATGAGCATTGAGAGTTTCTTGGGCAGGTCTGGTTGTATACACATATCA |
| 780 | 118_HRV64b | ACTAGAGATGAAATGAGCATTGAGAGTTTCTTGGGCAGGTCTGGTTGTATACACATATCA |

FIG. D12 CONT'D 08.trace                                                                                              9/20/2007 5:05 PM

```
781 119_HRV64    ACTAGAGATGAAATGAGCATTGAGAGTTTCTTGGGCAGGTCTGGTTGTATACACATATCA
782 120_HRV94a   ACAAGGGATGAAATGAGCATTGAAAGCTTCTTGGGAAGATCTGGCTGTATACACATAGCA
783 121_HRV94b   ACAAGGGATGAAATGAGCATTGAAAGCTTCTTGGGAAGATCTGGCTGTATACACATAGCA
784 122_HRV94    ACAAGGGATGAAATGAGCATTGAAAGCTTCTTGGGAAGATCTGGCTGTATACACATAGCA
785 123_HRV22    ACTAGAGATGAAATGAGTATTGAGAGCTTCCTGGGAAGATCTGGTTGCATACATATATCA
786 124_HRV22a   ACTAGAGATGAAATGAGTATTGAGAGCTTCCTGGGAAGATCTGGTTGCATACATATATCA
787 125_HRV22b   ACTAGAGATGAAATGAGTATTGAGAGCTTCCTGGGAAGATCTGGTTGCATACATATATCA
788 126_HRV82    ACTAGAGATGAGATGAGCCTTGAGAGTTTCCTAGGGAGATCTGGCTGCATACACATATCA
789 127_HRV82b   ACTAGAGATGAGATGAGCCTTGAGAGTTTCCTAGGGAGATCTGGCTGCATACACATATCA
790 128_HRV82a   ACTAGAGATGAGATGAGCCTTGAGAGTTTCCTAGGGAGATCTGGCTGCATACACATATCA
791 129_HRV19    ACTAGGGATGAAATGAGCATAGAAAGTTTTCTTGGCAGATCCGGTTGTGTACATGTTTCA
792 130_HRV19a   ACTAGGGATGAAATGAGCATAGAAAGTTTTCTTGGCAGATCCGGTTGTGTACATGTTTCA
793 131_HRV19b   ACTAGGGATGAAATGAGCATAGAAAGTTTTCTTGGCAGATCCGGTTGTGTACATGTTTCA
794 132_HRV13    ACTAGGGATGAAATGAGTGTTGAGAGCTTTTTAGGCAGATCTGGTTGTATACACATGTCT
795 133_HRV13a   ACTAGGGATGAAATGAGTGTTGAGAGCTTTTTAGGCAGATCTGGTTGTATACACATGTCT
796 134_HRV13b   ACTAGGGATGAAATGAGTGTTGAGAGCTTTTTAGGCAGATCTGGTTGTATACACATGTCT
797 135_HRV41    ACTAGAGATGAAATGAGCATAGAAAGCTTTTTAGGTAGATCAGGCTGTGTACATAAGTCC
798 136_HRV41a   ACTAGAGATGAAATGAGCATAGAAAGCTTTTTAGGTAGATCAGGCTGTGTACATAAGTCC
799 137_HRV41b   ACTAGAGATGAAATGAGCATAGAAAGCTTTTTAGGTAGATCAGGCTGTGTACATAAGTCC
800 138_HRV73    ACTAGAGATGAAATGAGCATTGAGAGCTTCCTTGGCAGGTCAGGTTGTATACACATGTCA
801 139_HRV73b   ACTAGAGATGAAATGAGCATTGAAAGCTTCCTTGGCAGGTCAGGTTGTATACACATGTCA
802 140_HRV73a   ACTAGAGATGAAATGAGCATTGAAAGCTTCCTTGGCAGGTCAGGTTGTATACACATGTCA
803 141_HRV61    ACAAGAGATGAAATGAGTGTAGAAAGTTTCTTGGGTAGATCAGGGTGCATACATATGTCA
804 142_HRV61a   ACAAGAGATGAAATGAGTGTAGAAAGTTTCTTGGGTAGATCAGGGTGCATACATATGTCA
805 143_HRV61b   ACAAGAGATGAAATGAGTGTAGAAAGTTTCTTGGGTAGATCAGGGTGCATACATATGTCA
806 144_HRV96    ACGAGAGATGAAATGAGCATTGAGAGCTTTTTGGGTAGATCAGGGTGTATACACATGTCA
807 145_HRV96b   ACGAGAGATGAAATGAGCATTGAGAGCTTTTTGGGTAGATCAGGGTGTATACACATGTCA
808 146_HRV96a   ACGAGAGATGAAATGAGCATTGAGAGCTTTTTGGGTAGATCAGGGTGTATACACATGTCA
809 90_HRV16a|   ACATTGGATGAAATGAGTGTGGAAAGCTTCCTAGGCAGATCGGGGTGCATCCATGAATCA
810 91_HRV16b|   ACATTGGATGAAATGAGTGTGGAAAGCTTCCTAGGCAGATCGGGGTGCATCCATGAATCA
811 92_1AYM_A    ACATTGGATGAAATGAGTGTGGAAAGCTTCCTAGGCAGATCGGGGTGCATCCATGAATCA
812 93_HRV81a|   ACACTGGATGAAATGAGTGTAGAAAGTTTTTTAGGCAGATCAGGTTGCATTCATGAATCC
813 94_HRV81b|   ACACTGGATGAAATGAGTGTAGAAAGTTTTTTAGGCAGATCAGGTTGCATTCATGAATCC
814 95_HRV81     ACACTGGATGAAATGAGTGTAGAAAGTTTTTTAGGCAGATCAGGTTGCATTCATGAATCC
815 GROUP_1      AC-----ATGA-ATG-G--T-GA--G-TT--T-GG-AG--C-GG-TG--T-CA-----C-
816
817 1_HRV1A1|d   AGAATAAAGGTTGATTACACTGAC---------------TATAATGGA---CAGGACATA
818 2_HRV1A2|d   AGAATAAAGGTTGATTACACTGAC---------------TATAATGGA---CAGGACATA
819 3_HRV1A|cD   AGAATAAAGGTTGATTACACTGAC---------------TATAATGGA---CAGGACATA
820 4_HRV1B1|d   AGAATAAAGGTTGATTACAATGAC---------------TACAATGGA---GTGAACAAA
821 5_HRV1B2|d   AGAATAAAGGTTGATTACAATGAC---------------TACAATGGA---GTGAACAAA
822 6_HRV1B      AGAATAAAGGTTGATTACAATGAC---------------TACAATGGA---GTGAACAAA
823 7_HRV40a|d   ACAATTACAGTGGATAACAGTTTG---------------GAATATG------ATGACCAC
824 8_HRV40b|d   ACAATTACAGTGGATAACAGTTTG---------------GAATATG------ATGACCAC
825 9_HRV40      ACAATTACAGTGGATAACAGTTTG---------------GAATATG------ATGACCAC
826 10_HRV85     ACAATTACTGTGAATAACAACCTA---------------GATTATG------ATGAAAAT
827 11_HRV85a|   ACAATTACTGTGAATAACAACCTA---------------GATTATG------ATGAAAAT
828 12_HRV85b|   ACAATTACTGTGAATAACAACCTA---------------GATTATG------ATGAAAAT
829 13_HRV56a|   ACTATAACTGTGGATAATGATGTA---------------GATTATA------ATTCAAAG
830 14_HRV56b|   ACTATAACTGTGGATAATGATGTA---------------GATTATA------ATTCAAAG
831 15_HRV56     ACTATAACTGTGGATAATGATGTA---------------GATTATA------ATTCAAAG
832 16_HRV54     ACCATTACAATTCAAAATGATGTA---------------GAATACA------ATGATCAC
833 17_HRV98     ACTATCACTATTCAAAATGATGTA---------------GAATATA------ACGATCAT
834 18_HRV59a|   ACTATTACTGTCAATAAAGACATA---------------AAATATG------ATGATGGA
835 19_HRV59b|   ACTATTACTGTCAATAAAGACATA---------------AAATATG------ATGATGGA
836 20_HRV59     ACTATTACTGTCAATAAAGACATA---------------AAATATG------ATGATGGA
837 21_HRV63     ACTATCACTGTTGACAAAACCATT---------------GACTATG------ACACTGGA
838 22_HRV63b|   ACTATCACTGTTGACAAAACCATT---------------GACTATG------ACACTGGA
839 23_HRV63a|   ACTATCACTGTTGACAAAACCATT---------------GACTATG------ACACTGGA
840 24_HRV39     ACAATTACTATGAAGAAGGAG------------------AACTATA------ATGATCAT
841 25_HRV39a|   ACAATTACTATGAAGAAGGAG------------------AACTATA------ATGATCAT
842 26_HRV39b|   ACAATTACTATGAAGAAGGAG------------------AACTATA------ATGAACAT
843 27_HRV10a|   ACAATAACTGTTAATAATACAAGA---------------CCCTACA------ATGAACAC
844 28_HRV10b|   ACAATAACTGTTAATAATACAAGA---------------CCCTACA------ATGAACAC
845 29_HRV10     ACAATAACTGTTAATAATACAAGA---------------CCCTACA------ATGAACAC
```

FIG. D12 CONT'D

```
08.trace                                                                                    9/20/2007 5:05 PM 846  30_HRV100a   ACAATTACTGTAAGTAAAATGAAA---------------AATTATA------ATGAGCAC
847  31_HRV100b   ACAATTACTGTAAGTAAAATGAAA---------------AATTATA------ATGAGCAC
848  32_HRV100    ACAATTACTGTAAGTAAAATGAAA---------------AATTATA------ATGAGCAC
849  33_HRV66     ACAATTAATGTGGATAGCACAAAA---------------ACATATG------ATGAATCC
850  34_HRV66b|   ACAATTAATGTGGATAGCACAAAA---------------ACATATG------ATGAATCC
851  35_HRV66a|   ACAATTAATGTGGATAGCACAAAA---------------ACATATG------ATGAATCC
852  36_HRV77a|   ACAATAAATGTAGAAGATGGTAAA---------------ACTTATG------ATGAATCT
853  37_HRV77b|   ACAATAAATGTAGAAGATGGTAAA---------------ACTTATG------ATGAATCT
854  38_HRV77     ACAATAAATGTAGAAGATGGTAAA---------------ACTTATG------ATGAATCT
855  39_HRV62a    ACAATTGAA---------ACAACG---------------CTTAGTC------ATAAAGAT
856  40_HRV62b    ACAATTGAA---------ACAACG---------------CTTAGTC------ATAAAGAT
857  41_HRV25     ACAATTGAA---------ACAAAA---------------CTTAAAC------ATGATGAA
858  42_HRV29a    ACAATAAAA---------GCAAAT---------------CAGGCAC------ATGACGCC
859  43_HRV29b    ACAATAAAA---------GCAAAT---------------CAGGCAC------ATGACGCC
860  44_HRV44a    ACAATAAAG---------ACAAAT---------------CAGGCAC------ACAATACC
861  45_HRV44b    ACAATAAAG---------ACAAAT---------------CAGGCAC------ACAATACC
862  46_HRV31     ATAATAGAA---------CCAGAT---------------GGACTCC------ATGATAGC
863  47_HRV31a|   ATAATAGAA---------CCAGAT---------------GGACTCC------ATGATAGC
864  48_HRV31b|   ATAATAGAA---------CCAGAT---------------GGACTCC------ATGATAGC
865  49_HRV47     ACAATAAAA---------TCAGAT---------------GAGCAAC------ACATTAAT
866  50_HRV47a|   ACAATAAAA---------TCAGAT---------------GAGCAAC------ACATTAAT
867  51_HRV47b|   ACAATACAA---------TCAAAT---------------GAGCAAC------ACATTAAT
868  52_HRV11     AAGTTAATTGTGCAGTATGAAGAA---------------TATAAT------GGAAAGAAA
869  53_HRV11b|   AAGTTAATTGTGCAGTATGAAGAC---------------TATAAT------GGAAAGAAA
870  54_HRV11a|   AAGTTAATTGTGCAGTATGAAGAC---------------TATAAT------GGAAAGAAA
871  55_HRV76     AAGCTAGTTGTAGAATATGAGGGA---------------TATGAT------GATACAAAA
872  56_HRV76b|   AAGCTAGTTGTAGAATATGAGGGA---------------TATGAT------GATACAAAA
873  57_HRV76a|   AAGCTAGTTGTAGAATATGAGGGA---------------TATGAT------GATACAAAA
874  58_HRV33     AAATTAGTAGTGAAATATGAAGAC---------------TATAAT------GAGAAAAAG
875  59_HRV33b|   AAATTAGTAGTGAAATATGAAGAC---------------TATAAT------GAGAAAAAG
876  60_HRV33a|   AAATTAGTAGTGAAATATGAAGAC---------------TATAAT------GAGAAAAAG
877  61_HRV24a|   AAGTTGACTGTGGATTAT---GAC---------------AATTAT------GATACAAAA
878  62_HRV24b|   AAGTTGACTGTGGATTAT---GAC---------------AATTAT------GATACAAAA
879  63_HRV24     AAGTTGACTGTGGATTAT---GAC---------------AATTAT------GATACAAAA
880  64_HRV90     AAATTAGTTGTAAACTAT---GAT---------------AATTAT------GATGAAAAC
881  65_HRV90a|   AAATTAGTTGTAAACTAT---GAT---------------AATTAT------GATGAAAAC
882  66_HRV90b|   AAATTAGTTGTAAACTAT---GAT---------------AATTAT------GATGAAAAC
883  67_HRV34     AAACTTGTTGTAGATTATGAAAAT---------------TACAATGCA---AAAACAAAG
884  68_HRV34b|   AAACTTGTTGTAGATTATGAAAAT---------------TACAATGCA---AAAACAAAG
885  69_HRV34a|   AAACTTGTTGTAGATTATGAAAAT---------------TACAATGCA---AAAACAAAG
886  70_HRV50a|   AAATTAGTTGTTGATTATGATGGT---------------TACAATGAG---GAAACAAAG
887  71_HRV50b|   AAATTAGTTGTTGATTATGATGGT---------------TACAATGAG---GAAACAAAG
888  72_HRV50     AAATTAGTTGTTGATTATGATGGT---------------TACAATGAG---GAAACAAAG
889  73_HRV18a|   AAGTTAGTTGTACATTATGAAGAT---------------TATAATGCA---GAAACAAGG
890  74_HRV18b|   AAGTTAGTTGTACATTATGAAGAT---------------TATAATGCA---GAAACAAGG
891  75_HRV18     AAGTTAGTTGTACATTATGAAGAT---------------TATAATGCA---GAAACAAGG
892  76_HRV55     GAGTTAGTTGTTCATTATGAAGAA---------------TATAACAAA---GAGGGAAAA
893  77_HRV55b|   GAGTTAGTTGTTCATTATGAAGAA---------------TATAACAAA---GAGGGAAAA
894  78_HRV55a|   GAGTTAGTTGTTCATTATGAAGAA---------------TATAACAAA---GAGGGAAAA
895  79_HRV57     GAGCTTAAGGTAAAATATGAAAAT---------------TACAACACA---GAG------
896  80_HRV57a|   GAGCTTAAGGTAAAATATGAAAAT---------------TACAACACA---GAG------
897  81_HRV57b|   GAGCTTAAGGTAAAATATGAAAAT---------------TACAACACA---GAG------
898  82_HRV21     AAATTAGTAGTTAACTATGATAAT---------------TACAATACT---GGAGAAAAT
899  83_HRVHan    AAATTAATAGTTAACTATGACAAC---------------TACAATACT---GGAGAAAAT
900  84_HRV43     ACACTTGAAGTAAATTATGATGAT---------------TATAATGGG---ACAGGCATA
901  85_HRV43b|   ACACTTGAAGTAAATTATGATGAT---------------TATAATGGG---ACAGGCATA
902  86_HRV43a|   ACACTTGAAGTAAATTATGATGAT---------------TATAATGGG---ACAGGCATA
903  87_HRV75     ACACTTGAGATGGATTATACAAAC---------------TATAATGGA---GAAGGCAAA
904  88_HRV75b|   ACACTTGAGATGGATTATACAAAC---------------TATAATGGA---GAAGGCAAA
905  89_HRV75a|   ACACTTGAGATGGATTATACAAAC---------------TATAATGGA---GAAGGCAAA
906  96_HRV9a|d   AAATTGAATATTGATTACAGTGAC---------------TATGATAAG---AGTGTTGAA
907  97_HRV9b|d   AAATTGAATATTGATTACAGTGAC---------------TATGATAAG---AGTGTTGAA
908  98_HRV9      AAATTGAATATTGATTACAGTGAC---------------TATGATAAG---AGTGTTGAA
909  99_HRV32     AAATTAGATATTGATTATACCAAT---------------TACAATAAA---AGTGTTAAG
910  100_HRV32a   AAATTAGATATTGATTATACCAAT---------------TACAATAAA---AGTGTTAAG
```

FIG. D12 CONT'D

```
08.trace                                                                               9/20/2007 5:05 PM 911  101_HRV32b    AAATTAGATATTGATTATACCAAT---------------TACAATAAA---AGTGTTAAG
    912  102_HRV67     AAATTGAATATTGATTATAATGCA---------------TATGATGAA---AGTAGGGAC
    913  103_HRV67a    AAATTGAATATTGATTATAATGCA---------------TATGATGAA---AGTAGGGAC
    914  104_HRV67b    AAATTGAATATTGATTATAATGCA---------------TATGATGAA---AGTAGGGAC
    915  105_HRV15     GATTTGAAAATACATTATGAAGAT---------------TATAATAAA---GATGGGAAA
    916  106_HRV15a    GATTTGAAAATACATTATGAAGAT---------------TATAATAAA---GATGGGAAA
    917  107_HRV15b    GATTTGAAAATACATTATGAAGAT---------------TATAATAAA---GATGGGAAA
    918  108_HRV74a    CATCTAAAAATTGATTATACAAAC---------------TATAATGTT---AAAGGGAAG
    919  109_HRV74b    CATCTAAAAATTGATTATACAAAC---------------TATAATGTT---AAAGGGAAG
    920  110_HRV74     CATCTAAAAATTGATTATACAAAC---------------TATAATGTT---AAAGGGAAG
    921  111_HRV38a    AATCTTGACATAGATTACATTAAT---------------TACAACTCT---GAAGACAAA
    922  112_HRV38b    AATCTTGACATAGATTACATTAAT---------------TACAACTCT---GAAGACAAA
    923  113_HRV38     AATCTTGACATAGATTACATTAAT---------------TACAACTCT---GAAGACAAA
    924  114_HRV60     AAATTAGAAATTGACTATAGTAAC---------------TACAATGAG---GAGAATAAA
    925  115_HRV60a    AAATTAGAAATTGACTATAGTAAC---------------TACAATGAG---GAGAATAAA
    926  116_HRV60b    AAATTAGAAATTGACTATAGTAAC---------------TACAATGAG---GAGAATAAA
    927  117_HRV64a    GATTTAAAAGTAAATTATACTGGG---------------TATAATGAT---GAAGGTAAC
    928  118_HRV64b    GATTTAAAAGTAAATTATACTGGG---------------TATAATGAT---GAAGGTAAC
    929  119_HRV64     GATTTAAAAGTAAATTATACTGGG---------------TATAATGAT---GAAGGTAAC
    930  120_HRV94a    CATCTAGAGATCAAGTATGATGGT---------------TACAATGAT---GCTGGCAAC
    931  121_HRV94b    CATCTAGAGATCAAGTATGATGGT---------------TACAATGAT---GCTGGCAAC
    932  122_HRV94     CATCTAGAGATCAAGTATGATGGT---------------TACAATGAT---GCTGGCAAC
    933  123_HRV22     CACTTAGAAGTAAAATACACAGGG---------------TATAATGAA---GAGGGTAAT
    934  124_HRV22a    CACTTAGAAGTAAAATACACAGGG---------------TATAATGAA---GAGGGTAAT
    935  125_HRV22b    CACTTAGAAGTAAAATACACAGGG---------------TATAATGAA---GAGGGTAAT
    936  126_HRV82     CACCTAAATGTCAGATACACTG-----------------ATTATAAT---GAAGGTAAT
    937  127_HRV82b    CACCTAAATGTCAGATACACTG-----------------ATTATAAT---GAAGGTAAT
    938  128_HRV82a    CACCTAAATGTCAGATACACTG-----------------ATTATAAT---GAAGGTAAT
    939  129_HRV19     GAGCTCCAATTAGATTATACCAAT---------------TACAATCAA---GAAAATAAT
    940  130_HRV19a    GAGCTCCAATTAGATTATACCAAT---------------TACAATCAA---GAAAATAAT
    941  131_HRV19b    GAGCTCCAATTAGATTATACCAAT---------------TACAATCAA---GAAAATAAT
    942  132_HRV13     ACCATGAACATAGATTATACTAAT---------------TATGATGAT---TCTGTTAAT
    943  133_HRV13a    ACCATGAACATAGATTATACTAAT---------------TATGATGAT---TCTGTTAAT
    944  134_HRV13b    ACCATGAACATAGATTATACTAAT---------------TATGATGAT---TCTGTTAAT
    945  135_HRV41     ACTTTGAATATAGATTATACTGAT---------------TATGATGAT---TCTATCCAG
    946  136_HRV41a    ACTTTGAATATAGATTATACTGAT---------------TATGATGAT---TCTATCCAG
    947  137_HRV41b    ACTTTGAATATAGATTATACTGAT---------------TATGATGAT---TCTATCCAG
    948  138_HRV73     ACTATGAATATAAATTATGAAAAT---------------TATGATGAT---GCTCCTGAA
    949  139_HRV73b    ACTATGAATATAAATTATGAAAAT---------------TATGATGAT---GCTCCTGAA
    950  140_HRV73a    ACTATGAATATAAATTATGAAAAT---------------TATGATGAT---GCTCCTGAA
    951  141_HRV61     ACATTAAATATAAACTATGATAAC---------------TATGATGAT---TCTATTGAA
    952  142_HRV61a    ACATTAAATATAAACTATGATAAC---------------TATGATGAT---TCTATTGAA
    953  143_HRV61b    ACATTAAATATAAACTATGATAAC---------------TATGATGAT---TCTATTGAA
    954  144_HRV96     ACATTAAACATAGATTATGACAAT---------------TATGATGAC---TCCCCTAAG
    955  145_HRV96b    ACATTAAACATAGATTATGACAAT---------------TATGATGAC---TCCCCTAAG
    956  146_HRV96a    ACATTAAACATAGATTATGACAAT---------------TATGATGAC---TCCCCTAAG
    957  90_HRV16a|    GTGTTGGATATTGTGGACAATTAC---------------AATGAT------------CAA
    958  91_HRV16b|    GTGTTGGATATTGTGGACAATTAC---------------AATGAT------------CAA
    959  92_1AYM_A     GTGTTGGATATTGTGGACAATTAC---------------AATGAT------------CAA
    960  93_HRV81a|    ATATTGGACATTAAAGAGGATTAC---------------AATACC------------CAG
    961  94_HRV81b|    ATATTGGACATTAAAGAGGATTAC---------------AATACC------------CAG
    962  95_HRV81      ATATTGGACATTAAAGAGGATTAC---------------AATACC------------CAG
    963  GROUP_1       ----T-----------------------...........--------...--------
    964
    965  1_HRV1A1|d    AATTTCACAAAATGGAAAATCACACTACAGGAAATGGCACAGATTAGGAGAAAATTTGAA
    966  2_HRV1A2|d    AATTTCACAAAATGGAAAATCACACTACAGGAAATGGCACAGATTAGGAGAAAATTTGAA
    967  3_HRV1A|cD    AATTTCACAAAATGGAAAATCACACTACAGGAAATGGCACAGATTAGGAGAAAATTTGAA
    968  4_HRV1B1|d    AACTTTACAACATGGAAAATCACACTGCAGGAGATGGCACAAATTAGAAGAAAATTCGAA
    969  5_HRV1B2|d    AACTTTACAACATGGAAAATCACACTGCAGGAGATGGCACAAATTAGAAGAAAATTCGAA
    970  6_HRV1B       AACTTTACAACATGGAAAATCACACTGCAAAATGGCACAAATTAGAAGAAAATTCGAA
    971  7_HRV40a|d    CACTTTGATAAGTGGCAGATAACCATACAAGAGATGTCACAAATTAGGAGAAAATTTGAA
    972  8_HRV40b|d    CACTTTGATAAGTGGCAGATAACCATACAAGAGATGTCACAAATTAGGAGAAAATTTGAA
    973  9_HRV40       CACTTTGATAAGTGGCAGATAACCATACAAGAGATGTCACAAATTAGGAGAAAATTTGAA
    974  10_HRV85      CACTTTGATCAGTGGCAGATAACTATACAGGAAATGGCACAAATTAGAAGGAAGTTTGAG
    975  11_HRV85a|    CACTTTGATCAGTGGCAGATAACTATACAGGAAATGGCACAAATTAGAAGGAAGTTTGAG
```

FIG. D12 CONT'D

```
08.trace                                                                           9/20/2007 5:05 PM 976 12_HRV85b|   CACTTTGATCAGTGGCAGATAACTATACAGGAAATGGCACAAATTAGAAGGAAGTTTGAG
 977 13_HRV56a|   CATTATAATAAATGGCAAATAACCTTACAAGAAATGGCTCAAGTTAGGCGTAAATTTGAA
 978 14_HRV56b|   CATTATAATAAATGGCAAATAACCTTACAAGAAATGGCTCAAGTTAGGCGTAAATTTGAA
 979 15_HRV56    CATTATAATAAATGGCAAATAACCTTACAAGAAATGGCTCAAGTTAGGCGTAAATTTGAA
 980 16_HRV54    CATTTTAAGAAATGGGATATAACATTACAAGAGATGGCACAAATACGAAGGAAATTTGAA
 981 17_HRV98    CATTTTAGACAATGGGATATAACATTACAAGAAATGGCACAAATTCGAAGAAAATTTGAA
 982 18_HRV59a|   CACTTTCTTAAATGGCCTATAACATTACAAGAGATGGCACAAATTAGGAGAAAATTTGAA
 983 19_HRV59b|   CACTTTCTTAAATGGCCTATAACATTACAAGAGATGGCACAAATTAGGAGAAAATTTGAA
 984 20_HRV59    CACTTTCTTAAATGGCCTATAACATTACAAGAGATGGCACAAATTAGGAGAAAATTTGAA
 985 21_HRV63    CATTTTAATAAATGGCAAATAACATTACAAGAGATGGCACAAATTAGAAGGAAATTTGAA
 986 22_HRV63b|   CATTTTAATAAATGGCAAATAACATTACAAGAGATGGCACAAATTAGAAGGAAATTTGAA
 987 23_HRV63a|   CATTTTAATAAATGGCAAATAACATTACAAGAGATGGCACAAATTAGAAGGAAATTTGAA
 988 24_HRV39    AATTTTGTGGATTGGAAAATTACTTTGCAGGAGATGGCACAGGTTAGAAGGAAATTTGAA
 989 25_HRV39a|   AATTTTGTGGATTGGAAAATTACTTTGCAGGAGATGGCACAGGTTAGAAGGAAATTTGAA
 990 26_HRV39b|   AATTTTGTGGATTGGAAAATTACTTTGCAGGAGATGGCACAGGTTAGGAGAAAATTTGAA
 991 27_HRV10a|   ACTTTTGACACATGGCAAATAACTCTACAAGAAATGGCCCAAATTAGAAGGAAATTTGAA
 992 28_HRV10b|   ACTTTTGACACATGGCAAATAACTCTACAAGAAATGGCCCAAATTAGAAGGAAATTTGAA
 993 29_HRV10    ACTTTTGACACATGGCAAATAACTCTACAAGAAATGGCCCAAATTAGAAGGAAATTTGAA
 994 30_HRV100a   ACTTTTGACAAATGGCAAATAACCCTACAGGAAATGGCCCAAATTAGAAGGAAATTTGAA
 995 31_HRV100b   ACTTTTGACAAATGGCAAATAACCCTACAGGAAATGGCCCAAATTAGAAGGAAATTTGAA
 996 32_HRV100   ACTTTTGACAAATGGCAAATAACCCTACAGGAAATGGCCCAAATTAGAAGGAAATTTGAA
 997 33_HRV66    AAATTTAGAACATGGCAAATTACATTGCAAGAAATGGCTCAAATCAGACGCAAATTTGAG
 998 34_HRV66b|   AAATTTAGAACATGGCAAATTACATTGCAAGAAATGGCTCAAATCAGACGCAAATTTGAG
 999 35_HRV66a|   AAATTTAGAACATGGCAAATTACATTGCAAGAAATGGCTCAAATCAGACGCAAATTTGAG
1000 36_HRV77a|   AAATTTAGAAAATGGCAAATTACACTACAAGAAATGGCTCAAATTAGGCGCAAATTTGAA
1001 37_HRV77b|   AAATTTAGAAAATGGCAAATTACACTACAAGAAATGGCTCAAATTAGGCGCAAATTTGAA
1002 38_HRV77    AAATTTAGAAAATGGCAAATTACACTACAAGAAATGGCTCAAATTAGGCGCAAATTTGAA
1003 39_HRV62a   AGATTCAAAACATGGAATATTAACTTACAAGAGATGGCTCAAATCAGGAGAAAGTTTGAA
1004 40_HRV62b   AGATTCAAAACATGGAATATTAACTTACAAGAGATGGCTCAAATCAGGAGAAAGTTTGAA
1005 41_HRV25    AGATTTAAAATATGGAATATCAATTTACAAGAAATGGCTCAAATTAGGAGAAAGTTTGAG
1006 42_HRV29a   AAGTTCGATAAATGGAATGTTAACTTACAAGAAATGGCTCAAATTAGGCGCAAATTTGAA
1007 43_HRV29b   AAGTTCGATAAATGGAATGTTAACTTACAAGAAATGGCTCAAATTAGGCGCAAATTTGAA
1008 44_HRV44a   AAGTTTGATAAATGGAATATCAACTTACAAGAAATGGCTCAAATTAGACGCAAATTTGAA
1009 45_HRV44b   AAGTTTGATAAATGGAATATCAACTTACAAGAAATGGCTCAAATTAGACGCAAATTTGAA
1010 46_HRV31    AAATATAAAGTATGGCACATTAATTTACAAGAGATGGCCCAGATTAGGCGAAAATTTGAA
1011 47_HRV31a|   AAATATAAAGTATGGCACATTAATTTACAAGAGATGGCCCAGATTAGGCGAAAATTTGAA
1012 48_HRV31b|   AAATATAAAGTATGGCACATTAATTTACAAGAGATGGCCCAGATTAGGCGAAAATTTGAA
1013 49_HRV47a   AAATTTAAAGTATGGCACATTAATTTACAAGAAATGGCCCAGATCAGGCGTAAATATGAA
1014 50_HRV47a|   AAATTTAAAGTATGGCACATTAATTTACAAGAAATGGCCCAGATCAGGCGTAAATATGAA
1015 51_HRV47b|   AAATTTAAAGTATGGCACATTAATTTACAAGAAATGGCCCAGATCAGGCGTAAATATGAA
1016 52_HRV11    AACTTTAACACATGGAAATAAACTTGCAAGAGATGGCACAAATTAGAAGGAAATTTGAA
1017 53_HRV11b|   AACTTTAACACATGGAAATAAACTTGCAAGAGATGGCACAAATTAGAAGGAAATTTGAA
1018 54_HRV11a|   AACTTTAACACATGGAAATAAACTTGCAAGAGATGGCACAAATTAGAAGGAAATTTGAA
1019 55_HRV76    AACTTTAAGACATGGAAATAAACCTACAAGAAATGGCACAAGTTAGAAGAAAATTTGAG
1020 56_HRV76b|   AACTTTAAGACATGGAAATAAACCTACAAGAAATGGCACAAGTTAGAAGAAAATTTGAG
1021 57_HRV76a|   AACTTTAAGACATGGAAATAAACCTACAAGAAATGGCACAAGTTAGAAGAAAATTTGAG
1022 58_HRV33    AATTTTATGACATGGAAAATAAATCTACAAGAGATGGCACAGATTAGGAGAAAATTTGAA
1023 59_HRV33b|   AATTTTATGACATGGAAAATAAATCTACAAGAGATGGCACAGATTAGGAGGAAATTTGAA
1024 60_HRV33a|   AATTTTATGACATGGAAAATAAATCTACAAGAGATGGCACAGATTAGGAGGAAATTTGAA
1025 61_HRV24a|   AATTTTTTCAAATGGCAAATAAATCTACAAGAAATGGCCCAAGTCAGAAGAAAATTTGAA
1026 62_HRV24b|   AATTTTTTCAAATGGCAAATAAATCTACAAGAAATGGCCCAAGTCAGAAGAAAATTTGAA
1027 63_HRV24    AATTTTTTCAAATGGCAAATAAATCTACAAGAAATGGCCCAAGTCAGAAGAAAATTTGAA
1028 64_HRV90    AACTTCCATAAATGGCAAATTAACCTGCAAGAGATGGCACAGATTAGAAGGAAATTTGAA
1029 65_HRV90a|   AACTTCCATAAATGGCAAATTAACCTGCAAGAGATGGCACAGATTAGAAGGAAATTTGAA
1030 66_HRV90b|   AACTTCCATAAATGGCAAATTAACCTGCAAGAGATGGCACAGATTAGAAGGAAATTTGAA
1031 67_HRV34    AACTTTATGACATGGCAAATTAATTTACAGGAAATGGCACAGATTAGAAGGAAATTTGAA
1032 68_HRV34b|   AACTTTATGACATGGCAAATTAATTTACAGGAAATGGCACAGATTAGAAGGAAATTTGAA
1033 69_HRV34a|   AACTTTATGACATGGCAAATTAATTTACAGGAAATGGCACAGATTAGAAGGAAATTTGAA
1034 70_HRV50a|   AACTTCAAGAAATGGCAAATCAACCTACAAGAAATGGCACAGATCAGAAGGAAATTTGAG
1035 71_HRV50b|   AACTTCAAGAAATGGCAAATCAACCTACAAGAAATGGCACAGATCAGAAGGAAATTTGAG
1036 72_HRV50    AACTTCAAGAAATGGCAAATCAACCTACAAGAAATGGCACAGATCAGAAGGAAATTTGAG
1037 73_HRV18a|   AACTTTGTAAAATGGCAAATAAATCTACAGGAAATGGCCCAGATTAGGAGAAAATTTGAG
1038 74_HRV18b|   AACTTTGTAAAATGGCAAATAAATCTACAGGAAATGGCCCAGATTAGGAGAAAATTTGAG
1039 75_HRV18    AACTTTGTAAAATGGCAAATAAATCTACAGGAAATGGCCCAGATTAGGAGAAAATTTGAG
1040 76_HRV55    AATTTTACTAAGTGGCAAGTAAACATCCAAGAGATGGCTCAGATTAGAAGAAAATTTGAA
```

FIG. D12 CONT'D

08.trace 9/20/2007 5:05 PM

```
1041  77_HRV55b|     AATTTTACTAAGTGGCAAGTAAACATCCAAGAGATGGCTCAGATTAGAAGAAAATTTGAA
1042  78_HRV55a|     AATTTTACTAAGTGGCAAGTAAACATCCAAGAGATGGCTCAGATTAGAAGAAAATTTGAA
1043  79_HRV57      AATTTCACTAAATGGGAAATAAATCTACAAGAAATGGCACAAATCAGAAGAAAATTTGAA
1044  80_HRV57a|    AATTTCACTAAATGGGAAATAAATCTACAAGAAATGGCACAAATCAGAAGAAAATTTGAA
1045  81_HRV57b|    AATTTCACTAAATGGGAAATAAATCTACAAGAAATGGCACAAATCAGAAGAAAATTTGAA
1046  82_HRV21      AACATTAGTACATGGCAAATAAATATTAAAGAGATGGCACAAATTAGGAGAAAATTTGAA
1047  83_HRVHan     AACATTAATACATGGCAAATAAATATTAAAGAGATGGCACAAATTGGGAGAAAATTTGAA
1048  84_HRV43      AATTTTACCCAATGGCCAATCAACTTGCAAGAAATGGCACAAATTAGAAGAAAGTATGAA
1049  85_HRV43b|    AATTTTACCCAATGGCCAATCAACTTGCAAGAAATGGCACAAATTAGAAGAAAGTATGAA
1050  86_HRV43a|    AATTTTACCCAATGGCCAATCAACTTGCAAGAAATGGCACAAATTAGAAGAAAGTATGAA
1051  87_HRV75      AACTTCACTCAGTGGCCAATCAATCTACAGGAAATGGCTCAAATTAGAAGGAAATATGAA
1052  88_HRV75b|    AACTTCACTCAGTGGCCAATCAATCTACAGGAAATGGCTCAAATTAGAAGGAAATATGAA
1053  89_HRV75a|    AACTTCACTCAGTGGCCAATCAATCTACAGGAAATGGCTCAAATTAGAAGGAAATATGAA
1054  96_HRV9a|d    AATTTCACAATCTGGAAATAAATATAAAGGAAATGGCCCAGATCAGGAGGAAATTTGAA
1055  97_HRV9b|d    AATTTCACAATCTGGAAATAAATATAAAGGAAATGGCCCAGATCAGGAGGAAATTTGAA
1056  98_HRV9       AATTTCACAATCTGGAAATAAATATAAAGGAAATGGCCCAGATCAGGAGGAAATTTGAA
1057  99_HRV32      AATTTCACAATTTGGAAGATAAATATAAAAGAAATGGCCCAGATTAGGAGAAAATTTGAG
1058  100_HRV32a    AATTTCACAATTTGGAAGATAAATATAAAAGAAATGGCCCAGATTAGGAGAAAATTTGAG
1059  101_HRV32b    AATTTCACAATTTGGAAGATAAATATAAAAGAAATGGCCCAGATTAGGAGAAAATTTGAG
1060  102_HRV67     AATTTCACAATTTGGAAAATAAATATAAAGAAATGGCCCAGATTAGGAGGAAATTTGAA
1061  103_HRV67a    AATTTCACAATTTGGAAAATAAATATAAAGAAATGGCCCAGATTAGGAGGAAATTTGAA
1062  104_HRV67b    AATTTCACAATTTGGAAAATAAATATAAAGAAATGGCCCAGATTAGGAGGAAATTTGAA
1063  105_HRV15     AACTTTACTAAATGGCAAATTAATCTCAAAGAAATGGCCCAGATTAGGAGAAAATTTGAG
1064  106_HRV15a    AACTTTACTAAATGGCAAATTAATCTCAAAGAAATGGCCCAGATTAGAAGGAAATTTGAG
1065  107_HRV15b    AACTTTACTAAATGGCAAATTAATCTCAAAGAAATGGCCCAGATTAGAAGGAAATTTGAG
1066  108_HRV74a    AATTTTACTAAATGGCAAATAAATCTTAAAGAAATGGCACAGATTAGGAGAAAATTTGAG
1067  109_HRV74b    AATTTTACTAAATGGCAAATAAATCTTAAAGAAATGGCACAGATTAGGAGAAAATTTGAG
1068  110_HRV74     AATTTTACTAAATGGCAAATAAATCTTAAAGAAATGGCACAGATTAGGAGAAAATTTGAG
1069  111_HRV38a    AACTTTACAACATGGCAAATCAATCTCAAAGAAATGGCTCAAATCAGAAGAAAGTTTGAA
1070  112_HRV38b    AACTTTACAACATGGCAAATCAATCTCAAAGAAATGGCTCAAATCAGAAGAAAGTTTGAA
1071  113_HRV38     AACTTTACAACATGGCAAATCAATCTCAAAGAAATGGCTCAAATCAGAAGAAAGTTTGAA
1072  114_HRV60     AATTTCACAACTTGGCAAATTAACCTAAAGGAAATGGCACAAATAAGAAGAAAGTTTGAA
1073  115_HRV60a    AATTTCACAACTTGGCAAATTAACCTAAAGGAAATGGCACAAATAAGAAGAAAGTTTGAA
1074  116_HRV60b    AATTTCACAACTTGGCAAATTAACCTAAAGGAAATGGCACAAATAAGAAGAAAGTTTGAA
1075  117_HRV64a    AATTTTAACAAATGGCAGATCACCTTGAAAGAAATGGCTCAGATAAGAAGGAAGTATGAA
1076  118_HRV64b    AATTTTAACAAATGGCAGATCACCTTGAAAGAAATGGCTCAGATAAGAAGGAAGTATGAA
1077  119_HRV64     AATTTTAACAAATGGCAGATCACCTTGAAAGAAATGGCTCAGATAAGAAGGAAGTATGAA
1078  120_HRV94a    AATTTCCAATCATGGCAAATTACCCTAAAAGAAATGGCACAAATAAGGAGAAATTTGAA
1079  121_HRV94b    AATTTCCAATCATGGCAAATTACCCTAAAAGAAATGGCACAAATAAGGAGGAAATTTGAA
1080  122_HRV94     AATTTCCAATCATGGCAAATTACCCTAAAAGAAATGGCACAAATAAGGAGGAAATTTGAA
1081  123_HRV22     AACTTTAACATATGGCAAATTAACCTTAAAGAGATGGCTCAGATAAGAAGGAAGTTTGAG
1082  124_HRV22a    AACTTTAACATATGGCAAATTAACCTTAAAGAGATGGCTCAGATAAGAAGGAAGTTTGAG
1083  125_HRV22b    AACTTTAACATATGGCAAATTAACCTTAAAGAGATGGCTCAGATAAGAAGGAAGTTTGAG
1084  126_HRV82     AACTTTAGATCATGGCAAATAAGCATAAAGGAAATGGCACAAATTAGAAGGAAGTTTGAA
1085  127_HRV82b    AACTTTAGATCATGGCAAATAAGCATAAAGGAAATGGCACAAATTAGAAGGAAGTTTGAA
1086  128_HRV82a    AACTTTAGATCATGGCAAATAAGCATAAAGGAAATGGCACAAATTAGAAGGAAGTTTGAA
1087  129_HRV19     AATTTCAAAACTTGGCAAATAAACTTGAAAGAAATGGCACAGATTAGAAGAAAATTTGAA
1088  130_HRV19a    AATTTCAAAACTTGGCAAATAAACTTGAAAGAAATGGCACAGATTAGAAGAAAATTTGAA
1089  131_HRV19b    AATTTCAAAACTTGGCAAATAAACTTGAAAGAAATGGCACAGATTAGAAGAAAATTTGAA
1090  132_HRV13     AATTTTGTGAAATGGAAAATAAGTTTGCAAGAAATGGCCCAAGTGCGCAGAAAATTTGAG
1091  133_HRV13a    AATTTTGTGAAATGGAAAATAAGTTTGCAAGAAATGGCCCAAGTGCGCAGAAAATTTGAG
1092  134_HRV13b    AATTTTGTGAAATGGAAAATAAGTTTGCAAGAAATGGCCCAAGTGCGCAGAAAATTTGAG
1093  135_HRV41     AACTTCAAGAAGTGGAAAATTAGCTTACAGGAGATGGCCCAAGTACGTAGAAAGTTTGAG
1094  136_HRV41a    AACTTCAAGAAGTGGAAAATTAGCTTACAGGAGATGGCCCAAGTACGTAGAAAGTTTGAG
1095  137_HRV41b    AACTTCAAGAAGTGGAAAATTAGCTTACAGGAGATGGCCCAAGTACGTAGAAAGTTTGAG
1096  138_HRV73     AATTTTACCAAATGGAAAATAAGTTTACAAGAGATGGCTCAAATACGTAGGAAATTTGAA
1097  139_HRV73b    AATTTTACCAAATGGAAAATAAGTTTACAAGAGATGGCTCAAATACGTAGGAAATTTGAA
1098  140_HRV73a    AATTTTACCAAATGGAAAATAAGTTTACAAGAGATGGCTCAAATACGTAGGAAATTTGAA
1099  141_HRV61     AACTTCAAGGTGTGGAAAATAAACCTGCAAGAGATGGCACAAATACGTAGAAAATTTGAG
1100  142_HRV61a    AACTTCAAGGTGTGGAAAATAAACCTGCAAGAGATGGCACAAATACGTAGAAAATTTGAG
1101  143_HRV61b    AACTTCAAGGTGTGGAAAATAAACCTGCAAGAGATGGCACAAATACGTAGAAAATTTGAG
1102  144_HRV96     AATTTTAAGGTGTGGAAAATAAATCTACAAGAAATGGCTCAAATTCGCAGGAAGTTTGAA
1103  145_HRV96b    AATTTTAAGGTGTGGAAAATAAATCTACAAGAAATGGCTCAAATTCGCAGGAAGTTTGAA
1104  146_HRV96a    AATTTTAAGGTGTGGAAAATAAATCTACAAGAAATGGCTCAAATTCGCAGGAAGTTTGAA
1105  90_HRV16a|    AGTTTCACTAAATGGAAGATAAACCTGCAAGAAATGGCACAAATTAGAAGAAAATTTGAA
```

FIG. D12 CONT'D 08.trace                                                                                            9/20/2007 5:05 PM

```
1106 91_HRV16b|   AGTTTCACTAAATGGAAGATAAACCTGCAAGAAATGGCACAAATTAGAAGAAAATTTGAA
1107 92_1AYM_A    AGTTTCACTAAATGGAAGATAAACCTGCAAGAAATGGCACAAATTAGAAGAAAATTTGAA
1108 93_HRV81a|   AGCTTTACTAAATGGAAAATTAACTTACAAGAGATGGCACAGATTAGGAGAAAGTTTGAA
1109 94_HRV81b|   AGCTTTACTAAATGGAAAATTAACTTACAAGAGATGGCACAGATTAGGAGAAAGTTTGAA
1110 95_HRV81     AGCTTTACTAAATGGAAAATTAACTTACAAGAGATGGCACAGATTAGGAGAAAGTTTGAA
1111 GROUP_1      ------------TGG----T-A---T--A-GA-ATG-C-CA--T--G--G-AA-T--GA-
1112
1113 1_HRV1A1|d   TTGTTTACATATGTCAGGTTTGACTCAGAAATAACCTTGG-TGCCTTGTATTGCTGGTAG
1114 2_HRV1A2|d   TTGTTTACATATGTCAGGTTTGACTCAGAAATAACCTTGG-TGCCTTGTATTGCTGGTAG
1115 3_HRV1A|cD   TTGTTTACATATGTCAGGTTTGACTCAGAAATAACCTTGG-TGCCTTGTATTGCTGGTAG
1116 4_HRV1B1|d   CTATTTACTTATGTTAGGTTTGATTCAGAAGTAACTTTAG-TACCCTGTATTGCTGGTAG
1117 5_HRV1B2|d   CTATTTACTTATGTTAGGTTTGATTCAGAAGTAACTTTAG-TACCCTGTATTGCTGGTAG
1118 6_HRV1B      CTATTTACTTATGTTAGGTTTGATTCAGAAGTAACTTTAG-TACCCTGTATTGCTGGTAG
1119 7_HRV40a|d   TTCTTTACATATGCTAGGTTTGATTCAGAAATTACCTTAG-TTCCTTGTATAGCCGGTAA
1120 8_HRV40b|d   TTCTTTACATATGCTAGGTTTGATTCAGAAATTACCTTAG-TTCCTTGTATAGCCGGTAA
1121 9_HRV40      TTCTTTACATATGCTAGGTTTGATTCAGAAATTACCTTAG-TTCCTTGTATAGCCGGTAA
1122 10_HRV85     TTCTTTACTTACACTAGATTTGATTCAGAAATCACTTTAG-TCCCTTGTATAGCTGGAAA
1123 11_HRV85a|   TTCTTTACTTACACTAGATTTGATTCAGAAATCACTTTAG-TCCCTTGTATAGCTGGAAA
1124 12_HRV85b|   TTCTTTACTTACACTAGATTTGATTCAGAAATCACTTTAG-TCCCTTGTATAGCTGGAAA
1125 13_HRV56a|   TTCTTTACTTATGTCAGATTTGATTCAGAGGTTACTTTGG-TACCTTGTGTAGCCGGCAA
1126 14_HRV56b|   TTCTTTACTTATGTCAGATTTGATTCAGAGGTTACTTTGG-TACCTTGTGTAGCCGGCAA
1127 15_HRV56     TTCTTTACTTATGTCAGATTTGATTCAGAGGTTACTTTGG-TACCTTGTGTAGCCGGCAA
1128 16_HRV54     TTCTTTACTTATGTTAGGTTTGATTCAGAAATTACTCTAG-TCCCCTGTATAGCTGGTAA
1129 17_HRV98     TTCTTTACTTATGTTAGATTTGATTCAGAAGTTACCTTAG-TTCCTTGCATAGCTGGCAA
1130 18_HRV59a|   TTCTTCACATATGTTAGATTTGACTCAGAAATCACTTTGG-TGCCTTGCATAGCTGGAAA
1131 19_HRV59b|   TTCTTCACATATGTTAGATTTGACTCAGAAATCACTTTGG-TGCCTTGCATAGCTGGAAA
1132 20_HRV59     TTCTTCACATATGTTAGATTTGACTCAGAAATCACTTTGG-TGCCTTGCATAGCTGGAAA
1133 21_HRV63     TTCTTCACATATGTCAGATTTGACTCAGAAGTCACTCTTG-TACCATGTATAGCAGGAAA
1134 22_HRV63b|   TTCTTCACATATGTCAGATTTGATTCAGAAGTCACTCTTG-TACCATGTATAGCAGGAAA
1135 23_HRV63a|   TTCTTCACATATGTCAGATTTGATTCAGAAGTCACTCTTG-TACCATGTATAGCAGGAAA
1136 24_HRV39     ATGTTCACCTATGTTAGATTTGACTCAGAAGATTACTTTAG-TCCCATGCATAGCTGGAAG
1137 25_HRV39a|   ATGTTCACCTATGTTAGATTTGACTCAGAGATTACTTTAG-TCCCATGCATAGCTGGAAG
1138 26_HRV39b|   ATGTTCACCTACGTTAGATTTGACTCAGAGATTACTTTAG-TCCCATGCATAGCTGGAAG
1139 27_HRV10a|   ATGTTTACATATGTTAGATTTGACTCAGAAGTCACTTTAG-TACCTTGCATCGCAGGCAA
1140 28_HRV10b|   ATGTTTACATATGTTAGATTTGACTCAGAAGTCACTTTAG-TACCTTGCATCGCAGGCAA
1141 29_HRV10     ATGTTTACATATGTTAGATTTGACTCAGAAGTCACTTTAG-TACCTTGCATCGCAGGCAA
1142 30_HRV100a   ATGTTTACATATGTCAGATTTGACTCAGAAATCACATTGG-TACCCTGTATTGCAGGAAA
1143 31_HRV100b   ATGTTTACATATGTCAGATTTGACTCAGAAATCACATTGG-TACCCTGTATTGCAGGAAA
1144 32_HRV100    ATGTTTACATATGTCAGATTTGACTCAGAAATCACATTGG-TACCCTGTATTGCAGGAAA
1145 33_HRV66     ATGTTCACATATGTTAGGTTTGATTCTGAAATTACATTAG-TCCCATGCATTGCAGGAAA
1146 34_HRV66b|   ATGTTCACATATGTTAGGTTTGATTCTGAAATTACATTAG-TCCCATGCATTGCAGGAAA
1147 35_HRV66a|   ATGTTCACATATGTTAGGTTTGATTCTGAAATTACATTAG-TCCCATGCATTGCAGGAAA
1148 36_HRV77a|   ATGTTTACATATGTAAGATTTGATTCAGAAATTACATTGG-TCCCATGTATTGCTGGAAA
1149 37_HRV77b|   ATGTTTACATATGTAAGATTTGATTCAGAAATTACATTGG-TCCCATGTATTGCTGGAAA
1150 38_HRV77     ATGTTTACATATGTAAGATTTGATTCAGAAATTACATTGG-TCCCATGTATTGCTGGAAA
1151 39_HRV62a    ATGTTTACATATGTAAGATTTGATTCAGAAATAACCCTGG-TTCCATCTATTGCAGGACG
1152 40_HRV62b    ATGTTTACATATGTAAGATTTGATTCAGAAATAACCCTGG-TTCCATCTATTGCAGGACG
1153 41_HRV25     ATGTTTACATATGTGAGATTTGATTCAGAGATAACCCTAG-TTCCATCTATTGCAGGACG
1154 42_HRV29a    ATGTTCACATATGTGAGATTTGACTCAGAAATAACTCTGG-TTCCTTTGCATTGCAGGACG
1155 43_HRV29b    ATGTTCACATATGTGAGATTTGACTCAGAAATAACTCTGG-TTCCATGCATTGCAGGACG
1156 44_HRV44a    ATGTTCACATATGTGAGATTTGATTCGGAAATAACTCTAG-TTCCATGCATTGCAGGACA
1157 45_HRV44b    ATGTTCACATATGTGAGATTTGATTCAGAAATAACTCTAG-TTCCATGCATTGCAGGACG
1158 46_HRV31     ATGTTCACATATGTAAGATTTGATTCAGAAGTGACCATAG-TTCCATGCATTGCAGGACA
1159 47_HRV31a|   ATGTTCACATATGTAAGATTTGATTCAGAAGTGACCATAG-TTCCATGCATTGCAGGACA
1160 48_HRV31b|   ATGTTCACATATGTAAGATTTGATTCAGAAGTGACCATAG-TTCCATGCATTGCAGGACA
1161 49_HRV47     ATGTTTACATATGTAAGATTTGATTCAGAAGTAACCATGG-TTCATGTATTGCAGGGTA
1162 50_HRV47a|   ATGTTTACATATGTAAGATTTGATTCAGAAGTAACCATGG-TTCCATGTATTGCAGGGTA
1163 51_HRV47b|   ATGTTTACATATGTAAGATTTGATTCAGAAGTAACCATGG-TTCCATGTATTGCAGGGTA
1164 52_HRV11     ATGTTCACATACACTAGATTTGATTCAGAGATCACATTGG-TGCCTTGTATAGCTGCAAA
1165 53_HRV11b|   ATGTTCACATACACTAGATTTGATTCAGAGATCACATTGG-TGCCTTGTATAGCTGCAAA
1166 54_HRV11a|   ATGTTCACATACACTAGATTTGATTCAGAGATCACATTGG-TGCCTTGTATAGCTGCAAA
1167 55_HRV76     ATGTTTACATATACTAGATTTGATTCAGAAGTTACTCTAG-TTCCTTCTATAGCTGCCAA
1168 56_HRV76b|   ATGTTTACATATACTAGATTTGATTCAGAAGTTACTCTAG-TTCCTTCTATAGCTGCCAA
1169 57_HRV76a|   ATGTTTACATATACTAGATTTGATTCAGAAGTTACTCTAG-TTCCTTCTATAGCTGCCAA
1170 58_HRV33     ATGTTTACATATGCCAGATTTGATTCAGAGATCACCCTAG-TCCCTTCTATAGCTGCCCA
```

FIG. D12 CONT'D 08.trace                                                                  9/20/2007 5:05 PM

```
1171  59_HRV33b|   ATGTTTACATATGCCAGATTTGATTCAGAGATCACCCTAG-TCCCTTCTATAGCTGCCCA
1172  60_HRV33a|   ATGTTTACATATGCCAGATTTGATTCAGAGATCACCCTAG-TCCCTTCTATAGCTGCCCA
1173  61_HRV24a|   TTATTCACATATACTAGATTTGACTCTGAGATTACAATAG-TTCCATCCATAGCTGGCAA
1174  62_HRV24b|   TTATTCACATATACTAGATTTGACTCTGAGATTACAATAG-TTCCATCCATAGCTGGCAA
1175  63_HRV24    TTATTCACATATACTAGATTTGACTCTGAGATTACAATAG-TTCCATCCATAGCTGGCAA
1176  64_HRV90    TTGTTTACATATGCTAGATTTGATTCTGAAATTACAATAG-TACCATCTATAGCTGGCAA
1177  65_HRV90a|   TTGTTTACATATGCTAGATTTGATTCTGAAATTACAATAG-TACCATCTATAGCTGGCAA
1178  66_HRV90b|   TTGTTTACATATGCTAGATTTGATTCTGAAATTACAATAG-TACCATCTATAGCTGGCAA
1179  67_HRV34    ATGTTCACCTACGTCAGATTTGATTCTGAAGTCACCCTAG-TACCATCAATAGCGGCCAA
1180  68_HRV34b|   ATGTTCACCTACGTCAGATTTGATTCTGAAGTCACCCTAG-TACCATCAATAGCGGCCAA
1181  69_HRV34a|   ATGTTCACCTACGTCAGATTTGATTCTGAAGTCACCCTAG-TACCATCAATAGCGGCCAA
1182  70_HRV50a|   ATGTTCACCTATGTGAGGTTTAATTCTGAGGTCACATTAG-TACCATCCATAGCTGCCAA
1183  71_HRV50b|   ATGTTCACCTATGTGAGGTTTAATTCTGAGGTCACATTAG-TACCATCCATAGCTGCCAA
1184  72_HRV50    ATGTTCACCTATGTGAGGTTTAATTCTGAGGTCACATTAG-TACCATCCATAGCTGCCAA
1185  73_HRV18a|   ATGTTTACATATGTTAGATTTGATTCAGAAATTACACTAG-TACCATCTGTAGCTGCTAA
1186  74_HRV18b|   ATGTTTACATATGTTAGATTTGATTCAGAAATTACACTAG-TACCATCTGTAGCTGCTAA
1187  75_HRV18    ATGTTTACATATGTTAGATTTGATTCAGAAATTACACTAG-TACCATCTGTAGCTGCTAA
1188  76_HRV55    ATGTTCACCTATACTAGATTTGATTCAGAAGTTACATTAG-TACCCTCTATTGCTGCAAA
1189  77_HRV55b|   ATGTTCACCTATACTAGATTTGATTCAGAAGTTACATTAG-TACCCTCTATTGCTGCAAA
1190  78_HRV55a|   ATGTTCACCTATACTAGATTTGATTCAGAAGTTACATTAG-TACCCTCTATTGCTGCAAA
1191  79_HRV57    CTATTTACATATGTTAGGTTTGATTCTGAAGTTACATTAG-TTCCCTCCATAGCTGCTCA
1192  80_HRV57a|   CTATTTACATATGTTAGGTTTGATTCTGAAGTTACATTAG-TTCCCTCCATAGCTGCTCA
1193  81_HRV57b|   CTATTTACATATGTTAGGTTTGATTCTGAAGTTACATTAG-TTCCCTCCATAGCTGCTCA
1194  82_HRV21    ATGTTCACCTATACTAGATTTGATTCAGAAATAACTTTGG-TGCCGTCAATTGCAGCTAG
1195  83_HRVHan   ATGTTCACCTATACTAGATTTGATTCAGAAATAACTTTGG-TACCGTCAATTGCAGCTAA
1196  84_HRV43    TTGTTCACATACTTAAGGTTTGATTCTGAAATTACCCTTG-TTCCTTGCATTGCAGCAAA
1197  85_HRV43b|   TTGTTCACATACTTAAGGTTTGATTCTGAAATTACCCTTG-TTCCTTGCATTGCAGCAAA
1198  86_HRV43a|   TTGTTCACATACTTAAGGTTTGATTCTGAAATTACCCTTG-TTCCTTGCATTGCAGCAAA
1199  87_HRV75    TTATTTACATATCTTAGATTTGATTCAGAGGTTACTCTGG-TGCCATGCATTGCAGCTAA
1200  88_HRV75b|   TTATTTACATATCTTAGATTTGATTCAGAGGTTACTCTGG-TGCCATGCATTGCAGCTAA
1201  89_HRV75a|   TTATTTACATATCTTAGATTTGATTCAGAGGTTACTCTGG-TGCCATGCATTGCAGCTAA
1202  96_HRV9a|d   TTGTTTACATATGCAAGATTTGACTCTGAAATAACATTGG-TCCCGTGTATAGCAGCAGA
1203  97_HRV9b|d   TTGTTTACATATGCAAGATTTGACTCTGAAATAACATTGG-TCCCGTGTATAGCAGCAGA
1204  98_HRV9     TTGTTTACATATGCAAGATTTGACTCTGAAATAACATTGG-TCCCGTGTATAGCAGCAGA
1205  99_HRV32    TTGTTTACATACACAAGGTTTGATTCTGAAATAACATTAG-TACCTTGTATAGCTGCAGA
1206  100_HRV32a   TTGTTTACATACACAAGGTTTGATTCTGAAATAACATTAG-TACCTTGTATAGCTGCAGA
1207  101_HRV32b   TTGTTTACATACACAAGGTTTGATTCTGAAATAACATTAG-TACCTTGTATAGCTGCAGA
1208  102_HRV67    CTATTCACATATACAAGATTTGATTCTGAGATAACACTGG-TACCATGCATAGCTGCAGA
1209  103_HRV67a   CTATTCACATATACAAGATTTGATTCTGAGATAACACTGG-TACCATGCATAGCTGCAGA
1210  104_HRV67b   CTATTCACATATACAAGATTTGATTCTGAGATAACACTGG-TACCATGCATAGCTGCAGA
1211  105_HRV15    TTATTCACATATGTAAGGTTTGATTCAGAAATAACACTTG-TACCATGCATTGCAGCAAA
1212  106_HRV15a   TTATTCACATATGTAAGGTTTGATTCAGAAATAACACTTG-TACCATGCATTGCAGCAAA
1213  107_HRV15b   TTATTCACATATGTAAGGTTTGATTCAGAAATAACACTTG-TACCATGCATTGCAGCAAA
1214  108_HRV74a   TTGTTCACATATGTTAGATTTGACTCAGAAGTGACATTAG-TTCCATGCATTGCTGCTAA
1215  109_HRV74b   TTGTTCACATATGTTAGATTTGACTCAGAAGTGACATTAG-TTCCATGCATTGCTGCTAA
1216  110_HRV74    TTGTTCACATATGTTAGATTTGACTCAGAAGTGACATTAG-TTCCATGCATTGCTGCTAA
1217  111_HRV38a   ATGTTTACATATGTGAGATTTGATTCAGAAGTTACATTAG-TCCCATGTATAGCAGCACA
1218  112_HRV38b   ATGTTTACATATGTGAGATTTGATTCAGAAGTTACATTAG-TCCCATGTATAGCAGCACA
1219  113_HRV38    ATGTTTACATATGTGAGATTTGATTCAGAAGTTACATTAG-TCCCATGTATAGCAGCACA
1220  114_HRV60    TTATTTACATATGTAAGATTTGATTCAGAATTGACTCTGG-TCCCATGCATAGCAGCAAA
1221  115_HRV60a   TTATTTACATATGTAAGATTTGATTCAGAATTGACTCTGG-TCCCATGCATAGCAGCAAA
1222  116_HRV60b   TTATTTACATATGTAAGATTTGATTCAGAATTGACTCTGG-TCCCATGCATAGCAGCAAA
1223  117_HRV64a   TTATTTACATATGTTAGATTTGATTCTGAAATAACCTTAG-TGCCTTGCATATCTTCTCA
1224  118_HRV64b   TTATTTACATATGTTAGATTTGATTCTGAAATAACCTTAG-TGCCTTGCATATCTTCTCA
1225  119_HRV64    TTATTTACATATGTTAGATTTGATTCTGAAATAACCTTAG-TGCCTTGCATATCTTCTCA
1226  120_HRV94a   CTATTTACTTATGTTAGATTTGATTCAGAAATAACTTTAG-TACCTTGCATATCATCTCA
1227  121_HRV94b   CTATTTACTTATGTTAGATTTGATTCAGAAATAACTTTAG-TACCTTGCATATCATCTCA
1228  122_HRV94    CTATTTACTTATGTTAGATTTGATTCAGAAATAACTTTAG-TACCTTGCATATCATCTCA
1229  123_HRV22    CTATTTACATATCTCAGGTTTGATTCTGAAATCACTTTGG-TACCATGCATTGCTTCACA
1230  124_HRV22a   CTATTTACATATCTCAGGTTTGATTCTGAAATCACTTTGG-TACCATGCATTGCTTCACA
1231  125_HRV22b   CTATTTACATATCTCAGGTTTGATTCTGAAATCACTTTGG-TACCATGCATTGCTTCACA
1232  126_HRV82    CTTTTCACATATGTGAGATTTGATTCAGAAATTACTTTAG-TGCCTTGCATAGCCTCTCA
1233  127_HRV82b   CTTTTCACATATGTGAGATTTGATTCAGAAATTACTTTAG-TGCCTTGCATAGCCTCTCA
1234  128_HRV82a   CTTTTCACATATGTGAGATTTGATTCAGAAATTACTTTAG-TGCCTTGCATAGCCTCTCA
1235  129_HRV19    CTTTTCACTTACCTCAGATTTGATTCAGAGGTAACATTAG-TCCCTTGCATAGCTGCTAA
```

FIG. D12 CONT'D

```
08.trace                                                              9/20/2007 5:05 PM 1236 130_HRV19a   CTTTTCACTTACCTCAGATTTGATTCAGAGGTAACATTAG-TCCCTTGCATAGCTGCTAA
1237 131_HRV19b   CTTTTCACTTACCTCAGATTTGATTCAGAGGTAACATTAG-TCCCTTGCATAGCTGCTAA
1238 132_HRV13    TTGTTCACCTATGTAAGATTTGATTCAGAAATAACAATTG-TGCCATGTATAGCCGGGCA
1239 133_HRV13a   TTGTTCACCTATGTAAGATTTGATTCAGAAATAACAATTG-TGCCATGTATAGCCGGGCA
1240 134_HRV13b   TTGTTCACCTATGTAAGATTTGATTCAGAAATAACAATTG-TGCCATGTATAGCCGGGCA
1241 135_HRV41    TTTTTTACGTATGTTAGATTTGACTCAGAAATAACAATTG-TGCCAAGTATAGCTGGACA
1242 136_HRV41a   TTTTTTACGTATGTTAGATTTGACTCAGAAATAACAATTG-TGCCAAGTATAGCTGGACA
1243 137_HRV41b   TTTTTTACGTATGTTAGATTTGACTCAGAAATAACAATTG-TGCCAAGTATAGCTGGACA
1244 138_HRV73    TTATTCACCTATGTAAGATTTGATTCAGAAGTGACAATTG-TACCATGTATAGCTGGTCA
1245 139_HRV73b   TTATTCACCTATGTAAGATTTGATTCAGAAGTGACAATTG-TACCATGTATAGCTGGTCA
1246 140_HRV73a   TTATTCACCTATGTAAGATTTGATTCAGAAGTGACAATTG-TACCATGTATAGCTGGTCA
1247 141_HRV61    TTGTTCACATATGCTAGATTTGATTCAGAGATTACAATTG-TACCTTGTGTTGCTGGGCA
1248 142_HRV61a   TTGTTCACATATGCTAGATTTGATTCAGAGATTACAATTG-TACCTTGTGTTGCTGGGCA
1249 143_HRV61b   TTGTTCACATATGCTAGATTTGATTCAGAGATTACAATTG-TACCTTGTGTTGCTGGGCA
1250 144_HRV96    CTGTTCACTTATGCTAGATTTGATTCAGAGATAACAATTG-TTCCATGTGTTGCTGTGCA
1251 145_HRV96b   CTGTTCACTTATGCTAGATTTGATTCAGAGATAACAATTG-TTCCATGTGTTGCTGTGCA
1252 146_HRV96a   CTGTTCACTTATGCTAGATTTGATTCAGAGATAACAATTG-TTCCATGTGTTGCTGTGCA
1253 90_HRV16a|   ATGTTTACTTATGCAAGATTTGACTCTGAAATTACTATGG-TACCAAGTGTAGCAGCCAA
1254 91_HRV16b|   ATGTTTACTTATGCAAGATTTGACTCTGAAATTACTATGG-TACCAAGTGTAGCAGCCAA
1255 92_1AYM_A    ATGTTTACTTATGCAAGATTTGACTCTGAAATTACTATGG-TACCAAGTGTAGCAGCCAA
1256 93_HRV81a|   ATGTTCACATACACTAGATTTAACTCTGAGATTACACTGG-TACCAAGTATTGCAAACAA
1257 94_HRV81b|   ATGTTCACATACACTAGATTTAACTCTGAGATTACACTGG-TACCAAGTATTGCAAACAA
1258 95_HRV81     ATGTTCACATACACTAGATTTAACTCTGAGATTACACTGG-TACCAAGTATTGCAAACAA
1259 GROUP_1      -T-TT-AC-TA----AG-TTT-A-TC-GA--T-AC--T-G.T-C------T--C------
1260
1261 1_HRV1A1|d   AGGAGACGACATTGGACATATTGTAATGCAATATATGTATGTTCCTCCAGGAGCTCCAAT
1262 2_HRV1A2|d   AGGAGACGACATTGGACATATTGTAATGCAATATATGTATGTTCCTCCAGGAGCTCCAAT
1263 3_HRV1A|cD   AGGAGACGACATTGGACATATTGTAATGCAATATATGTATGTTCCTCCAGGAGCTCCAAT
1264 4_HRV1B1|d   AGGAGATGACATTGGTCATGTTGTAATGCAGTATATGTATGTTCCCCCAGGAGCTCCAAT
1265 5_HRV1B2|d   AGGAGATGACATTGGTCATGTTGTAATGCAGTATATGTATGTTCCCCCAGGAGCTCCAAT
1266 6_HRV1B      AGGAGATGACATTGGTCATGTTGTAATGCAGTATATGTATGTTCCCCCAGGAGCTCCAAT
1267 7_HRV40a|d   GGGTGAAGACATTGGACACATTGTGATGCAATATATGTATGTACCCCCTGGCGCACCCAT
1268 8_HRV40b|d   GGGTGAAGACATTGGACACATTGTGATGCAATATATGTATGTACCCCCTGGCGCACCCAT
1269 9_HRV40      GGGTGAAGACATTGGACACATTGTGATGCAATATATGTATGTACCCCCTGGCGCACCCAT
1270 10_HRV85     GGGTGATGACATTGGACACATTGTAATGCAGTATATGTATGTGCCCCCCGGAGCACCAAT
1271 11_HRV85a|   GGGTGATGATATTGGACACATTGTAATGCAGTATATGTATGTGCCCCCCGGAGCACCAAT
1272 12_HRV85b|   GGGTGATGATATTGGACACATTGTAATGCAGTATATGTATGTGCCCCCCGGAGCACCAAT
1273 13_HRV56a|   GGGAGATGATATTGGACACATTGTAATGCAATACATGTATGTGCCTCCTGGTGCACCACT
1274 14_HRV56b|   GGGAGATGATATTGGACACATTGTAATGCAATACATGTATGTGCCTCCTGGTGCACCACT
1275 15_HRV56     GGGAGATGATATTGGACACATTGTAATGCAATACATGTATGTGCCTCCTGGTGCACCACT
1276 16_HRV54     GGGAGTTGATATTGGACACATTGTCATGCAATTCATGTATGTACCGCCTGGTGCACCAAA
1277 17_HRV98     GGGAGCTGACATTGGACACATTGTCATGCAATTCATGTATGTTCCACCTGGTGCACCTAA
1278 18_HRV59a|   AGGGGATGACATTGGTCATATAGTCATGCAATATATGTATGTTCCACCAGGTGCTCCACT
1279 19_HRV59b|   AGGGGATGACATTGGTCATATAGTCATGCAATATATGTATGTTCCACCAGGTGCTCCACT
1280 20_HRV59     AGGGGATGACATTGGTCATATAGTCATGCAATATATGTATGTTCCACCAGGTGCTCCACT
1281 21_HRV63     AGGTGATGACATTGGTCATATAGTTATGCAGTACATGTACGTTCCACCCGGTGCCCCTCT
1282 22_HRV63b|   AGGTGATGACATTGGTCATATAGTTATGCAGTACATGTACGTTCCACCCGGTGCCCCTCT
1283 23_HRV63a|   AGGTGATGACATTGGTCATATAGTTATGCAGTACATGTACGTTCCACCCGGTGCCCCTCT
1284 24_HRV39     AGGTGAAGATATTGGACACATAGTAATGCAATACATGTATGTCCCACCTGGTGCACCTGT
1285 25_HRV39a|   AGGTGAAGATATTGGACACATAGTAATGCAATACATGTATGTCCCACCTGGTGCACCTGT
1286 26_HRV39b|   AGGTGAAGATATTGGACACATAGTAATGCAATACATGTATGTCCCACCTGGTGCACCTGT
1287 27_HRV10a|   GGGCGATGACATAGGTCACATAGTTATGCAATATATGTATGTGCCACCTGGGGCTCCAGT
1288 28_HRV10b|   GGGCGATGACATAGGTCACATAGTTATGCAATATATGTATGTGCCACCTGGGGCTCCAGT
1289 29_HRV10     GGGCGATGACATAGGTCACATAGTTATGCAATATATGTATGTGCCACCTGGGGCTCCAGT
1290 30_HRV100a   AGGAGATGACATAGGGCATATCGTAATGCAGTACATGTATGTGCCACCTGGAGCTCCAGT
1291 31_HRV100b   AGGAGATGACATAGGGCATATCGTAATGCAGTACATGTATGTGCCACCTGGAGCTCCAGT
1292 32_HRV100    AGGAGATGACATAGGGCATATCGTAATGCAGTACATGTATGTGCCACCTGGAGCTCCAGT
1293 33_HRV66     GGGTGATGATATAGGACATATTGTGATGCAATACATGTATGTACCACCTGGAGCCCCAAT
1294 34_HRV66b|   GGGTGATGATATAGGACATATTGTGATGCAATACATGTATGTACCACCTGGAGCCCCAAT
1295 35_HRV66a|   GGGTGATGATATAGGACATATTGTGATGCAATACATGTATGTACCACCTGGAGCCCCAAT
1296 36_HRV77a|   AGGTGATGACATAGGACATGTTGTCATGCAATACATGTATGTACCACCAGGGGCACCCAT
1297 37_HRV77b|   AGGTGATGACATAGGACATGTTGTCATGCAATACATGTATGTACCACCAGGGGCACCCAT
1298 38_HRV77     AGGTGATGACATAGGACATGTTGTCATGCAATACATGTATGTACCACCAGGGGCACCCAT
1299 39_HRV62a    TGGTGCAGATATAGGTCACATAGTTATGCAATATATGTATGTACCACCTGGGGCTCCACT
1300 40_HRV62b    TGGTGCAGATATAGGTCACATAGTTATGCAATATATGTATGTACCACCTGGGGCTCCACT
```

FIG. D12 CONT'D

```
08.trace                                                                9/20/2007 5:05 PM 1301  41_HRV25    TGGTGCAGATATAGGTCACATAGTTATGCAATATATGTATGTGCCACCTGGAGCCCCATT
1302  42_HRV29a   TGGTAATGATATAGGTCACATAGTTATGCAGTACATGTATGTACCACCTGGAGCTCCAGT
1303  43_HRV29b   TGGTAATGATATAGGTCACATAGTTATGCAGTACATGTATGTACCACCTGGAGCTCCAGT
1304  44_HRV44a   TGGTGATGATATAGGCCACATAGTTATGCAGTACATGTATGTACCACCTGGAGCTCCAGT
1305  45_HRV44b   TGGTGATGATATAGGCCACATAGTTATGCAGTACATGTATGTACCACCTGGAGCTCCAGT
1306  46_HRV31    TGGTAGTGACATAGGCCATATAGTCATGCAATACATGTATGTACCACCTGGGGCCCCAGT
1307  47_HRV31a|  TGGTAGTGACATAGGCCATATAGTCATGCAATACATGTATGTACCACCTGGGGCCCCAGT
1308  48_HRV31b|  TGGTAGTGACATAGGCCATATAGTCATGCAATACATGTATGTACCACCTGGGGCCCCAGT
1309  49_HRV47    TGGTGATGACATAGGTCACATAGTTATGCAATACATGTATGTGCCGCCTGGGGCTCCAGT
1310  50_HRV47a|  TGGTGATGACATAGGTCACATAGTTATGCAATACATGTATGTGCCGCCTGGGGCTCCAGT
1311  51_HRV47b|  TGGTGATGACATAGGTCACATAGTTATGCAATACATGTATGTGCCGCCTGGGGCTCCAGT
1312  52_HRV11    AGGAAATGATATTGGTCATGTTGTAATGCAATATATGTATGTCCCACCAGGTGCTCCAGT
1313  53_HRV11b|  AGGAAATGATATTGGTCATGTTGTAATGCAATATATGTATGTCCCACCAGGTGCTCCAGT
1314  54_HRV11a|  AGGAAATGATATTGGTCATGTTGTAATGCAATATATGTATGTCCCACCAGGTGCTCCAGT
1315  55_HRV76    AGGGGATGACATTGGTCATGTAGTGATGCAATACATGTATGTCCCACCAGGCGCTCCAGT
1316  56_HRV76b|  AGGGGATGACATTGGTCATGTAGTGATGCAATACATGTATGTCCCACCAGGCGCTCCAGT
1317  57_HRV76a|  AGGGGATGACATTGGTCATGTAGTGATGCAATACATGTATGTCCCACCAGGCGCTCCAGT
1318  58_HRV33    GGGAGATGATGTTGGTCATGTTGTAATGCAGTACATGTATGTCCCACCAGGTGCACCAGC
1319  59_HRV33b|  GGGAGATGATGTTGGTCATGTTGTAATGCAGTACATGTATGTCCCACCAGGTGCACCAGC
1320  60_HRV33a|  GGGAGATGATGTTGGTCATGTTGTAATGCAGTACATGTATGTCCCACCAGGTGCACCAGC
1321  61_HRV24a|  GGGAGATGACATTGGACATGTTGTAATGCAGTACATGTATATACCACCTGGAGCACCAGT
1322  62_HRV24b|  GGGAGATGACATTGGACATGTTGTAATGCAGTACATGTATATACCACCTGGAGCACCAGT
1323  63_HRV24    GGGAGATGACATTGGACATGTTGTAATGCAGTACATGTATATACCACCTGGAGCACCAGT
1324  64_HRV90    GGGCAATGATATTGGACATGTTGTGATGCAATACATGTATATACCACCTGGGGCACCAGT
1325  65_HRV90a|  GGGCAATGATATTGGACATGTTGTGATGCAATACATGTATATACCACCTGGGGCACCAGT
1326  66_HRV90b|  GGGCAATGATATTGGACATGTTGTGATGCAATACATGTATATACCACCTGGGGCACCAGT
1327  67_HRV34    AGGTGATGATATTGGACATGTTGTGATGCAATACATGTATGTACCACCAGGTGCACCAAT
1328  68_HRV34b|  AGGTGATGATATTGGACATGTTGTGATGCAATACATGTATGTACCACCAGGTGCACCAAT
1329  69_HRV34a|  AGGTGATGATATTGGACATGTTGTGATGCAATACATGTATGTACCACCAGGTGCACCAAT
1330  70_HRV50a|  GGGTGTTGATATTGGACATGTTGTCATGCAATACATGTATGTCCCACCAGGTGCACCAAT
1331  71_HRV50b|  GGGTGTTGATATTGGACATGTTGTCATGCAATACATGTATGTCCCACCAGGTGCACCAAT
1332  72_HRV50    GGGTGTTGATATTGGACATGTTGTCATGCAATACATGTATGTCCCACCAGGTGCACCAAT
1333  73_HRV18a|  GGGTGATGACATAGGACATATTGTTATGCAGTACATGTATGTTCCTCCAGGAGCACCAAT
1334  74_HRV18b|  GGGTGATGACATAGGACATATTGTTATGCAGTACATGTATGTTCCTCCAGGAGCACCAAT
1335  75_HRV18    GGGTGATGACATAGGACATATTGTTATGCAGTACATGTATGTTCCTCCAGGAGCACCAAT
1336  76_HRV55    GGGAGATGACATTGGACATGTAGTCATGCAATACATGTATGTTCCACCTGGAGCACCAAT
1337  77_HRV55b|  GGGAGATGACATTGGACATGTAGTCATGCAATACATGTATGTTCCACCTGGAGCACCAAT
1338  78_HRV55a|  GGGAGATGACATTGGACATGTAGTCATGCAATACATGTATGTTCCACCTGGAGCACCAAT
1339  79_HRV57    AGGTGAGGATATAGGCCATGTTGTAATGCAATACATGTATGTCCCTCCTGGGGCACCAAT
1340  80_HRV57a|  AGGTGAGGATATAGGCCATGTTGTAATGCAATACATGTATGTCCCTCCTGGGGCACCAAT
1341  81_HRV57b|  AGGTGAGGATATAGGCCATGTTGTAATGCAATACATGTATGTCCCTCCTGGGGCACCAAT
1342  82_HRV21    AACGGGTGACATAGGCCATGTTGTCAATATATGTATGTCCCACCAGGTGCTCCAAT
1343  83_HRVHan   AGCGGGTGACATAGGACATGTTGTGATGCAATATATGTATGTCCCACCAGGTGCTCCAAT
1344  84_HRV43    AAGCAATGATATAGGCCATGTGGTAATGCAGTACATGTATGTACCACCAGGTGCGCCAAT
1345  85_HRV43b|  AAGCAATGATATAGGCCATGTGGTAATGCAGTACATGTATGTACCACCAGGTGCGCCAAT
1346  86_HRV43a|  AAGCAATGATATAGGCCATGTGGTAATGCAGTACATGTATGTACCACCAGGTGCGCCAAT
1347  87_HRV75    AGGGAATGACATAGGCCATGTAGTAATGCAATATATGTATGTACCACCAGGAGCACCAAT
1348  88_HRV75b|  AGGGAATGACATAGGCCATGTAGTAATGCAATATATGTATGTACCACCAGGAGCACCAAT
1349  89_HRV75a|  AGGGAATGACATAGGCCATGTAGTAATGCAATATATGTATGTACCACCAGGAGCACCAAT
1350  96_HRV9a|d  AAGTGATAGCGTTGGCCATGTTGTTATGCAGTACATGTATGTACCACCAGGGGCACCTTT
1351  97_HRV9b|d  AAGTGATAGCGTTGGCCATGTTGTTATGCAGTACATGTATGTACCACCAGGGGCACCTTT
1352  98_HRV9     AAGTGATAGCGTTGGCCATGTTGTTATGCAGTACATGTATGTACCACCAGGGGCACCTTT
1353  99_HRV32    AAGTGACAGCATTGGTCATGTTGTTATGCAGTACATGTATGTACCACCAGGGGCTCCTCT
1354  100_HRV32a  AAGTGACAGCATTGGTCATGTTGTTATGCAGTACATGTATGTACCACCAGGGGCTCCTCT
1355  101_HRV32b  AAGTGACAGCATTGGTCATGTTGTTATGCAGTACATGTATGTACCACCAGGGGCTCCTCT
1356  102_HRV67   GAGTGACAGCATTGGGCATGTTGTAATGCAATATATGTATGTACCTCCAGGAGCACCATT
1357  103_HRV67a  GAGTGACAGCATTGGGCATGTTGTAATGCAATATATGTATGTACCTCCAGGAGCACCATT
1358  104_HRV67b  GAGTGACAGCATTGGGCATGTTGTAATGCAATATATGTATGTACCTCCAGGAGCACCATT
1359  105_HRV15   GAGTGATAACATCGGTCATGTTGTCATGCAATATATGTATGTTCCTCCGGGAGCCCCTTT
1360  106_HRV15a  GAGTGATAACATCGGTCATGTTGTCATGCAATATATGTATGTTCCTCCGGGAGCCCCTTT
1361  107_HRV15b  GAGTGATAACATCGGTCATGTTGTCATGCAATATATGTATGTTCCTCCGGGAGCCCCTTT
1362  108_HRV74a  AAGTGACAACATTGGCCATGTTGTTATGCAATACATGTATGTCCCCCCAGGAGCACCTTT
1363  109_HRV74b  AAGTGACAACATTGGCCATGTTGTTATGCAATACATGTATGTCCCCCCAGGAGCACCTTT
1364  110_HRV74   AAGTGACAACATTGGCCATGTTGTTATGCAATACATGTATGTCCCCCCAGGAGCACCTTT
1365  111_HRV38a  AAATGAAGGTGTGGGGCATGTTGTTATGCAGTATATGTATGTCCCTCCAGGGGCACCATT
```

FIG. D12 CONT'D

```
08.trace                                                                              9/20/2007 5:05 PM 1366 112_HRV38b    AAATGAAGGTGTGGGGCATGTTGTTATGCAGTATATGTATGTCCCTCCAGGGGCACCATT
1367 113_HRV38     AAATGAAGGTGTGGGGCATGTTGTTATGCAGTATATGTATGTCCCTCCAGGGGCACCATT
1368 114_HRV60     AAATGATGGCATAGGTCATGTTGTCATGCAATACATGTATGTCCCCCCAGGAGCACCATT
1369 115_HRV60a    AAATGATGGCATAGGTCATGTTGTCATGCAATACATGTATGTCCCCCCAGGAGCACCATT
1370 116_HRV60b    AAATGATGGCATAGGTCATGTTGTCATGCAATACATGTATGTCCCCCCAGGAGCACCATT
1371 117_HRV64a    GAGTGCTAACATTGGTCATGTTGTTATGCAATATATGTATGTCCCTCCTGGAGCTCCAAT
1372 118_HRV64b    GAGTGCTAACATTGGTCATGTTGTTATGCAATATATGTATGTCCCTCCTGGAGCTCCAAT
1373 119_HRV64     GAGTGCTAACATTGGTCATGTTGTTATGCAATATATGTATGTCCCTCCTGGAGCTCCAAT
1374 120_HRV94a    AAGTGCTAATATTGGTCATGTTGTCATGCAGTACATGTATGTTCCTCCTGGAGCTCCAAA
1375 121_HRV94b    AAGTGCTAATATTGGTCATGTTGTCATGCAGTACATGTATGTTCCTCCTGGAGCTCCAAA
1376 122_HRV94     AAGTGCTAATATTGGTCATGTTGTCATGCAGTACATGTATGTTCCTCCTGGAGCTCCAAA
1377 123_HRV22     AAGTAAAAACATTGGTCATGTGGTCATGCAATACATGTATGTTCCGCCTGGAGCTCCTAA
1378 124_HRV22a    AAGTAAAAACATTGGTCATGTGGTCATGCAATACATGTATGTTCCGCCTGGAGCTCCTAA
1379 125_HRV22b    AAGTAAAAACATTGGTCATGTGGTCATGCAATACATGTATGTTCCGCCTGGAGCTCCTAA
1380 126_HRV82     AAGTAATGATATTGGGCATGTAGTGATGCAATACATGTATGTCCCACCAGGTGCTCCTAA
1381 127_HRV82b    AAGTAATGATATTGGGCATGTAGTGATGCAATACATGTATGTCCCACCAGGTGCTCCTAA
1382 128_HRV82a    AAGTAATGATATTGGGCATGTAGTGATGCAATACATGTATGTCCCACCAGGTGCTCCTAA
1383 129_HRV19     AAGTAAAAACATTGGACATGTTGTTATGCAATACATGTATGTGCCTCCTGGTGCTCCTAT
1384 130_HRV19a    AAGTAAAAACATTGGACATGTTGTTATGCAATACATGTATGTGCCTCCTGGTGCTCCTAT
1385 131_HRV19b    AAGTAAAAACATTGGACATGTTGTTATGCAATACATGTATGTGCCTCCTGGTGCTCCTAT
1386 132_HRV13     AGGTGGTGATGTCGGACATGTTGTTATGCAATACATGTATGTACCGCCCGGTGCACCCCT
1387 133_HRV13a    AGGTGGTGATGTCGGACATGTTGTTATGCAATACATGTATGTACCGCCCGGTGCACCCCT
1388 134_HRV13b    AGGTGGTGATGTCGGACATGTTGTTATGCAATACATGTATGTACCGCCCGGTGCACCCCT
1389 135_HRV41     GGGTAGTGATGTCGGACATGTTGTCATGCAATACATGTTCGTACCACCTGGCGCACCCCT
1390 136_HRV41a    GGGTAGTGATGTCGGACATGTTGTCATGCAATACATGTTCGTACCACCTGGCGCACCCCT
1391 137_HRV41b    GGGTAGTGATGTCGGACATGTTGTCATGCAATACATGTTCGTACCACCTGGCGCACCCCT
1392 138_HRV73     AAGTGGAGATGTGGGACATGTAGTTATGCAGTATATGTATGTCCCACCTGGAGCCCCTCT
1393 139_HRV73b    AAGTGGAGATGTGGGACATGTAGTTATGCAGTATATGTATGTCCCACCTGGAGCCCCTCT
1394 140_HRV73a    AAGTGGAGATGTGGGACATGTAGTTATGCAGTATATGTATGTCCCACCTGGAGCCCCTCT
1395 141_HRV61     AGGTGGTGACATTGGACACGTGGTCATGCAATACATGTATGTTCCACCTGGTGCACCTAC
1396 142_HRV61a    AGGTGGTGACATTGGACACGTGGTCATGCAATACATGTATGTTCCACCTGGTGCACCTAC
1397 143_HRV61b    AGGTGGTGACATTGGACACGTGGTCATGCAATACATGTATGTTCCACCTGGTGCACCTAC
1398 144_HRV96     GAGTGGTGATATTGGTCATGTGGTCATGCAATATATGTATGTTCCACCAGGTGCCCCCAC
1399 145_HRV96b    GAGTGGTGATATTGGTCATGTGGTCATGCAATATATGTATGTTCCACCAGGTGCCCCCAC
1400 146_HRV96a    GAGTGGTGATATTGGTCATGTGGTCATGCAATATATGTATGTTCCACCAGGTGCCCCCAC
1401  90_HRV16a|   AGATGGTCACATTGGTCATATAGTCATGCAATATATGTATGTACCACCAGGAGCACCTAT
1402  91_HRV16b|   AGATGGTCACATTGGTCATATAGTCATGCAATATATGTATGTACCACCAGGAGCACCTAT
1403  92_1AYM_A    AGATGGTCACATTGGTCATATAGTCATGCAATATATGTATGTACCACCAGGAGCACCTAT
1404  93_HRV81a|   GGAAGGTCATATTGGTCATATAGTAATGCAATACATGTATGTACCACCAGGAGCACCCAT
1405  94_HRV81b|   GGAAGGTCATATTGGTCATATAGTAATGCAATACATGTATGTACCACCAGGAGCACCCAT
1406  95_HRV81     GGAAGGTCATATTGGTCATATAGTAATGCAATACATGTATGTACCACCAGGAGCACCCAT
1407 GROUP_1       -----------T-GG-CA--T-GT-ATGCA-T--ATGT---T-CC-CC-GG-GC-CC---
1408
1409   1_HRV1A1|d  TCCTTCAAAAAGAAACGATTTCTCATGGCAATCAGGCACCAATATGTCAATATTCTGGCA
1410   2_HRV1A2|d  TCCTTCAAAAAGAAACGATTTCTCATGGCAATCAGGCACCAATATGTCAATATTCTGGCA
1411   3_HRV1A|cD  TCCTTCAAAAAGAAACGATTTCTCATGGCAATCAGGCACCAATATGTCAATATTCTGGCA
1412   4_HRV1B1|d  TCCAAAAACAAGAAATGATTTCTCATGGCAATCAGGCACTAATATGTCAATATTCTGGCA
1413   5_HRV1B2|d  TCCAAAAACAAGAAATGATTTCTCATGGCAATCAGGCACTAATATGTCAATATTCTGGCA
1414   6_HRV1B     TCCAAAAACAAGAAATGATTTCTCATGGCAATCAGGCACTAATATGTCAATATTCTGGCA
1415   7_HRV40a|d  ACCAAAGAAAAGAAATGATTACACATGGCAGTCAGGCACTAATGCTTCTGTATTCTGGCA
1416   8_HRV40b|d  ACCAAAGAAAAGAAATGATTACACATGGCAGTCAGGCACTAATGCTTCTGTATTCTGGCA
1417   9_HRV40     ACCAAAGAAAAGAAATGATTACACATGGCAGTCAGGCACTAATGCTTCTGTATTCTGGCA
1418  10_HRV85     ACCAAGGAAAAGAGATGATTACACATGGCAATCAGGTACTAATGCTTCCGTGTTTTGGCA
1419  11_HRV85a|   ACCAAGGAAAAGAGATGATTACACATGGCAATCAGGTACTAATGCTTCCGTGTTTTGGCA
1420  12_HRV85b|   ACCAAGGAAAAGAGATGATTACACATGGCAATCAGGTACTAATGCTTCCGTGTTTTGGCA
1421  13_HRV56a|   TCCAAACTCAAGAGATGATTTTACATGGCAATCTGGCACCAATGCTTCTGTCTTTTGGCA
1422  14_HRV56b|   TCCAAACTCAAGAGATGATTTTACATGGCAATCTGGCACCAATGCTTCTGTCTTTTGGCA
1423  15_HRV56     TCCAAACTCAAGAGATGATTTTACATGGCAATCTGGCACCAATGCTTCTGTCTTTTGGCA
1424  16_HRV54     ACCAGAAAAAAGGAATGATTATACTTGGGAATCAAGCACAAACCCTTCTATATTCTGGCA
1425  17_HRV98     ACCTAAAAAGAGGAATGATTATACTTGGGAATCAAGCACAAACCCTTCTATATTTGGCA
1426  18_HRV59a|   GCCCACAAAGAGAGATGATTACACATGGCAATCTGGTACTAATGCTTCAATATTCTGGCA
1427  19_HRV59b|   GCCCACAAAGAGAGATGATTACACATGGCAATCTGGTACTAATGCTTCAATATTCTGGCA
1428  20_HRV59     GCCCACAAAGAGAGATGATTACACATGGCAATCTGGTACTAATGCTTCAATATTCTGGCA
1429  21_HRV63     ACCCACCCGAAGAGAAGATTACACATGGCAATCTGGCACTAATGCTTCAATATTCTGGCA
1430  22_HRV63b|   ACCCACCCGAAGAGAAGATTACACATGGCAATCTGGCACTAATGCTTCAATATTCTGGCA
```

FIG. D12 CONT'D

```
08.trace                                                                    9/20/2007 5:05 PM 1431  23_HRV63a|   ACCCACCCGAAGAGAAGATTACACATGGCAATCTGGCACTAATGCTTCAATATTCTGGCA
1432  24_HRV39    ACCTAAGAAGAGAGATGATTACACATGGCAATCTGGAACAAATGCCTCAGTTTTCTGGCA
1433  25_HRV39a|   ACCTAAGAAGAGAGATGATTACACATGGCAATCTGGAACAAATGCCTCAGTTTTCTGGCA
1434  26_HRV39b|   ACCTAAGAAGAGAGATGATTACACATGGCAATCTGGAACAAATGCCTCAGTTTTCTGGCA
1435  27_HRV10a|   ACCAACTAAGAGAGATGATTTTGCTTGGCAGTCGGGAACAAATGCATCAGTCTTCTGGCA
1436  28_HRV10b|   ACCAACTAAGAGAGATGATTTTGCTTGGCAGTCGGGAACAAATGCATCAGTCTTCTGGCA
1437  29_HRV10    ACCAACTAAGAGAGATGATTTTGCTTGGCAGTCGGGAACAAATGCATCAGTCTTCTGGCA
1438  30_HRV100a   TCCAACAAAAAGGGATGATTTTGCATGGCAATCAGGCACAAATGCATCAGTTTTTTGGCA
1439  31_HRV100b   TCCAACAAAAAGGGATGATTTTGCATGGCAATCAGGCACAAATGCATCAGTTTTTTGGCA
1440  32_HRV100    TCCAACAAAAAGGGATGATTTTGCATGGCAATCAGGCACAAATGCATCAGTTTTTTGGCA
1441  33_HRV66    TCCAGATAATAGAACACACTTTGCTTGGCAATCAGGAACAAATGCATCTATATTCTGGCA
1442  34_HRV66b|   TCCAGATAATAGAACACACTTTGCTTGGCAATCAGGAACAAATGCATCTATATTCTGGCA
1443  35_HRV66a|   TCCAGATAATAGAACACACTTTGCTTGGCAATCAGGAACAAATGCATCTATATTCTGGCA
1444  36_HRV77a|   ACCAGATAGCAGGACTCATTTTGCATGGCAGTCAGGGACTAATGCATCAATATTCTGGCA
1445  37_HRV77b|   ACCAGATAGCAGGACTCATTTTGCATGGCAGTCAGGGACTAATGCATCAATATTCTGGCA
1446  38_HRV77    ACCAGATAGCAGGACTCATTTTGCATGGCAGTCAGGGACTAATGCATCAATATTCTGGCA
1447  39_HRV62a    ACCAACAGACAGAAAGCATTTTGCCTGGCAATCAAGTACTAATGCATCAATATTTTGGCA
1448  40_HRV62b    ACCAACAGACAGAAAGCATTTTGCCTGGCAATCAAGTACTAATGCATCAATATTTTGGCA
1449  41_HRV25    ACCAACAGACAGAAAACACTTTGCATGGCAATCAAGTACTAATGCATCAATATTTTGGCA
1450  42_HRV29a    ACCAAATGACAGAAATCATTTTGCATGGCAATCAGGGACTAATGCATCAATATTCTGGCA
1451  43_HRV29b    ACCAAATGACAGAAATCATTTTGCATGGCAATCAGGGACTAATGCATCAATATTCTGGCA
1452  44_HRV44a    ACCAGATGACAGAAACCACTTTGCATGGCAATCGGGGACTAATGCATCAATATTCTGGCA
1453  45_HRV44b    ACCAGATGACAGAATCCACTTTGCATGGCAATCGGGGAATAATGCATCAATATTCTGGCA
1454  46_HRV31    ACCAACAAATAGAAAACATTTTGCATGGCAATCAGGTACTAATGCATCGATTTTCTGGCA
1455  47_HRV31a|   ACCAACAAATAGAAAACATTTTGCATGGCAATCAGGTACTAATGCATCGATTTTCTGGCA
1456  48_HRV31b|   ACCAACAAATAGAAAACATTTTGCATGGCAATCAGGTACTAATGCATCGATTTTCTGGCA
1457  49_HRV47    GCCAACAAGTAGAGAGCACTTTGCATGGCAGTCAGGTACCAATGCATCAACTTTCTGGCA
1458  50_HRV47a|   GCCAACAAGTAGAGAGCACTTTGCATGGCAGTCAGGTACCAATGCATCAACTTTCTGGCA
1459  51_HRV47b|   GCCAACAAGTAGAGAGCACTTTGCATGGCAGTCAGGTACCAATGCATCAATTTTCTGGCA
1460  52_HRV11    TCCAGAGAAAAGAGATGATTATACATGGCAATCAGGAACAAATGCATCTATTTCTGGCA
1461  53_HRV11b|   TCCAGAGAAAAGAGATGATTATACATGGCAATCAGGAACAAATGCATCTATTTCTGGCA
1462  54_HRV11a|   TCCAGAGAAAAGAGATGATTATACATGGCAATCAGGAACAAATGCATCTATTTCTGGCA
1463  55_HRV76    TCCAAAGAAGAGAGATGACTACACATGGCAGTCAGGAACCAATGCATCTATTTCTGGCA
1464  56_HRV76b|   TCCAAAGAAGAGAGATGACTACACATGGCAGTCAGGAACCAATGCATCTATTTCTGGCA
1465  57_HRV76a|   TCCAAAGAAGAGAGATGACTACACATGGCAGTCAGGAACCAATGCATCTATTTCTGGCA
1466  58_HRV33    TCCAGAAAAGAGAGATGATTACACATGGCAATCAGGAACAAATGCATCTGTCTTTTGGCA
1467  59_HRV33b|   TCCAGAAAAGAGAGATGATTACACATGGCAATCAGGAACAAATGCATCTGTCTTTTGGCA
1468  60_HRV33a|   TCCAGAAAAGAGAGATGATTACACATGGCAATCAGGAACAAATGCATCTGTCTTTTGGCA
1469  61_HRV24a|   CCCAACAAAGAGAGATGATTATACATGGCAATCAGGAACAAATGCATCTGTCTTTTGGCA
1470  62_HRV24b|   CCCAACAAAGAGAGATGATTATACATGGCAATCAGGAACAAATGCATCTGTCTTTTGGCA
1471  63_HRV24    CCCAACAAAGAGAGATGATTATACATGGCAATCAGGAACAAATGCATCTGTCTTTTGGCA
1472  64_HRV90    ACCTGAGAAGAGGGATGATTATGCATGGCAATCAGGCACTAATGCATCTATCTTTTGGCA
1473  65_HRV90a|   ACCTGAGAAGAGGGATGATTATGCATGGCAATCAGGCACTAATGCATCTATCTTTTGGCA
1474  66_HRV90b|   ACCTGAGAAGAGGGATGATTATGCATGGCAATCAGGCACTAATGCATCTATCTTTTGGCA
1475  67_HRV34    ACCTAAAACTAGAGATGATTTTGCATGGCAATCTGGAACAAATGCCTCAATATTTTGGCA
1476  68_HRV34b|   ACCTAAAACTAGAGATGATTTTGCATGGCAATCTGGAACAAATGCCTCAATATTTTGGCA
1477  69_HRV34a|   ACCTAAAACTAGAGATGATTTTGCATGGCAATCTGGAACAAATGCCTCAATATTTTGGCA
1478  70_HRV50a|   ACCCAAGACTAGGGATGATTTTGCCTGGCAATCTGGAACTAATGCTTCAATCTTTTGGCA
1479  71_HRV50b|   ACCCAAGACTAGGGATGATTTTGCCTGGCAATCTGGAACTAATGCTTCAATCTTTTGGCA
1480  72_HRV50    ACCCAAGACTAGGGATGATTTTGCCTGGCAATCTGGAACTAATGCTTCAATCTTTTGGCA
1481  73_HRV18a|   ACCAAAAACCAGAGATGATTTTGCCTGGCAATCTGGAACAAATGCATCAATCTTCTGGCA
1482  74_HRV18b|   ACCAAAAACCAGAGATGATTTTGCCTGGCAATCTGGAACAAATGCATCAATCTTCTGGCA
1483  75_HRV18    ACCAAAAACCAGAGATGATTTTGCCTGGCAATCTGGAACAAATGCATCAATCTTCTGGCA
1484  76_HRV55    TCCAAAGACAAGAGAAGATTATGCTTGGCAATCAGGGACCAATGCATCTATCTTTTGGCA
1485  77_HRV55b|   TCCAAAGACAAGAGAAGATTATGCTTGGCAATCAGGGACCAATGCATCTATCTTTTGGCA
1486  78_HRV55a|   TCCAAAGACAAGAGAAGATTATGCTTGGCAATCAGGGACCAATGCATCTATCTTTTGGCA
1487  79_HRV57    TCCAAAAACAAGAGAGGATTATACATGGCAATCTGGTACCAATGCTTCAATATTTTGGCA
1488  80_HRV57a|   TCCAAAAACAAGAGAGGATTATACATGGCAATCTGGTACCAATGCTTCAATATTTTGGCA
1489  81_HRV57b|   TCCAAAAACAAGAGAGGATTATACATGGCAATCTGGTACCAATGCTTCAATATTTTGGCA
1490  82_HRV21    TCCAAAAACTAGGGAAGATTTTGCTTGGCAGTCAGGCACTAATGCATCCATTTTCTGGCA
1491  83_HRVHan    TCCAAAAACTAGGGAAGATTTTGCTTGGCAGTCAGGTACCAATGCATCCATTTTCTGGCA
1492  84_HRV43    TCCAAAAACTAGGAAAGATTATGCATGGCAATCTGGCACAAATGCATCTGTTTTCTGGCA
1493  85_HRV43b|   TCCAAAAACTAGGAAAGATTATGCATGGCAATCTGGCACAAATGCATCTGTTTTCTGGCA
1494  86_HRV43a|   TCCAAAAACTAGGAAAGATTATGCATGGCAATCTGGCACAAATGCATCTGTTTTCTGGCA
1495  87_HRV75    ACCAACAACTAGAAAAGATTATGCATGGCAATCTGGAACAAATGCATCTGTATTTTGGCA
```

FIG. D12 CONT'D

08.trace                                                                9/20/2007 5:05 PM

```
1496  88_HRV75b|    ACCAACAACTAGAAAAGATTATGCATGGCAATCTGGAACAAATGCATCTGTATTTTGGCA
1497  89_HRV75a|    ACCAACAACTAGAAAAGATTATGCATGGCAATCTGGAACAAATGCATCTGTATTTTGGCA
1498  96_HRV9a|d    ACCAAGGACTAGAGATGATTATGCATGGCAATCAGGCACAAATGCTTCCATCTTTTGGCA
1499  97_HRV9b|d    ACCAAGGACTAGAGATGATTATGCATGGCAATCAGGCACAAATGCTTCCATCTTTTGGCA
1500  98_HRV9       ACCAAGGACTAGAGATGATTATGCATGGCAATCAGGCACAAATGCTTCCATCTTTTGGCA
1501  99_HRV32      ACCACAAGCAAGAGATGACTACACATGGCAATCTGGCACGAATGCATCTATCTTTTGGCA
1502  100_HRV32a    ACCACAAGCAAGAGATGACTACACATGGCAATCTGGCACGAATGCATCTATCTTTTGGCA
1503  101_HRV32b    ACCACAAGCAAGAGATGACTACACATGGCAATCTGGCACGAATGCATCTATCTTTTGGCA
1504  102_HRV67     ACCAACAAAAGAGATGACTACACATGGCAATCAGGTACAAATGCCATCCATCTTTTGGCA
1505  103_HRV67a    ACCAACAAAAGAGATGACTACACATGGCAATCAGGTACAAATGCATCCATCTTTTGGCA
1506  104_HRV67b    ACCAACAAAAGAGATGACTACACATGGCAATCAGGTACAAATGCATCCATCTTTTGGCA
1507  105_HRV15     ACCCAATAAAAGGAATGATTACACATGGCAATCAGGTACAAATGCCTCTGTTTTCTGGCA
1508  106_HRV15a    ACCCAATAAAAGGAATGATTACACATGGCAATCAGGTACAAATGCCTCTGTTTTCTGGCA
1509  107_HRV15b    ACCCAATAAAAGGAATGATTACACATGGCAATCAGGTACAAATGCCTCTGTTTTCTGGCA
1510  108_HRV74a    ACCCAAGAAAAGAGATGATTACACATGGCAATCTGGCACAAATGCATCTGTGTTTTGGCA
1511  109_HRV74b    ACCCAAGAAAAGAGATGATTACACATGGCAATCTGGCACAAATGCATCTGTGTTTTGGCA
1512  110_HRV74     ACCCAAGAAAAGAGATGATTACACATGGCAATCTGGCACAAATGCATCTGTGTTTTGGCA
1513  111_HRV38a    ACCCAGGAAGAGAGATGATTACACTTGGCAATCTGGTACAAATGCCTCTGTTTTCTGGCA
1514  112_HRV38b    ACCCAGGAAGAGAGATGATTACACTTGGCAATCTGGTACAAATGCCTCTGTTTTCTGGCA
1515  113_HRV38     ACCCAGGAAGAGAGATGATTACACTTGGCAATCTGGTACAAATGCCTCTGTTTTCTGGCA
1516  114_HRV60     ACCTACTAAAAGAGACGATTACACATGGCAATCTGGCACAAATGCTTCTGTATTTTGGCA
1517  115_HRV60a    ACCTACTAAAAGAGACGATTACACATGGCAATCTGGCACAAATGCTTCTGTATTTTGGCA
1518  116_HRV60b    ACCTACTAAAAGAGACGATTACACATGGCAATCTGGCACAAATGCTTCTGTATTTTGGCA
1519  117_HRV64a    ACCAACCAAAAGAAATGATTACGTCTGGCAGTCAGGCACCAATGCATCCATCTTTTGGCA
1520  118_HRV64b    ACCAACCAAAAGAAATGATTACGTCTGGCAGTCAGGCACCAATGCATCCATCTTTTGGCA
1521  119_HRV64     ACCAACCAAAAGAAATGATTACGTCTGGCAGTCAGGCACCAATGCATCCATCTTTTGGCA
1522  120_HRV94a    ACCAGACAAAAGAGATGATTATGTTTGGCAATCAGGAACTAATGCATCTATATTCTGGCA
1523  121_HRV94b    ACCAGACAAAAGAGATGATTATGTTTGGCAATCAGGAACTAATGCATCTATATTCTGGCA
1524  122_HRV94     ACCAGACAAAAGAGATGATTATGTTTGGCAATCAGGAACTAATGCATCTATATTCTGGCA
1525  123_HRV22     ACCTGAAAAGAGAGATGACTACACATGGCAATCTGGCACTAATGCATCTGTTTTCTGGCA
1526  124_HRV22a    ACCTGAAAAGAGAGATGACTACACATGGCAATCTGGCACTAATGCATCTGTTTTCTGGCA
1527  125_HRV22b    ACCTGAAAAGAGAGATGACTACACATGGCAATCTGGCACTAATGCATCTGTTTTCTGGCA
1528  126_HRV82     ACCAGAAAAGAGAGACGACTACACTTGGCAATCTGGAACTAATGCTTCAATTTTCTGGCA
1529  127_HRV82b    ACCAGAAAAGAGAGACGACTACACTTGGCAATCTGGAACTAATGCTTCAATTTTCTGGCA
1530  128_HRV82a    ACCAGAAAAGAGAGACGACTACACTTGGCAATCTGGAACTAATGCTTCAATTTTCTGGCA
1531  129_HRV19     CCCAAAAACTAGAAATGATTACACATGGCAATCAGGTACTAATGCATCTATATTTTGGCA
1532  130_HRV19a    CCCAAAAACTAGAAATGATTACACATGGCAATCAGGTACTAATGCATCTATATTTTGGCA
1533  131_HRV19b    CCCAAAAACTAGAAATGATTACACATGGCAATCAGGTACTAATGCATCTATATTTTGGCA
1534  132_HRV13     TCCAACGAAGAGAAATGATTACACATGGCAATCTGGCACCAATGCATCTGTTTTCTGGCA
1535  133_HRV13a    TCCAACGAAGAGAAATGATTACACATGGCAATCTGGCACCAATGCATCTGTTTTCTGGCA
1536  134_HRV13b    TCCAACGAAGAGAAATGATTACACATGGCAATCTGGCACCAATGCATCTGTTTTCTGGCA
1537  135_HRV41     CCCAGAAAAGAGAGATGATTACACATGGCAATCTGGCACCAATGCATCTGTATTCTGGCA
1538  136_HRV41a    CCCAGAAAAGAGAGATGATTACACATGGCAATCTGGCACCAATGCATCTGTATTCTGGCA
1539  137_HRV41b    CCCAGAAAAGAGAGATGATTACACATGGCAATCTGGCACCAATGCATCTGTATTCTGGCA
1540  138_HRV73     ACCCACAAAAGAAATGACTACACATGGCAGTCCGGCACTAATGCATCAGTATTCTGGCA
1541  139_HRV73b    ACCCACAAAAGAAATGACTACACATGGCAGTCCGGCACTAATGCATCAGTATTCTGGCA
1542  140_HRV73a    ACCCACAAAAGAAATGACTACACATGGCAGTCCGGCACTAATGCATCAGTATTCTGGCA
1543  141_HRV61     ACCTGAGAAAAGAAATGATTTCACATGGCAATCAGGCACAAATGCATCTGTTTTCTGGCA
1544  142_HRV61a    ACCTGAGAAAAGAAATGATTTCACATGGCAATCAGGCACAAATGCATCTGTTTTCTGGCA
1545  143_HRV61b    ACCTGAGAAAAGAAATGATTTCACATGGCAATCAGGCACAAATGCATCTGTTTTCTGGCA
1546  144_HRV96     ACCTGAGAAGAGAGATGACTTTACATGGCAATCAGGCACAAATGCATCTGTGTTTTGGCA
1547  145_HRV96b    ACCTGAGAAGAGAGATGACTTTACATGGCAATCAGGCACAAATGCATCTGTGTTTTGGCA
1548  146_HRV96a    ACCTGAGAAGAGAGATGACTTTACATGGCAATCAGGCACAAATGCATCTGTGTTTTGGCA
1549  90_HRV16a|    ACCAACAACTAGAAATGACTATGCTTGGCAATCTGGAACAAATGCATCTGTATTTTGGCA
1550  91_HRV16b|    ACCAACAACTAGAAATGACTATGCTTGGCAATCTGGAACAAATGCATCTGTATTTTGGCA
1551  92_1AYM_A     ACCAACAACTAGAAATGACTATGCTTGGCAATCTGGAACAAATGCATCTGTATTTTGGCA
1552  93_HRV81a|    TCCAACAACTAGAGAAGACTATGCTTGGCAATCTGGAACAAATGCATCTATATTCTGGCA
1553  94_HRV81b|    TCCAACAACTAGAGAAGACTATGCTTGGCAATCTGGAACAAATGCATCTATATTCTGGCA
1554  95_HRV81      TCCAACAACTAGAGAAGACTATGCTTGGCAATCTGGAACAAATGCATCTATATTCTGGCA
1555  GROUP_1       -CC-------AG-----A-T-----TGG-A-TC--G-A--AA----TC----TT-TGGCA
1556
1557  1_HRV1A1|d    ACATGGACAGCCATTTCCTAGATTTTCTTTACCATTTCTTAGCATTGCATCAGCTTATTA
1558  2_HRV1A2|d    ACATGGACAGCCATTTCCTAGATTTTCTTTACCATTTCTTAGCATTGCATCAGCTTATTA
1559  3_HRV1A|cD    ACATGGACAGCCATTTCCTAGATTTTCTTTACCATTTCTTAGCATTGCATCAGCTTATTA
1560  4_HRV1B1|d    ACATGGACAACCGTTCCCTAGATTCTCTTTACCATTTCTTAGCATTGCATCAGCTTATTA
```

FIG. D12 CONT'D

```
08.trace                                                                    9/20/2007 5:05 PM 1561  5_HRV1B2|d    ACATGGACAACCGTTCCCTAGATTCTCTTTACCATTTCTTAGCATTGCATCAGCTTATTA
1562  6_HRV1B       ACATGGACAACCGTTCCCTAGATTCTCTTTACCATTTCTTAGCATTGCATCAGCTTATTA
1563  7_HRV40a|d    ACATGGTCAAACTTTCCCTAGATTTTCTTTACCTTTCCTAAGCATAGCTTCAGCATACTA
1564  8_HRV40b|d    ACATGGTCAAACTTTCCCTAGATTTTCTTTACCTTTCCTAAGCATAGCTTCAGCATACTA
1565  9_HRV40       ACATGGTCAAACTTTCCCTAGATTTTCTTTACCTTTCCTAAGCATAGCTTCAGCATACTA
1566 10_HRV85       ACATGGGCAAACTTTCCCCAGATTTTCCTTACCTTTCTTGAGTGTTGCTTCAGCATATTA
1567 11_HRV85a|     ACATGGGCAAACTTTCCCCAGATTTTCCTTACCTTTCTTGAGTGTTGCTTCAGCATATTA
1568 12_HRV85b|     ACATGGGCAAACTTTCCCCAGATTTTCCTTACCTTTCTTGAGTGTTGCTTCAGCATATTA
1569 13_HRV56a|     ACATGGCCAAGCTTTCCCCAGATCTCTCTACCTTTCTTAAGTATTGCTTCTGCTTATTA
1570 14_HRV56b|     ACATGGCCAAGCTTTCCCCAGATTCTCTCTACCTTTCTTAAGTATTGCTTCTGCTTATTA
1571 15_HRV56       ACATGGCCAAGCTTTCCCCAGATTCTCTCTACCTTTCTTAAGTATTGCTTCTGCTTATTA
1572 16_HRV54       ACATGGCCAAGCTTATCCAAGATTCTCTTTACCATTTTTAAGTATTGCATCTGCTTACTA
1573 17_HRV98       GCATGGTCAGGCCTATCCAAGATTTCTCTACCATTCTTTAGCATTGCATCTGCTTACTA
1574 18_HRV59a|     ACATGGACAAACATTCCCAAGATTTTCATTGCCCTTCCTGAGCATAGCATCAGCTTATTA
1575 19_HRV59b|     ACATGGACAAACATTCCCAAGATTTTCATTGCCCTTCCTGAGCATAGCATCAGCTTATTA
1576 20_HRV59       ACATGGACAAACATTCCCAAGATTTTCATTGCCCTTCCTGAGCATAGCATCAGCTTATTA
1577 21_HRV63       ACATGGACAAGCTTTTCCAAGGTTTTCTCTACCTTTCTTGAGTATTGCATCAGCATATTA
1578 22_HRV63b|     ACATGGACAAGCTTTTCCAAGGTTTTCTCTACCTTTCTTGAGTATTGCATCAGCATATTA
1579 23_HRV63a|     ACATGGACAAGCTTTTCCAAGGTTTTCTCTACCTTTCTTGAGTATTGCATCAGCATATTA
1580 24_HRV39       ACACGGACAGCCTTACCCTAGATTTTCATTACCATTTCTAAGCATAGCCTCAGCATATTA
1581 25_HRV39a|     ACACGGACAGCCTTACCCTAGATTTTCATTACCATTTCTAAGCATAGCCTCAGCATATTA
1582 26_HRV39b|     ACACGGACAGCCTTACCCTAGATTTTCATTACCATTTCTAAGCATAGCCTCAGCATATTA
1583 27_HRV10a|     ACATGGACAACCTTTCCCTAGATTTTCTTTACCCTTCTTAAGCATTGCATCTGCTTACTA
1584 28_HRV10b|     ACATGGACAACCTTTCCCTAGATTTTCTTTACCCTTCTTAAGCATTGCATCTGCTTACTA
1585 29_HRV10       ACATGGACAACCTTTCCCTAGATTTTCTTTACCCTTCTTAAGCATTGCATCTGCTTACTA
1586 30_HRV100a     GCATGGGCAGCCATTCCCTAGAATTTCTTTACCTTTCTTGAGCATTGCTTCTGCATACTA
1587 31_HRV100b     GCATGGGCAGCCATTCCCTAGAATTTCTTTACCTTTCTTGAGCATTGCTTCTGCATACTA
1588 32_HRV100      GCATGGGCAGCCATTCCCTAGAATTTCTTTACCTTTCTTGAGCATTGCTTCTGCATACTA
1589 33_HRV66       ACTTGGACAACCATTCCCAAGATTCTCGCTACCTTTTCTAGGCATAGCTTCAGCATATTA
1590 34_HRV66b|     ACTTGGACAACCATTCCCAAGATTCTCGCTACCCTTTTCTAGGCATAGCTTCAGCATATTA
1591 35_HRV66a|     ACTTGGACAACCATTCCCAAGATTCTCGCTACCCTTTTCTAGGCATAGCTTCAGCATATTA
1592 36_HRV77a|     ACATGGACAACCATTCCCAAGATTTTCACTACCTTTTCTGAGTATTGCTTCAGCTTACTA
1593 37_HRV77b|     ACATGGACAACCATTCCCAAGATTTTCACTACCTTTTCTGAGTATTGCTTCAGCTTACTA
1594 38_HRV77       ACATGGACAACCATTCCCAAGATTTTCACTACCTTTTCTGAGTATTGCTTCAGCTTACTA
1595 39_HRV62a      ACATGGGCAACCCTTTCCTAGATTTTCATTACCTTTTTTGAGTGTTGCATCTGCTTATTA
1596 40_HRV62b      ACATGGGCAACCCTTTCCTAGATTTTCATTACCTTTTTTGAGTGTTGCATCTGCTTATTA
1597 41_HRV25       ACATGGACAACCCTTCCCTAGATTTTCATTGCCATTTCTGAGTGTTGCATCTGCTTATTA
1598 42_HRV29a      ACATGGTCAGCCTTTCCCAAGATTTTCATTACCATTCCTAAGTGTTGCATCTGCTTATTA
1599 43_HRV29b      ACATGGTCAGCCTTTCCCAAGATTTTCATTACCATTCCTAAGTGTTGCATCTGCTTATTA
1600 44_HRV44a      ACATGGTCAACCTTTCCCAAGATTTTCATTGCCATTTCTAAGTGTTGCATCTGCTATTA
1601 45_HRV44b      ACATGGTCAACCTTTCCCAAGATTTTCATTGCCATTTCTAAGTGTTGCATCTGCCTATTA
1602 46_HRV31       ACATGGACAACCCTTTCCAAGATTTACATTACCCTTTTTGAGTGTCGCATCCGCTTATTA
1603 47_HRV31a|     ACATGGACAACCCTTTCCAAGATTTACATTACCCTTTTTGAGTGTCGCATCCGCTTATTA
1604 48_HRV31b|     ACATGGACAACCCTTTCCAAGATTTACATTACCCTTTTTGAGTGTCGCATCCGCTTATTA
1605 49_HRV47       ACAAGGGCAACCCTTTCCAAGATTTTCATTACCATTTTTGAGTGTTGCATCTGCTTATTA
1606 50_HRV47a|     ACAAGGGCAACCCTTTCCAAGATTTTCATTACCATTTTTGAGTGTTGCATCTGCTTATTA
1607 51_HRV47b|     ACAAGGGCAACCCTTTCCAAGATTTTCATTACCATTTTTGAGTGTTGCATCTGCTTATTA
1608 52_HRV11       ATATGGTCAAACATACCCAAGATTTTCTCTACCTTTCATGAGTATAGCCTCAGCATATTA
1609 53_HRV11b|     ATATGGTCAAACATACCCAAGATTTTCTCTACCTTTCATGAGTATAGCCTCAGCATATTA
1610 54_HRV11a|     ATATGGTCAAACATACCCAAGATTTTCTCTACCTTTCATGAGTATAGCCTCAGCATATTA
1611 55_HRV76       ATATGGACAAACATACCCTAGGTTTTCATTACCCTTTCTAAGTATAGCTTCAGCTTATTA
1612 56_HRV76b|     ATATGGACAAACATACCCTAGGTTTTCATTACCCTTTCTAAGTATAGCTTCAGCTTATTA
1613 57_HRV76a|     ATATGGACAAACATACCCTAGGTTTTCATTACCCTTTCTAAGTATAGCTTCAGCTTATTA
1614 58_HRV33       ATATGGACAAACATATCCTAGGTTCTCATTACCTTTCCTTAGCATAGCTTCAGCATATTA
1615 59_HRV33b|     ATATGGACAAACATATCCTAGGTTCTCATTACCTTTCCTTAGCATAGCTTCAGCATATTA
1616 60_HRV33a|     ATATGGACAAACATATCCTAGGTTCTCATTACCTTTCCTTAGCATAGCTTCAGCATATTA
1617 61_HRV24a|     ACATGGACAAACCTATCCTAGATTTCCCTTCCTTTTCTGAGTGTAGCCTCTGCATATTA
1618 62_HRV24b|     ACATGGACAAACCTATCCTAGATTTCCCTTCCTTTTCTGAGTGTAGCCCTCTGCATATTA
1619 63_HRV24       ACATGGACAAACCTATCCTAGATTTCCCTTCCTTTTCTGAGTGTAGCCTCTGCATATTA
1620 64_HRV90       ACATGGACAAACATACCCTAGATTTTCACTTCCTTTCTTAAGTATAGCTTCTGCATACTA
1621 65_HRV90a|     ACATGGACAAACATACCCTAGATTTTCACTTCCTTTCTTAAGTATAGCTTCTGCATACTA
1622 66_HRV90b|     ACATGGACAAACATACCCTAGATTTTCACTTCCTTTCTTAAGTATAGCTTCTGCATACTA
1623 67_HRV34       ACATGGTCAAACATACCCTAGATTTTCCCTCCCTTTCTTAAGCATAGCCTCAGCATACTA
1624 68_HRV34b|     ACATGGTCAAACATACCCTAGATTTTCCCTCCCTTTCTTAAGCATAGCCTCAGCATACTA
1625 69_HRV34a|     ACATGGTCAAACATACCCTAGATTTTCCCTCCCTTTCTTAAGCATAGCCTCAGCATACTA
```

FIG. D12 CONT'D

```
08.trace                                                                                    9/20/2007 5:05 PM 1626  70_HRV50a|    ACATGGTCAAACATACCCTAGATTCTCTCTACCATTCTTGAGTATAGCATCTGCATATTA
1627  71_HRV50b|    ACATGGTCAAACATACCCTAGATTCTCTCTACCATTCTTGAGTATAGCATCTGCATATTA
1628  72_HRV50     ACATGGTCAAACATACCCTAGATTCTCTCTACCATTCTTGAGTATAGCATCTGCATATTA
1629  73_HRV18a|    ACATGGTCAAACATACCCCAGATTTTCACTTCCTTTCCTCAGTATAGCATCAGCTTATTA
1630  74_HRV18b|    ACATGGTCAAACATACCCCAGATTTTCACTTCCTTTCCTCAGTATAGCATCAGCTTATTA
1631  75_HRV18     ACATGGTCAAACATACCCCAGATTTTCACTTCCTTTCCTCAGTATAGCATCAGCTTATTA
1632  76_HRV55     ACATGGGCAAACATACCCTAGATTTTCACTTCCTTTCCTAAGTATAGCTTCTGCTTATTA
1633  77_HRV55b|    ACATGGGCAAACATACCCTAGATTTTCACTTCCTTTCCTAAGTATAGCTTCTGCTTATTA
1634  78_HRV55a     ACATGGGCAAACATACCCTAGATTTTCACTTCCTTTCCTAAGTATAGCTTCTGCTTATTA
1635  79_HRV57     ACATGGTCAAACATACCCTAGATTTTCCTTGCCTTTCTTAAGTATAGCCTCAGCATATTA
1636  80_HRV57a|    ACATGGTCAAACATACCCTAGATTTTCCTTGCCTTTCTTAAGTATAGCCTCAGCATATTA
1637  81_HRV57b|    ACATGGTCAAACATACCCTAGATTTTCCTTGCCTTTCTTAAGTATAGCCTCAGCATATTA
1638  82_HRV21     GCATGGCCAGACTTATCCTAGATTTTCATTACCCTTCCTTAGTATAGCATCAGCATACTA
1639  83_HRVHan    GCATGGTCAAACTTATCCTAGATTTTCACTACCCTTCCTTAGTATAGCATCAGCATATTA
1640  84_HRV43     ACATGGTCAAACATTTCCAAGATTTTCCTTACCTTTTCTGAGCATAGCATCAGCATATTA
1641  85_HRV43b|    ACATGGTCAAACATTTCCAAGATTTTCCTTACCTTTTCTGAGCATAGCATCAGCATATTA
1642  86_HRV43a|    ACATGGTCAAACATTTCCTTACCTTTCTGAGCATAGCATCAGCATATTA
1643  87_HRV75     ACATGGACAAACATTTCCAAGATTTTCACTACCATTTCTGAGCATTGCATCAGCATATTA
1644  88_HRV75b|    ACATGGACAAACATTTCCAAGATTTTCACTACCATTTCTGAGCATTGCATCAGCATATTA
1645  89_HRV75a|    ACATGGACAAACATTTCCAAGATTTTCACTACCATTTCTGAGCATTGCATCAGCATATTA
1646  96_HRV9a|d    ACATGGACAATCATATCCCAGATTTTCACTTCCGTTTTTGAGCATTGCCTCTGCATATTA
1647  97_HRV9b|d    ACATGGACAATCATATCCCAGATTTTCACTTCCGTTTTTGAGCATTGCCTCTGCATATTA
1648  98_HRV9      ACATGGACAATCATATCCCAGATTTTCACTTCCGTTTTTGAGCATTGCCTCTGCATATTA
1649  99_HRV32     GCATGGACAGGCATATCCCAGGTTTTCACTTCCATTTCTAAGTATTGCCTCTGCATACTA
1650  100_HRV32a    GCATGGACAGGCATATCCCAGGTTTTCACTTCCATTTCTAAGTATTGCCTCTGCATACTA
1651  101_HRV32b    GCATGGACAGGCATATCCCAGGTTTTCACTTCCATTTCTAAGTATTGCCTCTGCATACTA
1652  102_HRV67    ACATGGACAATCATACCCCAGATTCTCACTACCATTCTTAAGTATTGCCTCTGCTTATTA
1653  103_HRV67a    ACATGGACAATCATACCCCAGATTCTCACTACCATTCTTAAGTATTGCCTCTGCTTATTA
1654  104_HRV67b    ACATGGACAATCATACCCCAGATTCTCACTACCATTCTTAAGTATTGCCTCTGCTTATTA
1655  105_HRV15    ACATGGTCAACCTTACCCCAGATTTTCTTTGCCTTTTCTCAGCATTGCATCTGCTTACTA
1656  106_HRV15a    ACATGGTCAACCTTACCCCAGATTTTCTTTGCCTTTTCTCAGCATTGCATCTGCTTACTA
1657  107_HRV15b    ACATGGTCAACCTTACCCCAGATTTTCTTTGCCTTTTCTCAGCATTGCATCTGCTTACTA
1658  108_HRV74a    GCATGGACAGCCATACCCTAGATTCTCATTACCTTTCCTTAGCATAGCATCTGCTTATTA
1659  109_HRV74b    GCATGGACAGCCATACCCTAGATTCTCATTACCTTTCCTTAGCATAGCATCTGCTTATTA
1660  110_HRV74    GCATGGACAGCCATACCCTAGATTCTCATTACCTTTCCTTAGCATAGCATCTGCTTATTA
1661  111_HRV38a    ATATGGTCAGACATATCCTCGATTTTCCTTACCTTTCTTAAGCATTGCATCTGTCTATTA
1662  112_HRV38b    ATATGGTCAGACATATCCTCGATTTTCCTTACCTTTCTTAAGCATTGCATCTGTCTATTA
1663  113_HRV38    ATATGGTCAGACATATCCTCGATTTTCCTTACCTTTCTTAAGCATTGCATCTGTCTATTA
1664  114_HRV60    GCATGGACAAACATACCCTAGATTCTCACTTCCATTTCTAAGTATTGCATCTGCCTACTA
1665  115_HRV60a    GCATGGACAAACATACCCTAGATTTTCACTTCCATTTCTAAGTATTGCATCTGCCTACTA
1666  116_HRV60b    GCATGGACAAACATACCCTAGATTTTCACTTCCATTTCTAAGTATTGCATCTGCCTACTA
1667  117_HRV64a    ACACGGTCAACCATACCCTCGATTTTCTCTCCCTTTCCTTAGCATAGCCTCAGCATATTA
1668  118_HRV64b    ACACGGTCAACCATACCCTCGATTTTCTCTCCCTTTCCTTAGCATAGCCTCAGCATATTA
1669  119_HRV64    ACACGGTCAACCATACCCTCGATTTTCTCTCCCTTTCCTTAGCATAGCCTCAGCATATTA
1670  120_HRV94a    ACATGGTCAACCCTACCCTCGATTCTCACTTCCATTTCTTAGTATAGCCTCAGCATATTA
1671  121_HRV94b    ACATGGTCAACCCTACCCTCGATTCTCACTTCCATTTCTTAGTATAGCCTCAGCATATTA
1672  122_HRV94    ACATGGTCAACCCTACCCTCGATTCTCACTTCCATTTCTTAGTATAGCCTCAGCATATTA
1673  123_HRV22    GCATGGTCAACCTTATCCCCGATTCTCACTCCCTTTCCTCAGTGTAGCTTCAGCATATTA
1674  124_HRV22a    GCATGGTCAACCTTATCCCCGATTCTCACTCCCTTTCCTCAGTGTAGCTTCAGCATATTA
1675  125_HRV22b    GCATGGTCAACCTTATCCCCGATTCTCACTCCCTTTCCTCAGTGTAGCTTCAGCATATTA
1676  126_HRV82    ACATGGACAAACCTTACCCTCGCTTCTCACTTCCTTTCTTGAGTATAGCCTCAGCTTACTA
1677  127_HRV82b    ACATGGACAACCTTACCCTCGCTTCTCACTTCCTTTCTTGAGTATAGCCTCAGCTTACTA
1678  128_HRV82a    ACATGGACAACCTTACCCTCGCTTCTCACTTCCTTTCTTGAGTATAGCCTCAGCTTACTA
1679  129_HRV19    ACATGGTCAACCATACCCAAGATTTTCATTACCTTTTCTAAGTATAGCCTTCTGCATATTA
1680  130_HRV19a    ACATGGTCAACCATACCCAAGATTTTCATTACCTTTTCTAAGTATAGCTTCTGCATATTA
1681  131_HRV19b    ACATGGTCAACCATACCCAAGATTTTCATTACCTTTTCTAAGTATAGCTTCTGCATATTA
1682  132_HRV13    ACATGGTCAAATTACCCCCGATTCTCTTTACCATTTCTTAGTATTGCATCTGCATATTA
1683  133_HRV13a    ACATGGTCAAATTTACCCCCGATTCTCTTTACCATTTCTTAGTATTGCATCTGCATATTA
1684  134_HRV13b    ACATGGTCAAATTTACCCCCGATTCTCTTTACCATTTCTTAGTATTGCATCTGCATATTA
1685  135_HRV41    GTATGGTCAAGTTTACCCTAGGTTTTCTCTACCATTTCTTAGCATTGCTTCCGCATATTA
1686  136_HRV41a    GTATGGTCAAGTTTACCCTAGGTTTTCTCTACCATTTCTTAGCATTGCTTCCGCATATTA
1687  137_HRV41b    GTATGGTCAAGTTTACCCTAGGTTTTCTCTACCATTTCTTAGCATTGCTTCCGCATATTA
1688  138_HRV73    ACATGGTCAAACTTACCCCAGATTCTCATTACCATTCCTTAGTATAGCATCCGCATATTA
1689  139_HRV73b    ACATGGTCAAACTTACCCCAGATTCTCATTACCATTCCTTAGTATAGCATCCGCATATTA
1690  140_HRV73a    ACATGGTCAAACTTACCCCAGATTCTCATTACCATTCCTTAGTATAGCATCCGCATATTA
```

FIG. D12 CONT'D

08.trace					9/20/2007 5:05 PM

```
1691  141_HRV61      ACATGGTCAAGCTTATCCCAGATTTTCATTACCATTCCTAAGTATTGCATCTGCATATTA
1692  142_HRV61a     ACATGGTCAAGCTTATCCCAGATTTTCATTACCATTCCTAAGTATTGCATCTGCATATTA
1693  143_HRV61b     ACATGGTCAAGCTTATCCCAGATTTTCATTACCATTCCTAAGTATTGCATCTGCATATTA
1694  144_HRV96      GCACGGGCAAGCATATCCTAGATTTTCACTGCCTTTCCTTAGTATTGCCTCTGCATATTA
1695  145_HRV96b     GCACGGGCAAGCATATCCTAGATTTTCACTGCCTTTCCTTAGTATTGCCTCTGCATATTA
1696  146_HRV96a     GCACGGGCAAGCATATCCTAGATTTTCACTGCCTTTCCTTAGTATTGCCTCTGCATATTA
1697  90_HRV16a|     GCATGGGCAACCTTTCCCTCGCTTTTCACTTCCCTTTTTGAGTATTGCATCAGCATATTA
1698  91_HRV16b|     GCATGGGCAACCTTTCCCTCGCTTTTCACTTCCCTTTTTGAGTATTGCATCAGCATATTA
1699  92_1AYM_A      GCATGGGCAACCTTTCCCTCGCTTTTCACTTCCCTTTTTGAGTATTGCATCAGCATATTA
1700  93_HRV81a|     ACATGGGCAACCTTTCCCGGTTTTCACTCCCTTTTCTAAGTGTAGCATCAGCATATTA
1701  94_HRV81b|     ACATGGGCAACCCTTTCCCCGGTTTTCACTCCCTTTTCTAAGTGTAGCATCAGCATATTA
1702  95_HRV81       ACATGGGCAACCCTTTCCCCGGTTTTCACTCCCTTTTCTAAGTGTAGCATCAGCATATTA
1703  GROUP_1        ----GG-CA----T--CC--G--T--C--T-CC-TT--T--G--T-GC-TC-G--TA-TA
1704
1705  1_HRV1A1|d     TATGTTTTATGATGGATATGATGGAGACAACACTTCTTCCAAGTATGGTAGCGTAGTTAC
1706  2_HRV1A2|d     TATGTTTTATGATGGATATGATGGAGACAACACTTCTTCCAAGTATGGTAGCGTAGTTAC
1707  3_HRV1A|cD     TATGTTTTATGATGGATATGATGGAGACAACACTTCTTCCAAGTATGGTAGCGTAGTTAC
1708  4_HRV1B1|d     CATGTTTTATGATGGATATGATGGAGATAATTCCTCTTCCAAATATGGTAGTATAGTCAC
1709  5_HRV1B2|d     CATGTTTTATGATGGATATGATGGAGATAATTCCTCTTCCAAATATGGTAGTATAGTCAC
1710  6_HRV1B        CATGTTTTATGATGGATATGATGGAGATAATTCCTCTTCCAAATATGGTAGTATAGTCAC
1711  7_HRV40a|d     CATGTTTTATGATGGATACGATGGTGATACATCGACCTCAAGATATGGCACATCAGTCAC
1712  8_HRV40b|d     CATGTTTTATGATGGATACGATGGTGATACATCGACCTCAAGATATGGCACATCAGTCAC
1713  9_HRV40        CATGTTTTATGATGGATACGATGGTGATACATCGACCTCAAGATATGGCACATCAGTCAC
1714  10_HRV85       CATGTTTTATGATGGTTATGATGGTGATACACCAGGCTCAATGTATGGGACGTCAGTCAC
1715  11_HRV85a|     CATGTTTTTATGATGGTTATGATGGTGATACACCAGGCTCAATGTATGGGACGTCAGTCAC
1716  12_HRV85b|     CATGTTTTATGATGGTTATGATGGTGATACACCAGGCTCAATGTATGGGACGTCAGTCAC
1717  13_HRV56a|     CATGTTTTATGATGGTTATGATGGAGACACTTCAAGCTCCAGATATGGTACATCAGTTAC
1718  14_HRV56b|     CATGTTTTATGATGGTTATGATGGAGACACTTCAAGCTCCAGATATGGTACATCAGTTAC
1719  15_HRV56       CATGTTTTATGATGGTTATGATGGAGACACTTCAAGCTCCAGATATGGTACATCAGTTAC
1720  16_HRV54       CATGTTTTATGATGGGTATGATGGTGACGCACCTGGATCAAGATATGGGACTTCAGTTAC
1721  17_HRV98       CATGTTTTACGATGGGTATGATGGTGATGCACCTGGATCAAGATATGGAACCTCAGTCAC
1722  18_HRV59a|     CATGTTTTTATGATGGTTATGATGGAGATAAATCTGAATCTAGGTATGGTGTGTCTGTAAC
1723  19_HRV59b|     CATGTTTTATGATGGTTATGATGGAGATAAATCTGAATCTAGGTATGGTGTGTCTGTAAC
1724  20_HRV59       CATGTTTTATGATGGTTATGATGGAGATAAATCTGAATCTAGGTATGGTGTGTCTGTAAC
1725  21_HRV63       CATGTTTTTATGATGGATATGATGGAGATAAATCAAGCTCTAGGTATGGTGTTTCAGTTAC
1726  22_HRV63b|     CATGTTTTATGATGGATATGATGGAGATAAATCAAGCTCTAGGTATGGTGTTTCAGTTAC
1727  23_HRV63a|     CATGTTTTATGATGGATATGATGGAGATAAATCAAGCTCTAGGTATGGTGTTTCAGTTAC
1728  24_HRV39       TATGTTCTATGATGGATATGATGGTGATAAATCGTCATCTAGGTATGGTGTTTCTGTCAC
1729  25_HRV39a|     TATGTTCTATGATGGATATGATGGTGATAAATCGTCATCTAGGTATGGTGTTTCTGTCAC
1730  26_HRV39b|     TATGTTCTATGATGGATATGATGGTGATAAATCGTCATCTAGGTATGGTGTTTCTGTCAC
1731  27_HRV10a|     CATGTTCTATGATGGTTATGATGGTGATACACATGACTCACGTTATGGCACAACAGTGAT
1732  28_HRV10b|     CATGTTCTATGATGGTTATGATGGTGATACACATGACTCACGTTATGGCACAACAGTGAT
1733  29_HRV10       CATGTTCTATGATGGTTATGATGGTGATACACATGACTCACGTTATGGCACAACAGTGAT
1734  30_HRV100a     CATGTTTTATGATGGATATGATGGTGATACACATGATTCACACTATGGTACTACTGTAAT
1735  31_HRV100b     CATGTTTTATGATGGATATGATGGTGATACACATGATTCACACTATGGTACTACTGTAAT
1736  32_HRV100      CATGTTTTATGATGGATATGATGGTGATACACATGATTCACACTATGGTACTACTGTAAT
1737  33_HRV66       CATGTTCTATGATGGTTATGATGGAGATACTCCTGGGTCTCGTTATGGCAACCACAGTAGT
1738  34_HRV66b|     CATGTTCTATGATGGTTATGATGGAGATACTCCTGGGTCTCGTTATGGCAACCACAGTAGT
1739  35_HRV66a|     CATGTTCTATGATGGTTATGATGGAGATACTCCTGGGTCTCGTTATGGCAACCACAGTAGT
1740  36_HRV77a|     CATGTTTTATGATGGCTATGATGGGGATACCTATGAATCACGTTATGGTACTACAGTGGT
1741  37_HRV77b|     CATGTTTTATGATGGCTATGATGGGGATACCTATGAATCACGTTATGGTACTACAGTGGT
1742  38_HRV77       CATGTTTTATGATGGCTATGATGGGGATACCTATGAATCACGTTATGGTACTACAGTGGT
1743  39_HRV62a      CATGTTTTATGATGGCTATAATGGTGATGACTATACAGCAAAATACGGTACCACCGTGGT
1744  40_HRV62b      CATGTTTTATGATGGCTATAATGGTGATGACTATACAGCAAAATACGGTACCACCGTGGT
1745  41_HRV25       CATGTTTTATGATGGCTATAATGGTGATGATCACACAGCGAGATATGGTACCACTGTGGT
1746  42_HRV29a      CATGTTTTATGATGGTTACAATGGAGGTGATCATACAGCAACTTATGGCACCACAGTGGT
1747  43_HRV29b      CATGTTTTATGATGGTTACAATGGAGGTGATCATACAGCAACTTATGGCACCACAGTGGT
1748  44_HRV44a      CATGTTTTATGACGGTTATAATGGAGGTGATCATACAGCAACTTATGGCACCACAGTGGT
1749  45_HRV44b      CATGTTTTATGACGGTTATAATGGAGGTGATCATACAGCAACTTATGGCACCACAGTGGT
1750  46_HRV31       CATGTTTTATGATGGTTATGATGGAGACAAAAGTGGAGCCAAGTATGGTACTACAGTAGT
1751  47_HRV31a|     CATGTTTTATGATGGTTATGATGGAGACAAAAGTGGAGCCAAGTATGGTACTACAGTAGT
1752  48_HRV31b|     CATGTTTTATGATGGTTATGATGGAGACAAAAGTGGAGCCAAGTATGGTACTACAGTAGT
1753  49_HRV47       CATGTTTTATGATGGCTATAATGGTGACAGAAGTGGAGCCAAGTATGGCACCACAGTGGT
1754  50_HRV47a|     CATGTTTTATGATGGCTATAATGGTGACAGAAGTGGAGCCAAGTATGGCACCACAGTGGT
1755  51_HRV47b|     CATGTTTTATGATGGCTATAATGGTGACAGAAGTGGAGCCAAGTATGGCACCACAGTGGT
```

FIG. D12 CONT'D 08.trace                                                                    9/20/2007 5:05 PM

```
1756  52_HRV11     CATGTTTTATGATGGATATGATGGAGATCAACCAAACTCCAGATATGGTAATATAGTTAC
1757  53_HRV11b|   CATGTTTTATGATGGATATGATGGAGATCAACCAAACTCCAGATATGGTAATATAGTTAC
1758  54_HRV11a|   CATGTTTTATGATGGATATGATGGAGATCAACCAAACTCCAGATATGGTAATATAGTTAC
1759  55_HRV76     CATGTTTTATGATGGATATGATGGAGACCAACCTAGTTCTAGGTATGGTAATATAGTTAC
1760  56_HRV76b|   CATGTTTTATGATGGATATGATGGAGACCAACCTAGTTCTAGGTATGGTAATATAGTTAC
1761  57_HRV76a|   CATGTTTTATGATGGATATGATGGAGACCAACCTAGTTCTAGGTATGGTAATATAGTTAC
1762  58_HRV33     CATGTTCTATGATGGATATGATGGGGACCAACCCAATTCCAGGTATGGTAATATGGTTAC
1763  59_HRV33b|   CATGTTCTATGATGGATATGATGGGGACCAACCCAATTCCAGGTATGGTAATATGGTTAC
1764  60_HRV33a|   CATGTTCTATGATGGATATGATGGGGACCAACCCAATTCCAGGTATGGTAATATGGTTAC
1765  61_HRV24a|   CATGTTTTATGATGGATATGATGGTGATCAACACGACTCAGTGTATGGTTCAGTTGTTAC
1766  62_HRV24b|   CATGTTTTATGATGGATATGATGGTGATCAACACGACTCAGTGTATGGTTCAGTTGTTAC
1767  63_HRV24     CATGTTTTATGATGGATATGATGGTGATCAACACGACTCAGTGTATGGTTCAGTTGTTAC
1768  64_HRV90     TATGTTTTATGATGGATATGATGGTGACCAAACTGATTCGAGATATGGTACCATTGTTAC
1769  65_HRV90a|   TATGTTTTATGATGGATATGATGGTGACCAAACTGATTCGAGATATGGTACCATTGTTAC
1770  66_HRV90b|   TATGTTTTATGATGGATATGATGGTGACCAAACTGATTCGAGATATGGTACCATTGTTAC
1771  67_HRV34     CATGTTTTATGATGGATATGATGGTGATCAACATGATTCAAGATATGGTACAGTAGTGAC
1772  68_HRV34b|   CATGTTTTATGATGGATATGATGGTGATCAACATGATTCAAGATATGGTACAGTAGTGAC
1773  69_HRV34a|   CATGTTTTATGATGGATATGATGGTGATCAACATGATTCAAGATATGGTACAGTAGTGAC
1774  70_HRV50a|   CATGTTTTATGATGGTTATGATGGTGATAAATCTACATCCAGGTATGGTACAGTAGTTAC
1775  71_HRV50b|   CATGTTTTATGATGGTTATGATGGTGATAAATCTACATCCAGGTATGGTACAGTAGTTAC
1776  72_HRV50     CATGTTTTATGATGGTTATGATGGTGATAAATCTACATCCAGGTATGGTACAGTAGTTAC
1777  73_HRV18a|   CATGTTCTATGATGGCTACGACGGTGACCAGACCTCATCGCGGTATGGCACAGTTGCAAC
1778  74_HRV18b|   CATGTTCTATGATGGCTACGACGGTGACCAGACCTCATCGCGGTATGGCACAGTTGCAAC
1779  75_HRV18     CATGTTCTATGATGGCTACGACGGTGACCAGACCTCATCGCGGTATGGCACAGTTGCAAC
1780  76_HRV55     CATGTTCTATGATGGATATGATGGTGACCAAACTGAGTCACGCTATGGCACTGTAGTCAC
1781  77_HRV55b|   CATGTTCTATGATGGATATGATGGTGACCAAACTGAGTCACGCTATGGCACTGTAGTCAC
1782  78_HRV55a|   CATGTTCTATGATGGATATGATGGTGACCAAACTGAGTCACGCTATGGCACTGTAGTCAC
1783  79_HRV57     CATGTTTTATGATGGATATGATGGTGACCAAACTGAATCAAGATATGGTACTGTAGTCAC
1784  80_HRV57a|   CATGTTTTATGATGGATATGATGGTGACCAAACTGAATCAAGATATGGTACTGTAGTCAC
1785  81_HRV57b|   CATGTTTTATGATGGATATGATGGTGACCAAACTGAATCAAGATATGGTACTGTAGTCAC
1786  82_HRV21     CATGTTTTATGGTTATGATGGTGACCAGACTGACTCACAATATGGTGCAGTGGTGAC
1787  83_HRVHan    CATGTTTTATGATGGTTATGATGGTGATCAGACTGACTCACAATATGGTGCAGTGGTGAC
1788  84_HRV43     CATGTTTTATGATGGATATGAAGGTGACCAAAAAACATCCCGTTATGGCACAATTGCAAG
1789  85_HRV43b|   CATGTTTTATGATGGATATGAAGGTGACCAAAAAACATCCCGTTATGGCACAATTGCAAG
1790  86_HRV43a|   CATGTTTTATGATGGATATGAAGGTGACCAAAAAACATCCCGTTATGGCACAATTGCAAG
1791  87_HRV75     CATGTTTTATGATGGATATGAAGGGATCAAAATACATCCCGTTATGGCACCATTGCTAG
1792  88_HRV75b|   CATGTTTTATGATGGATATGAAGGGATCAAAATACATCCCGTTATGGCACCATTGCTAG
1793  89_HRV75a|   CATGTTTTATGATGGATATGAAGGGGATCAAAATACATCCCGTTATGGCACCATTGCTAG
1794  96_HRV9a|d   CATGTTCTATGATGGTTATGATGGTGG---ACCAGATTCTCTGTATGGAACAATTGTAAC
1795  97_HRV9b|d   CATGTTCTATGATGGTTATGATGGTGG---ACCAGATTCTCTGTATGGAACAATTGTAAC
1796  98_HRV9      CATGTTCTATGATGGTTATGATGGTGG---ACCAGATTCTCTGTATGGAACAATTGTAAC
1797  99_HRV32     CATGTTTTATGATGGTTATGATGGTGG---ACCAGATTCACAATATGGAACAATTGTAAC
1798  100_HRV32a   CATGTTTTATGATGGTTATGATGGTGG---GCCAGATTCACAATATGGAACAATTGTAAC
1799  101_HRV32b   CATGTTTTATGATGGTTATGATGGTGG---GCCAGATTCACAATATGGAACAATTGTAAC
1800  102_HRV67    CATGTTTTATGATGGCTATGATGGTGG---ACCAGATTCACTATATGGCACCATAGTAAC
1801  103_HRV67a   CATGTTTTATGATGGCTATGATGGTGG---ACCAGATTCACTATATGGCACCATAGTAAC
1802  104_HRV67b   CATGTTTTATGATGGCTATGATGGTGG---ACCAGATTCACTATATGGCACCATAGTAAC
1803  105_HRV15    CATGTTCTATGATGGATATGATGGAGATTCCACTGAATCACATTATGGTACAGTGGTCAC
1804  106_HRV15a   CATGTTCTATGATGGATATGATGGAGATTCCACTGAATCACATTATGGTACAGTGGTCAC
1805  107_HRV15b   CATGTTCTATGATGGATATGATGGAGATTCCACTGAATCACATTATGGTACAGTGGTCAC
1806  108_HRV74a   CATGTTTTATGATGGATATGATGGAGACTCTACTGAATCACATTATGGTACAGTAGTAAC
1807  109_HRV74b   CATGTTTTATGATGGATATGATGGAGACTCTACTGAATCACATTATGGTACAGTAGTAAC
1808  110_HRV74    CATGTTTTATGATGGATATGATGGAGACTCTACTGAATCACATTATGGTACAGTAGTAAC
1809  111_HRV38a   TATGTTTTATGATGGATATGATGGGGACTCAACAGAATCACATTATGGGACAGCGGTGAC
1810  112_HRV38b   TATGTTTTATGATGGATATGATGGGGACTCAACAGAATCACATTATGGGACAGCGGTGAC
1811  113_HRV38    TATGTTTTATGATGGATATGATGGGGACTCAACAGAATCACATTATGGGACAGCGGTGAC
1812  114_HRV60    CATGTTTTATGATGGTTATGGTCACTCAACTGAATCACATTATGGGACGGTTGTGAC
1813  115_HRV60a   CATGTTTTATGATGGTTATGATGGTCACTCAACTGAATCACATTATGGGACGGTTGTGAC
1814  116_HRV60b   CATGTTTTATGATGGTTATGATGGTCACTCAACTGAATCACATTATGGGACGGTTGTGAC
1815  117_HRV64a   CATGTTTTATGATGGTTATGACGGTGG---ACCTGGTTCCCGTTATGGCGCAGTGGTGAC
1816  118_HRV64b   CATGTTTTATGATGGTTATGACGGTGG---ACCTGGTTCCCGTTATGGCGCAGTGGTGAC
1817  119_HRV64    CATGTTTTATGATGGTTATGACGGTGG---ACCTGGTTCCCGTTATGGCGCAGTGGTGAC
1818  120_HRV94a   CATGTTCTATGATGGTTATGATGGTGG---ACCTGGCTCACGCTATGGCACAGTGGTGAC
1819  121_HRV94b   CATGTTCTATGATGGTTATGATGGTGG---ACCTGGCTCACGCTATGGCACAGTGGTGAC
1820  122_HRV94    CATGTTCTATGATGGTTATGATGGTGG---ACCTGGCTCACGCTATGGCACAGTGGTGAC
```

FIG. D12 CONT'D

```
08.trace                                                                                              9/20/2007 5:05 PM 1821  123_HRV22      CATGTTTTATGATGGGTATGATGGAGG---TCCCGGATCACGTTATGGAGCAGTGGTAAC
1822  124_HRV22a     CATGTTTTATGATGGGTATGATGGAGG---TCCCGGATCACGTTATGGAGCAGTGGTAAC
1823  125_HRV22b     CATGTTTTATGATGGGTATGATGGAGG---TCCCGGATCACGTTATGGAGCAGTGGTAAC
1824  126_HRV82      TATGTTCTATGATGGCTATGATGGTGATGCTCCCGGATCGCGATACGGGACCATAGTGAC
1825  127_HRV82b     TATGTTCTATGATGGCTATGATGGTGATGCTCCCGGATCGCGATACGGGACCATAGTGAC
1826  128_HRV82a     TATGTTCTATGATGGCTATGATGGTGATGCTCCCGGATCGCGATACGGGACCATAGTGAC
1827  129_HRV19      CATGTTTTATGATGGGTATGATGGAGATTCACCAGGATCCCGCTATGGAACAATAGTAAC
1828  130_HRV19a     CATGTTTTATGATGGGTATGATGGAGATTCACCAGGATCCCGCTATGGAACAATAGTAAC
1829  131_HRV19b     CATGTTTTATGATGGGTATGATGGAGATTCACCAGGATCCCGCTATGGAACAATAGTAAC
1830  132_HRV13      TATGTTTTATGATGGATATAATGGAGATTCCTCAGATGCACGCTATGGGACAACAATCAC
1831  133_HRV13a     TATGTTTTATGATGGATATAATGGAGATTCCTCAGATGCACGCTATGGGACAACAATCAC
1832  134_HRV13b     TATGTTTTATGATGGATATAATGGAGATTCCTCAGATGCACGCTATGGGACAACAATCAC
1833  135_HRV41      CATGTTTTATGATGGTTATGAAGAAGGCTCTACAAATGCACGCTATGGAACAACAGTCAC
1834  136_HRV41a     CATGTTTTATGATGGTTATGAAGAAGGCTCTACAAATGCACGCTATGGAACAACAGTCAC
1835  137_HRV41b     CATGTTTTATGATGGTTATGAAGAAGGCTCTACAAATGCACGCTATGGAACAACAGTCAC
1836  138_HRV73      TATGTTTTATGATGGATATGATGGTGACTCCACACAATCACATTATGGCACCACAGTAGT
1837  139_HRV73b     TATGTTTTATGATGGATATGATGGTGACTCCACACAATCACATTATGGCACCACAGTAGT
1838  140_HRV73a     TATGTTTTATGATGGATATGATGGTGACTCCACACAATCACATTATGGCACCACAGTAGT
1839  141_HRV61      TATGTTTTATGATGGTTATGATGGAGATTCTGAAATAACGCGCTATGGAACATCAGTGAC
1840  142_HRV61a     TATGTTTTATGATGGTTATGATGGAGATTCTGAAATAACGCGCTATGGAACATCAGTGAC
1841  143_HRV61b     TATGTTTTATGATGGTTATGATGGAGATTCTGAAATAACGCGCTATGGAACATCAGTGAC
1842  144_HRV96      CATGTTTTATGATGGATATGATGGTGACTCTGAATCAACACGCTATGGAACATCTGTTAC
1843  145_HRV96b     CATGTTTTATGATGGATATGATGGTGACTCTGAATCAACACGCTATGGAACATCTGTTAC
1844  146_HRV96a     CATGTTTTATGATGGATATGATGGTGACTCTGAATCAACACGCTATGGAACATCTGTTAC
1845  90_HRV16a|     CATGTTTTATGATGGTTATGATGGAGACACATATAAATCCAGATATGGAACTGTAGTCAC
1846  91_HRV16b|     CATGTTTTATGATGGTTATGATGGAGACACATATAAATCCAGATATGGAACTGTAGTCAC
1847  92_1AYM_A      CATGTTTTATGATGGTTATGATGGAGACACATATAAATCCAGATATGGAACTGTAGTCAC
1848  93_HRV81a|     CATGTTCTATGATGGATATGATGGTGATACTTATCACTCCAGATACGGGACTGTAGTCAC
1849  94_HRV81b|     CATGTTCTATGATGGATATGATGGTGATACTTATCACTCCAGATACGGGACTGTAGTCAC
1850  95_HRV81       CATGTTCTATGATGGATATGATGGTGATACTTATCACTCCAGATACGGGACTGTAGTCAC
1851  GROUP_1        -ATGTT-TA-GA-GG-TA--A-G---------------C----TA-GG------------
1852
1853  1_HRV1A1|d     TAATGATATGGGTACTATATGCTCAAGAATAGTTACAGAAAAACAGAAACATTCTGTTGT
1854  2_HRV1A2|d     TAATGATATGGGTACTATATGCTCAAGAATAGTTACAGAAAAACAGAAACATTCTGTTGT
1855  3_HRV1A|cD     TAATGATATGGGTACTATATGCTCAAGAATAGTTACAGAAAAACAGAAACATTCTGTTGT
1856  4_HRV1B1|d     CAATGATATGGGAACCATATGTTCAAGAATAGTTACAGAGAAGCAGGAACACCCTGTCGT
1857  5_HRV1B2|d     CAATGATATGGGAACCATATGTTCAAGAATAGTTACAGAGAAGCAGGAACACCCTGTCGT
1858  6_HRV1B        CAATGATATGGGAACCATATGTTCAAGAATAGTTACAGAGAAGCAGGAACACCCTGTCGT
1859  7_HRV40a|d     TAACCATATGGGAACGCTATGCTCAAGAATAGTCACCAACAAGCAGCAGCATGAAGTTGA
1860  8_HRV40b|d     TAACCATATGGGAACGCTATGCTCAAGAATAGTCACCAACAAGCAGCAGCATGAAGTTGA
1861  9_HRV40        TAACCATATGGGAACGCTATGCTCAAGAATAGTCACCAACAAGCAGCAGCATGAAGTTGA
1862  10_HRV85       CAACCACATGGGAACACTGTGCTCGAGGATAGTTACCAACAAACAGCAGCATGAGGTTGA
1863  11_HRV85a|     CAACCACATGGGAACACTGTGCTCGAGGATAGTTACCAACAAACAGCAGCATGAGGTTGA
1864  12_HRV85b|     CAACCACATGGGAACACTGTGCTCGAGGATAGTTACCAACAAACAGCAGCATGAGGTTGA
1865  13_HRV56a|     AAACCACATGGGGACACTCTGTTCAAGAATTGTGACAAATAAACAACTTCATCCTGTTGA
1866  14_HRV56b|     AAACCACATGGGGACACTCTGTTCAAGAATTGTGACAAATAAACAACTTCATCCTGTTGA
1867  15_HRV56       AAACCACATGGGGACACTCTGTTCAAGAATTGTGACAAATAAACAACTTCATCCTGTTGA
1868  16_HRV54       CAATCATATGGGTACTTTGTGTTCAAGAGTGGTTACTGATAAACAAAAACACCCAGTTGA
1869  17_HRV98       TAATCACATGGGCACTTTGTGTTCAAGAGTAGTTACTGGCAAACAAGAACACCCAGTTGA
1870  18_HRV59a|     CAACCACATGGGCACTTTATGTTCTAGAATAGTTACAAACAGTCAGGAGCATCCAGTGGA
1871  19_HRV59b|     CAACCACATGGGCACTTTATGTTCTAGAATAGTTACAAACAGTCAGGAGCATCCAGTGGA
1872  20_HRV59       CAACCACATGGGCACTTTATGTTCTAGAATAGTTACAAACAGTCAGGAGCATCCAGTGGA
1873  21_HRV63       TAACCACATGGGGACTTTATGTTCTAGAATTGTAACAAACAGCCAAGAACATCCAGTTGA
1874  22_HRV63b|     TAACCACATGGGGACTTTATGTTCTAGAATTGTAACAAACAGCCAAGAACATCCAGTTGA
1875  23_HRV63a|     TAACCACATGGGGACTTTATGTTCTAGAATTGTAACAAACAGCCAAGAACATCCAGTTGA
1876  24_HRV39       TAATGATATGGGTACACTTTGCACTAGAATTGTAACAAACCAACAGGAACACCTAGTGGA
1877  25_HRV39a|     TAATGATATGGGTACACTTTGCACTAGAATTGTAACAAACCAACAGGAACACCTAGTGGA
1878  26_HRV39b|     TAATGATATGGGTACACTTTGCACTAGAATTGTAACAAACCAACAGAAACACCTAGTGGA
1879  27_HRV10a|     AAATCACATGGGCACTTTGTGCATGCGAATAGTCACAAACCAGCAAGCACATGAGGTGGA
1880  28_HRV10b|     AAATCACATGGGCACTTTGTGCATGCGAATAGTCACAAACCAGCAAGCACATGAGGTGGA
1881  29_HRV10       AAATCACATGGGCACTTTGTGCATGCGAATAGTCACAAACCAGCAAGCACATGAGGTGGA
1882  30_HRV100a     TAACCACATGGGTACACTTTGTATGAGGATAGTTACAAATCAGCAAGCACATGAGGTGGA
1883  31_HRV100b     TAACCACATGGGTACACTTTGTATGAGGATAGTTACAAATCAGCAAGCACATGAGGTGGA
1884  32_HRV100      TAACCACATGGGTACACTTTGTATGAGGATAGTTACAAATCAGCAAGCACATGAGGTGGA
1885  33_HRV66       TAATCATATGGGTACATTATGTATTAGGATTGTTACAAATGAACAGCACCATAATGTTGA
```

FIG. D12 CONT'D

| | | |
|---|---|---|
| 1886 | 34_HRV66b| | TAATCATATGGGTACATTATGTATTAGGATTGTTACAAATGAACAGCACCATAATGTTGA |
| 1887 | 35_HRV66a| | TAATCATATGGGTACATTATGTATTAGGATTGTTACAAATGAACAGCACCATAATGTTGA |
| 1888 | 36_HRV77a| | TAATCACATGGGCACACTGTGCATTAGAATAGTCACTAATCAGCAAAATCATGAGGTTGA |
| 1889 | 37_HRV77b| | TAATCACATGGGCACACTGTGCATTAGAATAGTCACTAATCAGCAAAATCATGAGGTTGA |
| 1890 | 38_HRV77 | TAATCACATGGGCACACTGTGCATTAGAATAGTCACTAATCAGCAAAATCATGAGGTTGA |
| 1891 | 39_HRV62a | TAATCGTATGGGGGCACTGTGTATGAGGATTGTCACAAACAAACAAGTTCATGATGTTGA |
| 1892 | 40_HRV62b | TAATCGTATGGGGGCACTGTGTATGAGGATTGTCACAAACAAACAAGTTCATGATGTTGA |
| 1893 | 41_HRV25 | TAACCGTATGGGAGCACTGTGCATGAGAATTGTCACAAATAAACAAGTCCATGATGTTGA |
| 1894 | 42_HRV29a | TAACCGGATGGGGACGCTTTGTGTCAGAATTGTTACAGGCAAACAAGCTCATGATGTTCA |
| 1895 | 43_HRV29b | TAACCGGATGGGGACGCTTTGTGTCAGAATTGTTACAGGCAAACAAGCTCATGATGTTCA |
| 1896 | 44_HRV44a | TAACCGGATGGGGACGCTTTGCGTCAGGATCGTTACGGGCAAACAGGCTCATGATGTCCA |
| 1897 | 45_HRV44b | TAACCGGATGGGGACGCTTTGCGTCAGGATCGTTACGGGCAAACAGGCTCATGATGTCCA |
| 1898 | 46_HRV31 | TAATCGCATGGGTGCACTATGCATGAGAGTTGTCACTAACAAACAAGCTCATAAAGTTGA |
| 1899 | 47_HRV31a| | TAATCGCATGGGTGCACTATGCATGAGAGTTGTCACTAACAAACAAGCTCATAAAGTTGA |
| 1900 | 48_HRV31b| | TAATCGCATGGGTGCACTATGCATGAGAGTTGTCACTAACAAACAAGCTCATAAAGTTGA |
| 1901 | 49_HRV47 | CAATCGCATGGGTGCATTGTGTATGAGAGTTGTAACAAACAAGCAACTCCATAAAGTTGA |
| 1902 | 50_HRV47a| | CAATCGCATGGGTGCATTGTGTATGAGAGTTGTAACAAACAAGCAACTCCATAAAGTTGA |
| 1903 | 51_HRV47b| | CAATCGCATGGGTGCATTGTGTATGAGAGTTGTAACAAACAAGCAACTCCATAAAGTTGA |
| 1904 | 52_HRV11 | CAATGATATGGGCACTCTGTGTTATAGAATAGTAACTGATGACCATAGACACAAAATTGA |
| 1905 | 53_HRV11b| | CAATGATATGGGCACTCTGTGTTATAGAATAGTAACTGATGACCATAGACACAAAATTGA |
| 1906 | 54_HRV11a| | CAATGATATGGGCACTCTGTGTTATAGAATAGTAACTGATGACCATAGACACAAAATTGA |
| 1907 | 55_HRV76 | CAATGACATGGGCACCCTATGTTCCAGGATAGTAACTGATGATCATAAGCACAAGATTGA |
| 1908 | 56_HRV76b| | CAATGACATGGGCACCCTATGTTCCAGGATAGTAACTGATGATCATAAGCACAAGATTGA |
| 1909 | 57_HRV76a| | CAATGACATGGGCACCCTATGTTCCAGGATAGTAACTGATGATCATAAGCACAAGATTGA |
| 1910 | 58_HRV33 | CAATGACATGGGCACTTTATGCTCTAGAATAGTTACAGATAATCATAAGCATCCAATAGA |
| 1911 | 59_HRV33b| | CAATGACATGGGCACTTTATGCTCTAGAATAGTTACAGATAATCATAAGCATCCAATAGA |
| 1912 | 60_HRV33a| | CAATGACATGGGCACTTTATGCTCTAGAATAGTTACAGATAATCATAAGCATCCAATAGA |
| 1913 | 61_HRV24a| | AAACGACATGGGAACTCTATGCTATAGAATAGTCACTGACAAGCATAATCACCAAATAGA |
| 1914 | 62_HRV24b| | AAACGACATGGGAACTCTATGCTATAGAATAGTCACTGACAAGCATAATCACCAAATAGA |
| 1915 | 63_HRV24 | AAACGACATGGGAACTCTATGCTATAGAATAGTCACTGACAAGCATAATCACCAAATAGA |
| 1916 | 64_HRV90 | TAATGATATGGGAACCTTATGTTATAGAATAGTTACAGATGAACATGCCCACAAAATAGA |
| 1917 | 65_HRV90a| | TAATGATATGGGAACCTTATGTTATAGAATAGTTACAGATGAACATGCCCACAAAATAGA |
| 1918 | 66_HRV90b| | TAATGATATGGGAACCTTATGTTATAGAATAGTTACAGATGAACATGCCCACAAAATAGA |
| 1919 | 67_HRV34 | TAATGACATGGGTACTTTATGCTCCAGAATTGTAACTGATGAACACCAAAACAGAGTAGA |
| 1920 | 68_HRV34b| | TAATGACATGGGTACTTTATGCTCCAGAATTGTAACTGATGAACACCAAAACAGAGTAGA |
| 1921 | 69_HRV34a| | TAATGACATGGGTACTTTATGCTCCAGAATTGTAACTGATGAACACCAAAACAGAGTAGA |
| 1922 | 70_HRV50a| | CAATGACATGGGCACTTTGTGTTCTAGGATTGTCACTGATGAGCACCAAAATAAAGTGGA |
| 1923 | 71_HRV50b| | CAATGACATGGGCACTTTGTGTTCTAGGATTGTCACTGATGAGCACCAAAATAAAGTGGA |
| 1924 | 72_HRV50 | CAATGACATGGGCACTTTGTGTTCTAGGATTGTCACTGATGAGCACCAAAATAAAGTGGA |
| 1925 | 73_HRV18a| | AAATGACATGGGTACCTTGTGCTCTAGAATAGTCACAGATAAACATAAGAATGAGGTGGA |
| 1926 | 74_HRV18b| | AAATGACATGGGTACCTTGTGCTCTAGAATAGTCACAGATAAACATAAGAATGAGGTGGA |
| 1927 | 75_HRV18 | AAATGACATGGGTACCTTGTGCTCTAGAATAGTCACAGATAAACATAAGAATGAGGTGGA |
| 1928 | 76_HRV55 | TAATGACATGGGCACTTTATGTTCTAGAATAATAACTGATAACCATAAGCACCCAATTGA |
| 1929 | 77_HRV55b| | TAATGACATGGGTACTTTATGTTCTAGAATAATAACTGATAACCATAAGCACCCAATTGA |
| 1930 | 78_HRV55a| | TAATGACATGGGTACTTTATGTTCTAGAATAATAACTGATAACCATAAGCACCCAATTGA |
| 1931 | 79_HRV57 | TAATGACATGGGCACTTTATGTTCTAGAATTGTTACTGACCAGCACACACATCCCATAAA |
| 1932 | 80_HRV57a| | TAATGACATGGGCACTTTATGTTCTAGAATTGTTACTGACCAGCACACACATCCCATAAA |
| 1933 | 81_HRV57b| | TAATGACATGGGCACTTTATGTTCTAGAATTGTTACTGACCAGCACACACATCCCATAAA |
| 1934 | 82_HRV21 | TAATGATATGGGATCTCTATGCTACAGAATAGTAACTGGCCAGCATAAGCATAAGATAGA |
| 1935 | 83_HRVHan | TAATGATATGGGATCTCTATGCTATAGAATAGTAACTGATCAGCATAAGCACAAGATAGA |
| 1936 | 84_HRV43 | CAACCACATGGGAACATTATGTTCTAGGATGTTACAGAAGAACACCAAAATCAAATCGA |
| 1937 | 85_HRV43b| | CAACCACATGGGAACATTATGTTCTAGGATAGTTACAGAAGAACACCAAAATCAAATCGA |
| 1938 | 86_HRV43a| | CAACCACATGGGAACATTATGTTCTAGGATAGTTACAGAAGAACACCAAAATCAAATCGA |
| 1939 | 87_HRV75 | TAATCACATGGGACACTGTGTTCTAGAATAGTTACAGAAGAACATCGAAATAAAGTTGA |
| 1940 | 88_HRV75b| | TAATCACATGGGGACACTGTGTTCTAGAATAGTTACAGAAGAACATCGAAATAAAGTTGA |
| 1941 | 89_HRV75a| | TAATCACATGGGGACACTGTGTTCTAGAATAGTTACAGAAGAACATCGAAATAAAGTTGA |
| 1942 | 96_HRV9a|d | AAATGATATGGGATCTTTATGTTCCCGTGTAGTTACTGAAGAGCATGGACCCCGTGTCAA |
| 1943 | 97_HRV9b|d | AAATGATATGGGATCTTTATGTTCCCGTGTAGTTACTGAAGAGCATGGACCCCGTGTCAA |
| 1944 | 98_HRV9 | AAATGATATGGGATCTTTATGTTCCCGTGTAGTTACTGAAGAGCATGGACCCCGTGTCAA |
| 1945 | 99_HRV32 | AAATGATATGGGTTCCCTGTGTTCTCGTATAGTCACCGAAGAGCACGGATCCCGTGTTGA |
| 1946 | 100_HRV32a | AAATGATATGGGTTCCCTGTGTTCTCGTATAGTCACCGAAGAGCACGGATCCCGTGTTGA |
| 1947 | 101_HRV32b | AAATGATATGGGTTCCCTGTGTTCTCGTATAGTCACCGAAGAGCACGGATCCCGTGTTGA |
| 1948 | 102_HRV67 | TAATGATATGGGTTCCTTGTGTTCGCGTATAGTTACTGAAGAACATGGTTCTCGCGTAAA |
| 1949 | 103_HRV67a | TAATGATATGGGTTCCTTGTGTTCGCGTATAGTTACTGAAGAACATGGTTCTCGCGTAAA |
| 1950 | 104_HRV67b | TAATGATATGGGTTCCTTGTGTTCGCGTATAGTTACTGAAGAACATGGTTCTCGCGTAAA |

FIG. D12 CONT'D

```
08.trace                                                                                                    9/20/2007 5:05 PM 1951 105_HRV15     TAATGACATGGGGACACTGTGTTCTAGAATAGTAACTGAAGAGCATGGGACACGTGTAGA
1952 106_HRV15a    TAATGACATGGGGACACTGTGTTCTAGAATAGTAACTGAAGAGCATGGGACACGTGTAGA
1953 107_HRV15b    TAATGACATGGGGACACTGTGTTCTAGAATAGTAACTGAAGAGCATGGGACACGTGTAGA
1954 108_HRV74a    AAATGACATGGGAACTCTATGTTCTAGAATTGTGACTGAAGAACACGATGCACGTGTGGA
1955 109_HRV74b    AAATGACATGGGAACTCTATGTTCTAGAATTGTGACTGAAGAACACGATGCACGTGTGGA
1956 110_HRV74     AAATGACATGGGAACTCTATGTTCTAGAATTGTGACTGAAGAACACGATGCACGTGTGGA
1957 111_HRV38a    CAATGATATGGGGACACTTTGTTCAAGAATAGTCACTGAAAATCATGGGACCCAAGTGAA
1958 112_HRV38b    CAATGATATGGGGACACTTTGTTCAAGAATAGTCACTGAAAATCATGGGACCCAAGTGAA
1959 113_HRV38     CAATGATATGGGGACACTTTGTTCAAGAATAGTCACTGAAAATCATGGGACCCAAGTGAA
1960 114_HRV60     CAATGACATGGGAACGTTGTGCTCCAGAATAGTTACTGAACACCATGGTACACAGGTTCA
1961 115_HRV60a    CAATGACATGGGAACGTTGTGCTCCAGAATAGTTACTGAACACCATGGTACACAGGTTCA
1962 116_HRV60b    CAATGACATGGGAACGTTGTGCTCCAGAATAGTTACTGAACACCATGGTACACAGGTTCA
1963 117_HRV64a    AAATGATATGGGCACTTTGTGTTCTAGAATTGTGACTGAGGAACACACAACACAGGTCAA
1964 118_HRV64b    AAATGATATGGGCACTTTGTGTTCTAGAATTGTGACTGAGGAACACACAACACAGGTCAA
1965 119_HRV64     AAATGATATGGGCACTTTGTGTTCTAGAATTGTGACTGAGGAACACACAACACAGGTCAA
1966 120_HRV94a    AAATGACATGGGAACATTATGCTCCAGGATTGTGACTGAGGAGCACAAGACACAGGTTAA
1967 121_HRV94b    AAATGACATGGGAACATTATGCTCCAGGATTGTGACTGAGGAGCACAAGACACAGGTTAA
1968 122_HRV94     AAATGACATGGGAACATTATGCTCCAGGATTGTGACTGAGGAGCACAAGACACAGGTTAA
1969 123_HRV22     AAATGATATGGGCACACTGTGCTCTAGGATTGTGACTGAAGAACACCAGACACAAGTCAA
1970 124_HRV22a    AAATGATATGGGCACACTGTGCTCTAGGATTGTGACTGAAGAACACCAGACACAAGTCAA
1971 125_HRV22b    AAATGATATGGGCACACTGTGCTCTAGGATTGTGACTGAAGAACACCAGACACAAGTCAA
1972 126_HRV82     AAATGACATGGGTACACTGTGTTCTAGAATTGTAACTGAAGAACACCAGACTCAAGTCAG
1973 127_HRV82b    AAATGACATGGGTACACTGTGTTCTAGAATTGTAACTGAAGAACACCAGACTCAAGTCAG
1974 128_HRV82a    AAATGACATGGGTACACTGTGTTCTAGAATTGTAACTGAAGAACACCAGACTCAAGTCAG
1975 129_HRV19     TAATGATATGGGAACCTTATGCTCCAGAATAGTAACTGATGAACACCAAACACAGGTTGC
1976 130_HRV19a    TAATGATATGGGAACCTTATGCTCCAGAATAGTAACTGATGAACACCAAACACAGGTTGC
1977 131_HRV19b    TAATGATATGGGAACCTTATGCTCCAGAATAGTAACTGATGAACACCAAACACAGGTTGC
1978 132_HRV13     TAATGATATGGGCACACTTTGCTTCAGAATAGTAACTGAAGAACATACTAACAAGGTCAA
1979 133_HRV13a    TAATGATATGGGCACACTTTGCTTCAGAATAGTAACTGAAGAACATACTAACAAGGTCAA
1980 134_HRV13b    TAATGATATGGGCACACTTTGCTTCAGAATAGTAACTGAAGAACATACTAACAAGGTCAA
1981 135_HRV41     AAATGACATGGGTACATTATGCTTTAGAATAGTTACTGAAGAACACACCAACAAAGTTAA
1982 136_HRV41a    AAATGACATGGGTACATTATGCTTTAGAATAGTTACTGAAGAACACACCAACAAAGTTAA
1983 137_HRV41b    AAATGACATGGGTACATTATGCTTTAGAATAGTTACTGAAGAACACACCAACAAAGTTAA
1984 138_HRV73     TAATGACATGGGCACATTATGCTTTAGGATAGTGACTGAAGAACACACTAGCAGGGTAAA
1985 139_HRV73b    TAATGACATGGGCACATTATGCTTTAGGATAGTGACTGAAGAACACACTAGCAGGGTAAA
1986 140_HRV73a    TAATGACATGGGCACATTATGCTTTAGGATAGTGACTGAAGAACACACTAGCAGGGTAAA
1987 141_HRV61     AAATGATATGGGTGCATTGTGCTTTAGAATAGTAACTGAACAGCATACAAATCAAGTTAA
1988 142_HRV61a    AAATGATATGGGTGCATTGTGCTTTAGAATAGTAACTGAACAGCATACAAATCAAGTTAA
1989 143_HRV61b    AAATGATATGGGTGCATTGTGCTTTAGAATAGTAACTGAACAGCATACAAATCAAGTTAA
1990 144_HRV96     CAATGACATGGGCACTTTATGTTTTAGAATAGTGACAGAGGAACACACCAACAAGGTCAA
1991 145_HRV96b    CAATGACATGGGCACTTTATGTTTTAGAATAGTGACAGAGGAACACACCAACAAGGTCAA
1992 146_HRV96a    CAATGACATGGGCACTTTATGTTTTAGAATAGTGACAGAGGAACACACCAACAAGGTCAA
1993 90_HRV16a|    CAATGACATGGGAACTTTGTGTTCGCGTATTGTGACCAGTGAGCAATTACACAAAGTCAA
1994 91_HRV16b|    CAATGACATGGGAACTTTGTGTTCGCGTATTGTGACCAGTGAGCAATTACACAAAGTCAA
1995 92_1AYM_A     CAATGACATGGGAACTTTGTGTTCGCGTATTGTGACCAGTGAGCAATTACACAAAGTCAA
1996 93_HRV81a|    TAATGATATGGGAACATTATGCTCACGGATAGTGACAAGTGAGCAAGTGCACAAGGTGAA
1997 94_HRV81b|    TAATGATATGGGAACATTATGCTCACGGATAGTGACAAGTGAGCAAGTGCACAAGGTGAA
1998 95_HRV81      TAATGATATGGGAACATTATGCTCACGGATAGTGACAAGTGAGCAAGTGCACAAGGTGAA
1999 GROUP_1       -AA----ATGGG--C--T-TG-----G--T--T-AC-------CA-----------T---
2000
2001 1_HRV1A1|d    CATCACAACACACATATATCATAAAGCTAAACACACAAAAGCTTGGTGTCCTAGGCCCCC
2002 2_HRV1A2|d    CATCACAACACACATATATCATAAAGCTAAACACACAAAAGCTTGGTGTCCTAGGCCCCC
2003 3_HRV1A|cD    CATCACAACACACATATATCATAAAGCTAAACACACAAAAGCTTGGTGTCCTAGGCCCCC
2004 4_HRV1B1|d    TATTACAACACACATATATCACAAAGCTAAACACACAAAAGCTTGGTGTCCTAGACCTCC
2005 5_HRV1B2|d    TATTACAACACACATATATCACAAAGCTAAACACACAAAAGCTTGGTGTCCTAGACCTCC
2006 6_HRV1B       TATTACAACACACATATATCACAAAGCTAAACACACAAAAGCTTGGTGTCCTAGACCTCC
2007 7_HRV40a|d    GATTACCACACGTATATATCACAAGGCCAAGCATATTAAAGCATGGTGTCCAAGGGCCCC
2008 8_HRV40b|d    GATTACCACACGTATATATCACAAGGCCAAGCATATTAAAGCATGGTGTCCAAGGGCCCC
2009 9_HRV40       GATTACCACACGTATATATCACAAGGCCAAGCATATTAAAGCATGGTGTCCAAGGGCCCC
2010 10_HRV85      AATCACCACGCGTGTGTATCATAAGGCCAAGCATGTAAAGGCTTGGTGTCCAAGAGCACC
2011 11_HRV85a     AATCACCACGCGTGTGTATCATAAGGCCAAGCATGTAAAGGCTTGGTGTCCAAGAGCACC
2012 12_HRV85b     AATCACCACGCGTGTGTATCATAAGGCCAAGCATGTAAAGGCTTGGTGTCCAAGAGCACC
2013 13_HRV56a|    AGTCACAACTCGTGTATATCATAAGGCAAAGCATATTCGAGCATGGTGTCCTAGAGCACC
2014 14_HRV56b|    AGTCACAACTCGTGTATATCATAAGGCAAAGCATATTCGAGCATGGTGTCCTAGAGCACC
2015 15_HRV56      AGTCACAACTCGTGTATATCATAAGGCAAAGCATATTCGAGCATGGTGTCCTAGAGCACC
```

FIG. D12 CONT'D

08.trace                                                                9/20/2007 5:05 PM

```
2016 16_HRV54    AATCACCACACGGGTGTATCACAAGGCAAAACACATTAGAGCATGGTGTCCACGTGCACC
2017 17_HRV98    AATCACTACACGTGTGTACCACAAAGCAAAACACATTAGAGCATGGTGTCCACGTGCACC
2018 18_HRV59a|  GGTTGTCACACGTGTGTATCACAAAGCTAAACACGTCAAAGCCTGGTGCCCTAGAGCTCC
2019 19_HRV59b|  GGTTGTCACACGTGTGTATCACAAAGCTAAACACGTCAAAGCCTGGTGCCCTAGAGCTCC
2020 20_HRV59    GGTTGTCACACGTGTGTATCACAAAGCTAAACACGTCAAAGCCTGGTGCCCTAGAGCTCC
2021 21_HRV63    GGTGACTACACGTGTATATCATAAAGCTAAACACATCAGAGCCTGGTGCCCAAGAGCTCC
2022 22_HRV63b|  GGTGACTACACGTGTATATCATAAAGCTAAACACATCAGAGCCTGGTGCCCAAGAGCTCC
2023 23_HRV63a|  GGTGACTACACGTGTATATCATAAAGCTAAACACATCAGAGCCTGGTGCCCAAGAGCTCC
2024 24_HRV39    GGTTACAACCAGAGTTTACCATAAAGCCAAGCATGTTAAAGCATGGTGCCCTAGGGCTCC
2025 25_HRV39a|  GGTTACAACCAGAGTTTACCATAAAGCCAAGCATGTTAAAGCATGGTGCCCTAGGGCTCC
2026 26_HRV39b|  GGTTACAACCAGAGTTTACCATAAAGCCAAGCATGTTAAAGCATGGTGCCCTAGGGCTCC
2027 27_HRV10a|  AATTACCACCAGTGTTTATCACAAAGCCAAGCATGTCAAAGCATGGTGTCCAAGACCACC
2028 28_HRV10b|  AATTACCACCAGTGTTTATCACAAAGCCAAGCATGTCAAAGCATGGTGTCCAAGACCACC
2029 29_HRV10    AATTACCACCAGTGTTTATCACAAAGCCAAGCATGTCAAAGCATGGTGTCCAAGACCACC
2030 30_HRV100a  AATTACTACTAATATCTATCACAAGGCCAAACATGTTAAAGCTTGGTGCCCAAGACCACC
2031 31_HRV100b  AATTACTACTAATATCTATCACAAGGCCAAACATGTTAAAGCTTGGTGCCCAAGACCACC
2032 32_HRV100   AATTACTACTAATATCTATCACAAGGCCAAACATGTTAAAGCTTGGTGCCCAAGACCACC
2033 33_HRV66    AATTACTACTAGAGTATACCATAAGGCTAAGCATGTTAAAGCCTGGTGTCCTAGACCACT
2034 34_HRV66b|  AATTACTACTAGAGTATACCATAAGGCTAAGCATGTTAAAGCCTGGTGTCCTAGACCACT
2035 35_HRV66a|  AATTACTACTAGAGTATACCATAAGGCTAAGCATGTTAAAGCCTGGTGTCCTAGACCACT
2036 36_HRV77a|  AATCACCACTAGAGTATACCACAAGGCTAAACATATTAAAGCTTGGTGTCCCAGACCACC
2037 37_HRV77b|  AATCACCACTAGAGTATACCACAAGGCTAAACATATTAAAGCTTGGTGTCCCAGACCACC
2038 38_HRV77    AATCACCACTAGAGTATACCACAAGGCTAAACATATTAAAGCTTGGTGCCCAGACCACC
2039 39_HRV62a   GGTCACAACTAATATTTACCACAAGGCTAAGCATGTAAAAGCGTGGTGCCCGCGGCCGCC
2040 40_HRV62b   GGTCACAACTAATATTTACCACAAGGCTAAGCATGTAAAAGCGTGGTGCCCTAGACCACC
2041 41_HRV25    GGTTACAACTAACATTTACCATAAAGCTAAGCATGTAAAAGCATGGTGCCCTAGACCACC
2042 42_HRV29a   AGTTACAACAAGTATCTATCATAAAGCTAAACATGTAAAGGCGTGGTGTCCTAGACCACC
2043 43_HRV29b   AGTTACAACAAGTATCTATCATAAAGCTAAACATGTAAAGGCGTGGTGTCCTAGACCACC
2044 44_HRV44a   AGTTACAACAAGCATTTATCACAAAGCTAAACATGTAAAAGCATGGTGCCCTAGACCACC
2045 45_HRV44b   AGTTACAACAAGCATTTATCACAAAGCTAAACATGTAAAAGCATGGTGCCCTAGACCACC
2046 46_HRV31    AATCACAACCAATATTTACCATAAGGCCAAACATGTTAAGGCATGGTGTCCTAGGCCCCC
2047 47_HRV31a|  AATCACAACCAATATTTACCATAAGGCCAAACATGTTAAGGCATGGTGTCCTAGGCCCCC
2048 48_HRV31b|  AATCACAACCAATATTTACCATAAGGCCAAACATGTAAAGGCATGGTGTCCTAGGCCACC
2049 49_HRV47    AATCACAACTAACATCTACCATAAAGCCAAGCATGTGAAAGCATGGTGTCCTAGACCACC
2050 50_HRV47a|  AATCACAACTAACATCTACCATAAAGCCAAGCATGTGAAAGCATGGTGTCCTAGACCACC
2051 51_HRV47b|  AATCACAACTAACATCTACCATAAAGCCAAGCATGTGAAAGCATGGTGTCCTAGACCACC
2052 52_HRV11    AGTCACAACTAGGGTGTATCATAAAGCAAAGCATGTGAAGGTGTGGTGTCCAAGACCACC
2053 53_HRV11b|  AGTCACAACTAGGGTGTATCATAAAGCAAAGCATGTGAAGGTGTGGTGTCCAAGACCACC
2054 54_HRV11a|  AGTCACAACTAGGGTGTATCATAAAGCAAAGCATGTGAAGGTGTGGTGTCCAAGACCACC
2055 55_HRV76    AGTTACAACAAGAATATATCACAAAGCAAAGCATGTTAAGGTATGGTGCCCGAGACCACC
2056 56_HRV76b|  AGTTACAACAAGAATATATCACAAAGCAAAGCATGTTAAGGTATGGTGCCCGAGACCACC
2057 57_HRV76a|  AGTTACAACAAGAATATATCACAAAGCAAAGCATGTTAAGGTATGGTGCCCGAGACCACC
2058 58_HRV33    AGTTACAACAAGAGTATACCATAAAGCAAAACATGTCAAAGTCTGGTGCCCAAGACCACC
2059 59_HRV33b|  AGTTACAACAAGAGTATACCATAAAGCAAAACATGTCAAAGTCTGGTGCCCAAGACCACC
2060 60_HRV33a|  AGTTACAACAAGAGTATACCATAAAGCAAAACATGTCAAAGTCTGGTGCCCAAGACCACC
2061 61_HRV24a|  AATTACAACAAGAATATACCACAAAGCAAAGCACATTAAGGTCTGGTGTCCAAGGCCACC
2062 62_HRV24b|  AATTACAACAAGAATATACCACAAAGCAAAGCACATTAAGGTCTGGTGTCCAAGGCCACC
2063 63_HRV24    AATTACAACAAGAATATACCACAAAGCAAAGCACATTAAGGTCTGGTGTCCAAGGCCACC
2064 64_HRV90    GATCACTACAAGAATATACCATAAAGCAAAACACATTAAGGTTTGGTGTCCAAGACCACC
2065 65_HRV90a|  GATCACTACAAGAATATACCATAAAGCAAAACACATTAAGGTTTGGTGTCCAAGACCACC
2066 66_HRV90b|  GATCACTACAAGAATATACCATAAAGCAAAACACATTAAGGTTTGGTGTCCAAGACCACC
2067 67_HRV34    AATAACAACTAGAGTTTATCACAAAGCTAAACATGTAAAAACCTGGTGTCCAAGACCACC
2068 68_HRV34b|  AATAACAACTAGAGTTTATCACAAAGCTAAACATGTAAAAACCTGGTGTCCAAGACCACC
2069 69_HRV34a|  AATAACAACTAGAGTTTATCACAAAGCTAAACATGTAAAAACCTGGTGTCCAAGACCACC
2070 70_HRV50a|  AATCACAACCAGAGTATACCATAAAGCCAAACACATAAAAGTCTGGTGTCCAAGACCACC
2071 71_HRV50b|  AATCACAACCAGAGTATACCATAAAGCCAAACACATAAAAGTCTGGTGTCCAAGACCACC
2072 72_HRV50    AATCACAACCAGAGTATACCATAAAGCCAAACACATAAAAGTCTGGTGTCCAAGACCACC
2073 73_HRV18a|  AATAACAACCAGAATATACCACAAGGCAAAACATGTTAAAGCATGGTGCCCAAGGCCACC
2074 74_HRV18b|  AATAACAACCAGAATATACCACAAGGCAAAACATGTTAAAGCATGGTGCCCAAGGCCACC
2075 75_HRV18    AATAACAACCAGAATATACCACAAGGCAAAACATGTTAAAGCATGGTGCCCAAGGCCACC
2076 76_HRV55    AGTGACGACAAGAGTCTATCATAAAGCTAAACACATCAAAGCATGGTGCCCACGACCACC
2077 77_HRV55b|  AGTGACGACAAGAGTCTATCATAAAGCTAAACACATCAAAGCATGGTGCCCACGACCACC
2078 78_HRV55a|  AGTGACGACAAGAGTCTATCATAAAGCTAAACACATCAAAGCATGGTGCCCACGACCACC
2079 79_HRV57    AATAACAACCAGAGTGTATCACAAAGCCAAACATGTCAAAGCCTGGTGCCCTAGACCACC
2080 80_HRV57a|  AATAACAACCAGAGTGTATCACAAAGCCAAACATGTCAAAGCCTGGTGCCCTAGACCACC
```

FIG. D12 CONT'D

08.trace                                                                 9/20/2007 5:05 PM

```
2081  81_HRV57b|    AATAACAACCAGAGTGTATCACAAAGCCAAACATGTCAAAGCCTGGTGCCCTAGACCACC
2082  82_HRV21      AGTGACCACAAGAATATACCATAAGGCAAAGCATGTTAAAGCTTGGTGCCCCAGACCACC
2083  83_HRVHan     AGTGACCACAAGAATATACCATAAGGCAAAGCATGTTAAAGCTTGGTGCCCTAGACCACC
2084  84_HRV43      GATAACTACCAGGATATATCATAAAGCCAAGCATATCAAAGCTTGGTGCCCAAGACCACC
2085  85_HRV43b|    GATAACTACCAGGATATATCATAAAGCCAAGCATATCAAAGCTTGGTGCCCAAGACCACC
2086  86_HRV43a|    GATAACTACCAGGATATATCATAAAGCCAAGCATATCAAAGCTTGGTGCCCAAGACCACC
2087  87_HRV75      AGTAACCACTAGAATATATCACAAAGCCAAACATATAAAAGCTTGGTGTCCGAGGCCGCC
2088  88_HRV75b|    AGTAACCACTAGAATATATCACAAAGCCAAACATATAAAAGCTTGGTGTCCGAGGCCGCC
2089  89_HRV75a|    AGTAACCACTAGAATATATCACAAAGCCAAACATATAAAAGCTTGGTGTCCGAGGCCGCC
2090  96_HRV9a|d    AATTTCAACCAGAATATATCACAAAGCCAAACATGTTAAAGCCTGGTGCCCAAGACCTCC
2091  97_HRV9b|d    AATTTCAACCAGAATATATCACAAAGCCAAACATGTTAAAGCCTGGTGCCCAAGACCTCC
2092  98_HRV9       AATTTCAACCAGAATATATCACAAAGCCAAACATGTTAAAGCCTGGTGCCCAAGACCTCC
2093  99_HRV32      TATTTCAACTAGGGTATATCACAAAGCTAAACACGTCAAAGCTTGGTGCCCACGACCACC
2094  100_HRV32a    TATTTCAACTAGGGTATATCACAAAGCTAAACACGTCAAAGCTTGGTGCCCACGACCACC
2095  101_HRV32b    TATTTCAACTAGGGTATATCACAAAGCTAAACACGTCAAAGCTTGGTGCCCACGACCACC
2096  102_HRV67     AATTGCAACGCGGGTGTATCATAAGGCTAAACATGTAAAAGCTTGGTGCCCAAGGCCCCC
2097  103_HRV67a    AATTGCAACGCGGGTGTATCATAAGGCTAAACATGTAAAAGCTTGGTGCCCAAGGCCCCC
2098  104_HRV67b    AATTGCAACGCGGGTGTATCATAAGGCTAAACATGTAAAAGCTTGGTGCCCAAGGCCCCC
2099  105_HRV15     GATTACAACTAGAGTGTATCACAAAGCTAAACATGTAAAGGCTTGGTGCCCCAGACCCCC
2100  106_HRV15a    GATTACAACTAGAGTGTATCACAAAGCTAAACATGTAAAGGCTTGGTGCCCCAGACCCCC
2101  107_HRV15b    GATTACAACTAGAGTGTATCACAAAGCTAAACATGTAAAGGCTTGGTGCCCCAGACCCCC
2102  108_HRV74a    AATTACAACTAGAGTGTACCATAAAGCAAAGCATGTGAAGGCATGGTGTCCTAGACCCCC
2103  109_HRV74b    AATTACAACTAGAGTGTACCATAAAGCAAAGCATGTGAAGGCATGGTGTCCTAGACCCCC
2104  110_HRV74     AATTACAACTAGAGTGTACCATAAAGCAAAGCATGTGAAGGCATGGTGTCCTAGACCCCC
2105  111_HRV38a    GATAACAACTAGAATTTATCATAAGGCAAAACATGTAAAAGCCTGGTGTCCAAGACCCCC
2106  112_HRV38b    GATAACAACTAGAATTTATCATAAGGCAAAACATGTAAAAGCCTGGTGTCCAAGACCCCC
2107  113_HRV38     GATAACAACTAGAATTTATCATAAGGCAAAACATGTAAAAGCCTGGTGTCCAAGACCCCC
2108  114_HRV60     CGTCGCAACAAGAATATATCATAAAGCAAAGCATGTTAAAGCTTGGTGTCCAAGACCTCC
2109  115_HRV60a    CGTCGCAACAAGAATATATCATAAAGCAAAGCATGTTAAGGCTTGGTGTCCAAGACCTCC
2110  116_HRV60b    CGTCGCAACAAGAATATATCATAAAGCAAAGCATGTTAAGGCTTGGTGTCCAAGACCTCC
2111  117_HRV64a    CATCACTACTAGGGTTTATCACAAAGCAAAACATGTCAAGGCATGGTGTCCACGGCCCCC
2112  118_HRV64b    CATCACTACTAGGGTTTATCACAAAGCAAAACATGTCAAGGCATGGTGTCCACGGCCCCC
2113  119_HRV64     CATCACTACTAGGGTTTATCACAAAGCAAAACATGTCAAGGCATGGTGTCCACGGCCCCC
2114  120_HRV94a    CATCACTACTAGAGTGTACCACAAAGCAAAACATGTGAAAGCGTGGTGCCCGCGCCCTCC
2115  121_HRV94b    CATCACTACTAGAGTGTACCACAAAGCAAAACATGTGAAAGCGTGGTGCCCGCGCCCTCC
2116  122_HRV94     CATCACTACTAGAGTGTACCACAAAGCAAAACATGTGAAAGCGTGGTGCCCGCGCCCTCC
2117  123_HRV22     AATTACAACTAGAGTGTACCACAAAGCAAAACATGTAAAGGCATGGTGCCCACGTCCTCC
2118  124_HRV22a    AATTACAACTAGAGTGTACCACAAAGCAAAACATGTAAAGGCATGGTGCCCACGTCCTCC
2119  125_HRV22b    AATTACAACTAGAGTGTACCACAAAGCAAAACATGTAAAGGCATGGTGCCCACGTCCTCC
2120  126_HRV82     CATTACCACAAGAATATATCACAAAGCAAAACATGTGAAAGCGTGGTGCCCACGACCCCC
2121  127_HRV82b    CATTACCACAAGAATATATCACAAAGCAAAACATGTGAAAGCGTGGTGTCCACGACCCCC
2122  128_HRV82a    CATTACCACAAGAATATATCACAAAGCAAAACATGTGAAAGCGTGGTGTCCACGACCCCC
2123  129_HRV19     AATCACAACTAGAGTATATCATAAAGCTAAACATATAAAAGCTTGGTGCCCACGACCACC
2124  130_HRV19a    AATCACAACTAGAGTATATCATAAAGCTAAACATATAAAAGCTTGGTGCCCACGACCACC
2125  131_HRV19b    AATCACAACTAGAGTATATCATAAAGCTAAACATATAAAAGCTTGGTGCCCACGACCACC
2126  132_HRV13     GGTTACAACTAGAATCTATCATAAAGCTAAACATGTCAAAGCATGGTGTCCTAGACCTCC
2127  133_HRV13a    GGTTACAACTAGAATCTATCATAAAGCTAAACATGTCAAAGCATGGTGTCCTAGACCTCC
2128  134_HRV13b    GGTTACAACTAGAATCTATCATAAAGCTAAACATGTCAAAGCATGGTGTCCTAGACCTCC
2129  135_HRV41     GGTCACAACTAGAGTTTACCACAAAGCTAAACATGTTAAAGCATGGTGTCCTAGACCTCC
2130  136_HRV41a    GGTCACAACTAGAGTTTACCACAAAGCTAAACATGTTAAAGCATGGTGTCCTAGACCTCC
2131  137_HRV41b    GGTCACAACTAGAGTTTACCACAAAGCTAAACATGTTAAAGCATGGTGTCCTAGACCTCC
2132  138_HRV73     GGTTACTACTAGAATCTATCATAAGGCTAAACATGTTAAAGCTTGGTGTCCAAGACCTCC
2133  139_HRV73b    GGTTACTACTAGAATCTATCATAAGGCTAAACATGTTAAAGCTTGGTGTCCAAGACCTCC
2134  140_HRV73a    GGTTACTACTAGAATCTATCATAAGGCTAAACATGTTAAAGCTTGGTGTCCAAGACCTCC
2135  141_HRV61     AATCACAACTAGGATTTACCATAAAGCTAAACATGTTAAAGTCTGGTGTCCTAGACCCCC
2136  142_HRV61a    AATCACAACTAGGATTTACCATAAAGCTAAACATGTTAAAGTCTGGTGTCCTAGACCCCC
2137  143_HRV61b    AATCACAACTAGGATTTACCATAAAGCTAAACATGTTAAAGTCTGGTGTCCTAGACCCCC
2138  144_HRV96     AATTACAACCAGAGTTTACCACAAAGCTAAACATGTTAAGGTGTGGTGCCCGAGACCCCC
2139  145_HRV96b    AATTACAACCAGAGTTTACCACAAAGCTAAACATGTTAAGGTGTGGTGCCCGAGACCCCC
2140  146_HRV96a    AATTACAACCAGAGTTTACCACAAAGCTAAACATGTTAAGGTGTGGTGCCCGAGACCCCC
2141  90_HRV16a|    AGTGGTAACAAGGATATATCACAAAGCCAAACACACCAAAGCTTGGTGCCCAAGACCACC
2142  91_HRV16b|    AGTGGTAACAAGGATATATCACAAAGCCAAACACACCAAAGCTTGGTGCCCAAGACCACC
2143  92_1AYM_A     AGTGGTAACAAGGATATATCACAAAGCCAAACACACCAAAGCTTGGTGCCCAAGACCACC
2144  93_HRV81a|    AATAGTAACAAGAATATATCACAAAGCTAAGCACACCAAAGCTTGGTGTCCAAGACCACC
2145  94_HRV81b|    AATAGTAACAAGAATATATCACAAAGCTAAGCACACCAAAGCTTGGTGTCCAAGACCACC
```

FIG. D12 CONT'D 08.trace                                                                    9/20/2007 5:05 PM

```
2146  95_HRV81      AATAGTAACAAGAATATATCACAAAGCTAAGCACACCAAAGCTTGGTGTCCAAGACCACC
2147  GROUP_1       --T----AC-----T-TA-CA-AA-GC-AA-CA----------TGGTG-CC--G--C-C-
2148
2149   1_HRV1A1|d   TAGAGCTGTCCCTTACACA-CATAGTCATGTGACTAATTATATGC-CAGAAA---CAGGT
2150   2_HRV1A2|d   TAGAGCTGTCCCTTACACA-CATAGTCATGTGACTAATTATATGC-CAGAAA---CAGGT
2151   3_HRV1A|cD   TAGAGCTGTCCCTTACACA-CATAGTCATGTGACTAATTATATGC-CAGAAA---CAGGT
2152   4_HRV1B1|d   TAGAGCTGTTCCTTACACA-CATAGTCGTGTAACTAATTATGTAC-CAAAAA---CAGGT
2153   5_HRV1B2|d   TAGAGCTGTTCCTTACACA-CATAGTCGTGTAACTAATTATGTAC-CAAAAA---CAGGT
2154   6_HRV1B      TAGAGCTGTTCCTTACACA-CATAGTCGTGTAACTAATTATGTAC-CAAAAA---CAGGT
2155   7_HRV40a|d   AAGAGCAGTACCTTACACA-CATACACACTCAACAAATTATAAAC-CTCAAG---AAGGT
2156   8_HRV40b|d   AAGAGCAGTACCTTACACA-CATACACACTCAACAAATTATAAAC-CTCAAG---AAGGT
2157   9_HRV40      AAGAGCAGTACCTTACACA-CATACACACTCAACAAATTATAAAC-CTCAAG---AAGGT
2158  10_HRV85      AAGAGCGGTGCCTTATACA-CACACACGCTCAACCAACTATGTGC-CACAAG---ATGGT
2159  11_HRV85a|    AAGAGCGGTGCCTTATACA-CACACACGCTCAACCAACTATGTGC-CACAAG---ATGGT
2160  12_HRV85b|    AAGAGCGGTGCCTTATACA-CACACACGCTCAACCAACTATGTGC-CACAAG---ATGGT
2161  13_HRV56a|    AAGGGCTGTGCCTTATACA-CATGCTCACGTCACCAATTATAAAC-CACAAG---ATGGT
2162  14_HRV56b|    AAGGGCTGTGCCTTATACA-CATGCTCACGTCACCAATTATAAAC-CACAAG---ATGGT
2163  15_HRV56      AAGGGCTGTGCCTTATACA-CATGCTCACGTCACCAATTATAAAC-CACAAG---ATGGT
2164  16_HRV54      TAGGGCTGTCCCATACACA-CATACTAGATCAACAAATTACATGC-CACGGG---AGGGT
2165  17_HRV98      TAGAGCTGTTCCAATACACA-CACTAGATCAACTAATTACATGC-CACAAG---ATGGT
2166  18_HRV59a|    TAGAGCAGTCCCTTACACA-CACAGCTACGTAACTAACTACAAGATTGCTGG---AAAA-
2167  19_HRV59b|    TAGAGCAGTCCCTTACACA-CACAGCTACGTAACTAACTACAAGATTGCTGG---AAAA-
2168  20_HRV59      TAGAGCAGTCCCTTACACA-CACAGCTACGTAACTAACTACAAGATTGCTGG---AAAA-
2169  21_HRV63      TAGGGCTGTTCCATACACA-CATAGTTATGTCACTAACTATAAAATTACAGG---ACAG-
2170  22_HRV63b|    TAGGGCTGTTCCATACACA-CATAGTTATGTCACTAACTATAAAATTACAGG---ACAG-
2171  23_HRV63a|    TAGGGCTGTTCCATACACA-CATAGTTATGTCACTAACTATAAAATTACAGG---ACAG-
2172  24_HRV39      CAGAGCAGTCCCTTACACA-CACAGCAATGTTACAAATTACAAAG-TACGGG---ACGGT
2173  25_HRV39a|    CAGAGCAGTCCCTTACACA-CACAGCAATGTTACAAATTACAAAG-TACGGG---ACGGT
2174  26_HRV39b|    CAGAGCAGTCCCTTACACA-CACAGCAATGTTACAAATTACAAAG-TACGGG---ACGGT
2175  27_HRV10a|    CAGAGCTGTACCATATACA-CATGCCCATTCCACAAATTACAAAC-CACATG---GCAAA
2176  28_HRV10b|    CAGAGCTGTACCATATACA-CATGCCCATTCCACAAATTACAAAC-CACATG---GCAAA
2177  29_HRV10      CAGAGCTGTACCATATACA-CATGCCCATTCCACAAATTACAAAC-CACATG---GCAAA
2178  30_HRV100a    TCGGGCTGTGCCGTACACA-CATAGTCACTCTACAAATTACAAAC-CACATG---AGGGT
2179  31_HRV100b    TCGGGCTGTGCCGTACACA-CATAGTCACTCTACAAATTACAAAC-CACATG---AGGGT
2180  32_HRV100     TCGGGCTGTGCCGTACACA-CATAGTCACTCTACAAATTACAAAC-CACATG---AGGGT
2181  33_HRV66      TAGAGCTGTACCATACACA-ACTGTAAACTCAACCAATTATATGC-CTCATA---CTGGT
2182  34_HRV66b|    TAGAGCTGTACCATACACA-ACTGTAAACTCAACCAATTATATGC-CTCATA---CTGGT
2183  35_HRV66a|    TAGAGCTGTACCATACACA-ACTGTAAACTCAACCAATTATATGC-CTCATA---CTGGT
2184  36_HRV77a|    TAGAGCTGTACCATACACA-GCAGTAGATTCAACAAATTACAAAC-CTATGA---GAGGG
2185  37_HRV77b|    TAGAGCTGTACCATACACA-GCAGTAGATTCAACAAATTACAAAC-CTATGA---GAGGG
2186  38_HRV77      TAGAGCTGTACCATACACA-GCAGTAGATTCAACAAATTACAAAC-CTATGA---GAGGG
2187  39_HRV62a     CAGAGCTGTTCCATATAAA-TATGTTGATTTCAATAATTATGCAG-CCAGTG---ATAGT
2188  40_HRV62b     TAGAGCTGTTCCATATAAA-TATGTTGATTTCAATAATTATGCAG-CCAGTG---ATAGT
2189  41_HRV25      TAGAGCTGTCCCATATAAA-TATGTTGACTTCAATAATTATGCAG-CCAGTG---ATAAT
2190  42_HRV29a     AAGAGTTGTCCCATACAAG-TATGTTGGCCTAACTAATTACACAC-TTAAAG---AAGAA
2191  43_HRV29b     AAGAGTTGTCCCATACAAG-TATGTTGGCCTAACTAATTACACAC-TTAAAG---AAGAA
2192  44_HRV44a     AAGGGTTGTCCCATACAAG-TATGTTGGCCTAACTAATTACACAC-TTAAAG---AAACA
2193  45_HRV44b     AAGGGTTGTCCCATACAAG-TATGTTGGCCTAACTAATTACACAC-TTAAAG---AAACA
2194  46_HRV31      TAGAGCAGTTCCATACAGGGTATG-TGGATCAACAAATACAAAC-CTGATG---AAAAT
2195  47_HRV31a|    TAGAGCAGTTCCATACAGGGTATG-TGGATCAACAAATACAAAC-CTGATG---AAAAT
2196  48_HRV31b|    TAGAGCAGTTCCATACAGG-TATGTTGGATCAACAAATACAAAC-CTGATG---AAAAT
2197  49_HRV47      TAGAGCTGTTCCATATAGA-TATGTTGGATCAACAAATTACAAAC-CTGATC---AAGGA
2198  50_HRV47a|    TAGAGCTGTTCCATATAGA-TATGTTGGATCAACAAATTACAAAC-CTGATC---AAGGA
2199  51_HRV47b|    TAGAGCTGTTCCATATAGA-TATGTTGGATCAACAAATTACAAAC-CTGATC---AAGGA
2200  52_HRV11      TAGAGCTGTAGAATATACT-CACACTCATGTAACCAATTACAAAC-CACAGG---AAGGA
2201  53_HRV11b|    TAGAGCTGTAGAATATACT-CACACTCATGTAACCAATTACAAAC-CACAGG---AAGGA
2202  54_HRV11a|    TAGAGCTGTAGAATATACT-CACACTCATGTAACCAATTACAAAC-CACAGG---AAGGA
2203  55_HRV76      TAGAGCTGTAGAGTATACA-TACACCCATGTAACAAACTACAAAC-CACATT---CTGGT
2204  56_HRV76b|    TAGAGCTGTAGAGTATACA-TACACCCATGTAACAAACTACAAAC-CACATT---CTGGT
2205  57_HRV76a|    TAGAGCTGTAGAGTATACA-TACACCCATGTAACAAACTACAAAC-CACATT---CTGGT
2206  58_HRV33      TAGAGCTGTGGAATACACC-CATACTCATGTTACAAATTATAAAT-CAACAA---CTCGT
2207  59_HRV33b|    TAGAGCTGTGGAATACACC-CATACTCATGTTACAAATTATAAAT-CAACAA---CTCGT
2208  60_HRV33a|    TAGAGCTGTGGAATACACC-CATACTCATGTTACAAATTATAAAT-CAACAA---CTCGT
2209  61_HRV24a|    CAGAGCTGTTGAGTATACA-CATACTCACGTGACCAATTATAAGC-ATCAGA---CTCGT
2210  62_HRV24b|    CAGAGCTGTTGAGTATACA-CATACTCACGTGACCAATTATAAGC-ATCAGA---CTCGT
```

FIG. D12 CONT'D

```
08.trace                                                                         9/20/2007 5:05 PM 2211  63_HRV24    CAGAGCTGTTGAGTATACA-CATACTCACGTGACCAATTATAAGC-ATCAGA---CTCGT
2212  64_HRV90    TAGGGCAGTTGAATACACA-CACACTCATGTAACAAACTACAAAC-ATGCAA---CACGT
2213  65_HRV90a|  TAGGGCAGTTGAATACACA-CACACTCATGTAACAAACTACAAAC-ATGCAA---CACGT
2214  66_HRV90b|  TAGGGCAGTTGAATACACA-CACACTCATGTAACAAACTACAAAC-ATGCAA---CACGT
2215  67_HRV34    AAGAGCTGTTGAGTACACA-CACACACATGTTACTAACTACAAAG-TTAGGG---GTAAA
2216  68_HRV34b|  AAGAGCTGTTGAGTACACA-CACACACATGTTACTAACTACAAAG-TTAGGG---GTAAA
2217  69_HRV34a|  AAGAGCTGTTGAGTACACA-CACACACATGTTACTAACTACAAAG-TTAGGG---GTAAA
2218  70_HRV50a|  AAGAGCTGTTGAATACACA-CACACCCATGTCACTAACTACAAGA-AAAGTG---ATGCT
2219  71_HRV50b|  AAGAGCTGTTGAATACACA-CACACCCATGTCACTAACTACAAGA-AAAGTG---ATGCT
2220  72_HRV50    AAGAGCTGTTGAATACACA-CACACCCATGTCACTAACTACAAGA-AAAGTG---ATGCT
2221  73_HRV18a|  GAGAGCTGTGGAGTACACA-CATACACATGTAACTAACTACAAGC-CTAAGG---AAGGA
2222  74_HRV18b|  GAGAGCTGTGGAGTACACA-CATACACATGTAACTAACTACAAGC-CTAAGG---AAGGA
2223  75_HRV18    GAGAGCTGTGGAGTACACA-CATACACATGTAACTAACTACAAGC-CTAAGG---AAGGA
2224  76_HRV55    TAGGGCTGTTGAATACACA-CACACACATGTCACAAATTACAAGA-AGACTG---ATGGC
2225  77_HRV55b|  TAGGGCTGTTGAATACACA-CACACACATGTCACAAATTACAAGA-AGACTG---ATGGC
2226  78_HRV55a|  TAGGGCTGTTGAATACACA-CACACACATGTCACAAATTACAAGA-AGACTG---ATGGC
2227  79_HRV57    ACGGGCTATCGAGTACACA-CATACACATGTTACTAATTATAAAA-TAAAAG---ATAGA
2228  80_HRV57a|  ACGGGCTATCGAGTACACA-CATACACATGTTACTAATTATAAAA-TAAAAG---ATAGA
2229  81_HRV57b|  ACGGGCTATCGAGTACACA-CATACACATGTTACTAATTATAAAA-TAAAAG---ATAGA
2230  82_HRV21    GAGGGCCGTTGAATACACA-CATACACACGTAACCAATTACAAAA-TTGCAA---ATCAT
2231  83_HRVHan   GAGGGCCGTTGAATACACA-CATACACATGTAACCAATTACAAAA-TTGCAA---ATAAA
2232  84_HRV43    CAGAGCTGTTGAATACACA-CACACACATGTCACAAATTATAAAA-GAGAAG---GAAAG
2233  85_HRV43b|  CAGAGCTGTTGAATACACA-CACACACATGTCACAAATTATAAAA-GAGAAG---GAAAG
2234  86_HRV43a|  CAGAGCTGTTGAATACACA-CACACACATGTCACAAATTATAAAA-GAGAAG---GAAAG
2235  87_HRV75    CAGGGCTGTTGAATACACA-TTTAGACGTGTAACAAATTACAAAA-GAGATG---GACAA
2236  88_HRV75b|  CAGGGCTGTTGAATACACA-TTTAGACGTGTAACAAATTACAAAA-GAGATG---GACAA
2237  89_HRV75a|  CAGGGCTGTTGAATACACA-TTTAGACGTGTAACAAATTACAAAA-GAGATG---GACAA
2238  96_HRV9a|d  TAGGGCAGTTGAGTATATA-CATACACATGTCACAAATTACAAGC-CAAGCA---CAGGC
2239  97_HRV9b|d  TAGGGCAGTTGAGTATATA-CATACACATGTCACAAATTACAAGC-CAAGCA---CAGGC
2240  98_HRV9     TAGGGCAGTTGAGTATATA-CATACACATGTCACAAATTACAAGC-CAAGCA---CAGGC
2241  99_HRV32    TAGGGCAGTTGAATATACA-CATACACATGTTACAAATTACAAAC-CAAGCA---CAGGT
2242  100_HRV32a  TAGGGCAGTTGAATATACA-CATACACATGTTACAAATTACAAAC-CAAGCA---CAGGT
2243  101_HRV32b  TAGGGCAGTTGAATATACA-CATACACATGTTACAAATTACAAAC-CAAGCA---CAGGT
2244  102_HRV67   TAGAGCAGTTGAATACATA-CACACACATGTTACAAACTATAGAC-CAGAAA---CAGGT
2245  103_HRV67a  TAGAGCAGTTGAATACACA-CACACACATGTTACAAACTATAGAC-CAGAAA---CAGGT
2246  104_HRV67b  TAGAGCAGTTGAATACATA-CACACACATGTTACAAACTATAGAC-CAGAAA---CAGGT
2247  105_HRV15   TAGAGCAGTGGAATATACA-CACACACATGTCACAAATTACAAAC-CACAAG---ATGGT
2248  106_HRV15a  TAGAGCAGTGGAATATACA-CACACACATGTCACAAATTACAAAC-CACAAG---ATGGT
2249  107_HRV15b  TAGAGCAGTGGAATATACA-CACACACATGTCACAAATTACAAAC-CACAAG---ATGGT
2250  108_HRV74a  TAGAGCAGTTGAATATACT-CACACACATGTCACAAATTACAAAC-CACAAG---AAGGT
2251  109_HRV74b  TAGAGCAGTTGAATATACT-CACACACATGTCACAAATTACAAAC-CACAAG---AAGGT
2252  110_HRV74   TAGAGCAGTTGAATATACT-CACACACATGTCACAAATTACAAAC-CACAAG---AAGGT
2253  111_HRV38a  AAGGGCAGTTGAATATAGA-CATACACATGTTAACAATTACAAAC-CAGACC---AAGGG
2254  112_HRV38b  AAGGGCAGTTGAATATAGA-CATACACATGTTAACAATTACAAAC-CAGACC---AAGGG
2255  113_HRV38   AAGGGCAGTTGAATATAGA-CATACACATGTTAACAATTACAAAC-CAGACC---AAGGG
2256  114_HRV60   AAGGGCAGTTGAATATAGA-CACACACATGTAAACAACTATAGAC-CAGATG---ATGGA
2257  115_HRV60a  AAGGGCAGTTGAATATAGA-CACACACATGTAAACAACTATAGAC-CAGATG---ATGGA
2258  116_HRV60b  AAGGGCAGTTGAATATAGA-CACACACATGTAAACAACTATAGAC-CAGATG---ATGGA
2259  117_HRV64a  AAGAGCTGTTGGATATACA-CATACAAATGTCACCAATTATAAAC-CATCCA---AAGGA
2260  118_HRV64b  AAGAGCTGTTGGATATACA-CATACAAATGTCACCAATTATAAAC-CATCCA---AAGGA
2261  119_HRV64   AAGAGCTGTTGGATATACA-CATACAAATGTCACCAATTATAAAC-CATCCA---AAGGA
2262  120_HRV94a  AAGAGCTGTTGGATACACA-CATACGCATGTCACTAATTACAAAC-CATCTG---AAGGG
2263  121_HRV94b  AAGAGCTGTTGGATACACA-CATACGCATGTCACTAATTACAAAC-CATCTG---AAGGG
2264  122_HRV94   AAGAGCTGTTGGATACACA-CATACGCATGTCACTAATTACAAAC-CATCTG---AAGGG
2265  123_HRV22   AAGAGCTGTTGGATATACA-CACACACATGTGACAAACTACAAAC-CATCTG---TAGGG
2266  124_HRV22a  AAGAGCTGTTGGATATACA-CACACACATGTGACAAACTACAAAC-CATCTG---TAGGG
2267  125_HRV22b  AAGAGCTGTTGGATATACA-CACACACATGTGACAAACTACAAAC-CATCTG---TAGGG
2268  126_HRV82   GAGGGCTGTGGGTTATACA-CACACACATGTTACCAACTACAAGC-CATCAC---AGGGA
2269  127_HRV82b  GAGGGCTGTGGGTTATACA-CACACACATGTTACCAACTACAAGC-CATCAC---AGGGA
2270  128_HRV82a  GAGGGCTGTGGGTTATACA-CACACACATGTTACCAACTACAAGC-CATCAC---AGGGA
2271  129_HRV19   CAGAGCCGTGGAATATACC-CACACTCATGTGACTAATTATAAAC-CCCAGA---CAGGT
2272  130_HRV19a  CAGAGCCGTGGAATATACC-CACACTCATGTGACTAATTATAAAC-CCCAGA---CAGGT
2273  131_HRV19b  CAGAGCCGTGGAATATACC-CACACTCATGTGACTAATTATAAAC-CCCAGA---CAGGT
2274  132_HRV13   CAGAGCTGTTGAATATACT-AATGTGCATGTTACAAACTACAAAC-CAGGGA---CAGGA
2275  133_HRV13a  CAGAGCTGTTGAATATACT-AATGTGCATGTTACAAACTACAAAC-CAGGGA---CAGGA
```

FIG. D12 CONT'D

```
08.trace                                                                    9/20/2007 5:05 PM 2276  134_HRV13b     CAGAGCTGTTGAATATACT-AATGTGCATGTTACAAACTACAAAC-CAGGGA---CAGGA
2277  135_HRV41      CAGGGCTGTGGAGTACACC-AATGTGCATGTCACAAATTACAAAC-CAAAAG---CAGGA
2278  136_HRV41a     CAGGGCTGTGGAGTACACC-AATGTGCATGTCACAAATTACAAAC-CAAAAG---CAGGA
2279  137_HRV41b     CAGGGCTGTGGAGTACACC-AATGTGCATGTCACAAATTACAAAC-CAAAAG---CAGGA
2280  138_HRV73      TAGGGCAGTAGAATATACA-AATGCACATGTGACCAATTATAAAC-CCACTG---ATGGA
2281  139_HRV73b     TAGGGCAGTAGAATATACA-AATGCACATGTGACCAATTATAAAC-CCACTG---ATGGA
2282  140_HRV73a     TAGGGCAGTAGAATATACA-AATGCACATGTGACCAATTATAAAC-CCACTG---ATGGA
2283  141_HRV61      CAGAGCAGTGGAATATACT-AATGTGCATTTGACCAATTACAAGC-CCAAAG---ATAGT
2284  142_HRV61a     CAGAGCAGTGGAATATACT-AATGTGCATTTGACCAATTACAAGC-CCAAAG---ATAGT
2285  143_HRV61b     CAGAGCAGTGGAATATACT-AATGTGCATTTGACCAATTACAAGC-CCAAAG---ATAGT
2286  144_HRV96      TAGAGCAGTTGAATACACA-AATGTGCATCTCACAAATTATAAAC-CCAACA---ATG--
2287  145_HRV96b     TAGAGCAGTTGAATACACA-AATGTGCATCTCACAAATTATAAAC-CCAACA---ATG--
2288  146_HRV96a     TAGAGCAGTTGAATACACA-AATGTGCATCTCACAAATTATAAAC-CCAACA---ATG--
2289  90_HRV16a|     CAGAGCTGTTCAATACTCA-CATACACATACCACCAACTACAAAT-TGAGTT---CAGAA
2290  91_HRV16b|     CAGAGCTGTTCAATACTCA-CATACACATACCACCAACTACAAAT-TGAGTT---CAGAA
2291  92_1AYM_A      CAGAGCTGTTCAATACTCA-CATACACATACCACCAACTACAAAT-TGAGTT---CAGAA
2292  93_HRV81a|     CAGGGCTGTTCAGTACACA-CATACACATGTAACTAATTATAAAT-TAGAAA---CAGAT
2293  94_HRV81b|     CAGGGCTGTTCAGTACACA-CATACACATGTAACTAATTATAAAT-TAGAAA---CAGAT
2294  95_HRV81       CAGGGCTGTTCAGTACACA-CATACACATGTAACTAATTATAAAT-TAGAAA---CAGAT
2295  GROUP_1        --G-G---T----TA----------------A--AA-TA-------------...-----
2296
2297  1_HRV1A1|d     GACG------TGACAACAG---CCATAGTCCGCAGAA------ACACTATAACAACTG--
2298  2_HRV1A2|d     GACG------TGACAACAG---CCATAGTCCGCAGAA------ACACTATAACAACTG--
2299  3_HRV1A|cD     GACG------TGACAACAG---CCATAGTCCGCAGAA------ACACTATAACAACTG--
2300  4_HRV1B1|d     GATG------TGACAACAG---CTATAGTTCCTAGAG------CTAGCATGAAAACTG--
2301  5_HRV1B2|d     GATG------TGACAACAG---CTATAGTTCCTAGAG------CTAGCATGAAAACTG--
2302  6_HRV1B        GATG------TGACAACAG---CTATAGTTCCTAGAG------CTAGCATGAAAACTG--
2303  7_HRV40a|d     GAAG------TCCAGATTT---TCCTCAAAGAGAGAG------CCAGCCTAACAACAG--
2304  8_HRV40b|d     GAAG------TCCAGATTT---TCCTCAAAGAGAGAG------CCAGCCTAACAACAG--
2305  9_HRV40        GAAG------TCCAGATTT---TCCTCAAAGAGAGAG------CCAGCCTAACAACAG--
2306  10_HRV85       GAAG------TTAAGATCT---TCCTCAAAGAGAGAG------CTAGTTTAACCACAG--
2307  11_HRV85a|     GAAG------TTAAGATCT---TCCTCAAAGAGAGAG------CTAGTTTAACCACAG--
2308  12_HRV85b|     GAAG------TTAAGATCT---TCCTCAAAGAGAGAG------CTAGTTTAACCACAG--
2309  13_HRV56a|     GATG------TACAGATCT---TCTTAAAACCCAGAC------CCAGCCTAACAACAT--
2310  14_HRV56b|     GATG------TACAGATCT---TCTTAAAACCCAGAC------CCAGCCTAACAACAT--
2311  15_HRV56       GATG------TACAGATCT---TCTTAAAACCCAGAC------CCAGCCTAACAACAT--
2312  16_HRV54       GATC------CAACAATTT---TCCTTAAACACAGGA------CAAACCTTGTAACAG--
2313  17_HRV98       GAAC------CAACAATCT---TTCTTAAGCATAGAA------AAGATCTTGTAACAG--
2314  18_HRV59a|     GAAC------CTGAAATTT---TCTTAAAACCAAGAA------TGAATATTACAACAG--
2315  19_HRV59b|     GAAC------CTGAAATTT---TCTTAAAACCAAGAA------TGAATATTACAACAG--
2316  20_HRV59       GAAC------CTGAAATTT---TCTTAAAACCAAGAA------TGAATATTACAACAG--
2317  21_HRV63       GAGA------CTGAAATTT---TCTTAAAACCTAGAG------CAACTATCAAGACAG--
2318  22_HRV63b|     GAGA------CTGAAATTT---TCTTAAAACCTAGAG------CAACTATCAAGACAG--
2319  23_HRV63a|     GAGA------CTGAAATTT---TCTTAAAACCTAGAG------CAACTATCAAGACAG--
2320  24_HRV39       GAAC------CAACACTCT---TTATAAAATCAAGAG------AGAATCTTACCACAG--
2321  25_HRV39a|     GAAC------CAACACTCT---TTATAAAATCAAGAG------AGAATCTTACCACAG--
2322  26_HRV39b|     GAAC------CAACACTCT---TTATAAAATCAAGAG------AGAATCTTACCACAG--
2323  27_HRV10a|     GAAT------TACAAATAT---TTATTAGGTCTAGAGATGATCCCAAAGTAGTAACTG--
2324  28_HRV10b|     GAAT------TACAAATAT---TTATTAGGTCTAGAGATGATCCCAAAGTAGTAACTG--
2325  29_HRV10       GAAT------TACAAATAT---TTATTAGGTCTAGAGATGATCCCAAAGTAGTAACTG--
2326  30_HRV100a     GATG------TAAAGATTT---TCATTAGACCCAGAGATGATCCCAAAGTTTGTAACTG--
2327  31_HRV100b     GATG------TAAAGATTT---TCATTAGACCCAGAGATGATCCCAAAGTTTGTAACTG--
2328  32_HRV100      GATG------TAAAGATTT---TCATTAGACCCAGAGATGATCCCAAAGTTTGTAACTG--
2329  33_HRV66       GATC------TGCAAATTT---TCATTAAACCTAGAACAGATCCAAAAGTAGTCAATG--
2330  34_HRV66b|     GATC------TGCAAATTT---TCATTAAACCTAGAACAGATCCAAAAGTAGTCAATG--
2331  35_HRV66a|     GATC------TGCAAATTT---TCATTAAACCTAGAACAGATCCAAAAGTAGTCAATG--
2332  36_HRV77a|     GATG------TACAAATCT---TTATTAAAGAGAGAGCAAGCCCAAAAGTAGTTACTT--
2333  37_HRV77b|     GATG------TACAAATCT---TTATTAAAGAGAGAGCAAGCCCAAAAGTAGTTACTT--
2334  38_HRV77       GATG------TACAAATCT---TTATTAAAGAGAGAGCAAGCCCAAAAGTAGTTACTT--
2335  39_HRV62a      ---G------TTGACATTT---TTATAAAATCAAGG------CAAAACTTGCAAACAG--
2336  40_HRV62b      ---G------TTGACATTT---TTATAAAATCAAGG------CAAAACTTGCAAACAG--
2337  41_HRV25       ---G------TTGACATCT---TTATACAACCAAGA------AACAGTTTAAAAACAG--
2338  42_HRV29a      ---G------AT-CCAG-----TTGTGGAATCCAGA------CCAAGCTTAATGACAG--
2339  43_HRV29b      ---G------AT-ACAG-----TTGTGGAATCCAGA------CCAAGCTTAATGACAG--
2340  44_HRV44a      ---G------AT-ACAG-----TTGTGGAACCTAGA------CACAGCATAATGACAG--
```

FIG. D12 CONT'D

```
08.trace                                                          9/20/2007 5:05 PM 2341  45_HRV44b    ---G------AT-ACAG-----TTGTGGAACCTAGA------CACAGCATAATGACAG--
2342  46_HRV31     GAAG------TTACAATCT---TTGTTAAACACAGGGATAATCCAAAGATTATCACAG--
2343  47_HRV31a|   GAAG------TTACAATCT---TTGTTAAACACAGGGATAATCCAAAGATTATCACAG--
2344  48_HRV31b|   GAAG------TTACAATCT---TTGTTAAACACAGGGATAATCCAAAGATTATCACAG--
2345  49_HRV47     GAAG------TTGCAATTT---TCATTGAGCATAGAGAAAATCCAAAATTCATTACAG--
2346  50_HRV47a|   GAAG------TTGCAATTT---TCATTGAGCATAGAGAAAATCCAAAATTCATTACAG--
2347  51_HRV47b|   GAAG------TTGCAATTT---TCATTGAGCATAGAGAAAATCCAAAATTCATTACAG--
2348  52_HRV11     CAGG------TGAAAACAG---CTGTCAAGGCTAGGAAAACAATTAAAACAGCA------
2349  53_HRV11b|   CAGG------TGAAAACAG---CTGTCAAGGCTAGGAAAACAATTAAAACAGCG------
2350  54_HRV11a|   CAGG------TGAAAACAG---CTGTCAAGGCTAGGAAAACAATTAAAACAGCT------
2351  55_HRV76     GATG------TGCAAACAG---CTATTAGACCAAGAGCAACAATTAAGACTGCA------
2352  56_HRV76b|   GATG------TGCAAACAG---CTATTAGACCAAGAGCAACAATTAAGACTGCG------
2353  57_HRV76a|   GATG------TGCAAACAG---CTATTAGACCAAGAGCAACAATTAAGACTGCT------
2354  58_HRV33     GAAG------TGAAGACAG---CTATTAGACCAAGAGCAACAATCAAGACTGCA------
2355  59_HRV33b|   GAAG------TGAAGACAG---CTATTAGACCAAGAGCAACAATCAAGACTGCG------
2356  60_HRV33a|   GAAG------TGAAGACAG---CTATTAGACCAAGAGCAACAATCAAGACTGCT------
2357  61_HRV24a|   GAAG------TCAAGACAG---CAATTGAACCTAGAAGAGGAATTAAAACAGTG------
2358  62_HRV24b|   GAAG------TCAAGACAG---CAATTGAACCTAGAAGAGGAATTAAAACAGTC------
2359  63_HRV24     GAAG------TCAAGACAG---CAATTGAACCTAGAAGAGGAATTAAAACAGTT------
2360  64_HRV90     GAAC------TTAAGACTG---CAATTAGGCCCAGGAAAACAATCACAACAGCA------
2361  65_HRV90a|   GAAC------TTAAGACTG---CAATTAGGCCCAGGAAAACAATCACAACAGCG------
2362  66_HRV90b|   GAAC------TTAAGACTG---CAATTAGGCCCAGGAAAACAATCACAACAGCT------
2363  67_HRV34     ACTG------AGAAGACTG---CAATCAAACACAGAGCAAAGATCACAATGGCC------
2364  68_HRV34b|   ACTG------AGAAGACTG---CAATCAAACACAGAGCAAAGATCACAATGGCA------
2365  69_HRV34a|   ACTG------AGAAGACTG---CAATCAAACACAGAGCAAAGATCACAATGGCT------
2366  70_HRV50a|   ACTG------AGAAGACTG---CAATTGCAACTAGACCAAAGATCACAGTGGCA------
2367  71_HRV50b|   ACTG------AGAAGACTG---CAATTGCAACTAGACCAAAGATCACAGTGGCG------
2368  72_HRV50     ACTG------AGAAGACTG---CAATTGCAACTAGACCAAAGATCACAGTGGCT------
2369  73_HRV18a|   AGAG------AGAAAACTG---CCATAGTACCCAGAGCAAGGATTACAATGGCA------
2370  74_HRV18b|   AGAG------AGAAAACTG---CCATAGTACCCAGAGCAAGGATTACAATGGCG------
2371  75_HRV18     AGAG------AGAAAACTG---CCATAGTACCCAGAGCAAGGATTACAATGGCT------
2372  76_HRV55     ACAG------AAAAGACAG---CAATTGAATACAGAAGGGACATTAAAACAGTG------
2373  77_HRV55b|   ACAG------AAAAGACAG---CAATTGAATACAGAAGGGACATTAAAACAGTC------
2374  78_HRV55a|   ACAG------AAAAGACAG---CAATTGAATACAGAAGGGACATTAAAACAGTA------
2375  79_HRV57     CAAG------AAGAAACAG---CAATTAAATATAGAAGGGACATTAAAATTGTTAAGA--
2376  80_HRV57a|   CAAG------AAGAAACAG---CAATTAAATATAGAAGGGACATTAAAATTGTTAAGA--
2377  81_HRV57b|   CAAG------AAGAAACAG---CAATTAAATATAGAAGGGACATTAAAATTGTTAAGA--
2378  82_HRV21     GAAG------TCACTTCTG---CAGTTGAGTCCAGAAGAACAATTGTCACAGTT------
2379  83_HRVHan    GATG------TCACTTCTG---CAGTTGAGTCCAGAAGAACAATTGTCACAGTT------
2380  84_HRV43     GAGG------TAGAAACAG---CCATAGTATCTAGGAGGGATATCAAAATTGTCAATG--
2381  85_HRV43b|   GAGG------TAGAAACAG---CCATAGTATCTAGGAGGGATATCAAAATTGTCAATG--
2382  86_HRV43a|   GAGG------TAGAAACAG---CCATAGTATCTAGGAGGGATATCAAAATTGTCAATG--
2383  87_HRV75     CAAG------TTGAGATTG---CTATTGAGCCCAGAAGAGATGTTAAGTTTGTAAATG--
2384  88_HRV75b|   CAAG------TTGAGATTG---CTATTGAGCCCAGAAGAGATGTTAAGTTTGTAAATG--
2385  89_HRV75a|   CAAG------TTGAGATTG---CTATTGAGCCCAGAAGAGATGTTAAGTTTGTAAATG--
2386  96_HRV9a|d   GATT------ATGCCACAG---TTATACCAGTTAGAGACAATGTTAGGGCAGTAAAGA--
2387  97_HRV9b|d   GATT------ATGCCACAG---TTATACCAGTTAGAGACAATGTTAGGGCAGTAAAGA--
2388  98_HRV9      GATT------ATGCCACAG---TTATACCAGTTAGAGACAATGTTAGGGCAGTAAAGA--
2389  99_HRV32     GATT------ACACCACAG---CCATACAAACCAGAGAGCATGTTAGAGCAGTCAAAA--
2390  100_HRV32a   GATT------ACACCACAG---CCATACAAACCAGAGAGCATGTTAGAGCAGTCAAAA--
2391  101_HRV32b   GATT------ACACCACAG---CCATACAAACCAGAGAGCATGTTAGAGCAGTCAAAA--
2392  102_HRV67    GAGG------CTCAAACGG---TTATACCTGTTAGAGCAGATGTTAGAACAATTAGAA--
2393  103_HRV67a   GAGG------CTCAAACGG---TTATACCTGTTAGAGCAGATGTTAGAACAATTAGAA--
2394  104_HRV67b   GAGG------CTCAAACGG---TTATACCTGTTAGAGCAGATGTTAGAACAATTAGAA--
2395  105_HRV15    GATG------TAACTACAG---TTATTCAACTAGAGAAAATGTTAGAGCTATAGTAA--
2396  106_HRV15a   GATG------TAACTACAG---TTATTCAACTAGAGAAAATGTTAGAGCTATAGTAA--
2397  107_HRV15b   GATG------TAACTACAG---TTATTCAACTAGAGAAAATGTTAGAGCTATAGTAA--
2398  108_HRV74a   GACG------TAACTACAG---TCATCCCAACTAGG---------AGATCAATAGTGA--
2399  109_HRV74b   GACG------TAACTACAG---TCATCCCAACTAGG---------AGATCAATAGTGA--
2400  110_HRV74    GACG------TAACTACAG---TCATCCCAACTAGG---------AGATCAATAGTGA--
2401  111_HRV38a   GAAG------TAACCACTA---TGATTCCAACTAGAACCAACATAAGAACCATCGTAA--
2402  112_HRV38b   GAAG------TAACCACTA---TGATTCCAACTAGAACCAACATAAGAACCATCGTAA--
2403  113_HRV38    GAAG------TAACCACTA---TGATTCCAACTAGAACCAACATAAGAACCATCGTAA--
2404  114_HRV60    GAAG------CAGCCATAA---CAATCCCCATTAGAACTGATATACGAGCAATCAGAA--
2405  115_HRV60a   GAAG------CAGCCATAA---CAATCCCCATTAGAACTGATATACGAGCAATCAGAA--
```

FIG. D12 CONT'D

08.trace                                                                                                  9/20/2007 5:05 PM

```
2406  116_HRV60b       GAAG------CAGCCATAA---CAATCCCCATTAGAACTGATATACGAGCAATCAGAA--
2407  117_HRV64a       GAAT------ACACACCAC---CCGTTCCGTCACGTAACAGCCCCAGAGATATTGTCA--
2408  118_HRV64b       GAAT------ACACACCAC---CCGTTCCGTCACGTAACAGCCCCAGAGATATTGTCA--
2409  119_HRV64        GAAT------ACACACCAC---CCGTTCCGTCACGTAACAGCCCCAGAGATATTGTCA--
2410  120_HRV94a       GAGT------ACAAGCCAC---CTGTCCCAGTTAGGAATAGCCCCAGAGACATTGTCA--
2411  121_HRV94b       GAGT------ACAAGCCAC---CTGTCCCAGTTAGGAATAGCCCCAGAGACATTGTCA--
2412  122_HRV94        GAGT------ACAAGCCAC---CTGTCCCAGTTAGGAATAGCCCCAGAGACATTGTCA--
2413  123_HRV22        GATT------ACACACTAC---CTATCCCAACAAGAGCCAACCCTAGACAAATTTTGA--
2414  124_HRV22a       GATT------ACACACTAC---CTATCCCAACAAGAGCCAACCCTAGACAAATTTTGA--
2415  125_HRV22b       GATT------ACACACTAC---CTATCCCAACAAGAGCCAACCCTAGACAAATTTTGA--
2416  126_HRV82        GATT------ACAGTGTTG---TTATTCCAGTTAGAGAGAGTCCCAGACAGATTCTTA--
2417  127_HRV82b       GATT------ACAGTGTTG---TTATTCCAGTTAGAGAGAGTCCCAGACAGATTCTTA--
2418  128_HRV82a       GATT------ACAGTGTTG---TTATTCCAGTTAGAGAGAGTCCCAGACAGATTCTTA--
2419  129_HRV19        GAAG------TCACTCTTC---CAATTGAAATAAGAGATAACCCTAGACATATAAAGA--
2420  130_HRV19a       GAAG------TCACTCTTC---CAATTGAAATAAGAGATAACCCTAGACATATAAAGA--
2421  131_HRV19b       GAAG------TCACTCTTC---CAATTGAAATAAGAGATAACCCTAGACATATAAAGA--
2422  132_HRV13        GATG------TTGCAGTCT---CCATTGTACCTAGAGCAAATGTTAGGGAAATTAGAA--
2423  133_HRV13a       GATG------TTGCAGTCT---CCATTGTACCTAGAGCAAATGTTAGGGAAATTAGAA--
2424  134_HRV13b       GATG------TTGCAGTCT---CCATTGTACCTAGAGCAAATGTTAGGGAAATTAGAA--
2425  135_HRV41        GCAGA---GATTGTGGCTT---CTGTCAGACCTAGAGACAATGTTAGACAAGTAAGAA--
2426  136_HRV41a       GCAGA---GATTGTGGCTT---CTGTCAGACCTAGAGACAATGTTAGACAAGTAAGAA--
2427  137_HRV41b       GCAGA---GATTGTGGCTT---CTGTCAGACCTAGAGACAATGTTAGACAAGTAAGAA--
2428  138_HRV73        GAAG------TTACTACTG---CCATTAGGCATAGAGATAATGTTAGAGCCATCCAAA--
2429  139_HRV73b       GAAG------TTACTACTG---CCATTAGGCATAGAGATAATGTTAGAGCCATCCAAA--
2430  140_HRV73a       GAAG------TTACTACTG---CCATTAGGCATAGAGATAATGTTAGAGCCATCCAAA--
2431  141_HRV61        GAAAAACAAGTTACCACTT---TCATCAAACCTAGAGCTAACTTAAGAGAGATTAGAA--
2432  142_HRV61a       GAAAAACAAGTTACCACTT---TCATCAAACCTAGAGCTAACTTAAGAGAGATTAGAA--
2433  143_HRV61b       GAAAAACAAGTTACCACTT---TCATCAAACCTAGAGCTAACTTAAGAGAGATTAGAA--
2434  144_HRV96        -------AGGTTACCACTT---TTATCAAACCTAGAGAAAATCTAAGGGATATTAGAA--
2435  145_HRV96b       -------AGGTTACCACTT---TTATCAAACCTAGAGAAAATCTAAGGGATATTAGAA--
2436  146_HRV96a       -------AGGTTACCACTT---TTATCAAACCTAGAGAAAATCTAAGGGATATTAGAA--
2437  90_HRV16a|       GTAC------ACAATGATGTGGCTATAAGACCTAGAACAAATCTAACAACTGTA------
2438  91_HRV16b|       GTAC------ACAATGATGTGGCTATAAGACCTAGAACAAATCTAACAACTGTC------
2439  92_1AYM_A        GTAC------ACAATGATGTGGCTATAAGACCTAGAACAAATCTAACAACTGTT------
2440  93_HRV81a|       GTCC------ACACTAGTGTAGCCATAAAACCTAGAACAAGTCTAACAAATGTG------
2441  94_HRV81b|       GTCC------ACACTAGTGTAGCCATAAAACCTAGAACAAGTCTAACAAATGTC------
2442  95_HRV81         GTCC------ACACTAGTGTAGCCATAAAACCTAGAACAAGTCTAACAAATGTT------
2443  GROUP_1          -------------------------T--------G--------------------..
2444
2445  1_HRV1A1|d       ----CA---------------
2446  2_HRV1A2|d       ----CG---------------
2447  3_HRV1A|cD       ----CT---------------
2448  4_HRV1B1|d       ----TA---------------
2449  5_HRV1B2|d       ----TC---------------
2450  6_HRV1B          ----TT---------------
2451  7_HRV40a|d       ----TA---------------
2452  8_HRV40b|d       ----TC---------------
2453  9_HRV40          ----TT---------------
2454  10_HRV85         ----CA---------------
2455  11_HRV85a|       ----CG---------------
2456  12_HRV85b|       ----CT---------------
2457  13_HRV56a|       ----TA---------------
2458  14_HRV56b|       ----TG---------------
2459  15_HRV56         ----TT---------------
2460  16_HRV54         ----CT---------------
2461  17_HRV98         ----CT---------------
2462  18_HRV59a|       ----CA---------------
2463  19_HRV59b|       ----CG---------------
2464  20_HRV59         ----CT---------------
2465  21_HRV63         ----CA---------------
2466  22_HRV63b|       ----CG---------------
2467  23_HRV63a|       ----CT---------------
2468  24_HRV39         ----CT---------------
2469  25_HRV39a|       ----CA---------------
2470  26_HRV39b|       ----CT---------------
```

FIG. D12 CONT'D 08.trace                                                                 9/20/2007 5:05 PM

```
2471 27_HRV10a|      ----CA--------------
2472 28_HRV10b|      ----CC--------------
2473 29_HRV10       ----CT--------------
2474 30_HRV100a     ----CA--------------
2475 31_HRV100b     ----CG--------------
2476 32_HRV100      ----CT--------------
2477 33_HRV66       ----TA--------------
2478 34_HRV66b|     ----TG--------------
2479 35_HRV66a|     ----TC--------------
2480 36_HRV77a|     ----TG--------------
2481 37_HRV77b|     ----TA--------------
2482 38_HRV77       ----TT--------------
2483 39_HRV62a      ----CT--------------
2484 40_HRV62b      ----C---------------
2485 41_HRV25       ----CT--------------
2486 42_HRV29a      ----CT--------------
2487 43_HRV29b      ----CT--------------
2488 44_HRV44a      ----CT--------------
2489 45_HRV44b      ----CT--------------
2490 46_HRV31       ----CA--------------
2491 47_HRV31a|     ----CT--------------
2492 48_HRV31b|     ----CA--------------
2493 49_HRV47       ----CA--------------
2494 50_HRV47a|     ----CT--------------
2495 51_HRV47b|     ----CA--------------
2496 52_HRV11       --------------------
2497 53_HRV11b|     --------------------
2498 54_HRV11a|     --------------------
2499 55_HRV76       --------------------
2500 56_HRV76b|     --------------------
2501 57_HRV76a|     --------------------
2502 58_HRV33       --------------------
2503 59_HRV33b|     --------------------
2504 60_HRV33a|     --------------------
2505 61_HRV24a|     --------------------
2506 62_HRV24b|     --------------------
2507 63_HRV24       --------------------
2508 64_HRV90       --------------------
2509 65_HRV90a|     --------------------
2510 66_HRV90b|     --------------------
2511 67_HRV34       --------------------
2512 68_HRV34b|     --------------------
2513 69_HRV34a|     --------------------
2514 70_HRV50a|     --------------------
2515 71_HRV50b|     --------------------
2516 72_HRV50       --------------------
2517 73_HRV18a|     --------------------
2518 74_HRV18b|     --------------------
2519 75_HRV18       --------------------
2520 76_HRV55       --------------------
2521 77_HRV55b|     --------------------
2522 78_HRV55a|     --------------------
2523 79_HRV57       ----ATGTG-----------
2524 80_HRV57a|     ----ATGTA-----------
2525 81_HRV57b|     ----ATGTC-----------
2526 82_HRV21       --------------------
2527 83_HRVHan      --------------------
2528 84_HRV43       ----CA--------------
2529 85_HRV43b|     ----CG--------------
2530 86_HRV43a|     ----CT--------------
2531 87_HRV75       ----CA--------------
2532 88_HRV75b|     ----CG--------------
2533 89_HRV75a|     ----CT--------------
2534 96_HRV9a|d     ----ATGTC-----------
2535 97_HRV9b|d     ----ATGTG-----------
```

FIG. D12 CONT'D

```
08.trace                                                              9/20/2007 5:05 PM 2536  98_HRV9      ----ATGTA-----------
2537  99_HRV32     ----ATGTA-----------
2538  100_HRV32a   ----ATGTG-----------
2539  101_HRV32b   ----ATGTC-----------
2540  102_HRV67    ----ATGTA-----------
2541  103_HRV67a   ----ATGTC-----------
2542  104_HRV67b   ----ATGTT-----------
2543  105_HRV15    ----ATGTT-----------
2544  106_HRV15a   ----ATGTA-----------
2545  107_HRV15b   ----ATGTC-----------
2546  108_HRV74a   ----ATGTA-----------
2547  109_HRV74b   ----ATGTC-----------
2548  110_HRV74    ----ATGTT-----------
2549  111_HRV38a   ----ATGTA-----------
2550  112_HRV38b   ----ATGTC-----------
2551  113_HRV38    ----ATGTT-----------
2552  114_HRV60    ----CAGTT-----------
2553  115_HRV60a   ----CAGTA-----------
2554  116_HRV60b   ----CAGTG-----------
2555  117_HRV64a   ----CAGTG-----------
2556  118_HRV64b   ----CAGTG-----------
2557  119_HRV64    ----CAGTA-----------
2558  120_HRV94a   ----CAGTG-----------
2559  121_HRV94b   ----CAGTC-----------
2560  122_HRV94    ----CAGTA-----------
2561  123_HRV22    ----ATGTA-----------
2562  124_HRV22a   ----ATGTG-----------
2563  125_HRV22b   ----ATGTC-----------
2564  126_HRV82    ----ATGTA-----------
2565  127_HRV82b   ----ATGTT-----------
2566  128_HRV82a   ----ATGTC-----------
2567  129_HRV19    ----ATGTA-----------
2568  130_HRV19a   ----ATGTG-----------
2569  131_HRV19b   ----ATGTC-----------
2570  132_HRV13    ----ACTTT-----------
2571  133_HRV13a   ----ACTTG-----------
2572  134_HRV13b   ----ACTTA-----------
2573  135_HRV41    ----ATTAT-----------
2574  136_HRV41a   ----ATTAG-----------
2575  137_HRV41b   ----ATTAC-----------
2576  138_HRV73    ----ATTTT-----------
2577  139_HRV73b   ----ATTTG-----------
2578  140_HRV73a   ----ATTTC-----------
2579  141_HRV61    ----CATTT-----------
2580  142_HRV61a   ----CATTT-----------
2581  143_HRV61b   ----CATTT-----------
2582  144_HRV96    ----ATTTT-----------
2583  145_HRV96b   ----ATTTA-----------
2584  146_HRV96a   ----ATTTC-----------
2585  90_HRV16a|   --------------------
2586  91_HRV16b|   --------------------
2587  92_1AYM_A    --------------------
2588  93_HRV81a|   --------------------
2589  94_HRV81b|   --------------------
2590  95_HRV81     --------------------
2591  GROUP_1      ....-----...........
2592
2593
2594
2595  Group 2:
2596
2597  147_HRV2     AACCCTGTTGAGAATTATATAGATGAAGTTCTTAATGAAGTTTTAGTTGTCCCAAATATT
2598  148_HRV2a|   AACCCTGTTGAGAATTATATAGATGAAGTTCTTAATGAAGTTTTAGTTGTCCCAAATATT
2599  149_HRV2b|   AACCCTGTTGAGAATTATATAGATGAAGTTCTTAATGAAGTTTTAGTTGTCCCAAATATT
2600  150_HRV49a   AATCCTGTTGAACACTACATAGATGAGGTCCTTAATGAGGTTTTAGTTGTTCCAAATATT
```

FIG. D12 CONT'D

```
08.trace                                                                    9/20/2007 5:05 PM 2601 151_HRV49b  AATCCTGTTGAACACTACATAGATGAGGTCCTTAATGAGGTTTTAGTTGTTCCAAATATT
2602 152_HRV49   AATCCTGTTGAACACTACATAGATGAGGTCCTTAATGAGGTTTTAGTTGTTCCAAATATT
2603 153_HRV23a  AATCCAATTGAGAACTATGTAGATGAAGTTCTTAATGAAGTCTTAGTTGTTCCCAATATC
2604 154_HRV23b  AATCCAATTGAGAACTATGTAGATGAAGTTCTTAATGAAGTCTTAGTTGTTCCCAATATC
2605 155_HRV23   AATCCAATTGAGAACTATGTAGATGAAGTTCTTAATGAAGTCTTAGTTGTTCCCAATATC
2606 156_HRV30a  AACCCGGTTGAAAATTTTGTAGATGAAGTTCTTAGTGAAGTTTTAGTTGTTCCAAACATT
2607 157_HRV30b  AACCCGGTTGAAAATTTTGTAGATGAAGTTCTTAGTGAAGTTTTAGTTGTTCCAAACATT
2608 158_HRV30   AACCCGGTTGAAAATTTTGTAGATGAAGTTCTTAGTGAAGTTTTAGTTGTTCCAAACATT
2609 GROUP_2     AA-CC--TTGA--A-T---TAGATGA-GT-CTTA-TGA-GT-TTAGTTGT-CC-AA-AT-
2610
2611 147_HRV2    AATAGTAGTAACCCCACAACATCAAATTCTGCCCCAGCATTAGATGCTGCAGAAACAGGG
2612 148_HRV2a|  AATAGTAGTAACCCCACAACATCAAATTCTGCCCCAGCATTAGATGCTGCAGAAACAGGG
2613 149_HRV2b|  AATAGTAGTAACCCCACAACATCAAATTCTGCCCCAGCATTAGATGCTGCAGAAACAGGG
2614 150_HRV49a  AATAGTAGTCACCCCACGACATCAAACTCTGCTCCAGCATTAGATGCTGCAGAAACAGGG
2615 151_HRV49b  AATAGTAGTCACCCCACGACATCAAACTCTGCTCCAGCATTAGATGCTGCAGAAACAGGG
2616 152_HRV49   AATAGTAGTCACCCCACGACATCAAACTCTGCTCCAGCATTAGATGCTGCAGAAACAGGG
2617 153_HRV23a  AATAGTAGTCATCCCACAACATCAAACTCTGCTCCAGCATTAGACGCTGCGGAAACGGGT
2618 154_HRV23b  AATAGTAGTCATCCCACAACATCAAACTCTGCTCCAGCATTAGACGCTGCGGAAACGGGT
2619 155_HRV23   AATAGTAGTCATCCCACAACATCAAACTCTGCTCCAGCATTAGACGCTGCGGAAACGGGT
2620 156_HRV30a  AACAGTAGTCACCCTACTACATCAAACTCTGCTCCGGCATTAGATGCTGCAGAAACAGGA
2621 157_HRV30b  AACAGTAGTCACCCTACTACATCAAACTCTGCTCCGGCATTAGATGCTGCAGAAACAGGA
2622 158_HRV30   AACAGTAGTCACCCTACTACATCAAACTCTGCTCCGGCATTAGATGCTGCAGAAACAGGA
2623 GROUP_2     AA-AGTAGT-A-CC-AC-ACATCAAA-TCTGC-CC-GCATTAGA-GCTGC-GAAAC-GG-
2624
2625 147_HRV2    CACACTAGTAGTGTTCAACCAGAGGATGTCATTGAAACTAGGTATGTGCAGACATCACAA
2626 148_HRV2a|  CACACTAGTAGTGTTCAACCAGAGGATGTCATTGAAACTAGGTATGTGCAGACATCACAA
2627 149_HRV2b|  CACACTAGTAGTGTTCAACCAGAGGATGTCATTGAAACTAGGTATGTGCAGACATCACAA
2628 150_HRV49a  CACACTAGCAATGTGCAACCTGAAGATGTCATTGAAACCAGATATGTACAGACATCACAA
2629 151_HRV49b  CACACTAGCAATGTGCAACCTGAAGATGTCATTGAAACCAGATATGTACAGACATCACAA
2630 152_HRV49   CACACTAGCAATGTGCAACCTGAAGATGTCATTGAAACCAGATATGTACAGACATCACAA
2631 153_HRV23a  CACACTAGTAATGTTCAACCAGAAGATGTCATTGAAACCAGGTACGTTCAAACATCACAA
2632 154_HRV23b  CACACTAGTAATGTTCAACCAGAAGATGTCATTGAAACCAGGTACGTTCAAACATCACAA
2633 155_HRV23   CACACTAGTAATGTTCAACCAGAAGATGTCATTGAAACCAGGTACGTTCAAACATCACAA
2634 156_HRV30a  CATACTAGTAATGTTCAACCTGAAGATGTCATTGAAACTAGATATGTTCAAACATCACAA
2635 157_HRV30b  CATACTAGTAATGTTCAACCTGAAGATGTCATTGAAACTAGATATGTTCAAACATCACAA
2636 158_HRV30   CATACTAGTAATGTTCAACCTGAAGATGTCATTGAAACTAGATATGTTCAAACATCACAA
2637 GROUP_2     CA-ACTAG-A-TGT-CAACC-GA-GATGTCATTGAAAC-AG-TA-GT-CA-ACATCACAA
2638
2639 147_HRV2    ACAAGAGATGAAATGAGTTTAGAGAGTTTTCTTGGCAGATCAGGATGCATACATGAATCT
2640 148_HRV2a|  ACAAGAGATGAAATGAGTTTAGAGAGTTTTCTTGGCAGATCAGGATGCATACATGAATCT
2641 149_HRV2b|  ACAAGAGATGAAATGAGTTTAGAGAGTTTTCTTGGCAGATCAGGATGCATACATGAATCT
2642 150_HRV49a  ACAAGAGATGAAATGAGTTTAGAGAGTTTTCTTGGTAGGTCAGGGTGTATACATGAATCC
2643 151_HRV49b  ACAAGAGATGAAATGAGTTTAGAGAGTTTTCTTGGTAGGTCAGGGTGTATACATGAATCC
2644 152_HRV49   ACAAGAGATGAAATGAGTTTAGAGAGTTTTCTTGGTAGGTCAGGGTGTATACATGAATCC
2645 153_HRV23a  ACAAGAGATGAAATGAGTTTAGAAAGTTTCCTTGGTAGGTCAGGGTGTATACATGAATCT
2646 154_HRV23b  ACAAGAGATGAAATGAGTTTAGAAAGTTTCCTTGGTAGGTCAGGGTGTATACATGAATCT
2647 155_HRV23   ACAAGAGATGAAATGAGTTTAGAAAGTTTCCTTGGTAGGTCAGGGTGTATACATGAATCT
2648 156_HRV30a  ACAAGGGATGAAATGAGTTTAGAAAGCTTTCTTGGTAGATCAGGATGTATACACGAGTCT
2649 157_HRV30b  ACAAGGGATGAAATGAGTTTAGAAAGCTTTCTTGGTAGATCAGGATGTATACACGAGTCT
2650 158_HRV30   ACAAGGGATGAAATGAGTTTAGAAAGCTTTCTTGGTAGATCAGGATGTATACACGAGTCT
2651 GROUP_2     ACAAG-GATGAAATGAGTTTAGA-AG-TT-CTTGG-AG-TCAGG-TG-ATACA-GA-TC-
2652
2653 147_HRV2    AAATTAGAGGTTACACTTGCAAAT---------------TATAACA---------AGGAG
2654 148_HRV2a|  AAATTAGAGGTTACACTTGCAAAT---------------TATAACA---------AGGAG
2655 149_HRV2b|  AAATTAGAGGTTACACTTGCAAAT---------------TATAACA---------AGGAG
2656 150_HRV49a  AAACTAGAGGTCACACTTACAAAT---------------TACAATG---------AAAAT
2657 151_HRV49b  AAACTAGAGGTCACACTTACAAAT---------------TACAATG---------AAAAT
2658 152_HRV49   AAACTAGAGGTCACACTTACAAAT---------------TACAATG---------AAAAT
2659 153_HRV23a  AAATTAAAAGTTGAGATCGGAAAC---------------TATGATG---------AAAAC
2660 154_HRV23b  AAATTAAAAGTTGAGATCGGAAAC---------------TATGATG---------AAAAC
2661 155_HRV23   AAATTAAAAGTTGAGATCGGAAAC---------------TATGATG---------AAAAC
2662 156_HRV30a  AAATTAGAACTTGAGCTTGCACAC---------------TATGATA---------AAAAG
2663 157_HRV30b  AAATTAGAACTTGAGCTTGCACAC---------------TATGATA---------AAAAG
2664 158_HRV30   AAATTAGAACTTGAGCTTGCACAC---------------TATGATA---------AAAAG
2665 GROUP_2     AAA-TA-A--T-----T---A-A-...........TA--A--.........A--A-
```

FIG. D12 CONT'D

```
08.trace                                                                    9/20/2007 5:05 PM 2666
2667 147_HRV2     AATTTTACAGTGTGGGCTATTAATATACAAGAAATGGCTCAAATTAGAAGGAAATTTGAA
2668 148_HRV2a|   AATTTTACAGTGTGGGCTATTAATATACAAGAAATGGCTCAAATTAGAAGGAAATTTGAA
2669 149_HRV2b|   AATTTTACAGTGTGGGCTATTAATATACAAGAAATGGCTCAAATTAGAAGGAAATTTGAA
2670 150_HRV49a   AATTTCAAAGTATGGAACATCAATTTGCAAGAAATGGCCCAGATCAGAAGAAAATTTGAA
2671 151_HRV49b   AATTTCAAAGTATGGAACATCAATTTGCAAGAAATGGCCCAGATCAGAAGAAAATTTGAA
2672 152_HRV49    AATTTCAAAGTATGGAACATCAATTTGCAAGAAATGGCCCAGATCAGAAGAAAATTTGAA
2673 153_HRV23a   AATTTTAATACTTGGAATATTAATTTACAGGAAATGGCCCAAATCAGAAGAAAGTTTGAA
2674 154_HRV23b   AATTTTAATACTTGGAATATTAATTTACAGGAAATGGCCCAAATCAGAAGAAAGTTTGAA
2675 155_HRV23    AATTTTAATACTTGGAATATTAATTTACAGGAAATGGCCCAAATCAGAAGAAAGTTTGAA
2676 156_HRV30a   AACTTTACCACATGGAATATTAATCTTCAAGAAATGGCCCAAATTAGAAGAAAATTTGAG
2677 157_HRV30b   AACTTTACCACATGGAATATTAATCTTCAAGAAATGGCCCAAATTAGAAGAAAATTTGAG
2678 158_HRV30    AACTTTACCACATGGAATATTAATCTTCAAGAAATGGCCCAAATTAGAAGAAAATTTGAG
2679 GROUP_2      AA-TT-A-----TGG---AT-AAT-T-CA-GAAATGGC-CA-AT-AGAAG-AA-TTTGA-
2680
2681 147_HRV2     TTGTTCACCTATACTAGGTTTGATTCTGAAATAACCCTAG-TTCCATGCATTTCCGCCCT
2682 148_HRV2a|   TTGTTCACCTATACTAGGTTTGATTCTGAAATAACCCTAG-TTCCATGCATTTCCGCCCT
2683 149_HRV2b|   TTGTTCACCTATACTAGGTTTGATTCTGAAATAACCCTAG-TTCCATGCATTTCCGCCCT
2684 150_HRV49a   CTGTTTACTTACACTAGATTCGATTCTGAAATAACCTTGG-TTCCATGCATTTCTGCACT
2685 151_HRV49b   CTGTTTACTTACACTAGATTCGATTCTGAAATAACCTTGG-TTCCATGCATTTCTGCACT
2686 152_HRV49    CTGTTTACTTACACTAGATTCGATTCTGAAATAACCTTGG-TTCCATGCATTTCTGCACT
2687 153_HRV23a   CTGTTTACTTACACTAGATTTGATTCTGAAATTACTTTGG-TTCCATGCATTTCTGCTCT
2688 154_HRV23b   CTGTTTACTTACACTAGATTTGATTCTGAAATTACTTTGG-TTCCATGCATTTCTGCTCT
2689 155_HRV23    CTGTTTACTTACACTAGATTTGATTCTGAAATTACTTTGG-TTCCATGCATTTCTGCTCT
2690 156_HRV30a   CTATTCACTTACACTAGATTTGATTCTGAGATAACCTTGG-TTCCGTGTATTTCAGCTCT
2691 157_HRV30b   CTATTCACTTACACTAGATTTGATTCTGAGATAACCTTGG-TTCCGTGTATTTCAGCTCT
2692 158_HRV30    CTATTCACTTACACTAGATTTGATTCTGAGATAACCTTGG-TTCCGTGTATTTCAGCTCT
2693 GROUP_2      -T-TT-AC-TA-ACTAG-TT-GATTCTGA-AT-AC--T-G.TTCC-TG-ATTTC-GC-CT
2694
2695 147_HRV2     TAGTCAGGACATTGGACACATCACAATGCAATACATGTATGTTCCACCTGGTGCACCGGT
2696 148_HRV2a|   TAGTCAGGACATTGGACACATCACAATGCAATACATGTATGTTCCACCTGGTGCACCGGT
2697 149_HRV2b|   TAGTCAGGACATTGGACACATCACAATGCAATACATGTATGTTCCACCTGGTGCACCGGT
2698 150_HRV49a   TAGCAAGGATATTGGACACATTACAATGCAATACATGTATGTGCCGCCAGGTGCACCTGT
2699 151_HRV49b   TAGCAAGGATATTGGACACATTACAATGCAATACATGTATGTGCCGCCAGGTGCACCTGT
2700 152_HRV49    TAGCAAGGATATTGGACACATTACAATGCAATACATGTATGTGCCGCCAGGTGCACCTGT
2701 153_HRV23a   TAGTCAAGATATTGGTCACATCACAATGCAGTATATGTATGTCCCACCAGGTGCTCCAAT
2702 154_HRV23b   TAGTCAAGATATTGGTCACATCACAATGCAGTATATGTATGTCCCACCAGGTGCTCCAAT
2703 155_HRV23    TAGTCAAGATATTGGTCACATCACAATGCAGTATATGTATGTCCCACCAGGTGCTCCAAT
2704 156_HRV30a   CAGCCAAGATATCGGACACATTACAATGCAGTATATGTATGTTCCACCTGGCGCTCCAAT
2705 157_HRV30b   CAGCCAAGATATCGGACACATTACAATGCAGTATATGTATGTTCCACCTGGCGCTCCAAT
2706 158_HRV30    CAGCCAAGATATCGGACACATTACAATGCAGTATATGTATGTTCCACCTGGCGCTCCAAT
2707 GROUP_2      -AG--A-GA-AT-GG-CACAT-ACAATGCA-TA-ATGTATGT-CC-CC-GG-GC-CC--T
2708
2709 147_HRV2     GCCCAATAGTAGGGACGATTATGCATGGCAGTCTGGCACTAATGCCTCTGTTTTCTGGCA
2710 148_HRV2a|   GCCCAATAGTAGGGACGATTATGCATGGCAGTCTGGCACTAATGCCTCTGTTTTCTGGCA
2711 149_HRV2b|   GCCCAATAGTAGGGACGATTATGCATGGCAGTCTGGCACTAATGCCTCTGTTTTCTGGCA
2712 150_HRV49a   ACCAAAGAGCAGAGATGATTATGCATGGCAGTCTGGCACTAATGCATCTGTTTTCTGGCA
2713 151_HRV49b   ACCAAAGAGCAGAGATGATTATGCATGGCAGTCTGGCACTAATGCATCTGTTTTCTGGCA
2714 152_HRV49    ACCAAAGAGCAGAGATGATTATGCATGGCAGTCTGGCACTAATGCATCTGTTTTCTGGCA
2715 153_HRV23a   ACCGGAAAGTAGAAATGACTATGCATGGCAATCTGGAACAAATGCGTCCATTTTTTGGCA
2716 154_HRV23b   ACCGGAAAGTAGAAATGACTATGCATGGCAATCTGGAACAAATGCGTCCATTTTTTGGCA
2717 155_HRV23    ACCGGAAAGTAGAAATGACTATGCATGGCAATCTGGAACAAATGCGTCCATTTTTTGGCA
2718 156_HRV30a   TCCCGAGAGCAGAAATGACTATGCATGGCAGTCTGGAACAAATGCATCTGTTTTTTGGCA
2719 157_HRV30b   TCCCGAGAGCAGAAATGACTATGCATGGCAGTCTGGAACAAATGCATCTGTTTTTTGGCA
2720 158_HRV30    TCCCGAGAGCAGAAATGACTATGCATGGCAGTCTGGAACAAATGCATCTGTTTTTTGGCA
2721 GROUP_2      -CC--A-AG-AG--A-GA-TATGCATGGCA-TCTGG-AC-AATGC-TC--TTTT-TGGCA
2722
2723 147_HRV2     ACATGGACAGGCTTATCCAAGATTTTCCTTACCTTTCCTAAGTGTGGCATCTGCTTATTA
2724 148_HRV2a|   ACATGGACAGGCTTATCCAAGATTTTCCTTACCTTTCCTAAGTGTGGCATCTGCTTATTA
2725 149_HRV2b|   ACATGGACAGGCTTATCCAAGATTTTCCTTACCTTTCCTAAGTGTGGCATCTGCTTATTA
2726 150_HRV49a   ACATGGGCAAGCATACCCAAGATTTTCTCTACCCTTTTGAGTGTAGCTTCAGCTTACTA
2727 151_HRV49b   ACATGGGCAAGCATACCCAAGATTTTCTCTACCCTTTTGAGTGTAGCTTCAGCTTACTA
2728 152_HRV49    ACATGGGCAAGCATACCCAAGATTTTCTCTACCCTTTTGAGTGTAGCTTCAGCTTACTA
2729 153_HRV23a   ACATGGACAAACATATCCAAGGTTCTCCTTACCCTTTTGAGTGTGGCATCTGCTTATTA
2730 154_HRV23b   ACATGGACAAACATATCCAAGGTTCTCCTTACCCTTTTGAGTGTGGCATCTGCTTATTA
```

FIG. D12 CONT'D

```
08.trace                                                                                    9/20/2007 5:05 PM 2731  155_HRV23    ACATGGACAAACATATCCAAGGTTCTCCTTACCCTTTTTGAGTGTGGCATCTGCTTATTA
2732  156_HRV30a   ACACGGACAAACATACCCAAGATTCTCCCTACCATTTTTGAGTGTAGCATCTGCTTATTA
2733  157_HRV30b   ACACGGACAAACATACCCAAGATTCTCCCTACCATTTTTGAGTGTAGCATCTGCTTATTA
2734  158_HRV30    ACACGGACAAACATACCCAAGATTCTCCCTACCATTTTTGAGTGTAGCATCTGCTTATTA
2735  GROUP_2      ACA-GG-CA--C-TA-CCAAG-TT-TC--TACC-TT--T-AGTGT-GC-TC-GCTTA-TA
2736
2737  147_HRV2     CATGTTTTATGATGGGTATGATG------AACAAGATCAAAACTATGGTACAGCAAGCAC
2738  148_HRV2a|   CATGTTTTATGATGGGTATGATG------AACAAGATCAAAACTATGGTACAGCAAGCAC
2739  149_HRV2b|   CATGTTTTATGATGGGTATGATG------AACAAGATCAAAACTATGGTACAGCAAGCAC
2740  150_HRV49a   CATGTTTTATGATGGATATAATG------AACAGGGCCAAAATTATGGTACGGTAAGTAC
2741  151_HRV49b   CATGTTTTATGATGGATATAATG------AACAGGGCCAAAATTATGGTACGGTAAGTAC
2742  152_HRV49    CATGTTTTATGATGGATATAATG------AACAGGGCCAAAATTATGGTACGGTAAGTAC
2743  153_HRV23a   CATGTTTTATGATGGATACAATG------AGAAAGGCACGCATTATGGAACAGTTAGCAC
2744  154_HRV23b   CATGTTTTATGATGGATACAATG------AGAAAGGCACGCATTATGGAACAGTTAGCAC
2745  155_HRV23    CATGTTTTATGATGGATACAATG------AGAAAGGCACGCATTATGGAACAGTTAGCAC
2746  156_HRV30a   CATGTTCTATGATGGATACAATG------AGGGAGGCACAAATTATGGTACAGTGAGCAC
2747  157_HRV30b   CATGTTCTATGATGGATACAATG------AGGGAGGCACAAATTATGGTACAGTGAGCAC
2748  158_HRV30    CATGTTCTATGATGGATACAATG------AGGGAGGCACAAATTATGGTACAGTGAGCAC
2749  GROUP_2      CATGTT-TATGATGG-TA--ATG......A----G------A-TATGG-AC-G--AG-AC
2750
2751  147_HRV2     AAATAACATGGGGTCACTATGCTCTAGGATAGTAACAGAGAAACACATTCATAAGGTACA
2752  148_HRV2a|   AAATAACATGGGGTCACTATGCTCTAGGATAGTAACAGAGAAACACATTCATAAGGTACA
2753  149_HRV2b|   AAATAACATGGGGTCACTATGCTCTAGGATAGTAACAGAGAAACACATTCATAAGGTACA
2754  150_HRV49a   AAACAACATGGGATCATTATGCTCTAGGATAGTAACAGAGAAACACATTCACAGTATGCA
2755  151_HRV49b   AAACAACATGGGATCATTATGCTCTAGGATAGTAACAGAGAAACACATTCACAGTATGCA
2756  152_HRV49    AAACAACATGGGATCATTATGCTCTAGGATAGTAACAGAGAAACACATTCACAGTATGCA
2757  153_HRV23a   AAACAACATGGGCACATTGTGCTCCAGAGTGGTAACAGAGAAACACATTCATGATATGCG
2758  154_HRV23b   AAACAACATGGGCACATTGTGCTCCAGAGTGGTAACAGAGAAACACATTCATGATATGCG
2759  155_HRV23    AAACAACATGGGCACATTGTGCTCCAGAGTGGTAACAGAGAAACACATTCATGATATGCG
2760  156_HRV30a   AAACAACATGGGCACACTGTGTTCCAGAGTGGTAACAGAAAAACACATTCATGATGTGCG
2761  157_HRV30b   AAACAACATGGGCACACTGTGTTCCAGAGTGGTAACAGAAAAACACATTCATGATGTGCG
2762  158_HRV30    AAACAACATGGGCACACTGTGTTCCAGAGTGGTAACAGAAAAACACATTCATGATGTGCG
2763  GROUP_2      AAA-AACATGGG--CA-T-TG-TC-AG---T-GTAACAGA-AAACACATTCA-----T-C-
2764
2765  147_HRV2     TATAATGACAAGAATCTATCACAAGGCTAAACATGTCAAGGCATGGTGTCCACGCCCACC
2766  148_HRV2a|   TATAATGACAAGAATCTATCACAAGGCTAAACATGTCAAGGCATGGTGTCCACGCCCACC
2767  149_HRV2b|   TATAATGACAAGAATCTATCACAAGGCTAAACATGTCAAGGCATGGTGTCCACGCCCACC
2768  150_HRV49a   TATCATGACAAGAATCTATCATAAAGCTAAACACGTCAAAGCATGGTGTCCGCGCCCACC
2769  151_HRV49b   TATCATGACAAGAATCTATCATAAAGCTAAACACGTCAAAGCATGGTGTCCGCGCCCACC
2770  152_HRV49    TATCATGACAAGAATCTATCATAAAGCTAAACACGTCAAAGCATGGTGTCCGCGCCCACC
2771  153_HRV23a   GATAATGACAAGGGTCTACCACAAAGCTAAACATGTCAAAGCATGGTGTCCGCGGCCACC
2772  154_HRV23b   GATAATGACAAGGGTCTACCACAAAGCTAAACATGTCAAAGCATGGTGTCCGCGGCCACC
2773  155_HRV23    GATAATGACAAGGGTCTACCACAAAGCTAAACATGTCAAAGCATGGTGTCCGCGGCCACC
2774  156_HRV30a   CATAATGACAAGGGTCTACCACAAGGCTAAACATGTCAAAGCGTGGTGTCCACGGCCACC
2775  157_HRV30b   CATAATGACAAGGGTCTACCACAAGGCTAAACATGTCAAAGCGTGGTGTCCACGGCCACC
2776  158_HRV30    CATAATGACAAGGGTCTACCACAAGGCTAAACATGTCAAAGCGTGGTGTCCACGGCCACC
2777  GROUP_2      -AT-ATGACAAG--TCTA-CA-AA-GCTAAACA-GTCAA-GC-TGGTGTCC-CG-CCACC
2778
2779  147_HRV2     CAGAGCGCTTGAGTATACT-CGTGCTCACCGCACTAATTTTAAAA-TTGAGG---ATAGG
2780  148_HRV2a|   CAGAGCGCTTGAGTATACT-CGTGCTCACCGCACTAATTTTAAAA-TTGAGG---ATAGG
2781  149_HRV2b|   CAGAGCGCTTGAGTATACT-CGTGCTCACCGCACTAATTTTAAAA-TTGAGG---ATAGG
2782  150_HRV49a   CAGAGCACTTGAATATACT-CGCGCTCACCGTACTAATTTCAAAG-TTGAAG---ACAGA
2783  151_HRV49b   CAGAGCACTTGAATATACT-CGCGCTCACCGTACTAATTTCAAAG-TTGAAG---ACAGA
2784  152_HRV49    CAGAGCACTTGAATATACT-CGCGCTCACCGTACTAATTTCAAAG-TTGAAG---ACAGA
2785  153_HRV23a   CAGAGCACTTGAATACACA-CGCGCTCACCGTACTAATTTCAAAA-TTGAAG---GTGAA
2786  154_HRV23b   CAGAGCACTTGAATACACA-CGCGCTCACCGTACTAATTTCAAAA-TTGAAG---GTGAA
2787  155_HRV23    CAGAGCACTTGAATACACA-CGCGCTCACCGTACTAATTTCAAAA-TTGAAG---GTGAA
2788  156_HRV30a   TAGGGCGCTTGAGTATACC-CGTGCTCATCGCACCAATTTTAAAA-TTGATG---GCAGG
2789  157_HRV30b   TAGGGCGCTTGAGTATACC-CGTGCTCATCGCACCAATTTTAAAA-TTGATG---GCAGG
2790  158_HRV30    TAGGGCGCTTGAGTATACC-CGTGCTCATCGCACCAATTTTAAAA-TTGATG---GCAGG
2791  GROUP_2      -AG-GC-CTTGA-TA-AC-.CG-GCTCA-CG-AC-AATTT-AAA-.TTGA-G...-----
2792
2793  147_HRV2     AGTA------TTCAGACAG---CAATTGTGACCAGACCAATTATCACTACAGCT------
2794  148_HRV2a|   AGTA------TTCAGACAG---CAATTGTGACCAGACCAATTATCACTACAGCA------
2795  149_HRV2b|   AGTA------TTCAGACAG---CAATTGTGACCAGACCAATTATCACTACAGCG------
```

FIG. D12 CONT'D

```
08.trace                                                              9/20/2007 5:05 PM 2796 150_HRV49a   GACA------TTAAAACAG---GAATCACATCCAGAGCAATTATTACAACAGCG------
2797 151_HRV49b   GACA------TTAAAACAG---GAATCACATCCAGAGCAATTATTACAACAGCA------
2798 152_HRV49    GACA------TTAAAACAG---GAATCACATCCAGAGCAATTATTACAACAGCT------
2799 153_HRV23a   AATG------TCAAATCAA---GGGTTGCACATAGACCTGCAGTGATAACAGCG------
2800 154_HRV23b   AATG------TCAAATCAA---GGGTTGCACATAGACCTGCAGTGATAACAGCA------
2801 155_HRV23    AATG------TCAAATCAA---GGGTTGCACATAGACCTGCAGTGATAACAGCT------
2802 156_HRV30a   GAAG------TTAAATCAA---GGGTTGAACACAGAGCTAGGGTGACGACAGCA------
2803 157_HRV30b   GAAG------TTAAATCAA---GGGTTGAACACAGAGCTAGGGTGACGACAGCG------
2804 158_HRV30    GAAG------TTAAATCAA---GGGTTGAACACAGAGCTAGGGTGACGACAGCT------
2805 GROUP_2      ----......T--A--CA-...---T-------AGA-C-----T-A--ACAGC-......
2806
2807 147_HRV2     --------------------
2808 148_HRV2a|   --------------------
2809 149_HRV2b|   --------------------
2810 150_HRV49a   --------------------
2811 151_HRV49b   --------------------
2812 152_HRV49    --------------------
2813 153_HRV23a   --------------------
2814 154_HRV23b   --------------------
2815 155_HRV23    --------------------
2816 156_HRV30a   --------------------
2817 157_HRV30b   --------------------
2818 158_HRV30    --------------------
2819 GROUP_2      ....................
2820
2821
2822
2823 Group 3:
2824
2825 159_HRV7     AACCCGGTAGAGAATTATGTAGATAGCTTACTAAATGAAGTATTAGTGGTACCTAATATT
2826 160_HRV7b|   AACCCGGTAGAGAATTATGTAGATAGCTTACTAAATGAAGTATTAGTGGTACCTAATATT
2827 161_HRV7a|   AACCCGGTAGAGAATTATGTAGATAGCTTACTAAATGAAGTATTAGTGGTACCTAATATT
2828 162_HRV88    AATCCAGTAGAAAACTATGTAGATAACTTGTTAAACGAAGTGCTAGTAGTTCCTAACATT
2829 163_HRV88a   AATCCAGTAGAAAACTATGTAGATAACTTGTTAAACGAAGTGCTAGTAGTTCCTAACATT
2830 164_HRV88b   AATCCAGTAGAAAACTATGTAGATAACTTGTTAAACGAAGTGCTAGTAGTTCCTAACATT
2831 165_HRV36a   AATCCAGTTGAAAATTACATAGATAATGTATTAAATGAAGTACTTGTAGTGCCAAACATC
2832 166_HRV36b   AATCCAGTTGAAAATTACATAGATAATGTATTAAATGAAGTACTTGTAGTGCCAAACATC
2833 167_HRV36    AATCCAGTTGAAAATTACATAGATAATGTATTAAATGAAGTACTTGTAGTGCCAAACATC
2834 168_HRV89a   AACCCAGTTGAAAATTATATAGATAGTGTATTAAATGAAGTTCTTGTGGTGCCAAATATC
2835 169_HRV89b   AACCCAGTTGAAAATTATATAGATAGTGTATTAAATGAAGTTCTTGTGGTGCCAAATATC
2836 170_HRV89    AACCCAGTTGAAAATTATATAGATAGTGTATTAAATGAAGTTCTTGTGGTGCCAAATATC
2837 171_HRV58    AATCCAGTAGAAAATTACATAGATAATGTTTAAATGAAGTACTTGTAGTTCCAAATATC
2838 172_HRV58a   AATCCAGTAGAAAATTACATAGATAATGTGTTAAATGAAGTACTTGTAGTTCCAAATATC
2839 173_HRV58b   AATCCAGTAGAAAATTACATAGATAATGTGTTAAATGAAGTACTTGTAGTTCCAAATATC
2840 GROUP_3      AA-CC-GT-GA-AA-TA--TAGATA---T--TAAA-GAAGT--T-GT-GT-CC-AA-AT-
2841
2842 159_HRV7     CAGCCAAGTACATCTGTTTCAAGTCACTCTGTACCAGCATTGGATGCTGCAGAGACTGGA
2843 160_HRV7b|   CAGCCAAGTACATCTGTTTCAAGTCACTCTGTACCAGCATTGGATGCTGCAGAGACTGGA
2844 161_HRV7a|   CAGCCAAGTACATCTGTTTCAAGTCACTCTGTACCAGCATTGGATGCTGCAGAGACTGGA
2845 162_HRV88    CAACCTAGCACATCCGTTTCAAGTCACTCTGTGCCAGCTCTGGATGCTGCGGAAACAGGG
2846 163_HRV88a   CAACCTAGCACATCCGTTTCAAGTCACTCTGTGCCAGCTCTGGATGCTGCGGAAACAGGG
2847 164_HRV88b   CAACCTAGCACATCCGTTTCAAGTCACTCTGTGCCAGCTCTGGATGCTGCGGAAACAGGG
2848 165_HRV36a   CAACCTAGTTCATCTGTGTCAAGTCATTCAGCTCCCGCCTTAGACGCTGCGGAAACTGGA
2849 166_HRV36b   CAACCTAGTTCATCTGTGTCAAGTCATTCAGCTCCCGCCTTAGACGCTGCGGAAACTGGA
2850 167_HRV36    CAACCTAGTTCATCTGTGTCAAGTCATTCAGCTCCCGCCTTAGACGCTGCGGAAACTGGA
2851 168_HRV89a   CAACCTAGCACATCTGTGTCAAGTCATGCAGCGCCTGCATTGGATGCTGCGGAAACCGGA
2852 169_HRV89b   CAACCTAGCACATCTGTGTCAAGTCATGCAGCGCCTGCATTGGATGCTGCGGAAACCGGA
2853 170_HRV89    CAACCTAGCACATCTGTGTCAAGTCATGCAGCGCCTGCATTGGATGCTGCGGAAACCGGA
2854 171_HRV58    CAACCTAGTACATCTGTATCAAGTCATTCTGTGCCTGCCTTGGATGCTGCAGAAACGGGA
2855 172_HRV58a   CAACCTAGTACATCTGTATCAAGTCATTCTGTGCCTGCCTTGGATGCTGCAGAAACGGGA
2856 173_HRV58b   CAACCTAGTACATCTGTATCAAGTCATTCTGTGCCTGCCTTGGATGCTGCAGAAACGGGA
2857 GROUP_3      CA-CC-AG--CATC-GT-TCAAGTCA--C-G--CC-GC--T-GA-GCTGC-GA--AC-GG-
2858
2859 159_HRV7     CATACTAGTTCTGTTCAACCTGAAGATATGATCGAGACAAGGTATGTCATAACAGACCAA
2860 160_HRV7b|   CATACTAGTTCTGTTCAACCTGAAGATATGATCGAGACAAGGTATGTCATAACAGACCAA
```

FIG. D12 CONT'D

08.trace                                                                9/20/2007 5:05 PM

```
2861 161_HRV7a|  CATACTAGTTCTGTTCAACCTGAAGATATGATCGAGACAAGGTATGTCATAACAGACCAA
2862 162_HRV88   CATACTAGTTCTGTTCAACCTGAAGATATGATAGAAACTAGATATGTTATAACAGATCAA
2863 163_HRV88a  CATACTAGTTCTGTTCAACCTGAAGATATGATAGAAACTAGATATGTTATAACAGATCAA
2864 164_HRV88b  CATACTAGTTCTGTTCAACCTGAAGATATGATAGAAACTAGATATGTTATAACAGATCAA
2865 165_HRV36a  CATACCAGCTCTGTCCAACCAGAGGACATGATCGAGACCAGATATGTCATAACTGATCAA
2866 166_HRV36b  CATACCAGCTCTGTCCAACCAGAGGACATGATCGAGACCAGATATGTCATAACTGATCAA
2867 167_HRV36   CATACCAGCTCTGTCCAACCAGAGGACATGATCGAGACCAGATATGTCATAACTGATCAA
2868 168_HRV89a  CACACCAGCTCTGTTCAACCTGAACATAGATTGAAACTAGATATGTTATAACTGATCAA
2869 169_HRV89b  CACACCAGCTCTGTTCAACCTGAAGATATGATTGAAACTAGATATGTTATAACTGATCAA
2870 170_HRV89   CACACCAGCTCTGTTCAACCTGAAGATATGATTGAAACTAGATATGTTATAACTGATCAA
2871 171_HRV58   CACACAAGTTCTGTTCAGCCTGAGGATATGATTGAAACTAGATATGTTATCACAGATCAA
2872 172_HRV58a  CACACAAGTTCTGTTCAGCCTGAGGATATGATTGAAACTAGATATGTTATCACAGATCAA
2873 173_HRV58b  CACACAAGTTCTGTTCAGCCTGAGGATATGATTGAAACTAGATATGTTATCACAGATCAA
2874 GROUP_3     CA-AC-AG-TCTGT-CA-CC-GA-GA-ATGAT-GA-AC-AG-TATGT-AT-AC-GA-CAA
2875
2876 159_HRV7    ACAAGGGATGAAACTAGTATAGAGAGTTTCTTAGGTAGATCTGGATGTATTGCTAAAGTT
2877 160_HRV7b|  ACAAGGGATGAAACTAGTATAGAGAGTTTCTTAGGTAGATCTGGATGTATTGCTAAAGTT
2878 161_HRV7a|  ACAAGGGATGAAACTAGTATAGAGAGTTTCTTAGGTAGATCTGGATGTATTGCTAAAGTT
2879 162_HRV88   ACAAGGGATGAAACCAGCATTGAAAGCTTTCTGGGTAGGTCTGGATGCATAGCAAAAATT
2880 163_HRV88a  ACAAGGGATGAAACCAGCATTGAAAGCTTTCTGGGTAGGTCTGGATGCATAGCAAAAATT
2881 164_HRV88b  ACAAGGGATGAAACCAGCATTGAAAGCTTTCTGGGTAGGTCTGGATGCATAGCAAAAATT
2882 165_HRV36a  ACAAGAGATGAGACAAGTATTGAAAGCTTCTTAGGTAGGTCAGGGTGCATAGCTATGATA
2883 166_HRV36b  ACAAGAGATGAGACAAGTATTGAAAGCTTCTTAGGTAGGTCAGGGTGCATAGCTATGATA
2884 167_HRV36   ACAAGAGATGAGACAAGTATTGAAAGCTTCTTAGGTAGGTCAGGGTGCATAGCTATGATA
2885 168_HRV89a  ACAAGGGATGAAACAAGTATTGAGAGTTTCTTAGGTAGGTCAGGGTGTATCGCTATGATA
2886 169_HRV89b  ACAAGGGATGAAACAAGTATTGAGAGTTTCTTAGGTAGGTCAGGGTGTATCGCTATGATA
2887 170_HRV89   ACAAGGGATGAAACAAGTATTGAGAGTTTCTTAGGTAGGTCAGGGTGTATCGCTATGATA
2888 171_HRV58   ACAAGAGATGAAACTAGCATTGAAAGCTTTTTAGGTAGATCTGGTTGCATTGCTATCATA
2889 172_HRV58a  ACAAGAGATGAAACTAGCATTGAAAGCTTTTTAGGTAGATCTGGTTGCATTGCTATCATA
2890 173_HRV58b  ACAAGAGATGAAACTAGCATTGAAAGCTTTTTAGGTAGATCTGGTTGCATTGCTATCATA
2891 GROUP_3     ACAAG-GATGA-AC-AG-AT-GA-AG-TT--T-GGTAG-TC-GG-TG-AT-GC-A---T-
2892
2893 159_HRV7    AAACTTGACACAA------CACAGGGT---------GACTATGACACAGGCAAAGGTGTT
2894 160_HRV7b|  AAACTTGACACAA------CACAGGGT---------GACTATGACACAGGCAAAGGTGTT
2895 161_HRV7a|  AAACTTGACACAA------CACAGGGT---------GACTATGACACAGGCAAAGGTGTT
2896 162_HRV88   AAACTTGACACAA------ATGAAGGT---------GATTACGACACA---ATAGGTGTT
2897 163_HRV88a  AAACTTGACACAA------ATGAAGGT---------GATTACGACACA---ATAGGTGTT
2898 164_HRV88b  AAACTTGACACAA------ATGAAGGT---------GATTACGACACA---ATAGGTGTT
2899 165_HRV36a  GAATTTAGCACAAGTAGTGATAAAGAT---------GAACATGATGAA---ATTGGCAAG
2900 166_HRV36b  GAATTTAGCACAAGTAGTGATAAAGAT---------GAACATGATGAA---ATTGGCAAG
2901 167_HRV36   GAATTTAGCACAAGTAGTGATAAAGAT---------GAACATGATGAA---ATTGGCAAG
2902 168_HRV89a  GAATTTAATACAAGTAGTGATAAAACT---------GAACATGATAAA---ATTGGTAAA
2903 169_HRV89b  GAATTTAATACAAGTAGTGATAAAACT---------GAACATGATAAA---ATTGGTAAA
2904 170_HRV89   GAATTTAATACAAGTAGTGATAAAACT---------GAACATGATAAA---ATTGGTAAA
2905 171_HRV58   AAATTTAACACAA------ATAAGACT---------AATTATGATGAC---ATAGGTGTA
2906 172_HRV58a  AAATTTAACACAA------ATAAGACT---------AATTATGATGAC---ATAGGTGTA
2907 173_HRV58b  AAATTTAACACAA------ATAAGACT---------AATTATGATGAC---ATAGGTGTA
2908 GROUP_3     -AA-TT---ACAA----------A---T.........-A--A-GA-------A--GG----
2909
2910 159_HRV7    GGTTTCACTACATGGAAAATCAGCTTACAAGAAATGGCACAAATCAGAAGAAAGTTTGAA
2911 160_HRV7b|  GGTTTCACTACATGGAAAATCAGCTTACAAGAAATGGCACAAATCAGAAGAAAGTTTGAA
2912 161_HRV7a|  GGTTTCACTACATGGAAAATCAGCTTACAAGAAATGGCACAAATCAGAAGAAAGTTTGAA
2913 162_HRV88   GGATTTGTAACATGGAAGATTAGCTTGCAAGAAATGGCACAAATCAGGAGAAAATTTGAA
2914 163_HRV88a  GGATTTGTAACATGGAAGATTAGCTTGCAAGAAATGGCACAAATCAGGAGAAAATTTGAA
2915 164_HRV88b  GGATTTGTAACATGGAAGATTAGCTTGCAAGAAATGGCACAAATCAGGAGAAAATTTGAA
2916 165_HRV36a  GGATTCAAAACATGGAAGATTAGTCTTCAAGAAATGGCACAAATTAGAAGGAAATATGAA
2917 166_HRV36b  GGATTCAAAACATGGAAGATTAGTCTTCAAGAAATGGCACAAATTAGAAGGAAATATGAA
2918 167_HRV36   GGATTCAAAACATGGAAGATTAGTCTTCAAGAAATGGCACAAATTAGAAGGAAATATGAA
2919 168_HRV89a  GGATTCAAAACATGGAAGGTTAGTCTTCAAGAAATGGCACAAATCAGAAGAAAAATATGAA
2920 169_HRV89b  GGATTCAAAACATGGAAGGTTAGTCTTCAAGAAATGGCACAAATCAGAAGAAAAATATGAA
2921 170_HRV89   GGATTCAAAACATGGAAGGTTAGTCTTCAAGAAATGGCACAAATCAGAAGAAAAATATGAA
2922 171_HRV58   GGATACAAAACATGGAAAATTAGCCTTCAAGAGATGGCACAAATTAGAAGGAAATTTGAG
2923 172_HRV58a  GGATACAAAACATGGAAAATTAGCCTTCAAGAGATGGCACAAATTAGAAGGAAATTTGAG
2924 173_HRV58b  GGATACAAAACATGGAAAATTAGCCTTCAAGAGATGGCACAAATTAGAAGGAAATTTGAG
2925 GROUP_3     GG-T-----ACATGGAA--T-AG--T-CAAGA-ATGGCACAAAT-AG-AG-AA-T-TGA-
```

FIG. D12 CONT'D

```
08.trace                                                                9/20/2007 5:05 PM 2926
2927 159_HRV7    CTATTCACATACACTAGATTTGATTCTGAGATAACAATAG-TCACAGCAGCAGCAGCACA
2928 160_HRV7b|  CTATTCACATACACTAGATTTGATTCTGAGATAACAATAG-TCACAGCAGCAGCAGCACA
2929 161_HRV7a|  CTATTCACATACACTAGATTTGATTCTGAGATAACAATAG-TCACAGCAGCAGCAGCACA
2930 162_HRV88   TTGTTTACATACACTAGATTTGACTCAGAAATAACAATAG-TCACAGCAGCTGCAGCACA
2931 163_HRV88a  TTGTTTACATACACTAGATTTGACTCAGAAATAACAATAG-TCACAGCAGCTGCAGCACA
2932 164_HRV88b  TTGTTTACATACACTAGATTTGACTCAGAAATAACAATAG-TCACAGCAGCTGCAGCACA
2933 165_HRV36a  TTGTTTACATACACAAGATTTGACTCAGAAATAACAATAG-TCACCGCAGCTGCAGTGCA
2934 166_HRV36b  TTGTTTACATACACAAGATTTGACTCAGAAATAACAATAG-TCACCGCAGCTGCAGTGCA
2935 167_HRV36   TTGTTTACATACACAAGATTTGACTCAGAAATAACAATAG-TCACCGCAGCTGCAGTGCA
2936 168_HRV89a  TTATTCACATATACAAGATTTGATTCAGAGATAACAATAG-TCACTGCAGCCGCAGCTCA
2937 169_HRV89b  TTATTCACATATACAAGATTTGATTCAGAGATAACAATAG-TCACTGCAGCCGCAGCTCA
2938 170_HRV89   TTATTCACATATACAAGATTTGATTCAGAGATAACAATAG-TCACTGCAGCCGCAGCTCA
2939 171_HRV58   TTGTTTACATATACAAGATTTGACTCAGAGATTACAATAG-TCACTGCAGCAGCTGCTCA
2940 172_HRV58a  TTGTTTACATATACAAGATTTGACTCAGAGATTACAATAG-TCACTGCAGCAGCTGCTCA
2941 173_HRV58b  TTGTTTACATATACAAGATTTGACTCAGAGATTACAATAG-TCACTGCAGCAGCTGCTCA
2942 GROUP_3     -T-TT-ACATA-AC-AGATTTGA-TC-GA-AT-ACAATAG.TCAC-GCAGC-GC-G--CA
2943
2944 159_HRV7    AGGTAATGATATTGGACATATAGTTATGCAATTTATGTATGTACCTCCAGGGGCCCCAGT
2945 160_HRV7b|  AGGTAATGATATTGGACATATAGTTATGCAATTTATGTATGTACCTCCAGGGGCCCCAGT
2946 161_HRV7a|  AGGTAATGATATTGGACATATAGTTATGCAATTTATGTATGTACCTCCAGGGGCCCCAGT
2947 162_HRV88   AGGTGATGATACTGGACATATAGTACTGCAATTCATGTATGTGCCTCCAGGTGCACCAAT
2948 163_HRV88a  AGGTGATGATACTGGACATATAGTACTGCAATTCATGTATGTGCCTCCAGGTGCACCAAT
2949 164_HRV88b  AGGTGATGATACTGGACATATAGTACTGCAATTCATGTATGTGCCTCCAGGTGCACCAAT
2950 165_HRV36a  GGGAGATGATAGTGGGCATGTAGTATTACAATTCATGTATGTACCTCCAGGAGCGCCTGT
2951 166_HRV36b  GGGAGATGATAGTGGGCATGTAGTATTACAATTCATGTATGTACCTCCAGGAGCGCCTGT
2952 167_HRV36   GGGAGATGATAGTGGGCATGTAGTATTACAATTCATGTATGTACCTCCAGGAGCGCCTGT
2953 168_HRV89a  AGGAAATGATAGTGGACATATAGTATTGCAATTTATGTATGTACCCCCAGGAGCACCTGT
2954 169_HRV89b  AGGAAATGATAGTGGACATATAGTATTGCAATTTATGTATGTACCCCCAGGAGCACCTGT
2955 170_HRV89   AGGAAATGATAGTGGACATATAGTATTGCAATTTATGTATGTACCCCCAGGAGCACCTGT
2956 171_HRV58   AGGAGAAGATAATGGACATATTGTGTTACAATTTATGTATGTACCCCCAGGAGCACCTGT
2957 172_HRV58a  AGGAGAAGATAATGGACATATTGTGTTACAATTTATGTATGTACCCCCAGGAGCACCTGT
2958 173_HRV58b  AGGAGAAGATAATGGACATATTGTGTTACAATTTATGTATGTACCCCCAGGAGCACCTGT
2959 GROUP_3     -GG--A-GATA-TGG-CAT-T-GT--T-CAATT-ATGTATGT-CC-CCAGG-GC-CC--T
2960
2961 159_HRV7    TCCAATAAAACGCGAAGATTATACATGGCAATCAGGAACAAATGCTTCTATATTTTGGCA
2962 160_HRV7b|  TCCAATAAAACGCGAAGATTATACATGGCAATCAGGAACAAATGCTTCTATATTTTGGCA
2963 161_HRV7a|  TCCAATAAAACGCGAAGATTATACATGGCAATCAGGAACAAATGCTTCTATATTTTGGCA
2964 162_HRV88   TCCCAAGAAACGTGATGATTACACATGGCAGTCAGGAACAAATGCATCTGTGTTCTGGCA
2965 163_HRV88a  TCCCAAGAAACGTGATGATTACACATGGCAGTCAGGAACAAATGCATCTGTGTTCTGGCA
2966 164_HRV88b  TCCCAAGAAACGTGATGATTACACATGGCAGTCAGGAACAAATGCATCTGTGTTCTGGCA
2967 165_HRV36a  TCCTGTGAAGCGTGATGACTACACATGGCAATCAGGGACAAATGCATCTGTGTTCTGGCA
2968 166_HRV36b  TCCTGTGAAGCGTGATGACTACACATGGCAATCAGGGACAAATGCATCTGTGTTCTGGCA
2969 167_HRV36   TCCTGTGAAGCGTGATGACTACACATGGCAATCAGGGACAAATGCATCTGTGTTCTGGCA
2970 168_HRV89a  CCCCGAAAAACGTGATGATTACACATGGCAATCAGGAACAAATGCATCTGTGTTCTGGCA
2971 169_HRV89b  CCCCGAAAAACGTGATGATTACACATGGCAATCAGGAACAAATGCATCTGTGTTCTGGCA
2972 170_HRV89   CCCCGAAAAACGTGATGATTACACATGGCAATCAGGAACAAATGCATCTGTGTTCTGGCA
2973 171_HRV58   ACCCAAGAATCGTGATGACTTTACATGGCAATCAGGCACAAATGCATCTGTTTTCTGGCA
2974 172_HRV58a  ACCCAAGAATCGTGATGACTTTACATGGCAATCAGGCACAAATGCATCTGTTTTCTGGCA
2975 173_HRV58b  ACCCAAGAATCGTGATGACTTTACATGGCAATCAGGCACAAATGCATCTGTTTTCTGGCA
2976 GROUP_3     -CC----AA-CG-GA-GA-T--ACATGGCA-TCAGG-ACAAATGC-TCT-T-TT-TGGCA
2977
2978 159_HRV7    GGAGGGTCAACCATACCCTAGATTCACAATTCCTTTTATGAGTATTGCATCAGCTTATTA
2979 160_HRV7b|  GGAGGGTCAACCATACCCTAGATTCACAATTCCTTTTATGAGTATTGCATCAGCTTATTA
2980 161_HRV7a|  GGAGGGTCAACCATACCCTAGATTCACAATTCCTTTTATGAGTATTGCATCAGCTTATTA
2981 162_HRV88   AGAAGGACAACCATACCCAAGATTTACCATTCCCTTTATGAGTATTGCATCAGCTTACTA
2982 163_HRV88a  AGAAGGACAACCATACCCAAGATTTACCATTCCCTTTATGAGTATTGCATCAGCTTACTA
2983 164_HRV88b  AGAAGGACAACCATACCCAAGATTTACCATTCCCTTTATGAGTATTGCATCAGCTTACTA
2984 165_HRV36a  AGAAGGGCAACCATATCCTAGATTTACAATCCCCTTTATGAGTATTGCATCAGCTTATTA
2985 166_HRV36b  AGAAGGGCAACCATATCCTAGATTTACAATCCCCTTTATGAGTATTGCATCAGCTTATTA
2986 167_HRV36   AGAAGGGCAACCATATCCTAGATTTACAATCCCCTTTATGAGTATTGCATCAGCTTATTA
2987 168_HRV89a  AGAAGGACAACCATACCCCAGATTCACAATCCCTTTTATGAGCATTGCATCAGCCTATTA
2988 169_HRV89b  AGAAGGACAACCATACCCCAGATTCACAATCCCTTTTATGAGCATTGCATCAGCCTATTA
2989 170_HRV89   AGAAGGACAACCATACCCCAGATTCACAATCCCTTTTATGAGCATTGCATCAGCCTATTA
2990 171_HRV58   GGAAGGACAACCATACCCTAGATTTACAATCCCTTTTATGAGCATTGCATCAGCTTACTA
```

FIG. D12 CONT'D

08.trace                                                                                     9/20/2007 5:05 PM

```
2991  172_HRV58a    GGAAGGACAACCATACCCTAGATTTACAATCCCTTTTATGAGCATTGCATCAGCTTACTA
2992  173_HRV58b    GGAAGGACAACCATACCCTAGATTTACAATCCCTTTTATGAGCATTGCATCAGCTTACTA
2993  GROUP_3       -GA-GG-CAACCATA-CC-AGATT-AC-AT-CC-TTTATGAG-ATTGCATCAGC-TA-TA
2994
2995  159_HRV7      TATGTTCTATGATGGATATGATGGTGATGATGCGTCATCCAAATATGGTTCCGTAGTAAC
2996  160_HRV7b|    TATGTTCTATGATGGATATGATGGTGATGATGCGTCATCCAAATATGGTTCCGTAGTAAC
2997  161_HRV7a|    TATGTTCTATGATGGATATGATGGTGATGATGCGTCATCCAAATATGGTTCCGTAGTAAC
2998  162_HRV88     TATGTTTTATGATGGATATGATGGTGATGCATCATCTAGGTATGGCTCAGTGGTAAC
2999  163_HRV88a    TATGTTTTATGATGGATATGATGGTGATGATGCATCATCTAGGTATGGCTCAGTGGTAAC
3000  164_HRV88b    TATGTTTTATGATGGATATGATGGTGATGATGCATCATCTAGGTATGGCTCAGTGGTAAC
3001  165_HRV36a    TATGTTTTATGATGGTTATGATGGTGATAATGCCGCATCAAAATATGGATCTGTGGTTAC
3002  166_HRV36b    TATGTTTTATGATGGTTATGATGGTGATAATGCCGCATCAAAATATGGATCTGTGGTTAC
3003  167_HRV36     TATGTTTTATGATGGTTATGATGGTGATAATGCCGCATCAAAATATGGATCTGTGGTTAC
3004  168_HRV89a    CATGTTTTATGATGGTTATGATGGTGATAGTGCAGCATCAAAATACGGTTCTGTAGTCAC
3005  169_HRV89b    CATGTTTTATGATGGTTATGATGGTGATAGTGCAGCATCAAAATACGGTTCTGTAGTCAC
3006  170_HRV89     CATGTTTTATGATGGTTATGATGGTGATAGTGCAGCATCAAAATACGGTTCTGTAGTCAC
3007  171_HRV58     TATGTTTTATGATGGCTATGATGGTGATGATGCTAAATCAATATATGGTTCTGTGGTAAC
3008  172_HRV58a    TATGTTTTATGATGGCTATGATGGTGATGATGCTAAATCAATATATGGTTCTGTGGTAAC
3009  173_HRV58b    TATGTTTTATGATGGCTATGATGGTGATGATGCTAAATCAATATATGGTTCTGTGGTAAC
3010  GROUP_3       -ATGTT-TATGATGG-TATGATGGTGAT--TGC---ATC-A--TA-GG-TC-GT-GT-AC
3011
3012  159_HRV7      CAATGACATGGGAACCATATGTGTTAGACTAGTTACATCTACACAAAAACACAATTTAAA
3013  160_HRV7b|    CAATGACATGGGAACCATATGTGTTAGACTAGTTACATCTACACAAAAACACAATTTAAA
3014  161_HRV7a|    CAATGACATGGGAACCATATGTGTTAGACTAGTTACATCTACACAAAAACACAATTTAAA
3015  162_HRV88     TAATGATATGGGAACTATATGTATTAGATTGGTCACCTCCACCCAAAAGCATAAACTGAA
3016  163_HRV88a    TAATGATATGGGAACTATATGTATTAGATTGGTCACCTCCACCCAAAAGCATAAACTGAA
3017  164_HRV88b    TAATGATATGGGAACTATATGTATTAGATTGGTCACCTCCACCCAAAAGCATAAACTGAA
3018  165_HRV36a    TAACGACATGGGAACCATATGTGTTAGAATAGTTACATCCAACCAAAAACATGATTTAAA
3019  166_HRV36b    TAACGACATGGGAACCATATGTGTTAGAATAGTTACATCCAACCAAAAACATGATTTAAA
3020  167_HRV36     TAACGACATGGGAACCATATGTGTTAGAATAGTTACATCCAACCAAAAACATGATTTAAA
3021  168_HRV89a    TAATGATATGGGAACCATATGTGTTAGAATAGTGACATCCAACCAAAAACATGATTTAAA
3022  169_HRV89b    TAATGATATGGGAACCATATGTGTTAGAATAGTGACATCCAACCAAAAACATGATTTAAA
3023  170_HRV89     TAATGATATGGGAACCATATGTGTTAGAATAGTGACATCCAACCAAAAACATGATTTAAA
3024  171_HRV58     AAATGACATGGGAACTATATGTGTTAGAATAGTCACATCCAAACAAAGACACAATTTAAA
3025  172_HRV58a    AAATGACATGGGAACTATATGTGTTAGAATAGTCACATCCAAACAAAGACACAATTTAAA
3026  173_HRV58b    AAATGACATGGGAACTATATGTGTTAGAATAGTCACATCCAAACAAAGACACAATTTAAA
3027  GROUP_3       -AA-GA-ATGGGAAC-ATATGT-TTAGA-T-GT-AC-TC-A--CAAA--CA--A--T-AA
3028
3029  159_HRV7      GATTGTGAGTCGCATTTACCACAAAGCCAAACATATAAAAGCATGGTGCCCACGCCCACC
3030  160_HRV7b|    GATTGTGAGTCGCATTTACCACAAAGCCAAACATATAAAAGCATGGTGCCCACGCCCACC
3031  161_HRV7a|    GATTGTGAGTCGCATTTACCACAAAGCCAAACATATAAAAGCATGGTGCCCACGCCCACC
3032  162_HRV88     TATCATTAGCCGTATATATCACAAGGCTAAACATATAAAGGCATGGTGTCCACGCCCACC
3033  163_HRV88a    TATCATTAGCCGTATATATCACAAGGCTAAACATATAAAGGCATGGTGTCCACGCCCACC
3034  164_HRV88b    TATCATTAGCCGTATATATCACAAGGCTAAACATATAAAGGCATGGTGTCCACGCCCACC
3035  165_HRV36a    TATTGTATGCCGCATTTATCATAAAGCTAAACACATAAAGGCCTGGTGCCCGCGTCCACC
3036  166_HRV36b    TATTGTATGCCGCATTTATCATAAACTAAACACATAAAGGCCTGGTGCCCGCGTCCACC
3037  167_HRV36     TATTGTATGCCGCATTTATCATAAAGCTAAACACATAAAGGCCTGGTGCCCGCGTCCACC
3038  168_HRV89a    TATTGTGTGCCGCATTTACCACAAGGCCAAACATATAAAAGCATGGTGTCCTCGCCCACC
3039  169_HRV89b    TATTGTGTGCCGCATTTACCACAAGGCCAAACATATAAAAGCATGGTGTCCTCGCCCACC
3040  170_HRV89     TATTGTGTGCCGCATTTACCACAAGGCCAAACATATAAAAGCATGGTGTCCTCGCCCACC
3041  171_HRV58     CATTGTCTGTCGCATTTACCACAAAGCCAAGCATATAAAAGCATGGTGTCCACGCCCACC
3042  172_HRV58a    CATTGTCTGTCGCATTTACCACAAAGCCAAGCATATAAAAGCATGGTGTCCACGCCCACC
3043  173_HRV58b    CATTGTCTGTCGCATTTACCACAAAGCCAAGCATATAAAAGCATGGTGTCCACGCCCACC
3044  GROUP_3       -AT--T--G-CG-AT-TA-CA-AA-GC-AA-CA-ATAAA-GC-TGGTG-CC-CG-CCACC
3045
3046  159_HRV7      ACGAGCTGTGCCTTATCAA-CACACTCACTCCACCAACTATGTGC-CACAAA---ATGGA
3047  160_HRV7b|    ACGAGCTGTGCCTTATCAA-CACACTCACTCCACCAACTATGTGC-CACAAA---ATGGA
3048  161_HRV7a|    ACGAGCTGTGCCTTATCAA-CACACTCACTCCACCAACTATGTGC-CACAAA---ATGGA
3049  162_HRV88     AAGAGCCGTACCTTATCAG-CACACACACTCCACCAATTATGTAC-CAACAG---ATGGG
3050  163_HRV88a    AAGAGCCGTACCTTATCAG-CACACACACTCCACCAATTATGTAC-CAACAG---ATGGG
3051  164_HRV88b    AAGAGCCGTACCTTATCAG-CACACACACTCCACCAATTATGTAC-CAACAG---ATGGG
3052  165_HRV36a    AAGGGCCGTTCCTTACCAA-CACACACATTCCACTAATTATATAC-CATACA---AAGGT
3053  166_HRV36b    AAGGGCCGTTCCTTACCAA-CACACACATTCCACTAATTATATAC-CATACA---AAGGT
3054  167_HRV36     AAGGGCCGTTCCTTACCAA-CACACACATTCCACTAATTATATAC-CATACA---AAGGT
3055  168_HRV89a    AAGGGCTGTTGCCTATCAA-CACACACACTCAACCAATTACATAC-CATCCA---ATGGT
```

FIG. D12 CONT'D

```
08.trace                                                                    9/20/2007 5:05 PM 3056  169_HRV89b   AAGGGCTGTTGCCTATCAA-CACACACACTCAACCAATTACATAC-CATCCA---ATGGT
3057  170_HRV89    AAGGGCTGTTGCCTATCAA-CACACACACTCAACCAATTACATAC-CATCCA---ATGGT
3058  171_HRV58    AAGGGCTGTTCCTTATCAA-TTCACACATTCTACTAATTACATAC-CAGATA---GTGGT
3059  172_HRV58a   AAGGGCTGTTCCTTATCAA-TTCACACATTCTACTAATTACATAC-CAGATA---GTGGT
3060  173_HRV58b   AAGGGCTGTTCCTTATCAA-TTCACACATTCTACTAATTACATAC-CAGATA---GTGGT
3061  GROUP_3      A-G-GC-GT--C-TA-CA-.--CAC-CA-TC-AC-AA-TA--T-C.CA----...--GG-
3062
3063  159_HRV7     GAGG------TCGCA---ACTCAAATCAAAACCAGAGCCAATCTTTTCACCCTCAAAT--
3064  160_HRV7b|   GAGG------TCGCA---ACTCAAATCAAAACCAGAGCCAATCTTTTCACCCTCAAAT--
3065  161_HRV7a|   GAGG------TCGCA---ACTCAAATCAAAACCAGAGCCAATCTTTTCACCCTCAAAT--
3066  162_HRV88    GAAG------TAGCA---ACTCAAATCAAAACCAGACGAGATGTTTACACTGTTACCA--
3067  163_HRV88a   GAAG------TAGCA---ACTCAAATCAAAACCAGACGAGATGTTTACACTGTTACCA--
3068  164_HRV88b   GAAG------TAGCA---ACTCAAATCAAAACCAGACGAGATGTTTACACTGTTACCA--
3069  165_HRV36a   GAGA------TCACA---ACCCAAATTAAAACCAGACCTAATGTCTTCACTGTA------
3070  166_HRV36b   GAGA------TCACA---ACCCAAATTAAAACCAGACCTAATGTCTTCACTGTG------
3071  167_HRV36    GAGA------TCACA---ACCCAAATTAAAACCAGACCTAATGTCTTCACTGTT------
3072  168_HRV89a   GAGG------CCACA---ACTCAGATTAAAACCAGACCTGATGTTTTTACCGTTACAA--
3073  169_HRV89b   GAGG------CCACA---ACTCAGATTAAAACCAGACCTGATGTTTTTACCGTTACAA--
3074  170_HRV89    GAGG------CCACA---ACTCAGATTAAAACCAGACCTGATGTTTTTACCGTTACAA--
3075  171_HRV58    GAGG------TAACA---ACACAAATCAAACCCAGAACCAATGTTTTTACTATTACAT--
3076  172_HRV58a   GAGG------TAACA---ACACAAATCAAACCCAGAACCAATGTTTTTACTATTACAT--
3077  173_HRV58b   GAGG------TAACA---ACACAAATCAAACCCAGAACCAATGTTTTTACTATTACAT--
3078  GROUP_3      GA--......---CA...AC-CA-AT-AAA-CCAGA----AT-T-T---AC--T-----..
3079
3080  159_HRV7     ----CAGCT------------
3081  160_HRV7b|   ----CAGCA------------
3082  161_HRV7a|   ----CAGCG------------
3083  162_HRV88    ----CTGCT------------
3084  163_HRV88a   ----CTGCA------------
3085  164_HRV88b   ----CTGCG------------
3086  165_HRV36a   ---------------------
3087  166_HRV36b   ---------------------
3088  167_HRV36    ---------------------
3089  168_HRV89a   ----ACGTG------------
3090  169_HRV89b   ----ACGTA------------
3091  170_HRV89    ----ACGTC------------
3092  171_HRV58    ----CTGCT------------
3093  172_HRV58a   ----CTGCA------------
3094  173_HRV58b   ----CTGCC------------
3095  GROUP_3      ....------...........
3096
3097
3098
3099  Group 4:
3100
3101  174_HRV12a   AATCCAGTAGAGAGATATGTTGATGAGGTGCTAAATGAAGTTCTAGTTGTTCCAAACATA
3102  175_HRV12b   AATCCAGTAGAGAGATATGTTGATGAGGTGCTAAATGAAGTTCTAGTTGTTCCAAACATA
3103  176_HRV12    AATCCAGTAGAGAGATATGTTGATGAGGTGCTAAATGAAGTTCTAGTTGTTCCAAACATA
3104  177_HRV78a   AATCCAGTGGAAGAATATGTTGATCAGGTTTTAAATGAGGTTTTAGTTGTTCCAAACATA
3105  178_HRV78b   AATCCAGTGGAAGAATATGTTGATCAGGTTTTAAATGAGGTTTTAGTTGTTCCAAACATA
3106  179_HRV78    AATCCAGTGGAAGAATATGTTGATCAGGTTTTAAATGAGGTTTTAGTTGTTCCAAACATA
3107  GROUP_4      AATCCAGT-GA---ATATGTTGAT-AGGT--TAAATGA-GTT-TAGTTGTTCCAAACATA
3108
3109  174_HRV12a   AACAAAAGTAATGGGCAGTTATCAAACGCAGCACCAGCGTTGGACGCTGCAGAAACTGGT
3110  175_HRV12b   AACAAAAGTAATGGGCAGTTATCAAACGCAGCACCAGCGTTGGACGCTGCAGAAACTGGT
3111  176_HRV12    AACAAAAGTAATGGGCAGTTATCAAACGCAGCACCAGCGTTGGACGCTGCAGAAACTGGT
3112  177_HRV78a   AAAGAAAGTAAACCCCAGTCTAGCAACTCCGCTCCAGTTTTGGACGCTGCAGAAACAGGT
3113  178_HRV78b   AAAGAAAGTAAACCCCAGTCTAGCAACTCCGCTCCAGTTTTGGACGCTGCAGAAACAGGT
3114  179_HRV78    AAAGAAAGTAAACCCCAGTCTAGCAACTCCGCTCCAGTTTTGGACGCTGCAGAAACAGGT
3115  GROUP_4      AA--AAAGTAA----CAGT-----AAC-C-GC-CCAG--TTGGACGCTGCAGAAAC-GGT
3116
3117  174_HRV12a   CATACCAGCCAAACACAACCAGAAGATGTGATTGAAACCAGGTATGTGATTACAGACCAG
3118  175_HRV12b   CATACCAGCCAAACACAACCAGAAGATGTGATTGAAACCAGGTATGTGATTACAGACCAG
3119  176_HRV12    CATACCAGCCAAACACAACCAGAAGATGTGATTGAAACCAGGTATGTGATTACAGACCAG
3120  177_HRV78a   CATACGAACCAAGTACAGCCTGAAGACACCATAGAAACTAGATATGTTATAACTGACCAA
```

FIG. D12 CONT'D

```
08.trace                                                                 9/20/2007 5:05 PM 3121  178_HRV78b   CATACGAACCAAGTACAGCCTGAAGACACCATAGAAACTAGATATGTTATAACTGACCAA
3122  179_HRV78    CATACGAACCAAGTACAGCCTGAAGACACCATAGAAACTAGATATGTTATAACTGACCAA
3123  GROUP_4     CATAC-A-CCAA--ACA-CC-GAAGA----AT-GAAAC-AG-TATGT-AT-AC-GACCA-
3124
3125  174_HRV12a   ACTAGAGATGAGATGTCAATTGAATCTTTCCTTGGTCGGTCCGGATGCATTTCAATTATC
3126  175_HRV12b   ACTAGAGATGAGATGTCAATTGAATCTTTCCTTGGTCGGTCCGGATGCATTTCAATTATC
3127  176_HRV12    ACTAGAGATGAGATGTCAATTGAATCTTTCCTTGGTCGGTCCGGATGCATTTCAATTATC
3128  177_HRV78a   ACAAGAGATGAAATGAGCATTGAAAGTTTCCTCGGAAGATCAGGTTGTGCAACAATTATG
3129  178_HRV78b   ACAAGAGATGAAATGAGCATTGAAAGTTTCCTCGGAAGATCAGGTTGTGCAACAATTATG
3130  179_HRV78    ACAAGAGATGAAATGAGCATTGAAAGTTTCCTCGGAAGATCAGGTTGTGCAACAATTATG
3131  GROUP_4     AC-AGAGATGA-ATG---ATTGAA--TTTCCT-GG--G-TC-GG-TG-----CAATTAT-
3132
3133  174_HRV12a   GAATTGGATTTAGACCATGAAGGT---------------TATTCAGCA---GAAGGGAAA
3134  175_HRV12b   GAATTGGATTTAGACCATGAAGGT---------------TATTCAGCA---GAAGGGAAA
3135  176_HRV12    GAATTGGATTTAGACCATGAAGGT---------------TATTCAGCA---GAAGGGAAA
3136  177_HRV78a   AGACTAGAATTGGACCACACTGAT---------------TACAATGCT---GAAGGGAAA
3137  178_HRV78b   AGACTAGAATTGGACCACACTGAT---------------TACAATGCT---GAAGGGAAA
3138  179_HRV78    AGACTAGAATTGGACCACACTGAT---------------TACAATGCT---GAAGGGAAA
3139  GROUP_4     --A-T-GA-TT-GACCA----G-T.............TA----GC-...GAAGGGAAA
3140
3141  174_HRV12a   AACTTTAAAACATGGAAGATAAATCTTAAGGAAATGGCCCAGATTAGAAGGAAAAATGAG
3142  175_HRV12b   AACTTTAAAACATGGAAGATAAATCTTAAGGAAATGGCCCAGATTAGAAGGAAAAATGAG
3143  176_HRV12    AACTTTAAAACATGGAAGATAAATCTTAAGGAAATGGCCCAGATTAGAAGGAAAAATGAG
3144  177_HRV78a   AATTTTACAACGTGGAAAATCAACTTACAGGAGATGGCCCAGATTAGAAGAAAGAATGAG
3145  178_HRV78b   AATTTTACAACGTGGAAAATCAACTTACAGGAGATGGCCCAGATTAGAAGAAAGAATGAG
3146  179_HRV78    AATTTTACAACGTGGAAAATCAACTTACAGGAGATGGCCCAGATTAGAAGAAAGAATGAG
3147  GROUP_4     AA-TTTA-AAC-TGGAA--AT-AA--T--AGGA-ATGGCCCAGATTAGAAG-AA-AATGAG
3148
3149  174_HRV12a   CTTTTCACCTACTTAAGGTTTGATTCTGAAATCACCATTGTTCCAAGCAATG-CAGCAAT
3150  175_HRV12b   CTTTTCACCTACTTAAGGTTTGATTCTGAAATCACCATTGTTCCAAGCAATG-CAGCAAT
3151  176_HRV12    CTTTTCACCTACTTAAGGTTTGATTCTGAAATCACCATTGTTCCAAGCAATG-CAGCAAT
3152  177_HRV78a   ATGTTCACATATCTCAGATTTGATTCAGAAATCACTCTTG-TGTGTGCAGTGGCCTCACA
3153  178_HRV78b   ATGTTCACATATCTCAGATTTGATTCAGAAATCACTCTTG-TGTGTGCAGTGGCCTCACA
3154  179_HRV78    ATGTTCACATATCTCAGATTTGATTCAGAAATCACTCTTG-TGTGTGCAGTGGCCTCACA
3155  GROUP_4     -T-TTCAC-TA--T-AG-TTTGATTC-GAAATCAC--TTG-T----GCA-TG-C--CA--
3156
3157  174_HRV12a   AGAAGGAAGCAATGGTCACGTGGTGGTCCAATACATGTATGTACCTCCTGGTGCCCCACT
3158  175_HRV12b   AGAAGGAAGCAATGGTCACGTGGTGGTCCAATACATGTATGTACCTCCTGGTGCCCCACT
3159  176_HRV12    AGAAGGAAGCAATGGTCACGTGGTGGTCCAATACATGTATGTACCTCCTGGTGCCCCACT
3160  177_HRV78a   AGGAGACAATAATGGACATGTGGTGCTTCAATTTATGTTTGTTCCACCTGGAGCCCCTAT
3161  178_HRV78b   AGGAGACAATAATGGACATGTGGTGCTTCAATTTATGTTTGTTCCACCTGGAGCCCCTAT
3162  179_HRV78    AGGAGACAATAATGGACATGTGGTGCTTCAATTTATGTTTGTTCCACCTGGAGCCCCTAT
3163  GROUP_4     AG-AG--A--AATGG-CA-GTGGTG-T-CAAT--ATGT-TGT-CC-CCTGG-GCCCC--T
3164
3165  174_HRV12a   ACCCAAAAAACGTGATGATTACACATGGCAATCTGGCACCAACGCCTCAGTTTTTTGGCA
3166  175_HRV12b   ACCCAAAAAACGTGATGATTACACATGGCAATCTGGCACCAACGCCTCAGTTTTTTGGCA
3167  176_HRV12    ACCCAAAAAACGTGATGATTACACATGGCAATCTGGCACCAACGCCTCAGTTTTTTGGCA
3168  177_HRV78a   ACCAAAGAAGAGAGATGACTATACTTGGCAGTCAGGCACCAATGCATCTGTGTTTTGGCA
3169  178_HRV78b   ACCAAAGAAGAGAGATGACTATACTTGGCAGTCAGGCACCAATGCATCTGTGTTTTGGCA
3170  179_HRV78    ACCAAAGAAGAGAGATGACTATACTTGGCAGTCAGGCACCAATGCATCTGTGTTTTGGCA
3171  GROUP_4     ACC-AA-AA--G-GATGA-TA-AC-TGGCA-TC-GGCACCAA-GC-TC-GT-TTTTGGCA
3172
3173  174_HRV12a   GGAAGGTCAACCTTACCCCAGATTCACAATCCCTTTTATTAGTATTGCCTCAGCATATTA
3174  175_HRV12b   GGAAGGTCAACCTTACCCCAGATTCACAATCCCTTTTATTAGTATTGCCTCAGCATATTA
3175  176_HRV12    GGAAGGTCAACCTTACCCCAGATTCACAATCCCTTTTATTAGTATTGCCTCAGCATATTA
3176  177_HRV78a   ACAAGGTCAAACATACCCCAGGTTCTCTATACCATTTTCTAGTATTGCCTCAGCTTATTA
3177  178_HRV78b   ACAAGGTCAAACATACCCCAGGTTCTCTATACCATTTTCTAGTATTGCCTCAGCTTATTA
3178  179_HRV78    ACAAGGTCAAACATACCCCAGGTTCTCTATACCATTTTCTAGTATTGCCTCAGCTTATTA
3179  GROUP_4     --AAGGTCAA-C-TACCCCAG-TTC-C-AT-CC-TTT--TAGTATTGCCTCAGC-TATTA
3180
3181  174_HRV12a   CATGTTTTATGATGGTTATGCTGATGACAACCCAAGTGCACCTTATGGAACTGTAGTTAC
3182  175_HRV12b   CATGTTTTATGATGGTTATGCTGATGACAACCCAAGTGCACCTTATGGAACTGTAGTTAC
3183  176_HRV12    CATGTTTTATGATGGTTATGCTGATGACAACCCAAGTGCACCTTATGGAACTGTAGTTAC
3184  177_HRV78a   CATGTTTTATGATGGATACTCGGATGACAGCACATCCTCTCCATATGGCACTGTAGTTAC
3185  178_HRV78b   CATGTTTTATGATGGATACTCGGATGACAGCACATCCTCTCCATATGGCACTGTAGTTAC
```

FIG. D12 CONT'D 08.trace                                                                                    9/20/2007 5:05 PM

```
3186  179_HRV78    CATGTTTTATGATGGATACTCGGATGACAGCACATCCTCTCCATATGGCACTGTAGTTAC
3187  GROUP_4      CATGTTTTATGATGG-TA--C-GATGACA-C-CA----C-CC-TATGG-ACTGTAGTTAC
3188
3189  174_HRV12a   CAATGACATGGGTTCACTGTGTGTCAGAATAGTTACAGACCAGCAAAAACATAAAGTTAA
3190  175_HRV12b   CAATGACATGGGTTCACTGTGTGTCAGAATAGTTACAGACCAGCAAAAACATAAAGTTAA
3191  176_HRV12    CAATGACATGGGTTCACTGTGTGTCAGAATAGTTACAGACCAGCAAAAACATAAAGTTAA
3192  177_HRV78a   CAATGACATGGGTACACTGTGTATGAGGATGGTTACAGATCAACAACAACATAAGGTCAC
3193  178_HRV78b   CAATGACATGGGTACACTGTGTATGAGGATGGTTACAGATCAACAACAACATAAGGTCAC
3194  179_HRV78    CAATGACATGGGTACACTGTGTATGAGGATGGTTACAGATCAACAACAACATAAGGTCAC
3195  GROUP_4      CAATGACATGGGT-CACTGTGT-T-AG-AT-GTTACAGA-CA-CAA-AACATAA-GT-A-
3196
3197  174_HRV12a   GATTACCAGTAGAATATACCATAAAGCAAAACATATCAGTGCCTGGGGCCCTAGACCACC
3198  175_HRV12b   GATTACCAGTAGAATATACCATAAAGCAAAACATATCAGTGCCTGGGGCCCTAGACCACC
3199  176_HRV12    GATTACCAGTAGAATATACCATAAAGCAAAACATATCAGTGCCTGGGGCCCTAGACCACC
3200  177_HRV78a   AATTACAGCTAGAGTCTACCACAAGGCCAAACATATTAGTGCATGGGGCCCAAGACCTCC
3201  178_HRV78b   AATTACAGCTAGAGTCTACCACAAGGCCAAACATATTAGTGCATGGGGCCCAAGACCTCC
3202  179_HRV78    AATTACAGCTAGAGTCTACCACAAGGCCAAACATATTAGTGCATGGGGCCCAAGACCTCC
3203  GROUP_4      -ATTAC---TAGA-T-TACCA-AA-GC-AAACATAT-AGTGC-TGGGGCCC-AGACC-CC
3204
3205  174_HRV12a   AAGAGCTGTACCATACCAG-CATATACACAATCCAAATTACAAGA-CAAGTA------AT
3206  175_HRV12b   AAGAGCTGTACCATACCAG-CATATACACAATCCAAATTACAAGA-CAAGTA------AT
3207  176_HRV12    AAGAGCTGTACCATACCAG-CATATACACAATCCAAATTACAAGA-CAAGTA------AT
3208  177_HRV78a   TAGAGCTGTACCTTATCAG-CACATATATAACCCTAATTATAAAA-CTGAAG------AA
3209  178_HRV78b   TAGAGCTGTACCTTATCAG-CACATATATAACCCTAATTATAAAA-CTGAAG------AA
3210  179_HRV78    TAGAGCTGTACCTTATCAG-CACATATATAACCCTAATTATAAAA-CTGAAG------AA
3211  GROUP_4      -AGAGCTGTACC-TA-CAG.CA-ATA-A-AA-CC-AATTA-AA-A.C-----......A-
3212
3213  174_HRV12a   GGAG------TTCCAGACAATAGAGTCAAACTCAGAGAGACACTCACCACAGTA------
3214  175_HRV12b   GGAG------TTCCAGACAATAGAGTCAAACTCAGAGAGACACTCACCACAGTG------
3215  176_HRV12    GGAG------TTCCAGACAATAGAGTCAAACTCAGAGAGACACTCACCACAGTT------
3216  177_HRV78a   GGAA------CTCCAGACACCAAAGTGGCAATTAGAGCTAATATTAAAACTGTA------
3217  178_HRV78b   GGAA------CTCCAGACACCAAAGTGGCAATTAGAGCTAATATTAAAACTGTG------
3218  179_HRV78    GGAA------CTCCAGACACCAAAGTGGCAATTAGAGCTAATATTAAAACTGTT------
3219  GROUP_4      GGA-......-TCCAGACA--A-AGT---A-T-AGAG--A---T-A--AC-GT-......
3220
3221  174_HRV12a   --------------------
3222  175_HRV12b   --------------------
3223  176_HRV12    --------------------
3224  177_HRV78a   --------------------
3225  178_HRV78b   --------------------
3226  179_HRV78    --------------------
3227  GROUP_4      ....................
3228
3229
3230
3231  Group_5:
3232
3233  180_HRV20    AACCCAGTGGAAAGGTACACAGAAGCTATTTTAAATGAAGTTCTTGTAGTTCCAAATATC
3234  181_HRV20a   AACCCAGTGGAAAGGTACACAGAAGCTATTTTAAATGAAGTTCTTGTAGTTCCAAATATC
3235  182_HRV20b   AACCCAGTGGAAAGGTACACAGAAGCTATTTTGTAGTTCTTGTAGTTCCAAATATC
3236  183_HRV68    AACCCAGTTGAAAAATACACAGAAGCCGTTCTTAATGAGGTCCTTGTGGTTCCAAACATA
3237  184_HRV68a   AACCCAGTTGAAAAATACACAGAAGCCGTTCTTAATGAGGTCCTTGTGGTTCCAAACATA
3238  185_HRV68b   AACCCAGTTGAAAAATACACAGAAGCCGTTCTTAATGAGGTCCTTGTGGTTCCAAACATA
3239  186_HRV28    AATCCAGTTGAAAAATATACTGAAGCACTACTTAATGAAGTGCTTGTTGTGCCAAACATC
3240  187_HRV28a   AATCCAGTTGAAAAATATACTGAAGCACTACTTAATGAAGTGCTTGTTGTGCCAAACATC
3241  188_HRV28b   AATCCAGTTGAAAAATATACTGAAGCACTACTTAATGAAGTGCTTGTTGTGCCAAACATC
3242  189_HRV53a   AACCCGGTAGAGAAATACACAGAGGCTATCTTAAATGAAGTATTAGTAGTCCCAAACATT
3243  190_HRV53b   AACCCGGTAGAGAAATACACAGAGGCTATCTTAAATGAAGTATTAGTAGTCCCAAACATT
3244  191_HRV53    AACCCGGTAGAGAAATACACAGAGGCTATCTTAAATGAAGTATTAGTAGTCCCAAACATT
3245  192_HRV46a   AATCCAGTGGAAAAATATACAGAAGCTGTTCTTAATGAGGTCCTTGTAGTACCTAACATC
3246  193_HRV46b   AATCCAGTGGAAAAATATACAGAAGCTGTTCTTAATGAGGTCCTTGTAGTACCTAACATC
3247  194_HRV46    AATCCAGTGGAAAAATATACAGAAGCTGTTCTTAATGAGGTCCTTGTAGTACCTAACATC
3248  195_HRV80a   AATCCAGTCGAAAAATACACAGAAGCAATCCTCAATGAAGTTCTTGTTGTACCAAACATC
3249  196_HRV80b   AATCCAGTCGAAAAATACACAGAAGCAATCCTCAATGAAGTTCTTGTTGTACCAAACATC
3250  197_HRV80    AATCCAGTCGAAAAATACACAGAAGCAATCCTCAATGAAGTTCTTGTTGTACCAAACATC
```

FIG. D12 CONT'D

```
08.trace                                                                9/20/2007 5:05 PM 3251 198_HRV51   AACCCTGTTGAAAAATATACAGAGGCTTTACTCAATGAAGTGTTGGTGGTTCCCAACATA
3252 199_HRV51a  AACCCTGTTGAAAAATATACAGAGGCTTTACTCAATGAAGTGTTGGTGGTTCCCAACATA
3253 200_HRV51b  AACCCTGTTGAAAAATATACAGAGGCTTTACTCAATGAAGTGTTGGTGGTTCCCAACATA
3254 201_HRV65a  AATCCAATTGAGAAGTATACAGAAGCTCTACTTAATGAAGTGTTGGTGGTCCCAAATATA
3255 202_HRV65b  AATCCAATTGAGAAGTATACAGAAGCTCTACTTAATGAAGTGTTGGTGGTCCCAAATATA
3256 203_HRV65   AATCCAATTGAGAAGTATACAGAAGCTCTACTTAATGAAGTGTTGGTGGTCCCAAATATA
3257 204_HRV71a  AATCCTGTAGAAAAATATACAGAAGCAATACTCAATGAGGTTCTAGTTGTGCCAAATATA
3258 205_HRV71b  AATCCTGTAGAAAAATATACAGAAGCAATACTCAATGAGGTTCTAGTTGTGCCAAATATA
3259 206_HRV71   AATCCTGTAGAAAAATATACAGAAGCAATACTCAATGAGGTTCTAGTTGTGCCAAATATA
3260 GROUP_5     AA-CC--T-GA-A--TA-AC-GA-GC--T--T-AATGA-GT--T-GT-GT-CC-AA-AT-
3261
3262 180_HRV20   ACATCTAGTAACTCCCAAACATCAAATGCAGCACCAGCACTAGATGCTGCTGAGACAGGA
3263 181_HRV20a  ACATCTAGTAACTCCCAAACATCAAATGCAGCACCAGCACTAGATGCTGCTGAGACAGGA
3264 182_HRV20b  ACATCTAGTAACTCCCAAACATCAAATGCAGCACCAGCACTAGATGCTGCTGAGACAGGA
3265 183_HRV68   CCAGCAAGTAATACCCAAACTTCAAATGCAGCCCCAGCCTTAGATGCTGCTGAGACTGGA
3266 184_HRV68a  CCAGCAAGTAATACCCAAACTTCAAATGCAGCCCCAGCCTTAGATGCTGCTGAGACTGGA
3267 185_HRV68b  CCAGCAAGTAATACCCAAACTTCAAATGCAGCCCCAGCCTTAGATGCTGCTGAGACTGGA
3268 186_HRV28   AATCCTAGCAACGCACAAACTACAAATGCAGCTCCCGCTCTCGATGCCGCTGAGACGGGG
3269 187_HRV28a  AATCCTAGCAACGCACAAACTACAAATGCAGCTCCCGCTCTCGATGCCGCTGAGACGGGG
3270 188_HRV28b  AATCCTAGCAACGCACAAACTACAAATGCAGCTCCCGCTCTCGATGCCGCTGAGACGGGG
3271 189_HRV53a  AATGCAAGCAATCCACAAACTTCAAATTCAGCACCAGCACTAGATGCTGCAGAAACGGGT
3272 190_HRV53b  AATGCAAGCAATCCACAAACTTCAAATTCAGCACCAGCACTAGATGCTGCAGAAACGGGT
3273 191_HRV53   AATGCAAGCAATCCACAAACTTCAAATTCAGCACCAGCACTAGATGCTGCAGAAACGGGT
3274 192_HRV46a  AATGCCAGTAGTGGACATACATCTAATTCAGCTCCAGCACTTGATGCAGCAGAAACTGGA
3275 193_HRV46b  AATGCCAGTAGTGGACATACATCTAATTCAGCTCCAGCACTTGATGCAGCAGAAACTGGA
3276 194_HRV46   AATGCCAGTAGTGGACATACATCTAATTCAGCTCCAGCACTTGATGCAGCAGAAACTGGA
3277 195_HRV80a  AGTGCTAGCAATGGACATACATCAAACTCAGCTCCAACACTTGATGCAGCAGAAACTGGT
3278 196_HRV80b  AGTGCTAGCAATGGACATACATCAAACTCAGCTCCAACACTTGATGCAGCAGAAACTGGT
3279 197_HRV80   AGTGCTAGCAATGGACATACATCAAACTCAGCTCCAACACTTGATGCAGCAGAAACTGGT
3280 198_HRV51   CAACCTAGCAGTGGGCACACATCTAATGCTGCACCAGCTCTAGATGCTGCTGAGACAGGA
3281 199_HRV51a  CAACCTAGCAGTGGGCACACATCTAATGCTGCACCAGCTCTAGATGCTGCTGAGACAGGA
3282 200_HRV51b  CAACCTAGCAGTGGGCACACATCTAATGCTGCACCAGCTCTAGATGCTGCTGAGACAGGA
3283 201_HRV65a  CAAGCTAGTAATGGGCATACATCTAATGCTGCACCAGCTTTAGATGCTGCTGAAACAGGA
3284 202_HRV65b  CAAGCTAGTAATGGGCATACATCTAATGCTGCACCAGCTTTAGATGCTGCTGAAACAGGA
3285 203_HRV65   CAAGCTAGTAATGGGCATACATCTAATGCTGCACCAGCTTTAGATGCTGCTGAAACAGGA
3286 204_HRV71a  CAACCTAGTAATGGACATACCTCAAACTCAGCACCAGCCTTAGATGCAGCAGAAACTGGG
3287 205_HRV71b  CAACCTAGTAATGGACATACCTCAAACTCAGCACCAGCCTTAGATGCAGCAGAAACTGGG
3288 206_HRV71   CAACCTAGTAATGGACATACCTCAAACTCAGCACCAGCCTTAGATGCAGCAGAAACTGGG
3289 GROUP_5     ----C-AG-A-----CA-AC--C-AA--C-GC-CC--C--T-GATGC-GC-GA-AC-GG-
3290
3291 180_HRV20   CACACAAACCAGGTCCAGCCAGAAGATATGGTCGAGACACGGTATGTAATTACTGATCAG
3292 181_HRV20a  CACACAAACCAGGTCCAGCCAGAAGATATGGTCGAGACACGGTATGTAATTACTGATCAG
3293 182_HRV20b  CACACAAACCAGGTCCAGCCAGAAGATATGGTCGAGACACGGTATGTAATTACTGATCAG
3294 183_HRV68   CATACAAACCAAGTCCAACCAGAAGATGTGGTCGAAACACGCTATGTCATAACAGACCAG
3295 184_HRV68a  CATACAAACCAAGTCCAACCAGAAGATGTGGTTGAAACACGCTATGTCATAACAGACCAG
3296 185_HRV68b  CATACAAACCAAGTCCAACCAGAAGATGTGGTTGAAACACGCTATGTCATAACAGACCAG
3297 186_HRV28   CACACAAGCCAAACACAACCTGAAGACATGGTCGAGACTAGGTATGTAATCACAGATCAG
3298 187_HRV28a  CACACAAGCCAAACACAACCTGAAGACATGGTTGAGACTAGGTATGTAATCACAGATCAG
3299 188_HRV28b  CACACAAGCCAAACACAACCTGAAGACATGGTTGAGACTAGGTATGTAATCACAGATCAG
3300 189_HRV53a  CATACAAGTCAGACACAACCTGAGGACATGCTGGAAACTAGATATGTCATCACAGACCAA
3301 190_HRV53b  CATACAAGTCAGACACAACCTGAGGACATGCTGGAAACTAGATATGTCATCACAGACCAA
3302 191_HRV53   CATACAAGTCAGACACAACCTGAGGACATGCTGGAAACTAGATATGTCATCACAGACCAA
3303 192_HRV46a  CACACTAGCCAGATACAACCAGAAGACATGATAGAAACCAGATATGTTATCACAGACCAA
3304 193_HRV46b  CACACTAGCCAGATACAACCAGAAGACATGATAGAAACCAGATATGTTATCACAGACCAA
3305 194_HRV46   CACACTAGCCAGATACAACCAGAAGACATGATAGAAACCAGATATGTTATCACAGACCAA
3306 195_HRV80a  CACACTAGCCAGGTGCAACCAGAAGACATGATAGAAACTAGATATGTTATTACTGATCAG
3307 196_HRV80b  CACACTAGCCAGGTGCAACCAGAAGACATGATAGAAACTAGATATGTTATTACTGATCAG
3308 197_HRV80   CACACTAGCCAGGTGCAACCAGAAGACATGATAGAAACTAGATATGTTATTACTGATCAG
3309 198_HRV51   CATACTAGTCAAGTTCAACCAGAAGATATGGTAGAGACCAGGTATGTTGTCACAGACCAA
3310 199_HRV51a  CATACTAGTCAAGTTCAACCAGAAGATATGGTAGAGACCAGGTATGTTGTCACAGACCAA
3311 200_HRV51b  CATACTAGTCAAGTTCAACCAGAAGATATGGTAGAGACCAGGTATGTTGTCACAGACCAA
3312 201_HRV65a  CACACTAGTCAAGTTCAACCAGGATGTGATAGAAACCAGATATGTCATCACAGATCAA
3313 202_HRV65b  CACACTAGTCAAGTTCAACCAGAGGATGTGATAGAAACCAGATATGTCATCACAGATCAA
3314 203_HRV65   CACACTAGTCAAGTTCAACCAGAGGATGTGATAGAAACCAGATATGTCATCACAGATCAA
3315 204_HRV71a  CATACCAACCAAGTACAACCAGAAGATGTTATGGAAACCAGATATGTGATCACTGATCAA
```

08.trace 9/20/2007 5:05 PM

```
3316 205_HRV71b   CATACCAACCAAGTACAACCAGAAGATGTTATGGAAACCAGATATGTGATCACTGATCAA
3317 206_HRV71    CATACCAACCAAGTACAACCAGAAGATGTTATGGAAACCAGATATGTGATCACTGATCAA
3318 GROUP_5      CA-AC-A--CA----CA-CC-GA-GA--T--T-GA-AC--G-TATGT--T-AC-GA-CA-
3319
3320 180_HRV20    ACCCGTGATGAAATGAGTGTGGAAAGTTTTCTTGGTAGATCTGGTTGCATTGCTATCATA
3321 181_HRV20a   ACCCGTGATGAAATGAGTGTGGAAAGTTTTCTTGGTAGATCTGGTTGCATTGCTATCATA
3322 182_HRV20b   ACCCGTGATGAAATGAGTGTGGAAAGTTTTCTTGGTAGATCTGGTTGCATTGCTATCATA
3323 183_HRV68    ACAAGGGATGAAATGAGCATAGAGAGCTTCCTCGGTAGGTCAGGTTGCATTGCAATCATA
3324 184_HRV68a   ACAAGGGATGAAATGAGCATAGAGAGCTTCCTCGGTAGGTCAGGTTGCATTGCAATCATA
3325 185_HRV68b   ACAAGGGATGAAATGAGCATAGAGAGCTTCCTCGGTAGGTCAGGTTGCATTGCAATCATA
3326 186_HRV28    ACCCGTGATGAAATGAGTATAGAGAGTTTCTTAGGTAGGTCTAGTTGCATTGCAATAATC
3327 187_HRV28a   ACCCGTGATGAAATGAGTATAGAGAGTTTCTTAGGTAGGTCTAGTTGCATTGCAATAATC
3328 188_HRV28b   ACCCGTGATGAAATGAGTATAGAGAGTTTCTTAGGTAGGTCTAGTTGCATTGCAATAATC
3329 189_HRV53a   ACCCGGGATGAAATGAGCATTGAAAGTTTCTTAGGCAGATCAAGTTGCATTGCTGAGATC
3330 190_HRV53b   ACCCGGGATGAAATGAGCATTGAAAGTTTCTTAGGCAGATCAAGTTGCATTGCTGAGATC
3331 191_HRV53    ACCCGGGATGAAATGAGCATTGAAAGTTTCTTAGGCAGATCAAGTTGCATTGCTGAGATC
3332 192_HRV46a   ACAAAAGATGAAATGAGTATAGAAAGTTTTCTAGGAAGGTCAGGCTGCATTGCCATTATT
3333 193_HRV46b   ACAAAAGATGAAATGAGTATAGAAAGTTTTCTAGGAAGGTCAGGCTGCATTGCCATTATT
3334 194_HRV46    ACAAAAGATGAAATGAGTATAGAAAGTTTTCTAGGAAGGTCAGGCTGCATTGCCATTATT
3335 195_HRV80a   ACAAAGGATGAGATGAGCATTGAAAGTTTCTTAGGAAGATCTGGTTGTGTTGCTATCATT
3336 196_HRV80b   ACAAAGGATGAGATGAGCATTGAAAGTTTTCTTAGGAAGATCTGGTTGTGTTGCTATCATT
3337 197_HRV80    ACAAAGGATGAGATGAGCATTGAAAGTTTCTTAGGAAGATCTGGTTGTGTTGCTATCATT
3338 198_HRV51    ACTAGAGATGAAATGAGTATAGAGAGTTTCTTGGGTAGATCTGCTTGCGTAGCAATCATC
3339 199_HRV51a   ACTAGAGATGAAATGAGTATAGAGAGTTTCTTGGGTAGATCTGCTTGCGTAGCAATCATC
3340 200_HRV51b   ACTAGAGATGAAATGAGTATAGAGAGTTTCTTGGGTAGATCTGCTTGCGTAGCAATCATC
3341 201_HRV65a   ACCAGAGATGAGATGAGCGTAGAGAGTTTCCTGGGCAGATCTGCCTGCATAGCAGTCATT
3342 202_HRV65b   ACCAGAGATGAGATGAGCGTAGAGAGTTTCCTGGGCAGATCTGCCTGCATAGCAGTCATT
3343 203_HRV65    ACCAGAGATGAGATGAGCGTAGAGAGTTTCCTGGGCAGATCTGCCTGCATAGCAGTCATT
3344 204_HRV71a   ACTAGGGATGAAATGAGCATTGAGAGCTTCTTGGGCAGATCTGCATGCATAGCTACCATA
3345 205_HRV71b   ACTAGGGATGAAATGAGCATTGAGAGCTTCTTGGGCAGATCTGCATGCATAGCTACCATA
3346 206_HRV71    ACTAGGGATGAAATGAGCATTGAGAGCTTCTTGGGCAGATCTGCATGCATAGCTACCATA
3347 GROUP_5      AC----GATGA-ATGAG--T-GA-AG-TT--T-GG-AG-TC----TG--T-GC----AT-
3348
3349 180_HRV20    CATACTGACTTAGATCATGAAGCACAA--------CAATATAATGCA---CCCGGAAAA
3350 181_HRV20a   CATACTGACTTAGATCATGAAGCACAA--------CAATATAATGCA---CCCGGAAAA
3351 182_HRV20b   CATACTGACTTAGATCATGAAGCACAA--------CAATATAATGCA---CCCGGAAAA
3352 183_HRV68    CATACTGACTTAGATCACAATGAGGAT--------CAGTACAATGCA---CCTGGAAAA
3353 184_HRV68a   CATACTGACTTAGATCACAATGAGGAT--------CAGTACAATGCA---CCTGGAAAA
3354 185_HRV68b   CATACTGACTTAGATCACAATGAGGAT--------CAGTACAATGCA---CCTGGAAAA
3355 186_HRV28    CATACTGATGTTGTGCATGAAACAGAC--------AAGTACAACCAC---CCAGGGAAG
3356 187_HRV28a   CATACTGATGTTGTGCATGAAACAGAC--------AAGTACAACCAC---CCAGGGAAG
3357 188_HRV28b   CATACTGATGTTGTGCATGAAACAGAC--------AAGTACAACCAC---CCAGGGAAG
3358 189_HRV53a   CATACCAATTTAGACCAT---ACTG-----------GATACAATGAG---CCTGGGAAA
3359 190_HRV53b   CATACCAATTTAGACCAT---ACTG-----------GATACAATGAG---CCTGGGAAA
3360 191_HRV53    CATACCAATTTAGACCAT---ACTG-----------GATACAATGAG---CCTGGGAAA
3361 192_HRV46a   GAGACAGAATTGAATCATGAAGAAGGG---------AAATACAATGCA---GAAGATCAA
3362 193_HRV46b   GAGACAGAATTGAATCATGAAGAAGGG---------AAATACAATGCA---GAAGATCAA
3363 194_HRV46    GAGACAGAATTGAATCATGAAGAAGGG---------AAATACAATGCA---GAAGATCAA
3364 195_HRV80a   GAAACCAAATTAAACCATGAAACAGAC---------ATGTACAATGCT---GATGGTCAG
3365 196_HRV80b   GAAACCAAATTAAACCATGAAACAGAC---------ATGTACAATGCT---GATGGTCAG
3366 197_HRV80    GAAACCAAATTAAACCATGAAACAGAC---------ATGTACAATGCT---GATGGTCAG
3367 198_HRV51    CATACAAACCTTGAGCATGTTGAAGCAGACAGACAAGCCTACAATGCA---AAAGGGAAA
3368 199_HRV51a   CATACAAACCTTGAGCATGTTGAAGCAGACAGACAAGCCTACAATGCA---AAAGGGAAA
3369 200_HRV51b   CATACAAACCTTGAGCATGTTGAAGCAGACAGACAAGCCTACAATGCA---AAAGGGAAA
3370 201_HRV65a   CACACAGATCTTAAACATGACCATGAAGGCCAAAATGTTTACAATGAC---GAAGGCAGA
3371 202_HRV65b   CACACAGATCTTAAACATGACCATGAAGGCCAAAATGTTTACAATGAC---GAAGGCAGA
3372 203_HRV65    CACACAGATCTTAAACATGACCATGAAGGCCAAAATGTTTACAATGAC---GAAGGCAGA
3373 204_HRV71a   CACACTAAATTAGTACATGGAGAGGAGG------TGTTTATAATATG---AAAGGTAAC
3374 205_HRV71b   CACACTAAATTAGTACATGGAGAGGAGG------TGTTTATAATATG---AAAGGTAAC
3375 206_HRV71    CACACTAAATTAGTACATGGAGAGGAGG------TGTTTATAATATG---AAAGGTAAC
3376 GROUP_5      -A-AC--A--T----CA----------------------TA-AA----...---G-----
3377
3378 180_HRV20    AATTTCTCTCAGTGGAAGATCACAATCAAGGAAATGGCTCAAATCAGAAGAAAATGTGAG
3379 181_HRV20a   AATTTCTCTCAGTGGAAGATCACAATCAAGGAAATGGCTCAAATCAGAAGAAAATGTGAG
3380 182_HRV20b   AATTTCTCTCAGTGGAAGATCACAATCAAGGAAATGGCTCAAATCAGAAGAAAATGTGAG
```

FIG. D12 CONT'D

```
08.trace                                                                    9/20/2007 5:05 PM 3381  183_HRV68     AACTTCTCCCAATGGAAAATTACAATTAAGGAAATGGCTCAAATTAGAAGAAAGTGTGAA
3382  184_HRV68a    AACTTCTCCCAATGGAAAATTAAGGAAATGGCTCAAATTAGAAGAAAGTGTGAA
3383  185_HRV68b    AACTTCTCCCAATGGAAAATTACAATTAAGGAAATGGCTCAAATTAGAAGAAAGTGTGAA
3384  186_HRV28     AATTTTAGTAAATGGAATATCACTCTCAAAGAAATGGCCCAAATCAGAAGAAAGTGTGAA
3385  187_HRV28a    AATTTTAGTAAATGGAATATCACTCTCAAAGAAATGGCCCAAATCAGAAGAAAGTGTGAA
3386  188_HRV28b    AATTTTAGTAAATGGAATATCACTCTCAAAGAAATGGCCCAAATCAGAAGAAAGTGTGAA
3387  189_HRV53a    AACCACTCAGAATGGAAGATTACACTCAAAGAAATGGCCCAGATTAGAAGGAAATGTGAG
3388  190_HRV53b    AACCACTCAGAATGGAAGATTACACTCAAAGAAATGGCCCAGATTAGAAGGAAATGTGAG
3389  191_HRV53     AACCACTCAGAATGGAAGATTACACTCAAAGAAATGGCCCAGATTAGAAGGAAATGTGAG
3390  192_HRV46a    AACTTCTCAAAATGGAAAATAACACTGTTGGAAATGGCACAAATCAGAAGAAAGTGTGAA
3391  193_HRV46b    AACTTCTCAAAATGGAAAATAACACTGTTGGAAATGGCACAAATCAGAAGAAAGTGTGAA
3392  194_HRV46     AACTTCTCAAAATGGAAAATAACACTGTTGGAAATGGCACAAATCAGAAGAAAGTGTGAA
3393  195_HRV80a    AATTTTTCAAAGTGGAAAATAACATTAATGGAAATGGCACAAATTAGAAGAAAGTGTGAG
3394  196_HRV80b    AATTTTTCAAAGTGGAAAATAACATTAATGGAAATGGCACAAATTAGAAGAAAGTGTGAG
3395  197_HRV80     AATTTTTCAAAGTGGAAAATAACATTAATGGAAATGGCACAAATTAGAAGAAAGTGTGAG
3396  198_HRV51     AATTTCTCTACATGGAAAATTACACTCAAAGAAATGGCTCAAATTAGAAGAAAGTGTGAA
3397  199_HRV51a    AATTTCTCTACATGGAAAATTACACTCAAAGAAATGGCTCAAATTAGAAGAAAGTGTGAA
3398  200_HRV51b    AATTTCTCTACATGGAAAATTACACTCAAAGAAATGGCTCAAATTAGAAGAAAGTGTGAA
3399  201_HRV65a    AATTTCTCTGCTTGGGAAATTACACTCAAAGAAATGGCTCAAATTAGGAGAAAGTGTGAA
3400  202_HRV65b    AATTTCTCTGCTTGGGAAATTACACTCAAGGAAATGGCTCAAATTAGGAGAAAGTGTGAA
3401  203_HRV65     AATTTCTCTGCTTGGGAAATTACACTCAAGGAAATGGCTCAAATTAGGAGAAAGTGTGAA
3402  204_HRV71a    AATCTCTCAAAGTGGCAGATTACACTCAAAGAAATGGCTCAGATCAGGAGGAAATGTGAA
3403  205_HRV71b    AATCTCTCAAAGTGGCAGATTACACTCAAAGAAATGGCTCAGATCAGGAGGAAATGTGAA
3404  206_HRV71     AATCTCTCAAAGTGGCAGATTACACTCAAAGAAATGGCTCAGATCAGGAGGAAATGTGAA
3405  GROUP_5       AA----------TGG-A-AT-AC--T----GAAATGGC-CA-AT-AG-AG-AA-TGTGA-
3406
3407  180_HRV20     CTCTTTACATACCTCAGATTTGATTCTGAGATTACAATAG-TAGCAACAGTAGCTGCACT
3408  181_HRV20a    CTCTTTACATACCTCAGATTTGATTCTGAGATTACAATAG-TAGCAACAGTAGCTGCACT
3409  182_HRV20b    CTCTTTACATACCTCAGATTTGATTCTGAGATTACAATAG-TAGCAACAGTAGCTGCACT
3410  183_HRV68     CTATTCACATACCTTAGGTTTGACTCTGAGATTACAATAG-TAGCAACAATAGCTGCTCT
3411  184_HRV68a    CTATTCACATACCTTAGGTTTGACTCTGAGATTACAATAG-TAGCAACAATAGCTGCTCT
3412  185_HRV68b    CTATTCACATACCTTAGGTTTGACTCTGAGATTACAATAG-TAGCAACAATAGCTGCTCT
3413  186_HRV28     ATGTTTACATATCTCAGATTTGATTCTGAAATTACTATAG-TGGTGTCAGTTGCAAGTAA
3414  187_HRV28a    ATGTTTACATATCTCAGATTTGATTCTGAAATTACTATAG-TGGTGTCAGTTGCAAGTAA
3415  188_HRV28b    ATGTTTACATATCTCAGATTTGATTCTGAAATTACTATAG-TGGTGTCAGTTGCAAGTAA
3416  189_HRV53a    ATGTTCACATATCTTAGATTTGATTCAGAAATAACTATAG-TGGTATCAGTGGCTAGTAA
3417  190_HRV53b    ATGTTCACATATCTTAGATTTGATTCAGAAATAACTATAG-TGGTATCAGTGGCTAGTAA
3418  191_HRV53     ATGTTCACATATCTTAGATTTGATTCAGAAATAACTATAG-TGGTATCAGTGGCTAGTAA
3419  192_HRV46a    CTTTTTACATATCTCAGATTTGATTCAGAAATAACAATAG-TCACCACATTGGCAGGCCA
3420  193_HRV46b    CTTTTTACATATCTCAGATTTGATTCAGAAATAACAATAG-TCACCACATTGGCAGGCCA
3421  194_HRV46     CTTTTTACATATCTCAGATTTGATTCAGAAATAACAATAG-TCACCACATTGGCAGGCCA
3422  195_HRV80a    CTTTTCACTTACCTCAGATTTGACTCAGAAATAACAATAG-TAACTACCTTAGCAGGACA
3423  196_HRV80b    CTTTTCACTTACCTCAGATTTGACTCAGAAATAACAATAG-TAACTACCTTAGCAGGACA
3424  197_HRV80     CTTTTCACTTACCTCAGATTTGACTCAGAAATAACAATAG-TAACTACCTTAGCAGGACA
3425  198_HRV51     CTTTTCACATACTTAAGATTTGATTCAGAGATCACTATAG-TTGCTACCATTGCTGGACA
3426  199_HRV51a    CTTTTCACATACTTAAGATTTGATTCAGAGATCACTATAG-TTGCTACCATTGCTGGACA
3427  200_HRV51b    CTTTTCACATACTTAAGATTTGATTCAGAGATCACTATAG-TTGCTACCATTGCTGGACA
3428  201_HRV65a    CTCTTCACCTATTTGCGCTTTGACTCAGAAATTACCATAG-TGGCTACTATAGCTGGACA
3429  202_HRV65b    CTCTTCACCTATTTGCGCTTTGACTCAGAAATTACCATAG-TGGCTACTATAGCTGGACA
3430  203_HRV65     CTCTTCACCTATTTGCGCTTTGACTCAGAAATTACCATAG-TGGCTACTATAGCTGGACA
3431  204_HRV71a    CTCTTCACATACCTGCGCTTTGATTCAGAGATAACAATTG-TAGCTACACTAGCAGGGCA
3432  205_HRV71b    CTCTTCACATACCTGCGCTTTGATTCAGAGATAACAATTG-TAGCTACACTAGCAGGGCA
3433  206_HRV71     CTCTTCACATACCTGCGCTTTGATTCAGAGATAACAATTG-TAGCTACACTAGCAGGGCA
3434  GROUP_5       -T-TT-AC-TA--T--G-TTTGA-TC-GA-AT-AC-AT-G.T-----C--T-GC------
3435
3436  180_HRV20     AGGTCGGGATAATGGGCATGTTGTTTTACAGTATATGTATGTACCACCAGGGGCACCAAT
3437  181_HRV20a    AGGTCGGGATAATGGGCATGTTGTTTTACAGTATATGTATGTACCACCAGGGGCACCAAT
3438  182_HRV20b    AGGTCGGGATAATGGGCATGTTGTTTTACAGTATATGTATGTACCACCAGGGGCACCAAT
3439  183_HRV68     TGGAAAAGATAATGGCCATGTGGTTTTACAGTACATGTATGTGCCGCCAGGGGCACCCAT
3440  184_HRV68a    TGGAAAAGATAATGGCCATGTGGTTTTACAGTACATGTATGTGCCGCCAGGGGCACCCAT
3441  185_HRV68b    TGGAAAAGATAATGGCCATGTGGTTTTACAGTACATGTATGTGCCGCCAGGGGCACCCAT
3442  186_HRV28     AGGTGATGATAATGGGCATGTAGTTATGCAATATATGTATGTACCTCCAGGAGCCCCCAT
3443  187_HRV28a    AGGTGATGATAATGGGCATGTAGTTATGCAATATATGTATGTACCTCCAGGAGCCCCCAT
3444  188_HRV28b    AGGTGATGATAATGGGCATGTAGTTATGCAATATATGTATGTACCTCCAGGAGCCCCCAT
3445  189_HRV53a    ACAAGGGAATAACGGGCACGTGGTGATACAATACATGTATGTACCACCGGGTGCTCCAAT
```

FIG. D12 CONT'D

```
08.trace                                                                9/20/2007 5:05 PM 3446 190_HRV53b   ACAAGGGAATAACGGGCACGTGGTGATACAATACATGTATGTACCACCGGGTGCTCCAAT
3447 191_HRV53    ACAAGGGAATAACGGGCACGTGGTGATACAATACATGTATGTACCACCGGGTGCTCCAAT
3448 192_HRV46a   AGGGGATGATATTGGACATGTGGTCATACAATATATGTATGTGCCTCCTGGTGCTCCATT
3449 193_HRV46b   AGGGGATGATATTGGACATGTGGTCATACAATATATGTATGTGCCTCCTGGTGCTCCATT
3450 194_HRV46    AGGGGATGATATTGGACATGTGGTCATACAATATATGTATGTGCCTCCTGGTGCTCCATT
3451 195_HRV80a   AGGGGAGGACATTGGTCATGTAGTTATTCAATACATGTACGTACCACCAGGGGCCCCGTT
3452 196_HRV80b   AGGGGAGGACATTGGTCATGTAGTTATTCAATACATGTACGTACCACCAGGGGCCCCGTT
3453 197_HRV80    AGGGGAGGACATTGGTCATGTAGTTATTCAATACATGTACGTACCACCAGGGGCCCCGTT
3454 198_HRV51    GGGTGATGACATAGGGCACATTGTACTTCAATACATGTATGTACCCCTGGAGGACCAGT
3455 199_HRV51a   GGGTGATGACATAGGGCACATTGTACTTCAATACATGTATGTACCCCTGGAGGACCAGT
3456 200_HRV51b   GGGTGATGACATAGGGCACATTGTACTTCAATACATGTATGTACCCCTGGAGGACCAGT
3457 201_HRV65a   AGGTGATGACATAGGGCACATAGTGCTTCAATATATGTATGTGCCTCCTGGTGGTCCTGT
3458 202_HRV65b   AGGTGATGACATAGGGCACATAGTGCTTCAATATATGTATGTGCCTCCTGGTGGTCCTGT
3459 203_HRV65    AGGTGATGACATAGGGCACATAGTGCTTCAATATATGTATGTGCCTCCTGGTGGTCCTGT
3460 204_HRV71a   AGGAGATGATTTAGGACATATTGTACTCCAGTACATGTATGTTCCCCCAGGTGGTCCAAT
3461 205_HRV71b   AGGAGATGATTTAGGACATATTGTACTCCAGTACATGTATGTTCCCCCAGGTGGTCCAAT
3462 206_HRV71    AGGAGATGATTTAGGACATATTGTACTCCAGTACATGTATGTTCCCCCAGGTGGTCCAAT
3463 GROUP_5      --------A----GG-CA--T-GT--T-CA-TA-ATGTA-GT-CC-CC-GG-G--CC--T
3464
3465 180_HRV20    ACCAAAGACTAGAGATGACTACACATGGCAATCAGGGACAAATGCATCAGTATTTTGGCA
3466 181_HRV20a   ACCAAAGACTAGAGATGACTACACATGGCAATCAGGGACAAATGCATCAGTATTTTGGCA
3467 182_HRV20b   ACCAAAGACTAGAGATGACTACACATGGCAATCAGGGACAAATGCATCAGTATTTTGGCA
3468 183_HRV68    ACCAAAAACTAGAGATGATTACACATGGCAGTCAGGCACTAATGCATCAGTGTTTTGGCA
3469 184_HRV68a   ACCAAAAACTAGAGATGATTACACATGGCAGTCAGGCACTAATGCATCAGTGTTTTGGCA
3470 185_HRV68b   ACCAAAAACTAGAGATGATTACACATGGCAGTCAGGCACTAATGCATCAGTGTTTTGGCA
3471 186_HRV28    CCCCACTACCAGAAATGATTACACATGGCAATCCAGTACCAATGCCTCTGTTTTCTGGCA
3472 187_HRV28a   CCCCACTACCAGAAATGATTACACATGGCAATCCAGTACCAATGCCTCTGTTTTCTGGCA
3473 188_HRV28b   CCCCACTACCAGAAATGATTACACATGGCAATCCAGTACCAATGCCTCTGTTTTCTGGCA
3474 189_HRV53a   ACCCAAAACCAGAGATGACTATACCTGGCAATCTGGAACTAATGCTTCAGTCTTTTGGCA
3475 190_HRV53b   ACCCAAAACCAGAGATGACTATACCTGGCAATCTGGAACTAATGCTTCAGTCTTTTGGCA
3476 191_HRV53    ACCCAAAACCAGAGATGACTATACCTGGCAATCTGGAACTAATGCTTCAGTCTTTTGGCA
3477 192_HRV46a   ACCGAGATATCGGAATGATTATACTTGGCAGTCTGGTACTAATGCTTCAGTGTTCTGGCA
3478 193_HRV46b   ACCGAGATATCGGAATGATTATACTTGGCAGTCTGGTACTAATGCTTCAGTGTTCTGGCA
3479 194_HRV46    ACCGAGATATCGGAATGATTATACTTGGCAGTCTGGTACTAATGCTTCAGTGTTCTGGCA
3480 195_HRV80a   GCCAAACAAACGCAATGATTATACTTGGCAGTCTGGCACGAATGCTTCAGTCTTCTGGCA
3481 196_HRV80b   GCCAAACAAACGCAATGATTATACTTGGCAGTCTGGCACGAATGCTTCAGTCTTCTGGCA
3482 197_HRV80    GCCAAACAAACGCAATGATTATACTTGGCAGTCTGGCACGAATGCTTCAGTCTTCTGGCA
3483 198_HRV51    TCCACTTACTAGGAAAGATGATGAGTGGCAATCAGGAACTAATGCTTCAGTATTCTGGCA
3484 199_HRV51a   TCCACTTACTAGGAAAGATGATGAGTGGCAATCAGGAACTAATGCTTCAGTATTCTGGCA
3485 200_HRV51b   TCCACTTACTAGGAAAGATGATGAGTGGCAATCAGGAACTAATGCTTCAGTATTCTGGCA
3486 201_HRV65a   TCCAAAAACTAGAAAAGATGAAGAGTGGCAGACAGGAACTAATGCTTCAGTCTTTTGGCA
3487 202_HRV65b   TCCAAAAACTAGAAAAGATGAAGAGTGGCAGACAGGAACTAATGCTTCAGTCTTTTGGCA
3488 203_HRV65    TCCAAAAACTAGAAAAGATGAAGAGTGGCAGACAGGAACTAATGCTTCAGTCTTTTGGCA
3489 204_HRV71a   ACCAGAGACCAGGGATGCCGATGAATGGCAGTCTGGAACTAATGCATCAGTCTTTTGGCA
3490 205_HRV71b   ACCAGAGACCAGGGATGCCGATGAATGGCAGTCTGGAACTAATGCATCAGTCTTTTGGCA
3491 206_HRV71    ACCAGAGACCAGGGATGCCGATGAATGGCAGTCTGGAACTAATGCATCAGTCTTTTGGCA
3492 GROUP_5      -CC--------G--A-G---A----TGGCA--C--G-AC-AATGC-TC-GT-TT-TGGCA
3493
3494 180_HRV20    GCAGGGCCAACCTTACCCCAGATTTACCATTCCATTTATGAGTATAGCTTCAGCATATTA
3495 181_HRV20a   GCAGGGCCAACCTTACCCCAGATTTACCATTCCATTTATGAGTATAGCTTCAGCATATTA
3496 182_HRV20b   GCAGGGCCAACCTTACCCCAGATTTACCATTCCATTTATGAGTATAGCTTCAGCATATTA
3497 183_HRV68    ACAAGGACAACCTTACCCCAGATTTACCATTCCATTTATGAGTATAGCTTCAGCATATTA
3498 184_HRV68a   ACAAGGACAACCTTACCCCAGATTTACCATTCCATTTATGAGTATAGCTTCAGCATATTA
3499 185_HRV68b   ACAAGGACAACCTTACCCCAGATTTACCATTCCATTTATGAGTATAGCTTCAGCATATTA
3500 186_HRV28    ACAAGGACAACCATATCCCAGATTCACTATACCTTTTATGAGTATTGCCTCAGCTTATTA
3501 187_HRV28a   ACAAGGACAACCATATCCCAGATTCACTATACCTTTTATGAGTATTGCCTCAGCTTATTA
3502 188_HRV28b   ACAAGGACAACCATATCCCAGATTCACTATACCTTTTATGAGTATTGCCTCAGCTTATTA
3503 189_HRV53a   ACAAGGACAACCATACCCTAGATTCACAATCCCTTTCATGAGTATTGCGTCAGCATATTA
3504 190_HRV53b   ACAAGGACAACCATACCCTAGATTCACAATCCCTTTCATGAGTATTGCGTCAGCATATTA
3505 191_HRV53    ACAAGGACAACCATACCCTAGATTCACAATCCCTTTCATGAGTATTGCGTCAGCATATTA
3506 192_HRV46a   GCAAGGGCAGCCATACCCTAGATTCACTATCCCGTTCATGAGTATAGCCTCAGCATATTA
3507 193_HRV46b   GCAAGGGCAGCCATACCCTAGATTCACTATCCCGTTCATGAGTATAGCCTCAGCATATTA
3508 194_HRV46    GCAAGGGCAGCCATACCCTAGATTCACTATCCCGTTCATGAGTATAGCCTCAGCATATTA
3509 195_HRV80a   ACAGGGTCAGCCATACCCCAGATTCACTATTCCATTCATGAGTATAGCCTCAGCTTATTA
3510 196_HRV80b   ACAGGGTCAGCCATACCCCAGATTCACTATTCCATTCATGAGTATAGCCTCAGCTTATTA
```

FIG. D12 CONT'D

```
08.trace                                                                  9/20/2007 5:05 PM 3511 197_HRV80   ACAGGGTCAGCCATACCCCAGATTCACTATTCCATTCATGAGTATAGCCTCAGCTTATTA
3512 198_HRV51   ACATGGACAACCATACCCTAGATTTACAATCCCTTTTGTAAGCATAGCCTCAGCATACTA
3513 199_HRV51a  ACATGGACAACCATACCCTAGATTTACAATCCCTTTTGTAAGCATAGCCTCAGCATACTA
3514 200_HRV51b  ACATGGACAACCATACCCTAGATTTACAATCCCTTTTGTAAGCATAGCCTCAGCATACTA
3515 201_HRV65a  GCATGGTCAACCATACCCCAGATTTACAATTCCTTTTGTGAGTATTGCCTCAGCATATTA
3516 202_HRV65b  GCATGGTCAACCATACCCCAGATTTACAATTCCTTTTGTGAGTATTGCCTCAGCATATTA
3517 203_HRV65   GCATGGTCAACCATACCCCAGATTTACAATTCCTTTTGTGAGTATTGCCTCAGCATATTA
3518 204_HRV71a  GCACGGCCAACCATACCCAAGGTTTACAATCCCCTTCATAAGCATTGCATCAGCATATTA
3519 205_HRV71b  GCACGGCCAACCATACCCAAGGTTTACAATCCCCTTCATAAGCATTGCATCAGCATATTA
3520 206_HRV71   GCACGGCCAACCATACCCAAGGTTTACAATCCCCTTCATAAGCATTGCATCAGCATATTA
3521 GROUP_5    -CA-GG-CA-CC-TA-CC-AG-TT-AC-AT-CC-TT--T-AG-AT-GC-TCAGC-TA-TA
3522
3523 180_HRV20   TATGTTTTATGATGGTTATGAAGATGATAAGG---GAAGTGTGTATGGGTCTGTTGTCAC
3524 181_HRV20a  TATGTTTTATGATGGTTATGAAGATGATAAGG---GAAGTGTGTATGGGTCTGTTGTCAC
3525 182_HRV20b  TATGTTTTATGATGGTTATGAAGATGATAAGG---GAAGTGTGTATGGGTCTGTTGTCAC
3526 183_HRV68   TATGTTTTATGATGGATATGAGGATGACAAAG---GAAGTGTGTATGGATCTGTTGTTAC
3527 184_HRV68a  TATGTTTTATGATGGATATGAGGATGACAAAG---GAAGTGTGTATGGATCTGTTGTTAC
3528 185_HRV68b  TATGTTTTATGATGGATATGAGGATGACAAAG---GAAGTGTGTATGGATCTGTTGTTAC
3529 186_HRV28   CATGTTTTATGATGGTTATGAAGATGACAATG---GAACTACCTATGGTGCAGTGGTTAC
3530 187_HRV28a  CATGTTTTATGATGGTTATGAAGATGACAATG---GAACTACCTATGGTGCAGTGGTTAC
3531 188_HRV28b  CATGTTTTATGATGGTTATGAAGATGACAATG---GAACTACCTATGGTGCAGTGGTTAC
3532 189_HRV53a  TATGTTCTATGATGGGTATGAAGATGACAATG---GCACCACTTATGGGGCTGTTGTTAC
3533 190_HRV53b  TATGTTCTATGATGGGTATGAAGATGACAATG---GCACCACTTATGGGGCTGTTGTTAC
3534 191_HRV53   TATGTTCTATGATGGGTATGAAGATGACAATG---GCACCACTTATGGGGCTGTTGTTAC
3535 192_HRV46a  CATGTTTTATGATGGCTACGAAAGTGATAAAG---GCAAGATCTATGGAACTGCAGTCAC
3536 193_HRV46b  CATGTTTTATGATGGCTACGAAAGTGATAAAG---GCAAGATCTATGGAACTGCAGTCAC
3537 194_HRV46   CATGTTTTATGATGGCTACGAAAGTGATAAAG---GCAAGATCTATGGAACTGCAGTCAC
3538 195_HRV80a  CATGTTCTATGATGGGTATGAGAGTGATAAAG---GCAACATTTATGGAACAGCAGTTAC
3539 196_HRV80b  CATGTTCTATGATGGGTATGAGAGTGATAAAG---GCAACATTTATGGAACAGCAGTTAC
3540 197_HRV80   CATGTTCTATGATGGGTATGAGAGTGATAAAG---GCAACATTTATGGAACAGCAGTTAC
3541 198_HRV51   CATGTTTTATGATGGGTATGAAGGTGATAGTTTGACCTCACAGTACGGTTCAGTAGTCAC
3542 199_HRV51a  CATGTTTTATGATGGGTATGAAGGTGATAGTTTGACCTCACAGTACGGTTCAGTAGTCAC
3543 200_HRV51b  CATGTTTTATGATGGGTATGAAGGTGATAGTTTGACCTCACAGTACGGTTCAGTAGTCAC
3544 201_HRV65a  CATGTTCTATGATGGTTATGAGGGTGATGACCCAAATTCAAAATATGGTTCAGTGGTTAC
3545 202_HRV65b  CATGTTCTATGATGGTTATGAGGGTGATGACCCAAATTCAAAATATGGTTCAGTGGTTAC
3546 203_HRV65   CATGTTCTATGATGGTTATGAGGGTGATGACCCAAATTCAAAATATGGTTCAGTGGTTAC
3547 204_HRV71a  CATGTTCTATGATGGGTATGAAGGTGATGCCCTCAGTTCTAAATATGGCTCAGTAGTTAC
3548 205_HRV71b  CATGTTCTATGATGGGTATGAAGGTGATGCCCTCAGTTCTAAATATGGCTCAGTAGTTAC
3549 206_HRV71   CATGTTCTATGATGGGTATGAAGGTGATGCCCTCAGTTCTAAATATGGCTCAGTAGTTAC
3550 GROUP_5    -ATGTT-TATGATGG--TA-GA---TGA--------------TA-GG--C-G--GT-AC
3551
3552 180_HRV20   AAACGATATGGGCACATTGTGTGTTCGTATTGTGACTGAGCAGCAGACACATAAGGTTAA
3553 181_HRV20a  AAACGATATGGGCACATTGTGTGTTCGTATTGTGACTGAGCAGCAGACACATAAGGTTAA
3554 182_HRV20b  AAACGATATGGGCACATTGTGTGTTCGTATTGTGACTGAGCAGCAGACACATAAGGTTAA
3555 183_HRV68   AAATGATATGGGCACATTATGTGTCCGTATTGTGACTGAGCAGCAGACACATAGGGTCAA
3556 184_HRV68a  AAATGATATGGGCACATTATGTGTCCGTATTGTGACTGAGCAGCAGACACATAGGGTCAA
3557 185_HRV68b  AAATGATATGGGCACATTATGTGTCCGTATTGTGACTGAGCAGCAGACACATAGGGTCAA
3558 186_HRV28   AAATCATATGGGAACACTCTGTGCTCGCATAGTAACTGAACAACAGAAGCATGAAGTCAA
3559 187_HRV28a  AAATCATATGGGAACACTCTGTGCTCGCATAGTAACTGAACAACAGAAGCATGAAGTCAA
3560 188_HRV28b  AAATCATATGGGAACACTCTGTGCTCGCATAGTAACTGAACAACAGAAGCATGAAGTCAA
3561 189_HRV53a  TAATGATATGGGAACACTTTGTGTGCGCATAGTGACTGAGCAACAGAAAAATGAGGTCAA
3562 190_HRV53b  TAATGATATGGGAACACTTTGTGTGCGCATAGTGACTGAGCAACAGAAAAATGAGGTCAA
3563 191_HRV53   TAATGATATGGGAACACTTTGTGTGCGCATAGTGACTGAGCAACAGAAAAATGAGGTCAA
3564 192_HRV46a  CAATGATATGGGAACTATATGTGTCAGAATTGTTACCGAACAACAAAAACATAAGGTTCT
3565 193_HRV46b  CAATGATATGGGAACTATATGTGTCAGAATTGTTACCGAACAACAAAAACATAAGGTTCT
3566 194_HRV46   CAATGATATGGGAACTATATGTGTCAGAATTGTTACCGAACAACAAAAACATAAGGTTCT
3567 195_HRV80a  CAATGATATGGGAACCCTGTGTGCTAGAATTGTTACAGAACAACAGAAACATAAAGTCCT
3568 196_HRV80b  CAATGATATGGGAACCCTGTGTGCTAGAATTGTTACAGAACAACAGAAACATAAAGTCCT
3569 197_HRV80   CAATGATATGGGAACCCTGTGTGCTAGAATTGTTACAGAACAACAGAAACATAAAGTCCT
3570 198_HRV51   AAATGCTATGGGGACACTATGTGTTCGTGTGGTCACAGAGCAACAAAAACATGAGGTTAA
3571 199_HRV51a  AAATGCTATGGGGACACTATGTGTTCGTGTGGTCACAGAGCAACAAAAACATGAGGTTAA
3572 200_HRV51b  AAATGCTATGGGGACACTATGTGTTCGTGTGGTCACAGAGCAACAAAAACATGAGGTTAA
3573 201_HRV65a  TAATGCTATGGGCACACTATATGTGCGTGTGGTTACAGAAAGGCAAAAACATGAAGTCAA
3574 202_HRV65b  TAATGCTATGGGCACACTATATGTGCGTGTGGTTACAGAAAGGCAAAAACATGAAGTCAA
3575 203_HRV65   TAATGCTATGGGCACACTATATGTGCGTGTGGTTACAGAAAGGCAAAAACATGAAGTCAA
```

FIG. D12 CONT'D

```
08.trace                                                                    9/20/2007 5:05 PM 3576  204_HRV71a   TAATGCCATGGGCACCTTATGTGTTCGTGTGGTTACAGAACAGCAAAGCAACACAGTCAA
3577  205_HRV71b   TAATGCCATGGGCACCTTATGTGTTCGTGTGGTTACAGAACAGCAAAGCAACACAGTCAA
3578  206_HRV71    TAATGCCATGGGCACCTTATGTGTTCGTGTGGTTACAGAACAGCAAAGCAACACAGTCAA
3579  GROUP_5      -AA----ATGGG-AC--T-T-TG---G--T-GT-AC-GA----CA-A---A----GT---
3580
3581  180_HRV20    GATAACCAGTAGGATATTCCACAAGGCAAAGCATATTAGTGCATGGTGTCCAAGGGCCCC
3582  181_HRV20a   GATAACCAGTAGGATATTCCACAAGGCAAAGCATATTAGTGCATGGTGTCCAAGGGCCCC
3583  182_HRV20b   GATAACCAGTAGGATATTCCACAAGGCAAAGCATATTAGTGCATGGTGTCCAAGGGCCCC
3584  183_HRV68    AATAACCAGCAGAATATTCCATAAAGCAAAACATATTAGTGCGTGGTGTCCAAGAGCTCC
3585  184_HRV68a   AATAACCAGCAGAATATTCCATAAAGCAAAACATATTAGTGCGTGGTGTCCAAGAGCTCC
3586  185_HRV68b   AATAACCAGCAGAATATTCCATAAAGCAAAACATATTAGTGCGTGGTGTCCAAGAGCTCC
3587  186_HRV28    AATAACCAGCATAATATTCCACAAAGCTAAACATGTCAGTGCATGGTGCCCCAGACCTCC
3588  187_HRV28a   AATAACCAGCATAATATTCCACAAAGCTAAACATGTCAGTGCATGGTGCCCCAGACCTCC
3589  188_HRV28b   AATAACCAGCATAATATTCCACAAAGCTAAACATGTCAGTGCATGGTGCCCCAGACCTCC
3590  189_HRV53a   GATAACCAGTAGGATTTATCACAAGGCTAAACATATCAGTGCATGGTGTCCAAGACCACC
3591  190_HRV53b   GATAACCAGTAGGATTTATCACAAGGCTAAACATATCAGTGCATGGTGTCCAAGACCACC
3592  191_HRV53    GATAACCAGTAGGATTTATCACAAGGCTAAACATATCAGTGCATGGTGTCCAAGACCACC
3593  192_HRV46a   TATAACTAGCAGAATATATCACAAGGCTAAACACATTAAAGCATGGTGCCCCAGGGCACC
3594  193_HRV46b   TATAACTAGCAGAATATATCACAAGGCTAAACACATTAAAGCATGGTGCCCCAGGGCACC
3595  194_HRV46    TATAACTAGCAGAATATATCACAAGGCTAAACACATTAAAGCATGGTGCCCCAGGGCACC
3596  195_HRV80a   AATCACCAGCAGAATATATCACAAAGCTAAACACATCAAAGCATGGTGTCCAAGAGCACC
3597  196_HRV80b   AATCACCAGCAGAATATATCACAAAGCTAAACACATCAAAGCATGGTGTCCAAGAGCACC
3598  197_HRV80    AATCACCAGCAGAATATATCACAAAGCTAAACACATCAAAGCATGGTGTCCAAGAGCACC
3599  198_HRV51    CATAACTAGCAGGATTTACCACAAAGCCAAACATGTCAGTGCATGGTGCCCTCGTCCTCC
3600  199_HRV51a   CATAACTAGCAGGATTTACCACAAAGCCAAACATGTCAGTGCATGGTGCCCTCGTCCTCC
3601  200_HRV51b   CATAACTAGCAGGATTTACCACAAAGCCAAACATGTCAGTGCATGGTGCCCTCGTCCTCC
3602  201_HRV65a   CATAACCAGTAGAATATATCATAAAGCTAAACACATCAGTGCTTGGTGTCCACGACCTCC
3603  202_HRV65b   CATAACCAGTAGAATATATCATAAAGCTAAACACATCAGTGCTTGGTGTCCACGACCTCC
3604  203_HRV65    CATAACCAGTAGAATATATCATAAAGCTAAACACATCAGTGCTTGGTGTCCACGACCTCC
3605  204_HRV71a   CATAACAAGTAGGATTTATCACAAAGCCAAACATGTCAGAGCATGGTGTCCTAGACCCCC
3606  205_HRV71b   CATAACAAGTAGGATTTATCACAAAGCCAAACATGTCAGAGCATGGTGTCCTAGACCCCC
3607  206_HRV71    CATAACAAGTAGGATTTATCACAAAGCCAAACATGTCAGAGCATGGTGTCCTAGACCCCC
3608  GROUP_5      -AT-AC-AG-A--AT-T--CA-AA-GC-AA-CA--T-A--GC-TGGTG-CC--G--C-CC
3609
3610  180_HRV20    AAGAGCAGTGCCTTATCAA-CACACTAAGAGCACAAACTTAGTGC-CAAGGA---CAGGT
3611  181_HRV20a   AAGAGCAGTGCCTTATCAA-CACACTAAGAGCACAAACTTAGTGC-CAAGGA---CAGGT
3612  182_HRV20b   AAGAGCAGTGCCTTATCAA-CACACTAAGAGCACAAACTTAGTGC-CAAGGA---CAGGT
3613  183_HRV68    AAGAGCAGTGCCCTACCAG-CACACCAGAAGTACAAACTTAGTAC-CAAAGG---AAGGT
3614  184_HRV68a   AAGAGCAGTGCCCTACCAG-CACACCAGAAGTACAAACTTAGTAC-CAAAGG---AAGGT
3615  185_HRV68b   AAGAGCAGTGCCCTACCAG-CACACCAGAAGTACAAACTTAGTAC-CAAAGG---AAGGT
3616  186_HRV28    ACGCGCTGTAGCTTATCAA-CATACATACAGTCCAAACTTTGTGC-CTCAGG---AAGGT
3617  187_HRV28a   ACGCGCTGTAGCTTATCAA-CATACATACAGTCCAAACTTTGTGC-CTCAGG---AAGGT
3618  188_HRV28b   ACGCGCTGTAGCTTATCAA-CATACATACAGTCCAAACTTTGTGC-CTCAGG---AAGGT
3619  189_HRV53a   AAGAGCAGTTGCATATCAA-CACACATATAGCCCAAATTTTGTAC-CGCAAA---CAGGA
3620  190_HRV53b   AAGAGCAGTTGCATATCAA-CACACATATAGCCCAAATTTTGTAC-CGCAAA---CAGGA
3621  191_HRV53    AAGAGCAGTTGCATATCAA-CACACATATAGCCCAAATTTTGTAC-CGCAAA---CAGGA
3622  192_HRV46a   CAGAGCAGTCCCATATCAA-CATATTTATAATCCAAATTTCAAGA-CTACTCAACCTGAG
3623  193_HRV46b   CAGAGCAGTCCCATATCAA-CATATTTATAATCCAAATTTCAAGA-CTACTCAACCTGAG
3624  194_HRV46    CAGAGCAGTCCCATATCAA-CATATTTATAATCCAAATTTCAAGA-CTACTCAACCTGAG
3625  195_HRV80a   TAGAGCAGTCCCATACCAA-CATACCTACAGCCCAAATTTCAAAA-ACACTG---ATGAA
3626  196_HRV80b   TAGAGCAGTCCCATACCAA-CATACCTACAGCCCAAATTTCAAAA-ACACTG---ATGAA
3627  197_HRV80    TAGAGCAGTCCCATACCAA-CATACCTACAGCCCAAATTTCAAAA-ACACTG---ATGAA
3628  198_HRV51    TCGTGCTGTAGCCTACCAA-CACACATACAGTACAAACTTCGTTC-CAAAAGAGGGATTT
3629  199_HRV51a   TCGTGCTGTAGCCTACCAA-CACACATACAGTACAAACTTCGTTC-CAAAAGAGGGATTT
3630  200_HRV51b   TCGTGCTGTAGCCTACCAA-CACACATACAGTACAAACTTCGTTC-CAAAAGAGGGATTT
3631  201_HRV65a   CCGAGCAGTAGCTTACCAA-CACACATACAGTACAAATTTTGTTC-CTAGCGGAGGTCTT
3632  202_HRV65b   CCGAGCAGTAGCTTACCAA-CACACATACAGTACAAATTTTGTTC-CTAGCGGAGGTCTT
3633  203_HRV65    CCGAGCAGTAGCTTACCAA-CACACATACAGTACAAATTTTGTTC-CTAGCGGAGGTCTT
3634  204_HRV71a   CAGAGCAGTAGCCTACCAA-TCAACATATACCACAAATTTTGTTC-CACAAGACGGGATC
3635  205_HRV71b   CAGAGCAGTAGCCTACCAA-TCAACATATACCACAAATTTTGTTC-CACAAGACGGGATC
3636  206_HRV71    CAGAGCAGTAGCCTACCAA-TCAACATATACCACAAATTTTGTTC-CACAAGACGGGATC
3637  GROUP_5      --G-GC-GT--C-TA-CA-.---A-----A---CAAA-TT-----.--------------
3638
3639  180_HRV20    GAAA------TTACA---ACTCATATCAGATTCAGAAACACTGTCAAAGATCTAACATAC
3640  181_HRV20a   GAAA------TTACA---ACTCATATCAGATTCAGAAACACTGTCAAAGATCTAACATAC
```

FIG. D12 CONT'D

```
08.trace                                                                9/20/2007 5:05 PM 3641 182_HRV20b    GAAA------TTACA---ACTCATATCAGATTCAGAAACACTGTCAAAGATCTAACATAC
3642 183_HRV68     GATA------TTAAA---ACTCATATTAAATTTAGGAATACTGTTAAAGATTTGGCATAT
3643 184_HRV68a    GATA------TTAAA---ACTCATATTAAATTTAGGAATACTGTTAAAGATTTGGCATAT
3644 185_HRV68b    GATA------TTAAA---ACTCATATTAAATTTAGGAATACTGTTAAAGATTTGGCATAT
3645 186_HRV28     GATG------TTGAG---ACTCATATTAAATTTAGAACAGATGTTAAACAGATCACAA--
3646 187_HRV28a    GATG------TTGAG---ACTCATATTAAATTTAGAACAGATGTTAAACAGATCACAA--
3647 188_HRV28b    GATG------TTGAG---ACTCATATTAAATTTAGAACAGATGTTAAACAGATCACAA--
3648 189_HRV53a    ACAG------TTGAA---ACTCACATTAAGTTCAGACCTGATGTTAAAGATGTAACAT--
3649 190_HRV53b    ACAG------TTGAA---ACTCACATTAAGTTCAGACCTGATGTTAAAGATGTAACAT--
3650 191_HRV53     ACAG------TTGAA---ACTCACATTAAGTTCAGACCTGATGTTAAAGATGTAACAT--
3651 192_HRV46a    ACTA------TACCAGATACTCATATTGGAATTAGAAGGGATATAAAGTACATTAAAA--
3652 193_HRV46b    ACTA------TACCAGATACTCATATTGGAATTAGAAGGGATATAAAGTACATTAAAA--
3653 194_HRV46     ACTA------TACCAGATACTCATATTGGAATTAGAAGGGATATAAAGTACATTAAAA--
3654 195_HRV80a    TCTA------TACCAGATACACAAATTAAAATCAGAGATAATATCAGGCAGGTTAGAA--
3655 196_HRV80b    TCTA------TACCAGATACACAAATTAAAATCAGAGATAATATCAGGCAGGTTAGAA--
3656 197_HRV80     TCTA------TACCAGATACACAAATTAAAATCAGAGATAATATCAGGCAGGTTAGAA--
3657 198_HRV51     GAAG------GCTTGAAAACTCAGATTAAAACTAGGGCAGACATCAAACTTGTGAACT--
3658 199_HRV51a    GAAG------GCTTGAAAACTCAGATTAAAACTAGGGCAGACATCAAACTTGTGAACT--
3659 200_HRV51b    GAAG------GCTTGAAAACTCAGATTAAAACTAGGGCAGACATCAAACTTGTGAACT--
3660 201_HRV65a    ACAA------ACCTAAGAACCCAAATTAAAACCAGAGATAACATTAAAATTGTAAACT--
3661 202_HRV65b    ACAA------ACCTAAGAACCCAAATTAAAACCAGAGATAACATTAAAATTGTAAACT--
3662 203_HRV65     ACAA------ACCTAAGAACCCAAATTAAAACCAGAGATAACATTAAAATTGTAAACT--
3663 204_HRV71a    AATT------CCATTAAAACCAAAATCAAAATCAGAAGAGACATTAAAGAGGTCAGCA--
3664 205_HRV71b    AATT------CCATTAAAACCAAAATCAAAATCAGAAGAGACATTAAAGAGGTCAGCA--
3665 206_HRV71     AATT------CCATTAAAACCAAAATCAAAATCAGAAGAGACATTAAAGAGGTCAGCA--
3666 GROUP_5       ----......--------AC--A-AT-------AG--------T-A------T-------
3667
3668 180_HRV20     CCCACAGAAATGACGAATGTT
3669 181_HRV20a    CCCACAGAAATGACGAATGTA
3670 182_HRV20b    CCCACAGAAATGACGAATGTG
3671 183_HRV68     CCTCCAGAATTAGCAAACCTT
3672 184_HRV68a    CCTCCAGAATTAGCAAACCTT
3673 185_HRV68b    CCTCCAGAATTAGCAAACCTT
3674 186_HRV28     ----CAGTT------------
3675 187_HRV28a    ----CAGTA------------
3676 188_HRV28b    ----CAGTC------------
3677 189_HRV53a    ----CAGTAATGACAGCT---
3678 190_HRV53b    ----CAGTAATGACAGCT---
3679 191_HRV53     ----CAGTAATGACAGCA---
3680 192_HRV46a    ----CAGCA------------
3681 193_HRV46b    ----CAGCC------------
3682 194_HRV46     ----CAGCT------------
3683 195_HRV80a    ----CAGTA------------
3684 196_HRV80b    ----CAGTC------------
3685 197_HRV80     ----CAGTT------------
3686 198_HRV51     -----TT--------------
3687 199_HRV51a    -----TA--------------
3688 200_HRV51b    -----TG--------------
3689 201_HRV65a    -----TG--------------
3690 202_HRV65b    -----TA--------------
3691 203_HRV65     -----TT--------------
3692 204_HRV71a    -----ACTAA-----------
3693 205_HRV71b    -----ACTAG-----------
3694 206_HRV71     -----ACTAT-----------
3695 GROUP_5       ---------------------
3696
3697
3698
3699 Group  6:
3700
3701 207_HRV8      AACCCTATTGAACAATTCACAGAGGCAGTATTAAACGAGGTTCTTGTAGTTCCAAACACA
3702 208_HRV95     AACCCTATTGAACAATTCACAGAGGCAGTATTAAACGAGGTTCTTGTAGTTCCAAATACA
3703 209_HRV45     AACCCTGTTGAACAATTTGCAGAAGCAGTCCTTGATCAAGTATTAGTAGTTCCAAACACT
3704 210_HRV45a    AACCCTGTTGAACAATTTGCAGAAGCAGTCCTTGATCAAGTATTAGTAGTTCCAAACACT
3705 211_HRV45b    AACCCTGTTGAACAATTTGCAGAAGCAGTCCTTGATCAAGTATTAGTAGTTCCAAACACT
```

FIG. D12 CONT'D

```
08.trace                                                                    9/20/2007 5:05 PM 3706  GROUP_6      AACCCT-TTGAACAATT--CAGA-GCAGT--T--A--A-GT--T-GTAGTTCCAAA-AC-
3707
3708  207_HRV8     CAAGCTAGTAATGGATCTATAGCAAATTCAGCACCAGCATTAGATGCAGCAGAGACTGGA
3709  208_HRV95    CAAGCCAGTAATGGATCTATAGCAAATTCAGCACCAGCATTAGATGCAGCAGAGACTGGA
3710  209_HRV45    CGACCCAGCGATGGGTTGATTGCAAACTCAGCCCCAGCTTTGGATGCAGCTGAAACTGGA
3711  210_HRV45a   CGACCCAGCGATGGGTTGATTGCAAACTCAGCCCCAGCTTTGGATGCAGCTGAAACTGGA
3712  211_HRV45b   CGACCCAGCGATGGGTTGATTGCAAACTCAGCCCCAGCTTTGGATGCAGCTGAAACTGGA
3713  GROUP_6      C-A-C-AG---ATGG-T--AT-GCAAA-TCAGC-CCAGC-TT-GATGCAGC-GA-ACTGGA
3714
3715  207_HRV8     CACACAAGTTCAGTGCAACCTGAAGATCTTATAGAGACTAGGTATGTAATTACAGATCAA
3716  208_HRV95    CACACAAGTTCAGTGCAACCTGAAGATCTTATAGAGACTAGGTATGTAATTACAGATCAA
3717  209_HRV45    CACACCAGTTCAGTGCAGCCTGAGGACCTTATAGAGACTAGATATGTGATTGCAGACCAA
3718  210_HRV45a   CACACCAGTTCAGTGCAGCCTGAGGACCTTATAGAGACTAGATATGTGATTGCAGACCAA
3719  211_HRV45b   CACACCAGTTCAGTGCAGCCTGAGGACCTTATAGAGACTAGATATGTGATTGCAGACCAA
3720  GROUP_6      CACAC-AGTTCAGTGCA-CCTGA-GA-CTTATAGAGACTAG-TATGT-ATT-CAGA-CAA
3721
3722  207_HRV8     ACTAGGCATGAGACATCACTGGAATCTTTCTTGGGTAGAGCAGGATGCATTAAAATCATT
3723  208_HRV95    ACTAGGTATGAGACATCACTGGAATCTTTCTTGGGTAGAGCAGGATGCATTAAAATTATT
3724  209_HRV45    ACCAGACATGAAACCTCCATTGAATCTTTTTTGGGTAGGGCTGGATGTGTGGCCAATATT
3725  210_HRV45a   ACCAGACATGAAACCTCCATTGAATCTTTTTTGGGTAGGGCTGGATGTGTGGCCAATATT
3726  211_HRV45b   ACCAGACATGAAACCTCCATTGAATCTTTTTTGGGTAGGGCTGGATGTGTGGCCAATATT
3727  GROUP_6      AC-AG--ATGA-AC-TC--T-GAATCTTT--TTGGGTAG-GC-GGATG--T----A--ATT
3728
3729  207_HRV8     GCATTAGAACTAGATCATGACAAC---------------TATGATGAA------------
3730  208_HRV95    GCATTAGAACTAGATCATGACAAC---------------TATGATAAA------------
3731  209_HRV45    AGTTTAGACATTAACCATGATGAC---------------TACCAAAAG------------
3732  210_HRV45a   AGTTTAGACATTAACCATGATGAC---------------TACCAAAAG------------
3733  211_HRV45b   AGTTTAGACATTAACCATGATGAC---------------TACCAAAAG------------
3734  GROUP_6      ---TTAGA--T--A-CATGA--AC.............TA--A--A-............
3735
3736  207_HRV8     AGTTTCAGGACCTGGGGAATAAACATACAAGAGATGTCACAAATTAGAAGGAAATTTGAG
3737  208_HRV95    AATTTCAGGACCTGGGGAATAAACATACAAGAGATGTCACAAATTAGAAGGAAATTTGAA
3738  209_HRV45    AATTACAAAAATTGGGCAATTAGTTTACAAGAAATGTCACAAATTAGGAGGAAATTTGAA
3739  210_HRV45a   AATTACAAAAATTGGGCAATTAGTTTACAAGAAATGTCACAAATTAGGAGGAAATTTGAA
3740  211_HRV45b   AATTACAAAAATTGGGCAATTAGTTTACAAGAAATGTCACAAATTAGGAGGAAATTTGAA
3741  GROUP_6      A-TT-CA--A--TGGG-AAT-A---TACAAGA-ATGTCACAAATTAG-AGGAAATTTGA-
3742
3743  207_HRV8     ATGTTCACTTATGTAAGATTTGATTCAGAGATAACAATTG-TACCATGTATTGCAGCTAT
3744  208_HRV95    ATGTTCACTTATGTAAGATTTGATTCAGAGATAACAATTG-TACCATGTATTGCAGCTAT
3745  209_HRV45    ATGTTTACATATGTCAGATTTGATTCCGAAATAACAATAG-TACCATGTGTTGCTGCCAC
3746  210_HRV45a   ATGTTTACATATGTCAGATTTGATTCCGAAATAACAATAG-TACCATGTGTTGCTGCCAC
3747  211_HRV45b   ATGTTTACATATGTCAGATTTGATTCCGAAATAACAATAG-TACCATGTGTTGCTGCCAC
3748  GROUP_6      ATGTT-AC-TATGT-AGATTTGATTC-GA-ATAACAAT-G.TACCATGT-TTGC-GC-A-
3749
3750  207_HRV8     AAAAGGTGACCTTGGACACATAGTCCTTCAATACATGTATGTTCCCCCGGGTGCACCTCT
3751  208_HRV95    AGAAGGTGACCTTGGACACATAGTCCTCCAATACATGTATGTTCCCCCGGGTGCACCTCT
3752  209_HRV45    AGAAGGTAACCTTGGGACACATTGTTGTGCAATACATGTTTGTACCACCAGGAGCACCTCT
3753  210_HRV45a   AGAAGGTAACCTTGGGACACATTGTTGTGCAATACATGTTTGTACCACCAGGAGCACCTCT
3754  211_HRV45b   AGAAGGTAACCTTGGGACACATTGTTGTGCAATACATGTTTGTACCACCAGGAGCACCTCT
3755  GROUP_6      A-AAGGT-AC-T-GGACACAT-GT--T-CAATACATGT-TGT-CC-CC-GG--GCACCTCT
3756
3757  207_HRV8     TCCAGATAAAAGGATGCACGATGCCTGGCAAACCAGTACAAATGCCTCAGTCTTCTGGCA
3758  208_HRV95    TCCAGATAAAAGGATGCACGATGCCTGGCAAACCAGTACAAATGCCTCAGTCTTCTGGCA
3759  209_HRV45    CCCTGTTAGTAGAACTGACAACACTTGGCAATCTAGCACAAATGCATCAGTCTTTTGGCA
3760  210_HRV45a   CCCTGTTAGTAGAACTGACAACACTTGGCAATCTAGCACAAATGCATCAGTCTTTTGGCA
3761  211_HRV45b   CCCTGTTAGTAGAACTGACAACACTTGGCAATCTAGCACAAATGCATCAGTCTTTTGGCA
3762  GROUP_6      -CC-G-TA--AG-A---AC-A--C-TGGCAA-C-AG-ACAAATGC-TCAGTCTT-TGGCA
3763
3764  207_HRV8     AGTTGGACAAACTTATCCCAGATTCACCATACCTTTCTCCAGCATAGCATCAGCTTATTA
3765  208_HRV95    AGTTGGACAGACTTATCCCAGATTCACCATACCTTTCTCCAGTATAGCATCAGCTTATTA
3766  209_HRV45    GGTTGGTCAAACTTATCCCAGATTTTCTATACCTTTCTCAAGTATAGCTTCAGCTTACTA
3767  210_HRV45a   GGTTGGTCAAACTTATCCCAGATTTTCTATACCTTTCTCAAGTATAGCTTCAGCTTACTA
3768  211_HRV45b   GGTTGGTCAAACTTATCCCAGATTTTCTATACCTTTCTCAAGTATAGCTTCAGCTTACTA
3769  GROUP_6      -GTTGG-CA-ACTTATCCCAGATT--C-ATACCTTTCTC-AG-ATAGC-TCAGCTTA-TA
3770
```

FIG. D12 CONT'D 08.trace                                                          9/20/2007 5:05 PM

```
3771 207_HRV8    CATGTTCTATGATGGTTATGATTCAGATGGTTTAGATGCTATTTATGGTATTCCTGTTAC
3772 208_HRV95   CATGTTCTATGATGGTTATGATTCAGATGGTTTAGATGCTATTTATGGTATTCCTGTTAC
3773 209_HRV45   CATGTTTTATGATGGATACGACACTGATGGCACAGATGCAGTGTATGGTGTTAGTGTGAC
3774 210_HRV45a  CATGTTTTATGATGGATACGACACTGATGGCACAGATGCAGTGTATGGTGTTAGTGTGAC
3775 211_HRV45b  CATGTTTTATGATGGATACGACACTGATGGCACAGATGCAGTGTATGGTGTTAGTGTGAC
3776 GROUP_6     CATGTT-TATGATGG-TA-GA--C-GATGG---AGATGC--T-TATGGT-TT--TGT-AC
3777
3778 207_HRV8    AAATCACATGGGCACAATATGTGTGAGAATGGTGACAGATAAACAGAAAATTAAAACTAA
3779 208_HRV95   AAATCACATGGGCACAATATGTGTGAGAATGGTGACAGATAAACAGAAAATTAAAACTAA
3780 209_HRV45   TAACCATATGGGGACTATATGTGTTAGAATTGTTACAGACCAACAACAACATAGAGTTAA
3781 210_HRV45a  TAACCATATGGGGACTATATGTGTTAGAATTGTTACAGACCAACAACAACATAGAGTTAA
3782 211_HRV45b  TAACCATATGGGGACTATATGTGTTAGAATTGTTACAGACCAACAACAACATAGAGTTAA
3783 GROUP_6     -AA-CA-ATGGG-AC-ATATGTGT-AGAAT-GT-ACAGA--AACA--AA--TA-A--TAA
3784
3785 207_HRV8    AATTGATTCAAGAATATACCTGAAAGCAAAGCACATTAAAGCTTGGTGTCCTAGACCCCC
3786 208_HRV95   AATTGATTCAAGAATATACCTGAAAGCAAAGCATATTAAAGCTTGGTGTCCTAGACCCCC
3787 209_HRV45   GATCGACTCCATGGTATATCTAAAAGCTAAACACATCAAGGCATGGTGTCCCAGACCTCC
3788 210_HRV45a  GATCGACTCCATGGTATATCTAAAAGCTAAACACATCAAGGCATGGTGTCCCAGACCTCC
3789 211_HRV45b  GATCGACTCCATGGTATATCTAAAAGCTAAACACATCAAGGCATGGTGTCCCAGACCTCC
3790 GROUP_6     -AT-GA-TC-A---TATA-CT-AAAGC-AA--CA-AT-AA-GC-TGGTGTCC-AGACC-CC
3791
3792 207_HRV8    CAGAGCAGTTACGTATAAC-CATATATACAACCCCAATTATGTTA-GAGAGG------GA
3793 208_HRV95   CAGAGCAGTTACGTATAAC-CATATATACAACCCCAATTATGTTA-GAGAGG------GA
3794 209_HRV45   AAGAGCAGTCACATATAAC-CATACATATAATCCAAATTATGTTA-GGGCTG------AT
3795 210_HRV45a  AAGAGCAGTCACATATAAC-CATACATATAATCCAAATTATGTTA-GGGCTG------AT
3796 211_HRV45b  AAGAGCAGTCACATATAAC-CATACATATAATCCAAATTATGTTA-GGGCTG------AT
3797 GROUP_6     -AGAGCAGT-AC-TATAAC.CATA-ATA-AA-CC-AATTATGTTA.G-G--G........--
3798
3799 207_HRV8    GTAA------CACCAGAAACTAAGGTTAAATATAGAGCTGAAGTCACAACCATT------
3800 208_HRV95   GTAA------CACCAGAAACTAAGGTCAAATATAGAGCTGAAGTCACAACCATT------
3801 209_HRV45   GAAA------CAGCC---ACAAAAGTCCAAACTAGAGCAAATGTCACAACAGTA------
3802 210_HRV45a  GAAA------CAGCC---ACAAAAGTCCAAACTAGAGCAAATGTCACAACAGTG------
3803 211_HRV45b  GAAA------CAGCC---ACAAAAGTCCAAACTAGAGCAAATGTCACAACAGTT------
3804 GROUP_6     G-AA......CA-C----AC-AA-GT--AA--TAGAGC--A-GTCACAAC--T-......
3805
3806 207_HRV8    --------------------
3807 208_HRV95   --------------------
3808 209_HRV45   --------------------
3809 210_HRV45a  --------------------
3810 211_HRV45b  --------------------
3811 GROUP_6     ....................
3812
3813
3814
3815 Summary:
3816
3817 GROUP_1      AA-CC--T-GA----T---T--A-----T--T-AA--A-GT--T--T-GT-CC--A----
3818 GROUP_2      AA-CC--TTGA--A-T---TAGATGA-GT-CTTA-TGA-GT-TTAGTTGT-CC-AA--AT-
3819 GROUP_3      AA-CC-GT-GA-AA-TA--TAGATA---T--TAAA-GAAGT--T-GT-GT-CC-AA-AT-
3820 GROUP_4      AATCCAGT-GA---ATATGTTGAT-AGGT-TAAATGA-GTT-TAAGTTGTTCCAAACATA
3821 GROUP_5      AA-CC--T-GA-A--TA-AC-GA-GC--T--T-AATGA--T--T-GT-GT-CC--AA-AT-
3822 GROUP_6      AACCCT-TTGAACAATT--CAGA-GCAGT--T--A--A-GT--T-GTAGTTCCAAA-AC-
3823 SUMMARY      AA-CC--T-GA----T---X--A-----T--T-----A-GT--T--T-GT-CC--A----
3824
3825 GROUP_1      ----A-AG----------A--TC-AA--C-GC--C-----T-GA-GC-GC-GA-AC-GG-
3826 GROUP_2      AA-AGTAGT-A-CC-AC-ACATCAAA-TCTGC-CC-GCATTAGA-GCTGC-GAAAC-GG-
3827 GROUP_3      CA-CC-AG--CATC-GT-TCAAGTCA--C-G--CC-GC--T-GA-GCTGC-GA-AC-GG-
3828 GROUP_4      AA--AAAGTAA----CAGT-----AAC-C-GC-CCAG--TTGGACGCTGCAGAAAC-GGT
3829 GROUP_5      ----C-AG-A-----CA-AC--C-AA--C-GC-CC--C--T-GATGC-GC--GA-AC-GG-
3830 GROUP_6      C-A-C-AG--ATGG-T--AT-GCAAA-TCAGC-CCAGC-TT-GATGCAGC-GA-ACTGGA
3831 SUMMARY      ----X-AG----------X-----XA--C-G---C-----T-GA-GC-GC-GA-AC-GG-
3832
3833 GROUP_1      CA-AC-A--------CA-CC-GA-GA-----T-GA-AC--G----GT----------A-
3834 GROUP_2      CA-ACTAG-A-TGT-CAACC-GA-GATGTCATTGAAAC-AG-TA-GT-CA-ACATGACAA
3835 GROUP_3      CA-AC-AG-TCTGT-CA-CC-GA-GA-ATGAT-GA-AC-AG-TATGT-AT-AC-GA-CAA
```

FIG. D12 CONT'D

```
08.trace                                                                          9/20/2007 5:05 PM 3836 GROUP_4     CATAC-A-CCAA--ACA-CC-GAAGA----AT-GAAAC-AG-TATGT-AT-AC-GACCA-
3837 GROUP_5     CA-AC-A--CA----CA-CC-GA-GA--T--T-GA-AC--G-TATGT--T-AC-GA-CA-
3838 GROUP_6     CACAC-AGTTCAGTGCA-CCTGA-GA-CTTATAGAGACTAG-TATGT-ATT-CAGA-CAA
3839 SUMMARY     CA-AC-A--------CA-CC-GA-GA-----T-GA-AC--G----GT----------A-
3840
3841 GROUP_1     AC-----ATGA-ATG-G--T-GA--G-TT--T-GG-AG--C-GG-TG--T-CA-----C-
3842 GROUP_2     ACAAG-GATGAAATGAGTTTAGA-AG-TT-CTTGG-AG-TCAGG-TG-ATACA-GA-TC-
3843 GROUP_3     ACAAG-GATGA-AC-AG-AT-GA-AG-TT--T-GGTAG-TC-GG-TG-AT-GC-A---T-
3844 GROUP_4     AC-AGAGATGA-ATG---ATTGAA--TTTCCT-GG--G-TC-GG-TG-----CAATTAT-
3845 GROUP_5     AC----GATGA-ATGAG--T-GA-AG-TT--T-GG-AG-TC----TG--T-GC----AT-
3846 GROUP_6     AC-AG--ATGA-AC-TC--T-GAATCTTT-TTGGGTAG-GC-GGATG--T----A--ATT
3847 SUMMARY     AC-----ATGA-AX-----T-GA----TT--T-GG--G--C----TG----------X-
3848
3849 GROUP_1     ----T-------------------.............---------...---------
3850 GROUP_2     AAA-TA-A--T-----T---A-A-.............TA--A---.........A--A-
3851 GROUP_3     -AA-TT---ACAA---------A---T.........-A--A-GA-------A--GG----
3852 GROUP_4     --A-T-GA-TT-GACCA----G-T.............TA----GC-...GAAGGGAAA
3853 GROUP_5     -A-AC--A--T----CA---------------------TA-AA----...--G-----
3854 GROUP_6     ---TTAGA--T--A-CATGA--AC.............TA--A--A-............
3855 SUMMARY     ----X-------------------------------------------------------
3856
3857 GROUP_1     ------------TGG----T-A---T--A-GA-ATG-C-CA--T--G--G-AA-T--GA-
3858 GROUP_2     AA-TT-A-----TGG---AT-AAT-T-CA-GAAATGGC-CA-AT-AGAAG-AA-TTTGA-
3859 GROUP_3     GG-T-----ACATGGAA--T-AG--T-CAAGA-ATGGCACAAAT-AG-AG-AA-T-TGA-
3860 GROUP_4     AA-TTTA-AAC-TGGAA-AT-AA--T--AGGA-ATGGCCCAGATTAGAAG-AA-AATGAG
3861 GROUP_5     AA---------TGG-A-AT-AC--T----GAAATGGC-CA-AT-AG-AG-AA-TGTGA-
3862 GROUP_6     A-TT-CA--A--TGGG-AAT-A---TACAAGA-ATGTCACAAATTAG-AGGAAATTGA-
3863 SUMMARY     ------------TGG----T-A---T----GA-ATG-C-CA--T--G--G-AA-X--GA-
3864
3865 GROUP_1     -T-TT-AC-TA----AG-TTT-A-TC-GA--T-AC--T-G.T-C------T--C------
3866 GROUP_2     -T-TT-AC-TA-ACTAG-TT-GATTCTGA-AT-AC--T-G.TTCC-TG-ATTTC-GC-CT
3867 GROUP_3     -T-TT-ACATA-AC-AGATTTGA-TC-GA-AT-ACAATAG.TCAC-GCAGC-GC-G--CA
3868 GROUP_4     -T-TTCAC-TA--T-AG-TTTGATTC-GAAATCAC--TTG-T----GCA-TG-C--CA--
3869 GROUP_5     -T-TT-AC-TA--T--G-TTTGA-TC-GA-AT-AC-AT-G.T-----C--T-GC-----
3870 GROUP_6     ATGTT-AC-TATGT-AGATTTGATTC-GA-ATAACAAT-G.TACCATGT--TTGC-GC-A-
3871 SUMMARY     -T-TT-AC-TA-----G-TT--A-TC-GA--T-AC--T-G-X--------X--C------
3872
3873 GROUP_1     ----------T-GG-CA--T-GT-ATGCA-T--ATGT---T-CC-CC-GG-GC-CC---
3874 GROUP_2     -AG--A-GA-AT-GG-CACAT-ACAATGCA-TA-ATGTATGT-CC-CC-GG-GC-CC--T
3875 GROUP_3     -GG--A-GATA-TGG-CAT-T-GT--T-CAATT-ATGTATGT-CC-CCAGG-GC-CC--T
3876 GROUP_4     AG-AG--A--AATGG-CA-GTGGTG-T-CAAT--ATGT-TGT-CC-CCTGG-GCCCC--T
3877 GROUP_5     --------A----GG-CA--T-GT-T-CA-TA-ATGTA-GT-CC-CC-GG-G--CC--T
3878 GROUP_6     A-AAGGT-AC-T-GGACACAT-GT--T-CAATACATGT-TGT-CC-CC-GG-GCACCTCT
3879 SUMMARY     ------------GG-CA--T-XX--T-CA-T--ATGT---T-CC-CC-GG-G--CC---
3880
3881 GROUP_1     -CC-------AG-----A-T-----TGG-A-TC--G-A--AA----TC----TT-TGGCA
3882 GROUP_2     -CC--A-AG-AG--A-GA-TATGCATGGCA-TCTGG-AC-AATGC-TC--TTTT-TGGCA
3883 GROUP_3     -CC----AA-CG-GA-GA-T--ACATGGCA-TCAGG-ACAAATGC-TCT-T-TT-TGGCA
3884 GROUP_4     ACC-AA-AA--G-GATGA-TA-AC-TGGCA-TC-GGCACCAA-GC-TC-GT-TTTTGGCA
3885 GROUP_5     -CC--------G--A-G---A----TGGCA--C--G-AC-AATGC-TC--GT-TT-TGGCA
3886 GROUP_6     -CC-G-TA--AG-A---AC-A--C-TGGCAA-C-AG-ACAAATGC-TCAGTCTT-TGGCA
3887 SUMMARY     -CC--------G-------------TGG-A--C--G-A--AA----TC----TT-TGGCA
3888
3889 GROUP_1     ----GG-CA----T--CC--G--T--C--T-CC-TT--T--G--T-GC-TC-G--TA-TA
3890 GROUP_2     ACA-GG-CA--C-TA-CCAAG-TT-TC--TACC-TT--T-AGTGT-GC-TC-GCTTA-TA
3891 GROUP_3     -GA-GG-CAACCATA-CC-AGATT-AC-AT-CC-TTTATGAG-ATTGCATCAGC-TA-TA
3892 GROUP_4     --AAGGTCAA-C-TACCCCAG-TTC-C-AT-CC-TTT--TAGTATTGCCTCAGC-TATTA
3893 GROUP_5     -CA-GG-CA-CC-TA-CC-AG-TT--AC-AT-CC-TT--T-AG-AT-GC-TCAGC-TA-TA
3894 GROUP_6     -GTTGG-CA--ACTTATCCCAGATT--C-ATACCTTTCTC-AG-ATAGC-TCAGCTTA-TA
3895 SUMMARY     ----GG-CA----T--CC--G--T--C--T-CC-TT-----G--T-GC-TC-G--TA-TA
3896
3897 GROUP_1     -ATGTT-TA-GA-GG-TA--A-G---------------C----TA-GG-----------
3898 GROUP_2     CATGTT-TATGATGG-TA--ATG......A----G------A-TATGG-AC-G--AG-AC
3899 GROUP_3     -ATGTT-TATGATGG-TATGATGGTGAT--TGC----ATC-A--TA-GG-TC-GT-GT-AC
3900 GROUP_4     CATGTTTTATGATGG-TA--C-GATGACA-C-CA----C-CC-TATGG-ACTGTAGTTAC
```

FIG. D12 CONT'D

```
08.trace                                                                      9/20/2007 5:05 PM 3901 GROUP_5      -ATGTT-TATGATGG-TA-GA---TGA----------------TA-GG---C-G--GT-AC
3902 GROUP_6      CATGTT-TATGATGG-TA-GA--C-GATGG----AGATGC--T-TATGGT-TT--TGT-AC
3903 SUMMARY      -ATGTT-TA-GA-GG-TA--X---------------------TA-GG------------
3904
3905 GROUP_1      -AA----ATGGG--C--T-TG-----G--T--T-AC-------CA-----------T---
3906 GROUP_2      AAA-AACATGGG--CA-T-TG-TC-AG--T-GTAACAGA-AAACACATTCA-----T-C-
3907 GROUP_3      -AA-GA-ATGGGAAC-ATATGT-TTAGA-T-GT-AC-TC-A--CAAA--CA--A--T-AA
3908 GROUP_4      CAATGACATGGGT-CACTGTGT-T-AG-AT-GTTACAGA-CA-CAA-AACATAA-GT-A-
3909 GROUP_5      -AA----ATGGG-AC--T-T-TG---G--T-GT-AC-GA----CA-A---A----GT---
3910 GROUP_6      -AA-CA-ATGGG--AC-ATATGTGT-AGAAT-GT-ACAGA--AACA--AA--TA-A--TAA
3911 SUMMARY      -AA----ATGGG--C--T-T------G--T--T-AC-------CA---------------
3912
3913 GROUP_1      --T----AC-----T-TA-CA-AA-GC-AA-CA----------TGGTG-CC--G--C-C-
3914 GROUP_2      -AT-ATGACAAG--TCTA-CA-AA-GCTAAACA-GTCAA-GC-TGGTGTCC-CG-CCACC
3915 GROUP_3      -AT--T--G-CG-AT-TA-CA-AA-GC-AA-CA-ATAAA-GC-TGGTG-CC--CG-CCACC
3916 GROUP_4      -ATTAC---TAGA-T-TACCA-AA-GC-AAACATAT-AGTGC-TGGGGCCC-AGACC-CC
3917 GROUP_5      -AT-AC-AG-A--AT-T--CA-AA-GC-AA-CA--T-A--GC-TGGTG-CC--G--C-CC
3918 GROUP_6      -AT-GA-TC-A---TATA-CT-AAAGC-AA-CA-AT-AA-GC-TGGTGTCC-AGACC-CC
3919 SUMMARY      --T----------T-T--CX-AA-GC-AA-CA----------TGGXG-CC--G--C-C-
3920
3921 GROUP_1      --G-G---T----TA----------------A--AA-TA-------------...-----
3922 GROUP_2      -AG-GC-CTTGA-TA-AC-.CG-GCTCA-CG-AC-AATTT-AAA-.TTGA-G...-----
3923 GROUP_3      A-G-GC-GT--C-TA-CA-.--CAC-CA-TC-AC-AA-TA--T-C.CA----...--GG-
3924 GROUP_4      -AGAGCTGTACC-TA-CAG.CA-ATA-A-AA-CC-AATTA-AA-A.C-----......A-
3925 GROUP_5      --G-GC-GT--C-TA-CA-.---A-----A---CAAA-TT-----.--------------
3926 GROUP_6      -AGAGCAGT-AC-TATAAC.CATA-ATA-AA-CC-AATTATGTTA.G-G--G......--
3927 SUMMARY      --G-G---T----TA--------------------AA-TX-------------------
3928
3929 GROUP_1      -----------------------T--------G-----------------------..
3930 GROUP_2      ----......T--A--CA-...---T-------AGA-C-----T-A--ACAGC-......
3931 GROUP_3      GA--......---CA...AC-CA-AT-AAA-CCAGA----AT-T-T--AC--T-----..
3932 GROUP_4      GGA-......-TCCAGACA--A-AGT---A-T-AGAG--A---T-A--AC-GT-......
3933 GROUP_5      ----......---------AC--A-AT-------AG--------T-A------T------
3934 GROUP_6      G-AA......CA-C----AC-AA-GT--AA--TAGAGC--A-GTCACAAC--T-......
3935 SUMMARY      -----------------------T--------G---------------------------
3936
3937 GROUP_1      ....-----............
3938 GROUP_2      .....................
3939 GROUP_3      ....-----............
3940 GROUP_4      .....................
3941 GROUP_5      ---------------------
3942 GROUP_6      .....................
3943 SUMMARY      ---------------------
3944
3945
```

FIG. D12 CONT'D

```
09.trace                                                             9/20/2007 5:05 PM 1  Group  1:   1_HRV1A1|d
     2  Group  1:   2_HRV1A2|d
     3  Group  1:   3_HRV1A|cD
     4  Group  1:   4_HRV1B1|d
     5  Group  1:   5_HRV1B2|d
     6  Group  1:   6_HRV1B
     7
     8  Group  2:   7_HRV40a|d
     9  Group  2:   8_HRV40b|d
    10  Group  2:   9_HRV40
    11  Group  2:  10_HRV85
    12  Group  2:  11_HRV85a|
    13  Group  2:  12_HRV85b|
    14
    15  Group  3:  13_HRV56a|
    16  Group  3:  14_HRV56b|
    17  Group  3:  15_HRV56
    18
    19  Group  4:  16_HRV54
    20  Group  4:  17_HRV98
    21
    22  Group  5:  18_HRV59a|
    23  Group  5:  19_HRV59b|
    24  Group  5:  20_HRV59
    25  Group  5:  21_HRV63
    26  Group  5:  22_HRV63b|
    27  Group  5:  23_HRV63a|
    28
    29  Group  6:  24_HRV39
    30  Group  6:  25_HRV39a|
    31  Group  6:  26_HRV39b|
    32
    33  Group  7:  27_HRV10a|
    34  Group  7:  28_HRV10b|
    35  Group  7:  29_HRV10
    36  Group  7:  30_HRV100a
    37  Group  7:  31_HRV100b
    38  Group  7:  32_HRV100
    39
    40  Group  8:  33_HRV66
    41  Group  8:  34_HRV66b|
    42  Group  8:  35_HRV66a|
    43  Group  8:  36_HRV77a|
    44  Group  8:  37_HRV77b|
    45  Group  8:  38_HRV77
    46
    47  Group  9:  39_HRV62a
    48  Group  9:  40_HRV62b
    49  Group  9:  41_HRV25
    50  Group  9:  42_HRV29a
    51  Group  9:  43_HRV29b
    52  Group  9:  44_HRV44a
    53  Group  9:  45_HRV44b
    54
    55  Group 10:  46_HRV31
    56  Group 10:  47_HRV31a|
    57  Group 10:  48_HRV31b|
    58  Group 10:  49_HRV47
    59  Group 10:  50_HRV47a|
    60  Group 10:  51_HRV47b|
    61
```

FIG. D13

09.trace                                                        9/20/2007 5:05 PM

```
 62 Group 11: 52_HRV11
 63 Group 11: 53_HRV11b|
 64 Group 11: 54_HRV11a|
 65 Group 11: 55_HRV76
 66 Group 11: 56_HRV76b|
 67 Group 11: 57_HRV76a|
 68 Group 11: 58_HRV33
 69 Group 11: 59_HRV33b|
 70 Group 11: 60_HRV33a|
 71
 72 Group 12: 61_HRV24a|
 73 Group 12: 62_HRV24b|
 74 Group 12: 63_HRV24
 75 Group 12: 64_HRV90
 76 Group 12: 65_HRV90a|
 77 Group 12: 66_HRV90b|
 78
 79 Group 13: 67_HRV34
 80 Group 13: 68_HRV34b|
 81 Group 13: 69_HRV34a|
 82 Group 13: 70_HRV50a|
 83 Group 13: 71_HRV50b|
 84 Group 13: 72_HRV50
 85 Group 13: 73_HRV18a|
 86 Group 13: 74_HRV18b|
 87 Group 13: 75_HRV18
 88
 89 Group 14: 76_HRV55
 90 Group 14: 77_HRV55b|
 91 Group 14: 78_HRV55a|
 92
 93 Group 15: 79_HRV57
 94 Group 15: 80_HRV57a|
 95 Group 15: 81_HRV57b|
 96
 97 Group 16: 82_HRV21
 98 Group 16: 83_HRVHan
 99
100 Group 17: 84_HRV43
101 Group 17: 85_HRV43b|
102 Group 17: 86_HRV43a|
103 Group 17: 87_HRV75
104 Group 17: 88_HRV75b|
105 Group 17: 89_HRV75a|
106
107 Group 18: 96_HRV9a|d
108 Group 18: 97_HRV9b|d
109 Group 18: 98_HRV9
110 Group 18: 99_HRV32
111 Group 18: 100_HRV32a
112 Group 18: 101_HRV32b
113 Group 18: 102_HRV67
114 Group 18: 103_HRV67a
115 Group 18: 104_HRV67b
116
117 Group 19: 105_HRV15
118 Group 19: 106_HRV15a
119 Group 19: 107_HRV15b
120 Group 19: 108_HRV74a
121 Group 19: 109_HRV74b
122 Group 19: 110_HRV74
123
124 Group 20: 111_HRV38a
125 Group 20: 112_HRV38b
126 Group 20: 113_HRV38
```

FIG. D13 CONT'D

```
09.trace                                                              9/20/2007 5:05 PM 127
128 Group 21: 114_HRV60
129 Group 21: 115_HRV60a
130 Group 21: 116_HRV60b
131
132 Group 22: 117_HRV64a
133 Group 22: 118_HRV64b
134 Group 22: 119_HRV64
135 Group 22: 120_HRV94a
136 Group 22: 121_HRV94b
137 Group 22: 122_HRV94
138 Group 22: 123_HRV22
139 Group 22: 124_HRV22a
140 Group 22: 125_HRV22b
141
142 Group 23: 126_HRV82
143 Group 23: 127_HRV82b
144 Group 23: 128_HRV82a
145
146 Group 24: 129_HRV19
147 Group 24: 130_HRV19a
148 Group 24: 131_HRV19b
149
150 Group 25: 132_HRV13
151 Group 25: 133_HRV13a
152 Group 25: 134_HRV13b
153 Group 25: 135_HRV41
154 Group 25: 136_HRV41a
155 Group 25: 137_HRV41b
156
157 Group 26: 138_HRV73
158 Group 26: 139_HRV73b
159 Group 26: 140_HRV73a
160
161 Group 27: 141_HRV61
162 Group 27: 142_HRV61a
163 Group 27: 143_HRV61b
164 Group 27: 144_HRV96
165 Group 27: 145_HRV96b
166 Group 27: 146_HRV96a
167
168 Group 28: 90_HRV16a|
169 Group 28: 91_HRV16b|
170 Group 28: 92_1AYM_A
171 Group 28: 93_HRV81a|
172 Group 28: 94_HRV81b|
173 Group 28: 95_HRV81
174
175 Group 29: 147_HRV2
176 Group 29: 148_HRV2a|
177 Group 29: 149_HRV2b|
178 Group 29: 150_HRV49a
179 Group 29: 151_HRV49b
180 Group 29: 152_HRV49
181 Group 29: 153_HRV23a
182 Group 29: 154_HRV23b
183 Group 29: 155_HRV23
184 Group 29: 156_HRV30a
185 Group 29: 157_HRV30b
186 Group 29: 158_HRV30
187
188 Group 30: 159_HRV7
189 Group 30: 160_HRV7b|
190 Group 30: 161_HRV7a|
191 Group 30: 162_HRV88
```

FIG. D13 CONT'D

```
09.trace                                                              9/20/2007 5:05 PM 192 Group 30: 163_HRV88a
  193 Group 30: 164_HRV88b
  194 Group 30: 165_HRV36a
  195 Group 30: 166_HRV36b
  196 Group 30: 167_HRV36
  197 Group 30: 168_HRV89a
  198 Group 30: 169_HRV89b
  199 Group 30: 170_HRV89
  200 Group 30: 171_HRV58
  201 Group 30: 172_HRV58a
  202 Group 30: 173_HRV58b
  203
  204 Group 31: 174_HRV12a
  205 Group 31: 175_HRV12b
  206 Group 31: 176_HRV12
  207
  208 Group 32: 177_HRV78a
  209 Group 32: 178_HRV78b
  210 Group 32: 179_HRV78
  211
  212 Group 33: 180_HRV20
  213 Group 33: 181_HRV20a
  214 Group 33: 182_HRV20b
  215 Group 33: 183_HRV68
  216 Group 33: 184_HRV68a
  217 Group 33: 185_HRV68b
  218
  219 Group 34: 186_HRV28
  220 Group 34: 187_HRV28a
  221 Group 34: 188_HRV28b
  222
  223 Group 35: 189_HRV53a
  224 Group 35: 190_HRV53b
  225 Group 35: 191_HRV53
  226
  227 Group 36: 192_HRV46a
  228 Group 36: 193_HRV46b
  229 Group 36: 194_HRV46
  230 Group 36: 195_HRV80a
  231 Group 36: 196_HRV80b
  232 Group 36: 197_HRV80
  233
  234 Group 37: 198_HRV51
  235 Group 37: 199_HRV51a
  236 Group 37: 200_HRV51b
  237 Group 37: 201_HRV65a
  238 Group 37: 202_HRV65b
  239 Group 37: 203_HRV65
  240
  241 Group 38: 204_HRV71a
  242 Group 38: 205_HRV71b
  243 Group 38: 206_HRV71
  244
  245 Group 39: 207_HRV8
  246 Group 39: 208_HRV95
  247
  248 Group 40: 209_HRV45
  249 Group 40: 210_HRV45a
  250 Group 40: 211_HRV45b
  251
  252
  253 >>>>>
  254
  255
```

FIG. D13 CONT'D 09.trace                                                                    9/20/2007 5:05 PM

```
256
257 Group 1:
258
259   1_HRV1A1|d    AATCCAGTAGAAAACTACATTGATGAAGTTTTAAATGAAGTTTTAGTAGTGCCGAATATA
260   2_HRV1A2|d    AATCCAGTAGAAAACTACATTGATGAAGTTTTAAATGAAGTTTTAGTAGTGCCGAATATA
261   3_HRV1A|cD    AATCCAGTAGAAAACTACATTGATGAAGTTTTAAATGAAGTTTTAGTAGTGCCGAATATA
262   4_HRV1B1|d    AATCCAGTGGAAAATTACATTGATGAAGTTTTAAATGAAGTTCTAGTAGTACCAAATATA
263   5_HRV1B2|d    AATCCAGTGGAAAATTACATTGATGAAGTTTTAAATGAAGTTCTAGTAGTACCAAATATA
264   6_HRV1B       AATCCAGTGGAAAATTACATTGATGAAGTTTTAAATGAAGTTCTAGTAGTACCAAATATA
265   GROUP_1       AATCCAGT-GAAAA-TACATTGATGAAGTTTTAAATGAAGTT-TAGTAGT-CC-AATATA
266
267   1_HRV1A1|d    AAAGAAAGTCATCACACTACATCAAACTCTGCCCCACTTTTAGATGCTGCAGAGACGGGA
268   2_HRV1A2|d    AAAGAAAGTCATCACACTACATCAAACTCTGCCCCACTTTTAGATGCTGCAGAGACGGGA
269   3_HRV1A|cD    AAAGAAAGTCATCACACTACATCAAACTCTGCCCCACTTTTAGATGCTGCAGAGACGGGA
270   4_HRV1B1|d    AAAGAAAGCCATCACACTACATCAAATTCTGCTCCACTCTTGGATGCTGCAGAGACAGGA
271   5_HRV1B2|d    AAAGAAAGCCATCACACTACATCAAATTCTGCTCCACTCTTGGATGCTGCAGAGACAGGA
272   6_HRV1B       AAAGAAAGCCATCACACTACATCAAATTCTGCTCCACTCTTGGATGCTGCAGAGACAGGA
273   GROUP_1       AAAGAAAG-CATCACACTACATCAAA-TCTGC-CCACT-TT-GATGCTGCAGAGAC-GGA
274
275   1_HRV1A1|d    CACACCAGTAATGTTCAACCAGAAGATGCTATAGAGACAAGGTATGTTATAACATCACAA
276   2_HRV1A2|d    CACACCAGTAATGTTCAACCAGAAGATGCTATAGAGACAAGGTATGTTATAACATCACAA
277   3_HRV1A|cD    CACACCAGTAATGTTCAACCAGAAGATGCTATAGAGACAAGGTATGTTATAACATCACAA
278   4_HRV1B1|d    CACACCAGTAATGTACAACCAGAGGATGCTATAGAAACAAGATATGTTATGACATCACAA
279   5_HRV1B2|d    CACACCAGTAATGTACAACCAGAGGATGCTATAGAAACAAGATATGTTATGACATCACAA
280   6_HRV1B       CACACCAGTAATGTACAACCAGAGGATGCTATAGAAACAAGATATGTTATGACATCACAA
281   GROUP_1       CACACCAGTAATGT-CAACCAGA-GATGCTATAGA-ACAAG-TATGTTAT-ACATCACAA
282
283   1_HRV1A1|d    ACAAGAGATGAGATGAGTATAGAAAGTTTCCTTGGTAGATCTGGTTGTGTCCACATCTCA
284   2_HRV1A2|d    ACAAGAGATGAGATGAGTATAGAAAGTTTCCTTGGTAGATCTGGTTGTGTCCACATCTCA
285   3_HRV1A|cD    ACAAGAGATGAGATGAGTATAGAAAGTTTCCTTGGTAGATCTGGTTGTGTCCACATCTCA
286   4_HRV1B1|d    ACAAGAGATGAGATGAGTATAGAAAGTTTTCTTGGTAGATCTGGCTGTGTGCATATTTCA
287   5_HRV1B2|d    ACAAGAGATGAGATGAGTATAGAAAGTTTTCTTGGTAGATCTGGCTGTGTGCATATTTCA
288   6_HRV1B       ACAAGAGATGAGATGAGTATAGAAAGTTTTCTTGGTAGATCTGGCTGTGTGCATATTTCA
289   GROUP_1       ACAAGAGATGAGATGAGTATAGAAAGTTT-CTTGGTAGATCTGG-TGTGT-CA-AT-TCA
290
291   1_HRV1A1|d    AGAATAAAGGTTGATTACACTGAC---------------TATAATGGA---CAGGACATA
292   2_HRV1A2|d    AGAATAAAGGTTGATTACACTGAC---------------TATAATGGA---CAGGACATA
293   3_HRV1A|cD    AGAATAAAGGTTGATTACACTGAC---------------TATAATGGA---CAGGACATA
294   4_HRV1B1|d    AGAATAAAGGTTGATTACAATGAC---------------TACAATGGA---GTGAACAAA
295   5_HRV1B2|d    AGAATAAAGGTTGATTACAATGAC---------------TACAATGGA---GTGAACAAA
296   6_HRV1B       AGAATAAAGGTTGATTACAATGAC---------------TACAATGGA---GTGAACAAA
297   GROUP_1       AGAATAAAGGTTGATTACA-TGAC...............TA-AATGGA...--G-ACA-A
298
299   1_HRV1A1|d    AATTTCACAAAATGGAAAATCACACTACAGGAAATGGCACAGATTAGGAGAAAATTTGAA
300   2_HRV1A2|d    AATTTCACAAAATGGAAAATCACACTACAGGAAATGGCACAGATTAGGAGAAAATTTGAA
301   3_HRV1A|cD    AATTTCACAAAATGGAAAATCACACTACAGGAAATGGCACAGATTAGGAGAAAATTTGAA
302   4_HRV1B1|d    AACTTTACAACATGGAAAATCACACTGCAGGAGATGGCACAAATTAGAAGAAAATTCGAA
303   5_HRV1B2|d    AACTTTACAACATGGAAAATCACACTGCAGGAGATGGCACAAATTAGAAGAAAATTCGAA
304   6_HRV1B       AACTTTACAACATGGAAAATCACACTGCAGGAGATGGCACAAATTAGAAGAAAATTCGAA
305   GROUP_1       AA-TT-ACAA-ATGGAAAATCACACT-CAGGA-ATGGCACA-ATTAG-AGAAAATT-GAA
306
307   1_HRV1A1|d    TTGTTTACATATGTCAGGTTTGACTCAGAAATAACCTTGG-TGCCTTGTATTGCTGGTAG
308   2_HRV1A2|d    TTGTTTACATATGTCAGGTTTGACTCAGAAATAACCTTGG-TGCCTTGTATTGCTGGTAG
309   3_HRV1A|cD    TTGTTTACATATGTCAGGTTTGACTCAGAAATAACCTTGG-TGCCTTGTATTGCTGGTAG
310   4_HRV1B1|d    CTATTTACTTATGTTAGGTTTGATTCAGAAGTAACCTTTAG-TACCCTGTATTGCTGGTAG
311   5_HRV1B2|d    CTATTTACTTATGTTAGGTTTGATTCAGAAGTAACCTTTAG-TACCCTGTATTGCTGGTAG
312   6_HRV1B       CTATTTACTTATGTTAGGTTTGATTCAGAAGTAACCTTTAG-TACCCTGTATTGCTGGTAG
313   GROUP_1       -T-TTTAC-TATGT-AGGTTTGA-TCAGAA-TAAC-TT-G.T-CC-TGTATTGCTGGTAG
314
315   1_HRV1A1|d    AGGAGACGACATTGGACATATTGTAATGCAATATATGTATGTTCCTCCAGGAGCTCCAAT
316   2_HRV1A2|d    AGGAGACGACATTGGACATATTGTAATGCAATATATGTATGTTCCTCCAGGAGCTCCAAT
317   3_HRV1A|cD    AGGAGACGACATTGGACATATTGTAATGCAATATATGTATGTTCCTCCAGGAGCTCCAAT
318   4_HRV1B1|d    AGGAGATGACATTGGTCATGTTGTAATGCAGTATATGTATGTTCCCCCAGGAGCTCCAAT
```

FIG. D13 CONT'D 09.trace                                                                                    9/20/2007 5:05 PM

```
319  5_HRV1B2|d   AGGAGATGACATTGGTCATGTTGTAATGCAGTATATGTATGTTCCCCCAGGAGCTCCAAT
320  6_HRV1B      AGGAGATGACATTGGTCATGTTGTAATGCAGTATATGTATGTTCCCCCAGGAGCTCCAAT
321  GROUP_1     AGGAGA-GACATTGG-CAT-TTGTAATGCA-TATATGTATGTTCC-CCAGGAGCTCCAAT
322
323  1_HRV1A1|d   TCCTTCAAAAAGAAACGATTTCTCATGGCAATCAGGCACCAATATGTCAATATTCTGGCA
324  2_HRV1A2|d   TCCTTCAAAAAGAAACGATTTCTCATGGCAATCAGGCACCAATATGTCAATATTCTGGCA
325  3_HRV1A|cD   TCCTTCAAAAAGAAACGATTTCTCATGGCAATCAGGCACCAATATGTCAATATTCTGGCA
326  4_HRV1B1|d   TCCAAAAACAAGAAATGATTTCTCATGGCAATCAGGCACTAATATGTCAATATTCTGGCA
327  5_HRV1B2|d   TCCAAAAACAAGAAATGATTTCTCATGGCAATCAGGCACTAATATGTCAATATTCTGGCA
328  6_HRV1B      TCCAAAAACAAGAAATGATTTCTCATGGCAATCAGGCACTAATATGTCAATATTCTGGCA
329  GROUP_1     TCC---AA--AAGAAA-GATTTCTCATGGCAATCAGGCAC-AATATGTCAATATTCTGGCA
330
331  1_HRV1A1|d   ACATGGACAGCCATTTCCTAGATTTTCTTTACCATTTCTTAGCATTGCATCAGCTTATTA
332  2_HRV1A2|d   ACATGGACAGCCATTTCCTAGATTTTCTTTACCATTTCTTAGCATTGCATCAGCTTATTA
333  3_HRV1A|cD   ACATGGACAGCCATTTCCTAGATTTTCTTTACCATTTCTTAGCATTGCATCAGCTTATTA
334  4_HRV1B1|d   ACATGGACAACCGTTCCCTAGATTCTCTTTACCATTTCTTAGCATTGCATCAGCTTATTA
335  5_HRV1B2|d   ACATGGACAACCGTTCCCTAGATTCTCTTTACCATTTCTTAGCATTGCATCAGCTTATTA
336  6_HRV1B      ACATGGACAACCGTTCCCTAGATTCTCTTTACCATTTCTTAGCATTGCATCAGCTTATTA
337  GROUP_1     ACATGGACA-CC-TT-CCTAGATT-TCTTTACCATTTCTTAGCATTGCATCAGCTTATTA
338
339  1_HRV1A1|d   TATGTTTTATGATGGATATGATGGAGACAACACTTCTTCCAAGTATGGTAGCGTAGTTAC
340  2_HRV1A2|d   TATGTTTTATGATGGATATGATGGAGACAACACTTCTTCCAAGTATGGTAGCGTAGTTAC
341  3_HRV1A|cD   TATGTTTTATGATGGATATGATGGAGACAACACTTCTTCCAAGTATGGTAGCGTAGTTAC
342  4_HRV1B1|d   CATGTTTTATGATGGATATGATGGAGATAATTCCTCTTCCAAATATGGTAGTATAGTCAC
343  5_HRV1B2|d   CATGTTTTATGATGGATATGATGGAGATAATTCCTCTTCCAAATATGGTAGTATAGTCAC
344  6_HRV1B      CATGTTTTATGATGGATATGATGGAGATAATTCCTCTTCCAAATATGGTAGTATAGTCAC
345  GROUP_1     -ATGTTTTATGATGGATATGATGGAGA-AA--C-TCTTCCAA-TATGGTAG--TAGT-AC
346
347  1_HRV1A1|d   TAATGATATGGGTACTATATGCTCAAGAATAGTTACAGAAAAACAGAAACATTCTGTTGT
348  2_HRV1A2|d   TAATGATATGGGTACTATATGCTCAAGAATAGTTACAGAAAAACAGAAACATTCTGTTGT
349  3_HRV1A|cD   TAATGATATGGGTACTATATGCTCAAGAATAGTTACAGAAAAACAGAAACATTCTGTTGT
350  4_HRV1B1|d   CAATGATATGGGAACCATATGTTCAAGAATAGTTACAGAGAAGCAGGAACACCCTGTCGT
351  5_HRV1B2|d   CAATGATATGGGAACCATATGTTCAAGAATAGTTACAGAGAAGCAGGAACACCCTGTCGT
352  6_HRV1B      CAATGATATGGGAACCATATGTTCAAGAATAGTTACAGAGAAGCAGGAACACCCTGTCGT
353  GROUP_1     -AATGATATGGG-AC-ATATG-TCAAGAATAGTTACAGA-AA-CAG-AACA--CTGT-GT
354
355  1_HRV1A1|d   CATCACAACACACATATATCATAAAGCTAAACACACAAAAGCTTGGTGTCCTAGGCCCCC
356  2_HRV1A2|d   CATCACAACACACATATATCATAAAGCTAAACACACAAAAGCTTGGTGTCCTAGGCCCCC
357  3_HRV1A|cD   CATCACAACACACATATATCATAAAGCTAAACACACAAAAGCTTGGTGTCCTAGGCCCCC
358  4_HRV1B1|d   TATTACAACACACATATATCACAAAGCTAAACACACAAAAGCTTGGTGTCCTAGACCTCC
359  5_HRV1B2|d   TATTACAACACACATATATCACAAAGCTAAACACACAAAAGCTTGGTGTCCTAGACCTCC
360  6_HRV1B      TATTACAACACACATATATCACAAAGCTAAACACACAAAAGCTTGGTGTCCTAGACCTCC
361  GROUP_1     -AT-ACAACACACATATATCA-AAAGCTAAACACACAAAAGCTTGGTGTCCTAG-CC-CC
362
363  1_HRV1A1|d   TAGAGCTGTCCCTTACACA-CATAGTCATGTGACTAATTATATGC-CAGAAA---CAGGT
364  2_HRV1A2|d   TAGAGCTGTCCCTTACACA-CATAGTCATGTGACTAATTATATGC-CAGAAA---CAGGT
365  3_HRV1A|cD   TAGAGCTGTCCCTTACACA-CATAGTCATGTGACTAATTATATGC-CAGAAA---CAGGT
366  4_HRV1B1|d   TAGAGCTGTTCCTTACACA-CATAGTCGTGTAACTAATTATGTAC-CAAAAA---CAGGT
367  5_HRV1B2|d   TAGAGCTGTTCCTTACACA-CATAGTCGTGTAACTAATTATGTAC-CAAAAA---CAGGT
368  6_HRV1B      TAGAGCTGTTCCTTACACA-CATAGTCGTGTAACTAATTATGTAC-CAAAAA---CAGGT
369  GROUP_1     TAGAGCTGT-CCTTACACA.CATAGTC-TGT-ACTAATTAT-T-C.CA-AAA...CAGGT
370
371  1_HRV1A1|d   GACG------TGACAACAG---CCATAGTCCGCAGAA------ACACTATAACAACTG--
372  2_HRV1A2|d   GACG------TGACAACAG---CCATAGTCCGCAGAA------ACACTATAACAACTG--
373  3_HRV1A|cD   GACG------TGACAACAG---CCATAGTCCGCAGAA------ACACTATAACAACTG--
374  4_HRV1B1|d   GATG------TGACAACAG---CTATAGTTCCTAGAG------CTAGCATGAAAACTG--
375  5_HRV1B2|d   GATG------TGACAACAG---CTATAGTTCCTAGAG------CTAGCATGAAAACTG--
376  6_HRV1B      GATG------TGACAACAG---CTATAGTTCCTAGAG------CTAGCATGAAAACTG--
377  GROUP_1     GA-G......TGACAACAG...C-ATAGT-C--AGA-........--A--AT-A-AACTG..
378
379  1_HRV1A1|d   ----CA---------------
380  2_HRV1A2|d   ----CG---------------
381  3_HRV1A|cD   ----CT---------------
382  4_HRV1B1|d   ----TA---------------
383  5_HRV1B2|d   ----TC---------------
```

FIG. D13 CONT'D 09.trace                                                                          9/20/2007 5:05 PM

```
384   6_HRV1B       ----TT---------------
385   GROUP_1       ....--...............
386
387
388
389   Group  2:
390
391   7_HRV40a|d    AACCCCGTTGAAAGGTATGTTGATGAGGTTCTTAATGAAGTTCTGGTAGTTCCAAATATC
392   8_HRV40b|d    AACCCCGTTGAAAGGTATGTTGATGAGGTTCTTAATGAAGTTCTGGTAGTTCCAAATATC
393   9_HRV40       AACCCCGTTGAAAGGTATGTTGATGAGGTTCTTAATGAAGTTCTGGTAGTTCCAAATATC
394   10_HRV85      AATCCTGTTGAAAAATACGTTGATGAAGTCCTTAATGAGGTTCTAGTGGTTCCAAATATC
395   11_HRV85a|    AATCCTGTTGAAAAATACGTTGATGAAGTCCTTAATGAGGTTCTAGTGGTTCCAAATATC
396   12_HRV85b|    AATCCTGTTGAAAAATACGTTGATGAAGTCCTTAATGAGGTTCTAGTGGTTCCAAATATC
397   GROUP_2       AA-CC-GTTGAAA--TA-GTTGATGA-GT-CTTAATGA-GTTCT-GT-GTTCCAAATATC
398
399   7_HRV40a|d    AGAGAGAGCCATCCAACTACATCAAATTCGGCCCCTGCCTTGGATGCAGCAGAGACTGGA
400   8_HRV40b|d    AGAGAGAGCCATCCAACTACATCAAATTCGGCCCCTGCCTTGGATGCAGCAGAGACTGGA
401   9_HRV40       AGAGAGAGCCATCCAACTACATCAAATTCGGCCCCTGCCTTGGATGCAGCAGAGACTGGA
402   10_HRV85      AAAGAGAGTCACCCAACTATATCAAATTCAGCTCCTGCTTTGGATGCAGCAGAGACTGGC
403   11_HRV85a|    AAAGAGAGTCACCCAACTATATCAAATTCAGCTCCTGCTTTGGATGCAGCAGAGACTGGC
404   12_HRV85b|    AAAGAGAGTCACCCAACTATATCAAATTCAGCTCCTGCTTTGGATGCAGCAGAGACTGGC
405   GROUP_2       A-AGAGAG-CA-CCAACTA-ATCAAATTC-GC-CCTGC-TTGGATGCAGCAGAGACTGG-
406
407   7_HRV40a|d    CATACAAGCAACATACAACCTGAAGATACAATAGAAACAAGATTTGTGCAGACATCACAA
408   8_HRV40b|d    CATACAAGCAACATACAACCTGAAGATACAATAGAAACAAGATTTGTGCAGACATCACAA
409   9_HRV40       CATACAAGCAACATACAACCTGAAGATACAATAGAAACAAGATTTGTGCAGACATCACAA
410   10_HRV85      CATACAAGTAGTACACAGCCCGAGGATACAATAGAGACCAGGTTTGTTCAAACTTCACAG
411   11_HRV85a|    CATACAAGTAGTACACAGCCCGAGGATACAATAGAGACCAGGTTTGTTCAAACTTCACAG
412   12_HRV85b|    CATACAAGTAGTACACAGCCCGAGGATACAATAGAGACCAGGTTTGTTCAAACTTCACAG
413   GROUP_2       CATACAAG-A--A-ACA-CC-GA-GATACAATAGA-AC-AG-TTTGT-CA-AC-TCACA-
414
415   7_HRV40a|d    ACTAGAGATGAAATGAGCATAGAGAGTTTCTTGGGAAGATCTGGGTGCATTCATATATCC
416   8_HRV40b|d    ACTAGAGATGAAATGAGCATAGAGAGTTTCTTGGGAAGATCTGGGTGCATTCATATATCC
417   9_HRV40       ACTAGAGATGAAATGAGCATAGAGAGTTTCTTGGGAAGATCTGGGTGCATTCATATATCC
418   10_HRV85      ACTAGGGATGAAATGAGTTTAGAAAGTTTCTTGGGAAGATCTGGATGTATCCATATATCT
419   11_HRV85a|    ACTAGGGATGAAATGAGTTTAGAAAGTTTCTTGGGAAGATCTGGATGTATCCATATATCT
420   12_HRV85b|    ACTAGGGATGAAATGAGTTTAGAAAGTTTCTTGGGAAGATCTGGATGTATCCATATATCT
421   GROUP_2       ACTAG-GATGAAATGAG--TAGA-AGTTTCTTGGGAAGATCTGG-TG-AT-CATATATC-
422
423   7_HRV40a|d    ACAATTACAGTGGATAACAGTTTG---------------GAATATG------ATGACCAC
424   8_HRV40b|d    ACAATTACAGTGGATAACAGTTTG---------------GAATATG------ATGACCAC
425   9_HRV40       ACAATTACAGTGGATAACAGTTTG---------------GAATATG------ATGACCAC
426   10_HRV85      ACAATTACTGTGAATAACAACCTA---------------GATTATG------ATGAAAAT
427   11_HRV85a|    ACAATTACTGTGAATAACAACCTA---------------GATTATG------ATGAAAAT
428   12_HRV85b|    ACAATTACTGTGAATAACAACCTA---------------GATTATG------ATGAAAAT
429   GROUP_2       ACAATTAC-GTG-ATAACA---T-...............GA-TATG......ATGA--A-
430
431   7_HRV40a|d    CACTTTGATAAGTGGCAGATAACCATCAAGAGATGTCACAAATTAGGAGAAAATTTGAA
432   8_HRV40b|d    CACTTTGATAAGTGGCAGATAACCATCAAGAGATGTCACAAATTAGGAGAAAATTTGAA
433   9_HRV40       CACTTTGATAAGTGGCAGATAACCATCAAGAGATGTCACAAATTAGGAGAAAATTTGAA
434   10_HRV85      CACTTTGATCAGTGGCAGATAACTATCAGGAAATGGCACAAATTAGAAGGAAGTTTGAG
435   11_HRV85a|    CACTTTGATCAGTGGCAGATAACTATCAGGAAATGGCACAAATTAGAAGGAAGTTTGAG
436   12_HRV85b|    CACTTTGATCAGTGGCAGATAACTATCAGGAAATGGCACAAATTAGAAGGAAGTTTGAG
437   GROUP_2       CACTTTGAT-AGTGGCAGATAAC-ATACA-GA-ATG-CACAAATTAG-AG-AA-TTTGA-
438
439   7_HRV40a|d    TTCTTTACATATGCTAGGTTTGATTCAGAAATTACCTTAG-TTCCTTGTATAGCCGGTAA
440   8_HRV40b|d    TTCTTTACATATGCTAGGTTTGATTCAGAAATTACCTTAG-TTCCTTGTATAGCCGGTAA
441   9_HRV40       TTCTTTACATATGCTAGGTTTGATTCAGAAATTACCTTAG-TTCCTTGTATAGCCGGTAA
442   10_HRV85      TTCTTTACTTACACTAGATTTGATTCAGAAATCACTTTAG-TCCCTTGTATAGCTGGAAA
443   11_HRV85a|    TTCTTTACTTACACTAGATTTGATTCAGAAATCACTTTAG-TCCCTTGTATAGCTGGAAA
444   12_HRV85b|    TTCTTTACTTACACTAGATTTGATTCAGAAATCACTTTAG-TCCCTTGTATAGCTGGAAA
445   GROUP_2       TTCTTTAC-TA--CTAG-TTTGATTCAGAAAT-AC-TTAG.T-CCTTGTATAGC-GG-AA
446
447   7_HRV40a|d    GGGTGAAGACATTGGACACATTGTGATGCAATATATGTATGTACCCCCTGGCGCACCCAT
448   8_HRV40b|d    GGGTGAAGACATTGGACACATTGTGATGCAATATATGTATGTACCCCCTGGCGCACCCAT
```

FIG. D13 CONT'D 09.trace                                                                        9/20/2007 5:05 PM

```
449  9_HRV40      GGGTGAAGACATTGGACACATTGTGATGCAATATATGTATGTACCCCCTGGCGCACCCAT
450  10_HRV85     GGGTGATGATATTGGACACATTGTAATGCAGTATATGTATGTGCCCCCCGGAGCACCAAT
451  11_HRV85a|   GGGTGATGATATTGGACACATTGTAATGCAGTATATGTATGTGCCCCCCGGAGCACCAAT
452  12_HRV85b|   GGGTGATGATATTGGACACATTGTAATGCAGTATATGTATGTGCCCCCCGGAGCACCAAT
453  GROUP_2      GGGTGA-GA-ATTGGACACATTGT-ATGCA-TATATGTATGT-CCCCC-GG-GCACC-AT
454
455  7_HRV40a|d   ACCAAAGAAAAGAAATGATTACACATGGCAGTCAGGCACTAATGCTTCTGTATTCTGGCA
456  8_HRV40b|d   ACCAAAGAAAAGAAATGATTACACATGGCAGTCAGGCACTAATGCTTCTGTATTCTGGCA
457  9_HRV40      ACCAAAGAAAAGAAATGATTACACATGGCAGTCAGGCACTAATGCTTCTGTATTCTGGCA
458  10_HRV85     ACCAAGGAAAAGAGATGATTACACATGGCAATCAGGTACTAATGCTTCCGTGTTTTGGCA
459  11_HRV85a|   ACCAAGGAAAAGAGATGATTACACATGGCAATCAGGTACTAATGCTTCCGTGTTTTGGCA
460  12_HRV85b|   ACCAAGGAAAAGAGATGATTACACATGGCAATCAGGTACTAATGCTTCCGTGTTTTGGCA
461  GROUP_2      ACCAA-GAAAAGA-ATGATTACACATGGCA-TCAGG-ACTAATGCTTC-GT-TT-TGGCA
462
463  7_HRV40a|d   ACATGGTCAAACTTTCCCTAGATTTTCTTTACCTTTCCTAAGCATAGCTTCAGCATACTA
464  8_HRV40b|d   ACATGGTCAAACTTTCCCTAGATTTTCTTTACCTTTCCTAAGCATAGCTTCAGCATACTA
465  9_HRV40      ACATGGTCAAACTTTCCCTAGATTTTCTTTACCTTTCCTAAGCATAGCTTCAGCATACTA
466  10_HRV85     ACATGGGCAAACTTTCCCCAGATTTTCCTTACCTTTCTTGAGTGTTGCTTCAGCATATTA
467  11_HRV85a|   ACATGGGCAAACTTTCCCCAGATTTTCCTTACCTTTCTTGAGTGTTGCTTCAGCATATTA
468  12_HRV85b|   ACATGGGCAAACTTTCCCCAGATTTTCCTTACCTTTCTTGAGTGTTGCTTCAGCATATTA
469  GROUP_2      ACATGG-CAAACTTTCCC-AGATTTC-TTACCTTTC-T-AG--T-GCTTCAGCATA-TA
470
471  7_HRV40a|d   CATGTTTTATGATGGATACGATGGTGATACATCGACCTCAAGATATGGCACATCAGTCAC
472  8_HRV40b|d   CATGTTTTATGATGGATACGATGGTGATACATCGACCTCAAGATATGGCACATCAGTCAC
473  9_HRV40      CATGTTTTATGATGGATACGATGGTGATACATCGACCTCAAGATATGGCACATCAGTCAC
474  10_HRV85     CATGTTTTATGATGGTTATGATGGTGATACACCAGGCTCAATGTATGGGACGTCAGTCAC
475  11_HRV85a|   CATGTTTTATGATGGTTATGATGGTGATACACCAGGCTCAATGTATGGGACGTCAGTCAC
476  12_HRV85b|   CATGTTTTATGATGGTTATGATGGTGATACACCAGGCTCAATGTATGGGACGTCAGTCAC
477  GROUP_2      CATGTTTTATGATGG-TA-GATGGTGATACA-C----CTCAA--TATGG--AC-TCAGTCAC
478
479  7_HRV40a|d   TAACCATATGGGAACGCTATGCTCAAGAATAGTCACCAACAAGCAGCAGCATGAAGTTGA
480  8_HRV40b|d   TAACCATATGGGAACGCTATGCTCAAGAATAGTCACCAACAAGCAGCAGCATGAAGTTGA
481  9_HRV40      TAACCATATGGGAACGCTATGCTCAAGAATAGTCACCAACAAGCAGCAGCATGAAGTTGA
482  10_HRV85     CAACCACATGGGAACACTGTGCTCGAGGATAGTTACCAACAAACAGCAGCATGAGGTTGA
483  11_HRV85a|   CAACCACATGGGAACACTGTGCTCGAGGATAGTTACCAACAAACAGCAGCATGAGGTTGA
484  12_HRV85b|   CAACCACATGGGAACACTGTGCTCGAGGATAGTTACCAACAAACAGCAGCATGAGGTTGA
485  GROUP_2      -AACCA-ATGGGAAC-CT-TGCTC-AG-ATAGT-ACCAACAA-CAGCAGCATGA-GTTGA
486
487  7_HRV40a|d   GATTACCACACGTATATATCACAAGGCCAAGCATATTAAAGCATGGTGTCCAAGGGCCCC
488  8_HRV40b|d   GATTACCACACGTATATATCACAAGGCCAAGCATATTAAAGCATGGTGTCCAAGGGCCCC
489  9_HRV40      GATTACCACACGTATATATCACAAGGCCAAGCATATTAAAGCATGGTGTCCAAGGGCCCC
490  10_HRV85     AATCACCACGCGTGTGTATCATAAGGCCAAGCATGTAAAGGCTTGGTGTCCAAGAGCACC
491  11_HRV85a|   AATCACCACGCGTGTGTATCATAAGGCCAAGCATGTAAAGGCTTGGTGTCCAAGAGCACC
492  12_HRV85b|   AATCACCACGCGTGTGTATCATAAGGCCAAGCATGTAAAGGCTTGGTGTCCAAGAGCACC
493  GROUP_2      -AT-ACCAC-CGT-T-TATCA-AAGGCCAAGCAT-T-AA-GC-TGGTGTCCAAG-GC-CC
494
495  7_HRV40a|d   AAGAGCAGTACCTTACACA-CATACACACTCAACAAATTATAAAC-CTCAAG---AAGGT
496  8_HRV40b|d   AAGAGCAGTACCTTACACA-CATACACACTCAACAAATTATAAAC-CTCAAG---AAGGT
497  9_HRV40      AAGAGCAGTACCTTACACA-CATACACACTCAACAAATTATAAAC-CTCAAG---AAGGT
498  10_HRV85     AAGAGCGGTGCCTTATACA-CACACACGCTCAACCAACTATGTGC-CACAAG---ATGGT
499  11_HRV85a|   AAGAGCGGTGCCTTATACA-CACACACGCTCAACCAACTATGTGC-CACAAG---ATGGT
500  12_HRV85b|   AAGAGCGGTGCCTTATACA-CACACACGCTCAACCAACTATGTGC-CACAAG---ATGGT
501  GROUP_2      AAGAGC-GT-CCTTA-ACA-CA-ACAC-CTCAAC-AA-TAT---C.C-CAAG...A-GGT
502
503  7_HRV40a|d   GAAG------TCCAGATTT---TCCTCAAAGAGAGAG------CCAGCCTAACAACAG--
504  8_HRV40b|d   GAAG------TCCAGATTT---TCCTCAAAGAGAGAG------CCAGCCTAACAACAG--
505  9_HRV40      GAAG------TCCAGATTT---TCCTCAAAGAGAGAG------CCAGCCTAACAACAG--
506  10_HRV85     GAAG------TTAAGATCT---TCCTCAAAGAGAGAG------CTAGTTTAACCACAG--
507  11_HRV85a|   GAAG------TTAAGATCT---TCCTCAAAGAGAGAG------CTAGTTTAACCACAG--
508  12_HRV85b|   GAAG------TTAAGATCT---TCCTCAAAGAGAGAG------CTAGTTTAACCACAG--
509  GROUP_2      GAAG......T--AGAT-T...TCCTCAAAGAGAGAG......C-AG--TAAC-ACAG..
510
511  7_HRV40a|d   ----TA---------------
512  8_HRV40b|d   ----TC---------------
513  9_HRV40      ----TT---------------
```

FIG. D13 CONT'D

```
09.trace                                                                                   9/20/2007 5:05 PM 514  10_HRV85      ----CA--------------
515  11_HRV85a|    ----CG--------------
516  12_HRV85b|    ----CT--------------
517  GROUP_2       ....--..............
518
519
520
521  GROUP  3:
522
523  13_HRV56a|    AACCCAGTTGAGAGATATGTAGATGATGTTTTAAATGAAGTTTTAGTTGTTCCAAATATT
524  14_HRV56b|    AACCCAGTTGAGAGATATGTAGATGATGTTTTAAATGAAGTTTTAGTTGTTCCAAATATT
525  15_HRV56      AACCCAGTTGAGAGATATGTAGATGATGTTTTAAATGAAGTTTTAGTTGTTCCAAATATT
526  GROUP_3       AACCCAGTTGAGAGATATGTAGATGATGTTTTAAATGAAGTTTTAGTTGTTCCAAATATT
527
528  13_HRV56a|    AGGGAGAGCCATCCATCCACATCAAATTCTGCCCCTGCATTAGATGCTGCTGAAACTGGC
529  14_HRV56b|    AGGGAGAGCCATCCATCCACATCAAATTCTGCCCCTGCATTAGATGCTGCTGAAACTGGC
530  15_HRV56      AGGGAGAGCCATCCATCCACATCAAATTCTGCCCCTGCATTAGATGCTGCTGAAACTGGC
531  GROUP_3       AGGGAGAGCCATCCATCCACATCAAATTCTGCCCCTGCATTAGATGCTGCTGAAACTGGC
532
533  13_HRV56a|    CATACTAGTGCAATCCAACCAGAAGACACTATAGAAACCAGATATGTACAGACATCACAA
534  14_HRV56b|    CATACTAGTGCAATCCAACCAGAAGACACTATAGAAACCAGATATGTACAGACATCACAA
535  15_HRV56      CATACTAGTGCAATCCAACCAGAAGACACTATAGAAACCAGATATGTACAGACATCACAA
536  GROUP_3       CATACTAGTGCAATCCAACCAGAAGACACTATAGAAACCAGATATGTACAGACATCACAA
537
538  13_HRV56a|    ACTAGGGATGAAATGAGTATAGAGAGTTTTCTAGGTAGATCAGGTTGTATACATATATCA
539  14_HRV56b|    ACTAGGGATGAAATGAGTATAGAGAGTTTTCTAGGTAGATCAGGTTGTATACATATATCA
540  15_HRV56      ACTAGGGATGAAATGAGTATAGAGAGTTTTCTAGGTAGATCAGGTTGTATACATATATCA
541  GROUP_3       ACTAGGGATGAAATGAGTATAGAGAGTTTTCTAGGTAGATCAGGTTGTATACATATATCA
542
543  13_HRV56a|    ACTATAACTGTGGATAATGATGTA---------------GATTATA------ATTCAAAG
544  14_HRV56b|    ACTATAACTGTGGATAATGATGTA---------------GATTATA------ATTCAAAG
545  15_HRV56      ACTATAACTGTGGATAATGATGTA---------------GATTATA------ATTCAAAG
546  GROUP_3       ACTATAACTGTGGATAATGATGTA...............GATTATA......ATTCAAAG
547
548  13_HRV56a|    CATTATAATAAATGGCAAATAACCTTACAAGAAATGGCTCAAGTTAGGCGTAAATTTGAA
549  14_HRV56b|    CATTATAATAAATGGCAAATAACCTTACAAGAAATGGCTCAAGTTAGGCGTAAATTTGAA
550  15_HRV56      CATTATAATAAATGGCAAATAACCTTACAAGAAATGGCTCAAGTTAGGCGTAAATTTGAA
551  GROUP_3       CATTATAATAAATGGCAAATAACCTTACAAGAAATGGCTCAAGTTAGGCGTAAATTTGAA
552
553  13_HRV56a|    TTCTTTACTTATGTCAGATTTGATTCAGAGGTTACTTTGG-TACCTTGTGTAGCCGGCAA
554  14_HRV56b|    TTCTTTACTTATGTCAGATTTGATTCAGAGGTTACTTTGG-TACCTTGTGTAGCCGGCAA
555  15_HRV56      TTCTTTACTTATGTCAGATTTGATTCAGAGGTTACTTTGG-TACCTTGTGTAGCCGGCAA
556  GROUP_3       TTCTTTACTTATGTCAGATTTGATTCAGAGGTTACTTTGG.TACCTTGTGTAGCCGGCAA
557
558  13_HRV56a|    GGGAGATGATATTGGACACATTGTAATGCAATACATGTATGTGCCTCCTGGTGCACCACT
559  14_HRV56b|    GGGAGATGATATTGGACACATTGTAATGCAATACATGTATGTGCCTCCTGGTGCACCACT
560  15_HRV56      GGGAGATGATATTGGACACATTGTAATGCAATACATGTATGTGCCTCCTGGTGCACCACT
561  GROUP_3       GGGAGATGATATTGGACACATTGTAATGCAATACATGTATGTGCCTCCTGGTGCACCACT
562
563  13_HRV56a|    TCCAAACTCAAGAGATGATTTTACATGGCAATCTGGCACCAATGCTTCTGTCTTTTGGCA
564  14_HRV56b|    TCCAAACTCAAGAGATGATTTTACATGGCAATCTGGCACCAATGCTTCTGTCTTTTGGCA
565  15_HRV56      TCCAAACTCAAGAGATGATTTTACATGGCAATCTGGCACCAATGCTTCTGTCTTTTGGCA
566  GROUP_3       TCCAAACTCAAGAGATGATTTTACATGGCAATCTGGCACCAATGCTTCTGTCTTTTGGCA
567
568  13_HRV56a|    ACATGGCCAAGCTTTCCCCAGATTCTCTCTACCTTTCTTAAGTATTGCTTCTGCTTATTA
569  14_HRV56b|    ACATGGCCAAGCTTTCCCCAGATTCTCTCTACCTTTCTTAAGTATTGCTTCTGCTTATTA
570  15_HRV56      ACATGGCCAAGCTTTCCCCAGATTCTCTCTACCTTTCTTAAGTATTGCTTCTGCTTATTA
571  GROUP_3       ACATGGCCAAGCTTTCCCCAGATTCTCTCTACCTTTCTTAAGTATTGCTTCTGCTTATTA
572
573  13_HRV56a|    CATGTTTTATGATGGTTATGATGGAGACACTTCAAGCTCCAGATATGGTACATCAGTTAC
574  14_HRV56b|    CATGTTTTATGATGGTTATGATGGAGACACTTCAAGCTCCAGATATGGTACATCAGTTAC
575  15_HRV56      CATGTTTTATGATGGTTATGATGGAGACACTTCAAGCTCCAGATATGGTACATCAGTTAC
576  GROUP_3       CATGTTTTATGATGGTTATGATGGAGACACTTCAAGCTCCAGATATGGTACATCAGTTAC
577
578  13_HRV56a|    AAACCACATGGGGACACTCTGTTCAAGAATTGTGACAAATAAACAACTTCATCCTGTTGA
```

FIG. D13 CONT'D

```
09.trace                                                                    9/20/2007 5:05 PM 579  14_HRV56b|   AAACCACATGGGGACACTCTGTTCAAGAATTGTGACAAATAAACAACTTCATCCTGTTGA
580  15_HRV56    AAACCACATGGGGACACTCTGTTCAAGAATTGTGACAAATAAACAACTTCATCCTGTTGA
581  GROUP_3     AAACCACATGGGGACACTCTGTTCAAGAATTGTGACAAATAAACAACTTCATCCTGTTGA
582
583  13_HRV56a|   AGTCACAACTCGTGTATATCATAAGGCAAAGCATATTCGAGCATGGTGTCCTAGAGCACC
584  14_HRV56b|   AGTCACAACTCGTGTATATCATAAGGCAAAGCATATTCGAGCATGGTGTCCTAGAGCACC
585  15_HRV56    AGTCACAACTCGTGTATATCATAAGGCAAAGCATATTCGAGCATGGTGTCCTAGAGCACC
586  GROUP_3     AGTCACAACTCGTGTATATCATAAGGCAAAGCATATTCGAGCATGGTGTCCTAGAGCACC
587
588  13_HRV56a|   AAGGGCTGTGCCTTATACA-CATGCTCACGTCACCAATTATAAAC-CACAAG---ATGGT
589  14_HRV56b|   AAGGGCTGTGCCTTATACA-CATGCTCACGTCACCAATTATAAAC-CACAAG---ATGGT
590  15_HRV56    AAGGGCTGTGCCTTATACA-CATGCTCACGTCACCAATTATAAAC-CACAAG---ATGGT
591  GROUP_3     AAGGGCTGTGCCTTATACA.CATGCTCACGTCACCAATTATAAAC.CACAAG...ATGGT
592
593  13_HRV56a|   GATG------TACAGATCT---TCTTAAAACCCAGAC------CCAGCCTAACAACAT--
594  14_HRV56b|   GATG------TACAGATCT---TCTTAAAACCCAGAC------CCAGCCTAACAACAT--
595  15_HRV56    GATG------TACAGATCT---TCTTAAAACCCAGAC------CCAGCCTAACAACAT--
596  GROUP_3     GATG......TACAGATCT...TCTTAAAACCCAGAC......CCAGCCTAACAACAT..
597
598  13_HRV56a|   ----TA---------------
599  14_HRV56b|   ----TG---------------
600  15_HRV56    ----TT---------------
601  GROUP_3     ....T-...............
602
603
604
605  Group  4:
606
607  16_HRV54    AATCCTGTAGAAAGATATGTTGATGAAGTGTTAAATGAAGTGTTAGTTGTCCCAAACATT
608  17_HRV98    AATCCTGTAGAGAGATATGTTGATGAAGTATTAAATGAAGTGTTAGTTGTTCCAAACATT
609  GROUP_4     AATCCTGTAGA-AGATATGTTGATGAAGT-TTAAATGAAGTGTTAGTTGT-CCAAACATT
610
611  16_HRV54    AGAGAAAGTCATCCAGCTACATCTAATTCAGCCCCTGCGCTAGATGCGGCAGAAACTGGA
612  17_HRV98    AAAGAAAGTCATCCAGCTACATCTAATTCGGCCCCTACACTAGATGCAGCAGAAACTGGG
613  GROUP_4     A-AGAAAGTCATCCAGCTACATCTAATTC-GCCCCT-C-CTAGATGC-GCAGAAACTGG-
614
615  16_HRV54    CACACTAGTGGAGTACAACCCGAGGACACCATAGAAACAAGATTTGTGCAGACATCACAA
616  17_HRV98    CACACTAGTGGAATACAACCTGAGGATACTATAGAAACAAGATATGTGCAGACATCACAA
617  GROUP_4     CACACTAGTGGA-TACAACC-GAGGA-AC-ATAGAAACAAGAT-TGTGCAGACATCACAA
618
619  16_HRV54    ACTAGAGATGAAATGAGCATAGAAAGTTTTCTAGGCAGGGCTGGTTGCATACATGAATCC
620  17_HRV98    ACCAGAGATGAAATGAGTATAGAAAGTTTTCTAGGTAGGGCCGGTTGTATACATGAATCT
621  GROUP_4     AC-AGAGATGAAATGAG-ATAGAAAGTTTTCTAGG-AGGGC-GGTTG-ATACATGAATC-
622
623  16_HRV54    ACCATTACAATTCAAAATGATGTA---------------GAATACA------ATGATCAC
624  17_HRV98    ACTATCACTATTCAAAATGATGTA---------------GAATATA------ACGATCAT
625  GROUP_4     AC-AT-AC-ATTCAAAATGATGTA...............GAATA-A......A-GATCA-
626
627  16_HRV54    CATTTAAGAAATGGGATATAACATTACAAGAGATGGCACAAATACGAAGGAAATTTGAA
628  17_HRV98    CATTTAGACAATGGGATATAACATTACAAGAAATGGCACAAATTCGAAGAAAATTTGAA
629  GROUP_4     CATTTTA---AATGGGATATAACATTACAAGA-ATGGCACAAAT-CGAAG-AAATTTGAA
630
631  16_HRV54    TTCTTTACTTATGTTAGGTTTGATTCAGAAATTACTCTAG-TCCCCTGTATAGCTGGTAA
632  17_HRV98    TTCTTTACTTATGTTAGATTTGATTCAGAAGTTACCTTAG-TTCCTTGCATAGCTGGCAA
633  GROUP_4     TTCTTTACTTATGTTAG-TTTGATTCAGAA-TTAC--TAG.T-CC-TG-ATAGCTGG-AA
634
635  16_HRV54    GGGAGTTGATATTGGACACATTGTCATGCAATTCATGTATGTACCGCCTGGTGCACCAAA
636  17_HRV98    GGGAGCTGACATTGGACACATTGTCATGCAATTCATGTATGTTCCACCTGGTGCACCTAA
637  GROUP_4     GGGAG-TGA-ATTGGACACATTGTCATGCAATTCATGTATGT-CC-CCTGGTGCACC-AA
638
639  16_HRV54    ACCAGAAAAAGGAATGATTACACCTGGGAGTCAAGCACAAACCCTTCTATATTTTGGCA
640  17_HRV98    ACCTAAAAAGAGGAATGATTATACTTGGGAATCAAGCACAAACCCTTCTATATTCTGGCA
641  GROUP_4     ACC--AAAA-AGGAATGATTA-AC-TGGGA-TCAAGCACAAACCCTTCTATATT-TGGCA
642
643  16_HRV54    ACATGGCCAAGCTTATCCAAGATTCTCTTTACCATTTTTAAGTATTGCATCTGCTTACTA
```

FIG. D13 CONT'D

```
09.trace                                                              9/20/2007 5:05 PM 644 17_HRV98    GCATGGTCAGGCCTATCCAAGATTTTCTCTACCATTCTTGAGCATTGCATCTGCTTACTA
645 GROUP_4     -CATGG-CA-GC-TATCCAAGATT-TCT-TACCATT-TT-AG-ATTGCATCTGCTTACTA
646
647 16_HRV54    CATGTTTTATGATGGGTATGATGGTGACGCACCTGGATCAAGATATGGGACTTCAGTTAC
648 17_HRV98    CATGTTTTACGATGGGTATGATGGTGATGCACCTGGATCAAGATATGGAACCTCAGTCAC
649 GROUP_4     CATGTTTTA-GATGGGTATGATGGTGA-GCACCTGGATCAAGATATGG-AC-TCAGT-AC
650
651 16_HRV54    CAATCATATGGGTACTTTGTGTTCAAGAGTGGTTACTGATAAACAAAAACACCCAGTTGA
652 17_HRV98    TAATCACATGGGCACTTTGTGTTCAAGAGTAGTTACTGGCAAACAAGAACACCCAGTTGA
653 GROUP_4     -AATCA-ATGGG-ACTTTGTGTTCAAGAGT-GTTACTG--AAACAA-AACACCCAGTTGA
654
655 16_HRV54    AATCACCACACGGGTGTATCACAAGGCAAAACACATTAGAGCATGGTGTCCACGTGCACC
656 17_HRV98    AATCACTACACGTGTGTACCACAAAGCAAAACACATTAGAGCATGGTGTCCACGTGCACC
657 GROUP_4     AATCAC-ACACG-GTGTA-CACAA-GCAAAACACATTAGAGCATGGTGTCCACGTGCACC
658
659 16_HRV54    TAGGGCTGTCCCATACACA-CATACTAGATCAACAAATTACATGC-CACGGG---AGGGT
660 17_HRV98    TAGAGCTGTTCCATACACA--CACACTAGATCAACTAATTACATGC-CTCAAG---ATGGT
661 GROUP_4     TAG-GCTGT-CCATACACA.CA-ACTAGATCAAC-AATTACATGC.C--C--G...A-GGT
662
663 16_HRV54    GATC------CAACAATTT---TCCTTAAACACAGGA------CAAACCTTGTAACAG--
664 17_HRV98    GAAC------CAACAATCT---TTCTTAAGCATAGAA------AAGATCTTGTAACAG--
665 GROUP_4     GA-C......CAACAAT-T...T-CTTAA-CA-AG-A.......-A-A-CTTGTAACAG..
666
667 16_HRV54    ----CT---------------
668 17_HRV98    ----CT---------------
669 GROUP_4     ....CT...............
670
671
672
673 GROUP 5:
674
675 18_HRV59a|   AACCCAGTGGAAAACTATGTTAATGATGTACTTAATGAGGTTTTAGTAGTACCAAATATA
676 19_HRV59b|   AACCCAGTGGAAAACTATGTTAATGATGTACTTAATGAGGTTTTAGTAGTACCAAATATA
677 20_HRV59     AACCCAGTGGAAAACTATGTTAATGATGTACTTAATGAGGTTTTAGTAGTACCAAATATA
678 21_HRV63     AATCCAGTAGAGAATTATGTAAATGATGTTCTTAATGAAGTGTTAGTTGTTCCAAACATA
679 22_HRV63b|   AATCCAGTAGAGAATTATGTAAATGATGTTCTTAATGAAGTGTTAGTTGTTCCAAACATA
680 23_HRV63a|   AATCCAGTAGAGAATTATGTAAATGATGTTCTTAATGAAGTGTTAGTTGTTCCAAACATA
681 GROUP_5      AA-CCAGT-GA-AA-TATGT-AATGATGT-CTTAATGA-GT-TTAGT-GT-CCAAA-ATA
682
683 18_HRV59a|   CAGGAAAGCCACCCAACCACCTCAAATGCTGCTCCAGCATTAGATGCAGCAGAGACTGGA
684 19_HRV59b|   CAGGAAAGCCACCCAACCACCTCAAATGCTGCTCCAGCATTAGATGCAGCAGAGACTGGA
685 20_HRV59     CAGGAAAGCCACCCAACCACCTCAAATGCTGCTCCAGCATTAGATGCAGCAGAGACTGGA
686 21_HRV63     CAAGAAAGCCATCCAACCACATCAAACGCTGCTCCTGTACTTGATGCTGCGGAAACAGGA
687 22_HRV63b|   CAAGAAAGCCATCCAACCACATCAAACGCTGCTCCTGTACTTGATGCTGCGGAAACAGGA
688 23_HRV63a|   CAAGAAAGCCATCCAACCACATCAAACGCTGCTCCTGTACTTGATGCTGCGGAAACAGGA
689 GROUP_5      CA-GAAAGCCA-CCAACCAC-TCAAA-GCTGCTCC-G-A-T-GATGC-GC-GA-AC-GGA
690
691 18_HRV59a|   CATACAAGCAGTATACAACCTGAGGATACCATAGAAACAAGATATGTTCAGACATCACAA
692 19_HRV59b|   CATACAAGCAGTATACAACCTGAGGATACCATAGAAACAAGATATGTTCAGACATCACAA
693 20_HRV59     CATACAAGCAGTATACAACCTGAGGATACCATAGAAACAAGATATGTTCAGACATCACAA
694 21_HRV63     CACACAAGCAGTATACAACCTGAGGATACTGTAGAAACTAGATATGTGCAAACGTCTCAA
695 22_HRV63b|   CACACAAGCAGTATACAACCTGAGGATACTGTAGAAACTAGATATGTGCAAACGTCTCAA
696 23_HRV63a|   CACACAAGCAGTATACAACCTGAGGATACTGTAGAAACTAGATATGTGCAAACGTCTCAA
697 GROUP_5      CA-ACAAGCAGTATACAACCTGAGGATAC--TAGAAAC-AGATATGT-CA-AC-TC-CAA
698
699 18_HRV59a|   ACTAGAGATGAGATGAGTGTAGAAAGTTTCTTAGGTAGATCTGGGTGTATACATATTTCA
700 19_HRV59b|   ACTAGAGATGAGATGAGTGTAGAAAGTTTCTTAGGTAGATCTGGGTGTATACATATTTCA
701 20_HRV59     ACTAGAGATGAGATGAGTGTAGAAAGTTTCTTAGGTAGATCTGGGTGTATACATATTTCA
702 21_HRV63     ACAAGGGATGAAATGAGTGTAGAGAGCTTTCTTGGTAGATCAGGATGCATACACATATCA
703 22_HRV63b|   ACAAGGGATGAAATGAGTGTAGAGAGCTTTCTTGGTAGATCAGGATGCATACACATATCA
704 23_HRV63a|   ACAAGGGATGAAATGAGTGTAGAGAGCTTTCTTGGTAGATCAGGATGCATACACATATCA
705 GROUP_5      AC-AG-GATGA-ATGAGTGTAGA-AG-TT--T-GGTAGATC-GG-TG-ATACA-AT-TCA
706
707 18_HRV59a|   ACTATTACTGTCAATAAAGACATA---------------AAATATG------ATGATGGA
708 19_HRV59b|   ACTATTACTGTCAATAAAGACATA---------------AAATATG------ATGATGGA
```

FIG. D13 CONT'D

```
09.trace                                                                              9/20/2007 5:05 PM 709  20_HRV59    ACTATTACTGTCAATAAAGACATA---------------AAATATG------ATGATGGA
710  21_HRV63    ACTATCACTGTTGACAAAACCATT---------------GACTATG------ACACTGGA
711  22_HRV63b|  ACTATCACTGTTGACAAAACCATT---------------GACTATG------ACACTGGA
712  23_HRV63a|  ACTATCACTGTTGACAAAACCATT---------------GACTATG------ACACTGGA
713  GROUP_5     ACTAT-ACTGT--A-AAA--CAT-.............-A-TATG......A---TGGA
714
715  18_HRV59a|  CACTTTCTTAAATGGCCTATAACATTACAAGAGATGGCACAAATTAGGAGAAAATTTGAA
716  19_HRV59b|  CACTTTCTTAAATGGCCTATAACATTACAAGAGATGGCACAAATTAGGAGAAAATTTGAA
717  20_HRV59    CACTTTCTTAAATGGCCTATAACATTACAAGAGATGGCACAAATTAGGAGAAAATTTGAA
718  21_HRV63    CATTTTAATAAATGGCAAATAACATTACAAGAGATGGCACAAATTAGAAGGAAATTTGAA
719  22_HRV63b|  CATTTTAATAAATGGCAAATAACATTACAAGAGATGGCACAAATTAGAAGGAAATTTGAA
720  23_HRV63a|  CATTTTAATAAATGGCAAATAACATTACAAGAGATGGCACAAATTAGAAGGAAATTTGAA
721  GROUP_5     CA-TTT--TAAATGGC--ATAACATTACAAGAGATGGCACAAATTAG-AG-AAATTTGAA
722
723  18_HRV59a|  TTCTTCACATATGTTAGATTTGACTCAGAAATCACTTTGG-TGCCTTGCATAGCTGGAAA
724  19_HRV59b|  TTCTTCACATATGTTAGATTTGACTCAGAAATCACTTTGG-TGCCTTGCATAGCTGGAAA
725  20_HRV59    TTCTTCACATATGTTAGATTTGACTCAGAAATCACTTTGG-TGCCTTGCATAGCTGGAAA
726  21_HRV63    TTCTTCACATATGTCAGATTTGATTCAGAAGTCACTCTTG-TACCATGTATAGCAGGAAA
727  22_HRV63b|  TTCTTCACATATGTCAGATTTGATTCAGAAGTCACTCTTG-TACCATGTATAGCAGGAAA
728  23_HRV63a|  TTCTTCACATATGTCAGATTTGATTCAGAAGTCACTCTTG-TACCATGTATAGCAGGAAA
729  GROUP_5     TTCTTCACATATGT-AGATTTGA-TCAGAA-TCACT-T-G.T-CC-TG-ATAGC-GGAAA
730
731  18_HRV59a|  AGGGGATGACATTGGTCATATAGTCATGCAATATATGTATGTTCCACCAGGTGCTCCACT
732  19_HRV59b|  AGGGGATGACATTGGTCATATAGTCATGCAATATATGTATGTTCCACCAGGTGCTCCACT
733  20_HRV59    AGGGGATGACATTGGTCATATAGTCATGCAATATATGTATGTTCCACCAGGTGCTCCACT
734  21_HRV63    AGGTGATGACATTGGTCATATAGTTATGCAGTACATGTACGTTCCACCCGGTGCCCCTCT
735  22_HRV63b|  AGGTGATGACATTGGTCATATAGTTATGCAGTACATGTACGTTCCACCCGGTGCCCCTCT
736  23_HRV63a|  AGGTGATGACATTGGTCATATAGTTATGCAGTACATGTACGTTCCACCCGGTGCCCCTCT
737  GROUP_5     AGG-GATGACATTGGTCATATAGT-ATGCA-TA-ATGTA-GTTCCACC-GGTGC-CC-CT
738
739  18_HRV59a|  GCCCACAAAGAGAGATGATTACACATGGCAATCTGGTACTAATGCTTCAATATTCTGGCA
740  19_HRV59b|  GCCCACAAAGAGAGATGATTACACATGGCAATCTGGTACTAATGCTTCAATATTCTGGCA
741  20_HRV59    GCCCACAAAGAGAGATGATTACACATGGCAATCTGGTACTAATGCTTCAATATTCTGGCA
742  21_HRV63    ACCCACCCGAAGAGAAGATTACACATGGCAATCTGGCACTAATGCTTCAATATTCTGGCA
743  22_HRV63b|  ACCCACCCGAAGAGAAGATTACACATGGCAATCTGGCACTAATGCTTCAATATTCTGGCA
744  23_HRV63a|  ACCCACCCGAAGAGAAGATTACACATGGCAATCTGGCACTAATGCTTCAATATTCTGGCA
745  GROUP_5     -CCCAC----AGAGA-GATTACACATGGCAATCTGG-ACTAATGCTTCAATATTCTGGCA
746
747  18_HRV59a|  ACATGGACAAACATTCCCAAGATTTTCATTGCCCTTCCTGAGCATAGCATCAGCTTATTA
748  19_HRV59b|  ACATGGACAAACATTCCCAAGATTTTCATTGCCCTTCCTGAGCATAGCATCAGCTTATTA
749  20_HRV59    ACATGGACAAACATTCCCAAGATTTTCATTGCCCTTCCTGAGCATAGCATCAGCTTATTA
750  21_HRV63    ACATGGACAAGCTTTTCCAAGGTTTTCTCTACCTTTCTTGAGTATTGCATCAGCATATTA
751  22_HRV63b|  ACATGGACAAGCTTTTCCAAGGTTTTCTCTACCTTTCTTGAGTATTGCATCAGCATATTA
752  23_HRV63a|  ACATGGACAAGCTTTTCCAAGGTTTTCTCTACCTTTCTTGAGTATTGCATCAGCATATTA
753  GROUP_5     ACATGGACAA-C-TT-CCAAG-TTTTC--T-CC-TTC-TGAG-AT-GCATCAGC-TATTA
754
755  18_HRV59a|  CATGTTTTATGATGGTTATGATGGAGATAAATCTGAATCTAGGTATGGTGTGTCTGTAAC
756  19_HRV59b|  CATGTTTTATGATGGTTATGATGGAGATAAATCTGAATCTAGGTATGGTGTGTCTGTAAC
757  20_HRV59    CATGTTTTATGATGGTTATGATGGAGATAAATCTGAATCTAGGTATGGTGTGTCTGTAAC
758  21_HRV63    CATGTTTTATGATGGATATGATGGAGATAAATCAAGCTCTAGGTATGGTGTTTCAGTTAC
759  22_HRV63b|  CATGTTTTATGATGGATATGATGGAGATAAATCAAGCTCTAGGTATGGTGTTTCAGTTAC
760  23_HRV63a|  CATGTTTTATGATGGATATGATGGAGATAAATCAAGCTCTAGGTATGGTGTTTCAGTTAC
761  GROUP_5     CATGTTTTATGATGG-TATGATGGAGATAAATC----TCTAGGTATGGTGT-TC-GT-AC
762
763  18_HRV59a|  CAACCACATGGGCACTTTATGTTCTAGAATAGTTACAAACAGTCAGGAGCATCCAGTGGA
764  19_HRV59b|  CAACCACATGGGCACTTTATGTTCTAGAATAGTTACAAACAGTCAGGAGCATCCAGTGGA
765  20_HRV59    CAACCACATGGGCACTTTATGTTCTAGAATAGTTACAAACAGTCAGGAGCATCCAGTGGA
766  21_HRV63    TAACCACATGGGGACTTTATGTTCTAGAATTGTAACAAACAGCCAAGAACATCCAGTTGA
767  22_HRV63b|  TAACCACATGGGGACTTTATGTTCTAGAATTGTAACAAACAGCCAAGAACATCCAGTTGA
768  23_HRV63a|  TAACCACATGGGGACTTTATGTTCTAGAATTGTAACAAACAGCCAAGAACATCCAGTTGA
769  GROUP_5     -AACCACATGGG-ACTTTATGTTCTAGAAT-GT-ACAAACAG-CA-GA-CATCCAGT-GA
770
771  18_HRV59a|  GGTTGTCACACGTGTGTATCACAAAGCTAAACACGTCAAAGCCTGGTGCCCTAGAGCTCC
772  19_HRV59b|  GGTTGTCACACGTGTGTATCACAAAGCTAAACACGTCAAAGCCTGGTGCCCTAGAGCTCC
773  20_HRV59    GGTTGTCACACGTGTGTATCACAAAGCTAAACACGTCAAAGCCTGGTGCCCTAGAGCTCC
```

FIG. D13 CONT'D

```
09.trace                                                                                    9/20/2007 5:05 PM 774  21_HRV63      GGTGACTACACGTGTATATCATAAAGCTAAACACATCAGAGCCTGGTGCCCAAGAGCTCC
775  22_HRV63b|    GGTGACTACACGTGTATATCATAAAGCTAAACACATCAGAGCCTGGTGCCCAAGAGCTCC
776  23_HRV63a|    GGTGACTACACGTGTATATCATAAAGCTAAACACATCAGAGCCTGGTGCCCAAGAGCTCC
777  GROUP_5       GGT----ACACGTGT-TATCA-AAAGCTAAACAC-TCA-AGCCTGGTGCCC-AGAGCTCC
778
779  18_HRV59a|    TAGAGCAGTCCCTTACACA-CACAGCTACGTAACTAACTACAAGATTGCTGG---AAAA-
780  19_HRV59b|    TAGAGCAGTCCCTTACACA-CACAGCTACGTAACTAACTACAAGATTGCTGG---AAAA-
781  20_HRV59      TAGAGCAGTCCCTTACACA-CACAGCTACGTAACTAACTACAAGATTGCTGG---AAAA-
782  21_HRV63      TAGGGCTGTTCCATACACA-CATAGTTATGTCACTAACTATAAAATTACAGG---ACAG-
783  22_HRV63b|    TAGGGCTGTTCCATACACA-CATAGTTATGTCACTAACTATAAAATTACAGG---ACAG-
784  23_HRV63a|    TAGGGCTGTTCCATACACA-CATAGTTATGTCACTAACTATAAAATTACAGG---ACAG
785  GROUP_5       TAG-GC-GT-CC-TACACA.CA-AG-TA-GT-ACTAACTA-AA-ATT-C-GG...A-A-.
786
787  18_HRV59a|    GAAC------CTGAAATTT---TCTTAAAACCAAGAA------TGAATATTACAACAG--
788  19_HRV59b|    GAAC------CTGAAATTT---TCTTAAAACCAAGAA------TGAATATTACAACAG--
789  20_HRV59      GAAC------CTGAAATTT---TCTTAAAACCAAGAA------TGAATATTACAACAG--
790  21_HRV63      GAGA------CTGAAATTT---TCTTAAAACCTAGAG------CAACTATCAAGACAG--
791  22_HRV63b|    GAGA------CTGAAATTT---TCTTAAAACCTAGAG------CAACTATCAAGACAG--
792  23_HRV63a|    GAGA------CTGAAATTT---TCTTAAAACCTAGAG------CAACTATCAAGACAG--
793  GROUP_5       GA--......CTGAAATTT...TCTTAAAACC-AGA-.......--A-TAT-A--ACAG..
794
795  18_HRV59a|    ----CA---------------
796  19_HRV59b|    ----CG---------------
797  20_HRV59      ----CT---------------
798  21_HRV63      ----CA---------------
799  22_HRV63b|    ----CG---------------
800  23_HRV63a|    ----CT---------------
801  GROUP_5       ....C-...............
802
803
804
805  Group  6:
806
807  24_HRV39      AATCCAGTAGAAAATTATATAGATGAAGTATTAAATGAGGTATTAGTTGTTCCTAATATA
808  25_HRV39a|    AATCCAGTAGAAAATTATATAGATGAAGTATTAAATGAGGTATTAGTTGTTCCTAATATA
809  26_HRV39b|    AATCCAGTAGAAAATTATATAGATGGAGTATTAAATGAGGTATTAGTTGTTCCTAATATA
810  GROUP_6       AATCCAGTAGAAAATTATATAGATG-AGTATTAAATGAGGTATTAGTTGTTCCTAATATA
811
812  24_HRV39      AGAGAGAGCCATCCAACTACATCTAATGCAGCTACAGCTTTGGATGCTGCTGAAACTGGA
813  25_HRV39a|    AGAGAGAGCCATCCAACTACATCTAATGCAGCTACAGCTTTGGATGCTGCTGAAACTGGA
814  26_HRV39b|    AGAGAGAGCCATCCAACTACATCTAATGCAGCTCCAGCTTTGGATGCTGCTGAAACTGGA
815  GROUP_6       AGAGAGAGCCATCCAACTACATCTAATGCAGCT-CAGCTTTGGATGCTGCTGAAACTGGA
816
817  24_HRV39      CACACAAGTAGCACCCAGCCTGAAGACACAATTGAAACAAGATATGTGCAAACCTCACAT
818  25_HRV39a|    CACACAAGTAGCACCCAGCCTGAAGACACAATTGAAACAAGATATGTGCAAACCTCACAT
819  26_HRV39b|    CACACAAGTAGCATCCAACCTGAAGACACAATTGAAACAAGATATGTGCAAACCTCACAT
820  GROUP_6       CACACAAGTAGCA-CCA-CCTGAAGACACAATTGAAACAAGATATGTGCAAACCTCACAT
821
822  24_HRV39      ACTAGGGATGAAATGAGCGTTGAAAGTTTCTTAGGCAGATCTGGCTGTATTCACATTTCC
823  25_HRV39a|    ACTAGGGATGAAATGAGCGTTGAAAGTTTCTTAGGCAGATCTGGCTGTATTCACATTTCC
824  26_HRV39b|    ACTAGGGATGAAATGAGTGTTGAAAGTTTCTTAGGCAGATCTGGCTGTATTCACATTTCC
825  GROUP_6       ACTAGGGATGAAATGAG-GTTGAAAGTTTCTTAGGCAGATCTGGCTGTATTCACATTTCC
826
827  24_HRV39      ACAATTACTATGAAGAAGGAG-----------------AACTATA------ATGATCAT
828  25_HRV39a|    ACAATTACTATGAAGAAGGAG-----------------AACTATA------ATGATCAT
829  26_HRV39b|    ACAATTACTATGAAGAAGGAG-----------------AACTATA------ATGAACAT
830  GROUP_6       ACAATTACTATGAAGAAGGAG.................AACTATA......ATGA-CAT
831
832  24_HRV39      AATTTTGTGGATTGGAAAATTACTTTGCAGGAGATGGCACAGGTTAGAAGGAAATTTGAA
833  25_HRV39a|    AATTTTGTGGATTGGAAAATTACTTTGCAGGAGATGGCACAGGTTAGAAGGAAATTTGAA
834  26_HRV39b|    AATTTTGTGGATTGGAAAATTACTTTGCAGGAGATGGCACAGGTTAGAAGGAAATTTGAA
835  GROUP_6       AATTTTGTGGATTGGAAAATTACTTTGCAGGAGATGGCACAGGTTAGAAGGAAATTTGAA
836
837  24_HRV39      ATGTTCACCTATGTTAGATTTGACTCAGAGATTACTTTAG-TCCCATGCATAGCTGGAAG
```

FIG. D13 CONT'D

```
09.trace                                                                 9/20/2007 5:05 PM 838  25_HRV39a|   ATGTTCACCTATGTTAGATTTGACTCAGAGATTACTTTAG-TCCCATGCATAGCTGGAAG
839  26_HRV39b|   ATGTTCACCTACGTTAGATTTGACTCAGAGATTACTTTAG-TCCCATGCATAGCTGGAAG
840  GROUP_6     ATGTTCACCTA-GTTAGATTTGACTCAGAGATTACTTTAG.TCCCATGCATAGCTGGAAG
841
842  24_HRV39    AGGTGAAGATATTGGACACATAGTAATGCAATACATGTATGTCCCACCTGGTGCACCTGT
843  25_HRV39a|   AGGTGAAGATATTGGACACATAGTAATGCAATACATGTATGTCCCACCTGGTGCACCTGT
844  26_HRV39b|   AGGTGAAGATATTGGACACATAGTAATGCAATACATGTATGTCCCACCGGTGCACCTGT
845  GROUP_6     AGGTGAAGATATTGGACACATAGTAATGCAATACATGTATGTCCCACC-GGTGCACCTGT
846
847  24_HRV39    ACCTAAGAAGAGAGATGATTACACATGGCAATCTGGAACAAATGCCTCAGTTTTCTGGCA
848  25_HRV39a|   ACCTAAGAAGAGAGATGATTACACATGGCAATCTGGAACAAATGCCTCAGTTTTCTGGCA
849  26_HRV39b|   ACCTAAGAAGAGAGATGATTACACATGGCAATCTGGAACAAATGCCTCAGTTTTCTGGCA
850  GROUP_6     ACCTAAGAAGAGAGATGATTACACATGGCAATCTGGAACAAATGCCTCAGTTTTCTGGCA
851
852  24_HRV39    ACACGGACAGCCTTACCCTAGATTTTCATTACCATTTCTAAGCATAGCCTCAGCATATTA
853  25_HRV39a|   ACACGGACAGCCTTACCCTAGATTTTCATTACCATTTCTAAGCATAGCCTCAGCATATTA
854  26_HRV39b|   ACACGGACAGCCTTACCCTAGATTTTCATTACCATTTCTAAGCATAGCCTCAGCATATTA
855  GROUP_6     ACACGGACAGCCTTACCCTAGATTTTCATTACCATTTCTAAGCATAGCCTCAGCATATTA
856
857  24_HRV39    TATGTTCTATGATGGATATGATGGTGATAAATCGTCATCTAGGTATGGTGTTTCTGTCAC
858  25_HRV39a|   TATGTTCTATGATGGATATGATGGTGATAAATCGTCATCTAGGTATGGTGTTTCTGTCAC
859  26_HRV39b|   TATGTTCTATGATGGATATGATGGTGATAAATCGTCATCTAGGTATGGTGTTTCTGTCAC
860  GROUP_6     TATGTTCTATGATGGATATGATGGTGATAAATCGTCATCTAGGTATGGTGTTTCTGTCAC
861
862  24_HRV39    TAATGATATGGGTACACTTTGCACTAGAATTGTAACAAACCAACAGGAACACCTAGTGGA
863  25_HRV39a|   TAATGATATGGGTACACTTTGCACTAGAATTGTAACAAACCAACAGGAACACCTAGTGGA
864  26_HRV39b|   TAATGATATGGGTACACTTTGCACTAGAATTGTAACAAACCAACAGAACACCTAGTGGA
865  GROUP_6     TAATGATATGGGTACACTTTGCACTAGAATTGTAACAAACCAACAG-AACACCTAGTGGA
866
867  24_HRV39    GGTTACAACCAGAGTTTACCATAAAGCCAAGCATGTTAAAGCATGGTGCCCTAGGGCTCC
868  25_HRV39a|   GGTTACAACCAGAGTTTACCATAAAGCCAAGCATGTTAAAGCATGGTGCCCTAGGGCTCC
869  26_HRV39b|   GGTTACAACCAGAGTTTACCATAAAGCCAAGCATGTTAAAGCATGGTGCCCTAGGGCTCC
870  GROUP_6     GGTTACAACCAGAGTTTACCATAAAGCCAAGCATGTTAAAGCATGGTGCCCTAGGGCTCC
871
872  24_HRV39    CAGAGCAGTCCCTTACACA-CACAGCAATGTTACAAATTACAAAG-TACGGG---ACGGT
873  25_HRV39a|   CAGAGCAGTCCCTTACACA-CACAGCAATGTTACAAATTACAAAG-TACGGG---ACGGT
874  26_HRV39b|   CAGAGCAGTCCCTTACACA-CACAGCAATGTTACAAATTACAAAG-TACGGG---ACGGT
875  GROUP_6     CAGAGCAGTCCCTTACACA.CACAGCAATGTTACAAATTACAAAG.TACGGG...ACGGT
876
877  24_HRV39    GAAC------CAACACTCT---TTATAAAATCAAGAG------AGAATCTTACCACAG--
878  25_HRV39a|   GAAC------CAACACTCT---TTATAAAATCAAGAG------AGAATCTTACCACAG--
879  26_HRV39b|   GAAC------CAACACTCT---TTATAAAACCAAGAG------AGAATCTTACCACAG--
880  GROUP_6     GAAC......CAACACTCT...TTATAAAA-CAAGAG......AGAATCTTACCACAG..
881
882  24_HRV39    ----CT---------------
883  25_HRV39a|   ----CA---------------
884  26_HRV39b|   ----CT---------------
885  GROUP_6     ....C-...............
886
887
888
889  Group  7:
890
891  27_HRV10a|   AATCCAGTTGAAAATTACATTGATAATGTACTTAATGAAGTCCTAGTGGTACCCAACATC
892  28_HRV10b|   AATCCAGTTGAAAATTACATTGATAATGTACTTAATGAAGTCCTAGTGGTACCCAACATC
893  29_HRV10     AATCCAGTTGAAAATTACATTGATAATGTACTTAATGAAGTCCTAGTGGTACCCAACATC
894  30_HRV100a   AATCCAGTAGAAAATTATGTTGAAGGTGTGCTGAATGAAGTACTAGTGGTACCTAATATT
895  31_HRV100b   AATCCAGTAGAAAATTATGTTGAAGGTGTGCTGAATGAAGTACTAGTGGTACCTAATATT
896  32_HRV100    AATCCAGTAGAAAATTATGTTGAAGGTGTGCTGAATGAAGTACTAGTGGTACCTAATATT
897  GROUP_7     AATCCAGT-GAAAATTA--TTGA---TGT-CT-AATGAAGT-CTAGTGGTACC-AA-AT-
898
899  27_HRV10a|   AGAGAAAGTCATCCAAGCACCTCTAACTCTGCCCCAATTCTCGATGCAGCTGAGACTGGT
900  28_HRV10b|   AGAGAAAGTCATCCAAGCACCTCTAACTCTGCCCCAATTCTCGATGCAGCTGAGACTGGT
901  29_HRV10     AGAGAAAGTCATCCAAGCACCTCTAACTCTGCCCCAATTCTCGATGCAGCTGAGACTGGT
902  30_HRV100a   AGAGAGAGCCATCCAAGCACCTCAAACTCTGCTCCAATCCTTGATGCTGCTGAAACTGGC
```

FIG. D13 CONT'D

09.trace                                                                                                        9/20/2007 5:05 PM

```
903  31_HRV100b  AGAGAGAGCCATCCAAGCACCTCAAACTCTGCTCCAATCCTTGATGCTGCTGAAACTGGC
904  32_HRV100   AGAGAGAGCCATCCAAGCACCTCAAACTCTGCTCCAATCCTTGATGCTGCTGAAACTGGC
905  GROUP_7     AGAGA-AG-CATCCAAGCACCTC-AACTCTGC-CCAAT-CT-GATGC-GCTGA-ACTGG-
906
907  27_HRV10a|  CATACCAGTAGTGTACAACCAGAAGATACGGTTGAAACACGATATGTGCAAACATCCCAG
908  28_HRV10b|  CATACCAGTAGTGTACAACCAGAAGATACGGTTGAAACACGATATGTGCAAACATCCCAG
909  29_HRV10    CATACCAGTAGTGTACAACCAGAAGATACGGTTGAAACACGATATGTGCAAACATCCCAG
910  30_HRV100a  CACACTAGTAATGTGCAACCTGAAGATACAGTTGAAACTCGATATGTGCAGACATCACAG
911  31_HRV100b  CACACTAGTAATGTGCAACCTGAAGATACAGTTGAAACTCGATATGTGCAGACATCACAG
912  32_HRV100   CACACTAGTAATGTGCAACCTGAAGATACAGTTGAAACTCGATATGTGCAGACATCACAG
913  GROUP_7     CA-AC-AGTA-TGT-CAACC-GAAGATAC-GTTGAAAC-CGATATGTGCA-ACATC-CAG
914
915  27_HRV10a|  ACGAGAGATGAAATGAGTATTGAAAGTTTTCTTGGCAGGTCAGGTTGTATACACACCTCA
916  28_HRV10b|  ACGAGAGATGAAATGAGTATTGAAAGTTTTCTTGGCAGGTCAGGTTGTATACACACCTCA
917  29_HRV10    ACGAGAGATGAAATGAGTATTGAAAGTTTTCTTGGCAGGTCAGGTTGTATACACACCTCA
918  30_HRV100a  ACCAGGGATGAAATGAGTATTGAGAGCTTTCTTGGAAGATCTGGTTGTATACACACCTCA
919  31_HRV100b  ACCAGGGATGAAATGAGTATTGAGAGCTTTCTTGGAAGATCTGGTTGTATACACACCTCA
920  32_HRV100   ACCAGGGATGAAATGAGTATTGAGAGCTTTCTTGGAAGATCTGGTTGTATACACACCTCA
921  GROUP_7     AC-AG-GATGAAATGAGTATTGA-AG-TTTCTTGG-AG-TC-GGTTGTATACACACCTCA
922
923  27_HRV10a|  ACAATAACTGTTAATAATACAAGA---------------CCCTACA------ATGAACAC
924  28_HRV10b|  ACAATAACTGTTAATAATACAAGA---------------CCCTACA------ATGAACAC
925  29_HRV10    ACAATAACTGTTAATAATACAAGA---------------CCCTACA------ATGAACAC
926  30_HRV100a  ACAATTACTGTAAGTAAAATGAAA---------------AATTATA------ATGAGCAC
927  31_HRV100b  ACAATTACTGTAAGTAAAATGAAA---------------AATTATA------ATGAGCAC
928  32_HRV100   ACAATTACTGTAAGTAAAATGAAA---------------AATTATA------ATGAGCAC
929  GROUP_7     ACAAT-ACTGT-A-TAA-A--A-A...............---TA-A......ATGA-CAC
930
931  27_HRV10a|  ACTTTTGACACATGGCAAATAACTCTACAAGAAATGGCCCAAATTAGAAGGAAATTTGAA
932  28_HRV10b|  ACTTTTGACACATGGCAAATAACTCTACAAGAAATGGCCCAAATTAGAAGGAAATTTGAA
933  29_HRV10    ACTTTTGACACATGGCAAATAACTCTACAAGAAATGGCCCAAATTAGAAGGAAATTTGAA
934  30_HRV100a  ACTTTTGACAAATGGCAAATAACCCTACAGGAAATGGCCCAAATTAGAAGGAAATTTGAA
935  31_HRV100b  ACTTTTGACAAATGGCAAATAACCCTACAGGAAATGGCCCAAATTAGAAGGAAATTTGAA
936  32_HRV100   ACTTTTGACAAATGGCAAATAACCCTACAGGAAATGGCCCAAATTAGAAGGAAATTTGAA
937  GROUP_7     ACTTTTGACA-ATGGCAAATAAC-CTACA-GAAATGGCCCAAATTAGAAGGAAATTTGAA
938
939  27_HRV10a|  ATGTTTACATATGTTAGATTTGACTCAGAAGTCACTTTAG-TACCTTGCATCGCAGGCAA
940  28_HRV10b|  ATGTTTACATATGTTAGATTTGACTCAGAAGTCACTTTAG-TACCTTGCATCGCAGGCAA
941  29_HRV10    ATGTTTACATATGTTAGATTTGACTCAGAAGTCACTTTAG-TACCTTGCATCGCAGGCAA
942  30_HRV100a  ATGTTTACATATGTCAGATTTGACTCAGAAATCACATTGG-TACCCTGTATTGCAGGAAA
943  31_HRV100b  ATGTTTACATATGTCAGATTTGACTCAGAAATCACATTGG-TACCCTGTATTGCAGGAAA
944  32_HRV100   ATGTTTACATATGTCAGATTTGACTCAGAAATCACATTGG-TACCCTGTATTGCAGGAAA
945  GROUP_7     ATGTTTACATATGT-AGATTTGACTCAGAA-TCAC-TT-G.TACC-TG-AT-GCAGG-AA
946
947  27_HRV10a|  GGGCGATGACATAGGTCACATAGTTATGCAATATATGTATGTGCCACCTGGGGCTCCAGT
948  28_HRV10b|  GGGCGATGACATAGGTCACATAGTTATGCAATATATGTATGTGCCACCTGGGGCTCCAGT
949  29_HRV10    GGGCGATGACATAGGTCACATAGTTATGCAATATATGTATGTGCCACCTGGGGCTCCAGT
950  30_HRV100a  AGGAGATGACATAGGGCATATCGTAATGCAGTACATGTATGTGCCACCTGGAGCTCCAGT
951  31_HRV100b  AGGAGATGACATAGGGCATATCGTAATGCAGTACATGTATGTGCCACCTGGAGCTCCAGT
952  32_HRV100   AGGAGATGACATAGGGCATATCGTAATGCAGTACATGTATGTGCCACCTGGAGCTCCAGT
953  GROUP_7     -GG-GATGACATAGG-CA-AT-GT-ATGCA-TA-ATGTATGTGCCACCTGG-GCTCCAGT
954
955  27_HRV10a|  ACCAACTAAGAGAGATGATTTTGCTTGGCAGTCGGGAACAAATGCATCAGTCTTCTGGCA
956  28_HRV10b|  ACCAACTAAGAGAGATGATTTTGCTTGGCAGTCGGGAACAAATGCATCAGTCTTCTGGCA
957  29_HRV10    ACCAACTAAGAGAGATGATTTTGCTTGGCAGTCGGGAACAAATGCATCAGTCTTCTGGCA
958  30_HRV100a  TCCAACAAAAAGGGATGATTTTGCATGGCAATCAGGCACAAATGCATCAGTTTTTTGGCA
959  31_HRV100b  TCCAACAAAAAGGGATGATTTTGCATGGCAATCAGGCACAAATGCATCAGTTTTTTGGCA
960  32_HRV100   TCCAACAAAAAGGGATGATTTTGCATGGCAATCAGGCACAAATGCATCAGTTTTTTGGCA
961  GROUP_7     -CCAAC-AA-AG-GATGATTTTGC-TGGCA-TC-GG-ACAAATGCATCAGT-TT-TGGCA
962
963  27_HRV10a|  ACATGGACAACCTTTCCCTAGATTTTCTTTACCCTTCTTAAGCATTGCATCTGCTTACTA
964  28_HRV10b|  ACATGGACAACCTTTCCCTAGATTTTCTTTACCCTTCTTAAGCATTGCATCTGCTTACTA
965  29_HRV10    ACATGGACAACCTTTCCCTAGATTTTCTTTACCCTTCTTAAGCATTGCATCTGCTTACTA
966  30_HRV100a  GCATGGGCAGCCATTCCCTAGAATTTCTTTACCTTTCTTGAGCATTGCTTCTGCATACTA
967  31_HRV100b  GCATGGGCAGCCATTCCCTAGAATTTCTTTACCTTTCTTGAGCATTGCTTCTGCATACTA
```

FIG. D13 CONT'D

```
09.trace                                                                                                    9/20/2007 5:05 PM 968  32_HRV100    GCATGGGCAGCCATTCCCTAGAATTTCTTTACCTTTCTTGAGCATTGCTTCTGCATACTA
 969  GROUP_7      -CATGG-CA-CC-TTCCCTAGA-TTTCTTTACC-TTCTT-AGCATTGC-TCTGC-TACTA
 970
 971  27_HRV10a|   CATGTTCTATGATGGTTATGATGGTGATACACATGACTCACGTTATGGCACAACAGTGAT
 972  28_HRV10b|   CATGTTCTATGATGGTTATGATGGTGATACACATGACTCACGTTATGGCACAACAGTGAT
 973  29_HRV10     CATGTTCTATGATGGTTATGATGGTGATACACATGACTCACGTTATGGCACAACAGTGAT
 974  30_HRV100a   CATGTTTTATGATGGATATGATGGTGATACACATGATTCACACTATGGTACTACTGTAAT
 975  31_HRV100b   CATGTTTTATGATGGATATGATGGTGATACACATGATTCACACTATGGTACTACTGTAAT
 976  32_HRV100    CATGTTTTATGATGGATATGATGGTGATACACATGATTCACACTATGGTACTACTGTAAT
 977  GROUP_7      CATGTT-TATGATGG-TATGATGGTGATACACATGA-TCAC--TATGG-AC-AC-GT-AT
 978
 979  27_HRV10a|   AAATCACATGGGCACTTTGTGCATGCGAATAGTCACAAACCAGCAAGCACATGAGGTGGA
 980  28_HRV10b|   AAATCACATGGGCACTTTGTGCATGCGAATAGTCACAAACCAGCAAGCACATGAGGTGGA
 981  29_HRV10     AAATCACATGGGCACTTTGTGCATGCGAATAGTCACAAACCAGCAAGCACATGAGGTGGA
 982  30_HRV100a   TAACCACATGGGTACACTTTGTATGAGGATAGTTACAAATCAGCAAGCACATGAGGTGGA
 983  31_HRV100b   TAACCACATGGGTACACTTTGTATGAGGATAGTTACAAATCAGCAAGCACATGAGGTGGA
 984  32_HRV100    TAACCACATGGGTACACTTTGTATGAGGATAGTTACAAATCAGCAAGCACATGAGGTGGA
 985  GROUP_7      -AA-CACATGGG-AC--T-TG-ATG-G-ATAGT-ACAAA-CAGCAAGCACATGAGGTGGA
 986
 987  27_HRV10a|   AATTACCACCAGTGTTTATCACAAAGCCAAGCATGTCAAAGCATGGTGTCCAAGACCACC
 988  28_HRV10b|   AATTACCACCAGTGTTTATCACAAAGCCAAGCATGTCAAAGCATGGTGTCCAAGACCACC
 989  29_HRV10     AATTACCACCAGTGTTTATCACAAAGCCAAGCATGTCAAAGCATGGTGTCCAAGACCACC
 990  30_HRV100a   AATTACTACTAATATCTATCACAAGCCCAAACATGTTAAAGCTTGGTGCCCAAGACCACC
 991  31_HRV100b   AATTACTACTAATATCTATCACAAGGCCAAACATGTTAAAGCTTGGTGCCCAAGACCACC
 992  32_HRV100    AATTACTACTAATATCTATCACAAGGCCAAACATGTTAAAGCTTGGTGCCCAAGACCACC
 993  GROUP_7      AATTAC-AC-A-T-T-TATCACAA-GCCAA-CATGT-AAAGC-TGGTG-CCAAGACCACC
 994
 995  27_HRV10a|   CAGAGCTGTACCATATACA-CATGCCCATTCCACAAATTACAAAC-CACATG---GCAAA
 996  28_HRV10b|   CAGAGCTGTACCATATACA-CATGCCCATTCCACAAATTACAAAC-CACATG---GCAAA
 997  29_HRV10     CAGAGCTGTACCATATACA-CATGCCCATTCCACAAATTACAAAC-CACATG---GCAAA
 998  30_HRV100a   TCGGGCTGTGCCGTACACA-CATAGTCACTCTACAAATTACAAAC-CACATG---AGGGT
 999  31_HRV100b   TCGGGCTGTGCCGTACACA-CATAGTCACTCTACAAATTACAAAC-CACATG---AGGGT
1000  32_HRV100    TCGGGCTGTGCCGTACACA-CATAGTCACTCTACAAATTACAAAC-CACATG---AGGGT
1001  GROUP_7      --G-GCTGT-CC-TA-ACA.CAT---CA-TC-ACAAATTACAAAC.CACATG...-----
1002
1003  27_HRV10a|   GAAT------TACAAATAT---TTATTAGGTCTAGAGATGATCCCAAAGTAGTAACTG--
1004  28_HRV10b|   GAAT------TACAAATAT---TTATTAGGTCTAGAGATGATCCCAAAGTAGTAACTG--
1005  29_HRV10     GAAT------TACAAATAT---TTATTAGGTCTAGAGATGATCCCAAAGTAGTAACTG--
1006  30_HRV100a   GATG------TAAAGATTT---TCATTAGACCCAGAGATGATCCAAAGTTTGTAACTG--
1007  31_HRV100b   GATG------TAAAGATTT---TCATTAGACCCAGAGATGATCCAAAGTTTGTAACTG--
1008  32_HRV100    GATG------TAAAGATTT---TCATTAGACCCAGAGATGATCCAAAGTTTGTAACTG--
1009  GROUP_7      GA--......TA-A-AT-T...T-ATTAG--C-AGAGATGATCC-AA--T-GTAACTG..
1010
1011  27_HRV10a|   ----CA---------------
1012  28_HRV10b|   ----CC---------------
1013  29_HRV10     ----CT---------------
1014  30_HRV100a   ----CA---------------
1015  31_HRV100b   ----CG---------------
1016  32_HRV100    ----CT---------------
1017  GROUP_7      ....C-...............
1018
1019
1020
1021 Group  8:
1022
1023  33_HRV66     AATCCAGTTGAAGATTATGTTGAGGGTGTTTTAAATGAAGTTTTAGTAGTACCAAACATC
1024  34_HRV66b|   AATCCAGTTGAAGATTATGTTGAGGGTGTTTTAAATGAAGTTTTAGTAGTACCAAACATC
1025  35_HRV66a|   AATCCAGTTGAAGATTATGTTGAGGGTGTTTTAAATGAAGTTTTAGTAGTACCAAACATC
1026  36_HRV77a|   AATCCAGTTGAGGACTATATCGATAATGTACTTAATGAAGTCTTAGTAGTACCAAATACC
1027  37_HRV77b|   AATCCAGTTGAGGACTATATCGATAATGTACTTAATGAAGTCTTAGTAGTACCAAATACC
1028  38_HRV77     AATCCAGTTGAGGACTATATCGATAATGTACTTAATGAAGTCTTAGTAGTACCAAATACC
1029  GROUP_8      AATCCAGTTGA-GA-TAT-T-GA---TGT--T-AATGAAGT-TTAGTAGTACCAAA-A-C
1030
1031  33_HRV66     AAGGAAAGCCATCCAAGCACATCAAATGCTGCCCCAATACTAGATGCAGCTGAAACAGGT
1032  34_HRV66b|   AAGGAAAGCCATCCAAGCACATCAAATGCTGCCCCAATACTAGATGCAGCTGAAACAGGT
```

FIG. D13 CONT'D

09.trace                                                                                          9/20/2007 5:05 PM

```
1033  35_HRV66a|   AAGGAAAGCCATCCAAGCACATCAAATGCTGCCCCAATACTAGATGCAGCTGAAACAGGT
1034  36_HRV77a|   AAGGAGAGTCATCCAAGCACTTCTAACTCTGCTCCTATACTAGATGCAGCTGAAACAGGC
1035  37_HRV77b|   AAGGAGAGTCATCCAAGCACTTCTAACTCTGCTCCTATACTAGATGCAGCTGAAACAGGC
1036  38_HRV77    AAGGAGAGTCATCCAAGCACTTCTAACTCTGCTCCTATACTAGATGCAGCTGAAACAGGC
1037  GROUP_8     AAGGA-AG-CATCCAAGCAC-TC-AA--CTGC-CC-ATACTAGATGCAGCTGAAACAGG-
1038
1039  33_HRV66    CACACTAGTAAAGTACAACCAGAAGATACAGTTGAGACTCGTTACGTGCAAACATCACAG
1040  34_HRV66b|  CACACTAGTAAAGTACAACCAGAAGATACAGTTGAGACTCGTTACGTGCAAACATCACAG
1041  35_HRV66a|  CACACTAGTAAAGTACAACCAGAAGATACAGTTGAGACTCGTTACGTGCAAACATCACAG
1042  36_HRV77a|  CATACTAGTAGTGTGCAACCAGAAGATACAGTTGAGACCCGCTATGTACAAACTTCCCAG
1043  37_HRV77b|  CATACTAGTAGTGTGCAACCAGAAGATACAGTTGAGACCCGCTATGTACAAACTTCCCAG
1044  38_HRV77    CATACTAGTAGTGTGCAACCAGAAGATACAGTTGAGACCCGCTATGTACAAACTTCCCAG
1045  GROUP_8     CA-ACTAGTA--GT-CAACCAGAAGATACAGTTGAGAC-CG-TA-GT-CAAAC-TC-CAG
1046
1047  33_HRV66    ACTAGAGATGAAATGAGCATAGAAAGTTTTCTAGGTAGGTCAGGATGTATCCATATATCA
1048  34_HRV66b|  ACTAGAGATGAAATGAGCATAGAAAGTTTTCTAGGTAGGTCAGGATGTATCCATATATCA
1049  35_HRV66a|  ACTAGAGATGAAATGAGCATAGAAAGTTTTCTAGGTAGGTCAGGATGTATCCATATATCA
1050  36_HRV77a|  ACAAGGGATGAGATGAGTATTGAGAGCTTTCTGGGTAGGTCTGGTTGTATTCACATTTCA
1051  37_HRV77b|  ACAAGGGATGAGATGAGTATTGAGAGCTTTCTGGGTAGGTCTGGTTGTATTCACATTTCA
1052  38_HRV77    ACAAGGGATGAGATGAGTATTGAGAGCTTTCTGGGTAGGTCTGGTTGTATTCACATTTCA
1053  GROUP_8     AC-AG-GATGA-ATGAG-AT-GA-AG-TTTCT-GGTAGGTC-GG-TGTAT-CA-AT-TCA
1054
1055  33_HRV66    ACAATTAATGTGGATAGCACAAAA---------------ACATATG------ATGAATCC
1056  34_HRV66b|  ACAATTAATGTGGATAGCACAAAA---------------ACATATG------ATGAATCC
1057  35_HRV66a|  ACAATTAATGTGGATAGCACAAAA---------------ACATATG------ATGAATCC
1058  36_HRV77a|  ACAATAAATGTAGAAGATGGTAAA---------------ACTTATG------ATGAATCT
1059  37_HRV77b|  ACAATAAATGTAGAAGATGGTAAA---------------ACTTATG------ATGAATCT
1060  38_HRV77    ACAATAAATGTAGAAGATGGTAAA---------------ACTTATG------ATGAATCT
1061  GROUP_8     ACAAT-AATGT-GA-------AAA...............AC-TATG......ATGAATC-
1062
1063  33_HRV66    AAATTTAGAACATGGCAAATTACATTGCAAGAAATGGCTCAAATCAGACGCAAATTTGAG
1064  34_HRV66b|  AAATTTAGAACATGGCAAATTACATTGCAAGAAATGGCTCAAATCAGACGCAAATTTGAG
1065  35_HRV66a|  AAATTTAGAACATGGCAAATTACATTGCAAGAAATGGCTCAAATCAGACGCAAATTTGAG
1066  36_HRV77a|  AAATTTAGAAAATGGCAAATTACACTACAAGAAATGGCTCAAATTAGGCGCAAATTTGAA
1067  37_HRV77b|  AAATTTAGAAAATGGCAAATTACACTACAAGAAATGGCTCAAATTAGGCGCAAATTTGAA
1068  38_HRV77    AAATTTAGAAAATGGCAAATTACACTACAAGAAATGGCTCAAATTAGGCGCAAATTTGAA
1069  GROUP_8     AAATTTAGAA-ATGGCAAATTACA-T-CAAGAAATGGCTCAAAT-AG-CGCAAATTTGA-
1070
1071  33_HRV66    ATGTTCACATATGTTAGGTTTGATTCTGAAATTACATTAG-TCCCATGCATTGCAGGAAA
1072  34_HRV66b|  ATGTTCACATATGTTAGGTTTGATTCTGAAATTACATTAG-TCCCATGCATTGCAGGAAA
1073  35_HRV66a|  ATGTTCACATATGTTAGGTTTGATTCTGAAATTACATTAG-TCCCATGCATTGCAGGAAA
1074  36_HRV77a|  ATGTTTACATATGTAAGATTTGATTCAGAAATTACATTGG-TCCCATGTATTGCTGGAAA
1075  37_HRV77b|  ATGTTTACATATGTAAGATTTGATTCAGAAATTACATTGG-TCCCATGTATTGCTGGAAA
1076  38_HRV77    ATGTTTACATATGTAAGATTTGATTCAGAAATTACATTGG-TCCCATGTATTGCTGGAAA
1077  GROUP_8     ATGTT-ACATATGT-AG-TTTGATTC-GAAATTACATT-G.TCCCATG-ATTGC-GGAAA
1078
1079  33_HRV66    GGGTGATGATATAGGACATATTGTGATGCAATACATGTATGTACCACCTGGAGCCCCAAT
1080  34_HRV66b|  GGGTGATGATATAGGACATATTGTGATGCAATACATGTATGTACCACCTGGAGCCCCAAT
1081  35_HRV66a|  GGGTGATGATATAGGACATATTGTGATGCAATACATGTATGTACCACCTGGAGCCCCAAT
1082  36_HRV77a|  AGGTGATGACATAGGACATGTTGTCATGCAATACATGTATGTACCACCAGGGGCACCCAT
1083  37_HRV77b|  AGGTGATGACATAGGACATGTTGTCATGCAATACATGTATGTACCACCAGGGGCACCCAT
1084  38_HRV77    AGGTGATGACATAGGACATGTTGTCATGCAATACATGTATGTACCACCAGGGGCACCCAT
1085  GROUP_8     -GGTGATGA-ATAGGACAT-TTGT-ATGCAATACATGTATGTACCACC-GG-GC-CC-AT
1086
1087  33_HRV66    TCCAGATAATAGAACACACTTTGCTTGGCAATCAGGAACAAATGCATCTATATTCTGGCA
1088  34_HRV66b|  TCCAGATAATAGAACACACTTTGCTTGGCAATCAGGAACAAATGCATCTATATTCTGGCA
1089  35_HRV66a|  TCCAGATAATAGAACACACTTTGCTTGGCAATCAGGAACAAATGCATCTATATTCTGGCA
1090  36_HRV77a|  ACCAGATAGCAGGACTCATTTTGCATGGCAGTCAGGGACTAATGCATCAATATTCTGGCA
1091  37_HRV77b|  ACCAGATAGCAGGACTCATTTTGCATGGCAGTCAGGGACTAATGCATCAATATTCTGGCA
1092  38_HRV77    ACCAGATAGCAGGACTCATTTTGCATGGCAGTCAGGGACTAATGCATCAATATTCTGGCA
1093  GROUP_8     -CCAGATA--AG-AC-CA-TTTGC-TGGCA-TCAGG-AC-AATGCATC-ATATTCTGGCA
1094
1095  33_HRV66    ACTTGGACAACCATTCCCAAGATTCTCGCTACCTTTTCTAGGCATAGCTTCAGCATATTA
1096  34_HRV66b|  ACTTGGACAACCATTCCCAAGATTCTCGCTACCTTTTCTAGGCATAGCTTCAGCATATTA
1097  35_HRV66a|  ACTTGGACAACCATTCCCAAGATTCTCGCTACCTTTTCTAGGCATAGCTTCAGCATATTA
```

FIG. D13 CONT'D

```
09.trace                                                                    9/20/2007 5:05 PM 1098 36_HRV77a|    ACATGGACAACCATTCCCAAGATTTTCACTACCTTTTCTGAGTATTGCTTCAGCTTACTA
1099 37_HRV77b|    ACATGGACAACCATTCCCAAGATTTTCACTACCTTTTCTGAGTATTGCTTCAGCTTACTA
1100 38_HRV77     ACATGGACAACCATTCCCAAGATTTTCACTACCTTTTCTGAGTATTGCTTCAGCTTACTA
1101 GROUP_8      AC-TGGACAACCATTCCCAAGATT-TC-CTACCTTTTCT--G-AT-GCTTCAGC-TA-TA
1102
1103 33_HRV66     CATGTTCTATGATGGTTATGATGGAGATACTCCTGGGTCTCGTTATGGAACCACAGTAGT
1104 34_HRV66b|   CATGTTCTATGATGGTTATGATGGAGATACTCCTGGGTCTCGTTATGGAACCACAGTAGT
1105 35_HRV66a|   CATGTTCTATGATGGTTATGATGGAGATACTCCTGGGTCTCGTTATGGAACCACAGTAGT
1106 36_HRV77a|   CATGTTTTATGATGGCTATGATGGGGATACCTATGAATCACGTTATGGTACTACAGTGGT
1107 37_HRV77b|   CATGTTTTATGATGGCTATGATGGGGATACCTATGAATCACGTTATGGTACTACAGTGGT
1108 38_HRV77     CATGTTTTATGATGGCTATGATGGGGATACCTATGAATCACGTTATGGTACTACAGTGGT
1109 GROUP_8      CATGTT-TATGATGG-TATGATGG-GATAC---TG--TC-CGTTATGG-AC-ACAGT-GT
1110
1111 33_HRV66     TAATCATATGGGTACATTATGTATTAGGATTGTTACAAATGAACAGCACCATAATGTTGA
1112 34_HRV66b|   TAATCATATGGGTACATTATGTATTAGGATTGTTACAAATGAACAGCACCATAATGTTGA
1113 35_HRV66a|   TAATCATATGGGTACATTATGTATTAGGATTGTTACAAATGAACAGCACCATAATGTTGA
1114 36_HRV77a|   TAATCACATGGGCACACTGTGCATTAGAATAGTCACTAATCAGCAAAATCATGAGGTTGA
1115 37_HRV77b|   TAATCACATGGGCACACTGTGCATTAGAATAGTCACTAATCAGCAAAATCATGAGGTTGA
1116 38_HRV77     TAATCACATGGGCACACTGTGCATTAGAATAGTCACTAATCAGCAAAATCATGAGGTTGA
1117 GROUP_8      TAATCA-ATGGG-ACA-T-TG-ATTAG-AT-GT-AC-AAT-A-CA--A-CAT-A-GTTGA
1118
1119 33_HRV66     AATTACTACTAGAGTATACCATAAGGCTAAGCATGTTAAAGCCTGGTGTCCTAGACCACT
1120 34_HRV66b|   AATTACTACTAGAGTATACCATAAGGCTAAGCATGTTAAAGCCTGGTGTCCTAGACCACT
1121 35_HRV66a|   AATTACTACTAGAGTATACCATAAGGCTAAGCATGTTAAAGCCTGGTGTCCTAGACCACT
1122 36_HRV77a|   AATCACCACTAGAGTATACCACAAGGCTAAACATATTAAAGCTTGGTGTCCCAGACCACC
1123 37_HRV77b|   AATCACCACTAGAGTATACCACAAGGCTAAACATATTAAAGCTTGGTGTCCCAGACCACC
1124 38_HRV77     AATCACCACTAGAGTATACCACAAGGCTAAACATATTAAAGCTTGGTGTCCCAGACCACC
1125 GROUP_8      AAT-AC-ACTAGAGTATACCA-AAGGCTAA-CAT-TTAAAGC-TGGTGTCC-AGACCAC-
1126
1127 33_HRV66     TAGAGCTGTACCATACACA-ACTGTAAACTCAACCAATTATATGC-CTCATA---CTGGT
1128 34_HRV66b|   TAGAGCTGTACCATACACA-ACTGTAAACTCAACCAATTATATGC-CTCATA---CTGGT
1129 35_HRV66a|   TAGAGCTGTACCATACACA-ACTGTAAACTCAACCAATTATATGC-CTCATA---CTGGT
1130 36_HRV77a|   TAGAGCTGTACCATACACA-GCAGTAGATTCAACAAATTACAAAC-CTATGA---GAGGG
1131 37_HRV77b|   TAGAGCTGTACCATACACA-GCAGTAGATTCAACAAATTACAAAC-CTATGA---GAGGG
1132 38_HRV77     TAGAGCTGTACCATACACA-GCAGTAGATTCAACAAATTACAAAC-CTATGA---GAGGG
1133 GROUP_8      TAGAGCTGTACCATACACA.-C-GTA-A-TCAAC-AATTA-A--C.CT---A...--GG-
1134
1135 33_HRV66     GATC------TGCAAATTT---TCATTAAACCTAGAACAGATCCAAAAGTAGTCAATG--
1136 34_HRV66b|   GATC------TGCAAATTT---TCATTAAACCTAGAACAGATCCAAAAGTAGTCAATG--
1137 35_HRV66a|   GATC------TGCAAATTT---TCATTAAACCTAGAACAGATCCAAAAGTAGTCAATG--
1138 36_HRV77a|   GATG------TACAAATCT---TTATTAAAGAGAGAGCAAGCCCAAAAGTAGTTACTT--
1139 37_HRV77b|   GATG------TACAAATCT---TTATTAAAGAGAGAGCAAGCCCAAAAGTAGTTACTT--
1140 38_HRV77     GATG------TACAAATCT---TTATTAAAGAGAGAGCAAGCCCAAAAGTAGTTACTT--
1141 GROUP_8      GAT-......T-CAAAT-T...T-ATTAAA---AGA-CA---CCAAAAGTAGT-A-T-..
1142
1143 33_HRV66     ----TA---------------
1144 34_HRV66b|   ----TG---------------
1145 35_HRV66a|   ----TC---------------
1146 36_HRV77a|   ----TG---------------
1147 37_HRV77b|   ----TA---------------
1148 38_HRV77     ----TT---------------
1149 GROUP_8      ....T-...............
1150
1151
1152
1153 Group 9:
1154
1155 39_HRV62a    AATCCAATTGAAAATTATGTAGATCAAGTACTTAATGAAGTTTTAGTTGTACCAAATATT
1156 40_HRV62b    AATCCAATTGAAAATTATGTAGATCAAGTACTTAATGAAGTTTTAGTTGTACCAAATATT
1157 41_HRV25     AATCCAATTGAAAATTATGTAGATCAAGTACTTAATGAGGTTCTAGTCGTACCAAATATT
1158 42_HRV29a    AACCCAGTTGAAAACTATGTGGATGAGGTGCTTAATGAAGTTTTAGTTGTGCCTAACATC
1159 43_HRV29b    AACCCAGTTGAAAACTATGTGGATGAGGTGCTTAATGAAGTTTTAGTTGTGCCTAACATC
1160 44_HRV44a    AACCCAGTTGAAAATTATGTGGATGAAGTACTTAATGAAGTCTTAGTTGTGCCTAATATC
1161 45_HRV44b    AACCCAGTTGAAAATTATGTGGATGAAGTACTTAATGAAGTCTTAGTTGTGCCTAATATC
1162 GROUP_9      AA-CCA-TTGAAAA-TATGT-GAT-A-GT-CTTAATGA-GT--TAGT-GT-CC-AA-AT-
```

FIG. D13 CONT'D

09.trace                                                                                              9/20/2007 5:05 PM

```
1163
1164 39_HRV62a    AAAGAAAGTCACCCTAGTACGTCAAACTCTGCCCCAATTCTAGATGCTGCTGAAACCGGA
1165 40_HRV62b    AAAGAAAGTCACCCTAGTACGTCAAACTCTGCCCCAATTCTAGATGCTGCTGAAACCGGA
1166 41_HRV25     AAAGAAAGTCACCCAAGCACATCAAATTCTGCCCCAATTCTAGATGCTGCTGAAACTGGA
1167 42_HRV29a    AGGGAGAGCCACCCAAGCACGTCCAACTCTGCACCAATCTTGGATGCTGCTGAGACTGGA
1168 43_HRV29b    AGGGAGAGCCACCCAAGCACGTCCAACTCTGCACCAATCTTGGATGCTGCTGAGACTGGA
1169 44_HRV44a    AGAGAGAGCCACCCAAGCACATCTAACTCTGCTCCAATTTTGGATGCTGCTGAAACTGGA
1170 45_HRV44b    AGAGAGAGCCACCCAAGCATATCTAACTCTGCTCCAATTTTGGATGCTGCTGAAACTGGA
1171 GROUP_9      A--GA-AG-CACCC-AG-A--TC-AA-TCTGC-CCAAT--T-GATGCTGCTGA-AC-GGA
1172
1173 39_HRV62a    CACACTAGTAATGTACAACCAGAAGACACTATTGAAACCCGTCATGTTCAAACCACACAA
1174 40_HRV62b    CACACTAGTAATGTACAACCAGAAGACACTATTGAAACCCGTTATGTTCAAACCACACAA
1175 41_HRV25     CACACTAGCAATGTGCAACCAGAGGATACCATTGAAACTCGTTATGTTCAAACCACACAA
1176 42_HRV29a    CATACTAGTAATGTACAACCAGAAGATACCATTGAGACTCGTTATGTACAAACCTCACAT
1177 43_HRV29b    CATACTAGTAATGTACAACCAGAAGATACCATTGAGACTCGTTATGTACAAACCTCACAT
1178 44_HRV44a    CATACTAGTAATGTACAACCAGAAGATACCATTGAGACTCGATATGTACAAACCTCACAA
1179 45_HRV44b    CATACTAGTAATGTACAACCAGAAGATACCATTGAGACTCGATATGTACAAACCTCACAA
1180 GROUP_9      CA-ACTAG-AATGT-CAACCAGA-GA-AC-ATTGA-AC-CG--ATGT-CAAACC-CACA-
1181
1182 39_HRV62a    ACTAGAGATGAAATGAGCATTGAGAGCTTTCTTGGTAGGTCAGGGTGCGTACACACTTCA
1183 40_HRV62b    ACTAGAGATGAAATGAGCATTGAGAGCTTTCTTGGTAGGTCAGGGTGCGTACACACTTCA
1184 41_HRV25     ACTAGAGATGAAATGAGTATTGAAAGTTTTCTTGGTAGGTCAGGGTGTGTACATACTTCA
1185 42_HRV29a    ACTAGAGATGAAATGAGCATTGAAAGTTTTCTTGGGTAGATCAGGATGTATACATGTTTCA
1186 43_HRV29b    ACTAGAGATGAAATGAGCATTGAAAGTTTTCTTGGGTAGATCAGGATGTATACATGTTTCA
1187 44_HRV44a    ACTAGAGATGAAATGAGCATTGAAAGTTTTCTTGGCAGATCAGGGTGTATACATGTTTCA
1188 45_HRV44b    ACTAGAGATGAAATGAGCATTGAAAGTTTTCTTGGCAGATCAGGGTGTATACATGTTTCA
1189 GROUP_9      ACTAGAGATGAAATGAG-ATTGA-AG-TT--T-GG-AG-TCAGG-TG--TACA---TTCA
1190
1191 39_HRV62a    ACAATTGAA---------ACAACG---------------CTTAGTC------ATAAAGAT
1192 40_HRV62b    ACAATTGAA---------ACAACG---------------CTTAGTC------ATAAAGAT
1193 41_HRV25     ACAATTAAA---------ACAAAA---------------CTTAAAC------ATGATGAA
1194 42_HRV29a    ACAATAAAA---------GCAAAT---------------CAGGCAC------ATGACGCC
1195 43_HRV29b    ACAATAAAA---------GCAAAT---------------CAGGCAC------ATGACGCC
1196 44_HRV44a    ACAATAAAG---------ACAAAT---------------CAGGCAC------ACAATACC
1197 45_HRV44b    ACAATAAAG---------ACAAAT---------------CAGGCAC------ACAATACC
1198 GROUP_9      ACAAT--A-.........-CAA--...............C-----C......A--A----
1199
1200 39_HRV62a    AGATTCAAAACATGGAATATTAACTTACAAGAGATGGCTCAAATCAGGAGAAAGTTTGAA
1201 40_HRV62b    AGATTCAAAACATGGAATATTAACTTACAAGAGATGGCTCAAATCAGGAGAAAGTTTGAA
1202 41_HRV25     AGATTTAAAATATGGAATATCAATTTACAAGAAATGGCTCAAATTAGGAGAAAGTTTGAG
1203 42_HRV29a    AAGTTCGATAAATGGAATGTTAACTTACAAGAAATGGCTCAAATTAGGCGCAAATTTGAA
1204 43_HRV29b    AAGTTCGATAAATGGAATGTTAACTTACAAGAAATGGCTCAAATTAGGCGCAAATTTGAA
1205 44_HRV44a    AAGTTTGATAAATGGAATATCAACTTACAAGAAATGGCTCAAATTAGACGCAAATTTGAA
1206 45_HRV44b    AAGTTTGATAAATGGAATATCAACTTACAAGAAATGGCTCAAATTAGACGCAAATTTGAA
1207 GROUP_9      A--TT--A-A-ATGGAAT-T-AA-TTACAAGA-ATGGCTCAAAT-AG--G-AA-TTTGA-
1208
1209 39_HRV62a    ATGTTTACATATGTAAGATTTGATTCAGAAATAACCCTGG-TTCCATCTATTGCAGGACG
1210 40_HRV62b    ATGTTTACATATGTAAGATTTGATTCAGAAATAACCCTGG-TTCCATCTATTGCAGGACG
1211 41_HRV25     ATGTTTACATATGTGAGATTTGATTCAGAGATAACCCTAG-TTCCATCTATTGCAGGACG
1212 42_HRV29a    ATGTTCACATATGTGAGATTTGACTCAGAAATAACTCTGG-TTCTTTGCATTGCAGGACG
1213 43_HRV29b    ATGTTCACATATGTGAGATTTGACTCAGAAATAACTCTGG-TTCCATGCATTGCAGGACG
1214 44_HRV44a    ATGTTCACATATGTGAGATTTGATTCGGAAATAACTCTAG-TTCCATGCATTGCAGGACA
1215 45_HRV44b    ATGTTCACATATGTGAGATTTGATTCAGAAATAACTCTAG-TTCCATGCATTGCAGGACG
1216 GROUP_9      ATGTT-ACATATGT-AGATTTGA-TC-GA-ATAAC-CT-G.TTC--T---ATTGCAGGAC-
1217
1218 39_HRV62a    TGGTGCAGATATAGGTCACATAGTTATGCAATATATGTATGTACCACCTGGGGCTCCACT
1219 40_HRV62b    TGGTGCAGATATAGGTCACATAGTTATGCAATATATGTATGTACCACCTGGGGCTCCACT
1220 41_HRV25     TGGTGCAGATATAGGTCACATAGTTATGCAATATATGTGTGCCACCTGGAGCCCCCATT
1221 42_HRV29a    TGGTAATGATATAGGTCACATAGTTATGCAGTACATGTATGTACCACCTGGAGCTCCAGT
1222 43_HRV29b    TGGTAATGATATAGGTCACATAGTTATGCAGTACATGTATGTACCACCTGGAGCTCCAGT
1223 44_HRV44a    TGGTGATGATATAGGCCACATAGTTATGCAGTACATGTATGTACCACCTGGAGCTCCAGT
1224 45_HRV44b    TGGTGATGATATAGGCCACATAGTTATGCAGTACATGTATGTACCACCTGGAGCTCCAGT
1225 GROUP_9      TGGT---GATATAGG-CACATAGTTATGCA-TA-ATGTATGT-CCACCTGG-GC-CCA-T
1226
1227 39_HRV62a    ACCAACAGACAGAAAGCATTTTGCCTGGCAATCAAGTACTAATGCATCAATATTTTGGCA
```

FIG. D13 CONT'D 09.trace                                                                                              9/20/2007 5:05 PM

```
1228 40_HRV62b    ACCAACAGACAGAAAGCATTTTGCCTGGCAATCAAGTACTAATGCATCAATATTTTGGCA
1229 41_HRV25     ACCAACAGACAGAAAACACTTTGCATGGCAATCAAGTACTAATGCATCAATATTTTGGCA
1230 42_HRV29a    ACCAAATGACAGAAATCATTTTGCATGGCAATCAGGGACTAATGCATCAATATTCTGGCA
1231 43_HRV29b    ACCAAATGACAGAAATCATTTTGCATGGCAATCAGGGACTAATGCATCAATATTCTGGCA
1232 44_HRV44a    ACCAGATGACAGAAACCACTTTGCATGGCAATCGGGGACTAATGCATCAATATTCTGGCA
1233 45_HRV44b    ACCAGATGACAGAATCCACTTTGCATGGCAATCGGGGAATAATGCATCAATATTCTGGCA
1234 GROUP_9      ACCA---GACAGAA--CA-TTTGC-TGGCAATC--G-A-TAATGCATCAATATT-TGGCA
1235
1236 39_HRV62a    ACATGGGCAACCCTTTCCTAGATTTTCATTACCTTTTTTGAGTGTTGCATCTGCTTATTA
1237 40_HRV62b    ACATGGGCAACCCTTTCCTAGATTTTCATTACCTTTTTTGAGTGTTGCATCTGCTTATTA
1238 41_HRV25     ACATGGACAACCCTTCCCTAGATTTTCATTGCCATTTCTGAGTGTTGCATCTGCTTATTA
1239 42_HRV29a    ACATGGTCAGCCTTTCCCAAGATTTTCATTACCATTCCTAAGTGTTGCATCTGCTTATTA
1240 43_HRV29b    ACATGGTCAGCCTTTCCCAAGATTTTCATTACCATTCCTAAGTGTTGCATCTGCTTATTA
1241 44_HRV44a    ACATGGTCAACCTTTCCCAAGATTTTCATTGCCATTTCTAAGTGTTGCATCTGCCTATTA
1242 45_HRV44b    ACATGGTCAACCTTTCCCAAGATTTTCATTGCCATTTCTAAGTGTTGCATCTGCCTATTA
1243 GROUP_9      ACATGG-CA-CC-TT-CC-AGATTTTCATT-CC-TT--T-AGTGTTGCATCTGC-TATTA
1244
1245 39_HRV62a    CATGTTTTATGATGGCTATAATGGTGATGACTATACAGCAAAATACGGTACCACCGTGGT
1246 40_HRV62b    CATGTTTTATGATGGCTATAATGGTGATGACTATACAGCAAAATACGGTACCACCGTGGT
1247 41_HRV25     CATGTTTTATGATGGCTATAATGGTGATGATCACACAGCGAGATATGGTACCACTGTGGT
1248 42_HRV29a    CATGTTTTATGATGGTTACAATGGAGGTGATCATACAGCAACTTATGGCACCACAGTGGT
1249 43_HRV29b    CATGTTTTATGATGGTTACAATGGAGGTGATCATACAGCAACTTATGGCACCACAGTGGT
1250 44_HRV44a    CATGTTTTATGACGGTTATAATGGAGGTGATCATACAGCAACTTATGGCACCACAGTGGT
1251 45_HRV44b    CATGTTTTATGACGGTTATAATGGAGGTGATCATACAGCAACTTATGGCACCACAGTGGT
1252 GROUP_9      CATGTTTTATGA-GG-TA-AATGG-G-TGA--A-ACAGC-A--TA-GG-ACCAC-GTGGT
1253
1254 39_HRV62a    TAATCGTATGGGGGCACTGTGTATGAGGATTGTCACAAACAAACAAGTTCATGATGTTGA
1255 40_HRV62b    TAATCGTATGGGGGCACTGTGTATGAGGATTGTCACAAACAAACAAGTTCATGATGTTGA
1256 41_HRV25     TAACCGTATGGGGAGCACTGTGCATGAGAATTGTCACAAATAAACAAGTCCATGATGTTGA
1257 42_HRV29a    TAACCGGATGGGGACGCTTTGTGTCAGAATTGTTACAGGCAAACAAGCTCATGATGTTCA
1258 43_HRV29b    TAACCGGATGGGGACGCTTTGTGTCAGAATTGTTACAGGCAAACAAGCTCATGATGTTCA
1259 44_HRV44a    TAACCGGATGGGGACGCTTTGCGTCAGGATCGTTACGGGCAAACAGGCTCATGATGTCCA
1260 45_HRV44b    TAACCGGATGGGGACGCTTTGCGTCAGGATCGTTACGGGCAAACAGGCTCATGATGTCCA
1261 GROUP_9      TAA-CG-ATGGG--C-CT-TG--T-AG-AT-GT-AC----AAACA-G--CATGATGT--A
1262
1263 39_HRV62a    GGTCACAACTAATATTTACCACAAGGCTAAGCATGTAAAAGCGTGGTGCCCGCGGCCGCC
1264 40_HRV62b    GGTCACAACTAATATTTACCACAAGGCTAAGCATGTAAAAGCGTGGTGCCCTAGACCACC
1265 41_HRV25     GGTTACAACTAACATTTACCATAAAGCTAAGCATGTAAAAGCATGGTGCCCTAGACCACC
1266 42_HRV29a    AGTTACAACAAGTATCTATCATAAAGCTAAACATGTAAAGGCGTGTGTCCTAGACCACC
1267 43_HRV29b    AGTTACAACAAGTATCTATCATAAAGCTAAACATGTAAAGGCGTGGTGTCCTAGACCACC
1268 44_HRV44a    AGTTACAACAAGCATTTATCACAAAGCTAAACATGTAAAAGCATGGTGCCCTAGACCACC
1269 45_HRV44b    AGTTACAACAAGCATTTATCACAAAGCTAAACATGTAAAAGCATGGTGCCCTAGACCACC
1270 GROUP_9      -GT-ACAAC-A--AT-TA-CA-AA-GCTAA-CATGTAAA-GC-TGGTG-CC--G-CC-CC
1271
1272 39_HRV62a    CAGAGCTGTTCCATATAAA-TATGTTGATTTCAATAATTATGCAG-CCAGTG---ATAGT
1273 40_HRV62b    TAGAGCTGTTCCATATAAA-TATGTTGATTTCAATAATTATGCAG-CCAGTG---ATAGT
1274 41_HRV25     TAGAGCTGTCCCATATAAA-TATGTTGACTTCAATAATTATGCAG-CCAGTG---ATAAT
1275 42_HRV29a    AAGAGTTGTCCCATACAAG-TATGTTGGCCTAACTAATTACACAC-TTAAAG---AAGAA
1276 43_HRV29b    AAGAGTTGTCCCATACAAG-TATGTTGGCCTAACTAATTACACAC-TTAAAG---AAGAA
1277 44_HRV44a    AAGGGTTGTCCCATACAAG-TATGTTGGCCTAACTAATTACACAC-TTAAAG---AAACA
1278 45_HRV44b    AAGGGTTGTCCCATACAAG-TATGTTGGCCTAACTAATTACACAC-TTAAAG---AAACA
1279 GROUP_9      -AG-G-TGT-CCATA-AA-.TATGTTG---T-A-TAATTA--CA-.--A--G...A----
1280
1281 39_HRV62a    ---G------TTGACATTT---TTATAAAATCAAGG------CAAAACTTGCAAACAG--
1282 40_HRV62b    ---G------TTGACATTT---TTATAAAATCAAGG------CAAAACTTGCAAACAG--
1283 41_HRV25     ---G------TTGACATCT---TTATACAACCAAGA------AACAGTTTAAAAACAG--
1284 42_HRV29a    ---G------AT-CCAG-----TTGTGGAATCCAGA------CCAAGCTTAATGACAG--
1285 43_HRV29b    ---G------AT-ACAG-----TTGTGGAATCCAGA------CCAAGCTTAATGACAG--
1286 44_HRV44a    ---G------AT-ACAG-----TTGTGGAACCTAGA------CACAGCATAATGACAG--
1287 45_HRV44b    ---G------AT-ACAG-----TTGTGGAACCTAGA------CACAGCATAATGACAG--
1288 GROUP_9      ...G......-T--CA---...TT-T--AA-C-AG-.......---A---T----ACAG..
1289
1290 39_HRV62a    ----CT--------------
1291 40_HRV62b    ----C---------------
1292 41_HRV25     ----CT--------------
```

FIG. D13 CONT'D 09.trace                                                                              9/20/2007 5:05 PM

```
1293 42_HRV29a       ----CT---------------
1294 43_HRV29b       ----CT---------------
1295 44_HRV44a       ----CT---------------
1296 45_HRV44b       ----CT---------------
1297 GROUP_9         ....C-...............
1298
1299
1300
1301 GROUP  10:
1302
1303 46_HRV31        AATCCAGTTGAAAACTATGTGGAAGAGGTTCTTAATGAAGTCTTAGTAGTACCTAATATC
1304 47_HRV31a|      AATCCAGTTGAAAACTATGTGGAAGAGGTTCTTAATGAAGTCTTAGTAGTACCTAATATC
1305 48_HRV31b|      AATCCAGTTGAAAACTATGTGGAAGAGGTTCTTAATGAAGTCTTAGTAGTACCTAATATC
1306 49_HRV47        AACCCAGTCGAAAATTATGTGGAAGAGGTACTTAATGAGGTCTTAGTTGTACCAAATATC
1307 50_HRV47a|      AACCCAGTCGAAAATTATGTGGAAGAGGTACTTAATGAGGTCTTAGTTGTACCAAATATC
1308 51_HRV47b|      AACCCAGTCGAAAATTATGTGGAAGAGGTACTTAATGAGGTCTTAGTTGTACCAAATATC
1309 GROUP_10        AA-CCAGT-GAAAA-TATGTGGAAGAGG-CTTAATGA-GTCTTAGT-GTACC-AATATC
1310
1311 46_HRV31        AAAGAAAGCCATCCAAGCACATCTAATTCTGCCCCAATCCTGGACGCTGCTGAAACTGGA
1312 47_HRV31a|      AAAGAAAGCCATCCAAGCACATCTAATTCTGCCCCAATCCTGGACGCTGCTGAAACTGGA
1313 48_HRV31b|      AAAGAAAGCCATCCAAGCACATCTAATTCTGCCCCAATCCTGGACGCTGCTGAAACTGGA
1314 49_HRV47        AAAGAAAGTCATCCAAGTACATCCAACTCTGCCCCGATTTTAGATGCTGCTGAAACTGGA
1315 50_HRV47a|      AAAGAAAGTCATCCAAGTACATCCAACTCTGCCCCGATTTTAGATGCTGCTGAAACTGGA
1316 51_HRV47b|      AAAGAAAGTCATCCAAGTACATCCAACTCTGCCCCGATTTTAGATGCTGCTGAAACTGGA
1317 GROUP_10        AAAGAAAG-CATCCAAG-ACATC-AA-TCTGCCCC-AT--T-GA-GCTGCTGAAACTGGA
1318
1319 46_HRV31        CACACTAGTAATGTACAACCAGAAGATACAATTGAAACTCGCTACGTGCAAACATCACAA
1320 47_HRV31a|      CACACTAGTAATGTACAACCAGAAGATACAATTGAAACTCGCTACGTGCAAACATCACAA
1321 48_HRV31b|      CACACTAGTAATGTACAACCAGAAGATACAATTGAAACTCGCTACGTGCAAACATCACAA
1322 49_HRV47        CACACTAGCAATGTACAGCCAGAAGATACAATTGAAACTCGATATGTACAAACAGCACAA
1323 50_HRV47a|      CACACTAGCAATGTACAGCCAGAAGATACAATTGAAACTCGATATGTACAAACAGCACAA
1324 51_HRV47b|      CACACTAGCAATGTACAGCCAGAAGATACAATTGAAACTCGATATGTACAAACAGCACAA
1325 GROUP_10        CACACTAG-AATGTACA-CCAGAAGATACAATTGAAACTCG-TA-GT-CAAACA-CACAA
1326
1327 46_HRV31        ACAAGAGATGAAATGAGCATTGAAAGTTTCCTTGGTAGGTCAGGATGTGTACATACTTCA
1328 47_HRV31a|      ACAAGAGATGAAATGAGCATTGAAAGTTTCCTTGGTAGGTCAGGATGTGTACATACTTCA
1329 48_HRV31b|      ACAAGAGATGAAATGAGCATTGAAAGTTTCCTTGGTAGGTCAGGATGTGTACATACTTCA
1330 49_HRV47        ACAAGAGATGAAATGAGCATTGAGAGCTTCCTTGGCAGGTCAGGATGTGTGCATTCCTCA
1331 50_HRV47a|      ACAAGAGATGAAATGAGCATTGAGAGCTTCCTTGGCAGGTCAGGATGTGTGCATTCCTCA
1332 51_HRV47b|      ACAAGAGATGAAATGAGCATTGAGAGCTTCCTTGGCAGGTCAGGATGTGTGCATTCCTCA
1333 GROUP_10        ACAAGAGATGAAATGAGCATTGA-AG-TTCCTTGG-AGGTCAGGATGTGT-CAT-C-TCA
1334
1335 46_HRV31        ATAATAGAA---------CCAGAT---------------GGACTCC------ATGATAGC
1336 47_HRV31a|      ATAATAGAA---------CCAGAT---------------GGACTCC------ATGATAGC
1337 48_HRV31b|      ATAATAGAA---------CCAGAT---------------GGACTCC------ATGATAGC
1338 49_HRV47        ACAATAAAA---------TCAGAT---------------GAGCAAC------ACATTAAT
1339 50_HRV47a|      ACAATAAAA---------TCAGAT---------------GAGCAAC------ACATTAAT
1340 51_HRV47b|      ACAATACAA---------TCAAAT---------------GAGCAAC------ACATTAAT
1341 GROUP_10        A-AATA-AA.........-CA-AT...............G--C--C......A---TA--
1342
1343 46_HRV31        AAATATAAAGTATGGCACATTAATTTACAAGAGATGGCCCAGATTAGGCGAAAATTTGAA
1344 47_HRV31a|      AAATATAAAGTATGGCACATTAATTTACAAGAGATGGCCCAGATTAGGCGAAAATTTGAA
1345 48_HRV31b|      AAATATAAAGTATGGCACATTAATTTACAAGAGATGGCCCAGATTAGGCGAAAATTTGAA
1346 49_HRV47        AAATTTAAAGTATGGCACATTAATTTACAAGAAATGGCCCAGATCAGGCGTAAATATGAA
1347 50_HRV47a|      AAATTTAAAGTATGGCACATTAATTTACAAGAAATGGCCCAGATCAGGCGTAAATATGAA
1348 51_HRV47b|      AAATTTAAAGTATGGCACATTAATTTACAAGAAATGGCCCAGATCAGGCGTAAATATGAA
1349 GROUP_10        AAAT-TAAAGTATGGCACATTAATTTACAAGA-ATGGCCCAGAT-AGGCG-AAAT-TGAA
1350
1351 46_HRV31        ATGTTCACATATGTAAGATTTGATTCAGAAGTGACCATAG-TTCCATGCATTGCAGGACA
1352 47_HRV31a|      ATGTTCACATATGTAAGATTTGATTCAGAAGTGACCATAG-TTCCATGCATTGCAGGACA
1353 48_HRV31b|      ATGTTCACATATGTAAGATTTGATTCAGAAGTGACCATAG-TTCCATGCATTGCAGGACA
1354 49_HRV47        ATGTTTACATATGTAAGATTTGATTCAGAAGTAACCATGG-TTCCATGTATTGCAGGGTA
1355 50_HRV47a|      ATGTTTACATATGTAAGATTTGATTCAGAAGTAACCATGG-TTCCATGTATTGCAGGGTA
1356 51_HRV47b|      ATGTTTACATATGTAAGATTTGATTCAGAAGTAACCATGG-TTCCATGTATTGCAGGGTA
1357 GROUP_10        ATGTT-ACATATGTAAGATTTGATTCAGAAGT-ACCAT-G.TTCCATG-ATTGCAGG--A
```

FIG. D13 CONT'D

09.trace                                                            9/20/2007 5:05 PM

```
1358
1359  46_HRV31      TGGTAGTGACATAGGCCATATAGTCATGCAATACATGTATGTACCACCTGGGGCCCCAGT
1360  47_HRV31a|    TGGTAGTGACATAGGCCATATAGTCATGCAATACATGTATGTACCACCTGGGGCCCCAGT
1361  48_HRV31b|    TGGTAGTGACATAGGCCATATAGTCATGCAATACATGTATGTACCACCTGGGGCCCCAGT
1362  49_HRV47      TGGTGATGACATAGGTCACATAGTTATGCAATACATGTATGTGCCGCCTGGGGCTCCAGT
1363  50_HRV47a|    TGGTGATGACATAGGTCACATAGTTATGCAATACATGTATGTGCCGCCTGGGGCTCCAGT
1364  51_HRV47b|    TGGTGATGACATAGGTCACATAGTTATGCAATACATGTATGTGCCGCCTGGGGCTCCAGT
1365  GROUP_10      TGGT--TGACATAGG-CA-ATAGT-ATGCAATACATGTATGT-CC--CCTGGGGC-CCAGT
1366
1367  46_HRV31      ACCAACAAATAGAAAACATTTTGCATGGCAATCAGGTACTAATGCATCGATTTTCTGGCA
1368  47_HRV31a|    ACCAACAAATAGAAAACATTTTGCATGGCAATCAGGTACTAATGCATCGATTTTCTGGCA
1369  48_HRV31b|    ACCAACAAATAGAAAACATTTTGCATGGCAATCAGGTACTAATGCATCGATTTTCTGGCA
1370  49_HRV47      GCCAACAAGTAGAGAGCACTTTGCATGGCAGTCAGGTACCAATGCATCAACTTTCTGGCA
1371  50_HRV47a|    GCCAACAAGTAGAGAGCACTTTGCATGGCAGTCAGGTACCAATGCATCAACTTTCTGGCA
1372  51_HRV47b|    GCCAACAAGTAGAGAGCACTTTGCATGGCAGTCAGGTACCAATGCATCAATTTTCTGGCA
1373  GROUP_10      -CCAACAA-TAGA-A-CA-TTTGCATGGCA-TCAGGTAC-AATGCATC-A-TTTCTGGCA
1374
1375  46_HRV31      ACATGGACAACCCTTTCCAAGATTTACATTACCCTTTTTGAGTGTCGCATCCGCTTATTA
1376  47_HRV31a|    ACATGGACAACCCTTTCCAAGATTTACATTACCCTTTTTGAGTGTCGCATCCGCTTATTA
1377  48_HRV31b|    ACATGGACAACCCTTTCCAAGATTTACATTACCCTTTTTGAGTGTCGCATCCGCTTATTA
1378  49_HRV47      ACAAGGGCAACCCTTTCCAAGATTTTCATTACCATTTTTGAGTGTTGCATCTGCTTATTA
1379  50_HRV47a|    ACAAGGGCAACCCTTTCCAAGATTTTCATTACCATTTTTGAGTGTTGCATCTGCTTATTA
1380  51_HRV47b|    ACAAGGGCAACCCTTTCCAAGATTTTCATTACCATTTTTGAGTGTTGCATCTGCTTATTA
1381  GROUP_10      ACA-GG-CAACCCTTTCCAAGATTT-CATTACC-TTTTTGAGTGT-GCATC-GCTTATTA
1382
1383  46_HRV31      CATGTTTTATGATGGTTATGATGGAGACAAAAGTGGAGCCAAGTATGGTACTACAGTAGT
1384  47_HRV31a|    CATGTTTTATGATGGTTATGATGGAGACAAAAGTGGAGCCAAGTATGGTACTACAGTAGT
1385  48_HRV31b|    CATGTTTTATGATGGTTATGATGGAGACAAAAGTGGAGCCAAGTATGGTACTACAGTAGT
1386  49_HRV47      CATGTTTTATGATGGCTATAATGGTGACAGAAGTGGAGCCAAGTATGGCACCACAGTGGT
1387  50_HRV47a|    CATGTTTTATGATGGCTATAATGGTGACAGAAGTGGAGCCAAGTATGGCACCACAGTGGT
1388  51_HRV47b|    CATGTTTTATGATGGCTATAATGGTGACAGAAGTGGAGCCAAGTATGGCACCACAGTGGT
1389  GROUP_10      CATGTTTTATGATGG-TAT-ATGG-GACA-AAGTGGAGCCAAGTATGG-AC-ACAGT-GT
1390
1391  46_HRV31      TAATCGCATGGGTGCACTATGCATGAGAGTTGTCACTAACAAACAAGCTCATAAAGTTGA
1392  47_HRV31a|    TAATCGCATGGGTGCACTATGCATGAGAGTTGTCACTAACAAACAAGCTCATAAAGTTGA
1393  48_HRV31b|    TAATCGCATGGGTGCACTATGCATGAGAGTTGTCACTAACAAACAAGCTCATAAAGTTGA
1394  49_HRV47      CAATCGCATGGGTGCATTGTGTATGAGAGTTGTAACAAACAAGCAACTCCATAAAGTTGA
1395  50_HRV47a|    CAATCGCATGGGTGCATTGTGTATGAGAGTTGTAACAAACAAGCAACTCCATAAAGTTGA
1396  51_HRV47b|    CAATCGCATGGGTGCATTGTGTATGAGAGTTGTAACAAACAAGCAACTCCATAAAGTTGA
1397  GROUP_10      -AATCGCATGGGTGCA-T-TG-ATGAGAGTTGT-AC-AACAA-CAA---CATAAAGTTGA
1398
1399  46_HRV31      AATCACAACCAATATTTACCATAAGGCCAAACATGTTAAGGCATGGTGTCCTAGGCCCCC
1400  47_HRV31a|    AATCACAACCAATATTTACCATAAGGCCAAACATGTTAAGGCATGGTGTCCTAGGCCCCC
1401  48_HRV31b|    AATCACAACCAATATTTACCATAAGGCCAAACATGTAAAGGCATGGTGTCCTAGGCCACC
1402  49_HRV47      AATCACAACTAACATCTACCATAAAGCCAAGCATGTGAAAGCATGGTGTCCTAGACCACC
1403  50_HRV47a|    AATCACAACTAACATCTACCATAAAGCCAAGCATGTGAAAGCATGGTGTCCTAGACCACC
1404  51_HRV47b|    AATCACAACTAACATCTACCATAAAGCCAAGCATGTGAAAGCATGGTGTCCTAGACCACC
1405  GROUP_10      AATCACAAC-AA-AT-TACCATAA-GCCAA-CATGT-AA-GCATGGTGTCCTAG-CC-CC
1406
1407  46_HRV31      TAGAGCAGTTCCATACAGGGTATG-TGGATCAACAAACTACAAAC-CTGATG---AAAAT
1408  47_HRV31a|    TAGAGCAGTTCCATACAGGGTATG-TGGATCAACAAACTACAAAC-CTGATG---AAAAT
1409  48_HRV31b|    TAGAGCAGTTCCATACAGG-TATGTTGGATCAACAAACTACAAAC-CTGATG---AAAAT
1410  49_HRV47      TAGAGCTGTTCCATATAGA-TATGTTGGATCAACAAATTACAAAC-CTGATC---AAGGA
1411  50_HRV47a|    TAGAGCTGTTCCATATAGA-TATGTTGGATCAACAAATTACAAAC-CTGATC---AAGGA
1412  51_HRV47b|    TAGAGCTGTTCCATATAGA-TATGTTGGATCAACAAATTACAAAC-CTGATC---AAGGA
1413  GROUP_10      TAGAGC-GTTCCATA-AG--TATG-TGGATCAACAAA-TACAAAC.CTGAT-...AA---
1414
1415  46_HRV31      GAAG------TTACAATCT---TTGTTAAACACAGGGATAATCCAAAGATTATCACAG--
1416  47_HRV31a|    GAAG------TTACAATCT---TTGTTAAACACAGGGATAATCCAAAGATTATCACAG--
1417  48_HRV31b|    GAAG------TTACAATCT---TTGTTAAACACAGGGATAATCCAAAGATTATCACAG--
1418  49_HRV47      GAAG------TTGCAATTT---TCATTGAGCATAGAGAAAATCCAAAATTCATTACAG--
1419  50_HRV47a|    GAAG------TTGCAATTT---TCATTGAGCATAGAGAAAATCCAAAATTCATTACAG--
1420  51_HRV47b|    GAAG------TTGCAATTT---TCATTGAGCATAGAGAAAATCCAAAATTCATTACAG--
1421  GROUP_10      GAAG......TT-CAAT-T...T--TT-A-CA-AG-GA-AATCCAAA--T-AT-ACAG..
1422
```

FIG. D13 CONT'D

```
09.trace                                                                                        9/20/2007 5:05 PM 1423  46_HRV31     ----CA---------------
1424  47_HRV31a|   ----CT---------------
1425  48_HRV31b|   ----CA---------------
1426  49_HRV47     ----CA---------------
1427  50_HRV47a|   ----CT---------------
1428  51_HRV47b|   ----CA---------------
1429  GROUP_10     ....C-...............
1430
1431
1432
1433  GROUP  11:
1434
1435  52_HRV11     AACCCAGTGGAGGATTATGTTGATGGAATTCTAAATGAGGTTTTAGTTGTACCTAATATA
1436  53_HRV11b|   AACCCAGTGGAGGATTATGTTGATGGAATTCTAAATGAGGTTTTAGTTGTACCTAATATA
1437  54_HRV11a|   AACCCAGTGGAGGATTATGTTGATGGAATTCTAAATGAGGTTTTAGTTGTACCTAATATA
1438  55_HRV76     AACCCAGTTGAAAATTACGTGGATGAGATATTAAATGAGGTTCTTGTAGTACCAAACATC
1439  56_HRV76b|   AACCCAGTTGAAAATTACGTGGATGAGATATTAAATGAGGTTCTTGTAGTACCAAACATC
1440  57_HRV76a|   AACCCAGTTGAAAATTACGTGGATGAGATATTAAATGAGGTTCTTGTAGTACCAAACATC
1441  58_HRV33     AATCCAGTAGAGAATTATATAGAAGAGGTGTTGAATGAGGTTTTAGTAGTGCCTAATATC
1442  59_HRV33b|   AATCCAGTAGAGAATTATATAGAAGAGGTGTTGAATGAGGTTTTAGTAGTGCCTAATATC
1443  60_HRV33a|   AATCCAGTAGAGAATTATATAGAAGAGGTGTTGAATGAGGTTTTAGTAGTGCCTAATATC
1444  GROUP_11     AA-CCAGT-GA--ATTA--T-GA-G---T--T-AATGAGGTT-T-GT-GT-CC-AA-AT-
1445
1446  52_HRV11     AAGGAGAGCCAAGCTACCACATCAAACTCAGCACCTGCTCTAGATGCAGCTGAAACCGGA
1447  53_HRV11b|   AAGGAGAGCCAAGCTACCACATCAAACTCAGCACCTGCTCTAGATGCAGCTGAAACCGGA
1448  54_HRV11a|   AAGGAGAGCCAAGCTACCACATCAAACTCAGCACCTGCTCTAGATGCAGCTGAAACCGGA
1449  55_HRV76     AAAGAGAGTCAGGCTACCACATCAAATGCAGCACCTGCTTTGGATGCAGCTGAGACTGGG
1450  56_HRV76b|   AAAGAGAGTCAGGCTACCACATCAAATGCAGCACCTGCTTTGGATGCAGCTGAGACTGGG
1451  57_HRV76a|   AAAGAGAGTCAGGCTACCACATCAAATGCAGCACCTGCTTTGGATGCAGCTGAGACTGGG
1452  58_HRV33     AGAGAGAGTCAAGCAACCACATCAAATTCAGCACCTGCCTTAGATGCAGCTGAGACTGGA
1453  59_HRV33b|   AGAGAGAGTCAAGCAACCACATCAAATTCAGCACCTGCCTTAGATGCAGCTGAGACTGGA
1454  60_HRV33a|   AGAGAGAGTCAAGCAACCACATCAAATTCAGCACCTGCCTTAGATGCAGCTGAGACTGGA
1455  GROUP_11     A--GAGAG-CA-GC-ACCACATCAAA--CAGCACCTGC--T-GATGCAGCTGA-AC-GG-
1456
1457  52_HRV11     CATACTAGCAAAGTGCAGCCAGAGGATATGATTGAGACTAGATATGTGCAGACTTCACAG
1458  53_HRV11b|   CATACTAGCAAAGTGCAGCCAGAGGATATGATTGAGACTAGATATGTGCAGACTTCACAG
1459  54_HRV11a|   CATACTAGCAAAGTGCAGCCAGAGGATATGATTGAGACTAGATATGTGCAGACTTCACAG
1460  55_HRV76     CACACAAGCAGCGTTCAACCAGAGGACATGGTTGAGACTAGGTATGTGCAAACATCACAA
1461  56_HRV76b|   CACACAAGCAGCGTTCAACCAGAGGACATGGTTGAGACTAGGTATGTGCAAACATCACAA
1462  57_HRV76a|   CACACAAGCAGCGTTCAACCAGAGGACATGGTTGAGACTAGGTATGTGCAAACATCACAA
1463  58_HRV33     CACACTAATAATGTACAACCAGAAGATATGATTGAAACAAGATATGTACAAACATCACAA
1464  59_HRV33b|   CACACTAATAATGTACAACCAGAAGATATGATTGAAACAAGATATGTACAAACATCACAA
1465  60_HRV33a|   CACACTAATAATGTACAACCAGAAGATATGATTGAAACAAGATATGTACAAACATCACAA
1466  GROUP_11     CA-AC-A--A--GT-CA-CCAGA-GA-ATG-TTGA-AC-AG-TATGT-CA-AC-TCACA-
1467
1468  52_HRV11     ACTCTTGATGAAATGAGCATTGAGAGCTTCCTAGGTAGATCTGGTTGTATTCACATGTCC
1469  53_HRV11b|   ACTCTTGATGAAATGAGCATTGAGAGCTTCCTAGGTAGATCTGGTTGTATTCACATGTCC
1470  54_HRV11a|   ACTCTTGATGAAATGAGCATTGAGAGCTTCCTAGGTAGATCTGGTTGTATTCACATGTCC
1471  55_HRV76     ACTCTTGATGAGATGTGTATGGAGAGTTTCTTAGGGAGATCTGGTTGTATTCATATTTCA
1472  56_HRV76b|   ACTCTTGATGAGATGTGTATGGAGAGTTTCTTAGGGAGATCTGGTTGTATTCATATTTCA
1473  57_HRV76a|   ACTCTTGATGAGATGTGTATGGAGAGTTTCTTAGGGAGATCTGGTTGTATTCATATTTCA
1474  58_HRV33     ACTCTTGATGAGATGAGTGTGGAAAGCTTCTTAGGAAGGTCTGGTTGCATTCACATGTCA
1475  59_HRV33b|   ACTCTTGATGAGATGAGTGTGGAAAGCTTCTTAGGAAGGTCTGGTTGCATTCACATGTCA
1476  60_HRV33a|   ACTCTTGATGAGATGAGTGTGGAAAGCTTCTTAGGAAGGTCTGGTTGCATTCACATGTCA
1477  GROUP_11     ACTCTTGATGA-ATG-G--T-GA-AG-TTC-TAGG-AG-TCTGGTTG-ATTCA-AT-TC-
1478
1479  52_HRV11     AAGTTAATTGTGCAGTATGAAGAC---------------TATAAT------GGAAAGAAA
1480  53_HRV11b|   AAGTTAATTGTGCAGTATGAAGAC---------------TATAAT------GGAAAGAAA
1481  54_HRV11a|   AAGTTAATTGTGCAGTATGAAGAC---------------TATAAT------GGAAAGAAA
1482  55_HRV76     AAGCTAGTTGTAGAATATGAGGGA---------------TATGAT------GATACAAAA
1483  56_HRV76b|   AAGCTAGTTGTAGAATATGAGGGA---------------TATGAT------GATACAAAA
1484  57_HRV76a|   AAGCTAGTTGTAGAATATGAGGGA---------------TATGAT------GATACAAAA
1485  58_HRV33     AAATTAGTAGTGAAATATGAAGAC---------------TATAAT------GAGAAAAAG
1486  59_HRV33b|   AAATTAGTAGTGAAATATGAAGAC---------------TATAAT------GAGAAAAAG
1487  60_HRV33a|   AAATTAGTAGTGAAATATGAAGAC---------------TATAAT------GAGAAAAAG
```

FIG. D13 CONT'D

09.trace                                                                9/20/2007 5:05 PM

```
1488 GROUP_11    AA--TA-T-GT--A-TATGA-G--...............TAT-AT......G--A--AA-
1489
1490 52_HRV11    AACTTTAACACATGGAAAATAAACTTGCAAGAGATGGCACAAATTAGAAGGAAATTTGAA
1491 53_HRV11b|  AACTTTAACACATGGAAAATAAACTTGCAAGAGATGGCACAAATTAGAAGGAAATTTGAA
1492 54_HRV11a|  AACTTTAACACATGGAAAATAAACTTGCAAGAGATGGCACAAATTAGAAGGAAATTTGAA
1493 55_HRV76    AACTTTAAGACATGGAAAATAAACCTACAAGAAATGGCACAAGTTAGAAGAAAATTTGAG
1494 56_HRV76b|  AACTTTAAGACATGGAAAATAAACCTACAAGAAATGGCACAAGTTAGAAGAAAATTTGAG
1495 57_HRV76a|  AACTTTAAGACATGGAAAATAAACCTACAAGAAATGGCACAAGTTAGAAGAAAATTTGAG
1496 58_HRV33    AATTTTATGACATGGAAAATAAATCTACAAGAGATGGCACAGATTAGGAGGAAATTTGAA
1497 59_HRV33b|  AATTTTATGACATGGAAAATAAATCTACAAGAGATGGCACAGATTAGGAGGAAATTTGAA
1498 60_HRV33a|  AATTTTATGACATGGAAAATAAATCTACAAGAGATGGCACAGATTAGGAGGAAATTTGAA
1499 GROUP_11    AA-TTTA--ACATGGAAAATAAA--T-CAAGA-ATGGCACA--TTAG-AG--AAATTTGA-
1500
1501 52_HRV11    ATGTTCACATACACTAGATTTGATTCAGAGATCACATTGG-TGCCTTGTATAGCTGCAAA
1502 53_HRV11b|  ATGTTCACATACACTAGATTTGATTCAGAGATCACATTGG-TGCCTTGTATAGCTGCAAA
1503 54_HRV11a|  ATGTTCACATACACTAGATTTGATTCAGAGATCACATTGG-TGCCTTGTATAGCTGCAAA
1504 55_HRV76    ATGTTTACATATACTAGATTTGATTCAGAAGTTACTCTAG-TTCCTTCTATAGCTGCCAA
1505 56_HRV76b|  ATGTTTACATATACTAGATTTGATTCAGAAGTTACTCTAG-TTCCTTCTATAGCTGCCAA
1506 57_HRV76a|  ATGTTTACATATACTAGATTTGATTCAGAAGTTACTCTAG-TTCCTTCTATAGCTGCCAA
1507 58_HRV33    ATGTTTACATATGCCAGATTTGATTCAGAGATCACCCTAG-TCCCTTCTATAGCTGCCCA
1508 59_HRV33b|  ATGTTTACATATGCCAGATTTGATTCAGAGATCACCCTAG-TCCCTTCTATAGCTGCCCA
1509 60_HRV33a|  ATGTTTACATATGCCAGATTTGATTCAGAGATCACCCTAG-TCCCTTCTATAGCTGCCCA
1510 GROUP_11    ATGTT-ACATA--C-AGATTTGATTCAGA--T-AC--T-G.T-CCTT-TATAGCTGC--A
1511
1512 52_HRV11    AGGAAATGATATTGGTCATGTTGTAATGCAATATATGTATGTCCCACCAGGTGCTCCAGT
1513 53_HRV11b|  AGGAAATGATATTGGTCATGTTGTAATGCAATATATGTATGTCCCACCAGGTGCTCCAGT
1514 54_HRV11a|  AGGAAATGATATTGGTCATGTTGTAATGCAATATATGTATGTCCCACCAGGTGCTCCAGT
1515 55_HRV76    AGGGGATGACATTGGTCATGTAGTGATGCAATACATGTATGTCCCACCAGGCGCTCCAGT
1516 56_HRV76b|  AGGGGATGACATTGGTCATGTAGTGATGCAATACATGTATGTCCCACCAGGCGCTCCAGT
1517 57_HRV76a|  AGGGGATGACATTGGTCATGTAGTGATGCAATACATGTATGTCCCACCAGGCGCTCCAGT
1518 58_HRV33    GGGAGATGATGTTGGTCATGTTGTAATGCAGTACATGTATGTCCCACCAGGTGCACCAGC
1519 59_HRV33b|  GGGAGATGATGTTGGTCATGTTGTAATGCAGTACATGTATGTCCCACCAGGTGCACCAGC
1520 60_HRV33a|  GGGAGATGATGTTGGTCATGTTGTAATGCAGTACATGTATGTCCCACCAGGTGCACCAGC
1521 GROUP_11    -GG--ATGA--TTGGTCATGT-GT-ATGCA-TA-ATGTATGTCCCACCAGG-GC-CCAG-
1522
1523 52_HRV11    TCCAGAGAAAAGAGATGATTATACATGGCAATCAGGAACAAATGCATCTATTTTCTGGCA
1524 53_HRV11b|  TCCAGAGAAAAGAGATGATTATACATGGCAATCAGGAACAAATGCATCTATTTTCTGGCA
1525 54_HRV11a|  TCCAGAGAAAAGAGATGATTATACATGGCAATCAGGAACAAATGCATCTATTTTCTGGCA
1526 55_HRV76    TCCAAAGAAGAGAGATGACTACACATGGCAGTCAGGAACCAATGCATCTATTTTCTGGCA
1527 56_HRV76b|  TCCAAAGAAGAGAGATGACTACACATGGCAGTCAGGAACCAATGCATCTATTTTCTGGCA
1528 57_HRV76a|  TCCAAAGAAGAGAGATGACTACACATGGCAGTCAGGAACCAATGCATCTATTTTCTGGCA
1529 58_HRV33    TCCAGAAAAGAGAGATGATTACACATGGCAATCAGGAACAAATGCATCTGTCTTTTGGCA
1530 59_HRV33b|  TCCAGAAAAGAGAGATGATTACACATGGCAATCAGGAACAAATGCATCTGTCTTTTGGCA
1531 60_HRV33a|  TCCAGAAAAGAGAGATGATTACACATGGCAATCAGGAACAAATGCATCTGTCTTTTGGCA
1532 GROUP_11    TCCA-A-AA-AGAGATGA-TA-ACATGGCA-TCAGGAAC--AATGCATCT-T-TT-TGGCA
1533
1534 52_HRV11    ATATGGTCAAACATACCCAAGATTTTCTCTACCTTTCATGAGTATAGCCTCAGCATATTA
1535 53_HRV11b|  ATATGGTCAAACATACCCAAGATTTTCTCTACCTTTCATGAGTATAGCCTCAGCATATTA
1536 54_HRV11a|  ATATGGTCAAACATACCCAAGATTTTCTCTACCTTTCATGAGTATAGCCTCAGCATATTA
1537 55_HRV76    ATATGGACAAACATACCCTAGGTTTTCATTACCCTTTCTAAGTATAGCTTCAGCTTATTA
1538 56_HRV76b|  ATATGGACAAACATACCCTAGGTTTTCATTACCCTTTCTAAGTATAGCTTCAGCTTATTA
1539 57_HRV76a|  ATATGGACAAACATACCCTAGGTTTTCATTACCCTTTCTAAGTATAGCTTCAGCTTATTA
1540 58_HRV33    ATATGGACAAACATATCCTAGGTTCTCATTACCTTTCCTTAGCATAGCTTCAGCATATTA
1541 59_HRV33b|  ATATGGACAAACATATCCTAGGTTCTCATTACCTTTCCTTAGCATAGCTTCAGCATATTA
1542 60_HRV33a|  ATATGGACAAACATATCCTAGGTTCTCATTACCTTTCCTTAGCATAGCTTCAGCATATTA
1543 GROUP_11    ATATGG-CAAACATA-CC-AG-TT-TC--TACC-TT--T-AG-ATAGC-TCAGC-TATTA
1544
1545 52_HRV11    CATGTTTTATGATGGATATGATGGAGATCAACCAAACTCCAGATATGGTAATATAGTTAC
1546 53_HRV11b|  CATGTTTTATGATGGATATGATGGAGATCAACCAAACTCCAGATATGGTAATATAGTTAC
1547 54_HRV11a|  CATGTTTTATGATGGATATGATGGAGATCAACCAAACTCCAGATATGGTAATATAGTTAC
1548 55_HRV76    CATGTTTTATGATGGATATGATGGAGACCAACCTAGTTCTAGGTATGGTAATATAGTTAC
1549 56_HRV76b|  CATGTTTTATGATGGATATGATGGAGACCAACCTAGTTCTAGGTATGGTAATATAGTTAC
1550 57_HRV76a|  CATGTTTTATGATGGATATGATGGAGACCAACCTAGTTCTAGGTATGGTAATATAGTTAC
1551 58_HRV33    CATGTTCTATGATGGATATGATGGGGACCAACCCAATTCCAGGTATGGTAATATGGTTAC
1552 59_HRV33b|  CATGTTCTATGATGGATATGATGGGGACCAACCCAATTCCAGGTATGGTAATATGGTTAC
```

FIG. D13 CONT'D

09.trace                                                                                         9/20/2007 5:05 PM

```
1553  60_HRV33a|    CATGTTCTATGATGGATATGATGGGGACCAACCCAATTCCAGGTATGGTAATATGGTTAC
1554  GROUP_11     CATGTT-TATGATGGATATGATGG-GA-CAACC-A---TC-AG-TATGGTAATAT-GTTAC
1555
1556  52_HRV11     CAATGATATGGGCACTCTGTGTTATAGAATAGTAACTGATGACCATAGACACAAAATTGA
1557  53_HRV11b|   CAATGATATGGGCACTCTGTGTTATAGAATAGTAACTGATGACCATAGACACAAAATTGA
1558  54_HRV11a|   CAATGATATGGGCACTCTGTGTTATAGAATAGTAACTGATGACCATAGACACAAAATTGA
1559  55_HRV76     CAATGACATGGGCACCCTATGTTCCAGGATAGTAACTGATGATCATAAGCACAAGATTGA
1560  56_HRV76b|   CAATGACATGGGCACCCTATGTTCCAGGATAGTAACTGATGATCATAAGCACAAGATTGA
1561  57_HRV76a|   CAATGACATGGGCACCCTATGTTCCAGGATAGTAACTGATGATCATAAGCACAAGATTGA
1562  58_HRV33     CAATGACATGGGCACTTTATGCTCTAGAATAGTTACAGATAATCATAAGCATCCAATAGA
1563  59_HRV33b|   CAATGACATGGGCACTTTATGCTCTAGAATAGTTACAGATAATCATAAGCATCCAATAGA
1564  60_HRV33a|   CAATGACATGGGCACTTTATGCTCTAGAATAGTTACAGATAATCATAAGCATCCAATAGA
1565
1566  GROUP_11     CAATGA-ATGGGCAC--T-TG-T--AG-ATAGT-AC-GAT-A-CATA--CA----AT-GA
1567  52_HRV11     AGTCACAACTAGGGTGTATCATAAAGCAAAGCATGTGAAGGTGTGGTGTCCAAGACCACC
1568  53_HRV11b|   AGTCACAACTAGGGTGTATCATAAAGCAAAGCATGTGAAGGTGTGGTGTCCAAGACCACC
1569  54_HRV11a|   AGTCACAACTAGGGTGTATCATAAAGCAAAGCATGTGAAGGTGTGGTGTCCAAGACCACC
1570  55_HRV76     AGTTACAACAAGAATATATCACAAAGCAAAGCATGTTAAGGTATGGTGCCCGAGACCACC
1571  56_HRV76b|   AGTTACAACAAGAATATATCACAAAGCAAAGCATGTTAAGGTATGGTGCCCGAGACCACC
1572  57_HRV76a|   AGTTACAACAAGAATATATCACAAAGCAAAGCATGTTAAGGTATGGTGCCCGAGACCACC
1573  58_HRV33     AGTTACAACAAGAGTATACCATAAAGCAAAACATGTCAAAGTCTGGTGCCCAAGACCACC
1574  59_HRV33b|   AGTTACAACAAGAGTATACCATAAAGCAAAACATGTCAAAGTCTGGTGCCCAAGACCACC
1575  60_HRV33a|   AGTTACAACAAGAGTATACCATAAAGCAAAACATGTCAAAGTCTGGTGCCCAAGACCACC
1576  GROUP_11     AGT-ACAAC-AG--T-TA-CA-AAAGCAAA-CATGT-AA-GT-TGGTG-CC-AGACCACC
1577
1578  52_HRV11     TAGAGCTGTAGAATATACT-CACACTCATGTAACCAATTACAAAC-CACAGG---AAGGA
1579  53_HRV11b|   TAGAGCTGTAGAATATACT-CACACTCATGTAACCAATTACAAAC-CACAGG---AAGGA
1580  54_HRV11a|   TAGAGCTGTAGAATATACT-CACACTCATGTAACCAATTACAAAC-CACAGG---AAGGA
1581  55_HRV76     TAGAGCTGTAGAGTATACA-TACACCCATGTAACAAACTACAAAC-CACATT---CTGGT
1582  56_HRV76b|   TAGAGCTGTAGAGTATACA-TACACCCATGTAACAAACTACAAAC-CACATT---CTGGT
1583  57_HRV76a|   TAGAGCTGTAGAGTATACA-TACACCCATGTAACAAACTACAAAC-CACATT---CTGGT
1584  58_HRV33     TAGAGCTGTGGAATACACC-CATACTCATGTTACAAATTATAAAT-CAACAA---CTCGT
1585  59_HRV33b|   TAGAGCTGTGGAATACACC-CATACTCATGTTACAAATTATAAAT-CAACAA---CTCGT
1586  60_HRV33a|   TAGAGCTGTGGAATACACC-CATACTCATGTTACAAATTATAAAT-CAACAA---CTCGT
1587  GROUP_11     TAGAGCTGT-GA-TA-AC-.-A-AC-CATGT-AC-AA-TA-AAA-.CA----...---G-
1588
1589  52_HRV11     CAGG------TGAAAACAG---CTGTCAAGGCTAGGAAAACAATTAAAACAGCA------
1590  53_HRV11b|   CAGG------TGAAAACAG---CTGTCAAGGCTAGGAAAACAATTAAAACAGCG------
1591  54_HRV11a|   CAGG------TGAAAACAG---CTGTCAAGGCTAGGAAAACAATTAAAACAGCT------
1592  55_HRV76     GATG------TGCAAACAG---CTATTAGACCAAGAGCAACAATTAAGACTGCA------
1593  56_HRV76b|   GATG------TGCAAACAG---CTATTAGACCAAGAGCAACAATTAAGACTGCG------
1594  57_HRV76a|   GATG------TGCAAACAG---CTATTAGACCAAGAGCAACAATTAAGACTGCT------
1595  58_HRV33     GAAG------TGAAGACAG---CTATTAGACCAAGAGCAACAATCAAGACTGCA------
1596  59_HRV33b|   GAAG------TGAAGACAG---CTATTAGACCAAGAGCAACAATCAAGACTGCG------
1597  60_HRV33a|   GAAG------TGAAGACAG---CTATTAGACCAAGAGCAACAATCAAGACTGCT------
1598  GROUP_11     -A-G......TG-A-ACAG...CT-T-A---C-AG---AACAAT-AA-AC-GC-......
1599
1600  52_HRV11     --------------------
1601  53_HRV11b|   --------------------
1602  54_HRV11a|   --------------------
1603  55_HRV76     --------------------
1604  56_HRV76b|   --------------------
1605  57_HRV76a|   --------------------
1606  58_HRV33     --------------------
1607  59_HRV33b|   --------------------
1608  60_HRV33a|   --------------------
1609  GROUP_11     ....................
1610
1611
1612
1613  GROUP  12:
1614
1615  61_HRV24a|   AACCCAGTAGAAAATTATATAGATGAGGTTTTGAATGAAGTACTGGTTGTGCCTAATATT
1616  62_HRV24b|   AACCCAGTAGAAAATTATATAGATGAGGTTTTGAATGAAGTACTGGTTGTGCCTAATATT
1617  63_HRV24     AACCCAGTAGAAAATTATATAGATGAGGTTTTGAATGAAGTACTGGTTGTGCCTAATATT
```

FIG. D13 CONT'D

```
09.trace                                                                    9/20/2007 5:05 PM 1618  64_HRV90    AATCCAGTGGAAAATTATATAGATGAAGTCCTAAATGAGGTATTGGTTGTCCCTAATATT
1619  65_HRV90a|  AATCCAGTGGAAAATTATATAGATGAAGTCCTAAATGAGGTATTGGTTGTCCCTAATATT
1620  66_HRV90b|  AATCCAGTGGAAAATTATATAGATGAAGTCCTAAATGAGGTATTGGTTGTCCCTAATATT
1621  GROUP_12    AA-CCAGT-GAAAATTATATAGATGA-GT--T-AATGA-GTA-TGGTTGT-CCTAATATT
1622
1623  61_HRV24a|  AAGGAAAGTAAACCATCAACATCAAACTCAGCACCAGCTTTGGATGCAGCAGAAACTGGA
1624  62_HRV24b|  AAGGAAAGTAAACCATCAACATCAAACTCAGCACCAGCTTTGGATGCAGCAGAAACTGGA
1625  63_HRV24    AAGGAAAGTAAACCATCAACATCAAACTCAGCACCAGCTTTGGATGCAGCAGAAACTGGA
1626  64_HRV90    AAGGAAAGTAAACCTTCAACTTCAAACTCAGCGCCAGCTTTAGATGCAGCAGAAACCGGA
1627  65_HRV90a|  AAGGAAAGTAAACCTTCAACTTCAAACTCAGCGCCAGCTTTAGATGCAGCAGAAACCGGA
1628  66_HRV90b|  AAGGAAAGTAAACCTTCAACTTCAAACTCAGCGCCAGCTTTAGATGCAGCAGAAACCGGA
1629  GROUP_12    AAGGAAAGTAAACC-TCAAC-TCAAACTCAGC-CCAGCTTT-GATGCAGCAGAAAC-GGA
1630
1631  61_HRV24a|  CATACGAGTAGCGTGCAGCCAGAAGATATGGTTGAAACTAGATATGTCCAAACATCACAA
1632  62_HRV24b|  CATACGAGTAGCGTGCAGCCAGAAGATATGGTTGAAACTAGATATGTCCAAACATCACAA
1633  63_HRV24    CATACGAGTAGCGTGCAGCCAGAAGATATGGTTGAAACTAGATATGTCCAAACATCACAA
1634  64_HRV90    CATACTAGTGATGTCCAGCCAGAAGATGTGGTAGAGACCAGATACGTGCAAACATCACAA
1635  65_HRV90a|  CATACTAGTGATGTCCAGCCAGAAGATGTGGTAGAGACCAGATACGTGCAAACATCACAA
1636  66_HRV90b|  CATACTAGTGATGTCCAGCCAGAAGATGTGGTAGAGACCAGATACGTGCAAACATCACAA
1637  GROUP_12    CATAC-AGT---GT-CAGCCAGAAGAT-TGGT-GA-AC-AGATA-GT-CAAACATCACAA
1638
1639  61_HRV24a|  ACATTACATGAGATGAGTGTTGAAAGTTTCTTGGGTAGATCAGGTTGCATACACATGTCC
1640  62_HRV24b|  ACATTACATGAGATGAGTGTTGAAAGTTTCTTGGGTAGATCAGGTTGCATACACATGTCC
1641  63_HRV24    ACATTACATGAGATGAGTGTTGAAAGTTTCTTGGGTAGATCAGGTTGCATACACATGTCC
1642  64_HRV90    ACAAGAGATGAAATGAGTGTTGAAAGTTTTCTAGGGAGATCAGGTTGCATTCATATGTCA
1643  65_HRV90a|  ACAAGAGATGAAATGAGTGTTGAAAGTTTTCTAGGGAGATCAGGTTGCATTCATATGTCA
1644  66_HRV90b|  ACAAGAGATGAAATGAGTGTTGAAAGTTTTCTAGGGAGATCAGGTTGCATTCATATGTCA
1645  GROUP_12    ACA--A-ATGA-ATGAGTGTTGAAAGTTT--T-GG-AGATCAGGTTGCAT-CA-ATGTC-
1646
1647  61_HRV24a|  AAGTTGACTGTGGATTAT---GAC--------------AATTAT------GATACAAAA
1648  62_HRV24b|  AAGTTGACTGTGGATTAT---GAC--------------AATTAT------GATACAAAA
1649  63_HRV24    AAGTTGACTGTGGATTAT---GAC--------------AATTAT------GATACAAAA
1650  64_HRV90    AAATTAGTTGTAAACTAT---GAT--------------AATTAT------GATGAAAAC
1651  65_HRV90a|  AAATTAGTTGTAAACTAT---GAT--------------AATTAT------GATGAAAAC
1652  66_HRV90b|  AAATTAGTTGTAAACTAT---GAT--------------AATTAT------GATGAAAAC
1653  GROUP_12    AA-TT---TGT--A-TAT...GA-..............AATTAT......GAT--AAA-
1654
1655  61_HRV24a|  AATTTTTTCAAATGGCAAATAAATCTACAAGAAATGGCCCAAGTCAGAAGAAAATTTGAA
1656  62_HRV24b|  AATTTTTTCAAATGGCAAATAAATCTACAAGAAATGGCCCAAGTCAGAAGAAAATTTGAA
1657  63_HRV24    AATTTTTTCAAATGGCAAATAAATCTACAAGAAATGGCCCAAGTCAGAAGAAAATTTGAA
1658  64_HRV90    AACTTCCATAAATGGCAAATTAACCTGCAAGAGATGGCACAGATTAGAAGAAAATTTGAA
1659  65_HRV90a|  AACTTCCATAAATGGCAAATTAACCTGCAAGAGATGGCACAGATTAGAAGAAAATTTGAA
1660  66_HRV90b|  AACTTCCATAAATGGCAAATTAACCTGCAAGAGATGGCACAGATTAGAAGAAAATTTGAA
1661  GROUP_12    AA-TT----AAATGGCAAAT-AA-CT-CAAGA-ATGGC-CA--T-AGAAGAAAATTTGAA
1662
1663  61_HRV24a|  TTATTCACATATACTAGATTTGACTCTGAGATTACAATAG-TTCCATCCATAGCTGGCAA
1664  62_HRV24b|  TTATTCACATATACTAGATTTGACTCTGAGATTACAATAG-TTCCATCCATAGCTGGCAA
1665  63_HRV24    TTATTCACATATACTAGATTTGACTCTGAGATTACAATAG-TTCCATCCATAGCTGGCAA
1666  64_HRV90    TTGTTTACATATGCTAGATTTGATTCTGAAATTACAATAG-TACCATCTATAGCTGGCAA
1667  65_HRV90a|  TTGTTTACATATGCTAGATTTGATTCTGAAATTACAATAG-TACCATCTATAGCTGGCAA
1668  66_HRV90b|  TTGTTTACATATGCTAGATTTGATTCTGAAATTACAATAG-TACCATCTATAGCTGGCAA
1669  GROUP_12    TT-TT-ACATAT-CTAGATTTGA-TCTGA-ATTACAATAG.T-CCATC-ATAGCTGGCAA
1670
1671  61_HRV24a|  GGGAGATGACATTGGACATGTTGTAATGCAGTACATGTATATACCACCTGGAGCACCAGT
1672  62_HRV24b|  GGGAGATGACATTGGACATGTTGTAATGCAGTACATGTATATACCACCTGGAGCACCAGT
1673  63_HRV24    GGGAGATGACATTGGACATGTTGTAATGCAGTACATGTATATACCACCTGGAGCACCAGT
1674  64_HRV90    GGGCAATGATATTGGACATGTTGTGATGCAATACATGTATATACCACCTGGGGCACCAGT
1675  65_HRV90a|  GGGCAATGATATTGGACATGTTGTGATGCAATACATGTATATACCACCTGGGGCACCAGT
1676  66_HRV90b|  GGGCAATGATATTGGACATGTTGTGATGCAATACATGTATATACCACCTGGGGCACCAGT
1677  GROUP_12    GGG--ATGA-ATTGGACATGTTGT-ATGCA-TACATGTATATACCACCTGG-GCACCAGT
1678
1679  61_HRV24a|  CCCAACAAAGAGAGATGATTATACATGGCAATCAGGAACAAATGCATCTGTCTTTTGGCA
1680  62_HRV24b|  CCCAACAAAGAGAGATGATTATACATGGCAATCAGGAACAAATGCATCTGTCTTTTGGCA
1681  63_HRV24    CCCAACAAAGAGAGATGATTATACATGGCAATCAGGAACAAATGCATCTGTCTTTTGGCA
1682  64_HRV90    ACCTGAGAAGAGGGATGATTATGCATGGCAATCAGGCACTAATGCATCTATCTTTTGGCA
```

FIG. D13 CONT'D

```
09.trace                                                                                     9/20/2007 5:05 PM 1683 65_HRV90a|    ACCTGAGAAGAGGGATGATTATGCATGGCAATCAGGCACTAATGCATCTATCTTTTGGCA
1684 66_HRV90b|    ACCTGAGAAGAGGGATGATTATGCATGGCAATCAGGCACTAATGCATCTATCTTTTGGCA
1685 GROUP_12     -CC----AAGAG-GATGATTAT-CATGGCAATCAGG-AC-AATGCATCT-TCTTTTGGCA
1686
1687 61_HRV24a|    ACATGGACAAACCTATCCTAGATTTTCCCTTCCTTTTCTGAGTGTAGCCTCTGCATATTA
1688 62_HRV24b|    ACATGGACAAACCTATCCTAGATTTTCCCTTCCTTTTCTGAGTGTAGCCTCTGCATATTA
1689 63_HRV24      ACATGGACAAACCTATCCTAGATTTTCCCTTCCTTTTCTGAGTGTAGCCTCTGCATATTA
1690 64_HRV90      ACATGGACAAACATACCCTAGATTTCCACTTCCTTTCTTAAGTATAGCTTCTGCATACTA
1691 65_HRV90a|    ACATGGACAAACATACCCTAGATTTTCACTTCCTTTCTTAAGTATAGCTTCTGCATACTA
1692 66_HRV90b|    ACATGGACAAACATACCCTAGATTTTCACTTCCTTTCTTAAGTATAGCTTCTGCATACTA
1693 GROUP_12     ACATGGACAAAC-TA-CCTAGATTTTC-CTTCCTTT--T-AGT-TAGC-TCTGCATA-TA
1694
1695 61_HRV24a|    CATGTTTTATGATGGATATGATGGTGATCAACACGACTCAGTGTATGGTTCAGTTGTTAC
1696 62_HRV24b|    CATGTTTTATGATGGATATGATGGTGATCAACACGACTCAGTGTATGGTTCAGTTGTTAC
1697 63_HRV24      CATGTTTTATGATGGATATGATGGTGATCAACACGACTCAGTGTATGGTTCAGTTGTTAC
1698 64_HRV90      TATGTTTTATGATGGATATGATGGTGACCAAACTGATTCGAGATATGGTACCATTGTTAC
1699 65_HRV90a|    TATGTTTTATGATGGATATGATGGTGACCAAACTGATTCGAGATATGGTACCATTGTTAC
1700 66_HRV90b|    TATGTTTTATGATGGATATGATGGTGACCAAACTGATTCGAGATATGGTACCATTGTTAC
1701 GROUP_12     -ATGTTTTATGATGGATATGATGGTGA-CAA---GA-TC----TATGGT-C--TTGTTAC
1702
1703 61_HRV24a|    AAACGACATGGGAACTCTATGCTATAGAATAGTCACTGACAAGCATAATCACCAAATAGA
1704 62_HRV24b|    AAACGACATGGGAACTCTATGCTATAGAATAGTCACTGACAAGCATAATCACCAAATAGA
1705 63_HRV24      AAACGACATGGGAACTCTATGCTATAGAATAGTCACTGACAAGCATAATCACCAAATAGA
1706 64_HRV90      TAATGATATGGGAACCTTATGTTATAGAATAGTTACAGATGAACATGCCCACAAAATAGA
1707 65_HRV90a|    TAATGATATGGGAACCTTATGTTATAGAATAGTTACAGATGAACATGCCCACAAAATAGA
1708 66_HRV90b|    TAATGATATGGGAACCTTATGTTATAGAATAGTTACAGATGAACATGCCCACAAAATAGA
1709 GROUP_12     -AA-GA-ATGGGAAC--TATG-TATAGAATAGT-AC-GA--A-CAT---CAC-AAATAGA
1710
1711 61_HRV24a|    AATTACAACAAGAATATACCACAAAGCAAAGCACATTAAGGTCTGGTGTCCAAGGCCACC
1712 62_HRV24b|    AATTACAACAAGAATATACCACAAAGCAAAGCACATTAAGGTCTGGTGTCCAAGGCCACC
1713 63_HRV24      AATTACAACAAGAATATACCACAAAGCAAAGCACATTAAGGTCTGGTGTCCAAGGCCACC
1714 64_HRV90      GATCACTACAAGAATATACCATAAAGCAAAACACATTAAGGTTTGGTGTCCAAGACCACC
1715 65_HRV90a|    GATCACTACAAGAATATACCATAAAGCAAAACACATTAAGGTTTGGTGTCCAAGACCACC
1716 66_HRV90b|    GATCACTACAAGAATATACCATAAAGCAAAACACATTAAGGTTTGGTGTCCAAGACCACC
1717 GROUP_12     -AT-AC-ACAAGAATATACCA-AAAGCAAA-CACATTAAGGT-TGGTGTCCAAG-CCACC
1718
1719 61_HRV24a|    CAGAGCTGTTGAGTATACA-CATACTCACGTGACCAATTATAAGC-ATCAGA---CTCGT
1720 62_HRV24b|    CAGAGCTGTTGAGTATACA-CATACTCACGTGACCAATTATAAGC-ATCAGA---CTCGT
1721 63_HRV24      CAGAGCTGTTGAGTATACA-CATACTCACGTGACCAATTATAAGC-ATCAGA---CTCGT
1722 64_HRV90      TAGGGCAGTTGAATACACA-CACACTCATGTAACAAACTACAAAC-ATGCAA---CACGT
1723 65_HRV90a|    TAGGGCAGTTGAATACACA-CACACTCATGTAACAAACTACAAAC-ATGCAA---CACGT
1724 66_HRV90b|    TAGGGCAGTTGAATACACA-CACACTCATGTAACAAACTACAAAC-ATGCAA---CACGT
1725 GROUP_12     -AG-GC-GTTGA-TA-ACA.CA-ACTCA-GT-AC-AA-TA-AA-C.AT---A...C-CGT
1726
1727 61_HRV24a|    GAAG------TCAAGACAG---CAATTGAACCTAGAAGAGGAATTAAAACAGTG------
1728 62_HRV24b|    GAAG------TCAAGACAG---CAATTGAACCTAGAAGAGGAATTAAAACAGTC------
1729 63_HRV24      GAAG------TCAAGACAG---CAATTGAACCTAGAAGAGGAATTAAAACAGTT------
1730 64_HRV90      GAAC------TTAAGACTG---CAATTAGGCCCAGGAAAACAATCACAACAGCA------
1731 65_HRV90a|    GAAC------TTAAGACTG---CAATTAGGCCCAGGAAAACAATCACAACAGCG------
1732 66_HRV90b|    GAAC------TTAAGACTG---CAATTAGGCCCAGGAAAACAATCACAACAGCT------
1733 GROUP_12     GAA-......T-AAGAC-G...CAATT---CC-AG-A-A--AAT-A-AACAG--......
1734
1735 61_HRV24a|    --------------------
1736 62_HRV24b|    --------------------
1737 63_HRV24      --------------------
1738 64_HRV90      --------------------
1739 65_HRV90a|    --------------------
1740 66_HRV90b|    --------------------
1741 GROUP_12     ....................
1742
1743
1744
1745 GROUP 13:
1746
1747 67_HRV34      AATCCAGTTGAAAATTACATAGATGAGGTACTAAATGAGGTATTGGTTGTACCAAACATT
```

FIG. D13 CONT'D 09.trace                                                              9/20/2007 5:05 PM

```
1748  68_HRV34b|   AATCCAGTTGAAAATTACATAGATGAGGTACTAAATGAGGTATTGGTTGTACCAAACATT
1749  69_HRV34a|   AATCCAGTTGAAAATTACATAGATGAGGTACTAAATGAGGTATTGGTTGTACCAAACATT
1750  70_HRV50a|   AATCCAGTGGAGAATTACATAGATGAAGTATTAAATGAGGTATTAGTTGTCCCAAATATC
1751  71_HRV50b|   AATCCAGTGGAGAATTACATAGATGAAGTATTAAATGAGGTATTAGTTGTCCCAAATATC
1752  72_HRV50     AATCCAGTGGAGAATTACATAGATGAAGTATTAAATGAGGTATTAGTTGTCCCAAATATC
1753  73_HRV18a|   AATCCAGTAGAGAATTATATAGATGAAGTACTTAATGAAGTGTTAGTGGTCCCAAATGTG
1754  74_HRV18b|   AATCCAGTAGAGAATTATATAGATGAAGTACTTAATGAAGTGTTAGTGGTCCCAAATGTG
1755  75_HRV18     AATCCAGTAGAGAATTATATAGATGAAGTACTTAATGAAGTGTTAGTGGTCCCAAATGTG
1756  GROUP_13    AATCCAGT-GA-AATTA-ATAGATGA-GTA-T-AATGA-GT-TT-GT-GT-CCAAA--T-
1757
1758  67_HRV34     AAAGAAAGCCAAGCCACCACATCAAACTCTGCCCCCGCACTGGATGCAGCTGAGACTGGT
1759  68_HRV34b|   AAAGAAAGCCAAGCCACCACATCAAACTCTGCCCCCGCACTGGATGCAGCTGAGACTGGT
1760  69_HRV34a|   AAAGAAAGCCAAGCCACCACATCAAACTCTGCCCCCGCACTGGATGCAGCTGAGACTGGT
1761  70_HRV50a|   AAGGAGAGTCAAGCCACTACATCAAACTCTGCCCCTGCTTTAGATGCAGCTGAAACTGGA
1762  71_HRV50b|   AAGGAGAGTCAAGCCACTACATCAAACTCTGCCCCTGCTTTAGATGCAGCTGAAACTGGA
1763  72_HRV50     AAGGAGAGTCAAGCCACTACATCAAACTCTGCCCCTGCTTTAGATGCAGCTGAAACTGGA
1764  73_HRV18a|   AATGAAAGTCACGCAATTACATCAAATTCAGCCCCTGCTTTAGATGCCGCTGAAACTGGT
1765  74_HRV18b|   AATGAAAGTCACGCAATTACATCAAATTCAGCCCCTGCTTTAGATGCCGCTGAAACTGGT
1766  75_HRV18     AATGAAAGTCACGCAATTACATCAAATTCAGCCCCTGCTTTAGATGCCGCTGAAACTGGT
1767  GROUP_13    AA-GA-AG-CA-GC-A--ACATCAAA-TC-GCCCC-GC--T-GATGC-GCTGA-ACTGG-
1768
1769  67_HRV34     CACACTAGCAGTGTACAACCTGAAGATATGATTGAGACCAGGTACGTACAAACATCACAA
1770  68_HRV34b|   CACACTAGCAGTGTACAACCTGAAGATATGATTGAGACCAGGTACGTACAAACATCACAA
1771  69_HRV34a|   CACACTAGCAGTGTACAACCTGAAGATATGATTGAGACCAGGTACGTACAAACATCACAA
1772  70_HRV50a|   CACACAAGTAATGTGCAGCCTGAAGATATGCTTGAAACTAGATATGTGCAAACATCGCAT
1773  71_HRV50b|   CACACAAGTAATGTGCAGCCTGAAGATATGCTTGAAACTAGATATGTGCAAACATCGCAT
1774  72_HRV50     CACACAAGTAATGTGCAGCCTGAAGATATGCTTGAAACTAGATATGTGCAAACATCGCAT
1775  73_HRV18a|   CACACCAGCAATGTGCAACCTGAAGATATGATTGAGACTAGGTATGTACAAACATCACAA
1776  74_HRV18b|   CACACCAGCAATGTGCAACCTGAAGATATGATTGAGACTAGGTATGTACAAACATCACAA
1777  75_HRV18     CACACCAGCAATGTGCAACCTGAAGATATGATTGAGACTAGGTATGTACAAACATCACAA
1778  GROUP_13    CACAC-AG-A-TGT-CA--CCTGAAGATATG-TTGA-AC-AG-TA-GT-CAAACATC-CA-
1779
1780  67_HRV34     ACAAGAGATGAAATGAGCATTGAGAGTTTCCTGGGTAGGTCTGGCTGTATACACATGTCC
1781  68_HRV34b|   ACAAGAGATGAAATGAGCATTGAGAGTTTCCTGGGTAGGTCTGGCTGTATACACATGTCC
1782  69_HRV34a|   ACAAGAGATGAAATGAGCATTGAGAGTTTCCTGGGTAGGTCTGGCTGTATACACATGTCC
1783  70_HRV50a|   ACAAGAGATGAAATGAGCATTGAAAGTTTCCTAGGTAGATCTGGTTGTATACATATATCT
1784  71_HRV50b|   ACAAGAGATGAAATGAGCATTGAAAGTTTCCTAGGTAGATCTGGTTGTATACATATATCT
1785  72_HRV50     ACAAGAGATGAAATGAGCATTGAAAGTTTCCTAGGTAGATCTGGTTGTATACATATATCT
1786  73_HRV18a|   ACAAGAGATGAAATGAGTATAGAGTGTTTTCTAGGCAGATCAGGGTGTATACATATCTCC
1787  74_HRV18b|   ACAAGAGATGAAATGAGTATAGAGTGTTTTCTAGGCAGATCAGGGTGTATACATATCTCC
1788  75_HRV18     ACAAGAGATGAAATGAGTATAGAGTGTTTTCTAGGCAGATCAGGGTGTATACATATCTCC
1789  GROUP_13    ACAAGAGATGAAATGAG-AT-GA--GTTT-CT-GG-AG-TC-GG-TGTATACA-AT-TC-
1790
1791  67_HRV34     AAACTTGTTGTAGATTATGAAAAT---------------TACAATGCA---AAAACAAAG
1792  68_HRV34b|   AAACTTGTTGTAGATTATGAAAAT---------------TACAATGCA---AAAACAAAG
1793  69_HRV34a|   AAACTTGTTGTAGATTATGAAAAT---------------TACAATGCA---AAAACAAAG
1794  70_HRV50a|   AAATTAGTTGTTGATTATGATGGT---------------TACAATGAG---GAAACAAAG
1795  71_HRV50b|   AAATTAGTTGTTGATTATGATGGT---------------TACAATGAG---GAAACAAAG
1796  72_HRV50     AAATTAGTTGTTGATTATGATGGT---------------TACAATGAG---GAAACAAAG
1797  73_HRV18a|   AAGTTAGTTGTACATTATGAAGAT---------------TATAATGCA---GAAACAAGG
1798  74_HRV18b|   AAGTTAGTTGTACATTATGAAGAT---------------TATAATGCA---GAAACAAGG
1799  75_HRV18     AAGTTAGTTGTACATTATGAAGAT---------------TATAATGCA---GAAACAAGG
1800  GROUP_13    AA--T-GTTGT--ATTATGA---T...............TA-AATG--...-AAACAA-G
1801
1802  67_HRV34     AACTTTATGACATGGCAAATTAATTTACAGGAAATGGCACAGATTAGAAGGAAATTTGAA
1803  68_HRV34b|   AACTTTATGACATGGCAAATTAATTTACAGGAAATGGCACAGATTAGAAGGAAATTTGAA
1804  69_HRV34a|   AACTTTATGACATGGCAAATTAATTTACAGGAAATGGCACAGATTAGAAGGAAATTTGAA
1805  70_HRV50a|   AACTTCAAGAAATGGCAAATCAACCTACAAGAAATGGCACAGATCAGAAGGAAATTTGAG
1806  71_HRV50b|   AACTTCAAGAAATGGCAAATCAACCTACAAGAAATGGCACAGATCAGAAGGAAATTTGAG
1807  72_HRV50     AACTTCAAGAAATGGCAAATCAACCTACAAGAAATGGCACAGATCAGAAGGAAATTTGAG
1808  73_HRV18a|   AACTTTGTAAAATGGCAAATAAATCTACAGGAAATGGCCCAGATTAGGAGAAAATTTGAG
1809  74_HRV18b|   AACTTTGTAAAATGGCAAATAAATCTACAGGAAATGGCCCAGATTAGGAGAAAATTTGAG
1810  75_HRV18     AACTTTGTAAAATGGCAAATAAATCTACAGGAAATGGCCCAGATTAGGAGAAAATTTGAG
1811  GROUP_13    AACTT----A-ATGGCAAAT-AA--TACA-GAAATGGC-CAGAT-AG-AG-AAATTTGA-
1812
```

FIG. D13 CONT'D 09.trace                                                                            9/20/2007 5:05 PM

```
1813 67_HRV34    ATGTTCACCTACGTCAGATTTGATTCTGAAGTCACCCTAG-TACCATCAATAGCGGCCAA
1814 68_HRV34b|  ATGTTCACCTACGTCAGATTTGATTCTGAAGTCACCCTAG-TACCATCAATAGCGGCCAA
1815 69_HRV34a|  ATGTTCACCTACGTCAGATTTGATTCTGAAGTCACCCTAG-TACCATCAATAGCGGCCAA
1816 70_HRV50a|  ATGTTCACCTATGTGAGGTTTAATTCTGAGGTCACATTAG-TACCATCCATAGCTGCCAA
1817 71_HRV50b|  ATGTTCACCTATGTGAGGTTTAATTCTGAGGTCACATTAG-TACCATCCATAGCTGCCAA
1818 72_HRV50    ATGTTCACCTATGTGAGGTTTAATTCTGAGGTCACATTAG-TACCATCCATAGCTGCCAA
1819 73_HRV18a|  ATGTTTACATATGTTAGATTTGATTCAGAAATTACACTAG-TACCATCTGTAGCTGCTAA
1820 74_HRV18b|  ATGTTTACATATGTTAGATTTGATTCAGAAATTACACTAG-TACCATCTGTAGCTGCTAA
1821 75_HRV18    ATGTTTACATATGTTAGATTTGATTCAGAAATTACACTAG-TACCATCTGTAGCTGCTAA
1822 GROUP_13    ATGTT-AC-TA-GT-AG-TTT-ATTC-GA--T-AC--TAG.TACCATC--TAGC-GC-AA
1823
1824 67_HRV34    AGGTGATGATATTGGACATGTTGTGATGCAATACATGTATGTACCACCAGGTGCACCAAT
1825 68_HRV34b|  AGGTGATGATATTGGACATGTTGTGATGCAATACATGTATGTACCACCAGGTGCACCAAT
1826 69_HRV34a|  AGGTGATGATATTGGACATGTTGTGATGCAATACATGTATGTACCACCAGGTGCACCAAT
1827 70_HRV50a|  GGGTGTTGATATTGGACATGTTGTCATGCAATACATGTATGTCCCACCAGGTGCACCAAT
1828 71_HRV50b|  GGGTGTTGATATTGGACATGTTGTCATGCAATACATGTATGTCCCACCAGGTGCACCAAT
1829 72_HRV50    GGGTGTTGATATTGGACATGTTGTCATGCAATACATGTATGTCCCACCAGGTGCACCAAT
1830 73_HRV18a|  GGGTGATGACATAGGACATATTGTTATGCAGTACATGTATGTTCCTCCAGGAGCACCAAT
1831 74_HRV18b|  GGGTGATGACATAGGACATATTGTTATGCAGTACATGTATGTTCCTCCAGGAGCACCAAT
1832 75_HRV18    GGGTGATGACATAGGACATATTGTTATGCAGTACATGTATGTTCCTCCAGGAGCACCAAT
1833 GROUP_13    -GGTG-TGA-AT-GGACAT-TTGT-ATGCA-TACATGTATGT-CC-CCAGG-GCACCAAT
1834
1835 67_HRV34    ACCTAAAACTAGAGATGATTTTGCATGGCAATCTGGAACAAATGCCTCAATATTTTGGCA
1836 68_HRV34b|  ACCTAAAACTAGAGATGATTTTGCATGGCAATCTGGAACAAATGCCTCAATATTTTGGCA
1837 69_HRV34a|  ACCTAAAACTAGAGATGATTTTGCATGGCAATCTGGAACAAATGCCTCAATATTTTGGCA
1838 70_HRV50a|  ACCCAAGACTAGGGATGATTTTGCCTGGCAATCTGGAACTAATGCTTCAATCTTTTGGCA
1839 71_HRV50b|  ACCCAAGACTAGGGATGATTTTGCCTGGCAATCTGGAACTAATGCTTCAATCTTTTGGCA
1840 72_HRV50    ACCCAAGACTAGGGATGATTTTGCCTGGCAATCTGGAACTAATGCTTCAATCTTTTGGCA
1841 73_HRV18a|  ACCAAAAACCAGAGATGATTTTGCCTGGCAATCTGGAACAAATGCATCAATCTTCTGGCA
1842 74_HRV18b|  ACCAAAAACCAGAGATGATTTTGCCTGGCAATCTGGAACAAATGCATCAATCTTCTGGCA
1843 75_HRV18    ACCAAAAACCAGAGATGATTTTGCCTGGCAATCTGGAACAAATGCATCAATCTTCTGGCA
1844 GROUP_13    ACC-AA-AC-AG-GATGATTTTGC-TGGCAATCTGGAAC-AATGC-TCAAT-TT-TGGCA
1845
1846 67_HRV34    ACATGGTCAAACATACCCTAGATTTTCCCTCCCTTTCTTAAGCATAGCCTCAGCATACTA
1847 68_HRV34b|  ACATGGTCAAACATACCCTAGATTTTCCCTCCCTTTCTTAAGCATAGCCTCAGCATACTA
1848 69_HRV34a|  ACATGGTCAAACATACCCTAGATTTTCCCTCCCTTTCTTAAGCATAGCCTCAGCATACTA
1849 70_HRV50a|  ACATGGTCAAACATACCCTAGATTCTCTCTACCATTCTTGAGTATAGCATCTGCATATTA
1850 71_HRV50b|  ACATGGTCAAACATACCCTAGATTCTCTCTACCATTCTTGAGTATAGCATCTGCATATTA
1851 72_HRV50    ACATGGTCAAACATACCCTAGATTCTCTCTACCATTCTTGAGTATAGCATCTGCATATTA
1852 73_HRV18a|  ACATGGTCAAACATACCCCAGATTTTCACTTCCTTTCCTCAGTATAGCATCAGCTTATTA
1853 74_HRV18b|  ACATGGTCAAACATACCCCAGATTTTCACTTCCTTTCCTCAGTATAGCATCAGCTTATTA
1854 75_HRV18    ACATGGTCAAACATACCCCAGATTTTCACTTCCTTTCCTCAGTATAGCATCAGCTTATTA
1855 GROUP_13    ACATGGTCAAACATACCC-AGATT-TC-CT-CC-TTC-T-AG-ATAGC-TC-GC-TA-TA
1856
1857 67_HRV34    CATGTTTTATGATGGATATGATGGTGATCAACATGATTCAAGATATGGTACAGTAGTGAC
1858 68_HRV34b|  CATGTTTTATGATGGATATGATGGTGATCAACATGATTCAAGATATGGTACAGTAGTGAC
1859 69_HRV34a|  CATGTTTTATGATGGATATGATGGTGATCAACATGATTCAAGATATGGTACAGTAGTGAC
1860 70_HRV50a|  CATGTTTTATGATGGTTATGATGGTGATAAATCTACATCCAGGTATGGTACAGTAGTTAC
1861 71_HRV50b|  CATGTTTTATGATGGTTATGATGGTGATAAATCTACATCCAGGTATGGTACAGTAGTTAC
1862 72_HRV50    CATGTTTTATGATGGTTATGATGGTGATAAATCTACATCCAGGTATGGTACAGTAGTTAC
1863 73_HRV18a|  CATGTTCTATGATGGCTACGACGGTGACCAGACCTCATCGCGGTATGGCACAGTTGCAAC
1864 74_HRV18b|  CATGTTCTATGATGGCTACGACGGTGACCAGACCTCATCGCGGTATGGCACAGTTGCAAC
1865 75_HRV18    CATGTTCTATGATGGCTACGACGGTGACCAGACCTCATCGCGGTATGGCACAGTTGCAAC
1866 GROUP_13    CATGTT-TATGATGG-TA-GA-GGTGA-A-------TC--G-TATGG-ACAGT-G--AC
1867
1868 67_HRV34    TAATGACATGGGTACTTTATGCTCCAGAATTGTAACTGATGAACACCAAAACAGAGTAGA
1869 68_HRV34b|  TAATGACATGGGTACTTTATGCTCCAGAATTGTAACTGATGAACACCAAAACAGAGTAGA
1870 69_HRV34a|  TAATGACATGGGTACTTTATGCTCCAGAATTGTAACTGATGAACACCAAAACAGAGTAGA
1871 70_HRV50a|  CAATGACATGGGCACTTTGTGTTCTAGGATTGTCACTGATGAGCACCAAAATAAAGTGGA
1872 71_HRV50b|  CAATGACATGGGCACTTTGTGTTCTAGGATTGTCACTGATGAGCACCAAAATAAAGTGGA
1873 72_HRV50    CAATGACATGGGCACTTTGTGTTCTAGGATTGTCACTGATGAGCACCAAAATAAAGTGGA
1874 73_HRV18a|  AAATGACATGGGTACCTTGTGCTCTAGAATAGTCACAGATAAACATAAGAATGAGGTGGA
1875 74_HRV18b|  AAATGACATGGGTACCTTGTGCTCTAGAATAGTCACAGATAAACATAAGAATGAGGTGGA
1876 75_HRV18    AAATGACATGGGTACCTTGTGCTCTAGAATAGTCACAGATAAACATAAGAATGAGGTGGA
1877 GROUP_13    -AATGACATGGG-AC-TT-TG-TC-AG-AT-GT-AC-GAT-A-CA--A-AA----GT-GA
```

FIG. D13 CONT'D 09.trace                                                              9/20/2007 5:05 PM

```
1878
1879 67_HRV34    AATAACAACTAGAGTTTATCACAAAGCTAAACATGTAAAAACCTGGTGTCCAAGACCACC
1880 68_HRV34b|  AATAACAACTAGAGTTTATCACAAAGCTAAACATGTAAAAACCTGGTGTCCAAGACCACC
1881 69_HRV34a|  AATAACAACTAGAGTTTATCACAAAGCTAAACATGTAAAAACCTGGTGTCCAAGACCACC
1882 70_HRV50a|  AATCACAACCAGAGTATACCATAAAGCCAAACACATAAAAGTCTGGTGTCCAAGACCACC
1883 71_HRV50b|  AATCACAACCAGAGTATACCATAAAGCCAAACACATAAAAGTCTGGTGTCCAAGACCACC
1884 72_HRV50    AATCACAACCAGAGTATACCATAAAGCCAAACACATAAAAGTCTGGTGTCCAAGACCACC
1885 73_HRV18a|  AATAACAACCAGAATATACCACAAGGCAAAACATGTTAAAGCATGGTGCCCAAGGCCACC
1886 74_HRV18b|  AATAACAACCAGAATATACCACAAGGCAAAACATGTTAAAGCATGGTGCCCAAGGCCACC
1887 75_HRV18    AATAACAACCAGAATATACCACAAGGCAAAACATGTTAAAGCATGGTGCCCAAGGCCACC
1888 GROUP_13    AAT-ACAAC-AGA-T-TA-CA-AA-GC-AAACA--T-AAA---TGGTG-CCAAG-CCACC
1889
1890 67_HRV34    AAGAGCTGTTGAGTACACA-CACACACATGTTACTAACTACAAAG-TTAGGG---GTAAA
1891 68_HRV34b|  AAGAGCTGTTGAGTACACA-CACACACATGTTACTAACTACAAAG-TTAGGG---GTAAA
1892 69_HRV34a|  AAGAGCTGTTGAGTACACA-CACACACATGTTACTAACTACAAAG-TTAGGG---GTAAA
1893 70_HRV50a|  AAGAGCTGTTGAATACACA-CACACCCATGTCACTAACTACAAGA-AAAGTG---ATGCT
1894 71_HRV50b|  AAGAGCTGTTGAATACACA-CACACCCATGTCACTAACTACAAGA-AAAGTG---ATGCT
1895 72_HRV50    AAGAGCTGTTGAATACACA-CACACCCATGTCACTAACTACAAGA-AAAGTG---ATGCT
1896 73_HRV18a|  GAGAGCTGTGGAGTACACA-CATACACATGTAACTAACTACAAGC-CTAAGG---AAGGA
1897 74_HRV18b|  GAGAGCTGTGGAGTACACA-CATACACATGTAACTAACTACAAGC-CTAAGG---AAGGA
1898 75_HRV18    GAGAGCTGTGGAGTACACA-CATACACATGTAACTAACTACAAGC-CTAAGG---AAGGA
1899 GROUP_13    -AGAGCTGT-GA-TACACA.CA-AC-CATGT-ACTAACTACAA--.--A---G...-----
1900
1901 67_HRV34    ACTG------AGAAGACTG---CAATCAAACACAGAGCAAAGATCACAATGGCC------
1902 68_HRV34b|  ACTG------AGAAGACTG---CAATCAAACACAGAGCAAAGATCACAATGGCA------
1903 69_HRV34a|  ACTG------AGAAGACTG---CAATCAAACACAGAGCAAAGATCACAATGGCT------
1904 70_HRV50a|  ACTG------AGAAGACTG---CAATTGCAACTAGACCAAAGATCACAGTGGCA------
1905 71_HRV50b|  ACTG------AGAAGACTG---CAATTGCAACTAGACCAAAGATCACAGTGGCG------
1906 72_HRV50    ACTG------AGAAGACTG---CAATTGCAACTAGACCAAAGATCACAGTGGCT------
1907 73_HRV18a|  AGAG------AGAAAACTG---CCATAGTACCCAGAGCAAGGATTACAATGGCA------
1908 74_HRV18b|  AGAG------AGAAAACTG---CCATAGTACCCAGAGCAAGGATTACAATGGCG------
1909 75_HRV18    AGAG------AGAAAACTG---CCATAGTACCCAGAGCAAGGATTACAATGGCT------
1910 GROUP_13    A--G......AGAA-ACTG...C-AT---A---AGA-CAA-GAT-ACA-TGGC-......
1911
1912 67_HRV34    --------------------
1913 68_HRV34b|  --------------------
1914 69_HRV34a|  --------------------
1915 70_HRV50a|  --------------------
1916 71_HRV50b|  --------------------
1917 72_HRV50    --------------------
1918 73_HRV18a|  --------------------
1919 74_HRV18b|  --------------------
1920 75_HRV18    --------------------
1921 GROUP_13    ....................
1922
1923
1924
1925 GROUP  14:
1926
1927 76_HRV55    AATCCTGTAGAGAGATATGTTGATGAAGTCCTGAATGAAGTGCTAGTAGTTCCAAATATT
1928 77_HRV55b|  AATCCTGTAGAGAGATATGTTGATGAAGTCCTGAATGAAGTGCTAGTAGTTCCAAATATT
1929 78_HRV55a|  AATCCTGTAGAGAGATATGTTGATGAAGTCCTGAATGAAGTGCTAGTAGTTCCAAATATT
1930 GROUP_14    AATCCTGTAGAGAGATATGTTGATGAAGTCCTGAATGAAGTGCTAGTAGTTCCAAATATT
1931
1932 76_HRV55    AGGGAGAGTCAAGCAGCAACATCAAATTCAGCTCCAGTACTAGATGCAGCAGAAACTGGG
1933 77_HRV55b|  AGGGAGAGTCAAGCAGCAACATCAAATTCAGCTCCAGTACTAGATGCAGCAGAAACTGGG
1934 78_HRV55a|  AGGGAGAGTCAAGCAGCAACATCAAATTCAGCTCCAGTACTAGATGCAGCAGAAACTGGG
1935 GROUP_14    AGGGAGAGTCAAGCAGCAACATCAAATTCAGCTCCAGTACTAGATGCAGCAGAAACTGGG
1936
1937 76_HRV55    CATACAAGCAATGTACAACCAGAAGATGTAATTGAGACAAGATATGTTCAGACATCACAA
1938 77_HRV55b|  CATACAAGCAATGTACAACCAGAAGATGTAATTGAGACAAGATATGTTCAGACATCACAA
1939 78_HRV55a|  CATACAAGCAATGTACAACCAGAAGATGTAATTGAGACAAGATATGTTCAGACATCACAA
1940 GROUP_14    CATACAAGCAATGTACAACCAGAAGATGTAATTGAGACAAGATATGTTCAGACATCACAA
1941
1942 76_HRV55    ACTCGTGATGAGATGAGCATTGAAAGTTTTCTAGGTAGATCAGGATGTGTACATATATCA
```

FIG. D13 CONT'D

```
09.trace                                                                    9/20/2007 5:05 PM 1943  77_HRV55b|    ACTCGTGATGAGATGAGCATTGAAAGTTTTCTAGGTAGATCAGGATGTGTACATATATCA
1944  78_HRV55a|    ACTCGTGATGAGATGAGCATTGAAAGTTTTCTAGGTAGATCAGGATGTGTACATATATCA
1945  GROUP_14     ACTCGTGATGAGATGAGCATTGAAAGTTTTCTAGGTAGATCAGGATGTGTACATATATCA
1946
1947  76_HRV55     GAGTTAGTTGTTCATTATGAAGAA---------------TATAACAAA---GAGGGAAAA
1948  77_HRV55b|   GAGTTAGTTGTTCATTATGAAGAA---------------TATAACAAA---GAGGGAAAA
1949  78_HRV55a|   GAGTTAGTTGTTCATTATGAAGAA---------------TATAACAAA---GAGGGAAAA
1950  GROUP_14     GAGTTAGTTGTTCATTATGAAGAA...............TATAACAAA...GAGGGAAAA
1951
1952  76_HRV55     AATTTTACTAAGTGGCAAGTAAACATCCAAGAGATGGCTCAGATTAGAAGAAAATTTGAA
1953  77_HRV55b|   AATTTTACTAAGTGGCAAGTAAACATCCAAGAGATGGCTCAGATTAGAAGAAAATTTGAA
1954  78_HRV55a|   AATTTTACTAAGTGGCAAGTAAACATCCAAGAGATGGCTCAGATTAGAAGAAAATTTGAA
1955  GROUP_14     AATTTTACTAAGTGGCAAGTAAACATCCAAGAGATGGCTCAGATTAGAAGAAAATTTGAA
1956
1957  76_HRV55     ATGTTCACCTATACTAGATTTGATTCAGAAGTTACATTAG-TACCCTCTATTGCTGCAAA
1958  77_HRV55b|   ATGTTCACCTATACTAGATTTGATTCAGAAGTTACATTAG-TACCCTCTATTGCTGCAAA
1959  78_HRV55a|   ATGTTCACCTATACTAGATTTGATTCAGAAGTTACATTAG-TACCCTCTATTGCTGCAAA
1960  GROUP_14     ATGTTCACCTATACTAGATTTGATTCAGAAGTTACATTAG.TACCCTCTATTGCTGCAAA
1961
1962  76_HRV55     GGGAGATGACATTGGACATGTAGTCATGCAATACATGTATGTTCCACCTGGAGCACCAAT
1963  77_HRV55b|   GGGAGATGACATTGGACATGTAGTCATGCAATACATGTATGTTCCACCTGGAGCACCAAT
1964  78_HRV55a|   GGGAGATGACATTGGACATGTAGTCATGCAATACATGTATGTTCCACCTGGAGCACCAAT
1965  GROUP_14     GGGAGATGACATTGGACATGTAGTCATGCAATACATGTATGTTCCACCTGGAGCACCAAT
1966
1967  76_HRV55     TCCAAAGACAAGAGAAGATTATGCTTGGCAATCAGGGACCAATGCATCTATCTTTTGGCA
1968  77_HRV55b|   TCCAAAGACAAGAGAAGATTATGCTTGGCAATCAGGGACCAATGCATCTATCTTTTGGCA
1969  78_HRV55a|   TCCAAAGACAAGAGAAGATTATGCTTGGCAATCAGGGACCAATGCATCTATCTTTTGGCA
1970  GROUP_14     TCCAAAGACAAGAGAAGATTATGCTTGGCAATCAGGGACCAATGCATCTATCTTTTGGCA
1971
1972  76_HRV55     ACATGGGCAAACATACCCTAGATTTTCACTTCCTTTCCTAAGTATAGCTTCTGCTTATTA
1973  77_HRV55b|   ACATGGGCAAACATACCCTAGATTTTCACTTCCTTTCCTAAGTATAGCTTCTGCTTATTA
1974  78_HRV55a|   ACATGGGCAAACATACCCTAGATTTTCACTTCCTTTCCTAAGTATAGCTTCTGCTTATTA
1975  GROUP_14     ACATGGGCAAACATACCCTAGATTTTCACTTCCTTTCCTAAGTATAGCTTCTGCTTATTA
1976
1977  76_HRV55     CATGTTCTATGATGGATATGATGGTGACCAAACTGAGTCACGCTATGGCACTGTAGTCAC
1978  77_HRV55b|   CATGTTCTATGATGGATATGATGGTGACCAAACTGAGTCACGCTATGGCACTGTAGTCAC
1979  78_HRV55a|   CATGTTCTATGATGGATATGATGGTGACCAAACTGAGTCACGCTATGGCACTGTAGTCAC
1980  GROUP_14     CATGTTCTATGATGGATATGATGGTGACCAAACTGAGTCACGCTATGGCACTGTAGTCAC
1981
1982  76_HRV55     TAATGACATGGGTACTTTATGTTCTAGAATAATAACTGATAACCATAAGCACCCAATTGA
1983  77_HRV55b|   TAATGACATGGGTACTTTATGTTCTAGAATAATAACTGATAACCATAAGCACCCAATTGA
1984  78_HRV55a|   TAATGACATGGGTACTTTATGTTCTAGAATAATAACTGATAACCATAAGCACCCAATTGA
1985  GROUP_14     TAATGACATGGGTACTTTATGTTCTAGAATAATAACTGATAACCATAAGCACCCAATTGA
1986
1987  76_HRV55     AGTGACGACAAGAGTCTATCATAAAGCTAAACACATCAAAGCATGGTGCCCACGACCACC
1988  77_HRV55b|   AGTGACGACAAGAGTCTATCATAAAGCTAAACACATCAAAGCATGGTGCCCACGACCACC
1989  78_HRV55a|   AGTGACGACAAGAGTCTATCATAAAGCTAAACACATCAAAGCATGGTGCCCACGACCACC
1990  GROUP_14     AGTGACGACAAGAGTCTATCATAAAGCTAAACACATCAAAGCATGGTGCCCACGACCACC
1991
1992  76_HRV55     TAGGGCTGTTGAATACACA-CACACACATGTCACAAATTACAAGA-AGACTG---ATGGC
1993  77_HRV55b|   TAGGGCTGTTGAATACACA-CACACACATGTCACAAATTACAAGA-AGACTG---ATGGC
1994  78_HRV55a|   TAGGGCTGTTGAATACACA-CACACACATGTCACAAATTACAAGA-AGACTG---ATGGC
1995  GROUP_14     TAGGGCTGTTGAATACACA.CACACACATGTCACAAATTACAAGA.AGACTG...ATGGC
1996
1997  76_HRV55     ACAG------AAAAGACAG---CAATTGAATACAGAAGGGACATTAAAACAGTG------
1998  77_HRV55b|   ACAG------AAAAGACAG---CAATTGAATACAGAAGGGACATTAAAACAGTC------
1999  78_HRV55a|   ACAG------AAAAGACAG---CAATTGAATACAGAAGGGACATTAAAACAGTA------
2000  GROUP_14     ACAG......AAAAGACAG...CAATTGAATACAGAAGGGACATTAAAACAGT-......
2001
2002  76_HRV55     --------------------
2003  77_HRV55b|   --------------------
2004  78_HRV55a|   --------------------
2005  GROUP_14     ....................
2006
2007
```

FIG. D13 CONT'D 09.trace	9/20/2007 5:05 PM

```
GROUP  15:

79_HRV57     AACCCAGTAGAAAATTTTGTGGATGAGATCTTGAATGAAGTTTTGGTGGTTCCAGATATC
80_HRV57a|   AACCCAGTAGAAAATTTTGTGGATGAGATCTTGAATGAAGTTTTGGTGGTTCCAGATATC
81_HRV57b|   AACCCAGTAGAAAATTTTGTGGATGAGATCTTGAATGAAGTTTTGGTGGTTCCAGATATC
GROUP_15     AACCCAGTAGAAAATTTTGTGGATGAGATCTTGAATGAAGTTTTGGTGGTTCCAGATATC

79_HRV57     AAACAAAGTCAAGCAACAACATCAAACTCAGCACCTGCATTGGATGCAGCTGAAACTGGA
80_HRV57a|   AAACAAAGTCAAGCAACAACATCAAACTCAGCACCTGCATTGGATGCAGCTGAAACTGGA
81_HRV57b|   AAACAAAGTCAAGCAACAACATCAAACTCAGCACCTGCATTGGATGCAGCTGAAACTGGA
GROUP_15     AAACAAAGTCAAGCAACAACATCAAACTCAGCACCTGCATTGGATGCAGCTGAAACTGGA

79_HRV57     CACACTAGTAATGTACAACCGGAAGACATGATTGAAACTAGATATGTCCAGACATCACAA
80_HRV57a|   CACACTAGTAATGTACAACCGGAAGACATGATTGAAACTAGATATGTCCAGACATCACAA
81_HRV57b|   CACACTAGTAATGTACAACCGGAAGACATGATTGAAACTAGATATGTCCAGACATCACAA
GROUP_15     CACACTAGTAATGTACAACCGGAAGACATGATTGAAACTAGATATGTCCAGACATCACAA

79_HRV57     ACACGTGATGAAATGAGTCTTGAGAGCTTCTTAGGAAGATCTGGCTGCATTCATATTTCA
80_HRV57a|   ACACGTGATGAAATGAGTCTTGAGAGCTTCTTAGGAAGATCTGGCTGCATTCATATTTCA
81_HRV57b|   ACACGTGATGAAATGAGTCTTGAGAGCTTCTTAGGAAGATCTGGCTGCATTCATATTTCA
GROUP_15     ACACGTGATGAAATGAGTCTTGAGAGCTTCTTAGGAAGATCTGGCTGCATTCATATTTCA

79_HRV57     GAGCTTAAGGTAAAATATGAAAAT---------------TACAACACA---GAG------
80_HRV57a|   GAGCTTAAGGTAAAATATGAAAAT---------------TACAACACA---GAG------
81_HRV57b|   GAGCTTAAGGTAAAATATGAAAAT---------------TACAACACA---GAG------
GROUP_15     GAGCTTAAGGTAAAATATGAAAAT...............TACAACACA...GAG......

79_HRV57     AATTTCACTAAATGGGAAATAAATCTACAAGAAATGGCACAAATCAGAAGAAAATTTGAA
80_HRV57a|   AATTTCACTAAATGGGAAATAAATCTACAAGAAATGGCACAAATCAGAAGAAAATTTGAA
81_HRV57b|   AATTTCACTAAATGGGAAATAAATCTACAAGAAATGGCACAAATCAGAAGAAAATTTGAA
GROUP_15     AATTTCACTAAATGGGAAATAAATCTACAAGAAATGGCACAAATCAGAAGAAAATTTGAA

79_HRV57     CTATTTACATATGTTAGGTTTGATTCTGAAGTTACATTAG-TTCCCTCCATAGCTGCTCA
80_HRV57a|   CTATTTACATATGTTAGGTTTGATTCTGAAGTTACATTAG-TTCCCTCCATAGCTGCTCA
81_HRV57b|   CTATTTACATATGTTAGGTTTGATTCTGAAGTTACATTAG-TTCCCTCCATAGCTGCTCA
GROUP_15     CTATTTACATATGTTAGGTTTGATTCTGAAGTTACATTAG.TTCCCTCCATAGCTGCTCA

79_HRV57     AGGTGAGGATATAGGCCATGTTGTAATGCAATACATGTATGTCCCTCCTGGGGCACCAAT
80_HRV57a|   AGGTGAGGATATAGGCCATGTTGTAATGCAATACATGTATGTCCCTCCTGGGGCACCAAT
81_HRV57b|   AGGTGAGGATATAGGCCATGTTGTAATGCAATACATGTATGTCCCTCCTGGGGCACCAAT
GROUP_15     AGGTGAGGATATAGGCCATGTTGTAATGCAATACATGTATGTCCCTCCTGGGGCACCAAT

79_HRV57     TCCAAAAACAAGAGAGGATTATACATGGCAATCTGGTACCAATGCTTCAATATTTTGGCA
80_HRV57a|   TCCAAAAACAAGAGAGGATTATACATGGCAATCTGGTACCAATGCTTCAATATTTTGGCA
81_HRV57b|   TCCAAAAACAAGAGAGGATTATACATGGCAATCTGGTACCAATGCTTCAATATTTTGGCA
GROUP_15     TCCAAAAACAAGAGAGGATTATACATGGCAATCTGGTACCAATGCTTCAATATTTTGGCA

79_HRV57     ACATGGTCAAACATACCCTAGATTTTCCTTGCCTTTCTTAAGTATAGCCTCAGCATATTA
80_HRV57a|   ACATGGTCAAACATACCCTAGATTTTCCTTGCCTTTCTTAAGTATAGCCTCAGCATATTA
81_HRV57b|   ACATGGTCAAACATACCCTAGATTTTCCTTGCCTTTCTTAAGTATAGCCTCAGCATATTA
GROUP_15     ACATGGTCAAACATACCCTAGATTTTCCTTGCCTTTCTTAAGTATAGCCTCAGCATATTA

79_HRV57     CATGTTTTATGATGGATATGATGGTGACCAAACTGAATCAAGATATGGTACTGTAGTCAC
80_HRV57a|   CATGTTTTATGATGGATATGATGGTGACCAAACTGAATCAAGATATGGTACTGTAGTCAC
81_HRV57b|   CATGTTTTATGATGGATATGATGGTGACCAAACTGAATCAAGATATGGTACTGTAGTCAC
GROUP_15     CATGTTTTATGATGGATATGATGGTGACCAAACTGAATCAAGATATGGTACTGTAGTCAC

79_HRV57     TAATGACATGGGCACTTTATGTTCTAGAATTGTTACTGACCAGCACACACATCCCATAAA
80_HRV57a|   TAATGACATGGGCACTTTATGTTCTAGAATTGTTACTGACCAGCACACACATCCCATAAA
81_HRV57b|   TAATGACATGGGCACTTTATGTTCTAGAATTGTTACTGACCAGCACACACATCCCATAAA
GROUP_15     TAATGACATGGGCACTTTATGTTCTAGAATTGTTACTGACCAGCACACACATCCCATAAA

79_HRV57     AATAACAACCAGAGTGTATCACAAAGCCAAACATGTCAAAGCCTGGTGCCCTAGACCACC
80_HRV57a|   AATAACAACCAGAGTGTATCACAAAGCCAAACATGTCAAAGCCTGGTGCCCTAGACCACC
```

FIG. D13 CONT'D

```
09.trace                                                           9/20/2007 5:05 PM 2073 81_HRV57b|   AATAACAACCAGAGTGTATCACAAAGCCAAACATGTCAAAGCCTGGTGCCCTAGACCACC
2074 GROUP_15    AATAACAACCAGAGTGTATCACAAAGCCAAACATGTCAAAGCCTGGTGCCCTAGACCACC
2075
2076 79_HRV57    ACGGGCTATCGAGTACACA-CATACACATGTTACTAATTATAAAA-TAAAAG---ATAGA
2077 80_HRV57a|  ACGGGCTATCGAGTACACA-CATACACATGTTACTAATTATAAAA-TAAAAG---ATAGA
2078 81_HRV57b|  ACGGGCTATCGAGTACACA-CATACACATGTTACTAATTATAAAA-TAAAAG---ATAGA
2079 GROUP_15    ACGGGCTATCGAGTACACA.CATACACATGTTACTAATTATAAAA.TAAAAG...ATAGA
2080
2081 79_HRV57    CAAG------AAGAAACAG---CAATTAAATATAGAAGGGACATTAAAATTGTTAAGA--
2082 80_HRV57a|  CAAG------AAGAAACAG---CAATTAAATATAGAAGGGACATTAAAATTGTTAAGA--
2083 81_HRV57b|  CAAG------AAGAAACAG---CAATTAAATATAGAAGGGACATTAAAATTGTTAAGA--
2084 GROUP_15    CAAG......AAGAAACAG...CAATTAAATATAGAAGGGACATTAAAATTGTTAAGA..
2085
2086 79_HRV57    ----ATGTG------------
2087 80_HRV57a|  ----ATGTA------------
2088 81_HRV57b|  ----ATGTC------------
2089 GROUP_15    ....ATGT-............
2090
2091
2092
2093 GROUP  16:
2094
2095 82_HRV21    AATCCTGTAGAGAATTATATAGATGAAGTCCTAAATGAAGTCTTAGTAGTGCCAAATATC
2096 83_HRVHan   AATCCTGTAGAGAATTACGTAGATGAAGTTCTAAATGAGGTCTTAGTAGTGCCAAATATC
2097 GROUP_16    AATCCTGTAGAGAATTA--TAGATGAAGT-CTAAATGA-GTCTTAGTAGTGCCAAATATC
2098
2099 82_HRV21    AGAGAGAGTCATGGAACAACATCAAACTCTGCTCCCGCACTTGATGCTGCAGAAACTGGA
2100 83_HRVHan   AGAGAGAGTCATGGAACAACATCAAACTCTGCTCCCGCACTTGATGCTGCAGAAACTGGG
2101 GROUP_16    AGAGAGAGTCATGGAACAACATCAAACTCTGCTCCCGCACTTGATGCTGCAGAAACTGG-
2102
2103 82_HRV21    CACACTAGTAATGTACAGCCGGAGGATATGGTTGAAACAAGGTATGTTCAGACATCACAA
2104 83_HRVHan   CACACTAGTAATGTACAACCAGAGGATATGGTTGAAACAAGGTATGTTCAGACATCACAA
2105 GROUP_16    CACACTAGTAATGTACA-CC-GAGGATATGGTTGAAACAAGGTATGTTCAGACATCACAA
2106
2107 82_HRV21    ACACGTGATGAAATGAGTATTGAAAGTTTTCTGGGCAGATCAGGGTGCATTCACATGTCA
2108 83_HRVHan   ACACGTGATGAAATGAGTATTGAAAGTTTTCTAGGCAGATCAGGGTGTATCCACATGTCA
2109 GROUP_16    ACACGTGATGAAATGAGTATTGAAAGTTTTCT-GGCAGATCAGGGTG-AT-CACATGTCA
2110
2111 82_HRV21    AAATTAGTAGTTAACTATGATAAT---------------TACAATACT---GGAGAAAAT
2112 83_HRVHan   AAATTAATAGTTAACTATGACAAC---------------TACAATACT---GGAGAAAAT
2113 GROUP_16    AAATTA-TAGTTAACTATGA-AA-...............TACAATACT...GGAGAAAAT
2114
2115 82_HRV21    AACATTAGTACATGGCAAATAAATATTAAAGAGATGGCACAAATTAGGAGAAAATTTGAA
2116 83_HRVHan   AACATTAATACATGGCAAATAAATATTAAAGAGATGGCACAAATTAGGAGAAAATTTGAA
2117 GROUP_16    AACATTA-TACATGGCAAATAAATATTAAAGAGATGGCACAAATTAGGAGAAAATTTGAA
2118
2119 82_HRV21    ATGTTCACCTATACTAGATTTGATTCAGAAATAACTTTGG-TGCCGTCAATTGCAGCTAG
2120 83_HRVHan   ATGTTCACCTATACTAGATTTGATTCAGAAATAACTTTGG-TACCGTCAATTGCAGCTAA
2121 GROUP_16    ATGTTCACCTATACTAGATTTGATTCAGAAATAACTTTGG.T-CCGTCAATTGCAGCTA-
2122
2123 82_HRV21    AACGGGTGACATAGGACATGTTGTAATGCAATATATGTATGTCCCACCAGGTGCTCCAAT
2124 83_HRVHan   AGCGGGTGACATAGGACATGTTGTGATGCAATATATGTATGTCCCACCAGGTGCTCCAAT
2125 GROUP_16    A-CGGGTGACATAGGACATGTTGT-ATGCAATATATGTATGTCCCACCAGGTGCTCCAAT
2126
2127 82_HRV21    TCCAAAAACTAGGGAAGATTTTGCTTGGCAGTCAGGCACTAATGCATCCATTTTCTGGCA
2128 83_HRVHan   TCCAAAAACTAGGGAAGATTTTGCTTGGCAATCAGGTACCAATGCATCCATTTTCTGGCA
2129 GROUP_16    TCCAAAAACTAGGGAAGATTTTGCTTGGCA-TCAGG-AC-AATGCATCCATTTTCTGGCA
2130
2131 82_HRV21    GCATGGCCAGACTTATCCTAGATTTTCATTACCCTTCCTTAGTATAGCATCAGCATACTA
2132 83_HRVHan   GCATGGTCAAACTTATCCTAGATTTTCACTACCCTTCCTTAGTATAGCATCAGCATATTA
2133 GROUP_16    GCATGG-CA-ACTTATCCTAGATTTTCA-TACCCTTCCTTAGTATAGCATCAGCATA-TA
2134
2135 82_HRV21    CATGTTTTATGATGGTTATGATGGTGACCAGACTGACTCACAATATGGTGCAGTAGTAAC
2136 83_HRVHan   CATGTTTTATGATGGTTATGATGGTGATCAGACTGACTCACAATATGGTGCAGTGGTGAC
2137 GROUP_16    CATGTTTTATGATGGTTATGATGGTGA-CAGACTGACTCACAATATGGTGCAGT-GT-AC
```

FIG. D13 CONT'D

```
09.trace                                                              9/20/2007 5:05 PM 2138
2139 82_HRV21    TAATGATATGGGATCTCTATGCTACAGAATAGTAACTGGCCAGCATAAGCATAAGATAGA
2140 83_HRVHan   TAATGATATGGGATCTCTATGCTATAGAATAGTAACTGATCAGCATAAGCACAAGATAGA
2141 GROUP_16    TAATGATATGGGATCTCTATGCTA-AGAATAGTAACTG--CAGCATAAGCA-AAGATAGA
2142
2143 82_HRV21    AGTGACCACAAGAATATACCATAAGGCAAAGCATGTTAAAGCTTGGTGCCCCAGACCACC
2144 83_HRVHan   AGTGACCACAAGAATATACCATAAGGCAAAGCATGTTAAAGCTTGGTGCCCTAGACCACC
2145 GROUP_16    AGTGACCACAAGAATATACCATAAGGCAAAGCATGTTAAAGCTTGGTGCCC-AGACCACC
2146
2147 82_HRV21    GAGGGCCGTTGAATACACA-CATACACACGTAACCAATTACAAAA-TTGCAA---ATCAT
2148 83_HRVHan   GAGGGCCGTTGAATACACA-CATACACATGTAACCAATTACAAAA-TTGCAA---ATAAA
2149 GROUP_16    GAGGGCCGTTGAATACACA.CATACACA-GTAACCAATTACAAAA.TTGCAA...AT-A-
2150
2151 82_HRV21    GAAG------TCACTTCTG---CAGTTGAGTCCAGAAGAACAATTGTCACAGTT------
2152 83_HRVHan   GATG------TCACTTCTG---CAGTTGAGTCCAGAAGAACAATTGTCACAGTT------
2153 GROUP_16    GA-G......TCACTTCTG...CAGTTGAGTCCAGAAGAACAATTGTCACAGTT......
2154
2155 82_HRV21    --------------------
2156 83_HRVHan   --------------------
2157 GROUP_16    ....................
2158
2159
2160
2161 GROUP  17:
2162
2163 84_HRV43    AATCCTGTTGAAAATTATGTTGATGAAATTTTAAATCAAGTTCTTGTAGTCCCAAACACT
2164 85_HRV43b|  AATCCTGTTGAAAATTATGTTGATGAAATTTTAAATCAAGTTCTTGTAGTCCCAAACACT
2165 86_HRV43a|  AATCCTGTTGAAAATTATGTTGATGAAATTTTAAATCAAGTTCTTGTAGTCCCAAACACT
2166 87_HRV75    AATCCAGTTGAAAATTATGTGGATGAAATTTTAAACCAAGTTCTGGTAGTTCCAAACACC
2167 88_HRV75b|  AATCCAGTTGAAAATTATGTGGATGAAATTTTAAACCAAGTTCTGGTAGTTCCAAACACC
2168 89_HRV75a|  AATCCAGTTGAAAATTATGTGGATGAAATTTTAAACCAAGTTCTGGTAGTTCCAAACACC
2169 GROUP_17    AATCC-GTTGAAAATTATGT-GATGAAATTTTAAA-CAAGTTCT-GTAGT-CCAAACAC-
2170
2171 84_HRV43    GTAGAAAGTCATTCAACAACATCCAATGCAGCCCCTGCACTTGATGCAGCTGAAACTGGG
2172 85_HRV43b|  GTAGAAAGTCATTCAACAACATCCAATGCAGCCCCTGCACTTGATGCAGCTGAAACTGGG
2173 86_HRV43a|  GTAGAAAGTCATTCAACAACATCCAATGCAGCCCCTGCACTTGATGCAGCTGAAACTGGG
2174 87_HRV75    ATGGAGAGCCATCCAACAACGTCTAATGCTGCTCCAGCTTTAGATGCAGCTGAAACTGGC
2175 88_HRV75b|  ATGGAGAGCCATCCAACAACGTCTAATGCTGCTCCAGCTTTAGATGCAGCTGAAACTGGC
2176 89_HRV75a|  ATGGAGAGCCATCCAACAACGTCTAATGCTGCTCCAGCTTTAGATGCAGCTGAAACTGGC
2177 GROUP_17    -T-GA-AG-CAT-CAACAAC-TC-AATGC-GC-CC-GC--T-GATGCAGCTGAAACTGG-
2178
2179 84_HRV43    CATACTAGCCAGGTGCAACCTGAAGACATGGTAGAGACAAGGTCAGTACATAATTTCCAA
2180 85_HRV43b|  CATACTAGCCAGGTGCAACCTGAAGACATGGTAGAGACAAGGTCAGTACATAATTTCCAA
2181 86_HRV43a|  CATACTAGCCAGGTGCAACCTGAAGACATGGTAGAGACAAGGTCAGTACATAATTTCCAA
2182 87_HRV75    CATACCAGCCATGTTCAACCAGAAGACATGTTAGAAACAAGGCAAGTACAAAATTTCCAA
2183 88_HRV75b|  CATACCAGCCATGTTCAACCAGAAGACATGTTAGAAACAAGGCAAGTACAAAATTTCCAA
2184 89_HRV75a|  CATACCAGCCATGTTCAACCAGAAGACATGTTAGAAACAAGGCAAGTACAAAATTTCCAA
2185 GROUP_17    CATAC-AGCCA-GT-CAACC-GAAGACATG-TAGA-ACAAGG--AGTACA-AATTTCCAA
2186
2187 84_HRV43    ACCAGAGATGAAATGAGTATTGAAAGTTTCTTGGGCAGATCTGGTTGCATACATATTTCA
2188 85_HRV43b|  ACCAGAGATGAAATGAGTATTGAAAGTTTCTTGGGCAGATCTGGTTGCATACATATTTCA
2189 86_HRV43a|  ACCAGAGATGAAATGAGTATTGAAAGTTTCTTGGGCAGATCTGGTTGCATACATATTTCA
2190 87_HRV75    ACTAGAGATGAGATGAGTATTGAGAGTTTCCTAGGCAGATCTGGATGTATTCATATTTCA
2191 88_HRV75b|  ACTAGAGATGAGATGAGTATTGAGAGTTTCCTAGGCAGATCTGGATGTATTCATATTTCA
2192 89_HRV75a|  ACTAGAGATGAGATGAGTATTGAGAGTTTCCTAGGCAGATCTGGATGTATTCATATTTCA
2193 GROUP_17    AC-AGAGATGA-ATGAGTATTGA-AGTTTC-T-GGCAGATCTGG-TG-AT-CATATTTCA
2194
2195 84_HRV43    ACACTTGAAGTAAATTATGATGAT---------------TATAATGGG---ACAGGCATA
2196 85_HRV43b|  ACACTTGAAGTAAATTATGATGAT---------------TATAATGGG---ACAGGCATA
2197 86_HRV43a|  ACACTTGAAGTAAATTATGATGAT---------------TATAATGGG---ACAGGCATA
2198 87_HRV75    ACACTTGAGATGGATTATACAAAC---------------TATAATGGA---GAAGGCAAA
2199 88_HRV75b|  ACACTTGAGATGGATTATACAAAC---------------TATAATGGA---GAAGGCAAA
2200 89_HRV75a|  ACACTTGAGATGGATTATACAAAC---------------TATAATGGA---GAAGGCAAA
2201 GROUP_17    ACACTTGA--T--ATTAT----A-...............TATAATGG-...--AGGCA-A
2202
```

FIG. D13 CONT'D

09.trace                                                                                       9/20/2007 5:05 PM

| | | |
|---|---|---|
| 2203 | 84_HRV43   | AATTTTACCCAATGGCCAATCAACTTGCAAGAAATGGCACAAATTAGAAGAAAGTATGAA |
| 2204 | 85_HRV43b\| | AATTTTACCCAATGGCCAATCAACTTGCAAGAAATGGCACAAATTAGAAGAAAGTATGAA |
| 2205 | 86_HRV43a\| | AATTTTACCCAATGGCCAATCAACTTGCAAGAAATGGCACAAATTAGAAGAAAGTATGAA |
| 2206 | 87_HRV75   | AACTTCACTCAGTGGCCAATCAATCTACAGGAAATGGCTCAAATTAGAAGGAAATATGAA |
| 2207 | 88_HRV75b\| | AACTTCACTCAGTGGCCAATCAATCTACAGGAAATGGCTCAAATTAGAAGGAAATATGAA |
| 2208 | 89_HRV75a\| | AACTTCACTCAGTGGCCAATCAATCTACAGGAAATGGCTCAAATTAGAAGGAAATATGAA |
| 2209 | GROUP_17   | AA--TT-AC-CA--TGGCCAATCAA---T-CA-GAAATGGC-CAAATTAGAAG--AA-TATGAA |
| 2210 | | |
| 2211 | 84_HRV43   | TTGTTCACATACTTAAGGTTTGATTCTGAAATTACCCTTG-TTCCTTGCATTGCAGCAAA |
| 2212 | 85_HRV43b\| | TTGTTCACATACTTAAGGTTTGATTCTGAAATTACCCTTG-TTCCTTGCATTGCAGCAAA |
| 2213 | 86_HRV43a\| | TTGTTCACATACTTAAGGTTTGATTCTGAAATTACCCTTG-TTCCTTGCATTGCAGCAAA |
| 2214 | 87_HRV75   | TTATTTACATATCTTAGATTTGATTCAGAGGTTACTCTGG-TGCCATGCATTGCAGCTAA |
| 2215 | 88_HRV75b\| | TTATTTACATATCTTAGATTTGATTCAGAGGTTACTCTGG-TGCCATGCATTGCAGCTAA |
| 2216 | 89_HRV75a\| | TTATTTACATATCTTAGATTTGATTCAGAGGTTACTCTGG-TGCCATGCATTGCAGCTAA |
| 2217 | GROUP_17   | TT-TT-ACATA--T-AG-TTTGATTC-GA--TTAC-CT-G.T-CC-TGCATTGCAGC-AA |
| 2218 | | |
| 2219 | 84_HRV43   | AAGCAATGATATAGGCCATGTGGTAATGCAGTACATGTATGTACCACCAGGTGCGCCAAT |
| 2220 | 85_HRV43b\| | AAGCAATGATATAGGCCATGTGGTAATGCAGTACATGTATGTACCACCAGGTGCGCCAAT |
| 2221 | 86_HRV43a\| | AAGCAATGATATAGGCCATGTGGTAATGCAGTACATGTATGTACCACCAGGTGCGCCAAT |
| 2222 | 87_HRV75   | AGGGAATGACATAGGCCATGTAGTAATGCAATATATGTATGTACCACCAGGAGCACCAAT |
| 2223 | 88_HRV75b\| | AGGGAATGACATAGGCCATGTAGTAATGCAATATATGTATGTACCACCAGGAGCACCAAT |
| 2224 | 89_HRV75a\| | AGGGAATGACATAGGCCATGTAGTAATGCAATATATGTATGTACCACCAGGAGCACCAAT |
| 2225 | GROUP_17   | A-G--AATGA--ATAGGCCATGT--GTAATGCA--TA-ATGTATGTACCACCAGG--GC-CCAAT |
| 2226 | | |
| 2227 | 84_HRV43   | TCCAAAAACTAGGAAAGATTATGCATGGCAATCTGGCACAAATGCATCTGTTTTCTGGCA |
| 2228 | 85_HRV43b\| | TCCAAAAACTAGGAAAGATTATGCATGGCAATCTGGCACAAATGCATCTGTTTTCTGGCA |
| 2229 | 86_HRV43a\| | TCCAAAAACTAGGAAAGATTATGCATGGCAATCTGGCACAAATGCATCTGTTTTCTGGCA |
| 2230 | 87_HRV75   | ACCAACAACTAGAAAAGATTATGCATGGCAATCTGGAACAAATGCATCTGTATTTTGGCA |
| 2231 | 88_HRV75b\| | ACCAACAACTAGAAAAGATTATGCATGGCAATCTGGAACAAATGCATCTGTATTTTGGCA |
| 2232 | 89_HRV75a\| | ACCAACAACTAGAAAAGATTATGCATGGCAATCTGGAACAAATGCATCTGTATTTTGGCA |
| 2233 | GROUP_17   | -CCAA--AACTAG-AAAGATTATGCATGGCAATCTGG-ACAAATGCATCTGT-TT-TGGCA |
| 2234 | | |
| 2235 | 84_HRV43   | ACATGGTCAAACATTTCCAAGATTTTCCTTACCTTTTCTGAGCATAGCATCAGCATATTA |
| 2236 | 85_HRV43b\| | ACATGGTCAAACATTTCCAAGATTTTCCTTACCTTTTCTGAGCATAGCATCAGCATATTA |
| 2237 | 86_HRV43a\| | ACATGGTCAAACATTTCCAAGATTTTCCTTACCTTTTCTGAGCATAGCATCAGCATATTA |
| 2238 | 87_HRV75   | ACATGGACAAACATTTCCAAGATTTTCACTACCATTTCTGAGCATTGCATCAGCATATTA |
| 2239 | 88_HRV75b\| | ACATGGACAAACATTTCCAAGATTTTCACTACCATTTCTGAGCATTGCATCAGCATATTA |
| 2240 | 89_HRV75a\| | ACATGGACAAACATTTCCAAGATTTTCACTACCATTTCTGAGCATTGCATCAGCATATTA |
| 2241 | GROUP_17   | ACATGG-CAAACATTTCCAAGATTTTC--TACC-TTTCTGAGCAT-GCATCAGCATATTA |
| 2242 | | |
| 2243 | 84_HRV43   | CATGTTTTATGATGGATATGAAGGTGACCAAAAAACATCCCGTTATGGCACAATTGCAAG |
| 2244 | 85_HRV43b\| | CATGTTTTATGATGGATATGAAGGTGACCAAAAAACATCCCGTTATGGCACAATTGCAAG |
| 2245 | 86_HRV43a\| | CATGTTTTATGATGGATATGAAGGTGACCAAAAAACATCCCGTTATGGCACAATTGCAAG |
| 2246 | 87_HRV75   | CATGTTTTATGATGGATATGAAGGGGATCAAAATACATCCCGTTATGGCACCATTGCTAG |
| 2247 | 88_HRV75b\| | CATGTTTTATGATGGATATGAAGGGGATCAAAATACATCCCGTTATGGCACCATTGCTAG |
| 2248 | 89_HRV75a\| | CATGTTTTATGATGGATATGAAGGGGATCAAAATACATCCCGTTATGGCACCATTGCTAG |
| 2249 | GROUP_17   | CATGTTTTATGATGGATATGAAGG-GA-CAAAA--ACATCCCGTTATGGCAC-ATTGC-AG |
| 2250 | | |
| 2251 | 84_HRV43   | CAACCACATGGGAACATTATGTTCTAGGATAGTTACAGAAGAACACCAAAATCAAATCGA |
| 2252 | 85_HRV43b\| | CAACCACATGGGAACATTATGTTCTAGGATAGTTACAGAAGAACACCAAAATCAAATCGA |
| 2253 | 86_HRV43a\| | CAACCACATGGGAACATTATGTTCTAGGATAGTTACAGAAGAACACCAAAATCAAATCGA |
| 2254 | 87_HRV75   | TAATCACATGGGGACACTGTGTTCTAGAATAGTTACAGAAGAACATCGAAATAAAGTTGA |
| 2255 | 88_HRV75b\| | TAATCACATGGGGACACTGTGTTCTAGAATAGTTACAGAAGAACATCGAAATAAAGTTGA |
| 2256 | 89_HRV75a\| | TAATCACATGGGGACACTGTGTTCTAGAATAGTTACAGAAGAACATCGAAATAAAGTTGA |
| 2257 | GROUP_17   | -AA-CACATGGG-ACA-T-TGTTCTAG-ATAGTTACAGAAGAACA-C-AAAT-AA-T-GA |
| 2258 | | |
| 2259 | 84_HRV43   | GATAACTACCAGGATATATCATAAAGCCAAGCATATCAAAGCTTGGTGCCCAAGACCACC |
| 2260 | 85_HRV43b\| | GATAACTACCAGGATATATCATAAAGCCAAGCATATCAAAGCTTGGTGCCCAAGACCACC |
| 2261 | 86_HRV43a\| | GATAACTACCAGGATATATCATAAAGCCAAGCATATCAAAGCTTGGTGCCCAAGACCACC |
| 2262 | 87_HRV75   | AGTAACCACTAGAATATATCACAAAGCCAAACATATAAAAGCTTGGTGTCCGAGGCCGCC |
| 2263 | 88_HRV75b\| | AGTAACCACTAGAATATATCACAAAGCCAAACATATAAAAGCTTGGTGTCCGAGGCCGCC |
| 2264 | 89_HRV75a\| | AGTAACCACTAGAATATATCACAAAGCCAAACATATAAAAGCTTGGTGTCCGAGGCCGCC |
| 2265 | GROUP_17   | --TAAC-AC-AG--ATATATCA-AAAGCCAA-CATAT-AAAGCTTGGTG-CC-AG-CC-CC |
| 2266 | | |
| 2267 | 84_HRV43   | CAGAGCTGTTGAATACACA-CACACACATGTCACAAATTATAAAA-GAGAAG---GAAAG |

FIG. D13 CONT'D

```
09.trace                                                                  9/20/2007 5:05 PM 2268  85_HRV43b|    CAGAGCTGTTGAATACACA-CACACACATGTCACAAATTATAAAA-GAGAAG---GAAAG
2269  86_HRV43a|    CAGAGCTGTTGAATACACA-CACACACATGTCACAAATTATAAAA-GAGAAG---GAAAG
2270  87_HRV75      CAGGGCTGTTGAATACACA-TTTAGACGTGTAACAAATTACAAAA-GAGATG---GACAA
2271  88_HRV75b|    CAGGGCTGTTGAATACACA-TTTAGACGTGTAACAAATTACAAAA-GAGATG---GACAA
2272  89_HRV75a|    CAGGGCTGTTGAATACACA-TTTAGACGTGTAACAAATTACAAAA-GAGATG---GACAA
2273  GROUP_17      CAG-GCTGTTGAATACACA.---A-AC-TGT-ACAAATTA-AAAA.GAGA-G...GA-A-
2274
2275  84_HRV43      GAGG------TAGAAACAG---CCATAGTATCTAGGAGGGATATCAAAATTGTCAATG--
2276  85_HRV43b|    GAGG------TAGAAACAG---CCATAGTATCTAGGAGGGATATCAAAATTGTCAATG--
2277  86_HRV43a|    GAGG------TAGAAACAG---CCATAGTATCTAGGAGGGATATCAAAATTGTCAATG--
2278  87_HRV75      CAAG------TTGAGATTG---CTATTGAGCCCAGAAGAGATGTTAAGTTTGTAAATG--
2279  88_HRV75b|    CAAG------TTGAGATTG---CTATTGAGCCCAGAAGAGATGTTAAGTTTGTAAATG--
2280  89_HRV75a|    CAAG------TTGAGATTG---CTATTGAGCCCAGAAGAGATGTTAAGTTTGTAAATG--
2281  GROUP_17      -A-G......T-GA-A--G...C-AT-G---C-AG-AG-GAT-T-AA--TTGT-AATG...
2282
2283  84_HRV43      ----CA---------------
2284  85_HRV43b|    ----CG---------------
2285  86_HRV43a|    ----CT---------------
2286  87_HRV75      ----CA---------------
2287  88_HRV75b|    ----CG---------------
2288  89_HRV75a|    ----CT---------------
2289  GROUP_17      ....C-...............

2290
2291
2292
2293  GROUP  18:
2294
2295  96_HRV9a|d    AATCCAGTGGAGAATTACATAGATCAGGTGCTTAATGAGGTTTTGGTAGTCCCAAACATT
2296  97_HRV9b|d    AATCCAGTGGAGAATTACATAGATCAGGTGCTTAATGAGGTTTTGGTAGTCCCAAACATT
2297  98_HRV9       AATCCAGTGGAGAATTACATAGATCAGGTGCTTAATGAGGTTTTGGTAGTCCCAAACATT
2298  99_HRV32      AATCCTGTGGAGAATTACATAGATCAAGTTTTAAATGAAGTTTTGGTAGTTCCAAACATC
2299  100_HRV32a    AATCCTGTGGAGAATTACATAGATCAAGTTTTAAATGAAGTTTTGGTAGTTCCAAACATC
2300  101_HRV32b    AATCCTGTGGAGAATTACATAGATCAAGTTTTAAATGAAGTTTTGGTAGTTCCAAACATC
2301  102_HRV67     AACCCAGTAGAAGATTATGTAGATCAGGTATTGAATGAGGTCCTGGTGGTGCCAAATATA
2302  103_HRV67a    AACCCAGTAGAAGATTATGTAGATCAGGTATTGAATGAGGTCCTGGTGGTGCCAAATATA
2303  104_HRV67b    AACCCAGTAGAAGATTATGTAGATCAGGTATTGAATGAGGTCCTGGTGGTGCCAAATATA
2304  GROUP_18      AA-CC-GT-GA--ATTA--TAGATCA-GT--T-AATGA-GT--TGGT-GT-CCAAA-AT-
2305
2306  96_HRV9a|d    AAAGAGAGCAACCCTACAACCTCTAACTCAGCTCCAGCTCTAGATGCTGCTGAGACAGGC
2307  97_HRV9b|d    AAAGAGAGCAACCCTACAACCTCTAACTCAGCTCCAGCTCTAGATGCTGCTGAGACAGGC
2308  98_HRV9       AAAGAGAGCAACCCTACAACCTCTAACTCAGCTCCAGCTCTAGATGCTGCTGAGACAGGC
2309  99_HRV32      AAAGAAAGCAATCCCACAACCTCTAATTCAGCCCCAGCCTTAGATGCTGCCGAAACAGGT
2310  100_HRV32a    AAAGAAAGCAATCCCACAACCTCTAATTCAGCCCCAGCCTTAGATGCTGCCGAAACAGGT
2311  101_HRV32b    AAAGAAAGCAATCCCACAACCTCTAATTCAGCCCCAGCCTTAGATGCTGCCGAAACAGGT
2312  102_HRV67     AAGCAAAGTGAACCCACGACTTCCAATTCAGCCCCAGCTCTAGATGCTGCTGAGACAGGT
2313  103_HRV67a    AAGCAAAGTGAACCCACGACTTCCAATTCAGCCCCAGCTCTAGATGCTGCTGAGACAGGT
2314  104_HRV67b    AAGCAAAGTGAACCCACGACTTCCAATTCAGCCCCAGCTCTAGATGCTGCTGAGACAGGT
2315  GROUP_18      AA--A-AG--A-CC-AC-AC-TC-AA-TCAGC-CCAGC--TAGATGCTGC-GA-ACAGG-
2316
2317  96_HRV9a|d    CATACTAGCAATGTTCAACCTGAAGACATGATTGAAACACGTTATGTGCAGACATCACAA
2318  97_HRV9b|d    CATACTAGCAATGTTCAACCTGAAGACATGATTGAAACACGTTATGTGCAGACATCACAA
2319  98_HRV9       CATACTAGCAATGTTCAACCTGAAGACATGATTGAAACACGTTATGTGCAGACATCACAA
2320  99_HRV32      CATACCAGTAATGTTCAACCTGAAGACATGATTGAAACACGTTATGTGCAAACAACACAC
2321  100_HRV32a    CATACCAGTAATGTTCAACCTGAAGACATGATTGAAACACGTTATGTGCAAACAACACAC
2322  101_HRV32b    CATACCAGTAATGTTCAACCTGAAGACATGATTGAAACACGTTATGTGCAAACAACACAC
2323  102_HRV67     CACACTAGCAGTGTACAACCTGAAGATATGATCGAGACTCGTTATGTACAGGCATCAAAT
2324  103_HRV67a    CACACTAGCAGTGTACAACCTGAAGATATGATCGAGACTCGTTATGTACAGGCATCAAAT
2325  104_HRV67b    CACACTAGCAGTGTACAACCTGAAGATATGATCGAGACTCGTTATGTACAGGCATCAAAT
2326  GROUP_18      CA-AC-AG-A-TGT-CAACCTGAAGA-ATGAT-GA-AC-CGTTATGT-CA--CA-CA-A-
2327
2328  96_HRV9a|d    ACCAGAGATGAAATGAGTCTTGAAAGCTTCTTAGGGAGATCAGGTTGTATACACATATCT
2329  97_HRV9b|d    ACCAGAGATGAAATGAGTCTTGAAAGCTTCTTAGGGAGATCAGGTTGTATACACATATCT
2330  98_HRV9       ACCAGAGATGAAATGAGTCTTGAAAGCTTCTTAGGGAGATCAGGTTGTATACACATATCT
2331  99_HRV32      ACTAGAGATGAGATGAGTCTTGAGAGCTTCTTAGGGAGGTCAGGATGTGTACATATATCC
2332  100_HRV32a    ACTAGAGATGAGATGAGTCTTGAGAGCTTCTTAGGGAGGTCAGGATGTGTACATATATCC
```

FIG. D13 CONT'D

```
09.trace                                                                                  9/20/2007 5:05 PM 2333  101_HRV32b    ACTAGAGATGAGATGAGTCTTGAGAGCTTCTTAGGGAGGTCAGGATGTGTACATATATCC
2334  102_HRV67     ACCAGAGATGAAATGAGTCTCGAGAGCTTTCTTGGAAGGTCAGGCTGTATTCATATATCA
2335  103_HRV67a    ACCAGAGATGAAATGAGTCTCGAGAGCTTTCTTGGAAGGTCAGGCTGTATTCATATATCA
2336  104_HRV67b    ACCAGAGATGAAATGAGTCTCGAGAGCTTTCTTGGAAGGTCAGGCTGTATTCATATATCA
2337  GROUP_18      AC-AGAGATGA-ATGAGTCT-GA-AGCTT--T-GG-AG-TCAGG-TGT-T-CA-ATATC-
2338
2339  96_HRV9a|d    AAATTGAATATTGATTACAGTGAC---------------TATGATAAG---AGTGTTGAA
2340  97_HRV9b|d    AAATTGAATATTGATTACAGTGAC---------------TATGATAAG---AGTGTTGAA
2341  98_HRV9       AAATTGAATATTGATTACAGTGAC---------------TATGATAAG---AGTGTTGAA
2342  99_HRV32      AAATTAGATATTGATTATACCAAT---------------TACAATAAA---AGTGTTAAG
2343  100_HRV32a    AAATTAGATATTGATTATACCAAT---------------TACAATAAA---AGTGTTAAG
2344  101_HRV32b    AAATTAGATATTGATTATACCAAT---------------TACAATAAA---AGTGTTAAG
2345  102_HRV67     AAATTGAATATTGATTATAATGCA---------------TATGATGAA---AGTAGGGAC
2346  103_HRV67a    AAATTGAATATTGATTATAATGCA---------------TATGATGAA---AGTAGGGAC
2347  104_HRV67b    AAATTGAATATTGATTATAATGCA---------------TATGATGAA---AGTAGGGAC
2348  GROUP_18      AAATT--ATATTGATTA-A-----...............TA--AT-A-...AGT----A-
2349
2350  96_HRV9a|d    AATTTCACAATCTGGAAAATAAATATAAAGGAAATGGCCCAGATCAGGAGGAAATTTGAA
2351  97_HRV9b|d    AATTTCACAATCTGGAAAATAAATATAAAGGAAATGGCCCAGATCAGGAGGAAATTTGAA
2352  98_HRV9       AATTTCACAATCTGGAAAATAAATATAAAGGAAATGGCCCAGATCAGGAGGAAATTTGAA
2353  99_HRV32      AATTTCACAATTTGGAAGATAAATATAAAGAAATGGCCCAGATTAGGAGAAAATTTGAG
2354  100_HRV32a    AATTTCACAATTTGGAAGATAAATATAAAAGAAATGGCCCAGATTAGGAGAAAATTTGAG
2355  101_HRV32b    AATTTCACAATTTGGAAGATAAATATAAAAGAAATGGCCCAGATTAGGAGAAAATTTGAG
2356  102_HRV67     AATTTCACAATTTGGAAAATAAATATAAAAGAAATGGCCCAGATTAGGAGGAAATTTGAA
2357  103_HRV67a    AATTTCACAATTTGGAAAATAAATATAAAAGAAATGGCCCAGATTAGGAGGAAATTTGAA
2358  104_HRV67b    AATTTCACAATTTGGAAAATAAATATAAAAGAAATGGCCCAGATTAGGAGGAAATTTGAA
2359  GROUP_18      AATTTCACAAT-TGGAA-ATAAATATAAA-GAAATGGCCCAGAT-AGGAG-AAATTTGA-
2360
2361  96_HRV9a|d    TTGTTTACATATGCAAGATTTGACTCTGAAATAACATTGG-TCCCGTGTATAGCAGCAGA
2362  97_HRV9b|d    TTGTTTACATATGCAAGATTTGACTCTGAAATAACATTGG-TCCCGTGTATAGCAGCAGA
2363  98_HRV9       TTGTTTACATATGCAAGATTTGACTCTGAAATAACATTGG-TCCCGTGTATAGCAGCAGA
2364  99_HRV32      TTGTTTACATACACAAGGTTTGATTCTGAAATAACATTAG-TACCTTGTATAGCTGCAGA
2365  100_HRV32a    TTGTTTACATACACAAGGTTTGATTCTGAAATAACATTAG-TACCTTGTATAGCTGCAGA
2366  101_HRV32b    TTGTTTACATACACAAGGTTTGATTCTGAAATAACATTAG-TACCTTGTATAGCTGCAGA
2367  102_HRV67     CTATTCACATATACAAGATTTGATTCTGAGATAACACTGG-TACCATGCATAGCTGCAGA
2368  103_HRV67a    CTATTCACATATACAAGATTTGATTCTGAGATAACACTGG-TACCATGCATAGCTGCAGA
2369  104_HRV67b    CTATTCACATATACAAGATTTGATTCTGAGATAACACTGG-TACCATGCATAGCTGCAGA
2370  GROUP_18      -T-TT-ACATA--CAAG-TTTGA-TCTGA-ATAACA-T-G.T-CC-TG-ATAGC-GCAGA
2371
2372  96_HRV9a|d    AAGTGATAGCGTTGGCCATGTTGTTATGCAGTACATGTATGTACCACCAGGGGCACCTTT
2373  97_HRV9b|d    AAGTGATAGCGTTGGCCATGTTGTTATGCAGTACATGTATGTACCACCAGGGGCACCTTT
2374  98_HRV9       AAGTGATAGCGTTGGCCATGTTGTTATGCAGTACATGTATGTACCACCAGGGGCACCTTT
2375  99_HRV32      AAGTGACAGCATTGGTCATGTTGTTATGCAGTACATGTATGTACCACCAGGGGCTCCTCT
2376  100_HRV32a    AAGTGACAGCATTGGTCATGTTGTTATGCAGTACATGTATGTACCACCAGGGGCTCCTCT
2377  101_HRV32b    AAGTGACAGCATTGGTCATGTTGTTATGCAGTACATGTATGTACCACCAGGGGCTCCTCT
2378  102_HRV67     GAGTGACAGCATTGGGCATGTTGTAATGCAATATATGTATGTACCTCCAGGAGCACCATT
2379  103_HRV67a    GAGTGACAGCATTGGGCATGTTGTAATGCAATATATGTATGTACCTCCAGGAGCACCATT
2380  104_HRV67b    GAGTGACAGCATTGGGCATGTTGTAATGCAATATATGTATGTACCTCCAGGAGCACCATT
2381  GROUP_18      -AGTGA-AGC-TTGG-CATGTTGT-ATGCA-TA-ATGTATGTACC-CCAGG-GC-CC--T
2382
2383  96_HRV9a|d    ACCAAGGACTAGAGATGATTATGCATGGCAATCAGGCACAAATGCTTCCATCTTTTGGCA
2384  97_HRV9b|d    ACCAAGGACTAGAGATGATTATGCATGGCAATCAGGCACAAATGCTTCCATCTTTTGGCA
2385  98_HRV9       ACCAAGGACTAGAGATGATTATGCATGGCAATCAGGCACAAATGCTTCCATCTTTTGGCA
2386  99_HRV32      ACCACAAGCAAGAGATGACTACACATGGCAATCTGGCACGAATGCATCTATCTTTTGGCA
2387  100_HRV32a    ACCACAAGCAAGAGATGACTACACATGGCAATCTGGCACGAATGCATCTATCTTTTGGCA
2388  101_HRV32b    ACCACAAGCAAGAGATGACTACACATGGCAATCTGGCACGAATGCATCTATCTTTTGGCA
2389  102_HRV67     ACCAACAAAAAGAGATGACTACACATGGCAATCAGGTACAAATGCATCCATCTTTTGGCA
2390  103_HRV67a    ACCAACAAAAAGAGATGACTACACATGGCAATCAGGTACAAATGCATCCATCTTTTGGCA
2391  104_HRV67b    ACCAACAAAAAGAGATGACTACACATGGCAATCAGGTACAAATGCATCCATCTTTTGGCA
2392  GROUP_18      ACCA------AGAGATGA-TA--CATGGCAATC-GG-AC-AATGC-TC-ATCTTTTGGCA
2393
2394  96_HRV9a|d    ACATGGACAATCATATCCCAGATTTTCACTTCCGTTTTTGAGCATTGCCTCTGCATATTA
2395  97_HRV9b|d    ACATGGACAATCATATCCCAGATTTTCACTTCCGTTTTTGAGCATTGCCTCTGCATATTA
2396  98_HRV9       ACATGGACAATCATATCCCAGATTTTCACTTCCGTTTTTGAGCATTGCCTCTGCATATTA
2397  99_HRV32      GCATGGACAGGCATATCCCAGGTTTTCACTTCCATTTCTAAGTATTGCCTCTGCATACTA
```

FIG. D13 CONT'D

09.trace 9/20/2007 5:05 PM

```
2398 100_HRV32a    GCATGGACAGGCATATCCCAGGTTTTCACTTCCATTTCTAAGTATTGCCTCTGCATACTA
2399 101_HRV32b    GCATGGACAGGCATATCCCAGGTTTTCACTTCCATTTCTAAGTATTGCCTCTGCATACTA
2400 102_HRV67     ACATGGACAATCATACCCCAGATTCTCACTACCATTCTTAAGTATTGCCTCTGCTTATTA
2401 103_HRV67a    ACATGGACAATCATACCCCAGATTCTCACTACCATTCTTAAGTATTGCCTCTGCTTATTA
2402 104_HRV67b    ACATGGACAATCATACCCCAGATTCTCACTACCATTCTTAAGTATTGCCTCTGCTTATTA
2403 GROUP_18      -CATGGACA--CATA-CCCAG-TT-TCACT-CC-TT--T-AG-ATTGCCTCTGC-TA-TA
2404
2405 96_HRV9a|d    CATGTTCTATGATGGTTATGATGGTGG---ACCAGATTCTCTGTATGGAACAATTGTAAC
2406 97_HRV9b|d    CATGTTCTATGATGGTTATGATGGTGG---ACCAGATTCTCTGTATGGAACAATTGTAAC
2407 98_HRV9       CATGTTCTATGATGGTTATGATGGTGG---ACCAGATTCTCTGTATGGAACAATTGTAAC
2408 99_HRV32      CATGTTTTATGATGGTTATGATGGTGG---GCCAGATTCACAATATGGAACAATTGTAAC
2409 100_HRV32a    CATGTTTTATGATGGTTATGATGGTGG---GCCAGATTCACAATATGGAACAATTGTAAC
2410 101_HRV32b    CATGTTTTATGATGGTTATGATGGTGG---GCCAGATTCACAATATGGAACAATTGTAAC
2411 102_HRV67     CATGTTTTATGATGGCTATGATGGTGG---ACCAGATTCACTATATGGCACCATAGTAAC
2412 103_HRV67a    CATGTTTTATGATGGCTATGATGGTGG---ACCAGATTCACTATATGGCACCATAGTAAC
2413 104_HRV67b    CATGTTTTATGATGGCTATGATGGTGG---ACCAGATTCACTATATGGCACCATAGTAAC
2414 GROUP_18      CATGTT-TATGATGG-TATGATGGTGG...-CCAGATTC-C---TATGG-AC-AT-GTAAC
2415
2416 96_HRV9a|d    AAATGATATGGGATCTTTATGTTCCCGTGTAGTTACTGAAGAGCATGGACCCCGTGTCAA
2417 97_HRV9b|d    AAATGATATGGGATCTTTATGTTCCCGTGTAGTTACTGAAGAGCATGGACCCCGTGTCAA
2418 98_HRV9       AAATGATATGGGATCTTTATGTTCCCGTGTAGTTACTGAAGAGCATGGACCCCGTGTCAA
2419 99_HRV32      AAATGATATGGGTTCCCTGTGTTCTCGTATAGTCACCGAAGAGCACGGATCCCGTGTTGA
2420 100_HRV32a    AAATGATATGGGTTCCCTGTGTTCTCGTATAGTCACCGAAGAGCACGGATCCCGTGTTGA
2421 101_HRV32b    AAATGATATGGGTTCCCTGTGTTCTCGTATAGTCACCGAAGAGCACGGATCCCGTGTTGA
2422 102_HRV67     TAATGATATGGGTTCCTTGTGTTCGCGTATAGTTACTGAAGAACATGGTTCTCGCGTAAA
2423 103_HRV67a    TAATGATATGGGTTCCTTGTGTTCGCGTATAGTTACTGAAGAACATGGTTCTCGCGTAAA
2424 104_HRV67b    TAATGATATGGGTTCCTTGTGTTCGCGTATAGTTACTGAAGAACATGGTTCTCGCGTAAA
2425 GROUP_18      -AATGATATGGG-TC--T-TGTTC-CGT-TAGT-AC-GAAGA-CA-GG--C-CG-GT--A
2426
2427 96_HRV9a|d    AATTTCAACCAGAATATATCACAAAGCCAAACATGTTAAAGCCTGGTGCCCAAGACCTCC
2428 97_HRV9b|d    AATTTCAACCAGAATATATCACAAAGCCAAACATGTTAAAGCCTGGTGCCCAAGACCTCC
2429 98_HRV9       AATTTCAACCAGAATATATCACAAAGCCAAACATGTTAAAGCCTGGTGCCCAAGACCTCC
2430 99_HRV32      TATTTCAACTAGGGTATATCACAAAGCTAAACACGTCAAAGCTTGGTGCCCACGACCACC
2431 100_HRV32a    TATTTCAACTAGGGTATATCACAAAGCTAAACACGTCAAAGCTTGGTGCCCACGACCACC
2432 101_HRV32b    TATTTCAACTAGGGTATATCACAAAGCTAAACACGTCAAAGCTTGGTGCCCACGACCACC
2433 102_HRV67     AATTGCAACGCGGGTGTATCATAAGGCTAAACATGTAAAAGCTTGGTGCCCAAGGCCCCC
2434 103_HRV67a    AATTGCAACGCGGGTGTATCATAAGGCTAAACATGTAAAAGCTTGGTGCCCAAGGCCCCC
2435 104_HRV67b    AATTGCAACGCGGGTGTATCATAAGGCTAAACATGTAAAAGCTTGGTGCCCAAGGCCCCC
2436 GROUP_18      -ATT-CAAC--G--T-TATCA-AA-GC-AAACA-GT-AAAGC-TGGTGCCCA-G-CC-CC
2437
2438 96_HRV9a|d    TAGGGCAGTTGAGTATATA-CATACACATGTCACAAATTACAAGC-CAAGCA---CAGGC
2439 97_HRV9b|d    TAGGGCAGTTGAGTATATA-CATACACATGTCACAAATTACAAGC-CAAGCA---CAGGC
2440 98_HRV9       TAGGGCAGTTGAGTATATA-CATACACATGTCACAAATTACAAGC-CAAGCA---CAGGC
2441 99_HRV32      TAGGGCAGTTGAATATACA-CATACACATGTTACAAATTACAAAC-CAAGCA---CAGGT
2442 100_HRV32a    TAGGGCAGTTGAATATACA-CATACACATGTTACAAATTACAAAC-CAAGCA---CAGGT
2443 101_HRV32b    TAGGGCAGTTGAATATACA-CATACACATGTTACAAATTACAAAC-CAAGCA---CAGGT
2444 102_HRV67     TAGAGCAGTTGAATACATA-CACACACATGTTACAAACTATAGAC-CAGAAA---CAGGT
2445 103_HRV67a    TAGAGCAGTTGAATACATA-CACACACATGTTACAAACTATAGAC-CAGAAA---CAGGT
2446 104_HRV67b    TAGAGCAGTTGAATACATA-CACACACATGTTACAAACTATAGAC-CAGAAA---CAGGT
2447 GROUP_18      TAG-GCAGTTGA-TA-A-.CA-ACACATGT-ACAAA-TA-A--C.CA---A...CAGG-
2448
2449 96_HRV9a|d    GATT------ATGCCACAG---TTATACCAGTTAGAGACAATGTTAGGGCAGTAAAGA--
2450 97_HRV9b|d    GATT------ATGCCACAG---TTATACCAGTTAGAGACAATGTTAGGGCAGTAAAGA--
2451 98_HRV9       GATT------ATGCCACAG---TTATACCAGTTAGAGACAATGTTAGGGCAGTAAAGA--
2452 99_HRV32      GATT------ACACCACAG---CCATACAAACCAGAGAGCATGTTAGAGCAGTCAAAA--
2453 100_HRV32a    GATT------ACACCACAG---CCATACAAACCAGAGAGCATGTTAGAGCAGTCAAAA--
2454 101_HRV32b    GATT------ACACCACAG---CCATACAAACCAGAGAGCATGTTAGAGCAGTCAAAA--
2455 102_HRV67     GAGG------CTCAAACGG---TTATACCTGTTAGAGCAGATGTTAGAACAATTAGAA--
2456 103_HRV67a    GAGG------CTCAAACGG---TTATACCTGTTAGAGCAGATGTTAGAACAATTAGAA--
2457 104_HRV67b    GAGG------CTCAAACGG---TTATACCTGTTAGAGCAGATGTTAGAACAATTAGAA--
2458 GROUP_18      GA--......------AC-G...--ATAC-----AGAG---ATGTTAG--CA-T-A--A..
2459
2460 96_HRV9a|d    ----ATGTC-----------
2461 97_HRV9b|d    ----ATGTG-----------
2462 98_HRV9       ----ATGTA-----------
```

FIG. D13 CONT'D

```
09.trace                                                                  9/20/2007 5:05 PM 2463  99_HRV32     ----ATGTA-----------
2464  100_HRV32a   ----ATGTG-----------
2465  101_HRV32b   ----ATGTC-----------
2466  102_HRV67    ----ATGTA-----------
2467  103_HRV67a   ----ATGTC-----------
2468  104_HRV67b   ----ATGTT-----------
2469  GROUP_18     ....ATGT-...........
2470
2471
2472
2473  GROUP 19:
2474
2475  105_HRV15    AACCCAGTGGAGAATTACATAGATGAAGTGTTAAATGAGGTTCTAGTAGTTCCAAACATT
2476  106_HRV15a   AACCCAGTGGAGAATTACATAGATGAAGTGTTAAATGAGGTTCTAGTAGTTCCAAACATT
2477  107_HRV15b   AACCCAGTGGAGAATTACATAGATGAAGTGTTAAATGAGGTTCTAGTAGTTCCAAACATT
2478  108_HRV74a   AACCCAGTGGAGAATTACATAGATGAAGTGTTGAATGAAGTGTTAGTTGTTCCAAATATT
2479  109_HRV74b   AACCCAGTGGAGAATTACATAGATGAAGTGTTGAATGAAGTGTTAGTTGTTCCAAATATT
2480  110_HRV74    AACCCAGTGGAGAATTACATAGATGAAGTGTTGAATGAAGTGTTAGTTGTTCCAAATATT
2481  GROUP_19     AACCCAGTGGAGAATTACATAGATGAAGTGTT-AATGA-GT--TAGT-GTTCCAAA-ATT
2482
2483  105_HRV15    AAGGAGAGTCACTCAAGCACATCCAACTCAGCACCAGCACTAGATGCAGCTGAGACCGGC
2484  106_HRV15a   AAGGAGAGTCACTCAAGCACATCCAACTCAGCACCAGCACTAGATGCAGCTGAGACCGGC
2485  107_HRV15b   AAGGAGAGTCACTCAAGCACATCCAACTCAGCACCAGCACTAGATGCAGCTGAGACCGGC
2486  108_HRV74a   AGAGAAAGCCATTCAAGTACTTCAAACTCAGCACCAGCACTGGATGCAGCTGAAACTGGC
2487  109_HRV74b   AGAGAAAGCCATTCAAGTACTTCAAACTCAGCACCAGCACTGGATGCAGCTGAAACTGGC
2488  110_HRV74    AGAGAAAGCCATTCAAGTACTTCAAACTCAGCACCAGCACTGGATGCAGCTGAAACTGGC
2489  GROUP_19     A--GA-AG-CA-TCAAG-AC-TC-AACTCAGCACCAGCACT-GATGCAGCTGA-AC-GGC
2490
2491  105_HRV15    CATACTAGCAGTGTTCAACCTGAGGATATGATTGAAACTCGTTACGTCCAAACATCACAG
2492  106_HRV15a   CATACTAGCAGTGTTCAACCTGAGGATATGATTGAAACTCGTTACGTCCAAACATCACAG
2493  107_HRV15b   CATACTAGCAGTGTTCAACCTGAGGATATGATTGAAACTCGTTACGTCCAAACATCACAG
2494  108_HRV74a   CATACCAGTAATGTGCAACCAGAAGATATGGTTGAGACACGCTATGTGCAAACCTCACAG
2495  109_HRV74b   CATACCAGTAATGTGCAACCAGAAGATATGGTTGAGACACGCTATGTGCAAACCTCACAG
2496  110_HRV74    CATACCAGTAATGTGCAACCAGAAGATATGGTTGAGACACGCTATGTGCAAACCTCACAG
2497  GROUP_19     CATAC-AG-A-TGT-CAACC-GA-GATATG-TTGA-AC-CG-TA-GT-CAAAC-TCACAG
2498
2499  105_HRV15    ACCAGAGATGAAATGAGTATTGAGAGCTTCCTTGGTAGATCAGGGTGTGTCCATATTTCT
2500  106_HRV15a   ACCAGAGATGAAATGAGTATTGAGAGCTTCCTTGGTAGATCAGGGTGTGTCCATATTTCT
2501  107_HRV15b   ACCAGAGATGAAATGAGTATTGAGAGCTTCCTTGGTAGATCAGGGTGTGTCCATATTTCT
2502  108_HRV74a   ACAAGAGATGAGATGAGTGTAGAAAGTTTTCTTGGAAGATCAGGATGCATCCATATCTCA
2503  109_HRV74b   ACAAGAGATGAGATGAGTGTAGAAAGTTTTCTTGGAAGATCAGGATGCATCCATATCTCA
2504  110_HRV74    ACAAGAGATGAGATGAGTGTAGAAAGTTTTCTTGGAAGATCAGGATGCATCCATATCTCA
2505  GROUP_19     AC-AGAGATGA-ATGAGT-T-GA-AG-TT-CTTGG-AGATCAGG-TG--TCCATAT-TC-
2506
2507  105_HRV15    GATTTGAAAATACATTATGAAGAT---------------TATAATAAA---GATGGGAAA
2508  106_HRV15a   GATTTGAAAATACATTATGAAGAT---------------TATAATAAA---GATGGGAAA
2509  107_HRV15b   GATTTGAAAATACATTATGAAGAT---------------TATAATAAA---GATGGGAAA
2510  108_HRV74a   CATCTAAAAATTGATTATACAAAC---------------TATAATGTT---AAAGGGAAG
2511  109_HRV74b   CATCTAAAAATTGATTATACAAAC---------------TATAATGTT---AAAGGGAAG
2512  110_HRV74    CATCTAAAAATTGATTATACAAAC---------------TATAATGTT---AAAGGGAAG
2513  GROUP_19     -AT-T-AAAAT--ATTAT--A-A-...........TATAAT---...-A-GGGAA-
2514
2515  105_HRV15    AACTTTACTAAATGGCAAATTAATCTCAAAGAAATGGCCCAGATTAGAAGGAAATTTGAG
2516  106_HRV15a   AACTTTACTAAATGGCAAATTAATCTCAAAGAAATGGCCCAGATTAGAAGGAAATTTGAG
2517  107_HRV15b   AACTTTACTAAATGGCAAATTAATCTCAAAGAAATGGCCCAGATTAGAAGGAAATTTGAG
2518  108_HRV74a   AATTTTACTAAATGGCAAATAAATCTTAAAGAAATGGCACAGATTAGGAGAAAATTTGAG
2519  109_HRV74b   AATTTTACTAAATGGCAAATAAATCTTAAAGAAATGGCACAGATTAGGAGAAAATTTGAG
2520  110_HRV74    AATTTTACTAAATGGCAAATAAATCTTAAAGAAATGGCACAGATTAGGAGAAAATTTGAG
2521  GROUP_19     AA-TTTACTAAATGGCAAAT-AATCT-AAAGAAATGGC-CAGATTAG-AG-AAATTTGAG
2522
2523  105_HRV15    TTATTCACATATGTAAGGTTTGATTCAGAAATAACACTTG-TACCATGCATTGCAGCAAA
2524  106_HRV15a   TTATTCACATATGTAAGGTTTGATTCAGAAATAACACTTG-TACCATGCATTGCAGCAAA
2525  107_HRV15b   TTATTCACATATGTAAGGTTTGATTCAGAAATAACACTTG-TACCATGCATTGCAGCAAA
2526  108_HRV74a   TTGTTCACATATGTTAGATTTGACTCAGAAGTGACATTAG-TTCCATGCATTGCTGCTAA
2527  109_HRV74b   TTGTTCACATATGTTAGATTTGACTCAGAAGTGACATTAG-TTCCATGCATTGCTGCTAA
```

FIG. D13 CONT'D

```
09.trace                                                                                                9/20/2007 5:05 PM 2528  110_HRV74    TTGTTCACATATGTTAGATTTGACTCAGAAGTGACATTAG-TTCCATGCATTGCTGCTAA
2529  GROUP_19     TT-TTCACATATGT-AG-TTTGA-TCAGAA-T-ACA-T-G.T-CCATGCATTGC-GC-AA
2530
2531  105_HRV15    GAGTGATAACATCGGTCATGTTGTCATGCAATATATGTATGTTCCTCCGGGAGCCCCTTT
2532  106_HRV15a   GAGTGATAACATCGGTCATGTTGTCATGCAATATATGTATGTTCCTCCGGGAGCCCCTTT
2533  107_HRV15b   GAGTGATAACATCGGTCATGTTGTCATGCAATATATGTATGTTCCTCCGGGAGCCCCTTT
2534  108_HRV74a   AAGTGACAACATTGGCCATGTTGTTATGCAATACATGTATGTCCCCCCAGGAGCACCTTT
2535  109_HRV74b   AAGTGACAACATTGGCCATGTTGTTATGCAATACATGTATGTCCCCCCAGGAGCACCTTT
2536  110_HRV74    AAGTGACAACATTGGCCATGTTGTTATGCAATACATGTATGTCCCCCCAGGAGCACCTTT
2537  GROUP_19     -AGTGA-AACAT-GG-CATGTTGT-ATGCAATA-ATGTATGT-CC-CC-GGAGC-CCTTT
2538
2539  105_HRV15    ACCCAATAAAAGGAATGATTACACATGGCAATCAGGTACAAATGCCTCTGTTTTCTGGCA
2540  106_HRV15a   ACCCAATAAAAGGAATGATTACACATGGCAATCAGGTACAAATGCCTCTGTTTTCTGGCA
2541  107_HRV15b   ACCCAATAAAAGGAATGATTACACATGGCAATCAGGTACAAATGCCTCTGTTTTCTGGCA
2542  108_HRV74a   ACCCAAGAAAAGAGATGATTACACATGGCAATCTGGCACAAATGCATCTGTGTTTTGGCA
2543  109_HRV74b   ACCCAAGAAAAGAGATGATTACACATGGCAATCTGGCACAAATGCATCTGTGTTTTGGCA
2544  110_HRV74    ACCCAAGAAAAGAGATGATTACACATGGCAATCTGGCACAAATGCATCTGTGTTTTGGCA
2545  GROUP_19     ACCCAA-AAAAG--ATGATTACACATGGCAATC-GG-ACAAATGC-TCTGT-TT-TGGCA
2546
2547  105_HRV15    ACATGGTCAACCTTACCCCAGATTTTCTTTGCCTTTTCTCAGCATTGCATCTGCTTACTA
2548  106_HRV15a   ACATGGTCAACCTTACCCCAGATTTTCTTTGCCTTTTCTCAGCATTGCATCTGCTTACTA
2549  107_HRV15b   ACATGGTCAACCTTACCCCAGATTTTCTTTGCCTTTTCTCAGCATTGCATCTGCTTACTA
2550  108_HRV74a   GCATGGACAGCCATACCCTAGATTCTCATTACCTTTCCTTAGCATAGCATCTGCTTATTA
2551  109_HRV74b   GCATGGACAGCCATACCCTAGATTCTCATTACCTTTCCTTAGCATAGCATCTGCTTATTA
2552  110_HRV74    GCATGGACAGCCATACCCTAGATTCTCATTACCTTTCCTTAGCATAGCATCTGCTTATTA
2553  GROUP_19     -CATGG-CA-CC-TACCC-AGATT-TC-TT-CCTTT-CT-AGCAT-GCATCTGCTTA-TA
2554
2555  105_HRV15    CATGTTCTATGATGGATATGATGGAGATTCCACTGAATCACATTATGGTACAGTGGTCAC
2556  106_HRV15a   CATGTTCTATGATGGATATGATGGAGATTCCACTGAATCACATTATGGTACAGTGGTCAC
2557  107_HRV15b   CATGTTCTATGATGGATATGATGGAGATTCCACTGAATCACATTATGGTACAGTGGTCAC
2558  108_HRV74a   CATGTTTTATGATGGATATGATGGAGACTCTACTGAATCACATTATGGTACAGTAGTAAC
2559  109_HRV74b   CATGTTTTATGATGGATATGATGGAGACTCTACTGAATCACATTATGGTACAGTAGTAAC
2560  110_HRV74    CATGTTTTATGATGGATATGATGGAGACTCTACTGAATCACATTATGGTACAGTAGTAAC
2561  GROUP_19     CATGTT-TATGATGGATATGATGGAGA-TC-ACTGAATCACATTATGGTACAGT-GT-AC
2562
2563  105_HRV15    TAATGACATGGGGACACTGTGTTCTAGAATAGTAACTGAAGAGCATGGGACACGTGTAGA
2564  106_HRV15a   TAATGACATGGGGACACTGTGTTCTAGAATAGTAACTGAAGAGCATGGGACACGTGTAGA
2565  107_HRV15b   TAATGACATGGGGACACTGTGTTCTAGAATAGTAACTGAAGAGCATGGGACACGTGTAGA
2566  108_HRV74a   AAATGACATGGGAACTCTATGTTCTAGAATTGTGACTGAAGAACACGATGCACGTGTGGA
2567  109_HRV74b   AAATGACATGGGAACTCTATGTTCTAGAATTGTGACTGAAGAACACGATGCACGTGTGGA
2568  110_HRV74    AAATGACATGGGAACTCTATGTTCTAGAATTGTGACTGAAGAACACGATGCACGTGTGGA
2569  GROUP_19     -AATGACATGGG-AC-CT-TGTTCTAGAAT-GT-ACTGAAGA-CA-G---CACGTGT-GA
2570
2571  105_HRV15    GATTACAACTAGAGTGTATCACAAAGCTAAACATGTAAAGGCTTGGTGCCCCAGACCCCC
2572  106_HRV15a   GATTACAACTAGAGTGTATCACAAAGCTAAACATGTAAAGGCTTGGTGCCCCAGACCCCC
2573  107_HRV15b   GATTACAACTAGAGTGTATCACAAAGCTAAACATGTAAAGGCTTGGTGCCCCAGACCCCC
2574  108_HRV74a   AATTACAACTAGAGTGTACCATAAAGCAAAGCATGTGAAGGCATGGTGTCCTAGACCCCC
2575  109_HRV74b   AATTACAACTAGAGTGTACCATAAAGCAAAGCATGTGAAGGCATGGTGTCCTAGACCCCC
2576  110_HRV74    AATTACAACTAGAGTGTACCATAAAGCAAAGCATGTGAAGGCATGGTGTCCTAGACCCCC
2577  GROUP_19     -ATTACAACTAGAGTGTA-CA-AAAGC-AA-CATGT-AAGGC-TGGTG-CC-AGACCCCC
2578
2579  105_HRV15    TAGAGCAGTGGAATATACA-CACACACATGTCACAAATTACAAAC-CACAAG---ATGGT
2580  106_HRV15a   TAGAGCAGTGGAATATACA-CACACACATGTCACAAATTACAAAC-CACAAG---ATGGT
2581  107_HRV15b   TAGAGCAGTGGAATATACA-CACACACATGTCACAAATTACAAAC-CACAAG---ATGGT
2582  108_HRV74a   TAGAGCAGTTGAATATACT-CACACACATGTCACAAATTACAAAC-CACAAG---AAGGT
2583  109_HRV74b   TAGAGCAGTTGAATATACT-CACACACATGTCACAAATTACAAAC-CACAAG---AAGGT
2584  110_HRV74    TAGAGCAGTTGAATATACT-CACACACATGTCACAAATTACAAAC-CACAAG---AAGGT
2585  GROUP_19     TAGAGCAGT-GAATATAC-.CACACACATGTCACAAATTACAAAC.CACAAG...A-GGT
2586
2587  105_HRV15    GATG------TAACTACAG---TTATTCCAACTAGAGAAAATGTTAGAGCTATAGTAA--
2588  106_HRV15a   GATG------TAACTACAG---TTATTCCAACTAGAGAAAATGTTAGAGCTATAGTAA--
2589  107_HRV15b   GATG------TAACTACAG---TTATTCCAACTAGAGAAAATGTTAGAGCTATAGTAA--
2590  108_HRV74a   GACG------TAACTACAG---TCATCCCAACTAGG---------AGATCAATAGTGA--
2591  109_HRV74b   GACG------TAACTACAG---TCATCCCAACTAGG---------AGATCAATAGTGA--
2592  110_HRV74    GACG------TAACTACAG---TCATCCCAACTAGG---------AGATCAATAGTGA--
```

FIG. D13 CONT'D

```
09.trace                                                                 9/20/2007 5:05 PM 2593 GROUP_19      GA-G......TAACTACAG...T-AT-CCAACTAG----------AGA-C-ATAGT-A..
2594
2595 105_HRV15     ----ATGTT------------
2596 106_HRV15a    ----ATGTA------------
2597 107_HRV15b    ----ATGTC------------
2598 108_HRV74a    ----ATGTA------------
2599 109_HRV74b    ----ATGTC------------
2600 110_HRV74     ----ATGTT------------
2601 GROUP_19      ....ATGT-............
2602
2603
2604
2605 GROUP  20:
2606
2607 111_HRV38a    AACCCAGTAGAGGAATACATAGATGGAGTCTTGAATGAGGTTCTTGTGGTTCCGAACATT
2608 112_HRV38b    AACCCAGTAGAGGAATACATAGATGGAGTCTTGAATGAGGTTCTTGTGGTTCCGAACATT
2609 113_HRV38     AACCCAGTAGAGGAATACATAGATGGAGTCTTGAATGAGGTTCTTGTGGTTCCGAACATT
2610 GROUP_20      AACCCAGTAGAGGAATACATAGATGGAGTCTTGAATGAGGTTCTTGTGGTTCCGAACATT
2611
2612 111_HRV38a    AAGGAAAGCCACTCCAGCACATCAAATTCAGCACCAGCATTAGATGCTGCTGAGACTGGA
2613 112_HRV38b    AAGGAAAGCCACTCCAGCACATCAAATTCAGCACCAGCATTAGATGCTGCTGAGACTGGA
2614 113_HRV38     AAGGAAAGCCACTCCAGCACATCAAATTCAGCACCAGCATTAGATGCTGCTGAGACTGGA
2615 GROUP_20      AAGGAAAGCCACTCCAGCACATCAAATTCAGCACCAGCATTAGATGCTGCTGAGACTGGA
2616
2617 111_HRV38a    CACACCAGTAATGTGCAGCCTGAGGATATGATTGAAACTCGCTATGTACAGACATCACAA
2618 112_HRV38b    CACACCAGTAATGTGCAGCCTGAGGATATGATTGAAACTCGCTATGTACAGACATCACAA
2619 113_HRV38     CACACCAGTAATGTGCAGCCTGAGGATATGATTGAAACTCGCTATGTACAGACATCACAA
2620 GROUP_20      CACACCAGTAATGTGCAGCCTGAGGATATGATTGAAACTCGCTATGTACAGACATCACAA
2621
2622 111_HRV38a    ACTAGAGATGAAATGAGTGTAGAAAGTTTTCTAGGAAGATCAGGTTGTGTACATATATCC
2623 112_HRV38b    ACTAGAGATGAAATGAGTGTAGAAAGTTTTCTAGGAAGATCAGGTTGTGTACATATATCC
2624 113_HRV38     ACTAGAGATGAAATGAGTGTAGAAAGTTTTCTAGGAAGATCAGGTTGTGTACATATATCC
2625 GROUP_20      ACTAGAGATGAAATGAGTGTAGAAAGTTTTCTAGGAAGATCAGGTTGTGTACATATATCC
2626
2627 111_HRV38a    AATCTTGACATAGATTACATTAAT---------------TACAACTCT---GAAGACAAA
2628 112_HRV38b    AATCTTGACATAGATTACATTAAT---------------TACAACTCT---GAAGACAAA
2629 113_HRV38     AATCTTGACATAGATTACATTAAT---------------TACAACTCT---GAAGACAAA
2630 GROUP_20      AATCTTGACATAGATTACATTAAT...............TACAACTCT...GAAGACAAA
2631
2632 111_HRV38a    AACTTTACAACATGGCAAATCAATCTCAAAGAAATGGCTCAAATCAGAAGAAAGTTTGAA
2633 112_HRV38b    AACTTTACAACATGGCAAATCAATCTCAAAGAAATGGCTCAAATCAGAAGAAAGTTTGAA
2634 113_HRV38     AACTTTACAACATGGCAAATCAATCTCAAAGAAATGGCTCAAATCAGAAGAAAGTTTGAA
2635 GROUP_20      AACTTTACAACATGGCAAATCAATCTCAAAGAAATGGCTCAAATCAGAAGAAAGTTTGAA
2636
2637 111_HRV38a    ATGTTTACATATGTGAGATTTGATTCAGAAGTTACATTAG-TCCCATGTATAGCAGCACA
2638 112_HRV38b    ATGTTTACATATGTGAGATTTGATTCAGAAGTTACATTAG-TCCCATGTATAGCAGCACA
2639 113_HRV38     ATGTTTACATATGTGAGATTTGATTCAGAAGTTACATTAG-TCCCATGTATAGCAGCACA
2640 GROUP_20      ATGTTTACATATGTGAGATTTGATTCAGAAGTTACATTAG.TCCCATGTATAGCAGCACA
2641
2642 111_HRV38a    AAATGAAGGTGTGGGGCATGTTGTTATGCAGTATATGTATGTCCCTCCAGGGGCACCATT
2643 112_HRV38b    AAATGAAGGTGTGGGGCATGTTGTTATGCAGTATATGTATGTCCCTCCAGGGGCACCATT
2644 113_HRV38     AAATGAAGGTGTGGGGCATGTTGTTATGCAGTATATGTATGTCCCTCCAGGGGCACCATT
2645 GROUP_20      AAATGAAGGTGTGGGGCATGTTGTTATGCAGTATATGTATGTCCCTCCAGGGGCACCATT
2646
2647 111_HRV38a    ACCCAGGAAGAGAGATGATTACACTTGGCAATCTGGTACAAATGCCTCTGTTTTCTGGCA
2648 112_HRV38b    ACCCAGGAAGAGAGATGATTACACTTGGCAATCTGGTACAAATGCCTCTGTTTTCTGGCA
2649 113_HRV38     ACCCAGGAAGAGAGATGATTACACTTGGCAATCTGGTACAAATGCCTCTGTTTTCTGGCA
2650 GROUP_20      ACCCAGGAAGAGAGATGATTACACTTGGCAATCTGGTACAAATGCCTCTGTTTTCTGGCA
2651
2652 111_HRV38a    ATATGGTCAGACATATCCTCGATTTTCCTTACCTTTCTTAAGCATTGCATCTGTCTATTA
2653 112_HRV38b    ATATGGTCAGACATATCCTCGATTTTCCTTACCTTTCTTAAGCATTGCATCTGTCTATTA
2654 113_HRV38     ATATGGTCAGACATATCCTCGATTTTCCTTACCTTTCTTAAGCATTGCATCTGTCTATTA
2655 GROUP_20      ATATGGTCAGACATATCCTCGATTTTCCTTACCTTTCTTAAGCATTGCATCTGTCTATTA
2656
2657 111_HRV38a    TATGTTTTATGATGGATATGATGGGGACTCAACAGAATCACATTATGGGACAGCGGTGAC
```

FIG. D13 CONT'D

```
09.trace                                                                                                9/20/2007 5:05 PM 2658  112_HRV38b   TATGTTTTATGATGGATATGATGGGGACTCAACAGAATCACATTATGGGACAGCGGTGAC
2659  113_HRV38    TATGTTTTATGATGGATATGATGGGGACTCAACAGAATCACATTATGGGACAGCGGTGAC
2660  GROUP_20     TATGTTTTATGATGGATATGATGGGGACTCAACAGAATCACATTATGGGACAGCGGTGAC
2661
2662  111_HRV38a   CAATGATATGGGGACACTTTGTTCAAGAATAGTCACTGAAAATCATGGGACCCAAGTGAA
2663  112_HRV38b   CAATGATATGGGGACACTTTGTTCAAGAATAGTCACTGAAAATCATGGGACCCAAGTGAA
2664  113_HRV38    CAATGATATGGGGACACTTTGTTCAAGAATAGTCACTGAAAATCATGGGACCCAAGTGAA
2665  GROUP_20     CAATGATATGGGGACACTTTGTTCAAGAATAGTCACTGAAAATCATGGGACCCAAGTGAA
2666
2667  111_HRV38a   GATAACAACTAGAATTTATCATAAGGCAAAACATGTAAAAGCCTGGTGTCCAAGACCCCC
2668  112_HRV38b   GATAACAACTAGAATTTATCATAAGGCAAAACATGTAAAAGCCTGGTGTCCAAGACCCCC
2669  113_HRV38    GATAACAACTAGAATTTATCATAAGGCAAAACATGTAAAAGCCTGGTGTCCAAGACCCCC
2670  GROUP_20     GATAACAACTAGAATTTATCATAAGGCAAAACATGTAAAAGCCTGGTGTCCAAGACCCCC
2671
2672  111_HRV38a   AAGGGCAGTTGAATATAGA-CATACACATGTTAACAATTACAAAC-CAGACC---AAGGG
2673  112_HRV38b   AAGGGCAGTTGAATATAGA-CATACACATGTTAACAATTACAAAC-CAGACC---AAGGG
2674  113_HRV38    AAGGGCAGTTGAATATAGA-CATACACATGTTAACAATTACAAAC-CAGACC---AAGGG
2675  GROUP_20     AAGGGCAGTTGAATATAGA.CATACACATGTTAACAATTACAAAC.CAGACC...AAGGG
2676
2677  111_HRV38a   GAAG------TAACCACTA---TGATTCCAACTAGAACCAACATAAGAACCATCGTAA--
2678  112_HRV38b   GAAG------TAACCACTA---TGATTCCAACTAGAACCAACATAAGAACCATCGTAA--
2679  113_HRV38    GAAG------TAACCACTA---TGATTCCAACTAGAACCAACATAAGAACCATCGTAA--
2680  GROUP_20     GAAG......TAACCACTA...TGATTCCAACTAGAACCAACATAAGAACCATCGTAA..
2681
2682  111_HRV38a   ----ATGTA------------
2683  112_HRV38b   ----ATGTC------------
2684  113_HRV38    ----ATGTT------------
2685  GROUP_20     ....ATGT-............
2686
2687
2688
2689  GROUP  21:
2690
2691  114_HRV60    AATCCAGTAGAAAGCTACATAGATGGGGTCTTAAACGAAGTCCTTGTGGTTCCAAACATT
2692  115_HRV60a   AATCCAGTAGAAAGCTACATAGATGGGGTCTTAAACGAAGTCCTTGTGGTTCCAAACATT
2693  116_HRV60b   AATCCAGTAGAAAGCTACATAGATGGGGTCTTAAACGAAGTCCTTGTGGTTCCAAACATT
2694  GROUP_21     AATCCAGTAGAAAGCTACATAGATGGGGTCTTAAACGAAGTCCTTGTGGTTCCAAACATT
2695
2696  114_HRV60    AGGGAGAGCCAACCCACTACTTCTAATTCTGCTCCAGCATTGGATGCTGCTGAGACTGGT
2697  115_HRV60a   AGGGAGAGCCAACCCACTACTTCTAATTCTGCTCCAGCATTGGATGCTGCTGAGACTGGT
2698  116_HRV60b   AGGGAGAGCCAACCCACTACTTCTAATTCTGCTCCAGCATTGGATGCTGCTGAGACTGGT
2699  GROUP_21     AGGGAGAGCCAACCCACTACTTCTAATTCTGCTCCAGCATTGGATGCTGCTGAGACTGGT
2700
2701  114_HRV60    CACACTAGTAATGTACAGCCTGAGGACGTGATTGAAACACGTTATGTGCAGATTACACAA
2702  115_HRV60a   CACACTAGTAATGTACAGCCTGAGGACGTGATTGAAACACGTTATGTGCAGATTACACAA
2703  116_HRV60b   CACACTAGTAATGTACAGCCTGAGGACGTGATTGAAACACGTTATGTGCAGATTACACAA
2704  GROUP_21     CACACTAGTAATGTACAGCCTGAGGACGTGATTGAAACACGTTATGTGCAGATTACACAA
2705
2706  114_HRV60    ACTAGAGATGAGATGAGTGTTGAGAGCTTCCTCGGCAGATCTGGATGTATTCATATTTCC
2707  115_HRV60a   ACTAGAGATGAGATGAGTGTTGAGAGCTTCCTCGGCAGATCTGGATGTATTCATATTTCC
2708  116_HRV60b   ACTAGAGATGAGATGAGTGTTGAGAGCTTCCTCGGCAGATCTGGATGTATTCATATTTCC
2709  GROUP_21     ACTAGAGATGAGATGAGTGTTGAGAGCTTCCTCGGCAGATCTGGATGTATTCATATTTCC
2710
2711  114_HRV60    AAATTAGAAATTGACTATAGTAAC---------------TACAATGAG---GAGAATAAA
2712  115_HRV60a   AAATTAGAAATTGACTATAGTAAC---------------TACAATGAG---GAGAATAAA
2713  116_HRV60b   AAATTAGAAATTGACTATAGTAAC---------------TACAATGAG---GAGAATAAA
2714  GROUP_21     AAATTAGAAATTGACTATAGTAAC...............TACAATGAG...GAGAATAAA
2715
2716  114_HRV60    AATTTCACAACTTGGCAAATTAACCTAAAGGAAATGGCACAAATAAGAAGAAAGTTTGAA
2717  115_HRV60a   AATTTCACAACTTGGCAAATTAACCTAAAGGAAATGGCACAAATAAGAAGAAAGTTTGAA
2718  116_HRV60b   AATTTCACAACTTGGCAAATTAACCTAAAGGAAATGGCACAAATAAGAAGAAAGTTTGAA
2719  GROUP_21     AATTTCACAACTTGGCAAATTAACCTAAAGGAAATGGCACAAATAAGAAGAAAGTTTGAA
2720
2721  114_HRV60    TTATTTACATATGTAAGATTTGATTCAGAATTGACTCTGG-TCCCATGCATAGCAGCAAA
2722  115_HRV60a   TTATTTACATATGTAAGATTTGATTCAGAATTGACTCTGG-TCCCATGCATAGCAGCAAA
```

FIG. D13 CONT'D

```
09.trace                                                                    9/20/2007 5:05 PM 2723 116_HRV60b   TTATTTACATATGTAAGATTTGATTCAGAATTGACTCTGG-TCCCCATGCATAGCAGCAAA
2724 GROUP_21    TTATTTACATATGTAAGATTTGATTCAGAATTGACTCTGG.TCCCCATGCATAGCAGCAAA
2725
2726 114_HRV60   AAATGATGGCATAGGTCATGTTGTCATGCAATACATGTATGTCCCCCCAGGAGCACCATT
2727 115_HRV60a  AAATGATGGCATAGGTCATGTTGTCATGCAATACATGTATGTCCCCCCAGGAGCACCATT
2728 116_HRV60b  AAATGATGGCATAGGTCATGTTGTCATGCAATACATGTATGTCCCCCCAGGAGCACCATT
2729 GROUP_21    AAATGATGGCATAGGTCATGTTGTCATGCAATACATGTATGTCCCCCCAGGAGCACCATT
2730
2731 114_HRV60   ACCTACTAAAAGAGACGATTACACATGGCAATCTGGCACAAATGCTTCTGTATTTTGGCA
2732 115_HRV60a  ACCTACTAAAAGAGACGATTACACATGGCAATCTGGCACAAATGCTTCTGTATTTTGGCA
2733 116_HRV60b  ACCTACTAAAAGAGACGATTACACATGGCAATCTGGCACAAATGCTTCTGTATTTTGGCA
2734 GROUP_21    ACCTACTAAAAGAGACGATTACACATGGCAATCTGGCACAAATGCTTCTGTATTTTGGCA
2735
2736 114_HRV60   GCATGGACAAACATACCCTAGATTTTCACTTCCATTTCTAAGTATTGCATCTGCCTACTA
2737 115_HRV60a  GCATGGACAAACATACCCTAGATTTTCACTTCCATTTCTAAGTATTGCATCTGCCTACTA
2738 116_HRV60b  GCATGGACAAACATACCCTAGATTTTCACTTCCATTTCTAAGTATTGCATCTGCCTACTA
2739 GROUP_21    GCATGGACAAACATACCCTAGATTTTCACTTCCATTTCTAAGTATTGCATCTGCCTACTA
2740
2741 114_HRV60   CATGTTTTATGATGGTTATGATGGTCACTCAACTGAATCACATTATGGGACGGTTGTGAC
2742 115_HRV60a  CATGTTTTATGATGGTTATGATGGTCACTCAACTGAATCACATTATGGGACGGTTGTGAC
2743 116_HRV60b  CATGTTTTATGATGGTTATGATGGTCACTCAACTGAATCACATTATGGGACGGTTGTGAC
2744 GROUP_21    CATGTTTTATGATGGTTATGATGGTCACTCAACTGAATCACATTATGGGACGGTTGTGAC
2745
2746 114_HRV60   CAATGACATGGGAACGTTGTGCTCCAGAATAGTTACTGAACACCATGGTACACAGGTTCA
2747 115_HRV60a  CAATGACATGGGAACGTTGTGCTCCAGAATAGTTACTGAACACCATGGTACACAGGTTCA
2748 116_HRV60b  CAATGACATGGGAACGTTGTGCTCCAGAATAGTTACTGAACACCATGGTACACAGGTTCA
2749 GROUP_21    CAATGACATGGGAACGTTGTGCTCCAGAATAGTTACTGAACACCATGGTACACAGGTTCA
2750
2751 114_HRV60   CGTCGCAACAAGAATATATCATAAAGCAAAGCATGTTAAGGCTTGGTGTCCAAGACCTCC
2752 115_HRV60a  CGTCGCAACAAGAATATATCATAAAGCAAAGCATGTTAAGGCTTGGTGTCCAAGACCTCC
2753 116_HRV60b  CGTCGCAACAAGAATATATCATAAAGCAAAGCATGTTAAGGCTTGGTGTCCAAGACCTCC
2754 GROUP_21    CGTCGCAACAAGAATATATCATAAAGCAAAGCATGTTAAGGCTTGGTGTCCAAGACCTCC
2755
2756 114_HRV60   AAGGGCAGTTGAATATAGA-CACACACATGTAAACAACTATAGAC-CAGATG---ATGGA
2757 115_HRV60a  AAGGGCAGTTGAATATAGA-CACACACATGTAAACAACTATAGAC-CAGATG---ATGGA
2758 116_HRV60b  AAGGGCAGTTGAATATAGA-CACACACATGTAAACAACTATAGAC-CAGATG---ATGGA
2759 GROUP_21    AAGGGCAGTTGAATATAGA.CACACACATGTAAACAACTATAGAC.CAGATG...ATGGA
2760
2761 114_HRV60   GAAG------CAGCCATAA---CAATCCCCATTAGAACTGATATACGAGCAATCAGAA--
2762 115_HRV60a  GAAG------CAGCCATAA---CAATCCCCATTAGAACTGATATACGAGCAATCAGAA--
2763 116_HRV60b  GAAG------CAGCCATAA---CAATCCCCATTAGAACTGATATACGAGCAATCAGAA--
2764 GROUP_21    GAAG......CAGCCATAA...CAATCCCCATTAGAACTGATATACGAGCAATCAGAA..
2765
2766 114_HRV60   ----CAGTT------------
2767 115_HRV60a  ----CAGTA------------
2768 116_HRV60b  ----CAGTG------------
2769 GROUP_21    ....CAGT-............
2770
2771
2772
2773 GROUP  22:
2774
2775 117_HRV64a  AACCCAGTTGAACAATACATTGATGGTGTGTTGAATGAAGTTTTGATTGTCCCAAACATC
2776 118_HRV64b  AACCCAGTTGAACAATACATTGATGGTGTGTTGAATGAAGTTTTGATTGTCCCAAACATC
2777 119_HRV64   AACCCAGTTGAACAATACATTGATGGTGTGTTGAATGAAGTTTTGATTGTCCCAAACATC
2778 120_HRV94a  AATCCAGTTGAGAAATACATTGATGGTGTATTGAATGAAGTTTTAGTTGTTCCAAATATC
2779 121_HRV94b  AATCCAGTTGAGAAATACATTGATGGTGTATTGAATGAAGTTTTAGTTGTTCCAAATATC
2780 122_HRV94   AATCCAGTTGAGAAATACATTGATGGTGTATTGAATGAAGTTTTAGTTGTTCCAAATATC
2781 123_HRV22   AACCCTGTAGAGAAATACATTGATGGTGTATTGAATGAAGTATTGGTTGTTCCAAACACA
2782 124_HRV22a  AACCCTGTAGAGAAATACATTGATGGTGTATTGAATGAAGTATTGGTTGTTCCAAACACA
2783 125_HRV22b  AACCCTGTAGAGAAATACATTGATGGTGTATTGAATGAAGTATTGGTTGTTCCAAACACA
2784 GROUP_22    AA-CC-GT-GA--AATACATTGATGGTGT-TTGAATGAAGT-TT--TTGT-CCAAA-A--
2785
2786 117_HRV64a  AATGAGAGCCATCCCAGCACTTCCAATGCAGCGCCAGCTTTAGATGCAGCTGAGACCGGA
2787 118_HRV64b  AATGAGAGCCATCCCAGCACTTCCAATGCAGCGCCAGCTTTAGATGCAGCTGAGACCGGA
```

```
09.trace                                                                         9/20/2007 5:05 PM 2788 119_HRV64    AATGAGAGCCATCCCAGCACTTCCAATGCAGCGCCAGCTTTAGATGCAGCTGAGACCGGA
2789 120_HRV94a   AATGAGAGTCACCCTAGCACATCCAATGCAGCGCCAGCCTTAGATGCTGCCGAAACTGGA
2790 121_HRV94b   AATGAGAGTCACCCTAGCACATCCAATGCAGCGCCAGCCTTAGATGCTGCCGAAACTGGA
2791 122_HRV94    AATGAGAGTCACCCTAGCACATCCAATGCAGCGCCAGCCTTAGATGCTGCCGAAACTGGA
2792 123_HRV22    AATGAAAGTCACCCCAGTACATCAAATGCTGCACCAGCACTAGATGCTGCTGAAACTGGA
2793 124_HRV22a   AATGAAAGTCACCCCAGTACATCAAATGCTGCACCAGCACTAGATGCTGCTGAAACTGGA
2794 125_HRV22b   AATGAAAGTCACCCCAGTACATCAAATGCTGCACCAGCACTAGATGCTGCTGAAACTGGA
2795 GROUP_22     AATGA-AG-CA-CC-AG-AC-TC-AATGC-GC-CCAGC--TAGATGC-GC-GA-AC-GGA
2796
2797 117_HRV64a   CACACCAGTAATGTACAGCCTGAAGATATGATTGAAACGCGCTATGTACAAAACACTCAA
2798 118_HRV64b   CACACCAGTAATGTACAGCCTGAAGATATGATTGAAACGCGCTATGTACAAAACACTCAA
2799 119_HRV64    CACACCAGTAATGTACAGCCTGAAGATATGATTGAAACGCGCTATGTACAAAACACTCAA
2800 120_HRV94a   CACACAAGCAATGTACAACCTGAGGATATGATTGAAACACGCTATGTACAAAACACTCAA
2801 121_HRV94b   CACACAAGCAATGTACAACCTGAGGATATGATTGAAACACGCTATGTACAAAACACTCAA
2802 122_HRV94    CACACAAGCAATGTACAACCTGAGGATATGATTGAAACACGCTATGTACAAAACACTCAA
2803 123_HRV22    CACACAAGCAATGTGCAGCCAGAAGACATGATAGAAACACGCTATGTGTTAAATTCACAA
2804 124_HRV22a   CACACAAGCAATGTGCAGCCAGAAGACATGATAGAAACACGCTATGTGTTAAATTCACAA
2805 125_HRV22b   CACACAAGCAATGTGCAGCCAGAAGACATGATAGAAACACGCTATGTGTTAAATTCACAA
2806 GROUP_22     CACAC-AG-AATGT-CA-CC-GA-GA-ATGAT-GAAAC-CGCTATGT---AAA--C-CAA
2807
2808 117_HRV64a   ACTAGAGATGAAATGAGCATTGAGAGTTTCTTGGGCAGGTCTGGTTGTATACACATATCA
2809 118_HRV64b   ACTAGAGATGAAATGAGCATTGAGAGTTTCTTGGGCAGGTCTGGTTGTATACACATATCA
2810 119_HRV64    ACTAGAGATGAAATGAGCATTGAGAGTTTCTTGGGCAGGTCTGGTTGTATACACATATCA
2811 120_HRV94a   ACAAGGGATGAAATGAGCATTGAAAGCTTCTTGGGAAGATCTGGCTGTATACACATAGCA
2812 121_HRV94b   ACAAGGGATGAAATGAGCATTGAAAGCTTCTTGGGAAGATCTGGCTGTATACACATAGCA
2813 122_HRV94    ACAAGGGATGAAATGAGCATTGAAAGCTTCTTGGGAAGATCTGGCTGTATACACATAGCA
2814 123_HRV22    ACTAGAGATGAAATGAGTATTGAGAGCTTCCTGGGAAGATCTGGTTGCATACATATATCA
2815 124_HRV22a   ACTAGAGATGAAATGAGTATTGAGAGCTTCCTGGGAAGATCTGGTTGCATACATATATCA
2816 125_HRV22b   ACTAGAGATGAAATGAGTATTGAGAGCTTCCTGGGAAGATCTGGTTGCATACATATATCA
2817 GROUP_22     AC-AG-GATGAAATGAG-ATTGA-AG-TTC-TGGG-AG-TCTGG-TG-ATACA-ATA-CA
2818
2819 117_HRV64a   GATTTAAAAGTAAATTATACTGGG---------------TATAATGAT---GAAGGTAAC
2820 118_HRV64b   GATTTAAAAGTAAATTATACTGGG---------------TATAATGAT---GAAGGTAAC
2821 119_HRV64    GATTTAAAAGTAAATTATACTGGG---------------TATAATGAT---GAAGGTAAC
2822 120_HRV94a   CATCTAGAGATCAAGTATGATGGT---------------TACAATGAT---GCTGGCAAC
2823 121_HRV94b   CATCTAGAGATCAAGTATGATGGT---------------TACAATGAT---GCTGGCAAC
2824 122_HRV94    CATCTAGAGATCAAGTATGATGGT---------------TACAATGAT---GCTGGCAAC
2825 123_HRV22    CACTTAGAAGTAAAATACACAGGG---------------TATAATGAA---GAGGGTAAT
2826 124_HRV22a   CACTTAGAAGTAAAATACACAGGG---------------TATAATGAA---GAGGGTAAT
2827 125_HRV22b   CACTTAGAAGTAAAATACACAGGG---------------TATAATGAA---GAGGGTAAT
2828 GROUP_22     -A--TA-A--T-AA-TA----GG-.........TA-AATGA-...G--GG-AA-
2829
2830 117_HRV64a   AATTTTAACAAATGGCAGATCACCTTGAAAGAAATGGCTCAGATAAGAAGGAAGTATGAA
2831 118_HRV64b   AATTTTAACAAATGGCAGATCACCTTGAAAGAAATGGCTCAGATAAGAAGGAAGTATGAA
2832 119_HRV64    AATTTTAACAAATGGCAGATCACCTTGAAAGAAATGGCTCAGATAAGAAGGAAGTATGAA
2833 120_HRV94a   AATTTCCAATCATGGCAAATTACCCTAAAAGAAATGGCACAAATAAGAAGGAAATTTGAA
2834 121_HRV94b   AATTTCCAATCATGGCAAATTACCCTAAAAGAAATGGCACAAATAAGAAGGAAATTTGAA
2835 122_HRV94    AATTTCCAATCATGGCAAATTACCCTAAAAGAAATGGCACAAATAAGAAGGAAATTTGAA
2836 123_HRV22    AACTTTAACATATGGCAAATTAACCCTTAAAGAGATGGCTCAGATAAGAAGGAAGTTTGAG
2837 124_HRV22a   AACTTTAACATATGGCAAATTAACCCTTAAAGAGATGGCTCAGATAAGAAGGAAGTTTGAG
2838 125_HRV22b   AACTTTAACATATGGCAAATTAACCCTTAAAGAGATGGCTCAGATAAGAAGGAAGTTTGAG
2839 GROUP_22     AA-TT--A---ATGGCA-AT-A-C-T-AAAGA-ATGGC-CA-ATAAGAAGGAA-T-TGA-
2840
2841 117_HRV64a   TTATTTACATATGTTAGATTTGATTCTGAAATAACCTTAG-TGCCTTGCATATCTTCTCA
2842 118_HRV64b   TTATTTACATATGTTAGATTTGATTCTGAAATAACCTTAG-TGCCTTGCATATCTTCTCA
2843 119_HRV64    TTATTTACATATGTTAGATTTGATTCTGAAATAACCTTAG-TGCCTTGCATATCTTCTCA
2844 120_HRV94a   CTATTTACTTATGTTAGATTTGATTCAGAAATAACTTTAG-TACCTTGCATATCATCTCA
2845 121_HRV94b   CTATTTACTTATGTTAGATTTGATTCAGAAATAACTTTAG-TACCTTGCATATCATCTCA
2846 122_HRV94    CTATTTACTTATGTTAGATTTGATTCAGAAATAACTTTAG-TACCTTGCATATCATCTCA
2847 123_HRV22    CTATTTACATATCTCAGGTTTGATTCTGAAATCACTTTGG-TACCATGCATTGCTTCACA
2848 124_HRV22a   CTATTTACATATCTCAGGTTTGATTCTGAAATCACTTTGG-TACCATGCATTGCTTCACA
2849 125_HRV22b   CTATTTACATATCTCAGGTTTGATTCTGAAATCACTTTGG-TACCATGCATTGCTTCACA
2850 GROUP_22     -TATTTAC-TAT-T-AG-TTTGATTC-GAAAT-AC-TT-G.T-CC-TGCAT--C-TC-CA
2851
2852 117_HRV64a   GAGTGCTAACATTGGTCATGTTGTTATGCAATATATGTATGTCCCTCCTGGAGCTCCAAT
```

FIG. D13 CONT'D

09.trace                                                                9/20/2007 5:05 PM

```
2853 118_HRV64b    GAGTGCTAACATTGGTCATGTTGTTATGCAATATATGTATGTCCCTCCTGGAGCTCCAAT
2854 119_HRV64     GAGTGCTAACATTGGTCATGTTGTTATGCAATATATGTATGTCCCTCCTGGAGCTCCAAT
2855 120_HRV94a    AAGTGCTAATATTGGTCATGTTGTCATGCAGTACATGTATGTTCCTCCTGGAGCTCCAAA
2856 121_HRV94b    AAGTGCTAATATTGGTCATGTTGTCATGCAGTACATGTATGTTCCTCCTGGAGCTCCAAA
2857 122_HRV94     AAGTGCTAATATTGGTCATGTTGTCATGCAGTACATGTATGTTCCTCCTGGAGCTCCAAA
2858 123_HRV22     AAGTAAAAACATTGGTCATGTGGTCATGCAATACATGTATGTTCCGCCTGGAGCTCCTAA
2859 124_HRV22a    AAGTAAAAACATTGGTCATGTGGTCATGCAATACATGTATGTTCCGCCTGGAGCTCCTAA
2860 125_HRV22b    AAGTAAAAACATTGGTCATGTGGTCATGCAATACATGTATGTTCCGCCTGGAGCTCCTAA
2861 GROUP_22      -AGT---AA-ATTGGTCATGT-GT-ATGCA-TA-ATGTATGT-CC-CCTGGAGCTCC-A-
2862
2863 117_HRV64a    ACCAACCAAAAGAAATGATTACGTCTGGCAGTCAGGCACCAATGCATCCATCTTTTGGCA
2864 118_HRV64b    ACCAACCAAAAGAAATGATTACGTCTGGCAGTCAGGCACCAATGCATCCATCTTTTGGCA
2865 119_HRV64     ACCAACCAAAAGAAATGATTACGTCTGGCAGTCAGGCACCAATGCATCCATCTTTTGGCA
2866 120_HRV94a    ACCAGACAAAAGAGATGATTATGTTTGGCAATCAGGAACTAATGCATCTATATTCTGGCA
2867 121_HRV94b    ACCAGACAAAAGAGATGATTATGTTTGGCAATCAGGAACTAATGCATCTATATTCTGGCA
2868 122_HRV94     ACCAGACAAAAGAGATGATTATGTTTGGCAATCAGGAACTAATGCATCTATATTCTGGCA
2869 123_HRV22     ACCTGAAAAGAGAGATGACTACACATGGCAATCTGGCACTAATGCATCTGTTTTCTGGCA
2870 124_HRV22a    ACCTGAAAAGAGAGATGACTACACATGGCAATCTGGCACTAATGCATCTGTTTTCTGGCA
2871 125_HRV22b    ACCTGAAAAGAGAGATGACTACACATGGCAATCTGGCACTAATGCATCTGTTTTCTGGCA
2872 GROUP_22      ACC----AA-AGA-ATGA-TA----TGGCA-TC-GG-AC-AATGCATC--T-TT-TGGCA
2873
2874 117_HRV64a    ACACGGTCAACCATACCCTCGATTTTCTCTCCCTTTCCTTAGCATAGCCTCAGCATATTA
2875 118_HRV64b    ACACGGTCAACCATACCCTCGATTTTCTCTCCCTTTCCTTAGCATAGCCTCAGCATATTA
2876 119_HRV64     ACACGGTCAACCATACCCTCGATTTTCTCTCCCTTTCCTTAGCATAGCCTCAGCATATTA
2877 120_HRV94a    ACATGGTCAACCCTACCCTCGATTCTCACTTCCATTCTTAGTATAGCCTCAGCATATTA
2878 121_HRV94b    ACATGGTCAACCCTACCCTCGATTCTCACTTCCATTCTTAGTATAGCCTCAGCATATTA
2879 122_HRV94     ACATGGTCAACCCTACCCTCGATTCTCACTTCCATTTCTTAGTATAGCCTCAGCATATTA
2880 123_HRV22     GCATGGTCAACCTTATCCCCGATTCTCACTCCCTTTCCTCAGTGTAGCTTCAGCATATTA
2881 124_HRV22a    GCATGGTCAACCTTATCCCCGATTCTCACTCCCTTTCCTCAGTGTAGCTTCAGCATATTA
2882 125_HRV22b    GCATGGTCAACCTTATCCCCGATTCTCACTCCCTTTCCTCAGTGTAGCTTCAGCATATTA
2883 GROUP_22      -CA-GGTCAACC-TA-CC-CGATT-TC-CT-CC-TT-CT-AG--TAGC-TCAGCATATTA
2884
2885 117_HRV64a    CATGTTTTATGATGGTTATGACGGTGG---ACCTGGTTCCCGTTATGGCGCAGTGGTGAC
2886 118_HRV64b    CATGTTTTATGATGGTTATGACGGTGG---ACCTGGTTCCCGTTATGGCGCAGTGGTGAC
2887 119_HRV64     CATGTTTTATGATGGTTATGACGGTGG---ACCTGGTTCCCGTTATGGCGCAGTGGTGAC
2888 120_HRV94a    CATGTTCTATGATGGTTATGATGGTGG---ACCTGGCTCACGCTATGGCACAGTGGTGAC
2889 121_HRV94b    CATGTTCTATGATGGTTATGATGGTGG---ACCTGGCTCACGCTATGGCACAGTGGTGAC
2890 122_HRV94     CATGTTCTATGATGGTTATGATGGTGG---ACCTGGCTCACGCTATGGCACAGTGGTGAC
2891 123_HRV22     CATGTTTTATGATGGGTATGATGGAGG---TCCCGATCACGTTATGGAGCAGTGGTAAC
2892 124_HRV22a    CATGTTTTATGATGGGTATGATGGAGG---TCCCGGATCACGTTATGGAGCAGTGGTAAC
2893 125_HRV22b    CATGTTTTATGATGGGTATGATGGAGG---TCCCGGATCACGTTATGGAGCAGTGGTAAC
2894 GROUP_22      CATGTT-TATGATGG-TATGA-GG-GG...-CC-GG-TC-CG-TATGG--CAGTGGT-AC
2895
2896 117_HRV64a    AAATGATATGGGCACTTTGTGTTCTAGAATTGTGACTGAGGAACACACAACACAGGTCAA
2897 118_HRV64b    AAATGATATGGGCACTTTGTGTTCTAGAATTGTGACTGAGGAACACACAACACAGGTCAA
2898 119_HRV64     AAATGATATGGGCACTTTGTGTTCTAGAATTGTGACTGAGGAACACACAACACAGGTCAA
2899 120_HRV94a    AAATGACATGGGAACATTATGCTCCAGGATTGTGACTGAGGAGCACAAGACACAGGTTAA
2900 121_HRV94b    AAATGACATGGGAACATTATGCTCCAGGATTGTGACTGAGGAGCACAAGACACAGGTTAA
2901 122_HRV94     AAATGACATGGGAACATTATGCTCCAGGATTGTGACTGAGGAGCACAAGACACAGGTTAA
2902 123_HRV22     AAATGATATGGGCACACTGTGCTCTAGGATTGTGACTGAAGAACACCAGACACAAGTCAA
2903 124_HRV22a    AAATGATATGGGCACACTGTGCTCTAGGATTGTGACTGAAGAACACCAGACACAAGTCAA
2904 125_HRV22b    AAATGATATGGGCACACTGTGCTCTAGGATTGTGACTGAAGAACACCAGACACAAGTCAA
2905 GROUP_22      AAATGA-ATGGG-AC--T-TG-TC-AG--ATTGTGACTGA-GA-CAC---ACACA-GT-AA
2906
2907 117_HRV64a    CATCACTACTAGGGTTTATCACAAAGCAAAACATGTCAAGGCATGGTGTCCACGGCCCCC
2908 118_HRV64b    CATCACTACTAGGGTTTATCACAAAGCAAAACATGTCAAGGCATGGTGTCCACGGCCCCC
2909 119_HRV64     CATCACTACTAGGGTTTATCACAAAGCAAAACATGTCAAGGCATGGTGTCCACGGCCCCC
2910 120_HRV94a    CATCACTACTAGAGTGTACCACAAAGCAAAACATGTGAAAGCGTGGTGCCCGCGCCCTCC
2911 121_HRV94b    CATCACTACTAGAGTGTACCACAAAGCAAAACATGTGAAAGCGTGGTGCCCGCGCCCTCC
2912 122_HRV94     CATCACTACTAGAGTGTACCACAAAGCAAAACATGTGAAAGCGTGGTGCCCGCGCCCTCC
2913 123_HRV22     AATTACAACTAGAGTGTACCACAAAGCAAAACATGTAAAGGCATGGTGCCCACGTCCTCC
2914 124_HRV22a    AATTACAACTAGAGTGTACCACAAAGCAAAACATGTAAAGGCATGGTGCCCACGTCCTCC
2915 125_HRV22b    AATTACAACTAGAGTGTACCACAAAGCAAAACATGTAAAGGCATGGTGCCCACGTCCTCC
2916 GROUP_22      -AT-AC-ACTAG-GT-TA-CACAAAGCAAAACATGT-AA-GC-TGGTG-CC-CG-CC-CC
2917
```

FIG. D13 CONT'D

```
09.trace                                                                      9/20/2007 5:05 PM 2918  117_HRV64a    AAGAGCTGTTGGATATACA-CATACAAATGTCACCAATTATAAAC-CATCCA---AAGGA
2919  118_HRV64b    AAGAGCTGTTGGATATACA-CATACAAATGTCACCAATTATAAAC-CATCCA---AAGGA
2920  119_HRV64     AAGAGCTGTTGGATATACA-CATACAAATGTCACCAATTATAAAC-CATCCA---AAGGA
2921  120_HRV94a    AAGAGCTGTTGGATACACA-CATACGCATGTCACTAATTACAAAC-CATCTG---AAGGG
2922  121_HRV94b    AAGAGCTGTTGGATACACA-CATACGCATGTCACTAATTACAAAC-CATCTG---AAGGG
2923  122_HRV94     AAGAGCTGTTGGATACACA-CATACGCATGTCACTAATTACAAAC-CATCTG---AAGGG
2924  123_HRV22     AAGAGCTGTTGGATATACA-CACACACATGTGACAAACTACAAAC-CATCTG---TAGGG
2925  124_HRV22a    AAGAGCTGTTGGATATACA-CACACACATGTGACAAACTACAAAC-CATCTG---TAGGG
2926  125_HRV22b    AAGAGCTGTTGGATATACA-CACACACATGTGACAAACTACAAAC-CATCTG---TAGGG
2927  GROUP_22      AAGAGCTGTTGGATA-ACA.CA-AC--ATGT-AC-AA-TA-AAAC.CATC--...-AGG-
2928
2929  117_HRV64a    GAAT------ACACACCAC---CCGTTCCGTCACGTAACAGCCCCAGAGATATTGTCA--
2930  118_HRV64b    GAAT------ACACACCAC---CCGTTCCGTCACGTAACAGCCCCAGAGATATTGTCA--
2931  119_HRV64     GAAT------ACACACCAC---CCGTTCCGTCACGTAACAGCCCCAGAGATATTGTCA--
2932  120_HRV94a    GAGT------ACAAGCCAC---CTGTCCCAGTTAGGAATAGCCCCAGAGACATTGTCA--
2933  121_HRV94b    GAGT------ACAAGCCAC---CTGTCCCAGTTAGGAATAGCCCCAGAGACATTGTCA--
2934  122_HRV94     GAGT------ACAAGCCAC---CTGTCCCAGTTAGGAATAGCCCCAGAGACATTGTCA--
2935  123_HRV22     GATT------ACACACTAC---CTATCCCAACAAGAGCCAACCCTAGACAAATTTTGA--
2936  124_HRV22a    GATT------ACACACTAC---CTATCCCAACAAGAGCCAACCCTAGACAAATTTTGA--
2937  125_HRV22b    GATT------ACACACTAC---CTATCCCAACAAGAGCCAACCCTAGACAAATTTTGA--
2938  GROUP_22      GA-T......ACA--C-AC...C--T-CC-----G----A-CCC-AGA-A-ATT-T-A..
2939
2940  117_HRV64a    ----CAGTG-----------
2941  118_HRV64b    ----CAGTG-----------
2942  119_HRV64     ----CAGTA-----------
2943  120_HRV94a    ----CAGTG-----------
2944  121_HRV94b    ----CAGTC-----------
2945  122_HRV94     ----CAGTA-----------
2946  123_HRV22     ----ATGTA-----------
2947  124_HRV22a    ----ATGTG-----------
2948  125_HRV22b    ----ATGTC-----------
2949  GROUP_22      ....--GT-...........
2950
2951
2952
2953  GROUP  23:
2954
2955  126_HRV82     AATCCAGTTGAAAAGTATGTTGATAGTGTTTTAAACGAGGTATTAGTTGTTCCTAACATT
2956  127_HRV82b    AATCCAGTTGAAAAGTATGTTGATAGTGTTTTAAACGAGGTATTAGTTGTTCCTAACATT
2957  128_HRV82a    AATCCAGTTGAAAAGTATGTTGATAGTGTTTTAAACGAGGTATTAGTTGTTCCTAACATT
2958  GROUP_23      AATCCAGTTGAAAAGTATGTTGATAGTGTTTTAAACGAGGTATTAGTTGTTCCTAACATT
2959
2960  126_HRV82     AATGAAAGTCATCCTAGTACTTCAAATTCAGCTCCTGCCTTGGACGCTGCAGAGACAGGA
2961  127_HRV82b    AATGAAAGTCATCCTAGTACTTCAAATTCAGCTCCTGCCTTGGACGCTGCAGAGACAGGA
2962  128_HRV82a    AATGAAAGTCATCCTAGTACTTCAAATTCAGCTCCTGCCTTGGACGCTGCAGAGACAGGA
2963  GROUP_23      AATGAAAGTCATCCTAGTACTTCAAATTCAGCTCCTGCCTTGGACGCTGCAGAGACAGGA
2964
2965  126_HRV82     CATACAAGTACTGTTCAACCTGAGGACATGATTGAAACACGGTATGTTCAAACATCACAA
2966  127_HRV82b    CATACAAGTACTGTTCAACCTGAGGACATGATTGAAACACGGTATGTTCAAACATCACAA
2967  128_HRV82a    CATACAAGTACTGTTCAACCTGAGGACATGATTGAAACACGGTATGTTCAAACATCACAA
2968  GROUP_23      CATACAAGTACTGTTCAACCTGAGGACATGATTGAAACACGGTATGTTCAAACATCACAA
2969
2970  126_HRV82     ACTAGAGATGAGATGAGCCTTGAGAGTTTCCTAGGGAGATCTGGCTGCATACACATATCA
2971  127_HRV82b    ACTAGAGATGAGATGAGCCTTGAGAGTTTCCTAGGGAGATCTGGCTGCATACACATATCA
2972  128_HRV82a    ACTAGAGATGAGATGAGCCTTGAGAGTTTCCTAGGGAGATCTGGCTGCATACACATATCA
2973  GROUP_23      ACTAGAGATGAGATGAGCCTTGAGAGTTTCCTAGGGAGATCTGGCTGCATACACATATCA
2974
2975  126_HRV82     CACCTAAATGTCAGATACACTG-----------------ATTATAAT---GAAGGTAAT
2976  127_HRV82b    CACCTAAATGTCAGATACACTG-----------------ATTATAAT---GAAGGTAAT
2977  128_HRV82a    CACCTAAATGTCAGATACACTG-----------------ATTATAAT---GAAGGTAAT
2978  GROUP_23      CACCTAAATGTCAGATACACTG.................ATTATAAT...GAAGGTAAT
2979
2980  126_HRV82     AACTTTAGATCATGGCAAATAAGCATAAAGGAAATGGCACAAATTAGAAGGAAGTTTGAA
2981  127_HRV82b    AACTTTAGATCATGGCAAATAAGCATAAAGGAAATGGCACAAATTAGAAGGAAGTTTGAA
2982  128_HRV82a    AACTTTAGATCATGGCAAATAAGCATAAAGGAAATGGCACAAATTAGAAGGAAGTTTGAA
```

FIG. D13 CONT'D

```
09.trace                                                                    9/20/2007 5:05 PM 2983  GROUP_23     AACTTTAGATCATGGCAAATAAGCATAAAGGAAATGGCACAAATTAGAAGGAAGTTTGAA
2984
2985  126_HRV82    CTTTTCACATATGTGAGATTTGATTCAGAAATTACTTTAG-TGCCTTGCATAGCCTCTCA
2986  127_HRV82b   CTTTTCACATATGTGAGATTTGATTCAGAAATTACTTTAG-TGCCTTGCATAGCCTCTCA
2987  128_HRV82a   CTTTTCACATATGTGAGATTTGATTCAGAAATTACTTTAG-TGCCTTGCATAGCCTCTCA
2988  GROUP_23     CTTTTCACATATGTGAGATTTGATTCAGAAATTACTTTAG.TGCCTTGCATAGCCTCTCA
2989
2990  126_HRV82    AAGTAATGATATTGGGCATGTAGTGATGCAATACATGTATGTCCCACCAGGTGCTCCTAA
2991  127_HRV82b   AAGTAATGATATTGGGCATGTAGTGATGCAATACATGTATGTCCCACCAGGTGCTCCTAA
2992  128_HRV82a   AAGTAATGATATTGGGCATGTAGTGATGCAATACATGTATGTCCCACCAGGTGCTCCTAA
2993  GROUP_23     AAGTAATGATATTGGGCATGTAGTGATGCAATACATGTATGTCCCACCAGGTGCTCCTAA
2994
2995  126_HRV82    ACCAGAAAAGAGAGACGACTACACTTGGCAATCTGGAACTAATGCTTCAATTTTCTGGCA
2996  127_HRV82b   ACCAGAAAAGAGAGACGACTACACTTGGCAATCTGGAACTAATGCTTCAATTTTCTGGCA
2997  128_HRV82a   ACCAGAAAAGAGAGACGACTACACTTGGCAATCTGGAACTAATGCTTCAATTTTCTGGCA
2998  GROUP_23     ACCAGAAAAGAGAGACGACTACACTTGGCAATCTGGAACTAATGCTTCAATTTTCTGGCA
2999
3000  126_HRV82    ACATGGACAACCTTACCCTCGCTTCTCACTTCCTTTCTTGAGTATAGCCTCAGCTTACTA
3001  127_HRV82b   ACATGGACAACCTTACCCTCGCTTCTCACTTCCTTTCTTGAGTATAGCCTCAGCTTACTA
3002  128_HRV82a   ACATGGACAACCTTACCCTCGCTTCTCACTTCCTTTCTTGAGTATAGCCTCAGCTTACTA
3003  GROUP_23     ACATGGACAACCTTACCCTCGCTTCTCACTTCCTTTCTTGAGTATAGCCTCAGCTTACTA
3004
3005  126_HRV82    TATGTTCTATGATGGCTATGATGGTGATGCTCCCGGATCGCGATACGGGACCATAGTGAC
3006  127_HRV82b   TATGTTCTATGATGGCTATGATGGTGATGCTCCCGGATCGCGATACGGGACCATAGTGAC
3007  128_HRV82a   TATGTTCTATGATGGCTATGATGGTGATGCTCCCGGATCGCGATACGGGACCATAGTGAC
3008  GROUP_23     TATGTTCTATGATGGCTATGATGGTGATGCTCCCGGATCGCGATACGGGACCATAGTGAC
3009
3010  126_HRV82    AAATGACATGGGTACACTGTGTTCTAGAATTGTAACTGAAGAACACCAGACTCAAGTCAG
3011  127_HRV82b   AAATGACATGGGTACACTGTGTTCTAGAATTGTAACTGAAGAACACCAGACTCAAGTCAG
3012  128_HRV82a   AAATGACATGGGTACACTGTGTTCTAGAATTGTAACTGAAGAACACCAGACTCAAGTCAG
3013  GROUP_23     AAATGACATGGGTACACTGTGTTCTAGAATTGTAACTGAAGAACACCAGACTCAAGTCAG
3014
3015  126_HRV82    CATTACCACAAGAATATATCACAAAGCAAAACATGTGAAAGCGTGGTGTCCACGACCCCC
3016  127_HRV82b   CATTACCACAAGAATATATCACAAAGCAAAACATGTGAAAGCGTGGTGTCCACGACCCCC
3017  128_HRV82a   CATTACCACAAGAATATATCACAAAGCAAAACATGTGAAAGCGTGGTGTCCACGACCCCC
3018  GROUP_23     CATTACCACAAGAATATATCACAAAGCAAAACATGTGAAAGCGTGGTGTCCACGACCCCC
3019
3020  126_HRV82    GAGGGCTGTGGGTTATACA-CACACACATGTTACCAACTACAAGC-CATCAC---AGGGA
3021  127_HRV82b   GAGGGCTGTGGGTTATACA-CACACACATGTTACCAACTACAAGC-CATCAC---AGGGA
3022  128_HRV82a   GAGGGCTGTGGGTTATACA-CACACACATGTTACCAACTACAAGC-CATCAC---AGGGA
3023  GROUP_23     GAGGGCTGTGGGTTATACA.CACACACATGTTACCAACTACAAGC.CATCAC...AGGGA
3024
3025  126_HRV82    GATT------ACAGTGTTG---TTATTCCAGTTAGAGAGAGTCCCAGACAGATTCTTA--
3026  127_HRV82b   GATT------ACAGTGTTG---TTATTCCAGTTAGAGAGAGTCCCAGACAGATTCTTA--
3027  128_HRV82a   GATT------ACAGTGTTG---TTATTCCAGTTAGAGAGAGTCCCAGACAGATTCTTA--
3028  GROUP_23     GATT......ACAGTGTTG...TTATTCCAGTTAGAGAGAGTCCCAGACAGATTCTTA...
3029
3030  126_HRV82    ----ATGTA------------
3031  127_HRV82b   ----ATGTT------------
3032  128_HRV82a   ----ATGTC------------
3033  GROUP_23     ....ATGT-............
3034
3035
3036
3037  GROUP  24:
3038
3039  129_HRV19    AATCCTGTAGAGAAATATGTGGACACCATTCTGAATGAGGTGCTAGTTGTCCCAAATATC
3040  130_HRV19a   AATCCTGTAGAGAAATATGTGGACACCATTCTGAATGAGGTGCTAGTTGTCCCAAATATC
3041  131_HRV19b   AATCCTGTAGAGAAATATGTGGACACCATTCTGAATGAGGTGCTAGTTGTCCCAAATATC
3042  GROUP_24     AATCCTGTAGAGAAATATGTGGACACCATTCTGAATGAGGTGCTAGTTGTCCCAAATATC
3043
3044  129_HRV19    AATGAAAGTCATCCAAGTACATCAAATGCTGCTCCTGCCTTAGATGCAGCCGAGACAGGA
3045  130_HRV19a   AATGAAAGTCATCCAAGTACATCAAATGCTGCTCCTGCCTTAGATGCAGCCGAGACAGGA
3046  131_HRV19b   AATGAAAGTCATCCAAGTACATCAAATGCTGCTCCTGCCTTAGATGCAGCCGAGACAGGA
3047  GROUP_24     AATGAAAGTCATCCAAGTACATCAAATGCTGCTCCTGCCTTAGATGCAGCCGAGACAGGA
```

FIG. D13 CONT'D

```
09.trace                                                                    9/20/2007 5:05 PM
3048
3049  129_HRV19    CATACTAGCAATGTACAGCCTGAGGACATGATCGAAACACGCTATGTTCAAACGTCCCAG
3050  130_HRV19a   CATACTAGCAATGTACAGCCTGAGGACATGATCGAAACACGCTATGTTCAAACGTCCCAG
3051  131_HRV19b   CATACTAGCAATGTACAGCCTGAGGACATGATCGAAACACGCTATGTTCAAACGTCCCAG
3052  GROUP_24     CATACTAGCAATGTACAGCCTGAGGACATGATCGAAACACGCTATGTTCAAACGTCCCAG
3053
3054  129_HRV19    ACTAGGGATGAAATGAGCATAGAAAGTTTTCTTGGCAGATCCGGTTGTGTACATGTTTCA
3055  130_HRV19a   ACTAGGGATGAAATGAGCATAGAAAGTTTTCTTGGCAGATCCGGTTGTGTACATGTTTCA
3056  131_HRV19b   ACTAGGGATGAAATGAGCATAGAAAGTTTTCTTGGCAGATCCGGTTGTGTACATGTTTCA
3057  GROUP_24     ACTAGGGATGAAATGAGCATAGAAAGTTTTCTTGGCAGATCCGGTTGTGTACATGTTTCA
3058
3059  129_HRV19    GAGCTCCAATTAGATTATACCAAT---------------TACAATCAA---GAAAATAAT
3060  130_HRV19a   GAGCTCCAATTAGATTATACCAAT---------------TACAATCAA---GAAAATAAT
3061  131_HRV19b   GAGCTCCAATTAGATTATACCAAT---------------TACAATCAA---GAAAATAAT
3062  GROUP_24     GAGCTCCAATTAGATTATACCAAT...............TACAATCAA...GAAAATAAT
3063
3064  129_HRV19    AATTTCAAAACTTGGCAAATAAACTTGAAAGAAATGGCACAGATTAGAAGAAAATTTGAA
3065  130_HRV19a   AATTTCAAAACTTGGCAAATAAACTTGAAAGAAATGGCACAGATTAGAAGAAAATTTGAA
3066  131_HRV19b   AATTTCAAAACTTGGCAAATAAACTTGAAAGAAATGGCACAGATTAGAAGAAAATTTGAA
3067  GROUP_24     AATTTCAAAACTTGGCAAATAAACTTGAAAGAAATGGCACAGATTAGAAGAAAATTTGAA
3068
3069  129_HRV19    CTTTTCACTTACCTCAGATTTGATTCAGAGGTAACATTAG-TCCCTTGCATAGCTGCTAA
3070  130_HRV19a   CTTTTCACTTACCTCAGATTTGATTCAGAGGTAACATTAG-TCCCTTGCATAGCTGCTAA
3071  131_HRV19b   CTTTTCACTTACCTCAGATTTGATTCAGAGGTAACATTAG-TCCCTTGCATAGCTGCTAA
3072  GROUP_24     CTTTTCACTTACCTCAGATTTGATTCAGAGGTAACATTAG.TCCCTTGCATAGCTGCTAA
3073
3074  129_HRV19    AAGTAAAAACATTGGACATGTTGTTATGCAATACATGTATGTGCCTCCTGGTGCTCCTAT
3075  130_HRV19a   AAGTAAAAACATTGGACATGTTGTTATGCAATACATGTATGTGCCTCCTGGTGCTCCTAT
3076  131_HRV19b   AAGTAAAAACATTGGACATGTTGTTATGCAATACATGTATGTGCCTCCTGGTGCTCCTAT
3077  GROUP_24     AAGTAAAAACATTGGACATGTTGTTATGCAATACATGTATGTGCCTCCTGGTGCTCCTAT
3078
3079  129_HRV19    CCCAAAAACTAGAAATGATTACACATGGCAATCAGGTACTAATGCATCTATATTTTGGCA
3080  130_HRV19a   CCCAAAAACTAGAAATGATTACACATGGCAATCAGGTACTAATGCATCTATATTTTGGCA
3081  131_HRV19b   CCCAAAAACTAGAAATGATTACACATGGCAATCAGGTACTAATGCATCTATATTTTGGCA
3082  GROUP_24     CCCAAAAACTAGAAATGATTACACATGGCAATCAGGTACTAATGCATCTATATTTTGGCA
3083
3084  129_HRV19    ACATGGTCAACCATACCCAAGATTTTCATTACCTTTTCTAAGTATAGCTTCTGCATATTA
3085  130_HRV19a   ACATGGTCAACCATACCCAAGATTTTCATTACCTTTTCTAAGTATAGCTTCTGCATATTA
3086  131_HRV19b   ACATGGTCAACCATACCCAAGATTTTCATTACCTTTTCTAAGTATAGCTTCTGCATATTA
3087  GROUP_24     ACATGGTCAACCATACCCAAGATTTTCATTACCTTTTCTAAGTATAGCTTCTGCATATTA
3088
3089  129_HRV19    CATGTTTTATGATGGGTATGATGGAGATTCACCAGGATCCCGCTATGGAACAATAGTAAC
3090  130_HRV19a   CATGTTTTATGATGGGTATGATGGAGATTCACCAGGATCCCGCTATGGAACAATAGTAAC
3091  131_HRV19b   CATGTTTTATGATGGGTATGATGGAGATTCACCAGGATCCCGCTATGGAACAATAGTAAC
3092  GROUP_24     CATGTTTTATGATGGGTATGATGGAGATTCACCAGGATCCCGCTATGGAACAATAGTAAC
3093
3094  129_HRV19    TAATGATATGGGAACCTTATGCTCCAGAATAGTAACTGATGAACACCAAACACAGGTTGC
3095  130_HRV19a   TAATGATATGGGAACCTTATGCTCCAGAATAGTAACTGATGAACACCAAACACAGGTTGC
3096  131_HRV19b   TAATGATATGGGAACCTTATGCTCCAGAATAGTAACTGATGAACACCAAACACAGGTTGC
3097  GROUP_24     TAATGATATGGGAACCTTATGCTCCAGAATAGTAACTGATGAACACCAAACACAGGTTGC
3098
3099  129_HRV19    AATCACAACTAGAGTATATCATAAAGCTAAACATATAAAAGCTTGGTGCCCACGACCACC
3100  130_HRV19a   AATCACAACTAGAGTATATCATAAAGCTAAACATATAAAAGCTTGGTGCCCACGACCACC
3101  131_HRV19b   AATCACAACTAGAGTATATCATAAAGCTAAACATATAAAAGCTTGGTGCCCACGACCACC
3102  GROUP_24     AATCACAACTAGAGTATATCATAAAGCTAAACATATAAAAGCTTGGTGCCCACGACCACC
3103
3104  129_HRV19    CAGAGCCGTGGAATATACC-CACACTCATGTGACTAATTATAAAC-CCCAGA---CAGGT
3105  130_HRV19a   CAGAGCCGTGGAATATACC-CACACTCATGTGACTAATTATAAAC-CCCAGA---CAGGT
3106  131_HRV19b   CAGAGCCGTGGAATATACC-CACACTCATGTGACTAATTATAAAC-CCCAGA---CAGGT
3107  GROUP_24     CAGAGCCGTGGAATATACC.CACACTCATGTGACTAATTATAAAC.CCCAGA...CAGGT
3108
3109  129_HRV19    GAAG------TCACTCTTC---CAATTGAAATAAGAGATAACCCTAGACATATAAAGA--
3110  130_HRV19a   GAAG------TCACTCTTC---CAATTGAAATAAGAGATAACCCTAGACATATAAAGA--
3111  131_HRV19b   GAAG------TCACTCTTC---CAATTGAAATAAGAGATAACCCTAGACATATAAAGA--
3112  GROUP_24     GAAG......TCACTCTTC...CAATTGAAATAAGAGATAACCCTAGACATATAAAGA..
```

FIG. D13 CONT'D 09.trace                                                                9/20/2007 5:05 PM

```
129_HRV19     ----ATGTA------------
130_HRV19a    ----ATGTG------------
131_HRV19b    ----ATGTC------------
GROUP_24      ....ATGT-............

GROUP 25:

132_HRV13     AATCCTGTTGAAAGGTATGTAGATGAAGTCTTGAATGAAGTTCTTGTAGTACCAAATATC
133_HRV13a    AATCCTGTTGAAAGGTATGTAGATGAAGTCTTGAATGAAGTTCTTGTAGTACCAAATATC
134_HRV13b    AATCCTGTTGAAAGGTATGTAGATGAAGTCTTGAATGAAGTTCTTGTAGTACCAAATATC
135_HRV41     AATCCTGTAGAAAGGTATGTGGATGAGGTCCTGAATGAGGTTCTTGTGGTACCAAATATT
136_HRV41a    AATCCTGTAGAAAGGTATGTGGATGAGGTCCTGAATGAGGTTCTTGTGGTACCAAATATT
137_HRV41b    AATCCTGTAGAAAGGTATGTGGATGAGGTCCTGAATGAGGTTCTTGTGGTACCAAATATT
GROUP_25      AATCCTGT-GAAAGGTATGT-GATGA-GTC-TGAATGA-GTTCTTGT-GTACCAAATAT-

132_HRV13     AGTGAAAGTAGCTCAACTACATCTAATTCAGCTCCAGCCTTAGATGCTGCAGAAACTGGC
133_HRV13a    AGTGAAAGTAGCTCAACTACATCTAATTCAGCTCCAGCCTTAGATGCTGCAGAAACTGGC
134_HRV13b    AGTGAAAGTAGCTCAACTACATCTAATTCAGCTCCAGCCTTAGATGCTGCAGAAACTGGC
135_HRV41     AGTGAAAGCAGTCCAACTACTTCTAATTCAGCTCCAGCCCTAGATGCAGCAGAGACTGGT
136_HRV41a    AGTGAAAGCAGTCCAACTACTTCTAATTCAGCTCCAGCCCTAGATGCAGCAGAGACTGGT
137_HRV41b    AGTGAAAGCAGTCCAACTACTTCTAATTCAGCTCCAGCCCTAGATGCAGCAGAGACTGGT
GROUP_25      AGTGAAAG-AG--CAACTAC-TCTAATTCAGCTCCAGCC-TAGATGC-GCAGA-ACTGG-

132_HRV13     CACACAAGCAGTGTACAACCAGAAGACATGGTTGAAACACGTTATGTCCAAACTTCACAA
133_HRV13a    CACACAAGCAGTGTACAACCAGAAGACATGGTTGAAACACGTTATGTCCAAACTTCACAA
134_HRV13b    CACACAAGCAGTGTACAACCAGAAGACATGGTTGAAACACGTTATGTCCAAACTTCACAA
135_HRV41     CATACCAGTAATGTACAACCAGAGGACATGATTGAAACACGATATGTCCAAACCTCACAA
136_HRV41a    CATACCAGTAATGTACAACCAGAGGACATGATTGAAACACGATATGTCCAAACCTCACAA
137_HRV41b    CATACCAGTAATGTACAACCAGAGGACATGATTGAAACACGATATGTCCAAACCTCACAA
GROUP_25      CA-AC-AG-A-TGTACAACCAGA-GACATG-TTGAAACACG-TATGTCCAAAC-TCACAA

132_HRV13     ACTAGGGATGAAATGAGTGTTGAGAGCTTTTTAGGCAGATCTCGGTTGTATACACATGTCT
133_HRV13a    ACTAGGGATGAAATGAGTGTTGAGAGCTTTTTAGGCAGATCTCGGTTGTATACACATGTCT
134_HRV13b    ACTAGGGATGAAATGAGTGTTGAGAGCTTTTTAGGCAGATCTCGGTTGTATACACATGTCT
135_HRV41     ACTAGAGATGAAATGAGCATAGAAAGCTTTTTAGGTAGATCAGGCTGTGTACATAAGTCC
136_HRV41a    ACTAGAGATGAAATGAGCATAGAAAGCTTTTTAGGTAGATCAGGCTGTGTACATAAGTCC
137_HRV41b    ACTAGAGATGAAATGAGCATAGAAAGCTTTTTAGGTAGATCAGGCTGTGTACATAAGTCC
GROUP_25      ACTAG-GATGAAATGAG--T-GA-AGCTTTTTAGG-AGATC-GG-TGT-TACA-A-GTC-

132_HRV13     ACCATGAACATAGATTATACTAAT---------------TATGATGAT---TCTGTTAAT
133_HRV13a    ACCATGAACATAGATTATACTAAT---------------TATGATGAT---TCTGTTAAT
134_HRV13b    ACCATGAACATAGATTATACTAAT---------------TATGATGAT---TCTGTTAAT
135_HRV41     ACTTTGAATATAGATTATACTGAT---------------TATGATGAT---TCTATCCAG
136_HRV41a    ACTTTGAATATAGATTATACTGAT---------------TATGATGAT---TCTATCCAG
137_HRV41b    ACTTTGAATATAGATTATACTGAT---------------TATGATGAT---TCTATCCAG
GROUP_25      AC--TGAA-ATAGATTATACT-AT...............TATGATGAT...TCT-T--A-

132_HRV13     AATTTTGTGAAATGGAAAATAAGTTTGCAAGAAATGGCCCAAGTGCGCAGAAAATTTGAG
133_HRV13a    AATTTTGTGAAATGGAAAATAAGTTTGCAAGAAATGGCCCAAGTGCGCAGAAAATTTGAG
134_HRV13b    AATTTTGTGAAATGGAAAATAAGTTTGCAAGAAATGGCCCAAGTGCGCAGAAAATTTGAG
135_HRV41     AACTTCAAGAAGTGGAAAATTAGCTTACAGGAGATGGCCCAAGTACGTAGAAAGTTTGAG
136_HRV41a    AACTTCAAGAAGTGGAAAATTAGCTTACAGGAGATGGCCCAAGTACGTAGAAAGTTTGAG
137_HRV41b    AACTTCAAGAAGTGGAAAATTAGCTTACAGGAGATGGCCCAAGTACGTAGAAAGTTTGAG
GROUP_25      AA-TT---GAA-TGGAAAAT-AG-TT-CA-GA-ATGGCCCAAGT-CG-AGAAA-TTTGAG

132_HRV13     TTGTTCACCTATGTAAGATTTGATTCAGAAATAACAATTG-TGCCATGTATAGCCGGGCA
133_HRV13a    TTGTTCACCTATGTAAGATTTGATTCAGAAATAACAATTG-TGCCATGTATAGCCGGGCA
134_HRV13b    TTGTTCACCTATGTAAGATTTGATTCAGAAATAACAATTG-TGCCATGTATAGCCGGGCA
135_HRV41     TTTTTTACGTATGTTAGATTTGACTCAGAAATAACAATTG-TGCCAAGTATAGCTGGACA
136_HRV41a    TTTTTTACGTATGTTAGATTTGACTCAGAAATAACAATTG-TGCCAAGTATAGCTGGACA
137_HRV41b    TTTTTTACGTATGTTAGATTTGACTCAGAAATAACAATTG-TGCCAAGTATAGCTGGACA
GROUP_25      TT-TT--AC-TATGT-AGATTTGA-TCAGAAATAACAATTG.TGCCA-GTATAGC-GG-CA
```

FIG. D13 CONT'D

09.trace                                                                 9/20/2007 5:05 PM

```
3178
3179 132_HRV13    AGGTGGTGATGTCGGACATGTTGTTATGCAATACATGTATGTACCGCCCGGTGCACCCCT
3180 133_HRV13a   AGGTGGTGATGTCGGACATGTTGTTATGCAATACATGTATGTACCGCCCGGTGCACCCCT
3181 134_HRV13b   AGGTGGTGATGTCGGACATGTTGTTATGCAATACATGTATGTACCGCCCGGTGCACCCCT
3182 135_HRV41    GGGTAGTGATGTCGGACATGTTGTCATGCAATACATGTTCGTACCACCTGGCGCACCCCT
3183 136_HRV41a   GGGTAGTGATGTCGGACATGTTGTCATGCAATACATGTTCGTACCACCTGGCGCACCCCT
3184 137_HRV41b   GGGTAGTGATGTCGGACATGTTGTCATGCAATACATGTTCGTACCACCTGGCGCACCCCT
3185 GROUP_25     -GGT-GTGATGTCGGACATGTTGT-ATGCAATACATGT--GTACC-CC-GG-GCACCCCT
3186
3187 132_HRV13    TCCAACGAAGAGAAATGATTACACATGGCAATCTGGCACCAATGCATCTGTTTTCTGGCA
3188 133_HRV13a   TCCAACGAAGAGAAATGATTACACATGGCAATCTGGCACCAATGCATCTGTTTTCTGGCA
3189 134_HRV13b   TCCAACGAAGAGAAATGATTACACATGGCAATCTGGCACCAATGCATCTGTTTTCTGGCA
3190 135_HRV41    CCCAGAAAAGAGAGATGATTACACATGGCAATCTGGCACCAATGCATCTGTATTCTGGCA
3191 136_HRV41a   CCCAGAAAAGAGAGATGATTACACATGGCAATCTGGCACCAATGCATCTGTATTCTGGCA
3192 137_HRV41b   CCCAGAAAAGAGAGATGATTACACATGGCAATCTGGCACCAATGCATCTGTATTCTGGCA
3193 GROUP_25     -CCA---AAGAGA-ATGATTACACATGGCAATCTGGCACCAATGCATCTGT-TTCTGGCA
3194
3195 132_HRV13    ACATGGTCAAATTTACCCCCGATTCTCTTTACCATTTCTTAGTATTGCATCTGCATATTA
3196 133_HRV13a   ACATGGTCAAATTTACCCCCGATTCTCTTTACCATTTCTTAGTATTGCATCTGCATATTA
3197 134_HRV13b   ACATGGTCAAATTTACCCCCGATTCTCTTTACCATTTCTTAGTATTGCATCTGCATATTA
3198 135_HRV41    GTATGGTCAAGTTTACCCTAGGTTTTCTCTACCATTTCTTAGCATTGCTTCCGCATATTA
3199 136_HRV41a   GTATGGTCAAGTTTACCCTAGGTTTTCTCTACCATTTCTTAGCATTGCTTCCGCATATTA
3200 137_HRV41b   GTATGGTCAAGTTTACCCTAGGTTTTCTCTACCATTTCTTAGCATTGCTTCCGCATATTA
3201 GROUP_25     --ATGGTCAA-TTTACCC--G-TT-TCT-TACCATTTCTTAG-ATTGC-TC-GCATATTA
3202
3203 132_HRV13    TATGTTTTATGATGGATATAATGGAGATTCCTCAGATGCACGCTATGGGACAACAATCAC
3204 133_HRV13a   TATGTTTTATGATGGATATAATGGAGATTCCTCAGATGCACGCTATGGGACAACAATCAC
3205 134_HRV13b   TATGTTTTATGATGGATATAATGGAGATTCCTCAGATGCACGCTATGGGACAACAATCAC
3206 135_HRV41    CATGTTTTATGATGGTTATGAAGAAGGCTCTACAAATGCACGCTATGGAACAACAGTCAC
3207 136_HRV41a   CATGTTTTATGATGGTTATGAAGAAGGCTCTACAAATGCACGCTATGGAACAACAGTCAC
3208 137_HRV41b   CATGTTTTATGATGGTTATGAAGAAGGCTCTACAAATGCACGCTATGGAACAACAGTCAC
3209 GROUP_25     -ATGTTTTATGATGG-TAT-A-G-AG--TC--CA-ATGCACGCTATGG-ACAACA-TCAC
3210
3211 132_HRV13    TAATGATATGGGCACACTTTGCTTCAGAATAGTAACTGAAGAACATACTAACAAGGTCAA
3212 133_HRV13a   TAATGATATGGGCACACTTTGCTTCAGAATAGTAACTGAAGAACATACTAACAAGGTCAA
3213 134_HRV13b   TAATGATATGGGCACACTTTGCTTCAGAATAGTAACTGAAGAACATACTAACAAGGTCAA
3214 135_HRV41    AAATGACATGGGTACATTATGCTTTAGAATAGTTACTGAAGAACACACCAACAAAGTTAA
3215 136_HRV41a   AAATGACATGGGTACATTATGCTTTAGAATAGTTACTGAAGAACACACCAACAAAGTTAA
3216 137_HRV41b   AAATGACATGGGTACATTATGCTTTAGAATAGTTACTGAAGAACACACCAACAAAGTTAA
3217 GROUP_25     -AATGA-ATGGG-ACA-T-TGCTT-AGAATAGT-ACTGAAGAACA-AC-AACAA-GT-AA
3218
3219 132_HRV13    GGTTACAACTAGAATCTATCATAAAGCTAAACATGTCAAAGCATGGTGTCCTAGACCTCC
3220 133_HRV13a   GGTTACAACTAGAATCTATCATAAAGCTAAACATGTCAAAGCATGGTGTCCTAGACCTCC
3221 134_HRV13b   GGTTACAACTAGAATCTATCATAAAGCTAAACATGTCAAAGCATGGTGTCCTAGACCTCC
3222 135_HRV41    GGTCACAACTAGAGTTTACCACAAAGCTAAACATGTTAAAGCATGGTGTCCTAGACCTCC
3223 136_HRV41a   GGTCACAACTAGAGTTTACCACAAAGCTAAACATGTTAAAGCATGGTGTCCTAGACCTCC
3224 137_HRV41b   GGTCACAACTAGAGTTTACCACAAAGCTAAACATGTTAAAGCATGGTGTCCTAGACCTCC
3225 GROUP_25     GGT-ACAACTAGA-T-TA-CA-AAAGCTAAACATGT-AAAGCATGGTGTCCTAGACCTCC
3226
3227 132_HRV13    CAGAGCTGTTGAATATACT-AATGTGCATGTTACAAACTACAAAC-CAGGGA---CAGGA
3228 133_HRV13a   CAGAGCTGTTGAATATACT-AATGTGCATGTTACAAACTACAAAC-CAGGGA---CAGGA
3229 134_HRV13b   CAGAGCTGTTGAATATACT-AATGTGCATGTTACAAACTACAAAC-CAGGGA---CAGGA
3230 135_HRV41    CAGGGCTGTGGAGTACACC-AATGTGCATGTCACAAATTACAAAC-CAAAAG---CAGGA
3231 136_HRV41a   CAGGGCTGTGGAGTACACC-AATGTGCATGTCACAAATTACAAAC-CAAAAG---CAGGA
3232 137_HRV41b   CAGGGCTGTGGAGTACACC-AATGTGCATGTCACAAATTACAAAC-CAAAAG---CAGGA
3233 GROUP_25     CAG-GCTGT-GA-TA-AC-.AATGTGCATGT-ACAAA-TACAAAC.CA----...CAGGA
3234
3235 132_HRV13    GATG------TTGCAGTCT---CCATTGTACCTAGAGCAAATGTTAGGGAAATTAGAA--
3236 133_HRV13a   GATG------TTGCAGTCT---CCATTGTACCTAGAGCAAATGTTAGGGAAATTAGAA--
3237 134_HRV13b   GATG------TTGCAGTCT---CCATTGTACCTAGAGCAAATGTTAGGGAAATTAGAA--
3238 135_HRV41    GCAGA---GATTGTGGCTT---CTGTCAGACCTAGAGACAATGTTAGACAAGTAAGAA--
3239 136_HRV41a   GCAGA---GATTGTGGCTT---CTGTCAGACCTAGAGACAATGTTAGACAAGTAAGAA--
3240 137_HRV41b   GCAGA---GATTGTGGCTT---CTGTCAGACCTAGAGACAATGTTAGACAAGTAAGAA--
3241 GROUP_25     G--G-...--TTG--G--T...C--T---ACCTAGAG--AATGTTAG--AA-T-AGAA..
3242
```

FIG. D13 CONT'D

09.trace                                                                    9/20/2007 5:05 PM

```
3243 132_HRV13      ----ACTTT------------
3244 133_HRV13a     ----ACTTG------------
3245 134_HRV13b     ----ACTTA------------
3246 135_HRV41      ----ATTAT------------
3247 136_HRV41a     ----ATTAG------------
3248 137_HRV41b     ----ATTAC------------
3249 GROUP_25       ....A-T--............
3250
3251
3252
3253 GROUP  26:
3254
3255 138_HRV73      AATCCTGTAGAAAGATATGTAGATGAAGTTTTGAATGAAGTCCTTGTAGTACCCAATATC
3256 139_HRV73b     AATCCTGTAGAAAGATATGTAGATGAAGTTTTGAATGAAGTCCTTGTAGTACCCAATATC
3257 140_HRV73a     AATCCTGTAGAAAGATATGTAGATGAAGTTTTGAATGAAGTCCTTGTAGTACCCAATATC
3258 GROUP_26       AATCCTGTAGAAAGATATGTAGATGAAGTTTTGAATGAAGTCCTTGTAGTACCCAATATC
3259
3260 138_HRV73      AATGAAAGTAATCCAACTACATCCAACTCAGCACCTGCACTGGACGCTGCAGAAACTGGC
3261 139_HRV73b     AATGAAAGTAATCCAACTACATCCAACTCAGCACCTGCACTGGACGCTGCAGAAACTGGC
3262 140_HRV73a     AATGAAAGTAATCCAACTACATCCAACTCAGCACCTGCACTGGACGCTGCAGAAACTGGC
3263 GROUP_26       AATGAAAGTAATCCAACTACATCCAACTCAGCACCTGCACTGGACGCTGCAGAAACTGGC
3264
3265 138_HRV73      CATACCAGTGGTGTACAACCAGAAGACATGATTGAGACCCGTTATGTCCAAACATCACAG
3266 139_HRV73b     CATACCAGTGGTGTACAACCAGAAGACATGATTGAGACCCGTTATGTCCAAACATCACAG
3267 140_HRV73a     CATACCAGTGGTGTACAACCAGAAGACATGATTGAGACCCGTTATGTCCAAACATCACAG
3268 GROUP_26       CATACCAGTGGTGTACAACCAGAAGACATGATTGAGACCCGTTATGTCCAAACATCACAG
3269
3270 138_HRV73      ACTAGAGATGAAATGAGCATTGAAAGCTTCCTTGGCAGGTCAGGTTGTATACACATGTCA
3271 139_HRV73b     ACTAGAGATGAAATGAGCATTGAAAGCTTCCTTGGCAGGTCAGGTTGTATACACATGTCA
3272 140_HRV73a     ACTAGAGATGAAATGAGCATTGAAAGCTTCCTTGGCAGGTCAGGTTGTATACACATGTCA
3273 GROUP_26       ACTAGAGATGAAATGAGCATTGAAAGCTTCCTTGGCAGGTCAGGTTGTATACACATGTCA
3274
3275 138_HRV73      ACTATGAATATAAATTATGAAAAT---------------TATGATGAT---GCTCCTGAA
3276 139_HRV73b     ACTATGAATATAAATTATGAAAAT---------------TATGATGAT---GCTCCTGAA
3277 140_HRV73a     ACTATGAATATAAATTATGAAAAT---------------TATGATGAT---GCTCCTGAA
3278 GROUP_26       ACTATGAATATAAATTATGAAAAT...............TATGATGAT...GCTCCTGAA
3279
3280 138_HRV73      AATTTTACCAAATGGAAATAAGTTTACAAGAGATGGCTCAAATACGTAGGAAATTTGAA
3281 139_HRV73b     AATTTTACCAAATGGAAATAAGTTTACAAGAGATGGCTCAAATACGTAGGAAATTTGAA
3282 140_HRV73a     AATTTTACCAAATGGAAATAAGTTTACAAGAGATGGCTCAAATACGTAGGAAATTTGAA
3283 GROUP_26       AATTTTACCAAATGGAAATAAGTTTACAAGAGATGGCTCAAATACGTAGGAAATTTGAA
3284
3285 138_HRV73      TTATTCACCTATGTAAGATTTGATTCAGAAGTGACAATTG-TACCATGTATAGCTGGTCA
3286 139_HRV73b     TTATTCACCTATGTAAGATTTGATTCAGAAGTGACAATTG-TACCATGTATAGCTGGTCA
3287 140_HRV73a     TTATTCACCTATGTAAGATTTGATTCAGAAGTGACAATTG-TACCATGTATAGCTGGTCA
3288 GROUP_26       TTATTCACCTATGTAAGATTTGATTCAGAAGTGACAATTG.TACCATGTATAGCTGGTCA
3289
3290 138_HRV73      AAGTGGAGATGTGGGACATGTAGTTATGCAGTATATGTATGTCCCACCTGGAGCCCCTCT
3291 139_HRV73b     AAGTGGAGATGTGGGACATGTAGTTATGCAGTATATGTATGTCCCACCTGGAGCCCCTCT
3292 140_HRV73a     AAGTGGAGATGTGGGACATGTAGTTATGCAGTATATGTATGTCCCACCTGGAGCCCCTCT
3293 GROUP_26       AAGTGGAGATGTGGGACATGTAGTTATGCAGTATATGTATGTCCCACCTGGAGCCCCTCT
3294
3295 138_HRV73      ACCCACAAAAAGAAATGACTACACATGGCAGTCCGGCACTAATGCATCAGTATTCTGGCA
3296 139_HRV73b     ACCCACAAAAAGAAATGACTACACATGGCAGTCCGGCACTAATGCATCAGTATTCTGGCA
3297 140_HRV73a     ACCCACAAAAAGAAATGACTACACATGGCAGTCCGGCACTAATGCATCAGTATTCTGGCA
3298 GROUP_26       ACCCACAAAAAGAAATGACTACACATGGCAGTCCGGCACTAATGCATCAGTATTCTGGCA
3299
3300 138_HRV73      ACATGGTCAAACTTACCCCAGATTCTCATTACCATTCCTTAGTATAGCATCCGCATATTA
3301 139_HRV73b     ACATGGTCAAACTTACCCCAGATTCTCATTACCATTCCTTAGTATAGCATCCGCATATTA
3302 140_HRV73a     ACATGGTCAAACTTACCCCAGATTCTCATTACCATTCCTTAGTATAGCATCCGCATATTA
3303 GROUP_26       ACATGGTCAAACTTACCCCAGATTCTCATTACCATTCCTTAGTATAGCATCCGCATATTA
3304
3305 138_HRV73      TATGTTTTATGATGGATATGATGGTGACTCCACACAATCACATTATGGCACCACAGTAGT
3306 139_HRV73b     TATGTTTTATGATGGATATGATGGTGACTCCACACAATCACATTATGGCACCACAGTAGT
3307 140_HRV73a     TATGTTTTATGATGGATATGATGGTGACTCCACACAATCACATTATGGCACCACAGTAGT
```

FIG. D13 CONT'D

```
09.trace                                                             9/20/2007 5:05 PM 3308 GROUP_26      TATGTTTTATGATGGATATGATGGTGACTCCACACAATCACATTATGGCACCACAGTAGT
3309
3310 138_HRV73     TAATGACATGGGCACATTATGCTTTAGGATAGTGACTGAAGAACACACTAGCAGGGTAAA
3311 139_HRV73b    TAATGACATGGGCACATTATGCTTTAGGATAGTGACTGAAGAACACACTAGCAGGGTAAA
3312 140_HRV73a    TAATGACATGGGCACATTATGCTTTAGGATAGTGACTGAAGAACACACTAGCAGGGTAAA
3313 GROUP_26      TAATGACATGGGCACATTATGCTTTAGGATAGTGACTGAAGAACACACTAGCAGGGTAAA
3314
3315 138_HRV73     GGTTACTACTAGAATCTATCATAAGGCTAAACATGTTAAAGCTTGGTGTCCAAGACCTCC
3316 139_HRV73b    GGTTACTACTAGAATCTATCATAAGGCTAAACATGTTAAAGCTTGGTGTCCAAGACCTCC
3317 140_HRV73a    GGTTACTACTAGAATCTATCATAAGGCTAAACATGTTAAAGCTTGGTGTCCAAGACCTCC
3318 GROUP_26      GGTTACTACTAGAATCTATCATAAGGCTAAACATGTTAAAGCTTGGTGTCCAAGACCTCC
3319
3320 138_HRV73     TAGGGCAGTAGAATATACA-AATGCACATGTGACCAATTATAAAC-CCACTG---ATGGA
3321 139_HRV73b    TAGGGCAGTAGAATATACA-AATGCACATGTGACCAATTATAAAC-CCACTG---ATGGA
3322 140_HRV73a    TAGGGCAGTAGAATATACA-AATGCACATGTGACCAATTATAAAC-CCACTG---ATGGA
3323 GROUP_26      TAGGGCAGTAGAATATACA.AATGCACATGTGACCAATTATAAAC.CCACTG...ATGGA
3324
3325 138_HRV73     GAAG------TTACTACTG---CCATTAGGCATAGAGATAATGTTAGAGCCATCCAAA--
3326 139_HRV73b    GAAG------TTACTACTG---CCATTAGGCATAGAGATAATGTTAGAGCCATCCAAA--
3327 140_HRV73a    GAAG------TTACTACTG---CCATTAGGCATAGAGATAATGTTAGAGCCATCCAAA--
3328 GROUP_26      GAAG......TTACTACTG...CCATTAGGCATAGAGATAATGTTAGAGCCATCCAAA..
3329
3330 138_HRV73     ----ATTTT------------
3331 139_HRV73b    ----ATTTG------------
3332 140_HRV73a    ----ATTTC------------
3333 GROUP_26      ....ATTT-............
3334
3335
3336
3337 GROUP  27:
3338
3339 141_HRV61     AACCCTGTGGAAAGATATGTAGATGAAGTTTTAAATGAAGTGCTTGTAGTCCCAAACATT
3340 142_HRV61a    AACCCTGTGGAAAGATATGTAGATGAAGTTTTAAATGAAGTGCTTGTAGTCCCAAACATT
3341 143_HRV61b    AACCCTGTGGAAAGATATGTAGATGAAGTTTTAAATGAAGTGCTTGTAGTCCCAAACATT
3342 144_HRV96     AACCCTGTAGAGAGATATGTAGATGAAGTCTTGAATGAGGTTCTTGTAGTCCCTAATATT
3343 145_HRV96b    AACCCTGTAGAGAGATATGTAGATGAAGTCTTGAATGAGGTTCTTGTAGTCCCTAATATT
3344 146_HRV96a    AACCCTGTAGAGAGATATGTAGATGAAGTCTTGAATGAGGTTCTTGTAGTCCCTAATATT
3345 GROUP_27      AACCCTGT-GA-AGATATGTAGATGAAGT-TT-AATGA-GT-CTTGTAGTCCC-AA-ATT
3346
3347 141_HRV61     AATCAGAGCAACCCTACAACATCCAACTCAGCACCAGTCTTAGACGCTGCTGAAACAGGT
3348 142_HRV61a    AATCAGAGCAACCCTACAACATCCAACTCAGCACCAGTCTTAGACGCTGCTGAAACAGGT
3349 143_HRV61b    AATCAGAGCAACCCTACAACATCCAACTCAGCACCAGTCTTAGACGCTGCTGAAACAGGT
3350 144_HRV96     AATGAAAGTTACCCAACAACTTCCAATTCAGCCCCAGTGCTAGATGCCGCTGAAACAGGT
3351 145_HRV96b    AATGAAAGTTACCCAACAACTTCCAATTCAGCCCCAGTGCTAGATGCCGCTGAAACAGGT
3352 146_HRV96a    AATGAAAGTTACCCAACAACTTCCAATTCAGCCCCAGTGCTAGATGCCGCTGAAACAGGT
3353 GROUP_27      AAT-A-AG--ACCC-ACAAC-TCCAA-TCAGC-CCAGT--TAGA-GC-GCTGAAACAGGT
3354
3355 141_HRV61     CATACCAGCAATGTTCAACCGGAGGACACGATTGAAACACGATATGTTCAAACCTCACAG
3356 142_HRV61a    CATACCAGCAATGTTCAACCGGAGGACACGATTGAAACACGATATGTTCAAACCTCACAG
3357 143_HRV61b    CATACCAGCAATGTTCAACCGGAGGACACGATTGAAACACGATATGTTCAAACCTCACAG
3358 144_HRV96     CATACTAGCAATGTCCAACCAGAGGATATGATTGAGACTCGATATGTTCAGACATCGCAG
3359 145_HRV96b    CATACTAGCAATGTCCAACCAGAGGATATGATTGAGACTCGATATGTTCAGACATCGCAG
3360 146_HRV96a    CATACTAGCAATGTCCAACCAGAGGATATGATTGAGACTCGATATGTTCAGACATCGCAG
3361 GROUP_27      CATAC-AGCAATGT-CAACC-GAGGA-A-GATTGA-AC-CGATATGTTCA-AC-TC-CAG
3362
3363 141_HRV61     ACAAGAGATGAAATGAGTGTAGAAAGTTTCTTGGGTAGATCAGGGTGCATACATATGTCA
3364 142_HRV61a    ACAAGAGATGAAATGAGTGTAGAAAGTTTCTTGGGTAGATCAGGGTGCATACATATGTCA
3365 143_HRV61b    ACAAGAGATGAAATGAGTGTAGAAAGTTTCTTGGGTAGATCAGGGTGCATACATATGTCA
3366 144_HRV96     ACGAGAGATGAAATGAGCATTGAGAGCTTTTTGGGTAGATCAGGGTGTATACACATGTCA
3367 145_HRV96b    ACGAGAGATGAAATGAGCATTGAGAGCTTTTTGGGTAGATCAGGGTGTATACACATGTCA
3368 146_HRV96a    ACGAGAGATGAAATGAGCATTGAGAGCTTTTTGGGTAGATCAGGGTGTATACACATGTCA
3369 GROUP_27      AC-AGAGATGAAATGAG--T-GA-AG-TT-TTGGGTAGATCAGGGTG-ATACA-ATGTCA
3370
3371 141_HRV61     ACATTAAATATAAACTATGATAAC---------------TATGATGAT---TCTATTGAA
3372 142_HRV61a    ACATTAAATATAAACTATGATAAC---------------TATGATGAT---TCTATTGAA
```

FIG. D13 CONT'D

```
09.trace                                                                                              9/20/2007 5:05 PM 3373 143_HRV61b   ACATTAAATATAAACTATGATAAC---------------TATGATGAT---TCTATTGAA
3374 144_HRV96    ACATTAAACATAGATTATGACAAT---------------TATGATGAC---TCCCCTAAG
3375 145_HRV96b   ACATTAAACATAGATTATGACAAT---------------TATGATGAC---TCCCCTAAG
3376 146_HRV96a   ACATTAAACATAGATTATGACAAT---------------TATGATGAC---TCCCCTAAG
3377 GROUP_27     ACATTAAA-ATA-A-TATGA-AA-...............TATGATGA-...TC---T-A-
3378
3379 141_HRV61    AACTTCAAGGTGTGGAAAATAAACCTGCAAGAGATGGCACAAATACGTAGAAAATTTGAG
3380 142_HRV61a   AACTTCAAGGTGTGGAAAATAAACCTGCAAGAGATGGCACAAATACGTAGAAAATTTGAG
3381 143_HRV61b   AACTTCAAGGTGTGGAAAATAAACCTGCAAGAGATGGCACAAATACGTAGAAAATTTGAG
3382 144_HRV96    AATTTTAAGGTGTGGAAAATAAATCTACAAGAAATGGCTCAAATTCGCAGGAAGTTTGAA
3383 145_HRV96b   AATTTTAAGGTGTGGAAAATAAATCTACAAGAAATGGCTCAAATTCGCAGGAAGTTTGAA
3384 146_HRV96a   AATTTTAAGGTGTGGAAAATAAATCTACAAGAAATGGCTCAAATTCGCAGGAAGTTTGAA
3385 GROUP_27     AA-TT-AAGGTGTGGAAAATAAA-CT-CAAGA-ATGGC-CAAAT-CG-AG-AA-TTTGA-
3386
3387 141_HRV61    TTGTTCACATATGCTAGATTTGATTCAGAGATTACAATTG-TACCTTGTGTTGCTGGGCA
3388 142_HRV61a   TTGTTCACATATGCTAGATTTGATTCAGAGATTACAATTG-TACCTTGTGTTGCTGGGCA
3389 143_HRV61b   TTGTTCACATATGCTAGATTTGATTCAGAGATTACAATTG-TACCTTGTGTTGCTGGGCA
3390 144_HRV96    CTGTTCACTTATGCTAGATTTGATTCAGAGATAACAATTG-TTCCATGTGTTGCTGTGCA
3391 145_HRV96b   CTGTTCACTTATGCTAGATTTGATTCAGAGATAACAATTG-TTCCATGTGTTGCTGTGCA
3392 146_HRV96a   CTGTTCACTTATGCTAGATTTGATTCAGAGATAACAATTG-TTCCATGTGTTGCTGTGCA
3393 GROUP_27     -TGTTCAC-TATGCTAGATTTGATTCAGAGAT-ACAATTG.T-CC-TGTGTTGCTG-GCA
3394
3395 141_HRV61    AGGTGGTGACATTGGACACGTGGTCATGCAATACATGTATGTTCCACCTGGTGCACCTAC
3396 142_HRV61a   AGGTGGTGACATTGGACACGTGGTCATGCAATACATGTATGTTCCACCTGGTGCACCTAC
3397 143_HRV61b   AGGTGGTGACATTGGACACGTGGTCATGCAATACATGTATGTTCCACCTGGTGCACCTAC
3398 144_HRV96    GAGTGGTGATATTGGTCATGTGGTCATGCAATATATGTATGTTCCACCAGGTGCCCCCAC
3399 145_HRV96b   GAGTGGTGATATTGGTCATGTGGTCATGCAATATATGTATGTTCCACCAGGTGCCCCCAC
3400 146_HRV96a   GAGTGGTGATATTGGTCATGTGGTCATGCAATATATGTATGTTCCACCAGGTGCCCCCAC
3401 GROUP_27     --GTGGTGA-ATTGG-CA-GTGGTCATGCAATA-ATGTATGTTCCACC-GGTGC-CC-AC
3402
3403 141_HRV61    ACCTGAGAAAAGAAATGATTTCACATGGCAATCAGGCACAAATGCATCTGTTTTCTGGCA
3404 142_HRV61a   ACCTGAGAAAAGAAATGATTTCACATGGCAATCAGGCACAAATGCATCTGTTTTCTGGCA
3405 143_HRV61b   ACCTGAGAAAAGAAATGATTTCACATGGCAATCAGGCACAAATGCATCTGTTTTCTGGCA
3406 144_HRV96    ACCTGAGAAGAGAGATGACTTTACATGGCAATCAGGCACAAATGCATCTGTGTTTTGGCA
3407 145_HRV96b   ACCTGAGAAGAGAGATGACTTTACATGGCAATCAGGCACAAATGCATCTGTGTTTTGGCA
3408 146_HRV96a   ACCTGAGAAGAGAGATGACTTTACATGGCAATCAGGCACAAATGCATCTGTGTTTTGGCA
3409 GROUP_27     ACCTGAGAA-AGA-ATGA-TT-ACATGGCAATCAGGCACAAATGCATCTGT-TT-TGGCA
3410
3411 141_HRV61    ACATGGTCAAGCTTATCCCAGATTTTCATTACCATTCCTAAGTATTGCATCTGCATATTA
3412 142_HRV61a   ACATGGTCAAGCTTATCCCAGATTTTCATTACCATTCCTAAGTATTGCATCTGCATATTA
3413 143_HRV61b   ACATGGTCAAGCTTATCCCAGATTTTCATTACCATTCCTAAGTATTGCATCTGCATATTA
3414 144_HRV96    GCACGGGCAAGCATATCCTAGATTTTCACTGCCTTTCCTTAGTATTGCCTCTGCATATTA
3415 145_HRV96b   GCACGGGCAAGCATATCCTAGATTTTCACTGCCTTTCCTTAGTATTGCCTCTGCATATTA
3416 146_HRV96a   GCACGGGCAAGCATATCCTAGATTTTCACTGCCTTTCCTTAGTATTGCCTCTGCATATTA
3417 GROUP_27     -CA-GG-CAAGC-TATCC-AGATTTTCA-T-CC-TTCCT-AGTATTGC-TCTGCATATTA
3418
3419 141_HRV61    TATGTTTTATGATGGTTATGATGGAGATTCTGAAATAACGCGCTATGGAACATCAGTGAC
3420 142_HRV61a   TATGTTTTATGATGGTTATGATGGAGATTCTGAAATAACGCGCTATGGAACATCAGTGAC
3421 143_HRV61b   TATGTTTTATGATGGTTATGATGGAGATTCTGAAATAACGCGCTATGGAACATCAGTGAC
3422 144_HRV96    CATGTTTTATGATGGATATGATGGTGACTCTGAATCAACACGCTATGGAACATCTGTTAC
3423 145_HRV96b   CATGTTTTATGATGGATATGATGGTGACTCTGAATCAACACGCTATGGAACATCTGTTAC
3424 146_HRV96a   CATGTTTTATGATGGATATGATGGTGACTCTGAATCAACACGCTATGGAACATCTGTTAC
3425 GROUP_27     -ATGTTTTATGATGG-TATGATGG-GA-TCTGAA--AAC-CGCTATGGAACATC-GT-AC
3426
3427 141_HRV61    AAATGATATGGGTGCATTGTGCTTTAGAATAGTAACTGAACAGCATACAAATCAAGTTAA
3428 142_HRV61a   AAATGATATGGGTGCATTGTGCTTTAGAATAGTAACTGAACAGCATACAAATCAAGTTAA
3429 143_HRV61b   AAATGATATGGGTGCATTGTGCTTTAGAATAGTAACTGAACAGCATACAAATCAAGTTAA
3430 144_HRV96    CAATGACATGGGCACTTTATGTTTTAGAATAGTGACAGAGGAACACACCAACAAGGTCAA
3431 145_HRV96b   CAATGACATGGGCACTTTATGTTTTAGAATAGTGACAGAGGAACACACCAACAAGGTCAA
3432 146_HRV96a   CAATGACATGGGCACTTTATGTTTTAGAATAGTGACAGAGGAACACACCAACAAGGTCAA
3433 GROUP_27     -AATGA-ATGGG--C-TT-TG-TTTAGAATAGT-AC-GA--A-CA-AC-AA--A-GT-AA
3434
3435 141_HRV61    AATCACAACTAGGATTTACCATAAAGCTAAACATGTTAAAGTCTGGTGTCCTAGACCCCC
3436 142_HRV61a   AATCACAACTAGGATTTACCATAAAGCTAAACATGTTAAAGTCTGGTGTCCTAGACCCCC
3437 143_HRV61b   AATCACAACTAGGATTTACCATAAAGCTAAACATGTTAAAGTCTGGTGTCCTAGACCCCC
```

FIG. D13 CONT'D 09.trace                                                                                          9/20/2007 5:05 PM

```
3438  144_HRV96     AATTACAACCAGAGTTTACCACAAAGCTAAACATGTTAAGGTGTGGTGCCCGAGACCCCC
3439  145_HRV96b    AATTACAACCAGAGTTTACCACAAAGCTAAACATGTTAAGGTGTGGTGCCCGAGACCCCC
3440  146_HRV96a    AATTACAACCAGAGTTTACCACAAAGCTAAACATGTTAAGGTGTGGTGCCCGAGACCCCC
3441  GROUP_27      AAT-ACAAC-AG--TTTACCA-AAAGCTAAACATGTTAA-GT-TGGTG-CC-AGACCCCC
3442
3443  141_HRV61     CAGAGCAGTGGAATATACT-AATGTGCATTTGACCAATTACAAGC-CCAAAG---ATAGT
3444  142_HRV61a    CAGAGCAGTGGAATATACT-AATGTGCATTTGACCAATTACAAGC-CCAAAG---ATAGT
3445  143_HRV61b    CAGAGCAGTGGAATATACT-AATGTGCATTTGACCAATTACAAGC-CCAAAG---ATAGT
3446  144_HRV96     TAGAGCAGTTGAATACACA-AATGTGCATCTCACAAATTATAAAC-CCAACA---ATG--
3447  145_HRV96b    TAGAGCAGTTGAATACACA-AATGTGCATCTCACAAATTATAAAC-CCAACA---ATG--
3448  146_HRV96a    TAGAGCAGTTGAATACACA-AATGTGCATCTCACAAATTATAAAC-CCAACA---ATG--
3449  GROUP_27      -AGAGCAGT-GAATA-AC-.AATGTGCAT-T-AC-AATTA-AA-C.CCAA--...AT---
3450
3451  141_HRV61     GAAAAACAAGTTACCACTT---TCATCAAACCTAGAGCTAACTTAAGAGAGATTAGAA--
3452  142_HRV61a    GAAAAACAAGTTACCACTT---TCATCAAACCTAGAGCTAACTTAAGAGAGATTAGAA--
3453  143_HRV61b    GAAAAACAAGTTACCACTT---TCATCAAACCTAGAGCTAACTTAAGAGAGATTAGAA--
3454  144_HRV96     -------AGGTTACCACTT---TTATCAAACCTAGAGAAAATCTAAGGGATATTAGAA--
3455  145_HRV96b    -------AGGTTACCACTT---TTATCAAACCTAGAGAAAATCTAAGGGATATTAGAA--
3456  146_HRV96a    -------AGGTTACCACTT---TTATCAAACCTAGAGAAAATCTAAGGGATATTAGAA--
3457  GROUP_27      -------A-GTTACCACTT...T-ATCAAACCTAGAG--AA--TAAG-GA-ATTAGAA..
3458
3459  141_HRV61     ----CATTT-----------
3460  142_HRV61a    ----CATTT-----------
3461  143_HRV61b    ----CATTT-----------
3462  144_HRV96     ----ATTTT-----------
3463  145_HRV96b    ----ATTTA-----------
3464  146_HRV96a    ----ATTTC-----------
3465  GROUP_27      ....--TT............
3466
3467
3468
3469  GROUP_28:
3470
3471  90_HRV16a|    AATCCAGTGGAAAGATATGTAGATGAAGTCTTAAATGAAGTGTTAGTAGTGCCCAATATT
3472  91_HRV16b|    AATCCAGTGGAAAGATATGTAGATGAAGTCTTAAATGAAGTGTTAGTAGTGCCCAATATT
3473  92_1AYM_A     AATCCAGTGGAAAGATATGTAGATGAAGTCTTAAATGAAGTGTTAGTAGTGCCCAATATT
3474  93_HRV81a|    AACCCAGTGGAGCGGTATGTGGATGAAGTCTTAAATGAGGTATTGGTAGTCCCTAATATT
3475  94_HRV81b|    AACCCAGTGGAGCGGTATGTGGATGAAGTCTTAAATGAGGTATTGGTAGTCCCTAATATT
3476  95_HRV81      AACCCAGTGGAGCGGTATGTGGATGAAGTCTTAAATGAGGTATTGGTAGTCCCTAATATT
3477  GROUP_28      AA-CCAGTGGA--G-TATGT-GATGAAGTCTTAAATGA-GT-TT-GTAGT-CC-AATATT
3478
3479  90_HRV16a|    AATGAGAGCCACCCTACCACATCAAATGCGGCCCCAGTTTTGGATGCTGCTGAAACAGGA
3480  91_HRV16b|    AATGAGAGCCACCCTACCACATCAAATGCGGCCCCAGTTTTGGATGCTGCTGAAACAGGA
3481  92_1AYM_A     AATGAGAGCCACCCTACCACATCAAATGCGGCCCCAGTTTTGGATGCTGCTGAAACAGGA
3482  93_HRV81a|    AATGAAAGCCACCCTACAACATCTAATTCAGCTCCTGTTTTAGATGCAGCTGAAACTGGA
3483  94_HRV81b|    AATGAAAGCCACCCTACAACATCTAATTCAGCTCCTGTTTTAGATGCAGCTGAAACTGGA
3484  95_HRV81      AATGAAAGCCACCCTACAACATCTAATTCAGCTCCTGTTTTAGATGCAGCTGAAACTGGA
3485  GROUP_28      AATGA-AGCCACCCTAC-ACATC-AAT-C-GC-CC-GTTTT-GATGC-GCTGAAAC-GGA
3486
3487  90_HRV16a|    CATACCAATAAGATACAGCCAGAAGACACTATAGAAACCAGATATGTGCAATCTTCACAG
3488  91_HRV16b|    CATACCAATAAGATACAGCCAGAAGACACTATAGAAACCAGATATGTGCAATCTTCACAG
3489  92_1AYM_A     CATACCAATAAGATACAGCCAGAAGACACTATAGAAACCAGATATGTGCAATCTTCACAG
3490  93_HRV81a|    CACACCAGTAATATACAACCTGAGGATACTATTGAGACCAGATATGTACAATCTTCACAG
3491  94_HRV81b|    CACACCAGTAATATACAACCTGAGGATACTATTGAGACCAGATATGTACAATCTTCACAG
3492  95_HRV81      CACACCAGTAATATACAACCTGAGGATACTATTGAGACCAGATATGTACAATCTTCACAG
3493  GROUP_28      CA-ACCA-TAA-ATACA-CC-GA-GA-ACTAT-GA-ACCAGATATGT-CAATCTTCACAG
3494
3495  90_HRV16a|    ACATTGGATGAAATGAGTGTGGAAAGCTTCCTAGGCAGATCGGGGTGCATCCATGAATCA
3496  91_HRV16b|    ACATTGGATGAAATGAGTGTGGAAAGCTTCCTAGGCAGATCGGGGTGCATCCATGAATCA
3497  92_1AYM_A     ACATTGGATGAAATGAGTGTGGAAAGCTTCCTAGGCAGATCGGGGTGCATCCATGAATCA
3498  93_HRV81a|    ACACTGGATGAAATGAGTGTAGAAAGTTTTTTAGGCAGATCAGGTTGCATTCATGAATCC
3499  94_HRV81b|    ACACTGGATGAAATGAGTGTAGAAAGTTTTTTAGGCAGATCAGGTTGCATTCATGAATCC
3500  95_HRV81      ACACTGGATGAAATGAGTGTAGAAAGTTTTTTAGGCAGATCAGGTTGCATTCATGAATCC
3501  GROUP_28      ACA-TGGATGAAATGAGTGT-GAAAG-TT--TAGGCAGATC-GG-TGCAT-CATGAATC-
3502
```

FIG. D13 CONT'D 09.trace                                                                9/20/2007 5:05 PM

```
3503  90_HRV16a|   GTGTTGGATATTGTGGACAATTAC---------------AATGAT------------CAA
3504  91_HRV16b|   GTGTTGGATATTGTGGACAATTAC---------------AATGAT------------CAA
3505  92_1AYM_A    GTGTTGGATATTGTGGACAATTAC---------------AATGAT------------CAA
3506  93_HRV81a|   ATATTGGACATTAAAGAGGATTAC---------------AATACC------------CAG
3507  94_HRV81b|   ATATTGGACATTAAAGAGGATTAC---------------AATACC------------CAG
3508  95_HRV81     ATATTGGACATTAAAGAGGATTAC---------------AATACC------------CAG
3509  GROUP_28     -T-TTGGA-ATT---GA--ATTAC...............AAT---...........CA-
3510
3511  90_HRV16a|   AGTTTCACTAAATGGAAGATAAACCTGCAAGAAATGGCACAAATTAGAAGAAAATTTGAA
3512  91_HRV16b|   AGTTTCACTAAATGGAAGATAAACCTGCAAGAAATGGCACAAATTAGAAGAAAATTTGAA
3513  92_1AYM_A    AGTTTCACTAAATGGAAGATAAACCTGCAAGAAATGGCACAAATTAGAAGAAAATTTGAA
3514  93_HRV81a|   AGCTTTACTAAATGGAAAATTAACTTACAAGAGATGGCACAGATTAGGAGAAAGTTTGAA
3515  94_HRV81b|   AGCTTTACTAAATGGAAAATTAACTTACAAGAGATGGCACAGATTAGGAGAAAGTTTGAA
3516  95_HRV81     AGCTTTACTAAATGGAAAATTAACTTACAAGAGATGGCACAGATTAGGAGAAAGTTTGAA
3517  GROUP_28     AG-TT-ACTAAATGGA-AT-AAC-T-CAAGA-ATGGCACA-ATTAG-AGAAA-TTTGAA
3518
3519  90_HRV16a|   ATGTTTACTTATGCAAGATTTGACTCTGAAATTACTATGG-TACCAAGTGTAGCAGCCAA
3520  91_HRV16b|   ATGTTTACTTATGCAAGATTTGACTCTGAAATTACTATGG-TACCAAGTGTAGCAGCCAA
3521  92_1AYM_A    ATGTTTACTTATGCAAGATTTGACTCTGAAATTACTATGG-TACCAAGTGTAGCAGCCAA
3522  93_HRV81a|   ATGTTCACATACACTAGATTTAACTCTGAGATTACACTGG-TACCAAGTATTGCAAACAA
3523  94_HRV81b|   ATGTTCACATACACTAGATTTAACTCTGAGATTACACTGG-TACCAAGTATTGCAAACAA
3524  95_HRV81     ATGTTCACATACACTAGATTTAACTCTGAGATTACACTGG-TACCAAGTATTGCAAACAA
3525  GROUP_28     ATGTT-AC-TA--C-AGATTT-ACTCTGA-ATTAC--TGG.TACCAAGT-T-GCA--CAA
3526
3527  90_HRV16a|   AGATGGTCACATTGGTCATATAGTCATGCAATATATGTATGTACCACCAGGAGCACCTAT
3528  91_HRV16b|   AGATGGTCACATTGGTCATATAGTCATGCAATATATGTATGTACCACCAGGAGCACCTAT
3529  92_1AYM_A    AGATGGTCACATTGGTCATATAGTCATGCAATATATGTATGTACCACCAGGAGCACCTAT
3530  93_HRV81a|   GGAAGGTCATATTGGTCATATAGTAATGCAATACATGTATGTACCACCAGGAGCACCCAT
3531  94_HRV81b|   GGAAGGTCATATTGGTCATATAGTAATGCAATACATGTATGTACCACCAGGAGCACCCAT
3532  95_HRV81     GGAAGGTCATATTGGTCATATAGTAATGCAATACATGTATGTACCACCAGGAGCACCCAT
3533  GROUP_28     -GA-GGTCA-ATTGGTCATATAGT-ATGCAATA-ATGTATGTACCACCAGGAGCACC-AT
3534
3535  90_HRV16a|   ACCAACAACTAGAAATGACTATGCTTGGCAATCTGGAACAAATGCATCTGTATTTTGGCA
3536  91_HRV16b|   ACCAACAACTAGAAATGACTATGCTTGGCAATCTGGAACAAATGCATCTGTATTTTGGCA
3537  92_1AYM_A    ACCAACAACTAGAAATGACTATGCTTGGCAATCTGGAACAAATGCATCTGTATTTTGGCA
3538  93_HRV81a|   TCCAACAACTAGAGAAGACTATGCTTGGCAATCTGGAACAAATGCATCTATATTCTGGCA
3539  94_HRV81b|   TCCAACAACTAGAGAAGACTATGCTTGGCAATCTGGAACAAATGCATCTATATTCTGGCA
3540  95_HRV81     TCCAACAACTAGAGAAGACTATGCTTGGCAATCTGGAACAAATGCATCTATATTCTGGCA
3541  GROUP_28     -CCAACAACTAGA-A-GACTATGCTTGGCAATCTGGAACAAATGCATCT-TATT-TGGCA
3542
3543  90_HRV16a|   GCATGGGCAACCTTTCCCTCGCTTTTCACTTCCCTTTTTGAGTATTGCATCAGCATATTA
3544  91_HRV16b|   GCATGGGCAACCTTTCCCTCGCTTTTCACTTCCCTTTTTGAGTATTGCATCAGCATATTA
3545  92_1AYM_A    GCATGGGCAACCTTTCCCTCGCTTTTCACTTCCCTTTTTGAGTATTGCATCAGCATATTA
3546  93_HRV81a|   ACATGGGCAACCCTTTCCCCGGTTTTCACTCCCTTTTCTAAGTGTAGCATCAGCATATTA
3547  94_HRV81b|   ACATGGGCAACCCTTTCCCCGGTTTTCACTCCCTTTTCTAAGTGTAGCATCAGCATATTA
3548  95_HRV81     ACATGGGCAACCCTTTCCCCGGTTTTCACTCCCTTTTCTAAGTGTAGCATCAGCATATTA
3549  GROUP_28     -CATGGGCAACC-TT-CC-CG-TTTTCACT-CC-TTT-T-AGT-T-GCATCAGCATATTA
3550
3551  90_HRV16a|   CATGTTTTATGATGGTTATGATGGAGACACATATAAATCCAGATATGGAACTGTAGTCAC
3552  91_HRV16b|   CATGTTTTATGATGGTTATGATGGAGACACATATAAATCCAGATATGGAACTGTAGTCAC
3553  92_1AYM_A    CATGTTTTATGATGGTTATGATGGAGACACATATAAATCCAGATATGGAACTGTAGTCAC
3554  93_HRV81a|   CATGTTCTATGATGGATATGATGGTGATACTTATCACTCCAGATACGGGACTGTAGTCAC
3555  94_HRV81b|   CATGTTCTATGATGGATATGATGGTGATACTTATCACTCCAGATACGGGACTGTAGTCAC
3556  95_HRV81     CATGTTCTATGATGGATATGATGGTGATACTTATCACTCCAGATACGGGACTGTAGTCAC
3557  GROUP_28     CATGTT-TATGATGG-TATGATGG-GA-AC-TAT-A-TCCAGATA-GG-ACTGTAGTCAC
3558
3559  90_HRV16a|   CAATGACATGGGAACTTTGTGTTCGCGTATTGTGACCAGTGAGCAATTACACAAAGTCAA
3560  91_HRV16b|   CAATGACATGGGAACTTTGTGTTCGCGTATTGTGACCAGTGAGCAATTACACAAAGTCAA
3561  92_1AYM_A    CAATGACATGGGAACTTTGTGTTCGCGTATTGTGACCAGTGAGCAATTACACAAAGTCAA
3562  93_HRV81a|   TAATGATATGGGAACATTATGCTCACGGATAGTGACAAGTGAGCAAGTGCACAAGGTGAA
3563  94_HRV81b|   TAATGATATGGGAACATTATGCTCACGGATAGTGACAAGTGAGCAAGTGCACAAGGTGAA
3564  95_HRV81     TAATGATATGGGAACATTATGCTCACGGATAGTGACAAGTGAGCAAGTGCACAAGGTGAA
3565  GROUP_28     -AATGA-ATGGGAAC-TT-TG-TC-CG-AT-GTGAC-AGTGAGCAA-T-CACAA-GT-AA
3566
3567  90_HRV16a|   AGTGGTAACAAGGATATATCACAAAGCCAAACACACCAAAGCTTGGTGCCCAAGACCACC
```

FIG. D13 CONT'D

```
09.trace                                                                    9/20/2007 5:05 PM 3568  91_HRV16b|    AGTGGTAACAAGGATATATCACAAAGCCAAACACACCAAAGCTTGGTGCCCAAGACCACC
3569  92_1AYM_A     AGTGGTAACAAGGATATATCACAAAGCCAAACACACCAAAGCTTGGTGCCCAAGACCACC
3570  93_HRV81a|    AATAGTAACAAGAATATATCACAAAGCTAAGCACACCAAAGCTTGGTGTCCAAGACCACC
3571  94_HRV81b|    AATAGTAACAAGAATATATCACAAAGCTAAGCACACCAAAGCTTGGTGTCCAAGACCACC
3572  95_HRV81      AATAGTAACAAGAATATATCACAAAGCTAAGCACACCAAAGCTTGGTGTCCAAGACCACC
3573  GROUP_28      A-T-GTAACAAG-ATATATCACAAAGC-AA-CACACCAAAGCTTGGTG-CCAAGACCACC
3574
3575  90_HRV16a|    CAGAGCTGTTCAATACTCA-CATACACATACCACCAACTACAAAT-TGAGTT---CAGAA
3576  91_HRV16b|    CAGAGCTGTTCAATACTCA-CATACACATACCACCAACTACAAAT-TGAGTT---CAGAA
3577  92_1AYM_A     CAGAGCTGTTCAATACTCA-CATACACATACCACCAACTACAAAT-TGAGTT---CAGAA
3578  93_HRV81a|    CAGGGCTGTTCAGTACACA-CATACACATGTAACTAATTATAAAT-TAGAAA---CAGAT
3579  94_HRV81b|    CAGGGCTGTTCAGTACACA-CATACACATGTAACTAATTATAAAT-TAGAAA---CAGAT
3580  95_HRV81      CAGGGCTGTTCAGTACACA-CATACACATGTAACTAATTATAAAT-TAGAAA---CAGAT
3581  GROUP_28      CAG-GCTGTTCA-TAC-CA.CATACACAT---AC-AA-TA-AAAT.T-----...CAGA-
3582
3583  90_HRV16a|    GTAC------ACAATGATGTGGCTATAAGACCTAGAACAAATCTAACAACTGTA------
3584  91_HRV16b|    GTAC------ACAATGATGTGGCTATAAGACCTAGAACAAATCTAACAACTGTC------
3585  92_1AYM_A     GTAC------ACAATGATGTGGCTATAAGACCTAGAACAAATCTAACAACTGTT------
3586  93_HRV81a|    GTCC------ACACTAGTGTAGCCATAAAACCTAGAACAAGTCTAACAAATGTG------
3587  94_HRV81b|    GTCC------ACACTAGTGTAGCCATAAAACCTAGAACAAGTCTAACAAATGTC------
3588  95_HRV81      GTCC------ACACTAGTGTAGCCATAAAACCTAGAACAAGTCTAACAAATGTT------
3589  GROUP_28      GT-C......ACA-T--TGT-GC-ATAA-ACCTAGAACAA-TCTAACAA-TGT-......
3590
3591  90_HRV16a|    --------------------
3592  91_HRV16b|    --------------------
3593  92_1AYM_A     --------------------
3594  93_HRV81a|    --------------------
3595  94_HRV81b|    --------------------
3596  95_HRV81      --------------------
3597  GROUP_28      ....................
3598
3599
3600
3601  GROUP  29:
3602
3603  147_HRV2      AACCCTGTTGAGAATTATATAGATGAAGTTCTTAATGAAGTTTTAGTTGTCCCAAATATT
3604  148_HRV2a|    AACCCTGTTGAGAATTATATAGATGAAGTTCTTAATGAAGTTTTAGTTGTCCCAAATATT
3605  149_HRV2b|    AACCCTGTTGAGAATTATATAGATGAAGTTCTTAATGAAGTTTTAGTTGTCCCAAATATT
3606  150_HRV49a    AATCCTGTTGAACACTACATAGATGAGGTCCTTAATGAGGTTTTAGTTGTTCCAAATATT
3607  151_HRV49b    AATCCTGTTGAACACTACATAGATGAGGTCCTTAATGAGGTTTTAGTTGTTCCAAATATT
3608  152_HRV49     AATCCTGTTGAACACTACATAGATGAGGTCCTTAATGAGGTTTTAGTTGTTCCAAATATT
3609  153_HRV23a    AATCCAATTGAGAACTATGTAGATGAAGTCTTAATGAAGTCTTAGTTGTTCCCAATATC
3610  154_HRV23b    AATCCAATTGAGAACTATGTAGATGAAGTTCTTAATGAAGTCTTAGTTGTTCCCAATATC
3611  155_HRV23     AATCCAATTGAGAACTATGTAGATGAAGTTCTTAATGAAGTCTTAGTTGTTCCCAATATC
3612  156_HRV30a    AACCCGGTTGAAAATTTTGTAGATGAAGTTCTTAGTGAAGTTTTAGTTGTTCCAAACATT
3613  157_HRV30b    AACCCGGTTGAAAATTTTGTAGATGAAGTTCTTAGTGAAGTTTTAGTTGTTCCAAACATT
3614  158_HRV30     AACCCGGTTGAAAATTTTGTAGATGAAGTTCTTAGTGAAGTTTTAGTTGTTCCAAACATT
3615  GROUP_29      AA-CC--TTGA--A-T---TAGATGA-GT-CTTA-TGA-GT-TTAGTTGT-CC-AA-AT-
3616
3617  147_HRV2      AATAGTAGTAACCCCACAACATCAAATTCTGCCCCAGCATTAGATGCTGCAGAAACAGGG
3618  148_HRV2a|    AATAGTAGTAACCCCACAACATCAAATTCTGCCCCAGCATTAGATGCTGCAGAAACAGGG
3619  149_HRV2b|    AATAGTAGTAACCCCACAACATCAAATTCTGCCCCAGCATTAGATGCTGCAGAAACAGGG
3620  150_HRV49a    AATAGTAGTCACCCCACGACATCAAACTCTGCTCCAGCATTAGATGCTGCAGAAACAGGG
3621  151_HRV49b    AATAGTAGTCACCCCACGACATCAAACTCTGCTCCAGCATTAGATGCTGCAGAAACAGGG
3622  152_HRV49     AATAGTAGTCACCCCACGACATCAAACTCTGCTCCAGCATTAGATGCTGCAGAAACAGGG
3623  153_HRV23a    AATAGTAGTCATCCCACAACATCAAACTCTGCTCCAGCATTAGACGCTGCGGAAACGGGT
3624  154_HRV23b    AATAGTAGTCATCCCACAACATCAAACTCTGCTCCAGCATTAGACGCTGCGGAAACGGGT
3625  155_HRV23     AATAGTAGTCATCCCACAACATCAAACTCTGCTCCAGCATTAGACGCTGCGGAAACGGGT
3626  156_HRV30a    AACAGTAGTCACCCTACTACATCAAACTCTGCTCCGGCATTAGATGCTGCAGAAACAGGA
3627  157_HRV30b    AACAGTAGTCACCCTACTACATCAAACTCTGCTCCGGCATTAGATGCTGCAGAAACAGGA
3628  158_HRV30     AACAGTAGTCACCCTACTACATCAAACTCTGCTCCGGCATTAGATGCTGCAGAAACAGGA
3629  GROUP_29      AA-AGTAGT-A-CC-AC-ACATCAAA-TCTGC-CC-GCATTAGA-GCTGC-GAAAC-GG-
3630
3631  147_HRV2      CACACTAGTAGTGTTCAACCAGAGGATGTCATTGAAACTAGGTATGTGCAGACATCACAA
3632  148_HRV2a|    CACACTAGTAGTGTTCAACCAGAGGATGTCATTGAAACTAGGTATGTGCAGACATCACAA
```

FIG. D13 CONT'D

```
09.trace                                                                    9/20/2007 5:05 PM 3633  149_HRV2b|    CACACTAGTAGTGTTCAACCAGAGGATGTCATTGAAACTAGGTATGTGCAGACATCACAA
3634  150_HRV49a    CACACTAGCAATGTGCAACCTGAAGATGTCATTGAAACCAGATATGTACAGACATCACAA
3635  151_HRV49b    CACACTAGCAATGTGCAACCTGAAGATGTCATTGAAACCAGATATGTACAGACATCACAA
3636  152_HRV49     CACACTAGCAATGTGCAACCTGAAGATGTCATTGAAACCAGATATGTACAGACATCACAA
3637  153_HRV23a    CACACTAGTAATGTTCAACCAGAAGATGTCATTGAAACCAGGTACGTTCAAACATCACAA
3638  154_HRV23b    CACACTAGTAATGTTCAACCAGAAGATGTCATTGAAACCAGGTACGTTCAAACATCACAA
3639  155_HRV23     CACACTAGTAATGTTCAACCAGAAGATGTCATTGAAACCAGGTACGTTCAAACATCACAA
3640  156_HRV30a    CATACTAGTAATGTTCAACCTGAAGATGTCATTGAAACTAGATATGTTCAAACATCACAA
3641  157_HRV30b    CATACTAGTAATGTTCAACCTGAAGATGTCATTGAAACTAGATATGTTCAAACATCACAA
3642  158_HRV30     CATACTAGTAATGTTCAACCTGAAGATGTCATTGAAACTAGATATGTTCAAACATCACAA
3643  GROUP_29      CA-ACTAG-A-TGT-CAACC-GA-GATGTCATTGAAAC-AG-TA-GT-CA-ACATCACAA
3644
3645  147_HRV2      ACAAGAGATGAAATGAGTTTAGAGAGTTTTCTTGGCAGATCAGGATGCATACATGAATCT
3646  148_HRV2a|    ACAAGAGATGAAATGAGTTTAGAGAGTTTTCTTGGCAGATCAGGATGCATACATGAATCT
3647  149_HRV2b|    ACAAGAGATGAAATGAGTTTAGAGAGTTTTCTTGGCAGATCAGGATGCATACATGAATCT
3648  150_HRV49a    ACAAGAGATGAAATGAGTTTAGAGAGTTTTCTTGGTAGGTCAGGGTGTATACATGAATCC
3649  151_HRV49b    ACAAGAGATGAAATGAGTTTAGAGAGTTTTCTTGGTAGGTCAGGGTGTATACATGAATCC
3650  152_HRV49     ACAAGAGATGAAATGAGTTTAGAGAGTTTTCTTGGTAGGTCAGGGTGTATACATGAATCC
3651  153_HRV23a    ACAAGAGATGAAATGAGTTTAGAAAGTTTCCTTGGTAGGTCAGGGTGTATACATGAATCT
3652  154_HRV23b    ACAAGAGATGAAATGAGTTTAGAAAGTTTCCTTGGTAGGTCAGGGTGTATACATGAATCT
3653  155_HRV23     ACAAGAGATGAAATGAGTTTAGAAAGTTTCCTTGGTAGGTCAGGGTGTATACATGAATCT
3654  156_HRV30a    ACAGGGATGAAATGAGTTTAGAAAGCTTTCTTGGTAGATCAGGATGTATACACGAGTCT
3655  157_HRV30b    ACAAGGGATGAAATGAGTTTAGAAAGCTTTCTTGGTAGATCAGGATGTATACACGAGTCT
3656  158_HRV30     ACAAGGGATGAAATGAGTTTAGAAAGCTTTCTTGGTAGATCAGGATGTATACACGAGTCT
3657  GROUP_29      ACAAG-GATGAAATGAGTTTAGA-AG-TT-CTTGG-AG-TCAGG-TG-ATACA-GA-TC-
3658
3659  147_HRV2      AAATTAGAGGTTACACTTGCAAAT---------------TATAACA---------AGGAG
3660  148_HRV2a|    AAATTAGAGGTTACACTTGCAAAT---------------TATAACA---------AGGAG
3661  149_HRV2b|    AAATTAGAGGTTACACTTGCAAAT---------------TATAACA---------AGGAG
3662  150_HRV49a    AAACTAGAGGTCACACTTACAAAT---------------TACAATG---------AAAAT
3663  151_HRV49b    AAACTAGAGGTCACACTTACAAAT---------------TACAATG---------AAAAT
3664  152_HRV49     AAACTAGAGGTCACACTTACAAAT---------------TACAATG---------AAAAT
3665  153_HRV23a    AAATTAAAAGTTGAGATCGGAAAC---------------TATGATG---------AAAAC
3666  154_HRV23b    AAATTAAAAGTTGAGATCGGAAAC---------------TATGATG---------AAAAC
3667  155_HRV23     AAATTAAAAGTTGAGATCGGAAAC---------------TATGATG---------AAAAC
3668  156_HRV30a    AAATTAGAACTTGAGCTTGCACAC---------------TATGATA---------AAAAG
3669  157_HRV30b    AAATTAGAACTTGAGCTTGCACAC---------------TATGATA---------AAAAG
3670  158_HRV30     AAATTAGAACTTGAGCTTGCACAC---------------TATGATA---------AAAAG
3671  GROUP_29      AAA-TA-A--T-----T---A-A-...............TA--A--.........A--A-
3672
3673  147_HRV2      AATTTTACAGTGTGGGCTATTAATATACAAGAAATGGCTCAAATTAGAAGGAAATTTGAA
3674  148_HRV2a|    AATTTTACAGTGTGGGCTATTAATATACAAGAAATGGCTCAAATTAGAAGGAAATTTGAA
3675  149_HRV2b|    AATTTTACAGTGTGGGCTATTAATATACAAGAAATGGCTCAAATTAGAAGGAAATTTGAA
3676  150_HRV49a    AATTTCAAAGTATGGAACATCAATTTGCAAGAAATGGCCCAGATCAGAAGAAAATTTGAA
3677  151_HRV49b    AATTTCAAAGTATGGAACATCAATTTGCAAGAAATGGCCCAGATCAGAAGAAAATTTGAA
3678  152_HRV49     AATTTCAAAGTATGGAACATCAATTTGCAAGAAATGGCCCAGATCAGAAGAAAATTTGAA
3679  153_HRV23a    AATTTTAATACTTGGAATATTAATTTACAGGAAATGGCCCAAATCAGAAGAAAAGTTTGAA
3680  154_HRV23b    AATTTTAATACTTGGAATATTAATTTACAGGAAATGGCCCAAATCAGAAGAAAAGTTTGAA
3681  155_HRV23     AATTTTAATACTTGGAATATTAATTTACAGGAAATGGCCCAAATCAGAAGAAAAGTTTGAA
3682  156_HRV30a    AACTTTACCACATGGAATATTAATCTTCAAGAAATGGCCCAAATTAGAAGAAAATTTGAG
3683  157_HRV30b    AACTTTACCACATGGAATATTAATCTTCAAGAAATGGCCCAAATTAGAAGAAAATTTGAG
3684  158_HRV30     AACTTTACCACATGGAATATTAATCTTCAAGAAATGGCCCAAATTAGAAGAAAATTTGAG
3685  GROUP_29      AA-TT-A-----TGG---AT-AAT-T-CA-GAAATGGC-CA-AT-AGAAG-AA-TTTGA-
3686
3687  147_HRV2      TTGTTCACCTATACTAGGTTTGATTCTGAAATAACCCTAG-TTCCATGCATTTCCGCCCT
3688  148_HRV2a|    TTGTTCACCTATACTAGGTTTGATTCTGAAATAACCCTAG-TTCCATGCATTTCCGCCCT
3689  149_HRV2b|    TTGTTCACCTATACTAGGTTTGATTCTGAAATAACCCTAG-TTCCATGCATTTCCGCCCT
3690  150_HRV49a    CTGTTTACTTACACTAGATTCGATTCTGAAATAACCTTGG-TTCCATGCATTTCTGCACT
3691  151_HRV49b    CTGTTTACTTACACTAGATTCGATTCTGAAATAACCTTGG-TTCCATGCATTTCTGCACT
3692  152_HRV49     CTGTTTACTTACACTAGATTCGATTCTGAAATAACCTTGG-TTCCATGCATTTCTGCACT
3693  153_HRV23a    CTGTTTACTTACACTAGATTTGATTCTGAAATTACTTTGG-TTCCATGCATTTCTGCTCT
3694  154_HRV23b    CTGTTTACTTACACTAGATTTGATTCTGAAATTACTTTGG-TTCCATGCATTTCTGCTCT
3695  155_HRV23     CTGTTTACTTACACTAGATTTGATTCTGAAATTACTTTGG-TTCCATGCATTTCTGCTCT
3696  156_HRV30a    CTATTCACTTACACTAGATTTGATTCTGAGATAACCTTGG-TTCCGTGTATTTCAGCTCT
3697  157_HRV30b    CTATTCACTTACACTAGATTTGATTCTGAGATAACCTTGG-TTCCGTGTATTTCAGCTCT
```

FIG. D13 CONT'D 09.trace                                                                                    9/20/2007 5:05 PM

```
3698  158_HRV30    CTATTCACTTACACTAGATTTGATTCTGAGATAACCTTGG-TTCCGTGTATTTCAGCTCT
3699  GROUP_29     -T-TT-AC-TA-ACTAG-TT-GATTCTGA-AT-AC--T-G.TTCC-TG-ATTTC-GC-CT
3700
3701  147_HRV2     TAGTCAGGACATTGGACACATCACAATGCAATACATGTATGTTCCACCTGGTGCACCGGT
3702  148_HRV2a|   TAGTCAGGACATTGGACACATCACAATGCAATACATGTATGTTCCACCTGGTGCACCGGT
3703  149_HRV2b|   TAGTCAGGACATTGGACACATCACAATGCAATACATGTATGTTCCACCTGGTGCACCGGT
3704  150_HRV49a   TAGCAAGGATATTGGACACATTACAATGCAATACATGTATGTGCCGCCAGGTGCACCTGT
3705  151_HRV49b   TAGCAAGGATATTGGACACATTACAATGCAATACATGTATGTGCCGCCAGGTGCACCTGT
3706  152_HRV49    TAGCAAGGATATTGGACACATTACAATGCAATACATGTATGTGCCGCCAGGTGCACCTGT
3707  153_HRV23a   TAGTCAAGATATTGGTCACATCACAATGCAGTATATGTATGTCCCACCAGGTGCTCCAAT
3708  154_HRV23b   TAGTCAAGATATTGGTCACATCACAATGCAGTATATGTATGTCCCACCAGGTGCTCCAAT
3709  155_HRV23    TAGTCAAGATATTGGTCACATCACAATGCAGTATATGTATGTCCCACCAGGTGCTCCAAT
3710  156_HRV30a   CAGCCAAGATATCGGACACATTACAATGCAGTATATGTATGTTCCACCTGGCGCTCCAAT
3711  157_HRV30b   CAGCCAAGATATCGGACACATTACAATGCAGTATATGTATGTTCCACCTGGCGCTCCAAT
3712  158_HRV30    CAGCCAAGATATCGGACACATTACAATGCAGTATATGTATGTTCCACCTGGCGCTCCAAT
3713  GROUP_29     -AG--A-GA-AT-GG-CACAT-ACAATGCA-TA-ATGTATGT-CC-CC-GG-GC-CC--T
3714
3715  147_HRV2     GCCCAATAGTAGGGACGATTATGCATGGCAGTCTGGCACTAATGCCTCTGTTTTCTGGCA
3716  148_HRV2a|   GCCCAATAGTAGGGACGATTATGCATGGCAGTCTGGCACTAATGCCTCTGTTTTCTGGCA
3717  149_HRV2b|   GCCCAATAGTAGGGACGATTATGCATGGCAGTCTGGCACTAATGCCTCTGTTTTCTGGCA
3718  150_HRV49a   ACCAAAGAGCAGAGATGATTATGCATGGCAGTCTGGCACTAATGCATCTGTTTTCTGGCA
3719  151_HRV49b   ACCAAAGAGCAGAGATGATTATGCATGGCAGTCTGGCACTAATGCATCTGTTTTCTGGCA
3720  152_HRV49    ACCAAAGAGCAGAGATGATTATGCATGGCAGTCTGGCACTAATGCATCTGTTTTCTGGCA
3721  153_HRV23a   ACCGGAAAGTAGAAATGACTATGCATGGCAATCTGGAACAAATGCGTCCATTTTTTGGCA
3722  154_HRV23b   ACCGGAAAGTAGAAATGACTATGCATGGCAATCTGGAACAAATGCGTCCATTTTTTGGCA
3723  155_HRV23    ACCGGAAAGTAGAAATGACTATGCATGGCAATCTGGAACAAATGCGTCCATTTTTTGGCA
3724  156_HRV30a   TCCCGAGAGCAGAAATGACTATGCATGGCAGTCTGGAACAAATGCATCTGTTTTTTGGCA
3725  157_HRV30b   TCCCGAGAGCAGAAATGACTATGCATGGCAGTCTGGAACAAATGCATCTGTTTTTTGGCA
3726  158_HRV30    TCCCGAGAGCAGAAATGACTATGCATGGCAGTCTGGAACAAATGCATCTGTTTTTTGGCA
3727  GROUP_29     -CC--A-AG-AG--A-GA-TATGCATGGCA-TCTGG-AC-AATGC-TC--TTTT-TGGCA
3728
3729  147_HRV2     ACATGGACAGGCTTATCCAAGATTTTCCTTACCTTTCCTAAGTGTGGCATCTGCTTATTA
3730  148_HRV2a|   ACATGGACAGGCTTATCCAAGATTTTCCTTACCTTTCCTAAGTGTGGCATCTGCTTATTA
3731  149_HRV2b|   ACATGGACAGGCTTATCCAAGATTTTCCTTACCTTTCCTAAGTGTGGCATCTGCTTATTA
3732  150_HRV49a   ACATGGGCAAGCATACCCAAGATTTCTCTACCCTTTTGAGTGTAGCTTCAGCTTACTA
3733  151_HRV49b   ACATGGGCAAGCATACCCAAGATTTTCTCTACCCTTTTTGAGTGTAGCTTCAGCTTACTA
3734  152_HRV49    ACATGGGCAAGCATACCCAAGATTTTCTCTACCCTTTTTGAGTGTAGCTTCAGCTTACTA
3735  153_HRV23a   ACATGGACAAACATATCCAAGGTTCTCCTTACCCTTTTTGAGTGTGGCATCTGCTTATTA
3736  154_HRV23b   ACATGGACAAACATATCCAAGGTTCTCCTTACCCTTTTTGAGTGTGGCATCTGCTTATTA
3737  155_HRV23    ACATGGACAAACATATCCAAGGTTCTCCTTACCCTTTTTGAGTGTGGCATCTGCTTATTA
3738  156_HRV30a   ACACGGACAAACATACCCAAGATTCTCCCTACCATTTTTGAGTGTAGCATCTGCTTATTA
3739  157_HRV30b   ACACGGACAAACATACCCAAGATTCTCCCTACCATTTTTGAGTGTAGCATCTGCTTATTA
3740  158_HRV30    ACACGGACAAACATACCCAAGATTCTCCCTACCATTTTTGAGTGTAGCATCTGCTTATTA
3741  GROUP_29     ACA-GG-CA--C-TA-CCAAG-TT-TC--TACC-TT--T-AGTGT-GC-TC-GCTTA-TA
3742
3743  147_HRV2     CATGTTTTATGATGGGTATGATG------AACAAGATCAAAACTATGGTACAGCAAGCAC
3744  148_HRV2a|   CATGTTTTATGATGGGTATGATG------AACAAGATCAAAACTATGGTACAGCAAGCAC
3745  149_HRV2b|   CATGTTTTATGATGGGTATGATG------AACAAGATCAAAACTATGGTACAGCAAGCAC
3746  150_HRV49a   CATGTTTTATGATGGATATAATG------AACAGGGCCAAAATTATGGTACGGTAAGTAC
3747  151_HRV49b   CATGTTTTATGATGGATATAATG------AACAGGGCCAAAATTATGGTACGGTAAGTAC
3748  152_HRV49    CATGTTTTATGATGGATATAATG------AACAGGGCCAAAATTATGGTACGGTAAGTAC
3749  153_HRV23a   CATGTTTTATGATGGATACAATG------AGAAAGGCACGCATTATGGAACAGTTAGCAC
3750  154_HRV23b   CATGTTTTATGATGGATACAATG------AGAAAGGCACGCATTATGGAACAGTTAGCAC
3751  155_HRV23    CATGTTTTATGATGGATACAATG------AGAAAGGCACGCATTATGGAACAGTTAGCAC
3752  156_HRV30a   CATGTTCTATGATGGATACAATG------AGGGAGGCACAAATTATGGTACAGTGAGCAC
3753  157_HRV30b   CATGTTCTATGATGGATACAATG------AGGGAGGCACAAATTATGGTACAGTGAGCAC
3754  158_HRV30    CATGTTCTATGATGGATACAATG------AGGGAGGCACAAATTATGGTACAGTGAGCAC
3755  GROUP_29     CATGTT-TATGATGG-TA--ATG......A----G------A-TATGG-AC-G--AG-AC
3756
3757  147_HRV2     AAATAACATGGGGTCACTATGCTCTAGGATAGTAACAGAGAAACACATTCATAAGGTACA
3758  148_HRV2a|   AAATAACATGGGGTCACTATGCTCTAGGATAGTAACAGAGAAACACATTCATAAGGTACA
3759  149_HRV2b|   AAATAACATGGGGTCACTATGCTCTAGGATAGTAACAGAGAAACACATTCATAAGGTACA
3760  150_HRV49a   AAACAACATGGGGATCATTATGCTCTAGGATAGTAACAGAGAAACACATTCACAGTATGCA
3761  151_HRV49b   AAACAACATGGGGATCATTATGCTCTAGGATAGTAACAGAGAAACACATTCACAGTATGCA
3762  152_HRV49    AAACAACATGGGGATCATTATGCTCTAGGATAGTAACAGAGAAACACATTCACAGTATGCA
```

FIG. D13 CONT'D

```
09.trace                                                                    9/20/2007 5:05 PM 3763  153_HRV23a    AAACAACATGGGCACATTGTGCTCCAGAGTGGTAACAGAGAAACACATTCATGATATGCG
3764  154_HRV23b    AAACAACATGGGCACATTGTGCTCCAGAGTGGTAACAGAGAAACACATTCATGATATGCG
3765  155_HRV23     AAACAACATGGGCACATTGTGCTCCAGAGTGGTAACAGAGAAACACATTCATGATATGCG
3766  156_HRV30a    AAACAACATGGGCACACTGTGTTCCAGAGTGGTAACAGAAAAACACATTCATGATGTGCG
3767  157_HRV30b    AAACAACATGGGCACACTGTGTTCCAGAGTGGTAACAGAAAAACACATTCATGATGTGCG
3768  158_HRV30     AAACAACATGGGCACACTGTGTTCCAGAGTGGTAACAGAAAAACACATTCATGATGTGCG
3769  GROUP_29      AAA-AACATGGG--CA-T-TG-TC-AG--T-GTAACAGA-AAACACATTCA-----T-C-
3770
3771  147_HRV2      TATAATGACAAGAATCTATCACAAGGCTAAACATGTCAAGGCATGGTGTCCACGCCCACC
3772  148_HRV2a|    TATAATGACAAGAATCTATCACAAGGCTAAACATGTCAAGGCATGGTGTCCACGCCCACC
3773  149_HRV2b|    TATAATGACAAGAATCTATCACAAGGCTAAACATGTCAAGGCATGGTGTCCACGCCCACC
3774  150_HRV49a    TATCATGACAAGAATCTATCATAAAGCTAAACACGTCAAAGCATGGTGTCCGCGCCCACC
3775  151_HRV49b    TATCATGACAAGAATCTATCATAAAGCTAAACACGTCAAAGCATGGTGTCCGCGCCCACC
3776  152_HRV49     TATCATGACAAGAATCTATCATAAAGCTAAACACGTCAAAGCATGGTGTCCGCGCCCACC
3777  153_HRV23a    GATAATGACAAGGGTCTACCACAAAGCTAAACATGTCAAAGCATGGTGTCCGCGGCCACC
3778  154_HRV23b    GATAATGACAAGGGTCTACCACAAAGCTAAACATGTCAAAGCATGGTGTCCGCGGCCACC
3779  155_HRV23     GATAATGACAAGGGTCTACCACAAAGCTAAACATGTCAAAGCATGGTGTCCGCGGCCACC
3780  156_HRV30a    CATAATGACAAGGGTCTACCACAAGGCTAAACATGTCAAAGCGTGGTGTCCACGGCCACC
3781  157_HRV30b    CATAATGACAAGGGTCTACCACAAGGCTAAACATGTCAAAGCGTGGTGTCCACGGCCACC
3782  158_HRV30     CATAATGACAAGGGTCTACCACAAGGCTAAACATGTCAAAGCGTGGTGTCCACGGCCACC
3783  GROUP_29      -AT-ATGACAAG--TCTA-CA-AA-GCTAAACA-GTCAA-GC-TGGTGTCC-CG-CCACC
3784
3785  147_HRV2      CAGAGCGCTTGAGTATACT-CGTGCTCACCGCACTAATTTTAAAA-TTGAGG---ATAGG
3786  148_HRV2a|    CAGAGCGCTTGAGTATACT-CGTGCTCACCGCACTAATTTTAAAA-TTGAGG---ATAGG
3787  149_HRV2b|    CAGAGCGCTTGAGTATACT-CGTGCTCACCGCACTAATTTTAAAA-TTGAGG---ATAGG
3788  150_HRV49a    CAGAGCACTTGAATATACT-CGCGCTCACCGTACTAATTTCAAAG-TTGAAG---ACAGA
3789  151_HRV49b    CAGAGCACTTGAATATACT-CGCGCTCACCGTACTAATTTCAAAG-TTGAAG---ACAGA
3790  152_HRV49     CAGAGCACTTGAATATACT-CGCGCTCACCGTACTAATTTCAAAG-TTGAAG---ACAGA
3791  153_HRV23a    CAGAGCACTTGAATACACA-CGCGCTCACCGTACTAATTTCAAAA-TTGAAG---GTGAA
3792  154_HRV23b    CAGAGCACTTGAATACACA-CGCGCTCACCGTACTAATTTCAAAA-TTGAAG---GTGAA
3793  155_HRV23     CAGAGCACTTGAATACACA-CGCGCTCACCGTACTAATTTCAAAA-TTGAAG---GTGAA
3794  156_HRV30a    TAGGGCGCTTGAGTATACC-CGTGCTCATCGCACCAATTTTAAAA-TTGATG---GCAGG
3795  157_HRV30b    TAGGGCGCTTGAGTATACC-CGTGCTCATCGCACCAATTTTAAAA-TTGATG---GCAGG
3796  158_HRV30     TAGGGCGCTTGAGTATACC-CGTGCTCATCGCACCAATTTTAAAA-TTGATG---GCAGG
3797  GROUP_29      -AG-GC-CTTGA-TA-AC-.CG-GCTCA-CG-AC-AATTT-AAA-.TTGA-G...-----
3798
3799  147_HRV2      AGTA------TTCAGACAG---CAATTGTGACCAGACCAATTATCACTACAGCT------
3800  148_HRV2a|    AGTA------TTCAGACAG---CAATTGTGACCAGACCAATTATCACTACAGCA------
3801  149_HRV2b|    AGTA------TTCAGACAG---CAATTGTGACCAGACCAATTATCACTACAGCG------
3802  150_HRV49a    GACA------TTAAAACAG---GAATCACATCCAGAGCAATTATTACAACAGCA------
3803  151_HRV49b    GACA------TTAAAACAG---GAATCACATCCAGAGCAATTATTACAACAGCA------
3804  152_HRV49     GACA------TTAAAACAG---GAATCACATCCAGAGCAATTATTACAACAGCT------
3805  153_HRV23a    AATG------TCAAATCAA---GGGTTGCACATAGACCTGCAGTGATAACAGCG------
3806  154_HRV23b    AATG------TCAAATCAA---GGGTTGCACATAGACCTGCAGTGATAACAGCA------
3807  155_HRV23     AATG------TCAAATCAA---GGGTTGCACATAGACCTGCAGTGATAACAGCT------
3808  156_HRV30a    GAAG------TTAAATCAA---GGGTTGAACACAGAGCTAGGGTGACGACAGCA------
3809  157_HRV30b    GAAG------TTAAATCAA---GGGTTGAACACAGAGCTAGGGTGACGACAGCG------
3810  158_HRV30     GAAG------TTAAATCAA---GGGTTGAACACAGAGCTAGGGTGACGACAGCT------
3811  GROUP_29      ----......T--A--CA-...---T-------AGA-C-----T-A--ACAGC-......
3812
3813  147_HRV2      --------------------
3814  148_HRV2a|    --------------------
3815  149_HRV2b|    --------------------
3816  150_HRV49a    --------------------
3817  151_HRV49b    --------------------
3818  152_HRV49     --------------------
3819  153_HRV23a    --------------------
3820  154_HRV23b    --------------------
3821  155_HRV23     --------------------
3822  156_HRV30a    --------------------
3823  157_HRV30b    --------------------
3824  158_HRV30     --------------------
3825  GROUP_29      ....................
3826
3827
```

FIG. D13 CONT'D

09.trace                                                                9/20/2007 5:05 PM

```
3828
3829  GROUP 30:
3830
3831  159_HRV7     AACCCGGTAGAGAATTATGTAGATAGCTTACTAAATGAAGTATTAGTGGTACCTAATATT
3832  160_HRV7b|   AACCCGGTAGAGAATTATGTAGATAGCTTACTAAATGAAGTATTAGTGGTACCTAATATT
3833  161_HRV7a|   AACCCGGTAGAGAATTATGTAGATAGCTTACTAAATGAAGTATTAGTGGTACCTAATATT
3834  162_HRV88    AATCCAGTAGAAAACTATGTAGATAACCTTGTTAAACGAAGTGCTAGTAGTTCCTAACATT
3835  163_HRV88a   AATCCAGTAGAAAACTATGTAGATAACTTGTTAAACGAAGTGCTAGTAGTTCCTAACATT
3836  164_HRV88b   AATCCAGTAGAAAACTATGTAGATAACTTGTTAAACGAAGTGCTAGTAGTTCCTAACATT
3837  165_HRV36a   AATCCAGTTGAAAATTACATAGATAATGTATTAAATGAAGTACTTGTAGTGCCAAACATC
3838  166_HRV36b   AATCCAGTTGAAAATTACATAGATAATGTATTAAATGAAGTACTTGTAGTGCCAAACATC
3839  167_HRV36    AATCCAGTTGAAAATTACATAGATAATGTATTAAATGAAGTACTTGTAGTGCCAAACATC
3840  168_HRV89a   AACCCAGTTGAAAATTATATAGATAGTGTATTAAATGAAGTTCTTGTGGTGCCAAATATC
3841  169_HRV89b   AACCCAGTTGAAAATTATATAGATAGTGTATTAAATGAAGTTCTTGTGGTGCCAAATATC
3842  170_HRV89    AACCCAGTTGAAAATTATATAGATAGTGTATTAAATGAAGTTCTTGTGGTGCCAAATATC
3843  171_HRV58    AATCCAGTAGAAAATTACATAGATAATGTGTTAAATGAAGTACTTGTAGTTCCAAATATC
3844  172_HRV58a   AATCCAGTAGAAAATTACATAGATAATGTGTTAAATGAAGTACTTGTAGTTCCAAATATC
3845  173_HRV58b   AATCCAGTAGAAAATTACATAGATAATGTGTTAAATGAAGTACTTGTAGTTCCAAATATC
3846  GROUP_30     AA-CC-GT-GA-AA-TA--TAGATA---T--TAAA-GAAGT--T-GT-GT-CC-AA-AT-
3847
3848  159_HRV7     CAGCCAAGTACATCTGTTTCAAGTCACTCTGTACCAGCATTGGATGCTGCAGAGACTGGA
3849  160_HRV7b|   CAGCCAAGTACATCTGTTTCAAGTCACTCTGTACCAGCATTGGATGCTGCAGAGACTGGA
3850  161_HRV7a|   CAGCCAAGTACATCTGTTTCAAGTCACTCTGTACCAGCATTGGATGCTGCAGAGACTGGA
3851  162_HRV88    CAACCTAGCACATCCGTTTCAAGTCACTCTGTGCCAGCTCTGGATGCTGCGGAAACAGGG
3852  163_HRV88a   CAACCTAGCACATCCGTTTCAAGTCACTCTGTGCCAGCTCTGGATGCTGCGGAAACAGGG
3853  164_HRV88b   CAACCTAGCACATCCGTTTCAAGTCACTCTGTGCCAGCTCTGGATGCTGCGGAAACAGGG
3854  165_HRV36a   CAACCTAGTTCATCTGTGTCAAGTCATTCAGCTCCCGCCTTAGACGCTGCGGAAACTGGA
3855  166_HRV36b   CAACCTAGTTCATCTGTGTCAAGTCATTCAGCTCCCGCCTTAGACGCTGCGGAAACTGGA
3856  167_HRV36    CAACCTAGTTCATCTGTGTCAAGTCATTCAGCTCCCGCCTTAGACGCTGCGGAAACTGGA
3857  168_HRV89a   CAACCTAGCACATCTGTGTCAAGTCATGCAGCGCCTGCATTGGATGCTGCGGAAACCGGA
3858  169_HRV89b   CAACCTAGCACATCTGTGTCAAGTCATGCAGCGCCTGCATTGGATGCTGCGGAAACCGGA
3859  170_HRV89    CAACCTAGCACATCTGTGTCAAGTCATGCAGCGCCTGCATTGGATGCTGCGGAAACCGGA
3860  171_HRV58    CAACCTAGTACATCTGTATCAAGTCATTCTGTGCCTGCCTTGGATGCTGCAGAAACGGGA
3861  172_HRV58a   CAACCTAGTACATCTGTATCAAGTCATTCTGTGCCTGCCTTGGATGCTGCAGAAACGGGA
3862  173_HRV58b   CAACCTAGTACATCTGTATCAAGTCATTCTGTGCCTGCCTTGGATGCTGCAGAAACGGGA
3863  GROUP_30     CA-CC-AG--CATC-GT-TCAAGTCA--C-G--CC-GC--T-GA-GCTGC-GA-AC-GG-
3864
3865  159_HRV7     CATACTAGTTCTGTTCAACCTGAAGATATGATCGAGACAAGGTATGTCATAACAGACCAA
3866  160_HRV7b|   CATACTAGTTCTGTTCAACCTGAAGATATGATCGAGACAAGGTATGTCATAACAGACCAA
3867  161_HRV7a|   CATACTAGTTCTGTTCAACCTGAAGATATGATCGAGACAAGGTATGTCATAACAGACCAA
3868  162_HRV88    CATACTAGTTCTGTTCAACCTGAAGATATGATAGAAACTAGATATGTTATAACAGATCAA
3869  163_HRV88a   CATACTAGTTCTGTTCAACCTGAAGATATGATAGAAACTAGATATGTTATAACAGATCAA
3870  164_HRV88b   CATACTAGTTCTGTTCAACCTGAAGATATGATAGAAACTAGATATGTTATAACAGATCAA
3871  165_HRV36a   CATACCAGCTCTGTCCAACCAGAGGACATGATCGAGACCAGATATGTCATAACTGATCAA
3872  166_HRV36b   CATACCAGCTCTGTCCAACCAGAGGACATGATCGAGACCAGATATGTCATAACTGATCAA
3873  167_HRV36    CATACCAGCTCTGTCCAACCAGAGGACATGATCGAGACCAGATATGTCATAACTGATCAA
3874  168_HRV89a   CACACCAGCTCTGTTCAACCTGAAGATATGATTGAAACTAGATATGTTATAACTGATCAA
3875  169_HRV89b   CACACCAGCTCTGTTCAACCTGAAGATATGATTGAAACTAGATATGTTATAACTGATCAA
3876  170_HRV89    CACACCAGCTCTGTTCAACCTGAAGATATGATTGAAACTAGATATGTTATAACTGATCAA
3877  171_HRV58    CACACAAGTTCTGTTCAGCCTGAGGATATGATTGAAACTAGATATGTTATCACAGATCAA
3878  172_HRV58a   CACACAAGTTCTGTTCAGCCTGAGGATATGATTGAAACTAGATATGTTATCACAGATCAA
3879  173_HRV58b   CACACAAGTTCTGTTCAGCCTGAGGATATGATTGAAACTAGATATGTTATCACAGATCAA
3880  GROUP_30     CA-AC-AG-TCTGT-CA-CC-GA-GA-ATGAT-GA-AC-AG-TATGT-AT-AC-GA-CAA
3881
3882  159_HRV7     ACAAGGGATGAAACTAGTATAGAGAGTTTCTTAGGTAGATCTGGATGTATTGCTAAAGTT
3883  160_HRV7b|   ACAAGGGATGAAACTAGTATAGAGAGTTTCTTAGGTAGATCTGGATGTATTGCTAAAGTT
3884  161_HRV7a|   ACAAGGGATGAAACTAGTATAGAGAGTTTCTTAGGTAGATCTGGATGTATTGCTAAAGTT
3885  162_HRV88    ACAAGGGATGAAACCAGCATTGAAAGCTTTCTGGGTAGGTCTGGATGCATAGCAAAAATT
3886  163_HRV88a   ACAAGGGATGAAACCAGCATTGAAAGCTTTCTGGGTAGGTCTGGATGCATAGCAAAAATT
3887  164_HRV88b   ACAAGGGATGAAACCAGCATTGAAAGCTTTCTGGGTAGGTCTGGATGCATAGCAAAAATT
3888  165_HRV36a   ACAAGAGATGAGACAAGTTATTGAAAGCTTCTTAGGTAGGTCAGGGTGCATAGCTATGATA
3889  166_HRV36b   ACAAGAGATGAGACAAGTATTGAAAGCTTCTTAGGTAGGTCAGGGTGCATAGCTATGATA
3890  167_HRV36    ACAAGAGATGAGACAAGTATTGAAAGCTTCTTAGGTAGGTCAGGGTGCATAGCTATGATA
3891  168_HRV89a   ACAAGGGATGAAACAAGTATTGAGAGTTTCTTAGGTAGGTCAGGGTGTATCGCTATGATA
3892  169_HRV89b   ACAAGGGATGAAACAAGTATTGAGAGTTTCTTAGGTAGGTCAGGGTGTATCGCTATGATA
```

```
09.trace                                                                9/20/2007 5:05 PM 3893  170_HRV89    ACAAGGGATGAAACAAGTATTGAGAGTTTCTTAGGTAGGTCAGGGTGTATCGCTATGATA
3894  171_HRV58    ACAAGAGATGAAACTAGCATTGAAAGCTTTTTAGGTAGATCTGGTTGCATTGCTATCATA
3895  172_HRV58a   ACAAGAGATGAAACTAGCATTGAAAGCTTTTTAGGTAGATCTGGTTGCATTGCTATCATA
3896  173_HRV58b   ACAAGAGATGAAACTAGCATTGAAAGCTTTTTAGGTAGATCTGGTTGCATTGCTATCATA
3897  GROUP_30     ACAAG-GATGA-AC-AG-AT-GA-AG-TT--T-GGTAG-TC-GG-TG-AT-GC-A---T-
3898
3899  159_HRV7     AAACTTGACACAA------CACAGGGT---------GACTATGACACAGGCAAAGGTGTT
3900  160_HRV7b|   AAACTTGACACAA------CACAGGGT---------GACTATGACACAGGCAAAGGTGTT
3901  161_HRV7a|   AAACTTGACACAA------CACAGGGT---------GACTATGACACAGGCAAAGGTGTT
3902  162_HRV88    AAACTTGACACAA------ATGAAGGT---------GATTACGACACA---ATAGGTGTT
3903  163_HRV88a   AAACTTGACACAA------ATGAAGGT---------GATTACGACACA---ATAGGTGTT
3904  164_HRV88b   AAACTTGACACAA------ATGAAGGT---------GATTACGACACA---ATAGGTGTT
3905  165_HRV36a   GAATTTAGCACAAGTAGTGATAAAGAT---------GAACATGATGAA---ATTGGCAAG
3906  166_HRV36b   GAATTTAGCACAAGTAGTGATAAAGAT---------GAACATGATGAA---ATTGGCAAG
3907  167_HRV36    GAATTTAGCACAAGTAGTGATAAAGAT---------GAACATGATGAA---ATTGGCAAG
3908  168_HRV89a   GAATTTAATACAAGTAGTGATAAAACT---------GAACATGATAAA---ATTGGTAAA
3909  169_HRV89b   GAATTTAATACAAGTAGTGATAAAACT---------GAACATGATAAA---ATTGGTAAA
3910  170_HRV89    GAATTTAATACAAGTAGTGATAAAACT---------GAACATGATAAA---ATTGGTAAA
3911  171_HRV58    AAATTTAACACAA------ATAAGACT---------AATTATGATGAC---ATAGGTGTA
3912  172_HRV58a   AAATTTAACACAA------ATAAGACT---------AATTATGATGAC---ATAGGTGTA
3913  173_HRV58b   AAATTTAACACAA------ATAAGACT---------AATTATGATGAC---ATAGGTGTA
3914  GROUP_30     -AA-TT---ACAA---------A---T.........-A--A-GA-------A--GG----
3915
3916  159_HRV7     GGTTTCACTACATGGAAAATCAGCTTACAAGAAATGGCACAAATCAGAAGAAAGTTTGAA
3917  160_HRV7b|   GGTTTCACTACATGGAAAATCAGCTTACAAGAAATGGCACAAATCAGAAGAAAGTTTGAA
3918  161_HRV7a|   GGTTTCACTACATGGAAAATCAGCTTACAAGAAATGGCACAAATCAGAAGAAAGTTTGAA
3919  162_HRV88    GGATTTGTAACATGGAAGATTAGCTTGCAAGAAATGGCACAAATCAGGAGAAAATTTGAA
3920  163_HRV88a   GGATTTGTAACATGGAAGATTAGCTTGCAAGAAATGGCACAAATCAGGAGAAAATTTGAA
3921  164_HRV88b   GGATTTGTAACATGGAAGATTAGCTTGCAAGAAATGGCACAAATCAGGAGAAAATTTGAA
3922  165_HRV36a   GGATTCAAAACATGGAAGATTAGTCTTCAAGAAATGGCACAAATTAGAAGGAAATATGAA
3923  166_HRV36b   GGATTCAAAACATGGAAGATTAGTCTTCAAGAAATGGCACAAATTAGAAGGAAATATGAA
3924  167_HRV36    GGATTCAAAACATGGAAGATTAGTCTTCAAGAAATGGCACAAATTAGAAGGAAATATGAA
3925  168_HRV89a   GGATTCAAAACATGGAAGGTTAGTCTTCAAGAAATGGCACAAATCAGAAGAAAAATATGAA
3926  169_HRV89b   GGATTCAAAACATGGAAGGTTAGTCTTCAAGAAATGGCACAAATCAGAAGAAAAATATGAA
3927  170_HRV89    GGATTCAAAACATGGAAGGTTAGTCTTCAAGAAATGGCACAAATCAGAAGAAAAATATGAA
3928  171_HRV58    GGATACAAAACATGGAAAATTAGCCTTCAAGAGATGGCACAAATTAGAAGGAAATTTGAG
3929  172_HRV58a   GGATACAAAACATGGAAAATTAGCCTTCAAGAGATGGCACAAATTAGAAGGAAATTTGAG
3930  173_HRV58b   GGATACAAAACATGGAAAATTAGCCTTCAAGAGATGGCACAAATTAGAAGGAAATTTGAG
3931  GROUP_30     GG-T-----ACATGGAA--T-AG--T-CAAGA-ATGGCACAAAT-AG-AG-AA-T-TGA-
3932
3933  159_HRV7     CTATTCACATACACTAGATTTGATTCTGAGATAACAATAG-TCACAGCAGCAGCAGCACA
3934  160_HRV7b|   CTATTCACATACACTAGATTTGATTCTGAGATAACAATAG-TCACAGCAGCAGCAGCACA
3935  161_HRV7a|   CTATTCACATACACTAGATTTGATTCTGAGATAACAATAG-TCACAGCAGCAGCAGCACA
3936  162_HRV88    TTGTTTACATACACTAGATTTGACTCAGAAATAACAATAG-TCACAGCAGCTGCAGCACA
3937  163_HRV88a   TTGTTTACATACACTAGATTTGACTCAGAAATAACAATAG-TCACAGCAGCTGCAGCACA
3938  164_HRV88b   TTGTTTACATACACTAGATTTGACTCAGAAATAACAATAG-TCACAGCAGCTGCAGCACA
3939  165_HRV36a   TTGTTTACATACACAAGATTTGACTCAGAAATAACAATAG-TCACCGCAGCTGCAGTGCA
3940  166_HRV36b   TTGTTTACATACACAAGATTTGACTCAGAAATAACAATAG-TCACCGCAGCTGCAGTGCA
3941  167_HRV36    TTGTTTACATACACAAGATTTGACTCAGAAATAACAATAG-TCACCGCAGCTGCAGTGCA
3942  168_HRV89a   TTATTCACATATACAAGATTTGATTCAGAGATAACAATAG-TCACTGCAGCCGCAGCTCA
3943  169_HRV89b   TTATTCACATATACAAGATTTGATTCAGAGATAACAATAG-TCACTGCAGCCGCAGCTCA
3944  170_HRV89    TTATTCACATATACAAGATTTGATTCAGAGATAACAATAG-TCACTGCAGCCGCAGCTCA
3945  171_HRV58    TTGTTTACATATACAAGATTTGACTCAGAGATTACAATAG-TCACTGCAGCAGCTGCTCA
3946  172_HRV58a   TTGTTTACATATACAAGATTTGACTCAGAGATTACAATAG-TCACTGCAGCAGCTGCTCA
3947  173_HRV58b   TTGTTTACATATACAAGATTTGACTCAGAGATTACAATAG-TCACTGCAGCAGCTGCTCA
3948  GROUP_30     -T-TT-ACATA-AC-AGATTTGA-TC-GA-AT-ACAATAG.TCAC-GCAGC-GC-G--CA
3949
3950  159_HRV7     AGGTAATGATATTGGACATATAGTTATGCAATTTATGTATGTACCTCCAGGGGCCCCAGT
3951  160_HRV7b|   AGGTAATGATATTGGACATATAGTTATGCAATTTATGTATGTACCTCCAGGGGCCCCAGT
3952  161_HRV7a|   AGGTAATGATATTGGACATATAGTTATGCAATTTATGTATGTACCTCCAGGGGCCCCAGT
3953  162_HRV88    AGGTGATGATACTGGACATATAGTACTGCAATTCATGTATGTGCCTCCAGGTGCACCAAT
3954  163_HRV88a   AGGTGATGATACTGGACATATAGTACTGCAATTCATGTATGTGCCTCCAGGTGCACCAAT
3955  164_HRV88b   AGGTGATGATACTGGACATATAGTACTGCAATTCATGTATGTGCCTCCAGGTGCACCAAT
3956  165_HRV36a   GGGAGATGATAGTGGGCATGTAGTATTACAATTCATGTATGTACCTCCAGGAGCGCCTGT
3957  166_HRV36b   GGGAGATGATAGTGGGCATGTAGTATTACAATTCATGTATGTACCTCCAGGAGCGCCTGT
```

09.trace 9/20/2007 5:05 PM

```
3958 167_HRV36    GGGAGATGATAGTGGGCATGTAGTATTACAATTCATGTATGTACCTCCAGGAGCGCCTGT
3959 168_HRV89a   AGGAAATGATAGTGGACATATAGTATTGCAATTTATGTATGTACCCCCAGGAGCACCTGT
3960 169_HRV89b   AGGAAATGATAGTGGACATATAGTATTGCAATTTATGTATGTACCCCCAGGAGCACCTGT
3961 170_HRV89    AGGAAATGATAGTGGACATATAGTATTGCAATTTATGTATGTACCCCCAGGAGCACCTGT
3962 171_HRV58    AGGAGAAGATAATGGACATATTGTGTTACAATTTATGTATGTACCCCCAGGAGCACCTGT
3963 172_HRV58a   AGGAGAAGATAATGGACATATTGTGTTACAATTTATGTATGTACCCCCAGGAGCACCTGT
3964 173_HRV58b   AGGAGAAGATAATGGACATATTGTGTTACAATTTATGTATGTACCCCCAGGAGCACCTGT
3965 GROUP_30     -GG--A-GATA-TGG-CAT-T-GT--T-CAATT-ATGTATGT-CC-CCAGG-GC-CC--T
3966
3967 159_HRV7     TCCAATAAAACGCGAAGATTATACATGGCAATCAGGAACAAATGCTTCTATATTTTGGCA
3968 160_HRV7b|   TCCAATAAAACGCGAAGATTATACATGGCAATCAGGAACAAATGCTTCTATATTTTGGCA
3969 161_HRV7a|   TCCAATAAAACGCGAAGATTATACATGGCAATCAGGAACAAATGCTTCTATATTTTGGCA
3970 162_HRV88    TCCCAAGAAACGTGATGATTACACATGGCAGTCAGGAACAAATGCATCTGTGTTCTGGCA
3971 163_HRV88a   TCCCAAGAAACGTGATGATTACACATGGCAGTCAGGAACAAATGCATCTGTGTTCTGGCA
3972 164_HRV88b   TCCCAAGAAACGTGATGATTACACATGGCAGTCAGGAACAAATGCATCTGTGTTCTGGCA
3973 165_HRV36a   TCCTGTGAAGCGTGATGACTACACATGGCAATCAGGGACAAATGCATCTGTGTTCTGGCA
3974 166_HRV36b   TCCTGTGAAGCGTGATGACTACACATGGCAATCAGGGACAAATGCATCTGTGTTCTGGCA
3975 167_HRV36    TCCTGTGAAGCGTGATGACTACACATGGCAATCAGGGACAAATGCATCTGTGTTCTGGCA
3976 168_HRV89a   CCCCGAAAAACGTGATGATTACACATGGCAATCAGGAACAAATGCATCTGTGTTCTGGCA
3977 169_HRV89b   CCCCGAAAAACGTGATGATTACACATGGCAATCAGGAACAAATGCATCTGTGTTCTGGCA
3978 170_HRV89    CCCCGAAAAACGTGATGATTACACATGGCAATCAGGAACAAATGCATCTGTGTTCTGGCA
3979 171_HRV58    ACCCAAGAATCGTGATGACTTTACATGGCAATCAGGCACAAATGCATCTGTTTTCTGGCA
3980 172_HRV58a   ACCCAAGAATCGTGATGACTTTACATGGCAATCAGGCACAAATGCATCTGTTTTCTGGCA
3981 173_HRV58b   ACCCAAGAATCGTGATGACTTTACATGGCAATCAGGCACAAATGCATCTGTTTTCTGGCA
3982 GROUP_30     -CC----AA-CG-GA-GA-T--ACATGGCA-TCAGG-ACAAATGC-TCT-T-TT-TGGCA
3983
3984 159_HRV7     GGAGGGTCAACCATACCCTAGATTCACAATTCCTTTTATGAGTATTGCATCAGCTTATTA
3985 160_HRV7b|   GGAGGGTCAACCATACCCTAGATTCACAATTCCTTTTATGAGTATTGCATCAGCTTATTA
3986 161_HRV7a|   GGAGGGTCAACCATACCCTAGATTCACAATTCCTTTTATGAGTATTGCATCAGCTTATTA
3987 162_HRV88    AGAAGGACAACCATACCCAAGATTTACCATTCCCTTTATGAGTATTGCATCAGCTTACTA
3988 163_HRV88a   AGAAGGACAACCATACCCAAGATTTACCATTCCCTTTATGAGTATTGCATCAGCTTACTA
3989 164_HRV88b   AGAAGGACAACCATACCCAAGATTTACCATTCCCTTTATGAGTATTGCATCAGCTTACTA
3990 165_HRV36a   AGAAGGGCAACCATATCCTAGATTTACAATCCCCTTTATGAGTATTGCATCAGCTTATTA
3991 166_HRV36b   AGAAGGGCAACCATATCCTAGATTTACAATCCCCTTTATGAGTATTGCATCAGCTTATTA
3992 167_HRV36    AGAAGGGCAACCATATCCTAGATTTACAATCCCCTTTATGAGTATTGCATCAGCTTATTA
3993 168_HRV89a   AGAAGGACAACCATACCCCAGATTCACAATCCCTTTTATGAGCATTGCATCAGCCTATTA
3994 169_HRV89b   AGAAGGACAACCATACCCCAGATTCACAATCCCTTTTATGAGCATTGCATCAGCCTATTA
3995 170_HRV89    AGAAGGACAACCATACCCCAGATTCACAATCCCTTTTATGAGCATTGCATCAGCCTATTA
3996 171_HRV58    GGAAGGACAACCATACCCCTTTTATGAGCATTGCATCAGCTTACTA
3997 172_HRV58a   GGAAGGACAACCATACCCTAGATTTACAATCCCTTTTATGAGCATTGCATCAGCTTACTA
3998 173_HRV58b   GGAAGGACAACCATACCCTAGATTTACAATCCCTTTTATGAGCATTGCATCAGCTTACTA
3999 GROUP_30     -GA-GG-CAACCATA-CC-AGATT-AC-AT-CC-TTTATGAG-ATTGCATCAGC-TA-TA
4000
4001 159_HRV7     TATGTTCTATGATGGATATGATGGTGATGATGCGTCATCCAAATATGGTTCCGTAGTAAC
4002 160_HRV7b|   TATGTTCTATGATGGATATGATGGTGATGATGCGTCATCCAAATATGGTTCCGTAGTAAC
4003 161_HRV7a|   TATGTTCTATGATGGATATGATGGTGATGATGCGTCATCCAAATATGGTTCCGTAGTAAC
4004 162_HRV88    TATGTTTTATGATGGATATGATGGTGATGATGCATCATCTAGGTATGGCTCAGTGGTAAC
4005 163_HRV88a   TATGTTTTATGATGGATATGATGGTGATGATGCATCATCTAGGTATGGCTCAGTGGTAAC
4006 164_HRV88b   TATGTTTTATGATGGATATGATGGTGATGATGCATCATCTAGGTATGGCTCAGTGGTAAC
4007 165_HRV36a   TATGTTTTATGATGGTTATGATGGTGATAATGCCGCATCAAAATATGGATCTGTGGTTAC
4008 166_HRV36b   TATGTTTTATGATGGTTATGATGGTGATAATGCCGCATCAAAATATGGATCTGTGGTTAC
4009 167_HRV36    TATGTTTTATGATGGTTATGATGGTGATAATGCCGCATCAAAATATGGATCTGTGGTTAC
4010 168_HRV89a   CATGTTTTATGATGGTTATGATGGTGATAGTGCAGCATCAAAATACGGTTCTGTAGTCAC
4011 169_HRV89b   CATGTTTTATGATGGTTATGATGGTGATAGTGCAGCATCAAAATACGGTTCTGTAGTCAC
4012 170_HRV89    CATGTTTTATGATGGTTATGATGGTGATAGTGCAGCATCAAAATACGGTTCTGTAGTCAC
4013 171_HRV58    TATGTTTTATGATGGCTATGATGGTGATGATGCTAAATCAATATATGGTTCTGTGGTAAC
4014 172_HRV58a   TATGTTTTATGATGGCTATGATGGTGATGATGCTAAATCAATATATGGTTCTGTGGTAAC
4015 173_HRV58b   TATGTTTTATGATGGCTATGATGGTGATGATGCTAAATCAATATATGGTTCTGTGGTAAC
4016 GROUP_30     -ATGTT-TATGATGG-TATGATGGTGAT--TGC---ATC-A--TA-GG-TC-GT-GT-AC
4017
4018 159_HRV7     CAATGACATGGGAACCATATGTGTTAGACTAGTTACATCTACACAAAAACACAATTTAAA
4019 160_HRV7b|   CAATGACATGGGAACCATATGTGTTAGACTAGTTACATCTACACAAAAACACAATTTAAA
4020 161_HRV7a|   CAATGACATGGGAACCATATGTGTTAGACTAGTTACATCTACACAAAAACACAATTTAAA
4021 162_HRV88    TAATGATATGGGAACTATATGTATTAGATTGGTCACCTCCACCCAAAAGCATAAACTGAA
4022 163_HRV88a   TAATGATATGGGAACTATATGTATTAGATTGGTCACCTCCACCCAAAAGCATAAACTGAA
```

FIG. D13 CONT'D

```
09.trace                                                                                    9/20/2007 5:05 PM 4023  164_HRV88b    TAATGATATGGGAACTATATGTATTAGATTGGTCACCTCCACCCAAAAGCATAAACTGAA
4024  165_HRV36a    TAACGACATGGGAACCATATGTGTTAGAATAGTTACATCCAACCAAAAACATGATTTAAA
4025  166_HRV36b    TAACGACATGGGAACCATATGTGTTAGAATAGTTACATCCAACCAAAAACATGATTTAAA
4026  167_HRV36     TAACGACATGGGAACCATATGTGTTAGAATAGTTACATCCAACCAAAAACATGATTTAAA
4027  168_HRV89a    TAATGATATGGGAACCATATGTGTTAGAATAGTGACATCCAACCAAAAACATGATTTAAA
4028  169_HRV89b    TAATGATATGGGAACCATATGTGTTAGAATAGTGACATCCAACCAAAAACATGATTTAAA
4029  170_HRV89     TAATGATATGGGAACCATATGTGTTAGAATAGTGACATCCAACCAAAAACATGATTTAAA
4030  171_HRV58     AAATGACACATGGGAACTATATGTGTTAGAATAGTCACATCCAAACAAAGACACAATTTAAA
4031  172_HRV58a    AAATGACATGGGAACTATATGTGTTAGAATAGTCACATCCAAACAAAGACACAATTTAAA
4032  173_HRV58b    AAATGACATGGGAACTATATGTGTTAGAATAGTCACATCCAAACAAAGACACAATTTAAA
4033  GROUP_30      -AA-GA-ATGGGAAC-ATATGT-TTAGA-T-GT-AC-TC-A--CAAA--CA--A--T-AA
4034
4035  159_HRV7      GATTGTGAGTCGCATTTACCACAAAGCCAAACATATAAAAGCATGGTGCCCACGCCCACC
4036  160_HRV7b|    GATTGTGAGTCGCATTTACCACAAAGCCAAACATATAAAAGCATGGTGCCCACGCCCACC
4037  161_HRV7a|    GATTGTGAGTCGCATTTACCACAAAGCCAAACATATAAAAGCATGGTGCCCACGCCCACC
4038  162_HRV88     TATCATTAGCCGTATATATCACAAGGCTAAACATATAAAGGCATGGTGTCCACGCCCACC
4039  163_HRV88a    TATCATTAGCCGTATATATCACAAGGCTAAACATATAAAGGCATGGTGTCCACGCCCACC
4040  164_HRV88b    TATCATTAGCCGTATATATCACAAGGCTAAACATATAAAGGCATGGTGTCCACGCCCACC
4041  165_HRV36a    TATTGTATGCCGCATTTATCATAAAGCTAAACACATAAAGGCCTGGTGCCCGCGTCCACC
4042  166_HRV36b    TATTGTATGCCGCATTTATCATAAAGCTAAACACATAAAGGCCTGGTGCCCGCGTCCACC
4043  167_HRV36     TATTGTATGCCGCATTTATCATAAAGCTAAACACATAAAGGCCTGGTGCCCGCGTCCACC
4044  168_HRV89a    TATTGTGTGCCGCATTTACCACAAGGCCAAACATATAAAAGCATGGTGTCCTCGCCCACC
4045  169_HRV89b    TATTGTGTGCCGCATTTACCACAAGGCCAAACATATAAAAGCATGGTGTCCTCGCCCACC
4046  170_HRV89     TATTGTGTGCCGCATTTACCACAAGGCCAAACATATAAAAGCATGGTGTCCTCGCCCACC
4047  171_HRV58     CATTGTCTGTCGCATTTACCACAAAGCCAAGCATATAAAAGCATGGTGTCCACGCCCACC
4048  172_HRV58a    CATTGTCTGTCGCATTTACCACAAAGCCAAGCATATAAAAGCATGGTGTCCACGCCCACC
4049  173_HRV58b    CATTGTCTGTCGCATTTACCACAAAGCCAAGCATATAAAAGCATGGTGTCCACGCCCACC
4050  GROUP_30      -AT--T--G-CG-AT-TA-CA-AA-GC-AA-CA-ATAAA-GC-TGGTG-CC-CG-CCACC
4051
4052  159_HRV7      ACGAGCTGTGCCTTATCAA-CACACTCACTCCACCAACTATGTGC-CACAAA---ATGGA
4053  160_HRV7b|    ACGAGCTGTGCCTTATCAA-CACACTCACTCCACCAACTATGTGC-CACAAA---ATGGA
4054  161_HRV7a|    ACGAGCTGTGCCTTATCAA-CACACTCACTCCACCAACTATGTGC-CACAAA---ATGGA
4055  162_HRV88     AAGAGCCGTACCTTATCAG-CACACACACTCCACCAATTATGTAC-CAACAG---ATGGG
4056  163_HRV88a    AAGAGCCGTACCTTATCAG-CACACACACTCCACCAATTATGTAC-CAACAG---ATGGG
4057  164_HRV88b    AAGAGCCGTACCTTATCAG-CACACACACTCCACCAATTATGTAC-CAACAG---ATGGG
4058  165_HRV36a    AAGGGCCGTTCCTTACCAA-CACACACATTCCACTAATTATATAC-CATACA---AAGGT
4059  166_HRV36b    AAGGGCCGTTCCTTACCAA-CACACACATTCCACTAATTATATAC-CATACA---AAGGT
4060  167_HRV36     AAGGGCCGTTCCTTACCAA-CACACACATTCCACTAATTATATAC-CATACA---AAGGT
4061  168_HRV89a    AAGGGCTGTTGCCTATCAA-CACACACACTCAACCAATTACATAC-CATCCA---ATGGT
4062  169_HRV89b    AAGGGCTGTTGCCTATCAA-CACACACACTCAACCAATTACATAC-CATCCA---ATGGT
4063  170_HRV89     AAGGGCTGTTGCCTATCAA-CACACACACTCAACCAATTACATAC-CATCCA---ATGGT
4064  171_HRV58     AAGGGCTGTTCCTTATCAA-TTCACACATTCTACTAATTACATAC-CAGATA---GTGGT
4065  172_HRV58a    AAGGGCTGTTCCTTATCAA-TTCACACATTCTACTAATTACATAC-CAGATA---GTGGT
4066  173_HRV58b    AAGGGCTGTTCCTTATCAA-TTCACACATTCTACTAATTACATAC-CAGATA---GTGGT
4067  GROUP_30      A-G-GC-GT--C-TA-CA-.--CAC-CA-TC-AC-AA-TA--T-C.CA----...--GG-
4068
4069  159_HRV7      GAGG------TCGCA---ACTCAAATCAAAACCAGAGCCAATCTTTTCACCCTCAAAT--
4070  160_HRV7b|    GAGG------TCGCA---ACTCAAATCAAAACCAGAGCCAATCTTTTCACCCTCAAAT--
4071  161_HRV7a|    GAGG------TCGCA---ACTCAAATCAAAACCAGAGCCAATCTTTTCACCCTCAAAT--
4072  162_HRV88     GAAG------TAGCA---ACTCAAATCAAAACCAGACGAGATGTTTACACTGTTACCA--
4073  163_HRV88a    GAAG------TAGCA---ACTCAAATCAAAACCAGACGAGATGTTTACACTGTTACCA--
4074  164_HRV88b    GAAG------TAGCA---ACTCAAATCAAAACCAGACGAGATGTTTACACTGTTACCA--
4075  165_HRV36a    GAGA------TCACA---ACCCAAATTAAAACCAGACCTAATGTCTTCACTGTA------
4076  166_HRV36b    GAGA------TCACA---ACCCAAATTAAAACCAGACCTAATGTCTTCACTGTG------
4077  167_HRV36     GAGA------TCACA---ACCCAAATTAAAACCAGACCTAATGTCTTCACTGTT------
4078  168_HRV89a    GAGG------CCACA---ACTCAGATTAAAACCAGACCTGATGTTTTACCGTTACAA--
4079  169_HRV89b    GAGG------CCACA---ACTCAGATTAAAACCAGACCTGATGTTTTACCGTTACAA--
4080  170_HRV89     GAGG------CCACA---ACTCAGATTAAAACCAGACCTGATGTTTTACCGTTACAA--
4081  171_HRV58     GAGG------TAACA---ACACAAATCAAACCCAGAACCAATGTTTTTACTATTACAT--
4082  172_HRV58a    GAGG------TAACA---ACACAAATCAAACCCAGAACCAATGTTTTTACTATTACAT--
4083  173_HRV58b    GAGG------TAACA---ACACAAATCAAACCCAGAACCAATGTTTTTACTATTACAT--
4084  GROUP_30      GA--......---CA...AC-CA-AT-AAA-CCAGA-----AT-T-T--AC--T-----..
4085
4086  159_HRV7      ----CAGCT-----------
4087  160_HRV7b|    ----CAGCA-----------
```

FIG. D13 CONT'D 09.trace                                                                                    9/20/2007 5:05 PM

```
4088  161_HRV7a     ----CAGCG------------
4089  162_HRV88     ----CTGCT------------
4090  163_HRV88a    ----CTGCA------------
4091  164_HRV88b    ----CTGCG------------
4092  165_HRV36a    ---------------------
4093  166_HRV36b    ---------------------
4094  167_HRV36     ---------------------
4095  168_HRV89a    ----ACGTG------------
4096  169_HRV89b    ----ACGTA------------
4097  170_HRV89     ----ACGTC------------
4098  171_HRV58     ----CTGCT------------
4099  172_HRV58a    ----CTGCA------------
4100  173_HRV58b    ----CTGCC------------
4101  GROUP_30      ....-----............
4102
4103
4104
4105  GROUP  31:
4106
4107  174_HRV12a    AATCCAGTAGAGAGATATGTTGATGAGGTGCTAAATGAAGTTCTAGTTGTTCCAAACATA
4108  175_HRV12b    AATCCAGTAGAGAGATATGTTGATGAGGTGCTAAATGAAGTTCTAGTTGTTCCAAACATA
4109  176_HRV12     AATCCAGTAGAGAGATATGTTGATGAGGTGCTAAATGAAGTTCTAGTTGTTCCAAACATA
4110  GROUP_31      AATCCAGTAGAGAGATATGTTGATGAGGTGCTAAATGAAGTTCTAGTTGTTCCAAACATA
4111
4112  174_HRV12a    AACAAAAGTAATGGGCAGTTATCAAACGCAGCACCAGCGTTGGACGCTGCAGAAACTGGT
4113  175_HRV12b    AACAAAAGTAATGGGCAGTTATCAAACGCAGCACCAGCGTTGGACGCTGCAGAAACTGGT
4114  176_HRV12     AACAAAAGTAATGGGCAGTTATCAAACGCAGCACCAGCGTTGGACGCTGCAGAAACTGGT
4115  GROUP_31      AACAAAAGTAATGGGCAGTTATCAAACGCAGCACCAGCGTTGGACGCTGCAGAAACTGGT
4116
4117  174_HRV12a    CATACCAGCCAAACACAACCAGAAGATGTGATTGAAACCAGGTATGTGATTACAGACCAG
4118  175_HRV12b    CATACCAGCCAAACACAACCAGAAGATGTGATTGAAACCAGGTATGTGATTACAGACCAG
4119  176_HRV12     CATACCAGCCAAACACAACCAGAAGATGTGATTGAAACCAGGTATGTGATTACAGACCAG
4120  GROUP_31      CATACCAGCCAAACACAACCAGAAGATGTGATTGAAACCAGGTATGTGATTACAGACCAG
4121
4122  174_HRV12a    ACTAGAGATGAGATGTCAATTGAATCTTTCCTTGGTCGGTCCGGATGCATTTCAATTATC
4123  175_HRV12b    ACTAGAGATGAGATGTCAATTGAATCTTTCCTTGGTCGGTCCGGATGCATTTCAATTATC
4124  176_HRV12     ACTAGAGATGAGATGTCAATTGAATCTTTCCTTGGTCGGTCCGGATGCATTTCAATTATC
4125  GROUP_31      ACTAGAGATGAGATGTCAATTGAATCTTTCCTTGGTCGGTCCGGATGCATTTCAATTATC
4126
4127  174_HRV12a    GAATTGGATTTAGACCATGAAGGT---------------TATTCAGCA---GAAGGGAAA
4128  175_HRV12b    GAATTGGATTTAGACCATGAAGGT---------------TATTCAGCA---GAAGGGAAA
4129  176_HRV12     GAATTGGATTTAGACCATGAAGGT---------------TATTCAGCA---GAAGGGAAA
4130  GROUP_31      GAATTGGATTTAGACCATGAAGGT...............TATTCAGCA...GAAGGGAAA
4131
4132  174_HRV12a    AACTTTAAAACATGGAAGATAAATCTTAAGGAAATGGCCCAGATTAGAAGGAAAAATGAG
4133  175_HRV12b    AACTTTAAAACATGGAAGATAAATCTTAAGGAAATGGCCCAGATTAGAAGGAAAAATGAG
4134  176_HRV12     AACTTTAAAACATGGAAGATAAATCTTAAGGAAATGGCCCAGATTAGAAGGAAAAATGAG
4135  GROUP_31      AACTTTAAAACATGGAAGATAAATCTTAAGGAAATGGCCCAGATTAGAAGGAAAAATGAG
4136
4137  174_HRV12a    CTTTTCACCTACTTAAGGTTTGATTCTGAAATCACCATTGTTCCAAGCAATG-CAGCAAT
4138  175_HRV12b    CTTTTCACCTACTTAAGGTTTGATTCTGAAATCACCATTGTTCCAAGCAATG-CAGCAAT
4139  176_HRV12     CTTTTCACCTACTTAAGGTTTGATTCTGAAATCACCATTGTTCCAAGCAATG-CAGCAAT
4140  GROUP_31      CTTTTCACCTACTTAAGGTTTGATTCTGAAATCACCATTGTTCCAAGCAATG.CAGCAAT
4141
4142  174_HRV12a    AGAAGGAAGCAATGGTCACGTGGTGGTCCAATACATGTATGTACCTCCTGGTGCCCCACT
4143  175_HRV12b    AGAAGGAAGCAATGGTCACGTGGTGGTCCAATACATGTATGTACCTCCTGGTGCCCCACT
4144  176_HRV12     AGAAGGAAGCAATGGTCACGTGGTGGTCCAATACATGTATGTACCTCCTGGTGCCCCACT
4145  GROUP_31      AGAAGGAAGCAATGGTCACGTGGTGGTCCAATACATGTATGTACCTCCTGGTGCCCCACT
4146
4147  174_HRV12a    ACCCAAAAAACGTGATGATTACACATGGCAATCTGGCACCAACGCCTCAGTTTTTTGGCA
4148  175_HRV12b    ACCCAAAAAACGTGATGATTACACATGGCAATCTGGCACCAACGCCTCAGTTTTTTGGCA
4149  176_HRV12     ACCCAAAAAACGTGATGATTACACATGGCAATCTGGCACCAACGCCTCAGTTTTTTGGCA
4150  GROUP_31      ACCCAAAAAACGTGATGATTACACATGGCAATCTGGCACCAACGCCTCAGTTTTTTGGCA
4151
4152  174_HRV12a    GGAAGGTCAACCTTACCCCAGATTCACAATCCCTTTTATTAGTATTGCCTCAGCATATTA
```

FIG. D13 CONT'D

```
09.trace                                                                9/20/2007 5:05 PM 4153  175_HRV12b    GGAAGGTCAACCTTACCCCAGATTCACAATCCCTTTTATTAGTATTGCCTCAGCATATTA
4154  176_HRV12     GGAAGGTCAACCTTACCCCAGATTCACAATCCCTTTTATTAGTATTGCCTCAGCATATTA
4155  GROUP_31      GGAAGGTCAACCTTACCCCAGATTCACAATCCCTTTTATTAGTATTGCCTCAGCATATTA
4156
4157  174_HRV12a    CATGTTTTATGATGGTTATGCTGATGACAACCCAAGTGCACCTTATGGAACTGTAGTTAC
4158  175_HRV12b    CATGTTTTATGATGGTTATGCTGATGACAACCCAAGTGCACCTTATGGAACTGTAGTTAC
4159  176_HRV12     CATGTTTTATGATGGTTATGCTGATGACAACCCAAGTGCACCTTATGGAACTGTAGTTAC
4160  GROUP_31      CATGTTTTATGATGGTTATGCTGATGACAACCCAAGTGCACCTTATGGAACTGTAGTTAC
4161
4162  174_HRV12a    CAATGACATGGGTTCACTGTGTGTCAGAATAGTTACAGACCAGCAAAAACATAAAGTTAA
4163  175_HRV12b    CAATGACATGGGTTCACTGTGTGTCAGAATAGTTACAGACCAGCAAAAACATAAAGTTAA
4164  176_HRV12     CAATGACATGGGTTCACTGTGTGTCAGAATAGTTACAGACCAGCAAAAACATAAAGTTAA
4165  GROUP_31      CAATGACATGGGTTCACTGTGTGTCAGAATAGTTACAGACCAGCAAAAACATAAAGTTAA
4166
4167  174_HRV12a    GATTACCAGTAGAATATACCATAAAGCAAAACATATCAGTGCCTGGGGCCCTAGACCACC
4168  175_HRV12b    GATTACCAGTAGAATATACCATAAAGCAAAACATATCAGTGCCTGGGGCCCTAGACCACC
4169  176_HRV12     GATTACCAGTAGAATATACCATAAAGCAAAACATATCAGTGCCTGGGGCCCTAGACCACC
4170  GROUP_31      GATTACCAGTAGAATATACCATAAAGCAAAACATATCAGTGCCTGGGGCCCTAGACCACC
4171
4172  174_HRV12a    AAGAGCTGTACCATACCAG-CATATACACAATCCAAATTACAAGA-CAAGTA------AT
4173  175_HRV12b    AAGAGCTGTACCATACCAG-CATATACACAATCCAAATTACAAGA-CAAGTA------AT
4174  176_HRV12     AAGAGCTGTACCATACCAG-CATATACACAATCCAAATTACAAGA-CAAGTA------AT
4175  GROUP_31      AAGAGCTGTACCATACCAG.CATATACACAATCCAAATTACAAGA.CAAGTA......AT
4176
4177  174_HRV12a    GGAG------TTCCAGACAATAGAGTCAAACTCAGAGAGACACTCACCACAGTA------
4178  175_HRV12b    GGAG------TTCCAGACAATAGAGTCAAACTCAGAGAGACACTCACCACAGTG------
4179  176_HRV12     GGAG------TTCCAGACAATAGAGTCAAACTCAGAGAGACACTCACCACAGTT------
4180  GROUP_31      GGAG......TTCCAGACAATAGAGTCAAACTCAGAGAGACACTCACCACAGT-......
4181
4182  174_HRV12a    --------------------
4183  175_HRV12b    --------------------
4184  176_HRV12     --------------------
4185  GROUP_31      ....................
4186
4187
4188
4189  GROUP  32:
4190
4191  177_HRV78a    AATCCAGTGGAAGAATATGTTGATCAGGTTTTAAATGAGGTTTTAGTTGTTCCAAACATA
4192  178_HRV78b    AATCCAGTGGAAGAATATGTTGATCAGGTTTTAAATGAGGTTTTAGTTGTTCCAAACATA
4193  179_HRV78     AATCCAGTGGAAGAATATGTTGATCAGGTTTTAAATGAGGTTTTAGTTGTTCCAAACATA
4194  GROUP_32      AATCCAGTGGAAGAATATGTTGATCAGGTTTTAAATGAGGTTTTAGTTGTTCCAAACATA
4195
4196  177_HRV78a    AAAGAAAGTAAACCCCAGTCTAGCAACTCCGCTCCAGTTTTGGACGCTGCAGAAACAGGT
4197  178_HRV78b    AAAGAAAGTAAACCCCAGTCTAGCAACTCCGCTCCAGTTTTGGACGCTGCAGAAACAGGT
4198  179_HRV78     AAAGAAAGTAAACCCCAGTCTAGCAACTCCGCTCCAGTTTTGGACGCTGCAGAAACAGGT
4199  GROUP_32      AAAGAAAGTAAACCCCAGTCTAGCAACTCCGCTCCAGTTTTGGACGCTGCAGAAACAGGT
4200
4201  177_HRV78a    CATACGAACCAAGTACAGCCTGAAGACACCATAGAAACTAGATATGTTATAACTGACCAA
4202  178_HRV78b    CATACGAACCAAGTACAGCCTGAAGACACCATAGAAACTAGATATGTTATAACTGACCAA
4203  179_HRV78     CATACGAACCAAGTACAGCCTGAAGACACCATAGAAACTAGATATGTTATAACTGACCAA
4204  GROUP_32      CATACGAACCAAGTACAGCCTGAAGACACCATAGAAACTAGATATGTTATAACTGACCAA
4205
4206  177_HRV78a    ACAAGAGATGAAATGAGCATTGAAAGTTTCCTCGGAAGATCAGGTTGTGCAACAATTATG
4207  178_HRV78b    ACAAGAGATGAAATGAGCATTGAAAGTTTCCTCGGAAGATCAGGTTGTGCAACAATTATG
4208  179_HRV78     ACAAGAGATGAAATGAGCATTGAAAGTTTCCTCGGAAGATCAGGTTGTGCAACAATTATG
4209  GROUP_32      ACAAGAGATGAAATGAGCATTGAAAGTTTCCTCGGAAGATCAGGTTGTGCAACAATTATG
4210
4211  177_HRV78a    AGACTAGAATTGGACCACACTGAT---------------TACAATGCT---GAAGGGAAA
4212  178_HRV78b    AGACTAGAATTGGACCACACTGAT---------------TACAATGCT---GAAGGGAAA
4213  179_HRV78     AGACTAGAATTGGACCACACTGAT---------------TACAATGCT---GAAGGGAAA
4214  GROUP_32      AGACTAGAATTGGACCACACTGAT...............TACAATGCT...GAAGGGAAA
4215
4216  177_HRV78a    AATTTTACAACGTGGAAAATCAACTTACAGGAGATGGCCCAGATTAGAAGAAAGAATGAG
4217  178_HRV78b    AATTTTACAACGTGGAAAATCAACTTACAGGAGATGGCCCAGATTAGAAGAAAGAATGAG
```

FIG. D13 CONT'D

```
09.trace                                                                                            9/20/2007 5:05 PM 4218   179_HRV78       AATTTTACAACGTGGAAAATCAACTTACAGGAGATGGCCCAGATTAGAAGAAAGAATGAG
4219   GROUP_32        AATTTTACAACGTGGAAAATCAACTTACAGGAGATGGCCCAGATTAGAAGAAAGAATGAG
4220
4221   177_HRV78a      ATGTTCACATATCTCAGATTTGATTCAGAAATCACTCTTG-TGTGTGCAGTGGCCTCACA
4222   178_HRV78b      ATGTTCACATATCTCAGATTTGATTCAGAAATCACTCTTG-TGTGTGCAGTGGCCTCACA
4223   179_HRV78       ATGTTCACATATCTCAGATTTGATTCAGAAATCACTCTTG-TGTGTGCAGTGGCCTCACA
4224   GROUP_32        ATGTTCACATATCTCAGATTTGATTCAGAAATCACTCTTG.TGTGTGCAGTGGCCTCACA
4225
4226   177_HRV78a      AGGAGACAATAATGGACATGTGGTGCTTCAATTTATGTTTGTTCCACCTGGAGCCCCTAT
4227   178_HRV78b      AGGAGACAATAATGGACATGTGGTGCTTCAATTTATGTTTGTTCCACCTGGAGCCCCTAT
4228   179_HRV78       AGGAGACAATAATGGACATGTGGTGCTTCAATTTATGTTTGTTCCACCTGGAGCCCCTAT
4229   GROUP_32        AGGAGACAATAATGGACATGTGGTGCTTCAATTTATGTTTGTTCCACCTGGAGCCCCTAT
4230
4231   177_HRV78a      ACCAAAGAAGAGAGATGACTATACTTGGCAGTCAGGCACCAATGCATCTGTGTTTTGGCA
4232   178_HRV78b      ACCAAAGAAGAGAGATGACTATACTTGGCAGTCAGGCACCAATGCATCTGTGTTTTGGCA
4233   179_HRV78       ACCAAAGAAGAGAGATGACTATACTTGGCAGTCAGGCACCAATGCATCTGTGTTTTGGCA
4234   GROUP_32        ACCAAAGAAGAGAGATGACTATACTTGGCAGTCAGGCACCAATGCATCTGTGTTTTGGCA
4235
4236   177_HRV78a      ACAAGGTCAAACATACCCCAGGTTCTCTATACCATTTTCTAGTATTGCCTCAGCTTATTA
4237   178_HRV78b      ACAAGGTCAAACATACCCCAGGTTCTCTATACCATTTTCTAGTATTGCCTCAGCTTATTA
4238   179_HRV78       ACAAGGTCAAACATACCCCAGGTTCTCTATACCATTTTCTAGTATTGCCTCAGCTTATTA
4239   GROUP_32        ACAAGGTCAAACATACCCCAGGTTCTCTATACCATTTTCTAGTATTGCCTCAGCTTATTA
4240
4241   177_HRV78a      CATGTTTTATGATGGATACTCGGATGACAGCACATCCTCTCCATATGGCACTGTAGTTAC
4242   178_HRV78b      CATGTTTTATGATGGATACTCGGATGACAGCACATCCTCTCCATATGGCACTGTAGTTAC
4243   179_HRV78       CATGTTTTATGATGGATACTCGGATGACAGCACATCCTCTCCATATGGCACTGTAGTTAC
4244   GROUP_32        CATGTTTTATGATGGATACTCGGATGACAGCACATCCTCTCCATATGGCACTGTAGTTAC
4245
4246   177_HRV78a      CAATGACATGGGTACACTGTGTATGAGGATGGTTACAGATCAACAACAACATAAGGTCAC
4247   178_HRV78b      CAATGACATGGGTACACTGTGTATGAGGATGGTTACAGATCAACAACAACATAAGGTCAC
4248   179_HRV78       CAATGACATGGGTACACTGTGTATGAGGATGGTTACAGATCAACAACAACATAAGGTCAC
4249   GROUP_32        CAATGACATGGGTACACTGTGTATGAGGATGGTTACAGATCAACAACAACATAAGGTCAC
4250
4251   177_HRV78a      AATTACAGCTAGAGTCTACCACAAGGCCAAACATATTAGTGCATGGGGCCCAAGACCTCC
4252   178_HRV78b      AATTACAGCTAGAGTCTACCACAAGGCCAAACATATTAGTGCATGGGGCCCAAGACCTCC
4253   179_HRV78       AATTACAGCTAGAGTCTACCACAAGGCCAAACATATTAGTGCATGGGGCCCAAGACCTCC
4254   GROUP_32        AATTACAGCTAGAGTCTACCACAAGGCCAAACATATTAGTGCATGGGGCCCAAGACCTCC
4255
4256   177_HRV78a      TAGAGCTGTACCTTATCAG-CACATATATAACCCTAATTATAAAA-CTGAAG------AA
4257   178_HRV78b      TAGAGCTGTACCTTATCAG-CACATATATAACCCTAATTATAAAA-CTGAAG------AA
4258   179_HRV78       TAGAGCTGTACCTTATCAG-CACATATATAACCCTAATTATAAAA-CTGAAG------AA
4259   GROUP_32        TAGAGCTGTACCTTATCAG.CACATATATAACCCTAATTATAAAA.CTGAAG......AA
4260
4261   177_HRV78a      GGAA------CTCCAGACACCAAAGTGGCAATTAGAGCTAATATTAAAACTGTA------
4262   178_HRV78b      GGAA------CTCCAGACACCAAAGTGGCAATTAGAGCTAATATTAAAACTGTG------
4263   179_HRV78       GGAA------CTCCAGACACCAAAGTGGCAATTAGAGCTAATATTAAAACTGTT------
4264   GROUP_32        GGAA......CTCCAGACACCAAAGTGGCAATTAGAGCTAATATTAAAACTGT-......
4265
4266   177_HRV78a      --------------------
4267   178_HRV78b      --------------------
4268   179_HRV78       --------------------
4269   GROUP_32        ....................
4270
4271
4272
4273   GROUP  33:
4274
4275   180_HRV20       AACCCAGTGGAAAGGTACACAGAAGCTATTTTAAATGAAGTTCTTGTAGTTCCAAATATC
4276   181_HRV20a      AACCCAGTGGAAAGGTACACAGAAGCTATTTTAAATGAAGTTCTTGTAGTTCCAAATATC
4277   182_HRV20b      AACCCAGTGGAAAGGTACACAGAAGCTATTTTAAATGAAGTTCTTGTAGTTCCAAATATC
4278   183_HRV68       AACCCAGTTGAAAAATACACAGAAGCCGTTCTTAATGAGGTCCTTGTGGTTCCAAACATA
4279   184_HRV68a      AACCCAGTTGAAAAATACACAGAAGCCGTTCTTAATGAGGTCCTTGTGGTTCCAAACATA
4280   185_HRV68b      AACCCAGTTGAAAAATACACAGAAGCCGTTCTTAATGAGGTCCTTGTGGTTCCAAACATA
4281   GROUP_33        AACCCAGT-GAAA--TACACAGAAGC--TT-T-AATGA-GT-CTTGT-GTTCCAAA-AT-
```

FIG. D13 CONT'D

```
09.trace                                                                                9/20/2007 5:05 PM 4282
4283 180_HRV20      ACATCTAGTAACTCCCAAACATCAAATGCAGCACCAGCACTAGATGCTGCTGAGACAGGA
4284 181_HRV20a     ACATCTAGTAACTCCCAAACATCAAATGCAGCACCAGCACTAGATGCTGCTGAGACAGGA
4285 182_HRV20b     ACATCTAGTAACTCCCAAACATCAAATGCAGCACCAGCACTAGATGCTGCTGAGACAGGA
4286 183_HRV68      CCAGCAAGTAATACCCAAACTTCAAATGCAGCCCCAGCCTTAGATGCTGCTGAGACTGGA
4287 184_HRV68a     CCAGCAAGTAATACCCAAACTTCAAATGCAGCCCCAGCCTTAGATGCTGCTGAGACTGGA
4288 185_HRV68b     CCAGCAAGTAATACCCAAACTTCAAATGCAGCCCCAGCCTTAGATGCTGCTGAGACTGGA
4289 GROUP_33       -CA-C-AGTAA--CCCAAAC-TCAAATGCAGC-CCAGC--TAGATGCTGCTGAGAC-GGA
4290
4291 180_HRV20      CACACAAACCAGGTCCAGCCAGAAGATATGGTCGAGACACGGTATGTAATTACTGATCAG
4292 181_HRV20a     CACACAAACCAGGTCCAGCCAGAAGATATGGTCGAGACACGGTATGTAATTACTGATCAG
4293 182_HRV20b     CACACAAACCAGGTCCAGCCAGAAGATATGGTCGAGACACGGTATGTAATTACTGATCAG
4294 183_HRV68      CATACAAACCAAGTCCAACCAGAAGATGTGGTTGAAACACGCTATGTCATAACAGACCAG
4295 184_HRV68a     CATACAAACCAAGTCCAACCAGAAGATGTGGTTGAAACACGCTATGTCATAACAGACCAG
4296 185_HRV68b     CATACAAACCAAGTCCAACCAGAAGATGTGGTTGAAACACGCTATGTCATAACAGACCAG
4297 GROUP_33       CA-ACAAACCA-GTCCA-CCAGAAGAT-TGGT-GA-ACACG-TATGT-AT-AC-GA-CAG
4298
4299 180_HRV20      ACCCGTGATGAAATGAGTGTGGAAAGTTTTCTTGGTAGATCTGGTTGCATTGCTATCATA
4300 181_HRV20a     ACCCGTGATGAAATGAGTGTGGAAAGTTTTCTTGGTAGATCTGGTTGCATTGCTATCATA
4301 182_HRV20b     ACCCGTGATGAAATGAGTGTGGAAAGTTTTCTTGGTAGATCTGGTTGCATTGCTATCATA
4302 183_HRV68      ACAAGGGATGAAATGAGCATAGAGAGCTTCCTCGGTAGGTCAGGTTGCATTGCAATCATA
4303 184_HRV68a     ACAAGGGATGAAATGAGCATAGAGAGCTTCCTCGGTAGGTCAGGTTGCATTGCAATCATA
4304 185_HRV68b     ACAAGGGATGAAATGAGCATAGAGAGCTTCCTCGGTAGGTCAGGTTGCATTGCAATCATA
4305 GROUP_33       AC--G-GATGAAATGAG--T-GA-AG-TT-CT-GGTAG-TC-GGTTGCATTGC-ATCATA
4306
4307 180_HRV20      CATACTGACTTAGATCATGAAGCACAA---------CAATATAATGCA---CCCGGAAAA
4308 181_HRV20a     CATACTGACTTAGATCATGAAGCACAA---------CAATATAATGCA---CCCGGAAAA
4309 182_HRV20b     CATACTGACTTAGATCATGAAGCACAA---------CAATATAATGCA---CCCGGAAAA
4310 183_HRV68      CATACTGACTTAGATCACAATGAGGAT---------CAGTACAATGCA---CCTGGAAAA
4311 184_HRV68a     CATACTGACTTAGATCACAATGAGGAT---------CAGTACAATGCA---CCTGGAAAA
4312 185_HRV68b     CATACTGACTTAGATCACAATGAGGAT---------CAGTACAATGCA---CCTGGAAAA
4313 GROUP_33       CATACTGACTTAGATCA--A-G---A-.........CA-TA-AATGCA...CC-GGAAAA
4314
4315 180_HRV20      AATTTCTCTCAGTGGAAGATCACAATCAAGGAAATGGCTCAAATCAGAAGAAAATGTGAG
4316 181_HRV20a     AATTTCTCTCAGTGGAAGATCACAATCAAGGAAATGGCTCAAATCAGAAGAAAATGTGAG
4317 182_HRV20b     AATTTCTCTCAGTGGAAGATCACAATCAAGGAAATGGCTCAAATCAGAAGAAAATGTGAG
4318 183_HRV68      AACTTCTCCCAATGGAAAATTACAATTAAGGAAATGGCTCAAATTAGAAGAAAGTGTGAA
4319 184_HRV68a     AACTTCTCCCAATGGAAAATTACAATTAAGGAAATGGCTCAAATTAGAAGAAAGTGTGAA
4320 185_HRV68b     AACTTCTCCCAATGGAAAATTACAATTAAGGAAATGGCTCAAATTAGAAGAAAGTGTGAA
4321 GROUP_33       AA-TTCTC-CA-TGGAA-AT-ACAAT-AAGGAAATGGCTCAAAT-AGAAGAAA-TGTGA-
4322
4323 180_HRV20      CTCTTTACATACCTCAGATTTGATTCTGAGATTACAATAG-TAGCAACAGTAGCTGCACT
4324 181_HRV20a     CTCTTTACATACCTCAGATTTGATTCTGAGATTACAATAG-TAGCAACAGTAGCTGCACT
4325 182_HRV20b     CTCTTTACATACCTCAGATTTGATTCTGAGATTACAATAG-TAGCAACAGTAGCTGCACT
4326 183_HRV68      CTATTCACATACCTTAGGTTTGACTCTGAGATTACAATAG-TAGCAACAATAGCTGCTCT
4327 184_HRV68a     CTATTCACATACCTTAGGTTTGACTCTGAGATTACAATAG-TAGCAACAATAGCTGCTCT
4328 185_HRV68b     CTATTCACATACCTTAGGTTTGACTCTGAGATTACAATAG-TAGCAACAATAGCTGCTCT
4329 GROUP_33       CT-TT-ACATACCT-AG-TTTGA-TCTGAGATTACAATAG.TAGCAACA-TAGCTGC-CT
4330
4331 180_HRV20      AGGTCGGGATAATGGGCATGTTGTTTTACAGTATATGTATGTACCACCAGGGGCACCAAT
4332 181_HRV20a     AGGTCGGGATAATGGGCATGTTGTTTTACAGTATATGTATGTACCACCAGGGGCACCAAT
4333 182_HRV20b     AGGTCGGGATAATGGGCATGTTGTTTTACAGTATATGTATGTACCACCAGGGGCACCAAT
4334 183_HRV68      TGGAAAAGATAATGGCCATGTGGTTTTACAGTACATGTATGTGCCGCCAGGGGCACCCAT
4335 184_HRV68a     TGGAAAAGATAATGGCCATGTGGTTTTACAGTACATGTATGTGCCGCCAGGGGCACCCAT
4336 185_HRV68b     TGGAAAAGATAATGGCCATGTGGTTTTACAGTACATGTATGTGCCGCCAGGGGCACCCAT
4337 GROUP_33       -GG----GATAATGG-CATGT-GTTTTACAGTA-ATGTATGT-CC-CCAGGGGCACC-AT
4338
4339 180_HRV20      ACCAAAGACTAGAGATGACTACACATGGCAATCAGGGACAAATGCATCAGTATTTTGGCA
4340 181_HRV20a     ACCAAAGACTAGAGATGACTACACATGGCAATCAGGGACAAATGCATCAGTATTTTGGCA
4341 182_HRV20b     ACCAAAGACTAGAGATGACTACACATGGCAATCAGGGACAAATGCATCAGTATTTTGGCA
4342 183_HRV68      ACCAAAAACTAGAGATGATTACACATGGCAGTCAGGCACTAATGCATCAGTGTTTTGGCA
4343 184_HRV68a     ACCAAAAACTAGAGATGATTACACATGGCAGTCAGGCACTAATGCATCAGTGTTTTGGCA
4344 185_HRV68b     ACCAAAAACTAGAGATGATTACACATGGCAGTCAGGCACTAATGCATCAGTGTTTTGGCA
4345 GROUP_33       ACCAAA-ACTAGAGATGA-TACACATGGCA-TCAGG-AC-AATGCATCAGT-TTTTGGCA
```

FIG. D13 CONT'D

```
09.trace                                                          9/20/2007 5:05 PM 4346
4347  180_HRV20    GCAGGGCCAACCTTACCCCAGATTTACCATTCCATTTATGAGTATAGCTTCAGCATATTA
4348  181_HRV20a   GCAGGGCCAACCTTACCCCAGATTTACCATTCCATTTATGAGTATAGCTTCAGCATATTA
4349  182_HRV20b   GCAGGGCCAACCTTACCCCAGATTTACCATTCCATTTATGAGTATAGCTTCAGCATATTA
4350  183_HRV68    ACAAGGACAACCTTACCCCAGATTTACCATTCCATTTATGAGTATAGCTTCAGCATATTA
4351  184_HRV68a   ACAAGGACAACCTTACCCCAGATTTACCATTCCATTTATGAGTATAGCTTCAGCATATTA
4352  185_HRV68b   ACAAGGACAACCTTACCCCAGATTTACCATTCCATTTATGAGTATAGCTTCAGCATATTA
4353  GROUP_33     -CA-GG-CAACCTTACCCCAGATTTACCATTCCATTTATGAGTATAGCTTCAGCATATTA
4354
4355  180_HRV20    TATGTTTTATGATGGTTATGAAGATGATAAGG---GAAGTGTGTATGGGTCTGTTGTCAC
4356  181_HRV20a   TATGTTTTATGATGGTTATGAAGATGATAAGG---GAAGTGTGTATGGGTCTGTTGTCAC
4357  182_HRV20b   TATGTTTTATGATGGTTATGAAGATGATAAGG---GAAGTGTGTATGGGTCTGTTGTCAC
4358  183_HRV68    TATGTTTTATGATGGATATGAGGATGACAAAG---GAAGTGTGTATGGATCTGTTGTTAC
4359  184_HRV68a   TATGTTTTATGATGGATATGAGGATGACAAAG---GAAGTGTGTATGGATCTGTTGTTAC
4360  185_HRV68b   TATGTTTTATGATGGATATGAGGATGACAAAG---GAAGTGTGTATGGATCTGTTGTTAC
4361  GROUP_33     TATGTTTTATGATGG-TATGA-GATGA-AA-G...GAAGTGTGTATGG-TCTGTTGT-AC
4362
4363  180_HRV20    AAACGATATGGGCACATTGTGTGTTCGTATTGTGACTGAGCAGCAGACACATAAGGTTAA
4364  181_HRV20a   AAACGATATGGGCACATTGTGTGTTCGTATTGTGACTGAGCAGCAGACACATAAGGTTAA
4365  182_HRV20b   AAACGATATGGGCACATTGTGTGTTCGTATTGTGACTGAGCAGCAGACACATAAGGTTAA
4366  183_HRV68    AAATGATATGGGCACATTATGTGTCCGTATTGTGACTGAGCAGCAGACACATAGGGTCAA
4367  184_HRV68a   AAATGATATGGGCACATTATGTGTCCGTATTGTGACTGAGCAGCAGACACATAGGGTCAA
4368  185_HRV68b   AAATGATATGGGCACATTATGTGTCCGTATTGTGACTGAGCAGCAGACACATAGGGTCAA
4369  GROUP_33     AAA-GATATGGGCACATT-TGTGT-CGTATTGTGACTGAGCAGCAGACACATA-GGT-AA
4370
4371  180_HRV20    GATAACCAGTAGGATATTCCACAAGGCAAAGCATATTAGTGCATGGTGTCCAAGGGCCCC
4372  181_HRV20a   GATAACCAGTAGGATATTCCACAAGGCAAAGCATATTAGTGCATGGTGTCCAAGGGCCCC
4373  182_HRV20b   GATAACCAGTAGGATATTCCACAAGGCAAAGCATATTAGTGCATGGTGTCCAAGGGCCCC
4374  183_HRV68    AATAACCAGCAGAATATTCCATAAAGCAAAACATATTAGTGCGTGGTGTCCAAGAGCTCC
4375  184_HRV68a   AATAACCAGCAGAATATTCCATAAAGCAAAACATATTAGTGCGTGGTGTCCAAGAGCTCC
4376  185_HRV68b   AATAACCAGCAGAATATTCCATAAAGCAAAACATATTAGTGCGTGGTGTCCAAGAGCTCC
4377  GROUP_33     -ATAACCAG-AG-ATATTCCA-AA-GCAAA-CATATTAGTGC-TGGTGTCCAAG-GC-CC
4378
4379  180_HRV20    AAGAGCAGTGCCTTATCAA-CACACTAAGAGCACAAACTTAGTGC-CAAGGA---CAGGT
4380  181_HRV20a   AAGAGCAGTGCCTTATCAA-CACACTAAGAGCACAAACTTAGTGC-CAAGGA---CAGGT
4381  182_HRV20b   AAGAGCAGTGCCTTATCAA-CACACTAAGAGCACAAACTTAGTGC-CAAGGA---CAGGT
4382  183_HRV68    AAGAGCAGTGCCCTACCAG-CACACCAGAAGTACAAACTTAGTAC-CAAAGG---AAGGT
4383  184_HRV68a   AAGAGCAGTGCCCTACCAG-CACACCAGAAGTACAAACTTAGTAC-CAAAGG---AAGGT
4384  185_HRV68b   AAGAGCAGTGCCCTACCAG-CACACCAGAAGTACAAACTTAGTAC-CAAAGG---AAGGT
4385  GROUP_33     AAGAGCAGTGCC-TA-CA-.CACAC-A--AG-ACAAACTTAGT-C.CAA-G-...-AGGT
4386
4387  180_HRV20    GAAA------TTACA---ACTCATATCAGATTCAGAAACACTGTCAAAGATCTAACATAC
4388  181_HRV20a   GAAA------TTACA---ACTCATATCAGATTCAGAAACACTGTCAAAGATCTAACATAC
4389  182_HRV20b   GAAA------TTACA---ACTCATATCAGATTCAGAAACACTGTCAAAGATCTAACATAC
4390  183_HRV68    GATA------TTAAA---ACTCATATTAAATTTAGGAATACTGTTAAAGATTTGGCATAT
4391  184_HRV68a   GATA------TTAAA---ACTCATATTAAATTTAGGAATACTGTTAAAGATTTGGCATAT
4392  185_HRV68b   GATA------TTAAA---ACTCATATTAAATTTAGGAATACTGTTAAAGATTTGGCATAT
4393  GROUP_33     GA-A......TTA-A...ACTCATAT-A-ATT-AG-AA-ACTGT-AAAGAT-T--CATA-
4394
4395  180_HRV20    CCCACAGAAATGACGAATGTT
4396  181_HRV20a   CCCACAGAAATGACGAATGTA
4397  182_HRV20b   CCCACAGAAATGACGAATGTG
4398  183_HRV68    CCTCCAGAATTAGCAAACCTT
4399  184_HRV68a   CCTCCAGAATTAGCAAACCTT
4400  185_HRV68b   CCTCCAGAATTAGCAAACCTT
4401  GROUP_33     CC--CAGAA-T--C-AA--T-
4402
4403
4404
4405  GROUP  34:
4406
4407  186_HRV28    AATCCAGTTGAAAAATATACTGAAGCACTACTTAATGAAGTGCTTGTTGTGCCAAACATC
```

FIG. D13 CONT'D 09.trace                                                                                        9/20/2007 5:05 PM

```
4408  187_HRV28a    AATCCAGTTGAAAAATATACTGAAGCACTACTTAATGAAGTGCTTGTTGTGCCAAACATC
4409  188_HRV28b    AATCCAGTTGAAAAATATACTGAAGCACTACTTAATGAAGTGCTTGTTGTGCCAAACATC
4410  GROUP_34      AATCCAGTTGAAAAATATACTGAAGCACTACTTAATGAAGTGCTTGTTGTGCCAAACATC
4411
4412  186_HRV28     AATCCTAGCAACGCACAAACTACAAATGCAGCTCCCGCTCTCGATGCCGCTGAGACGGGG
4413  187_HRV28a    AATCCTAGCAACGCACAAACTACAAATGCAGCTCCCGCTCTCGATGCCGCTGAGACGGGG
4414  188_HRV28b    AATCCTAGCAACGCACAAACTACAAATGCAGCTCCCGCTCTCGATGCCGCTGAGACGGGG
4415  GROUP_34      AATCCTAGCAACGCACAAACTACAAATGCAGCTCCCGCTCTCGATGCCGCTGAGACGGGG
4416
4417  186_HRV28     CACACAAGCCAAACACAACCTGAAGACATGGTTGAGACTAGGTATGTAATCACAGATCAG
4418  187_HRV28a    CACACAAGCCAAACACAACCTGAAGACATGGTTGAGACTAGGTATGTAATCACAGATCAG
4419  188_HRV28b    CACACAAGCCAAACACAACCTGAAGACATGGTTGAGACTAGGTATGTAATCACAGATCAG
4420  GROUP_34      CACACAAGCCAAACACAACCTGAAGACATGGTTGAGACTAGGTATGTAATCACAGATCAG
4421
4422  186_HRV28     ACCCGTGATGAAATGAGTATAGAGAGTTTCTTAGGTAGGTCTAGTTGCATTGCAATAATC
4423  187_HRV28a    ACCCGTGATGAAATGAGTATAGAGAGTTTCTTAGGTAGGTCTAGTTGCATTGCAATAATC
4424  188_HRV28b    ACCCGTGATGAAATGAGTATAGAGAGTTTCTTAGGTAGGTCTAGTTGCATTGCAATAATC
4425  GROUP_34      ACCCGTGATGAAATGAGTATAGAGAGTTTCTTAGGTAGGTCTAGTTGCATTGCAATAATC
4426
4427  186_HRV28     CATACTGATGTTGTGCATGAAACAGAC--------AAGTACAACCAC---CCAGGGAAG
4428  187_HRV28a    CATACTGATGTTGTGCATGAAACAGAC--------AAGTACAACCAC---CCAGGGAAG
4429  188_HRV28b    CATACTGATGTTGTGCATGAAACAGAC--------AAGTACAACCAC---CCAGGGAAG
4430  GROUP_34      CATACTGATGTTGTGCATGAAACAGAC.........AAGTACAACCAC...CCAGGGAAG
4431
4432  186_HRV28     AATTTTAGTAAATGGAATATCACTCTCAAAGAAATGGCCCAAATCAGAAGAAAGTGTGAA
4433  187_HRV28a    AATTTTAGTAAATGGAATATCACTCTCAAAGAAATGGCCCAAATCAGAAGAAAGTGTGAA
4434  188_HRV28b    AATTTTAGTAAATGGAATATCACTCTCAAAGAAATGGCCCAAATCAGAAGAAAGTGTGAA
4435  GROUP_34      AATTTTAGTAAATGGAATATCACTCTCAAAGAAATGGCCCAAATCAGAAGAAAGTGTGAA
4436
4437  186_HRV28     ATGTTTACATATCTCAGATTTGATTCTGAAATTACTATAG-TGGTGTCAGTTGCAAGTAA
4438  187_HRV28a    ATGTTTACATATCTCAGATTTGATTCTGAAATTACTATAG-TGGTGTCAGTTGCAAGTAA
4439  188_HRV28b    ATGTTTACATATCTCAGATTTGATTCTGAAATTACTATAG-TGGTGTCAGTTGCAAGTAA
4440  GROUP_34      ATGTTTACATATCTCAGATTTGATTCTGAAATTACTATAG.TGGTGTCAGTTGCAAGTAA
4441
4442  186_HRV28     AGGTGATGATAATGGGCATGTAGTTATGCAATATATGTATGTACCTCCAGGAGCCCCCAT
4443  187_HRV28a    AGGTGATGATAATGGGCATGTAGTTATGCAATATATGTATGTACCTCCAGGAGCCCCCAT
4444  188_HRV28b    AGGTGATGATAATGGGCATGTAGTTATGCAATATATGTATGTACCTCCAGGAGCCCCCAT
4445  GROUP_34      AGGTGATGATAATGGGCATGTAGTTATGCAATATATGTATGTACCTCCAGGAGCCCCCAT
4446
4447  186_HRV28     CCCCACTACCAGAAATGATTACACATGGCAATCCAGTACCAATGCCTCTGTTTTCTGGCA
4448  187_HRV28a    CCCCACTACCAGAAATGATTACACATGGCAATCCAGTACCAATGCCTCTGTTTTCTGGCA
4449  188_HRV28b    CCCCACTACCAGAAATGATTACACATGGCAATCCAGTACCAATGCCTCTGTTTTCTGGCA
4450  GROUP_34      CCCCACTACCAGAAATGATTACACATGGCAATCCAGTACCAATGCCTCTGTTTTCTGGCA
4451
4452  186_HRV28     ACAAGGACAACCATATCCCAGATTCACTATACCTTTTATGAGTATTGCCTCAGCTTATTA
4453  187_HRV28a    ACAAGGACAACCATATCCCAGATTCACTATACCTTTTATGAGTATTGCCTCAGCTTATTA
4454  188_HRV28b    ACAAGGACAACCATATCCCAGATTCACTATACCTTTTATGAGTATTGCCTCAGCTTATTA
4455  GROUP_34      ACAAGGACAACCATATCCCAGATTCACTATACCTTTTATGAGTATTGCCTCAGCTTATTA
4456
4457  186_HRV28     CATGTTTTATGATGGTTATGAAGATGACAATG---GAACTACCTATGGTGCAGTGGTTAC
4458  187_HRV28a    CATGTTTTATGATGGTTATGAAGATGACAATG---GAACTACCTATGGTGCAGTGGTTAC
4459  188_HRV28b    CATGTTTTATGATGGTTATGAAGATGACAATG---GAACTACCTATGGTGCAGTGGTTAC
4460  GROUP_34      CATGTTTTATGATGGTTATGAAGATGACAATG...GAACTACCTATGGTGCAGTGGTTAC
4461
4462  186_HRV28     AAATCATATGGGAACACTCTGTGCTCGCATAGTAACTGAACAACAGAAGCATGAAGTCAA
4463  187_HRV28a    AAATCATATGGGAACACTCTGTGCTCGCATAGTAACTGAACAACAGAAGCATGAAGTCAA
4464  188_HRV28b    AAATCATATGGGAACACTCTGTGCTCGCATAGTAACTGAACAACAGAAGCATGAAGTCAA
4465  GROUP_34      AAATCATATGGGAACACTCTGTGCTCGCATAGTAACTGAACAACAGAAGCATGAAGTCAA
4466
4467  186_HRV28     AATAACCAGCATAATATTCCACAAAGCTAAACATGTCAGTGCATGGTGCCCCAGACCTCC
4468  187_HRV28a    AATAACCAGCATAATATTCCACAAAGCTAAACATGTCAGTGCATGGTGCCCCAGACCTCC
4469  188_HRV28b    AATAACCAGCATAATATTCCACAAAGCTAAACATGTCAGTGCATGGTGCCCCAGACCTCC
4470  GROUP_34      AATAACCAGCATAATATTCCACAAAGCTAAACATGTCAGTGCATGGTGCCCCAGACCTCC
4471
4472  186_HRV28     ACGCGCTGTAGCTTATCAA-CATACATACAGTCCAAACTTTGTGC-CTCAGG---AAGGT
```

FIG. D13 CONT'D 09.trace                                                                              9/20/2007 5:05 PM

```
4473 187_HRV28a   ACGCGCTGTAGCTTATCAA-CATACATACAGTCCAAACTTTGTGC-CTCAGG---AAGGT
4474 188_HRV28b   ACGCGCTGTAGCTTATCAA-CATACATACAGTCCAAACTTTGTGC-CTCAGG---AAGGT
4475 GROUP_34     ACGCGCTGTAGCTTATCAA.CATACATACAGTCCAAACTTTGTGC.CTCAGG...AAGGT
4476
4477 186_HRV28    GATG------TTGAG---ACTCATATTAAATTTAGAACAGATGTTAAACAGATCACAA--
4478 187_HRV28a   GATG------TTGAG---ACTCATATTAAATTTAGAACAGATGTTAAACAGATCACAA--
4479 188_HRV28b   GATG------TTGAG---ACTCATATTAAATTTAGAACAGATGTTAAACAGATCACAA--
4480 GROUP_34     GATG......TTGAG...ACTCATATTAAATTTAGAACAGATGTTAAACAGATCACAA..
4481
4482 186_HRV28    ----CAGTT------------
4483 187_HRV28a   ----CAGTA------------
4484 188_HRV28b   ----CAGTC------------
4485 GROUP_34     ....CAGT-............
4486
4487
4488
4489 GROUP 35:
4490
4491 189_HRV53a   AACCCGGTAGAGAAATACACAGAGGCTATCTTAAATGAAGTATTAGTAGTCCCAAACATT
4492 190_HRV53b   AACCCGGTAGAGAAATACACAGAGGCTATCTTAAATGAAGTATTAGTAGTCCCAAACATT
4493 191_HRV53    AACCCGGTAGAGAAATACACAGAGGCTATCTTAAATGAAGTATTAGTAGTCCCAAACATT
4494 GROUP_35     AACCCGGTAGAGAAATACACAGAGGCTATCTTAAATGAAGTATTAGTAGTCCCAAACATT
4495
4496 189_HRV53a   AATGCAAGCAATCCACAAACTTCAAATTCAGCACCAGCACTAGATGCTGCAGAAACGGGT
4497 190_HRV53b   AATGCAAGCAATCCACAAACTTCAAATTCAGCACCAGCACTAGATGCTGCAGAAACGGGT
4498 191_HRV53    AATGCAAGCAATCCACAAACTTCAAATTCAGCACCAGCACTAGATGCTGCAGAAACGGGT
4499 GROUP_35     AATGCAAGCAATCCACAAACTTCAAATTCAGCACCAGCACTAGATGCTGCAGAAACGGGT
4500
4501 189_HRV53a   CATACAAGTCAGACACAACCTGAGGACATGCTGGAAACTAGATATGTCATCACAGACCAA
4502 190_HRV53b   CATACAAGTCAGACACAACCTGAGGACATGCTGGAAACTAGATATGTCATCACAGACCAA
4503 191_HRV53    CATACAAGTCAGACACAACCTGAGGACATGCTGGAAACTAGATATGTCATCACAGACCAA
4504 GROUP_35     CATACAAGTCAGACACAACCTGAGGACATGCTGGAAACTAGATATGTCATCACAGACCAA
4505
4506 189_HRV53a   ACCCGGGATGAAATGAGCATTGAAAGTTTCTTAGGCAGATCAAGTTGCATTGCTGAGATC
4507 190_HRV53b   ACCCGGGATGAAATGAGCATTGAAAGTTTCTTAGGCAGATCAAGTTGCATTGCTGAGATC
4508 191_HRV53    ACCCGGGATGAAATGAGCATTGAAAGTTTCTTAGGCAGATCAAGTTGCATTGCTGAGATC
4509 GROUP_35     ACCCGGGATGAAATGAGCATTGAAAGTTTCTTAGGCAGATCAAGTTGCATTGCTGAGATC
4510
4511 189_HRV53a   CATACCAATTTAGACCAT---ACTG-----------GATACAATGAG---CCTGGGAAA
4512 190_HRV53b   CATACCAATTTAGACCAT---ACTG-----------GATACAATGAG---CCTGGGAAA
4513 191_HRV53    CATACCAATTTAGACCAT---ACTG-----------GATACAATGAG---CCTGGGAAA
4514 GROUP_35     CATACCAATTTAGACCAT...ACTG...........GATACAATGAG...CCTGGGAAA
4515
4516 189_HRV53a   AACCACTCAGAATGGAAGATTACACTCAAAGAAATGGCCCAGATTAGAAGGAAATGTGAG
4517 190_HRV53b   AACCACTCAGAATGGAAGATTACACTCAAAGAAATGGCCCAGATTAGAAGGAAATGTGAG
4518 191_HRV53    AACCACTCAGAATGGAAGATTACACTCAAAGAAATGGCCCAGATTAGAAGGAAATGTGAG
4519 GROUP_35     AACCACTCAGAATGGAAGATTACACTCAAAGAAATGGCCCAGATTAGAAGGAAATGTGAG
4520
4521 189_HRV53a   ATGTTCACATATCTTAGATTTGATTCAGAAATAACTATAG-TGGTATCAGTGGCTAGTAA
4522 190_HRV53b   ATGTTCACATATCTTAGATTTGATTCAGAAATAACTATAG-TGGTATCAGTGGCTAGTAA
4523 191_HRV53    ATGTTCACATATCTTAGATTTGATTCAGAAATAACTATAG-TGGTATCAGTGGCTAGTAA
4524 GROUP_35     ATGTTCACATATCTTAGATTTGATTCAGAAATAACTATAG.TGGTATCAGTGGCTAGTAA
4525
4526 189_HRV53a   ACAAGGGAATAACGGGCACGTGGTGATACAATACATGTATGTACCACCGGGTGCTCCAAT
4527 190_HRV53b   ACAAGGGAATAACGGGCACGTGGTGATACAATACATGTATGTACCACCGGGTGCTCCAAT
4528 191_HRV53    ACAAGGGAATAACGGGCACGTGGTGATACAATACATGTATGTACCACCGGGTGCTCCAAT
4529 GROUP_35     ACAAGGGAATAACGGGCACGTGGTGATACAATACATGTATGTACCACCGGGTGCTCCAAT
4530
4531 189_HRV53a   ACCCAAAACCAGAGATGACTATACCTGGCAATCTGGAACTAATGCTTCAGTCTTTTGGCA
4532 190_HRV53b   ACCCAAAACCAGAGATGACTATACCTGGCAATCTGGAACTAATGCTTCAGTCTTTTGGCA
4533 191_HRV53    ACCCAAAACCAGAGATGACTATACCTGGCAATCTGGAACTAATGCTTCAGTCTTTTGGCA
4534 GROUP_35     ACCCAAAACCAGAGATGACTATACCTGGCAATCTGGAACTAATGCTTCAGTCTTTTGGCA
4535
4536 189_HRV53a   ACAAGGACAACCATACCCTAGATTCACAATCCCTTTCATGAGTATTGCGTCAGCATATTA
4537 190_HRV53b   ACAAGGACAACCATACCCTAGATTCACAATCCCTTTCATGAGTATTGCGTCAGCATATTA
```

FIG. D13 CONT'D

```
09.trace                                                                    9/20/2007 5:05 PM 4538  191_HRV53    ACAAGGACAACCATACCCTAGATTCACAATCCCTTTCATGAGTATTGCGTCAGCATATTA
4539  GROUP_35     ACAAGGACAACCATACCCTAGATTCACAATCCCTTTCATGAGTATTGCGTCAGCATATTA
4540
4541  189_HRV53a   TATGTTCTATGATGGGTATGAAGATGACAATG---GCACCACTTATGGGGCTGTTGTTAC
4542  190_HRV53b   TATGTTCTATGATGGGTATGAAGATGACAATG---GCACCACTTATGGGGCTGTTGTTAC
4543  191_HRV53    TATGTTCTATGATGGGTATGAAGATGACAATG---GCACCACTTATGGGGCTGTTGTTAC
4544  GROUP_35     TATGTTCTATGATGGGTATGAAGATGACAATG...GCACCACTTATGGGGCTGTTGTTAC
4545
4546  189_HRV53a   TAATGATATGGGAACACTTTGTGTGCGCATAGTGACTGAGCAACAGAAAAATGAGGTCAA
4547  190_HRV53b   TAATGATATGGGAACACTTTGTGTGCGCATAGTGACTGAGCAACAGAAAAATGAGGTCAA
4548  191_HRV53    TAATGATATGGGAACACTTTGTGTGCGCATAGTGACTGAGCAACAGAAAAATGAGGTCAA
4549  GROUP_35     TAATGATATGGGAACACTTTGTGTGCGCATAGTGACTGAGCAACAGAAAAATGAGGTCAA
4550
4551  189_HRV53a   GATAACCAGTAGGATTTATCACAAGGCTAAACATATCAGTGCATGGTGTCCAAGACCACC
4552  190_HRV53b   GATAACCAGTAGGATTTATCACAAGGCTAAACATATCAGTGCATGGTGTCCAAGACCACC
4553  191_HRV53    GATAACCAGTAGGATTTATCACAAGGCTAAACATATCAGTGCATGGTGTCCAAGACCACC
4554  GROUP_35     GATAACCAGTAGGATTTATCACAAGGCTAAACATATCAGTGCATGGTGTCCAAGACCACC
4555
4556  189_HRV53a   AAGAGCAGTTGCATATCAA-CACACATATAGCCCAAATTTTGTAC-CGCAAA---CAGGA
4557  190_HRV53b   AAGAGCAGTTGCATATCAA-CACACATATAGCCCAAATTTTGTAC-CGCAAA---CAGGA
4558  191_HRV53    AAGAGCAGTTGCATATCAA-CACACATATAGCCCAAATTTTGTAC-CGCAAA---CAGGA
4559  GROUP_35     AAGAGCAGTTGCATATCAA.CACACATATAGCCCAAATTTTGTAC.CGCAAA...CAGGA
4560
4561  189_HRV53a   ACAG------TTGAA---ACTCACATTAAGTTCAGACCTGATGTTAAAGATGTAACAT--
4562  190_HRV53b   ACAG------TTGAA---ACTCACATTAAGTTCAGACCTGATGTTAAAGATGTAACAT--
4563  191_HRV53    ACAG------TTGAA---ACTCACATTAAGTTCAGACCTGATGTTAAAGATGTAACAT--
4564  GROUP_35     ACAG......TTGAA...ACTCACATTAAGTTCAGACCTGATGTTAAAGATGTAACAT..
4565
4566  189_HRV53a   ----CAGTAATGACAGCT---
4567  190_HRV53b   ----CAGTAATGACAGCT---
4568  191_HRV53    ----CAGTAATGACAGCA---
4569  GROUP_35     ....CAGTAATGACAGC-...
4570
4571
4572
4573  GROUP  36:
4574
4575  192_HRV46a   AATCCAGTGGAAAAATATACAGAAGCTGTTCTTAATGAGGTCCTTGTAGTACCTAACATC
4576  193_HRV46b   AATCCAGTGGAAAAATATACAGAAGCTGTTCTTAATGAGGTCCTTGTAGTACCTAACATC
4577  194_HRV46    AATCCAGTGGAAAAATATACAGAAGCTGTTCTTAATGAGGTCCTTGTAGTACCTAACATC
4578  195_HRV80a   AATCCAGTCGAAAAATACACAGAAGCAATCCTCAATGAAGTTCTTGTTGTACCAAACATC
4579  196_HRV80b   AATCCAGTCGAAAAATACACAGAAGCAATCCTCAATGAAGTTCTTGTTGTACCAAACATC
4580  197_HRV80    AATCCAGTCGAAAAATACACAGAAGCAATCCTCAATGAAGTTCTTGTTGTACCAAACATC
4581  GROUP_36     AATCCAGT-GAAAAATA-ACAGAAGC--T-CT-AATGA-GT-CTTGT-GTACC-AACATC
4582
4583  192_HRV46a   AATGCCAGTAGTGGACATACATCTAATTCAGCTCCAGCACTTGATGCAGCAGAAACTGGA
4584  193_HRV46b   AATGCCAGTAGTGGACATACATCTAATTCAGCTCCAGCACTTGATGCAGCAGAAACTGGA
4585  194_HRV46    AATGCCAGTAGTGGACATACATCTAATTCAGCTCCAGCACTTGATGCAGCAGAAACTGGA
4586  195_HRV80a   AGTGCTAGCAATGGACATACATCAAACTCAGCTCCAACACTTGATGCAGCAGAAACTGGT
4587  196_HRV80b   AGTGCTAGCAATGGACATACATCAAACTCAGCTCCAACACTTGATGCAGCAGAAACTGGT
4588  197_HRV80    AGTGCTAGCAATGGACATACATCAAACTCAGCTCCAACACTTGATGCAGCAGAAACTGGT
4589  GROUP_36     A-TGC-AG-A-TGGACATACATC-AA-TCAGCTCCA-CACTTGATGCAGCAGAAACTGG-
4590
4591  192_HRV46a   CACACTAGCCAGATACAACCAGAAGACATGATAGAAACCAGATATGTTATCACAGACCAA
4592  193_HRV46b   CACACTAGCCAGATACAACCAGAAGACATGATAGAAACCAGATATGTTATCACAGACCAA
4593  194_HRV46    CACACTAGCCAGATACAACCAGAAGACATGATAGAAACCAGATATGTTATCACAGACCAA
4594  195_HRV80a   CACACTAGCCAGGTGCAACCAGAAGACATGATAGAAACTAGATATGTTATTACTGATCAG
4595  196_HRV80b   CACACTAGCCAGGTGCAACCAGAAGACATGATAGAAACTAGATATGTTATTACTGATCAG
4596  197_HRV80    CACACTAGCCAGGTGCAACCAGAAGACATGATAGAAACTAGATATGTTATTACTGATCAG
4597  GROUP_36     CACACTAGCCAG-T-CAACCAGAAGACATGATAGAAAC-AGATATGTTAT-AC-GA-CA-
4598
4599  192_HRV46a   ACAAAAGATGAAATGAGTATAGAAAGTTTTCTAGGAAGGTCAGGCTGCATTGCCATTATT
4600  193_HRV46b   ACAAAAGATGAAATGAGTATAGAAAGTTTTCTAGGAAGGTCAGGCTGCATTGCCATTATT
4601  194_HRV46    ACAAAAGATGAAATGAGTATAGAAAGTTTTCTAGGAAGGTCAGGCTGCATTGCCATTATT
4602  195_HRV80a   ACAAAGGATGAGATGAGCATTGAAAGTTTCTTAGGAAGATCTGGTTGTGTTGCTATCATT
```

FIG. D13 CONT'D

```
09.trace                                                                  9/20/2007 5:05 PM 4603  196_HRV80b    ACAAAGGATGAGATGAGCATTGAAAGTTTCTTAGGAAGATCTGGTTGTGTTGCTATCATT
4604  197_HRV80     ACAAAGGATGAGATGAGCATTGAAAGTTTCTTAGGAAGATCTGGTTGTGTTGCTATCATT
4605  GROUP_36     ACAAA-GATGA-ATGAG-AT-GAAAGTTT--TAGGAAG-TC-GG-TG--TTGC-AT-ATT
4606
4607  192_HRV46a    GAGACAGAATTGAATCATGAAGAAGGG---------AAATACAATGCA---GAAGATCAA
4608  193_HRV46b    GAGACAGAATTGAATCATGAAGAAGGG---------AAATACAATGCA---GAAGATCAA
4609  194_HRV46     GAGACAGAATTGAATCATGAAGAAGGG---------AAATACAATGCA---GAAGATCAA
4610  195_HRV80a    GAAACCAAATTAAACCATGAAACAGAC---------ATGTACAATGCT---GATGGTCAG
4611  196_HRV80b    GAAACCAAATTAAACCATGAAACAGAC---------ATGTACAATGCT---GATGGTCAG
4612  197_HRV80     GAAACCAAATTAAACCATGAAACAGAC---------ATGTACAATGCT---GATGGTCAG
4613  GROUP_36     GA-AC--AATT-AA-CATGAA--AG--.........A--TACAATGC-...GA-G-TCA-
4614
4615  192_HRV46a    AACTTCTCAAAATGGAAAATAACACTGTTGGAAATGGCACAAATCAGAAGAAAGTGTGAA
4616  193_HRV46b    AACTTCTCAAAATGGAAAATAACACTGTTGGAAATGGCACAAATCAGAAGAAAGTGTGAA
4617  194_HRV46     AACTTCTCAAAATGGAAAATAACACTGTTGGAAATGGCACAAATCAGAAGAAAGTGTGAA
4618  195_HRV80a    AATTTTTCAAAGTGGAAAATAACATTAATGGAAATGGCACAAATTAGAAGAAAGTGTGAG
4619  196_HRV80b    AATTTTTCAAAGTGGAAAATAACATTAATGGAAATGGCACAAATTAGAAGAAAGTGTGAG
4620  197_HRV80     AATTTTTCAAAGTGGAAAATAACATTAATGGAAATGGCACAAATTAGAAGAAAGTGTGAG
4621  GROUP_36     AA-TT-TCAAA-TGGAAAATAACA-T--TGGAAATGGCACAAAT-AGAAGAAAGTGTGA-
4622
4623  192_HRV46a    CTTTTTACATATCTCAGATTTGATTCAGAAATAACAATAG-TCACCACATTGGCAGGCCA
4624  193_HRV46b    CTTTTTACATATCTCAGATTTGATTCAGAAATAACAATAG-TCACCACATTGGCAGGCCA
4625  194_HRV46     CTTTTTACATATCTCAGATTTGATTCAGAAATAACAATAG-TCACCACATTGGCAGGCCA
4626  195_HRV80a    CTTTTCACTTACCTCAGATTTGACTCAGAAATAACAATAG-TAACTACCTTAGCAGGACA
4627  196_HRV80b    CTTTTCACTTACCTCAGATTTGACTCAGAAATAACAATAG-TAACTACCTTAGCAGGACA
4628  197_HRV80     CTTTTCACTTACCTCAGATTTGACTCAGAAATAACAATAG-TAACTACCTTAGCAGGACA
4629  GROUP_36     CTTTT-AC-TA-CTCAGATTTGA-TCAGAAATAACAATAG.T-AC-AC-TT-GCAGG-CA
4630
4631  192_HRV46a    AGGGGATGATATTGGACATGTGGTCATACAATATATGTATGTGCCTCCTGGTGCTCCATT
4632  193_HRV46b    AGGGGATGATATTGGACATGTGGTCATACAATATATGTATGTGCCTCCTGGTGCTCCATT
4633  194_HRV46     AGGGGATGATATTGGACATGTGGTCATACAATATATGTATGTGCCTCCTGGTGCTCCATT
4634  195_HRV80a    AGGGGAGGACATTGGTCATGTAGTTATTCAATACATGTACGTACCACCAGGGGCCCCGTT
4635  196_HRV80b    AGGGGAGGACATTGGTCATGTAGTTATTCAATACATGTACGTACCACCAGGGGCCCCGTT
4636  197_HRV80     AGGGGAGGACATTGGTCATGTAGTTATTCAATACATGTACGTACCACCAGGGGCCCCGTT
4637  GROUP_36     AGGGGA-GA-ATTGG-CATGT-GT-AT-CAATA-ATGTA-GT-CC-CC-GG-GC-CC-TT
4638
4639  192_HRV46a    ACCGAGATATCGGAATGATTATACTTGGCAGTCTGGTACTAATGCTTCAGTGTTCTGGCA
4640  193_HRV46b    ACCGAGATATCGGAATGATTATACTTGGCAGTCTGGTACTAATGCTTCAGTGTTCTGGCA
4641  194_HRV46     ACCGAGATATCGGAATGATTATACTTGGCAGTCTGGTACTAATGCTTCAGTGTTCTGGCA
4642  195_HRV80a    GCCAAACAAACGCAATGATTATACTTGGCAGTCTGGCACGAATGCTTCAGTCTTCTGGCA
4643  196_HRV80b    GCCAAACAAACGCAATGATTATACTTGGCAGTCTGGCACGAATGCTTCAGTCTTCTGGCA
4644  197_HRV80     GCCAAACAAACGCAATGATTATACTTGGCAGTCTGGCACGAATGCTTCAGTCTTCTGGCA
4645  GROUP_36     -CC-A---A-CG-AATGATTATACTTGGCAGTCTGG-AC-AATGCTTCAGT-TTCTGGCA
4646
4647  192_HRV46a    GCAAGGGCAGCCATACCCTAGATTCACTATCCCGTTCATGAGTATAGCCTCAGCATATTA
4648  193_HRV46b    GCAAGGGCAGCCATACCCTAGATTCACTATCCCGTTCATGAGTATAGCCTCAGCATATTA
4649  194_HRV46     GCAAGGGCAGCCATACCCTAGATTCACTATCCCGTTCATGAGTATAGCCTCAGCATATTA
4650  195_HRV80a    ACAGGGTCAGCCATACCCCAGATTCACTATTCCATTCATGAGTATAGCCTCAGCTTATTA
4651  196_HRV80b    ACAGGGTCAGCCATACCCCAGATTCACTATTCCATTCATGAGTATAGCCTCAGCTTATTA
4652  197_HRV80     ACAGGGTCAGCCATACCCCAGATTCACTATTCCATTCATGAGTATAGCCTCAGCTTATTA
4653  GROUP_36     -CA-GG-CAGCCATACCC-AGATTCACTAT-CC-TTCATGAGTATAGCCTCAGC-TATTA
4654
4655  192_HRV46a    CATGTTTTATGATGGCTACGAAAGTGATAAAG---GCAAGATCTATGGAACTGCAGTCAC
4656  193_HRV46b    CATGTTTTATGATGGCTACGAAAGTGATAAAG---GCAAGATCTATGGAACTGCAGTCAC
4657  194_HRV46     CATGTTTTATGATGGCTACGAAAGTGATAAAG---GCAAGATCTATGGAACTGCAGTCAC
4658  195_HRV80a    CATGTTCTATGATGGGTATGAGAGTGATAAAG---GCAACATTTATGGAACAGCAGTTAC
4659  196_HRV80b    CATGTTCTATGATGGGTATGAGAGTGATAAAG---GCAACATTTATGGAACAGCAGTTAC
4660  197_HRV80     CATGTTCTATGATGGGTATGAGAGTGATAAAG---GCAACATTTATGGAACAGCAGTTAC
4661  GROUP_36     CATGTT-TATGATGG-TA-GA-AGTGATAAAG...GCAA-AT-TATGGAAC-GCAGT-AC
4662
4663  192_HRV46a    CAATGATATGGGAACTATATGTGTCAGAATTGTTACCGAACAACAAAAACATAAGGTTCT
4664  193_HRV46b    CAATGATATGGGAACTATATGTGTCAGAATTGTTACCGAACAACAAAAACATAAGGTTCT
4665  194_HRV46     CAATGATATGGGAACTATATGTGTCAGAATTGTTACCGAACAACAAAAACATAAGGTTCT
```

FIG. D13 CONT'D

```
09.trace                                                                  9/20/2007 5:05 PM 4666  195_HRV80a   CAATGATATGGGAACCCTGTGTGCTAGAATTGTTACAGAACAACAGAAACATAAAGTCCT
4667  196_HRV80b   CAATGATATGGGAACCCTGTGTGCTAGAATTGTTACAGAACAACAGAAACATAAAGTCCT
4668  197_HRV80    CAATGATATGGGAACCCTGTGTGCTAGAATTGTTACAGAACAACAGAAACATAAAGTCCT
4669  GROUP_36     CAATGATATGGGAAC--T-TGTG--AGAATTGTTAC-GAACAACA-AAACATAA-GT-CT
4670
4671  192_HRV46a   TATAACTAGCAGAATATATCACAAGGCTAAACACATTAAAGCATGGTGCCCCAGGGCACC
4672  193_HRV46b   TATAACTAGCAGAATATATCACAAGGCTAAACACATTAAAGCATGGTGCCCCAGGGCACC
4673  194_HRV46    TATAACTAGCAGAATATATCACAAGGCTAAACACATTAAAGCATGGTGCCCCAGGGCACC
4674  195_HRV80a   AATCACCAGCAGAATATATCACAAAGCTAAACACATCAAAGCATGGTGTCCAAGAGCACC
4675  196_HRV80b   AATCACCAGCAGAATATATCACAAAGCTAAACACATCAAAGCATGGTGTCCAAGAGCACC
4676  197_HRV80    AATCACCAGCAGAATATATCACAAAGCTAAACACATCAAAGCATGGTGTCCAAGAGCACC
4677  GROUP_36     -AT-AC-AGCAGAATATATCACAA-GCTAAACACAT-AAAGCATGGTG-CC-AG-GCACC
4678
4679  192_HRV46a   CAGAGCAGTCCCATATCAA-CATATTTATAATCCAAATTTCAAGA-CTACTCAACCTGAG
4680  193_HRV46b   CAGAGCAGTCCCATATCAA-CATATTTATAATCCAAATTTCAAGA-CTACTCAACCTGAG
4681  194_HRV46    CAGAGCAGTCCCATATCAA-CATATTTATAATCCAAATTTCAAGA-CTACTCAACCTGAG
4682  195_HRV80a   TAGAGCAGTCCCATACCAA-CATACCTACAGCCCAAATTTCAAAA-ACACTG---ATGAA
4683  196_HRV80b   TAGAGCAGTCCCATACCAA-CATACCTACAGCCCAAATTTCAAAA-ACACTG---ATGAA
4684  197_HRV80    TAGAGCAGTCCCATACCAA-CATACCTACAGCCCAAATTTCAAAA-ACACTG---ATGAA
4685  GROUP_36     -AGAGCAGTCCCATA-CAA.CATA--TA-A--CCAAATTTCAA-A.--ACT-----TGA-
4686
4687  192_HRV46a   ACTA------TACCAGATACTCATATTGGAATTAGAAGGGATATAAAGTACATTAAAA--
4688  193_HRV46b   ACTA------TACCAGATACTCATATTGGAATTAGAAGGGATATAAAGTACATTAAAA--
4689  194_HRV46    ACTA------TACCAGATACTCATATTGGAATTAGAAGGGATATAAAGTACATTAAAA--
4690  195_HRV80a   TCTA------TACCAGATACACAAATTAAAATCAGAGATAATATCAGGCAGGTTAGAA--
4691  196_HRV80b   TCTA------TACCAGATACACAAATTAAAATCAGAGATAATATCAGGCAGGTTAGAA--
4692  197_HRV80    TCTA------TACCAGATACACAAATTAAAATCAGAGATAATATCAGGCAGGTTAGAA--
4693  GROUP_36     -CTA......TACCAGATAC-CA-ATT--AAT-AGA----ATAT-A-G-A--TTA-AA..
4694
4695  192_HRV46a   ----CAGCA-----------
4696  193_HRV46b   ----CAGCC-----------
4697  194_HRV46    ----CAGCT-----------
4698  195_HRV80a   ----CAGTA-----------
4699  196_HRV80b   ----CAGTC-----------
4700  197_HRV80    ----CAGTT-----------
4701  GROUP_36     ....CAG--...........
4702
4703
4704
4705  GROUP  37:
4706
4707  198_HRV51    AACCCTGTTGAAAAATATACAGAGGCTTTACTCAATGAAGTGTTGGTGGTTCCCAACATA
4708  199_HRV51a   AACCCTGTTGAAAAATATACAGAGGCTTTACTCAATGAAGTGTTGGTGGTTCCCAACATA
4709  200_HRV51b   AACCCTGTTGAAAAATATACAGAGGCTTTACTCAATGAAGTGTTGGTGGTTCCCAACATA
4710  201_HRV65a   AATCCAATTGAGAAGTATACAGAAGCTCTACTTAATGAAGTGTTGGTGGTCCCAAATATA
4711  202_HRV65b   AATCCAATTGAGAAGTATACAGAAGCTCTACTTAATGAAGTGTTGGTGGTCCCAAATATA
4712  203_HRV65    AATCCAATTGAGAAGTATACAGAAGCTCTACTTAATGAAGTGTTGGTGGTCCCAAATATA
4713  GROUP_37     AA-CC--TTGA-AA-TATACAGA-GCT-TACT-AATGAAGTGTTGGTGGT-CC-AA-ATA
4714
4715  198_HRV51    CAACCTAGCAGTGGGCACACATCTAATGCTGCACCAGCTCTAGATGCTGCTGAGACAGGA
4716  199_HRV51a   CAACCTAGCAGTGGGCACACATCTAATGCTGCACCAGCTCTAGATGCTGCTGAGACAGGA
4717  200_HRV51b   CAACCTAGCAGTGGGCACACATCTAATGCTGCACCAGCTCTAGATGCTGCTGAGACAGGA
4718  201_HRV65a   CAAGCTAGTAATGGGCATACATCTAATGCTGCACCAGCTTTAGATGCTGCTGAAACAGGA
4719  202_HRV65b   CAAGCTAGTAATGGGCATACATCTAATGCTGCACCAGCTTTAGATGCTGCTGAAACAGGA
4720  203_HRV65    CAAGCTAGTAATGGGCATACATCTAATGCTGCACCAGCTTTAGATGCTGCTGAAACAGGA
4721  GROUP_37     CAA-CTAG-A-TGGGCA-ACATCTAATGCTGCACCAGCT-TAGATGCTGCTGA-ACAGGA
4722
4723  198_HRV51    CATACTAGTCAAGTTCAACCAGAAGATATGGTAGAGACCAGGTATGTTGTCACAGACCAA
4724  199_HRV51a   CATACTAGTCAAGTTCAACCAGAAGATATGGTAGAGACCAGGTATGTTGTCACAGACCAA
4725  200_HRV51b   CATACTAGTCAAGTTCAACCAGAAGATATGGTAGAGACCAGGTATGTTGTCACAGACCAA
4726  201_HRV65a   CACACTAGTCAAGTTCAACCAGAGGATGTGATAGAAACCAGATATGTCATCACAGATCAA
4727  202_HRV65b   CACACTAGTCAAGTTCAACCAGAGGATGTGATAGAAACCAGATATGTCATCACAGATCAA
4728  203_HRV65    CACACTAGTCAAGTTCAACCAGAGGATGTGATAGAAACCAGATATGTCATCACAGATCAA
4729  GROUP_37     CA-ACTAGTCAAGTTCAACCAGA-GAT-TG-TAGA-ACCAG-TATGT--TCACAGA-CAA
4730
```

FIG. D13 CONT'D 09.trace                                                                 9/20/2007 5:05 PM

```
4731 198_HRV51    ACTAGAGATGAAATGAGTATAGAGAGTTTCTTGGGTAGATCTGCTTGCGTAGCAATCATC
4732 199_HRV51a   ACTAGAGATGAAATGAGTATAGAGAGTTTCTTGGGTAGATCTGCTTGCGTAGCAATCATC
4733 200_HRV51b   ACTAGAGATGAAATGAGTATAGAGAGTTTCTTGGGTAGATCTGCTTGCGTAGCAATCATC
4734 201_HRV65a   ACCAGAGATGAGATGAGCGTAGAGAGTTTCCTGGGCAGATCTGCCTGCATAGCAGTCATT
4735 202_HRV65b   ACCAGAGATGAGAGCGTAGAGAGTTTCCTGGGCAGATCTGCCTGCATAGCAGTCATT
4736 203_HRV65    ACCAGAGATGAGATGAGCGTAGAGAGTTTCCTGGGCAGATCTGCCTGCATAGCAGTCATT
4737 GROUP_37     AC-AGAGATGA-ATGAG--TAGAGAGTTTC-TGGG-AGATCTGC-TGC-TAGCA-TCAT-
4738
4739 198_HRV51    CATACAAACCTTGAGCATGTTGAAGCAGACAGACAAGCCTACAATGCA---AAAGGGAAA
4740 199_HRV51a   CATACAAACCTTGAGCATGTTGAAGCAGACAGACAAGCCTACAATGCA---AAAGGGAAA
4741 200_HRV51b   CATACAAACCTTGAGCATGTTGAAGCAGACAGACAAGCCTACAATGCA---AAAGGGAAA
4742 201_HRV65a   CACACAGATCTTAAACATGACCATGAAGGCCAAAATGTTTACAATGAC---GAAGGCAGA
4743 202_HRV65b   CACACAGATCTTAAACATGACCATGAAGGCCAAAATGTTTACAATGAC---GAAGGCAGA
4744 203_HRV65    CACACAGATCTTAAACATGACCATGAAGGCCAAAATGTTTACAATGAC---GAAGGCAGA
4745 GROUP_37     CA-ACA-A-CTT-A-CATG---A-G-AG-C---A-A-G--TACAATG--...-AAGG-A-A
4746
4747 198_HRV51    AATTTCTCTACATGGAAAATTACACTCAAAGAAATGGCTCAAATTAGAAGAAAGTGTGAA
4748 199_HRV51a   AATTTCTCTACATGGAAAATTACACTCAAAGAAATGGCTCAAATTAGAAGAAAGTGTGAA
4749 200_HRV51b   AATTTCTCTACATGGAAAATTACACTCAAAGAAATGGCTCAAATTAGAAGAAAGTGTGAA
4750 201_HRV65a   AATTTCTCTGCTTGGGAAATTACACTCAAGGAAATGGCTCAAATTAGGAGAAAGTGTGAA
4751 202_HRV65b   AATTTCTCTGCTTGGGAAATTACACTCAAGGAAATGGCTCAAATTAGGAGAAAGTGTGAA
4752 203_HRV65    AATTTCTCTGCTTGGGAAATTACACTCAAGGAAATGGCTCAAATTAGGAGAAAGTGTGAA
4753 GROUP_37     AATTTCTCT-C-TGG-AAATTACACTCAA-GAAATGGCTCAAATTAG-AGAAAGTGTGAA
4754
4755 198_HRV51    CTTTTCACATACTTAAGATTTGATTCAGAGATCACTATAG-TTGCTACCATTGCTGGACA
4756 199_HRV51a   CTTTTCACATACTTAAGATTTGATTCAGAGATCACTATAG-TTGCTACCATTGCTGGACA
4757 200_HRV51b   CTTTTCACATACTTAAGATTTGATTCAGAGATCACTATAG-TTGCTACCATTGCTGGACA
4758 201_HRV65a   CTCTTCACCTATTTGCGCTTTGACTCAGAAATTACCATAG-TGGCTACTATAGCTGGACA
4759 202_HRV65b   CTCTTCACCTATTTGCGCTTTGACTCAGAAATTACCATAG-TGGCTACTATAGCTGGACA
4760 203_HRV65    CTCTTCACCTATTTGCGCTTTGACTCAGAAATTACCATAG-TGGCTACTATAGCTGGACA
4761 GROUP_37     CT-TTCAC-TA-TT--G-TTTGA-TCAGA-AT-AC-ATAG.T-GCTAC-AT-GCTGGACA
4762
4763 198_HRV51    GGGTGATGACATAGGGCACATTGTACTTCAATACATGTATGTACCCCCTGGAGGACCAGT
4764 199_HRV51a   GGGTGATGACATAGGGCACATTGTACTTCAATACATGTATGTACCCCCTGGAGGACCAGT
4765 200_HRV51b   GGGTGATGACATAGGGCACATTGTACTTCAATACATGTATGTACCCCCTGGAGGACCAGT
4766 201_HRV65a   AGGTGATGACATAGGGCACATAGTGCTTCAATATATGTATGTGCCTCCTGGTGGTCCTGT
4767 202_HRV65b   AGGTGATGACATAGGGCACATAGTGCTTCAATATATGTATGTGCCTCCTGGTGGTCCTGT
4768 203_HRV65    AGGTGATGACATAGGGCACATAGTGCTTCAATATATGTATGTGCCTCCTGGTGGTCCTGT
4769 GROUP_37     -GGTGATGACATAGGGCACAT-GT-CTTCAATA-ATGTATGT-CC-CCTGG-GG-CC-GT
4770
4771 198_HRV51    TCCACTTACTAGGAAAGATGATGAGTGGCAATCAGGAACTAATGCTTCAGTATTCTGGCA
4772 199_HRV51a   TCCACTTACTAGGAAAGATGATGAGTGGCAATCAGGAACTAATGCTTCAGTATTCTGGCA
4773 200_HRV51b   TCCACTTACTAGGAAAGATGATGAGTGGCAATCAGGAACTAATGCTTCAGTATTCTGGCA
4774 201_HRV65a   TCCAAAACTAGAAAAGATGAAGAGTGGCAGACAGGAACTAATGCTTCAGTCTTTTGGCA
4775 202_HRV65b   TCCAAAACTAGAAAAGATGAAGAGTGGCAGACAGGAACTAATGCTTCAGTCTTTTGGCA
4776 203_HRV65    TCCAAAACTAGAAAAGATGAAGAGTGGCAGACAGGAACTAATGCTTCAGTCTTTTGGCA
4777 GROUP_37     TCCA---ACTAG-AAAGATGA-GAGTGGCA--CAGGAACTAATGCTTCAGT-TT-TGGCA
4778
4779 198_HRV51    ACATGGACAACCATACCCTAGATTTACAATCCCTTTTGTAAGCATAGCCTCAGCATACTA
4780 199_HRV51a   ACATGGACAACCATACCCTAGATTTACAATCCCTTTTGTAAGCATAGCCTCAGCATACTA
4781 200_HRV51b   ACATGGACAACCATACCCTAGATTTACAATCCCTTTTGTAAGCATAGCCTCAGCATACTA
4782 201_HRV65a   GCATGGTCAACCATACCCCAGATTTACAATTCCTTTTGTGAGTATTGCCTCAGCATATTA
4783 202_HRV65b   GCATGGTCAACCATACCCCAGATTTACAATTCCTTTTGTGAGTATTGCCTCAGCATATTA
4784 203_HRV65    GCATGGTCAACCATACCCCAGATTTACAATTCCTTTTGTGAGTATTGCCTCAGCATATTA
4785 GROUP_37     -CATGG-CAACCATACCCC-AGATTTACAAT-CCTTTTGT-AG-AT-GCCTCAGCATA-TA
4786
4787 198_HRV51    CATGTTTTATGATGGGTATGAAGGTGATAGTTTGACCTCACAGTACGGTTCAGTAGTCAC
4788 199_HRV51a   CATGTTTTATGATGGGTATGAAGGTGATAGTTTGACCTCACAGTACGGTTCAGTAGTCAC
4789 200_HRV51b   CATGTTTTATGATGGGTATGAAGGTGATAGTTTGACCTCACAGTACGGTTCAGTAGTCAC
4790 201_HRV65a   CATGTTCTATGATGGTTATGAGGGTGATGACCCAAATTCAAAATATGGTTCAGTGGTTAC
4791 202_HRV65b   CATGTTCTATGATGGTTATGAGGGTGATGACCCAAATTCAAAATATGGTTCAGTGGTTAC
4792 203_HRV65    CATGTTCTATGATGGTTATGAGGGTGATGACCCAAATTCAAAATATGGTTCAGTGGTTAC
4793 GROUP_37     CATGTT-TATGATGG-TATGA-GGTGAT------A--TCA-A-TA-GGTTCAGT-GT-AC
4794
4795 198_HRV51    AAATGCTATGGGGACACTATGTGTTCGTGTGGTCACAGAGCAACAAAAACATGAGGTTAA
```

FIG. D13 CONT'D

```
09.trace                                                                 9/20/2007  5:05 PM 4796  199_HRV51a   AAATGCTATGGGGACACTATGTGTTCGTGTGGTCACAGAGCAACAAAAACATGAGGTTAA
4797  200_HRV51b   AAATGCTATGGGGACACTATGTGTTCGTGTGGTCACAGAGCAACAAAAACATGAGGTTAA
4798  201_HRV65a   TAATGCTATGGGCACACTATATGTGCGTGTGGTTACAGAAAGGCAAAAACATGAAGTCAA
4799  202_HRV65b   TAATGCTATGGGCACACTATATGTGCGTGTGGTTACAGAAAGGCAAAAACATGAAGTCAA
4800  203_HRV65    TAATGCTATGGGCACACTATATGTGCGTGTGGTTACAGAAAGGCAAAAACATGAAGTCAA
4801  GROUP_37     -AATGCTATGGG-ACACTAT-TGT-CGTGTGGT-ACAGA----CAAAAACATGA-GT-AA
4802
4803  198_HRV51    CATAACTAGCAGGATTTACCACAAAGCCAAACATGTCAGTGCATGGTGCCCTCGTCCTCC
4804  199_HRV51a   CATAACTAGCAGGATTTACCACAAAGCCAAACATGTCAGTGCATGGTGCCCTCGTCCTCC
4805  200_HRV51b   CATAACTAGCAGGATTTACCACAAAGCCAAACATGTCAGTGCATGGTGCCCTCGTCCTCC
4806  201_HRV65a   CATAACCAGTAGAATATATCATAAAGCTAAACACATCAGTGCTTGGTGTCCACGACCTCC
4807  202_HRV65b   CATAACCAGTAGAATATATCATAAAGCTAAACACATCAGTGCTTGGTGTCCACGACCTCC
4808  203_HRV65    CATAACCAGTAGAATATATCATAAAGCTAAACACATCAGTGCTTGGTGTCCACGACCTCC
4809  GROUP_37     CATAAC-AG-AG-AT-TA-CA-AAAGC-AAACA--TCAGTGC-TGGTG-CC-CG-CCTCC
4810
4811  198_HRV51    TCGTGCTGTAGCCTACCAA-CACACATACAGTACAAACTTCGTTC-CAAAAGAGGGATTT
4812  199_HRV51a   TCGTGCTGTAGCCTACCAA-CACACATACAGTACAAACTTCGTTC-CAAAAGAGGGATTT
4813  200_HRV51b   TCGTGCTGTAGCCTACCAA-CACACATACAGTACAAACTTCGTTC-CAAAAGAGGGATTT
4814  201_HRV65a   CCGAGCAGTAGCTTACCAA-CACACATACAGTACAAATTTTGTTC-CTAGCGGAGGTCTT
4815  202_HRV65b   CCGAGCAGTAGCTTACCAA-CACACATACAGTACAAATTTTGTTC-CTAGCGGAGGTCTT
4816  203_HRV65    CCGAGCAGTAGCTTACCAA-CACACATACAGTACAAATTTTGTTC-CTAGCGGAGGTCTT
4817  GROUP_37     -CG-GC-GTAGC-TACCAA.CACACATACAGTACAAA-TT-GTTC.C-A--G--GG--TT
4818
4819  198_HRV51    GAAG------GCTTGAAAACTCAGATTAAAACTAGGGCAGACATCAAACTTGTGAACT--
4820  199_HRV51a   GAAG------GCTTGAAAACTCAGATTAAAACTAGGGCAGACATCAAACTTGTGAACT--
4821  200_HRV51b   GAAG------GCTTGAAAACTCAGATTAAAACTAGGGCAGACATCAAACTTGTGAACT--
4822  201_HRV65a   ACAA------ACCTAAGAACCCAAATTAAAACCAGAGATAACATTAAAATTGTAAACT--
4823  202_HRV65b   ACAA------ACCTAAGAACCCAAATTAAAACCAGAGATAACATTAAAATTGTAAACT--
4824  203_HRV65    ACAA------ACCTAAGAACCCAAATTAAAACCAGAGATAACATTAAAATTGTAAACT--
4825  GROUP_37     --A-......-C-T-A-AAC-CA-ATTAAAAC-AG-G---ACAT-AAA-TTGT-AACT..
4826
4827  198_HRV51    -----TT--------------
4828  199_HRV51a   -----TA--------------
4829  200_HRV51b   -----TG--------------
4830  201_HRV65a   -----TG--------------
4831  202_HRV65b   -----TA--------------
4832  203_HRV65    -----TT--------------
4833  GROUP_37     .....T-..............
4834
4835
4836
4837  GROUP  38:
4838
4839  204_HRV71a   AATCCTGTAGAAAAATATACAGAAGCAATACTCAATGAGGTTCTAGTTGTGCCAAATATA
4840  205_HRV71b   AATCCTGTAGAAAAATATACAGAAGCAATACTCAATGAGGTTCTAGTTGTGCCAAATATA
4841  206_HRV71    AATCCTGTAGAAAAATATACAGAAGCAATACTCAATGAGGTTCTAGTTGTGCCAAATATA
4842  GROUP_38     AATCCTGTAGAAAAATATACAGAAGCAATACTCAATGAGGTTCTAGTTGTGCCAAATATA
4843
4844  204_HRV71a   CAACCTAGTAATGGACATACCTCAAACTCAGCACCAGCCTTAGATGCAGCAGAAACTGGG
4845  205_HRV71b   CAACCTAGTAATGGACATACCTCAAACTCAGCACCAGCCTTAGATGCAGCAGAAACTGGG
4846  206_HRV71    CAACCTAGTAATGGACATACCTCAAACTCAGCACCAGCCTTAGATGCAGCAGAAACTGGG
4847  GROUP_38     CAACCTAGTAATGGACATACCTCAAACTCAGCACCAGCCTTAGATGCAGCAGAAACTGGG
4848
4849  204_HRV71a   CATACCAACCAAGTACAACCAGAAGATGTTATGGAAACCAGATATGTGATCACTGATCAA
4850  205_HRV71b   CATACCAACCAAGTACAACCAGAAGATGTTATGGAAACCAGATATGTGATCACTGATCAA
4851  206_HRV71    CATACCAACCAAGTACAACCAGAAGATGTTATGGAAACCAGATATGTGATCACTGATCAA
4852  GROUP_38     CATACCAACCAAGTACAACCAGAAGATGTTATGGAAACCAGATATGTGATCACTGATCAA
4853
4854  204_HRV71a   ACTAGGGATGAAATGAGCATTGAGAGCTTCTTGGGCAGATCTGCATGCATAGCTACCATA
4855  205_HRV71b   ACTAGGGATGAAATGAGCATTGAGAGCTTCTTGGGCAGATCTGCATGCATAGCTACCATA
4856  206_HRV71    ACTAGGGATGAAATGAGCATTGAGAGCTTCTTGGGCAGATCTGCATGCATAGCTACCATA
4857  GROUP_38     ACTAGGGATGAAATGAGCATTGAGAGCTTCTTGGGCAGATCTGCATGCATAGCTACCATA
4858
4859  204_HRV71a   CACACTAAATTAGTACATGGAGAGGAGGG------TGTTTATAATATG---AAAGGTAAC
4860  205_HRV71b   CACACTAAATTAGTACATGGAGAGGAGGG------TGTTTATAATATG---AAAGGTAAC
```

FIG. D13 CONT'D

```
09.trace                                                               9/20/2007 5:05 PM 4861 206_HRV71    CACACTAAATTAGTACATGGAGAGGAGGG------TGTTTATAATATG---AAAGGTAAC
4862 GROUP_38    CACACTAAATTAGTACATGGAGAGGAGGG......TGTTTATAATATG...AAAGGTAAC
4863
4864 204_HRV71a  AATCTCTCAAAGTGGCAGATTACACTCAAAGAAATGGCTCAGATCAGGAGGAAATGTGAA
4865 205_HRV71b  AATCTCTCAAAGTGGCAGATTACACTCAAAGAAATGGCTCAGATCAGGAGGAAATGTGAA
4866 206_HRV71   AATCTCTCAAAGTGGCAGATTACACTCAAAGAAATGGCTCAGATCAGGAGGAAATGTGAA
4867 GROUP_38    AATCTCTCAAAGTGGCAGATTACACTCAAAGAAATGGCTCAGATCAGGAGGAAATGTGAA
4868
4869 204_HRV71a  CTCTTCACATACCTGCGCTTTGATTCAGAGATAACAATTG-TAGCTACACTAGCAGGGCA
4870 205_HRV71b  CTCTTCACATACCTGCGCTTTGATTCAGAGATAACAATTG-TAGCTACACTAGCAGGGCA
4871 206_HRV71   CTCTTCACATACCTGCGCTTTGATTCAGAGATAACAATTG-TAGCTACACTAGCAGGGCA
4872 GROUP_38    CTCTTCACATACCTGCGCTTTGATTCAGAGATAACAATTG.TAGCTACACTAGCAGGGCA
4873
4874 204_HRV71a  AGGAGATGATTTAGGACATATTGTACTCCAGTACATGTATGTTCCCCCAGGTGGTCCAAT
4875 205_HRV71b  AGGAGATGATTTAGGACATATTGTACTCCAGTACATGTATGTTCCCCCAGGTGGTCCAAT
4876 206_HRV71   AGGAGATGATTTAGGACATATTGTACTCCAGTACATGTATGTTCCCCCAGGTGGTCCAAT
4877 GROUP_38    AGGAGATGATTTAGGACATATTGTACTCCAGTACATGTATGTTCCCCCAGGTGGTCCAAT
4878
4879 204_HRV71a  ACCAGAGACCAGGGATGCCGATGAATGGCAGTCTGGAACTAATGCATCAGTCTTTTGGCA
4880 205_HRV71b  ACCAGAGACCAGGGATGCCGATGAATGGCAGTCTGGAACTAATGCATCAGTCTTTTGGCA
4881 206_HRV71   ACCAGAGACCAGGGATGCCGATGAATGGCAGTCTGGAACTAATGCATCAGTCTTTTGGCA
4882 GROUP_38    ACCAGAGACCAGGGATGCCGATGAATGGCAGTCTGGAACTAATGCATCAGTCTTTTGGCA
4883
4884 204_HRV71a  GCACGGCCAACCATACCCAAGGTTTACAATCCCCTTCATAAGCATTGCATCAGCATATTA
4885 205_HRV71b  GCACGGCCAACCATACCCAAGGTTTACAATCCCCTTCATAAGCATTGCATCAGCATATTA
4886 206_HRV71   GCACGGCCAACCATACCCAAGGTTTACAATCCCCTTCATAAGCATTGCATCAGCATATTA
4887 GROUP_38    GCACGGCCAACCATACCCAAGGTTTACAATCCCCTTCATAAGCATTGCATCAGCATATTA
4888
4889 204_HRV71a  CATGTTCTATGATGGGTATGAAGGTGATGCCCTCAGTTCTAAATATGGCTCAGTAGTTAC
4890 205_HRV71b  CATGTTCTATGATGGGTATGAAGGTGATGCCCTCAGTTCTAAATATGGCTCAGTAGTTAC
4891 206_HRV71   CATGTTCTATGATGGGTATGAAGGTGATGCCCTCAGTTCTAAATATGGCTCAGTAGTTAC
4892 GROUP_38    CATGTTCTATGATGGGTATGAAGGTGATGCCCTCAGTTCTAAATATGGCTCAGTAGTTAC
4893
4894 204_HRV71a  TAATGCCATGGGCACCTTATGTGTTCGTGTGGTTACAGAACAGCAAAGCAACACAGTCAA
4895 205_HRV71b  TAATGCCATGGGCACCTTATGTGTTCGTGTGGTTACAGAACAGCAAAGCAACACAGTCAA
4896 206_HRV71   TAATGCCATGGGCACCTTATGTGTTCGTGTGGTTACAGAACAGCAAAGCAACACAGTCAA
4897 GROUP_38    TAATGCCATGGGCACCTTATGTGTTCGTGTGGTTACAGAACAGCAAAGCAACACAGTCAA
4898
4899 204_HRV71a  CATAACAAGTAGGATTTATCACAAAGCCAAACATGTCAGAGCATGGTGTCCTAGACCCCC
4900 205_HRV71b  CATAACAAGTAGGATTTATCACAAAGCCAAACATGTCAGAGCATGGTGTCCTAGACCCCC
4901 206_HRV71   CATAACAAGTAGGATTTATCACAAAGCCAAACATGTCAGAGCATGGTGTCCTAGACCCCC
4902 GROUP_38    CATAACAAGTAGGATTTATCACAAAGCCAAACATGTCAGAGCATGGTGTCCTAGACCCCC
4903
4904 204_HRV71a  CAGAGCAGTAGCCTACCAA-TCAACATATACCACAAATTTTGTTC-CACAAGACGGGATC
4905 205_HRV71b  CAGAGCAGTAGCCTACCAA-TCAACATATACCACAAATTTTGTTC-CACAAGACGGGATC
4906 206_HRV71   CAGAGCAGTAGCCTACCAA-TCAACATATACCACAAATTTTGTTC-CACAAGACGGGATC
4907 GROUP_38    CAGAGCAGTAGCCTACCAA.TCAACATATACCACAAATTTTGTTC.CACAAGACGGGATC
4908
4909 204_HRV71a  AATT------CCATTAAAACCAAAATCAAAATCAGAAGAGACATTAAAGAGGTCAGCA--
4910 205_HRV71b  AATT------CCATTAAAACCAAAATCAAAATCAGAAGAGACATTAAAGAGGTCAGCA--
4911 206_HRV71   AATT------CCATTAAAACCAAAATCAAAATCAGAAGAGACATTAAAGAGGTCAGCA--
4912 GROUP_38    AATT......CCATTAAAACCAAAATCAAAATCAGAAGAGACATTAAAGAGGTCAGCA..
4913
4914 204_HRV71a  -----ACTAA-----------
4915 205_HRV71b  -----ACTAG-----------
4916 206_HRV71   -----ACTAT-----------
4917 GROUP_38    .....ACTA-...........
4918
4919
4920
4921 GROUP  39:
4922
4923 207_HRV8    AACCCTATTGAACAATTCACAGAGGCAGTATTAAACGAGGTTCTTGTAGTTCCAAACACA
4924 208_HRV95   AACCCTATTGAACAATTCACAGAGGCAGTATTAAACGAGGTTCTTGTAGTTCCAAATACA
4925 GROUP_39    AACCCTATTGAACAATTCACAGAGGCAGTATTAAACGAGGTTCTTGTAGTTCCAAA-ACA
```

FIG. D13 CONT'D

```
09.trace                                                                  9/20/2007 5:05 PM
4926
4927 207_HRV8     CAAGCTAGTAATGGATCTATAGCAAATTCAGCACCAGCATTAGATGCAGCAGAGACTGGA
4928 208_HRV95    CAAGCCAGTAATGGATCTATAGCAAATTCAGCACCAGCATTAGATGCAGCAGAGACTGGA
4929 GROUP_39     CAAGC-AGTAATGGATCTATAGCAAATTCAGCACCAGCATTAGATGCAGCAGAGACTGGA
4930
4931 207_HRV8     CACACAAGTTCAGTGCAACCTGAAGATCTTATAGAGACTAGGTATGTAATTACAGATCAA
4932 208_HRV95    CACACAAGTTCAGTGCAACCTGAAGATCTTATAGAGACTAGGTATGTAATTACAGATCAA
4933 GROUP_39     CACACAAGTTCAGTGCAACCTGAAGATCTTATAGAGACTAGGTATGTAATTACAGATCAA
4934
4935 207_HRV8     ACTAGGCATGAGACATCACTGGAATCTTTCTTGGGTAGAGCAGGATGCATTAAAATCATT
4936 208_HRV95    ACTAGGTATGAGACATCACTGGAATCTTTCTTGGGTAGAGCAGGATGCATTAAAATTATT
4937 GROUP_39     ACTAGG-ATGAGACATCACTGGAATCTTTCTTGGGTAGAGCAGGATGCATTAAAAT-ATT
4938
4939 207_HRV8     GCATTAGAACTAGATCATGACAAC---------------TATGATGAA------------
4940 208_HRV95    GCATTAGAACTAGATCATGACAAC---------------TATGATAAA------------
4941 GROUP_39     GCATTAGAACTAGATCATGACAAC...............TATGAT-AA............
4942
4943 207_HRV8     AGTTTCAGGACCTGGGGAATAAACATACAAGAGATGTCACAAATTAGAAGGAAATTTGAG
4944 208_HRV95    AATTTCAGGACCTGGGGAATAAACATACAAGAGATGTCACAAATTAGAAGGAAATTTGAA
4945 GROUP_39     A-TTTCAGGACCTGGGGAATAAACATACAAGAGATGTCACAAATTAGAAGGAAATTTGA-
4946
4947 207_HRV8     ATGTTCACTTATGTAAGATTTGATTCAGAGATAACAATTG-TACCATGTATTGCAGCTAT
4948 208_HRV95    ATGTTCACTTATGTAAGATTTGATTCAGAGATAACAATTG-TACCATGTATTGCAGCTAT
4949 GROUP_39     ATGTTCACTTATGTAAGATTTGATTCAGAGATAACAATTG.TACCATGTATTGCAGCTAT
4950
4951 207_HRV8     AAAAGGTGACCTTGGACACATAGTCCTTCAATACATGTATGTTCCCCCGGGTGCACCTCT
4952 208_HRV95    AGAAGGTGACCTTGGACACATAGTCCTCCAATACATGTATGTTCCCCCGGGTGCACCTCT
4953 GROUP_39     A-AAGGTGACCTTGGACACATAGTCCT-CAATACATGTATGTTCCCCCGGGTGCACCTCT
4954
4955 207_HRV8     TCCAGATAAAAGGATGCACGATGCCTGGCAAACCAGTACAAATGCCTCAGTCTTCTGGCA
4956 208_HRV95    TCCAGATAAAAGGATGCACGATGCCTGGCAAACCAGTACAAATGCCTCAGTCTTCTGGCA
4957 GROUP_39     TCCAGATAAAAGGATGCACGATGCCTGGCAAACCAGTACAAATGCCTCAGTCTTCTGGCA
4958
4959 207_HRV8     AGTTGGACAAACTTATCCCAGATTCACCATACCTTTCTCCAGCATAGCATCAGCTTATTA
4960 208_HRV95    AGTTGGACAGACTTATCCCAGATTCACCATACCTTTCTCCAGTATAGCATCAGCTTATTA
4961 GROUP_39     AGTTGGACA-ACTTATCCCAGATTCACCATACCTTTCTCCAG-ATAGCATCAGCTTATTA
4962
4963 207_HRV8     CATGTTCTATGATGGTTATGATTCAGATGGTTTAGATGCTATTTATGGTATTCCTGTTAC
4964 208_HRV95    CATGTTCTATGATGGTTATGATTCAGATGGTTTAGATGCTATTTATGGTATTCCTGTTAC
4965 GROUP_39     CATGTTCTATGATGGTTATGATTCAGATGGTTTAGATGCTATTTATGGTATTCCTGTTAC
4966
4967 207_HRV8     AAATCACATGGGCACAATATGTGTGAGAATGGTGACAGATAAACAGAAAATTAAAACTAA
4968 208_HRV95    AAATCACATGGGCACAATATGTGTGAGAATGGTGACAGATAAACAGAAAATTAAAACTAA
4969 GROUP_39     AAATCACATGGGCACAATATGTGTGAGAATGGTGACAGATAAACAGAAAATTAAAACTAA
4970
4971 207_HRV8     AATTGATTCAAGAATATACCTGAAAGCAAAGCACATTAAAGCTTGGTGTCCTAGACCCCC
4972 208_HRV95    AATTGATTCAAGAATATACCTGAAAGCAAAGCACATTAAAGCTTGGTGTCCTAGACCCCC
4973 GROUP_39     AATTGATTCAAGAATATACCTGAAAGCAAAGCA-ATTAAAGCTTGGTGTCCTAGACCCCC
4974
4975 207_HRV8     CAGAGCAGTTACGTATAAC-CATATATACAACCCCAATTATGTTA-GAGAGG------GA
4976 208_HRV95    CAGAGCAGTTACGTATAAC-CATATATACAACCCCAATTATGTTA-GAGAGG------GA
4977 GROUP_39     CAGAGCAGTTACGTATAAC.CATATATACAACCCCAATTATGTTA.GAGAGG......GA
4978
4979 207_HRV8     GTAA------CACCAGAAACTAAGGTTAAATATAGAGCTGAAGTCACAACCATT------
4980 208_HRV95    GTAA------CACCAGAAACTAAGGTCAAATATAGAGCTGAAGTCACAACCATT------
4981 GROUP_39     GTAA......CACCAGAAACTAAGGT-AAATATAGAGCTGAAGTCACAACCATT......
4982
4983 207_HRV8     --------------------
4984 208_HRV95    --------------------
4985 GROUP_39     ....................
4986
4987
4988
4989 GROUP_40:
4990
```

FIG. D13 CONT'D

```
09.trace                                                              9/20/2007 5:05 PM 4991  209_HRV45     AACCCTGTTGAACAATTTGCAGAAGCAGTCCTTGATCAAGTATTAGTAGTTCCAAACACT
4992  210_HRV45a    AACCCTGTTGAACAATTTGCAGAAGCAGTCCTTGATCAAGTATTAGTAGTTCCAAACACT
4993  211_HRV45b    AACCCTGTTGAACAATTTGCAGAAGCAGTCCTTGATCAAGTATTAGTAGTTCCAAACACT
4994  GROUP_40     AACCCTGTTGAACAATTTGCAGAAGCAGTCCTTGATCAAGTATTAGTAGTTCCAAACACT
4995
4996  209_HRV45     CGACCCAGCGATGGGTTGATTGCAAACTCAGCCCCAGCTTTGGATGCAGCTGAAACTGGA
4997  210_HRV45a    CGACCCAGCGATGGGTTGATTGCAAACTCAGCCCCAGCTTTGGATGCAGCTGAAACTGGA
4998  211_HRV45b    CGACCCAGCGATGGGTTGATTGCAAACTCAGCCCCAGCTTTGGATGCAGCTGAAACTGGA
4999  GROUP_40     CGACCCAGCGATGGGTTGATTGCAAACTCAGCCCCAGCTTTGGATGCAGCTGAAACTGGA
5000
5001  209_HRV45     CACACCAGTTCAGTGCAGCCTGAGGACCTTATAGAGACTAGATATGTGATTGCAGACCAA
5002  210_HRV45a    CACACCAGTTCAGTGCAGCCTGAGGACCTTATAGAGACTAGATATGTGATTGCAGACCAA
5003  211_HRV45b    CACACCAGTTCAGTGCAGCCTGAGGACCTTATAGAGACTAGATATGTGATTGCAGACCAA
5004  GROUP_40     CACACCAGTTCAGTGCAGCCTGAGGACCTTATAGAGACTAGATATGTGATTGCAGACCAA
5005
5006  209_HRV45     ACCAGACATGAAACCTCCATTGAATCTTTTTTGGGTAGGGCTGGATGTGTGGCCAATATT
5007  210_HRV45a    ACCAGACATGAAACCTCCATTGAATCTTTTTTGGGTAGGGCTGGATGTGTGGCCAATATT
5008  211_HRV45b    ACCAGACATGAAACCTCCATTGAATCTTTTTTGGGTAGGGCTGGATGTGTGGCCAATATT
5009  GROUP_40     ACCAGACATGAAACCTCCATTGAATCTTTTTTGGGTAGGGCTGGATGTGTGGCCAATATT
5010
5011  209_HRV45     AGTTTAGACATTAACCATGATGAC---------------TACCAAAAG------------
5012  210_HRV45a    AGTTTAGACATTAACCATGATGAC---------------TACCAAAAG------------
5013  211_HRV45b    AGTTTAGACATTAACCATGATGAC---------------TACCAAAAG------------
5014  GROUP_40     AGTTTAGACATTAACCATGATGAC...............TACCAAAAG............
5015
5016  209_HRV45     AATTACAAAAATTGGGCAATTAGTTTACAAGAAATGTCACAAATTAGGAGGAAATTTGAA
5017  210_HRV45a    AATTACAAAAATTGGGCAATTAGTTTACAAGAAATGTCACAAATTAGGAGGAAATTTGAA
5018  211_HRV45b    AATTACAAAAATTGGGCAATTAGTTTACAAGAAATGTCACAAATTAGGAGGAAATTTGAA
5019  GROUP_40     AATTACAAAAATTGGGCAATTAGTTTACAAGAAATGTCACAAATTAGGAGGAAATTTGAA
5020
5021  209_HRV45     ATGTTTACATATGTCAGATTTGATTCCGAAATAACAATAG-TACCATGTGTTGCTGCCAC
5022  210_HRV45a    ATGTTTACATATGTCAGATTTGATTCCGAAATAACAATAG-TACCATGTGTTGCTGCCAC
5023  211_HRV45b    ATGTTTACATATGTCAGATTTGATTCCGAAATAACAATAG-TACCATGTGTTGCTGCCAC
5024  GROUP_40     ATGTTTACATATGTCAGATTTGATTCCGAAATAACAATAG.TACCATGTGTTGCTGCCAC
5025
5026  209_HRV45     AGAAGGTAACTTGGGACACATTGTTGTGCAATACATGTTTGTACCACCAGGAGCACCTCT
5027  210_HRV45a    AGAAGGTAACTTGGGACACATTGTTGTGCAATACATGTTTGTACCACCAGGAGCACCTCT
5028  211_HRV45b    AGAAGGTAACTTGGGACACATTGTTGTGCAATACATGTTTGTACCACCAGGAGCACCTCT
5029  GROUP_40     AGAAGGTAACTTGGGACACATTGTTGTGCAATACATGTTTGTACCACCAGGAGCACCTCT
5030
5031  209_HRV45     CCCTGTTAGTAGAACTGACAACACTTGGCAATCTAGCACAAATGCATCAGTCTTTTGGCA
5032  210_HRV45a    CCCTGTTAGTAGAACTGACAACACTTGGCAATCTAGCACAAATGCATCAGTCTTTTGGCA
5033  211_HRV45b    CCCTGTTAGTAGAACTGACAACACTTGGCAATCTAGCACAAATGCATCAGTCTTTTGGCA
5034  GROUP_40     CCCTGTTAGTAGAACTGACAACACTTGGCAATCTAGCACAAATGCATCAGTCTTTTGGCA
5035
5036  209_HRV45     GGTTGGTCAAACTTATCCCAGATTTTCTATACCTTTCTCAAGTATAGCTTCAGCTTACTA
5037  210_HRV45a    GGTTGGTCAAACTTATCCCAGATTTTCTATACCTTTCTCAAGTATAGCTTCAGCTTACTA
5038  211_HRV45b    GGTTGGTCAAACTTATCCCAGATTTTCTATACCTTTCTCAAGTATAGCTTCAGCTTACTA
5039  GROUP_40     GGTTGGTCAAACTTATCCCAGATTTTCTATACCTTTCTCAAGTATAGCTTCAGCTTACTA
5040
5041  209_HRV45     CATGTTTTATGATGGATACGACACTGATGGCACAGATGCAGTGTATGGTGTTAGTGTGAC
5042  210_HRV45a    CATGTTTTATGATGGATACGACACTGATGGCACAGATGCAGTGTATGGTGTTAGTGTGAC
5043  211_HRV45b    CATGTTTTATGATGGATACGACACTGATGGCACAGATGCAGTGTATGGTGTTAGTGTGAC
5044  GROUP_40     CATGTTTTATGATGGATACGACACTGATGGCACAGATGCAGTGTATGGTGTTAGTGTGAC
5045
5046  209_HRV45     TAACCATATGGGGACTATATGTGTTAGAATTGTTACAGACCAACAACAACATAGAGTTAA
5047  210_HRV45a    TAACCATATGGGGACTATATGTGTTAGAATTGTTACAGACCAACAACAACATAGAGTTAA
5048  211_HRV45b    TAACCATATGGGGACTATATGTGTTAGAATTGTTACAGACCAACAACAACATAGAGTTAA
5049  GROUP_40     TAACCATATGGGGACTATATGTGTTAGAATTGTTACAGACCAACAACAACATAGAGTTAA
5050
5051  209_HRV45     GATCGACTCCATGGTATATCTAAAAGCTAAACACATCAAGGCATGGTGTCCCAGACCTCC
5052  210_HRV45a    GATCGACTCCATGGTATATCTAAAAGCTAAACACATCAAGGCATGGTGTCCCAGACCTCC
5053  211_HRV45b    GATCGACTCCATGGTATATCTAAAAGCTAAACACATCAAGGCATGGTGTCCCAGACCTCC
5054  GROUP_40     GATCGACTCCATGGTATATCTAAAAGCTAAACACATCAAGGCATGGTGTCCCAGACCTCC
5055
```

FIG. D13 CONT'D

```
09.trace                                                                9/20/2007 5:05 PM 5056  209_HRV45    AAGAGCAGTCACATATAAC-CATACATATAATCCAAATTATGTTA-GGGCTG------AT
5057  210_HRV45a   AAGAGCAGTCACATATAAC-CATACATATAATCCAAATTATGTTA-GGGCTG------AT
5058  211_HRV45b   AAGAGCAGTCACATATAAC-CATACATATAATCCAAATTATGTTA-GGGCTG------AT
5059  GROUP_40     AAGAGCAGTCACATATAAC.CATACATATAATCCAAATTATGTTA.GGGCTG......AT
5060
5061  209_HRV45    GAAA------CAGCC---ACAAAAGTCCAAACTAGAGCAAATGTCACAACAGTA------
5062  210_HRV45a   GAAA------CAGCC---ACAAAAGTCCAAACTAGAGCAAATGTCACAACAGTG------
5063  211_HRV45b   GAAA------CAGCC---ACAAAAGTCCAAACTAGAGCAAATGTCACAACAGTT------
5064  GROUP_40     GAAA......CAGCC...ACAAAAGTCCAAACTAGAGCAAATGTCACAACAGT-......
5065
5066  209_HRV45    --------------------
5067  210_HRV45a   --------------------
5068  211_HRV45b   --------------------
5069  GROUP_40     ....................
5070
5071
5072
5073  Summary:
5074
5075  GROUP_1      AATCCAGT-GAAAA-TACATTGATGAAGTTTTAAATGAAGTT-TAGTAGT-CC-AATATA
5076  GROUP_2      AA-CC-GTTGAAA--TA-GTTGATGA-GT-CTTAATGA-GTTCT-GT-GTTCCAAATATC
5077  GROUP_3      AACCCAGTTGAGAGATATGTAGATGATGTTTTAAATGAAGTTTTAGTTGTTCCAAATATT
5078  GROUP_4      AATCCTGTAGA-AGATATGTTGATGAAGT-TTAAATGAAGTGTTAGTTGT-CCAAACATT
5079  GROUP_5      AA-CCAGT-GA-AA-TATGT-AATGATGT-CTTAATGA-GT-TTAGT-GT-CCAAA-ATA
5080  GROUP_6      AATCCAGTAGAAAATTATATAGATG-AGTATTAAATGAGGTATTAGTTGTTCCTAATATA
5081  GROUP_7      AATCCAGT-GAAAATTA--TTGA---TGT-CT-AATGAAGT-CTAGTGGTACC-AA-AT-
5082  GROUP_8      AATCCAGTTGA-GA-TAT-T-GA---TGT--T-AATGAAGT-TTAGTAGTACCAAA-A-C
5083  GROUP_9      AA-CCA-TTGAAAA-TATGT-GAT-A-GT-CTTAATGA-GT--TAGT-GT-CC-AA-AT-
5084  GROUP_10     AA-CCAGT-GAAAA-TATGTGGAAGAGGT-CTTAATGA-GTCTTAGT-GTACC-AATATC
5085  GROUP_11     AA-CCAGT-GA--ATTA--T-GA-G---T--T-AATGAGGTT-T-GT-GT-CC-AA-AT-
5086  GROUP_12     AA-CCAGT-GAAAATTATATAGATGA-GT--T-AATGA-GTA-TGGTTGT-CCTAATATT
5087  GROUP_13     AATCCAGT-GA-AATTA-ATAGATGA-GTA-T-AATGA-GT-TT-GT-GT-CCAAA--T
5088  GROUP_14     AATCCTGTAGAGAGATATGTTGATGAAGTCCTGAATGAAGTGCTAGTAGTTCCAAATATT
5089  GROUP_15     AACCCAGTAGAAAATTTTGTGGATGAGATCTTGAATGAAGTTTTGGTGGTTCCAGATATC
5090  GROUP_16     AATCCTGTAGAGAATTA--TAGATGAAGT-CTAAATGA-GTCTTAGTAGTGCCAAATATC
5091  GROUP_17     AATCC-GTTGAAAATTATGT-GATGAAATTTAAA-CAAGTTCT-GTAGT-CCAAACAC-
5092  GROUP_18     AA-CC-GT-GA--ATTA--TAGATCA-GT--T-AATGA-GT--TGGT-GT-CCAAA-AT-
5093  GROUP_19     AACCCAGTGGAGAATTACATAGATGAAGTGTT-AATGA-GT--TAGT-GTTCCAAA-ATT
5094  GROUP_20     AACCCAGTAGAGGAATACATAGATGGAGTCTTGAATGAGGTTCTTGTGGTTCCGAACATT
5095  GROUP_21     AATCCAGTAGAAAGCTACATAGATGGGTCTTAAACGAAGTCCTTGTGGTTCCAAACATT
5096  GROUP_22     AA-CC-GT-GA--AATACATTGATGGTGT-TTGAATGAAGT-TT--TTGT-CCAAA-A--
5097  GROUP_23     AATCCAGTTGAAAAGTATGTTGATAGTGTTTTAAACGAGGTATTAGTTGTTCCTAACATT
5098  GROUP_24     AATCCTGTAGAGAAATATGTGGACACCATTCTGAATGAGGTGCTAGTTGTCCCAAATATC
5099  GROUP_25     AATCCTGT-GAAAGGTATGT-GATGA-GTC-TGAATGA-GTTCTTGT-GTACCAAATAT-
5100  GROUP_26     AATCCTGTAGAAAGATATGTAGATGAAGTTTTGAATGAAGTCCTTGTAGTACCCAATATC
5101  GROUP_27     AACCCTGT-GA-AGATATGTAGATGAAGT-TT-AATGA-GT-CTTGTAGTCCC-AA-ATT
5102  GROUP_28     AA-CCAGTGGA--G-TATGT-GATGAAGTCTTAAATGA-GT-TT-GTAGT-CC-AATATT
5103  GROUP_29     AA-CC--TTGA--A-T---TAGATGA-GT-CTTA-TGA-GT-TTAGTTGT-CC-AA-AT-
5104  GROUP_30     AA-CC-GT-GA-AA-TA--TAGATA---T--TAAA-GAAGT--T-GT-GT-CC-AA-AT-
5105  GROUP_31     AATCCAGTAGAGAGATATGTTGATGAGGTGCTAAATGAAGTTCTAGTTGTTCCAAACATA
5106  GROUP_32     AATCCAGTGGAAGAATATGTTGATCAGGTTTTAAATGAGGTTTTAGTTGTTCCAAACATA
5107  GROUP_33     AACCCAGT-GAAA--TACACAGAGC--TT-T-AATGA-GT-CTTGT-GTTCCAAA-AT-
5108  GROUP_34     AATCCAGTTGAAAAATATACTGAAGCACTACTTAATGAAGTGCTTGTTGTGCCAAACATC
5109  GROUP_35     AACCCGGTAGAGAAATACACAGAGGCTATCTTAAATGAAGTATTAGTAGTCCCAAACATT
5110  GROUP_36     AATCCAGT-GAAAAATA-ACAGAAGC--T-CT-AATGA-GT-CTTGT-GTACC-AACATC
5111  GROUP_37     AA-CC--TTGA-AA-TATACAGA-GCT-TACT-AATGAAGTGTTGGTGGT-CC-AA-ATA
5112  GROUP_38     AATCCTGTAGAAAAATATACAGAAGCAATACTCAATGAGGTTCTAGTTGTGCCAAATATA
5113  GROUP_39     AACCCTATTGAACAATTCACAGAGGCAGTATTAAACGAGGTTCTTGTAGTTCCAAA-ACA
5114  GROUP_40     AACCCTGTTGAACAATTTGCAGAAGCAGTCCTTGATCAAGTATTAGTAGTTCCAAACACT
5115  SUMMARY      AA-CC--T-GA----T---X-XA-----T--T-X--XA-GT--T--T-GT-CC-XA----
5116
5117  GROUP_1      AAAGAAAG-CATCACACTACATCAAA-TCTGC-CCACT-TT-GATGCTGCAGAGAC-GGA
5118  GROUP_2      A-AGAGAG-CA-CCAACTA-ATCAAATTC-GC-CCTGC-TTGATGCAGCAGAGACTGG-
5119  GROUP_3      AGGGAGAGCCATCCATCCACATCAAATTCTGCCCCCTGCATTAGATGCTGCTGAAACTGGC
5120  GROUP_4      A-AGAAAGTCATCCAGCTACATCTAATTC-GCCCCCT-C-CTAGATGC-GCAGAAACTGG-
```

FIG. D13 CONT'D

```
09.trace                                                                                    9/20/2007 5:05 PM 5121 GROUP_5      CA-GAAAGCCA-CCAACCAC-TCAAA-GCTGCTCC-G-A-T-GATGC-GC-GA-AC-GGA
5122 GROUP_6      AGAGAGAGCCATCCAACTACATCTAATGCAGCT-CAGCTTTGGATGCTGCTGAAACTGGA
5123 GROUP_7      AGAGA-AG-CATCCAAGCACCTC-AACTCTGC-CCAAT-CT-GATGC-GCTGA-ACTGG-
5124 GROUP_8      AAGGA-AG-CATCCAAGCAC-TC-AA--CTGC-CC-ATACTAGATGCAGCTGAAACAGG-
5125 GROUP_9      A--GA-CA-CACCC-AG-A--TC-AA-TCTGC-CCAAT--T-GATGCTGCTGA-AC-GGA
5126 GROUP_10     AAAGAAAG-CATCCAAG-ACATC-AA-TCTGCCCC-AT--T-GA-GCTGCTGAAACTGGA
5127 GROUP_11     A--GAGAG-CA-GC-ACCACATCAAA--CAGCACCTGC--T-GATGCAGCTGA-AC-GG-
5128 GROUP_12     AAGGAAAGTAAACC-TCAAC-TCAAACTCAGC-CCAGCTTT-GATGCAGCAGAAAC-GGA
5129 GROUP_13     AA-GA-AG-CA-GC-A--ACATCAAA-TC-GCCCC-GC--T-GA-GCTGC-ACTGG-
5130 GROUP_14     AGGGAGAGTCAAGCAGCAACATCAAATTCAGCTCCAGTACTAGATGCAGCAGAAACTGGG
5131 GROUP_15     AAACAAAGTCAAGCAACAACATCAAACTCAGCACCTGCATTGGATGCAGCTGAAACTGGA
5132 GROUP_16     AGAGAGAGTCATGGAACAACATCAAACTCTGCTCCCGCACTTGATGCTGCAGAAACTGG-
5133 GROUP_17     -T-GA-AG-CAT-CAACAAC-TC-AATGC-GC-CC-GC--T-GATGCAGCTGAAACTGG-
5134 GROUP_18     AA--A-AG--A-CC-AC-AC-TC-AA-TCAGC-CCAGC--TAGATGCTGC-GA-ACAGG-
5135 GROUP_19     A--GA-AG-CA-TCAAG-AC-TC-AACTCAGCACCAGCACT-GATGCAGCTGA-AC-GGC
5136 GROUP_20     AAGGAAAGCCACTCCAGCACATCAAATTCAGCACCAGCATTAGATGCTGCTGAGACTGGA
5137 GROUP_21     AGGGAGAGCCAACCCACTACTTCTAATTCTGCTCCAGCATTGGATGCTGCTGAGACTGGT
5138 GROUP_22     AATGA-AG-CA-CC-AG-AC-TC-AATGC-GC-CCAGC--TAGATGC-GC-GA-AC-GGA
5139 GROUP_23     AATGAAAGTCATCCTAGTACTTCAAATTCAGCTCCTGCCTTGGACGCTGCAGAGACAGGA
5140 GROUP_24     AATGAAAGTCATCCAAGTACATCAAATGCTGCTCCTGCCTTAGATGCAGCCGAGACAGGA
5141 GROUP_25     AGTGAAAG-AG--CAACTAC-TCTAATTCAGCTCCAGCC-TAGATGC-GCAGA-ACTGG-
5142 GROUP_26     AATGAAAGTAATCCAACTACATCCAACTCAGCACCTGCACTGGACGCTGCAGAAACTGGC
5143 GROUP_27     AAT-A-AG--ACCC-ACAAC-TCCAA-TCAGC-CCAGT--TAGA-GC-GCTGAAACAGGT
5144 GROUP_28     AATGA-AGCCACCCTAC-ACATC-AAT-C-GC-CC-GTTTT-GATGC-GCTGAAAC-GGA
5145 GROUP_29     AA-AGTAGT-A-CC-AC-ACATCAAA-TCTGC-CC-GCATTAGA-GCTGC-GAAAC-GG-
5146 GROUP_30     CA-CC-AG--CATC-GT-TCAAGTCA--C-G--CC-GC--T-GA-GCTGC-GA-AC-GG-
5147 GROUP_31     AACAAAAGTAATGGGCAGTTATCAAACGCAGCACCAGCGTTGGACGCTGCAGAAACTGGT
5148 GROUP_32     AAAGAAAGTAAACCCCAGTCTAGCAACTCCGCTCCAGTTTTGGACGCTGCAGAAACAGGT
5149 GROUP_33     -CA-C-AGTAA--CCCAAAC-TCAAATGCAGC-CCAGC--TAGATGCTGCTGAGAC-GGA
5150 GROUP_34     AATCCTAGCAACGCACAAACTACAAATGCAGCTCCCGCTCTCGATGCCGCTGAGACGGGG
5151 GROUP_35     AATGCAAGCAATCCACAAACTTCAAATTCAGCACCAGCACTAGATGCTGCAGAAACGGGT
5152 GROUP_36     A-TGC-AG-A-TGGACATACATC-AA-TCAGCTCCA-CACTTGATGCAGCAGAAACTGG-
5153 GROUP_37     CAA-CTAG-A-TGGGCA-ACATCTAATGCTGCACCAGCT-TAGATGCTGCTGA-ACAGGA
5154 GROUP_38     CAACCTAGTAATGGACATACCTCAAACTCAGCACCAGCCTTAGATGCAGCAGAAACTGGG
5155 GROUP_39     CAAGC-AGTAATGGATCTATAGCAAATTCAGCACCAGCATTAGATGCAGCAGAGACTGGA
5156 GROUP_40     CGACCCAGCGATGGGTTGATTGCAAACTCAGCCCCAGCTTTGGATGCAGCTGAAACTGGA
5157 SUMMARY      ----X-AG-----X-X--X--XX-XA--C-G---C-----T-GA-GC-GC-GA-AC-GG-
5158
5159 GROUP_1      CACACCAGTAATGT-CAACCAGA-GATGCTATAGA-ACAAG-TATGTTAT-ACATCACAA
5160 GROUP_2      CATACAAG-A--A-ACA-CC-GA-GATACAATAGA-AC-AG-TTTGT-CA-AC-TCACA-
5161 GROUP_3      CATACTAGTGCAATCCAACCAGAAGACACTATAGAAACCAGATATGTACAGACATCACAA
5162 GROUP_4      CACACTAGTGGA-TACAACC-GAGGA-AC-ATAGAAACAAGAT-TGTGCAGACATCACAA
5163 GROUP_5      CA-ACAAGCAGTATACAACCTGAGGATAC--TAGAAAC-AGATAT-CA-AC-TC-CAA
5164 GROUP_6      CACACAAGTAGCA-CCA-CCTGAAGACACAATTGAAACAAGATATGTGCAAACCTCACAT
5165 GROUP_7      CA-AC-AGTA-TGT-CAACC-GAAGATAC-GTTGAAAC-CGATATGTGCA-ACATC-CAG
5166 GROUP_8      CA--ACTAGTA--GT-CAACCAGAAGATACAGTTGAGAC-CG-TA-GT-CAAAC-TC-CAG
5167 GROUP_9      CA-ACTAG-AATGT-CAACCAGA-AC-ATTGA-AC-CG--ATGT-CAAACC-CACA-
5168 GROUP_10     CACACTAG-AATGTACA-CCAGAAGATACAATTGAAACTCG-TA-GT-CAAACA-CACAA
5169 GROUP_11     CA-AC-A--A--GT-CA-CCAGA-GA-ATG-TTGA-AC-AG-TATGT-CA-AC-TCACA-
5170 GROUP_12     CATAC-AGT---GT-CAGCCAGAAGAT-TGGT-GA-AC-AGATA-GT-CAAACATCACAA
5171 GROUP_13     CACAC-AG-A-TGT-CA-CCTGAAGATATG-TTGA-AC-AG-TA-GT-CAAACATC-CA-
5172 GROUP_14     CATACAAGCAATGTACAACCAGAAGATGTAATTGAGACAAGATATGTTCAGACATCACAA
5173 GROUP_15     CACACTAGTAATGTACAACCGGAAGACATGATTGAAACTAGATATGTCCAGACATCACAA
5174 GROUP_16     CACACTAGTAATGTACA-CC-GAGGATATGGTTGAAACAAGGTATGTTCAGACATCACAA
5175 GROUP_17     CATAC-AGCCA-GT-CAACC-GAAGACATG-TAGA-ACAAGG--AGTACA-AATTTCCAA
5176 GROUP_18     CA-AC-AG-A-TGT-CAACCTGAAGA-ATGAT-GA-AC-CGTTATGT-CA--CA-CA-A-
5177 GROUP_19     CATAC-AG-A-TGT-CAACC-GA-GATATG-TTGA-AC-CG-TA-GT-CAAAC-TCACAG
5178 GROUP_20     CACACCAGTAATGTGCAGCCTGAGGATATGATTGAAACTCGCTATGTACAGACATCACAA
5179 GROUP_21     CACACTAGTAATGTACAGCCTGAGGACGATGATTGAAACACGTTATGTGCAGATTACACAA
5180 GROUP_22     CACAC-AG-AATGT-CA-CC-GA-GA-ATGAT-GAAAC-CGCTATGT---AAA--C-CAA
5181 GROUP_23     CATACAAGTACTGTTCAACCTGAGGACATGATTGAAACACGGTATGTTCAAACATCACAA
5182 GROUP_24     CATACTAGCAATGTACAGCCTGAGGACATGATCGAAACACGCTATGTTCAAACGTCCCAG
5183 GROUP_25     CA-AC-AG-A-TGTACAACCAGA-GACATG-TTGAAACACG-TATGTCCAAAC-TCACAG
5184 GROUP_26     CATACCAGTGGTGTACAACCAGAAGACATGATTGAGACCCGTTATGTCCAAACATCACAG
5185 GROUP_27     CATAC-AGCAATGT-CAACC-GAGGA-A-GATTGA-AC-CGATATGTTCA-AC-TC-CAG
```

FIG. D13 CONT'D

09.trace                                                                                                  9/20/2007 5:05 PM

```
5186  GROUP_28   CA-ACCA-TAA-ATACA-CC-GA-GA-ACTAT-GA-ACCAGATATGT-CAATCTTCACAG
5187  GROUP_29   CA-ACTAG-A-TGT-CAACC-GA-GATGTCATTGAAAC-AG-TA-GT-CA-ACATCACAA
5188  GROUP_30   CA-AC-AG-TCTGT-CA-CC-GA-GA-ATGAT-GA-AC-AG-TATGT-AT-AC-GA-CAA
5189  GROUP_31   CATACCAGCCAAACACAACCAGAAGATGTGATTGAAACCAGGTATGTGATTACAGACCAG
5190  GROUP_32   CATACGAACCAAGTACAGCCTGAAGACACCATAGAAACTAGATATGTTATAACTGACCAA
5191  GROUP_33   CA-ACAAACCA-GTCCA-CCAGAAGAT-TGGT-GA-ACACG-TATGT-AT-AC-GA-CAG
5192  GROUP_34   CACACAAGCCAAACACAACCTGAAGACATGTTGAGACTAGGTATGTAATTCACAGATCAG
5193  GROUP_35   CATACAAGTCAGACACAACCTGAGGACATGCTGGAAACTAGATATGTCATCACAGACCAA
5194  GROUP_36   CACACTAGCCAG-T-CAACCAGAAGACATGATAGAAAC-AGATATGTTAT-AC-GA-CA-
5195  GROUP_37   CA-ACTAGTCAAGTTCAACCAGA-GAT-TG-TAGA-ACCAG-TATGT--TCACAGA-CAA
5196  GROUP_38   CATACCAACCAAGTACAACCAGAAGATGTTATGGAAACCAGATATGTGATCACTGATCAA
5197  GROUP_39   CACACAAGTTCAGTGCAACCTGAAGATCTTATAGAGACTAGGTATGTAATTACAGATCAA
5198  GROUP_40   CACACCAGTTCAGTGCAGCCTGAGGACCTTATAGAGACTAGATATGTGATTGCAGACCAA
5199  SUMMARY    CA-AC-A--------CA-CC-GA-GA-----T-GA-AC-XG----GT-----X--X--A-
5200
5201  GROUP_1    ACAAGAGATGAGATGAGTATAGAAAGTTT-CTTGGTAGATCTGG-TGTGT-CA-AT-TCA
5202  GROUP_2    ACTAG-GATGAAATGAG--TAGA-AGTTTCTTGGGAAGATCTGG-TG-AT-CATATATC-
5203  GROUP_3    ACTAGGGATGAAATGAGAGTATAGAAGTTTTCTAGGTAGATCAGGTTGTATACATATATCA
5204  GROUP_4    AC-AGAGATGAAATGAG-ATAGAAAGTTTTCTAGG-AGGGC-GGTTG-ATACATGAATC-
5205  GROUP_5    AC-AG-GATGA-ATGAGTGTAGA-AG-TT--T-GGTAGATC-GG-TG-ATACA-AT-TCA
5206  GROUP_6    ACTAGGGATGAAATGAG-GTTGAAAGTTTCTTAGGCAGATCTGGCTGTATTCACATTTCC
5207  GROUP_7    AC-AG-GATGAAATGAGTATTGA-AG-TTTCTTGG-GA-TC-GGTTGTATACACACCTCA
5208  GROUP_8    AC-AG-GATGA-ATGAG-AT-GA-AG-TTTCT-GGTAGGTC-GG-TGTAT-CA-AT-TCA
5209  GROUP_9    ACTAGAGATGAAATGAG-ATTGA-AG-TT--T-GG-AG-TCAGG-TG--TACA---TTCA
5210  GROUP_10   ACAAGAGATGAAATGAGCATTGA-AG-TTCCTTGG-AGGTCAGGATGTGT-CAT-C-TCA
5211  GROUP_11   ACTCTTGATGA-ATG-G--T-GA-AG-TTC-TAGG-AG-TCTGGTTG-ATTCA-AT-TC-
5212  GROUP_12   ACA--A-ATGA-ATGAGTGTTGAAAGTTT--T-GG-AGATCAGGTTGCAT-CA-ATGTC-
5213  GROUP_13   ACAAGAGATGAAATGAG-AT--GTTT-CT-GG-AG-TC-GG-TGTATACA-AT-TC-
5214  GROUP_14   ACTCGTGATGAGATGAGCATTGAAAGTTTTCTAGGTAGATCAGGATGTGTACATATATCA
5215  GROUP_15   ACACGTGATGAAATGAGTCTTGAGAGCTTCTTAGGAAGATCTGGCTGCATTCATATTTCA
5216  GROUP_16   ACACGTGATGAAATGAGTATTGAAAGTTTTCT-GGCAGATCAGGGTG-AT-CACATGTCA
5217  GROUP_17   AC-AGAGATGA-ATGAGTATTGA-AGTTTC-T-GGCAGATCTGG-TG-AT-CATATTTCA
5218  GROUP_18   AC-AGAGATGA-ATGAGTCT-GA-AGCTT--T-GG-AG-TCAGG-TGT-T-CA-ATATC-
5219  GROUP_19   AC-AGAGATGA-ATGAGT-T-GA-AG-TT-CTTGG-AGATCAGG-TG--TCCATAT-TC-
5220  GROUP_20   ACTAGAGATGAAATGAGTGTAGAAAGTTTTCTAGGAGAGATCAGGTTGTGTACATATATCC
5221  GROUP_21   ACTAGAGATGAGATGAGTGTTGAGAGCTTCCTCGGCAGATCTGGATGTATTCATATTTCC
5222  GROUP_22   AC-AG-GATGAAATGAG-ATTGA-AG-TTC-TGGG-AG-TCTGG-TG-ATACA-ATA-CA
5223  GROUP_23   ACTAGAGATGAGATGAGCCTTGAGAGTTTCCTAGGGAGATCTGGCTGCATACACATATCA
5224  GROUP_24   ACTAGGGATGAAATGAGCATAGAAAGTTTTCTTGGCAGATCCGGTTGTGTACATGTTTCA
5225  GROUP_25   ACTAG-GATGAAATGAG--T-GA-AGCTTTTTAGG-AGATC-GG-TGT-TACA-A-GTC-
5226  GROUP_26   ACTAGAGATGAAATGAGCATTGAAAGCTTCCTTGGCAGGTCAGGTTGTATACACATGTCA
5227  GROUP_27   AC-AGAGATGAAATGAG--T-GA-AG-TT-TTGGGTAGATCAGGGTG-ATACA-ATGTCA
5228  GROUP_28   ACA-TGGATGAAATGAGTGT-GAAAG-TT--TAGGCAGATC-GG-TGCAT-CATGAATC-
5229  GROUP_29   ACAAG-GATGAAATGAGTTTAGA-AG-TT-CTTGG-AG-TCAGG-TG-ATACA-GA-TC-
5230  GROUP_30   ACAAG-GATGA-AC-AG-AT-GA-AG-TT--T-GGTAG-TC-GG-TG-AT-GC-A---T-
5231  GROUP_31   ACTAGAGATGAGATGTCAATTGAATCTTTCCTTGGTCGGTCCGGATGCATTTCAATTATC
5232  GROUP_32   ACAAGAGATGAAATGAGCATTGAAAGTTTCCTCGGAAGATCAGGTTGTGCAACAATTATG
5233  GROUP_33   AC--G-GATGAAATGAG--T-GA-AG-TT-CT-GGTAG-TC-GGTTGCATTGC-ATCATA
5234  GROUP_34   ACCCGTGATGAAATGAGTATAGAGAGTTTCTTAGGTAGGTCTAGTTGCATTGCAATAATC
5235  GROUP_35   ACCCGGGATGAAATGAGCATTGAAAGTTTCCTTAGGCAGATCAAGTTGCATTGCTGAGATC
5236  GROUP_36   ACAAA-GATGA-ATGAG-AT-GAAAGTTT--TAGGAAG-TC-GG-TG--TTGC-AT-ATT
5237  GROUP_37   AC-AGAGATGA-ATGAG--TAGAGAGTTTC-TGGG-AGATCTGC-TGC-TAGCA-TCAT-
5238  GROUP_38   ACTAGGGATGAAATGAGCATTGAGAGCTTCTTGGGCAGATCTGCATGCATAGCTACCATA
5239  GROUP_39   ACTAGG-ATGAGACATCACTGGAATCTTTCTTGGGTAGAGCAGGATGCATTAAAAT-ATT
5240  GROUP_40   ACCAGACATGAAACCTCCATTGAATCTTTTTGGGTAGGGCTGGATGTGTGGCCAATATT
5241
5242  SUMMARY    AC-----ATGA-AX--X--T-GA--X-TT--T-GG-XG-XC-XX-TG--X-XX-----X-
5243  GROUP_1    AGAATAAAGGTTGATTACA-TGAC................TA-AATGGA...--G-ACA-A
5244  GROUP_2    ACAATTAC-GTG-ATAACA---T-................GA-TATG......ATGA-A-
5245  GROUP_3    ACTATAACTGTGGATAATGATGTA................GATTATA......ATTCAAAG
5246  GROUP_4    AC-AT-AC-ATTCAAAATGATGTA................GAATA-A......A-GATCA-
5247  GROUP_5    ACTAT-ACTGT--A-AAA--CAT-................-A-TATG......A---TGGA
5248  GROUP_6    ACAATTACTATGAAGAAGGAG...................AACTATA......ATGA-CAT
5249  GROUP_7    ACAAT-ACTGT-A-TAA--A--A-A...............---TA-A......ATGA-CAC
5250  GROUP_8    ACAAT-AATGT-GA-------AAA................AC-TATG......ATGAATC-
```

FIG. D13 CONT'D

```
09.trace                                                                  9/20/2007 5:05 PM 5251 GROUP_9    ACAAT--A-..........-CAA--................C-----C......A--A----
5252 GROUP_10   A-AATA-AA..........-CA-AT...............G--C--C......A---TA--
5253 GROUP_11   AA--TA-T-GT--A-TATGA-G--................TAT-AT......G--A--AA-
5254 GROUP_12   AA--TT---TGT--A-TAT...GA-...............AATTAT......GAT--AAA-
5255 GROUP_13   AA--T-GTTGT--ATTATGA---T................TA-AATG--....-AAACAA-G
5256 GROUP_14   GAGTTAGTTGTTCATTATGAAGAA................TATAACAAA...GAGGGAAAA
5257 GROUP_15   GAGCTTAAGGTAAAATATGAAAAT................TACAACACA...GAG......
5258 GROUP_16   AAATTA-TAGTTAACTATGA-AA-................TACAATACT...GGAGAAAAT
5259 GROUP_17   ACACTTGA--T--ATTAT----A-................TATAATGG-...--AGGCA-A
5260 GROUP_18   AAATT--ATATTGATTA-A-----................TA--AT-A-...AGT----A-
5261 GROUP_19   -AT-T-AAAAT--ATTAT--A-A-................TATAAT---...-A-GGGAA-
5262 GROUP_20   AATCTTGACATAGATTACATTAAT................TACAACTCT...GAAGACAAA
5263 GROUP_21   AAATTAGAAATTGACTATAGTAAC................TACAATGAG...GAGAATAAA
5264 GROUP_22   -A--TA-A--T-AA-TA----GG-................TA-AATGA-...G--GG-AA-
5265 GROUP_23   CACCTAAATGTCAGATACACTG..................ATTATAAT...GAAGGTAAT
5266 GROUP_24   GAGCTCCAATTAGATTATACCAAT................TACAATCAA...GAAAATAAT
5267 GROUP_25   AC--TGAA-ATAGATTATACT-AT................TATGATGAT...TCT-T---A-
5268 GROUP_26   ACTATGAATATAAATTATGAAAAT................TATGATGAT...GCTCCTGAA
5269 GROUP_27   ACATTAAA-ATA-A-TATGA-AA-................TATGATGA-...TC---T-A-
5270 GROUP_28   -T--TTGGA-ATT---GA--ATTAC...............AAT---........CA-
5271 GROUP_29   AAA-TA-A--T-----T---A-A-................TA--A---.........A--A-
5272 GROUP_30   -AA-TT---ACAA---------A---T.........-A--A-GA-------A--GG----
5273 GROUP_31   GAATTGGATTTAGACCATGAAGGT................TATTCAGCA...GAAGGAAA
5274 GROUP_32   AGACTAGAATTGGACCACACTGAT................TACAATGCT...GAAGGGAAA
5275 GROUP_33   CATACTGACTTAGATCA--A-G---A-.........CA-TA-AATGCA...CC-GGAAAA
5276 GROUP_34   CATACTGATGTTGTGCATGAAACAGAC.........AAGTACAACCAC...CCAGGGAAG
5277 GROUP_35   CATACCAATTTAGACCAT...ACTG...........GATACAATGAG...CCTGGGAAA
5278 GROUP_36   GA-AC--AATT-AA-CATGAA--AG--.........A--TACAATGC-...GA-G-TCA-
5279 GROUP_37   CA-ACA-A-CTT-A-CATG---A-G-AG-C--A-A-G--TACAATG--...-AAGG-A-A
5280 GROUP_38   CACACTAAATTAGTACATGGAGAGGAGGG......TGTTTATAATATG...AAAGGTAAC
5281 GROUP_39   GCATTAGAACTAGATCATGACAAC................TATGAT-AA............
5282 GROUP_40   AGTTTAGACATTAACCATGATGAC................TACCAAAAG............
5283 SUMMARY    ----X-----X---------------X-X--X-X-------------------------
5284
5285 GROUP_1    AA-TT-ACAA-ATGGAAAATCACACT-CAGGA-ATGGCACA-ATTAG-AGAAAATT-GAA
5286 GROUP_2    CACTTTGAT-AGTGGCAGATAAC-ATACA-GA-ATG-CACAAATTAG-AG-AA-TTTGA-
5287 GROUP_3    CATTATAATAAATGGCAAATAACCTTACAAGAAATGGCTCAAGTTAGGCGTAAATTTGAA
5288 GROUP_4    CATTTTA---AATGGGATATAACATTACAAGA-ATGGCACAAAT-CGAAG-AAATTTGAA
5289 GROUP_5    CA-TTT--TAAATGGC--ATAACATTACAAGAGATGGCACAAATTAG-AG--AAATTTGAA
5290 GROUP_6    AATTTTGTGGATTGGAAAATTACTTTGCAGGAGATGGCACAGGTTAGAAGGAAATTTGAA
5291 GROUP_7    ACTTTTGACA-ATGGCAAATAAC-CTACA-GAAATGGCCCAAATTAGAAGGAAATTTGAA
5292 GROUP_8    AAATTTAGAA-ATGGCAAATTACA-T-CAAGAAATGCCT-CAAAT-AG-CGCAAATTTGA-
5293 GROUP_9    A---TT--A-A-ATGGAAT-T-AA-TTACAAGA-ATGGCTCAAAT-AG--G-AA-TTTGA-
5294 GROUP_10   AAAT-TAAAGTATGGCACATTAATTTACAAGA-ATGGCCCAGAT-AGGCG-AAAT-TGAA
5295 GROUP_11   AA-TTTA--ACATGGAAAATAAA--T-CAAGA-ATGGCACA--TTAG-AG-AAATTTGA-
5296 GROUP_12   AA-TT----AAATGGCAAAT-AA-CT-CAAGA-ATGGC-CA--T-AGAAGAAAATTTGAA
5297 GROUP_13   AACTT----A-ATGGCAAAT-AA--TACA-GAAATGGC-CAGAT-AG-AG-AAATTTGAA
5298 GROUP_14   AATTTTACTAAGTGGCAAGTAAACATCCAAGAGATGGCTCAGATTAGAAGAAAATTTGAA
5299 GROUP_15   AATTTCACTAAATGGGAAATAAATCTACAAGAAATGGCACAAATCAGAAGAAAATTTGAA
5300 GROUP_16   AACATTA-TACATGGCAAATAAATATTAAAGAGATGGCACAAATTAGGAGAAAATTTGAA
5301 GROUP_17   AA-TT-AC-CA-TGGCCAATCAA--T-CA-GAAATGGC-CAAATTAGAAG-AA-TATGAA
5302 GROUP_18   AATTTCACAAT-TGGAA-ATAAATATAAA-GAAATGGCCCAGAT-AGGAG-AAATTTGA-
5303 GROUP_19   AA-TTTACTAAATGGCAAAT-AATCT-AAAGAAATGGC-CAGATTAG-AG-AAATTTGAG
5304 GROUP_20   AACTTTACAACATGGCAAATCAATCTCAAAGAAATGGCTCAAATCAGAAGAACAAAGTTTGAA
5305 GROUP_21   AATTTCACAACTTGGCAAATTAACCTAAAGGAAATGGCACAAATAAGAAGAAAGTTTGAA
5306 GROUP_22   AA-TT--A---ATGGCA-AT-A-C-T-AAAGA-ATGGC-CA-ATAAGAAGGAA-T-TGA-
5307 GROUP_23   AACTTTAGATCATGGCAAATAAGCATAAAGGAAATGGCACAAATTAGAAGGAAGTTTGAA
5308 GROUP_24   AATTTCAAAACTTGGCAAATAAACTTGAAAGAAATGGCACAGATTAGAAGAAAATTTGAA
5309 GROUP_25   AA-TT---GAA-TGGAAAAT-AG-TT-CA-GA-ATGGCCCAAGT-CG-AGAAA-TTTGAG
5310 GROUP_26   AATTTTACCAAATGGAAAATAAGTTTACAAGAGATGGCTCAAATACGTAGGAAATTTGAA
5311 GROUP_27   AA-TT-AAGGTGTGGAAAATAAA--CT-CAAGA-ATGGC-CAAAT-CG-AG-AA-TTTGA-
5312 GROUP_28   AG-TT-ACTAAATGGAA-AT-AAC-T-CAAGA-ATGGCACAAATTAG-AGAAA-TTTGAA
5313 GROUP_29   AA-TT-A-----TGG---AT-AAT-T-CA-GAAATGGC-CA-AT-AGAAG-AA-TTTGA-
5314 GROUP_30   GG-T-----ACATGGAA--T-AG--T-CAAGA-ATGGCACAAAT-AG-AG-AA-T-TGA-
5315 GROUP_31   AACTTTAAAACATGGAAGATAAATCTTAAGGAAATGGCCCAGATTAGAAGGAAAAATGAG
```

FIG. D13 CONT'D

```
09.trace                                                                    9/20/2007 5:05 PM 5316  GROUP_32   AATTTTACAACGTGGAAAATCAACTTACAGGAGATGGCCCAGATTAGAAGAAAGAATGAG
5317  GROUP_33   AA-TTCTC-CA-TGGAA-AT-ACAAT-AAGGAAATGGCTCAAAT-AGAAGAAA-TGTGA-
5318  GROUP_34   AATTTTAGTAAATGGAATATCACTCTCAAAGAAATGGCCCAAATCAGAAGAAAGTGTGAA
5319  GROUP_35   AACCACTCAGAATGGAAGATTACACTCAAAGAAATGGCCCAGATTAGAAGGAAATGTGAG
5320  GROUP_36   AA-TT-TCAAA-TGGAAAATAACA-T--TGGAAATGGCACAAAT-AGAAGAAAGTGTGA-
5321  GROUP_37   AATTTCTCT-C-TGG-AAATTACACTCAA-GAAATGGCTCAAATTAG-AGAAAGTGTGAA
5322  GROUP_38   AATCTCTCAAAGTGGCAGATTACACTCAAAGAAATGGCTCAGATCAGGAGGAAATGTGAA
5323  GROUP_39   A-TTTCAGGACCTGGGGAATAAACATACAAGAGATGTCACAAATTAGAAGGAAATTTGA-
5324  GROUP_40   AATTACAAAAATTGGGCAATTAGTTTACAAGAAATGTCACAAATTAGGAGGAAATTTGAA
5325  SUMMARY    X--X--------TGG----T-A---T--X-GA-ATG-C-CA--T-XG--G-AA-X--GA-
5326
5327  GROUP_1    -T-TTTAC-TATGT-AGGTTTGA-TCAGAA-TAAC-TT-G.T-CC-TGTATTGCTGGTAG
5328  GROUP_2    TTCTTTAC-TA--CTAG-TTTGATTCAGAAAT-AC-TTAG.T-CCTTGTATAGC-GG-AA
5329  GROUP_3    TTCTTTACTTATGTCAGATTTGATTCAGAGGTTACTTTGG.TACCTTGTGTAGCCGGCAA
5330  GROUP_4    TTCTTTACTTATGTTAG-TTTGATTCAGAA-TTAC--TAG.T-CC-TG-ATAGCTGG-AA
5331  GROUP_5    TTCTTCACATATGT-AGATTTGA-TCAGAA-TCACT-T-G.T-CC-TG-ATAGC-GGAAA
5332  GROUP_6    ATGTTCACCTA-GTTAGATTTGACTCAGAGATTACTTTAG.TCCCATGCATAGCTGGAAG
5333  GROUP_7    ATGTTTACATATGT-AGATTTGACTCAGAA-TCAC-TT-G.TACC-TG-AT-GCAGG-AA
5334  GROUP_8    ATGTT-ACATATGT-AG-TTTGATTC-GAAATTACATT-G.TCCCATG-ATTGC-GGAAA
5335  GROUP_9    ATGTT-ACATATGT-AGATTTGA-TC-GA-ATAAC-CT-G.TTC--T--ATTGCAGGAC-
5336  GROUP_10   ATGTT-ACATATGTAAGATTTGATTCAGAAGT-ACCAT-G.TTCCATG-ATTGCAGG--A
5337  GROUP_11   ATGTT-ACATA--C-AGATTTGATTCAGA--T-AC--T-G.T-CCTT-TATAGCTGC--A
5338  GROUP_12   TT-TT-ACATAT-CTAGATTTGA-TCTGA-ATTACAATAG.T-CCATC-ATAGCTGGCAA
5339  GROUP_13   ATGTT-AC-TA-GT-AG-TTT-ATTC-GA--T-AC--TAG.TACCATC--TAGC-GC-AA
5340  GROUP_14   ATGTTCACCTATACTAGATTTGATTCAGAAGTTACATTAG.TACCCTCTATTGCTGCAAA
5341  GROUP_15   CTATTTACATATGTTAGGTTTGATTCTGAAGTTACATTAG.TTCCCTCCATAGCTGCTCA
5342  GROUP_16   ATGTTCACCTATACTAGATTTGATTCAGAAATAACTTTGG.T--CCGTCAATTGCAGCTA-
5343  GROUP_17   TT-TT-ACATA--T-AG-TTTGATTC-GA--TAAC-CT-G.T-CC-TGCATTGCAGC-AA
5344  GROUP_18   -T-TT-ACATA--CAAG-TTTGA-TCTGA-ATAACA-T-G.T-CC-TG-ATAGC-GCAGA
5345  GROUP_19   TT-TTCACATATGT-AG-TTTGA-TCAGAA-T-ACA-T-G.T-CCATGCATTGC-GC-AA
5346  GROUP_20   ATGTTTACATATGTGAGATTTGATTCAGAAGTTACATTAG.TCCCATGTATAGCAGCACA
5347  GROUP_21   TTATTTACATATGTAAGATTTGATTCAGAATTGACTCTGG.TCCCATGCATAGCAGCAAA
5348  GROUP_22   -TATTTAC-TAT-T-AG-TTTGATTC-GAAAT-AC-TT-G.T-CC-TGCAT--C-TC-CA
5349  GROUP_23   CTTTTCACATATGTGAGATTTGATTCAGAAATTACTTTAG.TGCCTTGCATAGCCTCTCA
5350  GROUP_24   CTTTTCACTTACCTCAGATTTGATTCAGAGGTAACATTAG.TCCCCTTGCATAGCTGCTAA
5351  GROUP_25   TT-TT-AC-TATGT-AGATTTGA-TCAGAAATAACAATTG.TGCCA-GTATAGC-GG-CA
5352  GROUP_26   TTATTCACCTATGTAAGATTTGATTCAGAAGTGACAATTG.TACCCTGTATAGCTGGTCA
5353  GROUP_27   -TGTTCAC-TATGCTAGATTTGATTCAGAGAT-ACAATTG.T-CC-TGTGTTGCTG-GCA
5354  GROUP_28   ATGTT-AC-TA--C-AGATTT-ACTCTGA-ATTAC--TGG.TACCAAGT-T-GCA--CAA
5355  GROUP_29   -T-TT-AC-TA-ACTAG-TT-GATTCTGA-AT-AC--T-G.TTCC-TG-ATTTC-GC-CT
5356  GROUP_30   -T-TT-ACATA-AC-AGATTTGA-TC-GA-AT-ACAATAG.TCAC-GCAGC-GC-G--CA
5357  GROUP_31   CTTTTCACCTACTTAAGGTTTGATTCTGAAATCACCATTGTTCCAAGCAATG.CAGCAAT
5358  GROUP_32   ATGTTCACATATCTCAGATTTGATTCAGAAATCACTCTTG.TGTGTGCAGTGGCCTCACA
5359  GROUP_33   CT-TT-ACATACCT-AG-TTTGA-TCTGAGATTACAATAG.TAGCAACA-TAGCTGC-CT
5360  GROUP_34   ATGTTTACATATCTCAGATTTGATTCTGAAATTACTATAG.TGGTGTCAGTTGCAAGTAA
5361  GROUP_35   ATGTTCACATATCTTAGATTTGATTCAGAAATAACTATAG.TGGTATCAGTGGCTAGTAA
5362  GROUP_36   CTTTT-AC-TA-CTCAGATTTGA-TCAGAAATAACAATAG.T-AC-AC-TT-GCAGG-CA
5363  GROUP_37   CT-TTCAC-TA-TT--G-TTTGA-TCAGA-AT-AC-ATAG.T-GCTAC-AT-GCTGGACA
5364  GROUP_38   CTCTTCACATACCTGCGCTTTGATTCAGAGATAACAATTG.TAGCTACACTAGCAGGGCA
5365  GROUP_39   ATGTTCACTTATGTAAGATTTGATTCAGAGATAACAATTG.TACCATGTATTGCAGCTAT
5366  GROUP_40   ATGTTTACATATGTCAGATTTGATTCCGAAATAACAATAG.TACCATGTGTTGCTGCCAC
5367  SUMMARY    -T-TT-AC-TA--X--G-TT--A-TC-GA--T-AC--T-GXT-X------X--C------
5368
5369  GROUP_1    AGGAGA-GACATTGG-CAT-TTGTAATGCA-TATATGTATGTTCC-CCAGGAGCTCCAAT
5370  GROUP_2    GGGTGA-GA-ATTGGACACATTGT-ATGCA-TATATGTATGT-CCCCC-GG-GCACC-AT
5371  GROUP_3    GGGAGATGATATTGGACACATTGTAATGCAATACATGTATGTGCCTCCTGGTGCACCACT
5372  GROUP_4    GGGAG-TGA-ATTGGACACATTGTCATGCAATTCATGTATGT-CC-CCTGGTGCAC-AA
5373  GROUP_5    AGG-GATGACATTGGTCATATAGT-ATGCA-TA-ATGTA-GTTCCACC-GGTGC-CC-CT
5374  GROUP_6    AGGTGAAGATATTGGACACATAGTAATGCAATACATGTATGTCCCACC-GGTGCACCTGT
5375  GROUP_7    -GG-GATGACATAGG-CA-AT-GT-ATGCA-TA-ATGTATGTGCCACCTGG-GCTCCAGT
5376  GROUP_8    -GGTGATGA-ATAGGACAT-TTGT-ATGCAATACATGTATGTACCACC-GG-GC-CC-AT
5377  GROUP_9    TGGT---GATATAGG-CACATAGTTATGCA-TA-ATGTATGT-CCACCTGG-GC-CCA-T
5378  GROUP_10   TGGT--TGACATAGG-CA-ATAGT-ATGCAATACATGTATGT-CC-CCTGGGGC-CCAGT
5379  GROUP_11   -GG--ATGA--TTGGTCATGT-GT-ATGCA-TA-ATGTATGTCCCACCAGG-GC-CCAG-
5380  GROUP_12   GGG--ATGA-ATTGGACATGTTGT-ATGCA-TACATGTATATACCACCTGG-GCACCAGT
```

FIG. D13 CONT'D 09.trace                                                                                           9/20/2007 5:05 PM

```
5381 GROUP_13    -GGTG-TGA-AT-GGACAT-TTGT-ATGCA-TACATGTATGT-CC-CCAGG-GCACCAAT
5382 GROUP_14    GGGAGATGACATTGGACATGTAGTCATGCAATACATGTATGTTCCACCTGGAGCACCAAT
5383 GROUP_15    AGGTGAGGATATAGGCCATGTTGTAATGCAATACATGTATGTCCCTCCTGGGGCACCAAT
5384 GROUP_16    A-CGGGTGACATAGGACATGTTGT-ATGCAATATATGTATGTCCCACCAGGTGCTCCAAT
5385 GROUP_17    A-G-AATGA-ATAGGCCATGT-GTAATGCA-TA-ATGTATGTACCACCAGG-GC-CCAAT
5386 GROUP_18    -AGTGA-AGC-TTGG-CATGTTGT-ATGCA-TA-ATGTATGTACC-CCAGG-GC-CC--T
5387 GROUP_19    -AGTGA-AACAT-GG-CATGTTGT-ATGCAATA-ATGTATGT-CC-CC-GGAGC-CCTTT
5388 GROUP_20    AAATGAAGGTGTGGGGCATGTTGTTATGCAGTATATGTATGTCCCTCCAGGGGCACCATT
5389 GROUP_21    AAATGATGGCATAGGTCATGTTGTCATGCAATACATGTATGTCCCCCCAGGAGCACCATT
5390 GROUP_22    -AGT---AA-ATTGGTCATGT-GT-ATGCA-TA-ATGTATGT-CC-CCTGGAGCTCC-A-
5391 GROUP_23    AAGTAATGATATTGGGCATGTAGTGATGCAATACATGTATGTCCCACCAGGTGCTCCTAA
5392 GROUP_24    AAGTAAAAACATTGGACATGTTGTTATGCAATACATGTATGTGCCTCCTGGTGCTCCTAT
5393 GROUP_25    -GGT-GTGATGTCGGACATGT-ATGCAATACATGT--GTACC-CC-GG-GCACCCCT
5394 GROUP_26    AAGTGGAGATGTGGGACATGTAGTTATGCAGTATATGTATGTCCCACCTGGAGCCCCTCT
5395 GROUP_27    --GTGGTGA-ATTGG-CA-GTGGTCATGCAATA-ATGTATGTTCCACC-GGTGC-CC-AC
5396 GROUP_28    -GA-GGTCA-ATTGGTCATATAGT-ATGCAATA-ATGTATGTACCACCAGGAGCACC-AT
5397 GROUP_29    -AG--A-GA-AT-GG-CACAT-ACAATGCA-TA-ATGTATGT-CC-CC-GG-GC-CC--T
5398 GROUP_30    -GG--A-GATA-TGG-CAT-T-GT--T-CAATT-ATGTATGT-CC-CCAGG-GC-CC--T
5399 GROUP_31    AGAAGGAAGCAATGGTCACGTGGTGGTCCAATACATGTATGTACCTCCTGGTGCCCCACT
5400 GROUP_32    AGGAGACAATAATGGACATGTGGTGCTTCAATTTATGTTGTTCCACCTGGAGCCCCTAT
5401 GROUP_33    -GG----GATAATGG-CATGT-GTTTTACAGTA-ATGTATGT-CC-CCAGGGGCACC-AT
5402 GROUP_34    AGGTGATGATAATGGGCATGTAGTTATGCAATATATGTATGTACCTCCAGGAGCCCCCAT
5403 GROUP_35    ACAAGGGAATAACGGGCACGTGGTGATACAATACATGTATGTACCACCGGGTGCTCCAAT
5404 GROUP_36    AGGGGA-GA-ATTGG-CATGT-GT-AT-CAATA-ATGTA-GT-CC-CC-GG-GC-CC-TT
5405 GROUP_37    -GGTGATGACATAGGGCACAT-GT-CTTCAATA-ATGTATGT-CC-CCTGG-GG-CC-GT
5406 GROUP_38    AGGAGATGATTTAGGACATATTGTACTCCAGTACATGTATGTTCCCCCAGGTGGTCCAAT
5407 GROUP_39    A-AAGGTGACCTTGGACACATAGTCCT-CAATACATGTATGTTCCCCCGGGTGCACCTCT
5408 GROUP_40    AGAAGGTAACTTGGGACACATTGTTGTGCAATACATGTTTGTACCACCAGGAGCACCTCT
5409 SUMMARY     --X----XX----GG-CA--T-XX--T-CA-TX-ATGT--XT-CC--CC-GG-GX-CC---
5410
5411 GROUP_1     TCC---AA-AAGAAA-GATTTCTCATGGCAATCAGGCAC-AATATGTCAATATTCTGGCA
5412 GROUP_2     ACCAA-GAAAAGA-ATGATTACACATGGCA-TCAGG-ACTAATGCTTC-GT-TT-TGGCA
5413 GROUP_3     TCCAAACTCAAGAGATGATTTTACATGGCAATCTGGCACCAATGCTTCTGTCTTTTGGCA
5414 GROUP_4     ACC--AAAA-AGGAATGATTA-AC-TGGGA-TCAAGCACAAAACCCTTCTATATT-TGGCA
5415 GROUP_5     -CCCAC----AGAGA-ATGATTACACATGGCAATCTGG-ACTAATGCTTCCAATATTCTGGCA
5416 GROUP_6     ACCTAAGAAGAGAGATGATTACACATGGCAATCTGGAACAAATGCCTCAGTTTTCTGGCA
5417 GROUP_7     -CCAAC-AA-AG-GATGATTTTGC-TGGCA-TC-GG-ACAAATGCATCAGT-TT-TGGCA
5418 GROUP_8     -CCAGATA--AG-AC-CA-TTTGC-TGGCA-TCAGG-AC-AATGCATC-ATATTCTGGCA
5419 GROUP_9     ACCA---GACAGAA--CA-TTTGC-TGGCAATC--G-A-TAATGCATCAATATT-TGGCA
5420 GROUP_10    -CCAACAA-TAGA-A-CA-TTTGCATGGCA-TCAGGTAC-AATGCATC-A-TTTCTGGCA
5421 GROUP_11    TCCA-A-AA-AGAGATGA-TA-ACATGGCA-TCAGGAAC-AATGCATCT-T-TT-TGGCA
5422 GROUP_12    -CC-----AAGAG-GATGATTAT-CATGGCAATCAGG-AC-AATGCATCT-TCTTTTGGCA
5423 GROUP_13    ACC-AA-AC-AG-GATGATTTTGC-TGGCAATCTGGAC-AATGC-TCAAT-TT-TGGCA
5424 GROUP_14    TCCAAAGACAAGAGAAGATTATGCTTGGCAATCAGGGACCAATGCATCTATCTTTTGGCA
5425 GROUP_15    TCCAAAAACAAGAGAGGATTATACATGGCAATCTGGTACCAATGCTTCAATATTTTGGCA
5426 GROUP_16    TCCAAAAACTAGGGAAGATTTTGCTTGGCA-TCAGG-AC-AATGCATCCATTTTCTGGCA
5427 GROUP_17    -CCAA-AACTAG-AAAGATTATGCATGGCAATCTGG-ACAAATGCATCGTCT-TT-TGGCA
5428 GROUP_18    ACCA------AGAGATGA-TA--CATGGCAATC-GG-AC-AATGC-TC-ATCTTTTGGCA
5429 GROUP_19    ACCCAA-AAAAG--ATGATTACACATGGCAATC-GG-ACAAATGC-TCTGT-TT-TGGCA
5430 GROUP_20    ACCCAGGAAGAGAGATGATTCAGCTGGCAATCTGGTACAAATGCCTCTGTTTTCTGGCA
5431 GROUP_21    ACCTACTAAAAGAGACGATTACACATGGCAATCTGGCACAAATGCTTCTGTATTTTGGCA
5432 GROUP_22    ACC----AA-AGA-ATGA-TA----TGGCA-TC-GG-AC-AATGCATC--T-TT-TGGCA
5433 GROUP_23    ACCAGAAAAGAGAGACGACTACACTTGGCAATCTGGAACTAATGCTTCAATTTTCTGGCA
5434 GROUP_24    CCCAAAAACTAGAAATGATTACACATGGCAATCAGGTACTAATGCATCTATATTTTGGCA
5435 GROUP_25    -CCA---AAGAGA-ATGATTACACATGGCAATCTGGCACCAATGCATCTGT-TTCTGGCA
5436 GROUP_26    ACCCACAAAAAGAAATGACTACACATGGCAGTCCGGCACTAATGCATCAGTATTCTGGCA
5437 GROUP_27    ACCTGAGAA-AGA-ATGA-TT-ACATGGCAATCAGGCACAAATGCATCTGT-TT-TGGCA
5438 GROUP_28    -CCAACAACTAGA-A-GACTAGCTTGCA-TCTGGAACAAAATGCATCT-TATT-TGGCA
5439 GROUP_29    -CC--A-AG-AG--A-GA-TATGCATGGCA-TCTGG-AC-AATGC-TC--TTTT-TGGCA
5440 GROUP_30    -CC----AA-CG-GA-GA-T--ACATGGCA-TCAGG-ACAAATGC-TCT-T-TT-TGGCA
5441 GROUP_31    ACCCAAAAAACGTGATGATTACACATGGCAATCTGGCACCAACGCCTCAGTTTTTTGGCA
5442 GROUP_32    ACCAAAGAAGAGAGATGACTATACTTGGCAGTCAGGCACCAATGCATCTGTGTTTTGGCA
5443 GROUP_33    ACCAAA--ACTAGAGATGA-TACACATGGCA-TCAGG-AC-AATGCATCAGT-TTTTGGCA
5444 GROUP_34    CCCCACTACCAGAAATGATTACACATGGCAATCCAGTACCAATGCCTCTGTTTTCTGGCA
5445 GROUP_35    ACCCAAAACCAGAGATGACTATACCTGGCAATCTGGAACTAATGCTTCAGTCTTTTGGCA
```

FIG. D13 CONT'D

09.trace                                                                  9/20/2007 5:05 PM

```
5446  GROUP_36    -CC-A---A-CG-AATGATTATACTTGGCAGTCTGG-AC-AATGCTTCAGT-TTCTGGCA
5447  GROUP_37    TCCA---ACTAG-AAAGATGA-GAGTGGCA--CAGGAACTAATGCTTCAGT-TT-TGGCA
5448  GROUP_38    ACCAGAGACCAGGGATGCCGATGAATGGCAGTCTGGAACTAATGCATCAGTCTTTTGGCA
5449  GROUP_39    TCCAGATAAAAGGATGCACGATGCCTGGCAAACCAGTACAAATGCCTCAGTCTTCTGGCA
5450  GROUP_40    CCCTGTTAGTAGAACTGACAACACTTGGCAATCTAGCACAAATGCATCAGTCTTTTGGCA
5451  SUMMARY     -CC-------XG----XX-X-----TGGXA--C--G-A--AAXXX-TC----TT-TGGCA
5452
5453  GROUP_1     ACATGGACA-CC-TT-CCTAGATT-TCTTTACCATTTCTTAGCATTGCATCAGCTTATTA
5454  GROUP_2     ACATGG-CAAACTTTCCC-AGATTTTC-TTACCTTTC-T-AG--T-GCTTCAGCATA-TA
5455  GROUP_3     ACATGGCCAAGCTTTCCCCAGATTCTCTCTACCTTTCTTAAGTATTGCTTCTGCTTATTA
5456  GROUP_4     -CATGG-CA-GC-TATCCAAGATT-TCT-TACCATT-TT-AG-ATTGCATCTGCTTACTA
5457  GROUP_5     ACATGGACAA-C-TT-CCAAG-TTTTC--T-CC-TTC-TGAG-AT-GCATCAGC-TATTA
5458  GROUP_6     ACACGGACAGCCTTACCCTAGATTTTCATTACCATTTCTAAGCATAGCCTCAGCATATTA
5459  GROUP_7     -CATGG-CA-CC-TTCCCTAGA-TTTCTTTACC-TTCTT-AGCATTGC-TCTGC-TACTA
5460  GROUP_8     AC-TGGACAACCATTCCCAAGATT-TC-CTACCTTTTCT--G-AT-GCTTCAGC-TA-TA
5461  GROUP_9     ACATGG-CA-CC-TT-CC-AGATTTTCATT-CC-TT--T-AGTGTTGCATCTGC-TATTA
5462  GROUP_10    ACA-GG-CAACCCTTTCCAAGATTT-CATTACC-TTTTTGAGTGT-GCATC-GCTTATTA
5463  GROUP_11    ATATGG-CAAACATA-CC-AG-TT-TC--TACC-TT--T-AG-ATAGC-TCAGC-TATTA
5464  GROUP_12    ACATGGACAAAC-TA-CCTAGATTTTC-CTTCCTTT--T-AGT-TAGC-TCTGCATA-TA
5465  GROUP_13    ACATGGTCAAACATACCC-AGATT-TC-CT-CC-TTC-T-AG-ATAGC-TC-GC-TA-TA
5466  GROUP_14    ACATGGGCAAACATACCCTAGATTTTCACTTCCTTTCCTAAGTATAGCTTCTGCTTATTA
5467  GROUP_15    ACATGGTCAAACATACCCTAGATTTTCCTTGCCTTTCTTAAGTATAGCCTCAGCATATTA
5468  GROUP_16    GCATGG-CA-ACTTATCCTAGATTTTCA-TACCCTTCCTTAGTATAGCATCAGCATA-TA
5469  GROUP_17    ACATGG-CAAACATTTCCAAGATTTTC--TACC-TTTCTGAGCAT-GCATCAGCATATTA
5470  GROUP_18    -CATGGACA--CATA-CCCAG-TT-TCACT-CC-TT--T-AG-ATTGCCTCTGC-TA-TA
5471  GROUP_19    -CATGG-CA-CC-TACCC-AGATT-TC-TT-CCTTT-CT-AGCAT-GCATCTGCTTA-TA
5472  GROUP_20    ATATGGTCAGACATATCCTCGATTTTCCTTACCTTTCTTAAGCATTGCATCTGTCTATTA
5473  GROUP_21    GCATGGCAAACATACCCTAGATTTTCACTTCCATTTCTAAGTATTGCATCTGCCTACTA
5474  GROUP_22    -CA-GGTCAACC-TA-CC-CGATT-TC-CT-CC-TT-CT-AG--TAGC-TCAGCATATTA
5475  GROUP_23    ACATGGACAACCTTACCCTCGCTTCTCACTTCCTTTCTTGAGTATAGCCTCAGCTTACTA
5476  GROUP_24    ACATGGTCAACCATACCCAAGATTTTCATTACCTTTTCTAAGTATAGCTTCTGCATATTA
5477  GROUP_25    --ATGGTCAA-TTTACCC--G-TT-TCT-TACCATTTCTTAG-ATTGC-TC-GCATATTA
5478  GROUP_26    ACATGGTCAAACTTACCCCAGATTCTCATTACCATTCCTTAGTATAGCATCCGCATATTA
5479  GROUP_27    -CA-GG-CAAGC-TATCC-AGATTTTCA-T-CC-TTCCT-AGTATTGC-TCTGCATATTA
5480  GROUP_28    -CATGGGCAACC-TT-CC-CG-TTTTCACT-CC-TTT-T-AGT-T-GCATCAGCATATTA
5481  GROUP_29    ACA-GG-CA--C-TA-CCAAG-TT-TC--TACC-TT--T-AGTGT-GC-TC-GCTTA-TA
5482  GROUP_30    -GA-GG-CAACCATA-CC-AGATT-AC-AT-CC-TTTATGAG-ATTGCATCAGC-TA-TA
5483  GROUP_31    GGAAGGTCAACCTTACCCCAGATTCACAATCCCTTTTATTAGTATTGCCTCAGCATATTA
5484  GROUP_32    ACAAGGTCAAACATACCCCAGGTTCTCTATACCATTTTCTAGTATTGCCTCAGCTTATTA
5485  GROUP_33    -CA-GG-CAACCTTACCCCAGATTTACCATTCCATTTATGAGTATAGCTTCAGCATATTA
5486  GROUP_34    ACAAGGACAACCATATCCCAGATTCACTATACCTTTTATGAGTATTGCCTCAGCTTATTA
5487  GROUP_35    ACAAGGACAACCATACCCTAGATTCACAATCCCTTTCATGAGTATTGCGTCAGCATATTA
5488  GROUP_36    -CA-GG-CAGCCATACCC-AGATTCACTAT-CC-TTCATGAGTATAGCCTCAGC-TATTA
5489  GROUP_37    -CATGG-CAACCATACCC-AGATTTACAAT-CCTTTTGT-AG-AT-GCCTCAGCATA-TA
5490  GROUP_38    GCACGGCCAACCATACCCAAGGTTTACAATCCCCTTCATAAGCATTGCATCAGCATATTA
5491  GROUP_39    AGTTGGACA-ACTTATCCCAGATTCACCATACCTTTCTCCAG-ATAGCATCAGCTTATTA
5492  GROUP_40    GGTTGGTCAAACTTATCCCAGATTTTCTATACCTTTCTCAAGTATAGCTTCAGCTTACTA
5493  SUMMARY     ----GG-CA--X-TX-CC--G--T---C--T-CC-TT--X--G--T-GC-TC-GX-TA-TA
5494
5495  GROUP_1     -ATGTTTTATGATGGATATGATGGAGA-AA--C-TCTTCCAA-TATGGTAG--TAGT-AC
5496  GROUP_2     CATGTTTTATGATGG-TA-GATGGTGATACA-C---CTCAA--TATGG-AC-TCAGTCAC
5497  GROUP_3     CATGTTTTATGATGGTTATGATGGAGACACTTCAAGCTCCAGATATGGTACATCAGTTAC
5498  GROUP_4     CATGTTTTA-GATGGGTATGATGGTGA-GCACCTGGATCAAGATATGG-AC-TCAGT-AC
5499  GROUP_5     CATGTTTTATGATGG-TATGATGGAGATAAATC----TCTAGGTATGGTGT-TC-GT-AC
5500  GROUP_6     TATGTTCTATGATGGATATGATGATAAATCGTCATCTAGGTATGGTGTTTCTGTCAC
5501  GROUP_7     CATGTT-TATGATGG-TATGATGGTGATACACATGA-TCAC--TATGG-AC-AC-GT-AT
5502  GROUP_8     CATGTT-TATGATGG-TATGATGG-GATAC---TG--TC-CGTTATGG-AC-ACAGT-GT
5503  GROUP_9     CATGTTTTATGA-GG-TA-AATGG-G-TGA--A-ACAGC-A--TA-GG-ACCAC-GTGGT
5504  GROUP_10    CATGTTTTATGATGG-TAT-ATGG-GACA-AAGTGGAGCCAAGTATGG-AC-ACAGT-GT
5505  GROUP_11    CATGTT-TATGATGGATATGATGG-GA-CAACC-A--TC-AG-TATGGTAATAT-GTTAC
5506  GROUP_12    -ATGTTTTATGATGGATATGATGGTGA-CAA---GA-TC----TATGGT-C--TTGTTAC
5507  GROUP_13    CATGTT-TATGATGG-TA-GA-GGTGA--A-------TC--G-TATGG-ACAGT-G--AC
5508  GROUP_14    CATGTTCTATGATGGATATGGTGACCAAACTGAGTCACGCTATGGCACTGTGTAGTCAC
5509  GROUP_15    CATGTTTTATGATGGATATGATGGTGACCAAACTGAATCAAGATATGGTACTGTAGTCAC
5510  GROUP_16    CATGTTTTATGATGGTTATGATGGTGA-CAGACTGACTCACAATATGGTGCAGT-GT-AC
```

FIG. D13 CONT'D

```
09.trace                                                                                            9/20/2007 5:05 PM 5511 GROUP_17      CATGTTTTATGATGGATATGAAGG-GA-CAAAA-ACATCCCGTTATGGCAC-ATTGC-AG
5512 GROUP_18      CATGTT-TATGATGG-TATGATGGTGG...-CCAGATTC-C--TATGG-AC-AT-GTAAC
5513 GROUP_19      CATGTT-TATGATGGATATGATGGAGA-TC-ACTGAATCACATTATGGTACAGT-GT-AC
5514 GROUP_20      TATGTTTTATGATGGATATGATGGGGACTCAACAGAATCACATTATGGGACAGCGGTGAC
5515 GROUP_21      CATGTTTTATGATGGTTATGATGGTCACTCAACTGAATCACATTATGGGACGGTTGTGAC
5516 GROUP_22      .CATGTT-TATGATGG-TATGA-GG-GG...-CC-GG-TC-CG-TATGG--CAGTGGT-AC
5517 GROUP_23      TATGTTCTATGATGGCTATGATGGTGATGCTCCCGGATCGCGATACGGGACCATAGTGAC
5518 GROUP_24      CATGTTTTATGATGGGTATGGAGATTCACCAGGATCCCGCTATGGAACAATAGTAAC
5519 GROUP_25      -ATGTTTTATGATGG-TAT-A-G-AG--TC--CA-ATGCACGCTATGG-ACAACA-TCAC
5520 GROUP_26      TATGTTTTATGATGGATATGATGGTGACTCCACACAATCACATTATGGCACCACAGTAGT
5521 GROUP_27      -ATGTTTTATGATGG-TATGATGG-GA-TCTGAA--AAC-CGCTATGGAACATC-GT-AC
5522 GROUP_28      CATGTT-TATGATGG-TATGATGG-GA-AC-TAT-A-TCCAGATA-GG-ACTGTAGTCAC
5523 GROUP_29      CATGTT-TATGATGG-TA--ATG......A----G------A-TATGG-AC-G--AG-AC
5524 GROUP_30      -ATGTT-TATGATGG-TATGATGGTGAT--TGC---ATC-A--TA-GG-TC-GT-GT-AC
5525 GROUP_31      CATGTTTTATGATGGTTATGCTGATGACAACCCAAGTGCACCTTATGGAACTGTAGTTAC
5526 GROUP_32      CATGTTTTATGATGATACTCGGATGACAGCACATCCTCTCCATATGGCACTGTAGTTAC
5527 GROUP_33      TATGTTTTATGATGG-TATGA-GATGA-AA-G...GAAGTGTGTATGG-TCTGTTGT-AC
5528 GROUP_34      CATGTTTTATGATGGTTATGAAGATGACAATG...GAACTACCTATGGTGCAGTGGTTAC
5529 GROUP_35      TATGTTCTATGATGGGTATGAAGATGACAATG...GCACCACTTATGGGGCTGTTGTTAC
5530 GROUP_36      CATGTT-TATGATGG-TA-GA-AGTGATAAAG...GCAA-AT-TATGGAAC-GCAGT-AC
5531 GROUP_37      CATGTT-TATGATGG-TATGA-GGTGAT------A--TCA-A-TA-GGTTCAGT-GT-AC
5532 GROUP_38      CATGTTCTATGATGGGTATGAAGGTGATGCCCTCAGTTCTAAATATGGCTCAGTAGTTAC
5533 GROUP_39      CATGTTCTATGATGGTTATGATTCAGATGGTTTAGATGCTATTTATGGTATTCCTGTTAC
5534 GROUP_40      CATGTTTTATGATGGATACGACACTGATGGCACAGATGCAGTGTATGGTGTTAGTGTGAC
5535 SUMMARY       -ATGTT-TA-GA-GG-TA--X-X--X---------------TA-GG--X------XX
5536
5537 GROUP_1       -AATGATATGGG-AC-ATATG-TCAAGAATAGTTACAGA-AA-CAG-AACA--CTGT-GT
5538 GROUP_2       -AACCA-ATGGGAAC-CT-TGCTC-AG-ATAGT-ACCAACAA-CAGCAGCATGA-GTTGA
5539 GROUP_3       AAACCACATGGGGACACTCTGTTCAAGAATTGTGACAAATAAACAACTTCATCCTGTTGA
5540 GROUP_4       -AATCA-ATGGG-ACTTTGTGTTCAAGAGT-GTTACTG--AAACAA-AACACCCAGTTGA
5541 GROUP_5       -AACCACATGGG-ACTTTGTGTTCTAGAAT-GT-ACAAACAG-CA-GA-CATCCAGT-GA
5542 GROUP_6       TAATGATATGGGTACACTTTGCACTAGAATTGTAACAAACCAACAG-AACACCTAGTGGA
5543 GROUP_7       -AA-CACATGGG-AC--T-TG-ATG-G-ATAGT-ACAAA-CAGCAAGCACATGAGGTGGA
5544 GROUP_8       TAATCA-ATGGG-ACA-T-TG-ATTAG-AT-GT-AC-AAT-A-CA--A-CAT-A-GTTGA
5545 GROUP_9       TAA-CG-ATGGG--C-CT-TG--T-AG-AT-GT-AC----AAACA-G--CATGATGT--A
5546 GROUP_10      -AATCGCATGGGTGCA-T-TG-ATGAGAGTTGT-AC-AACAA-CAA---CATAAAGTTGA
5547 GROUP_11      CAATGA-ATGGGCAC--T-TG-T--AG-ATAGT-AC-GAT-A-CATA--CA----AT-GA
5548 GROUP_12      -AA-GA-ATGGGAAC--TATG-TATAGAATAGT-AC-GA--A-CAT---CAC-AAATAGA
5549 GROUP_13      -AATGACATGGG-AC-TT-TG-TC-AG-AT-GT-AC-GAT-A-CA--A-AA----GT-GA
5550 GROUP_14      TAATGACATGGGTACTTTATGTTCTAGAATAATAACTGATAACCATAAGCACCCAATTGA
5551 GROUP_15      TAATGACATGGGCACTTTATGTTCTAGAATTGTTACTGACCAGCACACACATCCCATAAA
5552 GROUP_16      TAATGATATGGGATCTCTATGCTA-AGAATAGTAACTG--CAGCATAAGCA-AAGATAGA
5553 GROUP_17      -AA-CACATGGG-ACA-T-TGTTCTAG-ATAGTTACAGAAGAACA-C-AAAT-AA-T-GA
5554 GROUP_18      -AATGATATGGG-TC--T-TGTTC-CGT-TAGT-AC-GAAGA-CA-GG--C-CG-GT--A
5555 GROUP_19      -AATGACATGGG-AC-CT-TGTTCTAGAAT-GT-ACTGAAGA-CA-G---CACGTGT-GA
5556 GROUP_20      CAATGATATGGGGACACTTTGTTCAAGAATAGTCACTGAAAATCATGGGACCCAAGTGAA
5557 GROUP_21      CAATGACATGGGAACGTTGTGCTCCAGAATAGTTACTGAACACCATGGTACACAGGTTCA
5558 GROUP_22      AAATGA-ATGGG-AC--T-TG-TC-AG-ATTGTGACTGA-GA-CAC---ACACA-GT-AA
5559 GROUP_23      AAATGACATGGGTACACTGTGTTCTAGAATTGTAACTGAAGAACACCAGACTCAAGTCAG
5560 GROUP_24      TAATGATATGGGAACCTTATGCTCCAGAATAGTAACTGATGAACACCAAACACAGGTTGC
5561 GROUP_25      -AATGA-ATGGG-ACA-T-TGCTT-AGAATAGT-ACTGAAGAACA-AC-AACAA-GT-AA
5562 GROUP_26      TAATGACATGGGCACATTATGCTTTAGGATAGTGACTGAAGAACACACTAGCAGGGTAAA
5563 GROUP_27      -AATGA-ATGG---C-TT-TG-TTTAGAATAGT-AC-GA--A-CA-AC-AA--A-GT-AA
5564 GROUP_28      -AATGA-ATGGGAAC-TT-TG-TC-CG-AT-GTGAC-AGTGAGCAA-T-CACAA-GT-AA 5565 GROUP_29      AAA-AACATGGG--CA-T-TG-TC-AG--T-GTAACAGA-AAACACATTCA-----T-C-
5566 GROUP_30      -AA-GA-ATGGGAAC-ATATGT-TTAGA-T-GT-AC-TC-A--CAAA--CA--A--T-AA
5567 GROUP_31      CAATGACATGGGTTCACTGTGTGTCAGAATAGTTACAGACCAGCAAAAACATAAAGTTAA
5568 GROUP_32      CAATGACATGGGTACACTGTGTATGAGGATGGTTACAGATCAACAACAACATAAGGTCAC
5569 GROUP_33      AAA-GATATGGGCACATT-TGTGT-CGTATTGTGACTGAGCAGCAGACACATA-GGT-AA
5570 GROUP_34      AAATCATATGGGAACACTCTGTGCTCGCATAGTAACTGAACAACAGAAGCATGAAGTCAA
5571 GROUP_35      TAATGATATGGGCACACTTTGTGTGCGCATAGTGACTGAGCAACAGAAAAATGAGGTCAA
5572 GROUP_36      CAATGATATGGGAAC--T-TGTG--AGAATTGTTAC-GAACAACA--AACATAA-GT-CT
5573 GROUP_37      -AATGCTATGGG-ACACTAT-TGT-CGTGTGGT-ACAGA----CAAAAACATGA-GT-AA
5574 GROUP_38      TAATGCCATGGGCACCTTATGTGTTCGTGTGGTTACAGAACAGCAAAGCAACACAGTCAA
5575 GROUP_39      AAATCACATGGGCACAATATGTGTGAGAATGGTGACAGATAAACAGAAAATTAAAACTAA
```

09.trace                                                                       9/20/2007 5:05 PM

```
5576 GROUP_40    TAACCATATGGGGACTATATGTGTTAGAATTGTTACAGACCAACAACAACATAGAGTTAA
5577 SUMMARY     -AA-XX-ATGGG--C--T-T------G--T-XT-AC-------CA-----X-----X---
5578
5579 GROUP_1     -AT-ACAACACACATATATCA-AAAGCTAAACACACAAAAGCTTGGTGTCCTAG-CC-CC
5580 GROUP_2     -AT-ACCAC-CGT-T-TATCA-AAGGCCAAGCAT-T-AA-GC-TGGTGTCCAAG-GC-CC
5581 GROUP_3     AGTCACAACTCGTGTATATCATAAGGCAAAGCATATTCGAGCATGGTGTCCTAGAGCACC
5582 GROUP_4     AATCAC-ACACG-GTGTA-CACAA-GCAAAACACATTAGAGCATGGTGTCCACGTGCACC
5583 GROUP_5     GGT----ACACGTGT-TATCA-AAAGCTAAACAC-TCA-AGCCTGGTGCCC-AGAGCTCC
5584 GROUP_6     GGTTACAACCAGAGTTTACCATAAAGCCAAGCATGTTAAAGCATGGTGCCCTAGGGCTCC
5585 GROUP_7     AATTAC-AC-A-T-T-TATCACAA-GCCAA-CATGT-AAAGC-TGGTG-CCAAGACCACC
5586 GROUP_8     AAT-AC-ACTAGAGTATACCA-AAGGCTAA-CAT-TTAAAGC-TGGTGTCC-AGACCAC-
5587 GROUP_9     -GT-ACAAC-A--AT-TA-CA-AA-GCTAA-CATGTAAA-GC-TGGTG-CC--G-CC-CC
5588 GROUP_10    AATCACAAC-AA-AT-TACCATAA-GCCAA-CATGT-AA-GCATGGTGTCCTAG-CC-CC
5589 GROUP_11    AGT-ACAAC-AG--T-TA-CA-AAAGCAAA-CATGT-AA-GT-TGGTG-CC-AGACCACC
5590 GROUP_12    -AT-AC-ACAAGAATATACCA-AAAGCAAA-CACATTAAGGT-TGGTGTCCAAG-CCACC
5591 GROUP_13    AAT-ACAAC-AGA-T-TA-CA-AA-GC-AAACA--T-AAA---TGGTG-CCAAG-CCACC
5592 GROUP_14    AGTGACGACAAGAGTCTATCATAAAGCTAAACACATCAAAAGCATGGTGCCCACGACCACC
5593 GROUP_15    AATAACAACCAGAGTGTATCACAAAGCCAAACATGTCAAAGCCTGGTGCCCTAGACCACC
5594 GROUP_16    AGTGACCACAAGAATATACCATAAGGCAAAGCATGTTAAAGCTTGGTGCCC-AGACCACC
5595 GROUP_17    --TAAC-AC-AG-ATATATCA-AAAGCCAA-CATAT-AAAGCTTGGTG-CC-AG-CC-CC
5596 GROUP_18    -ATT-CAAC--G--T-TATCA-AA-GC-AAACA-GT-AAAGC-TGGTGCCCA-G-CC-CC
5597 GROUP_19    -ATTACAACTAGAGTGTA-CA-AAAGC-AA--CATGT-AAGGC-TGGTG-CC-AGACCCCC
5598 GROUP_20    GATAACAACTAGAATTTATCATAAGGCAAAACATGTAAAAGCCTGGTGTCCAAGACCCCC
5599 GROUP_21    CGTCGCAACAAGAATATATCATAAACAAAGCATGTTAAGGCTTGGTGTCCAAGACCTCC
5600 GROUP_22    -AT-AC-ACTAG-GT-TA-CACAAAGCAAAACATGT-AA-GC-TGGTG-CC-CG-CC-CC
5601 GROUP_23    CATTACCACAAGAATATATCACAAAGCAAAACATGTGAAAGCGTGGTGTCCACGACCCCC
5602 GROUP_24    AATCACAACTAGAGTATATCATAAAGCTAAACATATAAAAGCTTGGTGCCCACGACCACC
5603 GROUP_25    GGT-ACAACTAGA-T-TA-CA-AAAGCTAAACATGT-AAAGCATGGTGTCCTAGACCTCC
5604 GROUP_26    GGTTACTACTAGAATCTATCATAAGGCTAAACATGTTAAAGCTTGGTGTCCAAGACCTCC
5605 GROUP_27    AAT-ACAAC-AG--TTTACCA-AAAGCTAAACATGTTAA-GT-TGGTG-CC-AGACCCCC
5606 GROUP_28    A-T-GTAACAAG-ATATATCACAAAGC-AA-CACACCAAAGCTTGGTG-CCAAGACCACC
5607 GROUP_29    -AT-ATGACAAG--TCTA-CA-AA-GCTAAACA-GTCAA-GC-TGGTGTCC-CG-CCACC
5608 GROUP_30    -AT--T--G-CG-AT-TA-CA-AA-GC-AA-CA-ATAAA-GC-TGGTG-CC-CG-CCACC
5609 GROUP_31    GATTACCAGTAGAATATACCATAAAGCAAAACATATCAGTGCCTGGGGCCCTAGACCACC
5610 GROUP_32    AATTACAGTAGAGTCTACCACAAGGCCAAACATATTAGTGCATGGGGCCCAAGACCTCC
5611 GROUP_33    -ATAACCAG-AG-ATATTCCA-AA-GCAAA-CATATTAGTGC-TGGTGTCCAAG-GC-CC
5612 GROUP_34    AATAACCAGCATAATATTCCACAAAGCTAAACATGTCAGTGCATGGTGCCCCAGACCTCC
5613 GROUP_35    GATAACCAGTAGGATTTATCACAAGGCTAAACATATCAGTGCATGGTGTCCAAGACCACC
5614 GROUP_36    -AT-AC-AGCAGAATATCACAA-GCTAAACACAT-AAAGC-TGGTG-CC-AG-GCACC
5615 GROUP_37    CATAAC-AG-AG-AT-TA-CA-AAAGC-AAACA--TCAGTGC-TGGTG-CC-CG-CCTCC
5616 GROUP_38    CATAACAAGTAGGATTTATCACAAAGCCAAACATGTCAGAGCATGGTGTCCTAGACCCCC
5617 GROUP_39    AATTGATTCAAGAATATACCTGAAAGCAAAGCA-ATTAAAGCTTGGTGTCCTAGACCCCC
5618 GROUP_40    GATCGACTCCATGGTATATCTAAAAGCTAAACACTCAAGGCATGGTGTCCCAGACCTCC
5619 SUMMARY     --T-----X-----T-TX-CX-AA-GC-AA-CA--X-X-----TGGXG-CC--G-XC-C-
5620
5621 GROUP_1     TAGAGCTGT-CCTTACACA.CATAGTC-TGT-ACTAATTAT-T-C.CA-AAA...CAGGT
5622 GROUP_2     AAGAGC-GT-CCTTA-ACA.CA-ACAC-CTCAAC-AA-TAT---C.C-CAAG...A-GGT
5623 GROUP_3     AAGGGCTGTGCCTTATACA.CATGCTCACGTCACCAATTATAAAC.CACAAG...ATGGT
5624 GROUP_4     TAG-GCTGT-CCATACACA.CA-ACTAGATCAAC-AATTACATGC.C-C---G...A-GGT
5625 GROUP_5     TAG-GC-GT-CC-TACACA.CA-AG-TA-GT-ACTAACTA-AA-ATT-C-GG...A-A-.
5626 GROUP_6     CAGAGCAGTCCCTTACACA.CACAGCAATGTTACAAATTACAAAG.TACGGG...ACGGT
5627 GROUP_7     --G-GCTGT-CC-TA-ACA.CAT---CA-TC-ACAAATTACAAAC.CACATG...------
5628 GROUP_8     TAGAGCTGTACCATACACA.-C-GTA-A-TCAAC-AATTA-A--C.CT----A...--GG-
5629 GROUP_9     -AG-G-TGT-CCATA-AA-.TATGTTG---T-A-TAATTA--CA-.--A--G...A----
5630 GROUP_10    TAGAGC-GTTCCATA-AG--TATG-TGGATCAACAAA-TACAAAC.CTGAT-....AA---
5631 GROUP_11    TAGAGCTGT-GA-TA-AC-.-A-AC-CATGT-AC-AA-TA-AAA-.CA----....---G-
5632 GROUP_12    -AG-GC-GTTGA-TA-ACA.CA-ACTCA-GT-AC-AA-TA-AA-C.AT---A...C-CGT
5633 GROUP_13    -AGAGCTGT-GA-TACACA.CA-AC-CATGT-ACTAACTACAA--.--A--G...A-GGT
5634 GROUP_14    TAGGGCTGTTGAATACACA.CACACACATGTCACAAATTACAAGA.AGACTG...ATGGC
5635 GROUP_15    ACGGGCTATCGAGTACACA.CATACACATGTTACTAATTATAAAA.TAAAAG...ATAGA
5636 GROUP_16    GAGGGCCGTTGAATACACA.CA-ACACA-GTAACCAATTACAAAA.TTGCAA...AT-A-
5637 GROUP_17    CAG-GCTGTTGAATACACA.---A-AC-TGT-ACAAATTA-AAAA.GAGA-G...GA-A-
5638 GROUP_18    TAG-GCAGTTGA-TA-A-A.CA-ACACATGT-ACAAA-TA-A--C.CA---A....CAGG-
5639 GGROUP_19   TAGAGCAGT-GAATATAC-.CACACACATGTCACAAATTACAAAC.CACAAG...A-GGT
5640 GROUP_20    AAGGGCAGTTGAATATAGA.CATACACATGTTAACAATTACAAAC.CAGACC...AAGGG
```

FIG. D13 CONT'D

```
09.trace                                                                                9/20/2007 5:05 PM 5641 GROUP_21    AAGGGCAGTTGAATATAGA.CACACACATGTAAACAACTATAGAC.CAGATG...ATGGA
5642 GROUP_22    AAGAGCTGTTGGATA-ACA.CA-AC--ATGT-AC-AA-TA-AAAC.CATC--...-AGG-
5643 GROUP_23    GAGGGCTGTGGGTTATACA.CACACACATGTTACCAACTACAAGC.CATCAC...AGGGA
5644 GROUP_24    CAGAGCCGTGGAATATACC.CACACTCATGTGACTAATTATAAAC.CCCAGA...CAGGT
5645 GROUP_25    CAG-GCTGT-GA-TA-AC-.AATGTGCATGT-ACAAA-TACAAAC.CA-----...CAGGA
5646 GROUP_26    TAGGGCAGTAGAATATACA.AATGCACATGTGACCAATTATAAAC.CCACTG...ATGGA
5647 GROUP_27    -AGAGCAGT-GAATA-AC-.AATGTGCAT-T-AC-AATTA-AA-C.CCAA--...AT---
5648 GROUP_28    CAG-GCTGTTCA-TAC-CA.CATACACAT---AC-AA-TA-AAAT.T-----...CAGA-
5649 GROUP_29    -AG-GC-CTTGA-TA-AC-.CG-GCTCA-CG-AC-AATTT-AAA-.TTGA-G...-----
5650 GROUP_30    A-G-GC-GT--C-TA-CA-.--CAC-CA-TC-AC-AA-TA--T-C.CA----...--GG-
5651 GROUP_31    AAGAGCTGTACCATACCAG.CATATACACAATCCAAATTACAAGA.CAAGTA.....AT
5652 GROUP_32    TAGAGCTGTACCTTATCAG.CACATATATAACCCTAATTATAAAA.CTGAAG.....AA
5653 GROUP_33    AAGAGCAGTGCC-TA-CA-.CACAC-A--AG-ACAAACTTAGT-C.CAA-G-...-AGGT
5654 GROUP_34    ACGCGCTGTAGCTTATCAA.CATACATACAGTCCAAACTTTGTGC.CTCAGG...AAGGT
5655 GROUP_35    AAGAGCAGTTGCATATCAA.CACACATATAGCCCAAATTTTGTAC.CGCAAA...CAGGA
5656 GROUP_36    -AGAGCAGTCCCATA-CAA.CATA--TA-A--CCAAATTTCAA-A.--ACT-----TGA-
5657 GROUP_37    -CG-GC-GTAGC-TACCAA.CACACACATACAGTACAAA-TT-GTTC.C-A--G--GG--TT
5658 GROUP_38    CAGAGCAGTAGCCTACCAA.TCAACATATACCACAAATTTTGTTC.CACAAGACGGGATC
5659 GROUP_39    CAGAGCAGTTACGTATAAC.CATATATACAACCCCAATTATGTTA.GAGAGG......GA
5660 GROUP_40    AAGAGCAGTCACATATAAC.CATACATATAATCCAAATTATGTTA.GGGCTG......AT
5661 SUMMARY     --G-G--XT--X-TA----------------X--AA-TX-----X------------
5662
5663 GROUP_1     GA-G......TGACAACAG...C-ATAGT-C--AGA-.......--A--AT-A-AACTG..
5664 GROUP_2     GAAG......T--AGAT-T...TCCTCAAAGAGAGAG......C-AG--TAAC-ACAG..
5665 GROUP_3     GATG......TACAGATCT...TCTTAAAACCCAGAC......CCAGCCTAACAACAT..
5666 GROUP_4     GA-C......CAACAAT-T...T-CTTAA-CA-AG-A......-A-A-CTTGTAACAG..
5667 GROUP_5     GA--......CTGAAATTT...TCTTAAAACC-AGA-.......--A-TAT-A--ACAG..
5668 GROUP_6     GAAC......CAACACTCT...TTATAAAA-CAAGAG......AGAATCTTACCACAG..
5669 GROUP_7     GA--......TA-A-AT-T...T-ATTAG--C-AGAGATGATCC-AA--T-GTAACTG..
5670 GROUP_8     GAT-......T-CAAAT-T...T-ATTAAA---AGA-CA---CCAAAAGTAGT-A-T-..
5671 GROUP_9     ...G......-T--CA---...TT-T--AA-C-AG-........---A---T----ACAG..
5672 GROUP_10    GAAG......TT-CAAT-T...T--TT-A-CA-AG-GA-AATCCAAA--T-AT-ACAG..
5673 GROUP_11    -A-G......TG-A-ACAG...CT-T-A---C-AG---AACAAT-AA-AC-GC-......
5674 GROUP_12    GAA-......T-AAGAC-G...CAATT---CC-AG-A-A--AAT-A-AACAG--......
5675 GROUP_13    A--G......AGAA-ACTG...C-AT---A---AGA-CAA-GAT-ACA-TGGC-......
5676 GROUP_14    ACAG......AAAAGACAG...CAATTGAATACAAGAGGACATTAAAACAGT-......
5677 GROUP_15    CAAG......AAGAAACAG...CAATTAAATATAGAAGGGACATTAAAATTGTTAAGA..
5678 GROUP_16    GA-G......TCACTTCTG...CAGTTGAGTCCAGAAGAACAATTGTCACAGTT......
5679 GROUP_17    -A-G......T-GA-A--G...C-AT-G---C-AG-AG-GAT-T-AA--TTGT-AATG..
5680 GROUP_18    GA--......----AC-G...--ATAC-----AGAG---ATGTTAG--CA-T-A--A..
5681 GROUP_19    GA-G......TAACTACAG...T-AT-CCAACTAG---------AGA-C-ATAGT-A..
5682 GROUP_20    GAAG......TAACCACTA...TGATTCAACTAGAACCAACATAAGAACCATCGTAA..
5683 GROUP_21    GAAG......CAGCCATAA...CAATCCCCATTAGAACTGATATACGAGCAATCAGAA..
5684 GROUP_22    GA-T......ACA--C-AC...C--T-CC-----G----A-CCC-AGA-A-ATT-T-A..
5685 GROUP_23    GATT......ACAGTGTTG...TTATTCCAGTTAGAGAGAGTCCCAGACAGATTCTTA..
5686 GROUP_24    GAAG......TCACTCTTC...CAATTGAAATAAGAGATAACCCTAGACATATAAAGA..
5687 GROUP_25    G--G-...--TTG--G--T...C--T--AA--ACCTAGAG--AATGTTAG--AA--T-AGAA..
5688 GROUP_26    GAAG......TTACTACTG...CCATTAGGCATAGAGATAATGTTAGAGCCATCCAAA..
5689 GROUP_27    -------A-GTTACCACTT...T-ATCAAACCTAGAG--AA--TAAG-GA-ATTAGAA..
5690 GROUP_28    GT-C......ACA-T--TGT-GC-ATAA-ACCTAGAACAA-TCTAACAA-TGT-......
5691 GROUP_29    ----......T--A--CA-...---T-------AGA-C-----T-A--ACAGC-......
5692 GROUP_30    GA--......---CA...AC-CA-AT-AAA-CCAGA----AT-T-T--AC--T-----..
5693 GROUP_31    GGAG......TTCCAGACAATAGAGTCAAACTCAGAGAGACACTCACCACAGT-......
5694 GROUP_32    GGAA......CTCCAGACACCAAAGTGGCAATTAGAGCTAATATTAAAACTGT-......
5695 GROUP_33    GA-A......TTA-A...ACTCATAT-A-ATT-AG-AA-ACTGT-AAAGAT-T--CATA-
5696 GROUP_34    GATG......TTGAG...TTCATATTAAATTTAGAACAGATGTTAAACAGATCACAA..
5697 GROUP_35    ACAG......TTGAA...ACTCACATTAAGTTCAGACCTCGATGTTAAAGATGTAACAT..
5698 GROUP_36    -CTA......TACCAGATAC-CA-ATT--AAT-AGA----ATAT-A-G-A-TTA-AA..
5699 GROUP_37    --A-......-C-T-A-AAC-CA-ATTAAAAC-AG-G---ACAT-AAA-TTGT-AACT..
5700 GROUP_38    AATT......CCATTAAAAACCAAAATCAAAATCAGAAGAGACATTAAAGAGGTCAGCA..
5701 GROUP_39    GTAA......CACCAGAAACTAAGGT-AAATATAGAGCTGAAGTCACAACCATT......
5702 GROUP_40    GAAA......CAGCC...ACAAAAGTCCAAACTAGAGCAAATGTCACAACAGT-......
5703 SUMMARY     -------X-----------X-X---T--------G---------------------X-
5704
5705 GROUP_1     ....--...............
```

FIG. D13 CONT'D

```
09.trace                                                           9/20/2007 5:05 PM
5706 GROUP_2           ....--..............
5707 GROUP_3           ....T-..............
5708 GROUP_4           ....CT..............
5709 GROUP_5           ....C-..............
5710 GROUP_6           ....C-..............
5711 GROUP_7           ....C-..............
5712 GROUP_8           ....T-..............
5713 GROUP_9           ....C-..............
5714 GROUP_10          ....C-..............
5715 GROUP_11          ....................
5716 GROUP_12          ....................
5717 GROUP_13          ....................
5718 GROUP_14          ....................
5719 GROUP_15          ....ATGT-...........
5720 GROUP_16          ....................
5721 GROUP_17          ....C-..............
5722 GROUP_18          ....ATGT-...........
5723 GROUP_19          ....ATGT-...........
5724 GROUP_20          ....ATGT-...........
5725 GROUP_21          ....CAGT-...........
5726 GROUP_22          .....--GT-..........
5727 GROUP_23          ....ATGT-...........
5728 GROUP_24          ....ATGT-...........
5729 GROUP_25          ....A-T--...........
5730 GROUP_26          ....ATTT-...........
5731 GROUP_27          .....--TT-..........
5732 GROUP_28          ....................
5733 GROUP_29          ....................
5734 GROUP_30          ....-----...........
5735 GROUP_31          ....................
5736 GROUP_32          ....................
5737 GROUP_33          CC--CAGAA-T--C-AA--T-
5738 GROUP_34          ....CAGT-...........
5739 GROUP_35          ....CAGTAATGACAGC-...
5740 GROUP_36          ....CAG--...........
5741 GROUP_37          .....T-.............
5742 GROUP_38          .....ACTA-..........
5743 GROUP_39          ....................
5744 GROUP_40          ....................
5745 SUMMARY           XX--------X--X-XX--X-
5746
5747
```

FIG. D13 CONT'D

```
10.trace                                                                    9/20/2007 5:05 PM 1 Group  1:  1_HRV1A1|d
   2 Group  1:  2_HRV1A2|d
   3 Group  1:  3_HRV1A|cD
   4
   5 Group  2:  4_HRV1B1|d
   6 Group  2:  5_HRV1B2|d
   7 Group  2:  6_HRV1B
   8
   9 Group  3:  7_HRV40a|d
  10 Group  3:  8_HRV40b|d
  11 Group  3:  9_HRV40
  12
  13 Group  4:  10_HRV85
  14 Group  4:  11_HRV85a|
  15 Group  4:  12_HRV85b|
  16
  17 Group  5:  13_HRV56a|
  18 Group  5:  14_HRV56b|
  19 Group  5:  15_HRV56
  20
  21 Group  6:  18_HRV59a|
  22 Group  6:  19_HRV59b|
  23 Group  6:  20_HRV59
  24
  25 Group  7:  21_HRV63
  26 Group  7:  22_HRV63b|
  27 Group  7:  23_HRV63a|
  28
  29 Group  8:  24_HRV39
  30 Group  8:  25_HRV39a|
  31 Group  8:  26_HRV39b|
  32
  33 Group  9:  27_HRV10a|
  34 Group  9:  28_HRV10b|
  35 Group  9:  29_HRV10
  36
  37 Group 10:  30_HRV100a
  38 Group 10:  31_HRV100b
  39 Group 10:  32_HRV100
  40
  41 Group 11:  33_HRV66
  42 Group 11:  34_HRV66b|
  43 Group 11:  35_HRV66a|
  44
  45 Group 12:  36_HRV77a|
  46 Group 12:  37_HRV77b|
  47 Group 12:  38_HRV77
  48
  49 Group 13:  39_HRV62a
  50 Group 13:  40_HRV62b
  51 Group 13:  41_HRV25
  52
  53 Group 14:  42_HRV29a
  54 Group 14:  43_HRV29b
  55 Group 14:  44_HRV44a
  56 Group 14:  45_HRV44b
  57
  58 Group 15:  46_HRV31
  59 Group 15:  47_HRV31a|
  60 Group 15:  48_HRV31b|
  61
```

FIG. D14

```
10.trace                                                               9/20/2007 5:05 PM 62 Group 16: 49_HRV47
 63 Group 16: 50_HRV47a|
 64 Group 16: 51_HRV47b|
 65
 66 Group 17: 52_HRV11
 67 Group 17: 53_HRV11b|
 68 Group 17: 54_HRV11a|
 69
 70 Group 18: 55_HRV76
 71 Group 18: 56_HRV76b|
 72 Group 18: 57_HRV76a|
 73
 74 Group 19: 58_HRV33
 75 Group 19: 59_HRV33b|
 76 Group 19: 60_HRV33a|
 77
 78 Group 20: 61_HRV24a|
 79 Group 20: 62_HRV24b|
 80 Group 20: 63_HRV24
 81
 82 Group 21: 64_HRV90
 83 Group 21: 65_HRV90a|
 84 Group 21: 66_HRV90b|
 85
 86 Group 22: 67_HRV34
 87 Group 22: 68_HRV34b|
 88 Group 22: 69_HRV34a|
 89
 90 Group 23: 70_HRV50a|
 91 Group 23: 71_HRV50b|
 92 Group 23: 72_HRV50
 93
 94 Group 24: 73_HRV18a|
 95 Group 24: 74_HRV18b|
 96 Group 24: 75_HRV18
 97
 98 Group 25: 76_HRV55
 99 Group 25: 77_HRV55b|
100 Group 25: 78_HRV55a|
101
102 Group 26: 79_HRV57
103 Group 26: 80_HRV57a|
104 Group 26: 81_HRV57b|
105
106 Group 27: 82_HRV21
107 Group 27: 83_HRVHan
108
109 Group 28: 84_HRV43
110 Group 28: 85_HRV43b|
111 Group 28: 86_HRV43a|
112
113 Group 29: 87_HRV75
114 Group 29: 88_HRV75b|
115 Group 29: 89_HRV75a|
116
117 Group 30: 96_HRV9a|d
118 Group 30: 97_HRV9b|d
119 Group 30: 98_HRV9
120
121 Group 31: 99_HRV32
122 Group 31: 100_HRV32a
123 Group 31: 101_HRV32b
124
125 Group 32: 102_HRV67
126 Group 32: 103_HRV67a
```

FIG. D14 CONT'D

```
10.trace                                                              9/20/2007 5:05 PM 127 Group 32: 104_HRV67b
    128
    129 Group 33: 105_HRV15
    130 Group 33: 106_HRV15a
    131 Group 33: 107_HRV15b
    132
    133 Group 34: 108_HRV74a
    134 Group 34: 109_HRV74b
    135 Group 34: 110_HRV74
    136
    137 Group 35: 111_HRV38a
    138 Group 35: 112_HRV38b
    139 Group 35: 113_HRV38
    140
    141 Group 36: 114_HRV60
    142 Group 36: 115_HRV60a
    143 Group 36: 116_HRV60b
    144
    145 Group 37: 117_HRV64a
    146 Group 37: 118_HRV64b
    147 Group 37: 119_HRV64
    148
    149 Group 38: 120_HRV94a
    150 Group 38: 121_HRV94b
    151 Group 38: 122_HRV94
    152
    153 Group 39: 123_HRV22
    154 Group 39: 124_HRV22a
    155 Group 39: 125_HRV22b
    156
    157 Group 40: 126_HRV82
    158 Group 40: 127_HRV82b
    159 Group 40: 128_HRV82a
    160
    161 Group 41: 129_HRV19
    162 Group 41: 130_HRV19a
    163 Group 41: 131_HRV19b
    164
    165 Group 42: 132_HRV13
    166 Group 42: 133_HRV13a
    167 Group 42: 134_HRV13b
    168
    169 Group 43: 135_HRV41
    170 Group 43: 136_HRV41a
    171 Group 43: 137_HRV41b
    172
    173 Group 44: 138_HRV73
    174 Group 44: 139_HRV73b
    175 Group 44: 140_HRV73a
    176
    177 Group 45: 141_HRV61
    178 Group 45: 142_HRV61a
    179 Group 45: 143_HRV61b
    180
    181 Group 46: 144_HRV96
    182 Group 46: 145_HRV96b
    183 Group 46: 146_HRV96a
    184
    185 Group 47: 90_HRV16a|
    186 Group 47: 91_HRV16b|
    187 Group 47: 92_1AYM_A
    188
    189 Group 48: 93_HRV81a|
    190 Group 48: 94_HRV81b|
    191 Group 48: 95_HRV81
```

FIG. D14 CONT'D

```
10.trace                                                              9/20/2007 5:05 PM
192
193 Group 49:  147_HRV2
194 Group 49:  148_HRV2a|
195 Group 49:  149_HRV2b|
196
197 Group 50:  150_HRV49a
198 Group 50:  151_HRV49b
199 Group 50:  152_HRV49
200
201 Group 51:  153_HRV23a
202 Group 51:  154_HRV23b
203 Group 51:  155_HRV23
204
205 Group 52:  156_HRV30a
206 Group 52:  157_HRV30b
207 Group 52:  158_HRV30
208
209 Group 53:  159_HRV7
210 Group 53:  160_HRV7b|
211 Group 53:  161_HRV7a|
212
213 Group 54:  162_HRV88
214 Group 54:  163_HRV88a
215 Group 54:  164_HRV88b
216
217 Group 55:  165_HRV36a
218 Group 55:  166_HRV36b
219 Group 55:  167_HRV36
220
221 Group 56:  168_HRV89a
222 Group 56:  169_HRV89b
223 Group 56:  170_HRV89
224
225 Group 57:  171_HRV58
226 Group 57:  172_HRV58a
227 Group 57:  173_HRV58b
228
229 Group 58:  174_HRV12a
230 Group 58:  175_HRV12b
231 Group 58:  176_HRV12
232
233 Group 59:  177_HRV78a
234 Group 59:  178_HRV78b
235 Group 59:  179_HRV78
236
237 Group 60:  180_HRV20
238 Group 60:  181_HRV20a
239 Group 60:  182_HRV20b
240
241 Group 61:  183_HRV68
242 Group 61:  184_HRV68a
243 Group 61:  185_HRV68b
244
245 Group 62:  186_HRV28
246 Group 62:  187_HRV28a
247 Group 62:  188_HRV28b
248
249 Group 63:  189_HRV53a
250 Group 63:  190_HRV53b
251 Group 63:  191_HRV53
252
253 Group 64:  192_HRV46a
254 Group 64:  193_HRV46b
255 Group 64:  194_HRV46
```

FIG. D14 CONT'D 10.trace    9/20/2007 5:05 PM

```
256
257 Group 65: 195_HRV80a
258 Group 65: 196_HRV80b
259 Group 65: 197_HRV80
260
261 Group 66: 198_HRV51
262 Group 66: 199_HRV51a
263 Group 66: 200_HRV51b
264
265 Group 67: 201_HRV65a
266 Group 67: 202_HRV65b
267 Group 67: 203_HRV65
268
269 Group 68: 204_HRV71a
270 Group 68: 205_HRV71b
271 Group 68: 206_HRV71
272
273 Group 69: 207_HRV8
274 Group 69: 208_HRV95
275
276 Group 70: 209_HRV45
277 Group 70: 210_HRV45a
278 Group 70: 211_HRV45b
279
280
281 >>>>>
282
283
284
285 Group 1:
286
287 1_HRV1A1|d    AATCCAGTAGAAAACTACATTGATGAAGTTTTAAATGAAGTTTTAGTAGTGCCGAATATA
288 2_HRV1A2|d    AATCCAGTAGAAAACTACATTGATGAAGTTTTAAATGAAGTTTTAGTAGTGCCGAATATA
289 3_HRV1A|cD    AATCCAGTAGAAAACTACATTGATGAAGTTTTAAATGAAGTTTTAGTAGTGCCGAATATA
290 GROUP_1       AATCCAGTAGAAAACTACATTGATGAAGTTTTAAATGAAGTTTTAGTAGTGCCGAATATA
291
292 1_HRV1A1|d    AAAGAAAGTCATCACACTACATCAAACTCTGCCCCACTTTTAGATGCTGCAGAGACGGGA
293 2_HRV1A2|d    AAAGAAAGTCATCACACTACATCAAACTCTGCCCCACTTTTAGATGCTGCAGAGACGGGA
294 3_HRV1A|cD    AAAGAAAGTCATCACACTACATCAAACTCTGCCCCACTTTTAGATGCTGCAGAGACGGGA
295 GROUP_1       AAAGAAAGTCATCACACTACATCAAACTCTGCCCCACTTTTAGATGCTGCAGAGACGGGA
296
297 1_HRV1A1|d    CACACCAGTAATGTTCAACCAGAAGATGCTATAGAGACAAGGTATGTTATAACATCACAA
298 2_HRV1A2|d    CACACCAGTAATGTTCAACCAGAAGATGCTATAGAGACAAGGTATGTTATAACATCACAA
299 3_HRV1A|cD    CACACCAGTAATGTTCAACCAGAAGATGCTATAGAGACAAGGTATGTTATAACATCACAA
300 GROUP_1       CACACCAGTAATGTTCAACCAGAAGATGCTATAGAGACAAGGTATGTTATAACATCACAA
301
302 1_HRV1A1|d    ACAAGAGATGAGATGAGTATAGAAAGTTTCCTTGGTAGATCTGGTTGTGTCCACATCTCA
303 2_HRV1A2|d    ACAAGAGATGAGATGAGTATAGAAAGTTTCCTTGGTAGATCTGGTTGTGTCCACATCTCA
304 3_HRV1A|cD    ACAAGAGATGAGATGAGTATAGAAAGTTTCCTTGGTAGATCTGGTTGTGTCCACATCTCA
305 GROUP_1       ACAAGAGATGAGATGAGTATAGAAAGTTTCCTTGGTAGATCTGGTTGTGTCCACATCTCA
306
307 1_HRV1A1|d    AGAATAAAGGTTGATTACACTGAC---------------TATAATGGA---CAGGACATA
308 2_HRV1A2|d    AGAATAAAGGTTGATTACACTGAC---------------TATAATGGA---CAGGACATA
309 3_HRV1A|cD    AGAATAAAGGTTGATTACACTGAC---------------TATAATGGA---CAGGACATA
310 GROUP_1       AGAATAAAGGTTGATTACACTGAC...............TATAATGGA...CAGGACATA
311
312 1_HRV1A1|d    AATTTCACAAAATGGAAAATCACACTACAGGAAATGGCACAGATTAGGAGAAAATTTGAA
313 2_HRV1A2|d    AATTTCACAAAATGGAAAATCACACTACAGGAAATGGCACAGATTAGGAGAAAATTTGAA
314 3_HRV1A|cD    AATTTCACAAAATGGAAAATCACACTACAGGAAATGGCACAGATTAGGAGAAAATTTGAA
315 GROUP_1       AATTTCACAAAATGGAAAATCACACTACAGGAAATGGCACAGATTAGGAGAAAATTTGAA
316
317 1_HRV1A1|d    TTGTTTACATATGTCAGGTTTGACTCAGAAATAACCTTGG-TGCCTTGTATTGCTGGTAG
318 2_HRV1A2|d    TTGTTTACATATGTCAGGTTTGACTCAGAAATAACCTTGG-TGCCTTGTATTGCTGGTAG
```

FIG. D14 CONT'D

```
10.trace                                                                    9/20/2007 5:05 PM 319   3_HRV1A|cD    TTGTTTACATATGTCAGGTTTGACTCAGAAATAACCTTGG-TGCCTTGTATTGCTGGTAG
320   GROUP_1       TTGTTTACATATGTCAGGTTTGACTCAGAAATAACCTTGG.TGCCTTGTATTGCTGGTAG
321
322   1_HRV1A1|d    AGGAGACGACATTGGACATATTGTAATGCAATATATGTATGTTCCTCCAGGAGCTCCAAT
323   2_HRV1A2|d    AGGAGACGACATTGGACATATTGTAATGCAATATATGTATGTTCCTCCAGGAGCTCCAAT
324   3_HRV1A|cD    AGGAGACGACATTGGACATATTGTAATGCAATATATGTATGTTCCTCCAGGAGCTCCAAT
325   GROUP_1       AGGAGACGACATTGGACATATTGTAATGCAATATATGTATGTTCCTCCAGGAGCTCCAAT
326
327   1_HRV1A1|d    TCCTTCAAAAAGAAACGATTTCTCATGGCAATCAGGCACCAATATGTCAATATTCTGGCA
328   2_HRV1A2|d    TCCTTCAAAAAGAAACGATTTCTCATGGCAATCAGGCACCAATATGTCAATATTCTGGCA
329   3_HRV1A|cD    TCCTTCAAAAAGAAACGATTTCTCATGGCAATCAGGCACCAATATGTCAATATTCTGGCA
330   GROUP_1       TCCTTCAAAAAGAAACGATTTCTCATGGCAATCAGGCACCAATATGTCAATATTCTGGCA
331
332   1_HRV1A1|d    ACATGGACAGCCATTTCCTAGATTTTCTTTACCATTTCTTAGCATTGCATCAGCTTATTA
333   2_HRV1A2|d    ACATGGACAGCCATTTCCTAGATTTTCTTTACCATTTCTTAGCATTGCATCAGCTTATTA
334   3_HRV1A|cD    ACATGGACAGCCATTTCCTAGATTTTCTTTACCATTTCTTAGCATTGCATCAGCTTATTA
335   GROUP_1       ACATGGACAGCCATTTCCTAGATTTTCTTTACCATTTCTTAGCATTGCATCAGCTTATTA
336
337   1_HRV1A1|d    TATGTTTTATGATGGATATGATGGAGACAACACTTCTTCCAAGTATGGTAGCGTAGTTAC
338   2_HRV1A2|d    TATGTTTTATGATGGATATGATGGAGACAACACTTCTTCCAAGTATGGTAGCGTAGTTAC
339   3_HRV1A|cD    TATGTTTTATGATGGATATGATGGAGACAACACTTCTTCCAAGTATGGTAGCGTAGTTAC
340   GROUP_1       TATGTTTTATGATGGATATGATGGAGACAACACTTCTTCCAAGTATGGTAGCGTAGTTAC
341
342   1_HRV1A1|d    TAATGATATGGGTACTATATGCTCAAGAATAGTTACAGAAAAACAGAAACATTCTGTTGT
343   2_HRV1A2|d    TAATGATATGGGTACTATATGCTCAAGAATAGTTACAGAAAAACAGAAACATTCTGTTGT
344   3_HRV1A|cD    TAATGATATGGGTACTATATGCTCAAGAATAGTTACAGAAAAACAGAAACATTCTGTTGT
345   GROUP_1       TAATGATATGGGTACTATATGCTCAAGAATAGTTACAGAAAAACAGAAACATTCTGTTGT
346
347   1_HRV1A1|d    CATCACAACACACATATATCATAAAGCTAAACACACAAAAGCTTGGTGTCCTAGGCCCCC
348   2_HRV1A2|d    CATCACAACACACATATATCATAAAGCTAAACACACAAAAGCTTGGTGTCCTAGGCCCCC
349   3_HRV1A|cD    CATCACAACACACATATATCATAAAGCTAAACACACAAAAGCTTGGTGTCCTAGGCCCCC
350   GROUP_1       CATCACAACACACATATATCATAAAGCTAAACACACAAAAGCTTGGTGTCCTAGGCCCCC
351
352   1_HRV1A1|d    TAGAGCTGTCCCTTACACA-CATAGTCATGTGACTAATTATATGC-CAGAAA---CAGGT
353   2_HRV1A2|d    TAGAGCTGTCCCTTACACA-CATAGTCATGTGACTAATTATATGC-CAGAAA---CAGGT
354   3_HRV1A|cD    TAGAGCTGTCCCTTACACA-CATAGTCATGTGACTAATTATATGC-CAGAAA---CAGGT
355   GROUP_1       TAGAGCTGTCCCTTACACA.CATAGTCATGTGACTAATTATATGC.CAGAAA...CAGGT
356
357   1_HRV1A1|d    GACG------TGACAACAG---CCATAGTCCGCAGAA------ACACTATAACAACTG--
358   2_HRV1A2|d    GACG------TGACAACAG---CCATAGTCCGCAGAA------ACACTATAACAACTG--
359   3_HRV1A|cD    GACG------TGACAACAG---CCATAGTCCGCAGAA------ACACTATAACAACTG--
360   GROUP_1       GACG......TGACAACAG...CCATAGTCCGCAGAA......ACACTATAACAACTG..
361
362   1_HRV1A1|d    ----CA---------------
363   2_HRV1A2|d    ----CG---------------
364   3_HRV1A|cD    ----CT---------------
365   GROUP_1       ....C-...............
366
367
368
369   Group  2:
370
371   4_HRV1B1|d    AATCCAGTGGAAAATTACATTGATGAAGTTTTAAATGAAGTTCTAGTAGTACCAAATATA
372   5_HRV1B2|d    AATCCAGTGGAAAATTACATTGATGAAGTTTTAAATGAAGTTCTAGTAGTACCAAATATA
373   6_HRV1B       AATCCAGTGGAAAATTACATTGATGAAGTTTTAAATGAAGTTCTAGTAGTACCAAATATA
374   GROUP_2       AATCCAGTGGAAAATTACATTGATGAAGTTTTAAATGAAGTTCTAGTAGTACCAAATATA
375
376   4_HRV1B1|d    AAAGAAAGCCATCACACTACATCAAATTCTGCTCCACTCTTGGATGCTGCAGAGACAGGA
377   5_HRV1B2|d    AAAGAAAGCCATCACACTACATCAAATTCTGCTCCACTCTTGGATGCTGCAGAGACAGGA
378   6_HRV1B       AAAGAAAGCCATCACACTACATCAAATTCTGCTCCACTCTTGGATGCTGCAGAGACAGGA
379   GROUP_2       AAAGAAAGCCATCACACTACATCAAATTCTGCTCCACTCTTGGATGCTGCAGAGACAGGA
380
381   4_HRV1B1|d    CACACCAGTAATGTACAACCAGAGGATGCTATAGAAACAAGATATGTTATGACATCACAA
382   5_HRV1B2|d    CACACCAGTAATGTACAACCAGAGGATGCTATAGAAACAAGATATGTTATGACATCACAA
383   6_HRV1B       CACACCAGTAATGTACAACCAGAGGATGCTATAGAAACAAGATATGTTATGACATCACAA
```

FIG. D14 CONT'D

```
10.trace                                                                    9/20/2007 5:05 PM 384 GROUP_2         CACACCAGTAATGTACAACCAGAGGATGCTATAGAAACAAGATATGTTATGACATCACAA
385
386 4_HRV1B1|d      ACAAGAGATGAGATGAGTATAGAAAGTTTTCTTGGTAGATCTGGCTGTGTGCATATTTCA
387 5_HRV1B2|d      ACAAGAGATGAGATGAGTATAGAAAGTTTTCTTGGTAGATCTGGCTGTGTGCATATTTCA
388 6_HRV1B         ACAAGAGATGAGATGAGTATAGAAAGTTTTCTTGGTAGATCTGGCTGTGTGCATATTTCA
389 GROUP_2         ACAAGAGATGAGATGAGTATAGAAAGTTTTCTTGGTAGATCTGGCTGTGTGCATATTTCA
390
391 4_HRV1B1|d      AGAATAAAGGTTGATTACAATGAC---------------TACAATGGA---GTGAACAAA
392 5_HRV1B2|d      AGAATAAAGGTTGATTACAATGAC---------------TACAATGGA---GTGAACAAA
393 6_HRV1B         AGAATAAAGGTTGATTACAATGAC---------------TACAATGGA---GTGAACAAA
394 GROUP_2         AGAATAAAGGTTGATTACAATGAC...............TACAATGGA...GTGAACAAA
395
396 4_HRV1B1|d      AACTTTACAACATGGAAAATCACACTGCAGGAGATGGCACAAATTAGAAGAAAATTCGAA
397 5_HRV1B2|d      AACTTTACAACATGGAAAATCACACTGCAGGAGATGGCACAAATTAGAAGAAAATTCGAA
398 6_HRV1B         AACTTTACAACATGGAAAATCACACTGCAGGAGATGGCACAAATTAGAAGAAAATTCGAA
399 GROUP_2         AACTTTACAACATGGAAAATCACACTGCAGGAGATGGCACAAATTAGAAGAAAATTCGAA
400
401 4_HRV1B1|d      CTATTTACTTATGTTAGGTTTGATTCAGAAGTAACTTTAG-TACCCTGTATTGCTGGTAG
402 5_HRV1B2|d      CTATTTACTTATGTTAGGTTTGATTCAGAAGTAACTTTAG-TACCCTGTATTGCTGGTAG
403 6_HRV1B         CTATTTACTTATGTTAGGTTTGATTCAGAAGTAACTTTAG-TACCCTGTATTGCTGGTAG
404 GROUP_2         CTATTTACTTATGTTAGGTTTGATTCAGAAGTAACTTTAG.TACCCTGTATTGCTGGTAG
405
406 4_HRV1B1|d      AGGAGATGACATTGGTCATGTTGTAATGCAGTATATGTATGTTCCCCCAGGAGCTCCAAT
407 5_HRV1B2|d      AGGAGATGACATTGGTCATGTTGTAATGCAGTATATGTATGTTCCCCCAGGAGCTCCAAT
408 6_HRV1B         AGGAGATGACATTGGTCATGTTGTAATGCAGTATATGTATGTTCCCCCAGGAGCTCCAAT
409 GROUP_2         AGGAGATGACATTGGTCATGTTGTAATGCAGTATATGTATGTTCCCCCAGGAGCTCCAAT
410
411 4_HRV1B1|d      TCCAAAAACAAGAAATGATTTCTCATGGCAATCAGGCACTAATATGTCAATATTCTGGCA
412 5_HRV1B2|d      TCCAAAAACAAGAAATGATTTCTCATGGCAATCAGGCACTAATATGTCAATATTCTGGCA
413 6_HRV1B         TCCAAAAACAAGAAATGATTTCTCATGGCAATCAGGCACTAATATGTCAATATTCTGGCA
414 GROUP_2         TCCAAAAACAAGAAATGATTTCTCATGGCAATCAGGCACTAATATGTCAATATTCTGGCA
415
416 4_HRV1B1|d      ACATGGACAACCGTTCCCTAGATTCTCTTTACCATTTCTTAGCATTGCATCAGCTTATTA
417 5_HRV1B2|d      ACATGGACAACCGTTCCCTAGATTCTCTTTACCATTTCTTAGCATTGCATCAGCTTATTA
418 6_HRV1B         ACATGGACAACCGTTCCCTAGATTCTCTTTACCATTTCTTAGCATTGCATCAGCTTATTA
419 GROUP_2         ACATGGACAACCGTTCCCTAGATTCTCTTTACCATTTCTTAGCATTGCATCAGCTTATTA
420
421 4_HRV1B1|d      CATGTTTTATGATGGATATGATGGAGATAATTCCTCTTCCAAATATGGTAGTATAGTCAC
422 5_HRV1B2|d      CATGTTTTATGATGGATATGATGGAGATAATTCCTCTTCCAAATATGGTAGTATAGTCAC
423 6_HRV1B         CATGTTTTATGATGGATATGATGGAGATAATTCCTCTTCCAAATATGGTAGTATAGTCAC
424 GROUP_2         CATGTTTTATGATGGATATGATGGAGATAATTCCTCTTCCAAATATGGTAGTATAGTCAC
425
426 4_HRV1B1|d      CAATGATATGGGAACCATATGTTCAAGAATAGTTACAGAGAAGCAGGAACACCCTGTCGT
427 5_HRV1B2|d      CAATGATATGGGAACCATATGTTCAAGAATAGTTACAGAGAAGCAGGAACACCCTGTCGT
428 6_HRV1B         CAATGATATGGGAACCATATGTTCAAGAATAGTTACAGAGAAGCAGGAACACCCTGTCGT
429 GROUP_2         CAATGATATGGGAACCATATGTTCAAGAATAGTTACAGAGAAGCAGGAACACCCTGTCGT
430
431 4_HRV1B1|d      TATTACAACACACATATATCACAAAGCTAAACACACAAAAGCTTGGTGTCCTAGACCTCC
432 5_HRV1B2|d      TATTACAACACACATATATCACAAAGCTAAACACACAAAAGCTTGGTGTCCTAGACCTCC
433 6_HRV1B         TATTACAACACACATATATCACAAAGCTAAACACACAAAAGCTTGGTGTCCTAGACCTCC
434 GROUP_2         TATTACAACACACATATATCACAAAGCTAAACACACAAAAGCTTGGTGTCCTAGACCTCC
435
436 4_HRV1B1|d      TAGAGCTGTTCCTTACACA-CATAGTCGTGTAACTAATTATGTAC-CAAAAA---CAGGT
437 5_HRV1B2|d      TAGAGCTGTTCCTTACACA-CATAGTCGTGTAACTAATTATGTAC-CAAAAA---CAGGT
438 6_HRV1B         TAGAGCTGTTCCTTACACA-CATAGTCGTGTAACTAATTATGTAC-CAAAAA---CAGGT
439 GROUP_2         TAGAGCTGTTCCTTACACA.CATAGTCGTGTAACTAATTATGTAC.CAAAAA...CAGGT
440
441 4_HRV1B1|d      GATG------TGACAACAG---CTATAGTTCCTAGAG------CTAGCATGAAAACTG--
442 5_HRV1B2|d      GATG------TGACAACAG---CTATAGTTCCTAGAG------CTAGCATGAAAACTG--
443 6_HRV1B         GATG------TGACAACAG---CTATAGTTCCTAGAG------CTAGCATGAAAACTG--
444 GROUP_2         GATG......TGACAACAG...CTATAGTTCCTAGAG......CTAGCATGAAAACTG..
445
446 4_HRV1B1|d      ----TA---------------
447 5_HRV1B2|d      ----TC---------------
448 6_HRV1B         ----TT---------------
```

FIG. D14 CONT'D 10.trace                                                                    9/20/2007 5:05 PM

```
449 GROUP_2      ....T-..............
450
451
452
453 Group  3:
454
455 7_HRV40a|d   AACCCCGTTGAAAGGTATGTTGATGAGGTTCTTAATGAAGTTCTGGTAGTTCCAAATATC
456 8_HRV40b|d   AACCCCGTTGAAAGGTATGTTGATGAGGTTCTTAATGAAGTTCTGGTAGTTCCAAATATC
457 9_HRV40      AACCCCGTTGAAAGGTATGTTGATGAGGTTCTTAATGAAGTTCTGGTAGTTCCAAATATC
458 GROUP_3      AACCCCGTTGAAAGGTATGTTGATGAGGTTCTTAATGAAGTTCTGGTAGTTCCAAATATC
459
460 7_HRV40a|d   AGAGAGAGCCATCCAACTACATCAAATTCGGCCCCTGCCTTGGATGCAGCAGAGACTGGA
461 8_HRV40b|d   AGAGAGAGCCATCCAACTACATCAAATTCGGCCCCTGCCTTGGATGCAGCAGAGACTGGA
462 9_HRV40      AGAGAGAGCCATCCAACTACATCAAATTCGGCCCCTGCCTTGGATGCAGCAGAGACTGGA
463 GROUP_3      AGAGAGAGCCATCCAACTACATCAAATTCGGCCCCTGCCTTGGATGCAGCAGAGACTGGA
464
465 7_HRV40a|d   CATACAAGCAACATACAACCTGAAGATACAATAGAAACAAGATTTGTGCAGACATCACAA
466 8_HRV40b|d   CATACAAGCAACATACAACCTGAAGATACAATAGAAACAAGATTTGTGCAGACATCACAA
467 9_HRV40      CATACAAGCAACATACAACCTGAAGATACAATAGAAACAAGATTTGTGCAGACATCACAA
468 GROUP_3      CATACAAGCAACATACAACCTGAAGATACAATAGAAACAAGATTTGTGCAGACATCACAA
469
470 7_HRV40a|d   ACTAGAGATGAAATGAGCATAGAGAGTTTCTTGGGAAGATCTGGGTGCATTCATATATCC
471 8_HRV40b|d   ACTAGAGATGAAATGAGCATAGAGAGTTTCTTGGGAAGATCTGGGTGCATTCATATATCC
472 9_HRV40      ACTAGAGATGAAATGAGCATAGAGAGTTTCTTGGGAAGATCTGGGTGCATTCATATATCC
473 GROUP_3      ACTAGAGATGAAATGAGCATAGAGAGTTTCTTGGGAAGATCTGGGTGCATTCATATATCC
474
475 7_HRV40a|d   ACAATTACAGTGGATAACAGTTTG---------------GAATATG------ATGACCAC
476 8_HRV40b|d   ACAATTACAGTGGATAACAGTTTG---------------GAATATG------ATGACCAC
477 9_HRV40      ACAATTACAGTGGATAACAGTTTG---------------GAATATG------ATGACCAC
478 GROUP_3      ACAATTACAGTGGATAACAGTTTG...............GAATATG......ATGACCAC
479
480 7_HRV40a|d   CACTTTGATAAGTGGCAGATAACCATACAAGAGATGTCACAAATTAGGAGAAAATTTGAA
481 8_HRV40b|d   CACTTTGATAAGTGGCAGATAACCATACAAGAGATGTCACAAATTAGGAGAAAATTTGAA
482 9_HRV40      CACTTTGATAAGTGGCAGATAACCATACAAGAGATGTCACAAATTAGGAGAAAATTTGAA
483 GROUP_3      CACTTTGATAAGTGGCAGATAACCATACAAGAGATGTCACAAATTAGGAGAAAATTTGAA
484
485 7_HRV40a|d   TTCTTTACATATGCTAGGTTTGATTCAGAAATTACCTTAG-TTCCTTGTATAGCCGGTAA
486 8_HRV40b|d   TTCTTTACATATGCTAGGTTTGATTCAGAAATTACCTTAG-TTCCTTGTATAGCCGGTAA
487 9_HRV40      TTCTTTACATATGCTAGGTTTGATTCAGAAATTACCTTAG-TTCCTTGTATAGCCGGTAA
488 GROUP_3      TTCTTTACATATGCTAGGTTTGATTCAGAAATTACCTTAG.TTCCTTGTATAGCCGGTAA
489
490 7_HRV40a|d   GGGTGAAGACATTGGACACATTGTGATGCAATATATGTATGTACCCCCTGGCGCACCCAT
491 8_HRV40b|d   GGGTGAAGACATTGGACACATTGTGATGCAATATATGTATGTACCCCCTGGCGCACCCAT
492 9_HRV40      GGGTGAAGACATTGGACACATTGTGATGCAATATATGTATGTACCCCCTGGCGCACCCAT
493 GROUP_3      GGGTGAAGACATTGGACACATTGTGATGCAATATATGTATGTACCCCCTGGCGCACCCAT
494
495 7_HRV40a|d   ACCAAAGAAAAGAAATGATTACACATGGCAGTCAGGCACTAATGCTTCTGTATTCTGGCA
496 8_HRV40b|d   ACCAAAGAAAAGAAATGATTACACATGGCAGTCAGGCACTAATGCTTCTGTATTCTGGCA
497 9_HRV40      ACCAAAGAAAAGAAATGATTACACATGGCAGTCAGGCACTAATGCTTCTGTATTCTGGCA
498 GROUP_3      ACCAAAGAAAAGAAATGATTACACATGGCAGTCAGGCACTAATGCTTCTGTATTCTGGCA
499
500 7_HRV40a|d   ACATGGTCAAACTTTCCCTAGATTTTCTTTACCTTTCCTAAGCATAGCTTCAGCATACTA
501 8_HRV40b|d   ACATGGTCAAACTTTCCCTAGATTTTCTTTACCTTTCCTAAGCATAGCTTCAGCATACTA
502 9_HRV40      ACATGGTCAAACTTTCCCTAGATTTTCTTTACCTTTCCTAAGCATAGCTTCAGCATACTA
503 GROUP_3      ACATGGTCAAACTTTCCCTAGATTTTCTTTACCTTTCCTAAGCATAGCTTCAGCATACTA
504
505 7_HRV40a|d   CATGTTTTATGATGGATACGATGGTGATACATCGACCTCAAGATATGGCACATCAGTCAC
506 8_HRV40b|d   CATGTTTTATGATGGATACGATGGTGATACATCGACCTCAAGATATGGCACATCAGTCAC
507 9_HRV40      CATGTTTTATGATGGATACGATGGTGATACATCGACCTCAAGATATGGCACATCAGTCAC
508 GROUP_3      CATGTTTTATGATGGATACGATGGTGATACATCGACCTCAAGATATGGCACATCAGTCAC
509
510 7_HRV40a|d   TAACCATATGGGAACGCTATGCTCAAGAATAGTCACCAACAAGCAGCAGCATGAAGTTGA
511 8_HRV40b|d   TAACCATATGGGAACGCTATGCTCAAGAATAGTCACCAACAAGCAGCAGCATGAAGTTGA
512 9_HRV40      TAACCATATGGGAACGCTATGCTCAAGAATAGTCACCAACAAGCAGCAGCATGAAGTTGA
513 GROUP_3      TAACCATATGGGAACGCTATGCTCAAGAATAGTCACCAACAAGCAGCAGCATGAAGTTGA
```

FIG. D14 CONT'D

```
10.trace                                                                                    9/20/2007 5:05 PM
514
515  7_HRV40a|d    GATTACCACACGTATATATCACAAGGCCAAGCATATTAAAGCATGGTGTCCAAGGGCCCC
516  8_HRV40b|d    GATTACCACACGTATATATCACAAGGCCAAGCATATTAAAGCATGGTGTCCAAGGGCCCC
517  9_HRV40       GATTACCACACGTATATATCACAAGGCCAAGCATATTAAAGCATGGTGTCCAAGGGCCCC
518  GROUP_3       GATTACCACACGTATATATCACAAGGCCAAGCATATTAAAGCATGGTGTCCAAGGGCCCC
519
520  7_HRV40a|d    AAGAGCAGTACCTTACACA-CATACACACTCAACAAATTATAAAC-CTCAAG---AAGGT
521  8_HRV40b|d    AAGAGCAGTACCTTACACA-CATACACACTCAACAAATTATAAAC-CTCAAG---AAGGT
522  9_HRV40       AAGAGCAGTACCTTACACA-CATACACACTCAACAAATTATAAAC-CTCAAG---AAGGT
523  GROUP_3       AAGAGCAGTACCTTACACA.CATACACACTCAACAAATTATAAAC.CTCAAG...AAGGT
524
525  7_HRV40a|d    GAAG------TCCAGATTT---TCCTCAAAGAGAGAG------CCAGCCTAACAACAG--
526  8_HRV40b|d    GAAG------TCCAGATTT---TCCTCAAAGAGAGAG------CCAGCCTAACAACAG--
527  9_HRV40       GAAG------TCCAGATTT---TCCTCAAAGAGAGAG------CCAGCCTAACAACAG--
528  GROUP_3       GAAG......TCCAGATTT...TCCTCAAAGAGAGAG......CCAGCCTAACAACAG..
529
530  7_HRV40a|d    ----TA---------------
531  8_HRV40b|d    ----TC---------------
532  9_HRV40       ----TT---------------
533  GROUP_3       ....T-...............
534
535
536
537  Group  4:
538
539  10_HRV85      AATCCTGTTGAAAAATACGTTGATGAAGTCCTTAATGAGGTTCTAGTGGTTCCAAATATC
540  11_HRV85a|    AATCCTGTTGAAAAATACGTTGATGAAGTCCTTAATGAGGTTCTAGTGGTTCCAAATATC
541  12_HRV85b|    AATCCTGTTGAAAAATACGTTGATGAAGTCCTTAATGAGGTTCTAGTGGTTCCAAATATC
542  GROUP_4       AATCCTGTTGAAAAATACGTTGATGAAGTCCTTAATGAGGTTCTAGTGGTTCCAAATATC
543
544  10_HRV85      AAAGAGAGTCACCCAACTATATCAAATTCAGCTCCTGCTTTGGATGCAGCAGAGACTGGC
545  11_HRV85a|    AAAGAGAGTCACCCAACTATATCAAATTCAGCTCCTGCTTTGGATGCAGCAGAGACTGGC
546  12_HRV85b|    AAAGAGAGTCACCCAACTATATCAAATTCAGCTCCTGCTTTGGATGCAGCAGAGACTGGC
547  GROUP_4       AAAGAGAGTCACCCAACTATATCAAATTCAGCTCCTGCTTTGGATGCAGCAGAGACTGGC
548
549  10_HRV85      CATACAAGTAGTACACAGCCCGAGGATACAATAGAGACCAGGTTTGTTCAAACTTCACAG
550  11_HRV85a|    CATACAAGTAGTACACAGCCCGAGGATACAATAGAGACCAGGTTTGTTCAAACTTCACAG
551  12_HRV85b|    CATACAAGTAGTACACAGCCCGAGGATACAATAGAGACCAGGTTTGTTCAAACTTCACAG
552  GROUP_4       CATACAAGTAGTACACAGCCCGAGGATACAATAGAGACCAGGTTTGTTCAAACTTCACAG
553
554  10_HRV85      ACTAGGGATGAAATGAGTTTAGAAAGTTTCTTGGGAAGATCTGGATGTATCCATATATCT
555  11_HRV85a|    ACTAGGGATGAAATGAGTTTAGAAAGTTTCTTGGGAAGATCTGGATGTATCCATATATCT
556  12_HRV85b|    ACTAGGGATGAAATGAGTTTAGAAAGTTTCTTGGGAAGATCTGGATGTATCCATATATCT
557  GROUP_4       ACTAGGGATGAAATGAGTTTAGAAAGTTTCTTGGGAAGATCTGGATGTATCCATATATCT
558
559  10_HRV85      ACAATTACTGTGAATAACAACCTA---------------GATTATG------ATGAAAAT
560  11_HRV85a|    ACAATTACTGTGAATAACAACCTA---------------GATTATG------ATGAAAAT
561  12_HRV85b|    ACAATTACTGTGAATAACAACCTA---------------GATTATG------ATGAAAAT
562  GROUP_4       ACAATTACTGTGAATAACAACCTA...............GATTATG......ATGAAAAT
563
564  10_HRV85      CACTTTGATCAGTGGCAGATAACTATACAGGAAATGGCACAAATTAGAAGGAAGTTTGAG
565  11_HRV85a|    CACTTTGATCAGTGGCAGATAACTATACAGGAAATGGCACAAATTAGAAGGAAGTTTGAG
566  12_HRV85b|    CACTTTGATCAGTGGCAGATAACTATACAGGAAATGGCACAAATTAGAAGGAAGTTTGAG
567  GROUP_4       CACTTTGATCAGTGGCAGATAACTATACAGGAAATGGCACAAATTAGAAGGAAGTTTGAG
568
569  10_HRV85      TTCTTTACTTACACTAGATTTGATTCAGAAATCACTTTAG-TCCCTTGTATAGCTGGAAA
570  11_HRV85a|    TTCTTTACTTACACTAGATTTGATTCAGAAATCACTTTAG-TCCCTTGTATAGCTGGAAA
571  12_HRV85b|    TTCTTTACTTACACTAGATTTGATTCAGAAATCACTTTAG-TCCCTTGTATAGCTGGAAA
572  GROUP_4       TTCTTTACTTACACTAGATTTGATTCAGAAATCACTTTAG.TCCCTTGTATAGCTGGAAA
573
574  10_HRV85      GGGTGATGATATTGGACACATTGTAATGCAGTATATGTATGTGCCCCCCGGAGCACCAAT
575  11_HRV85a|    GGGTGATGATATTGGACACATTGTAATGCAGTATATGTATGTGCCCCCCGGAGCACCAAT
576  12_HRV85b|    GGGTGATGATATTGGACACATTGTAATGCAGTATATGTATGTGCCCCCCGGAGCACCAAT
577  GROUP_4       GGGTGATGATATTGGACACATTGTAATGCAGTATATGTATGTGCCCCCCGGAGCACCAAT
578
```

FIG. D14 CONT'D 10.trace                                                                                           9/20/2007 5:05 PM

```
579  10_HRV85      ACCAAGGAAAAGAGATGATTACACATGGCAATCAGGTACTAATGCTTCCGTGTTTTGGCA
580  11_HRV85a|    ACCAAGGAAAAGAGATGATTACACATGGCAATCAGGTACTAATGCTTCCGTGTTTTGGCA
581  12_HRV85b|    ACCAAGGAAAAGAGATGATTACACATGGCAATCAGGTACTAATGCTTCCGTGTTTTGGCA
582  GROUP_4       ACCAAGGAAAAGAGATGATTACACATGGCAATCAGGTACTAATGCTTCCGTGTTTTGGCA
583
584  10_HRV85      ACATGGGCAAACTTTCCCCAGATTTTCCTTACCTTTCTTGAGTGTTGCTTCAGCATATTA
585  11_HRV85a|    ACATGGGCAAACTTTCCCCAGATTTTCCTTACCTTTCTTGAGTGTTGCTTCAGCATATTA
586  12_HRV85b|    ACATGGGCAAACTTTCCCCAGATTTTCCTTACCTTTCTTGAGTGTTGCTTCAGCATATTA
587  GROUP_4       ACATGGGCAAACTTTCCCCAGATTTTCCTTACCTTTCTTGAGTGTTGCTTCAGCATATTA
588
589  10_HRV85      CATGTTTTATGATGGTTATGATGGTGATACACCAGGCTCAATGTATGGGACGTCAGTCAC
590  11_HRV85a|    CATGTTTTATGATGGTTATGATGGTGATACACCAGGCTCAATGTATGGGACGTCAGTCAC
591  12_HRV85b|    CATGTTTTATGATGGTTATGATGGTGATACACCAGGCTCAATGTATGGGACGTCAGTCAC
592  GROUP_4       CATGTTTTATGATGGTTATGATGGTGATACACCAGGCTCAATGTATGGGACGTCAGTCAC
593
594  10_HRV85      CAACCACATGGGAACACTGTGCTCGAGGATAGTTACCAACAAACAGCAGCATGAGGTTGA
595  11_HRV85a|    CAACCACATGGGAACACTGTGCTCGAGGATAGTTACCAACAAACAGCAGCATGAGGTTGA
596  12_HRV85b|    CAACCACATGGGAACACTGTGCTCGAGGATAGTTACCAACAAACAGCAGCATGAGGTTGA
597  GROUP_4       CAACCACATGGGAACACTGTGCTCGAGGATAGTTACCAACAAACAGCAGCATGAGGTTGA
598
599  10_HRV85      AATCACCACGCGTGTGTATCATAAGGCCAAGCATGTAAAGGCTTGGTGTCCAAGAGCACC
600  11_HRV85a|    AATCACCACGCGTGTGTATCATAAGGCCAAGCATGTAAAGGCTTGGTGTCCAAGAGCACC
601  12_HRV85b|    AATCACCACGCGTGTGTATCATAAGGCCAAGCATGTAAAGGCTTGGTGTCCAAGAGCACC
602  GROUP_4       AATCACCACGCGTGTGTATCATAAGGCCAAGCATGTAAAGGCTTGGTGTCCAAGAGCACC
603
604  10_HRV85      AAGAGCGGTGCCTTATACA-CACACACGCTCAACCAACTATGTGC-CACAAG---ATGGT
605  11_HRV85a|    AAGAGCGGTGCCTTATACA-CACACACGCTCAACCAACTATGTGC-CACAAG---ATGGT
606  12_HRV85b|    AAGAGCGGTGCCTTATACA-CACACACGCTCAACCAACTATGTGC-CACAAG---ATGGT
607  GROUP_4       AAGAGCGGTGCCTTATACA.CACACACGCTCAACCAACTATGTGC.CACAAG...ATGGT
608
609  10_HRV85      GAAG------TTAAGATCT---TCCTCAAAGAGAGAG------CTAGTTTAACCACAG--
610  11_HRV85a|    GAAG------TTAAGATCT---TCCTCAAAGAGAGAG------CTAGTTTAACCACAG--
611  12_HRV85b|    GAAG------TTAAGATCT---TCCTCAAAGAGAGAG------CTAGTTTAACCACAG--
612  GROUP_4       GAAG......TTAAGATCT...TCCTCAAAGAGAGAG......CTAGTTTAACCACAG..
613
614  10_HRV85      ----CA--------------
615  11_HRV85a|    ----CG--------------
616  12_HRV85b|    ----CT--------------
617  GROUP_4       ....C-..............
618
619
620
621  Group  5:
622
623  13_HRV56a|    AACCCAGTTGAGAGATATGTAGATGATGTTTTAAATGAAGTTTTAGTTGTTCCAAATATT
624  14_HRV56b|    AACCCAGTTGAGAGATATGTAGATGATGTTTTAAATGAAGTTTTAGTTGTTCCAAATATT
625  15_HRV56      AACCCAGTTGAGAGATATGTAGATGATGTTTTAAATGAAGTTTTAGTTGTTCCAAATATT
626  GROUP_5       AACCCAGTTGAGAGATATGTAGATGATGTTTTAAATGAAGTTTTAGTTGTTCCAAATATT
627
628  13_HRV56a|    AGGGAGAGCCATCCATCCACATCAAATTCTGCCCCTGCATTAGATGCTGCTGAAACTGGC
629  14_HRV56b|    AGGGAGAGCCATCCATCCACATCAAATTCTGCCCCTGCATTAGATGCTGCTGAAACTGGC
630  15_HRV56      AGGGAGAGCCATCCATCCACATCAAATTCTGCCCCTGCATTAGATGCTGCTGAAACTGGC
631  GROUP_5       AGGGAGAGCCATCCATCCACATCAAATTCTGCCCCTGCATTAGATGCTGCTGAAACTGGC
632
633  13_HRV56a|    CATACTAGTGCAATCCAACCAGAAGACACTATAGAAACCAGATATGTACAGACATCACAA
634  14_HRV56b|    CATACTAGTGCAATCCAACCAGAAGACACTATAGAAACCAGATATGTACAGACATCACAA
635  15_HRV56      CATACTAGTGCAATCCAACCAGAAGACACTATAGAAACCAGATATGTACAGACATCACAA
636  GROUP_5       CATACTAGTGCAATCCAACCAGAAGACACTATAGAAACCAGATATGTACAGACATCACAA
637
638  13_HRV56a|    ACTAGGGATGAAATGAGTATAGAGAGTTTTCTAGGTAGATCAGGTTGTATACATATATCA
639  14_HRV56b|    ACTAGGGATGAAATGAGTATAGAGAGTTTTCTAGGTAGATCAGGTTGTATACATATATCA
640  15_HRV56      ACTAGGGATGAAATGAGTATAGAGAGTTTTCTAGGTAGATCAGGTTGTATACATATATCA
641  GROUP_5       ACTAGGGATGAAATGAGTATAGAGAGTTTTCTAGGTAGATCAGGTTGTATACATATATCA
642
643  13_HRV56a|    ACTATAACTGTGGATAATGATGTA--------------GATTATA------ATTCAAAG
```

FIG. D14 CONT'D

```
10.trace                                                           9/20/2007 5:05 PM 644 14_HRV56b|  ACTATAACTGTGGATAATGATGTA---------------GATTATA------ATTCAAAG
645 15_HRV56   ACTATAACTGTGGATAATGATGTA---------------GATTATA------ATTCAAAG
646 GROUP_5    ACTATAACTGTGGATAATGATGTA...............GATTATA......ATTCAAAG
647
648 13_HRV56a| CATTATAATAAATGGCAAATAACCTTACAAGAAATGGCTCAAGTTAGGCGTAAATTTGAA
649 14_HRV56b| CATTATAATAAATGGCAAATAACCTTACAAGAAATGGCTCAAGTTAGGCGTAAATTTGAA
650 15_HRV56   CATTATAATAAATGGCAAATAACCTTACAAGAAATGGCTCAAGTTAGGCGTAAATTTGAA
651 GROUP_5    CATTATAATAAATGGCAAATAACCTTACAAGAAATGGCTCAAGTTAGGCGTAAATTTGAA
652
653 13_HRV56a| TTCTTTACTTATGTCAGATTTGATTCAGAGGTTACTTTGG-TACCTTGTGTAGCCGGCAA
654 14_HRV56b| TTCTTTACTTATGTCAGATTTGATTCAGAGGTTACTTTGG-TACCTTGTGTAGCCGGCAA
655 15_HRV56   TTCTTTACTTATGTCAGATTTGATTCAGAGGTTACTTTGG-TACCTTGTGTAGCCGGCAA
656 GROUP_5    TTCTTTACTTATGTCAGATTTGATTCAGAGGTTACTTTGG.TACCTTGTGTAGCCGGCAA
657
658 13_HRV56a| GGGAGATGATATTGGACACATTGTAATGCAATACATGTATGTGCCTCCTGGTGCACCACT
659 14_HRV56b| GGGAGATGATATTGGACACATTGTAATGCAATACATGTATGTGCCTCCTGGTGCACCACT
660 15_HRV56   GGGAGATGATATTGGACACATTGTAATGCAATACATGTATGTGCCTCCTGGTGCACCACT
661 GROUP_5    GGGAGATGATATTGGACACATTGTAATGCAATACATGTATGTGCCTCCTGGTGCACCACT
662
663 13_HRV56a| TCCAAACTCAAGAGATGATTTTACATGGCAATCTGGCACCAATGCTTCTGTCTTTTGGCA
664 14_HRV56b| TCCAAACTCAAGAGATGATTTTACATGGCAATCTGGCACCAATGCTTCTGTCTTTTGGCA
665 15_HRV56   TCCAAACTCAAGAGATGATTTTACATGGCAATCTGGCACCAATGCTTCTGTCTTTTGGCA
666 GROUP_5    TCCAAACTCAAGAGATGATTTTACATGGCAATCTGGCACCAATGCTTCTGTCTTTTGGCA
667
668 13_HRV56a| ACATGGCCAAGCTTTCCCCAGATTCTCTCTACCTTTCTTAAGTATTGCTTCTGCTTATTA
669 14_HRV56b| ACATGGCCAAGCTTTCCCCAGATTCTCTCTACCTTTCTTAAGTATTGCTTCTGCTTATTA
670 15_HRV56   ACATGGCCAAGCTTTCCCCAGATTCTCTCTACCTTTCTTAAGTATTGCTTCTGCTTATTA
671 GROUP_5    ACATGGCCAAGCTTTCCCCAGATTCTCTCTACCTTTCTTAAGTATTGCTTCTGCTTATTA
672
673 13_HRV56a| CATGTTTTATGATGGTTATGATGGAGACACTTCAAGCTCCAGATATGGTACATCAGTTAC
674 14_HRV56b| CATGTTTTATGATGGTTATGATGGAGACACTTCAAGCTCCAGATATGGTACATCAGTTAC
675 15_HRV56   CATGTTTTATGATGGTTATGATGGAGACACTTCAAGCTCCAGATATGGTACATCAGTTAC
676 GROUP_5    CATGTTTTATGATGGTTATGATGGAGACACTTCAAGCTCCAGATATGGTACATCAGTTAC
677
678 13_HRV56a| AAACCACATGGGGACACTCTGTTCAAGAATTGTGACAAATAAACAACTTCATCCTGTTGA
679 14_HRV56b| AAACCACATGGGGACACTCTGTTCAAGAATTGTGACAAATAAACAACTTCATCCTGTTGA
680 15_HRV56   AAACCACATGGGGACACTCTGTTCAAGAATTGTGACAAATAAACAACTTCATCCTGTTGA
681 GROUP_5    AAACCACATGGGGACACTCTGTTCAAGAATTGTGACAAATAAACAACTTCATCCTGTTGA
682
683 13_HRV56a| AGTCACAACTCGTGTATATCATAAGGCAAAGCATATTCGAGCATGGTGTCCTAGAGCACC
684 14_HRV56b| AGTCACAACTCGTGTATATCATAAGGCAAAGCATATTCGAGCATGGTGTCCTAGAGCACC
685 15_HRV56   AGTCACAACTCGTGTATATCATAAGGCAAAGCATATTCGAGCATGGTGTCCTAGAGCACC
686 GROUP_5    AGTCACAACTCGTGTATATCATAAGGCAAAGCATATTCGAGCATGGTGTCCTAGAGCACC
687
688 13_HRV56a| AAGGGCTGTGCCTTATACA-CATGCTCACGTCACCAATTATAAAC-CACAAG---ATGGT
689 14_HRV56b| AAGGGCTGTGCCTTATACA-CATGCTCACGTCACCAATTATAAAC-CACAAG---ATGGT
690 15_HRV56   AAGGGCTGTGCCTTATACA-CATGCTCACGTCACCAATTATAAAC-CACAAG---ATGGT
691 GROUP_5    AAGGGCTGTGCCTTATACA.CATGCTCACGTCACCAATTATAAAC.CACAAG...ATGGT
692
693 13_HRV56a| GATG------TACAGATCT---TCTTAAAACCCAGAC------CCAGCCTAACAACAT--
694 14_HRV56b| GATG------TACAGATCT---TCTTAAAACCCAGAC------CCAGCCTAACAACAT--
695 15_HRV56   GATG------TACAGATCT---TCTTAAAACCCAGAC------CCAGCCTAACAACAT--
696 GROUP_5    GATG......TACAGATCT...TCTTAAAACCCAGAC......CCAGCCTAACAACAT..
697
698 13_HRV56a| ----TA---------------
699 14_HRV56b| ----TG---------------
700 15_HRV56   ----TT---------------
701 GROUP_5    ....T................
702
703
704
705 Group 6:
706
707 18_HRV59a| AACCCAGTGGAAAACTATGTTAATGATGTACTTAATGAGGTTTTAGTAGTACCAAATATA
708 19_HRV59b| AACCCAGTGGAAAACTATGTTAATGATGTACTTAATGAGGTTTTAGTAGTACCAAATATA
```

FIG. D14 CONT'D

```
10.trace                                                                9/20/2007 5:05 PM 709  20_HRV59     AACCCAGTGGAAAACTATGTTAATGATGTACTTAATGAGGTTTTAGTAGTACCAAATATA
710  GROUP_6      AACCCAGTGGAAAACTATGTTAATGATGTACTTAATGAGGTTTTAGTAGTACCAAATATA
711
712  18_HRV59a|   CAGGAAAGCCACCCAACCACCTCAAATGCTGCTCCAGCATTAGATGCAGCAGAGACTGGA
713  19_HRV59b|   CAGGAAAGCCACCCAACCACCTCAAATGCTGCTCCAGCATTAGATGCAGCAGAGACTGGA
714  20_HRV59     CAGGAAAGCCACCCAACCACCTCAAATGCTGCTCCAGCATTAGATGCAGCAGAGACTGGA
715  GROUP_6      CAGGAAAGCCACCCAACCACCTCAAATGCTGCTCCAGCATTAGATGCAGCAGAGACTGGA
716
717  18_HRV59a|   CATACAAGCAGTATACAACCTGAGGATACCATAGAAACAAGATATGTTCAGACATCACAA
718  19_HRV59b|   CATACAAGCAGTATACAACCTGAGGATACCATAGAAACAAGATATGTTCAGACATCACAA
719  20_HRV59     CATACAAGCAGTATACAACCTGAGGATACCATAGAAACAAGATATGTTCAGACATCACAA
720  GROUP_6      CATACAAGCAGTATACAACCTGAGGATACCATAGAAACAAGATATGTTCAGACATCACAA
721
722  18_HRV59a|   ACTAGAGATGAGATGAGTGTAGAAAGTTTCTTAGGTAGATCTGGGTGTATACATATTTCA
723  19_HRV59b|   ACTAGAGATGAGATGAGTGTAGAAAGTTTCTTAGGTAGATCTGGGTGTATACATATTTCA
724  20_HRV59     ACTAGAGATGAGATGAGTGTAGAAAGTTTCTTAGGTAGATCTGGGTGTATACATATTTCA
725  GROUP_6      ACTAGAGATGAGATGAGTGTAGAAAGTTTCTTAGGTAGATCTGGGTGTATACATATTTCA
726
727  18_HRV59a|   ACTATTACTGTCAATAAAGACATA---------------AAATATG------ATGATGGA
728  19_HRV59b|   ACTATTACTGTCAATAAAGACATA---------------AAATATG------ATGATGGA
729  20_HRV59     ACTATTACTGTCAATAAAGACATA---------------AAATATG------ATGATGGA
730  GROUP_6      ACTATTACTGTCAATAAAGACATA...............AAATATG......ATGATGGA
731
732  18_HRV59a|   CACTTTCTTAAATGGCCTATAACATTACAAGAGATGGCACAAATTAGGAGAAAATTTGAA
733  19_HRV59b|   CACTTTCTTAAATGGCCTATAACATTACAAGAGATGGCACAAATTAGGAGAAAATTTGAA
734  20_HRV59     CACTTTCTTAAATGGCCTATAACATTACAAGAGATGGCACAAATTAGGAGAAAATTTGAA
735  GROUP_6      CACTTTCTTAAATGGCTATAACATTACAAGAGATGGCACAAATTAGGAGAAAATTTGAA
736
737  18_HRV59a|   TTCTTCACATATGTTAGATTTGACTCAGAAATCACTTTGG-TGCCTTGCATAGCTGGAAA
738  19_HRV59b|   TTCTTCACATATGTTAGATTTGACTCAGAAATCACTTTGG-TGCCTTGCATAGCTGGAAA
739  20_HRV59     TTCTTCACATATGTTAGATTTGACTCAGAAATCACTTTGG-TGCCTTGCATAGCTGGAAA
740  GROUP_6      TTCTTCACATATGTTAGATTTGACTCAGAAATCACTTTGG.TGCCTTGCATAGCTGGAAA
741
742  18_HRV59a|   AGGGGATGACATTGGTCATATAGTCATGCAATATATGTATGTTCCACCAGGTGCTCCACT
743  19_HRV59b|   AGGGGATGACATTGGTCATATAGTCATGCAATATATGTATGTTCCACCAGGTGCTCCACT
744  20_HRV59     AGGGGATGACATTGGTCATATAGTCATGCAATATATGTATGTTCCACCAGGTGCTCCACT
745  GROUP_6      AGGGGATGACATTGGTCATATAGTCATGCAATATATGTATGTTCCACCAGGTGCTCCACT
746
747  18_HRV59a|   GCCCACAAAGAGAGATGATTACACATGGCAATCTGGTACTAATGCTTCAATATTCTGGCA
748  19_HRV59b|   GCCCACAAAGAGAGATGATTACACATGGCAATCTGGTACTAATGCTTCAATATTCTGGCA
749  20_HRV59     GCCCACAAAGAGAGATGATTACACATGGCAATCTGGTACTAATGCTTCAATATTCTGGCA
750  GROUP_6      GCCCACAAAGAGAGATGATTACACATGGCAATCTGGTACTAATGCTTCAATATTCTGGCA
751
752  18_HRV59a|   ACATGGACAAACATTCCCAAGATTTTCATTGCCCTTCCTGAGCATAGCATCAGCTTATTA
753  19_HRV59b|   ACATGGACAAACATTCCCAAGATTTTCATTGCCCTTCCTGAGCATAGCATCAGCTTATTA
754  20_HRV59     ACATGGACAAACATTCCCAAGATTTTCATTGCCCTTCCTGAGCATAGCATCAGCTTATTA
755  GROUP_6      ACATGGACAAACATTCCCAAGATTTTCATTGCCCTTCCTGAGCATAGCATCAGCTTATTA
756
757  18_HRV59a|   CATGTTTTATGATGGTTATGATGGAGATAAATCTGAATCTAGGTATGGTGTGTCTGTAAC
758  19_HRV59b|   CATGTTTTATGATGGTTATGATGGAGATAAATCTGAATCTAGGTATGGTGTGTCTGTAAC
759  20_HRV59     CATGTTTTATGATGGTTATGATGGAGATAAATCTGAATCTAGGTATGGTGTGTCTGTAAC
760  GROUP_6      CATGTTTTATGATGGTTATGATGGAGATAAATCTGAATCTAGGTATGGTGTGTCTGTAAC
761
762  18_HRV59a|   CAACCACATGGGCACTTTATGTTCTAGAATAGTTACAAACAGTCAGGAGCATCCAGTGGA
763  19_HRV59b|   CAACCACATGGGCACTTTATGTTCTAGAATAGTTACAAACAGTCAGGAGCATCCAGTGGA
764  20_HRV59     CAACCACATGGGCACTTTATGTTCTAGAATAGTTACAAACAGTCAGGAGCATCCAGTGGA
765  GROUP_6      CAACCACATGGGCACTTTATGTTCTAGAATAGTTACAAACAGTCAGGAGCATCCAGTGGA
766
767  18_HRV59a|   GGTTGTCACACGTGTGTATCACAAAGCTAAACACGTCAAAGCCTGGTGCCCTAGAGCTCC
768  19_HRV59b|   GGTTGTCACACGTGTGTATCACAAAGCTAAACACGTCAAAGCCTGGTGCCCTAGAGCTCC
769  20_HRV59     GGTTGTCACACGTGTGTATCACAAAGCTAAACACGTCAAAGCCTGGTGCCCTAGAGCTCC
770  GROUP_6      GGTTGTCACACGTGTGTATCACAAAGCTAAACACGTCAAAGCCTGGTGCCCTAGAGCTCC
771
772  18_HRV59a|   TAGAGCAGTCCCTTACACA-CACAGCTACGTAACTAACTACAAGATTGCTGG---AAAA-
773  19_HRV59b|   TAGAGCAGTCCCTTACACA-CACAGCTACGTAACTAACTACAAGATTGCTGG---AAAA-
```

FIG. D14 CONT'D

```
10.trace                                                                                    9/20/2007 5:05 PM 774  20_HRV59    TAGAGCAGTCCCTTACACA-CACAGCTACGTAACTAACTACAAGATTGCTGG---AAAA
775  GROUP_6    TAGAGCAGTCCCTTACACA.CACAGCTACGTAACTAACTACAAGATTGCTGG...AAAA.
776
777  18_HRV59a|  GAAC------CTGAAATTT---TCTTAAAACCAAGAA------TGAATATTACAACAG--
778  19_HRV59b|  GAAC------CTGAAATTT---TCTTAAAACCAAGAA------TGAATATTACAACAG--
779  20_HRV59    GAAC------CTGAAATTT---TCTTAAAACCAAGAA------TGAATATTACAACAG--
780  GROUP_6    GAAC......CTGAAATTT...TCTTAAAACCAAGAA......TGAATATTACAACAG..
781
782  18_HRV59a|  ----CA---------------
783  19_HRV59b|  ----CG---------------
784  20_HRV59    ----CT---------------
785  GROUP_6    ....C-...............
786
787
788
789  Group  7:
790
791  21_HRV63    AATCCAGTAGAGAATTATGTAAATGATGTTCTTAATGAAGTGTTAGTTGTTCCAAACATA
792  22_HRV63b|  AATCCAGTAGAGAATTATGTAAATGATGTTCTTAATGAAGTGTTAGTTGTTCCAAACATA
793  23_HRV63a|  AATCCAGTAGAGAATTATGTAAATGATGTTCTTAATGAAGTGTTAGTTGTTCCAAACATA
794  GROUP_7    AATCCAGTAGAGAATTATGTAAATGATGTTCTTAATGAAGTGTTAGTTGTTCCAAACATA
795
796  21_HRV63    CAAGAAAGCCATCCAACCACATCAAACGCTGCTCCTGTACTTGATGCTGCGGAAACAGGA
797  22_HRV63b|  CAAGAAAGCCATCCAACCACATCAAACGCTGCTCCTGTACTTGATGCTGCGGAAACAGGA
798  23_HRV63a|  CAAGAAAGCCATCCAACCACATCAAACGCTGCTCCTGTACTTGATGCTGCGGAAACAGGA
799  GROUP_7    CAAGAAAGCCATCCAACCACATCAAACGCTGCTCCTGTACTTGATGCTGCGGAAACAGGA
800
801  21_HRV63    CACACAAGCAGTATACAACCTGAGGATACTGTAGAAACTAGATATGTGCAAACGTCTCAA
802  22_HRV63b|  CACACAAGCAGTATACAACCTGAGGATACTGTAGAAACTAGATATGTGCAAACGTCTCAA
803  23_HRV63a|  CACACAAGCAGTATACAACCTGAGGATACTGTAGAAACTAGATATGTGCAAACGTCTCAA
804  GROUP_7    CACACAAGCAGTATACAACCTGAGGATACTGTAGAAACTAGATATGTGCAAACGTCTCAA
805
806  21_HRV63    ACAAGGGATGAAATGAGTGTAGAGAGCTTTCTTGGTAGATCAGGATGCATACACATATCA
807  22_HRV63b|  ACAAGGGATGAAATGAGTGTAGAGAGCTTTCTTGGTAGATCAGGATGCATACACATATCA
808  23_HRV63a|  ACAAGGGATGAAATGAGTGTAGAGAGCTTTCTTGGTAGATCAGGATGCATACACATATCA
809  GROUP_7    ACAAGGGATGAAATGAGTGTAGAGAGCTTTCTTGGTAGATCAGGATGCATACACATATCA
810
811  21_HRV63    ACTATCACTGTTGACAAAACCATT---------------GACTATG------ACACTGGA
812  22_HRV63b|  ACTATCACTGTTGACAAAACCATT---------------GACTATG------ACACTGGA
813  23_HRV63a|  ACTATCACTGTTGACAAAACCATT---------------GACTATG------ACACTGGA
814  GROUP_7    ACTATCACTGTTGACAAAACCATT...............GACTATG......ACACTGGA
815
816  21_HRV63    CATTTTAATAAATGGCAAATAACATTACAAGAGATGGCACAAATTAGAAGGAAATTTGAA
817  22_HRV63b|  CATTTTAATAAATGGCAAATAACATTACAAGAGATGGCACAAATTAGAAGGAAATTTGAA
818  23_HRV63a|  CATTTTAATAAATGGCAAATAACATTACAAGAGATGGCACAAATTAGAAGGAAATTTGAA
819  GROUP_7    CATTTTAATAAATGGCAAATAACATTACAAGAGATGGCACAAATTAGAAGGAAATTTGAA
820
821  21_HRV63    TTCTTCACATATGTCAGATTTGATTCAGAAGTCACTCTTG-TACCATGTATAGCAGGAAA
822  22_HRV63b|  TTCTTCACATATGTCAGATTTGATTCAGAAGTCACTCTTG-TACCATGTATAGCAGGAAA
823  23_HRV63a|  TTCTTCACATATGTCAGATTTGATTCAGAAGTCACTCTTG-TACCATGTATAGCAGGAAA
824  GROUP_7    TTCTTCACATATGTCAGATTTGATTCAGAAGTCACTCTTG.TACCATGTATAGCAGGAAA
825
826  21_HRV63    AGGTGATGACATTGGTCATATAGTTATGCAGTACATGTACGTTCCACCCGGTGCCCCTCT
827  22_HRV63b|  AGGTGATGACATTGGTCATATAGTTATGCAGTACATGTACGTTCCACCCGGTGCCCCTCT
828  23_HRV63a|  AGGTGATGACATTGGTCATATAGTTATGCAGTACATGTACGTTCCACCCGGTGCCCCTCT
829  GROUP_7    AGGTGATGACATTGGTCATATAGTTATGCAGTACATGTACGTTCCACCCGGTGCCCCTCT
830
831  21_HRV63    ACCCACCCGAAGAGAAGATTACACATGGCAATCTGGCACTAATGCTTCAATATTCTGGCA
832  22_HRV63b|  ACCCACCCGAAGAGAAGATTACACATGGCAATCTGGCACTAATGCTTCAATATTCTGGCA
833  23_HRV63a|  ACCCACCCGAAGAGAAGATTACACATGGCAATCTGGCACTAATGCTTCAATATTCTGGCA
834  GROUP_7    ACCCACCCGAAGAGAAGATTACACATGGCAATCTGGCACTAATGCTTCAATATTCTGGCA
835
836  21_HRV63    ACATGGACAAGCTTTTCCAAGGTTTTCTCTACCTTTCTTGAGTATTGCATCAGCATATTA
837  22_HRV63b|  ACATGGACAAGCTTTTCCAAGGTTTTCTCTACCTTTCTTGAGTATTGCATCAGCATATTA
```

FIG. D14 CONT'D

```
10.trace                                                             9/20/2007 5:05 PM 838  23_HRV63a|    ACATGGACAAGCTTTTCCAAGGTTTTCTCTACCTTTCTTGAGTATTGCATCAGCATATTA
839  GROUP_7      ACATGGACAAGCTTTTCCAAGGTTTTCTCTACCTTTCTTGAGTATTGCATCAGCATATTA
840
841  21_HRV63     CATGTTTTATGATGGATATGATGGAGATAAATCAAGCTCTAGGTATGGTGTTTCAGTTAC
842  22_HRV63b|   CATGTTTTATGATGGATATGATGGAGATAAATCAAGCTCTAGGTATGGTGTTTCAGTTAC
843  23_HRV63a|   CATGTTTTATGATGGATATGATGGAGATAAATCAAGCTCTAGGTATGGTGTTTCAGTTAC
844  GROUP_7      CATGTTTTATGATGGATATGATGGAGATAAATCAAGCTCTAGGTATGGTGTTTCAGTTAC
845
846  21_HRV63     TAACCACATGGGGACTTTATGTTCTAGAATTGTAACAAACAGCCAAGAACATCCAGTTGA
847  22_HRV63b|   TAACCACATGGGGACTTTATGTTCTAGAATTGTAACAAACAGCCAAGAACATCCAGTTGA
848  23_HRV63a|   TAACCACATGGGGACTTTATGTTCTAGAATTGTAACAAACAGCCAAGAACATCCAGTTGA
849  GROUP_7      TAACCACATGGGGACTTTATGTTCTAGAATTGTAACAAACAGCCAAGAACATCCAGTTGA
850
851  21_HRV63     GGTGACTACACGTGTATATCATAAAGCTAAACACATCAGAGCCTGGTGCCCAAGAGCTCC
852  22_HRV63b|   GGTGACTACACGTGTATATCATAAAGCTAAACACATCAGAGCCTGGTGCCCAAGAGCTCC
853  23_HRV63a|   GGTGACTACACGTGTATATCATAAAGCTAAACACATCAGAGCCTGGTGCCCAAGAGCTCC
854  GROUP_7      GGTGACTACACGTGTATATCATAAAGCTAAACACATCAGAGCCTGGTGCCCAAGAGCTCC
855
856  21_HRV63     TAGGGCTGTTCCATACACA-CATAGTTATGTCACTAACTATAAAATTACAGG---ACAG-
857  22_HRV63b|   TAGGGCTGTTCCATACACA-CATAGTTATGTCACTAACTATAAAATTACAGG---ACAG-
858  23_HRV63a|   TAGGGCTGTTCCATACACA-CATAGTTATGTCACTAACTATAAAATTACAGG---ACAG
859  GROUP_7      TAGGGCTGTTCCATACACA.CATAGTTATGTCACTAACTATAAAATTACAGG...ACAG.
860
861  21_HRV63     GAGA------CTGAAATTT---TCTTAAAACCTAGAG------CAACTATCAAGACAG--
862  22_HRV63b|   GAGA------CTGAAATTT---TCTTAAAACCTAGAG------CAACTATCAAGACAG--
863  23_HRV63a|   GAGA------CTGAAATTT---TCTTAAAACCTAGAG------CAACTATCAAGACAG--
864  GROUP_7      GAGA......CTGAAATTT...TCTTAAAACCTAGAG......CAACTATCAAGACAG..
865
866  21_HRV63     ----CA---------------
867  22_HRV63b|   ----CG---------------
868  23_HRV63a|   ----CT---------------
869  GROUP_7      ....C-...............
870
871
872
873  Group 8:
874
875  24_HRV39     AATCCAGTAGAAAATTATATAGATGAAGTATTAAATGAGGTATTAGTTGTTCCTAATATA
876  25_HRV39a|   AATCCAGTAGAAAATTATATAGATGAAGTATTAAATGAGGTATTAGTTGTTCCTAATATA
877  26_HRV39b|   AATCCAGTAGAAAATTATATAGATGGAGTATTAAATGAGGTATTAGTTGTTCCTAATATA
878  GROUP_8      AATCCAGTAGAAAATTATATAGATG-AGTATTAAATGAGGTATTAGTTGTTCCTAATATA
879
880  24_HRV39     AGAGAGAGCCATCCAACTACATCTAATGCAGCTACAGCTTTGGATGCTGCTGAAACTGGA
881  25_HRV39a|   AGAGAGAGCCATCCAACTACATCTAATGCAGCTACAGCTTTGGATGCTGCTGAAACTGGA
882  26_HRV39b|   AGAGAGAGCCATCCAACTACATCTAATGCAGCTCCAGCTTTGGATGCTGCTGAAACTGGA
883  GROUP_8      AGAGAGAGCCATCCAACTACATCTAATGCAGCT-CAGCTTTGGATGCTGCTGAAACTGGA
884
885  24_HRV39     CACACAAGTAGCACCCAGCCTGAAGACACAATTGAAACAAGATATGTGCAAACCTCACAT
886  25_HRV39a|   CACACAAGTAGCACCCAGCCTGAAGACACAATTGAAACAAGATATGTGCAAACCTCACAT
887  26_HRV39b|   CACACAAGTAGCATCCAACCTGAAGACACAATTGAAACAAGATATGTGCAAACCTCACAT
888  GROUP_8      CACACAAGTAGCA-CCA-CCTGAAGACACAATTGAAACAAGATATGTGCAAACCTCACAT
889
890  24_HRV39     ACTAGGGATGAAATGAGCGTTGAAAGTTTCTTAGGCAGATCTGGCTGTATTCACATTTCC
891  25_HRV39a|   ACTAGGGATGAAATGAGCGTTGAAAGTTTCTTAGGCAGATCTGGCTGTATTCACATTTCC
892  26_HRV39b|   ACTAGGGATGAAATGAGTGTTGAAAGTTTCTTAGGCAGATCTGGCTGTATTCACATTTCC
893  GROUP_8      ACTAGGGATGAAATGAG-GTTGAAAGTTTCTTAGGCAGATCTGGCTGTATTCACATTTCC
894
895  24_HRV39     ACAATTACTATGAAGAAGGAG----------------AACTATA------ATGATCAT
896  25_HRV39a|   ACAATTACTATGAAGAAGGAG----------------AACTATA------ATGATCAT
897  26_HRV39b|   ACAATTACTATGAAGAAGGAG----------------AACTATA------ATGAACAT
898  GROUP_8      ACAATTACTATGAAGAAGGAG................AACTATA......ATGA-CAT
899
900  24_HRV39     AATTTTGTGGATTGGAAAATTACTTTGCAGGAGATGGCACAGGTTAGAAGGAAATTTGAA
901  25_HRV39a|   AATTTTGTGGATTGGAAAATTACTTTGCAGGAGATGGCACAGGTTAGAAGGAAATTTGAA
902  26_HRV39b|   AATTTTGTGGATTGGAAAATTACTTTGCAGGAGATGGCACAGGTTAGAAGGAAATTTGAA
```

FIG. D14 CONT'D

10.trace                                                                                9/20/2007 5:05 PM

```
903 GROUP_8      AATTTTGTGGATTGGAAAATTACTTTGCAGGAGATGGCACAGGTTAGAAGGAAATTTGAA
904
905 24_HRV39     ATGTTCACCTATGTTAGATTTGACTCAGAGATTACTTTAG-TCCCATGCATAGCTGGAAG
906 25_HRV39a|   ATGTTCACCTATGTTAGATTTGACTCAGAGATTACTTTAG-TCCCATGCATAGCTGGAAG
907 26_HRV39b|   ATGTTCACCTACGTTAGATTTGACTCAGAGATTACTTTAG-TCCCATGCATAGCTGGAAG
908 GROUP_8      ATGTTCACCTA-GTTAGATTTGACTCAGAGATTACTTTAG.TCCCATGCATAGCTGGAAG
909
910 24_HRV39     AGGTGAAGATATTGGACACATAGTAATGCAATACATGTATGTCCCACCTGGTGCACCTGT
911 25_HRV39a|   AGGTGAAGATATTGGACACATAGTAATGCAATACATGTATGTCCCACCTGGTGCACCTGT
912 26_HRV39b|   AGGTGAAGATATTGGACACATAGTAATGCAATACATGTATGTCCCACCCGGTGCACCTGT
913 GROUP_8      AGGTGAAGATATTGGACACATAGTAATGCAATACATGTATGTCCCACC-GGTGCACCTGT
914
915 24_HRV39     ACCTAAGAAGAGAGATGATTACACATGGCAATCTGGAACAAATGCCTCAGTTTTCTGGCA
916 25_HRV39a|   ACCTAAGAAGAGAGATGATTACACATGGCAATCTGGAACAAATGCCTCAGTTTTCTGGCA
917 26_HRV39b|   ACCTAAGAAGAGAGATGATTACACATGGCAATCTGGAACAAATGCCTCAGTTTTCTGGCA
918 GROUP_8      ACCTAAGAAGAGAGATGATTACACATGGCAATCTGGAACAAATGCCTCAGTTTTCTGGCA
919
920 24_HRV39     ACACGGACAGCCTTACCCTAGATTTTCATTACCATTTCTAAGCATAGCCTCAGCATATTA
921 25_HRV39a|   ACACGGACAGCCTTACCCTAGATTTTCATTACCATTTCTAAGCATAGCCTCAGCATATTA
922 26_HRV39b|   ACACGGACAGCCTTACCCTAGATTTTCATTACCATTTCTAAGCATAGCCTCAGCATATTA
923 GROUP_8      ACACGGACAGCCTTACCCTAGATTTTCATTACCATTTCTAAGCATAGCCTCAGCATATTA
924
925 24_HRV39     TATGTTCTATGATGGATATGATGGTGATAAATCGTCATCTAGGTATGGTGTTTCTGTCAC
926 25_HRV39a|   TATGTTCTATGATGGATATGATGGTGATAAATCGTCATCTAGGTATGGTGTTTCTGTCAC
927 26_HRV39b|   TATGTTCTATGATGGATATGATGGTGATAAATCGTCATCTAGGTATGGTGTTTCTGTCAC
928 GROUP_8      TATGTTCTATGATGGATATGATGGTGATAAATCGTCATCTAGGTATGGTGTTTCTGTCAC
929
930 24_HRV39     TAATGATATGGGTACACTTTGCACTAGAATTGTAACAAACCAACAGGAACACCTAGTGGA
931 25_HRV39a|   TAATGATATGGGTACACTTTGCACTAGAATTGTAACAAACCAACAGGAACACCTAGTGGA
932 26_HRV39b|   TAATGATATGGGTACACTTTGCACTAGAATTGTAACAAACCAACAGAAACACCTAGTGGA
933 GROUP_8      TAATGATATGGGTACACTTTGCACTAGAATTGTAACAAACCAACAG-AACACCTAGTGGA
934
935 24_HRV39     GGTTACAACCAGAGTTTACCATAAAGCCAAGCATGTTAAAGCATGGTGCCCTAGGGCTCC
936 25_HRV39a|   GGTTACAACCAGAGTTTACCATAAAGCCAAGCATGTTAAAGCATGGTGCCCTAGGGCTCC
937 26_HRV39b|   GGTTACAACCAGAGTTTACCATAAAGCCAAGCATGTTAAAGCATGGTGCCCTAGGGCTCC
938 GROUP_8      GGTTACAACCAGAGTTTACCATAAAGCCAAGCATGTTAAAGCATGGTGCCCTAGGGCTCC
939
940 24_HRV39     CAGAGCAGTCCCTTACACA-CACAGCAATGTTACAAATTACAAAG-TACGGG---ACGGT
941 25_HRV39a|   CAGAGCAGTCCCTTACACA-CACAGCAATGTTACAAATTACAAAG-TACGGG---ACGGT
942 26_HRV39b|   CAGAGCAGTCCCTTACACA-CACAGCAATGTTACAAATTACAAAG-TACGGG---ACGGT
943 GROUP_8      CAGAGCAGTCCCTTACACA.CACAGCAATGTTACAAATTACAAAG.TACGGG...ACGGT
944
945 24_HRV39     GAAC------CAACACTCT---TTATAAAATCAAGAG------AGAATCTTACCACAG--
946 25_HRV39a|   GAAC------CAACACTCT---TTATAAAATCAAGAG------AGAATCTTACCACAG--
947 26_HRV39b|   GAAC------CAACACTCT---TTATAAAACCAAGAG------AGAATCTTACCACAG--
948 GROUP_8      GAAC......CAACACTCT...TTATAAAA-CAAGAG......AGAATCTTACCACAG..
949
950 24_HRV39     ----CT---------------
951 25_HRV39a|   ----CA---------------
952 26_HRV39b|   ----CT---------------
953 GROUP_8      ....C-...............
954
955
956
957 Group 9:
958
959 27_HRV10a|   AATCCAGTTGAAAATTACATTGATAATGTACTTAATGAAGTCCTAGTGGTACCCAACATC
960 28_HRV10b|   AATCCAGTTGAAAATTACATTGATAATGTACTTAATGAAGTCCTAGTGGTACCCAACATC
961 29_HRV10     AATCCAGTTGAAAATTACATTGATAATGTACTTAATGAAGTCCTAGTGGTACCCAACATC
962 GROUP_9      AATCCAGTTGAAAATTACATTGATAATGTACTTAATGAAGTCCTAGTGGTACCCAACATC
963
964 27_HRV10a|   AGAGAAAGTCATCCAAGCACCTCTAACTCTGCCCCAATTCTCGATGCAGCTGAGACTGGT
965 28_HRV10b|   AGAGAAAGTCATCCAAGCACCTCTAACTCTGCCCCAATTCTCGATGCAGCTGAGACTGGT
966 29_HRV10     AGAGAAAGTCATCCAAGCACCTCTAACTCTGCCCCAATTCTCGATGCAGCTGAGACTGGT
967 GROUP_9      AGAGAAAGTCATCCAAGCACCTCTAACTCTGCCCCAATTCTCGATGCAGCTGAGACTGGT
```

FIG. D14 CONT'D

```
10.trace                                                                    9/20/2007 5:05 PM
 968
 969  27_HRV10a|    CATACCAGTAGTGTACAACCAGAAGATACGGTTGAAACACGATATGTGCAAACATCCCAG
 970  28_HRV10b|    CATACCAGTAGTGTACAACCAGAAGATACGGTTGAAACACGATATGTGCAAACATCCCAG
 971  29_HRV10     CATACCAGTAGTGTACAACCAGAAGATACGGTTGAAACACGATATGTGCAAACATCCCAG
 972  GROUP_9      CATACCAGTAGTGTACAACCAGAAGATACGGTTGAAACACGATATGTGCAAACATCCCAG
 973
 974  27_HRV10a|    ACGAGAGATGAAATGAGTATTGAAAGTTTTCTTGGCAGGTCAGGTTGTATACACACCTCA
 975  28_HRV10b|    ACGAGAGATGAAATGAGTATTGAAAGTTTTCTTGGCAGGTCAGGTTGTATACACACCTCA
 976  29_HRV10     ACGAGAGATGAAATGAGTATTGAAAGTTTTCTTGGCAGGTCAGGTTGTATACACACCTCA
 977  GROUP_9      ACGAGAGATGAAATGAGTATTGAAAGTTTTCTTGGCAGGTCAGGTTGTATACACACCTCA
 978
 979  27_HRV10a|    ACAATAACTGTTAATAATACAAGA---------------CCCTACA------ATGAACAC
 980  28_HRV10b|    ACAATAACTGTTAATAATACAAGA---------------CCCTACA------ATGAACAC
 981  29_HRV10     ACAATAACTGTTAATAATACAAGA---------------CCCTACA------ATGAACAC
 982  GROUP_9      ACAATAACTGTTAATAATACAAGA...............CCCTACA......ATGAACAC
 983
 984  27_HRV10a|    ACTTTTGACACATGGCAAATAACTCTACAAGAAATGGCCCAAATTAGAAGGAAATTTGAA
 985  28_HRV10b|    ACTTTTGACACATGGCAAATAACTCTACAAGAAATGGCCCAAATTAGAAGGAAATTTGAA
 986  29_HRV10     ACTTTTGACACATGGCAAATAACTCTACAAGAAATGGCCCAAATTAGAAGGAAATTTGAA
 987  GROUP_9      ACTTTTGACACATGGCAAATAACTCTACAAGAAATGGCCCAAATTAGAAGGAAATTTGAA
 988
 989  27_HRV10a|    ATGTTTACATATGTTAGATTTGACTCAGAAGTCACTTTAG-TACCTTGCATCGCAGGCAA
 990  28_HRV10b|    ATGTTTACATATGTTAGATTTGACTCAGAAGTCACTTTAG-TACCTTGCATCGCAGGCAA
 991  29_HRV10     ATGTTTACATATGTTAGATTTGACTCAGAAGTCACTTTAG-TACCTTGCATCGCAGGCAA
 992  GROUP_9      ATGTTTACATATGTTAGATTTGACTCAGAAGTCACTTTAG.TACCTTGCATCGCAGGCAA
 993
 994  27_HRV10a|    GGGCGATGACATAGGTCACATAGTTATGCAATATATGTATGTGCCACCTGGGGCTCCAGT
 995  28_HRV10b|    GGGCGATGACATAGGTCACATAGTTATGCAATATATGTATGTGCCACCTGGGGCTCCAGT
 996  29_HRV10     GGGCGATGACATAGGTCACATAGTTATGCAATATATGTATGTGCCACCTGGGGCTCCAGT
 997  GROUP_9      GGGCGATGACATAGGTCACATAGTTATGCAATATATGTATGTGCCACCTGGGGCTCCAGT
 998
 999  27_HRV10a|    ACCAACTAAGAGAGATGATTTTGCTTGGCAGTCGGGAACAAATGCATCAGTCTTCTGGCA
1000  28_HRV10b|    ACCAACTAAGAGAGATGATTTTGCTTGGCAGTCGGGAACAAATGCATCAGTCTTCTGGCA
1001  29_HRV10     ACCAACTAAGAGAGATGATTTTGCTTGGCAGTCGGGAACAAATGCATCAGTCTTCTGGCA
1002  GROUP_9      ACCAACTAAGAGAGATGATTTTGCTTGGCAGTCGGGAACAAATGCATCAGTCTTCTGGCA
1003
1004  27_HRV10a|    ACATGGACAACCTTTCCCTAGATTTTCTTTACCCTTCTTAAGCATTGCATCTGCTTACTA
1005  28_HRV10b|    ACATGGACAACCTTTCCCTAGATTTTCTTTACCCTTCTTAAGCATTGCATCTGCTTACTA
1006  29_HRV10     ACATGGACAACCTTTCCCTAGATTTTCTTTACCCTTCTTAAGCATTGCATCTGCTTACTA
1007  GROUP_9      ACATGGACAACCTTTCCCTAGATTTTCTTTACCCTTCTTAAGCATTGCATCTGCTTACTA
1008
1009  27_HRV10a|    CATGTTCTATGATGGTTATGATGGTGATACACATGACTCACGTTATGGCACAACAGTGAT
1010  28_HRV10b|    CATGTTCTATGATGGTTATGATGGTGATACACATGACTCACGTTATGGCACAACAGTGAT
1011  29_HRV10     CATGTTCTATGATGGTTATGATGGTGATACACATGACTCACGTTATGGCACAACAGTGAT
1012  GROUP_9      CATGTTCTATGATGGTTATGATGGTGATACACATGACTCACGTTATGGCACAACAGTGAT
1013
1014  27_HRV10a|    AAATCACATGGGCACTTTGTGCATGCGAATAGTCACAAACCAGCAAGCACATGAGGTGGA
1015  28_HRV10b|    AAATCACATGGGCACTTTGTGCATGCGAATAGTCACAAACCAGCAAGCACATGAGGTGGA
1016  29_HRV10     AAATCACATGGGCACTTTGTGCATGCGAATAGTCACAAACCAGCAAGCACATGAGGTGGA
1017  GROUP_9      AAATCACATGGGCACTTTGTGCATGCGAATAGTCACAAACCAGCAAGCACATGAGGTGGA
1018
1019  27_HRV10a|    AATTACCACCAGTGTTTATCACAAAGCCAAGCATGTCAAAGCATGGTGTCCAAGACCACC
1020  28_HRV10b|    AATTACCACCAGTGTTTATCACAAAGCCAAGCATGTCAAAGCATGGTGTCCAAGACCACC
1021  29_HRV10     AATTACCACCAGTGTTTATCACAAAGCCAAGCATGTCAAAGCATGGTGTCCAAGACCACC
1022  GROUP_9      AATTACCACCAGTGTTTATCACAAAGCCAAGCATGTCAAAGCATGGTGTCCAAGACCACC
1023
1024  27_HRV10a|    CAGAGCTGTACCATATACA-CATGCCCATTCCACAAATTACAAAC-CACATG---GCAAA
1025  28_HRV10b|    CAGAGCTGTACCATATACA-CATGCCCATTCCACAAATTACAAAC-CACATG---GCAAA
1026  29_HRV10     CAGAGCTGTACCATATACA-CATGCCCATTCCACAAATTACAAAC-CACATG---GCAAA
1027  GROUP_9      CAGAGCTGTACCATATACA.CATGCCCATTCCACAAATTACAAAC.CACATG...GCAAA
1028
1029  27_HRV10a|    GAAT------TACAAATAT---TTATTAGGTCTAGAGATGATCCCAAAGTAGTAACTG--
1030  28_HRV10b|    GAAT------TACAAATAT---TTATTAGGTCTAGAGATGATCCCAAAGTAGTAACTG--
1031  29_HRV10     GAAT------TACAAATAT---TTATTAGGTCTAGAGATGATCCCAAAGTAGTAACTG--
1032  GROUP_9      GAAT......TACAAATAT...TTATTAGGTCTAGAGATGATCCCAAAGTAGTAACTG..
```

FIG. D14 CONT'D

```
10.trace                                                          9/20/2007 5:05 PM
1033
1034  27_HRV10a|     ----CA---------------
1035  28_HRV10b|     ----CC---------------
1036  29_HRV10       ----CT---------------
1037  GROUP_9        ....C-...............
1038
1039
1040
1041  Group 10:
1042
1043  30_HRV100a     AATCCAGTAGAAAATTATGTTGAAGGTGTGCTGAATGAAGTACTAGTGGTACCTAATATT
1044  31_HRV100b     AATCCAGTAGAAAATTATGTTGAAGGTGTGCTGAATGAAGTACTAGTGGTACCTAATATT
1045  32_HRV100      AATCCAGTAGAAAATTATGTTGAAGGTGTGCTGAATGAAGTACTAGTGGTACCTAATATT
1046  GROUP_10       AATCCAGTAGAAAATTATGTTGAAGGTGTGCTGAATGAAGTACTAGTGGTACCTAATATT
1047
1048  30_HRV100a     AGAGAGAGCCATCCAAGCACCTCAAACTCTGCTCCAATCCTTGATGCTGCTGAAACTGGC
1049  31_HRV100b     AGAGAGAGCCATCCAAGCACCTCAAACTCTGCTCCAATCCTTGATGCTGCTGAAACTGGC
1050  32_HRV100      AGAGAGAGCCATCCAAGCACCTCAAACTCTGCTCCAATCCTTGATGCTGCTGAAACTGGC
1051  GROUP_10       AGAGAGAGCCATCCAAGCACCTCAAACTCTGCTCCAATCCTTGATGCTGCTGAAACTGGC
1052
1053  30_HRV100a     CACACTAGTAATGTGCAACCTGAAGATACAGTTGAAACTCGATATGTGCAGACATCACAG
1054  31_HRV100b     CACACTAGTAATGTGCAACCTGAAGATACAGTTGAAACTCGATATGTGCAGACATCACAG
1055  32_HRV100      CACACTAGTAATGTGCAACCTGAAGATACAGTTGAAACTCGATATGTGCAGACATCACAG
1056  GROUP_10       CACACTAGTAATGTGCAACCTGAAGATACAGTTGAAACTCGATATGTGCAGACATCACAG
1057
1058  30_HRV100a     ACCAGGGATGAAATGAGTATTGAGAGCTTTCTTGGAAGATCTGGTTGTATACACACCTCA
1059  31_HRV100b     ACCAGGGATGAAATGAGTATTGAGAGCTTTCTTGGAAGATCTGGTTGTATACACACCTCA
1060  32_HRV100      ACCAGGGATGAAATGAGTATTGAGAGCTTTCTTGGAAGATCTGGTTGTATACACACCTCA
1061  GROUP_10       ACCAGGGATGAAATGAGTATTGAGAGCTTTCTTGGAAGATCTGGTTGTATACACACCTCA
1062
1063  30_HRV100a     ACAATTACTGTAAGTAAAATGAAA---------------AATTATA------ATGAGCAC
1064  31_HRV100b     ACAATTACTGTAAGTAAAATGAAA---------------AATTATA------ATGAGCAC
1065  32_HRV100      ACAATTACTGTAAGTAAAATGAAA---------------AATTATA------ATGAGCAC
1066  GROUP_10       ACAATTACTGTAAGTAAAATGAAA...............AATTATA......ATGAGCAC
1067
1068  30_HRV100a     ACTTTTGACAAATGGCAAATAACCCTACAGGAAATGGCCCAAATTAGAAGGAAATTTGAA
1069  31_HRV100b     ACTTTTGACAAATGGCAAATAACCCTACAGGAAATGGCCCAAATTAGAAGGAAATTTGAA
1070  32_HRV100      ACTTTTGACAAATGGCAAATAACCCTACAGGAAATGGCCCAAATTAGAAGGAAATTTGAA
1071  GROUP_10       ACTTTTGACAAATGGCAAATAACCCTACAGGAAATGGCCCAAATTAGAAGGAAATTTGAA
1072
1073  30_HRV100a     ATGTTTACATATGTCAGATTTGACTCAGAAATCACATTGG-TACCCTGTATTGCAGGAAA
1074  31_HRV100b     ATGTTTACATATGTCAGATTTGACTCAGAAATCACATTGG-TACCCTGTATTGCAGGAAA
1075  32_HRV100      ATGTTTACATATGTCAGATTTGACTCAGAAATCACATTGG-TACCCTGTATTGCAGGAAA
1076  GROUP_10       ATGTTTACATATGTCAGATTTGACTCAGAAATCACATTGG.TACCCTGTATTGCAGGAAA
1077
1078  30_HRV100a     AGGAGATGACATAGGGCATATCGTAATGCAGTACATGTATGTGCCACCTGGAGCTCCAGT
1079  31_HRV100b     AGGAGATGACATAGGGCATATCGTAATGCAGTACATGTATGTGCCACCTGGAGCTCCAGT
1080  32_HRV100      AGGAGATGACATAGGGCATATCGTAATGCAGTACATGTATGTGCCACCTGGAGCTCCAGT
1081  GROUP_10       AGGAGATGACATAGGGCATATCGTAATGCAGTACATGTATGTGCCACCTGGAGCTCCAGT
1082
1083  30_HRV100a     TCCAACAAAAAGGGATGATTTTGCATGGCAATCAGGCACAAATGCATCAGTTTTTTGGCA
1084  31_HRV100b     TCCAACAAAAAGGGATGATTTTGCATGGCAATCAGGCACAAATGCATCAGTTTTTTGGCA
1085  32_HRV100      TCCAACAAAAAGGGATGATTTTGCATGGCAATCAGGCACAAATGCATCAGTTTTTTGGCA
1086  GROUP_10       TCCAACAAAAAGGGATGATTTTGCATGGCAATCAGGCACAAATGCATCAGTTTTTTGGCA
1087
1088  30_HRV100a     GCATGGGCAGCCATTCCCTAGAATTTCTTTACCTTTCTTGAGCATTGCTTCTGCATACTA
1089  31_HRV100b     GCATGGGCAGCCATTCCCTAGAATTTCTTTACCTTTCTTGAGCATTGCTTCTGCATACTA
1090  32_HRV100      GCATGGGCAGCCATTCCCTAGAATTTCTTTACCTTTCTTGAGCATTGCTTCTGCATACTA
1091  GROUP_10       GCATGGGCAGCCATTCCCTAGAATTTCTTTACCTTTCTTGAGCATTGCTTCTGCATACTA
1092
1093  30_HRV100a     CATGTTTTATGATGGATATGATGGTGATACACATGATTCACACTATGGTACTACTGTAAT
1094  31_HRV100b     CATGTTTTATGATGGATATGATGGTGATACACATGATTCACACTATGGTACTACTGTAAT
1095  32_HRV100      CATGTTTTATGATGGATATGATGGTGATACACATGATTCACACTATGGTACTACTGTAAT
1096  GROUP_10       CATGTTTTATGATGGATATGATGGTGATACACATGATTCACACTATGGTACTACTGTAAT
1097
```

FIG. D14 CONT'D

```
10.trace                                                                       9/20/2007 5:05 PM 1098  30_HRV100a    TAACCACATGGGTACACTTTGTATGAGGATAGTTACAAATCAGCAAGCACATGAGGTGGA
1099  31_HRV100b    TAACCACATGGGTACACTTTGTATGAGGATAGTTACAAATCAGCAAGCACATGAGGTGGA
1100  32_HRV100     TAACCACATGGGTACACTTTGTATGAGGATAGTTACAAATCAGCAAGCACATGAGGTGGA
1101  GROUP_10      TAACCACATGGGTACACTTTGTATGAGGATAGTTACAAATCAGCAAGCACATGAGGTGGA
1102
1103  30_HRV100a    AATTACTACTAATATCTATCACAAGGCCAAACATGTTAAAGCTTGGTGCCCAAGACCACC
1104  31_HRV100b    AATTACTACTAATATCTATCACAAGGCCAAACATGTTAAAGCTTGGTGCCCAAGACCACC
1105  32_HRV100     AATTACTACTAATATCTATCACAAGGCCAAACATGTTAAAGCTTGGTGCCCAAGACCACC
1106  GROUP_10      AATTACTACTAATATCTATCACAAGGCCAAACATGTTAAAGCTTGGTGCCCAAGACCACC
1107
1108  30_HRV100a    TCGGGCTGTGCCGTACACA-CATAGTCACTCTACAAATTACAAAC-CACATG---AGGGT
1109  31_HRV100b    TCGGGCTGTGCCGTACACA-CATAGTCACTCTACAAATTACAAAC-CACATG---AGGGT
1110  32_HRV100     TCGGGCTGTGCCGTACACA-CATAGTCACTCTACAAATTACAAAC-CACATG---AGGGT
1111  GROUP_10      TCGGGCTGTGCCGTACACA.CATAGTCACTCTACAAATTACAAAC.CACATG...AGGGT
1112
1113  30_HRV100a    GATG------TAAAGATTT---TCATTAGACCCAGAGATGATCCAAAGTTTGTAACTG--
1114  31_HRV100b    GATG------TAAAGATTT---TCATTAGACCCAGAGATGATCCAAAGTTTGTAACTG--
1115  32_HRV100     GATG------TAAAGATTT---TCATTAGACCCAGAGATGATCCAAAGTTTGTAACTG--
1116  GROUP_10      GATG......TAAAGATTT...TCATTAGACCCAGAGATGATCCAAAGTTTGTAACTG..
1117
1118  30_HRV100a    ----CA---------------
1119  31_HRV100b    ----CG---------------
1120  32_HRV100     ----CT---------------
1121  GROUP_10      ....C-...............
1122
1123
1124
1125  Group 11:
1126
1127  33_HRV66      AATCCAGTTGAAGATTATGTTGAGGGTGTTTTAAATGAAGTTTTAGTAGTACCAAACATC
1128  34_HRV66b|    AATCCAGTTGAAGATTATGTTGAGGGTGTTTTAAATGAAGTTTTAGTAGTACCAAACATC
1129  35_HRV66a|    AATCCAGTTGAAGATTATGTTGAGGGTGTTTTAAATGAAGTTTTAGTAGTACCAAACATC
1130  GROUP_11      AATCCAGTTGAAGATTATGTTGAGGGTGTTTTAAATGAAGTTTTAGTAGTACCAAACATC
1131
1132  33_HRV66      AAGGAAAGCCATCCAAGCACATCAAATGCTGCCCCAATACTAGATGCAGCTGAAACAGGT
1133  34_HRV66b|    AAGGAAAGCCATCCAAGCACATCAAATGCTGCCCCAATACTAGATGCAGCTGAAACAGGT
1134  35_HRV66a|    AAGGAAAGCCATCCAAGCACATCAAATGCTGCCCCAATACTAGATGCAGCTGAAACAGGT
1135  GROUP_11      AAGGAAAGCCATCCAAGCACATCAAATGCTGCCCCAATACTAGATGCAGCTGAAACAGGT
1136
1137  33_HRV66      CACACTAGTAAAGTACAACCAGAAGATACAGTTGAGACTCGTTACGTGCAAACATCACAG
1138  34_HRV66b|    CACACTAGTAAAGTACAACCAGAAGATACAGTTGAGACTCGTTACGTGCAAACATCACAG
1139  35_HRV66a|    CACACTAGTAAAGTACAACCAGAAGATACAGTTGAGACTCGTTACGTGCAAACATCACAG
1140  GROUP_11      CACACTAGTAAAGTACAACCAGAAGATACAGTTGAGACTCGTTACGTGCAAACATCACAG
1141
1142  33_HRV66      ACTAGAGATGAAATGAGCATAGAAAGTTTTCTAGGTAGGTCAGGATGTATCCATATATCA
1143  34_HRV66b|    ACTAGAGATGAAATGAGCATAGAAAGTTTTCTAGGTAGGTCAGGATGTATCCATATATCA
1144  35_HRV66a|    ACTAGAGATGAAATGAGCATAGAAAGTTTTCTAGGTAGGTCAGGATGTATCCATATATCA
1145  GROUP_11      ACTAGAGATGAAATGAGCATAGAAAGTTTTCTAGGTAGGTCAGGATGTATCCATATATCA
1146
1147  33_HRV66      ACAATTAATGTGGATAGCACAAAA---------------ACATATG------ATGAATCC
1148  34_HRV66b|    ACAATTAATGTGGATAGCACAAAA---------------ACATATG------ATGAATCC
1149  35_HRV66a|    ACAATTAATGTGGATAGCACAAAA---------------ACATATG------ATGAATCC
1150  GROUP_11      ACAATTAATGTGGATAGCACAAAA...............ACATATG......ATGAATCC
1151
1152  33_HRV66      AAATTTAGAACATGGCAAATTACATTGCAAGAAATGGCTCAAATCAGACGCAAATTTGAG
1153  34_HRV66b|    AAATTTAGAACATGGCAAATTACATTGCAAGAAATGGCTCAAATCAGACGCAAATTTGAG
1154  35_HRV66a|    AAATTTAGAACATGGCAAATTACATTGCAAGAAATGGCTCAAATCAGACGCAAATTTGAG
1155  GROUP_11      AAATTTAGAACATGGCAAATTACATTGCAAGAAATGGCTCAAATCAGACGCAAATTTGAG
1156
1157  33_HRV66      ATGTTCACATATGTTAGGTTTGATTCTGAAATTACATTAG-TCCCATGCATTGCAGGAAA
1158  34_HRV66b|    ATGTTCACATATGTTAGGTTTGATTCTGAAATTACATTAG-TCCCATGCATTGCAGGAAA
1159  35_HRV66a|    ATGTTCACATATGTTAGGTTTGATTCTGAAATTACATTAG-TCCCATGCATTGCAGGAAA
1160  GROUP_11      ATGTTCACATATGTTAGGTTTGATTCTGAAATTACATTAG.TCCCATGCATTGCAGGAAA
1161
1162  33_HRV66      GGGTGATGATATAGGACATATTGTGATGCAATACATGTATGTACCACCTGGAGCCCCAAT
```

FIG. D14 CONT'D

```
10.trace                                                                                    9/20/2007 5:05 PM 1163  34_HRV66b|    GGGTGATGATATAGGACATATTGTGATGCAATACATGTATGTACCACCTGGAGCCCCAAT
1164  35_HRV66a|    GGGTGATGATATAGGACATATTGTGATGCAATACATGTATGTACCACCTGGAGCCCCAAT
1165  GROUP_11     GGGTGATGATATAGGACATATTGTGATGCAATACATGTATGTACCACCTGGAGCCCCAAT
1166
1167  33_HRV66     TCCAGATAATAGAACACACTTTGCTTGGCAATCAGGAACAAATGCATCTATATTCTGGCA
1168  34_HRV66b|    TCCAGATAATAGAACACACTTTGCTTGGCAATCAGGAACAAATGCATCTATATTCTGGCA
1169  35_HRV66a|    TCCAGATAATAGAACACACTTTGCTTGGCAATCAGGAACAAATGCATCTATATTCTGGCA
1170  GROUP_11     TCCAGATAATAGAACACACTTTGCTTGGCAATCAGGAACAAATGCATCTATATTCTGGCA
1171
1172  33_HRV66     ACTTGGACAACCATTCCCAAGATTCTCGCTACCTTTTCTAGGCATAGCTTCAGCATATTA
1173  34_HRV66b|    ACTTGGACAACCATTCCCAAGATTCTCGCTACCTTTTCTAGGCATAGCTTCAGCATATTA
1174  35_HRV66a|    ACTTGGACAACCATTCCCAAGATTCTCGCTACCTTTTCTAGGCATAGCTTCAGCATATTA
1175  GROUP_11     ACTTGGACAACCATTCCCAAGATTCTCGCTACCTTTTCTAGGCATAGCTTCAGCATATTA
1176
1177  33_HRV66     CATGTTCTATGATGGTTATGATGGAGATACTCCTGGGTCTCGTTATGGAACCACAGTAGT
1178  34_HRV66b|    CATGTTCTATGATGGTTATGATGGAGATACTCCTGGGTCTCGTTATGGAACCACAGTAGT
1179  35_HRV66a|    CATGTTCTATGATGGTTATGATGGAGATACTCCTGGGTCTCGTTATGGAACCACAGTAGT
1180  GROUP_11     CATGTTCTATGATGGTTATGATGGAGATACTCCTGGGTCTCGTTATGGAACCACAGTAGT
1181
1182  33_HRV66     TAATCATATGGGTACATTATGTATTAGGATTGTTACAAATGAACAGCACCATAATGTTGA
1183  34_HRV66b|    TAATCATATGGGTACATTATGTATTAGGATTGTTACAAATGAACAGCACCATAATGTTGA
1184  35_HRV66a|    TAATCATATGGGTACATTATGTATTAGGATTGTTACAAATGAACAGCACCATAATGTTGA
1185  GROUP_11     TAATCATATGGGTACATTATGTATTAGGATTGTTACAAATGAACAGCACCATAATGTTGA
1186
1187  33_HRV66     AATTACTACTAGAGTATACCATAAGGCTAAGCATGTTAAAGCCTGGTGTCCTAGACCACT
1188  34_HRV66b|    AATTACTACTAGAGTATACCATAAGGCTAAGCATGTTAAAGCCTGGTGTCCTAGACCACT
1189  35_HRV66a|    AATTACTACTAGAGTATACCATAAGGCTAAGCATGTTAAAGCCTGGTGTCCTAGACCACT
1190  GROUP_11     AATTACTACTAGAGTATACCATAAGGCTAAGCATGTTAAAGCCTGGTGTCCTAGACCACT
1191
1192  33_HRV66     TAGAGCTGTACCATACACA-ACTGTAAACTCAACCAATTATATGC-CTCATA---CTGGT
1193  34_HRV66b|    TAGAGCTGTACCATACACA-ACTGTAAACTCAACCAATTATATGC-CTCATA---CTGGT
1194  35_HRV66a|    TAGAGCTGTACCATACACA-ACTGTAAACTCAACCAATTATATGC-CTCATA---CTGGT
1195  GROUP_11     TAGAGCTGTACCATACACA.ACTGTAAACTCAACCAATTATATGC.CTCATA...CTGGT
1196
1197  33_HRV66     GATC------TGCAAATTT---TCATTAAACCTAGAACAGATCCAAAAGTAGTCAATG--
1198  34_HRV66b|    GATC------TGCAAATTT---TCATTAAACCTAGAACAGATCCAAAAGTAGTCAATG--
1199  35_HRV66a|    GATC------TGCAAATTT---TCATTAAACCTAGAACAGATCCAAAAGTAGTCAATG--
1200  GROUP_11     GATC......TGCAAATTT...TCATTAAACCTAGAACAGATCCAAAAGTAGTCAATG..
1201
1202  33_HRV66     ----TA---------------
1203  34_HRV66b|    ----TG---------------
1204  35_HRV66a|    ----TC---------------
1205  GROUP_11     ....T-...............
1206
1207
1208
1209  Group 12:
1210
1211  36_HRV77a|    AATCCAGTTGAGGACTATATCGATAATGTACTTAATGAAGTCTTAGTAGTACCAAATACC
1212  37_HRV77b|    AATCCAGTTGAGGACTATATCGATAATGTACTTAATGAAGTCTTAGTAGTACCAAATACC
1213  38_HRV77     AATCCAGTTGAGGACTATATCGATAATGTACTTAATGAAGTCTTAGTAGTACCAAATACC
1214  GROUP_12     AATCCAGTTGAGGACTATATCGATAATGTACTTAATGAAGTCTTAGTAGTACCAAATACC
1215
1216  36_HRV77a|    AAGGAGAGTCATCCAAGCACTTCTAACTCTGCTCCTATACTAGATGCAGCTGAAACAGGC
1217  37_HRV77b|    AAGGAGAGTCATCCAAGCACTTCTAACTCTGCTCCTATACTAGATGCAGCTGAAACAGGC
1218  38_HRV77     AAGGAGAGTCATCCAAGCACTTCTAACTCTGCTCCTATACTAGATGCAGCTGAAACAGGC
1219  GROUP_12     AAGGAGAGTCATCCAAGCACTTCTAACTCTGCTCCTATACTAGATGCAGCTGAAACAGGC
1220
1221  36_HRV77a|    CATACTAGTAGTGTGCAACCAGAAGATACAGTTGAGACCCGCTATGTACAAACTTCCCAG
1222  37_HRV77b|    CATACTAGTAGTGTGCAACCAGAAGATACAGTTGAGACCCGCTATGTACAAACTTCCCAG
1223  38_HRV77     CATACTAGTAGTGTGCAACCAGAAGATACAGTTGAGACCCGCTATGTACAAACTTCCCAG
1224  GROUP_12     CATACTAGTAGTGTGCAACCAGAAGATACAGTTGAGACCCGCTATGTACAAACTTCCCAG
1225
1226  36_HRV77a|    ACAAGGGATGAGATGAGTATTGAGAGCTTTCTGGGTAGGTCTGGTTGTATTCACATTTCA
1227  37_HRV77b|    ACAAGGGATGAGATGAGTATTGAGAGCTTTCTGGGTAGGTCTGGTTGTATTCACATTTCA
```

FIG. D14 CONT'D

```
10.trace                                                              9/20/2007 5:05 PM 1228  38_HRV77      ACAAGGGATGAGATGAGTATTGAGAGCTTTCTGGGTAGGTCTGGTTGTATTCACATTTCA
1229  GROUP_12     ACAAGGGATGAGATGAGTATTGAGAGCTTTCTGGGTAGGTCTGGTTGTATTCACATTTCA
1230
1231  36_HRV77a|    ACAATAAATGTAGAAGATGGTAAA---------------ACTTATG------ATGAATCT
1232  37_HRV77b|    ACAATAAATGTAGAAGATGGTAAA---------------ACTTATG------ATGAATCT
1233  38_HRV77      ACAATAAATGTAGAAGATGGTAAA---------------ACTTATG------ATGAATCT
1234  GROUP_12     ACAATAAATGTAGAAGATGGTAAA...............ACTTATG......ATGAATCT
1235
1236  36_HRV77a|    AAATTTAGAAAATGGCAAATTACACTACAAGAAATGGCTCAAATTAGGCGCAAATTTGAA
1237  37_HRV77b|    AAATTTAGAAAATGGCAAATTACACTACAAGAAATGGCTCAAATTAGGCGCAAATTTGAA
1238  38_HRV77      AAATTTAGAAAATGGCAAATTACACTACAAGAAATGGCTCAAATTAGGCGCAAATTTGAA
1239  GROUP_12     AAATTTAGAAAATGGCAAATTACACTACAAGAAATGGCTCAAATTAGGCGCAAATTTGAA
1240
1241  36_HRV77a|    ATGTTTACATATGTAAGATTTGATTCAGAAATTACATTGG-TCCCATGTATTGCTGGAAA
1242  37_HRV77b|    ATGTTTACATATGTAAGATTTGATTCAGAAATTACATTGG-TCCCATGTATTGCTGGAAA
1243  38_HRV77      ATGTTTACATATGTAAGATTTGATTCAGAAATTACATTGG-TCCCATGTATTGCTGGAAA
1244  GROUP_12     ATGTTTACATATGTAAGATTTGATTCAGAAATTACATTGG.TCCCATGTATTGCTGGAAA
1245
1246  36_HRV77a|    AGGTGATGACATAGGACATGTTGTCATGCAATACATGTATGTACCACCAGGGGCACCCAT
1247  37_HRV77b|    AGGTGATGACATAGGACATGTTGTCATGCAATACATGTATGTACCACCAGGGGCACCCAT
1248  38_HRV77      AGGTGATGACATAGGACATGTTGTCATGCAATACATGTATGTACCACCAGGGGCACCCAT
1249  GROUP_12     AGGTGATGACATAGGACATGTTGTCATGCAATACATGTATGTACCACCAGGGGCACCCAT
1250
1251  36_HRV77a|    ACCAGATAGCAGGACTCATTTTGCATGGCAGTCAGGGACTAATGCATCAATATTCTGGCA
1252  37_HRV77b|    ACCAGATAGCAGGACTCATTTTGCATGGCAGTCAGGGACTAATGCATCAATATTCTGGCA
1253  38_HRV77      ACCAGATAGCAGGACTCATTTTGCATGGCAGTCAGGGACTAATGCATCAATATTCTGGCA
1254  GROUP_12     ACCAGATAGCAGGACTCATTTTGCATGGCAGTCAGGGACTAATGCATCAATATTCTGGCA
1255
1256  36_HRV77a|    ACATGGACAACCATTCCCAAGATTTTCACTACCTTTTCTGAGTATTGCTTCAGCTTACTA
1257  37_HRV77b|    ACATGGACAACCATTCCCAAGATTTTCACTACCTTTTCTGAGTATTGCTTCAGCTTACTA
1258  38_HRV77      ACATGGACAACCATTCCCAAGATTTTCACTACCTTTTCTGAGTATTGCTTCAGCTTACTA
1259  GROUP_12     ACATGGACAACCATTCCCAAGATTTTCACTACCTTTTCTGAGTATTGCTTCAGCTTACTA
1260
1261  36_HRV77a|    CATGTTTTATGATGGCTATGATGGGGATACCTATGAATCACGTTATGGTACTACAGTGGT
1262  37_HRV77b|    CATGTTTTATGATGGCTATGATGGGGATACCTATGAATCACGTTATGGTACTACAGTGGT
1263  38_HRV77      CATGTTTTATGATGGCTATGATGGGGATACCTATGAATCACGTTATGGTACTACAGTGGT
1264  GROUP_12     CATGTTTTATGATGGCTATGATGGGGATACCTATGAATCACGTTATGGTACTACAGTGGT
1265
1266  36_HRV77a|    TAATCACATGGGCACACTGTGCATTAGAATAGTCACTAATCAGCAAAATCATGAGGTTGA
1267  37_HRV77b|    TAATCACATGGGCACACTGTGCATTAGAATAGTCACTAATCAGCAAAATCATGAGGTTGA
1268  38_HRV77      TAATCACATGGGCACACTGTGCATTAGAATAGTCACTAATCAGCAAAATCATGAGGTTGA
1269  GROUP_12     TAATCACATGGGCACACTGTGCATTAGAATAGTCACTAATCAGCAAAATCATGAGGTTGA
1270
1271  36_HRV77a|    AATCACCACTAGAGTATACCACAAGGCTAAACATATTAAAGCTTGGTGTCCCAGACCACC
1272  37_HRV77b|    AATCACCACTAGAGTATACCACAAGGCTAAACATATTAAAGCTTGGTGTCCCAGACCACC
1273  38_HRV77      AATCACCACTAGAGTATACCACAAGGCTAAACATATTAAAGCTTGGTGTCCCAGACCACC
1274  GROUP_12     AATCACCACTAGAGTATACCACAAGGCTAAACATATTAAAGCTTGGTGTCCCAGACCACC
1275
1276  36_HRV77a|    TAGAGCTGTACCATACACA-GCAGTAGATTCAACAAATTACAAAC-CTATGA---GAGGG
1277  37_HRV77b|    TAGAGCTGTACCATACACA-GCAGTAGATTCAACAAATTACAAAC-CTATGA---GAGGG
1278  38_HRV77      TAGAGCTGTACCATACACA-GCAGTAGATTCAACAAATTACAAAC-CTATGA---GAGGG
1279  GROUP_12     TAGAGCTGTACCATACACA.GCAGTAGATTCAACAAATTACAAAC.CTATGA...GAGGG
1280
1281  36_HRV77a|    GATG------TACAAATCT---TTATTAAAGAGAGAGCAAGCCCAAAAGTAGTTACTT--
1282  37_HRV77b|    GATG------TACAAATCT---TTATTAAAGAGAGAGCAAGCCCAAAAGTAGTTACTT--
1283  38_HRV77      GATG------TACAAATCT---TTATTAAAGAGAGAGCAAGCCCAAAAGTAGTTACTT--
1284  GROUP_12     GATG......TACAAATCT...TTATTAAAGAGAGAGCAAGCCCAAAAGTAGTTACTT..
1285
1286  36_HRV77a|    ----TG---------------
1287  37_HRV77b|    ----TA---------------
1288  38_HRV77      ----TT---------------
1289  GROUP_12     ....T-...............
1290
1291
1292
```

FIG. D14 CONT'D 10.trace                                                                        9/20/2007 5:05 PM

```
1293 Group 13:
1294
1295 39_HRV62a    AATCCAATTGAAAATTATGTAGATCAAGTACTTAATGAAGTTTTAGTTGTACCAAATATT
1296 40_HRV62b    AATCCAATTGAAAATTATGTAGATCAAGTACTTAATGAAGTTTTAGTTGTACCAAATATT
1297 41_HRV25     AATCCAATTGAAAATTATGTAGATCAAGTACTTAATGAGGTTCTAGTCGTACCAAATATT
1298 GROUP_13     AATCCAATTGAAAATTATGTAGATCAAGTACTTAATGA-GTT-TAGT-GTACCAAATATT
1299
1300 39_HRV62a    AAAGAAAGTCACCCTAGTACGTCAAACTCTGCCCCAATTCTAGATGCTGCTGAAACCGGA
1301 40_HRV62b    AAAGAAAGTCACCCTAGTACGTCAAACTCTGCCCCAATTCTAGATGCTGCTGAAACCGGA
1302 41_HRV25     AAAGAAAGTCACCCAAGCACATCAAATTCTGCCCCAATTCTAGATGCTGCTGAAACTGGA
1303 GROUP_13     AAAGAAAGTCACCC-AG-AC-TCAAA-TCTGCCCCAATTCTAGATGCTGCTGAAAC-GGA
1304
1305 39_HRV62a    CACACTAGTAATGTACAACCAGAAGCACTATTGAAACCCGTCATGTTCAAACCACACAA
1306 40_HRV62b    CACACTAGTAATGTACAACCAGAAGCACTATTGAAACCCGTTATGTTCAAACCACACAA
1307 41_HRV25     CACACTAGCAATGTGCAACCAGAGGATACCATTGAAACTCGTTATGTTCAAACCACACAA
1308 GROUP_13     CACACTAG-AATGT-CAACCAGA-GA-AC-ATTGAAAC-CGT-ATGTTCAAACCACACAA
1309
1310 39_HRV62a    ACTAGAGATGAAATGAGCATTGAGAGCTTTCTTGGTAGGTCAGGGTGCGTACACACTTCA
1311 40_HRV62b    ACTAGAGATGAAATGAGCATTGAGAGCTTTCTTGGTAGGTCAGGGTGCGTACACACTTCA
1312 41_HRV25     ACTAGAGATGAAATGAGTATTGAAAGTTTTCTTGGTAGGTCAGGGTGTGTACATACTTCA
1313 GROUP_13     ACTAGAGATGAAATGAG-ATTGA-AG-TTTCTTGGTAGGTCAGGGTG-GTACA-ACTTCA
1314
1315 39_HRV62a    ACAATTGAA---------ACAACG---------------CTTAGTC------ATAAAGAT
1316 40_HRV62b    ACAATTGAA---------ACAACG---------------CTTAGTC------ATAAAGAT
1317 41_HRV25     ACAATTGAA---------ACAAAA---------------CTTAAAC------ATGATGAA
1318 GROUP_13     ACAATTGAA.........ACAA--...............CTTA--C......AT-A-GA-
1319
1320 39_HRV62a    AGATTCAAAACATGGAATATTAACTTACAAGAGATGGCTCAAATCAGGAGAAAGTTTGAA
1321 40_HRV62b    AGATTCAAAACATGGAATATTAACTTACAAGAGATGGCTCAAATCAGGAGAAAGTTTGAA
1322 41_HRV25     AGATTTAAAATATGGAATATCAATTTACAAGAAATGGCTCAAATTAGGAGAAAGTTTGAG
1323 GROUP_13     AGATT-AAAA-ATGGAATAT-AA-TTACAAGA-ATGGCTCAAAT-AGGAGAAAGTTTGA-
1324
1325 39_HRV62a    ATGTTTACATATGTAAGATTTGATTCAGAAATAACCCTGG-TTCCATCTATTGCAGGACG
1326 40_HRV62b    ATGTTTACATATGTAAGATTTGATTCAGAAATAACCCTGG-TTCCATCTATTGCAGGACG
1327 41_HRV25     ATGTTTACATATGTAAGATTTGATTCAGAGATAACCCTAG-TTCCATCTATTGCAGGACG
1328 GROUP_13     ATGTTTACATATGT-AGATTTGATTCAGA-ATAACCCT-G.TTCCATCTATTGCAGGACG
1329
1330 39_HRV62a    TGGTGCAGATATAGGTCACATAGTTATGCAATATATGTATGTACCACCTGGGGCTCCACT
1331 40_HRV62b    TGGTGCAGATATAGGTCACATAGTTATGCAATATATGTATGTACCACCTGGGGCTCCACT
1332 41_HRV25     TGGTGCAGATATAGGTCACATAGTTATGCAATATATGTATGTGCCACCTGGAGCCCCATT
1333 GROUP_13     TGGTGCAGATATAGGTCACATAGTTATGCAATATATGTATGT-CCACCTGG-GC-CCA-T
1334
1335 39_HRV62a    ACCAACAGACAGAAAGCATTTTGCCTGGCAATCAAGTACTAATGCATCAATATTTTGGCA
1336 40_HRV62b    ACCAACAGACAGAAAGCATTTTGCCTGGCAATCAAGTACTAATGCATCAATATTTTGGCA
1337 41_HRV25     ACCAACAGACAGAAAACACTTTGCATGGCAATCAAGTACTAATGCATCAATATTTTGGCA
1338 GROUP_13     ACCAACAGACAGAAA-CA-TTTGC-TGGCAATCAAGTACTAATGCATCAATATTTTGGCA
1339
1340 39_HRV62a    ACATGGGCAACCCTTTCCTAGATTTTCATTACCTTTTTTGAGTGTTGCATCTGCTTATTA
1341 40_HRV62b    ACATGGGCAACCCTTTCCTAGATTTTCATTACCTTTTTTGAGTGTTGCATCTGCTTATTA
1342 41_HRV25     ACATGGACAACCCTTCCCTAGATTTTCATTCCCATTTCTGAGTGTTGCATCTGCTTATTA
1343 GROUP_13     ACATGG-CAACCCTT-CCTAGATTTTCATT-CC-TTT-TGAGTGTTGCATCTGCTTATTA
1344
1345 39_HRV62a    CATGTTTTATGATGGCTATAATGGTGATGACTATACAGCAAAATACGGTACCACCGTGGT
1346 40_HRV62b    CATGTTTTATGATGGCTATAATGGTGATGACTATACAGCAAAATACGGTACCACCGTGGT
1347 41_HRV25     CATGTTTTATGATGGCTATAATGGTGATGATCACACAGCGAGATATGGTACCACTGTGGT
1348 GROUP_13     CATGTTTTATGATGGCTATAATGGTGATGA--A-ACAGC-A-ATA-GGTACCAC-GTGGT
1349
1350 39_HRV62a    TAATCGTATGGGGGCACTGTGTATGAGGATTGTCACAAACAAACAAGTTCATGATGTTGA
1351 40_HRV62b    TAATCGTATGGGGGCACTGTGTATGAGGATTGTCACAAACAAACAAGTTCATGATGTTGA
1352 41_HRV25     TAACCGTATGGGGAGCACTGTGCATGAGAATTGTCACAAATAAACAAGTCCATGATGTTGA
1353 GROUP_13     TAA-CGTATGGG-GCACTGTG-ATGAG-ATTGTCACAAA-AAACAAGT-CATGATGTTGA
1354
1355 39_HRV62a    GGTCACAACTAATATATTACCACAAGGCTAAGCATGTAAAAGCGTGGTGCCCGCGGCCGCC
1356 40_HRV62b    GGTCACAACTAATATATTACCACAAGGCTAAGCATGTAAAAGCGTGGTGCCCTAGACCACC
1357 41_HRV25     GGTTACAACTAACATTTACCATAAAGCTAAGCATGTAAAAGCATGGTGCCCTAGACCACC
```

FIG. D14 CONT'D

```
1358 GROUP_13    GGT-ACAACTAA-ATTTACCA-AA-GCTAAGCATGTAAAAGC-TGGTGCCC--G-CC-CC
1359
1360 39_HRV62a   CAGAGCTGTTCCATATAAA-TATGTTGATTTCAATAATTATGCAG-CCAGTG---ATAGT
1361 40_HRV62b   TAGAGCTGTTCCATATAAA-TATGTTGATTTCAATAATTATGCAG-CCAGTG---ATAGT
1362 41_HRV25    TAGAGCTGTCCCATATAAA-TATGTTGACTTCAATAATTATGCAG-CCAGTG---ATAAT
1363 GROUP_13    -AGAGCTGT-CCATATAAA.TATGTTGA-TTCAATAATTATGCAG.CCAGTG...ATA-T
1364
1365 39_HRV62a   ---G------TTGACATTT---TTATAAAATCAAGG------CAAAACTTGCAAACAG--
1366 40_HRV62b   ---G------TTGACATTT---TTATAAAATCAAGG------CAAAACTTGCAAACAG--
1367 41_HRV25    ---G------TTGACATCT---TTATACAACCAAGA------AACAGTTTAAAAACAG--
1368 GROUP_13    ...G......TTGACAT-T...TTATA-AA-CAAG-.......-A-A--TT--AAACAG..
1369
1370 39_HRV62a   ----CT---------------
1371 40_HRV62b   ----C----------------
1372 41_HRV25    ----CT---------------
1373 GROUP_13    ....C-...............
1374
1375
1376
1377 Group 14:
1378
1379 42_HRV29a   AACCCAGTTGAAAACTATGTGGATGAGGTGCTTAATGAAGTTTTAGTTGTGCCTAACATC
1380 43_HRV29b   AACCCAGTTGAAAACTATGTGGATGAGGTGCTTAATGAAGTTTTAGTTGTGCCTAACATC
1381 44_HRV44a   AACCCAGTTGAAAATTATGTGGATGAAGTACTTAATGAAGTCTTAGTTGTGCCTAATATC
1382 45_HRV44b   AACCCAGTTGAAAATTATGTGGATGAAGTACTTAATGAAGTCTTAGTTGTGCCTAATATC
1383 GROUP_14    AACCCAGTTGAAAA-TATGTGGATGA-GT-CTTAATGAAGT-TTAGTTGTGCCTAA-ATC
1384
1385 42_HRV29a   AGGGAGAGCCACCCAAGCACGTCCAACTCTGCACCAATCTTGGATGCTGCTGAGACTGGA
1386 43_HRV29b   AGGGAGAGCCACCCAAGCACGTCCAACTCTGCACCAATCTTGGATGCTGCTGAGACTGGA
1387 44_HRV44a   AGAGAGAGCCACCCAAGCACACTAACTCTGCTCCAATTTTGGATGCTGCTGAAACTGGA
1388 45_HRV44b   AGAGAGAGCCACCCAAGCATATCTAACTCTGCTCCAATTTTGGATGCTGCTGAAACTGGA
1389 GROUP_14    AG-GAGAGCCACCCAAGCA--TC-AACTCTGC-CCAAT-TTGGATGCTGCTGA-ACTGGA
1390
1391 42_HRV29a   CATACTAGTAATGTACAACCAGAAGATACCATTGAGACTCGTTATGTACAAACCTCACAT
1392 43_HRV29b   CATACTAGTAATGTACAACCAGAAGATACCATTGAGACTCGTTATGTACAAACCTCACAT
1393 44_HRV44a   CATACTAGTAATGTACAACCAGAAGATACCATTGAGACTCGATATGTACAAACCTCACAA
1394 45_HRV44b   CATACTAGTAATGTACAACCAGAAGATACCATTGAGACTCGATATGTACAAACCTCACAA
1395 GROUP_14    CATACTAGTAATGTACAACCAGAAGATACCATTGAGACTCG-TATGTACAAACCTCACA-
1396
1397 42_HRV29a   ACTAGAGATGAAATGAGCATTGAAAGTTTCTTGGGTAGATCAGGATGTATACATGTTTCA
1398 43_HRV29b   ACTAGAGATGAAATGAGCATTGAAAGTTTTCTTGGTAGATCAGGATGTATACATGTTTCA
1399 44_HRV44a   ACTAGAGATGAAATGAGCATTGAAAGTTTTCTTGGCAGATCAGGGTGTATACATGTTTCA
1400 45_HRV44b   ACTAGAGATGAAATGAGCATTGAAAGTTTTCTTGGCAGATCAGGGTGTATACATGTTTCA
1401 GROUP_14    ACTAGAGATGAAATGAGCATTGAAAGTTTT--T-GG-AGATCAGG-TGTATACATGTTTCA
1402
1403 42_HRV29a   ACAATAAAA---------GCAAAT---------------CAGGCAC------ATGACGCC
1404 43_HRV29b   ACAATAAAA---------GCAAAT---------------CAGGCAC------ATGACGCC
1405 44_HRV44a   ACAATAAAG---------ACAAAT---------------CAGGCAC------ACAATACC
1406 45_HRV44b   ACAATAAAG---------ACAAAT---------------CAGGCAC------ACAATACC
1407 GROUP_14    ACAATAAA-.........-CAAAT...............CAGGCAC......A--A--CC
1408
1409 42_HRV29a   AAGTTCGATAAATGGAATGTTAACTTACAAGAAATGGCTCAAATTAGGCGCAAATTTGAA
1410 43_HRV29b   AAGTTCGATAAATGGAATGTTAACTTACAAGAAATGGCTCAAATTAGGCGCAAATTTGAA
1411 44_HRV44a   AAGTTTGATAAATGGAATATCAACTTACAAGAAATGGCTCAAATTAGACGCAAATTTGAA
1412 45_HRV44b   AAGTTTGATAAATGGAATATCAACTTACAAGAAATGGCTCAAATTAGACGCAAATTTGAA
1413 GROUP_14    AAGTT-GATAAATGGAAT-T-AACTTACAAGAAATGGCTCAAATTAG-CGCAAATTTGAA
1414
1415 42_HRV29a   ATGTTCACATATGTGAGATTTGACTCAGAAATAACTCTGG-TTCTTTGCATTGCAGGACG
1416 43_HRV29b   ATGTTCACATATGTGAGATTTGACTCAGAAATAACTCTGG-TTCCATGCATTGCAGGACG
1417 44_HRV44a   ATGTTCACATATGTGAGATTTGATTCGGAAATAACTCTAG-TTCCATGCATTGCAGGACA
1418 45_HRV44b   ATGTTCACATATGTGAGATTTGATTCAGAAATAACTCTAG-TTCCATGCATTGCAGGACG
1419 GROUP_14    ATGTTCACATATGTGAGATTTGA-TC-GAAATAACTCT-G.TTC--TGCATTGCAGGAC-
1420
1421 42_HRV29a   TGGTAATGATATAGGTCACATAGTTATGCAGTACATGTATGTACCACCTGGAGCTCCAGT
1422 43_HRV29b   TGGTAATGATATAGGTCACATAGTTATGCAGTACATGTATGTACCACCTGGAGCTCCAGT
```

FIG. D14 CONT'D

```
10.trace                                                                    9/20/2007 5:05 PM 1423  44_HRV44a     TGGTGATGATATAGGCCACATAGTTATGCAGTACATGTATGTACCACCTGGAGCTCCAGT
1424  45_HRV44b     TGGTGATGATATAGGCCACATAGTTATGCAGTACATGTATGTACCACCTGGAGCTCCAGT
1425  GROUP_14      TGGT-ATGATATAGG-CACATAGTTATGCAGTACATGTATGTACCACCTGGAGCTCCAGT
1426
1427  42_HRV29a     ACCAAATGACAGAAATCATTTTGCATGGCAATCAGGGACTAATGCATCAATATTCTGGCA
1428  43_HRV29b     ACCAAATGACAGAAATCATTTTGCATGGCAATCAGGGACTAATGCATCAATATTCTGGCA
1429  44_HRV44a     ACCAGATGACAGAAACCACTTTGCATGGCAATCGGGGACTAATGCATCAATATTCTGGCA
1430  45_HRV44b     ACCAGATGACAGAATCCACTTTGCATGGCAATCGGGGAATAATGCATCAATATTCTGGCA
1431  GROUP_14      ACCA--ATGACAGAA--CA-TTTGCATGGCAATC-GGGA-TAATGCATCAATATTCTGGCA
1432
1433  42_HRV29a     ACATGGTCAGCCTTTCCCAAGATTTTCATTACCATTCCTAAGTGTTGCATCTGCTTATTA
1434  43_HRV29b     ACATGGTCAGCCTTTCCCAAGATTTTCATTACCATTCCTAAGTGTTGCATCTGCTTATTA
1435  44_HRV44a     ACATGGTCAACCTTTCCCAAGATTTTCATTGCCATTTCTAAGTGTTGCATCTGCCTATTA
1436  45_HRV44b     ACATGGTCAACCTTTCCCAAGATTTTCATTGCCATTTCTAAGTGTTGCATCTGCCTATTA
1437  GROUP_14      ACATGGTCA-CCTTTCCCAAGATTTTCATT-CCATT-CTAAGTGTTGCATCTGC-TATTA
1438
1439  42_HRV29a     CATGTTTTATGATGGTTACAATGGAGGTGATCATACAGCAACTTATGGCACCACAGTGGT
1440  43_HRV29b     CATGTTTTATGATGGTTACAATGGAGGTGATCATACAGCAACTTATGGCACCACAGTGGT
1441  44_HRV44a     CATGTTTTATGACGGTTATAATGGAGGTGATCATACAGCAACTTATGGCACCACAGTGGT
1442  45_HRV44b     CATGTTTTATGACGGTTATAATGGAGGTGATCATACAGCAACTTATGGCACCACAGTGGT
1443  GROUP_14      CATGTTTTATGA-GGTTA--AATGGAGGTGATCATACAGCAACTTATGGCACCACAGTGGT
1444
1445  42_HRV29a     TAACCGGATGGGGACGCTTTGTGTCAGAATTGTTACAGGCAAACAAGCTCATGATGTTCA
1446  43_HRV29b     TAACCGGATGGGGACGCTTTGTGTCAGAATTGTTACAGGCAAACAAGCTCATGATGTTCA
1447  44_HRV44a     TAACCGGATGGGGACGCTTTGCGTCAGGATCGTTACGGGCAAACAGGCTCATGATGTCCA
1448  45_HRV44b     TAACCGGATGGGGACGCTTTGCGTCAGGATCGTTACGGGCAAACAGGCTCATGATGTCCA
1449  GROUP_14      TAACCGGATGGGGACGCTTTG-GTCAG-AT-GTTAC-GGCAAACA-GCTCATGATGT-CA
1450
1451  42_HRV29a     AGTTACAACAAGTATCTATCATAAAGCTAAACATGTAAAGGCGTGGTGTCCTAGACCACC
1452  43_HRV29b     AGTTACAACAAGTATCTATCATAAAGCTAAACATGTAAAGGCGTGGTGTCCTAGACCACC
1453  44_HRV44a     AGTTACAACAAGCATTTATCACAAAGCTAAACATGTAAAAGCATGGTGCCCTAGACCACC
1454  45_HRV44b     AGTTACAACAAGCATTTATCACAAAGCTAAACATGTAAAAGCATGGTGCCCTAGACCACC
1455  GROUP_14      AGTTACAACAAG-AT-TATCA-AAAGCTAAACATGTAAA-GC-TGGTG-CCTAGACCACC
1456
1457  42_HRV29a     AAGAGTTGTCCCATACAAG-TATGTTGGCCTAACTAATTACACAC-TTAAAG---AAGAA
1458  43_HRV29b     AAGAGTTGTCCCATACAAG-TATGTTGGCCTAACTAATTACACAC-TTAAAG---AAGAA
1459  44_HRV44a     AAGGGTTGTCCCATACAAG-TATGTTGGCCTAACTAATTACACAC-TTAAAG---AAACA
1460  45_HRV44b     AAGGGTTGTCCCATACAAG-TATGTTGGCCTAACTAATTACACAC-TTAAAG---AAACA
1461  GROUP_14      AAG-GTTGTCCCATACAAG.TATGTTGGCCTAACTAATTACACAC.TTAAAG...AA--A
1462
1463  42_HRV29a     ---G------AT-CCAG-----TTGTGGAATCCAGA------CCAAGCTTAATGACAG--
1464  43_HRV29b     ---G------AT-ACAG-----TTGTGGAATCCAGA------CCAAGCTTAATGACAG--
1465  44_HRV44a     ---G------AT-ACAG-----TTGTGGAACCTAGA------CACAGCATAATGACAG--
1466  45_HRV44b     ---G------AT-ACAG-----TTGTGGAACCTAGA------CACAGCATAATGACAG--
1467  GROUP_14      ...G......AT.-CAG.....TTGTGGAA-C-AGA......C--AGC-TAATGACAG..
1468
1469  42_HRV29a     ----CT---------------
1470  43_HRV29b     ----CT---------------
1471  44_HRV44a     ----CT---------------
1472  45_HRV44b     ----CT---------------
1473  GROUP_14      ....CT...............
1474
1475
1476
1477  Group 15:
1478
1479  46_HRV31      AATCCAGTTGAAAACTATGTGGAAGAGGTTCTTAATGAAGTCTTAGTAGTACCTAATATC
1480  47_HRV31a|    AATCCAGTTGAAAACTATGTGGAAGAGGTTCTTAATGAAGTCTTAGTAGTACCTAATATC
1481  48_HRV31b|    AATCCAGTTGAAAACTATGTGGAAGAGGTTCTTAATGAAGTCTTAGTAGTACCTAATATC
1482  GROUP_15      AATCCAGTTGAAAACTATGTGGAAGAGGTTCTTAATGAAGTCTTAGTAGTACCTAATATC
1483
1484  46_HRV31      AAAGAAAGCCATCCAAGCACATCTAATTCTGCCCCAATCCTGGACGCTGCTGAAACTGGA
1485  47_HRV31a|    AAAGAAAGCCATCCAAGCACATCTAATTCTGCCCCAATCCTGGACGCTGCTGAAACTGGA
1486  48_HRV31b|    AAAGAAAGCCATCCAAGCACATCTAATTCTGCCCCAATCCTGGACGCTGCTGAAACTGGA
1487  GROUP_15      AAAGAAAGCCATCCAAGCACATCTAATTCTGCCCCAATCCTGGACGCTGCTGAAACTGGA
```

FIG. D14 CONT'D

10.trace                                                                9/20/2007 5:05 PM

```
1488
1489 46_HRV31      CACACTAGTAATGTACAACCAGAAGATACAATTGAAACTCGCTACGTGCAAACATCACAA
1490 47_HRV31a|    CACACTAGTAATGTACAACCAGAAGATACAATTGAAACTCGCTACGTGCAAACATCACAA
1491 48_HRV31b|    CACACTAGTAATGTACAACCAGAAGATACAATTGAAACTCGCTACGTGCAAACATCACAA
1492 GROUP_15      CACACTAGTAATGTACAACCAGAAGATACAATTGAAACTCGCTACGTGCAAACATCACAA
1493
1494 46_HRV31      ACAAGAGATGAAATGAGCATTGAAAGTTTCCTTGGTAGGTCAGGATGTGTACATACTTCA
1495 47_HRV31a|    ACAAGAGATGAAATGAGCATTGAAAGTTTCCTTGGTAGGTCAGGATGTGTACATACTTCA
1496 48_HRV31b|    ACAAGAGATGAAATGAGCATTGAAAGTTTCCTTGGTAGGTCAGGATGTGTACATACTTCA
1497 GROUP_15      ACAAGAGATGAAATGAGCATTGAAAGTTTCCTTGGTAGGTCAGGATGTGTACATACTTCA
1498
1499 46_HRV31      ATAATAGAA--------CCAGAT---------------GGACTCC------ATGATAGC
1500 47_HRV31a|    ATAATAGAA--------CCAGAT---------------GGACTCC------ATGATAGC
1501 48_HRV31b|    ATAATAGAA--------CCAGAT---------------GGACTCC------ATGATAGC
1502 GROUP_15      ATAATAGAA.........CCAGAT...............GGACTCC......ATGATAGC
1503
1504 46_HRV31      AAATATAAAGTATGGCACATTAATTTACAAGAGATGGCCCAGATTAGGCGAAAATTTGAA
1505 47_HRV31a|    AAATATAAAGTATGGCACATTAATTTACAAGAGATGGCCCAGATTAGGCGAAAATTTGAA
1506 48_HRV31b|    AAATATAAAGTATGGCACATTAATTTACAAGAGATGGCCCAGATTAGGCGAAAATTTGAA
1507 GROUP_15      AAATATAAAGTATGGCACATTAATTTACAAGAGATGGCCCAGATTAGGCGAAAATTTGAA
1508
1509 46_HRV31      ATGTTCACATATGTAAGATTTGATTCAGAAGTGACCATAG-TTCCATGCATTGCAGGACA
1510 47_HRV31a|    ATGTTCACATATGTAAGATTTGATTCAGAAGTGACCATAG-TTCCATGCATTGCAGGACA
1511 48_HRV31b|    ATGTTCACATATGTAAGATTTGATTCAGAAGTGACCATAG-TTCCATGCATTGCAGGACA
1512 GROUP_15      ATGTTCACATATGTAAGATTTGATTCAGAAGTGACCATAG.TTCCATGCATTGCAGGACA
1513
1514 46_HRV31      TGGTAGTGACATAGGCCATATAGTCATGCAATACATGTATGTACCACCTGGGGCCCCAGT
1515 47_HRV31a|    TGGTAGTGACATAGGCCATATAGTCATGCAATACATGTATGTACCACCTGGGGCCCCAGT
1516 48_HRV31b|    TGGTAGTGACATAGGCCATATAGTCATGCAATACATGTATGTACCACCTGGGGCCCCAGT
1517 GROUP_15      TGGTAGTGACATAGGCCATATAGTCATGCAATACATGTATGTACCACCTGGGGCCCCAGT
1518
1519 46_HRV31      ACCAACAAATAGAAAACATTTTGCATGGCAATCAGGTACTAATGCATCGATTTTCTGGCA
1520 47_HRV31a|    ACCAACAAATAGAAAACATTTTGCATGGCAATCAGGTACTAATGCATCGATTTTCTGGCA
1521 48_HRV31b|    ACCAACAAATAGAAAACATTTTGCATGGCAATCAGGTACTAATGCATCGATTTTCTGGCA
1522 GROUP_15      ACCAACAAATAGAAAACATTTTGCATGGCAATCAGGTACTAATGCATCGATTTTCTGGCA
1523
1524 46_HRV31      ACATGGACAACCCTTTCCAAGATTTACATTACCCTTTTTGAGTGTCGCATCCGCTTATTA
1525 47_HRV31a|    ACATGGACAACCCTTTCCAAGATTTACATTACCCTTTTTGAGTGTCGCATCCGCTTATTA
1526 48_HRV31b|    ACATGGACAACCCTTTCCAAGATTTACATTACCCTTTTTGAGTGTCGCATCCGCTTATTA
1527 GROUP_15      ACATGGACAACCCTTTCCAAGATTTACATTACCCTTTTTGAGTGTCGCATCCGCTTATTA
1528
1529 46_HRV31      CATGTTTTATGATGGTTATGATGGAGACAAAAGTGGAGCCAAGTATGGTACTACAGTAGT
1530 47_HRV31a|    CATGTTTTATGATGGTTATGATGGAGACAAAAGTGGAGCCAAGTATGGTACTACAGTAGT
1531 48_HRV31b|    CATGTTTTATGATGGTTATGATGGAGACAAAAGTGGAGCCAAGTATGGTACTACAGTAGT
1532 GROUP_15      CATGTTTTATGATGGTTATGATGGAGACAAAAGTGGAGCCAAGTATGGTACTACAGTAGT
1533
1534 46_HRV31      TAATCGCATGGGTGCACTATGCATGAGAGTTGTCACTAACAAACAAGCTCATAAAGTTGA
1535 47_HRV31a|    TAATCGCATGGGTGCACTATGCATGAGAGTTGTCACTAACAAACAAGCTCATAAAGTTGA
1536 48_HRV31b|    TAATCGCATGGGTGCACTATGCATGAGAGTTGTCACTAACAAACAAGCTCATAAAGTTGA
1537 GROUP_15      TAATCGCATGGGTGCACTATGCATGAGAGTTGTCACTAACAAACAAGCTCATAAAGTTGA
1538
1539 46_HRV31      AATCACAACCAATATTTACCATAAGGCCAAACATGTTAAGGCATGGTGTCCTAGGCCCCC
1540 47_HRV31a|    AATCACAACCAATATTTACCATAAGGCCAAACATGTTAAGGCATGGTGTCCTAGGCCCCC
1541 48_HRV31b|    AATCACAACCAATATTTACCATAAGGCCAAACATGTAAAGGCATGGTGTCCTAGGCCACC
1542 GROUP_15      AATCACAACCAATATTTACCATAAGGCCAAACATGT-AAGGCATGGTGTCCTAGGCC-CC
1543
1544 46_HRV31      TAGAGCAGTTCCATACAGGGTATG-TGGATCAACAAACTACAAAC-CTGATG---AAAAT
1545 47_HRV31a|    TAGAGCAGTTCCATACAGGGTATG-TGGATCAACAAACTACAAAC-CTGATG---AAAAT
1546 48_HRV31b|    TAGAGCAGTTCCATACAGG-TATGTTGGATCAACAAACTACAAAC-CTGATG---AAAAT
1547 GROUP_15      TAGAGCAGTTCCATACAGG-TATG-TGGATCAACAAACTACAAAC.CTGATG...AAAAT
1548
1549 46_HRV31      GAAG------TTACAATCT---TTGTTAAACACAGGGATAATCCAAAGATTATCACAG--
1550 47_HRV31a|    GAAG------TTACAATCT---TTGTTAAACACAGGGATAATCCAAAGATTATCACAG--
1551 48_HRV31b|    GAAG------TTACAATCT---TTGTTAAACACAGGGATAATCCAAAGATTATCACAG--
1552 GROUP_15      GAAG......TTACAATCT...TTGTTAAACACAGGGATAATCCAAAGATTATCACAG..
```

FIG. D14 CONT'D 10.trace                                                              9/20/2007 5:05 PM

```
1553
1554 46_HRV31     ----CA---------------
1555 47_HRV31a|   ----CT---------------
1556 48_HRV31b|   ----CA---------------
1557 GROUP_15    ....C-...............
1558
1559
1560
1561 Group 16:
1562
1563 49_HRV47     AACCCAGTCGAAAATTATGTGGAAGAGGTACTTAATGAGGTCTTAGTTGTACCAAATATC
1564 50_HRV47a|   AACCCAGTCGAAAATTATGTGGAAGAGGTACTTAATGAGGTCTTAGTTGTACCAAATATC
1565 51_HRV47b|   AACCCAGTCGAAAATTATGTGGAAGAGGTACTTAATGAGGTCTTAGTTGTACCAAATATC
1566 GROUP_16     AACCCAGTCGAAAATTATGTGGAAGAGGTACTTAATGAGGTCTTAGTTGTACCAAATATC
1567
1568 49_HRV47     AAAGAAAGTCATCCAAGTACATCCAACTCTGCCCCGATTTTAGATGCTGCTGAAACTGGA
1569 50_HRV47a|   AAAGAAAGTCATCCAAGTACATCCAACTCTGCCCCGATTTTAGATGCTGCTGAAACTGGA
1570 51_HRV47b|   AAAGAAAGTCATCCAAGTACATCCAACTCTGCCCCGATTTTAGATGCTGCTGAAACTGGA
1571 GROUP_16     AAAGAAAGTCATCCAAGTACATCCAACTCTGCCCCGATTTTAGATGCTGCTGAAACTGGA
1572
1573 49_HRV47     CACACTAGCAATGTACAGCCAGAAGATACAATTGAAACTCGATATGTACAAACAGCACAA
1574 50_HRV47a|   CACACTAGCAATGTACAGCCAGAAGATACAATTGAAACTCGATATGTACAAACAGCACAA
1575 51_HRV47b|   CACACTAGCAATGTACAGCCAGAAGATACAATTGAAACTCGATATGTACAAACAGCACAA
1576 GROUP_16     CACACTAGCAATGTACAGCCAGAAGATACAATTGAAACTCGATATGTACAAACAGCACAA
1577
1578 49_HRV47     ACAAGAGATGAAATGAGCATTGAGAGCTTCCTTGGCAGGTCAGGATGTGTGCATTCCTCA
1579 50_HRV47a|   ACAAGAGATGAAATGAGCATTGAGAGCTTCCTTGGCAGGTCAGGATGTGTGCATTCCTCA
1580 51_HRV47b|   ACAAGAGATGAAATGAGCATTGAGAGCTTCCTTGGCAGGTCAGGATGTGTGCATTCCTCA
1581 GROUP_16     ACAAGAGATGAAATGAGCATTGAGAGCTTCCTTGGCAGGTCAGGATGTGTGCATTCCTCA
1582
1583 49_HRV47     ACAATAAAA---------TCAGAT---------------GAGCAAC------ACATTAAT
1584 50_HRV47a|   ACAATAAAA---------TCAGAT---------------GAGCAAC------ACATTAAT
1585 51_HRV47b|   ACAATACAA---------TCAAAT---------------GAGCAAC------ACATTAAT
1586 GROUP_16     ACAATA-AA.........TCA-AT...............GAGCAAC......ACATTAAT
1587
1588 49_HRV47     AAATTTAAAGTATGGCACATTAATTTACAAGAAATGGCCCAGATCAGGCGTAAATATGAA
1589 50_HRV47a|   AAATTTAAAGTATGGCACATTAATTTACAAGAAATGGCCCAGATCAGGCGTAAATATGAA
1590 51_HRV47b|   AAATTTAAAGTATGGCACATTAATTTACAAGAAATGGCCCAGATCAGGCGTAAATATGAA
1591 GROUP_16     AAATTTAAAGTATGGCACATTAATTTACAAGAAATGGCCCAGATCAGGCGTAAATATGAA
1592
1593 49_HRV47     ATGTTTACATATGTAAGATTTGATTCAGAAGTAACCATGG-TTCCATGTATTGCAGGGTA
1594 50_HRV47a|   ATGTTTACATATGTAAGATTTGATTCAGAAGTAACCATGG-TTCCATGTATTGCAGGGTA
1595 51_HRV47b|   ATGTTTACATATGTAAGATTTGATTCAGAAGTAACCATGG-TTCCATGTATTGCAGGGTA
1596 GROUP_16     ATGTTTACATATGTAAGATTTGATTCAGAAGTAACCATGG.TTCCATGTATTGCAGGGTA
1597
1598 49_HRV47     TGGTGATGACATAGGTCACATAGTTATGCAATACATGTATGTGCCGCCTGGGGCTCCAGT
1599 50_HRV47a|   TGGTGATGACATAGGTCACATAGTTATGCAATACATGTATGTGCCGCCTGGGGCTCCAGT
1600 51_HRV47b|   TGGTGATGACATAGGTCACATAGTTATGCAATACATGTATGTGCCGCCTGGGGCTCCAGT
1601 GROUP_16     TGGTGATGACATAGGTCACATAGTTATGCAATACATGTATGTGCCGCCTGGGGCTCCAGT
1602
1603 49_HRV47     GCCAACAAGTAGAGAGCACTTTGCATGGCAGTCAGGTACCAATGCATCAACTTTCTGGCA
1604 50_HRV47a|   GCCAACAAGTAGAGAGCACTTTGCATGGCAGTCAGGTACCAATGCATCAACTTTCTGGCA
1605 51_HRV47b|   GCCAACAAGTAGAGAGCACTTTGCATGGCAGTCAGGTACCAATGCATCAATTTTCTGGCA
1606 GROUP_16     GCCAACAAGTAGAGAGCACTTTGCATGGCAGTCAGGTACCAATGCATCAA-TTTCTGGCA
1607
1608 49_HRV47     ACAAGGGCAACCCTTTCCAAGATTTTCATTACCATTTTTGAGTGTTGCATCTGCTTATTA
1609 50_HRV47a|   ACAAGGGCAACCCTTTCCAAGATTTTCATTACCATTTTTGAGTGTTGCATCTGCTTATTA
1610 51_HRV47b|   ACAAGGGCAACCCTTTCCAAGATTTTCATTACCATTTTTGAGTGTTGCATCTGCTTATTA
1611 GROUP_16     ACAAGGGCAACCCTTTCCAAGATTTTCATTACCATTTTTGAGTGTTGCATCTGCTTATTA
1612
1613 49_HRV47     CATGTTTTATGATGGCTATAATGGTGACAGAAGTGGAGCCAAGTATGGCACCACAGTGGT
1614 50_HRV47a|   CATGTTTATGATGGCTATAATGGTGACAGAAGTGGAGCCAAGTATGGCACCACAGTGGT
1615 51_HRV47b|   CATGTTTATGATGGCTATAATGGTGACAGAAGTGGAGCCAAGTATGGCACCACAGTGGT
1616 GROUP_16     CATGTTTTATGATGGCTATAATGGTGACAGAAGTGGAGCCAAGTATGGCACCACAGTGGT
1617
```

FIG. D14 CONT'D

```
10.trace                                                                    9/20/2007 5:05 PM 1618  49_HRV47     CAATCGCATGGGTGCATTGTGTATGAGAGTTGTAACAAACAAGCAACTCCATAAAGTTGA
1619  50_HRV47a|   CAATCGCATGGGTGCATTGTGTATGAGAGTTGTAACAAACAAGCAACTCCATAAAGTTGA
1620  51_HRV47b|   CAATCGCATGGGTGCATTGTGTATGAGAGTTGTAACAAACAAGCAACTCCATAAAGTTGA
1621  GROUP_16     CAATCGCATGGGTGCATTGTGTATGAGAGTTGTAACAAACAAGCAACTCCATAAAGTTGA
1622
1623  49_HRV47     AATCACAACTAACATCTACCATAAAGCCAAGCATGTGAAAGCATGGTGTCCTAGACCACC
1624  50_HRV47a|   AATCACAACTAACATCTACCATAAAGCCAAGCATGTGAAAGCATGGTGTCCTAGACCACC
1625  51_HRV47b|   AATCACAACTAACATCTACCATAAAGCCAAGCATGTGAAAGCATGGTGTCCTAGACCACC
1626  GROUP_16     AATCACAACTAACATCTACCATAAAGCCAAGCATGTGAAAGCATGGTGTCCTAGACCACC
1627
1628  49_HRV47     TAGAGCTGTTCCATATAGA-TATGTTGGATCAACAAATTACAAAC-CTGATC---AAGGA
1629  50_HRV47a|   TAGAGCTGTTCCATATAGA-TATGTTGGATCAACAAATTACAAAC-CTGATC---AAGGA
1630  51_HRV47b|   TAGAGCTGTTCCATATAGA-TATGTTGGATCAACAAATTACAAAC-CTGATC---AAGGA
1631  GROUP_16     TAGAGCTGTTCCATATAGA.TATGTTGGATCAACAAATTACAAAC.CTGATC...AAGGA
1632
1633  49_HRV47     GAAG------TTGCAATTT---TCATTGAGCATAGAGAAAATCCAAAATTCATTACAG--
1634  50_HRV47a|   GAAG------TTGCAATTT---TCATTGAGCATAGAGAAAATCCAAAATTCATTACAG--
1635  51_HRV47b|   GAAG------TTGCAATTT---TCATTGAGCATAGAGAAAATCCAAAATTCATTACAG--
1636  GROUP_16     GAAG......TTGCAATTT...TCATTGAGCATAGAGAAAATCCAAAATTCATTACAG..
1637
1638  49_HRV47     ----CA--------------
1639  50_HRV47a|   ----CT--------------
1640  51_HRV47b|   ----CA--------------
1641  GROUP_16     ....C-..............
1642
1643
1644
1645  Group 17:
1646
1647  52_HRV11     AACCCAGTGGAGGATTATGTTGATGGAATTCTAAATGAGGTTTTAGTTGTACCTAATATA
1648  53_HRV11b|   AACCCAGTGGAGGATTATGTTGATGGAATTCTAAATGAGGTTTTAGTTGTACCTAATATA
1649  54_HRV11a|   AACCCAGTGGAGGATTATGTTGATGGAATTCTAAATGAGGTTTTAGTTGTACCTAATATA
1650  GROUP_17     AACCCAGTGGAGGATTATGTTGATGGAATTCTAAATGAGGTTTTAGTTGTACCTAATATA
1651
1652  52_HRV11     AAGGAGAGCCAAGCTACCACATCAAACTCAGCACCTGCTCTAGATGCAGCTGAAACCGGA
1653  53_HRV11b|   AAGGAGAGCCAAGCTACCACATCAAACTCAGCACCTGCTCTAGATGCAGCTGAAACCGGA
1654  54_HRV11a|   AAGGAGAGCCAAGCTACCACATCAAACTCAGCACCTGCTCTAGATGCAGCTGAAACCGGA
1655  GROUP_17     AAGGAGAGCCAAGCTACCACATCAAACTCAGCACCTGCTCTAGATGCAGCTGAAACCGGA
1656
1657  52_HRV11     CATACTAGCAAAGTGCAGCCAGAGGATATGATTGAGACTAGATATGTGCAGACTTCACAG
1658  53_HRV11b|   CATACTAGCAAAGTGCAGCCAGAGGATATGATTGAGACTAGATATGTGCAGACTTCACAG
1659  54_HRV11a|   CATACTAGCAAAGTGCAGCCAGAGGATATGATTGAGACTAGATATGTGCAGACTTCACAG
1660  GROUP_17     CATACTAGCAAAGTGCAGCCAGAGGATATGATTGAGACTAGATATGTGCAGACTTCACAG
1661
1662  52_HRV11     ACTCTTGATGAAATGAGCATTGAGAGCTTCCTAGGTAGATCTGGTTGTATTCACATGTCC
1663  53_HRV11b|   ACTCTTGATGAAATGAGCATTGAGAGCTTCCTAGGTAGATCTGGTTGTATTCACATGTCC
1664  54_HRV11a|   ACTCTTGATGAAATGAGCATTGAGAGCTTCCTAGGTAGATCTGGTTGTATTCACATGTCC
1665  GROUP_17     ACTCTTGATGAAATGAGCATTGAGAGCTTCCTAGGTAGATCTGGTTGTATTCACATGTCC
1666
1667  52_HRV11     AAGTTAATTGTGCAGTATGAAGAC---------------TATAAT------GGAAAGAAA
1668  53_HRV11b|   AAGTTAATTGTGCAGTATGAAGAC---------------TATAAT------GGAAAGAAA
1669  54_HRV11a|   AAGTTAATTGTGCAGTATGAAGAC---------------TATAAT------GGAAAGAAA
1670  GROUP_17     AAGTTAATTGTGCAGTATGAAGAC...............TATAAT......GGAAAGAAA
1671
1672  52_HRV11     AACTTTAACACATGGAAAATAAACTTGCAAGAGATGGCACAAATTAGAAGGAAATTTGAA
1673  53_HRV11b|   AACTTTAACACATGGAAAATAAACTTGCAAGAGATGGCACAAATTAGAAGGAAATTTGAA
1674  54_HRV11a|   AACTTTAACACATGGAAAATAAACTTGCAAGAGATGGCACAAATTAGAAGGAAATTTGAA
1675  GROUP_17     AACTTTAACACATGGAAAATAAACTTGCAAGAGATGGCACAAATTAGAAGGAAATTTGAA
1676
1677  52_HRV11     ATGTTCACATACACTAGATTTGATTCAGAGATCACATTGG-TGCCTTGTATAGCTGCAAA
1678  53_HRV11b|   ATGTTCACATACACTAGATTTGATTCAGAGATCACATTGG-TGCCTTGTATAGCTGCAAA
1679  54_HRV11a|   ATGTTCACATACACTAGATTTGATTCAGAGATCACATTGG-TGCCTTGTATAGCTGCAAA
1680  GROUP_17     ATGTTCACATACACTAGATTTGATTCAGAGATCACATTGG.TGCCTTGTATAGCTGCAAA
1681
1682  52_HRV11     AGGAAATGATATTGGTCATGTTGTAATGCAATATATGTATGTCCCACCAGGTGCTCCAGT
```

FIG. D14 CONT'D

```
10.trace                                                                9/20/2007 5:05 PM 1683 53_HRV11b|    AGGAAATGATATTGGTCATGTTGTAATGCAATATATGTATGTCCCACCAGGTGCTCCAGT
1684 54_HRV11a|    AGGAAATGATATTGGTCATGTTGTAATGCAATATATGTATGTCCCACCAGGTGCTCCAGT
1685 GROUP_17     AGGAAATGATATTGGTCATGTTGTAATGCAATATATGTATGTCCCACCAGGTGCTCCAGT
1686
1687 52_HRV11     TCCAGAGAAAAGAGATGATTATACATGGCAATCAGGAACAAATGCATCTATTTTCTGGCA
1688 53_HRV11b|    TCCAGAGAAAAGAGATGATTATACATGGCAATCAGGAACAAATGCATCTATTTTCTGGCA
1689 54_HRV11a|    TCCAGAGAAAAGAGATGATTATACATGGCAATCAGGAACAAATGCATCTATTTTCTGGCA
1690 GROUP_17     TCCAGAGAAAAGAGATGATTATACATGGCAATCAGGAACAAATGCATCTATTTTCTGGCA
1691
1692 52_HRV11     ATATGGTCAAACATACCCAAGATTTTCTCTACCTTTCATGAGTATAGCCTCAGCATATTA
1693 53_HRV11b|    ATATGGTCAAACATACCCAAGATTTTCTCTACCTTTCATGAGTATAGCCTCAGCATATTA
1694 54_HRV11a|    ATATGGTCAAACATACCCAAGATTTTCTCTACCTTTCATGAGTATAGCCTCAGCATATTA
1695 GROUP_17     ATATGGTCAAACATACCCAAGATTTTCTCTACCTTTCATGAGTATAGCCTCAGCATATTA
1696
1697 52_HRV11     CATGTTTTATGATGGATATGATGGAGATCAACCAAACTCCAGATATGGTAATATAGTTAC
1698 53_HRV11b|    CATGTTTTATGATGGATATGATGGAGATCAACCAAACTCCAGATATGGTAATATAGTTAC
1699 54_HRV11a|    CATGTTTTATGATGGATATGATGGAGATCAACCAAACTCCAGATATGGTAATATAGTTAC
1700 GROUP_17     CATGTTTTATGATGGATATGATGGAGATCAACCAAACTCCAGATATGGTAATATAGTTAC
1701
1702 52_HRV11     CAATGATATGGGCACTCTGTGTTATAGAATAGTAACTGATGACCATAGACACAAAATTGA
1703 53_HRV11b|    CAATGATATGGGCACTCTGTGTTATAGAATAGTAACTGATGACCATAGACACAAAATTGA
1704 54_HRV11a|    CAATGATATGGGCACTCTGTGTTATAGAATAGTAACTGATGACCATAGACACAAAATTGA
1705 GROUP_17     CAATGATATGGGCACTCTGTGTTATAGAATAGTAACTGATGACCATAGACACAAAATTGA
1706
1707 52_HRV11     AGTCACAACTAGGGTGTATCATAAAGCAAAGCATGTGAAGGTGTGGTGTCCAAGACCACC
1708 53_HRV11b|    AGTCACAACTAGGGTGTATCATAAAGCAAAGCATGTGAAGGTGTGGTGTCCAAGACCACC
1709 54_HRV11a|    AGTCACAACTAGGGTGTATCATAAAGCAAAGCATGTGAAGGTGTGGTGTCCAAGACCACC
1710 GROUP_17     AGTCACAACTAGGGTGTATCATAAAGCAAAGCATGTGAAGGTGTGGTGTCCAAGACCACC
1711
1712 52_HRV11     TAGAGCTGTAGAATATACT-CACACTCATGTAACCAATTACAAAC-CACAGG---AAGGA
1713 53_HRV11b|    TAGAGCTGTAGAATATACT-CACACTCATGTAACCAATTACAAAC-CACAGG---AAGGA
1714 54_HRV11a|    TAGAGCTGTAGAATATACT-CACACTCATGTAACCAATTACAAAC-CACAGG---AAGGA
1715 GROUP_17     TAGAGCTGTAGAATATACT.CACACTCATGTAACCAATTACAAAC.CACAGG...AAGGA
1716
1717 52_HRV11     CAGG------TGAAAACAG---CTGTCAAGGCTAGGAAAACAATTAAAACAGCA------
1718 53_HRV11b|    CAGG------TGAAAACAG---CTGTCAAGGCTAGGAAAACAATTAAAACAGCG------
1719 54_HRV11a|    CAGG------TGAAAACAG---CTGTCAAGGCTAGGAAAACAATTAAAACAGCT------
1720 GROUP_17     CAGG......TGAAAACAG...CTGTCAAGGCTAGGAAAACAATTAAAACAGC-......
1721
1722 52_HRV11     --------------------
1723 53_HRV11b|    --------------------
1724 54_HRV11a|    --------------------
1725 GROUP_17     ....................
1726
1727
1728
1729 Group 18:
1730
1731 55_HRV76     AACCCAGTTGAAAATTACGTGGATGAGATATTAAATGAGGTTCTTGTAGTACCAAACATC
1732 56_HRV76b|    AACCCAGTTGAAAATTACGTGGATGAGATATTAAATGAGGTTCTTGTAGTACCAAACATC
1733 57_HRV76a|    AACCCAGTTGAAAATTACGTGGATGAGATATTAAATGAGGTTCTTGTAGTACCAAACATC
1734 GROUP_18     AACCCAGTTGAAAATTACGTGGATGAGATATTAAATGAGGTTCTTGTAGTACCAAACATC
1735
1736 55_HRV76     AAAGAGAGTCAGGCTACCACATCAAATGCAGCACCTGCTTTGGATGCAGCTGAGACTGGG
1737 56_HRV76b|    AAAGAGAGTCAGGCTACCACATCAAATGCAGCACCTGCTTTGGATGCAGCTGAGACTGGG
1738 57_HRV76a|    AAAGAGAGTCAGGCTACCACATCAAATGCAGCACCTGCTTTGGATGCAGCTGAGACTGGG
1739 GROUP_18     AAAGAGAGTCAGGCTACCACATCAAATGCAGCACCTGCTTTGGATGCAGCTGAGACTGGG
1740
1741 55_HRV76     CACACAAGCAGCGTTCAACCAGAGGACATGGTTGAGACTAGGTATGTGCAAACATCACAA
1742 56_HRV76b|    CACACAAGCAGCGTTCAACCAGAGGACATGGTTGAGACTAGGTATGTGCAAACATCACAA
1743 57_HRV76a|    CACACAAGCAGCGTTCAACCAGAGGACATGGTTGAGACTAGGTATGTGCAAACATCACAA
1744 GROUP_18     CACACAAGCAGCGTTCAACCAGAGGACATGGTTGAGACTAGGTATGTGCAAACATCACAA
1745
1746 55_HRV76     ACTCTTGATGAGATGTGTATGGAGAGTTTCTTAGGGAGATCTGGTTGTATTCATATTTCA
1747 56_HRV76b|    ACTCTTGATGAGATGTGTATGGAGAGTTTCTTAGGGAGATCTGGTTGTATTCATATTTCA
```

FIG. D14 CONT'D

```
10.trace                                                                    9/20/2007 5:05 PM 1748 57_HRV76a|    ACTCTTGATGAGATGTGTATGGAGAGTTTCTTAGGGAGATCTGGTTGTATTCATATTTCA
1749 GROUP_18     ACTCTTGATGAGATGTGTATGGAGAGTTTCTTAGGGAGATCTGGTTGTATTCATATTTCA
1750
1751 55_HRV76     AAGCTAGTTGTAGAATATGAGGGA---------------TATGAT------GATACAAAA
1752 56_HRV76b|   AAGCTAGTTGTAGAATATGAGGGA---------------TATGAT------GATACAAAA
1753 57_HRV76a|   AAGCTAGTTGTAGAATATGAGGGA---------------TATGAT------GATACAAAA
1754 GROUP_18     AAGCTAGTTGTAGAATATGAGGGA...............TATGAT......GATACAAAA
1755
1756 55_HRV76     AACTTTAAGACATGGAAAATAAACCTACAAGAAATGGCACAAGTTAGAAGAAAATTTGAG
1757 56_HRV76b|   AACTTTAAGACATGGAAAATAAACCTACAAGAAATGGCACAAGTTAGAAGAAAATTTGAG
1758 57_HRV76a|   AACTTTAAGACATGGAAAATAAACCTACAAGAAATGGCACAAGTTAGAAGAAAATTTGAG
1759 GROUP_18     AACTTTAAGACATGGAAAATAAACCTACAAGAAATGGCACAAGTTAGAAGAAAATTTGAG
1760
1761 55_HRV76     ATGTTTACATATACTAGATTTGATTCAGAAGTTACTCTAG-TTCCTTCTATAGCTGCCAA
1762 56_HRV76b|   ATGTTTACATATACTAGATTTGATTCAGAAGTTACTCTAG-TTCCTTCTATAGCTGCCAA
1763 57_HRV76a|   ATGTTTACATATACTAGATTTGATTCAGAAGTTACTCTAG-TTCCTTCTATAGCTGCCAA
1764 GROUP_18     ATGTTTACATATACTAGATTTGATTCAGAAGTTACTCTAG.TTCCTTCTATAGCTGCCAA
1765
1766 55_HRV76     AGGGGATGACATTGGTCATGTAGTGATGCAATACATGTATGTCCCACCAGGCGCTCCAGT
1767 56_HRV76b|   AGGGGATGACATTGGTCATGTAGTGATGCAATACATGTATGTCCCACCAGGCGCTCCAGT
1768 57_HRV76a|   AGGGGATGACATTGGTCATGTAGTGATGCAATACATGTATGTCCCACCAGGCGCTCCAGT
1769 GROUP_18     AGGGGATGACATTGGTCATGTAGTGATGCAATACATGTATGTCCCACCAGGCGCTCCAGT
1770
1771 55_HRV76     TCCAAAGAAGAGAGATGACTACACATGGCAGTCAGGAACCAATGCATCTATTTTCTGGCA
1772 56_HRV76b|   TCCAAAGAAGAGAGATGACTACACATGGCAGTCAGGAACCAATGCATCTATTTTCTGGCA
1773 57_HRV76a|   TCCAAAGAAGAGAGATGACTACACATGGCAGTCAGGAACCAATGCATCTATTTTCTGGCA
1774 GROUP_18     TCCAAAGAAGAGAGATGACTACACATGGCAGTCAGGAACCAATGCATCTATTTTCTGGCA
1775
1776 55_HRV76     ATATGGACAAACATACCCTAGGTTTTCATTACCCTTTCTAAGTATAGCTTCAGCTTATTA
1777 56_HRV76b|   ATATGGACAAACATACCCTAGGTTTTCATTACCCTTTCTAAGTATAGCTTCAGCTTATTA
1778 57_HRV76a|   ATATGGACAAACATACCCTAGGTTTTCATTACCCTTTCTAAGTATAGCTTCAGCTTATTA
1779 GROUP_18     ATATGGACAAACATACCCTAGGTTTTCATTACCCTTTCTAAGTATAGCTTCAGCTTATTA
1780
1781 55_HRV76     CATGTTTTATGATGGATATGATGGAGACCAACCTAGTTCTAGGTATGGTAATATAGTTAC
1782 56_HRV76b|   CATGTTTTATGATGGATATGATGGAGACCAACCTAGTTCTAGGTATGGTAATATAGTTAC
1783 57_HRV76a|   CATGTTTTATGATGGATATGATGGAGACCAACCTAGTTCTAGGTATGGTAATATAGTTAC
1784 GROUP_18     CATGTTTTATGATGGATATGATGGAGACCAACCTAGTTCTAGGTATGGTAATATAGTTAC
1785
1786 55_HRV76     CAATGACATGGGCACCCTATGTTCCAGGATAGTAACTGATGATCATAAGCACAAGATTGA
1787 56_HRV76b|   CAATGACATGGGCACCCTATGTTCCAGGATAGTAACTGATGATCATAAGCACAAGATTGA
1788 57_HRV76a|   CAATGACATGGGCACCCTATGTTCCAGGATAGTAACTGATGATCATAAGCACAAGATTGA
1789 GROUP_18     CAATGACATGGGCACCCTATGTTCCAGGATAGTAACTGATGATCATAAGCACAAGATTGA
1790
1791 55_HRV76     AGTTACAACAAGAATATATCACAAAGCAAAGCATGTTAAGGTATGGTGCCCGAGACCACC
1792 56_HRV76b|   AGTTACAACAAGAATATATCACAAAGCAAAGCATGTTAAGGTATGGTGCCCGAGACCACC
1793 57_HRV76a|   AGTTACAACAAGAATATATCACAAAGCAAAGCATGTTAAGGTATGGTGCCCGAGACCACC
1794 GROUP_18     AGTTACAACAAGAATATATCACAAAGCAAAGCATGTTAAGGTATGGTGCCCGAGACCACC
1795
1796 55_HRV76     TAGAGCTGTAGAGTATACA-TACACCCATGTAACAAACTACAAAC-CACATT---CTGGT
1797 56_HRV76b|   TAGAGCTGTAGAGTATACA-TACACCCATGTAACAAACTACAAAC-CACATT---CTGGT
1798 57_HRV76a|   TAGAGCTGTAGAGTATACA-TACACCCATGTAACAAACTACAAAC-CACATT---CTGGT
1799 GROUP_18     TAGAGCTGTAGAGTATACA.TACACCCATGTAACAAACTACAAAC.CACATT...CTGGT
1800
1801 55_HRV76     GATG------TGCAAACAG---CTATTAGACCAAGAGCAACAATTAAGACTGCA------
1802 56_HRV76b|   GATG------TGCAAACAG---CTATTAGACCAAGAGCAACAATTAAGACTGCG------
1803 57_HRV76a|   GATG------TGCAAACAG---CTATTAGACCAAGAGCAACAATTAAGACTGCT------
1804 GROUP_18     GATG......TGCAAACAG...CTATTAGACCAAGAGCAACAATTAAGACTGC-......
1805
1806 55_HRV76     --------------------
1807 56_HRV76b|   --------------------
1808 57_HRV76a|   --------------------
1809 GROUP_18     ....................
1810
1811
1812
```

FIG. D14 CONT'D

10.trace                                                                9/20/2007 5:05 PM

```
1813 Group 19:
1814
1815 58_HRV33    AATCCAGTAGAGAATTATATAGAAGAGGTGTTGAATGAGGTTTTAGTAGTGCCTAATATC
1816 59_HRV33b|  AATCCAGTAGAGAATTATATAGAAGAGGTGTTGAATGAGGTTTTAGTAGTGCCTAATATC
1817 60_HRV33a|  AATCCAGTAGAGAATTATATAGAAGAGGTGTTGAATGAGGTTTTAGTAGTGCCTAATATC
1818 GROUP_19    AATCCAGTAGAGAATTATATAGAAGAGGTGTTGAATGAGGTTTTAGTAGTGCCTAATATC
1819
1820 58_HRV33    AGAGAGAGTCAAGCAACCACATCAAATTCAGCACCTGCCTTAGATGCAGCTGAGACTGGA
1821 59_HRV33b|  AGAGAGAGTCAAGCAACCACATCAAATTCAGCACCTGCCTTAGATGCAGCTGAGACTGGA
1822 60_HRV33a|  AGAGAGAGTCAAGCAACCACATCAAATTCAGCACCTGCCTTAGATGCAGCTGAGACTGGA
1823 GROUP_19    AGAGAGAGTCAAGCAACCACATCAAATTCAGCACCTGCCTTAGATGCAGCTGAGACTGGA
1824
1825 58_HRV33    CACACTAATAATGTACAACCAGAAGATATGATTGAAACAAGATATGTACAAACATCACAA
1826 59_HRV33b|  CACACTAATAATGTACAACCAGAAGATATGATTGAAACAAGATATGTACAAACATCACAA
1827 60_HRV33a|  CACACTAATAATGTACAACCAGAAGATATGATTGAAACAAGATATGTACAAACATCACAA
1828 GROUP_19    CACACTAATAATGTACAACCAGAAGATATGATTGAAACAAGATATGTACAAACATCACAA
1829
1830 58_HRV33    ACTCTTGATGAGATGAGTGTGGAAAGCTTCTTAGGAAGGTCTGGTTGCATTCACATGTCA
1831 59_HRV33b|  ACTCTTGATGAGATGAGTGTGGAAAGCTTCTTAGGAAGGTCTGGTTGCATTCACATGTCA
1832 60_HRV33a|  ACTCTTGATGAGATGAGTGTGGAAAGCTTCTTAGGAAGGTCTGGTTGCATTCACATGTCA
1833 GROUP_19    ACTCTTGATGAGATGAGTGTGGAAAGCTTCTTAGGAAGGTCTGGTTGCATTCACATGTCA
1834
1835 58_HRV33    AAATTAGTAGTGAAATATGAAGAC---------------TATAAT------GAGAAAAAG
1836 59_HRV33b|  AAATTAGTAGTGAAATATGAAGAC---------------TATAAT------GAGAAAAAG
1837 60_HRV33a|  AAATTAGTAGTGAAATATGAAGAC---------------TATAAT------GAGAAAAAG
1838 GROUP_19    AAATTAGTAGTGAAATATGAAGAC...............TATAAT......GAGAAAAAG
1839
1840 58_HRV33    AATTTTATGACATGGAAAATAAATCTACAAGAGATGGCACAGATTAGGAGGAAATTTGAA
1841 59_HRV33b|  AATTTTATGACATGGAAAATAAATCTACAAGAGATGGCACAGATTAGGAGGAAATTTGAA
1842 60_HRV33a|  AATTTTATGACATGGAAAATAAATCTACAAGAGATGGCACAGATTAGGAGGAAATTTGAA
1843 GROUP_19    AATTTTATGACATGGAAAATAAATCTACAAGAGATGGCACAGATTAGGAGGAAATTTGAA
1844
1845 58_HRV33    ATGTTTACATATGCCAGATTTGATTCAGAGATCACCCTAG-TCCCTTCTATAGCTGCCCA
1846 59_HRV33b|  ATGTTTACATATGCCAGATTTGATTCAGAGATCACCCTAG-TCCCTTCTATAGCTGCCCA
1847 60_HRV33a|  ATGTTTACATATGCCAGATTTGATTCAGAGATCACCCTAG-TCCCTTCTATAGCTGCCCA
1848 GROUP_19    ATGTTTACATATGCCAGATTTGATTCAGAGATCACCCTAG.TCCCTTCTATAGCTGCCCA
1849
1850 58_HRV33    GGGAGATGATGTTGGTCATGTTGTAATGCAGTACATGTATGTCCCACCAGGTGCACCAGC
1851 59_HRV33b|  GGGAGATGATGTTGGTCATGTTGTAATGCAGTACATGTATGTCCCACCAGGTGCACCAGC
1852 60_HRV33a|  GGGAGATGATGTTGGTCATGTTGTAATGCAGTACATGTATGTCCCACCAGGTGCACCAGC
1853 GROUP_19    GGGAGATGATGTTGGTCATGTTGTAATGCAGTACATGTATGTCCCACCAGGTGCACCAGC
1854
1855 58_HRV33    TCCAGAAAAGAGAGATGATTACACATGGCAATCAGGAACAAATGCATCTGTCTTTTGGCA
1856 59_HRV33b|  TCCAGAAAAGAGAGATGATTACACATGGCAATCAGGAACAAATGCATCTGTCTTTTGGCA
1857 60_HRV33a|  TCCAGAAAAGAGAGATGATTACACATGGCAATCAGGAACAAATGCATCTGTCTTTTGGCA
1858 GROUP_19    TCCAGAAAAGAGAGATGATTACACATGGCAATCAGGAACAAATGCATCTGTCTTTTGGCA
1859
1860 58_HRV33    ATATGGACAAACATATCCTAGGTTCTCATTACCTTTCCTTAGCATAGCTTCAGCATATTA
1861 59_HRV33b|  ATATGGACAAACATATCCTAGGTTCTCATTACCTTTCCTTAGCATAGCTTCAGCATATTA
1862 60_HRV33a|  ATATGGACAAACATATCCTAGGTTCTCATTACCTTTCCTTAGCATAGCTTCAGCATATTA
1863 GROUP_19    ATATGGACAAACATATCCTAGGTTCTCATTACCTTTCCTTAGCATAGCTTCAGCATATTA
1864
1865 58_HRV33    CATGTTCTATGATGGATATGATGGGGACCAACCCAATTCCAGGTATGGTAATATGGTTAC
1866 59_HRV33b|  CATGTTCTATGATGGATATGATGGGGACCAACCCAATTCCAGGTATGGTAATATGGTTAC
1867 60_HRV33a|  CATGTTCTATGATGGATATGATGGGGACCAACCCAATTCCAGGTATGGTAATATGGTTAC
1868 GROUP_19    CATGTTCTATGATGGATATGATGGGGACCAACCCAATTCCAGGTATGGTAATATGGTTAC
1869
1870 58_HRV33    CAATGACATGGGCACTTTATGCTCTAGAATAGTTACAGATAATCATAAGCATCCAATAGA
1871 59_HRV33b|  CAATGACATGGGCACTTTATGCTCTAGAATAGTTACAGATAATCATAAGCATCCAATAGA
1872 60_HRV33a|  CAATGACATGGGCACTTTATGCTCTAGAATAGTTACAGATAATCATAAGCATCCAATAGA
1873 GROUP_19    CAATGACATGGGCACTTTATGCTCTAGAATAGTTACAGATAATCATAAGCATCCAATAGA
1874
1875 58_HRV33    AGTTACAACAAGAGTATACCATAAAGCAAAACATGTCAAAGTCTGGTGCCCAAGACCACC
1876 59_HRV33b|  AGTTACAACAAGAGTATACCATAAAGCAAAACATGTCAAAGTCTGGTGCCCAAGACCACC
1877 60_HRV33a|  AGTTACAACAAGAGTATACCATAAAGCAAAACATGTCAAAGTCTGGTGCCCAAGACCACC
```

FIG. D14 CONT'D

```
10.trace                                                                                    9/20/2007 5:05 PM 1878 GROUP_19       AGTTACAACAAGAGTATACCATAAAGCAAAACATGTCAAAGTCTGGTGCCCAAGACCACC
1879
1880 58_HRV33       TAGAGCTGTGGAATACACC-CATACTCATGTTACAAATTATAAAT-CAACAA---CTCGT
1881 59_HRV33b|     TAGAGCTGTGGAATACACC-CATACTCATGTTACAAATTATAAAT-CAACAA---CTCGT
1882 60_HRV33a|     TAGAGCTGTGGAATACACC-CATACTCATGTTACAAATTATAAAT-CAACAA---CTCGT
1883 GROUP_19       TAGAGCTGTGGAATACACC.CATACTCATGTTACAAATTATAAAT.CAACAA...CTCGT
1884
1885 58_HRV33       GAAG------TGAAGACAG---CTATTAGACCAAGAGCAACAATCAAGACTGCA------
1886 59_HRV33b|     GAAG------TGAAGACAG---CTATTAGACCAAGAGCAACAATCAAGACTGCG------
1887 60_HRV33a|     GAAG------TGAAGACAG---CTATTAGACCAAGAGCAACAATCAAGACTGCT------
1888 GROUP_19       GAAG......TGAAGACAG...CTATTAGACCAAGAGCAACAATCAAGACTGC-......
1889
1890 58_HRV33       --------------------
1891 59_HRV33b|     --------------------
1892 60_HRV33a|     --------------------
1893 GROUP_19       ....................
1894
1895
1896
1897 Group 20:
1898
1899 61_HRV24a|     AACCCAGTAGAAAATTATATAGATGAGGTTTTGAATGAAGTACTGGTTGTGCCTAATATT
1900 62_HRV24b|     AACCCAGTAGAAAATTATATAGATGAGGTTTTGAATGAAGTACTGGTTGTGCCTAATATT
1901 63_HRV24       AACCCAGTAGAAAATTATATAGATGAGGTTTTGAATGAAGTACTGGTTGTGCCTAATATT
1902 GROUP_20       AACCCAGTAGAAAATTATATAGATGAGGTTTTGAATGAAGTACTGGTTGTGCCTAATATT
1903
1904 61_HRV24a|     AAGGAAAGTAAACCATCAACATCAAACTCAGCACCAGCTTTGGATGCAGCAGAAACTGGA
1905 62_HRV24b|     AAGGAAAGTAAACCATCAACATCAAACTCAGCACCAGCTTTGGATGCAGCAGAAACTGGA
1906 63_HRV24       AAGGAAAGTAAACCATCAACATCAAACTCAGCACCAGCTTTGGATGCAGCAGAAACTGGA
1907 GROUP_20       AAGGAAAGTAAACCATCAACATCAAACTCAGCACCAGCTTTGGATGCAGCAGAAACTGGA
1908
1909 61_HRV24a|     CATACGAGTAGCGTGCAGCCAGAAGATATGGTTGAAACTAGATATGTCCAAACATCACAA
1910 62_HRV24b|     CATACGAGTAGCGTGCAGCCAGAAGATATGGTTGAAACTAGATATGTCCAAACATCACAA
1911 63_HRV24       CATACGAGTAGCGTGCAGCCAGAAGATATGGTTGAAACTAGATATGTCCAAACATCACAA
1912 GROUP_20       CATACGAGTAGCGTGCAGCCAGAAGATATGGTTGAAACTAGATATGTCCAAACATCACAA
1913
1914 61_HRV24a|     ACATTACATGAGATGAGTGTTGAAAGTTTCTTGGGTAGATCAGGTTGCATACACATGTCC
1915 62_HRV24b|     ACATTACATGAGATGAGTGTTGAAAGTTTCTTGGGTAGATCAGGTTGCATACACATGTCC
1916 63_HRV24       ACATTACATGAGATGAGTGTTGAAAGTTTCTTGGGTAGATCAGGTTGCATACACATGTCC
1917 GROUP_20       ACATTACATGAGATGAGTGTTGAAAGTTTCTTGGGTAGATCAGGTTGCATACACATGTCC
1918
1919 61_HRV24a|     AAGTTGACTGTGGATTAT---GAC---------------AATTAT------GATACAAAA
1920 62_HRV24b|     AAGTTGACTGTGGATTAT---GAC---------------AATTAT------GATACAAAA
1921 63_HRV24       AAGTTGACTGTGGATTAT---GAC---------------AATTAT------GATACAAAA
1922 GROUP_20       AAGTTGACTGTGGATTAT...GAC...............AATTAT......GATACAAAA
1923
1924 61_HRV24a|     AATTTTTTCAAATGGCAAATAAATCTACAAGAAATGGCCCAAGTCAGAAGAAAATTTGAA
1925 62_HRV24b|     AATTTTTTCAAATGGCAAATAAATCTACAAGAAATGGCCCAAGTCAGAAGAAAATTTGAA
1926 63_HRV24       AATTTTTTCAAATGGCAAATAAATCTACAAGAAATGGCCCAAGTCAGAAGAAAATTTGAA
1927 GROUP_20       AATTTTTTCAAATGGCAAATAAATCTACAAGAAATGGCCCAAGTCAGAAGAAAATTTGAA
1928
1929 61_HRV24a|     TTATTCACATATACTAGATTTGACTCTGAGATTACAATAG-TTCCATCCATAGCTGGCAA
1930 62_HRV24b|     TTATTCACATATACTAGATTTGACTCTGAGATTACAATAG-TTCCATCCATAGCTGGCAA
1931 63_HRV24       TTATTCACATATACTAGATTTGACTCTGAGATTACAATAG-TTCCATCCATAGCTGGCAA
1932 GROUP_20       TTATTCACATATACTAGATTTGACTCTGAGATTACAATAG.TTCCATCCATAGCTGGCAA
1933
1934 61_HRV24a|     GGGAGATGACATTGGACATGTTGTAATGCAGTACATGTATATACCACCTGGAGCACCAGT
1935 62_HRV24b|     GGGAGATGACATTGGACATGTTGTAATGCAGTACATGTATATACCACCTGGAGCACCAGT
1936 63_HRV24       GGGAGATGACATTGGACATGTTGTAATGCAGTACATGTATATACCACCTGGAGCACCAGT
1937 GROUP_20       GGGAGATGACATTGGACATGTTGTAATGCAGTACATGTATATACCACCTGGAGCACCAGT
1938
1939 61_HRV24a|     CCCAACAAAGAGAGATGATTATACATGGCAATCAGGAACAAATGCATCTGTCTTTTGGCA
1940 62_HRV24b|     CCCAACAAAGAGAGATGATTATACATGGCAATCAGGAACAAATGCATCTGTCTTTTGGCA
1941 63_HRV24       CCCAACAAAGAGAGATGATTATACATGGCAATCAGGAACAAATGCATCTGTCTTTTGGCA
1942 GROUP_20       CCCAACAAAGAGAGATGATTATACATGGCAATCAGGAACAAATGCATCTGTCTTTTGGCA
```

FIG. D14 CONT'D 10.trace                                                                       9/20/2007 5:05 PM

```
1943
1944 61_HRV24a|   ACATGGACAAACCTATCCTAGATTTTCCCTTCCTTTTCTGAGTGTAGCCTCTGCATATTA
1945 62_HRV24b|   ACATGGACAAACCTATCCTAGATTTTCCCTTCCTTTTCTGAGTGTAGCCTCTGCATATTA
1946 63_HRV24    ACATGGACAAACCTATCCTAGATTTTCCCTTCCTTTTCTGAGTGTAGCCTCTGCATATTA
1947 GROUP_20    ACATGGACAAACCTATCCTAGATTTTCCCTTCCTTTTCTGAGTGTAGCCTCTGCATATTA
1948
1949 61_HRV24a|   CATGTTTTATGATGGATATGATGGTGATCAACACGACTCAGTGTATGGTTCAGTTGTTAC
1950 62_HRV24b|   CATGTTTTATGATGGATATGATGGTGATCAACACGACTCAGTGTATGGTTCAGTTGTTAC
1951 63_HRV24    CATGTTTTATGATGGATATGATGGTGATCAACACGACTCAGTGTATGGTTCAGTTGTTAC
1952 GROUP_20    CATGTTTTATGATGGATATGATGGTGATCAACACGACTCAGTGTATGGTTCAGTTGTTAC
1953
1954 61_HRV24a|   AAACGACATGGGAACTCTATGCTATAGAATAGTCACTGACAAGCATAATCACCAAATAGA
1955 62_HRV24b|   AAACGACATGGGAACTCTATGCTATAGAATAGTCACTGACAAGCATAATCACCAAATAGA
1956 63_HRV24    AAACGACATGGGAACTCTATGCTATAGAATAGTCACTGACAAGCATAATCACCAAATAGA
1957 GROUP_20    AAACGACATGGGAACTCTATGCTATAGAATAGTCACTGACAAGCATAATCACCAAATAGA
1958
1959 61_HRV24a|   AATTACAACAAGAATATACCACAAAGCAAAGCACATTAAGGTCTGGTGTCCAAGGCCACC
1960 62_HRV24b|   AATTACAACAAGAATATACCACAAAGCAAAGCACATTAAGGTCTGGTGTCCAAGGCCACC
1961 63_HRV24    AATTACAACAAGAATATACCACAAAGCAAAGCACATTAAGGTCTGGTGTCCAAGGCCACC
1962 GROUP_20    AATTACAACAAGAATATACCACAAAGCAAAGCACATTAAGGTCTGGTGTCCAAGGCCACC
1963
1964 61_HRV24a|   CAGAGCTGTTGAGTATACA-CATACTCACGTGACCAATTATAAGC-ATCAGA---CTCGT
1965 62_HRV24b|   CAGAGCTGTTGAGTATACA-CATACTCACGTGACCAATTATAAGC-ATCAGA---CTCGT
1966 63_HRV24    CAGAGCTGTTGAGTATACA-CATACTCACGTGACCAATTATAAGC-ATCAGA---CTCGT
1967 GROUP_20    CAGAGCTGTTGAGTATACA.CATACTCACGTGACCAATTATAAGC.ATCAGA...CTCGT
1968
1969 61_HRV24a|   GAAG------TCAAGACAG---CAATTGAACCTAGAAGAGGAATTAAAACAGTG------
1970 62_HRV24b|   GAAG------TCAAGACAG---CAATTGAACCTAGAAGAGGAATTAAAACAGTC------
1971 63_HRV24    GAAG------TCAAGACAG---CAATTGAACCTAGAAGAGGAATTAAAACAGTT------
1972 GROUP_20    GAAG......TCAAGACAG...CAATTGAACCTAGAAGAGGAATTAAAACAGT-......
1973
1974 61_HRV24a|   --------------------
1975 62_HRV24b|   --------------------
1976 63_HRV24    --------------------
1977 GROUP_20    ....................
1978
1979
1980
1981 Group  21:
1982
1983 64_HRV90     AATCCAGTGGAAAATTATATAGATGAAGTCCTAAATGAGGTATTGGTTGTCCCTAATATT
1984 65_HRV90a|   AATCCAGTGGAAAATTATATAGATGAAGTCCTAAATGAGGTATTGGTTGTCCCTAATATT
1985 66_HRV90b|   AATCCAGTGGAAAATTATATAGATGAAGTCCTAAATGAGGTATTGGTTGTCCCTAATATT
1986 GROUP_21    AATCCAGTGGAAAATTATATAGATGAAGTCCTAAATGAGGTATTGGTTGTCCCTAATATT
1987
1988 64_HRV90     AAGGAAAGTAAACCTTCAACTTCAAACTCAGCGCCAGCTTTAGATGCAGCAGAAACCGGA
1989 65_HRV90a|   AAGGAAAGTAAACCTTCAACTTCAAACTCAGCGCCAGCTTTAGATGCAGCAGAAACCGGA
1990 66_HRV90b|   AAGGAAAGTAAACCTTCAACTTCAAACTCAGCGCCAGCTTTAGATGCAGCAGAAACCGGA
1991 GROUP_21    AAGGAAAGTAAACCTTCAACTTCAAACTCAGCGCCAGCTTTAGATGCAGCAGAAACCGGA
1992
1993 64_HRV90     CATACTAGTGATGTCCAGCCAGAAGATGTGGTAGAGACCAGATACGTGCAAACATCACAA
1994 65_HRV90a|   CATACTAGTGATGTCCAGCCAGAAGATGTGGTAGAGACCAGATACGTGCAAACATCACAA
1995 66_HRV90b|   CATACTAGTGATGTCCAGCCAGAAGATGTGGTAGAGACCAGATACGTGCAAACATCACAA
1996 GROUP_21    CATACTAGTGATGTCCAGCCAGAAGATGTGGTAGAGACCAGATACGTGCAAACATCACAA
1997
1998 64_HRV90     ACAAGAGATGAAATGAGTGTTGAAAGTTTTCTAGGGAGATCAGGTTGCATTCATATGTCA
1999 65_HRV90a|   ACAAGAGATGAAATGAGTGTTGAAAGTTTTCTAGGGAGATCAGGTTGCATTCATATGTCA
2000 66_HRV90b|   ACAAGAGATGAAATGAGTGTTGAAAGTTTTCTAGGGAGATCAGGTTGCATTCATATGTCA
2001 GROUP_21    ACAAGAGATGAAATGAGTGTTGAAAGTTTTCTAGGGAGATCAGGTTGCATTCATATGTCA
2002
2003 64_HRV90     AAATTAGTTGTAAACTAT---GAT--------------AATTAT------GATGAAAAC
2004 65_HRV90a|   AAATTAGTTGTAAACTAT---GAT--------------AATTAT------GATGAAAAC
2005 66_HRV90b|   AAATTAGTTGTAAACTAT---GAT--------------AATTAT------GATGAAAAC
2006 GROUP_21    AAATTAGTTGTAAACTAT...GAT..............AATTAT......GATGAAAAC
2007
```

FIG. D14 CONT'D 10.trace                                                              9/20/2007 5:05 PM

```
2008 64_HRV90    AACTTCCATAAATGGCAAATTAACCTGCAAGAGATGGCACAGATTAGAAGAAAATTTGAA
2009 65_HRV90a|  AACTTCCATAAATGGCAAATTAACCTGCAAGAGATGGCACAGATTAGAAGAAAATTTGAA
2010 66_HRV90b|  AACTTCCATAAATGGCAAATTAACCTGCAAGAGATGGCACAGATTAGAAGAAAATTTGAA
2011 GROUP_21    AACTTCCATAAATGGCAAATTAACCTGCAAGAGATGGCACAGATTAGAAGAAAATTTGAA
2012
2013 64_HRV90    TTGTTTACATATGCTAGATTTGATTCTGAAATTACAATAG-TACCATCTATAGCTGGCAA
2014 65_HRV90a|  TTGTTTACATATGCTAGATTTGATTCTGAAATTACAATAG-TACCATCTATAGCTGGCAA
2015 66_HRV90b|  TTGTTTACATATGCTAGATTTGATTCTGAAATTACAATAG-TACCATCTATAGCTGGCAA
2016 GROUP_21    TTGTTTACATATGCTAGATTTGATTCTGAAATTACAATAG.TACCATCTATAGCTGGCAA
2017
2018 64_HRV90    GGGCAATGATATTGGACATGTTGTGATGCAATACATGTATATACCACCTGGGGCACCAGT
2019 65_HRV90a|  GGGCAATGATATTGGACATGTTGTGATGCAATACATGTATATACCACCTGGGGCACCAGT
2020 66_HRV90b|  GGGCAATGATATTGGACATGTTGTGATGCAATACATGTATATACCACCTGGGGCACCAGT
2021 GROUP_21    GGGCAATGATATTGGACATGTTGTGATGCAATACATGTATATACCACCTGGGGCACCAGT
2022
2023 64_HRV90    ACCTGAGAAGAGGGATGATTATGCATGGCAATCAGGCACTAATGCATCTATCTTTTGGCA
2024 65_HRV90a|  ACCTGAGAAGAGGGATGATTATGCATGGCAATCAGGCACTAATGCATCTATCTTTTGGCA
2025 66_HRV90b|  ACCTGAGAAGAGGGATGATTATGCATGGCAATCAGGCACTAATGCATCTATCTTTTGGCA
2026 GROUP_21    ACCTGAGAAGAGGGATGATTATGCATGGCAATCAGGCACTAATGCATCTATCTTTTGGCA
2027
2028 64_HRV90    ACATGGACAAACATACCCTAGATTTTCACTTCCTTTCTTAAGTATAGCTTCTGCATACTA
2029 65_HRV90a|  ACATGGACAAACATACCCTAGATTTTCACTTCCTTTCTTAAGTATAGCTTCTGCATACTA
2030 66_HRV90b|  ACATGGACAAACATACCCTAGATTTTCACTTCCTTTCTTAAGTATAGCTTCTGCATACTA
2031 GROUP_21    ACATGGACAAACATACCCTAGATTTTCACTTCCTTTCTTAAGTATAGCTTCTGCATACTA
2032
2033 64_HRV90    TATGTTTTATGATGGATATGATGGTGACCAAACTGATTCGAGATATGGTACCATTGTTAC
2034 65_HRV90a|  TATGTTTTATGATGGATATGATGGTGACCAAACTGATTCGAGATATGGTACCATTGTTAC
2035 66_HRV90b|  TATGTTTTATGATGGATATGATGGTGACCAAACTGATTCGAGATATGGTACCATTGTTAC
2036 GROUP_21    TATGTTTTATGATGGATATGATGGTGACCAAACTGATTCGAGATATGGTACCATTGTTAC
2037
2038 64_HRV90    TAATGATATGGGAACCTTATGTTATAGAATAGTTACAGATGAACATGCCCACAAAATAGA
2039 65_HRV90a|  TAATGATATGGGAACCTTATGTTATAGAATAGTTACAGATGAACATGCCCACAAAATAGA
2040 66_HRV90b|  TAATGATATGGGAACCTTATGTTATAGAATAGTTACAGATGAACATGCCCACAAAATAGA
2041 GROUP_21    TAATGATATGGGAACCTTATGTTATAGAATAGTTACAGATGAACATGCCCACAAAATAGA
2042
2043 64_HRV90    GATCACTACAAGAATATACCATAAAGCAAAACACATTAAGGTTTGGTGTCCAAGACCACC
2044 65_HRV90a|  GATCACTACAAGAATATACCATAAAGCAAAACACATTAAGGTTTGGTGTCCAAGACCACC
2045 66_HRV90b|  GATCACTACAAGAATATACCATAAAGCAAAACACATTAAGGTTTGGTGTCCAAGACCACC
2046 GROUP_21    GATCACTACAAGAATATACCATAAAGCAAAACACATTAAGGTTTGGTGTCCAAGACCACC
2047
2048 64_HRV90    TAGGGCAGTTGAATACACA-CACACTCATGTAACAAACTACAAAC-ATGCAA---CACGT
2049 65_HRV90a|  TAGGGCAGTTGAATACACA-CACACTCATGTAACAAACTACAAAC-ATGCAA---CACGT
2050 66_HRV90b|  TAGGGCAGTTGAATACACA-CACACTCATGTAACAAACTACAAAC-ATGCAA---CACGT
2051 GROUP_21    TAGGGCAGTTGAATACACA.CACACTCATGTAACAAACTACAAAC.ATGCAA...CACGT
2052
2053 64_HRV90    GAAC------TTAAGACTG---CAATTAGGCCCAGGAAAACAATCACAACAGCA------
2054 65_HRV90a|  GAAC------TTAAGACTG---CAATTAGGCCCAGGAAAACAATCACAACAGCG------
2055 66_HRV90b|  GAAC------TTAAGACTG---CAATTAGGCCCAGGAAAACAATCACAACAGCT------
2056 GROUP_21    GAAC......TTAAGACTG...CAATTAGGCCCAGGAAAACAATCACAACAGC-......
2057
2058 64_HRV90    --------------------
2059 65_HRV90a|  --------------------
2060 66_HRV90b|  --------------------
2061 GROUP_21    ....................
2062
2063
2064
2065 Group 22:
2066
2067 67_HRV34    AATCCAGTTGAAAATTACATAGATGAGGTACTAAATGAGGTATTGGTTGTACCAAACATT
2068 68_HRV34b|  AATCCAGTTGAAAATTACATAGATGAGGTACTAAATGAGGTATTGGTTGTACCAAACATT
2069 69_HRV34a|  AATCCAGTTGAAAATTACATAGATGAGGTACTAAATGAGGTATTGGTTGTACCAAACATT
2070 GROUP_22    AATCCAGTTGAAAATTACATAGATGAGGTACTAAATGAGGTATTGGTTGTACCAAACATT
2071
2072 67_HRV34    AAAGAAAGCCAAGCCACCACATCAAACTCTGCCCCCGCACTGGATGCAGCTGAGACTGGT
```

FIG. D14 CONT'D

```
10.trace                                                                9/20/2007 5:05 PM 2073 68_HRV34b|   AAAGAAAGCCAAGCCACCACATCAAACTCTGCCCCCGCACTGGATGCAGCTGAGACTGGT
2074 69_HRV34a|   AAAGAAAGCCAAGCCACCACATCAAACTCTGCCCCCGCACTGGATGCAGCTGAGACTGGT
2075 GROUP_22    AAAGAAAGCCAAGCCACCACATCAAACTCTGCCCCCGCACTGGATGCAGCTGAGACTGGT
2076
2077 67_HRV34    CACACTAGCAGTGTACAACCTGAAGATATGATTGAGACCAGGTACGTACAAACATCACAA
2078 68_HRV34b|   CACACTAGCAGTGTACAACCTGAAGATATGATTGAGACCAGGTACGTACAAACATCACAA
2079 69_HRV34a|   CACACTAGCAGTGTACAACCTGAAGATATGATTGAGACCAGGTACGTACAAACATCACAA
2080 GROUP_22    CACACTAGCAGTGTACAACCTGAAGATATGATTGAGACCAGGTACGTACAAACATCACAA
2081
2082 67_HRV34    ACAAGAGATGAAATGAGCATTGAGAGTTTCCTGGGTAGGTCTGGCTGTATACACATGTCC
2083 68_HRV34b|   ACAAGAGATGAAATGAGCATTGAGAGTTTCCTGGGTAGGTCTGGCTGTATACACATGTCC
2084 69_HRV34a|   ACAAGAGATGAAATGAGCATTGAGAGTTTCCTGGGTAGGTCTGGCTGTATACACATGTCC
2085 GROUP_22    ACAAGAGATGAAATGAGCATTGAGAGTTTCCTGGGTAGGTCTGGCTGTATACACATGTCC
2086
2087 67_HRV34    AAACTTGTTGTAGATTATGAAAAT---------------TACAATGCA---AAAACAAAG
2088 68_HRV34b|   AAACTTGTTGTAGATTATGAAAAT---------------TACAATGCA---AAAACAAAG
2089 69_HRV34a|   AAACTTGTTGTAGATTATGAAAAT---------------TACAATGCA---AAAACAAAG
2090 GROUP_22    AAACTTGTTGTAGATTATGAAAAT...............TACAATGCA...AAAACAAAG
2091
2092 67_HRV34    AACTTTATGACATGGCAAATTAATTTACAGGAAATGGCACAGATTAGAAGGAAATTTGAA
2093 68_HRV34b|   AACTTTATGACATGGCAAATTAATTTACAGGAAATGGCACAGATTAGAAGGAAATTTGAA
2094 69_HRV34a|   AACTTTATGACATGGCAAATTAATTTACAGGAAATGGCACAGATTAGAAGGAAATTTGAA
2095 GROUP_22    AACTTTATGACATGGCAAATTAATTTACAGGAAATGGCACAGATTAGAAGGAAATTTGAA
2096
2097 67_HRV34    ATGTTCACCTACGTCAGATTTGATTCTGAAGTCACCCTAG-TACCATCAATAGCGGCCAA
2098 68_HRV34b|   ATGTTCACCTACGTCAGATTTGATTCTGAAGTCACCCTAG-TACCATCAATAGCGGCCAA
2099 69_HRV34a|   ATGTTCACCTACGTCAGATTTGATTCTGAAGTCACCCTAG-TACCATCAATAGCGGCCAA
2100 GROUP_22    ATGTTCACCTACGTCAGATTTGATTCTGAAGTCACCCTAG.TACCATCAATAGCGGCCAA
2101
2102 67_HRV34    AGGTGATGATATTGGACATGTTGTGATGCAATACATGTATGTACCACCAGGTGCACCAAT
2103 68_HRV34b|   AGGTGATGATATTGGACATGTTGTGATGCAATACATGTATGTACCACCAGGTGCACCAAT
2104 69_HRV34a|   AGGTGATGATATTGGACATGTTGTGATGCAATACATGTATGTACCACCAGGTGCACCAAT
2105 GROUP_22    AGGTGATGATATTGGACATGTTGTGATGCAATACATGTATGTACCACCAGGTGCACCAAT
2106
2107 67_HRV34    ACCTAAAACTAGAGATGATTTTGCATGGCAATCTGGAACAAATGCCTCAATATTTTGGCA
2108 68_HRV34b|   ACCTAAAACTAGAGATGATTTTGCATGGCAATCTGGAACAAATGCCTCAATATTTTGGCA
2109 69_HRV34a|   ACCTAAAACTAGAGATGATTTTGCATGGCAATCTGGAACAAATGCCTCAATATTTTGGCA
2110 GROUP_22    ACCTAAAACTAGAGATGATTTTGCATGGCAATCTGGAACAAATGCCTCAATATTTTGGCA
2111
2112 67_HRV34    ACATGGTCAAACATACCCTAGATTTTCCCTCCCTTTCTTAAGCATAGCCTCAGCATACTA
2113 68_HRV34b|   ACATGGTCAAACATACCCTAGATTTTCCCTCCCTTTCTTAAGCATAGCCTCAGCATACTA
2114 69_HRV34a|   ACATGGTCAAACATACCCTAGATTTTCCCTCCCTTTCTTAAGCATAGCCTCAGCATACTA
2115 GROUP_22    ACATGGTCAAACATACCCTAGATTTTCCCTCCCTTTCTTAAGCATAGCCTCAGCATACTA
2116
2117 67_HRV34    CATGTTTTATGATGGATATGATGGTGATCAACATGATTCAAGATATGGTACAGTAGTGAC
2118 68_HRV34b|   CATGTTTTATGATGGATATGATGGTGATCAACATGATTCAAGATATGGTACAGTAGTGAC
2119 69_HRV34a|   CATGTTTTATGATGGATATGATGGTGATCAACATGATTCAAGATATGGTACAGTAGTGAC
2120 GROUP_22    CATGTTTTATGATGGATATGATGGTGATCAACATGATTCAAGATATGGTACAGTAGTGAC
2121
2122 67_HRV34    TAATGACATGGGTACTTTATGCTCCAGAATTGTAACTGATGAACACCAAAACAGAGTAGA
2123 68_HRV34b|   TAATGACATGGGTACTTTATGCTCCAGAATTGTAACTGATGAACACCAAAACAGAGTAGA
2124 69_HRV34a|   TAATGACATGGGTACTTTATGCTCCAGAATTGTAACTGATGAACACCAAAACAGAGTAGA
2125 GROUP_22    TAATGACATGGGTACTTTATGCTCCAGAATTGTAACTGATGAACACCAAAACAGAGTAGA
2126
2127 67_HRV34    AATAACAACTAGAGTTTATCACAAAGCTAAACATGTAAAAACCTGGTGTCCAAGACCACC
2128 68_HRV34b|   AATAACAACTAGAGTTTATCACAAAGCTAAACATGTAAAAACCTGGTGTCCAAGACCACC
2129 69_HRV34a|   AATAACAACTAGAGTTTATCACAAAGCTAAACATGTAAAAACCTGGTGTCCAAGACCACC
2130 GROUP_22    AATAACAACTAGAGTTTATCACAAAGCTAAACATGTAAAAACCTGGTGTCCAAGACCACC
2131
2132 67_HRV34    AAGAGCTGTTGAGTACACA-CACACACATGTTACTAACTACAAAG-TTAGGG---GTAAA
2133 68_HRV34b|   AAGAGCTGTTGAGTACACA-CACACACATGTTACTAACTACAAAG-TTAGGG---GTAAA
2134 69_HRV34a|   AAGAGCTGTTGAGTACACA-CACACACATGTTACTAACTACAAAG-TTAGGG---GTAAA
2135 GROUP_22    AAGAGCTGTTGAGTACACA.CACACACATGTTACTAACTACAAAG.TTAGGG...GTAAA
2136
2137 67_HRV34    ACTG------AGAAGACTG---CAATCAAACACAGAGCAAAGATCACAATGGCC------
```

FIG. D14 CONT'D

```
10.trace                                                                                          9/20/2007 5:05 PM 2138  68_HRV34b|    ACTG------AGAAGACTG---CAATCAAACACAGAGCAAAGATCACAATGGCA------
2139  69_HRV34a|    ACTG------AGAAGACTG---CAATCAAACACAGAGCAAAGATCACAATGGCT------
2140  GROUP_22     ACTG......AGAAGACTG...CAATCAAACACAGAGCAAAGATCACAATGGC-......
2141
2142  67_HRV34     --------------------
2143  68_HRV34b|   --------------------
2144  69_HRV34a|   --------------------
2145  GROUP_22     ....................
2146
2147
2148
2149  Group  23:
2150
2151  70_HRV50a|    AATCCAGTGGAGAATTACATAGATGAAGTATTAAATGAGGTATTAGTTGTCCCAAATATC
2152  71_HRV50b|    AATCCAGTGGAGAATTACATAGATGAAGTATTAAATGAGGTATTAGTTGTCCCAAATATC
2153  72_HRV50      AATCCAGTGGAGAATTACATAGATGAAGTATTAAATGAGGTATTAGTTGTCCCAAATATC
2154  GROUP_23     AATCCAGTGGAGAATTACATAGATGAAGTATTAAATGAGGTATTAGTTGTCCCAAATATC
2155
2156  70_HRV50a|    AAGGAGAGTCAAGCCACTACATCAAACTCTGCCCCTGCTTTAGATGCAGCTGAAACTGGA
2157  71_HRV50b|    AAGGAGAGTCAAGCCACTACATCAAACTCTGCCCCTGCTTTAGATGCAGCTGAAACTGGA
2158  72_HRV50      AAGGAGAGTCAAGCCACTACATCAAACTCTGCCCCTGCTTTAGATGCAGCTGAAACTGGA
2159  GROUP_23     AAGGAGAGTCAAGCCACTACATCAAACTCTGCCCCTGCTTTAGATGCAGCTGAAACTGGA
2160
2161  70_HRV50a|    CACACAAGTAATGTGCAGCCTGAAGATATGCTTGAAACTAGATATGTGCAAACATCGCAT
2162  71_HRV50b|    CACACAAGTAATGTGCAGCCTGAAGATATGCTTGAAACTAGATATGTGCAAACATCGCAT
2163  72_HRV50      CACACAAGTAATGTGCAGCCTGAAGATATGCTTGAAACTAGATATGTGCAAACATCGCAT
2164  GROUP_23     CACACAAGTAATGTGCAGCCTGAAGATATGCTTGAAACTAGATATGTGCAAACATCGCAT
2165
2166  70_HRV50a|    ACAAGAGATGAAATGAGCATTGAAAGTTTCCTAGGTAGATCTGGTTGTATACATATATCT
2167  71_HRV50b|    ACAAGAGATGAAATGAGCATTGAAAGTTTCCTAGGTAGATCTGGTTGTATACATATATCT
2168  72_HRV50      ACAAGAGATGAAATGAGCATTGAAAGTTTCCTAGGTAGATCTGGTTGTATACATATATCT
2169  GROUP_23     ACAAGAGATGAAATGAGCATTGAAAGTTTCCTAGGTAGATCTGGTTGTATACATATATCT
2170
2171  70_HRV50a|    AAATTAGTTGTTGATTATGATGGT---------------TACAATGAG---GAAACAAAG
2172  71_HRV50b|    AAATTAGTTGTTGATTATGATGGT---------------TACAATGAG---GAAACAAAG
2173  72_HRV50      AAATTAGTTGTTGATTATGATGGT---------------TACAATGAG---GAAACAAAG
2174  GROUP_23     AAATTAGTTGTTGATTATGATGGT...............TACAATGAG...GAAACAAAG
2175
2176  70_HRV50a|    AACTTCAAGAAATGGCAAATCAACCTACAAGAAATGGCACAGATCAGAAGGAAATTTGAG
2177  71_HRV50b|    AACTTCAAGAAATGGCAAATCAACCTACAAGAAATGGCACAGATCAGAAGGAAATTTGAG
2178  72_HRV50      AACTTCAAGAAATGGCAAATCAACCTACAAGAAATGGCACAGATCAGAAGGAAATTTGAG
2179  GROUP_23     AACTTCAAGAAATGGCAAATCAACCTACAAGAAATGGCACAGATCAGAAGGAAATTTGAG
2180
2181  70_HRV50a|    ATGTTCACCTATGTGAGGTTTAATTCTGAGGTCACATTAG-TACCATCCATAGCTGCCAA
2182  71_HRV50b|    ATGTTCACCTATGTGAGGTTTAATTCTGAGGTCACATTAG-TACCATCCATAGCTGCCAA
2183  72_HRV50      ATGTTCACCTATGTGAGGTTTAATTCTGAGGTCACATTAG-TACCATCCATAGCTGCCAA
2184  GROUP_23     ATGTTCACCTATGTGAGGTTTAATTCTGAGGTCACATTAG.TACCATCCATAGCTGCCAA
2185
2186  70_HRV50a|    GGGTGTTGATATTGGACATGTTGTCATGCAATACATGTATGTCCCACCAGGTGCACCAAT
2187  71_HRV50b|    GGGTGTTGATATTGGACATGTTGTCATGCAATACATGTATGTCCCACCAGGTGCACCAAT
2188  72_HRV50      GGGTGTTGATATTGGACATGTTGTCATGCAATACATGTATGTCCCACCAGGTGCACCAAT
2189  GROUP_23     GGGTGTTGATATTGGACATGTTGTCATGCAATACATGTATGTCCCACCAGGTGCACCAAT
2190
2191  70_HRV50a|    ACCCAAGACTAGGGATGATTTTGCCTGGCAATCTGGAACTAATGCTTCAATCTTTTGGCA
2192  71_HRV50b|    ACCCAAGACTAGGGATGATTTTGCCTGGCAATCTGGAACTAATGCTTCAATCTTTTGGCA
2193  72_HRV50      ACCCAAGACTAGGGATGATTTTGCCTGGCAATCTGGAACTAATGCTTCAATCTTTTGGCA
2194  GROUP_23     ACCCAAGACTAGGGATGATTTTGCCTGGCAATCTGGAACTAATGCTTCAATCTTTTGGCA
2195
2196  70_HRV50a|    ACATGGTCAAACATACCCTAGATTCTCTCTACCATTCTTGAGTATAGCATCTGCATATTA
2197  71_HRV50b|    ACATGGTCAAACATACCCTAGATTCTCTCTACCATTCTTGAGTATAGCATCTGCATATTA
2198  72_HRV50      ACATGGTCAAACATACCCTAGATTCTCTCTACCATTCTTGAGTATAGCATCTGCATATTA
2199  GROUP_23     ACATGGTCAAACATACCCTAGATTCTCTCTACCATTCTTGAGTATAGCATCTGCATATTA
2200
2201  70_HRV50a|    CATGTTTTATGATGGTTATGATGGTGATAAATCTACATCCAGGTATGGTACAGTAGTTAC
2202  71_HRV50b|    CATGTTTTATGATGGTTATGATGGTGATAAATCTACATCCAGGTATGGTACAGTAGTTAC
```

FIG. D14 CONT'D

```
10.trace                                                               9/20/2007 5:05 PM 2203 72_HRV50      CATGTTTTATGATGGTTATGATGGTGATAAATCTACATCCAGGTATGGTACAGTAGTTAC
2204 GROUP_23     CATGTTTTATGATGGTTATGATGGTGATAAATCTACATCCAGGTATGGTACAGTAGTTAC
2205
2206 70_HRV50a|   CAATGACATGGGCACTTTGTGTTCTAGGATTGTCACTGATGAGCACCAAAATAAAGTGGA
2207 71_HRV50b|   CAATGACATGGGCACTTTGTGTTCTAGGATTGTCACTGATGAGCACCAAAATAAAGTGGA
2208 72_HRV50      CAATGACATGGGCACTTTGTGTTCTAGGATTGTCACTGATGAGCACCAAAATAAAGTGGA
2209 GROUP_23     CAATGACATGGGCACTTTGTGTTCTAGGATTGTCACTGATGAGCACCAAAATAAAGTGGA
2210
2211 70_HRV50a|   AATCACAACCAGAGTATACCATAAAGCCAAACACATAAAAGTCTGGTGTCCAAGACCACC
2212 71_HRV50b|   AATCACAACCAGAGTATACCATAAAGCCAAACACATAAAAGTCTGGTGTCCAAGACCACC
2213 72_HRV50      AATCACAACCAGAGTATACCATAAAGCCAAACACATAAAAGTCTGGTGTCCAAGACCACC
2214 GROUP_23     AATCACAACCAGAGTATACCATAAAGCCAAACACATAAAAGTCTGGTGTCCAAGACCACC
2215
2216 70_HRV50a|   AAGAGCTGTTGAATACACA-CACACCCATGTCACTAACTACAAGA-AAAGTG---ATGCT
2217 71_HRV50b|   AAGAGCTGTTGAATACACA-CACACCCATGTCACTAACTACAAGA-AAAGTG---ATGCT
2218 72_HRV50      AAGAGCTGTTGAATACACA-CACACCCATGTCACTAACTACAAGA-AAAGTG---ATGCT
2219 GROUP_23     AAGAGCTGTTGAATACACA.CACACCCATGTCACTAACTACAAGA.AAAGTG...ATGCT
2220
2221 70_HRV50a|   ACTG------AGAAGACTG---CAATTGCAACTAGACCAAAGATCACAGTGGCA------
2222 71_HRV50b|   ACTG------AGAAGACTG---CAATTGCAACTAGACCAAAGATCACAGTGGCG------
2223 72_HRV50      ACTG------AGAAGACTG---CAATTGCAACTAGACCAAAGATCACAGTGGCT------
2224 GROUP_23     ACTG......AGAAGACTG...CAATTGCAACTAGACCAAAGATCACAGTGGC-......
2225
2226 70_HRV50a|   --------------------
2227 71_HRV50b|   --------------------
2228 72_HRV50      --------------------
2229 GROUP_23     ....................
2230
2231
2232
2233 Group 24:
2234
2235 73_HRV18a|   AATCCAGTAGAGAATTATATAGATGAAGTACTTAATGAAGTGTTAGTGGTCCCAAATGTG
2236 74_HRV18b|   AATCCAGTAGAGAATTATATAGATGAAGTACTTAATGAAGTGTTAGTGGTCCCAAATGTG
2237 75_HRV18      AATCCAGTAGAGAATTATATAGATGAAGTACTTAATGAAGTGTTAGTGGTCCCAAATGTG
2238 GROUP_24     AATCCAGTAGAGAATTATATAGATGAAGTACTTAATGAAGTGTTAGTGGTCCCAAATGTG
2239
2240 73_HRV18a|   AATGAAAGTCACGCAATTACATCAAATTCAGCCCCTGCTTTAGATGCCGCTGAAACTGGT
2241 74_HRV18b|   AATGAAAGTCACGCAATTACATCAAATTCAGCCCCTGCTTTAGATGCCGCTGAAACTGGT
2242 75_HRV18      AATGAAAGTCACGCAATTACATCAAATTCAGCCCCTGCTTTAGATGCCGCTGAAACTGGT
2243 GROUP_24     AATGAAAGTCACGCAATTACATCAAATTCAGCCCCTGCTTTAGATGCCGCTGAAACTGGT
2244
2245 73_HRV18a|   CACACCAGCAATGTGCAACCTGAAGATATGATTGAGACTAGGTATGTACAAACATCACAA
2246 74_HRV18b|   CACACCAGCAATGTGCAACCTGAAGATATGATTGAGACTAGGTATGTACAAACATCACAA
2247 75_HRV18      CACACCAGCAATGTGCAACCTGAAGATATGATTGAGACTAGGTATGTACAAACATCACAA
2248 GROUP_24     CACACCAGCAATGTGCAACCTGAAGATATGATTGAGACTAGGTATGTACAAACATCACAA
2249
2250 73_HRV18a|   ACAAGAGATGAAATGAGTATAGAGTGTTTTCTAGGCAGATCAGGGTGTATACATATCTCC
2251 74_HRV18b|   ACAAGAGATGAAATGAGTATAGAGTGTTTTCTAGGCAGATCAGGGTGTATACATATCTCC
2252 75_HRV18      ACAAGAGATGAAATGAGTATAGAGTGTTTTCTAGGCAGATCAGGGTGTATACATATCTCC
2253 GROUP_24     ACAAGAGATGAAATGAGTATAGAGTGTTTTCTAGGCAGATCAGGGTGTATACATATCTCC
2254
2255 73_HRV18a|   AAGTTAGTTGTACATTATGAAGAT---------------TATAATGCA---GAAACAAGG
2256 74_HRV18b|   AAGTTAGTTGTACATTATGAAGAT---------------TATAATGCA---GAAACAAGG
2257 75_HRV18      AAGTTAGTTGTACATTATGAAGAT---------------TATAATGCA---GAAACAAGG
2258 GROUP_24     AAGTTAGTTGTACATTATGAAGAT...............TATAATGCA...GAAACAAGG
2259
2260 73_HRV18a|   AACTTTGTAAAATGGCAAATAAATCTACAGGAAATGGCCCAGATTAGGAGAAAATTTGAG
2261 74_HRV18b|   AACTTTGTAAAATGGCAAATAAATCTACAGGAAATGGCCCAGATTAGGAGAAAATTTGAG
2262 75_HRV18      AACTTTGTAAAATGGCAAATAAATCTACAGGAAATGGCCCAGATTAGGAGAAAATTTGAG
2263 GROUP_24     AACTTTGTAAAATGGCAAATAAATCTACAGGAAATGGCCCAGATTAGGAGAAAATTTGAG
2264
2265 73_HRV18a|   ATGTTTACATATGTTAGATTTGATTCAGAAATTACACTAG-TACCATCTGTAGCTGCTAA
2266 74_HRV18b|   ATGTTTACATATGTTAGATTTGATTCAGAAATTACACTAG-TACCATCTGTAGCTGCTAA
2267 75_HRV18      ATGTTTACATATGTTAGATTTGATTCAGAAATTACACTAG-TACCATCTGTAGCTGCTAA
```

FIG. D14 CONT'D

```
10.trace                                                              9/20/2007 5:05 PM 2268 GROUP_24     ATGTTTACATATGTTAGATTTGATTCAGAAATTACACTAG.TACCATCTGTAGCTGCTAA
2269
2270 73_HRV18a|   GGGTGATGACATAGGACATATTGTTATGCAGTACATGTATGTTCCTCCAGGAGCACCAAT
2271 74_HRV18b|   GGGTGATGACATAGGACATATTGTTATGCAGTACATGTATGTTCCTCCAGGAGCACCAAT
2272 75_HRV18     GGGTGATGACATAGGACATATTGTTATGCAGTACATGTATGTTCCTCCAGGAGCACCAAT
2273 GROUP_24     GGGTGATGACATAGGACATATTGTTATGCAGTACATGTATGTTCCTCCAGGAGCACCAAT
2274
2275 73_HRV18a|   ACCAAAAACCAGAGATGATTTTGCCTGGCAATCTGGAACAAATGCATCAATCTTCTGGCA
2276 74_HRV18b|   ACCAAAAACCAGAGATGATTTTGCCTGGCAATCTGGAACAAATGCATCAATCTTCTGGCA
2277 75_HRV18     ACCAAAAACCAGAGATGATTTTGCCTGGCAATCTGGAACAAATGCATCAATCTTCTGGCA
2278 GROUP_24     ACCAAAAACCAGAGATGATTTTGCCTGGCAATCTGGAACAAATGCATCAATCTTCTGGCA
2279
2280 73_HRV18a|   ACATGGTCAAACATACCCCAGATTTTCACTTCCTTTCCTCAGTATAGCATCAGCTTATTA
2281 74_HRV18b|   ACATGGTCAAACATACCCCAGATTTTCACTTCCTTTCCTCAGTATAGCATCAGCTTATTA
2282 75_HRV18     ACATGGTCAAACATACCCCAGATTTTCACTTCCTTTCCTCAGTATAGCATCAGCTTATTA
2283 GROUP_24     ACATGGTCAAACATACCCCAGATTTTCACTTCCTTTCCTCAGTATAGCATCAGCTTATTA
2284
2285 73_HRV18a|   CATGTTCTATGATGGCTACGACGGTGACCAGACCTCATCGCGGTATGGCACAGTTGCAAC
2286 74_HRV18b|   CATGTTCTATGATGGCTACGACGGTGACCAGACCTCATCGCGGTATGGCACAGTTGCAAC
2287 75_HRV18     CATGTTCTATGATGGCTACGACGGTGACCAGACCTCATCGCGGTATGGCACAGTTGCAAC
2288 GROUP_24     CATGTTCTATGATGGCTACGACGGTGACCAGACCTCATCGCGGTATGGCACAGTTGCAAC
2289
2290 73_HRV18a|   AAATGACATGGGTACCTTGTGCTCTAGAATAGTCACAGATAAACATAAGAATGAGGTGGA
2291 74_HRV18b|   AAATGACATGGGTACCTTGTGCTCTAGAATAGTCACAGATAAACATAAGAATGAGGTGGA
2292 75_HRV18     AAATGACATGGGTACCTTGTGCTCTAGAATAGTCACAGATAAACATAAGAATGAGGTGGA
2293 GROUP_24     AAATGACATGGGTACCTTGTGCTCTAGAATAGTCACAGATAAACATAAGAATGAGGTGGA
2294
2295 73_HRV18a|   AATAACAACCAGAATATACCACAAGGCAAAACATGTTAAAGCATGGTGCCCAAGGCCACC
2296 74_HRV18b|   AATAACAACCAGAATATACCACAAGGCAAAACATGTTAAAGCATGGTGCCCAAGGCCACC
2297 75_HRV18     AATAACAACCAGAATATACCACAAGGCAAAACATGTTAAAGCATGGTGCCCAAGGCCACC
2298 GROUP_24     AATAACAACCAGAATATACCACAAGGCAAAACATGTTAAAGCATGGTGCCCAAGGCCACC
2299
2300 73_HRV18a|   GAGAGCTGTGGAGTACACA-CATACACATGTAACTAACTACAAGC-CTAAGG---AAGGA
2301 74_HRV18b|   GAGAGCTGTGGAGTACACA-CATACACATGTAACTAACTACAAGC-CTAAGG---AAGGA
2302 75_HRV18     GAGAGCTGTGGAGTACACA-CATACACATGTAACTAACTACAAGC-CTAAGG---AAGGA
2303 GROUP_24     GAGAGCTGTGGAGTACACA.CATACACATGTAACTAACTACAAGC.CTAAGG...AAGGA
2304
2305 73_HRV18a|   AGAG------AGAAAACTG---CCATAGTACCCAGAGCAAGGATTACAATGGCA------
2306 74_HRV18b|   AGAG------AGAAAACTG---CCATAGTACCCAGAGCAAGGATTACAATGGCG------
2307 75_HRV18     AGAG------AGAAAACTG---CCATAGTACCCAGAGCAAGGATTACAATGGCT------
2308 GROUP_24     AGAG......AGAAAACTG...CCATAGTACCCAGAGCAAGGATTACAATGGC-......
2309
2310 73_HRV18a|   --------------------
2311 74_HRV18b|   --------------------
2312 75_HRV18     --------------------
2313 GROUP_24     ....................
2314
2315
2316
2317 Group 25:
2318
2319 76_HRV55     AATCCTGTAGAGAGATATGTTGATGAAGTCCTGAATGAAGTGCTAGTAGTTCCAAATATT
2320 77_HRV55b|   AATCCTGTAGAGAGATATGTTGATGAAGTCCTGAATGAAGTGCTAGTAGTTCCAAATATT
2321 78_HRV55a|   AATCCTGTAGAGAGATATGTTGATGAAGTCCTGAATGAAGTGCTAGTAGTTCCAAATATT
2322 GROUP_25     AATCCTGTAGAGAGATATGTTGATGAAGTCCTGAATGAAGTGCTAGTAGTTCCAAATATT
2323
2324 76_HRV55     AGGGAGAGTCAAGCAGCAACATCAAATTCAGCTCCAGTACTAGATGCAGCAGAAACTGGG
2325 77_HRV55b|   AGGGAGAGTCAAGCAGCAACATCAAATTCAGCTCCAGTACTAGATGCAGCAGAAACTGGG
2326 78_HRV55a|   AGGGAGAGTCAAGCAGCAACATCAAATTCAGCTCCAGTACTAGATGCAGCAGAAACTGGG
2327 GROUP_25     AGGGAGAGTCAAGCAGCAACATCAAATTCAGCTCCAGTACTAGATGCAGCAGAAACTGGG
2328
2329 76_HRV55     CATACAAGCAATGTACAACCAGAAGATGTAATTGAGACAAGATATGTTCAGACATCACAA
2330 77_HRV55b|   CATACAAGCAATGTACAACCAGAAGATGTAATTGAGACAAGATATGTTCAGACATCACAA
2331 78_HRV55a|   CATACAAGCAATGTACAACCAGAAGATGTAATTGAGACAAGATATGTTCAGACATCACAA
2332 GROUP_25     CATACAAGCAATGTACAACCAGAAGATGTAATTGAGACAAGATATGTTCAGACATCACAA
```

FIG. D14 CONT'D 10.trace                                                                                     9/20/2007 5:05 PM

```
2333
2334  76_HRV55      ACTCGTGATGAGATGAGCATTGAAAGTTTTCTAGGTAGATCAGGATGTGTACATATATCA
2335  77_HRV55b|    ACTCGTGATGAGATGAGCATTGAAAGTTTTCTAGGTAGATCAGGATGTGTACATATATCA
2336  78_HRV55a|    ACTCGTGATGAGATGAGCATTGAAAGTTTTCTAGGTAGATCAGGATGTGTACATATATCA
2337  GROUP_25      ACTCGTGATGAGATGAGCATTGAAAGTTTTCTAGGTAGATCAGGATGTGTACATATATCA
2338
2339  76_HRV55      GAGTTAGTTGTTCATTATGAAGAA---------------TATAACAAA---GAGGGAAAA
2340  77_HRV55b|    GAGTTAGTTGTTCATTATGAAGAA---------------TATAACAAA---GAGGGAAAA
2341  78_HRV55a|    GAGTTAGTTGTTCATTATGAAGAA---------------TATAACAAA---GAGGGAAAA
2342  GROUP_25      GAGTTAGTTGTTCATTATGAAGAA...............TATAACAAA...GAGGGAAAA
2343
2344  76_HRV55      AATTTTACTAAGTGGCAAGTAAACATCCAAGAGATGGCTCAGATTAGAAGAAAATTTGAA
2345  77_HRV55b|    AATTTTACTAAGTGGCAAGTAAACATCCAAGAGATGGCTCAGATTAGAAGAAAATTTGAA
2346  78_HRV55a|    AATTTTACTAAGTGGCAAGTAAACATCCAAGAGATGGCTCAGATTAGAAGAAAATTTGAA
2347  GROUP_25      AATTTTACTAAGTGGCAAGTAAACATCCAAGAGATGGCTCAGATTAGAAGAAAATTTGAA
2348
2349  76_HRV55      ATGTTCACCTATACTAGATTTGATTCAGAAGTTACATTAG-TACCCTCTATTGCTGCAAA
2350  77_HRV55b|    ATGTTCACCTATACTAGATTTGATTCAGAAGTTACATTAG-TACCCTCTATTGCTGCAAA
2351  78_HRV55a|    ATGTTCACCTATACTAGATTTGATTCAGAAGTTACATTAG-TACCCTCTATTGCTGCAAA
2352  GROUP_25      ATGTTCACCTATACTAGATTTGATTCAGAAGTTACATTAG.TACCCTCTATTGCTGCAAA
2353
2354  76_HRV55      GGGAGATGACATTGGACATGTAGTCATGCAATACATGTATGTTCCACCTGGAGCACCAAT
2355  77_HRV55b|    GGGAGATGACATTGGACATGTAGTCATGCAATACATGTATGTTCCACCTGGAGCACCAAT
2356  78_HRV55a|    GGGAGATGACATTGGACATGTAGTCATGCAATACATGTATGTTCCACCTGGAGCACCAAT
2357  GROUP_25      GGGAGATGACATTGGACATGTAGTCATGCAATACATGTATGTTCCACCTGGAGCACCAAT
2358
2359  76_HRV55      TCCAAAGACAAGAGAAGATTATGCTTGGCAATCAGGGACCAATGCATCTATCTTTTGGCA
2360  77_HRV55b|    TCCAAAGACAAGAGAAGATTATGCTTGGCAATCAGGGACCAATGCATCTATCTTTTGGCA
2361  78_HRV55a|    TCCAAAGACAAGAGAAGATTATGCTTGGCAATCAGGGACCAATGCATCTATCTTTTGGCA
2362  GROUP_25      TCCAAAGACAAGAGAAGATTATGCTTGGCAATCAGGGACCAATGCATCTATCTTTTGGCA
2363
2364  76_HRV55      ACATGGGCAAACATACCCTAGATTTTCACTTCCTTTCCTAAGTATAGCTTCTGCTTATTA
2365  77_HRV55b|    ACATGGGCAAACATACCCTAGATTTTCACTTCCTTTCCTAAGTATAGCTTCTGCTTATTA
2366  78_HRV55a|    ACATGGGCAAACATACCCTAGATTTTCACTTCCTTTCCTAAGTATAGCTTCTGCTTATTA
2367  GROUP_25      ACATGGGCAAACATACCCTAGATTTTCACTTCCTTTCCTAAGTATAGCTTCTGCTTATTA
2368
2369  76_HRV55      CATGTTCTATGATGGATATGATGGTGACCAAACTGAGTCACGCTATGGCACTGTAGTCAC
2370  77_HRV55b|    CATGTTCTATGATGGATATGATGGTGACCAAACTGAGTCACGCTATGGCACTGTAGTCAC
2371  78_HRV55a|    CATGTTCTATGATGGATATGATGGTGACCAAACTGAGTCACGCTATGGCACTGTAGTCAC
2372  GROUP_25      CATGTTCTATGATGGATATGATGGTGACCAAACTGAGTCACGCTATGGCACTGTAGTCAC
2373
2374  76_HRV55      TAATGACATGGGTACTTTATGTTCTAGAATAATAACTGATAACCATAAGCACCCAATTGA
2375  77_HRV55b|    TAATGACATGGGTACTTTATGTTCTAGAATAATAACTGATAACCATAAGCACCCAATTGA
2376  78_HRV55a|    TAATGACATGGGTACTTTATGTTCTAGAATAATAACTGATAACCATAAGCACCCAATTGA
2377  GROUP_25      TAATGACATGGGTACTTTATGTTCTAGAATAATAACTGATAACCATAAGCACCCAATTGA
2378
2379  76_HRV55      AGTGACGACAAGAGTCTATCATAAAGCTAAACACATCAAAGCATGGTGCCCACGACCACC
2380  77_HRV55b|    AGTGACGACAAGAGTCTATCATAAAGCTAAACACATCAAAGCATGGTGCCCACGACCACC
2381  78_HRV55a|    AGTGACGACAAGAGTCTATCATAAAGCTAAACACATCAAAGCATGGTGCCCACGACCACC
2382  GROUP_25      AGTGACGACAAGAGTCTATCATAAAGCTAAACACATCAAAGCATGGTGCCCACGACCACC
2383
2384  76_HRV55      TAGGGCTGTTGAATACACA-CACACACATGTCACAAATTACAAGA-AGACTG---ATGGC
2385  77_HRV55b|    TAGGGCTGTTGAATACACA-CACACACATGTCACAAATTACAAGA-AGACTG---ATGGC
2386  78_HRV55a|    TAGGGCTGTTGAATACACA-CACACACATGTCACAAATTACAAGA-AGACTG---ATGGC
2387  GROUP_25      TAGGGCTGTTGAATACACA.CACACACATGTCACAAATTACAAGA.AGACTG...ATGGC
2388
2389  76_HRV55      ACAG------AAAAGACAG---CAATTGAATACAGAAGGGACATTAAAACAGTG------
2390  77_HRV55b|    ACAG------AAAAGACAG---CAATTGAATACAGAAGGGACATTAAAACAGTC------
2391  78_HRV55a|    ACAG------AAAAGACAG---CAATTGAATACAGAAGGGACATTAAAACAGTA------
2392  GROUP_25      ACAG......AAAAGACAG...CAATTGAATACAGAAGGGACATTAAAACAGT-......
2393
2394  76_HRV55      --------------------
2395  77_HRV55b|    --------------------
2396  78_HRV55a|    --------------------
2397  GROUP_25      ....................
```

FIG. D14 CONT'D 10.trace                                                                                      9/20/2007 5:05 PM

```
Group  26:

79_HRV57     AACCCAGTAGAAAATTTTGTGGATGAGATCTTGAATGAAGTTTTGGTGGTTCCAGATATC
80_HRV57a|   AACCCAGTAGAAAATTTTGTGGATGAGATCTTGAATGAAGTTTTGGTGGTTCCAGATATC
81_HRV57b|   AACCCAGTAGAAAATTTTGTGGATGAGATCTTGAATGAAGTTTTGGTGGTTCCAGATATC
GROUP_26     AACCCAGTAGAAAATTTTGTGGATGAGATCTTGAATGAAGTTTTGGTGGTTCCAGATATC

79_HRV57     AAACAAAGTCAAGCAACAACATCAAACTCAGCACCTGCATTGGATGCAGCTGAAACTGGA
80_HRV57a|   AAACAAAGTCAAGCAACAACATCAAACTCAGCACCTGCATTGGATGCAGCTGAAACTGGA
81_HRV57b|   AAACAAAGTCAAGCAACAACATCAAACTCAGCACCTGCATTGGATGCAGCTGAAACTGGA
GROUP_26     AAACAAAGTCAAGCAACAACATCAAACTCAGCACCTGCATTGGATGCAGCTGAAACTGGA

79_HRV57     CACACTAGTAATGTACAACCGGAAGACATGATTGAAACTAGATATGTCCAGACATCACAA
80_HRV57a|   CACACTAGTAATGTACAACCGGAAGACATGATTGAAACTAGATATGTCCAGACATCACAA
81_HRV57b|   CACACTAGTAATGTACAACCGGAAGACATGATTGAAACTAGATATGTCCAGACATCACAA
GROUP_26     CACACTAGTAATGTACAACCGGAAGACATGATTGAAACTAGATATGTCCAGACATCACAA

79_HRV57     ACACGTGATGAAATGAGTCTTGAGAGCTTCTTAGGAAGATCTGGCTGCATTCATATTTCA
80_HRV57a|   ACACGTGATGAAATGAGTCTTGAGAGCTTCTTAGGAAGATCTGGCTGCATTCATATTTCA
81_HRV57b|   ACACGTGATGAAATGAGTCTTGAGAGCTTCTTAGGAAGATCTGGCTGCATTCATATTTCA
GROUP_26     ACACGTGATGAAATGAGTCTTGAGAGCTTCTTAGGAAGATCTGGCTGCATTCATATTTCA

79_HRV57     GAGCTTAAGGTAAAATATGAAAAT---------------TACAACACA---GAG------
80_HRV57a|   GAGCTTAAGGTAAAATATGAAAAT---------------TACAACACA---GAG------
81_HRV57b|   GAGCTTAAGGTAAAATATGAAAAT---------------TACAACACA---GAG------
GROUP_26     GAGCTTAAGGTAAAATATGAAAAT...............TACAACACA...GAG......

79_HRV57     AATTTCACTAAATGGGAAATAAATCTACAAGAAATGGCACAAATCAGAAGAAAATTTGAA
80_HRV57a|   AATTTCACTAAATGGGAAATAAATCTACAAGAAATGGCACAAATCAGAAGAAAATTTGAA
81_HRV57b|   AATTTCACTAAATGGGAAATAAATCTACAAGAAATGGCACAAATCAGAAGAAAATTTGAA
GROUP_26     AATTTCACTAAATGGGAAATAAATCTACAAGAAATGGCACAAATCAGAAGAAAATTTGAA

79_HRV57     CTATTTACATATGTTAGGTTTGATTCTGAAGTTACATTAG-TTCCCTCCATAGCTGCTCA
80_HRV57a|   CTATTTACATATGTTAGGTTTGATTCTGAAGTTACATTAG-TTCCCTCCATAGCTGCTCA
81_HRV57b|   CTATTTACATATGTTAGGTTTGATTCTGAAGTTACATTAG-TTCCCTCCATAGCTGCTCA
GROUP_26     CTATTTACATATGTTAGGTTTGATTCTGAAGTTACATTAG.TTCCCTCCATAGCTGCTCA

79_HRV57     AGGTGAGGATATAGGCCATGTTGTAATGCAATACATGTATGTCCCTCCTGGGGCACCAAT
80_HRV57a|   AGGTGAGGATATAGGCCATGTTGTAATGCAATACATGTATGTCCCTCCTGGGGCACCAAT
81_HRV57b|   AGGTGAGGATATAGGCCATGTTGTAATGCAATACATGTATGTCCCTCCTGGGGCACCAAT
GROUP_26     AGGTGAGGATATAGGCCATGTTGTAATGCAATACATGTATGTCCCTCCTGGGGCACCAAT

79_HRV57     TCCAAAAACAAGAGAGGATTATACATGGCAATCTGGTACCAATGCTTCAATATTTTGGCA
80_HRV57a|   TCCAAAAACAAGAGAGGATTATACATGGCAATCTGGTACCAATGCTTCAATATTTTGGCA
81_HRV57b|   TCCAAAAACAAGAGAGGATTATACATGGCAATCTGGTACCAATGCTTCAATATTTTGGCA
GROUP_26     TCCAAAAACAAGAGAGGATTATACATGGCAATCTGGTACCAATGCTTCAATATTTTGGCA

79_HRV57     ACATGGTCAAACATACCCTAGATTTTCCTTGCCTTTCTTAAGTATAGCCTCAGCATATTA
80_HRV57a|   ACATGGTCAAACATACCCTAGATTTTCCTTGCCTTTCTTAAGTATAGCCTCAGCATATTA
81_HRV57b|   ACATGGTCAAACATACCCTAGATTTTCCTTGCCTTTCTTAAGTATAGCCTCAGCATATTA
GROUP_26     ACATGGTCAAACATACCCTAGATTTTCCTTGCCTTTCTTAAGTATAGCCTCAGCATATTA

79_HRV57     CATGTTTTATGATGGATATGATGGTGACCAAACTGAATCAAGATATGGTACTGTAGTCAC
80_HRV57a|   CATGTTTTATGATGGATATGATGGTGACCAAACTGAATCAAGATATGGTACTGTAGTCAC
81_HRV57b|   CATGTTTTATGATGGATATGATGGTGACCAAACTGAATCAAGATATGGTACTGTAGTCAC
GROUP_26     CATGTTTTATGATGGATATGATGGTGACCAAACTGAATCAAGATATGGTACTGTAGTCAC

79_HRV57     TAATGACATGGGCACTTTATGTTCTAGAATTGTTACTGACCAGCACACACATCCCATAAA
80_HRV57a|   TAATGACATGGGCACTTTATGTTCTAGAATTGTTACTGACCAGCACACACATCCCATAAA
81_HRV57b|   TAATGACATGGGCACTTTATGTTCTAGAATTGTTACTGACCAGCACACACATCCCATAAA
GROUP_26     TAATGACATGGGCACTTTATGTTCTAGAATTGTTACTGACCAGCACACACATCCCATAAA
```

FIG. D14 CONT'D

```
10.trace                                                                 9/20/2007 5:05 PM 2463  79_HRV57      AATAACAACCAGAGTGTATCACAAAGCCAAACATGTCAAAGCCTGGTGCCCTAGACCACC
2464  80_HRV57a|    AATAACAACCAGAGTGTATCACAAAGCCAAACATGTCAAAGCCTGGTGCCCTAGACCACC
2465  81_HRV57b|    AATAACAACCAGAGTGTATCACAAAGCCAAACATGTCAAAGCCTGGTGCCCTAGACCACC
2466  GROUP_26      AATAACAACCAGAGTGTATCACAAAGCCAAACATGTCAAAGCCTGGTGCCCTAGACCACC
2467
2468  79_HRV57      ACGGGCTATCGAGTACACA-CATACACATGTTACTAATTATAAAA-TAAAAG---ATAGA
2469  80_HRV57a|    ACGGGCTATCGAGTACACA-CATACACATGTTACTAATTATAAAA-TAAAAG---ATAGA
2470  81_HRV57b|    ACGGGCTATCGAGTACACA-CATACACATGTTACTAATTATAAAA-TAAAAG---ATAGA
2471  GROUP_26      ACGGGCTATCGAGTACACA.CATACACATGTTACTAATTATAAAA.TAAAAG...ATAGA
2472
2473  79_HRV57      CAAG------AAGAAACAG---CAATTAAATATAGAAGGGACATTAAAATTGTTAAGA--
2474  80_HRV57a|    CAAG------AAGAAACAG---CAATTAAATATAGAAGGGACATTAAAATTGTTAAGA--
2475  81_HRV57b|    CAAG------AAGAAACAG---CAATTAAATATAGAGGGACATTAAAATTGTTAAGA--
2476  GROUP_26      CAAG......AAGAAACAG...CAATTAAATATAGAAGGGACATTAAAATTGTTAAGA..
2477
2478  79_HRV57      ----ATGTG-----------
2479  80_HRV57a|    ----ATGTA-----------
2480  81_HRV57b|    ----ATGTC-----------
2481  GROUP_26      ....ATGT-...........
2482
2483
2484
2485  Group  27:
2486
2487  82_HRV21      AATCCTGTAGAGAATTATATAGATGAAGTCCTAAATGAAGTCTTAGTAGTGCCAAATATC
2488  83_HRVHan     AATCCTGTAGAGAATTACGTAGATGAAGTTCTAAATGAGGTCTTAGTAGTGCCAAATATC
2489  GROUP_27      AATCCTGTAGAGAATTA--TAGATGAAGT-CTAAATGA-GTCTTAGTAGTGCCAAATATC
2490
2491  82_HRV21      AGAGAGAGTCATGGAACAACATCAAACTCTGCTCCCGCACTTGATGCTGCAGAAACTGGA
2492  83_HRVHan     AGAGAGAGTCATGGAACAACATCAAACTCTGCTCCCGCACTTGATGCTGCAGAAACTGGG
2493  GROUP_27      AGAGAGAGTCATGGAACAACATCAAACTCTGCTCCCGCACTTGATGCTGCAGAAACTGG-
2494
2495  82_HRV21      CACACTAGTAATGTACAGCCGGAGGATATGGTTGAAACAAGGTATGTTCAGACATCACAA
2496  83_HRVHan     CACACTAGTAATGTACAACCAGAGGATATGGTTGAAACAAGGTATGTTCAGACATCACAA
2497  GROUP_27      CACACTAGTAATGTACA-CC-GAGGATATGGTTGAAACAAGGTATGTTCAGACATCACAA
2498
2499  82_HRV21      ACACGTGATGAAATGAGTATTGAAAGTTTTCTGGGCAGATCAGGGTGCATTCACATGTCA
2500  83_HRVHan     ACACGTGATGAAATGAGTATTGAAAGTTTTCTAGGCAGATCAGGGTGTATCCACATGTCA
2501  GROUP_27      ACACGTGATGAAATGAGTATTGAAAGTTTTCT-GGCAGATCAGGGTG-AT-CACATGTCA
2502
2503  82_HRV21      AAATTAGTAGTTAACTATGATAAT---------------TACAATACT---GGAGAAAAT
2504  83_HRVHan     AAATTAATAGTTAACTATGACAAC---------------TACAATACT---GGAGAAAAT
2505  GROUP_27      AAATTA-TAGTTAACTATGA-AA-...............TACAATACT...GGAGAAAAT
2506
2507  82_HRV21      AACATTAGTACATGGCAAATAAATATTAAAGAGATGGCACAAATTAGGAGAAAATTTGAA
2508  83_HRVHan     AACATTAATACATGGCAAATAAATATTAAAGAGATGGCACAAATTAGGAGAAAATTTGAA
2509  GROUP_27      AACATTA-TACATGGCAAATAAATATTAAAGAGATGGCACAAATTAGGAGAAAATTTGAA
2510
2511  82_HRV21      ATGTTCACCTATACTAGATTTGATTCAGAAATAACTTTGG-TGCCGTCAATTGCAGCTAG
2512  83_HRVHan     ATGTTCACCTATACTAGATTTGATTCAGAAATAACTTTGG-TACCGTCAATTGCAGCTAA
2513  GROUP_27      ATGTTCACCTATACTAGATTTGATTCAGAAATAACTTTGG.T-CCGTCAATTGCAGCTA-
2514
2515  82_HRV21      AACGGGTGACATAGGACATGTTGTAATGCAATATATGTATGTCCCACCAGGTGCTCCAAT
2516  83_HRVHan     AGCGGGTGACATAGGACATGTTGTGATGCAATATATGTATGTCCCACCAGGTGCTCCAAT
2517  GROUP_27      A-CGGGTGACATAGGACATGTTGT-ATGCAATATATGTATGTCCCACCAGGTGCTCCAAT
2518
2519  82_HRV21      TCCAAAAACTAGGGAAGATTTTGCTTGGCAGTCAGGCACTAATGCATCCATTTTCTGGCA
2520  83_HRVHan     TCCAAAAACTAGGGAAGATTTTGCTTGGCA-TCAGG-AC-AATGCATCCATTTTCTGGCA
2521  GROUP_27      TCCAAAAACTAGGGAAGATTTTGCTTGGCA-TCAGG-AC-AATGCATCCATTTTCTGGCA
2522
2523  82_HRV21      GCATGGCCAGACTTATCCTAGATTTTCATTACCCTTCCTTAGTATAGCATCAGCATACTA
2524  83_HRVHan     GCATGGTCAAACTTATCCTAGATTTTCACTACCCTTCCTTAGTATAGCATCAGCATATTA
2525  GROUP_27      GCATGG-CA-ACTTATCCTAGATTTTCA-TACCCTTCCTTAGTATAGCATCAGCATA-TA
2526
2527  82_HRV21      CATGTTTTATGATGGTTATGATGGTGACCAGACTGACTCACAATATGGTGCAGTAGTAAC
```

FIG. D14 CONT'D

10.trace                                                                                  9/20/2007 5:05 PM

```
2528 83_HRVHan        CATGTTTTATGATGGTTATGATGGTGATCAGACTGACTCACAATATGGTGCAGTGGTGAC
2529 GROUP_27         CATGTTTTATGATGGTTATGATGGTGA-CAGACTGACTCACAATATGGTGCAGT-GT-AC
2530
2531 82_HRV21         TAATGATATGGGATCTCTATGCTACAGAATAGTAACTGGCCAGCATAAGCATAAGATAGA
2532 83_HRVHan        TAATGATATGGGATCTCTATGCTATAGAATAGTAACTGATCAGCATAAGCACAAGATAGA
2533 GROUP_27         TAATGATATGGGATCTCTATGCTA-AGAATAGTAACTG--CAGCATAAGCA-AAGATAGA
2534
2535 82_HRV21         AGTGACCACAAGAATATACCATAAGGCAAAGCATGTTAAAGCTTGGTGCCCCAGACCACC
2536 83_HRVHan        AGTGACCACAAGAATATACCATAAGGCAAAGCATGTTAAAGCTTGGTGCCCTAGACCACC
2537 GROUP_27         AGTGACCACAAGAATATACCATAAGGCAAAGCATGTTAAAGCTTGGTGCCC-AGACCACC
2538
2539 82_HRV21         GAGGGCCGTTGAATACACA-CATACACACGTAACCAATTACAAAA-TTGCAA---ATCAT
2540 83_HRVHan        GAGGGCCGTTGAATACACA-CATACACATGTAACCAATTACAAAA-TTGCAA---ATAAA
2541 GROUP_27         GAGGGCCGTTGAATACACA.CATACACA-GTAACCAATTACAAAA.TTGCAA...AT-A-
2542
2543 82_HRV21         GAAG------TCACTTCTG---CAGTTGAGTCCAGAAGAACAATTGTCACAGTT------
2544 83_HRVHan        GATG------TCACTTCTG---CAGTTGAGTCCAGAAGAACAATTGTCACAGTT------
2545 GROUP_27         GA-G......TCACTTCTG...CAGTTGAGTCCAGAAGAACAATTGTCACAGTT......
2546
2547 82_HRV21         --------------------
2548 83_HRVHan        --------------------
2549 GROUP_27         ....................
2550
2551
2552
2553 Group 28:
2554
2555 84_HRV43         AATCCTGTTGAAAATTATGTTGATGAAATTTTAAATCAAGTTCTTGTAGTCCCAAACACT
2556 85_HRV43b|       AATCCTGTTGAAAATTATGTTGATGAAATTTTAAATCAAGTTCTTGTAGTCCCAAACACT
2557 86_HRV43a|       AATCCTGTTGAAAATTATGTTGATGAAATTTTAAATCAAGTTCTTGTAGTCCCAAACACT
2558 GROUP_28         AATCCTGTTGAAAATTATGTTGATGAAATTTTAAATCAAGTTCTTGTAGTCCCAAACACT
2559
2560 84_HRV43         GTAGAAAGTCATTCAACAACATCCAATGCAGCCCCTGCACTTGATGCAGCTGAAACTGGG
2561 85_HRV43b|       GTAGAAAGTCATTCAACAACATCCAATGCAGCCCCTGCACTTGATGCAGCTGAAACTGGG
2562 86_HRV43a|       GTAGAAAGTCATTCAACAACATCCAATGCAGCCCCTGCACTTGATGCAGCTGAAACTGGG
2563 GROUP_28         GTAGAAAGTCATTCAACAACATCCAATGCAGCCCCTGCACTTGATGCAGCTGAAACTGGG
2564
2565 84_HRV43         CATACTAGCCAGGTGCAACCTGAAGACATGGTAGAGACAAGGTCAGTACATAATTTCCAA
2566 85_HRV43b|       CATACTAGCCAGGTGCAACCTGAAGACATGGTAGAGACAAGGTCAGTACATAATTTCCAA
2567 86_HRV43a|       CATACTAGCCAGGTGCAACCTGAAGACATGGTAGAGACAAGGTCAGTACATAATTTCCAA
2568 GROUP_28         CATACTAGCCAGGTGCAACCTGAAGACATGGTAGAGACAAGGTCAGTACATAATTTCCAA
2569
2570 84_HRV43         ACCAGAGATGAAATGAGTATTGAAAGTTTCTTGGGCAGATCTGGTTGCATACATATTTCA
2571 85_HRV43b|       ACCAGAGATGAAATGAGTATTGAAAGTTTCTTGGGCAGATCTGGTTGCATACATATTTCA
2572 86_HRV43a|       ACCAGAGATGAAATGAGTATTGAAAGTTTCTTGGGCAGATCTGGTTGCATACATATTTCA
2573 GROUP_28         ACCAGAGATGAAATGAGTATTGAAAGTTTCTTGGGCAGATCTGGTTGCATACATATTTCA
2574
2575 84_HRV43         ACACTTGAAGTAAATTATGATGAT---------------TATAATGGG---ACAGGCATA
2576 85_HRV43b|       ACACTTGAAGTAAATTATGATGAT---------------TATAATGGG---ACAGGCATA
2577 86_HRV43a|       ACACTTGAAGTAAATTATGATGAT---------------TATAATGGG---ACAGGCATA
2578 GROUP_28         ACACTTGAAGTAAATTATGATGAT...............TATAATGGG...ACAGGCATA
2579
2580 84_HRV43         AATTTTACCCAATGGCCAATCAACTTGCAAGAAATGGCACAAATTAGAAGAAAGTATGAA
2581 85_HRV43b|       AATTTTACCCAATGGCCAATCAACTTGCAAGAAATGGCACAAATTAGAAGAAAGTATGAA
2582 86_HRV43a|       AATTTTACCCAATGGCCAATCAACTTGCAAGAAATGGCACAAATTAGAAGAAAGTATGAA
2583 GROUP_28         AATTTTACCCAATGGCCAATCAACTTGCAAGAAATGGCACAAATTAGAAGAAAGTATGAA
2584
2585 84_HRV43         TTGTTCACATACTTAAGGTTTGATTCTGAAATTACCCTTG-TTCCTTGCATTGCAGCAAA
2586 85_HRV43b|       TTGTTCACATACTTAAGGTTTGATTCTGAAATTACCCTTG-TTCCTTGCATTGCAGCAAA
2587 86_HRV43a|       TTGTTCACATACTTAAGGTTTGATTCTGAAATTACCCTTG-TTCCTTGCATTGCAGCAAA
2588 GROUP_28         TTGTTCACATACTTAAGGTTTGATTCTGAAATTACCCTTG.TTCCTTGCATTGCAGCAAA
2589
2590 84_HRV43         AAGCAATGATATAGGCCATGTGGTAATGCAGTACATGTATGTACCACCAGGTGCGCCAAT
2591 85_HRV43b|       AAGCAATGATATAGGCCATGTGGTAATGCAGTACATGTATGTACCACCAGGTGCGCCAAT
2592 86_HRV43a|       AAGCAATGATATAGGCCATGTGGTAATGCAGTACATGTATGTACCACCAGGTGCGCCAAT
```

FIG. D14 CONT'D

```
10.trace                                                                    9/20/2007 5:05 PM 2593 GROUP_28      AAGCAATGATATAGGCCATGTGGTAATGCAGTACATGTATGTACCACCAGGTGCGCCAAT
2594
2595 84_HRV43      TCCAAAAACTAGGAAAGATTATGCATGGCAATCTGGCACAAATGCATCTGTTTTCTGGCA
2596 85_HRV43b|    TCCAAAAACTAGGAAAGATTATGCATGGCAATCTGGCACAAATGCATCTGTTTTCTGGCA
2597 86_HRV43a|    TCCAAAAACTAGGAAAGATTATGCATGGCAATCTGGCACAAATGCATCTGTTTTCTGGCA
2598 GROUP_28      TCCAAAAACTAGGAAAGATTATGCATGGCAATCTGGCACAAATGCATCTGTTTTCTGGCA
2599
2600 84_HRV43      ACATGGTCAAACATTTCCAAGATTTTCCTTACCTTTTCTGAGCATAGCATCAGCATATTA
2601 85_HRV43b|    ACATGGTCAAACATTTCCAAGATTTTCCTTACCTTTTCTGAGCATAGCATCAGCATATTA
2602 86_HRV43a|    ACATGGTCAAACATTTCCAAGATTTTCCTTACCTTTTCTGAGCATAGCATCAGCATATTA
2603 GROUP_28      ACATGGTCAAACATTTCCAAGATTTTCCTTACCTTTTCTGAGCATAGCATCAGCATATTA
2604
2605 84_HRV43      CATGTTTTATGATGGATATGAAGGTGACCAAAAAACATCCCGTTATGGCACAATTGCAAG
2606 85_HRV43b|    CATGTTTTATGATGGATATGAAGGTGACCAAAAAACATCCCGTTATGGCACAATTGCAAG
2607 86_HRV43a|    CATGTTTTATGATGGATATGAAGGTGACCAAAAAACATCCCGTTATGGCACAATTGCAAG
2608 GROUP_28      CATGTTTTATGATGGATATGAAGGTGACCAAAAAACATCCCGTTATGGCACAATTGCAAG
2609
2610 84_HRV43      CAACCACATGGGAACATTATGTTCTAGGATAGTTACAGAAGAACACCAAAATCAAATCGA
2611 85_HRV43b|    CAACCACATGGGAACATTATGTTCTAGGATAGTTACAGAAGAACACCAAAATCAAATCGA
2612 86_HRV43a|    CAACCACATGGGAACATTATGTTCTAGGATAGTTACAGAAGAACACCAAAATCAAATCGA
2613 GROUP_28      CAACCACATGGGAACATTATGTTCTAGGATAGTTACAGAAGAACACCAAAATCAAATCGA
2614
2615 84_HRV43      GATAACTACCAGGATATATCATAAAGCCAAGCATATCAAAGCTTGGTGCCCAAGACCACC
2616 85_HRV43b|    GATAACTACCAGGATATATCATAAAGCCAAGCATATCAAAGCTTGGTGCCCAAGACCACC
2617 86_HRV43a|    GATAACTACCAGGATATATCATAAAGCCAAGCATATCAAAGCTTGGTGCCCAAGACCACC
2618 GROUP_28      GATAACTACCAGGATATATCATAAAGCCAAGCATATCAAAGCTTGGTGCCCAAGACCACC
2619
2620 84_HRV43      CAGAGCTGTTGAATACACA-CACACACATGTCACAAATTATAAAA-GAGAAG---GAAAG
2621 85_HRV43b|    CAGAGCTGTTGAATACACA-CACACACATGTCACAAATTATAAAA-GAGAAG---GAAAG
2622 86_HRV43a|    CAGAGCTGTTGAATACACA-CACACACATGTCACAAATTATAAAA-GAGAAG---GAAAG
2623 GROUP_28      CAGAGCTGTTGAATACACA.CACACACATGTCACAAATTATAAAA.GAGAAG...GAAAG
2624
2625 84_HRV43      GAGG------TAGAAACAG---CCATAGTATCTAGGAGGGATATCAAAATTGTCAATG--
2626 85_HRV43b|    GAGG------TAGAAACAG---CCATAGTATCTAGGAGGGATATCAAAATTGTCAATG--
2627 86_HRV43a|    GAGG------TAGAAACAG---CCATAGTATCTAGGAGGGATATCAAAATTGTCAATG--
2628 GROUP_28      GAGG......TAGAAACAG...CCATAGTATCTAGGAGGGATATCAAAATTGTCAATG..
2629
2630 84_HRV43      ----CA---------------
2631 85_HRV43b|    ----CG---------------
2632 86_HRV43a|    ----CT---------------
2633 GROUP_28      ....C-...............
2634
2635
2636
2637 Group 29:
2638
2639 87_HRV75      AATCCAGTTGAAAATTATGTGGATGAAATTTTAAACCAAGTTCTGGTAGTTCCAAACACC
2640 88_HRV75b|    AATCCAGTTGAAAATTATGTGGATGAAATTTTAAACCAAGTTCTGGTAGTTCCAAACACC
2641 89_HRV75a|    AATCCAGTTGAAAATTATGTGGATGAAATTTTAAACCAAGTTCTGGTAGTTCCAAACACC
2642 GROUP_29      AATCCAGTTGAAAATTATGTGGATGAAATTTTAAACCAAGTTCTGGTAGTTCCAAACACC
2643
2644 87_HRV75      ATGGAGAGCCATCCAACAACGTCTAATGCTGCTCCAGCTTTAGATGCAGCTGAAACTGGC
2645 88_HRV75b|    ATGGAGAGCCATCCAACAACGTCTAATGCTGCTCCAGCTTTAGATGCAGCTGAAACTGGC
2646 89_HRV75a|    ATGGAGAGCCATCCAACAACGTCTAATGCTGCTCCAGCTTTAGATGCAGCTGAAACTGGC
2647 GROUP_29      ATGGAGAGCCATCCAACAACGTCTAATGCTGCTCCAGCTTTAGATGCAGCTGAAACTGGC
2648
2649 87_HRV75      CATACCAGCCATGTTCAACCAGAAGACATGTTAGAAACAAGGCAAGTACAAAATTTCCAA
2650 88_HRV75b|    CATACCAGCCATGTTCAACCAGAAGACATGTTAGAAACAAGGCAAGTACAAAATTTCCAA
2651 89_HRV75a|    CATACCAGCCATGTTCAACCAGAAGACATGTTAGAAACAAGGCAAGTACAAAATTTCCAA
2652 GROUP_29      CATACCAGCCATGTTCAACCAGAAGACATGTTAGAAACAAGGCAAGTACAAAATTTCCAA
2653
2654 87_HRV75      ACTAGAGATGAGATGAGTATTGAGAGTTTCCTAGGCAGATCTGGATGTATTCATATTTCA
2655 88_HRV75b|    ACTAGAGATGAGATGAGTATTGAGAGTTTCCTAGGCAGATCTGGATGTATTCATATTTCA
2656 89_HRV75a|    ACTAGAGATGAGATGAGTATTGAGAGTTTCCTAGGCAGATCTGGATGTATTCATATTTCA
2657 GROUP_29      ACTAGAGATGAGATGAGTATTGAGAGTTTCCTAGGCAGATCTGGATGTATTCATATTTCA
```

FIG. D14 CONT'D

10.trace                                                                9/20/2007 5:05 PM

```
2658
2659  87_HRV75      ACACTTGAGATGGATTATACAAAC---------------TATAATGGA---GAAGGCAAA
2660  88_HRV75b|    ACACTTGAGATGGATTATACAAAC---------------TATAATGGA---GAAGGCAAA
2661  89_HRV75a|    ACACTTGAGATGGATTATACAAAC---------------TATAATGGA---GAAGGCAAA
2662  GROUP_29      ACACTTGAGATGGATTATACAAAC...............TATAATGGA...GAAGGCAAA
2663
2664  87_HRV75      AACTTCACTCAGTGGCCAATCAATCTACAGGAAATGGCTCAAATTAGAAGGAAATATGAA
2665  88_HRV75b|    AACTTCACTCAGTGGCCAATCAATCTACAGGAAATGGCTCAAATTAGAAGGAAATATGAA
2666  89_HRV75a|    AACTTCACTCAGTGGCCAATCAATCTACAGGAAATGGCTCAAATTAGAAGGAAATATGAA
2667  GROUP_29      AACTTCACTCAGTGGCCAATCAATCTACAGGAAATGGCTCAAATTAGAAGGAAATATGAA
2668
2669  87_HRV75      TTATTTACATATCTTAGATTTGATTCAGAGGTTACTCTGG-TGCCATGCATTGCAGCTAA
2670  88_HRV75b|    TTATTTACATATCTTAGATTTGATTCAGAGGTTACTCTGG-TGCCATGCATTGCAGCTAA
2671  89_HRV75a|    TTATTTACATATCTTAGATTTGATTCAGAGGTTACTCTGG-TGCCATGCATTGCAGCTAA
2672  GROUP_29      TTATTTACATATCTTAGATTTGATTCAGAGGTTACTCTGG.TGCCATGCATTGCAGCTAA
2673
2674  87_HRV75      AGGGAATGACATAGGCCATGTAGTAATGCAATATATGTATGTACCACCAGGAGCACCAAT
2675  88_HRV75b|    AGGGAATGACATAGGCCATGTAGTAATGCAATATATGTATGTACCACCAGGAGCACCAAT
2676  89_HRV75a|    AGGGAATGACATAGGCCATGTAGTAATGCAATATATGTATGTACCACCAGGAGCACCAAT
2677  GROUP_29      AGGGAATGACATAGGCCATGTAGTAATGCAATATATGTATGTACCACCAGGAGCACCAAT
2678
2679  87_HRV75      ACCAACAACTAGAAAAGATTATGCATGGCAATCTGGAACAAATGCATCTGTATTTTGGCA
2680  88_HRV75b|    ACCAACAACTAGAAAAGATTATGCATGGCAATCTGGAACAAATGCATCTGTATTTTGGCA
2681  89_HRV75a|    ACCAACAACTAGAAAAGATTATGCATGGCAATCTGGAACAAATGCATCTGTATTTTGGCA
2682  GROUP_29      ACCAACAACTAGAAAAGATTATGCATGGCAATCTGGAACAAATGCATCTGTATTTTGGCA
2683
2684  87_HRV75      ACATGGACAAACATTTCCAAGATTTTCACTACCATTTCTGAGCATTGCATCAGCATATTA
2685  88_HRV75b|    ACATGGACAAACATTTCCAAGATTTTCACTACCATTTCTGAGCATTGCATCAGCATATTA
2686  89_HRV75a|    ACATGGACAAACATTTCCAAGATTTTCACTACCATTTCTGAGCATTGCATCAGCATATTA
2687  GROUP_29      ACATGGACAAACATTTCCAAGATTTTCACTACCATTTCTGAGCATTGCATCAGCATATTA
2688
2689  87_HRV75      CATGTTTTATGATGGATATGAAGGGGATCAAAATACATCCCGTTATGGCACCATTGCTAG
2690  88_HRV75b|    CATGTTTTATGATGGATATGAAGGGGATCAAAATACATCCCGTTATGGCACCATTGCTAG
2691  89_HRV75a|    CATGTTTTATGATGGATATGAAGGGGATCAAAATACATCCCGTTATGGCACCATTGCTAG
2692  GROUP_29      CATGTTTTATGATGGATATGAAGGGGATCAAAATACATCCCGTTATGGCACCATTGCTAG
2693
2694  87_HRV75      TAATCACATGGGGACACTGTGTTCTAGAATAGTTACAGAAGAACATCGAAATAAAGTTGA
2695  88_HRV75b|    TAATCACATGGGGACACTGTGTTCTAGAATAGTTACAGAAGAACATCGAAATAAAGTTGA
2696  89_HRV75a|    TAATCACATGGGGACACTGTGTTCTAGAATAGTTACAGAAGAACATCGAAATAAAGTTGA
2697  GROUP_29      TAATCACATGGGGACACTGTGTTCTAGAATAGTTACAGAAGAACATCGAAATAAAGTTGA
2698
2699  87_HRV75      AGTAACCACTAGAATATATCACAAAGCCAAACATATAAAAGCTTGGTGTCCGAGGCCGCC
2700  88_HRV75b|    AGTAACCACTAGAATATATCACAAAGCCAAACATATAAAAGCTTGGTGTCCGAGGCCGCC
2701  89_HRV75a|    AGTAACCACTAGAATATATCACAAAGCCAAACATATAAAAGCTTGGTGTCCGAGGCCGCC
2702  GROUP_29      AGTAACCACTAGAATATATCACAAAGCCAAACATATAAAAGCTTGGTGTCCGAGGCCGCC
2703
2704  87_HRV75      CAGGGCTGTTGAATACACA-TTTAGACGTGTAACAAATTACAAAA-GAGATG---GACAA
2705  88_HRV75b|    CAGGGCTGTTGAATACACA-TTTAGACGTGTAACAAATTACAAAA-GAGATG---GACAA
2706  89_HRV75a|    CAGGGCTGTTGAATACACA-TTTAGACGTGTAACAAATTACAAAA-GAGATG---GACAA
2707  GROUP_29      CAGGGCTGTTGAATACACA.TTTAGACGTGTAACAAATTACAAAA.GAGATG...GACAA
2708
2709  87_HRV75      CAAG------TTGAGATTG---CTATTGAGCCCAGAAGAGATGTTAAGTTTGTAAATG--
2710  88_HRV75b|    CAAG------TTGAGATTG---CTATTGAGCCCAGAAGAGATGTTAAGTTTGTAAATG--
2711  89_HRV75a|    CAAG------TTGAGATTG---CTATTGAGCCCAGAAGAGATGTTAAGTTTGTAAATG--
2712  GROUP_29      CAAG......TTGAGATTG...CTATTGAGCCCAGAAGAGATGTTAAGTTTGTAAATG..
2713
2714  87_HRV75      ----CA---------------
2715  88_HRV75b|    ----CG---------------
2716  89_HRV75a|    ----CT---------------
2717  GROUP_29      ....C-...............
2718
2719
2720
2721  Group  30:
2722
```

FIG. D14 CONT'D 10.trace                                                                                              9/20/2007 5:05 PM

```
2723  96_HRV9a|d    AATCCAGTGGAGAATTACATAGATCAGGTGCTTAATGAGGTTTTGGTAGTCCCAAACATT
2724  97_HRV9b|d    AATCCAGTGGAGAATTACATAGATCAGGTGCTTAATGAGGTTTTGGTAGTCCCAAACATT
2725  98_HRV9       AATCCAGTGGAGAATTACATAGATCAGGTGCTTAATGAGGTTTTGGTAGTCCCAAACATT
2726  GROUP_30     AATCCAGTGGAGAATTACATAGATCAGGTGCTTAATGAGGTTTTGGTAGTCCCAAACATT
2727
2728  96_HRV9a|d    AAAGAGAGCAACCCTACAACCTCTAACTCAGCTCCAGCTCTAGATGCTGCTGAGACAGGC
2729  97_HRV9b|d    AAAGAGAGCAACCCTACAACCTCTAACTCAGCTCCAGCTCTAGATGCTGCTGAGACAGGC
2730  98_HRV9       AAAGAGAGCAACCCTACAACCTCTAACTCAGCTCCAGCTCTAGATGCTGCTGAGACAGGC
2731  GROUP_30     AAAGAGAGCAACCCTACAACCTCTAACTCAGCTCCAGCTCTAGATGCTGCTGAGACAGGC
2732
2733  96_HRV9a|d    CATACTAGCAATGTTCAACCTGAAGACATGATTGAAACACGTTATGTGCAGACATCACAA
2734  97_HRV9b|d    CATACTAGCAATGTTCAACCTGAAGACATGATTGAAACACGTTATGTGCAGACATCACAA
2735  98_HRV9       CATACTAGCAATGTTCAACCTGAAGACATGATTGAAACACGTTATGTGCAGACATCACAA
2736  GROUP_30     CATACTAGCAATGTTCAACCTGAAGACATGATTGAAACACGTTATGTGCAGACATCACAA
2737
2738  96_HRV9a|d    ACCAGAGATGAAATGAGTCTTGAAAGCTTCTTAGGGAGATCAGGTTGTATACACATATCT
2739  97_HRV9b|d    ACCAGAGATGAAATGAGTCTTGAAAGCTTCTTAGGGAGATCAGGTTGTATACACATATCT
2740  98_HRV9       ACCAGAGATGAAATGAGTCTTGAAAGCTTCTTAGGGAGATCAGGTTGTATACACATATCT
2741  GROUP_30     ACCAGAGATGAAATGAGTCTTGAAAGCTTCTTAGGGAGATCAGGTTGTATACACATATCT
2742
2743  96_HRV9a|d    AAATTGAATATTGATTACAGTGAC---------------TATGATAAG---AGTGTTGAA
2744  97_HRV9b|d    AAATTGAATATTGATTACAGTGAC---------------TATGATAAG---AGTGTTGAA
2745  98_HRV9       AAATTGAATATTGATTACAGTGAC---------------TATGATAAG---AGTGTTGAA
2746  GROUP_30     AAATTGAATATTGATTACAGTGAC...............TATGATAAG...AGTGTTGAA
2747
2748  96_HRV9a|d    AATTTCACAATCTGGAAAATAAATATAAAGGAAATGGCCCAGATCAGGAGGAAATTTGAA
2749  97_HRV9b|d    AATTTCACAATCTGGAAAATAAATATAAAGGAAATGGCCCAGATCAGGAGGAAATTTGAA
2750  98_HRV9       AATTTCACAATCTGGAAAATAAATATAAAGGAAATGGCCCAGATCAGGAGGAAATTTGAA
2751  GROUP_30     AATTTCACAATCTGGAAAATAAATATAAAGGAAATGGCCCAGATCAGGAGGAAATTTGAA
2752
2753  96_HRV9a|d    TTGTTTACATATGCAAGATTTGACTCTGAAATAACATTGG-TCCCGTGTATAGCAGCAGA
2754  97_HRV9b|d    TTGTTTACATATGCAAGATTTGACTCTGAAATAACATTGG-TCCCGTGTATAGCAGCAGA
2755  98_HRV9       TTGTTTACATATGCAAGATTTGACTCTGAAATAACATTGG-TCCCGTGTATAGCAGCAGA
2756  GROUP_30     TTGTTTACATATGCAAGATTTGACTCTGAAATAACATTGG.TCCCGTGTATAGCAGCAGA
2757
2758  96_HRV9a|d    AAGTGATAGCGTTGGCCATGTTGTTATGCAGTACATGTATGTACCACCAGGGGCACCTTT
2759  97_HRV9b|d    AAGTGATAGCGTTGGCCATGTTGTTATGCAGTACATGTATGTACCACCAGGGGCACCTTT
2760  98_HRV9       AAGTGATAGCGTTGGCCATGTTGTTATGCAGTACATGTATGTACCACCAGGGGCACCTTT
2761  GROUP_30     AAGTGATAGCGTTGGCCATGTTGTTATGCAGTACATGTATGTACCACCAGGGGCACCTTT
2762
2763  96_HRV9a|d    ACCAAGGACTAGAGATGATTATGCATGGCAATCAGGCACAAATGCTTCCATCTTTTGGCA
2764  97_HRV9b|d    ACCAAGGACTAGAGATGATTATGCATGGCAATCAGGCACAAATGCTTCCATCTTTTGGCA
2765  98_HRV9       ACCAAGGACTAGAGATGATTATGCATGGCAATCAGGCACAAATGCTTCCATCTTTTGGCA
2766  GROUP_30     ACCAAGGACTAGAGATGATTATGCATGGCAATCAGGCACAAATGCTTCCATCTTTTGGCA
2767
2768  96_HRV9a|d    ACATGGACAATCATATCCCAGATTTTCACTTCCGTTTTTGAGCATTGCCTCTGCATATTA
2769  97_HRV9b|d    ACATGGACAATCATATCCCAGATTTTCACTTCCGTTTTTGAGCATTGCCTCTGCATATTA
2770  98_HRV9       ACATGGACAATCATATCCCAGATTTTCACTTCCGTTTTTGAGCATTGCCTCTGCATATTA
2771  GROUP_30     ACATGGACAATCATATCCCAGATTTTCACTTCCGTTTTTGAGCATTGCCTCTGCATATTA
2772
2773  96_HRV9a|d    CATGTTCTATGATGGTTATGATGGTGG---ACCAGATTCTCTGTATGGAACAATTGTAAC
2774  97_HRV9b|d    CATGTTCTATGATGGTTATGATGGTGG---ACCAGATTCTCTGTATGGAACAATTGTAAC
2775  98_HRV9       CATGTTCTATGATGGTTATGATGGTGG---ACCAGATTCTCTGTATGGAACAATTGTAAC
2776  GROUP_30     CATGTTCTATGATGGTTATGATGGTGG...ACCAGATTCTCTGTATGGAACAATTGTAAC
2777
2778  96_HRV9a|d    AAATGATATGGGATCTTTATGTTCCCGTGTAGTTACTGAAGAGCATGGACCCCGTGTCAA
2779  97_HRV9b|d    AAATGATATGGGATCTTTATGTTCCCGTGTAGTTACTGAAGAGCATGGACCCCGTGTCAA
2780  98_HRV9       AAATGATATGGGATCTTTATGTTCCCGTGTAGTTACTGAAGAGCATGGACCCCGTGTCAA
2781  GROUP_30     AAATGATATGGGATCTTTATGTTCCCGTGTAGTTACTGAAGAGCATGGACCCCGTGTCAA
2782
2783  96_HRV9a|d    AATTTCAACCAGAATATATCACAAAGCCAAACATGTTAAAGCCTGGTGCCCAAGACCTCC
2784  97_HRV9b|d    AATTTCAACCAGAATATATCACAAAGCCAAACATGTTAAAGCCTGGTGCCCAAGACCTCC
2785  98_HRV9       AATTTCAACCAGAATATATCACAAAGCCAAACATGTTAAAGCCTGGTGCCCAAGACCTCC
2786  GROUP_30     AATTTCAACCAGAATATATCACAAAGCCAAACATGTTAAAGCCTGGTGCCCAAGACCTCC
2787
```

FIG. D14 CONT'D

10.trace                                                                                        9/20/2007 5:05 PM

```
2788  96_HRV9a|d     TAGGGCAGTTGAGTATATA-CATACACATGTCACAAATTACAAGC-CAAGCA---CAGGC
2789  97_HRV9b|d     TAGGGCAGTTGAGTATATA-CATACACATGTCACAAATTACAAGC-CAAGCA---CAGGC
2790  98_HRV9        TAGGGCAGTTGAGTATATA-CATACACATGTCACAAATTACAAGC-CAAGCA---CAGGC
2791  GROUP_30       TAGGGCAGTTGAGTATATA.CATACACATGTCACAAATTACAAGC.CAAGCA...CAGGC
2792
2793  96_HRV9a|d     GATT------ATGCCACAG---TTATACCAGTTAGAGACAATGTTAGGGCAGTAAAGA--
2794  97_HRV9b|d     GATT------ATGCCACAG---TTATACCAGTTAGAGACAATGTTAGGGCAGTAAAGA--
2795  98_HRV9        GATT------ATGCCACAG---TTATACCAGTTAGAGACAATGTTAGGGCAGTAAAGA--
2796  GROUP_30       GATT......ATGCCACAG...TTATACCAGTTAGAGACAATGTTAGGGCAGTAAAGA..
2797
2798  96_HRV9a|d     ----ATGTC------------
2799  97_HRV9b|d     ----ATGTG------------
2800  98_HRV9        ----ATGTA------------
2801  GROUP_30       ....ATGT-............
2802
2803
2804
2805  Group 31:
2806
2807  99_HRV32       AATCCTGTGGAGAATTACATAGATCAAGTTTTAAATGAAGTTTTGGTAGTTCCAAACATC
2808  100_HRV32a     AATCCTGTGGAGAATTACATAGATCAAGTTTTAAATGAAGTTTTGGTAGTTCCAAACATC
2809  101_HRV32b     AATCCTGTGGAGAATTACATAGATCAAGTTTTAAATGAAGTTTTGGTAGTTCCAAACATC
2810  GROUP_31       AATCCTGTGGAGAATTACATAGATCAAGTTTTAAATGAAGTTTTGGTAGTTCCAAACATC
2811
2812  99_HRV32       AAAGAAAGCAATCCCACAACCTCTAATTCAGCCCCAGCCTTAGATGCTGCCGAAACAGGT
2813  100_HRV32a     AAAGAAAGCAATCCCACAACCTCTAATTCAGCCCCAGCCTTAGATGCTGCCGAAACAGGT
2814  101_HRV32b     AAAGAAAGCAATCCCACAACCTCTAATTCAGCCCCAGCCTTAGATGCTGCCGAAACAGGT
2815  GROUP_31       AAAGAAAGCAATCCCACAACCTCTAATTCAGCCCCAGCCTTAGATGCTGCCGAAACAGGT
2816
2817  99_HRV32       CATACCAGTAATGTTCAACCTGAAGACATGATTGAAACACGTTATGTGCAAACAACACAC
2818  100_HRV32a     CATACCAGTAATGTTCAACCTGAAGACATGATTGAAACACGTTATGTGCAAACAACACAC
2819  101_HRV32b     CATACCAGTAATGTTCAACCTGAAGACATGATTGAAACACGTTATGTGCAAACAACACAC
2820  GROUP_31       CATACCAGTAATGTTCAACCTGAAGACATGATTGAAACACGTTATGTGCAAACAACACAC
2821
2822  99_HRV32       ACTAGAGATGAGATGAGTCTTGAGAGCTTCTTAGGGAGGTCAGGATGTGTACATATATCC
2823  100_HRV32a     ACTAGAGATGAGATGAGTCTTGAGAGCTTCTTAGGGAGGTCAGGATGTGTACATATATCC
2824  101_HRV32b     ACTAGAGATGAGATGAGTCTTGAGAGCTTCTTAGGGAGGTCAGGATGTGTACATATATCC
2825  GROUP_31       ACTAGAGATGAGATGAGTCTTGAGAGCTTCTTAGGGAGGTCAGGATGTGTACATATATCC
2826
2827  99_HRV32       AAATTAGATATTGATTATACCAAT---------------TACAATAAA---AGTGTTAAG
2828  100_HRV32a     AAATTAGATATTGATTATACCAAT---------------TACAATAAA---AGTGTTAAG
2829  101_HRV32b     AAATTAGATATTGATTATACCAAT---------------TACAATAAA---AGTGTTAAG
2830  GROUP_31       AAATTAGATATTGATTATACCAAT...............TACAATAAA...AGTGTTAAG
2831
2832  99_HRV32       AATTTCACAATTTGGAAGATAAATATAAAAGAAATGGCCCAGATTAGGAGAAAATTTGAG
2833  100_HRV32a     AATTTCACAATTTGGAAGATAAATATAAAAGAAATGGCCCAGATTAGGAGAAAATTTGAG
2834  101_HRV32b     AATTTCACAATTTGGAAGATAAATATAAAAGAAATGGCCCAGATTAGGAGAAAATTTGAG
2835  GROUP_31       AATTTCACAATTTGGAAGATAAATATAAAAGAAATGGCCCAGATTAGGAGAAAATTTGAG
2836
2837  99_HRV32       TTGTTTACATACACAAGGTTTGATTCTGAAATAACATTAG-TACCTTGTATAGCTGCAGA
2838  100_HRV32a     TTGTTTACATACACAAGGTTTGATTCTGAAATAACATTAG-TACCTTGTATAGCTGCAGA
2839  101_HRV32b     TTGTTTACATACACAAGGTTTGATTCTGAAATAACATTAG-TACCTTGTATAGCTGCAGA
2840  GROUP_31       TTGTTTACATACACAAGGTTTGATTCTGAAATAACATTAG.TACCTTGTATAGCTGCAGA
2841
2842  99_HRV32       AAGTGACAGCATTGGTCATGTTGTTATGCAGTACATGTATGTACCACCAGGGGCTCCTCT
2843  100_HRV32a     AAGTGACAGCATTGGTCATGTTGTTATGCAGTACATGTATGTACCACCAGGGGCTCCTCT
2844  101_HRV32b     AAGTGACAGCATTGGTCATGTTGTTATGCAGTACATGTATGTACCACCAGGGGCTCCTCT
2845  GROUP_31       AAGTGACAGCATTGGTCATGTTGTTATGCAGTACATGTATGTACCACCAGGGGCTCCTCT
2846
2847  99_HRV32       ACCACAAGCAAGAGATGACTACACATGGCAATCTGGCACGAATGCATCTATCTTTTGGCA
2848  100_HRV32a     ACCACAAGCAAGAGATGACTACACATGGCAATCTGGCACGAATGCATCTATCTTTTGGCA
2849  101_HRV32b     ACCACAAGCAAGAGATGACTACACATGGCAATCTGGCACGAATGCATCTATCTTTTGGCA
2850  GROUP_31       ACCACAAGCAAGAGATGACTACACATGGCAATCTGGCACGAATGCATCTATCTTTTGGCA
2851
2852  99_HRV32       GCATGGACAGGCATATCCCAGGTTTTCACTTCCATTTCTAAGTATTGCCTCTGCATACTA
```

FIG. D14 CONT'D

```
10.trace                                                                  9/20/2007 5:05 PM 2853 100_HRV32a    GCATGGACAGGCATATCCCAGGTTTTCACTTCCATTTCTAAGTATTGCCTCTGCATACTA
2854 101_HRV32b    GCATGGACAGGCATATCCCAGGTTTTCACTTCCATTTCTAAGTATTGCCTCTGCATACTA
2855 GROUP_31      GCATGGACAGGCATATCCCAGGTTTTCACTTCCATTTCTAAGTATTGCCTCTGCATACTA
2856
2857 99_HRV32      CATGTTTTATGATGGTTATGATGGTGG---GCCAGATTCACAATATGGAACAATTGTAAC
2858 100_HRV32a    CATGTTTTATGATGGTTATGATGGTGG---GCCAGATTCACAATATGGAACAATTGTAAC
2859 101_HRV32b    CATGTTTTATGATGGTTATGATGGTGG---GCCAGATTCACAATATGGAACAATTGTAAC
2860 GROUP_31      CATGTTTTATGATGGTTATGATGGTGG...GCCAGATTCACAATATGGAACAATTGTAAC
2861
2862 99_HRV32      AAATGATATGGGTTCCCTGTGTTCTCGTATAGTCACCGAAGAGCACGGATCCCGTGTTGA
2863 100_HRV32a    AAATGATATGGGTTCCCTGTGTTCTCGTATAGTCACCGAAGAGCACGGATCCCGTGTTGA
2864 101_HRV32b    AAATGATATGGGTTCCCTGTGTTCTCGTATAGTCACCGAAGAGCACGGATCCCGTGTTGA
2865 GROUP_31      AAATGATATGGGTTCCCTGTGTTCTCGTATAGTCACCGAAGAGCACGGATCCCGTGTTGA
2866
2867 99_HRV32      TATTTCAACTAGGGTATATCACAAAGCTAAACACGTCAAAGCTTGGTGCCCACGACCACC
2868 100_HRV32a    TATTTCAACTAGGGTATATCACAAAGCTAAACACGTCAAAGCTTGGTGCCCACGACCACC
2869 101_HRV32b    TATTTCAACTAGGGTATATCACAAAGCTAAACACGTCAAAGCTTGGTGCCCACGACCACC
2870 GROUP_31      TATTTCAACTAGGGTATATCACAAAGCTAAACACGTCAAAGCTTGGTGCCCACGACCACC
2871
2872 99_HRV32      TAGGGCAGTTGAATATACA-CATACACATGTTACAAATTACAAAC-CAAGCA---CAGGT
2873 100_HRV32a    TAGGGCAGTTGAATATACA-CATACACATGTTACAAATTACAAAC-CAAGCA---CAGGT
2874 101_HRV32b    TAGGGCAGTTGAATATACA-CATACACATGTTACAAATTACAAAC-CAAGCA---CAGGT
2875 GROUP_31      TAGGGCAGTTGAATATACA.CATACACATGTTACAAATTACAAAC.CAAGCA...CAGGT
2876
2877 99_HRV32      GATT------ACACCACAG---CCATACAAACCAGAGAGCATGTTAGAGCAGTCAAAA--
2878 100_HRV32a    GATT------ACACCACAG---CCATACAAACCAGAGAGCATGTTAGAGCAGTCAAAA--
2879 101_HRV32b    GATT------ACACCACAG---CCATACAAACCAGAGAGCATGTTAGAGCAGTCAAAA--
2880 GROUP_31      GATT......ACACCACAG...CCATACAAACCAGAGAGCATGTTAGAGCAGTCAAAA..
2881
2882 99_HRV32      ----ATGTA-----------
2883 100_HRV32a    ----ATGTG-----------
2884 101_HRV32b    ----ATGTC-----------
2885 GROUP_31      ....ATGT-...........
2886
2887
2888
2889 Group 32:
2890
2891 102_HRV67     AACCCAGTAGAAGATTATGTAGATCAGGTATTGAATGAGGTCCTGGTGGTGCCAAATATA
2892 103_HRV67a    AACCCAGTAGAAGATTATGTAGATCAGGTATTGAATGAGGTCCTGGTGGTGCCAAATATA
2893 104_HRV67b    AACCCAGTAGAAGATTATGTAGATCAGGTATTGAATGAGGTCCTGGTGGTGCCAAATATA
2894 GROUP_32      AACCCAGTAGAAGATTATGTAGATCAGGTATTGAATGAGGTCCTGGTGGTGCCAAATATA
2895
2896 102_HRV67     AAGCAAAGTGAACCCACGACTTCCAATTCAGCCCCAGCTCTAGATGCTGCTGAGACAGGT
2897 103_HRV67a    AAGCAAAGTGAACCCACGACTTCCAATTCAGCCCCAGCTCTAGATGCTGCTGAGACAGGT
2898 104_HRV67b    AAGCAAAGTGAACCCACGACTTCCAATTCAGCCCCAGCTCTAGATGCTGCTGAGACAGGT
2899 GROUP_32      AAGCAAAGTGAACCCACGACTTCCAATTCAGCCCCAGCTCTAGATGCTGCTGAGACAGGT
2900
2901 102_HRV67     CACACTAGCAGTGTACAACCTGAAGATATGATCGAGACTCGTTATGTACAGGCATCAAAT
2902 103_HRV67a    CACACTAGCAGTGTACAACCTGAAGATATGATCGAGACTCGTTATGTACAGGCATCAAAT
2903 104_HRV67b    CACACTAGCAGTGTACAACCTGAAGATATGATCGAGACTCGTTATGTACAGGCATCAAAT
2904 GROUP_32      CACACTAGCAGTGTACAACCTGAAGATATGATCGAGACTCGTTATGTACAGGCATCAAAT
2905
2906 102_HRV67     ACCAGAGATGAAATGAGTCTCGAGAGCTTTCTTGGAAGGTCAGGCTGTATTCATATATCA
2907 103_HRV67a    ACCAGAGATGAAATGAGTCTCGAGAGCTTTCTTGGAAGGTCAGGCTGTATTCATATATCA
2908 104_HRV67b    ACCAGAGATGAAATGAGTCTCGAGAGCTTTCTTGGAAGGTCAGGCTGTATTCATATATCA
2909 GROUP_32      ACCAGAGATGAAATGAGTCTCGAGAGCTTTCTTGGAAGGTCAGGCTGTATTCATATATCA
2910
2911 102_HRV67     AAATTGAATATTGATTATAATGCA---------------TATGATGAA---AGTAGGGAC
2912 103_HRV67a    AAATTGAATATTGATTATAATGCA---------------TATGATGAA---AGTAGGGAC
2913 104_HRV67b    AAATTGAATATTGATTATAATGCA---------------TATGATGAA---AGTAGGGAC
2914 GROUP_32      AAATTGAATATTGATTATAATGCA...............TATGATGAA...AGTAGGGAC
2915
2916 102_HRV67     AATTTCACAATTTGGAAAATAAATATAAAAGAAATGGCCCAGATTAGGAGGAAATTTGAA
2917 103_HRV67a    AATTTCACAATTTGGAAAATAAATATAAAAGAAATGGCCCAGATTAGGAGGAAATTTGAA
```

FIG. D14 CONT'D

```
10.trace                                                                    9/20/2007 5:05 PM 2918  104_HRV67b    AATTTCACAATTTGGAAAATAAATATAAAAGAAATGGCCCAGATTAGGAGGAAATTTGAA
2919  GROUP_32     AATTTCACAATTTGGAAAATAAATATAAAAGAAATGGCCCAGATTAGGAGGAAATTTGAA
2920
2921  102_HRV67    CTATTCACATATACAAGATTTGATTCTGAGATAACACTGG-TACCATGCATAGCTGCAGA
2922  103_HRV67a   CTATTCACATATACAAGATTTGATTCTGAGATAACACTGG-TACCATGCATAGCTGCAGA
2923  104_HRV67b   CTATTCACATATACAAGATTTGATTCTGAGATAACACTGG-TACCATGCATAGCTGCAGA
2924  GROUP_32     CTATTCACATATACAAGATTTGATTCTGAGATAACACTGG.TACCATGCATAGCTGCAGA
2925
2926  102_HRV67    GAGTGACAGCATTGGGCATGTTGTAATGCAATATATGTATGTACCTCCAGGAGCACCATT
2927  103_HRV67a   GAGTGACAGCATTGGGCATGTTGTAATGCAATATATGTATGTACCTCCAGGAGCACCATT
2928  104_HRV67b   GAGTGACAGCATTGGGCATGTTGTAATGCAATATATGTATGTACCTCCAGGAGCACCATT
2929  GROUP_32     GAGTGACAGCATTGGGCATGTTGTAATGCAATATATGTATGTACCTCCAGGAGCACCATT
2930
2931  102_HRV67    ACCAACAAAAGAGATGACTACACATGGCAATCAGGTACAAATGCATCCATCTTTTGGCA
2932  103_HRV67a   ACCAACAAAAGAGATGACTACACATGGCAATCAGGTACAAATGCATCCATCTTTTGGCA
2933  104_HRV67b   ACCAACAAAAGAGATGACTACACATGGCAATCAGGTACAAATGCATCCATCTTTTGGCA
2934  GROUP_32     ACCAACAAAAGAGATGACTACACATGGCAATCAGGTACAAATGCATCCATCTTTTGGCA
2935
2936  102_HRV67    ACATGGACAATCATACCCCAGATTCTCACTACCATTCTTAAGTATTGCCTCTGCTTATTA
2937  103_HRV67a   ACATGGACAATCATACCCCAGATTCTCACTACCATTCTTAAGTATTGCCTCTGCTTATTA
2938  104_HRV67b   ACATGGACAATCATACCCCAGATTCTCACTACCATTCTTAAGTATTGCCTCTGCTTATTA
2939  GROUP_32     ACATGGACAATCATACCCCAGATTCTCACTACCATTCTTAAGTATTGCCTCTGCTTATTA
2940
2941  102_HRV67    CATGTTTTATGATGGCTATGATGGTGG---ACCAGATTCACTATATGGCACCATAGTAAC
2942  103_HRV67a   CATGTTTTATGATGGCTATGATGGTGG---ACCAGATTCACTATATGGCACCATAGTAAC
2943  104_HRV67b   CATGTTTTATGATGGCTATGATGGTGG---ACCAGATTCACTATATGGCACCATAGTAAC
2944  GROUP_32     CATGTTTTATGATGGCTATGATGGTGG...ACCAGATTCACTATATGGCACCATAGTAAC
2945
2946  102_HRV67    TAATGATATGGGTTCCTTGTGTTCGCGTATAGTTACTGAAGAACATGGTTCTCGCGTAAA
2947  103_HRV67a   TAATGATATGGGTTCCTTGTGTTCGCGTATAGTTACTGAAGAACATGGTTCTCGCGTAAA
2948  104_HRV67b   TAATGATATGGGTTCCTTGTGTTCGCGTATAGTTACTGAAGAACATGGTTCTCGCGTAAA
2949  GROUP_32     TAATGATATGGGTTCCTTGTGTTCGCGTATAGTTACTGAAGAACATGGTTCTCGCGTAAA
2950
2951  102_HRV67    AATTGCAACGCGGGTGTATCATAAGGCTAAACATGTAAAAGCTTGGTGCCCAAGGCCCCC
2952  103_HRV67a   AATTGCAACGCGGGTGTATCATAAGGCTAAACATGTAAAAGCTTGGTGCCCAAGGCCCCC
2953  104_HRV67b   AATTGCAACGCGGGTGTATCATAAGGCTAAACATGTAAAAGCTTGGTGCCCAAGGCCCCC
2954  GROUP_32     AATTGCAACGCGGGTGTATCATAAGGCTAAACATGTAAAAGCTTGGTGCCCAAGGCCCCC
2955
2956  102_HRV67    TAGAGCAGTTGAATACATA-CACACACATGTTACAAACTATAGAC-CAGAAA---CAGGT
2957  103_HRV67a   TAGAGCAGTTGAATACATA-CACACACATGTTACAAACTATAGAC-CAGAAA---CAGGT
2958  104_HRV67b   TAGAGCAGTTGAATACATA-CACACACATGTTACAAACTATAGAC-CAGAAA---CAGGT
2959  GROUP_32     TAGAGCAGTTGAATACATA.CACACACATGTTACAAACTATAGAC.CAGAAA...CAGGT
2960
2961  102_HRV67    GAGG------CTCAAACGG---TTATACCTGTTAGAGCAGATGTTAGAACAATTAGAA--
2962  103_HRV67a   GAGG------CTCAAACGG---TTATACCTGTTAGAGCAGATGTTAGAACAATTAGAA--
2963  104_HRV67b   GAGG------CTCAAACGG---TTATACCTGTTAGAGCAGATGTTAGAACAATTAGAA--
2964  GROUP_32     GAGG......CTCAAACGG...TTATACCTGTTAGAGCAGATGTTAGAACAATTAGAA..
2965
2966  102_HRV67    ----ATGTA------------
2967  103_HRV67a   ----ATGTC------------
2968  104_HRV67b   ----ATGTT------------
2969  GROUP_32     ....ATGT-............
2970
2971
2972
2973  Group 33:
2974
2975  105_HRV15    AACCCAGTGGAGAATTACATAGATGAAGTGTTAAATGAGGTTCTAGTAGTTCCAAACATT
2976  106_HRV15a   AACCCAGTGGAGAATTACATAGATGAAGTGTTAAATGAGGTTCTAGTAGTTCCAAACATT
2977  107_HRV15b   AACCCAGTGGAGAATTACATAGATGAAGTGTTAAATGAGGTTCTAGTAGTTCCAAACATT
2978  GROUP_33     AACCCAGTGGAGAATTACATAGATGAAGTGTTAAATGAGGTTCTAGTAGTTCCAAACATT
2979
2980  105_HRV15    AAGGAGAGTCACTCAAGCACATCCAACTCAGCACCAGCACTAGATGCAGCTGAGACCGGC
2981  106_HRV15a   AAGGAGAGTCACTCAAGCACATCCAACTCAGCACCAGCACTAGATGCAGCTGAGACCGGC
2982  107_HRV15b   AAGGAGAGTCACTCAAGCACATCCAACTCAGCACCAGCACTAGATGCAGCTGAGACCGGC
```

FIG. D14 CONT'D

```
10.trace                                                            9/20/2007 5:05 PM 2983 GROUP_33     AAGGAGAGTCACTCAAGCACATCCAACTCAGCACCAGCACTAGATGCAGCTGAGACCGGC
2984
2985 105_HRV15    CATACTAGCAGTGTTCAACCTGAGGATATGATTGAAACTCGTTACGTCCAAACATCACAG
2986 106_HRV15a   CATACTAGCAGTGTTCAACCTGAGGATATGATTGAAACTCGTTACGTCCAAACATCACAG
2987 107_HRV15b   CATACTAGCAGTGTTCAACCTGAGGATATGATTGAAACTCGTTACGTCCAAACATCACAG
2988 GROUP_33     CATACTAGCAGTGTTCAACCTGAGGATATGATTGAAACTCGTTACGTCCAAACATCACAG
2989
2990 105_HRV15    ACCAGAGATGAAATGAGTATTGAGAGCTTCCTTGGTAGATCAGGGTGTGTCCATATTTCT
2991 106_HRV15a   ACCAGAGATGAAATGAGTATTGAGAGCTTCCTTGGTAGATCAGGGTGTGTCCATATTTCT
2992 107_HRV15b   ACCAGAGATGAAATGAGTATTGAGAGCTTCCTTGGTAGATCAGGGTGTGTCCATATTTCT
2993 GROUP_33     ACCAGAGATGAAATGAGTATTGAGAGCTTCCTTGGTAGATCAGGGTGTGTCCATATTTCT
2994
2995 105_HRV15    GATTTGAAAATACATTATGAAGAT---------------TATAATAAA---GATGGGAAA
2996 106_HRV15a   GATTTGAAAATACATTATGAAGAT---------------TATAATAAA---GATGGGAAA
2997 107_HRV15b   GATTTGAAAATACATTATGAAGAT---------------TATAATAAA---GATGGGAAA
2998 GROUP_33     GATTTGAAAATACATTATGAAGAT...............TATAATAAA...GATGGGAAA
2999
3000 105_HRV15    AACTTTACTAAATGGCAAATTAATCTCAAAGAAATGGCCCAGATTAGAAGGAAATTTGAG
3001 106_HRV15a   AACTTTACTAAATGGCAAATTAATCTCAAAGAAATGGCCCAGATTAGAAGGAAATTTGAG
3002 107_HRV15b   AACTTTACTAAATGGCAAATTAATCTCAAAGAAATGGCCCAGATTAGAAGGAAATTTGAG
3003 GROUP_33     AACTTTACTAAATGGCAAATTAATCTCAAAGAAATGGCCCAGATTAGAAGGAAATTTGAG
3004
3005 105_HRV15    TTATTCACATATGTAAGGTTTGATTCAGAAATAACACTTG-TACCATGCATTGCAGCAAA
3006 106_HRV15a   TTATTCACATATGTAAGGTTTGATTCAGAAATAACACTTG-TACCATGCATTGCAGCAAA
3007 107_HRV15b   TTATTCACATATGTAAGGTTTGATTCAGAAATAACACTTG-TACCATGCATTGCAGCAAA
3008 GROUP_33     TTATTCACATATGTAAGGTTTGATTCAGAAATAACACTTG.TACCATGCATTGCAGCAAA
3009
3010 105_HRV15    GAGTGATAACATCGGTCATGTTGTCATGCAATATATGTATGTTCCTCCGGGAGCCCCTTT
3011 106_HRV15a   GAGTGATAACATCGGTCATGTTGTCATGCAATATATGTATGTTCCTCCGGGAGCCCCTTT
3012 107_HRV15b   GAGTGATAACATCGGTCATGTTGTCATGCAATATATGTATGTTCCTCCGGGAGCCCCTTT
3013 GROUP_33     GAGTGATAACATCGGTCATGTTGTCATGCAATATATGTATGTTCCTCCGGGAGCCCCTTT
3014
3015 105_HRV15    ACCCAATAAAAGGAATGATTACACATGGCAATCAGGTACAAATGCCTCTGTTTTCTGGCA
3016 106_HRV15a   ACCCAATAAAAGGAATGATTACACATGGCAATCAGGTACAAATGCCTCTGTTTTCTGGCA
3017 107_HRV15b   ACCCAATAAAAGGAATGATTACACATGGCAATCAGGTACAAATGCCTCTGTTTTCTGGCA
3018 GROUP_33     ACCCAATAAAAGGAATGATTACACATGGCAATCAGGTACAAATGCCTCTGTTTTCTGGCA
3019
3020 105_HRV15    ACATGGTCAACCTTACCCCAGATTTTCTTTGCCTTTTCTCAGCATTGCATCTGCTTACTA
3021 106_HRV15a   ACATGGTCAACCTTACCCCAGATTTTCTTTGCCTTTTCTCAGCATTGCATCTGCTTACTA
3022 107_HRV15b   ACATGGTCAACCTTACCCCAGATTTTCTTTGCCTTTTCTCAGCATTGCATCTGCTTACTA
3023 GROUP_33     ACATGGTCAACCTTACCCCAGATTTTCTTTGCCTTTTCTCAGCATTGCATCTGCTTACTA
3024
3025 105_HRV15    CATGTTCTATGATGGATATGATGGAGATTCCACTGAATCACATTATGGTACAGTGGTCAC
3026 106_HRV15a   CATGTTCTATGATGGATATGATGGAGATTCCACTGAATCACATTATGGTACAGTGGTCAC
3027 107_HRV15b   CATGTTCTATGATGGATATGATGGAGATTCCACTGAATCACATTATGGTACAGTGGTCAC
3028 GROUP_33     CATGTTCTATGATGGATATGATGGAGATTCCACTGAATCACATTATGGTACAGTGGTCAC
3029
3030 105_HRV15    TAATGACATGGGGACACTGTGTTCTAGAATAGTAACTGAAGAGCATGGGACACGTGTAGA
3031 106_HRV15a   TAATGACATGGGGACACTGTGTTCTAGAATAGTAACTGAAGAGCATGGGACACGTGTAGA
3032 107_HRV15b   TAATGACATGGGGACACTGTGTTCTAGAATAGTAACTGAAGAGCATGGGACACGTGTAGA
3033 GROUP_33     TAATGACATGGGGACACTGTGTTCTAGAATAGTAACTGAAGAGCATGGGACACGTGTAGA
3034
3035 105_HRV15    GATTACAACTAGAGTGTATCACAAAGCTAAACATGTAAAGGCTTGGTGCCCCAGACCCCC
3036 106_HRV15a   GATTACAACTAGAGTGTATCACAAAGCTAAACATGTAAAGGCTTGGTGCCCCAGACCCCC
3037 107_HRV15b   GATTACAACTAGAGTGTATCACAAAGCTAAACATGTAAAGGCTTGGTGCCCCAGACCCCC
3038 GROUP_33     GATTACAACTAGAGTGTATCACAAAGCTAAACATGTAAAGGCTTGGTGCCCCAGACCCCC
3039
3040 105_HRV15    TAGAGCAGTGGAATATACA-CACACACATGTCACAAATTACAAAC-CACAAG---ATGGT
3041 106_HRV15a   TAGAGCAGTGGAATATACA-CACACACATGTCACAAATTACAAAC-CACAAG---ATGGT
3042 107_HRV15b   TAGAGCAGTGGAATATACA-CACACACATGTCACAAATTACAAAC-CACAAG---ATGGT
3043 GROUP_33     TAGAGCAGTGGAATATACA.CACACACATGTCACAAATTACAAAC.CACAAG...ATGGT
3044
3045 105_HRV15    GATG------TAACTACAG---TTATTCCAACTAGAGAAAATGTTAGAGCTATAGTAA--
3046 106_HRV15a   GATG------TAACTACAG---TTATTCCAACTAGAGAAAATGTTAGAGCTATAGTAA--
3047 107_HRV15b   GATG------TAACTACAG---TTATTCCAACTAGAGAAAATGTTAGAGCTATAGTAA--
```

FIG. D14 CONT'D

```
10.trace                                                                                          9/20/2007 5:05 PM 3048 GROUP_33        GATG......TAACTACAG...TTATTCCAACTAGAGAAAATGTTAGAGCTATAGTAA..
3049
3050 105_HRV15       ----ATGTT------------
3051 106_HRV15a      ----ATGTA------------
3052 107_HRV15b      ----ATGTC------------
3053 GROUP_33        ....ATGT-............
3054
3055
3056
3057 Group  34:
3058
3059 108_HRV74a      AACCCAGTGGAGAATTACATAGATGAAGTGTTGAATGAAGTGTTAGTTGTTCCAAATATT
3060 109_HRV74b      AACCCAGTGGAGAATTACATAGATGAAGTGTTGAATGAAGTGTTAGTTGTTCCAAATATT
3061 110_HRV74       AACCCAGTGGAGAATTACATAGATGAAGTGTTGAATGAAGTGTTAGTTGTTCCAAATATT
3062 GROUP_34        AACCCAGTGGAGAATTACATAGATGAAGTGTTGAATGAAGTGTTAGTTGTTCCAAATATT
3063
3064 108_HRV74a      AGAGAAAGCCATTCAAGTACTTCAAACTCAGCACCAGCACTGGATGCAGCTGAAACTGGC
3065 109_HRV74b      AGAGAAAGCCATTCAAGTACTTCAAACTCAGCACCAGCACTGGATGCAGCTGAAACTGGC
3066 110_HRV74       AGAGAAAGCCATTCAAGTACTTCAAACTCAGCACCAGCACTGGATGCAGCTGAAACTGGC
3067 GROUP_34        AGAGAAAGCCATTCAAGTACTTCAAACTCAGCACCAGCACTGGATGCAGCTGAAACTGGC
3068
3069 108_HRV74a      CATACCAGTAATGTGCAACCAGAAGATATGGTTGAGACACGCTATGTGCAAACCTCACAG
3070 109_HRV74b      CATACCAGTAATGTGCAACCAGAAGATATGGTTGAGACACGCTATGTGCAAACCTCACAG
3071 110_HRV74       CATACCAGTAATGTGCAACCAGAAGATATGGTTGAGACACGCTATGTGCAAACCTCACAG
3072 GROUP_34        CATACCAGTAATGTGCAACCAGAAGATATGGTTGAGACACGCTATGTGCAAACCTCACAG
3073
3074 108_HRV74a      ACAAGAGATGAGATGAGTGTAGAAAGTTTTCTTGGAAGATCAGGATGCATCCATATCTCA
3075 109_HRV74b      ACAAGAGATGAGATGAGTGTAGAAAGTTTTCTTGGAAGATCAGGATGCATCCATATCTCA
3076 110_HRV74       ACAAGAGATGAGATGAGTGTAGAAAGTTTTCTTGGAAGATCAGGATGCATCCATATCTCA
3077 GROUP_34        ACAAGAGATGAGATGAGTGTAGAAAGTTTTCTTGGAAGATCAGGATGCATCCATATCTCA
3078
3079 108_HRV74a      CATCTAAAAATTGATTATACAAAC---------------TATAATGTT---AAAGGGAAG
3080 109_HRV74b      CATCTAAAAATTGATTATACAAAC---------------TATAATGTT---AAAGGGAAG
3081 110_HRV74       CATCTAAAAATTGATTATACAAAC---------------TATAATGTT---AAAGGGAAG
3082 GROUP_34        CATCTAAAAATTGATTATACAAAC...............TATAATGTT...AAAGGGAAG
3083
3084 108_HRV74a      AATTTTACTAAATGGCAAATAAATCTTAAAGAAATGGCACAGATTAGGAGAAAATTTGAG
3085 109_HRV74b      AATTTTACTAAATGGCAAATAAATCTTAAAGAAATGGCACAGATTAGGAGAAAATTTGAG
3086 110_HRV74       AATTTTACTAAATGGCAAATAAATCTTAAAGAAATGGCACAGATTAGGAGAAAATTTGAG
3087 GROUP_34        AATTTTACTAAATGGCAAATAAATCTTAAAGAAATGGCACAGATTAGGAGAAAATTTGAG
3088
3089 108_HRV74a      TTGTTCACATATGTTAGATTTGACTCAGAAGTGACATTAG-TTCCATGCATTGCTGCTAA
3090 109_HRV74b      TTGTTCACATATGTTAGATTTGACTCAGAAGTGACATTAG-TTCCATGCATTGCTGCTAA
3091 110_HRV74       TTGTTCACATATGTTAGATTTGACTCAGAAGTGACATTAG-TTCCATGCATTGCTGCTAA
3092 GROUP_34        TTGTTCACATATGTTAGATTTGACTCAGAAGTGACATTAG.TTCCATGCATTGCTGCTAA
3093
3094 108_HRV74a      AAGTGACAACATTGGCCATGTTGTTATGCAATACATGTATGTCCCCCCAGGAGCACCTTT
3095 109_HRV74b      AAGTGACAACATTGGCCATGTTGTTATGCAATACATGTATGTCCCCCCAGGAGCACCTTT
3096 110_HRV74       AAGTGACAACATTGGCCATGTTGTTATGCAATACATGTATGTCCCCCCAGGAGCACCTTT
3097 GROUP_34        AAGTGACAACATTGGCCATGTTGTTATGCAATACATGTATGTCCCCCCAGGAGCACCTTT
3098
3099 108_HRV74a      ACCCAAGAAAAGAGATGATTACACATGGCAATCTGGCACAAATGCATCTGTGTTTTGGCA
3100 109_HRV74b      ACCCAAGAAAAGAGATGATTACACATGGCAATCTGGCACAAATGCATCTGTGTTTTGGCA
3101 110_HRV74       ACCCAAGAAAAGAGATGATTACACATGGCAATCTGGCACAAATGCATCTGTGTTTTGGCA
3102 GROUP_34        ACCCAAGAAAAGAGATGATTACACATGGCAATCTGGCACAAATGCATCTGTGTTTTGGCA
3103
3104 108_HRV74a      GCATGGACAGCCATACCCTAGATTCTCATTACCTTTCCTTAGCATAGCATCTGCTTATTA
3105 109_HRV74b      GCATGGACAGCCATACCCTAGATTCTCATTACCTTTCCTTAGCATAGCATCTGCTTATTA
3106 110_HRV74       GCATGGACAGCCATACCCTAGATTCTCATTACCTTTCCTTAGCATAGCATCTGCTTATTA
3107 GROUP_34        GCATGGACAGCCATACCCTAGATTCTCATTACCTTTCCTTAGCATAGCATCTGCTTATTA
3108
3109 108_HRV74a      CATGTTTTATGATGGATATGATGGAGACTCTACTGAATCACATTATGGTACAGTAGTAAC
3110 109_HRV74b      CATGTTTTATGATGGATATGATGGAGACTCTACTGAATCACATTATGGTACAGTAGTAAC
3111 110_HRV74       CATGTTTTATGATGGATATGATGGAGACTCTACTGAATCACATTATGGTACAGTAGTAAC
3112 GROUP_34        CATGTTTTATGATGGATATGATGGAGACTCTACTGAATCACATTATGGTACAGTAGTAAC
```

FIG. D14 CONT'D 10.trace                                                                  9/20/2007 5:05 PM

```
3113
3114 108_HRV74a    AAATGACATGGGAACTCTATGTTCTAGAATTGTGACTGAAGAACACGATGCACGTGTGGA
3115 109_HRV74b    AAATGACATGGGAACTCTATGTTCTAGAATTGTGACTGAAGAACACGATGCACGTGTGGA
3116 110_HRV74     AAATGACATGGGAACTCTATGTTCTAGAATTGTGACTGAAGAACACGATGCACGTGTGGA
3117 GROUP_34      AAATGACATGGGAACTCTATGTTCTAGAATTGTGACTGAAGAACACGATGCACGTGTGGA
3118
3119 108_HRV74a    AATTACAACTAGAGTGTACCATAAAGCAAAGCATGTGAAGGCATGGTGTCCTAGACCCCC
3120 109_HRV74b    AATTACAACTAGAGTGTACCATAAAGCAAAGCATGTGAAGGCATGGTGTCCTAGACCCCC
3121 110_HRV74     AATTACAACTAGAGTGTACCATAAAGCAAAGCATGTGAAGGCATGGTGTCCTAGACCCCC
3122 GROUP_34      AATTACAACTAGAGTGTACCATAAAGCAAAGCATGTGAAGGCATGGTGTCCTAGACCCCC
3123
3124 108_HRV74a    TAGAGCAGTTGAATATACT-CACACACATGTCACAAATTACAAAC-CACAAG---AAGGT
3125 109_HRV74b    TAGAGCAGTTGAATATACT-CACACACATGTCACAAATTACAAAC-CACAAG---AAGGT
3126 110_HRV74     TAGAGCAGTTGAATATACT-CACACACATGTCACAAATTACAAAC-CACAAG---AAGGT
3127 GROUP_34      TAGAGCAGTTGAATATACT.CACACACATGTCACAAATTACAAAC.CACAAG...AAGGT
3128
3129 108_HRV74a    GACG------TAACTACAG---TCATCCCAACTAGG---------AGATCAATAGTGA--
3130 109_HRV74b    GACG------TAACTACAG---TCATCCCAACTAGG---------AGATCAATAGTGA--
3131 110_HRV74     GACG------TAACTACAG---TCATCCCAACTAGG---------AGATCAATAGTGA--
3132 GROUP_34      GACG......TAACTACAG...TCATCCCAACTAGG.........AGATCAATAGTGA..
3133
3134 108_HRV74a    ----ATGTA------------
3135 109_HRV74b    ----ATGTC------------
3136 110_HRV74     ----ATGTT------------
3137 GROUP_34      ....ATGT-............
3138
3139
3140 Group  35:
3141
3142
3143 111_HRV38a    AACCCAGTAGAGGAATACATAGATGGAGTCTTGAATGAGGTTCTTGTGGTTCCGAACATT
3144 112_HRV38b    AACCCAGTAGAGGAATACATAGATGGAGTCTTGAATGAGGTTCTTGTGGTTCCGAACATT
3145 113_HRV38     AACCCAGTAGAGGAATACATAGATGGAGTCTTGAATGAGGTTCTTGTGGTTCCGAACATT
3146 GROUP_35      AACCCAGTAGAGGAATACATAGATGGAGTCTTGAATGAGGTTCTTGTGGTTCCGAACATT
3147
3148 111_HRV38a    AAGGAAAGCCACTCCAGCACATCAAATTCAGCACCAGCATTAGATGCTGCTGAGACTGGA
3149 112_HRV38b    AAGGAAAGCCACTCCAGCACATCAAATTCAGCACCAGCATTAGATGCTGCTGAGACTGGA
3150 113_HRV38     AAGGAAAGCCACTCCAGCACATCAAATTCAGCACCAGCATTAGATGCTGCTGAGACTGGA
3151 GROUP_35      AAGGAAAGCCACTCCAGCACATCAAATTCAGCACCAGCATTAGATGCTGCTGAGACTGGA
3152
3153 111_HRV38a    CACACCAGTAATGTGCAGCCTGAGGATATGATTGAAACTCGCTATGTACAGACATCACAA
3154 112_HRV38b    CACACCAGTAATGTGCAGCCTGAGGATATGATTGAAACTCGCTATGTACAGACATCACAA
3155 113_HRV38     CACACCAGTAATGTGCAGCCTGAGGATATGATTGAAACTCGCTATGTACAGACATCACAA
3156 GROUP_35      CACACCAGTAATGTGCAGCCTGAGGATATGATTGAAACTCGCTATGTACAGACATCACAA
3157
3158 111_HRV38a    ACTAGAGATGAAATGAGTGTAGAAAGTTTTCTAGGAAGATCAGGTTGTGTACATATATCC
3159 112_HRV38b    ACTAGAGATGAAATGAGTGTAGAAAGTTTTCTAGGAAGATCAGGTTGTGTACATATATCC
3160 113_HRV38     ACTAGAGATGAAATGAGTGTAGAAAGTTTTCTAGGAAGATCAGGTTGTGTACATATATCC
3161 GROUP_35      ACTAGAGATGAAATGAGTGTAGAAAGTTTTCTAGGAAGATCAGGTTGTGTACATATATCC
3162
3163 111_HRV38a    AATCTTGACATAGATTACATTAAT---------------TACAACTCT---GAAGACAAA
3164 112_HRV38b    AATCTTGACATAGATTACATTAAT---------------TACAACTCT---GAAGACAAA
3165 113_HRV38     AATCTTGACATAGATTACATTAAT---------------TACAACTCT---GAAGACAAA
3166 GROUP_35      AATCTTGACATAGATTACATTAAT...............TACAACTCT...GAAGACAAA
3167
3168 111_HRV38a    AACTTTACAACATGGCAAATCAATCTCAAAGAAATGGCTCAAATCAGAAGAAAGTTTGAA
3169 112_HRV38b    AACTTTACAACATGGCAAATCAATCTCAAAGAAATGGCTCAAATCAGAAGAAAGTTTGAA
3170 113_HRV38     AACTTTACAACATGGCAAATCAATCTCAAAGAAATGGCTCAAATCAGAAGAAAGTTTGAA
3171 GROUP_35      AACTTTACAACATGGCAAATCAATCTCAAAGAAATGGCTCAAATCAGAAGAAAGTTTGAA
3172
3173 111_HRV38a    ATGTTTACATATGTGAGATTTGATTCAGAAGTTACATTAG-TCCCATGTATAGCAGCACA
3174 112_HRV38b    ATGTTTACATATGTGAGATTTGATTCAGAAGTTACATTAG-TCCCATGTATAGCAGCACA
3175 113_HRV38     ATGTTTACATATGTGAGATTTGATTCAGAAGTTACATTAG-TCCCATGTATAGCAGCACA
3176 GROUP_35      ATGTTTACATATGTGAGATTTGATTCAGAAGTTACATTAG.TCCCATGTATAGCAGCACA
3177
```

FIG. D14 CONT'D

```
10.trace                                                                    9/20/2007 5:05 PM 3178  111_HRV38a   AAATGAAGGTGTGGGGCATGTTGTTATGCAGTATATGTATGTCCCTCCAGGGGCACCATT
3179  112_HRV38b   AAATGAAGGTGTGGGGCATGTTGTTATGCAGTATATGTATGTCCCTCCAGGGGCACCATT
3180  113_HRV38    AAATGAAGGTGTGGGGCATGTTGTTATGCAGTATATGTATGTCCCTCCAGGGGCACCATT
3181  GROUP_35     AAATGAAGGTGTGGGGCATGTTGTTATGCAGTATATGTATGTCCCTCCAGGGGCACCATT
3182
3183  111_HRV38a   ACCCAGGAAGAGAGATGATTACACTTGGCAATCTGGTACAAATGCCTCTGTTTTCTGGCA
3184  112_HRV38b   ACCCAGGAAGAGAGATGATTACACTTGGCAATCTGGTACAAATGCCTCTGTTTTCTGGCA
3185  113_HRV38    ACCCAGGAAGAGAGATGATTACACTTGGCAATCTGGTACAAATGCCTCTGTTTTCTGGCA
3186  GROUP_35     ACCCAGGAAGAGAGATGATTACACTTGGCAATCTGGTACAAATGCCTCTGTTTTCTGGCA
3187
3188  111_HRV38a   ATATGGTCAGACATATCCTCGATTTTCCTTACCTTTCTTAAGCATTGCATCTGTCTATTA
3189  112_HRV38b   ATATGGTCAGACATATCCTCGATTTTCCTTACCTTTCTTAAGCATTGCATCTGTCTATTA
3190  113_HRV38    ATATGGTCAGACATATCCTCGATTTTCCTTACCTTTCTTAAGCATTGCATCTGTCTATTA
3191  GROUP_35     ATATGGTCAGACATATCCTCGATTTTCCTTACCTTTCTTAAGCATTGCATCTGTCTATTA
3192
3193  111_HRV38a   TATGTTTTATGATGGATATGATGGGGACTCAACAGAATCACATTATGGGACAGCGGTGAC
3194  112_HRV38b   TATGTTTTATGATGGATATGATGGGGACTCAACAGAATCACATTATGGGACAGCGGTGAC
3195  113_HRV38    TATGTTTTATGATGGATATGATGGGGACTCAACAGAATCACATTATGGGACAGCGGTGAC
3196  GROUP_35     TATGTTTTATGATGGATATGATGGGGACTCAACAGAATCACATTATGGGACAGCGGTGAC
3197
3198  111_HRV38a   CAATGATATGGGGACACTTTGTTCAAGAATAGTCACTGAAAATCATGGGACCCAAGTGAA
3199  112_HRV38b   CAATGATATGGGGACACTTTGTTCAAGAATAGTCACTGAAAATCATGGGACCCAAGTGAA
3200  113_HRV38    CAATGATATGGGGACACTTTGTTCAAGAATAGTCACTGAAAATCATGGGACCCAAGTGAA
3201  GROUP_35     CAATGATATGGGGACACTTTGTTCAAGAATAGTCACTGAAAATCATGGGACCCAAGTGAA
3202
3203  111_HRV38a   GATAACAACTAGAATTTATCATAAGGCAAAACATGTAAAAGCCTGGTGTCCAAGACCCCC
3204  112_HRV38b   GATAACAACTAGAATTTATCATAAGGCAAAACATGTAAAAGCCTGGTGTCCAAGACCCCC
3205  113_HRV38    GATAACAACTAGAATTTATCATAAGGCAAAACATGTAAAAGCCTGGTGTCCAAGACCCCC
3206  GROUP_35     GATAACAACTAGAATTTATCATAAGGCAAAACATGTAAAAGCCTGGTGTCCAAGACCCCC
3207
3208  111_HRV38a   AAGGGCAGTTGAATATAGA-CATACACATGTTAACAATTACAAAC-CAGACC---AAGGG
3209  112_HRV38b   AAGGGCAGTTGAATATAGA-CATACACATGTTAACAATTACAAAC-CAGACC---AAGGG
3210  113_HRV38    AAGGGCAGTTGAATATAGA-CATACACATGTTAACAATTACAAAC-CAGACC---AAGGG
3211  GROUP_35     AAGGGCAGTTGAATATAGA.CATACACATGTTAACAATTACAAAC.CAGACC...AAGGG
3212
3213  111_HRV38a   GAAG------TAACCACTA---TGATTCCAACTAGAACCAACATAAGAACCATCGTAA--
3214  112_HRV38b   GAAG------TAACCACTA---TGATTCCAACTAGAACCAACATAAGAACCATCGTAA--
3215  113_HRV38    GAAG------TAACCACTA---TGATTCCAACTAGAACCAACATAAGAACCATCGTAA--
3216  GROUP_35     GAAG......TAACCACTA...TGATTCCAACTAGAACCAACATAAGAACCATCGTAA..
3217
3218  111_HRV38a   ----ATGTA------------
3219  112_HRV38b   ----ATGTC------------
3220  113_HRV38    ----ATGTT------------
3221  GROUP_35     ....ATGT-............
3222
3223
3224
3225  Group 36:
3226
3227  114_HRV60    AATCCAGTAGAAAGCTACATAGATGGGGTCTTAAACGAAGTCCTTGTGGTTCCAAACATT
3228  115_HRV60a   AATCCAGTAGAAAGCTACATAGATGGGGTCTTAAACGAAGTCCTTGTGGTTCCAAACATT
3229  116_HRV60b   AATCCAGTAGAAAGCTACATAGATGGGGTCTTAAACGAAGTCCTTGTGGTTCCAAACATT
3230  GROUP_36     AATCCAGTAGAAAGCTACATAGATGGGGTCTTAAACGAAGTCCTTGTGGTTCCAAACATT
3231
3232  114_HRV60    AGGGAGAGCCAACCCACTACTTCTAATTCTGCTCCAGCATTGGATGCTGCTGAGACTGGT
3233  115_HRV60a   AGGGAGAGCCAACCCACTACTTCTAATTCTGCTCCAGCATTGGATGCTGCTGAGACTGGT
3234  116_HRV60b   AGGGAGAGCCAACCCACTACTTCTAATTCTGCTCCAGCATTGGATGCTGCTGAGACTGGT
3235  GROUP_36     AGGGAGAGCCAACCCACTACTTCTAATTCTGCTCCAGCATTGGATGCTGCTGAGACTGGT
3236
3237  114_HRV60    CACACTAGTAATGTACAGCCTGAGGACGTGATTGAAACACGTTATGTGCAGATTACACAA
3238  115_HRV60a   CACACTAGTAATGTACAGCCTGAGGACGTGATTGAAACACGTTATGTGCAGATTACACAA
3239  116_HRV60b   CACACTAGTAATGTACAGCCTGAGGACGTGATTGAAACACGTTATGTGCAGATTACACAA
3240  GROUP_36     CACACTAGTAATGTACAGCCTGAGGACGTGATTGAAACACGTTATGTGCAGATTACACAA
3241
3242  114_HRV60    ACTAGAGATGAGATGAGTGTTGAGAGCTTCCTCGGCAGATCTGGATGTATTCATATTTCC
```

FIG. D14 CONT'D

```
10.trace                                                          9/20/2007 5:05 PM 3243  115_HRV60a   ACTAGAGATGAGATGAGTGTTGAGAGCTTCCTCGGCAGATCTGGATGTATTCATATTTCC
3244  116_HRV60b   ACTAGAGATGAGATGAGTGTTGAGAGCTTCCTCGGCAGATCTGGATGTATTCATATTTCC
3245  GROUP_36    ACTAGAGATGAGATGAGTGTTGAGAGCTTCCTCGGCAGATCTGGATGTATTCATATTTCC
3246
3247  114_HRV60    AAATTAGAAATTGACTATAGTAAC---------------TACAATGAG---GAGAATAAA
3248  115_HRV60a   AAATTAGAAATTGACTATAGTAAC---------------TACAATGAG---GAGAATAAA
3249  116_HRV60b   AAATTAGAAATTGACTATAGTAAC---------------TACAATGAG---GAGAATAAA
3250  GROUP_36    AAATTAGAAATTGACTATAGTAAC...............TACAATGAG...GAGAATAAA
3251
3252  114_HRV60    AATTTCACAACTTGGCAAATTAACCTAAAGGAAATGGCACAAATAAGAAGAAAGTTTGAA
3253  115_HRV60a   AATTTCACAACTTGGCAAATTAACCTAAAGGAAATGGCACAAATAAGAAGAAAGTTTGAA
3254  116_HRV60b   AATTTCACAACTTGGCAAATTAACCTAAAGGAAATGGCACAAATAAGAAGAAAGTTTGAA
3255  GROUP_36    AATTTCACAACTTGGCAAATTAACCTAAAGGAAATGGCACAAATAAGAAGAAAGTTTGAA
3256
3257  114_HRV60    TTATTTACATATGTAAGATTTGATTCAGAATTGACTCTGG-TCCCATGCATAGCAGCAAA
3258  115_HRV60a   TTATTTACATATGTAAGATTTGATTCAGAATTGACTCTGG-TCCCATGCATAGCAGCAAA
3259  116_HRV60b   TTATTTACATATGTAAGATTTGATTCAGAATTGACTCTGG-TCCCATGCATAGCAGCAAA
3260  GROUP_36    TTATTTACATATGTAAGATTTGATTCAGAATTGACTCTGG.TCCCATGCATAGCAGCAAA
3261
3262  114_HRV60    AAATGATGGCATAGGTCATGTTGTCATGCAATACATGTATGTCCCCCCAGGAGCACCATT
3263  115_HRV60a   AAATGATGGCATAGGTCATGTTGTCATGCAATACATGTATGTCCCCCCAGGAGCACCATT
3264  116_HRV60b   AAATGATGGCATAGGTCATGTTGTCATGCAATACATGTATGTCCCCCCAGGAGCACCATT
3265  GROUP_36    AAATGATGGCATAGGTCATGTTGTCATGCAATACATGTATGTCCCCCCAGGAGCACCATT
3266
3267  114_HRV60    ACCTACTAAAAGAGACGATTACACATGGCAATCTGGCACAAATGCTTCTGTATTTTGGCA
3268  115_HRV60a   ACCTACTAAAAGAGACGATTACACATGGCAATCTGGCACAAATGCTTCTGTATTTTGGCA
3269  116_HRV60b   ACCTACTAAAAGAGACGATTACACATGGCAATCTGGCACAAATGCTTCTGTATTTTGGCA
3270  GROUP_36    ACCTACTAAAAGAGACGATTACACATGGCAATCTGGCACAAATGCTTCTGTATTTTGGCA
3271
3272  114_HRV60    GCATGGACAAACATACCCTAGATTTTCACTTCCATTTCTAAGTATTGCATCTGCCTACTA
3273  115_HRV60a   GCATGGACAAACATACCCTAGATTTTCACTTCCATTTCTAAGTATTGCATCTGCCTACTA
3274  116_HRV60b   GCATGGACAAACATACCCTAGATTTTCACTTCCATTTCTAAGTATTGCATCTGCCTACTA
3275  GROUP_36    GCATGGACAAACATACCCTAGATTTTCACTTCCATTTCTAAGTATTGCATCTGCCTACTA
3276
3277  114_HRV60    CATGTTTTATGATGGTTATGATGGTCACTCAACTGAATCACATTATGGGACGGTTGTGAC
3278  115_HRV60a   CATGTTTTATGATGGTTATGATGGTCACTCAACTGAATCACATTATGGGACGGTTGTGAC
3279  116_HRV60b   CATGTTTTATGATGGTTATGATGGTCACTCAACTGAATCACATTATGGGACGGTTGTGAC
3280  GROUP_36    CATGTTTTATGATGGTTATGATGGTCACTCAACTGAATCACATTATGGGACGGTTGTGAC
3281
3282  114_HRV60    CAATGACATGGGAACGTTGTGCTCCAGAATAGTTACTGAACACCATGGTACACAGGTTCA
3283  115_HRV60a   CAATGACATGGGAACGTTGTGCTCCAGAATAGTTACTGAACACCATGGTACACAGGTTCA
3284  116_HRV60b   CAATGACATGGGAACGTTGTGCTCCAGAATAGTTACTGAACACCATGGTACACAGGTTCA
3285  GROUP_36    CAATGACATGGGAACGTTGTGCTCCAGAATAGTTACTGAACACCATGGTACACAGGTTCA
3286
3287  114_HRV60    CGTCGCAACAAGAATATATCATAAAGCAAAGCATGTTAAGGCTTGGTGTCCAAGACCTCC
3288  115_HRV60a   CGTCGCAACAAGAATATATCATAAAGCAAAGCATGTTAAGGCTTGGTGTCCAAGACCTCC
3289  116_HRV60b   CGTCGCAACAAGAATATATCATAAAGCAAAGCATGTTAAGGCTTGGTGTCCAAGACCTCC
3290  GROUP_36    CGTCGCAACAAGAATATATCATAAAGCAAAGCATGTTAAGGCTTGGTGTCCAAGACCTCC
3291
3292  114_HRV60    AAGGGCAGTTGAATATAGA-CACACACATGTAAACAACTATAGAC-CAGATG---ATGGA
3293  115_HRV60a   AAGGGCAGTTGAATATAGA-CACACACATGTAAACAACTATAGAC-CAGATG---ATGGA
3294  116_HRV60b   AAGGGCAGTTGAATATAGA-CACACACATGTAAACAACTATAGAC-CAGATG---ATGGA
3295  GROUP_36    AAGGGCAGTTGAATATAGA.CACACACATGTAAACAACTATAGAC.CAGATG...ATGGA
3296
3297  114_HRV60    GAAG------CAGCCATAA---CAATCCCCATTAGAACTGATATACGAGCAATCAGAA--
3298  115_HRV60a   GAAG------CAGCCATAA---CAATCCCCATTAGAACTGATATACGAGCAATCAGAA--
3299  116_HRV60b   GAAG------CAGCCATAA---CAATCCCCATTAGAACTGATATACGAGCAATCAGAA--
3300  GROUP_36    GAAG......CAGCCATAA...CAATCCCCATTAGAACTGATATACGAGCAATCAGAA..
3301
3302  114_HRV60    ----CAGTT------------
3303  115_HRV60a   ----CAGTA------------
3304  116_HRV60b   ----CAGTG------------
3305  GROUP_36    ....CAGT-............
3306
3307
```

FIG. D14 CONT'D 10.trace                                                                9/20/2007 5:05 PM

```
3308
3309 Group  37:
3310
3311 117_HRV64a    AACCCAGTTGAACAATACATTGATGGTGTGTTGAATGAAGTTTTGATTGTCCCAAACATC
3312 118_HRV64b    AACCCAGTTGAACAATACATTGATGGTGTGTTGAATGAAGTTTTGATTGTCCCAAACATC
3313 119_HRV64     AACCCAGTTGAACAATACATTGATGGTGTGTTGAATGAAGTTTTGATTGTCCCAAACATC
3314 GROUP_37      AACCCAGTTGAACAATACATTGATGGTGTGTTGAATGAAGTTTTGATTGTCCCAAACATC
3315
3316 117_HRV64a    AATGAGAGCCATCCCAGCACTTCCAATGCAGCGCCAGCTTTAGATGCAGCTGAGACCGGA
3317 118_HRV64b    AATGAGAGCCATCCCAGCACTTCCAATGCAGCGCCAGCTTTAGATGCAGCTGAGACCGGA
3318 119_HRV64     AATGAGAGCCATCCCAGCACTTCCAATGCAGCGCCAGCTTTAGATGCAGCTGAGACCGGA
3319 GROUP_37      AATGAGAGCCATCCCAGCACTTCCAATGCAGCGCCAGCTTTAGATGCAGCTGAGACCGGA
3320
3321 117_HRV64a    CACACCAGTAATGTACAGCCTGAAGATATGATTGAAACGCGCTATGTACAAAACACTCAA
3322 118_HRV64b    CACACCAGTAATGTACAGCCTGAAGATATGATTGAAACGCGCTATGTACAAAACACTCAA
3323 119_HRV64     CACACCAGTAATGTACAGCCTGAAGATATGATTGAAACGCGCTATGTACAAAACACTCAA
3324 GROUP_37      CACACCAGTAATGTACAGCCTGAAGATATGATTGAAACGCGCTATGTACAAAACACTCAA
3325
3326 117_HRV64a    ACTAGAGATGAAATGAGCATTGAGAGTTTCTTGGGCAGGTCTGGTTGTATACACATATCA
3327 118_HRV64b    ACTAGAGATGAAATGAGCATTGAGAGTTTCTTGGGCAGGTCTGGTTGTATACACATATCA
3328 119_HRV64     ACTAGAGATGAAATGAGCATTGAGAGTTTCTTGGGCAGGTCTGGTTGTATACACATATCA
3329 GROUP_37      ACTAGAGATGAAATGAGCATTGAGAGTTTCTTGGGCAGGTCTGGTTGTATACACATATCA
3330
3331 117_HRV64a    GATTTAAAAGTAAATTATACTGGG---------------TATAATGAT---GAAGGTAAC
3332 118_HRV64b    GATTTAAAAGTAAATTATACTGGG---------------TATAATGAT---GAAGGTAAC
3333 119_HRV64     GATTTAAAAGTAAATTATACTGGG---------------TATAATGAT---GAAGGTAAC
3334 GROUP_37      GATTTAAAAGTAAATTATACTGGG...............TATAATGAT...GAAGGTAAC
3335
3336 117_HRV64a    AATTTTAACAAATGGCAGATCACCTTGAAAGAAATGGCTCAGATAAGAAGGAAGTATGAA
3337 118_HRV64b    AATTTTAACAAATGGCAGATCACCTTGAAAGAAATGGCTCAGATAAGAAGGAAGTATGAA
3338 119_HRV64     AATTTTAACAAATGGCAGATCACCTTGAAAGAAATGGCTCAGATAAGAAGGAAGTATGAA
3339 GROUP_37      AATTTTAACAAATGGCAGATCACCTTGAAAGAAATGGCTCAGATAAGAAGGAAGTATGAA
3340
3341 117_HRV64a    TTATTTACATATGTTAGATTTGATTCTGAAATAACCTTAG-TGCCTTGCATATCTTCTCA
3342 118_HRV64b    TTATTTACATATGTTAGATTTGATTCTGAAATAACCTTAG-TGCCTTGCATATCTTCTCA
3343 119_HRV64     TTATTTACATATGTTAGATTTGATTCTGAAATAACCTTAG-TGCCTTGCATATCTTCTCA
3344 GROUP_37      TTATTTACATATGTTAGATTTGATTCTGAAATAACCTTAG.TGCCTTGCATATCTTCTCA
3345
3346 117_HRV64a    GAGTGCTAACATTGGTCATGTTGTTATGCAATATATGTATGTCCCTCCTGGAGCTCCAAT
3347 118_HRV64b    GAGTGCTAACATTGGTCATGTTGTTATGCAATATATGTATGTCCCTCCTGGAGCTCCAAT
3348 119_HRV64     GAGTGCTAACATTGGTCATGTTGTTATGCAATATATGTATGTCCCTCCTGGAGCTCCAAT
3349 GROUP_37      GAGTGCTAACATTGGTCATGTTGTTATGCAATATATGTATGTCCCTCCTGGAGCTCCAAT
3350
3351 117_HRV64a    ACCAACCAAAAGAAATGATTACGTCTGGCAGTCAGGCACCAATGCATCCATCTTTTGGCA
3352 118_HRV64b    ACCAACCAAAAGAAATGATTACGTCTGGCAGTCAGGCACCAATGCATCCATCTTTTGGCA
3353 119_HRV64     ACCAACCAAAAGAAATGATTACGTCTGGCAGTCAGGCACCAATGCATCCATCTTTTGGCA
3354 GROUP_37      ACCAACCAAAAGAAATGATTACGTCTGGCAGTCAGGCACCAATGCATCCATCTTTTGGCA
3355
3356 117_HRV64a    ACACGGTCAACCATACCCTCGATTTTCTCTCCCTTTCCTTAGCATAGCCTCAGCATATTA
3357 118_HRV64b    ACACGGTCAACCATACCCTCGATTTTCTCTCCCTTTCCTTAGCATAGCCTCAGCATATTA
3358 119_HRV64     ACACGGTCAACCATACCCTCGATTTTCTCTCCCTTTCCTTAGCATAGCCTCAGCATATTA
3359 GROUP_37      ACACGGTCAACCATACCCTCGATTTTCTCTCCCTTTCCTTAGCATAGCCTCAGCATATTA
3360
3361 117_HRV64a    CATGTTTATGATGGTTATGACGGTGG---ACCTGGTTCCCGTTATGGCGCAGTGGTGAC
3362 118_HRV64b    CATGTTTATGATGGTTATGACGGTGG---ACCTGGTTCCCGTTATGGCGCAGTGGTGAC
3363 119_HRV64     CATGTTTATGATGGTTATGACGGTGG---ACCTGGTTCCCGTTATGGCGCAGTGGTGAC
3364 GROUP_37      CATGTTTATGATGGTTATGACGGTGG...ACCTGGTTCCCGTTATGGCGCAGTGGTGAC
3365
3366 117_HRV64a    AAATGATATGGGCACTTTGTGTTCTAGAATTGTGACTGAGGAACACACAACACAGGTCAA
3367 118_HRV64b    AAATGATATGGGCACTTTGTGTTCTAGAATTGTGACTGAGGAACACACAACACAGGTCAA
3368 119_HRV64     AAATGATATGGGCACTTTGTGTTCTAGAATTGTGACTGAGGAACACACAACACAGGTCAA
3369 GROUP_37      AAATGATATGGGCACTTTGTGTTCTAGAATTGTGACTGAGGAACACACAACACAGGTCAA
3370
3371 117_HRV64a    CATCACTACTAGGGTTTATCACAAAGCAAAACATGTCAAGGCATGGTGTCCACGGCCCCC
3372 118_HRV64b    CATCACTACTAGGGTTTATCACAAAGCAAAACATGTCAAGGCATGGTGTCCACGGCCCCC
```

FIG. D14 CONT'D

```
10.trace                                                          9/20/2007 5:05 PM 3373  119_HRV64    CATCACTACTAGGGTTTATCACAAAGCAAAACATGTCAAGGCATGGTGTCCACGGCCCCC
3374  GROUP_37     CATCACTACTAGGGTTTATCACAAAGCAAAACATGTCAAGGCATGGTGTCCACGGCCCCC
3375
3376  117_HRV64a   AAGAGCTGTTGGATATACA-CATACAAATGTCACCAATTATAAAC-CATCCA---AAGGA
3377  118_HRV64b   AAGAGCTGTTGGATATACA-CATACAAATGTCACCAATTATAAAC-CATCCA---AAGGA
3378  119_HRV64    AAGAGCTGTTGGATATACA-CATACAAATGTCACCAATTATAAAC-CATCCA---AAGGA
3379  GROUP_37     AAGAGCTGTTGGATATACA.CATACAAATGTCACCAATTATAAAC.CATCCA...AAGGA
3380
3381  117_HRV64a   GAAT------ACACACCAC---CCGTTCCGTCACGTAACAGCCCCAGAGATATTGTCA--
3382  118_HRV64b   GAAT------ACACACCAC---CCGTTCCGTCACGTAACAGCCCCAGAGATATTGTCA--
3383  119_HRV64    GAAT------ACACACCAC---CCGTTCCGTCACGTAACAGCCCCAGAGATATTGTCA--
3384  GROUP_37     GAAT......ACACACCAC...CCGTTCCGTCACGTAACAGCCCCAGAGATATTGTCA..
3385
3386  117_HRV64a   ----CAGTG-----------
3387  118_HRV64b   ----CAGTG-----------
3388  119_HRV64    ----CAGTA-----------
3389  GROUP_37     ....CAGT-...........
3390
3391
3392
3393  Group  38:
3394
3395  120_HRV94a   AATCCAGTTGAGAAATACATTGATGGTGTATTGAATGAAGTTTTAGTTGTTCCAAATATC
3396  121_HRV94b   AATCCAGTTGAGAAATACATTGATGGTGTATTGAATGAAGTTTTAGTTGTTCCAAATATC
3397  122_HRV94    AATCCAGTTGAGAAATACATTGATGGTGTATTGAATGAAGTTTTAGTTGTTCCAAATATC
3398  GROUP_38     AATCCAGTTGAGAAATACATTGATGGTGTATTGAATGAAGTTTTAGTTGTTCCAAATATC
3399
3400  120_HRV94a   AATGAGAGTCACCCTAGCACATCCAATGCAGCGCCAGCCTTAGATGCTGCCGAAACTGGA
3401  121_HRV94b   AATGAGAGTCACCCTAGCACATCCAATGCAGCGCCAGCCTTAGATGCTGCCGAAACTGGA
3402  122_HRV94    AATGAGAGTCACCCTAGCACATCCAATGCAGCGCCAGCCTTAGATGCTGCCGAAACTGGA
3403  GROUP_38     AATGAGAGTCACCCTAGCACATCCAATGCAGCGCCAGCCTTAGATGCTGCCGAAACTGGA
3404
3405  120_HRV94a   CACACAAGCAATGTACAACCTGAGGATATGATTGAAACACGCTATGTACAAAACACTCAA
3406  121_HRV94b   CACACAAGCAATGTACAACCTGAGGATATGATTGAAACACGCTATGTACAAAACACTCAA
3407  122_HRV94    CACACAAGCAATGTACAACCTGAGGATATGATTGAAACACGCTATGTACAAAACACTCAA
3408  GROUP_38     CACACAAGCAATGTACAACCTGAGGATATGATTGAAACACGCTATGTACAAAACACTCAA
3409
3410  120_HRV94a   ACAAGGGATGAAATGAGCATTGAAAGCTTCTTGGGAAGATCTGGCTGTATACACATAGCA
3411  121_HRV94b   ACAAGGGATGAAATGAGCATTGAAAGCTTCTTGGGAAGATCTGGCTGTATACACATAGCA
3412  122_HRV94    ACAAGGGATGAAATGAGCATTGAAAGCTTCTTGGGAAGATCTGGCTGTATACACATAGCA
3413  GROUP_38     ACAAGGGATGAAATGAGCATTGAAAGCTTCTTGGGAAGATCTGGCTGTATACACATAGCA
3414
3415  120_HRV94a   CATCTAGAGATCAAGTATGATGGT---------------TACAATGAT---GCTGGCAAC
3416  121_HRV94b   CATCTAGAGATCAAGTATGATGGT---------------TACAATGAT---GCTGGCAAC
3417  122_HRV94    CATCTAGAGATCAAGTATGATGGT---------------TACAATGAT---GCTGGCAAC
3418  GROUP_38     CATCTAGAGATCAAGTATGATGGT...............TACAATGAT...GCTGGCAAC
3419
3420  120_HRV94a   AATTTCCAATCATGGCAAATTACCCTAAAAGAAATGGCACAAATAAGAAGGAAATTTGAA
3421  121_HRV94b   AATTTCCAATCATGGCAAATTACCCTAAAAGAAATGGCACAAATAAGAAGGAAATTTGAA
3422  122_HRV94    AATTTCCAATCATGGCAAATTACCCTAAAAGAAATGGCACAAATAAGAAGGAAATTTGAA
3423  GROUP_38     AATTTCCAATCATGGCAAATTACCCTAAAAGAAATGGCACAAATAAGAAGGAAATTTGAA
3424
3425  120_HRV94a   CTATTTACTTATGTTAGATTTGATTCAGAAATAACTTTAG-TACCTTGCATATCATCTCA
3426  121_HRV94b   CTATTTACTTATGTTAGATTTGATTCAGAAATAACTTTAG-TACCTTGCATATCATCTCA
3427  122_HRV94    CTATTTACTTATGTTAGATTTGATTCAGAAATAACTTTAG-TACCTTGCATATCATCTCA
3428  GROUP_38     CTATTTACTTATGTTAGATTTGATTCAGAAATAACTTTAG.TACCTTGCATATCATCTCA
3429
3430  120_HRV94a   AAGTGCTAATATTGGTCATGTTGTCATGCAGTACATGTATGTTCCTCCTGGAGCTCCAAA
3431  121_HRV94b   AAGTGCTAATATTGGTCATGTTGTCATGCAGTACATGTATGTTCCTCCTGGAGCTCCAAA
3432  122_HRV94    AAGTGCTAATATTGGTCATGTTGTCATGCAGTACATGTATGTTCCTCCTGGAGCTCCAAA
3433  GROUP_38     AAGTGCTAATATTGGTCATGTTGTCATGCAGTACATGTATGTTCCTCCTGGAGCTCCAAA
3434
3435  120_HRV94a   ACCAGACAAAAGAGATGATTATGTTTGGCAATCAGGAACTAATGCATCTATATTCTGGCA
3436  121_HRV94b   ACCAGACAAAAGAGATGATTATGTTTGGCAATCAGGAACTAATGCATCTATATTCTGGCA
3437  122_HRV94    ACCAGACAAAAGAGATGATTATGTTTGGCAATCAGGAACTAATGCATCTATATTCTGGCA
```

FIG. D14 CONT'D

```
10.trace                                                                                         9/20/2007 5:05 PM 3438 GROUP_38     ACCAGACAAAAGAGATGATTATGTTTGGCAATCAGGAACTAATGCATCTATATTCTGGCA
3439
3440 120_HRV94a   ACATGGTCAACCCTACCCTCGATTCTCACTTCCATTTCTTAGTATAGCCTCAGCATATTA
3441 121_HRV94b   ACATGGTCAACCCTACCCTCGATTCTCACTTCCATTTCTTAGTATAGCCTCAGCATATTA
3442 122_HRV94    ACATGGTCAACCCTACCCTCGATTCTCACTTCCATTTCTTAGTATAGCCTCAGCATATTA
3443 GROUP_38     ACATGGTCAACCCTACCCTCGATTCTCACTTCCATTTCTTAGTATAGCCTCAGCATATTA
3444
3445 120_HRV94a   CATGTTCTATGATGGTTATGATGGTGG---ACCTGGCTCACGCTATGGCACAGTGGTGAC
3446 121_HRV94b   CATGTTCTATGATGGTTATGATGGTGG---ACCTGGCTCACGCTATGGCACAGTGGTGAC
3447 122_HRV94    CATGTTCTATGATGGTTATGATGGTGG---ACCTGGCTCACGCTATGGCACAGTGGTGAC
3448 GROUP_38     CATGTTCTATGATGGTTATGATGGTGG...ACCTGGCTCACGCTATGGCACAGTGGTGAC
3449
3450 120_HRV94a   AAATGACATGGGAACATTATGCTCCAGGATTGTGACTGAGGAGCACAAGACACAGGTTAA
3451 121_HRV94b   AAATGACATGGGAACATTATGCTCCAGGATTGTGACTGAGGAGCACAAGACACAGGTTAA
3452 122_HRV94    AAATGACATGGGAACATTATGCTCCAGGATTGTGACTGAGGAGCACAAGACACAGGTTAA
3453 GROUP_38     AAATGACATGGGAACATTATGCTCCAGGATTGTGACTGAGGAGCACAAGACACAGGTTAA
3454
3455 120_HRV94a   CATCACTACTAGAGTGTACCACAAAGCAAAACATGTGAAAGCGTGGTGCCCGCGCCCTCC
3456 121_HRV94b   CATCACTACTAGAGTGTACCACAAAGCAAAACATGTGAAAGCGTGGTGCCCGCGCCCTCC
3457 122_HRV94    CATCACTACTAGAGTGTACCACAAAGCAAAACATGTGAAAGCGTGGTGCCCGCGCCCTCC
3458 GROUP_38     CATCACTACTAGAGTGTACCACAAAGCAAAACATGTGAAAGCGTGGTGCCCGCGCCCTCC
3459
3460 120_HRV94a   AAGAGCTGTTGGATACACA-CATACGCATGTCACTAATTACAAAC-CATCTG---AAGGG
3461 121_HRV94b   AAGAGCTGTTGGATACACA-CATACGCATGTCACTAATTACAAAC-CATCTG---AAGGG
3462 122_HRV94    AAGAGCTGTTGGATACACA-CATACGCATGTCACTAATTACAAAC-CATCTG---AAGGG
3463 GROUP_38     AAGAGCTGTTGGATACACA.CATACGCATGTCACTAATTACAAAC.CATCTG...AAGGG
3464
3465 120_HRV94a   GAGT------ACAAGCCAC---CTGTCCCAGTTAGGAATAGCCCCAGAGACATTGTCA--
3466 121_HRV94b   GAGT------ACAAGCCAC---CTGTCCCAGTTAGGAATAGCCCCAGAGACATTGTCA--
3467 122_HRV94    GAGT------ACAAGCCAC---CTGTCCCAGTTAGGAATAGCCCCAGAGACATTGTCA--
3468 GROUP_38     GAGT......ACAAGCCAC...CTGTCCCAGTTAGGAATAGCCCCAGAGACATTGTCA...
3469
3470 120_HRV94a   ----CAGTG------------
3471 121_HRV94b   ----CAGTC------------
3472 122_HRV94    ----CAGTA------------
3473 GROUP_38     ....CAGT-............
3474
3475
3476
3477 Group 39:
3478
3479 123_HRV22    AACCCTGTAGAGAAATACATTGATGGTGTATTGAATGAAGTATTGGTTGTTCCAAACACA
3480 124_HRV22a   AACCCTGTAGAGAAATACATTGATGGTGTATTGAATGAAGTATTGGTTGTTCCAAACACA
3481 125_HRV22b   AACCCTGTAGAGAAATACATTGATGGTGTATTGAATGAAGTATTGGTTGTTCCAAACACA
3482 GROUP_39     AACCCTGTAGAGAAATACATTGATGGTGTATTGAATGAAGTATTGGTTGTTCCAAACACA
3483
3484 123_HRV22    AATGAAAGTCACCCCAGTACATCAAATGCTGCACCAGCACTAGATGCTGCTGAAACTGGA
3485 124_HRV22a   AATGAAAGTCACCCCAGTACATCAAATGCTGCACCAGCACTAGATGCTGCTGAAACTGGA
3486 125_HRV22b   AATGAAAGTCACCCCAGTACATCAAATGCTGCACCAGCACTAGATGCTGCTGAAACTGGA
3487 GROUP_39     AATGAAAGTCACCCCAGTACATCAAATGCTGCACCAGCACTAGATGCTGCTGAAACTGGA
3488
3489 123_HRV22    CACACAAGCAATGTGCAGCCAGAAGACATGATAGAAACACGCTATGTGTTAAATTCACAA
3490 124_HRV22a   CACACAAGCAATGTGCAGCCAGAAGACATGATAGAAACACGCTATGTGTTAAATTCACAA
3491 125_HRV22b   CACACAAGCAATGTGCAGCCAGAAGACATGATAGAAACACGCTATGTGTTAAATTCACAA
3492 GROUP_39     CACACAAGCAATGTGCAGCCAGAAGACATGATAGAAACACGCTATGTGTTAAATTCACAA
3493
3494 123_HRV22    ACTAGAGATGAAATGAGTATTGAGAGCTTCCTGGGAAGATCTGGTTGCATACATATATCA
3495 124_HRV22a   ACTAGAGATGAAATGAGTATTGAGAGCTTCCTGGGAAGATCTGGTTGCATACATATATCA
3496 125_HRV22b   ACTAGAGATGAAATGAGTATTGAGAGCTTCCTGGGAAGATCTGGTTGCATACATATATCA
3497 GROUP_39     ACTAGAGATGAAATGAGTATTGAGAGCTTCCTGGGAAGATCTGGTTGCATACATATATCA
3498
3499 123_HRV22    CACTTAGAAGTAAAATACACAGGG--------------TATAATGAA---GAGGGTAAT
3500 124_HRV22a   CACTTAGAAGTAAAATACACAGGG--------------TATAATGAA---GAGGGTAAT
3501 125_HRV22b   CACTTAGAAGTAAAATACACAGGG--------------TATAATGAA---GAGGGTAAT
3502 GROUP_39     CACTTAGAAGTAAAATACACAGGG..............TATAATGAA...GAGGGTAAT
```

FIG. D14 CONT'D

```
10.trace                                                               9/20/2007 5:05 PM 123_HRV22    AACTTTAACATATGGCAAATTAACCTTAAAGAGATGGCTCAGATAAGAAGGAAGTTTGAG
124_HRV22a   AACTTTAACATATGGCAAATTAACCTTAAAGAGATGGCTCAGATAAGAAGGAAGTTTGAG
125_HRV22b   AACTTTAACATATGGCAAATTAACCTTAAAGAGATGGCTCAGATAAGAAGGAAGTTTGAG
GROUP_39     AACTTTAACATATGGCAAATTAACCTTAAAGAGATGGCTCAGATAAGAAGGAAGTTTGAG 123_HRV22    CTATTTACATATCTCAGGTTTGATTCTGAAATCACTTTGG-TACCATGCATTGCTTCACA
124_HRV22a   CTATTTACATATCTCAGGTTTGATTCTGAAATCACTTTGG-TACCATGCATTGCTTCACA
125_HRV22b   CTATTTACATATCTCAGGTTTGATTCTGAAATCACTTTGG-TACCATGCATTGCTTCACA
GROUP_39     CTATTTACATATCTCAGGTTTGATTCTGAAATCACTTTGG.TACCATGCATTGCTTCACA 123_HRV22    AAGTAAAAACATTGGTCATGTGGTCATGCAATACATGTATGTTCCGCCTGGAGCTCCTAA
124_HRV22a   AAGTAAAAACATTGGTCATGTGGTCATGCAATACATGTATGTTCCGCCTGGAGCTCCTAA
125_HRV22b   AAGTAAAAACATTGGTCATGTGGTCATGCAATACATGTATGTTCCGCCTGGAGCTCCTAA
GROUP_39     AAGTAAAAACATTGGTCATGTGGTCATGCAATACATGTATGTTCCGCCTGGAGCTCCTAA 123_HRV22    ACCTGAAAAGAGAGATGACTACACATGGCAATCTGGCACTAATGCATCTGTTTTCTGGCA
124_HRV22a   ACCTGAAAAGAGAGATGACTACACATGGCAATCTGGCACTAATGCATCTGTTTTCTGGCA
125_HRV22b   ACCTGAAAAGAGAGATGACTACACATGGCAATCTGGCACTAATGCATCTGTTTTCTGGCA
GROUP_39     ACCTGAAAAGAGAGATGACTACACATGGCAATCTGGCACTAATGCATCTGTTTTCTGGCA 123_HRV22    GCATGGTCAACCTTATCCCCGATTCTCACTCCCTTTCCTCAGTGTAGCTTCAGCATATTA
124_HRV22a   GCATGGTCAACCTTATCCCCGATTCTCACTCCCTTTCCTCAGTGTAGCTTCAGCATATTA
125_HRV22b   GCATGGTCAACCTTATCCCCGATTCTCACTCCCTTTCCTCAGTGTAGCTTCAGCATATTA
GROUP_39     GCATGGTCAACCTTATCCCCGATTCTCACTCCCTTTCCTCAGTGTAGCTTCAGCATATTA 123_HRV22    CATGTTTTATGATGGGTATGATGGAGG---TCCCGGATCACGTTATGGAGCAGTGGTAAC
124_HRV22a   CATGTTTTATGATGGGTATGATGGAGG---TCCCGGATCACGTTATGGAGCAGTGGTAAC
125_HRV22b   CATGTTTTATGATGGGTATGATGGAGG---TCCCGGATCACGTTATGGAGCAGTGGTAAC
GROUP_39     CATGTTTTATGATGGGTATGATGGAGG...TCCCGGATCACGTTATGGAGCAGTGGTAAC 123_HRV22    AAATGATATGGGCACACTGTGCTCTAGGATTGTGACTGAAGAACACCAGACACAAGTCAA
124_HRV22a   AAATGATATGGGCACACTGTGCTCTAGGATTGTGACTGAAGAACACCAGACACAAGTCAA
125_HRV22b   AAATGATATGGGCACACTGTGCTCTAGGATTGTGACTGAAGAACACCAGACACAAGTCAA
GROUP_39     AAATGATATGGGCACACTGTGCTCTAGGATTGTGACTGAAGAACACCAGACACAAGTCAA 123_HRV22    AATTACAACTAGAGTGTACCACAAAGCAAAACATGTAAAGGCATGGTGCCCACGTCCTCC
124_HRV22a   AATTACAACTAGAGTGTACCACAAAGCAAAACATGTAAAGGCATGGTGCCCACGTCCTCC
125_HRV22b   AATTACAACTAGAGTGTACCACAAAGCAAAACATGTAAAGGCATGGTGCCCACGTCCTCC
GROUP_39     AATTACAACTAGAGTGTACCACAAAGCAAAACATGTAAAGGCATGGTGCCCACGTCCTCC 123_HRV22    AAGAGCTGTTGGATATACA-CACACACATGTGACAAACTACAAAC-CATCTG---TAGGG
124_HRV22a   AAGAGCTGTTGGATATACA-CACACACATGTGACAAACTACAAAC-CATCTG---TAGGG
125_HRV22b   AAGAGCTGTTGGATATACA-CACACACATGTGACAAACTACAAAC-CATCTG---TAGGG
GROUP_39     AAGAGCTGTTGGATATACA.CACACACATGTGACAAACTACAAAC.CATCTG...TAGGG 123_HRV22    GATT------ACACACTAC---CTATCCCAACAAGAGCCAACCCTAGACAAATTTTGA--
124_HRV22a   GATT------ACACACTAC---CTATCCCAACAAGAGCCAACCCTAGACAAATTTTGA--
125_HRV22b   GATT------ACACACTAC---CTATCCCAACAAGAGCCAACCCTAGACAAATTTTGA--
GROUP_39     GATT......ACACACTAC...CTATCCCAACAAGAGCCAACCCTAGACAAATTTTGA..

123_HRV22    ----ATGTA------------
124_HRV22a   ----ATGTG------------
125_HRV22b   ----ATGTC------------
GROUP_39     ....ATGT-............

Group  40:

126_HRV82    AATCCAGTTGAAAAGTATGTTGATAGTGTTTTAAACGAGGTATTAGTTGTTCCTAACATT
127_HRV82b   AATCCAGTTGAAAAGTATGTTGATAGTGTTTTAAACGAGGTATTAGTTGTTCCTAACATT
128_HRV82a   AATCCAGTTGAAAAGTATGTTGATAGTGTTTTAAACGAGGTATTAGTTGTTCCTAACATT
GROUP_40     AATCCAGTTGAAAAGTATGTTGATAGTGTTTTAAACGAGGTATTAGTTGTTCCTAACATT
```

FIG. D14 CONT'D

```
10.trace                                                          9/20/2007 5:05 PM 3568  126_HRV82    AATGAAAGTCATCCTAGTACTTCAAATTCAGCTCCTGCCTTGGACGCTGCAGAGACAGGA
3569  127_HRV82b   AATGAAAGTCATCCTAGTACTTCAAATTCAGCTCCTGCCTTGGACGCTGCAGAGACAGGA
3570  128_HRV82a   AATGAAAGTCATCCTAGTACTTCAAATTCAGCTCCTGCCTTGGACGCTGCAGAGACAGGA
3571  GROUP_40     AATGAAAGTCATCCTAGTACTTCAAATTCAGCTCCTGCCTTGGACGCTGCAGAGACAGGA
3572
3573  126_HRV82    CATACAAGTACTGTTCAACCTGAGGACATGATTGAAACACGGTATGTTCAAACATCACAA
3574  127_HRV82b   CATACAAGTACTGTTCAACCTGAGGACATGATTGAAACACGGTATGTTCAAACATCACAA
3575  128_HRV82a   CATACAAGTACTGTTCAACCTGAGGACATGATTGAAACACGGTATGTTCAAACATCACAA
3576  GROUP_40     CATACAAGTACTGTTCAACCTGAGGACATGATTGAAACACGGTATGTTCAAACATCACAA
3577
3578  126_HRV82    ACTAGAGATGAGATGAGCCTTGAGAGTTTCCTAGGGAGATCTGGCTGCATACACATATCA
3579  127_HRV82b   ACTAGAGATGAGATGAGCCTTGAGAGTTTCCTAGGGAGATCTGGCTGCATACACATATCA
3580  128_HRV82a   ACTAGAGATGAGATGAGCCTTGAGAGTTTCCTAGGGAGATCTGGCTGCATACACATATCA
3581  GROUP_40     ACTAGAGATGAGATGAGCCTTGAGAGTTTCCTAGGGAGATCTGGCTGCATACACATATCA
3582
3583  126_HRV82    CACCTAAATGTCAGATACACTG------------------ATTATAAT---GAAGGTAAT
3584  127_HRV82b   CACCTAAATGTCAGATACACTG------------------ATTATAAT---GAAGGTAAT
3585  128_HRV82a   CACCTAAATGTCAGATACACTG------------------ATTATAAT---GAAGGTAAT
3586  GROUP_40     CACCTAAATGTCAGATACACTG..................ATTATAAT...GAAGGTAAT
3587
3588  126_HRV82    AACTTTAGATCATGGCAAATAAGCATAAAGGAAATGGCACAAATTAGAAGGAAGTTTGAA
3589  127_HRV82b   AACTTTAGATCATGGCAAATAAGCATAAAGGAAATGGCACAAATTAGAAGGAAGTTTGAA
3590  128_HRV82a   AACTTTAGATCATGGCAAATAAGCATAAAGGAAATGGCACAAATTAGAAGGAAGTTTGAA
3591  GROUP_40     AACTTTAGATCATGGCAAATAAGCATAAAGGAAATGGCACAAATTAGAAGGAAGTTTGAA
3592
3593  126_HRV82    CTTTTCACATATGTGAGATTTGATTCAGAAATTACTTTAG-TGCCTTGCATAGCCTCTCA
3594  127_HRV82b   CTTTTCACATATGTGAGATTTGATTCAGAAATTACTTTAG-TGCCTTGCATAGCCTCTCA
3595  128_HRV82a   CTTTTCACATATGTGAGATTTGATTCAGAAATTACTTTAG-TGCCTTGCATAGCCTCTCA
3596  GROUP_40     CTTTTCACATATGTGAGATTTGATTCAGAAATTACTTTAG.TGCCTTGCATAGCCTCTCA
3597
3598  126_HRV82    AAGTAATGATATTGGGCATGTAGTGATGCAATACATGTATGTCCCACCAGGTGCTCCTAA
3599  127_HRV82b   AAGTAATGATATTGGGCATGTAGTGATGCAATACATGTATGTCCCACCAGGTGCTCCTAA
3600  128_HRV82a   AAGTAATGATATTGGGCATGTAGTGATGCAATACATGTATGTCCCACCAGGTGCTCCTAA
3601  GROUP_40     AAGTAATGATATTGGGCATGTAGTGATGCAATACATGTATGTCCCACCAGGTGCTCCTAA
3602
3603  126_HRV82    ACCAGAAAAGAGAGACGACTACACTTGGCAATCTGGAACTAATGCTTCAATTTTCTGGCA
3604  127_HRV82b   ACCAGAAAAGAGAGACGACTACACTTGGCAATCTGGAACTAATGCTTCAATTTTCTGGCA
3605  128_HRV82a   ACCAGAAAAGAGAGACGACTACACTTGGCAATCTGGAACTAATGCTTCAATTTTCTGGCA
3606  GROUP_40     ACCAGAAAAGAGAGACGACTACACTTGGCAATCTGGAACTAATGCTTCAATTTTCTGGCA
3607
3608  126_HRV82    ACATGGACAACCTTACCCTCGCTTCTCACTTCCTTTCTTGAGTATAGCCTCAGCTTACTA
3609  127_HRV82b   ACATGGACAACCTTACCCTCGCTTCTCACTTCCTTTCTTGAGTATAGCCTCAGCTTACTA
3610  128_HRV82a   ACATGGACAACCTTACCCTCGCTTCTCACTTCCTTTCTTGAGTATAGCCTCAGCTTACTA
3611  GROUP_40     ACATGGACAACCTTACCCTCGCTTCTCACTTCCTTTCTTGAGTATAGCCTCAGCTTACTA
3612
3613  126_HRV82    TATGTTCTATGATGGCTATGATGGTGATGCTCCCGGATCGCGATACGGGACCATAGTGAC
3614  127_HRV82b   TATGTTCTATGATGGCTATGATGGTGATGCTCCCGGATCGCGATACGGGACCATAGTGAC
3615  128_HRV82a   TATGTTCTATGATGGCTATGATGGTGATGCTCCCGGATCGCGATACGGGACCATAGTGAC
3616  GROUP_40     TATGTTCTATGATGGCTATGATGGTGATGCTCCCGGATCGCGATACGGGACCATAGTGAC
3617
3618  126_HRV82    AAATGACATGGGTACACTGTGTTCTAGAATTGTAACTGAAGAACACCAGACTCAAGTCAG
3619  127_HRV82b   AAATGACATGGGTACACTGTGTTCTAGAATTGTAACTGAAGAACACCAGACTCAAGTCAG
3620  128_HRV82a   AAATGACATGGGTACACTGTGTTCTAGAATTGTAACTGAAGAACACCAGACTCAAGTCAG
3621  GROUP_40     AAATGACATGGGTACACTGTGTTCTAGAATTGTAACTGAAGAACACCAGACTCAAGTCAG
3622
3623  126_HRV82    CATTACCACAAGAATATATCACAAAGCAAAACATGTGAAAGCGTGGTGTCCACGACCCCC
3624  127_HRV82b   CATTACCACAAGAATATATCACAAAGCAAAACATGTGAAAGCGTGGTGTCCACGACCCCC
3625  128_HRV82a   CATTACCACAAGAATATATCACAAAGCAAAACATGTGAAAGCGTGGTGTCCACGACCCCC
3626  GROUP_40     CATTACCACAAGAATATATCACAAAGCAAAACATGTGAAAGCGTGGTGTCCACGACCCCC
3627
3628  126_HRV82    GAGGGCTGTGGGTTATACA-CACACACATGTTACCAACTACAAGC-CATCAC---AGGGA
3629  127_HRV82b   GAGGGCTGTGGGTTATACA-CACACACATGTTACCAACTACAAGC-CATCAC---AGGGA
3630  128_HRV82a   GAGGGCTGTGGGTTATACA-CACACACATGTTACCAACTACAAGC-CATCAC---AGGGA
3631  GROUP_40     GAGGGCTGTGGGTTATACA.CACACACATGTTACCAACTACAAGC.CATCAC...AGGGA
3632
```

FIG. D14 CONT'D

```
10.trace                                                                                  9/20/2007 5:05 PM 3633  126_HRV82    GATT------ACAGTGTTG---TTATTCCAGTTAGAGAGAGTCCCAGACAGATTCTTA--
3634  127_HRV82b   GATT------ACAGTGTTG---TTATTCCAGTTAGAGAGAGTCCCAGACAGATTCTTA--
3635  128_HRV82a   GATT------ACAGTGTTG---TTATTCCAGTTAGAGAGAGTCCCAGACAGATTCTTA--
3636  GROUP_40     GATT......ACAGTGTTG...TTATTCCAGTTAGAGAGAGTCCCAGACAGATTCTTA..
3637
3638  126_HRV82    ----ATGTA------------
3639  127_HRV82b   ----ATGTT------------
3640  128_HRV82a   ----ATGTC------------
3641  GROUP_40     ....ATGT-............
3642
3643
3644
3645  Group 41:
3646
3647  129_HRV19    AATCCTGTAGAGAAATATGTGGACACCATTCTGAATGAGGTGCTAGTTGTCCCAAATATC
3648  130_HRV19a   AATCCTGTAGAGAAATATGTGGACACCATTCTGAATGAGGTGCTAGTTGTCCCAAATATC
3649  131_HRV19b   AATCCTGTAGAGAAATATGTGGACACCATTCTGAATGAGGTGCTAGTTGTCCCAAATATC
3650  GROUP_41     AATCCTGTAGAGAAATATGTGGACACCATTCTGAATGAGGTGCTAGTTGTCCCAAATATC
3651
3652  129_HRV19    AATGAAAGTCATCCAAGTACATCAAATGCTGCTCCTGCCTTAGATGCAGCCGAGACAGGA
3653  130_HRV19a   AATGAAAGTCATCCAAGTACATCAAATGCTGCTCCTGCCTTAGATGCAGCCGAGACAGGA
3654  131_HRV19b   AATGAAAGTCATCCAAGTACATCAAATGCTGCTCCTGCCTTAGATGCAGCCGAGACAGGA
3655  GROUP_41     AATGAAAGTCATCCAAGTACATCAAATGCTGCTCCTGCCTTAGATGCAGCCGAGACAGGA
3656
3657  129_HRV19    CATACTAGCAATGTACAGCCTGAGGACATGATCGAAACACGCTATGTTCAAACGTCCCAG
3658  130_HRV19a   CATACTAGCAATGTACAGCCTGAGGACATGATCGAAACACGCTATGTTCAAACGTCCCAG
3659  131_HRV19b   CATACTAGCAATGTACAGCCTGAGGACATGATCGAAACACGCTATGTTCAAACGTCCCAG
3660  GROUP_41     CATACTAGCAATGTACAGCCTGAGGACATGATCGAAACACGCTATGTTCAAACGTCCCAG
3661
3662  129_HRV19    ACTAGGGATGAAATGAGCATAGAAAGTTTTCTTGGCAGATCCGGTTGTGTACATGTTTCA
3663  130_HRV19a   ACTAGGGATGAAATGAGCATAGAAAGTTTTCTTGGCAGATCCGGTTGTGTACATGTTTCA
3664  131_HRV19b   ACTAGGGATGAAATGAGCATAGAAAGTTTTCTTGGCAGATCCGGTTGTGTACATGTTTCA
3665  GROUP_41     ACTAGGGATGAAATGAGCATAGAAAGTTTTCTTGGCAGATCCGGTTGTGTACATGTTTCA
3666
3667  129_HRV19    GAGCTCCAATTAGATTATACCAAT---------------TACAATCAA---GAAAATAAT
3668  130_HRV19a   GAGCTCCAATTAGATTATACCAAT---------------TACAATCAA---GAAAATAAT
3669  131_HRV19b   GAGCTCCAATTAGATTATACCAAT---------------TACAATCAA---GAAAATAAT
3670  GROUP_41     GAGCTCCAATTAGATTATACCAAT...............TACAATCAA...GAAAATAAT
3671
3672  129_HRV19    AATTTCAAAACTTGGCAAATAAACTTGAAAGAAATGGCACAGATTAGAAGAAAATTTGAA
3673  130_HRV19a   AATTTCAAAACTTGGCAAATAAACTTGAAAGAAATGGCACAGATTAGAAGAAAATTTGAA
3674  131_HRV19b   AATTTCAAAACTTGGCAAATAAACTTGAAAGAAATGGCACAGATTAGAAGAAAATTTGAA
3675  GROUP_41     AATTTCAAAACTTGGCAAATAAACTTGAAAGAAATGGCACAGATTAGAAGAAAATTTGAA
3676
3677  129_HRV19    CTTTTCACTTACCTCAGATTTGATTCAGAGGTAACATTAG-TCCCTTGCATAGCTGCTAA
3678  130_HRV19a   CTTTTCACTTACCTCAGATTTGATTCAGAGGTAACATTAG-TCCCTTGCATAGCTGCTAA
3679  131_HRV19b   CTTTTCACTTACCTCAGATTTGATTCAGAGGTAACATTAG-TCCCTTGCATAGCTGCTAA
3680  GROUP_41     CTTTTCACTTACCTCAGATTTGATTCAGAGGTAACATTAG.TCCCTTGCATAGCTGCTAA
3681
3682  129_HRV19    AAGTAAAAACATTGGACATGTTGTTATGCAATACATGTATGTGCCTCCTGGTGCTCCTAT
3683  130_HRV19a   AAGTAAAAACATTGGACATGTTGTTATGCAATACATGTATGTGCCTCCTGGTGCTCCTAT
3684  131_HRV19b   AAGTAAAAACATTGGACATGTTGTTATGCAATACATGTATGTGCCTCCTGGTGCTCCTAT
3685  GROUP_41     AAGTAAAAACATTGGACATGTTGTTATGCAATACATGTATGTGCCTCCTGGTGCTCCTAT
3686
3687  129_HRV19    CCCAAAAACTAGAAATGATTACACATGGCAATCAGGTACTAATGCATCTATATTTTGGCA
3688  130_HRV19a   CCCAAAAACTAGAAATGATTACACATGGCAATCAGGTACTAATGCATCTATATTTTGGCA
3689  131_HRV19b   CCCAAAAACTAGAAATGATTACACATGGCAATCAGGTACTAATGCATCTATATTTTGGCA
3690  GROUP_41     CCCAAAAACTAGAAATGATTACACATGGCAATCAGGTACTAATGCATCTATATTTTGGCA
3691
3692  129_HRV19    ACATGGTCAACCATACCCAAGATTTTCATTACCTTTTCTAAGTATAGCTTCTGCATATTA
3693  130_HRV19a   ACATGGTCAACCATACCCAAGATTTTCATTACCTTTTCTAAGTATAGCTTCTGCATATTA
3694  131_HRV19b   ACATGGTCAACCATACCCAAGATTTTCATTACCTTTTCTAAGTATAGCTTCTGCATATTA
3695  GROUP_41     ACATGGTCAACCATACCCAAGATTTTCATTACCTTTTCTAAGTATAGCTTCTGCATATTA
3696
3697  129_HRV19    CATGTTTTATGATGGGTATGATGGAGATTCACCAGGATCCCGCTATGGAACAATAGTAAC
```

FIG. D14 CONT'D

```
10.trace                                                                                    9/20/2007 5:05 PM 3698  130_HRV19a   CATGTTTTATGATGGGTATGATGGAGATTCACCAGGATCCCGCTATGGAACAATAGTAAC
3699  131_HRV19b   CATGTTTTATGATGGGTATGATGGAGATTCACCAGGATCCCGCTATGGAACAATAGTAAC
3700  GROUP_41     CATGTTTTATGATGGGTATGATGGAGATTCACCAGGATCCCGCTATGGAACAATAGTAAC
3701
3702  129_HRV19    TAATGATATGGGAACCTTATGCTCCAGAATAGTAACTGATGAACACCAAACACAGGTTGC
3703  130_HRV19a   TAATGATATGGGAACCTTATGCTCCAGAATAGTAACTGATGAACACCAAACACAGGTTGC
3704  131_HRV19b   TAATGATATGGGAACCTTATGCTCCAGAATAGTAACTGATGAACACCAAACACAGGTTGC
3705  GROUP_41     TAATGATATGGGAACCTTATGCTCCAGAATAGTAACTGATGAACACCAAACACAGGTTGC
3706
3707  129_HRV19    AATCACAACTAGAGTATATCATAAAGCTAAACATATAAAAGCTTGGTGCCCACGACCACC
3708  130_HRV19a   AATCACAACTAGAGTATATCATAAAGCTAAACATATAAAAGCTTGGTGCCCACGACCACC
3709  131_HRV19b   AATCACAACTAGAGTATATCATAAAGCTAAACATATAAAAGCTTGGTGCCCACGACCACC
3710  GROUP_41     AATCACAACTAGAGTATATCATAAAGCTAAACATATAAAAGCTTGGTGCCCACGACCACC
3711
3712  129_HRV19    CAGAGCCGTGGAATATACC-CACACTCATGTGACTAATTATAAAC-CCCAGA---CAGGT
3713  130_HRV19a   CAGAGCCGTGGAATATACC-CACACTCATGTGACTAATTATAAAC-CCCAGA---CAGGT
3714  131_HRV19b   CAGAGCCGTGGAATATACC-CACACTCATGTGACTAATTATAAAC-CCCAGA---CAGGT
3715  GROUP_41     CAGAGCCGTGGAATATACC.CACACTCATGTGACTAATTATAAAC.CCCAGA...CAGGT
3716
3717  129_HRV19    GAAG------TCACTCTTC---CAATTGAAATAAGAGATAACCCTAGACATATAAAGA--
3718  130_HRV19a   GAAG------TCACTCTTC---CAATTGAAATAAGAGATAACCCTAGACATATAAAGA--
3719  131_HRV19b   GAAG------TCACTCTTC---CAATTGAAATAAGAGATAACCCTAGACATATAAAGA--
3720  GROUP_41     GAAG......TCACTCTTC...CAATTGAAATAAGAGATAACCCTAGACATATAAAGA..
3721
3722  129_HRV19    ----ATGTA------------
3723  130_HRV19a   ----ATGTG------------
3724  131_HRV19b   ----ATGTC------------
3725  GROUP_41     ....ATGT-............
3726
3727
3728
3729  Group 42:
3730
3731  132_HRV13    AATCCTGTTGAAAGGTATGTAGATGAAGTCTTGAATGAAGTTCTTGTAGTACCAAATATC
3732  133_HRV13a   AATCCTGTTGAAAGGTATGTAGATGAAGTCTTGAATGAAGTTCTTGTAGTACCAAATATC
3733  134_HRV13b   AATCCTGTTGAAAGGTATGTAGATGAAGTCTTGAATGAAGTTCTTGTAGTACCAAATATC
3734  GROUP_42     AATCCTGTTGAAAGGTATGTAGATGAAGTCTTGAATGAAGTTCTTGTAGTACCAAATATC
3735
3736  132_HRV13    AGTGAAAGTAGCTCAACTACATCTAATTCAGCTCCAGCCTTAGATGCTGCAGAAACTGGC
3737  133_HRV13a   AGTGAAAGTAGCTCAACTACATCTAATTCAGCTCCAGCCTTAGATGCTGCAGAAACTGGC
3738  134_HRV13b   AGTGAAAGTAGCTCAACTACATCTAATTCAGCTCCAGCCTTAGATGCTGCAGAAACTGGC
3739  GROUP_42     AGTGAAAGTAGCTCAACTACATCTAATTCAGCTCCAGCCTTAGATGCTGCAGAAACTGGC
3740
3741  132_HRV13    CACACAAGCAGTGTACAACCAGAAGACATGGTTGAAACACGTTATGTCCAAACTTCACAA
3742  133_HRV13a   CACACAAGCAGTGTACAACCAGAAGACATGGTTGAAACACGTTATGTCCAAACTTCACAA
3743  134_HRV13b   CACACAAGCAGTGTACAACCAGAAGACATGGTTGAAACACGTTATGTCCAAACTTCACAA
3744  GROUP_42     CACACAAGCAGTGTACAACCAGAAGACATGGTTGAAACACGTTATGTCCAAACTTCACAA
3745
3746  132_HRV13    ACTAGGGATGAAATGAGTGTTGAGAGCTTTTTAGGCAGATCTGGTTGTATACACATGTCT
3747  133_HRV13a   ACTAGGGATGAAATGAGTGTTGAGAGCTTTTTAGGCAGATCTGGTTGTATACACATGTCT
3748  134_HRV13b   ACTAGGGATGAAATGAGTGTTGAGAGCTTTTTAGGCAGATCTGGTTGTATACACATGTCT
3749  GROUP_42     ACTAGGGATGAAATGAGTGTTGAGAGCTTTTTAGGCAGATCTGGTTGTATACACATGTCT
3750
3751  132_HRV13    ACCATGAACATAGATTATACTAAT---------------TATGATGAT---TCTGTTAAT
3752  133_HRV13a   ACCATGAACATAGATTATACTAAT---------------TATGATGAT---TCTGTTAAT
3753  134_HRV13b   ACCATGAACATAGATTATACTAAT---------------TATGATGAT---TCTGTTAAT
3754  GROUP_42     ACCATGAACATAGATTATACTAAT...............TATGATGAT...TCTGTTAAT
3755
3756  132_HRV13    AATTTTGTGAAATGGAAAATAAGTTTGCAAGAAATGGCCCAAGTGCGCAGAAAATTTGAG
3757  133_HRV13a   AATTTTGTGAAATGGAAAATAAGTTTGCAAGAAATGGCCCAAGTGCGCAGAAAATTTGAG
3758  134_HRV13b   AATTTTGTGAAATGGAAAATAAGTTTGCAAGAAATGGCCCAAGTGCGCAGAAAATTTGAG
3759  GROUP_42     AATTTTGTGAAATGGAAAATAAGTTTGCAAGAAATGGCCCAAGTGCGCAGAAAATTTGAG
3760
3761  132_HRV13    TTGTTCACCTATGTAAGATTTGATTCAGAAATAACAATTG-TGCCATGTATAGCCGGGCA
3762  133_HRV13a   TTGTTCACCTATGTAAGATTTGATTCAGAAATAACAATTG-TGCCATGTATAGCCGGGCA
```

FIG. D14 CONT'D

```
10.trace                                                          9/20/2007 5:05 PM 3763 134_HRV13b  TTGTTCACCTATGTAAGATTTGATTCAGAAATAACAATTG-TGCCATGTATAGCCGGGCA
3764 GROUP_42    TTGTTCACCTATGTAAGATTTGATTCAGAAATAACAATTG.TGCCATGTATAGCCGGGCA
3765
3766 132_HRV13   AGGTGGTGATGTCGGACATGTTGTTATGCAATACATGTATGTACCGCCCGGTGCACCCCT
3767 133_HRV13a  AGGTGGTGATGTCGGACATGTTGTTATGCAATACATGTATGTACCGCCCGGTGCACCCCT
3768 134_HRV13b  AGGTGGTGATGTCGGACATGTTGTTATGCAATACATGTATGTACCGCCCGGTGCACCCCT
3769 GROUP_42    AGGTGGTGATGTCGGACATGTTGTTATGCAATACATGTATGTACCGCCCGGTGCACCCCT
3770
3771 132_HRV13   TCCAACGAAGAGAAATGATTACACATGGCAATCTGGCACCAATGCATCTGTTTTCTGGCA
3772 133_HRV13a  TCCAACGAAGAGAAATGATTACACATGGCAATCTGGCACCAATGCATCTGTTTTCTGGCA
3773 134_HRV13b  TCCAACGAAGAGAAATGATTACACATGGCAATCTGGCACCAATGCATCTGTTTTCTGGCA
3774 GROUP_42    TCCAACGAAGAGAAATGATTACACATGGCAATCTGGCACCAATGCATCTGTTTTCTGGCA
3775
3776 132_HRV13   ACATGGTCAAATTTACCCCCGATTCTCTTTACCATTTCTTAGTATTGCATCTGCATATTA
3777 133_HRV13a  ACATGGTCAAATTTACCCCCGATTCTCTTTACCATTTCTTAGTATTGCATCTGCATATTA
3778 134_HRV13b  ACATGGTCAAATTTACCCCCGATTCTCTTTACCATTTCTTAGTATTGCATCTGCATATTA
3779 GROUP_42    ACATGGTCAAATTTACCCCCGATTCTCTTTACCATTTCTTAGTATTGCATCTGCATATTA
3780
3781 132_HRV13   TATGTTTTATGATGGATATAATGGAGATTCCTCAGATGCACGCTATGGGACAACAATCAC
3782 133_HRV13a  TATGTTTTATGATGGATATAATGGAGATTCCTCAGATGCACGCTATGGGACAACAATCAC
3783 134_HRV13b  TATGTTTTATGATGGATATAATGGAGATTCCTCAGATGCACGCTATGGGACAACAATCAC
3784 GROUP_42    TATGTTTTATGATGGATATAATGGAGATTCCTCAGATGCACGCTATGGGACAACAATCAC
3785
3786 132_HRV13   TAATGATATGGGCACACTTTGCTTCAGAATAGTAACTGAAGAACATACTAACAAGGTCAA
3787 133_HRV13a  TAATGATATGGGCACACTTTGCTTCAGAATAGTAACTGAAGAACATACTAACAAGGTCAA
3788 134_HRV13b  TAATGATATGGGCACACTTTGCTTCAGAATAGTAACTGAAGAACATACTAACAAGGTCAA
3789 GROUP_42    TAATGATATGGGCACACTTTGCTTCAGAATAGTAACTGAAGAACATACTAACAAGGTCAA
3790
3791 132_HRV13   GGTTACAACTAGAATCTATCATAAAGCTAAACATGTCAAAGCATGGTGTCCTAGACCTCC
3792 133_HRV13a  GGTTACAACTAGAATCTATCATAAAGCTAAACATGTCAAAGCATGGTGTCCTAGACCTCC
3793 134_HRV13b  GGTTACAACTAGAATCTATCATAAAGCTAAACATGTCAAAGCATGGTGTCCTAGACCTCC
3794 GROUP_42    GGTTACAACTAGAATCTATCATAAAGCTAAACATGTCAAAGCATGGTGTCCTAGACCTCC
3795
3796 132_HRV13   CAGAGCTGTTGAATATACT-AATGTGCATGTTACAAACTACAAAC-CAGGGA---CAGGA
3797 133_HRV13a  CAGAGCTGTTGAATATACT-AATGTGCATGTTACAAACTACAAAC-CAGGGA---CAGGA
3798 134_HRV13b  CAGAGCTGTTGAATATACT-AATGTGCATGTTACAAACTACAAAC-CAGGGA---CAGGA
3799 GROUP_42    CAGAGCTGTTGAATATACT.AATGTGCATGTTACAAACTACAAAC.CAGGGA...CAGGA
3800
3801 132_HRV13   GATG------TTGCAGTCT---CCATTGTACCTAGAGCAAATGTTAGGGAAATTAGAA--
3802 133_HRV13a  GATG------TTGCAGTCT---CCATTGTACCTAGAGCAAATGTTAGGGAAATTAGAA--
3803 134_HRV13b  GATG------TTGCAGTCT---CCATTGTACCTAGAGCAAATGTTAGGGAAATTAGAA--
3804 GROUP_42    GATG......TTGCAGTCT...CCATTGTACCTAGAGCAAATGTTAGGGAAATTAGAA..
3805
3806 132_HRV13   ----ACTTT------------
3807 133_HRV13a  ----ACTTG------------
3808 134_HRV13b  ----ACTTA------------
3809 GROUP_42    ....ACTT-............
3810
3811
3812
3813 Group 43:
3814
3815 135_HRV41   AATCCTGTAGAAAGGTATGTGGATGAGGTCCTGAATGAGGTTCTTGTGGTACCAAATATT
3816 136_HRV41a  AATCCTGTAGAAAGGTATGTGGATGAGGTCCTGAATGAGGTTCTTGTGGTACCAAATATT
3817 137_HRV41b  AATCCTGTAGAAAGGTATGTGGATGAGGTCCTGAATGAGGTTCTTGTGGTACCAAATATT
3818 GROUP_43    AATCCTGTAGAAAGGTATGTGGATGAGGTCCTGAATGAGGTTCTTGTGGTACCAAATATT
3819
3820 135_HRV41   AGTGAAAGCAGTCCAACTACTTCTAATTCAGCTCCAGCCCTAGATGCAGCAGAGACTGGT
3821 136_HRV41a  AGTGAAAGCAGTCCAACTACTTCTAATTCAGCTCCAGCCCTAGATGCAGCAGAGACTGGT
3822 137_HRV41b  AGTGAAAGCAGTCCAACTACTTCTAATTCAGCTCCAGCCCTAGATGCAGCAGAGACTGGT
3823 GROUP_43    AGTGAAAGCAGTCCAACTACTTCTAATTCAGCTCCAGCCCTAGATGCAGCAGAGACTGGT
3824
3825 135_HRV41   CATACCAGTAATGTACAACCAGAGGACATGATTGAAACACGATATGTCCAAACCTCACAA
3826 136_HRV41a  CATACCAGTAATGTACAACCAGAGGACATGATTGAAACACGATATGTCCAAACCTCACAA
3827 137_HRV41b  CATACCAGTAATGTACAACCAGAGGACATGATTGAAACACGATATGTCCAAACCTCACAA
```

FIG. D14 CONT'D

```
10.trace                                                                          9/20/2007 5:05 PM 3828 GROUP_43      CATACCAGTAATGTACAACCAGAGGACATGATTGAAACACGATATGTCCAAACCTCACAA
3829
3830 135_HRV41     ACTAGAGATGAAATGAGCATAGAAAGCTTTTTAGGTAGATCAGGCTGTGTACATAAGTCC
3831 136_HRV41a    ACTAGAGATGAAATGAGCATAGAAAGCTTTTTAGGTAGATCAGGCTGTGTACATAAGTCC
3832 137_HRV41b    ACTAGAGATGAAATGAGCATAGAAAGCTTTTTAGGTAGATCAGGCTGTGTACATAAGTCC
3833 GROUP_43      ACTAGAGATGAAATGAGCATAGAAAGCTTTTTAGGTAGATCAGGCTGTGTACATAAGTCC
3834
3835 135_HRV41     ACTTTGAATATAGATTATACTGAT---------------TATGATGAT---TCTATCCAG
3836 136_HRV41a    ACTTTGAATATAGATTATACTGAT---------------TATGATGAT---TCTATCCAG
3837 137_HRV41b    ACTTTGAATATAGATTATACTGAT---------------TATGATGAT---TCTATCCAG
3838 GROUP_43      ACTTTGAATATAGATTATACTGAT...............TATGATGAT...TCTATCCAG
3839
3840 135_HRV41     AACTTCAAGAAGTGGAAAATTAGCTTACAGGAGATGGCCCAAGTACGTAGAAAGTTTGAG
3841 136_HRV41a    AACTTCAAGAAGTGGAAAATTAGCTTACAGGAGATGGCCCAAGTACGTAGAAAGTTTGAG
3842 137_HRV41b    AACTTCAAGAAGTGGAAAATTAGCTTACAGGAGATGGCCCAAGTACGTAGAAAGTTTGAG
3843 GROUP_43      AACTTCAAGAAGTGGAAAATTAGCTTACAGGAGATGGCCCAAGTACGTAGAAAGTTTGAG
3844
3845 135_HRV41     TTTTTTACGTATGTTAGATTTGACTCAGAAATAACAATTG-TGCCAAGTATAGCTGGACA
3846 136_HRV41a    TTTTTTACGTATGTTAGATTTGACTCAGAAATAACAATTG-TGCCAAGTATAGCTGGACA
3847 137_HRV41b    TTTTTTACGTATGTTAGATTTGACTCAGAAATAACAATTG-TGCCAAGTATAGCTGGACA
3848 GROUP_43      TTTTTTACGTATGTTAGATTTGACTCAGAAATAACAATTG.TGCCAAGTATAGCTGGACA
3849
3850 135_HRV41     GGGTAGTGATGTCGGACATGTTGTCATGCAATACATGTTCGTACCACCTGGCGCACCCCT
3851 136_HRV41a    GGGTAGTGATGTCGGACATGTTGTCATGCAATACATGTTCGTACCACCTGGCGCACCCCT
3852 137_HRV41b    GGGTAGTGATGTCGGACATGTTGTCATGCAATACATGTTCGTACCACCTGGCGCACCCCT
3853 GROUP_43      GGGTAGTGATGTCGGACATGTTGTCATGCAATACATGTTCGTACCACCTGGCGCACCCCT
3854
3855 135_HRV41     CCCAGAAAAGAGAGATGATTACACATGGCAATCTGGCACCAATGCATCTGTATTCTGGCA
3856 136_HRV41a    CCCAGAAAAGAGAGATGATTACACATGGCAATCTGGCACCAATGCATCTGTATTCTGGCA
3857 137_HRV41b    CCCAGAAAAGAGAGATGATTACACATGGCAATCTGGCACCAATGCATCTGTATTCTGGCA
3858 GROUP_43      CCCAGAAAAGAGAGATGATTACACATGGCAATCTGGCACCAATGCATCTGTATTCTGGCA
3859
3860 135_HRV41     GTATGGTCAAGTTTACCCTAGGTTTTCTCTACCATTTCTTAGCATTGCTTCCGCATATTA
3861 136_HRV41a    GTATGGTCAAGTTTACCCTAGGTTTTCTCTACCATTTCTTAGCATTGCTTCCGCATATTA
3862 137_HRV41b    GTATGGTCAAGTTTACCCTAGGTTTTCTCTACCATTTCTTAGCATTGCTTCCGCATATTA
3863 GROUP_43      GTATGGTCAAGTTTACCCTAGGTTTTCTCTACCATTTCTTAGCATTGCTTCCGCATATTA
3864
3865 135_HRV41     CATGTTTTATGATGGTTATGAAGAAGGCTCTACAAATGCACGCTATGGAACAACAGTCAC
3866 136_HRV41a    CATGTTTTATGATGGTTATGAAGAAGGCTCTACAAATGCACGCTATGGAACAACAGTCAC
3867 137_HRV41b    CATGTTTTATGATGGTTATGAAGAAGGCTCTACAAATGCACGCTATGGAACAACAGTCAC
3868 GROUP_43      CATGTTTTATGATGGTTATGAAGAAGGCTCTACAAATGCACGCTATGGAACAACAGTCAC
3869
3870 135_HRV41     AAATGACATGGGTACATTATGCTTTAGAATAGTTACTGAAGAACACACCAACAAAGTTAA
3871 136_HRV41a    AAATGACATGGGTACATTATGCTTTAGAATAGTTACTGAAGAACACACCAACAAAGTTAA
3872 137_HRV41b    AAATGACATGGGTACATTATGCTTTAGAATAGTTACTGAAGAACACACCAACAAAGTTAA
3873 GROUP_43      AAATGACATGGGTACATTATGCTTTAGAATAGTTACTGAAGAACACACCAACAAAGTTAA
3874
3875 135_HRV41     GGTCACAACTAGAGTTTACCACAAAGCTAAACATGTTAAAGCATGGTGTCCTAGACCTCC
3876 136_HRV41a    GGTCACAACTAGAGTTTACCACAAAGCTAAACATGTTAAAGCATGGTGTCCTAGACCTCC
3877 137_HRV41b    GGTCACAACTAGAGTTTACCACAAAGCTAAACATGTTAAAGCATGGTGTCCTAGACCTCC
3878 GROUP_43      GGTCACAACTAGAGTTTACCACAAAGCTAAACATGTTAAAGCATGGTGTCCTAGACCTCC
3879
3880 135_HRV41     CAGGGCTGTGGAGTACACC-AATGTGCATGTCACAAATTACAAAC-CAAAAG---CAGGA
3881 136_HRV41a    CAGGGCTGTGGAGTACACC-AATGTGCATGTCACAAATTACAAAC-CAAAAG---CAGGA
3882 137_HRV41b    CAGGGCTGTGGAGTACACC-AATGTGCATGTCACAAATTACAAAC-CAAAAG---CAGGA
3883 GROUP_43      CAGGGCTGTGGAGTACACC.AATGTGCATGTCACAAATTACAAAC.CAAAAG...CAGGA
3884
3885 135_HRV41     GCAGA---GATTGTGGCTT---CTGTCAGACCTAGAGACAATGTTAGACAAGTAAGAA--
3886 136_HRV41a    GCAGA---GATTGTGGCTT---CTGTCAGACCTAGAGACAATGTTAGACAAGTAAGAA--
3887 137_HRV41b    GCAGA---GATTGTGGCTT---CTGTCAGACCTAGAGACAATGTTAGACAAGTAAGAA--
3888 GROUP_43      GCAGA...GATTGTGGCTT...CTGTCAGACCTAGAGACAATGTTAGACAAGTAAGAA..
3889
3890 135_HRV41     ----ATTAT-----------
3891 136_HRV41a    ----ATTAG-----------
3892 137_HRV41b    ----ATTAC-----------
```

FIG. D14 CONT'D

```
10.trace                                                                         9/20/2007 5:05 PM 3893 GROUP_43        ....ATTA-............
3894
3895
3896
3897 Group 44:
3898
3899 138_HRV73       AATCCTGTAGAAAGATATGTAGATGAAGTTTTGAATGAAGTCCTTGTAGTACCCAATATC
3900 139_HRV73b      AATCCTGTAGAAAGATATGTAGATGAAGTTTTGAATGAAGTCCTTGTAGTACCCAATATC
3901 140_HRV73a      AATCCTGTAGAAAGATATGTAGATGAAGTTTTGAATGAAGTCCTTGTAGTACCCAATATC
3902 GROUP_44        AATCCTGTAGAAAGATATGTAGATGAAGTTTTGAATGAAGTCCTTGTAGTACCCAATATC
3903
3904 138_HRV73       AATGAAAGTAATCCAACTACATCCAACTCAGCACCTGCACTGGACGCTGCAGAAACTGGC
3905 139_HRV73b      AATGAAAGTAATCCAACTACATCCAACTCAGCACCTGCACTGGACGCTGCAGAAACTGGC
3906 140_HRV73a      AATGAAAGTAATCCAACTACATCCAACTCAGCACCTGCACTGGACGCTGCAGAAACTGGC
3907 GROUP_44        AATGAAAGTAATCCAACTACATCCAACTCAGCACCTGCACTGGACGCTGCAGAAACTGGC
3908
3909 138_HRV73       CATACCAGTGGTGTACAACCAGAAGACATGATTGAGACCCGTTATGTCCAAACATCACAG
3910 139_HRV73b      CATACCAGTGGTGTACAACCAGAAGACATGATTGAGACCCGTTATGTCCAAACATCACAG
3911 140_HRV73a      CATACCAGTGGTGTACAACCAGAAGACATGATTGAGACCCGTTATGTCCAAACATCACAG
3912 GROUP_44        CATACCAGTGGTGTACAACCAGAAGACATGATTGAGACCCGTTATGTCCAAACATCACAG
3913
3914 138_HRV73       ACTAGAGATGAAATGAGCATTGAAAGCTTCCTTGGCAGGTCAGGTTGTATACACATGTCA
3915 139_HRV73b      ACTAGAGATGAAATGAGCATTGAAAGCTTCCTTGGCAGGTCAGGTTGTATACACATGTCA
3916 140_HRV73a      ACTAGAGATGAAATGAGCATTGAAAGCTTCCTTGGCAGGTCAGGTTGTATACACATGTCA
3917 GROUP_44        ACTAGAGATGAAATGAGCATTGAAAGCTTCCTTGGCAGGTCAGGTTGTATACACATGTCA
3918
3919 138_HRV73       ACTATGAATATAAATTATGAAAAT---------------TATGATGAT---GCTCCTGAA
3920 139_HRV73b      ACTATGAATATAAATTATGAAAAT---------------TATGATGAT---GCTCCTGAA
3921 140_HRV73a      ACTATGAATATAAATTATGAAAAT---------------TATGATGAT---GCTCCTGAA
3922 GROUP_44        ACTATGAATATAAATTATGAAAAT...............TATGATGAT...GCTCCTGAA
3923
3924 138_HRV73       AATTTTACCAAATGGAAAATAAGTTTACAAGAGATGGCTCAAATACGTAGGAAATTTGAA
3925 139_HRV73b      AATTTTACCAAATGGAAAATAAGTTTACAAGAGATGGCTCAAATACGTAGGAAATTTGAA
3926 140_HRV73a      AATTTTACCAAATGGAAAATAAGTTTACAAGAGATGGCTCAAATACGTAGGAAATTTGAA
3927 GROUP_44        AATTTTACCAAATGGAAAATAAGTTTACAAGAGATGGCTCAAATACGTAGGAAATTTGAA
3928
3929 138_HRV73       TTATTCACCTATGTAAGATTTGATTCAGAAGTGACAATTG-TACCATGTATAGCTGGTCA
3930 139_HRV73b      TTATTCACCTATGTAAGATTTGATTCAGAAGTGACAATTG-TACCATGTATAGCTGGTCA
3931 140_HRV73a      TTATTCACCTATGTAAGATTTGATTCAGAAGTGACAATTG-TACCATGTATAGCTGGTCA
3932 GROUP_44        TTATTCACCTATGTAAGATTTGATTCAGAAGTGACAATTG.TACCATGTATAGCTGGTCA
3933
3934 138_HRV73       AAGTGGAGATGTGGGACATGTAGTTATGCAGTATATGTATGTCCCACCTGGAGCCCCTCT
3935 139_HRV73b      AAGTGGAGATGTGGGACATGTAGTTATGCAGTATATGTATGTCCCACCTGGAGCCCCTCT
3936 140_HRV73a      AAGTGGAGATGTGGGACATGTAGTTATGCAGTATATGTATGTCCCACCTGGAGCCCCTCT
3937 GROUP_44        AAGTGGAGATGTGGGACATGTAGTTATGCAGTATATGTATGTCCCACCTGGAGCCCCTCT
3938
3939 138_HRV73       ACCCACAAAAAGAAATGACTACACATGGCAGTCCGGCACTAATGCATCAGTATTCTGGCA
3940 139_HRV73b      ACCCACAAAAAGAAATGACTACACATGGCAGTCCGGCACTAATGCATCAGTATTCTGGCA
3941 140_HRV73a      ACCCACAAAAAGAAATGACTACACATGGCAGTCCGGCACTAATGCATCAGTATTCTGGCA
3942 GROUP_44        ACCCACAAAAAGAAATGACTACACATGGCAGTCCGGCACTAATGCATCAGTATTCTGGCA
3943
3944 138_HRV73       ACATGGTCAAACTTACCCCAGATTCTCATTACCATTCCTTAGTATAGCATCCGCATATTA
3945 139_HRV73b      ACATGGTCAAACTTACCCCAGATTCTCATTACCATTCCTTAGTATAGCATCCGCATATTA
3946 140_HRV73a      ACATGGTCAAACTTACCCCAGATTCTCATTACCATTCCTTAGTATAGCATCCGCATATTA
3947 GROUP_44        ACATGGTCAAACTTACCCCAGATTCTCATTACCATTCCTTAGTATAGCATCCGCATATTA
3948
3949 138_HRV73       TATGTTTTATGATGGATATGATGGTGACTCCACACAATCACATTATGGCACCACAGTAGT
3950 139_HRV73b      TATGTTTTATGATGGATATGATGGTGACTCCACACAATCACATTATGGCACCACAGTAGT
3951 140_HRV73a      TATGTTTTATGATGGATATGATGGTGACTCCACACAATCACATTATGGCACCACAGTAGT
3952 GROUP_44        TATGTTTTATGATGGATATGATGGTGACTCCACACAATCACATTATGGCACCACAGTAGT
3953
3954 138_HRV73       TAATGACATGGGCACATTATGCTTTAGGATAGTGACTGAAGAACACACTAGCAGGGTAAA
3955 139_HRV73b      TAATGACATGGGCACATTATGCTTTAGGATAGTGACTGAAGAACACACTAGCAGGGTAAA
3956 140_HRV73a      TAATGACATGGGCACATTATGCTTTAGGATAGTGACTGAAGAACACACTAGCAGGGTAAA
3957 GROUP_44        TAATGACATGGGCACATTATGCTTTAGGATAGTGACTGAAGAACACACTAGCAGGGTAAA
```

FIG. D14 CONT'D

```
10.trace                                                        9/20/2007 5:05 PM 3958
3959 138_HRV73     GGTTACTACTAGAATCTATCATAAGGCTAAACATGTTAAAGCTTGGTGTCCAAGACCTCC
3960 139_HRV73b    GGTTACTACTAGAATCTATCATAAGGCTAAACATGTTAAAGCTTGGTGTCCAAGACCTCC
3961 140_HRV73a    GGTTACTACTAGAATCTATCATAAGGCTAAACATGTTAAAGCTTGGTGTCCAAGACCTCC
3962 GROUP_44      GGTTACTACTAGAATCTATCATAAGGCTAAACATGTTAAAGCTTGGTGTCCAAGACCTCC
3963
3964 138_HRV73     TAGGGCAGTAGAATATACA-AATGCACATGTGACCAATTATAAAC-CCACTG---ATGGA
3965 139_HRV73b    TAGGGCAGTAGAATATACA-AATGCACATGTGACCAATTATAAAC-CCACTG---ATGGA
3966 140_HRV73a    TAGGGCAGTAGAATATACA-AATGCACATGTGACCAATTATAAAC-CCACTG---ATGGA
3967 GROUP_44      TAGGGCAGTAGAATATACA.AATGCACATGTGACCAATTATAAAC.CCACTG...ATGGA
3968
3969 138_HRV73     GAAG------TTACTACTG---CCATTAGGCATAGAGATAATGTTAGAGCCATCCAAA--
3970 139_HRV73b    GAAG------TTACTACTG---CCATTAGGCATAGAGATAATGTTAGAGCCATCCAAA--
3971 140_HRV73a    GAAG------TTACTACTG---CCATTAGGCATAGAGATAATGTTAGAGCCATCCAAA--
3972 GROUP_44      GAAG......TTACTACTG...CCATTAGGCATAGAGATAATGTTAGAGCCATCCAAA..
3973
3974 138_HRV73     ----ATTTT------------
3975 139_HRV73b    ----ATTTG------------
3976 140_HRV73a    ----ATTTC------------
3977 GROUP_44      ....ATTT-............
3978
3979
3980
3981 Group  45:
3982
3983 141_HRV61     AACCCTGTGGAAAGATATGTAGATGAAGTTTTAAATGAAGTGCTTGTAGTCCCAAACATT
3984 142_HRV61a    AACCCTGTGGAAAGATATGTAGATGAAGTTTTAAATGAAGTGCTTGTAGTCCCAAACATT
3985 143_HRV61b    AACCCTGTGGAAAGATATGTAGATGAAGTTTTAAATGAAGTGCTTGTAGTCCCAAACATT
3986 GROUP_45      AACCCTGTGGAAAGATATGTAGATGAAGTTTTAAATGAAGTGCTTGTAGTCCCAAACATT
3987
3988 141_HRV61     AATCAGAGCAACCCTACAACATCCAACTCAGCACCAGTCTTAGACGCTGCTGAAACAGGT
3989 142_HRV61a    AATCAGAGCAACCCTACAACATCCAACTCAGCACCAGTCTTAGACGCTGCTGAAACAGGT
3990 143_HRV61b    AATCAGAGCAACCCTACAACATCCAACTCAGCACCAGTCTTAGACGCTGCTGAAACAGGT
3991 GROUP_45      AATCAGAGCAACCCTACAACATCCAACTCAGCACCAGTCTTAGACGCTGCTGAAACAGGT
3992
3993 141_HRV61     CATACCAGCAATGTTCAACCGGAGGACACGATTGAAACACGATATGTTCAAACCTCACAG
3994 142_HRV61a    CATACCAGCAATGTTCAACCGGAGGACACGATTGAAACACGATATGTTCAAACCTCACAG
3995 143_HRV61b    CATACCAGCAATGTTCAACCGGAGGACACGATTGAAACACGATATGTTCAAACCTCACAG
3996 GROUP_45      CATACCAGCAATGTTCAACCGGAGGACACGATTGAAACACGATATGTTCAAACCTCACAG
3997
3998 141_HRV61     ACAAGAGATGAAATGAGTGTAGAAAGTTTCTTGGGTAGATCAGGGTGCATACATATGTCA
3999 142_HRV61a    ACAAGAGATGAAATGAGTGTAGAAAGTTTCTTGGGTAGATCAGGGTGCATACATATGTCA
4000 143_HRV61b    ACAAGAGATGAAATGAGTGTAGAAAGTTTCTTGGGTAGATCAGGGTGCATACATATGTCA
4001 GROUP_45      ACAAGAGATGAAATGAGTGTAGAAAGTTTCTTGGGTAGATCAGGGTGCATACATATGTCA
4002
4003 141_HRV61     ACATTAAATATAAACTATGATAAC---------------TATGATGAT---TCTATTGAA
4004 142_HRV61a    ACATTAAATATAAACTATGATAAC---------------TATGATGAT---TCTATTGAA
4005 143_HRV61b    ACATTAAATATAAACTATGATAAC---------------TATGATGAT---TCTATTGAA
4006 GROUP_45      ACATTAAATATAAACTATGATAAC...............TATGATGAT...TCTATTGAA
4007
4008 141_HRV61     AACTTCAAGGTGTGGAAAATAAACCTGCAAGAGATGGCACAAATACGTAGAAAATTTGAG
4009 142_HRV61a    AACTTCAAGGTGTGGAAAATAAACCTGCAAGAGATGGCACAAATACGTAGAAAATTTGAG
4010 143_HRV61b    AACTTCAAGGTGTGGAAAATAAACCTGCAAGAGATGGCACAAATACGTAGAAAATTTGAG
4011 GROUP_45      AACTTCAAGGTGTGGAAAATAAACCTGCAAGAGATGGCACAAATACGTAGAAAATTTGAG
4012
4013 141_HRV61     TTGTTCACATATGCTAGATTTGATTCAGAGATTACAATTG-TACCTTGTGTTGCTGGGCA
4014 142_HRV61a    TTGTTCACATATGCTAGATTTGATTCAGAGATTACAATTG-TACCTTGTGTTGCTGGGCA
4015 143_HRV61b    TTGTTCACATATGCTAGATTTGATTCAGAGATTACAATTG-TACCTTGTGTTGCTGGGCA
4016 GROUP_45      TTGTTCACATATGCTAGATTTGATTCAGAGATTACAATTG.TACCTTGTGTTGCTGGGCA
4017
4018 141_HRV61     AGGTGGTGACATTGGACACGTGGTCATGCAATACATGTATGTTCCACCTGGTGCACCTAC
4019 142_HRV61a    AGGTGGTGACATTGGACACGTGGTCATGCAATACATGTATGTTCCACCTGGTGCACCTAC
4020 143_HRV61b    AGGTGGTGACATTGGACACGTGGTCATGCAATACATGTATGTTCCACCTGGTGCACCTAC
4021 GROUP_45      AGGTGGTGACATTGGACACGTGGTCATGCAATACATGTATGTTCCACCTGGTGCACCTAC
4022
```

FIG. D14 CONT'D 10.trace 9/20/2007 5:05 PM

```
4023 141_HRV61     ACCTGAGAAAAGAAATGATTTCACATGGCAATCAGGCACAAATGCATCTGTTTTCTGGCA
4024 142_HRV61a    ACCTGAGAAAAGAAATGATTTCACATGGCAATCAGGCACAAATGCATCTGTTTTCTGGCA
4025 143_HRV61b    ACCTGAGAAAAGAAATGATTTCACATGGCAATCAGGCACAAATGCATCTGTTTTCTGGCA
4026 GROUP_45      ACCTGAGAAAAGAAATGATTTCACATGGCAATCAGGCACAAATGCATCTGTTTTCTGGCA
4027
4028 141_HRV61     ACATGGTCAAGCTTATCCCAGATTTTCATTACCATTCCTAAGTATTGCATCTGCATATTA
4029 142_HRV61a    ACATGGTCAAGCTTATCCCAGATTTTCATTACCATTCCTAAGTATTGCATCTGCATATTA
4030 143_HRV61b    ACATGGTCAAGCTTATCCCAGATTTTCATTACCATTCCTAAGTATTGCATCTGCATATTA
4031 GROUP_45      ACATGGTCAAGCTTATCCCAGATTTTCATTACCATTCCTAAGTATTGCATCTGCATATTA
4032
4033 141_HRV61     TATGTTTTATGATGGTTATGATGGAGATTCTGAAATAACGCGCTATGGAACATCAGTGAC
4034 142_HRV61a    TATGTTTTATGATGGTTATGATGGAGATTCTGAAATAACGCGCTATGGAACATCAGTGAC
4035 143_HRV61b    TATGTTTTATGATGGTTATGATGGAGATTCTGAAATAACGCGCTATGGAACATCAGTGAC
4036 GROUP_45      TATGTTTTATGATGGTTATGATGGAGATTCTGAAATAACGCGCTATGGAACATCAGTGAC
4037
4038 141_HRV61     AAATGATATGGGTGCATTGTGCTTTAGAATAGTAACTGAACAGCATACAAATCAAGTTAA
4039 142_HRV61a    AAATGATATGGGTGCATTGTGCTTTAGAATAGTAACTGAACAGCATACAAATCAAGTTAA
4040 143_HRV61b    AAATGATATGGGTGCATTGTGCTTTAGAATAGTAACTGAACAGCATACAAATCAAGTTAA
4041 GROUP_45      AAATGATATGGGTGCATTGTGCTTTAGAATAGTAACTGAACAGCATACAAATCAAGTTAA
4042
4043 141_HRV61     AATCACAACTAGGATTTACCATAAAGCTAAACATGTTAAAGTCTGGTGTCCTAGACCCCC
4044 142_HRV61a    AATCACAACTAGGATTTACCATAAAGCTAAACATGTTAAAGTCTGGTGTCCTAGACCCCC
4045 143_HRV61b    AATCACAACTAGGATTTACCATAAAGCTAAACATGTTAAAGTCTGGTGTCCTAGACCCCC
4046 GROUP_45      AATCACAACTAGGATTTACCATAAAGCTAAACATGTTAAAGTCTGGTGTCCTAGACCCCC
4047
4048 141_HRV61     CAGAGCAGTGGAATATACT-AATGTGCATTTGACCAATTACAAGC-CCAAAG---ATAGT
4049 142_HRV61a    CAGAGCAGTGGAATATACT-AATGTGCATTTGACCAATTACAAGC-CCAAAG---ATAGT
4050 143_HRV61b    CAGAGCAGTGGAATATACT-AATGTGCATTTGACCAATTACAAGC-CCAAAG---ATAGT
4051 GROUP_45      CAGAGCAGTGGAATATACT.AATGTGCATTTGACCAATTACAAGC.CCAAAG...ATAGT
4052
4053 141_HRV61     GAAAAACAAGTTACCACTT---TCATCAAACCTAGAGCTAACTTAAGAGAGATTAGAA--
4054 142_HRV61a    GAAAAACAAGTTACCACTT---TCATCAAACCTAGAGCTAACTTAAGAGAGATTAGAA--
4055 143_HRV61b    GAAAAACAAGTTACCACTT---TCATCAAACCTAGAGCTAACTTAAGAGAGATTAGAA--
4056 GROUP_45      GAAAAACAAGTTACCACTT...TCATCAAACCTAGAGCTAACTTAAGAGAGATTAGAA..
4057
4058 141_HRV61     ----CATTT------------
4059 142_HRV61a    ----CATTT------------
4060 143_HRV61b    ----CATTT------------
4061 GROUP_45      ....CATTT............
4062
4063
4064
4065 Group  46:
4066
4067 144_HRV96     AACCCTGTAGAGAGATATGTAGATGAAGTCTTGAATGAGGTTCTTGTAGTCCCTAATATT
4068 145_HRV96b    AACCCTGTAGAGAGATATGTAGATGAAGTCTTGAATGAGGTTCTTGTAGTCCCTAATATT
4069 146_HRV96a    AACCCTGTAGAGAGATATGTAGATGAAGTCTTGAATGAGGTTCTTGTAGTCCCTAATATT
4070 GROUP_46      AACCCTGTAGAGAGATATGTAGATGAAGTCTTGAATGAGGTTCTTGTAGTCCCTAATATT
4071
4072 144_HRV96     AATGAAAGTTACCCAACAACTTCCAATTCAGCCCCAGTGCTAGATGCCGCTGAAACAGGT
4073 145_HRV96b    AATGAAAGTTACCCAACAACTTCCAATTCAGCCCCAGTGCTAGATGCCGCTGAAACAGGT
4074 146_HRV96a    AATGAAAGTTACCCAACAACTTCCAATTCAGCCCCAGTGCTAGATGCCGCTGAAACAGGT
4075 GROUP_46      AATGAAAGTTACCCAACAACTTCCAATTCAGCCCCAGTGCTAGATGCCGCTGAAACAGGT
4076
4077 144_HRV96     CATACTAGCAATGTCCAACCAGAGGATATGATTGAGACTCGATATGTTCAGACATCGCAG
4078 145_HRV96b    CATACTAGCAATGTCCAACCAGAGGATATGATTGAGACTCGATATGTTCAGACATCGCAG
4079 146_HRV96a    CATACTAGCAATGTCCAACCAGAGGATATGATTGAGACTCGATATGTTCAGACATCGCAG
4080 GROUP_46      CATACTAGCAATGTCCAACCAGAGGATATGATTGAGACTCGATATGTTCAGACATCGCAG
4081
4082 144_HRV96     ACGAGAGATGAAATGAGCATTGAGAGCTTTTTGGGTAGATCAGGGTGTATACACATGTCA
4083 145_HRV96b    ACGAGAGATGAAATGAGCATTGAGAGCTTTTTGGGTAGATCAGGGTGTATACACATGTCA
4084 146_HRV96a    ACGAGAGATGAAATGAGCATTGAGAGCTTTTTGGGTAGATCAGGGTGTATACACATGTCA
4085 GROUP_46      ACGAGAGATGAAATGAGCATTGAGAGCTTTTTGGGTAGATCAGGGTGTATACACATGTCA
4086
4087 144_HRV96     ACATTAAACATAGATTATGACAAT---------------TATGATGAC---TCCCCTAAG
```

FIG. D14 CONT'D

```
10.trace                                                                                    9/20/2007 5:05 PM 4088  145_HRV96b    ACATTAAACATAGATTATGACAAT---------------TATGATGAC---TCCCCTAAG
4089  146_HRV96a    ACATTAAACATAGATTATGACAAT---------------TATGATGAC---TCCCCTAAG
4090  GROUP_46      ACATTAAACATAGATTATGACAAT...............TATGATGAC...TCCCCTAAG
4091
4092  144_HRV96     AATTTTAAGGTGTGGAAAATAAATCTACAAGAAATGGCTCAAATTCGCAGGAAGTTTGAA
4093  145_HRV96b    AATTTTAAGGTGTGGAAAATAAATCTACAAGAAATGGCTCAAATTCGCAGGAAGTTTGAA
4094  146_HRV96a    AATTTTAAGGTGTGGAAAATAAATCTACAAGAAATGGCTCAAATTCGCAGGAAGTTTGAA
4095  GROUP_46      AATTTTAAGGTGTGGAAAATAAATCTACAAGAAATGGCTCAAATTCGCAGGAAGTTTGAA
4096
4097  144_HRV96     CTGTTCACTTATGCTAGATTTGATTCAGAGATAACAATTG-TTCCATGTGTTGCTGTGCA
4098  145_HRV96b    CTGTTCACTTATGCTAGATTTGATTCAGAGATAACAATTG-TTCCATGTGTTGCTGTGCA
4099  146_HRV96a    CTGTTCACTTATGCTAGATTTGATTCAGAGATAACAATTG-TTCCATGTGTTGCTGTGCA
4100  GROUP_46      CTGTTCACTTATGCTAGATTTGATTCAGAGATAACAATTG.TTCCATGTGTTGCTGTGCA
4101
4102  144_HRV96     GAGTGGTGATATTGGTCATGTGGTCATGCAATATATGTATGTTCCACCAGGTGCCCCCAC
4103  145_HRV96b    GAGTGGTGATATTGGTCATGTGGTCATGCAATATATGTATGTTCCACCAGGTGCCCCCAC
4104  146_HRV96a    GAGTGGTGATATTGGTCATGTGGTCATGCAATATATGTATGTTCCACCAGGTGCCCCCAC
4105  GROUP_46      GAGTGGTGATATTGGTCATGTGGTCATGCAATATATGTATGTTCCACCAGGTGCCCCCAC
4106
4107  144_HRV96     ACCTGAGAAGAGAGATGACTTTACATGGCAATCAGGCACAAATGCATCTGTGTTTTGGCA
4108  145_HRV96b    ACCTGAGAAGAGAGATGACTTTACATGGCAATCAGGCACAAATGCATCTGTGTTTTGGCA
4109  146_HRV96a    ACCTGAGAAGAGAGATGACTTTACATGGCAATCAGGCACAAATGCATCTGTGTTTTGGCA
4110  GROUP_46      ACCTGAGAAGAGAGATGACTTTACATGGCAATCAGGCACAAATGCATCTGTGTTTTGGCA
4111
4112  144_HRV96     GCACGGGCAAGCATATCCTAGATTTTCACTGCCTTTCCTTAGTATTGCCTCTGCATATTA
4113  145_HRV96b    GCACGGGCAAGCATATCCTAGATTTTCACTGCCTTTCCTTAGTATTGCCTCTGCATATTA
4114  146_HRV96a    GCACGGGCAAGCATATCCTAGATTTTCACTGCCTTTCCTTAGTATTGCCTCTGCATATTA
4115  GROUP_46      GCACGGGCAAGCATATCCTAGATTTTCACTGCCTTTCCTTAGTATTGCCTCTGCATATTA
4116
4117  144_HRV96     CATGTTTTATGATGGATATGATGGTGACTCTGAATCAACACGCTATGGAACATCTGTTAC
4118  145_HRV96b    CATGTTTTATGATGGATATGATGGTGACTCTGAATCAACACGCTATGGAACATCTGTTAC
4119  146_HRV96a    CATGTTTTATGATGGATATGATGGTGACTCTGAATCAACACGCTATGGAACATCTGTTAC
4120  GROUP_46      CATGTTTTATGATGGATATGATGGTGACTCTGAATCAACACGCTATGGAACATCTGTTAC
4121
4122  144_HRV96     CAATGACATGGGCACTTTATGTTTTAGAATAGTGACAGAGGAACACACCAACAAGGTCAA
4123  145_HRV96b    CAATGACATGGGCACTTTATGTTTTAGAATAGTGACAGAGGAACACACCAACAAGGTCAA
4124  146_HRV96a    CAATGACATGGGCACTTTATGTTTTAGAATAGTGACAGAGGAACACACCAACAAGGTCAA
4125  GROUP_46      CAATGACATGGGCACTTTATGTTTTAGAATAGTGACAGAGGAACACACCAACAAGGTCAA
4126
4127  144_HRV96     AATTACAACCAGAGTTTACCACAAAGCTAAACATGTTAAGGTGTGGTGCCCGAGACCCCC
4128  145_HRV96b    AATTACAACCAGAGTTTACCACAAAGCTAAACATGTTAAGGTGTGGTGCCCGAGACCCCC
4129  146_HRV96a    AATTACAACCAGAGTTTACCACAAAGCTAAACATGTTAAGGTGTGGTGCCCGAGACCCCC
4130  GROUP_46      AATTACAACCAGAGTTTACCACAAAGCTAAACATGTTAAGGTGTGGTGCCCGAGACCCCC
4131
4132  144_HRV96     TAGAGCAGTTGAATACACA-AATGTGCATCTCACAAATTATAAAC-CCAACA---ATG--
4133  145_HRV96b    TAGAGCAGTTGAATACACA-AATGTGCATCTCACAAATTATAAAC-CCAACA---ATG--
4134  146_HRV96a    TAGAGCAGTTGAATACACA-AATGTGCATCTCACAAATTATAAAC-CCAACA---ATG--
4135  GROUP_46      TAGAGCAGTTGAATACACA.AATGTGCATCTCACAAATTATAAAC.CCAACA...ATG..
4136
4137  144_HRV96     -------AGGTTACCACTT---TTATCAAACCTAGAGAAAATCTAAGGGATATTAGAA--
4138  145_HRV96b    -------AGGTTACCACTT---TTATCAAACCTAGAGAAAATCTAAGGGATATTAGAA--
4139  146_HRV96a    -------AGGTTACCACTT---TTATCAAACCTAGAGAAAATCTAAGGGATATTAGAA--
4140  GROUP_46      .......AGGTTACCACTT...TTATCAAACCTAGAGAAAATCTAAGGGATATTAGAA..
4141
4142  144_HRV96     ----ATTTT------------
4143  145_HRV96b    ----ATTTA------------
4144  146_HRV96a    ----ATTTC------------
4145  GROUP_46      ....ATTT-............
4146
4147
4148
4149  Group_47:
4150
4151  90_HRV16a|    AATCCAGTGGAAAGATATGTAGATGAAGTCTTAAATGAAGTGTTAGTAGTGCCCAATATT
4152  91_HRV16b|    AATCCAGTGGAAAGATATGTAGATGAAGTCTTAAATGAAGTGTTAGTAGTGCCCAATATT
```

FIG. D14 CONT'D

10.trace                                                                                            9/20/2007 5:05 PM

```
4153 92_1AYM_A      AATCCAGTGGAAAGATATGTAGATGAAGTCTTAAATGAAGTGTTAGTAGTGCCCAATATT
4154 GROUP_47      AATCCAGTGGAAAGATATGTAGATGAAGTCTTAAATGAAGTGTTAGTAGTGCCCAATATT
4155
4156 90_HRV16a|    AATGAGAGCCACCCTACCACATCAAATGCGGCCCCAGTTTTGGATGCTGCTGAAACAGGA
4157 91_HRV16b|    AATGAGAGCCACCCTACCACATCAAATGCGGCCCCAGTTTTGGATGCTGCTGAAACAGGA
4158 92_1AYM_A     AATGAGAGCCACCCTACCACATCAAATGCGGCCCCAGTTTTGGATGCTGCTGAAACAGGA
4159 GROUP_47      AATGAGAGCCACCCTACCACATCAAATGCGGCCCCAGTTTTGGATGCTGCTGAAACAGGA
4160
4161 90_HRV16a|    CATACCAATAAGATACAGCCAGAAGACACTATAGAAACCAGATATGTGCAATCTTCACAG
4162 91_HRV16b|    CATACCAATAAGATACAGCCAGAAGACACTATAGAAACCAGATATGTGCAATCTTCACAG
4163 92_1AYM_A     CATACCAATAAGATACAGCCAGAAGACACTATAGAAACCAGATATGTGCAATCTTCACAG
4164 GROUP_47      CATACCAATAAGATACAGCCAGAAGACACTATAGAAACCAGATATGTGCAATCTTCACAG
4165
4166 90_HRV16a|    ACATTGGATGAAATGAGTGTGGAAAGCTTCCTAGGCAGATCGGGGTGCATCCATGAATCA
4167 91_HRV16b|    ACATTGGATGAAATGAGTGTGGAAAGCTTCCTAGGCAGATCGGGGTGCATCCATGAATCA
4168 92_1AYM_A     ACATTGGATGAAATGAGTGTGGAAAGCTTCCTAGGCAGATCGGGGTGCATCCATGAATCA
4169 GROUP_47      ACATTGGATGAAATGAGTGTGGAAAGCTTCCTAGGCAGATCGGGGTGCATCCATGAATCA
4170
4171 90_HRV16a|    GTGTTGGATATTGTGGACAATTAC---------------AATGAT------------CAA
4172 91_HRV16b|    GTGTTGGATATTGTGGACAATTAC---------------AATGAT------------CAA
4173 92_1AYM_A     GTGTTGGATATTGTGGACAATTAC---------------AATGAT------------CAA
4174 GROUP_47      GTGTTGGATATTGTGGACAATTAC...............AATGAT............CAA
4175
4176 90_HRV16a|    AGTTTCACTAAATGGAAGATAAACCTGCAAGAAATGGCACAAATTAGAAGAAAATTTGAA
4177 91_HRV16b|    AGTTTCACTAAATGGAAGATAAACCTGCAAGAAATGGCACAAATTAGAAGAAAATTTGAA
4178 92_1AYM_A     AGTTTCACTAAATGGAAGATAAACCTGCAAGAAATGGCACAAATTAGAAGAAAATTTGAA
4179 GROUP_47      AGTTTCACTAAATGGAAGATAAACCTGCAAGAAATGGCACAAATTAGAAGAAAATTTGAA
4180
4181 90_HRV16a|    ATGTTTACTTATGCAAGATTTGACTCTGAAATTACTATGG-TACCAAGTGTAGCAGCCAA
4182 91_HRV16b|    ATGTTTACTTATGCAAGATTTGACTCTGAAATTACTATGG-TACCAAGTGTAGCAGCCAA
4183 92_1AYM_A     ATGTTTACTTATGCAAGATTTGACTCTGAAATTACTATGG-TACCAAGTGTAGCAGCCAA
4184 GROUP_47      ATGTTTACTTATGCAAGATTTGACTCTGAAATTACTATGG.TACCAAGTGTAGCAGCCAA
4185
4186 90_HRV16a|    AGATGGTCACATTGGTCATATAGTCATGCAATATATGTATGTACCACCAGGAGCACCTAT
4187 91_HRV16b|    AGATGGTCACATTGGTCATATAGTCATGCAATATATGTATGTACCACCAGGAGCACCTAT
4188 92_1AYM_A     AGATGGTCACATTGGTCATATAGTCATGCAATATATGTATGTACCACCAGGAGCACCTAT
4189 GROUP_47      AGATGGTCACATTGGTCATATAGTCATGCAATATATGTATGTACCACCAGGAGCACCTAT
4190
4191 90_HRV16a|    ACCAACAACTAGAAATGACTATGCTTGGCAATCTGGAACAAATGCATCTGTATTTTGGCA
4192 91_HRV16b|    ACCAACAACTAGAAATGACTATGCTTGGCAATCTGGAACAAATGCATCTGTATTTTGGCA
4193 92_1AYM_A     ACCAACAACTAGAAATGACTATGCTTGGCAATCTGGAACAAATGCATCTGTATTTTGGCA
4194 GROUP_47      ACCAACAACTAGAAATGACTATGCTTGGCAATCTGGAACAAATGCATCTGTATTTTGGCA
4195
4196 90_HRV16a|    GCATGGGCAACCTTTCCCTCGCTTTTCACTTCCCTTTTTGAGTATTGCATCAGCATATTA
4197 91_HRV16b|    GCATGGGCAACCTTTCCCTCGCTTTTCACTTCCCTTTTTGAGTATTGCATCAGCATATTA
4198 92_1AYM_A     GCATGGGCAACCTTTCCCTCGCTTTTCACTTCCCTTTTTGAGTATTGCATCAGCATATTA
4199 GROUP_47      GCATGGGCAACCTTTCCCTCGCTTTTCACTTCCCTTTTTGAGTATTGCATCAGCATATTA
4200
4201 90_HRV16a|    CATGTTTTATGATGGTTATGATGGAGACACATATAAATCCAGATATGGAACTGTAGTCAC
4202 91_HRV16b|    CATGTTTTATGATGGTTATGATGGAGACACATATAAATCCAGATATGGAACTGTAGTCAC
4203 92_1AYM_A     CATGTTTTATGATGGTTATGATGGAGACACATATAAATCCAGATATGGAACTGTAGTCAC
4204 GROUP_47      CATGTTTTATGATGGTTATGATGGAGACACATATAAATCCAGATATGGAACTGTAGTCAC
4205
4206 90_HRV16a|    CAATGACATGGGAACTTTGTGTTCGCGTATTGTGACCAGTGAGCAATTACACAAAGTCAA
4207 91_HRV16b|    CAATGACATGGGAACTTTGTGTTCGCGTATTGTGACCAGTGAGCAATTACACAAAGTCAA
4208 92_1AYM_A     CAATGACATGGGAACTTTGTGTTCGCGTATTGTGACCAGTGAGCAATTACACAAAGTCAA
4209 GROUP_47      CAATGACATGGGAACTTTGTGTTCGCGTATTGTGACCAGTGAGCAATTACACAAAGTCAA
4210
4211 90_HRV16a|    AGTGGTAACAAGGATATATCACAAAGCCAAACACACCAAAGCTTGGTGCCCAAGACCACC
4212 91_HRV16b|    AGTGGTAACAAGGATATATCACAAAGCCAAACACACCAAAGCTTGGTGCCCAAGACCACC
4213 92_1AYM_A     AGTGGTAACAAGGATATATCACAAAGCCAAACACACCAAAGCTTGGTGCCCAAGACCACC
4214 GROUP_47      AGTGGTAACAAGGATATATCACAAAGCCAAACACACCAAAGCTTGGTGCCCAAGACCACC
4215
4216 90_HRV16a|    CAGAGCTGTTCAATACTCA-CATACACATACCACCAACTACAAAT-TGAGTT---CAGAA
4217 91_HRV16b|    CAGAGCTGTTCAATACTCA-CATACACATACCACCAACTACAAAT-TGAGTT---CAGAA
```

FIG. D14 CONT'D

```
10.trace                                                                       9/20/2007 5:05 PM 4218  92_1AYM_A    CAGAGCTGTTCAATACTCA-CATACACATACCACCAACTACAAAT-TGAGTT---CAGAA
4219  GROUP_47     CAGAGCTGTTCAATACTCA.CATACACATACCACCAACTACAAAT.TGAGTT...CAGAA
4220
4221  90_HRV16a|   GTAC------ACAATGATGTGGCTATAAGACCTAGAACAAATCTAACAACTGTA------
4222  91_HRV16b|   GTAC------ACAATGATGTGGCTATAAGACCTAGAACAAATCTAACAACTGTC------
4223  92_1AYM_A    GTAC------ACAATGATGTGGCTATAAGACCTAGAACAAATCTAACAACTGTT------
4224  GROUP_47     GTAC......ACAATGATGTGGCTATAAGACCTAGAACAAATCTAACAACTGT-......
4225
4226  90_HRV16a|   --------------------
4227  91_HRV16b|   --------------------
4228  92_1AYM_A    --------------------
4229  GROUP_47     ....................
4230
4231
4232
4233  Group 48:
4234
4235  93_HRV81a|   AACCCAGTGGAGCGGTATGTGGATGAAGTCTTAAATGAGGTATTGGTAGTCCCTAATATT
4236  94_HRV81b|   AACCCAGTGGAGCGGTATGTGGATGAAGTCTTAAATGAGGTATTGGTAGTCCCTAATATT
4237  95_HRV81     AACCCAGTGGAGCGGTATGTGGATGAAGTCTTAAATGAGGTATTGGTAGTCCCTAATATT
4238  GROUP_48     AACCCAGTGGAGCGGTATGTGGATGAAGTCTTAAATGAGGTATTGGTAGTCCCTAATATT
4239
4240  93_HRV81a|   AATGAAAGCCACCCTACAACATCTAATTCAGCTCCTGTTTTAGATGCAGCTGAAACTGGA
4241  94_HRV81b|   AATGAAAGCCACCCTACAACATCTAATTCAGCTCCTGTTTTAGATGCAGCTGAAACTGGA
4242  95_HRV81     AATGAAAGCCACCCTACAACATCTAATTCAGCTCCTGTTTTAGATGCAGCTGAAACTGGA
4243  GROUP_48     AATGAAAGCCACCCTACAACATCTAATTCAGCTCCTGTTTTAGATGCAGCTGAAACTGGA
4244
4245  93_HRV81a|   CACACCAGTAATATACAACCTGAGGATACTATTGAGACCAGATATGTACAATCTTCACAG
4246  94_HRV81b|   CACACCAGTAATATACAACCTGAGGATACTATTGAGACCAGATATGTACAATCTTCACAG
4247  95_HRV81     CACACCAGTAATATACAACCTGAGGATACTATTGAGACCAGATATGTACAATCTTCACAG
4248  GROUP_48     CACACCAGTAATATACAACCTGAGGATACTATTGAGACCAGATATGTACAATCTTCACAG
4249
4250  93_HRV81a|   ACACTGGATGAAATGAGTGTAGAAAGTTTTTTAGGCAGATCAGGTTGCATTCATGAATCC
4251  94_HRV81b|   ACACTGGATGAAATGAGTGTAGAAAGTTTTTTAGGCAGATCAGGTTGCATTCATGAATCC
4252  95_HRV81     ACACTGGATGAAATGAGTGTAGAAAGTTTTTTAGGCAGATCAGGTTGCATTCATGAATCC
4253  GROUP_48     ACACTGGATGAAATGAGTGTAGAAAGTTTTTTAGGCAGATCAGGTTGCATTCATGAATCC
4254
4255  93_HRV81a|   ATATTGGACATTAAAGAGGATTAC---------------AATACC------------CAG
4256  94_HRV81b|   ATATTGGACATTAAAGAGGATTAC---------------AATACC------------CAG
4257  95_HRV81     ATATTGGACATTAAAGAGGATTAC---------------AATACC------------CAG
4258  GROUP_48     ATATTGGACATTAAAGAGGATTAC...............AATACC............CAG
4259
4260  93_HRV81a|   AGCTTTACTAAATGGAAAATTAACTTACAAGAGATGGCACAGATTAGGAGAAAGTTTGAA
4261  94_HRV81b|   AGCTTTACTAAATGGAAAATTAACTTACAAGAGATGGCACAGATTAGGAGAAAGTTTGAA
4262  95_HRV81     AGCTTTACTAAATGGAAAATTAACTTACAAGAGATGGCACAGATTAGGAGAAAGTTTGAA
4263  GROUP_48     AGCTTTACTAAATGGAAAATTAACTTACAAGAGATGGCACAGATTAGGAGAAAGTTTGAA
4264
4265  93_HRV81a|   ATGTTCACATACACTAGATTTAACTCTGAGATTACACTGG-TACCAAGTATTGCAAACAA
4266  94_HRV81b|   ATGTTCACATACACTAGATTTAACTCTGAGATTACACTGG-TACCAAGTATTGCAAACAA
4267  95_HRV81     ATGTTCACATACACTAGATTTAACTCTGAGATTACACTGG-TACCAAGTATTGCAAACAA
4268  GROUP_48     ATGTTCACATACACTAGATTTAACTCTGAGATTACACTGG.TACCAAGTATTGCAAACAA
4269
4270  93_HRV81a|   GGAAGGTCATATTGGTCATATAGTAATGCAATACATGTATGTACCACCAGGAGCACCCAT
4271  94_HRV81b|   GGAAGGTCATATTGGTCATATAGTAATGCAATACATGTATGTACCACCAGGAGCACCCAT
4272  95_HRV81     GGAAGGTCATATTGGTCATATAGTAATGCAATACATGTATGTACCACCAGGAGCACCCAT
4273  GROUP_48     GGAAGGTCATATTGGTCATATAGTAATGCAATACATGTATGTACCACCAGGAGCACCCAT
4274
4275  93_HRV81a|   TCCAACAACTAGAGAAGACTATGCTTGGCAATCTGGAACAAATGCATCTATATTCTGGCA
4276  94_HRV81b|   TCCAACAACTAGAGAAGACTATGCTTGGCAATCTGGAACAAATGCATCTATATTCTGGCA
4277  95_HRV81     TCCAACAACTAGAGAAGACTATGCTTGGCAATCTGGAACAAATGCATCTATATTCTGGCA
4278  GROUP_48     TCCAACAACTAGAGAAGACTATGCTTGGCAATCTGGAACAAATGCATCTATATTCTGGCA
4279
4280  93_HRV81a|   ACATGGGCAACCCTTTCCCCGGTTTTCACTCCCTTTTCTAAGTGTAGCATCAGCATATTA
4281  94_HRV81b|   ACATGGGCAACCCTTTCCCCGGTTTTCACTCCCTTTTCTAAGTGTAGCATCAGCATATTA
4282  95_HRV81     ACATGGGCAACCCTTTCCCCGGTTTTCACTCCCTTTTCTAAGTGTAGCATCAGCATATTA
```

FIG. D14 CONT'D

```
10.trace                                                                  9/20/2007 5:05 PM 4283 GROUP_48      ACATGGGCAACCCTTTCCCCGGTTTTCACTCCCTTTTCTAAGTGTAGCATCAGCATATTA
4284
4285 93_HRV81a|    CATGTTCTATGATGGATATGATGGTGATACTTATCACTCCAGATACGGGACTGTAGTCAC
4286 94_HRV81b|    CATGTTCTATGATGGATATGATGGTGATACTTATCACTCCAGATACGGGACTGTAGTCAC
4287 95_HRV81      CATGTTCTATGATGGATATGATGGTGATACTTATCACTCCAGATACGGGACTGTAGTCAC
4288 GROUP_48      CATGTTCTATGATGGATATGATGGTGATACTTATCACTCCAGATACGGGACTGTAGTCAC
4289
4290 93_HRV81a|    TAATGATATGGGAACATTATGCTCACGGATAGTGACAAGTGAGCAAGTGCACAAGGTGAA
4291 94_HRV81b|    TAATGATATGGGAACATTATGCTCACGGATAGTGACAAGTGAGCAAGTGCACAAGGTGAA
4292 95_HRV81      TAATGATATGGGAACATTATGCTCACGGATAGTGACAAGTGAGCAAGTGCACAAGGTGAA
4293 GROUP_48      TAATGATATGGGAACATTATGCTCACGGATAGTGACAAGTGAGCAAGTGCACAAGGTGAA
4294
4295 93_HRV81a|    AATAGTAACAAGAATATATCACAAAGCTAAGCACACCAAAGCTTGGTGTCCAAGACCACC
4296 94_HRV81b|    AATAGTAACAAGAATATATCACAAAGCTAAGCACACCAAAGCTTGGTGTCCAAGACCACC
4297 95_HRV81      AATAGTAACAAGAATATATCACAAAGCTAAGCACACCAAAGCTTGGTGTCCAAGACCACC
4298 GROUP_48      AATAGTAACAAGAATATATCACAAAGCTAAGCACACCAAAGCTTGGTGTCCAAGACCACC
4299
4300 93_HRV81a|    CAGGGCTGTTCAGTACACA-CATACACATGTAACTAATTATAAAT-TAGAAA---CAGAT
4301 94_HRV81b|    CAGGGCTGTTCAGTACACA-CATACACATGTAACTAATTATAAAT-TAGAAA---CAGAT
4302 95_HRV81      CAGGGCTGTTCAGTACACA-CATACACATGTAACTAATTATAAAT-TAGAAA---CAGAT
4303 GROUP_48      CAGGGCTGTTCAGTACACA.CATACACATGTAACTAATTATAAAT.TAGAAA...CAGAT
4304
4305 93_HRV81a|    GTCC------ACACTAGTGTAGCCATAAAACCTAGAACAAGTCTAACAAATGTG------
4306 94_HRV81b|    GTCC------ACACTAGTGTAGCCATAAAACCTAGAACAAGTCTAACAAATGTC------
4307 95_HRV81      GTCC------ACACTAGTGTAGCCATAAAACCTAGAACAAGTCTAACAAATGTT------
4308 GROUP_48      GTCC......ACACTAGTGTAGCCATAAAACCTAGAACAAGTCTAACAAATGT-......
4309
4310 93_HRV81a|    --------------------
4311 94_HRV81b|    --------------------
4312 95_HRV81      --------------------
4313 GROUP_48      ....................
4314
4315
4316
4317 Group 49:
4318
4319 147_HRV2      AACCCTGTTGAGAATTATATAGATGAAGTTCTTAATGAAGTTTTAGTTGTCCCAAATATT
4320 148_HRV2a|    AACCCTGTTGAGAATTATATAGATGAAGTTCTTAATGAAGTTTTAGTTGTCCCAAATATT
4321 149_HRV2b|    AACCCTGTTGAGAATTATATAGATGAAGTTCTTAATGAAGTTTTAGTTGTCCCAAATATT
4322 GROUP_49      AACCCTGTTGAGAATTATATAGATGAAGTTCTTAATGAAGTTTTAGTTGTCCCAAATATT
4323
4324 147_HRV2      AATAGTAGTAACCCCACAACATCAAATTCTGCCCCAGCATTAGATGCTGCAGAAACAGGG
4325 148_HRV2a|    AATAGTAGTAACCCCACAACATCAAATTCTGCCCCAGCATTAGATGCTGCAGAAACAGGG
4326 149_HRV2b|    AATAGTAGTAACCCCACAACATCAAATTCTGCCCCAGCATTAGATGCTGCAGAAACAGGG
4327 GROUP_49      AATAGTAGTAACCCCACAACATCAAATTCTGCCCCAGCATTAGATGCTGCAGAAACAGGG
4328
4329 147_HRV2      CACACTAGTAGTGTTCAACCAGAGGATGTCATTGAAACTAGGTATGTGCAGACATCACAA
4330 148_HRV2a|    CACACTAGTAGTGTTCAACCAGAGGATGTCATTGAAACTAGGTATGTGCAGACATCACAA
4331 149_HRV2b|    CACACTAGTAGTGTTCAACCAGAGGATGTCATTGAAACTAGGTATGTGCAGACATCACAA
4332 GROUP_49      CACACTAGTAGTGTTCAACCAGAGGATGTCATTGAAACTAGGTATGTGCAGACATCACAA
4333
4334 147_HRV2      ACAAGAGATGAAATGAGTTTAGAGAGTTTTCTTGGCAGATCAGGATGCATACATGAATCT
4335 148_HRV2a|    ACAAGAGATGAAATGAGTTTAGAGAGTTTTCTTGGCAGATCAGGATGCATACATGAATCT
4336 149_HRV2b|    ACAAGAGATGAAATGAGTTTAGAGAGTTTTCTTGGCAGATCAGGATGCATACATGAATCT
4337 GROUP_49      ACAAGAGATGAAATGAGTTTAGAGAGTTTTCTTGGCAGATCAGGATGCATACATGAATCT
4338
4339 147_HRV2      AAATTAGAGGTTACACTTGCAAAT---------------TATAACA---------AGGAG
4340 148_HRV2a|    AAATTAGAGGTTACACTTGCAAAT---------------TATAACA---------AGGAG
4341 149_HRV2b|    AAATTAGAGGTTACACTTGCAAAT---------------TATAACA---------AGGAG
4342 GROUP_49      AAATTAGAGGTTACACTTGCAAAT...............TATAACA.........AGGAG
4343
4344 147_HRV2      AATTTTACAGTGTGGGCTATTAATATACAAGAAATGGCTCAAATTAGAAGGAAATTTGAA
4345 148_HRV2a|    AATTTTACAGTGTGGGCTATTAATATACAAGAAATGGCTCAAATTAGAAGGAAATTTGAA
4346 149_HRV2b|    AATTTTACAGTGTGGGCTATTAATATACAAGAAATGGCTCAAATTAGAAGGAAATTTGAA
4347 GROUP_49      AATTTTACAGTGTGGGCTATTAATATACAAGAAATGGCTCAAATTAGAAGGAAATTTGAA
```

FIG. D14 CONT'D

10.trace                                                                9/20/2007 5:05 PM

```
4348
4349 147_HRV2      TTGTTCACCTATACTAGGTTTGATTCTGAAATAACCCTAG-TTCCATGCATTTCCGCCCT
4350 148_HRV2a|    TTGTTCACCTATACTAGGTTTGATTCTGAAATAACCCTAG-TTCCATGCATTTCCGCCCT
4351 149_HRV2b|    TTGTTCACCTATACTAGGTTTGATTCTGAAATAACCCTAG-TTCCATGCATTTCCGCCCT
4352 GROUP_49      TTGTTCACCTATACTAGGTTTGATTCTGAAATAACCCTAG.TTCCATGCATTTCCGCCCT
4353
4354 147_HRV2      TAGTCAGGACATTGGACACATCACAATGCAATACATGTATGTTCCACCTGGTGCACCGGT
4355 148_HRV2a|    TAGTCAGGACATTGGACACATCACAATGCAATACATGTATGTTCCACCTGGTGCACCGGT
4356 149_HRV2b|    TAGTCAGGACATTGGACACATCACAATGCAATACATGTATGTTCCACCTGGTGCACCGGT
4357 GROUP_49      TAGTCAGGACATTGGACACATCACAATGCAATACATGTATGTTCCACCTGGTGCACCGGT
4358
4359 147_HRV2      GCCCAATAGTAGGGACGATTATGCATGGCAGTCTGGCACTAATGCCTCTGTTTTCTGGCA
4360 148_HRV2a|    GCCCAATAGTAGGGACGATTATGCATGGCAGTCTGGCACTAATGCCTCTGTTTTCTGGCA
4361 149_HRV2b|    GCCCAATAGTAGGGACGATTATGCATGGCAGTCTGGCACTAATGCCTCTGTTTTCTGGCA
4362 GROUP_49      GCCCAATAGTAGGGACGATTATGCATGGCAGTCTGGCACTAATGCCTCTGTTTTCTGGCA
4363
4364 147_HRV2      ACATGGACAGGCTTATCCAAGATTTTCCTTACCTTTCCTAAGTGTGGCATCTGCTTATTA
4365 148_HRV2a|    ACATGGACAGGCTTATCCAAGATTTTCCTTACCTTTCCTAAGTGTGGCATCTGCTTATTA
4366 149_HRV2b|    ACATGGACAGGCTTATCCAAGATTTTCCTTACCTTTCCTAAGTGTGGCATCTGCTTATTA
4367 GROUP_49      ACATGGACAGGCTTATCCAAGATTTTCCTTACCTTTCCTAAGTGTGGCATCTGCTTATTA
4368
4369 147_HRV2      CATGTTTTATGATGGGTATGATG------AACAAGATCAAAACTATGGTACAGCAAGCAC
4370 148_HRV2a|    CATGTTTTATGATGGGTATGATG------AACAAGATCAAAACTATGGTACAGCAAGCAC
4371 149_HRV2b|    CATGTTTTATGATGGGTATGATG------AACAAGATCAAAACTATGGTACAGCAAGCAC
4372 GROUP_49      CATGTTTTATGATGGGTATGATG......AACAAGATCAAAACTATGGTACAGCAAGCAC
4373
4374 147_HRV2      AAATAACATGGGGTCACTATGCTCTAGGATAGTAACAGAGAAACACATTCATAAGGTACA
4375 148_HRV2a|    AAATAACATGGGGTCACTATGCTCTAGGATAGTAACAGAGAAACACATTCATAAGGTACA
4376 149_HRV2b|    AAATAACATGGGGTCACTATGCTCTAGGATAGTAACAGAGAAACACATTCATAAGGTACA
4377 GROUP_49      AAATAACATGGGGTCACTATGCTCTAGGATAGTAACAGAGAAACACATTCATAAGGTACA
4378
4379 147_HRV2      TATAATGACAAGAATCTATCACAAGGCTAAACATGTCAAGGCATGGTGTCCACGCCCACC
4380 148_HRV2a|    TATAATGACAAGAATCTATCACAAGGCTAAACATGTCAAGGCATGGTGTCCACGCCCACC
4381 149_HRV2b|    TATAATGACAAGAATCTATCACAAGGCTAAACATGTCAAGGCATGGTGTCCACGCCCACC
4382 GROUP_49      TATAATGACAAGAATCTATCACAAGGCTAAACATGTCAAGGCATGGTGTCCACGCCCACC
4383
4384 147_HRV2      CAGAGCGCTTGAGTATACT-CGTGCTCACCGCACTAATTTTAAAA-TTGAGG---ATAGG
4385 148_HRV2a|    CAGAGCGCTTGAGTATACT-CGTGCTCACCGCACTAATTTTAAAA-TTGAGG---ATAGG
4386 149_HRV2b|    CAGAGCGCTTGAGTATACT-CGTGCTCACCGCACTAATTTTAAAA-TTGAGG---ATAGG
4387 GROUP_49      CAGAGCGCTTGAGTATACT.CGTGCTCACCGCACTAATTTTAAAA.TTGAGG...ATAGG
4388
4389 147_HRV2      AGTA------TTCAGACAG---CAATTGTGACCAGACCAATTATCACTACAGCT------
4390 148_HRV2a|    AGTA------TTCAGACAG---CAATTGTGACCAGACCAATTATCACTACAGCA------
4391 149_HRV2b|    AGTA------TTCAGACAG---CAATTGTGACCAGACCAATTATCACTACAGCG------
4392 GROUP_49      AGTA......TTCAGACAG...CAATTGTGACCAGACCAATTATCACTACAGC-......
4393
4394 147_HRV2      --------------------
4395 148_HRV2a|    --------------------
4396 149_HRV2b|    --------------------
4397 GROUP_49      ....................
4398
4399
4400
4401 Group 50:
4402
4403 150_HRV49a     AATCCTGTTGAACACTACATAGATGAGGTCCTTAATGAGGTTTTAGTTGTTCCAAATATT
4404 151_HRV49b     AATCCTGTTGAACACTACATAGATGAGGTCCTTAATGAGGTTTTAGTTGTTCCAAATATT
4405 152_HRV49      AATCCTGTTGAACACTACATAGATGAGGTCCTTAATGAGGTTTTAGTTGTTCCAAATATT
4406 GROUP_50       AATCCTGTTGAACACTACATAGATGAGGTCCTTAATGAGGTTTTAGTTGTTCCAAATATT
4407
4408 150_HRV49a     AATAGTAGTCACCCCACGACATCAAACTCTGCTCCAGCATTAGATGCTGCAGAAACAGGG
4409 151_HRV49b     AATAGTAGTCACCCCACGACATCAAACTCTGCTCCAGCATTAGATGCTGCAGAAACAGGG
4410 152_HRV49      AATAGTAGTCACCCCACGACATCAAACTCTGCTCCAGCATTAGATGCTGCAGAAACAGGG
```

FIG. D14 CONT'D

```
10.trace                                                         9/20/2007 5:05 PM 4411 GROUP_50      AATAGTAGTCACCCCACGACATCAAACTCTGCTCCAGCATTAGATGCTGCAGAAACAGGG
4412
4413 150_HRV49a    CACACTAGCAATGTGCAACCTGAAGATGTCATTGAAACCAGATATGTACAGACATCACAA
4414 151_HRV49b    CACACTAGCAATGTGCAACCTGAAGATGTCATTGAAACCAGATATGTACAGACATCACAA
4415 152_HRV49     CACACTAGCAATGTGCAACCTGAAGATGTCATTGAAACCAGATATGTACAGACATCACAA
4416 GROUP_50      CACACTAGCAATGTGCAACCTGAAGATGTCATTGAAACCAGATATGTACAGACATCACAA
4417
4418 150_HRV49a    ACAAGAGATGAAATGAGTTTAGAGAGTTTTCTTGGTAGGTCAGGGTGTATACATGAATCC
4419 151_HRV49b    ACAAGAGATGAAATGAGTTTAGAGAGTTTTCTTGGTAGGTCAGGGTGTATACATGAATCC
4420 152_HRV49     ACAAGAGATGAAATGAGTTTAGAGAGTTTTCTTGGTAGGTCAGGGTGTATACATGAATCC
4421 GROUP_50      ACAAGAGATGAAATGAGTTTAGAGAGTTTTCTTGGTAGGTCAGGGTGTATACATGAATCC
4422
4423 150_HRV49a    AAACTAGAGGTCACACTTACAAAT---------------TACAATG---------AAAAT
4424 151_HRV49b    AAACTAGAGGTCACACTTACAAAT---------------TACAATG---------AAAAT
4425 152_HRV49     AAACTAGAGGTCACACTTACAAAT---------------TACAATG---------AAAAT
4426 GROUP_50      AAACTAGAGGTCACACTTACAAAT...............TACAATG.........AAAAT
4427
4428 150_HRV49a    AATTTCAAAGTATGGAACATCAATTTGCAAGAAATGGCCCAGATCAGAAGAAAATTTGAA
4429 151_HRV49b    AATTTCAAAGTATGGAACATCAATTTGCAAGAAATGGCCCAGATCAGAAGAAAATTTGAA
4430 152_HRV49     AATTTCAAAGTATGGAACATCAATTTGCAAGAAATGGCCCAGATCAGAAGAAAATTTGAA
4431 GROUP_50      AATTTCAAAGTATGGAACATCAATTTGCAAGAAATGGCCCAGATCAGAAGAAAATTTGAA
4432
4433 150_HRV49a    CTGTTTACTTACACTAGATTCGATTCTGAAATAACCTTGG-TTCCATGCATTTCTGCACT
4434 151_HRV49b    CTGTTTACTTACACTAGATTCGATTCTGAAATAACCTTGG-TTCCATGCATTTCTGCACT
4435 152_HRV49     CTGTTTACTTACACTAGATTCGATTCTGAAATAACCTTGG-TTCCATGCATTTCTGCACT
4436 GROUP_50      CTGTTTACTTACACTAGATTCGATTCTGAAATAACCTTGG.TTCCATGCATTTCTGCACT
4437
4438 150_HRV49a    TAGCAAGGATATTGGACACATTACAATGCAATACATGTATGTGCCGCCAGGTGCACCTGT
4439 151_HRV49b    TAGCAAGGATATTGGACACATTACAATGCAATACATGTATGTGCCGCCAGGTGCACCTGT
4440 152_HRV49     TAGCAAGGATATTGGACACATTACAATGCAATACATGTATGTGCCGCCAGGTGCACCTGT
4441 GROUP_50      TAGCAAGGATATTGGACACATTACAATGCAATACATGTATGTGCCGCCAGGTGCACCTGT
4442
4443 150_HRV49a    ACCAAAGAGCAGAGATGATTATGCATGGCAGTCTGGCACTAATGCATCTGTTTTCTGGCA
4444 151_HRV49b    ACCAAAGAGCAGAGATGATTATGCATGGCAGTCTGGCACTAATGCATCTGTTTTCTGGCA
4445 152_HRV49     ACCAAAGAGCAGAGATGATTATGCATGGCAGTCTGGCACTAATGCATCTGTTTTCTGGCA
4446 GROUP_50      ACCAAAGAGCAGAGATGATTATGCATGGCAGTCTGGCACTAATGCATCTGTTTTCTGGCA
4447
4448 150_HRV49a    ACATGGGCAAGCATACCCAAGATTTTCTCTACCCTTTTTGAGTGTAGCTTCAGCTTACTA
4449 151_HRV49b    ACATGGGCAAGCATACCCAAGATTTTCTCTACCCTTTTTGAGTGTAGCTTCAGCTTACTA
4450 152_HRV49     ACATGGGCAAGCATACCCAAGATTTTCTCTACCCTTTTTGAGTGTAGCTTCAGCTTACTA
4451 GROUP_50      ACATGGGCAAGCATACCCAAGATTTTCTCTACCCTTTTTGAGTGTAGCTTCAGCTTACTA
4452
4453 150_HRV49a    CATGTTTTATGATGGATATAATG------AACAGGGCCAAAATTATGGTACGGTAAGTAC
4454 151_HRV49b    CATGTTTTATGATGGATATAATG------AACAGGGCCAAAATTATGGTACGGTAAGTAC
4455 152_HRV49     CATGTTTTATGATGGATATAATG------AACAGGGCCAAAATTATGGTACGGTAAGTAC
4456 GROUP_50      CATGTTTTATGATGGATATAATG......AACAGGGCCAAAATTATGGTACGGTAAGTAC
4457
4458 150_HRV49a    AAACAACATGGGATCATTATGCTCTAGGATAGTAACAGAGAAACACATTCACAGTATGCA
4459 151_HRV49b    AAACAACATGGGATCATTATGCTCTAGGATAGTAACAGAGAAACACATTCACAGTATGCA
4460 152_HRV49     AAACAACATGGGATCATTATGCTCTAGGATAGTAACAGAGAAACACATTCACAGTATGCA
4461 GROUP_50      AAACAACATGGGATCATTATGCTCTAGGATAGTAACAGAGAAACACATTCACAGTATGCA
4462
4463 150_HRV49a    TATCATGACAAGAATCTATCATAAAGCTAAACACGTCAAAGCATGGTGTCCGCGCCCACC
4464 151_HRV49b    TATCATGACAAGAATCTATCATAAAGCTAAACACGTCAAAGCATGGTGTCCGCGCCCACC
4465 152_HRV49     TATCATGACAAGAATCTATCATAAAGCTAAACACGTCAAAGCATGGTGTCCGCGCCCACC
4466 GROUP_50      TATCATGACAAGAATCTATCATAAAGCTAAACACGTCAAAGCATGGTGTCCGCGCCCACC
4467
4468 150_HRV49a    CAGAGCACTTGAATATACT-CGCGCTCACCGTACTAATTTCAAAG-TTGAAG---ACAGA
4469 151_HRV49b    CAGAGCACTTGAATATACT-CGCGCTCACCGTACTAATTTCAAAG-TTGAAG---ACAGA
4470 152_HRV49     CAGAGCACTTGAATATACT-CGCGCTCACCGTACTAATTTCAAAG-TTGAAG---ACAGA
4471 GROUP_50      CAGAGCACTTGAATATACT.CGCGCTCACCGTACTAATTTCAAAG.TTGAAG...ACAGA
4472
4473 150_HRV49a    GACA------TTAAAACAG---GAATCACATCCAGAGCAATTATTACAACAGCG------
4474 151_HRV49b    GACA------TTAAAACAG---GAATCACATCCAGAGCAATTATTACAACAGCA------
```

FIG. D14 CONT'D

```
10.trace                                                                      9/20/2007 5:05 PM 4475  152_HRV49    GACA------TTAAAACAG---GAATCACATCCAGAGCAATTATTACAACAGCT------
4476  GROUP_50     GACA......TTAAAACAG...GAATCACATCCAGAGCAATTATTACAACAGC-......
4477
4478  150_HRV49a   --------------------
4479  151_HRV49b   --------------------
4480  152_HRV49    --------------------
4481  GROUP_50     ....................
4482
4483
4484  Group  51:
4485
4486
4487  153_HRV23a   AATCCAATTGAGAACTATGTAGATGAAGTTCTTAATGAAGTCTTAGTTGTTCCCAATATC
4488  154_HRV23b   AATCCAATTGAGAACTATGTAGATGAAGTTCTTAATGAAGTCTTAGTTGTTCCCAATATC
4489  155_HRV23    AATCCAATTGAGAACTATGTAGATGAAGTTCTTAATGAAGTCTTAGTTGTTCCCAATATC
4490  GROUP_51     AATCCAATTGAGAACTATGTAGATGAAGTTCTTAATGAAGTCTTAGTTGTTCCCAATATC
4491
4492  153_HRV23a   AATAGTAGTCATCCCACAACATCAAACTCTGCTCCAGCATTAGACGCTGCGGAAACGGGT
4493  154_HRV23b   AATAGTAGTCATCCCACAACATCAAACTCTGCTCCAGCATTAGACGCTGCGGAAACGGGT
4494  155_HRV23    AATAGTAGTCATCCCACAACATCAAACTCTGCTCCAGCATTAGACGCTGCGGAAACGGGT
4495  GROUP_51     AATAGTAGTCATCCCACAACATCAAACTCTGCTCCAGCATTAGACGCTGCGGAAACGGGT
4496
4497  153_HRV23a   CACACTAGTAATGTTCAACCAGAAGATGTCATTGAAACCAGGTACGTTCAAACATCACAA
4498  154_HRV23b   CACACTAGTAATGTTCAACCAGAAGATGTCATTGAAACCAGGTACGTTCAAACATCACAA
4499  155_HRV23    CACACTAGTAATGTTCAACCAGAAGATGTCATTGAAACCAGGTACGTTCAAACATCACAA
4500  GROUP_51     CACACTAGTAATGTTCAACCAGAAGATGTCATTGAAACCAGGTACGTTCAAACATCACAA
4501
4502  153_HRV23a   ACAAGAGATGAAATGAGTTTAGAAAGTTTCCTTGGTAGGTCAGGGTGTATACATGAATCT
4503  154_HRV23b   ACAAGAGATGAAATGAGTTTAGAAAGTTTCCTTGGTAGGTCAGGGTGTATACATGAATCT
4504  155_HRV23    ACAAGAGATGAAATGAGTTTAGAAAGTTTCCTTGGTAGGTCAGGGTGTATACATGAATCT
4505  GROUP_51     ACAAGAGATGAAATGAGTTTAGAAAGTTTCCTTGGTAGGTCAGGGTGTATACATGAATCT
4506
4507  153_HRV23a   AAATTAAAAGTTGAGATCGGAAAC---------------TATGATG---------AAAAC
4508  154_HRV23b   AAATTAAAAGTTGAGATCGGAAAC---------------TATGATG---------AAAAC
4509  155_HRV23    AAATTAAAAGTTGAGATCGGAAAC---------------TATGATG---------AAAAC
4510  GROUP_51     AAATTAAAAGTTGAGATCGGAAAC...............TATGATG.........AAAAC
4511
4512  153_HRV23a   AATTTTAATACTTGGAATATTAATTTACAGGAAATGGCCCAAATCAGAAGAAAGTTTGAA
4513  154_HRV23b   AATTTTAATACTTGGAATATTAATTTACAGGAAATGGCCCAAATCAGAAGAAAGTTTGAA
4514  155_HRV23    AATTTTAATACTTGGAATATTAATTTACAGGAAATGGCCCAAATCAGAAGAAAGTTTGAA
4515  GROUP_51     AATTTTAATACTTGGAATATTAATTTACAGGAAATGGCCCAAATCAGAAGAAAGTTTGAA
4516
4517  153_HRV23a   CTGTTTACTTACACTAGATTTGATTCTGAAATTACTTTGG-TTCCATGCATTTCTGCTCT
4518  154_HRV23b   CTGTTTACTTACACTAGATTTGATTCTGAAATTACTTTGG-TTCCATGCATTTCTGCTCT
4519  155_HRV23    CTGTTTACTTACACTAGATTTGATTCTGAAATTACTTTGG-TTCCATGCATTTCTGCTCT
4520  GROUP_51     CTGTTTACTTACACTAGATTTGATTCTGAAATTACTTTGG.TTCCATGCATTTCTGCTCT
4521
4522  153_HRV23a   TAGTCAAGATATTGGTCACATCACAATGCAGTATATGTATGTCCCACCAGGTGCTCCAAT
4523  154_HRV23b   TAGTCAAGATATTGGTCACATCACAATGCAGTATATGTATGTCCCACCAGGTGCTCCAAT
4524  155_HRV23    TAGTCAAGATATTGGTCACATCACAATGCAGTATATGTATGTCCCACCAGGTGCTCCAAT
4525  GROUP_51     TAGTCAAGATATTGGTCACATCACAATGCAGTATATGTATGTCCCACCAGGTGCTCCAAT
4526
4527  153_HRV23a   ACCGGAAAGTAGAAATGACTATGCATGGCAATCTGGAACAAATGCGTCCATTTTTTGGCA
4528  154_HRV23b   ACCGGAAAGTAGAAATGACTATGCATGGCAATCTGGAACAAATGCGTCCATTTTTTGGCA
4529  155_HRV23    ACCGGAAAGTAGAAATGACTATGCATGGCAATCTGGAACAAATGCGTCCATTTTTTGGCA
4530  GROUP_51     ACCGGAAAGTAGAAATGACTATGCATGGCAATCTGGAACAAATGCGTCCATTTTTTGGCA
4531
4532  153_HRV23a   ACATGGACAAACATATCCAAGGTTCTCCTTACCCTTTTTGAGTGTGGCATCTGCTTATTA
4533  154_HRV23b   ACATGGACAAACATATCCAAGGTTCTCCTTACCCTTTTTGAGTGTGGCATCTGCTTATTA
4534  155_HRV23    ACATGGACAAACATATCCAAGGTTCTCCTTACCCTTTTTGAGTGTGGCATCTGCTTATTA
4535  GROUP_51     ACATGGACAAACATATCCAAGGTTCTCCTTACCCTTTTTGAGTGTGGCATCTGCTTATTA
4536
```

FIG. D14 CONT'D

```
10.trace                                                                                     9/20/2007 5:05 PM 4537  153_HRV23a    CATGTTTTATGATGGATACAATG------AGAAAGGCACGCATTATGGAACAGTTAGCAC
4538  154_HRV23b    CATGTTTTATGATGGATACAATG------AGAAAGGCACGCATTATGGAACAGTTAGCAC
4539  155_HRV23     CATGTTTTATGATGGATACAATG------AGAAAGGCACGCATTATGGAACAGTTAGCAC
4540  GROUP_51      CATGTTTTATGATGGATACAATG......AGAAAGGCACGCATTATGGAACAGTTAGCAC
4541
4542  153_HRV23a    AAACAACATGGGCACATTGTGCTCCAGAGTGGTAACAGAGAAACACATTCATGATATGCG
4543  154_HRV23b    AAACAACATGGGCACATTGTGCTCCAGAGTGGTAACAGAGAAACACATTCATGATATGCG
4544  155_HRV23     AAACAACATGGGCACATTGTGCTCCAGAGTGGTAACAGAGAAACACATTCATGATATGCG
4545  GROUP_51      AAACAACATGGGCACATTGTGCTCCAGAGTGGTAACAGAGAAACACATTCATGATATGCG
4546
4547  153_HRV23a    GATAATGACAAGGGTCTACCACAAAGCTAAACATGTCAAAGCATGGTGTCCGCGGCCACC
4548  154_HRV23b    GATAATGACAAGGGTCTACCACAAAGCTAAACATGTCAAAGCATGGTGTCCGCGGCCACC
4549  155_HRV23     GATAATGACAAGGGTCTACCACAAAGCTAAACATGTCAAAGCATGGTGTCCGCGGCCACC
4550  GROUP_51      GATAATGACAAGGGTCTACCACAAAGCTAAACATGTCAAAGCATGGTGTCCGCGGCCACC
4551
4552  153_HRV23a    CAGAGCACTTGAATACACA-CGCGCTCACCGTACTAATTTCAAAA-TTGAAG---GTGAA
4553  154_HRV23b    CAGAGCACTTGAATACACA-CGCGCTCACCGTACTAATTTCAAAA-TTGAAG---GTGAA
4554  155_HRV23     CAGAGCACTTGAATACACA-CGCGCTCACCGTACTAATTTCAAAA-TTGAAG---GTGAA
4555  GROUP_51      CAGAGCACTTGAATACACA.CGCGCTCACCGTACTAATTTCAAAA.TTGAAG...GTGAA
4556
4557  153_HRV23a    AATG------TCAAATCAA---GGGTTGCACATAGACCTGCAGTGATAACAGCG------
4558  154_HRV23b    AATG------TCAAATCAA---GGGTTGCACATAGACCTGCAGTGATAACAGCA------
4559  155_HRV23     AATG------TCAAATCAA---GGGTTGCACATAGACCTGCAGTGATAACAGCT------
4560  GROUP_51      AATG......TCAAATCAA...GGGTTGCACATAGACCTGCAGTGATAACAGC-......
4561
4562  153_HRV23a    --------------------
4563  154_HRV23b    --------------------
4564  155_HRV23     --------------------
4565  GROUP_51      ....................
4566
4567
4568
4569  Group  52:
4570
4571  156_HRV30a    AACCCGGTTGAAAATTTTGTAGATGAAGTTCTTAGTGAAGTTTTAGTTGTTCCAAACATT
4572  157_HRV30b    AACCCGGTTGAAAATTTTGTAGATGAAGTTCTTAGTGAAGTTTTAGTTGTTCCAAACATT
4573  158_HRV30     AACCCGGTTGAAAATTTTGTAGATGAAGTTCTTAGTGAAGTTTTAGTTGTTCCAAACATT
4574  GROUP_52      AACCCGGTTGAAAATTTTGTAGATGAAGTTCTTAGTGAAGTTTTAGTTGTTCCAAACATT
4575
4576  156_HRV30a    AACAGTAGTCACCCTACTACATCAAACTCTGCTCCGGCATTAGATGCTGCAGAAACAGGA
4577  157_HRV30b    AACAGTAGTCACCCTACTACATCAAACTCTGCTCCGGCATTAGATGCTGCAGAAACAGGA
4578  158_HRV30     AACAGTAGTCACCCTACTACATCAAACTCTGCTCCGGCATTAGATGCTGCAGAAACAGGA
4579  GROUP_52      AACAGTAGTCACCCTACTACATCAAACTCTGCTCCGGCATTAGATGCTGCAGAAACAGGA
4580
4581  156_HRV30a    CATACTAGTAATGTTCAACCTGAAGATGTCATTGAAACTAGATATGTTCAAACATCACAA
4582  157_HRV30b    CATACTAGTAATGTTCAACCTGAAGATGTCATTGAAACTAGATATGTTCAAACATCACAA
4583  158_HRV30     CATACTAGTAATGTTCAACCTGAAGATGTCATTGAAACTAGATATGTTCAAACATCACAA
4584  GROUP_52      CATACTAGTAATGTTCAACCTGAAGATGTCATTGAAACTAGATATGTTCAAACATCACAA
4585
4586  156_HRV30a    ACAAGGGATGAAATGAGTTTAGAAAGCTTTCTTGGTAGATCAGGATGTATACACGAGTCT
4587  157_HRV30b    ACAAGGGATGAAATGAGTTTAGAAAGCTTTCTTGGTAGATCAGGATGTATACACGAGTCT
4588  158_HRV30     ACAAGGGATGAAATGAGTTTAGAAAGCTTTCTTGGTAGATCAGGATGTATACACGAGTCT
4589  GROUP_52      ACAAGGGATGAAATGAGTTTAGAAAGCTTTCTTGGTAGATCAGGATGTATACACGAGTCT
4590
4591  156_HRV30a    AAATTAGAACTTGAGCTTGCACAC---------------TATGATA---------AAAAG
4592  157_HRV30b    AAATTAGAACTTGAGCTTGCACAC---------------TATGATA---------AAAAG
4593  158_HRV30     AAATTAGAACTTGAGCTTGCACAC---------------TATGATA---------AAAAG
4594  GROUP_52      AAATTAGAACTTGAGCTTGCACAC...............TATGATA.........AAAAG
4595
4596  156_HRV30a    AACTTTACCACATGGAATATTAATCTTCAAGAAATGGCCCAAATTAGAAGAAAATTTGAG
4597  157_HRV30b    AACTTTACCACATGGAATATTAATCTTCAAGAAATGGCCCAAATTAGAAGAAAATTTGAG
4598  158_HRV30     AACTTTACCACATGGAATATTAATCTTCAAGAAATGGCCCAAATTAGAAGAAAATTTGAG
4599  GROUP_52      AACTTTACCACATGGAATATTAATCTTCAAGAAATGGCCCAAATTAGAAGAAAATTTGAG
4600
4601  156_HRV30a    CTATTCACTTACACTAGATTTGATTCTGAGATAACCTTGG-TTCCGTGTATTTCAGCTCT
```

FIG. D14 CONT'D

```
10.trace                                                                                      9/20/2007 5:05 PM 4602  157_HRV30b   CTATTCACTTACACTAGATTTGATTCTGAGATAACCTTGG-TTCCGTGTATTTCAGCTCT
4603  158_HRV30    CTATTCACTTACACTAGATTTGATTCTGAGATAACCTTGG-TTCCGTGTATTTCAGCTCT
4604  GROUP_52     CTATTCACTTACACTAGATTTGATTCTGAGATAACCTTGG.TTCCGTGTATTTCAGCTCT
4605
4606  156_HRV30a   CAGCCAAGATATCGGACACATTACAATGCAGTATATGTATGTTCCACCTGGCGCTCCAAT
4607  157_HRV30b   CAGCCAAGATATCGGACACATTACAATGCAGTATATGTATGTTCCACCTGGCGCTCCAAT
4608  158_HRV30    CAGCCAAGATATCGGACACATTACAATGCAGTATATGTATGTTCCACCTGGCGCTCCAAT
4609  GROUP_52     CAGCCAAGATATCGGACACATTACAATGCAGTATATGTATGTTCCACCTGGCGCTCCAAT
4610
4611  156_HRV30a   TCCCGAGAGCAGAAATGACTATGCATGGCAGTCTGGAACAAATGCATCTGTTTTTTGGCA
4612  157_HRV30b   TCCCGAGAGCAGAAATGACTATGCATGGCAGTCTGGAACAAATGCATCTGTTTTTTGGCA
4613  158_HRV30    TCCCGAGAGCAGAAATGACTATGCATGGCAGTCTGGAACAAATGCATCTGTTTTTTGGCA
4614  GROUP_52     TCCCGAGAGCAGAAATGACTATGCATGGCAGTCTGGAACAAATGCATCTGTTTTTTGGCA
4615
4616  156_HRV30a   ACACGGACAAACATACCCAAGATTCTCCCTACCATTTTTGAGTGTAGCATCTGCTTATTA
4617  157_HRV30b   ACACGGACAAACATACCCAAGATTCTCCCTACCATTTTTGAGTGTAGCATCTGCTTATTA
4618  158_HRV30    ACACGGACAAACATACCCAAGATTCTCCCTACCATTTTTGAGTGTAGCATCTGCTTATTA
4619  GROUP_52     ACACGGACAAACATACCCAAGATTCTCCCTACCATTTTTGAGTGTAGCATCTGCTTATTA
4620
4621  156_HRV30a   CATGTTCTATGATGGATACAATG------AGGGAGGCACAAATTATGGTACAGTGAGCAC
4622  157_HRV30b   CATGTTCTATGATGGATACAATG------AGGGAGGCACAAATTATGGTACAGTGAGCAC
4623  158_HRV30    CATGTTCTATGATGGATACAATG------AGGGAGGCACAAATTATGGTACAGTGAGCAC
4624  GROUP_52     CATGTTCTATGATGGATACAATG......AGGGAGGCACAAATTATGGTACAGTGAGCAC
4625
4626  156_HRV30a   AAACAACATGGGCACACTGTGTTCCAGAGTGGTAACAGAAAAACACATTCATGATGTGCG
4627  157_HRV30b   AAACAACATGGGCACACTGTGTTCCAGAGTGGTAACAGAAAAACACATTCATGATGTGCG
4628  158_HRV30    AAACAACATGGGCACACTGTGTTCCAGAGTGGTAACAGAAAAACACATTCATGATGTGCG
4629  GROUP_52     AAACAACATGGGCACACTGTGTTCCAGAGTGGTAACAGAAAAACACATTCATGATGTGCG
4630
4631  156_HRV30a   CATAATGACAAGGGTCTACCACAAGGCTAAACATGTCAAAGCGTGGTGTCCACGGCCACC
4632  157_HRV30b   CATAATGACAAGGGTCTACCACAAGGCTAAACATGTCAAAGCGTGGTGTCCACGGCCACC
4633  158_HRV30    CATAATGACAAGGGTCTACCACAAGGCTAAACATGTCAAAGCGTGGTGTCCACGGCCACC
4634  GROUP_52     CATAATGACAAGGGTCTACCACAAGGCTAAACATGTCAAAGCGTGGTGTCCACGGCCACC
4635
4636  156_HRV30a   TAGGGCGCTTGAGTATACC-CGTGCTCATCGCACCAATTTTAAAA-TTGATG---GCAGG
4637  157_HRV30b   TAGGGCGCTTGAGTATACC-CGTGCTCATCGCACCAATTTTAAAA-TTGATG---GCAGG
4638  158_HRV30    TAGGGCGCTTGAGTATACC-CGTGCTCATCGCACCAATTTTAAAA-TTGATG---GCAGG
4639  GROUP_52     TAGGGCGCTTGAGTATACC.CGTGCTCATCGCACCAATTTTAAAA.TTGATG...GCAGG
4640
4641  156_HRV30a   GAAG------TTAAATCAA---GGGTTGAACACAGAGCTAGGGTGACGACAGCA------
4642  157_HRV30b   GAAG------TTAAATCAA---GGGTTGAACACAGAGCTAGGGTGACGACAGCG------
4643  158_HRV30    GAAG------TTAAATCAA---GGGTTGAACACAGAGCTAGGGTGACGACAGCT------
4644  GROUP_52     GAAG......TTAAATCAA...GGGTTGAACACAGAGCTAGGGTGACGACAGC-......
4645
4646  156_HRV30a   --------------------
4647  157_HRV30b   --------------------
4648  158_HRV30    --------------------
4649  GROUP_52     ....................
4650
4651
4652
4653  Group  53:
4654
4655  159_HRV7     AACCCGGTAGAGAATTATGTAGATAGCTTACTAAATGAAGTATTAGTGGTACCTAATATT
4656  160_HRV7b|   AACCCGGTAGAGAATTATGTAGATAGCTTACTAAATGAAGTATTAGTGGTACCTAATATT
4657  161_HRV7a|   AACCCGGTAGAGAATTATGTAGATAGCTTACTAAATGAAGTATTAGTGGTACCTAATATT
4658  GROUP_53     AACCCGGTAGAGAATTATGTAGATAGCTTACTAAATGAAGTATTAGTGGTACCTAATATT
4659
4660  159_HRV7     CAGCCAAGTACATCTGTTTCAAGTCACTCTGTACCAGCATTGGATGCTGCAGAGACTGGA
4661  160_HRV7b|   CAGCCAAGTACATCTGTTTCAAGTCACTCTGTACCAGCATTGGATGCTGCAGAGACTGGA
4662  161_HRV7a|   CAGCCAAGTACATCTGTTTCAAGTCACTCTGTACCAGCATTGGATGCTGCAGAGACTGGA
4663  GROUP_53     CAGCCAAGTACATCTGTTTCAAGTCACTCTGTACCAGCATTGGATGCTGCAGAGACTGGA
4664
4665  159_HRV7     CATACTAGTTCTGTTCAACCTGAAGATATGATCGAGACAAGGTATGTCATAACAGACCAA
4666  160_HRV7b|   CATACTAGTTCTGTTCAACCTGAAGATATGATCGAGACAAGGTATGTCATAACAGACCAA
```

FIG. D14 CONT'D

```
10.trace                                                                    9/20/2007 5:05 PM 4667 161_HRV7a|   CATACTAGTTCTGTTCAACCTGAAGATATGATCGAGACAAGGTATGTCATAACAGACCAA
4668 GROUP_53    CATACTAGTTCTGTTCAACCTGAAGATATGATCGAGACAAGGTATGTCATAACAGACCAA
4669
4670 159_HRV7    ACAAGGGATGAAACTAGTATAGAGAGTTTCTTAGGTAGATCTGGATGTATTGCTAAAGTT
4671 160_HRV7b|  ACAAGGGATGAAACTAGTATAGAGAGTTTCTTAGGTAGATCTGGATGTATTGCTAAAGTT
4672 161_HRV7a|  ACAAGGGATGAAACTAGTATAGAGAGTTTCTTAGGTAGATCTGGATGTATTGCTAAAGTT
4673 GROUP_53    ACAAGGGATGAAACTAGTATAGAGAGTTTCTTAGGTAGATCTGGATGTATTGCTAAAGTT
4674
4675 159_HRV7    AAACTTGACACAA------CACAGGGT---------GACTATGACACAGGCAAAGGTGTT
4676 160_HRV7b|  AAACTTGACACAA------CACAGGGT---------GACTATGACACAGGCAAAGGTGTT
4677 161_HRV7a|  AAACTTGACACAA------CACAGGGT---------GACTATGACACAGGCAAAGGTGTT
4678 GROUP_53    AAACTTGACACAA......CACAGGGT.........GACTATGACACAGGCAAAGGTGTT
4679
4680 159_HRV7    GGTTTCACTACATGGAAAATCAGCTTACAAGAAATGGCACAAATCAGAAGAAAGTTTGAA
4681 160_HRV7b|  GGTTTCACTACATGGAAAATCAGCTTACAAGAAATGGCACAAATCAGAAGAAAGTTTGAA
4682 161_HRV7a|  GGTTTCACTACATGGAAAATCAGCTTACAAGAAATGGCACAAATCAGAAGAAAGTTTGAA
4683 GROUP_53    GGTTTCACTACATGGAAAATCAGCTTACAAGAAATGGCACAAATCAGAAGAAAGTTTGAA
4684
4685 159_HRV7    CTATTCACATACACTAGATTTGATTCTGAGATAACAATAG-TCACAGCAGCAGCAGCACA
4686 160_HRV7b|  CTATTCACATACACTAGATTTGATTCTGAGATAACAATAG-TCACAGCAGCAGCAGCACA
4687 161_HRV7a|  CTATTCACATACACTAGATTTGATTCTGAGATAACAATAG-TCACAGCAGCAGCAGCACA
4688 GROUP_53    CTATTCACATACACTAGATTTGATTCTGAGATAACAATAG.TCACAGCAGCAGCAGCACA
4689
4690 159_HRV7    AGGTAATGATATTGGACATATAGTTATGCAATTTATGTATGTACCTCCAGGGGCCCCAGT
4691 160_HRV7b|  AGGTAATGATATTGGACATATAGTTATGCAATTTATGTATGTACCTCCAGGGGCCCCAGT
4692 161_HRV7a|  AGGTAATGATATTGGACATATAGTTATGCAATTTATGTATGTACCTCCAGGGGCCCCAGT
4693 GROUP_53    AGGTAATGATATTGGACATATAGTTATGCAATTTATGTATGTACCTCCAGGGGCCCCAGT
4694
4695 159_HRV7    TCCAATAAAACGCGAAGATTATACATGGCAATCAGGAACAAATGCTTCTATATTTTGGCA
4696 160_HRV7b|  TCCAATAAAACGCGAAGATTATACATGGCAATCAGGAACAAATGCTTCTATATTTTGGCA
4697 161_HRV7a|  TCCAATAAAACGCGAAGATTATACATGGCAATCAGGAACAAATGCTTCTATATTTTGGCA
4698 GROUP_53    TCCAATAAAACGCGAAGATTATACATGGCAATCAGGAACAAATGCTTCTATATTTTGGCA
4699
4700 159_HRV7    GGAGGGTCAACCATACCCTAGATTCACAATTCCTTTTATGAGTATTGCATCAGCTTATTA
4701 160_HRV7b|  GGAGGGTCAACCATACCCTAGATTCACAATTCCTTTTATGAGTATTGCATCAGCTTATTA
4702 161_HRV7a|  GGAGGGTCAACCATACCCTAGATTCACAATTCCTTTTATGAGTATTGCATCAGCTTATTA
4703 GROUP_53    GGAGGGTCAACCATACCCTAGATTCACAATTCCTTTTATGAGTATTGCATCAGCTTATTA
4704
4705 159_HRV7    TATGTTCTATGATGGATATGATGGTGATGATGCGTCATCCAAATATGGTTCCGTAGTAAC
4706 160_HRV7b|  TATGTTCTATGATGGATATGATGGTGATGATGCGTCATCCAAATATGGTTCCGTAGTAAC
4707 161_HRV7a|  TATGTTCTATGATGGATATGATGGTGATGATGCGTCATCCAAATATGGTTCCGTAGTAAC
4708 GROUP_53    TATGTTCTATGATGGATATGATGGTGATGATGCGTCATCCAAATATGGTTCCGTAGTAAC
4709
4710 159_HRV7    CAATGACATGGGAACCATATGTGTTAGACTAGTTACATCTACACAAAAACACAATTTAAA
4711 160_HRV7b|  CAATGACATGGGAACCATATGTGTTAGACTAGTTACATCTACACAAAAACACAATTTAAA
4712 161_HRV7a|  CAATGACATGGGAACCATATGTGTTAGACTAGTTACATCTACACAAAAACACAATTTAAA
4713 GROUP_53    CAATGACATGGGAACCATATGTGTTAGACTAGTTACATCTACACAAAAACACAATTTAAA
4714
4715 159_HRV7    GATTGTGAGTCGCATTTACCACAAAGCCAAACATATAAAAGCATGGTGCCCACGCCCACC
4716 160_HRV7b|  GATTGTGAGTCGCATTTACCACAAAGCCAAACATATAAAAGCATGGTGCCCACGCCCACC
4717 161_HRV7a|  GATTGTGAGTCGCATTTACCACAAAGCCAAACATATAAAAGCATGGTGCCCACGCCCACC
4718 GROUP_53    GATTGTGAGTCGCATTTACCACAAAGCCAAACATATAAAAGCATGGTGCCCACGCCCACC
4719
4720 159_HRV7    ACGAGCTGTGCCTTATCAA-CACACTCACTCCACCAACTATGTGC-CACAAA---ATGGA
4721 160_HRV7b|  ACGAGCTGTGCCTTATCAA-CACACTCACTCCACCAACTATGTGC-CACAAA---ATGGA
4722 161_HRV7a|  ACGAGCTGTGCCTTATCAA-CACACTCACTCCACCAACTATGTGC-CACAAA---ATGGA
4723 GROUP_53    ACGAGCTGTGCCTTATCAA.CACACTCACTCCACCAACTATGTGC.CACAAA...ATGGA
4724
4725 159_HRV7    GAGG------TCGCA---ACTCAAATCAAAACCAGAGCCAATCTTTTCACCCTCAAAT--
4726 160_HRV7b|  GAGG------TCGCA---ACTCAAATCAAAACCAGAGCCAATCTTTTCACCCTCAAAT--
4727 161_HRV7a|  GAGG------TCGCA---ACTCAAATCAAAACCAGAGCCAATCTTTTCACCCTCAAAT--
4728 GROUP_53    GAGG......TCGCA...ACTCAAATCAAAACCAGAGCCAATCTTTTCACCCTCAAAT..
4729
4730 159_HRV7    ----CAGCT-----------
4731 160_HRV7b|  ----CAGCA-----------
```

FIG. D14 CONT'D

```
10.trace                                                              9/20/2007 5:05 PM 4732  161_HRV7a|    ----CAGCG-----------
4733  GROUP_53     ....CAGC-...........
4734
4735
4736
4737  Group  54:
4738
4739  162_HRV88     AATCCAGTAGAAAACTATGTAGATAACTTGTTAAACGAAGTGCTAGTAGTTCCTAACATT
4740  163_HRV88a    AATCCAGTAGAAAACTATGTAGATAACTTGTTAAACGAAGTGCTAGTAGTTCCTAACATT
4741  164_HRV88b    AATCCAGTAGAAAACTATGTAGATAACTTGTTAAACGAAGTGCTAGTAGTTCCTAACATT
4742  GROUP_54      AATCCAGTAGAAAACTATGTAGATAACTTGTTAAACGAAGTGCTAGTAGTTCCTAACATT
4743
4744  162_HRV88     CAACCTAGCACATCCGTTTCAAGTCACTCTGTGCCAGCTCTGGATGCTGCGGAAACAGGG
4745  163_HRV88a    CAACCTAGCACATCCGTTTCAAGTCACTCTGTGCCAGCTCTGGATGCTGCGGAAACAGGG
4746  164_HRV88b    CAACCTAGCACATCCGTTTCAAGTCACTCTGTGCCAGCTCTGGATGCTGCGGAAACAGGG
4747  GROUP_54      CAACCTAGCACATCCGTTTCAAGTCACTCTGTGCCAGCTCTGGATGCTGCGGAAACAGGG
4748
4749  162_HRV88     CATACTAGTTCTGTTCAACCTGAAGATATGATAGAAACTAGATATGTTATAACAGATCAA
4750  163_HRV88a    CATACTAGTTCTGTTCAACCTGAAGATATGATAGAAACTAGATATGTTATAACAGATCAA
4751  164_HRV88b    CATACTAGTTCTGTTCAACCTGAAGATATGATAGAAACTAGATATGTTATAACAGATCAA
4752  GROUP_54      CATACTAGTTCTGTTCAACCTGAAGATATGATAGAAACTAGATATGTTATAACAGATCAA
4753
4754  162_HRV88     ACAAGGGATGAAACCAGCATTGAAAGCTTTCTGGGTAGGTCTGGATGCATAGCAAAAATT
4755  163_HRV88a    ACAAGGGATGAAACCAGCATTGAAAGCTTTCTGGGTAGGTCTGGATGCATAGCAAAAATT
4756  164_HRV88b    ACAAGGGATGAAACCAGCATTGAAAGCTTTCTGGGTAGGTCTGGATGCATAGCAAAAATT
4757  GROUP_54      ACAAGGGATGAAACCAGCATTGAAAGCTTTCTGGGTAGGTCTGGATGCATAGCAAAAATT
4758
4759  162_HRV88     AAACTTGACACAA------ATGAAGGT---------GATTACGACACA---ATAGGTGTT
4760  163_HRV88a    AAACTTGACACAA------ATGAAGGT---------GATTACGACACA---ATAGGTGTT
4761  164_HRV88b    AAACTTGACACAA------ATGAAGGT---------GATTACGACACA---ATAGGTGTT
4762  GROUP_54      AAACTTGACACAA......ATGAAGGT.........GATTACGACACA...ATAGGTGTT
4763
4764  162_HRV88     GGATTTGTAACATGGAAGATTAGCTTGCAAGAAATGGCACAAATCAGGAGAAAATTTGAA
4765  163_HRV88a    GGATTTGTAACATGGAAGATTAGCTTGCAAGAAATGGCACAAATCAGGAGAAAATTTGAA
4766  164_HRV88b    GGATTTGTAACATGGAAGATTAGCTTGCAAGAAATGGCACAAATCAGGAGAAAATTTGAA
4767  GROUP_54      GGATTTGTAACATGGAAGATTAGCTTGCAAGAAATGGCACAAATCAGGAGAAAATTTGAA
4768
4769  162_HRV88     TTGTTTACATACACTAGATTTGACTCAGAAATAACAATAG-TCACAGCAGCTGCAGCACA
4770  163_HRV88a    TTGTTTACATACACTAGATTTGACTCAGAAATAACAATAG-TCACAGCAGCTGCAGCACA
4771  164_HRV88b    TTGTTTACATACACTAGATTTGACTCAGAAATAACAATAG-TCACAGCAGCTGCAGCACA
4772  GROUP_54      TTGTTTACATACACTAGATTTGACTCAGAAATAACAATAG.TCACAGCAGCTGCAGCACA
4773
4774  162_HRV88     AGGTGATGATACTGGACATATAGTACTGCAATTCATGTATGTGCCTCCAGGTGCACCAAT
4775  163_HRV88a    AGGTGATGATACTGGACATATAGTACTGCAATTCATGTATGTGCCTCCAGGTGCACCAAT
4776  164_HRV88b    AGGTGATGATACTGGACATATAGTACTGCAATTCATGTATGTGCCTCCAGGTGCACCAAT
4777  GROUP_54      AGGTGATGATACTGGACATATAGTACTGCAATTCATGTATGTGCCTCCAGGTGCACCAAT
4778
4779  162_HRV88     TCCCAAGAAACGTGATGATTACACATGGCAGTCAGGAACAAATGCATCTGTGTTCTGGCA
4780  163_HRV88a    TCCCAAGAAACGTGATGATTACACATGGCAGTCAGGAACAAATGCATCTGTGTTCTGGCA
4781  164_HRV88b    TCCCAAGAAACGTGATGATTACACATGGCAGTCAGGAACAAATGCATCTGTGTTCTGGCA
4782  GROUP_54      TCCCAAGAAACGTGATGATTACACATGGCAGTCAGGAACAAATGCATCTGTGTTCTGGCA
4783
4784  162_HRV88     AGAAGGACAACCATACCCAAGATTTACCATTCCCTTTATGAGTATTGCATCAGCTTACTA
4785  163_HRV88a    AGAAGGACAACCATACCCAAGATTTACCATTCCCTTTATGAGTATTGCATCAGCTTACTA
4786  164_HRV88b    AGAAGGACAACCATACCCAAGATTTACCATTCCCTTTATGAGTATTGCATCAGCTTACTA
4787  GROUP_54      AGAAGGACAACCATACCCAAGATTTACCATTCCCTTTATGAGTATTGCATCAGCTTACTA
4788
4789  162_HRV88     TATGTTTTATGATGGATATGATGGTGATGATGCATCATCTAGGTATGGCTCAGTGGTAAC
4790  163_HRV88a    TATGTTTTATGATGGATATGATGGTGATGATGCATCATCTAGGTATGGCTCAGTGGTAAC
4791  164_HRV88b    TATGTTTTATGATGGATATGATGGTGATGATGCATCATCTAGGTATGGCTCAGTGGTAAC
4792  GROUP_54      TATGTTTTATGATGGATATGATGGTGATGATGCATCATCTAGGTATGGCTCAGTGGTAAC
4793
4794  162_HRV88     TAATGATATGGGAACTATATGTATTAGATTGGTCACCTCCACCCAAAAGCATAAACTGAA
4795  163_HRV88a    TAATGATATGGGAACTATATGTATTAGATTGGTCACCTCCACCCAAAAGCATAAACTGAA
4796  164_HRV88b    TAATGATATGGGAACTATATGTATTAGATTGGTCACCTCCACCCAAAAGCATAAACTGAA
```

FIG. D14 CONT'D

```
10.trace                                                                       9/20/2007 5:05 PM 4797 GROUP_54      TAATGATATGGGAACTATATGTATTAGATTGGTCACCTCCACCCAAAAGCATAAACTGAA
4798
4799 162_HRV88     TATCATTAGCCGTATATATCACAAGGCTAAACATATAAAGGCATGGTGTCCACGCCCACC
4800 163_HRV88a    TATCATTAGCCGTATATATCACAAGGCTAAACATATAAAGGCATGGTGTCCACGCCCACC
4801 164_HRV88b    TATCATTAGCCGTATATATCACAAGGCTAAACATATAAAGGCATGGTGTCCACGCCCACC
4802 GROUP_54      TATCATTAGCCGTATATATCACAAGGCTAAACATATAAAGGCATGGTGTCCACGCCCACC
4803
4804 162_HRV88     AAGAGCCGTACCTTATCAG-CACACACACTCCACCAATTATGTAC-CAACAG---ATGGG
4805 163_HRV88a    AAGAGCCGTACCTTATCAG-CACACACACTCCACCAATTATGTAC-CAACAG---ATGGG
4806 164_HRV88b    AAGAGCCGTACCTTATCAG-CACACACACTCCACCAATTATGTAC-CAACAG---ATGGG
4807 GROUP_54      AAGAGCCGTACCTTATCAG.CACACACACTCCACCAATTATGTAC.CAACAG...ATGGG
4808
4809 162_HRV88     GAAG------TAGCA---ACTCAAATCAAAACCAGACGAGATGTTTACACTGTTACCA--
4810 163_HRV88a    GAAG------TAGCA---ACTCAAATCAAAACCAGACGAGATGTTTACACTGTTACCA--
4811 164_HRV88b    GAAG------TAGCA---ACTCAAATCAAAACCAGACGAGATGTTTACACTGTTACCA--
4812 GROUP_54      GAAG......TAGCA...ACTCAAATCAAAACCAGACGAGATGTTTACACTGTTACCA..
4813
4814 162_HRV88     ----CTGCT------------
4815 163_HRV88a    ----CTGCA------------
4816 164_HRV88b    ----CTGCG------------
4817 GROUP_54      ....CTGC-............
4818
4819
4820
4821 Group 55:
4822
4823 165_HRV36a    AATCCAGTTGAAAATTACATAGATAATGTATTAAATGAAGTACTTGTAGTGCCAAACATC
4824 166_HRV36b    AATCCAGTTGAAAATTACATAGATAATGTATTAAATGAAGTACTTGTAGTGCCAAACATC
4825 167_HRV36     AATCCAGTTGAAAATTACATAGATAATGTATTAAATGAAGTACTTGTAGTGCCAAACATC
4826 GROUP_55      AATCCAGTTGAAAATTACATAGATAATGTATTAAATGAAGTACTTGTAGTGCCAAACATC
4827
4828 165_HRV36a    CAACCTAGTTCATCTGTGTCAAGTCATTCAGCTCCCGCCTTAGAGCGCTGCGGAAACTGGA
4829 166_HRV36b    CAACCTAGTTCATCTGTGTCAAGTCATTCAGCTCCCGCCTTAGACGCTGCGGAAACTGGA
4830 167_HRV36     CAACCTAGTTCATCTGTGTCAAGTCATTCAGCTCCCGCCTTAGACGCTGCGGAAACTGGA
4831 GROUP_55      CAACCTAGTTCATCTGTGTCAAGTCATTCAGCTCCCGCCTTAGACGCTGCGGAAACTGGA
4832
4833 165_HRV36a    CATACCAGCTCTGTCCAACCAGAGGACATGATCGAGACCAGATATGTCATAACTGATCAA
4834 166_HRV36b    CATACCAGCTCTGTCCAACCAGAGGACATGATCGAGACCAGATATGTCATAACTGATCAA
4835 167_HRV36     CATACCAGCTCTGTCCAACCAGAGGACATGATCGAGACCAGATATGTCATAACTGATCAA
4836 GROUP_55      CATACCAGCTCTGTCCAACCAGAGGACATGATCGAGACCAGATATGTCATAACTGATCAA
4837
4838 165_HRV36a    ACAAGAGATGAGACAAGTATTGAAAGCTTCTTAGGTAGGTCAGGGTGCATAGCTATGATA
4839 166_HRV36b    ACAAGAGATGAGACAAGTATTGAAAGCTTCTTAGGTAGGTCAGGGTGCATAGCTATGATA
4840 167_HRV36     ACAAGAGATGAGACAAGTATTGAAAGCTTCTTAGGTAGGTCAGGGTGCATAGCTATGATA
4841 GROUP_55      ACAAGAGATGAGACAAGTATTGAAAGCTTCTTAGGTAGGTCAGGGTGCATAGCTATGATA
4842
4843 165_HRV36a    GAATTTAGCACAAGTAGTGATAAAGAT---------GAACATGATGAA---ATTGGCAAG
4844 166_HRV36b    GAATTTAGCACAAGTAGTGATAAAGAT---------GAACATGATGAA---ATTGGCAAG
4845 167_HRV36     GAATTTAGCACAAGTAGTGATAAAGAT---------GAACATGATGAA---ATTGGCAAG
4846 GROUP_55      GAATTTAGCACAAGTAGTGATAAAGAT.........GAACATGATGAA...ATTGGCAAG
4847
4848 165_HRV36a    GGATTCAAAACATGGAAGATTAGTCTTCAAGAAATGGCACAAATTAGAAGGAAATATGAA
4849 166_HRV36b    GGATTCAAAACATGGAAGATTAGTCTTCAAGAAATGGCACAAATTAGAAGGAAATATGAA
4850 167_HRV36     GGATTCAAAACATGGAAGATTAGTCTTCAAGAAATGGCACAAATTAGAAGGAAATATGAA
4851 GROUP_55      GGATTCAAAACATGGAAGATTAGTCTTCAAGAAATGGCACAAATTAGAAGGAAATATGAA
4852
4853 165_HRV36a    TTGTTTACATACACAAGATTTGACTCAGAAATAACAATAG-TCACCGCAGCTGCAGTGCA
4854 166_HRV36b    TTGTTTACATACACAAGATTTGACTCAGAAATAACAATAG-TCACCGCAGCTGCAGTGCA
4855 167_HRV36     TTGTTTACATACACAAGATTTGACTCAGAAATAACAATAG-TCACCGCAGCTGCAGTGCA
4856 GROUP_55      TTGTTTACATACACAAGATTTGACTCAGAAATAACAATAG.TCACCGCAGCTGCAGTGCA
4857
4858 165_HRV36a    GGGAGATGATAGTGGGCATGTAGTATTACAATTCATGTATGTACCTCCAGGAGCGCCTGT
```

FIG. D14 CONT'D

```
10.trace                                                              9/20/2007 5:05 PM 4859  166_HRV36b   GGGAGATGATAGTGGGCATGTAGTATTACAATTCATGTATGTACCTCCAGGAGCGCCTGT
4860  167_HRV36    GGGAGATGATAGTGGGCATGTAGTATTACAATTCATGTATGTACCTCCAGGAGCGCCTGT
4861  GROUP_55     GGGAGATGATAGTGGGCATGTAGTATTACAATTCATGTATGTACCTCCAGGAGCGCCTGT
4862
4863  165_HRV36a   TCCTGTGAAGCGTGATGACTACACATGGCAATCAGGGACAAATGCATCTGTGTTCTGGCA
4864  166_HRV36b   TCCTGTGAAGCGTGATGACTACACATGGCAATCAGGGACAAATGCATCTGTGTTCTGGCA
4865  167_HRV36    TCCTGTGAAGCGTGATGACTACACATGGCAATCAGGGACAAATGCATCTGTGTTCTGGCA
4866  GROUP_55     TCCTGTGAAGCGTGATGACTACACATGGCAATCAGGGACAAATGCATCTGTGTTCTGGCA
4867
4868  165_HRV36a   AGAAGGGCAACCATATCCTAGATTTACAATCCCCTTTATGAGTATTGCATCAGCTTATTA
4869  166_HRV36b   AGAAGGGCAACCATATCCTAGATTTACAATCCCCTTTATGAGTATTGCATCAGCTTATTA
4870  167_HRV36    AGAAGGGCAACCATATCCTAGATTTACAATCCCCTTTATGAGTATTGCATCAGCTTATTA
4871  GROUP_55     AGAAGGGCAACCATATCCTAGATTTACAATCCCCTTTATGAGTATTGCATCAGCTTATTA
4872
4873  165_HRV36a   TATGTTTTATGATGGTTATGATGGTGATAATGCCGCATCAAAATATGGATCTGTGGTTAC
4874  166_HRV36b   TATGTTTTATGATGGTTATGATGGTGATAATGCCGCATCAAAATATGGATCTGTGGTTAC
4875  167_HRV36    TATGTTTTATGATGGTTATGATGGTGATAATGCCGCATCAAAATATGGATCTGTGGTTAC
4876  GROUP_55     TATGTTTTATGATGGTTATGATGGTGATAATGCCGCATCAAAATATGGATCTGTGGTTAC
4877
4878  165_HRV36a   TAACGACATGGGAACCATATGTGTTAGAATAGTTACATCCAACCAAAAACATGATTTAAA
4879  166_HRV36b   TAACGACATGGGAACCATATGTGTTAGAATAGTTACATCCAACCAAAAACATGATTTAAA
4880  167_HRV36    TAACGACATGGGAACCATATGTGTTAGAATAGTTACATCCAACCAAAAACATGATTTAAA
4881  GROUP_55     TAACGACATGGGAACCATATGTGTTAGAATAGTTACATCCAACCAAAAACATGATTTAAA
4882
4883  165_HRV36a   TATTGTATGCCGCATTTATCATAAAGCTAAACACATAAAGGCCTGGTGCCCGCGTCCACC
4884  166_HRV36b   TATTGTATGCCGCATTTATCATAAAGCTAAACACATAAAGGCCTGGTGCCCGCGTCCACC
4885  167_HRV36    TATTGTATGCCGCATTTATCATAAAGCTAAACACATAAAGGCCTGGTGCCCGCGTCCACC
4886  GROUP_55     TATTGTATGCCGCATTTATCATAAAGCTAAACACATAAAGGCCTGGTGCCCGCGTCCACC
4887
4888  165_HRV36a   AAGGGCCGTTCCTTACCAA-CACACACATTCCACTAATTATATAC-CATACA---AAGGT
4889  166_HRV36b   AAGGGCCGTTCCTTACCAA-CACACACATTCCACTAATTATATAC-CATACA---AAGGT
4890  167_HRV36    AAGGGCCGTTCCTTACCAA-CACACACATTCCACTAATTATATAC-CATACA---AAGGT
4891  GROUP_55     AAGGGCCGTTCCTTACCAA.CACACACATTCCACTAATTATATAC.CATACA...AAGGT
4892
4893  165_HRV36a   GAGA------TCACA---ACCCAAATTAAAACCAGACCTAATGTCTTCACTGTA------
4894  166_HRV36b   GAGA------TCACA---ACCCAAATTAAAACCAGACCTAATGTCTTCACTGTG------
4895  167_HRV36    GAGA------TCACA---ACCCAAATTAAAACCAGACCTAATGTCTTCACTGTT------
4896  GROUP_55     GAGA......TCACA...ACCCAAATTAAAACCAGACCTAATGTCTTCACTGT-......
4897
4898  165_HRV36a   --------------------
4899  166_HRV36b   --------------------
4900  167_HRV36    --------------------
4901  GROUP_55     ....................
4902
4903
4904
4905  Group  56:
4906
4907  168_HRV89a   AACCCAGTTGAAAATTATATAGATAGTGTATTAAATGAAGTTCTTGTGGTGCCAAATATC
4908  169_HRV89b   AACCCAGTTGAAAATTATATAGATAGTGTATTAAATGAAGTTCTTGTGGTGCCAAATATC
4909  170_HRV89    AACCCAGTTGAAAATTATATAGATAGTGTATTAAATGAAGTTCTTGTGGTGCCAAATATC
4910  GROUP_56     AACCCAGTTGAAAATTATATAGATAGTGTATTAAATGAAGTTCTTGTGGTGCCAAATATC
4911
4912  168_HRV89a   CAACCTAGCACATCTGTGTCAAGTCATGCAGCGCCTGCATTGGATGCTGCGGAAACCGGA
4913  169_HRV89b   CAACCTAGCACATCTGTGTCAAGTCATGCAGCGCCTGCATTGGATGCTGCGGAAACCGGA
4914  170_HRV89    CAACCTAGCACATCTGTGTCAAGTCATGCAGCGCCTGCATTGGATGCTGCGGAAACCGGA
4915  GROUP_56     CAACCTAGCACATCTGTGTCAAGTCATGCAGCGCCTGCATTGGATGCTGCGGAAACCGGA
4916
4917  168_HRV89a   CACACCAGCTCTGTTCAACCTGAAGATATGATTGAAACTAGATATGTTATAACTGATCAA
4918  169_HRV89b   CACACCAGCTCTGTTCAACCTGAAGATATGATTGAAACTAGATATGTTATAACTGATCAA
4919  170_HRV89    CACACCAGCTCTGTTCAACCTGAAGATATGATTGAAACTAGATATGTTATAACTGATCAA
4920  GROUP_56     CACACCAGCTCTGTTCAACCTGAAGATATGATTGAAACTAGATATGTTATAACTGATCAA
4921
4922  168_HRV89a   ACAAGGGATGAAACAAGTATTGAGAGTTTCTTAGGTAGGTCAGGGTGTATCGCTATGATA
4923  169_HRV89b   ACAAGGGATGAAACAAGTATTGAGAGTTTCTTAGGTAGGTCAGGGTGTATCGCTATGATA
```

FIG. D14 CONT'D

```
10.trace                                                                              9/20/2007 5:05 PM 4924  170_HRV89   ACAAGGGATGAAACAAGTATTGAGAGTTTCTTAGGTAGGTCAGGGTGTATCGCTATGATA
4925  GROUP_56    ACAAGGGATGAAACAAGTATTGAGAGTTTCTTAGGTAGGTCAGGGTGTATCGCTATGATA
4926
4927  168_HRV89a  GAATTTAATACAAGTAGTGATAAAACT--------GAACATGATAAA---ATTGGTAAA
4928  169_HRV89b  GAATTTAATACAAGTAGTGATAAAACT--------GAACATGATAAA---ATTGGTAAA
4929  170_HRV89   GAATTTAATACAAGTAGTGATAAAACT--------GAACATGATAAA---ATTGGTAAA
4930  GROUP_56    GAATTTAATACAAGTAGTGATAAAACT.........GAACATGATAAA...ATTGGTAAA
4931
4932  168_HRV89a  GGATTCAAAACATGGAAGGTTAGTCTTCAAGAAATGGCACAAATCAGAAGAAAATATGAA
4933  169_HRV89b  GGATTCAAAACATGGAAGGTTAGTCTTCAAGAAATGGCACAAATCAGAAGAAAATATGAA
4934  170_HRV89   GGATTCAAAACATGGAAGGTTAGTCTTCAAGAAATGGCACAAATCAGAAGAAAATATGAA
4935  GROUP_56    GGATTCAAAACATGGAAGGTTAGTCTTCAAGAAATGGCACAAATCAGAAGAAAATATGAA
4936
4937  168_HRV89a  TTATTCACATATACAAGATTTGATTCAGAGATAACAATAG-TCACTGCAGCCGCAGCTCA
4938  169_HRV89b  TTATTCACATATACAAGATTTGATTCAGAGATAACAATAG-TCACTGCAGCCGCAGCTCA
4939  170_HRV89   TTATTCACATATACAAGATTTGATTCAGAGATAACAATAG-TCACTGCAGCCGCAGCTCA
4940  GROUP_56    TTATTCACATATACAAGATTTGATTCAGAGATAACAATAG.TCACTGCAGCCGCAGCTCA
4941
4942  168_HRV89a  AGGAAATGATAGTGGACATATAGTATTGCAATTTATGTATGTACCCCCAGGAGCACCTGT
4943  169_HRV89b  AGGAAATGATAGTGGACATATAGTATTGCAATTTATGTATGTACCCCCAGGAGCACCTGT
4944  170_HRV89   AGGAAATGATAGTGGACATATAGTATTGCAATTTATGTATGTACCCCCAGGAGCACCTGT
4945  GROUP_56    AGGAAATGATAGTGGACATATAGTATTGCAATTTATGTATGTACCCCCAGGAGCACCTGT
4946
4947  168_HRV89a  CCCCGAAAAACGTGATGATTACACATGGCAATCAGGAACAAATGCATCTGTGTTCTGGCA
4948  169_HRV89b  CCCCGAAAAACGTGATGATTACACATGGCAATCAGGAACAAATGCATCTGTGTTCTGGCA
4949  170_HRV89   CCCCGAAAAACGTGATGATTACACATGGCAATCAGGAACAAATGCATCTGTGTTCTGGCA
4950  GROUP_56    CCCCGAAAAACGTGATGATTACACATGGCAATCAGGAACAAATGCATCTGTGTTCTGGCA
4951
4952  168_HRV89a  AGAAGGACAACCATACCCCAGATTCACAATCCCTTTTATGAGCATTGCATCAGCCTATTA
4953  169_HRV89b  AGAAGGACAACCATACCCCAGATTCACAATCCCTTTTATGAGCATTGCATCAGCCTATTA
4954  170_HRV89   AGAAGGACAACCATACCCCAGATTCACAATCCCTTTTATGAGCATTGCATCAGCCTATTA
4955  GROUP_56    AGAAGGACAACCATACCCCAGATTCACAATCCCTTTTATGAGCATTGCATCAGCCTATTA
4956
4957  168_HRV89a  CATGTTTTATGATGGTTATGATGGTGATAGTGCAGCATCAAAATACGGTTCTGTAGTCAC
4958  169_HRV89b  CATGTTTTATGATGGTTATGATGGTGATAGTGCAGCATCAAAATACGGTTCTGTAGTCAC
4959  170_HRV89   CATGTTTTATGATGGTTATGATGGTGATAGTGCAGCATCAAAATACGGTTCTGTAGTCAC
4960  GROUP_56    CATGTTTTATGATGGTTATGATGGTGATAGTGCAGCATCAAAATACGGTTCTGTAGTCAC
4961
4962  168_HRV89a  TAATGATATGGGAACCATATGTGTTAGAATAGTGACATCCAACCAAAAACATGATTTAAA
4963  169_HRV89b  TAATGATATGGGAACCATATGTGTTAGAATAGTGACATCCAACCAAAAACATGATTTAAA
4964  170_HRV89   TAATGATATGGGAACCATATGTGTTAGAATAGTGACATCCAACCAAAAACATGATTTAAA
4965  GROUP_56    TAATGATATGGGAACCATATGTGTTAGAATAGTGACATCCAACCAAAAACATGATTTAAA
4966
4967  168_HRV89a  TATTGTGTGCCGCATTTACCACAAGGCCAAACATATAAAAGCATGGTGTCCTCGCCCACC
4968  169_HRV89b  TATTGTGTGCCGCATTTACCACAAGGCCAAACATATAAAAGCATGGTGTCCTCGCCCACC
4969  170_HRV89   TATTGTGTGCCGCATTTACCACAAGGCCAAACATATAAAAGCATGGTGTCCTCGCCCACC
4970  GROUP_56    TATTGTGTGCCGCATTTACCACAAGGCCAAACATATAAAAGCATGGTGTCCTCGCCCACC
4971
4972  168_HRV89a  AAGGGCTGTTGCCTATCAA-CACACACACTCAACCAATTACATAC-CATCCA---ATGGT
4973  169_HRV89b  AAGGGCTGTTGCCTATCAA-CACACACACTCAACCAATTACATAC-CATCCA---ATGGT
4974  170_HRV89   AAGGGCTGTTGCCTATCAA-CACACACACTCAACCAATTACATAC-CATCCA---ATGGT
4975  GROUP_56    AAGGGCTGTTGCCTATCAA.CACACACACTCAACCAATTACATAC.CATCCA...ATGGT
4976
4977  168_HRV89a  GAGG------CCACA---ACTCAGATTAAAACCAGACCTGATGTTTTTACCGTTACAA--
4978  169_HRV89b  GAGG------CCACA---ACTCAGATTAAAACCAGACCTGATGTTTTTACCGTTACAA--
4979  170_HRV89   GAGG------CCACA---ACTCAGATTAAAACCAGACCTGATGTTTTTACCGTTACAA--
4980  GROUP_56    GAGG......CCACA...ACTCAGATTAAAACCAGACCTGATGTTTTTACCGTTACAA..
4981
4982  168_HRV89a  ----ACGTG-----------
4983  169_HRV89b  ----ACGTA-----------
4984  170_HRV89   ----ACGTC-----------
4985  GROUP_56    ....ACGT-...........
4986
4987
4988
```

FIG. D14 CONT'D

```
10.trace                                                                 9/20/2007 5:05 PM 4989  Group 57:
4990
4991  171_HRV58     AATCCAGTAGAAAATTACATAGATAATGTGTTAAATGAAGTACTTGTAGTTCCAAATATC
4992  172_HRV58a    AATCCAGTAGAAAATTACATAGATAATGTGTTAAATGAAGTACTTGTAGTTCCAAATATC
4993  173_HRV58b    AATCCAGTAGAAAATTACATAGATAATGTGTTAAATGAAGTACTTGTAGTTCCAAATATC
4994  GROUP_57      AATCCAGTAGAAAATTACATAGATAATGTGTTAAATGAAGTACTTGTAGTTCCAAATATC
4995
4996  171_HRV58     CAACCTAGTACATCTGTATCAAGTCATTCTGTGCCTGCCTTGGATGCTGCAGAAACGGGA
4997  172_HRV58a    CAACCTAGTACATCTGTATCAAGTCATTCTGTGCCTGCCTTGGATGCTGCAGAAACGGGA
4998  173_HRV58b    CAACCTAGTACATCTGTATCAAGTCATTCTGTGCCTGCCTTGGATGCTGCAGAAACGGGA
4999  GROUP_57      CAACCTAGTACATCTGTATCAAGTCATTCTGTGCCTGCCTTGGATGCTGCAGAAACGGGA
5000
5001  171_HRV58     CACACAAGTTCTGTTCAGCCTGAGGATATGATTGAAACTAGATATGTTATCACAGATCAA
5002  172_HRV58a    CACACAAGTTCTGTTCAGCCTGAGGATATGATTGAAACTAGATATGTTATCACAGATCAA
5003  173_HRV58b    CACACAAGTTCTGTTCAGCCTGAGGATATGATTGAAACTAGATATGTTATCACAGATCAA
5004  GROUP_57      CACACAAGTTCTGTTCAGCCTGAGGATATGATTGAAACTAGATATGTTATCACAGATCAA
5005
5006  171_HRV58     ACAAGAGATGAAACTAGCATTGAAAGCTTTTTAGGTAGATCTGGTTGCATTGCTATCATA
5007  172_HRV58a    ACAAGAGATGAAACTAGCATTGAAAGCTTTTTAGGTAGATCTGGTTGCATTGCTATCATA
5008  173_HRV58b    ACAAGAGATGAAACTAGCATTGAAAGCTTTTTAGGTAGATCTGGTTGCATTGCTATCATA
5009  GROUP_57      ACAAGAGATGAAACTAGCATTGAAAGCTTTTTAGGTAGATCTGGTTGCATTGCTATCATA
5010
5011  171_HRV58     AAATTTAACACAA------ATAAGACT---------AATTATGATGAC---ATAGGTGTA
5012  172_HRV58a    AAATTTAACACAA------ATAAGACT---------AATTATGATGAC---ATAGGTGTA
5013  173_HRV58b    AAATTTAACACAA------ATAAGACT---------AATTATGATGAC---ATAGGTGTA
5014  GROUP_57      AAATTTAACACAA......ATAAGACT.........AATTATGATGAC...ATAGGTGTA
5015
5016  171_HRV58     GGATACAAAACATGGAAAATTAGCCTTCAAGAGATGGCACAAATTAGAAGGAAATTTGAG
5017  172_HRV58a    GGATACAAAACATGGAAAATTAGCCTTCAAGAGATGGCACAAATTAGAAGGAAATTTGAG
5018  173_HRV58b    GGATACAAAACATGGAAAATTAGCCTTCAAGAGATGGCACAAATTAGAAGGAAATTTGAG
5019  GROUP_57      GGATACAAAACATGGAAAATTAGCCTTCAAGAGATGGCACAAATTAGAAGGAAATTTGAG
5020
5021  171_HRV58     TTGTTTACATATACAAGATTTGACTCAGAGATTACAATAG-TCACTGCAGCAGCTGCTCA
5022  172_HRV58a    TTGTTTACATATACAAGATTTGACTCAGAGATTACAATAG-TCACTGCAGCAGCTGCTCA
5023  173_HRV58b    TTGTTTACATATACAAGATTTGACTCAGAGATTACAATAG-TCACTGCAGCAGCTGCTCA
5024  GROUP_57      TTGTTTACATATACAAGATTTGACTCAGAGATTACAATAG.TCACTGCAGCAGCTGCTCA
5025
5026  171_HRV58     AGGAGAAGATAATGGACATATTGTGTTACAATTTATGTATGTACCCCCAGGAGCACCTGT
5027  172_HRV58a    AGGAGAAGATAATGGACATATTGTGTTACAATTTATGTATGTACCCCCAGGAGCACCTGT
5028  173_HRV58b    AGGAGAAGATAATGGACATATTGTGTTACAATTTATGTATGTACCCCCAGGAGCACCTGT
5029  GROUP_57      AGGAGAAGATAATGGACATATTGTGTTACAATTTATGTATGTACCCCCAGGAGCACCTGT
5030
5031  171_HRV58     ACCCAAGAATCGTGATGACTTTACATGGCAATCAGGCACAAATGCATCTGTTTTCTGGCA
5032  172_HRV58a    ACCCAAGAATCGTGATGACTTTACATGGCAATCAGGCACAAATGCATCTGTTTTCTGGCA
5033  173_HRV58b    ACCCAAGAATCGTGATGACTTTACATGGCAATCAGGCACAAATGCATCTGTTTTCTGGCA
5034  GROUP_57      ACCCAAGAATCGTGATGACTTTACATGGCAATCAGGCACAAATGCATCTGTTTTCTGGCA
5035
5036  171_HRV58     GGAAGGACAACCATACCCTAGATTTACAATCCCTTTTATGAGCATTGCATCAGCTTACTA
5037  172_HRV58a    GGAAGGACAACCATACCCTAGATTTACAATCCCTTTTATGAGCATTGCATCAGCTTACTA
5038  173_HRV58b    GGAAGGACAACCATACCCTAGATTTACAATCCCTTTTATGAGCATTGCATCAGCTTACTA
5039  GROUP_57      GGAAGGACAACCATACCCTAGATTTACAATCCCTTTTATGAGCATTGCATCAGCTTACTA
5040
5041  171_HRV58     TATGTTTTATGATGGCTATGATGGTGATGATGCTAAATCAATATATGGTTCTGTGGTAAC
5042  172_HRV58a    TATGTTTTATGATGGCTATGATGGTGATGATGCTAAATCAATATATGGTTCTGTGGTAAC
5043  173_HRV58b    TATGTTTTATGATGGCTATGATGGTGATGATGCTAAATCAATATATGGTTCTGTGGTAAC
5044  GROUP_57      TATGTTTTATGATGGCTATGATGGTGATGATGCTAAATCAATATATGGTTCTGTGGTAAC
5045
5046  171_HRV58     AAATGACATGGGAACTATATGTGTTAGAATAGTCACATCCAAACAAAGACACAATTTAAA
5047  172_HRV58a    AAATGACATGGGAACTATATGTGTTAGAATAGTCACATCCAAACAAAGACACAATTTAAA
5048  173_HRV58b    AAATGACATGGGAACTATATGTGTTAGAATAGTCACATCCAAACAAAGACACAATTTAAA
5049  GROUP_57      AAATGACATGGGAACTATATGTGTTAGAATAGTCACATCCAAACAAAGACACAATTTAAA
5050
5051  171_HRV58     CATTGTCTGTCGCATTTACCACAAAGCCAAGCATATAAAAGCATGGTGTCCACGCCCACC
5052  172_HRV58a    CATTGTCTGTCGCATTTACCACAAAGCCAAGCATATAAAAGCATGGTGTCCACGCCCACC
5053  173_HRV58b    CATTGTCTGTCGCATTTACCACAAAGCCAAGCATATAAAAGCATGGTGTCCACGCCCACC
```

FIG. D14 CONT'D

10.trace                                                                                          9/20/2007 5:05 PM

```
5054 GROUP_57     CATTGTCTGTCGCATTTACCACAAAGCCAAGCATATAAAAGCATGGTGTCCACGCCCACC
5055
5056 171_HRV58    AAGGGCTGTTCCTTATCAA-TTCACACATTCTACTAATTACATAC-CAGATA---GTGGT
5057 172_HRV58a   AAGGGCTGTTCCTTATCAA-TTCACACATTCTACTAATTACATAC-CAGATA---GTGGT
5058 173_HRV58b   AAGGGCTGTTCCTTATCAA-TTCACACATTCTACTAATTACATAC-CAGATA---GTGGT
5059 GROUP_57     AAGGGCTGTTCCTTATCAA.TTCACACATTCTACTAATTACATAC.CAGATA...GTGGT
5060
5061 171_HRV58    GAGG------TAACA---ACACAAATCAAACCCAGAACCAATGTTTTTACTATTACAT--
5062 172_HRV58a   GAGG------TAACA---ACACAAATCAAACCCAGAACCAATGTTTTTACTATTACAT--
5063 173_HRV58b   GAGG------TAACA---ACACAAATCAAACCCAGAACCAATGTTTTTACTATTACAT--
5064 GROUP_57     GAGG......TAACA...ACACAAATCAAACCCAGAACCAATGTTTTTACTATTACAT..
5065
5066 171_HRV58    ----CTGCT------------
5067 172_HRV58a   ----CTGCA------------
5068 173_HRV58b   ----CTGCC------------
5069 GROUP_57     ....CTGC-............
5070
5071
5072
5073 Group 58:
5074
5075 174_HRV12a    AATCCAGTAGAGAGATATGTTGATGAGGTGCTAAATGAAGTTCTAGTTGTTCCAAACATA
5076 175_HRV12b    AATCCAGTAGAGAGATATGTTGATGAGGTGCTAAATGAAGTTCTAGTTGTTCCAAACATA
5077 176_HRV12     AATCCAGTAGAGAGATATGTTGATGAGGTGCTAAATGAAGTTCTAGTTGTTCCAAACATA
5078 GROUP_58      AATCCAGTAGAGAGATATGTTGATGAGGTGCTAAATGAAGTTCTAGTTGTTCCAAACATA
5079
5080 174_HRV12a    AACAAAAGTAATGGGCAGTTATCAAACGCAGCACCAGCGTTGGACGCTGCAGAAACTGGT
5081 175_HRV12b    AACAAAAGTAATGGGCAGTTATCAAACGCAGCACCAGCGTTGGACGCTGCAGAAACTGGT
5082 176_HRV12     AACAAAAGTAATGGGCAGTTATCAAACGCAGCACCAGCGTTGGACGCTGCAGAAACTGGT
5083 GROUP_58      AACAAAAGTAATGGGCAGTTATCAAACGCAGCACCAGCGTTGGACGCTGCAGAAACTGGT
5084
5085 174_HRV12a    CATACCAGCCAAACACAACCAGAAGATGTGATTGAAACCAGGTATGTGATTACAGACCAG
5086 175_HRV12b    CATACCAGCCAAACACAACCAGAAGATGTGATTGAAACCAGGTATGTGATTACAGACCAG
5087 176_HRV12     CATACCAGCCAAACACAACCAGAAGATGTGATTGAAACCAGGTATGTGATTACAGACCAG
5088 GROUP_58      CATACCAGCCAAACACAACCAGAAGATGTGATTGAAACCAGGTATGTGATTACAGACCAG
5089
5090 174_HRV12a    ACTAGAGATGAGATGTCAATTGAATCTTTCCTTGGTCGGTCCGGATGCATTTCAATTATC
5091 175_HRV12b    ACTAGAGATGAGATGTCAATTGAATCTTTCCTTGGTCGGTCCGGATGCATTTCAATTATC
5092 176_HRV12     ACTAGAGATGAGATGTCAATTGAATCTTTCCTTGGTCGGTCCGGATGCATTTCAATTATC
5093 GROUP_58      ACTAGAGATGAGATGTCAATTGAATCTTTCCTTGGTCGGTCCGGATGCATTTCAATTATC
5094
5095 174_HRV12a    GAATTGGATTTAGACCATGAAGGT---------------TATTCAGCA---GAAGGGAAA
5096 175_HRV12b    GAATTGGATTTAGACCATGAAGGT---------------TATTCAGCA---GAAGGGAAA
5097 176_HRV12     GAATTGGATTTAGACCATGAAGGT---------------TATTCAGCA---GAAGGGAAA
5098 GROUP_58      GAATTGGATTTAGACCATGAAGGT...............TATTCAGCA...GAAGGGAAA
5099
5100 174_HRV12a    AACTTTAAAACATGGAAGATAAATCTTAAGGAAATGGCCCAGATTAGAAGGAAAAATGAG
5101 175_HRV12b    AACTTTAAAACATGGAAGATAAATCTTAAGGAAATGGCCCAGATTAGAAGGAAAAATGAG
5102 176_HRV12     AACTTTAAAACATGGAAGATAAATCTTAAGGAAATGGCCCAGATTAGAAGGAAAAATGAG
5103 GROUP_58      AACTTTAAAACATGGAAGATAAATCTTAAGGAAATGGCCCAGATTAGAAGGAAAAATGAG
5104
5105 174_HRV12a    CTTTTCACCTACTTAAGGTTTGATTCTGAAATCACCATTGTTCCAAGCAATG-CAGCAAT
5106 175_HRV12b    CTTTTCACCTACTTAAGGTTTGATTCTGAAATCACCATTGTTCCAAGCAATG-CAGCAAT
5107 176_HRV12     CTTTTCACCTACTTAAGGTTTGATTCTGAAATCACCATTGTTCCAAGCAATG-CAGCAAT
5108 GROUP_58      CTTTTCACCTACTTAAGGTTTGATTCTGAAATCACCATTGTTCCAAGCAATG.CAGCAAT
5109
5110 174_HRV12a    AGAAGGAAGCAATGGTCACGTGGTGGTCCAATACATGTATGTACCTCCTGGTGCCCCACT
5111 175_HRV12b    AGAAGGAAGCAATGGTCACGTGGTGGTCCAATACATGTATGTACCTCCTGGTGCCCCACT
5112 176_HRV12     AGAAGGAAGCAATGGTCACGTGGTGGTCCAATACATGTATGTACCTCCTGGTGCCCCACT
5113 GROUP_58      AGAAGGAAGCAATGGTCACGTGGTGGTCCAATACATGTATGTACCTCCTGGTGCCCCACT
5114
5115 174_HRV12a    ACCCAAAAAACGTGATGATTACACATGGCAATCTGGCACCAACGCCTCAGTTTTTTGGCA
5116 175_HRV12b    ACCCAAAAAACGTGATGATTACACATGGCAATCTGGCACCAACGCCTCAGTTTTTTGGCA
5117 176_HRV12     ACCCAAAAAACGTGATGATTACACATGGCAATCTGGCACCAACGCCTCAGTTTTTTGGCA
5118 GROUP_58      ACCCAAAAAACGTGATGATTACACATGGCAATCTGGCACCAACGCCTCAGTTTTTTGGCA
```

FIG. D14 CONT'D

10.trace                                                                    9/20/2007 5:05 PM

```
5119
5120  174_HRV12a   GGAAGGTCAACCTTACCCCAGATTCACAATCCCTTTTATTAGTATTGCCTCAGCATATTA
5121  175_HRV12b   GGAAGGTCAACCTTACCCCAGATTCACAATCCCTTTTATTAGTATTGCCTCAGCATATTA
5122  176_HRV12    GGAAGGTCAACCTTACCCCAGATTCACAATCCCTTTTATTAGTATTGCCTCAGCATATTA
5123  GROUP_58     GGAAGGTCAACCTTACCCCAGATTCACAATCCCTTTTATTAGTATTGCCTCAGCATATTA
5124
5125  174_HRV12a   CATGTTTTATGATGGTTATGCTGATGACAACCCAAGTGCACCTTATGGAACTGTAGTTAC
5126  175_HRV12b   CATGTTTTATGATGGTTATGCTGATGACAACCCAAGTGCACCTTATGGAACTGTAGTTAC
5127  176_HRV12    CATGTTTTATGATGGTTATGCTGATGACAACCCAAGTGCACCTTATGGAACTGTAGTTAC
5128  GROUP_58     CATGTTTTATGATGGTTATGCTGATGACAACCCAAGTGCACCTTATGGAACTGTAGTTAC
5129
5130  174_HRV12a   CAATGACATGGGTTCACTGTGTGTCAGAATAGTTACAGACCAGCAAAAACATAAAGTTAA
5131  175_HRV12b   CAATGACATGGGTTCACTGTGTGTCAGAATAGTTACAGACCAGCAAAAACATAAAGTTAA
5132  176_HRV12    CAATGACATGGGTTCACTGTGTGTCAGAATAGTTACAGACCAGCAAAAACATAAAGTTAA
5133  GROUP_58     CAATGACATGGGTTCACTGTGTGTCAGAATAGTTACAGACCAGCAAAAACATAAAGTTAA
5134
5135  174_HRV12a   GATTACCAGTAGAATATACCATAAAGCAAAACATATCAGTGCCTGGGGCCCTAGACCACC
5136  175_HRV12b   GATTACCAGTAGAATATACCATAAAGCAAAACATATCAGTGCCTGGGGCCCTAGACCACC
5137  176_HRV12    GATTACCAGTAGAATATACCATAAAGCAAAACATATCAGTGCCTGGGGCCCTAGACCACC
5138  GROUP_58     GATTACCAGTAGAATATACCATAAAGCAAAACATATCAGTGCCTGGGGCCCTAGACCACC
5139
5140  174_HRV12a   AAGAGCTGTACCATACCAG-CATATACACAATCCAAATTACAAGA-CAAGTA------AT
5141  175_HRV12b   AAGAGCTGTACCATACCAG-CATATACACAATCCAAATTACAAGA-CAAGTA------AT
5142  176_HRV12    AAGAGCTGTACCATACCAG-CATATACACAATCCAAATTACAAGA-CAAGTA------AT
5143  GROUP_58     AAGAGCTGTACCATACCAG.CATATACACAATCCAAATTACAAGA.CAAGTA......AT
5144
5145  174_HRV12a   GGAG------TTCCAGACAATAGAGTCAAACTCAGAGAGACACTCACCACAGTA------
5146  175_HRV12b   GGAG------TTCCAGACAATAGAGTCAAACTCAGAGAGACACTCACCACAGTG------
5147  176_HRV12    GGAG------TTCCAGACAATAGAGTCAAACTCAGAGAGACACTCACCACAGTT------
5148  GROUP_58     GGAG......TTCCAGACAATAGAGTCAAACTCAGAGAGACACTCACCACAGT-......
5149
5150  174_HRV12a   --------------------
5151  175_HRV12b   --------------------
5152  176_HRV12    --------------------
5153  GROUP_58     ....................
5154
5155
5156
5157  Group  59:
5158
5159  177_HRV78a   AATCCAGTGGAAGAATATGTTGATCAGGTTTTAAATGAGGTTTTAGTTGTTCCAAACATA
5160  178_HRV78b   AATCCAGTGGAAGAATATGTTGATCAGGTTTTAAATGAGGTTTTAGTTGTTCCAAACATA
5161  179_HRV78    AATCCAGTGGAAGAATATGTTGATCAGGTTTTAAATGAGGTTTTAGTTGTTCCAAACATA
5162  GROUP_59     AATCCAGTGGAAGAATATGTTGATCAGGTTTTAAATGAGGTTTTAGTTGTTCCAAACATA
5163
5164  177_HRV78a   AAAGAAAGTAAACCCCAGTCTAGCAACTCCGCTCCAGTTTTGGACGCTGCAGAAACAGGT
5165  178_HRV78b   AAAGAAAGTAAACCCCAGTCTAGCAACTCCGCTCCAGTTTTGGACGCTGCAGAAACAGGT
5166  179_HRV78    AAAGAAAGTAAACCCCAGTCTAGCAACTCCGCTCCAGTTTTGGACGCTGCAGAAACAGGT
5167  GROUP_59     AAAGAAAGTAAACCCCAGTCTAGCAACTCCGCTCCAGTTTTGGACGCTGCAGAAACAGGT
5168
5169  177_HRV78a   CATACGAACCAAGTACAGCCTGAAGACACCATAGAAACTAGATATGTTATAACTGACCAA
5170  178_HRV78b   CATACGAACCAAGTACAGCCTGAAGACACCATAGAAACTAGATATGTTATAACTGACCAA
5171  179_HRV78    CATACGAACCAAGTACAGCCTGAAGACACCATAGAAACTAGATATGTTATAACTGACCAA
5172  GROUP_59     CATACGAACCAAGTACAGCCTGAAGACACCATAGAAACTAGATATGTTATAACTGACCAA
5173
5174  177_HRV78a   ACAAGAGATGAAATGAGCATTGAAAGTTTCCTCGGAAGATCAGGTTGTGCAACAATTATG
5175  178_HRV78b   ACAAGAGATGAAATGAGCATTGAAAGTTTCCTCGGAAGATCAGGTTGTGCAACAATTATG
5176  179_HRV78    ACAAGAGATGAAATGAGCATTGAAAGTTTCCTCGGAAGATCAGGTTGTGCAACAATTATG
5177  GROUP_59     ACAAGAGATGAAATGAGCATTGAAAGTTTCCTCGGAAGATCAGGTTGTGCAACAATTATG
5178
5179  177_HRV78a   AGACTAGAATTGGACCACACTGAT---------------TACAATGCT---GAAGGGAAA
5180  178_HRV78b   AGACTAGAATTGGACCACACTGAT---------------TACAATGCT---GAAGGGAAA
5181  179_HRV78    AGACTAGAATTGGACCACACTGAT---------------TACAATGCT---GAAGGGAAA
5182  GROUP_59     AGACTAGAATTGGACCACACTGAT...............TACAATGCT...GAAGGGAAA
5183
```

FIG. D14 CONT'D 10.trace                                                              9/20/2007 5:05 PM

```
5184  177_HRV78a   AATTTTACAACGTGGAAAATCAACTTACAGGAGATGGCCCAGATTAGAAGAAAGAATGAG
5185  178_HRV78b   AATTTTACAACGTGGAAAATCAACTTACAGGAGATGGCCCAGATTAGAAGAAAGAATGAG
5186  179_HRV78    AATTTTACAACGTGGAAAATCAACTTACAGGAGATGGCCCAGATTAGAAGAAAGAATGAG
5187  GROUP_59     AATTTTACAACGTGGAAAATCAACTTACAGGAGATGGCCCAGATTAGAAGAAAGAATGAG
5188
5189  177_HRV78a   ATGTTCACATATCTCAGATTTGATTCAGAAATCACTCTTG-TGTGTGCAGTGGCCTCACA
5190  178_HRV78b   ATGTTCACATATCTCAGATTTGATTCAGAAATCACTCTTG-TGTGTGCAGTGGCCTCACA
5191  179_HRV78    ATGTTCACATATCTCAGATTTGATTCAGAAATCACTCTTG-TGTGTGCAGTGGCCTCACA
5192  GROUP_59     ATGTTCACATATCTCAGATTTGATTCAGAAATCACTCTTG.TGTGTGCAGTGGCCTCACA
5193
5194  177_HRV78a   AGGAGACAATAATGGACATGTGGTGCTTCAATTTATGTTTGTTCCACCTGGAGCCCCTAT
5195  178_HRV78b   AGGAGACAATAATGGACATGTGGTGCTTCAATTTATGTTTGTTCCACCTGGAGCCCCTAT
5196  179_HRV78    AGGAGACAATAATGGACATGTGGTGCTTCAATTTATGTTTGTTCCACCTGGAGCCCCTAT
5197  GROUP_59     AGGAGACAATAATGGACATGTGGTGCTTCAATTTATGTTTGTTCCACCTGGAGCCCCTAT
5198
5199  177_HRV78a   ACCAAAGAAGAGAGATGACTATACTTGGCAGTCAGGCACCAATGCATCTGTGTTTTGGCA
5200  178_HRV78b   ACCAAAGAAGAGAGATGACTATACTTGGCAGTCAGGCACCAATGCATCTGTGTTTTGGCA
5201  179_HRV78    ACCAAAGAAGAGAGATGACTATACTTGGCAGTCAGGCACCAATGCATCTGTGTTTTGGCA
5202  GROUP_59     ACCAAAGAAGAGAGATGACTATACTTGGCAGTCAGGCACCAATGCATCTGTGTTTTGGCA
5203
5204  177_HRV78a   ACAAGGTCAAACATACCCCAGGTTCTCTATACCATTTTCTAGTATTGCCTCAGCTTATTA
5205  178_HRV78b   ACAAGGTCAAACATACCCCAGGTTCTCTATACCATTTTCTAGTATTGCCTCAGCTTATTA
5206  179_HRV78    ACAAGGTCAAACATACCCCAGGTTCTCTATACCATTTTCTAGTATTGCCTCAGCTTATTA
5207  GROUP_59     ACAAGGTCAAACATACCCCAGGTTCTCTATACCATTTTCTAGTATTGCCTCAGCTTATTA
5208
5209  177_HRV78a   CATGTTTTATGATGGATACTCGGATGACAGCACATCCTCTCCATATGGCACTGTAGTTAC
5210  178_HRV78b   CATGTTTTATGATGGATACTCGGATGACAGCACATCCTCTCCATATGGCACTGTAGTTAC
5211  179_HRV78    CATGTTTTATGATGGATACTCGGATGACAGCACATCCTCTCCATATGGCACTGTAGTTAC
5212  GROUP_59     CATGTTTTATGATGGATACTCGGATGACAGCACATCCTCTCCATATGGCACTGTAGTTAC
5213
5214  177_HRV78a   CAATGACATGGGTACACTGTGTATGAGGATGGTTACAGATCAACAACAACATAAGGTCAC
5215  178_HRV78b   CAATGACATGGGTACACTGTGTATGAGGATGGTTACAGATCAACAACAACATAAGGTCAC
5216  179_HRV78    CAATGACATGGGTACACTGTGTATGAGGATGGTTACAGATCAACAACAACATAAGGTCAC
5217  GROUP_59     CAATGACATGGGTACACTGTGTATGAGGATGGTTACAGATCAACAACAACATAAGGTCAC
5218
5219  177_HRV78a   AATTACAGCTAGAGTCTACCACAAGGCCAAACATATTAGTGCATGGGGCCCAAGACCTCC
5220  178_HRV78b   AATTACAGCTAGAGTCTACCACAAGGCCAAACATATTAGTGCATGGGGCCCAAGACCTCC
5221  179_HRV78    AATTACAGCTAGAGTCTACCACAAGGCCAAACATATTAGTGCATGGGGCCCAAGACCTCC
5222  GROUP_59     AATTACAGCTAGAGTCTACCACAAGGCCAAACATATTAGTGCATGGGGCCCAAGACCTCC
5223
5224  177_HRV78a   TAGAGCTGTACCTTATCAG-CACATATATAACCCTAATTATAAAA-CTGAAG------AA
5225  178_HRV78b   TAGAGCTGTACCTTATCAG-CACATATATAACCCTAATTATAAAA-CTGAAG------AA
5226  179_HRV78    TAGAGCTGTACCTTATCAG-CACATATATAACCCTAATTATAAAA-CTGAAG------AA
5227  GROUP_59     TAGAGCTGTACCTTATCAG.CACATATATAACCCTAATTATAAAA.CTGAAG......AA
5228
5229  177_HRV78a   GGAA------CTCCAGACACCAAAGTGGCAATTAGAGCTAATATTAAAACTGTA------
5230  178_HRV78b   GGAA------CTCCAGACACCAAAGTGGCAATTAGAGCTAATATTAAAACTGTG------
5231  179_HRV78    GGAA------CTCCAGACACCAAAGTGGCAATTAGAGCTAATATTAAAACTGTT------
5232  GROUP_59     GGAA......CTCCAGACACCAAAGTGGCAATTAGAGCTAATATTAAAACTGT-......
5233
5234  177_HRV78a   --------------------
5235  178_HRV78b   --------------------
5236  179_HRV78    --------------------
5237  GROUP_59     ....................
5238
5239
5240
5241  Group 60:
5242
5243  180_HRV20    AACCCAGTGGAAAGGTACACAGAAGCTATTTAAATGAAGTTCTTGTAGTTCCAAATATC
5244  181_HRV20a   AACCCAGTGGAAAGGTACACAGAAGCTATTTAAATGAAGTTCTTGTAGTTCCAAATATC
5245  182_HRV20b   AACCCAGTGGAAAGGTACACAGAAGCTATTTAAATGAAGTTCTTGTAGTTCCAAATATC
5246  GROUP_60     AACCCAGTGGAAAGGTACACAGAAGCTATTTTAAATGAAGTTCTTGTAGTTCCAAATATC
5247
5248  180_HRV20    ACATCTAGTAACTCCCAAACATCAAATGCAGCACCAGCACTAGATGCTGCTGAGACAGGA
```

FIG. D14 CONT'D

```
10.trace                                                                9/20/2007 5:05 PM 5249  181_HRV20a  ACATCTAGTAACTCCCAAACATCAAATGCAGCACCAGCACTAGATGCTGCTGAGACAGGA
5250  182_HRV20b  ACATCTAGTAACTCCCAAACATCAAATGCAGCACCAGCACTAGATGCTGCTGAGACAGGA
5251  GROUP_60    ACATCTAGTAACTCCCAAACATCAAATGCAGCACCAGCACTAGATGCTGCTGAGACAGGA
5252
5253  180_HRV20   CACACAAACCAGGTCCAGCCAGAAGATATGGTCGAGACACGGTATGTAATTACTGATCAG
5254  181_HRV20a  CACACAAACCAGGTCCAGCCAGAAGATATGGTCGAGACACGGTATGTAATTACTGATCAG
5255  182_HRV20b  CACACAAACCAGGTCCAGCCAGAAGATATGGTCGAGACACGGTATGTAATTACTGATCAG
5256  GROUP_60    CACACAAACCAGGTCCAGCCAGAAGATATGGTCGAGACACGGTATGTAATTACTGATCAG
5257
5258  180_HRV20   ACCCGTGATGAAATGAGTGTGGAAAGTTTTCTTGGTAGATCTGGTTGCATTGCTATCATA
5259  181_HRV20a  ACCCGTGATGAAATGAGTGTGGAAAGTTTTCTTGGTAGATCTGGTTGCATTGCTATCATA
5260  182_HRV20b  ACCCGTGATGAAATGAGTGTGGAAAGTTTTCTTGGTAGATCTGGTTGCATTGCTATCATA
5261  GROUP_60    ACCCGTGATGAAATGAGTGTGGAAAGTTTTCTTGGTAGATCTGGTTGCATTGCTATCATA
5262
5263  180_HRV20   CATACTGACTTAGATCATGAAGCACAA---------CAATATAATGCA---CCCGGAAAA
5264  181_HRV20a  CATACTGACTTAGATCATGAAGCACAA---------CAATATAATGCA---CCCGGAAAA
5265  182_HRV20b  CATACTGACTTAGATCATGAAGCACAA---------CAATATAATGCA---CCCGGAAAA
5266  GROUP_60    CATACTGACTTAGATCATGAAGCACAA.........CAATATAATGCA...CCCGGAAAA
5267
5268  180_HRV20   AATTTCTCTCAGTGGAAGATCACAATCAAGGAAATGGCTCAAATCAGAAGAAAATGTGAG
5269  181_HRV20a  AATTTCTCTCAGTGGAAGATCACAATCAAGGAAATGGCTCAAATCAGAAGAAAATGTGAG
5270  182_HRV20b  AATTTCTCTCAGTGGAAGATCACAATCAAGGAAATGGCTCAAATCAGAAGAAAATGTGAG
5271  GROUP_60    AATTTCTCTCAGTGGAAGATCACAATCAAGGAAATGGCTCAAATCAGAAGAAAATGTGAG
5272
5273  180_HRV20   CTCTTTACATACCTCAGATTTGATTCTGAGATTACAATAG-TAGCAACAGTAGCTGCACT
5274  181_HRV20a  CTCTTTACATACCTCAGATTTGATTCTGAGATTACAATAG-TAGCAACAGTAGCTGCACT
5275  182_HRV20b  CTCTTTACATACCTCAGATTTGATTCTGAGATTACAATAG-TAGCAACAGTAGCTGCACT
5276  GROUP_60    CTCTTTACATACCTCAGATTTGATTCTGAGATTACAATAG.TAGCAACAGTAGCTGCACT
5277
5278  180_HRV20   AGGTCGGGATAATGGGCATGTTGTTTTACAGTATATGTATGTACCACCAGGGGCACCAAT
5279  181_HRV20a  AGGTCGGGATAATGGGCATGTTGTTTTACAGTATATGTATGTACCACCAGGGGCACCAAT
5280  182_HRV20b  AGGTCGGGATAATGGGCATGTTGTTTTACAGTATATGTATGTACCACCAGGGGCACCAAT
5281  GROUP_60    AGGTCGGGATAATGGGCATGTTGTTTTACAGTATATGTATGTACCACCAGGGGCACCAAT
5282
5283  180_HRV20   ACCAAAGACTAGAGATGACTACACATGGCAATCAGGGACAAATGCATCAGTATTTTGGCA
5284  181_HRV20a  ACCAAAGACTAGAGATGACTACACATGGCAATCAGGGACAAATGCATCAGTATTTTGGCA
5285  182_HRV20b  ACCAAAGACTAGAGATGACTACACATGGCAATCAGGGACAAATGCATCAGTATTTTGGCA
5286  GROUP_60    ACCAAAGACTAGAGATGACTACACATGGCAATCAGGGACAAATGCATCAGTATTTTGGCA
5287
5288  180_HRV20   GCAGGGCCAACCTTACCCCAGATTTACCATTCCATTTATGAGTATAGCTTCAGCATATTA
5289  181_HRV20a  GCAGGGCCAACCTTACCCCAGATTTACCATTCCATTTATGAGTATAGCTTCAGCATATTA
5290  182_HRV20b  GCAGGGCCAACCTTACCCCAGATTTACCATTCCATTTATGAGTATAGCTTCAGCATATTA
5291  GROUP_60    GCAGGGCCAACCTTACCCCAGATTTACCATTCCATTTATGAGTATAGCTTCAGCATATTA
5292
5293  180_HRV20   TATGTTTTATGATGGTTATGAAGATGATAAGG---GAAGTGTGTATGGGTCTGTTGTCAC
5294  181_HRV20a  TATGTTTTATGATGGTTATGAAGATGATAAGG---GAAGTGTGTATGGGTCTGTTGTCAC
5295  182_HRV20b  TATGTTTTATGATGGTTATGAAGATGATAAGG---GAAGTGTGTATGGGTCTGTTGTCAC
5296  GROUP_60    TATGTTTTATGATGGTTATGAAGATGATAAGG...GAAGTGTGTATGGGTCTGTTGTCAC
5297
5298  180_HRV20   AAACGATATGGGCACATTGTGTGTTCGTATTGTGACTGAGCAGCAGACACATAAGGTTAA
5299  181_HRV20a  AAACGATATGGGCACATTGTGTGTTCGTATTGTGACTGAGCAGCAGACACATAAGGTTAA
5300  182_HRV20b  AAACGATATGGGCACATTGTGTGTTCGTATTGTGACTGAGCAGCAGACACATAAGGTTAA
5301  GROUP_60    AAACGATATGGGCACATTGTGTGTTCGTATTGTGACTGAGCAGCAGACACATAAGGTTAA
5302
5303  180_HRV20   GATAACCAGTAGGATATTCCACAAGGCAAAGCATATTAGTGCATGGTGTCCAAGGGCCCC
5304  181_HRV20a  GATAACCAGTAGGATATTCCACAAGGCAAAGCATATTAGTGCATGGTGTCCAAGGGCCCC
5305  182_HRV20b  GATAACCAGTAGGATATTCCACAAGGCAAAGCATATTAGTGCATGGTGTCCAAGGGCCCC
5306  GROUP_60    GATAACCAGTAGGATATTCCACAAGGCAAAGCATATTAGTGCATGGTGTCCAAGGGCCCC
5307
5308  180_HRV20   AAGAGCAGTGCCTTATCAA-CACACTAAGAGCACAAACTTAGTGC-CAAGGA---CAGGT
5309  181_HRV20a  AAGAGCAGTGCCTTATCAA-CACACTAAGAGCACAAACTTAGTGC-CAAGGA---CAGGT
5310  182_HRV20b  AAGAGCAGTGCCTTATCAA-CACACTAAGAGCACAAACTTAGTGC-CAAGGA---CAGGT
5311  GROUP_60    AAGAGCAGTGCCTTATCAA.CACACTAAGAGCACAAACTTAGTGC.CAAGGA...CAGGT
5312
5313  180_HRV20   GAAA------TTACA---ACTCATATCAGATTCAGAAACACTGTCAAAGATCTAACATAC
```

FIG. D14 CONT'D

```
10.trace                                                                    9/20/2007 5:05 PM 181_HRV20a      GAAA------TTACA---ACTCATATCAGATTCAGAAACACTGTCAAAGATCTAACATAC
182_HRV20b      GAAA------TTACA---ACTCATATCAGATTCAGAAACACTGTCAAAGATCTAACATAC
GROUP_60        GAAA......TTACA...ACTCATATCAGATTCAGAAACACTGTCAAAGATCTAACATAC 180_HRV20       CCCACAGAAATGACGAATGTT
181_HRV20a      CCCACAGAAATGACGAATGTA
182_HRV20b      CCCACAGAAATGACGAATGTG
GROUP_60        CCCACAGAAATGACGAATGT Group 61:

183_HRV68       AACCCAGTTGAAAAATACACAGAAGCCGTTCTTAATGAGGTCCTTGTGGTTCCAAACATA
184_HRV68a      AACCCAGTTGAAAAATACACAGAAGCCGTTCTTAATGAGGTCCTTGTGGTTCCAAACATA
185_HRV68b      AACCCAGTTGAAAAATACACAGAAGCCGTTCTTAATGAGGTCCTTGTGGTTCCAAACATA
GROUP_61        AACCCAGTTGAAAAATACACAGAAGCCGTTCTTAATGAGGTCCTTGTGGTTCCAAACATA

183_HRV68       CCAGCAAGTAATACCCAAACTTCAAATGCAGCCCCAGCCTTAGATGCTGCTGAGACTGGA
184_HRV68a      CCAGCAAGTAATACCCAAACTTCAAATGCAGCCCCAGCCTTAGATGCTGCTGAGACTGGA
185_HRV68b      CCAGCAAGTAATACCCAAACTTCAAATGCAGCCCCAGCCTTAGATGCTGCTGAGACTGGA
GROUP_61        CCAGCAAGTAATACCCAAACTTCAAATGCAGCCCCAGCCTTAGATGCTGCTGAGACTGGA

183_HRV68       CATACAAACCAAGTCCAACCAGAAGATGTGGTTGAAACACGCTATGTCATAACAGACCAG
184_HRV68a      CATACAAACCAAGTCCAACCAGAAGATGTGGTTGAAACACGCTATGTCATAACAGACCAG
185_HRV68b      CATACAAACCAAGTCCAACCAGAAGATGTGGTTGAAACACGCTATGTCATAACAGACCAG
GROUP_61        CATACAAACCAAGTCCAACCAGAAGATGTGGTTGAAACACGCTATGTCATAACAGACCAG

183_HRV68       ACAAGGGATGAAATGAGCATAGAGAGCTTCCTCGGTAGGTCAGGTTGCATTGCAATCATA
184_HRV68a      ACAAGGGATGAAATGAGCATAGAGAGCTTCCTCGGTAGGTCAGGTTGCATTGCAATCATA
185_HRV68b      ACAAGGGATGAAATGAGCATAGAGAGCTTCCTCGGTAGGTCAGGTTGCATTGCAATCATA
GROUP_61        ACAAGGGATGAAATGAGCATAGAGAGCTTCCTCGGTAGGTCAGGTTGCATTGCAATCATA

183_HRV68       CATACTGACTTAGATCACAATGAGGAT---------CAGTACAATGCA---CCTGGAAAA
184_HRV68a      CATACTGACTTAGATCACAATGAGGAT---------CAGTACAATGCA---CCTGGAAAA
185_HRV68b      CATACTGACTTAGATCACAATGAGGAT---------CAGTACAATGCA---CCTGGAAAA
GROUP_61        CATACTGACTTAGATCACAATGAGGAT.........CAGTACAATGCA...CCTGGAAAA

183_HRV68       AACTTCTCCCAATGGAAAATTACAATTAAGGAAATGGCTCAAATTAGAAGAAAGTGTGAA
184_HRV68a      AACTTCTCCCAATGGAAAATTACAATTAAGGAAATGGCTCAAATTAGAAGAAAGTGTGAA
185_HRV68b      AACTTCTCCCAATGGAAAATTACAATTAAGGAAATGGCTCAAATTAGAAGAAAGTGTGAA
GROUP_61        AACTTCTCCCAATGGAAAATTACAATTAAGGAAATGGCTCAAATTAGAAGAAAGTGTGAA

183_HRV68       CTATTCACATACCTTAGGTTTGACTCTGAGATTACAATAG-TAGCAACAATAGCTGCTCT
184_HRV68a      CTATTCACATACCTTAGGTTTGACTCTGAGATTACAATAG-TAGCAACAATAGCTGCTCT
185_HRV68b      CTATTCACATACCTTAGGTTTGACTCTGAGATTACAATAG-TAGCAACAATAGCTGCTCT
GROUP_61        CTATTCACATACCTTAGGTTTGACTCTGAGATTACAATAG.TAGCAACAATAGCTGCTCT

183_HRV68       TGGAAAAGATAATGGCCATGTGGTTTTACAGTACATGTATGTGCCGCCAGGGGCACCCAT
184_HRV68a      TGGAAAAGATAATGGCCATGTGGTTTTACAGTACATGTATGTGCCGCCAGGGGCACCCAT
185_HRV68b      TGGAAAAGATAATGGCCATGTGGTTTTACAGTACATGTATGTGCCGCCAGGGGCACCCAT
GROUP_61        TGGAAAAGATAATGGCCATGTGGTTTTACAGTACATGTATGTGCCGCCAGGGGCACCCAT

183_HRV68       ACCAAAAACTAGAGATGATTACACATGGCAGTCAGGCACTAATGCATCAGTGTTTTGGCA
184_HRV68a      ACCAAAAACTAGAGATGATTACACATGGCAGTCAGGCACTAATGCATCAGTGTTTTGGCA
185_HRV68b      ACCAAAAACTAGAGATGATTACACATGGCAGTCAGGCACTAATGCATCAGTGTTTTGGCA
GROUP_61        ACCAAAAACTAGAGATGATTACACATGGCAGTCAGGCACTAATGCATCAGTGTTTTGGCA

183_HRV68       ACAAGGACAACCTTACCCCAGATTTACCATTCCATTTATGAGTATAGCTTCAGCATATTA
184_HRV68a      ACAAGGACAACCTTACCCCAGATTTACCATTCCATTTATGAGTATAGCTTCAGCATATTA
185_HRV68b      ACAAGGACAACCTTACCCCAGATTTACCATTCCATTTATGAGTATAGCTTCAGCATATTA
GROUP_61        ACAAGGACAACCTTACCCCAGATTTACCATTCCATTTATGAGTATAGCTTCAGCATATTA

183_HRV68       TATGTTTTATGATGGATATGAGGATGACAAAG---GAAGTGTGTATGGATCTGTTGTTAC
184_HRV68a      TATGTTTTATGATGGATATGAGGATGACAAAG---GAAGTGTGTATGGATCTGTTGTTAC
```

FIG. D14 CONT'D

```
10.trace                                                                                          9/20/2007 5:05 PM 5379  185_HRV68b  TATGTTTTATGATGGATATGAGGATGACAAAG---GAAGTGTGTATGGATCTGTTGTTAC
5380  GROUP_61   TATGTTTTATGATGGATATGAGGATGACAAAG...GAAGTGTGTATGGATCTGTTGTTAC
5381
5382  183_HRV68   AAATGATATGGGCACATTATGTGTCCGTATTGTGACTGAGCAGCAGACACATAGGGTCAA
5383  184_HRV68a  AAATGATATGGGCACATTATGTGTCCGTATTGTGACTGAGCAGCAGACACATAGGGTCAA
5384  185_HRV68b  AAATGATATGGGCACATTATGTGTCCGTATTGTGACTGAGCAGCAGACACATAGGGTCAA
5385  GROUP_61   AAATGATATGGGCACATTATGTGTCCGTATTGTGACTGAGCAGCAGACACATAGGGTCAA
5386
5387  183_HRV68   AATAACCAGCAGAATATTCCATAAAGCAAAACATATTAGTGCGTGGTGTCCAAGAGCTCC
5388  184_HRV68a  AATAACCAGCAGAATATTCCATAAAGCAAAACATATTAGTGCGTGGTGTCCAAGAGCTCC
5389  185_HRV68b  AATAACCAGCAGAATATTCCATAAAGCAAAACATATTAGTGCGTGGTGTCCAAGAGCTCC
5390  GROUP_61   AATAACCAGCAGAATATTCCATAAAGCAAAACATATTAGTGCGTGGTGTCCAAGAGCTCC
5391
5392  183_HRV68   AAGAGCAGTGCCCTACCAG-CACACCAGAAGTACAAACTTAGTAC-CAAAGG---AAGGT
5393  184_HRV68a  AAGAGCAGTGCCCTACCAG-CACACCAGAAGTACAAACTTAGTAC-CAAAGG---AAGGT
5394  185_HRV68b  AAGAGCAGTGCCCTACCAG-CACACCAGAAGTACAAACTTAGTAC-CAAAGG---AAGGT
5395  GROUP_61   AAGAGCAGTGCCCTACCAG.CACACCAGAAGTACAAACTTAGTAC.CAAAGG...AAGGT
5396
5397  183_HRV68   GATA------TTAAA---ACTCATATTAAATTTAGGAATACTGTTAAAGATTTGGCATAT
5398  184_HRV68a  GATA------TTAAA---ACTCATATTAAATTTAGGAATACTGTTAAAGATTTGGCATAT
5399  185_HRV68b  GATA------TTAAA---ACTCATATTAAATTTAGGAATACTGTTAAAGATTTGGCATAT
5400  GROUP_61   GATA......TTAAA...ACTCATATTAAATTTAGGAATACTGTTAAAGATTTGGCATAT
5401
5402  183_HRV68   CCTCCAGAATTAGCAAACCTT
5403  184_HRV68a  CCTCCAGAATTAGCAAACCTT
5404  185_HRV68b  CCTCCAGAATTAGCAAACCTT
5405  GROUP_61   CCTCCAGAATTAGCAAACCTT
5406
5407
5408
5409  Group_62:
5410
5411  186_HRV28   AATCCAGTTGAAAAATATACTGAAGCACTACTTAATGAAGTGCTTGTTGTGCCAAACATC
5412  187_HRV28a  AATCCAGTTGAAAAATATACTGAAGCACTACTTAATGAAGTGCTTGTTGTGCCAAACATC
5413  188_HRV28b  AATCCAGTTGAAAAATATACTGAAGCACTACTTAATGAAGTGCTTGTTGTGCCAAACATC
5414  GROUP_62   AATCCAGTTGAAAAATATACTGAAGCACTACTTAATGAAGTGCTTGTTGTGCCAAACATC
5415
5416  186_HRV28   AATCCTAGCAACGCACAAACTACAAATGCAGCTCCCGCTCTCGATGCCGCTGAGACGGGG
5417  187_HRV28a  AATCCTAGCAACGCACAAACTACAAATGCAGCTCCCGCTCTCGATGCCGCTGAGACGGGG
5418  188_HRV28b  AATCCTAGCAACGCACAAACTACAAATGCAGCTCCCGCTCTCGATGCCGCTGAGACGGGG
5419  GROUP_62   AATCCTAGCAACGCACAAACTACAAATGCAGCTCCCGCTCTCGATGCCGCTGAGACGGGG
5420
5421  186_HRV28   CACACAAGCCAAACACAACCTGAAGACATGGTTGAGACTAGGTATGTAATCACAGATCAG
5422  187_HRV28a  CACACAAGCCAAACACAACCTGAAGACATGGTTGAGACTAGGTATGTAATCACAGATCAG
5423  188_HRV28b  CACACAAGCCAAACACAACCTGAAGACATGGTTGAGACTAGGTATGTAATCACAGATCAG
5424  GROUP_62   CACACAAGCCAAACACAACCTGAAGACATGGTTGAGACTAGGTATGTAATCACAGATCAG
5425
5426  186_HRV28   ACCCGTGATGAAATGAGTATAGAGAGTTTCTTAGGTAGGTCTAGTTGCATTGCAATAATC
5427  187_HRV28a  ACCCGTGATGAAATGAGTATAGAGAGTTTCTTAGGTAGGTCTAGTTGCATTGCAATAATC
5428  188_HRV28b  ACCCGTGATGAAATGAGTATAGAGAGTTTCTTAGGTAGGTCTAGTTGCATTGCAATAATC
5429  GROUP_62   ACCCGTGATGAAATGAGTATAGAGAGTTTCTTAGGTAGGTCTAGTTGCATTGCAATAATC
5430
5431  186_HRV28   CATACTGATGTTGTGCATGAAACAGAC---------AAGTACAACCAC---CCAGGGAAG
5432  187_HRV28a  CATACTGATGTTGTGCATGAAACAGAC---------AAGTACAACCAC---CCAGGGAAG
5433  188_HRV28b  CATACTGATGTTGTGCATGAAACAGAC---------AAGTACAACCAC---CCAGGGAAG
5434  GROUP_62   CATACTGATGTTGTGCATGAAACAGAC.........AAGTACAACCAC...CCAGGGAAG
5435
5436  186_HRV28   AATTTTAGTAAATGGAATATCACTCTCAAAGAAATGGCCCAAATCAGAAGAAAGTGTGAA
5437  187_HRV28a  AATTTTAGTAAATGGAATATCACTCTCAAAGAAATGGCCCAAATCAGAAGAAAGTGTGAA
5438  188_HRV28b  AATTTTAGTAAATGGAATATCACTCTCAAAGAAATGGCCCAAATCAGAAGAAAGTGTGAA
5439  GROUP_62   AATTTTAGTAAATGGAATATCACTCTCAAAGAAATGGCCCAAATCAGAAGAAAGTGTGAA
5440
5441  186_HRV28   ATGTTTACATATCTCAGATTTGATTCTGAAATTACTATAG-TGGTGTCAGTTGCAAGTAA
5442  187_HRV28a  ATGTTTACATATCTCAGATTTGATTCTGAAATTACTATAG-TGGTGTCAGTTGCAAGTAA
5443  188_HRV28b  ATGTTTACATATCTCAGATTTGATTCTGAAATTACTATAG-TGGTGTCAGTTGCAAGTAA
```

FIG. D14 CONT'D

```
10.trace                                                              9/20/2007 5:05 PM 5444  GROUP_62     ATGTTTACATATCTCAGATTTGATTCTGAAATTACTATAG.TGGTGTCAGTTGCAAGTAA
5445
5446  186_HRV28    AGGTGATGATAATGGGCATGTAGTTATGCAATATATGTATGTACCTCCAGGAGCCCCCAT
5447  187_HRV28a   AGGTGATGATAATGGGCATGTAGTTATGCAATATATGTATGTACCTCCAGGAGCCCCCAT
5448  188_HRV28b   AGGTGATGATAATGGGCATGTAGTTATGCAATATATGTATGTACCTCCAGGAGCCCCCAT
5449  GROUP_62     AGGTGATGATAATGGGCATGTAGTTATGCAATATATGTATGTACCTCCAGGAGCCCCCAT
5450
5451  186_HRV28    CCCCACTACCAGAAATGATTACACATGGCAATCCAGTACCAATGCCTCTGTTTTCTGGCA
5452  187_HRV28a   CCCCACTACCAGAAATGATTACACATGGCAATCCAGTACCAATGCCTCTGTTTTCTGGCA
5453  188_HRV28b   CCCCACTACCAGAAATGATTACACATGGCAATCCAGTACCAATGCCTCTGTTTTCTGGCA
5454  GROUP_62     CCCCACTACCAGAAATGATTACACATGGCAATCCAGTACCAATGCCTCTGTTTTCTGGCA
5455
5456  186_HRV28    ACAAGGACAACCATATCCCAGATTCACTATACCTTTTATGAGTATTGCCTCAGCTTATTA
5457  187_HRV28a   ACAAGGACAACCATATCCCAGATTCACTATACCTTTTATGAGTATTGCCTCAGCTTATTA
5458  188_HRV28b   ACAAGGACAACCATATCCCAGATTCACTATACCTTTTATGAGTATTGCCTCAGCTTATTA
5459  GROUP_62     ACAAGGACAACCATATCCCAGATTCACTATACCTTTTATGAGTATTGCCTCAGCTTATTA
5460
5461  186_HRV28    CATGTTTTATGATGGTTATGAAGATGACAATG---GAACTACCTATGGTGCAGTGGTTAC
5462  187_HRV28a   CATGTTTTATGATGGTTATGAAGATGACAATG---GAACTACCTATGGTGCAGTGGTTAC
5463  188_HRV28b   CATGTTTTATGATGGTTATGAAGATGACAATG---GAACTACCTATGGTGCAGTGGTTAC
5464  GROUP_62     CATGTTTTATGATGGTTATGAAGATGACAATG...GAACTACCTATGGTGCAGTGGTTAC
5465
5466  186_HRV28    AAATCATATGGGAACACTCTGTGCTCGCATAGTAACTGAACAACAGAAGCATGAAGTCAA
5467  187_HRV28a   AAATCATATGGGAACACTCTGTGCTCGCATAGTAACTGAACAACAGAAGCATGAAGTCAA
5468  188_HRV28b   AAATCATATGGGAACACTCTGTGCTCGCATAGTAACTGAACAACAGAAGCATGAAGTCAA
5469  GROUP_62     AAATCATATGGGAACACTCTGTGCTCGCATAGTAACTGAACAACAGAAGCATGAAGTCAA
5470
5471  186_HRV28    AATAACCAGCATAATATTCCACAAAGCTAAACATGTCAGTGCATGGTGCCCCAGACCTCC
5472  187_HRV28a   AATAACCAGCATAATATTCCACAAAGCTAAACATGTCAGTGCATGGTGCCCCAGACCTCC
5473  188_HRV28b   AATAACCAGCATAATATTCCACAAAGCTAAACATGTCAGTGCATGGTGCCCCAGACCTCC
5474  GROUP_62     AATAACCAGCATAATATTCCACAAAGCTAAACATGTCAGTGCATGGTGCCCCAGACCTCC
5475
5476  186_HRV28    ACGCGCTGTAGCTTATCAA-CATACATACAGTCCAAACTTTGTGC-CTCAGG---AAGGT
5477  187_HRV28a   ACGCGCTGTAGCTTATCAA-CATACATACAGTCCAAACTTTGTGC-CTCAGG---AAGGT
5478  188_HRV28b   ACGCGCTGTAGCTTATCAA-CATACATACAGTCCAAACTTTGTGC-CTCAGG---AAGGT
5479  GROUP_62     ACGCGCTGTAGCTTATCAA.CATACATACAGTCCAAACTTTGTGC.CTCAGG...AAGGT
5480
5481  186_HRV28    GATG------TTGAG---ACTCATATTAAATTTAGAACAGATGTTAAACAGATCACAA--
5482  187_HRV28a   GATG------TTGAG---ACTCATATTAAATTTAGAACAGATGTTAAACAGATCACAA--
5483  188_HRV28b   GATG------TTGAG---ACTCATATTAAATTTAGAACAGATGTTAAACAGATCACAA--
5484  GROUP_62     GATG......TTGAG...ACTCATATTAAATTTAGAACAGATGTTAAACAGATCACAA..
5485
5486  186_HRV28    ----CAGTT-----------
5487  187_HRV28a   ----CAGTA-----------
5488  188_HRV28b   ----CAGTC-----------
5489  GROUP_62     ....CAGT-...........
5490
5491
5492
5493  Group  63:
5494
5495  189_HRV53a   AACCCGGTAGAGAAATACACAGAGGCTATCTTAAATGAAGTATTAGTAGTCCCAAACATT
5496  190_HRV53b   AACCCGGTAGAGAAATACACAGAGGCTATCTTAAATGAAGTATTAGTAGTCCCAAACATT
5497  191_HRV53    AACCCGGTAGAGAAATACACAGAGGCTATCTTAAATGAAGTATTAGTAGTCCCAAACATT
5498  GROUP_63     AACCCGGTAGAGAAATACACAGAGGCTATCTTAAATGAAGTATTAGTAGTCCCAAACATT
5499
5500  189_HRV53a   AATGCAAGCAATCCACAAACTTCAAATTCAGCACCAGCACTAGATGCTGCAGAAACGGGT
5501  190_HRV53b   AATGCAAGCAATCCACAAACTTCAAATTCAGCACCAGCACTAGATGCTGCAGAAACGGGT
5502  191_HRV53    AATGCAAGCAATCCACAAACTTCAAATTCAGCACCAGCACTAGATGCTGCAGAAACGGGT
5503  GROUP_63     AATGCAAGCAATCCACAAACTTCAAATTCAGCACCAGCACTAGATGCTGCAGAAACGGGT
5504
5505  189_HRV53a   CATACAAGTCAGACACAACCTGAGGACATGCTGGAAACTAGATATGTCATCACAGACCAA
5506  190_HRV53b   CATACAAGTCAGACACAACCTGAGGACATGCTGGAAACTAGATATGTCATCACAGACCAA
5507  191_HRV53    CATACAAGTCAGACACAACCTGAGGACATGCTGGAAACTAGATATGTCATCACAGACCAA
5508  GROUP_63     CATACAAGTCAGACACAACCTGAGGACATGCTGGAAACTAGATATGTCATCACAGACCAA
```

FIG. D14 CONT'D

```
10.trace                                                                                        9/20/2007 5:05 PM 5509
5510  189_HRV53a    ACCCGGGATGAAATGAGCATTGAAAGTTTCTTAGGCAGATCAAGTTGCATTGCTGAGATC
5511  190_HRV53b    ACCCGGGATGAAATGAGCATTGAAAGTTTCTTAGGCAGATCAAGTTGCATTGCTGAGATC
5512  191_HRV53     ACCCGGGATGAAATGAGCATTGAAAGTTTCTTAGGCAGATCAAGTTGCATTGCTGAGATC
5513  GROUP_63      ACCCGGGATGAAATGAGCATTGAAAGTTTCTTAGGCAGATCAAGTTGCATTGCTGAGATC
5514
5515  189_HRV53a    CATACCAATTTAGACCAT---ACTG-----------GATACAATGAG---CCTGGGAAA
5516  190_HRV53b    CATACCAATTTAGACCAT---ACTG-----------GATACAATGAG---CCTGGGAAA
5517  191_HRV53     CATACCAATTTAGACCAT---ACTG-----------GATACAATGAG---CCTGGGAAA
5518  GROUP_63      CATACCAATTTAGACCAT...ACTG...........GATACAATGAG...CCTGGGAAA
5519
5520  189_HRV53a    AACCACTCAGAATGGAAGATTACACTCAAAGAAATGGCCCAGATTAGAAGGAAATGTGAG
5521  190_HRV53b    AACCACTCAGAATGGAAGATTACACTCAAAGAAATGGCCCAGATTAGAAGGAAATGTGAG
5522  191_HRV53     AACCACTCAGAATGGAAGATTACACTCAAAGAAATGGCCCAGATTAGAAGGAAATGTGAG
5523  GROUP_63      AACCACTCAGAATGGAAGATTACACTCAAAGAAATGGCCCAGATTAGAAGGAAATGTGAG
5524
5525  189_HRV53a    ATGTTCACATATCTTAGATTTGATTCAGAAATAACTATAG-TGGTATCAGTGGCTAGTAA
5526  190_HRV53b    ATGTTCACATATCTTAGATTTGATTCAGAAATAACTATAG-TGGTATCAGTGGCTAGTAA
5527  191_HRV53     ATGTTCACATATCTTAGATTTGATTCAGAAATAACTATAG-TGGTATCAGTGGCTAGTAA
5528  GROUP_63      ATGTTCACATATCTTAGATTTGATTCAGAAATAACTATAG.TGGTATCAGTGGCTAGTAA
5529
5530  189_HRV53a    ACAAGGGAATAACGGGCACGTGGTGATACAATACATGTATGTACCACCGGGTGCTCCAAT
5531  190_HRV53b    ACAAGGGAATAACGGGCACGTGGTGATACAATACATGTATGTACCACCGGGTGCTCCAAT
5532  191_HRV53     ACAAGGGAATAACGGGCACGTGGTGATACAATACATGTATGTACCACCGGGTGCTCCAAT
5533  GROUP_63      ACAAGGGAATAACGGGCACGTGGTGATACAATACATGTATGTACCACCGGGTGCTCCAAT
5534
5535  189_HRV53a    ACCCAAAACCAGAGATGACTATACCTGGCAATCTGGAACTAATGCTTCAGTCTTTTGGCA
5536  190_HRV53b    ACCCAAAACCAGAGATGACTATACCTGGCAATCTGGAACTAATGCTTCAGTCTTTTGGCA
5537  191_HRV53     ACCCAAAACCAGAGATGACTATACCTGGCAATCTGGAACTAATGCTTCAGTCTTTTGGCA
5538  GROUP_63      ACCCAAAACCAGAGATGACTATACCTGGCAATCTGGAACTAATGCTTCAGTCTTTTGGCA
5539
5540  189_HRV53a    ACAAGGACAACCATACCCTAGATTCACAATCCCTTTCATGAGTATTGCGTCAGCATATTA
5541  190_HRV53b    ACAAGGACAACCATACCCTAGATTCACAATCCCTTTCATGAGTATTGCGTCAGCATATTA
5542  191_HRV53     ACAAGGACAACCATACCCTAGATTCACAATCCCTTTCATGAGTATTGCGTCAGCATATTA
5543  GROUP_63      ACAAGGACAACCATACCCTAGATTCACAATCCCTTTCATGAGTATTGCGTCAGCATATTA
5544
5545  189_HRV53a    TATGTTCTATGATGGGTATGAAGATGACAATG---GCACCACTTATGGGGCTGTTGTTAC
5546  190_HRV53b    TATGTTCTATGATGGGTATGAAGATGACAATG---GCACCACTTATGGGGCTGTTGTTAC
5547  191_HRV53     TATGTTCTATGATGGGTATGAAGATGACAATG---GCACCACTTATGGGGCTGTTGTTAC
5548  GROUP_63      TATGTTCTATGATGGGTATGAAGATGACAATG...GCACCACTTATGGGGCTGTTGTTAC
5549
5550  189_HRV53a    TAATGATATGGGAACACTTTGTGTGCGCATAGTGACTGAGCAACAGAAAAATGAGGTCAA
5551  190_HRV53b    TAATGATATGGGAACACTTTGTGTGCGCATAGTGACTGAGCAACAGAAAAATGAGGTCAA
5552  191_HRV53     TAATGATATGGGAACACTTTGTGTGCGCATAGTGACTGAGCAACAGAAAAATGAGGTCAA
5553  GROUP_63      TAATGATATGGGAACACTTTGTGTGCGCATAGTGACTGAGCAACAGAAAAATGAGGTCAA
5554
5555  189_HRV53a    GATAACCAGTAGGATTTATCACAAGGCTAAACATATCAGTGCATGGTGTCCAAGACCACC
5556  190_HRV53b    GATAACCAGTAGGATTTATCACAAGGCTAAACATATCAGTGCATGGTGTCCAAGACCACC
5557  191_HRV53     GATAACCAGTAGGATTTATCACAAGGCTAAACATATCAGTGCATGGTGTCCAAGACCACC
5558  GROUP_63      GATAACCAGTAGGATTTATCACAAGGCTAAACATATCAGTGCATGGTGTCCAAGACCACC
5559
5560  189_HRV53a    AAGAGCAGTTGCATATCAA-CACACATATAGCCCAAATTTTGTAC-CGCAAA---CAGGA
5561  190_HRV53b    AAGAGCAGTTGCATATCAA-CACACATATAGCCCAAATTTTGTAC-CGCAAA---CAGGA
5562  191_HRV53     AAGAGCAGTTGCATATCAA-CACACATATAGCCCAAATTTTGTAC-CGCAAA---CAGGA
5563  GROUP_63      AAGAGCAGTTGCATATCAA.CACACATATAGCCCAAATTTTGTAC.CGCAAA...CAGGA
5564
5565  189_HRV53a    ACAG------TTGAA---ACTCACATTAAGTTCAGACCTGATGTTAAAGATGTAACAT--
5566  190_HRV53b    ACAG------TTGAA---ACTCACATTAAGTTCAGACCTGATGTTAAAGATGTAACAT--
5567  191_HRV53     ACAG------TTGAA---ACTCACATTAAGTTCAGACCTGATGTTAAAGATGTAACAT--
5568  GROUP_63      ACAG......TTGAA...ACTCACATTAAGTTCAGACCTGATGTTAAAGATGTAACAT..
5569
5570  189_HRV53a    ----CAGTAATGACAGCT---
5571  190_HRV53b    ----CAGTAATGACAGCT---
5572  191_HRV53     ----CAGTAATGACAGCA---
5573  GROUP_63      ....CAGTAATGACAGC-...
```

FIG. D14 CONT'D 10.trace                                                                                          9/20/2007 5:05 PM

```
Group 64:

192_HRV46a   AATCCAGTGGAAAAATATACAGAAGCTGTTCTTAATGAGGTCCTTGTAGTACCTAACATC
193_HRV46b   AATCCAGTGGAAAAATATACAGAAGCTGTTCTTAATGAGGTCCTTGTAGTACCTAACATC
194_HRV46    AATCCAGTGGAAAAATATACAGAAGCTGTTCTTAATGAGGTCCTTGTAGTACCTAACATC
GROUP_64     AATCCAGTGGAAAAATATACAGAAGCTGTTCTTAATGAGGTCCTTGTAGTACCTAACATC

192_HRV46a   AATGCCAGTAGTGGACATACATCTAATTCAGCTCCAGCACTTGATGCAGCAGAAACTGGA
193_HRV46b   AATGCCAGTAGTGGACATACATCTAATTCAGCTCCAGCACTTGATGCAGCAGAAACTGGA
194_HRV46    AATGCCAGTAGTGGACATACATCTAATTCAGCTCCAGCACTTGATGCAGCAGAAACTGGA
GROUP_64     AATGCCAGTAGTGGACATACATCTAATTCAGCTCCAGCACTTGATGCAGCAGAAACTGGA

192_HRV46a   CACACTAGCCAGATACAACCAGAAGACATGATAGAAACCAGATATGTTATCACAGACCAA
193_HRV46b   CACACTAGCCAGATACAACCAGAAGACATGATAGAAACCAGATATGTTATCACAGACCAA
194_HRV46    CACACTAGCCAGATACAACCAGAAGACATGATAGAAACCAGATATGTTATCACAGACCAA
GROUP_64     CACACTAGCCAGATACAACCAGAAGACATGATAGAAACCAGATATGTTATCACAGACCAA

192_HRV46a   ACAAAAGATGAAATGAGTATAGAAAGTTTTCTAGGAAGGTCAGGCTGCATTGCCATTATT
193_HRV46b   ACAAAAGATGAAATGAGTATAGAAAGTTTTCTAGGAAGGTCAGGCTGCATTGCCATTATT
194_HRV46    ACAAAAGATGAAATGAGTATAGAAAGTTTTCTAGGAAGGTCAGGCTGCATTGCCATTATT
GROUP_64     ACAAAAGATGAAATGAGTATAGAAAGTTTTCTAGGAAGGTCAGGCTGCATTGCCATTATT

192_HRV46a   GAGACAGAATTGAATCATGAAGAAGGG--------AAATACAATGCA---GAAGATCAA
193_HRV46b   GAGACAGAATTGAATCATGAAGAAGGG--------AAATACAATGCA---GAAGATCAA
194_HRV46    GAGACAGAATTGAATCATGAAGAAGGG--------AAATACAATGCA---GAAGATCAA
GROUP_64     GAGACAGAATTGAATCATGAAGAAGGG.........AAATACAATGCA...GAAGATCAA

192_HRV46a   AACTTCTCAAAATGGAAAATAACACTGTTGGAAATGGCACAAATCAGAAGAAAGTGTGAA
193_HRV46b   AACTTCTCAAAATGGAAAATAACACTGTTGGAAATGGCACAAATCAGAAGAAAGTGTGAA
194_HRV46    AACTTCTCAAAATGGAAAATAACACTGTTGGAAATGGCACAAATCAGAAGAAAGTGTGAA
GROUP_64     AACTTCTCAAAATGGAAAATAACACTGTTGGAAATGGCACAAATCAGAAGAAAGTGTGAA

192_HRV46a   CTTTTTACATATCTCAGATTTGATTCAGAAATAACAATAG-TCACCACATTGGCAGGCCA
193_HRV46b   CTTTTTACATATCTCAGATTTGATTCAGAAATAACAATAG-TCACCACATTGGCAGGCCA
194_HRV46    CTTTTTACATATCTCAGATTTGATTCAGAAATAACAATAG-TCACCACATTGGCAGGCCA
GROUP_64     CTTTTTACATATCTCAGATTTGATTCAGAAATAACAATAG.TCACCACATTGGCAGGCCA

192_HRV46a   AGGGGATGATATTGGACATGTGGTCATACAATATATGTATGTGCCTCCTGGTGCTCCATT
193_HRV46b   AGGGGATGATATTGGACATGTGGTCATACAATATATGTATGTGCCTCCTGGTGCTCCATT
194_HRV46    AGGGGATGATATTGGACATGTGGTCATACAATATATGTATGTGCCTCCTGGTGCTCCATT
GROUP_64     AGGGGATGATATTGGACATGTGGTCATACAATATATGTATGTGCCTCCTGGTGCTCCATT

192_HRV46a   ACCGAGATATCGGAATGATTATACTTGGCAGTCTGGTACTAATGCTTCAGTGTTCTGGCA
193_HRV46b   ACCGAGATATCGGAATGATTATACTTGGCAGTCTGGTACTAATGCTTCAGTGTTCTGGCA
194_HRV46    ACCGAGATATCGGAATGATTATACTTGGCAGTCTGGTACTAATGCTTCAGTGTTCTGGCA
GROUP_64     ACCGAGATATCGGAATGATTATACTTGGCAGTCTGGTACTAATGCTTCAGTGTTCTGGCA

192_HRV46a   GCAAGGGCAGCCATACCCTAGATTCACTATCCCGTTCATGAGTATAGCCTCAGCATATTA
193_HRV46b   GCAAGGGCAGCCATACCCTAGATTCACTATCCCGTTCATGAGTATAGCCTCAGCATATTA
194_HRV46    GCAAGGGCAGCCATACCCTAGATTCACTATCCCGTTCATGAGTATAGCCTCAGCATATTA
GROUP_64     GCAAGGGCAGCCATACCCTAGATTCACTATCCCGTTCATGAGTATAGCCTCAGCATATTA

192_HRV46a   CATGTTTTATGATGGCTACGAAAGTGATAAAG---GCAAGATCTATGGAACTGCAGTCAC
193_HRV46b   CATGTTTTATGATGGCTACGAAAGTGATAAAG---GCAAGATCTATGGAACTGCAGTCAC
194_HRV46    CATGTTTTATGATGGCTACGAAAGTGATAAAG---GCAAGATCTATGGAACTGCAGTCAC
GROUP_64     CATGTTTTATGATGGCTACGAAAGTGATAAAG...GCAAGATCTATGGAACTGCAGTCAC

192_HRV46a   CAATGATATGGGAACTATATGTGTCAGAATTGTTACCGAACAACAAAAACATAAGGTTCT
193_HRV46b   CAATGATATGGGAACTATATGTGTCAGAATTGTTACCGAACAACAAAAACATAAGGTTCT
194_HRV46    CAATGATATGGGAACTATATGTGTCAGAATTGTTACCGAACAACAAAAACATAAGGTTCT
GROUP_64     CAATGATATGGGAACTATATGTGTCAGAATTGTTACCGAACAACAAAAACATAAGGTTCT
```

FIG. D14 CONT'D 10.trace                                                                 9/20/2007 5:05 PM

| | | |
|---|---|---|
| 5639 | 192_HRV46a | TATAACTAGCAGAATATATCACAAGGCTAAACACATTAAAGCATGGTGCCCCAGGGCACC |
| 5640 | 193_HRV46b | TATAACTAGCAGAATATATCACAAGGCTAAACACATTAAAGCATGGTGCCCCAGGGCACC |
| 5641 | 194_HRV46  | TATAACTAGCAGAATATATCACAAGGCTAAACACATTAAAGCATGGTGCCCCAGGGCACC |
| 5642 | GROUP_64   | TATAACTAGCAGAATATATCACAAGGCTAAACACATTAAAGCATGGTGCCCCAGGGCACC |
| 5643 | | |
| 5644 | 192_HRV46a | CAGAGCAGTCCCATATCAA-CATATTTATAATCCAAATTTCAAGA-CTACTCAACCTGAG |
| 5645 | 193_HRV46b | CAGAGCAGTCCCATATCAA-CATATTTATAATCCAAATTTCAAGA-CTACTCAACCTGAG |
| 5646 | 194_HRV46  | CAGAGCAGTCCCATATCAA-CATATTTATAATCCAAATTTCAAGA-CTACTCAACCTGAG |
| 5647 | GROUP_64   | CAGAGCAGTCCCATATCAA.CATATTTATAATCCAAATTTCAAGA.CTACTCAACCTGAG |
| 5648 | | |
| 5649 | 192_HRV46a | ACTA------TACCAGATACTCATATTGGAATTAGAAGGGATATAAAGTACATTAAAA-- |
| 5650 | 193_HRV46b | ACTA------TACCAGATACTCATATTGGAATTAGAAGGGATATAAAGTACATTAAAA-- |
| 5651 | 194_HRV46  | ACTA------TACCAGATACTCATATTGGAATTAGAAGGGATATAAAGTACATTAAAA-- |
| 5652 | GROUP_64   | ACTA......TACCAGATACTCATATTGGAATTAGAAGGGATATAAAGTACATTAAAA.. |
| 5653 | | |
| 5654 | 192_HRV46a | ----CAGCA------------ |
| 5655 | 193_HRV46b | ----CAGCC------------ |
| 5656 | 194_HRV46  | ----CAGCT------------ |
| 5657 | GROUP_64   | ....CAGC-............ |
| 5658 | | |
| 5659 | | |
| 5660 | | |
| 5661 | Group 65: | |
| 5662 | | |
| 5663 | 195_HRV80a | AATCCAGTCGAAAAATACACAGAAGCAATCCTCAATGAAGTTCTTGTTGTACCAAACATC |
| 5664 | 196_HRV80b | AATCCAGTCGAAAAATACACAGAAGCAATCCTCAATGAAGTTCTTGTTGTACCAAACATC |
| 5665 | 197_HRV80  | AATCCAGTCGAAAAATACACAGAAGCAATCCTCAATGAAGTTCTTGTTGTACCAAACATC |
| 5666 | GROUP_65   | AATCCAGTCGAAAAATACACAGAAGCAATCCTCAATGAAGTTCTTGTTGTACCAAACATC |
| 5667 | | |
| 5668 | 195_HRV80a | AGTGCTAGCAATGGACATACATCAAACTCAGCTCCAACACTTGATGCAGCAGAAACTGGT |
| 5669 | 196_HRV80b | AGTGCTAGCAATGGACATACATCAAACTCAGCTCCAACACTTGATGCAGCAGAAACTGGT |
| 5670 | 197_HRV80  | AGTGCTAGCAATGGACATACATCAAACTCAGCTCCAACACTTGATGCAGCAGAAACTGGT |
| 5671 | GROUP_65   | AGTGCTAGCAATGGACATACATCAAACTCAGCTCCAACACTTGATGCAGCAGAAACTGGT |
| 5672 | | |
| 5673 | 195_HRV80a | CACACTAGCCAGGTGCAACCAGAAGACATGATAGAAACTAGATATGTTATTACTGATCAG |
| 5674 | 196_HRV80b | CACACTAGCCAGGTGCAACCAGAAGACATGATAGAAACTAGATATGTTATTACTGATCAG |
| 5675 | 197_HRV80  | CACACTAGCCAGGTGCAACCAGAAGACATGATAGAAACTAGATATGTTATTACTGATCAG |
| 5676 | GROUP_65   | CACACTAGCCAGGTGCAACCAGAAGACATGATAGAAACTAGATATGTTATTACTGATCAG |
| 5677 | | |
| 5678 | 195_HRV80a | ACAAAGGATGAGATGAGCATTGAAAGTTTCTTAGGAAGATCTGGTTGTGTTGCTATCATT |
| 5679 | 196_HRV80b | ACAAAGGATGAGATGAGCATTGAAAGTTTCTTAGGAAGATCTGGTTGTGTTGCTATCATT |
| 5680 | 197_HRV80  | ACAAAGGATGAGATGAGCATTGAAAGTTTCTTAGGAAGATCTGGTTGTGTTGCTATCATT |
| 5681 | GROUP_65   | ACAAAGGATGAGATGAGCATTGAAAGTTTCTTAGGAAGATCTGGTTGTGTTGCTATCATT |
| 5682 | | |
| 5683 | 195_HRV80a | GAAACCAAATTAAACCATGAAACAGAC---------ATGTACAATGCT---GATGGTCAG |
| 5684 | 196_HRV80b | GAAACCAAATTAAACCATGAAACAGAC---------ATGTACAATGCT---GATGGTCAG |
| 5685 | 197_HRV80  | GAAACCAAATTAAACCATGAAACAGAC---------ATGTACAATGCT---GATGGTCAG |
| 5686 | GROUP_65   | GAAACCAAATTAAACCATGAAACAGAC.........ATGTACAATGCT...GATGGTCAG |
| 5687 | | |
| 5688 | 195_HRV80a | AATTTTTCAAAGTGGAAAATAACATTAATGGAAATGGCACAAATTAGAAGAAAGTGTGAG |
| 5689 | 196_HRV80b | AATTTTTCAAAGTGGAAAATAACATTAATGGAAATGGCACAAATTAGAAGAAAGTGTGAG |
| 5690 | 197_HRV80  | AATTTTTCAAAGTGGAAAATAACATTAATGGAAATGGCACAAATTAGAAGAAAGTGTGAG |
| 5691 | GROUP_65   | AATTTTTCAAAGTGGAAAATAACATTAATGGAAATGGCACAAATTAGAAGAAAGTGTGAG |
| 5692 | | |
| 5693 | 195_HRV80a | CTTTTCACTTACCTCAGATTTGACTCAGAAATAACAATAG-TAACTACCTTAGCAGGACA |
| 5694 | 196_HRV80b | CTTTTCACTTACCTCAGATTTGACTCAGAAATAACAATAG-TAACTACCTTAGCAGGACA |
| 5695 | 197_HRV80  | CTTTTCACTTACCTCAGATTTGACTCAGAAATAACAATAG-TAACTACCTTAGCAGGACA |
| 5696 | GROUP_65   | CTTTTCACTTACCTCAGATTTGACTCAGAAATAACAATAG.TAACTACCTTAGCAGGACA |
| 5697 | | |
| 5698 | 195_HRV80a | AGGGGAGGACATTGGTCATGTAGTTATTCAATACATGTACGTACCACCAGGGGCCCCGTT |
| 5699 | 196_HRV80b | AGGGGAGGACATTGGTCATGTAGTTATTCAATACATGTACGTACCACCAGGGGCCCCGTT |
| 5700 | 197_HRV80  | AGGGGAGGACATTGGTCATGTAGTTATTCAATACATGTACGTACCACCAGGGGCCCCGTT |
| 5701 | GROUP_65   | AGGGGAGGACATTGGTCATGTAGTTATTCAATACATGTACGTACCACCAGGGGCCCCGTT |
| 5702 | | |
| 5703 | 195_HRV80a | GCCAAACAAACGCAATGATTATACTTGGCAGTCTGGCACGAATGCTTCAGTCTTCTGGCA |

FIG. D14 CONT'D

```
10.trace                                                             9/20/2007 5:05 PM 5704  196_HRV80b    GCCAAACAAACGCAATGATTATACTTGGCAGTCTGGCACGAATGCTTCAGTCTTCTGGCA
5705  197_HRV80     GCCAAACAAACGCAATGATTATACTTGGCAGTCTGGCACGAATGCTTCAGTCTTCTGGCA
5706  GROUP_65      GCCAAACAAACGCAATGATTATACTTGGCAGTCTGGCACGAATGCTTCAGTCTTCTGGCA
5707
5708  195_HRV80a    ACAGGGTCAGCCATACCCCAGATTCACTATTCCATTCATGAGTATAGCCTCAGCTTATTA
5709  196_HRV80b    ACAGGGTCAGCCATACCCCAGATTCACTATTCCATTCATGAGTATAGCCTCAGCTTATTA
5710  197_HRV80     ACAGGGTCAGCCATACCCCAGATTCACTATTCCATTCATGAGTATAGCCTCAGCTTATTA
5711  GROUP_65      ACAGGGTCAGCCATACCCCAGATTCACTATTCCATTCATGAGTATAGCCTCAGCTTATTA
5712
5713  195_HRV80a    CATGTTCTATGATGGGTATGAGAGTGATAAAG---GCAACATTTATGGAACAGCAGTTAC
5714  196_HRV80b    CATGTTCTATGATGGGTATGAGAGTGATAAAG---GCAACATTTATGGAACAGCAGTTAC
5715  197_HRV80     CATGTTCTATGATGGGTATGAGAGTGATAAAG---GCAACATTTATGGAACAGCAGTTAC
5716  GROUP_65      CATGTTCTATGATGGGTATGAGAGTGATAAAG...GCAACATTTATGGAACAGCAGTTAC
5717
5718  195_HRV80a    CAATGATATGGGAACCCTGTGTGCTAGAATTGTTACAGAACAACAGAAACATAAAGTCCT
5719  196_HRV80b    CAATGATATGGGAACCCTGTGTGCTAGAATTGTTACAGAACAACAGAAACATAAAGTCCT
5720  197_HRV80     CAATGATATGGGAACCCTGTGTGCTAGAATTGTTACAGAACAACAGAAACATAAAGTCCT
5721  GROUP_65      CAATGATATGGGAACCCTGTGTGCTAGAATTGTTACAGAACAACAGAAACATAAAGTCCT
5722
5723  195_HRV80a    AATCACCAGCAGAATATATCACAAAGCTAAACACATCAAAGCATGGTGTCCAAGAGCACC
5724  196_HRV80b    AATCACCAGCAGAATATATCACAAAGCTAAACACATCAAAGCATGGTGTCCAAGAGCACC
5725  197_HRV80     AATCACCAGCAGAATATATCACAAAGCTAAACACATCAAAGCATGGTGTCCAAGAGCACC
5726  GROUP_65      AATCACCAGCAGAATATATCACAAAGCTAAACACATCAAAGCATGGTGTCCAAGAGCACC
5727
5728  195_HRV80a    TAGAGCAGTCCCATACCAA-CATACCTACAGCCCAAATTTCAAAA-ACACTG---ATGAA
5729  196_HRV80b    TAGAGCAGTCCCATACCAA-CATACCTACAGCCCAAATTTCAAAA-ACACTG---ATGAA
5730  197_HRV80     TAGAGCAGTCCCATACCAA-CATACCTACAGCCCAAATTTCAAAA-ACACTG---ATGAA
5731  GROUP_65      TAGAGCAGTCCCATACCAA.CATACCTACAGCCCAAATTTCAAAA.ACACTG...ATGAA
5732
5733  195_HRV80a    TCTA------TACCAGATACACAAATTAAAATCAGAGATAATATCAGGCAGGTTAGAA--
5734  196_HRV80b    TCTA------TACCAGATACACAAATTAAAATCAGAGATAATATCAGGCAGGTTAGAA--
5735  197_HRV80     TCTA------TACCAGATACACAAATTAAAATCAGAGATAATATCAGGCAGGTTAGAA--
5736  GROUP_65      TCTA......TACCAGATACACAAATTAAAATCAGAGATAATATCAGGCAGGTTAGAA..
5737
5738  195_HRV80a    ----CAGTA------------
5739  196_HRV80b    ----CAGTC------------
5740  197_HRV80     ----CAGTT------------
5741  GROUP_65      ....CAGT-............
5742
5743
5744
5745  Group  66:
5746
5747  198_HRV51     AACCCTGTTGAAAAATATACAGAGGCTTTACTCAATGAAGTGTTGGTGGTTCCCAACATA
5748  199_HRV51a    AACCCTGTTGAAAAATATACAGAGGCTTTACTCAATGAAGTGTTGGTGGTTCCCAACATA
5749  200_HRV51b    AACCCTGTTGAAAAATATACAGAGGCTTTACTCAATGAAGTGTTGGTGGTTCCCAACATA
5750  GROUP_66      AACCCTGTTGAAAAATATACAGAGGCTTTACTCAATGAAGTGTTGGTGGTTCCCAACATA
5751
5752  198_HRV51     CAACCTAGCAGTGGGCACACATCTAATGCTGCACCAGCTCTAGATGCTGCTGAGACAGGA
5753  199_HRV51a    CAACCTAGCAGTGGGCACACATCTAATGCTGCACCAGCTCTAGATGCTGCTGAGACAGGA
5754  200_HRV51b    CAACCTAGCAGTGGGCACACATCTAATGCTGCACCAGCTCTAGATGCTGCTGAGACAGGA
5755  GROUP_66      CAACCTAGCAGTGGGCACACATCTAATGCTGCACCAGCTCTAGATGCTGCTGAGACAGGA
5756
5757  198_HRV51     CATACTAGTCAAGTTCAACCAGAAGATATGGTAGAGACCAGGTATGTTGTCACAGACCAA
5758  199_HRV51a    CATACTAGTCAAGTTCAACCAGAAGATATGGTAGAGACCAGGTATGTTGTCACAGACCAA
5759  200_HRV51b    CATACTAGTCAAGTTCAACCAGAAGATATGGTAGAGACCAGGTATGTTGTCACAGACCAA
5760  GROUP_66      CATACTAGTCAAGTTCAACCAGAAGATATGGTAGAGACCAGGTATGTTGTCACAGACCAA
5761
5762  198_HRV51     ACTAGAGATGAAATGAGTATAGAGAGTTTCTTGGGTAGATCTGCTTGCGTAGCAATCATC
5763  199_HRV51a    ACTAGAGATGAAATGAGTATAGAGAGTTTCTTGGGTAGATCTGCTTGCGTAGCAATCATC
5764  200_HRV51b    ACTAGAGATGAAATGAGTATAGAGAGTTTCTTGGGTAGATCTGCTTGCGTAGCAATCATC
5765  GROUP_66      ACTAGAGATGAAATGAGTATAGAGAGTTTCTTGGGTAGATCTGCTTGCGTAGCAATCATC
5766
5767  198_HRV51     CATACAAACCTTGAGCATGTTGAAGCAGACAGACAAGCCTACAATGCA---AAAGGGAAA
5768  199_HRV51a    CATACAAACCTTGAGCATGTTGAAGCAGACAGACAAGCCTACAATGCA---AAAGGGAAA
```

FIG. D14 CONT'D

10.trace 9/20/2007 5:05 PM

```
5769 200_HRV51b    CATACAAACCTTGAGCATGTTGAAGCAGACAGACAAGCCTACAATGCA---AAAGGGAAA
5770 GROUP_66      CATACAAACCTTGAGCATGTTGAAGCAGACAGACAAGCCTACAATGCA...AAAGGGAAA
5771
5772 198_HRV51     AATTTCTCTACATGGAAAATTACACTCAAAGAAATGGCTCAAATTAGAAGAAAGTGTGAA
5773 199_HRV51a    AATTTCTCTACATGGAAAATTACACTCAAAGAAATGGCTCAAATTAGAAGAAAGTGTGAA
5774 200_HRV51b    AATTTCTCTACATGGAAAATTACACTCAAAGAAATGGCTCAAATTAGAAGAAAGTGTGAA
5775 GROUP_66      AATTTCTCTACATGGAAAATTACACTCAAAGAAATGGCTCAAATTAGAAGAAAGTGTGAA
5776
5777 198_HRV51     CTTTTCACATACTTAAGATTTGATTCAGAGATCACTATAG-TTGCTACCATTGCTGGACA
5778 199_HRV51a    CTTTTCACATACTTAAGATTTGATTCAGAGATCACTATAG-TTGCTACCATTGCTGGACA
5779 200_HRV51b    CTTTTCACATACTTAAGATTTGATTCAGAGATCACTATAG-TTGCTACCATTGCTGGACA
5780 GROUP_66      CTTTTCACATACTTAAGATTTGATTCAGAGATCACTATAG.TTGCTACCATTGCTGGACA
5781
5782 198_HRV51     GGGTGATGACATAGGGCACATTGTACTTCAATACATGTATGTACCCCCTGGAGGACCAGT
5783 199_HRV51a    GGGTGATGACATAGGGCACATTGTACTTCAATACATGTATGTACCCCCTGGAGGACCAGT
5784 200_HRV51b    GGGTGATGACATAGGGCACATTGTACTTCAATACATGTATGTACCCCCTGGAGGACCAGT
5785 GROUP_66      GGGTGATGACATAGGGCACATTGTACTTCAATACATGTATGTACCCCCTGGAGGACCAGT
5786
5787 198_HRV51     TCCACTTACTAGGAAAGATGATGAGTGGCAATCAGGAACTAATGCTTCAGTATTCTGGCA
5788 199_HRV51a    TCCACTTACTAGGAAAGATGATGAGTGGCAATCAGGAACTAATGCTTCAGTATTCTGGCA
5789 200_HRV51b    TCCACTTACTAGGAAAGATGATGAGTGGCAATCAGGAACTAATGCTTCAGTATTCTGGCA
5790 GROUP_66      TCCACTTACTAGGAAAGATGATGAGTGGCAATCAGGAACTAATGCTTCAGTATTCTGGCA
5791
5792 198_HRV51     ACATGGACAACCATACCCTAGATTTACAATCCCTTTTGTAAGCATAGCCTCAGCATACTA
5793 199_HRV51a    ACATGGACAACCATACCCTAGATTTACAATCCCTTTTGTAAGCATAGCCTCAGCATACTA
5794 200_HRV51b    ACATGGACAACCATACCCTAGATTTACAATCCCTTTTGTAAGCATAGCCTCAGCATACTA
5795 GROUP_66      ACATGGACAACCATACCCTAGATTTACAATCCCTTTTGTAAGCATAGCCTCAGCATACTA
5796
5797 198_HRV51     CATGTTTTATGATGGGTATGAAGGTGATAGTTTGACCTCACAGTACGGTTCAGTAGTCAC
5798 199_HRV51a    CATGTTTTATGATGGGTATGAAGGTGATAGTTTGACCTCACAGTACGGTTCAGTAGTCAC
5799 200_HRV51b    CATGTTTTATGATGGGTATGAAGGTGATAGTTTGACCTCACAGTACGGTTCAGTAGTCAC
5800 GROUP_66      CATGTTTTATGATGGGTATGAAGGTGATAGTTTGACCTCACAGTACGGTTCAGTAGTCAC
5801
5802 198_HRV51     AAATGCTATGGGGACACTATGTGTTCGTGTGGTCACAGAGCAACAAAAACATGAGGTTAA
5803 199_HRV51a    AAATGCTATGGGGACACTATGTGTTCGTGTGGTCACAGAGCAACAAAAACATGAGGTTAA
5804 200_HRV51b    AAATGCTATGGGGACACTATGTGTTCGTGTGGTCACAGAGCAACAAAAACATGAGGTTAA
5805 GROUP_66      AAATGCTATGGGGACACTATGTGTTCGTGTGGTCACAGAGCAACAAAAACATGAGGTTAA
5806
5807 198_HRV51     CATAACTAGCAGGATTTACCACAAAGCCAAACATGTCAGTGCATGGTGCCCTCGTCCTCC
5808 199_HRV51a    CATAACTAGCAGGATTTACCACAAAGCCAAACATGTCAGTGCATGGTGCCCTCGTCCTCC
5809 200_HRV51b    CATAACTAGCAGGATTTACCACAAAGCCAAACATGTCAGTGCATGGTGCCCTCGTCCTCC
5810 GROUP_66      CATAACTAGCAGGATTTACCACAAAGCCAAACATGTCAGTGCATGGTGCCCTCGTCCTCC
5811
5812 198_HRV51     TCGTGCTGTAGCCTACCAA-CACACATACAGTACAAACTTCGTTC-CAAAAGAGGGATTT
5813 199_HRV51a    TCGTGCTGTAGCCTACCAA-CACACATACAGTACAAACTTCGTTC-CAAAAGAGGGATTT
5814 200_HRV51b    TCGTGCTGTAGCCTACCAA-CACACATACAGTACAAACTTCGTTC-CAAAAGAGGGATTT
5815 GROUP_66      TCGTGCTGTAGCCTACCAA.CACACATACAGTACAAACTTCGTTC.CAAAAGAGGGATTT
5816
5817 198_HRV51     GAAG------GCTTGAAAACTCAGATTAAAACTAGGGCAGACATCAAACTTGTGAACT--
5818 199_HRV51a    GAAG------GCTTGAAAACTCAGATTAAAACTAGGGCAGACATCAAACTTGTGAACT--
5819 200_HRV51b    GAAG------GCTTGAAAACTCAGATTAAAACTAGGGCAGACATCAAACTTGTGAACT--
5820 GROUP_66      GAAG......GCTTGAAAACTCAGATTAAAACTAGGGCAGACATCAAACTTGTGAACT..
5821
5822 198_HRV51     -----TT--------------
5823 199_HRV51a    -----TA--------------
5824 200_HRV51b    -----TG--------------
5825 GROUP_66      .....T-..............
5826
5827
5828
5829 Group  67:
5830
5831 201_HRV65a    AATCCAATTGAGAAGTATACAGAAGCTCTACTTAATGAAGTGTTGGTGGTCCCAAATATA
5832 202_HRV65b    AATCCAATTGAGAAGTATACAGAAGCTCTACTTAATGAAGTGTTGGTGGTCCCAAATATA
5833 203_HRV65     AATCCAATTGAGAAGTATACAGAAGCTCTACTTAATGAAGTGTTGGTGGTCCCAAATATA
```

FIG. D14 CONT'D 10.trace                                                                      9/20/2007 5:05 PM

```
5834 GROUP_67       AATCCAATTGAGAAGTATACAGAAGCTCTACTTAATGAAGTGTTGGTGGTCCCAAATATA
5835
5836 201_HRV65a     CAAGCTAGTAATGGGCATACATCTAATGCTGCACCAGCTTTAGATGCTGCTGAAACAGGA
5837 202_HRV65b     CAAGCTAGTAATGGGCATACATCTAATGCTGCACCAGCTTTAGATGCTGCTGAAACAGGA
5838 203_HRV65      CAAGCTAGTAATGGGCATACATCTAATGCTGCACCAGCTTTAGATGCTGCTGAAACAGGA
5839 GROUP_67       CAAGCTAGTAATGGGCATACATCTAATGCTGCACCAGCTTTAGATGCTGCTGAAACAGGA
5840
5841 201_HRV65a     CACACTAGTCAAGTTCAACCAGAGGATGTGATAGAAACCAGATATGTCATCACAGATCAA
5842 202_HRV65b     CACACTAGTCAAGTTCAACCAGAGGATGTGATAGAAACCAGATATGTCATCACAGATCAA
5843 203_HRV65      CACACTAGTCAAGTTCAACCAGAGGATGTGATAGAAACCAGATATGTCATCACAGATCAA
5844 GROUP_67       CACACTAGTCAAGTTCAACCAGAGGATGTGATAGAAACCAGATATGTCATCACAGATCAA
5845
5846 201_HRV65a     ACCAGAGATGAGATGAGCGTAGAGAGTTTCCTGGGCAGATCTGCCTGCATAGCAGTCATT
5847 202_HRV65b     ACCAGAGATGAGATGAGCGTAGAGAGTTTCCTGGGCAGATCTGCCTGCATAGCAGTCATT
5848 203_HRV65      ACCAGAGATGAGATGAGCGTAGAGAGTTTCCTGGGCAGATCTGCCTGCATAGCAGTCATT
5849 GROUP_67       ACCAGAGATGAGATGAGCGTAGAGAGTTTCCTGGGCAGATCTGCCTGCATAGCAGTCATT
5850
5851 201_HRV65a     CACACAGATCTTAAACATGACCATGAAGGCCAAAATGTTTACAATGAC---GAAGGCAGA
5852 202_HRV65b     CACACAGATCTTAAACATGACCATGAAGGCCAAAATGTTTACAATGAC---GAAGGCAGA
5853 203_HRV65      CACACAGATCTTAAACATGACCATGAAGGCCAAAATGTTTACAATGAC---GAAGGCAGA
5854 GROUP_67       CACACAGATCTTAAACATGACCATGAAGGCCAAAATGTTTACAATGAC...GAAGGCAGA
5855
5856 201_HRV65a     AATTTCTCTGCTTGGGAAATTACACTCAAGGAAATGGCTCAAATTAGGAGAAAGTGTGAA
5857 202_HRV65b     AATTTCTCTGCTTGGGAAATTACACTCAAGGAAATGGCTCAAATTAGGAGAAAGTGTGAA
5858 203_HRV65      AATTTCTCTGCTTGGGAAATTACACTCAAGGAAATGGCTCAAATTAGGAGAAAGTGTGAA
5859 GROUP_67       AATTTCTCTGCTTGGGAAATTACACTCAAGGAAATGGCTCAAATTAGGAGAAAGTGTGAA
5860
5861 201_HRV65a     CTCTTCACCTATTTGCGCTTTGACTCAGAAATTACCATAG-TGGCTACTATAGCTGGACA
5862 202_HRV65b     CTCTTCACCTATTTGCGCTTTGACTCAGAAATTACCATAG-TGGCTACTATAGCTGGACA
5863 203_HRV65      CTCTTCACCTATTTGCGCTTTGACTCAGAAATTACCATAG-TGGCTACTATAGCTGGACA
5864 GROUP_67       CTCTTCACCTATTTGCGCTTTGACTCAGAAATTACCATAG.TGGCTACTATAGCTGGACA
5865
5866 201_HRV65a     AGGTGATGACATAGGGCACATAGTGCTTCAATATATGTATGTGCCTCCTGGTGGTCCTGT
5867 202_HRV65b     AGGTGATGACATAGGGCACATAGTGCTTCAATATATGTATGTGCCTCCTGGTGGTCCTGT
5868 203_HRV65      AGGTGATGACATAGGGCACATAGTGCTTCAATATATGTATGTGCCTCCTGGTGGTCCTGT
5869 GROUP_67       AGGTGATGACATAGGGCACATAGTGCTTCAATATATGTATGTGCCTCCTGGTGGTCCTGT
5870
5871 201_HRV65a     TCCAAAAACTAGAAAAGATGAAGAGTGGCAGACAGGAACTAATGCTTCAGTCTTTTGGCA
5872 202_HRV65b     TCCAAAAACTAGAAAAGATGAAGAGTGGCAGACAGGAACTAATGCTTCAGTCTTTTGGCA
5873 203_HRV65      TCCAAAAACTAGAAAAGATGAAGAGTGGCAGACAGGAACTAATGCTTCAGTCTTTTGGCA
5874 GROUP_67       TCCAAAAACTAGAAAAGATGAAGAGTGGCAGACAGGAACTAATGCTTCAGTCTTTTGGCA
5875
5876 201_HRV65a     GCATGGTCAACCATACCCCAGATTTACAATTCCTTTTGTGAGTATTGCCTCAGCATATTA
5877 202_HRV65b     GCATGGTCAACCATACCCCAGATTTACAATTCCTTTTGTGAGTATTGCCTCAGCATATTA
5878 203_HRV65      GCATGGTCAACCATACCCCAGATTTACAATTCCTTTTGTGAGTATTGCCTCAGCATATTA
5879 GROUP_67       GCATGGTCAACCATACCCCAGATTTACAATTCCTTTTGTGAGTATTGCCTCAGCATATTA
5880
5881 201_HRV65a     CATGTTCTATGATGGTTATGAGGGTGATGACCCAAATTCAAAATATGGTTCAGTGGTTAC
5882 202_HRV65b     CATGTTCTATGATGGTTATGAGGGTGATGACCCAAATTCAAAATATGGTTCAGTGGTTAC
5883 203_HRV65      CATGTTCTATGATGGTTATGAGGGTGATGACCCAAATTCAAAATATGGTTCAGTGGTTAC
5884 GROUP_67       CATGTTCTATGATGGTTATGAGGGTGATGACCCAAATTCAAAATATGGTTCAGTGGTTAC
5885
5886 201_HRV65a     TAATGCTATGGGCACACTATATGTGCGTGTGGTTACAGAAAGGCAAAAACATGAAGTCAA
5887 202_HRV65b     TAATGCTATGGGCACACTATATGTGCGTGTGGTTACAGAAAGGCAAAAACATGAAGTCAA
5888 203_HRV65      TAATGCTATGGGCACACTATATGTGCGTGTGGTTACAGAAAGGCAAAAACATGAAGTCAA
5889 GROUP_67       TAATGCTATGGGCACACTATATGTGCGTGTGGTTACAGAAAGGCAAAAACATGAAGTCAA
5890
5891 201_HRV65a     CATAACCAGTAGAATATATCATAAAGCTAAACACATCAGTGCTTGGTGTCCACGACCTCC
5892 202_HRV65b     CATAACCAGTAGAATATATCATAAAGCTAAACACATCAGTGCTTGGTGTCCACGACCTCC
5893 203_HRV65      CATAACCAGTAGAATATATCATAAAGCTAAACACATCAGTGCTTGGTGTCCACGACCTCC
5894 GROUP_67       CATAACCAGTAGAATATATCATAAAGCTAAACACATCAGTGCTTGGTGTCCACGACCTCC
5895
5896 201_HRV65a     CCGAGCAGTAGCTTACCAA-CACACATACAGTACAAATTTTGTTC-CTAGCGGAGGTCTT
5897 202_HRV65b     CCGAGCAGTAGCTTACCAA-CACACATACAGTACAAATTTTGTTC-CTAGCGGAGGTCTT
5898 203_HRV65      CCGAGCAGTAGCTTACCAA-CACACATACAGTACAAATTTTGTTC-CTAGCGGAGGTCTT
```

FIG. D14 CONT'D 10.trace                                                                              9/20/2007 5:05 PM

```
5899 GROUP_67       CCGAGCAGTAGCTTACCAA.CACACATACAGTACAAATTTTGTTC.CTAGCGGAGGTCTT
5900
5901 201_HRV65a     ACAA------ACCTAAGAACCCAAATTAAAACCAGAGATAACATTAAAATTGTAAACT--
5902 202_HRV65b     ACAA------ACCTAAGAACCCAAATTAAAACCAGAGATAACATTAAAATTGTAAACT--
5903 203_HRV65      ACAA------ACCTAAGAACCCAAATTAAAACCAGAGATAACATTAAAATTGTAAACT--
5904 GROUP_67       ACAA......ACCTAAGAACCCAAATTAAAACCAGAGATAACATTAAAATTGTAAACT..
5905
5906 201_HRV65a     -----TG--------------
5907 202_HRV65b     -----TA--------------
5908 203_HRV65      -----TT--------------
5909 GROUP_67       .....T-..............
5910
5911
5912
5913 Group 68:
5914
5915 204_HRV71a     AATCCTGTAGAAAAATATACAGAAGCAATACTCAATGAGGTTCTAGTTGTGCCAAATATA
5916 205_HRV71b     AATCCTGTAGAAAAATATACAGAAGCAATACTCAATGAGGTTCTAGTTGTGCCAAATATA
5917 206_HRV71      AATCCTGTAGAAAAATATACAGAAGCAATACTCAATGAGGTTCTAGTTGTGCCAAATATA
5918 GROUP_68       AATCCTGTAGAAAAATATACAGAAGCAATACTCAATGAGGTTCTAGTTGTGCCAAATATA
5919
5920 204_HRV71a     CAACCTAGTAATGGACATACCTCAAACTCAGCACCAGCCTTAGATGCAGCAGAAACTGGG
5921 205_HRV71b     CAACCTAGTAATGGACATACCTCAAACTCAGCACCAGCCTTAGATGCAGCAGAAACTGGG
5922 206_HRV71      CAACCTAGTAATGGACATACCTCAAACTCAGCACCAGCCTTAGATGCAGCAGAAACTGGG
5923 GROUP_68       CAACCTAGTAATGGACATACCTCAAACTCAGCACCAGCCTTAGATGCAGCAGAAACTGGG
5924
5925 204_HRV71a     CATACCAACCAAGTACAACCAGAAGATGTTATGGAAACCAGATATGTGATCACTGATCAA
5926 205_HRV71b     CATACCAACCAAGTACAACCAGAAGATGTTATGGAAACCAGATATGTGATCACTGATCAA
5927 206_HRV71      CATACCAACCAAGTACAACCAGAAGATGTTATGGAAACCAGATATGTGATCACTGATCAA
5928 GROUP_68       CATACCAACCAAGTACAACCAGAAGATGTTATGGAAACCAGATATGTGATCACTGATCAA
5929
5930 204_HRV71a     ACTAGGGATGAAATGAGCATTGAGAGCTTCTTGGGCAGATCTGCATGCATAGCTACCATA
5931 205_HRV71b     ACTAGGGATGAAATGAGCATTGAGAGCTTCTTGGGCAGATCTGCATGCATAGCTACCATA
5932 206_HRV71      ACTAGGGATGAAATGAGCATTGAGAGCTTCTTGGGCAGATCTGCATGCATAGCTACCATA
5933 GROUP_68       ACTAGGGATGAAATGAGCATTGAGAGCTTCTTGGGCAGATCTGCATGCATAGCTACCATA
5934
5935 204_HRV71a     CACACTAAATTAGTACATGGAGAGGAGGG------TGTTTATAATATG---AAAGGTAAC
5936 205_HRV71b     CACACTAAATTAGTACATGGAGAGGAGGG------TGTTTATAATATG---AAAGGTAAC
5937 206_HRV71      CACACTAAATTAGTACATGGAGAGGAGGG------TGTTTATAATATG---AAAGGTAAC
5938 GROUP_68       CACACTAAATTAGTACATGGAGAGGAGGG......TGTTTATAATATG...AAAGGTAAC
5939
5940 204_HRV71a     AATCTCTCAAAGTGGCAGATTACACTCAAAGAAATGGCTCAGATCAGGAGGAAATGTGAA
5941 205_HRV71b     AATCTCTCAAAGTGGCAGATTACACTCAAAGAAATGGCTCAGATCAGGAGGAAATGTGAA
5942 206_HRV71      AATCTCTCAAAGTGGCAGATTACACTCAAAGAAATGGCTCAGATCAGGAGGAAATGTGAA
5943 GROUP_68       AATCTCTCAAAGTGGCAGATTACACTCAAAGAAATGGCTCAGATCAGGAGGAAATGTGAA
5944
5945 204_HRV71a     CTCTTCACATACCTGCGCTTTGATTCAGAGATAACAATTG-TAGCTACACTAGCAGGGCA
5946 205_HRV71b     CTCTTCACATACCTGCGCTTTGATTCAGAGATAACAATTG-TAGCTACACTAGCAGGGCA
5947 206_HRV71      CTCTTCACATACCTGCGCTTTGATTCAGAGATAACAATTG-TAGCTACACTAGCAGGGCA
5948 GROUP_68       CTCTTCACATACCTGCGCTTTGATTCAGAGATAACAATTG.TAGCTACACTAGCAGGGCA
5949
5950 204_HRV71a     AGGAGATGATTTAGGACATATTGTACTCCAGTACATGTATGTTCCCCCAGGTGGTCCAAT
5951 205_HRV71b     AGGAGATGATTTAGGACATATTGTACTCCAGTACATGTATGTTCCCCCAGGTGGTCCAAT
5952 206_HRV71      AGGAGATGATTTAGGACATATTGTACTCCAGTACATGTATGTTCCCCCAGGTGGTCCAAT
5953 GROUP_68       AGGAGATGATTTAGGACATATTGTACTCCAGTACATGTATGTTCCCCCAGGTGGTCCAAT
5954
5955 204_HRV71a     ACCAGAGACCAGGGATGCCGATGAATGGCAGTCTGGAACTAATGCATCAGTCTTTTGGCA
5956 205_HRV71b     ACCAGAGACCAGGGATGCCGATGAATGGCAGTCTGGAACTAATGCATCAGTCTTTTGGCA
5957 206_HRV71      ACCAGAGACCAGGGATGCCGATGAATGGCAGTCTGGAACTAATGCATCAGTCTTTTGGCA
5958 GROUP_68       ACCAGAGACCAGGGATGCCGATGAATGGCAGTCTGGAACTAATGCATCAGTCTTTTGGCA
5959
5960 204_HRV71a     GCACGGCCAACCATACCCAAGGTTTACAATCCCCTTCATAAGCATTGCATCAGCATATTA
5961 205_HRV71b     GCACGGCCAACCATACCCAAGGTTTACAATCCCCTTCATAAGCATTGCATCAGCATATTA
5962 206_HRV71      GCACGGCCAACCATACCCAAGGTTTACAATCCCCTTCATAAGCATTGCATCAGCATATTA
5963 GROUP_68       GCACGGCCAACCATACCCAAGGTTTACAATCCCCTTCATAAGCATTGCATCAGCATATTA
```

FIG. D14 CONT'D 10.trace                                                                9/20/2007 5:05 PM

```
5964
5965  204_HRV71a    CATGTTCTATGATGGGTATGAAGGTGATGCCCTCAGTTCTAAATATGGCTCAGTAGTTAC
5966  205_HRV71b    CATGTTCTATGATGGGTATGAAGGTGATGCCCTCAGTTCTAAATATGGCTCAGTAGTTAC
5967  206_HRV71     CATGTTCTATGATGGGTATGAAGGTGATGCCCTCAGTTCTAAATATGGCTCAGTAGTTAC
5968  GROUP_68      CATGTTCTATGATGGGTATGAAGGTGATGCCCTCAGTTCTAAATATGGCTCAGTAGTTAC
5969
5970  204_HRV71a    TAATGCCATGGGCACCTTATGTGTTCGTGTGGTTACAGAACAGCAAAGCAACACAGTCAA
5971  205_HRV71b    TAATGCCATGGGCACCTTATGTGTTCGTGTGGTTACAGAACAGCAAAGCAACACAGTCAA
5972  206_HRV71     TAATGCCATGGGCACCTTATGTGTTCGTGTGGTTACAGAACAGCAAAGCAACACAGTCAA
5973  GROUP_68      TAATGCCATGGGCACCTTATGTGTTCGTGTGGTTACAGAACAGCAAAGCAACACAGTCAA
5974
5975  204_HRV71a    CATAACAAGTAGGATTTATCACAAAGCCAAACATGTCAGAGCATGGTGTCCTAGACCCCC
5976  205_HRV71b    CATAACAAGTAGGATTTATCACAAAGCCAAACATGTCAGAGCATGGTGTCCTAGACCCCC
5977  206_HRV71     CATAACAAGTAGGATTTATCACAAAGCCAAACATGTCAGAGCATGGTGTCCTAGACCCCC
5978  GROUP_68      CATAACAAGTAGGATTTATCACAAAGCCAAACATGTCAGAGCATGGTGTCCTAGACCCCC
5979
5980  204_HRV71a    CAGAGCAGTAGCCTACCAA-TCAACATATACCACAAATTTTGTTC-CACAAGACGGGATC
5981  205_HRV71b    CAGAGCAGTAGCCTACCAA-TCAACATATACCACAAATTTTGTTC-CACAAGACGGGATC
5982  206_HRV71     CAGAGCAGTAGCCTACCAA-TCAACATATACCACAAATTTTGTTC-CACAAGACGGGATC
5983  GROUP_68      CAGAGCAGTAGCCTACCAA.TCAACATATACCACAAATTTTGTTC.CACAAGACGGGATC
5984
5985  204_HRV71a    AATT------CCATTAAAACCAAAATCAAAATCAGAAGAGACATTAAAGAGGTCAGCA--
5986  205_HRV71b    AATT------CCATTAAAACCAAAATCAAAATCAGAAGAGACATTAAAGAGGTCAGCA--
5987  206_HRV71     AATT------CCATTAAAACCAAAATCAAAATCAGAAGAGACATTAAAGAGGTCAGCA--
5988  GROUP_68      AATT......CCATTAAAACCAAAATCAAAATCAGAAGAGACATTAAAGAGGTCAGCA..
5989
5990  204_HRV71a    -----ACTAA-----------
5991  205_HRV71b    -----ACTAG-----------
5992  206_HRV71     -----ACTAT-----------
5993  GROUP_68      .....ACTA-...........
5994
5995
5996
5997  Group 69:
5998
5999  207_HRV8      AACCCTATTGAACAATTCACAGAGGCAGTATTAAACGAGGTTCTTGTAGTTCCAAACACA
6000  208_HRV95     AACCCTATTGAACAATTCACAGAGGCAGTATTAAACGAGGTTCTTGTAGTTCCAAATACA
6001  GROUP_69      AACCCTATTGAACAATTCACAGAGGCAGTATTAAACGAGGTTCTTGTAGTTCCAAA-ACA
6002
6003  207_HRV8      CAAGCTAGTAATGGATCTATAGCAAATTCAGCACCAGCATTAGATGCAGCAGAGACTGGA
6004  208_HRV95     CAAGCTAGTAATGGATCTATAGCAAATTCAGCACCAGCATTAGATGCAGCAGAGACTGGA
6005  GROUP_69      CAAGC-AGTAATGGATCTATAGCAAATTCAGCACCAGCATTAGATGCAGCAGAGACTGGA
6006
6007  207_HRV8      CACACAAGTTCAGTGCAACCTGAAGATCTTATAGAGACTAGGTATGTAATTACAGATCAA
6008  208_HRV95     CACACAAGTTCAGTGCAACCTGAAGATCTTATAGAGACTAGGTATGTAATTACAGATCAA
6009  GROUP_69      CACACAAGTTCAGTGCAACCTGAAGATCTTATAGAGACTAGGTATGTAATTACAGATCAA
6010
6011  207_HRV8      ACTAGGCATGAGACATCACTGGAATCTTTCTTGGGTAGAGCAGGATGCATTAAAATCATT
6012  208_HRV95     ACTAGGTATGAGACATCACTGGAATCTTTCTTGGGTAGAGCAGGATGCATTAAAATTATT
6013  GROUP_69      ACTAGG-ATGAGACATCACTGGAATCTTTCTTGGGTAGAGCAGGATGCATTAAAT-ATT
6014
6015  207_HRV8      GCATTAGAACTAGATCATGACAAC---------------TATGATGAA-----------
6016  208_HRV95     GCATTAGAACTAGATCATGACAAC---------------TATGATAAA-----------
6017  GROUP_69      GCATTAGAACTAGATCATGACAAC...............TATGAT-AA...........
6018
6019  207_HRV8      AGTTTCAGGACCTGGGGAATAAACATACAAGAGATGTCACAAATTAGAAGGAAATTTGAG
6020  208_HRV95     AATTTCAGGACCTGGGGAATAAACATACAAGAGATGTCACAAATTAGAAGGAAATTTGAA
6021  GROUP_69      A-TTTCAGGACCTGGGGAATAAACATACAAGAGATGTCACAAATTAGAAGGAAATTTGA-
6022
6023  207_HRV8      ATGTTCACTTATGTAAGATTTGATTCAGAGATAACAATTG-TACCATGTATTGCAGCTAT
6024  208_HRV95     ATGTTCACTTATGTAAGATTTGATTCAGAGATAACAATTG-TACCATGTATTGCAGCTAT
6025  GROUP_69      ATGTTCACTTATGTAAGATTTGATTCAGAGATAACAATTG.TACCATGTATTGCAGCTAT
6026
6027  207_HRV8      AAAAGGTGACCTTGGACACATAGTCCTTCAATACATGTATGTTCCCCGGGTGCACCTCT
6028  208_HRV95     AGAAGGTGACCTTGGACACATAGTCCTCCAATACATGTATGTTCCCCGGGTGCACCTCT
```

FIG. D14 CONT'D

```
10.trace                                                                 9/20/2007 5:05 PM 6029 GROUP_69      A-AAGGTGACCTTGGACACATAGTCCT-CAATACATGTATGTTCCCCCGGGTGCACCTCT
6030
6031 207_HRV8      TCCAGATAAAAGGATGCACGATGCCTGGCAAACCAGTACAAATGCCTCAGTCTTCTGGCA
6032 208_HRV95     TCCAGATAAAAGGATGCACGATGCCTGGCAAACCAGTACAAATGCCTCAGTCTTCTGGCA
6033 GROUP_69      TCCAGATAAAAGGATGCACGATGCCTGGCAAACCAGTACAAATGCCTCAGTCTTCTGGCA
6034
6035 207_HRV8      AGTTGGACAAACTTATCCCAGATTCACCATACCTTTCTCCAGCATAGCATCAGCTTATTA
6036 208_HRV95     AGTTGGACAGACTTATCCCAGATTCACCATACCTTTCTCCAGTATAGCATCAGCTTATTA
6037 GROUP_69      AGTTGGACA-ACTTATCCCAGATTCACCATACCTTTCTCCAG-ATAGCATCAGCTTATTA
6038
6039 207_HRV8      CATGTTCTATGATGGTTATGATTCAGATGGTTTAGATGCTATTTATGGTATTCCTGTTAC
6040 208_HRV95     CATGTTCTATGATGGTTATGATTCAGATGGTTTAGATGCTATTTATGGTATTCCTGTTAC
6041 GROUP_69      CATGTTCTATGATGGTTATGATTCAGATGGTTTAGATGCTATTTATGGTATTCCTGTTAC
6042
6043 207_HRV8      AAATCACATGGGCACAATATGTGTGAGAATGGTGACAGATAAACAGAAAATTAAAACTAA
6044 208_HRV95     AAATCACATGGGCACAATATGTGTGAGAATGGTGACAGATAAACAGAAAATTAAAACTAA
6045 GROUP_69      AAATCACATGGGCACAATATGTGTGAGAATGGTGACAGATAAACAGAAAATTAAAACTAA
6046
6047 207_HRV8      AATTGATTCAAGAATATACCTGAAAGCAAAGCACATTAAAGCTTGGTGTCCTAGACCCCC
6048 208_HRV95     AATTGATTCAAGAATATACCTGAAAGCAAAGCATATTAAAGCTTGGTGTCCTAGACCCCC
6049 GROUP_69      AATTGATTCAAGAATATACCTGAAAGCAAAGCA-ATTAAAGCTTGGTGTCCTAGACCCCC
6050
6051 207_HRV8      CAGAGCAGTTACGTATAAC-CATATATACAACCCCAATTATGTTA-GAGAGG------GA
6052 208_HRV95     CAGAGCAGTTACGTATAAC-CATATATACAACCCCAATTATGTTA-GAGAGG------GA
6053 GROUP_69      CAGAGCAGTTACGTATAAC.CATATATACAACCCCAATTATGTTA.GAGAGG......GA
6054
6055 207_HRV8      GTAA------CACCAGAAACTAAGGTTAAATATAGAGCTGAAGTCACAACCATT------
6056 208_HRV95     GTAA------CACCAGAAACTAAGGTCAAATATAGAGCTGAAGTCACAACCATT------
6057 GROUP_69      GTAA......CACCAGAAACTAAGGT-AAATATAGAGCTGAAGTCACAACCATT......
6058
6059 207_HRV8      --------------------
6060 208_HRV95     --------------------
6061 GROUP_69      ....................
6062
6063
6064
6065 Group 70:
6066
6067 209_HRV45     AACCCTGTTGAACAATTTGCAGAAGCAGTCCTTGATCAAGTATTAGTAGTTCCAAACACT
6068 210_HRV45a    AACCCTGTTGAACAATTTGCAGAAGCAGTCCTTGATCAAGTATTAGTAGTTCCAAACACT
6069 211_HRV45b    AACCCTGTTGAACAATTTGCAGAAGCAGTCCTTGATCAAGTATTAGTAGTTCCAAACACT
6070 GROUP_70      AACCCTGTTGAACAATTTGCAGAAGCAGTCCTTGATCAAGTATTAGTAGTTCCAAACACT
6071
6072 209_HRV45     CGACCCAGCGATGGGTTGATTGCAAACTCAGCCCCAGCTTTGGATGCAGCTGAAACTGGA
6073 210_HRV45a    CGACCCAGCGATGGGTTGATTGCAAACTCAGCCCCAGCTTTGGATGCAGCTGAAACTGGA
6074 211_HRV45b    CGACCCAGCGATGGGTTGATTGCAAACTCAGCCCCAGCTTTGGATGCAGCTGAAACTGGA
6075 GROUP_70      CGACCCAGCGATGGGTTGATTGCAAACTCAGCCCCAGCTTTGGATGCAGCTGAAACTGGA
6076
6077 209_HRV45     CACACCAGTTCAGTGCAGCCTGAGGACCTTATAGAGACTAGATATGTGATTGCAGACCAA
6078 210_HRV45a    CACACCAGTTCAGTGCAGCCTGAGGACCTTATAGAGACTAGATATGTGATTGCAGACCAA
6079 211_HRV45b    CACACCAGTTCAGTGCAGCCTGAGGACCTTATAGAGACTAGATATGTGATTGCAGACCAA
6080 GROUP_70      CACACCAGTTCAGTGCAGCCTGAGGACCTTATAGAGACTAGATATGTGATTGCAGACCAA
6081
6082 209_HRV45     ACCAGACATGAAACCTCCATTGAATCTTTTTTGGGTAGGGCTGGATGTGTGGCCAATATT
6083 210_HRV45a    ACCAGACATGAAACCTCCATTGAATCTTTTTTGGGTAGGGCTGGATGTGTGGCCAATATT
6084 211_HRV45b    ACCAGACATGAAACCTCCATTGAATCTTTTTTGGGTAGGGCTGGATGTGTGGCCAATATT
6085 GROUP_70      ACCAGACATGAAACCTCCATTGAATCTTTTTTGGGTAGGGCTGGATGTGTGGCCAATATT
6086
6087 209_HRV45     AGTTTAGACATTAACCATGATGAC---------------TACCAAAAG-----------
6088 210_HRV45a    AGTTTAGACATTAACCATGATGAC---------------TACCAAAAG-----------
6089 211_HRV45b    AGTTTAGACATTAACCATGATGAC---------------TACCAAAAG-----------
6090 GROUP_70      AGTTTAGACATTAACCATGATGAC...............TACCAAAAG...........
6091
6092 209_HRV45     AATTACAAAAATTGGGCAATTAGTTTACAAGAAATGTCACAAATTAGGAGGAAATTTGAA
6093 210_HRV45a    AATTACAAAAATTGGGCAATTAGTTTACAAGAAATGTCACAAATTAGGAGGAAATTTGAA
```

FIG. D14 CONT'D

```
10.trace                                                                    9/20/2007 5:05 PM 6094  211_HRV45b   AATTACAAAAATTGGGCAATTAGTTTACAAGAAATGTCACAAATTAGGAGGAAATTTGAA
6095  GROUP_70    AATTACAAAAATTGGGCAATTAGTTTACAAGAAATGTCACAAATTAGGAGGAAATTTGAA
6096
6097  209_HRV45    ATGTTTACATATGTCAGATTTGATTCCGAAATAACAATAG-TACCATGTGTTGCTGCCAC
6098  210_HRV45a   ATGTTTACATATGTCAGATTTGATTCCGAAATAACAATAG-TACCATGTGTTGCTGCCAC
6099  211_HRV45b   ATGTTTACATATGTCAGATTTGATTCCGAAATAACAATAG-TACCATGTGTTGCTGCCAC
6100  GROUP_70    ATGTTTACATATGTCAGATTTGATTCCGAAATAACAATAG.TACCATGTGTTGCTGCCAC
6101
6102  209_HRV45    AGAAGGTAACTTGGGACACATTGTTGTGCAATACATGTTTGTACCACCAGGAGCACCTCT
6103  210_HRV45a   AGAAGGTAACTTGGGACACATTGTTGTGCAATACATGTTTGTACCACCAGGAGCACCTCT
6104  211_HRV45b   AGAAGGTAACTTGGGACACATTGTTGTGCAATACATGTTTGTACCACCAGGAGCACCTCT
6105  GROUP_70    AGAAGGTAACTTGGGACACATTGTTGTGCAATACATGTTTGTACCACCAGGAGCACCTCT
6106
6107  209_HRV45    CCCTGTTAGTAGAACTGACAACACTTGGCAATCTAGCACAAATGCATCAGTCTTTTGGCA
6108  210_HRV45a   CCCTGTTAGTAGAACTGACAACACTTGGCAATCTAGCACAAATGCATCAGTCTTTTGGCA
6109  211_HRV45b   CCCTGTTAGTAGAACTGACAACACTTGGCAATCTAGCACAAATGCATCAGTCTTTTGGCA
6110  GROUP_70    CCCTGTTAGTAGAACTGACAACACTTGGCAATCTAGCACAAATGCATCAGTCTTTTGGCA
6111
6112  209_HRV45    GGTTGGTCAAACTTATCCCAGATTTTCTATACCTTTCTCAAGTATAGCTTCAGCTTACTA
6113  210_HRV45a   GGTTGGTCAAACTTATCCCAGATTTTCTATACCTTTCTCAAGTATAGCTTCAGCTTACTA
6114  211_HRV45b   GGTTGGTCAAACTTATCCCAGATTTTCTATACCTTTCTCAAGTATAGCTTCAGCTTACTA
6115  GROUP_70    GGTTGGTCAAACTTATCCCAGATTTTCTATACCTTTCTCAAGTATAGCTTCAGCTTACTA
6116
6117  209_HRV45    CATGTTTTATGATGGATACGACACTGATGGCACAGATGCAGTGTATGGTGTTAGTGTGAC
6118  210_HRV45a   CATGTTTTATGATGGATACGACACTGATGGCACAGATGCAGTGTATGGTGTTAGTGTGAC
6119  211_HRV45b   CATGTTTTATGATGGATACGACACTGATGGCACAGATGCAGTGTATGGTGTTAGTGTGAC
6120  GROUP_70    CATGTTTTATGATGGATACGACACTGATGGCACAGATGCAGTGTATGGTGTTAGTGTGAC
6121
6122  209_HRV45    TAACCATATGGGGACTATATGTGTTAGAATTGTTACAGACCAACAACAACATAGAGTTAA
6123  210_HRV45a   TAACCATATGGGGACTATATGTGTTAGAATTGTTACAGACCAACAACAACATAGAGTTAA
6124  211_HRV45b   TAACCATATGGGGACTATATGTGTTAGAATTGTTACAGACCAACAACAACATAGAGTTAA
6125  GROUP_70    TAACCATATGGGGACTATATGTGTTAGAATTGTTACAGACCAACAACAACATAGAGTTAA
6126
6127  209_HRV45    GATCGACTCCATGGTATATCTAAAAGCTAAACACATCAAGGCATGGTGTCCCAGACCTCC
6128  210_HRV45a   GATCGACTCCATGGTATATCTAAAAGCTAAACACATCAAGGCATGGTGTCCCAGACCTCC
6129  211_HRV45b   GATCGACTCCATGGTATATCTAAAAGCTAAACACATCAAGGCATGGTGTCCCAGACCTCC
6130  GROUP_70    GATCGACTCCATGGTATATCTAAAAGCTAAACACATCAAGGCATGGTGTCCCAGACCTCC
6131
6132  209_HRV45    AAGAGCAGTCACATATAAC-CATACATATAATCCAAATTATGTTA-GGGCTG------AT
6133  210_HRV45a   AAGAGCAGTCACATATAAC-CATACATATAATCCAAATTATGTTA-GGGCTG------AT
6134  211_HRV45b   AAGAGCAGTCACATATAAC-CATACATATAATCCAAATTATGTTA-GGGCTG------AT
6135  GROUP_70    AAGAGCAGTCACATATAAC.CATACATATAATCCAAATTATGTTA.GGGCTG......AT
6136
6137  209_HRV45    GAAA------CAGCC---ACAAAAGTCCAAACTAGAGCAAATGTCACAACAGTA------
6138  210_HRV45a   GAAA------CAGCC---ACAAAAGTCCAAACTAGAGCAAATGTCACAACAGTG------
6139  211_HRV45b   GAAA------CAGCC---ACAAAAGTCCAAACTAGAGCAAATGTCACAACAGTT------
6140  GROUP_70    GAAA......CAGCC...ACAAAAGTCCAAACTAGAGCAAATGTCACAACAGT-......
6141
6142  209_HRV45    --------------------
6143  210_HRV45a   --------------------
6144  211_HRV45b   --------------------
6145  GROUP_70    ....................
6146
6147
6148
6149  Summary:
6150
6151  GROUP_1     AATCCAGTAGAAAACTACATTGATGAAGTTTTAAATGAAGTTTTAGTAGTGCCGAATATA
6152  GROUP_2     AATCCAGTGGAAAATTACATTGATGAAGTTTTAAATGAAGTTCTAGTAGTACCAAATATA
6153  GROUP_3     AACCCCGTTGAAAAGGTATGTTGATGAGGTTCTTAATGAAGTTCTGGTAGTTCCAAATATC
6154  GROUP_4     AATCCTGTTGAAAAATACGTTGATGAAGTCCTTAATGAGGTTCTAGTGGTTCCAAATATC
6155  GROUP_5     AACCCAGTTGAGAGATATGTAGATGATGTTTTAAATGAAGTTTTAGTTGTTCCAAATATT
6156  GROUP_6     AACCCAGTGGAAAACTATGTTAATGATGTACTTAATGAGGTTTTAGTAGTACCAAATATA
6157  GROUP_7     AATCCAGTAGAGAATTATGTAAATGATGTTCTTAATGAAGTGTTAGTTGTTCCAAACATA
6158  GROUP_8     AATCCAGTAGAAAATTATATAGATG-AGTATTAAATGAGGTATTAGTTGTTCCTAATATA
```

FIG. D14 CONT'D 10.trace                                                                                    9/20/2007 5:05 PM

```
6159 GROUP_9    AATCCAGTTGAAAATTACATTGATAATGTACTTAATGAAGTCCTAGTGGTACCCAACATC
6160 GROUP_10   AATCCAGTAGAAAATTATGTTGAAGGTGTGCTGAATGAAGTACTAGTGGTACCTAATATT
6161 GROUP_11   AATCCAGTTGAAGATTATGTTGAGGGTGTTTTAAATGAAGTTTTAGTAGTACCAAACATC
6162 GROUP_12   AATCCAGTTGAGGACTATATCGATAATGTACTTAATGAAGTCTTAGTAGTACCAAATACC
6163 GROUP_13   AATCCAATTGAAAATTATGTAGATCAAGTACTTAATGA-GTT-TAGT-GTACCAAATATT
6164 GROUP_14   AACCCAGTTGAAAA-TATGTGGATGA-GT-CTTAATGAAGT-TTAGTTGTGCCTAA-ATC
6165 GROUP_15   AATCCAGTTGAAAACTATGTGGAAGAGGTTCTTAATGAAGTCTTAGTAGTACCTAATATC
6166 GROUP_16   AACCCAGTCGAAAATTATGTGGAAGAGGTACTTAATGAAGTCTTAGTTGTACCAAATATC
6167 GROUP_17   AACCCAGTGGAGGATTATGTTGATGGAATTCTAAATGAGGTTTTAGTTGTACCTAATATA
6168 GROUP_18   AACCCAGTTGAAAATTACGTGGATGAGATATTAAATGAGGTTCTTGTAGTACCAAACATC
6169 GROUP_19   AATCCAGTAGAGAATTATATGAAGAGGTGTTGAATGAGGTTTTAGTAGTGCCTAATATC
6170 GROUP_20   AACCCAGTAGAAAATTATATAGAGAGGTTTTGAATGAAGTACTGGTTGTGCCTAATATT
6171 GROUP_21   AATCCAGTGGAAAATTATATAGATGAAGTCCTAAATGAGGTATTGGTTGTCCCTAATATT
6172 GROUP_22   AATCCAGTTGAAAATTACATAGATGAGGTACTAAATGAGGTATTGGTTGTACCAAACATT
6173 GROUP_23   AATCCAGTGGAATTACATAGATGAAGTATTAAATGAGGTATTAGTTGTCCCAAATATC
6174 GROUP_24   AATCCAGTAGAGAATTATATAGATGAAGTACTTAATGAAGTGTTAGTGGTCCCAAATGTG
6175 GROUP_25   AATCCTGTAGAGAGATATGTTGATGAAGTCCTGAATGAAGTGCTAGTAGTTCCAAATATT
6176 GROUP_26   AACCCAGTAGAAAATTTTGTGGATGAGATCTTGAATGAAGTTTTGGTGGTTCCAGATATC
6177 GROUP_27   AATCCTGTAGAGAATTA--TAGATGAAGT-CTAAATGA-GTCTTAGTAGTGCCAAATATC
6178 GROUP_28   AATCCTGTTGAAAATTATGTTGATGAAATTTTAAATGAAGTTCTTGTAGTCCCAAACACT
6179 GROUP_29   AATCCAGTTGAAAATTATGTGGATGAAATTTTAAACCAAGTTCTGGTAGTTCCAAACACC
6180 GROUP_30   AATCCAGTGGAGAATTACATAGATCAGGTGCTTAATGAGGTTTTGGTAGTCCCAAACATT
6181 GROUP_31   AATCCTGTGGAGAATTACATAGATCAAGTTTTAAATGAAGTTTTGGTAGTTCCAAACATC
6182 GROUP_32   AACCCAGTAGAAGATTATGTAGATCAGGTATTGAATGGAGTCCTGGTGGTGCCAAATATA
6183 GROUP_33   AACCCAGTGGAGAATTACATAGATGAAGTGTTAAATGAGGTTCTAGTAGTTCCAAACATT
6184 GROUP_34   AACCCAGTGGAGAATTACATAGATGAAGTGTTGAATGAAGTGTTAGTTGTTCCAAATATT
6185 GROUP_35   AACCCAGTAGAGGAGTACATAGATGGAGTCCTTGAATGAAGGTTCTTGTGGTTCCGAACATT
6186 GROUP_36   AATCCAGTAGAAAGCTACATAGATGGGGTCTTAAACGAAGTCCTTGTGGTTCCAAACATT
6187 GROUP_37   AACCCAGTTGAACAATACATTGATGGTGTGTTGAATGAAGTTTTGATTGTCCCAAACATC
6188 GROUP_38   AATCCAGTTGAGAAATACATTGATGGTGTATTGAATGAAGTTTTAGTTGTTCCAAATATC
6189 GROUP_39   AACCCTGTAGAGAAATATGTAGATGAAGTGTATTGAATGAAGTATTGGTTGTCCAAACACA
6190 GROUP_40   AATCCAGTTGAAAAGTATGTTGATAGTGTTTTAAACGAGGTATTAGTTGTTCCTAACATT
6191 GROUP_41   AATCCTGTAGAGAAATATGTGGACACCATTCTGAATGAGGTGCTAGTGTGTCCCAAATATC
6192 GROUP_42   AATCCTGTTGAAAGGTATGTAGATGAAGTCTTGAATGAAGTTCTTGTAGTACCAAATATC
6193 GROUP_43   AATCCTGTAGAAAGGTATGTGGATGAGGTCCTGAATGAGGTTCTTGTGGTACCAAATATT
6194 GROUP_44   AATCCTGTAGAAAGATATGTAGATGAAGTTTTGAATGAAGTCCTTGTAGTACCCAATATC
6195 GROUP_45   AACCCTGTGGAAAGATATGTAGATGAAGTTTTAAATGAAGTGCTTGTAGTCCCAAACATT
6196 GROUP_46   AACCCTGTAGAGAGATATGTAGATGAAGTCTTGAATGAGGTTCTTGTAGTCCCTAATATT
6197 GROUP_47   AATCCAGTGGAAAGATATGTAGATGAAGTCTTAATGAAGTGTTAGTGCCCAATATT
6198 GROUP_48   AACCCAGTGGAGCGGTATGTGGATGAAGTCTTAAATGAGGTATTGGTAGTCCCTAATATT
6199 GROUP_49   AACCCTGTTGAGAATTATATAGATGAAGTTCTTAATGAAGTTTAGTTGTCCCAAATATT
6200 GROUP_50   AATCCTGTTGAACACTACATAGATGAGGTCCTTAATGAGGTTTTAGTTGTTCCAAATATT
6201 GROUP_51   AATCCAATTGAGAACTATGTAGATGAAGTTCTTAATGAAGTCTTAGTTGTTCCCAATATC
6202 GROUP_52   AACCCGGTTGAAAATTTTGTAGATGAAGTTCTTAGTGAAGTTTTTAGTTGTTCCAAACATT
6203 GROUP_53   AACCCGGTAGAGAATTATGTAGATAGCTTACTAAATGAAGTATTAGTGGTACCTAATATT
6204 GROUP_54   AATCCAGTAGAAAACTATGTAGATAACTTGTTAAACGAAGTGCTAGTAGTTCCTAACATT
6205 GROUP_55   AATCCAGTTGAAAATTACATAGATAATGTATTAAATGAAGTACTTGTAGTGCCAAACATC
6206 GROUP_56   AACCCAGTTGAAAATTATATAGATAGTGTATTAAATGAAGTTCTTGTGGTGCCAAATATC
6207 GROUP_57   AATCCAGTAGAAAATTACATAGATAATGTGTTAAATGAAGTACTTGTAGTTCCAAATATC
6208 GROUP_58   AATCCAGTAGAGAGATATGTTGATGAGGTGCTAAATGAAGTTCTAGTTGTTCCAAACATA
6209 GROUP_59   AATCCAGTGGAAGAATATGTTGATCAGGTTTTAAATGAGGTTTTAGTTGTTCCAAACATA
6210 GROUP_60   AACCCAGTGGAAAGGTACACAGAAGCTATTTTAAATGAAGTTCTTGTAGTTCCAAATATC
6211 GROUP_61   AACCCAGTTGAAAAATACACAGAAGCCGTTCTTAATGAGGTCCTTGTGGTTCCAAACATA
6212 GROUP_62   AATCCAGTTGAAAAATATACTGAAGCACTACTTAATGAAGTGCTTGTTGTGCCAAACATC
6213 GROUP_63   AACCCGGTAGAGAATTACACAGAGGCTATCTTAAATGAAGTATTAGTAGTCCCAAACATT
6214 GROUP_64   AATCCAGTGGAAAAATATACAGAAGCTGTTCTTAATGAGGTCCTTGTAGTACCTAACATC
6215 GROUP_65   AATCCAGTCGAAAAATACACAGAAGCAATCCTCAATGAAGTTCTTGTTGTACCAAACATC
6216 GROUP_66   AACCCTGTTGAAAAATATACAGAGGCTTTACTCAATGAAGTGTTGGTGGTTCCCAACATA
6217 GROUP_67   AATCCAATTGAGAAGTATACAGAAGCTCTACTTAATGAAGTGTTAGTGGTCCCAAATATA
6218 GROUP_68   AATCCTGTAGAAAAATATACAGAAGCAATACTCAATGAGGTTCTAGTTGTGCCAAATATA
6219 GROUP_69   AACCCTATTGAACAATTCACAGAGGCAGTATTAAACGAGGTCTTGTAGTTCCAAA-ACA
6220 GROUP_70   AACCCTGTTGAACAATTTGCAGAAGCAGTCCTTGATCAAGTATTAGTAGTTCCAAACACT
6221 SUMMARY    AAXCCXXTXGAXXX-TX--XXXAXX--XT-XTXXXXXA-GT--TXXT-GTXCCXXA-XXX
6222
6223 GROUP_1    AAAGAAAGTCATCACACTACATCAAACTCTGCCCCACTTTTAGATGCTGCAGAGACGGGA
```

FIG. D14 CONT'D

```
10.trace                                                                9/20/2007 5:05 PM 6224 GROUP_2   AAAGAAAGCCATCACACTACATCAAATTCTGCTCCACTCTTGGATGCTGCAGAGACAGGA
6225 GROUP_3   AGAGAGAGCCATCCAACTACATCAAATTCGGCCCCTGCCTTGGATGCAGCAGAGACTGGA
6226 GROUP_4   AAAGAGAGTCACCCAACTATATCAAATTCAGCTCCTGCTTTGGATGCAGCAGAGACTGGC
6227 GROUP_5   AGGGAGAGCCATCCATCCACATCAAATTCTGCCCCTGCATTAGATGCTGCTGAAACTGGC
6228 GROUP_6   CAGGAAAGCCACCCAACCACCTCAAATGCTGCTCCAGCATTAGATGCAGCAGAGACTGGA
6229 GROUP_7   CAAGAAAGCCATCCAACCACATCAAACGCTGCTCCTGTACTTGATGCTGCGGAAACAGGA
6230 GROUP_8   AGAGAGAGCCATCCAACTACATCTAATGCAGCT-CAGCTTTGGATGCTGCTGAAACTGGA
6231 GROUP_9   AGAGAAAGTCATCCAAGCACCTCTAACTCTGCCCCAATTCTCGATGCAGCTGAGACTGGT
6232 GROUP_10  AGAGAGAGCCATCCAAGCACCTCAAACTCTGCTCCAATCCTTGATGCTGCTGAAACTGGC
6233 GROUP_11  AAGGAAAGCCATCCAAGCACATCAAATGCTGCCCCAATACTAGATGCAGCTGAAACAGGT
6234 GROUP_12  AAGGAGAGTCATCCAAGCACTTCTAACTCTGCTCCTATACTAGATGCAGCTGAAACAGGC
6235 GROUP_13  AAAGAAAGTCACCC-AG-AC-TCAAA-TCTGCCCCAATTCTAGATGCTGCTGAAAC-GGA
6236 GROUP_14  AG-GAGAGCCACCCAAGCA--TC-AACTCTGC-CCAAT-TTGGATGCTGCTGA-ACTGGA
6237 GROUP_15  AAAGAAAGCCATCCAAGCACATCTAATTCTGCCCCAATCCTGGACGCTGCTGAAACTGGA
6238 GROUP_16  AAAGAAAGTCATCCAAGTACATCCAACTCTGCCCCGATTTTAGATGCTGCTGAAACTGGA
6239 GROUP_17  AAGGAGAGCCAAGCTACCACATCAAACTCAGCACCTGCTCTAGATGCAGCTGAAACCGGA
6240 GROUP_18  AAAGAGAGTCAGGCTACCACATCAAATGCAGCACCTGCTTTGGATGCAGCTGAGACTGGG
6241 GROUP_19  AGAGAGAGTCAAGCAACCACATCAAATTCAGCACCTGCCTTAGATGCAGCTGAGACTGGA
6242 GROUP_20  AAGGAAAGTAAACCATCAACATCAAACTCAGCACCAGCTTTGGATGCAGCAGAAACTGGA
6243 GROUP_21  AAGGAAAGTAAACCTTCAACTTCAAACTCAGCGCCAGCTTTAGATGCAGCAGAAACCGGA
6244 GROUP_22  AAAGAAAGCCAAGCCACCACATCAAACTCTGCCCCCGCACTGGATGCAGCTGAGACTGGT
6245 GROUP_23  AAGGAGAGTCAAGCCACTACATCAAACTCTGCCCCTGCTTTAGATGCAGCTGAAACTGGA
6246 GROUP_24  AATGAAAGTCACGCAATTACATCAAATTCAGCCCCTGCTTTAGATGCCGCTGAAACTGGT
6247 GROUP_25  AGGGAGAGTCAAGCAGCAACATCAAATTCAGCTCCAGTACTAGCAGCAGAAACTGGG
6248 GROUP_26  AAACAAAGTCAAGCAACAACATCAAACTCAGCACCTGCATTGGATGCAGCTGAAACTGGA
6249 GROUP_27  AGAGAGAGTCATGGAACAACATCAAACTCTGCTCCCGCACTTGATGCTGCAGAAACTGG-
6250 GROUP_28  GTAGAAAGTCATTCAACAACATCCAAGTGCAGCCCCTGCACTTGATGCAGCTGAAACTGGG
6251 GROUP_29  ATGGAGAGCCATCCAACAACGTCTAATGCTGCTCCAGCTTTAGATGCTGCTGAAACTGGC
6252 GROUP_30  AAAGAGAGCAACCCTACAACCTCTAACTCAGCTCCAGCTCTAGATGCTGCTGAGACAGGC
6253 GROUP_31  AAAGAAAGCAATCCCACAACCTCTAATTCAGCCCCAGCCTTAGATGCTGCCGAAACAGGT
6254 GROUP_32  AAGCAAAGTGAACCCACGACTTCCAATTCAGCCCCAGCTCTAGATGCTGCTGAGACAGGT
6255 GROUP_33  AAGGAGAGTCACTCAAGCACATCCAACTCAGCACCAGCACTAGATGCAGCTGAGACCGGC
6256 GROUP_34  AGAGAAAGCCATTCAAGTACTTCAAACTCAGCACCAGCACTGGATGCAGCTGAAACTGGC
6257 GROUP_35  AAGGAAAGCCACTCCAGCACATCAAATTCAGCACCAGCATTAGATGCTGCTGAGACTGGA
6258 GROUP_36  AGGGAGAGCCAACCCACTACTTCTAATTCTGCTCCAGCATTGGATGCTGCTGAGACTGGT
6259 GROUP_37  AATGAGAGCCATCCCAGCACTTCCAATGCAGCGCCAGCTTTAGATGCAGCTGAGACCGGA
6260 GROUP_38  AATGAGAGTCACCCTAGCACATCCAATGCAGCGCCAGCCTTAGATGCTGCCGAAACTGGA
6261 GROUP_39  AATGAAAGTCACCCCAGTACATCAAATGCTGCACCAGCACTAGATGCTGCTGAAACTGGA
6262 GROUP_40  AATGAAAGTCATCCTAGTACTTCCAAATTCAGCTCCTGCCTTGGACGCTGCAGAGACAGGA
6263 GROUP_41  AATGAAAGTCATCCAAGTACATCAAATGCTGCTCCTGCCTTAGATGCAGCCGAGACAGGA
6264 GROUP_42  AGTGAAAGTAGCTCAACTACATCTAATTCAGCTCCAGCCTTAGATGCTGCAGAAACTGGC
6265 GROUP_43  AGTGAAAGCAGTCCAACTACTTCTAATTCAGCTCCAGCCCTAGATGCAGCAGAGACTGGT
6266 GROUP_44  AATGAAAGTAATCCAACTACTCCAACTCAGCCACCTGCACTGGACGCTGCAGAAACTGGC
6267 GROUP_45  AATCAGAGCAACCCTACACATCCAACTCAGCACCAGTCTTAGACGCTGCTGAAACAGGT
6268 GROUP_46  AATGAAAGTTACCCAACAACTTCCAATTCAGCCCCAGTGCTAGATGCCGCTGAAACAGGT
6269 GROUP_47  AATGAGAGCCACCCTACCACATCAAATGCGGCCCCAGTTTTGGATGCTGCTGAAACAGGA
6270 GROUP_48  AATGAAAGCCACCCTACAACATCTAATTCAGCTCCTGTTTTAGATGCAGCTGAAACTGGA
6271 GROUP_49  AATAGTAGTAACCCCACAACATCAAATTCTGCCCCAGCATTAGATGCTGCAGAAACAGGG
6272 GROUP_50  AATAGTAGTCACCCCACGACATCAAACTCTGCTCCAGCATTAGATGCTGCAGAAACAGGG
6273 GROUP_51  AATAGTAGTCATCCCACAACATCAAACTCTGCTCCAGCATTAGACGCTGCGGAAACGGGT
6274 GROUP_52  AACAGTAGTCACCCTACTACATCAAACTCTGCTCCGGCATTAGATGCTGCAGAAACAGGA
6275 GROUP_53  CAGCCAAGTACATCTGTTTCAAGTCACTCTGTACCAGCATTGGATGCTGCAGAGACTGGA
6276 GROUP_54  CAACCTAGCACATCCGTTTCAAGTCACTCTGTGCCAGCTCTGGATGCTGCGGAAACAGGG
6277 GROUP_55  CAACCTAGTTCATCTGTGTCAAGTCATTCAGCTCCCGCCTTAGACGCTGCGGAAACTGGA
6278 GROUP_56  CAACCTAGCACATCTGTGTCAAGTCATGCAGCGCCTGCATTGGATGCTGCGGAAACCGGA
6279 GROUP_57  CAACCTAGTACATCTGTATCAAGTCATTCTGTGCCTGCCTTGGATGCTGCAGAAACGGGA
6280 GROUP_58  AACAAAAGTAATGGGCAGTTATCAAACGCAGCACCAGCGTTGGACGCTGCAGAAACTGGT
6281 GROUP_59  AAAGAAAGTAAACCCCAGTCTAGCAACTCCGCTCCAGTTTTGGACGCTGCAGAAACAGGT
6282 GROUP_60  ACATCTAGTAACTCCCAAACATCAAATGCAGCACCAGCACTAGATGCTGCTGAGACAGGA
6283 GROUP_61  CCAGCAAGTAATACCCAAACTTCAAATGCAGCCCCAGCTTTAGATGCTGCTGAGACTGGA
6284 GROUP_62  AATCCTAGCAACGCACAAACTACAAATGCAGCTCCCGCTCTCGATGCCGCTGAGACGGGG
6285 GROUP_63  AATGCAAGCAATCCACAAACTTCAAATTCAGCACCAGCACTAGATGCTGCAGAAACGGGT
6286 GROUP_64  AATGCCAGTAGTGGACATACATCTAATTCAGCTCCAGCACTTGATGCAGCAGAAACTGGA
```

FIG. D14 CONT'D

10.trace                                                                                        9/20/2007 5:05 PM

```
6287 GROUP_65    AGTGCTAGCAATGGACATACATCAAACTCAGCTCCAACACTTGATGCAGCAGAAACTGGT
6288 GROUP_66    CAACCTAGCAGTGGGCACACATCTAATGCTGCACCAGCTCTAGATGCTGCTGAGACAGGA
6289 GROUP_67    CAAGCTAGTAATGGGCATACATCTAATGCTGCACCAGCTTTAGATGCTGCTGAAACAGGA
6290 GROUP_68    CAACCTAGTAATGGACATACCTCAAACTCAGCACCAGCCTTAGATGCAGCAGAAACTGGG
6291 GROUP_69    CAAGC-AGTAATGGATCTATAGCAAATTCAGCACCAGCATTAGATGCAGCAGAGACTGGA
6292 GROUP_70    CGACCCAGCGATGGGTTGATTGCAAACTCAGCCCCAGCTTTGGATGCAGCTGAAACTGGA
6293 SUMMARY     XX-XX-AGXXXXXX-XX-X--XX-XA-XCXGX--CXXX-XTXGAXGCXGCXGA-AC-GG-
6294
6295 GROUP_1     CACACCAGTAATGTTCAACCAGAAGATGCTATAGAGACAAGGTATGTTATAACATCACAA
6296 GROUP_2     CACACCAGTAATGTACAACCAGAGGATGCTATAGAAACAAGATATGTTATGACATCACAA
6297 GROUP_3     CATACAAGCAACATACAACCTGAAGATACAATAGAAACAAGATTTGTGCAGACATCACAA
6298 GROUP_4     CATACAAGTAGTACACAGCCCGAGGATACAATAGAGACCAGGTTTGTTCAAACTTCACAG
6299 GROUP_5     CATACTAGTGCAATCCAACCAGAAGACACTATAGAAACCAGATATGTACAGACATCACAA
6300 GROUP_6     CATACAAGCAGTATACAACCTGAGGATACCATAGAAACAAGATATGTTCAGACATCACAA
6301 GROUP_7     CACACAAGCAGTATACAACCTGAGGATACTGTAGAAACTAGATATGTGCAAACGTCTCAA
6302 GROUP_8     CACACAAGTAGCA-CCA-CCTGAAGACACAATTGAAACAAGATATGTGCAAACCTCACAT
6303 GROUP_9     CATACCAGTAGTGTACAACCAGAAGATACGGTTGAAACACGATATGTGCAAACATCCCAG
6304 GROUP_10    CACACTAGTAATGTGCAACCTGAAGATACAGTTGAAACTCGATATGTGCAGACATCACAG
6305 GROUP_11    CACACTAGTAAAGTACAACCAGAAGATACAGTTGAGACTCGTTACGTGCAAACATCACAG
6306 GROUP_12    CATACTAGTAGTGTGCAACCAGAAGATACAGTTGAGACCCGCTATGTACAAACTTCCCAG
6307 GROUP_13    CACACTAG-AATGT-CAACCAGA-GA-AC-ATTGAAAC-CGT-ATGTTCAAACCACACAA
6308 GROUP_14    CATACTAGTAATGTACAACCAGAAGATACCATTGAGACTCG-TATGTACAAACCTCACA
6309 GROUP_15    CACACTAGTAATGTACAACCAGAAGATACAATTGAAACTCGCTACGTGCAAACATCACAA
6310 GROUP_16    CACACTAGCAATGTACAGCCAGAAGATACAATTGAAACTCGATATGTACAAACAGCACAA
6311 GROUP_17    CATACTAGCAAAGTGCAGCCAGGAGGATATGATTGAGACTAGATATGTGCAGACTTCACAG
6312 GROUP_18    CACACAAGCAGCGTTCAACCAGAGGACATGGTTGAGACTAGGTATGTGCAAACATCACAA
6313 GROUP_19    CACACTAATAATGTACAACCAGAAGATATGATTGAAACAAGATATGTACAAACATCACAA
6314 GROUP_20    CATACGAGTAGCGTGCAGCCAGAAGATATGGTTGAAACTAGATATGTCCAAACATCACAA
6315 GROUP_21    CATACTAGTGATGTCCAGCCAGAAGATGTGCTAGAGACCAGATACGTGCAAACATCACAA
6316 GROUP_22    CACACTAGCAGTGTACAACCTGAAGATATGATTGAGACCAGGTACGTACAAACATCACAA
6317 GROUP_23    CACACAAGTAATGTGCAGCCTGAAGATATGCTTGAAACTAGATATGTGCAAACATCGCAT
6318 GROUP_24    CACACCAGCAATGTCCAACCTGAAGATATGATTGAGACTAGGTATGTACAAACATCACAA
6319 GROUP_25    CATACAAGCAATGTACAACCAGAAGATGTAATTGAGACAAGATATGTTCAGACATCACAA
6320 GROUP_26    CACACTAGTAATGTACAACCGGAAGACATGATTGAAACTAGATATGTCCAGACATCACAA
6321 GROUP_27    CACACTAGTAATGTACA-CC-GAGGATATGGTTGAAACAAGGTATGTTCAGACATCACAA
6322 GROUP_28    CATACTAGCCAGGTGCAACATGGTAGAGACAAGGTCAGTACATAATTTCCAA
6323 GROUP_29    CATACCAGCCATGTTCAACCAGAAGACATGTTAGAAACAAGGCAAGTACAAAATTTCCAA
6324 GROUP_30    CATACTAGCAATGTTCAACCTGAAGACATGATTGAAACACGTTATGTGCAGACATCACAA
6325 GROUP_31    CATACCAGTAATGTTCAACCTGAAGACATGATTGAAACACGTTATGTGCAAACAACACAC
6326 GROUP_32    CACACTAGCAGTGTACAACCTGAAGATATGATCGAGACTCGTTATGTACAGGCATCAAAT
6327 GROUP_33    CATACTAGCAGTGTTCAACCTGAGGATATGATTGAAACTCGTTACGTCCAAACATCACAG
6328 GROUP_34    CATACCAGTAATGTGCAACCAGAAGATATGGTTGAGACACGCTATGTGCAAACCTCACAG
6329 GROUP_35    CACACCAGTAATGTGCAGCCTGAGGATATGATTGAAACTCGCTATGTACAGACATCACAA
6330 GROUP_36    CACACTAGTAATGTACAGCCTGAGGACGTGATTGAAACACGTTATGTGCAGATTACACAA
6331 GROUP_37    CACACCAGTAATGTTACAGCCTGAAGATATGATTGAAACGCGCTATGTACAAAACACTCAA
6332 GROUP_38    CACACAAGCAATGTACAACCTGAGGATATGATTGAAACACGCTATGTACAAAACACTCAA
6333 GROUP_39    CACACAAGCAATGTGCAGCCAGAAGACACTATAGAAACACGTTATGTGTTAAATTCACAA
6334 GROUP_40    CATACAAGTACTGTTCAACCTGAGGACATGATTGAAACACGGTATGTTCAAACATCACAA
6335 GROUP_41    CATACTAGCAATGTACAGCCTGAGGACATGATCGAAACACGCTATGTTCAAACGTCCCAG
6336 GROUP_42    CACACAAGCAGTGTACAACCAGAAGACATGGTTGAAACACGTTATGTCCAAACTTCACAA
6337 GROUP_43    CATACCAGTAATGTACAACCAGAAGATATGATTGAAACTCGTTACGTGCAAACCTCACAA
6338 GROUP_44    CATACCAGTGGTGTACAACCAGAAGACATGATTGAGACCCGTTATGTCCAAACATCACAG
6339 GROUP_45    CATACCAGCAATGTTCAACCGGAGGACACGATTGAAACACGATATGTTCAAACCTCACAG
6340 GROUP_46    CATACTAGCAATGTCCAACCAGAGGATATGATTGAGACTCGATATGTTCAGACATCGCAG
6341 GROUP_47    CATACCAATAAGATACAGCCAGAAGACACTATAGAAACCAGATATGCAATCTTCACAG
6342 GROUP_48    CACACCAGTAATATACAACCTGAGGATACTATTGAGACCAGATATGTACAATCTTCACAG
6343 GROUP_49    CACACTAGTAGTGTTCAACCAGAGGATGTCATTGAAACTAGGTATGTGCAGACATCACAA
6344 GROUP_50    CACACTAGCAATGTGCAACCTGAAGATGTCATTGAAACCAGATATGTACAGACATCACAA
6345 GROUP_51    CACACTAGTAATGTTCAACCAGAAGATGTCATTGAAACCAGGTACGTTCAAACATCACAA
6346 GROUP_52    CATACTAGTAATGTTCAACCTGAAGATGTCATTGAAACTAGATATGTTCAAACATCACAA
6347 GROUP_53    CATACTAGTTCTGTTCAACCTGAAGATATGATCGAGACAAGGTATGTCATAACAGACCAA
6348 GROUP_54    CATACTAGTTCTGTTCAACCTGAAGATATGATAGAAACTAGATATGTTATAACAGATCAA
6349 GROUP_55    CATACCAGCTCTGTCCAACCAGAGGACATGATCGAGACCAGATATGTCATAACTGATCAA
```

FIG. D14 CONT'D

10.trace                                                                                              9/20/2007 5:05 PM

```
6350  GROUP_56    CACACCAGCTCTGTTCAACCTGAAGATATGATTGAAACTAGATATGTTATAACTGATCAA
6351  GROUP_57    CACACAAGTTCTGTTCAGCCTGAGGATATGATTGAAACTAGATATGTTATCACAGATCAA
6352  GROUP_58    CATACCAGCCAAACACAACCAGAAGATGTGATTGAAACCAGGTATGTGATTACAGACCAG
6353  GROUP_59    CATACGAACCAAGTACAGCCTGAAGACACCATAGAAACTAGATATGTTTATAACTGACCAA
6354  GROUP_60    CACACAAACCAGGTCCAGCCAGAAGATATGGTCGAGACACGGTATGTAATTACTGATCAG
6355  GROUP_61    CATACAAACCAAGTCCAACCAGAAGATGTGGTTGAAACACGCTATGTCATAACAGACCAG
6356  GROUP_62    CACACAAGCCAAACACAACCTGAAGACATGGTTGAGACTAGGTATGTAATCACAGATCAG
6357  GROUP_63    CATACAAGTCAGACACAACCTGAGGACATGCTGGAAACTAGATATGTCATCACAGACCAA
6358  GROUP_64    CACACTAGCCAGATACAACCAGAAGACATGATAGAAACCAGATATGTTATCACAGACCAA
6359  GROUP_65    CACACTAGCCAGGTGCAACCAGAAGACATGATAGAAACTAGATATGTTATTACTGATCAG
6360  GROUP_66    CATACTAGTCAAGTTCAACCAGAAGATATGGTAGAGACCAGGTATGTTGTCACAGACCAA
6361  GROUP_67    CACACTAGTCAAGTTCAACCAGAGGATGTGATAGAAACCAGATATGTCATCACAGATCAA
6362  GROUP_68    CATACCAACCAAGTACAACCAGAAGATGTTATGGAAACCAGATATGTGATCACTGATCAA
6363  GROUP_69    CACACAAGTTCAGTGCAACCTGAAGATCTTATAGAGACTAGGTATGTAATTACAGATCAA
6364  GROUP_70    CACACCAGTTCAGTGCAGCCTGAGGACCTTATAGAGACTAGATATGTGATTGCAGACCAA
6365  SUMMARY     CAXACXAX-XXXX--CA-CC-GA-GA-XX-XTXGAXAC-XG--XXGTXXXXXXXXXXXA
6366
6367  GROUP_1     ACAAGAGATGAGATGAGTATAGAAAGTTTCCTTGGTAGATCTGGTTGTGTCCACATCTCA
6368  GROUP_2     ACAAGAGATGAGATGAGTATAGAAAGTTTTCTTGGTAGATCTGGCTGTGTGCATATTTCA
6369  GROUP_3     ACTAGAGATGAAATGAGCATAGAGAGTTTCTTGGGAAGATCTGGGTGCATTCATATATCC
6370  GROUP_4     ACTAGGGATGAAATGAGTTTAGAAAGTTTCTTGGGAAGATCTGGATGTATCCATATATCT
6371  GROUP_5     ACTAGGGATGAAATGAGTATAGAGAGTTTTCTAGGTAGATCAGGTTGTATACATATATCA
6372  GROUP_6     ACTAGAGATGAGTGTAGAAAGTTTCTTAGGTAGATCTGGGTGTATACATATTTCA
6373  GROUP_7     ACAAGGGATGAAATGAGTGTAGAGAGCTTTCTTGGTAGATCAGGATGCATACACATATCA
6374  GROUP_8     ACTAGGGATGAAATGAG-GTTGAAAGTTTCTTAGGCAGATCTGGCTGTATTCACATTTCC
6375  GROUP_9     ACGAGAGATGAAATGAGTATTGAAAGTTTTCTTGGCAGGTCAGGTTGTATACACACCTCA
6376  GROUP_10    ACCAGGGATGAAATGAGTATTGAGAGCTTTCTTGGAAGATCTGGTTGTATACACACCTCA
6377  GROUP_11    ACTAGAGATGAAATGAGCATAGAAAGTTTTCTAGGTAGGTCAGGATGTATCCATATATCA
6378  GROUP_12    ACAAGGGATGAGATGAGTATTGAGAGCTTTCTGGGTAGGTCTGGTTGTATTCACATTTCA
6379  GROUP_13    ACTAGAGATGAAATGAG-ATTGA-AG-TTTCTTGGTAGGTCAGGGTG-GTACA-ACTTCA
6380  GROUP_14    ACTAGAGATGAAATGAGCATTGAAAGTTT--T-GG-AGATCAGG-TGTATACATGTTTCA
6381  GROUP_15    ACAAGAGATGAAATGAGCATTGAAAGTTTCCTTGGTAGGTCAGGATGTGTACATACTTCA
6382  GROUP_16    ACAAGAGATGAAATGAGCATTGAGAGCTTCCTTGGCAGGTCAGGATGTGTGCATTCCTCA
6383  GROUP_17    ACTCTTGATGAAATGAGCATTGAGAGCTTCCTAGGTAGATCTGGTTGTATTCACATGTCC
6384  GROUP_18    ACTCTTGATGAGATGTATGGAGAGTTTCTTAGGGAGATCTGGTTGTATTCATATTTCA
6385  GROUP_19    ACTCTTGATGAGATGAGTGTGGAAAGCTTCTTAGGAAGGTCTGGTTGCATTCACATGTCA
6386  GROUP_20    ACATTACATGAGATGAGTGTTGAAAGTTTCTTGGGTAGATCAGGTTGCATACACATGTCC
6387  GROUP_21    ACAAGAGATGAAATGAGTGTTGAAAGTTTTCTTAGGGAGATCAGGTTGCATTCATATGTCA
6388  GROUP_22    ACAAGAGATGAAATGAGCATTGAGAGTTTCCTGGGTAGGTCTGGCTGTATACACATGTCC
6389  GROUP_23    ACAAGAGATGAAATGAGCATTGAAAGTTTCCTAGGTAGATCTGGTTGTATACATATATCT
6390  GROUP_24    ACAAGAGATGAAATGAGTATAGAGTGTTTCTAGGCAGATCAGGGTGTATACATATCTCC
6391  GROUP_25    ACTCGTGATGAGATGAGCATTGAAAGTTTCTTAGGTAGATCAGGATGTATACATATCA
6392  GROUP_26    ACACGTGATGAAATGAGTCTTGAGAGCTTCTTAGGAAGATCTGGCTGCATTCATATTTCA
6393  GROUP_27    ACACGTGATGAAATGAGTATTGAAAGTTTTCT-GGCAGATCAGGGTG-AT-CACATGTCA
6394  GROUP_28    ACCAGAGATGAAATGAGTATTGAAAGTTTCTTGGGCAGATCTGGTTGCATACATATTTCA
6395  GROUP_29    ACTAGAGATGAGATGAGTATTGAGAGCTTCCTAGGCAGATCAGGATGTGTATTCATATTTCA
6396  GROUP_30    ACCAGAGATGAAATGAGTCTTGAAAGCTTCTTAGGGAGATCAGGTTGTATACACATATCT
6397  GROUP_31    ACTAGAGATGAGATGAGTCTTGAGAGCTTCTTAGGGAGGTCAGGATGTGTACATATATCC
6398  GROUP_32    ACCAGAGATGAAATGAGTCTCGAGAGCTTTCTTGGAAGGTCAGGCTGTATTCATATATCA
6399  GROUP_33    ACCAGAGATGAAATGAGTATTGAGAGCTTCCTTGGTAGATCAGGGTGTGTCCATATTTCT
6400  GROUP_34    ACAAGAGATGAGATGAGTGTAGAAAGTTTTCTTGGAAGATCAGGGTGCATCCATATCTCA
6401  GROUP_35    ACTAGAGATGAAATGAGTGTAGAAAGTTTTCTAGGAAGATCAGGTTGTGTACATATATCC
6402  GROUP_36    ACTAGAGATGAGATGAGTGTTGAGAGCTTCCTCGGCAGATCTGGATGTATTCATATTTCC
6403  GROUP_37    ACTAGAGATGAAATGAGCATTGAAAGTTTCTGGGCAGGTCTGGTTGTATACATATCA
6404  GROUP_38    ACAAGGGATGAAATGAGCATTGAAAGCTTCTTGGGAAGATCTGGCTGTATACACATAGCA
6405  GROUP_39    ACTAGAGATGAAATGAGTATTGAGAGCTTCCTGGGAAGATCTGGTTGCATACATATATCA
6406  GROUP_40    ACTAGAGATGAGATGAGCCTTGAGAGTTTCCTAGGGAGATCTGGCTGCATACACATATCA
6407  GROUP_41    ACTAGGGATGAAATGAGCATAGAAAGTTTCTTGGCAGATCCGGTTGTGTACATGTTTCA
6408  GROUP_42    ACTAGGGATGAAATGAGTGTTGAGAGCTTTTTAGGCAGATCTGGTTGTATACACATGTCT
6409  GROUP_43    ACTAGAGATGAAATGAGCATAGAAAGCTTTTTAGGTAGATCAGGCTGTGTACATAAGTCC
6410  GROUP_44    ACTAGAGATGAAATGAGCATTGAAAGCTTCCTTGGCAGGTCAGGTTGTATACACATGTCA
6411  GROUP_45    ACAAGAGATGAAATGAGTGTAGAAAGTTTCTTGGGTAGATCAGGGTGTATACATATGTCA
6412  GROUP_46    ACGAGAGATGAAATGAGCATTGAGAGCTTTTTGGGTAGATCAGGGTGTATACACATGTCA
6413  GROUP_47    ACATTGGATGAAATGAGTGTGGAAAGCTTCCTAGGCAGATCGGGGTGCATCCATGAATCA
6414  GROUP_48    ACACTGGATGAAATGAGTGTAGAAAGTTTTTTAGGCAGATCAGGTTGCATTCATGAATCC
```

FIG. D14 CONT'D 10.trace                                                                                   9/20/2007 5:05 PM

```
6415 GROUP_49   ACAAGAGATGAAATGAGTTTAGAGAGTTTTCTTGGCAGATCAGGATGCATACATGAATCT
6416 GROUP_50   ACAAGAGATGAAATGAGTTTAGAGAGTTTTCTTGGTAGGTCAGGGTGTATACATGAATCC
6417 GROUP_51   ACAAGAGATGAAATGAGTTTAGAAAGTTTCCTTGGTAGGTCAGGGTGTATACATGAATCT
6418 GROUP_52   ACAAGGGATGAAATGAGTTTAGAAAGCTTTCTTGGTAGATCAGGATGTATACACGAGTCT
6419 GROUP_53   ACAAGGGATGAAACTAGTATAGAGAGTTTCTTAGGTAGATCTGGATGTATTGCTAAAGTT
6420 GROUP_54   ACAAGGGATGAAACCAGCATTGAAAGCTTTCTGGGTAGGTCTGGATGCATAGCAAAAATT
6421 GROUP_55   ACAAGAGATGAGACAAGTATTGAAAGCTTCTTAGGTAGGTCAGGGTGCATAGCTATGATA
6422 GROUP_56   ACAAGGGATGAAACAAGTATTGAGAGTTTCTTAGGTAGGTCAGGGTGTATCGCTATGATA
6423 GROUP_57   ACAAGAGATGAAACTAGCATTGAAAGCTTTTTAGGTAGATCTGGTTGCATTGCTATCATA
6424 GROUP_58   ACTAGAGATGAGATGTCAATTGAATCTTCCTTGGTCGGTCCGGATGCATTTCAATTATC
6425 GROUP_59   ACAAGAGATGAAATGAGCATTGAAAGTTTCCTCGGAAGATCAGGTTGTGCAACAATTATG
6426 GROUP_60   ACCCGTGATGAAATGAGTGTGGAAAGTTTTCTTGGTAGATCTGGTTGCATTGCTATCATA
6427 GROUP_61   ACAAGGGATGAAATGAGCATAGAGAGCTTCCTCGGTAGGTCAGGTTGCATTGCAATCATA
6428 GROUP_62   ACCCGTGATGAAATGAGTATAGAGAGTTTCTTAGGTAGGTCTAGTTGCATTGCAATAATC
6429 GROUP_63   ACCCGGGATGAAATGAGCATTGAAAGTTTCTTAGGCAGATCAAGTTGCATTGCTGAGATC
6430 GROUP_64   ACAAAAGATGAAATGAGTATAGAAAGTTTTCTACGGAAGGTCAGGCTGCATTGCCATTATT
6431 GROUP_65   ACAAAGGATGAGATGAGCATTGAAAGTTTCTTAGGAAGATCTGGTTGTGTTGCTATCATT
6432 GROUP_66   ACTAGAGAAATGATATAGAGAGTTTCTTGGGTAGATCTGCTTGCGTAGCAATCATC
6433 GROUP_67   ACCAGAGATGAGATGAGCGTAGAGAGTTTCCTGGGCAGATCTGCCTGCATAGCAGTCATT
6434 GROUP_68   ACTAGGGATGAAATGAGCATTGAGAGCTTCTTGGGCAGATCTGCATGCATAGCTACCATA
6435 GROUP_69   ACTAGG-ATGAGACATCACTGGAATCTTTCTTGGGTAGAGCAGGATGCATTAAAAT-ATT
6436 GROUP_70   ACCAGACATGAAACCTCCATTGAATCTTTTTGGGTAGGGCTGGATGTGTGGCCAATATT
6437 SUMMARY    ACXXXX-ATGAXAXXXX-XTXGA-XX-TT--T-GG-XGXXCXXX-TG-XX-XX-XX-XXX
6438
6439 GROUP_1    AGAATAAAGGTTGATTACACTGAC...............TATAATGGA...CAGGACATA
6440 GROUP_2    AGAATAAAGGTTGATTACAATGAC...............TACAATGGA...GTGAACAAA
6441 GROUP_3    ACAATTACAGTGGATAACAGTTTG...............GAATATG......ATGACCAC
6442 GROUP_4    ACAATTACTGTGAATAACAACCTA...............GATTATG......ATGAAAAT
6443 GROUP_5    ACTATAACTGTGGATAATGATGTA...............GATTATA......ATTCAAAG
6444 GROUP_6    ACTATTACTGTCAATAAAGACATA...............AAATATG......ATGATGGA
6445 GROUP_7    ACTATCACTGTTGACAAAACCATT...............GACTATG......ACACTGGA
6446 GROUP_8    ACAATTACTATGAAGAAGGAG..................AACTATA......ATGA-CAT
6447 GROUP_9    ACAATAACTGTTAATAATACAAGA...............CCCTACA......ATGAACAC
6448 GROUP_10   ACAATTCTGTAAGTAAAATGAAA................AATTATA......ATGAGCAC
6449 GROUP_11   ACAATTAATGTGGATAGCACAAAA...............ACATATG......ATGAATCC
6450 GROUP_12   ACAATAAATGTAGAAGATGGTAAA...............ACTTATG......ATGAATCT
6451 GROUP_13   ACAATTGAA.........ACAA--...............CTTA--C.....AT-A-GA-
6452 GROUP_14   ACAATAAA-.........-CAAAT...............CAGGCAC.....A--A--CC
6453 GROUP_15   ATAATAGAA.........CCAGAT...............GGACTCC.....ATGATAGC
6454 GROUP_16   ACAATA-AA.........TCA-AT...............GAGCAAC.....ACATTAAT
6455 GROUP_17   AAGTTAATTGTGCAGTATGAAGAC...............TATAAT......GGAAAGAAA
6456 GROUP_18   AAGCTAGTTGTAGAAATATGAGGA...............TATGAT......GATACAAAA
6457 GROUP_19   AAATTAGTAGTGAAATATGAAGAC...............TATAAT......GAGAAAAAG
6458 GROUP_20   AAGTTGACTGTGGATTAT...GAC...............AATTAT......GATACAAAA
6459 GROUP_21   AAATTAGTTGTAAACTAT...GAT...............AATTAT......GATGAAAAC
6460 GROUP_22   AAACTTGTTGTAGATTATGAAAAT...............TACAATGCA...AAAACAAAG
6461 GROUP_23   AAATTAGTTGTTGATTATGATGGT...............TACAATGAG...GAAACAAAG
6462 GROUP_24   AAGTTAGTTGTACATTATGAAGAT...............TATAATGCA...GAAACAAGG
6463 GROUP_25   GAGTTAGTTGTTCATTATGAAGAA...............TATAACAAA...GAGGGAAAA
6464 GROUP_26   GAGCTTAAGGTAAAATATGAAAAT...............TACAACACA...GAG......
6465 GROUP_27   AAATTA-TAGTTAACTATGA-AA-...............TACAATACT...GGAGAAAAT
6466 GROUP_28   ACACTTGAAGTAAATTATGATGAT...............TATAATGGG...ACAGGCATA
6467 GROUP_29   ACACTTGAGATGGATTATACAAAC...............TATAATGGA...GAAGGCAAA
6468 GROUP_30   AAATTGAATATTGATTACAGTGAC...............TATGATAAG...AGTGTTGAA
6469 GROUP_31   AAATTAGATATTGATTATACCAAT...............TACAATAAA...AGTGTTAAG
6470 GROUP_32   AAATTGAATATTGATTATAATGCA...............TATGATGAA...AGTAGGGAC
6471 GROUP_33   GATTTGAAAATACATTATGAAGAT...............TATAATAAA...GATGGGAAA
6472 GROUP_34   CATCTAAAAATTGATTATACAAAC...............TATAATGTT...AAAGGGAAG
6473 GROUP_35   AATCTTGACATAGATTACATTAAT...............TACAACTCT...GAAGACAAA
6474 GROUP_36   AAATTAGAAATTGACTATAGTAAC...............TACAATGAG...GAGAATAAA
6475 GROUP_37   GATTTAAAAGTAAATTATACTGGG...............TATAATGAT...GAAGGTAAC
6476 GROUP_38   CATCTAGAGATCAAGTATGATGGT...............TACAATGAT...GCTGGCAAC
6477 GROUP_39   CACTTAGAAGTAAAATACACAGGG...............TATAATGAA...GAGGGTAAT
6478 GROUP_40   CACCTAAATGTCAGATACACTG.................ATTATAAT...GAAGGTAAT
6479 GROUP_41   GAGCTCCAATTAGATTATACCAAT...............TACAATCAA...GAAAATAAT
```

FIG. D14 CONT'D 10.trace                                                                    9/20/2007 5:05 PM

```
6480 GROUP_42    ACCATGAACATAGATTATACTAAT...............TATGATGAT...TCTGTTAAT
6481 GROUP_43    ACTTTGAATATAGATTATACTGAT...............TATGATGAT...TCTATCCAG
6482 GROUP_44    ACTATGAATATAAATTATGAAAT................TATGATGAT...GCTCCTGAA
6483 GROUP_45    ACATTAAATATAAACTATGATAAC...............TATGATGAT...TCTATTGAA
6484 GROUP_46    ACATTAAACATAGATTATGACAAT...............TATGATGAC...TCCCCTAAG
6485 GROUP_47    GTGTTGGATATTGTGGACAATTAC...............AATGAT............CAA
6486 GROUP_48    ATATTGGACATTAAAGAGGATTAC...............AATACC............CAG
6487 GROUP_49    AAATTAGAGGTTACACTTGCAAAT...............TATAACA.........AGGAG
6488 GROUP_50    AAACTAGAGGTCACACTTACAAAT...............TACAATG.........AAAAT
6489 GROUP_51    AAATTAAAAGTTGAGATCGGAAAC...............TATGATG.........AAAAC
6490 GROUP_52    AAATTAGAACTTGAGCTTGCACAC...............TATGATA.........AAAAG
6491 GROUP_53    AAACTTGACACAA......CACAGGGT.........GACTATGACACAGGCAAAGGTGTT
6492 GROUP_54    AAACTTGACACAA......ATGAAGGT.........GATTACGACACA...ATAGGTGTT
6493 GROUP_55    GAATTTAGCACAAGTAGTGATAAAGAT.........GAACATGATGAA...ATTGGCAAG
6494 GROUP_56    GAATTTAATACAAGTAGTGATAAAACT.........GAACATGATAAA...ATTGGTAAA
6495 GROUP_57    AAATTTAACACAA......ATAAGACT.........AATTATGATGAC...ATAGGTGTA
6496 GROUP_58    GAATTGGATTTAGACCATGAAGGT...............TATTCAGCA...GAAGGGAAA
6497 GROUP_59    AGACTAGAATTGGACCACACTGAT...............TACAATGCT...GAAGGGAAA
6498 GROUP_60    CATACTGACTTAGATCATGAAGCACAA.........CAATATAATGCA...CCCGGAAAA
6499 GROUP_61    CATACTGACTTAGATCACAATGAGGAT.........CAGTACAATGCA...CCTGGAAAA
6500 GROUP_62    CATACTGATGTTGTGCATGAAACAGAC.........AAGTACAACCAC...CCAGGGAAG
6501 GROUP_63    CATACCAATTTAGACCAT...ACTG.........GATACAATGAG...CCTGGGAAA
6502 GROUP_64    GAGACAGAATTGAATCATGAAGAAGGG.........AAATACAATGCA...GAAGATCAA
6503 GROUP_65    GAAACCAAATTAAACCATGAAACAGAC.........ATGTACAATGCT...GATGGTCAG
6504 GROUP_66    CATACAAACCTTGAGCATGTTGAAGCAGACAGACAAGCCTACAATGCA...AAAGGGAAA
6505 GROUP_67    CACACAGATCTTAAACATGACCATGAAGGCCAAAATGTTTACAATGAC...GAAGGCAGA
6506 GROUP_68    CACACTAAATTAGTACATGGAGAGGAGGG......TGTTTATAATATG...AAAGGTAAC
6507 GROUP_69    GCATTAGAACTAGATCATGACAAC...............TATGAT-AA............
6508 GROUP_70    AGTTTAGACATTAACCATGATGAC...............TACCAAAAG............
6509 SUMMARY     XXXXXX-X-XXXXXXXXX-X----XXXXXXXXXXXXXXXXXXX---XXXXXX--X--X-
6510
6511 GROUP_1     AATTTCACAAAATGGAAAATCACACTACAGGAAATGGCACAGATTAGGAGAAAATTTGAA
6512 GROUP_2     AACTTTACAACATGGAAAATCACACTGCAGGAGATGGCACAAATTAGAAGAAAATTCGAA
6513 GROUP_3     CACTTTGATAAGTGGCAGATAACCATACAAGAGATGTCACAAATTAGGAGAAAATTTGAA
6514 GROUP_4     CACTTTGATCAGTGGCAGATAACTATACAGGAAATGGCACAAATTAGAAGGAAGTTTGAG
6515 GROUP_5     CATTATAATAAATGGCAAATAACCTTACAGAAAATGGCTCAAGTTAGGCGTAAATTTGAA
6516 GROUP_6     CACTTTCTTAAATGGCCTATAACATTACAAGAGATGGCACAAATTAGGAGAAAATTTGAA
6517 GROUP_7     CATTTTAATAAATGGCAAATAACATTACAAGAGATGGCACAAATTAGAAGGAAATTTGAA
6518 GROUP_8     AATTTTGTGGATTGGAAAATTACTTTGCAGGAGATGGCACAGGTTAGAAGGAAATTTGAA
6519 GROUP_9     ACTTTTGACACATGGCAAATAACTCTACAAGAAATGGCCCAAATTAGAAGGAAATTTGAA
6520 GROUP_10    ACTTTTGACAAATGGCAAATAACCCTACAGGAAATGGCCCAAATTAGAAGGAAATTTGAA
6521 GROUP_11    AAATTTAGAACATGGCAAATTACATTGCAAGAAATGGCTCAAATCAGACGCAAATTTGAG
6522 GROUP_12    AAATTTAGAAAATGGCAAATTACACTACAAGAAATGGCTCAAATTAGGCGCAAATTTGAA
6523 GROUP_13    AGATT-AAAA-ATGGAATAT-AA-TTACAAGA-ATGGCTCAAAT-AGGAGAAAGTTTGA
6524 GROUP_14    AAGTT-GATAAATGGAAT-T-AACTTACAAGAAATGGCTCAAATTAG-CGCAAATTTGAA
6525 GROUP_15    AAATATAAAGTATGGCACATTAATTTACAAGAGATGGCCCAGATTAGGCGAAAATTTGAA
6526 GROUP_16    AAATTTAAAGTATGGCACATTAATTTACAAGAAATGGCCCAGATCAGGCGTAAATATGAA
6527 GROUP_17    AACTTTAACACATGGAAAATAAACTTGCAAGAGATGGCACAAATTAGAAGGAAATTTGAA
6528 GROUP_18    AACTTTAAGACATGGAAAATAAACCTACAAGAAATGGCACAAGTTAGAAGAAAATTTGAG
6529 GROUP_19    AATTTTATGACATGGAAAATAAATCTACAAGATGGCACAGATTAGGAGGAAATTTGAA
6530 GROUP_20    AATTTTTTCAAATGGCAAATAAATCTACAAGAAATGGCCAAGTCAGAAGAAAATTTGAA
6531 GROUP_21    AACTTCCATAAATGGCAAATTAACCTGCAAGAGATGGCACAGATTAGAAGAAAATTTGAA
6532 GROUP_22    AACTTTATGACATGGCAAATTAATTTACAGGAAATGGCACAGATTAGAAGGAAATTTGAA
6533 GROUP_23    AACTTCAAGAAATGGCAAATCAACCTACAAGAAATGGCACAGATCAGAAGGAAATTTGAG
6534 GROUP_24    AACTTTGTAAAATGGCAAATAAATCTACAGGAAATGGCCCAGATTAGGAGGAAATTTGAG
6535 GROUP_25    AATTTTACTAAGTGGCAAGTAAACATCCAAGAGATGGCTCAGATTAGAAGAAAATTTGAA
6536 GROUP_26    AATTTCACTAAATGGGAAATAAATCTACAAGAAATGGCACAAATCAGAAGAAAATTTGAA
6537 GROUP_27    AACATTA-TACATGGCAAATAAATATTAAAGAGATGGCACAGATTAGGAGAAAATTTGAA
6538 GROUP_28    AATTTTACCCAATGGCCAATCAACTTGCAAGAAATGGCACAAATTAGAAGAAAGTATGAA
6539 GROUP_29    AACTTCACTCAGTGGCCAATCAATCTACAGGAAATGGCTCAAATTAGAAGGAAATATGAA
6540 GROUP_30    AATTTCACAATCTGGAAAATAAATATAAAGGAAATGGCCCAGATCAGGAGGAAATTTGAA
6541 GROUP_31    AATTTCACAATTTGGAAGATAAATATAAAGAAATGGCCCAGATTAGGAGAAAATTTGAG
```

FIG. D14 CONT'D

```
10.trace                                                                    9/20/2007 5:05 PM 6542 GROUP_32    AATTTCACAATTTGGAAAATAAATATAAAAGAAATGGCCCAGATTAGGAGGAAATTTGAA
6543 GROUP_33    AACTTTACTAAATGGCAAATTAATCTCAAAGAAATGGCCCAGATTAGAAGGAAATTTGAG
6544 GROUP_34    AATTTTACTAAATGGCAAATAAATCTTAAAGAAATGGCACAGATTAGGAGAAAATTTGAG
6545 GROUP_35    AACTTTACAACATGGCAAATCAATCTCAAAGAAATGGCTCAAATCAGAAGAAAGTTTGAA
6546 GROUP_36    AATTTCACAACTTGGCAAATTAACCTAAAGGAAATGGCACAAATAAGAAGAAAGTTTGAA
6547 GROUP_37    AATTTTAACAAATGGCAGATCACCTTGAAAGAAATGGCTCAGATAAGAAGGAAGTATGAA
6548 GROUP_38    AATTTCCAATCATGGCAAATTACCCTAAAAGAAATGGCACAAATAAGAAGGAAATTTGAA
6549 GROUP_39    AACTTTAACATATGGCAAATTAACCTTAAAGAGATGGCTCAGATAAGAAGGAAGTTTGAA
6550 GROUP_40    AACTTTAGATCATGGCAAATAAGCATAAAGGAAATGGCACAAATTAGAAGGAAGTTTGAA
6551 GROUP_41    AATTTCAAAACTTGGCAAATAAACTTGAAAGAAATGGCACAGATTAGAAGAAAATTTGAA
6552 GROUP_42    AATTTTGTGAAATGGAAAATAAGTTTGCAAGAAATGGCCCAAGTGCGCAGAAAATTTGAG
6553 GROUP_43    AACTTCAAGAAGTGGAAAATTAGCTTACAGGAGATGGCCCAAGTACGCTAGAAAGTTTGAG
6554 GROUP_44    AATTTTACCAAATGGAAAATAAGTTTACAAGAGATGGCTCAAATACGTAGGAAATTTGAA
6555 GROUP_45    AACTTCAAGGTGTGGAAAATAAACCTGCAAGAGATGGCACAAATACGTAGAAAATTTGAG
6556 GROUP_46    AATTTTAAGGTGTGGAAAATAAATCTACAAGAAATGGCTCAAATTCGCAGGAAGTTTGAA
6557 GROUP_47    AGTTTCACTAAATGGAAGATAAACCTCAAAGAAATGGCACAAATTAGAAGAAAATTTGAA
6558 GROUP_48    AGCTTTACTAAATGGAAAATTAACTTACAAGAGATGGCACAGATTAGGAGAAAGTTTGAA
6559 GROUP_49    AATTTTACAGTGTGGGCTATTAATATACAAGAAATGGCTCAAATTAGAAGGAAATTTGAA
6560 GROUP_50    AATTTCAAAGTATGGAACATCAATTTGCAAGAAATGGCCCAGATCAGAAGAAAATTTGAA
6561 GROUP_51    AATTTTAATACTTGGAATATTAATTTACAGGAAATGGCCCACAATCAGAAGAAATTTGAA
6562 GROUP_52    AACTTTACCACATGGAATATTAATCTTCAAGAAATGGCCCAAATTAGAAGAAAATTTGAG
6563 GROUP_53    GGTTTCACTACATGGAAAATCAGCTTACAAGAAATGGCACAAATCAGAAGAAAGTTTGAA
6564 GROUP_54    GGATTTGTAACATGGAAGATTAGCTTGCAAGAAATGGCACAAATCAGGAGAAAATTTGAA
6565 GROUP_55    GGATTCAAAACATGGAAGATTAGTCTTCAAGAAATGGCACAAATTAGAAGGAAATATGAA
6566 GROUP_56    GGATTCAAAACATGGAAGGTTAGTCTTCAAGAAATGGCACAAATCAGAAGAAAATATGAA
6567 GROUP_57    GGATACAAAACATGGAAAATTAGCCTTCAAGAGATGGCACAAATTAGAAGGAAATTTGAG
6568 GROUP_58    AACTTTAAAACATGGAAGATAAATCTTAAGGAAATGGCCCAGATTAGAAGGAAAAATGAG
6569 GROUP_59    AATTTTACAACGTGGAAAATCAACTTACAGGAGATGGCCCAGATTAGAAGAAAGAATGAG
6570 GROUP_60    AATTTCTCTCAGTGGAAGATCACAATCAAGGAAATGGCTCAAATCAGAAGAAAATGTGAG
6571 GROUP_61    AACTTCTCCCAATGGAAAATTACAATTAAGGAAATGGCTCAAATTAGAAGAAAGTGTGAA
6572 GROUP_62    AATTTTAGTAAATGGAATATCACTCTCAAAGAAATGGCCCAAATCAGAAGAAAGTGTGAG
6573 GROUP_63    AACCACTCAGAATGGAAGATTACACTCAAAGAAATGGCCCAGATTAGAAGGAAATGTGAG
6574 GROUP_64    AACTTCTCAAAATGGAAAATAACACTGTTGGAAATGGCACAAATCAGAAGAAAGTGTGAA
6575 GROUP_65    AATTTTTCAAAGTGGAAAATAACATTAATGGAAATGGCACAAATTAGAAGAAAGTGTGAG
6576 GROUP_66    AATTTCTCTACATGGAAAATTACACTCAAAGAAATGGCTCAAATTAGAAGAAAGTGTGAA
6577 GROUP_67    AATTTCTCTGCTTGGGAAATTACAAGCAAGGAAATGGCTCAAATTAGGAGAAAGTGTGAA
6578 GROUP_68    AATCTCTCAAAGTGGCAGATTACACTCAAAGAAATGGCTCAGATCAGGAGGAAATGTGAA
6579 GROUP_69    A-TTTCAGGACCTGGGGAATAAACATACAAGAGATGTCACAAATTAGAAGGAAATTTGA-
6580 GROUP_70    AATTACAAAAATTGGGCAATTAGTTTACAAGAAATGTCACAAATTAGGAGGAAATTTGAA
6581 SUMMARY     X-XXX-X-XX-XTGGXXX-T-AX-XTXXXXGA-ATGXCXCAXXT-XG-XGXAAXXXXGA-
6582
6583 GROUP_1     TTGTTTACATATGTCAGGTTTGACTCAGAAATAACCTTGG.TGCCTTGTATTGCTGGTAG
6584 GROUP_2     CTATTTACTTATGTTAGGTTTGATTCAGAAGTAACTTTAG.TACCCTGTATTGCTGGTAG
6585 GROUP_3     TTCTTTACATATGCTAGGTTTGATTCAGAAACTACCTTAG.TTCCTTGTATAGCCGGTAA
6586 GROUP_4     TTCTTTACTTACACTAGATTTGATTCAGAAATCACTTTAG.TCCCTTGTATAGCTGGAAA
6587 GROUP_5     TTCTTTACTTATGTCAGATTTGATTCAGAGGTTACTTTGG.TACCTTGTGTAGCCGGCAA
6588 GROUP_6     TTCTTCACATATGTTAGATTTGACTCAGAAATCACTTTGG.TGCCTTGCATAGCTGGAAA
6589 GROUP_7     TTCTTCACATATGTCAGATTTGATTCAGAACTCACTCTTG.TACCATGTATAGCAGGAAA
6590 GROUP_8     ATGTTCACCTA-GTTAGATTTGACTCAGAGATTACTTTAG.TCCCATGCATAGCTGGAAG
6591 GROUP_9     ATGTTTACATATGTTAGATTTGACTCAGAAGTCACTTTAG.TACCTTGCATCGCAGGCAA
6592 GROUP_10    ATGTTTACATATGTCAGATTTGACTCAGAAATCACATTGG.TACCCTGTATTGCAGGAAA
6593 GROUP_11    ATGTTCACATATGTTAGGTTTGATTCTGAAATTACCATAG.TCCCATGCATTGCAGGAAA
6594 GROUP_12    ATGTTTACATATGTAAGATTTGATTCAGAAATTACATTGG.TCCCATGTATTGCTGGAAA
6595 GROUP_13    ATGTTTACATATGT-AGATTTGATTCAGA-ATAACCCT-G.TTCCATCTATTGCAGGACG
6596 GROUP_14    ATGTTCACATATGTGAGATTTGA-TC-GAAATAACTCT-G.TTC--TGCATTGCAGGAC-
6597 GROUP_15    ATGTTTACATATGTAAGATTTGATTCAGAAGTGACCATAG.TTCCATGCATTGCAGGACA
6598 GROUP_16    ATGTTTACATATGTAAGATTTGATTCAGAAGTAACCATAG.TTCCATGTATTGCAGGGTA
6599 GROUP_17    ATGTTCACATACACTAGATTTGATTCAGAGATCACATTGG.TGCCTTGTATAGCTGCAAA
6600 GROUP_18    ATGTTTACATATACTAGATTTGATTCAGAAGTTACTCTAG.TTCCTTCTATAGCTGCCAA
6601 GROUP_19    ATGTTTACATATGCCAGATTTGATTCAGAGATCACCCTAG.TCCCTTCTATAGCTGCCCA
6602 GROUP_20    TTATTCACATATACTAGATTTGACTCTGAGATTACAATAG.TCCCATCCATAGCTGGCAA
6603 GROUP_21    TTGTTTACATATGCTAGATTTGATTCTGAAATTACAATAG.TACCATCTATAGCTGGCAA
6604 GROUP_22    ATGTTCACCTACGTCAGATTTGATTCTGAAGTCACCCTAG.TACCATCAATAGCGGCCAA
6605 GROUP_23    ATGTTCACCTATGTGAGGTTAATTCTGAGGTCACATTAG.TACCATCCATAGCTGCCAA
6606 GROUP_24    ATGTTTACATATGTTAGATTTGATTCAGAAATTACACTAG.TACCATCTGTAGCTGCTAA
```

FIG. D14 CONT'D

```
10.trace                                                                                        9/20/2007 5:05 PM 6607 GROUP_25    ATGTTCACCTATACTAGATTTGATTCAGAAGTTACATTAG.TACCCTCTATTGCTGCAAA
6608 GROUP_26    CTATTTACATATGTTAGGTTTGATTCTGAAGTTACATTAG.TTCCCTCCATAGCTGCTCA
6609 GROUP_27    ATGTTCACCTATACTAGATTTGATTCAGAAATAACTTTGG.T-CCGTCAATTGCAGCTA
6610 GROUP_28    TTGTTCACATACTTAAGGTTTGATTCTGAAATTACCCTTG.TTCCTTGCATTGCAGCAAA
6611 GROUP_29    TTATTTACATATCTTAGATTTGATTCAGAGGTTACTCTGG.TGCCATGCATTGCAGCTAA
6612 GROUP_30    TTGTTTACATATGCAAGATTTGACTCTGAAATAACATTGG.TCCCGTGTATAGCAGCAGA
6613 GROUP_31    TTGTTTACATACACAAGGTTTGATTCTGAAATAACATTAG.TACCTTGTATAGCTGCAGA
6614 GROUP_32    CTATTCACATATACAAGATTTGATTCTGAGATAACACTGG.TACCATGCATAGCTGCAGA
6615 GROUP_33    TTATTCACATATGTAAGGTTTGATTCAGAAATAACACTTG.TACCATGCATTGCAGCAAA
6616 GROUP_34    TTGTTCACATATGTTAGATTTGACTCAGAAGTGACATTAG.TTCCATGCATTGCTGCTAA
6617 GROUP_35    ATGTTTACATATGTGAGATTTGATTCAGAAGTTACATTAG.TCCCATGTATAGCAGCACA
6618 GROUP_36    TTATTTACATATGTAAGATTTGATTCAGAATTGACTCTGG.TCCCATGCATAGCAGCAAA
6619 GROUP_37    TTATTTACATATGTTAGATTTCTGAAATAACCTTAG.TGCCTTGCATATCTTCTCA
6620 GROUP_38    CTATTTACTTATGTTAGATTTGATTCAGAAATAACTTTAG.TACCTTGCATATCATCTCA
6621 GROUP_39    CTATTTACATATCTCAGGTTTGATTCTGAAATCACTTTGG.TACCATGCATTGCTTCACA
6622 GROUP_40    CTTTTCACATATGTGAGATTTGATTCAGAAATTACTTTAG.TGCCTTGCATAGCCTCTCA
6623 GROUP_41    CTTTTCACTTACCTCAGATTTGATTCAGAGGTAACATTAG.TCCCTTGCATAGCTGCTAA
6624 GROUP_42    TTGTTCACCTATGTAAGATTTGATTCAGAAATAACAATTG.TGCCATGTATAGCCGGGCA
6625 GROUP_43    TTTTTTACGTATGTTAGATTTGACTCAGAAATAACAATTG.TGCCAAGTATAGCTGGACA
6626 GROUP_44    TTATTCACCTATGTAAGATTTCAGAAGTGACAATTG.TACCATGTATAGCTGGTCA
6627 GROUP_45    TTGTTCACATATGCTAGATTTGATTCAGAGATTACAATTG.TACCTTGTGTTGCTGGGCA
6628 GROUP_46    CTGTTCACTTATGCTAGATTTGATTCAGAGATAACAATTG.TTCCATGTGTTGCTGTGCA
6629 GROUP_47    ATGTTTACTTATGCAAGATTTGACTCTGAAATTACTATGG.TACCAAGTGTAGCAGCCAA
6630 GROUP_48    ATGTTCACATACACTAGATTTAACTCTGAGATTACACTGG.TACCAAGTATTGCAAACAA
6631 GROUP_49    TTGTTCACCTATACTAGGTTTGATTCTGAAATAACCCTAG.TTCCATGCATTTCCGCCCT
6632 GROUP_50    CTGTTTACTTACACTAGATTCGATTCTGAAATAACCTTGG.TTCCATGCATTTCTGCACT
6633 GROUP_51    CTGTTTACTTACACTAGATTTGATTCTGAAATTACTTTGG.TTCCATGCATTTCTGCTCT
6634 GROUP_52    CTATTCACTTACACTAGATTTGATGAGATAACCTTGG.TTCCGTGTATTTCAGCTCT
6635 GROUP_53    CTATTCACATACACTAGATTTGATTCTGAGATAACAATAG.TCACAGCAGCAGCAGCACA
6636 GROUP_54    TTGTTTACATACACTAGATTTGACTCAGAAATAACAATAG.TCACAGCAGCTGCAGCACA
6637 GROUP_55    TTGTTTACATACAAGATTTGACTCAGAAATAACAATAG.TCACCGCAGCTGCAGTGCA
6638 GROUP_56    TTATTCACATATACAAGATTTGATTCAGAGATAACAATAG.TCACTGCAGCCGCAGCTCA
6639 GROUP_57    TTGTTTACATATACAAGATTTGACTCAGAGATTACAATAG.TCACTGCAGCAGCTGCTCA
6640 GROUP_58    CTTTTCACCTACTTAAGGTTTGATTCTGAAATCACCATTGTTCCAAGCAATG.CAGCAAT
6641 GROUP_59    ATGTTCACATATCTCAGATTTGATTCAGAAATCACTCTTG.TGTGTGCAGTGGCCTCACA
6642 GROUP_60    CTCTTTACATACCTCAGATTTGATTCTGAGATTACAATAG.TAGCAACAGTAGCTGCACT
6643 GROUP_61    CTATTCACATACCTTAGGTTTGACTCTGAGATTACAATAG.TAGCAACAATAGCTGCTCT
6644 GROUP_62    CTATTTACATATCTCAGATTTGATTCTGAAATTACTATAG.TGGTGTCAGTTGCAAGTAA
6645 GROUP_63    ATGTTCACATACTTAGATTTGATTCAGAAATAACTATAG.TGGTATCAGTGGCTAGTAA
6646 GROUP_64    CTTTTACATATCTCAGATTTGATTCAGAAATAACAATAG.TCACCACATTGGCAGGCCA
6647 GROUP_65    CTTTTCACTTACCTCAGATTTGACTCAGAAATAACAATAG.TAACTACCTTAGCAGGACA
6648 GROUP_66    CTTTTCACATACTTAAGATTTGATTCAGAGATCACTATAG.TTGCTACCATTGCTGGACA
6649 GROUP_67    CTCTTCACCTATTTGCGCTTTGACTCAGAAATTACCATAG.TGGCTACTATAGCTGGACA
6650 GROUP_68    CTCTTCACATACCTGCGCTTTGATTCAGAGATAACAATTG.TAGCTACACTAGCAGGGCA
6651 GROUP_69    ATGTTCACTTATGTAAGATTTGATTCAGAGATAACAATTG.TACCATGTATTGCAGCTAT
6652 GROUP_70    ATGTTTACATATGTCAGATTTGATTCCGAAATAACAATAG.TACCATGTGTTGCTGCCAC
6653 SUMMARY     XTXTTXACXTA-XX-XGXTTXXA-TC-GA-XTXACXXT-GXT-X--XXXXXXXCXXXXX
6654
6655 GROUP_1     AGGAGACGACATTGGACATATTGTAATGCAATATATGTATGTTCCTCCAGGAGCTCCAAT
6656 GROUP_2     AGGAGATGACATTGGTCATGTTGTAATGCAATATATGTATGTTCCCCCAGGAGCTCCAAT
6657 GROUP_3     GGGTGAAGACATTGGACACATTGTGATGCAATATATGTATGTTACCCCCTGGCGCACCCAT
6658 GROUP_4     GGGTGATGATATTGGACACATTGTAATGCAGTATATGTATGTGCCCCCCGGAGCACCAAT
6659 GROUP_5     GGGAGATGATATTGGACACATTGTAATGCAATACATGTATGTGCCTCCTGGTGCACCACT
6660 GROUP_6     AGGGGATGACATTGGTCATATAGTCGCAATATATGTATGTTCCACCAGGTGCTCCACT
6661 GROUP_7     AGGTGATGACATTGGTCATATAGTTATGCAGTACATGTACGTTCCACCCGGTGCCCCTCT
6662 GROUP_8     AGGTGAAGATATTGGACACATAGTAATGCAATACATGTATGTCCCACC-GGTGCACCTGT
6663 GROUP_9     GGGCGATGACATAGGTCACATAGTTATGCAATATATGTATGTGCCACCTGGGGCTCCAGT
6664 GROUP_10    AGGAGATGACATAGGGCATACGTAATGCAGTACATGTATGTGCCCACCTGGAGCTCCAGT
6665 GROUP_11    GGGTGATGATATAGGACATATTGTGATGCAATACATGTATGTACCACCTGGAGCCCCAAT
6666 GROUP_12    AGGTGATGACATAGGACATGTTGTCATGCAATACATGTATGTACCACCAGGGGCACCCAT
6667 GROUP_13    TGGTGCAGATATAGGTCACATAGTTATGCAATATATGTATGT-CCACCTGG-GC-CCA-T
6668 GROUP_14    TGGT-ATGATATAGG-CACATAGTTATGCAGTACATGTATGTACCACCTGGACCCTCCAGT
6669 GROUP_15    TGGTAGTGACATAGGCCATATAGTCATGCAATACATGTATGTACCACCTGGGGCCCCAGT
6670 GROUP_16    TGGTGATGACATAGGTCACATAGTTATGCAATACATGTATGTGCCGCCTGGGGCTCCAGT
6671 GROUP_17    AGGAAATGATATTGGTCATGTTGTAATGCAATATATGTATGTCCCACCAGGTGCTCCAGT
```

FIG. D14 CONT'D

10.trace                                                                9/20/2007 5:05 PM

```
6672   GROUP_18     AGGGGATGACATTGGTCATGTAGTGATGCAATACATGTATGTCCCACCAGGCGCTCCAGT
6673   GROUP_19     GGGAGATGATGTTGGTCATGTTGTAATGCAGTACATGTATGTCCCACCAGGTGCACCAGC
6674   GROUP_20     GGGAGATGACATTGGACATGTTGTAATGCAGTACATGTATATACCACCTGGAGCACCAGT
6675   GROUP_21     GGGCAATGATATTGGACATGTTGTGATGCAATACATGTATACCACCTGGGGCACCAGT
6676   GROUP_22     AGGTGATGATATTGGACATGTTGTGATGCAATACATGTATGTACCACCAGGTGCACCAAT
6677   GROUP_23     GGGTGTTGATATTGGACATGTTGTCATGCAATACATGTATGTCCCACCAGGTGCACCAAT
6678   GROUP_24     GGGTGATGACATAGGACATATTGTTATGCAGTACATGTATGTTCCTCCAGGAGCACCAAT
6679   GROUP_25     GGGAGATGACATTGGACATGTAGTCATGCAATACATGTATGTTCCACCTGGAGCACCAAT
6680   GROUP_26     AGGTGAGGATATAGGCCATGTTGTAATGCAATACATGTATGTCCCTCCTGGGGCACCAAT
6681   GROUP_27     A-CGGGTGACATAGGACATGTTGT-ATGCAATATATGTATGTCCCACCAGGTGCTCCAAT
6682   GROUP_28     AAGCAATGATATAGGCCATGTGGTAATGCAGTACATGTATGTACCACCAGGTGCGCCAAT
6683   GROUP_29     AGGGAATGACATAGGCCATGTAGTAATGCAATATATGTATGTACCACCAGGAGCACCAAT
6684   GROUP_30     AAGTGATAGCGTTGGCCATGTTGTTATGCAGTACATGTATGTACCACCAGGGGCACCTTT
6685   GROUP_31     AAGTGACAGCATTGGTCATGTTGTTATGCAGTACATGTATGTACCACCAGGGGCTCCTCT
6686   GROUP_32     GAGTGACAGCATTGGGCATGTTGTAATGCAATATATGTATGTACCTCCAGGAGCACCATT
6687   GROUP_33     GAGTGATAACATCGGTCATGTTGTCATGCAATATATGTATGTTCCTCCGGGAGCCCCTTT
6688   GROUP_34     AAGTGACAACATTGGCCATGTTGTTATGCAATACATGTATGTCCCCCCAGGAGCACCTTT
6689   GROUP_35     AAATGAAGGTGTGGGGCATGTTGTTATGCAGTATATGTATGTCCCTCCAGGGGCACCATT
6690   GROUP_36     AAATGATGGCATAGGTCATGTTGTCATGCAATACATGTATGTCCCCCCAGGAGCACCATT
6691   GROUP_37     GAGTGCTAACATTGGTCATGTTGTTCATGCAATATATGTATGTCCCTCCTGGAGCTCCAAT
6692   GROUP_38     AAGTGCTAATATTGGTCATGTTGTCATGCAGTACATGTATGTTCCTCCTGGAGCTCCAAA
6693   GROUP_39     AAGTAAAAACATTGGTCATGTGGTCATGCAATACATGTATGTTCCGCCTGGAGCTCCTAA
6694   GROUP_40     AAGTAATGATATTGGGCATGTAGTGATGCAATACATGTATGTCCCACCAGGTGCTCCTAA
6695   GROUP_41     AAGTAAAAACATTGGACATGTTGTTATGCAATACATGTATGTGCCTCCTGGTGCTCCTAT
6696   GROUP_42     AGGTGGTGATGTCGGACATGTTGTTATGCAATACATGTATGTACCGCCCGGTGCACCCCT
6697   GROUP_43     GGGTAGTGATGTCGGACATGTTGTCATGCAATACATGTTCGTACCACCTGGCGCACCCCT
6698   GROUP_44     AAGTGGAGATGTGGGACATGTAGTTATGCAGTATATGTATGTCCCACCTGGAGCCCCTCT
6699   GROUP_45     AGGTGGTGACATTGGACACGTGGTCATGCAATACATGTATGTTCCACCTGGTGCACCTAC
6700   GROUP_46     GAGTGGTGATATTGGTCATGTGGTCATGCAATATATGTATGTTCCACCAGGTGCCCCCAC
6701   GROUP_47     AGATGGTCACATTGGTCATATAGTCATGCAATATATGTATGTACCACCAGGAGCACCTAT
6702   GROUP_48     GGAAGGTCATATTGGTCATATAGTAATGCAATACATGTATGTACCACCAGGAGCACCCAT
6703   GROUP_49     TAGTCAGGACATTGGACACATCACAATGCAATACATGTATGTTCCACCTGGTGCACCGGT
6704   GROUP_50     TAGCAAGGATATTGGACACATTACAATGCAATACATGTATGTGCCCGCCAGGTGCACCTGT
6705   GROUP_51     TAGTCAAGATATTGGTCACATCACAATGCAGTATATGTATGTCCCACCAGGTGCTCCAAT
6706   GROUP_52     CAGCCAAGATATCGGACACATTACAATGCAGTATATGTATGTTCCACCTGGCGCTCCAAT
6707   GROUP_53     AGGTAATGATATTGGACATATAGTTATGCAATTTATGTATGTACCTCCAGGGGCCCCAGT
6708   GROUP_54     AGGTGATGATACTGGACATATAGTACTGCAATTCATGTATGTGCCTCCAGGTGCACCAAT
6709   GROUP_55     GGGAGATGATAGTGGGCATGTAGTATTACAATTCATGTATGTACCTCCAGGAGCGCCTGT
6710   GROUP_56     AGGAAATGATAGTGGACATATATTGCAATTTATGTATGTACCCCCAGGAGCACCTGT
6711   GROUP_57     AGGAGAAGATAATGGACATATTGTGTTACAATTTATGTATGTACCCCCAGGAGCACCTGT
6712   GROUP_58     AGAAGGAAGCAATGGTCACGTGGTGGTCCAATACATGTATGTACCTCCTGGTGCCCCACT
6713   GROUP_59     AGGAGACAATAATGGACATGTGGTGCTTCAATTTATGTTTGTTCCACCTGGAGCCCCTAT
6714   GROUP_60     AGGTCGGGATAATGGGCATGTTGTTTTACAGTACATGTATGTGCCGCCAGGGGCACCAAT
6715   GROUP_61     TGGAAAAGATAATGGCCATGTGGTTTTACAGTACATGTATGTGCCGCCAGGGGCACCCAT
6716   GROUP_62     AGGTGATGATAATGGGCATGTAGTTTATGCAATATATGTATGTACCTCCAGGAGCCCCCAT
6717   GROUP_63     ACAAGGGAATAACGGGCACGTGGTGATACAATACATGTATGTACCACCGGGTGCTCCAAT
6718   GROUP_64     AGGGGATGATATTGGACATGTGGTCATACAATATATGTATGTCCTCCTGGTGCTCCATT
6719   GROUP_65     AGGGGAGGACATTGGTCATGTAGTTATTCAATACATGTACGTACCACCAGGGGCCCCGTT
6720   GROUP_66     GGGTGATGACATAGGGCACATTGTACTTCAATACATGTATGTACCCCCTGGAGGACCAGT
6721   GROUP_67     AGGTGATGACATAGGGCACATAGTGCTTCAATATATGTATGTGCCTCCTGGTGGTCCTGT
6722   GROUP_68     AGGAGATGATTTAGGACATATTGTACTCCAGTACATGTATGTTCCCCCAGGTGGTCCAAT
6723   GROUP_69     A-AAGGTGACCTTGGACACATAGTCCT-CAATACATGTATGTTCCCCCGGGTGCACCTCT
6724   GROUP_70     AGAAGGTAACTTGGGACACATTGTTGTGCAATACATGTTTGTACCACCAGGAGCACCTCT
6725   SUMMARY      X-XX-XXXXXXXXGG-CAXXTXXX-XT-CAXTXXATGTXXXT-CCXCC-GG-GX-CCX-X
6726
6727   GROUP_1      TCCTTCAAAAAGAAACGATTTCTCATGGCAATCAGGCACCAATATGTCAATATTCTGGCA
6728   GROUP_2      TCCAAAAACAAGAAATGATTTCTCATGGCAATCAGGCACTAATATGTCAATATTCTGGCA
6729   GROUP_3      ACCAAAGAAAAGAAATGATTACACATGGCAGTCAGGCACTAATGCTTCTGTATTCTGGCA
6730   GROUP_4      ACCAAGGAAAAGAGATGATTACACATGGCAATCAGGCACTAATGCTTCCGTGTTTTGGCA
6731   GROUP_5      TCCAAACTCAAGAGATGATTTTACATGGCAATCTGGCACCAATGCTTCTGTCTTTTGGCA
6732   GROUP_6      GCCCACAAAGAGAGATGATTACACATGGCAATCTGGTACTAATGCTTCAATATTCTGGCA
6733   GROUP_7      ACCCACCCGAAGAGAAGATTACACATGGCAATCTGGCACTAATGCTTCAATATTCTGGCA
6734   GROUP_8      ACCTAAGAAGAGAGATGATTACACATGGCAATCTGGAACAAATGCCTCAGTTTTCTGGCA
6735   GROUP_9      ACCAACTAAGAGAGATGATTTGCTTGGCAGTCGGGAACAAATGCATCAGTCTTCTGGCA
6736   GROUP_10     TCCAACAAAAAGGGATGATTTTGCATGGCAATCAGGCACAAATGCATCAGTTTTTTGGCA
```

FIG. D14 CONT'D 10.trace                                                                                          9/20/2007 5:05 PM

| | | |
|---|---|---|
| 6737 | GROUP_11 | TCCAGATAATAGAACACACTTTGCTTGGCAATCAGGAACAAATGCATCTATATTCTGGCA |
| 6738 | GROUP_12 | ACCAGATAGCAGGACTCATTTTGCATGGCAGTCAGGGACTAATGCATCAATATTCTGGCA |
| 6739 | GROUP_13 | ACCAACAGACAGAAA-CA-TTTGC-TGGCAATCAAGTACTAATGCATCAATATTTTGGCA |
| 6740 | GROUP_14 | ACCA-ATGACAGAA--CA-TTTGCATGGCAATC-GGGA-TAATGCATCAATATTCTGGCA |
| 6741 | GROUP_15 | ACCAACAAATAGAAAACATTTTGCATGGCAATCAGGTACTAATGCATCGATTTTCTGGCA |
| 6742 | GROUP_16 | GCCAACAAGTAGAGAGCACTTTGCATGGCAGTCAGGTACCAATGCATCAA-TTTCTGGCA |
| 6743 | GROUP_17 | TCCAGAGAAAAGAGATGATTATACATGGCAATCAGGAACAAATGCATCTATTTTCTGGCA |
| 6744 | GROUP_18 | TCCAAAGAAGAGAGATGACTACACATGGCAGTCAGGAACCAATGCATCTATTTTCTGGCA |
| 6745 | GROUP_19 | TCCAGAAAAGAGAGATGATTACACATGGCAATCAGGAACAAATGCATCTGTCTTTTGGCA |
| 6746 | GROUP_20 | CCCAACAAAGAGAGATGATTATACATGGCAATCAGGAACAAATGCATCTGTCTTTTGGCA |
| 6747 | GROUP_21 | ACCTGAGAAGAGGGATGATTATGCATGGCAATCAGGCACTAATGCATCTATCTTTTGGCA |
| 6748 | GROUP_22 | ACCTAAAACTAGAGATGATTTTGCATGGCAATCTGGAACAAATGCCTCAATATTTTGGCA |
| 6749 | GROUP_23 | ACCCAAGACTAGGGATGATTTTGCCTGGCAATCTGGAACTAATGCTTCAATCTTTTGGCA |
| 6750 | GROUP_24 | ACCAAAAACCAGAGATGATTTTGCCTGGCAATCTGGAACAAATGCATCAATCTTCTGGCA |
| 6751 | GROUP_25 | TCCAAAGACAAGAGAAGATTATGCTTGGCAATCAGGGACCAATGCATCTATCTTTTGGCA |
| 6752 | GROUP_26 | TCCAAAAACAAGAGAGGATTATACATGGCAATCTGGTACCAATGCTTCAATATTTTGGCA |
| 6753 | GROUP_27 | TCCAAAAACTAGGGAAGATTTTGCTTGGCA-TCAGG-AC-AATGCATCCATTTTCTGGCA |
| 6754 | GROUP_28 | TCCAAAAACTAGGAAAGATTATGCATGGCAATCTGGCACAAATGCATCTGTTTTCTGGCA |
| 6755 | GROUP_29 | ACCAACAACTAGAAAAGATTATGCATGGCAATCTGGAACAAATGCATCTGTATTTTGGCA |
| 6756 | GROUP_30 | ACCAAGGACTAGAGATGATTGCAATCAGGCACAAATGCTTCCATCTTTTGGCA |
| 6757 | GROUP_31 | ACCACAAGCAAGAGATGACTACACATGGCAATCTGGCACGAATGCATCTATCTTTTGGCA |
| 6758 | GROUP_32 | ACCAACAAAAGAGATGACTACACATGGCAATCAGGTACAAATGCATCCATCTTTTGGCA |
| 6759 | GROUP_33 | ACCCAATAAAAGGAATGATTACACATGGCAATCAGGTACAAATGCCTCTGTTTTCTGGCA |
| 6760 | GROUP_34 | ACCCAAGAAAAGAGATGATTACACATGGCAATCTGGCACAAATGCATCTGTGTTTTGGCA |
| 6761 | GROUP_35 | ACCCAGGAAGAGAGATGATTACACTTGGCAATCTGGTACAAATGCCTCTGTTTTCTGGCA |
| 6762 | GROUP_36 | ACCTACTAAAAGAGACGATTACACATGGCAATCTGGCACAAATGCTTCTGTATTTTGGCA |
| 6763 | GROUP_37 | ACCAACCAAAAGAGATTACGTCTGGCAGTCAGGCACCAATGCATCCATCTTTTGGCA |
| 6764 | GROUP_38 | ACCAGACAAAAGAGATGATTATGTTTGGCAATCAGGAACTAATGCATCTATATTCTGGCA |
| 6765 | GROUP_39 | ACCTGAAAAGAGAGATGACTACACATGGCAATCTGGCACTAATGCATCTGTTTTCTGGCA |
| 6766 | GROUP_40 | ACCAGAAAAGAGAGACGACTACACTTGGCAATCTGGAACTAATGCTTCAATTTTCTGGCA |
| 6767 | GROUP_41 | CCCAAAAACTAGAAACATGATTACACATGGCAATCAGGTACTAATGCATCTATATTTTGGCA |
| 6768 | GROUP_42 | TCCAACGAAGAGAAATGATTACACATGGCAATCTGGCACCAATGCATCTGTTTTCTGGCA |
| 6769 | GROUP_43 | CCCAGAAAAGAGAGATGATTACACATGGCAATCTGGCACCAATGCATCTGTATTCTGGCA |
| 6770 | GROUP_44 | ACCCACAAAAGAAATGACTACACATGGCAGTCCGGCACTAATGCATCAGTATTCTGGCA |
| 6771 | GROUP_45 | ACCTGAGAAAAGAGATGATTTCACATGGCAATCAGGCACAAATGCATCTGTTTTCTGGCA |
| 6772 | GROUP_46 | ACCTGAGAAGAGAGATGACTTTACATGGCAATCAGGCACAAATGCATCTGTGTTTTGGCA |
| 6773 | GROUP_47 | ACCAACAACTAGAAATGACTATGCTTGGCAATCTGGAACAAATGCATCTGTATTTTGGCA |
| 6774 | GROUP_48 | TCCAACAACTAGAGAAGACTATGCTTGGCAATCTGGAACAAATGCATCTATATTCTGGCA |
| 6775 | GROUP_49 | GCCCAATAGTAGGGACGATTATGCATGGCAGTCTGGCACTAATGCCTCTGTTTTCTGGCA |
| 6776 | GROUP_50 | ACCAAAGAGCAGAGATGATTATGCATGGCAGTCTGGCACTAATGCATCTGTTTTCTGGCA |
| 6777 | GROUP_51 | ACCGGAAAGTAGAAATGACTATGCATGGCAATCTGGAACAAATGCGTCCATTTTTTGGCA |
| 6778 | GROUP_52 | TCCGAGAGCAGAAATGACTATGCATGGCTCTGGAACAAATGCATCTGTTTTTTGGCA |
| 6779 | GROUP_53 | TCCAATAAAACGCGAAGATTATACATGGCAATCAGGAACAAATGCTTCTATATTTTGGCA |
| 6780 | GROUP_54 | TCCCAAGAAACGTGATGATTACACATGGCAGTCAGGAACAAATGCATCTGTGTTCTGGCA |
| 6781 | GROUP_55 | TCCTGTGAAGCGTGATGACTACACATGGCAATCAGGGACAAATGCATCTGTGTTCTGGCA |
| 6782 | GROUP_56 | CCCCGAAAAACGTGATGATTACACATGGCAATCAGGAACAAATGCATCTGTGTTCTGGCA |
| 6783 | GROUP_57 | ACCCAAGAATCGTGATGACTTTACATGGCAATCAGGCACAAATGCATCTGTTTTCTGGCA |
| 6784 | GROUP_58 | ACCCAAAAAACGTGATGATTACACATGGCAATCTGGCACCAACGCCTCAGTTTTTTGGCA |
| 6785 | GROUP_59 | ACCAAAGAAGAGAGATGACTATACTTGGCAGTCAGGCACCAATGCATCTGTGTTTTGGCA |
| 6786 | GROUP_60 | ACCAAAGACTAGAGATGACTACACATGGCAATCAGGGACAAATGCATCAGTATTTTGGCA |
| 6787 | GROUP_61 | ACCAAAAACTAGAGATGATTACACATGGCAGTCAGGCACTAATGCATCAGTGTTTTGGCA |
| 6788 | GROUP_62 | CCCCACTACCAGAAATGATTACACATGGCAATCCAGTACCAATGCCTCTGTTTTCTGGCA |
| 6789 | GROUP_63 | ACCCAAAACCAGAGATGACTATACCTGGCAATCTGGAACTAATGCTTCAGTCTTTTGGCA |
| 6790 | GROUP_64 | ACCGAGATATCGGAATGATTATACTTGGCAGTCTGGTACTAATGCTTCAGTGTTCTGGCA |
| 6791 | GROUP_65 | GCCAAACAAACGCAATGATTACTTGGCTGGCACGAATGCTTCAGTCTTCTGGCA |
| 6792 | GROUP_66 | TCCACTTACTAGGAAAGATGATGAGTGGCAATCAGGAACTAATGCTTCAGTATTCTGGCA |
| 6793 | GROUP_67 | TCCAAAAACTAGAAAAGATGAAGAGTGGCAGACAGGAACTAATGCTTCAGTCTTTTGGCA |
| 6794 | GROUP_68 | ACCAGAGACCAGGGATGCCGATGAATGGCAGTCTGGAACTAATGCATCAGTCTTTTGGCA |
| 6795 | GROUP_69 | TCCAGATAAAGGATGCACGATGCCTGGCAAACCAGTACAAATGCCTCAGTTTCTGGCA |
| 6796 | GROUP_70 | CCCTGTTAGTAGAACTGACAACACTTGGCAATCTAGCACAAATGCATCAGTCTTTTGGCA |
| 6797 | SUMMARY  | XCCX-XXXXXXGXX--XX-XXXXX-TGGCA-XC-XG-A--AAXXXXTCXX-XTTXTGGCA |
| 6798 | | |
| 6799 | GROUP_1  | ACATGGACAGCCATTTCCTAGATTTTCTTTACCATTCTTAGCATTGCATCAGCTTATTA |
| 6800 | GROUP_2  | ACATGGACAACCGTTCCCTAGATTCTCTTTACCATTCTTAGCATTGCATCAGCTTATTA |
| 6801 | GROUP_3  | ACATGGTCAAACTTTCCCTAGATTTTCTTTACCTTTCCTAAGCATAGCTTCAGCATACTA |

FIG. D14 CONT'D

```
10.trace                                                                                      9/20/2007 5:05 PM 6802 GROUP_4    ACATGGGCAAACTTTCCCCAGATTTTCCTTACCTTTCTTGAGTGTTGCTTCAGCATATTA
6803 GROUP_5    ACATGGCCAAGCTTTCCCCAGATTCTCTCTACCTTTCTTAAGTATTGCTTCTGCTTATTA
6804 GROUP_6    ACATGGACAAACATTCCCAAGATTTTCATTGCCCTTCCTGAGCATAGCCATCAGCTTATTA
6805 GROUP_7    ACATGGACAAGCTTTTCCAAGGTTTTCTCTACCTTTCTTGAGTATTGCATCAGCATATTA
6806 GROUP_8    ACACGGACAGCCTTACCCTAGATTTTCATTACCATTTCTAAGCATAGCCTCAGCATATTA
6807 GROUP_9    ACATGGACAACCTTTCCCTAGATTTTCTTTACCCTTCTTAAGCATTGCATCTGCTTACTA
6808 GROUP_10   GCATGGGCAGCCATTCCCTAGAATTCTTTACCTTTCTTGAGCATTGCTTCTGCATACTA
6809 GROUP_11   ACTTGGACAACCATTCCCAAGATTCTCGCTACCTTTTCTAGGCATAGCCTTCAGCATATTA
6810 GROUP_12   ACATGGACAACCATTCCTAGACCTTTCTGAGTATTGCTTCAGCTTACTA
6811 GROUP_13   ACATGG-CAACCCTT-CCTAGATTTTCATT-CC-TTT-TGAGTGTTGCATCTGCTTATTA
6812 GROUP_14   ACATGGTCA-CCTTTCCCAAGATTTTCATT-CCATT-CTAAGTGTTGCATCTGC-TATTA
6813 GROUP_15   ACATGGACAACCCTTTCCCAAGATTTACATTACCCTTTTGAGTGTCGCATCCGCTTATTA
6814 GROUP_16   ACAAGGGCAACCCTTTCCCAAGATTTTCATTACCATTTTGAGTGTTGCATCTGCTTATTA
6815 GROUP_17   ATATGGTCAAACATACCCAAGATTTTCTCTACCTTTCATGAGTATAGCCTCAGCATATTA
6816 GROUP_18   ATATGGACAAACATACCCTAGGTTTTCATTACCCTTTCTAAGTATAGCCTTCAGCTTATTA
6817 GROUP_19   ATATGGACAAACATATCCTAGGTTCTCATTACCTTTCCTTAGCATAGCCTTCAGCATATTA
6818 GROUP_20   ACATGGACAAACCTATCCTAGATTTTCCCTTCCTTTTCTGAGTGTAGCCTCTGCATATTA
6819 GROUP_21   ACATGGACAAACATACCCTAGATTTTCACTTCCTTTCTTAAGTATAGCCTTCTGCATACTA
6820 GROUP_22   ACATGGTCAAACATACCCTAGATTTTCCCTCCCTTTCTTAAGCATAGCCCTCAGCATACTA
6821 GROUP_23   ACATGGTCAAACATACCTAGATTCTCTCTACCATTCTTGAGTATAGCCATCTGCATATTA
6822 GROUP_24   ACATGGTCAAACATACCCCAGATTTTCACTTCCTTTCCTCAGTATAGCCATCAGCTTATTA
6823 GROUP_25   ACATGGGCAAACATACCCTAGATTTTCACTTCCTTTCCTAAGTATAGCCTTCTGCTTATTA
6824 GROUP_26   ACATGGTCAAACATACCCTAGATTTTCCTTGCCTTTCTTAAGTATAGCCCTCAGCATATTA
6825 GROUP_27   GCATGG-CA-ACTTATCCTAGATTTTCA-TACCCTTCCTTAGTATAGCATCAGCATA-TA
6826 GROUP_28   ACATGGTCAAACATTTCCAAGATTTTCCTTACCTTTTCTGAGCATAGCCATCAGCATATTA
6827 GROUP_29   ACATGGACAAACATTTCCAAGATTTTCACTACCATTTCTGAGCATTGCATCAGCATATTA
6828 GROUP_30   ACATGGACAATCATATCCCAGATTTTCACTTCCGTTTTTGAGCATTGCCTCTGCATATTA
6829 GROUP_31   GCATGGACAGGCATATCCCAGGTTTTCACTTCCATTTCTAAGTATAGCATTGCCTCTGCATACTA
6830 GROUP_32   ACATGGACAATCATACCCCAGATTCTCACTACCATTCTTAAGTATTGCCTCTGCTTATTA
6831 GROUP_33   ACATGGTCAACCTTACCCCAGATTTTCTTTGCCTTTTCTCAGCATTGCATCTGCTTACTA
6832 GROUP_34   GCATGGACAGCCATACCCTAGATTCTCATTACCTTTCCTTAGCATAGCCATCTGCTTATTA
6833 GROUP_35   ATATGGTCAGACATATCCTCGATTTTCCTTACCTTTCTAAGCATAGCCATCTGTCTATTA
6834 GROUP_36   GCATGGACAAACATACCCTAGATTTTCACTTCCATTTCTAAGTATTGCATCTGCCTACTA
6835 GROUP_37   ACACGGTCAACCATACCCTCGATTTTCTCTCCCTTTCCTTAGCATAGCCCTCAGCATATTA
6836 GROUP_38   ACATGGTCAACCCTACCCTCGATTCTCACTTCCATTTCTTAGTATAGCCTCAGCATATTA
6837 GROUP_39   GCATGGTCAACCTTATCCCCGATTCTCACTCCCTTTCCTCAGTGTAGCCTTCAGCATATTA
6838 GROUP_40   ACATGGACAACCTTACCCTCGCTTCTCACTTCCTTTCTTGAGTATAGCCCTCAGCTTACTA
6839 GROUP_41   ACATGGTCAACCATACCCAAGATTTTCATTACCTTTTCTAAGTATAGCCTTCTGCATATTA
6840 GROUP_42   ACATGGTCAAATTTACCCCCAGATTCTCTTTACCATTCTTAGTATTGCATCTGCATATTA
6841 GROUP_43   GTATGGTCAAGTTTACCCTAGGTTTTCTCTACCATTTCTTAGCATTGCTTCCGCATATTA
6842 GROUP_44   ACATGGTCAAACTTACCCCAGATTCTCATTACCATTCCTTAGTATAGCCATCCGCTTATTA
6843 GROUP_45   ACATGGTCAAGCTTATCCCAGATTTTCATTACCATTCCTAAGTATTGCATCTGCTTATTA
6844 GROUP_46   GCACGGGCAAGCATATCCTAGATTTTCACTGCCTTCCTTAGTATTGCCTCTGCATATTA
6845 GROUP_47   GCATGGGCAACCTTTCCCCTCGCTTTTCACTTCCCTTTTGAGTATTGCATCAGCATATTA
6846 GROUP_48   ACATGGGCAACCCTTTCCCCGGTTTTCACTCCCTTTTCTAAGTGTAGCATCAGCATATTA
6847 GROUP_49   ACATGGACAGGCTTATCCAAGATTTTCCTTACCTTTCCTAAGTGTGGCATCTGCTTATTA
6848 GROUP_50   ACATGGGCAAGCATACCCAAGATTTTCTCTACCCTTCCTTAGTGTAGCCTCAGCTTACTA
6849 GROUP_51   ACATGGACAAACATATCCAAGGTTCTCCTTACCCTTTTGAGTGTGGCATCTGCTTATTA
6850 GROUP_52   ACACGGACAAACATACCCAAGATTCTCCCTACCATTTTTGAGTGTAGCATCTGCTTATTA
6851 GROUP_53   GGAGGGTCAACCATACCCTAGATTCACAATTCTTTTATGAGTATTGCATCAGCTTATTA
6852 GROUP_54   AGAAGGACAACCATACCCAAGATTTACCATTCCCTTTATGAGTATTGCATCAGCTTACTA
6853 GROUP_55   AGAAGGGCAACCATATCCTAGATTTACAATCCCCTTTATGAGTATTGCATCAGCTTATTA
6854 GROUP_56   AGAAGGACAACCATACCCCAGATTCACAATCCCTTTTATGAGCATTGCATCAGCCTATTA
6855 GROUP_57   GGAAGGACAACCATACCCTAGATTTACAATCCCTTTTATGAGTATTGCATCAGCTTACTA
6856 GROUP_58   GGAAGGTCAACCTTACCCCAGATTCACAATCCCTTTTATTAGTATTGCCTCAGCATATTA
6857 GROUP_59   ACAAGGTCAAACATACCCAGGTTCTCTATACCATTTTCTAGTATTGCCTCAGCTTATTA
6858 GROUP_60   GCAGGGCCAACCTTACCCCAGATTTACCATTCCATTTATGAGTATAGCCTTCAGCATATTA
6859 GROUP_61   ACAAGGACAACCTTACCCCAGATTTACCATTCCATTTATGAGTATAGCCTTCAGCATATTA
6860 GROUP_62   ACAAGGACAACCATACCCAGATTCACTATACCTTTTATGAGTATTGCCTCAGCTTATTA
6861 GROUP_63   ACAAGGACAACCATACCCTAGATTCACAATCCCCTTTCATGAGTATTGCGTCAGCATATTA
6862 GROUP_64   GCAAGGGCAGCCATACCCTAGATTCACTATCCCGTTCATGAGTATAGCCTCAGCATATTA
6863 GROUP_65   ACAGGGTCAGCCATACCCCAGATTCACTATTCATTCATGAGTATAGCCTCAGCATATTA
6864 GROUP_66   ACATGGACAACCATACCCTAGATTTACAATCCCTTTTGTAAGCATAGCCTCAGCATACTA
6865 GROUP_67   GCATGGTCAACCATACCCCAGATTTACAATTCCTTTTGTGAGTATTGCCTCAGCATATTA
6866 GROUP_68   GCACGGCCAACCATACCCAAGGTTTACAATCCCCTTCATAAGCATTGCATCAGCATATTA
```

FIG. D14 CONT'D

10.trace                                                                    9/20/2007 5:05 PM

```
6867 GROUP_69    AGTTGGACA-ACTTATCCCAGATTCACCATACCTTTCTCCAG-ATAGCATCAGCTTATTA
6868 GROUP_70    GGTTGGTCAAACTTATCCCAGATTTTCTATACCTTTCTCAAGTATAGCTTCAGCTTACTA
6869 SUMMARY     XXXXGG-CA-XXXTX-CCXXGXXTXXCX-T-CC-TT--XXXG-XTXGCXTCXGX-TA-TA
6870
6871 GROUP_1     TATGTTTTATGATGGATATGATGGAGACAACACTTCTTCCAAGTATGGTAGCGTAGTTAC
6872 GROUP_2     CATGTTTTATGATGGATATGATGGAGATAATTCCTCTTCCAAATATGGTAGTATAGTCAC
6873 GROUP_3     CATGTTTTATGATGGATACGATGGTGATACATCGACCTCAAGATATGGCACATCAGTCAC
6874 GROUP_4     CATGTTTTATGATGGTTATGATGGTGATACACCAGGCTCAATGTATGGGACGTCAGTCAC
6875 GROUP_5     CATGTTTTATGATGGTTATGATGGAGACACTTCAAGCTCCAGATATGGTACATCAGTTAC
6876 GROUP_6     CATGTTTTATGATGGTTATGATGGAGATAAATCTGAATCTAGGTATGGTGTGTCTGTAAC
6877 GROUP_7     CATGTTTTATGATGGATATGATGGAGATAAATCAAGCTCTAGGTATGGTGTTTCAGTTAC
6878 GROUP_8     TATGTTCTATGATGGATATGATGGTGATAAATCGTCATCTAGGTATGGTGTTTCTGTCAC
6879 GROUP_9     CATGTTCTATGATGGTTATGATGGTGATACACATGACTCACGTTATGGCACAACAGTGAT
6880 GROUP_10    CATGTTTTATGATGGATATGATGGTGATACACATGATTCACACTATGGTACTACTGTAAT
6881 GROUP_11    CATGTTCTATGATGGTTATGATGGAGATACTCCTGGGTCTCGTTATGGAACCACAGTAGT
6882 GROUP_12    CATGTTTTATGATGGCTATGATGGGGATACCTATGAATCACGTTATGGTACTACAGTGGT
6883 GROUP_13    CATGTTTTATGATGGCTATAATGGTGATGA--A-ACAGC-A-ATA-GGTACCAC-GTGGT
6884 GROUP_14    CATGTTTTATGA-GGTTA-AATGGAGGTGATCATACAGCAACTTATGGCACCACAGTGGT
6885 GROUP_15    CATGTTTTATGATGGTTATGATGGAGACAAAAGTGGAGCCAAGTATGGTACTACAGTAGT
6886 GROUP_16    CATGTTTTATGATGGCTATAATGGTGACAGAAGTGGAGCCAAGTATGGCACCACAGTGGT
6887 GROUP_17    CATGTTTTATGATGGTTATGATGGAGATCAACCAAACTCCAGATATGGTAATATAGTTAC
6888 GROUP_18    CATGTTTTATGATGGATATGATGGAGACCAACCTAGTTCTAGGTATGGTAATATAGTTAC
6889 GROUP_19    CATGTTCTATGATGGATATGATGGGGACCAACCCAATTCCAGGTATGGTAATATGGTTAC
6890 GROUP_20    CATGTTTTATGATGGATATGATGGTGATCAACACGACTCAGTGTATAGGTTCAGTTGTTAC
6891 GROUP_21    TATGTTTTATGATGGATATGATGGTGACCAAACTGATTCGAGATATGGTACCATTGTTAC
6892 GROUP_22    CATGTTTTATGATGGATATGATGGTGATCAACATGATTCAAGATATGGTACAGTAGTGAC
6893 GROUP_23    CATGTTTTATGATGGTTATGATGGTGATAAATCTACATCCAGGTATGGTACAGTAGTTAC
6894 GROUP_24    CATGTTCTATGATGGCTACGACGGTGACCAGACCTCATCGCGGTATGGCACAGTTGCAAC
6895 GROUP_25    CATGTTCTATGATGGATATGATGGTGACCAAACTGAGTCACGCTATGGCACTGTAGTCAC
6896 GROUP_26    CATGTTTTATGATGGATATGATGGTGACCAAACTGAATCAAGATATGGTACTGTAGTCAC
6897 GROUP_27    CATGTTTTATGATGGTTATGATGGTGA-CAGACTGACTCACAATATGGTGCAGT-GT-AC
6898 GROUP_28    CATGTTTTATGATGGATATGAAGGTGACCAAAAAACATCCCGTTATGGCACAATTGCAAG
6899 GROUP_29    CATGTTTTATGATGGATATGAAGGGGATCAAAATACATCCCGTTATGGCACCATTGCTAG
6900 GROUP_30    CATGTTCTATGATGGTTATGATGGTGG...ACCAGATTCTCTGTATGGAACAATTGTAAC
6901 GROUP_31    CATGTTTTATGATGGTTATGATGGTGG...GCCAGATTCACAATATGGAACAATTGTAAC
6902 GROUP_32    CATGTTTTATGATGGCTATGATGGTGG...ACCAGATTCACTATATGGCACCATAGTGAC
6903 GROUP_33    CATGTTCTATGATGGATATGATGGAGATTCCACTGAATCACATTATGGTACAGTGGTCAC
6904 GROUP_34    CATGTTTTATGATGGATATGATGGAGACTCTACTGAATCACATTATGGTACAGTAGTAAC
6905 GROUP_35    TATGTTTTATGATGGATATGATGGGGACTCAACAGAATCACATTGGGACAGCGGTGAC
6906 GROUP_36    CATGTTTTATGATGGTTATGGTCACTCAACTGAATCACATTATGGGACGGTTGTGAC
6907 GROUP_37    CATGTTTTATGATGGTTATGACGGTGG...ACCTGGTTCCCGTTATGGCGCAGTGGTGAC
6908 GROUP_38    CATGTTCTATGATGGTTATGATGGTGG...ACCTGGCTCACGCTATGGCACAGTGGTGAC
6909 GROUP_39    CATGTTTTATGATGGGTATGATGGAGG...TCCCGGATCACGTTATGGAGCAGTGGTAAC
6910 GROUP_40    TATGTTCTATGATGGCTATGATGGTGATGCTCCCGGATCGCGATACGGGACCATAGTGAC
6911 GROUP_41    CATGTTTTATGATGGGTATGATGGAGATTCACCAGGATCCCGCTATGAACAATAGTAAC
6912 GROUP_42    TATGTTTTATGATGGATATAATGGAGATTCCTCAGATGCACGCTATGGGACAACAATCAC
6913 GROUP_43    CATGTTTTATGATGGTTATGAAGAAGGCTCTACAAATGCACGCTATGGAACAACAGTCAC
6914 GROUP_44    TATGTTTTATGATGGATATGATGGTGACTCCACACAATCACATTATGGCACCACAGTAGT
6915 GROUP_45    TATGTTTTATGATGGTTATGATGGAGATTCTGAAATAACGCGCTATGGAACATCAGTGAC
6916 GROUP_46    CATGTTTTATGATGGATATGATGGTGACTCTGAATCAACACGCTATGGAACATCTGTTAC
6917 GROUP_47    CATGTTTTATGATGGTTATGATGGAGACACATATAAATCCAGATATGGAACTGTAGTCAC
6918 GROUP_48    CATGTTCTATGATGGATATGATGGTGATACTTATCACTCCAGATACGGGACTGTAGTCAC
6919 GROUP_49    CATGTTTTATGATGGGTATGATG......AACAAGATCAAAACTATGGTACAGCAAGCAC
6920 GROUP_50    CATGTTTTATGATGGATATAATG......AACAGGGCCAAAATTATGGTACGGTAAGTAC
6921 GROUP_51    CATGTTTTATGATGGATACAATG......AGAAAGGCACGCATTATGGAACAGTTAGCAC
6922 GROUP_52    CATGTTCTATGATGGATACAATG......AGGGAGGCACAAATTATGGTACAGTGAGCAC
6923 GROUP_53    TATGTTCTATGATGGATATGATGGTGATGATGCGTCATCCAAATATGGTTCCGTAGTAAC
6924 GROUP_54    TATGTTTTATGATGGATATGATGGTGATGATGCATCATCTAGGTATGGCTCAGTGGTAAC
6925 GROUP_55    TATGTTTTATGATGGTTATGATGGTGATAATGCGCATCAAAATATGGATCTGTGGTTAC
6926 GROUP_56    CATGTTTTATGATGGTTATGATGGTGATAGTGCAGCATCAAAATACGGTTCTGTAGTCAC
6927 GROUP_57    TATGTTTTATGATGGCTATGATGGTGATGATGCTAAATCAATATATGGTTCTGTGGTAAC
6928 GROUP_58    CATGTTTTATGATGGTTATGCTGATGACAACCCAAGTGCACCTTATGGAACTGTAGTTAC
6929 GROUP_59    CATGTTTTATGATGGATACTCGGATGACAGCACATCCTCTCATATGGCACTGTAGTTAC
6930 GROUP_60    TATGTTTTATGATGGTTATGAAGATGATAAGG...GAAGTGTGTATGGGTCTGTTGTCAC
6931 GROUP_61    TATGTTTTATGATGGATATGAGGATGACAAAG...GAAGTGTGTATGGATCTGTTGTTAC
```

FIG. D14 CONT'D 10.trace                                                              9/20/2007 5:05 PM

```
6932 GROUP_62    CATGTTTTATGATGGTTATGAAGATGACAATG...GAACTACCTATGGTGCAGTGGTTAC
6933 GROUP_63    TATGTTCTATGATGGGTATGAAGATGACAATG...GCACCACTTATGGGGCTGTTGTTAC
6934 GROUP_64    CATGTTTTATGATGGCTACGAAAGTGATAAAG...GCAAGATCTATGGAACTGCAGTCAC
6935 GROUP_65    CATGTTCTATGATGGGTATGAGAGTGATAAAG...GCAACATTTATGGAACAGCAGTTAC
6936 GROUP_66    CATGTTTTATGATGGGTATGAAGGTGATAGTTTGACCTCACAGTACGGTTCAGTAGTCAC
6937 GROUP_67    CATGTTCTATGATGGTTATGAGGGTGATGACCCAAATTCAAAATATGGTTCAGTGGTTAC
6938 GROUP_68    CATGTTCTATGATGGGTATGAAGGTGATGCCCTCAGTTCTAAATATGGCTCAGTAGTTAC
6939 GROUP_69    CATGTTCTATGATGGTTATGATTCAGATGGTTTAGATGCTATTTATGGTATTCCTGTTAC
6940 GROUP_70    CATGTTTTATGATGGATACGACACTGATGGCACAGATGCAGTGTATGGTGTTAGTGTGAC
6941 SUMMARY     XATGTTXTATGA-GGXTA-XXXXXXXX-XX--X-XXXXX-X-XTA-GGXXXXXX-XX-XX
6942
6943 GROUP_1     TAATGATATGGGTACTATATGCTCAAGAATAGTTACAGAAAAACAGAAACATTCTGTTGT
6944 GROUP_2     CAATGATATGGGAACCATATGTTCAAGAATAGTTACAGAGAAGCAGGAACACCCTGTCGT
6945 GROUP_3     TAACCATATGGGAACGCTATGCTCAAGAATAGTCACCAACAAGCAGCAGCATGAAGTTGA
6946 GROUP_4     CAACCACATGGGAACACTGTGCTCGAGGATAGTTACCAACAAACAGCAGCATGAGGTTGA
6947 GROUP_5     AAACCACATGGGGACACTCTGTTCAAGAATTGTGACAAATAAACAACTTCATCCTGTTGA
6948 GROUP_6     CAACCACATGGGCACTTTATGTTCTAGAATAGTTACAAACAGTCAGGAGCATCCAGTGGA
6949 GROUP_7     TAACCACATGGGGACTTTATGTTCTAGAATTGTAACAAACAGCCAAGAACATCCAGTTGA
6950 GROUP_8     TAATGATATGGGTACACTTTGCACTAGAATTGTAACAAACCAACAG-AACACCTAGTGGA
6951 GROUP_9     AAATCACATGGGCACTTTGTGCATGCGAATAGTCACAAACCAGCAAGCACATGAGGTGGA
6952 GROUP_10    TAACCACATGGGTACACTTTGTATGAGGATAGTTACAAATCAGCAAGCACATGAGGTGGA
6953 GROUP_11    TAATCATATGGGTATATTAGGATTGTTACAAATGAACAGCACCATAATGTTGA
6954 GROUP_12    TAATCACATGGGCACACTGTGCATTAGAATAGTCACTAATCAGCAAAATCATGAGGTTGA
6955 GROUP_13    TAA-CGTATGGG-GCACTGTG-ATGAG-ATTGTCACAAA-AAACAAGT-CATGATGTTGA
6956 GROUP_14    TAACCGGATGGGGACGCTTTG-GTCAG-AT-GTTAC-GGCAAACA-GCTCATGATGT-CA
6957 GROUP_15    TAATCGCATGGGTGCACTATGCATGAGAGTTGTCACTAACAAACAAGCTCATAAAGTTGA
6958 GROUP_16    CAATCGCATGGGTGCATTGTGTATGAGAGTTGTAACAAACAAGCAACTCCATAAAGTTGA
6959 GROUP_17    CAATGATATGGGCACTCTGTGTTATAGAATAGTAACTGATGACCATAGACACAAAATTGA
6960 GROUP_18    CAATGACATGGGCACCCTATGTTCCAGGATAGTAACTGATGATCATAAGCACAAGATTGA
6961 GROUP_19    CAATGACATGGGCACTTTATGCTCTAGAATAGTTACAGATAATCATAAGCATCCAATAGA
6962 GROUP_20    AAACGACATGGGAACTCTATGCTATAGAATAGTCACTGACAAGCATAATCACCAAATAGA
6963 GROUP_21    TAATGATATGGGAACCTTATGTTATAGAATAGTTACAGATGAACATGCCCACAAAATAGA
6964 GROUP_22    TAATGACATGGGTACTTTATGCTCCAGAATTGTAACTGATGAACACCAAAACAGAGTAGA
6965 GROUP_23    CAATGACATGGGCACTTTGTGTTCTAGGATTGTCACTGATGAGCACCAAAATAAAGTGGA
6966 GROUP_24    AAATGACATGGGTACCTTGTGCTCTAGAATAGTCACAGATAAACATAAGAATGAGGTGGA
6967 GROUP_25    TAATGACATGGGTACTTTATGTTCTAGAATAATAACTGATAACCATAAGCACCCAATTGA
6968 GROUP_26    TAATGACATGGGCACTTTATGTTCTAGAATTGTTACTGACCAGCACACACATCCCATAAA
6969 GROUP_27    TAATGATATGGGATCTCTATGCTA-AGAATAGTAACTG--CAGCATAAGCA-AAGATAGA
6970 GROUP_28    CAACCACATGGGAACATTATGTTCTAGGATAGTTACAGAAGAACACCAAAATCAAATCGA
6971 GROUP_29    TAATCACATGGGGACACTGTGTTCTAGAATAGTTACAGAAGAACATCGAAATAAAGTTGA
6972 GROUP_30    AAATGATATGGGATCTTTATGTTCCCGTGTAGTTACTGAAGAGCATGGACCCCGTGTCAA
6973 GROUP_31    AAATGATATGGGTTCCCTGTGTTCTCGTATAGTCACCGAAGAGCACGGATCCCGTGTTGA
6974 GROUP_32    TAATGATATGGGTTCCTTGTGTTCGCGTATAGTTACTGAAGAACATGGTTCTCGCGTAAA
6975 GROUP_33    TAATGACATGGGGACACTGTGTTCTAGAATAGTCGAAGAGCATGGGACACGTGTAGA
6976 GROUP_34    AAATGACATGGGAACTCTATGTTCTAGAATTGTGACTGAAGAACACGATGCACGTGTGGA
6977 GROUP_35    CAATGATATGGGGACACTTTGTTCAAGAATAGTCACTGAAAATCATGGGACCCAAGTGAA
6978 GROUP_36    CAATGACATGGGAACGTTGTGCTCCAGAATAGTTACTGAACACCATGGTACACAGGTTCA
6979 GROUP_37    AAATGATATGGGCACTTTTGTGCTCTAGAATTGTGACTGAGGAACACACACACAGGTCAA
6980 GROUP_38    AAATGACATGGGAACATTATGCTCCAGGATTGTGACTGAGGAGCACAAGACACAGGTTAA
6981 GROUP_39    AAATGATATGGGCACACTGTGCTCTAGGATTGTGACTGAAGAACACCAGACACAAGTCAA
6982 GROUP_40    AAATGACATGGGTACACTGTGTTCTAGAATTGTAACTGAAGAACACCAGACTCAAGTCAG
6983 GROUP_41    TAATGATATGGGAACCTTATGCTCCAGAATAGTAACTGATGAACACCAACAGGTTGC
6984 GROUP_42    TAATGATATGGGCACACTTTGCTTCAGAATAGTAACTGAAGAACATACTAACAAGGTCAA
6985 GROUP_43    AAATGACATGGGTACATTATGCTTTAGAATAGTTACTGAAGAACACACCAACAAAGTTAA
6986 GROUP_44    TAATGACATGGGCACATTATGCTTTAGGATAGTGACTGAAGAACACACTAGCAGGGTAAA
6987 GROUP_45    AAATGATATGGGTGCATTGTGCTTTAGAATAACTGAACAGCATACAAATCAAGTTAA
6988 GROUP_46    CAATGACATGGGCACTTTATGTTTTAGAATAGTGACAGAGGAACACACCAACAAGGTCAA
6989 GROUP_47    CAATGACATGGGAACTTTGTGTTCGCGTATTGTGACCAGTGAGCAATTACACAAAGTCAA
6990 GROUP_48    TAATGATATGGGAACATTATGCTCACGGATATGACAAGTGACGAAGTGCACAAGGTGAA
6991 GROUP_49    AAATAACATGGGGTCACTATGCTCTAGGATAGTAACAGAGAAACACATTCATAAGGTACA
6992 GROUP_50    AAACAACATGGGATCATTATGCTCTAGGATAGTAACAGAGAAACACATTCACAGTATGCA
6993 GROUP_51    AAACAACATGGGCACATTGTGCTCCAGAGTGGTAACAGAGAAACACATTCATGATATGCG
6994 GROUP_52    AAACAACATGGGCACACTGTGTTCCAGAGTGTAACAGAAAAACACATTCATGATGTGCG
6995 GROUP_53    CAATGACATGGGAACCATATGTGTTAGACTAGTTACATCTACACAAAAACACAATTTAAA
6996 GROUP_54    TAATGATATGGGAACTATATGTATTAGATTGGTCACCTCCACCCAAAAGCATAAACTGAA
```

FIG. D14 CONT'D

```
10.trace                                                         9/20/2007 5:05 PM 6997 GROUP_55    TAACGACATGGGAACCATATGTGTTAGAATAGTTACATCCAACCAAAAACATGATTTAAA
6998 GROUP_56    TAATGATATGGGAACCATATGTGTTAGAATAGTGACATCCAACCAAAAACATGATTTAAA
6999 GROUP_57    AAATGACATGGGAACTATATGTGTTAGAATAGTCACATCCAAACAAAGACACAATTTAAA
7000 GROUP_58    CAATGACATGGGTTCACTGTGTGTCAGAATAGTTACAGACCAGCAAAAACATAAAGTTAA
7001 GROUP_59    CAATGACATGGGTACACTGTGTATGAGGATGGTTACAGATCAACAACAACATAAGGTCAC
7002 GROUP_60    AAACGATATGGGCACATTGTGTGTTCGTATTGTGACTGAGCAGCAGACACATAAGGTTAA
7003 GROUP_61    AAATGATATGGGCACATTATGTGTCCGTATTGTGACTGAGCAGCAGACACATAGGGTCAA
7004 GROUP_62    AAATCATATGGGAACACTCTGTGCTCGCATAGTAACTGAACAACAGAAGCATGAAGTCAA
7005 GROUP_63    TAATGATATGGGACATTTGTGTGCGCATAGTGACTGAGCAACAGAAAAATGAGGTCAA
7006 GROUP_64    CAATGATATGGGAACTATATGTGTCAGAATTGTTACCGAACAACAAAAACATAAGGTTCT
7007 GROUP_65    CAATGATATGGGAACCCTGTGTGCTAGAATTGTTACAGAACAACAGAAACATAAAGTCCT
7008 GROUP_66    AAATGCTATGGGGACACTATGTGTTCGTGTGGTCACAGAGCAACAAAAACATGAGGTTAA
7009 GROUP_67    TAATGCTATGGGCACACTATATGTGCGTGTGGTTACAGAAAGGCAAAAACATGAAGTCAA
7010 GROUP_68    TAATGCCATGGGCACCTTATGTGTTCGTGTGGTTACAGAACAGCAAAGCAACACAGTCAA
7011 GROUP_69    AAATCACATGGGCACAATATGTGTGAGAATGGTGACAGATAAACAGAAAATTAAAACTAA
7012 GROUP_70    TAACCATATGGGGACTATATGTGTTAGAATTGTTACAGACCAACAACAACATAGAGTTAA
7013 SUMMARY     XAA-XXXATGGG-XCXXTXTX-XX-XG-XT-XTXAC-X--XXXCA--X-XX-XXXXX-XX
7014
7015 GROUP_1     CATCACAACACACATATATCATAAAGCTAAACACACAAAAGCTTGGTGTCCTAGGCCCCC
7016 GROUP_2     TATTACAACACACATATATCACAAAGCTAAACACACAAAAGCTTGGTGTCCTAGACCTCC
7017 GROUP_3     GATTACCACACGTATATATCACAAGGCCAAGCATATTAAAGCATGGTGTCCAAGGGCCCC
7018 GROUP_4     AATCACCACGCGTGTGTATCATAAGGCCAAGCATGTAAAGGCTTGGTGTCCAAGAGCACC
7019 GROUP_5     AGTCACAACTCGTGTATATCATAAGGCAAAGCATATTCGAGCATGGTGTCCTAGAGCACC
7020 GROUP_6     GGTTGTCACACGTGTGTATCACAAAGCTAAACACGTCAAAGCCTGGTGCCCTAGAGCTCC
7021 GROUP_7     GGTGACTACACGTGTATATCATAAAGCTAAACACATCAGAGCCTGGTGCCCAAGAGCTCC
7022 GROUP_8     GGTTACAACCAGAGTTTACCATAAAGCCAAGCATGTTAAAGCATGGTGCCCTAGGGCTCC
7023 GROUP_9     AATTACCACCAGTGTTTATCACAAAGCCAAGCATGTCAAAGCATGGTGTCCAAGACCACC
7024 GROUP_10    AATTACTACTAATATCTATCACAAAAGCAAACATGTTAAAGCTTGGTGCCCAAGACCACC
7025 GROUP_11    AATTACTACTAGAGTATACCATAAGGCTAAGCATGTTAAAGCCTGGTGTCCTAGACCACT
7026 GROUP_12    AATCACCACTAGAGTATACCACAAGGCTAAACATATTAAAGCTTGGTGTCCCAGACCACC
7027 GROUP_13    GGT-ACAACTAA-ATTTACCA-AA-GCTAAGCATGTAAAAGC-TGGTGCCC--G-CC-CC
7028 GROUP_14    AGTTACAACAAG-AT-TATCA-AAAGCTAAACATGTAAA-GC-TGGTG-CCTAGACCACC
7029 GROUP_15    AATCACAACCAATATTTACCATAAGGCCAAACATGT-AAGGCATGGTGTCCTAGGCC-CC
7030 GROUP_16    AATCACAACTAACATCTACCATAAAGCCAAGCATGTGAAAGCATGGTGTCCTAGACCACC
7031 GROUP_17    AGTCACAACTAGGGTGTATCATAAAGCAAAGCATGTGAAGGTGTGGTGTCCAAGACCACC
7032 GROUP_18    AGTTACAACAAGAATATATCACAAAAGCAAAGCATGTTAAGGTATGGTGCCCGAGACCACC
7033 GROUP_19    AGTTACAACAAGAGTATACCATAAAGCAAAGCATGTCAAAGTCTGGTGCCCAAGACCACC
7034 GROUP_20    AATTACAACAAGAATATACCACAAAGCAAAGCACATTAAGGTCTGGTGTCCAAGGCCACC
7035 GROUP_21    GATCACTACAAGAATATACCATAAAGCAAAACACATTAAGGTTTGGTGTCCAAGACCACC
7036 GROUP_22    AATAACAACTAGAGTTTATCACAAAGCTAAACATGTAAAAACCTGGTGTCCAAGACCACC
7037 GROUP_23    AATCACAACCAGAGTATACCATAAAGCCAAACACATAAAAGTCTGGTGTCCAAGACCACC
7038 GROUP_24    AATAACAACCAGAATATACCACAAGGCAAAACATGTTAAAGCATGGTGCCCAAGGCCACC
7039 GROUP_25    AGTGACGACAAGAGTCTATCAAAGCTAAACACATCAAAGCATGGTGCCCACGACCACCC
7040 GROUP_26    AATAACAACCAGAGTGTATCACAAAGCCAAACATGTCAAAGCCTGGTGCCCTAGACCACC
7041 GROUP_27    AGTGACCACAAGAATATACCATAAGGCAAAGCATGTTAAAGCTTGGTGCCC-AGACCACC
7042 GROUP_28    GATAACTACCAGGATATATCATAAAGCCAAGCATATCAAAGCTTGGTGCCCAAGACCACC
7043 GROUP_29    AGTAACCACTAGATATATCACAAAGCCAAACATATAAAAGCTTGGTGTCCGAGGCCGCC
7044 GROUP_30    AATTCAACCAGAATATATCACAAAGCCAAACATGTTAAAGCCTGGTGCCCAAGACCTCC
7045 GROUP_31    TATTTCAACTAGGGTATATCACAAAGCTAAACACGTCAAAGCTTGGTGCCCACGACCACC
7046 GROUP_32    AATTGCAACGCGGGTGTATCATAAGGCTAAACATGTAAAAGCTTGGTGCCCAAGGCCCCC
7047 GROUP_33    GATTACAACTAGAGTGTATCACAAACATGTAAAGGCTTGGTGCCCCGAGACCCCC
7048 GROUP_34    AATTACAACTAGAGTGTACCATAAAGCAAAGCATGTGAAGGCATGGTGTCCTAGACCCCC
7049 GROUP_35    GATAACAACTAGAATTTATCATAAGGCAAAACATGTAAAAGCCTGGTGTCCAAGACCCCC
7050 GROUP_36    CGTCGCAACAAGAATATATCACAAAGCAAAGCATGTTAAGGCTTGGTGTCCAAGACCTCC
7051 GROUP_37    CATCACTACTAGGGTTTATCACAAAGCAAAACATGTCAAGGCATGGTGTCCACGGCCCCC
7052 GROUP_38    CATCACTACTAGAGTGTACCACAAAGCAAAACATGTGAAAGCGTGGTGCCCGCGCCCTCC
7053 GROUP_39    AATTACAACTAGAGTGTACCACAAAGCAAAACATGTAAAGGCATGGTGCCCACGTCCTCC
7054 GROUP_40    CATTACCACAAGAATATATCACAAAGCAAAACATGTGAAAGCGTGGTGTCCACGACCCCC
7055 GROUP_41    AATCACAACTAGAGTATATCATAAAGCTAAACATATAAAAGCTTGGTGCCCACGACCACC
7056 GROUP_42    GGTTACAACTAGATCTATCATAAAGCTAAACATGTCAAAGCATGGTGTCCTAGACCCTCC
7057 GROUP_43    GGTCACAACTAGAGTTTACCAAAAGCTAAACATGTTAAAGCATGGTGTCCTAGACCCTCC
7058 GROUP_44    GGTTACTACTAGAATCTATCATAAGGCTAAACATGTTAAAGCTTGGTGTCCAAGACCTCC
7059 GROUP_45    AATCACAACTAGGATTTACCATAAAGCTAAACATGTTAAAGTCTGGTGTCCTAGACCCCC
7060 GROUP_46    AATTACAACCAGAGTTTACCACAAAGCTAAACATGTTAAGGTGTGGTGCCCGAGACCCCC
7061 GROUP_47    AGTGGTAACAAGGATATATCACAAAGCCAAACACACCAAAGCTTGGTGCCCAAGACCACC
```

FIG. D14 CONT'D

10.trace                                                                                     9/20/2007 5:05 PM

```
7062  GROUP_48   AATAGTAACAAGAATATATCACAAAGCTAAGCACACCAAAGCTTGGTGTCCAAGACCACC
7063  GROUP_49   TATAATGACAAGAATCTATCACAAGGCTAAACATGTCAAGGCATGGTGTCCACGCCCACC
7064  GROUP_50   TATCATGACAAGAATCTATCATAAAGCTAAACACGTCAAAGCATGGTGTCCGCGCCCACC
7065  GROUP_51   GATAATGACAAGGGTCTACCACAAAGCTAAACATGTCAAAGCATGGTGTCCGCGGCCACC
7066  GROUP_52   CATAATGACAAGGGTCTACCACAAGGCTAAACATGTCAAAGCGTGGTGTCCACGGCCACC
7067  GROUP_53   GATTGTGAGTCGCATTTACCACAAAGCCAAACATATAAAAGCATGGTGCCCACGCCCACC
7068  GROUP_54   TATCATTAGCCGTATATATCACAAGGCTAAACATATAAAGGCATGGTGTCCACGCCCACC
7069  GROUP_55   TATTGTATGCCGCATTTATCATAAAGCTAAACACATAAAGGCCTGGTGCCCGCGTCCACC
7070  GROUP_56   TATTGTGTGCCGCATTTACCACAAGGCCAAACATATAAAAGCATGGTGTCCTCGCCCACC
7071  GROUP_57   CATTGTCTGTCGCATTTACCACAAAGCCAAGCATATAAAAGCATGGTGTCCACGCCCACC
7072  GROUP_58   GATTACCAGTAGAATATACCATAAAGCAAAACATATCAGTGCCTGGGGCCCTAGACCACC
7073  GROUP_59   AATTACAGCTAGAGTCTACCACAAGGCCAAACATATTAGTGCATGGGGCCCAAGACCTCC
7074  GROUP_60   GATAACCAGTAGGATATTCCACAAGGCAAAGCATATTAGTGCATGGTGTCCAAGGGCCCC
7075  GROUP_61   AATAACCAGCAGAATATTCCATAAAGCAAAACATATTAGTGCGTGGTGTCCAAGAGCTCC
7076  GROUP_62   AATAACCAGCATAATATTCCACAAAGCTAAACATGTCAGTGCATGGTGCCCCAGACCTCC
7077  GROUP_63   GATAACCAGTAGGATTTATCACAAGGCTAAACATATCAGTGCATGGTGTCCAAGACCACC
7078  GROUP_64   TATAACTAGCAGAATATATCACAAGGCTAAACACATTAAAGCATGGTGCCCCAGGGCACC
7079  GROUP_65   AATCACCAGCAGAATATATCACAAAGCTAAACACATCAAAGCATGGTGTCCAAGAGCACC
7080  GROUP_66   CATAACTAGCAGGATTTACCACAAAGCCAAACATGTCAGTGCATGGTGCCCTCGTCCTCC
7081  GROUP_67   CATAACCAGTAGAATATATCACAAAGCTAAACACATCAGTGCTTGGTGTCCACGACCTCC
7082  GROUP_68   CATAACAAGTAGGATTTATCACAAAGCCAAACATGTCAGAGCATGGTGTCCTAGACCCCC
7083  GROUP_69   AATTGATTCAAGAATATACCTGAAAGCAAAGCA-ATTAAAGCTTGGTGTCCTAGACCCCC
7084  GROUP_70   GATCGACTCCATGGTATATCTAAAAGCTAAACACATCAAGGCATGGTGTCCCAGACCTCC
7085  SUMMARY    XXT-XXXXXXXX-XT-TXXCX-AA-GCXAAXCA-XX-XX-XX-TGGXG-CC--G-XC-CX
7086
7087  GROUP_1    TAGAGCTGTCCCTTACACA.CATAGTCATGTGACTAATTATATGC.CAGAAA...CAGGT
7088  GROUP_2    TAGAGCTGTTCCTTACACA.CATAGTCGTGTAACTAATTATGTAC.CAAAAA...CAGGT
7089  GROUP_3    AAGAGCAGTACCTTACACA.CATACACACTCAACAAATTATAAAC.CTCAAG...AAGGT
7090  GROUP_4    AAGAGCGGTGCCTTATACA.CACACACGCTCAACCAACTATGTGC.CACAAG...ATGGT
7091  GROUP_5    AAGGGCTGTGCCTTATACA.CATGCTCACGTCACCAATTATAAAC.CACAAG...ATGGT
7092  GROUP_6    TAGAGCAGTCCCTTACACA.CACAGCTACGTAACTACAAGATTGCTGG...AAAA.
7093  GROUP_7    TAGGGCTGTTCCATACACA.CATAGTTATGTCACTAACTATAAAATTACAGG...ACAG.
7094  GROUP_8    CAGAGCAGTCCCTTACACA.CACAGCAATGTTACAAATTACAAAG.TACGGG...ACGGT
7095  GROUP_9    CAGAGCTGTACCATATACA.CATGCCCATTCCACAAATTACAAAC.CACATG...GCAAA
7096  GROUP_10   TCGGGCTGTGCCGTACACA.CATAGTCACTCTACAAATTACAAAC.CACATG...AGGGT
7097  GROUP_11   TAGAGCTGTACCATACACA.ACTGTAAACTCAACCAATTATATGC.CTCATA...CTGGT
7098  GROUP_12   TAGAGCTGTACCATACACA.GCAGTAGATTCAACAAATTACAAAC.CTATGA...GAGGG
7099  GROUP_13   -AGAGCTGT-CCATATAAA.TATGTTGA-TTCAATAATTATGCAG.CCAGTG...ATA-T
7100  GROUP_14   AAG-GTTGTCCCATACAAG.TATGTTGGCCTAACTAATTACACAC.TTAAAG...AA--A
7101  GROUP_15   TAGAGCAGTTCCATACAGG-TATG-TGGATCAACAAACTACAAAC.CTGATG...AAAAT
7102  GROUP_16   TAGAGCTGTTCCATATAGA.TATGTTGGATCAACAAACTACAAAC.CTGATC...AAGGA
7103  GROUP_17   TAGAGCTGTAGAATATACT.CACACTCATGTAACCAATTACAAAC.CACAGG...AAGGA
7104  GROUP_18   TAGAGCTGTAGAGTATACA.TACACCCATGTAACAAACTACAAAC.CACATT...CTGGT
7105  GROUP_19   TAGAGCTGTGGAATACACC.CATACTCATGTTACAAATTATAAAT.CAACAA...CTCGT
7106  GROUP_20   CAGAGCTGTTGAGTATACA.CATACTCACGTGACCAATTATAAGC.ATCAGA...CTCGT
7107  GROUP_21   TAGGGCAGTTGAATACACA.CACACTCATGTAACAACTACAAAC.ATGCAA...CACGT
7108  GROUP_22   AAGAGCTGTTGAGTACACA.CACACACATGTTACTAACTACAAAG.TTAGGG...GTAAA
7109  GROUP_23   AAGAGCTGTTGAATACACA.CACACCCATGTCACTAACTACAAGA.AAAGTG...ATGCT
7110  GROUP_24   GAGAGCTGTGGAGTACACA.CATACACATGTAACTAACTACAAGC.CTAAGG...AAGGA
7111  GROUP_25   TAGGGCTGTTGAATACACA.CACACACATGTCACAAATTACAAGA.AGACTG...ATGGC
7112  GROUP_26   ACGGGCTATCGAGTACACA.CATACACATGTTACTAATTATAAAA.TAAAAG...ATAGA
7113  GROUP_27   GAGGGCCGTTGAATACACA.CATACACA-GTAACCAATTACAAAA.TTGCAA...AT-A
7114  GROUP_28   CAGAGCTGTTGAATACACA.CCTACATGTCACAAATTATAAAA.GAGAAG...GAAAG
7115  GROUP_29   CAGGGCTGTTGAATACACA.TTTAGACGTGTAACAAATTACAAAA.GAGATG...GACAA
7116  GROUP_30   TAGGGCAGTTGAGTATATA.CATACACATGTCACAAATTACAAGC.CAAGCA...CAGGC
7117  GROUP_31   TAGGGCAGTTGAATATACA.CATACACATGTTACAAATTACAAAC.CAAGCA...CAGGT
7118  GROUP_32   TAGAGCAGTTGAATACATA.CACACACATGTCACAATATAGAC.CAGAAA...CAGGT
7119  GROUP_33   TAGAGCAGTGGAATATACA.CACACACATGTCACAAATTACAAAC.CACAAG...ATGGT
7120  GROUP_34   TAGAGCAGTTGAATATACT.CACACACATGTCACAAATTACAAAC.CACAAG...AAGGT
7121  GROUP_35   AAGGGCAGTTGAATATAGA.CATACATGTTAACAATTACAAAC.CAGACC...AAGGG
7122  GROUP_36   AAGGGCAGTTGAATATAGA.CACACACATGTAAACAACTATAGAC.CAGATG...ATGGA
7123  GROUP_37   AAGAGCTGTTGGATATACA.CATACAAATGTCACCAATTATAAAC.CATCCA...AAGGA
7124  GROUP_38   AAGAGCTGTTGGATACACA.CATACGCATGTCACTAATTACAAAC.CATCTG...AAGGG
7125  GROUP_39   AAGAGCTGTTGGATATACA.CACACACATGTGACAAACTACAAAC.CATCTG...TAGGG
7126  GROUP_40   GAGGGCTGTGGGTTATACA.CACACACATGTTACCAACTACAAGC.CATCAC...AGGGA
```

FIG. D14 CONT'D 10.trace                                                                                                        9/20/2007 5:05 PM

```
7127 GROUP_41    CAGAGCCGTGGAATATACC.CACACTCATGTGACTAATTATAAAC.CCCAGA...CAGGT
7128 GROUP_42    CAGAGCTGTTGAATATACT.AATGTGCATGTTACAAACTACAAAC.CAGGGA..CAGGA
7129 GROUP_43    CAGGGCTGTGGAGTACACC.AATGTGCATGTCACAAATTACAAAC.CAAAAG...CAGGA
7130 GROUP_44    TAGGGCAGTAGAATATACA.AATGCACATGTGACCAATTATAAAC.CCACTG...ATGGA
7131 GROUP_45    CAGAGCAGTGGAATATACT.AATGTGCATTTGACCAATTACAAGC.CCAAAG...ATAGT
7132 GROUP_46    TAGAGCAGTTGAATACACA.AATGTGCATCTCACAAATTATAAAC.CCAACA...ATG..
7133 GROUP_47    CAGAGCTGTTCAATACTCA.CATACACATACCACCAACTACAAAT.TGAGTT...CAGAA
7134 GROUP_48    CAGGGCTGTTCAGTACACA.CATACACATGTAACTAATTATAAAT.TAGAAA...CAGAT
7135 GROUP_49    CAGAGCGCTTGAGTATACT.CGTGCTCACCGCACTAATTTTAAAA.TTGAGG...ATAGG
7136 GROUP_50    CAGAGCACTTGAATATACT.CGCGCTCACCGTACTAATTTCAAAG.TTGAAG...ACAGA
7137 GROUP_51    CAGAGCACTTGAATATACA.CGCGCTCACCGTACTAATTTCAAAA.TTGAAG...GTGAA
7138 GROUP_52    TAGGGCGCTTGAGTATACC.CGTGCTCATCGCACCAATTTTAAAA.TTGATG...GCAGG
7139 GROUP_53    ACGAGCTGTGCCTTATCAA.CACACTCACTCCACCAACTATGTGC.CACAAA...ATGGA
7140 GROUP_54    AAGAGCCGTACCTTATCAG.CACACACACTCCACCAATTATGTAC.CAACAG...ATGGG
7141 GROUP_55    AAGGGCCGTTCCTTACCAA.CACACACATTCCACTAATTATATAC.CATACA...AAGGT
7142 GROUP_56    AAGGGCTGTGCCTATCAA.CACACACCTCAACCAATTACAC.CATCCA...ATGGT
7143 GROUP_57    AAGGGCTGTTCCTTATCAA.TTCACACATTCTACTAATTACATAC.CAGATA...GTGGT
7144 GROUP_58    AAGAGCTGTACCATACCAG.CATATACACAATCCAAATTACAAGA.CAAGTA......AT
7145 GROUP_59    TAGAGCTGTACCTTATCAG.CACATATATAACCCTAATTATAAAA.CTGAAG......AA
7146 GROUP_60    AAGAGCAGTGCCTTATCAA.CACACTAAGAGCACAAACTTAGTGC.CAAGGA...CAGGT
7147 GROUP_61    AAGAGCAGTGCCCTACCAG.CACACCAGAAGTACAAACTTAGTAC.CAAAGG...AAGGT
7148 GROUP_62    ACGCGCTGTAGCTTATCAA.CATACATACAGTCCAAACTTTGTGC.CTCAGG...AAGGT
7149 GROUP_63    AAGAGCAGTTGCATATCAA.CACACATATAGCCCAAATTTTGTAC.CGCAAA...CAGGA
7150 GROUP_64    CAGAGCAGTCCCATATCAA.CATATTTATAATCCAAATTACAAG.CTACTCAACCTGAG
7151 GROUP_65    TAGAGCAGTCCCATACCAA.CATACCTACAGCCCAAATTTCAAAA.ACACTG...ATGAA
7152 GROUP_66    TCGTGCTGTAGCCTACCAA.CACACATACAGTACAAACTTCGTTC.CAAAAGAGGGATTT
7153 GROUP_67    CCGAGCAGTAGCTTACCAA.CACACATACAGTACAAATTTTGTTC.CTAGCGGAGGTCTT
7154 GROUP_68    CAGAGCAGTAGCCTACCAA.TCAACATACCACAAATTTTGTTC.CACAAGACGGATC
7155 GROUP_69    CAGAGCAGTTACGTATAAC.CATATATACAACCCCAATTATGTTA.GAGAGG......GA
7156 GROUP_70    AAGAGCAGTCACATATAAC.CATACATATAATCCAAATTATGTTA.GGGCTG......AT
7157 SUMMARY     -XG-GXXXT-XXXTAXXXX-XXXX-XXX-XXXXXXAAXTXXXXXXXXXXXXXXXXX---
7158
7159 GROUP_1     GACG......TGACAACAG...CCATAGTCCGCAGAA......ACACTATAACAACTG..
7160 GROUP_2     GATG......TGACAACAG...CTATAGTTCCTAGAG......CTAGCATGAAAACTG..
7161 GROUP_3     GAAG......TCCAGATTT...TCCTCAAAGAGAGAG......CCAGCCTAACAACAG..
7162 GROUP_4     GAAG......TTAAGATCT...TCCTCAAAGAGAGAG......CTAGTTTAACCACAG..
7163 GROUP_5     GATG......TACAGATCT...TCTTAAAACCCAGAC......CCAGCCTAACAACAT..
7164 GROUP_6     GAAC......CTGAAATTT...TCTTAAAACCAAGAA......TGAATATTACAACAG..
7165 GROUP_7     GAGA......CTGAAATTT...TCTTAAAACCTAGAG......CAACTATCAAGACAG..
7166 GROUP_8     GAAC......CAACACTCT...TTATAAAA-CAAGAG......AGAATCTTACCACAG..
7167 GROUP_9     GAAT......TACAAATAT...TTATTAGGTCTAGAGATGATCCCAAAGTAGTAACTG..
7168 GROUP_10    GATG......TAAAGATTT...TCATTAGACCCAGAGATGATCCAAAGTTTGTAACTG..
7169 GROUP_11    GATC......TGCAAATTT...TCATTAAACCTAGAACAGATCCAAAAGTAGTCAATG..
7170 GROUP_12    GATG......TACAAATCT...TTATTAAAGAGAGAGCAAGCCCAAAAGTAGTTACTT..
7171 GROUP_13    ...G......TTGACAT-T...TTATA-AA-CAAG-......-A-A--TT--AAACAG..
7172 GROUP_14    ...G......AT.-CAG.....TTGTGGAA-C-AGA......C--AGC-TAATGACAG..
7173 GROUP_15    GAAG......TTACAATCT...TTGTTAAACACAGGGATAATCCAAAGATTATCACAG..
7174 GROUP_16    GAAG......TTGCAATTT...TCATTGAGCATAGAGAAAATCCAAAATTCATTACAG..
7175 GROUP_17    CAGG......TGAAAACAG...CTGTCAAGGCTAGGAAAACAATTAAAACAGC-......
7176 GROUP_18    GATG......TGCAAACAG...CTATTAGACCAAGAGCAACAATTAAGACTGC-......
7177 GROUP_19    GAAG......TGAAGACAG...CTATTAGACCAAGAGCAACAATCAAGACTGC-......
7178 GROUP_20    GAAG......TCAAGACAG...CAATTGAACCTAGAAGAGGAATTAAAACAGT-......
7179 GROUP_21    GAAC......TTAAGACTG...CAATTAGGCCCAGGAAAACAATCACAACAGC-......
7180 GROUP_22    ACTG......AGAAGACTG...CAATCAAACACAGCAAAGATCACAATGGC-......
7181 GROUP_23    ACTG......AGAAGACTG...CAATTGCAACTAGACCAAAGATCACAGTGGC-......
7182 GROUP_24    AGAG......AGAAAACTG...CCATAGTACCCAGAGCAAGGATTACAATGGC-......
7183 GROUP_25    ACAG......AAAAGACAG...CAATTGAATACAGAAGGGACATTAAAACAGT-......
7184 GROUP_26    CAAG......AAGAAACAG...CAATTAAATATAGAAGGGACATTAAAATTGTTAAGA..
7185 GROUP_27    GA-G......TCACTTCTG...CAGTTGAGTCCAGAAGAACAATTGTCACAGTT......
7186 GROUP_28    GAGG......TAGAAACAG...CCATAGTATCTAGGAGGGATATCAAAATTGTCAATG..
7187 GROUP_29    CAAG......TTGAGATTG...CTATTGAGCCAGAGAGATGTTAAGTTTGTAAATG..
7188 GROUP_30    GATT......ATGCCACAG...TTATACCAGTTAGAGACAATGTTAGGGCAGTAAAGA..
7189 GROUP_31    GATT......ACACCACAG...CCATACAAACCAGAGAGCATGTTAGAGCAGTCAAAA..
7190 GROUP_32    GAGG......CTCAAACGG...TTATACCTGTTAGAGCAGATGTTAGAACAATTAGAA..
7191 GROUP_33    GATG......TAACTACAG...TTATTCCAACTAGAGAAAATGTTAGAGCTATAGTAA..
```

FIG. D14 CONT'D

```
10.trace                                                                                        9/20/2007 5:05 PM 7192 GROUP_34    GACG......TAACTACAG...TCATCCCAACTAGG.........AGATCAATAGTGA..
7193 GROUP_35    GAAG......TAACCACTA...TGATTCCAACTAGAACCAACATAAGAACCATCGTAA..
7194 GROUP_36    GAAG......CAGCCATAA...CAATCCCCATTAGAACTGATATACGAGCAATCAGAA..
7195 GROUP_37    GAAT......ACACACCAC...CCGTTCCGTCACGTAACAGCCCCAGAGATATTGTCA..
7196 GROUP_38    GAGT......ACAAGCCAC...CTGTCCCAGTTAGGAATAGCCCCAGAGACATTGTCA..
7197 GROUP_39    GATT......ACACACTAC...CTATCCCAACAAGAGCCAACCCTAGACAAATTTTGA..
7198 GROUP_40    GATT......ACAGTGTTG...TTATTCCAGTTAGAGAGAGTCCCAGACAGATTCTTA..
7199 GROUP_41    GAAG......TCACTCTTC...CAATTGAAATAAGAGATAACCCTAGACATATAAAGA..
7200 GROUP_42    GATG......TTGCAGTCT...CCATTGTACCTAGAGCAAATGTTAGGGAAATTAGAA..
7201 GROUP_43    GCAGA.....GATTGTGGCTT...CTGTCAGACCTAGAGACAATGTTAGACAAGTAAGAA..
7202 GROUP_44    GAAG......TTACTACTG...CCATTAGGCATAGAGATAATGTTAGAGCCATCCAAA..
7203 GROUP_45    GAAAAACAAGTTACCACTT...TCATCAAACCTAGAGCTAACTTAAGAGAGATTAGAA..
7204 GROUP_46    .......AGGTTACCACTT...TTATCAAACCTAGAGAAAATCTAAGGGATATTAGAA..
7205 GROUP_47    GTAC......ACAATGATGTGGCTATAAGACCTAGAACAAATCTAACAACTGT-......
7206 GROUP_48    GTCC......ACACTAGTGTAGCCATAAAACCTAGAACAAGTCTAACAAATGT-......
7207 GROUP_49    AGTA......TTCAGACAG...CAATTGTGACCAGACCAATTATCACTACAGC-......
7208 GROUP_50    GACA......TTAAAACAG...GAATCACATCCAGAGCAATTATTACAACAGC-......
7209 GROUP_51    AATG......TCAAATCAA...GGGTTGCACATAGACCTGCAGTGATAACAGC-......
7210 GROUP_52    GAAG......TTAAATCAA...GGGTTGAACACAGAGCTAGGGTGACGACAGC-......
7211 GROUP_53    GAGG......TCGCA...ACTCAAATCAAAACCAGAGCCAATCTTTTCACCCTCAAAT..
7212 GROUP_54    GAAG......TAGCA...ACTCAAATCAAAACCAGACGAGATGTTTACACTGTTACCA..
7213 GROUP_55    GAGA......TCACA...ACCCAAATTAAAACCAGACCTAATGTCTTCACTGT-......
7214 GROUP_56    GAGG......CCACA...ACTCAGATTAAAACCAGACCTGATGTTTTTACCGTTACAA..
7215 GROUP_57    GAGG......TAACA...ACACAAATCAAACCCAGAACCAATGTTTTTACTATTACAT..
7216 GROUP_58    GGAG......TTCCAGACAATAGAGTCAAACTCAGAGAGACACTCACCACAGT-......
7217 GROUP_59    GGAA......CTCCAGACACCAAAGTGGCAATTAGAGCTAATATTAAAACTGT-......
7218 GROUP_60    GAAA......TTACA...ACTCATATCAGATTCAGAAACACTGTCAAAGATCTAACATAC
7219 GROUP_61    GATA......TTAAA...ACTCATATTAAATTTAGGAATACTGTTAAAGATTTGGCATAT
7220 GROUP_62    GATG......TTGAG...ACTCATATTAAATTTAGAACAGATGTTAAACAGATCACAA..
7221 GROUP_63    ACAG......TTGAA...ACTCACATTAAGTTCAGACCTGATGTTAAAGATGTAACAT..
7222 GROUP_64    ACTA......TACCAGATACTCATATTGGAATTAGAAGGGATATAAAGTACATTAAAA..
7223 GROUP_65    TCTA......TACCAGATACACAAATTAAAATCAGAGATAATATCAGGCAGGTTAGAA..
7224 GROUP_66    GAAG......GCTTGAAAACTCAGATTAAAACTAGGGCAGACATCAAACTTGTGAACT..
7225 GROUP_67    ACAA......ACCTAAGAACCCAAATTAAAACCAGAGATAACATTAAAATTGTAAACT..
7226 GROUP_68    AATT......CCATTAAAACCAAAATCAAAATCAGAGAGACATTAAAGAGGTCAGCA..
7227 GROUP_69    GTAA......CACCAGAAACTAAGGT-AAATATAGAGCTGAAGTCACAACCATT......
7228 GROUP_70    GAAA......CAGCC...ACAAAAGTCCAAACTAGAGCAAATGTCACAACAGT-......
7229 SUMMARY     XX-XXXXXXXXXX-XXX-XXXXXXXT--XX-X-XG-XXXXXX---X---X--X-XXXXXX
7230
7231 GROUP_1     ....C-..............
7232 GROUP_2     ....T-..............
7233 GROUP_3     ....T-..............
7234 GROUP_4     ....C-..............
7235 GROUP_5     ....T-..............
7236 GROUP_6     ....C-..............
7237 GROUP_7     ....C-..............
7238 GROUP_8     ....C-..............
7239 GROUP_9     ....C-..............
7240 GROUP_10    ....C-..............
7241 GROUP_11    ....T-..............
7242 GROUP_12    ....T-..............
7243 GROUP_13    ....C-..............
7244 GROUP_14    ....CT..............
7245 GROUP_15    ....C-..............
7246 GROUP_16    ....C-..............
7247 GROUP_17    ....................
7248 GROUP_18    ....................
7249 GROUP_19    ....................
7250 GROUP_20    ....................
7251 GROUP_21    ....................
7252 GROUP_22    ....................
7253 GROUP_23    ....................
7254 GROUP_24    ....................
7255 GROUP_25    ....................
7256 GROUP_26    ....ATGT-...........
```

FIG. D14 CONT'D

```
10.trace                                                              9/20/2007 5:05 PM 7257 GROUP_27       .....................
7258 GROUP_28       ....C-...............
7259 GROUP_29       ....C-...............
7260 GROUP_30       ....ATGT-............
7261 GROUP_31       ....ATGT-............
7262 GROUP_32       ....ATGT-............
7263 GROUP_33       ....ATGT-............
7264 GROUP_34       ....ATGT-............
7265 GROUP_35       ....ATGT-............
7266 GROUP_36       ....CAGT-............
7267 GROUP_37       ....CAGT-............
7268 GROUP_38       ....CAGT-............
7269 GROUP_39       ....ATGT-............
7270 GROUP_40       ....ATGT-............
7271 GROUP_41       ....ATGT-............
7272 GROUP_42       ....ACTT-............
7273 GROUP_43       ....ATTA-............
7274 GROUP_44       ....ATTT-............
7275 GROUP_45       ....CATTT............
7276 GROUP_46       ....ATTT-............
7277 GROUP_47       .....................
7278 GROUP_48       .....................
7279 GROUP_49       .....................
7280 GROUP_50       .....................
7281 GROUP_51       .....................
7282 GROUP_52       .....................
7283 GROUP_53       ....CAGC-............
7284 GROUP_54       ....CTGC-............
7285 GROUP_55       .....................
7286 GROUP_56       ....ACGT-............
7287 GROUP_57       ....CTGC-............
7288 GROUP_58       .....................
7289 GROUP_59       .....................
7290 GROUP_60       CCCACAGAAATGACGAATGT
7291 GROUP_61       CCTCCAGAATTAGCAAACCTT
7292 GROUP_62       ....CAGT-............
7293 GROUP_63       ....CAGTAATGACAGC-...
7294 GROUP_64       ....CAGC-............
7295 GROUP_65       ....CAGT-............
7296 GROUP_66       .....T-..............
7297 GROUP_67       .....T-..............
7298 GROUP_68       .....ACTA-...........
7299 GROUP_69       .....................
7300 GROUP_70       .....................
7301 SUMMARY        XXXXX--X--XXXXXXX-XX-
7302
7303
```

FIG. D14 CONT'D

APPLICATION PACKAGE TO AUTOMATICALLY IDENTIFY SOME SINGLE STRANDED RNA VIRUSES FROM CHARACTERISTIC RESIDUES OF CAPSID PROTEIN OR NUCLEOTIDE SEQUENCES

RELATED APPLICATIONS

This application claims priority to U.S. Provisional Patent Application Ser. No. 60/846,206, filed 21 Sep. 2006 (Sep. 21, 2006).

Sequence Listing

The specification includes a list of sequences including sequence ID numbers

Computer Code Listing

The specification includes a listing of a representative program for implementing the methods of this invention.

GOVERNMENTAL INTEREST

Governmental entities may have certain rights in and to the contents of this application due to funding from the Texas Learning and Computational Center (TLCC), grants from the National Aeronautics and Space Administration Office of Exploratory Research (NNJ04HF43G) and the Department of Homeland Security Advanced Research Projects Agency (W81XWH-05-2-0040).

BACKGROUND OF THE INVENTION

1. Field of the Invention

The present invention relates to a software product that uses unique characterizing residues to automatically identify strains of partial or complete capsid sequences of picorna viruses and calici viruses, two of the most highly diverse single stranded RNA (ssRNA) virus families.

More particularly, the present invention relates to a computer program product stored on a computer readable medium for predicting strains of some ssRNA viruses from their limited sequence data, said computer product including a graphical user interface (GUI) code operable to carry out all data input-output (I/O) operations; storage codes operable to store virus sequence databases in the form of multiple data arrays containing information about phylogenetic trees, sequence groups and characteristic residues of these groups; sequence comparison codes operable to compare input virus sequences with the stored database sequences on a residue-by-residue basis; identification codes operable to identify the strains of input virus sequences based on comparisons (iii) and subsequent decision making algorithms.

2. Description of the Related Art

Currently, no equipments or kits can unambiguously distinguish among a particularly important class of viruses that cause alarming epidemic outbreaks all over the world and consequently, pose high bio-terrorism related threats. This class comprises of the single-stranded RNA (ssRNA) viruses which include diverse virus families ranging from those that cause flu (including the cruise-ship flu and the bird flu) to the AIDS causing viruses. The main difficulty in distinguishing among these viruses and detecting them lies in their molecular details. As the name suggests, each of these viruses consists of a single genomic RNA strand enclosed within a protein shell called the capsid. This encapsidated RNA strand undergoes rapid sequence mutations to generate a large number of virus strains that are often associated with different epidemic outbreaks. Sequence differences among these strains are so subtle and intricate that they appear to be almost random. There are no reliable methods to unambiguously distinguish among the strains by systematically tracking these variations. Most often, the capsid sequences show the maximum variations relative to the other genomic regions for a given ssRNA virus families. This is mainly because the capsid residues undergo most mutations in response to host immunity. Consequently, capsid sequences provide the best regions to identify strains as they truly represent the diversity of ssRNA virus families. Thus, any reliable method to uniquely identify the ssRNA virus strains would be based on capsid sequences even though the problem of strain identification on the basis of these sequences may appear intractable.

Two diagnostic methods are most widely used to detect ssRNA viruses. One of them relies on immuno-based techniques while the other is based on reverse transcriptase polymerase chain reaction (RT-PCR) assays. The immuno-based assays distinguish strains on the basis of epitope differences in the capsid protein while the RT-PCR based assays use nucleotide primers to amplify differences in the viral genome. However, experimental constraints limit the ability of both of these assays in distinguishing among the strains. Most often, these methods are useful in detecting only significant sequence differences but they fail to detect subtle sequence variations among the strains which occurs, for example, when the sequence identity falls to approximately 10% or below as in the case of noroviruses Accurate strain recognition in uncharacterized target capsid sequences is essential in understanding the epidemiology and diagnostics of these viruses and for efficient vaccine development. Experimental techniques to detect ssRNA virus strains are inadequate when the number of strains are very large as is the case with picornaviruses and caliciviruses, or, the strains are non-cultivable like those of the human caliciviruses. Additionally, existing homology comparison based computational methods to recognize strains are of limited use as they most often rely on similarity scores between target sequences and sequences of homology matched reference strains. Methods based on such scores are often time consuming and ambiguous especially if only partial target sequences are available or, if different ssRNA virus families are jointly analyzed. In such cases, knowledge of residues that uniquely distinguish among known reference strains is critical for rapid and unambiguous strain recognition of target capsid sequences. Conventional sequence comparisons are unable to identify such capsid residues due to high sequence divergence among the ssRNA virus reference strains. Consequently, automated general methods to predict strains from sequence data of such viruses on the basis of strain distinguishing residues are not available.

One of the main challenges, therefore, in making efficient detection systems for ssRNA viruses is to devise methods to unambiguously distinguish subtle sequence variations among the different ssRNA virus strains using stain distinguishing residues. This challenge becomes significantly tough when only partial sequences of these viruses are available. The only feasible way to address this problem is through computational techniques. However, all such known techniques are based on criteria that allow them to distinguish only significantly different strains. In contrast, the intellectual property described here is a software product based on different computational criteria. The product successfully demonstrates a way to distinguish among very closely related virus strains of two important ssRNA virus families. The only requirements of the software are the availability of accurately known (complete or partial) genomic or protein capsid sequences of these viruses. Given the rapidly improving sequencing techniques, this should not be a major problem, and, it should therefore be possible to design and manufacture efficient ssRNA virus detection systems based on the described software. It is anticipated that the software will reduce both time and costs in identifying closely related ssRNA viruses from their sequences by substantially reducing the throughput time.

Most non-bacterial epidemic outbreaks are caused by single stranded RNA (ssRNA) viruses. Typically, these viruses undergo rapid genetic mutations that result in a large and dynamic population diversity seen as different virus strains utilizing multiple hosts [1]. Caliciviruses and picornaviruses are two of the most highly divergent ssRNA virus families each containing several hundred reference strains showing very low sequence identity even within families [2-4]. The software determines relationships among the strains using a unique algorithm in contrast to existing methods. Relationships among the strains are usually inferred through conventional homology based comparisons using complete capsid sequences or other genomic regions. These comparisons seek to identify clusters of similar sequences that comprise the major sequence groups (genogroups or genera) and their sub-groups leading to various diagnostics [5-16] and classification schemes for these viruses.

The four calicivirus genera (noroviruses, sapoviruses, lagoviruses and vesiviruses) [3, 4, 17] and the nine picornavirus genera (apthoviruses, cardioviruses, enteroviruses, erboviruses, hepatoviruses, kobuviruses, parechoviruses, rhinoviruses and teschoviruses) [2] are classified using such schemes [2, 4]. Further divisions of these genera reflect more detailed sequence relatedness among these viruses. For example, among the diverse caliciviruses [17], noroviruses are divided into two genogroups GI and GII [18-20] each of which contains seven sequence clusters (GI.1-GI.7 and GII.1-GII.7) [4], sapovirus sequences are grouped into 2-5 genogroups each of which contains several clusters [2]-23], vesivirus sequences are known to contain at least 40 immune response related antigenic serotypes and lagovirus sequences cluster into proposed sero-specific groups [24]. Similarly, classification of the 9 picornavirus genera into species, each of which consists of several serotypes [2, 25] reflects finer relations among these virus sequences (Table 1).

TABLE 1

Species and Serotypes of All Picornavirus Genera

| Genera | Species (Abbreviation) [Number of serotypes] |
|---|---|
| Aphthoviruses | Foot-and-mouth disease virus (FMDV) [7] |
| | Equine rhinitis A virus (ERAV) [1] |
| Cardioviruses | Encephalomyocarditis virus (EMCV) [1] |
| | Theilovirus [2 or 3] |
| Enteroviruses | Human enterovirus A (HEV-A) [12] |
| | Human enterovirus B (HEV-B) [36] |
| | Human enterovirus C (HEV-C) [11] |
| | Human enterovirus D (HEV-D) [2] |
| | Bovine enterovirus (BEV) [2] |
| | Porcine enterovirus A (PEV-A) [2] |
| | Porcine enterovirus B (PEV-B) [2] |
| Hepatoviruses | Hepatitis A virus (HAV) [1] |
| Kobuviruses | Aichi kobuviruses (AKV) [1] |
| | Bovine kobuviruses (BKV) [1] |
| Parechoviruses | Human parechoviruses (HPeV) [3] |
| Cardioviruses | Encephalomyocarditis virus (EMCV) [1] |
| | Ljungan viruses [1] |
| Rhinoviruses | Human rhinovirus A (HRV-A) [75] |
| | Human rhinovirus B (HRV-B) [25] |
| Teschoviruses | Porcine Teschoviruses (PTEV) [11] |

Abbreviations for species are shown within parentheses and the number of serotypes for given species are shown within square brackets.

The available crystal structures of several calici and picornavirus capsids [26-32] further help understand such sequence relationships including those among the four subunits (VP1-VP4) of the picornavirus capsids [2].

Strain and genogroup predictions in uncharacterized target sequences of calici and picornaviruses depend critically on their sequence relationships. Most often, such predictions use conventional homology comparisons between the target and a large number of known reference sequences. However, there are difficulties in these approaches when applied to caliciviruses. Most prediction methods for these viruses are based on sequence similarity cut-off values that are arbitrarily derived from the homology based sequence comparisons [19]. Although recent reports indicate statistically significant estimation of such cut-off values in distinguishing the major norovirus genogroups [33], no uniform criteria exist to accurately estimate these values for the other caliciviruses. In addition, homology based sequence similarity cut-off values are even more difficult to estimate when different virus genera need to be analyzed together in situations for example, where the genus of the target sequences may not be known. These difficulties are compounded while determining the strains of partial sequences mainly because experimental considerations usually restrict these partial sequences to smaller and relatively more conserved regions [15, 19, 34-37] whose comparisons may often introduce ambiguities in strain identification.

Even if complete sequences of target virus capsids are compared [33, 38], strain determination using homology based similarity scores is still computationally challenging. This is because comparisons of a large number of complete capsid sequences demands significant computation time which increases exponentially with increasing sequence lengths and the number of sequences that are compared together. Such limitations may severely reduce the number of usable reference capsid sequences thereby creating major computational bottlenecks.

Recent methods to genotype sequences belonging to certain virus families [39] suggest ways to reduce such bottlenecks. These methods efficiently align sliding windows of target sequences with databases of reference sequences and genotype the target sequences essentially using highest overall alignment scores. However, such methods, primarily designed to detect recombination breakpoints within virus genomes, critically depend on parameters such as window sizes and choice of reference sequences. Smaller windows may significantly increase the computation time while larger windows may overlook fine sequence variations. Similarly, incorrect choices of reference sequences may introduce possible error inducing biases. Time consuming repetitive runs using different trial settings of these parameters may be necessary to correctly genotype virus strains in such cases [39].

Thus, strain recognition methods using sequence identity based scores have not been easily amenable to reliable and robust automation across ssRNA virus families. Based on earlier analysis of noroviruses [40], we describe here the generalized implementation of a residue-wise comparison based approach to automate strain predictions in complete and partial amino acid capsid sequences of calici and picornaviruses.

SUMMARY OF THE INVENTION

The present invention provides a software product implemented on a computer or a distributed computer environment such as an intranet (e.g., secure institution, corporate, etc. network) or an internet (e.g., the world wide web) that uses unique characterizing residues to automatically identify strains of partial or complete sequences of pathogens or non-pathogens, where the sequences can be nucleic acid sequence (DNA, RNA, DNA/RNA hybrids, RNA/protein hybrids, DNA/protein hybrids or any other biomolecules that include a sequencable nucleotide moiety), proteins, or any other biomolecule that includes a sequence of monomers that is unique to an organism or virus, e.g., a pathogen. These residues are possible adaptive mutation sites in the pathogens considered.

The present invention provides a software product implemented on a computer or a distributed computer environment such as an intranet (e.g., secure institution, corporate, etc. network) or an internet (e.g., the world wide web) that uses unique characterizing residues to automatically identify strains of partial or complete capsid sequences of picorna and caliciviruses, two of the most highly diverse ssRNA virus families.

The present invention also provides a computer program product stored on a computer readable medium for predicting strains of some single stranded RNA viruses from their limited sequence data, the computer product including a graphical user interface (GUI) code operable to carry out all data input-output (I/O) operations; a storage code operable to store pathogen sequences such as viral sequences, in one sequence database or a plurality of sequence database in the form of multiple data arrays containing information about phylogenetic trees, sequence groups and characteristic residues of these groups; a sequence comparison code operable to compare input sequences such as viral sequences with the stored database sequences on a residue-by-residue basis; an identification code operable to identify the strains of the input sequences such as viral sequences based on comparisons (iii) and subsequent decision making algorithms.

The present invention also provides a method of evaluating comparisons including the steps of identifying tree branches containing maximum number of characteristic residue matches obtained from comparisons; identifying tree branches to carry out further searches after identifying maximally matching tree branches; identifying tree branches to carry out further searches in case there are no unique maximally matching tree branches; and confirming that the chosen maximally matching tree branches do not lead to ambiguous comparisons.

BRIEF DESCRIPTION OF DRAWINGS

The invention can be better understood with reference to the following detailed description together with the appended illustrative drawings in which like elements are numbered the same.

Figures for the Capsid Embodiment

FIG. 2B depict detailed partition-wise mapping of characteristic residue locations of aligned target sequence (norovirus "Seacroft"; NCBI accession no. AJ277620) on to reference Norwalk virus (PDB ID: 1IHM) sequence. The last residue in each line is numbered and every tenth residue is marked using the V symbol. The symbols ●,◆,▮,●,and ⬢map all of such residues from partitions 1, 2, 3, 4, 5 and 6 respectively of FIG. 2A where these symbols are shown near the edge of each partition.

FIG. 3 depicts a sample output from 'overall classification' button in GUI: Output summary of partition-wise matches of characteristic residues for a typical norovirus query sequence with output line numbers shown within parentheses in red. Details of the query sequence such as its number, input file, organism and sequence accession number are shown in lines 1-3. The partition-wise search results are shown in line 4. Each arrow indicates search progression to partition 'Pn' shown in blue, where n is the partition number. Line 5 shows the matched sequence groups of FIG. 2A within parentheses and in magenta color. The '.' symbol indicates a partition which is identical with the previous one. The block of lines indicated as "6" shows the identified strain of the target sequence and details the sequences of the strain containing group.

Figure for the Adaptive Mutations Embodiment of this Invention

Figure 4A:
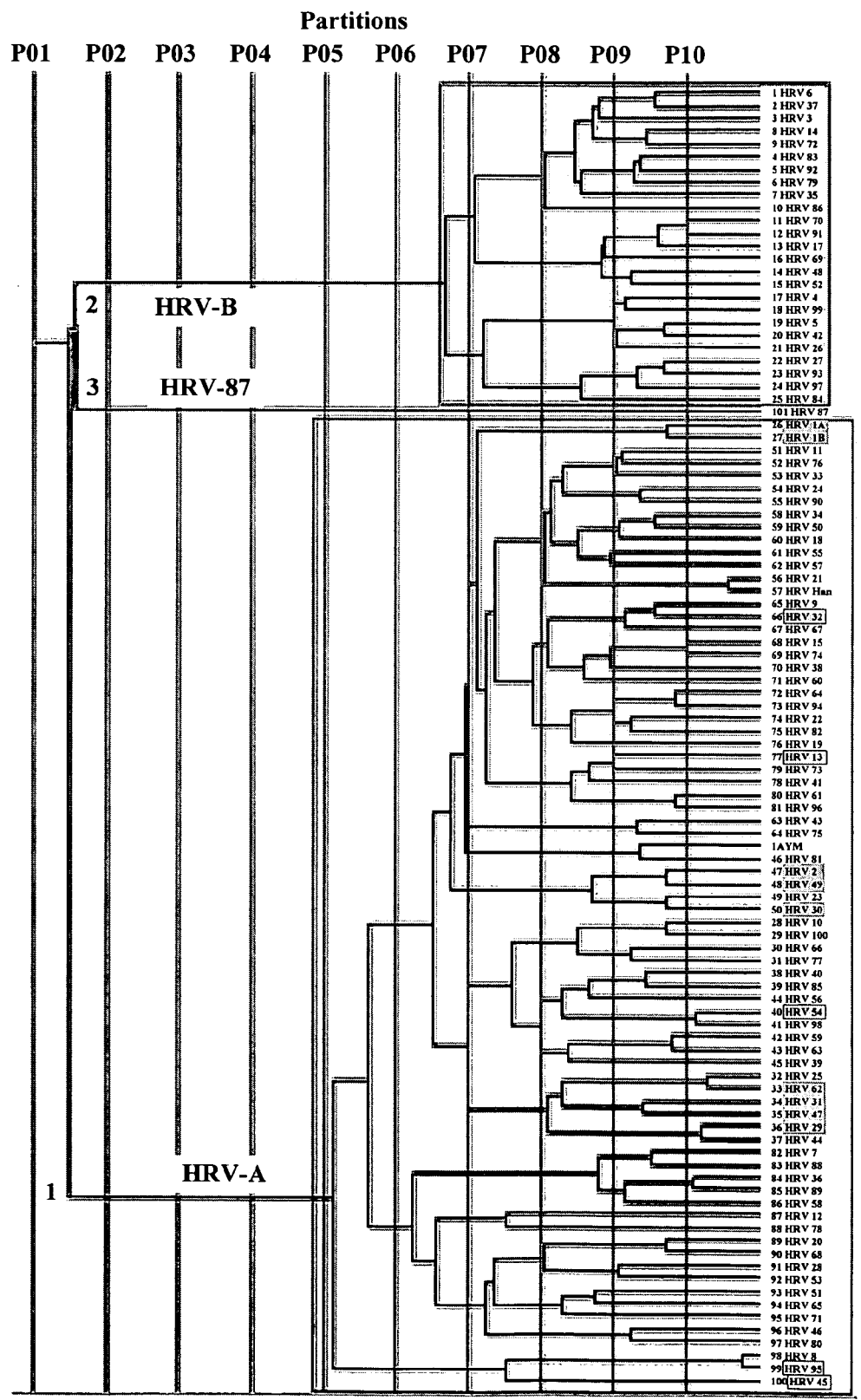

Strain Diversifying Locations in Human Rhinovirus (HRV) and Schematics to Explain Proposed Adaptations Through Strain Diversifying Mutations FIG. 4A depicts a partitioned phylogenetic tree of 100 HRV-VP1 capsid sequences of serotypes denoted using numbers. Red lines indicate the 10 partitions P01-P10. The P02 classes A and B (nodes 1 and 2) are boxed. Green highlighted strains belong to the minor group while the remaining strains constitute the major group. The orange highlighted HRV-A strains are not consistent with the anti-viral grouping of Andries et al. (1990). 1AYM (PDB code) denotes HRV16 serotype.

Figure 4B:
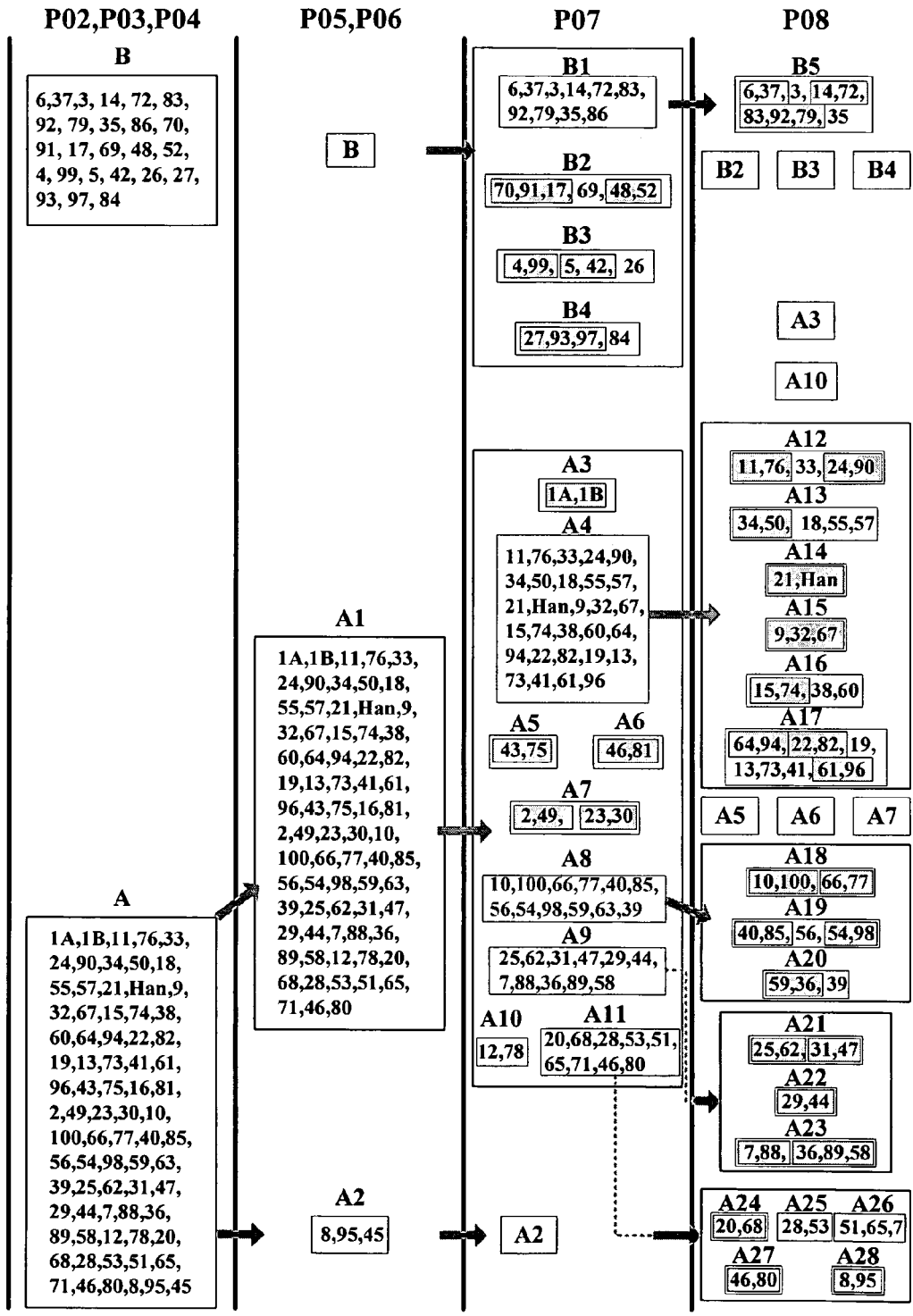

FIG. 4B depicts HRV serotypes belonging to different classes (shown boxed and alphanumerically labeled: A, B A1-A29, B1-B5) in P02-P08 partitions of FIG. 1a. Boxes with these labels inside them indicate classes that remain unchanged in subsequent partitions. Emerging classes are colored green. Boxes highlighted in green indicate P09 classes.

Figure 1A:
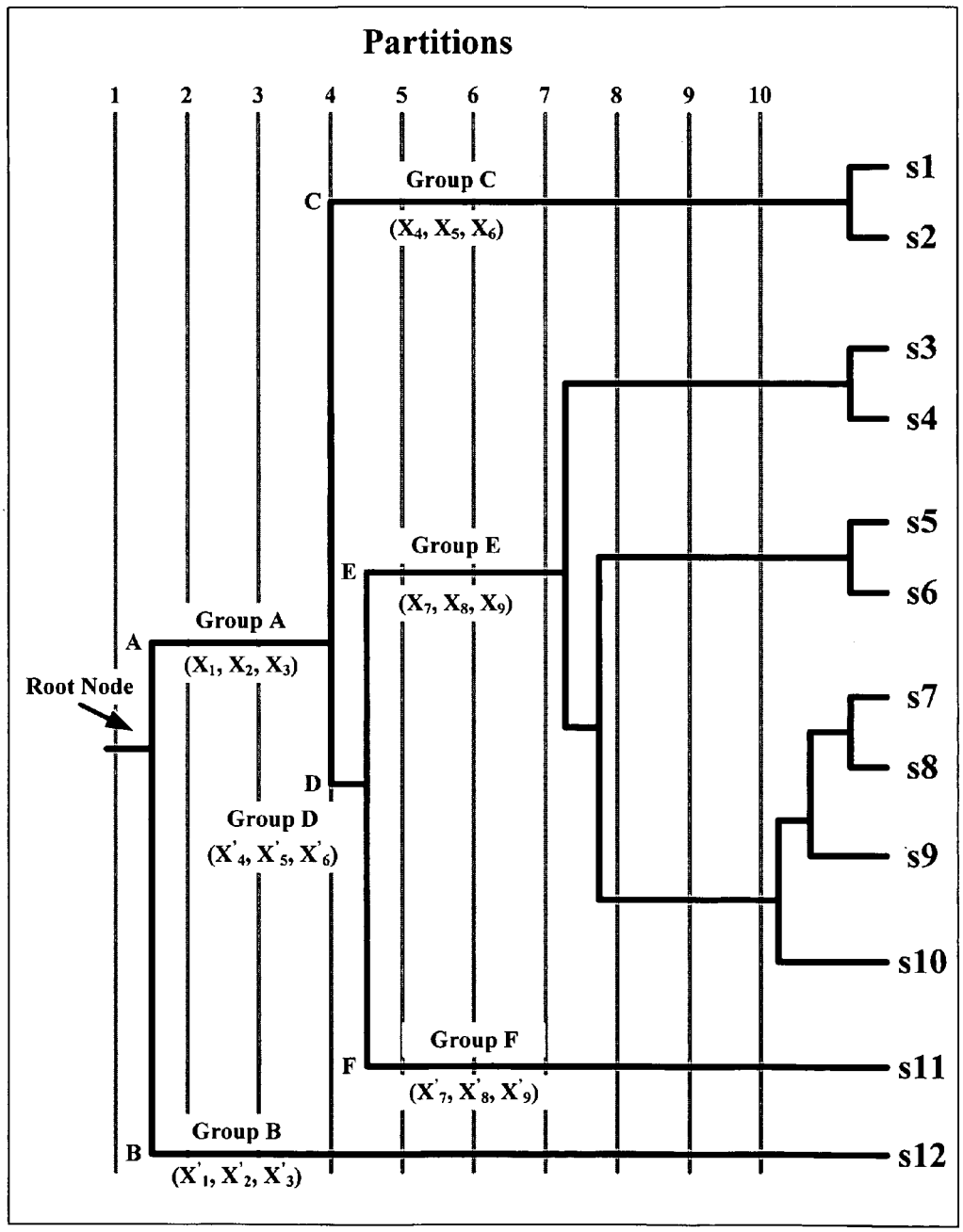
FIG. 1A depicts sequence groups and characteristic residues in partitioned phylogenetic tree: Representative phylogenetic tree with sequence groups s1-s12 forming the branches of the tree. Each group may consist of one or more sequence clusters. Vertical lines divide the tree into phylogenetic distance based partitions 1-10. Nodes closest to a given partition line and located to the left of the lines define the sequence groups belonging to that partition. Root node and other nodes (A-F) up to partition 5 are shown. Groups corresponding to the different nodes are denoted as "Group n" where n is the node name. For a given partition, characteristic residues (i.e. those residues which are conserved within individual groups but not across the groups) are designated as X and color matched with their node and group names. Subscripts of X denote residue locations which are numbered with respect to a user-defined reference sequence.
Figure 1B:
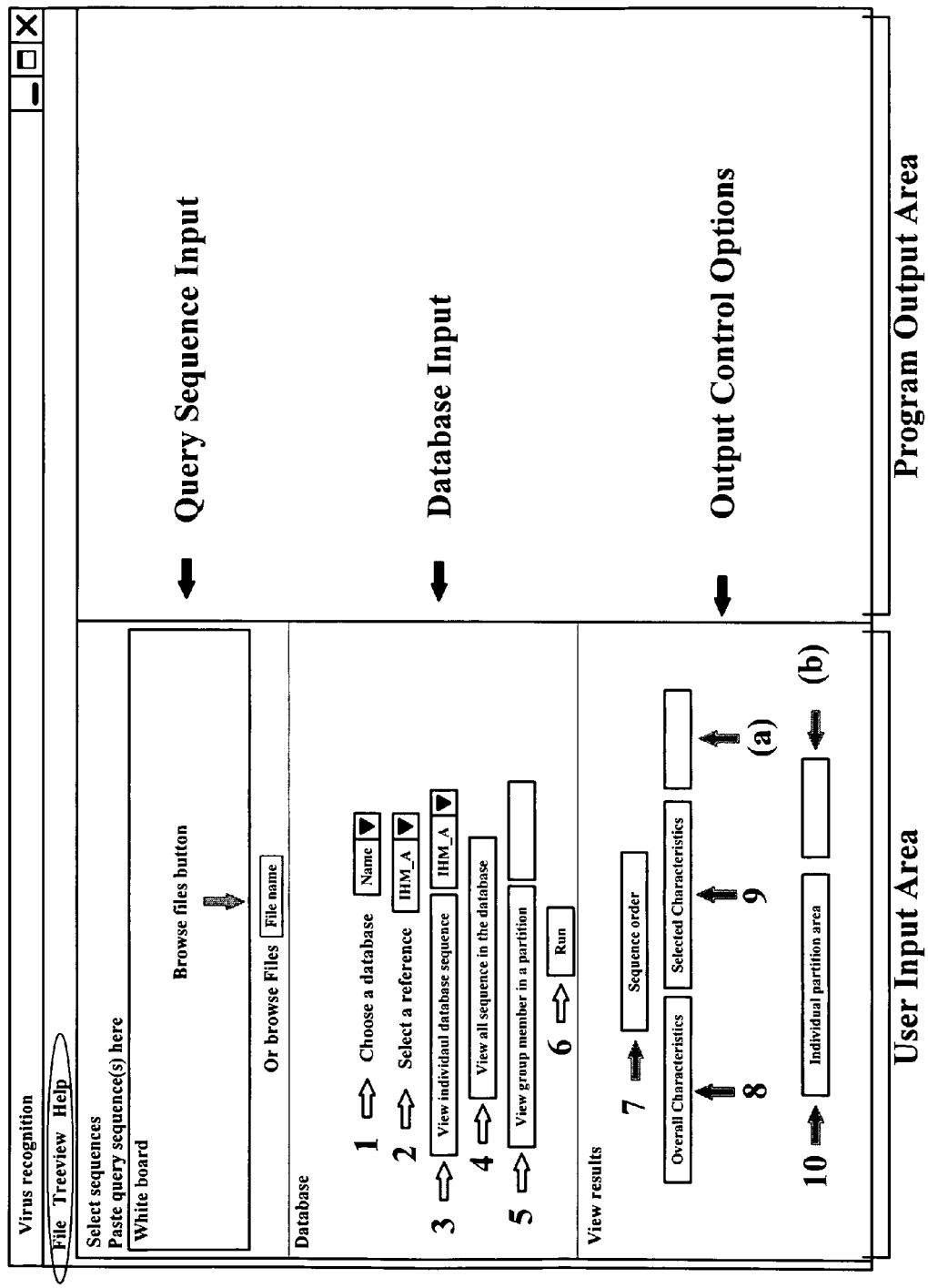
FIG. 1B depicts a software package GUI screenshot of this invention. Three options are shown in the orange encircled region at the top left hand corner of the GUI; File: Allows the output display to be saved in a file; Tree view: Displays genus tree in database; Help: Provides only limited help as most of the GUI options are self-explanatory through mouse attached tips. The user input and the program output parts of the GUI are indicated at the bottom. The program output part of the GUI displays the output results of the program. The user input area is divided into three parts shown using green arrows: "query sequence input", "database input" and the "output control options". These three parts correspond to the "select sequences", "database" and "view results" options in the GUI. Details of each of these parts are shown using differently colored arrows. The white board/"browse files" button (grey arrow) is used to input query sequence(s). Drop-down menus and toolbars in GUI's database input part are shown using orange arrows along with accompanying numbers; 1: "Choose a database" drop-down menu allows users to select the input target sequence genus, if known. An "unknown" option may be chosen if the genus is not known; 2: "Select a reference" allows users to select a reference sequence from the drop-down menu; 3: "View individual database sequence" option allows users to display a sequence from the selected database; 4: "View all sequences in the database" option allows users to display all the sequences in the selected database; 5: "View group members in a partition" allows users to select a partition whose all sequences within the different groups are displayed; 6: "Run" button allows program activation. The yellow arrows and their accompanying numbers in GUI's "View results" part indicate output display options: 7: "Sequence order": displays ID number of each input target sequence; 8/9: Display brief summary/details respectively of partition-wise matches of characteristic residues for an input target sequence identified by its ID in box shown using arrow '(a)'; 10: Displays details of characteristic residue matches for a chosen partition specified in box shown using arrow (b).
Figure 4C:
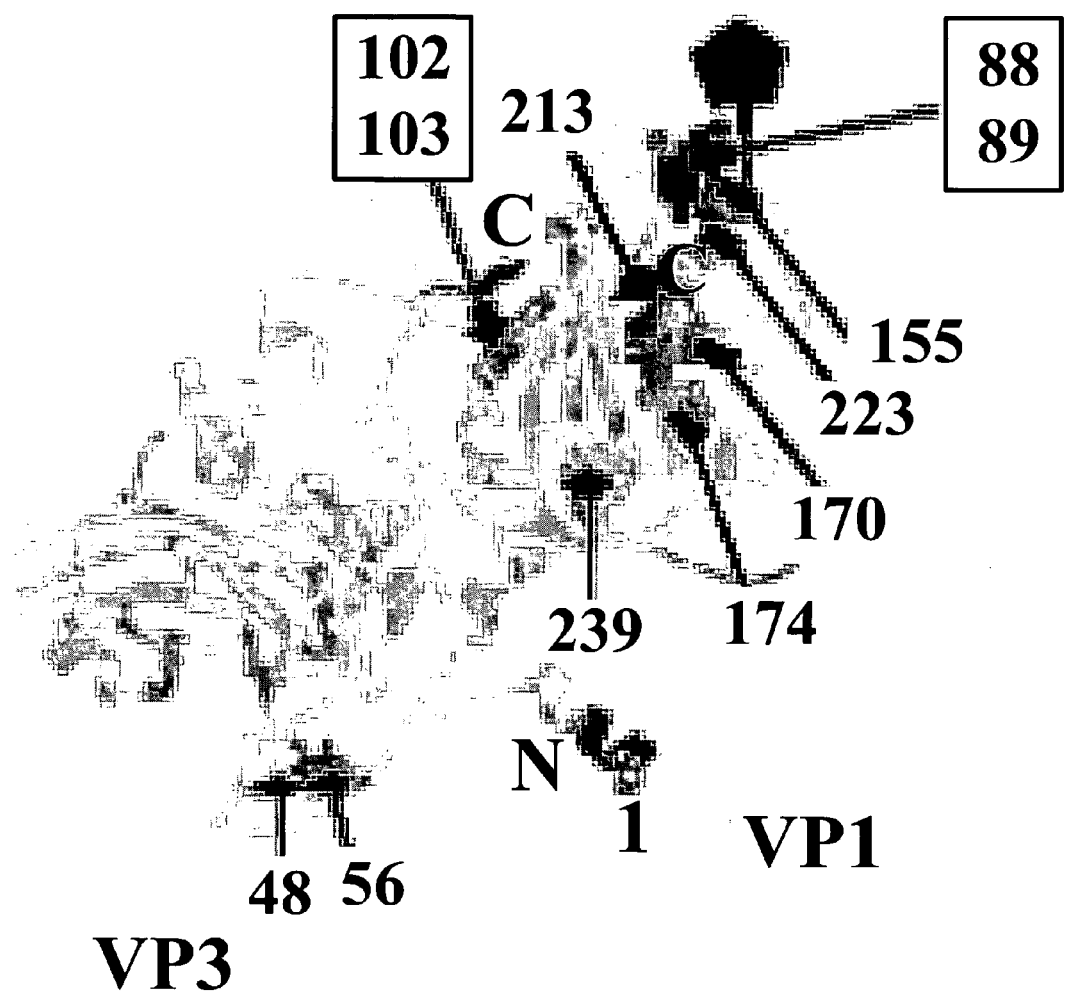

FIG. 4C depicts green spheres indicate some of the HRV-VP1 class-specific (or strain diversifying mutation) locations (HRV16 numbering) that distinguish between the serotypes of A and B classes of partition P02 (FIGS. 1a, 1b). The N- and C-termini are shown in blue and red respectively. The red spheres marked as 88 and 89 within a red box indicate the HRV16 locations corresponding to the NIm-IA sites of HRV14. Strain diversifying residue 213 (magenta) interacts with HRV16 receptor. The magenta colored pentagon denotes the approximate icosahedral 5-fold axis location.

FIG. 4D depicts structural pockets (P1, P3) and cavities (C2) localize strain diversifying mutation residues that are also involved in receptor binding (RB) and antigenicity. This causes interplay between strain diversification and the capsid related functions in and around the pockets and cavities, thereby, facilitating adaptations. Capsid region (green) depicting strain diversifying, RB and antigenic sites bound to receptor and antibody. Pockets P1 & P3 are solvent-accessible through regions N1 and N4 respectively while cavity C2 is solvent-inaccessible. However, cavity C2 is connected with pockets P1 & P3 through residues in regions N2 & N3 thereby depicting a network of cavities and pockets. Blue dots on P1, C2 and P3 indicate strain diversifying residues.

FIG. 4E depicts arrow showing strain diversifying mutations induced by host immune responses. These mutations may create altered receptor binding and antigenic characteristics by changing the surface and possibly regions N1 and N2. The altered regions are indicated within the red rectangle.

Partitioned Tree of Poliovirus Serotypes

Figure 5:
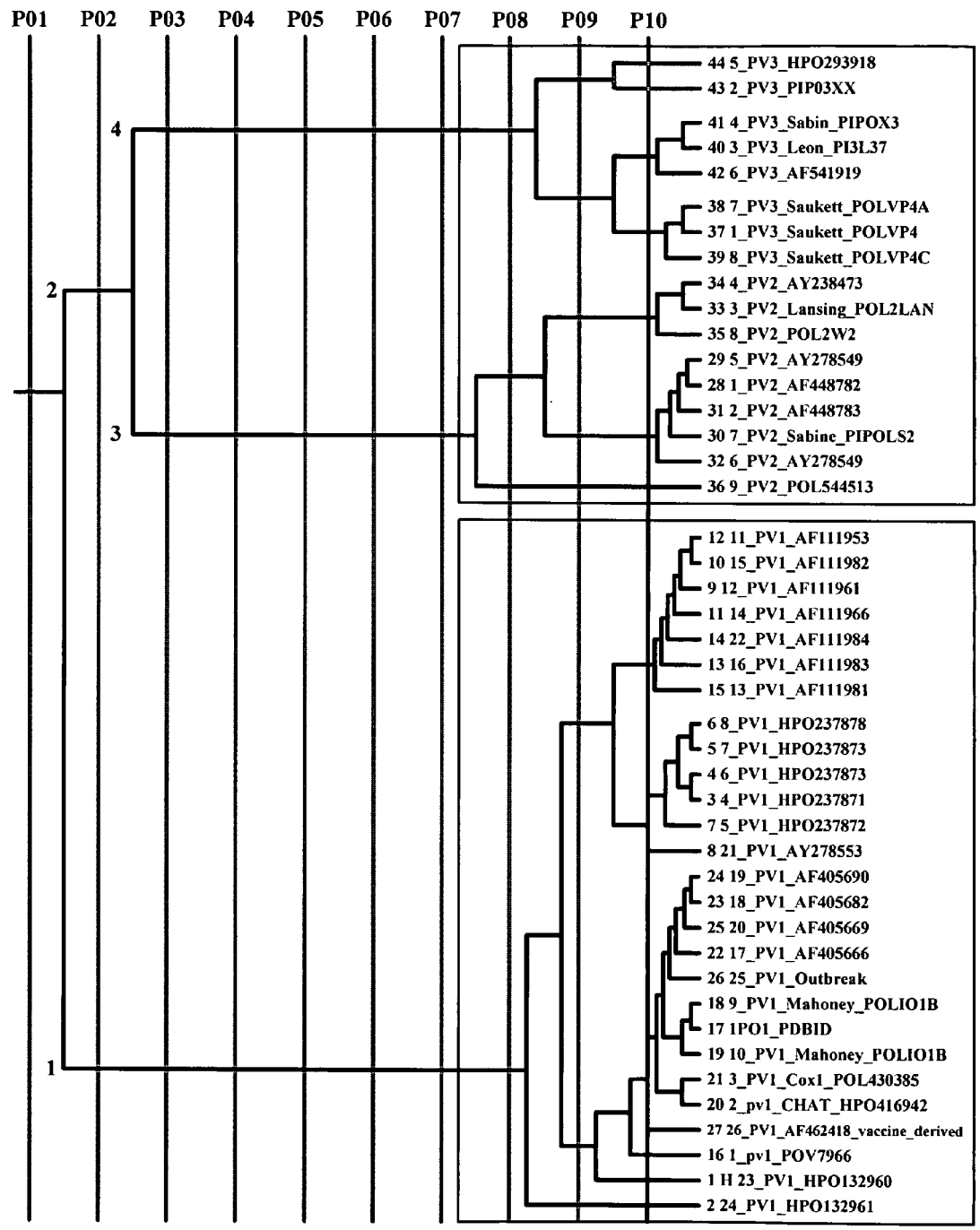

FIG. 5 depicts partitions are shown as P01-P10. The two P02 classes PV1 and PV2+3 are boxed. These two classes originate from nodes 1 and 2 respectively. The three poliovirus serotypes 1, 2 and 3 are denoted as PV 1, PV2 and PV3 respectively. Nodes 3 and 4 which separate the PV2 and PV3 respectively are shown in partition P03. Names of some of the well known serotypes are explicitly shown. Sequence accession numbers are appended at the end of each entry. Partitions are shown as P01-P10.

Rhinovirus Class-specific Capsid Residues Lining the Largest VP1 Pocket

Figure 6A:
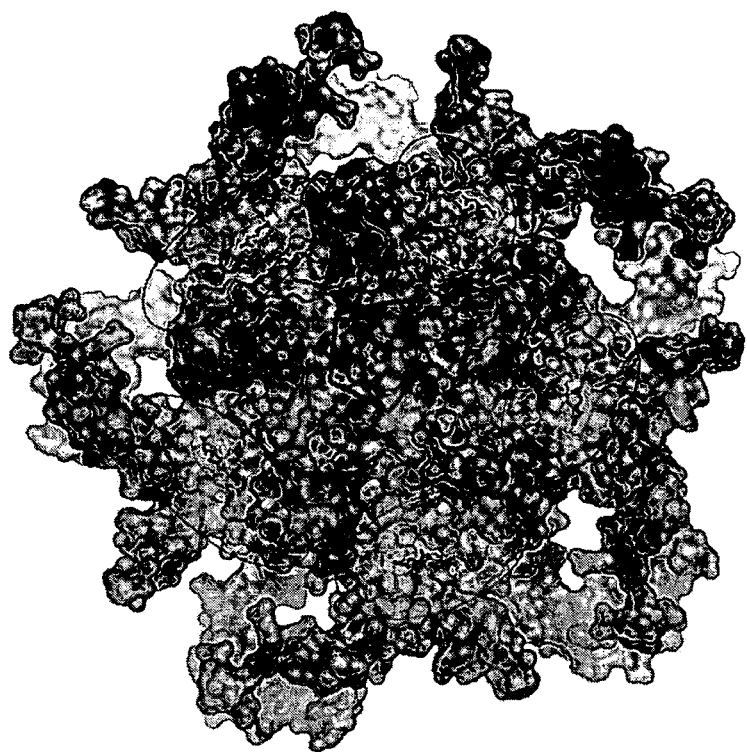

FIG. 6A depicts a surface representation of five copies of the largest computed VP 1 pocket viewed down the icosahedral 5-fold axis denoted by the magenta pentagon. The VP 1 residues lining each of these pockets are (I77, W96, I98, N99, L100, Q101, R107, F110, E111, F118, D119, S120, I122, M124, Y142, M143, Y144, P147, A166, S167, V168, F179, L181, P182, L184, S185, I186, A187, A189, Y190, Y191, M192, F193, Y194, Y206, G207, T208, T211, N212, D213 (contacts HRV16 receptor), M214, L217, I236, H238, R252, Y256, H260, T261, T262 and N263) (HRV16-numbering). These residues are not shown. The pockets are enclosed within the magenta ellipses and their exposed parts are colored green.

Figure 6B:
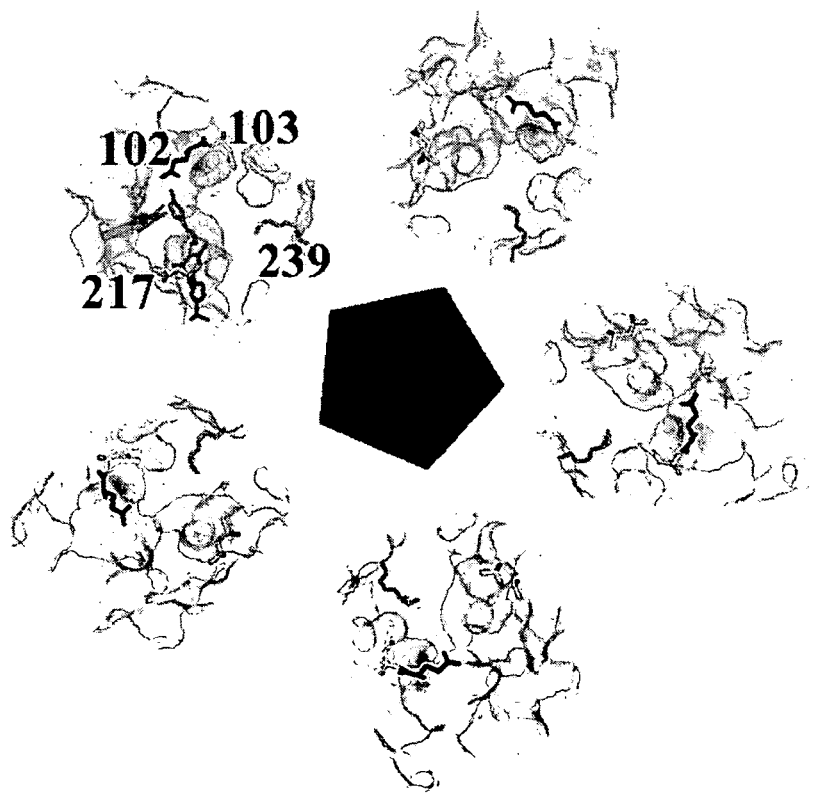

FIG. 6B depicts details of FIG. 6A pockets: The P02 class-specific (strain diversifying) VP1 residues 102, 103 and 239 (FIG. 1c) are shown in each of the 5 icosahedral symmetry related copies of the largest computed pocket. These residues, along with residue 217, form parts of the roofs and the floors of the pockets. Labels are shown for only one of the pockets. Orange arrow points to representative antiviral compound (PDB ID: 1ND3) shown in the largest computed pocket.

Class-Specific (Strain Diversifying) Capsid Residues Line Most Norovirus Pockets FIG. 7A depicts sphere representation of norovirus S, P1 and P2 domain class-specific (strain diversifying) residues in P02-P06 partitions superposed on the A-B dimer of the Norwalk virus capsid (PDB ID: 1IHM). Residues of partitions P02-P04, P05 and P06 are shown in green, red and cyan respectively. The vertical arrow shows the dimer axis. Letters N and C indicate corresponding termini in the two monomers. The purple colored residues (44 and 514) are the only exposed P02 class-specific residues (Chakravarty et al. (2005))

FIG. 7B depicts some of the exposed parts of the largest pockets in Norwalk virus dimer surface (wheat color). Exposed regions in S and the P1-domain pockets are shown in blue and green. Similar regions in the P2-domain pocket (#161 in Table 3) are indicated using a cyan arrow. Orange colors indicate the exposed regions near pockets around P1-P2 domain interface while the magenta colored region indicates the exposed parts of the hinge region pocket. Dimer orientation is that of FIG. 4a.

Figure 7C:
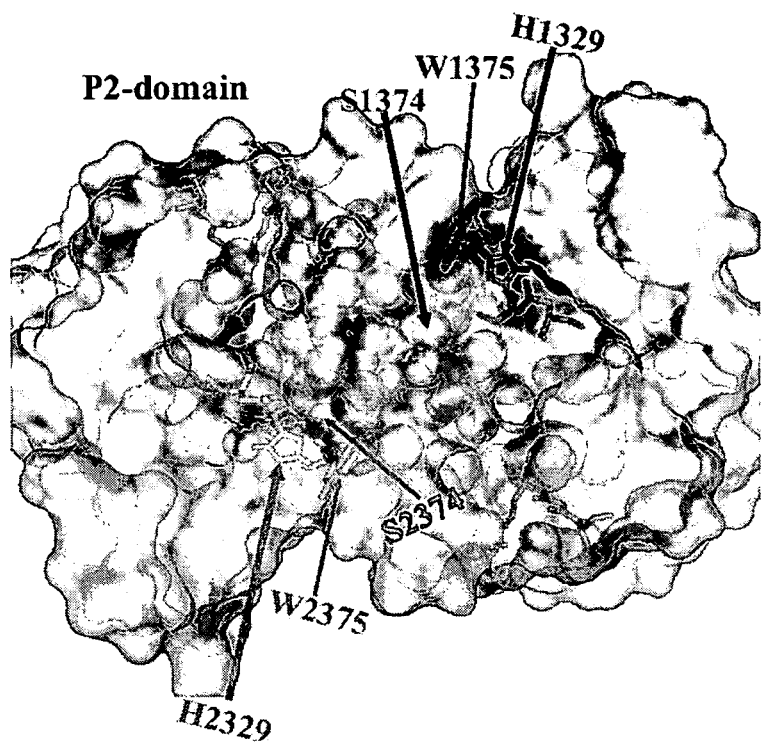

FIG. 7C depicts P2-domain pocket of FIG. 4B. Green spheres represent inaccessible atoms of the pocket. Some class-specific (strain diversifying) residues that putatively bind norovirus receptor, line this pocket. These residues are indicated using arrows. The 4-letter codes denote subunit and residue numbers, e.g. W1375 and W2375 indicate residue 375 in subunits A and B respectively. The view is a 90° rotation of FIG. 4b about the horizontal direction.

Figure 7D:
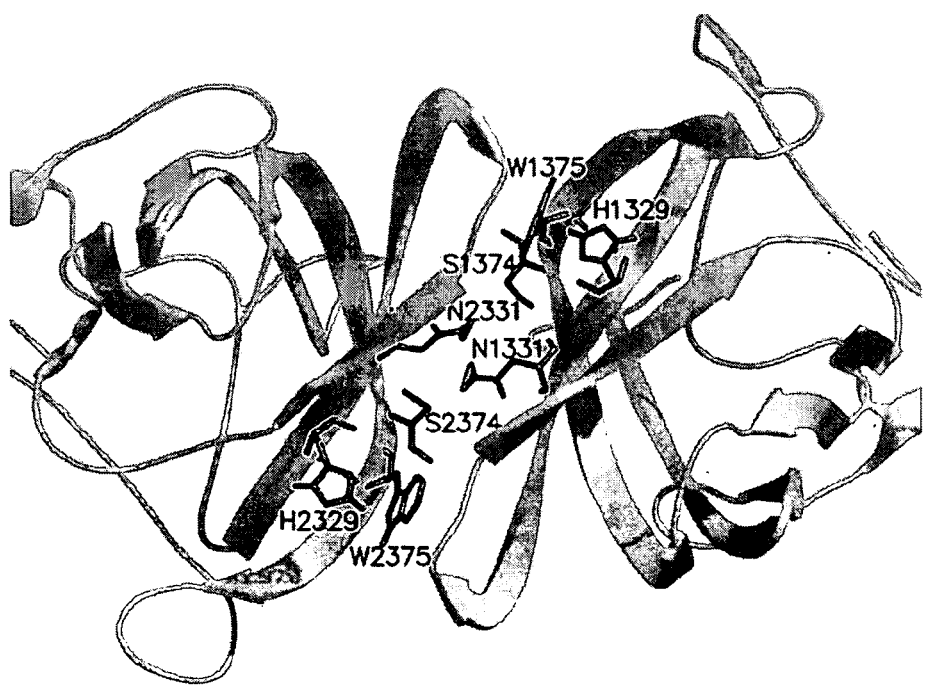

FIG. 7D depicts the P2-domain pocket and class-specific residues (CSRs) of FIG. 4c shown against secondary structure of the domain. The view is that of FIG. 4c. Residue 331 forms part of the class-specific region formed by the CSRs shown and their neighbors.

Figure 7E:
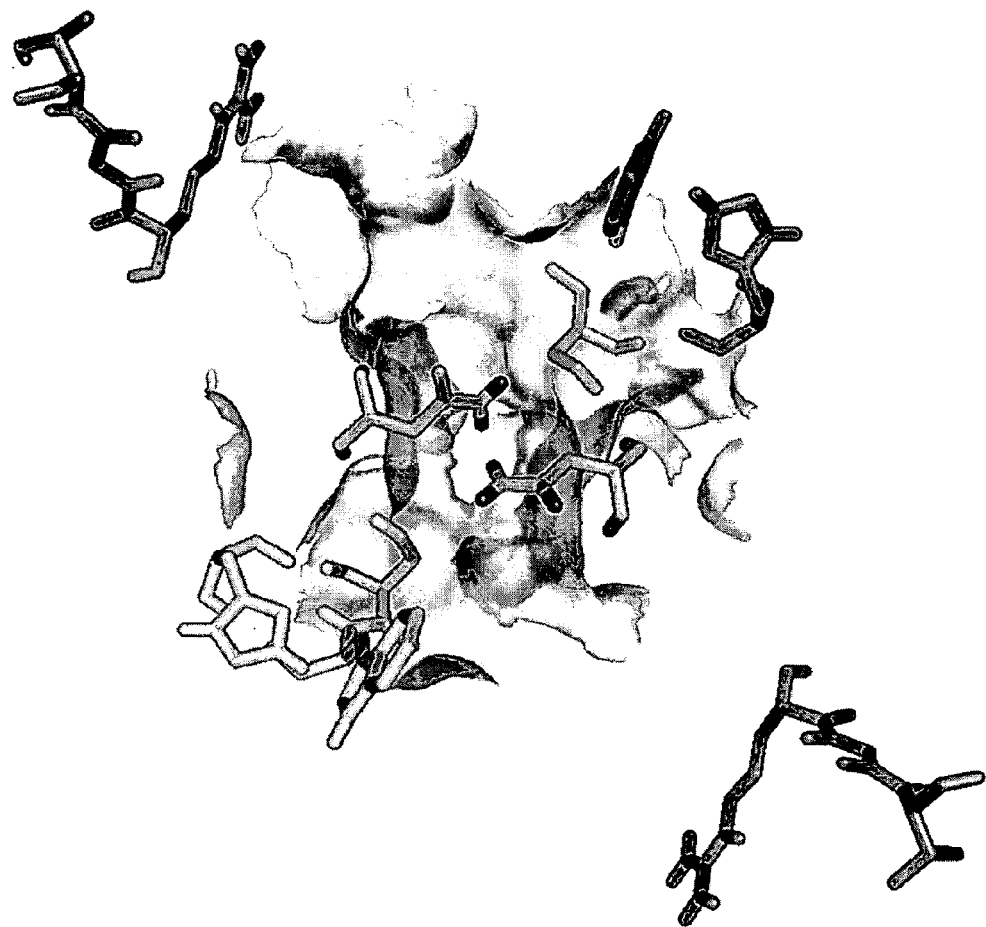

FIG. 7E depicts close-up of the green colored P2-domain pocket region of FIG. 4C. The 4-letter codes of FIG. 4C are used to number the residues. Additional exposed residues 291-293 (purple) are located in the vicinity of the pocket.

Figure 8:
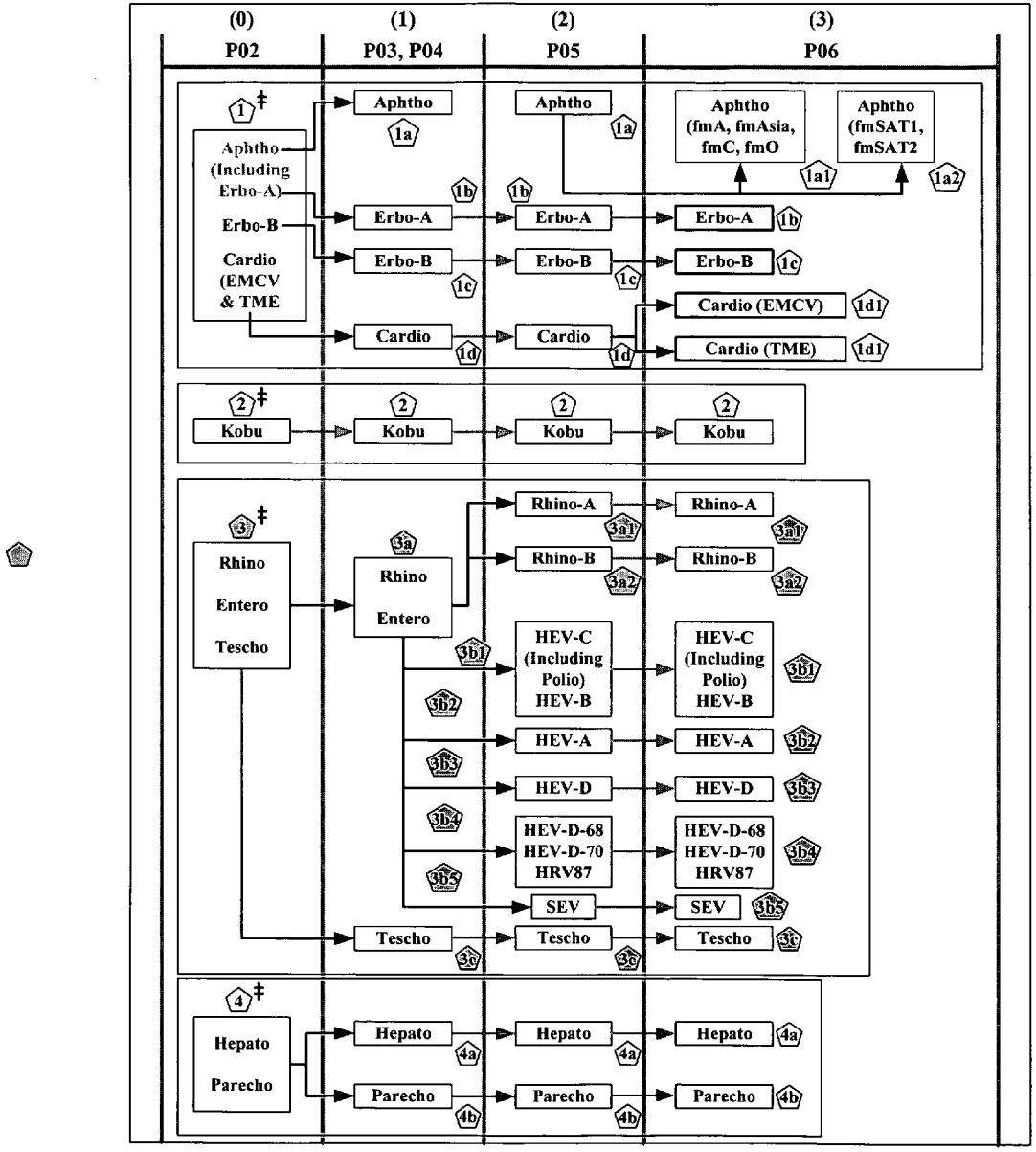

Picornavirus Diversity Obtained by Partition-Wise Comparisons of Capsid Sequences FIG. 8 depicts only 5 partitions P02-P06 are shown. Numbers in cyan within parentheses above each partition indicate the number of iterative sequence comparisons required to generate new P02 classes that are identical with that of the given partition. The starting P02 partition for such iterations is indicated in orange with an iteration number 0. Each rectangular box represents a class within the partition. Each class is separately numbered using color-coded pentagons. All P02 classes are shown within boxes that are outlined in magenta. Symbol used: ‡: Possible genera (P02 classes); Abbreviations used: HRV: Human rhinoviruses; Entero (HEV-A, B, C, D): enterovirus genus (A-D species); The HEV-D-68 & 70 represent serotypes 68 and 70 of the HEV-D species; Rhino-A and B: Rhinovirus genus and A & B species; Cardio (EMCV & TME): cardiovirus genus (encephalomyocarditis and the Theiler murine encephalitis species); Erbo (A & B): Erbovirus genus (A & B species); Aphtho (fmA, fm-Asia, fmC, fmO, fmSAT1, fmSAT2): aphthovirus (fm(Foot-and-mouth) species and A, Asia, C, O and South African (SAT) serotypes 1 & 2); SEV: Simian enteroviruses. Abbreviations of the remaining genera (hepatovirus, parechovirus, erbovirus, kobuvirus and the teschovirus) are self explanatory. Arrows indicate emergent classes in different partitions. Classes that show changes in subsequent partitions are connected using magenta arrows while classes that remain unchanged are connected using grey arrows.

Supplementary Figures

FIG. S1 depicts partition P02 insertions contain a human rhinovirus (HRV) neutralizing immunogenic (NIm) site of VP1 capsid protein: Conservation patterns among HRV classes for partitions P02-P09 are shown. Classes that are horizontally shaded in light blue and light green color contain the HRV14 and HRV16 (PDBID: 1AYM) sequences respectively. These classes are also indicated within parentheses next to each partition header. Square brackets show classes 1-35 that emerge in partitions P06-P09 from the two P02 classes A and B (shown within black square boxes). Dots (.) and dashes (-) indicate insertions and variable regions respectively. Highlighted green and red vertical bars indicate residues 91 and 95 respectively that belong to the NIm-Ia site of HRV14 serotype. Symbols "X" refer to class-specific locations.

FIG. S2 depicts a partitioned (P01-P10) tree of the human enterovirus (HEV) A and B species: Partition P02 classes are boxed as HEV-A and HEV-B. Nodes corresponding to these classes are shown using green circles. The HEV-C sequence 1Z7S has been included to serve as a marker as it does not belong to any one of these classes. Accession numbers are appended at the end of each sequence. Abbreviations used: cox: Coxsachievirus; echo: Echovirus; pHEV-nn: Proposed HEV-nn where nn is the serotype number; HK__1: Hongkong strain; PDBID: Protein Data Bank 4-letter code (the subunit name is also shown); SVDV: Swine vesicular disease virus.

FIG. S3 depicts partitions P01-P10 of the human enterovirus (HEV) A, B and C serotypes: The two boxes "HEV-A" and "HEV-(B&C)" denote the two P02 classes. The former consists of strains of the known A serotype while the latter consists of B and C serotypes together. A1-A4 indicates nodes from which HEV-A classes originate in subsequent partitions. The HEV-C strains are shown using a square bracket. B' and C' indicate nodes from which the HEV-B and C serotypes originate. Polioviruses are indicated within a red box. Accession numbers are appended at the end of each sequence entry. Abbreviations used: pv: Poliovirus; cv: Coxsachievirus; echo: Echovirus; pA, pB, pEcho: Sequences currently proposed as HEV-A, HEV-B and echovirus respectively; pEcho: Proposed echovirus; pB: Proposed HEV-B species; HK__1: Hongkong strain; PDB: Protein Data Bank 4-letter code. Serotypes are appended to these abbreviations e.g. cv_B3 implies coxsachievirus B3 serotype.

FIG. S4 depicts partitioned comparisons of the human enterovirus (HEV) A, B, C and D species: Species A, B, and C form two P02 classes that are shown within 2 boxes. One of these classes contains strains of HEV-A species while the other one contains HEV-B & HEV-C species together. The HEV-D class is indicated separately. Accession numbers are appended at the end of each sequence entry. Abbreviations used: cv: Coxsachievirus; echo: Echovirus; pA, pB, pEcho: Sequences currently proposed as HEV-A, HEV-B and echovirus respectively; pHEV-nn: Proposed HEV-nn where nn is the serotype number; PDB: Protein Data Bank 4-letter code. Serotypes are appended to these abbreviations e.g. cv_B3 implies coxsachievirus B3 serotype. The square bracket indicates HEV-C serotypes. The polioviruses have been omitted for clarity.

Database Structure Used in Adaptive Mutations Embodiment

FIG. D1 depicts the rhino cDNA database used in the adaptive embodiment.

FIG. D2 depicts the code used read the database used in the adaptive embodiment.

FIG. D3 depicts the group information used in the structured data of the database used in the adaptive embodiment.

FIG. D4 depicts the partition trees of the database used in the adaptive embodiment, consisting to ten partitions.

FIG. D5 depicts partition one (P1) of the database used in the adaptive embodiment.

FIG. D6 depicts Partition one (P2) of the database used in the adaptive embodiment.

FIG. D7 depicts Partition one (P3) of the database used in the adaptive embodiment.

FIG. D8 depicts Partition one (P4) of the database used in the adaptive embodiment.

FIG. D9 depicts Partition one (P5) of the database used in the adaptive embodiment.

FIG. D10 depicts Partition one (P6) of the database used in the adaptive embodiment.

FIG. D11 depicts Partition one (P7) of the database used in the adaptive embodiment.

FIG. D12 depicts Partition one (P8) of the database used in the adaptive embodiment.

FIG. D13 depicts Partition one (P9) of the database used in the adaptive embodiment.

FIG. D14 depicts Partition one (P10) of the database used in the adaptive embodiment.

DETAILED DESCRIPTION OF THE INVENTION

The inventors have found that a software product can be constructed and implemented on or in computer or a distributed computer network, where the software product encodes an unique method for characterizing residues constructed to automatically identify strains of partial or complete sequences of pathogens. The product includes databases of pathogen residues that uniquely characterize strains of the pathogens and were created by constructing partitioned phylogenetic trees of available complete capsid sequences of these viruses. Partition-wise comparisons of the database residues with the corresponding residues of complete and partial sequences of unknown pathogens results in correct strain identification for all pathogens for which data are stored in the software database. A Java based user-friendly graphical console interfaced with Perl-coded computational parts ensures high portability of the software. The package has been successfully tested on MS-Windows XP and the Linux and UNIX platforms. The code used in this implementation is attached as Appendix 1.

The inventors have found that a software product that uses unique characterizing residues can be constructed to automatically identify strains of partial or complete capsid sequences of picorna and caliciviruses, two of the most highly diverse ssRNA virus families. The software is an efficient implementation of an algorithm outlined in earlier by on of the inventors in structure based phylogenic analysis of some human calicivirus sequences. Databases of capsid residues that uniquely characterize strains of picorna and caliciviruses were created by constructing partitioned phylogenetic trees of available complete capsid sequences of these viruses. Partition-wise comparisons of the database residues with the corresponding residues of more than 300 complete and partial sequences of these viruses resulted in correct strain identification for all of these sequences.

In one embodiment, the present invention relates to creating databases of capsid residues uniquely distinguishing among virus reference strains and using these databases to automatically predict strains of other closely resembling target sequences. The method is demonstrated for complete and partial capsid sequences of calici and picornaviruses, which are two of the most highly divergent ssRNA virus families and therefore especially difficult to unambiguously identify using a uniform method.

Capsid Embodiment of the Invention

METHOD

Basis

The method relies on creating databases of capsid residues that uniquely distinguish among the reference calici and picornavirus sequences. Residue-wise comparisons of the complete or partial input target sequences with the databases yield those reference sequences that are closest to the target sequences. Such reference sequences, in turn, yield the genogroup and other classification characteristics of the target sequences thereby identifying their strains.

Partitioned Phylogenetic Trees Yield Groups of Similar Sequences

Following the procedure described earlier [40], evolutionary trace [41] based partitioned phylogenetic trees were constructed for each of the 4 calicivirus genera and the 9 picornavirus genera using a large number of complete capsid sequences from public domain databases [25, 42]. These sequences will be called the "reference" sequences and the corresponding trees will be called the "reference" or the "genus" trees as each such reference tree represents a calici or a picornavirus genus.

By sieving the reference sequences of a genus tree through "similarity filters", sequence groups, each of which contains several similar reference sequences, were created in every partition of the tree. Examples of such sequence groups are illustrated for a hypothetical representative tree (FIG. 1A). Starting from the root node, the partition 1 contains all of the aligned sequences. Sequence comparisons in this partition, therefore, are equivalent to conventional sequence comparisons that consider all of the sequences together. Partitions 2 and 3 are identical and contain the sequence groups s1-s11 and s12 belonging to nodes A and B respectively. Similarly, the two nodes C and D belong to partition 4 while nodes E and F belong to partition 5. Node C of partition 4 contains sequence groups s1 and s2 while node D of the same partition contains nine (s3-s11) of the remaining groups. Similarly, the eight groups (s3-s10) in partition 5 belong to node E while group s11 belongs to node F in the same partition (FIG. 1A). Henceforth, sequence clusters or sequence groups will be referred to simply as groups.

Sequence Groups Comparisons Reveal Characteristic Residues Within Genus Trees

For each genus tree, partition-wise comparisons among the different groups identified "characteristic residues" that are conserved within each group but not among the different groups of the partition. For example, characteristic residue X1 at location 1 of partition 2 of a given tree may be a conserved Ala for Group A of node A in contrast to a conserved Gly (X1') for Group B of node B (FIG. 1A). Such residues were generated for each genus tree following the procedure described earlier [40].

Database Creation

Entire information about the genus trees including their partitions, all the sequence groups for each partition along with all characteristic residues taken group-wise, were stored in multiple 2-dimensional arrays that formed the calici and the picornavirus databases.

Strain Identification Through Partition-Wise Comparisons

To identify the strain of the input query ("target") sequence whose genus is known, the program matches the target residues with the characteristic residues of each group of a given partition stored in the appropriate genus database. This is done by first aligning the target sequence with a reference sequence of the database. Then, starting with the second partition from the root (partition 2 in FIG. 1A), each characteristic residue of a given group in this partition is compared with the target residue at the corresponding location. Such comparisons are carried out for all the groups of this partition. The group showing the maximum number of matches is accepted by the program as the most probable sequence cluster resembling the input target sequence in that partition.

The program proceeds to the next partition, where, instead of similarly testing all the groups present in the partition, the program tests only those groups that are directly tree-linked with the most recently accepted group. This considerably reduces the number of groups to be searched in the next partition. The process continues until all partitions have been searched. Testing only a limited number of connected groups per partition guarantees an optimal tree search time thereby making the program quite efficient.

Within a given partition, input target sequence residues once matched are flagged as "marked" and are never used again for residue matching in subsequent partitions. Exceptions to the flagging procedure are carried out only in case of ambiguities. For example, if all of the groups in a partition show an identical number of characteristic residue matches, an ambiguity is declared and no match is flagged. This ensures that all such matched residues of the input sequence are available again for matching purposes in subsequent partitions thereby helping resolve the ambiguity. Ambiguities may also occur when all groups within a given partition show no matches with the input sequence, or, if two successive partitions show identical numbers of characteristic residue matches. In both these cases, the program ignores the ambiguous partition(s) and proceeds to the next one without marking any residue at all. This allows all of the unmarked residues in the current partition to be compared again in subsequent partitions.

To illustrate the method, let us assume that the input sequence corresponds to a known genus whose characteristic residues X1, X2 and X3 for partition 2 are Ala, Pro and Ser respectively for group A and the corresponding group B residues (X1', X2' and X3') are Gly, Thr and Met, respectively (FIG. 1A). If the aligned target sequence shows more matches for X1, X2 and X3 of group A in comparison with that of X1', X2' and X3' of group B, it implies that the input sequence belongs to group A in partition 2 and not to group B. Thus, residues X1, X2 and X3 are flagged and comparisons in subsequent partitions follow along those branches that are connected to group A (FIG. 1A). The program therefore proceeds to groups C and D in partition 4 ignoring partition 3 as it is identical to the previous partition 2 (FIG. 1A).

In partition 4, if both groups C and D show equal number of matches i.e. say, X4 and X4' are both Trp and X5 and X5' are both Leu (FIG. 1A) and the aligned target sequence also contains Trp and Leu at these locations, then the program will not flag these characteristic residues but will instead carry them over to partition 5 where these residues will again be matched in groups E and F (FIG. 1A) to determine which of these two groups maximally matches the target sequence. Similar comparisons in subsequent partitions 6-10 unambiguously identify the database strain that most closely resembles the input target sequence thereby yielding its strain characteristics.

In case the genus of the target sequence is not known, this sequence is first compared with groups of representative reference sequences (<3 sequences per group) from each of the genus trees in the database using ClustalW [43] and the alignment scores computed for each group. The highest alignment score indicates the genus of the input sequence which allows the appropriate genus tree to be selected from the databases for further strain identification using the earlier described procedure. A low number of sequences per group ensure rapid genus determination regardless of the number of reference sequences present in the genus tree.

Detecting Recombination and Spontaneous Mutations

Figure 1C:
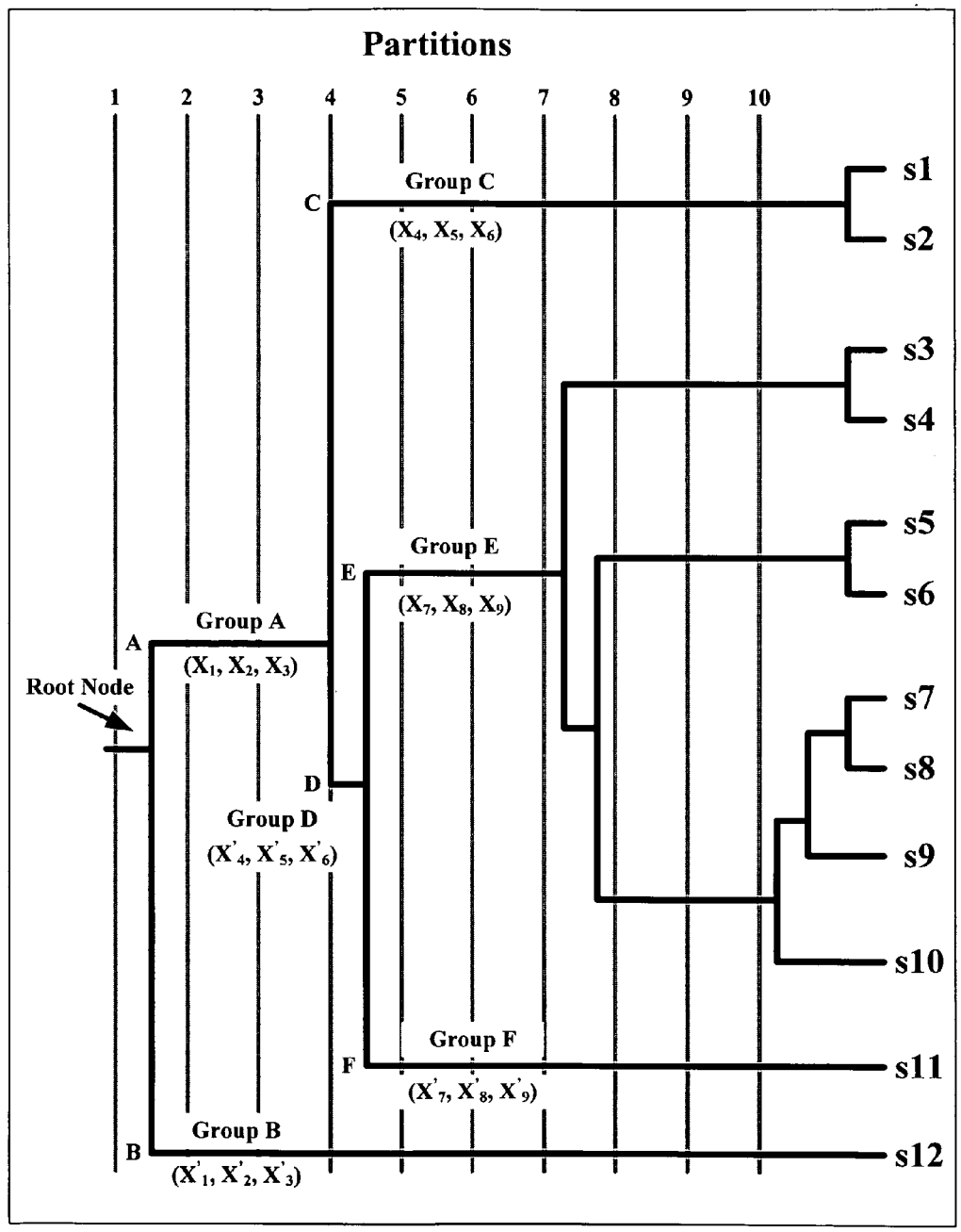
FIGS. 1C&D depict incongruous phylogenetic trees to explain recombination detection using the software: Representative phylogenetic tree with sequence groups s1-s12 forming the branches of the trees. Sequences s1 and s10 are interchanged in the two hypothetical trees to highlight a simple case of recombination-induced incongruities between the two trees.
Figure 1D:
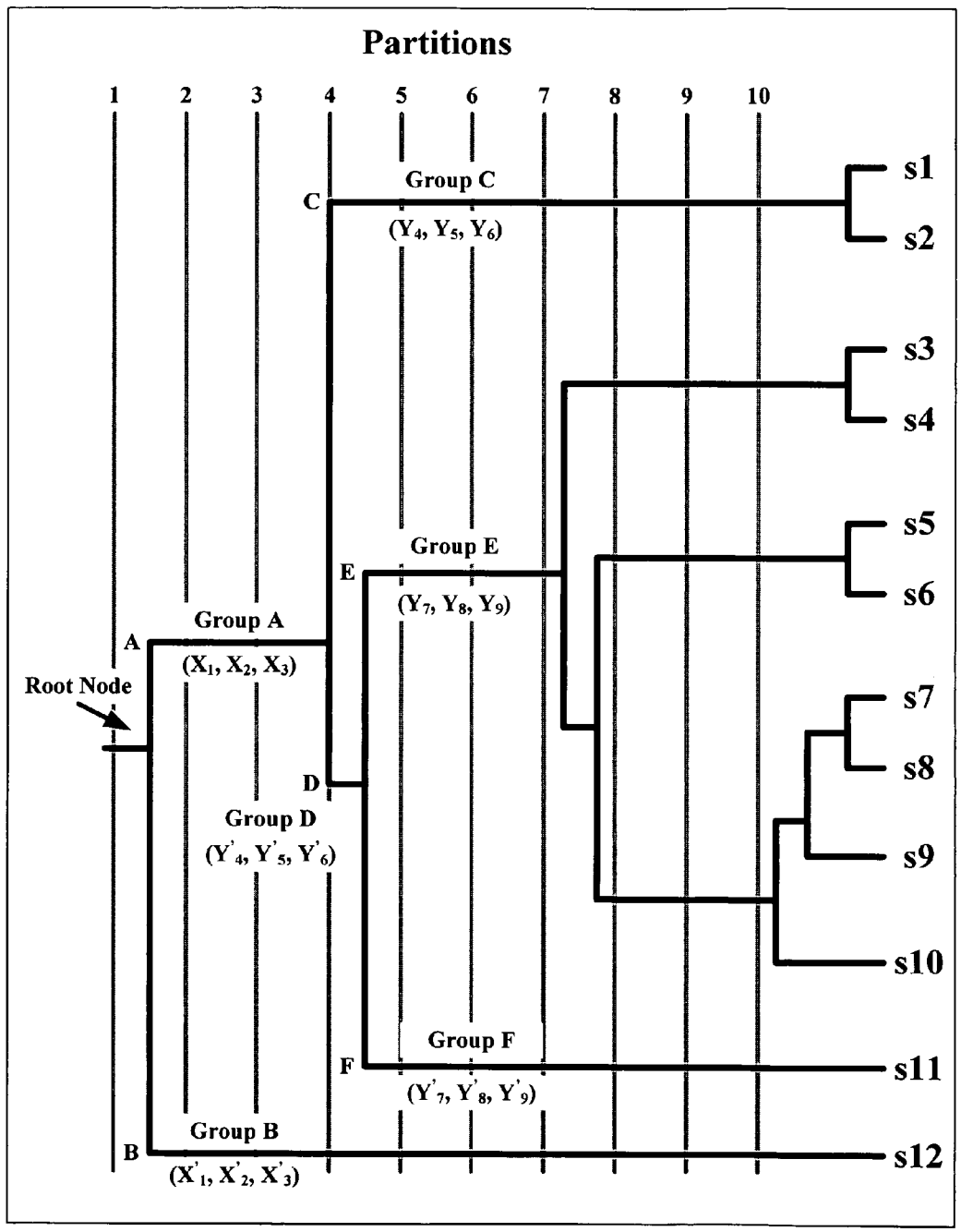

Partition-wise comparisons allow RECOVIR to detect abrupt changes in phylogenetic sequence groupings among different trees. Assuming that absence of recombination creates similar phylogenetic relationships among sequences from different regions of multiple sequence alignments, these abrupt changes indicate nodes that may possibly contain recombination sites. Such abrupt changes are shown schematically using a pair of hypothetical trees (FIGS. 1C&D). These trees may represent, for example, two different genomic regions of the same virus strains. A simple example of incongruence has artificially been built in by interchanging sequence group s1 and s10 between the two trees. Consequently, sequence groups belonging to nodes A and B may be distinguished by the same set of residues (X1, X2, X3) and (X1', X2', X3') in both the trees. However, subsequent nodes C, D, E, and F have different strain distinguishing residues up to partition 5 of the two trees that correspond to the two genomic parts being compared (FIGS. 1C&D). For example, nodes C and D are distinguished by residues (X4, X5, X6) and (X4', X5' X6') in one part of the genome (FIG. 1C) and by (Y4, Y5, Y6) and (Y4', Y5', Y6') in the other genome part (FIG. 1D). Similarly, nodes E and F are distinguished by residues (X7, X8, X9) and (X7', X8', X9') in one part of the genome (FIG. 1C) and by (Y7, Y8, Y9) and (Y7', Y8', Y9') in the other genome part (FIG. 1D). Systematic node-wise comparisons of such strain distinguishing residues in all of the partitions P2-P10 clearly show the genomic regions that result in the incongruence between the two trees and thus, indicate parent strains along with their possible recombination or spontaneous mutation sites. Detection of these sites and the corresponding parent strains is done manually at present as an automated version of this feature has not yet been built into the software.

Program Testing and Validation

The program was initially validated by identifying the closest strains for five noro and five enteroviruses of known genera from their respective complete and partial amino acid sequences of the capsids (Table 2). These viruses were chosen because of their wide sequence divergence and their large number of strains or serotypes many of which have multiple sequences available in public databases. The enteroviruses included the complete VP1 sequences of Poliovirus-2 (serotype), human enterovirus (HEV)-B including the Coxsackie viruses, HEV-D (serotype) and the simian enteroviruses.

The program was then further validated using more than 200 complete and partial sequences of different caliciviruses and more than 100 such picornavirus sequences. Among the calicivirus sequences, nearly 120 sequences were those of noroviruses with the remaining ones being those of other caliciviruses. Similarly, in the case of picornavirus sequences, nearly 50 were enterovirus partial sequences including those of echoviruses and of other HEV-B serotypes [25] while the remaining sequences were chosen from the other picornavirus genera and species (Table 1).

Most of the partial sequences were randomly chosen from different regions of the capsid with the sequence lengths being only ~20% of the sizes of the corresponding complete capsid sequences. All of the noro and enterovirus sequences were selected from the NCBI databases [42] taking care that possible errors due to biased choice of these sequences were minimized by ensuring that none of the selected sequences were included in the program databases.

Software Description

All functional modules of RECOVIR were written in the Perl programming language on Windows XP, Linux, and UNIX platforms. A Java based graphical user interface (GUI) has been designed to wrap all functionalities and allow user-friendly I/O options (FIG. 1B).

Program Input and Output

Input selections on the GUI have been divided into 3 categories: sequence, databases and options to control output (FIG. 1B). Any number of query sequences may be input by either pasting them on the white board area or by browsing one or more directories for single or multiple sequence files. A given sequence file may contain any number of complete and partial sequences. Only FASTA formatted sequence files are accepted and all white spaces and non-alphabet characters are ignored in input sequence files.

A dropdown menu in the database section of the GUI allows the user to specify the input sequence genus, if known (FIG. 1B). A default reference sequence, used for aligning the input sequences and for assigning the aligned location numbers to the input sequence, then pops up in the "Select a reference" box (FIG. 1B). This default reference may be changed if required. In case genus of the input sequence is not known, the "unknown" option in this box (FIG. 1B) allows the program to automatically determine the genus and an appropriate reference sequence from the built-in databases.

The "Run" button activates the program, displays a progress bar indicating the percentage of input sequences processed and outputs results on the GUI's output section (FIG. 1B). Depending on the "View results" options chosen, the output may include a summary or the complete details of partition-wise matches between the database characteristic residues and the residues of the input target sequences. Many other details about the partitioned databases and run results may be viewed using various user-friendly options in GUI's output control section (FIG. 1B).

Results and Discussion

Strain Identification of Complete and Partial Norovirus Capsid Sequences

Databases

Detailed strain identification results are described for only some norovirus strains among caliciviruses and some enterovirus strains among the picornaviruses. Complete details for the other calici and picornaviruses can be found at web site prion.bchs.uh.edu/recovir.

Figure 2A:
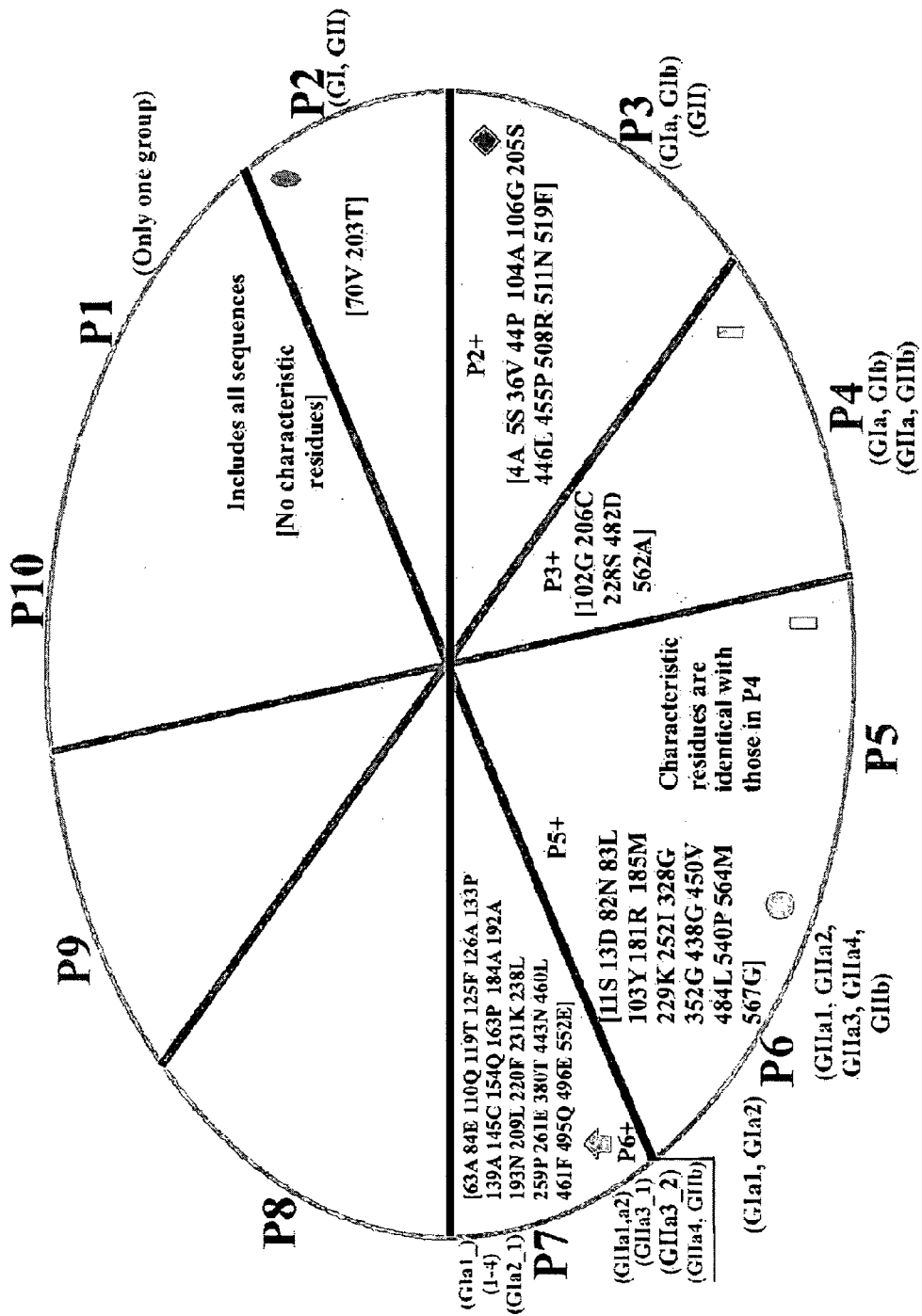
FIG. 2A depicts partition-wise matching of norovirus characteristic residues using the software. The matches are shown as a wheel representation of the 10 partitions P1-P10 showing partition-wise matches for the aligned input target sequence (norovirus "Seacroft"; NCBI accession no. AJ277620). Single letter codes of input target sequence residues that match the characteristic residues in the norovirus database are shown within square brackets for partitions P1-P7. For each partition P1-P6, all sequence groups Gn, where n represents letter combinations, are color coded within parentheses outside the wheel. Of these, sequence groups that match the database characteristic residues are shown in black. Details about the remaining partitions are available from website prion.bchs.uh.edu/recovir. Symbols Pn+ indicates that all characteristic residues of the previous partition "n" are also included in the current partition.

Sequences belonging to the norovirus genus tree have been described elsewhere [40]. Briefly, these sequences form a single group in partition P1 (FIG. 2A). Partition P2 splits this sequence group into the 2 known major genogroups GI and GII of noroviruses (See additional file 1: Supplementary Table 1) [4, 40]. Group GI further divides into GIa and GIb in partition P3 while group GII divides into GIIa and GIIb in partition P4 (or P5 that is identical with P4) (FIG. 2A & See additional file 1: Supplementary Table 1). Partition 6 further splits both GI and GII groups. Group GIa is divided into GIa1 and GIa2 while the group GIa splits into 4 groups (GIIa1-a4). In partition 7, Group GIa splits into 4 groups GIa1-a4 while GIIa3 splits further into the GIIa3_1 and GIIa3_2 groups (FIG. 2A & See additional file 1: Supplementary Table 1). Groups GIb, GIIa4 and GIIb do not split up any further in this partition. Details of the remaining partitions P8-P10 are available at website prion.bchs.uh.edu/recovir.

SUPPLEMENTARY TABLE 1

| Partitions | Sequence groups | Norovirus sequences in groups |
|---|---|---|
| P2 | GI | Norwalk_1IHM, Aichi_Aic[AB010145), Kyoto89_Ky89[L23828), Chiba_Chb[AB042808), Koblenz_Kob[Q91185), Valetta_Val[CAB89102), Thistlehall_Thi[CAB89102), Musgrove_Mus [CAB89095), Southampton_Sou[Q04542), Whiterose_Wh1[CAB89091), bs5_bs5[AF093797), Sindlesham_Si [CAB89096), Norway Stav_Nor[AF145709), Potsdam_Pot[Q8VA02), VA115_Va1[AY038598), Birmingham_Bi[CAB89093), DSV_Sa[U04538), Winchester_Wi[CAB89090), Jena_Bovine_Jen[AJ011099), Bovine_BO [AF542083) |
|  | GII | Beeskow_Bee [Q915C5), Dijon171_Dij[Q8QY55), Berlin_Ber[Q915C2), Altenkirchen_Al[Q916E8), Frankfurt_Fr[Q915D1), Grimsby_Gr [AJ004864), VA387_Va3[AY038600), Parkroyal_Pa[Q9IV44), Ludwigs_Lu[Q915C9), Koenigs_Ko[Q915C4), Symgreen_Sy[Q9IV38), Bristol_Br[S40111), Lordsdale_Lo[P54635), MD145_Md[Q8V0P2), Camberwell_Ca[Q68537), Idaho_Id[Q913B7), VA207_Va2[Q91H09), Amsterdam_Am[AF195848), Leeds_Le[Q9IV49), Gwynedd_GW[AAL12980), Chesterfield_Ch[Q913B6), Mexico[Q68291), Snow Mountain_Sn[U70059), Hillingdon_Hi[Q9IV50), MOH_MO[AF397156), White River_Wh2[AF414423), Erfurt_Er[Q915C7), Chitta_Cht[Q9QMK6), Schwerin_Sc[Q91I15), Wortley_Wo[Q9IV39), Pirna_Pi[Q915C6), Dillingen_Di[Q916E6), Wiesbaden_Wi[Q916E4), Hawaii_Ha[Q68104), Seacroft_Se[Q9IV37), Bham132_Bh[Q9IV46), Rbh_Rb[Q9IV40), Minireo_Re[U02030), Toronto_To[Q66296), Melksham_Mel[X81879), Auckland_Au[U46039), Bitburg_Bi[Q915D2), Ober_Ob[Q916E5), Japan_Ja[23830), Arg320_Ar_Mex[Q9PYA7), Swine_Sw1[Q8V713), Swine_Sw2[BAB83516), Alphatron_Al[AF195847), Ft Lauderdale_Ft[AAL13031) |
| P3 | GIa | 1IHM, Aic, Ky89, Chb, Kob, Val, Thi, Mus, Sou, Wh1, bs5, Si, Nor, Pot, VA1, Bi, Sa, Wi |
|  | GIb | Jen, BO |
|  | GII | Bee, Dij, Ber, Al, Fr, Gr, Va3, Pa, Lu, Ko, Sy, Br, Lo, Md, Ca, Id, Va2, Am, Le, GW, Ch, Mex, Sn, Hi, MO, Wh2, Er, Cht, Sc, Wo, Pi, Di, Wi, Ha, Se, Bh, Rb, Re, To, Mel, Au, Bi, Ob, Ja, Ar, Sw1, Sw2, Al, Ft |
| P4 & P5 | GIa & Ib | Same as in P3 |
|  | GIIa | Bee, Dij, Ber, Al, Fr, Gr, Va3, Pa, Lu, Ko, Sy, Br, Lo, Md, Ca, Id, Va2, Am, Le, GW, Ch, Mex, Sn, Hi, MO, Wh2, Er, Cht, Sc, Wo, Pi, Di, Wi, Ha, Se, Bh, Rb, Re, To, Mel, Au, Bi, Ob, Ja, Ar, Sw1, Sw2 |
|  | GIIb | Al, Ft |

-continued

SUPPLEMENTARY TABLE 1

| Partitions | Sequence groups | Norovirus sequences in groups |
|---|---|---|
| P6 | | |
| | GIa1 | 1IHM, Aic, Ky89, Chb, Kob, Val, Thi, Mus, Sou, Wh1, bs5, Si |
| | GIa2 | Nor, Pot, VA1, Bi, Sa, Wi |
| | GIIa1 | Bee, Dij, Ber, Al, Fr, Gr, Va3, Pa, Lu, Ko, Sy, Br, Lo, Md, Ca |
| | GIIa2 | Id, Va2, Am, Le, GW |
| | GIIa3 | Ch, Mex, Sn, Hi, MO, Wh2, Er, Cht, Sc, Wo, Pi, Di, Wi, Ha, Se, Bh, Rb, Re, To, Mel, Au, Bi, Ob, Ja, Ar |
| | GIIa4 | Sw1, Sw2 |
| | GIIb | Al, Ft |
| P7 | G ((Ia1_1)) to [Ia1_4] | ((1IHM, Aic, Ky89)) (Chb, Kob, Val, Thi, Mus) {Sou, Wh1} [bs5, Si] |
| | GIIa1 & a2 | Same as in P6 |
| | GIIa3_1 | Ch, Mex, Sn, Hi, MO, Wh2, Er, Cht, Sc, Wo, Pi, Di, Wi, Ha |
| | GIIa3_2 | Bh, Rb, Re, To, Mel, Au, Bi, Ob, Ja, Ar |
| | GIIa4 & IIb | Same as in P6 |

Norovirus strains in different sequence groups in partitions P2-P7. This distribution is based on norovirus capsid residues. Partition P2 entries show complete strain names along with their NCBI accession numbers enclosed within square brackets and strain codes that are indicated as "_X" where X refers to the 2 or 3 letter codes e.g X id 1IHM for Norwalk strain and it is Aic for the Aichi strain. These strain codes are used in all subsequent partitions P3-P7. The different GIa1 sequence groups in P7 are enclosed in different types of parentheses: GIa1__1: (( . . . )); GIa1__2: ( . . . ); GIa1__3: { . . . }; GIa1__4: [ . . . ]. The red boldfaced code in P7 indicates the minireovirus strain (NCBI accession no. U02030).

Characteristic Residue Comparisons and Strain Identification for Complete Sequences The characteristic residues of the norovirus genus tree stored in the program databases unambiguously identified the closest strains of target norovirus complete capsid sequences (Table 2).

accession codes are enclosed within square brackets for all capsid sequences except for Norwalk virus whose PDB code is correspondingly shown. The enterovirus capsid sequences refer to those of VP1 subunits. Abbreviations used: HEV: Human enterovirus; Cox; Coxsackievirus.

As an example, the results for norovirus "Seacroft" sequence (NCBI: AJ277620) are described here. Comparisons of the characteristic residue locations with the corresponding residues of this sequence showed that the maximum number of matches in partition P2 occurred in the aligned locations 70V and 203T of group GII and not for GI (FIG. 2A). The corresponding GI locations were 701 and 201V respectively when mapped to the unaligned reference Norwalk virus (PDB ID: 1IHM) sequence (FIG. 2B). Thus, the program searched only along the GII branch of the norovirus genus tree in subsequent partitions. In partition P3, the query sequence maximally matched the GII characteristic residues 4A, 5S, 36V, 44P, 104A, 106G, 205S, 446I, 455P, 508R, 511N

TABLE 2

Strains Detected for Some Partial and Complete Amino Acid Residues of Noro and Enterovirus Capsids

| Input amino acid | | | | Output | | | |
|---|---|---|---|---|---|---|---|
| Complete capsid sequence | | Partial capsid sequence | | Detected strains corresponding to input cols | | | |
| Col (1) Noro | Col (2) Entero | Col (3) Noro | Col (4) Entero | Col (1) Noro | Col (2) Entero | Col (3) Noro | Col (4) Entero |
| Seacroft [AJ277620] | Polio__2 [DQ841140] | 1UK1 [DQ665819] | Cox-B5 [AF114383] | Minireovirus [U02030] | Polio__3 [AF448782] | Beeskow [Q915C5] | Cox-B5 [AF114383] |
| Appalachicola [AF414406] | Simian__A [NP__714932] | 2JP1 [AB264170] | Echo-11 [AB239122] | Chiba [AB042808] | Simian-7 [AF326759] | Chiba [AB042808] | Echo-11 [AF081326] |
| Baltimore__a [AF414408] | HEV-D [NP__740741] | 3JP2 [AB264158] | Echo-13 [AB239091] | Minireovirus [U02030] | HEV-D [D17595] | Norwalk [1IHM] | Echo-13 [AF081327] |
| Baltimore__b [AF414404] | HEV-71 [AAY59418] | 4JP3 [AB264152] | HEV-B [DQ842180] | Chiba [AB042808] | HEV-A71 [AF135944] | Potsdam [AF439267] | Cox-B3 [AF231763] |
| Boxer [AF538679] | Cox-B5 [AAW71476] | 5TP1 [DQ263739] | HEV-75 [DQ468142] | Potsdam [AF439267] | Cox__B5 [AF114383] | Bitburg [AF427112] | Proposed HEV-75 [AF152298] |

Input target complete capsid sequences are shown in cols 1 and 2 while the input partial sequences are shown in cols 3 and 4. The corresponding closest database strains detected by the program are shown in the last 4 cols whose headers are color matched with those of the input sequence cols. The NCBI and 519F while the corresponding GI residues in the reference Norwalk virus sequence are 4A, 5S, 36V, 44A, 104V, 106N, 203A, 405L, 414F, 460H, 463D and 471G respectively (FIGS. 2*a* & 2*b*). In partitions P4 and P5, the maximum number of matches (102G 206C 228S 482D 562A) occurred in GIIa, indicating that further database searches in subsequent partitions should be restricted only to those groups that originate from GIIa.

Of the 4 possible GIIa choices (GIIa1-a4) in the following partition P6, the maximum number of characteristic residue matches occurred in group GIIa3 (FIG. 2A) corresponding to residues 11S, 13D, 82D, 83L, 103W, 181R, 185M, 227K, 250I, 306G, 329H, 397S, 409V, 436L, 492P, 516V and 519A of the unaligned reference sequence (FIG. 2B). Comparisons in partition P7 showed that of the 2 groups GIIa3_1 and GIIa3_2 originating from the GIIa3 group of the previous partition P6, the GIIa3_2 group maximally matched the characteristic residues (FIG. 2A). These matches occurred at 63A, 84S, 110R, 119T, 125V, 126S, 133G, 139I, 145F, 154T, 163E, 184C, 192T, 193G, 207M, 218F, 229R, 236L, 257P, 259N, 347T, 402A, 419V, 420F, 447S, 448E and 504V of the unaligned reference sequence (FIG. 2B). Similar comparisons in partitions P8-P10 conclusively showed that the query sequence is most similar to the minireovirus-like norovirus strain (FIG. 3)

Similarly, the input Appalachicola Bay, the Baltimore 'a' and 'b' and the Boxer strain sequences most closely resembled the Chiba, minireovirus and the Potsdam strains of noroviruses (see Table 2). Strains were also correctly predicted after removing random stretches of 10-15 amino acids from these sequences indicating thereby that the strain prediction capability of the program is quite robust and is independent of the locations of the input target sequences.

Strain Identification of Input Partial Amino Acid Target Sequences of Noroviruses Strains of five partial amino acid capsid sequences of noroviruses were consistently predicted using both the "noro" and "unknown" database options of the GUI (FIG. 1B). Only one of the 5 input sequences (1UK1) explicitly included the N-terminus residues while the remaining sequences 2JP1, 3JP2, 4JP3 and 5TP1 were from different capsid regions (Table 3).

TABLE 3

Input Target Partial Capsid Sequences of Noroviruses (A) and Partition-wise Distribution of Maximally Matching Residues (B)

Target Partial Amino Acid Residues of Norovirus Capsid Sequences -A-

>1UK1|[NCBI:DQ665819]
MKMASSDANPSDGSTANLVPEVNNEVMALEPVVGAAIAAPVAGQQNVIDPWIRNNFVQAPGGEFTVSP
RNAPGEILWSAPLGPDLNPYLSHLAR

>2JP1|[NCBI:AB264170]
SADGATGAGQLVPEVNTADPIPIDPVAGSSTALATAGQVNLIDPWI INNFVQAPQGEFTISPNNTPGDV

>3JP2|[NCBI:AB264158]
GASGAGQLVPEVNASDPLAMDPVAGSSTAVATAGQVNPIDPWIINNFVQAPQGEFTISPNNTPGDV

>4JP3|[NCBI:AB264152]
GTSGAGQLVPEANTAEPISMDPVAGAATAVATAGQINMIDPWIMSNFVQAPQGEFTVSPNNTPGDV

>5TP1|[NCBI:DQ263739]
DGAAGLVPEINNEAMALDPVAGAAIAAPLTGQQNIIDPWIMNNFVQAPGGEFTVSPRNSPGEVLLNLEL
GPEI

-B-

| Partial Sequence | Partition-wise maximally matching characteristic residues (Corresponding sequence group) | | | | | |
|---|---|---|---|---|---|---|
| | P2 | P3 | P4 | P5 | P6 | P7 |
| 1UK1 | 70V (GII) | 4A, 5S, 36V, 44P (GII) | | | ** | 11S, 46A, 63A, 65G, 82S, 83A, 84P, 89L (GIIa1) |
| 2JP1 | 20Q, (GI) | 70I 26N, 36V, 44A (GIa) | — | — | 11S, 13D, 14G (GIa1) | ** |
| 2JP2 | 20Q, (GI) | 70I 26N, 36V, 44A (GIa) | — | — | ** | ## |
| 4JP3 | ** | 26N, 36V, 44A (GIa) | — | — | ** | ## |

TABLE 3-continued

Input Target Partial Capsid Sequences of Noroviruses (A) and
Partition-wise Distribution of Maximally Matching Residues (B)

| 5TP1 | 70V (GII) | 36V, 44P (GII) | ## | 13D, 14G, 46T, 63A, 65G, 82N, 83L, 84E, 89I (GIIa3_2) |
|------|-----------|----------------|-----|------------------------------------------------------|

Ambiguities detected during search process:
\*\*: Equal number of characteristic residue matches found in all of the groups
Blank entry: No matches found for the characteristic residues
—: Identical to previous partition
: Ambiguity detected: More than one relevant group had equal no. of highest matches In Table 3, part B above, the maximally matching sequence groups for each partition are shown within parentheses. Residues and sequence groups in Table 3, part B above use notations of FIGS. 2A & 2B. Residues are color matched in Table 3, parts A & B above.

Despite the short sizes of the input partial sequences and the variations in their capsid locations, the program unambiguously recognized the strains of all of them from their matches with the characteristic location residues. Location 70 in partition P2 determined the major genogroup in all but one sequence. Sequences 1UK1 and 5TP1, both containing 70V, belonged to genogroup GII while 2JP1 and 3JP2 belonged to genogroup GI based on the corresponding 70I residue (Table 3; FIGS. 2A&B). All of the GI residues (2JP1 & 3JP2) contained 20Q in partition P2. However, the major genogroup of sequence 4JP3 appeared to be ambiguous as it showed features of both GI and GII groups in partition P2 (ambiguity shown as \*\* in Table 3). It contained not only 70V, typical of GII sequences, but also the GI-indicator 20Q. In addition, this sequence also presented the additional ambiguity of having an equal number of characteristic residue matches in both GI and GII groups for partition P2 (Table 3). To resolve this ambiguity, the program carried over the partition P2 matches of this sequence (4JP3) to partition P3.

In partition P3, the program examined characteristic residue locations 4, 5, 26, 36 and 44 for all of the sequences (FIGS. 2A&B). Residue 44 unambiguously confirmed the distinction between the GI and the GII group sequences in this partition. Sequences 2JP1, 3JP2 and 4JP3, by virtue of 44A, were all characterized as GI sequences similar to the reference Norwalk virus sequence (FIG. 2B; Table 3). In contrast, sequences 1UK1 and 5TP1, containing 44P, are genogroup GII sequences. In addition, because 1UK1 has 4A and 5S and sequences 2JP1, 3JP2 and 4JP3 have 26N in partition P3, choices of their genogroups were unambiguously confirmed in this partition (FIGS. 2A&B; Table 3). Residue 36V, being conserved in all of the sequences in P3, was not of much help in determining the sequence groups in this partition (Table 3).

The program ignored partitions P4 and P5 for the 1UK1 and 5TP1 sequences due to ambiguities in residue matches. The next partition P6 showed another ambiguity of having more than one group with the highest number of matches for both these sequences (Table 3). However, matches in partition P7 clearly indicated that sequence 1 UK1 belongs to GIIa1 while 5TP1 belongs to group GIIa3_2 (Table 3; FIGS. 2A&B). Further matches in partitions P8-P10 (Table 3) confirmed that 1UK1 and 5TP1 were most similar to the Beeskow and the Bitburg strains respectively (Tables 2, 3; See additional file 1: Supplementary Table 1).

Thus, the identified strain of the partial sequence 1UK1 is consistent with its NCBI classification as a member of the GII.4 cluster. However, 5TP1 appears to belong to the GII.3 sequence cluster according to the present analysis and not to GII.4 as shown in the NCBI database. Similarly, partitions P6-P10 allowed the program to confirm that the remaining sequences 2JP1, 3JP2 and 4JP3 indeed belong to genogroup GI (Tables 2 & 3) which is consistent with the NCBI classification of these sequences. In addition, the program determined from residue comparisons that these sequences 2JP1, 3JP2 and 4JP3 are most similar to the norovirus GI Chiba, Norwalk and the Potsdam strains respectively (Tables 2 & 3). Such detailed strain information is seldom available for partial sequences in public domain databases.

Strain Detection Complete/Partial AA Sequences of Capsids

The program first correctly identified the strains for 5 complete and 5 partial enterovirus capsid sequences. The complete capsid sequences were those of the VP 1 subunits of poliovirus, simian enterovirus, echovirus and the coxsackievirus strains (one sequence per strain) (Table 2). Different reference sequences were tested for aligning the target sequences. The target sequence strains were all correctly identified regardless of the choice of the reference sequences (Tables 2 & 3). As an example, strain identification for the poliovirus strain (NCBI: DQ841140) using the porcine enterovirus-8 sequence (PEV-8: NCBI accession number AF406813) as reference is briefly described. The second partition P2 of enteroviruses contains only 2 reference groups 1 and 2 in the program database (Table 4). Of these, group 2 contains only the porcine enteroviruses (PEV) serotype 9 (PEV-9; NCBI: AF363453) indicating that the PEV-9 strains are distinct from the other enterovirus strains all of which (including the PEV-8 strain) belong to group 1. This group is characterized by nine residues 40P, 42L, 44A, 46E, 48G, 72E, 124T, 125Y, 127R, 150Q, 155P, 157G, 169W, 176S, 191P, 199Y, 202F and 203Y (reference sequence PEV-8 numbering) in the database (Table 4). Because all of these residues match the corresponding locations in the target poliovirus sequence, the program assigns group 1 to the target sequence in partition P2 and skips the next partition P3 as it is identical to P2 (Table 4).

TABLE 4

Partition-Wise Strain Determination of a Poliovirus-2 (PV-2) Sequence

| Partition | Total no. of groups (Maximally matching group no.) | Matching residues (Numbering based on reference PEV-8¶ sequence) | Reference database strains present in maximally matching group |
|---|---|---|---|
| P2, P3 | 2(1) | 40P 42L 44A 46E 48G 72E 124T 125Y 127R 150Q 155P 157G 169W 176S 191P 199Y 202F 203Y | All enteroviruses including various human (Coxsackie, echo and polio) strains and some animal strains like bovine and simian enteroviruses. Includes the PEV-8 strain but does not include the PEV-9 strain (More than 100 strains) |
| P4 | 3(2) | P3+ [61L 62Q 78L 106S 115S 131D 152L 170N 174S] | All of the P2/P3 partition strains except PEV-8 strains |
| P5 | 7(6) | P4+[43T 55G 64T 84L 156H] | 32 echoviruses, 21 coxsackieviruses, all polioviruses and 7 other human and animal enteroviruses (Total of ~60 strains) |
| P6 | 8(7) | P5+[158G] | All polioviruses, 12 coxsackieviruses and 1 echovirus |
| P7, P8 | 14, 44£ | ** | |
| P9 | 72(62) | P6+[4K 19L 35N 47T 49E 51D 52T 60E 63A 66C 68F 69S 70L 73T 77Y 79M 80S 81R 83S 85M 90L 109T 113S 117I 119K 120F 123F 126W 129D 137L 138E 140K 153F 154T 166S 167Q 171A 172P 173N 175T 178Y 180R 184C 185P 187S 189R 192F 195V 197N 198Y 206D 207G 209F 216Y 217G 218I 221G 222D 225G 228S 230R 233N 242G 249F 250L 252P 253V 254N 256E 258Y 262P 264V 266Y 268A] | Poliovirus-2 strains |
| P10 | 75(64) | P9+[11I 17N 33M 36Q 37G 45A 50S 57S 58T 71R 76E 103Y 121K 122A 130L 146N 147L 159A 179T 186A 200T 210D 227I 231M 232A 248I 251R 263L 265S 281P] | Poliovirus-2 strains |

**Ambiguity: 2 or more groups have identical number of matches in both these partitions.
¶Porcine enterovirus (NCBI accession no.: AF406813)
£No matching reference group for partitions P07, P08 due to ambiguity; Strains not shown for these two partitions. All strains of poliovirus serotypes (1, 2 & 3) cluster as an independent group in partition P8.

The complete capsid sequence of input PV-2 target sequence (NCBI accession: DQ841140) was used as input. Symbol Pn+: Indicates "including all matching residues of the earlier partition Pn".

The program detects the separation of group 1 into two groups 1a and 1b in partition P4. This creates a total of 3 groups (1a, 1b and 2) in this partition (Table 4). While group 1a contains only the PEV-8 sequences which have independently diverged from group 1 of partition P2/P3, group 1b contains the remaining group 1 sequences of these partitions. Group 2 of partition P2/P3 remains unaltered in partition P4. On comparing the characteristic residues of these three groups, the program determines that the target sequence most closely resemble group 2 in partition P4 because of the matches with residues 61L, 62Q, 78L, 106S, 115S, 131D, 152L, 170N and 174S (PEV-8 numbering) that characterize this group (Table 4). Similarly, matches with residues 43T 55G 64T 84L 156H in partition P5 allow the program to assign group 6 to the target sequence in this partition which contains nearly 60 other similar enterovirus sequences including those of polioviruses (Table 4). Similarly, residue 158G distinguishes group 7 as the maximally matching group out of the eight groups in partition P6. This group includes many similar strains in the program database including 12 strains of different coxsackievirus serotypes, one echovirus strain and strains of all 3 poliovirus serotypes (Table 4).

The three poliovirus serotypes which remain clustered with several other human enteroviruses in partition P7 finally separate as an independent group in partition P8 (group details not shown). However, partitions P7 and P8 showed an ambiguity with reference to the input target sequence. Both of these partitions have more than one group having identical highest number of residue matches with the target. This ambiguity did not allow the program to decide the best group in these partitions. Consequently, all group information of these partitions was carried over to the subsequent partition P9 (Table 4).

Partition P9 contains a total of 72 sequence groups including an independent group (#62) containing only the poliovirus-2 strains. The program detected this group to be the maximally matching group for the target sequence and this detection was confirmed in the next partition P10. Thus, the input target sequence was correctly detected as a poliovirus-2 strain (Table 4). Strains for the remaining picornaviruses (Tables 2 & 3) were also unambiguously detected regardless of the choice of the reference strains.

Recombination and Spontaneous Mutations

Only a few enterovirus strains could be analyzed for recombination and spontaneous mutations using RECOVIR due to the manual nature of such analysis in the present version of the software. Partition-wise comparisons of strain diversifying residues VP1-VP3 genes of the hepatitis-A (HAV) strains at the nucleotide and the amino acid levels indicated that the SLF88 (AY032861) and the MBB (M20273) strains may be putative parental strains that yield the recombinant product strain 9F94 (AJ519487) (data not shown). This is consistent with recent results obtained using conventional topology comparisons of phylogenetic trees by sliding windows across the corresponding multiple aligned sequences [44].

Similarly, partition-wise matches in the norovirus partial sequence 6ST1 indicated spontaneous mutations. While residue 20Q in partition P2 indicates that 6ST1 belongs to GI, residue 70V in the same partition indicates that this sequence may belong to GII as seen for sequence 5TP1 (Table 3). The program, therefore, checks both these possibilities for maximum number of matches in subsequent partitions. Each subsequent partition confirms that this sequence indeed belongs to GI and is closest to the Potsdam strain (NCBI accession AF439267). Therefore, location 70, which is an iso-leucine for other GI sequences (Table 3), may be a spontaneous mutation site.

Despite the limited results, it appears that the present software may provide a more efficient way to detect recombination sites than those provided by most of the current widely used methods. This is because such methods are inherently time consuming as their accuracy depends on multiple runs with different sequence window parameters In addition, the entire procedure must be repeated every time a new sequence needs to be analyzed. In contrast, the present method does not repeatedly compare phylogenetic trees using sliding sequence windows. Instead, it efficiently performs node-wise comparisons of the trees using a one-time created database of strain distinguishing residues.

Approximate Processing Times

The program rapidly identified the calici and the picornavirus strains. In typical runs on outbreak sequence data available from public databases, it took only 6 and 9 minutes of real time respectively to identify the strains of a number of norovirus sequences contained in 2 files. The first file had 71 complete norovirus capsid sequences while the second file had 117 norovirus capsid sequences of which 22 were complete sequences while the remaining 95 were partial sequences each of which was between 75 and 85 residues long. This indicates a real time (including I/O) of approximately 5 seconds per sequence. Comparable speeds were also observed in processing other calicivirus and picornavirus sequences processed separately in different files as well as in files containing sequences of these virus families together. The "unknown" database option (FIG. 1B) was selected in all of these runs. Selecting the known database type in the GUI reduced the processing times even further. Complete benchmark details of such strain identification runs are available at website prion.bchs.uh.edu/recovir.

CONCLUSIONS

A software package RECOVIR that can efficiently and accurately characterize strains of the highly divergent caliciviruses and picornaviruses is described here. In contrast to the currently existing techniques that mainly use sequence similarity scores to identify strains in these viruses, this package relies on capsid residues that unambiguously distinguish among a large number of calici and the picornavirus reference strains. Such strain distinguishing residues are stored in partitioned databases and compared with the residues of target capsid sequences using efficient tree based search techniques to rapidly identify strains of the target sequences. This method implements a generalized algorithm of a method outlined earlier for noroviruses [40]. Consequently, the program allows strain identification of not only norovirus sequences but of all other caliciviruses and of the picornavirus sequences as well. Strains were recognized for more than 300 complete and partial capsid sequences of calici and picornaviruses with the average strain identification time (real time including I/O) being approximately 5 seconds per sequence. The method is general enough to be applicable to the nucleotide sequences of calici and picornavirus capsids thereby providing powerful alternatives that complement current strain determination techniques.

Availability and Requirements

Project home pages: http://prion.bchs.uh.edu/recovir

Operating systems: Windows-XP, Linux and UNIX

Programming language: Perl and Java

Other requirements: X-Windows support (such as Cygwin) is needed for remotely running the program under Linux/UNIX environments.

Author Contributions

Dianhui Zhu coded the software and designed the GUI. Sugoto Chakravarty developed the concept, designed the algorithm and its implementation and created the initial databases. Sugoto Chakravarty and Dianhui Zhu performed extensive troubleshooting with both synthetic and real data. Sugoto Chakravarty and George E. Fox wrote the paper. All authors suggested improvements at different stages of manuscript preparation and read and approved the final version of the manuscript.

REFERENCES CITED IN CAPSID EMBODIMENT

The following references are cited within the text:

1. Drake J W, Holland J J: Mutation rates among RNA viruses. *Proc Natl Acad Sci USA* 1999, 96(24):13910-13913.
2. King A M Q, Brown F, Christian P, Hovi T, Hyypiä T, Knowles N J, Lemon S M, Minor P D, Palmenberg A C, Skem T et al: Picornaviridae. In: *Virus Taxonomy Seventh Report of the International Committee for the Taxonomy of Viruses*. Edited by Van Regenmortel M H V, Fauquet, C. M., Bishop, D. H. L., Calisher, C. H., Carsten, E. B., Estes, M. K., Lemon, S. M., Maniloff, J., Mayo, M. A., McGeoch, D. J., Pringle, C. R., Wickner, R. B. New-York, San Diego: Academic Press; 2000: 657-673.
3. Buchen-Osmond C (ed.): Caliciviridae. New York, N.Y., USA; 2003.
4. Green K Y, R. M. Chanock, Kapiakan A Z: Human caliciviruses. In: *Fields virology.* 4 edn. Baltimore, Md.: Lippincott, Williams & Wilkins; 2001: 841-874.
5. Matson D O, Szucs G: Calicivirus infections in children. *Curr Opin Infect Dis* 2003, 16:241-246.
6. Asanaka M, Atmar R L, Ruvolo V, Crawford S E, Neill F H, Estes M K: Replication and packaging of Norwalk virus RNA in cultured mammalian cells. *PNAS* 2005, 102(29): 10327-10332.
7. Wirblich C, Meyers G, Ohlinger V F, Capucci L, Eskens U, Haas B, Thiel H J: European brown hare syndrome virus: relationship to rabbit hemorrhagic disease virus and other caliciviruses. *J Virol* 1994, 68(8):5164-5173.

8. Green K Y, Vinje J, Gallimore C I, Koopmans M, Hale A, Brown D W G: Capsid protein diversity among Norwalk-like viruses. *Virus Genes* 2000,20:227-236.
9. Ando T, Noel J S, Fankhauser R L: Genetic Classification of "Norwalk-like Viruses. *The Journal of Infectious Diseases* 2000, 181:S336-S348.
10. Katayama K, Shirato-Horikoshi H, Kojima S, Kageyama T, Oka T, Hoshino F, Fukushi S, Shinohara M, Uchida K, Suzuki Y et al: Phylogenetic analysis of the complete genome of 18 Norwalk-like viruses. *Virology* 2002, 299 (2):225-239.
11. Okada M, Shinozaki K, Ogawa T, Kaiho I: Molecular epidemiology and phylogenetic analysis of Sapporo-like viruses. *Arch Virol* 2002, 147(7):1445-1451.
12. Knowles N: IAH Virus pages. In: Institute for Animal Health, U.K., at www website iah.bbsrc.ac.uk/virus/; 2003.
13. Prasad B V V, Hardy M E, Dokland T, Bella J, Rossmann M G, Estes M K: X-ray Crystallographic Structure of the Norwalk Virus Capsid. *Science* 1999, 286(5438):287-290.
14. Chen R, Neill J D, Estes M K, Prasad B V V: X-ray structure of a native calicivirus: Structural insights into antigenic diversity and host specificity. *PNAS* 2006, 103 (21):8048-8053.
15. Hadfield A T, Lee W, Zhao R, Olivera M A, Minor I, Rueckert R R, Rossmann M G: The refined structure of human rhinovirus 16 at 2.15 A resolution: implications for the viral life cycle. *Structure* 1997, 5:427-441.
16. Kim S S, Smith T J, Chapman M S, Rossmann M G, Pevear D C, Dutko F J, Felock P J, Diana G D, McKinlay M A: Crystal structure of human rhinovirus serotype 1A (HRV1A). *J Mol Biol* 1989, 210:91-111.
17. Rossmann M G, Arnold E, Erickson J W, Frankenberger E A, Griffith J P, Hecht H J, Johnson J E, Kamer G, Luo M, al. AGMe: Structure of a human common cold virus and functional relationship to other picornaviruses. *Nature* 1985, 317(145-153).
18. Verdaguer N, Blaas D, Fita. I: Structure of human rhinovirus serotype 2 (HRV2). *J Mol Biol* 2000, 300:1179-1194.
19. Zhao R, Pevear D C, Kremer M J, Giranda V L, Kofron J A, Kuhn R J, Rossmann. M G: Human rhinovirus 3 at 3.0 A resolution. *Structure* 1996, 4:1205-1220.
20. Zheng D-P, Ando T, Fankhauser R L, Beard R S, Glass R I, Monroe S S: Norovirus classification and proposed strain nomenclature. *Virology* 2006, 346(2):312-323.
21. Vinje' J, Hamidjaja R A, Sobsey M D: Development and application of a capsid VP1 (region D) based reverse transcription PCR assay for genotyping of genogroup I and II Noroviruses. *J Virol Methods* 2004, 116:109-117.
22. Kageyama T, Kojima S, Shinohara M, Uchida K, Fukushi S, Hoshino F, Takeda N, Katayama K: Broadly reactive and highly sensitive assay for Norwalk-like viruses based on real-time quantitative reverse transcription PCR. *J Clin Microbiol* 2003, 41(1548-1557).
23. Richards G P, Watson M A, Kingsley D H: A SYBR green, real-time RT-PCR method to detect and quantitate Norwalk virus in stools. *J Virol Methods* 2004, 116:63-70.
24. Fankhauser R L, Monroe S S, Noel J S, Humphrey C D, Bresee. J S, Parashar U D, Ando T, Glass R I: Epidemiologic and Molecular Trends of "Norwalk-like Viruses" Associated with Outbreaks of Gastroenteritis in the United States. *J Infect Dis* 2002, 186:1-7.
25. Kageyama T, Shinohara M, Uchida K, Fukushi S, Hoshino F B, Kojima S, Takai R, Oka T, Takeda N, Katayama K: Coexistence of multiple genotypes, including newly identified genotypes, in outbreaks of gastroenteritis due to norovirus in Japan. *J Clin Microbiol* 2004, 42:2988-2995.
26. Chakravarty S, Hutson A M, Estes M K, Prasad B V V: Evolutionary Trace Residues in Noroviruses: Importance in Receptor Binding, Antigenicity, Virion Assembly, and Strain Diversity. *J Virol* 2005, 79:554-568.
27. Lichtarge O, Bourne H R, Cohen F E: An evolutionary trace method defines binding surfaces common to protein families. *J Mol Biol* 1996, 257(342-358).
28. NCBI: Life sciences databases at the National Center for Biotechnology Information (NCBI), USA. In: NCBI, National Center for Biotechnology Information, see website on the world wide web ncbi.nlm.nih.gov.
29. Thompson J D, Higgins D G, Gibson T J: CLUSTAL W: improving the sensitivity of progressive multiple sequence alignment through sequence weighting, position-specific gap penalties and weight matrix choice. *Nucl Acids Res* 1994, 22(22):4673-4680.

Adaptive Mutations Embodiment of this Invention

Adaptive Mutations Explain Strain Diversification in Rhinoviruses and Noroviruses Most single stranded RNA viruses adapt to host immune responses by rapidly mutating their capsid proteins to generate a large number of strains. An effective way to understand this strain diversity would be to decipher those capsid residues whose mutations may be linked to important determinants of host immune responses such as receptor binding and antigenicity. In the present study, we show using evolutionary trace based approach that a large number of the strain diversifying residues belong to the known receptor binding sites and some of the neutralizing sites of human rhinoviruses (HRV) thereby validating the ET approach earlier applied to noroviruses NoV). In both NoV and HRV, these capsid residues mostly line structurally spacious and inter-connected pockets. These pockets, perhaps, define major adaptation sites that structurally facilitate strain diversification. The adaptive sites explain the antigenic diversity of HRV by uniquely distinguishing among phylogenetic groups of antigenically related serotypes. Therefore, similarly constructed groups of NoV may indicate antigenically related strains, none of which have been identified for these non-cultivatable viruses. When applied to sequences of other caliciviruses and picornaviruses, the present approach reveals significant relationships among the currently known genera and species of these viruses on the basis of unique strain diversifying residues. Such residues may therefore distinguish and classify these distinct virus families.

Introduction

Rapid mutations in coat protein residues allow most single stranded RNA (ssRNA) viruses to adapt to host immune responses. Tracking and deciphering these mutation patterns is important in understanding adaptations in these viruses. However, this is seemingly impossible because of the apparent randomness of sequence locations where these mutations occur, especially when different ssRNA virus families are considered.

One way to understand adaptations in these viruses is to identify those capsid residues whose mutations may generate new strains and modulate important determinants of host immune responses such as receptor binding and antigenicity. For some ssRNA viruses having only a few serotypes, experimental approaches that combine analysis of neutralization escape mutants and conventional sequence alignment may identify such strain diversifying capsid residues, as has been done for polioviruses (6, 19, 21, 24, 58). However, these approaches are impractical when a large or unknown number of serotypes exist as in human rhinoviruses (HRV) and the noroviruses (NoV) of the Picornaviridae and the Caliciviridae families respectively.

Computational techniques effectively identify strain diversifying residues in such cases. However, conventional sequence comparisons among NoV and HRV (1, 17, 20, 23, 29, 42, 48, 72, 75) have not been able to identify these residues. This is because such comparisons attempt to identify maximally conserved regions across phylogenetic trees thereby masking biologically significant capsid regions in HRV and NoV due to high sequence divergence.

Evolutionary trace (ET) techniques appear to address these issues while determining functionally important residues in simpler protein systems (60, 67). This is done by identifying node-wise sequence conservation in phylogenetic trees followed by structural mapping of the conserved residues (45). We earlier applied ET-based techniques to predict capsid residues putatively involved in receptor binding, antigenicity and strain diversification in NoV (12). Recent confirmation of some of these results (3, 10, 31, 46, 53) indicated that such predictive approaches may be used to understand ssRNA virus strain diversification in a more general way provided the NoV approach is successful for viruses belonging to a different ssRNA family.

The relatively well characterized HRV have been chosen in the present study to reliably validate the NoV approach and extend it to other picornaviruses. Each serotype of HRV belongs to either the HRV-A or the HRV-B species (36, 61, 68). Capsid structures of five of the serotypes show that each icosahedral capsid consists of 60 copies of each of the four monomers VP 1-4 (26, 35, 59, 71, 74). The receptors bind in or near structural 'canyons' surrounding the icosahedral 5-fold axes in VP1 subunit and drug binding pockets are located underneath the canyons (4, 11, 25, 28, 65). Of the four neutralizing immunogenic (NIm) sites (IA, IB, II and III) (54, 59), only the NIm-IA and IB sites are located in VP1 towards the exposed parts of the canyons (59). We analyze here the capsids of HRV and other picornaviruses and caliciviruses in order to elucidate adaptations in ssRNA viruses.

Method

Partitioned phylogenetic trees of VP1 capsid sequences of 100 HRV serotypes were created following the ET method (45) applied earlier to NoV (12). The VP1 sequences were obtained from public databases (38, 51) where only one sequence per serotype was available. The sequences were first aligned using ClustalW (70) and Gonnet-250 series identity matrices were used to create phylogenetic distances. Penalties for gap opening, closing, extension and separation were set to 10, −1, 0.2 and 4 respectively for amino acid sequences. Rooted phylogenetic trees of the aligned sequences were created using the Kitsch algorithm on Phylip distances as implemented on the Cambridge server (33). Assuming uniform evolutionary rates of the sequences, these trees were divided into ten equally spaced partitions (P01-P10) with the inter-partition distance in any given tree being computed from the maximum evolutionary distance within the tree. Ten partitions sufficed for all trees as no further changes in node distributions were observed in any tree with further increase in partition numbers.

Every partition created classes each of which contained groups of similar sequences. Sequences belonging to different classes of a given partition were separately aligned and the resulting aligned classes were compared to obtain the consensus (trace) residues for that partition. Those sequences that remained strictly conserved within a class but differed between various classes were denoted as 'class-specific'. These residues were mapped onto the HRV-16 (PDB ID: 1AYM) structure where class-specific residue (CSR) clusters were analyzed following the procedure described earlier (12).

To identify structural location preferences of the CSRs, void volume cavities and pockets were separately computed for the HRV-16 and the Norwalk virus (PDB ID: 1IHM) capsids. For HRV16, pseudo-dimers composed of the VP1 and VP3 subunits and other VP1-VP4 subunit assemblies were used while for the Norwalk virus capsid, dimers composed of the A and the B subunits (55), trimers (A, B and the C subunits) and the A-subunit pentamers were used. These calculations were done using 1.41 radius probes in the VOIDOO package (37) and on the CASTp server (5). Cavities were defined as void contiguous regions formed by atoms not in touch with surface atoms while pockets were defined as the corresponding regions partly or wholly accessible to surface atoms. Therefore, a pocket, by definition, must have at least one opening that allows access to the interior of the pocket while cavities have no such openings (5). Consequently, exposed regions smaller than the probe size were considered parts of cavities. Accessible and inaccessible surface areas and volumes of the pockets and cavities were computed using definitions of Lee and Richards (43) and Connolly (13, 14).

Capsids of Other Picornaviruses and Caliciviruses

Amino acid sequences of capsids of known serotypes of the human enterovirus (HEV) species A-D were partition-wise analyzed. A total of 388 capsid sequences of all nine known picornavirus genera (68) were then similarly analyzed. The procedure was repeated for a large number of amino acid sequences of all known genera of caliciviruses.

Results and Discussion

Partition-Dependent Classes Show Antigenic Relationships Among Serotypes of HRV

Known Antigenic Relationships

Various antigenic relationships are known among serotypes of HRV. Some serotype pairs (1A and 1B, 2 and 49, 3 and 14, 9 and 32, 12 and 78, 13 and 41, 15 and 74, 29 and 44, and 36 and 58) share reciprocal cross-neutralization with heterotypic antisera while other pairs share one-way antigenic relationships between the pair members (Table 1 & FIG. 4B). Still others, like serotypes 9, 32 and 67 are antigenically related because serotypes 9 and 32 are cross-reciprocally related while serotypes 9 and 67 show one-way relationships (15) (Table 5). In addition, four groups of serotypes share cross-reactivity among the group members as seen in neutralizations with antibodies raised against serotypes obtained from natural infections (50) (Table 5) (15, 16, 62).

TABLE 5

Known Antigenically Related Serotypes of HRV Group Together in Partition dependent Classes

| Reciprocal Cross-Neutralization (15) | | One-way Cross-Neutralization (15) | | Cross-Neutralization After Natural Infection (62) | |
|---|---|---|---|---|---|
| | | | | Serotype | |
| Serotype Pair | Class/Partition | Serotype Pair | Class/Partition | Group | Class/Partition |
| 1A, 1B | A3/P07+ | 5, 42 | B3/P07+ | 1A, 1B | A3/P07+ |
| 2, 49 | A7/P07+ | 6, 14 | B5/P08* | 2, 49 | A7/P07+ |
| 3, 14 | B5/P08+ | 9, 67 | A15/P08+ | 23, 30 | A7/P07+ |
| 9, 32 | A15/P08+ | 11, 40 | A1* → A12, | 13, 41, 82 | A8/P08+ |
| 12, 78 | A10/P07+ | | A19/P06* | 29, 44, 62 | A9* → A21 & |
| 13, 41 | A17/P08+ | 11, 74 | A4* → A12, | | A22/P07* |
| 15, 74 | A16/P08+ | | A16/P07* | | |
| 29, 44 | A22/P08+ | 17, 42 | B* → B2, B3 | | |
| 36, 58 | A23/P08+ | | /P06* | | |
| | | 17, 70 | B2/P07+ | | |
| | | 22, 61 | A17/P08* | | |
| | | 32, 67 | A15/P08* | | |
| | | 36, 50 | A1* → A23, | | |
| | | | A13/P06* | | |
| | | 36, 89 | A23/P08+ | | |
| | | 39, 54 | A8* → A20, | | |
| | | | A19/P07* | | |
| | | 60, 38 | A16/P08* | | |
| | | 66, 77 | A18/P08+ | | |
| | | 76, 11 | A12/P08+ | | |

These serotypes are known using rabbit hyperimmune sera raised against prototype strains for serotypes 1A to 89 of HRV. Pairs having antigenic relationships that lead to mutual antigenic relationships among three or four serotypes are shaded using the same color e.g., relationships between serotypes 3 and 14 (cross-reciprocal) and serotypes 6 and 14 (one-way) ensures that serotypes 3, 6 and 14 are antigenically related. Therefore, the pairs (3, 14) and (6, 14) are shaded using the same color. The + sign indicates that these serotype pairs continue to remain grouped together in subsequent partition classes while the * indicate that the corresponding serotype pairs do not group together in the same class in subsequent partitions. Arrows indicate the target partitions and classes into which some of the one-way related serotype groups get split up from their parent partitions and classes.

Classes Group Antigenically Related Serotypes

Antigenically related serotypes of HRV group together in distinct partition-dependent classes. For example, in P02, serotypes 3 & 14 group together in class B (HRV-B species) while all of the remaining antigenically related pairs belong to class A (HRV-A species) (Table 5, FIGS. 4A & 4B). Subsequent partitions continue to cluster most of these related serotypes and also cluster those antigenically related serotypes that are obtained from natural infections (Table 5; FIG. 4B). Even serotypes sharing antigenic relationships with multiple other serotypes, like serotypes 9, 32 and 67, are grouped together in the same class in at least one partition (Table 5; FIG. 4B).

Classes Distinguish Between Reciprocal Vs. One-Way Related Serotypes

The different partitions distinguish between the reciprocally related serotypes from the one-way related ones. The reciprocal serotypes remain grouped together in a larger number of partitions as compared to the one-way related ones. For example, the mutually reciprocal serotypes 1A and 1B remain together in classes A (P02-P04), A1 (P05, P06) and A3 (P07-P09) (Table 5; FIG. 4B). In contrast, the one-way related serotypes 11 and 74 split up after class A4 in partition P07. These serotypes get distributed into classes A12 and A16 in P08 (FIG. 4B). Similar splits are seen in other one-way related serotype pairs ((11 & 40), (17 & 42), (36 & 50) and (39 & 54)) (Table 5).

Strain Diversifying Locations Include Known Neutralization and Receptor Binding Sites Csrs are Strain Diversifying Locations While partitioned classes show that the phylogenetic trees of HRV portray antigenic diversity, the CSRs define the antigenic diversification locations. This is because class-specific conservation in these residues may be viewed as strain diversifying mutations that generate the antigenically related classes (FIG. 4B). For example, location 1, which is conserved as either Asn or Gly in partition P02, may be equivalently viewed as two possible mutations in this location: Asn generates all class A sequences while Gly generates sequences of class B. Similarly, class-specific mutations in locations 48, 56, 102, 103, 155, 170, 174, 223 and 239 (HRV16 numbering is followed throughout unless stated otherwise) generate the HRV-A and HRV classes in partitions P02-P04 (FIGS. 4B, 4C) while class-specific mutations in the other partition-dependent CSRs generate classes in the remaining partitions (data available with authors from bchs.uh.edu/HRVET).

P02 Class-specific Insertions Define Neutralization Sites

The two major neutralizing immunogenic (NIm) sites 1a & 1b (59, 63) share a common feature in sequence comparisons: both these sites appear as insertion regions that are class-specific in P02 and remain so in most subsequent partitions. Site 1a, which is common to immunogenic site 1 in polioviruses and consists of the VP1 residues 91 and 95 (HRV14 numbering), occurs as insertions in a majority of the HRV-A and HRV-B classes (FIG. S1). Similarly, of the residues 83, 85, 138 and 139 (HRV14 numbering) belonging to the NIm-1b site in VP1(2), residues 138 and 139 are class-specific insertions for the HRV-A class but not for the HRV-B class (data available from the website bchs.uh.edu/HRVET).

Structurally, neutralization sites 1a and 1b belong to exposed VP1 loop regions in HRV (2, 59). This makes the corresponding P02 class-specific insertion locations amenable to strain diversifying mutations. Thus, exposed P02 class-specific insertions/deletions are good indicators of important neutralizing strain diversification sites. However, these conditions alone are not enough to predict the neutralization properties of sites located at subunit interface regions. This is clearly seen in the NIm II & III sites located near the VP1-VP2 and VP1-VP3 interfaces respectively (63). These neutralization sites do involve exposed VP1 residues (210 and 287 of HRV14) but they do not involve class-specific insertions (FIG. S1). Therefore, exposed P02 class-specific insertions/deletions are good indicators of neutralizing strain diversification sites provided these sites are not located in subunit interfaces.

CSRs Identify Receptor Binding Regions as Important Strain Diversifying Sites

The class-specific residue D213 (FIG. 4C), whose mutations generate classes in HRV beginning partition P09, contacts the major group receptor in HRV16 (4, 41). Similarly, the P09-class-specific residue 226Q of HRV 16 (or 225H in HRV2 serotype), that is located near but outside the canyon (28), contacts the minor group receptor in HRV2. Thus, CSRs correctly identify receptor contacting residues in both major and minor group HRV indicating that the receptor binding regions constitute important strain diversifying sites.

Strain Diversifying Residues are not Randomly Located But are Structurally Well Localized Some of the strain diversifying locations include known and putative capsid related function sites in HRV (present analysis) and in NoV respectively (12). The remaining such locations appear to be randomly distributed in sequences as seen from the CSRs. However, closer examination of the capsid structures reveals that the strain diversifying mutations do not occur at random sequence locations. Instead, a majority of such mutations are localized in and around cavities and pockets enclosed by the capsids of HRV and NoV.

Cavities and Pockets in HRV

The VP1-VP3 pseudo-dimer of the HRV16 capsid (34) consists of nearly 27 cavities and 49 pockets. All cavities are small but their sizes are consistent with those found in smaller proteins (30, 44, 57). In contrast, all pockets are larger. Thirteen pockets have inaccessible and accessible volumes less than 20Å3 and 3Å3 respectively while twenty two of the remaining pockets are larger having inaccessible volumes varying between 20Å3 and 100Å3. Nine of the remaining 15 pockets are still larger with volumes between 100Å3 and 500Å3.

Each of the five largest pockets has inaccessible volumes greater than 500Å3 with three of them (#71, #74 and #75) having volumes between 800Å3 and 1400Å3 (Table 6). The largest pocket (#75) encompasses the known anti-viral binding region (25, 34, 49, 65, 73) as seen from the agreement between computed parameters such as the pocket openings and the roof and floor residues of the pocket (Table 6; FIGS. 6A & 6B) with the corresponding known results (26, 34, 59, 65).

TABLE 6

HRV-VP1 Capsid Class-specific Residues Lining the Largest Pockets

| Partitions | Class-specific capsid residues (HRV16 numbering) |
|---|---|
| P02-P04 | 1N, 48E(#71), 56V(#68), 102E, 103M, 155R, 170W, 174Q, 223T, 239K(#73, #74) |
| P05 | P02+ 238H(#75, #73)) |
| P06 | P05+ 28N, 65M(#74), 90T, 181L (#75) |
| P07 | P06+ 108R(#69, #73), 125V |
| P08 | P07+ 13E, 29N, 35D, 75G(#73), 78H, 126P, 136G, 149A, 171Q, 192M (#75); 250P(#69), 264Y(#70) |
| P09 | P08+ 2P, 11L(#74), 13V, 17V, 19N, 26T(#71), 28S(#71), 74S(#73), 82L, 2M, 9A, 142Y(#75), 144Y(#75), 145V, 157D, 161Q, 162S, 163G, 166A(#75), 183F, 199G, 210V, 211T(#75), 213D(#75), 218C, 226Q, 237Y, 254V(#70, #72), 262T(#75) |

Pockets in HRV16 VP1-VP3 dimer

| # | No. of mouths $[S_1][S_2]$* | $(V_1)(V_2)$¶ | Residues lining the cavities/pockets (HRV16 numbering) |
|---|---|---|---|

TABLE 6-continued

HRV-VP1 Capsid Class-specific Residues Lining the Largest Pockets

| # | No. of mouths | [S₁][S₂]* | (V₁)(V₂)¶ | Residues |
|---|---|---|---|---|
| #75 | 6 | [538] [1289] | (202) (1359) | 77I(8*), 96W, 98I, 99N, 100L, 101Q(2*), 107R, 108R, 111E, 118F, 119D, 120S, 122I, 124M(7*), 142Y(9*), 143M, 144Y(9*), 147P, 166A(9^), 167S, 168V, 179F, 181L(6^), 182P, 184L, 185S, 186I, 187A, 189A, 190Y, 191Y, 192M(8^), 193F, 194Y, 206Y, 207G, 208T, 211T(^9), 212N, 213D(#75), 214M, 217L, 236I, 238H(2*, 5^), 252R, 256Y, 260H, 261T, 262T(^9), 263N(8*) |
| #74 | 2 | [289] [437] | (336) (826) | 9E, 11L(^9), 12N, 14V, 15L, 61T, 62L, 63D, 64E, 65M(6^), 66S, 68E, 69S, 72G, 74S, 75G(2^), 240A, 241K |
| #73 | 2 | [181] [502] | (56) (504) | 64E, 69S, 70F, 71L, 72G, 74S(^9), 75G, 76C, 104A, 105Q, 106I, 108R(^9), 109K, 111E, 238H(^9), 239(^2), 240A |
| #72 | 4 | [183] [334] | (97) (448) | 253A, 254V(^9), 255Q, 272N, 273D, 274V, 275A, 277R |
| #71 | 3 | [268] [398] | (372) (818) | 23S, 24H, 25P, 26T(^9), 27T, 28S(^9), 30A, 31A, 32P, 33V, 34L, 48(^2), 49D, 50T, 51I, 52E |
| #70 | 1 | [83] [179] | (36) (219) | 104A(*2), 254V(^9), 255Q, 256Y, 257S, 264Y(*8), 265K |
| #69 | 1 | [139] [278] | (76) (346) | 108R(^8), 250P(*8), 251P, 252R, 253A, 274V, 275A, 276I |
| #68 | 2 | [117] [235] | (61) (300) | 20I, 47P, 51I, 53T, 54R, 56V(^2), 57Q, 58S, 60Q |

*S₁, S₂: Solvent-accessible & solvent-inaccessible surfaces respectively (Å²) of cavity/pocket
¶V₁, V₂: Solvent-accessible & solvent-inaccessible volumes respectively (Å³) of cavity/pocket The upper part of the table shows the partition-wise (P02-P09) distribution of HRV16-VP1 class-specific residues (CSRs) and the lower part of the table shows eight of the largest computed structural pockets in the VP1-VP3 pseudo-dimer of HRV16 capsid. In the upper part of the table, any CSR that also lines one of the pockets is clearly indicated by the # sign and the corresponding pocket number within parentheses. Similarly, each pocket residue that is also a CSR, or, its sequence neighbor, is highlighted in the lower part of the table using matching colors of the corresponding partitions in the upper part of the table and one of the (^) or (*) signs along with the partition number. The (^) sign denotes CSRs while the (*) sign denotes sequence neighbors of CSRs in color-matched partitions. The bold-faced residue 213 directly contacts the major group receptor (ICAM) molecules. Blue highlighted residues indicate representatives lining more than one pocket.

Cavities and Pockets in NoV

The A-B dimer of the Norwalk virus capsid (55) contains 86 cavities and 77 pockets. All cavities are smaller than most of the pockets, among which, 64 are relatively small pockets having inaccessible volumes less than 10013 and ten are somewhat larger with volumes varying between 10013 and 40013. All pockets, including two of the largest ones (#160 and #162 in Table 7), involve only the S and/or the P1 domain residues. Only one major pocket (#161 in Table 7; FIG. 7B) involves P2 domain residues.

TABLE 7

NOV Capsid Class-specific Residues Lining the Largest Pockets

Pockets in Norwalk virus capsid
(1IHM) A-B dimer

| # | No. of mouths | [S₁][S₂]* | (V₁)(V₂)¶ | Residues lining the cavities/pockets (Norwalk numbering) |
|---|---|---|---|---|
| #162 | 5 | [2459] [3722] | (2954) (6839) | 64P(*7), 65Q(^7), 84S, 85L, 86G, 87P, 88H, 91P, 94L, 95H, 97S, 98Q, 103W, 171H, 172N, 173N, 174D, 175R, 177Q, 179T, 221P, 222P, 223T(^7), 224V, 226Q(^2), 227K (^5), 228T(*5), 229R(^6), 230P(*6), 231F, 232T, 233L, 234P, 235N(*6), 236L(^6), 242S, 247R, 284L, 439Q, 440E, 443S, 444H, 447S, 448Q, 450A, 451P, 453V, 462V, 464P, 500V, 501F, 502V, 503F, 504V(^7), 505S, 502X |

TABLE 7-continued

NOV Capsid Class-specific Residues Lining the Largest Pockets

Pockets in Norwalk virus capsid
(1IHM) A-B dimer

| # | No. of mouths | $[S_1][S_2]$* | $(V_1)(V_2)$¶ | Residues lining the cavities/pockets (Norwalk numbering) |
|---|---|---|---|---|
| #161 | 2 | [989] [1673] | (950) (2764) | 239S(^7), 240S(^7), 246A(^7), 247P, 248L, 249P, 250I, 251S, 276L, 280T, 281P, 282V, 284E, 286H, 289R, 291R, 303E, 304L, 305D, 307T, 308P, 310H, 313E, 318I, 331N(*2), 333T, 335F, 370V, 372V, 373S, 374S(*2), 423S, 424K, 425M, 426P, 465D, 498N, 2237P |
| #160 | 2 | [316] [618] | (216) (853) | 65Q(^7), 67E, 68F, 69T, 74N, 77G, 78D, 79V, 80L, 81F, 82D(^7), 83L(^5), 128I, 132F, 133G(^7), 134S, 135H, 136N, 137L, 181R, 183V, 185M, 206V, 454G, 455E, 465E, 507V, 508S, 510F, 511Y |

*$S_1$, $S_2$: Solvent accessible & solvent inaccessible surfaces respectively ($Å^2$) of pocket
¶$V_1$, $V_2$: Solvent accessible & solvent inaccessible volumes respectively ($Å^3$) of pocket Three of the largest computed structural pockets in the A-B dimer of Norwalk capsid (PDB ID: 1IHM). Pockets #161 and #162 are lined by residues of both the A and the B subunits. Pocket #160 is lined by only the A subunit residues. Only the A-subunit residues are shown for each pocket. Each pocket residue that is also a class-specific residue (CSR), or, its sequence neighbor, is highlighted using the partition coloring scheme of Table 6. The (^) sign denotes the CSRs while the (*) sign denotes some of the sequence neighbors of CSRs in color-matched partitions. Blue highlighted residues indicate representative residues lining more than one pocket.

CSRs Line the Inter-connected Pockets in HRV and NoV

A majority of the CSRs and their sequence neighbors line the pockets in HRV and NoV indicating that these pockets localize most of the strain diversifying mutations. Most of the cavities and pockets are inter-connected through common CSRs. Additionally, some of the CSRs lining the largest pockets are also involved in, or are putatively involved in, capsid related functions in HRV and NoV respectively (Tables 6 & 7; FIGS. 7C-7E) (12, 31, 53). Thus, capsids of HRV and NoV enclose a network of inter-connected cavities and pockets, the largest of which define regions where three major determinants of adaptations, namely, strain diversifying mutations, receptor binding and antigenicity occur together.

Pockets and Cavities May Define Capsid Adaptation Sites in HRV and NoV

The occurrence of strain diversifying mutations and capsid related functions in the largest pockets has important implications in HRV and NoV. The inter-connected pockets and cavities may be schematically represented as trapped bubbles in regions whose surface contains the receptor binding and antigenic sites (FIG. 4D). Upon binding the receptor, strain diversifying mutations occur in these regions in order to escape host immune responses. These mutations may change the shapes of the bubbles by squeezing or expanding them. This, in turn, modifies the capsid surface to create altered receptor binding and antigenic characteristics (FIG. 4E). The pockets and cavities, therefore, define regions where capsid related functions and strain diversifying mutations mutually influence each other. Hence, these pockets and cavities may define important adaptation sites in HRV and NoV. Interconnectivity among such sites indicates that adaptations in one site may affect other distantly located sites, perhaps facilitated by solvent molecules in a manner similar to the influence of protein cavities on ligand binding (9, 22, 66, 69).

Analysis of all known capsid structures of HRV indicates that the number of CSRs lining the pockets increases with increase in the pocket sizes (Tables 6 & 7 and data available from bchs.uh.edu/HRVET). Thus, the size of a given pocket approximately determines the number of different types of strain diversifying mutations that the pocket may tolerate, indicating thereby, the relative evolutionary importance of the different adaptation sites.

Adaptive Sites May Reveal Strain Diversification in Enteroviruses

Because both HRV and HEV mutate at uniform rates that are well within limits proposed for ssRNA viruses (18), the HEV may be compared using evolutionarily equidistant partitions in a similar way as the HRV. Such comparisons reveal the strain diversifying sites in HEV.

Partitioned Comparisons Reveal Antigenic Relationships Among Species of HEV

Comparisons of different HEV species reveal known and unidentified antigenic relationships. When serotypes of species HEV-A and B are compared, the two P02 classes (A & B) correctly group the serotypes in their respective species (FIG. S2) each of which contains antigenically related serotypes (32). Even strains with unconfirmed species (HEV-75, 76, 78, 89, 90 and 91) are correctly placed in classes that correspond to their respective proposed species. The CSRs, which are also the strain diversifying locations, are clearly revealed for the two species (data available with authors at http://bchs.uh.edu/HRVET).

HEV-B and C May be Antigenically Related Through CSRs

Inclusion of the HEV-C species (Coxsackie-A1, A 1, A13, A15, A17-A22, A24, echovirus-34) in partitioned comparisons along with the HEV-A and the HEV-B species indicates new antigenic relationships in partition P02. The HEV-B and the HEV-C species group together in the same class (FIG. S3) thereby indicating that the capsids of these two species antigenically resemble each other more closely than the HEV-A capsids. This is further confirmed when serotypes of the known four species, HEV-A, B, C and D, are compared together. Only three P02 classes are observed, of which, the B and C species group together in the HEV-(B+C) class (FIG.

S4). The remaining two classes respectively contain the HEV-A and the HEV-D species. The P02 class-specific residues 34, 40, 52, 81 and 157 (PDBID: 1Z7S numbering) are the strain diversifying locations that explain the similarities and differences among the classes. It is only in P03 that the HEV-B and the HEV-C serotypes are distinguished as individual species through their respective CSRs (details available with authors: prion.bchs.uh.edu/HRVET).

Polioviruses are Similar to HEV-C

Partition P02 shows correct antigenicity for polioviruses with respect to the HEV species. Polioviruses are grouped together with the HEV-C class in P02 (FIG. S3) indicating that the these viruses belong to the HEV-C species, in agreement with the current consensus about the identity of polioviruses (56) as well as with recently approved recommendations (8, 68). Interestingly, when all three known poliovirus serotypes PV-1, 2 and 3 (7, 32) are compared, only two distinct P02 classes are created (FIG. 5). Of these, the PV2+3 class shows that the PV-2 and the PV-3 serotypes share closer antigenic similarities among each other than with the PV-1 serotypes due to the class-specific locations 6, 76, 213, 278 and 290 (PDBID: 1P01 numbering). Such similarities may indicate shared epitopes among the PV-2 and PV-3 classes that separate into distinct serotypes only in P03 (FIG. 5).

Evolutionary Importance of Partition P02

The present analysis places the greatest emphasis on sequence relationships in partition P02. This is because it is assumed throughout that among all the partitions, P02 has the highest evolutionary importance or rank in determining such relationships. By definition, the evolutionary rank of a residue is inversely related to the minimum number of classes required to denote the residue class-specific (47). Thus, lower the rank of a residue, higher is its evolutionary importance and vice-versa. This is because a low rank indicates conservation of a residue even among distantly related sequence classes, whereas, a high ranking residue indicates that the residue varies even among closely related sequences implying a relatively lower evolutionary significance for the residue due to a high probability that random chance events may create such residue variations.

Consequently, the first partition P01, which compares sequences in one group like in conventional sequence comparisons, has negligible evolutionary importance because class-specificity cannot be defined for this partition. More simply, P01 intrinsically masks evolutionarily important residues that may define phylogenetic strain diversification. In contrast, the second partition P02 is evolutionarily most significant because each P02 class contains the maximum number of distantly related sequences. The CSRs have become fixed to the distantly related classes so early in phylogeny that they acquire the greatest evolutionary importance in defining class-specific functions such as receptor binding and antigenicity that drive strain diversification. Therefore, partition P02 displays the most significant sequence relationships in its classes that, in turn, spawn other relatively less significant classes in subsequent partitions (FIGS. 4A, 5, S1-S3).

P02 Classes May Indicate Adaptive Basis of Strain Diversification in Other Picornaviruses If partitioned comparisons reveal possible adaptive sites that are responsible for strain diversification in each of the two different genera HEV and HRV of the Picornaviridae family, it should also be possible to partition-wise compare two or more genera of this family together. This is because it is reasonable to assume that each of the nine genera (enteroviruses, rhinoviruses, cardioviruses, aphthoviruses, hepatoviruses, parechoviruses, erboviruses, kobuviruses and the teschoviruses (36)) of the Picornaviridae family has comparably uniform mutation rates. If so, then, the P02 classes arising out of the partitioned comparisons multiple genera together will yield evolutionarily significant strain diversification patterns. Additionally, such joint comparisons may be useful for checking the consistency of the results obtained earlier individually for HRV and the HEV in the present analysis.

HRV and HEV are Similar

When amino acid sequences of the VP1-capsids of all nine genera of picornaviruses are compared together, four P02 classes (1-4) are created (FIG. 8). The HRV and the HEV group together in class 3 of partition P02 and continue to remain grouped in class 3a of subsequent partitions P03 and P04. This indicates significant similarities among the HRV and the HEV, in agreement with recently accepted recommendations (39, 68).

It is only in P05 that the HRV separate from the HEV to create the HRV-A and the HRV-B species in classes 3a1 and 3a2 respectively which remain unchanged in P06 (FIG. 8). Similarly, the HEV split into five classes (3b1-3b5) in P05. Of these, classes 3b2 and 3b3 consist of the HEV-A and the HEV-D species respectively and class 3b5 consists of the simian enteroviruses (SEV). Class 3b1 groups the HEV-B and the HEV-C species together including the polioviruses (FIG. 8) confirming the earlier results of the present analysis using HEV alone (FIG. S2, S3).

HRV87 Serotype is Similar to HEV-D Species

Among the HEV classes 3b1-3b5, class 3b4 shows that a current rhinovirus serotype (HRV87) is more similar to two HEV-D serotypes 68 and 70 (FIG. 8) than it is to other rhinoviruses, in agreement with recent recommendations (42, 61, 68). Such non-rhinovirus like characteristics of HRV87 is confirmed in comparisons among the HRV, where, this serotype independently branches off at node 3 in partition P02 (FIG. 4A).

More P02-Based Predicted Relationships Among Picornavirus Genera

The importance of partition P02 in correctly elucidating so many sequence relationships among the HRV and the HEV allows predictions of more P02-based sequence relationships and the consequent strain diversification in other picornaviruses. The P02 class 1 (FIG. 8) indicates that the aphthovirus genus (including the erbovirus-A species), the erbovirus-B species and the cardiovirus genus (including the encephalomyocarditis (EMC) viruses and the Theiler's murine encephalomyelitis (TME) viruses) are closely related, consistent with some known sequence comparisons and cleavage mechanisms of some of these viruses (27, 40).

While kobuviruses alone form class 2 of P02 showing their distinctiveness from the other genera, the teschoviruses (TEV) group together in class 3 along with HRV and the HEV (FIG. 8). This shows that the TEV genus may share important adaptive function similarities with the HRV and the HEV. Similarly, class 4 shows that the hepatoviruses and the parechoviruses are closer to each other than they are to the other genera.

Later Partitions Reveal Species of Picornaviruses

Unlike partition P02 which reveals inter-relationships among the currently known genera, the later partitions systematically show the emergence of other classification hierarchies such as the species. For example, the P02 class 1 splits up into the aphthovirus genus (class 1a), Erbo-A species (class 1b), Erbo-B species (class 1c) and the cardiovirus genus (class 1d) in P03 and P04 (FIG. 8). Of these, classes 1c and 1d remain unchanged in all subsequent partitions while the aphthovirus genus (class 1a) further splits up into the known A, C, O, Asian and the African species. Similarly, the cardiovirus class 1d splits up into the known EMCV and the TME species in partition P06 (FIG. 8). Of the other P02 classes, class 4 splits up into the respective hepatoviruses and the parechoviruses genera in P03 (classes 4a and 4b). These remain unchanged in P05 and P06 after which further species emerge (data not shown).

Thus, comparisons of the picornavirus VP1 amino acid sequences indicate partition-dependent relationships among the currently known genera and species. Such relationships among the known genera in P02 may reflect shared receptors, antigenicity or both, unlike comparisons within a given genus where the P02 classes primarily yield antigenic relationships as seen for HRV and the HEV. It is only in later partitions that all of the currently known species and serotypes emerge independently (FIG. 8).

P02 Classes in Caliciviruses

Comparisons of amino acid sequences of all caliciviruses shows that the lagoviruses and the noroviruses form independent classes while the sapoviruses and the vesiviruses together form the third class (data not shown). This indicates that the sapoviruses and the vesiviruses share similarities in their capsid adaptation sites Need for Partition Based Classification to Indicate Adaptive Sites Thus, partition-dependent classes and the CSRs explain strain diversification in picornaviruses and caliciviruses by distinguish these viruses on the basis of adaptation site residues. Therefore, classification schemes based on capsid sequences should explicitly indicate partitions in sequence classes in order to reflect these adaptive sites.

One way of doing so would be to represent the genus of a virus as Gn, where the uppercase G denotes the genus and n denotes the genus number. As each genus has its own phylogenetic tree, any sequence class (or cluster) on these genus trees may be uniquely represented using a partition number and a class number in the format P(xx).g(n), where the lowercase g is used to denote clusters belonging to a given genus, xx denotes the partition number and n denotes the class number within the partition.

As an illustration, the four genera of the Caliciviridae family are represented by G1 (noroviruses), G2 (lagoviruses), G3 (sapoviruses) and G4 (vesiviruses) with each genus having its own partitioned tree. In the norovirus (G1) tree, class #4 in partition P05 would be denoted as G1.P05.g4 that represents all sequences in class 4 (g4) of partition P05 of the norovirus tree. Similarly, G1.P02.g2 would represent those noroviruses that belong to class g2 of partition P02. Likewise, the symbol G3.P06.g2 would represent class #2 (g2) in partition P06 of the sapovirus (G3) tree. Such a representation would uniquely reflect all partition-dependent classes within a given virus family.

Norovirus Classes May Reflect Antigenic Relationships

The present analysis shows that the phylogenetic trees of the two genera (HRV and HEV) of picornaviruses portray antigenic diversity. The partitioned classes of a given genus correspond to groups of antigenically related serotypes. Therefore, the phylogenetic trees of capsid sequences of NoV may reflect antigenic diversity among noroviruses. The corresponding partitioned classes of NoV (12) may actually represent antigenic relationships among groups none of which are identified due to the non-cultivability of these viruses. For example, genogroup I strains Norwalk (PDB: 1IHM), Aichi (NCBI: AB010145) and Kyoto-89 (NCBI: L23828) which cluster together in partitions P02-P10 (12), may be antigenically related to each other. Similarly, the genogroup II strains Chesterfield (NCBI: Q91386), Melksham (NCBI: X81879) and Snow Mountain (NCBI: U700059) may also be antigenically related (12). Additionally, the exposed regions that correspond to P02 class-specific insertions, such as those occurring in the P-domains near residues 298, 339, 362, 426 of Norwalk virus (12), may play important roles in neutralizing NoV.

CONCLUSIONS

The present study uses evolutionary trace based approach to show that although noroviruses (NoV) and human rhinoviruses (HRV) belong to different families of single stranded RNA (ssRNA) viruses, their coat protein sequences do not mutate at random residue locations to create strain diversification. Instead, these mutations are mostly localized in and around inter-connected structural pockets in the capsids of both NoV and HRV. Many of the strain diversifying residues belonging to the largest pockets are involved in capsid related functions such as receptor binding and antigenicity. Thus, these pockets may structurally facilitate adaptations in response to host immune responses. The pockets are, therefore, called adaptation sites. Combinations of strain diversifying residues belonging to different adaptation sites explain the antigenic diversity in HRV by uniquely identifying each phylogenetic group of antigenically related serotypes. Therefore, known phylogenetic groups of NoV may reveal unidentified antigenic relationships. Extension to other picornaviruses and caliciviruses reveals significant sequence relationships among different genera and species on the basis of unique strain diversifying residues. Such residues may, therefore, be used to distinguish and classify these viruses and other ssRNA virus families as well.

Database Partitioning for Rhino cDNA

The rhino cDNA database is shown in FIG. D1. The code used read the database is shown in FIG. D2. The group information used in the structured data is shown in FIG. D3. The partition trees is shown in FIG. D4, which consists of ten partitions. Partition one (P1) is shown in FIG. D5. Partition one (P2) is shown in FIG. D6. Partition one (P3) is shown in FIG. D7. Partition one (P4) is shown in FIG. D8. Partition one (P5) is shown in FIG. D9. Partition one (P6) is shown in FIG. D10. Partition one (P7) is shown in FIG. D11. Partition one (P8) is shown in FIG. D12. Partition one (P9) is shown in FIG. D13. Partition one (P10) is shown in FIG. D14. This data and the partitions was used above in the analysis of adaptive mutations.

REFERENCES CITED IN ADAPTIVE MUTATIONS EMBODIMENT

1. Ando, T., J. S. Noel, and R. L. Fankhauser. 2000. Genetic Classification of "Norwalk-like Viruses. The Journal of Infectious Diseases 181:S336-S348.
2. Andries, K., B. Dewindt, J. Snoeks, L. Wouters, H. Moereels, P. J. Lewi, and P. A. Janssen. 1990. Two groups of rhinoviruses revealed by a panel of antiviral compounds present sequence divergence and differential pathogenicity. J. Virol. 64:1117-1123.
3. Ausar, S. F., T. R. Foubert, M. H. Hudson, T. S. Vedvick, and C. R. Middaugh. 2006. Conformational Stability and Disassembly of Norwalk Virus-like Particles: EFFECT OF pH AND TEMPERATURE. J. Biol. Chem. 281:19478-19488.
4. Bella, J., P. R. Kolatkar, C. W. Marlor, J. M. Greve, and M. G. Rossmann. 1998. The structure of the two amino-terminal domains of human ICAM-1 suggests how it functions as a rhinovirus receptor and as an LFA-1 integrin ligand. Proc. Natl Acad. Sci. (USA) 95:4140-4145.
5. Binkowski, T. A., S. Naghibzadeh, and J. Liang. 2003. CASTp: Computed Atlas of Surface Topography of proteins. Nucl. Acids Res. 31:3352-3355.
6. Blomqvist, S., A.-L. Bruu, M. Stenvik, and T. Hovi. 2003. Characterization of a recombinant type 3/type 2 poliovirus isolated from a healthy vaccinee and containing a chimeric capsid protein VP1. J Gen Virol 84:573-580.
7. Bodian, D., I. M. Morgan, and H. A. Howe. 1949. Differentiation of types of poliomyelitis viruses. III. The grouping of fourteen strains into three basic immunologic types. Am. J. Hyg. 49:234-245.
8. Brown, B., M. S. Oberste, K. Maher, and M. A. Pallansch. 2003. Complete Genomic Sequencing Shows that Polioviruses and Members of Human Enterovirus Species C Are Closely Related in the Noncapsid Coding Region. J. Virol. 77:8973-8984.
9. Brunori, M., B. Vallone, F. Cutruzzola, C. Travaglini-Allocatelli, J. Berendzen, K. Chu, R. M. Sweet, and I. Schlichting. 2000. The role of cavities in protein dynamics: Crystal structure of a photolytic intermediate of a mutant myoglobin. PNAS 97:2058-2063.
10. Cao, S., Z. Lou, M. Tan, Y. Chen, Y. Liu, Z. Zhang, X. C. Zhang, X. Jiang, X. Li, and Z. Rao. 2007. Structural Basis for the Recognition of Blood Group Trisaccharides by Norovirus. J. Virol. 81:5949-5957.
11. Casasnovas, J. M., T. Stehle, J.-h. Liu, J.-h. Wang, and T. A. Springer. 1998. A dimeric crystal structure for the N-terminal two domains of intercellular adhesion molecule-1. PNAS 95:4134-4139.
12. Chakravarty, S., A. M. Hutson, M. K. Estes, and B. V. V. Prasad. 2005. Evolutionary Trace Residues in Noroviruses: Importance in Receptor Binding, Antigenicity, Virion Assembly, and Strain Diversity. J. Virol. 79:554-568.
13. Connolly, M. L. 1996. Molecular Surfaces: A Review.
14. Connolly, M. L. 1983. Solvent-Accessible Surfaces of Proteins and Nucleic Acids. Science 221:709-713.
15. Cooney, M. K., J. P. Fox, and G. E. Kenny. 1982. Antigenic groupings of 90 rhinovirus serotypes. Infect Immun 37:642-7.
16. Cooney, M. K., G. E. Kenny, R. Tam, and J. P. Fox. 1973. Cross relationships among 37 rhinoviruses demonstrated byvirus neutralization with potent monotypic rabbit antisera. Infect Immun 7:335-40.
17. Duechler, M., T. Skem, W. Sommergruber, C. Neubauer, P. Gruendler, I. Fogy, D. Blaas, and E. Kuechler. 1987. Evolutionary Relationships within the Human Rhinovirus Genus: Comparison of Serotypes 89, 2, and 14. PNAS 84:2605-2609.
18. Eigen, M., and C. K. C. K. Biebricher. 1988. Sequence space and quasispecies distribution, p. 211-245. In E. Domingo, J. J. Holland, and P. Ahlquist (ed.), RNA Genetics: Variability of RNA Genomes, vol. 3. CRC Press Inc., Boca Raton, La.
19. Equestre, M., D. Genovese, F. Cavalieri, L. Fiore, R. Santoro, and R. Perez Bercoff. 1991. Identification of a consistent pattern of mutations in neurovirulent variants derived from the sabin vaccine strain of poliovirus type 2. J. Virol. 65:2707-2710.
20. Fankhauser, R. L., S. S. Monroe, J. S. Noel, C. D. Humphrey, J. S. Bresee, U. D. Parashar, T. Ando, and R. I. Glass. 2002. Epidemiologic and Molecular Trends of "Norwalk-like Viruses" Associated with Outbreaks of Gastroenteritis in the United States. J. Infect. Dis. 186:1-7.
21. Fiore, L., D. Genovese, E. Diamanti, S. Catone, B. Ridolfi, B. Ibrahimi, R. konomi, H. G. A. M. van der Avoort, T. Hovi, R. Crainic, P. Simeoni, and C. Amato. 1998. Antigenic and Molecular Characterization of Wild Type 1 Poliovirus Causing Outbreaks of Poliomyelitis in Albania and Neighboring Countries in 1996. J. Clin. Microbiol. 36:1912-1918.
22. Friedman, R., E. Nachliel, and M. Gutman. 2003. The Role of Small Intraprotein Cavities in the Catalytic Cycle of Bacteriorhodopsin. Biophys. J. 85:886-896.
23. Gallimore, C. I., J. Green, D. Lewis, A. F. Richards, B. A. Lopman, A. D. Hale, R. Eglin, J. J. Gray, and D. W. G. Brown. 2004. Diversity of Noroviruses Cocirculating in the North of England from 1998 to 2001. J. Clin. Microbiol. 42:1396-1401.
24. Georgescu, M. M., J. Balanant, A. Macadam, D. Otelea, M. Combiescu, A. A. Combiescu, R. Crainic, and F. Delpeyroux. 1997. Evolution of the Sabin type 1 poliovirus in humans: characterization of strains isolated from patients with vaccine-associated paralytic poliomyelitis. J. Virol. 71:7758-7768.
25. Hadfield, A. T., G. D. Diana, and M. G. Rossmann. 1999. Analysis of three structurally related antiviral compounds in complex with human rhinovirus 16. PNAS 96:14730-14735.
26. Hadfield, A. T., W. Lee, R. Zhao, M. A. Olivera, I. Minor, R. R. Rueckert, and M. G. Rossmann. 1997. The refined structure of human rhinovirus 16 at 2.15 A resolution: implications for the viral life cycle. Structure 5:427-441.
27. Hahn, H., and A. C. Palmenberg. 1996. Mutational analysis of the encephalomyocarditis virus primary cleavage. J Virol 70:6870-5.
28. Hewat, E. A., E. Neumann, J. F. Conway, R. Moser, B. Ronacher, T. C. Marlovits, and D. Blaas. 2000. The cellular receptor to human rhinovirus 2 binds around the 5-fold axis and not in the canyon: a structural view. Embo J 19:6317-25.
29. Horsnell, C., R. E. Gama, P. J. Hughes, and G. Stanway. 1995. Molecular relationships between 21 human rhinovirus serotypes. J Gen Virol 76:2549-2555.
30. Hubbard, S. J., and P. Argos. 1994. Cavities and packing at protein interfaces. Protein Sci 3:2194-2206.
31. Hutson, A. M., S. Chakravarty, R. Atmar, L, B. V. Prasad, and M. K. Estes. 2004. Loss of carbohydrate binding with point mutations of Norwalk virus virus-like particles. Second International Calicivirus Conference, Dijon, France.
32. Hyypia, T., T. Hovi, N. J. Knowles, and G. Stanway. 1997. Classification of enteroviruses based on molecular and biological properties. J Gen Virol 78:1-11.
33. Innis, C. A., J. Shi, and T. L. Blundell. 2000. Evolutionary trace analysis of TGF-beta and related growth factors: implications for site-directed mutagenesis. Protein Eng 13:839-47.
34. Kim, K. H., P. Willingmann, Z. X. Gong, M. J. Kremer, M. S. Chapman, I. Minor, M. A. Oliveira, M. G. Rossmann, K. Andries, and G. D. Diana. 1993. A Comparison of the Anti-rhinoviral Drug Binding Pocket in HRV14 and HRV1A. Journal of Molecular Biology 230:206-227.
35. Kim, S. S., T. J. Smith, M. S. Chapman, M. G. Rossmann, D. C. Pevear, F. J. Dutko, P. J. Felock, G. D. Diana, and M. A. McKinlay. 1989. Crystal structure of human rhinovirus serotype 1A (HRV1A). J Mol Biol 210:91-111.
36. King, A. M. Q., F. Brown, P. Christian, T. Hovi, T. Hyypiii, N. J. Knowles, S. M. Lemon, P. D. Minor, A. C. Palmenberg, T. Skern, and G. Stanway. 2000. Picornaviridae, p. 657-673. In M. H. V. Van Regenmortel, Fauquet, C. M., Bishop, D. H. L., Calisher, C. H., Carsten, E. B., Estes, M.

K., Lemon, S. M., Maniloff, J., Mayo, M. A., McGeoch, D. J., Pringle, C. R., Wickner, R. B. (ed.), Virus Taxonomy. Seventh Report of the International Committee for the Taxonomy of Viruses. Academic Press, New-York, San Diego.
37. Kleywegt, G. J., and T. A. Jones; 1994. Detection, delineation, measurement and display of cavities in macromolecular structures. Acta Crystallogr D50: 178-185.
38. Knowles, N. 2003. IAH Virus pages. Institute for Animal Health, U.K., www.iah.bbsrc.ac.uk/virus/.
39. Knowles, N. 2007. Rhinoviruses: IAH Virus pages; Institue for Animal health, U.K. www.picornastudygroup.com/proposals/2007/proposals_2007.htm.
40. Knowles, N. J. 1997. Cardiovirus. Institute for Animal Health, U.K.; http://www.picornaviridae.com/cardiovirus/cardiovirus.htm.
41. Kolatkar, P. R., J. Bella, N. H. Olson, C. M. Bator, T. S. Baker, and M. G. Rossmann. 1999. Structural studies of two rhinovirus serotypes complexed with fragments of their cellular receptor. Embo J 18:6249-59.
42. Laine, P., S. Blomqvist, C. Savolainen, K. Andries, and T. Hovi. 2006. Alignment of capsid protein VP1 sequences of all human rhinovirus prototype strains: conserved motifs and functional domains. J Gen Virol 87:129-138.
43. Lee, B., and F. M. Richards. 1971. The interpretation of protein structures: Estimation of static accessibility. Journal of Molecular Biology 55:379-380.
44. Liang, J., H. Edelsbrunner, and C. Woodward. 1998. Anatomy of protein pockets and cavities: Measurement of binding site geometry and implications for ligand design. Protein Sci 7:1884-1897.
45. Lichtarge, O., H. R. Bourne, and F. E. Cohen. 1996. An evolutionary trace method defines binding surfaces common to protein families. J Mol Biol 257.
46. Lochridge, V. P., K. L. Jutila, J. W. Graff, and M. E. Hardy. 2005. Epitopes in the P2 domain of norovirus VP1 recognized by monoclonal antibodies that block cell interactions. J Gen Virol 86:2799-2806.
47. Madabushi, S., H. Yao, M. Marsh, D. M. Kristensen, A. Philippi, M. E. Sowa, and O. Lichtarge. 2002. Structural clusters of evolutionary trace residues are statistically significant and common in proteins. Journal of Molecular Biology 316:139-154.
48. Maguire, A. J., J. Green, D. W. G. Brown, U. Desselberger, and J. J. Gray. 1999. Molecular Epidemiology of Outbreaks of Gastroenteritis Associated with Small Round-Structured Viruses in East Anglia, United Kingdom, During the 1996-1997 Season. J. Clin. Microbiol. 37:81-89.
49. McKinlay, M. A., D. C. Pevear, and M. G. Rossmann. 1992. Treatment of the picornavirus common cold by inhibitors of viral uncoating and attachment. Annual Review of Microbiology 46:635-654.
50. Mogabgab, W. J., B. J. Holmes, and B. Pollock. 1975. Antigenic relationships of common rhinovirus types from disabling upper respiratory illnesses. Dev. Biol. Stand. 28:400-411.
51. NCBI. Life sciences databases at the National Center for Biotechnology Information (NCBI), USA. NCBI, National Center for Biotechnology Information, http://www.ncbi.nlm.nih.gov/.
52. Oberste, M., D. Schnurr, K. Maher, S. al-Busaidy, and M. Pallansch. 2001. Molecular identification of new picornaviruses and characterization of a proposed enterovirus 73 serotype. J Gen Virol 82:409-16.
53. Parker, T. D., N. Kitamoto, T. Tanaka, A. M. Hutson, and M. K. Estes. 2005. Identification of Genogroup I and Genogroup II Broadly Reactive Epitopes on the Norovirus Capsid. J. Virol. 79:7402-7409.
54. Pevear, D. C., M. J. Fancher, P. J. Felock, M. G. Rossmann, M. S. Miller, G. Diana, A. M. Treasurywala, M. A. McKinlay, and F. J. Dutko. 1989. Conformational change in the floor of the human rhinovirus canyon blocks adsorption to HeLa cell receptors. J. Virol. 63:2002-2007.
55. Prasad, B. V. V., M. E. Hardy, T. Dokland, J. Bella, M. G. Rossmann, and M. K. Estes. 1999. X-ray Crystallographic Structure of the Norwalk Virus Capsid. Science 286:287-290.
56. Racaniello, V. R. 2001. Picornaviridae: the viruses and their replication, p. 685-722. In D. M. Knipe, P. M. Howley, D. E. Griffin, R. A. Lamb, M. A. Martin, B. Roizman, and S. E. Straus (ed.), Fields Virology. Lippincott Williams & Wilkins, Philadelphia.
57. Rashin, A. A., M. Iofin, and B. Honig. 1986. Internal cavities and buried waters in globular proteins. Biochemistry 25:3619-3625.
58. Reuer, Q., R. J. Kuhn, and E. Wimmer. 1990. Characterization of poliovirus clones containing lethal and nonlethal mutations in the genome-linked protein VPg. J. Virol. 64:2967-2975.
59. Rossmann, M. G., E. Arnold, J. W. Erickson, E. A. Frankenberger, J. P. Griffith, H. J. Hecht, J. E. Johnson, G. Kamer, M. Luo, and A. G. M. e. al. 1985. Structure of a human common cold virus and functional relationship to other picornaviruses. Nature 317.
60. Saito, M., T. Oyama, and T. Shirai. 2005. Detection of subunit interfacial modifications by tracing the evolution of clamp-loader complex. Protein Engineering, Design and Selection 18:139-145.
61. Savolainen, C., S. Blomqvist, M. N. Mulders, and T. Hovi. 2002. Genetic clustering of all 102 human rhinovirus prototype strains: serotype 87 is close to human enterovirus 70. J Gen Virol 83:333-40.
62. Schieble, J. H., V. L. Fox, F. Lester, and E. H. Lennette. 1974. Rhinoviruses: an antigenic study of the prototype virus strains. Proc Soc Exp Biol Med 147:541-5.
63. Sherry, B., A. G. Mosser, R. J. Colonno, and R. R. Rueckert. 1986. Use of monoclonal antibodies to identify four neutralization immunogens on a common cold picornavirus, human rhinovirus 14. J Virol 57:246-257.
64. Smith, D. B., and S. C. Inglis. 1987. The Mutation Rate and Variability of Eukaryotic Viruses An Analytical Review. J Gen Virol 68:2729-2740.
65. Smith, T. J., M. J. Kremer, M. Luo, G. Vriend, E. Arnold, G. Kamer, M. G. Rossmann, M. A. McKinlay, G. D. Diana, and M. J. Otto. 1986. The Site of Attachment in Human Rhinovirus 14 for Antiviral Agents that Inhibit Uncoating. Science 233:1286-1293.
66. Song, J.-L., J. Li, Y.-S. Huang, and D. T. Chuang. 2003. Encapsulation of an 86-kDa Assembly Intermediate inside the Cavities of GroEL and Its Single-ring Variant SR1 by GroES. J. Biol. Chem. 278:2515-2521.
67. Sowa, M. E., W. He, K. C. Slep, M. A. Kercher, O. Lichtarge, and T. G. Wensel. 2001. Prediction and confirmation of a site critical for effector regulation of RGS domain activity. Nat Struct Mol Biol 8:234-237.
68. Stanway, G., F. Brown, P. Christian, T. Hovi, T. Hyypiii, A. M. Q. King, N. J. Knowles, S. M. Lemon, P. D. Minor, M. A. Pallansch, A. C. Palmenberg, and T. Skem. 2005. Family Picornaviridae. Virus Taxonomy. Eighth Report of the International Committee on Taxonomy of Viruses. Elsevier Academic Press.
69. Teeter, M. M. 2004. Myoglobin cavities provide interior ligand pathway. Protein Sci 13:313-318.

70. Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucl. Acids Res. 22:4673-4680.
71. Verdaguer, N., D. Blaas, and I. Fita. 2000. Structure of human rhinovirus serotype 2 (HRV2). J Mol Biol 300: 1179-1194.
72. Vinje', J., J. Green, D. C. Lewis, C. I. Gallimore, D. W. Brown, and M. P. Koopmans. 2000. Genetic polymorphism across regions of the three open reading frames of "Norwalk-like viruses". Arch Virol 145:223-41.
73. Zhang, Y., A. A. Simpson, R. M. Ledford, C. M. Bator, S. Chakravarty, G. A. Skochko, T. M. Demenczuk, A. Watanyar, D. C. Pevear, and M. G. Rossmann. 2004. Structural and Virological Studies of the Stages of Virus Replication That Are Affected by Antirhinovirus Compounds. J. Virol. 78:11061-11069.
74. Zhao, R., D. C. Pevear, M. J. Kremer, V. L. Giranda, J. A. Kofron, R. J. Kuhn, and M. G. Rossmann. 1996. Human rhinovirus 3 at 3.0 A resolution. Structure 4:1205-1220.
75. Zheng, D.-P., T. Ando, R. L. Fankhauser, R. S. Beard, R. I. Glass, and S. S. Monroe. 2006. Norovirus classification and proposed strain nomenclature. Virology 346:312-323.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A computer program product implemented on a computer or stored on a computer readable storage medium for predicting strains of some pathogens from limited sequence data, the computer product comprising:
   a graphical user interface (GUI) code implemented on the computer or encoded on the computer readable storage medium and operable to carry out all data input-output (I/O) operations, where the GUI code uses a sequence category region of a screen of a display of an implementing computer to allow users to input sequence data in a specified format using a paste option or by reading in files containing the data, where the GUI code uses a database category region of the screen to use default reference sequences or allow users to pre-select specific reference sequence to facilitate sequence comparisons, and where the GUI code uses an output options category region of the screen to allow users to selectively display identifiers of each input sequence and summary/details of matches of characteristic residues for an input query sequence specified by its identifier;
   a storage code implemented on the computer or encoded on the computer readable storage medium and operable to identify characteristic residues of individual virus sequences or their groups from program supplied external files and to store virus sequence databases in the form of multiple data arrays including information about phylogenetic trees, sequence groups and characteristic residues of these groups, where arrays are in the form tree-like multiple 2-dimensional arrays for efficient referencing and retrieval;
   a sequence comparison code implemented on the computer or encoded on the computer readable storage medium and operable to compare input pathogen sequences with the stored database sequences on a residue-by-residue basis to produce comparisons corresponding to all pathogens or pathogen strains stored in the database that include some or all of the input pathogen sequences; and an identification code implemented on the computer or encoded on the computer readable storage medium and operable to identify the pathogens or pathogen strains of input pathogen sequences based on the comparisons and subsequent decision making algorithms, where the algorithms identifies the comparison pathogens or pathogen strains that include maximal sequence identify.

2. The product of claim 1, wherein the pathogens or strains comprise single stranded RNA viruses.

3. The product of claim 2, wherein the storage code numbers the characteristic residues and the storage code identifies characteristic residues of individual virus sequences or their groups from program supplied external files and stores these residues, groups and other related information in tree-like multiple 2-dimensional arrays for efficient referencing and retrieval with respect to the GUI code, which uses the database category region of the screen to use default reference sequences or allow users to pre-select specific reference sequences to facilitate sequence comparisons for sequence comparison purposes.

4. The product of claim 2, where the sequence comparison code selects individual residues of input sequences where the GUI code uses a sequence category region of a screen of a display associated with an implementing computer to allow users to input sequence data in a specified format using a paste option or by reading in files containing the data and compares these residues with the characteristic residues in the storage code numbers the characteristic residues and a storage code identifies characteristic residues of individual virus sequences or their groups from program supplied external files and stores these residues, groups and other related information in tree-like multiple 2-dimensional arrays for efficient referencing and retrieval with respect to the GUI code, which uses a database category region of the screen to use default reference sequences or to allow users to pre-select specific reference sequences to facilitate sequence comparisons for sequence comparison purposes using a tree-like search method.

5. The product of claim 1, wherein the GUI code is adapted to divide the screen into 3 distinct categories including the sequence category, the database category and the output options category adapted to simplify data input/output (I/O).

6. The product of claim 5, wherein the GUI code uses the database category region of the screen to allow users to pre-select specific sequence databases that might contain close matches to the input sequence strain.

7. The product of claim 5, wherein the GUI code uses the database category region of the screen to allow users to specify "Unknown" in case sequence databases that might contain close matches to the input sequence strain are not known.

8. The product of claim 5, wherein the GUI code uses the database category region of the screen to allow users to select and display a particular sequence or all sequences from a database of sequences using a drop down menu.

9. The product of claim 5, wherein the GUI code uses the database category region of the screen to allow users to view groups of similar sequences.

10. The product of claim 5, wherein the GUI code uses the database category region of the screen to allow users to activate execution of the program.

11. The product of claim 5, wherein the GUI code uses the database category region of the screen to allow users to activate execution of the program.

12. The product of claim 1, wherein the identification code identifies the best strain matching the input sequences.

13. A computer program product implemented on a computer or stored on a computer readable storage medium for predicting strains of some pathogens from limited sequence data, the computer product comprising:

a graphical user interface (GUI) code implemented on a computer or encoded on a computer readable storage medium and operable to carry out all data input-output (I/O) operations, where the GUI code uses a database category region of a screen of a display of an implementing computer to allow a user to pre-select specific sequence databases that might contain close matches to the input sequence strain and to use default reference sequences or allow the user to pre-select specific reference sequence to facilitate sequence comparisons;

a storage code implemented on the computer or encoded on the computer readable storage medium and operable to number and to identify characteristic residues of individual virus sequences or their groups from program supplied external files and to store the residues, groups and other related information in one or a plurality of pathogen sequence databases in the form of multiple data arrays including information about phylogenetic trees, sequence groups and characteristic residues of the groups for efficient referencing and retrieval, where the arrays comprise tree-like multiple 2-dimensional arrays;

a sequence comparison code implemented on the computer or encoded on the computer readable storage medium and operable to compare input pathogen sequences with the stored database sequences on a residue-by-residue basis to produce comparisons corresponding to all pathogens or pathogen strains stored in the database that include some or all of the input pathogen sequences; and an identification code implemented on the computer or encoded on the computer readable storage medium and operable to identify the pathogens or pathogen strains of input pathogen sequences based on the comparisons and subsequent decision making algorithms, where the algorithms identifies the comparison pathogens or pathogen strains that include maximal sequence identify.

14. The product of claim 13, wherein the pathogens or strains comprises single stranded RNA viruses.

15. The product of claim 14, wherein the GUI code is adapted to divide a screen of a display device connected to a computer implementing the GUI code into 3 distinct categories including a sequence category, a database category and an output options category adapted to simplify data input/output (I/O).

16. The product of claim 15, wherein the GUI code uses the sequence category region of the screen to allow users to input sequence data in a specified format using a paste option or by reading in files containing the data.

17. The product of claim 15, wherein the GUI code uses the database category region of the screen to allow users to specify "Unknown" in case sequence databases that might contain close matches to the input sequence strain are not known.

18. The product of claim 15, wherein the GUI code uses the database category region of the screen to use default reference sequences or allow users to pre-select specific reference sequence to facilitate sequence comparisons.

19. The product of claim 15, wherein the GUI code uses the database category region of the screen to allow users to select and display a particular sequence or all sequences from a database of sequences using a drop down menu.

20. The product of claim 15, wherein the GUI code uses the database category region of the screen to allow users to view groups of similar sequences.

21. The product of claim 15, wherein the GUI code uses the output options category region of the screen to allow users to selectively display identifiers associated with each input sequence and a summary/details of matches of characteristic residues for an input query sequence identified by its identifier.

22. The product of claim 14, wherein the storage code identifies characteristic residues of individual virus sequences or their groups from program supplied external files and stores these residues, groups and other related information in tree-like multiple 2-dimensional arrays for efficient referencing and retrieval.

23. The product of claim 14, where the sequence comparison code selects individual residues of input sequences where the GUI code uses a sequence category region of a screen of a display associated with an implementing computer to allow users to input sequence data in a specified format using a paste option or by reading in files containing the data and compares these residues with the characteristic residues in the storage code numbers the characteristic residues and a storage code identifies characteristic residues of individual virus sequences or their groups from program supplied external files and stores these residues, groups and other related information in tree-like multiple 2-dimensional arrays for efficient referencing and retrieval with respect to the GUI code, which uses a database category region of the screen to use default reference sequences or to allow users to pre-select specific reference sequences to facilitate sequence comparisons for sequence comparison purposes using a tree-like search method.

24. A computer program product implemented on a computer or stored on a computer readable storage medium for predicting strains of some pathogens from limited sequence data, the computer product comprising:

a graphical user interface (GUI) code implemented on a computer or encoded on a computer readable storage medium and operable to carry out all data input-output (I/O) operations, where the GUI code uses a sequence category region of a screen of a display associated with an implementing computer to allow a user to input sequence data of one or a plurality of input sequences in a specified format using a paste option or by reading in files containing the data and where the GUI code uses a database category region of the screen to use default reference sequences or to allow users to pre-select specific reference sequences to form selected individual residues of the input sequences to facilitate sequence comparisons;

a storage code implemented on the computer or encoded on the computer readable storage medium and operable to store virus sequence databases in the form of multiple data arrays including information about phylogenetic trees, sequence groups and characteristic residues of these groups and to number and to identify characteristic residues of individual virus sequences or their groups;

a sequence comparison code implemented on the computer or encoded on the computer readable storage medium and operable to compare the input pathogen sequences with the stored database sequences of known pathogen and pathogen strains on a residue-by-residue basis using a tree-like search method to produce comparisons, where the sequence comparison code selected individual residues of the input sequences and compares the selected residues with the characteristic residues to form comparisons comprising characteristic residues including their identifiers assigned by the storage code and stores the comparisons tree-like multiple 2-dimensional arrays for efficient referencing and retrieval; and an identification code implemented on the computer or encoded on the computer readable storage medium and operable to identify the pathogens or pathogen strains of input pathogen sequences based on the comparisons and subsequent decision making algorithms, where the algorithms identifies the comparison pathogens or pathogen strains that include maximal sequence identify.

25. The product of claim 24, wherein the pathogens or strains comprise single stranded RNA viruses.

26. The product of claim 25, wherein the GUI code is adapted to divide a screen of a display device connected to a computer implementing the GUI code into 3 distinct categories including a sequence category, a database category and an output options category adapted to simplify data input/output (I/O).

27. The product of claim 26, wherein the GUI code uses the sequence category region of the screen to allow users to input sequence data in a specified format using a paste option or by reading in files containing the data.

28. The product of claim 26, wherein the GUI code uses the database category region of the screen to allow users to pre-select specific sequence databases that might contain close matches to the input sequence strain.

29. The product of claim 26, wherein the GUI code uses the database category region of the screen to allow users to specify "Unknown" in case sequence databases that might contain close matches to the input sequence strain are not known.

30. The product of claim 26, wherein the GUI code uses the database category region of the screen to use default reference sequences or allow users to pre-select specific reference sequence to facilitate sequence comparisons.

31. The product of claim 26, wherein the GUI code uses the database category region of the screen to allow users to select and display a particular sequence or all sequences from a database of sequences using a drop down menu.

32. The product of claim 26, wherein the GUI code uses the database category region of the screen to allow users to view groups of similar sequences.

33. The product of claim 26, wherein the GUI code uses the database category region of the screen to allow users to activate execution of the program.

34. The product of claim 26, wherein the GUI code uses the output options category region of the screen to allow users to selectively display identifiers associated with each input sequence and a summary/details of matches of characteristic residues for an input query sequence identified by its identifier.

35. The product of claim 25, wherein the storage code identifies characteristic residues of individual virus sequences or their groups from program supplied external files and stores these residues, groups and other related information in tree-like multiple 2-dimensional arrays for efficient referencing and retrieval.

36. The product of claim 25, wherein the storage code numbers the characteristic residues and the storage code identifies characteristic residues of individual virus sequences or their groups from program supplied external files and stores these residues, groups and other related information in tree-like multiple 2-dimensional arrays for efficient referencing and retrieval with respect to the GUI code, which uses the database category region of the screen to use default reference sequences or allow users to pre-select specific reference sequences to facilitate sequence comparisons for sequence comparison purposes.

37. A method of evaluating comparisons implemented on a computer or encoded on a computer readable storage medium, the method comprising the steps of:

identifying tree branches including maximum number of characteristic residue matches between an input sequence or a plural using a viral pathogen identification computer product implemented on the computer or encoded on the computer readable storage medium, where the product includes:

a storage code adapted to identify characteristic residues of individual virus sequences or their groups from program supplied external files and stores these residues, groups and other related information in tree-like multiple 2-dimensional arrays for efficient referencing and retrieval;

a sequence comparison code adapted to select individual residues of an input sequence or a plurality of input sequences and to compare the selected residues with the characteristic residues of the input sequence or sequences to generate comparisons including maximum number of characteristic residue matches using a tree-like search and to store the matches in tree-like multiple 2-dimensional arrays for efficient referencing and retrieval, a graphics user interface (GUI) code adapted to allow a user to enter the input sequence or sequences in a sequence category region of a screen of a display associated with an implementing computer in a specified format using a paste option or by reading in files, to allow a user to select default reference sequences or to pre-select specific reference sequences to facilitate sequence comparisons in a database category region of the screen, and to allow the comparisons to be displayed in the database category region of the screen, searching the matches to identify maximally matching tree branches, carrying out further searches in the case where no unique maximally matching tree branches from the identifying step are found, and confirming that the chosen maximally matching tree branches do not lead to ambiguous comparisons.

\* \* \* \* \*

SEQUENCE LISTING

<160> NUMBER OF SEQ ID NOS: 211

<210> SEQ ID NO 1
<211> LENGTH: 861
<212> TYPE: DNA
<213> ORGANISM: rhinovirus

<400> SEQUENCE: 1
aatccagtag aaaactacat tgatgaagtt ttaaatgaag ttttagtagt gccgaatata      60
aaagaaagtc atcacactac atcaaactct gccccacttt tagatgctgc agagacggga     120
cacaccagta atgttcaacc agaagatgct atagagacaa ggtatgttat aacatcacaa     180
acaagagatg agatgagtat agaaagtttc cttggtagat ctggttgtgt ccacatctca     240
agaataaagg ttgattacac tgactataat ggacaggaca taaatttcac aaaatggaaa     300
atcacactac aggaaatggc acagattagg agaaaatttg aattgtttac atatgtcagg     360
tttgactcag aaataacctt ggtgccttgt attgctggta gaggagacga cattggacat     420
attgtaatgc aatatatgta tgttcctcca ggagctccaa ttccttcaaa aagaaacgat     480
ttctcatggc aatcaggcac caatatgtca atattctggc aacatggaca gccatttcct     540
agattttctt taccatttct tagcattgca tcagcttatt atatgtttta tgatggatat     600
gatggagaca cacttcttc caagtatggt agcgtagtta ctaatgatat gggtactata     660
tgctcaagaa tagttacaga aaaacagaaa cattctgttg tcatcacaac acacatatat     720
cataaagcta aacacacaaa agcttggtgt cctaggcccc ctagagctgt cccttacaca     780
catagtcatg tgactaatta tatgccagaa acaggtgacg tgacaacagc catagtccgc     840
agaaacacta taacaactgc a                                                861

<210> SEQ ID NO 2
<211> LENGTH: 861
<212> TYPE: DNA
<213> ORGANISM: rhinovirus

<400> SEQUENCE: 2
aatccagtag aaaactacat tgatgaagtt ttaaatgaag ttttagtagt gccgaatata      60
aaagaaagtc atcacactac atcaaactct gccccacttt tagatgctgc agagacggga     120
cacaccagta atgttcaacc agaagatgct atagagacaa ggtatgttat aacatcacaa     180
acaagagatg agatgagtat agaaagtttc cttggtagat ctggttgtgt ccacatctca     240

-continued

```
agaataaagg ttgattacac tgactataat ggacaggaca taaatttcac aaaatggaaa      300
atcacactac aggaaatggc acagattagg agaaaatttg aattgtttac atatgtcagg      360
tttgactcag aaataacctt ggtgccttgt attgctggta gaggagacga cattggacat      420
attgtaatgc aatatatgta tgttcctcca ggagctccaa ttccttcaaa aagaaacgat      480
ttctcatggc aatcaggcac caatatgtca atattctggc aacatggaca gccatttcct      540
agattttctt taccatttct tagcattgca tcagcttatt atatgtttta tgatggatat      600
gatggagaca cacttcttc caagtatggt agcgtagtta ctaatgatat gggtactata       660
tgctcaagaa tagttacaga aaacagaaa cattctgttg tcatcacaac acacatatat       720
cataaagcta acacacaaa agcttggtgt cctaggcccc ctagagctgt cccttacaca       780
catagtcatg tgactaatta tatgccagaa acaggtgacg tgacaacagc catagtccgc      840
agaaacacta taacaactgc g                                                861
```

<210> SEQ ID NO 3
<211> LENGTH: 861
<212> TYPE: DNA
<213> ORGANISM: rhinovirus

<400> SEQUENCE: 3

```
aatccagtag aaaactacat tgatgaagtt ttaaatgaag ttttagtagt gccgaatata       60
aaagaaagtc atcacactac atcaaactct gccccacttt tagatgctgc agagacggga      120
cacaccagta atgttcaacc agaagatgct atagagacaa ggtatgttat aacatcacaa      180
acaagagatg agatgagtat agaaagtttc cttggtagat ctggttgtgt ccacatctca      240
agaataaagg ttgattacac tgactataat ggacaggaca taaatttcac aaaatggaaa      300
atcacactac aggaaatggc acagattagg agaaaatttg aattgtttac atatgtcagg      360
tttgactcag aaataacctt ggtgccttgt attgctggta gaggagacga cattggacat      420
attgtaatgc aatatatgta tgttcctcca ggagctccaa ttccttcaaa aagaaacgat      480
ttctcatggc aatcaggcac caatatgtca atattctggc aacatggaca gccatttcct      540
agattttctt taccatttct tagcattgca tcagcttatt atatgtttta tgatggatat      600
gatggagaca cacttcttc caagtatggt agcgtagtta ctaatgatat gggtactata       660
tgctcaagaa tagttacaga aaacagaaa cattctgttg tcatcacaac acacatatat       720
cataaagcta acacacaaa agcttggtgt cctaggcccc ctagagctgt cccttacaca       780
catagtcatg tgactaatta tatgccagaa acaggtgacg tgacaacagc catagtccgc      840
agaaacacta taacaactgc t                                                861
```

<210> SEQ ID NO 4
<211> LENGTH: 861
<212> TYPE: DNA
<213> ORGANISM: rhinovirus

<400> SEQUENCE: 4

```
aatccagtgg aaaattacat tgatgaagtt ttaaatgaag ttctagtagt accaaatata       60 aagaaagcc atcacactac atcaaattct gctccactct ggatgctgc agagacagga       120 cacaccagta atgtacaacc agaggatgct atagaaacaa gatatgttat gacatcacaa      180
acaagagatg agatgagtat agaaagttt cttggtagat ctggctgtgt gcatatttca       240
agaataaagg ttgattacaa tgactacaat ggagtgaaca aaaactttac aacatggaaa      300
atcacactgc aggagatggc acaaattaga agaaaattcg aactatttac ttatgttagg      360
```

```
tttgattcag aagtaacttt agtaccctgt attgctggta gaggagatga cattggtcat    420
gttgtaatgc agtatatgta tgttccccca ggagctccaa ttccaaaaac aagaaatgat    480
ttctcatggc aatcaggcac taatatgtca atattctggc aacatggaca accgttccct    540
agattctctt taccatttct tagcattgca tcagcttatt acatgtttta tgatggatat    600
gatggagata attcctcttc caaatatggt agtatagtca ccaatgatat gggaaccata    660
tgttcaagaa tagttacaga gaagcaggaa caccctgtcg ttattacaac acacatatat    720
cacaaagcta aacacacaaa agcttggtgt cctagacctc ctagagctgt tccttacaca    780
catagtcgtg taactaatta tgtaccaaaa acaggtgatg tgacaacagc tatagttcct    840
agagctagca tgaaaactgt a

| | |
|---|---:|
| gttgtaatgc agtatatgta tgttccccca ggagctccaa ttccaaaaac aagaaatgat | 480 |
| ttctcatggc aatcaggcac taatatgtca atattctggc aacatggaca accgttccct | 540 |
| agattctctt taccatttct tagcattgca tcagcttatt acatgttta tgatggatat | 600 |
| gatggagata attcctcttc caaatatggt agtatagtca ccaatgatat gggaaccata | 660 |
| tgttcaagaa tagttacaga gaagcaggaa caccctgtcg ttattacaac acacatatat | 720 |
| cacaaagcta aacacacaaa agcttggtgt cctagacctc ctagagctgt tccttacaca | 780 |
| catagtcgtg taactaatta tgtaccaaaa acaggtgatg tgacaacagc tatagttcct | 840 |
| agagctagca tgaaaactgt t | 861 |

```
<210> SEQ ID NO 7
<211> LENGTH: 858
<212> TYPE: DNA
<213> ORGANISM: rhinovirus

<400> SEQUENCE: 7
```

| | |
|---|---:|
| aaccccgttg aaaggtatgt tgatgaggtt cttaatgaag ttctggtagt tccaaatatc | 60 |
| agagagagcc atccaactac atcaaattcg gcccctgcct tggatgcagc agagactgga | 120 |
| catacaagca acatacaacc tgaagataca atagaaacaa gatttgtgca gacatcacaa | 180 |
| actagagatg aaatgagcat agagagtttc ttgggaagat ctgggtgcat tcatatatcc | 240 |
| acaattacag tggataacag tttggaatat gatgaccacc actttgataa gtggcagata | 300 |
| accatacaag agatgtcaca aattaggaga aaatttgaat tctttacata tgctaggttt | 360 |
| gattcagaaa ttaccttagt tccttgtata gccggtaagg gtgaagacat tggacacatt | 420 |
| gtgatgcaat atatgtatgt accccctggc gcacccatac caagaaaaag aaatgattac | 480 |
| acatggcagt caggcactaa tgcttctgta ttctggcaac atggtcaaac tttccctaga | 540 |
| ttttctttac ctttcctaag catagcttca gcatactaca tgttttatga tggatacgat | 600 |
| ggtgatacat cgacctcaag atatggcaca tcagtcacta accatatggg aacgctatgc | 660 |
| tcaagaatag tcaccaacaa gcagcagcat gaagttgaga ttaccacacg tatatatcac | 720 |
| aaggccaagc atattaaagc atggtgtcca agggccccaa gagcagtacc ttacacacat | 780 |
| acacactcaa caaattataa acctcaagaa ggtgaagtcc agattttcct caaagagaga | 840 |
| gccagcctaa caacagta | 858 |

```
<210> SEQ ID NO 8
<211> LENGTH: 858
<212> TYPE: DNA
<213> ORGANISM: rhinovirus

<400> SEQUENCE: 8
```

| | |
|---|---:|
| aaccccgttg aaaggtatgt tgatgaggtt cttaatgaag ttctggtagt tccaaatatc | 60 |
| agagagagcc atccaactac atcaaattcg gcccctgcct tggatgcagc agagactgga | 120 |
| catacaagca acatacaacc tgaagataca atagaaacaa gatttgtgca gacatcacaa | 180 |
| actagagatg aaatgagcat agagagtttc ttgggaagat ctgggtgcat tcatatatcc | 240 |
| acaattacag tggataacag tttggaatat gatgaccacc actttgataa gtggcagata | 300 |
| accatacaag agatgtcaca aattaggaga aaatttgaat tctttacata tgctaggttt | 360 |
| gattcagaaa ttaccttagt tccttgtata gccggtaagg gtgaagacat tggacacatt | 420 |
| gtgatgcaat atatgtatgt accccctggc gcacccatac caagaaaaag aaatgattac | 480 |
| acatggcagt caggcactaa tgcttctgta ttctggcaac atggtcaaac tttccctaga | 540 |

```
ttttctttac ctttcctaag catagcttca gcatactaca tgttttatga tggatacgat    600
ggtgatacat cgacctcaag atatggcaca tcagtcacta accatatggg aacgctatgc    660
tcaagaatag tcaccaacaa gcagcagcat gaagttgaga ttaccacacg tatatatcac    720
aaggccaagc atattaaagc atggtgtcca agggccccaa gagcagtacc ttacacacat    780
acacactcaa caaattataa acctcaagaa ggtgaagtcc agattttcct caaagagaga    840
gccagcctaa caacagtc                                                  858
```

```
<210> SEQ ID NO 9
<211> LENGTH: 858
<212> TYPE: DNA
<213> ORGANISM: rhinovirus

<400> SEQUENCE: 9
aaccccgttg aaaggtatgt tgatgaggtt cttaatgaag ttctggtagt tccaaatatc     60
agagagagcc atccaactac atcaaattcg gcccctgcct tggatgcagc agagactgga    120
catacaagca acatcaaacc tgaagataca atagaaacaa gatttgtgca gacatcacaa    180
actagagatg aaatgagcat agagagtttc ttgggaagat ctgggtgcat tcatatatcc    240
acaattacag tggataacag tttggaatat gatgaccacc actttgataa gtggcagata    300
accatacaag agatgtcaca aattaggaga aaatttgaat tctttacata tgctaggttt    360
gattcagaaa ttaccttagt tccttgtata gccggtaagg gtgaagacat tggacacatt    420
gtgatgcaat atatgtatgt accccctggc gcacccatac caagaaaaag aaatgattac    480
acatggcagt caggcactaa tgcttctgta ttctggcaac atggtcaaac tttccctaga    540
ttttctttac ctttcctaag catagcttca gcatactaca tgttttatga tggatacgat    600
ggtgatacat cgacctcaag atatggcaca tcagtcacta accatatggg aacgctatgc    660
tcaagaatag tcaccaacaa gcagcagcat gaagttgaga ttaccacacg tatatatcac    720
aaggccaagc atattaaagc atggtgtcca agggccccaa gagcagtacc ttacacacat    780
acacactcaa caaattataa acctcaagaa ggtgaagtcc agattttcct caaagagaga    840
gccagcctaa caacagtt                                                  858
```

```
<210> SEQ ID NO 10
<211> LENGTH: 858
<212> TYPE: DNA
<213> ORGANISM: rhinovirus

<400> SEQUENCE: 10
aatcctgttg aaaaatacgt tgatgaagtc cttaatgagg ttctagtggt tccaaatatc     60
aaagagagtc acccaactat atcaaattca gctcctgctt tggatgcagc agagactggc    120
catacaagta gtacacagcc cgaggataca atagagacca ggtttgttca aacttcacag    180
actagggatg aaatgagttt agaaagtttc ttgggaagat ctggatgtat ccatatatct    240
acaattactg tgaataacaa cctagattat gatgaaaatc actttgatca gtggcagata    300
actatacagg aaatggcaca aattagaagg aagtttgagt tctttactta cactagattt    360
gattcagaaa tcactttagt cccttgtata gctggaaagg gtgatgatat tggacacatt    420
gtaatgcagt atatgtatgt gccccccgga gcaccaatac caaggaaaag agatgattac    480
acatggcaat caggtactaa tgcttccgtg ttttggcaac atgggcaaac tttccccaga    540
ttttccttac ctttcttgag tgttgcttca gcatattaca tgttttatga tggttatgat    600
```

| | |
|---|---|
| ggtgatacac caggctcaat gtatgggacg tcagtcacca accacatggg aacactgtgc | 660 |
| tcgaggatag ttaccaacaa acagcagcat gaggttgaaa tcaccacgcg tgtgtatcat | 720 |
| aaggccaagc atgtaaaggc ttggtgtcca agagcaccaa gagcggtgcc ttatacacac | 780 |
| acacgctcaa ccaactatgt gccacaagat ggtgaagtta agatcttcct caaagagaga | 840 |
| gctagtttaa ccacagca | 858 |

<210> SEQ ID NO 11
<211> LENGTH: 858
<212> TYPE: DNA
<213> ORGANISM: rhinovirus

<400> SEQUENCE: 11

| | |
|---|---|
| aatcctgttg aaaatacgt tgatgaagtc cttaatgagg ttctagtggt tccaaatatc | 60 |
| aaagagagtc acccaactat atcaaattca gctcctgctt tggatgcagc agagactggc | 120 |
| catacaagta gtacacagcc cgaggataca atagagacca ggtttgttca aacttcacag | 180 |
| actagggatg aaatgagttt agaaagtttc ttgggaagat ctggatgtat ccatatatct | 240 |
| acaattactg tgaataacaa cctagattat gatgaaaatc actttgatca gtggcagata | 300 |
| actatacagg aaatggcaca aattagaagg aagtttgagt tctttactta cactagattt | 360 |
| gattcagaaa tcactttagt cccttgtata gctggaaagg gtgatgatat tggacacatt | 420 |
| gtaatgcagt atatgtatgt gccccccgga gcaccaatac caaggaaaag agatgattac | 480 |
| acatggcaat caggtactaa tgcttccgtg ttttggcaac atgggcaaac tttccccaga | 540 |
| ttttccttac ctttcttgag tgttgcttca gcatattaca tgtttttatga tggttatgat | 600 |
| ggtgatacac caggctcaat gtatgggacg tcagtcacca accacatggg aacactgtgc | 660 |
| tcgaggatag ttaccaacaa acagcagcat gaggttgaaa tcaccacgcg tgtgtatcat | 720 |
| aaggccaagc atgtaaaggc ttggtgtcca agagcaccaa gagcggtgcc ttatacacac | 780 |
| acacgctcaa ccaactatgt gccacaagat ggtgaagtta agatcttcct caaagagaga | 840 |
| gctagtttaa ccacagcg | 858 |

<210> SEQ ID NO 12
<211> LENGTH: 858
<212> TYPE: DNA
<213> ORGANISM: rhinovirus

<400> SEQUENCE: 12

| | |
|---|---|
| aatcctgttg aaaatacgt tgatgaagtc cttaatgagg ttctagtggt tccaaatatc | 60 |
| aaagagagtc acccaactat atcaaattca gctcctgctt tggatgcagc agagactggc | 120 |
| catacaagta gtacacagcc cgaggataca atagagacca ggtttgttca aacttcacag | 180 |
| actagggatg aaatgagttt agaaagtttc ttgggaagat ctggatgtat ccatatatct | 240 |
| acaattactg tgaataacaa cctagattat gatgaaaatc actttgatca gtggcagata | 300 |
| actatacagg aaatggcaca aattagaagg aagtttgagt tctttactta cactagattt | 360 |
| gattcagaaa tcactttagt cccttgtata gctggaaagg gtgatgatat tggacacatt | 420 |
| gtaatgcagt atatgtatgt gccccccgga gcaccaatac caaggaaaag agatgattac | 480 |
| acatggcaat caggtactaa tgcttccgtg ttttggcaac atgggcaaac tttccccaga | 540 |
| ttttccttac ctttcttgag tgttgcttca gcatattaca tgtttttatga tggttatgat | 600 |
| ggtgatacac caggctcaat gtatgggacg tcagtcacca accacatggg aacactgtgc | 660 |
| tcgaggatag ttaccaacaa acagcagcat gaggttgaaa tcaccacgcg tgtgtatcat | 720 |

| | |
|---|---|
| aaggccaagc atgtaaaggc ttggtgtcca agagcaccaa gagcggtgcc ttatacacac | 780 |
| acacgctcaa ccaactatgt gccacaagat ggtgaagtta agatcttcct caaagagaga | 840 |
| gctagtttaa ccacagct | 858 |

<210> SEQ ID NO 13
<211> LENGTH: 858
<212> TYPE: DNA
<213> ORGANISM: rhinovirus

<400> SEQUENCE: 13

| | |
|---|---|
| aacccagttg agagatatgt agatgatgtt ttaaatgaag ttttagttgt tccaaatatt | 60 |
| agggagagcc atccatccac atcaaattct gcccctgcat tagatgctgc tgaaactggc | 120 |
| catactagtg caatccaacc agaagacact atagaaacca gatatgtaca gacatcacaa | 180 |
| actagggatg aaatgagtat agagagtttt ctaggtagat caggttgtat acatatatca | 240 |
| actataactg tggataatga tgtagattat aattcaaagc attataataa atggcaaata | 300 |
| accttacaag aaatggctca agttaggcgt aaatttgaat tctttactta tgtcagattt | 360 |
| gattcagagg ttactttggt accttgtgta gccggcaagg gagatgatat tggacacatt | 420 |
| gtaatgcaat acatgtatgt gcctcctggt gcaccacttc caaactcaag agatgatttt | 480 |
| acatggcaat ctggcaccaa tgcttctgtc ttttggcaac atggccaagc tttccccaga | 540 |
| ttctctctac ctttcttaag tattgcttct gcttattaca tgttttatga tggttatgat | 600 |
| ggagacactt caagctccag atatggtaca tcagttacaa accacatggg gacactctgt | 660 |
| tcaagaattg tgacaaataa acaacttcat cctgttgaag tcacaactcg tgtatatcat | 720 |
| aaggcaaagc atattcgagc atggtgtcct agagcaccaa gggctgtgcc ttatacacat | 780 |
| gctcacgtca ccaattataa accacaagat ggtgatgtac agatcttctt aaaacccaga | 840 |
| cccagcctaa caacatta | 858 |

<210> SEQ ID NO 14
<211> LENGTH: 858
<212> TYPE: DNA
<213> ORGANISM: rhinovirus

<400> SEQUENCE: 14

| | |
|---|---|
| aacccagttg agagatatgt agatgatgtt ttaaatgaag ttttagttgt tccaaatatt | 60 |
| agggagagcc atccatccac atcaaattct gcccctgcat tagatgctgc tgaaactggc | 120 |
| catactagtg caatccaacc agaagacact atagaaacca gatatgtaca gacatcacaa | 180 |
| actagggatg aaatgagtat agagagtttt ctaggtagat caggttgtat acatatatca | 240 |
| actataactg tggataatga tgtagattat aattcaaagc attataataa atggcaaata | 300 |
| accttacaag aaatggctca agttaggcgt aaatttgaat tctttactta tgtcagattt | 360 |
| gattcagagg ttactttggt accttgtgta gccggcaagg gagatgatat tggacacatt | 420 |
| gtaatgcaat acatgtatgt gcctcctggt gcaccacttc caaactcaag agatgatttt | 480 |
| acatggcaat ctggcaccaa tgcttctgtc ttttggcaac atggccaagc tttccccaga | 540 |
| ttctctctac ctttcttaag tattgcttct gcttattaca tgttttatga tggttatgat | 600 |
| ggagacactt caagctccag atatggtaca tcagttacaa accacatggg gacactctgt | 660 |
| tcaagaattg tgacaaataa acaacttcat cctgttgaag tcacaactcg tgtatatcat | 720 |
| aaggcaaagc atattcgagc atggtgtcct agagcaccaa gggctgtgcc ttatacacat | 780 |

```
gctcacgtca ccaattataa accacaagat ggtgatgtac agatcttctt aaaacccaga    840
cccagcctaa caacattg                                                  858
```

<210> SEQ ID NO 15
<211> LENGTH: 858
<212> TYPE: DNA
<213> ORGANISM: rhinovirus

<400> SEQUENCE: 15

```
aacccagttg agagatatgt agatgatgtt ttaaatgaag ttttagttgt tccaaatatt     60
agggagagcc atccatccac atcaaattct gcccctgcat tagatgctgc tgaaactggc    120
catactagtg caatccaacc agaagacact atagaaacca gatatgtaca gacatcacaa    180
actagggatg aaatgagtat agagagtttt ctaggtagat caggttgtat acatatatca    240
actataactg tggataatga tgtagattat aattcaaagc attataataa atggcaaata    300
accttacaag aaatggctca agttaggcgt aaatttgaat tctttactta tgtcagattt    360
gattcagagg ttactttggt accttgtgta gccggcaagg agatgatat tggacacatt     420 gtaatgcaat acatgtatgt gcctcctggt gcaccacttc caaactcaag agatgatttt    480
acatggcaat ctggcaccaa tgcttctgtc ttttggcaac atggccaagc tttccccaga    540
ttctctctac ctttcttaag tattgcttct gcttattaca tgtttatga tggttatgat     600 ggagacactt caagctccag atatggtaca tcagttacaa accacatggg gacactctgt    660
tcaagaattg tgacaaataa acaacttcat cctgttgaag tcacaactcg tgtatatcat    720
aaggcaaagc atattcgagc atggtgtcct agagcaccaa gggctgtgcc ttatacacat    780
gctcacgtca ccaattataa accacaagat ggtgatgtac agatcttctt aaaacccaga    840
cccagcctaa caacattt                                                  858
```

<210> SEQ ID NO 16
<211> LENGTH: 858
<212> TYPE: DNA
<213> ORGANISM: rhinovirus

<400> SEQUENCE: 16

```
aatcctgtag aaagatatgt tgatgaagtg ttaaatgaag tgttagttgt cccaaacatt     60
agagaaagtc atccagctac atctaattca gcccctgcgc tagatgcggc agaaactgga    120
cacactagtg gagtacaacc cgaggacacc atagaaacaa gatttgtgca gacatcacaa    180
actagagatg aaatgagcat agaaagtttt ctaggcaggg ctggttgcat acatgaatcc    240
accattacaa ttcaaaatga tgtagaatac aatgatcacc attttaagaa atgggatata    300
acattacaag agatggcaca aatacgaagg aaatttgaat tctttactta tgttaggttt    360
gattcagaaa ttactctagt ccctgtata gctggtaagg gagttgatat tggacacatt      420
gtcatgcaat tcatgtatgt accgcctggt gcaccaaaac cagaaaaaag gaatgattac    480
acctgggagt caagcacaaa cccttctata ttttggcaac atggccaagc ttatccaaga    540 ttctctcttac catttttaag tattgcatct gcttactaca tgtttatga tgggtatgat    600 ggtgacgcac ctggatcaag atatgggact tcagttacca atcatatggg tactttgtgt    660
tcaagagtgg ttactgataa acaaaaacac ccagttaaa tcaccacacg ggtgtatcac     720
aaggcaaaac acattagagc atggtgtcca cgtgcaccta gggctgtccc atacacacat    780
actagatcaa caaattacat gccacgggag ggtgatccaa caattttcct taaacacagg    840
acaaaccttg taacagct                                                  858
```

<210> SEQ ID NO 17
<211> LENGTH: 858
<212> TYPE: DNA
<213> ORGANISM: rhinovirus

<400> SEQUENCE: 17

```
aatcctgtag agagatatgt tgatgaagta ttaaatgaag tgttagttgt tccaaacatt      60
aaagaaagtc atccagctac atctaattcg gccsctacac tagatgcagc agaaactggg     120
cacactagtg aatacaacc tgaggatact atagaaacaa gatatgtgca gacatcacaa     180
accagagatg aaatgagtat agaaagtttt ctaggtaggg ccggttgtat acatgaatct     240
actatcacta ttcaaaatga tgtagaatat aacgatcatc attttagaca atgggatata     300
acattacaag aaatggcaca aattcgaaga aaatttgaat tctttactta tgttagattt     360
gattcagaag ttaccttagt tccttgcata gctggcaagg gagctgacat tggacacatt     420
gtcatgcaat tcatgtatgt tccacctggt gcacctaaac ctaaaaagag gaatgattat     480
acttgggaat caagcacaaa cccttctata ttctggcagc atggtcaggc ctatccaaga     540
ttttctctac cattcttgag cattgcatct gcttactaca tgttttacga tgggtatgat     600
ggtgatgcac ctggatcaag atatggaacc tcagtcacta atcacatggg cactttgtgt     660
tcaagagtag ttactggcaa acaagaacac ccagttgaaa tcactacacg tgtgtaccac     720
aaagcaaaac acattagagc atggtgtcca cgtgcaccta gagctgttcc atacacacac     780
actagatcaa ctaattacat gcctcaagat ggtgaaccaa caatcttctct taagcataga     840
aaagatcttg taacagct                                                    858
```

<210> SEQ ID NO 18
<211> LENGTH: 858
<212> TYPE: DNA
<213> ORGANISM: rhinovirus

<400> SEQUENCE: 18

```
aacccagtgg aaaactatgt taatgatgta cttaatgagg ttttagtagt accaaatata      60
caggaaagcc acccaaccac ctcaaatgct gctccagcat tagatgcagc agagactgga     120
catacaagca gtatacaacc tgaggatacc atagaaacaa gatatgttca gacatcacaa     180
actagagatg agatgagtgt agaaagtttc ttaggtagat ctgggtgtat acatatttca     240
actattactg tcaataaaga cataaaaatat gatgatggac acttctcttaa atggcctata     300
acattacaag agatggcaca aattaggaga aaatttgaat tcttcacata tgttagattt     360
gactcagaaa tcactttggt gccttgcata gctggaaaag gggatgacat tggtcatata     420
gtcatgcaat atatgtatgt tccaccaggt gctccactgc ccacaaagag agatgattac     480
acatggcaat ctggtactaa tgcttcaata ttctggcaac atggacaaac attcccaaga     540
ttttcattgc ccttcctgag catagcatca gcttattaca tgttttatga tggttatgat     600
ggagatataat ctgaatctag gtatggtgtg tctgtaacca accacatggg cactttatgt     660
tctagaatag ttacaaacag tcaggagcat ccagtggagg ttgtcacacg tgtgtatcac     720
aaagctaaac acgtcaaagc ctggtgccct agagctccta gagcagtccc ttacacacac     780
agctacgtaa ctaactacaa gattgctgga aaagaacctg aaatttttctt aaaaccaaga     840
atgaatatta caacagca                                                    858
```

<210> SEQ ID NO 19

<211> LENGTH: 858
<212> TYPE: DNA
<213> ORGANISM: rhinovirus

<400> SEQUENCE: 19

```
aacccagtgg aaaactatgt taatgatgta cttaatgagg ttttagtagt accaaatata      60
caggaaagcc acccaaccac ctcaaatgct gctccagcat tagatgcagc agagactgga     120
catacaagca gtatacaacc tgaggatacc atagaaacaa gatatgttca gacatcacaa     180
actagagatg agatgagtgt agaaagtttc ttaggtagat ctgggtgtat acatatttca     240
actattactg tcaataaaga cataaaatat gatgatggac actttcttaa atggcctata     300
acattacaag agatggcaca aattaggaga aaatttgaat tcttcacata tgttagattt     360
gactcagaaa tcactttggt gccttgcata gctggaaaag gggatgacat tggtcatata     420
gtcatgcaat atatgtatgt tccaccaggt gctccactgc ccacaaagag agatgattac     480
acatggcaat ctggtactaa tgcttcaata ttctggcaac atggacaaac attcccaaga     540
ttttcattgc ccttcctgag catagcatca gcttattaca tgttttatga tggttatgat     600
ggagataaat ctgaatctag gtatggtgtg tctgtaacca accacatggg cactttatgt     660
tctagaatag ttacaaacag tcaggagcat ccagtggagg ttgtcacacg tgtgtatcac     720
aaagctaaac acgtcaaagc ctggtgccct agagctccta gagcagtccc ttacacacac     780
agctacgtaa ctaactacaa gattgctgga aaagaacctg aaattttctt aaaaccaaga     840
atgaatatta caacagcg                                                    858
```

<210> SEQ ID NO 20
<211> LENGTH: 858
<212> TYPE: DNA
<213> ORGANISM: rhinovirus

<400> SEQUENCE: 20

```
aacccagtgg aaaactatgt taatgatgta cttaatgagg ttttagtagt accaaatata      60
caggaaagcc acccaaccac ctcaaatgct gctccagcat tagatgcagc agagactgga     120
catacaagca gtatacaacc tgaggatacc atagaaacaa gatatgttca gacatcacaa     180
actagagatg agatgagtgt agaaagtttc ttaggtagat ctgggtgtat acatatttca     240
actattactg tcaataaaga cataaaatat gatgatggac actttcttaa atggcctata     300
acattacaag agatggcaca aattaggaga aaatttgaat tcttcacata tgttagattt     360
gactcagaaa tcactttggt gccttgcata gctggaaaag gggatgacat tggtcatata     420
gtcatgcaat atatgtatgt tccaccaggt gctccactgc ccacaaagag agatgattac     480
acatggcaat ctggtactaa tgcttcaata ttctggcaac atggacaaac attcccaaga     540
ttttcattgc ccttcctgag catagcatca gcttattaca tgttttatga tggttatgat     600
ggagataaat ctgaatctag gtatggtgtg tctgtaacca accacatggg cactttatgt     660
tctagaatag ttacaaacag tcaggagcat ccagtggagg ttgtcacacg tgtgtatcac     720
aaagctaaac acgtcaaagc ctggtgccct agagctccta gagcagtccc ttacacacac     780
agctacgtaa ctaactacaa gattgctgga aaagaacctg aaattttctt aaaaccaaga     840
atgaatatta caacagct                                                    858
```

<210> SEQ ID NO 21
<211> LENGTH: 858
<212> TYPE: DNA
<213> ORGANISM: rhinovirus

<400> SEQUENCE: 21

```
aatccagtag agaattatgt aaatgatgtt cttaatgaag tgttagttgt tccaaacata      60
caagaaagcc atccaaccac atcaaacgct gctcctgtac ttgatgctgc ggaaacagga     120
cacacaagca gtatacaacc tgaggatact gtagaaacta gatatgtgca acgtctcaa     180
acaagggatg aaatgagtgt agagagcttt cttggtagat caggatgcat acacatatca     240
actatcactg ttgacaaaac cattgactat gacactggac attttaataa atggcaaata     300
acattacaag agatggcaca aattagaagg aaatttgaat tcttcacata tgtcagattt     360
gattcagaag tcactcttgt accatgtata gcaggaaaag gtgatgacat tggtcatata     420
gttatgcagt acatgtacgt tccacccggt gccctctac ccacccgaag agaagattac     480
acatggcaat ctggcactaa tgcttcaata ttctggcaac atggacaagc ttttccaagg     540
ttttctctac ctttcttgag tattgcatca gcatattaca tgttttatga tggatatgat     600
ggagataaat caagctctag gtatggtgtt tcagttacta ccacatggg actttatgt     660
tctagaattg taacaaacag ccaagaacat ccagttgagg tgactacacg tgtatatcat     720
aaagctaaac acatcagagc ctggtgccca agagctccta gggctgttcc atacacacat     780
agttatgtca ctaactataa aattacagga caggagactg aaattttctt aaaacctaga     840
gcaactatca agacagca                                                    858
```

<210> SEQ ID NO 22
<211> LENGTH: 858
<212> TYPE: DNA
<213> ORGANISM: rhinovirus

<400> SEQUENCE: 22

```
aatccagtag agaattatgt aaatgatgtt cttaatgaag tgttagttgt tccaaacata      60
caagaaagcc atccaaccac atcaaacgct gctcctgtac ttgatgctgc ggaaacagga     120
cacacaagca gtatacaacc tgaggatact gtagaaacta gatatgtgca acgtctcaa     180
acaagggatg aaatgagtgt agagagcttt cttggtagat caggatgcat acacatatca     240
actatcactg ttgacaaaac cattgactat gacactggac attttaataa atggcaaata     300
acattacaag agatggcaca aattagaagg aaatttgaat tcttcacata tgtcagattt     360
gattcagaag tcactcttgt accatgtata gcaggaaaag gtgatgacat tggtcatata     420
gttatgcagt acatgtacgt tccacccggt gccctctac ccacccgaag agaagattac     480
acatggcaat ctggcactaa tgcttcaata ttctggcaac atggacaagc ttttccaagg     540
ttttctctac ctttcttgag tattgcatca gcatattaca tgttttatga tggatatgat     600
ggagataaat caagctctag gtatggtgtt tcagttacta ccacatggg actttatgt     660
tctagaattg taacaaacag ccaagaacat ccagttgagg tgactacacg tgtatatcat     720
aaagctaaac acatcagagc ctggtgccca agagctccta gggctgttcc atacacacat     780
agttatgtca ctaactataa aattacagga caggagactg aaattttctt aaaacctaga     840
gcaactatca agacagcg                                                    858
```

<210> SEQ ID NO 23
<211> LENGTH: 858
<212> TYPE: DNA
<213> ORGANISM: rhinovirus

<400> SEQUENCE: 23

-continued

```
aatccagtag agaattatgt aaatgatgtt cttaatgaag tgttagttgt tccaaacata      60
caagaaagcc atccaaccac atcaaacgct gctcctgtac ttgatgctgc ggaaacagga     120
cacacaagca gtatacaacc tgaggatact gtagaaacta gatatgtgca aacgtctcaa     180
acaagggatg aaatgagtgt agagagcttt cttggtagat caggatgcat acacatatca     240
actatcactg ttgacaaaac cattgactat gacactggac attttaataa atggcaaata     300
acattacaag agatggcaca aattagaagg aaatttgaat tcttcacata tgtcagattt     360
gattcagaag tcactcttgt accatgtata gcaggaaaag gtgatgacat tggtcatata     420
gttatgcagt acatgtacgt tccacccggt gcccctctac ccacccgaag agaagattac     480
acatggcaat ctggcactaa tgcttcaata ttctggcaac atggacaagc ttttccaagg     540
ttttctctac ctttcttgag tattgcatca gcatattaca tgttttatga tggatatgat     600
ggagataaat caagctctag gtatggtgtt tcagttacta accacatggg gactttatgt     660
tctagaattg taacaaacag ccaagaacat ccagttgagg tgactacacg tgtatatcat     720
aaagctaaac acatcagagc ctggtgccca agagctccta gggctgttcc atacacacat     780
agttatgtca ctaactataa aattacagga caggagactg aaattttctt aaaacctaga     840
gcaactatca agacagct                                                   858

<210> SEQ ID NO 24
<211> LENGTH: 855
<212> TYPE: DNA
<213> ORGANISM: rhinovirus

<400> SEQUENCE: 24
aatccagtag aaaattatat agatgaagta ttaaatgagg tattagttgt tcctaatata      60
agagagagcc atccaactac atctaatgca gctacagctt tggatgctgc tgaaactgga     120
cacacaagta gcacccagcc tgaagacaca attgaaacaa gatatgtgca aacctcacat     180
actagggatg aaatgagcgt tgaaagtttc ttaggcagat ctggctgtat tcacatttcc     240
acaattacta tgaagaagga gaactataat gatcataatt ttgtggattg gaaaattact     300
ttgcaggaga tggcacaggt tagaaggaaa tttgaaatgt tcacctatgt tagatttgac     360
tcagagatta ctttagtccc catgcatagc tggaagaggtg aagatattgg acacatagta     420
atgcaataca tgtatgtccc acctggtgca cctgtaccta agaagagaga tgattacaca     480
tggcaatctg gaacaaatgc ctcagttttc tggcaacacg gacagcctta ccctagattt     540
tcattaccat ttctaagcat agcctcagca tattatatgt tctatgatgg atatgatggt     600
gataaatcgt catctaggta tggtgtttct gtcactaatg atatgggtac actttgcact     660
agaattgtaa caaaccaaca ggaacaccta gtggaggtta caaccagagt ttaccataaa     720
gccaagcatg ttaaagcatg gtgccctagg gctcccagag cagtccctta cacacacagc     780
aatgttacaa attacaaagt acgggacggt gaaccaacac tctttataaa atcaagagag     840
aatcttacca cagct                                                      855

<210> SEQ ID NO 25
<211> LENGTH: 855
<212> TYPE: DNA
<213> ORGANISM: rhinovirus

<400> SEQUENCE: 25
aatccagtag aaaattatat agatgaagta ttaaatgagg tattagttgt tcctaatata      60
agagagagcc atccaactac atctaatgca gctacagctt tggatgctgc tgaaactgga     120
```

| | |
|---|---|
| cacacaagta gcacccagcc tgaagacaca attgaaacaa gatatgtgca aacctcacat | 180 |
| actagggatg aaatgagcgt tgaaagtttc ttaggcagat ctggctgtat tcacatttcc | 240 |
| acaattacta tgaagaagga gaactataat gatcataatt ttgtggattg aaaaattact | 300 |
| ttgcaggaga tggcacaggt tagaaggaaa tttgaaatgt tcacctatgt tagatttgac | 360 |
| tcagagatta ctttagtccc atgcatagct ggaagaggtg aagatattgg acacatagta | 420 |
| atgcaataca tgtatgtccc acctggtgca cctgtaccta agaagagaga tgattacaca | 480 |
| tggcaatctg gaacaaatgc ctcagttttc tggcaacacg gacagcctta ccctagattt | 540 |
| tcattaccat ttctaagcat agcctcagca tattatatgt tctatgatgg atatgatggt | 600 |
| gataaatcgt catctaggta tggtgtttct gtcactaatg atatgggtac actttgcact | 660 |
| agaattgtaa caaaccaaca ggaacaccta gtggaggtta caaccagagt ttaccataaa | 720 |
| gccaagcatg ttaaagcatg gtgccctagg gctcccagag cagtcccctta cacacacagc | 780 |
| aatgttacaa attacaaagt acgggacggt gaaccaacac tctttataaa atcaagagag | 840 |
| aatcttacca cagca | 855 |

<210> SEQ ID NO 26
<211> LENGTH: 855
<212> TYPE: DNA
<213> ORGANISM: rhinovirus

<400> SEQUENCE: 26

| | |
|---|---|
| aatccagtag aaaattatat agatggagta ttaaatgagg tattagttgt tcctaatata | 60 |
| agagagagcc atccaactac atctaatgca gctccagctt tggatgctgc tgaaactgga | 120 |
| cacacaagta gcatccaacc tgaagacaca attgaaacaa gatatgtgca aacctcacat | 180 |
| actagggatg aaatgagtgt tgaaagtttc ttaggcagat ctggctgtat tcacatttcc | 240 |
| acaattacta tgaagaagga gaactataat gaacataatt ttgtggattg aaaaattact | 300 |
| ttgcaggaga tggcacaggt tagaaggaaa tttgaaatgt tcacctacgt tagatttgac | 360 |
| tcagagatta ctttagtccc atgcatagct ggaagaggtg aagatattgg acacatagta | 420 |
| atgcaataca tgtatgtccc acccggtgca cctgtaccta agaagagaga tgattacaca | 480 |
| tggcaatctg gaacaaatgc ctcagttttc tggcaacacg gacagcctta ccctagattt | 540 |
| tcattaccat ttctaagcat agcctcagca tattatatgt tctatgatgg atatgatggt | 600 |
| gataaatcgt catctaggta tggtgtttct gtcactaatg atatgggtac actttgcact | 660 |
| agaattgtaa caaaccaaca gaaacaccta gtggaggtta caaccagagt ttaccataaa | 720 |
| gccaagcatg ttaaagcatg gtgccctagg gctcccagag cagtcccctta cacacacagc | 780 |
| aatgttacaa attacaaagt acgggacggt gaaccaacac tctttataaa accaagagag | 840 |
| aatcttacca cagct | 855 |

<210> SEQ ID NO 27
<211> LENGTH: 864
<212> TYPE: DNA
<213> ORGANISM: rhinovirus

<400> SEQUENCE: 27

| | |
|---|---|
| aatccagttg aaaattacat tgataatgta cttaatgaag tcctagtggt acccaacatc | 60 |
| agagaaagtc atccaagcac ctctaactct gccccaattc tcgatgcagc tgagactggt | 120 |
| cataccagta gtgtacaacc agaagatacg gttgaaacac gatatgtgca aacatcccag | 180 |

-continued

```
acgagagatg aaatgagtat tgaaagtttt cttggcaggt caggttgtat acacacctca    240
acaataactg ttaataatac aagaccctac aatgaacaca cttttgacac atggcaaata    300
actctacaag aaatggccca aattagaagg aaatttgaaa tgtttacata tgttagattt    360
gactcagaag tcactttagt accttgcatc gcaggcaagg gcgatgacat aggtcacata    420
gttatgcaat atatgtatgt gccacctggg gctccagtac caactaagag agatgatttt    480
gcttggcagt cgggaacaaa tgcatcagtc ttctggcaac atggacaacc tttccctaga    540
ttttctttac ccttcttaag cattgcatct gcttactaca tgttctatga tggttatgat    600
ggtgatacac atgactcacg ttatggcaca acagtgataa atcacatggg cactttgtgc    660
atgcgaatag tcacaaacca gcaagcacat gaggtggaaa ttaccaccag tgtttatcac    720
aaagccaagc atgtcaaagc atggtgtcca agaccaccca gagctgtacc atatacacat    780
gcccattcca caaattacaa accacatggc aaagaattac aaatatttat taggtctaga    840
gatgatccca aagtagtaac tgca                                           864
```

<210> SEQ ID NO 28
<211> LENGTH: 864
<212> TYPE: DNA
<213> ORGANISM: rhinovirus

<400> SEQUENCE: 28

```
aatccagttg aaaattacat tgataatgta cttaatgaag tcctagtggt acccaacatc     60
agagaaagtc atccaagcac ctctaactct gccccaattc tcgatgcagc tgagactggt    120
cataccagta gtgtacaacc agaagatacg gttgaaacac gatatgtgca aacatcccag    180
acgagagatg aaatgagtat tgaaagtttt cttggcaggt caggttgtat acacacctca    240
acaataactg ttaataatac aagaccctac aatgaacaca cttttgacac atggcaaata    300
actctacaag aaatggccca aattagaagg aaatttgaaa tgtttacata tgttagattt    360
gactcagaag tcactttagt accttgcatc gcaggcaagg gcgatgacat aggtcacata    420
gttatgcaat atatgtatgt gccacctggg gctccagtac caactaagag agatgatttt    480
gcttggcagt cgggaacaaa tgcatcagtc ttctggcaac atggacaacc tttccctaga    540
ttttctttac ccttcttaag cattgcatct gcttactaca tgttctatga tggttatgat    600
ggtgatacac atgactcacg ttatggcaca acagtgataa atcacatggg cactttgtgc    660
atgcgaatag tcacaaacca gcaagcacat gaggtggaaa ttaccaccag tgtttatcac    720
aaagccaagc atgtcaaagc atggtgtcca agaccaccca gagctgtacc atatacacat    780
gcccattcca caaattacaa accacatggc aaagaattac aaatatttat taggtctaga    840
gatgatccca aagtagtaac tgcc                                           864
```

<210> SEQ ID NO 29
<211> LENGTH: 864
<212> TYPE: DNA
<213> ORGANISM: rhinovirus

<400> SEQUENCE: 29

```
aatccagttg aaaattacat tgataatgta cttaatgaag tcctagtggt acccaacatc     60
agagaaagtc atccaagcac ctctaactct gccccaattc tcgatgcagc tgagactggt    120
cataccagta gtgtacaacc agaagatacg gttgaaacac gatatgtgca aacatcccag    180
acgagagatg aaatgagtat tgaaagtttt cttggcaggt caggttgtat acacacctca    240
acaataactg ttaataatac aagaccctac aatgaacaca cttttgacac atggcaaata    300
```

```
actctacaag aaatggccca aattagaagg aaatttgaaa tgtttacata tgttagattt      360
gactcagaag tcactttagt accttgcatc gcaggcaagg gcgatgacat aggtcacata      420
gttatgcaat atatgtatgt gccacctggg gctccagtac caactaagag agatgatttt      480
gcttggcagt cgggaacaaa tgcatcagtc ttctggcaac atggacaacc tttccctaga      540
ttttctttac ccttcttaag cattgcatct gcttactaca tgttctatga tggttatgat      600
ggtgatacac atgactcacg ttatggcaca acagtgataa atcacatggg cactttgtgc      660
atgcgaatag tcacaaacca gcaagcacat gaggtggaaa ttaccaccag tgtttatcac      720
aaagccaagc atgtcaaagc atggtgtcca agaccaccca gagctgtacc atatacacat      780
gcccattcca caaattacaa accacatggc aaagaattac aaatatttat taggtctaga      840
gatgatccca agtagtaac tgct                                              864

<210> SEQ ID NO 30
<211> LENGTH: 864
<212> TYPE: DNA
<213> ORGANISM: rhinovirus

<400> SEQUENCE: 30
aatccagtag aaaattatgt tgaaggtgtg ctgaatgaag tactagtggt acctaatatt       60
agagagagcc atccaagcac ctcaaactct gctccaatcc ttgatgctgc tgaaactggc      120
cacactagta atgtgcaacc tgaagataca gttgaaactc gatatgtgca gacatcacag      180
accagggatg aaatgagtat tgagagcttt cttggaagat ctggttgtat acacacctca      240
acaattactg taagtaaaat gaaaaattat aatgagcaca cttttgacaa atggcaaata      300
accctacagg aaatggccca aattagaagg aaatttgaaa tgtttacata tgtcagattt      360
gactcagaaa tcacattggt accctgtatt gcaggaaaag gagatgacat agggcatatc      420
gtaatgcagt acatgtatgt gccacctgga gctccagttc aacaaaaag ggatgatttt      480 gcatggcaat caggcacaaa tgcatcagtt ttttggcagc atgggcagcc attccctaga      540
atttctttac ctttccttgag cattgcttct gcatactaca tgttttatga tggatatgat      600
ggtgatacac atgattcaca ctatggtact actgtaatta ccacatggg tacactttgt      660 atgaggatag ttcaaaatca gcaagcacat gaggtggaaa ttactactaa tatctatcac      720
aaggccaaac atgttaaagc ttggtgccca agaccacctc gggctgtgcc gtacacacat      780
agtcactcta caaattacaa accacatgag ggtgatgtaa agatttttcat tagacccaga      840 gatgatccaa agtttgtaac tgca                                             864

<210> SEQ ID NO 31
<211> LENGTH: 864
<212> TYPE: DNA
<213> ORGANISM: rhinovirus

<400> SEQUENCE: 31
aatccagtag aaaattatgt tgaaggtgtg ctgaatgaag tactagtggt acctaatatt       60
agagagagcc atccaagcac ctcaaactct gctccaatcc ttgatgctgc tgaaactggc      120
cacactagta atgtgcaacc tgaagataca gttgaaactc gatatgtgca gacatcacag      180
accagggatg aaatgagtat tgagagcttt cttggaagat ctggttgtat acacacctca      240
acaattactg taagtaaaat gaaaaattat aatgagcaca cttttgacaa atggcaaata      300
accctacagg aaatggccca aattagaagg aaatttgaaa tgtttacata tgtcagattt      360
```

-continued

| | |
|---|---|
| gactcagaaa tcacattggt accctgtatt gcaggaaaag gagatgacat agggcatatc | 420 |
| gtaatgcagt acatgtatgt gccacctgga gctccagttc aacaaaaag ggatgatttt | 480 |
| gcatggcaat caggcacaaa tgcatcagtt ttttggcagc atgggcagcc attccctaga | 540 |
| atttctttac ctttcttgag cattgcttct gcatactaca tgttttatga tggatatgat | 600 |
| ggtgatacac atgattcaca ctatggtact actgtaatta accacatggg tacactttgt | 660 |
| atgaggatag ttacaaatca gcaagcacat gaggtggaaa ttactactaa tatctatcac | 720 |
| aaggccaaac atgttaaagc ttggtgccca agaccacctc gggctgtgcc gtacacacat | 780 |
| agtcactcta caaattacaa accacatgag ggtgatgtaa agattttcat tagacccaga | 840 |
| gatgatccaa agtttgtaac tgcg | 864 |

<210> SEQ ID NO 32
<211> LENGTH: 864
<212> TYPE: DNA
<213> ORGANISM: rhinovirus

<400> SEQUENCE: 32

| | |
|---|---|
| aatccagtag aaaattatgt tgaaggtgtg ctgaatgaag tactagtggt acctaatatt | 60 |
| agagagagcc atccaagcac ctcaaactct gctccaatcc ttgatgctgc tgaaactggc | 120 |
| cacactagta atgtgcaacc tgaagataca gttgaaactc gatatgtgca gacatcacag | 180 |
| accagggatg aaatgagtat tgagagcttt cttggaagat ctggttgtat acacacctca | 240 |
| acaattactg taagtaaaat gaaaaattat aatgagcaca cttttgacaa atggcaaata | 300 |
| accctacagg aaatggccca attagaagg aaatttgaaa tgtttacata tgtcagattt | 360 |
| gactcagaaa tcacattggt accctgtatt gcaggaaaag gagatgacat agggcatatc | 420 |
| gtaatgcagt acatgtatgt gccacctgga gctccagttc aacaaaaag ggatgatttt | 480 |
| gcatggcaat caggcacaaa tgcatcagtt ttttggcagc atgggcagcc attccctaga | 540 |
| atttctttac ctttcttgag cattgcttct gcatactaca tgttttatga tggatatgat | 600 |
| ggtgatacac atgattcaca ctatggtact actgtaatta accacatggg tacactttgt | 660 |
| atgaggatag ttacaaatca gcaagcacat gaggtggaaa ttactactaa tatctatcac | 720 |
| aaggccaaac atgttaaagc ttggtgccca agaccacctc gggctgtgcc gtacacacat | 780 |
| agtcactcta caaattacaa accacatgag ggtgatgtaa agattttcat tagacccaga | 840 |
| gatgatccaa agtttgtaac tgct | 864 |

<210> SEQ ID NO 33
<211> LENGTH: 864
<212> TYPE: DNA
<213> ORGANISM: rhinovirus

<400> SEQUENCE: 33

| | |
|---|---|
| aatccagttg aagattatgt tgagggtgtt ttaaatgaag ttttagtagt accaaacatc | 60 |
| aaggaaagcc atccaagcac atcaaatgct gccccaatac tagatgcagc tgaaacaggt | 120 |
| cacactagta agtacaacc agaagataca gttgagactc gttacgtgca acatcacag | 180 |
| actagagatg aaatgagcat agaaagtttt ctaggtaggt caggatgtat ccatatatca | 240 |
| acaattaatg tggatagcac aaaaacatat gatgaatcca atttagaac atggcaaatt | 300 |
| acattgcaag aaatggctca atcagacgc aaatttgaga tgttcacata tgttaggttt | 360 |
| gattctgaaa ttacattagt cccatgcatt gcaggaaagg gtgatgatat aggacatatt | 420 |
| gtgatgcaat acatgtatgt accacctgga gccccaattc cagataatag aacacacttt | 480 |

```
gcttggcaat caggaacaaa tgcatctata ttctggcaac ttggacaacc attcccaaga      540
ttctcgctac cttttctagg catagcttca gcatattaca tgttctatga tggttatgat      600
ggagatactc ctgggtctcg ttatggaacc acagtagtta atcatatggg tacattatgt      660
attaggattg ttacaaatga acagcaccat aatgttgaaa ttactactag agtataccat      720
aaggctaagc atgttaaagc ctggtgtcct agaccactta gagctgtacc atacacaact      780
gtaaactcaa ccaattatat gcctcatact ggtgatctgc aaattttcat taaacctaga      840
acagatccaa aagtagtcaa tgta                                             864

<210> SEQ ID NO 34
<211> LENGTH: 864
<212> TYPE: DNA
<213> ORGANISM: rhinovirus

<400> SEQUENCE: 34
aatccagttg aagattatgt tgagggtgtt ttaaatgaag ttttagtagt accaaacatc       60
aaggaaagcc atccaagcac atcaaatgct gccccaatac tagatgcagc tgaaacaggt      120
cacactagta aagtacaacc agaagataca gttgagactc gttacgtgca acatcacag       180 actagagatg aaatgagcat agaaagtttt ctaggtaggt caggatgtat ccatatatca      240
acaattaatg tggatagcac aaaaacatat gatgaatcca aatttagaac atggcaaatt      300
acattgcaag aaatggctca atcagacgc aaatttgaga tgttcacata tgttaggttt       360
gattctgaaa ttacattagt cccatgcatt gcaggaaagg gtgatgatat aggacatatt      420
gtgatgcaat acatgtatgt accacctgga gccccaattc cagataatag aacacacttt      480
gcttggcaat caggaacaaa tgcatctata ttctggcaac ttggacaacc attcccaaga      540
ttctcgctac cttttctagg catagcttca gcatattaca tgttctatga tggttatgat      600
ggagatactc ctgggtctcg ttatggaacc acagtagtta atcatatggg tacattatgt      660
attaggattg ttacaaatga acagcaccat aatgttgaaa ttactactag agtataccat      720
aaggctaagc atgttaaagc ctggtgtcct agaccactta gagctgtacc atacacaact      780
gtaaactcaa ccaattatat gcctcatact ggtgatctgc aaattttcat taaacctaga      840
acagatccaa aagtagtcaa tgtg                                             864

<210> SEQ ID NO 35
<211> LENGTH: 864
<212> TYPE: DNA
<213> ORGANISM: rhinovirus

<400> SEQUENCE: 35
aatccagttg aagattatgt tgagggtgtt ttaaatgaag ttttagtagt accaaacatc       60
aaggaaagcc atccaagcac atcaaatgct gccccaatac tagatgcagc tgaaacaggt      120
cacactagta aagtacaacc agaagataca gttgagactc gttacgtgca acatcacag       180 actagagatg aaatgagcat agaaagtttt ctaggtaggt caggatgtat ccatatatca      240
acaattaatg tggatagcac aaaaacatat gatgaatcca aatttagaac atggcaaatt      300
acattgcaag aaatggctca atcagacgc aaatttgaga tgttcacata tgttaggttt       360
gattctgaaa ttacattagt cccatgcatt gcaggaaagg gtgatgatat aggacatatt      420
gtgatgcaat acatgtatgt accacctgga gccccaattc cagataatag aacacacttt      480
gcttggcaat caggaacaaa tgcatctata ttctggcaac ttggacaacc attcccaaga      540
```

| | |
|---|---|
| ttctcgctac cttttctagg catagcttca gcatattaca tgttctatga tggttatgat | 600 |
| ggagatactc ctgggtctcg ttatggaacc acagtagtta atcatatggg tacattatgt | 660 |
| attaggattg ttacaaatga acagcaccat aatgttgaaa ttactactag agtataccat | 720 |
| aaggctaagc atgttaaagc ctggtgtcct agaccactta gagctgtacc atacacaact | 780 |
| gtaaactcaa ccaattatat gcctcatact ggtgatctgc aaattttcat taaacctaga | 840 |
| acagatccaa aagtagtcaa tgtc | 864 |

```
<210> SEQ ID NO 36
<211> LENGTH: 864
<212> TYPE: DNA
<213> ORGANISM: rhinovirus

<400> SEQUENCE: 36
```

| | |
|---|---|
| aatccagttg aggactatat cgataatgta cttaatgaag tcttagtagt accaaatacc | 60 |
| aaggagagtc atccaagcac ttctaactct gctcctatac tagatgcagc tgaaacaggc | 120 |
| catactagta gtgtgcaacc agaagataca gttgagaccc gctatgtaca aacttcccag | 180 |
| acaagggatg agatgagtat tgagagcttt ctgggtaggt ctggttgtat tcacatttca | 240 |
| acaataaatg tagaagatgg taaaacttat gatgaatcta aatttagaaa atggcaaatt | 300 |
| acactacaag aaatggctca aattaggcgc aaatttgaaa tgtttacata tgtaagattt | 360 |
| gattcagaaa ttacattggt cccatgtatt gctggaaaag gtgatgacat aggacatgtt | 420 |
| gtcatgcaat acatgtatgt accaccaggg gcacccatac cagatagcag gactcatttt | 480 |
| gcatggcagt cagggactaa tgcatcaata ttctggcaac atggacaacc attcccaaga | 540 |
| ttttcactac cttttctgag tattgcttca gcttactaca tgttttatga tggctatgat | 600 |
| ggggatacct atgaatcacg ttatggtact acagtggtta atcacatggg cacactgtgc | 660 |
| attagaatag tcactaatca gcaaaatcat gaggttgaaa tcaccactag agtataccac | 720 |
| aaggctaaac atattaaagc ttggtgtccc agaccaccta gagctgtacc atacacagca | 780 |
| gtagattcaa caaattacaa acctatgaga ggggatgtac aaatctttat taaagagaga | 840 |
| gcaagcccaa aagtagttac tttg | 864 |

```
<210> SEQ ID NO 37
<211> LENGTH: 864
<212> TYPE: DNA
<213> ORGANISM: rhinovirus

<400> SEQUENCE: 37
```

| | |
|---|---|
| aatccagttg aggactatat cgataatgta cttaatgaag tcttagtagt accaaatacc | 60 |
| aaggagagtc atccaagcac ttctaactct gctcctatac tagatgcagc tgaaacaggc | 120 |
| catactagta gtgtgcaacc agaagataca gttgagaccc gctatgtaca aacttcccag | 180 |
| acaagggatg agatgagtat tgagagcttt ctgggtaggt ctggttgtat tcacatttca | 240 |
| acaataaatg tagaagatgg taaaacttat gatgaatcta aatttagaaa atggcaaatt | 300 |
| acactacaag aaatggctca aattaggcgc aaatttgaaa tgtttacata tgtaagattt | 360 |
| gattcagaaa ttacattggt cccatgtatt gctggaaaag gtgatgacat aggacatgtt | 420 |
| gtcatgcaat acatgtatgt accaccaggg gcacccatac cagatagcag gactcatttt | 480 |
| gcatggcagt cagggactaa tgcatcaata ttctggcaac atggacaacc attcccaaga | 540 |
| ttttcactac cttttctgag tattgcttca gcttactaca tgttttatga tggctatgat | 600 |
| ggggatacct atgaatcacg ttatggtact acagtggtta atcacatggg cacactgtgc | 660 |

```
attagaatag tcactaatca gcaaaatcat gaggttgaaa tcaccactag agtataccac    720
aaggctaaac atattaaagc ttggtgtccc agaccaccta gagctgtacc atacacagca    780
gtagattcaa caaattacaa acctatgaga ggggatgtac aaatctttat taaagagaga    840
gcaagcccaa aagtagttac ttta                                           864
```

<210> SEQ ID NO 38
<211> LENGTH: 864
<212> TYPE: DNA
<213> ORGANISM: rhinovirus

<400> SEQUENCE: 38

```
aatccagttg aggactatat cgataatgta cttaatgaag tcttagtagt accaaatacc     60
aaggagagtc atccaagcac ttctaactct gctcctatac tagatgcagc tgaaacaggc    120
catactagta gtgtgcaacc agaagataca gttgagaccc gctatgtaca aacttcccag    180
acaagggatg agatgagtat tgagagcttt ctgggtaggt ctggttgtat tcacatttca    240
acaataaatg tagaagatgg taaaacttat gatgaatcta aatttagaaa atggcaaatt    300
acactacaag aaatggctca aattaggcgc aaatttgaaa tgtttacata tgtaagattt    360
gattcagaaa ttacattggt cccatgtatt gctggaaaag gtgatgacat aggacatgtt    420
gtcatgcaat acatgtatgt accaccaggg gcacccatac cagatagcag gactcatttt    480
gcatggcagt cagggactaa tgcatcaata ttctggcaac atggacaacc attcccaaga    540
ttttcactac cttttctgag tattgcttca gcttactaca tgttttatga tggctatgat    600
ggggatacct atgaatcacg ttatggtact acagtggtta atcacatggg cacactgtgc    660
attagaatag tcactaatca gcaaaatcat gaggttgaaa tcaccactag agtataccac    720
aaggctaaac atattaaagc ttggtgtccc agaccaccta gagctgtacc atacacagca    780
gtagattcaa caaattacaa acctatgaga ggggatgtac aaatctttat taaagagaga    840
gcaagcccaa aagtagttac tttt                                           864
```

<210> SEQ ID NO 39
<211> LENGTH: 846
<212> TYPE: DNA
<213> ORGANISM: rhinovirus

<400> SEQUENCE: 39

```
aatccaattg aaaattatgt agatcaagta cttaatgaag ttttagttgt accaaatatt     60
aaagaaagtc accctagtac gtcaaactct gccccaattc tagatgctgc tgaaaccgga    120
cacactagta atgtacaacc agaagacact attgaaaccc gtcatgttca aaccacacaa    180
actagagatg aaatgagcat tgagagcttt cttggtaggt cagggtgcgt acacacttca    240
acaattgaaa caacgcttag tcataaagat agattcaaaa catggaatat taacttacaa    300
gagatggctc aaatcaggag aaagtttgaa atgtttacat atgtaagatt tgattcagaa    360
ataaccctgg ttccatctat tgcaggacgt ggtgcagata taggtcacat agttatgcaa    420
tatatgtatg taccacctgg ggctccacta ccaacagaca gaaagcattt tgcctggcaa    480
tcaagtacta atgcatcaat attttggcaa catgggcaac cctttcctag attttcatta    540 cctttttga gtgttgcatc tgcttattac atgttttatg atggctataa tggtgatgac    600
tatacagcaa aatacggtac caccgtggtt aatcgtatgg gggcactgtg tatgaggatt    660
gtcacaaaca aacaagttca tgatgttgag gtcacaacta atatttacca caaggctaag    720
```

-continued

```
catgtaaaag cgtggtgccc gcggccgccc agagctgttc catataaata tgttgatttc    780
aataattatg cagccagtga tagtgttgac attttttataa aatcaaggca aaacttgcaa    840
acagct                                                                846
```

<210> SEQ ID NO 40
<211> LENGTH: 845
<212> TYPE: DNA
<213> ORGANISM: rhinovirus

<400> SEQUENCE: 40

```
aatccaattg aaaattatgt agatcaagta cttaatgaag ttttagttgt accaaatatt     60
aaagaaagtc accctagtac gtcaaactct gccccaattc tagatgctgc tgaaaccgga    120
cacactagta atgtacaacc agaagacact attgaaaccc gttatgttca aaccacacaa    180
actagagatg aaatgagcat tgagagcttt cttggtaggt cagggtgcgt acacacttca    240
acaattgaaa caacgcttag tcataaagat agattcaaaa catggaatat taacttacaa    300
gagatggctc aaatcaggag aaagtttgaa atgtttacat atgtaagatt tgattcagaa    360
ataaccctgg ttccatctat tgcaggacgt ggtgcagata taggtcacat agttatgcaa    420
tatatgtatg taccacctgg ggctccacta ccaacagaca gaaagcattt tgcctggcaa    480
tcaagtacta atgcatcaat attttggcaa catgggcaac cctttcctag attttcatta    540
ccttttttga gtgttgcatc tgcttattac atgttttatg atggctataa tggtgatgac    600
tatacagcaa aatacggtac caccgtggtt aatcgtatgg gggcactgtg tatgaggatt    660
gtcacaaaca aacaagttca tgatgttgag gtcacaacta atatttacca caaggctaag    720
catgtaaaag cgtggtgccc tagaccacct agagctgttc catataaata tgttgatttc    780
aataattatg cagccagtga tagtgttgac attttttataa aatcaaggca aaacttgcaa    840
acagc                                                                 845
```

<210> SEQ ID NO 41
<211> LENGTH: 846
<212> TYPE: DNA
<213> ORGANISM: rhinovirus

<400> SEQUENCE: 41

```
aatccaattg aaaattatgt agatcaagta cttaatgagg ttctagtcgt accaaatatt     60
aaagaaagtc acccaagcac atcaaattct gccccaattc tagatgctgc tgaaactgga    120
cacactagca atgtgcaacc agaggatacc attgaaactc gttatgttca aaccacacaa    180
actagagatg aaatgagtat tgaaagttttt cttggtaggt cagggtgtgt acatacttca    240
acaattgaaa caaacttaa acatgatgaa agatttaaaa tatggaatat caatttacaa    300
gaaatggctc aaattaggag aaagtttgag atgtttacat atgtgagatt tgattcagag    360
ataaccctag ttccatctat tgcaggacgt ggtgcagata taggtcacat agttatgcaa    420
tatatgtatg tgccacctgg agccccatta ccaacagaca gaaaacactt tgcatggcaa    480
tcaagtacta atgcatcaat attttggcaa catggacaac ccttccctag attttcattg    540
ccatttctga gtgttgcatc tgcttattac atgttttatg atggctataa tggtgatgat    600
cacacagcga gatatggtac cactgtggtt aaccgtatgg gagcactgtg catgagaatt    660
gtcacaaata aacaagtcca tgatgttgag gttacaacta acatttacca taaagctaag    720
catgtaaaag catggtgccc tagaccacct agagctgtcc catataaata tgttgacttc    780
aataattatg cagccagtga taatgttgac atctttatac aaccaagaaa cagtttaaaa    840
``` acagct 846

<210> SEQ ID NO 42
<211> LENGTH: 843
<212> TYPE: DNA
<213> ORGANISM: rhinovirus

<400> SEQUENCE: 42

```
aacccagttg aaaactatgt ggatgaggtg cttaatgaag ttttagttgt gcctaacatc    60
agggagagcc acccaagcac gtccaactct gcaccaatct tggatgctgc tgagactgga   120
catactagta atgtacaacc agaagatacc attgagactc gttatgtaca aacctcacat   180
actagagatg aaatgagcat tgaaagtttt cttgggtaga tcaggatgtat acatgtttca   240
acaataaaag caaatcaggc acatgacgcc aagttcgata aatggaatgt taacttacaa   300
gaaatggctc aaattaggcg caaatttgaa atgttcacat atgtgagatt tgactcagaa   360
ataactctgg ttcttttgcat tgcaggacgt ggtaatgata taggtcacat agttatgcag   420
tacatgtatg taccacctgg agctccagta ccaaatgaca gaaatcattt tgcatggcaa   480
tcagggacta atgcatcaat attctggcaa catggtcagc ctttcccaag attttcatta   540
ccattcctaa gtgttgcatc tgcttattac atgttttatg atggttacaa tggaggtgat   600
catacagcaa cttatggcac cacagtggtt aaccggatgg ggacgctttg tgtcagaatt   660
gttacaggca acaagctca tgatgttcaa gttacaacaa gtatctatca taaagctaaa   720
catgtaaagg cgtggtgtcc tagaccacca agagttgtcc catacaagta tgttggccta   780
actaattaca cacttaaaga agaagatcca gttgtggaat ccagaccaag cttaatgaca   840
gct                                                                 843
```

<210> SEQ ID NO 43
<211> LENGTH: 843
<212> TYPE: DNA
<213> ORGANISM: rhinovirus

<400> SEQUENCE: 43

```
aacccagttg aaaactatgt ggatgaggtg cttaatgaag ttttagttgt gcctaacatc    60
agggagagcc acccaagcac gtccaactct gcaccaatct tggatgctgc tgagactgga   120
catactagta atgtacaacc agaagatacc attgagactc gttatgtaca aacctcacat   180
actagagatg aaatgagcat tgaaagtttt cttgggtaga tcaggatgtat acatgtttca   240
acaataaaag caaatcaggc acatgacgcc aagttcgata aatggaatgt taacttacaa   300
gaaatggctc aaattaggcg caaatttgaa atgttcacat atgtgagatt tgactcagaa   360
ataactctgg ttccatgcat tgcaggacgt ggtaatgata taggtcacat agttatgcag   420
tacatgtatg taccacctgg agctccagta ccaaatgaca gaaatcattt tgcatggcaa   480
tcagggacta atgcatcaat attctggcaa catggtcagc ctttcccaag attttcatta   540
ccattcctaa gtgttgcatc tgcttattac atgttttatg atggttacaa tggaggtgat   600
catacagcaa cttatggcac cacagtggtt aaccggatgg ggacgctttg tgtcagaatt   660
gttacaggca acaagctca tgatgttcaa gttacaacaa gtatctatca taaagctaaa   720
catgtaaagg cgtggtgtcc tagaccacca agagttgtcc catacaagta tgttggccta   780
actaattaca cacttaaaga agaagataca gttgtggaat ccagaccaag cttaatgaca   840
gct                                                                 843
```

<210> SEQ ID NO 44
<211> LENGTH: 843
<212> TYPE: DNA
<213> ORGANISM: rhinovirus

<400> SEQUENCE: 44

```
aacccagttg aaaattatgt ggatgaagta cttaatgaag tcttagttgt gcctaatatc    60
agagagagcc acccaagcac atctaactct gctccaattt tggatgctgc tgaaactgga   120
catactagta atgtacaacc agaagatacc attgagactc gatatgtaca aacctcacaa   180
actagagatg aaatgagcat tgaaagtttt cttggcagat cagggtgtat acatgtttca   240
acaataaaga caaatcaggc acacaatacc aagtttgata atggaatat caacttacaa    300
gaaatggctc aaattagacg caaatttgaa atgttcacat atgtgagatt tgattcggaa   360
ataactctag ttccatgcat tgcaggacat ggtgatgata taggccacat agttatgcag   420
tacatgtatg taccacctgg agctccagta ccagatgaca gaaaccactt tgcatggcaa   480
tcggggacta atgcatcaat attctggcaa catggtcaac ctttcccaag attttcattg   540
ccatttctaa gtgttgcatc tgcctattac atgttttatg acggttataa tggaggtgat   600
catacagcaa cttatggcac cacagtggtt aaccggatgg ggacgctttg cgtcaggatc   660
gttacgggca acaggctca tgatgtccaa gttacaacaa gcatttatca caaagctaaa    720
catgtaaaag catggtgccc tagaccacca agggttgtcc catacaagta tgttggccta   780
actaattaca cacttaaaga aacagataca gttgtggaac ctagacacag cataatgaca   840
gct                                                                 843
```

<210> SEQ ID NO 45
<211> LENGTH: 843
<212> TYPE: DNA
<213> ORGANISM: rhinovirus

<400> SEQUENCE: 45

```
aacccagttg aaaattatgt ggatgaagta cttaatgaag tcttagttgt gcctaatatc    60
agagagagcc acccaagcat atctaactct gctccaattt tggatgctgc tgaaactgga   120
catactagta atgtacaacc agaagatacc attgagactc gatatgtaca aacctcacaa   180
actagagatg aaatgagcat tgaaagtttt cttggcagat cagggtgtat acatgtttca   240
acaataaaga caaatcaggc acacaatacc aagtttgata atggaatat caacttacaa    300
gaaatggctc aaattagacg caaatttgaa atgttcacat atgtgagatt tgattcagaa   360
ataactctag ttccatgcat tgcaggacgt ggtgatgata taggccacat agttatgcag   420
tacatgtatg taccacctgg agctccagta ccagatgaca gaatccactt tgcatggcaa   480
tcggggaata atgcatcaat attctggcaa catggtcaac ctttcccaag attttcattg   540
ccatttctaa gtgttgcatc tgcctattac atgttttatg acggttataa tggaggtgat   600
catacagcaa cttatggcac cacagtggtt aaccggatgg ggacgctttg cgtcaggatc   660
gttacgggca acaggctca tgatgtccaa gttacaacaa gcatttatca caaagctaaa    720
catgtaaaag catggtgccc tagaccacca agggttgtcc catacaagta tgttggccta   780
actaattaca cacttaaaga aacagataca gttgtggaac ctagacacag cataatgaca   840
gct                                                                 843
```

<210> SEQ ID NO 46
<211> LENGTH: 855

```
<212> TYPE: DNA
<213> ORGANISM: rhinovirus

<400> SEQUENCE: 46
aatccagttg aaaactatgt ggaagaggtt cttaatgaag tcttagtagt acctaatatc      60
aaagaaagcc atccaagcac atctaattct gccccaatcc tggacgctgc tgaaactgga     120
cacactagta atgtacaacc agaagataca attgaaactc gctacgtgca acatcacaa     180
acaagagatg aaatgagcat tgaaagtttc cttggtaggt caggatgtgt acatacttca     240
ataatagaac cagatggact ccatgatagc aaatataaag tatggcacat taatttacaa     300
gagatggccc agattaggcg aaaatttgaa atgttcacat atgtaagatt tgattcagaa     360
gtgaccatag ttccatgcat tgcaggacat ggtagtgaca taggccatat agtcatgcaa     420
tacatgtatg taccacctgg ggccccagta ccaacaaata gaaaacattt tgcatggcaa     480
tcaggtacta atgcatcgat tttctggcaa catggacaac cctttccaag atttacatta     540
cccttttga gtgtcgcatc cgcttattac atgttttatg atggttatga tggagacaaa     600
agtggagcca gtatggtac tacagtagtt aatcgcatgg gtgcactatg catgagagtt     660
gtcactaaca aacaagctca taagttgaa atcacaacca atatttacca taaggccaaa     720
catgttaagg catggtgtcc taggcccct agagcagttc catacagggt atgtggatca     780
acaaactaca aacctgatga aatgaagtt acaatctttg ttaaacacag ggataatcca     840
aagattatca cagca                                                     855

<210> SEQ ID NO 47
<211> LENGTH: 855
<212> TYPE: DNA
<213> ORGANISM: rhinovirus

<400> SEQUENCE: 47
aatccagttg aaaactatgt ggaagaggtt cttaatgaag tcttagtagt acctaatatc      60
aaagaaagcc atccaagcac atctaattct gccccaatcc tggacgctgc tgaaactgga     120
cacactagta atgtacaacc agaagataca attgaaactc gctacgtgca acatcacaa     180
acaagagatg aaatgagcat tgaaagtttc cttggtaggt caggatgtgt acatacttca     240
ataatagaac cagatggact ccatgatagc aaatataaag tatggcacat taatttacaa     300
gagatggccc agattaggcg aaaatttgaa atgttcacat atgtaagatt tgattcagaa     360
gtgaccatag ttccatgcat tgcaggacat ggtagtgaca taggccatat agtcatgcaa     420
tacatgtatg taccacctgg ggccccagta ccaacaaata gaaaacattt tgcatggcaa     480
tcaggtacta atgcatcgat tttctggcaa catggacaac cctttccaag atttacatta     540
cccttttga gtgtcgcatc cgcttattac atgttttatg atggttatga tggagacaaa     600
agtggagcca gtatggtac tacagtagtt aatcgcatgg gtgcactatg catgagagtt     660
gtcactaaca aacaagctca taagttgaa atcacaacca atatttacca taaggccaaa     720
catgttaagg catggtgtcc taggcccct agagcagttc catacagggt atgtggatca     780
acaaactaca aacctgatga aatgaagtt acaatctttg ttaaacacag ggataatcca     840
aagattatca cagct                                                     855

<210> SEQ ID NO 48
<211> LENGTH: 855
<212> TYPE: DNA
<213> ORGANISM: rhinovirus
```

<400> SEQUENCE: 48

```
aatccagttg aaaactatgt ggaagaggtt cttaatgaag tcttagtagt acctaatatc        60
aaagaaagcc atccaagcac atctaattct gccccaatcc tggacgctgc tgaaactgga       120
cacactagta atgtacaacc agaagataca attgaaactc gctacgtgca acatcacaa        180
acaagagatg aaatgagcat tgaaagtttc cttggtaggt caggatgtgt acatacttca       240
ataatagaac cagatggact ccatgatagc aaatataaag tatggcacat taatttacaa       300
gagatggccc agattaggcg aaaatttgaa atgttcacat atgtaagatt tgattcagaa       360
gtgaccatag ttccatgcat tgcaggacat ggtagtgaca taggccatat agtcatgcaa       420
tacatgtatg taccacctgg ggccccagta ccaacaaata gaaaacattt tgcatggcaa       480
tcaggtacta atgcatcgat tttctggcaa catggacaac cctttccaag atttacatta       540
ccctttttga gtgtcgcatc cgcttattac atgttttatg atggttatga tggagacaaa       600
agtggagcca gtatggtac tacagtagtt aatcgcatgg gtgcactatg catgagagtt        660
gtcactaaca acaagctca taaagttgaa atcacaacca atatttacca taaggccaaa        720
catgtaaagg catggtgtcc taggccacct agagcagttc catacaggta tgttggatca       780
acaaactaca aacctgatga aaatgaagtt acaatctttg ttaaacacag ggataatcca       840
aagattatca cagca                                                        855
```

<210> SEQ ID NO 49
<211> LENGTH: 855
<212> TYPE: DNA
<213> ORGANISM: rhinovirus

<400> SEQUENCE: 49

```
aacccagtcg aaaattatgt ggaagaggta cttaatgagg tcttagttgt accaaatatc        60
aaagaaagtc atccaagtac atccaactct gccccgattt tagatgctgc tgaaactgga       120
cacactagca atgtacagcc agaagataca attgaaactc gatatgtaca aacagcacaa       180
acaagagatg aaatgagcat tgagagcttc cttggcaggt caggatgtgt gcattcctca       240
acaataaaat cagatgagca acacattaat aaatttaaag tatggcacat taatttacaa       300
gaaatggccc agatcaggcg taaatatgaa atgtttacat atgtaagatt tgattcagaa       360
gtaaccatgg ttccatgtat tgcagggtat ggtgatgaca taggtcacat agttatgcaa       420
tacatgtatg tgccgcctgg ggctccagtg ccaacaagta gagagcactt tgcatggcag       480
tcaggtacca atgcatcaac tttctggcaa caagggcaac cctttccaag atttttcatta      540
ccatttttga gtgttgcatc tgcttattac atgttttatg atggctataa tggtgacaga       600
agtggagcca gtatggcac cacagtgtc aatcgcatgg gtgcattgtg tatgagagtt         660
gtaacaaaca agcaactcca taaagttgaa atcacaacta acatctacca taaagccaag       720
catgtgaaag catggtgtcc tagaccacct agagctgttc catatagata tgttggatca       780
acaaattaca aacctgatca aggagaagtt gcaattttca ttgagcatag agaaaatcca       840
aaattcatta cagca                                                        855
```

<210> SEQ ID NO 50
<211> LENGTH: 855
<212> TYPE: DNA
<213> ORGANISM: rhinovirus

<400> SEQUENCE: 50

```
aacccagtcg aaaattatgt ggaagaggta cttaatgagg tcttagttgt accaaatatc        60
```

```
aaagaaagtc atccaagtac atccaactct gccccgattt tagatgctgc tgaaactgga      120
cacactagca atgtacagcc agaagataca attgaaactc gatatgtaca acagcacaa       180 acaagagatg aaatgagcat tgagagcttc cttggcaggt caggatgtgt gcattcctca      240
acaataaaat cagatgagca acacattaat aaatttaaag tatggcacat taatttacaa      300
gaaatggccc agatcaggcg taaatatgaa atgtttacat atgtaagatt tgattcagaa      360
gtaaccatgg ttccatgtat tgcagggtat ggtgatgaca taggtcacat agttatgcaa      420
tacatgtatg tgccgcctgg ggctccagtg ccaacaagta gagagcactt tgcatggcag      480
tcaggtacca atgcatcaac tttctggcaa caagggcaac cctttccaag attttcatta      540 ccattttga gtgttgcatc tgcttattac atgttttatg atggctataa tggtgacaga       600
agtggagcca gtatggcac cacagtggtc aatcgcatgg gtgcattgtg tatgagagtt       660
gtaacaaaca agcaactcca taaagttgaa atcacaacta acatctacca taaagccaag      720
catgtgaaag catggtgtcc tagaccacct agagctgttc catatagata tgttggatca      780
acaaattaca aacctgatca aggagaagtt gcaattttca ttgagcatag agaaaatcca      840
aaattcatta cagct                                                      855

<210> SEQ ID NO 51
<211> LENGTH: 855
<212> TYPE: DNA
<213> ORGANISM: rhinovirus

<400> SEQUENCE: 51
aacccagtcg aaaattatgt ggaagaggta cttaatgagg tcttagttgt accaaatatc       60
aaagaaagtc atccaagtac atccaactct gccccgattt tagatgctgc tgaaactgga      120
cacactagca atgtacagcc agaagataca attgaaactc gatatgtaca acagcacaa       180 acaagagatg aaatgagcat tgagagcttc cttggcaggt caggatgtgt gcattcctca      240
acaatacaat caaatgagca acacattaat aaatttaaag tatggcacat taatttacaa      300
gaaatggccc agatcaggcg taaatatgaa atgtttacat atgtaagatt tgattcagaa      360
gtaaccatgg ttccatgtat tgcagggtat ggtgatgaca taggtcacat agttatgcaa      420
tacatgtatg tgccgcctgg ggctccagtg ccaacaagta gagagcactt tgcatggcag      480
tcaggtacca atgcatcaat tttctggcaa caagggcaac cctttccaag attttcatta      540 ccattttga gtgttgcatc tgcttattac atgttttatg atggctataa tggtgacaga       600
agtggagcca gtatggcac cacagtggtc aatcgcatgg gtgcattgtg tatgagagtt       660
gtaacaaaca agcaactcca taaagttgaa atcacaacta acatctacca taaagccaag      720
catgtgaaag catggtgtcc tagaccacct agagctgttc catatagata tgttggatca      780
acaaattaca aacctgatca aggagaagtt gcaattttca ttgagcatag agaaaatcca      840
aaattcatta cagca                                                      855

<210> SEQ ID NO 52
<211> LENGTH: 858
<212> TYPE: DNA
<213> ORGANISM: rhinovirus

<400> SEQUENCE: 52
aacccagtgg aggattatgt tgatggaatt ctaaatgagg ttttagttgt acctaatata       60
aaggagagcc aagctaccac atcaaactca gcacctgctc tagatgcagc tgaaaccgga      120
```

```
catactagca aagtgcagcc agaggatatg attgagacta gatatgtgca gacttcacag    180
actcttgatg aaatgagcat tgagagcttc ctaggtagat ctggttgtat tcacatgtcc    240
aagttaattg tgcagtatga agactataat ggaagaaaaa actttaacac atggaaaata    300
aacttgcaag agatggcaca aattagaagg aaatttgaaa tgttcacata cactagattt    360
gattcagaga tcacattggt gccttgtata gctgcaaaag gaaatgatat tggtcatgtt    420
gtaatgcaat atatgtatgt cccaccaggt gctccagttc agagaaaag agatgattat     480 acatggcaat caggaacaaa tgcatctatt ttctggcaat atggtcaaac atacccaaga    540
ttttctctac ctttcatgag tatagcctca gcatattaca tgtttttatga tggatatgat   600 ggagatcaac caaactccag atatggtaat atagttacca atgatatggg cactctgtgt    660
tatagaatag taactgatga ccatagacac aaaattgaag tcacaactag ggtgtatcat    720
aaagcaaagc atgtgaaggt gtggtgtcca agaccaccta gagctgtaga atatactcac    780
actcatgtaa ccaattacaa accacaggaa ggacaggtga aaacagctgt caaggctagg    840
aaaacaatta aaacagca                                                  858

<210> SEQ ID NO 53
<211> LENGTH: 858
<212> TYPE: DNA
<213> ORGANISM: rhinovirus

<400> SEQUENCE: 53
aacccagtgg aggattatgt tgatggaatt ctaaatgagg ttttagttgt acctaatata     60
aaggagagcc aagctaccac atcaaactca gcacctgctc tagatgcagc tgaaaccgga   120
catactagca aagtgcagcc agaggatatg attgagacta gatatgtgca gacttcacag    180
actcttgatg aaatgagcat tgagagcttc ctaggtagat ctggttgtat tcacatgtcc    240
aagttaattg tgcagtatga agactataat ggaagaaaaa actttaacac atggaaaata    300
aacttgcaag agatggcaca aattagaagg aaatttgaaa tgttcacata cactagattt    360
gattcagaga tcacattggt gccttgtata gctgcaaaag gaaatgatat tggtcatgtt    420
gtaatgcaat atatgtatgt cccaccaggt gctccagttc agagaaaag agatgattat     480 acatggcaat caggaacaaa tgcatctatt ttctggcaat atggtcaaac atacccaaga    540
ttttctctac ctttcatgag tatagcctca gcatattaca tgtttttatga tggatatgat   600 ggagatcaac caaactccag atatggtaat atagttacca atgatatggg cactctgtgt    660
tatagaatag taactgatga ccatagacac aaaattgaag tcacaactag ggtgtatcat    720
aaagcaaagc atgtgaaggt gtggtgtcca agaccaccta gagctgtaga atatactcac    780
actcatgtaa ccaattacaa accacaggaa ggacaggtga aaacagctgt caaggctagg    840
aaaacaatta aaacagcg                                                  858

<210> SEQ ID NO 54
<211> LENGTH: 858
<212> TYPE: DNA
<213> ORGANISM: rhinovirus

<400> SEQUENCE: 54
aacccagtgg aggattatgt tgatggaatt ctaaatgagg ttttagttgt acctaatata     60
aaggagagcc aagctaccac atcaaactca gcacctgctc tagatgcagc tgaaaccgga   120
catactagca aagtgcagcc agaggatatg attgagacta gatatgtgca gacttcacag    180
actcttgatg aaatgagcat tgagagcttc ctaggtagat ctggttgtat tcacatgtcc    240
```

-continued

```
aagttaattg tgcagtatga agactataat ggaaagaaaa actttaacac atggaaaata      300
aacttgcaag agatggcaca aattagaagg aaatttgaaa tgttcacata cactagattt      360
gattcagaga tcacattggt gccttgtata gctgcaaaag gaaatgatat tggtcatgtt      420
gtaatgcaat atatgtatgt cccaccaggt gctccagttc agagaaaag agatgattat       480 acatggcaat caggaacaaa tgcatctatt ttctggcaat atggtcaaac atacccaaga      540
ttttctctac ctttcatgag tatagcctca gcatattaca tgttttatga tggatatgat      600
ggagatcaac caaactccag atatggtaat atagttacca atgatatggg cactctgtgt      660
tatagaatag taactgatga ccatagacac aaaattgaag tcacaactag ggtgtatcat      720
aaagcaaagc atgtgaaggt gtggtgtcca agaccaccta gagctgtaga atatactcac      780
actcatgtaa ccaattacaa accacaggaa ggacaggtga aaacagctgt caaggctagg      840
aaaacaatta aaacagct                                                    858
```

<210> SEQ ID NO 55
<211> LENGTH: 858
<212> TYPE: DNA
<213> ORGANISM: rhinovirus

<400> SEQUENCE: 55

```
aacccagttg aaaattacgt ggatgagata ttaaatgagg ttcttgtagt accaaacatc       60
aaagagagtc aggctaccac atcaaatgca gcacctgctt tggatgcagc tgagactggg      120
cacacaagca gcgttcaacc agaggacatg gttgagacta ggtatgtgca acatcacaa       180 actcttgatg agatgtgtat ggagagtttc ttagggagat ctggttgtat tcatatttca      240
aagctagttt agaatatga gggatatgat gatacaaaaa actttaagac atggaaaata      300
aacctacaag aaatggcaca agttagaaga aaatttgaga tgtttacata tactagattt      360
gattcagaag ttactctagt tccttctata gctgccaaag gggatgacat tggtcatgta      420
gtgatgcaat acatgtatgt cccaccaggc gctccagttc caaagaagag agatgactac      480
acatggcagt caggaaccaa tgcatctatt ttctggcaat atggacaaac atacccctagg     540 ttttcattac cctttctaag tatagcttca gcttattaca tgttttatga tggatatgat      600
ggagaccaac ctagttctag gtatggtaat atagttacca atgacatggg cacctatgt      660 tccaggatag taactgatga tcataagcac aagattgaag ttacaacaag aatatatcac      720
aaagcaaagc atgttaaggt atggtgcccg agaccaccta gagctgtaga gtatacatac      780
acccatgtaa caaactacaa accacattct ggtgatgtgc aaacagctat tagaccaaga      840
gcaacaatta agactgca                                                    858
```

<210> SEQ ID NO 56
<211> LENGTH: 858
<212> TYPE: DNA
<213> ORGANISM: rhinovirus

<400> SEQUENCE: 56

```
aacccagttg aaaattacgt ggatgagata ttaaatgagg ttcttgtagt accaaacatc       60
aaagagagtc aggctaccac atcaaatgca gcacctgctt tggatgcagc tgagactggg      120
cacacaagca gcgttcaacc agaggacatg gttgagacta ggtatgtgca acatcacaa       180 actcttgatg agatgtgtat ggagagtttc ttagggagat ctggttgtat tcatatttca      240
aagctagttt agaatatga gggatatgat gatacaaaaa actttaagac atggaaaata      300
```

```
aacctacaag aaatggcaca agttagaaga aaatttgaga tgtttacata tactagattt    360
gattcagaag ttactctagt tccttctata gctgccaaag gggatgacat tggtcatgta    420
gtgatgcaat acatgtatgt cccaccaggc gctccagttc aaagaagag agatgactac     480 acatggcagt caggaaccaa tgcatctatt ttctggcaat atggacaaac atacccagg     540 tttcattac cctttctaag tatagcttca gcttattaca tgtttatga tggatatgat      600 ggagaccaac ctagttctag gtatggtaat atagttacca atgacatggg caccctatgt    660
tccaggatag taactgatga tcataagcac aagattgaag ttacaacaag aatatatcac    720
aaagcaaagc atgttaaggt atggtgcccg agaccaccta gagctgtaga gtatacatac    780
acccatgtaa caaactacaa accacattct ggtgatgtgc aaacagctat tagaccaaga    840
gcaacaatta agactgcg                                                  858

<210> SEQ ID NO 57
<211> LENGTH: 858
<212> TYPE: DNA
<213> ORGANISM: rhinovirus

<400> SEQUENCE: 57
aacccagttg aaaattacgt ggatgagata ttaaatgagg ttcttgtagt accaaacatc     60
aaagagagtc aggctaccac atcaaatgca gcacctgctt tggatgcagc tgagactggg    120
cacacaagca gcgttcaacc agaggacatg gttgagacta ggtatgtgca acatcacaa    180 actcttgatg agatgtgtat ggagagtttc ttagggagag ctggttgtat tcatatttca    240
aagctagttg tagaatatga gggatatgat gatacaaaaa actttaagac atggaaaata    300
aacctacaag aaatggcaca agttagaaga aaatttgaga tgtttacata tactagattt    360
gattcagaag ttactctagt tccttctata gctgccaaag gggatgacat tggtcatgta    420
gtgatgcaat acatgtatgt cccaccaggc gctccagttc aaagaagag agatgactac     480 acatggcagt caggaaccaa tgcatctatt ttctggcaat atggacaaac atacccagg     540 tttcattac cctttctaag tatagcttca gcttattaca tgtttatga tggatatgat      600 ggagaccaac ctagttctag gtatggtaat atagttacca atgacatggg caccctatgt    660
tccaggatag taactgatga tcataagcac aagattgaag ttacaacaag aatatatcac    720
aaagcaaagc atgttaaggt atggtgcccg agaccaccta gagctgtaga gtatacatac    780
acccatgtaa caaactacaa accacattct ggtgatgtgc aaacagctat tagaccaaga    840
gcaacaatta agactgct                                                  858

<210> SEQ ID NO 58
<211> LENGTH: 858
<212> TYPE: DNA
<213> ORGANISM: rhinovirus

<400> SEQUENCE: 58
aatccagtag agaattatat agaagaggtg ttgaatgagg ttttagtagt gcctaatatc     60
agagagagtc aagcaaccac atcaaattca gcacctgcct tagatgcagc tgagactgga    120
cacactaata atgtacaacc agaagatatg attgaaacaa gatatgtaca aacatcacaa    180
actcttgatg agatgagtgt ggaaagcttc ttaggaaggt ctggttgcat tcacatgtca    240
aaattagtag tgaaatatga agactataat gagaaaaaga attttatgac atggaaaata    300
aatctacaag agatggcaca gattaggagg aaatttgaaa tgtttacata tgccagattt    360
gattcagaga tcaccctagt cccttctata gctgcccagg gagatgatgt tggtcatgtt    420
```

| | |
|---|---|
| gtaatgcagt acatgtatgt cccaccaggt gcaccagctc cagaaaagag agatgattac | 480 |
| acatggcaat caggaacaaa tgcatctgtc ttttggcaat atggacaaac atatcctagg | 540 |
| ttctcattac ctttccttag catagcttca gcatattaca tgttctatga tggatatgat | 600 |
| ggggaccaac ccaattccag gtatggtaat atggttacca atgacatggg cactttatgc | 660 |
| tctagaatag ttacagataa tcataagcat ccaatagaag ttacaacaag agtataccat | 720 |
| aaagcaaaac atgtcaaagt ctggtgccca agaccaccta gagctgtgga atacacccat | 780 |
| actcatgtta caaattataa atcaacaact cgtgaagtga agacagctat tagaccaaga | 840 |
| gcaacaatca agactgca | 858 |

```
<210> SEQ ID NO 59
<211> LENGTH: 858
<212> TYPE: DNA
<213> ORGANISM: rhionvirus

<400> SEQUENCE: 59
```

| | |
|---|---|
| aatccagtag agaattatat agaagaggtg ttgaatgagg ttttagtagt gcctaatatc | 60 |
| agagagagtc aagcaaccac atcaaattca gcacctgcct tagatgcagc tgagactgga | 120 |
| cacactaata atgtacaacc agaagatatg attgaaacaa gatatgtaca acatcacaa | 180 |
| actcttgatg agatgagtgt ggaaagcttc ttaggaaggt ctggttgcat tcacatgtca | 240 |
| aaattagtag tgaaatatga agactataat gagaaaaaga attttatgac atggaaaata | 300 |
| aatctacaag agatggcaca gattaggagg aaatttgaaa tgtttacata tgccagattt | 360 |
| gattcagaga tcaccctagt cccttctata gctgcccagg gagatgatgt tggtcatgtt | 420 |
| gtaatgcagt acatgtatgt cccaccaggt gcaccagctc cagaaaagag agatgattac | 480 |
| acatggcaat caggaacaaa tgcatctgtc ttttggcaat atggacaaac atatcctagg | 540 |
| ttctcattac ctttccttag catagcttca gcatattaca tgttctatga tggatatgat | 600 |
| ggggaccaac ccaattccag gtatggtaat atggttacca atgacatggg cactttatgc | 660 |
| tctagaatag ttacagataa tcataagcat ccaatagaag ttacaacaag agtataccat | 720 |
| aaagcaaaac atgtcaaagt ctggtgccca agaccaccta gagctgtgga atacacccat | 780 |
| actcatgtta caaattataa atcaacaact cgtgaagtga agacagctat tagaccaaga | 840 |
| gcaacaatca agactgcg | 858 |

```
<210> SEQ ID NO 60
<211> LENGTH: 858
<212> TYPE: DNA
<213> ORGANISM: rhinovirus

<400> SEQUENCE: 60
```

| | |
|---|---|
| aatccagtag agaattatat agaagaggtg ttgaatgagg ttttagtagt gcctaatatc | 60 |
| agagagagtc aagcaaccac atcaaattca gcacctgcct tagatgcagc tgagactgga | 120 |
| cacactaata atgtacaacc agaagatatg attgaaacaa gatatgtaca acatcacaa | 180 |
| actcttgatg agatgagtgt ggaaagcttc ttaggaaggt ctggttgcat tcacatgtca | 240 |
| aaattagtag tgaaatatga agactataat gagaaaaaga attttatgac atggaaaata | 300 |
| aatctacaag agatggcaca gattaggagg aaatttgaaa tgtttacata tgccagattt | 360 |
| gattcagaga tcaccctagt cccttctata gctgcccagg gagatgatgt tggtcatgtt | 420 |
| gtaatgcagt acatgtatgt cccaccaggt gcaccagctc cagaaaagag agatgattac | 480 |

| | |
|---|---|
| acatggcaat caggaacaaa tgcatctgtc ttttggcaat atggacaaac atatcctagg | 540 |
| ttctcattac ctttccttag catagcttca gcatattaca tgttctatga tggatatgat | 600 |
| ggggaccaac ccaattccag gtatggtaat atggttacca atgacatggg cactttatgc | 660 |
| tctagaatag ttacagataa tcataagcat ccaatagaag ttacaacaag agtataccat | 720 |
| aaagcaaaac atgtcaaagt ctggtgccca agaccaccta gagctgtgga atacacccat | 780 |
| actcatgtta caaattataa atcaacaact cgtgaagtga agacagctat tagaccaaga | 840 |
| gcaacaatca agactgct | 858 |

<210> SEQ ID NO 61
<211> LENGTH: 855
<212> TYPE: DNA
<213> ORGANISM: rhinovirus

<400> SEQUENCE: 61

| | |
|---|---|
| aacccagtag aaaattatat agatgaggtt ttgaatgaag tactggttgt gcctaatatt | 60 |
| aaggaaagta aaccatcaac atcaaactca gcaccagctt tggatgcagc agaaactgga | 120 |
| catacgagta gcgtgcagcc agaagatatg gttgaaacta gatatgtcca acatcacaa | 180 |
| acattacatg agatgagtgt tgaaagtttc ttgggtagat caggttgcat acacatgtcc | 240 |
| aagttgactg tggattatga caattatgat acaaaaaatt ttttcaaatg gcaaataaat | 300 |
| ctacaagaaa tggcccaagt cagaagaaaa tttgaattat tcacatatac tagatttgac | 360 |
| tctgagatta caatagttcc atccatagct ggcaagggag atgacattgg acatgttgta | 420 |
| atgcagtaca tgtatatacc acctggagca ccagtcccaa caaagagaga tgattataca | 480 |
| tggcaatcag gaacaaatgc atctgtcttt tggcaacatg gacaaaccta tcctagattt | 540 |
| tcccttcctt ttctgagtgt agcctctgca tattacatgt tttatgatgg atatgatggt | 600 |
| gatcaacacg actcagtgta tggttcagtt gttacaaacg catgggaac tctatgctat | 660 |
| agaatagtca ctgacaagca taatcaccaa atagaaatta caacaagaat ataccacaaa | 720 |
| gcaaagcaca ttaaggtctg gtgtccaagg ccacccagag ctgttgagta tacacatact | 780 |
| cacgtgacca attataagca tcagactcgt gaagtcaaga cagcaattga acctagaaga | 840 |
| ggaattaaaa cagtg | 855 |

<210> SEQ ID NO 62
<211> LENGTH: 855
<212> TYPE: DNA
<213> ORGANISM: rhinovirus

<400> SEQUENCE: 62

| | |
|---|---|
| aacccagtag aaaattatat agatgaggtt ttgaatgaag tactggttgt gcctaatatt | 60 |
| aaggaaagta aaccatcaac atcaaactca gcaccagctt tggatgcagc agaaactgga | 120 |
| catacgagta gcgtgcagcc agaagatatg gttgaaacta gatatgtcca acatcacaa | 180 |
| acattacatg agatgagtgt tgaaagtttc ttgggtagat caggttgcat acacatgtcc | 240 |
| aagttgactg tggattatga caattatgat acaaaaaatt ttttcaaatg gcaaataaat | 300 |
| ctacaagaaa tggcccaagt cagaagaaaa tttgaattat tcacatatac tagatttgac | 360 |
| tctgagatta caatagttcc atccatagct ggcaagggag atgacattgg acatgttgta | 420 |
| atgcagtaca tgtatatacc acctggagca ccagtcccaa caaagagaga tgattataca | 480 |
| tggcaatcag gaacaaatgc atctgtcttt tggcaacatg gacaaaccta tcctagattt | 540 |
| tcccttcctt ttctgagtgt agcctctgca tattacatgt tttatgatgg atatgatggt | 600 |

```
gatcaacacg actcagtgta tggttcagtt gttacaaacg acatgggaac tctatgctat    660
agaatagtca ctgacaagca taatcaccaa atagaaatta caacaagaat ataccacaaa    720
gcaaagcaca ttaaggtctg gtgtccaagg ccacccagag ctgttgagta tacacatact    780
cacgtgacca attataagca tcagactcgt gaagtcaaga cagcaattga acctagaaga    840
ggaattaaaa cagtc                                                     855

<210> SEQ ID NO 63
<211> LENGTH: 855
<212> TYPE: DNA
<213> ORGANISM: rhinovirus

<400> SEQUENCE: 63
aacccagtag aaaattatat agatgaggtt ttgaatgaag tactggttgt gcctaatatt     60
aaggaaagta aaccatcaac atcaaactca gcaccagctt tggatgcagc agaaactgga    120
catacgagta gcgtgcagcc agaagatatg gttgaaacta gatatgtcca acatcacaa     180 acattacatg agatgagtgt tgaaagtttc ttgggtagat caggttgcat acacatgtcc    240
aagttgactg tggattatga caattatgat acaaaaaatt ttttcaaatg gcaaataaat    300
ctacaagaaa tggcccaagt cagaagaaaa tttgaattat tcacatatac tagatttgac    360
tctgagatta caatagttcc atccatagct ggcaagggag atgacattgg acatgttgta    420
atgcagtaca tgtatatacc acctggagca ccagtcccaa caaagagaga tgattataca    480
tggcaatcag gaacaaatgc atctgtcttt tggcaacatg gacaaaccta tcctagattt    540
tcccttcctt ttctgagtgt agcctctgca tattacatgt tttatgatgg atatgatggt    600
gatcaacacg actcagtgta tggttcagtt gttacaaacg acatgggaac tctatgctat    660
agaatagtca ctgacaagca taatcaccaa atagaaatta caacaagaat ataccacaaa    720
gcaaagcaca ttaaggtctg gtgtccaagg ccacccagag ctgttgagta tacacatact    780
cacgtgacca attataagca tcagactcgt gaagtcaaga cagcaattga acctagaaga    840
ggaattaaaa cagtt                                                     855

<210> SEQ ID NO 64
<211> LENGTH: 855
<212> TYPE: DNA
<213> ORGANISM: rhinovirus

<400> SEQUENCE: 64
aatccagtgg aaaattatat agatgaagtc ctaaatgagg tattggttgt ccctaatatt     60
aaggaaagta aaccttcaac ttcaaactca gcgccagctt tagatgcagc agaaaccgga    120
catactagtg atgtccagcc agaagatgtg gtagagacca gatacgtgca acatcacaa     180 acaagagatg aaatgagtgt tgaaagtttt ctagggagat caggttgcat tcatatgtca    240
aaattagttg taaactatga taattatgat gaaaacaact tccataaatg gcaaattaac    300
ctgcaagaga tggcacagat tagaagaaaa tttgaattgt ttacatatgc tagatttgat    360
tctgaaatta caatagtacc atctatagct ggcaagggca atgatattgg acatgttgtg    420
atgcaataca tgtatatacc acctgggggca ccagtacctg agaagaggga tgattatgca    480
tggcaatcag gcactaatgc atctatcttt tggcaacatg gacaaacata ccctagattt    540
tcacttcctt tcttaagtat agcttctgca tactatatgt tttatgatgg atatgatggt    600 gaccaaaactg attcgagata tggtaccatt gttactaatg atatgggaac cttatgttat    660
```

```
agaatagtta cagatgaaca tgcccacaaa atagagatca ctacaagaat ataccataaa    720
gcaaaacaca ttaaggtttg gtgtccaaga ccacctaggg cagttgaata cacacacact    780
catgtaacaa actacaaaca tgcaacacgt gaacttaaga ctgcaattag gcccaggaaa    840
acaatcacaa cagca                                                     855

<210> SEQ ID NO 65
<211> LENGTH: 855
<212> TYPE: DNA
<213> ORGANISM: rhinovirus

<400> SEQUENCE: 65
aatccagtgg aaaattatat agatgaagtc ctaaatgagg tattggttgt ccctaatatt     60
aaggaaagta aaccttcaac ttcaaactca gcgccagctt tagatgcagc agaaaccgga    120
catactagtg atgtccagcc agaagatgtg gtagagacca gatacgtgca aacatcacaa    180
acaagagatg aaatgagtgt tgaaagtttt ctagggagat caggttgcat tcatatgtca    240
aaattagttg taaactatga taattatgat gaaaacaact tccataaatg gcaaattaac    300
ctgcaagaga tggcacagat tagaagaaaa tttgaattgt ttacatatgc tagatttgat    360
tctgaaatta caatagtacc atctatagct ggcaagggca atgatattgg acatgttgtg    420
atgcaataca tgtatatacc acctgggggca ccagtacctg agaagaggga tgattatgca    480
tggcaatcag gcactaatgc atctatcttt tggcaacatg gacaaacata ccctagattt    540
tcacttcctt tcttaagtat agcttctgca tactatatgt tttatgatgg atatgatggt    600
gaccaaactg attcgagata tggtaccatt gttactaatg atatgggaac cttatgttat    660
agaatagtta cagatgaaca tgcccacaaa atagagatca ctacaagaat ataccataaa    720
gcaaaacaca ttaaggtttg gtgtccaaga ccacctaggg cagttgaata cacacacact    780
catgtaacaa actacaaaca tgcaacacgt gaacttaaga ctgcaattag gcccaggaaa    840
acaatcacaa cagcg                                                     855

<210> SEQ ID NO 66
<211> LENGTH: 855
<212> TYPE: DNA
<213> ORGANISM: rhinovirus

<400> SEQUENCE: 66
aatccagtgg aaaattatat agatgaagtc ctaaatgagg tattggttgt ccctaatatt     60
aaggaaagta aaccttcaac ttcaaactca gcgccagctt tagatgcagc agaaaccgga    120
catactagtg atgtccagcc agaagatgtg gtagagacca gatacgtgca aacatcacaa    180
acaagagatg aaatgagtgt tgaaagtttt ctagggagat caggttgcat tcatatgtca    240
aaattagttg taaactatga taattatgat gaaaacaact tccataaatg gcaaattaac    300
ctgcaagaga tggcacagat tagaagaaaa tttgaattgt ttacatatgc tagatttgat    360
tctgaaatta caatagtacc atctatagct ggcaagggca atgatattgg acatgttgtg    420
atgcaataca tgtatatacc acctgggggca ccagtacctg agaagaggga tgattatgca    480
tggcaatcag gcactaatgc atctatcttt tggcaacatg gacaaacata ccctagattt    540
tcacttcctt tcttaagtat agcttctgca tactatatgt tttatgatgg atatgatggt    600
gaccaaactg attcgagata tggtaccatt gttactaatg atatgggaac cttatgttat    660
agaatagtta cagatgaaca tgcccacaaa atagagatca ctacaagaat ataccataaa    720
gcaaaacaca ttaaggtttg gtgtccaaga ccacctaggg cagttgaata cacacacact    780
```

| catgtaacaa actacaaaca tgcaacacgt gaacttaaga ctgcaattag gcccaggaaa | 840 |
| acaatcacaa cagct | 855 |

<210> SEQ ID NO 67
<211> LENGTH: 861
<212> TYPE: DNA
<213> ORGANISM: rhinovirus

<400> SEQUENCE: 67

| aatccagttg aaaattacat agatgaggta ctaaatgagg tattggttgt accaaacatt | 60 |
| aaagaaagcc aagccaccac atcaaactct gcccccgcac tggatgcagc tgagactggt | 120 |
| cacactagca gtgtacaacc tgaagatatg attgagacca ggtacgtaca acatcacaa | 180 |
| acaagagatg aaatgagcat tgagagtttc ctgggtaggt ctggctgtat acacatgtcc | 240 |
| aaacttgttg tagattatga aaattacaat gcaaaaacaa gaactttat gacatggcaa | 300 |
| attaatttac aggaaatggc acagattaga aggaaatttg aatgttcac ctacgtcaga | 360 |
| tttgattctg aagtcaccct agtaccatca atagcggcca aaggtgatga tattggacat | 420 |
| gttgtgatgc aatacatgta tgtaccacca ggtgcaccaa tacctaaaac tagagatgat | 480 |
| tttgcatggc aatctggaac aaatgcctca atattttggc aacatggtca aacatacctt | 540 |
| agattttccc tcccttttctt aagcatagcc tcagcatact acatgtttta tgatggatat | 600 |
| gatggtgatc aacatgattc aagatatggt acagtagtga ctaatgacat gggtacttta | 660 |
| tgctccagaa ttgtaactga tgaacaccaa aacagagtag aaataacaac tagagtttat | 720 |
| cacaaagcta acatgtaaa aacctggtgt ccaagaccac caagagctgt tgagtacaca | 780 |
| cacacacatg ttactaacta caaagttagg ggtaaaactg agaagactgc aatcaaacac | 840 |
| agagcaaaga tcacaatggc c | 861 |

<210> SEQ ID NO 68
<211> LENGTH: 861
<212> TYPE: DNA
<213> ORGANISM: rhinovirus

<400> SEQUENCE: 68

| aatccagttg aaaattacat agatgaggta ctaaatgagg tattggttgt accaaacatt | 60 |
| aaagaaagcc aagccaccac atcaaactct gcccccgcac tggatgcagc tgagactggt | 120 |
| cacactagca gtgtacaacc tgaagatatg attgagacca ggtacgtaca acatcacaa | 180 |
| acaagagatg aaatgagcat tgagagtttc ctgggtaggt ctggctgtat acacatgtcc | 240 |
| aaacttgttg tagattatga aaattacaat gcaaaaacaa gaactttat gacatggcaa | 300 |
| attaatttac aggaaatggc acagattaga aggaaatttg aatgttcac ctacgtcaga | 360 |
| tttgattctg aagtcaccct agtaccatca atagcggcca aaggtgatga tattggacat | 420 |
| gttgtgatgc aatacatgta tgtaccacca ggtgcaccaa tacctaaaac tagagatgat | 480 |
| tttgcatggc aatctggaac aaatgcctca atattttggc aacatggtca aacatacctt | 540 |
| agattttccc tcccttttctt aagcatagcc tcagcatact acatgtttta tgatggatat | 600 |
| gatggtgatc aacatgattc aagatatggt acagtagtga ctaatgacat gggtacttta | 660 |
| tgctccagaa ttgtaactga tgaacaccaa aacagagtag aaataacaac tagagtttat | 720 |
| cacaaagcta acatgtaaa aacctggtgt ccaagaccac caagagctgt tgagtacaca | 780 |
| cacacacatg ttactaacta caaagttagg ggtaaaactg agaagactgc aatcaaacac | 840 | agagcaaaga tcacaatggc a                                                861

<210> SEQ ID NO 69
<211> LENGTH: 861
<212> TYPE: DNA
<213> ORGANISM: rhinovirus

<400> SEQUENCE: 69

```
aatccagttg aaaattacat agatgaggta ctaaatgagg tattggttgt accaaacatt        60
aaagaaagcc aagccaccac atcaaactct gcccccgcac tggatgcagc tgagactggt       120
cacactagca gtgtacaacc tgaagatatg attgagacca ggtacgtaca acatcacaa        180
acaagagatg aaatgagcat tgagagtttc ctgggtaggt ctggctgtat acacatgtcc       240
aaacttgttg tagattatga aaattacaat gcaaaaacaa gaactttat gacatggcaa        300
attaatttac aggaaatggc acagattaga aggaaatttg aaatgttcac ctacgtcaga       360
tttgattctg aagtcaccct agtaccatca atagcggcca aggtgatga tattggacat        420
gttgtgatgc aatacatgta tgtaccacca ggtgcaccaa tacctaaaac tagagatgat       480
tttgcatggc aatctggaac aaatgcctca atattttggc aacatggtca aacatacct        540
agattttccc tcccttttctt aagcatagcc tcagcatact acatgtttta tgatggatat       600
gatggtgatc aacatgattc aagatatggt acagtagtga ctaatgacat gggtacttta       660
tgctccagaa ttgtaactga tgaacaccaa aacagagtag aaataacaac tagagtttat       720
cacaaagcta aacatgtaaa aacctggtgt ccaagaccac caagagctgt tgagtacaca       780
cacacacatg ttactaacta caaagttagg ggtaaaactg agaagactgc aatcaaacac       840
agagcaaaga tcacaatggc t                                                861
```

<210> SEQ ID NO 70
<211> LENGTH: 861
<212> TYPE: DNA
<213> ORGANISM: rhinovirus

<400> SEQUENCE: 70

```
aatccagtgg agaattacat agatgaagta ttaaatgagg tattagttgt cccaaatatc        60
aaggagagtc aagccactac atcaaactct gcccctgctt tagatgcagc tgaaactgga       120
cacacaagta atgtgcagcc tgaagatatg cttgaaacta gatatgtgca acatcgcat        180
acaagagatg aaatgagcat tgaaagtttc ctaggtagat ctggttgtat acatatatct       240
aaattagttg ttgattatga tggttacaat gaggaaacaa agaacttcaa gaatggcaa        300
atcaacctac aagaaatggc acagatcaga aggaaatttg agatgttcac ctatgtgagg       360
tttaattctg aggtcacatt agtaccatcc atagctgcca aggtgttga tattggacat        420
gttgtcatgc aatacatgta tgtcccacca ggtgcaccaa tacccaagac tagggatgat       480
tttgcctggc aatctggaac taatgcttca atcttttggc aacatggtca aacatacct        540
agattctctc taccattctt gagtatagca tctgcatatt acatgtttta tgatggttat       600
gatggtgata atctcacatc caggtatggt acagtagtta ccaatgacat ggcactttg        660
tgttctagga ttgtcactga tgagcaccaa aataaagtgg aaatcacaac cagagtatac       720
cataaagcca aacacataaa agtctggtgt ccaagaccac caagagctgt tgaatacaca       780
cacacccatg tcactaacta caagaaaagt gatgctactg agaagactgc aattgcaact       840
agaccaaaga tcacagtggc a                                                861
```

<210> SEQ ID NO 71
<211> LENGTH: 861
<212> TYPE: DNA
<213> ORGANISM: rhinovirus

<400> SEQUENCE: 71

| | | | | | |
|---|---|---|---|---|---|
| aatccagtgg | agaattacat | agatgaagta | ttaaatgagg | tattagttgt | cccaaatatc | 60 |
| aaggagagtc | aagccactac | atcaaactct | gcccctgctt | tagatgcagc | tgaaactgga | 120 |
| cacacaagta | atgtgcagcc | tgaagatatg | cttgaaacta | gatatgtgca | acatcgcat | 180 |
| acaagagatt | aaatgagcat | tgaaagtttc | ctaggtagat | ctggttgtat | acatatatct | 240 |
| aaattagttg | ttgattatga | tggttacaat | gaggaaacaa | agaacttcaa | gaaatggcaa | 300 |
| atcaacctac | aagaaatggc | acagatcaga | aggaaatttg | agatgttcac | ctatgtgagg | 360 |
| tttaattctg | aggtcacatt | agtaccatcc | atagctgcca | agggtgttga | tattggacat | 420 |
| gttgtcatgc | aatacatgta | tgtcccacca | ggtgcaccaa | tacccaagac | tagggatgat | 480 |
| tttgcctggc | aatctggaac | taatgcttca | atcttttggc | aacatggtca | aacatacct | 540 |
| agattctctc | taccattctt | gagtatagca | tctgcatatt | acatgtttta | tgatggttat | 600 |
| gatggtgata | aatctacatc | caggtatggt | acagtagtta | ccaatgacat | gggcactttg | 660 |
| tgttctagga | ttgtcactga | tgagcaccaa | aataaagtgg | aaatcacaac | cagagtatac | 720 |
| cataaagcca | aacacataaa | agtctggtgt | ccaagaccac | caagagctgt | tgaatacaca | 780 |
| cacacccatg | tcactaacta | caagaaaagt | gatgctactg | agaagactgc | aattgcaact | 840 |
| agaccaaaga | tcacagtggc | g | | | | 861 |

<210> SEQ ID NO 72
<211> LENGTH: 861
<212> TYPE: DNA
<213> ORGANISM: rhinovirus

<400> SEQUENCE: 72

| | | | | | |
|---|---|---|---|---|---|
| aatccagtgg | agaattacat | agatgaagta | ttaaatgagg | tattagttgt | cccaaatatc | 60 |
| aaggagagtc | aagccactac | atcaaactct | gcccctgctt | tagatgcagc | tgaaactgga | 120 |
| cacacaagta | atgtgcagcc | tgaagatatg | cttgaaacta | gatatgtgca | acatcgcat | 180 |
| acaagagatt | aaatgagcat | tgaaagtttc | ctaggtagat | ctggttgtat | acatatatct | 240 |
| aaattagttg | ttgattatga | tggttacaat | gaggaaacaa | agaacttcaa | gaaatggcaa | 300 |
| atcaacctac | aagaaatggc | acagatcaga | aggaaatttg | agatgttcac | ctatgtgagg | 360 |
| tttaattctg | aggtcacatt | agtaccatcc | atagctgcca | agggtgttga | tattggacat | 420 |
| gttgtcatgc | aatacatgta | tgtcccacca | ggtgcaccaa | tacccaagac | tagggatgat | 480 |
| tttgcctggc | aatctggaac | taatgcttca | atcttttggc | aacatggtca | aacatacct | 540 |
| agattctctc | taccattctt | gagtatagca | tctgcatatt | acatgtttta | tgatggttat | 600 |
| gatggtgata | aatctacatc | caggtatggt | acagtagtta | ccaatgacat | gggcactttg | 660 |
| tgttctagga | ttgtcactga | tgagcaccaa | aataaagtgg | aaatcacaac | cagagtatac | 720 |
| cataaagcca | aacacataaa | agtctggtgt | ccaagaccac | caagagctgt | tgaatacaca | 780 |
| cacacccatg | tcactaacta | caagaaaagt | gatgctactg | agaagactgc | aattgcaact | 840 |
| agaccaaaga | tcacagtggc | t | | | | 861 |

<210> SEQ ID NO 73
<211> LENGTH: 861
<212> TYPE: DNA

<213> ORGANISM: rhinovirus

<400> SEQUENCE: 73

```
aatccagtag agaattatat agatgaagta cttaatgaag tgttagtggt cccaaatgtg     60
aatgaaagtc acgcaattac atcaaattca gcccctgctt tagatgccgc tgaaactggt    120
cacaccagca atgtgcaacc tgaagatatg attgagacta ggtatgtaca acatcacaa    180
acaagagatg aaatgagtat agagtgtttt ctaggcagat cagggtgtat acatatctcc    240
aagttagttg tacattatga agattataat gcagaaacaa ggaactttgt aaaatggcaa    300
ataaatctac aggaaatggc ccagattagg agaaaatttg agatgtttac atatgttaga    360
tttgattcag aaattacact agtaccatct gtagctgcta agggtgatga cataggacat    420
attgttatgc agtacatgta tgttcctcca ggagcaccaa taccaaaaac cagagatgat    480
tttgcctggc aatctggaac aaatgcatca atcttctggc aacatggtca aacataccccc    540
agattttcac ttcctttcct cagtatagca tcagcttatt acatgttcta tgatggctac    600
gacggtgacc agacctcatc gcggtatggc acagttgcaa caaatgacat gggtaccttg    660
tgctctagaa tagtcacaga taaacataag aatgaggtgg aaataacaac cagaatatac    720
cacaaggcaa acatgttaa agcatggtgc ccaaggccac cgagagctgt ggagtacaca    780
catacacatg taactaacta caagcctaag gaaggaagag agaaaactgc catagtaccc    840
agagcaagga ttacaatggc a                                              861
```

<210> SEQ ID NO 74
<211> LENGTH: 861
<212> TYPE: DNA
<213> ORGANISM: rhinovirus

<400> SEQUENCE: 74

```
aatccagtag agaattatat agatgaagta cttaatgaag tgttagtggt cccaaatgtg     60
aatgaaagtc acgcaattac atcaaattca gcccctgctt tagatgccgc tgaaactggt    120
cacaccagca atgtgcaacc tgaagatatg attgagacta ggtatgtaca acatcacaa    180
acaagagatg aaatgagtat agagtgtttt ctaggcagat cagggtgtat acatatctcc    240
aagttagttg tacattatga agattataat gcagaaacaa ggaactttgt aaaatggcaa    300
ataaatctac aggaaatggc ccagattagg agaaaatttg agatgtttac atatgttaga    360
tttgattcag aaattacact agtaccatct gtagctgcta agggtgatga cataggacat    420
attgttatgc agtacatgta tgttcctcca ggagcaccaa taccaaaaac cagagatgat    480
tttgcctggc aatctggaac aaatgcatca atcttctggc aacatggtca aacataccccc    540
agattttcac ttcctttcct cagtatagca tcagcttatt acatgttcta tgatggctac    600
gacggtgacc agacctcatc gcggtatggc acagttgcaa caaatgacat gggtaccttg    660
tgctctagaa tagtcacaga taaacataag aatgaggtgg aaataacaac cagaatatac    720
cacaaggcaa acatgttaa agcatggtgc ccaaggccac cgagagctgt ggagtacaca    780
catacacatg taactaacta caagcctaag gaaggaagag agaaaactgc catagtaccc    840
agagcaagga ttacaatggc g                                              861
```

<210> SEQ ID NO 75
<211> LENGTH: 861
<212> TYPE: DNA
<213> ORGANISM: rhinovirus

<400> SEQUENCE: 75

```
aatccagtag agaattatat agatgaagta cttaatgaag tgttagtggt cccaaatgtg    60
aatgaaagtc acgcaattac atcaaattca gcccctgctt tagatgccgc tgaaactggt   120
cacaccagca atgtgcaacc tgaagatatg attgagacta ggtatgtaca acatcacaa   180 acaagagatg aaatgagtat agagtgtttt ctaggcagat cagggtgtat acatatctcc   240
aagttagttg tacattatga agattataat gcagaaacaa ggaactttgt aaaatggcaa   300
ataaatctac aggaaatggc ccagattagg agaaaatttg agatgtttac atatgttaga   360
tttgattcag aaattacact agtaccatct gtagctgcta agggtgatga cataggacat   420
attgttatgc agtacatgta tgttcctcca ggagcaccaa taccaaaaac cagagatgat   480
tttgcctggc aatctggaac aaatgcatca atcttctggc aacatggtca aacataccc   540 agattttcac ttcctttcct cagtatagca tcagcttatt acatgttcta tgatggctac   600
gacggtgacc agacctcatc gcggtatggc acagttgcaa caaatgacat gggtaccttg   660
tgctctagaa tagtcacaga taaacataag aatgaggtgg aaataacaac cagaatatac   720
cacaaggcaa acatgttaa agcatggtgc ccaaggccac cgagagctgt ggagtacaca    780
catacacatg taactaacta caagcctaag gaaggaagag agaaaactgc catagtaccc   840
agagcaagga ttacaatggc t                                             861

<210> SEQ ID NO 76
<211> LENGTH: 861
<212> TYPE: DNA
<213> ORGANISM: rhinovirus

<400> SEQUENCE: 76
aatcctgtag agagatatgt tgatgaagtc ctgaatgaag tgctagtagt tccaaatatt    60
agggagagtc aagcagcaac atcaaattca gctccagtac tagatgcagc agaaactggg   120
catacaagca atgtacaacc agaagatgta attgagacaa gatatgttca gacatcacaa   180
actcgtgatg agatgagcat tgaaagtttt ctaggtagat caggatgtgt acatatatca   240
gagttagttt tcattatga agaatataac aaagagggaa aaaattttac taagtggcaa   300
gtaaacatcc aagagatggc tcagattaga agaaaatttg aaatgttcac ctatactaga   360
tttgattcag aagttacatt agtaccctct attgctgcaa aggagatga cattggacat   420 gtagtcatgc aatacatgta tgttccacct ggagcaccaa ttccaaagac aagagaagat   480
tatgcttggc aatcagggac caatgcatct atcttttggc aacatgggca aacataccct   540
agattttcac ttcctttcct aagtatagct tctgcttatt acatgttcta tgatggatat   600
gatggtgacc aaactgagtc acgctatggc actgtagtca ctaatgacat gggtacttta   660
tgttctagaa taataactga taaccataag cacccaattg aagtgacgac aagagtctat   720
cataaagcta aacacatcaa agcatggtgc cacgaccac ctagggctgt gaatacaca   780 cacacacatg tcacaaatta caagaagact gatggcacag aaaagacagc aattgaatac   840
agaagggaca ttaaaacagt g                                             861

<210> SEQ ID NO 77
<211> LENGTH: 861
<212> TYPE: DNA
<213> ORGANISM: rhinovirus

<400> SEQUENCE: 77
aatcctgtag agagatatgt tgatgaagtc ctgaatgaag tgctagtagt tccaaatatt    60
```

```
agggagagtc aagcagcaac atcaaattca gctccagtac tagatgcagc agaaactggg      120
catacaagca atgtacaacc agaagatgta attgagacaa gatatgttca gacatcacaa      180
actcgtgatg agatgagcat tgaaagtttt ctaggtagat caggatgtgt acatatatca      240
gagttagttg ttcattatga agaatataac aaagagggaa aaaattttac taagtggcaa      300
gtaaacatcc aagagatggc tcagattaga agaaaatttg aaatgttcac ctatactaga      360
tttgattcag aagttacatt agtaccctct attgctgcaa agggagatga cattggacat      420
gtagtcatgc aatacatgta tgttccacct ggagcaccaa ttccaaagac aagagaagat      480
tatgcttggc aatcagggac caatgcatct atcttttggc aacatgggca aacataccct      540
agattttcac ttccttttcct aagtatagct tctgcttatt acatgttcta tgatggatat      600
gatggtgacc aaactgagtc acgctatggc actgtagtca ctaatgacat gggtacttta      660
tgttctagaa taataactga taaccataag cacccaattg aagtgacgac aagagtctat      720
cataaagcta aacacatcaa agcatggtgc ccacgaccac ctagggctgt tgaatacaca      780
cacacacatg tcacaaatta caagaagact gatggcacag aaaagacagc aattgaatac      840
agaagggaca ttaaaacagt c                                                861

<210> SEQ ID NO 78
<211> LENGTH: 861
<212> TYPE: DNA
<213> ORGANISM: rhinovirus

<400> SEQUENCE: 78
aatcctgtag agagatatgt tgatgaagtc ctgaatgaag tgctagtagt tccaaatatt      60
agggagagtc aagcagcaac atcaaattca gctccagtac tagatgcagc agaaactggg      120
catacaagca atgtacaacc agaagatgta attgagacaa gatatgttca gacatcacaa      180
actcgtgatg agatgagcat tgaaagtttt ctaggtagat caggatgtgt acatatatca      240
gagttagttg ttcattatga agaatataac aaagagggaa aaaattttac taagtggcaa      300
gtaaacatcc aagagatggc tcagattaga agaaaatttg aaatgttcac ctatactaga      360
tttgattcag aagttacatt agtaccctct attgctgcaa agggagatga cattggacat      420
gtagtcatgc aatacatgta tgttccacct ggagcaccaa ttccaaagac aagagaagat      480
tatgcttggc aatcagggac caatgcatct atcttttggc aacatgggca aacataccct      540
agattttcac ttccttttcct aagtatagct tctgcttatt acatgttcta tgatggatat      600
gatggtgacc aaactgagtc acgctatggc actgtagtca ctaatgacat gggtacttta      660
tgttctagaa taataactga taaccataag cacccaattg aagtgacgac aagagtctat      720
cataaagcta aacacatcaa agcatggtgc ccacgaccac ctagggctgt tgaatacaca      780
cacacacatg tcacaaatta caagaagact gatggcacag aaaagacagc aattgaatac      840
agaagggaca ttaaaacagt a                                                861

<210> SEQ ID NO 79
<211> LENGTH: 864
<212> TYPE: DNA
<213> ORGANISM: rhinovirus

<400> SEQUENCE: 79
aacccagtag aaaattttgt ggatgagatc ttgaatgaag ttttggtggt tccagatatc       60
aaacaaagtc aagcaacaac atcaaactca gcacctgcat tggatgcagc tgaaactgga      120
cacactagta atgtacaacc ggaagacatg attgaaacta gatatgtcca gacatcacaa      180
```

| | |
|---|---:|
| acacgtgatg aaatgagtct tgagagcttc ttaggaagat ctggctgcat tcatatttca | 240 |
| gagcttaagg taaaatatga aaattacaac acagagaatt tcactaaatg ggaaataaat | 300 |
| ctacaagaaa tggcacaaat cagaagaaaa tttgaactat ttacatatgt taggtttgat | 360 |
| tctgaagtta cattagttcc ctccatagct gctcaaggtg aggatatagg ccatgttgta | 420 |
| atgcaataca tgtatgtccc tcctggggca ccaattccaa aaacaagaga ggattataca | 480 |
| tggcaatctg gtaccaatgc ttcaatattt tggcaacatg gtcaaacata ccctagattt | 540 |
| tccttgcctt tcttaagtat agcctcagca tattacatgt tttatgatgg atatgatggt | 600 |
| gaccaaactg aatcaagata tggtactgta gtcactaatg acatgggcac tttatgttct | 660 |
| agaattgtta ctgaccagca cacacatccc ataaaaataa caaccagagt gtatcacaaa | 720 |
| gccaaacatg tcaaagcctg gtgccctaga ccaccacggg ctatcgagta cacacataca | 780 |
| catgttacta attataaaat aaaagataga caagaagaaa cagcaattaa atatagaagg | 840 |
| gacattaaaa ttgttaagaa tgtg | 864 |

<210> SEQ ID NO 80
<211> LENGTH: 864
<212> TYPE: DNA
<213> ORGANISM: rhinovirus

<400> SEQUENCE: 80

| | |
|---|---:|
| aacccagtag aaaattttgt ggatgagatc ttgaatgaag ttttggtggt tccagatatc | 60 |
| aaacaaagtc aagcaacaac atcaaactca gcacctgcat ggatgcagc tgaaactgga | 120 |
| cacactagta atgtacaacc ggaagacatg attgaaacta gatatgtcca gacatcacaa | 180 |
| acacgtgatg aaatgagtct tgagagcttc ttaggaagat ctggctgcat tcatatttca | 240 |
| gagcttaagg taaaatatga aaattacaac acagagaatt tcactaaatg ggaaataaat | 300 |
| ctacaagaaa tggcacaaat cagaagaaaa tttgaactat ttacatatgt taggtttgat | 360 |
| tctgaagtta cattagttcc ctccatagct gctcaaggtg aggatatagg ccatgttgta | 420 |
| atgcaataca tgtatgtccc tcctggggca ccaattccaa aaacaagaga ggattataca | 480 |
| tggcaatctg gtaccaatgc ttcaatattt tggcaacatg gtcaaacata ccctagattt | 540 |
| tccttgcctt tcttaagtat agcctcagca tattacatgt tttatgatgg atatgatggt | 600 |
| gaccaaactg aatcaagata tggtactgta gtcactaatg acatgggcac tttatgttct | 660 |
| agaattgtta ctgaccagca cacacatccc ataaaaataa caaccagagt gtatcacaaa | 720 |
| gccaaacatg tcaaagcctg gtgccctaga ccaccacggg ctatcgagta cacacataca | 780 |
| catgttacta attataaaat aaaagataga caagaagaaa cagcaattaa atatagaagg | 840 |
| gacattaaaa ttgttaagaa tgta | 864 |

<210> SEQ ID NO 81
<211> LENGTH: 864
<212> TYPE: DNA
<213> ORGANISM: rhinovirus

<400> SEQUENCE: 81

| | |
|---|---:|
| aacccagtag aaaattttgt ggatgagatc ttgaatgaag ttttggtggt tccagatatc | 60 |
| aaacaaagtc aagcaacaac atcaaactca gcacctgcat ggatgcagc tgaaactgga | 120 |
| cacactagta atgtacaacc ggaagacatg attgaaacta gatatgtcca gacatcacaa | 180 |
| acacgtgatg aaatgagtct tgagagcttc ttaggaagat ctggctgcat tcatatttca | 240 |

```
gagcttaagg taaaatatga aaattacaac acagagaatt tcactaaatg ggaaataaat      300
ctacaagaaa tggcacaaat cagaagaaaa tttgaactat ttacatatgt taggtttgat      360
tctgaagtta cattagttcc ctccatagct gctcaaggtg aggatatagg ccatgttgta      420
atgcaataca tgtatgtccc tcctggggca ccaattccaa aaacaagaga ggattataca      480
tggcaatctg gtaccaatgc ttcaatattt tggcaacatg gtcaaacata ccctagattt      540
tccttgcctt tcttaagtat agcctcagca tattacatgt tttatgatgg atatgatggt      600
gaccaaactg aatcaagata tggtactgta gtcactaatg acatgggcac tttatgttct      660
agaattgtta ctgaccagca cacacatccc ataaaaataa caaccagagt gtatcacaaa      720
gccaaacatg tcaaagcctg gtgccctaga ccaccacggg ctatcgagta cacacataca      780
catgttacta attataaaat aaagatagaa caagaagaaa cagcaattaa atatagaagg      840
gacattaaaa ttgttaagaa tgtc                                             864

<210> SEQ ID NO 82
<211> LENGTH: 861
<212> TYPE: DNA
<213> ORGANISM: rhinovirus

<400> SEQUENCE: 82
aatcctgtag agaattatat agatgaagtc ctaaatgaag tcttagtagt gccaaatatc       60
agagagagtc atggaacaac atcaaactct gctcccgcac ttgatgctgc agaaactgga      120
cacactagta atgtacagcc ggaggatatg gttgaaacaa ggtatgttca gacatcacaa      180
acacgtgatg aaatgagtat tgaaagtttt ctgggcagat cagggtgcat tcacatgtca      240
aaattagtag ttaactatga taattacaat actggagaaa ataacattag tacatggcaa      300
ataaatatta agagatggc acaaattagg agaaaatttg aaatgttcac ctatactaga      360
tttgattcag aaataacttt ggtgccgtca attgcagcta gaacgggtga cataggacat      420
gttgtaatgc aatatatgta tgtcccacca ggtgctccaa ttccaaaaac tagggaagat      480
tttgcttggc agtcaggcac taatgcatcc attttctggc agcatggcca gacttatcct      540
agattttcat taccccttcct tagtatagca tcagcatact acatgtttta tgatggttat      600
gatggtgacc agactgactc acaatatggt gcagtagtaa ctaatgatat gggatctcta      660
tgctacagaa tagtaactgg ccagcataag cataagatag aagtgaccac aagaatatac      720
cataaggcaa agcatgttaa agcttggtgc cccagaccac cgagggccgt tgaatacaca      780
catacacacg taaccaatta caaaattgca aatcatgaag tcacttctgc agttgagtcc      840
agaagaacaa ttgtcacagt t                                                861

<210> SEQ ID NO 83
<211> LENGTH: 861
<212> TYPE: DNA
<213> ORGANISM: rhinovirus

<400> SEQUENCE: 83
aatcctgtag agaattacgt agatgaagtt ctaaatgagg tcttagtagt gccaaatatc       60
agagagagtc atggaacaac atcaaactct gctcccgcac ttgatgctgc agaaactggg      120
cacactagta atgtacaacc agaggatatg gttgaaacaa ggtatgttca gacatcacaa      180
acacgtgatg aaatgagtat tgaaagtttt ctaggcagat cagggtgtat ccacatgtca      240
aaattaatag ttaactatga caactacaat actggagaaa ataacattaa tacatggcaa      300
ataaatatta agagatggc acaaattagg agaaaatttg aaatgttcac ctatactaga      360
```

```
tttgattcag aaataacttt ggtaccgtca attgcagcta aagcgggtga catagggacat    420 gttgtgatgc aatatatgta tgtcccacca ggtgctccaa ttccaaaaac tagggaagat    480
tttgcttggc aatcaggtac caatgcatcc attttctggc agcatggtca aacttatcct    540
agattttcac taccccttcct tagtatagca tcagcatatt acatgtttta tgatggttat    600
gatggtgatc agactgactc acaatatggt gcagtggtga ctaatgatat gggatctcta    660
tgctatagaa tagtaactga tcagcataag cacaagatag aagtgaccac aagaatatac    720
cataaggcaa agcatgttaa agcttggtgc cctagaccac cgagggccgt tgaatacaca    780
catacacatg taaccaatta caaaattgca aataaagatg tcacttctgc agttgagtcc    840
agaagaacaa ttgtcacagt t                                              861

<210> SEQ ID NO 84
<211> LENGTH: 867
<212> TYPE: DNA
<213> ORGANISM: rhinovirus

<400> SEQUENCE: 84
aatcctgttg aaaattatgt tgatgaaatt ttaaatcaag ttcttgtagt cccaaacact     60
gtagaaagtc attcaacaac atccaatgca gcccctgcac ttgatgcagc tgaaactggg    120
catactagcc aggtgcaacc tgaagacatg gtagagacaa ggtcagtaca aatttccaa    180 accagagatg aaatgagtat tgaaagtttc ttgggcagat ctggttgcat acatatttca    240
acacttgaag taaattatga tgattataat gggacaggca taaattttac ccaatggcca    300
atcaacttgc aagaaatggc acaaattaga agaaagtatg aattgttcac atacttaagg    360
tttgattctg aaattaccct tgttccttgc attgcagcaa aaagcaatga tataggccat    420
gtggtaatgc agtacatgta tgtaccacca ggtgcgccaa ttccaaaaac taggaaagat    480
tatgcatggc aatctggcac aaatgcatct gttttctggc aacatggtca aacatttcca    540
agattttcct taccttttct gagcatagca tcagcatatt acatgtttta tgatggatat    600
gaaggtgacc aaaaaacatc ccgttatggc acaattgcaa gcaaccacat gggaacatta    660
tgttctagga tagttacaga agaacaccaa aatcaaatcg ataactac caggatatat    720 cataaagcca agcatatcaa agcttggtgc ccaagaccac ccagagctgt tgaatacaca    780
cacacacatg tcacaaatta taaaagagaa ggaaaggagg tagaaacagc catagtatct    840
aggagggata tcaaaattgt caatgca                                        867

<210> SEQ ID NO 85
<211> LENGTH: 867
<212> TYPE: DNA
<213> ORGANISM: rhinovirus

<400> SEQUENCE: 85
aatcctgttg aaaattatgt tgatgaaatt ttaaatcaag ttcttgtagt cccaaacact     60
gtagaaagtc attcaacaac atccaatgca gcccctgcac ttgatgcagc tgaaactggg    120
catactagcc aggtgcaacc tgaagacatg gtagagacaa ggtcagtaca aatttccaa    180 accagagatg aaatgagtat tgaaagtttc ttgggcagat ctggttgcat acatatttca    240
acacttgaag taaattatga tgattataat gggacaggca taaattttac ccaatggcca    300
atcaacttgc aagaaatggc acaaattaga agaaagtatg aattgttcac atacttaagg    360
tttgattctg aaattaccct tgttccttgc attgcagcaa aaagcaatga tataggccat    420
```

| | |
|---|---|
| gtggtaatgc agtacatgta tgtaccacca ggtgcgccaa ttccaaaaac taggaaagat | 480 |
| tatgcatggc aatctggcac aaatgcatct gttttctggc aacatggtca acatttcca | 540 |
| agatttcct taccttttct gagcatagca tcagcatatt acatgtttta tgatggatat | 600 |
| gaaggtgacc aaaaaacatc ccgttatggc acaattgcaa gcaaccacat gggaacatta | 660 |
| tgttctagga tagttacaga agaacaccaa atcaaatcg ataactac caggatatat | 720 |
| cataaagcca agcatatcaa agcttggtgc ccaagaccac ccagagctgt tgaatacaca | 780 |
| cacacacatg tcacaaatta taaaagagaa ggaaaggagg tagaaacagc catagtatct | 840 |
| aggagggata tcaaaattgt caatgcg | 867 |

<210> SEQ ID NO 86
<211> LENGTH: 867
<212> TYPE: DNA
<213> ORGANISM: rhinovirus

<400> SEQUENCE: 86

| | |
|---|---|
| aatcctgttg aaaattatgt tgatgaaatt ttaaatcaag ttcttgtagt cccaaacact | 60 |
| gtagaaagtc attcaacaac atccaatgca gcccctgcac ttgatgcagc tgaaactggg | 120 |
| catactagcc aggtgcaacc tgaagacatg gtagagacaa ggtcagtaca taatttccaa | 180 |
| accagagatg aaatgagtat tgaaagtttc ttgggcagat ctggttgcat acatatttca | 240 |
| acacttgaag taaattatga tgattataat gggacaggca taaattttac ccaatggcca | 300 |
| atcaacttgc aagaaatggc acaaattaga agaaagtatg aattgttcac atacttaagg | 360 |
| tttgattctg aaattaccct tgttccttgc attgcagcaa aaagcaatga tataggccat | 420 |
| gtggtaatgc agtacatgta tgtaccacca ggtgcgccaa ttccaaaaac taggaaagat | 480 |
| tatgcatggc aatctggcac aaatgcatct gttttctggc aacatggtca acatttcca | 540 |
| agatttcct taccttttct gagcatagca tcagcatatt acatgtttta tgatggatat | 600 |
| gaaggtgacc aaaaaacatc ccgttatggc acaattgcaa gcaaccacat gggaacatta | 660 |
| tgttctagga tagttacaga agaacaccaa atcaaatcg ataactac caggatatat | 720 |
| cataaagcca agcatatcaa agcttggtgc ccaagaccac ccagagctgt tgaatacaca | 780 |
| cacacacatg tcacaaatta taaaagagaa ggaaaggagg tagaaacagc catagtatct | 840 |
| aggagggata tcaaaattgt caatgct | 867 |

<210> SEQ ID NO 87
<211> LENGTH: 867
<212> TYPE: DNA
<213> ORGANISM: rhinovirus

<400> SEQUENCE: 87

| | |
|---|---|
| aatccagttg aaaattatgt ggatgaaatt ttaaaccaag ttctggtagt tccaaacacc | 60 |
| atggagagcc atccaacaac gtctaatgct gctccagctt tagatgcagc tgaaactggc | 120 |
| cataccagcc atgttcaacc agaagacatg ttagaaacaa ggcaagtaca aaatttccaa | 180 |
| actagagatg agatgagtat tgagagtttc ctaggcagat ctggatgtat tcatatttca | 240 |
| acacttgaga tggattatac aaactataat ggagaaggca aaacttcac tcagtggcca | 300 |
| atcaatctac aggaaatggc tcaaattaga aggaaatatg aattatttac atatcttaga | 360 |
| tttgattcag aggttactct ggtgccatgc attgcagcta aagggaatga cataggccat | 420 |
| gtagtaatgc aatatatgta tgtaccacca ggagcaccaa taccaacaac tagaaaagat | 480 |
| tatgcatggc aatctggaac aaatgcatct gtattttggc aacatggaca acatttcca | 540 |

```
agattttcac taccatttct gagcattgca tcagcatatt acatgtttta tgatggatat    600 gaagggatc aaaatacatc ccgttatggc accattgcta gtaatcacat ggggacactg    660
tgttctagaa tagttacaga agaacatcga aataaagttg aagtaaccac tagaatatat    720
cacaaagcca aacatataaa agcttggtgt ccgaggccgc ccagggctgt gaatacaca    780 tttagacgtg taacaaatta caaaagagat ggacaacaag ttgagattgc tattgagccc    840
agaagagatg ttaagtttgt aaatgca                                         867

<210> SEQ ID NO 88
<211> LENGTH: 867
<212> TYPE: DNA
<213> ORGANISM: rhinovirus

<400> SEQUENCE: 88
aatccagttg aaaattatgt ggatgaaatt ttaaaccaag ttctggtagt tccaaacacc     60
atggagagcc atccaacaac gtctaatgct gctccagctt tagatgcagc tgaaactggc    120
cataccagcc atgttcaacc agaagacatg ttagaaacaa ggcaagtaca aaatttccaa    180
actagagatg agatgagtat tgagagtttc ctaggcagat ctggatgtat tcatatttca    240
acacttgaga tggattatac aaactataat ggagaaggca aaaacttcac tcagtggcca    300
atcaatctac aggaaatggc tcaaattaga aggaaatatg aattatttac atatcttaga    360
tttgattcag aggttactct ggtgccatgc attgcagcta agggaatga cataggccat    420 gtagtaatgc aatatatgta tgtaccacca ggagcaccaa taccaacaac tagaaaagat    480
tatgcatggc aatctggaac aaatgcatct gtattttggc aacatggaca aacatttcca    540
agattttcac taccatttct gagcattgca tcagcatatt acatgtttta tgatggatat    600 gaagggatc aaaatacatc ccgttatggc accattgcta gtaatcacat ggggacactg    660
tgttctagaa tagttacaga agaacatcga aataaagttg aagtaaccac tagaatatat    720
cacaaagcca aacatataaa agcttggtgt ccgaggccgc ccagggctgt gaatacaca    780 tttagacgtg taacaaatta caaaagagat ggacaacaag ttgagattgc tattgagccc    840
agaagagatg ttaagtttgt aaatgcg                                         867

<210> SEQ ID NO 89
<211> LENGTH: 867
<212> TYPE: DNA
<213> ORGANISM: rhinovirus

<400> SEQUENCE: 89
aatccagttg aaaattatgt ggatgaaatt ttaaaccaag ttctggtagt tccaaacacc     60
atggagagcc atccaacaac gtctaatgct gctccagctt tagatgcagc tgaaactggc    120
cataccagcc atgttcaacc agaagacatg ttagaaacaa ggcaagtaca aaatttccaa    180
actagagatg agatgagtat tgagagtttc ctaggcagat ctggatgtat tcatatttca    240
acacttgaga tggattatac aaactataat ggagaaggca aaaacttcac tcagtggcca    300
atcaatctac aggaaatggc tcaaattaga aggaaatatg aattatttac atatcttaga    360
tttgattcag aggttactct ggtgccatgc attgcagcta agggaatga cataggccat    420 gtagtaatgc aatatatgta tgtaccacca ggagcaccaa taccaacaac tagaaaagat    480
tatgcatggc aatctggaac aaatgcatct gtattttggc aacatggaca aacatttcca    540
agattttcac taccatttct gagcattgca tcagcatatt acatgtttta tgatggatat    600
```

| | |
|---|---|
| gaaggggatc aaaatacatc ccgttatggc accattgcta gtaatcacat ggggacactg | 660 |
| tgttctagaa tagttacaga agaacatcga aataaagttg aagtaaccac tagaatatat | 720 |
| cacaaagcca aacatataaa agcttggtgt ccgaggccgc ccagggctgt tgaatacaca | 780 |
| tttagacgtg taacaaatta caaaagagat ggacaacaag ttgagattgc tattgagccc | 840 |
| agaagagatg ttaagtttgt aaatgct | 867 |

<210> SEQ ID NO 90
<211> LENGTH: 867
<212> TYPE: DNA
<213> ORGANISM: rhinovirus

<400> SEQUENCE: 90

| | |
|---|---|
| aatccagtgg agaattacat agatcaggtg cttaatgagg ttttggtagt cccaaacatt | 60 |
| aaagagagca accctacaac ctctaactca gctccagctc tagatgctgc tgagacaggc | 120 |
| catactagca atgttcaacc tgaagacatg attgaaacac gttatgtgca gacatcacaa | 180 |
| accagagatg aaatgagtct tgaaagcttc ttagggagat caggttgtat acacatatct | 240 |
| aaattgaata ttgattacag tgactatgat aagagtgttg aaaatttcac aatctggaaa | 300 |
| ataaatataa aggaaatggc ccagatcagg aggaaatttg aattgtttac atatgcaaga | 360 |
| tttgactctg aaataacatt ggtcccgtgt atagcagcag aaagtgatag cgttggccat | 420 |
| gttgttatgc agtacatgta tgtaccacca ggggcacctt accaaggac tagagatgat | 480 |
| tatgcatggc aatcaggcac aaatgcttcc atcttttggc aacatggaca atcatatccc | 540 |
| agattttcac ttccgttttt gagcattgcc tctgcatatt acatgttcta tgatggttat | 600 |
| gatggtggac cagattctct gtatggaaca attgtaacaa atgatatggg atctttatgt | 660 |
| tcccgtgtag ttactgaaga gcatggaccc cgtgtcaaaa tttcaaccag aatatatcac | 720 |
| aaagccaaac atgttaaagc ctggtgccca agacctccta gggcagttga gtatatacat | 780 |
| acacatgtca caaattacaa gccaagcaca ggcgattatg ccacagttat accagttaga | 840 |
| gacaatgtta gggcagtaaa gaatgtc | 867 |

<210> SEQ ID NO 91
<211> LENGTH: 867
<212> TYPE: DNA
<213> ORGANISM: rhinovirus

<400> SEQUENCE: 91

| | |
|---|---|
| aatccagtgg agaattacat agatcaggtg cttaatgagg ttttggtagt cccaaacatt | 60 |
| aaagagagca accctacaac ctctaactca gctccagctc tagatgctgc tgagacaggc | 120 |
| catactagca atgttcaacc tgaagacatg attgaaacac gttatgtgca gacatcacaa | 180 |
| accagagatg aaatgagtct tgaaagcttc ttagggagat caggttgtat acacatatct | 240 |
| aaattgaata ttgattacag tgactatgat aagagtgttg aaaatttcac aatctggaaa | 300 |
| ataaatataa aggaaatggc ccagatcagg aggaaatttg aattgtttac atatgcaaga | 360 |
| tttgactctg aaataacatt ggtcccgtgt atagcagcag aaagtgatag cgttggccat | 420 |
| gttgttatgc agtacatgta tgtaccacca ggggcacctt accaaggac tagagatgat | 480 |
| tatgcatggc aatcaggcac aaatgcttcc atcttttggc aacatggaca atcatatccc | 540 |
| agattttcac ttccgttttt gagcattgcc tctgcatatt acatgttcta tgatggttat | 600 |
| gatggtggac cagattctct gtatggaaca attgtaacaa atgatatggg atctttatgt | 660 |
| tcccgtgtag ttactgaaga gcatggaccc cgtgtcaaaa tttcaaccag aatatatcac | 720 |

| | |
|---|---|
| aaagccaaac atgttaaagc ctggtgccca agacctccta gggcagttga gtatatacat | 780 |
| acacatgtca caaattacaa gccaagcaca ggcgattatg ccacagttat accagttaga | 840 |
| gacaatgtta gggcagtaaa gaatgtg | 867 |

<210> SEQ ID NO 92
<211> LENGTH: 867
<212> TYPE: DNA
<213> ORGANISM: rhinovirus

<400> SEQUENCE: 92

| | |
|---|---|
| aatccagtgg agaattacat agatcaggtg cttaatgagg ttttggtagt cccaaacatt | 60 |
| aaagagagca accctacaac ctctaactca gctccagctc tagatgctgc tgagacaggc | 120 |
| catactagca atgttcaacc tgaagacatg attgaaacac gttatgtgca gacatcacaa | 180 |
| accagagatg aaatgagtct tgaaagcttc ttagggagat caggttgtat acacatatct | 240 |
| aaattgaata ttgattacag tgactatgat aagagtgttg aaaatttcac aatctggaaa | 300 |
| ataaatataa aggaaatggc ccagatcagg aggaaatttg aattgtttac atatgcaaga | 360 |
| tttgactctg aaataacatt ggtcccgtgt atagcagcag aaagtgatag cgttggccat | 420 |
| gttgttatgc agtacatgta tgtaccacca ggggcacctt taccaaggac tagagatgat | 480 |
| tatgcatggc aatcaggcac aaatgcttcc atcttttggc aacatggaca atcatatccc | 540 |
| agattttcac ttccgttttt gagcattgcc tctgcatatt acatgttcta tgatggttat | 600 |
| gatggtggac cagattctct gtatggaaca attgtaacaa atgatatggg atctttatgt | 660 |
| tcccgtgtag ttactgaaga gcatggaccc cgtgtcaaaa tttcaaccag aatatatcac | 720 |
| aaagccaaac atgttaaagc ctggtgccca agacctccta gggcagttga gtatatacat | 780 |
| acacatgtca caaattacaa gccaagcaca ggcgattatg ccacagttat accagttaga | 840 |
| gacaatgtta gggcagtaaa gaatgta | 867 |

<210> SEQ ID NO 93
<211> LENGTH: 867
<212> TYPE: DNA
<213> ORGANISM: rhinovirus

<400> SEQUENCE: 93

| | |
|---|---|
| aatcctgtgg agaattacat agatcaagtt ttaaatgaag ttttggtagt tccaaacatc | 60 |
| aaagaaagca atcccacaac ctctaattca gccccagcct tagatgctgc cgaaacaggt | 120 |
| cataccagta atgttcaacc tgaagacatg attgaaacac gttatgtgca aacaacacac | 180 |
| actagagatg agatgagtct tgagagcttc ttagggaggt caggatgtgt acatatatcc | 240 |
| aaattagata ttgattatac caattacaat aaaagtgtta agaatttcac aatttggaag | 300 |
| ataaatataa agaaatggc ccagattagg agaaaatttg agttgtttac atacacaagg | 360 |
| tttgattctg aaataacatt agtaccttgt atagctgcag aaagtgacag cattggtcat | 420 |
| gttgttatgc agtacatgta tgtaccacca ggggctcctc taccacaagc aagagatgac | 480 |
| tacacatggc aatctggcac gaatgcatct atcttttggc agcatggaca ggcatatccc | 540 |
| aggttttcac ttccatttct aagtattgcc tctgcatact acatgtttta tgatggttat | 600 |
| gatggtgggc cagattcaca atatggaaca attgtaacaa atgatatggg ttccctgtgt | 660 |
| tctcgtatag tcaccgaaga gcacggatcc cgtgttgata tttcaactag ggtatatcac | 720 |
| aaagctaaac acgtcaaagc ttggtgccca cgaccaccta gggcagttga aatatacat | 780 |

```
acacatgtta caaattacaa accaagcaca ggtgattaca ccacagccat acaaaccaga    840
gagcatgtta gagcagtcaa aaatgta                                       867

<210> SEQ ID NO 94
<211> LENGTH: 867
<212> TYPE: DNA
<213> ORGANISM: rhinovirus

<400> SEQUENCE: 94
aatcctgtgg agaattacat agatcaagtt ttaaatgaag ttttggtagt tccaaacatc     60
aaagaaagca atcccacaac ctctaattca gccccagcct tagatgctgc cgaaacaggt    120
cataccagta atgttcaacc tgaagacatg attgaaacac gttatgtgca acaacacac    180 actagagatg agatgagtct tgagagcttc ttagggaggt caggatgtgt acatatatcc    240
aaattagata ttgattatac caattacaat aaaagtgtta agaatttcac aatttggaag    300
ataaatataa aagaaatggc ccagattagg agaaaatttg agttgtttac atacacaagg    360
tttgattctg aaataacatt agtaccttgt atagctgcag aaagtgacag cattggtcat    420
gttgttatgc agtacatgta tgtaccacca ggggctcctc taccacaagc aagagatgac    480
tacacatggc aatctggcac gaatgcatct atcttttggc agcatggaca ggcatatccc    540
aggttttcac ttccatttct aagtattgcc tctgcatact acatgttta tgatggttat    600 gatggtgggc cagattcaca atatggaaca attgtaacaa atgatatggg ttccctgtgt    660
tctcgtatag tcaccgaaga gcacggatcc cgtgttgata tttcaactag ggtatatcac    720
aaagctaaac acgtcaaagc ttggtgccca cgaccaccta gggcagttga atatacacat    780
acacatgtta caaattacaa accaagcaca ggtgattaca ccacagccat acaaaccaga    840
gagcatgtta gagcagtcaa aaatgtg                                       867

<210> SEQ ID NO 95
<211> LENGTH: 867
<212> TYPE: DNA
<213> ORGANISM: rhinovirus

<400> SEQUENCE: 95
aatcctgtgg agaattacat agatcaagtt ttaaatgaag ttttggtagt tccaaacatc     60
aaagaaagca atcccacaac ctctaattca gccccagcct tagatgctgc cgaaacaggt    120
cataccagta atgttcaacc tgaagacatg attgaaacac gttatgtgca acaacacac    180 actagagatg agatgagtct tgagagcttc ttagggaggt caggatgtgt acatatatcc    240
aaattagata ttgattatac caattacaat aaaagtgtta agaatttcac aatttggaag    300
ataaatataa aagaaatggc ccagattagg agaaaatttg agttgtttac atacacaagg    360
tttgattctg aaataacatt agtaccttgt atagctgcag aaagtgacag cattggtcat    420
gttgttatgc agtacatgta tgtaccacca ggggctcctc taccacaagc aagagatgac    480
tacacatggc aatctggcac gaatgcatct atcttttggc agcatggaca ggcatatccc    540
aggttttcac ttccatttct aagtattgcc tctgcatact acatgttta tgatggttat    600 gatggtgggc cagattcaca atatggaaca attgtaacaa atgatatggg ttccctgtgt    660
tctcgtatag tcaccgaaga gcacggatcc cgtgttgata tttcaactag ggtatatcac    720
aaagctaaac acgtcaaagc ttggtgccca cgaccaccta gggcagttga atatacacat    780
acacatgtta caaattacaa accaagcaca ggtgattaca ccacagccat acaaaccaga    840
gagcatgtta gagcagtcaa aaatgtc                                       867
```

<210> SEQ ID NO 96
<211> LENGTH: 867
<212> TYPE: DNA
<213> ORGANISM: rhinovirus

<400> SEQUENCE: 96

```
aacccagtag aagattatgt agatcaggta ttgaatgagg tcctggtggt gccaaatata      60
aagcaaagtg aacccacgac ttccaattca gccccagctc tagatgctgc tgagacaggt     120
cacactagca gtgtacaacc tgaagatatg atcgagactc gttatgtaca ggcatcaaat     180
accagagatg aaatgagtct cgagagcttt cttggaaggt caggctgtat tcatatatca     240
aaattgaata ttgattataa tgcatatgat gaaagtaggg acaatttcac aatttggaaa     300
ataaatataa aagaaatggc ccagattagg aggaaatttg aactattcac atatacaaga     360
tttgattctg agataacact ggtaccatgc atagctgcag agagtgacag cattgggcat     420
gttgtaatgc aatatatgta tgtacctcca ggagcaccat taccaacaaa aagagatgac     480
tacacatggc aatcaggtac aaatgcatcc atcttttggc aacatggaca atcatacccc     540
agattctcac taccattctt aagtattgcc tctgcttatt acatgtttta tgatggctat     600
gatggtggac cagattcact atatggcacc atagtaacta atgatatggg ttccttgtgt     660
tcgcgtatag ttactgaaga acatggttct cgcgtaaaaa ttgcaacgcg ggtgtatcat     720
aaggctaaac atgtaaaagc ttggtgccca aggcccccta gagcagttga atacatacac     780
acacatgtta caaactatag accagaaaca ggtgaggctc aaacggttat acctgttaga     840
gcagatgtta gaacaattag aaatgta                                         867
```

<210> SEQ ID NO 97
<211> LENGTH: 867
<212> TYPE: DNA
<213> ORGANISM: rhinovirus

<400> SEQUENCE: 97

```
aacccagtag aagattatgt agatcaggta ttgaatgagg tcctggtggt gccaaatata      60
aagcaaagtg aacccacgac ttccaattca gccccagctc tagatgctgc tgagacaggt     120
cacactagca gtgtacaacc tgaagatatg atcgagactc gttatgtaca ggcatcaaat     180
accagagatg aaatgagtct cgagagcttt cttggaaggt caggctgtat tcatatatca     240
aaattgaata ttgattataa tgcatatgat gaaagtaggg acaatttcac aatttggaaa     300
ataaatataa aagaaatggc ccagattagg aggaaatttg aactattcac atatacaaga     360
tttgattctg agataacact ggtaccatgc atagctgcag agagtgacag cattgggcat     420
gttgtaatgc aatatatgta tgtacctcca ggagcaccat taccaacaaa aagagatgac     480
tacacatggc aatcaggtac aaatgcatcc atcttttggc aacatggaca atcatacccc     540
agattctcac taccattctt aagtattgcc tctgcttatt acatgtttta tgatggctat     600
gatggtggac cagattcact atatggcacc atagtaacta atgatatggg ttccttgtgt     660
tcgcgtatag ttactgaaga acatggttct cgcgtaaaaa ttgcaacgcg ggtgtatcat     720
aaggctaaac atgtaaaagc ttggtgccca aggcccccta gagcagttga atacatacac     780
acacatgtta caaactatag accagaaaca ggtgaggctc aaacggttat acctgttaga     840
gcagatgtta gaacaattag aaatgtc                                         867
```

<210> SEQ ID NO 98

```
<211> LENGTH: 867
<212> TYPE: DNA
<213> ORGANISM: rhinovirus

<400> SEQUENCE: 98
aacccagtag aagattatgt agatcaggta ttgaatgagg tcctggtggt gccaaatata    60
aagcaaagtg aacccacgac ttccaattca gccccagctc tagatgctgc tgagacaggt   120
cacactagca gtgtacaacc tgaagatatg atcgagactc gttatgtaca ggcatcaaat   180
accagagatg aaatgagtct cgagagcttt cttggaaggt caggctgtat tcatatatca   240
aaattgaata ttgattataa tgcatatgat gaaagtaggg acaatttcac aatttggaaa   300
ataaatataa aagaaatggc ccagattagg aggaaatttg aactattcac atatacaaga   360
tttgattctg agataacact ggtaccatgc atagctgcag agagtgacag cattgggcat   420
gttgtaatgc aatatatgta tgtacctcca ggagcaccat taccaacaaa aagagatgac   480
tacacatggc aatcaggtac aaatgcatcc atcttttggc aacatggaca atcatacccc   540
agattctcac taccattctt aagtattgcc tctgcttatt acatgtttta tgatggctat   600
gatggtggac cagattcact atatggcacc atagtaacta atgatatggg ttccttgtgt   660
tcgcgtatag ttactgaaga acatggttct cgcgtaaaaa ttgcaacgcg ggtgtatcat   720
aaggctaaac atgtaaaagc ttggtgccca aggccccta gagcagttga atacatacac   780
acacatgtta caaactatag accagaaaca ggtgaggctc aaacggttat acctgttaga   840
gcagatgtta gaacaattag aaatgtt                                      867

<210> SEQ ID NO 99
<211> LENGTH: 870
<212> TYPE: DNA
<213> ORGANISM: rhinovirus

<400> SEQUENCE: 99
aacccagtgg agaattacat agatgaagtg ttaaatgagg ttctagtagt tccaaacatt    60
aaggagagtc actcaagcac atccaactca gcaccagcac tagatgcagc tgagaccggc   120
catactagca gtgttcaacc tgaggatatg attgaaactc gttacgtcca acatcacag    180
accagagatg aaatgagtat tgagagcttc cttggtagat cagggtgtgt ccatatttct   240
gatttgaaaa tacattatga agattataat aaagatggga aaaactttac taaatggcaa   300
attaatctca agaaatggc ccagattaga aggaaatttg agttattcac atatgtaagg   360
tttgattcag aaataacact tgtaccatgc attgcagcaa agagtgataa catcggtcat   420
gttgtcatgc aatatatgta tgttcctccg ggagcccctt tacccaataa aggaatgat   480
tacacatggc aatcaggtac aaatgcctct gtttctggc aacatggtca accttacccc   540
agattttctt tgccttttct cagcattgca tctgcttact acatgttcta tgatggatat   600
gatggagatt ccactgaatc acattatggt acagtggtca ctaatgacat ggggacactg   660
tgttctagaa tagtaactga gagcatggg acacgtgtag agattacaac tagagtgtat   720
cacaaagcta acatgtaaa ggcttggtgc cccagacccc ctagagcagt ggaatataca   780
cacacacatg tcacaaatta caaaccacaa gatggtgatg taactacagt tattccaact   840
agagaaaatg ttagagctat agtaaatgtt                                   870

<210> SEQ ID NO 100
<211> LENGTH: 870
<212> TYPE: DNA
<213> ORGANISM: rhinovirus
```

<400> SEQUENCE: 100

```
aacccagtgg agaattacat agatgaagtg ttaaatgagg ttctagtagt tccaaacatt      60
aaggagagtc actcaagcac atccaactca gcaccagcac tagatgcagc tgagaccggc     120
catactagca gtgttcaacc tgaggatatg attgaaactc gttacgtcca acatcacag     180
accagagatg aaatgagtat tgagagcttc cttggtagat cagggtgtgt ccatatttct     240
gatttgaaaa tacattatga agattataat aaagatggga aaaactttac taaatggcaa     300
attaatctca aagaaatggc ccagattaga aggaaatttg agttattcac atatgtaagg     360
tttgattcag aaataacact tgtaccatgc attgcagcaa agagtgataa catcggtcat     420
gttgtcatgc aatatatgta tgttcctccg ggagcccctt acccaataa aaggaatgat     480
tacacatggc aatcaggtac aaatgcctct gttttctggc aacatggtca accttacccc     540
agatttctt tgcctttct cagcattgca tctgcttact acatgttcta tgatggatat     600
gatggagatt ccactgaatc acattatggt acagtggtca ctaatgacat ggggacactg     660
tgttctagaa tagtaactga agagcatggg acacgtgtag agattacaac tagagtgtat     720
cacaaagcta acatgtaaa ggcttggtgc cccagacccc ctagagcagt ggaatataca     780
cacacacatg tcacaaatta caaaccacaa gatggtgatg taactacagt tattccaact     840
agagaaaatg ttagagctat agtaaatgta                                      870
```

<210> SEQ ID NO 101
<211> LENGTH: 870
<212> TYPE: DNA
<213> ORGANISM: rhinovirus

<400> SEQUENCE: 101

```
aacccagtgg agaattacat agatgaagtg ttaaatgagg ttctagtagt tccaaacatt      60
aaggagagtc actcaagcac atccaactca gcaccagcac tagatgcagc tgagaccggc     120
catactagca gtgttcaacc tgaggatatg attgaaactc gttacgtcca acatcacag     180
accagagatg aaatgagtat tgagagcttc cttggtagat cagggtgtgt ccatatttct     240
gatttgaaaa tacattatga agattataat aaagatggga aaaactttac taaatggcaa     300
attaatctca aagaaatggc ccagattaga aggaaatttg agttattcac atatgtaagg     360
tttgattcag aaataacact tgtaccatgc attgcagcaa agagtgataa catcggtcat     420
gttgtcatgc aatatatgta tgttcctccg ggagcccctt acccaataa aaggaatgat     480
tacacatggc aatcaggtac aaatgcctct gttttctggc aacatggtca accttacccc     540
agatttctt tgcctttct cagcattgca tctgcttact acatgttcta tgatggatat     600
gatggagatt ccactgaatc acattatggt acagtggtca ctaatgacat ggggacactg     660
tgttctagaa tagtaactga agagcatggg acacgtgtag agattacaac tagagtgtat     720
cacaaagcta acatgtaaa ggcttggtgc cccagacccc ctagagcagt ggaatataca     780
cacacacatg tcacaaatta caaaccacaa gatggtgatg taactacagt tattccaact     840
agagaaaatg ttagagctat agtaaatgtc                                      870
```

<210> SEQ ID NO 102
<211> LENGTH: 861
<212> TYPE: DNA
<213> ORGANISM: rhinovirus

<400> SEQUENCE: 102

| aacccagtgg agaattacat agatgaagtg ttgaatgaag tgttagttgt tccaaatatt | 60 |
| agagaaagcc attcaagtac ttcaaactca gcaccagcac tggatgcagc tgaaactggc | 120 |
| cataccagta atgtgcaacc agaagatatg gttgagacac gctatgtgca aacctcacag | 180 |
| acaagagatg agatgagtgt agaaagtttt cttggaagat caggatgcat ccatatctca | 240 |
| catctaaaaa ttgattatac aaactataat gttaaaggga agaattttac taaatggcaa | 300 |
| ataaatctta agaaatggc acagattagg agaaaatttg agttgttcac atatgttaga | 360 |
| tttgactcag aagtgacatt agttccatgc attgctgcta aaagtgacaa cattggccat | 420 |
| gttgttatgc aatacatgta tgtccccca ggagcacctt tacccaagaa aagagatgat | 480 |
| tacacatggc aatctggcac aaatgcatct gtgttttggc agcatggaca gccataccct | 540 |
| agattctcat taccttcct tagcatagca tctgcttatt acatgtttta tgatggatat | 600 |
| gatggagact ctactgaatc acattatggt acagtagtaa caaatgacat gggaactcta | 660 |
| tgttctagaa ttgtgactga agaacacgat gcacgtgtgg aaattacaac tagagtgtac | 720 |
| cataaagcaa agcatgtgaa ggcatggtgt cctagaccc ctagagcagt tgaatatact | 780 |
| cacacacatg tcacaaatta caaaccacaa gaaggtgacg taactacagt catcccaact | 840 |
| aggagatcaa tagtgaatgt a | 861 |

<210> SEQ ID NO 103
<211> LENGTH: 861
<212> TYPE: DNA
<213> ORGANISM: rhinovirus

<400> SEQUENCE: 103

| aacccagtgg agaattacat agatgaagtg ttgaatgaag tgttagttgt tccaaatatt | 60 |
| agagaaagcc attcaagtac ttcaaactca gcaccagcac tggatgcagc tgaaactggc | 120 |
| cataccagta atgtgcaacc agaagatatg gttgagacac gctatgtgca aacctcacag | 180 |
| acaagagatg agatgagtgt agaaagtttt cttggaagat caggatgcat ccatatctca | 240 |
| catctaaaaa ttgattatac aaactataat gttaaaggga agaattttac taaatggcaa | 300 |
| ataaatctta agaaatggc acagattagg agaaaatttg agttgttcac atatgttaga | 360 |
| tttgactcag aagtgacatt agttccatgc attgctgcta aaagtgacaa cattggccat | 420 |
| gttgttatgc aatacatgta tgtccccca ggagcacctt tacccaagaa aagagatgat | 480 |
| tacacatggc aatctggcac aaatgcatct gtgttttggc agcatggaca gccataccct | 540 |
| agattctcat taccttcct tagcatagca tctgcttatt acatgtttta tgatggatat | 600 |
| gatggagact ctactgaatc acattatggt acagtagtaa caaatgacat gggaactcta | 660 |
| tgttctagaa ttgtgactga agaacacgat gcacgtgtgg aaattacaac tagagtgtac | 720 |
| cataaagcaa agcatgtgaa ggcatggtgt cctagaccc ctagagcagt tgaatatact | 780 |
| cacacacatg tcacaaatta caaaccacaa gaaggtgacg taactacagt catcccaact | 840 |
| aggagatcaa tagtgaatgt c | 861 |

<210> SEQ ID NO 104
<211> LENGTH: 861
<212> TYPE: DNA
<213> ORGANISM: rhinovirus

<400> SEQUENCE: 104

| aacccagtgg agaattacat agatgaagtg ttgaatgaag tgttagttgt tccaaatatt | 60 |
| agagaaagcc attcaagtac ttcaaactca gcaccagcac tggatgcagc tgaaactggc | 120 |

| | |
|---|---|
| cataccagta atgtgcaacc agaagatatg gttgagacac gctatgtgca aacctcacag | 180 |
| acaagagatg agatgagtgt agaaagtttt cttggaagat caggatgcat ccatatctca | 240 |
| catctaaaaa ttgattatac aaactataat gttaaaggga agaattttac taaatggcaa | 300 |
| ataaatctta agaaatggc acagattagg agaaaatttg agttgttcac atatgttaga | 360 |
| tttgactcag aagtgacatt agttccatgc attgctgcta aaagtgacaa cattggccat | 420 |
| gttgttatgc aatacatgta tgtcccccca ggagcacctt acccaagaa aagagatgat | 480 |
| tacacatggc aatctggcac aaatgcatct gtgttttggc agcatggaca gccatacccct | 540 |
| agattctcat tacctttcct tagcatagca tctgcttatt acatgtttta tgatggatat | 600 |
| gatggagact ctactgaatc acattatggt acagtagtaa caaatgacat ggaactcta | 660 |
| tgttctagaa ttgtgactga agaacacgat gcacgtgtgg aaattacaac tagagtgtac | 720 |
| cataaagcaa agcatgtgaa ggcatggtgt cctagacccc ctagagcagt tgaatatact | 780 |
| cacacacatg tcacaaatta caaaccacaa gaaggtgacg taactacagt catcccaact | 840 |
| aggagatcaa tagtgaatgt t | 861 |

<210> SEQ ID NO 105
<211> LENGTH: 870
<212> TYPE: DNA
<213> ORGANISM: rhinovirus

<400> SEQUENCE: 105

| | |
|---|---|
| aacccagtag aggaatacat agatggagtc ttgaatgagg ttcttgtggt tccgaacatt | 60 |
| aaggaaagcc actccagcac atcaaattca gcaccagcat tagatgctgc tgagactgga | 120 |
| cacaccagta atgtgcagcc tgaggatatg attgaaactc gctatgtaca gacatcacaa | 180 |
| actagagatg aaatgagtgt agaaagtttt ctaggaagat caggttgtgt acatatatcc | 240 |
| aatcttgaca tagattacat taattacaac tctgaagaca aaaactttac aacatggcaa | 300 |
| atcaatctca agaaatggc tcaaatcaga agaaagtttg aaatgtttac atatgtgaga | 360 |
| tttgattcag aagttacatt agtcccatgt atagcagcac aaaatgaagg tgtgggcat | 420 |
| gttgttatgc agtatatgta tgtccctcca ggggcaccat acccaggaa gagagatgat | 480 |
| tacacttggc aatctggtac aaatgcctct gtttctggc aatatggtca gacatatcct | 540 |
| cgatttttcct tacctttctt aagcattgca tctgtctatt atatgtttta tgatggatat | 600 |
| gatgggact caacagaatc acattatggg acagcggtga ccaatgatat ggggacactt | 660 |
| tgttcaagaa tagtcactga aaatcatggg acccaagtga agataacaac tagaatttat | 720 |
| cataaggcaa aacatgtaaa agcctggtgt ccaagacccc caagggcagt tgaatataga | 780 |
| catacacatg ttaacaatta caaaccagac caaggggaag taaccactat gattccaact | 840 |
| agaaccaaca taagaaccat cgtaaatgta | 870 |

<210> SEQ ID NO 106
<211> LENGTH: 870
<212> TYPE: DNA
<213> ORGANISM: rhinovirus

<400> SEQUENCE: 106

| | |
|---|---|
| aacccagtag aggaatacat agatggagtc ttgaatgagg ttcttgtggt tccgaacatt | 60 |
| aaggaaagcc actccagcac atcaaattca gcaccagcat tagatgctgc tgagactgga | 120 |
| cacaccagta atgtgcagcc tgaggatatg attgaaactc gctatgtaca gacatcacaa | 180 |

```
actagagatg aaatgagtgt agaaagtttt ctaggaagat caggttgtgt acatatatcc    240
aatcttgaca tagattacat taattacaac tctgaagaca aaaactttac aacatggcaa    300
atcaatctca aagaaatggc tcaaatcaga agaaagtttg aatgtttac atatgtgaga     360 tttgattcag aagttacatt agtcccatgt atagcagcac aaaatgaagg tgtggggcat    420
gttgttatgc agtatatgta tgtccctcca ggggcaccat acccaggaa gagagatgat     480 tacacttggc aatctggtac aaatgcctct gttttctggc aatatggtca gacatatcct    540 cgatttcct tacctttctt aagcattgca tctgtctatt atatgtttta tgatggatat      600 gatgggact caacagaatc acattatggg acagcggtga ccaatgatat ggggacactt     660
tgttcaagaa tagtcactga aaatcatggg acccaagtga agataacaac tagaatttat     720
cataaggcaa aacatgtaaa agcctggtgt ccaagacccc caagggcagt tgaatataga    780
catacacatg ttaacaatta caaaccagac caaggggaag taaccactat gattccaact    840
agaaccaaca taagaaccat cgtaaatgtc                                      870

<210> SEQ ID NO 107
<211> LENGTH: 870
<212> TYPE: DNA
<213> ORGANISM: rhinovirus

<400> SEQUENCE: 107
aacccagtag aggaatacat agatggagtc ttgaatgagg ttcttgtggt tccgaacatt    60
aaggaaagcc actccagcac atcaaattca gcaccagcat tagatgctgc tgagactgga    120
cacaccagta atgtgcagcc tgaggatatg attgaaactc gctatgtaca gacatcacaa    180
actagagatg aaatgagtgt agaaagtttt ctaggaagat caggttgtgt acatatatcc    240
aatcttgaca tagattacat taattacaac tctgaagaca aaaactttac aacatggcaa    300
atcaatctca aagaaatggc tcaaatcaga agaaagtttg aatgtttac atatgtgaga     360 tttgattcag aagttacatt agtcccatgt atagcagcac aaaatgaagg tgtggggcat    420
gttgttatgc agtatatgta tgtccctcca ggggcaccat acccaggaa gagagatgat     480 tacacttggc aatctggtac aaatgcctct gttttctggc aatatggtca gacatatcct    540 cgatttcct tacctttctt aagcattgca tctgtctatt atatgtttta tgatggatat      600 gatgggact caacagaatc acattatggg acagcggtga ccaatgatat ggggacactt     660
tgttcaagaa tagtcactga aaatcatggg acccaagtga agataacaac tagaatttat     720
cataaggcaa aacatgtaaa agcctggtgt ccaagacccc caagggcagt tgaatataga    780
catacacatg ttaacaatta caaaccagac caaggggaag taaccactat gattccaact    840
agaaccaaca taagaaccat cgtaaatgtt                                      870

<210> SEQ ID NO 108
<211> LENGTH: 870
<212> TYPE: DNA
<213> ORGANISM: rhinovirus

<400> SEQUENCE: 108
aatccagtag aaagctacat agatggggtc ttaaacgaag tccttgtggt tccaaacatt    60
agggagagcc aacccactac ttctaattct gctccagcat tggatgctgc tgagactggt    120
cacactagta atgtacagcc tgaggacgtg attgaaacac gttatgtgca gattacacaa    180
actagagatg agatgagtgt tgagagcttc ctcggcagat ctggatgtat tcatatttcc    240
aaattagaaa ttgactatag taactacaat gaggagaata aaaatttcac aacttggcaa    300
```

```
attaaccutaa aggaaatggc acaaataaga agaaagtttg aattatttac atatgtaaga      360
tttgattcag aattgactct ggtcccatgc atagcagcaa aaaatgatgg cataggtcat      420
gttgtcatgc aatacatgta tgtcccccca ggagcaccat tacctactaa aagagacgat      480
tacacatggc aatctggcac aaatgcttct gtattttggc agcatggaca aacataccct      540
agattttcac ttccatttct aagtattgca tctgcctact acatgtttta tgatggttat      600
gatggtcact caactgaatc acattatggg acggttgtga ccaatgacat gggaacgttg      660
tgctccagaa tagttactga acaccatggt acacaggttc acgtcgcaac aagaatatat      720
cataaagcaa agcatgttaa ggcttggtgt ccaagacctc caagggcagt tgaatataga      780
cacacacatg taaacaacta tagaccagat gatggagaag cagccataac aatccccatt      840
agaactgata tacgagcaat cagaacagtt                                       870

<210> SEQ ID NO 109
<211> LENGTH: 870
<212> TYPE: DNA
<213> ORGANISM: rhinovirus

<400> SEQUENCE: 109
aatccagtag aaagctacat agatggggtc ttaaacgaag tccttgtggt tccaaacatt       60
agggagagcc aacccactac ttctaattct gctccagcat tggatgctgc tgagactggt      120
cacactagta atgtacagcc tgaggacgtg attgaaacac gttatgtgca gattacacaa      180
actagagatg agatgagtgt tgagagcttc ctcggcagat ctggatgtat tcatatttcc      240
aaattagaaa ttgactatag taactacaat gaggagaata aaaatttcac aacttggcaa      300 attaaccutaa aggaaatggc acaaataaga agaaagtttg aattatttac atatgtaaga      360
tttgattcag aattgactct ggtcccatgc atagcagcaa aaaatgatgg cataggtcat      420
gttgtcatgc aatacatgta tgtcccccca ggagcaccat tacctactaa aagagacgat      480
tacacatggc aatctggcac aaatgcttct gtattttggc agcatggaca aacataccct      540
agattttcac ttccatttct aagtattgca tctgcctact acatgtttta tgatggttat      600
gatggtcact caactgaatc acattatggg acggttgtga ccaatgacat gggaacgttg      660
tgctccagaa tagttactga acaccatggt acacaggttc acgtcgcaac aagaatatat      720
cataaagcaa agcatgttaa ggcttggtgt ccaagacctc caagggcagt tgaatataga      780
cacacacatg taaacaacta tagaccagat gatggagaag cagccataac aatccccatt      840
agaactgata tacgagcaat cagaacagta                                       870

<210> SEQ ID NO 110
<211> LENGTH: 870
<212> TYPE: DNA
<213> ORGANISM: rhinovirus

<400> SEQUENCE: 110
aatccagtag aaagctacat agatggggtc ttaaacgaag tccttgtggt tccaaacatt       60
agggagagcc aacccactac ttctaattct gctccagcat tggatgctgc tgagactggt      120
cacactagta atgtacagcc tgaggacgtg attgaaacac gttatgtgca gattacacaa      180
actagagatg agatgagtgt tgagagcttc ctcggcagat ctggatgtat tcatatttcc      240
aaattagaaa ttgactatag taactacaat gaggagaata aaaatttcac aacttggcaa      300 attaaccutaa aggaaatggc acaaataaga agaaagtttg aattatttac atatgtaaga      360
```

```
tttgattcag aattgactct ggtcccatgc atagcagcaa aaaatgatgg cataggtcat    420
gttgtcatgc aatacatgta tgtcccccca ggagcaccat tacctactaa aagagacgat    480
tacacatggc aatctggcac aaatgcttct gtattttggc agcatggaca acatacccct    540
agattttcac ttccatttct aagtattgca tctgcctact acatgtttta tgatggttat    600
gatggtcact caactgaatc acattatggg acggttgtga ccaatgacat gggaacgttg    660
tgctccagaa tagttactga acaccatggt acacaggttc acgtcgcaac aagaatatat    720
cataaagcaa agcatgttaa ggcttggtgt ccaagacctc caagggcagt tgaatataga    780
cacacacatg taaacaacta tagaccagat gatggagaag cagccataac aatccccatt    840
agaactgata tacgagcaat cagaacagtg                                     870

<210> SEQ ID NO 111
<211> LENGTH: 867
<212> TYPE: DNA
<213> ORGANISM: rhinovirus

<400> SEQUENCE: 111
aacccagttg aacaatacat tgatggtgtg ttgaatgaag ttttgattgt cccaaacatc     60
aatgagagcc atcccagcac ttccaatgca gcgccagctt tagatgcagc tgagaccgga    120
cacaccagta atgtacagcc tgaagatatg attgaaacgc gctatgtaca aaacactcaa    180
actagagatg aaatgagcat tgagagtttc ttgggcaggt ctggttgtat acacatatca    240
gatttaaaag taaattatac tgggtataat gatgaaggta acaattttaa caaatggcag    300
atcaccttga agaaatggc tcagataaga aggaagtatg aattatttac atatgttaga    360
tttgattctg aaataacctt agtgccttgc atatcttctc agagtgctaa cattggtcat    420
gttgttatgc aatatatgta tgtccctcct ggagctccaa taccaaccaa aagaaatgat    480
tacgtctggc agtcaggcac caatgcatcc atcttttggc aacacggtca accatacccct   540 cgattttctc tcccttcct tagcatagcc tcagcatatt acatgtttta tgatggttat    600
gacggtggac ctggttcccg ttatggcgca gtggtgacaa atgatatggg cactttgtgt    660
tctagaattg tgactgagga acacacaaca caggtcaaca tcactactag ggtttatcac    720
aaagcaaaac atgtcaaggc atggtgtcca cggcccccaa gagctgttgg atatacacat    780
acaaatgtca ccaattataa accatccaaa ggagaataca caccacccgt tccgtcacgt    840
aacagcccca gagatattgt cacagtg                                        867

<210> SEQ ID NO 112
<211> LENGTH: 867
<212> TYPE: DNA
<213> ORGANISM: rhinovirus

<400> SEQUENCE: 112
aacccagttg aacaatacat tgatggtgtg ttgaatgaag ttttgattgt cccaaacatc     60
aatgagagcc atcccagcac ttccaatgca gcgccagctt tagatgcagc tgagaccgga    120
cacaccagta atgtacagcc tgaagatatg attgaaacgc gctatgtaca aaacactcaa    180
actagagatg aaatgagcat tgagagtttc ttgggcaggt ctggttgtat acacatatca    240
gatttaaaag taaattatac tgggtataat gatgaaggta acaattttaa caaatggcag    300
atcaccttga agaaatggc tcagataaga aggaagtatg aattatttac atatgttaga    360
tttgattctg aaataacctt agtgccttgc atatcttctc agagtgctaa cattggtcat    420
gttgttatgc aatatatgta tgtccctcct ggagctccaa taccaaccaa aagaaatgat    480
```

```
tacgtctggc agtcaggcac caatgcatcc atcttttggc aacacggtca accatacect    540
cgatttctc tcccttcct  tagcatagcc tcagcatatt acatgtttta tgatggttat    600
gacggtggac ctggttccg ttatggcgca gtggtgacaa atgatatggg cactttgtgt    660
tctagaattg tgactgagga acacacaaca caggtcaaca tcactactag ggtttatcac    720
aaagcaaaac atgtcaaggc atggtgtcca cggcccccaa gagctgttgg atatacacat    780
acaaatgtca ccaattataa accatccaaa ggagaataca caccacccgt tccgtcacgt    840
aacagcccca gagatattgt cacagtg                                        867

<210> SEQ ID NO 113
<211> LENGTH: 867
<212> TYPE: DNA
<213> ORGANISM: rhinovirus

<400> SEQUENCE: 113
aacccagttg aacaatacat tgatggtgtg ttgaatgaag ttttgattgt cccaaacatc     60
aatgagagcc atcccagcac ttccaatgca gcgccagctt tagatgcagc tgagaccgga    120
cacaccagta atgtacagcc tgaagatatg attgaaacgc gctatgtaca aaacactcaa    180
actagagatg aaatgagcat tgagagtttc ttgggcaggt ctggttgtat acacatatca    240
gatttaaaag taaattatac tgggtataat gatgaaggta acaattttaa caaatggcag    300
atcaccttga agaaatggc tcagataaga aggaagtatg aattatttac atatgttaga    360
tttgattctg aaataacctt agtgccttgc atatcttctc agagtgctaa cattggtcat    420
gttgttatgc aatatatgta tgtccctcct ggagctccaa taccaaccaa agaaatgat    480
tacgtctggc agtcaggcac caatgcatcc atcttttggc aacacggtca accatacect    540
cgatttctc tcccttcct  tagcatagcc tcagcatatt acatgtttta tgatggttat    600
gacggtggac ctggttccg ttatggcgca gtggtgacaa atgatatggg cactttgtgt    660
tctagaattg tgactgagga acacacaaca caggtcaaca tcactactag ggtttatcac    720
aaagcaaaac atgtcaaggc atggtgtcca cggcccccaa gagctgttgg atatacacat    780
acaaatgtca ccaattataa accatccaaa ggagaataca caccacccgt tccgtcacgt    840
aacagcccca gagatattgt cacagta                                        867

<210> SEQ ID NO 114
<211> LENGTH: 867
<212> TYPE: DNA
<213> ORGANISM: rhinovirus

<400> SEQUENCE: 114
aatccagttg agaaatacat tgatggtgta ttgaatgaag ttttagttgt tccaaatatc     60
aatgagagtc accctagcac atccaatgca gcgccagcct tagatgctgc cgaaactgga    120
cacacaagca atgtacaacc tgaggatatg attgaaacac gctatgtaca aaacactcaa    180
acaagggatg aaatgagcat tgaaagcttc ttgggaagat ctggctgtat acacatagca    240
catctagaga tcaagtatga tggttacaat gatgctggca acaatttcca atcatggcaa    300
attacccctaa agaaatggc acaaataaga aggaaatttg aactatttac ttatgttaga    360
tttgattcag aaataacttt agtaccttgc atatcatctc aaagtgctaa tattggtcat    420
gttgtcatgc agtacatgta tgttcctcct ggagctccaa aaccagacaa aagagatgat    480
tatgtttggc aatcaggaac taatgcatct atattctgga acatggtca accctaccct    540
```

```
cgattctcac ttccatttct tagtatagcc tcagcatatt acatgttcta tgatggttat    600
gatggtggac ctggctcacg ctatggcaca gtggtgacaa atgacatggg aacattatgc    660
tccaggattg tgactgagga gcacaagaca caggttaaca tcactactag agtgtaccac    720
aaagcaaaac atgtgaaagc gtggtgcccg cgccctccaa gagctgttgg atacacacat    780
acgcatgtca ctaattacaa accatctgaa ggggagtaca agccacctgt cccagttagg    840
aatagcccca gagacattgt cacagtg                                        867

<210> SEQ ID NO 115
<211> LENGTH: 867
<212> TYPE: DNA
<213> ORGANISM: rhinovirus

<400> SEQUENCE: 115
aatccagttg agaaatacat tgatggtgta ttgaatgaag ttttagttgt tccaaatatc     60
aatgagagtc accctagcac atccaatgca gcgccagcct tagatgctgc cgaaactgga    120
cacacaagca atgtacaacc tgaggatatg attgaaacac gctatgtaca aaacactcaa    180
acaagggatg aaatgagcat tgaaagcttc ttgggaagat ctggctgtat acacatagca    240
catctagaga tcaagtatga tggttacaat gatgctggca acaatttcca atcatggcaa    300 attacccctaa agaaatggc acaaataaga aggaaatttg aactatttac ttatgttaga    360
tttgattcag aaataacttt agtaccttgc atatcatctc aaagtgctaa tattggtcat    420
gttgtcatgc agtacatgta tgttcctcct ggagctccaa accagacaa aagagatgat    480 tatgtttggc aatcaggaac taatgcatct atattctggc aacatggtca accctaccct    540
cgattctcac ttccatttct tagtatagcc tcagcatatt acatgttcta tgatggttat    600
gatggtggac ctggctcacg ctatggcaca gtggtgacaa atgacatggg aacattatgc    660
tccaggattg tgactgagga gcacaagaca caggttaaca tcactactag agtgtaccac    720
aaagcaaaac atgtgaaagc gtggtgcccg cgccctccaa gagctgttgg atacacacat    780
acgcatgtca ctaattacaa accatctgaa ggggagtaca agccacctgt cccagttagg    840
aatagcccca gagacattgt cacagtc                                        867

<210> SEQ ID NO 116
<211> LENGTH: 867
<212> TYPE: DNA
<213> ORGANISM: rhinovirus

<400> SEQUENCE: 116
aatccagttg agaaatacat tgatggtgta ttgaatgaag ttttagttgt tccaaatatc     60
aatgagagtc accctagcac atccaatgca gcgccagcct tagatgctgc cgaaactgga    120
cacacaagca atgtacaacc tgaggatatg attgaaacac gctatgtaca aaacactcaa    180
acaagggatg aaatgagcat tgaaagcttc ttgggaagat ctggctgtat acacatagca    240
catctagaga tcaagtatga tggttacaat gatgctggca acaatttcca atcatggcaa    300 attacccctaa agaaatggc acaaataaga aggaaatttg aactatttac ttatgttaga    360
tttgattcag aaataacttt agtaccttgc atatcatctc aaagtgctaa tattggtcat    420
gttgtcatgc agtacatgta tgttcctcct ggagctccaa accagacaa aagagatgat    480 tatgtttggc aatcaggaac taatgcatct atattctggc aacatggtca accctaccct    540
cgattctcac ttccatttct tagtatagcc tcagcatatt acatgttcta tgatggttat    600
gatggtggac ctggctcacg ctatggcaca gtggtgacaa atgacatggg aacattatgc    660
```

```
tccaggattg tgactgagga gcacaagaca caggttaaca tcactactag agtgtaccac    720
aaagcaaaac atgtgaaagc gtggtgcccg cgccctccaa gagctgttgg atacacacat    780
acgcatgtca ctaattacaa accatctgaa ggggagtaca agccacctgt cccagttagg    840
aatagcccca gagacattgt cacagta                                        867
```

<210> SEQ ID NO 117
<211> LENGTH: 867
<212> TYPE: DNA
<213> ORGANISM: rhinovirus

<400> SEQUENCE: 117

```
aaccctgtag agaaatacat tgatggtgta ttgaatgaag tattggttgt tccaaacaca     60
aatgaaagtc accccagtac atcaaatgct gcaccagcac tagatgctgc tgaaactgga    120
cacacaagca atgtgcagcc agaagacatg atagaaacac gctatgtgtt aaattcacaa    180
actagagatg aaatgagtat tgagagcttc ctgggaagat ctggttgcat acatatatca    240
cacttagaag taaatacac agggtataat gaagagggta ataactttaa catatggcaa    300 attaaccttta aagagatggc tcagataaga aggaagtttg agctatttac atatctcagg    360
tttgattctg aaatcacttt ggtaccatgc attgcttcac aaagtaaaaa cattggtcat    420
gtggtcatgc aatacatgta tgttccgcct ggagctccta aacctgaaaa gagagatgac    480
tacacatggc aatctggcac taatgcatct gttttctggc agcatggtca accttatccc    540
cgattctcac tccctttcct cagtgtagct tcagcatatt acatgtttta tgatgggtat    600
gatggaggtc ccggatcacg ttatggagca gtggtaacaa atgatatggg cacactgtgc    660
tctaggattg tgactgaaga acaccagaca caagtcaaaa ttacaactag agtgtaccac    720
aaagcaaaac atgtaaaggc atggtgccca cgtcctccaa gagctgttgg atatacacac    780
acacatgtga caaactacaa accatctgta ggggattaca cactacctat cccaacaaga    840
gccaacccta gacaaatttt gaatgta                                        867
```

<210> SEQ ID NO 118
<211> LENGTH: 867
<212> TYPE: DNA
<213> ORGANISM: rhinovirus

<400> SEQUENCE: 118

```
aaccctgtag agaaatacat tgatggtgta ttgaatgaag tattggttgt tccaaacaca     60
aatgaaagtc accccagtac atcaaatgct gcaccagcac tagatgctgc tgaaactgga    120
cacacaagca atgtgcagcc agaagacatg atagaaacac gctatgtgtt aaattcacaa    180
actagagatg aaatgagtat tgagagcttc ctgggaagat ctggttgcat acatatatca    240
cacttagaag taaatacac agggtataat gaagagggta ataactttaa catatggcaa    300 attaaccttta aagagatggc tcagataaga aggaagtttg agctatttac atatctcagg    360
tttgattctg aaatcacttt ggtaccatgc attgcttcac aaagtaaaaa cattggtcat    420
gtggtcatgc aatacatgta tgttccgcct ggagctccta aacctgaaaa gagagatgac    480
tacacatggc aatctggcac taatgcatct gttttctggc agcatggtca accttatccc    540
cgattctcac tccctttcct cagtgtagct tcagcatatt acatgtttta tgatgggtat    600
gatggaggtc ccggatcacg ttatggagca gtggtaacaa atgatatggg cacactgtgc    660
tctaggattg tgactgaaga acaccagaca caagtcaaaa ttacaactag agtgtaccac    720
```

```
aaagcaaaac atgtaaaggc atggtgccca cgtcctccaa gagctgttgg atatacacac    780
acacatgtga caaactacaa accatctgta ggggattaca cactacctat cccaacaaga    840
gccaaccccta gacaaatttt gaatgtg                                       867
```

<210> SEQ ID NO 119
<211> LENGTH: 867
<212> TYPE: DNA
<213> ORGANISM: rhinovirus

<400> SEQUENCE: 119

```
aaccctgtag agaaatacat tgatggtgta ttgaatgaag tattggttgt tccaaacaca     60
aatgaaagtc accccagtac atcaaatgct gcaccagcac tagatgctgc tgaaactgga    120
cacacaagca atgtgcagcc agaagacatg atagaaacac gctatgtgtt aaattcacaa    180
actagagatg aaatgagtat tgagagcttc ctgggaagat ctggttgcat acatatatca    240
cacttagaag taaatacac agggtataat gaagagggta taactttaa catatggcaa     300
attaacctta agagatggc tcagataaga aggaagtttg agctatttac atatctcagg    360
tttgattctg aaatcacttt ggtaccatgc attgcttcac aaagtaaaaa cattggtcat    420
gtggtcatgc aatacatgta tgttccgcct ggagctccta aacctgaaaa gagagatgac    480
tacacatggc aatctggcac taatgcatct gttttctggc agcatggtca acctatccc     540
cgattctcac tccctttcct cagtgtagct tcagcatatt acatgtttta tgatgggtat    600
gatggaggtc ccggatcacg ttatggagca gtggtaacaa atgatatggg cacactgtgc    660
tctaggattg tgactgaaga acaccagaca caagtcaaaa ttacaactag agtgtaccac    720
aaagcaaaac atgtaaaggc atggtgccca cgtcctccaa gagctgttgg atatacacac    780
acacatgtga caaactacaa accatctgta ggggattaca cactacctat cccaacaaga    840
gccaaccccta gacaaatttt gaatgtc                                       867
```

<210> SEQ ID NO 120
<211> LENGTH: 867
<212> TYPE: DNA
<213> ORGANISM: rhinovirus

<400> SEQUENCE: 120

```
aatccagttg aaaagtatgt tgatagtgtt ttaaacgagg tattagttgt tcctaacatt     60
aatgaaagtc atcctagtac ttcaaattca gctcctgcct tggacgctgc agagacagga    120
catacaagta ctgttcaacc tgaggacatg attgaaacac ggtatgttca aacatcacaa    180
actagagatg agatgagcct tgagagtttc ctagggagat ctggctgcat acacatatca    240
cacctaaatg tcagatacac tgattataat gaaggtaata actttagatc atggcaaata    300
agcataaagg aaatggcaca aattagaagg aagtttgaac ttttcacata tgtgagattt    360
gattcagaaa ttactttagt gccttgcata gcctctcaaa gtaatgatat tgggcatgta    420
gtgatgcaat acatgtatgt cccaccaggt gctcctaaac cagaaaagag agacgactac    480
acttggcaat ctggaactaa tgcttcaatt ttctggcaac atggacaacc ttaccctcgc    540
ttctcacttc ctttcttgag tatagcctca gcttactata tgttctatga tggctatgat    600
ggtgatgctc ccggatcgcg atacgggacc atagtgacaa atgacatggg tacactgtgt    660
tctagaattg taactgaaga acaccagact caagtcagca ttaccacaag aatatatcac    720
aaagcaaaac atgtgaaagc gtggtgtcca cgaccccga gggctgtggg ttatacacac    780
acacatgtta ccaactacaa gccatcacag ggagattaca gtgttgttat tccagttaga    840
```
gagagtccca gacagattct taatgta                                              867

<210> SEQ ID NO 121
<211> LENGTH: 867
<212> TYPE: DNA
<213> ORGANISM: rhinovirus

<400> SEQUENCE: 121
aatccagttg aaaagtatgt tgatagtgtt ttaaacgagg tattagttgt tcctaacatt    60
aatgaaagtc atcctagtac ttcaaattca gctcctgcct tggacgctgc agagacagga   120
catacaagta ctgttcaacc tgaggacatg attgaaacac ggtatgttca acatcacaa   180
actagagatg agatgagcct tgagagtttc ctagggagat ctggctgcat acacatatca   240
cacctaaatg tcagatacac tgattataat gaaggtaata actttagatc atggcaaata   300
agcataaagg aaatggcaca aattagaagg aagtttgaac ttttcacata tgtgagattt   360
gattcagaaa ttactttagt gccttgcata gcctctcaaa gtaatgatat tgggcatgta   420
gtgatgcaat acatgtatgt cccaccaggt gctcctaaac cagaaaagag agacgactac   480
acttggcaat ctggaactaa tgcttcaatt ttctggcaac atggacaacc ttaccctcgc   540
ttctcacttc ctttcttgag tatagcctca gcttactata tgttctatga tggctatgat   600
ggtgatgctc ccggatcgcg atacgggacc atagtgacaa atgacatggg tacactgtgt   660
tctagaattg taactgaaga acaccagact caagtcagca ttaccacaag aatatatcac   720
aaagcaaaac atgtgaaagc gtggtgtcca cgacccccga gggctgtggg ttatacacac   780
acacatgtta ccaactacaa gccatcacag ggagattaca gtgttgttat tccagttaga   840
gagagtccca gacagattct taatgtt                                        867

<210> SEQ ID NO 122
<211> LENGTH: 867
<212> TYPE: DNA
<213> ORGANISM: rhinovirus

<400> SEQUENCE: 122
aatccagttg aaaagtatgt tgatagtgtt ttaaacgagg tattagttgt tcctaacatt    60
aatgaaagtc atcctagtac ttcaaattca gctcctgcct tggacgctgc agagacagga   120
catacaagta ctgttcaacc tgaggacatg attgaaacac ggtatgttca acatcacaa   180
actagagatg agatgagcct tgagagtttc ctagggagat ctggctgcat acacatatca   240
cacctaaatg tcagatacac tgattataat gaaggtaata actttagatc atggcaaata   300
agcataaagg aaatggcaca aattagaagg aagtttgaac ttttcacata tgtgagattt   360
gattcagaaa ttactttagt gccttgcata gcctctcaaa gtaatgatat tgggcatgta   420
gtgatgcaat acatgtatgt cccaccaggt gctcctaaac cagaaaagag agacgactac   480
acttggcaat ctggaactaa tgcttcaatt ttctggcaac atggacaacc ttaccctcgc   540
ttctcacttc ctttcttgag tatagcctca gcttactata tgttctatga tggctatgat   600
ggtgatgctc ccggatcgcg atacgggacc atagtgacaa atgacatggg tacactgtgt   660
tctagaattg taactgaaga acaccagact caagtcagca ttaccacaag aatatatcac   720
aaagcaaaac atgtgaaagc gtggtgtcca cgacccccga gggctgtggg ttatacacac   780
acacatgtta ccaactacaa gccatcacag ggagattaca gtgttgttat tccagttaga   840
gagagtccca gacagattct taatgtc                                        867

<210> SEQ ID NO 123
<211> LENGTH: 870
<212> TYPE: DNA
<213> ORGANISM: rhinovirus

<400> SEQUENCE: 123

| | | |
|---|---|---|
| aatcctgtag agaaatatgt ggacaccatt ctgaatgagg tgctagttgt cccaaatatc | 60 |
| aatgaaagtc atccaagtac atcaaatgct gctcctgcct tagatgcagc cgagacagga | 120 |
| catactagca atgtacagcc tgaggacatg atcgaaacac gctatgttca aacgtcccag | 180 |
| actagggatg aaatgagcat agaaagtttt cttggcagat ccggttgtgt acatgtttca | 240 |
| gagctccaat tagattatac caattacaat caagaaaata ataatttcaa aacttggcaa | 300 |
| ataaacttga agaaatggc acagattaga agaaaatttg aacttttcac ttacctcaga | 360 |
| tttgattcag aggtaacatt agtcccttgc atagctgcta aaagtaaaaa cattggacat | 420 |
| gttgttatgc aatacatgta tgtgcctcct ggtgctccta tcccaaaaac tagaaatgat | 480 |
| tacacatggc aatcaggtac taatgcatct atattttggc aacatggtca accataccca | 540 |
| agattttcat tacctttct aagtatagct tctgcatatt acatgttta tgatgggtat | 600 |
| gatggagatt caccaggatc ccgctatgga acaatagtaa ctaatgatat gggaacctta | 660 |
| tgctccagaa tagtaactga tgaacaccaa acacaggttg caatcacaac tagagtatat | 720 |
| cataaagcta aacatataaa agcttggtgc ccacgaccac ccagagccgt ggaatatacc | 780 |
| cacactcatg tgactaatta taaaccccag acaggtgaag tcactcttcc aattgaaata | 840 |
| agagataacc ctagacatat aaagaatgta | 870 |

<210> SEQ ID NO 124
<211> LENGTH: 870
<212> TYPE: DNA
<213> ORGANISM: rhinovirus

<400> SEQUENCE: 124

| | | |
|---|---|---|
| aatcctgtag agaaatatgt ggacaccatt ctgaatgagg tgctagttgt cccaaatatc | 60 |
| aatgaaagtc atccaagtac atcaaatgct gctcctgcct tagatgcagc cgagacagga | 120 |
| catactagca atgtacagcc tgaggacatg atcgaaacac gctatgttca aacgtcccag | 180 |
| actagggatg aaatgagcat agaaagtttt cttggcagat ccggttgtgt acatgtttca | 240 |
| gagctccaat tagattatac caattacaat caagaaaata ataatttcaa aacttggcaa | 300 |
| ataaacttga agaaatggc acagattaga agaaaatttg aacttttcac ttacctcaga | 360 |
| tttgattcag aggtaacatt agtcccttgc atagctgcta aaagtaaaaa cattggacat | 420 |
| gttgttatgc aatacatgta tgtgcctcct ggtgctccta tcccaaaaac tagaaatgat | 480 |
| tacacatggc aatcaggtac taatgcatct atattttggc aacatggtca accataccca | 540 |
| agattttcat tacctttct aagtatagct tctgcatatt acatgttta tgatgggtat | 600 |
| gatggagatt caccaggatc ccgctatgga acaatagtaa ctaatgatat gggaacctta | 660 |
| tgctccagaa tagtaactga tgaacaccaa acacaggttg caatcacaac tagagtatat | 720 |
| cataaagcta aacatataaa agcttggtgc ccacgaccac ccagagccgt ggaatatacc | 780 |
| cacactcatg tgactaatta taaaccccag acaggtgaag tcactcttcc aattgaaata | 840 |
| agagataacc ctagacatat aaagaatgtg | 870 |

<210> SEQ ID NO 125
<211> LENGTH: 870

<210> SEQ ID NO 125
<211> LENGTH: 870
<212> TYPE: DNA
<213> ORGANISM: rhinovirus

<400> SEQUENCE: 125

```
aatcctgtag agaaatatgt ggacaccatt ctgaatgagg tgctagttgt cccaaatatc      60
aatgaaagtc atccaagtac atcaaatgct gctcctgcct tagatgcagc cgagacagga     120
catactagca atgtacagcc tgaggacatg atcgaaacac gctatgttca aacgtcccag     180
actagggatg aaatgagcat agaaagtttt cttggcagat ccggttgtgt acatgtttca     240
gagctccaat tagattatac caattacaat caagaaaata taatttcaa aacttggcaa      300
ataaacttga agaaatggc acagattaga agaaaatttg aacttttcac ttacctcaga     360
tttgattcag aggtaacatt agtcccttgc atagctgcta aaagtaaaaa cattggacat     420
gttgttatgc aatacatgta tgtgcctcct ggtgctccta tcccaaaaac tagaaatgat     480
tacacatggc aatcaggtac taatgcatct atattttggc aacatggtca accatacccca    540
agattttcat tacctttct aagtatagct tctgcatatt acatgtttta tgatgggtat      600
gatggagatt caccaggatc ccgctatgga acaatagtaa ctaatgatat gggaacctta     660
tgctccagaa tagtaactga tgaacaccaa acacaggttg caatcacaac tagagtatat     720
cataaagcta acatataaa agcttggtgc ccacgaccac ccagagccgt ggaatatacc      780
cacactcatg tgactaatta taaaccccag acaggtgaag tcactcttcc aattgaaata     840
agagataacc ctagacatat aaagaatgtc                                      870
```

<210> SEQ ID NO 126
<211> LENGTH: 870
<212> TYPE: DNA
<213> ORGANISM: rhinovirus

<400> SEQUENCE: 126

```
aatcctgttg aaaggtatgt agatgaagtc ttgaatgaag ttcttgtagt accaaatatc      60
agtgaaagta gctcaactac atctaattca gctccagcct tagatgctgc agaaactggc     120
cacacaagca gtgtacaacc agaagacatg gttgaaacac gttatgtcca aacttcacaa     180
actagggatg aaatgagtgt tgagagcttt ttaggcagat ctggttgtat acacatgtct     240
accatgaaca tagattatac taattatgat gattctgtta ataattttgt gaaatggaaa     300
ataagtttgc aagaaatggc ccaagtgcgc agaaaatttg agttgttcac ctatgtaaga     360
tttgattcag aaataacaat tgtgccatgt atagccgggc aaggtggtga tgtcggacat     420
gttgttatgc aatacatgta tgtaccgccc ggtgcacccc ttccaacgaa gagaaatgat     480
tacacatggc aatctggcac caatgcatct gttttctggc aacatggtca aatttacccc     540
cgattctctt taccatttct tagtattgca tctgcatatt atatgtttta tgatggatat     600
aatggagatt cctcagatgc acgctatggg acaacaatca ctaatgatat gggcacactt     660
tgcttcagaa tagtaactga agaacatact aacaaggtca aggttacaac tagaatctat     720
cataaagcta acatgtcaa agcatggtgt cctagacctc ccagagctgt tgaatatact      780
aatgtgcatg ttacaaacta caaaccaggg acaggagatg ttgcagtctc cattgtacct     840
agagcaaatg ttagggaaat tagaaacttt                                      870
```

<210> SEQ ID NO 127
<211> LENGTH: 870
<212> TYPE: DNA
<213> ORGANISM: rhinovirus

<400> SEQUENCE: 127

```
aatcctgttg aaaggtatgt agatgaagtc ttgaatgaag ttcttgtagt accaaatatc    60
agtgaaagta gctcaactac atctaattca gctccagcct tagatgctgc agaaactggc   120
cacacaagca gtgtacaacc agaagacatg gttgaaacac gttatgtcca aacttcacaa   180
actagggatg aaatgagtgt tgagagcttt ttaggcagat ctggttgtat acacatgtct   240
accatgaaca tagattatac taattatgat gattctgtta ataattttgt gaaatggaaa   300
ataagtttgc aagaaatggc ccaagtgcgc agaaaatttg agttgttcac ctatgtaaga   360
tttgattcag aaataacaat tgtgccatgt atagccgggc aaggtggtga tgtcggacat   420
gttgttatgc aatacatgta tgtaccgccc ggtgcacccc ttccaacgaa gagaaatgat   480
tacacatggc aatctggcac caatgcatct gttttctggc aacatggtca aatttacccc   540
cgattctctt taccatttct tagtattgca tctgcatatt atatgtttta tgatggatat   600
aatgagatt cctcagatgc acgctatggg acaacaatca ctaatgatat gggcacactt   660
tgcttcagaa tagtaactga agaacatact aacaaggtca aggttacaac tagaatctat   720
cataaagcta acatgtcaa agcatggtgt cctagacctc ccagagctgt tgaatatact   780
aatgtgcatg ttacaaacta caaaccaggg acaggagatg ttgcagtctc cattgtacct   840
agagcaaatg ttagggaaat tagaaacttg                                    870
```

<210> SEQ ID NO 128
<211> LENGTH: 870
<212> TYPE: DNA
<213> ORGANISM: rhinovirus

<400> SEQUENCE: 128

```
aatcctgttg aaaggtatgt agatgaagtc ttgaatgaag ttcttgtagt accaaatatc    60
agtgaaagta gctcaactac atctaattca gctccagcct tagatgctgc agaaactggc   120
cacacaagca gtgtacaacc agaagacatg gttgaaacac gttatgtcca aacttcacaa   180
actagggatg aaatgagtgt tgagagcttt ttaggcagat ctggttgtat acacatgtct   240
accatgaaca tagattatac taattatgat gattctgtta ataattttgt gaaatggaaa   300
ataagtttgc aagaaatggc ccaagtgcgc agaaaatttg agttgttcac ctatgtaaga   360
tttgattcag aaataacaat tgtgccatgt atagccgggc aaggtggtga tgtcggacat   420
gttgttatgc aatacatgta tgtaccgccc ggtgcacccc ttccaacgaa gagaaatgat   480
tacacatggc aatctggcac caatgcatct gttttctggc aacatggtca aatttacccc   540
cgattctctt taccatttct tagtattgca tctgcatatt atatgtttta tgatggatat   600
aatgagatt cctcagatgc acgctatggg acaacaatca ctaatgatat gggcacactt   660
tgcttcagaa tagtaactga agaacatact aacaaggtca aggttacaac tagaatctat   720
cataaagcta acatgtcaa agcatggtgt cctagacctc ccagagctgt tgaatatact   780
aatgtgcatg ttacaaacta caaaccaggg acaggagatg ttgcagtctc cattgtacct   840
agagcaaatg ttagggaaat tagaaactta                                    870
```

<210> SEQ ID NO 129
<211> LENGTH: 873
<212> TYPE: DNA
<213> ORGANISM: rhinovirus

<400> SEQUENCE: 129

```
aatcctgtag aaaggtatgt ggatgaggtc ctgaatgagg ttcttgtggt accaaatatt    60
```

| | |
|---|---:|
| agtgaaagca gtccaactac ttctaattca gctccagccc tagatgcagc agagactggt | 120 |
| cataccagta atgtacaacc agaggacatg attgaaacac gatatgtcca aacctcacaa | 180 |
| actagagatg aaatgagcat agaaagcttt ttaggtagat caggctgtgt acataagtcc | 240 |
| actttgaata tagattatac tgattatgat gattctatcc agaacttcaa gaagtggaaa | 300 |
| attagcttac aggagatggc ccaagtacgt agaaagtttg agtttttttac gtatgttaga | 360 |
| tttgactcag aaataacaat tgtgccaagt atagctggac agggtagtga tgtcggacat | 420 |
| gttgtcatgc aatacatgtt cgtaccacct ggcgcacccc tcccagaaaa gagagatgat | 480 |
| tacacatggc aatctggcac caatgcatct gtattctggc agtatggtca agtttaccct | 540 |
| aggttttctc taccatttct tagcattgct tccgcatatt acatgtttta tgatggttat | 600 |
| gaagaaggct ctacaaatgc acgctatgga acaacagtca caaatgacat gggtacatta | 660 |
| tgctttagaa tagttactga agaacacacc aacaaagtta aggtcacaac tagagtttac | 720 |
| cacaaagcta acatgttaa agcatggtgt cctagacctc ccagggctgt ggagtacacc | 780 |
| aatgtgcatg tcacaaatta caaaccaaaa gcaggagcag agattgtggc ttctgtcaga | 840 |
| cctagagaca atgttagaca agtaagaaat tat | 873 |

```
<210> SEQ ID NO 130
<211> LENGTH: 873
<212> TYPE: DNA
<213> ORGANISM: rhinovirus

<400> SEQUENCE: 130
```

| | |
|---|---:|
| aatcctgtag aaaggtatgt ggatgaggtc ctgaatgagg ttcttgtggt accaaatatt | 60 |
| agtgaaagca gtccaactac ttctaattca gctccagccc tagatgcagc agagactggt | 120 |
| cataccagta atgtacaacc agaggacatg attgaaacac gatatgtcca aacctcacaa | 180 |
| actagagatg aaatgagcat agaaagcttt ttaggtagat caggctgtgt acataagtcc | 240 |
| actttgaata tagattatac tgattatgat gattctatcc agaacttcaa gaagtggaaa | 300 |
| attagcttac aggagatggc ccaagtacgt agaaagtttg agtttttttac gtatgttaga | 360 |
| tttgactcag aaataacaat tgtgccaagt atagctggac agggtagtga tgtcggacat | 420 |
| gttgtcatgc aatacatgtt cgtaccacct ggcgcacccc tcccagaaaa gagagatgat | 480 |
| tacacatggc aatctggcac caatgcatct gtattctggc agtatggtca agtttaccct | 540 |
| aggttttctc taccatttct tagcattgct tccgcatatt acatgtttta tgatggttat | 600 |
| gaagaaggct ctacaaatgc acgctatgga acaacagtca caaatgacat gggtacatta | 660 |
| tgctttagaa tagttactga agaacacacc aacaaagtta aggtcacaac tagagtttac | 720 |
| cacaaagcta acatgttaa agcatggtgt cctagacctc ccagggctgt ggagtacacc | 780 |
| aatgtgcatg tcacaaatta caaaccaaaa gcaggagcag agattgtggc ttctgtcaga | 840 |
| cctagagaca atgttagaca agtaagaaat tag | 873 |

```
<210> SEQ ID NO 131
<211> LENGTH: 873
<212> TYPE: DNA
<213> ORGANISM: rhinovirus

<400> SEQUENCE: 131
```

| | |
|---|---:|
| aatcctgtag aaaggtatgt ggatgaggtc ctgaatgagg ttcttgtggt accaaatatt | 60 |
| agtgaaagca gtccaactac ttctaattca gctccagccc tagatgcagc agagactggt | 120 |

```
cataccagta atgtacaacc agaggacatg attgaaacac gatatgtcca aacctcacaa    180
actagagatg aaatgagcat agaaagcttt ttaggtagat caggctgtgt acataagtcc    240
actttgaata tagattatac tgattatgat gattctatcc agaacttcaa gaagtggaaa    300
attagcttac aggagatggc ccaagtacgt agaaagtttg agttttttac gtatgttaga    360
tttgactcag aaataacaat tgtgccaagt atagctggac agggtagtga tgtcggacat    420
gttgtcatgc aatacatgtt cgtaccacct ggcgcacccc tcccagaaaa gagagatgat    480
tacacatggc aatctggcac caatgcatct gtattctggc agtatggtca agtttaccct    540
aggttttctc taccatttct tagcattgct tccgcatatt acatgtttta tgatggttat    600
gaagaaggct ctacaaatgc acgctatgga caacagtca  caaatgacat gggtacatta    660
tgctttagaa tagttactga agaacacacc aacaaagtta aggtcacaac tagagtttac    720
cacaaagcta acatgttaa  agcatggtgt cctagacctc ccagggctgt ggagtacacc    780
aatgtgcatg tcacaaatta caaaccaaaa gcaggagcag agattgtggc ttctgtcaga    840
cctagagaca atgttagaca agtaagaaat tac                                 873

<210> SEQ ID NO 132
<211> LENGTH: 870
<212> TYPE: DNA
<213> ORGANISM: rhinovirus

<400> SEQUENCE: 132
aatcctgtag aaagatatgt agatgaagtt ttgaatgaag tccttgtagt acccaatatc     60
aatgaaagta atccaactac atccaactca gcacctgcac tggacgctgc agaaactggc    120
cataccagtg gtgtacaacc agaagacatg attgagaccc gttatgtcca acatcacag    180 actagagatg aaatgagcat tgaaagcttc cttggcaggt caggttgtat acacatgtca    240
actatgaata taaattatga aaattatgat gatgctcctg aaaattttac caaatggaaa    300
ataagtttac aagagatggc tcaaatacgt aggaaatttg aattattcac ctatgtaaga    360
tttgattcag aagtgacaat tgtaccatgt atagctggtc aaagtggaga tgtgggacat    420
gtagttatgc agtatatgta tgtcccacct ggagcccctc tacccacaaa aagaaatgac    480
tacacatggc agtccggcac taatgcatca gtattctggc aacatggtca aacttacccc    540
agattctcat taccattcct tagtatagca tccgcatatt atatgtttta tgatggatat    600
gatggtgact ccacacaatc acattatggc accacagtag ttaatgacat gggcacatta    660
tgctttagga tagtgactga agaacacact agcagggtaa aggttactac tagaatctat    720
cataaggcta acatgttaa  agcttggtgt ccaagacctc ctagggcagt agaatataca    780
aatgcacatg tgaccaatta taaacccact gatggagaag ttactactgc cattaggcat    840
agagataatg ttagagccat ccaaaatttt                                     870

<210> SEQ ID NO 133
<211> LENGTH: 870
<212> TYPE: DNA
<213> ORGANISM: rhinovirus

<400> SEQUENCE: 133
aatcctgtag aaagatatgt agatgaagtt ttgaatgaag tccttgtagt acccaatatc     60
aatgaaagta atccaactac atccaactca gcacctgcac tggacgctgc agaaactggc    120
cataccagtg gtgtacaacc agaagacatg attgagaccc gttatgtcca acatcacag    180 actagagatg aaatgagcat tgaaagcttc cttggcaggt caggttgtat acacatgtca    240
```

| | |
|---|---|
| actatgaata taaattatga aaattatgat gatgctcctg aaaatttac caaatggaaa | 300 |
| ataagtttac aagagatggc tcaaatacgt aggaaatttg aattattcac ctatgtaaga | 360 |
| tttgattcag aagtgacaat tgtaccatgt atagctggtc aaagtggaga tgtgggacat | 420 |
| gtagttatgc agtatatgta tgtcccacct ggagcccctc tacccacaaa agaaatgac | 480 |
| tacacatggc agtccggcac taatgcatca gtattctggc aacatggtca aacttacccc | 540 |
| agattctcat taccattcct tagtatagca tccgcatatt atatgtttta tgatggatat | 600 |
| gatggtgact ccacacaatc acattatggc accacagtag ttaatgacat gggcacatta | 660 |
| tgctttagga tagtgactga agaacacact agcagggtaa aggttactac tagaatctat | 720 |
| cataaggcta acatgttaa agcttggtgt ccaagacctc ctagggcagt agaatataca | 780 |
| aatgcacatg tgaccaatta taaacccact gatggagaag ttactactgc cattaggcat | 840 |
| agagataatg ttagagccat ccaaaatttg | 870 |

<210> SEQ ID NO 134
<211> LENGTH: 870
<212> TYPE: DNA
<213> ORGANISM: rhinovirus

<400> SEQUENCE: 134

| | |
|---|---|
| aatcctgtag aaagatatgt agatgaagtt ttgaatgaag tccttgtagt acccaatatc | 60 |
| aatgaaagta atccaactac atccaactca gcacctgcac tggacgctgc agaaactggc | 120 |
| cataccagtg gtgtacaacc agaagacatg attgagaccc gttatgtcca acatcacag | 180 |
| actagagatg aaatgagcat tgaaagcttc cttggcaggt caggttgtat acacatgtca | 240 |
| actatgaata taaattatga aaattatgat gatgctcctg aaaatttac caaatggaaa | 300 |
| ataagtttac aagagatggc tcaaatacgt aggaaatttg aattattcac ctatgtaaga | 360 |
| tttgattcag aagtgacaat tgtaccatgt atagctggtc aaagtggaga tgtgggacat | 420 |
| gtagttatgc agtatatgta tgtcccacct ggagcccctc tacccacaaa agaaatgac | 480 |
| tacacatggc agtccggcac taatgcatca gtattctggc aacatggtca aacttacccc | 540 |
| agattctcat taccattcct tagtatagca tccgcatatt atatgtttta tgatggatat | 600 |
| gatggtgact ccacacaatc acattatggc accacagtag ttaatgacat gggcacatta | 660 |
| tgctttagga tagtgactga agaacacact agcagggtaa aggttactac tagaatctat | 720 |
| cataaggcta acatgttaa agcttggtgt ccaagacctc ctagggcagt agaatataca | 780 |
| aatgcacatg tgaccaatta taaacccact gatggagaag ttactactgc cattaggcat | 840 |
| agagataatg ttagagccat ccaaaatttc | 870 |

<210> SEQ ID NO 135
<211> LENGTH: 876
<212> TYPE: DNA
<213> ORGANISM: rhinovirus

<400> SEQUENCE: 135

| | |
|---|---|
| aaccctgtgg aaagatatgt agatgaagtt ttaaatgaag tgcttgtagt cccaaacatt | 60 |
| aatcagagca accctacaac atccaactca gcaccagtct tagacgctgc tgaaacaggt | 120 |
| cataccagca atgttcaacc ggaggacacg attgaaacac gatatgttca aacctcacag | 180 |
| acaagagatg aaatgagtgt agaaagtttc ttgggtagat cagggtgcat acatatgtca | 240 |
| acattaaata taaactatga taactatgat gattctattg aaaacttcaa ggtgtggaaa | 300 |

```
ataaacctgc aagagatggc acaaatacgt agaaaatttg agttgttcac atatgctaga    360
tttgattcag agattacaat tgtaccttgt gttgctgggc aaggtggtga cattggacac    420
gtggtcatgc aatacatgta tgttccacct ggtgcaccta cacctgagaa aagaaatgat    480
ttcacatggc aatcaggcac aaatgcatct gttttctggc aacatggtca agcttatccc    540
agattttcat taccattcct aagtattgca tctgcatatt atatgtttta tgatggttat    600
gatggagatt ctgaaataac gcgctatgga acatcagtga caaatgatat gggtgcattg    660
tgctttagaa tagtaactga acagcataca aatcaagtta aaatcacaac taggatttac    720
cataaagcta aacatgttaa agtctggtgt cctagacccc ccagagcagt ggaatatact    780
aatgtgcatt tgaccaatta caagcccaaa gatagtgaaa acaagttac cactttcatc    840 aaacctagag ctaacttaag agagattaga acattt                              876

<210> SEQ ID NO 136
<211> LENGTH: 876
<212> TYPE: DNA
<213> ORGANISM: rhinovirus

<400> SEQUENCE: 136
aaccctgtgg aaagatatgt agatgaagtt ttaaatgaag tgcttgtagt cccaaacatt     60
aatcagagca accctacaac atccaactca gcaccagtct tagacgctgc tgaaacaggt    120
cataccagca atgttcaacc ggaggacacg attgaaacac gatatgttca aacctcacag    180
acaagagatg aaatgagtgt agaaagtttc ttgggtagat cagggtgcat acatatgtca    240
acattaaata taaactatga taactatgat gattctattg aaaacttcaa ggtgtggaaa    300
ataaacctgc aagagatggc acaaatacgt agaaaatttg agttgttcac atatgctaga    360
tttgattcag agattacaat tgtaccttgt gttgctgggc aaggtggtga cattggacac    420
gtggtcatgc aatacatgta tgttccacct ggtgcaccta cacctgagaa aagaaatgat    480
ttcacatggc aatcaggcac aaatgcatct gttttctggc aacatggtca agcttatccc    540
agattttcat taccattcct aagtattgca tctgcatatt atatgtttta tgatggttat    600
gatggagatt ctgaaataac gcgctatgga acatcagtga caaatgatat gggtgcattg    660
tgctttagaa tagtaactga acagcataca aatcaagtta aaatcacaac taggatttac    720
cataaagcta aacatgttaa agtctggtgt cctagacccc ccagagcagt ggaatatact    780
aatgtgcatt tgaccaatta caagcccaaa gatagtgaaa acaagttac cactttcatc    840 aaacctagag ctaacttaag agagattaga acattt                              876

<210> SEQ ID NO 137
<211> LENGTH: 876
<212> TYPE: DNA
<213> ORGANISM: rhinovirus

<400> SEQUENCE: 137
aaccctgtgg aaagatatgt agatgaagtt ttaaatgaag tgcttgtagt cccaaacatt     60
aatcagagca accctacaac atccaactca gcaccagtct tagacgctgc tgaaacaggt    120
cataccagca atgttcaacc ggaggacacg attgaaacac gatatgttca aacctcacag    180
acaagagatg aaatgagtgt agaaagtttc ttgggtagat cagggtgcat acatatgtca    240
acattaaata taaactatga taactatgat gattctattg aaaacttcaa ggtgtggaaa    300
ataaacctgc aagagatggc acaaatacgt agaaaatttg agttgttcac atatgctaga    360
tttgattcag agattacaat tgtaccttgt gttgctgggc aaggtggtga cattggacac    420
```

```
gtggtcatgc aatacatgta tgttccacct ggtgcaccta cacctgagaa aagaaatgat    480
ttcacatggc aatcaggcac aaatgcatct gttttctggc aacatggtca agcttatccc    540
agattttcat taccattcct aagtattgca tctgcatatt atatgtttta tgatggttat    600
gatggagatt ctgaaataac gcgctatgga acatcagtga caaatgatat gggtgcattg    660
tgctttagaa tagtaactga acagcataca aatcaagtta aaatcacaac taggatttac    720
cataaagcta acatgttaaa gtctggtgt cctagacccc ccagagcagt ggaatatact    780
aatgtgcatt tgaccaatta caagcccaaa gatagtgaaa acaagttac cactttcatc    840 aaacctagag ctaacttaag agagattaga acattt                              876

<210> SEQ ID NO 138
<211> LENGTH: 867
<212> TYPE: DNA
<213> ORGANISM: rhinovirus

<400> SEQUENCE: 138
aaccctgtag agagatatgt agatgaagtc ttgaatgagg ttcttgtagt ccctaatatt     60
aatgaaagtt acccaacaac ttccaattca gccccagtgc tagatgccgc tgaaacaggt    120
catactagca atgtccaacc agaggatatg attgagactc gatatgttca gacatcgcag    180
acgagagatg aaatgagcat tgagagcttt ttgggtagat cagggtgtat acacatgtca    240
acattaaaca tagattatga caattatgat gactccccta agaatttaa ggtgtggaaa    300 ataaatctac aagaaatggc tcaaattcgc aggaagtttg aactgttcac ttatgctaga    360
tttgattcag ataacaat tgttccatgt gttgctgtgc agagtggtga tattggtcat    420
gtggtcatgc aatatatgta tgttccacca ggtgccccca cacctgagaa gagagatgac    480
tttacatggc aatcaggcac aaatgcatct gtgttttggc agcacgggca agcatatcct    540
agattttcac tgcctttcct tagtattgcc tctgcatatt acatgtttta tgatggtat    600 gatggtgact ctgaatcaac acgctatgga acatctgtta ccaatgacat gggcacttta    660
tgttttagaa tagtgacaga ggaacacacc aacaaggtca aaattacaac cagagtttac    720
cacaaagcta acatgttaag ggtgtggtgc ccgagacccc ctagagcagt tgaatacaca    780
aatgtgcatc tcacaaatta taaacccaac aatgaggtta ccacttttat caaacctaga    840
gaaaatctaa gggatattag aaattttt                                        867

<210> SEQ ID NO 139
<211> LENGTH: 867
<212> TYPE: DNA
<213> ORGANISM: rhinovirus

<400> SEQUENCE: 139
aaccctgtag agagatatgt agatgaagtc ttgaatgagg ttcttgtagt ccctaatatt     60
aatgaaagtt acccaacaac ttccaattca gccccagtgc tagatgccgc tgaaacaggt    120
catactagca atgtccaacc agaggatatg attgagactc gatatgttca gacatcgcag    180
acgagagatg aaatgagcat tgagagcttt ttgggtagat cagggtgtat acacatgtca    240
acattaaaca tagattatga caattatgat gactccccta agaatttaa ggtgtggaaa    300 ataaatctac aagaaatggc tcaaattcgc aggaagtttg aactgttcac ttatgctaga    360
tttgattcag ataacaat tgttccatgt gttgctgtgc agagtggtga tattggtcat    420
gtggtcatgc aatatatgta tgttccacca ggtgccccca cacctgagaa gagagatgac    480
```

```
tttacatggc aatcaggcac aaatgcatct gtgttttggc agcacgggca agcatatcct    540
agattttcac tgcctttcct tagtattgcc tctgcatatt acatgtttta tgatggatat    600
gatggtgact ctgaatcaac acgctatgga acatctgtta ccaatgacat gggcacttta    660
tgttttagaa tagtgacaga ggaacacacc aacaaggtca aaattacaac cagagtttac    720
cacaaagcta acatgttaa ggtgtggtgc ccgagacccc ctagagcagt tgaatacaca    780
aatgtgcatc tcacaaatta taaacccaac aatgaggtta ccacttttat caaacctaga    840
gaaaatctaa gggatattag aaattta                                       867

<210> SEQ ID NO 140
<211> LENGTH: 867
<212> TYPE: DNA
<213> ORGANISM: rhinovirus

<400> SEQUENCE: 140
aaccctgtag agagatatgt agatgaagtc ttgaatgagg ttcttgtagt ccctaatatt     60
aatgaaagtt acccaacaac ttccaattca gccccagtgc tagatgccgc tgaaacaggt    120
catactagca atgtccaacc agaggatatg attgagactc gatatgttca gacatcgcag    180
acgagagatg aaatgagcat tgagagcttt ttgggtagat cagggtgtat acacatgtca    240
acattaaaca tagattatga caattatgat gactccccta gaattttaa ggtgtggaaa     300 ataaatctac aagaaatggc tcaaattcgc aggaagtttg aactgttcac ttatgctaga    360
tttgattcag agataacaat tgttccatgt gttgctgtgc agagtggtga tattggtcat    420
gtggtcatgc aatatatgta tgttccacca ggtgccccca cacctgagaa gagagatgac    480
tttacatggc aatcaggcac aaatgcatct gtgttttggc agcacgggca agcatatcct    540
agattttcac tgcctttcct tagtattgcc tctgcatatt acatgtttta tgatggatat    600
gatggtgact ctgaatcaac acgctatgga acatctgtta ccaatgacat gggcacttta    660
tgttttagaa tagtgacaga ggaacacacc aacaaggtca aaattacaac cagagtttac    720
cacaaagcta acatgttaa ggtgtggtgc ccgagacccc ctagagcagt tgaatacaca    780
aatgtgcatc tcacaaatta taaacccaac aatgaggtta ccacttttat caaacctaga    840
gaaaatctaa gggatattag aaatttc                                       867

<210> SEQ ID NO 141
<211> LENGTH: 855
<212> TYPE: DNA
<213> ORGANISM: rhinovirus

<400> SEQUENCE: 141
aatccagtgg aaagatatgt agatgaagtc ttaaatgaag tgttagtagt gcccaatatt     60
aatgagagcc accctaccac atcaaatgcg gccccagttt tggatgctgc tgaaacagga    120
cataccaata agatacagcc agaagacact atagaaacca gatatgtgca atcttcacag    180
acattggatg aaatgagtgt ggaaagcttc ctaggcagat cggggtgcat ccatgaatca    240
gtgttggata ttgtggacaa ttacaatgat caaagtttca ctaaatggaa gataaacctg    300
caagaaatgg cacaaattag aagaaaattt gaaatgtta cttatgcaag atttgactct    360
gaaattacta tggtaccaag tgtagcagcc aaagatggtc acattggtca tatagtcatg    420
caatatatgt atgtaccacc aggagcacct ataccaacaa ctagaaatga ctatgcttgg    480
caatctggaa caaatgcatc tgtattttgg cagcatgggc aaccttcc tcgcttttca    540 cttccctttt tgagtattgc atcagcatat tacatgttt atgatggtta tgatggagac    600
```

```
acatataaat ccagatatgg aactgtagtc accaatgaca tgggaacttt gtgttcgcgt      660
attgtgacca gtgagcaatt acacaaagtc aaagtggtaa caaggatata tcacaaagcc      720
aaacacacca aagcttggtg cccaagacca cccagagctg ttcaatactc acatacacat      780
accaccaact acaaattgag ttcagaagta cacaatgatg tggctataag acctagaaca      840
aatctaacaa ctgta                                                       855

<210> SEQ ID NO 142
<211> LENGTH: 855
<212> TYPE: DNA
<213> ORGANISM: rhinovirus

<400> SEQUENCE: 142
aatccagtgg aaagatatgt agatgaagtc ttaaatgaag tgttagtagt gcccaatatt       60
aatgagagcc accctaccac atcaaatgcg gccccagttt tggatgctgc tgaaacagga      120
cataccaata agatacagcc agaagacact atagaaacca gatatgtgca atcttcacag      180
acattggatg aaatgagtgt ggaaagcttc ctaggcagat cggggtgcat ccatgaatca      240
gtgttggata ttgtggacaa ttacaatgat caaagtttca ctaaatggaa gataaacctg      300
caagaaatgg cacaaattag aagaaaattt gaaatgttta cttatgcaag atttgactct      360
gaaattacta tggtaccaag tgtagcagcc aaagatggtc acattggtca tatagtcatg      420
caatatatgt atgtaccacc aggagcacct ataccaacaa ctagaaatga ctatgcttgg      480
caatctggaa caaatgcatc tgtatttttgg cagcatgggc aacctttccc tcgcttttca      540
cttccctttt tgagtattgc atcagcatat tacatgtttt atgatggtta tgatggagac      600
acatataaat ccagatatgg aactgtagtc accaatgaca tgggaacttt gtgttcgcgt      660
attgtgacca gtgagcaatt acacaaagtc aaagtggtaa caaggatata tcacaaagcc      720
aaacacacca aagcttggtg cccaagacca cccagagctg ttcaatactc acatacacat      780
accaccaact acaaattgag ttcagaagta cacaatgatg tggctataag acctagaaca      840
aatctaacaa ctgtc                                                       855

<210> SEQ ID NO 143
<211> LENGTH: 855
<212> TYPE: DNA
<213> ORGANISM: rhinovirus

<400> SEQUENCE: 143
aatccagtgg aaagatatgt agatgaagtc ttaaatgaag tgttagtagt gcccaatatt       60
aatgagagcc accctaccac atcaaatgcg gccccagttt tggatgctgc tgaaacagga      120
cataccaata agatacagcc agaagacact atagaaacca gatatgtgca atcttcacag      180
acattggatg aaatgagtgt ggaaagcttc ctaggcagat cggggtgcat ccatgaatca      240
gtgttggata ttgtggacaa ttacaatgat caaagtttca ctaaatggaa gataaacctg      300
caagaaatgg cacaaattag aagaaaattt gaaatgttta cttatgcaag atttgactct      360
gaaattacta tggtaccaag tgtagcagcc aaagatggtc acattggtca tatagtcatg      420
caatatatgt atgtaccacc aggagcacct ataccaacaa ctagaaatga ctatgcttgg      480
caatctggaa caaatgcatc tgtatttttgg cagcatgggc aacctttccc tcgcttttca      540
cttccctttt tgagtattgc atcagcatat tacatgtttt atgatggtta tgatggagac      600
acatataaat ccagatatgg aactgtagtc accaatgaca tgggaacttt gtgttcgcgt      660
```

```
attgtgacca gtgagcaatt acacaaagtc aaagtggtaa caaggatata tcacaaagcc      720
aaacacacca aagcttggtg cccaagacca cccagagctg ttcaatactc acatacacat      780
accaccaact acaaattgag ttcagaagta cacaatgatg tggctataag acctagaaca      840
aatctaacaa ctgtt                                                       855

<210> SEQ ID NO 144
<211> LENGTH: 855
<212> TYPE: DNA
<213> ORGANISM: rhinovirus

<400> SEQUENCE: 144
aacccagtgg agcggtatgt ggatgaagtc ttaaatgagg tattggtagt ccctaatatt       60
aatgaaagcc accctacaac atctaattca gctcctgttt tagatgcagc tgaaactgga      120
cacaccagta atatacaacc tgaggatact attgagacca gatatgtaca atcttcacag      180
acactggatg aaatgagtgt agaaagtttt ttaggcagat caggttgcat tcatgaatcc      240
atattggaca ttaaagagga ttacaatacc cagagcttta ctaaatggaa aattaactta      300
caagagatgg cacagattag gagaaagttt gaaatgttca catacactag atttaactct      360
gagattacac tggtaccaag tattgcaaac aaggaaggtc atattggtca tatagtaatg      420
caatacatgt atgtaccacc aggagcaccc attccaacaa ctagagaaga ctatgcttgg      480
caatctggaa caaatgcatc tatattctgg caacatgggc aaccctttcc ccggttttca      540
ctcccttttc taagtgtagc atcagcatat tacatgttct atgatggata tgatggtgat      600
acttatcact ccagatacgg gactgtagtc actaatgata tgggaacatt atgctcacgg      660
atagtgacaa gtgagcaagt gcacaaggtg aaaatagtaa caagaatata tcacaaagct      720
aagcacacca aagcttggtg tccaagacca cccagggctg ttcagtacac acatacacat      780
gtaactaatt ataaattaga aacagatgtc cacactagtg tagccataaa acctagaaca      840
agtctaacaa atgtg                                                       855

<210> SEQ ID NO 145
<211> LENGTH: 855
<212> TYPE: DNA
<213> ORGANISM: rhinovirus

<400> SEQUENCE: 145
aacccagtgg agcggtatgt ggatgaagtc ttaaatgagg tattggtagt ccctaatatt       60
aatgaaagcc accctacaac atctaattca gctcctgttt tagatgcagc tgaaactgga      120
cacaccagta atatacaacc tgaggatact attgagacca gatatgtaca atcttcacag      180
acactggatg aaatgagtgt agaaagtttt ttaggcagat caggttgcat tcatgaatcc      240
atattggaca ttaaagagga ttacaatacc cagagcttta ctaaatggaa aattaactta      300
caagagatgg cacagattag gagaaagttt gaaatgttca catacactag atttaactct      360
gagattacac tggtaccaag tattgcaaac aaggaaggtc atattggtca tatagtaatg      420
caatacatgt atgtaccacc aggagcaccc attccaacaa ctagagaaga ctatgcttgg      480
caatctggaa caaatgcatc tatattctgg caacatgggc aaccctttcc ccggttttca      540
ctcccttttc taagtgtagc atcagcatat tacatgttct atgatggata tgatggtgat      600
acttatcact ccagatacgg gactgtagtc actaatgata tgggaacatt atgctcacgg      660
atagtgacaa gtgagcaagt gcacaaggtg aaaatagtaa caagaatata tcacaaagct      720
aagcacacca aagcttggtg tccaagacca cccagggctg ttcagtacac acatacacat      780
```

```
gtaactaatt ataaattaga aacagatgtc cacactagtg tagccataaa acctagaaca      840
agtctaacaa atgtc                                                       855

<210> SEQ ID NO 146
<211> LENGTH: 855
<212> TYPE: DNA
<213> ORGANISM: rhinovirus

<400> SEQUENCE: 146
aacccagtgg agcggtatgt ggatgaagtc ttaaatgagg tattggtagt ccctaatatt       60
aatgaaagcc accctacaac atctaattca gctcctgttt tagatgcagc tgaaactgga      120
cacaccagta atatacaacc tgaggatact attgagacca gatatgtaca atcttcacag      180
acactggatg aaatgagtgt agaaagtttt ttaggcagat caggttgcat tcatgaatcc      240
atattggaca ttaaagagga ttacaatacc cagagcttta ctaaatggaa aattaactta      300
caagagatgg cacagattag gagaaagttt gaaatgttca catacactag atttaactct      360
gagattacac tggtaccaag tattgcaaac aaggaaggtc atattggtca tatagtaatg      420
caatacatgt atgtaccacc aggagcaccc attccaacaa ctagagaaga ctatgcttgg      480
caatctggaa caaatgcatc tatattctgg caacatgggc aaccctttcc ccggttttca      540 ctccctttc taagtgtagc atcagcatat acatgttct atgatggata tgatggtgat       600
acttatcact ccagatacgg gactgtagtc actaatgata tgggaacatt atgctcacgg      660
atagtgacaa gtgagcaagt gcacaaggtg aaaatagtaa caagaatata tcacaaagct      720
aagcacacca agcttggtg tccaagacca cccagggctg ttcagtacac acatacacat      780
gtaactaatt ataaattaga aacagatgtc cacactagtg tagccataaa acctagaaca      840
agtctaacaa atgtt                                                       855

<210> SEQ ID NO 147
<211> LENGTH: 849
<212> TYPE: DNA
<213> ORGANISM: rhinovirus

<400> SEQUENCE: 147
aaccctgttg agaattatat agatgaagtt cttaatgaag ttttagttgt cccaaatatt       60
aatagtagta accccacaac atcaaattct gccccagcat tagatgctgc agaaacaggg      120
cacactagta gtgttcaacc agaggatgtc attgaaacta gtatgtgca gacatcacaa       180 acaagagatg aaatgagttt agagagtttt cttggcagat caggatgcat acatgaatct      240
aaattagagg ttacacttgc aaattataac aaggagaatt ttacagtgtg gctattaat       300 atacaagaaa tggctcaaat tagaaggaaa tttgaattgt tcacctatac taggtttgat      360
tctgaaataa ccctagttcc atgcatttcc gcccttagtc aggacattgg acacatcaca      420
atgcaataca tgtatgttcc acctggtgca ccggtgccca atagtaggga cgattatgca      480
tggcagtctg gcactaatgc ctctgttttc tggcaacatg gacaggctta tccaagattt      540
tccttacctt tcctaagtgt ggcatctgct tattacatgt tttatgatgg gtatgatgaa      600
caagatcaaa actatggtac agcaagcaca aataacatgg ggtcactatg ctctaggata      660
gtaacagaga aacacattca taggtacat ataatgacaa gaatctatca caaggctaaa       720
catgtcaagg catggtgtcc acgcccaccc agagcgcttg agtatactcg tgctcaccgc      780
actaatttta aaattgagga taggagtatt cagacagcaa ttgtgaccag accaattatc      840
```

```
<210> SEQ ID NO 148
<211> LENGTH: 849
<212> TYPE: DNA
<213> ORGANISM: rhinovirus

<400> SEQUENCE: 148
aaccctgttg agaattatat agatgaagtt cttaatgaag ttttagttgt cccaaatatt      60
aatagtagta accccacaac atcaaattct gccccagcat tagatgctgc agaaacaggg    120
cacactagta gtgttcaacc agaggatgtc attgaaacta ggtatgtgca gacatcacaa    180
acaagagatg aaatgagttt agagagtttt cttggcagat caggatgcat acatgaatct    240
aaattagagg ttacacttgc aaattataac aaggagaatt ttacagtgtg ggctattaat    300
atacaagaaa tggctcaaat tagaaggaaa tttgaattgt tcacctatac taggtttgat    360
tctgaaataa ccctagttcc atgcatttcc gcccttagtc aggacattgg acacatcaca    420
atgcaataca tgtatgttcc acctggtgca ccggtgccca atagtaggga cgattatgca    480
tggcagtctg gcactaatgc ctctgttttc tggcaacatg gacaggctta tccaagattt    540
tccttacctt tcctaagtgt ggcatctgct tattacatgt tttatgatgg gtatgatgaa    600
caagatcaaa actatggtac agcaagcaca aataacatgg ggtcactatg ctctaggata    660
gtaacagaga aacacattca taaggtacat ataatgacaa gaatctatca caaggctaaa    720
catgtcaagg catggtgtcc acgcccaccc agagcgcttg agtatactcg tgctcaccgc    780
actaattta aaattgagga taggagtatt cagacagcaa ttgtgaccag accaattatc    840
actacagca                                                             849

<210> SEQ ID NO 149
<211> LENGTH: 849
<212> TYPE: DNA
<213> ORGANISM: rhinovirus

<400> SEQUENCE: 149
aaccctgttg agaattatat agatgaagtt cttaatgaag ttttagttgt cccaaatatt      60
aatagtagta accccacaac atcaaattct gccccagcat tagatgctgc agaaacaggg    120
cacactagta gtgttcaacc agaggatgtc attgaaacta ggtatgtgca gacatcacaa    180
acaagagatg aaatgagttt agagagtttt cttggcagat caggatgcat acatgaatct    240
aaattagagg ttacacttgc aaattataac aaggagaatt ttacagtgtg ggctattaat    300
atacaagaaa tggctcaaat tagaaggaaa tttgaattgt tcacctatac taggtttgat    360
tctgaaataa ccctagttcc atgcatttcc gcccttagtc aggacattgg acacatcaca    420
atgcaataca tgtatgttcc acctggtgca ccggtgccca atagtaggga cgattatgca    480
tggcagtctg gcactaatgc ctctgttttc tggcaacatg gacaggctta tccaagattt    540
tccttacctt tcctaagtgt ggcatctgct tattacatgt tttatgatgg gtatgatgaa    600
caagatcaaa actatggtac agcaagcaca aataacatgg ggtcactatg ctctaggata    660
gtaacagaga aacacattca taaggtacat ataatgacaa gaatctatca caaggctaaa    720
catgtcaagg catggtgtcc acgcccaccc agagcgcttg agtatactcg tgctcaccgc    780
actaattta aaattgagga taggagtatt cagacagcaa ttgtgaccag accaattatc    840
actacagcg                                                             849
```

<210> SEQ ID NO 150
<211> LENGTH: 849
<212> TYPE: DNA
<213> ORGANISM: rhinovirus

<400> SEQUENCE: 150

```
aatcctgttg aacactacat agatgaggtc cttaatgagg ttttagttgt tccaaatatt      60
aatagtagtc accccacgac atcaaactct gctccagcat tagatgctgc agaaacaggg     120
cacactagca atgtgcaacc tgaagatgtc attgaaacca gatatgtaca gacatcacaa     180
acaagagatg aaatgagttt agagagtttt cttggtaggt cagggtgtat acatgaatcc     240
aaactagagg tcacacttac aaattacaat gaaaataatt tcaaagtatg gaacatcaat     300
ttgcaagaaa tggcccagat cagaagaaaa tttgaactgt ttacttacac tagattcgat     360
tctgaaataa ccttggttcc atgcatttct gcacttagca aggatattgg acacattaca     420
atgcaataca tgtatgtgcc gccaggtgca cctgtaccaa agagcagaga tgattatgca     480
tggcagtctg gcactaatgc atctgttttc tggcaacatg ggcaagcata cccaagattt     540
tctctacccct ttttgagtgt agcttcagct tactacatgt tttatgatgg atataatgaa     600
cagggccaaa attatggtac ggtaagtaca acaacatgg gatcattatg ctctaggata      660
gtaacagaga aacacattca cagtatgcat atcatgacaa gaatctatca taaagctaaa     720
cacgtcaaag catggtgtcc gcgcccaccc agagcacttg aatatactcg cgctcaccgt     780
actaatttca agttgaaga cagagacatt aaaacaggaa tcacatccag agcaattatt     840
acaacagcg                                                              849
```

<210> SEQ ID NO 151
<211> LENGTH: 849
<212> TYPE: DNA
<213> ORGANISM: rhinovirus

<400> SEQUENCE: 151

```
aatcctgttg aacactacat agatgaggtc cttaatgagg ttttagttgt tccaaatatt      60
aatagtagtc accccacgac atcaaactct gctccagcat tagatgctgc agaaacaggg     120
cacactagca atgtgcaacc tgaagatgtc attgaaacca gatatgtaca gacatcacaa     180
acaagagatg aaatgagttt agagagtttt cttggtaggt cagggtgtat acatgaatcc     240
aaactagagg tcacacttac aaattacaat gaaaataatt tcaaagtatg gaacatcaat     300
ttgcaagaaa tggcccagat cagaagaaaa tttgaactgt ttacttacac tagattcgat     360
tctgaaataa ccttggttcc atgcatttct gcacttagca aggatattgg acacattaca     420
atgcaataca tgtatgtgcc gccaggtgca cctgtaccaa agagcagaga tgattatgca     480
tggcagtctg gcactaatgc atctgttttc tggcaacatg ggcaagcata cccaagattt     540
tctctacccct ttttgagtgt agcttcagct tactacatgt tttatgatgg atataatgaa     600
cagggccaaa attatggtac ggtaagtaca acaacatgg gatcattatg ctctaggata      660
gtaacagaga aacacattca cagtatgcat atcatgacaa gaatctatca taaagctaaa     720
cacgtcaaag catggtgtcc gcgcccaccc agagcacttg aatatactcg cgctcaccgt     780
actaatttca agttgaaga cagagacatt aaaacaggaa tcacatccag agcaattatt     840
acaacagca                                                              849
```

<210> SEQ ID NO 152
<211> LENGTH: 849
<212> TYPE: DNA

<213> ORGANISM: rhinovirus

<400> SEQUENCE: 152

```
aatcctgttg aacactacat agatgaggtc cttaatgagg ttttagttgt tccaaatatt    60
aatagtagtc accccacgac atcaaactct gctccagcat tagatgctgc agaaacaggg   120
cacactagca atgtgcaacc tgaagatgtc attgaaacca gatatgtaca gacatcacaa   180
acaagagatg aaatgagttt agagagtttt cttggtaggt cagggtgtat acatgaatcc   240
aaactagagg tcacacttac aaattacaat gaaataatt tcaaagtatg aacatcaat    300
ttgcaagaaa tggcccagat cagaagaaaa tttgaactgt ttacttacac tagattcgat   360
tctgaaataa ccttggttcc atgcatttct gcacttagca aggatattgg acacattaca   420
atgcaataca tgtatgtgcc gccaggtgca cctgtaccaa agagcagaga tgattatgca   480
tggcagtctg gcactaatgc atctgttttc tggcaacatg ggcaagcata cccaagattt   540
tctctaccct ttttgagtgt agcttcagct tactacatgt tttatgatgg atataatgaa   600
cagggccaaa attatggtac ggtaagtaca acaacatgg gatcattatg ctctaggata   660
gtaacagaga aacacattca cagtatgcat atcatgacaa gaatctatca taaagctaaa   720
cacgtcaaag catggtgtcc gcgcccaccc agagcacttg aatatactcg cgctcaccgt   780
actaatttca aagttgaaga cagagacatt aaaacaggaa tcacatccag agcaattatt   840
acaacagct                                                            849
```

<210> SEQ ID NO 153
<211> LENGTH: 849
<212> TYPE: DNA
<213> ORGANISM: rhinovirus

<400> SEQUENCE: 153

```
aatccaattg agaactatgt agatgaagtt cttaatgaag tcttagttgt tcccaatatc    60
aatagtagtc atcccacaac atcaaactct gctccagcat tagacgctgc ggaaacgggt   120
cacactagta atgttcaacc agaagatgtc attgaaacca ggtacgttca acatcacaa    180
acaagagatg aaatgagttt agaaagtttc cttggtaggt cagggtgtat acatgaatct   240
aaattaaaag ttgagatcgg aaactatgat gaaaacaatt ttaatacttg gaatattaat   300
ttacaggaaa tggcccaaat cagaagaaag tttgaactgt ttacttacac tagatttgat   360
tctgaaatta cttttggttcc atgcatttct gctcttagtc aagatattgg tcacatcaca   420
atgcagtata tgtatgtccc accaggtgct ccaataccgg aaagtagaaa tgactatgca   480
tggcaatctg gaacaaatgc gtccattttt tggcaacatg gacaaacata tccaaggttc   540
tccttaccct ttttgagtgt ggcatctgct tattacatgt tttatgatgg atacaatgag   600
aaaggcacgc attatggaac agttagcaca acaacatgg gcacattgtg ctccagagtg   660
gtaacagaga aacacattca tgatatgcgg ataatgacaa gggtctacca caaagctaaa   720
catgtcaaag catggtgtcc gcggccaccc agagcacttg aatacacacg cgctcaccgt   780
actaatttca aaattgaagg tgaaaatgtc aaatcaaggg ttgcacatag acctgcagtg   840
ataacagcg                                                            849
```

<210> SEQ ID NO 154
<211> LENGTH: 849
<212> TYPE: DNA
<213> ORGANISM: rhinovirus

<400> SEQUENCE: 154

```
aatccaattg agaactatgt agatgaagtt cttaatgaag tcttagttgt tcccaatatc      60
aatagtagtc atcccacaac atcaaactct gctccagcat tagacgctgc ggaaacgggt     120
cacactagta atgttcaacc agaagatgtc attgaaacca ggtacgttca acatcacaa     180 acaagagatg aaatgagttt agaaagtttc cttggtaggt cagggtgtat acatgaatct     240
aaattaaaag ttgagatcgg aaactatgat gaaaacaatt ttaatacttg gaatattaat     300
ttacaggaaa tgcccaaat cagaagaaag tttgaactgt ttacttacac tagatttgat     360
tctgaaatta ctttggttcc atgcatttct gctcttagtc aagatattgg tcacatcaca     420
atgcagtata tgtatgtccc accaggtgct ccaataccgg aaagtagaaa tgactatgca     480
tggcaatctg gaacaaatgc gtccattttt tggcaacatg gacaaacata tccaaggttc     540
tccttaccct ttttgagtgt ggcatctgct tattacatgt tttatgatgg atacaatgag     600
aaaggcacgc attatggaac agttagcaca acaacatgg gcacattgtg ctccagagtg     660
gtaacagaga aacacattca tgatatgcgg ataatgacaa gggtctacca caaagctaaa     720
catgtcaaag catggtgtcc gcggccaccc agagcacttg aatacacacg cgctcaccgt     780
actaatttca aaattgaagg tgaaaatgtc aaatcaaggg ttgcacatag acctgcagtg     840
ataacagca                                                             849

<210> SEQ ID NO 155
<211> LENGTH: 849
<212> TYPE: DNA
<213> ORGANISM: rhinovirus

<400> SEQUENCE: 155
aatccaattg agaactatgt agatgaagtt cttaatgaag tcttagttgt tcccaatatc      60
aatagtagtc atcccacaac atcaaactct gctccagcat tagacgctgc ggaaacgggt     120
cacactagta atgttcaacc agaagatgtc attgaaacca ggtacgttca acatcacaa     180 acaagagatg aaatgagttt agaaagtttc cttggtaggt cagggtgtat acatgaatct     240
aaattaaaag ttgagatcgg aaactatgat gaaaacaatt ttaatacttg gaatattaat     300
ttacaggaaa tgcccaaat cagaagaaag tttgaactgt ttacttacac tagatttgat     360
tctgaaatta ctttggttcc atgcatttct gctcttagtc aagatattgg tcacatcaca     420
atgcagtata tgtatgtccc accaggtgct ccaataccgg aaagtagaaa tgactatgca     480
tggcaatctg gaacaaatgc gtccattttt tggcaacatg gacaaacata tccaaggttc     540
tccttaccct ttttgagtgt ggcatctgct tattacatgt tttatgatgg atacaatgag     600
aaaggcacgc attatggaac agttagcaca acaacatgg gcacattgtg ctccagagtg     660
gtaacagaga aacacattca tgatatgcgg ataatgacaa gggtctacca caaagctaaa     720
catgtcaaag catggtgtcc gcggccaccc agagcacttg aatacacacg cgctcaccgt     780
actaatttca aaattgaagg tgaaaatgtc aaatcaaggg ttgcacatag acctgcagtg     840
ataacagct                                                             849

<210> SEQ ID NO 156
<211> LENGTH: 849
<212> TYPE: DNA
<213> ORGANISM: rhinovirus

<400> SEQUENCE: 156
aacccggttg aaaattttgt agatgaagtt cttagtgaag ttttagttgt tccaaacatt      60
```

```
aacagtagtc accctactac atcaaactct gctccggcat tagatgctgc agaaacagga      120
catactagta atgttcaacc tgaagatgtc attgaaacta gatatgttca acatcacaa      180 acaagggatg aaatgagttt agaaagcttt cttggtagat caggatgtat acacgagtct      240
aaattagaac ttgagcttgc acactatgat aaaaagaact ttaccacatg gaatattaat      300
cttcaagaaa tggcccaaat tagaagaaaa tttgagctat tcacttacac tagatttgat      360
tctgagataa ccttggttcc gtgtatttca gctctcagcc aagatatcgg acacattaca      420
atgcagtata tgtatgttcc acctggcgct ccaattcccg agagcagaaa tgactatgca      480
tggcagtctg gaacaaatgc atctgttttt tggcaacacg gacaaacata cccaagattc      540
tccctaccat ttttgagtgt agcatctgct tattacatgt tctatgatgg atacaatgag      600
ggaggcacaa attatggtac agtgagcaca acaacatgg gcacactgtg ttccagagtg      660
gtaacagaaa aacacattca tgatgtgcgc ataatgacaa gggtctacca caaggctaaa      720
catgtcaaag cgtggtgtcc acggccacct agggcgcttg agtatacccg tgctcatcgc      780 accaattttta aaattgatgg cagggaagtt aaatcaaggg ttgaacacag agctagggtg      840
acgacagca                                                              849

<210> SEQ ID NO 157
<211> LENGTH: 849
<212> TYPE: DNA
<213> ORGANISM: rhinovirus

<400> SEQUENCE: 157
aacccggttg aaaattttgt agatgaagtt cttagtgaag ttttagttgt tccaaacatt       60
aacagtagtc accctactac atcaaactct gctccggcat tagatgctgc agaaacagga      120
catactagta atgttcaacc tgaagatgtc attgaaacta gatatgttca acatcacaa      180 acaagggatg aaatgagttt agaaagcttt cttggtagat caggatgtat acacgagtct      240
aaattagaac ttgagcttgc acactatgat aaaaagaact ttaccacatg gaatattaat      300
cttcaagaaa tggcccaaat tagaagaaaa tttgagctat tcacttacac tagatttgat      360
tctgagataa ccttggttcc gtgtatttca gctctcagcc aagatatcgg acacattaca      420
atgcagtata tgtatgttcc acctggcgct ccaattcccg agagcagaaa tgactatgca      480
tggcagtctg gaacaaatgc atctgttttt tggcaacacg gacaaacata cccaagattc      540
tccctaccat ttttgagtgt agcatctgct tattacatgt tctatgatgg atacaatgag      600
ggaggcacaa attatggtac agtgagcaca acaacatgg gcacactgtg ttccagagtg      660
gtaacagaaa aacacattca tgatgtgcgc ataatgacaa gggtctacca caaggctaaa      720
catgtcaaag cgtggtgtcc acggccacct agggcgcttg agtatacccg tgctcatcgc      780 accaattttta aaattgatgg cagggaagtt aaatcaaggg ttgaacacag agctagggtg      840
acgacagcg                                                              849

<210> SEQ ID NO 158
<211> LENGTH: 849
<212> TYPE: DNA
<213> ORGANISM: rhinovirus

<400> SEQUENCE: 158
aacccggttg aaaattttgt agatgaagtt cttagtgaag ttttagttgt tccaaacatt       60
aacagtagtc accctactac atcaaactct gctccggcat tagatgctgc agaaacagga      120
catactagta atgttcaacc tgaagatgtc attgaaacta gatatgttca acatcacaa      180
```

```
acaagggatg aaatgagttt agaaagcttt cttggtagat caggatgtat acacgagtct    240
aaattagaac ttgagcttgc acactatgat aaaaagaact ttaccacatg gaatattaat    300
cttcaagaaa tggcccaaat tagaagaaaa tttgagctat tcacttacac tagatttgat    360
tctgagataa ccttggttcc gtgtatttca gctctcagcc aagatatcgg acacattaca    420
atgcagtata tgtatgttcc acctggcgct ccaattcccg agagcagaaa tgactatgca    480
tggcagtctg aacaaatgc atctgttttt tggcaacacg gacaaacata cccaagattc    540
tccctaccat ttttgagtgt agcatctgct tattacatgt tctatgatgg atacaatgag    600
ggaggcacaa attatggtac agtgagcaca acaacatgg gcacactgtg ttccagagtg    660
gtaacagaaa aacacattca tgatgtgcgc ataatgacaa gggtctacca caaggctaaa    720
catgtcaaag cgtggtgtcc acggccacct agggcgcttg agtatacccg tgctcatcgc    780 accaattta aaattgatgg cagggaagtt aaatcaaggg ttgaacacag agctagggtg    840
acgacagct                                                            849

<210> SEQ ID NO 159
<211> LENGTH: 873
<212> TYPE: DNA
<213> ORGANISM: rhinovirus

<400> SEQUENCE: 159
aacccggtag agaattatgt agatagctta ctaaatgaag tattagtggt acctaatatt     60
cagccaagta catctgtttc aagtcactct gtaccagcat tggatgctgc agagactgga    120
catactagtt ctgttcaacc tgaagatatg atcgagacaa ggtatgtcat aacagaccaa    180
acaagggatg aaactagtat agagagtttc ttaggtagat ctggatgtat tgctaaagtt    240
aaacttgaca caacacaggg tgactatgac acaggcaaag gtgttggttt cactacatgg    300
aaaatcagct acaagaaat ggcacaaatc agaagaaagt ttgaactatt cacatacact    360
agatttgatt ctgagataac aatagtcaca gcagcagcag cacaaggtaa tgatattgga    420
catatagtta tgcaatttat gtatgtacct ccaggggccc cagttccaat aaaacgcgaa    480
gattatacat ggcaatcagg aacaaatgct tctatatttt ggcaggaggg tcaaccatac    540
cctagattca caattccttt tatgagtatt gcatcagctt attatatgtt ctatgatgga    600
tatgatggtg atgatgcgtc atccaaatat ggttccgtag taaccaatga catgggaacc    660
atatgtgtta gactagttac atctacacaa aaacacaatt aaagattgt gagtcgcatt    720 taccacaaag ccaaacatat aaaagcatgg tgcccacgcc caccacgagc tgtgccttat    780
caacacactc actccaccaa ctatgtgcca caaaatggag aggtcgcaac tcaaatcaaa    840
accagagcca atcttttcac cctcaaatca gct                                 873

<210> SEQ ID NO 160
<211> LENGTH: 873
<212> TYPE: DNA
<213> ORGANISM: rhinovirus

<400> SEQUENCE: 160
aacccggtag agaattatgt agatagctta ctaaatgaag tattagtggt acctaatatt     60
cagccaagta catctgtttc aagtcactct gtaccagcat tggatgctgc agagactgga    120
catactagtt ctgttcaacc tgaagatatg atcgagacaa ggtatgtcat aacagaccaa    180
acaagggatg aaactagtat agagagtttc ttaggtagat ctggatgtat tgctaaagtt    240
```

```
aaacttgaca caacacaggg tgactatgac acaggcaaag gtgttggttt cactacatgg    300
aaaatcagct tacaagaaat ggcacaaatc agaagaaagt ttgaactatt cacatacact    360
agatttgatt ctgagataac aatagtcaca gcagcagcag cacaaggtaa tgatattgga    420
catatagtta tgcaatttat gtatgtacct ccaggggccc cagttccaat aaaacgcgaa    480
gattatacat ggcaatcagg aacaaatgct tctatatttt ggcaggaggg tcaaccatac    540
cctagattca caattccttt tatgagtatt gcatcagctt attatatgtt ctatgatgga    600
tatgatggtg atgatgcgtc atccaaatat ggttccgtag taaccaatga catgggaacc    660
atatgtgtta gactagttac atctacacaa aaacacaatt taaagattgt gagtcgcatt    720
taccacaaag ccaaacatat aaaagcatgg tgcccacgcc caccacgagc tgtgccttat    780
caacacactc actccaccaa ctatgtgcca caaaatggag aggtcgcaac tcaaatcaaa    840
accagagcca atcttttcac cctcaaatca gca                                873
```

<210> SEQ ID NO 161
<211> LENGTH: 873
<212> TYPE: DNA
<213> ORGANISM: rhinovirus

<400> SEQUENCE: 161

```
aacccggtag agaattatgt agatagctta ctaaatgaag tattagtggt acctaatatt     60
cagccaagta catctgtttc aagtcactct gtaccagcat ggatgctgc agagactgga    120 catactagtt ctgttcaacc tgaagatatg atcgagacaa ggtatgtcat aacagaccaa    180
acaagggatg aaactagtat agagagtttc ttaggtagat ctggatgtat tgctaaagtt    240
aaacttgaca caacacaggg tgactatgac acaggcaaag gtgttggttt cactacatgg    300
aaaatcagct tacaagaaat ggcacaaatc agaagaaagt ttgaactatt cacatacact    360
agatttgatt ctgagataac aatagtcaca gcagcagcag cacaaggtaa tgatattgga    420
catatagtta tgcaatttat gtatgtacct ccaggggccc cagttccaat aaaacgcgaa    480
gattatacat ggcaatcagg aacaaatgct tctatatttt ggcaggaggg tcaaccatac    540
cctagattca caattccttt tatgagtatt gcatcagctt attatatgtt ctatgatgga    600
tatgatggtg atgatgcgtc atccaaatat ggttccgtag taaccaatga catgggaacc    660
atatgtgtta gactagttac atctacacaa aaacacaatt taaagattgt gagtcgcatt    720
taccacaaag ccaaacatat aaaagcatgg tgcccacgcc caccacgagc tgtgccttat    780
caacacactc actccaccaa ctatgtgcca caaaatggag aggtcgcaac tcaaatcaaa    840
accagagcca atcttttcac cctcaaatca gcg                                873
```

<210> SEQ ID NO 162
<211> LENGTH: 870
<212> TYPE: DNA
<213> ORGANISM: rhinovirus

<400> SEQUENCE: 162

```
aatccagtag aaaactatgt agataacttg ttaaacgaag tgctagtagt tcctaacatt     60
caacctagca catccgtttc aagtcactct gtgccagctc tggatgctgc ggaaacaggg    120
catactagtt ctgttcaacc tgaagatatg atagaaacta gatatgttat aacagatcaa    180
acaagggatg aaaccagcat tgaaagcttt ctgggtaggt ctggatgcat agcaaaaatt    240
aaacttgaca caaatgaagg tgattacgac acaataggtg ttggatttgt aacatggaag    300
attagcttgc aagaaatggc acaaatcagg agaaaatttg aattgtttac atacactaga    360
```

```
tttgactcag aaataacaat agtcacagca gctgcagcac aaggtgatga tactggacat    420
atagtactgc aattcatgta tgtgcctcca ggtgcaccaa ttcccaagaa acgtgatgat    480
tacacatggc agtcaggaac aaatgcatct gtgttctggc aagaaggaca accatatccca   540 agatttacca ttcccttat gagtattgca tcagcttact atatgtttta tgatggatat    600
gatggtgatg atgcatcatc taggtatggc tcagtggtaa ctaatgatat gggaactata    660
tgtattagat tggtcacctc cacccaaaag cataaactga atatcattag ccgtatatat    720
cacaaggcta acatataaa ggcatggtgt ccacgcccac caagagccgt accttatcag    780
cacacacact ccaccaatta tgtaccaaca gatggggaag tagcaactca aatcaaaacc    840
agacgagatg tttacactgt taccactgct                                     870

<210> SEQ ID NO 163
<211> LENGTH: 870
<212> TYPE: DNA
<213> ORGANISM: rhinovirus

<400> SEQUENCE: 163
aatccagtag aaaactatgt agataacttg ttaaacgaag tgctagtagt tcctaacatt     60
caacctagca catccgtttc aagtcactct gtgccagctc tggatgctgc ggaaacaggg    120
catactagtt ctgttcaacc tgaagatatg atagaaacta gatatgttat aacagatcaa    180
acaagggatg aaaccagcat tgaaagcttt ctgggtaggt ctggatgcat agcaaaaatt    240
aaacttgaca caaatgaagg tgattacgac acaataggtg ttggatttgt aacatggaag    300
attagcttgc aagaaatggc acaaatcagg agaaaatttg aattgtttac atacactaga    360
tttgactcag aaataacaat agtcacagca gctgcagcac aaggtgatga tactggacat    420
atagtactgc aattcatgta tgtgcctcca ggtgcaccaa ttcccaagaa acgtgatgat    480
tacacatggc agtcaggaac aaatgcatct gtgttctggc aagaaggaca accatatccca   540 agatttacca ttcccttat gagtattgca tcagcttact atatgtttta tgatggatat    600
gatggtgatg atgcatcatc taggtatggc tcagtggtaa ctaatgatat gggaactata    660
tgtattagat tggtcacctc cacccaaaag cataaactga atatcattag ccgtatatat    720
cacaaggcta acatataaa ggcatggtgt ccacgcccac caagagccgt accttatcag    780
cacacacact ccaccaatta tgtaccaaca gatggggaag tagcaactca aatcaaaacc    840
agacgagatg tttacactgt taccactgca                                     870

<210> SEQ ID NO 164
<211> LENGTH: 870
<212> TYPE: DNA
<213> ORGANISM: rhinovirus

<400> SEQUENCE: 164
aatccagtag aaaactatgt agataacttg ttaaacgaag tgctagtagt tcctaacatt     60
caacctagca catccgtttc aagtcactct gtgccagctc tggatgctgc ggaaacaggg    120
catactagtt ctgttcaacc tgaagatatg atagaaacta gatatgttat aacagatcaa    180
acaagggatg aaaccagcat tgaaagcttt ctgggtaggt ctggatgcat agcaaaaatt    240
aaacttgaca caaatgaagg tgattacgac acaataggtg ttggatttgt aacatggaag    300
attagcttgc aagaaatggc acaaatcagg agaaaatttg aattgtttac atacactaga    360
tttgactcag aaataacaat agtcacagca gctgcagcac aaggtgatga tactggacat    420
```

| atagtactgc aattcatgta tgtgcctcca ggtgcaccaa ttcccaagaa acgtgatgat | 480 |
| tacacatggc agtcaggaac aaatgcatct gtgttctggc aagaaggaca accatacccc | 540 |
| agatttacca ttcccttat gagtattgca tcagcttact atatgtttta tgatggatat | 600 |
| gatggtgatg atgcatcatc taggtatggc tcagtggtaa ctaatgatat gggaactata | 660 |
| tgtattagat tggtcacctc cacccaaaag cataaactga atatcattag ccgtatatat | 720 |
| cacaaggcta acatataaa ggcatggtgt ccacgcccac caagagccgt accttatcag | 780 |
| cacacacact ccaccaatta tgtaccaaca gatggggaag tagcaactca aatcaaaacc | 840 |
| agacgagatg tttacactgt taccactgcg | 870 |

<210> SEQ ID NO 165
<211> LENGTH: 867
<212> TYPE: DNA
<213> ORGANISM: rhinovirus

<400> SEQUENCE: 165

| aatccagttg aaaattacat agataatgta ttaaatgaag tacttgtagt gccaaacatc | 60 |
| caacctagtt catctgtgtc aagtcattca gctcccgcct tagacgctgc ggaaactgga | 120 |
| cataccagct ctgtccaacc agaggacatg atcgagacca gatatgtcat aactgatcaa | 180 |
| acaagagatg agacaagtat tgaaagcttc ttaggtaggt cagggtgcat agctatgata | 240 |
| gaatttagca caagtagtga taaagatgaa catgatgaaa ttggcaaggg attcaaaaca | 300 |
| tggaagatta gtcttcaaga aatggcacaa attagaagga aatatgaatt gtttacatac | 360 |
| acaagatttg actcagaaat aacaatagtc accgcagctg cagtgcaggg agatgatagt | 420 |
| gggcatgtag tattacaatt catgtatgta cctccaggag cgcctgttcc tgtgaagcgt | 480 |
| gatgactaca catggcaatc agggacaaat gcatctgtgt tctggcaaga agggcaacca | 540 |
| tatcctagat ttacaatccc ctttatgagt attgcatcag cttattatat gttttatgat | 600 |
| ggttatgatg gtgataatgc cgcatcaaaa tatggatctg tggttactaa cgacatggga | 660 |
| accatatgtg ttagaatagt tacatccaac caaaaacatg atttaaatat tgtatgccgc | 720 |
| atttatcata aagctaaaca cataaaggcc tggtgcccgc gtccaccaag ggccgttcct | 780 |
| taccaacaca cacattccac taattatata ccatacaaag gtgagatcac aacccaaatt | 840 |
| aaaaccagac ctaatgtctt cactgta | 867 |

<210> SEQ ID NO 166
<211> LENGTH: 867
<212> TYPE: DNA
<213> ORGANISM: rhinovirus

<400> SEQUENCE: 166

| aatccagttg aaaattacat agataatgta ttaaatgaag tacttgtagt gccaaacatc | 60 |
| caacctagtt catctgtgtc aagtcattca gctcccgcct tagacgctgc ggaaactgga | 120 |
| cataccagct ctgtccaacc agaggacatg atcgagacca gatatgtcat aactgatcaa | 180 |
| acaagagatg agacaagtat tgaaagcttc ttaggtaggt cagggtgcat agctatgata | 240 |
| gaatttagca caagtagtga taaagatgaa catgatgaaa ttggcaaggg attcaaaaca | 300 |
| tggaagatta gtcttcaaga aatggcacaa attagaagga aatatgaatt gtttacatac | 360 |
| acaagatttg actcagaaat aacaatagtc accgcagctg cagtgcaggg agatgatagt | 420 |
| gggcatgtag tattacaatt catgtatgta cctccaggag cgcctgttcc tgtgaagcgt | 480 |
| gatgactaca catggcaatc agggacaaat gcatctgtgt tctggcaaga agggcaacca | 540 |

| | |
|---|---:|
| tatcctagat ttacaatccc ctttatgagt attgcatcag cttattatat gttttatgat | 600 |
| ggttatgatg gtgataatgc cgcatcaaaa tatggatctg tggttactaa cgacatggga | 660 |
| accatatgtg ttagaatagt tacatccaac caaaaacatg atttaaatat tgtatgccgc | 720 |
| atttatcata aagctaaaca cataaaggcc tggtgcccgc gtccaccaag ggccgttcct | 780 |
| taccaacaca cacattccac taattatata ccatacaaag gtgagatcac aacccaaatt | 840 |
| aaaaccagac ctaatgtctt cactgtg | 867 |

<210> SEQ ID NO 167
<211> LENGTH: 867
<212> TYPE: DNA
<213> ORGANISM: rhinovirus

<400> SEQUENCE: 167

| | |
|---|---:|
| aatccagttg aaaattacat agataatgta ttaaatgaag tacttgtagt gccaaacatc | 60 |
| caacctagtt catctgtgtc aagtcattca gctcccgcct tagacgctgc ggaaactgga | 120 |
| cataccagct ctgtccaacc agaggacatg atcgagacca gatatgtcat aactgatcaa | 180 |
| acaagagatg agacaagtat tgaaagcttc ttaggtaggt cagggtgcat agctatgata | 240 |
| gaatttagca caagtagtga taaagatgaa catgatgaaa ttggcaaggg attcaaaaca | 300 |
| tggaagatta gtcttcaaga aatggcacaa attagaagga aatatgaatt gtttacatac | 360 |
| acaagatttg actcagaaat aacaatagtc accgcagctg cagtgcaggg agatgatagt | 420 |
| gggcatgtag tattacaatt catgtatgta cctccaggag cgcctgttcc tgtgaagcgt | 480 |
| gatgactaca catggcaatc agggacaaat gcatctgtgt tctggcaaga agggcaacca | 540 |
| tatcctagat ttacaatccc ctttatgagt attgcatcag cttattatat gttttatgat | 600 |
| ggttatgatg gtgataatgc cgcatcaaaa tatggatctg tggttactaa cgacatggga | 660 |
| accatatgtg ttagaatagt tacatccaac caaaaacatg atttaaatat tgtatgccgc | 720 |
| atttatcata aagctaaaca cataaaggcc tggtgcccgc gtccaccaag ggccgttcct | 780 |
| taccaacaca cacattccac taattatata ccatacaaag gtgagatcac aacccaaatt | 840 |
| aaaaccagac ctaatgtctt cactgtt | 867 |

<210> SEQ ID NO 168
<211> LENGTH: 876
<212> TYPE: DNA
<213> ORGANISM: rhinovirus

<400> SEQUENCE: 168

| | |
|---|---:|
| aacccagttg aaaattatat agatagtgta ttaaatgaag ttcttgtggt gccaaatatc | 60 |
| caacctagca catctgtgtc aagtcatgca gcgcctgcat tggatgctgc ggaaaccgga | 120 |
| cacaccagct ctgttcaacc tgaagatatg attgaaacta gatatgttat aactgatcaa | 180 |
| acaagggatg aaacaagtat tgagagtttc ttaggtaggt cagggtgtat cgctatgata | 240 |
| gaatttaata caagtagtga taaaactgaa catgataaaa ttggtaaagg attcaaaaca | 300 |
| tggaaggtta gtcttcaaga aatggcacaa atcagaagaa aatatgaatt attcacatat | 360 |
| acaagatttg attcagagat aacaatagtc actgcagccg cagctcaagg aaatgatagt | 420 |
| ggacatatag tattgcaatt tatgtatgta cccccaggag cacctgtccc cgaaaaacgt | 480 |
| gatgattaca catggcaatc aggaacaaat gcatctgtgt tctggcaaga aggacaacca | 540 |
| tacccccagat tcacaatccc ttttatgagc attgcatcag cctattacat gttttatgat | 600 |

```
ggttatgatg gtgatagtgc agcatcaaaa tacggttctg tagtcactaa tgatatggga    660
accatatgtg ttagaatagt gacatccaac caaaaacatg atttaaatat tgtgtgccgc    720
atttaccaca aggccaaaca tataaaagca tggtgtcctc gcccaccaag ggctgttgcc    780
tatcaacaca cacactcaac caattacata ccatccaatg gtgaggccac aactcagatt    840
aaaaccagac ctgatgtttt taccgttaca aacgtg                              876
```

<210> SEQ ID NO 169
<211> LENGTH: 876
<212> TYPE: DNA
<213> ORGANISM: rhinovirus

<400> SEQUENCE: 169

```
aacccagttg aaaattatat agatagtgta ttaaatgaag ttcttgtggt gccaaatatc     60
caacctagca catctgtgtc aagtcatgca gcgcctgcat tggatgctgc ggaaaccgga    120
cacaccagct ctgttcaacc tgaagatatg attgaaacta gatatgttat aactgatcaa    180
acaagggatg aaacaagtat tgagagtttc ttaggtaggt cagggtgtat cgctatgata    240
gaatttaata caagtagtga taaaactgaa catgataaaa ttggtaaagg attcaaaaca    300
tggaaggtta gtcttcaaga aatggcacaa atcagaagaa aatatgaatt attcacatat    360
acaagatttg attcagagat aacaatagtc actgcagccg cagctcaagg aaatgatagt    420
ggacatatag tattgcaatt tatgtatgta cccccaggag cacctgtccc cgaaaaacgt    480
gatgattaca catggcaatc aggaacaaat gcatctgtgt tctggcaaga aggacaacca    540
taccccagat tcacaatccc ttttatgagc attgcatcag cctattacat gttttatgat    600
ggttatgatg gtgatagtgc agcatcaaaa tacggttctg tagtcactaa tgatatggga    660
accatatgtg ttagaatagt gacatccaac caaaaacatg atttaaatat tgtgtgccgc    720
atttaccaca aggccaaaca tataaaagca tggtgtcctc gcccaccaag ggctgttgcc    780
tatcaacaca cacactcaac caattacata ccatccaatg gtgaggccac aactcagatt    840
aaaaccagac ctgatgtttt taccgttaca aacgta                              876
```

<210> SEQ ID NO 170
<211> LENGTH: 876
<212> TYPE: DNA
<213> ORGANISM: rhinovirus

<400> SEQUENCE: 170

```
aacccagttg aaaattatat agatagtgta ttaaatgaag ttcttgtggt gccaaatatc     60
caacctagca catctgtgtc aagtcatgca gcgcctgcat tggatgctgc ggaaaccgga    120
cacaccagct ctgttcaacc tgaagatatg attgaaacta gatatgttat aactgatcaa    180
acaagggatg aaacaagtat tgagagtttc ttaggtaggt cagggtgtat cgctatgata    240
gaatttaata caagtagtga taaaactgaa catgataaaa ttggtaaagg attcaaaaca    300
tggaaggtta gtcttcaaga aatggcacaa atcagaagaa aatatgaatt attcacatat    360
acaagatttg attcagagat aacaatagtc actgcagccg cagctcaagg aaatgatagt    420
ggacatatag tattgcaatt tatgtatgta cccccaggag cacctgtccc cgaaaaacgt    480
gatgattaca catggcaatc aggaacaaat gcatctgtgt tctggcaaga aggacaacca    540
taccccagat tcacaatccc ttttatgagc attgcatcag cctattacat gttttatgat    600
ggttatgatg gtgatagtgc agcatcaaaa tacggttctg tagtcactaa tgatatggga    660
accatatgtg ttagaatagt gacatccaac caaaaacatg atttaaatat tgtgtgccgc    720
```

| | |
|---|---|
| atttaccaca aggccaaaca tataaaagca tggtgtcctc gcccaccaag ggctgttgcc | 780 |
| tatcaacaca cacactcaac caattacata ccatccaatg gtgaggccac aactcagatt | 840 |
| aaaaccagac ctgatgtttt taccgttaca aacgtc | 876 |

<210> SEQ ID NO 171
<211> LENGTH: 870
<212> TYPE: DNA
<213> ORGANISM: rhinovirus

<400> SEQUENCE: 171

| | |
|---|---|
| aatccagtag aaaattacat agataatgtg ttaaatgaag tacttgtagt tccaaatatc | 60 |
| caacctagta catctgtatc aagtcattct gtgcctgcct tggatgctgc agaaacggga | 120 |
| cacacaagtt ctgttcagcc tgaggatatg attgaaacta gatatgttat cacagatcaa | 180 |
| acaagagatg aaactagcat tgaaagcttt ttaggtagat ctggttgcat tgctatcata | 240 |
| aaatttaaca caaataagac taattatgat gacataggtg taggatacaa acatggaaa | 300 |
| attagccttc aagagatggc acaaattaga aggaaatttg agttgtttac atatacaaga | 360 |
| tttgactcag agattacaat agtcactgca gcagctgctc aaggagaaga taatggacat | 420 |
| attgtgttac aatttatgta tgtaccccca ggagcacctg tacccaagaa tcgtgatgac | 480 |
| tttacatggc aatcaggcac aaatgcatct gttttctggc aggaaggaca accatacct | 540 |
| agatttacaa tccctttat gagcattgca tcagcttact atatgtttta tgatggctat | 600 |
| gatggtgatg atgctaaatc aatatatggt tctgtggtaa caaatgacat gggaactata | 660 |
| tgtgttagaa tagtcacatc caaacaaaga cacaatttaa acattgtctg tcgcatttac | 720 |
| cacaaagcca agcatataaa agcatggtgt ccacgcccac caagggctgt tccttatcaa | 780 |
| ttcacacatt ctactaatta cataccagat agtggtgagg taacaacaca aatcaaaccc | 840 |
| agaaccaatg tttttactat tacatctgct | 870 |

<210> SEQ ID NO 172
<211> LENGTH: 870
<212> TYPE: DNA
<213> ORGANISM: rhinovirus

<400> SEQUENCE: 172

| | |
|---|---|
| aatccagtag aaaattacat agataatgtg ttaaatgaag tacttgtagt tccaaatatc | 60 |
| caacctagta catctgtatc aagtcattct gtgcctgcct tggatgctgc agaaacggga | 120 |
| cacacaagtt ctgttcagcc tgaggatatg attgaaacta gatatgttat cacagatcaa | 180 |
| acaagagatg aaactagcat tgaaagcttt ttaggtagat ctggttgcat tgctatcata | 240 |
| aaatttaaca caaataagac taattatgat gacataggtg taggatacaa acatggaaa | 300 |
| attagccttc aagagatggc acaaattaga aggaaatttg agttgtttac atatacaaga | 360 |
| tttgactcag agattacaat agtcactgca gcagctgctc aaggagaaga taatggacat | 420 |
| attgtgttac aatttatgta tgtaccccca ggagcacctg tacccaagaa tcgtgatgac | 480 |
| tttacatggc aatcaggcac aaatgcatct gttttctggc aggaaggaca accatacct | 540 |
| agatttacaa tccctttat gagcattgca tcagcttact atatgtttta tgatggctat | 600 |
| gatggtgatg atgctaaatc aatatatggt tctgtggtaa caaatgacat gggaactata | 660 |
| tgtgttagaa tagtcacatc caaacaaaga cacaatttaa acattgtctg tcgcatttac | 720 |
| cacaaagcca agcatataaa agcatggtgt ccacgcccac caagggctgt tccttatcaa | 780 |

| | |
|---|---|
| ttcacacatt ctactaatta cataccagat agtggtgagg taacaacaca aatcaaaccc | 840 |
| agaaccaatg ttttactat tacatctgca | 870 |

<210> SEQ ID NO 173
<211> LENGTH: 870
<212> TYPE: DNA
<213> ORGANISM: rhinovirus

<400> SEQUENCE: 173

| | |
|---|---|
| aatccagtag aaaattacat agataatgtg ttaaatgaag tacttgtagt tccaaatatc | 60 |
| caacctagta catctgtatc aagtcattct gtgcctgcct tggatgctgc agaaacggga | 120 |
| cacacaagtt ctgttcagcc tgaggatatg attgaaacta gatatgttat cacagatcaa | 180 |
| acaagagatg aaactagcat tgaaagcttt ttaggtagat ctggttgcat tgctatcata | 240 |
| aaatttaaca caaataagac taattatgat gacataggtg taggatacaa aacatggaaa | 300 |
| attagccttc aagagatggc acaaattaga aggaaatttg agttgtttac atatacaaga | 360 |
| tttgactcag agattacaat agtcactgca gcagctgctc aaggagaaga taatggacat | 420 |
| attgtgttac aatttatgta tgtaccccca ggagcacctg tacccaagaa tcgtgatgac | 480 |
| tttacatggc aatcaggcac aaatgcatct gttttctggc aggaaggaca accataccct | 540 |
| agatttacaa tccctttat gagcattgca tcagcttact atatgtttta tgatggctat | 600 |
| gatggtgatg atgctaaatc aatatatggt tctgtggtaa caaatgacat gggaactata | 660 |
| tgtgttagaa tagtcacatc caaacaaaga cacaatttaa acattgtctg tcgcatttac | 720 |
| cacaaagcca agcatataaa agcatggtgt ccacgcccac caagggctgt tccttatcaa | 780 |
| ttcacacatt ctactaatta cataccagat agtggtgagg taacaacaca aatcaaaccc | 840 |
| agaaccaatg ttttactat tacatctgcc | 870 |

<210> SEQ ID NO 174
<211> LENGTH: 861
<212> TYPE: DNA
<213> ORGANISM: rhinovirus

<400> SEQUENCE: 174

| | |
|---|---|
| aatccagtag agagatatgt tgatgaggtg ctaaatgaag ttctagttgt tccaaacata | 60 |
| aacaaaagta atgggcagtt atcaaacgca gcaccagcgt tggacgctgc agaaactggt | 120 |
| cataccagcc aaaacacaacc agaagatgtg attgaaacca ggtatgtgat tacagaccag | 180 |
| actagagatg agatgtcaat tgaatctttc cttggtcggt ccggatgcat ttcaattatc | 240 |
| gaattggatt tagaccatga aggttattca gcagaaggga aaactttaa aacatggaag | 300 |
| ataaatctta aggaaatggc ccagattaga aggaaaaatg agcttttcac ctacttaagg | 360 |
| tttgattctg aaatcaccat tgttccaagc aatgcagcaa tagaaggaag caatggtcac | 420 |
| gtggtggtcc aatacatgta tgtacctcct ggtgccccac tacccaaaaa acgtgatgat | 480 |
| tacacatggc aatctggcac caacgcctca gttttttggc aggaaggtca accttacccc | 540 |
| agattcacaa tcccttttat tagtattgcc tcagcatatt acatgttta tgatggttat | 600 |
| gctgatgaca acccaagtgc accttatgga actgtagtta ccaatgacat gggttcactg | 660 |
| tgtgtcagaa tagttacaga ccagcaaaaa cataaagtta agattaccag tagaatatac | 720 |
| cataaagcaa aacatatcag tgcctggggc cctagaccac caagagctgt accataccag | 780 |
| catatacaca atccaaatta caagacaagt aatggagttc cagacaatag agtcaaactc | 840 |
| agagagacac tcaccacagt a | 861 |

<210> SEQ ID NO 175
<211> LENGTH: 861
<212> TYPE: DNA
<213> ORGANISM: rhinovirus

<400> SEQUENCE: 175

| | | | | | |
|---|---|---|---|---|---|
| aatccagtag | agagatatgt | tgatgaggtg | ctaaatgaag | ttctagttgt | tccaaacata | 60 |
| aacaaaagta | atgggcagtt | atcaaacgca | gcaccagcgt | tggacgctgc | agaaactggt | 120 |
| cataccagcc | aaaacacaacc | agaagatgtg | attgaaacca | ggtatgtgat | tacagaccag | 180 |
| actagagatg | agatgtcaat | tgaatctttc | cttggtcggt | ccggatgcat | ttcaattatc | 240 |
| gaattggatt | tagaccatga | aggttattca | gcagaaggga | aaaactttaa | acatggaag | 300 |
| ataaatctta | aggaaatggc | ccagattaga | aggaaaaatg | agcttttcac | ctacttaagg | 360 |
| tttgattctg | aaatcaccat | tgttccaagc | aatgcagcaa | tagaaggaag | caatggtcac | 420 |
| gtggtggtcc | aatacatgta | tgtacctcct | ggtgccccac | tacccaaaaa | acgtgatgat | 480 |
| tacacatggc | aatctggcac | caacgcctca | gttttttggc | aggaaggtca | accttacccc | 540 |
| agattcacaa | tccctttat | tagtattgcc | tcagcatatt | acatgtttta | tgatggttat | 600 |
| gctgatgaca | acccaagtgc | accttatgga | actgtagtta | ccaatgacat | gggttcactg | 660 |
| tgtgtcagaa | tagttacaga | ccagcaaaaa | cataaagtta | agattaccag | tagaatatac | 720 |
| cataaagcaa | aacatatcag | tgcctggggc | cctagaccac | caagagctgt | accataccag | 780 |
| catatacaca | atccaaatta | caagacaagt | aatggagttc | cagacaatag | agtcaaactc | 840 |
| agagagacac | tcaccacagt | g | | | | 861 |

<210> SEQ ID NO 176
<211> LENGTH: 861
<212> TYPE: DNA
<213> ORGANISM: rhinovirus

<400> SEQUENCE: 176

| | | | | | |
|---|---|---|---|---|---|
| aatccagtag | agagatatgt | tgatgaggtg | ctaaatgaag | ttctagttgt | tccaaacata | 60 |
| aacaaaagta | atgggcagtt | atcaaacgca | gcaccagcgt | tggacgctgc | agaaactggt | 120 |
| cataccagcc | aaaacacaacc | agaagatgtg | attgaaacca | ggtatgtgat | tacagaccag | 180 |
| actagagatg | agatgtcaat | tgaatctttc | cttggtcggt | ccggatgcat | ttcaattatc | 240 |
| gaattggatt | tagaccatga | aggttattca | gcagaaggga | aaaactttaa | acatggaag | 300 |
| ataaatctta | aggaaatggc | ccagattaga | aggaaaaatg | agcttttcac | ctacttaagg | 360 |
| tttgattctg | aaatcaccat | tgttccaagc | aatgcagcaa | tagaaggaag | caatggtcac | 420 |
| gtggtggtcc | aatacatgta | tgtacctcct | ggtgccccac | tacccaaaaa | acgtgatgat | 480 |
| tacacatggc | aatctggcac | caacgcctca | gttttttggc | aggaaggtca | accttacccc | 540 |
| agattcacaa | tccctttat | tagtattgcc | tcagcatatt | acatgtttta | tgatggttat | 600 |
| gctgatgaca | acccaagtgc | accttatgga | actgtagtta | ccaatgacat | gggttcactg | 660 |
| tgtgtcagaa | tagttacaga | ccagcaaaaa | cataaagtta | agattaccag | tagaatatac | 720 |
| cataaagcaa | aacatatcag | tgcctggggc | cctagaccac | caagagctgt | accataccag | 780 |
| catatacaca | atccaaatta | caagacaagt | aatggagttc | cagacaatag | agtcaaactc | 840 |
| agagagacac | tcaccacagt | t | | | | 861 |

<210> SEQ ID NO 177

```
<211> LENGTH: 861
<212> TYPE: DNA
<213> ORGANISM: rhinovirus

<400> SEQUENCE: 177
aatccagtgg aagaatatgt tgatcaggtt ttaaatgagg ttttagttgt tccaaacata      60
aaagaaagta aacccagtc tagcaactcc gctccagttt tggacgctgc agaaacaggt     120
catacgaacc aagtacagcc tgaagacacc atagaaacta gatatgttat aactgaccaa     180
acaagagatg aaatgagcat tgaaagtttc ctcggaagat caggttgtgc aacaattatg     240
agactagaat tggaccacac tgattacaat gctgaaggga aaaattttac aacgtggaaa     300
atcaacttac aggagatggc ccagattaga agaaagaatg agatgttcac atatctcaga     360
tttgattcag aaatcactct tgtgtgtgca gtggcctcac aaggagacaa taatggacat     420
gtggtgcttc aatttatgtt tgttccacct ggagccccta taccaaagaa gagagatgac     480
tatacttggc agtcaggcac caatgcatct gtgttttggc aacaaggtca aacataccc     540
aggttctcta taccattttc tagtattgcc tcagcttatt acatgtttta tgatggatac     600
tcggatgaca gcacatcctc tccatatggc actgtagtta ccaatgacat gggtacactg     660
tgtatgagga tggttacaga tcaacaacaa cataaggtca caattacagc tagagtctac     720
cacaaggcca aacatattag tgcatggggc ccaagacctc ctagagctgt accttatcag     780
cacatatata accctaatta taaaactgaa gaaggaactc cagacaccaa agtggcaatt     840
agagctaata ttaaaactgt a                                                861

<210> SEQ ID NO 178
<211> LENGTH: 861
<212> TYPE: DNA
<213> ORGANISM: rhinovirus

<400> SEQUENCE: 178
aatccagtgg aagaatatgt tgatcaggtt ttaaatgagg ttttagttgt tccaaacata      60
aaagaaagta aacccagtc tagcaactcc gctccagttt tggacgctgc agaaacaggt     120
catacgaacc aagtacagcc tgaagacacc atagaaacta gatatgttat aactgaccaa     180
acaagagatg aaatgagcat tgaaagtttc ctcggaagat caggttgtgc aacaattatg     240
agactagaat tggaccacac tgattacaat gctgaaggga aaaattttac aacgtggaaa     300
atcaacttac aggagatggc ccagattaga agaaagaatg agatgttcac atatctcaga     360
tttgattcag aaatcactct tgtgtgtgca gtggcctcac aaggagacaa taatggacat     420
gtggtgcttc aatttatgtt tgttccacct ggagccccta taccaaagaa gagagatgac     480
tatacttggc agtcaggcac caatgcatct gtgttttggc aacaaggtca aacataccc     540
aggttctcta taccattttc tagtattgcc tcagcttatt acatgtttta tgatggatac     600
tcggatgaca gcacatcctc tccatatggc actgtagtta ccaatgacat gggtacactg     660
tgtatgagga tggttacaga tcaacaacaa cataaggtca caattacagc tagagtctac     720
cacaaggcca aacatattag tgcatggggc ccaagacctc ctagagctgt accttatcag     780
cacatatata accctaatta taaaactgaa gaaggaactc cagacaccaa agtggcaatt     840
agagctaata ttaaaactgt g                                                861

<210> SEQ ID NO 179
<211> LENGTH: 861
<212> TYPE: DNA
<213> ORGANISM: rhinovirus
```

<400> SEQUENCE: 179

```
aatccagtgg aagaatatgt tgatcaggtt ttaaatgagg ttttagttgt tccaaacata      60
aaagaaagta aacccagtc tagcaactcc gctccagttt tggacgctgc agaaacaggt     120
catacgaacc aagtacagcc tgaagacacc atagaaacta gatatgttat aactgaccaa     180
acaagagatg aaatgagcat tgaaagtttc ctcggaagat caggttgtgc aacaattatg     240
agactagaat tggaccacac tgattacaat gctgaaggga aaaattttac aacgtggaaa     300
atcaacttac aggagatggc ccagattaga agaaagaatg agatgttcac atatctcaga     360
tttgattcag aaatcactct tgtgtgtgca gtggcctcac aaggagacaa taatggacat     420
gtggtgcttc aatttatgtt tgttccacct ggagccccta taccaaagaa gagagatgac     480
tatacttggc agtcaggcac caatgcatct gtgttttggc aacaaggtca aacatacccc     540
aggttctcta taccattttc tagtattgcc tcagcttatt acatgtttta tgatggatac     600
tcggatgaca gcacatcctc tccatatggc actgtagtta ccaatgacat gggtacactg     660
tgtatgagga tggttacaga tcaacaacaa cataaggtca caattacagc tagagtctac     720
cacaaggcca aacatattag tgcatggggc ccaagacctc ctagagctgt accttatcag     780
cacatatata accctaatta taaaactgaa gaaggaactc cagacaccaa agtggcaatt     840
agagctaata ttaaaactgt t                                                861
```

<210> SEQ ID NO 180
<211> LENGTH: 891
<212> TYPE: DNA
<213> ORGANISM: rhinovirus

<400> SEQUENCE: 180

```
aacccagtgg aaaggtacac agaagctatt ttaaatgaag ttcttgtagt tccaaatatc      60
acatctagta actcccaaac atcaaatgca gcaccagcac tagatgctgc tgagacagga     120
cacacaaacc aggtccagcc agaagatatg gtcgagacac ggtatgtaat tactgatcag     180
acccgtgatg aaatgagtgt ggaaagtttt cttggtagat ctggttgcat tgctatcata     240
catactgact tagatcatga agcacaacaa tataatgcac ccggaaaaaa tttctctcag     300
tggaagatca caatcaagga aatggctcaa atcagaagaa aatgtgagct ctttacatac     360
ctcagatttg attctgagat tacaatagta gcaacagtag ctgcactagg tcgggataat     420
gggcatgttg ttttacagta tatgtatgta ccaccagggg caccaatacc aaagactaga     480
gatgactaca catggcaatc agggacaaat gcatcagtat tttggcagca gggccaacct     540
tacccccagat ttaccattcc atttatgagt atagcttcag catattatat gtttttatgat     600
ggttatgaag atgataaggg aagtgtgtat gggtctgttg tcacaaacga tatgggcaca     660
ttgtgtgttc gtattgtgac tgagcagcag acacataagg ttaagataac cagtaggata     720
ttccacaagg caaagcatat tagtgcatgg tgtccaaggg ccccaagagc agtgccttat     780
caacacacta gagcacaaa cttagtgcca aggacaggtg aaattacaac tcatatcaga     840
ttcagaaaca ctgtcaaaga tctaacatac cccacagaaa tgacgaatgt t                891
```

<210> SEQ ID NO 181
<211> LENGTH: 891
<212> TYPE: DNA
<213> ORGANISM: rhinovirus

<400> SEQUENCE: 181

```
aacccagtgg aaaggtacac agaagctatt ttaaatgaag ttcttgtagt tccaaatatc        60
acatctagta actcccaaac atcaaatgca gcaccagcac tagatgctgc tgagacagga       120
cacacaaacc aggtccagcc agaagatatg gtcgagacac ggtatgtaat tactgatcag       180
acccgtgatg aaatgagtgt ggaaagtttt cttggtagat ctggttgcat tgctatcata       240
catactgact tagatcatga agcacaacaa tataatgcac ccggaaaaaa tttctctcag       300
tggaagatca caatcaagga aatggctcaa atcagaagaa aatgtgagct ctttacatac       360
ctcagatttg attctgagat tacaatagta gcaacagtag ctgcactagg tcgggataat       420
gggcatgttg ttttacagta tatgtatgta ccaccagggg caccaatacc aaagactaga       480
gatgactaca catggcaatc agggacaaat gcatcagtat tttggcagca gggccaacct       540
taccccagat ttaccattcc atttatgagt atagcttcag catattatat gttttatgat       600
ggttatgaag atgataaggg aagtgtgtat gggtctgttg tcacaaacga tatgggcaca       660
ttgtgtgttc gtattgtgac tgagcagcag acacataagg ttaagataac cagtaggata       720
ttccacaagg caaagcatat tagtgcatgg tgtccaaggg ccccaagagc agtgccttat       780
caacacacta agagcacaaa cttagtgcca aggacaggtg aaattacaac tcatatcaga       840
ttcagaaaca ctgtcaaaga tctaacatac cccacagaaa tgacgaatgt a               891

<210> SEQ ID NO 182
<211> LENGTH: 891
<212> TYPE: DNA
<213> ORGANISM: rhinovirus

<400> SEQUENCE: 182
aacccagtgg aaaggtacac agaagctatt ttaaatgaag ttcttgtagt tccaaatatc        60
acatctagta actcccaaac atcaaatgca gcaccagcac tagatgctgc tgagacagga       120
cacacaaacc aggtccagcc agaagatatg gtcgagacac ggtatgtaat tactgatcag       180
acccgtgatg aaatgagtgt ggaaagtttt cttggtagat ctggttgcat tgctatcata       240
catactgact tagatcatga agcacaacaa tataatgcac ccggaaaaaa tttctctcag       300
tggaagatca caatcaagga aatggctcaa atcagaagaa aatgtgagct ctttacatac       360
ctcagatttg attctgagat tacaatagta gcaacagtag ctgcactagg tcgggataat       420
gggcatgttg ttttacagta tatgtatgta ccaccagggg caccaatacc aaagactaga       480
gatgactaca catggcaatc agggacaaat gcatcagtat tttggcagca gggccaacct       540
taccccagat ttaccattcc atttatgagt atagcttcag catattatat gttttatgat       600
ggttatgaag atgataaggg aagtgtgtat gggtctgttg tcacaaacga tatgggcaca       660
ttgtgtgttc gtattgtgac tgagcagcag acacataagg ttaagataac cagtaggata       720
ttccacaagg caaagcatat tagtgcatgg tgtccaaggg ccccaagagc agtgccttat       780
caacacacta agagcacaaa cttagtgcca aggacaggtg aaattacaac tcatatcaga       840
ttcagaaaca ctgtcaaaga tctaacatac cccacagaaa tgacgaatgt g               891

<210> SEQ ID NO 183
<211> LENGTH: 891
<212> TYPE: DNA
<213> ORGANISM: rhinovirus

<400> SEQUENCE: 183
aacccagttg aaaatacac agaagccgtt cttaatgagg tccttgtggt tccaaacata        60
ccagcaagta ataccccaaac ttcaaatgca gccccagcct tagatgctgc tgagactgga       120
```

```
catacaaacc aagtccaacc agaagatgtg gttgaaacac gctatgtcat aacagaccag    180
acaagggatg aaatgagcat agagagcttc ctcggtaggt caggttgcat tgcaatcata    240
catactgact tagatcacaa tgaggatcag tacaatgcac ctggaaaaaa cttctcccaa    300
tggaaaatta caattaagga aatggctcaa attagaagaa agtgtgaact attcacatac    360
cttaggtttg actctgagat tacaatagta gcaacaatag ctgctcttgg aaaagataat    420
ggccatgtgg ttttacagta catgtatgtg ccgccagggg cacccatacc aaaaactaga    480
gatgattaca catggcagtc aggcactaat gcatcagtgt tttggcaaca aggcaaacct    540
taccccagat ttaccattcc atttatgagt atagcttcag catattatat gttttatgat    600
ggatatgagg atgacaaagg aagtgtgtat ggatctgttg ttacaaatga tatgggcaca    660
ttatgtgtcc gtattgtgac tgagcagcag acacataggg tcaaaataac cagcagaata    720
ttccataaag caaaacatat tagtgcgtgg tgtccaagag ctccaagagc agtgccctac    780
cagcacacca gaagtacaaa cttagtacca aaggaaggtg atattaaaac tcatattaaa    840
tttaggaata ctgttaaaga tttggcatat cctccagaat tagcaaacct t              891
```

```
<210> SEQ ID NO 184
<211> LENGTH: 891
<212> TYPE: DNA
<213> ORGANISM: rhinovirus

<400> SEQUENCE: 184
```

```
aacccagttg aaaaatacac agaagccgtt cttaatgagg tccttgtggt tccaaacata     60
ccagcaagta atacccaaac ttcaaatgca gccccagcct tagatgctgc tgagactgga    120
catacaaacc aagtccaacc agaagatgtg gttgaaacac gctatgtcat aacagaccag    180
acaagggatg aaatgagcat agagagcttc ctcggtaggt caggttgcat tgcaatcata    240
catactgact tagatcacaa tgaggatcag tacaatgcac ctggaaaaaa cttctcccaa    300
tggaaaatta caattaagga aatggctcaa attagaagaa agtgtgaact attcacatac    360
cttaggtttg actctgagat tacaatagta gcaacaatag ctgctcttgg aaaagataat    420
ggccatgtgg ttttacagta catgtatgtg ccgccagggg cacccatacc aaaaactaga    480
gatgattaca catggcagtc aggcactaat gcatcagtgt tttggcaaca aggcaaacct    540
taccccagat ttaccattcc atttatgagt atagcttcag catattatat gttttatgat    600
ggatatgagg atgacaaagg aagtgtgtat ggatctgttg ttacaaatga tatgggcaca    660
ttatgtgtcc gtattgtgac tgagcagcag acacataggg tcaaaataac cagcagaata    720
ttccataaag caaaacatat tagtgcgtgg tgtccaagag ctccaagagc agtgccctac    780
cagcacacca gaagtacaaa cttagtacca aaggaaggtg atattaaaac tcatattaaa    840
tttaggaata ctgttaaaga tttggcatat cctccagaat tagcaaacct t              891
```

```
<210> SEQ ID NO 185
<211> LENGTH: 891
<212> TYPE: DNA
<213> ORGANISM: rhinovirus

<400> SEQUENCE: 185
```

```
aacccagttg aaaaatacac agaagccgtt cttaatgagg tccttgtggt tccaaacata     60
ccagcaagta atacccaaac ttcaaatgca gccccagcct tagatgctgc tgagactgga    120
catacaaacc aagtccaacc agaagatgtg gttgaaacac gctatgtcat aacagaccag    180
```

| | |
|---|---|
| acaagggatg aaatgagcat agagagcttc ctcggtaggt caggttgcat tgcaatcata | 240 |
| catactgact tagatcacaa tgaggatcag tacaatgcac ctggaaaaaa cttctcccaa | 300 |
| tggaaaatta caattaagga aatggctcaa attagaagaa agtgtgaact attcacatac | 360 |
| cttaggtttg actctgagat tacaatagta gcaacaatag ctgctcttgg aaaagataat | 420 |
| ggccatgtgg ttttacagta catgtatgtg ccgccagggg cacccatacc aaaaactaga | 480 |
| gatgattaca catggcagtc aggcactaat gcatcagtgt tttggcaaca aggacaacct | 540 |
| taccccagat ttaccattcc atttatgagt atagcttcag catattatat gttttatgat | 600 |
| ggatatgagg atgacaaagg aagtgtgtat ggatctgttg ttacaaatga tatgggcaca | 660 |
| ttatgtgtcc gtattgtgac tgagcagcag acacataggg tcaaaataac cagcagaata | 720 |
| ttccataaag caaaacatat tagtgcgtgg tgtccaagca ctccaagagc agtgccctac | 780 |
| cagcacacca gaagtacaaa cttagtacca aaggaaggtg atattaaaac tcatattaaa | 840 |
| tttaggaata ctgttaaaga tttggcatat cctccagaat tagcaaacct t | 891 |

<210> SEQ ID NO 186
<211> LENGTH: 873
<212> TYPE: DNA
<213> ORGANISM: rhinovirus

<400> SEQUENCE: 186

| | |
|---|---|
| aatccagttg aaaaatatac tgaagcacta cttaatgaag tgcttgttgt gccaaacatc | 60 |
| aatcctagca acgcacaaac tacaaatgca gctcccgctc tcgatgccgc tgagacgggg | 120 |
| cacacaagcc aaacacaacc tgaagacatg gttgagacta ggtatgtaat cacagatcag | 180 |
| acccgtgatg aaatgagtat agagagtttc ttaggtaggt ctagttgcat tgcaataatc | 240 |
| catactgatg ttgtgcatga aacagacaag tacaaccacc cagggaagaa ttttagtaaa | 300 |
| tggaatatca ctctcaaaga aatggcccaa atcagaagaa agtgtgaaat gtttacatat | 360 |
| ctcagatttg attctgaaat tactatagtg gtgtcagttg caagtaaagg tgatgataat | 420 |
| gggcatgtag ttatgcaata tatgtatgta cctccaggag ccccccatccc cactaccaga | 480 |
| aatgattaca catggcaatc cagtaccaat gcctctgttt tctggcaaca aggacaacca | 540 |
| tatcccagat tcactatacc ttttatgagt attgcctcag cttattacat gttttatgat | 600 |
| ggttatgaag atgacaatgg aactacctat ggtgcagtgg ttacaaatca tatgggaaca | 660 |
| ctctgtgctc gcatagtaac tgaacaacag aagcatgaag tcaaaataac cagcataata | 720 |
| ttccacaaag ctaaacatgt cagtgcatgg tgccccagac ctccacgcgc tgtagcttat | 780 |
| caacatacat acagtccaaa ctttgtgcct caggaaggtg atgttgagac tcatattaaa | 840 |
| tttagaacag atgttaaaca gatcacaaca gtt | 873 |

<210> SEQ ID NO 187
<211> LENGTH: 873
<212> TYPE: DNA
<213> ORGANISM: rhinovirus

<400> SEQUENCE: 187

| | |
|---|---|
| aatccagttg aaaaatatac tgaagcacta cttaatgaag tgcttgttgt gccaaacatc | 60 |
| aatcctagca acgcacaaac tacaaatgca gctcccgctc tcgatgccgc tgagacgggg | 120 |
| cacacaagcc aaacacaacc tgaagacatg gttgagacta ggtatgtaat cacagatcag | 180 |
| acccgtgatg aaatgagtat agagagtttc ttaggtaggt ctagttgcat tgcaataatc | 240 |
| catactgatg ttgtgcatga aacagacaag tacaaccacc cagggaagaa ttttagtaaa | 300 |

| | |
|---|---|
| tggaatatca ctctcaaaga aatggcccaa atcagaagaa agtgtgaaat gtttacatat | 360 |
| ctcagatttg attctgaaat tactatagtg gtgtcagttg caagtaaagg tgatgataat | 420 |
| gggcatgtag ttatgcaata tatgtatgta cctccaggag cccccatccc cactaccaga | 480 |
| aatgattaca catggcaatc cagtaccaat gcctctgttt tctggcaaca aggacaacca | 540 |
| tatcccagat tcactatacc ttttatgagt attgcctcag cttattacat gttttatgat | 600 |
| ggttatgaag atgacaatgg aactacctat ggtgcagtgg ttacaaatca tatgggaaca | 660 |
| ctctgtgctc gcatagtaac tgaacaacag aagcatgaag tcaaaataac cagcataata | 720 |
| ttccacaaag ctaaacatgt cagtgcatgg tgccccagac ctccacgcgc tgtagcttat | 780 |
| caacatacat acagtccaaa ctttgtgcct caggaaggtg atgttgagac tcatattaaa | 840 |
| tttagaacag atgttaaaca gatcacaaca gta | 873 |

<210> SEQ ID NO 188
<211> LENGTH: 873
<212> TYPE: DNA
<213> ORGANISM: rhinovirus

<400> SEQUENCE: 188

| | |
|---|---|
| aatccagttg aaaatatac tgaagcacta cttaatgaag tgcttgttgt gccaaacatc | 60 |
| aatcctagca acgcacaaac tacaaatgca gctcccgctc tcgatgccgc tgagacgggg | 120 |
| cacacaagcc aaacacaacc tgaagacatg gttgagacta ggtatgtaat cacagatcag | 180 |
| acccgtgatg aaatgagtat agagagtttc ttaggtaggt ctagttgcat tgcaataatc | 240 |
| catactgatg ttgtgcatga acagacaag tacaaccacc cagggaagaa ttttagtaaa | 300 |
| tggaatatca ctctcaaaga aatggcccaa atcagaagaa agtgtgaaat gtttacatat | 360 |
| ctcagatttg attctgaaat tactatagtg gtgtcagttg caagtaaagg tgatgataat | 420 |
| gggcatgtag ttatgcaata tatgtatgta cctccaggag cccccatccc cactaccaga | 480 |
| aatgattaca catggcaatc cagtaccaat gcctctgttt tctggcaaca aggacaacca | 540 |
| tatcccagat tcactatacc ttttatgagt attgcctcag cttattacat gttttatgat | 600 |
| ggttatgaag atgacaatgg aactacctat ggtgcagtgg ttacaaatca tatgggaaca | 660 |
| ctctgtgctc gcatagtaac tgaacaacag aagcatgaag tcaaaataac cagcataata | 720 |
| ttccacaaag ctaaacatgt cagtgcatgg tgccccagac ctccacgcgc tgtagcttat | 780 |
| caacatacat acagtccaaa ctttgtgcct caggaaggtg atgttgagac tcatattaaa | 840 |
| tttagaacag atgttaaaca gatcacaaca gtc | 873 |

<210> SEQ ID NO 189
<211> LENGTH: 876
<212> TYPE: DNA
<213> ORGANISM: rhinovirus

<400> SEQUENCE: 189

| | |
|---|---|
| aacccggtag agaaatacac agaggctatc ttaaatgaag tattagtagt cccaaacatt | 60 |
| aatgcaagca atccacaaac ttcaaattca gcaccagcac tagatgctgc agaaacgggt | 120 |
| catacaagtc agacacaacc tgaggacatg ctggaaacta gatatgtcat cacagaccaa | 180 |
| acccgggatg aaatgagcat tgaaagtttc ttaggcagat caagttgcat tgctgagatc | 240 |
| cataccaatt tagaccatac tggatacaat gagcctggga aaaaccactc agaatggaag | 300 |
| attacactca agaaatggc ccagattaga aggaaatgtg agatgttcac atatcttaga | 360 |

| | |
|---|---|
| tttgattcag aaataactat agtggtatca gtggctagta aacaagggaa taacgggcac | 420 |
| gtggtgatac aatacatgta tgtaccaccg ggtgctccaa tacccaaaac cagagatgac | 480 |
| tatacctggc aatctggaac taatgcttca gtcttttggc aacaaggaca accataccct | 540 |
| agattcacaa tccctttcat gagtattgcg tcagcatatt atatgttcta tgatgggtat | 600 |
| gaagatgaca atggcaccac ttatggggct gttgttacta atgatatggg aacactttgt | 660 |
| gtgcgcatag tgactgagca acagaaaaat gaggtcaaga taaccagtag gatttatcac | 720 |
| aaggctaaac atatcagtgc atggtgtcca agaccaccaa gagcagttgc atatcaacac | 780 |
| acatatagcc caaattttgt accgcaaaca ggaacagttg aaactcacat taagttcaga | 840 |
| cctgatgtta aagatgtaac atcagtaatg acagct | 876 |

<210> SEQ ID NO 190
<211> LENGTH: 876
<212> TYPE: DNA
<213> ORGANISM: rhinovirus

<400> SEQUENCE: 190

| | |
|---|---|
| aacccggtag agaaatacac agaggctatc ttaaatgaag tattagtagt cccaaacatt | 60 |
| aatgcaagca atccacaaac ttcaaattca gcaccagcac tagatgctgc agaaacgggt | 120 |
| catacaagtc agacacaacc tgaggacatg ctggaaacta gatatgtcat cacagaccaa | 180 |
| acccgggatg aaatgagcat tgaaagtttc ttaggcagat caagttgcat tgctgagatc | 240 |
| cataccaatt tagaccatac tggatacaat gagcctggga aaaaccactc agaatggaag | 300 |
| attacactca agaaatggc ccagattaga aggaaatgtg agatgttcac atatcttaga | 360 |
| tttgattcag aaataactat agtggtatca gtggctagta acaagggaa taacgggcac | 420 |
| gtggtgatac aatacatgta tgtaccaccg ggtgctccaa tacccaaaac cagagatgac | 480 |
| tatacctggc aatctggaac taatgcttca gtcttttggc aacaaggaca accataccct | 540 |
| agattcacaa tccctttcat gagtattgcg tcagcatatt atatgttcta tgatgggtat | 600 |
| gaagatgaca atggcaccac ttatggggct gttgttacta atgatatggg aacactttgt | 660 |
| gtgcgcatag tgactgagca acagaaaaat gaggtcaaga taaccagtag gatttatcac | 720 |
| aaggctaaac atatcagtgc atggtgtcca agaccaccaa gagcagttgc atatcaacac | 780 |
| acatatagcc caaattttgt accgcaaaca ggaacagttg aaactcacat taagttcaga | 840 |
| cctgatgtta aagatgtaac atcagtaatg acagct | 876 |

<210> SEQ ID NO 191
<211> LENGTH: 876
<212> TYPE: DNA
<213> ORGANISM: rhinovirus

<400> SEQUENCE: 191

| | |
|---|---|
| aacccggtag agaaatacac agaggctatc ttaaatgaag tattagtagt cccaaacatt | 60 |
| aatgcaagca atccacaaac ttcaaattca gcaccagcac tagatgctgc agaaacgggt | 120 |
| catacaagtc agacacaacc tgaggacatg ctggaaacta gatatgtcat cacagaccaa | 180 |
| acccgggatg aaatgagcat tgaaagtttc ttaggcagat caagttgcat tgctgagatc | 240 |
| cataccaatt tagaccatac tggatacaat gagcctggga aaaaccactc agaatggaag | 300 |
| attacactca agaaatggc ccagattaga aggaaatgtg agatgttcac atatcttaga | 360 |
| tttgattcag aaataactat agtggtatca gtggctagta acaagggaa taacgggcac | 420 |
| gtggtgatac aatacatgta tgtaccaccg ggtgctccaa tacccaaaac cagagatgac | 480 |

```
tatacctggc aatctggaac taatgcttca gtcttttggc aacaaggaca accatacect      540 agattcacaa tcccttttcat gagtattgcg tcagcatatt atatgttcta tgatgggtat     600
gaagatgaca atggcaccac ttatggggct gttgttacta atgatatggg aacactttgt     660
gtgcgcatag tgactgagca acagaaaaat gaggtcaaga taaccagtag gatttatcac     720
aaggctaaac atatcagtgc atggtgtcca agaccaccaa gagcagttgc atatcaacac     780
acatatagcc caaattttgt accgcaaaca ggaacagttg aaactcacat taagttcaga     840
cctgatgtta aagatgtaac atcagtaatg acagca                                876
```

<210> SEQ ID NO 192
<211> LENGTH: 879
<212> TYPE: DNA
<213> ORGANISM: rhinovirus

<400> SEQUENCE: 192

```
aatccagtgg aaaaatatac agaagctgtt cttaatgagg tccttgtagt acctaacatc     60
aatgccagta gtggacatac atctaattca gctccagcac ttgatgcagc agaaactgga    120
cacactagcc agatacaacc agaagacatg atagaaacca gatatgttat cacagaccaa    180
acaaaagatg aaatgagtat agaaagtttt ctaggaaggt caggctgcat tgccattatt    240
gagacagaat tgaatcatga agagggaaa tacaatgcag aagatcaaaa cttctcaaaa     300
tggaaaataa cactgttgga aatggcacaa atcagaagaa agtgtgaact ttttacatat    360
ctcagatttg attcagaaat aacaatagtc accacattgg caggccaagg ggatgatatt    420
ggacatgtgg tcatacaata tatgtatgtg cctcctggtg ctccattacc gagatatcgg    480
aatgattata cttggcagtc tggtactaat gcttcagtgt tctggcagca agggcagcca    540
taccctagat tcactatccc gttcatgagt atagcctcag catattacat gttttatgat    600
ggctacgaaa gtgataaagg caagatctat ggaactgcag tcaccaatga tatgggaact    660
atatgtgtca gaattgttac cgaacaacaa aaacataagg ttcttataac tagcagaata    720
tatcacaagg ctaaacacat taaagcatgg tgccccaggg cacccagagc agtcccatat    780
caacatattt taatccaaa tttcaagact actcaacctg agactatacc agatactcat     840
attggaatta gaagggatat aaagtacatt aaaacagca                            879
```

<210> SEQ ID NO 193
<211> LENGTH: 879
<212> TYPE: DNA
<213> ORGANISM: rhinovirus

<400> SEQUENCE: 193

```
aatccagtgg aaaaatatac agaagctgtt cttaatgagg tccttgtagt acctaacatc     60
aatgccagta gtggacatac atctaattca gctccagcac ttgatgcagc agaaactgga    120
cacactagcc agatacaacc agaagacatg atagaaacca gatatgttat cacagaccaa    180
acaaaagatg aaatgagtat agaaagtttt ctaggaaggt caggctgcat tgccattatt    240
gagacagaat tgaatcatga agagggaaa tacaatgcag aagatcaaaa cttctcaaaa     300
tggaaaataa cactgttgga aatggcacaa atcagaagaa agtgtgaact ttttacatat    360
ctcagatttg attcagaaat aacaatagtc accacattgg caggccaagg ggatgatatt    420
ggacatgtgg tcatacaata tatgtatgtg cctcctggtg ctccattacc gagatatcgg    480
aatgattata cttggcagtc tggtactaat gcttcagtgt tctggcagca agggcagcca    540
```

```
tacccctagat tcactatccc gttcatgagt atagcctcag catattacat gttttatgat      600
ggctacgaaa gtgataaagg caagatctat ggaactgcag tcaccaatga tatgggaact      660
atatgtgtca gaattgttac cgaacaacaa aaacataagg ttcttataac tagcagaata      720
tatcacaagg ctaaacacat taaagcatgg tgccccaggg cacccagagc agtcccatat      780
caacatattt ataatccaaa tttcaagact actcaacctg agactatacc agatactcat      840
attggaatta gaagggatat aaagtacatt aaaacagcc                             879

<210> SEQ ID NO 194
<211> LENGTH: 879
<212> TYPE: DNA
<213> ORGANISM: rhinovirus

<400> SEQUENCE: 194
aatccagtgg aaaaatatac agaagctgtt cttaatgagg tccttgtagt acctaacatc      60
aatgccagta gtggacatac atctaattca gctccagcac ttgatgcagc agaaactgga     120
cacactagcc agatacaacc agaagacatg atagaaacca gatatgttat cacagaccaa     180
acaaaagatg aaatgagtat agaaagtttt ctaggaaggt caggctgcat tgccattatt     240
gagacagaat tgaatcatga agaagggaaa tacaatgcag aagatcaaaa cttctcaaaa     300
tggaaaataa cactgttgga aatggcacaa atcagaagaa agtgtgaact ttttacatat     360
ctcagatttg attcagaaat aacaatagtc accacattgg caggccaagg ggatgatatt     420
ggacatgtgg tcatacaata tatgtatgtg cctcctggtg ctccattacc gagatatcgg     480
aatgattata cttggcagtc tggtactaat gcttcagtgt tctggcagca agggcagcca     540 tacccctagat tcactatccc gttcatgagt atagcctcag catattacat gttttatgat      600
ggctacgaaa gtgataaagg caagatctat ggaactgcag tcaccaatga tatgggaact      660
atatgtgtca gaattgttac cgaacaacaa aaacataagg ttcttataac tagcagaata      720
tatcacaagg ctaaacacat taaagcatgg tgccccaggg cacccagagc agtcccatat      780
caacatattt ataatccaaa tttcaagact actcaacctg agactatacc agatactcat      840
attggaatta gaagggatat aaagtacatt aaaacagct                             879

<210> SEQ ID NO 195
<211> LENGTH: 876
<212> TYPE: DNA
<213> ORGANISM: rhinovirus

<400> SEQUENCE: 195
aatccagtcg aaaaatacac agaagcaatc ctcaatgaag ttcttgttgt accaaacatc      60
agtgctagca atggacatac atcaaactca gctccaacac ttgatgcagc agaaactggt     120
cacactagcc aggtgcaacc agaagacatg atagaaacta gatatgttat tactgatcag     180
acaaaggatg agatgagcat tgaaagtttc ttaggaagat ctggttgtgt tgctatcatt     240
gaaaccaaat taaccatgaa acagacatg tacaatgctg atggtcagaa tttttcaaag     300
tggaaaataa cattaatgga aatggcacaa attagaagaa agtgtgagct tttcacttac     360
ctcagatttg actcagaaat aacaatagta actacccttag caggacaagg ggaggacatt     420
ggtcatgtag ttattcaata catgtacgta ccaccagggg ccccgttgcc aaacaaacgc     480
aatgattata cttggcagtc tggcacgaat gcttcagtct tctggcaaca gggtcagcca     540
taccccagat tcactattcc attcatgagt atagcctcag cttattacat gttctatgat      600
gggtatgaga gtgataaagg caacatttat ggaacagcag ttaccaatga tatgggaacc      660
```

| | |
|---|---:|
| ctgtgtgcta gaattgttac agaacaacag aaacataaag tcctaatcac cagcagaata | 720 |
| tatcacaaag ctaaacacat caaagcatgg tgtccaagag cacctagagc agtcccatac | 780 |
| caacatacct acagcccaaa tttcaaaaac actgatgaat ctataccaga tacacaaatt | 840 |
| aaaatcagag ataatatcag gcaggttaga acagta | 876 |

<210> SEQ ID NO 196
<211> LENGTH: 876
<212> TYPE: DNA
<213> ORGANISM: rhinovirus

<400> SEQUENCE: 196

| | |
|---|---:|
| aatccagtcg aaaatacac agaagcaatc ctcaatgaag ttcttgttgt accaaacatc | 60 |
| agtgctagca atggacatac atcaaactca gctccaacac ttgatgcagc agaaactggt | 120 |
| cacactagcc aggtgcaacc agaagacatg atagaaacta gatatgttat tactgatcag | 180 |
| acaaaggatg agatgagcat tgaaagtttc ttaggaagat ctggttgtgt tgctatcatt | 240 |
| gaaaccaaat taaccatga aacagacatg tacaatgctg atggtcagaa ttttttcaaag | 300 |
| tggaaaataa cattaatgga aatggcacaa attagaagaa agtgtgagct tttcacttac | 360 |
| ctcagatttg actcagaaat aacaatagta actaccttag caggacaagg ggaggacatt | 420 |
| ggtcatgtag ttattcaata catgtacgta ccaccagggg ccccgttgcc aaacaaacgc | 480 |
| aatgattata cttggcagtc tggcacgaat gcttcagtct tctggcaaca gggtcagcca | 540 |
| taccccagat tcactattcc attcatgagt atagcctcag cttattacat gttctatgat | 600 |
| gggtatgaga gtgataaagg caacatttat ggaacagcag ttaccaatga tatgggaacc | 660 |
| ctgtgtgcta gaattgttac agaacaacag aaacataaag tcctaatcac cagcagaata | 720 |
| tatcacaaag ctaaacacat caaagcatgg tgtccaagag cacctagagc agtcccatac | 780 |
| caacatacct acagcccaaa tttcaaaaac actgatgaat ctataccaga tacacaaatt | 840 |
| aaaatcagag ataatatcag gcaggttaga acagtc | 876 |

<210> SEQ ID NO 197
<211> LENGTH: 876
<212> TYPE: DNA
<213> ORGANISM: rhinovirus

<400> SEQUENCE: 197

| | |
|---|---:|
| aatccagtcg aaaatacac agaagcaatc ctcaatgaag ttcttgttgt accaaacatc | 60 |
| agtgctagca atggacatac atcaaactca gctccaacac ttgatgcagc agaaactggt | 120 |
| cacactagcc aggtgcaacc agaagacatg atagaaacta gatatgttat tactgatcag | 180 |
| acaaaggatg agatgagcat tgaaagtttc ttaggaagat ctggttgtgt tgctatcatt | 240 |
| gaaaccaaat taaccatga aacagacatg tacaatgctg atggtcagaa ttttttcaaag | 300 |
| tggaaaataa cattaatgga aatggcacaa attagaagaa agtgtgagct tttcacttac | 360 |
| ctcagatttg actcagaaat aacaatagta actaccttag caggacaagg ggaggacatt | 420 |
| ggtcatgtag ttattcaata catgtacgta ccaccagggg ccccgttgcc aaacaaacgc | 480 |
| aatgattata cttggcagtc tggcacgaat gcttcagtct tctggcaaca gggtcagcca | 540 |
| taccccagat tcactattcc attcatgagt atagcctcag cttattacat gttctatgat | 600 |
| gggtatgaga gtgataaagg caacatttat ggaacagcag ttaccaatga tatgggaacc | 660 |
| ctgtgtgcta gaattgttac agaacaacag aaacataaag tcctaatcac cagcagaata | 720 |

```
tatcacaaag ctaaacacat caaagcatgg tgtccaagag cacctagagc agtcccatac    780
caacatacct acagcccaaa tttcaaaaac actgatgaat ctataccaga tacacaaatt    840
aaaatcagag ataatatcag gcaggttaga acagtt                              876
```

<210> SEQ ID NO 198
<211> LENGTH: 888
<212> TYPE: DNA
<213> ORGANISM: rhinovirus

<400> SEQUENCE: 198

```
aaccctgttg aaaatatac agaggcttta ctcaatgaag tgttggtggt tcccaacata     60
caacctagca gtgggcacac atctaatgct gcaccagctc tagatgctgc tgagacagga   120
catactagtc aagttcaacc agaagatatg gtagagacca ggtatgttgt cacagaccaa   180
actagagatg aaatgagtat agagagtttc ttgggtagat ctgcttgcgt agcaatcatc   240
catacaaacc ttgagcatgt tgaagcagac agacaagcct acaatgcaaa agggaaaaat   300
ttctctacat ggaaaattac actcaaagaa atggctcaaa ttagaagaaa gtgtgaactt   360
ttcacatact taagatttga ttcagagatc actatagttg ctaccattgc tggacagggt   420
gatgacatag ggcacattgt acttcaatac atgtatgtac cccctggagg accagttcca   480
cttactagga aagatgatga gtggcaatca ggaactaatg cttcagtatt ctggcaacat   540
ggacaaccat accctagatt tacaatccct tttgtaagca tagcctcagc atactacatg   600
ttttatgatg ggtatgaagg tgatagtttg acctcacagt acggttcagt agtcacaaat   660
gctatgggga cactatgtgt tcgtgtggtc acagagcaac aaaaacatga ggttaacata   720
actagcagga tttaccacaa agccaaacat gtcagtgcat ggtgccctcg tcctcctcgt   780
gctgtagcct accaacacac atacagtaca aacttcgttc caaaagaggg atttgaaggc   840
ttgaaaactc agattaaaac tagggcagac atcaaacttg tgaactttt                888
```

<210> SEQ ID NO 199
<211> LENGTH: 888
<212> TYPE: DNA
<213> ORGANISM: rhinovirus

<400> SEQUENCE: 199

```
aaccctgttg aaaatatac agaggcttta ctcaatgaag tgttggtggt tcccaacata     60
caacctagca gtgggcacac atctaatgct gcaccagctc tagatgctgc tgagacagga   120
catactagtc aagttcaacc agaagatatg gtagagacca ggtatgttgt cacagaccaa   180
actagagatg aaatgagtat agagagtttc ttgggtagat ctgcttgcgt agcaatcatc   240
catacaaacc ttgagcatgt tgaagcagac agacaagcct acaatgcaaa agggaaaaat   300
ttctctacat ggaaaattac actcaaagaa atggctcaaa ttagaagaaa gtgtgaactt   360
ttcacatact taagatttga ttcagagatc actatagttg ctaccattgc tggacagggt   420
gatgacatag ggcacattgt acttcaatac atgtatgtac cccctggagg accagttcca   480
cttactagga aagatgatga gtggcaatca ggaactaatg cttcagtatt ctggcaacat   540
ggacaaccat accctagatt tacaatccct tttgtaagca tagcctcagc atactacatg   600
ttttatgatg ggtatgaagg tgatagtttg acctcacagt acggttcagt agtcacaaat   660
gctatgggga cactatgtgt tcgtgtggtc acagagcaac aaaaacatga ggttaacata   720
actagcagga tttaccacaa agccaaacat gtcagtgcat ggtgccctcg tcctcctcgt   780
gctgtagcct accaacacac atacagtaca aacttcgttc caaaagaggg atttgaaggc   840
```
ttgaaaactc agattaaaac tagggcagac atcaaacttg tgaactta            888

<210> SEQ ID NO 200
<211> LENGTH: 888
<212> TYPE: DNA
<213> ORGANISM: rhinovirus

<400> SEQUENCE: 200
aaccctgttg aaaatatac agaggcttta ctcaatgaag tgttggtggt tcccaacata    60
caacctagca gtgggcacac atctaatgct gcaccagctc tagatgctgc tgagacagga   120
catactagtc aagttcaacc agaagatatg gtagagacca ggtatgttgt cacagaccaa   180
actagagatg aaatgagtat agagagtttc ttgggtagat ctgcttgcgt agcaatcatc   240
catacaaacc ttgagcatgt tgaagcagac agacaagcct acaatgcaaa agggaaaaat   300
ttctctacat ggaaaattac actcaaagaa atggctcaaa ttagaagaaa gtgtgaactt   360
ttcacatact taagatttga ttcagagatc actatagttg ctaccattgc tggacagggt   420
gatgacatag gcacattgt acttcaatac atgtatgtac ccctggagg accagttcca    480 cttactagga aagatgatga gtggcaatca ggaactaatg cttcagtatt ctggcaacat   540
ggacaaccat accctagatt tacaatccct tttgtaagca tagcctcagc atactacatg   600
ttttatgatg ggtatgaagg tgatagtttg acctcacagt acggttcagt agtcacaaat   660
gctatgggga cactatgtgt tcgtgtggtc acagagcaac aaaaacatga ggttaacata   720
actagcagga tttaccacaa agccaaacat gtcagtgcat ggtgccctcg tcctcctcgt   780
gctgtagcct accaacacac atacagtaca aacttcgttc caaagagggg atttgaaggc   840
ttgaaaactc agattaaaac tagggcagac atcaaacttg tgaacttg              888

<210> SEQ ID NO 201
<211> LENGTH: 888
<212> TYPE: DNA
<213> ORGANISM: rhinovirus

<400> SEQUENCE: 201
aatccaattg agaagtatac agaagctcta cttaatgaag tgttggtggt cccaaatata    60
caagctagta atgggcatac atctaatgct gcaccagctt tagatgctgc tgaaacagga   120
cacactagtc aagttcaacc agaggatgtg atagaaacca gatatgtcat cacagatcaa   180
accagagatg agatgagcgt agagagtttc ctgggcagat ctgcctgcat agcagtcatt   240
cacacagatc ttaaacatga ccatgaaggc caaaatgttt acaatgacga aggcagaaat   300
ttctctgctt gggaaattac actcaaggaa atggctcaaa ttaggagaaa gtgtgaactc   360
ttcacctatt tgcgctttga ctcagaaatt accatagtgg ctactatagc tggacaaggt   420
gatgacatag gcacatagt gcttcaatat atgtatgtgc ctcctggtgg tcctgttcca   480
aaaactagaa aagatgaaga gtggcagaca ggaactaatg cttcagtctt ttggcagcat   540
ggtcaaccat accccagatt tacaattcct tttgtgagta ttgcctcagc atattacatg   600
ttctatgatg gttatgaggg tgatgaccca aattcaaaat atggttcagt ggttactaat   660
gctatgggca cactatatgt gcgtgtggtt acagaaaggc aaaaacatga agtcaacata   720
accagtagaa tatatcataa agctaaacac atcagtgctt ggtgtccacg acctccccga   780
gcagtagctt accaacacac atacagtaca aattttgttc ctagcggagg tcttacaaac   840
ctaagaaccc aaattaaaac cagagataac attaaaattg taaacttg                888

<210> SEQ ID NO 202
<211> LENGTH: 888
<212> TYPE: DNA
<213> ORGANISM: rhinovirus

<400> SEQUENCE: 202

```
aatccaattg agaagtatac agaagctcta cttaatgaag tgttggtggt cccaaatata    60
caagctagta atgggcatac atctaatgct gcaccagctt tagatgctgc tgaaacagga   120
cacactagtc aagttcaacc agaggatgtg atagaaacca gatatgtcat cacagatcaa   180
accagagatg agatgagcgt agagagtttc ctgggcagat ctgcctgcat agcagtcatt   240
cacacagatc ttaaacatga ccatgaaggc caaaatgttt acaatgacga aggcagaaat   300
ttctctgctt gggaaattac actcaaggaa atggctcaaa ttaggagaaa gtgtgaactc   360
ttcacctatt tgcgctttga ctcagaaatt accatagtgg ctactatagc tggacaaggt   420
gatgacatag gcacatagt gcttcaatat atgtatgtgc ctcctggtgg tcctgttcca   480
aaaactagaa aagatgaaga gtggcagaca ggaactaatg cttcagtctt ttggcagcat   540
ggtcaaccat accccagatt tacaattcct tttgtgagta ttgcctcagc atattacatg   600
ttctatgatg gttatgaggg tgatgaccca aattcaaaat atggttcagt ggttactaat   660
gctatgggca cactatatgt gcgtgtggtt acagaaaggc aaaaacatga agtcaacata   720
accagtagaa tatatcataa agctaaacac atcagtgctt ggtgtccacg acctccccga   780
gcagtagctt accaacacac atacagtaca aattttgttc ctagcggagg tcttacaaac   840
ctaagaaccc aaattaaaac cagagataac attaaaattg taaactta              888
```

<210> SEQ ID NO 203
<211> LENGTH: 888
<212> TYPE: DNA
<213> ORGANISM: rhinovirus

<400> SEQUENCE: 203

```
aatccaattg agaagtatac agaagctcta cttaatgaag tgttggtggt cccaaatata    60
caagctagta atgggcatac atctaatgct gcaccagctt tagatgctgc tgaaacagga   120
cacactagtc aagttcaacc agaggatgtg atagaaacca gatatgtcat cacagatcaa   180
accagagatg agatgagcgt agagagtttc ctgggcagat ctgcctgcat agcagtcatt   240
cacacagatc ttaaacatga ccatgaaggc caaaatgttt acaatgacga aggcagaaat   300
ttctctgctt gggaaattac actcaaggaa atggctcaaa ttaggagaaa gtgtgaactc   360
ttcacctatt tgcgctttga ctcagaaatt accatagtgg ctactatagc tggacaaggt   420
gatgacatag gcacatagt gcttcaatat atgtatgtgc ctcctggtgg tcctgttcca   480
aaaactagaa aagatgaaga gtggcagaca ggaactaatg cttcagtctt ttggcagcat   540
ggtcaaccat accccagatt tacaattcct tttgtgagta ttgcctcagc atattacatg   600
ttctatgatg gttatgaggg tgatgaccca aattcaaaat atggttcagt ggttactaat   660
gctatgggca cactatatgt gcgtgtggtt acagaaaggc aaaaacatga agtcaacata   720
accagtagaa tatatcataa agctaaacac atcagtgctt ggtgtccacg acctccccga   780
gcagtagctt accaacacac atacagtaca aattttgttc ctagcggagg tcttacaaac   840
ctaagaaccc aaattaaaac cagagataac attaaaattg taaacttt              888
```

<210> SEQ ID NO 204
<211> LENGTH: 885

```
<212> TYPE: DNA
<213> ORGANISM: rhinovirus

<400> SEQUENCE: 204
aatcctgtag aaaaatatac agaagcaata ctcaatgagg ttctagttgt gccaaatata      60
caacctagta atggacatac ctcaaactca gcaccagcct tagatgcagc agaaactggg     120
cataccaacc aagtacaacc agaagatgtt atggaaacca gatatgtgat cactgatcaa     180
actagggatg aaatgagcat tgagagcttc ttgggcagat ctgcatgcat agctaccata     240
cacactaaat tagtacatgg agaggagggt gtttataata tgaaaggtaa caatctctca     300
aagtggcaga ttacactcaa agaaatggct cagatcagga ggaaatgtga actcttcaca     360
tacctgcgct ttgattcaga gataacaatt gtagctacac tagcagggca aggagatgat     420
ttaggacata ttgtactcca gtacatgtat gttcccccag gtggtccaat accagagacc     480
agggatgccg atgaatggca gtctggaact aatgcatcag tcttttggca gcacggccaa     540
ccatacccaa ggtttacaat cccccttcata agcattgcat cagcatatta catgttctat     600
gatgggtatg aaggtgatgc cctcagttct aaatatggct cagtagttac taatgccatg     660
ggcaccttat gtgttcgtgt ggttacagaa cagcaaagca acacagtcaa cataacaagt     720
aggatttatc acaaagccaa acatgtcaga gcatggtgtc ctagaccccc cagagcagta     780
gcctaccaat caacatatac cacaaatttt gttccacaag acgggatcaa ttccattaaa     840
accaaaatca aaatcagaag agacattaaa gaggtcagca actaa                     885

<210> SEQ ID NO 205
<211> LENGTH: 885
<212> TYPE: DNA
<213> ORGANISM: rhinovirus

<400> SEQUENCE: 205
aatcctgtag aaaaatatac agaagcaata ctcaatgagg ttctagttgt gccaaatata      60
caacctagta atggacatac ctcaaactca gcaccagcct tagatgcagc agaaactggg     120
cataccaacc aagtacaacc agaagatgtt atggaaacca gatatgtgat cactgatcaa     180
actagggatg aaatgagcat tgagagcttc ttgggcagat ctgcatgcat agctaccata     240
cacactaaat tagtacatgg agaggagggt gtttataata tgaaaggtaa caatctctca     300
aagtggcaga ttacactcaa agaaatggct cagatcagga ggaaatgtga actcttcaca     360
tacctgcgct ttgattcaga gataacaatt gtagctacac tagcagggca aggagatgat     420
ttaggacata ttgtactcca gtacatgtat gttcccccag gtggtccaat accagagacc     480
agggatgccg atgaatggca gtctggaact aatgcatcag tcttttggca gcacggccaa     540
ccatacccaa ggtttacaat cccccttcata agcattgcat cagcatatta catgttctat     600
gatgggtatg aaggtgatgc cctcagttct aaatatggct cagtagttac taatgccatg     660
ggcaccttat gtgttcgtgt ggttacagaa cagcaaagca acacagtcaa cataacaagt     720
aggatttatc acaaagccaa acatgtcaga gcatggtgtc ctagaccccc cagagcagta     780
gcctaccaat caacatatac cacaaatttt gttccacaag acgggatcaa ttccattaaa     840
accaaaatca aaatcagaag agacattaaa gaggtcagca actag                     885

<210> SEQ ID NO 206
<211> LENGTH: 885
<212> TYPE: DNA
<213> ORGANISM: rhinovirus
```

```
<400> SEQUENCE: 206
aatcctgtag aaaaatatac agaagcaata ctcaatgagg ttctagttgt gccaaatata    60
caacctagta atggacatac ctcaaactca gcaccagcct tagatgcagc agaaactggg   120
cataccaacc aagtacaacc agaagatgtt atggaaacca gatatgtgat cactgatcaa   180
actagggatg aaatgagcat tgagagcttc ttgggcagat ctgcatgcat agctaccata   240
cacactaaat tagtacatgg agaggagggt gtttataata tgaaaggtaa caatctctca   300
aagtggcaga ttacactcaa agaaatggct cagatcagga ggaaatgtga actcttcaca   360
tacctgcgct ttgattcaga gataacaatt gtagctacac tagcagggca aggagatgat   420
ttaggacata ttgtactcca gtacatgtat gttcccccag gtggtccaat accagagacc   480
agggatgccg atgaatggca gtctggaact aatgcatcag tcttttggca gcacggccaa   540 ccataccaa ggtttacaat ccccttcata agcattgcat cagcatatta catgttctat   600
gatgggtatg aaggtgatgc cctcagttct aaatatggct cagtagttac taatgccatg   660
ggcaccttat gtgttcgtgt ggttacagaa cagcaaagca acacagtcaa cataacaagt   720
aggatttatc acaaagccaa acatgtcaga gcatggtgtc ctagaccccc cagagcagta   780
gcctaccaat caacatatac cacaaatttt gttccacaag acgggatcaa ttccattaaa   840
accaaaatca aaatcagaag agacattaaa gaggtcagca actat                   885

<210> SEQ ID NO 207
<211> LENGTH: 852
<212> TYPE: DNA
<213> ORGANISM: rhinovirus

<400> SEQUENCE: 207
aaccctattg aacaattcac agaggcagta ttaaacgagg ttcttgtagt tccaaacaca    60
caagctagta atggatctat agcaaattca gcaccagcat tagatgcagc agagactgga   120
cacacaagtt cagtgcaacc tgaagatctt atagagacta ggtatgtaat tacagatcaa   180
actaggcatg agacatcact ggaatctttc ttgggtagag caggatgcat taaaatcatt   240
gcattagaac tagatcatga caactatgat gaaagtttca ggacctgggg aataaacata   300
caagagatgt cacaaattag aaggaaattt gagatgttca cttatgtaag atttgattca   360
gagataacaa ttgtaccatg tattgcagct ataaaaggtg accttggaca catagtcctt   420
caatacatgt atgttccccc gggtgcacct cttccagata aaaggatgca cgatgcctgg   480
caaaccagta caaatgcctc agtcttctgg caagttggac aaacttatcc cagattcacc   540
atacctttct ccagcatagc atcagcttat tacatgttct atgatggtta tgattcagat   600
ggtttagatg ctatttatgg tattcctgtt acaaatcaca tgggcacaat atgtgtgaga   660
atggtgacag ataaacagaa aattaaaact aaaattgatt caagaatata cctgaaagca   720
aagcacatta agcttggtg tcctagaccc cccagagcag ttacgtataa ccatatatac   780
aaccccaatt atgttagaga gggagtaaca ccagaaacta aggttaaata tagagctgaa   840
gtcacaacca tt                                                        852

<210> SEQ ID NO 208
<211> LENGTH: 852
<212> TYPE: DNA
<213> ORGANISM: rhinovirus

<400> SEQUENCE: 208
aaccctattg aacaattcac agaggcagta ttaaacgagg ttcttgtagt tccaaataca    60
```

-continued

```
caagccagta atggatctat agcaaattca gcaccagcat tagatgcagc agagactgga      120
cacacaagtt cagtgcaacc tgaagatctt atagagacta ggtatgtaat tacagatcaa      180
actaggtatg agacatcact ggaatctttc ttgggtagag caggatgcat taaaattatt      240
gcattagaac tagatcatga caactatgat aaaaatttca ggacctgggg aataaacata      300
caagagatgt cacaaattag aaggaaattt gaaatgttca cttatgtaag atttgattca      360
gagataacaa ttgtaccatg tattgcagct atagaaggtg accttggaca catagtcctc      420
caatacatgt atgttccccc gggtgcacct cttccagata aaaggatgca cgatgcctgg      480
caaaccagta caaatgcctc agtcttctgg caagttggac agacttatcc cagattcacc      540
atacctttct ccagtatagc atcagcttat tacatgttct atgatggtta tgattcagat      600
ggtttagatg ctatttatgg tattcctgtt acaaatcaca tgggcacaat atgtgtgaga      660
atggtgacag ataaacagaa aattaaaact aaaattgatt caagaatata cctgaaagca      720
aagcatatta aagcttggtg tcctagaccc cccagagcag ttacgtataa ccatatatac      780
aaccccaatt atgttagaga gggagtaaca ccagaaacta aggtcaaata tagagctgaa      840
gtcacaacca tt                                                          852

<210> SEQ ID NO 209
<211> LENGTH: 849
<212> TYPE: DNA
<213> ORGANISM: rhinovirus

<400> SEQUENCE: 209
aaccctgttg aacaatttgc agaagcagtc cttgatcaag tattagtagt tccaaacact       60
cgacccagcg atgggttgat tgcaaactca gccccagctt tggatgcagc tgaaactgga      120
cacaccagtt cagtgcagcc tgaggacctt atagagacta gatatgtgat tgcagaccaa      180
accagacatg aaacctccat tgaatctttt ttgggtaggg ctggatgtgt ggccaatatt      240
agtttagaca ttaaccatga tgactaccaa agaattaca aaaattgggc aattagttta      300
caagaaatgt cacaaattag gaggaaattt gaaatgttta catatgtcag atttgattcc      360
gaaataacaa tagtaccatg tgttgctgcc acagaaggta acttgggaca cattgttgtg      420
caatacatgt ttgtaccacc aggagcacct ctccctgtta gtagaactga caacacttgg      480
caatctagca caaatgcatc agtctttgg caggttggtc aaacttatcc cagatttct      540 atacctttct caagtatagc ttcagcttac tacatgtttt atgatggata cgacactgat      600
ggcacagatg cagtgtatgg tgttagtgtg actaaccata tggggactat atgtgttaga      660
attgttacag accaacaaca acatagagtt aagatcgact ccatggtata tctaaaagct      720
aaacacatca aggcatggtg tcccagacct ccaagagcag tcacatataa ccatacatat      780
aatccaaatt atgttagggc tgatgaaaca gccacaaaag tccaaactag agcaaatgtc      840
acaacagta                                                              849

<210> SEQ ID NO 210
<211> LENGTH: 849
<212> TYPE: DNA
<213> ORGANISM: rhinovirus
```

<400> SEQUENCE: 210

```
aaccctgttg aacaatttgc agaagcagtc cttgatcaag tattagtagt tccaaacact    60
cgacccagcg atgggttgat tgcaaactca gccccagctt tggatgcagc tgaaactgga   120
cacaccagtt cagtgcagcc tgaggacctt atagagacta gatatgtgat tgcagaccaa   180
accagacatg aaacctccat tgaatctttt ttgggtaggg ctggatgtgt ggccaatatt   240
agtttagaca ttaaccatga tgactaccaa aagaattaca aaaattgggc aattagttta   300
caagaaatgt cacaaattag gaggaaattt gaaatgttta catatgtcag atttgattcc   360
gaaataacaa tagtaccatg tgttgctgcc acagaaggta acttgggaca cattgttgtg   420
caatacatgt ttgtaccacc aggagcacct ctccctgtta gtagaactga caacacttgg   480
caatctagca caaatgcatc agtcttttgg caggttggtc aaacttatcc cagattttct   540
atacctttct caagtatagc ttcagcttac tacatgtttt atgatggata cgacactgat   600
ggcacagatg cagtgtatgg tgttagtgtg actaaccata tggggactat atgtgttaga   660
attgttacag accaacaaca acatagagtt aagatcgact ccatggtata tctaaaagct   720
aaacacatca aggcatggtg tcccagacct ccaagagcag tcacatataa ccatacatat   780
aatccaaatt atgttagggc tgatgaaaca gccacaaaag tccaaactag agcaaatgtc   840
acaacagtg                                                          849
```

<210> SEQ ID NO 211
<211> LENGTH: 849
<212> TYPE: DNA
<213> ORGANISM: rhinovirus

<400> SEQUENCE: 211

```
aaccctgttg aacaatttgc agaagcagtc cttgatcaag tattagtagt tccaaacact    60
cgacccagcg atgggttgat tgcaaactca gccccagctt tggatgcagc tgaaactgga   120
cacaccagtt cagtgcagcc tgaggacctt atagagacta gatatgtgat tgcagaccaa   180
accagacatg aaacctccat tgaatctttt ttgggtaggg ctggatgtgt ggccaatatt   240
agtttagaca ttaaccatga tgactaccaa aagaattaca aaaattgggc aattagttta   300
caagaaatgt cacaaattag gaggaaattt gaaatgttta catatgtcag atttgattcc   360
gaaataacaa tagtaccatg tgttgctgcc acagaaggta acttgggaca cattgttgtg   420
caatacatgt ttgtaccacc aggagcacct ctccctgtta gtagaactga caacacttgg   480
caatctagca caaatgcatc agtcttttgg caggttggtc aaacttatcc cagattttct   540
atacctttct caagtatagc ttcagcttac tacatgtttt atgatggata cgacactgat   600
ggcacagatg cagtgtatgg tgttagtgtg actaaccata tggggactat atgtgttaga   660
attgttacag accaacaaca acatagagtt aagatcgact ccatggtata tctaaaagct   720
aaacacatca aggcatggtg tcccagacct ccaagagcag tcacatataa ccatacatat   780
aatccaaatt atgttagggc tgatgaaaca gccacaaaag tccaaactag agcaaatgtc   840
acaacagtt                                                          849
```